(12) United States Patent
Mainolfi et al.

(10) Patent No.: US 10,874,743 B2
(45) Date of Patent: Dec. 29, 2020

(54) IRAK DEGRADERS AND USES THEREOF

(71) Applicant: Kymera Therapeutics, Inc., Cambridge, MA (US)

(72) Inventors: Nello Mainolfi, Belmont, MA (US); Nan Ji, Arlington, MA (US); Arthur F. Kluge, Concord, MA (US); Matthew M. Weiss, Boston, MA (US); Yi Zhang, Belmont, MA (US)

(73) Assignee: KYMERA THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 16/230,792

(22) Filed: Dec. 21, 2018

(65) Prior Publication Data

US 2019/0192668 A1 Jun. 27, 2019

Related U.S. Application Data

(60) Provisional application No. 62/610,397, filed on Dec. 26, 2017, provisional application No. 62/653,178, filed on Apr. 5, 2018, provisional application No. 62/694,955, filed on Jul. 6, 2018, provisional application No. 62/712,377, filed on Jul. 31, 2018.

(51) Int. Cl.
| | |
|---|---|
| *A61P 35/00* | (2006.01) |
| *A61K 31/404* | (2006.01) |
| *A61K 31/422* | (2006.01) |
| *A61K 31/427* | (2006.01) |
| *A61K 31/4439* | (2006.01) |
| *A61K 31/444* | (2006.01) |
| *A61K 31/454* | (2006.01) |
| *A61K 31/472* | (2006.01) |
| *A61K 31/496* | (2006.01) |
| *A61K 31/519* | (2006.01) |
| *A61K 31/53* | (2006.01) |
| *A61K 31/5377* | (2006.01) |
| *A61K 47/54* | (2017.01) |

(52) U.S. Cl.
CPC .......... *A61K 47/545* (2017.08); *A61K 31/404* (2013.01); *A61K 31/422* (2013.01); *A61K 31/427* (2013.01); *A61K 31/444* (2013.01); *A61K 31/4439* (2013.01); *A61K 31/454* (2013.01); *A61K 31/472* (2013.01); *A61K 31/496* (2013.01); *A61K 31/519* (2013.01); *A61K 31/53* (2013.01); *A61K 31/5377* (2013.01); *A61P 35/00* (2018.01)

(58) Field of Classification Search
CPC .. A61K 47/545; A61K 31/404; A61K 31/422; A61K 31/427; A61K 31/4439; A61K 31/444; A61K 31/454; A61K 31/472; A61K 31/496; A61K 31/519; A61K 31/53; A61K 31/5377; A61P 35/00
USPC .................................................. 514/210.18
See application file for complete search history.

(56) References Cited

U.S. PATENT DOCUMENTS

| | | | |
|---|---|---|---|
| 4,650,750 | A | 3/1987 | Giese |
| 4,709,016 | A | 11/1987 | Giese |
| 5,360,811 | A | 11/1994 | Tegeler et al. |
| 5,360,819 | A | 11/1994 | Giese |
| 5,516,931 | A | 5/1996 | Giese et al. |
| 5,602,273 | A | 2/1997 | Giese et al. |
| 5,604,104 | A | 2/1997 | Giese et al. |
| 5,610,020 | A | 3/1997 | Giese et al. |
| 5,650,270 | A | 7/1997 | Giese et al. |
| 5,721,246 | A | 2/1998 | Yoshino et al. |
| 6,306,663 | B1 | 10/2001 | Kenten et al. |
| 6,552,065 | B2 | 4/2003 | Remiszewski et al. |
| 6,559,280 | B2 | 5/2003 | Kenten et al. |
| 6,627,754 | B2 | 9/2003 | Blumenkopf et al. |
| 6,949,537 | B2 | 9/2005 | Garlich et al. |
| 7,041,298 | B2 | 5/2006 | Deshaies et al. |
| 7,071,189 | B2 | 7/2006 | Kawashima et al. |
| 7,074,620 | B2 | 7/2006 | Kenten et al. |
| 7,173,015 | B2 | 2/2007 | Schreiber et al. |
| 7,208,157 | B2 | 4/2007 | Deshaies et al. |
| 7,273,920 | B2 | 9/2007 | Kenten et al. |
| 7,307,077 | B2 | 12/2007 | Kawashima et al. |
| 7,390,799 | B2 | 6/2008 | Bruncko et al. |
| 7,402,325 | B2 | 7/2008 | Addington |
| 7,449,458 | B2 | 11/2008 | Bhamidipati et al. |
| 7,501,496 | B1 | 3/2009 | Endl et al. |
| 7,514,444 | B2 | 4/2009 | Honigberg et al. |
| 7,528,143 | B2 | 5/2009 | Noronha et al. |
| 7,557,210 | B2 | 7/2009 | Singh et al. |
| 7,598,257 | B2 | 10/2009 | Rodgers et al. |
| 7,622,496 | B2 | 11/2009 | Larsen et al. |
| 7,667,039 | B2 | 2/2010 | Garcia-Echeverria et al. |
| 7,713,943 | B2 | 5/2010 | Klippel-Giese et al. |
| 7,781,433 | B2 | 8/2010 | Chuckowree et al. |

(Continued)

FOREIGN PATENT DOCUMENTS

| | | |
|---|---|---|
| CN | 105085620 | 5/2018 |
| WO | WO2001042246 | 6/2001 |

(Continued)

OTHER PUBLICATIONS

Aruri et al., "Metal-free Cross-Dehydrogenative Coupling of HN-azoles with a-C(sp3)-H Amides via C—H Activation and Its Mechanistic and Application Studies," The Journal of Organic Chemistry, vol. 82, No. 2, 2016 (pp. 1000-1012).

(Continued)

*Primary Examiner* — Kristin A Vajda

(74) *Attorney, Agent, or Firm* — Dechert LLP; Andrea L. C. Reid; Todd K. Macklin

(57) ABSTRACT

The present invention provides compounds, compositions thereof, and methods of using the same.

20 Claims, 10 Drawing Sheets

(56) References Cited

U.S. PATENT DOCUMENTS

| | | |
|---|---|---|
| 7,932,260 B2 | 4/2011 | Fowler et al. |
| 7,989,622 B2 | 8/2011 | Bajjalieh et al. |
| 8,138,347 B2 | 3/2012 | Knight et al. |
| 8,185,616 B2 | 5/2012 | Nagata et al. |
| 8,217,035 B2 | 7/2012 | Burger et al. |
| 8,338,439 B2 | 12/2012 | Singh et al. |
| 8,486,941 B2 | 7/2013 | Burns et al. |
| 8,906,682 B2 | 12/2014 | June et al. |
| 9,500,653 B2 | 11/2016 | Crews et al. |
| 9,632,089 B2 | 4/2017 | Crews et al. |
| 9,694,084 B2 | 4/2017 | Bradner et al. |
| 9,750,816 B2 | 9/2017 | Bradner et al. |
| 9,770,512 B2 | 9/2017 | Bradner et al. |
| 9,821,068 B2 | 11/2017 | Bradner et al. |
| 9,969,710 B2 | 5/2018 | Jorand-Lebrun et al. |
| 10,125,114 B2 | 11/2018 | Bradner et al. |
| 10,336,744 B2 | 7/2019 | Harling et al. |
| 2001/0053782 A1 | 12/2001 | Blumenkopf et al. |
| 2002/0042427 A1 | 4/2002 | Tang et al. |
| 2002/0068063 A1 | 6/2002 | Deshaies et al. |
| 2002/0183360 A1 | 12/2002 | Muller et al. |
| 2004/0029902 A1 | 2/2004 | Singh et al. |
| 2004/0048859 A1 | 3/2004 | Germann et al. |
| 2004/0106569 A1 | 6/2004 | Klippel-Giese et al. |
| 2004/0116421 A1 | 6/2004 | Kawashima et al. |
| 2004/0242631 A1 | 12/2004 | Garlich et al. |
| 2005/0014802 A1 | 1/2005 | Attardo et al. |
| 2005/0075306 A1 | 4/2005 | Schreiber et al. |
| 2006/0211657 A1 | 9/2006 | Singh et al. |
| 2007/0098719 A1 | 5/2007 | Smith et al. |
| 2007/0135461 A1 | 6/2007 | Rodgers et al. |
| 2007/0191405 A1 | 8/2007 | Noronha et al. |
| 2008/0076768 A1 | 3/2008 | Chuckowree et al. |
| 2008/0108636 A1 | 6/2008 | Honigberg et al. |
| 2008/0194579 A1 | 8/2008 | Garcia-Echeverria et al. |
| 2008/0275067 A1 | 11/2008 | Fowler et al. |
| 2009/0055944 A1 | 2/2009 | Korman et al. |
| 2009/0136494 A1 | 5/2009 | Ponath et al. |
| 2009/0233903 A1 | 9/2009 | Rodgers et al. |
| 2010/0197671 A1 | 2/2010 | Burns et al. |
| 2010/0197686 A1 | 2/2010 | Xing et al. |
| 2010/0203056 A1 | 2/2010 | Irving et al. |
| 2010/0087440 A1 | 4/2010 | Bajjalieh et al. |
| 2010/0150892 A1 | 6/2010 | Han |
| 2010/0233183 A1 | 9/2010 | Triebel et al. |
| 2010/0247554 A1 | 9/2010 | Lemke et al. |
| 2010/0249092 A1 | 9/2010 | Singh et al. |
| 2010/0249126 A1 | 9/2010 | Burger et al. |
| 2010/0279316 A1 | 11/2010 | Gorelik et al. |
| 2011/0008331 A1 | 1/2011 | Triebel et al. |
| 2011/0053941 A1 | 3/2011 | Mautino et al. |
| 2011/0136796 A1 | 6/2011 | Mautino et al. |
| 2011/0165156 A1 | 7/2011 | Dimoudis et al. |
| 2011/0223611 A1 | 9/2011 | Salamone et al. |
| 2011/0274683 A1 | 11/2011 | Wong et al. |
| 2012/0015962 A1 | 1/2012 | Arora et al. |
| 2012/0189639 A1 | 7/2012 | Schebye et al. |
| 2012/0277217 A1 | 11/2012 | Mautino et al. |
| 2012/0283238 A1 | 11/2012 | Romero et al. |
| 2012/0329997 A1 | 12/2012 | Fertig et al. |
| 2013/0005949 A1 | 1/2013 | Fertig et al. |
| 2013/0149236 A1 | 6/2013 | Johnson et al. |
| 2013/0190340 A1 | 7/2013 | Hedstrom et al. |
| 2013/0231328 A1 | 9/2013 | Harriman et al. |
| 2013/0274241 A1 | 10/2013 | Jorand-Lebrun et al. |
| 2014/0018343 A1 | 1/2014 | Romero et al. |
| 2014/0018357 A1 | 1/2014 | Harriman et al. |
| 2014/0018361 A1 | 1/2014 | Harriman et al. |
| 2014/0066625 A1 | 3/2014 | Mautino et al. |
| 2014/0079699 A1 | 3/2014 | Wong et al. |
| 2014/0079706 A1 | 3/2014 | Cannarile et al. |
| 2014/0093511 A1 | 4/2014 | Lonberg et al. |
| 2014/0155379 A1 | 6/2014 | Ho et al. |
| 2014/0194404 A1 | 7/2014 | McElroy et al. |
| 2014/0302523 A1 | 10/2014 | Crews et al. |
| 2014/0329799 A1 | 11/2014 | Seganish et al. |
| 2014/0336363 A1 | 11/2014 | Fertig et al. |
| 2014/0341917 A1 | 11/2014 | Nastri et al. |
| 2014/0356322 A1 | 12/2014 | Crews et al. |
| 2015/0011532 A1 | 1/2015 | Paidi et al. |
| 2015/0018344 A1 | 1/2015 | Paidi et al. |
| 2015/0045347 A1 | 2/2015 | Dodd et al. |
| 2015/0094305 A1 | 4/2015 | Romero et al. |
| 2015/0133451 A1 | 5/2015 | Yoshida et al. |
| 2015/0141396 A1 | 5/2015 | Crosignani et al. |
| 2015/0191464 A1 | 7/2015 | Santella et al. |
| 2015/0225449 A1 | 8/2015 | Donnell et al. |
| 2015/0274708 A1 | 10/2015 | Seganish et al. |
| 2015/0274738 A1 | 10/2015 | Gray et al. |
| 2015/0284382 A1 | 10/2015 | Bhide et al. |
| 2015/0284405 A1 | 10/2015 | Trzupek et al. |
| 2015/0291562 A1 | 10/2015 | Crew et al. |
| 2015/0299224 A1 | 10/2015 | Seganish et al. |
| 2015/0329498 A1 | 11/2015 | Romero et al. |
| 2015/0374678 A1 | 12/2015 | Chamberlain et al. |
| 2015/0376167 A1 | 12/2015 | Jorand-Lebrun et al. |
| 2015/0376206 A1 | 12/2015 | Jorand-Lebrun et al. |
| 2016/0002265 A1 | 1/2016 | Jenkins et al. |
| 2016/0022642 A1 | 1/2016 | Crews et al. |
| 2016/0045607 A1 | 2/2016 | Crews et al. |
| 2016/0058872 A1 | 3/2016 | Crew et al. |
| 2016/0145252 A1 | 5/2016 | Jorand-Lebrun et al. |
| 2016/0176916 A1 | 6/2016 | Bradner et al. |
| 2016/0214972 A1 | 7/2016 | Jin et al. |
| 2016/0235730 A1 | 8/2016 | Bradner et al. |
| 2016/0235731 A1 | 8/2016 | Bradner et al. |
| 2016/0243247 A1 | 8/2016 | Bradner et al. |
| 2016/0272596 A1 | 9/2016 | Chen et al. |
| 2016/0272639 A1 | 9/2016 | Crew et al. |
| 2016/0311833 A1 | 10/2016 | Bothe et al. |
| 2016/0311839 A1 | 10/2016 | Li et al. |
| 2016/0326151 A1 | 11/2016 | Gummadi et al. |
| 2016/0340366 A1 | 11/2016 | Gummadi et al. |
| 2017/0001990 A1 | 1/2017 | Chen et al. |
| 2017/0008904 A1 | 1/2017 | Crew et al. |
| 2017/0022189 A1 | 1/2017 | Zhang |
| 2017/0037004 A1 | 2/2017 | Crew et al. |
| 2017/0121321 A1 | 5/2017 | Crews et al. |
| 2017/0152263 A1 | 6/2017 | Gummadi et al. |
| 2017/0204093 A1 | 7/2017 | Chan et al. |
| 2017/0247388 A1 | 8/2017 | Altman et al. |
| 2017/0281784 A1 | 10/2017 | Wang et al. |
| 2017/0327469 A1 | 11/2017 | Crew et al. |
| 2017/0369476 A1 | 12/2017 | Chen et al. |
| 2018/0009779 A1 | 1/2018 | Bradner et al. |
| 2018/0015087 A1 | 1/2018 | Liu et al. |
| 2018/0051027 A1 | 2/2018 | Lim et al. |
| 2018/0051028 A1 | 2/2018 | Lim et al. |
| 2018/0051029 A1 | 2/2018 | Lim et al. |
| 2018/0051030 A1 | 2/2018 | Lim et al. |
| 2018/0051035 A1 | 2/2018 | Lim et al. |
| 2018/0085465 A1 | 3/2018 | Bradner et al. |
| 2018/0118733 A1 | 5/2018 | Harling et al. |
| 2018/0134684 A1 | 5/2018 | Bradner et al. |
| 2018/0147202 A1 | 5/2018 | Crew et al. |
| 2018/0186799 A1 | 7/2018 | Gardner et al. |
| 2018/0201609 A1 | 7/2018 | Gummadi et al. |
| 2018/0208605 A1 | 7/2018 | Gummadi et al. |
| 2018/0228907 A1 | 8/2018 | Crew et al. |
| 2018/0230157 A1 | 8/2018 | Bacon et al. |
| 2019/0071415 A1 | 3/2019 | Bradner et al. |
| 2019/0076539 A1 | 3/2019 | Phillips et al. |
| 2019/0076540 A1 | 3/2019 | Phillips et al. |
| 2019/0076541 A1 | 3/2019 | Phillips et al. |
| 2019/0076542 A1 | 3/2019 | Phillips et al. |
| 2019/0151457 A1 | 5/2019 | Bradner et al. |
| 2019/0276474 A1 | 9/2019 | Chan et al. |
| 2020/0010468 A1 | 1/2020 | Ji et al. |

FOREIGN PATENT DOCUMENTS

| | | |
|---|---|---|
| WO | WO2002020740 | 3/2002 |
| WO | WO2002088112 | 11/2002 |
| WO | WO2003063794 | 8/2003 |

(56) References Cited

FOREIGN PATENT DOCUMENTS

| | | |
|---|---|---|
| WO | WO2004019973 | 3/2004 |
| WO | WO2004089925 | 10/2004 |
| WO | WO2004106328 | 12/2004 |
| WO | WO2005007623 | 1/2005 |
| WO | WO2005113554 | 12/2005 |
| WO | WO2006029879 | 3/2006 |
| WO | WO2006078846 | 7/2006 |
| WO | WO2006105021 | 10/2006 |
| WO | WO2006122806 | 11/2006 |
| WO | WO2007005874 | 1/2007 |
| WO | WO2007016176 | 2/2007 |
| WO | WO2007044729 | 4/2007 |
| WO | WO2007053452 | 5/2007 |
| WO | WO2007070514 | 6/2007 |
| WO | WO2007084786 | 7/2007 |
| WO | WO2007129161 | 11/2007 |
| WO | WO2008039218 | 4/2008 |
| WO | WO2008109943 | 9/2008 |
| WO | WO2008118802 | 10/2008 |
| WO | WO2008132601 | 11/2008 |
| WO | WO2009009116 | 1/2009 |
| WO | WO2009044273 | 4/2009 |
| WO | WO2009073620 | 6/2009 |
| WO | WO2009114512 | 10/2009 |
| WO | WO2009132238 | 10/2009 |
| WO | WO2010019570 | 2/2010 |
| WO | WO2010077634 | 7/2010 |
| WO | WO2011028683 | 3/2011 |
| WO | WO2011043371 | 4/2011 |
| WO | WO2011056652 | 5/2011 |
| WO | WO2011070024 | 6/2011 |
| WO | WO2011090760 | 7/2011 |
| WO | WO2011107553 | 9/2011 |
| WO | WO2011109400 | 9/2011 |
| WO | WO2011131407 | 10/2011 |
| WO | WO2011140249 | 11/2011 |
| WO | WO2012003281 | 1/2012 |
| WO | WO2012007375 | 1/2012 |
| WO | WO2012032433 | 3/2012 |
| WO | WO2012068546 | 5/2012 |
| WO | WO2012078559 | 6/2012 |
| WO | WO2012084704 | 6/2012 |
| WO | WO2012097013 | 7/2012 |
| WO | WO2012129258 | 9/2012 |
| WO | WO2012142237 | 10/2012 |
| WO | WO2012145493 | 10/2012 |
| WO | WO2013042137 | 3/2013 |
| WO | WO2013066729 | 5/2013 |
| WO | WO2013079174 | 6/2013 |
| WO | WO2013087699 | 6/2013 |
| WO | WO2013106535 | 7/2013 |
| WO | WO2013106612 | 7/2013 |
| WO | WO2013106614 | 7/2013 |
| WO | WO2013106641 | 7/2013 |
| WO | WO2013106643 | 7/2013 |
| WO | WO2013106646 | 7/2013 |
| WO | WO2013119716 | 8/2013 |
| WO | WO2013132044 | 9/2013 |
| WO | WO2013169264 | 11/2013 |
| WO | WO2014008218 | 1/2014 |
| WO | WO2014008992 | 1/2014 |
| WO | WO2014011902 | 1/2014 |
| WO | WO2014011906 | 1/2014 |
| WO | WO2014011911 | 1/2014 |
| WO | WO2014036357 | 3/2014 |
| WO | WO2014044622 | 3/2014 |
| WO | WO2014058685 | 4/2014 |
| WO | WO2014058691 | 4/2014 |
| WO | WO2014063061 | 4/2014 |
| WO | WO2014074675 | 5/2014 |
| WO | WO2014108452 | 7/2014 |
| WO | WO2014121931 | 8/2014 |
| WO | WO2014121942 | 8/2014 |
| WO | WO2014143672 | 9/2014 |
| WO | WO2015048281 | 4/2015 |
| WO | WO2015068856 | 5/2015 |
| WO | WO2015071393 | 5/2015 |
| WO | WO2015091426 | 6/2015 |
| WO | WO2015103453 | 7/2015 |
| WO | WO2015104662 | 7/2015 |
| WO | WO2015104688 | 7/2015 |
| WO | WO2015150995 | 10/2015 |
| WO | WO2015160845 | 10/2015 |
| WO | WO2015164374 | 10/2015 |
| WO | WO2015193846 | 12/2015 |
| WO | WO2016011390 | 1/2016 |
| WO | WO2016053769 | 4/2016 |
| WO | WO2016053770 | 4/2016 |
| WO | WO2016053771 | 4/2016 |
| WO | WO2016053772 | 4/2016 |
| WO | WO2016081679 | 5/2016 |
| WO | WO2016105518 | 6/2016 |
| WO | WO2016118666 | 7/2016 |
| WO | WO2016144844 | 9/2016 |
| WO | WO2016144846 | 9/2016 |
| WO | WO2016144847 | 9/2016 |
| WO | WO2016144848 | 9/2016 |
| WO | WO2016144849 | 9/2016 |
| WO | WO2016149668 | 9/2016 |
| WO | WO2016169989 | 10/2016 |
| WO | WO2016172560 | 10/2016 |
| WO | WO2016174183 | 11/2016 |
| WO | WO2016197032 | 12/2016 |
| WO | WO2016197114 | 12/2016 |
| WO | WO2016210034 | 12/2016 |
| WO | WO2017004133 | 1/2017 |
| WO | WO2017004134 | 1/2017 |
| WO | WO2017007612 | 1/2017 |
| WO | WO2017009798 | 1/2017 |
| WO | WO2017009806 | 1/2017 |
| WO | WO2017011371 | 1/2017 |
| WO | WO2017011590 | 1/2017 |
| WO | WO2017030814 | 2/2017 |
| WO | WO2017033093 | 3/2017 |
| WO | WO2017049068 | 3/2017 |
| WO | WO2017059280 | 4/2017 |
| WO | WO2017079267 | 5/2017 |
| WO | WO2017108723 | 6/2017 |
| WO | WO2017117473 | 7/2017 |
| WO | WO2017117474 | 7/2017 |
| WO | WO2017127430 | 7/2017 |
| WO | WO2017161119 | 9/2017 |
| WO | WO2017176708 | 10/2017 |
| WO | WO2017176957 | 10/2017 |
| WO | WO2017176958 | 10/2017 |
| WO | WO2017197036 | 11/2017 |
| WO | WO2017197046 | 11/2017 |
| WO | WO2017197051 | 11/2017 |
| WO | WO2017197055 | 11/2017 |
| WO | WO2017197056 | 11/2017 |
| WO | WO2017201449 | 11/2017 |
| WO | WO2017205762 | 11/2017 |
| WO | WO2017205766 | 11/2017 |
| WO | WO2017207385 | 12/2017 |
| WO | WO2017211924 | 12/2017 |
| WO | WO2018052058 | 3/2018 |
| WO | WO2018098367 | 5/2018 |
| WO | WO2018144649 | 8/2018 |
| WO | WO2018209012 | 11/2018 |
| WO | WO2018237026 | 12/2018 |
| WO | WO2019043214 | 3/2019 |
| WO | WO2019060693 | 3/2019 |
| WO | WO2019060742 | 3/2019 |
| WO | WO2019084026 | 5/2019 |
| WO | WO2019084030 | 5/2019 |
| WO | WO2019099868 | 5/2019 |
| WO | WO2019099926 | 5/2019 |
| WO | WO2019140380 | 7/2019 |
| WO | WO2019140387 | 7/2019 |
| WO | WO2019165229 | 8/2019 |
| WO | WO2020010177 | 1/2020 |

(56) References Cited

FOREIGN PATENT DOCUMENTS

| WO | WO2020010210 | 1/2020 |
|---|---|---|
| WO | WO2020010227 | 1/2020 |

OTHER PUBLICATIONS

Boichenko et al. "A FRET-Based Assay for the Identification and Characterization of Cereblon Ligands," Journal of Medicinal Chemistry, vol. 59, No. 2, 2016 (pp. 770-774).
Chang et al., "What is the functional role of the thalidomide binding protein cereblon?", International Journal of Biochemistry and Molecular Biology, vol. 2, No. 3, 2011 (pp. 287-294).
Connolly et al., "Complexities of TGF-β Targeted Cancer Therapy," International Journal of Biological Sciences, vol. 8, 2012 (pp. 964-978).
Hagner et al., "CC-122, a pleiotropic pathway modifier, mimics an interferon response and has antitumor activity in DLBCL," Blood, vol. 126, 2015 (pp. 779-789).
Iconomou et al., "Systematic approaches to identify E3 ligase substrates," Biochemical Journal, vol. 473, 2016 (pp. 4083-4101).
International Search Report and Written Opinion issued by the United States Patent and Trademark Office as International Searching Authority for International Patent Application No. PCT/US2018/052181, dated Feb. 26, 2019 (14 pages).
International Search Report and Written Opinion issued by the United States Patent and Trademark Office as International Searching Authority for International Patent Application No. PCT/US2018/052242, dated Jan. 30, 2019 (8 pages).
International Search Report and Written Opinion issued by the United States Patent and Trademark Office as International Searching Authority for International Patent Application No. PCT/US2019/013481, dated Mar. 15, 2019 (9 pages).
International Search Report and Written Opinion issued by the United States Patent and Trademark Office as International Searching Authority for International Patent Application No. PCT/US2019/013491, dated Mar. 18, 2019 (9 pages).
International Search Report and Written Opinion issued by the United States Patent and Trademark Office as International Searching Authority for International Patent Application No. PCT/US2019/040462, dated Sep. 20, 2019 (14 pages).
International Search Report and Written Opinion issued by the United States Patent and Trademark Office as International Searching Authority for International Patent Application No. PCT/US2019/040520, dated Nov. 13, 2019 (11 pages).
International Search Report and Written Opinion issued by the United States Patent and Trademark Office as International Searching Authority for International Patent Application No. PCT/US2019/040545, dated Oct. 21, 2019 (8 pages).
Kester et al., "Optimization of Benzodiazepinones as Selective Inhibitors of the X-Linked Inhibitor of Apoptosis Protein (XIAP) Second Baculovirus IAP Repeat (BIR2) Domain," Journal of Medicinal Chemistry, vol. 56, No. 20, 2013 (pp. 7788-7803).
Kou et al., "Effects of RuPeng15 Powder (RPP15) on Monosodium Urate Crystal-Induced Gouty Arthritis in Rats," Evidence-Based Complementary and Alternative Medicine, vol. 2015, art. 527019, 2015 (7 pages).
Krönke et al., "Lenalidomide causes selective degradation of IKZF1 and IKZF3 in multiple myeloma cells" Science, vol. 343, No. 6168, 2014 (pp. 301-305).
Li et al., "IRAK-4: A novel member of the IRAK family with the properties of an IRAK-kinase," PNAS, vol. 99, No. 8, 2002 (pp. 5567-5572).
Lu et al., "Hijacking the E3 Ubiquitin Ligase Cereblon to Efficiently Target BRD4," Chemistry & Biology, vol. 22, No. 6. 2015 (pp. 755-763).
Lu et al., "The myeloma drug lenalidomide promotes the cereblon-dependent destruction of Ikaros proteins," Science, vol. 343, No. 6168 2014 (pp. 305-309).

Muller et al. "Amino-Substituted Thalidomide Analogs: Potent Inhibitors of TNF-α Production," Bioorganic & Medicinal Chemistry Letters, vol. 9, 1999 (pp. 1625-1630).
Priyadarshini et al., "Copper catalyzed oxidative cross-coupling of aromatic amines with 2-pyrrolidinone: a facile synthesis of N-aryl-r-amino-r-lactams," Tetrahedron, vol. 70, No. 36, 2014 (pp. 6068-6074).
Pubmed Compound Summary for CID 101524675, "(2R)-3-Fluoro-2-(2-methylpropyl)-3-phenyl-1,3-azasilinan-6-one," U.S. National Library of Medicine, created Dec. 18, 2015, https://pubchem.ncbi.nlm.nih.gov/compound/101524675. Date Accessed: Sep. 5, 2019 (5 pages).
Pubmed Compound Summary for CID 138728787, "3-(6-Ethylpyrido[2,3-b]indol-9-yl)piperidine-2,6-dione," U.S. National Library of Medicine, created Jul. 20, 2019, https://pubchem.ncbi.nlm.nih.gov/compound/138728787. Date Accessed: Sep. 5, 2019 (6 pages).
Pubmed Compound Summary for CID 63661260,"5-[2-(1-Chloroethyl)benzimidazol-1-yl]piperidin-2-one," U.S. National Library of Medicine, created Oct. 22, 2012, https://pubchem.ncbi.nlm.nih.gov/compound/63661260. Date Accessed: Sep. 4, 2019 (6 pages).
Pubmed Compound Summary for CID 65968760, "1-(2,6-Dioxopiperidin-3-yl)benzimidazole-5-carboxylic acid," U.S. National Library of Medicine, created Oct. 24, 2012, https://pubchem.ncbi.nlm.nih.gov/compound/65968760. Date Accessed: Sep. 4, 2019 (6 pages).
Pubmed Compound Summary for CID 102164987, "3-[(4S)-2,5-Dioxo-4-phenylimidazolidine-1-yl]-2,6-piperidinedione," U.S. National Library of Medicine, created Dec. 24, 2015, https://pubchem.ncbi.nlm.nih.gov/compound/102164987. Date Accessed: Feb. 25, 2020 (7 pages).
Pubmed Compound Summary for CID 115370667, "5-(2-Oxoimidazolidin-1-yl)piperidin-2-one." U.S. National Library of Medicine, created Jan. 29, 2016, https://pubchem.ncbi.nlm.nih.gov/compound/115370667. Date Accessed: Feb. 25, 2020 (10 pages).
Pubmed Compound Summary for CID 17607528, "4-(Carbazol-9-ylmethyl)-1,3-oxazolidin-2-one," U.S. National Library of Medicine, Nov. 13, 2007, https://pubchem.ncbi.nlm.nih.gov/compound/17607528. Date Accessed: Feb. 25, 2020 (6 pages).
Pubmed Compound Summary for CID 63661460, "6-Oxo-1-(6-oxopiperidin-3-yl)piperidine-3-carboxylic acid," U.S. National Library of Medicine, created Oct. 22, 2012, https://pubchem.ncbi.nlm.nih.gov/compound/63661460. Date Accessed: Feb. 25, 2020 (7 pages).
Pubmed Compound Summary for CID 65967733, "3-(2,5-Dioxo-3-phenylpyrrolidin-1-yl)piperidine-2,6-dione," U.S. National Library of Medicine, created Dec. 24, 2015, https://pubchem.ncbi.nlm.nih.gov/compound/65967733. Date Accessed: Feb. 25, 2020 (7 pages).
Pubmed Compound Summary for CID 67258040, "[1-(9H-Fluoren-9-yl)-1-(6-oxopiperidin-3-yl)ethyl] hydrogen carbonate," U.S. National Library of Medicine, Nov. 30, 2012, https://pubchem.ncbi.nlm.nih.gov/compound/67258040. Date Accessed: Feb. 25, 2020 (9 pages).
Pubmed Compound Summary for CID 83543479, "5(Aminomethyl)-5-(1H-indol-3-yl)piperidin-2-one," U.S. National Library of Medicine, created Oct. 20, 2014, https://pubchem.ncbi.nlm.nih.gov/compound/83543479. Date Accessed: Feb. 25, 2020 (6 pages).
Pubmed Compound Summary for CID 110491408, "3-(5-Amino-2-oxo-3H-benzimidazol-1-yl)piperidine-2,6-dione," U.S. Library of Medicine, created Jan. 18, 2016, https://pubchem.ncbi.nlm.nih.gov/compound/110491408. Date Accessed: Feb. 25, 2020 (7 pages).
Pubmed Compound Summary for CID 110491555, "3-(6-Amino-2-oxo-3H-benzimidazol-1-yl)piperidine-2,6-dione," U.S. Library of Medicine, created Jan. 18, 2016, https://pubchem.ncbi.nlm.nih.gov/compound/110491555. Date Accessed: Feb. 25, 2020 (7 pages).
Pubmed Compound Summary for CID 84036945, "1-Piperidin-3-yl-3H-indol-2-one," U.S. Library of Medicine, created Oct. 20, 2014, https://pubchem.ncbi.nlm.nih.gov/compound/84036945. Date Accessed: Feb. 25, 2020 (7 pages).
Ronnebaum et al., "Synthesis of 1, 2, 3-triazole 'click' analogues of thalidomide," Tetrahedron, vol. 72, No. 40, 2016 (pp. 6136-6141).
Ross et al., "Bispecific T cell engager (BiTE® ) antibody constructs can mediate bystander tumor cell killing", PLoS One, vol. 12, No. 8, (e0183390), Aug. 24, 2017, https://doi.org/10.1371/journal.pone.0183390. Date Accessed: Feb. 12, 2020 (24 pages).

(56) References Cited

OTHER PUBLICATIONS

Shanmugasundaram, K. et al. "A modular PROTAC design for target destruction using a degradation signal based on a single amino acid," Journal of Biochemical Chemistry, Sep. 11, 2019, https://www.jbc.org/content/early/2019/09/11/jbc.AC119.010790.full.pdf. Date Accessed: Feb. 11, 2020 (10 pages).
Yang et al., "Exploiting synthetic lethality for the therapy of ABC diffuse large B cell lymphoma" Cancer Cell, vol. 21, No. 6, 2012 (pp. 723-737).
Adams, et al., "Big opportunities for small molecules in immuno-oncology," Nature Reviews: Drug Discovery, vol. 14, No. 9, 2015 (pp. 603-622).
Aurigene Discovery Tech. Ltd. Presentation: Novel IRAK-4 Inhibitors exhibit highly potent anti-proliferative activity in DLBCL cell lines with activation MYD88 L264P mutation 2015.
Berge et al., "Pharmaceutical Salts," Journal of Pharmaceutical Sciences, vol. 66, No. 1, 1977 (pp. 1-19).
Berndsen et al., "New insights into ubiquitin E3 ligase mechanism, Nature Structural and Molecular Biology," vol. 21, No. 4, 2014 (pp. 301-307).
Buckley et al., "IRAK-4 inhibitors. Part 1: a series of amides," Bioorganic and Medicinal Chemistry Letters, vol. 18, No. 11, 2008 (pp. 3211-3214).
Buckley et al., "IRAK-4 inhibitors. Part II: a structure-based assessment of imidazo[1,2-a]pyridine binding," Bioorganic and Medicinal Chemistry Letters, vol. 18, No. 11, 2008, (pp. 3291-3295).
Buckley et al., "IRAK-4 inhibitors. Part III: a series of imidazo[1,2-a]pyridines," Bioorganic and Medicinal Chemistry Letters, vol. 18, No. 12., 2008, (pp. 3656-3660).
Cameron et al. "Loss of Interleukin Receptor-Associated Kinase 4 Signaling Suppresses Amyloid Pathology and Alters Microglial Phenotype in a Mouse Model of Alzheimer's Disease" Journal of Neuroscience, vol. 32, No. 43, 2012 (pp. 15112-15123).
Cario, E., "Therapeutic Impact of Toll-like Receptors on Inflammatory Bowel Diseases: A Multiple-edged Sword," Inflammatory Bowel Diseases, vol. 14, No. 3, 2008 (pp. 411-421).
Chaudhary et al., "Recent Advances in the Discovery of Small Molecule Inhibitors of Interleukin-1 Receptor-Associated Kinase 4 (IRAK4) as a Therapeutic Target for Inflammation and Oncology Disorders," Journal of Medicinal Chemistry, vol. 58, No. 1, 2015 (pp. 96-110).
Chiang, E.Y. et al., "Immune Complex-Mediated Cell Activation from Systemic Lupus Erythematosus and Rheumatoid Arthritis Patients Elaborate Different Requirements for IRAK1/4 Kinase Activity across human Cell Types," The Journal of Immunology, vol. 186, No. 2, 2011 (pp. 1279-1288).
Cohen et al., "Targeting protein kinases for the development of anti-inflammatory drugs," Current Opinion Cell Biology, vol. 21, No. 2, 2009 (pp. 317-324).
Contino-Pepin et al., "Preliminary biological evaluations of new thalidomide analogues for multiple sclerosis application," Bioorganic & Medicinal Chemistry Letters, vol. 19, No. 2, 2009 (pp. 878-881).
Crews et al., "Targeting the Undruggable Proteome: The Small Molecules of My Dreams," Chemistry & Biology, vol. 17, No. 6, 2010 (pp. 551-555).
Cushing et al.,"IRAK4 kinase controls Toll-like receptor induced inflammation through the transcription factor IRF5 in primary human monocytes," Journal of Biological Chemistry, vol. 292, No. 45, 2017 (pp. 18689-18698).
Dalbeth et al., "Hyperuricaemia and gout: state of the art and future perspectives," Annals of Rheumatic Diseases, vol. 69, No. 10, 2010 (pp. 1738-1743).
Degorce et al., "Optimization of permeability in a series of pyrrolotriazine inhibitors of IRAK4," Bioorganic and Medicinal Chemistry, vol. 26, No. 4, 2018 (pp. 913-924).
Deshaies et al., "RING domain E3 ubiquitin ligases," Annual Review of Biochemistry, vol. 78, 2009 (pp. 399-434).
Dinarello, C. "IL-1: Discoveries, controversies and future directions," European Journal of Immunology, vol. 40, 2010 (pp. 595-653).
Dinarello, C. "Interleukin 1 and interleukin 18 as mediators of inflammation and the aging process," The American Journal of Clinical Nutrition, vol. 83, 2006 (pp. 447S-455S).
Dinarello, C., "Interleukin-18 and the Pathogenesis of Inflammatory Diseases," Seminars in Nephrology, vol. 27, No. 1, 2007 (pp. 98-114).
Dudhgaonkar et al., "Selective IRAK4 Inhibition Attenuates Disease in Murine Lupus Models and Demonstrates Steroid Sparing Activity," Journal of Immunology, vol. 198, No. 3, 2017 (pp. 1308-1319).
Dunne et al., "IRAK1 and IRAK4 Promote Phosphorylation, Ubiquitation, and Degradation of MyD88 Adaptor-like (Mal)," The Journal of Biological Chemistry, 2010, vol. 285, No. 24, 2010 (pp. 18276-18282).
Fischer et al., "Structure of the DDB1-CRBN E3 ubiquitin ligase in complex with thalidomide," Nature, vol. 512, No. 7512, 2014 (pp. 49-53).
Flannery et al., "The interleukin-1 receptor-associated kinases: Critical regulators of innate immune signaling" Biochemical Pharmacology, vol. 80, No. 12, 2010 (pp. 1981-1991).
Gearing, A. "Targeting toll-like receptors for drug development: a summary of commercial approaches," Immunology and Cell Biology, vol. 85, No. 6, 2007 (pp. 490-494).
Geyer, M. et al., "Actual status of antiinterleukin-1 therapies in rheumatic diseases," Current Opinion in Rheumatology, vol. 22, No. 3, 2010 (pp. 246-251).
Gottipati et al., "IRAK1: A critical signaling mediator of innate immunity," Cellular Signaling, vol. 20, No. 2, 2008 (pp. 269-276).
Hennessy et al., "Targeting Toll-like receptors: emerging therapeutics?" Nature Reviews Drug Discovery, vol. 9, 2010 (pp. 293-307).
Hines et al., "MDM2-Recruiting PROTAC Offers Superior, Synergistic Antiproliferative Activity via Simultaneous Degradation of BRD4 and Stabilization of p53," Cancer Research, vol. 79. No. 1, 2019 (pp. 251-262) DOI: 10.1158/0008-5472.CAN-18-2918.
Hoffman, H. et al., "Efficacy and Safety of Rilonacept (Interleukin-1 Trap) in Patients with Cryopyrin-Associated Periodic Syndromes," Arthritis & Rheumatism, vol. 58, No. 8, 2008 (pp. 2443-2452).
Iannello et al., "Role of Interleukin-18 in the Development and Pathogenesis of AIDS," AIDS Reviews, vol. 11, No. 3, 2009 (pp. 115-125).
International Search Report and Written Opinion issued by the United States Patent and Trademark Office as International Searching Authority for International Patent Application No. PCT/US2018/067304, dated Apr. 30, 2019 (13 pages).
Iriyama et al., "Clinical significance of genetic mutations of CD79B, CARD11, MYD88, and EZH2 genes in diffuse large B-cell lymphoma patients" 53rd ASH Annual Meeting, San Diego, California, Dec. 10-13, 2011.
Ito et al, "Identification of a primary target of thalidomide teratogenicity," Science, vol. 327, No. 5971, 2010 (pp. 1345-1350).
Kelly et al., "Selective interleukin-1 receptor-associated kinase 4 inhibitors for the treatment of autoimmune disorders and lymphoid malignancy," Journal of Experimental Medicine, vol. 212, No. 13, 2015 (pp. 2189-2201).
Kim et al., "A critical role for IRAK4 kinase activity in Toll-like receptor-mediated innate immunity," Journal of Experimental Medicine, vol. 204, No. 5, 2007 (pp. 1025-1036).
Kondo et al., "Renoprotective effects of novel interleukin-1 receptor-associated kinase 4 inhibitor AS2444697 through anti-inflammatory action in 5/6 nephrectomized rats," Naunyn-Schmiedeberg's Archives of Pharmacology, vol. 387, No. 10, 2014 (pp. 909-919).
Koziczak-Holbro et al., "IRAK-4 Kinase Activity Is Required for Interleukin-1 (IL-1) Receptor- and Toll-like Receptor 7-mediated Signaling and Gene Expression," Journal of Biological Chemistry, vol. 282, No. 18, 2007 (pp. 13552-13560).
Ku et al., "Selective predisposition to bacterial infections in IRAK-4-deficient children: IRAK-4-dependent TLRs are otherwise redundant in protective immunity," Journal of Experiemental Medicine, vol. 204, No. 10, 2007 (pp. 2407-2422).
Kubo-Murai et al., "IRAK-4-dependent Degradation of IRAK-1 is a Negative Feedback Signal for TLR-mediated NF-kB Activation," The Journal of Biochemistry, vol. 143, No. 3, 2008 (pp. 295-302).

(56) References Cited

OTHER PUBLICATIONS

Küppers R., IRAK inhibition to shut down TLR signaling in autoimmunity and MyD88-dependent lymphomas, Journal of Experimental Medicine, vol. 212, No. 13, 2015 (pp. 2184-2188).
Lebakken et al., "A Fluorescence Lifetime Based Binding Assay to Characterize Kinase Inhibitors," Journal of Biomedical Screening, vol. 12, No. 6, 2007 (pp. 828-841).
Lee et al., "Discovery of Clinical Candidate 1-{[2S,3S,4S)-3-ethyl-4-fluoro-5-oxopyrrolidin-2-yl]methoxy}-7-methoxyisoquinoine-6-carboxamide (PF-06650833), a Potent, Selective Inhibitor of Interleukin-1 Receptor Associated Kinase 4 9IRAK4), by Fragment-Based Drug Design," Journal of Medicinal Chemistry, vol. 60, No. 13, 2017 (pp. 5521-5542).
Li et al., "Genome-Wide and Functional Annotation of Human E3 Ubiquitin Ligases Identifies MULAN, a Mitochondrial E3 that Regulates the Organelle's Dynamics and Signaling," PLOS One, vol. 3, No. 1, 2008 (e1847).
Li, "IRAK4 in TLR/IL-1R signaling: Possible clinical applications," European Journal of Immunology, vol. 38, 2008 (pp. 614-618).
Li, N. et al., "Targeting interleukin-1 receptor-associated kinase for human hepatocellular carcinoma," Journal of Experimental and Clinical Cancer Research, vol. 35, No. 1, 2016 (pp. 140-150).
Lim et al. "Discovery of 5-Amino-N-(1H-pyrazol-4-yl)pyrazolo[1,5-a]pyrimidine-3-carboxamide Inhibitors of IRAK4," ACS Medicinal Chemistry Letters, 2015, vol. 6., No. 6, 2015 (pp. 683-688).
Lin et al., "Helical assembly in the MyD88-IRAK4-IRAK2 complex in TLR /IL-1R signalling," Nature, vol. 465, No. 17, 2010 (pp. 885-891).
Lust et al., "Induction of a Chronic Disease State in patients With Smoldering of Indolent Multiple Myeloma by Targeting Interleukin 1β-Induced Interleukin 6 Production and the Myeloma Proliferative Component," Mayo Clinic Proceedings, vol. 84, No. 2, 2009 (pp. 114-122).
Martinon et al., "Gout-associated uric acid crystals activate the NALP3 inflammasome," Nature, vol. 440, 2006 (pp. 237-241).
Maschera et al., "Overexpression of an enzymatically inactive interleukin-1-receptor-associated kinase activates nuclear factor-kB," Biochemical Journal, vol. 339, No. 2, 1999 (pp. 227-231).
McElroy et al., "Discovery and hit-to-lead optimization of 2,6-diaminopyrimidine Inhibitors of interleukin-1 receptor-associated kinase 4," Bioorganic and Medicinal Chemistry Letters, vol. 25, No. 9, 2015 (pp. 1836-1841).
McElroy et al., "Potent and Selective Amidopyrazole Inhibitors of IRAK4 That Are Efficacious in a Rodent Model of Inflammation," ACS Medicinal Chemistry Letters, vol. 6, No. 6, 2015 (pp. 677-682).
Ngo et al., "Oncogenically active MYD88 mutations in human lymphoma," Nature, vol. 470, No. 7332, 2011 (pp. 115-119).
Ohoka et al., "In Vivo Knockdown of Pathogenic Proteins via Specific and Nongenetic Inhibitor of Apoptosis Protein (IAP)-dependent Protein Erasers (SNIPERs)," Journal of Biological Chemistry, vol. 292, No. 11, Mar. 2017 (pp. 4556-4570).
Okazaki, T. et al., "A rheostat for immune responses: the unique properties of PD1 and their advantages for clinical application," Nature Immunology, vol. 14, No. 12, Dec. 2013 (pp. 1212-1218).
Picard et al., "Clinical features and outcome of patients with IRAK-4 and MyD88 deficiency," Medicine (Baltimore), vol. 89, No. 6, 2010 (pp. 043-25).
Picard et al., "Inherited human IRAK-4 deficiency: an update," Immunologic Research, 2007, vol. 38, No. 1-3, 2007 (pp. 347-352).
Piya et al., "BRD4 Proteolysis Targeting Chimera (PROTAC) Leads to Sustained Degradation of BRD4 with Broad Activity Against Acute Leukemias and Overcomes Stroma Mediated Resistance by Modulating Surface Expression of CXCR4," Blood, American Society of Hematology, vol. 126, No. 23, 2015, (pp. 675-676).
Powers et al., "Discovery and initial SAR of inhibitors of interleukin-1 receptor-associated kinase-4," Bioorganic & Medicinal Chemistry Letters, vol. 16, No. 11, 2006 (pp. 2842-2845).
Raina et al., "Chemical Inducers of Targeted Protein Degradation," Journal of Biological Chemistry, vol. 285, No. 15, 2010 (pp. 11057-11060).
Ramirez, et al., "Defining causative factors contributing in the activation of hedgehog signaling in diffuse large B-cell lymphoma" Leukemia Research, vol. 36, No. 10, 2012 (pp. 1267-1273).
Rokosz et al., "Kinase inhibitors as drugs for chronic inflammatory and immunological diseases: progress and challenges," Expert Opinions on Therapeutic Targets, vol. 12, No. 7, 2008 (pp. 883-903).
Rostovtsev et al., "A Stepwise Huisgen Cycloaddition Process: Copper(I)-Catalyzed Regioselective "Ligation" of Azides and Terminal Alkynes," Angewandte Chemie International Edition, vol. 41, No. 14, 2002 (pp. 2596-2599).
Schnnekloth et al., "Chemical approaches to controlling intracellular protein degradation," Chembiochem: a European Journal of Chemical Biology, vol. 6, No. 1, 2005 (pp. 40-46).
Scott et al., "Discovery and Optimization of Pyrrolopyrimidine Inhibitors of Interleukin-1 Receptor Associated Kinase 4 (IRAK4) for the Treatment of Mutant MYD88L265P Diffuse Large B-Cell Lymphoma," Journal of Medicinal Chemistry, 2017, vol. 60, No. 24, 2017 (pp. 10071-10091).
Seganish et al., "Discovery and Structure Enabled Synthesis of 2,6-diaminopyrimidine-4-one IRAK4 Inhibitors," ACS Medicinal Chemistry Letters, vol. 6, No. 8, 2015 (pp. 942-947).
Seganish et al., "Initial optimization and series evolution of diaminopyrimidine inhibitors of interleukin-1 receptor associated kinase 4," Bioorganic and Medicinal Chemistry Letters, vol. 25, No. 16, 2015 (pp. 3203-3207).
Sen et al., "Transcriptional signaling by double-stranded RNA: role of TLR3," Cytokine & Growth Factor Reviews, vol. 16, No. 1, 2005 (pp. 1-14).
Smith et al., "Identification of quinazoline based inhibitors of IRAK4 for the treatment of inflammation," Bioorganic and Medicinal Chemistry Letters, vol. 27, No. 12, 2017 (pp. 2721-2726).
So et al., "A pilot study of IL-1 inhibition by anakinra in acute gout," Arthritis Research & Therapy, vol. 9, No. 2, 2007 (6 pages).
Song et al., "The kinase activities of interleukin-e receptor associated kinase (IRAK)-1 and 4 are redundant in the control of inflammatory cytokine expression in human cells," Molecular Immunology, vol. 46, No. 7, 2009 (pp. 1458-1466).
Spradin et al., "Harnessing the Anti-Cancer Natural Product Nimbolide for Targeted Protein Degradation," bioRxiv.org (doi: https://doi.org/10.1101/436998), First Posted, Oct. 15, 2018, https://www.biorxiv.org/content/biorxiv/early/2019/04/09/436998.full.pdf. Date Accessed, Oct. 3, 2019 (41 pages).
Spratt et al., "RBR E3 ubiquitin ligases: new structures, new insights, new question," Biochemical Journal, vol. 458, Pt. 3, 2014 (pp. 421-437).
Stewart et al., "Efforts toward elucidating Thalidomide's molecular target: an expedient synthesis of the first Thalidomide biotin analogue," Organic & Biomolecular Chemistry, vol. 8, No. 18, 2010, 4059-4062.
Sun et al., Bioconjugate Chem., "Carbohydrate and protein immobilization onto solid surfaces by sequential Diels-Alder and azide-alkyne cycloadditions," vol. 17, No. 1, 2006 (pp. 52-57).
Suzuki et al., "IRAK-4 as the central TIR signaling mediator in innate immunity," Trends in Immunology, vol. 23, No. 10, 2002 (pp. 503-506).
Suzuki et al., "Severe impairment of interleukin-1 and Toll-like receptor signalling in mice lacking IRAK-4," Nature, vol. 416, No. 6882, 2002 (pp. 750-756).
Swantek et al., "IL-1 Receptor-Associated Kinase Modulates Host Responsiveness to Endotoxin," The Journal of Immunology. 2000, vol. 164, 2000 (pp. 4301-4306).
Terkeltaub et al., "The interleukin 1 inhibitor rilonacept in treatment of chronic gouty arthritis: results of a placebo-controlled, monosequence crossover, non-randomised, single-blind pilot study," Annals of Rheumatic Diseases, vol. 68, No. 10, 2009 (pp. 1613-1617).
Terkeltaub, R., "Update on gout: new therapeutic strategies and options," Nature, vol. 6, 2010 (pp. 30-38).

(56) References Cited

OTHER PUBLICATIONS

Toogood, P., "Small molecule immuno-oncology therapeutic agents," Bioorganic & Medicinal Chemistry Letters, vol. 28, No. 3, 2017 (pp. 319-329).
Torres, R. et al., "Hyperalgesia, synovitis and multiple biomarkers of inflammation are suppressed by interleukin 1 inhibition in a novel animal model of gouty arthritis," Annals of Rheumatic Diseases, vol. 68, No. 10, 2009 (pp. 1602-1608).
Toure et al., "Small-Molecule PROTACS: New Approaches to Protein Degradation," Angewandte Chemie International Edition, vol. 55, No. 6, 2016 (pp. 1966-1973).
Treon, et al., "Whole genome sequencing reveals a widely expressed mutation (MYD88 L265P) with oncogenic activity in Waldenström's Macroglobulinemia" 53rd ASH Annual Meeting, San Diego, California, Dec. 10-13, 2011 [abstract].
Troseid, M., "The role of interleukin-18 in the metabolic syndrome," Cardiovascular Diabetology, vol. 9., No. 11, 2010 (8 pages).
Tumey et al., "Identification and optimization of indolo[2,3-c]quinoline inhibitors of IRAK4," Bioorganic and Medicinal Chemistry Letters, vol. 24, No. 9, 2014 (pp. 2066-2072).
Uehara et al., "Selective degradation of splicing factor CAPERα by anticancer sulfonamides," Nature Chemical Biology, vol. 13, No. 6, 2017 (pp. 675-680).
Varfolomeev et al., "IAP Antagonists Induce Autoubiquitination of c-IAPs, NF-κB activation, and TNFα-Dependent Apoptosis," Cell, vol. 131, No. 4, 2007 (pp. 669-681).
Vollmer, S., "The mechanism of activation of IRAK1 and IRAK4 by interleukin-1 and Toll-like receptor agonists," The Biochemical Journal, vol. 474, No. 12, 2017 (pp. 2027-2038).
Wang et al., "Crystal Structure of IRAK-4 Kinase in Complex with Inhibitors: Serine/Threonine Kinase with Tyrosine as a Gatekeeper," Structure, vol. 14, No. 12, 2006 (pp. 1835-1844).
Wang et al., "Discovery of potent, selective, and orally bioavailable inhibitors of interleukin-1 receptor-associated kinase 4," Bioorganic & Medicinal Chemistry Letters, vol. 25, No. 23, 2015 (pp. 5546-5550).
Wang et al., "IRAK-4 Inhibitors for Inflammation," Current Topics in Medicinal Chemistry, vol. 9, No. 8, 2009 (pp. 724-737).
Wang et al., "Roles of F-box proteins in cancer," Nature Reviews. Cancer, vol. 14, No. 4, 2014 (pp. 233-247).
Ward et al., "Covalent Ligand Screening Uncovers a RNF4 E3 Ligase Recruiter for Targeted Protein Degradation Applications," bioRxiv.org (doi: https://doi.org/10.1101/439125) First Posted, Oct. 16, 2018, https://www.biorxiv.org/content/biorxiv/early/2018/11/16/439125.full.pdf. Date Accessed, Oct. 3, 2019 (24 pages).
Weaver, A. "Epidemiology of gout," Cleveland Clinic Journal of Medicine, vol. 75, suppl. 5, 2008 (pp. S9-S12).
Winter et al., "Selective Target Protein Degradation via Phthalimide Conjugation," Science, vol. 348, No. 6241, 2015 (pp. 1376-1381).
Xu, et al., "A somatic variant in MYD88 (L256P) revealed by whole genome sequencing differentiates lymphoplasmacytic lymphoma from marginal zone lymphomas" 53rd ASH Annual Meeting, San Diego, California, Dec. 10-13, 2011.
Yang et al., "Disruption of MYD88 pathway signaling leads to loss of constitutive IRAK1, NK-kB and JAK/STAT signaling and induces apoptosis of cells expressing the MYD88 L265P mutation in Waldenström's Macroglobulinemia" 53rd ASH Annual Meeting, San Diego, California, Dec. 10-13, 2011.
Zhang et al., "Electrophilic PROTACs that degrade nuclear proteins by engaging DCAF16," bioRxiv.org (doi: https://doi.org/10.1101/443804), First Posted, Oct. 15, 2018, https://www.biorxiv.org/content/biorxiv/early/2018/10/15/443804.full.pdf. Date Accessed, Oct. 3, 2019 (38 pages).
Zhang et al., Constitutive IRAK4 Activation Underlies Poor Prognosis and Chemoresistance in Pancreatic Ductal Adenocarcinoma, Clinical Cancer Research: an Official Journal of the American Association for Cancer Research, vol. 23, No. 7, 2017 (pp. 1748-1759).
Zhou et al., "Targets of curcumin," Current Drug Targets, vol. 12, No. 3, 2011 (pp. 332-347).
Zou et al., "PD-L1 (B7-H1) and PD-1 Pathway Blockade for Cancer Therapy: Mechanisms, Response Biomarkers and Combinations," Science Translatonal Medicine, vol. 8., No. 328, Mar. 2016 (pp. 1-34).
U.S. Appl. No. 62/832,103, filed Apr. 10, 2019, Nello Mainolfi.
U.S. Appl. No. 62/912,252, filed Oct. 8, 2019, Nello Mainolfi.
U.S. Appl. No. 62/948,936, filed Dec. 17, 2019, Nello Mainolfi.
U.S. Appl. No. 62/948,992, filed Dec. 17, 2019, Nello Mainolfi.
U.S. Appl. No. 62/949,195, filed Dec. 17, 2019, Nello Mainolfi.
U.S. Appl. No. 62/949,298, filed Dec. 17, 2019, Matthew M. Weiss.
U.S. Appl. No. 62/949,320, filed Dec. 17, 2019, Matthew M. Weiss.
U.S. Appl. No. 62/959,332, filed Jan. 10, 2020, Nello Mainolfi.
U.S. Appl. No. 62/964,955, filed Jan. 23, 2020, Nello Mainolfi.
U.S. Appl. No. 62/969,418, filed Feb. 3, 2020, Matthew M. Weiss.

IRAK DEGRADERS AND USES THEREOF

CROSS-REFERENCE TO RELATED APPLICATIONS

This application claims the benefit under 35 U.S.C. § 119(e) of U.S. Provisional Application No. 62/610,397, filed Dec. 26, 2017, U.S. Provisional Application No. 62/653,178, filed Apr. 5, 2018, U.S. Provisional Application No. 62/694,955, filed Jul. 6, 2018, and U.S. Provisional Application No. 62/712,377, filed Jul. 31, 2018, the content of each of which is incorporated herein in its entirety by reference.

TECHNICAL FIELD OF THE INVENTION

The present invention relates to compounds and methods useful for the modulation of one or more interleukin-1 receptor-associated kinases ("IRAK") via ubiquitination and/or degradation by compounds according to the present invention. The invention also provides pharmaceutically acceptable compositions comprising compounds of the present invention and methods of using said compositions in the treatment of various disorders.

BACKGROUND OF THE INVENTION

Ubiquitin-Proteasome Pathway (UPP) is a critical pathway that regulates key regulator proteins and degrades misfolded or abnormal proteins. UPP is central to multiple cellular processes, and if defective or imbalanced, it leads to pathogenesis of a variety of diseases. The covalent attachment of ubiquitin to specific protein substrates is achieved through the action of E3 ubiquitin ligases.

There are over 600 E3 ubiquitin ligases which facilitate the ubiquitination of different proteins in vivo, which can be divided into four families: HECT-domain E3s, U-box E3s, monomeric RING E3s and multi-subunit E3s. See generally Li et al. (PLOS One, 2008, 3, 1487) titled "Genome-wide and functional annotation of human E3 ubiquitin ligases identifies MULAN, a mitochondrial E3 that regulates the organelle's dynamics and signaling."; Berndsen et al. (Nat. Struct. Mol. Biol., 2014, 21, 301-307) titled "New insights into ubiquitin E3 ligase mechanism"; Deshaies et al. (Ann. Rev. Biochem., 2009, 78, 399-434) titled "RING domain E3 ubiquitin ligases."; Spratt et al. (Biochem. 2014, 458, 421-437) titled "RBR E3 ubiquitin ligases: new structures, new insights, new questions."; and Wang et al. (Nat. Rev. Cancer., 2014, 14, 233-347) titled "Roles of F-box proteins in cancer."

UPP plays a key role in the degradation of short-lived and regulatory proteins important in a variety of basic cellular processes, including regulation of the cell cycle, modulation of cell surface receptors and ion channels, and antigen presentation. The pathway has been implicated in several forms of malignancy, in the pathogenesis of several genetic diseases (including cystic fibrosis, Angelman's syndrome, and Liddle syndrome), in immune surveillance/viral pathogenesis, and in the pathology of muscle wasting. Many diseases are associated with an abnormal UPP and negatively affect cell cycle and division, the cellular response to stress and to extracellular modulators, morphogenesis of neuronal networks, modulation of cell surface receptors, ion channels, the secretory pathway, DNA repair and biogenesis of organelles.

Aberrations in the process have recently been implicated in the pathogenesis of several diseases, both inherited and acquired. These diseases fall into two major groups: (a) those that result from loss of function with the resultant stabilization of certain proteins, and (b) those that result from gain of function, i.e. abnormal or accelerated degradation of the protein target.

The UPP is used to induce selective protein degradation, including use of fusion proteins to artificially ubiquitinate target proteins and synthetic small-molecule probes to induce proteasome-dependent degradation. Bifunctional compounds composed of a target protein-binding ligand and an E3 ubiquitin ligase ligand, induced proteasome-mediated degradation of selected proteins via their recruitment to E3 ubiquitin ligase and subsequent ubiquitination. These drug-like molecules offer the possibility of temporal control over protein expression. Such compounds are capable of inducing the inactivation of a protein of interest upon addition to cells or administration to an animal or human, and could be useful as biochemical reagents and lead to a new paradigm for the treatment of diseases by removing pathogenic or oncogenic proteins (Crews C, Chemistry & Biology, 2010, 17 (6):551-555; Schnnekloth J S Jr., Chembiochem, 2005, 6 (1):40-46).

An ongoing need exists in the art for effective treatments for disease, especially hyperplasias and cancers, such as multiple myeloma. However, non-specific effects, and the inability to target and modulate certain classes of proteins altogether, such as transcription factors, remain as obstacles to the development of effective anti-cancer agents. As such, small molecule therapeutic agents that leverage E3 ligase mediated protein degradation to target cancer-associated proteins such as interleukin-1 receptor-associated kinases ("IRAK") hold promise as therapeutic agents. Accordingly, there remains a need to find bifunctional compounds that are IRAK degraders useful as therapeutic agents.

SUMMARY OF THE INVENTION

The present application relates novel bifunctional compounds, which function to recruit IRAK kinases to E3 Ubiquitin Ligase for degradation, and methods of preparation and uses thereof. In particular, the present disclosure provides bifunctional compounds, which find utility as modulators of targeted ubiquitination of IRAK kinases, which are then degraded and/or otherwise inhibited by the bifunctional compounds as described herein. An advantage of the compounds provided herein is that a broad range of pharmacological activities is possible, consistent with the degradation/inhibition of IRAK kinases. In addition, the description provides methods of using an effective amount of the compounds as described herein for the treatment or amelioration of a disease condition, such as cancer, e.g., multiple myeloma.

The present application further relates to targeted degradation of IRAK kinases through the use of bifunctional molecules, including bifunctional molecules that link a cereblon-binding moiety to a ligand that binds IRAK kinasses.

It has now been found that compounds of this invention, and pharmaceutically acceptable compositions thereof, are effective as degraders of IRAK kinases. Such compounds have the general formula I:

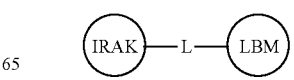

I or a pharmaceutically acceptable salt thereof, wherein each variable is as defined and described herein.

Compounds of the present invention, and pharmaceutically acceptable compositions thereof, are useful for treating a variety of diseases, disorders or conditions, associated with regulation of signaling pathways implicating IRAK kinases. Such diseases, disorders, or conditions include those described herein.

Compounds provided by this invention are also useful for the study of IRAK enzymes in biological and pathological phenomena; the study of intracellular signal transduction pathways occurring in bodily tissues; and the comparative evaluation of new IRAK inhibitors or IRAK degraders or other regulators of kinases, signaling pathways, and cytokine levels in vitro or in vivo.

DETAILED DESCRIPTION OF CERTAIN EMBODIMENTS

Figure 1:
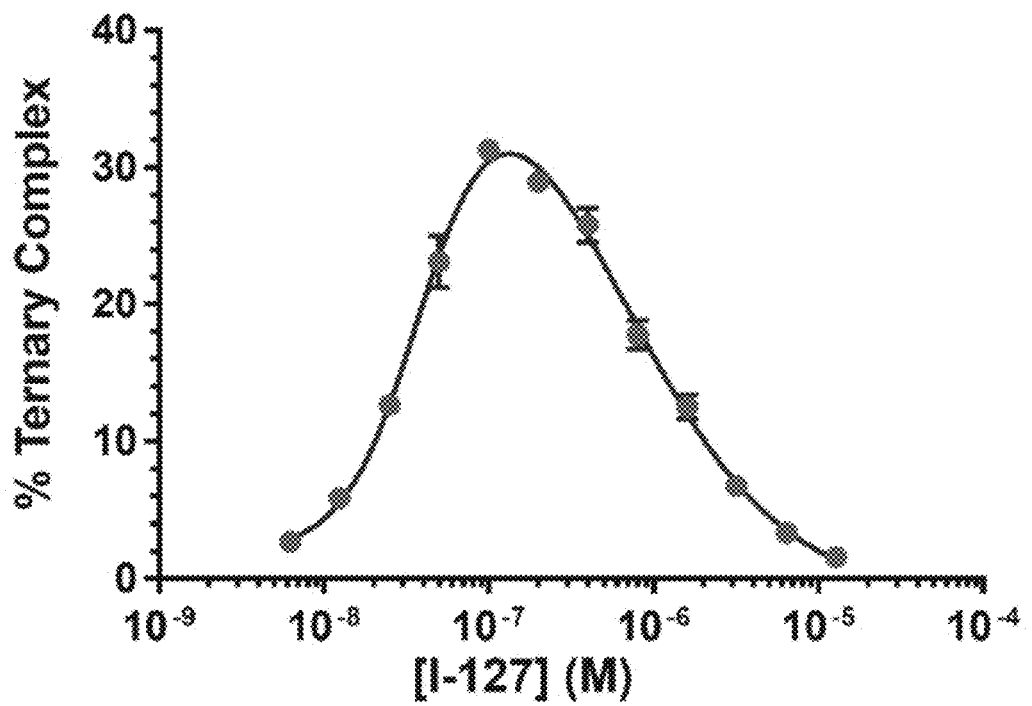
FIG. 1 depicts the ternary complex formation (as a percentage of total IRAK4) mediated by I-127.

1. General Description of Certain Embodiments of the Invention

Compounds of the present invention, and compositions thereof, are useful as degraders and/or inhibitors of one or more IRAK protein kinases. In some embodiments, a provided compound degrades and/or inhibits IRAK-1/2/3/4.

In certain embodiments, the present invention provides a compound of formula I:

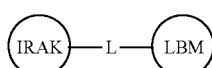

I or a pharmaceutically acceptable salt thereof, wherein:
IRAK is an IRAK binding moiety capable of binding to one or more of IRAK-1, -2, -3, or -4;
L is a bivalent moiety that connects IRAK to LBM; and
LBM is a ligase binding moiety.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

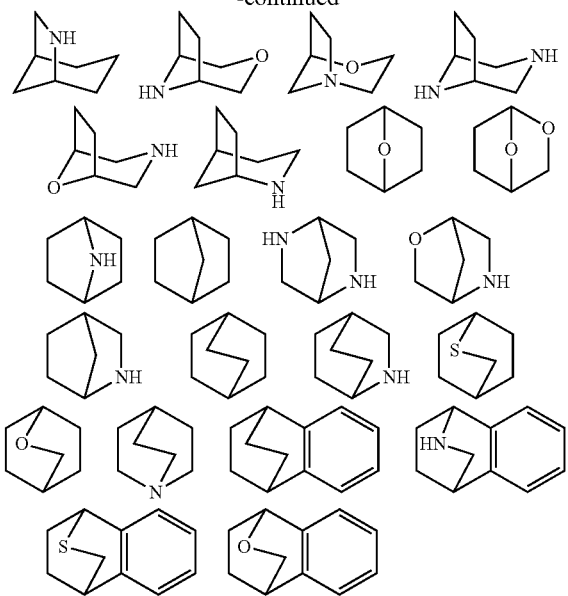

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

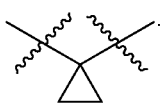 [SMILES: *C1(*)CC1]

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3 (4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched alkylene)$O-N(R^\circ)_2$; or $-(C_{1-4}$ straight or branched alkylene)$C(O)O-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention As used herein, the term "inhibitor" is defined as a compound that binds to and/or inhibits an IRAK kinase with measurable affinity. In certain embodiments, an inhibitor has an IC$_{50}$ and/or binding constant of less than about 50 µM, less than about 1 µM, less than about 500 nM, less than about 100 nM, less than about 10 nM, or less than about 1 nM.

As used herein, the term "degrader" is defined as a heterobifunctional compound that binds to and/or inhibits both an IRAK kinase and an E3 ligase with measurable affinity resulting in the ubiqitination and subsequent degradation of the IRAK kinase. In certain embodiments, a degrader has an DC$_{50}$ of less than about 50 µM, less than about 1 µM, less than about 500 nM, less than about 100 nM, less than about 10 nM, or less than about 1 nM.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}$P, $^{33}$P, $^{35}$S, or $^{14}$C), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360, 8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in an IRAK protein kinase activity between a sample comprising a compound of the present invention, or composition thereof, and an IRAK protein kinase, and an equivalent sample comprising an IRAK protein kinase, in the absence of said compound, or composition thereof.

3. Description of Exemplary Embodiments

As described above, in certain embodiments, the present invention provides a compound of formula I:

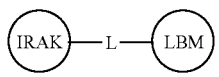

I or a pharmaceutically acceptable salt thereof, wherein:
IRAK is an IRAK binding moiety capable of binding to one or more of IRAK-1, -2, -3, or -4;
L is a bivalent moiety that connects IRAK to LBM; and
LBM is a ligase binding moiety.

In some embodiments, the present invention provides a compound of formula I:

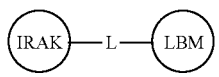

I or a pharmaceutically acceptable salt thereof, wherein:
IRAK is an IRAK-4 binding moiety;
L is a bivalent moiety that connects IRAK to LBM; and
LBM is a cereblon ligase binding moiety.

In some embodiments, LBM is an E3 ligase ligand. Such E3 ligase ligands are well known to one of ordinary skill in the art and include those described in M. Toure, C. M. Crews, *Angew. Chem. Int. Ed.* 2016, 55, 1966, T. Uehara et al. *Nature Chemical Biology* 2017, 13, 675, WO 2017/176708, US 2017/0281784, WO 2017/161119, WO 2017/176957, WO 2017/176958, WO 2015/160845, US 2015/0291562, WO 2016/197032, WO 2016/105518, US 2018/0009779, WO 2017/007612, 2018/0134684, WO 2013/106643, US 2014/0356322, WO 2002/020740, US 2002/0068063, WO 2012/078559, US 2014/0302523, WO 2012/003281, US 2013/0190340, US 2016/0022642, WO 2014/063061, US 2015/0274738, WO 2016/118666, US 2016/0214972, WO 2016/149668, US 2016/0272639, WO 2016/169989, US 2018/0118733, WO 2016/197114, US 2018/0147202, WO 2017/011371, US 2017/0008904, WO 2017/011590, US 2017/0037004, WO 2017/079267, US 2017/0121321, WO 2017/117473, WO 2017/117474, WO 2013/106646, WO 2014/108452, WO 2017/197036, WO 2017/197046, WO 2017/197051, WO 2017/197055, and WO 2017/197056 each of, the entirety of each of which is herein incorporated by reference.

In certain embodiments, the present invention provides a compound of Formula I, wherein LBM is an E3 ubiquitin ligase (cereblon) binding moiety

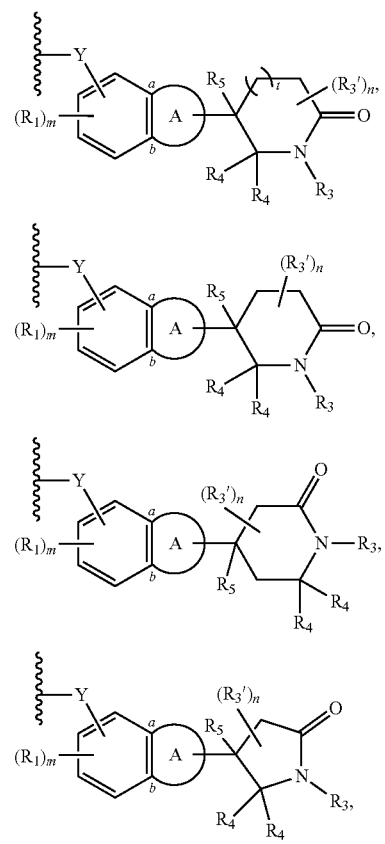

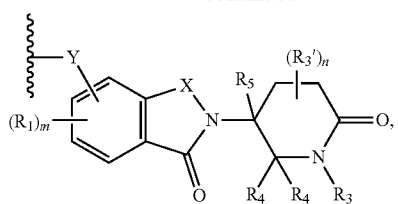
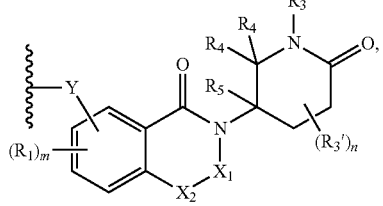
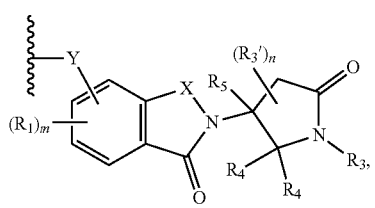
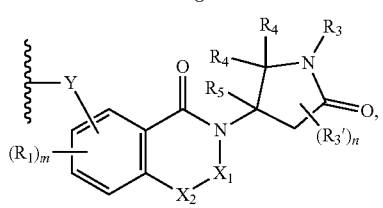
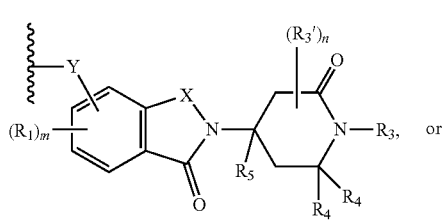
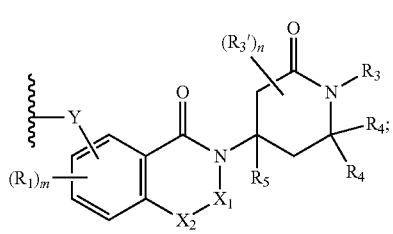
thereby forming a compound of formula I-a-1, I-a-2, I-a-3, I-a-4, I-a-5, I-a-6, I-a-7, I-a-8, I-a-9, or I-a-10 respectively:
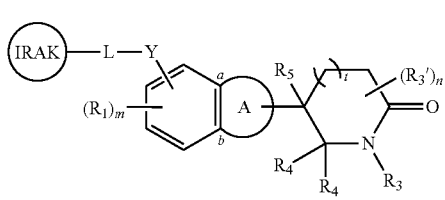
I-a-1
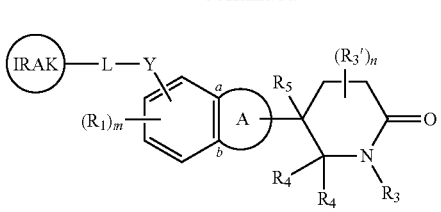
I-a-2
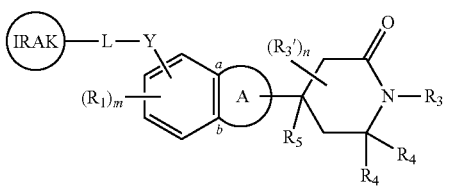
I-a-3
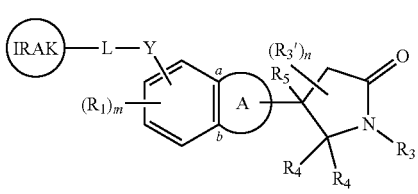
I-a-4
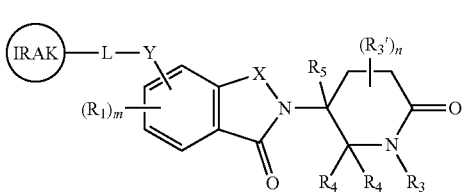
I-a-5
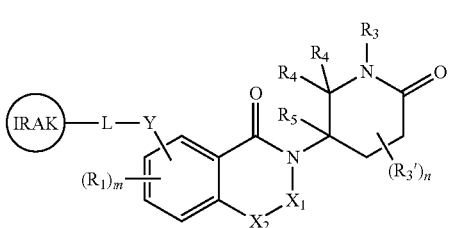
I-a-6
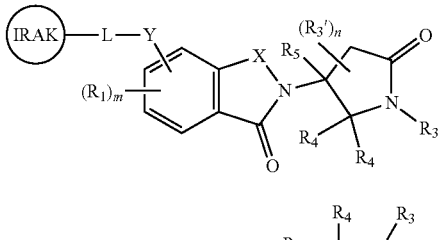
I-a-7
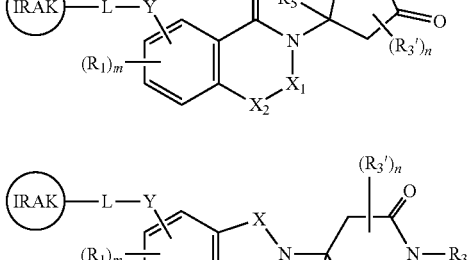
I-a-8
I-a-9

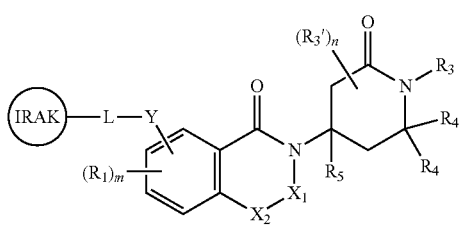
I-a-10 or a pharmaceutically acceptable salt thereof, wherein L and IRAK are as defined above and described in embodiments herein, and wherein each of the variables

X, $X_1$, $X_2$, Y, $R_1$, $R_3$, $R_3'$, $R_4$, $R_5$, t, m and n is as defined and described in WO 2017/007612 and US 2018/0134684, the entirety of each of which is herein incorporated by reference.

In certain embodiments, the present invention provides a compound of Formula I, wherein LBM is an E3 ubiquitin ligase (cereblon) binding moiety

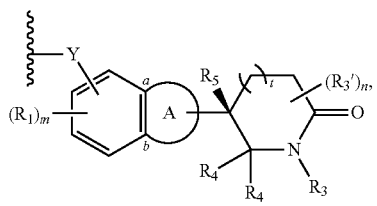

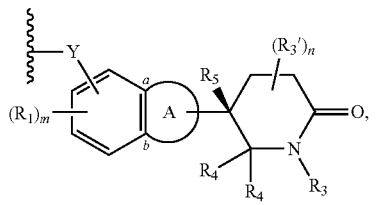

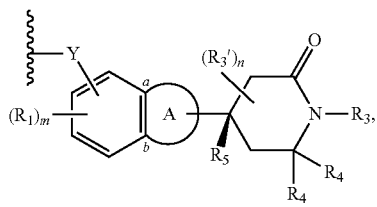

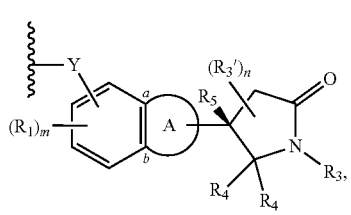

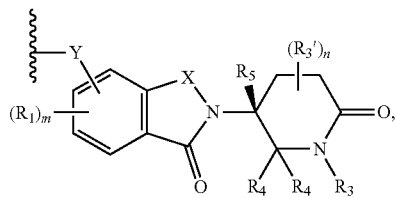

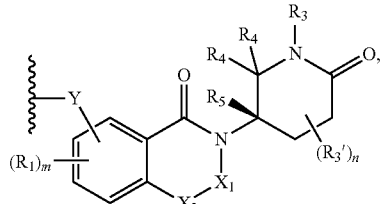

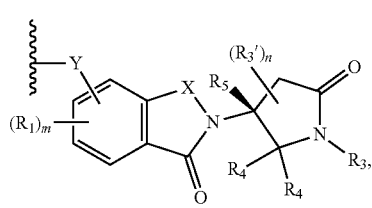

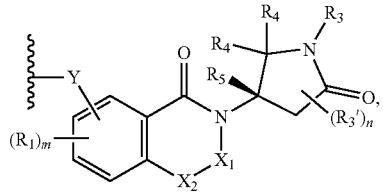

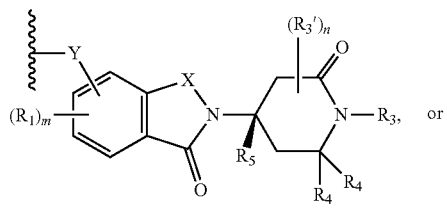

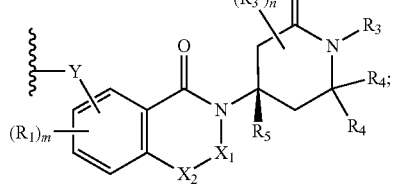

thereby forming a compound of formula I-a'-1, I-a'-2, I-a'-3, I-a'-4, I-a'-5, I-a'-6, I-a'-7, I-a'-8, I-a'-9, or I-a'-10 respectively:

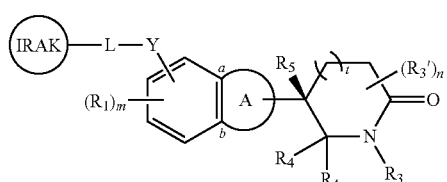
I-a'-1

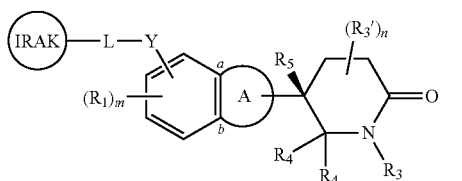
I-a'-2

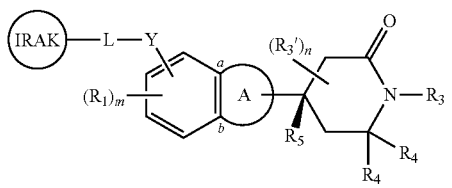
I-a'-3

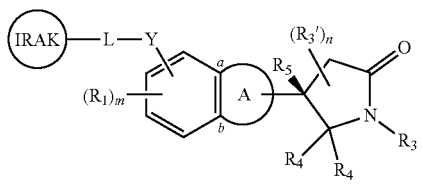
I-a'-4

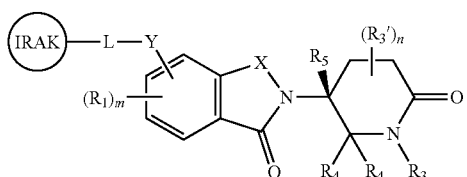
I-a'-5

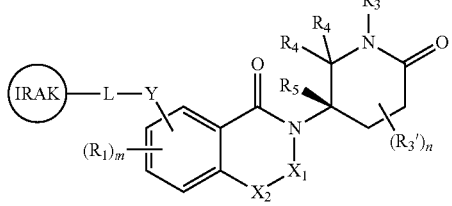
I-a'-6

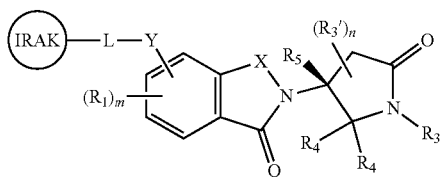
I-a'-7

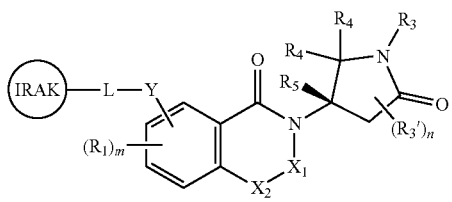
I-a'-8

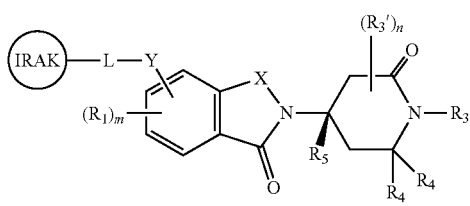
I-a'-9

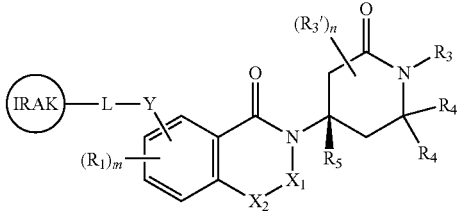
I-a'-10 or a pharmaceutically acceptable salt thereof, wherein L and IRAK are as defined above and described in embodiments herein, and wherein each of the variables

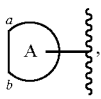

X, $X_1$, $X_2$, Y, $R_1$, $R_3$, $R_3'$, $R_4$, $R_5$, t, m and n is as defined and described in WO 2017/007612 and US 2018/0134684, the entirety of each of which is herein incorporated by reference.

In certain embodiments, the present invention provides a compound of Formula I, wherein LBM is an E3 ubiquitin ligase (cereblon) binding moiety

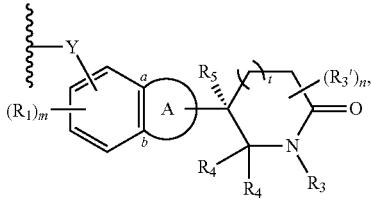

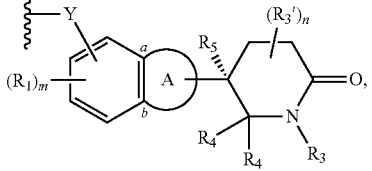

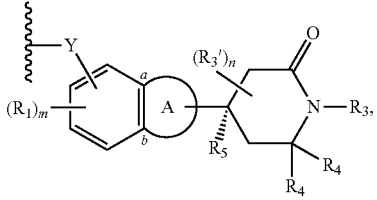

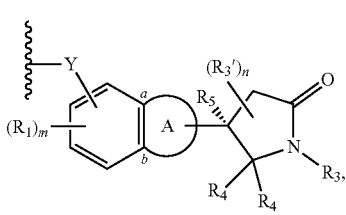

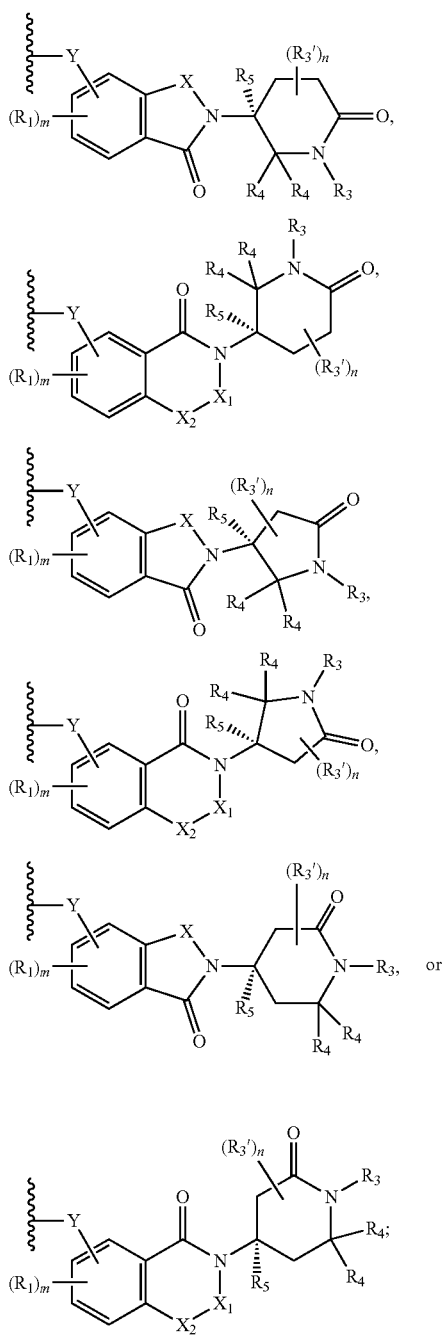
thereby forming a compound of formula I-a″-1, I-a″-2, I-a″-3, I-a″-4, I-a″-5, I-a″-6, I-a″-7, I-a″-8, I-a″-9, or I-a′-10 respectively:
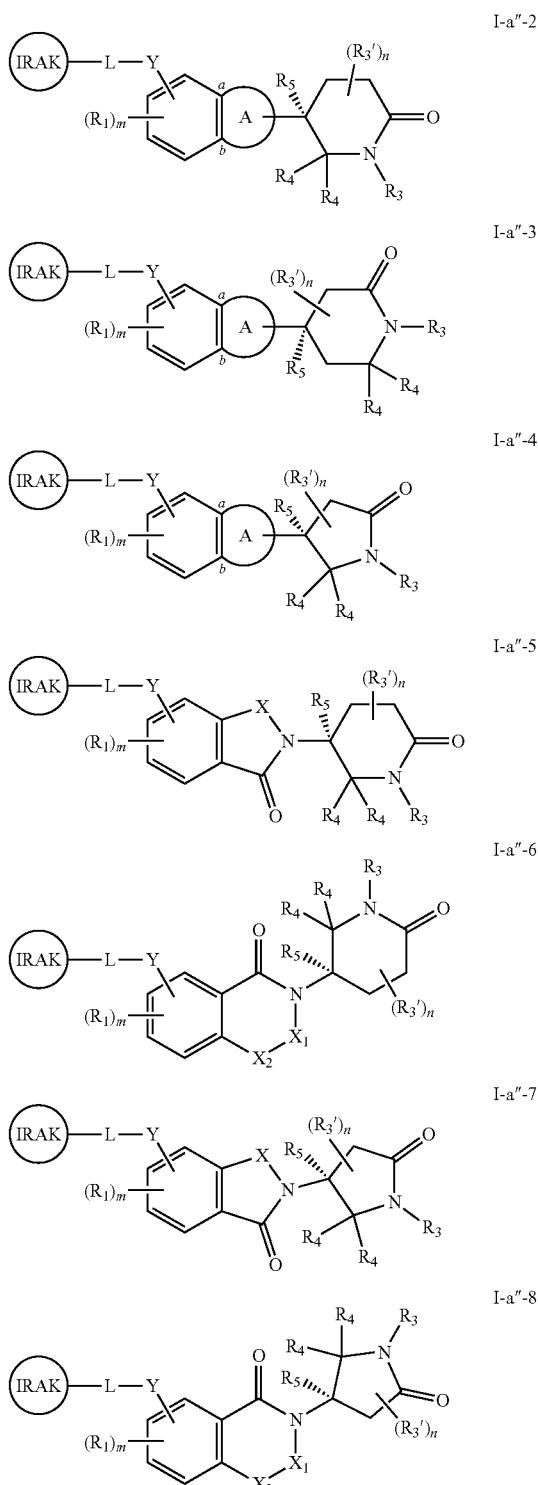

-continued

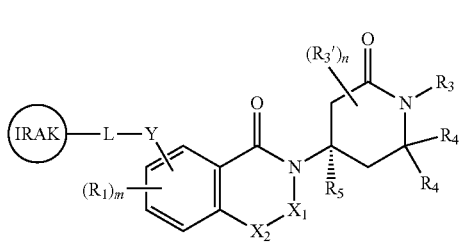
I-a″-10

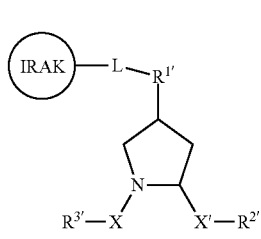
I-b-1 or a pharmaceutically acceptable salt thereof, wherein L and IRAK are as defined above and described in embodiments herein, and wherein each of the variables

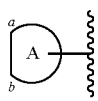

X, $X_1$, $X_2$, Y, $R_1$, $R_3$, $R_3'$, $R_4$, $R_5$, t, m and n is as defined and described in WO 2017/007612 and US 2018/0134684, the entirety of each of which is herein incorporated by reference.

In certain embodiments, the present invention provides a compound of Formula I, wherein LBM is a VHL E3 ubiquitin ligase binding moiety

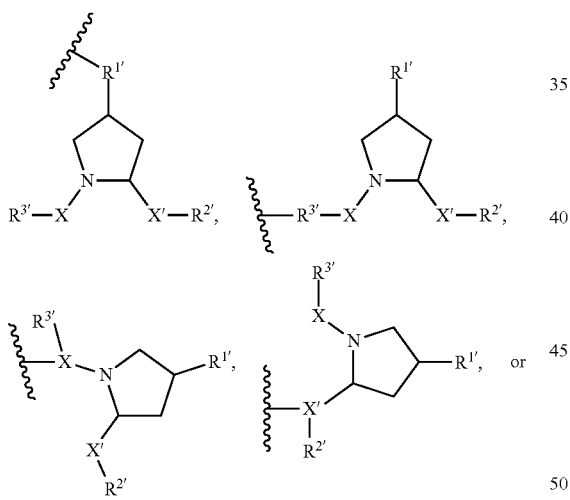

thereby forming a compound of formula I-b-1, I-b-2, I-b-3, I-b-4, or I-b-5 respectively:

or a pharmaceutically acceptable salt thereof, wherein L and IRAK are as defined above and described in embodiments herein, and wherein each of the variables $R^{1'}$, $R^{2'}$, $R^{3'}$, X, and X' is as defined and described in WO 2013/106643 and US 2014/0356322, the entirety of each of which is herein incorporated by reference.

In certain embodiments, the present invention provides a compound of Formula I, wherein LBM is an E3 ubiquitin ligase (cereblon) binding moiety thereby forming a compound of formula I-c:

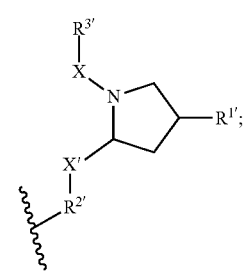

-continued

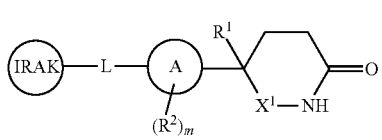

or a pharmaceutically acceptable salt thereof, wherein L and IRAK are as defined above and described in embodiments herein, and wherein:

$X^1$ is a bivalent moiety selected from a covalent bond, —$CH_2$—, —C(O)—, —C(S)—, or

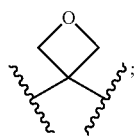

$R^1$ is hydrogen, deuterium, halogen, —CN, —OR, —SR, —S(O)R, —S(O)$_2$R, —NR$_2$, or an optionally substituted $C_{1-4}$ aliphatic;

each $R^2$ is independently hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

Ring A is a bi- or tricyclic ring selected from

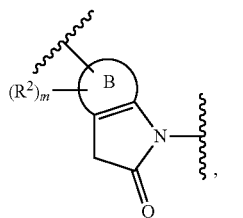 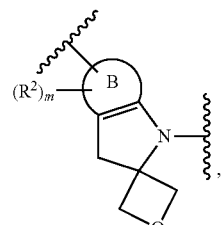

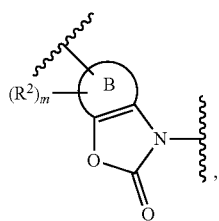 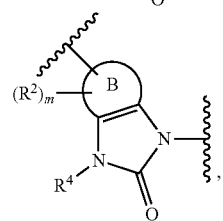

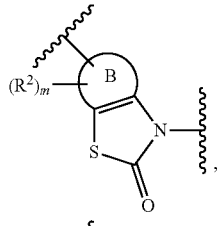 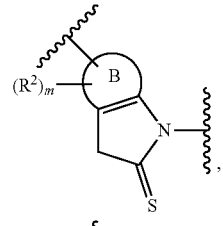

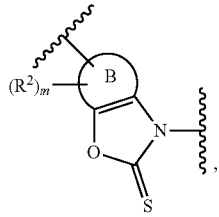 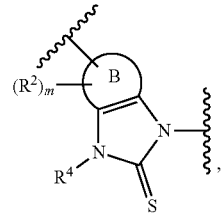

-continued

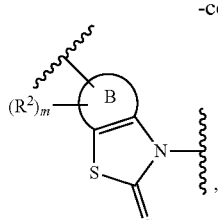

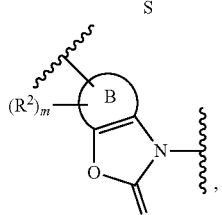 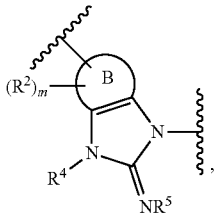

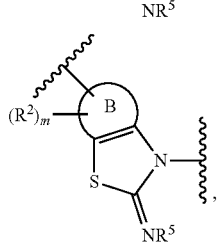 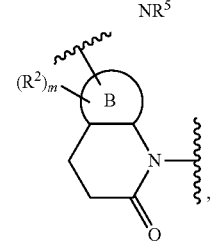

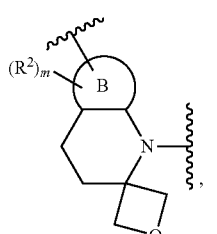 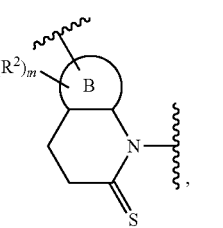

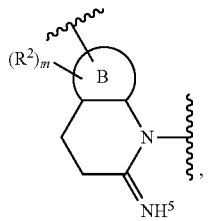 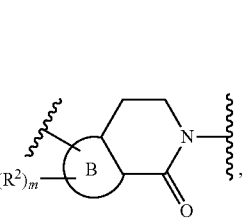

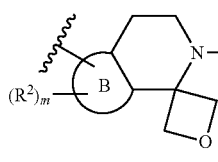

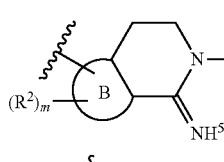 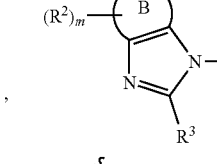

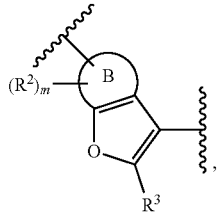 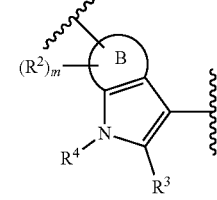

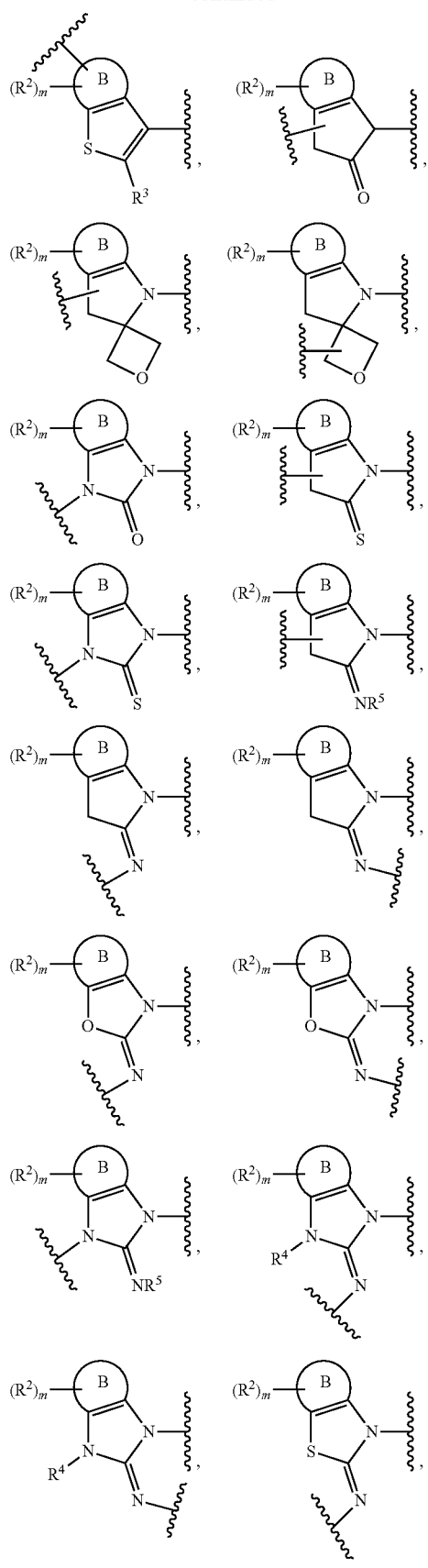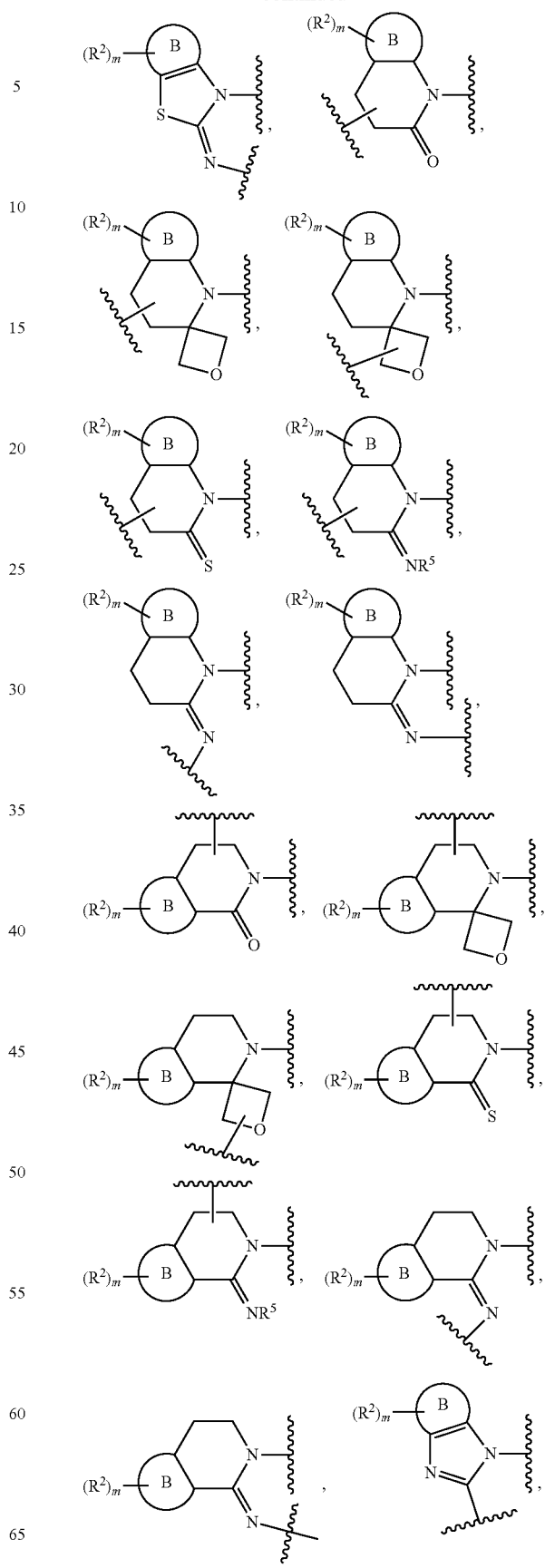

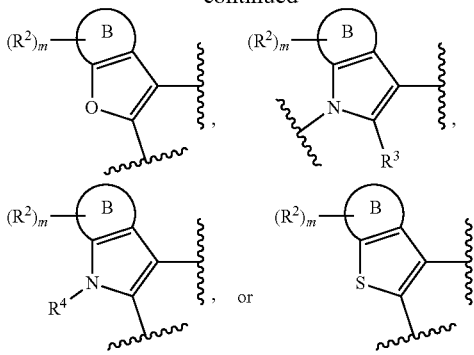

wherein
Ring B is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur;

$R^3$ is selected from hydrogen, halogen, —OR, —N(R)$_2$, or —SR;

each $R^4$ is independently hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^5$ is hydrogen, C$_{1-4}$ aliphatic, or —CN;

each $R^6$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, 2, 3 or 4; and each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In certain embodiments, the present invention provides a compound of Formula I, wherein LBM is an E3 ubiquitin ligase (cereblon) binding moiety

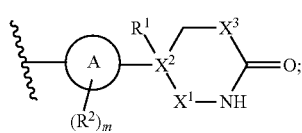

thereby forming a compound of formula I-c':

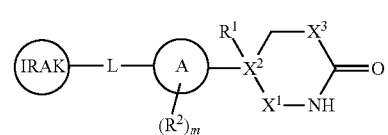

I-c' or a pharmaceutically acceptable salt thereof, wherein L and IRAK are as defined above and described in embodiments herein, and wherein:

$X^1$ is a bivalent moiety selected from a covalent bond, —CH$_2$—, —C(O)—, —C(S)—, or

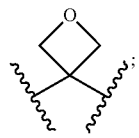 [SMILES: *C1(*)COC1]

$X^2$ is a carbon atom or silicon atom;

$X^3$ is a bivalent moiety selected from —CH$_2$— or —Si(R$_2$)—;

$R^1$ is hydrogen, deuterium, halogen, —CN, —OR, —SR, —S(O)R, —S(O)$_2$R, —N(R)$_2$, —Si(R)$_3$, or an optionally substituted C$_{1-4}$ aliphatic;

each $R^2$ is independently hydrogen, deuterium, —$R^6$, halogen, —CN, —NO$_2$, —OR, —SR, —NR$_2$, —Si(R)$_3$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

Ring A is a bi- or tricyclic ring selected from

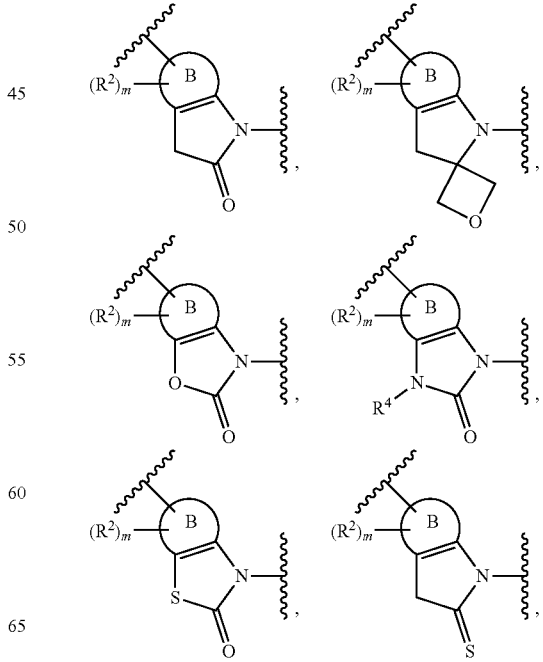

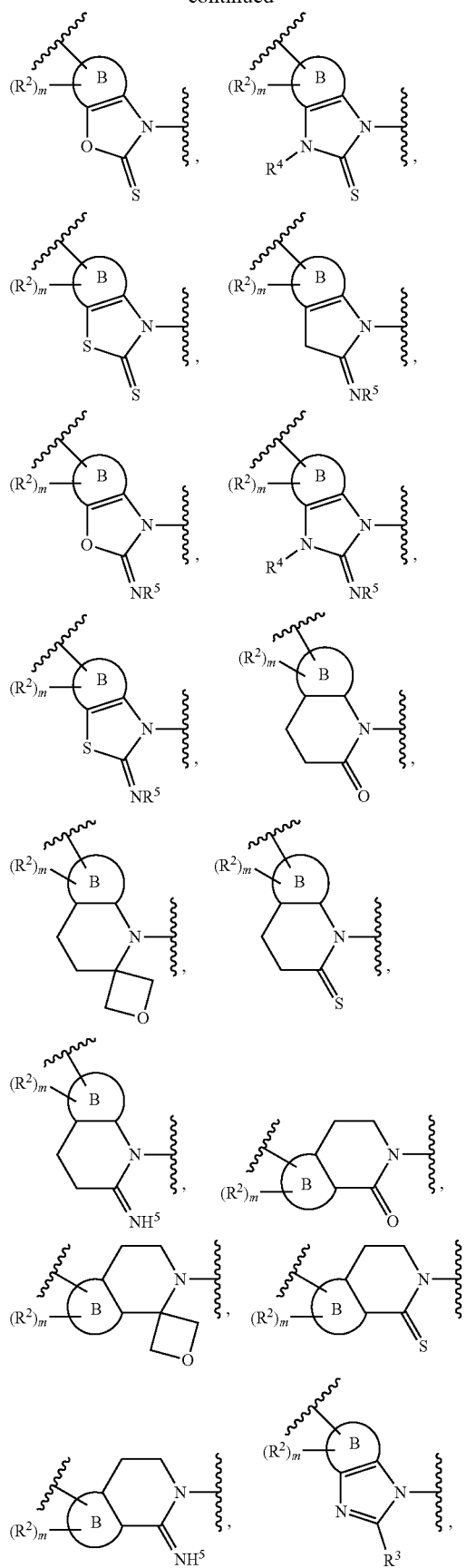
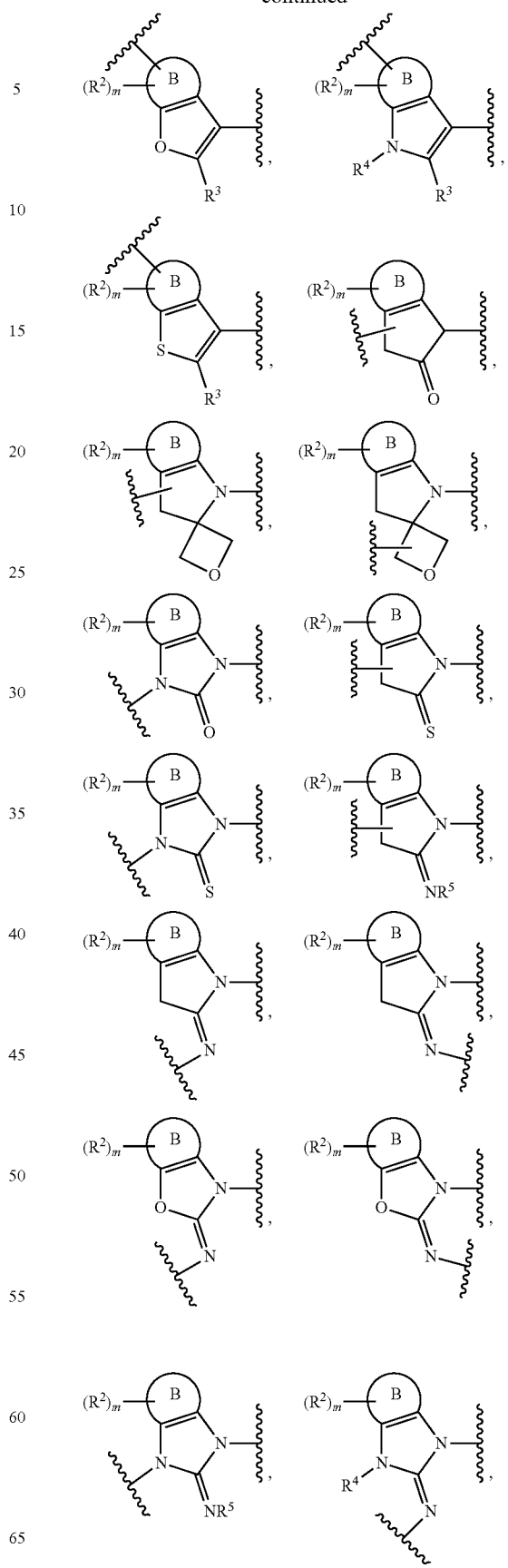

-continued

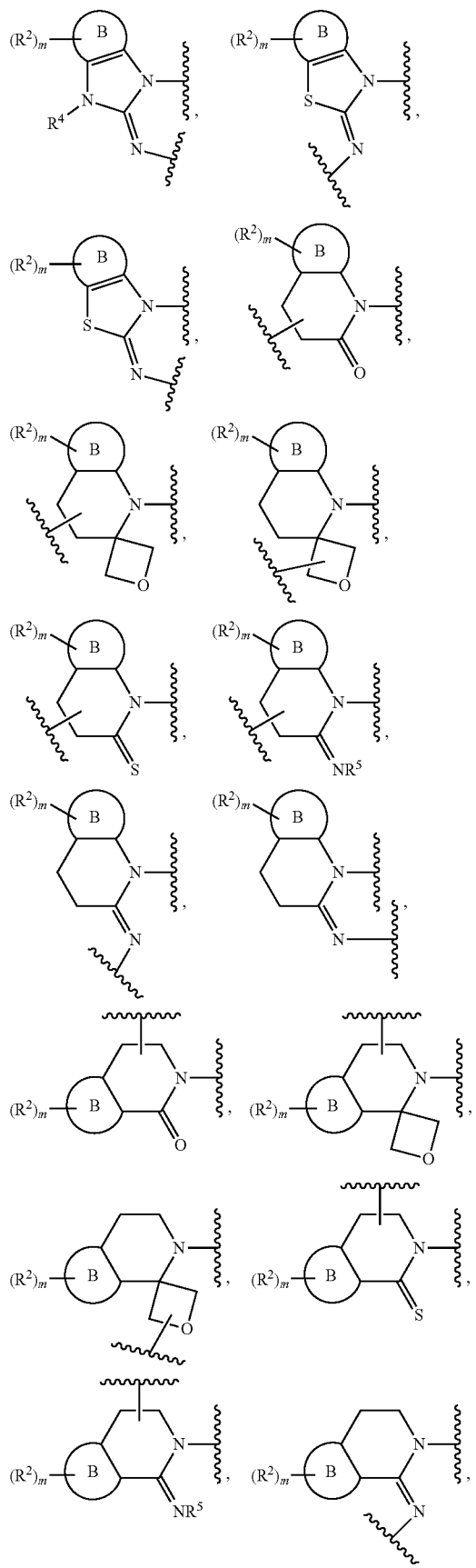

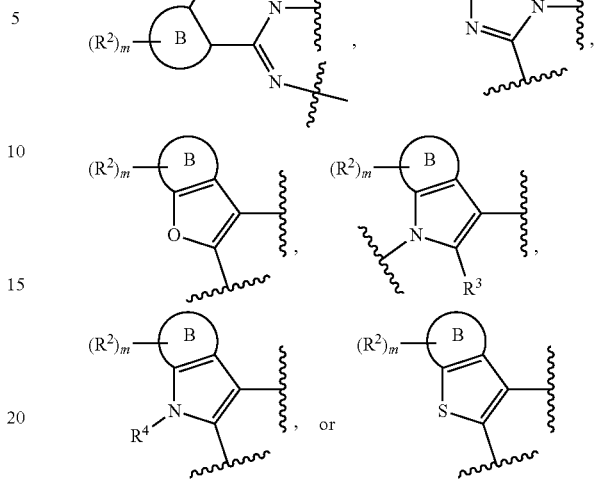

wherein

Ring B is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from boron, nitrogen, oxygen, silicon, or sulfur, or 5-membered heteroaryl with 1-3 heteroatoms independently selected from nitrogen, oxygen or sulfur;

$R^3$ is selected from hydrogen, halogen, —OR, —N(R)$_2$, or —SR;

each $R^4$ is independently hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^5$ is hydrogen, C$_{1-4}$ aliphatic, or —CN;

each $R^6$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, 2, 3 or 4; and each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, the compound of formula I-c' above is provided as a compound of formula I-c" or formula I-c''':

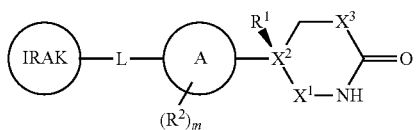

I-c″

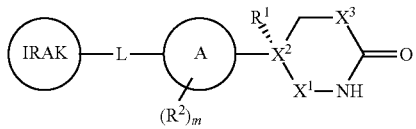

I-c‴ or a pharmaceutically acceptable salt thereof, wherein: each of IRAK, Ring A, L, $R^1$, $R^2$, $X^1$, $X^2$, $X^3$, and m is as defined above.

In certain embodiments, the present invention provides a compound of Formula I, wherein LBM is an E3 ubiquitin ligase (cereblon) binding moiety

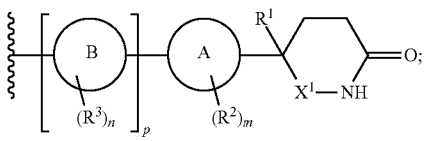

thereby forming a compound of formula I-d:

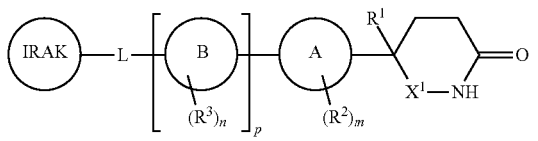

I-d or a pharmaceutically acceptable salt thereof, wherein L and IRAK are as defined above and described in embodiments herein, and wherein:

$X^1$ is a bivalent moiety selected from a covalent bond, —CH$_2$—, —C(O)—, —C(S)—, or

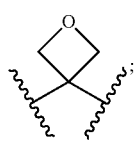 [SMILES: *C1(*)COC1]

$R^1$ is hydrogen, deuterium, halogen, —CN, —OR, —SR, —S(O)R, —S(O)$_2$R, —NR$_2$, or an optionally substituted $C_{1-4}$ aliphatic;

Ring A is a mono- or bicyclic ring selected from

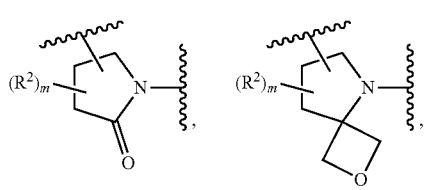


-continued

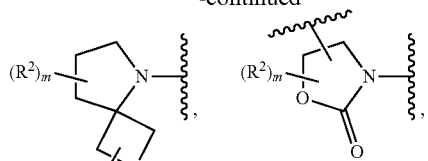

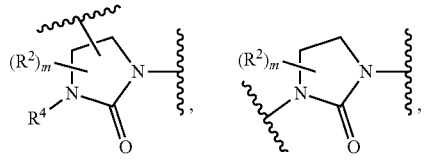

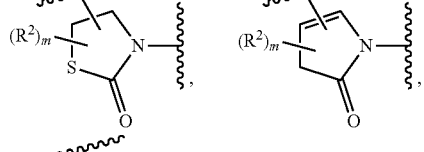


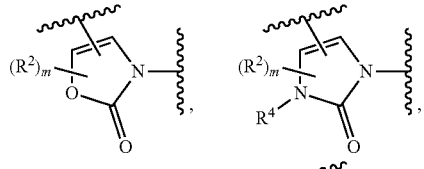


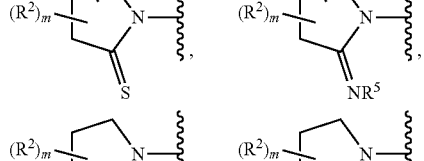


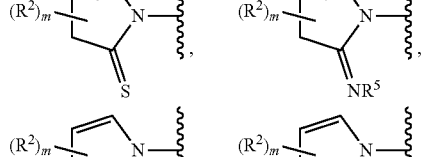

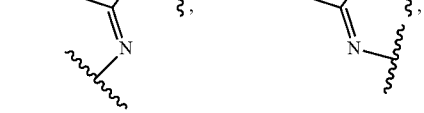

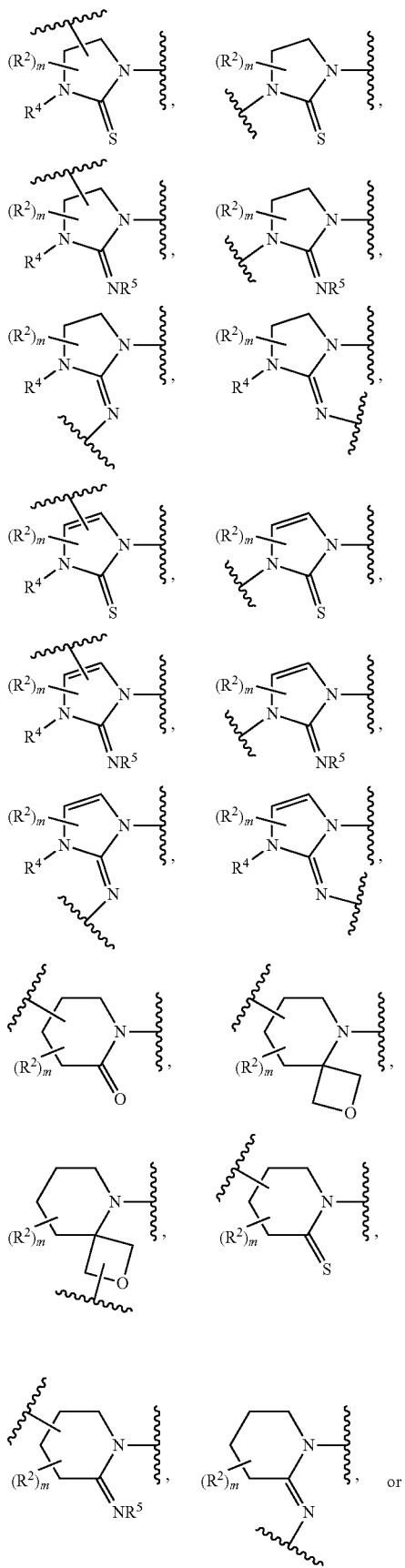

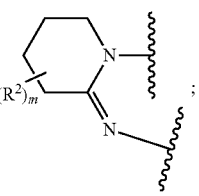

each $R^2$ is independently hydrogen, $-R^6$, halogen, $-CN$, $-NO_2$, $-OR$, $-SR$, $-NR_2$, $-S(O)_2R$, $-S(O)_2NR_2$, $-S(O)R$, $-C(O)R$, $-C(O)OR$, $-C(O)NR_2$, $-C(O)N(R)OR$, $-OC(O)R$, $-OC(O)NR_2$, $-N(R)C(O)OR$, $-N(R)C(O)R$, $-N(R)C(O)NR_2$, or $-N(R)S(O)_2R$;

Ring B is selected from a 6-membered aryl containing 0-2 nitrogen atoms or a 5-membered heteroaryl with 1-3 heteroatoms independently selected from nitrogen, oxygen or sulfur;

each of $R^3$ and $R^4$ is independently hydrogen, $-R^6$, halogen, $-CN$, $-NO_2$, $-OR$, $-SR$, $-NR_2$, $-S(O)_2R$, $-S(O)_2NR_2$, $-S(O)R$, $-C(O)R$, $-C(O)OR$, $-C(O)NR_2$, $-C(O)N(R)OR$, $-OC(O)R$, $-OC(O)NR_2$, $-N(R)C(O)OR$, $-N(R)C(O)R$, $-N(R)C(O)NR_2$, or $-N(R)S(O)_2R$;

$R^5$ is hydrogen, $C_{1-4}$ aliphatic, or $-CN$;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, or 2;

n is 0, 1, 2, 3, or 4;

p is 0 or 1, wherein when p is 0, the bond connecting Ring A and Ring B is connected to

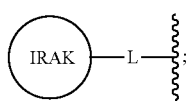

and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In certain embodiments, the present invention provides a compound of Formula I, wherein LBM is an E3 ubiquitin ligase (cereblon) binding moiety

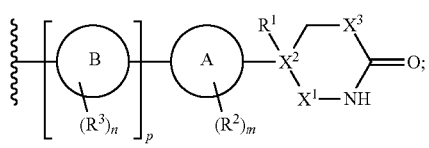

thereby forming a compound of formula I-d':

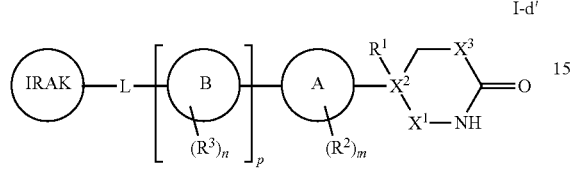

I-d' or a pharmaceutically acceptable salt thereof, wherein L and IRAK are as defined above and described in embodiments herein, and wherein:

$X^1$ is a bivalent moiety selected from a covalent bond, —CH$_2$—, —C(O)—, —C(S)—, or

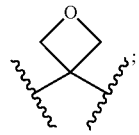

$X^2$ is a carbon atom or silicon atom;
$X^3$ is a bivalent moiety selected from —CH$_2$— or —Si(R$_2$)—;
$R^1$ is hydrogen, deuterium, halogen, —CN, —OR, —SR, —S(O)R, —S(O)$_2$R, —N(R)$_2$, —Si(R)$_3$, or an optionally substituted C$_{1-4}$ aliphatic;
Ring A is a mono- or bicyclic ring selected from

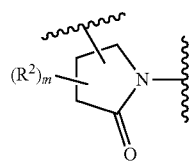 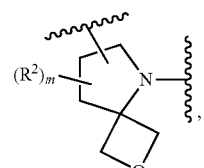

-continued

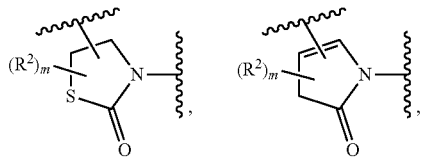
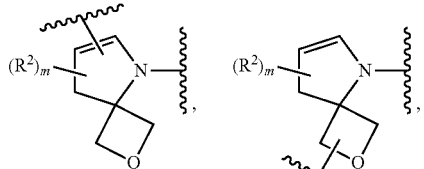
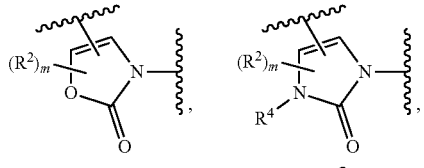
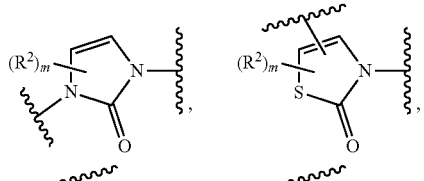
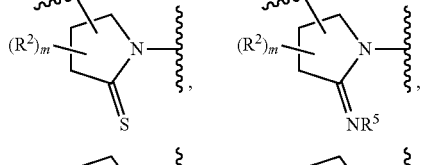
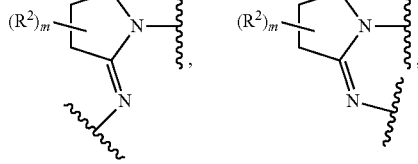
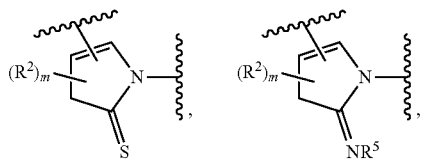
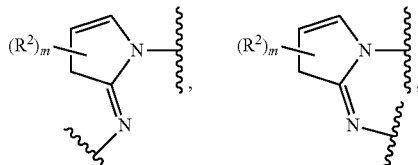
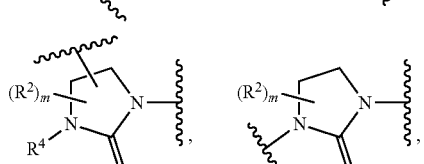
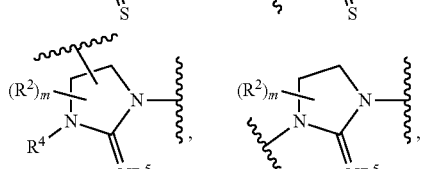
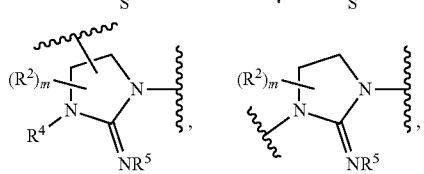

-continued

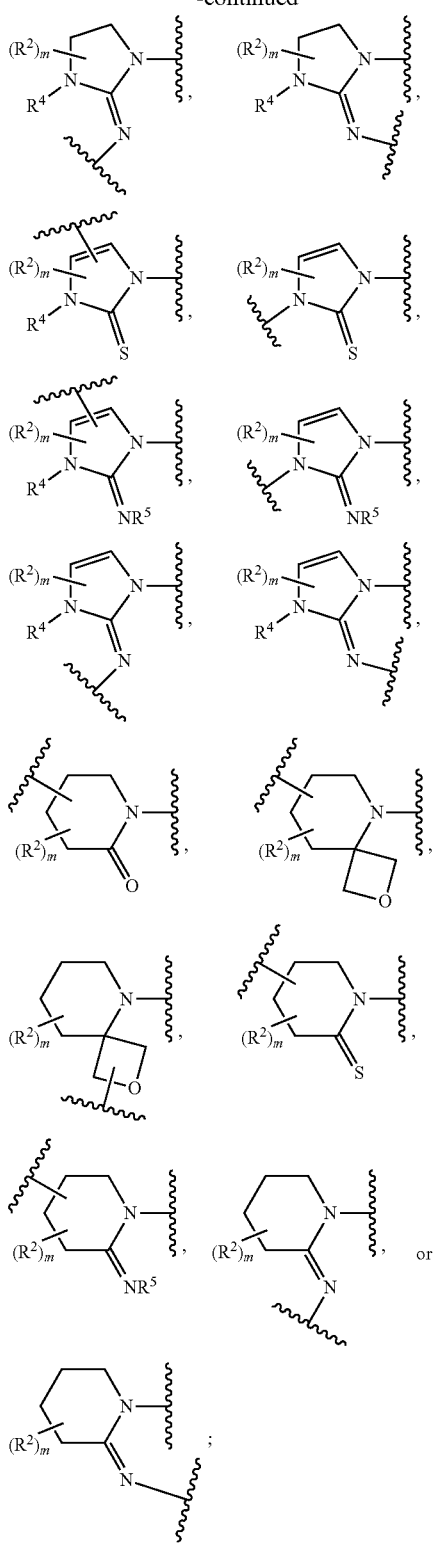

each R² is independently hydrogen, deuterium, —R⁶, halogen, —CN, —NO₂, —OR, —SR, —NR₂, —Si(R)₃, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

Ring B is selected from a 6-membered aryl containing 0-2 nitrogen atoms or a 5-membered heteroaryl with 1-3 heteroatoms independently selected from nitrogen, oxygen or sulfur;

each of R³ and R⁴ is independently hydrogen, —R⁶, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

R⁵ is hydrogen, C₁₋₄ aliphatic, or —CN;

each R⁶ is independently an optionally substituted group selected from C₁₋₆ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, or 2;

n is 0, 1, 2, 3, or 4;

p is 0 or 1, wherein when p is 0, the bond connecting Ring A and Ring B is connected to

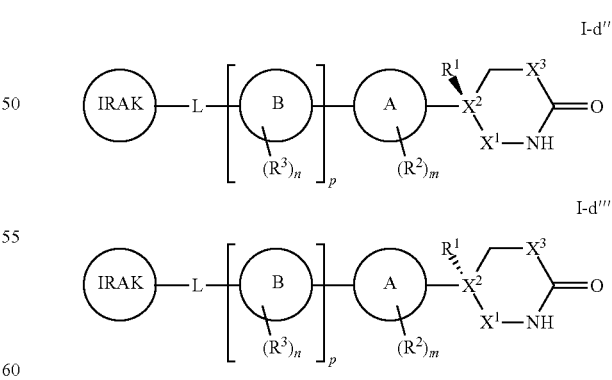

and each R is independently hydrogen, or an optionally substituted group selected from C₁₋₆ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, the compound of formula I-d' above is provided as a compound of formula I-d" or formula I-d'":

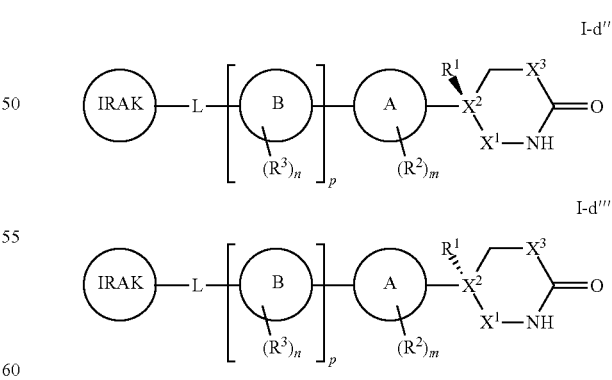

or a pharmaceutically acceptable salt thereof, wherein:
each of IRAK, Ring A, Ring B, L, R¹, R², R³, X¹, X², X³, m, and p is as defined above.

In certain embodiments, the present invention provides a compound of Formula I, wherein LBM is an E3 ubiquitin ligase (cereblon) binding moiety

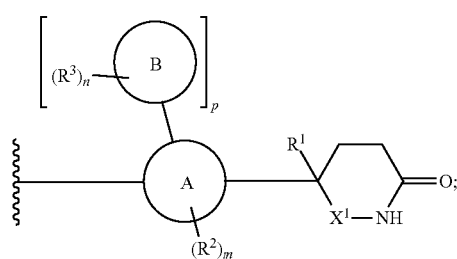

thereby forming a compound of formula I-e:

I-e

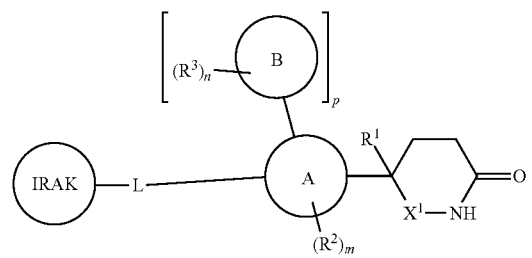

or a pharmaceutically acceptable salt thereof, wherein L and IRAK are as defined above and described in embodiments herein, and wherein:

$X^1$ is a bivalent moiety selected from a covalent bond, —$CH_2$—, —C(O)—, —C(S)—, or

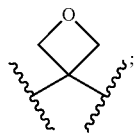 [SMILES: *C1(*)COC1]

$R^1$ is hydrogen, deuterium, halogen, —CN, —OR, —SR, —S(O)R, —S(O)$_2$R, —$NR_2$, or an optionally substituted $C_{1-4}$ aliphatic;

Ring A is a mono- or bicyclic ring selected from

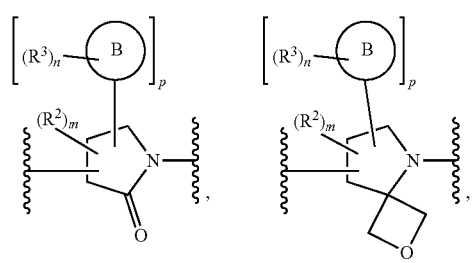

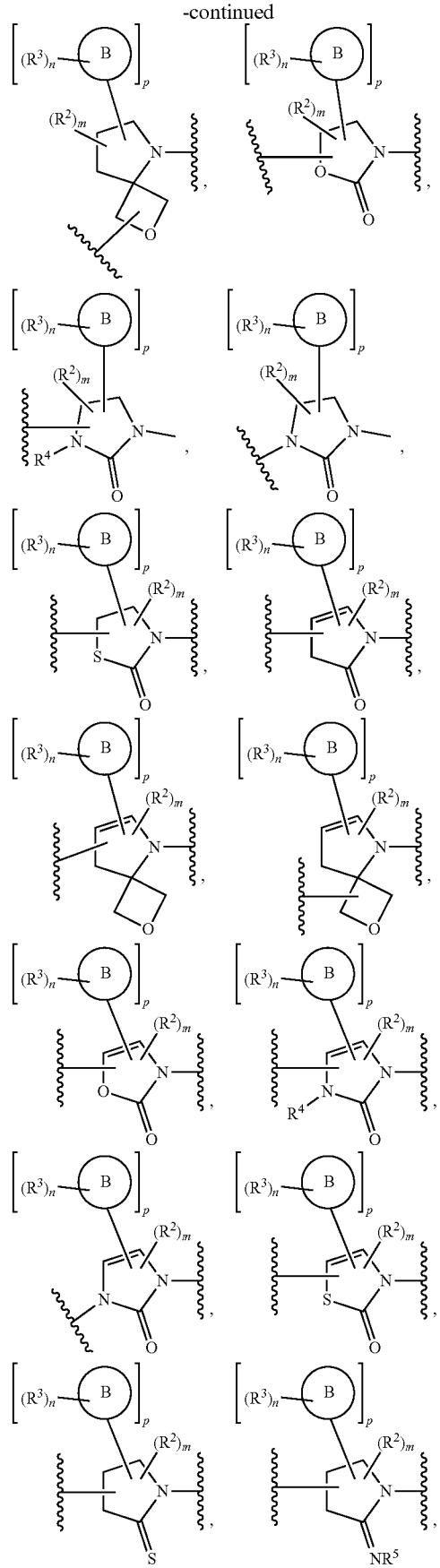

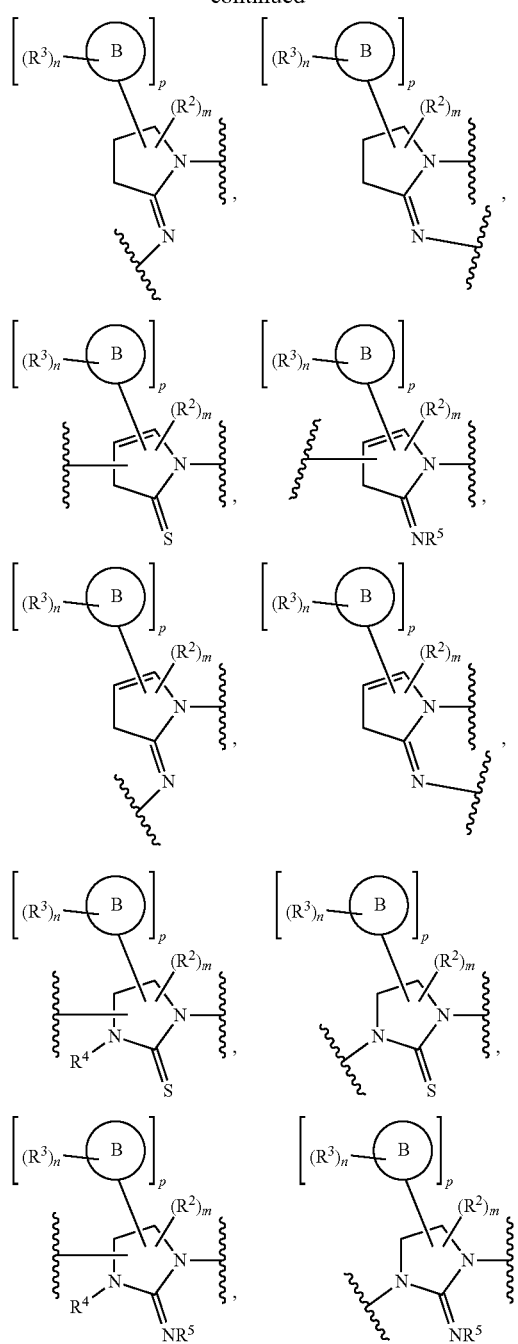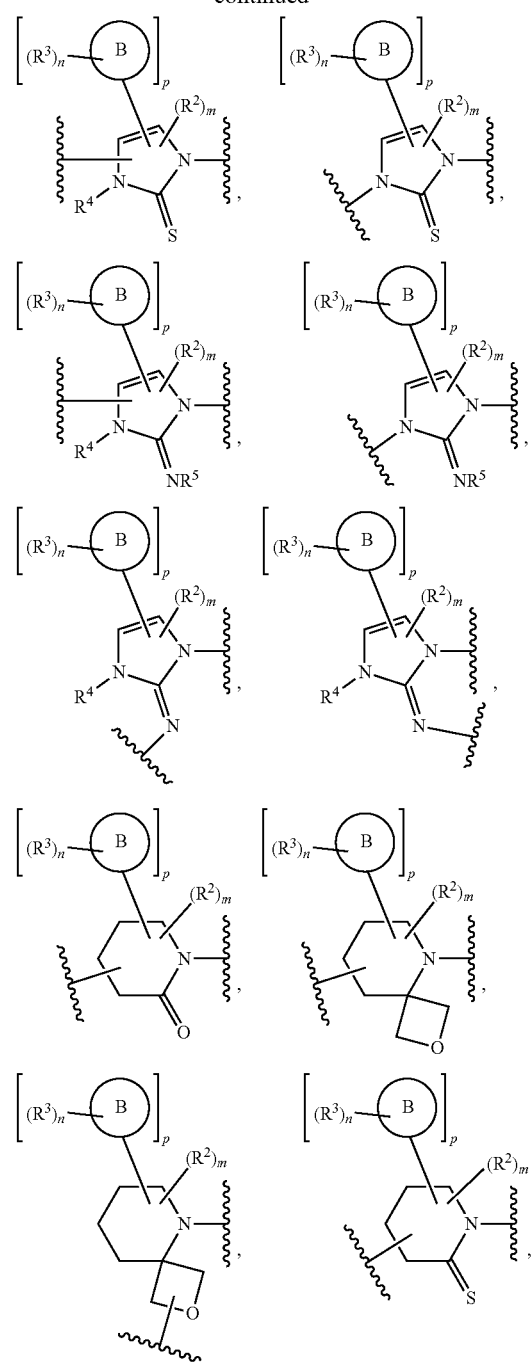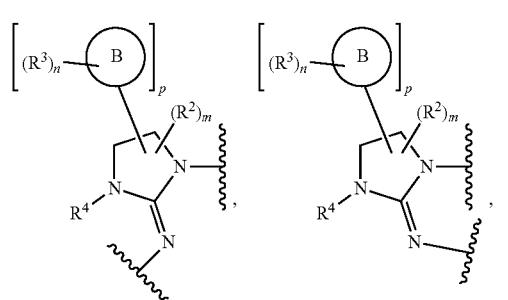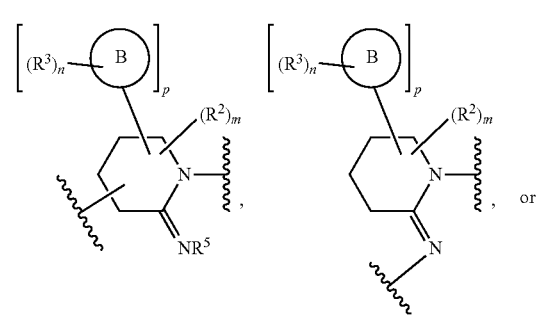

-continued

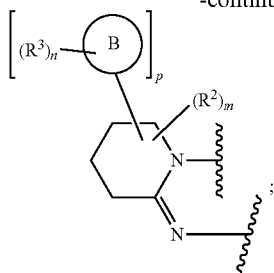

each R² is independently hydrogen, —R⁶, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

Ring B is selected from a 6-membered aryl containing 0-2 nitrogen atoms or a 5-membered heteroaryl with 1-3 heteroatoms independently selected from nitrogen, oxygen or sulfur;

each of R³ and R⁴ is independently hydrogen, —R⁶, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

R⁵ is hydrogen, C₁₋₄ aliphatic, or —CN;

each R⁶ is independently an optionally substituted group selected from C₁₋₆ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, or 2;

n is 0, 1, 2, 3, or 4;

p is 0 or 1; and each R is independently hydrogen, or an optionally substituted group selected from C₁₋₆ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In certain embodiments, the present invention provides a compound of Formula I, wherein LBM is an E3 ubiquitin ligase (cereblon) binding moiety

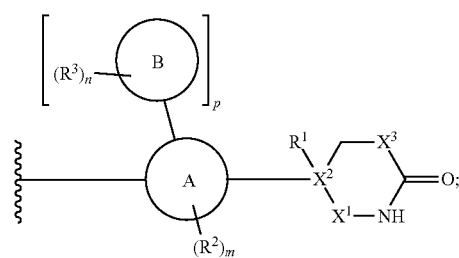

thereby forming a compound of formula I-e':

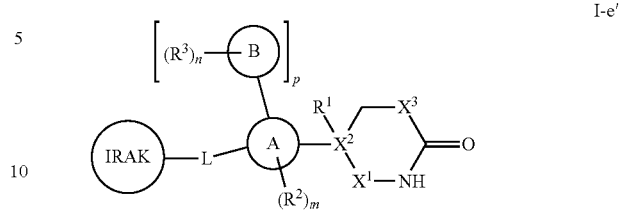

or a pharmaceutically acceptable salt thereof, wherein L and IRAK are as defined above and described in embodiments herein, and wherein:

X¹ is a bivalent moiety selected from a covalent bond, —CH₂—, —C(O)—, —C(S)—, or

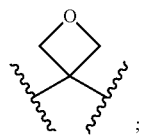 [SMILES: *C1(*)COC1]

X² is a carbon atom or silicon atom;

X³ is a bivalent moiety selected from —CH₂— or —Si(R₂)—;

R¹ is hydrogen, deuterium, halogen, —CN, —OR, —SR, —S(O)R, —S(O)₂R, —N(R)₂, —Si(R)₃, or an optionally substituted C₁₋₄ aliphatic;

Ring A is a mono- or bicyclic ring selected from

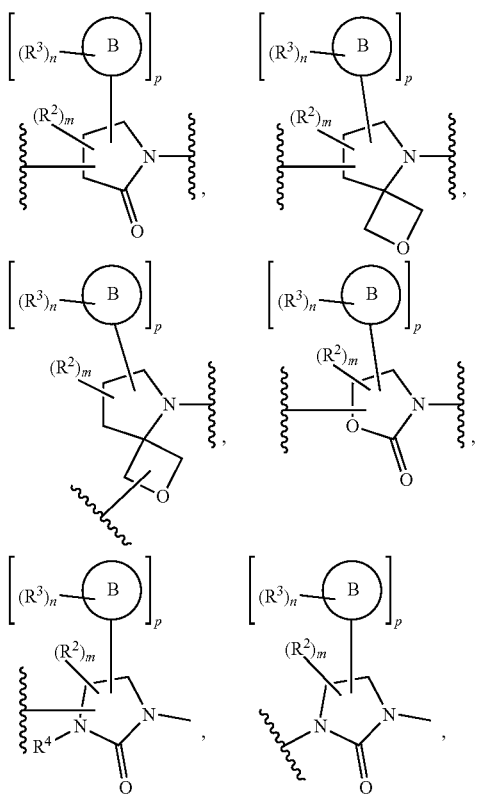

-continued
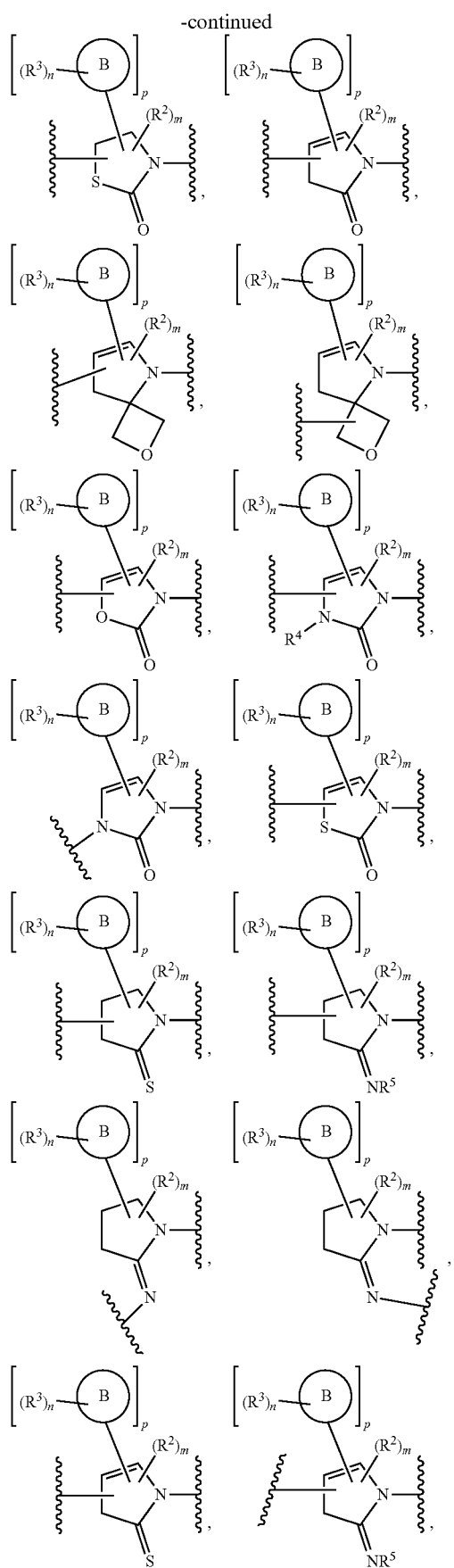
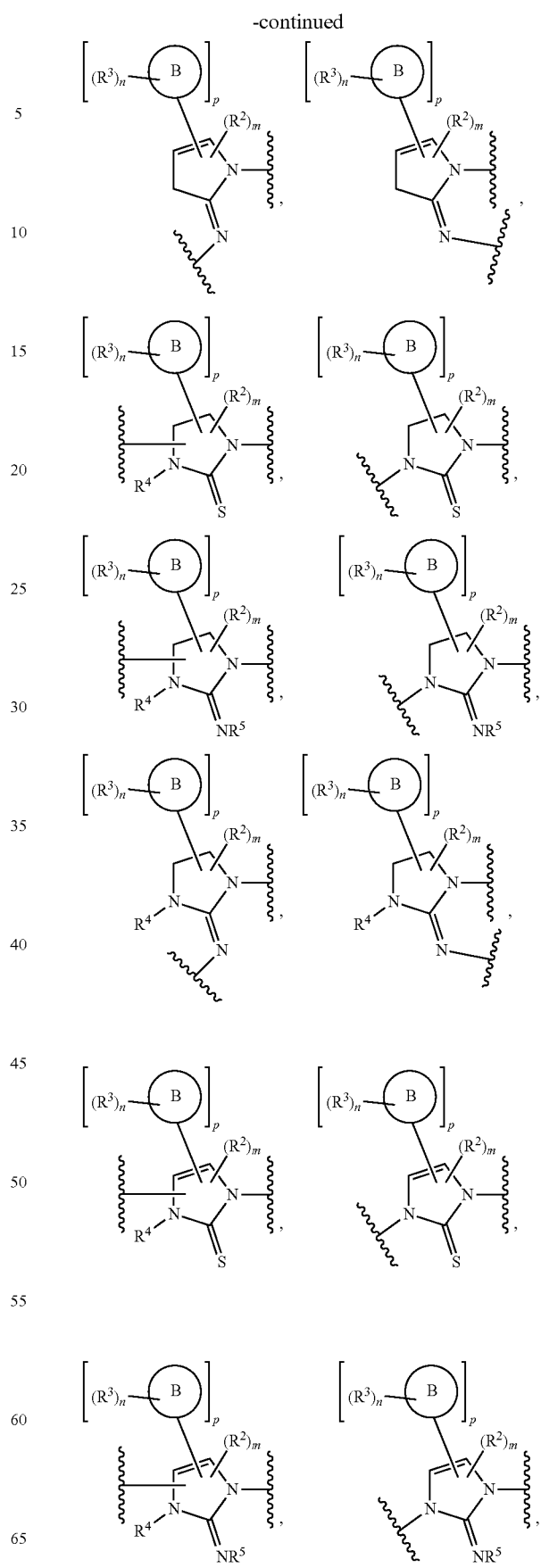

-continued

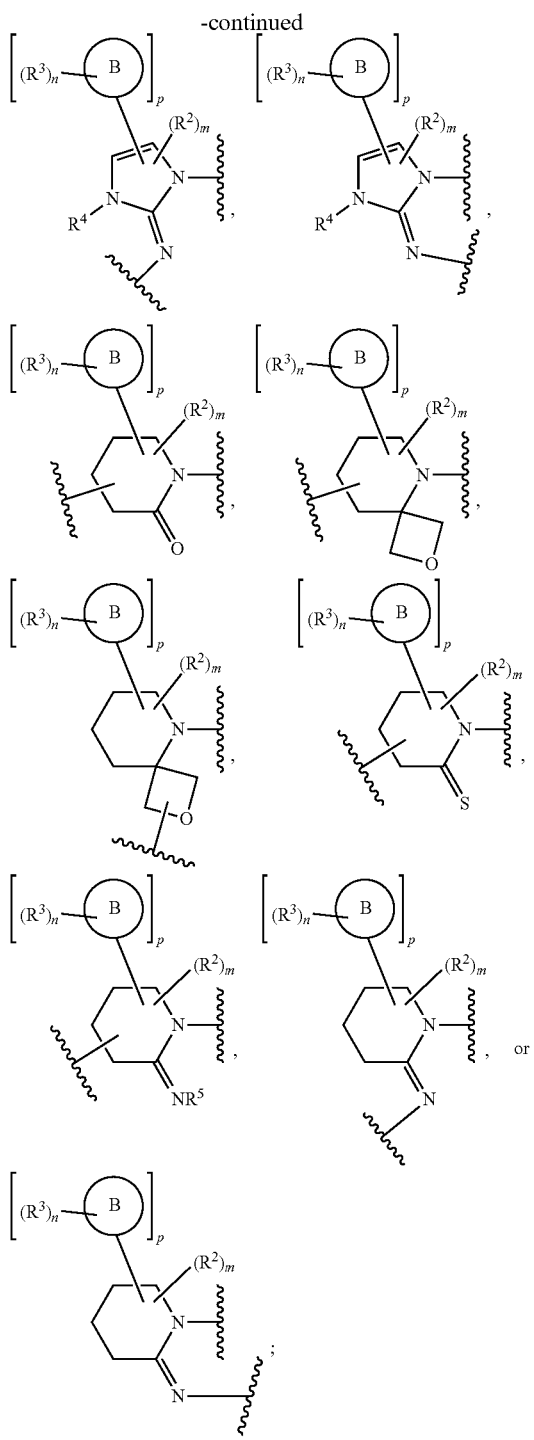

each R² is independently hydrogen, deuterium, —R⁶, halogen, —CN, —NO₂, —OR, —SR, —NR₂, —Si(R)₃, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

Ring B is selected from a 6-membered aryl containing 0-2 nitrogen atoms or a 5-membered heteroaryl with 1-3 heteroatoms independently selected from nitrogen, oxygen or sulfur;

each of R³ and R⁴ is independently hydrogen, —R⁶, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

R⁵ is hydrogen, C₁₋₄ aliphatic, or —CN;

each R⁶ is independently an optionally substituted group selected from C₁₋₆ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, or 2;

n is 0, 1, 2, 3, or 4;

p is 0 or 1; and each R is independently hydrogen, or an optionally substituted group selected from C₁₋₆ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, the compound of formula I-e' above is provided as a compound of formula I-e" or formula I-e''':

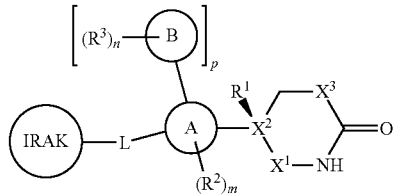

I-e"

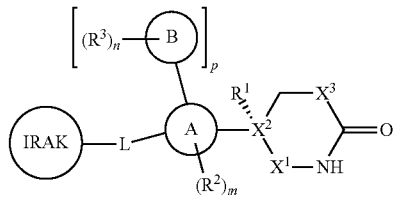

I-e''' or a pharmaceutically acceptable salt thereof, wherein:
each of IRAK, Ring A, Ring B, L, R¹, R², R³, X¹, X², X³, p, and m is as defined above.

In certain embodiments, the present invention provides a compound of Formula I, wherein LBM is a VHL E3 ubiquitin ligase binding moiety

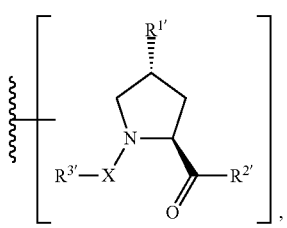

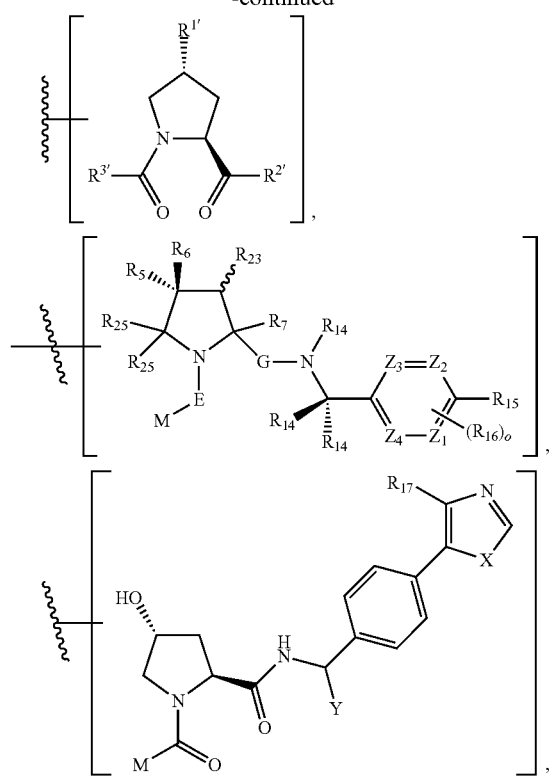
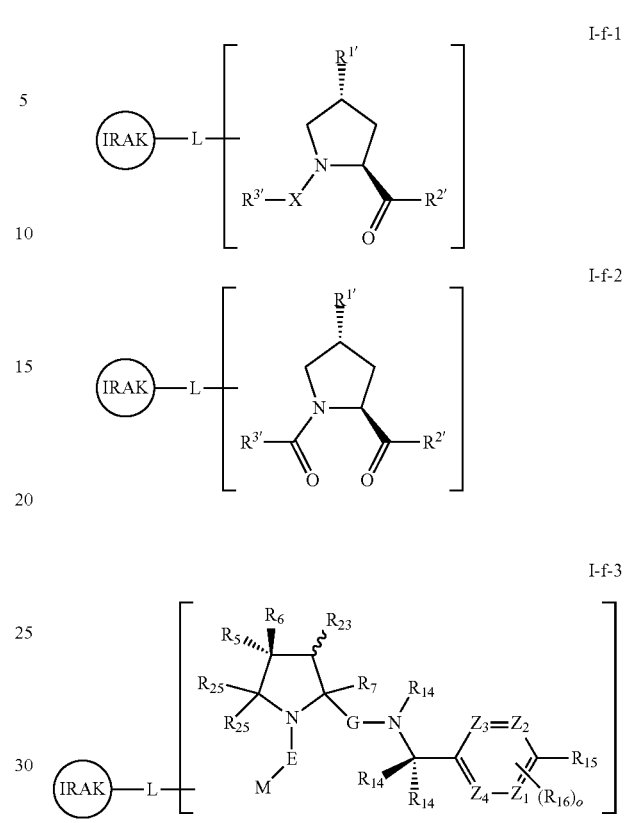
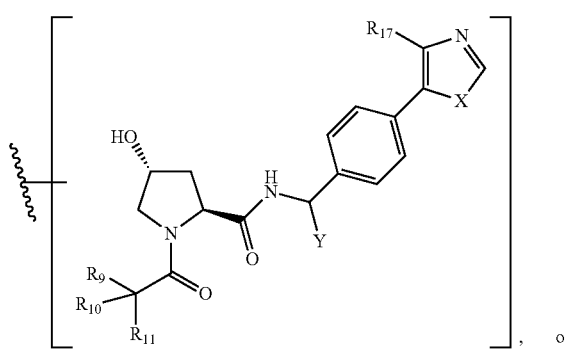
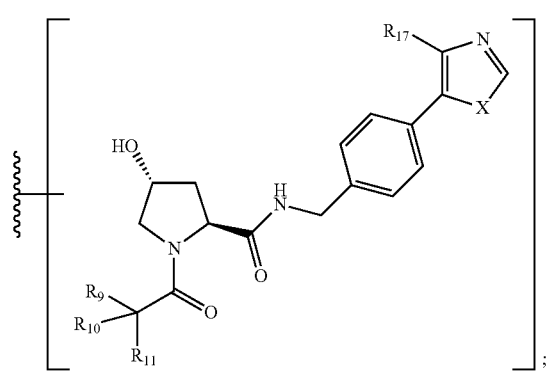
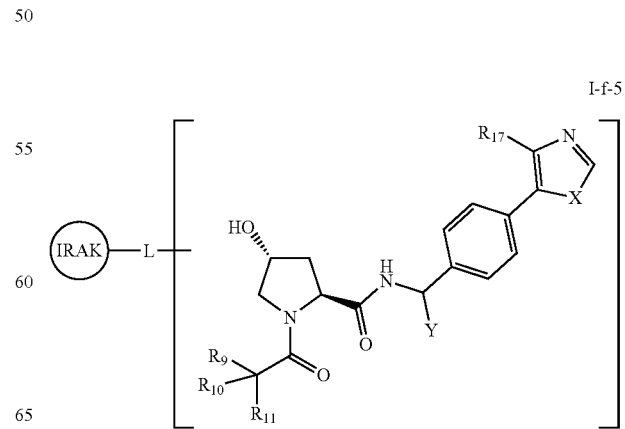
thereby forming a compound of formula I-f-1, I-f-2, I-f-3, I-f-4, I-f-5 or I-f-6 respectively:

-continued

I-f-6

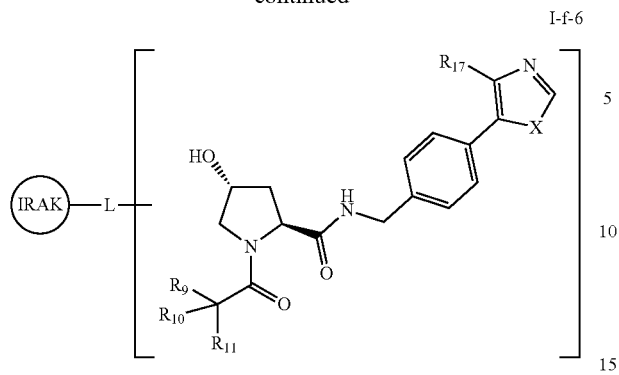

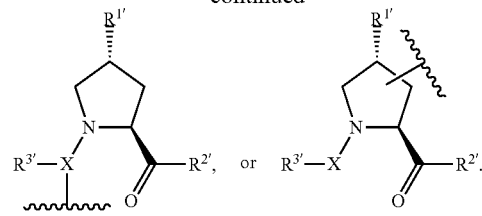

or a pharmaceutically acceptable salt thereof, wherein L and IRAK are as defined above and described in embodiments herein, and wherein each of the variables $R^{1'}$, $R^{2'}$, $R^{3'}$, $R_5$, $R_6$, $R_7$, $R_9$, $R_{10}$, $R_{11}$, $R_{14}$, $R_{15}$, $R_{16}$, $R_{17}$, $R_{23}$, $R_{25}$, E, G, M, X, X', Y, $Z_1$, $Z_2$, $Z_3$, $Z_4$, and o is as defined and described in WO 2016/149668 and US 2016/0272639, the entirety of each of which is herein incorporated by reference.

As used herein, depiction of brackets around any LBM

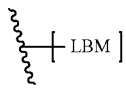

means that the

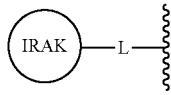

moiety is covalently attached to said LBM at any available modifiable carbon, nitrogen, oxygen, or sulfur atom. For purposes of clarity and by way of example, such available modifiable carbon, nitrogen, oxygen, or sulfur atoms in the following LBM compound structure are depicted below, wherein each wavy bond defines the point of attachment to said

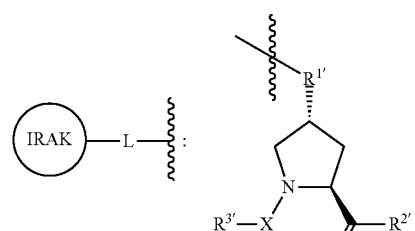

In certain embodiments, the present invention provides a compound of Formula I, wherein LBM is a VHL E3 ubiquitin ligase binding moiety

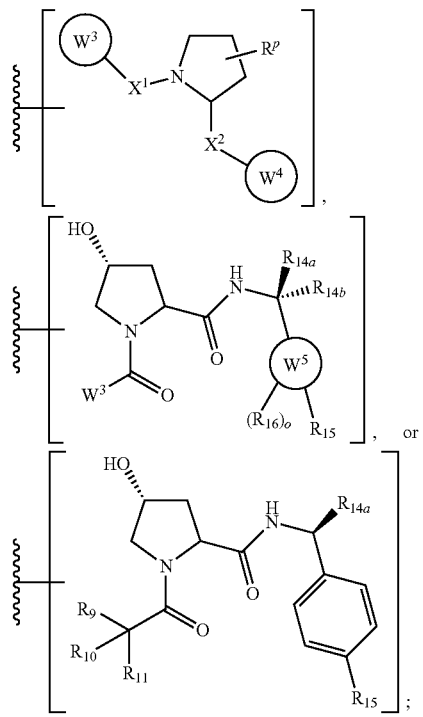

thereby forming a compound of formula I-g-1, I-g-2, or I-g-3 respectively:

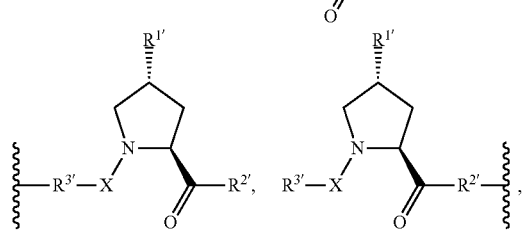

I-g-1

I-g-2

I-g-3

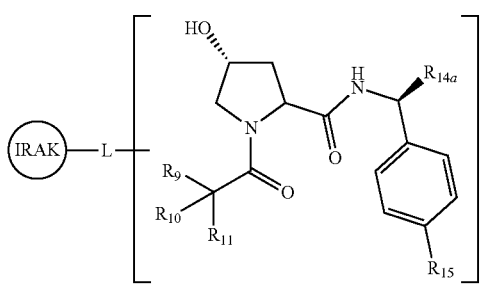

or a pharmaceutically acceptable salt thereof, wherein L and IRAK are as defined above and described in embodiments herein, and wherein each of the variables $R^p$, $R_9$, $R_{10}$, $R_{11}$, $R_{14a}$, $R_{14b}$, $R_{15}$, $R_{16}$, $W^3$, $W^4$, $W^5$, $X^1$, $X^2$, and o is as defined and described in WO 2016/118666 and US 2016/0214972, the entirety of each of which is herein incorporated by reference.

In certain embodiments, the present invention provides a compound of Formula I, wherein LBM is an E3 ubiquitin ligase (cereblon) binding moiety

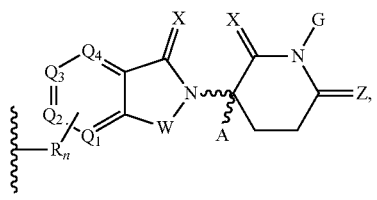

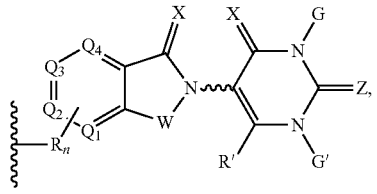

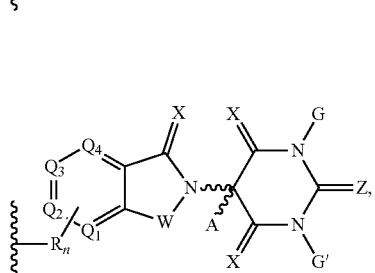

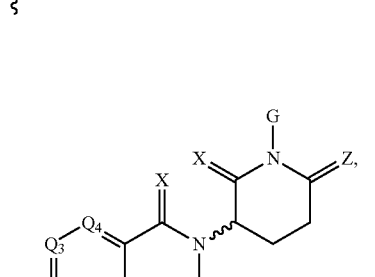

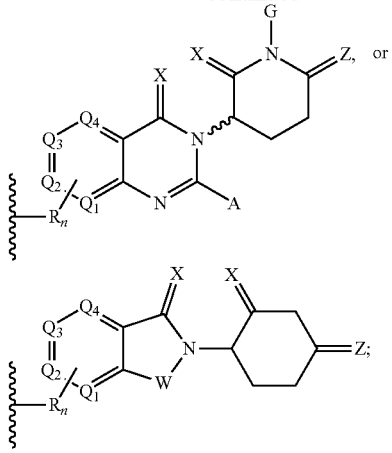

thereby forming a compound of formula I-h-1, I-h-2, I-h-3, I-h-4, I-h-5, or I-h-6 respectively:

I-h-1

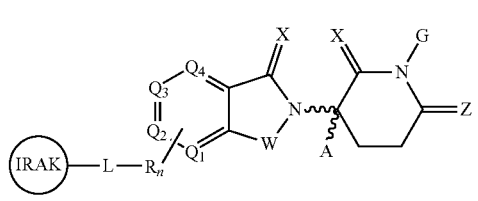

I-h-2

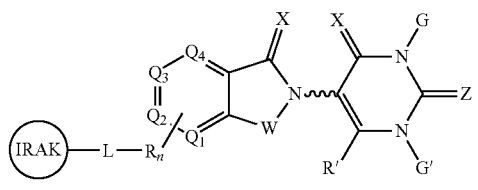

I-h-3

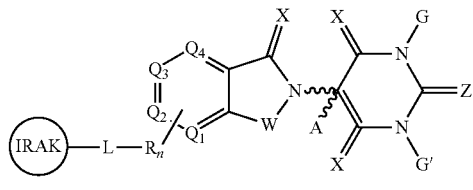

I-h-4

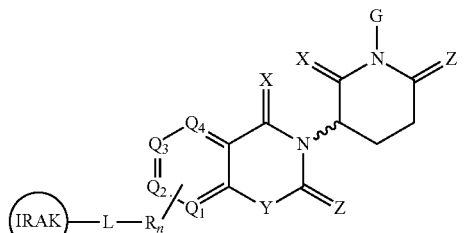

I-h-5

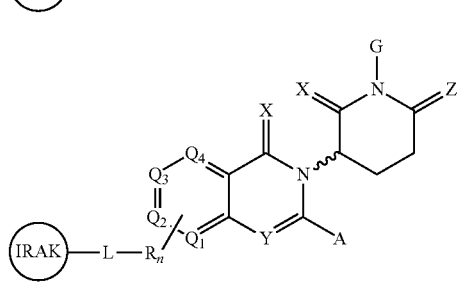

-continued

I-h-6

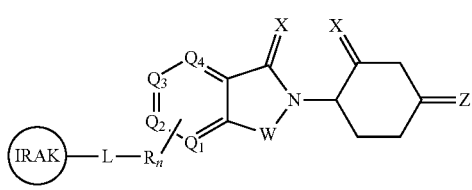

or a pharmaceutically acceptable salt thereof, wherein L and IRAK are as defined above and described in embodiments herein, and wherein W is independently selected from the group $CH_2$, CHR, C=O, $SO_2$, NH, and N-alkyl;
X is independently selected from the group O, S and $H_2$;
Y is independently selected from the group NH, N-alkyl, N-aryl, N-hetaryl, N-cycloalkyl, N-heterocyclyl, O, and S;
Z is independently selected from the group O, and S or $H_2$, except that both X and Z cannot be $H_2$;
G and G' are independently selected from the group H, alkyl, OH, $CH_2$-heterocyclyl optionally substituted with R', and benzyl optionally substituted with R';
Q1-Q4 represent a carbon C substituted with a group independently selected from R', N or N-oxide;
A is independently selected from the group H, alkyl, cycloalkyl, Cl and F;
R comprises, but is not limited to: —CONR'R", —OR', —NR'R", —SR', —$SO_2$R', —$SO_2$NR'R", —CR'R"—, —CR'NR'R"—, -aryl, -hetaryl, -alkyl, -cycloalkyl, -heterocyclyl, —P(O)(OR')R", —P(O)R'R", —OP(O)(OR')R", —OP(O)R'R", —Cl, —F, —Br, —I, —$CF_3$, —CN, —NR'$SO_2$NR'R", —NR'CONR'R", —CONR'COR", —NR'C(=N—CN)NR'R", —C(=N—CN)NR'R", —NR'C(=N—CN)R", —NR'C(=C—$NO_2$)NR'R", —$SO_2$NR'COR", —$NO_2$, —$CO_2$R', —C(C=N—OR')R", —CR'=CR'R", —CCR', —S(C=O)(C=N—R')R", —$SF_5$ and —$OCF_3$;
R' and R" are independently selected from a bond, H, alkyl, cycloalkyl, aryl, hetaryl, heterocyclyl;
n is an integer from 1-4;
〜 represents a bond that may be stereospecific ((R) or (S)) or non-stereospecific; and
$R_n$ comprises 1-4 independent functional groups or atoms; as defined and described in WO 2016/197114 and US 2018/0147202, the entirety of each of which is herein incorporated by reference.

In certain embodiments, the present invention provides a compound of Formula I, wherein LBM is a MDM2 (i.e. human double minute 2 or HDM2) E3 ligase binding moiety

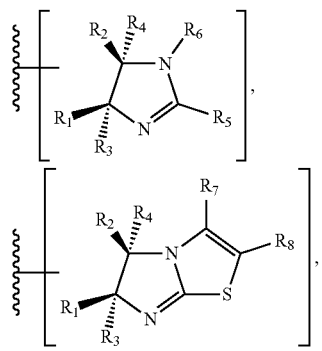

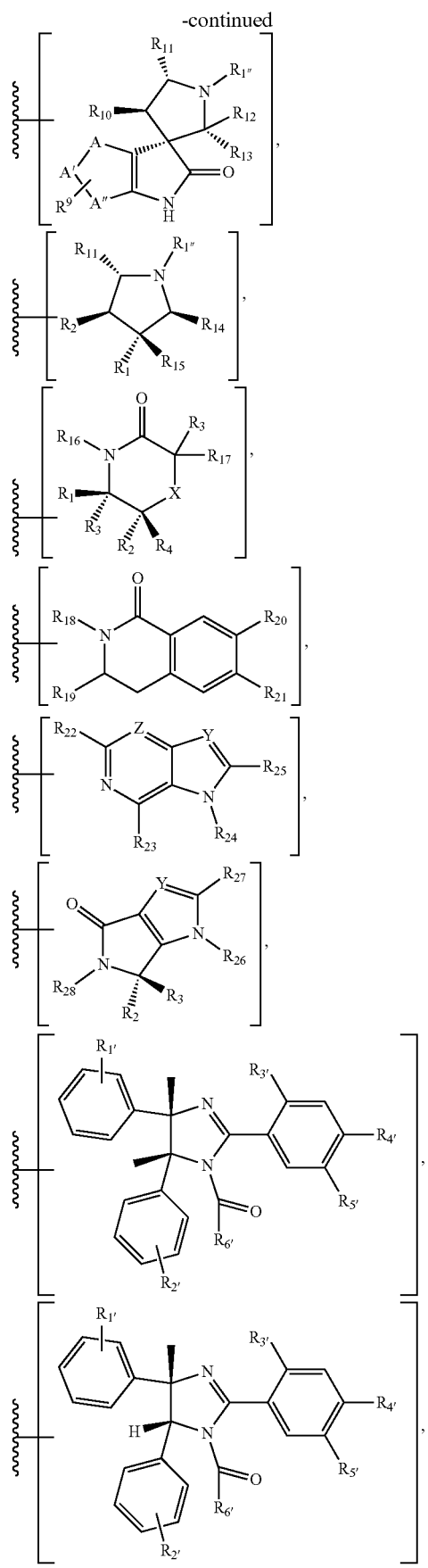

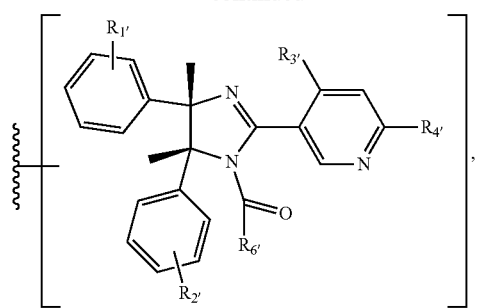
,
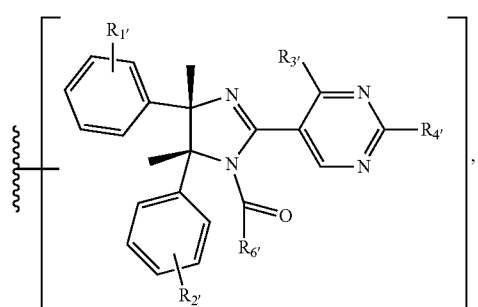
,
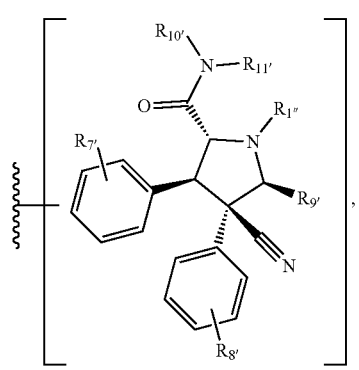
,
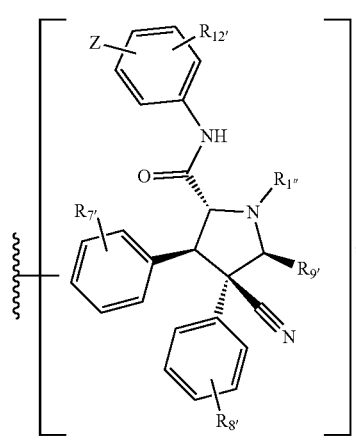
,
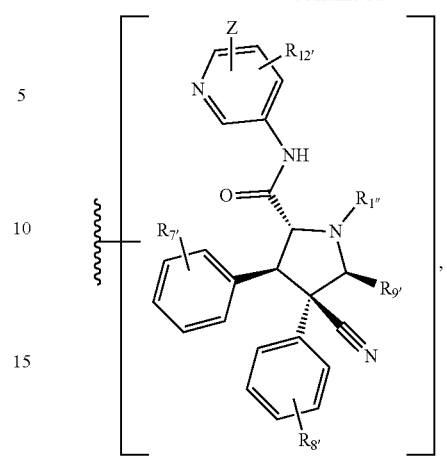
,
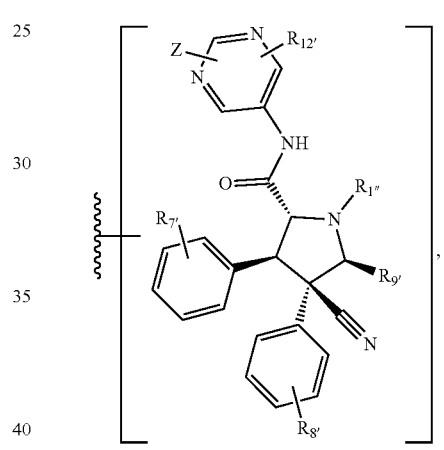
,
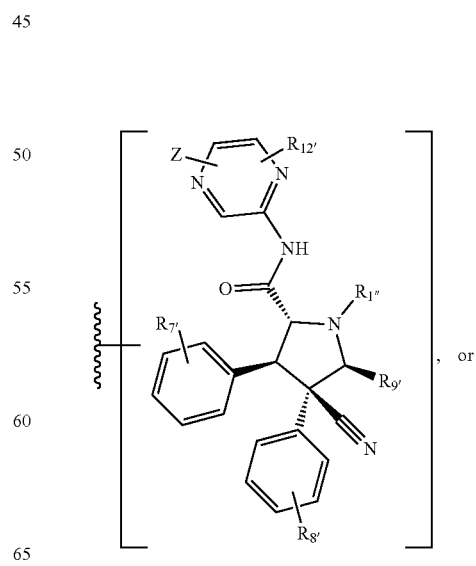
, or -continued
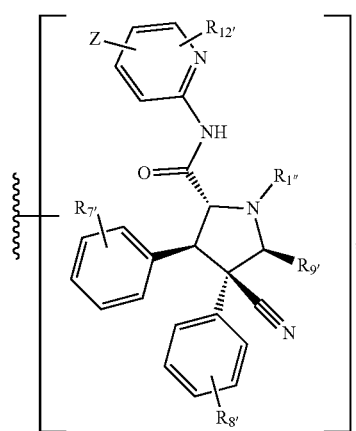
thereby forming a compound of formula I-i-1, I-i-2, I-i-3, I-i-4, I-i-5, I-i-6, I-i-7, I-i-8, I-i-9, I-i-10, I-i-11, I-i-12, I-i-13, I-i-14, I-i-15, I-i-16, I-i-17, or I-i-18 respectively:
I-i-1
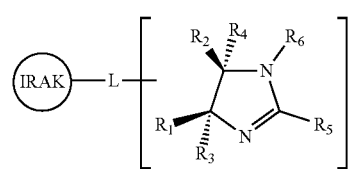
I-i-2
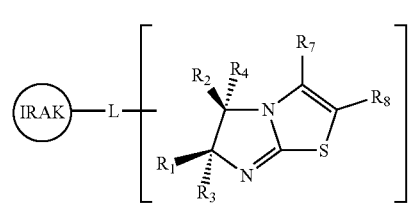
I-i-3
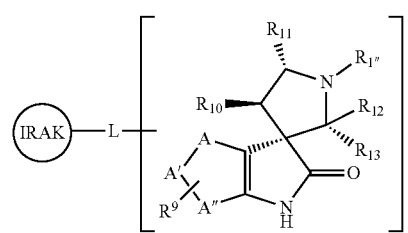
I-i-4
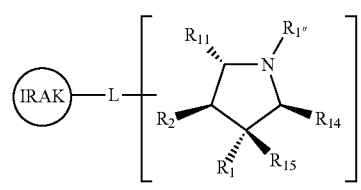
I-i-5
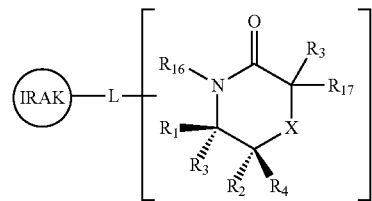
-continued
I-i-6
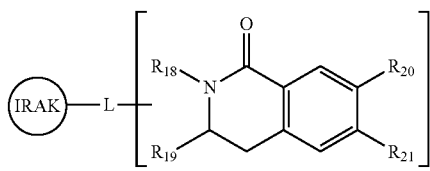
I-i-7
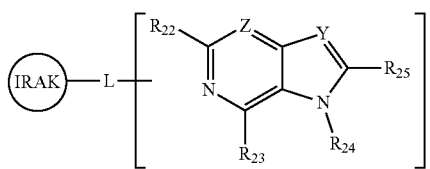
I-i-8
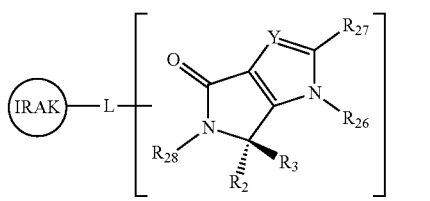
I-i-9
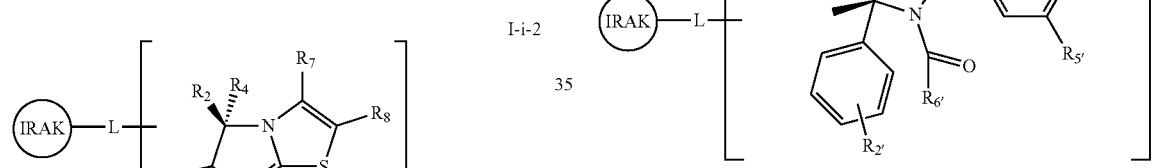
I-i-10
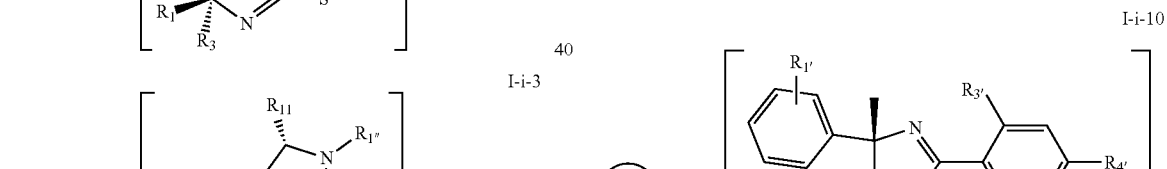
I-i-11
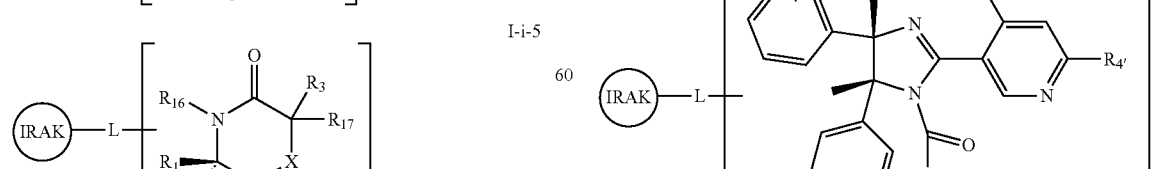

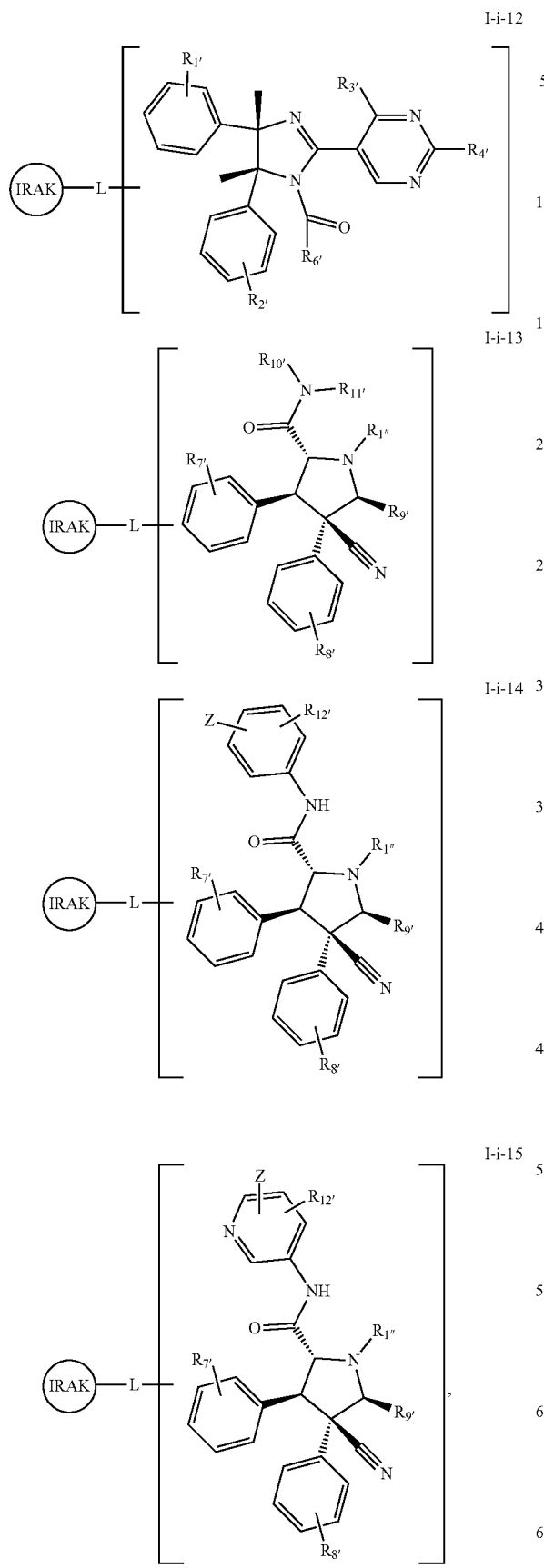
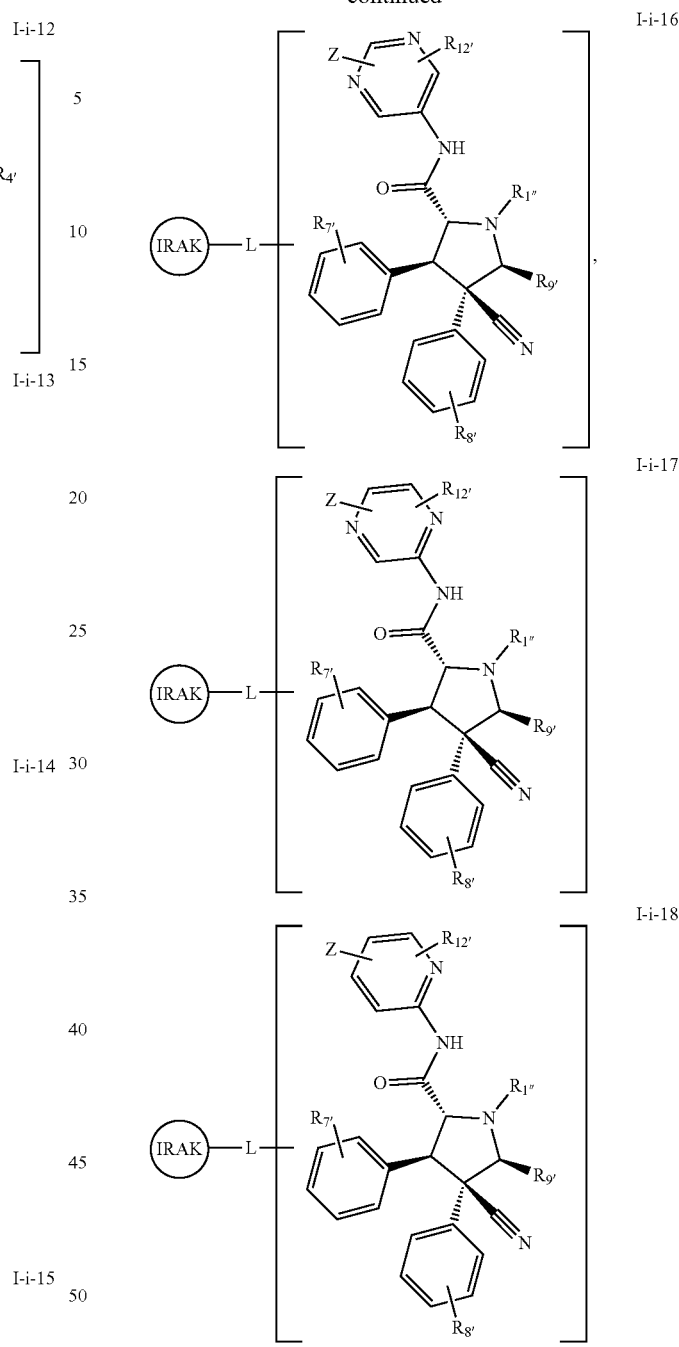

or a pharmaceutically acceptable salt thereof, wherein L and IRAK are as defined above and described in embodiments herein, and wherein each of the variables $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{1'}$, $R_{2'}$, $R_{3'}$, $R_{4'}$, $R_{5'}$, $R_{6'}$, $R_{7'}$, $R_{8'}$, $R_{9'}$, $R_{10'}$, $R_{11'}$, $R_{12'}$, $R_{1'''}$, A, A', A'', X, Y, and Z is as defined and described in WO 2017/011371 and US 2017/0008904, the entirety of each of which is herein incorporated by reference.

In certain embodiments, the present invention provides a compound of Formula I, wherein LBM is a CRBN or VHL E3 ubiquitin ligase binding moiety selected from the group consisting of

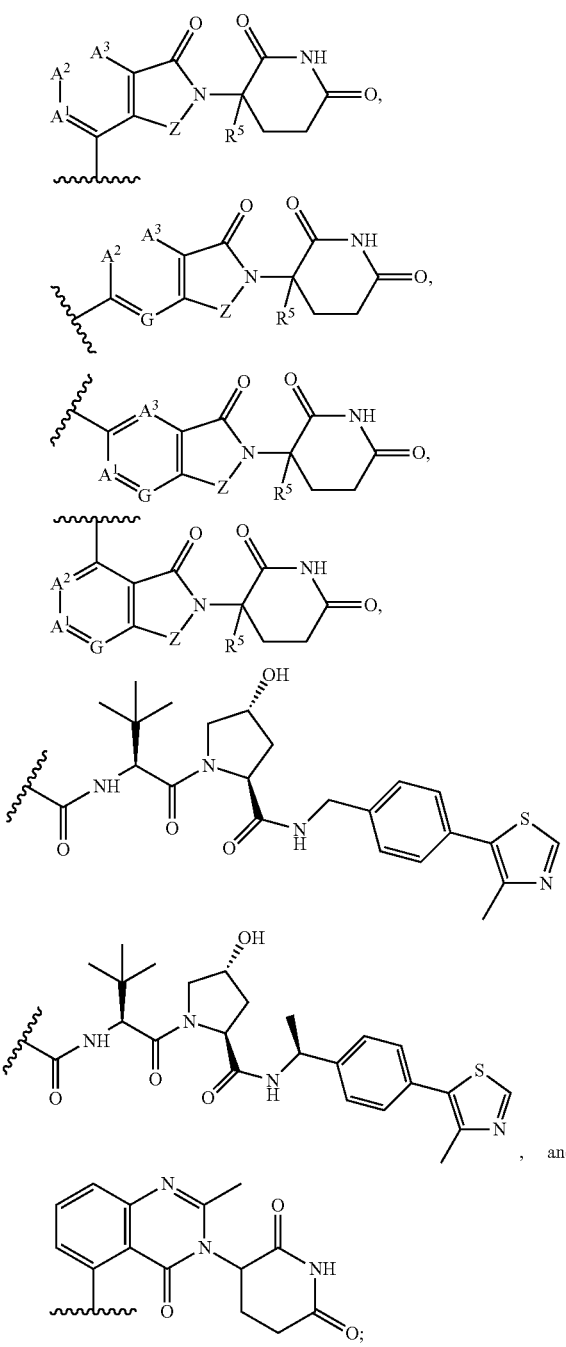

thereby forming a compound of formula I-j-1, I-j-2, I-j-3, I-j-4, I-j-5, I-j-6, or I-j-7 respectively:

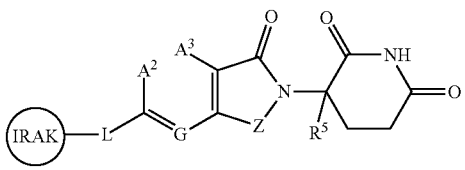

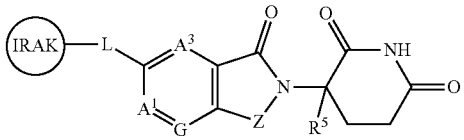

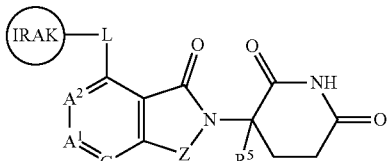

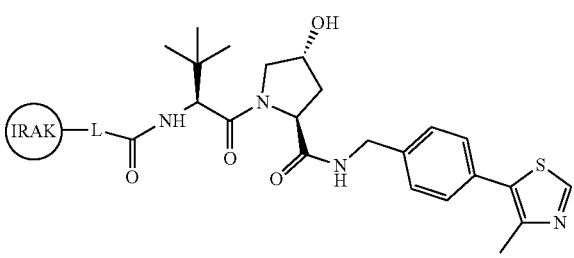

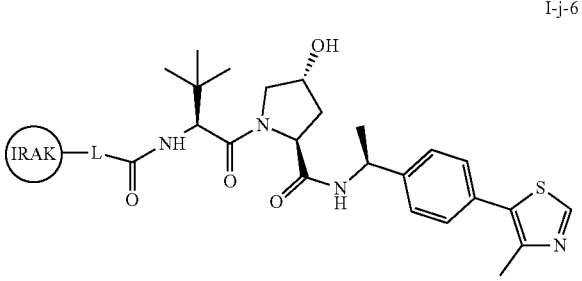

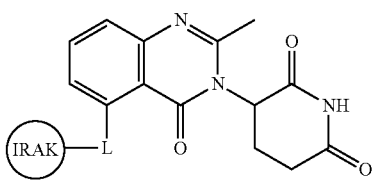

or a pharmaceutically acceptable salt thereof, wherein L and IRAK are as defined above and described in embodiments herein, and wherein $A^1$ is selected from the group consisting of —C($R^{16a}$)═ and —N═;

$A^2$ is selected from the group consisting of —C($R^{16b}$)═ and —N═;

$A^3$ is selected from the group consisting of —C($R^{16}$)═ and —N═;

G is selected from the group consisting of —C($R^{16d}$)═ and —N═;

Z is selected from the group consisting of —CH$_2$ and —C(═O)—;

$R^5$ is selected from the group consisting of hydrogen, methyl, and fluoro;

$R^{16a}$ is selected from the group consisting of hydrogen, halo, and $C_{1-4}$ alkyl;

$R^{16b}$ is selected from the group consisting of hydrogen, halo, and $C_{1-4}$ alkyl;

$R^{16c}$ is selected from the group consisting of hydrogen, halo, and $C_{1-4}$ alkyl; and $R^{16d}$ is selected from the group consisting of hydrogen, halo, and $C_{1-4}$ alkyl;

as defined and described in WO 2017/176958, the entirety of which is herein incorporated by reference.

In certain embodiments, the present invention provides a compound of Formula I, wherein LBM is a CRBN or VHL E3 ubiquitin ligase binding moiety selected from the group consisting of

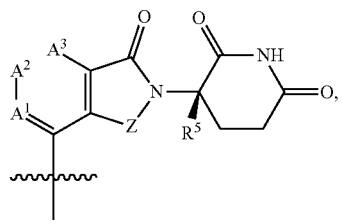

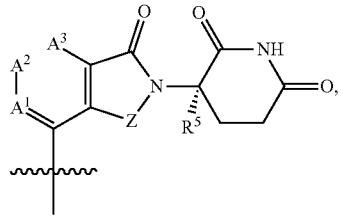

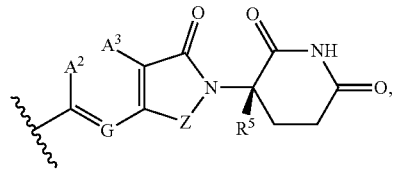

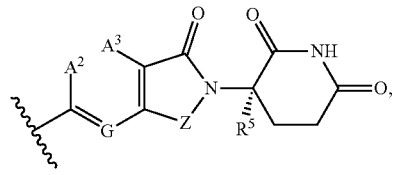

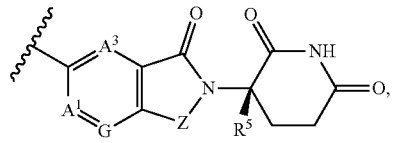

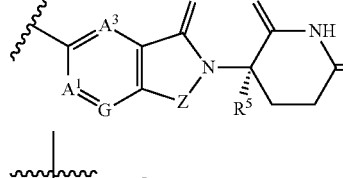

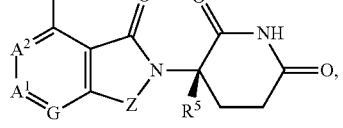

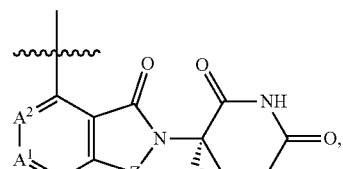

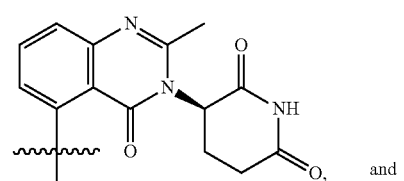

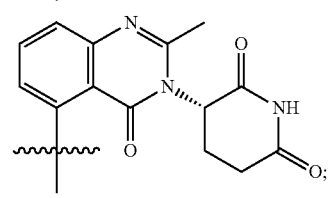

thereby forming a compound of formula I-j'-1, I-j"-1, I-j'-2, I-j"-2, I-j'-3, I-j"-3, I-j'-4, I-j"-4, I-j'-7, or I-j"-7 respectively:

I-j'-1

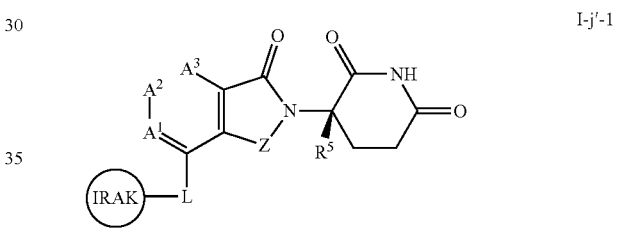

I-j"-1


I-j'-2

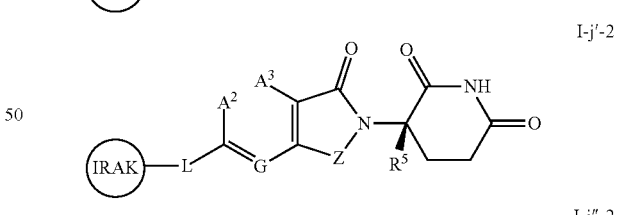

I-j"-2

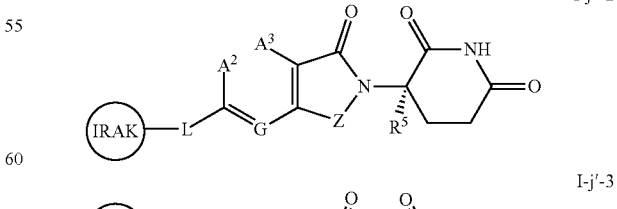

I-j'-3

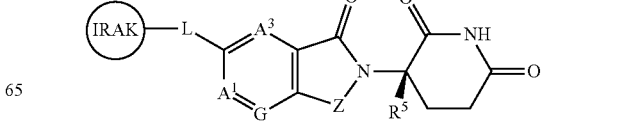

-continued

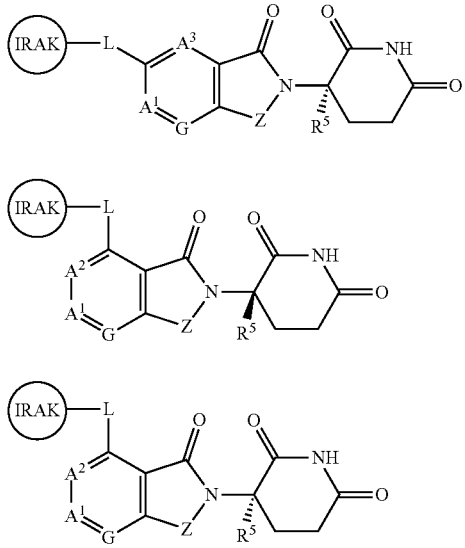

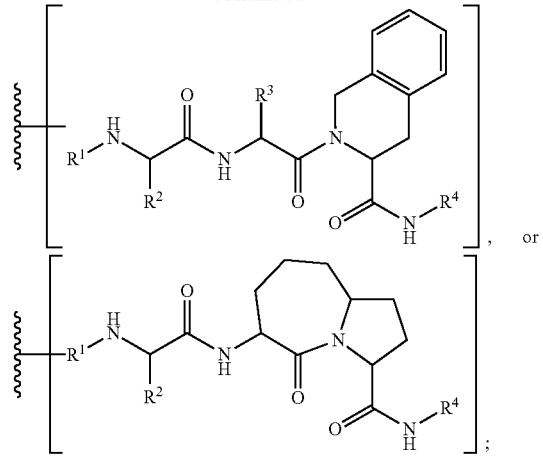

thereby forming a compound of formula I-k-1, I-k-2, I-k-3, or I-k-4 respectively:

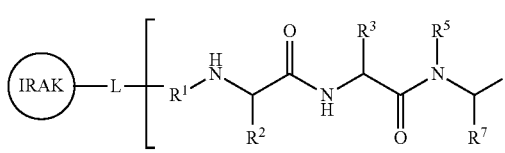

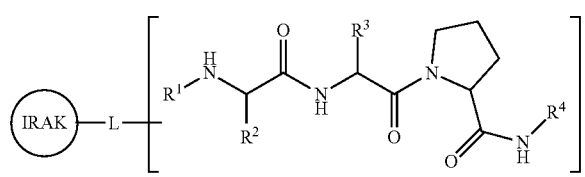

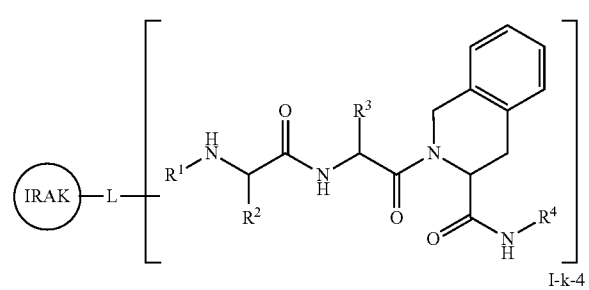

or a pharmaceutically acceptable salt thereof, wherein L and IRAK are as defined above and described in embodiments herein, and wherein each of the variables $A^1$, $A^2$, $A^3$, $R^5$, G and Z is as defined and described in WO 2017/176958, the entirety of which is herein incorporated by reference.

In certain embodiments, the present invention provides a compound of Formula I, wherein LBM is an IAP E3 ubiquitin ligase binding moiety

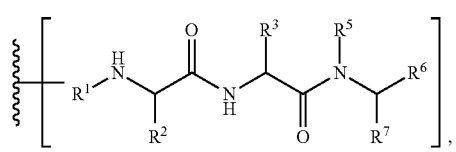

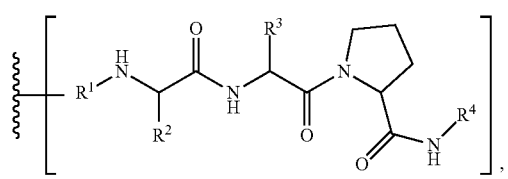

or a pharmaceutically acceptable salt thereof, wherein L and IRAK are as defined above and described in embodiments herein, and wherein each of the variables $R^1$, $R^2$, $R^3$, $R^4$, $R^5$, $R^6$, and $R^7$, is as defined and described in WO 2017/011590 and US 2017/0037004, the entirety of each of which is herein incorporated by reference.

In certain embodiments, the present invention provides a compound of Formula I, wherein LBM is an IAP E3 ubiquitin ligase binding moiety

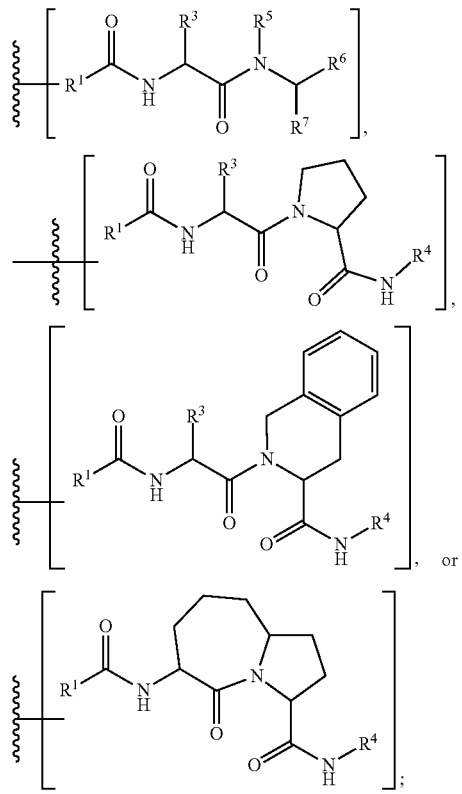

thereby forming a compound of formula I-k'-1, I-k'-2, I-k'-3, or I-k'-4 respectively:

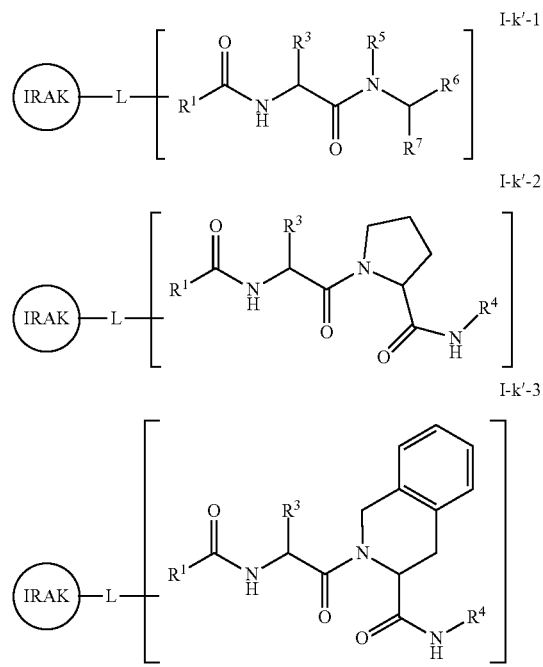

I-k'-1

I-k'-2

I-k'-3

I-k'-4

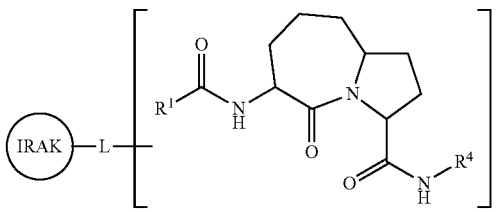

or a pharmaceutically acceptable salt thereof, wherein L and IRAK are as defined above and described in embodiments herein, and wherein each of the variables $R^1$, $R^3$, $R^4$, $R^5$, $R^6$, and $R^7$, is as defined and described in WO 2017/011590 and US 2017/0037004, the entirety of each of which is herein incorporated by reference.

In certain embodiments, the present invention provides a compound of formula I, wherein LBM is an E3 ubiquitin ligase (cereblon) binding moiety

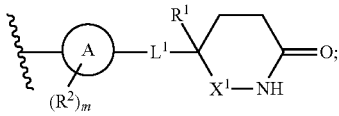

Thereby forming a compound of formula I-1:

I-1

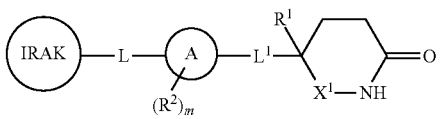

or a pharmaceutically acceptable salt thereof, wherein L and IRAK are as defined above and described herein, and wherein:

$X^1$ is a bivalent moiety selected from a covalent bond, —CH$_2$—, —C(O)—, —C(S)—, or

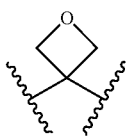

$R^1$ is hydrogen, deuterium, halogen, —CN, —OR, —SR, —S(O)R, —S(O)$_2$R, —NR$_2$, or an optionally substituted C$_{1-4}$ aliphatic;

each $R^2$ is independently hydrogen, —R$^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

Ring A is a bi- or tricyclic ring selected from
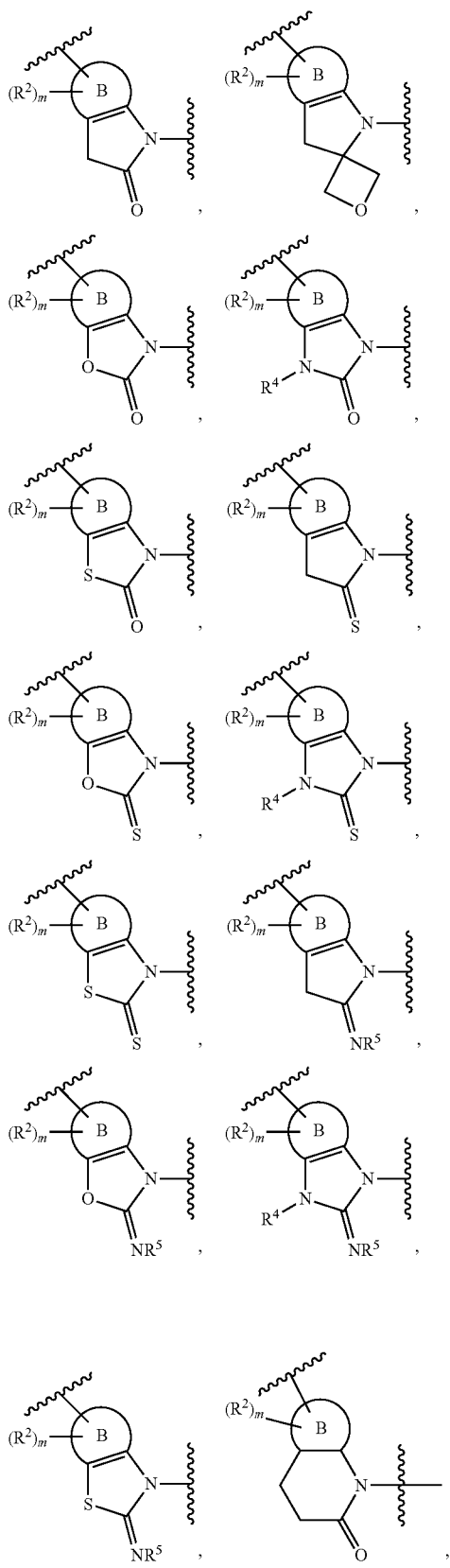
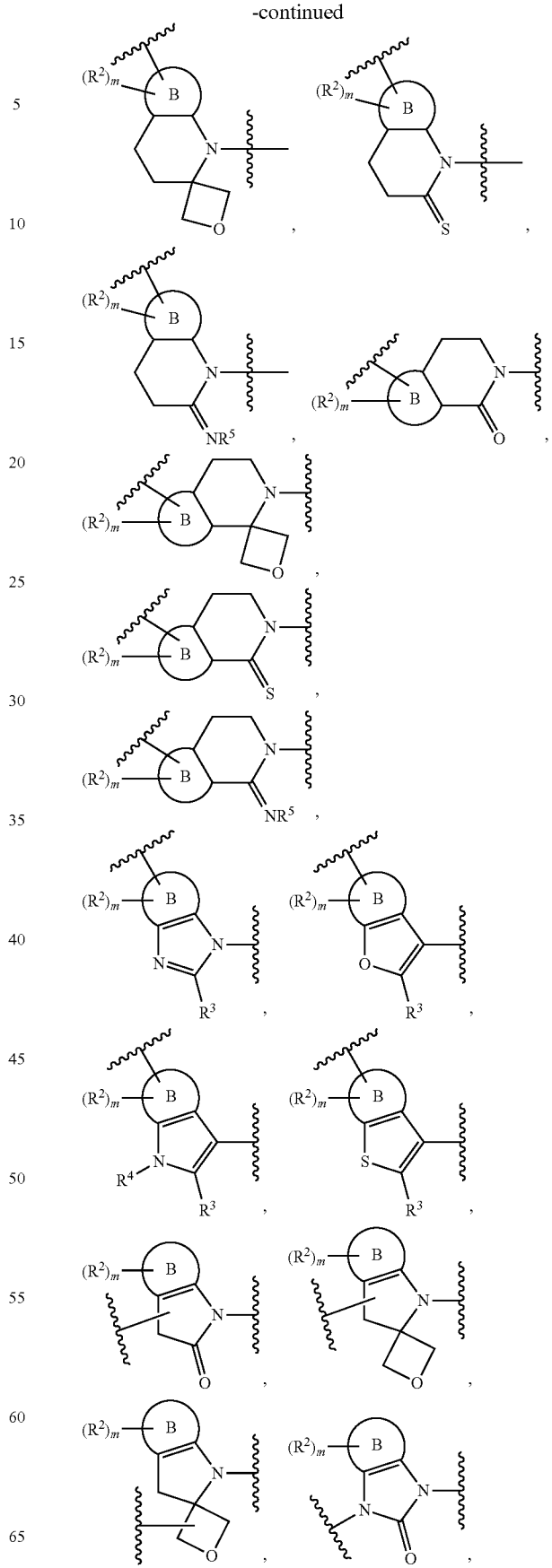

-continued
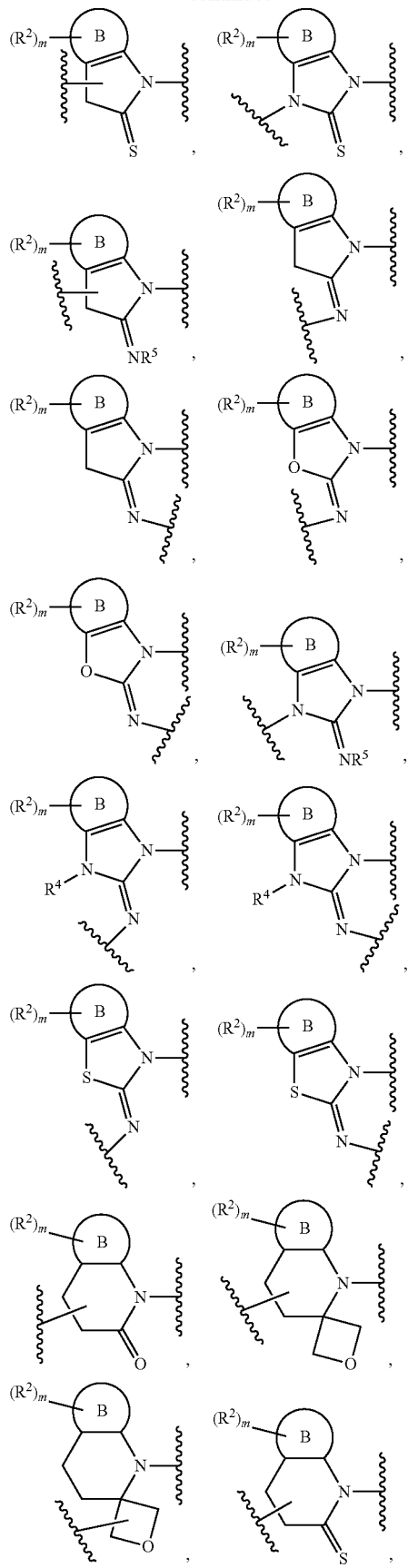
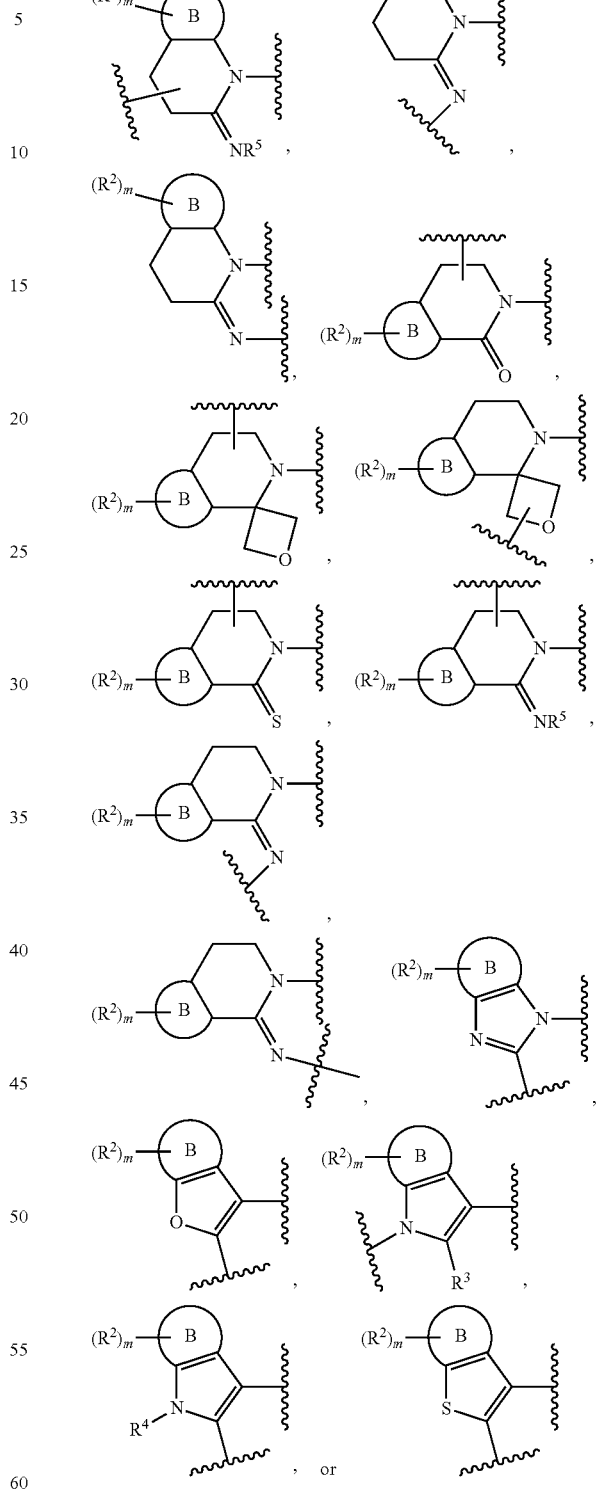
wherein
Ring B is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur;

$R^3$ is selected from hydrogen, halogen, —OR, —N(R)$_2$, or —SR;

each $R^4$ is independently hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$L^1$ is a covalent bond or a bivalent, saturated or unsaturated, straight or branched $C_{1-50}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

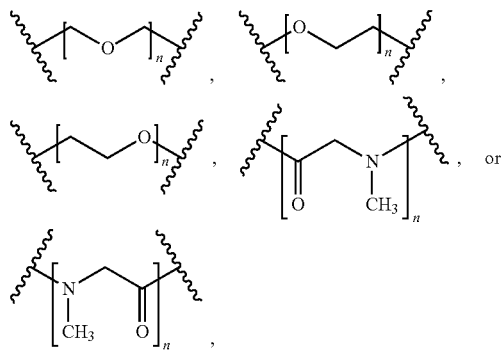

wherein:
each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

m is 0, 1, 2, 3 or 4;
each of n is independently 1, 2, 3, 4, 5, 6, 7, 8, 9, or 10; and
each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

Where a point of attachment of —(R$^2$)$_n$ is depicted on Ring B, it is intended, and one of ordinary skill in the art would appreciate, that the point of attachment of —(R$^2$)$_n$ may be on Ring A and may also be at any available carbon or nitrogen atom on Ring A including the ring to which Ring B is fused. Where —R$^2$ is attached to a nitrogen atom bound to R$^4$ or R$^5$, R$^4$ or R$^5$ is absent and —R$^2$ takes the place of the R$^4$ or R$^5$ group. Where —R$^2$ is attached to a carbon atom bound to R$^3$, R$^3$ is absent and —R$^2$ takes the place of the R$^3$ group.

In certain embodiments, the present invention provides a compound of formula I, wherein LBM is an E3 ubiquitin ligase (cereblon) binding moiety

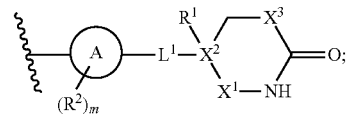

Thereby forming a compound of formula I-1':

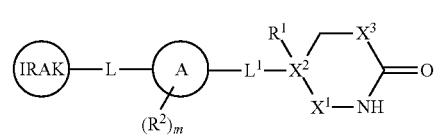

or a pharmaceutically acceptable salt thereof, wherein L and IRAK are as defined above and described herein, and wherein:

$X^1$ is a bivalent moiety selected from a covalent bond, —CH$_2$—, —C(O)—, —C(S)—, or

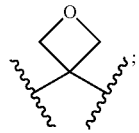 [SMILES: *C1(*)COC1]

$X^2$ is a carbon atom or silicon atom;
$X^3$ is a bivalent moiety selected from —CH$_2$— or —Si(R$_2$)—;
$R^1$ is hydrogen, deuterium, halogen, —CN, —OR, —SR, —S(O)R, —S(O)$_2$R, —N(R)$_2$, —Si(R)$_3$, or an optionally substituted $C_{1-4}$ aliphatic;
each $R^2$ is independently hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

Ring A is a bi- or tricyclic ring selected from
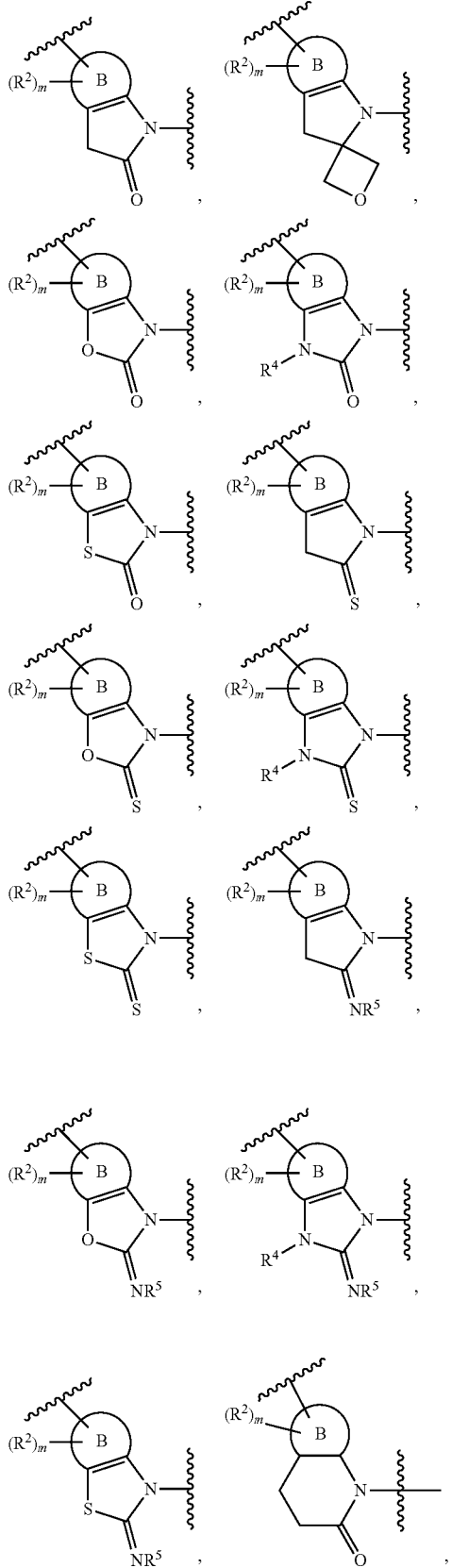
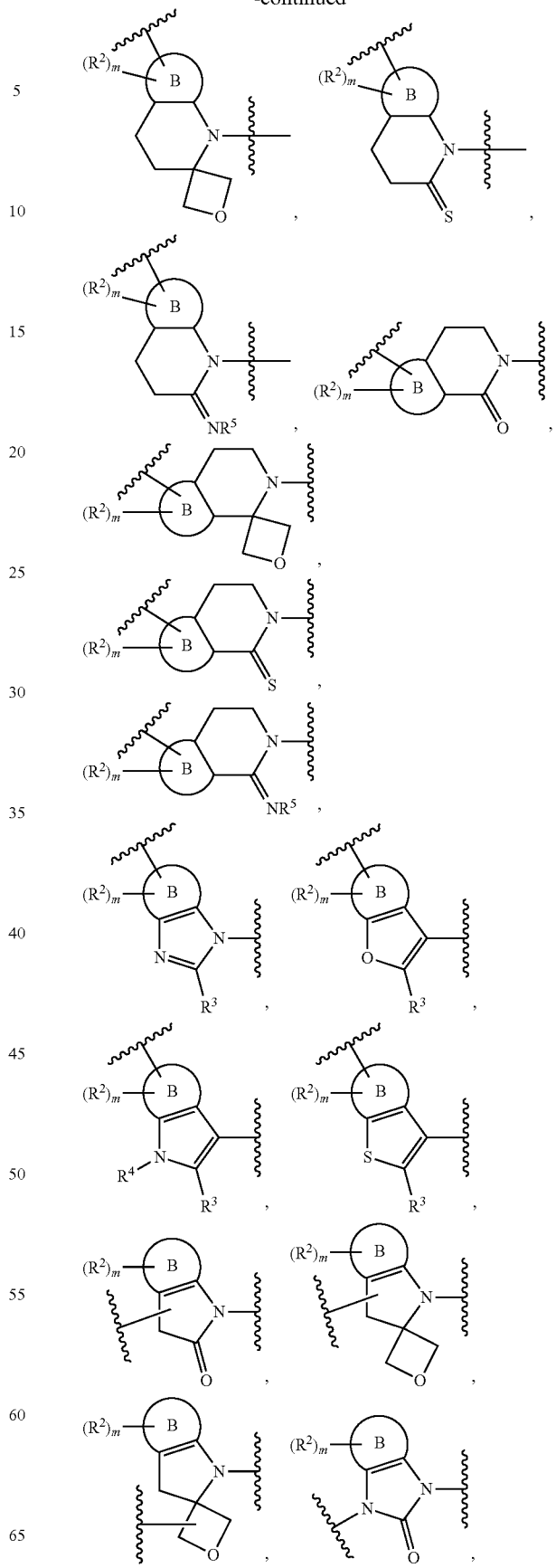

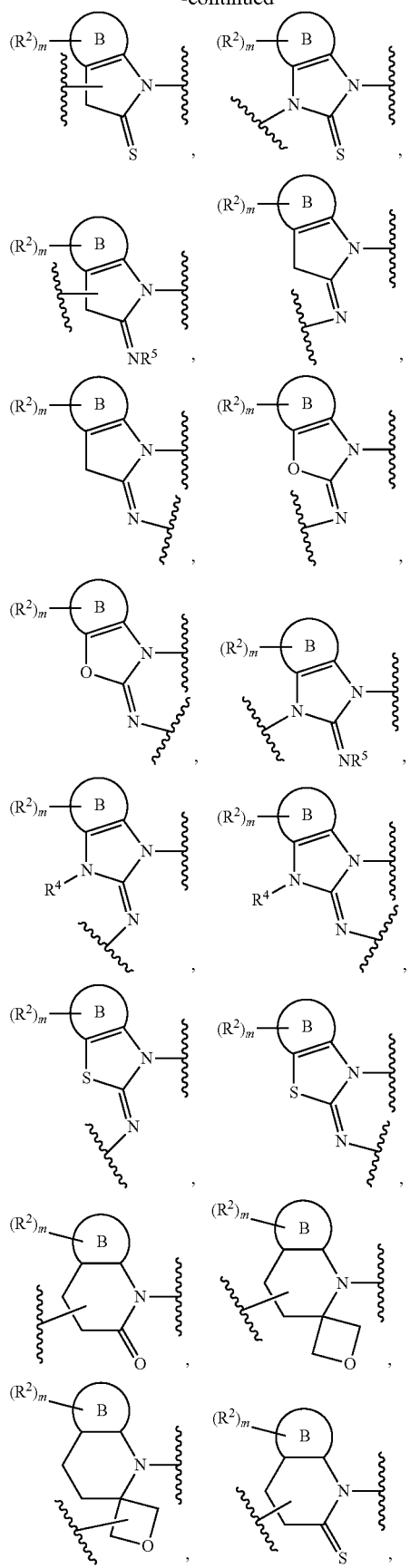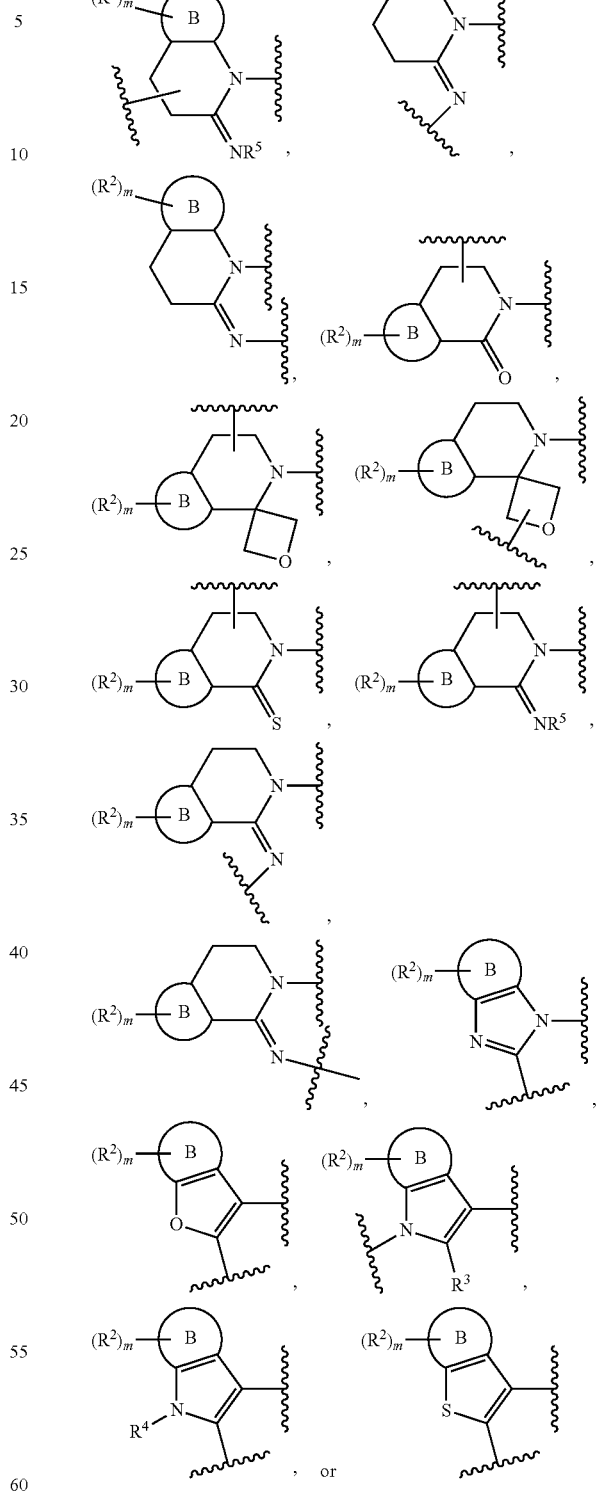
wherein
Ring B is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur;

$R^3$ is selected from hydrogen, halogen, —OR, —N(R)$_2$, or —SR;

each $R^4$ is independently hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$L^1$ is a covalent bond or a bivalent, saturated or unsaturated, straight or branched $C_{1-50}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

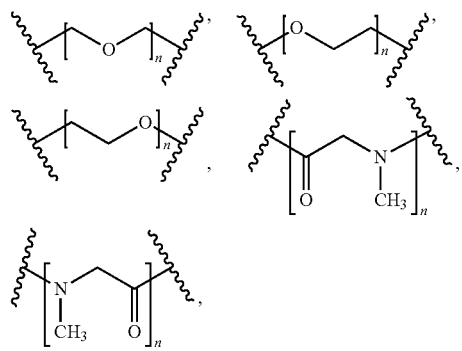

wherein:

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

m is 0, 1, 2, 3 or 4;

each of n is independently 1, 2, 3, 4, 5, 6, 7, 8, 9, or 10; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

Where a point of attachment of —(R$^2$)$_n$ is depicted on Ring B, it is intended, and one of ordinary skill in the art would appreciate, that the point of attachment of —(R$^2$)$_n$ may be on Ring A and may also be at any available carbon or nitrogen atom on Ring A including the ring to which Ring B is fused. Where —R$^2$ is attached to a nitrogen atom bound to R$^4$ or R$^5$, R$^4$ or R$^5$ is absent and —R$^2$ takes the place of the R$^4$ or R$^5$ group. Where —R$^2$ is attached to a carbon atom bound to R$^3$, R$^3$ is absent and —R$^2$ takes the place of the R$^3$ group.

In some embodiments, a compound of formula I-l' above is provided as a compound of formula I-l" or formula I-l'":

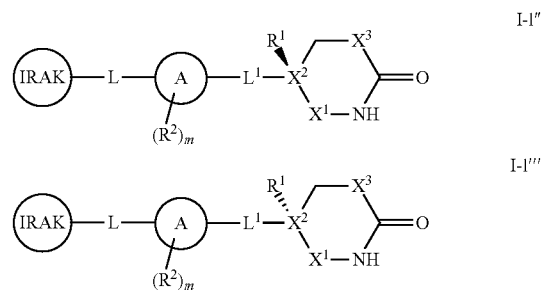

or a pharmaceutically acceptable salt thereof, wherein:
each of IRAK, Ring A, L, L$^1$, R$^1$, R$^2$, X$^1$, and m is as defined above.

In certain embodiments, the present invention provides a compound of formula I, wherein LBM is an E3 ubiquitin ligase (cereblon) binding moiety

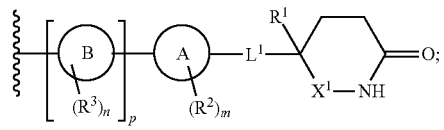

Thereby forming a compound of formula I-m:

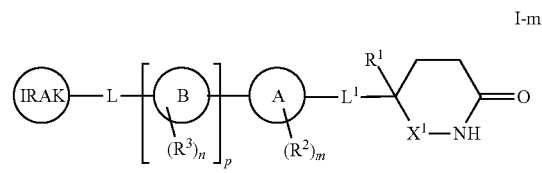

I-m or a pharmaceutically acceptable salt thereof, wherein, L and IRAK are as defined above and described in embodiments herein, and wherein:

$X^1$ is a bivalent moiety selected from a covalent bond, —CH$_2$—, —C(O)—, —C(S)—, or
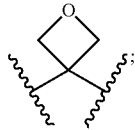 [SMILES: *C1(*)COC1];
$R^1$ is hydrogen, deuterium, halogen, —CN, —OR, —SR, —S(O)R, —S(O)$_2$R, —NR$_2$, or an optionally substituted C$_{1-4}$ aliphatic;
Ring A is a mono- or bicyclic ring selected from
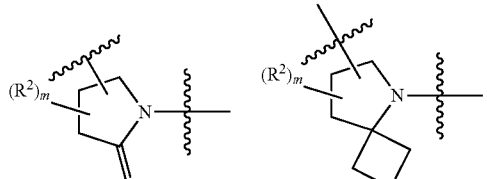
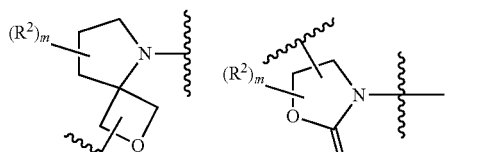
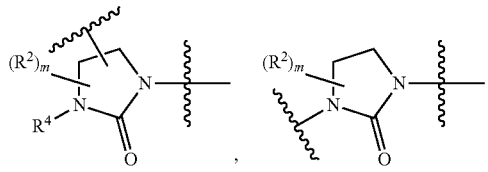
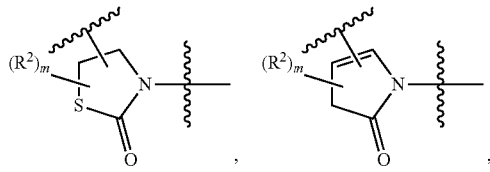
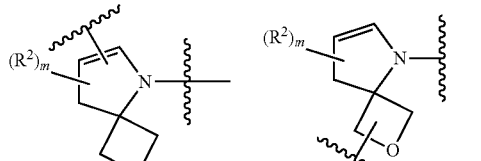
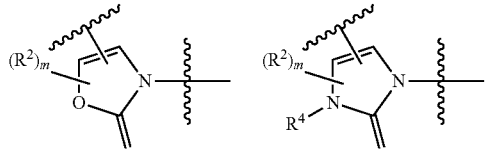
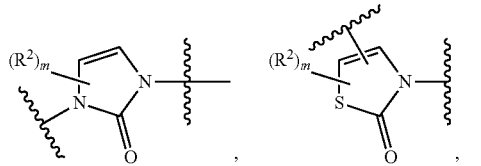
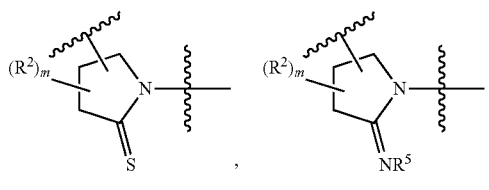
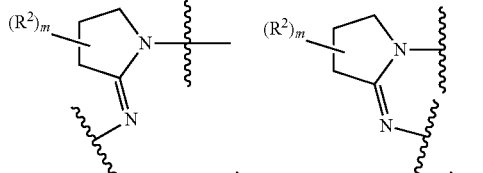
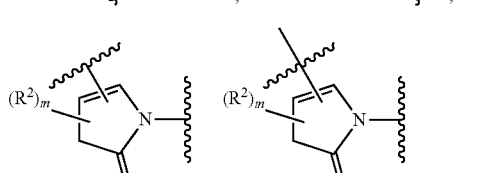
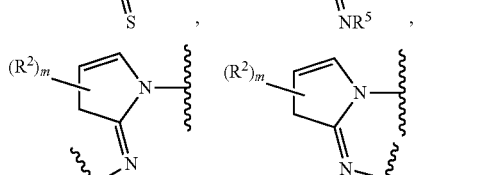
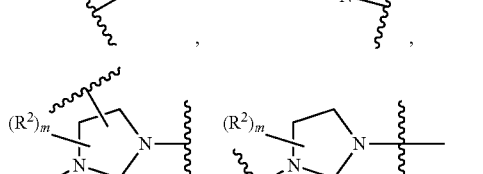
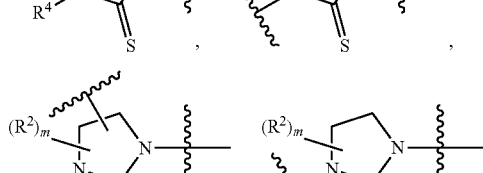
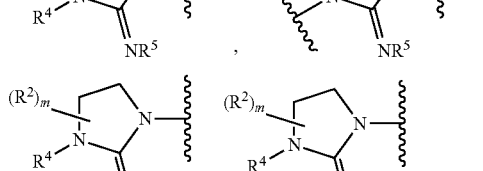
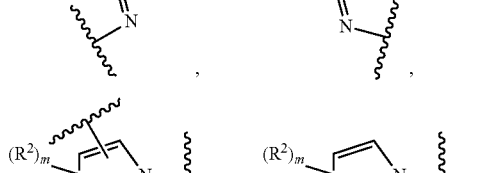
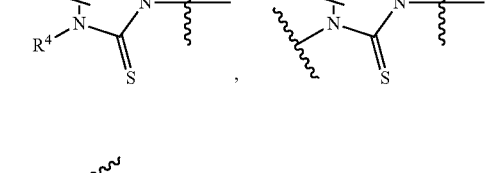
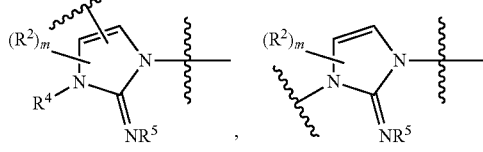

-continued

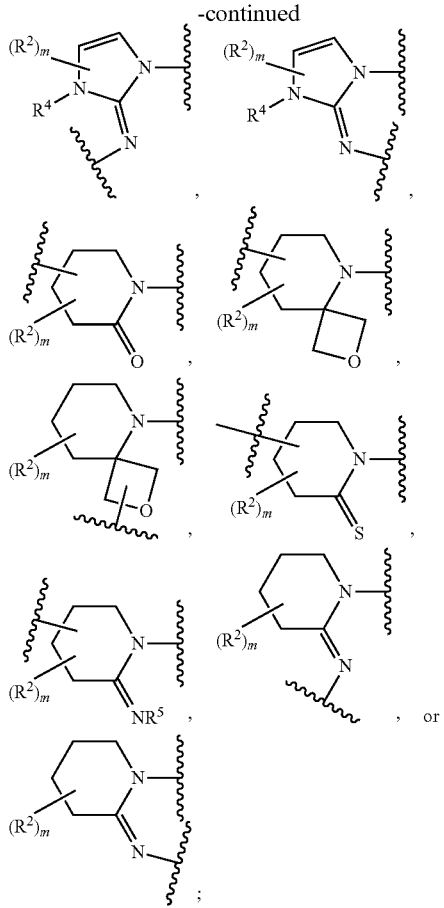

,

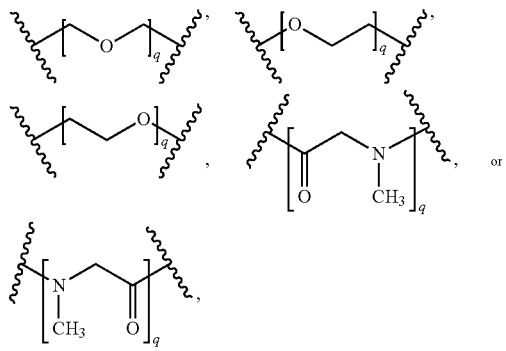

each R² is independently hydrogen, —R⁶, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

Ring B is selected from a 6-membered aryl containing 0-2 nitrogen atoms or a 5-membered heteroaryl with 1-3 heteroatoms independently selected from nitrogen, oxygen or sulfur;

each of R³ and R⁴ is independently hydrogen, —R⁶, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

R⁵ is hydrogen, C₁₋₄ aliphatic, or —CN;

each R⁶ is independently an optionally substituted group selected from C₁₋₆ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

L¹ is a covalent bond or a bivalent, saturated or unsaturated, straight or branched C₁₋₅₀ hydrocarbon chain, wherein 0-6 methylene units of L are independently replaced by -Cy-, —O—, —NR—, —S—, —OC(O)—, —C(O)O—, —C(O)—, —S(O)—, —S(O)₂—, —NRS(O)₂—, —S(O)₂ NR—, —NRC(O)—, —C(O)NR—, —OC(O) NR—, —NRC(O)O—, wherein:

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

m is 0, 1, or 2;

n is 0, 1, 2, 3, or 4;

p is 0 or 1, wherein when p is 0, the bond connecting Ring A and Ring B is connected to

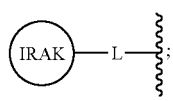

each of q is independently 1, 2, 3, 4, 5, 6, 7, 8, 9, or 10; and each R is independently hydrogen, or an optionally substituted group selected from C₁₋₆ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In certain embodiments, the present invention provides a compound of formula I, wherein LBM is an E3 ubiquitin ligase (cereblon) binding moiety

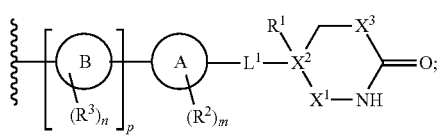

Thereby forming a compound of formula I-m':

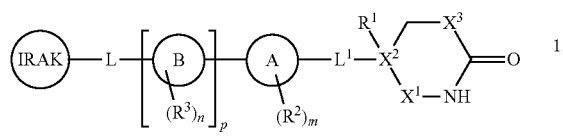

I-m' or a pharmaceutically acceptable salt thereof, wherein, L and IRAK are as defined above and described in embodiments herein, and wherein:

X¹ is a bivalent moiety selected from a covalent bond, —CH₂—, —C(O)—, —C(S)—, or

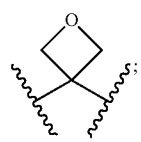 [SMILES: *C1(*)COC1]

X² is a carbon atom or silicon atom;

X³ is a bivalent moiety selected from —CH₂— or —Si(R₂)—;

R¹ is hydrogen, deuterium, halogen, —CN, —OR, —SR, —S(O)R, —S(O)₂R, —N(R)₂, —Si(R)₃, or an optionally substituted C₁₋₄ aliphatic;

Ring A is a mono- or bicyclic ring selected from

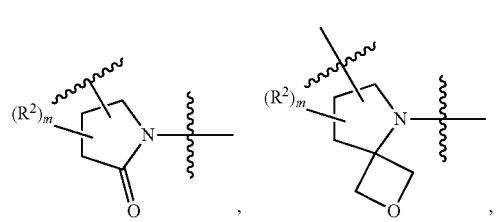

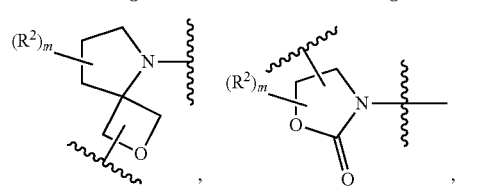

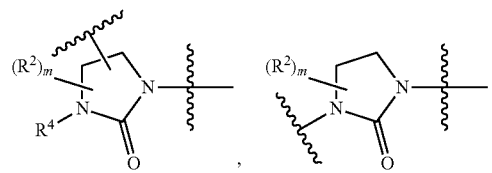

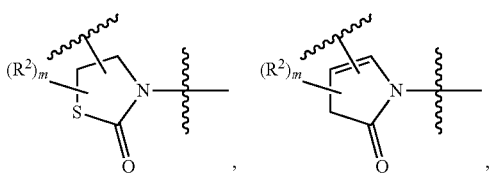

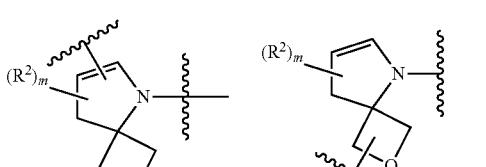

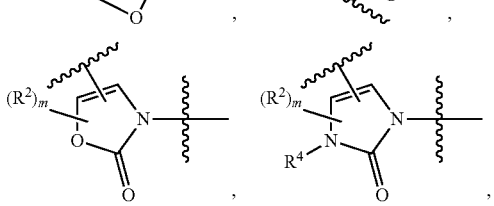

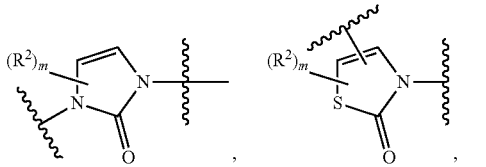

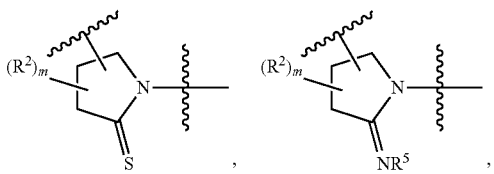

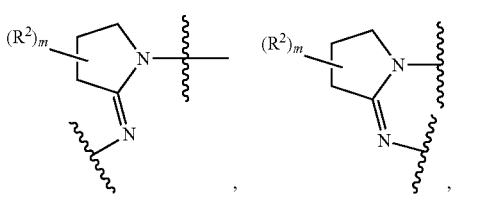

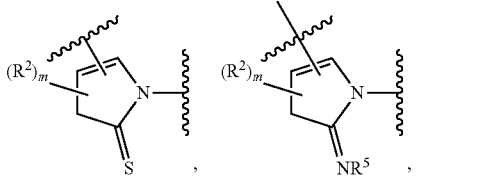

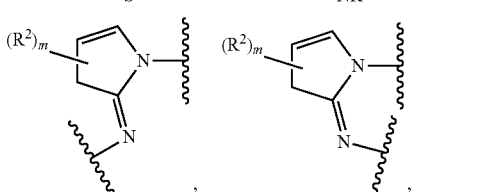

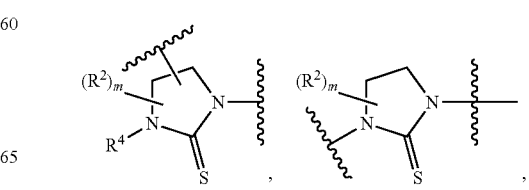

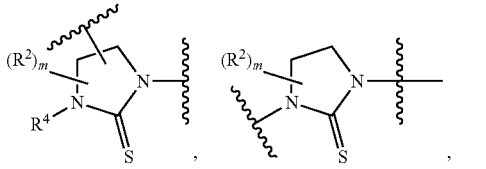

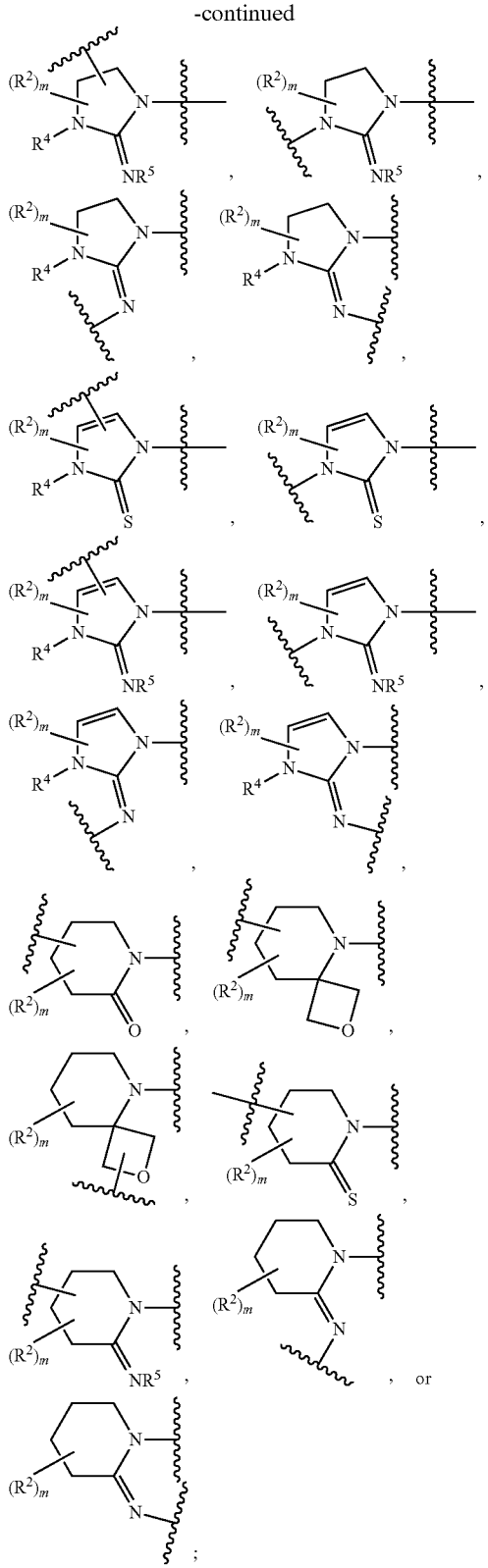

each $R^2$ is independently hydrogen, $-R^6$, halogen, $-CN$, $-NO_2$, $-OR$, $-SR$, $-NR_2$, $-S(O)_2R$, $-S(O)_2NR_2$, $-S(O)R$, $-C(O)R$, $-C(O)OR$, $-C(O)NR_2$, $-C(O)N(R)OR$, $-OC(O)R$, $-OC(O)NR_2$, $-N(R)C(O)OR$, $-N(R)C(O)R$, $-N(R)C(O)NR_2$, or $-N(R)S(O)_2R$;

Ring B is selected from a 6-membered aryl containing 0-2 nitrogen atoms or a 5-membered heteroaryl with 1-3 heteroatoms independently selected from nitrogen, oxygen or sulfur;

each of $R^3$ and $R^4$ is independently hydrogen, $-R^6$, halogen, $-CN$, $-NO_2$, $-OR$, $-SR$, $-NR_2$, $-S(O)_2R$, $-S(O)_2NR_2$, $-S(O)R$, $-C(O)R$, $-C(O)OR$, $-C(O)NR_2$, $-C(O)N(R)OR$, $-OC(O)R$, $-OC(O)NR_2$, $-N(R)C(O)OR$, $-N(R)C(O)R$, $-N(R)C(O)NR_2$, or $-N(R)S(O)_2R$;

$R^5$ is hydrogen, $C_{1-4}$ aliphatic, or $-CN$;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$L^1$ is a covalent bond or a bivalent, saturated or unsaturated, straight or branched $C_{1-50}$ hydrocarbon chain, wherein 0-6 methylene units of L are independently replaced by -Cy-, $-O-$, $-NR-$, $-S-$, $-OC(O)-$, $-C(O)O-$, $-C(O)-$, $-S(O)-$, $-S(O)_2-$, $-NRS(O)_2-$, $-S(O)_2NR-$, $-NRC(O)-$, $-C(O)NR-$, $-OC(O)NR-$, $-NRC(O)O-$,

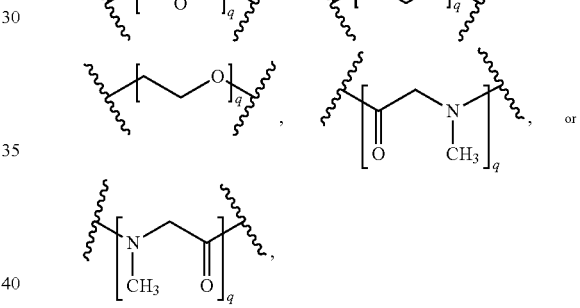

wherein:

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

m is 0, 1, or 2;

n is 0, 1, 2, 3, or 4;

p is 0 or 1 wherein when p is 0, the bond connecting Ring A and Ring B is connected to

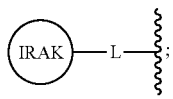

each of q is independently 1, 2, 3, 4, 5, 6, 7, 8, 9, or 10; and
each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-m' above is provided as a compound of formula I-m" or formula I-m'":

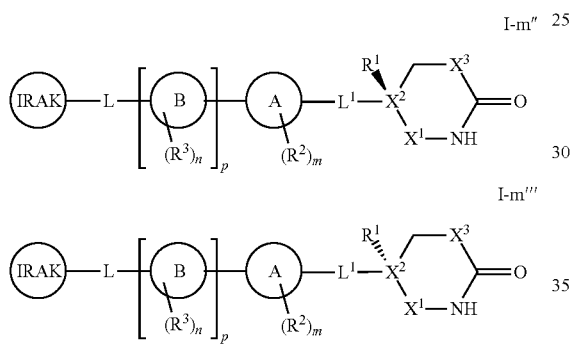

or a pharmaceutically acceptable salt thereof, wherein:
each of IRAK, Ring A, Ring B, L, $L^1$, $R^1$, $R^2$, $R^3$, $X^1$, p, and m is as defined above.

In certain embodiments, the present invention provides a compound of formula I, wherein LBM is an E3 ubiquitin ligase (cereblon) binding moiety

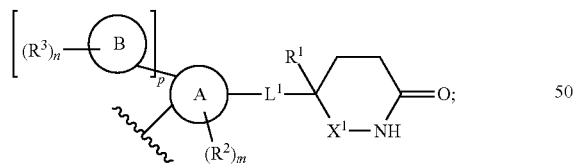

Thereby forming a compound of formula I-n:

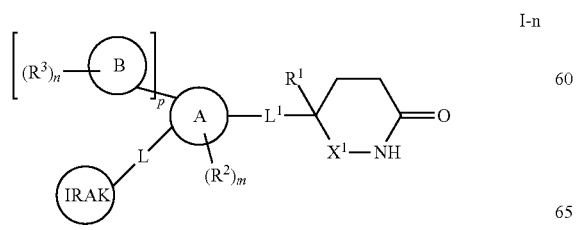

or a pharmaceutically acceptable salt thereof, wherein L and IRAK are as defined above and described in embodiments herein, and wherein:

$X^1$ is a bivalent moiety selected from a covalent bond, —$CH_2$—, —C(O)—, —C(S)—, or

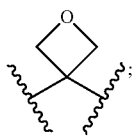 [SMILES: *C1(*)COC1]

$R^1$ is hydrogen, deuterium, halogen, —CN, —OR, —SR, —S(O)R, —S(O)$_2$R, —$NR_2$, or an optionally substituted $C_{1-4}$ aliphatic;

Ring A is a mono- or bicyclic ring selected from

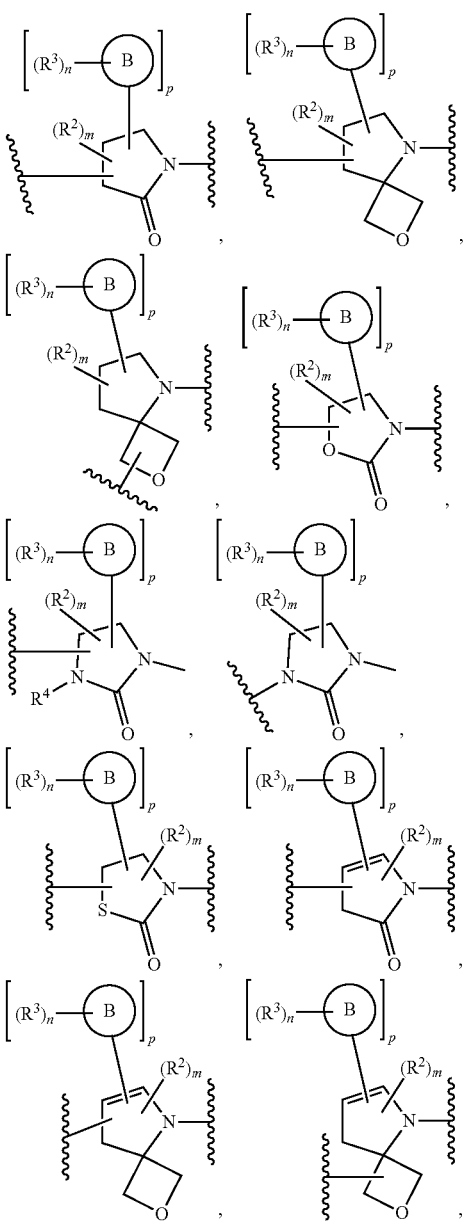

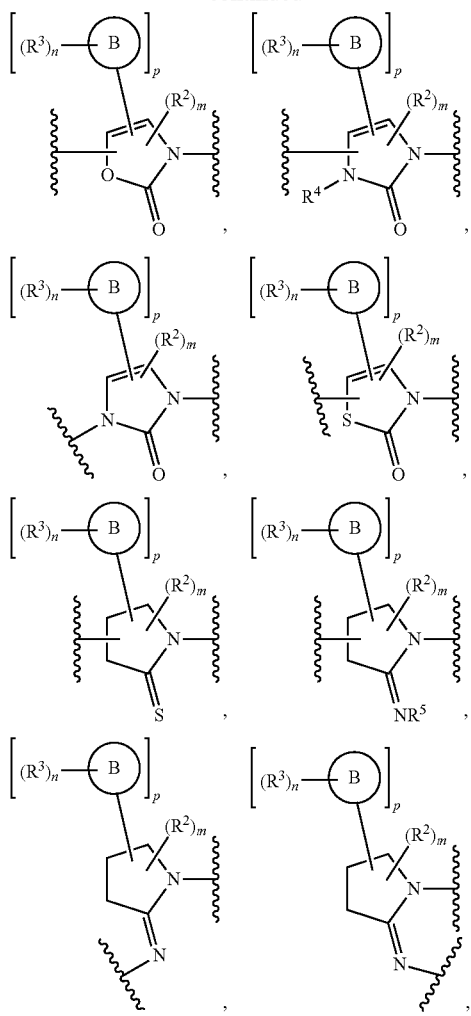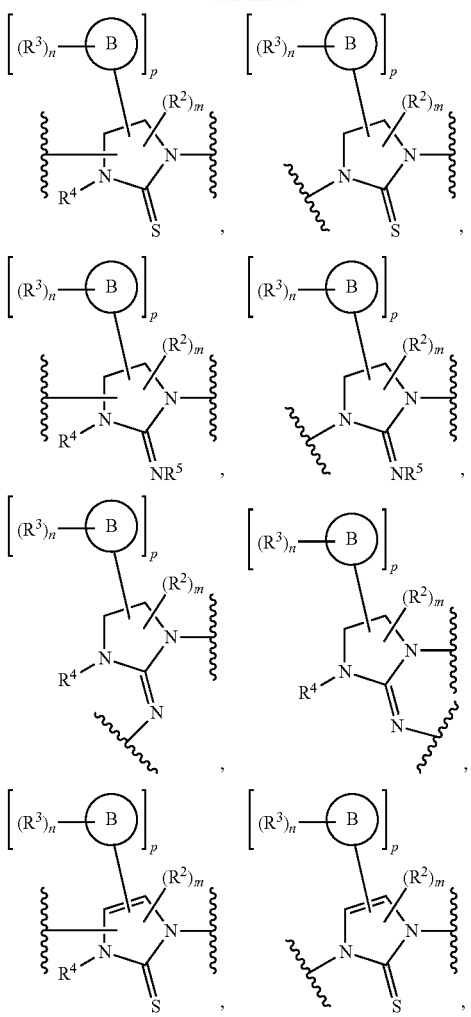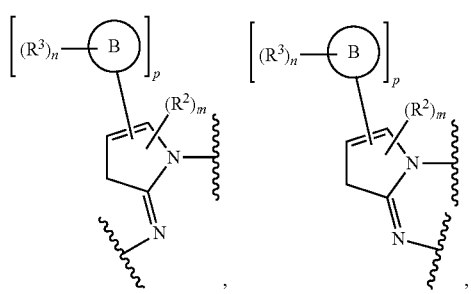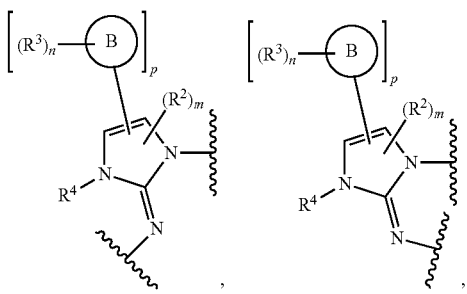

-continued

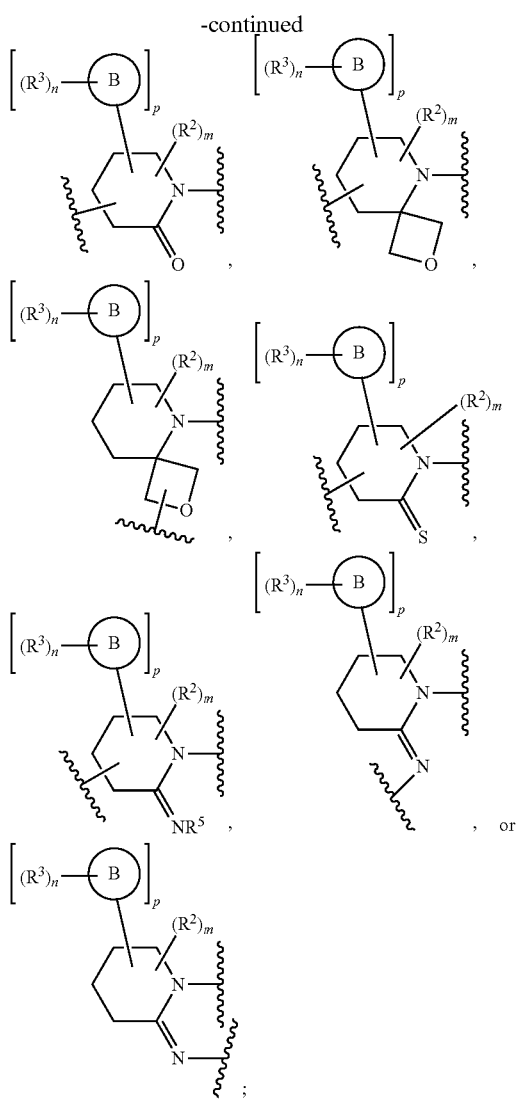

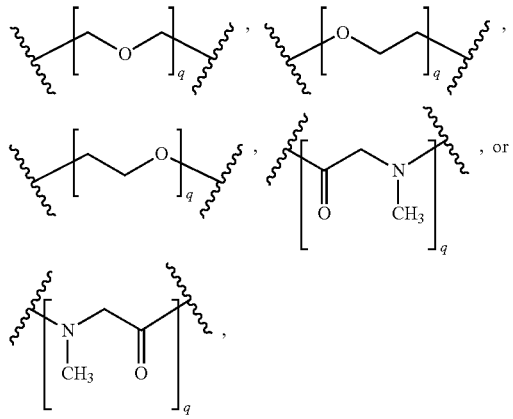

methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$ NR—, —NRC(O)—, —C(O)NR—, —OC(O)NR—, —NRC(O)O—, wherein:
each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;
m is 0, 1, or 2;
n is 0, 1, 2, 3, or 4;
p is 0 or 1;
each of q is independently 1, 2, 3, 4, 5, 6, 7, 8, 9, or 10; and
each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In certain embodiments, the present invention provides a compound of formula I, wherein LBM is an E3 ubiquitin ligase (cereblon) binding moiety each $R^2$ is independently hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;
Ring B is selected from a 6-membered aryl containing 0-2 nitrogen atoms or a 5-membered heteroaryl with 1-3 heteroatoms independently selected from nitrogen, oxygen or sulfur;
each of $R^3$ and $R^4$ is independently hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;
$R^5$ is hydrogen, $C_{1-4}$ aliphatic, or —CN;
each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
$L^1$ is a covalent bond or a bivalent, saturated or unsaturated, straight or branched $C_{1-50}$ hydrocarbon chain, wherein 0-6

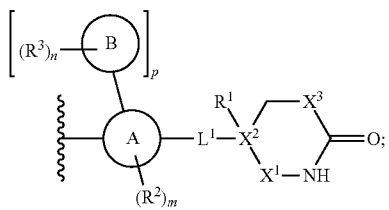

Thereby forming a compound of formula I-n':

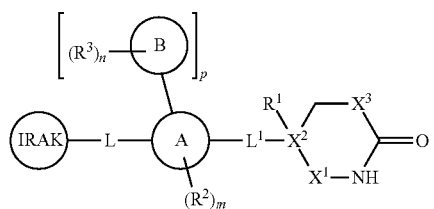
I-n' or a pharmaceutically acceptable salt thereof, wherein L and IRAK are as defined above and described in embodiments herein, and wherein:

$X^1$ is a bivalent moiety selected from a covalent bond, —CH$_2$—, —C(O)—, —C(S)—, or

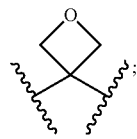;

$X^2$ is a carbon atom or silicon atom;
$X^3$ is a bivalent moiety selected from —CH$_2$— or —Si(R$_2$)—;
$R^1$ is hydrogen, deuterium, halogen, —CN, —OR, —SR, —S(O)R, —S(O)$_2$R, —N(R)$_2$, —Si(R)$_3$, or an optionally substituted C$_{L-4}$ aliphatic;
Ring A is a mono- or bicyclic ring selected from

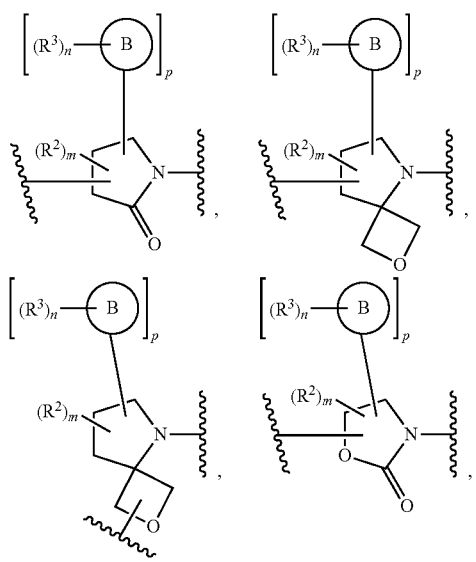

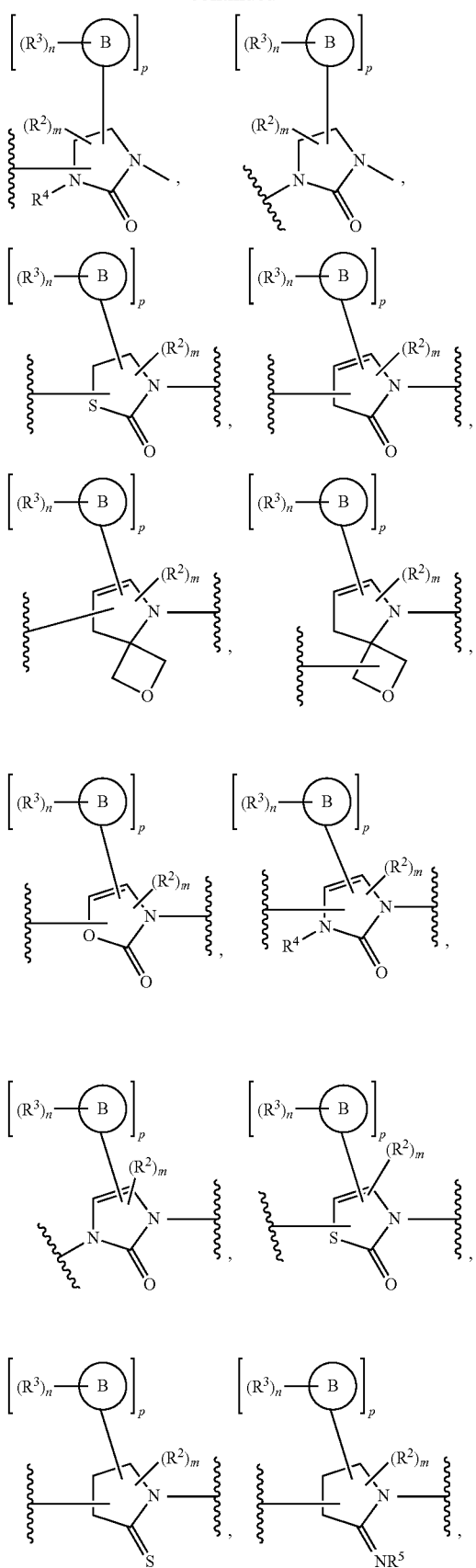

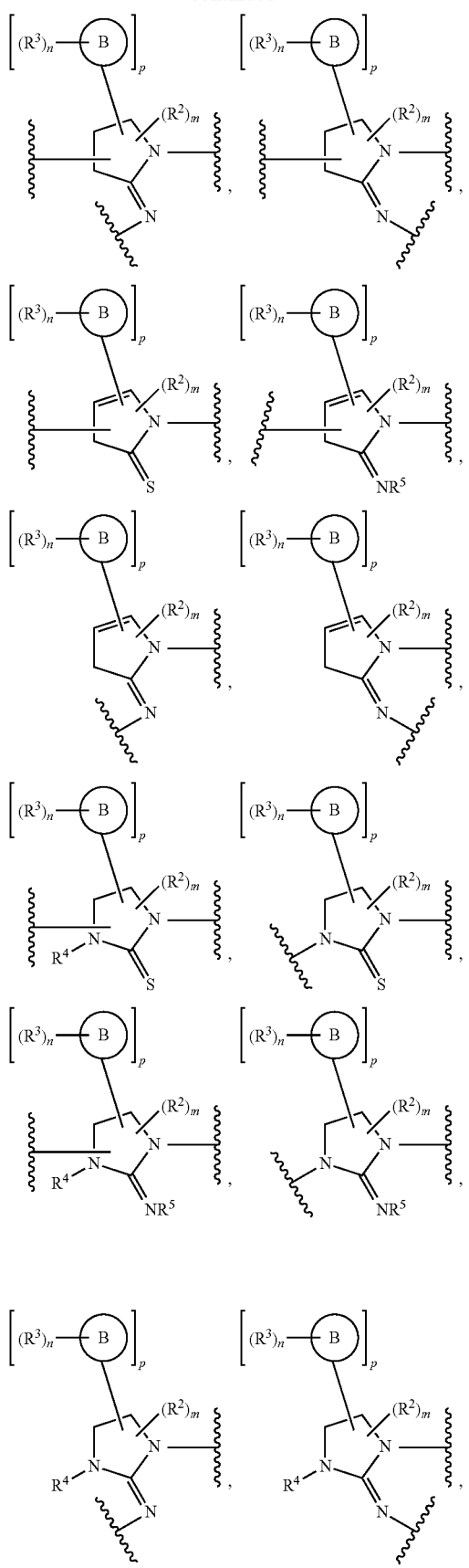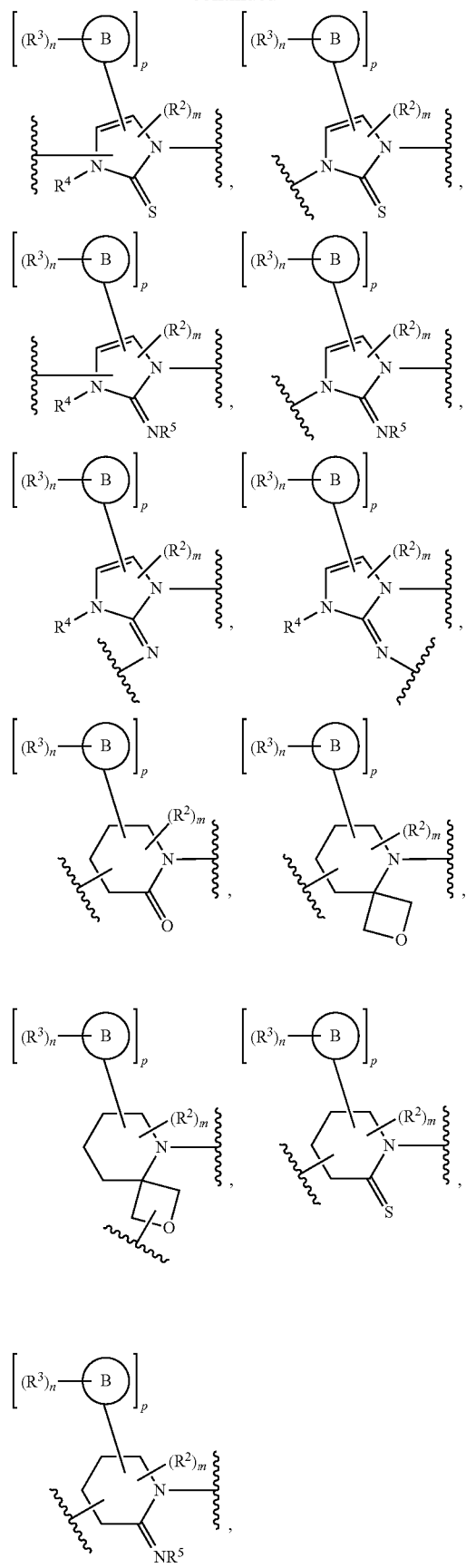

-continued

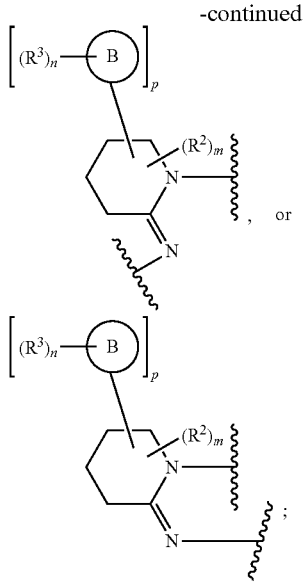, or each R² is independently hydrogen, —R⁶, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

Ring B is selected from a 6-membered aryl containing 0-2 nitrogen atoms or a 5-membered heteroaryl with 1-3 heteroatoms independently selected from nitrogen, oxygen or sulfur;

each of R³ and R⁴ is independently hydrogen, —R⁶, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

R⁵ is hydrogen, $C_{1-4}$ aliphatic, or —CN;

each R⁶ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

L¹ is a covalent bond or a bivalent, saturated or unsaturated, straight or branched $C_{1-50}$ hydrocarbon chain, wherein 0-6 methylene units of L are independently replaced by -Cy-, —O—, —NR—, —S—, —OC(O)—, —C(O)O—, —C(O)—, —S(O)—, —S(O)₂—, —NRS(O)₂—, —S(O)₂NR—, —NRC(O)—, —C(O)NR—, —OC(O)NR—, —NRC(O)O—,

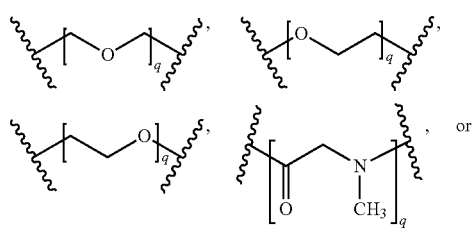

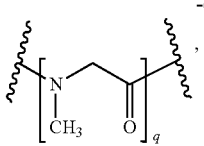, wherein:
each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

m is 0, 1, or 2;
n is 0, 1, 2, 3, or 4;
p is 0 or 1;
each of q is independently 1, 2, 3, 4, 5, 6, 7, 8, 9, or 10; and
each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-n' above is provided as a compound of formula I-n" or formula I-n'":

I-n"

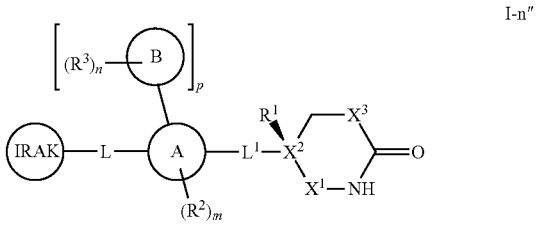

I-n'"

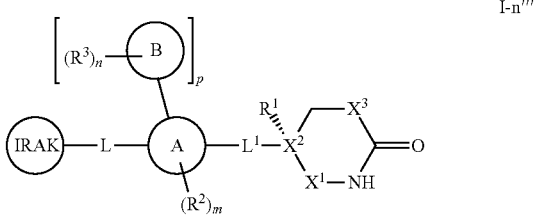

or a pharmaceutically acceptable salt thereof, wherein:
each of IRAK, Ring A, Ring B, L, L¹, R¹, R², R³, X¹, p, and m is as defined above.

In certain embodiments, the present invention provides a compound of formula I, wherein LBM is an E3 ubiquitin ligase (cereblon) binding moiety

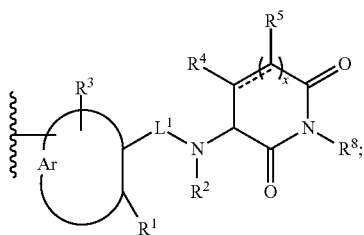

thereby forming a compound of formula I-o:

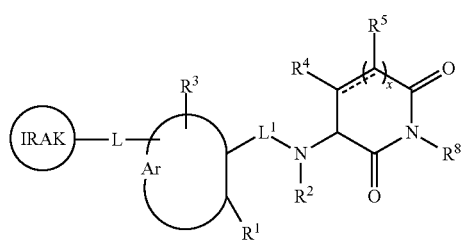

I-o or a pharmaceutically acceptable salt thereof, wherein L and IRAK are as defined above and described in embodiments herein, and wherein:

Ar is aryl, heteroaryl, cycloalkyl, or heterocyclyl;

L¹ is absent or a linker selected from the group consisting of —SO₂, —SO₂R'; SO₂R'R", —SO₂NR'R"; —SO₂NR'R"C(=O); —NR'SO₂R"; —R'SO₂NR'R'"; —C(=O); —C(=O)R'; —OC(=O)R'; —C(=O)NR'R"; —NR'C(=O)R"; —NR'C(=O)R"C(=O); —OR'; —NR'R"; —SR'; —N₃—C(=O)OR'; —O(CR'R")ᵣC(=O)R'; —O(CR'R")ᵣNR"C(=O)R'; —O(CR'R")ᵣNR"SO₂R'; —OC(=O)NR'R"; —NR'C(=O)OR"; and substituted or unsubstituted C₁-C₆ aliphatic alkyl;

wherein R', R", and R'" are individually selected from hydrogen; substituted or unsubstituted alkyl; substituted or unsubstituted alkenyl; substituted or unsubstituted ether; substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine; and r is an integer from 1 to 6;

R¹, R², and R³ are individually selected from the group consisting of hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, and combinations thereof; or wherein R¹ and R² combine to form a 5-7 membered heterocyclic ring; and wherein when R¹ and R² combine to form a 5-7 membered heterocyclic ring, Ar is optionally not fused to the 5-7 membered heterocyclic ring but is a substituent of the 5-7 membered heterocyclic ring;

R⁴ and R⁵ are individually selected from the group consisting of hydrogen, halogen, hydroxyl, azide, ether, alkoxyl, sulfhydryl, alkylthio, sulfonyl, sulfonamido, ketone, aldehyde, ester, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, and combinations thereof;

R⁸ is selected from the group consisting of hydrogen, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, substituted or unsubstituted aryl, substituted or unsubstituted alkylaryl, and combinations thereof; and x is 0, 1, or 2;

as described and defined in WO 2017/161119, the entirety of which is herein incorporated by reference.

In certain embodiments, the present invention provides a compound of formula I, wherein LBM is an E3 ubiquitin ligase (cereblon) binding moiety

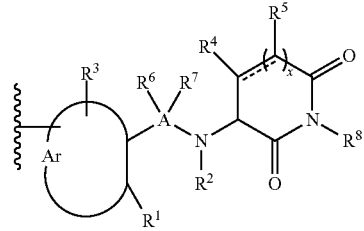

thereby forming a compound of formula I-p:

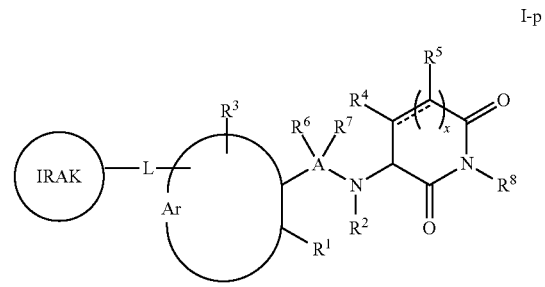

I-p or a pharmaceutically acceptable salt thereof, wherein L and IRAK are as defined above and described in embodiments herein, and further wherein:

A is C, S; substituted of unsubstituted C₁-C₈ alkyl, or combinations thereof;

R⁶ and R⁷ are individually =O, hydrogen, C₁-C₈ alkyl, or R⁶ and R⁷ combine to form =O; and each of the variables Ar, $R^1$, $R^2$, $R^3$, $R^4$, $R^5$, $R^8$, x, and the bond --- is as described above and as described and defined in WO 2017/161119, the entirety of each of which is herein incorporated by reference.

In certain embodiments, the present invention provides a compound of formula I, wherein LBM is an E3 ubiquitin ligase (cereblon) binding moiety

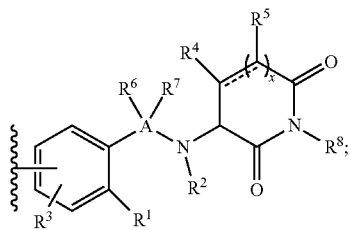

thereby forming a compound of formula I-q:

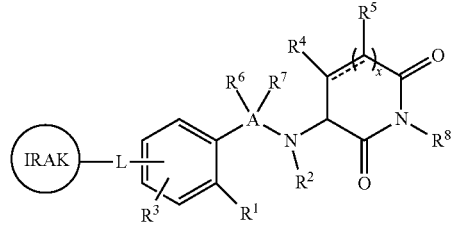

I-q or a pharmaceutically acceptable salt thereof, wherein L and IRAK are as defined above and described in embodiments herein, and wherein each of the variables $R^1$, $R^2$, $R^3$, $R^4$, $R^5$, $R^6$, $R^7$, $R^8$, A, x, and the bond --- is as described above described and defined in WO 2017/161119, the entirety of each of which is herein incorporated by reference.

In certain embodiments, the present invention provides a compound of formula I, wherein LBM is an E3 ubiquitin ligase (cereblon) binding moiety

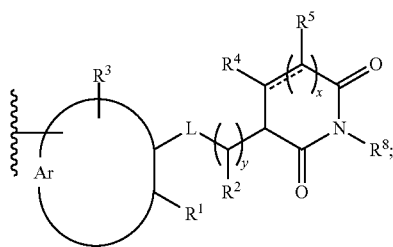

thereby forming a compound of formula I-r:

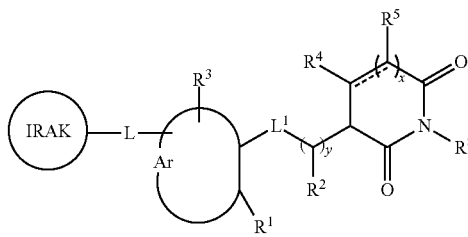

I-r or a pharmaceutically acceptable salt thereof, wherein L and IRAK are as defined above and described in embodiments herein, and wherein each of the variables Ar, $R^1$, $R^2$, $R^3$, $R^4$, $R^5$, $R^8$, L, x, y, and the bond --- is as described above and described and defined in WO 2017/161119, the entirety of each of which is herein incorporated by reference.

In certain embodiments, the present invention provides a compound of formula I, wherein LBM is an E3 ubiquitin ligase (cereblon) binding moiety

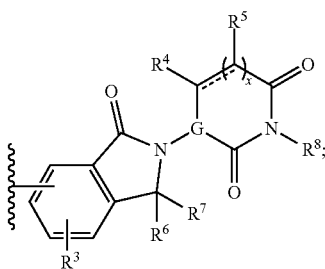

thereby forming a compound of formula I-s:

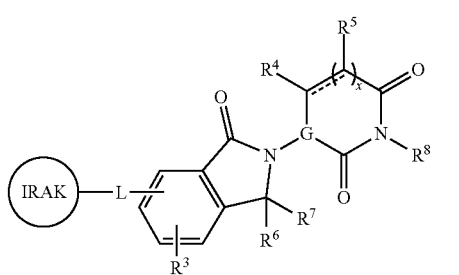

I-s or a pharmaceutically acceptable salt thereof, wherein L and IRAK are as defined above and described in embodiments herein, and wherein:
G comprises C, S, N, substituted of unsubstituted C1-C8 alkyl, or combinations thereof, $R^3$ is selected from the group consisting of hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, and combinations thereof; and each of the variables $R^3$, $R^4$, $R^5$, $R^6$, $R^7$, $R^8$, x, and the bond --- is as described above and described and defined in WO 2017/161119, the entirety of each of which is herein incorporated by reference.

In certain embodiments, the present invention provides a compound of formula I, wherein LBM is an E3 ubiquitin ligase (cereblon) binding moiety

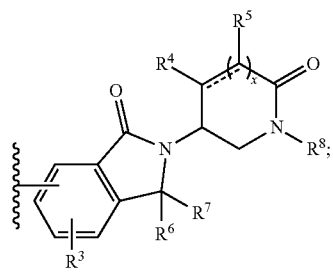

thereby forming a compound of formula I-t:

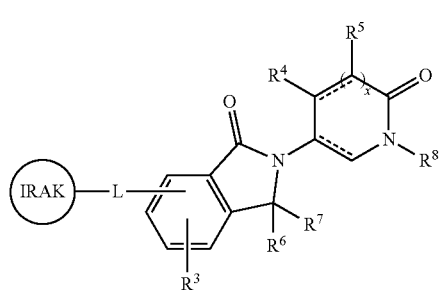

I-t or a pharmaceutically acceptable salt thereof, wherein L and IRAK are as defined above and described in embodiments herein, and wherein each of the variables $R^3$, $R^4$, $R^5$, $R^6$, $R^7$, $R^8$, x, and the bond --- is as described above for I-o and described and defined in WO 2017/161119, the entirety of each of which is herein incorporated by reference.

In certain embodiments, the present invention provides a compound of formula I, wherein LBM is an E3 ubiquitin ligase (cereblon) binding moiety

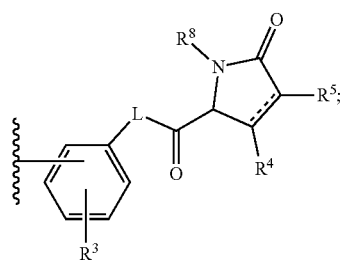

thereby forming a compound of formula I-u:

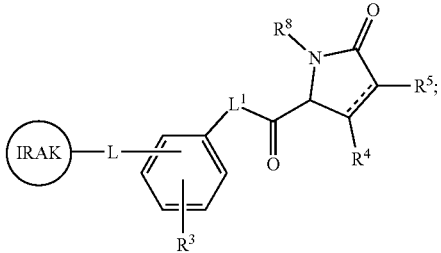

I-u or a pharmaceutically acceptable salt thereof, wherein L and IRAK are as defined above and described in embodiments herein, and wherein each of the variables $R^3$, $R^4$, $R^5$, $R^8$, L, and the bond --- is as described above for I-o and described and defined in WO 2017/161119, the entirety of each of which is herein incorporated by reference.

In certain embodiments, the present invention provides a compound of formula I, wherein LBM is an E3 ubiquitin ligase (cereblon) binding moiety

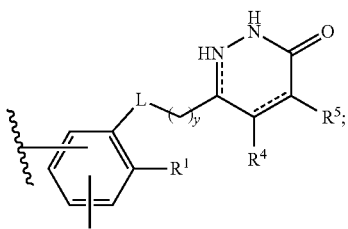

thereby forming a compound of formula I-v:

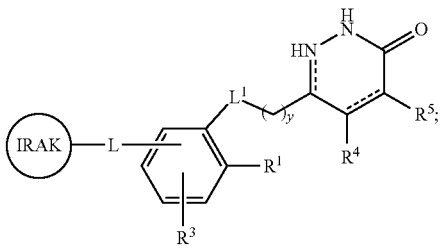

I-v or a pharmaceutically acceptable salt thereof, wherein L and IRAK are as defined above and described in embodiments herein, and wherein each of the variables $R^1$, $R^3$, $R^4$, $R^5$, L, y, and the bond --- is as described above for I-o and described and defined in WO 2017/161119, the entirety of each of which is herein incorporated by reference.

In certain embodiments, the present invention provides a compound of formula I, wherein LBM is an E3 ubiquitin ligase (cereblon) binding moiety

111

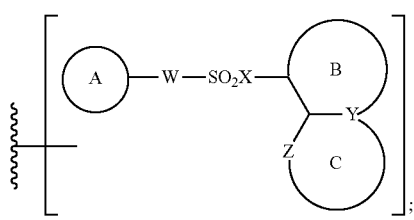

thereby forming a compound of formula I-x:

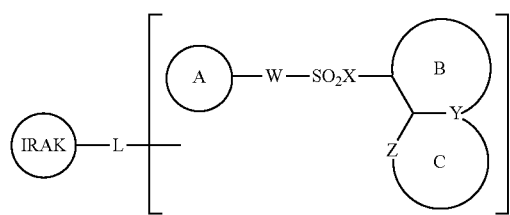

I-x or a pharmaceutically acceptable salt thereof, wherein L and IRAK are as defined above and described in embodiments herein, and wherein each of the variables A, B, C, W, X, Y, and Z is as described and defined in U.S. Pat. No. 5,721,246, the entirety of each of which is herein incorporated by reference.

In certain embodiments, the present invention provides a compound of Formula I, wherein LBM is an E3 ubiquitin ligase (cereblon) binding moiety

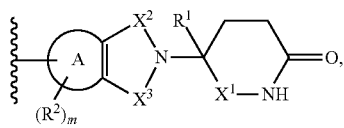

a DCAF15 E3 ubiquitin ligase binding moiety

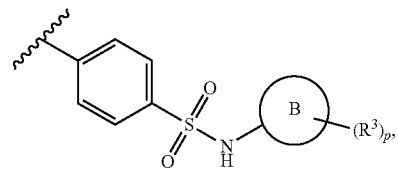

or a VHL E3 ubiquitin ligase binding moiety

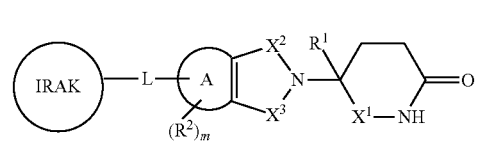

thereby forming a compound of formula I-y-1, I-y-2, or I-y-3:

I-y-1

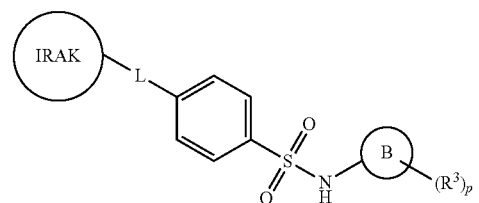

I-y-2

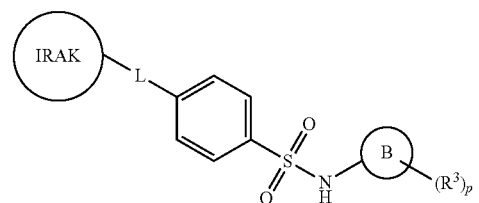

I-y-3 or a pharmaceutically acceptable salt thereof, wherein IRAK is as defined above and described in embodiments herein, and wherein:

each of $X^1$, $X^2$, and $X^3$ is independently a bivalent moiety selected from a covalent bond, —$CH_2$—, —C(O)—, —C(S)—, or

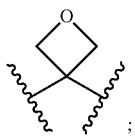 [SMILES: *C1(*)COC1]

each of $X^4$ and $X^5$ is independently a bivalent moiety selected from —$CH_2$—, —C(O)—, —C(S)—, or

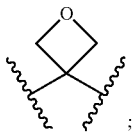 [SMILES: *C1(*)COC1]

$R^1$ is hydrogen, deuterium, halogen, —CN, —OR, —SR, —S(O)R, —S(O)$_2$R, —NR$_2$, or an optionally substituted $C_{1-4}$ aliphatic;

each of $R^2$, $R^3$, and $R^4$ is independently hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^5$ is hydrogen or $C_{1-6}$ aliphatic;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur;

Ring B is selected from 6-membered aryl containing 0-2 nitrogen atoms or a 8-10 membered bicyclic heteroaryl having 1-5 heteroatoms independently selected from nitrogen, oxygen, or sulfur;

Ring C is a selected from 6-membered aryl containing 0-2 nitrogen atoms or a 5-membered heteroaryl with 1-3 heteroatoms independently selected from nitrogen, oxygen or sulfur;

L is a covalent bond or a bivalent, saturated or unsaturated, straight or branched $C_{1-50}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

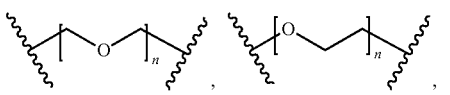

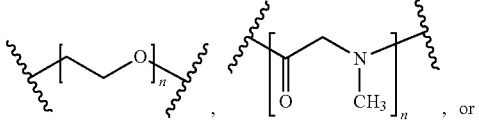

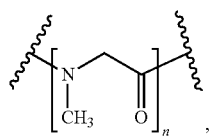

wherein:

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

m is 0, 1, 2, 3 or 4;

each of n is independently 1, 2, 3, 4, 5, 6, 7, 8, 9, or 10;

p is 0, 1, 2, 3 or 4;

q is 0, 1, 2, 3 or 4; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In certain embodiments, the present invention provides a compound of Formula I, wherein LBM is an E3 ubiquitin ligase (cereblon) binding moiety

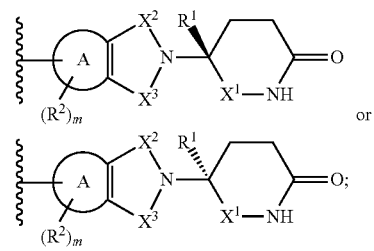

thereby forming a compound of formula I-y'-1 or I-y"-1:

I-y'-1

I-y"-1

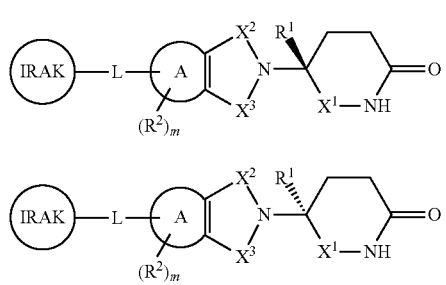

or a pharmaceutically acceptable salt thereof, wherein IRAK, L, Ring A, $X^1$, $X^2$, $X^3$, $R^1$, $R^2$ and m are as described above.

In certain embodiments, the present invention provides a compound of Formula I, wherein LBM is an E3 ubiquitin ligase (cereblon) binding moiety

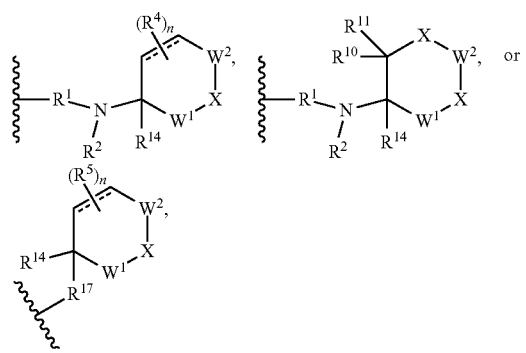

thereby forming a compound of formula I-z-1, I-z-2, or I-z-3 respectively:

I-z-1

I-z-2

I-z-3

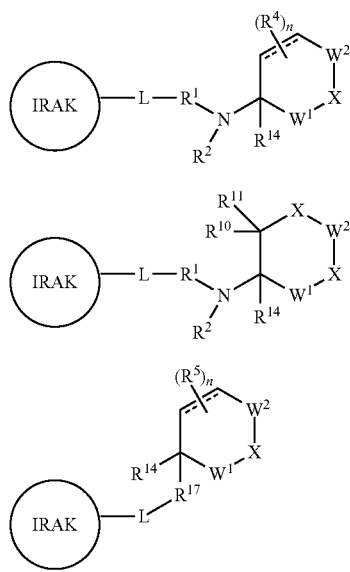

or a pharmaceutically acceptable salt thereof, wherein L and IRAK are as defined above and described herein, and wherein:

$W^1$ is $CR^6R^7$, C=O, C=S, C=CH$_2$, SO$_2$, S(O), P(O)Oalkyl, P(O)NHalkyl, P(O)N(alkyl)$_2$, P(O)alkyl, P(O)OH, P(O)NH$_2$;

$W^2$ is $CR^8R^9$, C=O, C=S, C=CH$_2$, SO2, S(O), P(O)Oalkyl, P(O)NHalkyl, P(O)N(alkyl)$_2$, P(O)alkyl, P(O)OH, P(O)NH$_2$;

X is independently selected from NH, $NR^3$, CH$_2$, $CHR^3$, $C(R^3)_2$, O, and S;

n is 0, 1, 2, or 3;

=== is a single or double bond;

wherein when === represents a single bond, n is 0, 1, 2, or 3;

wherein when === represents a double bond, n is 0, 1, or 2;

$R^1$ is selected from:

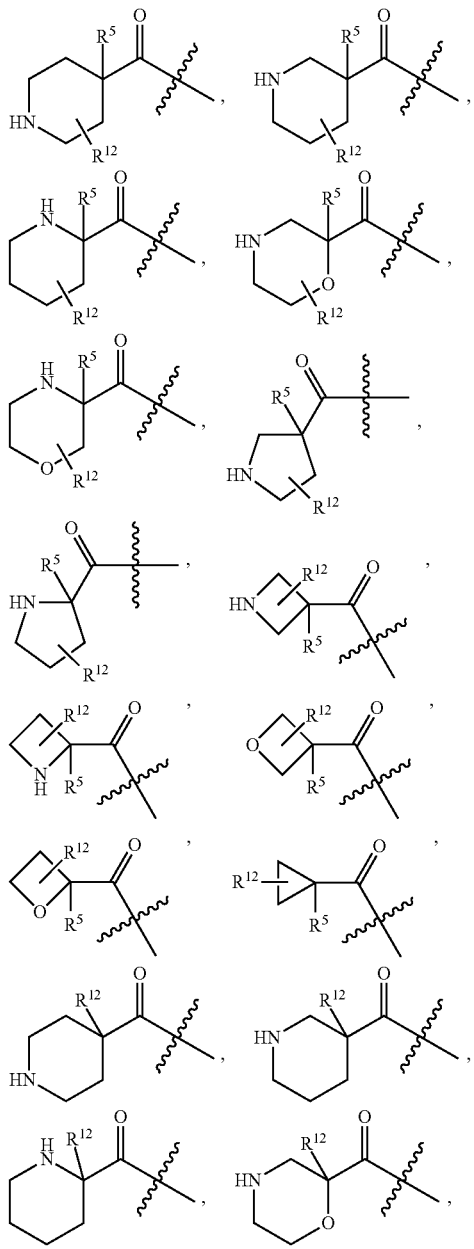

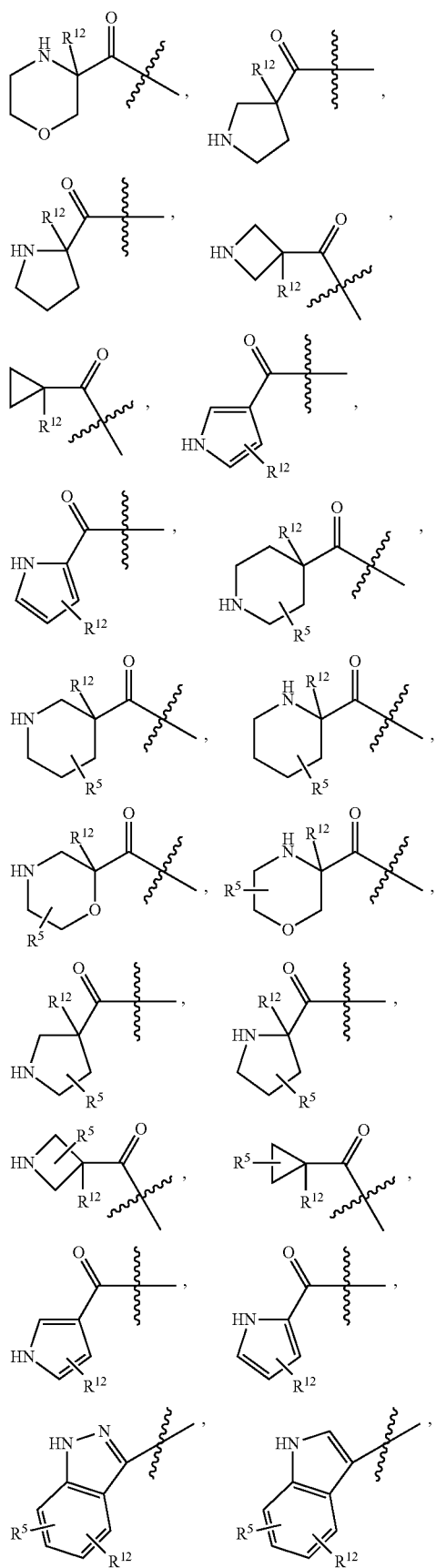
-continued
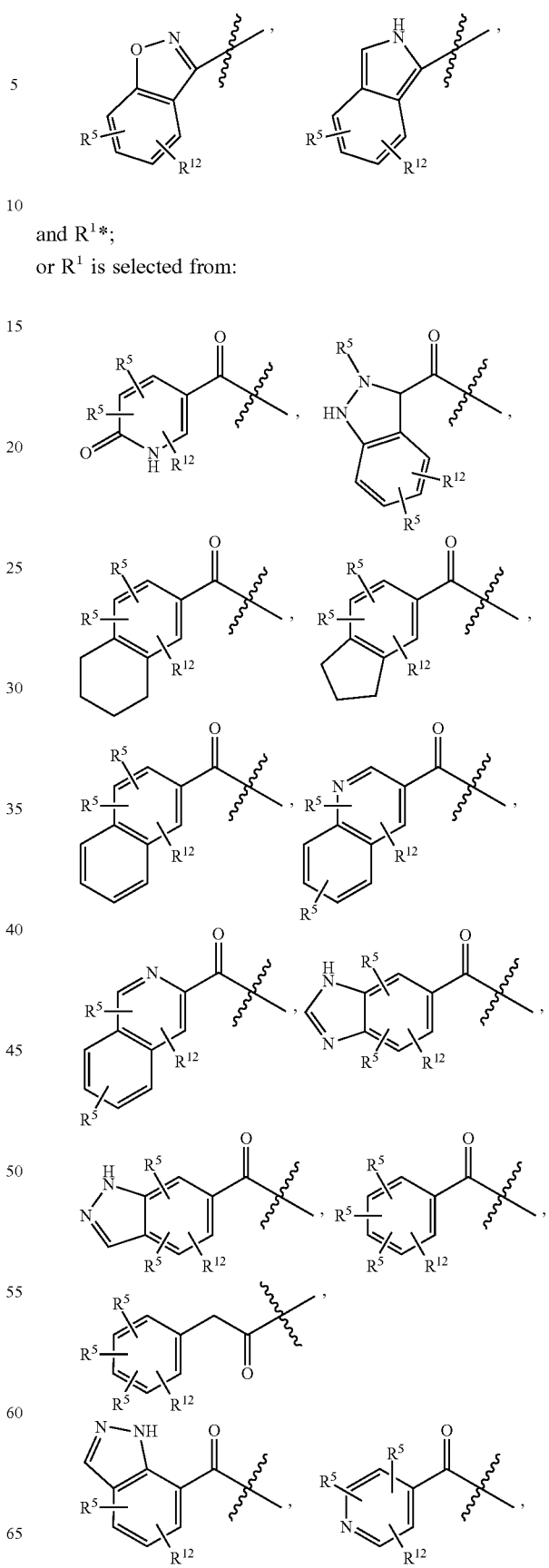
and R[1]*;
or R[1] is selected from:

-continued

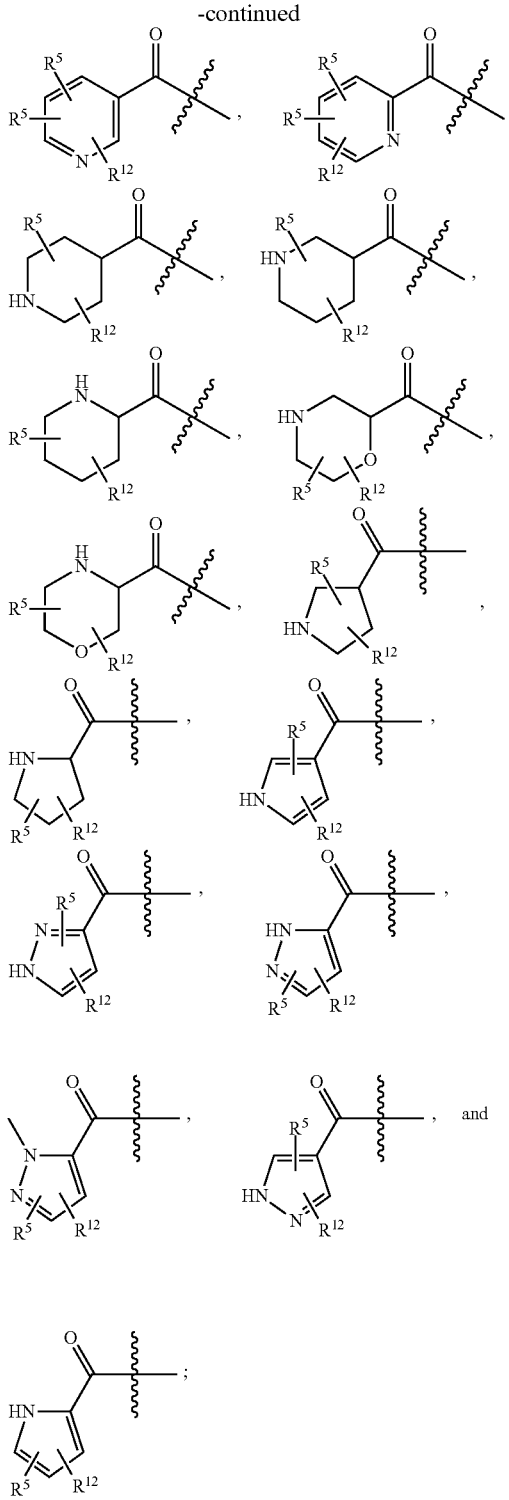

R² is alkyl, hydrogen, aliphatic, heteroaliphatic, aryl, heteroaryl or heterocyclic;

or R¹ and R² are combined to form a 4, 5, 6, 7, 8, 9, or 10 membered heterocyclo or heteroaryl species, wherein the heterocyclo or heteroaryl species is substituted with $R^{12}$ at any desired position, wherein the heterocyclo or heteroaryl species is optionally further substituted with one or more substituents selected from $R^5$;

$R^{1*}$ is selected from:

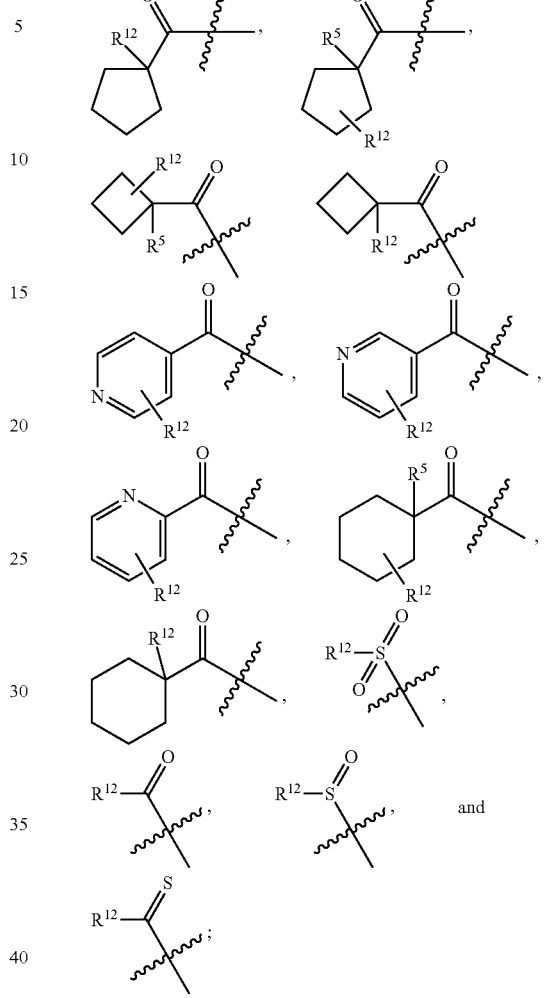

$R^3$ is selected at each instance from: alkyl, —C(O)H, —C(O)OH, —C(O)alkyl, —C(O)Oalkyl, alkene, and alkyne, aliphatic, heteroaliphatic, aryl, heteroaryl and heteroalkyl;

$R^4$ is selected at each instance from: alkyl, alkene, alkyne, halogen, hydroxyl, alkoxy, azide, amino, cyano, —NH(aliphatic), —N(aliphatic)₂, —NHSO₂(aliphatic), —N(aliphatic)SO₂alkyl, —NHSO₂(aryl, heteroaryl or heterocyclic), —N(alkyl)SO₂(aryl, heteroaryl or heterocyclic) —NHSO₂alkenyl, —N(alkyl)SO₂alkenyl, —NHSO₂alkynyl, —N(alkyl)SO₂alkynyl, and haloalkyl; aliphatic, heteroaliphatic, aryl, heteroaryl, heteroalkyl and carbocyclic;

or two $R^4$ substituents together with the carbon atom(s) to which they are bound can form a 3, 4, 5 or 6 membered ring; $R^5$ and $R^{14}$ are selected at each instance from: hydrogen, alkyl, alkene, alkyne, halogen, hydroxyl, alkoxy, azide, amino, cyano, —NH(aliphatic), —N(aliphatic)₂, —NHSO₂(aliphatic), —N(aliphatic)SO₂alkyl, —NHSO₂(aryl, heteroaryl or heterocyclic), —N(alkyl)SO₂(aryl, heteroaryl or heterocyclic) —NHSO₂alkenyl, —N(alkyl)SO₂alkenyl, —NHSO2alkynyl, —N(alkyl)SO₂alkynyl, and haloalkyl; aliphatic, heteroaliphatic, aryl, heteroaryl, heteroalkyl and carbocyclic;

or $R^5$ is independently selected from $C(O)R^4$, cyano, aryl, aryloxy, heterocyclo, heteroaryl, arylalkyl, alkoxy, hydroxyl, O-arylalkyl, or cycloalkyl;

$R^6$, $R^7$, $R^8$, $R^9$, $R^{10}$, and $R^{11}$, are independently selected from hydrogen, alkyl, aliphatic, heteroaliphatic, hydroxyl, alkoxy, amine, —NH(aliphatic), and —N(aliphatic)$_2$;

or $R^6$ and $R^7$ together with the carbon to which they are bound form a 3-, 4-, 5-, or 6-membered spirocarbocycle, or a 4-, 5-, or 6-membered spiroheterocycle comprising 1 or 2 heteroatoms selected from N and O;

or $R^8$ and $R^9$ together with the carbon to which they are bound form a 3-, 4-, 5-, or 6-membered spirocarbocycle, or a 4-, 5-, or 6-membered spiroheterocycle comprising 1 or 2 heteroatoms selected from N and O;

or $R^{10}$ and $R^{11}$ together with the carbon to which they are bound form a 3-, 4-, 5-, or 6-membered spirocarbocycle, or a 4-, 5-, or 6-membered spiroheterocycle comprising 1 or 2 heteroatoms selected from N and O;

or $R^6$ and $R^8$ form a 1 or 2 carbon bridged ring;

or $R^6$ and $R^{10}$ form a 1 or 2 carbon bridged ring;

or $R^8$ and $R^{10}$ form a 1 or 2 carbon bridged ring;

or $R^{14}$ and $R^6$ form a 3, 4, 5, or 6 carbon fused ring;

or $R^{14}$ and $R^{10}$ form a 3, 4, 5, or 6 carbon fused ring;

or $R^{14}$ and $R^8$ form a 1 or 2 carbon bridged ring;

or $R^{14}$ and $R^4$ form a 3, 4, 5, or 6 carbon fused ring wherein $R^5$ is on the carbon alpha to $R^{14}$ or a 1, 2, 3, or 4 carbon bridged ring wherein $R^5$ is not on the carbon alpha to $R^{14}$;

$R^{12}$ is L;

$R^{17}$ is selected from:

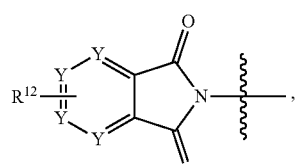

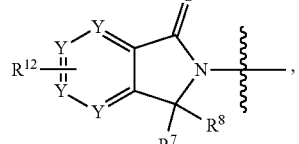

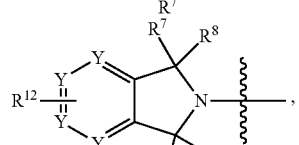

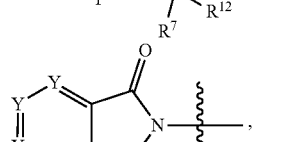

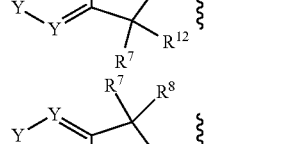

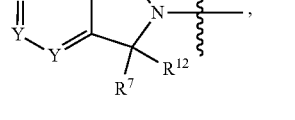

-continued

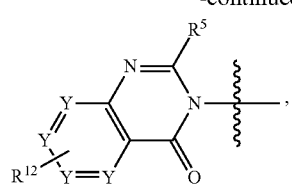

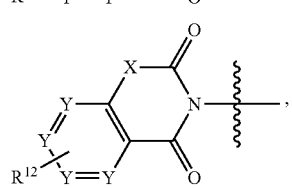

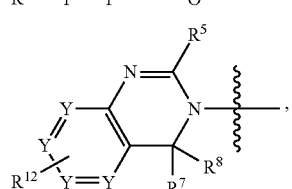

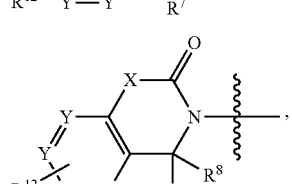

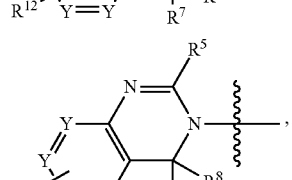

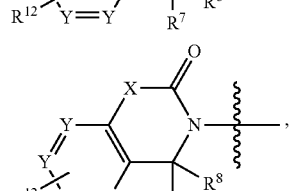

Y is independently selected from N, CH, or $CR^{101}$, wherein 0, 1, 2, or 3 instances of Y are selected to be N;

$R^{101}$ is independently selected at each occurrence from hydrogen, alkyl, alkene, alkyne, haloalkyl, alkoxy, hydroxyl, aryl, heteroaryl, heterocycle, arylalkyl, heteroarylalkyl, heterocycloalkyl, aryloxy, heteroaryloxy, CN, —COOalkyl, COOH, $NO_2$, F, Cl, Br, I, $CF_3$, $NH_2$, NHalkyl, N(alkyl)$_2$, aliphatic, and heteroaliphatic as defined in WO 2017/197051, the entirety of which is herein incorporated by reference, and wherein

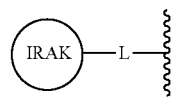

is attached to $R^1$, the ring formed by combining $R^1$ and $R^2$, or $R^{17}$ at the site of attachment of $R^{12}$ as defined in WO 2017/197051 such that

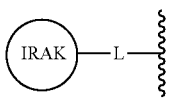

takes the place of the $R^{12}$ substituent.

In certain embodiments, the present invention provides a compound of Formula I, wherein LBM is an E3 ubiquitin ligase (cereblon) binding moiety

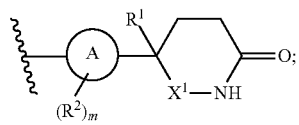

thereby forming a compound of formula I-aa:

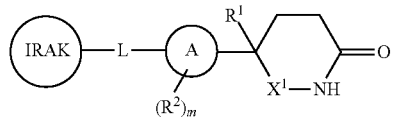

I-aa or a pharmaceutically acceptable salt thereof, wherein L and IRAK are as defined above and described in embodiments herein, and wherein:

$X^1$ is a bivalent moiety selected from a covalent bond, —$CH_2$—, —C(O)—, —C(S)—, or

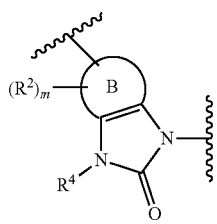

$R^1$ is hydrogen, deuterium, halogen, —CN, —OR, —SR, —S(O)R, —S(O)$_2$R, —NR$_2$, or an optionally substituted $C_{1-4}$ aliphatic;

each $R^2$ is independently hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

Ring A is a bi- or tricyclic ring selected from

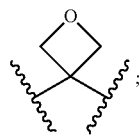 [SMILES: *C1(*)COC1]

wherein Ring B is other than imidazo or benzo,

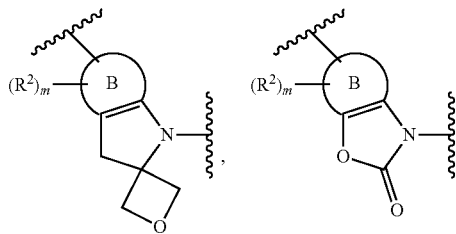

wherein Ring B is other than benzo,

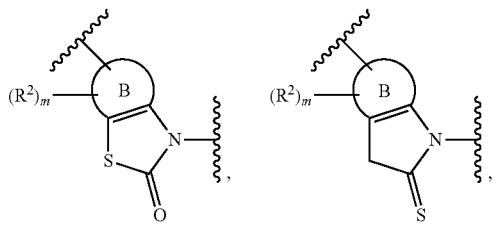

wherein Ring B is other than benzo,

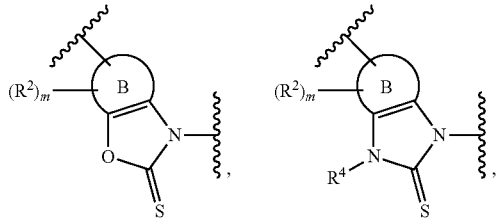

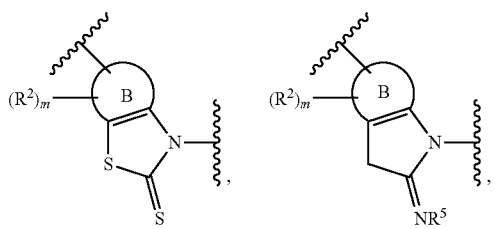

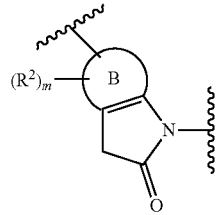

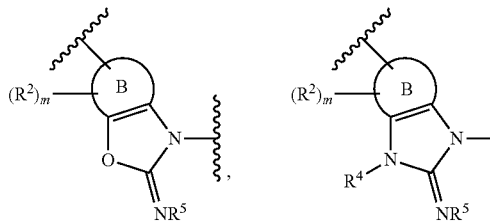

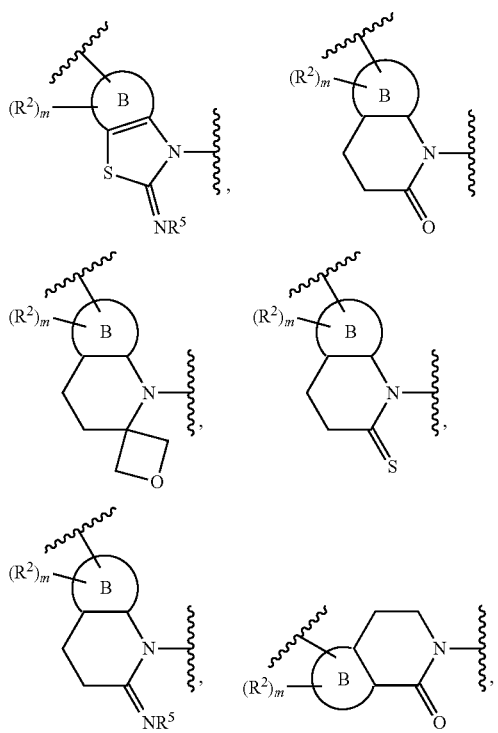
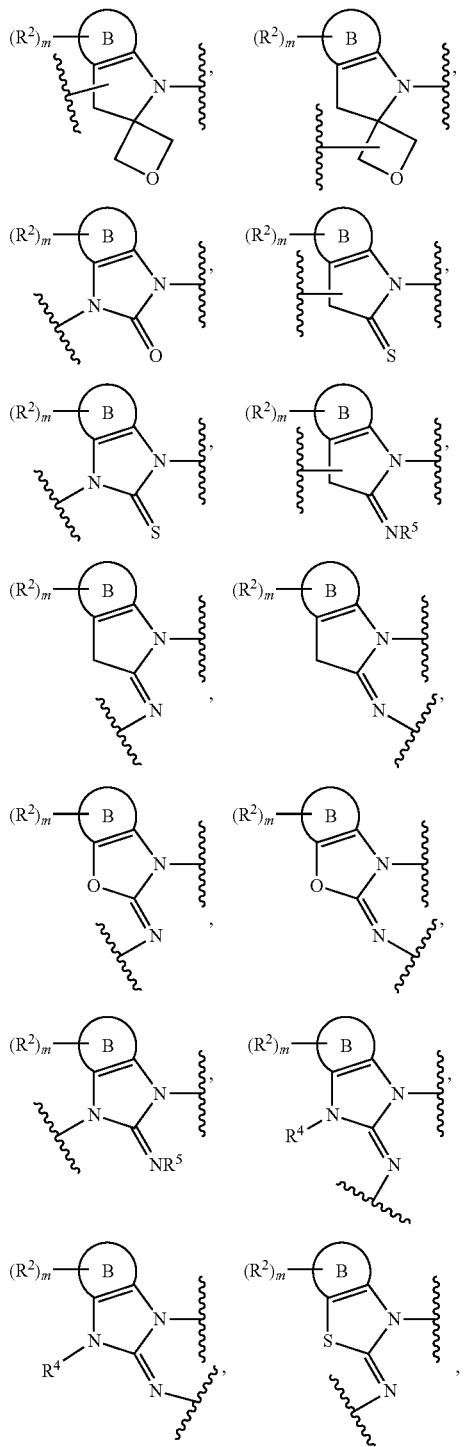
wherein Ring B is other than benzo,
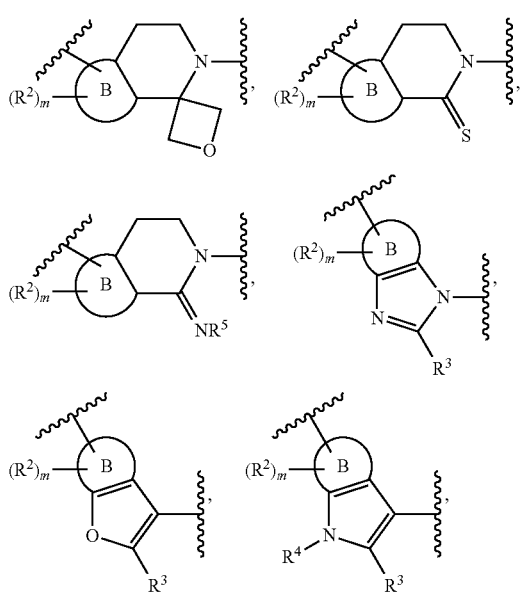
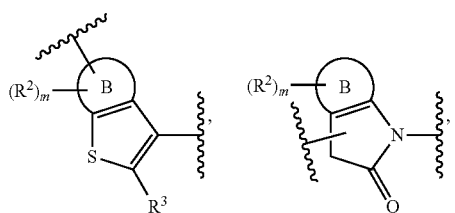
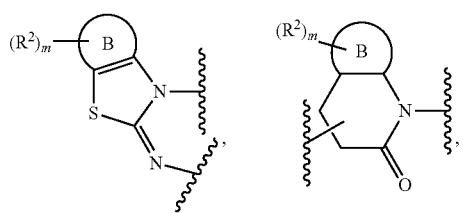

-continued

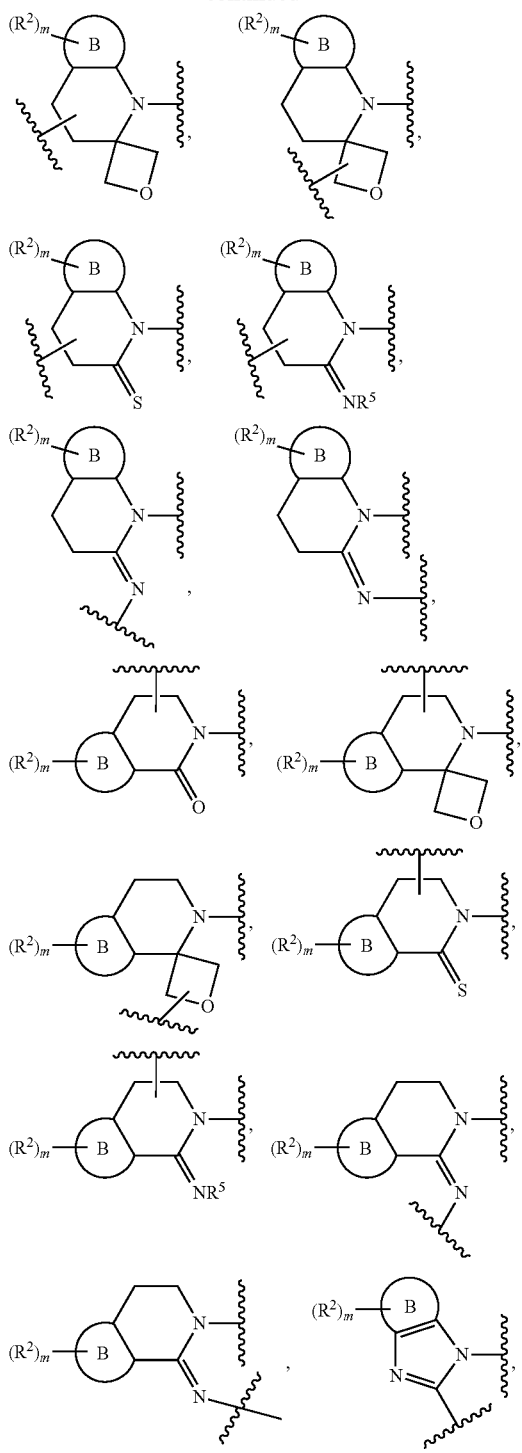

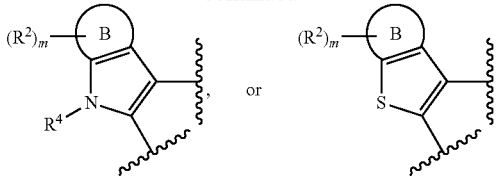

wherein
Ring B is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur;

$R^3$ is selected from hydrogen, halogen, —OR, —N(R)$_2$, or —SR;

each $R^4$ is independently hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, 2, 3 or 4; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In certain embodiments, the present invention provides a compound of Formula I, wherein LBM is an E3 ubiquitin ligase (cereblon) binding moiety

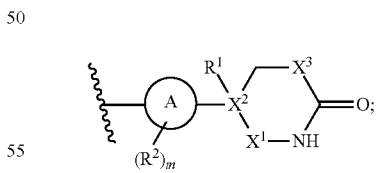

thereby forming a compound of formula I-aa':

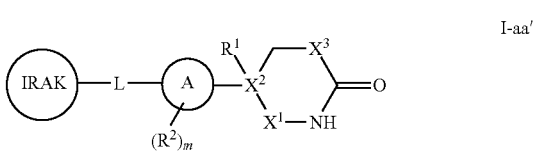

I-aa' or a pharmaceutically acceptable salt thereof, wherein L and IRAK are as defined above and described in embodiments herein, and wherein:

$X^1$ is a bivalent moiety selected from a covalent bond, —CH$_2$—, —C(O)—, —C(S)—, or

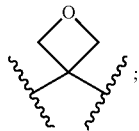

$X^2$ is a carbon atom or silicon atom;

$X^3$ is a bivalent moiety selected from —CH$_2$— or —Si(R$_2$)—;

$R^1$ is hydrogen, deuterium, halogen, —CN, —OR, —SR, —S(O)R, —S(O)$_2$R, —N(R)$_2$, —Si(R)$_3$, or an optionally substituted C$_{1-4}$ aliphatic;

each $R^2$ is independently hydrogen, deuterium, —R$^6$, halogen, —CN, —NO$_2$, —OR, —SR, —NR$_2$, —Si(R)$_3$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

Ring A is a bi- or tricyclic ring selected from

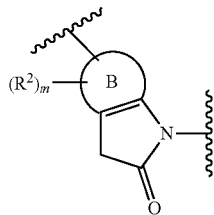

wherein Ring B is other than imidazo or benzo,

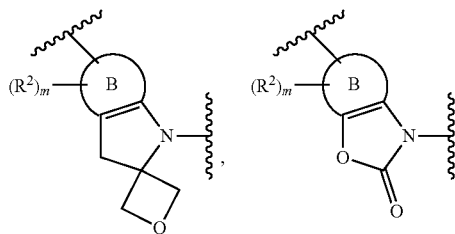

wherein Ring B is other than benzo,

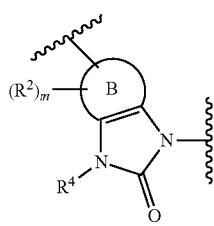

wherein Ring B is other than benzo,

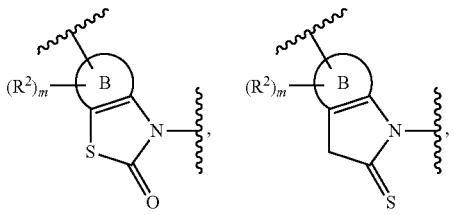

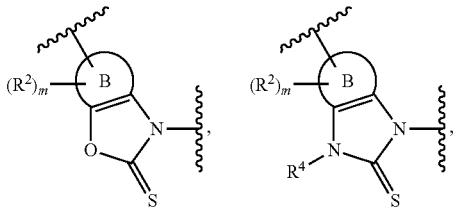

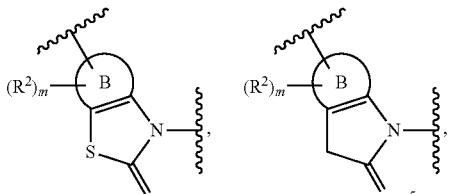

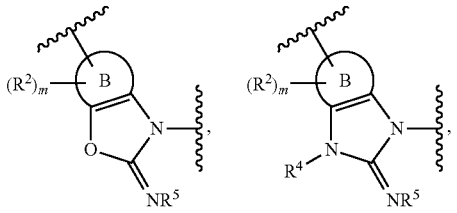

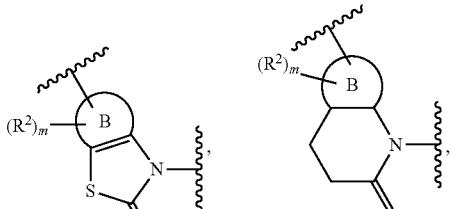

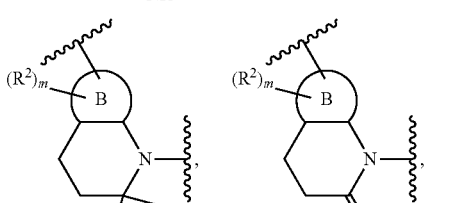

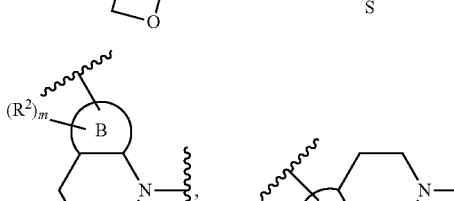

wherein Ring B is other than benzo,
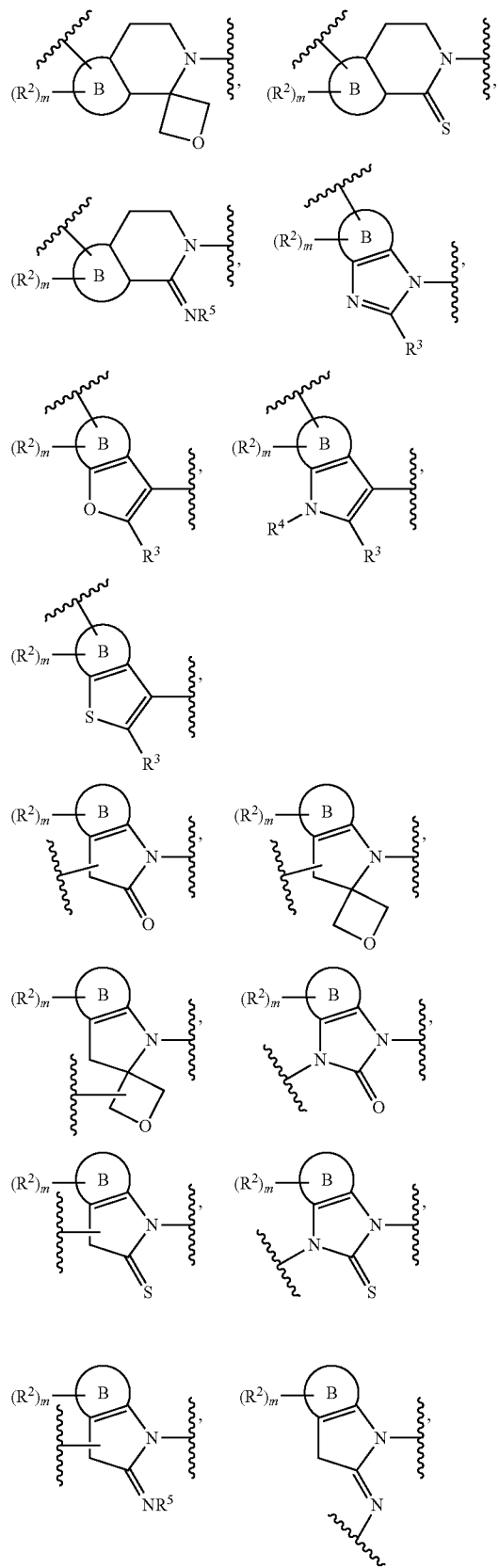
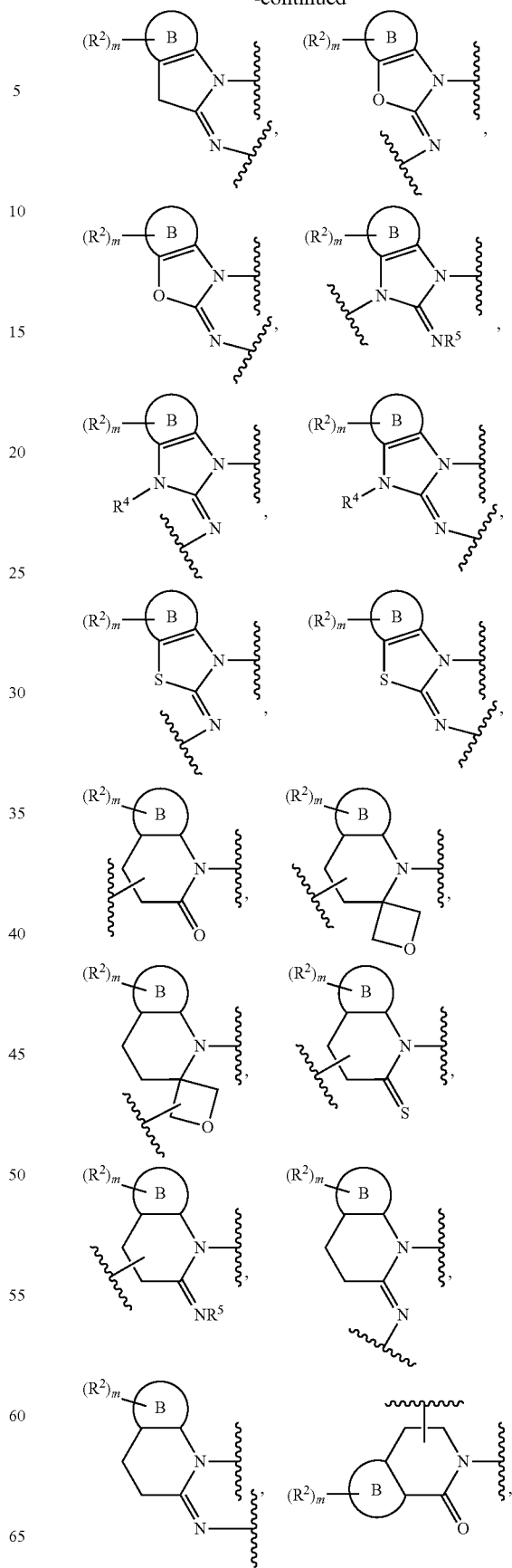

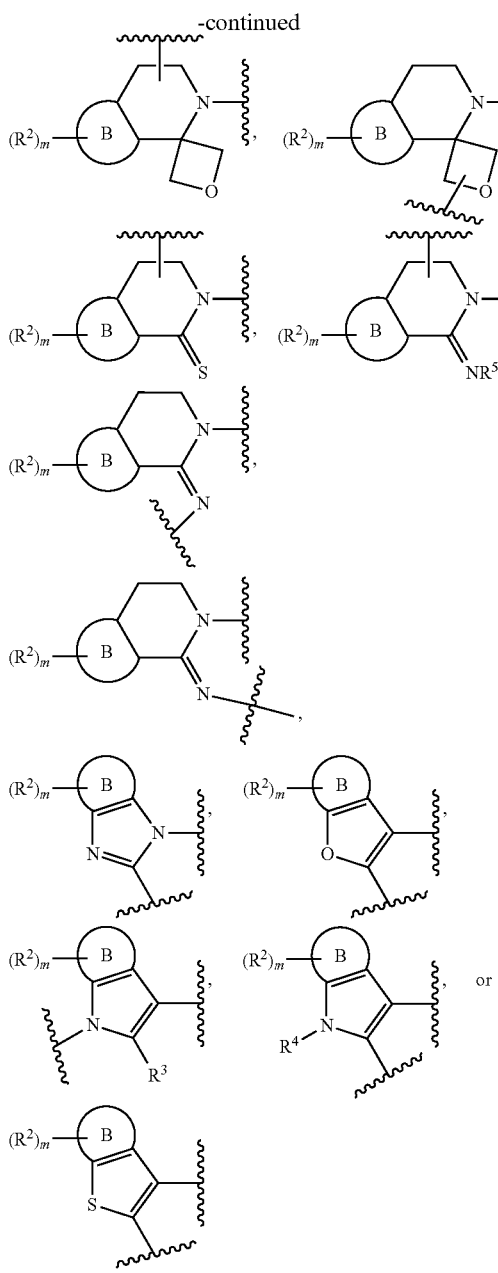

wherein

Ring B is a fused ring selected from 6-membered aryl containing 0-2 nitrogen atoms, 5 to 7-membered partially saturated carbocyclyl, 5 to 7-membered partially saturated heterocyclyl with 1-3 heteroatoms independently selected from boron, nitrogen, oxygen, silicon, or sulfur, or 5-membered heteroaryl with 1-3 heteroatoms independently selected from nitrogen, oxygen or sulfur;

$R^3$ is selected from hydrogen, halogen, —OR, —N(R)$_2$, or —SR;

each $R^4$ is independently hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^5$ is hydrogen, C$_{1-4}$ aliphatic, or —CN;

each $R^6$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, 2, 3 or 4; and each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, the compound of formula I-aa' above is provided as a compound of formula I-aa" or formula I-aa'":

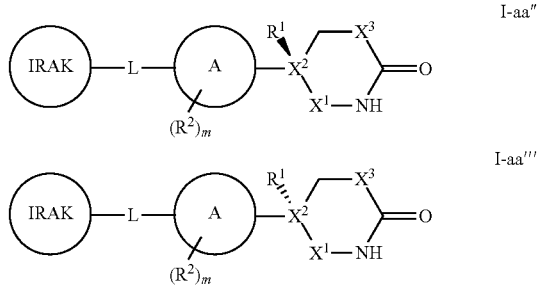

or a pharmaceutically acceptable salt thereof, wherein:
each of IRAK, Ring A, L, $R^1$, $R^2$, $X^1$, $X^2$, $X^3$, and m is as defined above.

In certain embodiments, the present invention provides a compound of Formula I, wherein LBM is an E3 ubiquitin ligase (cereblon) binding moiety

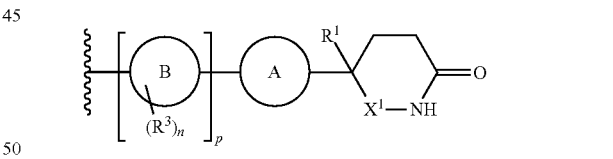

thereby forming a compound of formula I-bb:

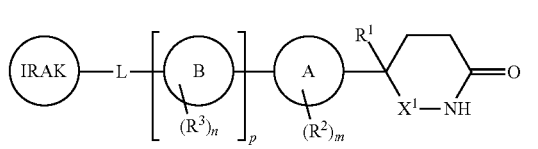

or a pharmaceutically acceptable salt thereof, wherein L and IRAK are as defined above and described in embodiments herein, and wherein:

$X^1$ is a bivalent moiety selected from a covalent bond, —CH$_2$—, —C(O)—, —C(S)—, or

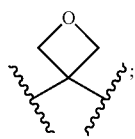 [SMILES: *C1(*)COC1]
R¹ is hydrogen, deuterium, halogen, —CN, —OR, —SR, —S(O)R, —S(O)₂R, —NR₂, or an optionally substituted C₁₋₄ aliphatic;
Ring A is a mono- or bicyclic ring selected from
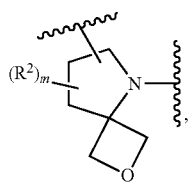
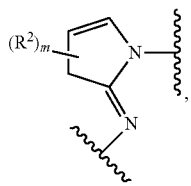 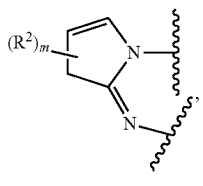
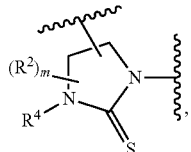 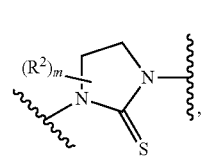
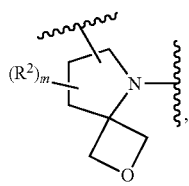
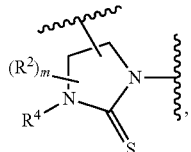
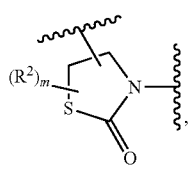
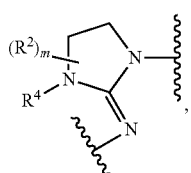 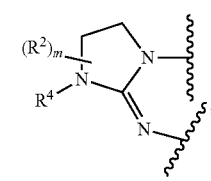
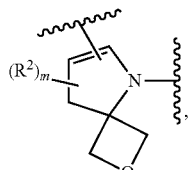
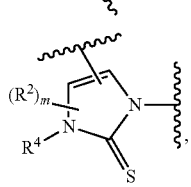 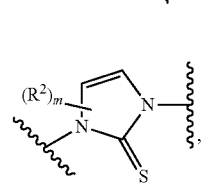
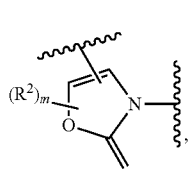
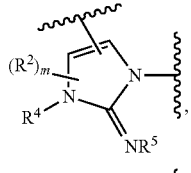 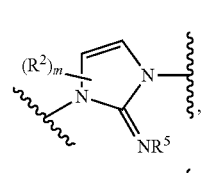
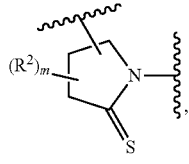
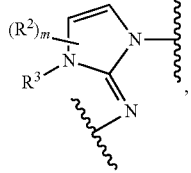 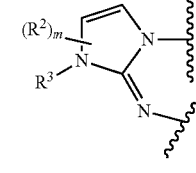
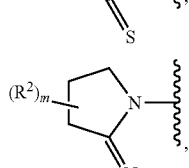
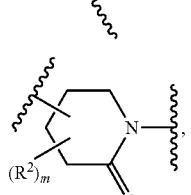 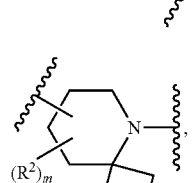
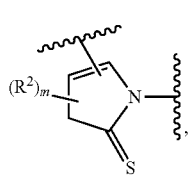
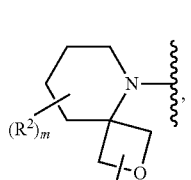 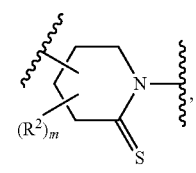

-continued

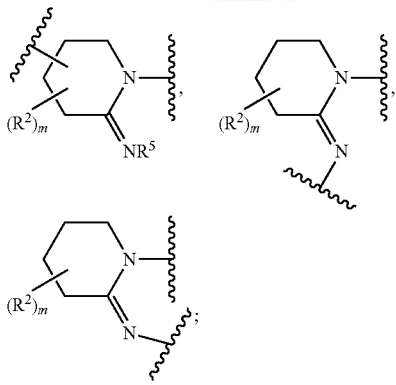

or

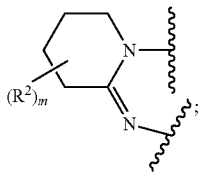

each R² is independently hydrogen, —R⁶, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

Ring B is selected from a 6-membered aryl containing 0-2 nitrogen atoms or a 5-membered heteroaryl with 1-3 heteroatoms independently selected from nitrogen, oxygen or sulfur;

each of R³ and R⁴ is independently hydrogen, —R⁶, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

R⁵ is hydrogen, C₁₋₄ aliphatic, or —CN;

each R⁶ is independently an optionally substituted group selected from C₁₋₆ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, or 2;

n is 0, 1, 2, 3, or 4;

p is 0 or 1, wherein when p is 0, the bond connecting Ring A and Ring B is connected to

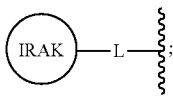

and each R is independently hydrogen, or an optionally substituted group selected from C₁₋₆ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In certain embodiments, the present invention provides a compound of Formula I, wherein LBM is an E3 ubiquitin ligase (cereblon) binding moiety

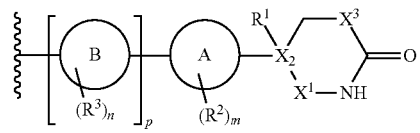

thereby forming a compound of formula I-bb':

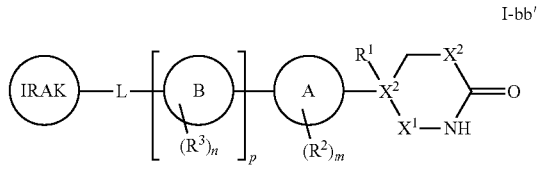

I-bb' or a pharmaceutically acceptable salt thereof, wherein L and IRAK are as defined above and described in embodiments herein, and wherein:

X¹ is a bivalent moiety selected from a covalent bond, —CH₂—, —C(O)—, —C(S)—, or

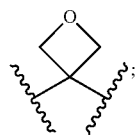 [SMILES: *C1(*)COC1]

X² is a carbon atom or silicon atom;

X³ is a bivalent moiety selected from —CH₂— or —Si(R₂)—;

R¹ is hydrogen, deuterium, halogen, —CN, —OR, —SR, —S(O)R, —S(O)₂R, —N(R)₂, —Si(R)₃, or an optionally substituted C₁₋₄ aliphatic;

Ring A is a mono- or bicyclic ring selected from

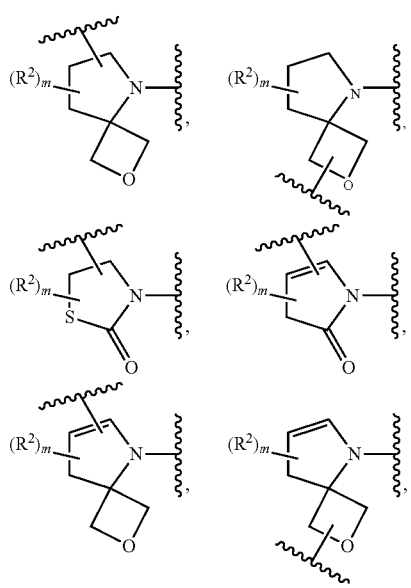

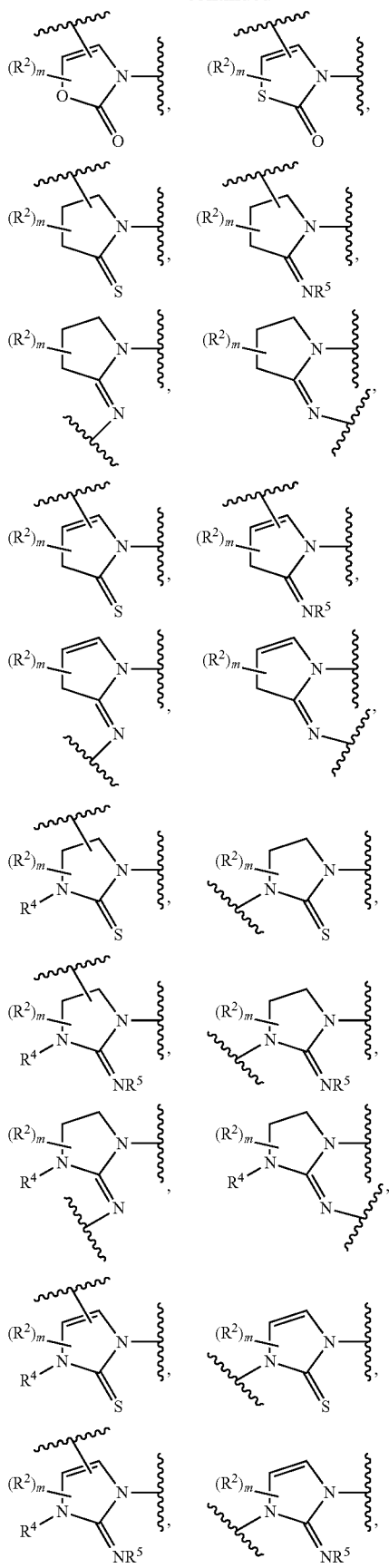

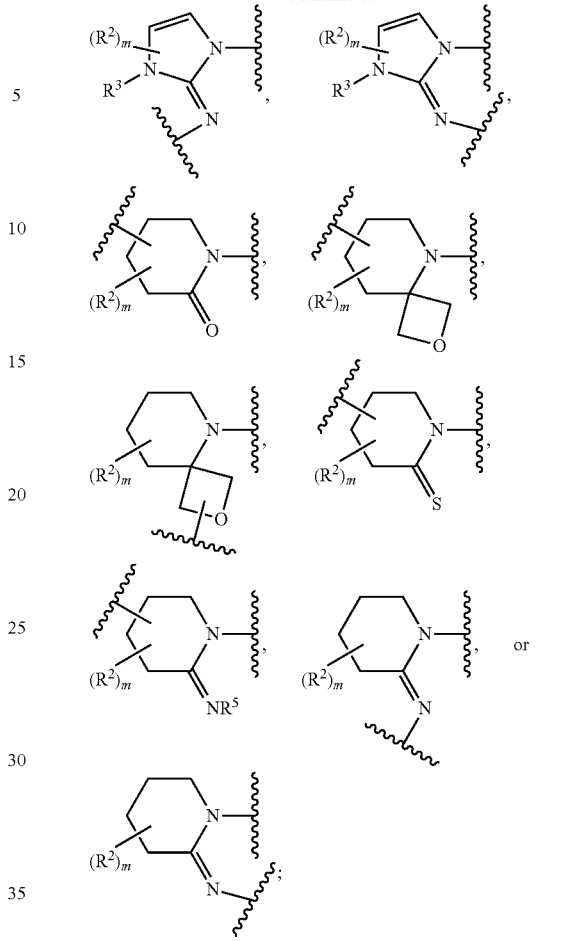

each R² is independently hydrogen, deuterium, —R⁶, halogen, —CN, —NO₂, —OR, —SR, —Si(R)₃, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or N(R)S(O)₂R;

Ring B is selected from a 6-membered aryl containing 0-2 nitrogen atoms or a 5-membered heteroaryl with 1-3 heteroatoms independently selected from nitrogen, oxygen or sulfur;

each of R³ and R⁴ is independently hydrogen, —R⁶, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

R⁵ is hydrogen, $C_{1-4}$ aliphatic, or —CN;

each R⁶ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, or 2;

n is 0, 1, 2, 3, or 4;

p is 0 or 1, wherein when p is 0, the bond connecting Ring A and Ring B is connected to

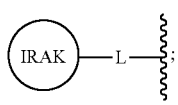

and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In certain embodiments, the present invention provides a compound of Formula I, wherein LBM is an E3 ubiquitin ligase (cereblon) binding moiety

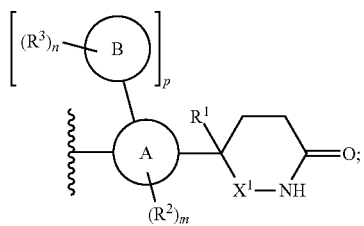

thereby forming a compound of formula I-cc:

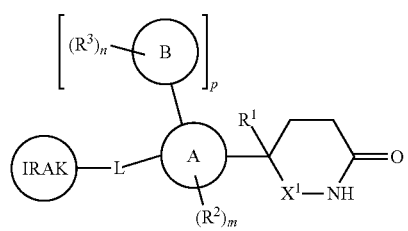

I-cc or a pharmaceutically acceptable salt thereof, wherein L and IRAK are as defined above and described in embodiments herein, and wherein:

$X^1$ is a bivalent moiety selected from a covalent bond, —$CH_2$—, —C(O)—, —C(S)—, or

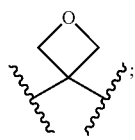

;

$R^1$ is hydrogen, deuterium, halogen, —CN, —OR, —SR, —S(O)R, —S(O)$_2$R, —NR$_2$, or an optionally substituted $C_{1-4}$ aliphatic;

Ring A is a mono- or bicyclic ring selected from

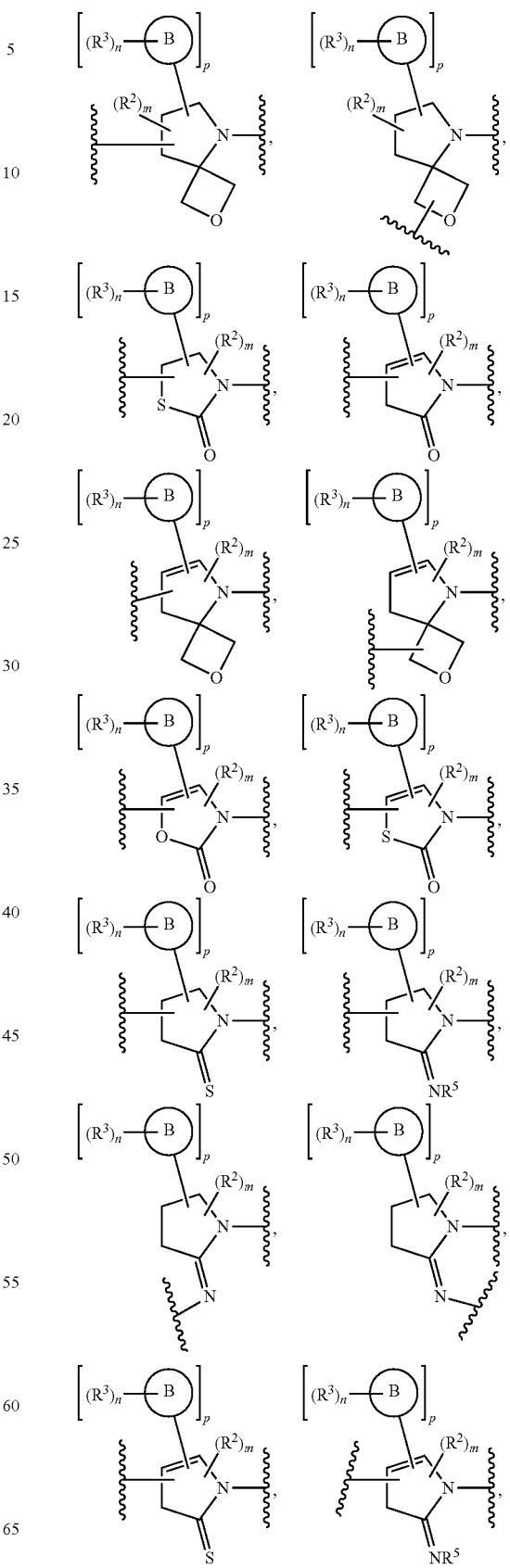

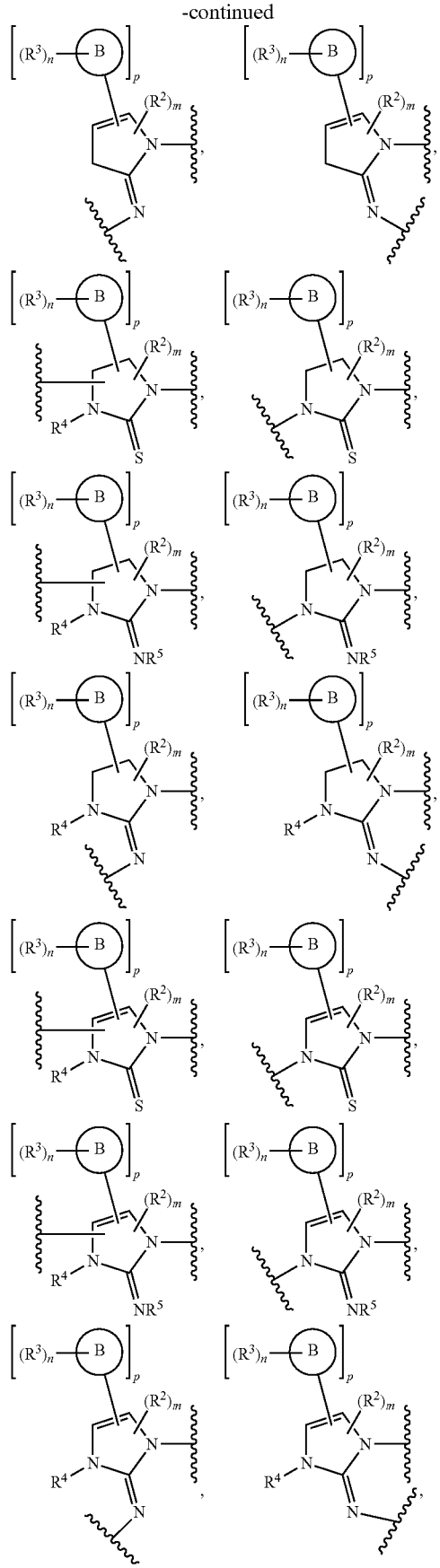
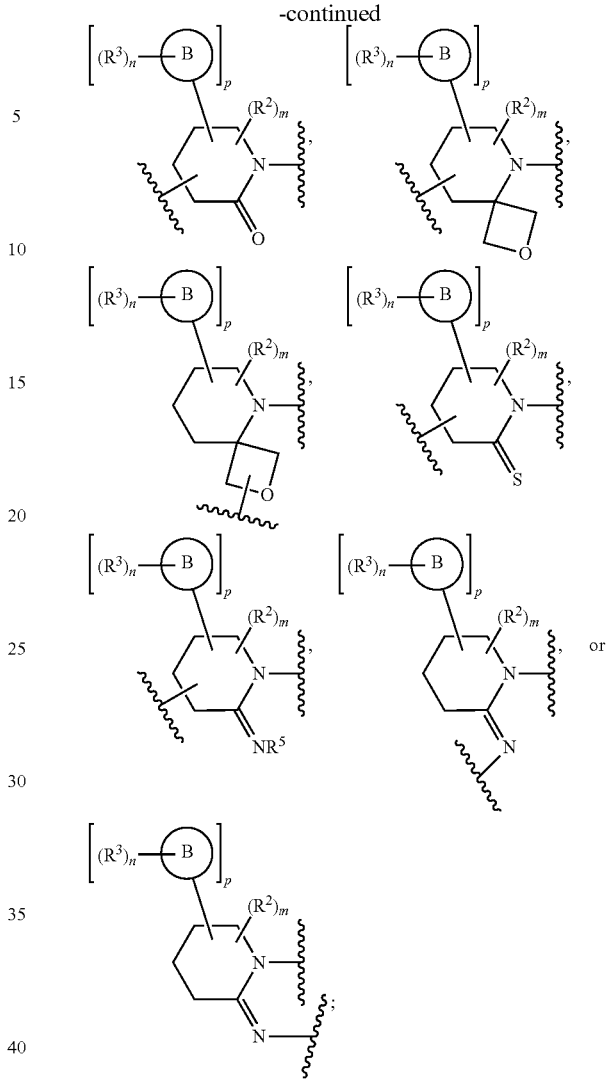

each R² is independently hydrogen, —R⁶, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

Ring B is selected from a 6-membered aryl containing 0-2 nitrogen atoms or a 5-membered heteroaryl with 1-3 heteroatoms independently selected from nitrogen, oxygen or sulfur;

each of R³ and R⁴ is independently hydrogen, —R⁶, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

R⁵ is hydrogen, $C_{1-4}$ aliphatic, or —CN;

each R⁶ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, or 2;
n is 0, 1, 2, 3, or 4;
p is 0 or 1; and
each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, the compound of formula I-bb' above is provided as a compound of formula I-bb" or formula I-bb"':

I-bb"

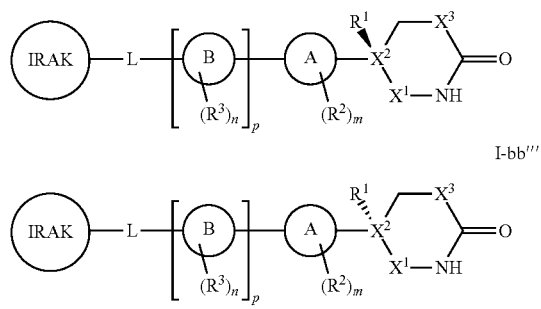

I-bb"'

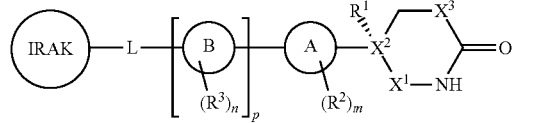

or a pharmaceutically acceptable salt thereof, wherein:
each of IRAK, Ring A, Ring B, L, $R^1$, $R^2$, $R^3$, $X^1$, $X^2$, $X^3$, p, and m is as defined above.

In certain embodiments, the present invention provides a compound of Formula I, wherein LBM is an E3 ubiquitin ligase (cereblon) binding moiety

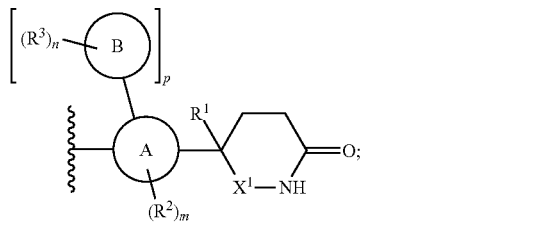

thereby forming a compound of formula I-cc':

I-cc'

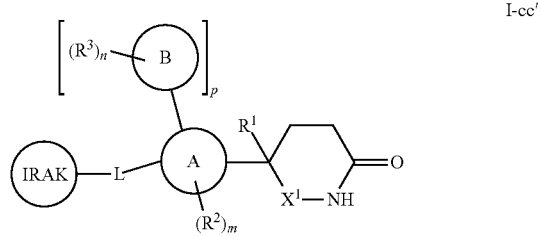

or a pharmaceutically acceptable salt thereof, wherein L and IRAK are as defined above and described in embodiments herein, and wherein:

$X^1$ is a bivalent moiety selected from a covalent bond, —$CH_2$—, —C(O)—, —C(S)—, or

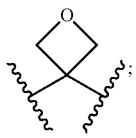 [SMILES: *C1(*)COC1]

$X^2$ is a carbon atom or silicon atom;

$X^3$ is a bivalent moiety selected from —$CH_2$— or —Si($R_2$)—;

$R^1$ is hydrogen, deuterium, halogen, —CN, —OR, —SR, —S(O)R, —S(O)$_2$R, —N(R)$_2$, —Si(R)$_3$, or an optionally substituted $C_{1-4}$ aliphatic;

Ring A is a mono- or bicyclic ring selected from

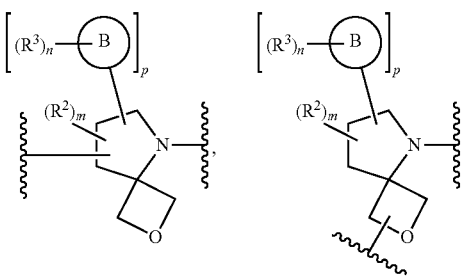

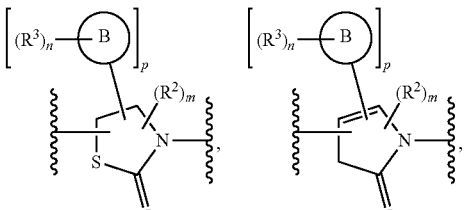

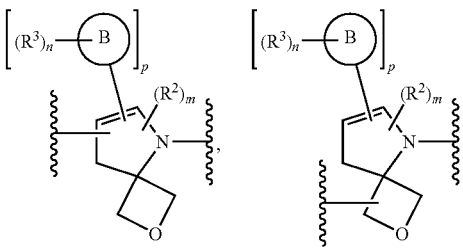

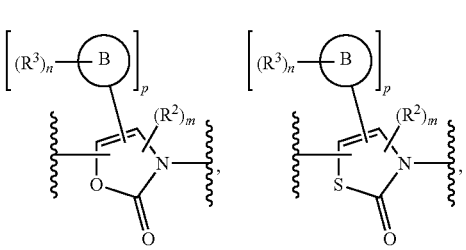

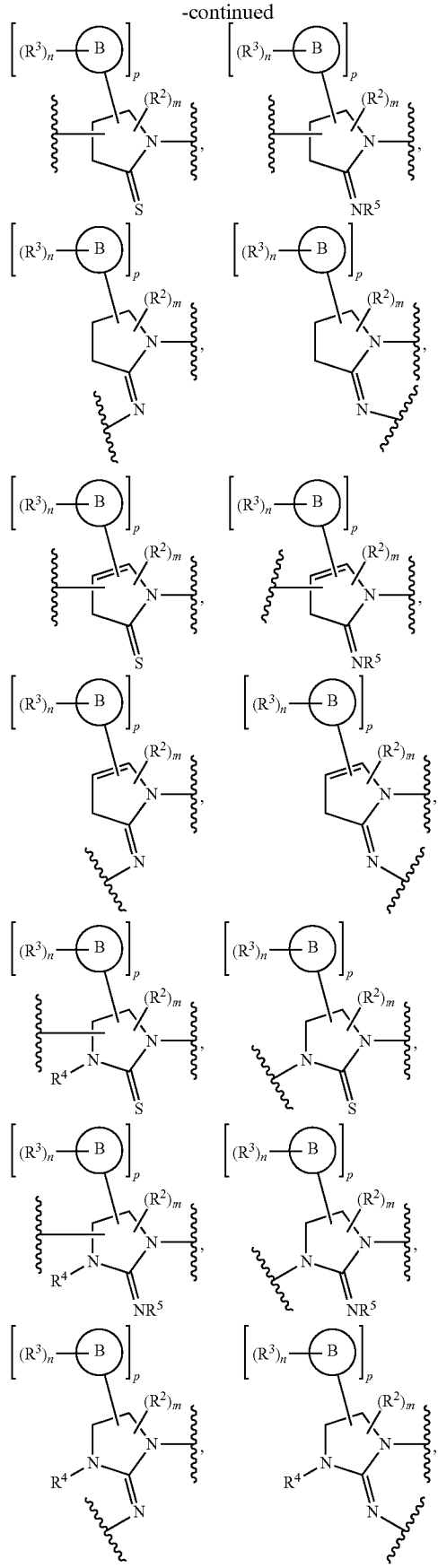
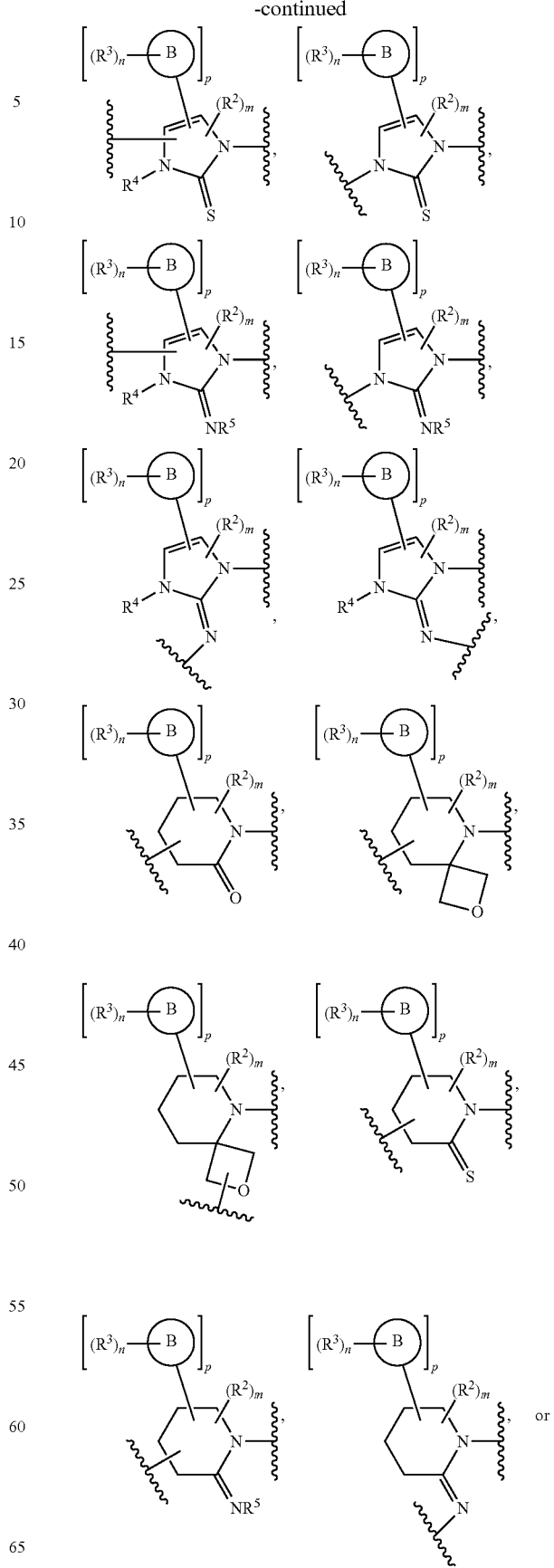

-continued

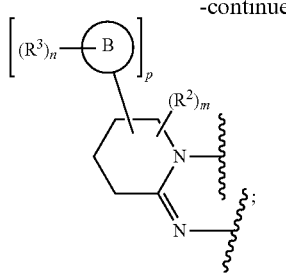

each R[2] is independently hydrogen, deuterium, —R[6], halogen, —CN, —NO$_2$, —OR, —SR, —NR$_2$, —Si(R)$_3$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

Ring B is selected from a 6-membered aryl containing 0-2 nitrogen atoms or a 5-membered heteroaryl with 1-3 heteroatoms independently selected from nitrogen, oxygen or sulfur;

each of R[3] and R[4] is independently hydrogen, —R[6], halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

R[5] is hydrogen, C$_{1-4}$ aliphatic, or —CN;

each R[6] is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, or 2;

n is 0, 1, 2, 3, or 4;

p is 0 or 1; and each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-cc' above is provided as a compound of formula I-cc" or formula I-cc''':

I-cc"

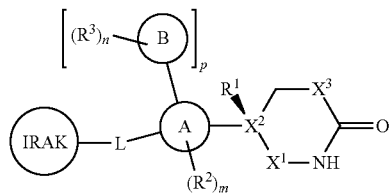

I-cc'''

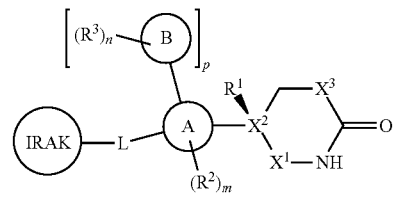

or a pharmaceutically acceptable salt thereof, wherein:
each of IRAK, Ring A, Ring B, L, R[1], R[2], R[3], X[1], X[2], X[3], p, n, and m is as defined above.

In certain embodiments, the present invention provides a compound of Formula I, wherein IRAK is an IRAK-4 inhibitor or

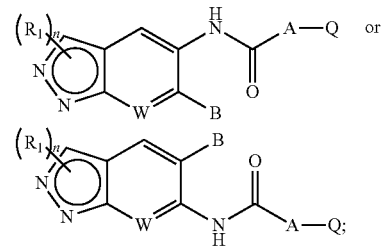

thereby forming a compound of formula I-dd-1 or I-dd-2 respectively:

I-dd-1

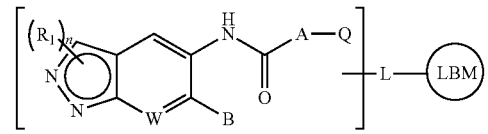

I-dd-2

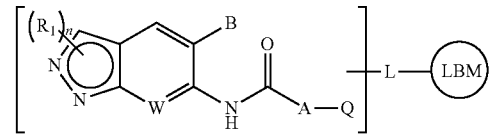

or a pharmaceutically acceptable salt thereof, wherein L and LBM are as defined above and described in embodiments herein, and wherein:

A is optionally substituted heteroaryl, optionally substituted aryl, optionally substituted heterocycloalkyl, optionally substituted cycloalkyl, optionally substituted (cycloalkyl)alkyl, optionally substituted (heterocycloalkyl)alkyl, optionally substituted aralkyl, optionally substituted heteroaralkyl, optionally substituted cycloalkyl-NR$_x$—, optionally substituted heterocycloalkyl-NR$_x$—, optionally substituted aryl-NR$_x$—, optionally substituted heteroaryl-NR$_x$—, optionally substituted cycloalkyl-O—, optionally substituted heterocycloalkyl-O—, optionally substituted aryl-O— or optionally substituted heteroaryl-O—; e.g., wherein each optional substituent independently represents an occurrence of R$_z$;

B is hydrogen, halogen, cyano, optionally substituted alkyl, optionally substituted alkenyl, optionally substituted alkoxy, —NR$_a$R$_b$, optionally substituted cycloalkyl, optionally substituted aryl, optionally substituted heterocycloalkyl, optionally substituted heteroaryl, optionally substituted (cycloalkyl)alkyl, optionally substituted (heterocycloalkyl)alkyl, optionally substituted aralkyl, optionally substituted heteroaralkyl, optionally substituted cycloalkyl-$NR_x$—, optionally substituted heterocycloalkyl-$NR_x$—, optionally substituted aryl-$NR_x$—, optionally substituted heteroaryl-$NR_x$—, optionally substituted cycloalkyl-O—, optionally substituted heterocycloalkyl-O—, optionally substituted aryl-O—, optionally substituted heteroaryl-O—; e.g., wherein each optional substituent independently represents an occurrence of $R_y$;

Q is absent or optionally substituted heterocycloalkyl, optionally substituted heteroaryl, optionally substituted aryl, optionally substituted cycloalkyl, optionally substituted (heterocycloalkyl)alkyl, optionally substituted (heteroaryl)alkyl, optionally substituted aralkyl, optionally substituted (cycloalkyl)alkyl, —$NR_3R_4$, —O—$R_3$ or —S—R; e.g., wherein each optional substituent independently represents an occurrence of $R_z$;

W is N or CH;

$R_1$ is hydrogen, optionally substituted alkyl, optionally substituted cycloalkyl, optionally substituted (cycloalkyl)alkyl, optionally substituted (heterocycloalkyl)alkyl, optionally substituted heterocycloalkyl, optionally substituted aralkyl, optionally substituted (heteroaryl)alkyl-, optionally substituted alkoxyalkyl, optionally substituted aminoalkyl, or —$(CH_2)_m$—$R_2$; e.g., wherein each optional substituent independently represents halo, hydroxy, alkoxy, amino, nitro, cycloalkyl, aryl, heterocycloalkyl or heteroaryl;

$R_2$ is hydrogen, —$NR_aR_b$, alkoxy, hydroxy, optionally substituted heteroaryl or optionally substituted heterocycloalkyl; e.g., wherein each optional substituent independently represents an occurrence of $R_y$;

each $R_3$ and $R_4$ is independently selected from optionally substituted aryl, optionally substituted cycloalkyl, optionally substituted heteroaryl, optionally substituted heterocycloalkyl, optionally substituted aralkyl, optionally substituted (cycloalkyl)alkyl, optionally substituted (heteroaryl)alkyl and optionally substituted (heterocycloalkyl)alkyl; e.g., wherein each optional substituent is independently selected from alkyl, halo, haloalkyl, hydroxy, hydroxyalkyl, alkoxy, alkoxyalkyl, amino, nitro, cycloalkyl, (cycloalkyl)alkyl, aryl, aralkyl, heterocycloalkyl, (heterocycloalkyl)alkyl, heteroaryl and (heteroaryl)alkyl;

each $R_a$ and $R_b$ is independently selected from hydrogen, alkyl, aminoalkyl, acyl and heterocyclyl; or $R_a$ and $R_b$ are taken together with the nitrogen to which they are attached to form an optionally substituted ring;

$R_x$ is hydrogen, alkyl, hydroxy, hydroxyalkyl, acyl or cycloalkyl;

each $R_y$ and $R_z$ is independently selected from hydroxy, hydroxyalkyl, halo, alkyl, oxo, haloalkyl, alkoxy, alkenyloxy, amino, nitro, cyano, —SH, —S(alkyl), glycinate, ester, thioester, cycloalkyl, heterocycloalkyl, aryl, heteroaryl, (cycloalkyl)alkyl, (heterocycloalkyl)alkyl, aralkyl, and (heteroaryl)alkyl; optionally wherein the hydroxy, hydroxyalkyl, alkoxy, cycloalkyl, heterocycloalkyl, aryl and heteroaryl are further substituted by one or more substituents selected from alkyl, halo, alkenyl, amino, nitro, cycloalkyl and (cycloalkyl)alkyl; or $R_y$ and $R_z$ taken together with the atoms to which they are attached form an alkyl chain having 1-10 carbon atoms; optionally wherein 1-3 carbon atoms are replaced by O, NH or S;

m is 1, 2, or 3; and n is 1 or 2;

as defined and described in WO 2017/009798 and US 2018/0201609, the entirety of each of which is herein incorporated by reference.

In certain embodiments, the present invention provides a compound of Formula I, wherein IRAK is an IRAK4 inhibitor

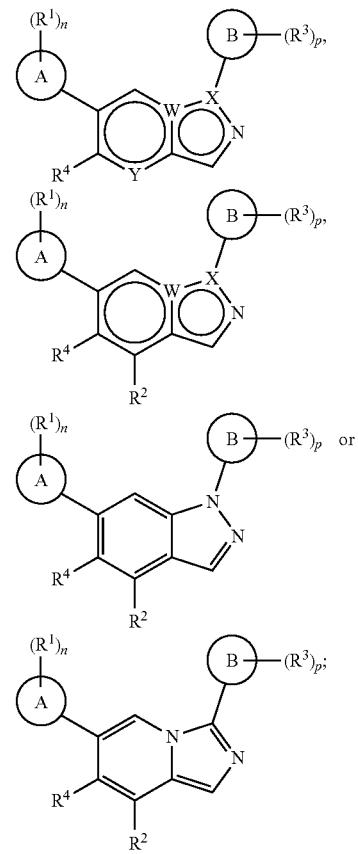

thereby forming a compound of formula I-ee-1, I-ee-2, I-ee-3, or I-ee-4 respectively:

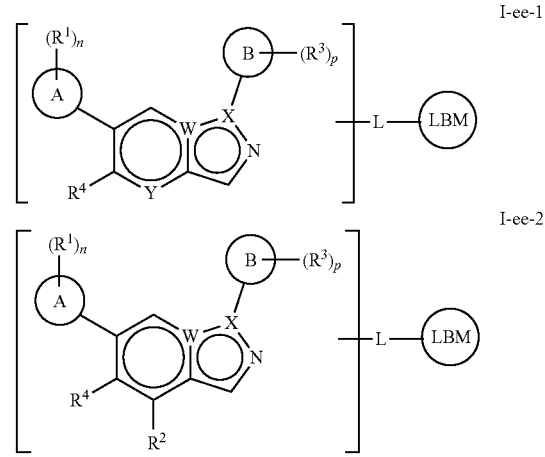

153

-continued

I-ee-3

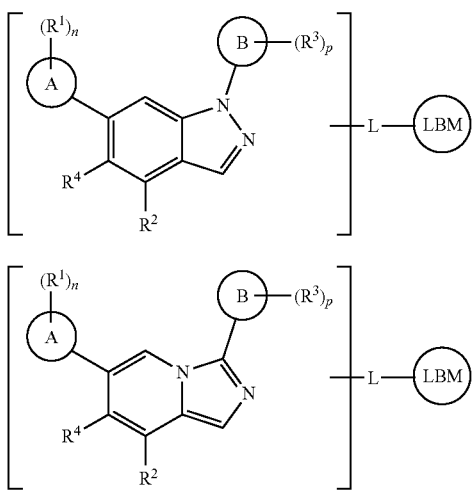

I-ee-4 or a pharmaceutically acceptable salt thereof, wherein L and LBM are as defined above and described in embodiments herein, and wherein:

Ring A is selected from phenyl and 5- or 6-membered heteroaryl;

Ring B is selected from phenyl and 5- or 6-membered heteroaryl;

n is 0, 1, or 2;

p is 0, 1, or 2;

one of W and X is N, and the other of W and X is C;

Y is N or C—$R^2$;

$R^1$ is selected from $C_{1-6}$alkyl, $C_{2-6}$alkenyl, $C_{2-6}$alkynyl, $C_{3-6}$cycloalkyl, 3- to 6-membered saturated heterocyclyl, halo, —CN, —C($R^{1a}$)=NR(O$R^{1a}$), —C($R^{1a}$)=N($R^{1a}$), —C(O)$R^{1a}$, —C(O)$_2R^{1a}$, —C(O)N($R^{1a}$)$_2$, —NO$_2$, —N($R^{1a}$)$_2$, —N($R^{1a}$)C(O)$R^{1a}$, —N($R^{1a}$)C(O)$_2R^{1a}$, —N($R^{1a}$)C(O)N($R^{1a}$)$_2$, —N($R^{1a}$)S(O)$_2R^{1a}$, —O$R^{1a}$, —OC(O)$R^{1a}$, —OC(O)N($R^{1a}$)$_2$, —S$R^{1a}$, —S(O)$R^{1a}$, —S(O)$_2R^{1a}$, —S(O)N($R^{1a}$)$_2$, and —S(O)$_2$N($R^{1a}$)$_2$, wherein said $C_{1-6}$alkyl, $C_{2-6}$alkenyl, $C_{2-6}$alkynyl, $C_{3-6}$cycloalkyl, and 3- to 6-membered saturated heterocyclyl are optionally substituted with one or more $R^{10}$; or two $R^1$ substituents, together with their intervening atoms, form a $C_{5-7}$cycloalkyl or a saturated 5- to 7-membered heterocyclic ring, wherein said $C_{5-7}$cycloalkyl or a saturated 5- to 7-membered heterocyclic ring are optionally substituted with one or more $R^{15}$;

$R^{1a}$ in each occurrence is independently selected from H, $C_{1-6}$alkyl, $C_{2-6}$alkenyl, $C_{2-6}$alkynyl, 3- to 6-membered monocyclic carbocyclyl, and 3- to 6-membered monocyclic heterocyclyl wherein said $C_{1-6}$alkyl, $C_{2-6}$alkenyl, $C_{2-6}$alkynyl, 3- to 6-membered monocyclic carbocyclyl, and 3- to 6-membered monocyclic heterocyclyl in each occurrence are optionally and independently substituted with one or more $R^{10}$;

$R^{10}$ in each occurrence is independently selected from $C_{1-6}$alkyl, $C_{2-6}$alkenyl, $C_{2-6}$alkynyl, 3- to 6-membered carbocyclyl, 3- to 6-membered heterocyclyl, halo, —CN, —C($R^{10a}$)=NR(O$R^{10a}$), —C($R^{10a}$)=N($R^{10a}$), —C(O)$R^{10a}$, —C(O)$_2R^{10a}$, —C(O)N($R^{10a}$)$_2$, —NO$_2$, —N($R^{10a}$)$_2$, —N($R^{10a}$)C(O)$R_a$, —N($R^{10a}$)C(O)$_2R^{10a}$, —N($R^{10a}$)C(O)N($R^{10a}$)$_2$, —N($R^{10a}$)S(O)$_2R^{10a}$, —O$R^{10a}$, —OC(O)$R^{10a}$, —OC(O)N($R^{10a}$)$_2$, —S$R^{10a}$, —S(O)$R^{10a}$, —S(O)$_2R^{1a}$, —S(O)N($R^{10a}$)$_2$, and —S(O)$_2$N($R^{10a}$)$_2$;

154

$R^{10a}$ in each occurrence is independently selected from H and $C_{1-6}$alkyl, wherein said $C_{1-6}$alkyl is optionally substituted with one or more halo;

$R^{15}$ in each occurrence is independently selected from $C_{1-6}$alkyl, $C_{2-6}$alkenyl, $C_{2-6}$alkynyl, 3- to 6-membered carbocyclyl, 3- to 6-membered heterocyclyl, halo, —CN, —C($R^{15a}$)=NR(O$R^{15a}$), —C($R^{15a}$)=N($R^{15a}$), —C(O)$R^{15a}$, —C(O)$_2R^{15a}$, —C(O)N($R^{15a}$)$_2$, —NO$_2$, —N($R^{15a}$)$_2$, —N($R^{15a}$)C(O)$R^{15a}$, —N($R^{15a}$)C(O)$_2R^{15a}$, —N($R^{15a}$)C(O)N($R^{15a}$)$_2$, —N($R^{15a}$)S(O)$_2R^{15a}$, —O$R^{15a}$, —OC(O)$R^{15a}$, —OC(O)N($R^{15a}$)$_2$, —S$R^{15a}$, —S(O)$R^{15a}$, —S(O)$_2R^{15a}$, —S(O)N($R^{15a}$)$_2$, and —S(O)$_2$N($R^{15a}$)$_2$;

$R^{15a}$ in each occurrence is independently selected from H and $C_{1-6}$alkyl, wherein said $C_{1-6}$alkyl is optionally substituted with one or more halo;

$R^2$ is selected from H, $C_{1-6}$alkyl, $C_{2-6}$alkenyl, $C_{2-6}$alkynyl, 3- to 7-membered carbocyclyl, 3- to 7-membered heterocyclyl, halo, —CN, —C($R^{2a}$)=NR(O$R^{2a}$), —C($R^{2a}$)=N($R^2$), —C(O)$R^{2a}$, —C(O)$_2R^{2a}$, —C(O)N($R^{2a}$)$_2$, —NO$_2$, —N($R^{2a}$)$_2$, —N($R^{2a}$)C(O)$R^{2a}$, —N($R^{2a}$)C(O)$_2R^{2a}$, —N($R^{2a}$)C(O)N($R^{2a}$)$_2$, —N($R^{2a}$)S(O)$_2R^{2a}$, —O$R^{2a}$, —OC(O)$R^{2a}$, —OC(O)N($R^{2a}$)$_2$, —S$R^{2a}$, —S(O)$R^{2a}$, —S(O)$_2R^{2a}$, —S(O)N($R^{2a}$)$_2$, and —S(O)$_2$N($R^{2a}$)$_2$, wherein said $C_{1-6}$alkyl, $C_{2-6}$alkenyl, $C_{2-6}$alkynyl, 3- to 7-membered carbocyclyl, and 3-7 membered heterocyclyl are optionally substituted with one or more $R^{20}$;

$R^{2a}$ in each occurrence is independently selected from H and $C_{1-6}$alkyl, wherein said $C_{1-6}$alkyl in each occurrence is optionally and independently substituted with one or more $R^{20}$;

$R^{20}$ in each occurrence is independently selected from $C_{1-6}$alkyl, $C_{2-6}$alkenyl, $C_{2-6}$alkynyl, $C_{3-7}$cycloalkyl, 3- to 7-membered saturated heterocyclyl, halo, —CN, —C($R^{20a}$)=NR(O$R^{20a}$), —C($R^{20a}$)=N($R^{20a}$), —C(O)$R^{20a}$, —C(O)$_2R^{20a}$, —C(O)N($R^{20a}$)$_2$, —NO$_2$, —N($R^{20a}$)$_2$, —N($R^{20a}$)C(O)$R^{2a}$, N($R^{20a}$)C(O)$_2R^{20a}$, —N($R^{20a}$)C(O)N($R^{20a}$)$_2$, —N($R^{20a}$)S(O)$_2R^{20a}$, —O$R^{20a}$, —OC(O)$R^{20a}$, —OC(O)N($R^{20a}$)$_2$, —S$R^{20a}$, —S(O)$R^{20a}$, —S(O)$_2R^{20a}$, —S(O)N($R^{20a}$)$_2$, and —S(O)$_2$N($R^{20a}$)$_2$, wherein said $C_{1-6}$alkyl, $C_{2-6}$alkenyl, $C_{2-6}$alkynyl, $C_{3-7}$cycloalkyl, and 3-7 membered saturated heterocyclyl in each occurrence are optionally and independently substituted with one or more $R^{25}$;

$R^{20a}$ in each occurrence is independently selected from H and $C_{1-6}$alkyl, wherein said $C_{1-6}$alkyl is optionally substituted with $R^{25}$;

$R^{25}$ is selected from halo and O$R^{25a}$;

$R^{25a}$ is selected from H and $C_{1-6}$alkyl;

$R^3$ is selected from $C_{1-6}$alkyl, $C_{2-6}$alkenyl, $C_{2-6}$alkynyl, $C_{3-6}$cycloalkyl, 3- to 6-membered saturated heterocyclyl, halo, —CN, —C($R^{3a}$)=NR(O$R^{3a}$), —C($R^{3a}$)=N($R^{3a}$), —C(O)$R^{3a}$, —C(O)$_2R^{3a}$, —C(O)N($R^{3a}$)$_2$, —NO$_2$, —N($R^{3a}$)$_2$, —N($R^{3a}$)C(O)$R^{3a}$, —N($R^{3a}$)C(O)$_2R^{3a}$, —N($R^{3a}$)C(O)N($R^{3a}$)$_2$, —N($R^{3a}$)S(O)$_2R^{3a}$, —O$R^{3a}$, —OC(O)$R^{3a}$, —OC(O)N($R^{3a}$)$_2$, —S$R^{3a}$, —S(O)$R^{3a}$, —S(O)$_2R^{3a}$, —S(O)N($R^{3a}$)$_2$, and —S(O)$_2$N($R^{3a}$)$_2$, wherein said $C_{1-6}$alkyl, $C_{2-6}$alkenyl, $C_{2-6}$alkynyl, $C_{3-6}$cycloalkyl, and 3- to 6-membered saturated heterocyclyl are optionally substituted with one or more $R^{30}$;

$R^{3a}$ in each occurrence is independently selected from H, $C_{1-6}$alkyl, 3- to 6-membered carbocyclyl, and 3- to 6-membered heterocyclyl, wherein said $C_{1-6}$alkyl, 3- to 6-membered carbocyclyl, and 3- to 6-membered heterocyclyl in each occurrence are optionally and independently substituted with one or more $R^{30}$;

$R^{30}$ in each occurrence is independently selected from $C_{1-6}$alkyl, $C_{2-6}$alkenyl, $C_{2-6}$alkynyl, 3- to 6-membered carbocyclyl, 3- to 6-membered heterocyclyl, halo, —CN, —C($R^{30a}$)=NR($OR^{30a}$), —C($R^{30a}$)=N($R^{30a}$), —C(O)$R^{30a}$, —C(O)$_2R^{30a}$, —C(O)N($R^{30a}$)$_2$, —NO$_2$, —N($R^{30a}$)$_2$, —N($R^{30a}$)C(O)$R^{30a}$, —N($R^{30a}$)C(O)$_2R^{30a}$, —N($R^{30a}$)C(O)N($R^{30a}$)$_2$, —N($R^{30a}$)S(O)$_2R^{30a}$, —$OR^{30a}$, —OC(O)$R^{30a}$, —OC(O)N($R^{30a}$)$_2$, —$SR^{30a}$, —S(O)$R^{30a}$S(O)$_2R^{30a}$, —S(O)N($R^{30a}$)$_2$, and —S(O)$_2$N($R^{30a}$)$_2$, wherein said $C_{1-6}$alkyl, $C_{2-6}$alkenyl, $C_{2-6}$alkynyl, 3-6 membered carboyclyl, 3- to 6-membered heterocyclyl in each occurrence are optionally and independently substituted with one or more $R^{35}$;

$R^{30a}$ in each occurrence is independently selected from H and $C_{1-4}$alkyl, wherein $C_{1-4}$alkyl is optionally substituted with one or more $R^{35}$;

$R^{35}$ in each occurrence is independently selected from halo and —$OR^{35a}$;

$R^{35a}$ in each occurrence is independently selected from H and $C_{1-6}$alkyl;

$R^4$ is selected from H, halo, $C_{1-6}$alkyl, N($R^{4a}$)$_2$, and —$OR^{4a}$; and $R^{4a}$ in each occurrence is independently selected from H and $C_{1-6}$alkyl;

as defined and described in WO 2016/011390 and US 2017/0204093, the entirety of each of which is herein incorporated by reference.

In certain embodiments, the present invention provides a compound of Formula I, wherein IRAK is an IRAK4 inhibitor

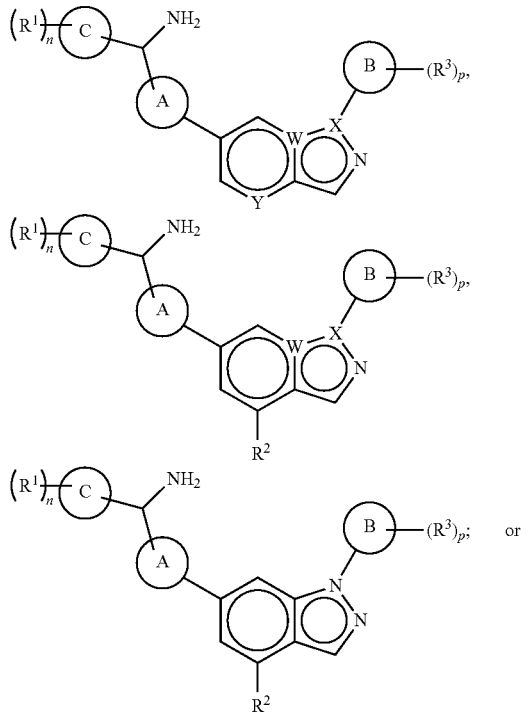

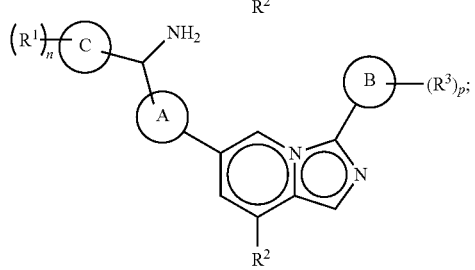

thereby forming a compound of formula I-ff-1, I-ff-2, I-ff-3, or I-ff-4 respectively I-ff-1

I-ff-2
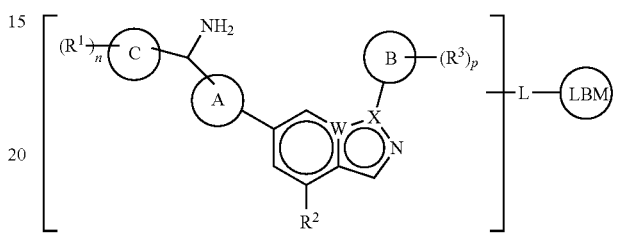

I-ff-3

I-ff-4
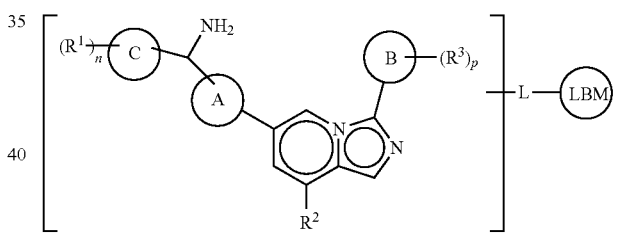

or a pharmaceutically acceptable salt thereof, wherein L and LBM are as defined above and described in embodiments herein, and wherein:

Ring A is selected from phenyl and 5- or 6-membered heteroaryl;

Ring B is selected from phenyl and 5- or 6-membered heteroaryl;

Ring C is a 3- to 6-membered carbocyclyl, n is 1, 2 or 3;

p is 0, 1, or 2;

one of W and X is N, and the other of W and X is C;

Y is N or C—$R^2$;

$R^1$ is selected from $C_{1-6}$alkyl, $C_{2-6}$alkenyl, $C_{2-6}$alkynyl, halo, —CN, —C($R^{1a}$)=NR($OR^{1a}$), —C($R^{1a}$)=N($R^{1a}$), —C(O)$R^{1a}$, —C(O)$_2R_{1a}$, —C(O)N($R^{1a}$)$_2$, —NO$_2$, —N($R^{1a}$)$_2$, —N($R^{1a}$)C(O)$R^{1a}$, —N($R^{1a}$)C(O)$_2R^{1a}$, —N($R^{1a}$)C(O)N($R^{1a}$)$_2$, —N($R^{1a}$)S(O)$_2R^{1a}$, —$OR^{1a}$, —OC(O)$R^{1a}$, —OC(O)N($R^{1a}$)$_2$, —$SR^{1a}$, —S(O)$R^{1a}$, —S(O)$_2R^{1a}$, —S(O)N($R^{1a}$)$_2$, and —S(O)$_2$N($R^{1a}$)$_2$, wherein said $C_{1-6}$alkyl, $C_{2-6}$alkenyl, and $C_{2-6}$alkynyl are optionally substituted with one or more $R^{10}$;

$R^{1a}$ in each occurrence is independently selected from H or $C_{1-6}$alkyl wherein said $C_{1-6}$alkyl in each occurrence are optionally and independently substituted with one or more $R^{10}$;

$R^{10}$ in each occurrence is independently selected from halo, —CN, —C($R^{10a}$)=NR(OR)$^{10a}$, —C($R^{10a}$)=N($R^{10a}$), —C(O)$R^{10a}$, —C(O)$_2R^{10a}$, —C(O)N($R^{10a}$)$_2$, —NO$_2$, —N($R^{10a}$)$_2$, —N($R^{10a}$)C(O)$R^{10a}$, —N($R^{10a}$)C(O)$_2R^{10a}$, —N($R^{10a}$)C(O)N($R^{10a}$)$_2$, —N($R^{10a}$)S(O)$_2R^{10a}$, —OR$^{10a}$, —OC(O)$R^{10a}$, —OC(O)N($R^{10a}$)$_2$, —SR$^{10a}$, —S(O)$R^{10a}$, —S(O)$_2R^{1a}$, —S(O)N($R^{1a}$)$_2$, and —S(O)$_2$N($R^{10a}$)$_2$;

$R^{10a}$ in each occurrence is independently selected from H and $C_{1-6}$alkyl, wherein said $C_{1-6}$alkyl is optionally substituted with one or more halo;

R is selected from H, $C_{1-6}$alkyl, $C_2$-6alkenyl, $C_2$-6alkynyl, 3- to 7-membered carbocyclyl, 3- to 7-membered heterocyclyl, halo, —CN, —C($R^{2a}$)=NR(OR$^{2a}$), —C($R^{2a}$)=N($R^{2a}$), —C(O)$R^{2a}$, —C(O)$_2R^{2a}$, —C(O)N($R^{2a}$)$_2$, —NO$_2$, —N($R^{2a}$)$_2$, —N($R^{2a}$)C(O)$R^{2a}$, —N($R^{2a}$)C(O)$_2R^{2a}$, —N($R^{2a}$)C(O)N($R^{2a}$)$_2$, —N($R^{2a}$)S(O)$_2R^{2a}$, —OR$^{2a}$, —OC(O)$R^{2a}$, —OC(O)N($R^{2a}$)$_2$, —SR$^{2a}$, —S(O)$R^{2a}$, —S(O)$_2R^{2a}$, —S(O)N($R^{2a}$)$_2$, and —S(O)$_2$N($R^{2a}$)$_2$, wherein said $C_{1-6}$alkyl, $C_{2-6}$alkenyl, $C_2$-6alkynyl, 3- to 7-membered carbocyclyl, and 3-7 membered heterocyclyl are optionally substituted with one or more $R^{20}$;

$R^{2a}$ in each occurrence is independently selected from H and $C_{1-6}$alkyl, wherein said $C_{1-6}$alkyl in each occurrence is optionally and independently substituted with one or more R20;

$R^{20}$ in each occurrence is independently selected from $C_{1-6}$alkyl, $C_{2-6}$alkenyl, $C_{2-6}$alkynyl, $C_{3-7}$cycloalkyl, 3- to 7-membered saturated heterocyclyl, halo, —CN, —C($R^{20a}$)=NR(OR$^{20a}$), —C($R^{20a}$)=N($R^{20a}$), —C(O)$R^{20a}$, —C(O)$_2R^{20a}$, —C(O)N($R^{20a}$)$_2$, —NO$_2$, —N($R^{20a}$)$_2$, —N($R^{20a}$)C(O)$R^{20a}$, —N($R^{20a}$)C(O)$_2R^{20a}$, —N($R^{20a}$)C(O)N($R^{20a}$)$_2$, —N($R^{20a}$)S(O)$_2R_{20a}$, —OR$^{20a}$, —OC(O)$R^{20a}$, —OC(O)N($R^{20a}$)$_2$, —SR$^{20a}$, —S(O)$R^{20a}$, —S(O)$_2R^{20a}$, —S(O)N($R^{20a}$)$_2$, and —S(O)$_2$N($R^{20a}$)$_2$, wherein said $C_{1-6}$alkyl, $C_{2-6}$alkenyl, $C_{2-6}$alkynyl, $C_{3-7}$cycloalkyl, and 3-7 membered saturated heterocyclyl in each occurrence are optionally and independently substituted with one or more $R^{25}$;

$R^{20a}$ in each occurrence is independently selected from H and $C_{1-6}$alkyl, wherein said $C_{1-6}$alkyl is optionally substituted with $R^{25}$;

$R^{25}$ is selected from halo and —OR$^{25a}$;

$R^{25a}$ is selected from H and $C_{1-6}$alkyl;

R is selected from $C_{1-6}$alkyl, $C_{2-6}$alkenyl, $C_{2-6}$alkynyl, $C_{3-6}$cycloalkyl, 3- to 6-membered saturated heterocyclyl, halo, —CN, —C($R^{3a}$)=NR(OR$^{3a}$), —C($R^{3a}$)=N($R^{3a}$), —C(O)$R^{3a}$, —C(O)$_2R^{3a}$, —C(O)N($R^{3a}$)$_2$, —NO$_2$, —N($R^{3a}$)$_2$, —N($R^{3a}$)C(O)$R^{3a}$, —N($R^{3a}$)C(O)$_2R^{3a}$, —N($R^{3a}$)C(O)N($R^{3a}$)$_2$, —N($R^{3a}$)S(O)$_2R^{3a}$, —OR$^{3a}$, —OC(O)$R^{3a}$, —OC(O)N($R^{3a}$)$_2$, —SR$^{3a}$, —S(O)$R^{3a}$, —S(O)$_2R^{3a}$, —S(O)N($R^{3a}$)$_2$, and —S(O)$_2$N($R^{3a}$)$_2$, wherein said $C_{1-6}$alkyl, $C_{2-6}$alkenyl, $C_{2-6}$alkynyl, $C_{3-6}$cycloalkyl, and 3- to 6-membered saturated heterocyclyl are optionally substituted with one or more $R^{30}$;

$R^{3a}$ in each occurrence is independently selected from H, $C_{1-6}$alkyl, 3- to 6-membered carbocyclyl, and 3- to 6-membered heterocyclyl, wherein said $C_{1-6}$alkyl, 3- to 6-membered carbocyclyl, and 3- to 6-membered heterocyclyl in each occurrence are optionally and independently substituted with one or more $R^{30}$;

$R^{30}$ in each occurrence is independently selected from $C_{1-6}$alkyl, $C_{2-6}$alkenyl, $C_{2-6}$alkynyl, 3- to 6-membered carbocyclyl, 3- to 6-membered heterocyclyl, halo, —CN, —C($R^{30a}$)=NR(OR$^{30a}$), —C($R^{30a}$)=N($R^{30a}$), —C(O)$R^{30a}$, —C(O)$_2R^{30a}$, —C(O)N($R^{30a}$)$_2$, —NO$_2$, —N($R^{30a}$)$_2$, —N($R^{30a}$)C(O)$R^{30a}$, —N($R^{30a}$)C(O)$_2R^{30a}$, —N($R^{30a}$)C(O)N($R^{30a}$)$_2$, —N($R^{30a}$)S(O)$_2R^{30a}$, —OR$^{30a}$, —OC(O)$R^{30a}$, —OC(O)N($R^{30a}$)$_2$, —SR$^{30a}$, —S(O)$R^{30a}$, —S(O)$_2R^{30a}$, —S(O)N($R^{30a}$)$_2$, and —S(O)$_2$N($R^{30a}$)$_2$, wherein said $C_{1-6}$alkyl, $C_{2-6}$alkenyl, $C_{2-6}$alkynyl, 3-6 membered carbocyclyl, 3- to 6-membered heterocyclyl in each occurrence are optionally and independently substituted with one or more $R^{35}$;

$R^{30a}$ in each occurrence is independently selected from H and $C_{1-4}$alkyl, wherein $C_{1-4}$alkyl is optionally substituted with one or more $R^{35}$;

$R^{35}$ in each occurrence is independently selected from halo and —OR$^{35a}$; and $R^{35a}$ in each occurrence is independently selected from H and $C_{1-6}$alkyl;

as defined and described in WO 2017/127430, the entirety of which is herein incorporated by reference.

In certain embodiments, the present invention provides a compound of Formula I, wherein IRAK is an IRAK4 inhibitor

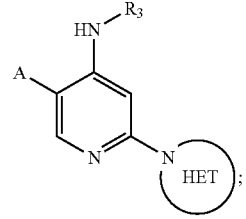

thereby forming a compound of formula I-gg-1:

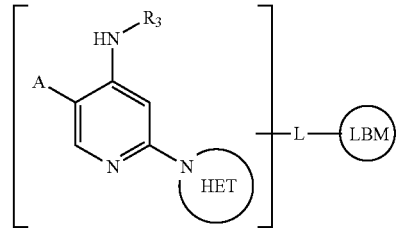

or a pharmaceutically acceptable salt thereof, wherein L and LBM are as defined above and described in embodiments herein, and wherein:

HET is a heteroaryl selected from pyrrolo[2,3-b]pyridinyl, pyrrolo[2,3-d]pyrimidinyl, pyrazolo[3,4-b]pyridinyl, pyrazolo[3,4-d]pyrimidinyl, imidazolo[4,5-b]pyridinyl, and imidazolo[4,5-d]pyrimidinyl, wherein said heteroaryl is attached to the pyridinyl group in the compound of Formula (I) by a nitrogen ring atom in said heteroaryl and wherein said heteroaryl is substituted with zero to 2 $R_b$;

A is pyrazolyl, imidazolyl, triazolyl, isoxazolyl, oxadiazolyl or dihydroisoxazolyl, each substituted with $R_a$;

$R_3$ is $C_{2-3}$ alkyl, $C_{2-3}$ fluoroalkyl, $C_{3-4}$ hydroxyalkyl, or a cyclic group selected from $C_{3-6}$ cycloalkyl, oxetanyl, tetrahydrofuranyl, tetrahydropyranyl, and pyrazolyl, wherein said cyclic group is substituted with zero to 2 substituents independently selected from F, —OH, $C_{1-2}$ alkyl, and —CH$_2$CHF$_2$;

$R_a$ is:

(i) H, F, $C_1$, —OH, —CN, $C_{1-6}$ alkyl, $C_{1-6}$ fluoroalkyl, $C_{1-4}$ cyanoalkyl, $C_{1-6}$ hydroxyalkyl, $C_{1-5}$ hydroxy-fluoroalkyl, $C_{2-4}$ alkenyl, $C_{1-6}$aminoalkyl, —(CH$_2$)$_{1-3}$NHR$_y$, —(CH$_2$)$_{1-3}$NR$_y$R$_y$, —CH$_2$CH(OH)(phenyl), —CH(CH$_2$OH)(phenyl), —CH$_2$CH(OH)CH$_2$(phenyl), —CH$_2$CH(OH)CH$_2$O(methoxyphenyl), —CH$_2$CH(NH$_2$)CH$_2$(phenyl), —(CH$_2$CH$_2$O)$_4$H, —(CH$_2$)$_{1-3}$O(C$_{1-3}$ alkyl), —CH$_2$CH(OH)CH$_2$O(C$_{1-3}$alkyl), —CH$_2$C(O)(C$_{1-3}$ alkyl), —CH$_2$C(O)NR$_y$R$_y$, —(CH$_2$)$_{1-3}$NR$_y$C(O)(C$_{1-3}$ alkyl), —CH$_2$C(O)O(C$_{1-3}$ alkyl), —C(O)NH$_2$, —CH$_2$NR$_y$C(O)NH$_2$, —(CH$_2$)$_{1-2}$NR$_y$C(O)O(C$_{1-2}$ alkyl), —(CR$_y$R$_y$)$_{1-5}$OC(O)CH$_2$NR$_y$R$_y$, —CH$_2$CH$_2$S(O)$_2$CH$_3$, —CH$_2$S(O)$_2$(C$_{1-3}$ alkyl), —CH$_2$S(O)$_2$(phenyl), or NH(aminocyclohexyl); or (ii) —(CH$_2$)$_{0-3}$R$_z$ or —(CH$_2$)$_{0-1}$C(O)R$_z$, wherein R$_z$ is $C_{3-6}$ cycloalkyl, azetidinyl, oxetanyl, tetrahydrofuranyl, tetrahydropyranyl, piperidinyl, piperazinyl, pyrrolyl, pyrrolidinonyl, morpholinyl, pyrrolidinyl, phenyl, pyrazolyl, imidazolyl, pyridinyl, pyrimidinyl, dioxopyrimidinyl, benzo[d]imidazolyl, benzo[d]thiazolyl, 1,3-dioxolanyl, or 8-azabicyclo[3.2.1]octanyl, each substituted with zero to 4 substituents independently from F, —CN, —OH, —NR$_y$R$_y$, $C_{1-3}$ alkyl, $C_{1-3}$ fluoroalkyl, $C_{1-3}$ hydroxyalkyl, —CH(phenyl)$_2$, —O(C$_{1-4}$ alkyl), —C(O)(C$_{1-4}$ alkyl), —C(O)(C$_{1-4}$ deuteroalkyl), —C(O)(C$_{1-5}$ hydroxyalkyl), —C(O)(C$_{1-3}$ fluoroalkyl), —C(O)(C$_{3-6}$cycloalkyl), —C(O)O(C$_{1-3}$ alkyl), —C(O)NR$_y$R$_y$, —C(O)(phenyl), —C(O)(pyridinyl), —C(O)CH$_2$(C$_{3-6}$ cycloalkyl), —C(O)O(C$_{1-4}$ alkyl), —NH(C$_{1-4}$ alkyl), —NH(C$_{1-3}$ fluoroalkyl), —NHC(O)CH$_3$, —NHC(O)O(C$_{1-3}$ alkyl), —NHC(O)OC(CH$_3$)$_3$, —S(O)$_2$(C$_{1-3}$ alkyl), —OS(O)$_2$(C$_{1-3}$ alkyl), methyl oxadiazolyl, and pyrimidinyl;

each R$_b$ is independently selected from H, Cl, —CN, —NH$_2$, and —C(O)NH$_2$, wherein said heteroaryl is attached to the pyridinyl group by a nitrogen atom in said heteroaryl; and each R$_y$ is independently H or C$_{1-2}$ alkyl;

as defined and described in WO 2016/210034 and US 2018/0186799, the entirety of each of which is herein incorporated by reference.

In certain embodiments, the present invention provides a compound of Formula I, wherein IRAK is an IRAK4 inhibitor

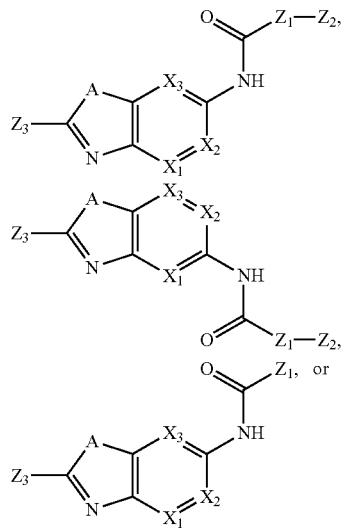

-continued

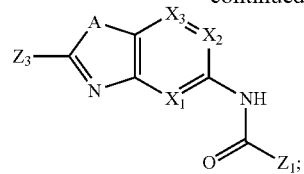

thereby forming a compound of formula I-hh-1, I-hh-2, I-hh-3, or I-hh-4 respectively:

I-hh-1

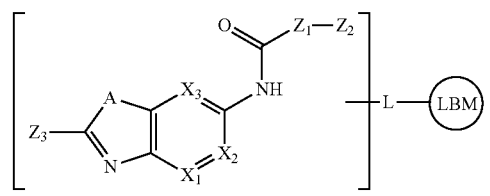

I-hh-2

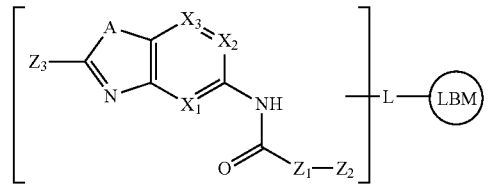

I-hh-3

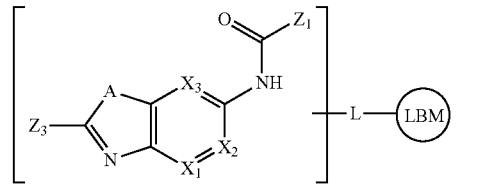

I-hh-4

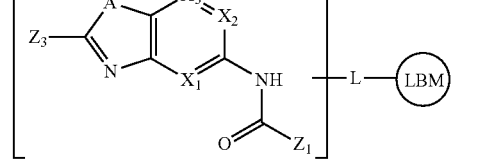

or a pharmaceutically acceptable salt thereof, wherein L and LBM are as defined above and described in embodiments herein, and wherein:

each $X_1$, $X_2$ and $X_3$ are independently CR$^2$ or N;

A is O, S, S(O) or S(O)$_2$;

$Z_1$ is optionally substituted heteroaryl, optionally substituted heterocycloalkyl, optionally substituted aryl, optionally substituted cycloalkyl, optionally substituted (heterocycloalkyl)alkyl-, optionally substituted aralkyl-, optionally substituted heteroaralkyl-, optionally substituted (cycloalkyl)alkyl-, optionally substituted aryloxy-, optionally substituted heteroaryloxy-, optionally substituted heterocycloalkyloxy-, optionally substituted cycloalkyloxy-, optionally substituted aryl-NR'—, optionally substituted heteroaryl-NR'—, optionally substituted heterocycloalkyl-NR'—, optionally substituted cycloalkyl-NR'—, optionally substituted aryl-S—, optionally substituted heteroaryl-S—, optionally substituted heterocycloalkyl-S—, optionally substituted cycloalkyl-S—, optionally substituted (cycloalkyl)alkyl-NR'—, optionally substituted aralkyl-NR'—, optionally substituted (heterocycloalkyl)alkyl-NR'—, optionally substituted heteroaralkyl-NR'—, optionally substituted (cycloalkyl)alkyl-S—, optionally substituted aralkyl-S—, optionally substituted (heterocycloalkyl)alkyl-S—, optionally substituted heteroaralkyl-S—, optionally substituted (cycloalkyl)alkyl-O—, optionally substituted aralkyl-O—, optionally substituted (heterocycloalkyl)alkyl-O—, optionally substituted heteroaralkyl-O—; e.g., wherein each optional substituent independently represents an occurrence of $R_x$;

$Z_2$ is absent or optionally substituted cycloalkyl, optionally substituted aryl, optionally substituted heterocycloalkyl, optionally substituted heteroaryl, optionally substituted aryloxy-, optionally substituted heteroaryloxy-, optionally substituted cycloalkyloxy-, optionally substituted heterocycloalkyloxy-, optionally substituted (cycloalkyl)alkyl-, optionally substituted aralkyl-, optionally substituted (heterocycloalkyl)alkyl-, optionally substituted heteroaralkyl-, optionally substituted (cycloalkyl)alkyl-NR"—, optionally substituted aralkyl-NR"—, optionally substituted (heterocycloalkyl)alkyl-NR"—, optionally substituted heteroaralkyl-NR"—, optionally substituted (cycloalkyl)alkyl-O—, optionally substituted aralkyl-O—, optionally substituted (heterocycloalkyl)alkyl-O—, optionally substituted heteroaralkyl-O—, optionally substituted (cycloalkyl)alkyl-S—, optionally substituted aralkyl-S—, optionally substituted (heterocycloalkyl)alkyl-S— or optionally substituted heteroaralkyl-S—; e.g., wherein each optional substituent independently represents an occurrence of $R_y$;

$Z_3$ is optionally substituted cycloalkyl, optionally substituted aryl, optionally substituted heterocycloalkyl, optionally substituted heteroaryl, optionally substituted aryloxy-, optionally substituted heteroaryloxy-, optionally substituted cycloalkyloxy-, optionally substituted heterocycloalkyloxy-, optionally substituted (cycloalkyl)alkyl-, optionally substituted aralkyl-, optionally substituted (heterocycloalkyl)alkyl-, optionally substituted heteroaralkyl-, optionally substituted (cycloalkyl)-NR'''—, optionally substituted aryl-NR'''—, optionally substituted heteroaryl-NR'''—, optionally substituted heterocycloalkyl-NR'''—, optionally substituted aryl-S—, optionally substituted heteroaryl-S—, optionally substituted cycloalkyl-S—, optionally substituted heterocycloalkyl-S—, optionally substituted (cycloalkyl)alkyl-NR'''—, optionally substituted aralkyl-NR'''—, optionally substituted (heterocycloalkyl)alkyl-NR'''—, optionally substituted heteroaralkyl-NR'''—, optionally substituted (cycloalkyl)alkyl-O—, optionally substituted aralkyl-O—, optionally substituted (heterocycloalkyl)alkyl-O—, optionally substituted heteroaralkyl-O—, optionally substituted (cycloalkyl)alkyl-S—, optionally substituted aralkyl-S—, optionally substituted (heterocycloalkyl)alkyl-S— or optionally substituted heteroaralkyl-S—; e.g., wherein each optional substituent independently represents an occurrence of $R_z$;

each $R^2$ is independently selected from hydrogen, alkyl, haloalkyl, halo, cyano, optionally substituted alkoxy, optionally substituted cycloalkyl, optionally substituted (cycloalkyl)alkyl-, optionally substituted cycloalkyloxy-, optionally substituted aryl, optionally substituted aralkyl-, optionally substituted heterocycloalkyl, optionally substituted heteroaryl, optionally substituted (heterocycloalkyl)alkyl-, optionally substituted heteroaralkyl-, —$NR_aR_b$, —O—$R_3$ and —S—$R_3$; e.g., wherein each optional substituent independently represents alkyl, alkoxy, halo, haloalkyl, hydroxy, hydroxyalkyl, —SH, —S(alkyl), cyano, amido, amino, carboxylate, glycinate, alaninate, oxo, aryl, cycloalkyl, heterocycloalkyl or heteroaryl;

each R', R" and R'" is independently selected from hydrogen, alkyl, hydroxy, hydroxyalkyl, acyl and cycloalkyl;

each $R_x$, $R_y$ and $R_z$ is independently selected from alkyl, alkenyl, alkynyl, halo, hydroxy, haloalkyl, hydroxyalkyl, aminoalkyl, alkoxy, —SH, —S(alkyl), cyano, amido, carboxylic acid, carboxylate, ester, thioester, alkoxycarbonyl, —C(O)NH(alkyl), oxo, cycloalkyl, cycloalkyloxy, (cycloalkyl)alkyl-, aryl, aralkyl-, heterocycloalkyl, heteroaryl, (heterocycloalkyl)alkyl-, heteroaralkyl-, —$NR_aR_b$, —O—$R_4$ or —S—$R_4$; optionally wherein the cycloalkyl, aryl, heterocycloalkyl, and heteroaryl are further substituted by one or more substituents selected from halo, haloalkyl, amino, hydroxy, alkyl, cyano, nitro, alkenyl, aminoalkyl, hydroxyalkyl and haloalkoxy;

each $R_a$ and $R_b$ is independently selected from hydrogen, alkyl, aminoalkyl, acyl, aminoacyl, halo, haloalkyl, hydroxy, haloalkoxy, hydroxyalkyl, nitro, cyano, cycloalkyl, heterocycloalkyl, aryl, heteroaryl, (cycloalkyl)alkyl-, (heterocycloalkyl)alkyl-, aralkyl-, and (heteroaryl)alkyl-; optionally wherein the cycloalkyl, heterocycloalkyl, aryl and heteroaryl are further substituted by one or more substituents selected from alkyl, halo, alkenyl, cyano, hydroxy, hydroxyalkyl, alkoxy, amino and nitro; or $R_a$ and $R_b$ are taken together along with the atoms which they are attached to form a 3 to 8 membered optionally substituted ring; and each $R_3$ and $R_4$ is independently selected from hydrogen, alkyl, aminoacyl, phosphate, phosphonate, alkylphosphate, alkoxycarbonyl, cycloalkyl, (cycloalkyl)alkyl-, aryl, heteroaryl, heterocycloalkyl, aralkyl-, heteroaralkyl and (heterocycloalkyl)alkyl-;

as defined and described in WO 2017/009806 and US 2018/0208605, the entirety of each of which is herein incorporated by reference.

In certain embodiments, the present invention provides a compound of Formula I, wherein IRAK is an IRAK4 inhibitor

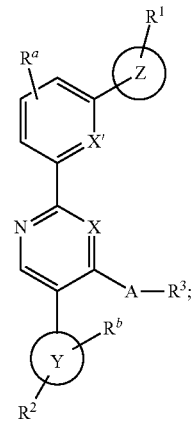

thereby forming a compound of formula I-ii-1:

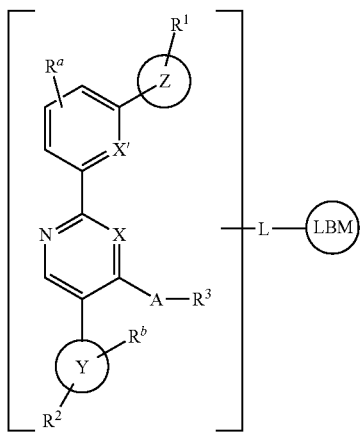

or a pharmaceutically acceptable salt thereof, wherein L and LBM are as defined above and described in embodiments herein, and wherein:

X is CR or N;
A is O, S, SO$_2$, SO, —NRC(O), —NRSO$_2$, or N(R); or A is absent;
R$^3$ is —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$; or
when A is —NRC(O), —NRSO$_2$, or N(R); then R and R$^3$, together with the atoms to which each is attached, may form a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;
X' is CR or N;
Ring Z is a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;
R$^1$ is —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;
R$^a$ is absent, —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;
Ring Y is an optionally substituted 5-6 membered monocyclic heteroaryl ring having 2-4 heteroatoms independently selected from nitrogen, oxygen, or sulfur;
R$^2$ is —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;
R$^b$ is absent, —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;
each R is independently hydrogen, C$_{1-6}$ aliphatic, C$_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or two R groups on the same atom are taken together with the atom to which they are attached to form a C$_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;

as defined and described in WO 2016/081679 and US 2016/0145252, the entirety of each of which is herein incorporated by reference.

In certain embodiments, the present invention provides a compound of Formula I, wherein IRAK is an IRAK4 inhibitor or

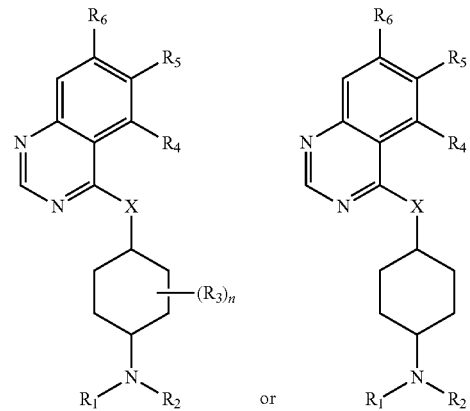

thereby forming a compound of formula I-jj-1 or I-jj-2 respectively:

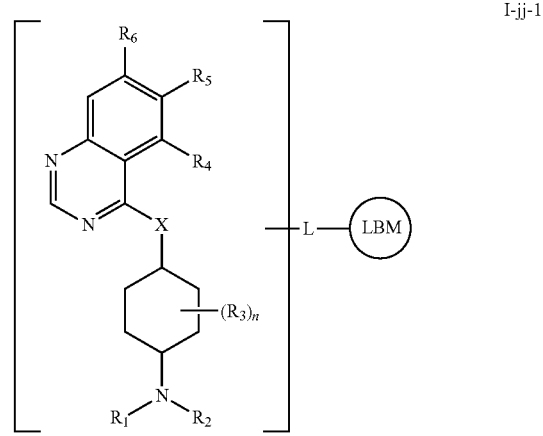

-continued

I-jj-2

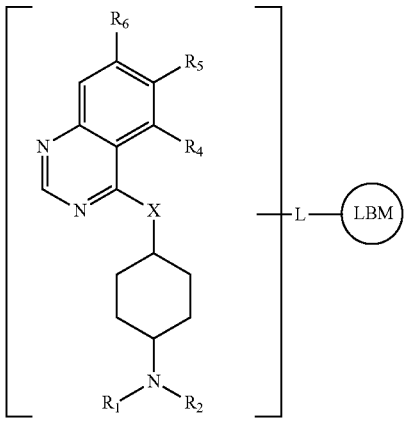

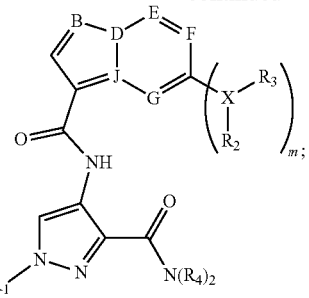

thereby forming a compound of formula I-kk-1 or I-kk-2 respectively:

I-kk-1

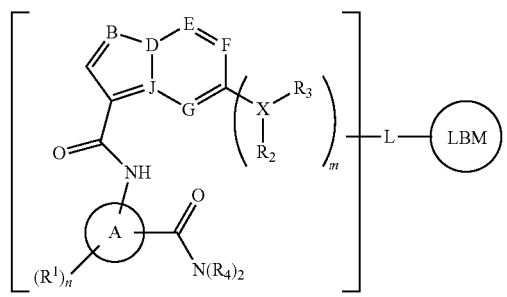

I-kk-2

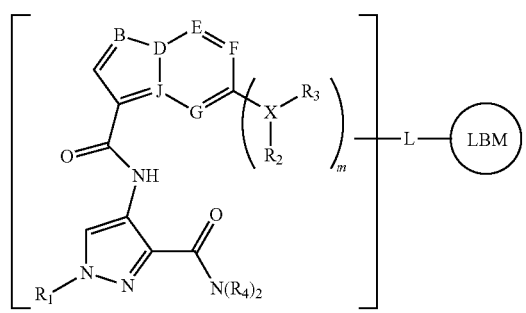

or a pharmaceutically acceptable salt thereof, wherein L and LBM are as defined above and described in embodiments herein, and wherein:
X is NH or O;
b is 0 or 1;
n is 0, 1, 2, 3 or 4;
$R_1$ and $R_2$ are independently H, $(C_1-C_4)$alkyl and heterocyclyl, or $R_1$ and $R_2$ can be taken together with the nitrogen to which they are attached to form a monocyclic or bicyclic (fused, bridged or spirocyclic) heterocycle containing 3-8 carbon atoms optionally containing, in addition to the nitrogen, one or two additional heteroatoms selected from N, O and S, said alkyl and heterocycle are optionally substituted with one or more substituents selected from $R_a$;
$R_3$ is $(C_1-C_4)$alkyl wherein two adjacent alkyl groups can join together and form a bridged moiety of 3-6 carbon atoms;
$R_4$ is absent, halo or $O_b(C_1-C_4)$alkyl;
$R_5$ is selected from $C_1-C_4$ alkyl and $C_2-C_4$ alkenyl which are optionally substituted with one or more substituents selected from $R_b$;
$R_6$ is absent, halo, or $O(C_1-C_4)$alkyl;
$R_a$ is halo, oxo, OH, $O_b(C_1-C_4)$alkyl, $CF_3$, $SO_2(C_1-C_4)$alkyl, or heterocyclyl, said heterocyclyl optionally substituted with one or more substituents independently selected from F, and $(C_1-C_4)$alkyl; and
$R_b$ is independently selected from OH, halo, $O_b(C_1-C_4)$ alkyl, and CN;
as defined and described in WO 2016/053769 and US 2017/0247388, the entirety of each of which is herein incorporated by reference.

In certain embodiments, the present invention provides a compound of Formula I,
wherein IRAK is an IRAK4 inhibitor or

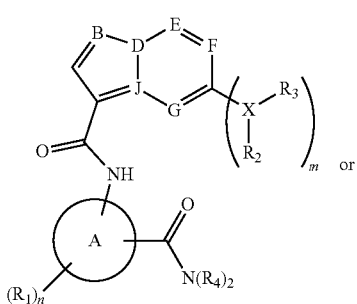

or a pharmaceutically acceptable salt thereof, wherein L and LBM are as defined above and described in embodiments herein, and wherein:
B is CH, N or S; D is CH or N; E is CH or N; F is CH or N; G is CH or N; and J is C or N, wherein when B is S then D is CH, E is N, F is CH, G is N and J is C;
X is O, S, $CH_2$ or N;
m is 0 or 1; n is 0, 1 or 2;
Ring A is pyridinyl, pyrazolyl, thiophenyl, furanyl or phenyl;
$R_1$ is independently selected from $(C_1-C_4)$alkyl, pyrimidine, piperidine and phenyl, each optionally substituted with $(C_1-C_4)$alkyl, OH, halo, $O(C_1-C_4)$alkyl, methylpiperidine, $S(O)_2R_c$, $C(O)N(R_b)_2$, or $C(O)O(C_1-C_4)$alkyl;
$R_2$ is absent or H and $R_3$ is independently selected from: $(C_1-C_4)$alkyl, pyranyl, cyclopentyl, cyclohexyl, cycloheptyl, thiopyranyl, pyrazolyl, piperidinyl, morpholinyl, piperazinyl each optionally substituted with one or more substituents independently selected from halo, OH, oxo, $N(R_b)_2$, oxopyrrolidinyl, or morpholinyl, or $R_2$ and $R_3$ can be taken together with the nitrogen to which they are attached to form piperazine or morpholine, each optionally substituted with oxo;

$R_4$ is independently H or methyl;
$R_b$ is independently selected from H and $(C_1-C_4)$alkyl; and
$R_c$ is methyl;
as defined and described in WO 2016/144844 and US 2018/0051027, the entirety of each of which is herein incorporated by reference.

In certain embodiments, the present invention provides a compound of Formula I, wherein IRAK is an IRAK4 inhibitor

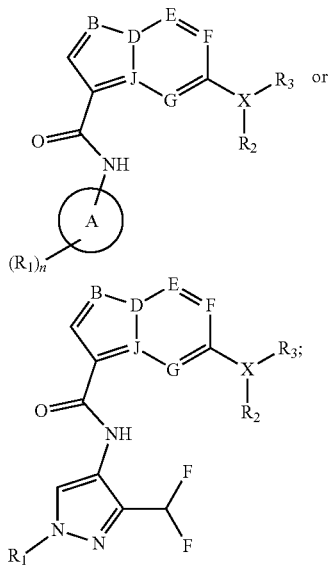

thereby forming a compound of formula I-kk'-1 or I-kk'-2 respectively:

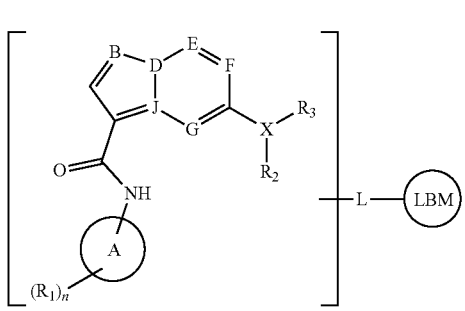

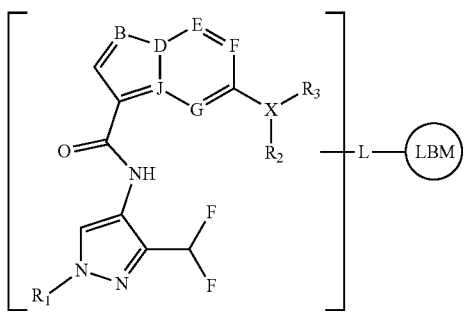

or a pharmaceutically acceptable salt thereof, wherein L and LBM are as defined above and described in embodiments herein, and wherein each of the variables A, B, D, E, F, G, J, X, $R_1$, $R_2$, $R_3$ and n is as defined and described in WO 2016/144844 and US 2018/0051027, the entirety of each of which is herein incorporated by reference. Such IRAK4 inhibitors are well known to one of ordinary skill in the art and include those described in Smith et al., *Bioorg. Med. Chem.*, 2017, 27 (12): 2721-2726 and Lim et al., *ACS Med. Chem. Lett.*, 2015, 6 (6): 683-688.

In certain embodiments, the present invention provides a compound of Formula I, wherein IRAK is an IRAK4 inhibitor

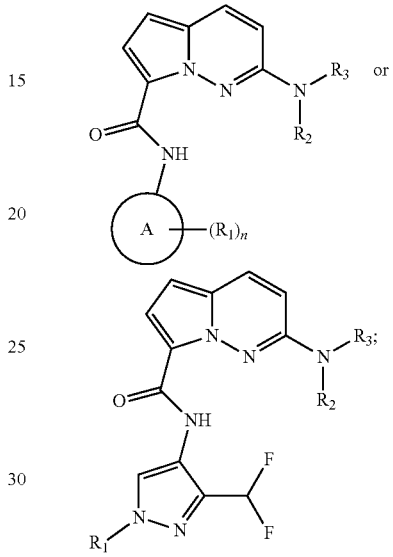

thereby forming a compound of formula I-ll-1 or I-ll'-2 respectively:

or a pharmaceutically acceptable salt thereof, wherein L and LBM are as defined above and described in embodiments herein, and wherein:

Ring A is aryl or heterocyclyl;

n is 0, 1, 2, 3 or 4;

$R_1$ is independently selected from: $(C_1\text{-}C_4)$alkyl, $(C_3\text{-}C_6)$ cycloalkyl, heterocyclyl, $CF_3$, $CHF_2$, CN, halo, said alkyl, cycloalkyl and heterocyclyl optionally substituted with halo, OH, $CH_3$, and $OCH_3$;

$R_2$ is H and $R_3$ is independently selected from: $(C_1\text{-}C_6)$alkyl, $(C_3\text{-}C_8)$cycloalkyl, and heterocyclyl each optionally substituted with one or more halo, OH, $N(R_b)_2$, or morpholinyl, or $R_2$ and $R_3$ can be taken together with the nitrogen to which they are attached to form a heterocyclyl, said heterocyclyl optionally substituted with one or more substituents selected from $R_a$;

$R_a$ is independently selected from $(C_1\text{-}C_4)$alkyl, $(C_3\text{-}C_6)$ cycloalkyl, $CF_3$, $CHF_2$, OH, halo and $NH_2$, said alkyl optionally substituted with $(C_3\text{-}C_6)$cycloalkyl and $CF_3$; and $R_b$ is independently selected from H and $(C_1\text{-}C_4)$alkyl;

as defined and described in WO 2016/144847 and US 2018/0051029, the entirety of each of which is herein incorporated by reference.

In certain embodiments, the present invention provides a compound of Formula I, wherein IRAK is an IRAK4 inhibitor

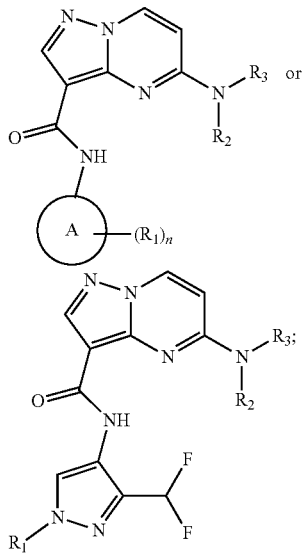

thereby forming a compound of formula I-mm-1 or I-mm'-2 respectively:

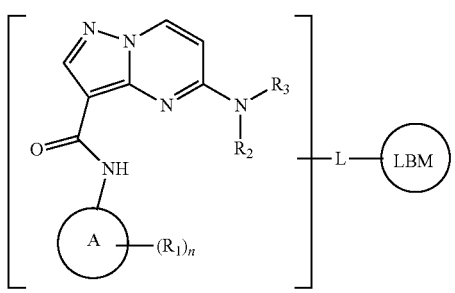

I-mm-1

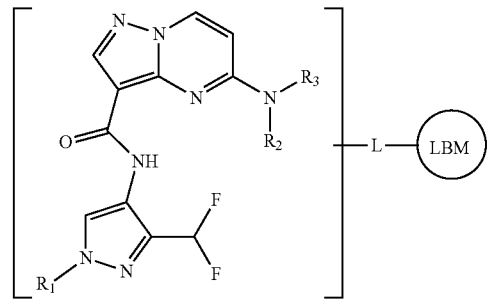

I-mm'-2 or a pharmaceutically acceptable salt thereof, wherein L and LBM are as defined above and described in embodiments herein, and wherein:

Ring A is aryl or heterocyclyl;

n is 0, 1, 2, 3 or 4;

$R_1$ is independently selected from: $(C_1\text{-}C_4)$alkyl, $(C_3\text{-}C_6)$ cycloalkyl, heterocyclyl, $CF_3$, $CHF_2$, CN and halo, said alkyl, cycloalkyl and heterocyclyl optionally substituted with halo, OH, $CH_3$, and $OCH_3$;

$R_2$ is H and $R_3$ is independently selected from: $(C_1\text{-}C_6)$alkyl, $(C_3\text{-}C_8)$cycloalkyl, and heterocyclyl each optionally substituted with one or more halo, OH, $N(R_b)_2$, or morpholinyl, or $R_2$ and $R_3$ can be taken together with the nitrogen to which they are attached to form a heterocyclyl, said heterocyclyl optionally substituted with one or more substituents selected from $R_a$;

$R_a$ is independently selected from $(C_1\text{-}C_4)$alkyl, $(C_3\text{-}C_6)$ cycloalkyl, $CF_3$, $CHF_2$, OH, halo and $NH_2$, said alkyl optionally substituted with $(C_3\text{-}C_6)$cycloalkyl or $CF_3$; and $R_b$ is independently selected from H and $(C_1\text{-}C_4)$alkyl;

as defined and described in WO 2016/144846 and US 2018/0051028, the entirety of each of which is herein incorporated by reference.

In certain embodiments, the present invention provides a compound of Formula I, wherein IRAK is an IRAK4 inhibitor

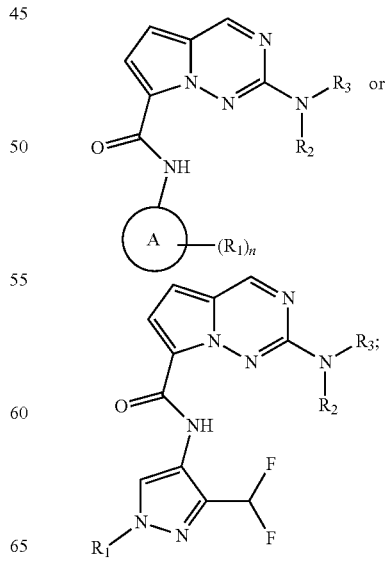

thereby forming a compound of formula I-nn-1 or I-nn'-2 respectively:

I-nn-1

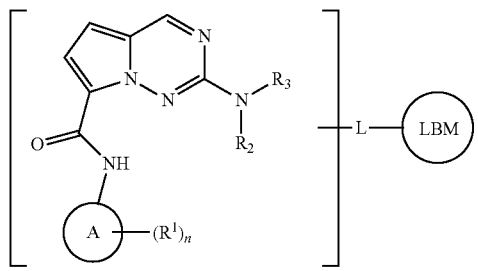

or a pharmaceutically acceptable salt thereof, wherein L and LBM are as defined above and described in embodiments herein, and wherein:

Ring A is aryl or heterocyclyl;

n is 0, 1, 2, 3 or 4;

$R_1$ is independently selected from: $(C_1-C_4)$alkyl, $(C_3-C_6)$ cycloalkyl, heterocyclyl, $CF_3$, $CHF_2$, CN, halo, said alkyl, cycloalkyl and heterocyclyl optionally substituted with halo, OH, $CH_3$, and $OCH_3$;

$R_2$ is H and $R_3$ is independently selected from: $(C_1-C_6)$alkyl, $(C_3-C_8)$cycloalkyl, and heterocyclyl each optionally substituted with one or more halo, OH, $N(R_b)_2$, or morpholinyl, or $R_2$ and $R_3$ can be taken together with the nitrogen to which they are attached to form a heterocyclyl, said heterocyclyl optionally substituted with one or more substituents selected from $R_a$;

$R_a$ is independently selected from $(C_1-C_4)$alkyl, $(C_3-C_6)$ cycloalkyl, $CF_3$, $CHF_2$, OH, halo and $NH_2$, said alkyl optionally substituted with $(C_3-C_6)$cycloalkyl and $CF_3$; and $R_b$ is independently selected from H and $(C_1-C_4)$alkyl;

as defined and described in WO 2016/144848 and US 2018/0051030, the entirety of each of which is herein incorporated by reference.

In certain embodiments, the present invention provides a compound of Formula I, wherein IRAK is an IRAK4 inhibitor I-nn'-2

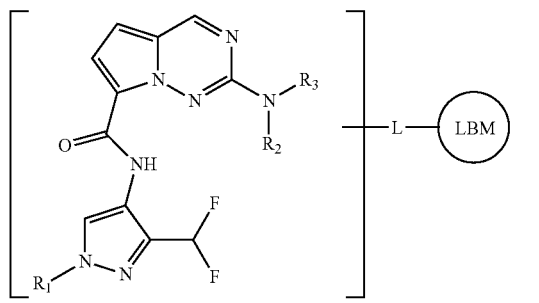

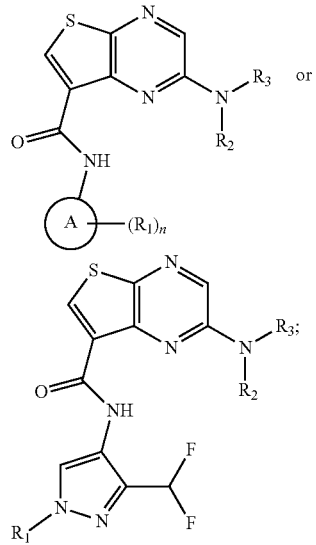

thereby forming a compound of formula I-oo-1 or I-oo'-2 respectively:

I-oo-1

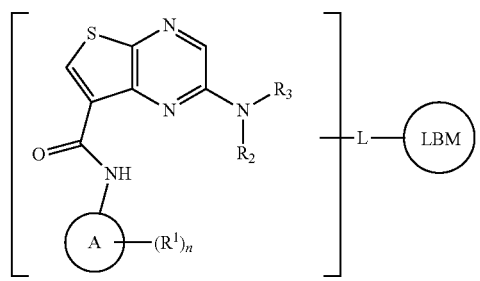

I-oo'-2

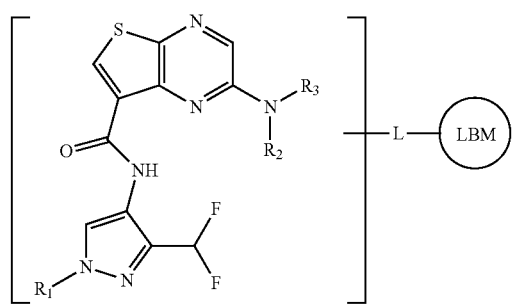

or a pharmaceutically acceptable salt thereof, wherein L and LBM are as defined above and described in embodiments herein, and wherein:

Ring A is aryl or heterocyclyl;

n is 0, 1, 2, 3 or 4;

$R_1$ is independently selected from: $(C_1-C_4)$alkyl, $(C_3-C_6)$ cycloalkyl, heterocyclyl, $CF_3$, $CHF_2$, CN, halo, said alkyl, cycloalkyl and heterocyclyl optionally substituted with halo, OH, $CH_3$, and $OCH_3$;

$R_2$ is H and $R_3$ is independently selected from: $(C_1-C_6)$alkyl, $(C_3-C_8)$cycloalkyl and heterocyclyl each optionally substituted with one or more halo, OH, $N(R_b)_2$, or morpholinyl, or $R_2$ and $R_3$ can be taken together with the nitrogen to which they are attached to form a heterocyclyl, said heterocyclyl optionally substituted with one or more substituents selected from $R_a$;

$R_a$ is independently selected from $(C_1-C_4)$alkyl, $(C_3-C_6)$cycloalkyl, $CF_3$, $CHF_2$, OH, halo and $NH_2$, said alkyl optionally substituted with $(C_3-C_6)$cycloalkyl and $CF_3$; and $R_b$ is independently selected from H and $(C_1-C_4)$alkyl;

as defined and described in WO 2016/144849 and US 2018/0051035, the entirety of each of which is herein incorporated by reference.

In certain embodiments, the present invention provides a compound of Formula I, wherein IRAK is an IRAK1 and IRAK4 inhibitor

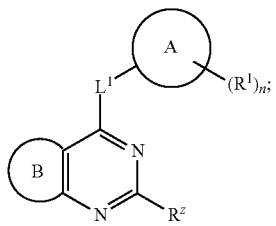

thereby forming a compound of formula I-pp-1:

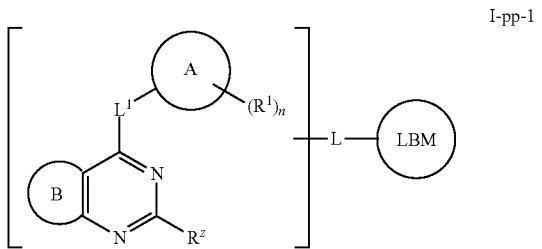

I-pp-1 or a pharmaceutically acceptable salt thereof, wherein L and LBM are as defined above and described in embodiments herein, and wherein:

Ring A is a 3-7 membered saturated or partially unsaturated carbocyclic ring or a 4-7 membered saturated or partially unsaturated heterocyclic ring having 1-3 heteroatoms independently selected from nitrogen, oxygen, or sulfur;

Ring B is

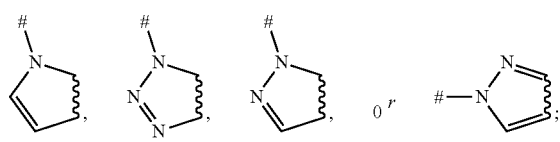

wherein ⁓ represents the portion of the ring fused to the pyrimidine ring and # is $-L^2(R^4)_p-R^x$; each $R^1$ and $R^{1'}$ is independently $-R^2$, halogen, $-CN$, $-NO_2$, $-OR$, $-SR$, $-N(R)_2$, $-S(O)_2R$, $-S(O)_2N(R)_2$, $-S(O)R$, $-C(O)R$, $-C(O)OR$, $-C(O)N(R)_2$, $-C(O)N(R)OR$, $-N(R)C(O)OR$, $-N(R)C(O)N(R)_2$, Cy, or $-N(R)S(O)_2R$; or $R^1$ is selected from one of the following formulae:

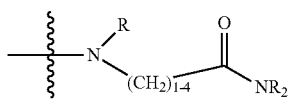

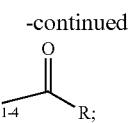

two $R^1$ groups are taken together with their intervening atoms to form an optionally substituted 4-7 membered fused, spiro-fused, or bridged bicyclic ring having 0-2 heteroatoms independently selected from nitrogen, oxygen, or sulfur;

each Cy is independently an optionally substituted ring selected from a 3-7 membered saturated or partially unsaturated carbocyclic ring or a 4-10 membered saturated or partially unsaturated heterocyclic ring having 1-3 heteroatoms independently selected from nitrogen, oxygen, or sulfur; each R is independently hydrogen, or an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur;

each $R^2$ is independently an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur;

each $R^4$ is independently halogen, $-CN$, $-NO_2$, $-OR$, $-SR$, $-N(R)_2$, $-S(O)_2R$, $-S(O)_2N(R)_2$, $-S(O)R$, $-C(O)R$, $-C(O)OR$, $-C(O)N(R)_2$, $-N(R)C(O)R$, $-N(R)C(O)N(R)_2$, $-C(O)N(R)OR$, $-N(R)C(O)OR$, $-N(R)S(O)_2N(R)_2$, $-N(R)S(O)_2R$, or an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur;

$R^x$ is hydrogen, $-R^2$, $-CN$, $-NO_2$, halogen, $-C(O)N(R)_2$, $-C(O)OR$, $-C(O)R$, $-N(R)_2$, $-NH[Ar]$, $-OR$, or $-S(O)_2N(R)_2$;

$R^z$ is hydrogen, $-R^2$, $-CN$, $-NO_2$, halogen, $-C(O)N(R)_2$, $-C(O)OR$, $-C(O)R$, $-N(R)_2$, $-NH[Ar]$, $-OR$, or $-S(O)_2N(R)_2$;

[Ar] is phenyl or a 5-6 membered heteroaromatic ring having 1-4 heteroatoms independently selected from nitrogen, oxygen, and sulfur, wherein [Ar] is substituted by m instances of $R^1$;

$L^1$ is a covalent bond or a $C_{1-6}$ bivalent hydrocarbon chain wherein one or two methylene units of the chain are optionally and independently replaced by $-N(R)-$, $-N(R)C(O)-$, $-C(O)N(R)-$, $-N(R)S(O)_2-$, $-S(O)_2N(R)-$, $-O-$, $-C(O)-$, $-OC(O)-$, $-C(O)O-$, $-S-$, $-S(O)-$ or $-S(O)_2-$;

$L^2$ is a covalent bond or a $C_{1-6}$ bivalent hydrocarbon chain wherein one or two methylene units of the chain are optionally and independently replaced by $-N(R)-$, $-N(R)C(O)-$, $-C(O)N(R)-$, $-N(R)S(O)_2-$, —S(O)$_2$N(R)—, —O—, —C(O)—, —OC(O)—, —C(O)O—, —S—, —S(O)— or —S(O)$_2$—;

m is 0-4;

n is 0-4; and p is 0-2;

as defined and described in WO 2017/004133, the entirety of each of which is herein incorporated by reference.

In certain embodiments, the present invention provides a compound of Formula I, wherein IRAK is an IRAK1 and IRAK4 inhibitor

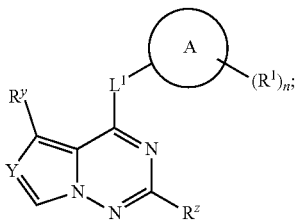

thereby forming a compound of formula I-qq-1:

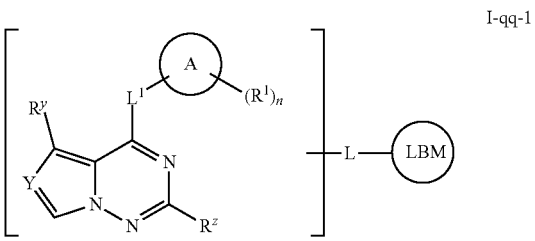

I-qq-1 or a pharmaceutically acceptable salt thereof, wherein L and LBM are as defined above and described in embodiments herein, and wherein:

Y is N or C—R$^x$;

Ring A is a 3-7 membered saturated or partially unsaturated carbocyclic ring or a 4-7 membered saturated or partially unsaturated heterocyclic ring having 1-3 heteroatoms independently selected from nitrogen, oxygen, or sulfur;

each R$^1$ and R$^v$ is independently —R$^2$, halogen, —CN, —NO$_2$, —OR, —SR, —N(R)$_2$, —S(O)$_2$R, —S(O)$_2$N(R)$_2$, —S(O)R, —C(O)R, —C(O)OR, —C(O)N(R)$_2$, —C(O)N(R)OR, —N(R)C(O)OR, —N(R)C(O)N(R)$_2$, Cy, or —N(R)S(O)$_2$R; or R$^1$ is selected from one of the following formulas:

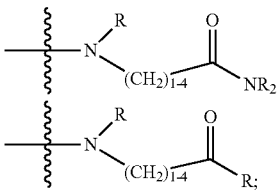

or two R$^1$ groups are taken together with their intervening atoms to form an optionally substituted 4-7 membered fused, spiro-fused, or bridged bicyclic ring having 0-2 heteroatoms independently selected from nitrogen, oxygen, or sulfur;

each Cy is independently an optionally substituted ring selected from a 3-7 membered saturated or partially unsaturated carbocyclic ring or a 4-10 membered saturated or partially unsaturated heterocyclic ring having 1-3 heteroatoms independently selected from nitrogen, oxygen, or sulfur;

each R is independently hydrogen, or an optionally substituted group selected from C$_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur, or: two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur;

each R$^2$ is independently an optionally substituted group selected from C$_{1-6}$aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur;

each of R$^x$ and R$^y$ is independently hydrogen, —R$^2$, —CN, —NO$_2$, halogen, —C(O)N(R)$_2$, —C(O)OR, —C(O)R, —N(R)$_2$, —H[Ar], —OR, or —S(O)$_2$N(R)$_2$; or R$^x$ and R$^y$ are taken together with their intervening atoms to form a 4-7 membered partially unsaturated carbocyclic ring or a partially unsaturated heterocyclic ring having 1-3 heteroatoms independently selected from nitrogen, oxygen, and sulfur;

R$^z$ is hydrogen, —R$^2$, —CN, —NO$_2$, halogen, —C(O)N(R)$_2$, —C(O)OR, —C(O)R, —N(R)$_2$, —NH[Ar], —OR, or —S(O)$_2$N(R)$_2$;

[Ar] is phenyl or a 5-6 membered heteroaromatic ring having 1-4 heteroatoms independently selected from nitrogen, oxygen, and sulfur, wherein said [Ar] is substituted by m instances of R$^r$;

L$^1$ is a covalent bond or a C$_{1-6}$ bivalent hydrocarbon chain wherein one or two methylene units of the chain are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—;

m is 0-4; and n is 0-4;

as defined and described in WO 2017/004134, the entirety of each of which is herein incorporated by reference.

In certain embodiments, the present invention provides a compound of Formula I, wherein IRAK is an IRAK inhibitor

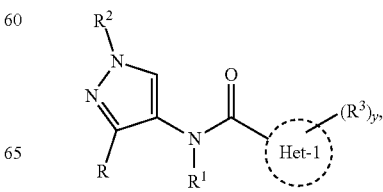

-continued

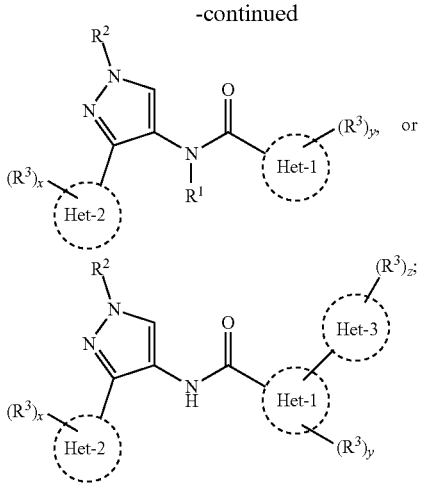

thereby forming a compound of formula I-rr-1, I-rr-2, or I-rr-3:

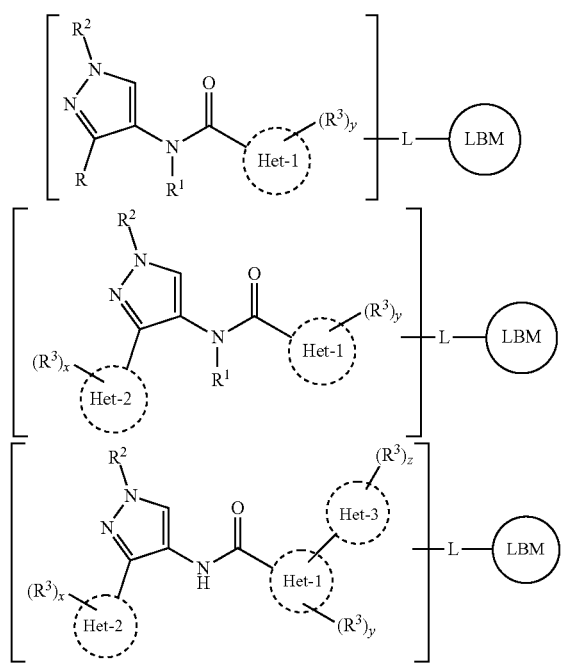

or a pharmaceutically acceptable salt thereof, wherein L and LBM are as defined above and described in embodiments herein, and wherein:
R is aliphatic, heteroaliphatic, heteroaryl, aryl, halo, amide or CN;
$R^1$ is H, aliphatic or heteroaliphatic;
or R and $R^1$, together with the atoms to which they are attached, form a heterocyclyl ring;
$R^2$ is H, aliphatic, heteroaliphatic, heterocycloaliphatic, aryl, amide, heterocyclyl or araliphatic;
each $R^3$ independently is H, aliphatic, halogen, heteroaliphatic, —O-aliphatic, heterocyclyl, aryl, araliphatic, —O-heterocyclyl, hydroxyl, nitro, cyano, carboxyl, carboxyl ester, acyl, amide, amino, sulfonyl, sulfonamide, sulfanyl, sulfinyl, haloalkyl, alkylphosphate, or alkylphosphonate;
y is from 1 to 6;

as defined and described in WO 2016/172560 and US 2016/0311839, the entirety of each of which is herein incorporated by reference.

In certain embodiments, the present invention provides a compound of Formula I, wherein IRAK is an IRAK4 inhibitor

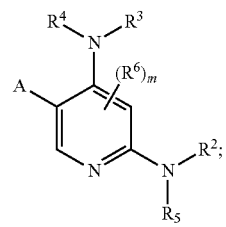

thereby forming a compound of formula I-ss-1:

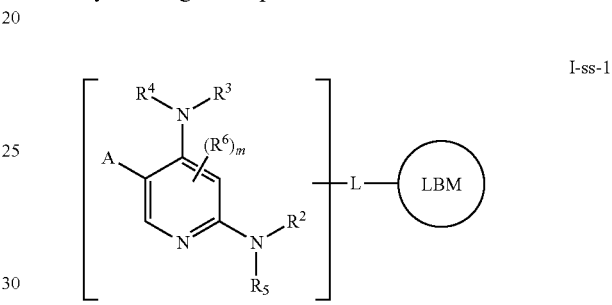

or a pharmaceutically acceptable salt thereof, wherein L and LBM are as defined above and described in embodiments herein, and wherein:

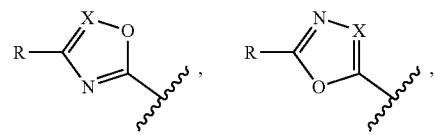

or
A is

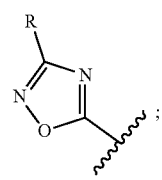

X is N or C—$R^7$;
R is hydrogen, $R^1$, halogen, cyano, nitro, —$OR^1$, —C(=O)—$R^1$, —C(=O)O—$R^1$, —C(=O)$NR^{11}$—$R^1$, —S(=O)$_2$—$R^1$, —$NR^{11}$C(=O)—$R^1$, —$NR^{11}$C(=O)$NR^{11}R^{11}$, —$NR^{11}$C(=O)O—$R^1$, —$NR^{11}$S(=O)$_2R^1$ or —$NR^{11}R^{11}$;
$R^1$ is $C_{1-6}$ alkyl substituted with 0-4 $R^{1a}$, $C_{1-6}$ haloalkyl, $C_{2-6}$ alkenyl substituted with 0-3 $R^{1a}$, $C_{2-6}$ alkynyl substituted with 0-3 $R^{1a}$, $C_{3-10}$ cycloalkyl substituted with 0-3 $R^{1a}$, $C_{6-10}$ aryl substituted with 0-3 $R^{1a}$, a 5-10 membered heterocycle containing 1-4 heteroatoms selected from N, O, and S, substituted with 0-3 $R^{1a}$, or a 5-10 membered heteroaryl containing 1-4 heteroatoms selected from N, O, and S, substituted with 0-3 $R^{1a}$;

$R^{1a}$ is hydrogen, =O, F, Cl, Br, $OCF_3$, CN, $NO_2$, $-(CH_2)_rOR^b$, $-(CH_2)_rSR^b$, $-(CH_2)_rC(O)R^b$, $-(CH_2)_rC(O)OR^b$, $-(CH_2)_rOC(O)R^b$, $-(CH_2)_rNR^{11}R^{11}$, $-(CH_2)_rC(O)NR^{11}R^{11}$, $-(CH_2)_rNR^bC(O)R^c$, $-(CH_2)_rNR^bC(O)OR^c$, $-NR^bC(O)NR^{11}R^{11}$, $-S(O)_pNR^{11}R^{11}$, $-NR^bS(O)_pR^c$, $-S(O)R^c$, $-S(O)_2R^c$, $C_{1-6}$ alkyl substituted with 0-2 $R^a$, $C_{1-6}$ haloalkyl, $-(CH_2)_r$-3-14 membered carbocycle substituted with 0-3 $R^a$, or $-(CH_2)_r$-5-7 membered heterocycle or heteroaryl, each comprising carbon atoms and 1-4 heteroatoms selected from N, O, and $S(O)_p$ substituted with 0-3 $R^a$;

$R^2$ is $C_{6-10}$ aryl substituted with 0-4 $R^{2a}$, a 5-10 membered heterocycle containing 1-4 heteroatoms selected from N, O, and S, substituted with 1-4 $R^{2a}$, or a 5-10 membered heteroaryl containing 1-4 heteroatoms selected from N, O, and S, substituted with 0-4 $R^{2a}$;

$R^{2a}$ at each occurrence is independently selected from hydrogen, =O, halo, $OCF_3$, CN, $NO_2$, $-(CH_2)_rOR^b$, $-(CH_2)_rSR^b$, $-(CH_2)_rC(O)R^b$, $-(CH_2)_rC(O)OR^b$, $-(CH_2)_rOC(O)R^b$, $-(CH_2)_rNR^{11}R^{11}$, $-(CH_2)_rC(O)NR^{11}R^{11}$, $-(CH_2)_rNR^bC(O)R^c$, $-(CH_2)_rNR^bC(O)OR^c$, $-NR^bC(O)NR^{11}R^{11}$, $-S(O)_pNR^{11}R^{11}$, $-NR^bS(O)_pR^c$, $-S(O)R^c$, $-S(O)_2R^c$, $C_{1-6}$ alkyl substituted with 0-2 $R^a$, $C_{1-6}$ haloalkyl, $-(CH_2)_r$-3-14 membered carbocycle substituted with 0-1 $R^a$, or $-(CH_2)_r$-5-7 membered heterocycle or heteroaryl, each comprising carbon atoms and 1-4 heteroatoms selected from N, O, and $S(O)_p$ substituted with 0-2 $R^a$;

$R^3$ is $C_{1-6}$ alkyl substituted with 0-3 $R^{3a}$, $C_{1-6}$ haloalkyl, $C_{2-6}$ alkenyl substituted with 0-3 $R^{3a}$, $C_{2-6}$ alkynyl substituted with 0-3 $R^{3a}$, $C_{3-10}$ cycloalkyl substituted with 0-3 $R^{3a}$, $C_{6-10}$ aryl substituted with 0-3 $R^{3a}$, a 5-10 membered heterocyclyl containing 1-4 heteroatoms selected from N, O, and S, substituted with 0-3 $R^{3a}$ or a 5-10 membered heteroaryl containing 1-4 heteroatoms selected from N, O, and S, substituted with 0-3 $R^{3a}$;

$R^{3a}$ is hydrogen, =O, F, Cl, Br, $OCF_3$, CN, $NO_2$, $-(CH_2)_rOR^b$, $-(CH_2)_rSR^b$, $-(CH_2)_rC(O)R^b$, $-(CH_2)_rC(O)OR^b$, $-(CH_2)_rOC(O)R^b$, $-(CH_2)_rNR^{11}R^{11}$, $-(CH_2)_rC(O)NR^{11}R^{11}$, $-(CH_2)_rNR^bC(O)R^c$, $-(CH_2)_rNR^bC(O)OR^c$, $-NR^bC(O)NR^{11}R^{11}$, $-S(O)_pNR^{11}R^{11}$, $-NR^bS(O)_pR^c$, $-S(O)R^c$, $-S(O)_2R^c$, $C_{1-6}$ alkyl substituted with 0-2 $R^a$, $C_{1-6}$ haloalkyl, $-(CH_2)_r$-3-14 membered carbocycle substituted with 0-1 $R^a$, or $-(CH_2)_r$-5-7 membered heterocycle or heteroaryl, each comprising carbon atoms and 1-4 heteroatoms selected from N, O, and $S(O)_p$ substituted with 0-1 $R^a$;

$R^4$ and $R^5$ are independently selected from hydrogen, $C_{1-4}$ alkyl substituted with 0-1 $R^f$, $(CH_2)$-phenyl substituted with 0-3 $R^d$, and a $-(CH_2)$-5-7 membered heterocycle comprising carbon atoms and 1-4 heteroatoms selected from N, O, and $S(O)_p$;

$R^6$ and $R^7$ are independently at each occurrence is selected from hydrogen, =O, F, Cl, Br, $OCF_3$, CN, $NO_2$, $-(CH_2)_rOR^b$, $-(CH_2)_rSR^b$, $-(CH_2)_rC(O)R^b$, $-(CH_2)_rC(O)OR^b$, $-(CH_2)_rOC(O)R^b$, $-(CH_2)_rNR^{11}R^{11}$, $-(CH_2)_rC(O)NR^{11}R^{11}$, $-(CH_2)_rNR^bC(O)R^c$, $-(CH_2)_rNR^bC(O)OR^c$, $NR^bC(O)NR^{11}R^{11}$, $-S(O)_pNR^{11}R^{11}$, $-NR^bS(O)_pR^c$, $-S(O)_2R^c$, $-S(O)_2R^c$, $C_{1-6}$ alkyl substituted with 0-2 $R^a$, $C_{1-6}$ haloalkyl, $-(CH_2)_r$-3-14 membered carbocycle substituted with 0-3 $R^a$, or $-(CH_2)_r$-5-7 membered heterocycle or heteroaryl, each comprising carbon atoms and 1-4 heteroatoms selected from N, O, and $S(O)_p$ substituted with 0-3 $R^a$, provided $R^6$ and Rare not both hydrogen;

$R^{11}$ at each occurrence is independently hydrogen, $R^e$, $C_{1-4}$ alkyl substituted with 0-1 $R^f$, $CH_2$-phenyl substituted with 0-3 $R^d$, or $-(CH_2)$-5-7 membered heterocycle comprising carbon atoms and 1-4 heteroatoms selected from N, O, and $S(O)_p$ substituted with 0-3 $R^d$; or $R^{11}$ and along with another $R^{11}$, $R^1$, or $R^2$ on the same nitrogen atom may join to form an optionally substituted heterocycle;

$R^a$ is hydrogen, F, Cl, Br, $OCF_3$, $CF_3$, $CHF_2$, CN, $NO_2$, $-(CH_2)_rOR^b$, $-(CH_2)_rSR^b$, $-(CH_2)_rC(O)R^b$, $-(CH_2)_rC(O)OR^b$, $-(CH_2)_rOC(O)R^b$, $-(CH_2)_rNR^{11}R^{11}$, $-(CH_2)_rC(O)NR^{11}R^{11}$, $-(CH_2)_rNR^bC(O)R^c$, $-(CH_2)_rNR^bC(O)OR^c$, $-NR^bC(O)NR^{11}R^{11}$, $-(O)_pNR^{11}R^{11}$, $-NR^bS(O)_pR^c$, $-S(O)R^c$, $-S(O)_2R^c$, $C_{1-6}$ alkyl substituted with 0-1 $R^f$, $C_{1-6}$ haloalkyl, $-(CH_2)_r$-3-14 membered carbocycle, or $-(CH_2)_r$-5-7 membered heterocycle or heteroaryl, each comprising carbon atoms and 1-4 heteroatoms selected from N, O, and $S(O)_p$; or two $R_a$ on adjacent or the same carbon atom form a cyclic acetal of the formula $-O-(CH_2)_n-O-$, or $-O-CF_2-O-$, wherein n is selected from 1 or 2;

$R^b$ is hydrogen, $R^e$, $C_{1-6}$ alkyl substituted with 0-2 $R^d$, $C_{1-6}$ haloalkyl, $C_{3-6}$ cycloalkyl substituted with 0-2 $R^d$, or $(CH_2)_r$-phenyl substituted with 0-3 $R^d$;

$R^c$ is $C_{1-6}$ alkyl substituted with 0-1 $R^f$, $C_{3-6}$ cycloalkyl, or $(CH_2)_r$-phenyl substituted with 0-3 $R^f$;

Rd is hydrogen, F, Cl, Br, $OCF_3$, $CF_3$, CN, $NO_2$, $-OR^e$, $-(CH_2)_rC(O)R^c$, $-NR^eR^e$, $-NR^eC(O)OR^c$, $C_{1-6}$ alkyl, or $(CH_2)_r$-phenyl substituted with 0-3 $R^f$;

$R^e$ is selected from hydrogen, $C_{1-6}$ alkyl, $C_{3-6}$ cycloalkyl, and $(CH_2)_r$-phenyl substituted with 0-3 $R^f$;

$R^f$ is hydrogen, halo, $NH_2$, OH, or $O(C_{1-6}alkyl)$;

p is 0, 1, or 2;

r is 0, 1, 2, 3, or 4; and m is 0, 1, or 2;

as defined and described in WO 2013/106612 and US 2015/0011532, the entirety of each of which is herein incorporated by reference.

In certain embodiments, the present invention provides a compound of Formula I, wherein IRAK is an IRAK4 inhibitor

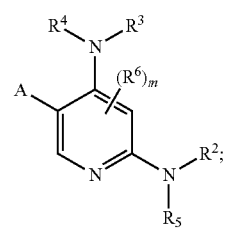

thereby forming a compound of formula I-tt-1:

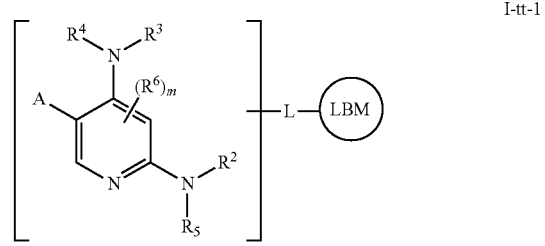

or a pharmaceutically acceptable salt thereof, wherein L and LBM are as defined above and described in embodiments herein, and wherein:

A is a triazole optionally substituted by 0-2R;

X is N or C—$R^7$;

R is hydrogen, R', halogen, cyano, nitro, —$OR^1$, —C(=O)—R, —C(=O)O—$R^1$, —C(=O)$NR^{11}$—$R^1$, —S(=O)$_2$—$R^1$, —$NR^{11}$C(=O)—R', —$NR^{11}$C(=O)$NR^{11}R^1$, —$NR^{11}$C(=O)O—R', —$NR^{11}$S(=O)$_2R^1$ or —$NR^{11}R^1$;

$R^1$ is $C_{1-6}$ alkyl substituted with 0-4 $R^{1a}$, $C_{1-6}$ haloalkyl, $C_{2-6}$ alkenyl substituted with 0-3 $R^{1a}$, $C_{2-6}$ alkynyl substituted with 0-3 $R^{1a}$, $C_{3-10}$cycloalkyl substituted with 0-3 $R^{1a}$, $C_{6-10}$ aryl substituted with 0-3 $R^{1a}$, a 5-10 membered heterocycle containing 1-4 heteroatoms selected from N, O, and S, substituted with 0-3 $R^{1a}$, or a 5-10 membered heteroaryl containing 1-4 heteroatoms selected from N, O, and S, substituted with 0-3 $R^{1a}$;

$R^{1a}$ is hydrogen, =O, F, Cl, Br, $OCF_3$, CN, $NO_2$, —$(CH_2)_r$$OR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(C)R^c$, —$S(O)_2R^c$, $C_{1-6}$ alkyl substituted with 0-2 $R^a$, $C_{1-6}$ haloalkyl, —$(CH_2)_r$-3-14 membered carbocycle substituted with 0-3 $R^a$, or —$(CH_2)_r$-5-7 membered heterocycle or heteroaryl, each comprising carbon atoms and 1-4 heteroatoms selected from N, O, and $S(O)_p$ substituted with 0-3 $R^a$;

$R^2$ is $C_{6-10}$ aryl substituted with 0-4 $R^{2a}$, a 5-10 membered heterocycle containing 1-4 heteroatoms selected from N, O, and S, substituted with 1-4 $R^{2a}$, or a 5-10 membered heteroaryl containing 1-4 heteroatoms selected from N, O, and S, substituted with 0-4 $R^{2a}$;

$R^{2a}$ at each occurrence is independently selected from hydrogen, =O, halo, $OCF_3$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl substituted with 0-2 $R^a$, $C_{1-6}$ haloalkyl, —$(CH_2)_r$-3-14 membered carbocycle substituted with 0-1 $R^a$, or —$(CH_2)_r$-5-7 membered heterocycle or heteroaryl, each comprising carbon atoms and 1-4 heteroatoms selected from N, O, and $S(O)_p$ substituted with 0-2 $R^a$;

$R^3$ is $C_{1-6}$ alkyl substituted with 0-3 $R^{3a}$, $C_{1-6}$ haloalkyl, $C_{2-6}$ alkenyl substituted with 0-3 $R^{3a}$, $C_{2-6}$ alkynyl substituted with 0-3 $R^{3a}$, $C_{3-10}$cycloalkyl substituted with 0-3 $R^{3a}$, $C_{6-10}$ aryl substituted with 0-3 $R^{3a}$, a 5-10 membered heterocyclyl containing 1-4 heteroatoms selected from N, O, and S, substituted with 0-3 $R^{3'}$ or a 5-10 membered heteroaryl containing 1-4 heteroatoms selected from N, O, and S, substituted with 0-3 $R^{3a}$;

$R^{3a}$ is hydrogen, =O, F, Cl, Br, $OCF_3$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl substituted with 0-2 $R^a$, $C_{1-6}$haloalkyl, —$(CH_2)_r$-3-14 membered carbocycle substituted with 0-1 $R^a$, or —$(CH_2)_r$-5-7 membered heterocycle or heteroaryl, each comprising carbon atoms and 1-4 heteroatoms selected from N, O, and $S(O)_p$ substituted with 0-1 $R^a$;

$R^4$ and $R^5$ are independently selected from hydrogen, $C_{1-4}$ alkyl substituted with 0-1 $R^f$, $(CH_2)$-phenyl substituted with 0-3 $R^d$, and a —$(CH_2)$-5-7 membered heterocycle comprising carbon atoms and 1-4 heteroatoms selected from N, O, and $S(O)_p$;

$R^6$ and $R^7$ are independently at each occurrence is selected from hydrogen, =O, F, Cl, Br, $OCF_3$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl substituted with 0-2 $R_a$, $C_{1-6}$haloalkyl, —$(CH_2)_r$-3-14 membered carbocycle substituted with 0-3 $R^a$, or —$(CH_2)_r$-5-7 membered heterocycle or heteroaryl, each comprising carbon atoms and 1-4 heteroatoms selected from N, O, and $S(O)_p$ substituted with 0-3 $R^a$, provided $R^6$ and $R^7$ are not both hydrogen;

$R^{11}$ at each occurrence is independently hydrogen, $R^e$, $C_{1-4}$ alkyl substituted with 0-1 $R^f$, $CH_2$-phenyl substituted with 0-3 $R^d$, or —$(CH_2)$-5-7 membered heterocycle comprising carbon atoms and 1-4 heteroatoms selected from N, O, and $S(O)_p$ substituted with 0-3 $R^d$; or $R^{11}$ and along with another $R^{11}$, $R^1$, or $R^2$ on the same nitrogen atom may join to form an optionally substituted heterocycle;

$R^a$ is hydrogen, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl substituted with 0-1 $R^f$, $C_{1-6}$ haloalkyl, —$(CH_2)_r$-3-14 membered carbocycle, or —$(CH_2)_r$-5-7 membered heterocycle or heteroaryl, each comprising carbon atoms and 1-4 heteroatoms selected from N, O, and $S(O)_p$; or two $R^a$ on adjacent or the same carbon atom form a cyclic acetal of the formula —O—$(CH_2)_n$—O—, or —O—$CF_2$—O—, wherein n is selected from 1 or 2;

$R^b$ is hydrogen, $R^e$, $C_{1-6}$ alkyl substituted with 0-2 $R^d$, $C_{1-6}$ haloalkyl, $C_{3-6}$ cycloalkyl substituted with 0-2 $R^d$, or $(CH_2)_r$-phenyl substituted with 0-3 $R^d$;

$R^c$ is $C_{1-6}$ alkyl substituted with 0-1 $R^f$, $C_{3-6}$ cycloalkyl, or $(CH_2)_r$-phenyl substituted with 0-3 $R^f$;

$R^d$ is hydrogen, F, Cl, Br, $OCF_3$, $CF_3$, CN, $NO_2$, —$OR^e$, —$(CH_2)_rC(O)R^c$, —$NR^eR^e$, —$NR^eC(O)OR^c$, $C_{1-6}$ alkyl, or $(CH_2)_r$-phenyl substituted with 0-3 $R^f$;

$R^e$ is selected from hydrogen, $C_{1-6}$ alkyl, $C_{3-6}$ cycloalkyl, and $(CH_2)_r$-phenyl substituted with 0-3 $R^f$;

$R^f$ is hydrogen, halo, $NH_2$, OH, or $O(C_{1-6}alkyl)$;

p is 0, 1, or 2;

r is 0, 1, 2, 3, or 4; and m is 0, 1, or 2;

as defined and described in WO 2013/106614 and US 2015/0045347, the entirety of each of which is herein incorporated by reference.

In certain embodiments, the present invention provides a compound of Formula I, wherein IRAK is an IRAK4 inhibitor

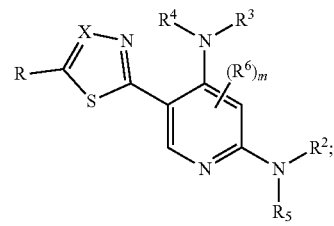

thereby forming a compound of formula I-uu-1:

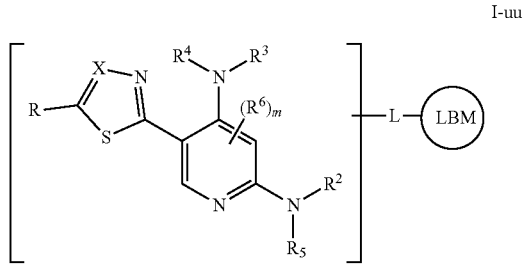

I-uu-1 or a pharmaceutically acceptable salt thereof, wherein L and LBM are as defined above and described in embodiments herein, and wherein:

X is N or C—$R^7$;

R is $R^1$, halogen, cyano, nitro, —O—$R^1$, —C(=O)—$R^1$, —C(=O)O—$R^1$, —C(=O)$NR^{11}$—$R^1$, —S(=O)$_2$—$R^1$, —$NR^{11}$C(=O)—$R^1$, —$NR^{11}$C(=O)$NR^{11}$—$R^1$, —$NR^{11}$C(=O)O—$R^1$, —$NR^{11}$S(=O)$_2$—$R^1$, or —$NR^{11}$—$R^1$;

$R^1$ is $C_{1-6}$ alkyl substituted with 0-4 $R^{1a}$, $C_{1-6}$ haloalkyl, $C_{2-6}$ alkenyl substituted with 0-3 $R^{1a}$, $C_{2-6}$ alkynyl substituted with 0-3 $R^{1a}$, $C_{3-10}$cycloalkyl substituted with 0-3 $R^{1a}$, $C_{6-10}$ aryl substituted with 0-3 $R^{1a}$, a 5-10 membered heterocycle containing 1-4 heteroatoms selected from N, O, and S, substituted with 0-3 $R^{1a}$, a 5-10 membered heteroaryl containing 1-4 heteroatoms selected from N, O, and S, substituted with 0-3 $R^{1a}$;

$R^{1a}$ is hydrogen, =O, F, Cl, Br, $OCF_3$, CN, $NO_2$, —$(CH_2)_r$$OR^b$, —$(CH_2)_r SR^b$, —$(CH_2)_r C(O)R^b$, —$(CH_2)_r C(O)OR^b$, —$(CH_2)_r OC(O)R^b$, —$(CH_2)_r NR^{11}R^{11}$, —$(CH_2)_r C(O)NR^{11}R^{11}$, —$(CH_2)_r NR^b C(O)R^c$, —$(CH_2)_r NR^b C(O)OR^c$, —$NR^b C(O)NR^{11}R^{11}$, —$S(O)_p NR^{11}R^{11}$, —$NR^b S(O)_p R^c$, —$S(O)R^c$, —$S(O)_2 R^c$, $C_{1-6}$ alkyl substituted with 0-2 $R^a$, $C_{1-6}$ haloalkyl, —$(CH_2)_r$-3-14 membered carbocycle substituted with 0-3 $R^a$, or —$(CH_2)_r$-5-7 membered heterocycle comprising carbon atoms and 1-4 heteroatoms selected from N, O, and $S(O)_p$ substituted with 0-3 $R^a$;

$R^2$ is $C_{6-10}$ aryl substituted with 0-4 $R^{2a}$, a 5-10 membered heterocycle containing 1-4 heteroatoms selected from N, O, and S, substituted with 0-4 $R^{2a}$, a 5-10 membered heteroaryl containing 1-4 heteroatoms selected from N, O, and S, substituted with 0-4 $R^{2a}$;

$R^{2a}$ at each occurrence is independently selected from hydrogen, =O, halo, $OCF_3$, CN, $NO_2$, —$(CH_2)_r OR^b$, —$(CH_2)_r SR^b$, —$(CH_2)_r C(O)R^b$, —$(CH_2)_r C(O)OR^b$, —$(CH_2)_r OC(O)R^b$, —$(CH_2)_r NR^{11}R^{11}$, —$(CH_2)_r C(O)NR^{11}R^{11}$, —$(CH_2)_r NR^b C(O)R^c$, —$(CH_2)_r NR^b C(O)OR^c$, —$NR^b C(O)NR^{11}R^{11}$, —$S(O)_p NR^{11}R^{11}$, —$NR^b S(O)_p R^c$, —$S(O)R^c$, —$S(O)_2 R^c$, $C_{1-6}$ alkyl substituted with 0-2 $R^a$, $C_{1-6}$ haloalkyl, —$(CH_2)_r$-3-14 membered carbocycle substituted with 0-1 $R^a$, or —$(CH_2)_r$-5-7 membered heterocycle or heteroaryl, each comprising carbon atoms and 1-4 heteroatoms selected from N, O, and $S(O)_p$ substituted with 0-2 $R^a$;

$R^3$ is $C_{1-6}$ alkyl substituted with 0-3 $R^{3a}$, $C_{1-6}$ haloalkyl, $C_{2-6}$ alkenyl substituted with 0-3 $R^{3a}$, $C_{2-6}$ alkynyl substituted with 0-3 $R^{3a}$, $C_{3-10}$cycloalkyl substituted with 0-3 $R^{3a}$, $C_{6-10}$ aryl substituted with 0-3 $R^{3a}$, a 5-10 membered heterocycle containing 1-4 heteroatoms selected from N, O, and S, substituted with 0-3 $R^{3a}$, or a 5-10 membered heteroaryl containing 1-4 heteroatoms selected from N, O, and S, substituted with 0-3 $R^{3a}$;

$R^{3a}$ is hydrogen, =O, F, Cl, Br, $OCF_3$, CN, $NO_2$, —$(CH_2)_r OR^b$, —$(CH_2)_r SR^b$, —$(CH_2)_r C(O)R^b$, —$(CH_2)_r C(O)OR^b$, —$(CH_2)_r OC(O)R^b$, —$(CH_2)_r NR^{11}R^{11}$, —$(CH_2)_r C(O)NR^{11}R^{11}$, —$(CH_2)_r NR^b C(O)R^c$, —$(CH_2)_r NR^b C(O)OR^c$, —$NR^b C(O)NR^{11}R^{11}$, —$S(O)_p NR^{11}R^{11}$, —$NR^b S(O)_p R^c$, —$S(O)R^c$, —$S(O)_2 R^c$, $C_{1-6}$ alkyl substituted with 0-2 $R^a$, $C_{1-6}$ haloalkyl, —$(CH_2)_r$-3-14 membered carbocycle substituted with 0-1 $R^a$, or —$(CH_2)_r$-5-7 membered heterocycle or heteroaryl, each comprising carbon atoms and 1-4 heteroatoms selected from N, O, and $S(O)_p$ substituted with 0-1 $R^a$;

$R^4$ and $R^5$ are independently selected from hydrogen, $C_{1-4}$ alkyl substituted with 0-1 $R^f$, $(CH_2)$-phenyl substituted with 0-3 $R^d$, and a —$(CH_2)$-5-7 membered heterocycle comprising carbon atoms and 1-4 heteroatoms selected from N, O, and $S(O)_p$;

$R^6$ and $R^7$ are independently at each occurrence is selected from hydrogen, =O, F, Cl, Br, $OCF_3$, CN, $NO_2$, —$(CH_2)_r OR^b$, —$(CH_2)_r SR^b$, —$(CH_2)_r C(O)R^b$, —$(CH_2)_r C(O)OR^b$, $(CH_2)_r OC(O)R^b$, —$(CH_2)_r NR^{11}R^{11}$, —$(CH_2)_r C(O)NR^{11}R^{11}$, —$(CH_2)_r NR^b C(O)R^c$, —$(CH_2)_r NR^b C(O)OR^c$, —$NR^b C(O)NR^{11}R^{11}$, —$S(O)_p NR^{11}R^{11}$, —$NR^b S(O)_p R^c$, —$S(O)R^c$, —$S(O)_2 R^c$, $C_{1-6}$ alkyl substituted with 0-2 $R^a$, $C_{1-6}$ haloalkyl, —$(CH_2)_r$-3-14 membered carbocycle substituted with 0-3 $R^a$, or —$(CH_2)_r$-5-7 membered heterocycle or heteroaryl, each comprising carbon atoms and 1-4 heteroatoms selected from N, O, and $S(O)_p$ substituted with 0-3 $R^a$, provided $R^6$ and $R^7$ are not both hydrogen;

$R^{11}$ at each occurrence is independently $R^e$, $C_{1-4}$ alkyl substituted with 0-1 $R^f$, $CH_2$-phenyl substituted with 0-3 $R^d$, or —$(CH_2)$-5-7 membered heterocycle or heteroaryl, each comprising carbon atoms and 1-4 heteroatoms selected from N, O, and $S(O)_p$ substituted with 0-3 $R^d$;

alternatively, $R^{11}$ and along with another $R^{11}$, $R^1$, or $R^2$ on the same nitrogen atom may join to form an optionally substituted azetidinyl, pyrrolidinyl, piperidinyl, morpholinyl, or 4-($C_{1-6}$ alkyl)piperazinyl;

$R^a$ is $R^d$, F, Cl, Br, $OCF_3$, $CF_3$, $CHF_2$, CN, $NO_2$, —$(CH_2)_r OR^b$, —$(CH_2)_r SR^b$, —$(CH_2)_r C(O)R^b$, —$(CH_2)_r C(O)OR^b$, —$(CH_2)_r OC(O)R^b$, —$(CH_2)_r NR^{11}R^{11}$, —$(CH_2)_r C(O)NR^{11}R^{11}$, —$(CH_2)_r NR^b C(O)R^c$, —$(CH_2)_r NR^b C(O)OR^c$, —$NR^b C(O)NR^{11}R^{11}$, —$S(O)_p NR^{11}R^{11}$, —$NR^b S(O)_p R^c$, —$S(O)_2 R^c$, —$S(O)_2 R^c$, $C_{1-6}$ alkyl substituted with 0-1 $R^f$, $C_{1-6}$ haloalkyl, —$(CH_2)_r$-3-14 membered carbocycle, or —$(CH_2)_r$-5-7 membered heterocycle comprising carbon atoms and 1-4 heteroatoms selected from N, O, and $S(O)_p$; alternatively two $R^a$ on adjacent or the same carbon atom form a cyclic acetal of the formula —O—$(CH_2)_n$—O—, or —O—$CF_2$—O—, wherein n is selected from 1 or 2;

$R^b$ is $R^c$, $C_{1-6}$ alkyl substituted with 0-2 $R^d$, $C_{1-6}$ haloalkyl, $C_{3-6}$cycloalkyl substituted with 0-2 $R^d$, or $(CH_2)_r$-phenyl substituted with 0-3 $R^d$;

$R^c$ is $C_{1-6}$ alkyl substituted with 0-1 $R^f$, $C_{3-6}$ cycloalkyl, or $(CH_2)_r$-phenyl substituted with 0-3 $R^f$;

$R^d$ is hydrogen, F, Cl, Br, $OCF_3$, $CF_3$, CN, $NO_2$, —$OR^e$, —$(CH_2)_r C(O)R^c$, —$NR^e R^e$, —$NR^e C(O)OR^c$, $C_{1-6}$ alkyl, or $(CH_2)_r$-phenyl substituted with 0-3 $R^f$;

$R^e$ is selected from hydrogen, $C_{1-6}$ alkyl, $C_{3-6}$ cycloalkyl, and $(CH_2)_r$-phenyl substituted with 0-3 $R^f$;

$R^f$ is hydrogen, halo, $NH_2$, OH, or $O(C_{1-6}$alkyl);

p is 0, 1, or 2;

r is 0, 1, 2, 3, or 4; and m is 0, 1, or 2;

as defined and described in WO 2013/106641 and US 2015/0018344, the entirety of each of which is herein incorporated by reference.

In certain embodiments, the present invention provides a compound of Formula I, wherein IRAK is an IRAK4 inhibitor

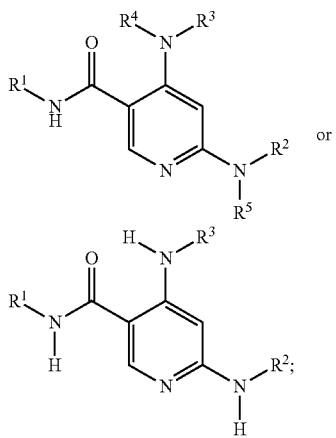

thereby forming a compound of formula I-vv-1 or I-vv-2:

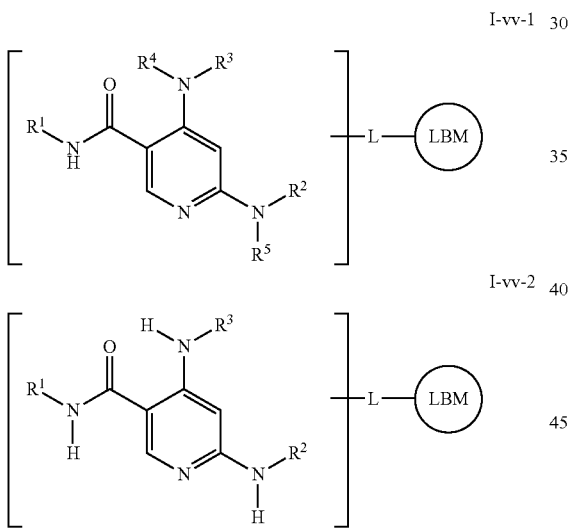

or a pharmaceutically acceptable salt thereof, wherein L and LBM are as defined above and described in embodiments herein, and wherein:

$R^1$ is:
(a) $C_{2-3}$ hydroxyalkyl substituted with zero to 4 $R^{1a}$ wherein $R^{1a}$ is independently selected from F, Cl, —OH, —CHF$_2$, —CN, —CF$_3$, —OCH$_3$, and cyclopropyl;
(b) $C_{1-3}$alkyl substituted with —O($C_{1-3}$alkyl) and zero to 4 $R^{1a}$ wherein $R^{1a}$ is independently selected from F, Cl, —OH, —CHF$_2$, —CN, —CF$_3$, and cyclopropyl;
(c) $C_{4-8}$ alkyl substituted with zero to 7 $R^{1a}$ wherein $R^{1a}$ is independently selected from F, Cl, —OH, —CHF$_2$, —CF$_3$, —CN—OCH$_3$, cyclopropyl, and —OP(O)(OH)$_2$;
(d) —(CH$_2$)$_{2-4}$NHC(O)(C$_{1-6}$ alkyl), —(CH$_2$)$_2$CH(CH$_3$)NHC(O)(C$_{1-6}$alkyl), —(CH$_2$)$_2$CH(CH$_3$)NHC(O)(CH$_2$)$_{0-1}$NH(C$_{1-6}$ alkyl), or —(CH$_2$)$_2$CH(CH$_3$)NHC(O)(CH$_2$)$_{0-1}$N(C$_{1-4}$ alkyl)$_2$;
(e) cyclohexyl substituted with zero to 2 substituents independently selected from —OH, —OCH$_3$, C$_{1-6}$ alkyl, C$_{1-6}$hydroxyalkyl, —C(O)NH$_2$, —C(O)NH(C$_{1-3}$ alkyl), —C(O)NH(C$_{1-6}$hydroxyalkyl), —C(O)NH(C$_{3-6}$ cycloalkyl), —C(O)NH(C$_{3-6}$ fluoro cycloalkyl), —NHC(O)(C$_{1-3}$ alkyl), —NHC(O)O(C$_{1-3}$ alkyl), —NHS(O)$_2$CH$_3$, —S(O)$_2$NH$_2$, —S(O)$_2$(C$_{1-3}$ alkyl), —S(C$_{1-3}$ alkyl), thiazolyl, methyl pyrazolyl, and C$_{1-3}$ alkyl substituted with —OH and cyclopropyl;
(f) —(CH$_2$)$_2$(phenyl) wherein said phenyl is substituted with —C(O)NH$_2$, —C(O)NH(C$_{1-3}$ alkyl), or —S(O)$_2$NH$_2$; or
(g) piperidinyl substituted with —C(O)(C$_{1-3}$ alkyl);

$R^2$ is phenyl, pyridinyl, pyridazinyl, pyrimidinyl, pyrazolyl, thiazolyl, or triazolyl, each substituted with zero to 2 substituents independently selected from F, Cl, —OH, —CN, C$_{1-3}$ alkyl, CH$_2$C(O)OCH$_3$, —O(C$_{1-3}$alkyl), —NH$_2$, —NH(C$_{1-3}$ alkyl), —NH(cyclopropyl), —C(O)NH$_2$, —NHC(O)(C$_{1-3}$ alkyl), —NH(tetrahydropyranyl), hydroxypyrrolidinyl, =O, —O(piperidinyl), and pyridinyl; and $R^3$ is:
(a) $C_{1-6}$ alkyl substituted with zero to 4 substituents independently selected from F, OH, —CH$_3$, —CF$_3$, and C$_{3-6}$cycloalkyl;
(b) $C_{3-6}$ cycloalkyl substituted with zero to 2 substituents independently selected from F, —OH, C$_{1-3}$ hydroxyalkyl, —CH$_3$, —CF$_2$H, —NH$_2$, and —C(O)OCH$_2$CH$_3$;
(c) oxetanyl, tetrahydropyranyl, or fluoro tetrahydropyranyl;
(d) phenyl substituted with zero to 2 substituents independently selected from —OH, —CN, —O(C$_{1-3}$ alkyl), C$_{1-3}$ hydroxyalkyl, —C(O)NH$_2$, —S(O)$_2$NH$_2$, —NHS(O)$_2$(C$_{1-3}$ alkyl), pyrazolyl, imidazolyl, and methyl tetrazolyl; or

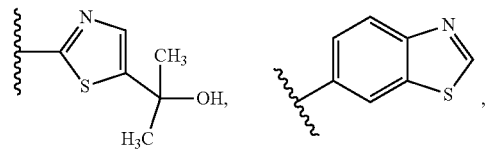

(e)

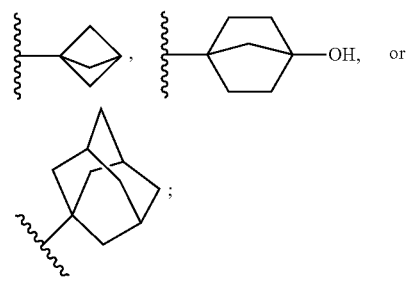

as defined and described in WO 2014/074675 and US 2015/0284382, the entirety of each of which is herein incorporated by reference.

In certain embodiments, the present invention provides a compound of Formula I, wherein IRAK is an IRAK4 inhibitor

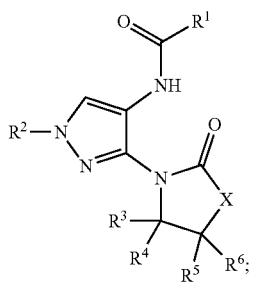

thereby forming a compound of formula I-xx-1

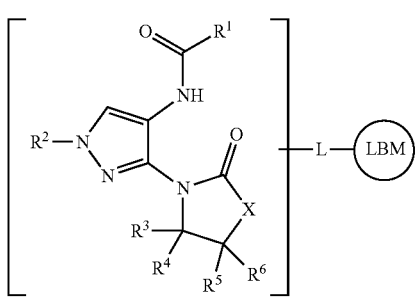

I-xx-1 or a pharmaceutically acceptable salt thereof, wherein L and LBM are as defined above and described in embodiments herein, and wherein:

$R^1$ is an optionally substituted aromatic heterocyclic group or an optionally substituted $C_{6-14}$ aryl group;

$R^2$ is a hydrogen atom or a substituent;

$R^3$ and $R^4$ are independently a hydrogen atom or a substituent, or $R^3$ and $R^4$ in combination optionally form an optionally substituted ring;

$R^5$ and $R^6$ are independently a hydrogen atom or a substituent, or $R^5$ and $R^6$ in combination optionally form an optionally substituted ring;

X is $CR^7R^8$, $NR^9$, O or S;

$R^7$ and $R^8$ are independently a hydrogen atom or a substituent, or $R^7$ and $R^8$ in combination optionally form an optionally substituted ring; and $R^9$ is a hydrogen atom or a substituent;

as defined and described in WO 2015/068856 and US 2015/0133451, the entirety of each of which is herein incorporated by reference.

In certain embodiments, the present invention provides a compound of Formula I, wherein LBM is an E3 ubiquitin ligase (IAP) binding moiety

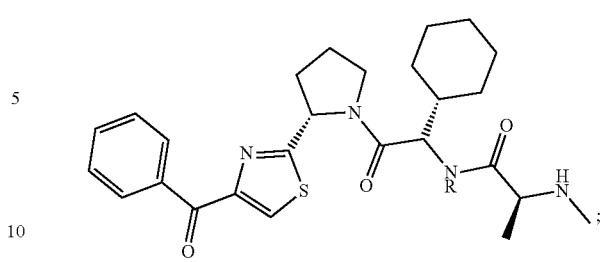

thereby forming a compound of formula I-yy-1

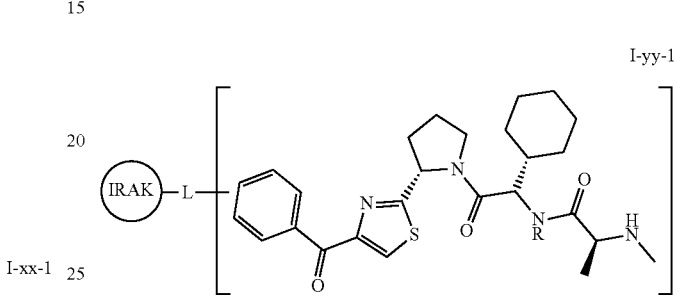

I-yy-1 or a pharmaceutically acceptable salt thereof, wherein L and IRAK are as defined above and described in embodiments herein, and wherein the variable Ris as defined and described in Ohoka, N. et al. (2017). In Vivo Knockdown of Pathogenic Proteins via Specific and Nongenetic Inhibitor of Apoptosis Protein (IAP)-dependent Protein Erasers (SNIP-ERs). *Journal of Biological Chemistry*, 292 (11), 4556-4570, the entirety of each of which is herein incorporated by reference.

In certain embodiments, the present invention provides a compound of Formula I, wherein IRAK is an IRAK4 inhibitor

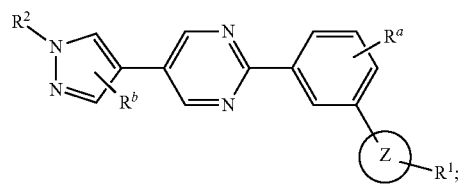

thereby forming a compound of formula I-zz-1

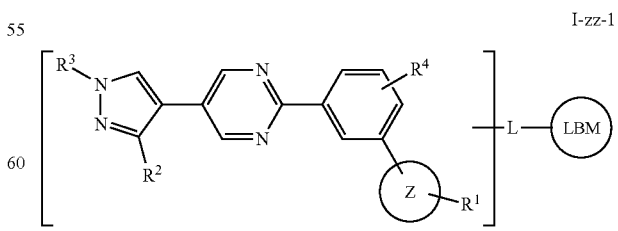

I-zz-1 or a pharmaceutically acceptable salt thereof, wherein L and LBM are as defined above and described in embodiments herein, and wherein:

R¹ denotes absent, A or Q-Het,
Z is

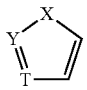

wherein
X denotes O, S or N,
Y denotes C or N,
T denotes C or N, or
Z denotes a pyridine or a pyridazine group,
$R^a$ is absent, $OR^3$, $CF_3$, Hal, or $NO_2$,
$R^b$ is absent, A, or COHet,
R² denotes H, Het, Q-Het, Cyc, A or OA,
each Het is independently a 4-9 membered monocyclic ring or a fused, spiro or bridged bicyclic ring, which is saturated, unsaturated, or aromatic, which contains 1 to 3 heteroatoms independently selected from N, O, and S, and a group CO, SO or $SO_2$, and wherein 1 or 2 H atoms may be replaced by A, OA, COA, CN, Hal, $NO_2$, $OR^3$, SOA and/or $SO_2A$,
Cyc denotes a 4-8 saturated carbocyclic ring optionally containing a group SO, $SO_2$, or CO, and optionally substituted once or twice by a group selected from $CO(NR^3)_2$, COHet, $OR^3$, $Het^1$, A, $CH_2Het^1$, $NH_2$, NHCOA, $OCH_2Cyc^1$, $SO_2A$ and -SA(=NH)(=O),
each Q is independently a linear or branched alkylene, having 1 to 6 carbon atoms wherein 1-5H atoms may be replaced by a group independently selected from $OR^3$, Hal, and $N(R^3)_2$, and wherein 1 or 2 $CH_2$ groups may be replaced by a group independently selected from CO, SO, $SO_2$ and $NR^3$, or Q denotes a 4-8-membered bivalent heterocyclic ring, which is saturated, unsaturated or aromatic and which contains 1 to 3 heteroatoms independently selected from N, O and S,
each A is independently a linear or branched alkyl having 1 to 10 carbon atoms wherein 1 to 7H atoms may be replaced by a group independently selected from —$OR^3$, Hal, $NHSO_2A$, $SO_2A$, SOA, and $N(R^3)_2$, and wherein 1, 2 or 3 non-adjacent —$CH_2$— groups may be replaced by a group independently selected from —CO—, $NR^3$ and —O—,
each Hal is independently F, Cl, Br or I,
each $R^3$ is independently H or $C_1$-$C_6$-alkyl wherein 1H atom may be replaced by a group selected from OH, O—$C_1$-$C_6$-alkyl, and Hal,
each $Het^1$ is independently a five- or six membered saturated monocyclic heterocycle which contains 1-3 N- and/or O-atoms, which optionally is monosubstituted by A,
$Cyc^1$ denotes cycloalkyl with 3-7 atoms; as defined and described in WO 2014/008992 and US 2015/0141396, the entirety of each of which is herein incorporated by reference.

In certain embodiments, the present invention provides a compound of Formula I, wherein IRAK is an IRAK4 inhibitor

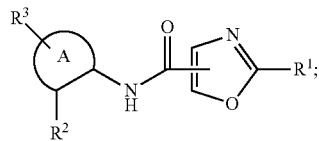

thereby forming a compound of formula I-aaa-1

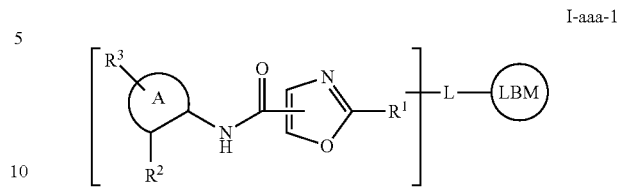

or a pharmaceutically acceptable salt thereof, wherein L and LBM are as defined above and described in embodiments herein, and wherein:

Ring A is a monocyclic heteroaryl;

R¹ is one to three optionally substituted with $R^{10}$ monocyclic or bicyclic heteroaryl;

R² is, —C(O)NH₂, —C(O)NH—R⁰, —C(O)NH—R⁰—OH, —C(O)NH—R⁰⁰—OR⁰, —C(O)N(R⁰)₂, —C(O)NH—cycloalkyl, —C(O)NH-heterocycloalkyl, —C(O)NH-(pyrazolyl optionally substituted with R⁰), —C(O)—R⁰, —C(O)-cycloalkyl, —S(O)₂NH₂, —S(O)₂NH—R, —S(O)₂NH-cycloalkyl, —R⁰⁰—OH, —R⁰⁰—OR⁰, —R⁰⁰-(morpholin-4-yl) phenyl, oxadiazolyl, or tetrazolyl optionally substituted with R⁰, wherein oxadiazolyl in R² is, R⁰, R⁰⁰—OH or may be substituted with R⁰—OR⁰;

R³ is, H, R⁰, halogeno-lower alkyl, cycloalkyl, heterocycloalkyl, phenyl, pyridyl, pyrimidinyl, pyrazinyl, —C(O)N(R⁰)₂, —R⁰⁰-cycloalkyl, —R⁰⁰-heterocycloalkyl, —R⁰⁰-phenyl, —R⁰⁰—OH or a —R⁰⁰—OR⁰, wherein the cycloalkyl in R³, heterocycloalkyl, phenyl and pyridyl, R⁰, halogen, —C(O)OR⁰, —C(O)—R⁰, —OH, —OR⁰, —S(O)₂—R, —O-halogeno-lower alkyl, —OR⁰⁰-(morpholin-4-yl), —R⁰—OH, —R⁰⁰—OR, morpholin-4-yl or, —R⁰⁰-(morpholin-4-yl) may be substituted;

R¹⁰ may be the same or different from each other, R⁰, halogen, halogeno-lower alkyl, cycloalkyl, —OR⁰, optionally substituted amino, —O-halogeno-lower alkyl, —R⁰—OH, —R⁰⁰—OR⁰ or, —R⁰⁰— is optionally amino substituted, R⁰ is the same or different from each other, lower alkyl, R⁰⁰ are identical or different from each other, it is a lower alkylene;

as defined and described in WO 2011/043371, the entirety of which is herein incorporated by reference.

In some embodiments, the compound of formula I-aaa-1 above is provided as a compound of formula I-aaa-2, I-aaa-3, or I-aaa-4:

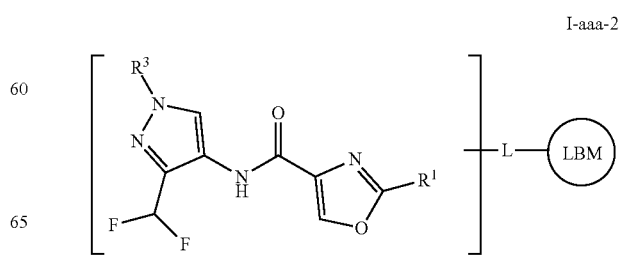

-continued

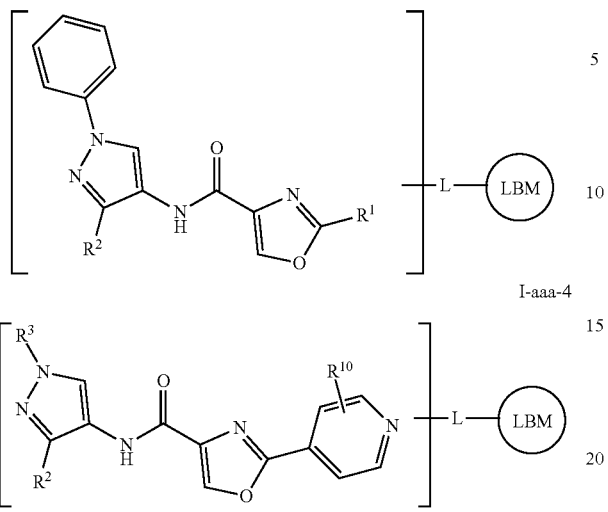

or a pharmaceutically acceptable salt thereof, wherein: each of LBM, L, $R^1$, $R^2$, $R^3$, and $R^{10}$ is as defined above.

In some embodiments, In certain embodiments, the present invention provides a compound of Formula I, wherein IRAK is an IRAK4 inhibitor

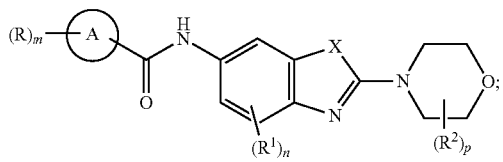

thereby forming a compound of formula I-bbb-1

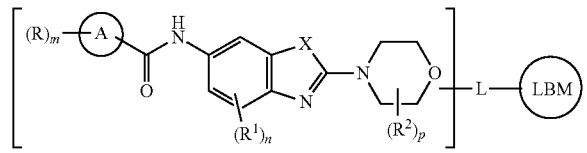

or a pharmaceutically acceptable salt thereof, wherein L and LBM are as defined above and described in embodiments herein, and wherein:

X is selected from O, S, and NH;
A is selected from aryl or heteroaryl;
R at each occurrence is independently selected from hydrogen, cyano, halo, hydroxy, —$NO_2$, —$NR^3R^4$, optionally substituted alkyl, optionally substituted aryl, optionally substituted cycloalkyl, optionally substituted heterocycloalkyl or optionally substituted heteroaryl;
wherein the optional substituent, in each occurrence, is independently selected from halo, alkyl, haloalkyl, cyano, —$NR^5R^6$ or —$COOR^7$;
$R^1$ at each occurrence is independently selected from hydrogen, halogen, alkyl, aryl, heterocycloalkyl, heterocycloalkylalkyl, heteroaryl, Y-arylalkyl or —Y-cycloalkyl; wherein cycloalkyl, aryl, heterocycloalkyl, heterocycloalkylalkyl, heteroaryl and arylalkyl can be optionally substituted with hydroxy, alkyl, haloalkyl, cyano or halo;
Y is selected from direct bond, O, —C(O)— or $NR^7$;
$R^2$ at each occurrence is independently selected from hydrogen, carboxy, cyano, hydroxy, hydroxyalkyl, alkyl, aryl, heteroaryl, —$SO^2R^5$ or oxo;
$R^3$ and $R^4$ are independently selected from hydrogen, hydroxyalkyl, aminoalkyl, optionally substituted alkyl, optionally substituted heterocyclyl, optionally substituted aryl; wherein the optional substituent, in each occurrence, is independently selected from halo, haloalkyl or —$COOR^7$;
$R^5$ and $R^6$ are independently selected from hydrogen, alkyl, $COR^7$ or —$COOR^7$;
$R^7$ at each occurrence is independently selected from hydrogen or alkyl; and
m, n and p are selected from 1, 2 or 3;
as defined and described in WO 2013/042137, the entirety of which is herein incorporated by reference.

In certain embodiments, the present invention provides a compound of Formula I, wherein IRAK is an IRAK4 inhibitor

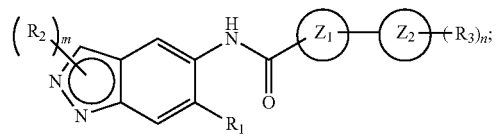

thereby forming a compound of formula I-ccc-1

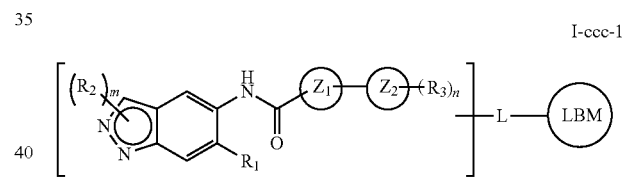

or a pharmaceutically acceptable salt thereof, wherein L and LBM are as defined above and described in embodiments herein, and wherein:

Ring $Z_1$ is an optionally substituted heteroaryl;
Ring $Z_2$ is an optionally substituted heterocycloalkyl, optionally substituted heteroaryl or a direct bond;
$R_1$ is alkyl, cyano, —$NR_aR_b$ or optionally substituted groups selected from cycloalkyl, aryl or heterocyclyl; wherein the substituent, at each occurrence, independently is alkyl, alkoxy, halogen, hydroxyl, hydroxyalkyl, amino, aminoalkyl, nitro, cyano, haloalkyl, haloalkoxy, —OCO—$CH_2$—O-alkyl, —OP(O)(O-alkyl)$_2$ or —$CH_2$—OP(O)(O-alkyl)$_2$;
$R_2$, at each occurrence, independently is an optionally substituted group selected from alkyl or cycloalkyl; wherein the substituent, at each occurrence, is independently halogen, alkoxy, hydroxyl, hydroxyalkyl, haloalkyl or haloalkoxy;
$R_3$, at each occurrence, independently is hydrogen, halogen, alkyl, haloalkyl, haloalkoxy, alkoxy, —$NR_aR_b$, hydroxyl or hydroxyalkyl;
$R_a$ is hydrogen or alkyl;
$R_b$ is hydrogen, alkyl, acyl, hydroxyalkyl, —$SO_2$-alkyl or optionally substituted cycloalkyl;
m and n are independently 1 or 2;

as defined and described in WO 2015/104662 and US 2016/0326151, the entirety of each of which is herein incorporated by reference.

In certain embodiments, the present invention provides a compound of Formula I, wherein IRAK is an IRAK4 inhibitor

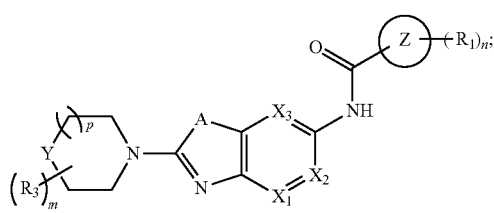

thereby forming a compound of formula I-ddd-1

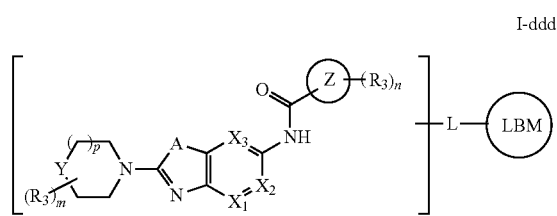

or a pharmaceutically acceptable salt thereof, wherein L and LBM are as defined above and described in embodiments herein, and wherein:
$X_1$ and $X_3$ independently are CH or N; $X_2$ is $CR_2$ or N; provided one and not more than one of $X_1$, $X_2$ or $X_3$ is N;
A is O or S;
Y is —$CH_2$— or O;
Ring Z is aryl or heterocyclyl;
$R_1$, at each occurrence, is independently halo or optionally substituted heterocyclyl; wherein the substituent is alkyl, alkoxy, aminoalkyl, halo, hydroxyl, hydroxyalkyl or —$NR_aR_b$;
$R_2$ is hydrogen, optionally substituted cycloalkyl, optionally substituted aryl, optionally substituted heterocyclyl or —$NR_aR_b$; wherein the substituent is alkyl, amino, halo or hydroxyl;
$R_3$, at each occurrence, is alkyl or hydroxyl;
$R_a$ and $R_b$ are independently hydrogen, alkyl, acyl or heterocyclyl;
m and n are independently 0, 1 or 2;
p is 0 or 1;
as defined and described in WO 2015/104688 and US 2016/0340366, the entirety of each of which is herein incorporated by reference.

In certain embodiments, the present invention provides a compound of Formula I, wherein IRAK is an IRAK4 inhibitor

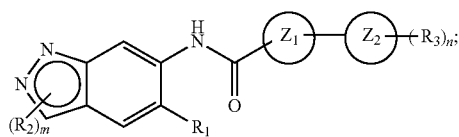

thereby forming a compound of formula I-eee-1

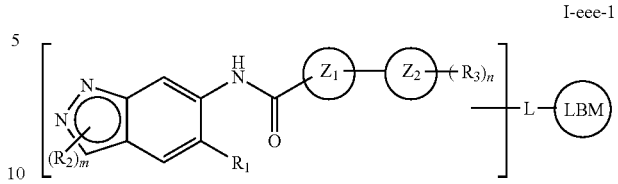

or a pharmaceutically acceptable salt thereof, wherein L and LBM are as defined above and described in embodiments herein, and wherein:
$Z_1$ is optionally substituted cycloalkyl, optionally substituted aryl, optionally substituted heterocyclyl or is absent;
$Z_2$ is optionally substituted cycloalkyl, aryl or heterocyclyl;
$R_1$ is hydrogen, optionally substituted alkyl, amino, halogen, cyano, optionally substituted cycloalkyl, optionally substituted aryl, optionally substituted heterocyclyl, optionally substituted arylalkyl or optionally substituted heterocyclylalkyl;
$R_2$ at each occurrence is hydrogen, halogen, amino, optionally substituted alkyl, optionally substituted cycloalkyl, optionally substituted aryl, optionally substituted heterocyclyl, optionally substituted arylalkyl or optionally substituted heterocyclylalkyl;
$R_3$ at each occurrence is hydroxy, halogen, optionally substituted alkyl, optionally substituted alkoxy, optionally substituted cycloalkyl or —$NR_aR_b$;
$R_a$ and $R_b$, independently for each occurrence, are hydrogen, optionally substituted alkyl, optionally substituted acyl, optionally substituted cycloalkyl, optionally substituted aryl, optionally substituted heterocyclyl, optionally substituted arylalkyl or optionally substituted heterocyclylalkyl;
m at each occurrence, is 0, 1 or 2; and
n at each occurrence, is 0, 1, or 2;
as defined and described in WO 2015/193846 and US 2017/0152263, the entirety of each of which is herein incorporated by reference.

In certain embodiments, the present invention provides a compound of Formula I, wherein IRAK is an IRAK4 inhibitor

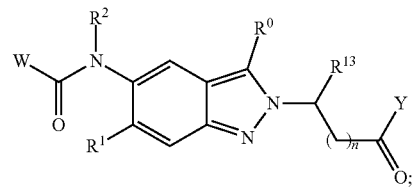

thereby forming a compound of formula I-fff-1

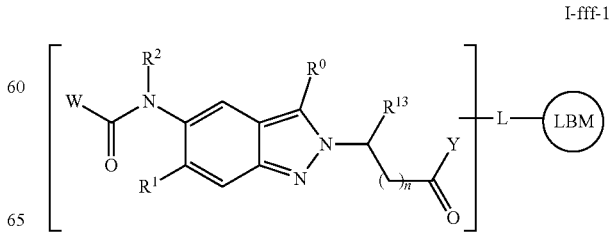

or a pharmaceutically acceptable salt thereof, wherein L and LBM are as defined above and described in embodiments herein, and wherein $R^0$ represents hydrogen or $C_1$-$C_4$-alkyl, where the $C_1$-$C_4$-alkyl radical may optionally be mono- or polysubstituted by identical or different radicals from the group consisting of hydroxy and halogen;

$R^1$ represents hydrogen, halogen, cyano, C(=O)OH, C(=O)OR$^a$, C(=O)NH$_2$, C(=O)N(H)R$^a$, C(=O)N(R$^a$)R$^b$, C(=O)R$^d$, hydroxy or $C_1$-$C_6$-alkyl, where the $C_1$-$C_6$-alkyl radical is optionally mono- or polysubstituted by identical or different radicals from the group consisting of hydroxy, halogen, cyano, C(=O)OH, C(=O)OR$^a$, S(=O)$_2$—$C_1$-$C_6$-alkyl, NH$_2$, NHR$^a$, N(R$^a$)R$^b$, $C_1$-$C_6$-alkoxy which is optionally mono- or polysubstituted by identical or different radicals from the group consisting of halogen, $C_3$-$C_8$-cycloalkoxy which is optionally mono- or polysubstituted by identical or different radicals from the group consisting of halogen, heterocycloalkyl which is optionally mono- or polysubstituted by identical or different radicals from the group consisting of R$^c$, or represents $C_1$-$C_6$-alkoxy, where the $C_1$-$C_6$-alkoxy radical may optionally be mono- or polysubstituted by identical or different radicals from the group consisting of hydroxy, halogen, cyano, C(=O)OH, C(=O)OR$^a$, S(=O)$_2$—$C_1$-$C_6$-alkyl, NH$_2$, NHR$^a$, N(R$^a$)R$^b$, $C_3$-$C_8$-cycloalkyl which is optionally mono- or polysubstituted by identical or different radicals from the group consisting of halogen, $C_1$-$C_6$-alkoxy which is optionally mono- or polysubstituted by identical or different radicals from the group consisting of halogen, $C_3$-$C_8$-cycloalkoxy which is optionally mono- or polysubstituted by identical or different radicals from the group consisting of halogen, heterocycloalkyl which is optionally mono- or polysubstituted by identical or different radicals from the group consisting of R$^c$, aryl which is optionally mono- or polysubstituted by identical or different radicals from the group consisting of R$^c$, or 5- or 6-membered heteroaryl which is optionally mono- or polysubstituted by identical or different radicals from the group consisting of R$^c$, or represents $C_3$-$C_8$-cycloalkoxy or heterocycloalkoxy which may optionally be mono- or polysubstituted by identical or different radicals from the group consisting of hydroxy, halogen, cyano and $C_1$-$C_6$-alkyl, or represents aryloxy or 5- or 6-membered heteroaryloxy in which aryloxy and 5- or 6-membered heteroaryloxy may optionally be mono- or polysubstituted by identical or different radicals from the group consisting of hydroxy, halogen, cyano, C(=O)OH, C(=O)OR$^a$, $C_1$-$C_6$-alkyl and $C_1$-$C_6$-alkoxy, or represents $C_3$-$C_8$-cycloalkyl or heterocycloalkyl which may optionally be mono- or polysubstituted by identical or different radicals from the group consisting of hydroxy, halogen, cyano and $C_1$-$C_6$-alkyl, or represents $C_2$-$C_6$-alkenyl or $C_2$-$C_6$-alkynyl, or represents aryl, 5- to 10-membered heteroaryl, aryl-$C_1$-$C_4$-alkyl or 5- or 6-membered heteroaryl-$C_1$-$C_4$-alkyl, where aryl and heteroaryl may optionally be mono- or polysubstituted by identical or different radicals from the group consisting of halogen, hydroxy, cyano, C(=O)OH, C(=O)OR$^a$, $C_1$-$C_6$-alkyl, $C_3$-$C_8$-cycloalkyl and $C_1$-$C_6$-alkoxy;

$R^a$ represents $C_1$-$C_6$-alkyl, $C_3$-$C_{10}$-cycloalkyl, heterocycloalkyl, aryl or heteroaryl, where alkyl, cycloalkyl, heterocycloalkyl, aryl and heteroaryl may optionally be mono- or polysubstituted by identical or different radicals from the group consisting of halogen, hydroxy, cyano, $C_1$-$C_3$-alkyl, $C_1$-$C_3$-alkoxy, heterocycloalkyl, —C(=O)O—$C_1$-$C_6$-alkyl and S(=O)$_2$—$C_1$-$C_6$-alkyl;

$R^b$ represents $C_1$-$C_6$-alkyl or $C_3$-$C_{10}$-cycloalkyl;

or R$^a$ and R$^b$ together with the nitrogen atom form a 5- or 6-membered heterocycle which may optionally be mono- or polysubstituted by identical or different radicals from the group consisting of hydroxy, halogen, cyano, and $C_1$-$C_6$-alkyl;

$R^c$ represents hydroxy, halogen, cyano, $C_1$-$C_3$-alkyl or $C_1$-$C_3$-alkoxy;

$R^d$ represents hydrogen, $C_1$-$C_6$-alkyl or $C_3$-$C_{10}$-cycloalkyl;

$R^2$ represents hydrogen, $C_1$-$C_6$-alkyl or $C_3$-$C_6$-cycloalkyl;

$R^{13}$ represents hydrogen or $C_1$-$C_6$-alkyl;

W represents 5-membered heteroaryl which contains one to three heteroatoms selected from the group consisting of N, O and S and may optionally be monosubstituted by $R^3$ and optionally be mono- or polysubstituted by identical or different radicals $R^4$ or W represents pyridyl, pyrazinyl, pyridazinyl, 1,2,4-triazinyl or 1,3,5-triazinyl which may optionally be monosubstituted by $R^3$ and optionally be mono- or polysubstituted by identical or different radicals $R^4$;

$R^3$ represents hydrogen, halogen, cyano, C(=O)R$_a$, NH$_2$, NHR$^a$, N(R$_a$)R$^b$, N(H)C(=O)R$_a$ or $C_1$-$C_6$-alkyl, where $C_1$-$C_6$-alkyl may optionally be mono- or polysubstituted by identical or different radicals from the group consisting of hydroxy, halogen, cyano, C(=O)R$^a$, C(=O)OH, C(=O)OR$^a$, S(=O)$_2$—$C_1$-$C_6$-alkyl, NH$_2$, NHR$^a$, N(R$^a$)R$^b$, $C_1$-$C_6$-alkoxy, $C_3$-$C_8$-cycloalkoxy, where $C_1$-$C_6$-alkoxy and $C_3$-$C_8$-cycloalkoxy may optionally be mono- or polysubstituted by identical or different halogen radicals;

or $C_1$-$C_6$-alkyl is optionally mono- or polysubstituted by identical or radicals from the group consisting of $C_3$-$C_6$-cycloalkyl and heterocycloalkyl, where $C_3$-$C_6$-cycloalkyl and heterocycloalkyl may optionally be mono-, di- or trisubstituted by identical or different radicals from the group consisting of halogen, cyano, $C_1$-$C_3$-alkyl and $C_1$-$C_3$-alkoxy, or $C_1$-$C_6$-alkyl is optionally mono- or polysubstituted by identical or different radicals from the group consisting of aryl and 5- or 6-membered heteroaryl, where aryl and 5- or 6-membered heteroaryl may optionally be mono-, di- or trisubstituted by identical or different radicals from the group consisting of halogen, cyano, $C_1$-$C_3$-alkyl and $C_1$-$C_3$-alkoxy, or $R^3$ represents $C_1$-$C_6$-alkoxy, where $C_1$-$C_6$-alkoxy may optionally be mono- or polysubstituted by identical or different radicals from the group consisting of hydroxy, halogen, cyano, C(=O)OR$^a$, S(=O)$_2$—$C_1$-$C_6$-alkyl, N(R$^a$)R$^b$, $C_3$-$C_8$-cycloalkyl, $C_1$-$C_4$-alkoxy, $C_3$-$C_8$-cycloalkoxy, or represents $C_3$-$C_6$-cycloalkyl, heterocycloalkyl or $C_5$-$C_{11}$-spirocycloalkyl, where cycloalkyl, heterocycloalkyl and spirocycloalkyl may optionally be mono- or polysubstituted by identical or different radicals from the group consisting of hydroxy, halogen, cyano, C(=O)R$_a$, C(=O)OH, C(=O)OR$^a$, $C_1$-$C_6$-alkyl and $C_1$-$C_4$-alkoxy;

or represents aryl or 5- to 10-membered heteroaryl, where aryl and heteroaryl may optionally be mono- or polysubstituted by identical or different radicals from the group consisting of halogen, hydroxy, cyano, C(=O)OR$^a$, S(=O)$_2$—$C_1$-$C_6$-alkyl, NO$_2$, NH$_2$, NHR$^a$, N(R$_a$)R$^b$, N(H)C(=O)R$_a$, $C_3$-$C_8$-cycloalkyl, $C_1$-$C_3$-alkoxy and $C_1$-$C_3$-alkyl, where $C_1$-$C_3$-alkyl may optionally be mono- or polysubstituted by identical or different halogen radicals;

$R^4$ represents halogen, hydroxy, cyano or $C_1$-$C_6$-alkyl, where $C_1$-$C_6$-alkyl may optionally be mono- or polysubstituted by identical or different radicals from the group consisting of halogen, $C_1$-$C_6$-alkoxy, where $C_1$-$C_6$-alkoxy may optionally be mono- or polysubstituted by identical or different radicals from the group consisting of halogen, $C_2$-$C_6$-alkenyl, $C_2$-$C_6$-alkynyl, $C_3$-$C_{10}$-cycloalkyl, 3- to 10-membered heterocycloalkyl and aryl, where aryl may optionally be mono- or polysubstituted by identical or different radicals R;

or $R^4$ represents aryl or heteroaryl which may optionally be mono- or polysubstituted by identical or different radicals R;

or $R^4$ represents $C(=O)R^a$, $C(=O)NH_2$, $C(=O)N(H)R^a$, $C(=O)N(R^a)R^b$, $C(=O)OR^a$, $NH_2$, $NHR^a$, $N(R^a)R^b$, $N(H)C(=O)R^a$, $N(R^a)C(=O)R^a$, $N(H)C(=O)NH_2$, $N(H)C(=O)NHR^a$, $N(H)C(=O)N(R^a)R^b$, $N(R^a)C(=O)NH_2$, $N(R^a)C(=O)NHR^a$, $N(R^a)C(=O)N(R^a)R^b$, $N(H)C(=O)OR^a$, $N(R^a)C(=O)OR^a$, $NO_2$, $N(H)S(=O)R^a$, $N(R^a)S(=O)R^a$, $N(H)S(=O)_2R^a$, $N(R^a)S(=O)_2R^a$, $N=S(=O)(R^a)R^b$, $OC(=O)R^a$, $OC(=O)NH_2$, $OC(=O)NHR^a$, $OC(=O)N(R^a)R^b$, SH, $SR^a$, $S(=O)R^a$, $S(=O)_2R^a$, $S(=O)_2NH_2$, $S(=O)_2NHR^a$, $S(=O)_2N(R^a)R^b$ or $S(=O)(=N-R^a)R^b$;

R represents halogen, cyano, $C_1$-$C_6$-alkyl, $C_2$-$C_6$-alkenyl, $C_2$-$C_6$-alkynyl, $C_3$-$C_{10}$-cycloalkyl, 3- to 10-membered heterocycloalkyl, aryl, heteroaryl, $C(=O)R^a$, $C(=O)NH_2$, $C(=O)N(H)R^a$, $C(=O)N(R^a)R^b$, $C(=O)OR^a$, $NH_2$, $NHR^a$, $N(R^a)R^b$, $N(H)C(=O)R^a$, $N(R^a)C(=O)R^a$, $N(H)C(=O)NH_2$, $N(H)C(=O)NHR^a$, $N(H)C(=O)N(R^a)R^b$, $N(R^a)C(=O)NH_2$, $N(R^a)C(=O)NHR^a$, $N(R^a)C(=O)N(R^a)R^b$, $N(H)C(=O)OR^a$, $N(R^a)C(=O)OR^a$, $NO_2$, $N(H)S(=O)R^a$, $N(R^a)S(=O)R^a$, $N(H)S(=O)_2R^a$, $N(R^a)S(=O)_2R^a$, $N=S(=O)(R^a)R^b$, OH, $C_1$-$C_6$-alkoxy, $OC(=O)R^a$, $OC(=O)NH_2$, $OC(=O)NHR^a$, $OC(=O)N(R^a)R^b$, SH, $SR^a$, $S(=O)R^a$, $S(=O)_2R^a$, $S(=O)_2NH_2$, $S(=O)_2NHR^a$, $S(=O)_2N(R^a)R^b$ or $S(=O)(=NR^a)R^b$;

n represents 0 or 1;

Y represents a group selected from:

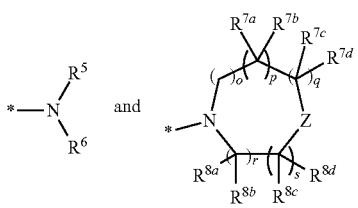

(II)

where * represents the point of attachment of the group to the remainder of the molecule;

$R^5$ represents hydrogen, $C_1$-$C_6$-alkyl or $C_3$-$C_{10}$-cycloalkyl, where
  $C_1$-$C_6$-alkyl may optionally be mono- or polysubstituted by identical or different radicals from the group consisting of hydroxy, halogen, cyano, $C(=O)OH$, $C(=O)OR^a$, $S(=O)_2$—$C_1$-$C_6$-alkyl, $N(R^a)R^b$, $C_1$-$C_4$-alkoxy and $C_3$-$C_8$-cycloalkyl;

$R^6$ represents hydrogen or $C_1$-$C_6$-alkyl, where
  $C_1$-$C_6$-alkyl may optionally be mono- or polysubstituted by identical or different radicals from the group consisting of hydroxy, halogen, cyano, $C_3$-$C_{10}$-cycloalkyl, $C(=O)R^a$, $C(=O)OH$, $C(=O)OR^a$, $S(=O)_2$—$C_1$-$C_6$-alkyl, $N(R^a)R^b$, $C_1$-$C_4$-alkoxy and $C_3$-$C_8$-cycloalkoxy, or represents $C_3$-$C_{10}$-cycloalkyl, where
  $C_3$-$C_{10}$-cycloalkyl may optionally be mono- or polysubstituted by identical or different radicals from the group consisting of hydroxy, halogen, cyano and $C_1$-$C_6$-alkyl, where
  $C_1$-$C_6$-alkyl may optionally be substituted by hydroxy, or represents heterocycloalkyl, where
  heterocycloalkyl may optionally be mono- or polysubstituted by identical or different radicals from the group consisting of halogen, cyano, $C_1$-$C_3$-alkyl and $C_1$-$C_3$-alkoxy, or represents aryl or 5- or 6-membered heteroaryl, where
  aryl and 5- or 6-membered heteroaryl may optionally be mono- or polysubstituted by identical or different radicals from the group consisting of halogen, cyano, $C_1$-$C_3$-alkyl, $C_1$-$C_3$-alkoxy, $S(=O)_2NH_2$, $S(=O)_2NHR^a$ and $S(=O)_2N(R^a)R^b$;

$R^{7a}$ represents hydrogen, halogen, $N(R^a)R^b$, $C_1$-$C_6$-alkyl or $C_3$-$C_{10}$-cycloalkyl, where $C_1$-$C_6$-alkyl may optionally be mono- or polysubstituted by identical or different radicals from the group consisting of hydroxy, halogen, cyano, $C(=O)OH$, $C(=O)OR^a$, $S(=O)_2$—$C_1$-$C_6$-alkyl, $N(R^a)R^b$, $C_1$-$C_4$-alkoxy, $C_3$-$C_8$-cycloalkyl and heterocycloalkyl;

$R^{7b}$ represents hydrogen, halogen or $C_1$-$C_6$-alkyl, where $C_1$-$C_6$-alkyl may optionally be mono- or polysubstituted by identical or different radicals from the group consisting of hydroxy, halogen, cyano, $C(=O)OH$, $C(=O)OR^a$, $S(=O)_2$—$C_1$-$C_6$-alkyl, $N(R^a)R^b$, $C_1$-$C_4$-alkoxy, $C_3$-$C_8$-cycloalkyl and heterocycloalkyl;

or $R^{7a}$ and $R^{7b}$ together with the carbon atom form $C_3$-$C_6$-cycloalkyl which may optionally be mono- or polysubstituted by identical or different radicals from the group consisting of hydroxy, halogen, cyano and $C_1$-$C_6$-alkyl, or $R^{7a}$ and $R^{7b}$ together represent an oxo group;

$R^{7c}$ represents hydrogen, halogen, $N(R^a)R^b$, $C_1$-$C_6$-alkyl or $C_3$-$C_{10}$-cycloalkyl, where
  $C_1$-$C_6$-alkyl may optionally be mono- or polysubstituted by identical or different radicals from the group consisting of hydroxy, halogen, cyano, $C(=O)OH$, $C(=O)OR^a$, $S(=O)_2$—$C_1$-$C_6$-alkyl, $N(R^a)R^b$, $C_1$-$C_4$-alkoxy, $C_3$-$C_8$-cycloalkyl and heterocycloalkyl;

$R^{7d}$ represents hydrogen, halogen or $C_1$-$C_6$-alkyl, where
  $C_1$-$C_6$-alkyl may optionally be mono- or polysubstituted by identical or different radicals from the group consisting of hydroxy, halogen, cyano, $C(=O)OH$, $C(=O)OR^a$, $S(=O)_2$—$C_1$-$C_6$-alkyl, $N(R^a)R^b$, $C_1$-$C_4$-alkoxy, $C_3$-$C_8$-cycloalkyl and heterocycloalkyl;

or $R^{7c}$ and $R^{7d}$ together with the carbon atom form $C_3$-$C_6$-cycloalkyl which may optionally be mono- or polysubstituted by identical or different radicals from the group consisting of hydroxy, halogen, cyano and $C_1$-$C_6$-alkyl, or $R^{7c}$ and $R^{7d}$ together represent an oxo group;

$R^{8a}$ represents hydrogen, halogen, $N(R^a)R^b$, $C_1$-$C_6$-alkyl or $C_3$-$C_{10}$-cycloalkyl, where
  $C_1$-$C_6$-alkyl may optionally be mono- or polysubstituted by identical or different radicals from the group consisting of hydroxy, halogen, cyano, $C(=O)OH$, $C(=O)OR^a$, $S(=O)_2$—$C_1$-$C_6$-alkyl, $N(R^a)R^b$, $C_1$-$C_4$-alkoxy, $C_3$-$C_8$-cycloalkyl and heterocycloalkyl;

$R^{8b}$ represents hydrogen, halogen or $C_1$-$C_6$-alkyl, where
  $C_1$-$C_6$-alkyl may optionally be mono- or polysubstituted by identical or different radicals from the group consisting of hydroxy, halogen, cyano, $C(=O)OH$, $C(=O)OR^a$, $S(=O)_2$—$C_1$-$C_6$-alkyl, $N(R^a)R^b$, $C_1$-$C_4$-alkoxy, $C_3$-$C_8$-cycloalkyl and heterocycloalkyl;

or $R^{8a}$ and $R^{8b}$ together with the carbon atom form $C_3$-$C_6$-cycloalkyl which may optionally be mono- or polysubstituted by identical or different radicals from the group consisting of hydroxy, halogen, cyano and $C_1$-$C_6$-alkyl, $R^{8c}$ represents hydrogen, halogen, $N(R^a)R^b$, $C_1$-$C_6$-alkyl or $C_3$-$C_{10}$-cycloalkyl, where
  $C_1$-$C_6$-alkyl may optionally be mono- or polysubstituted by identical or different radicals from the group consisting of hydroxy, halogen, cyano, C(=O)OH, C(=O)OR$^a$, S(=O)$_2$—$C_1$-$C_6$-alkyl, $N(R^a)R^b$, $C_1$-$C_4$-alkoxy, $C_3$-$C_8$-cycloalkyl and heterocycloalkyl;

$R^{8d}$ represents hydrogen, halogen or $C_1$-$C_6$-alkyl, where
  $C_1$-$C_6$-alkyl may optionally be mono- or polysubstituted by identical or different radicals from the group consisting of hydroxy, halogen, cyano, C(=O)OH, C(=O)OR$^a$, S(=O)$_2$—$C_1$-$C_6$-alkyl, $N(R^a)R^b$, $C_1$-$C_4$-alkoxy, $C_3$-$C_8$-cycloalkyl and heterocycloalkyl;

or $R^{8c}$ and $R^{8d}$ together with the carbon atom form $C_3$-$C_6$-cycloalkyl which may optionally be mono- or polysubstituted by identical or different radicals from the group consisting of hydroxy, halogen, cyano and $C_1$-$C_6$-alkyl, or $R^{8c}$ and $R^{8d}$ together represent an oxo group;

o represents 0, 1 or 2,
p represents 0, 1 or 2,
q represents 0, 1 or 2,
r represents 0, 1 or 2,
s represents 0, 1 or 2,
where o, p, q, r and s do not simultaneously represent 0;

Z represents a group selected from C(=O), CR$^9$R$^{10}$, NR$^{11}$, O, S, S(=O) and S(=O)$_2$;

$R^9$ represents hydrogen or $C_1$-$C_6$-alkyl, $R^{10}$ represents hydrogen, halogen, cyano, C(=O)R$^a$, C(=O)OH, C(=O)OR$^a$, C(=O)NH$_2$, C(=O)N(H)R$^a$, C(=O)N(R$^a$)R$^b$, N(H)C(=O)R$^a$, N(R$^b$)C(=O)R$^a$, S(=O)$_2$R$^a$, hydroxy, N(R$^a$)R$^b$ and $C_1$-$C_6$-alkyl, where
  $C_1$-$C_6$-alkyl may optionally be mono- or polysubstituted by identical or different radicals from the group consisting of hydroxy, halogen, cyano, C(=O)R$^a$, C(=O)OH, C(=O)OR$^a$, S(=O)$_2$—$C_1$-$C_6$-alkyl, $N(R^a)R^b$, $C_1$-$C_4$-alkoxy and $C_3$-$C_8$-cycloalkoxy, or represents $C_1$-$C_6$-alkoxy, where
  $C_1$-$C_6$-alkoxy may optionally be mono- or polysubstituted by identical or different radicals from the group consisting of hydroxy, halogen, cyano, C(=O)OH, C(=O)OR$^a$, S(=O)$_2$—$C_1$-$C_6$-alkyl, $N(R^a)R^b$, $C_3$-$C_8$-cycloalkyl, $C_1$-$C_4$-alkoxy, $C_3$-$C_8$-cycloalkoxy, heterocycloalkyl, aryl and 5- or 6-membered heteroaryl, where
    aryl and 5- or 6-membered heteroaryl may optionally be mono- or polysubstituted by identical or different radicals from the group consisting of halogen, cyano, $C_1$-$C_3$-alkyl and $C_1$-$C_3$-alkoxy, or represents aryloxy or 5- or 6-membered heteroaryloxy in which aryloxy and 5- or 6-membered heteroaryloxy may optionally be mono- or polysubstituted by identical or different radicals from the group consisting of hydroxy, halogen, cyano, C(=O)OH, C(=O)OR$^a$, $C_1$-$C_3$-alkyl and $C_1$-$C_3$-alkoxy,
  or represents $C_3$-$C_8$-cycloalkyl, $C_3$-$C_8$-cycloalkyl-$C_1$-$C_4$-alkyl, heterocycloalkyl or heterocycloalkyl-$C_1$-$C_4$-alkyl, which may optionally be mono- or polysubstituted by identical or different radicals from the group consisting of hydroxy, halogen, cyano, C(=O)R$^a$, C(=O)OH, C(=O)OR$^a$, $C_1$-$C_6$-alkyl and $C_1$-$C_6$-alkoxy, where
    $C_1$-$C_6$-alkoxy may optionally be mono- or polysubstituted by identical or different halogen radicals or an oxo group;
  or represents $C_2$-$C_6$-alkenyl or $C_2$-$C_6$-alkynyl,
  or represents aryl, 5- to 10-membered heteroaryl, aryl-$C_1$-$C_4$-alkyl or 5- or 6-membered heteroaryl-$C_1$-$C_4$-alkyl, where
    aryl and heteroaryl may optionally be mono- or polysubstituted by identical or different radicals from the group consisting of halogen, hydroxy, cyano, C(=O)OH, C(=O)OR$^a$, NHR$^a$, N(R$^a$)R$^b$, $C_1$-$C_3$-alkyl, $C_3$-$C_8$-cycloalkyl and $C_1$-$C_3$-alkoxy;

or $R^9$ and $R^{10}$ together with the carbon atom form $C_3$-$C_8$-cycloalkyl or a 4- to 6-membered heterocycle, where
  the $C_3$-$C_8$-cycloalkyl radical or the 4- to 6-membered heterocycle may optionally be mono- or polysubstituted by identical or different radicals from the group consisting of hydroxy, halogen, cyano, $C_1$-$C_6$-alkyl, C(=O)R$^a$ and an oxo group;

$R^{11}$ represents hydrogen, C(=O)R$^a$, C(=O)OR$^a$, C(=O)NH$_2$, C(=O)N(H)R$^a$, C(=O)N(R$^a$)R$^b$, S(=O)$_2$R$^a$, S(=O)$_2$N(R$^a$)R$^b$ or $C_1$-$C_6$-alkyl, where
  $C_1$-$C_6$-alkyl may optionally be mono- or polysubstituted by identical or different radicals from the group consisting of hydroxy, halogen, cyano, C(=O)R$^a$, C(=O)OR$^a$, C(=O)NH$_2$, C(=O)N(H)R$^a$, C(=O)N(R$^a$)R$^b$, S(=O)$_2$—$C_1$-$C_6$-alkyl, $N(R^a)R^b$, $C_3$-$C_8$-cycloalkyl, $C_1$-$C_4$-alkoxy and $C_3$-$C_8$-cycloalkoxy, where
    $C_3$-$C_8$-cycloalkyl, $C_1$-$C_4$-alkoxy and $C_3$-$C_8$-cycloalkoxy may optionally be mono- or polysubstituted by identical or different radicals from the group consisting of hydroxy and halogen;
  or represents $C_3$-$C_8$-cycloalkyl, heterocycloalkyl or heterocycloalkyl-$C_1$-$C_4$-alkyl which may optionally be mono- or polysubstituted by identical or different radicals from the group consisting of hydroxy, halogen, cyano, $C_1$-$C_6$-alkyl, $C_1$-$C_6$-alkoxy, where alkyl and alkoxy may optionally be mono- or polysubstituted by identical or different radicals from the group consisting of halogen and an oxo group,
  or represents $C_2$-$C_6$-alkenyl or $C_2$-$C_6$-alkynyl,
  or represents aryl, 5- to 10-membered heteroaryl, aryl-$C_1$-$C_4$-alkyl or 5- or 6-membered heteroaryl-$C_1$-$C_4$-alkyl, where
    aryl and heteroaryl may optionally be mono- or polysubstituted by identical or different radicals from the group consisting of halogen, hydroxy, cyano, C(=O)OH, C(=O)OR$^a$, $C_1$-$C_3$-alkyl, $C_3$-$C_8$-cycloalkyl and $C_1$-$C_3$-alkoxy;

as defined and described in WO 2015/091426 and US 2016/0311833, the entirety of each of which is herein incorporated by reference.

In certain embodiments, the present invention provides a compound of Formula I, wherein IRAK is an IRAK4 inhibitor

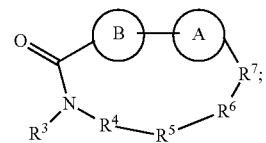

thereby forming a compound of formula I-ggg-1

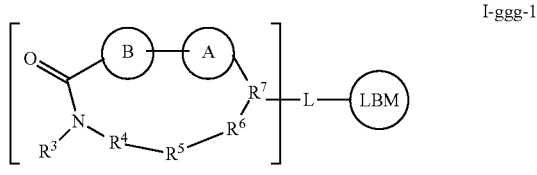

or a pharmaceutically acceptable salt thereof, wherein L and LBM are as defined above and described in embodiments herein, and wherein:

Ring A is phenylene or 5- to 6-membered heteroarylene containing 1-3 heteroatoms chosen from O, S, and N, wherein ring A is optionally substituted with lower alkyl that is further optionally substituted, Ring B is phenylene, 5- to 6-membered heterocycloalkylene containing 1-3 heteroatoms chosen from O, S, and N, or 5- to 6-membered heteroarylene containing 1-3 heteroatoms chosen from O, S, and N, wherein ring B is optionally substituted with lower alkyl that is further optionally substituted, $R^3$ is chosen from hydrogen, lower alkyl optionally substituted with alkoxy, amino, N-(alkyl)amino, N,N-(dialkyl)amino, or phenyl, heterocycloalkyl, and heteroaryl, wherein phenyl, heterocycloalkyl, and heteroaryl are optionally substituted with one or two groups independently chosen from lower alkyl and wherein alkoxy is optionally substituted with tri(alkyl)silyl, $R^4$ is chosen from heteroarylene and arylene, each of which is optionally substituted, or $R^4$ and $R^3$ taken together with the nitrogen to which they are bound, form an optionally substituted 3- to 7-membered heterocycloalkyl ring, or $R^4$ is an alkylene chain having 1-3 carbon atoms that is optionally substituted with one or two groups independently chosen from lower alkyl and cycloalkyl, each of which groups is optionally substituted with hydroxyl or alkoxy, or $R^4$ is absent, $R^5$ is chosen from $C(O)NR^{51}$, $NR^{52}$, and O or $R^5$ is absent, provided that if $R^4$ is absent, then $R^5$ is absent, $R^6$ is an alkylene or alkenylene chain having one or two double bonds, wherein the alkylene or alkenylene chain has 2 to 10 carbon atoms, wherein the alkylene or alkenylene chain is optionally substituted with one or two groups independently chosen from lower alkyl and cycloalkyl, each of which groups is optionally substituted with hydroxyl or alkoxy, and further wherein one or two of the carbon atoms in the alkylene chain is optionally replaced by an O, S, SO, $SO_2$, or $NR^{61}$, and wherein two of the carbon atoms in the alkylene chain, are optionally connected by a two or three carbon atom alkylene chain to form a 5- to 7-membered ring.

$R^7$ is chosen from $NR^{71}$ and O or $R^7$ is absent,
$R^{51}$ is chosen from hydrogen and lower alkyl,
$R^{52}$ is chosen from hydrogen, lower alkyl, and $-C(O)OR^{81}$,
$R^{61}$ is chosen from hydrogen, lower alkyl, and $-C(O)OR^{81}$,
$R^{71}$ is chosen from hydrogen, lower alkyl, and $-C(O)OR^{81}$, and
$R^{81}$ is lower alkyl;

as defined and described in WO 2014/143672 and US 2016/0002265, the entirety of each of which is herein incorporated by reference.

In certain embodiments, the present invention provides a compound of Formula I, wherein IRAK is an IRAK4 inhibitor

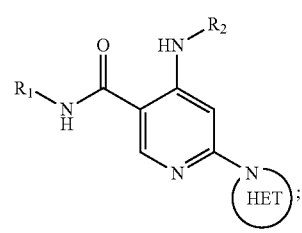

thereby forming a compound of formula I-hhh-1

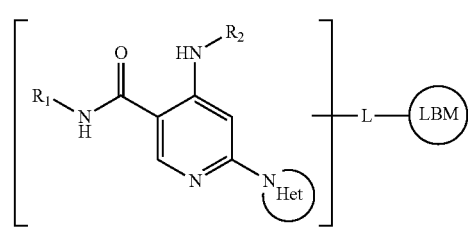

or a pharmaceutically acceptable salt thereof, wherein L and LBM are as defined above and described in embodiments herein, and wherein HET is a heteroaryl selected from pyrazolyl, indolyl, pyrrolo[2,3-b]pyridinyl, pyrrolo[2,3-d]pyrimidinyl, pyrazolo[3,4-b]pyridinyl, pyrazolo[3,4-d]pyrimidinyl, 2,3-dihydro-1H-pyrrolo[2,3-b]pyridinyl, imidazo[4,5-b]pyridinyl, and purinyl, wherein said heteroaryl is substituted with $R_a$ and $R_b$;

$R_a$ is H, F, Cl, Br, $-CN$, $-OH$, $C_{1-4}$ alkyl, $C_{1-4}$ fluoroalkyl, $C_{1-4}$hydroxyalkyl, $C_{1-4}$ alkoxy, $-NH_2$, $-NH(C_{1-4}$ alkyl), $-N(C_{1-4}$ alkyl$)_2$, $-NH(C_{1-4}$ hydroxyalkyl), $-NH(C_{1-4}$ fluoroalkyl), $-NH(C_{1-6}$ hydroxy-fluoroalkyl), $-C(O)NH_2$, $-CH_2NHC(O)(C_{1-6}$ alkyl), $-CH_2NHC(O)(C_{1-6}$ hydroxyalkyl), $-CH_2NHC(O)NH(C_{1-6}$ alkyl), $-CH_2NHC(O)NHCH_2$(phenyl), $-CH_2NHC(O)N(C_{1-4}$ alkyl$)_2$, $-CH_2NHC(O)O(C_{1-4}$ alkyl), $-CH_2NHC(O)(C_{3-6}$ cycloalkyl), $-CH_2NHC(O)$(tetrahydrofuranyl), $-CH_2NHC(O)CH_2(C_{3-6}$ cycloalkyl), $-CH_2NHC(O)CH_2$(tetrahydropyranyl), $-CH_2NHC(O)CH_2$(phenyl), $-NHC(O)(C_{1-4}$ alkyl), pyrrolidinyl, hydroxypyrrolidinyl, or pyridazinyl;

$R_b$ is H or $-NH_2$;

$R_1$ is:
(i) $C_{1-6}$ alkyl, $C_{1-6}$ fluoroalkyl, $C_{1-6}$ hydroxyalkyl, $C_{1-8}$ hydroxy-fluoroalkyl, $-(C_{1-6}$ alkylenyl)$O(C_{1-4}$ alkyl), $-(C_{1-6}$ alkylenyl)$O(C_{1-4}$ fluoroalkyl), $-(C_{1-6}$ fluoroalkylenyl)$O(C_{1-4}$ alkyl), $-(C_{1-6}$ fluoroalkylenyl)$O(C_{1-4}$ deuteroalkyl), $-(C_{1-6}$ fluoroalkylenyl)$O(C_{1-4}$ fluoroalkyl), $-(C_{1-4}$ fluoroalkylenyl)$C(C_{3-6}$ cycloalkyl$)_2(OH)$, $-(C_{1-4}$alkylenyl)$NHC(O)(C_{1-4}$ alkylenyl)$OC(O)(C_{1-3}$ alkyl), $-(C_{1-6}$alkylenyl)$NHS(O)_2(C_{1-4}$ alkyl), $-(C_{1-6}$ alkylenyl)$P(O)(C_{1-4}$ alkoxy$)_2$, $-(C_{1-6}$ fluoroalkylenyl)$NH(C_{1-4}$ alkyl), $-(C_{1-6}$ alkylenyl)$C(O)NH(C_{1-4}$ alkyl), $-(C_{1-6}$ fluoroalkylenyl)$C(O)NH(C_{1-4}$ alkyl), $-(C_{1-6}$fluoroalkylenyl)$C(O)NH(C_{1-4}$ hydroxyalkyl), or $-(C_{1-6}$fluoroalkylenyl)$OP(O)(OH)_2$;

(ii) $-(C_{1-3}$ alkylenyl)$R_x$, $-(C_{1-3}$ fluoroalkylenyl)$R_x$, $-(C_{1-3}$alkylenyl)$C(O)R_x$, $-(C_{1-3}$ alkylenyl)$C(O)$ NHR$_x$, —(C$_{1-3}$fluoroalkylenyl)C(O)R$_x$, or —CH$_2$CF= (tetrahydropyranyl), wherein R$_x$ is a cyclic group selected from C$_{3-6}$ cycloalkyl, tetrazolyl, 1,1-dioxido-tetrahydrothiophenyl, 1,1-dioxidothiomorpholinyl, oxadiazolyl, piperidinyl, piperazinyl, pyrrolidinyl, oxetanyl, tetrahydrofuranyl, tetrahydropyranyl, pyridinyl, imidazolyl, morpholinyl, phenyl, and triazinyl, wherein each cyclic group is substituted with zero to 3 substituents independently selected from F, —OH, —CH$_3$, —C(CH$_2$)$_2$OH, —OCH$_3$, —C(O)CH$_2$CN, —S(O)$_2$CH$_3$, —S(O)$_2$NH$_2$, —NHC(O)CH$_3$, —N(S(O)$_2$CH$_3$)$_2$, —CH$_2$CH$_2$(acetamidophenyl), —CH$_2$CH$_2$(methoxyphenyl), —CH$_2$CH$_2$(sulfamoylphenyl), oxetanyl, benzyl, and morpholinyl;

(iii) C$_{3-6}$ cycloalkyl or C$_{4-6}$ cycloalkenyl, each substituted with zero to 3 substituents independently selected from F, —OH, —CN, C$_{1-3}$alkyl, C$_{1-3}$ alkoxy, —S(C$_{1-3}$ alkyl), —NO$_2$, —S(O)$_2$(C$_{1-3}$ alkyl), C$_{1-4}$hydroxyalkyl, —C(C$_{1-3}$ alkyl)(OH)(C$_{3-6}$ cycloalkyl), —CH$_2$C(O)NH(C$_{1-3}$ alkyl), —NHC(O)(C$_{1-3}$ alkyl), —NHC(O)(C$_{1-4}$ hydroxyalkyl), —C(O)NH(C$_{1-3}$ alkyl), —C(O)NH(C$_{1-3}$ deuteroalkyl), —C(O)NH(C$_{3-6}$ cycloalkyl), —NHC(O)O(C$_{1-3}$ alkyl), —NHS(O)$_2$(C$_{1-3}$alkyl), pyridinyl, imidazolyl, pyrazolyl, methylimidazolyl, methylpyrazolyl, and thiazolyl;

(iv) tetrahydropyranyl, piperidinyl, pyrazolyl, phenyl, pyridinyl, or pyrimidinyl, each substituted with zero to 1 substituent selected from —OH, C$_{1-3}$ alkyl, C$_{1-3}$ fluoroalkyl, C$_{1-4}$ hydroxyalkyl, C$_{1-3}$alkoxy, —C(O)(C$_{1-4}$ alkyl), —S(O)$_2$(C$_{1-4}$ alkyl), —S(O)$_2$NH(C$_{1-4}$ alkyl), —NH(C$_{1-3}$ alkyl), —N(C$_{1-3}$ alkyl)$_2$, —O(C$_{1-3}$ alkylenyl)N(C$_{1-3}$ alkyl)$_2$, —CH$_2$ (morpholinyl), azetidinyl, oxetanyl, tetrahydropyranyl, morpholinyl, piperazinyl, piperidinyl, methylpiperazinyl, methoxypiperidinyl, pyridinyl, pyrimidinyl, methylsulfonyl azetidinyl, and —C(O)(methylsulfonyl azetidinyl); or (v) pyrrolo[2,3-c]pyridinyl, bicyclo[2.2.1]heptan-1-ol, tetrahydrobenzo[d]thiazol-2-amine, or 1,3-diazaspiro[4.5]decane-2,4-dione; and R$_2$ is:
(i) C$_{1-7}$ alkyl or C$_{2-6}$ alkenyl, each substituted with zero to three substituents independently selected from F, —OH, and —CN; —(C$_{1-4}$ alkylenyl)O(C$_{1-4}$ alkyl), —(C$_{1-4}$ alkylenyl)O(C$_{1-4}$ fluoroalkyl), —(C$_{1-6}$ alkylenyl)NH$_2$, —(C$_{1-6}$ alkylenyl)S(O)$_2$(C$_{1-3}$ alkyl), —(C$_{1-6}$ fluoroalkylenyl)NH(C$_{1-3}$ alkyl), or —(C$_{1-6}$ alkylenyl)NHC(O)(C$_{1-4}$fluoroalkyl);

(ii) —(C$_{1-4}$ alkylenyl)R$_y$, wherein R$_y$ is C$_{3-6}$ cycloalkyl, azetidinyl, oxetanyl, oxazolyl, pyridinyl, tetrahydropyranyl, or morpholinyl, each substituted with zero to 2 substituents independently selected from F, —OH, and C$_{1-3}$ alkyl;

(iii) C$_{3-6}$ cycloalkyl, azetidinyl, oxetanyl, furanyl, tetrahydrofuranyl, pyrrolidinyl, piperidinyl, or tetrahydropyranyl, each substituted with zero to 3 substituents independently selected from F, —OH, C$_{1-3}$alkyl, C$_{1-3}$hydroxyalkyl, —C(O)(C$_{1-3}$ alkyl), —C(O)(C$_{1-3}$ fluoroalkyl), —C(O)(C$_{1-3}$ cyanoalkyl), —C(O)O(C$_{1-3}$ alkyl), —C(O)NH$_2$, —C(O)NH(C$_{1-3}$ alkyl), —C(O)(difluorophenyl), —NH$_2$, —NH(C$_{1-3}$ alkyl), —NH(C$_{1-3}$ fluoroalkyl), —NH(oxetanyl), —NHC(O)(C$_{1-3}$ alkyl), —NHC(O)(C$_{1-3}$ fluoroalkyl), —NHC(O)(C$_{3-6}$ cycloalkyl), —NHC(O)(fluorophenyl), —S(O)$_2$(C$_{1-3}$ alkyl), imidazolyl, phenyl, pyrimidinyl, fluoropyrimidinyl, chloropyrimidinyl, and methoxypyrimidinyl;

(iv) adamantanyl, hydroxyadamantanyl, benzo[d]imidazolyl, benzo[d]oxazolyl, benzo[d]triazolyl, benzothiazolyl, bicyclo[1.1.1]pentanyl, or hydroxy-bicyclo[2.2.1]heptanyl; or (v) phenyl, pyrazolyl, thiazolyl, thiadiazolyl, or indazolyl, each substituted with 0 to 2 substituents independently selected from F, Cl, —OH, —CN, C$_{1-4}$ alkyl, C$_{1-4}$ hydroxyalkyl, C$_{1-4}$fluoroalkyl, C$_{1-4}$cyanoalkyl, C$_{1-3}$ alkoxy, C$_{3-6}$ cycloalkyl, —(C$_{1-3}$ alkylenyl)O(C$_{1-3}$alkyl), —(C$_{1-3}$ alkylenyl)O(C$_{1-3}$ fluoroalkyl), —C(O)NH$_2$, —C(O)NH(C$_{1-3}$ alkyl), —NHC(O)(C$_{1-3}$ alkyl), —NHC(O)S(O)$_2$(C$_{1-3}$alkyl), —S(O)$_2$NH$_2$, —S(O)$_2$(C$_{1-3}$ alkyl), pyrazolyl, methyl pyrazolyl, imidazolyl, triazolyl, methyl tetrazolyl, ethyl tetrazolyl, phenyl, pyrimidinyl, fluoropyrimidinyl, and tetrahydropyranyl;

as defined and described in WO 2015/103453 and US 2015/0191464, the entirety of each of which is herein incorporated by reference.

In certain embodiments, the present invention provides a compound of Formula I, wherein IRAK is an IRAK4 inhibitor

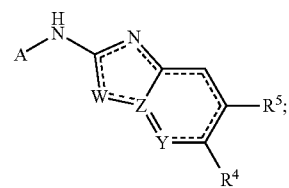

thereby forming a compound of formula I-iii-1

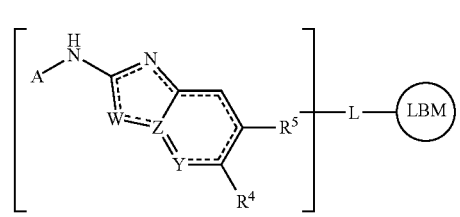

or a pharmaceutically acceptable salt thereof, wherein L and LBM are as defined above and described in embodiments herein, and wherein ═══ is a single or double bond;

W is selected from CH, CH—CH, O, S, NR$^6$, and CO;
Y is N or CR$^9$;
Z is N or C, and Z is N if W is CH and Y is CR$^9$;
R$^4$ is selected from hydrogen, halogen, OR$^6$, CN, NR$^7$R$^8$, CH$_2$OR$^6$, an optionally substituted aryl, an optionally substituted heteroaryl, an optionally substituted non-aromatic ring, an optionally substituted carbocycle, an optionally substituted C$_1$-C$_6$ alkyl, an optionally substituted C$_1$-C$_6$ haloalkyl, an optionally substituted C$_1$-C$_6$heteroalkyl, an optionally substituted C$_1$-C$_6$ alkenyl, an optionally substituted C$_1$-C$_6$ alkynyl, CO$_2$R$^6$, SO$_3$R$^6$, —SO$_2$R$^6$ and SO$_2$NR$^7$R$^8$;
R$^5$ is selected from hydrogen, halogen, OR$^6$, an optionally substituted C$_1$-C$_6$ alkyl, an optionally substituted C$_1$-C$_6$ haloalkyl, an optionally substituted C$_1$-C$_6$heteroalkyl, an optionally substituted C$_1$-C$_6$haloheteroalkyl, an optionally substituted C$_1$-C$_6$ alkenyl, and an optionally substituted C$_1$-C$_6$ alkynyl;
or R$^4$ and R$^5$ are linked to form an optionally substituted non-aromatic ring;
each R$^6$ is independently selected from an optionally substituted aryl, an optionally substituted heteroaryl, and an optionally substituted non-aromatic ring, each optionally fused with a substituted aryl or a substituted heteroaryl, hydrogen, an optionally substituted C$_1$-C$_{10}$alkyl, an optionally substituted C$_1$-C$_{10}$ haloalkyl, and an optionally substituted C$_1$-C$_{10}$ heteroalkyl;

each $R^7$ and $R^8$ is independently selected from an optionally substituted aryl, an optionally substituted heteroaryl, an optionally substituted non-aromatic ring, each optionally fused with a substituted aryl or a substituted heteroaryl, hydrogen, an optionally substituted $C_1$-$C_{10}$ alkyl, an optionally substituted $C_1$-$C_{10}$ haloalkyl, an optionally substituted $C_1$-$C_{10}$ alkenyl, an optionally substituted $C_1$-$C_{10}$ alkynyl, and an optionally substituted $C_1$-$C_{10}$ heteroalkyl, or $R^7$ and $R^8$ are linked to form an optionally substituted non-aromatic ring;

$R^9$ is selected from hydrogen, halogen, $OR^6$, CN, $NR^7R^8$, $CH_2OR^6$, an optionally substituted aryl, an optionally substituted heteroaryl, an optionally substituted non-aromatic ring, an optionally substituted $C_1$-$C_6$ alkyl, an optionally substituted $C_1$-$C_6$ haloalkyl, an optionally substituted $C_1$-$C_6$heteroalkyl, an optionally substituted $C_1$-$C_6$ alkenyl, an optionally substituted $C_1$-$C_6$ alkynyl, $CO_2R_6$, $SO_3R_6$, and $SO_2NR^7R^8$;

A is an optionally substituted aryl or an optionally substituted heteroaryl group;

each optionally substituted group is either unsubstituted or substituted with one or more groups independently selected from alkyl, heteroalkyl, alkenyl, alkynyl, haloalkyl, heterohaloalkyl, aryl, arylalkyl, heteroaryl, non-aromatic ring, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, $=O$, $=S$, amino, and protected derivatives of amino groups;

as defined and described in WO 2012/068546 and US 2014/0155379, the entirety of each of which is herein incorporated by reference.

In certain embodiments, the present invention provides a compound of Formula I, wherein IRAK is an IRAK4 inhibitor

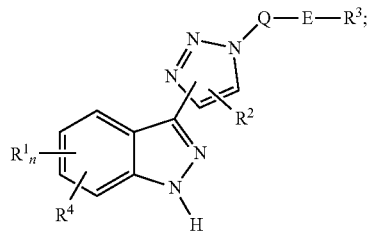

thereby forming a compound of formula I-jjj-1

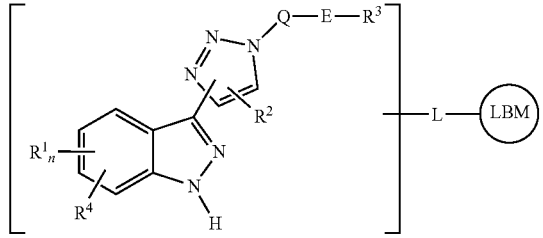

or a pharmaceutically acceptable salt thereof, wherein L and LBM are as defined above and described in embodiments herein, and wherein:

Q denotes Ar or Het;

E denotes —$(CH_2)_mCO$—, —$(CH_2)_mSO_2$—, —$(CH_2)_q$—, —$(CH_2)_mNHCO$—, or a single bond;

$R^1$ denotes H, OH, NH—$C_1$-$C_6$-alkyl, $OC_1$-$C_6$-alkyl, $C_1$-$C_6$-alkyl, $C_2$-$C_6$-alkenyl, $C_2$-$C_6$-alkynyl, Cyc, Hal, $Het^1$, O-$Het^1$, CO-$Het^1$, NH-$Het^1$, CO—$Ar^1$, O—$Ar^1$, $Ar^1$, NH—$Ar^1$, —$(CH_2)_qHet^1$, —$CONH$—$(CH_2)_qHet^1$, —$CONH$-$Het^1$, —$(CH_2)_qO$-$Het^1$, —$(CH_2)_qO$—$Ar^1$, —$(CH_2)_qAr^1$, —$CONH$—$(CH_2)_qAr^1$, —$CONH$—$Ar^1$, —$CONHC_3$-$C_6$-cycloalkyl, —$(CH_2)_qHal$, —$(CH_2)_qCyc$, $CF_3$, —$(CH_2)_sNH$—$(CH_2)_q$-$Het^1$, —$(CH_2)_sNH$—$(CH_2)_q$—$Ar^1$, wherein NH—$C_1$-$C_6$-alkyl, $OC_1$-$C_6$-alkyl, $C_1$-$C_6$-alkyl, $C_2$-$C_6$-alkenyl, $C_2$-$C_6$-alkynyl, $C_3$-$C_6$-cycloalkyl may be substituted by 1 to 3 groups independently selected from $OC_1$-$C_3$-alkyl, OH, $CONH_2$, $NH_2$;

$R^2$ denotes H, $C_1$-$C_6$-alkyl, $C_2$-$C_6$-alkenyl, $C_2$-$C_6$-alkynyl, Hal, $CF_3$, preferably H;

$R^3$ denotes $Het^1$, $Ar^1$, $NR^aR^b$, COOH, —$(CH_2)_qHet^1$, —$(CH_2)_qAr^1$, —$(CH_2)_qNR^aR^b$, —$(CH_2)_qCOOH$, or $C_1$-$C_6$-alkyl wherein 1 to 3 hydrogen atoms may be independently replaced by OH or $CF_3$;

$R^4$ denotes H, $C_1$-$C_6$-alkyl, $C_2$-$C_6$-alkenyl, Hal;

$R^a$ denotes H, linear, branched or cyclic $C_1$-$C_6$-alkyl;

$R^b$ denotes H, $Het^b$, $Ar^b$, —CO-$Het^b$, —CO—$Ar^b$, a $C_3$-$C_8$-cycloalkyl or a linear or branched alkyl having 1 to 6 carbon atoms, wherein 1 to 3 hydrogen atoms may be replaced by $Het^b$, $Ar^b$, $NH_2$, $N(C_1$-$C_6$-alkyl$)_2$, $NH(C_1$-$C_6$-alkyl), $N(C_1$-$C_6$-alkyl)($C_3$-$C_8$-cycloalkyl), $NH(C_3$-$C_8$-cycloalkyl), $O(C_1$-$C_6$-alkyl), CN, OH, $CF_3$, Hal;

n is 0, 1, 2, 3 or 4;

m is 0, 1, 2, 3 or 4;

q is 1, 2, or 3;

s is 0, 1, 2 or 3;

Hal denotes Cl, Br, I, F, preferably Cl or F;

Ar denotes a divalent monocyclic or fused bicyclic arylen group having 6 to 14 carbon atoms, which may be further substituted with 1 to 4 substitutents selected from Hal, $C_1$-$C_6$-alkyl, —$(CH_2)_mOC_1$-$C_6$-alkyl, CN, OH, $NO_2$, $CF_3$, —$(CH_2)_mCOOH$, —$(CH_2)_mCOOC_1$-$C_6$-alkyl;

Het denotes a divalent monocyclic or fused bicyclic unsaturated, saturated or aromatic heterocyclic group having 1 to 5 heteroatom independently selected from N, O, S and/or a group —C=O, which may be further substituted with 1 to 4 substituent selected from Hal, $C_1$-$C_6$-alkyl, —$(CH_2)_mOC_1$-$C_6$-alkyl, CN, OH, $NO_2$, $CF_3$, —$(CH_2)_mCOOH$, —$(CH_2)_mCOOC_1$-$C_6$-alkyl;

$Ar^1$ denotes a monocyclic or bicyclic, aromatic carbocyclic ring having 6 to 14 carbon atoms, which is unsubstituted or monosubstituted, disubstituted or trisubstituted by Hal, —$CF_3$, —$OCF_3$, —$NO_2$, —CN, perfluoroalkyl, Hal, —$CF_3$, —$OCF_3$, —$NO_2$, —CN, perfluoroalkyl, linear or branched $C_1$-$C_6$-alkyl, cycloalkyl, —OH, —$OC_1$-$C_6$-alkyl, —$COC_1$-$C_6$-alkyl, —$NH_2$, —COH, —COOH, —$CONH_2$, a group $R^b$ such as —$CH_2O(C_1$-$C_6$-alkyl), —$SO_2NR^aR^b$ or $SO_2(C_1$-$C_6$alkyl);

$Het^1$ denotes a monocyclic or bicyclic (fused, bridged or spiro) saturated, unsaturated or aromatic heterocyclic ring having 1 to 4 heteroatom independently selected from N, O, S and/or a CO group, which is unsubstituted or monosubstituted, disubstituted or trisubstituted by Hal, —$CF_3$, —$OCF_3$, —$NO_2$, —CN, perfluoroalkyl, linear or branched $C_1$-$C_6$-alkyl, $C_3$-$C_8$-cycloalkyl, —OH, —$OC_1$-$C_6$-alkyl, —$NH_2$, —$N(C_1$-$C_6$-alkyl$)_2$, —COH, —COOH, —$CONH_2$, —$COC_1$-$C_6$-alkyl, —$NHCO(C_3$-$C_6$cycloalkyl), a group $R^b$—$SO_2NR^aR^b$ or $SO_2(C_1$-$C_6$alkyl);

$Het^b$ denotes a monocyclic or bicyclic (fused or spiro) saturated, unsaturated or aromatic heterocyclic having 1 to 4 heteroatom independently selected from N, O, S and/or a CO group, which is unsubstituted or mono-substituted, disubstituted or trisubstituted by Hal, —$CF_3$, —$OCF_3$, —$NO_2$, —CN, perfluoroalkyl, —OH, —$OC_1$-$C_6$-alkyl, —$NH_2$, —COH, —COOH, —$CONH_2$, or by a linear or branched $C_1$-$C_6$-alkyl wherein 1 to 3 hydrogen atoms may be replaced by $NH_2$, $N(C_1$-$C_6$-alkyl$)_2$, $NH(C_1$-$C_6$-alkyl), $N(C_1$-$C_6$-alkyl)($C_3$-$C_8$-cycloalkyl), $NH(C_3$-$C_8$-cycloalkyl), $O(C_1$-$C_6$-alkyl), CN, OH, $CF_3$, Hal, $C_3$-$C_8$-cycloalkyl, or by a 4 to 8-membered heterocyclic ring containing an heteroatom selected from O, S and N;

$Ar^b$ denotes a monocyclic or bicyclic, aromatic carbocyclic ring having 6 to 14 carbon atoms, which is unsubstituted or monosubstituted, disubstituted or trisubstituted by Hal, —$CF_3$, —$OCF_3$, —$NO_2$, —CN, perfluoroalkyl, Hal, —$CF_3$, —$OCF_3$, —$NO_2$, —CN, perfluoroalkyl, —OH, —$OC_1$-$C_6$-alkyl, —$NH_2$, —COH, —COOH, —$CONH_2$, or by a linear or branched $C_1$-$C_6$-alkyl wherein 1 to 3 hydrogen atoms may be replaced by $NH_2$, $N(C_1$-$C_6$-alkyl$)_2$, $NH(C_1$-$C_6$-alkyl), $N(C_1$-$C_6$-alkyl)($C_3$-$C_8$-cycloalkyl), $NH(C_3$-$C_8$-cycloalkyl), $O(C_1$-$C_6$-alkyl), CN, OH, $CF_3$, Hal, $C_3$-$C_8$-cycloalkyl, or by a 4 to 8-membered heterocyclic ring containing an heteroatom selected from O, S and N;

Cyc denotes a saturated or unsaturated carbocyclic ring having 3 to 8 carbon atoms, preferably 5 or 6 carbon atoms, wherein 1 to 5H atoms are replaced by Hal, —$CF_3$, —$OCF_3$, —$NO_2$, —CN, perfluoroalkyl, Hal, —$CF_3$, —$OCF_3$, —$NO_2$, —CN, perfluoroalkyl, linear or branched $C_1$-$C_6$-alkyl, cycloalkyl, —OH, —$OC_1$-$C_6$-alkyl, —$COC_1$-$C_6$-alkyl, —$NH_2$, —COH, —COOH, —$CONH_2$, a group $R^b$ such as —$CH_2O(C_1$-$C_6$-alkyl), —$SO_2NR^aR^b$ or $SO_2(C_1$-$C_6$alkyl); or as defined and described in WO 2012/084704 and US 2013/0274241, the entirety of each of which is herein incorporated by reference.

In certain embodiments, the present invention provides a compound of Formula I, wherein IRAK is an IRAK4 inhibitor

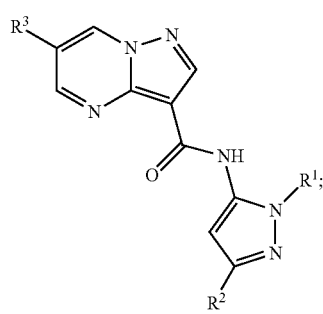

thereby forming a compound of formula I-kkk-1

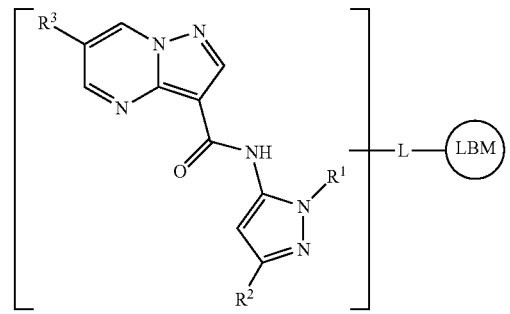

I-kkk-1 or a pharmaceutically acceptable salt thereof, wherein L and LBM are as defined above and described in embodiments herein, and wherein:

$R^1$ is aryl, heteroaryl, heterocyclyl or ($C_{1-6}$ alkyl)$R^6$, wherein said aryl, heteroaryl, and heterocyclyl groups are optionally substituted with one or two substituents selected from the group consisting of halo, cyano, $R^4$, $C_{3-8}$ cycloalkyl, $C_{1-3}$ aminoalkyl, $C_{1-3}$hydroxyalkyl, $OR^4$, $NR^4R^5$, $NR^4COR^6$, $NR^4SO_2R_6$, $SO_2NR^4R^5$, $CONR^4R^5$ and $CONR^4R^5$;

$R^2$ is aryl, heteroaryl, $C_{3-8}$ cycloalkyl, heterocyclyl or ($C_{1-6}$ alkyl)$R^6$, wherein said aryl, heteroaryl, cycloalkyl and heterocyclyl groups are optionally substituted with one or two substituents selected from the group consisting of halo, cyano, oxo, hydroxyl, imino, hydroxyimino, $R^4$, $OR^4$, $O(C_{3-8}$ cycloalkyl), (C=O)$OR^4$, $SO_mR^6$, $SO_mR^4$, $NR^4R^5$, $SO_2NR^4R^5$ and $NR^4SO_2R_6$;

$R^3$ is halo, cyano, oxo, hydroxyl, imino, hydroxyimino, $R^4$, $OR^4$, $C_{3-8}$cycloalkyl, $SO_mR^6$, $SO_mR^4NR^4R^5$ or (C=O) $NR^4R^5$, $NR^4(CO)R^6$, SOm$NR^4R^5$ and $NR^4SO_2R_6$;

$R^4$ is hydrogen or $C_{1-6}$ alkyl, wherein said alkyl is optionally substituted with one to three halo or hydroxyl;

$R^5$ is hydrogen or $C_{1-6}$ alkyl, wherein said alkyl is optionally substituted with halo or hydroxyl;

$R^6$ is aryl, heteroaryl, $C_{3-8}$ cycloalkyl or heterocyclyl;

m is an integer from zero to two;

as defined and described in WO 2012/129258 and US 2014/0194404, the entirety of each of which is herein incorporated by reference.

In certain embodiments, the present invention provides a compound of Formula I, wherein IRAK is an IRAK4 inhibitor

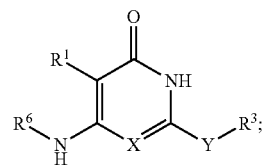

thereby forming a compound of formula I-lll-1

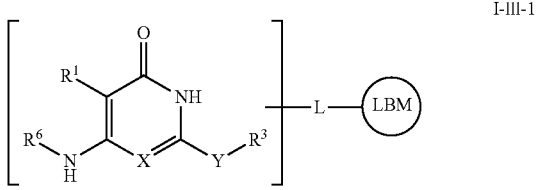

or a pharmaceutically acceptable salt thereof, wherein L and LBM are as defined above and described in embodiments herein, and wherein:

X is —N= or —CH=;

Y is selected from the group consisting of —NR$^2$—, —CH$_2$—, —CHR— and —O—, such that when Y is —CHR—, R and R$^3$ together with the carbon to which they are attached optionally form a 4- to 6-membered cycloalkyl, cycloalkenyl or heterocyclic ring, wherein the 4- to 6-membered cycloalkyl, cycloalkenyl, or heterocyclic ring is optionally substituted with one to three substituents independently selected from the group consisting of C$_{1-4}$ alkyl, C$_{3-6}$ cycloalkyl, phenyl, CF$_3$, heterocyclyl, halogen, —COOR$^8$, —NHR$^8$, —SR$^8$, —OR$^8$, —SO$_2$R$_8$, —COR$^8$, —NHCOR$^8$, and —CONHR$^8$; or when Y is —NR$^2$—, R$^2$ and R$^3$ together with the nitrogen to which they are attached optionally form a 4- to 6-membered heterocyclic ring, wherein the 4- to 6-membered heterocyclic ring is optionally substituted with one to three substituents independently selected from the group consisting of C$_{1-4}$ alkyl, C$_{3-6}$ cycloalkyl, phenyl, CF$_3$, heterocyclyl, halogen, —COOR$^8$, —NHR$^8$, —SR$^8$, —OR$^8$, —SO$_2$R$_8$, —COR$^8$, —NHCOR$^8$, and —CONHR$^8$;

R$^1$ is selected from the group consisting of hydrogen, C$_{1-10}$ alkyl, C$_{3-8}$cycloalkyl, aryl, heterocyclyl, halogen, —COOR$^7$, —NHR$^7$, —SR$^7$, —OR$^7$, —SO$_2$R$_7$, —COR$^7$, —NHCOR$^7$, and —CONHR$^7$; wherein said alkyl, cycloalkyl, aryl and heterocyclyl are optionally substituted with one to three substituents independently selected from the group consisting of C$_{1-4}$ alkyl, C$_{3-6}$ cycloalkyl, CN, phenyl, CF$_3$, heterocyclyl, halogen, —COOR$^8$, —NHR$^8$, SR$^8$, —OR$^8$, —SO$_2$R$_8$, —COR$^8$, —NHCOR$^8$, and —CONHR, wherein said —NHR$^8$ is optionally substituted with —N(C$_{1-4}$alkyl)NH$_2$ or —N(C$_{3-6}$ cycloalkyl)NH$_2$;

R$^2$ is selected from the group consisting of hydrogen, C$_{1-10}$ alkyl, and C$_{3-8}$ cycloalkyl;

R$^3$ is selected from the group consisting of hydrogen, C$_{1-10}$ alkyl, C$_{3-8}$cycloalkyl, aryl, heterocyclyl, and —COOR$^7$; wherein said alkyl, cycloalkyl, aryl and heterocyclyl are optionally substituted with one to three substituents independently selected from the group consisting of C$_{1-4}$ alkyl, C$_{3-6}$ cycloalkyl, phenyl, CF$_3$, heterocyclyl, halogen, —COOR$^8$, —NHR$^8$, —SR$^8$, —OR$^8$, —SO$_2$R$_8$, —COR$^8$, —NHCOR$^8$, and —CONHR$^8$;

R$^6$ is selected from the group consisting of C$_{1-10}$ alkyl, C$_{3-8}$ cycloalkyl, aryl, heterocyclyl, COOR$^7$, —SO$_2$R$_7$, and —COR$^7$; wherein said alkyl, cycloalkyl, aryl and heterocyclyl are optionally substituted with one to three substituents independently selected from the group consisting of C$_{1-4}$ alkyl, C$_{3-6}$ cycloalkyl, phenyl, CF$_3$, heterocyclyl, halogen, —COOR$^8$, —NHR$^8$, —SR$^8$, —OR$^8$, —SO$_2$R$_8$, —COR$^8$, —NHCOR$^8$, and —CONHR$^8$;

R$^7$ is selected from the group consisting of hydrogen, C$_{1-10}$ alkyl, C$_{3-8}$cycloalkyl, aryl, and heteroaryl; wherein said alkyl, cycloalkyl, aryl and heterocyclyl are optionally substituted with one to three substituents independently selected from the group consisting of C$_{1-4}$ alkyl, C$_{3-6}$cycloalkyl, phenyl, CF$_3$, heterocyclyl, halogen, —COOR$^8$, —NHR$^8$, —SR$^8$, —OR$^8$, —SO$_2$R$_8$, —COR$^8$, —NH-COR$^8$, and —CONHR$^8$; and R$^8$ is selected from the group consisting of hydrogen, C$_{1-6}$ alkyl and C$_{3-6}$ cycloalkyl;

as defined and described in WO 2013/066729 and US 2014/0329799, the entirety of each of which is herein incorporated by reference.

In certain embodiments, the present invention provides a compound of Formula I, wherein IRAK is an IRAK4 inhibitor

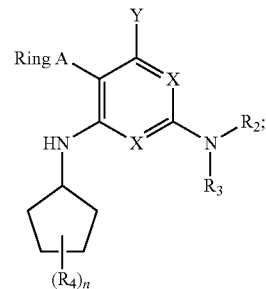

thereby forming a compound of formula I-mmm-1

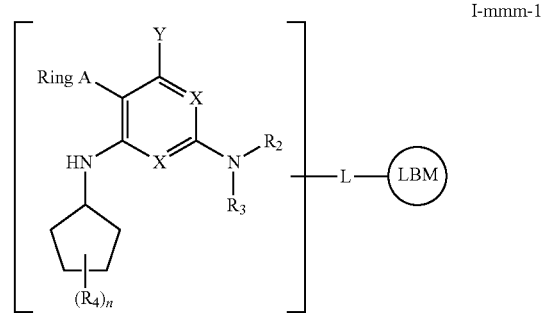

or a pharmaceutically acceptable salt thereof, wherein L and LBM are as defined above and described in embodiments herein, and wherein:

X is independently CH or N;

Y is H or methyl;

a is 0 or 1; b is 0 or 1; m is 0, 1 or 2; n is 0, 1, 2, 3 or 4;

Ring A is (C$_3$-C$_8$)cycloalkenyl, aryl or heterocycle optionally substituted with one to three substituents independently selected from R$_1$;

R$_1$ is selected from: H, oxo, (C=O)$_a$O$_b$(C$_1$-C$_{10}$)alkyl, (C=O)$_a$O$_b$-aryl, (C=O)$_a$O$_b$(C$_2$-C$_{10}$)alkenyl, (C=O)$_a$O$_b$(C$_2$-C$_{10}$)alkynyl, CO$_2$H, halo, OH, O$_b$(C$_1$-C$_6$)fluoroalkyl, (C=O)$_a$NR$_5$R$_6$, CN, (C=O)$_a$O$_b$(C$_3$-C$_8$)cycloalkyl, S(O)$_m$ NR$_5$R$_6$, SH, S(O)$_m$—(C$_1$-C$_{10}$)alkyl and (C=O)$_a$O$_b$-heterocyclyl, said alkyl, aryl, alkenyl, alkynyl, cycloalkyl, and heterocyclyl are optionally substituted with one or more substituents selected from R$^a$;

R$_2$ and R$_3$ are independently selected from: H, (C=O)$_a$O$_b$C$_1$-C$_{10}$ alkyl, (C=O)$_a$O$_b$aryl, C$_2$-C$_{10}$ alkenyl, C$_2$-C$_{10}$ alkynyl, (C=O)$_a$O$_b$ heterocyclyl, CO$_2$H, CN, O$_b$C$_1$-C$_6$fluoroalkyl, O$_a$(C=O)$_b$NR$_5$R$_6$, CHO, (N=O)R$_5$R$_6$, S(O)$_m$NR$_5$R$_6$, SH, S(O)$_m$ (C$_1$-C$_{10}$)alkyl, (C=O)$_a$O$_b$C$_3$-

$C_8$ cycloalkyl, optionally substituted with one or more substituents selected from $R_1$; or $R_2$ and $R_3$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one or more substituents selected from $R_1$;

$R_4$ is independently selected from: $(C_1$-$C_6)$alkyl, OH, methoxy, $CF_3$ and F, said alkyl optionally substituted with OH;

$R_5$ and $R_6$ are independently selected from H, $(C=O)_aO_b$ $(C_1$-$C_{10})$alkyl, $(C=O)_aO_b$-aryl, $(C=O)_aO_b(C_2$-$C_{10})$alkenyl, $(C=O)_aO_b(C_2$-$C_{10})$alkynyl, $CO_2H$, $O_b(C_1$-$C_6)$fluoroalkyl, $(C=O)_aN(R^a)_2$, CN, $(C=O)_aO_b(C_3$-$C_8)$cycloalkyl, $S(O)_mN(R^a)_2$, SH, $S(O)_m$ $(C_1$-$C_{10})$alkyl and $(C=O)_aO_b$-heterocyclyl, said alkyl, aryl, alkenyl, alkynyl, cycloalkyl, and heterocyclyl are optionally substituted with one or more substituents selected from $R^a$;

$R_a$ is independently selected from $R^b$, OH, $(C_1$-$C_6)$alkoxy, halogen, cyclopropyl, $CO_2H$, CN, $O_a(C=O)_b(C_1$-$C_6)$alkyl, oxo, and $N(R^b)_2$; and $R^b$ is independently selected from H and $(C_1$-$C_6)$alkyl; as defined and described in WO 2014/058685 and US 2015/0299224, the entirety of each of which is herein incorporated by reference.

In certain embodiments, the present invention provides a compound of Formula I, wherein IRAK is an IRAK4 inhibitor

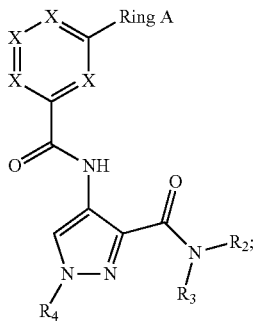

thereby forming a compound of formula I-nnn-1

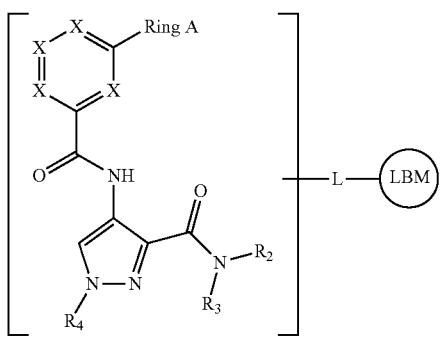

I-nnn-1 or a pharmaceutically acceptable salt thereof, wherein L and LBM are as defined above and described in embodiments herein, and wherein:

X is CH or N;

a is 0 or 1; b is 0 or 1; m is 0, 1 or 2;

Ring A is $(C_3$-$C_8)$cycloalkyl, $(C_3$-$C_8)$cycloalkenyl, aryl or heterocycle optionally substituted with one to three substituents independently selected from $R_1$;

$R_1$ is selected from: H, oxo, $(C=O)_aO_b(C_1$-$C_{10})$alkyl, $(C=O)_aO_b$-aryl, $(C=O)_aO_b(C_2$-$C_{10})$alkenyl, $(C=O)_aO_b$ $(C_2$-$C_{10})$alkynyl, $CO_2H$, halo, OH, $O_b(C_1$-$C_6)$fluoroalkyl, $(C=O)_aNR_5R_6$, CN, $(C=O)_aO_b(C_3$-$C_8)$cycloalkyl, $S(O)_m$ $NR_5R_6$, SH, $S(O)_m$—$(C_1$-$C_{10})$alkyl and $(C=O)_a$ $O_b$-heterocyclyl, said alkyl, aryl, alkenyl, alkynyl, cycloalkyl, and heterocyclyl are optionally substituted with one or more substituents selected from $R_a$;

$R_2$ and $R_3$ are independently selected from: H, $(C=O)_a$ $O_bC_1$-$C_{10}$ alkyl, $(C=O)_aO_b$aryl, $C_2$-$C_{10}$ alkenyl, $C_2$-$C_{10}$ alkynyl, $(C=O)_aO_b$ heterocyclyl, $CO_2H$, CN, $O_bC_1$-$C_6$ fluoroalkyl, $O_a(C=O)_bNR_5R_6$, CHO, $(N=O)R_5R_6$, $S(O)_m$ $NR_5R_6$, SH, $S(O)_m$ $(C_1$-$C_{10})$alkyl, $(C=O)_aO_bC_3$-$C_8$ cycloalkyl, optionally substituted with one or more substituents selected from $R_1$; or $R_2$ and $R_3$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one or more substituents selected from $R_1$;

$R_4$ is selected from: $(C_1$-$C_6)$alkyl and $(C_3$-$C_6)$cycloalkyl, optionally substituted with $R_a$;

$R_5$ and $R_6$ are independently selected from: H, oxo, $(C=O)_a$ $O_b(C_1$-$C_{10})$alkyl, $(C=O)_aO_b$-aryl, $(C=O)_aO_b(C_2$-$C_{10})$ alkenyl, $(C=O)_aO_b(C_2$-$C_{10})$alkynyl, $CO_2H$, $O_b(C_1$-$C_6)$ fluoroalkyl, $(C=O)_aN(R^a)_2$, CN, $(C=O)_aO_b(C_3$-$C_8)$cycloalkyl, $S(O)_mN(R^a)_2$, SH, $S(O)_m$ $(C_1$-$C_{10})$alkyl and $(C=O)_aO_b$-heterocyclyl, said alkyl, aryl, alkenyl, alkynyl, cycloalkyl, and heterocyclyl are optionally substituted with one or more substituents selected from $R_a$;

$R_a$ is independently selected from $R_b$, OH, $(C_1$-$C_6)$alkoxy, halogen, cyclopropyl, $CO_2H$, CN, $O_a(C=O)_b(C_1$-$C_6)$alkyl, oxo, and $N(R_b)_2$; and $R^b$ is independently selected from H and $(C_1$-$C_6)$alkyl;

as defined and described in WO 2014/058691 and US 2015/0274708, the entirety of each of which is herein incorporated by reference.

In certain embodiments, the present invention provides a compound of Formula I, wherein IRAK is an IRAK4 inhibitor

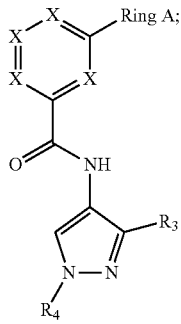

thereby forming a compound of formula I-nnn'-1

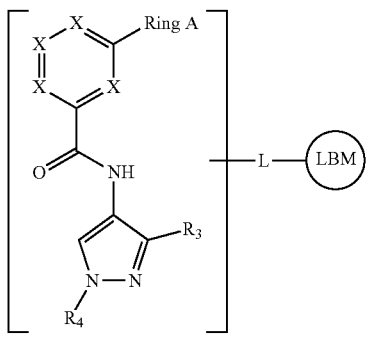

I-nnn'-1 or a pharmaceutically acceptable salt thereof, wherein L and LBM are as defined above and described in embodiments herein, and wherein each of the variables $R_3$, $R_4$, X, and Ring A is as defined and described in WO 2014/058691, the entirety of each of which is herein incorporated by reference.

In certain embodiments, the present invention provides a compound of Formula I, wherein IRAK is an IRAK4 inhibitor

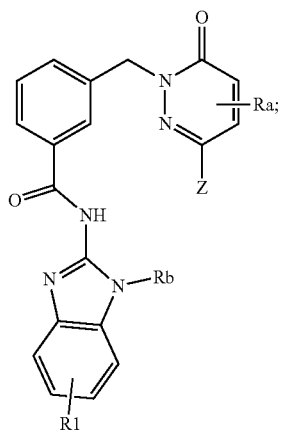

thereby forming a compound of formula I-ooo-1

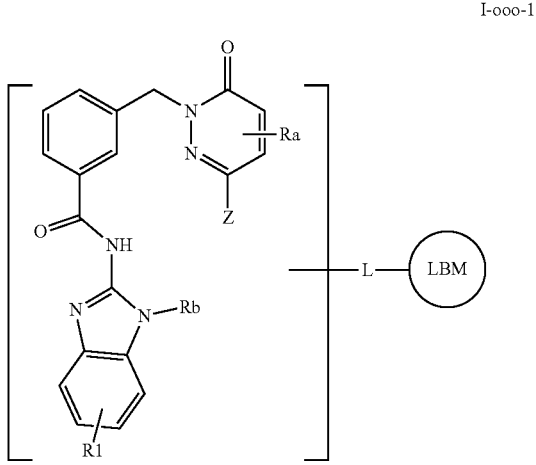

I-ooo-1 or a pharmaceutically acceptable salt thereof, wherein L and LBM are as defined above and described in embodiments herein, and wherein:

Z denotes a group

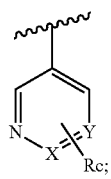

wherein

X is CH or N;

Y is CH or N;

Ra, Rc, R1 denote each independently H, Hal or A1;

Rb is H or alkyl;

A1 is branched or linear alkyl having 1 to 12 C-atoms, wherein one or more, such as 1 to 7, H atoms may be replaced by Hal, ORb, COORb, CN or N(Rb)$_2$ and wherein one or more, preferably 1 to 5 CH$_2$-groups may be replaced by O, CO, NRb or S, SO, SO$_2$, 1,2-, 1,3- or 1,4-phenylen, —CH═CH— or —C≡C—; and Hal denotes F, Cl, Br, I;

as defined and described in WO 2014/121931 and US 2015/0376167, the entirety of each of which is herein incorporated by reference.

In certain embodiments, the present invention provides a compound of Formula I, wherein IRAK is an IRAK4 inhibitor

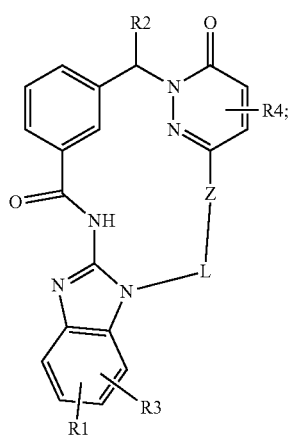

thereby forming a compound of formula I-ppp-1

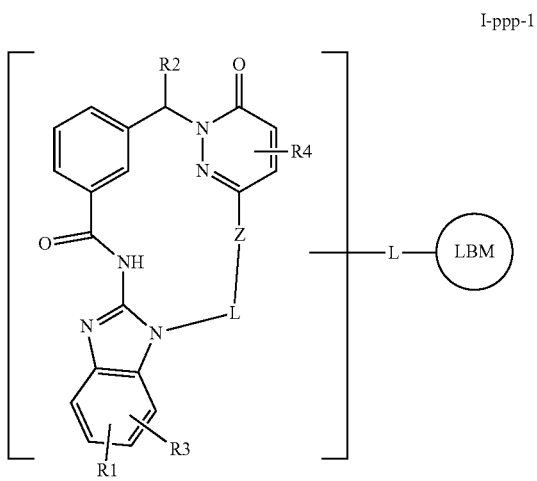

or a pharmaceutically acceptable salt thereof, wherein L and LBM are as defined above and described in embodiments herein, and wherein:

R1, R3 denote each, independently of one another H, $(CH_2)_p CON(R5)_2$, OA, Hal, COOH, COOA, $(CH_2)_p NH$-COA, $(CH_2)_p Het1$, $(CH_2)_p NR2R5$, or OH;

R2 denotes H or linear or branched alkyl with 1, 2 or 3 C atoms, wherein one or two H atoms of the alkyl group are optionally replaced by OR6, NR5R6, NHCOR5, CONR5R6;

R4 denotes H or A;

R5 denotes H or linear or branched alkyl with 1, 2 or 3 C atoms;

R6 denotes H or linear or branched alkyl with 1, 2 or 3 C atoms;

Z is absent or denotes Ar-diyl or Het-diyl;

L denotes $(CH_2)_n$ wherein one or two $CH_2$ groups are optionally replaced by O and/or a CH=CH— group, and/or wherein one or two H atoms are optionally replaced by OR2, NR2R5 or Het1;

Ar-diyl denotes 1,2-, 1,3- or 1,4-phenylen optionally substituted with from 1 to 5 groups independently selected from the group consisting of Hal, CN, —$CF_3$, —$OCF_3$, OH, O-A, $SO_2$-A, COOH, COOA, —CO-A, O-phenyl, $SO_2$-phenyl, $SO_2$—$CF_3$, Het2 and A;

Het-diyl denotes an unsaturated, saturated or aromatic 5- or 6-membered heterocycle comprising 1 to 2 N, O and/or S atoms, which are optionally unsubstituted or mono-, di- or trisubstituted by Hal, CN, —$CF_3$, —$OCF_3$, O-A, $SO_2$-A, COOH, COOA, —CO-A, O-phenyl, $SO_2$-phenyl, $SO_2$—$CF_3$, Het2 and/or A;

A denotes an unbranched or branched alkyl comprising 1 to 10 C atoms, in which 1 to 5H atoms are optionally replaced by F and/or in which one or two non-adjacent $CH_2$ groups are optionally replaced by O;

Het1 denotes morpholinyl, piperidinyl or pyrrolidinyl;
Het2 denotes morpholinyl, piperidinyl or pyrrolidinyl;
Hal denotes F, Cl, Br, I;
n denotes 1, 2, 3, 4, 5 or 6;
p denotes 0, 1 or 2;
as defined and described in WO 2014/121942 and US 2015/0376206, the entirety of each of which is herein incorporated by reference.

In certain embodiments, the present invention provides a compound of Formula I, wherein IRAK is an IRAK1 and/or IRAK4 inhibitor

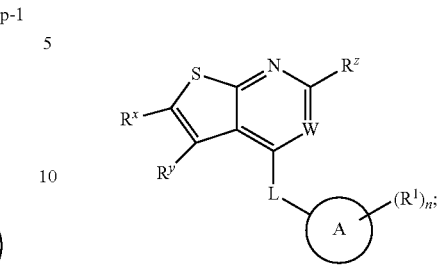

thereby forming a compound of formula I-qqq-1

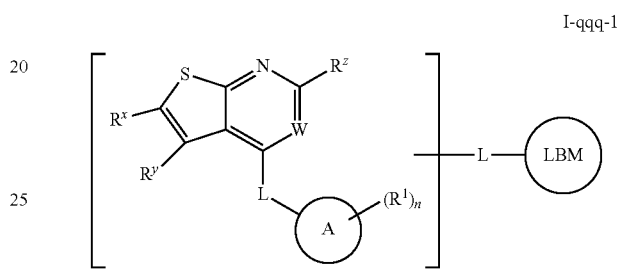

or a pharmaceutically acceptable salt thereof, wherein L and LBM are as defined above and described in embodiments herein, and wherein Ring A is a 3-7 membered saturated or partially unsaturated carbocyclic ring or a 4-7 membered saturated or partially unsaturated heterocyclic ring having 1-3 heteroatoms independently selected from nitrogen, oxygen, or sulfur;

n is 0-4;

each $R^1$ is independently —R, halogen, —CN, —$NO_2$, —OR, —$CH_2OR$, —SR, —$N(R)_2$, —$SO_2R$, —$SO_2N(R)_2$, —SOR, —C(O)R, —COIR, —C(O)N(R)$_2$, —C(O)N(R)—OR, —NRC(O)R, —NRC(O)N(R)$_2$, Cy, or —$NRSO_2R$; or $R^1$ is selected from one of the following formulas:

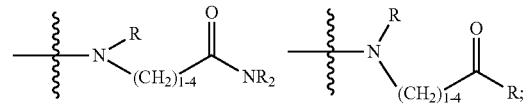

or two $R^1$ groups are taken together with their intervening atoms to form an optionally substituted 4-7 membered fused, spiro-fused, or bridged bicyclic ring having 0-2 heteroatoms independently selected from nitrogen, oxygen, or sulfur;

each Cy is an optionally substituted ring selected from a 3-7 membered saturated or partially unsaturated carbocyclic ring or a 4-7 membered saturated or partially unsaturated heterocyclic ring having 1-3 heteroatoms independently selected from nitrogen, oxygen, or sulfur;

each R is independently hydrogen or an optionally substituted group selected from $C_{1-6}$ aliphatic, aryl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur;

$R^z$ is —R, —CN, —NO$_2$, halogen, —C(O)N(R)$_2$, —C(O)OR, —C(O)R, —N(R)$_2$, —OR, or —SO$^2$N(R)$_2$;

Ring B is an unsubstituted 4-8 membered partially unsaturated carbocyclic fused ring; and L is a C$_{1-6}$ bivalent hydrocarbon chain wherein one or two methylene units of the chain are optionally and independently replaced by —NR—, —N(R)C(O)—, —C(O)N(R)—, —N(R)SO$_2$—, —SO$_2$N(R)—, —O—, —C(O)—, —OC(O)—, —C(O)O—, —S—, —SO— or —SO$_2$—, as defined and described in WO 2012/097013 and US 2012/0283238, the entirety of each of which is herein incorporated by reference.

In certain embodiments, the present invention provides a compound of Formula I, wherein IRAK is an IRAK1 and/or IRAK4 inhibitor

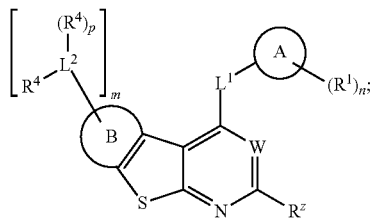

thereby forming a compound of formula I-rrr-1

I-rrr-1

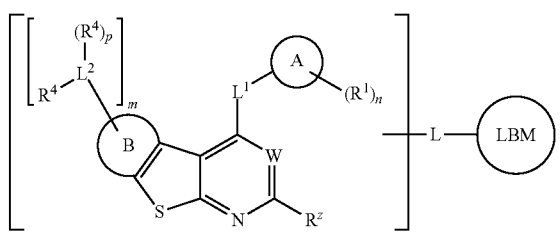

or a pharmaceutically acceptable salt thereof, wherein L and LBM are as defined above and described in embodiments herein, and wherein:

Ring A is a 3-7 membered saturated or partially unsaturated carbocyclic ring or a 4-7 membered saturated or partially unsaturated heterocyclic ring having 1-3 heteroatoms independently selected from nitrogen, oxygen, or sulfur;

n is 0-4;

each $R^1$ is independently —R, halogen, —CN, —NO$_2$, —OR, —CH$_2$OR, —SR, —N(R)$_2$, —SO$_2$R, —SO$_2$N(R)$_2$, —SOR, —C(O)R, —CO$_2$R, —C(O)N(R)$_2$, —C(O)N(R)—OR, —NRC(O)OR, —NRC(O)N(R)$_2$, Cy, or —NRSO$_2$R; or $R^1$ is selected from one of the following formulas:

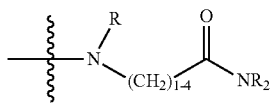

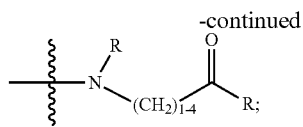

-continued or two $R^1$ groups are taken together with their intervening atoms to form an optionally substituted 4-7 membered fused, spiro-fused, or bridged bicyclic ring having 0-2 heteroatoms independently selected from nitrogen, oxygen, or sulfur;

each Cy is an optionally substituted ring selected from a 3-7 membered saturated or partially unsaturated carbocyclic ring or a 4-7 membered saturated or partially unsaturated heterocyclic ring having 1-3 heteroatoms independently selected from nitrogen, oxygen, or sulfur;

each R is independently hydrogen, or an optionally substituted group selected from C$_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur;

Ring B is a cyclopento or cyclohexo fused ring;

m is 1-2;

p is 0-2;

W is N;

$R^z$ is R, CN, NO$_2$, halogen, —C(O)N(R)$_2$, —C(O)OR, —C(O)R, —N(R)C(O)OR, —NRC(O)N(R)$_2$, —OR, or —SO$_2$N(R)$_2$;

$L^1$ is a covalent bond or a C$_{1-6}$ bivalent hydrocarbon chain wherein one or two methylene units of the chain are optionally and independently replaced by —NR—, —N(R)C(O)—, —C(O)N(R)—, —N(R)SO$_2$—, —SO$_2$N(R)—, —O—, —C(O)—, —OC(O)—, —C(O)O—, —S—, —SO— or —SO$_2$—;

each $L^2$ is independently a covalent bond or a C$_{1-6}$ bivalent hydrocarbon chain wherein one or two methylene units of the chain are optionally and independently replaced by —NR—, —N(R)C(O)—, —C(O)N(R)—, —N(R)SO$_2$—, —SO$_2$N(R)—, —O—, —C(O)—, —OC(O)—, —C(O)O—, —S—, —SO— or —SO$_2$—;

each $R^4$ is independently halogen, —CN, —NO$_2$, —OR, —SR, —N(R)$_2$, —SO$_2$R, —SO$_2$N(R)$_2$, —SOR, —C(O)R, —CO$_2$R, —C(O)N(R)$_2$, —NRC(O)R, —NRC(O)N(R)$_2$, C(O)N(R)OR, —N(R)C(O)OR, —N(R)S(O)$_2$N(R)$_2$, —NRSO$_2$R, or an optionally substituted group selected from C$_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur, or:

two -L$^2$(R$^4$)$_p$R$^4$ groups are taken together with their intervening atoms to form an optionally substituted 4-7 membered fused, spiro-fused, or bridged bicyclic ring having 0-2 heteroatoms independently selected from nitrogen, oxygen, or sulfur;

as defined and described in WO 2013/106535 and US 2013/0231328, the entirety of each of which is herein incorporated by reference.

In certain embodiments, the present invention provides a compound of Formula I, wherein IRAK is an IRAK1 and/or IRAK4 inhibitor

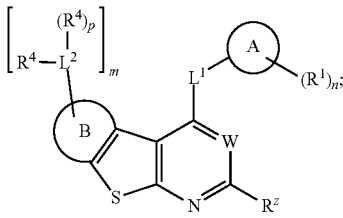

thereby forming a compound of formula I-sss-1

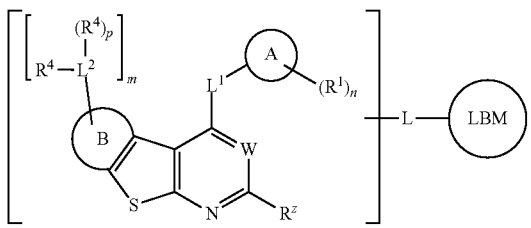

I-sss-1 or a pharmaceutically acceptable salt thereof, wherein L and LBM are as defined above and described in embodiments herein, and wherein Ring A is a 3-7 membered saturated or partially unsaturated carbocyclic ring or a 4-7 membered saturated or partially unsaturated heterocyclic ring having 1-3 heteroatoms independently selected from nitrogen, oxygen, and sulfur;
n is 0-4;
each $R^1$ is independently —R, halogen, —CN, —NO$_2$, —OR, —CH$_2$OR, —SR, —N(R)$_2$, —S(O)$_2$R, —S(O)$_2$N(R)$_2$, —SOR, —C(O)R, —CO$_2$R, —C(O)N(R)$_2$, —C(O)N(R)—OR, —N(R)C(O)R, —N(R)C(O)OR, —N(R)C(O)N(R)$_2$, Cy, or —N(R)S(O)$_2$R, or $R^1$ is selected from one of the following formulas:

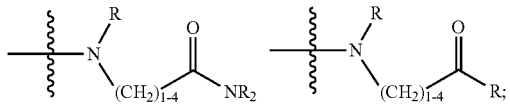

or two $R^1$ groups are taken together with their intervening atoms to form an optionally substituted 4-7 membered fused, spiro-fused, or bridged bicyclic ring having 0-2 heteroatoms independently selected from nitrogen, oxygen, and sulfur;
each Cy is an optionally substituted ring selected from a 3-7 membered saturated or partially unsaturated carbocyclic ring or a 4-7 membered saturated or partially unsaturated heterocyclic ring having 1-3 heteroatoms independently selected from nitrogen, oxygen, and sulfur;
each R is independently hydrogen, or an optionally substituted group selected from $C_{1-6}$ aliphatic, phenyl, 4-7 membered saturated or partially unsaturated heterocyclic having 1-2 heteroatoms independently selected from nitrogen, oxygen, and sulfur, or 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;
Ring B is selected from a benzo fused ring and a 5-6 membered heteroaromatic fused ring having 1-3 heteroatoms independently selected from nitrogen, oxygen, and sulfur; wherein said Ring B may be optionally substituted by one or more oxo, thiono, or imino groups;
m is 0-4;
p is 0-2;
W is N or —C($R^3$);
$R^z$ is R, CN, NO$_2$, halogen, —C(O)N(R)$_2$, —C(O)OR, —C(O)R, —N(R)$_2$, —N(R)C(O)OR, —N(R)C(O)N(R)$_2$, —OR, or —S(O)$_2$N(R)$_2$;
$R^3$ is hydrogen, halogen, —CN, $C_{1-4}$ aliphatic, $C_{1-4}$haloaliphatic, —OR, —C(O)R, or —C(O)N(R)$_2$;
$L^1$ is a covalent bond or a $C_{1-6}$ bivalent hydrocarbon chain wherein one or two methylene units of the chain are optionally and independently replaced by —N(R)—, —N(R)C(O)—, —C(O)N(R)—, —N(R)S(O)$_2$—, —S(O)$_2$ N(R)—, —O—, —C(O)—, —OC(O)—, —C(O)O—, —S—, —S(O)— or —S(O)$_2$—;
each $L^2$ is independently a covalent bond or a $C_{1-6}$ bivalent hydrocarbon chain wherein one or two methylene units of the chain are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—; and
each $R^4$ is independently halogen, —CN, —NO$_2$, —OR, —SR, —N(R)$_2$, —S(O)$_2$R, —S(O)$_2$N(R)$_2$, —S(O)R, —C(O)R, —CO$_2$R, —C(O)N(R)$_2$, —N(R)C(O)R, —N(R)C(O)N(R)$_2$, —C(O)N(R)OR, —N(R)C(O)OR, —N(R)S(O)$_2$N(R)$_2$, —N(R)S(O)$_2$R, or an optionally substituted group selected from $C_{1-6}$ aliphatic, phenyl, 4-7 membered saturated or partially unsaturated heterocyclic having 1-2 heteroatoms independently selected from nitrogen, oxygen, and sulfur, or 5-6 membered heteroaryl ring having 1-4 heteroatoms independently selected from nitrogen, oxygen, and sulfur, or
two -$L^2(R^4)_p$—$R^4$ groups are taken together with their intervening atoms to form an optionally substituted 4-7 membered fused, or bridged bicyclic ring having 0-2 heteroatoms independently selected from nitrogen, oxygen, and sulfur;
as defined and described in WO 2014/011902 and US 2014/0018343, the entirety of each of which is herein incorporated by reference.

In certain embodiments, the present invention provides a compound of Formula I, wherein IRAK is an IRAK1 and/or IRAK4 inhibitor

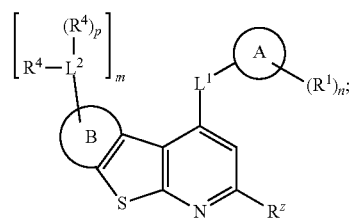

thereby forming a compound of formula I-ttt-1

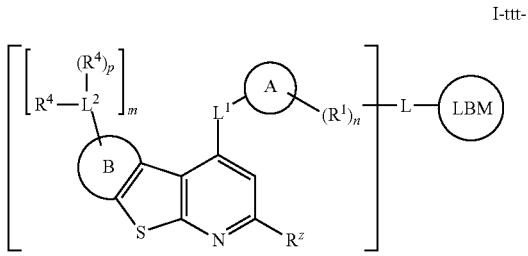

I-ttt-1 or a pharmaceutically acceptable salt thereof, wherein L and LBM are as defined above and described in embodiments herein, and wherein Ring A is a 3-7 membered saturated or partially unsaturated carbocyclic ring or a 4-7 membered saturated or partially unsaturated heterocyclic ring having 1-3 heteroatoms independently selected from nitrogen, oxygen, and sulfur;
n is 0-4;
each $R^1$ is independently —R, halogen, —CN, —NO$_2$, —OR, —CH$_2$OR, —SR, —N(R)$_2$, —S(O)$_2$R, —S(O)$_2$N(R)$_2$, —S(O)R, —C(O)R, —C(O)OR, —C(O)N(R)$_2$, —C(O)N(R)—OR, —N(R)C(O)R, —N(R)C(O)OR, —N(R)C(O)N(R)$_2$, Cy, or —N(R)S(O)$_2$R; or $R^1$ is selected from one of the following formulas:

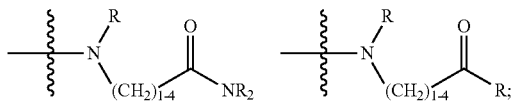

two $R^1$ groups are taken together with their intervening atoms to form an optionally substituted 4-7 membered fused, spiro-fused, or bridged bicyclic ring having 0-2 heteroatoms independently selected from nitrogen, oxygen, and sulfur;
each Cy is an optionally substituted ring selected from a 3-7 membered saturated or partially unsaturated carbocyclic ring or a 4-7 membered saturated or partially unsaturated heterocyclic ring having 1-3 heteroatoms independently selected from nitrogen, oxygen, and sulfur;
each R is independently hydrogen, or an optionally substituted group selected from $C_{1-6}$ aliphatic, phenyl, 4-7 membered saturated or partially unsaturated heterocyclic having 1-2 heteroatoms independently selected from nitrogen, oxygen, and sulfur, or 5-6 membered heteroaryl ring having 1-4 heteroatoms independently selected from nitrogen, oxygen, and sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;
Ring B is selected from a 4-8 membered partially unsaturated carbocyclic fused ring and a 4-7 membered partially unsaturated heterocyclic fused ring having 1-2 heteroatoms selected from nitrogen, oxygen, and sulfur; wherein said Ring B may be optionally substituted by one or more oxo, thiono, or imino groups;
m is 0-4;
p is 0-2;

$R^z$ is —R, —CN, —NO$_2$, halogen, —C(O)N(R)$_2$, —C(O)OR, —C(O)R, —N(R)$_2$, —N(R)C(O)OR, —N(R)C(O)N(R)$_2$, —OR, or —S(O)$_2$N(R)$_2$;
$R^3$ is hydrogen, halogen, —CN, $C_{1-4}$ aliphatic, $C_{1-4}$ haloaliphatic, —OR, —C(O)R, or —C(O)N(R)$_2$;
$L^1$ is a covalent bond or a $C_{1-6}$ bivalent hydrocarbon chain wherein one or two methylene units of the chain are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—;
each $L^2$ is independently a covalent bond or a $C_{1-6}$ bivalent hydrocarbon chain wherein one or two methylene units of the chain are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—; and
each $R^4$ is independently halogen, —CN, —NO$_2$, —OR, —SR, —N(R)$_2$, —S(O)$_2$R, —S(O)$_2$N(R)$_2$, —S(O)R, —C(O)R, —C(O)OR, —C(O)N(R)$_2$, —N(R)C(O)R, —N(R)C(O)N(R)$_2$, —C(O)N(R)OR, —N(R)C(O)OR, —N(R)S(O)$_2$N(R)$_2$, —N(R)S(O)$_2$R, or an optionally substituted group selected from $C_{1-6}$ aliphatic, phenyl, 4-7 membered saturated or partially unsaturated heterocyclic having 1-2 heteroatoms independently selected from nitrogen, oxygen, and sulfur, or 5-6 membered heteroaryl ring having 1-4 heteroatoms independently selected from nitrogen, oxygen, and sulfur, or
two -$L^2(R^4)_pR^4$ groups are taken together with their intervening atoms to form an optionally substituted 4-7 membered fused, spiro-fused, or bridged bicyclic ring having 0-2 heteroatoms independently selected from nitrogen, oxygen, and sulfur;
as defined and described in WO 2014/011906 and US 2014/0018357, the entirety of each of which is herein incorporated by reference.

In certain embodiments, the present invention provides a compound of Formula I, wherein IRAK is an IRAK1 and/or IRAK4 inhibitor

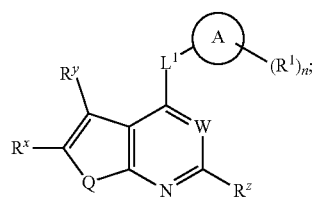

thereby forming a compound of formula I-uuu-1

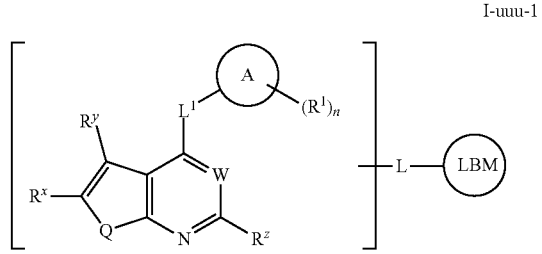

I-uuu-1 or a pharmaceutically acceptable salt thereof, wherein L and LBM are as defined above and described in embodiments herein, and wherein:

Ring A is a 3-7 membered saturated or partially unsaturated carbocyclic ring or a 4-7 membered saturated or partially unsaturated heterocyclic ring having 1-3 heteroatoms independently selected from nitrogen, oxygen, and sulfur;

n is 0-4;

each $R^1$ is independently —R, halogen, —CN, —NO$_2$, —OR, —CH$_2$OR, —SR, —N(R)$_2$, —S(O)$_2$R, —S(O)$_2$N(R)$_2$, —S(O)R, —C(O)R, —C(O)OR, —C(O)N(R)$_2$, —C(O)N(R)—OR, —N(R)C(O)R, —N(R)C(O)OR, —N(R)C(O)N(R)$_2$, Cy, or —N(R)S(O)$_2$R; or $R^1$ is selected from one of the following formulas:

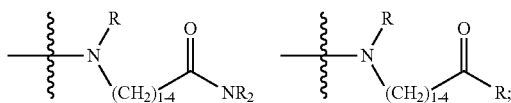

or two $R^1$ groups are taken together with their intervening atoms to form an optionally substituted 4-7 membered fused, spiro-fused, or bridged bicyclic ring having 0-2 heteroatoms independently selected from nitrogen, oxygen, and sulfur;

each Cy is an optionally substituted ring selected from a 3-7 membered saturated or partially unsaturated carbocyclic ring or a 4-7 membered saturated or partially unsaturated heterocyclic ring having 1-3 heteroatoms independently selected from nitrogen, oxygen, and sulfur;

each R is independently hydrogen, or an optionally substituted group selected from $C_{1-6}$ aliphatic, phenyl, 4-7 membered saturated or partially unsaturated heterocyclic having 1-2 heteroatoms independently selected from nitrogen, oxygen, and sulfur, or 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each of $R^x$ and $R^y$ is independently —R, halogen, —CN, —NO$_2$, —OR, —SR, —N(R)$_2$, —S(O)$_2$R, —S(O)$_2$N(R)$_2$, —S(O)R, —C(O)R, —C(O)OR, —C(O)N(R)$_2$, —N(R)C(O)R, —N(R)C(O)N(R)$_2$, or —N(R)S(O)$_2$R, or:

$R^x$ and $R^y$ are taken together with their intervening atoms to form Ring B substituted with m occurrences of

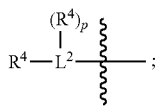

Ring B is selected from a benzo fused ring, a 4-8 membered partially unsaturated carbocyclic fused ring, a 4-8 membered partially unsaturated heterocyclic fused ring having one or two heteroatoms independently selected from nitrogen oxygen and sulfur, and a 5-6 membered heteroaromatic fused ring having 1-3 heteroatoms independently selected from nitrogen, oxygen, and sulfur; wherein said Ring B may be optionally substituted by one or more oxo, thiono, or imino groups;

m is 0-4;

p is 0-2;

Q is —O— or —N(R)—

W is N or —C($R^3$)—;

$R^z$ is —R, —CN, —NO$_2$, halogen, —C(O)N(R)$_2$, —C(O)OR, —C(O)R, —N(R)$_2$, —N(R)C(O)OR, —N(R)C(O)N(R)$_2$, —OR, or —S(O)$_2$N(R)$_2$;

$R^3$ is hydrogen, halogen, —CN, $C_{1-4}$ aliphatic, $C_{1-4}$ haloaliphatic, —OR, —C(O)R, or —C(O)N(R)$_2$;

$L^1$ is a covalent bond or a $C_{1-6}$ bivalent hydrocarbon chain wherein one or two methylene units of the chain are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—;

each $L^2$ is independently a covalent bond or a $C_{1-6}$ bivalent hydrocarbon chain wherein one or two methylene units of the chain are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—; and each $R^4$ is independently halogen, —CN, —NO$_2$, —OR, —SR, —N(R)$_2$, —S(O)$_2$R, —S(O)$_2$N(R)$_2$, —S(O)R, —C(O)R, —C(O)OR, —C(O)N(R)$_2$, —N(R)C(O)R, —N(R)C(O)N(R)$_2$, —C(O)N(R)OR, —N(R)C(O)OR, —N(R)S(O)$_2$N(R)$_2$, —N(R)S(O)$_2$R, or an optionally substituted group selected from $C_{1-6}$ aliphatic, phenyl, 4-7 membered saturated or partially unsaturated heterocyclic having 1-2 heteroatoms independently selected from nitrogen, oxygen, and sulfur, or 5-6 membered heteroaryl ring having 1-4 heteroatoms independently selected from nitrogen, oxygen, and sulfur, or two -$L^2$($R^4$)$_p$—$R^4$ groups are taken together with their intervening atoms to form an optionally substituted 4-7 membered fused, spiro, or bridged bicyclic ring having 0-2 heteroatoms independently selected from nitrogen, oxygen, and sulfur;

as defined and described in WO 2014/011911 and US 2014/0018361, the entirety of each of which is herein incorporated by reference.

In certain embodiments, the present invention provides a compound of Formula I, wherein IRAK is an IRAK1 and/or IRAK4 inhibitor

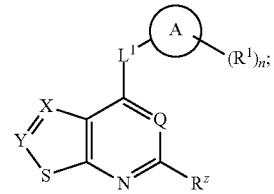

thereby forming a compound of formula I-vvv-1

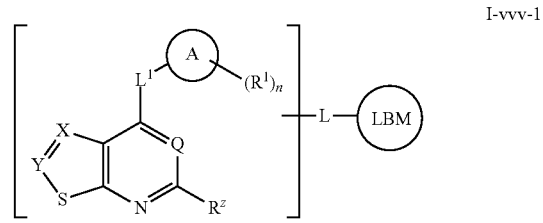

I-vvv-1 or a pharmaceutically acceptable salt thereof, wherein L and LBM are as defined above and described in embodiments herein, and wherein:

Q is CH, C—CN, or N;

X is C-L²(R⁴)ₚ—Rˣ and Y is N; or

X is N and Y is C-Rx;

Ring A is a 3-7 membered saturated or partially unsaturated carbocyclic ring or a 4-7 membered saturated or partially unsaturated heterocyclic ring having 1-3 heteroatoms independently selected from nitrogen, oxygen, or sulfur;

each $R^1$ and $R^{1'}$ is independently —$R^2$, halogen, —CN, —NO₂, —OR, —SR, —N(R)₂, —S(O)₂R, —S(O)₂N(R)₂, —S(O)R, —C(O)R, —C(O)OR, —C(O)N(R)₂, —C(O)N(R)OR, —N(R)C(O)OR, —N(R)C(O)N(R)₂, Cy, or —N(R)S(O)₂R; or $R^1$ is selected from one of the following formulas:

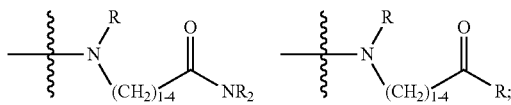

or two $R^1$ groups are taken together with their intervening atoms to form an optionally substituted 4-7 membered fused, spiro-fused, or bridged bicyclic ring having 0-2 heteroatoms independently selected from nitrogen, oxygen, or sulfur;

each Cy is an optionally substituted ring selected from a 3-7 membered saturated or partially unsaturated carbocyclic ring or a 4-10 membered saturated or partially unsaturated heterocyclic ring having 1-3 heteroatoms independently selected from nitrogen, oxygen, or sulfur;

each R is independently hydrogen, or an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur;

each $R^2$ is independently an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur;

each $R^4$ is independently halogen, —CN, —NO₂, —OR, —SR, —N(R)₂, —S(O)₂R, —S(O)₂N(R)₂, —S(O)R, —C(O)R, —C(O)OR, —C(O)N(R)₂, —N(R)C(O)R, N(R)C(O)N(R)₂, —C(O)N(R)OR, —N(R)C(O)OR, —N(R)S(O)₂N(R)₂, —N(R)S(O)₂R, or an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur;

$R^x$ is hydrogen, —$R^2$, —CN, —NO₂, halogen, —C(O)N(R)₂, —C(O)OR, —C(O)R, —N(R)₂, —NH[Ar], —OR, or —S(O)₂N(R)₂;

$R^z$ is hydrogen, —$R^2$, —CN, —NO₂, halogen, —C(O)N(R)₂, —C(O)OR, —C(O)R, —N(R)₂, —NH[Ar], —OR, or —S(O)₂N(R)₂;

[Ar] is a phenyl or heteroaromatic ring substituted by m instances of $R^{1'}$;

$L^1$ is a covalent bond or a $C_{1-6}$ bivalent hydrocarbon chain wherein one or two methylene units of the chain are optionally and independently replaced by —N(R)—, —N(R)C(O)—, —C(O)N(R)—, —N(R)S(O)₂—, —S(O)₂N(R)—, —O—, —C(O)—, —OC(O)—, —C(O)O—, —S—, —S(O)— or —S(O)₂—;

$L^2$ is a covalent bond or a $C_{1-6}$ bivalent hydrocarbon chain wherein one or two methylene units of the chain are optionally and independently replaced by —N(R)—, —N(R)C(O)—, —C(O)N(R)—, —N(R)S(O)₂—, —S(O)₂N(R)—, —O—, —C(O)—, —OC(O)—, —C(O)O—, —S—, —S(O)— or —S(O)₂—;

m is 0-4;

n is 0-4; and p is 0-2;

as defined and described in WO 2015/048281 and US 2015/0094305, the entirety of each of which is herein incorporated by reference.

In some embodiments, the present invention provides a compound of Formula I, wherein IRAK is an IRAK4 inhibitor

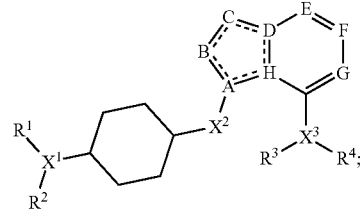

thereby forming a compound of formula I-vvv'-1:

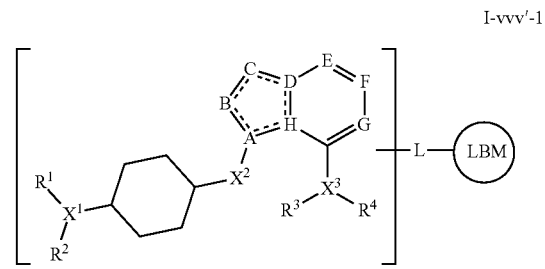

I-vvv'-1 or a pharmaceutically acceptable salt thereof, wherein

L and LBM are as defined above and described in embodiments herein;

each A, B, C, D, E, F, G, H, $X^1$, $X^2$, and $X^3$ are independently a carbon atom, a nitrogen atom, an oxygen atom, or a sulfur atom; and each $R^1$, $R^2$, $R^3$, and $R^4$ are independently hydrogen or a substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

$R^1$ and $R^2$ and $R^3$ and $R^4$ are each optionally taken together with their intervening atoms to form a 4-7 membered saturated, partially unsaturated, or heteroaryl ring having 0-3 heteroatoms, independently selected from nitrogen, oxygen, and sulfur.

Such IRAK4 inhibitors are well known to one of ordinary skill in the art and include those described in Scott et al., *J. Med. Chem.*, 2017, 60 (24): 10071-10091 and Degorce et al., *Bioorg. Med. Chem.*, 2018, 26 (4): 913-924.
In certain embodiments, the present invention provides a compound of Formula I, wherein IRAK is an IRAK4 inhibitor
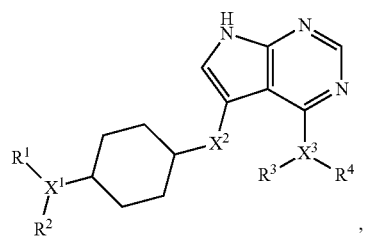
,
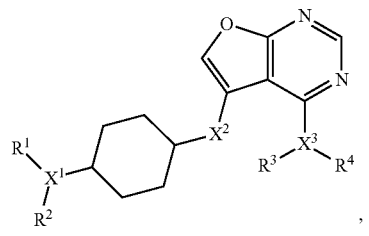
,
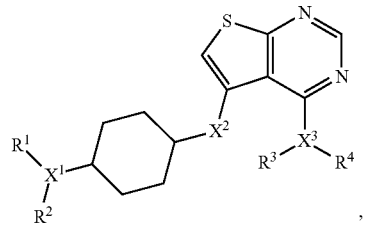
,
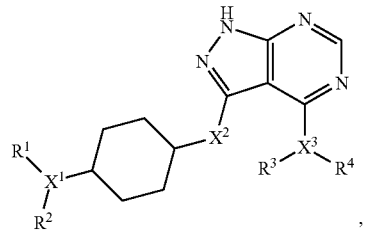
,
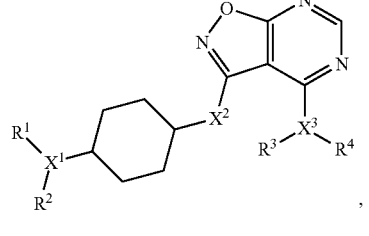
,
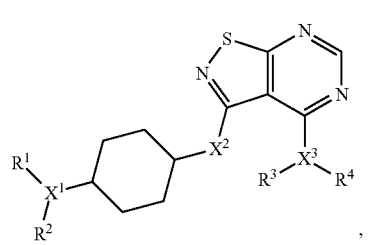
,
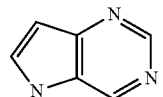
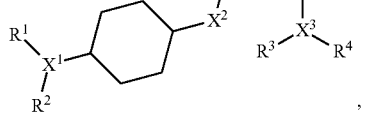
,
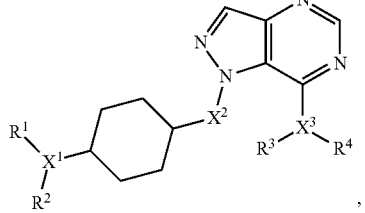
,
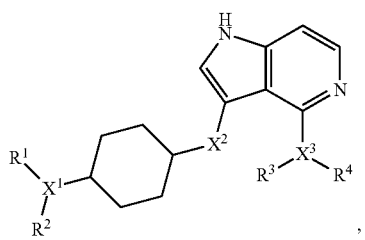
,
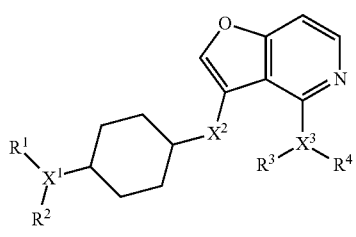
,
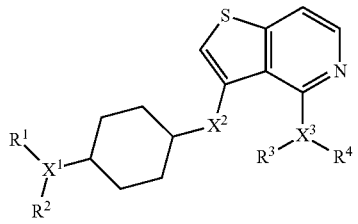
,
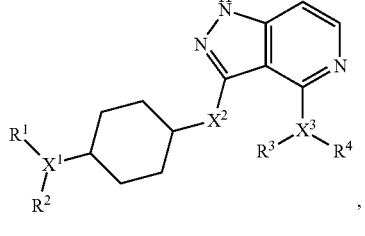
,
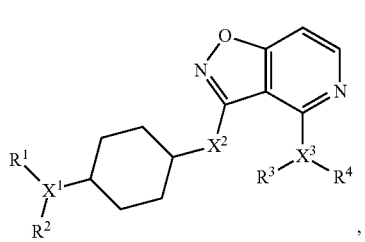
, -continued
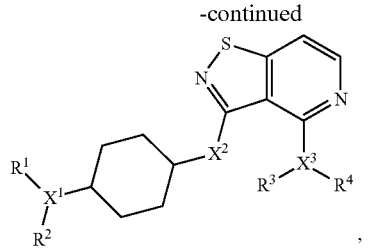
,
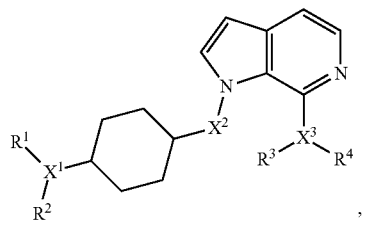
,
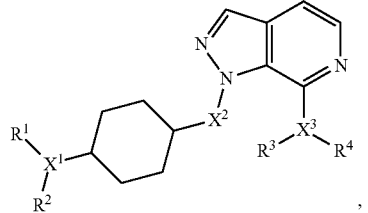
,
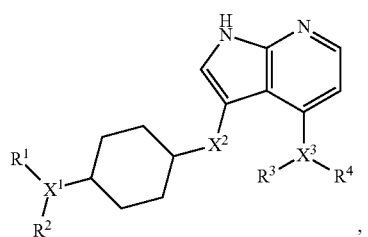
,
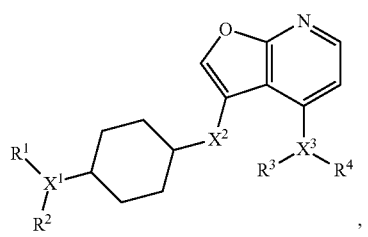
,
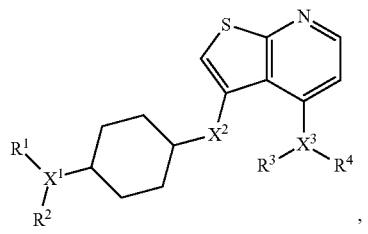
,
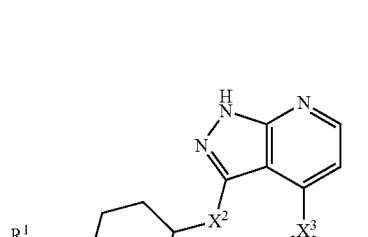
,
-continued
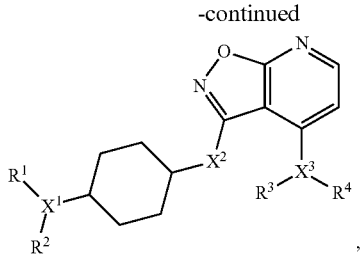
,
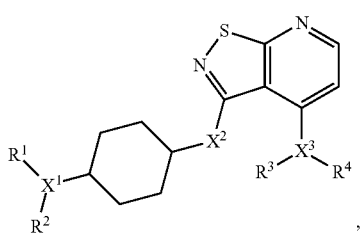
,
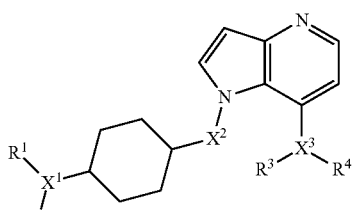
,
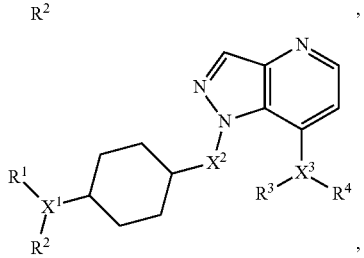
,
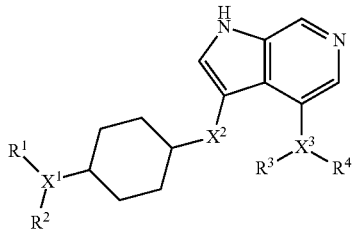
,
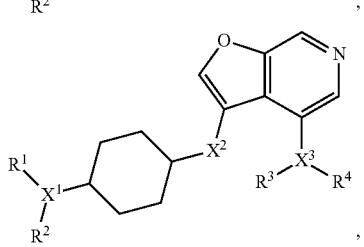
,
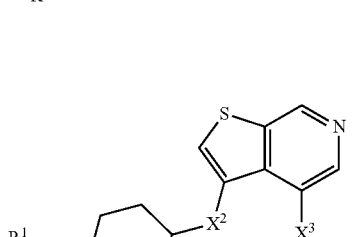
,

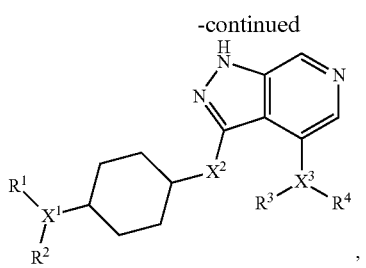
,
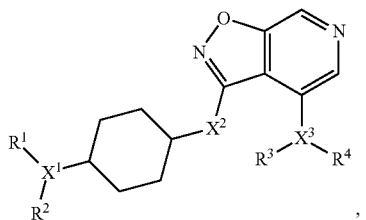
,
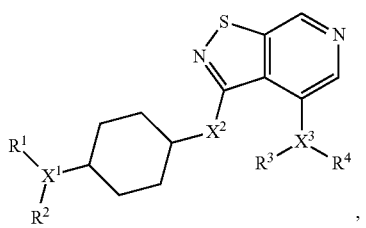
,
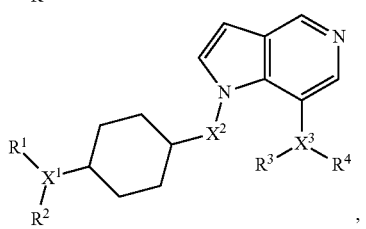
,
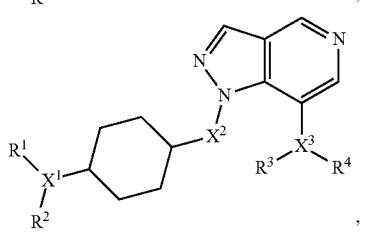
,
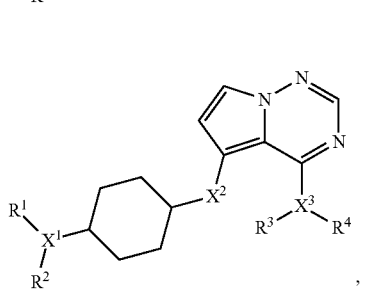
,
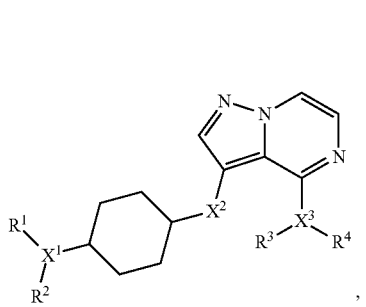
,
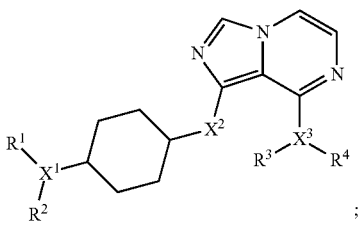
;
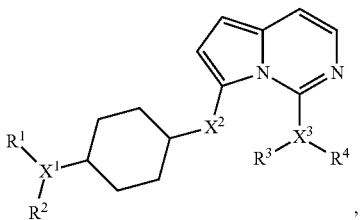
,
,
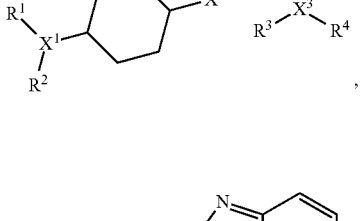
,
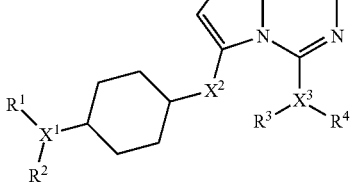
,
thereby forming a compound of formula I-vvv'-2, I-vvv'-3, I-vvv'-4, I-vvv'-5, I-vvv'-6, I-vvv'-7, I-vvv'-8, I-vvv'-9, I-vvv'-10, I-vvv'-11, I-vvv'-12, I-vvv'-13, I-vvv'-14, I-vvv'-15, I-vvv'-16, I-vvv'-17, I-vvv'-18, I-vvv'-19, I-vvv'-20, I-vvv'-21, I-vvv'-22, I-vvv'-23, I-vvv'-24, I-vvv'-25, I-vvv'-26, I-vvv'-27, I-vvv'-28, I-vvv'-29, I-vvv'-30, I-vvv'-31, I-vvv'-32, I-vvv'-33, I-vvv'-34, I-vvv'-35, I-vvv'-36, I-vvv'-37, I-vvv'-38, and I-vvv'-39:
I-vvv'-2
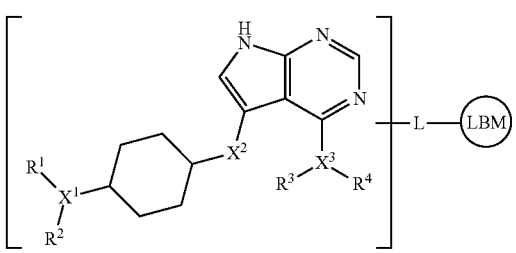

I-vvv'-3
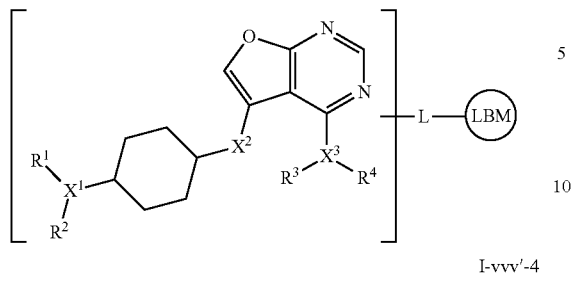
I-vvv'-4

I-vvv'-5

I-vvv'-6
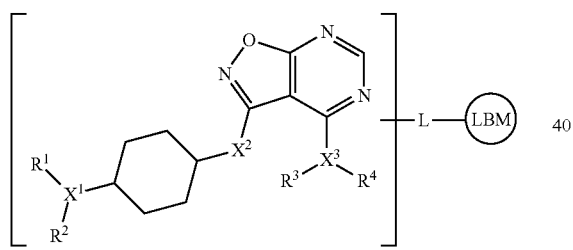
I-vvv'-7
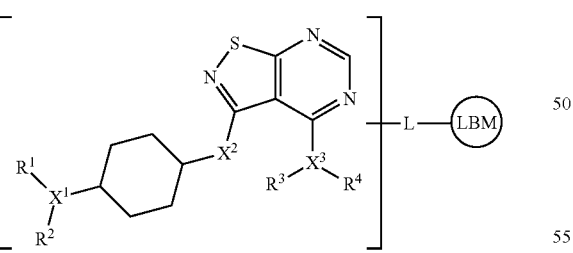
I-vvv'-8
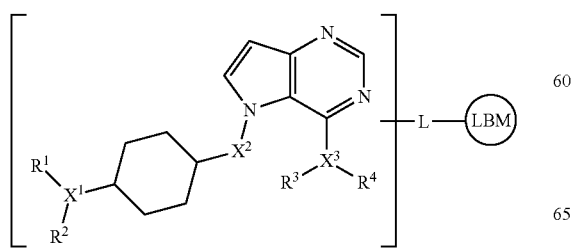
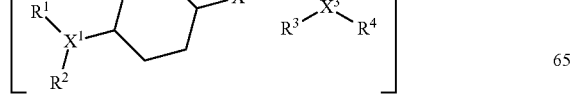
I-vvv'-9
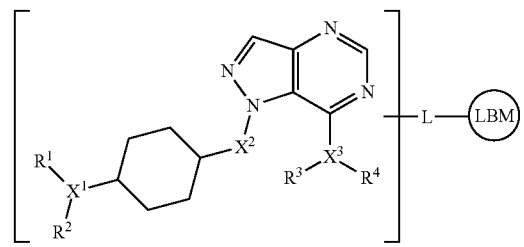
I-vvv'-10
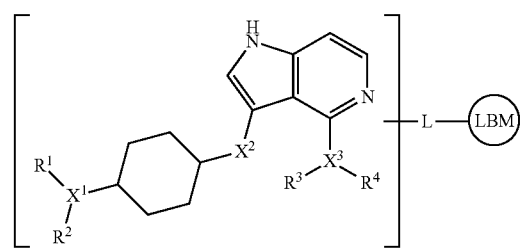
I-vvv'-11
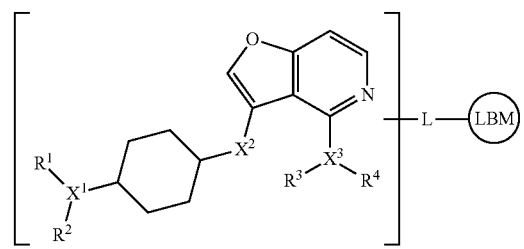
I-vvv'-12
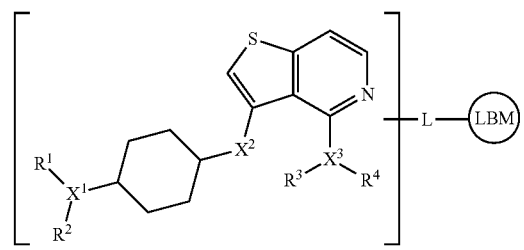
I-vvv'-13
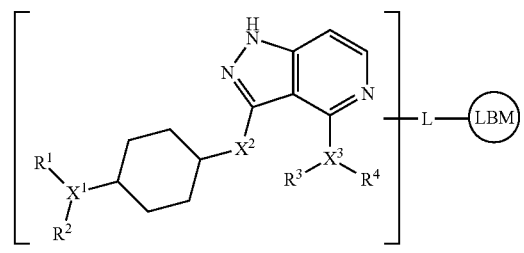
I-vvv'-14
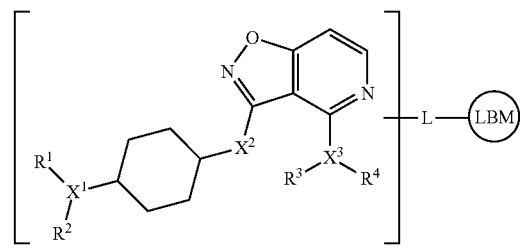

I-vvv'-15
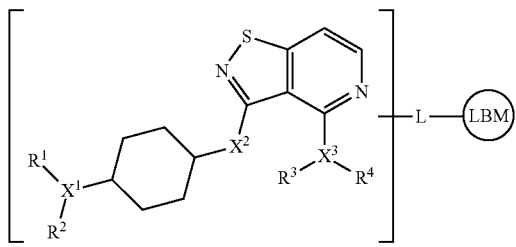
I-vvv'-16
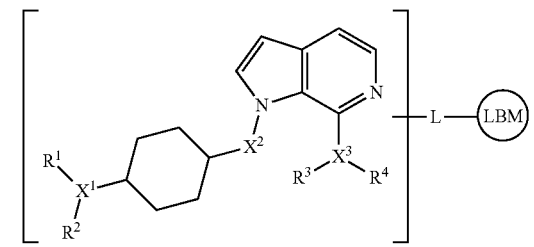
I-vvv'-17
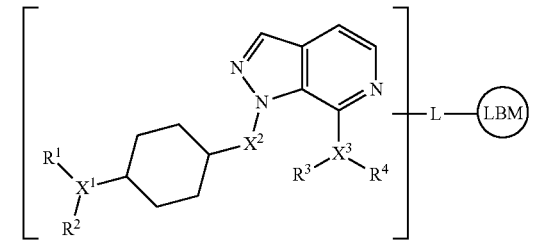
I-vvv'-18
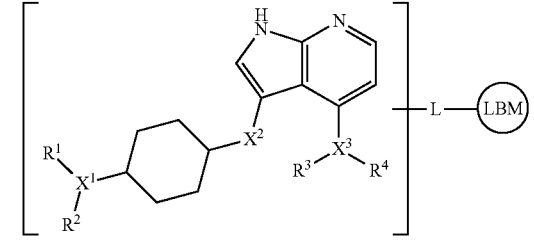
I-vvv'-19
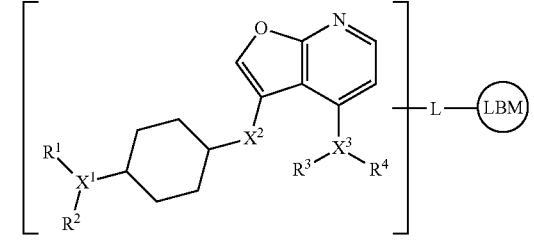
I-vvv'-20
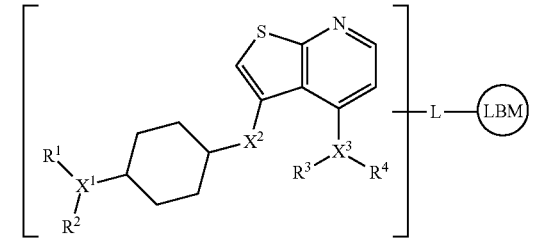
I-vvv'-21
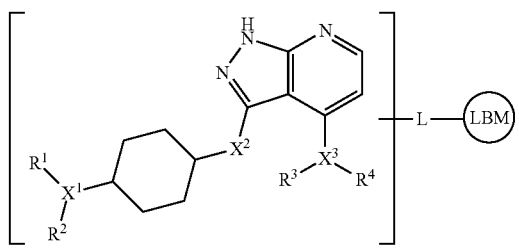
I-vvv'-22
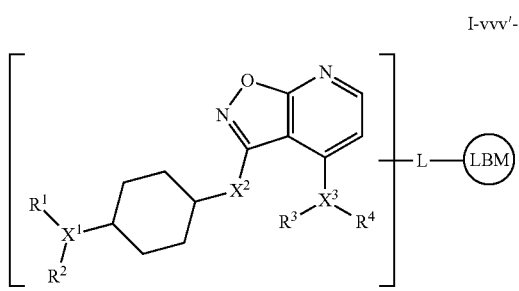
I-vvv'-23
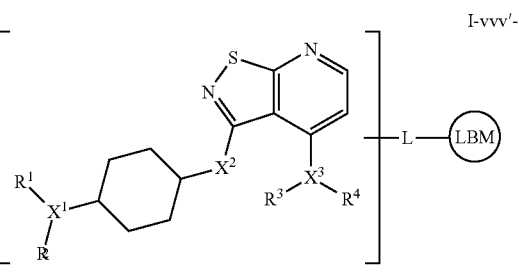
I-vvv'-24
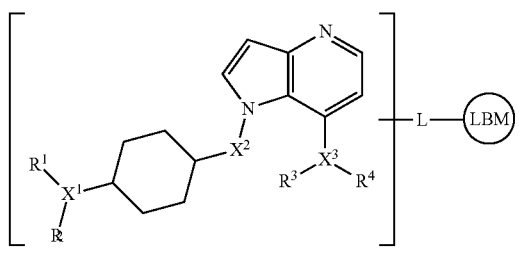
I-vvv'-25
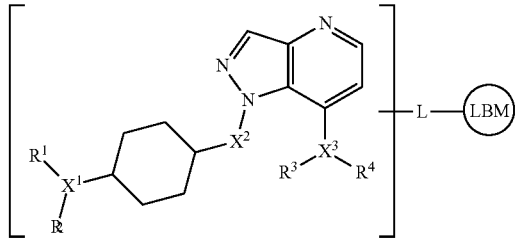
I-vvv'-26
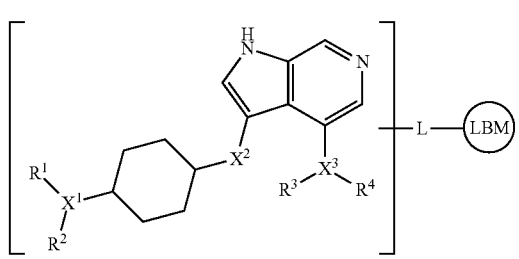

I-vvv'-27
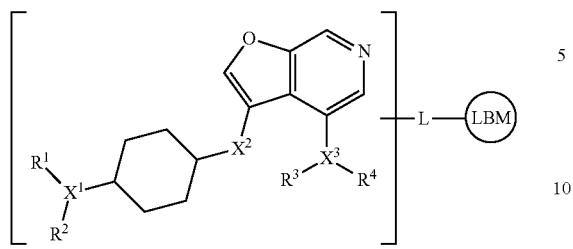
I-vvv'-28
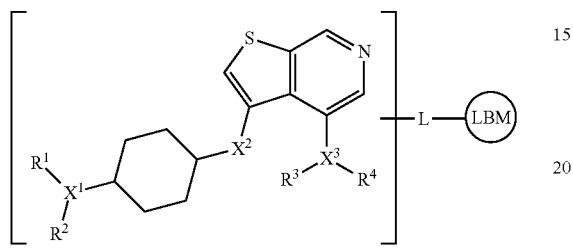
I-vvv'-29
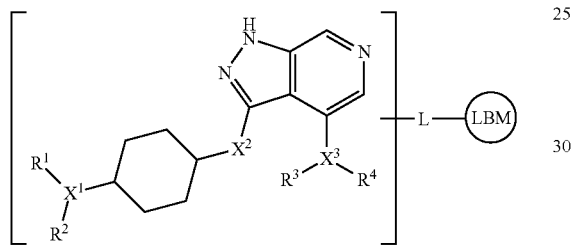
I-vvv'-30
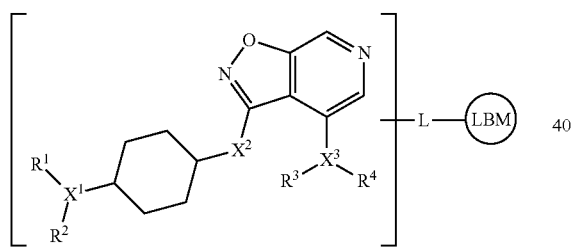
I-vvv'-31
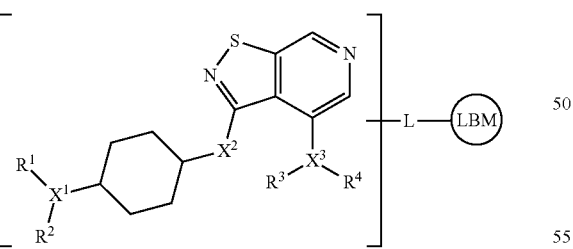
I-vvv'-32
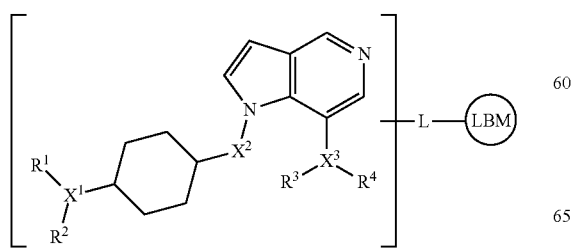
I-vvv'-33
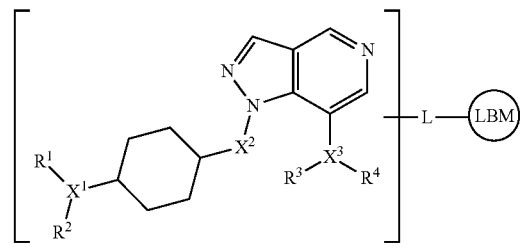
I-vvv'-34
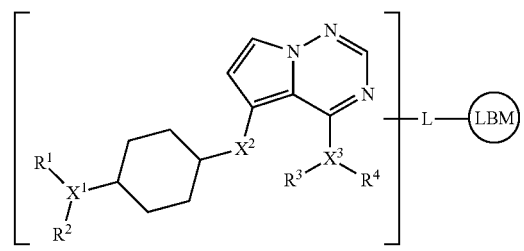
I-vvv'-35
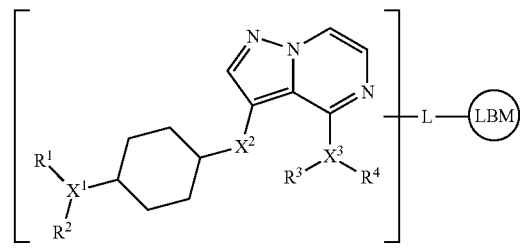
I-vvv'-36
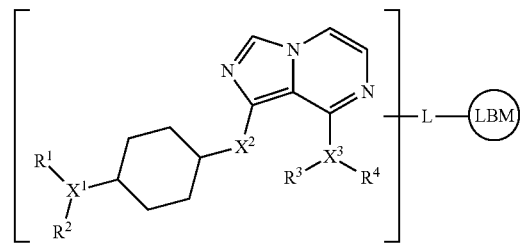
I-vvv'-37
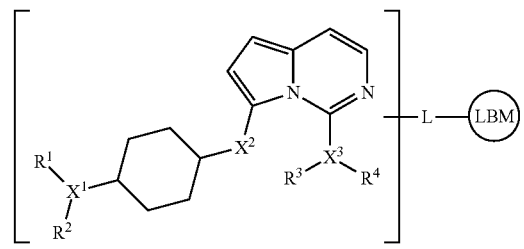
I-vvv'-38
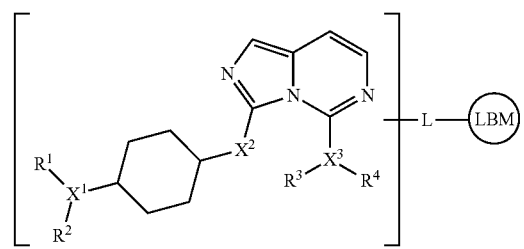

-continued

I-vvv'-39

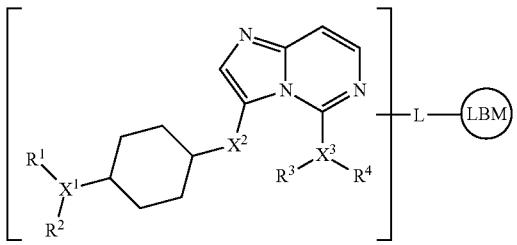

or a pharmaceutically acceptable salt thereof, wherein
L and LBM are as defined above and described in embodiments herein;
each $X^1$, $X^2$, and $X^3$ are independently a carbon atom, a nitrogen atom, an oxygen atom, or a sulfur atom; and
each $R^1$, $R^2$, $R^3$, and $R^4$ are independently hydrogen or a substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
$R^1$ and $R^2$ or $R^3$ and $R^4$ are optionally taken together with their intervening atoms to form a 4-7 membered saturated, partially unsaturated, or heteroaryl ring having 0-3 heteroatoms, independently selected from nitrogen, oxygen, and sulfur.

In certain embodiments, the present invention provides a compound of Formula I, wherein IRAK is an IRAK1 and/or IRAK4 inhibitor

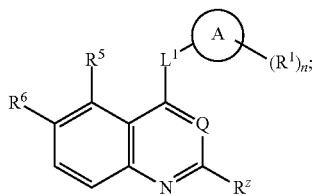

thereby forming a compound of formula I-www-1

I-www-1

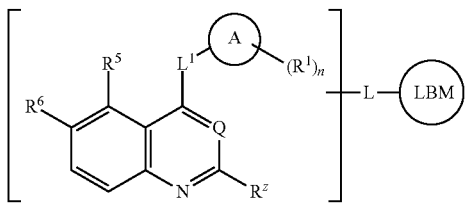

or a pharmaceutically acceptable salt thereof, wherein L and LBM are as defined above and described in embodiments herein, and wherein:
Q is =N— or =CH—;
Ring A is a 3-7 membered saturated or partially unsaturated carbocyclic ring or a 4-7 membered saturated or partially unsaturated heterocyclic ring having 1-3 heteroatoms independently selected from nitrogen, oxygen, or sulfur;

each $R^1$ is independently —$R^2$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —N(R)C(O)OR, —$N(R)C(O)NR_2$, Cy, or —$N(R)S(O)_2$ R; or $R^1$ is selected from one of the following formulas:

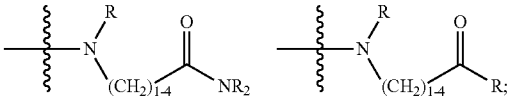

or two $R^1$ groups are taken together with their intervening atoms to form an optionally substituted 4-7 membered fused, spiro-fused, or bridged bicyclic ring having 0-2 heteroatoms independently selected from nitrogen, oxygen, or sulfur;
each Cy is independently an optionally substituted ring selected from a 3-7 membered saturated or partially unsaturated carbocyclic ring or a 4-10 membered saturated or partially unsaturated heterocyclic ring having 1-3 heteroatoms independently selected from nitrogen, oxygen, or sulfur;
each R is independently hydrogen, or an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur;
each $R^2$ is independently an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur;
each of $R^5$ and $R^6$ is independently hydrogen or -$L^2(R^4)_p$—$R^x$; or
$R^5$ and $R^6$ are taken together with their intervening atoms to form a 4-7 membered partially unsaturated, or aromatic ring having 0-3 heteroatoms independently selected from nitrogen, oxygen, or sulfur;
each $R^4$ is independently halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —N(R)C(O)R, —$N(R)C(O)NR_2$, —C(O)N(R)OR, —N(R)C(O)OR, —$N(R)S(O)_2NR_2$, —$N(R)S(O)_2R$, or an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, and sulfur;
$R^x$ is hydrogen, —$R^2$, —CN, —$NO_2$, halogen, —$C(O)NR_2$, —C(O)OR, —C(O)R, —$NR_2$, —NH[Ar], —OR, or —$S(O)_2NR_2$;
$R^z$ is hydrogen, —$R^2$, —CN, —$NO_2$, halogen, —$C(O)NR_2$, —C(O)OR, —C(O)R, —$NR_2$, —NH[Ar], —OR, or —$S(O)_2NR_2$;

[Ar] is an optionally substituted phenyl or an optionally substituted 5-6 membered heteroaryl ring having 1-4 heteroatoms independently selected from nitrogen, oxygen, and sulfur;

$L^1$ is a covalent bond or a $C_{1-6}$ bivalent hydrocarbon chain wherein one or two methylene units of the chain are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—;

$L^2$ is a covalent bond or a $C_{1-6}$ bivalent hydrocarbon chain wherein one or two methylene units of the chain are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—;

m is 0-4;
n is 0-4; and
p is 0-2;

as defined and described in WO 2015/164374 and US 2015/0329498, the entirety of each of which is herein incorporated by reference.

In certain embodiments, the present invention provides a compound of Formula I, wherein IRAK is an IRAK4 inhibitor

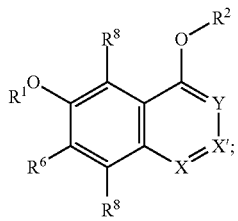

thereby forming a compound of formula I-xxx-1

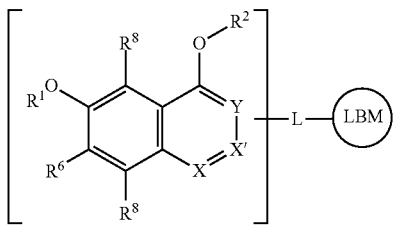

or a pharmaceutically acceptable salt thereof, wherein L and LBM are as defined above and described in embodiments herein, and wherein:

X and X' are each independently $CR^8$, N or —N$^+$—O$^-$; Y is independently N, —N$^+$—O$^-$ or $CR^{8'}$; provided that at least one of X, X' or Y is neither N nor —N$^+$—O$^-$ and that no more than one of X, X' or Y is —N$^+$—O$^-$;

$R^1$ is $C_1$-$C_6$alkyl; $C_2$-$C_6$alkenyl; $C_2$-$C_6$alkynyl; —(CR$^{3a}$R$^{3b}$)$_m$-(3- to 7-membered cycloalkyl); —(CR$^{3a}$R$^{3b}$)$_m$-(3- to 7-membered heterocycloalkyl) having one to three heteroatoms; —(CR$^{3a}$R$^{3b}$)$_m$-(5- to 10-membered heteroaryl), having one to three heteroatoms; or —(CR$^{3a}$R$^{3b}$)$_m$-$C_6$-$C_{12}$aryl; wherein said alkyl, alkenyl, alkynyl, cycloalkyl, heterocycloalkyl, heteroaryl or aryl is optionally substituted with one to five halogen, deuterium, —OR$^5$, —SR$^5$, —NR$^{11a}$R$^{11b}$, cyano, $C_1$-$C_6$alkyl, $C_3$-$C_6$cycloalkyl or —$C_1$-$C_6$alkoxy;

$R^2$ is —(CR$^{3a}$R$^{3b}$)$_m$-(3- to 10-membered cycloalkyl); —(CR$^{3a}$R$^{3b}$)$_m$-(3- to 10-membered heterocycloalkyl) having one to three heteroatoms; —(CR$^{3a}$R$^{3b}$)$_m$-(5- to 10 membered heteroaryl) having one to three heteroatoms; or —(CR$^{3a}$R$^{3b}$)$_m$—$C_6$-$C_{12}$aryl; wherein said cycloalkyl, heterocycloalkyl, heteroaryl or aryl is optionally substituted with one to five R$^4$; and wherein, if the heteroatom on said heterocycloalkyl and heteroaryl is N, said N is optionally substituted with R$^{4'}$; or R$^2$ is $C_1$-$C_6$alkyl, wherein said alkyl is optionally substituted with NH$_2$, OH or cyano;

$R^{3a}$ and $R^{3b}$ for each occurrence are independently hydrogen or $C_1$-$C_3$alkyl;

$R^4$ for each occurrence is independently a bond, deuterium halogen, cyano, $C_1$-$C_6$alkyl, $C_2$-$C_6$alkenyl, oxo, —OR$^5$, —SR$^5$, —S(O)R$^9$, —S(O)$_2$R$^9$, —NR$^{11a}$R$^{11b}$, —C(O)R$^{10}$, —(CR$^{3a}$R$^{3b}$)$_n$-(3- to 7-membered cycloalkyl), —(CR$^{3a}$R$^{3b}$)$_n$-(4- to 10-membered heterocycloalkyl), having one to three heteroatoms, —(CR$^{3a}$R$^{3b}$)$_n$-(5- to 10 membered heteroaryl), having one to three heteroatoms, or —(CR$^{3a}$R$^{3b}$)$_n$—$C_6$-$C_{12}$aryl wherein said alkyl, cycloalkyl, heterocycloalkyl, heteroaryl or aryl is each optionally and independently substituted with one to five deuterium, halogen, OR$^5$, —SR$^5$, —NR$^{11a}$R$^{11b}$, cyano, $C_1$-$C_6$alkyl, $C_3$-$C_6$cycloalkyl or —$C_1$-$C_6$alkoxy; or two R$^4$ taken together with the respective carbons to which each are bonded form a 3- to 6-membered cycloalkyl or 4- to 6-membered heterocycloalkyl, wherein said cycloalkyl or heterocycloalkyl is optionally substituted with one to three halogen, deuterium, —OR$^5$, —SR$^5$, —NR$^{11a}$R$^{11b}$, cyano or $C_1$-$C_6$alkyl or $C_1$-$C_6$alkoxy, wherein the alkyl or alkoxy is optionally substituted with halogen, deuterium, —OR$^5$, —SR$^5$, —NR$^{11a}$R$^{11b}$, or cyano; and wherein, if a heteroatom on said heterocycloalkyl is N, said N is optionally substituted with R$^{4'}$;

$R^{4'}$ is independently $C_1$-$C_6$alkyl, $C_2$-$C_6$alkenyl, —C(O)R$^{10}$, —S(O)$_2$R$_9$, —(CR$^{3a}$R$^{3b}$)$_n$-(3- to 7-membered cycloalkyl), —(CR$^{3a}$R$^{3b}$)$_n$-(4- to 10-membered heterocycloalkyl) or C(O)(CH$_2$)$_t$CN; wherein said alkyl, alkenyl, cycloalkyl, or heterocycloalkyl is each optionally and independently substituted with one to five deuterium, halogen, OH, cyano or $C_1$-$C_6$alkoxy; or R$^4$ and R$^{4'}$ taken together with the respective atoms to which each are bonded form a 3- to 6-membered cycloalkyl or 4- to 6-membered heterocycloalkyl, wherein said cycloalkyl or heterocycloalkyl is optionally substituted with one to three halogen, deuterium, —OR$^5$, —SR$^5$, —NR$^{11a}$R$^{11b}$, cyano, $C_1$-$C_6$alkyl or $C_1$-$C_6$alkoxy, wherein the alkyl or alkoxy is optionally substituted with halogen, deuterium, —OR$^5$, —SR$^5$, —NR$^{11a}$R$^{11b}$, or cyano;

$R^5$ is independently hydrogen or $C_1$-$C_6$alkyl, wherein said alkyl is optionally substituted with halogen, deuterium, $C_1$-$C_6$alkoxy, $C_1$-$C_6$alkylthiolyl, —NR$^{11a}$R$^{11b}$, cyano, $C_1$-$C_6$alkyl or $C_3$-$C_6$cycloalkyl; or two R$^5$ taken together with the oxygen atoms to which they are bonded form a 5- or 6-membered heterocycloalkyl;

$R^6$ is —C(O)NHR$^7$, CO$_2$R$^7$ or cyano;

$R^7$ is hydrogen or $C_1$-$C_6$alkyl;

each $R^8$ is independently hydrogen, halogen, cyano, —OR$^5$, —SR$^5$, —NR$^{11a}$R$^{11b}$, $C_6$alkyl, $C_3$-$C_6$cycloalkyl, 3- to 10-membered heterocycloalkyl or 5- to 6-membered heteroaryl or aryl, wherein said alkyl, cycloalkyl, heterocycloalkyl, heteroaryl or aryl is optionally substituted with one to three halogen, —NR$^{11a}$R$^{11b}$, OR$^5$, —SR$^5$, cyano, $C_1$-$C_3$ alkyl, —C(O)R$^{10}$ or oxo;

$R^{8'}$ is hydrogen, deuterium, halogen, cyano, —$OR^5$, —$SR^5$ or $NR^{11a}R^{11b}$;

$R^9$ is —$(CR^{3a}R^{3b})_p$—$(C_1$-$C_3$alkyl), —$(CR^{3a}R^{3b})_p$-(4- to 6-membered cycloalkyl), —$(CR^{3a}R^{3b})_p$-(4- to 6-membered heterocycloalkyl) or —$(CR^{3a}R^{3b})_p$—$(C_5$-$C_9$aryl), wherein said alkyl, cycloalkyl, heterocycloalkyl or aryl are each optionally substituted with fluoro or $C_1$-$C_3$alkyl;

$R^{10}$ is $C_1$-$C_6$alkyl, wherein said alkyl is optionally substituted with deuterium, halogen, OH, $C_1$-$C_6$alkoxy or cyano;

$R^{11a}$ and $R^{11b}$ are each independently hydrogen or $C_1$-$C_6$alkyl, wherein said alkyl is optionally substituted with deuterium, $C_1$-$C_6$alkoxy or cyano; and if $C_2$-$C_6$alkyl, said alkyl is optionally substituted with deuterium, $C_1$-$C_6$alkoxy, cyano, halogen or OH;

m is independently 0, 1, 2 or 3;
n is independently 0, 1, 2 or 3;
p is independently 0 or 1; and
t is 1, 2 or 3;

as defined and described in WO 2015/150995 and US 2015/0284405, the entirety of each of which is herein incorporated by reference.

In certain embodiments, the present invention provides a compound of Formula I, wherein IRAK is an IRAK4 inhibitor

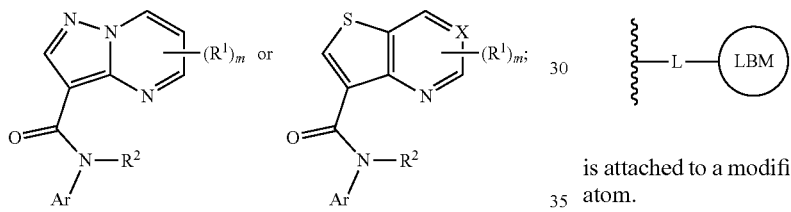

thereby forming a compound of formula I-yyy-1 or I-yyy-2:

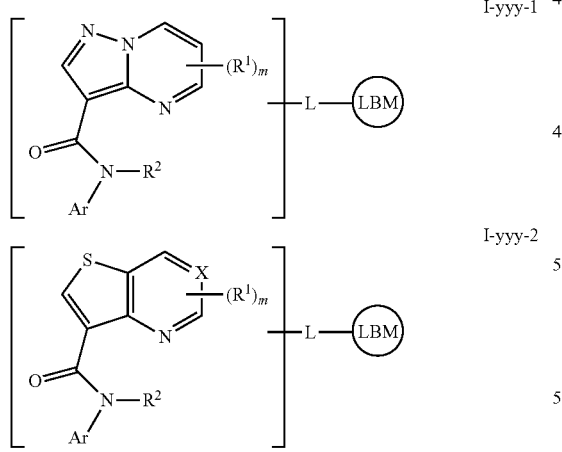

I-yyy-1

I-yyy-2 or a pharmaceutically acceptable salt thereof, wherein L and LBM are as defined above and described in embodiments herein, and wherein:

X is N or CH
m is 1 or 2;
Ar is optionally substituted aryl or optionally substituted heteroaryl;
$R^1$ is hydrogen, $C_{1-6}$alkyl, $C_{1-6}$alkoxy, hydroxyl, hydroxy-$C_{1-6}$alkyl, $C_{1-6}$alkyl-amino, amino-$C_{1-6}$ alkyl, amino-$C_{1-6}$ alkyl-amino, hydroxy-$C_{1-6}$alkylamino, $C_{3-6}$cycloalkylamino, amino-$C_{3-6}$cycloalkylamino, amino-$C_{3-6}$ heterocycloalkylamino, aminocarbonyl, halo, hydroxy-$C_{1-6}$alkyl, or hydroxy-$C_{1-6}$alkoxy; and $R^2$ is hydrogen or $C_{1-6}$alkyl;

as defined and described in WO 2012/007375 and US 2012/0015962, the entirety of each of which is herein incorporated by reference.

As defined above and described herein, IRAK is an IRAK binding moiety capable of binding to one or more of IRAK-1, -2, -3, or -4.

In some embodiments, IRAK is an IRAK binding moiety capable of binding to IRAK-1. In some embodiments, IRAK is an IRAK binding moiety capable of binding to IRAK-2. In some embodiments, IRAK is an IRAK binding moiety capable of binding to IRAK-3. In some embodiments, IRAK is an IRAK binding moiety capable of binding to IRAK-4.

In some embodiments, IRAK is selected from a moiety recited in Aurigene Discovery Tech. Ltd. Presentation: *Novel IRAK-4 Inhibitors exhibit highly potent anti-proliferative activity in DLBCL cell lines with activation MYD88 L264P mutation*, such as, for example: AU-5850, AU-2807, AU-6686, and AU-5792, wherein

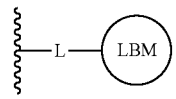

is attached to a modifiable carbon, oxygen, nitrogen or sulfur atom.

In some embodiments, IRAK is selected from a moiety recited in Scott, J. S. et al. *Discovery and Optimization of Pyrrolopyrimidine Inhibitors of Interleukin-1 Receptor Associated Kinase 4 (IRAK4) for the Treatment of Mutant MYD88 Diffuse Large B-cell Lymphoma*. J. Med. Chem. Manuscript, Nov. 29, 2017, 10.1021/acs.jmedchem.7b01290 such as, for example:

Cmp 1

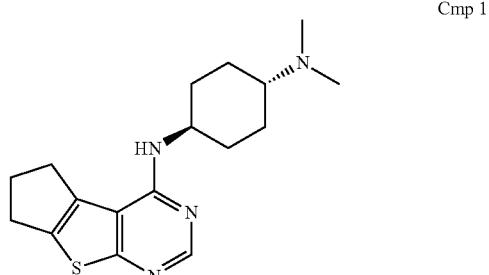

Cmp 2

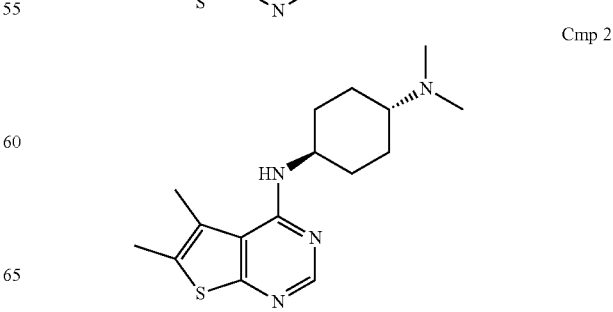

Cmp 3
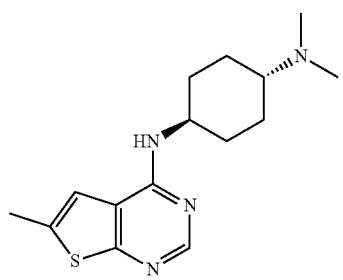
Cmp 4
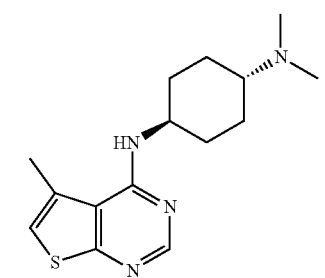
Cmp 5
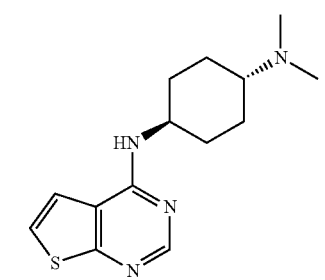
Cmp 6
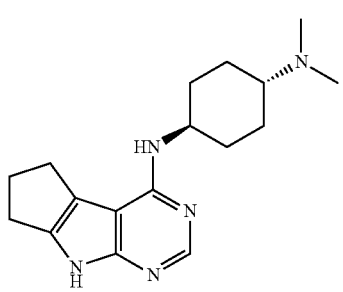
Cmp 7
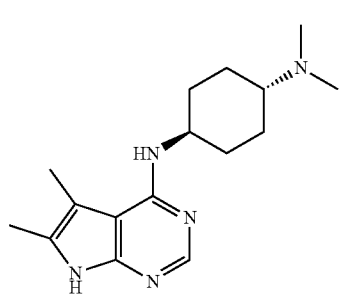
Cmp 8
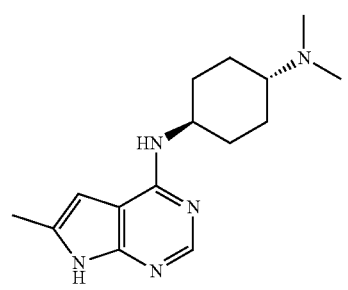
Cmp 9
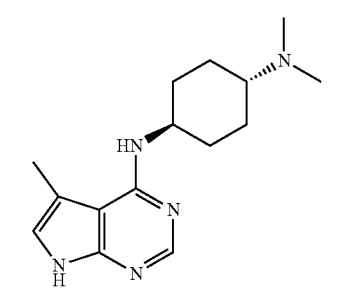
Cmp 10
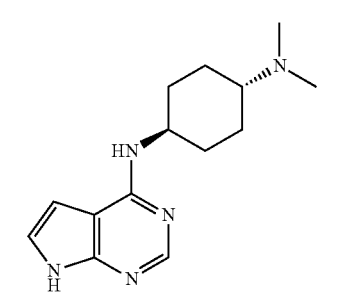
Cmp 11
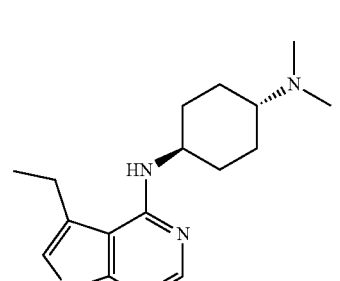
Cmp 12
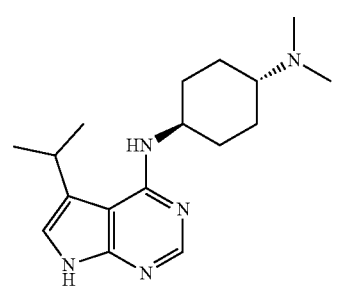

Cmp 13
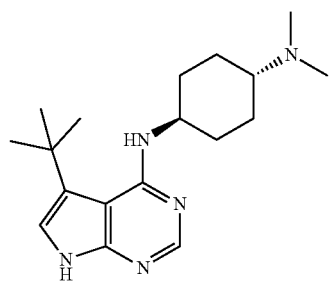
Cmp 14
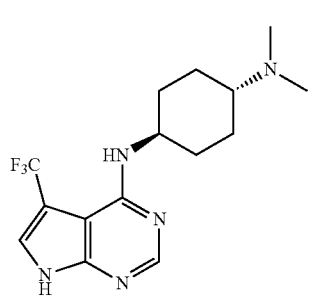
Cmp 15
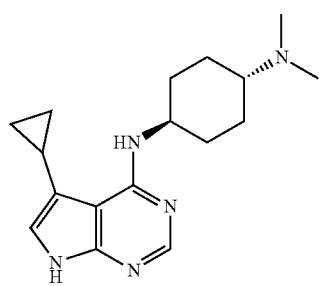
Cmp 16
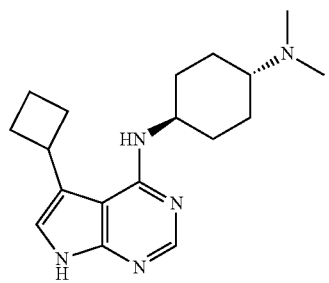
Cmp 17
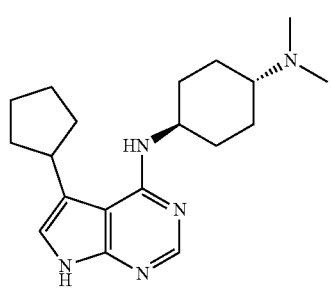
Cmp 18a/b
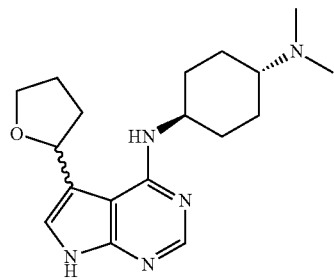
Cmp 19a/b
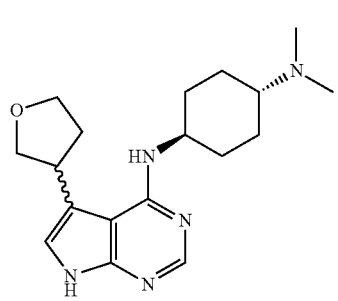
Cmp 20
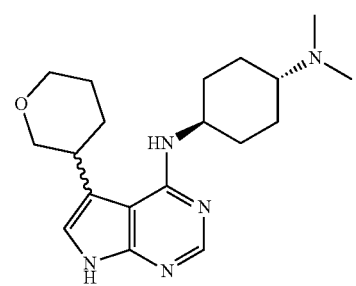
Cmp 21
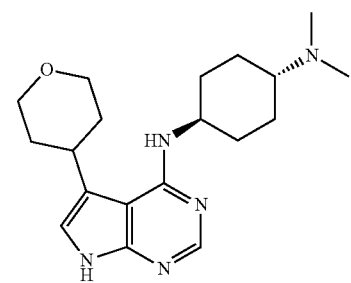
Cmp 22
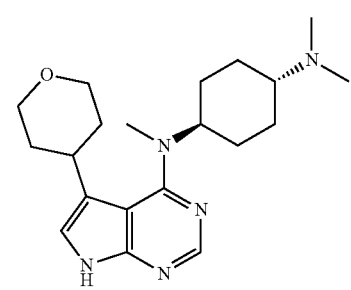

-continued
Cmp 23
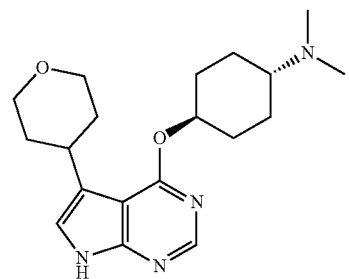
Cmp 24
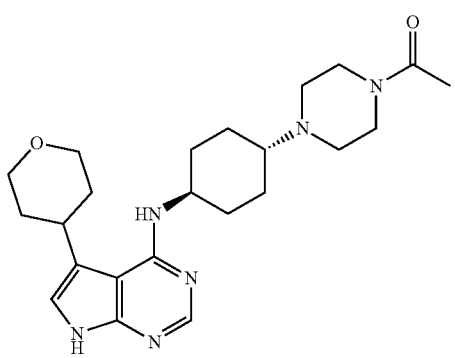
Cmp 25
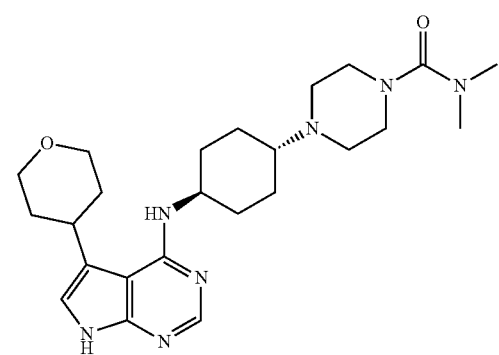
Cmp 26
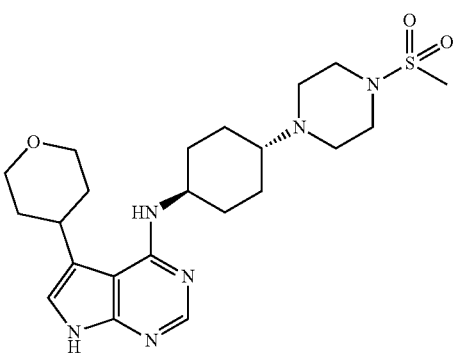
-continued
Cmp 27
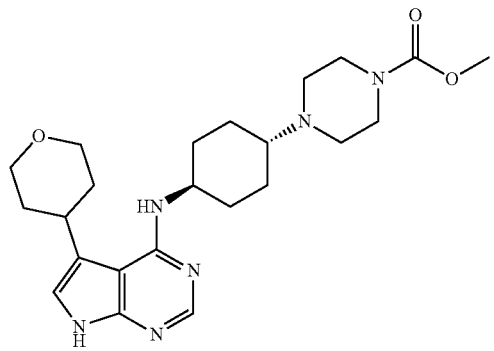
Cmp 28
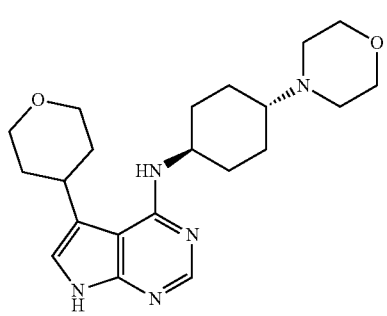
Cmp 29
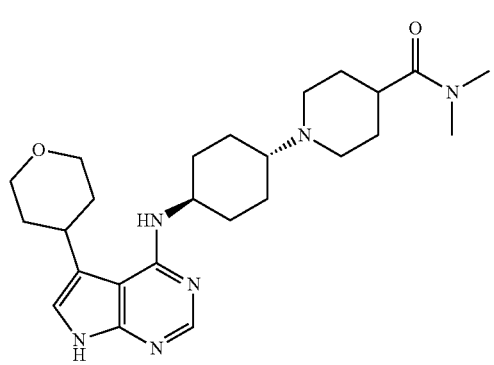
Cmp 30
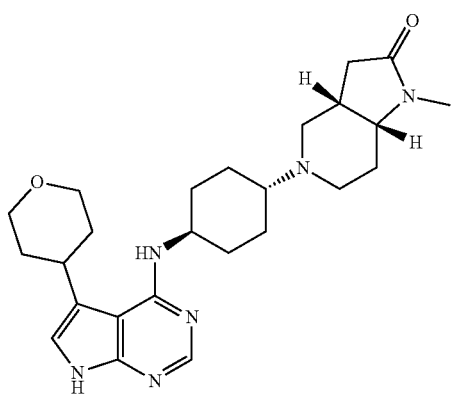

-continued
Cmp 31
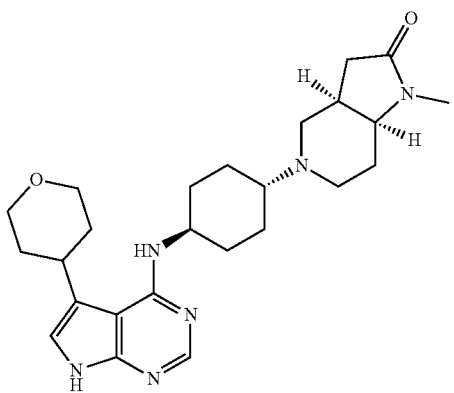
Cmp 32
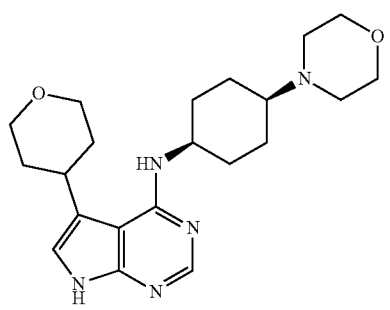
Cmp 33
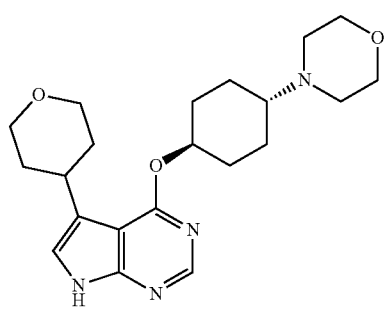
Cmp 34
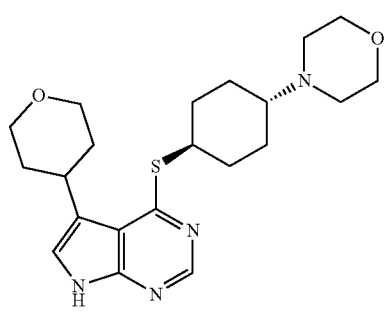
Cmp 35
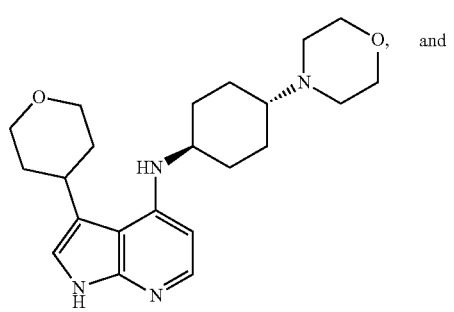
-continued
Cmp 36
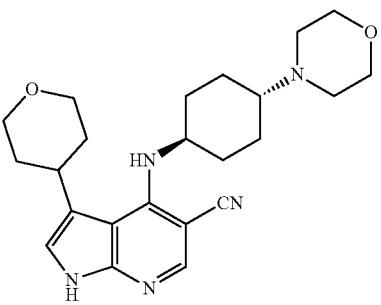
wherein
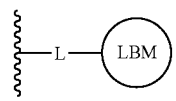
is attached to a modifiable carbon, oxygen, nitrogen or sulfur atom.
In some embodiments, IRAK is selected from a moiety recited in Powers, J. P. et al., *Discovery and initial SAR of inhibitors of interleukin*-1 *receptor-associated kinase*-4, Bioorg. Med Chem Lett. (2006) 16 (11): 2842-45, such as, for example:
Compound 1
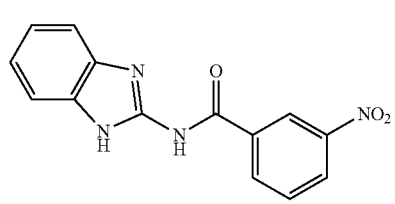
Compound 2
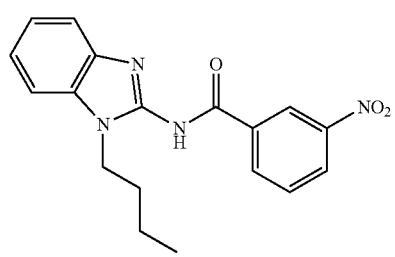
Compound 3
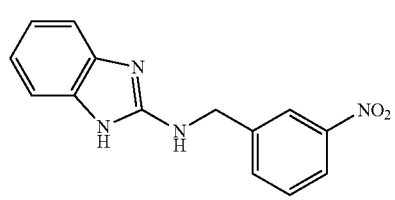
Compound 4
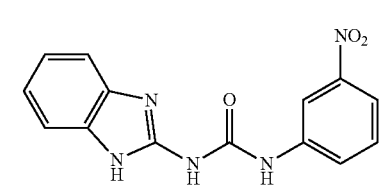

Compound 5
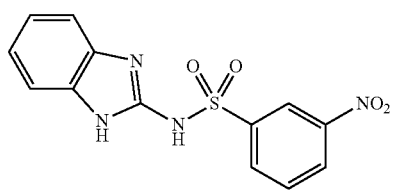
Compound 6
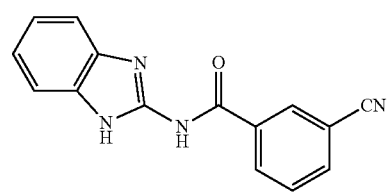
Compound 7
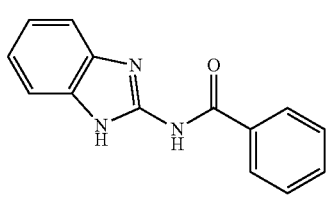
Compound 8
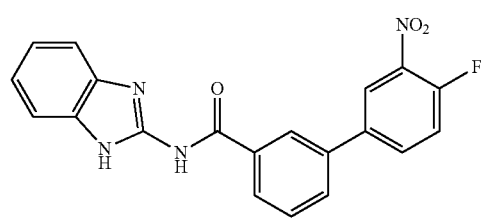
Compound 9
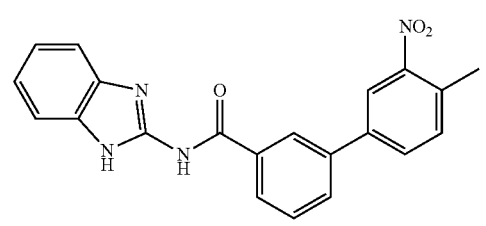
Compound 10
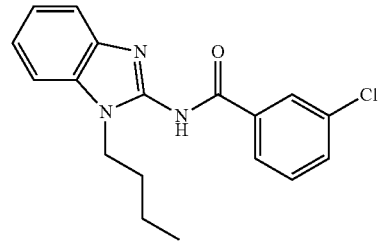
Compound 11
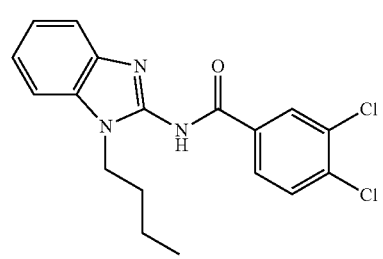
Compound 12
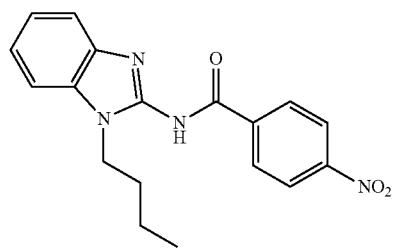
Compound 13
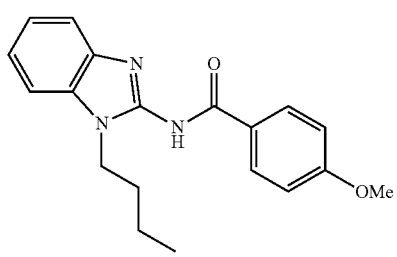
Compound 14
Compound 15
Compound 16
Compound 17
Compound 18
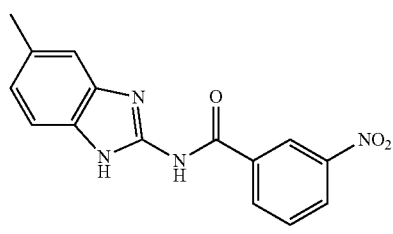

Compound 19
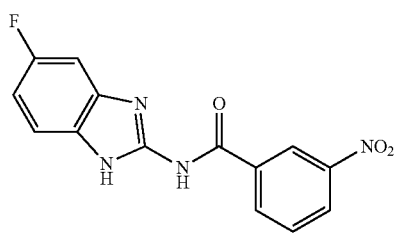
Compound 20
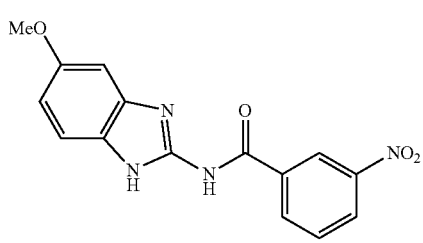
Compound 21
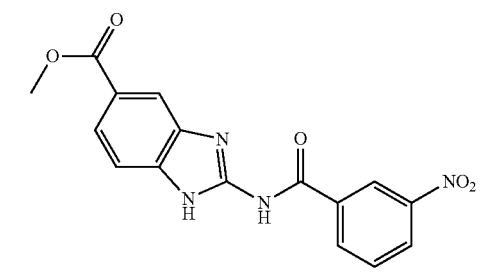
Compound 22
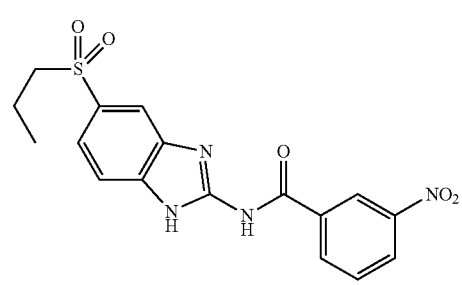
Compound 23
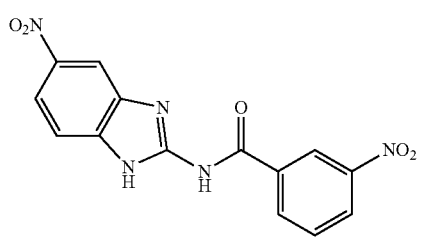
Compound 24
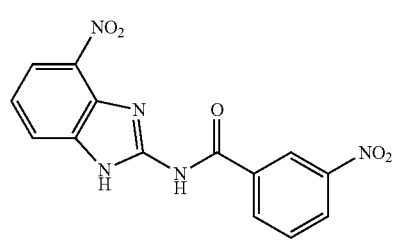
Compound 25
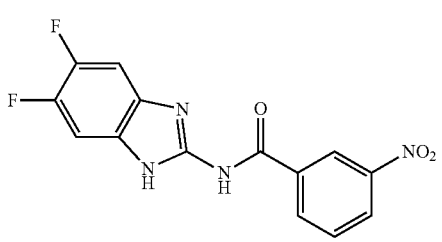
Compound 26
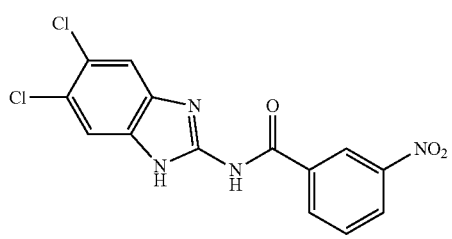
Compound 27
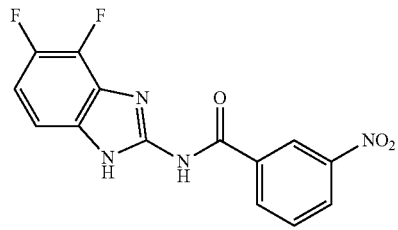
Compound 28
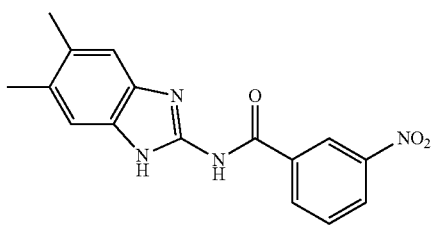
Compound 29
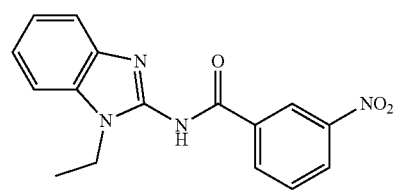
Compound 30
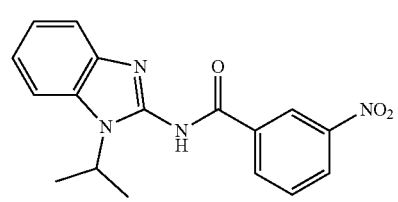
Compound 31
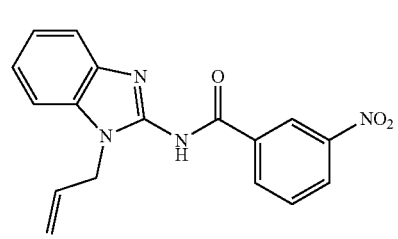

Compound 32
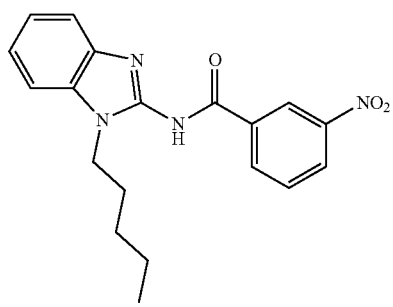
Compound 33
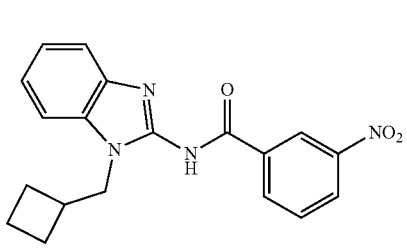
Compound 34
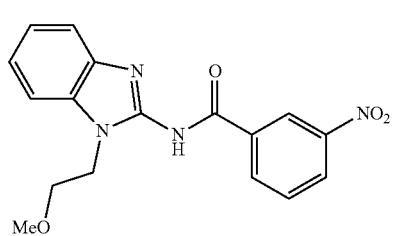
Compound 35
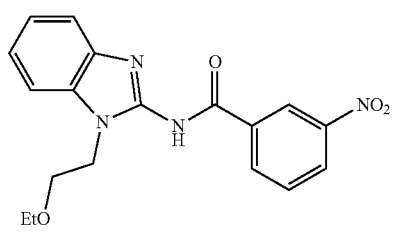
Compound 36
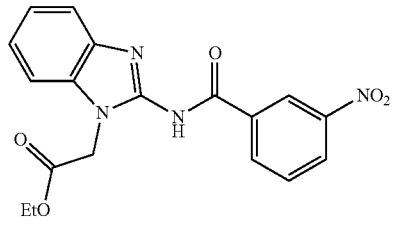
Compound 37
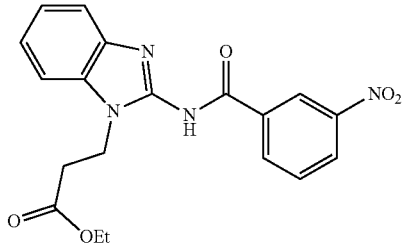
Compound 38
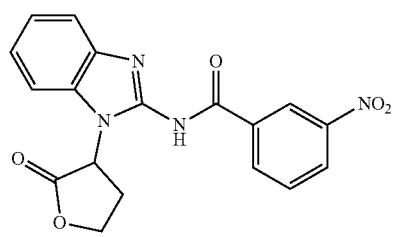
Compound 39
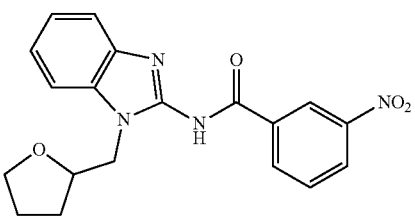
Compound 40
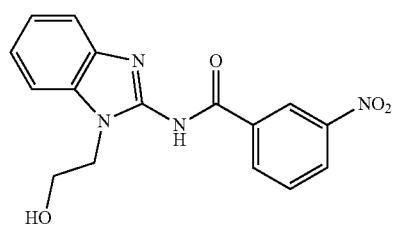
Compound 41
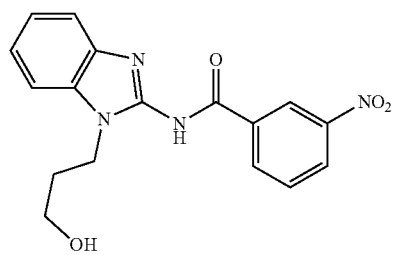
Compound 42
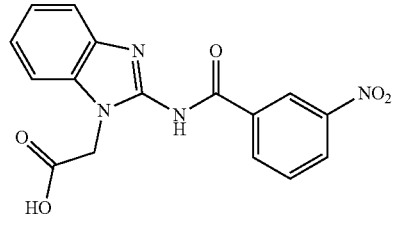
Compound 43
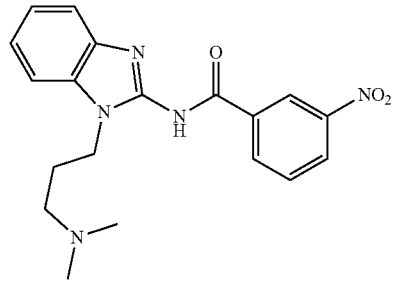

-continued

Compound 44

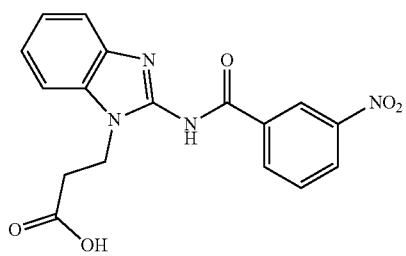

Compound 45

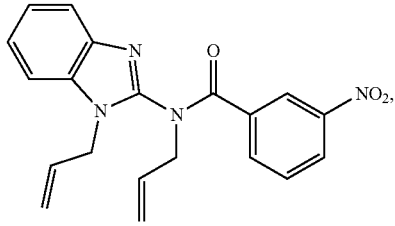

Compound 46

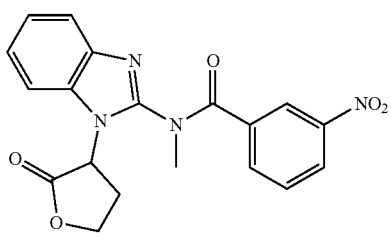

Compound 47

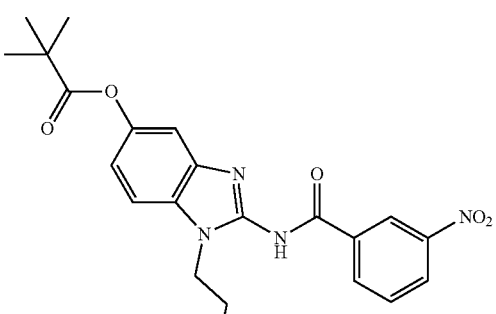, and

Compound 48 wherein

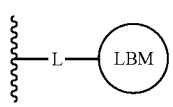

is attached to a modifiable carbon, oxygen, nitrogen or sulfur atom.

In some embodiments, IRAK is selected from a moiety recited in Wang, et al., *Crystal Structure of IRAK-4 Kinase in Complex with Inhibitors: Serine/Threonine Kinase with Tyrosine as a Gatekeeper*, Structure, 2006, 14 (12): 1835-44, such as, for example:

Compound 1

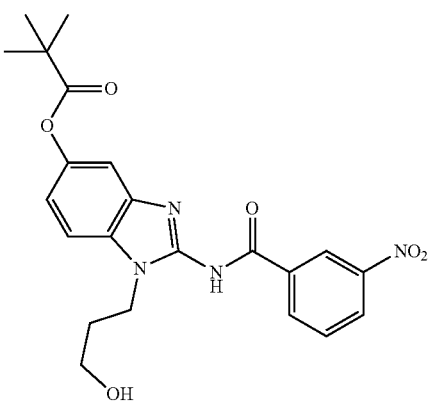

wherein

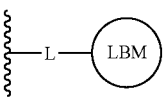

is attached to a modifiable carbon, oxygen, nitrogen or sulfur atom.

In some embodiments, IRAK is selected from a moiety recited in Wang, Z. et al., *Discovery of potent, selective, and orally bioavailable inhibitors of interleukin-1 receptor-associated kinase 4*, Bioorg. Med. Chem Lett., 2015, 25 (23): 5546-50, such as, for example:

Compound 1

Compound 2
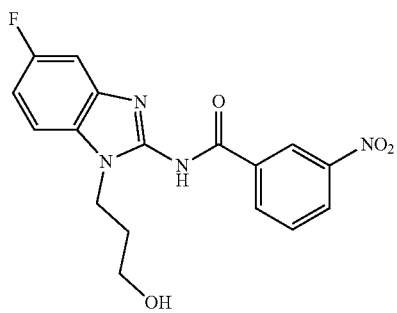
Compound 3
Compound 4
Compound 5
Compound 6
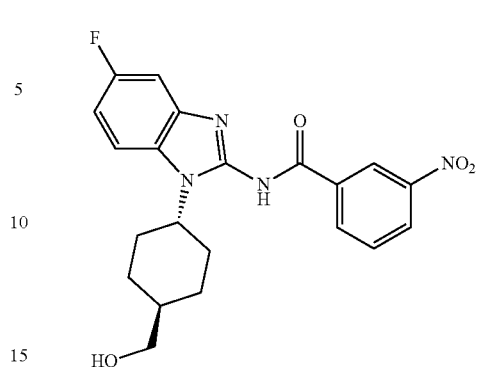
Compound 7
Compound 8
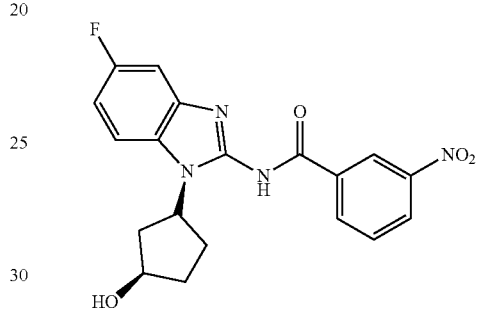
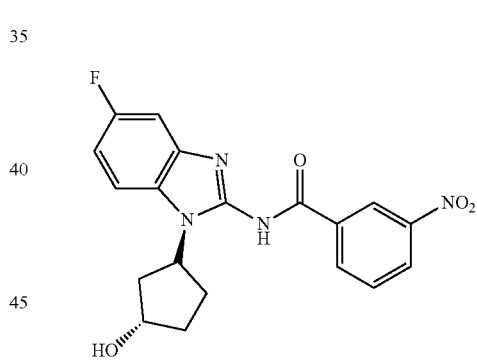
Compound 9
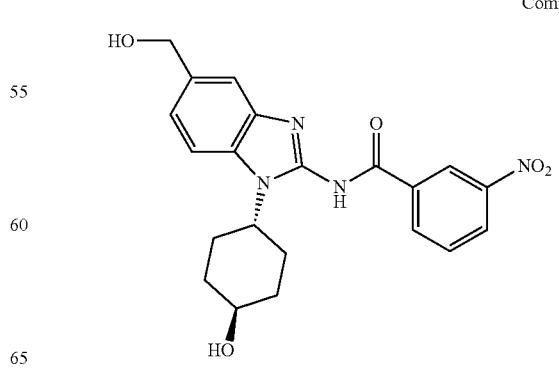

Compound 10
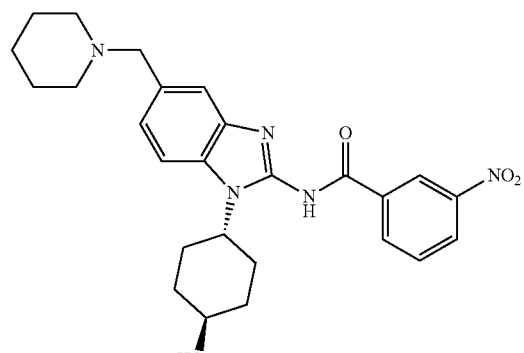
Compound 11
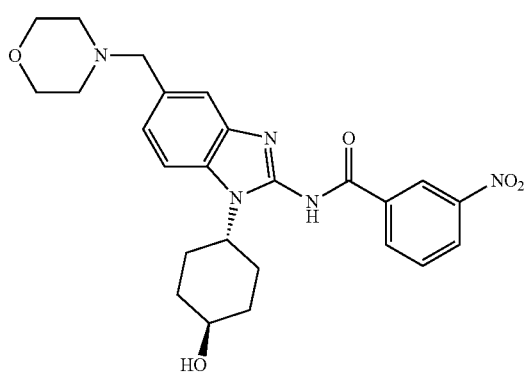
Compound 12
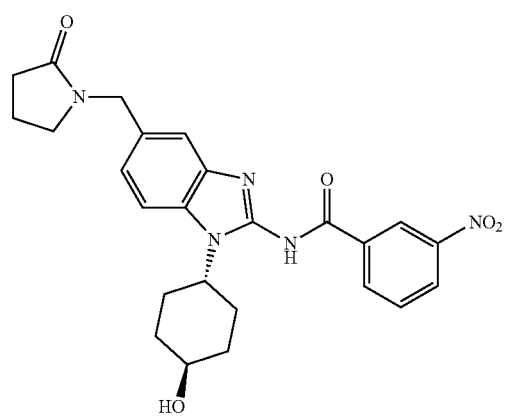
Compound 13
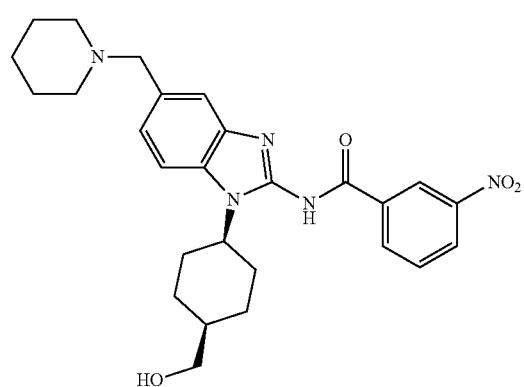
Compound 14
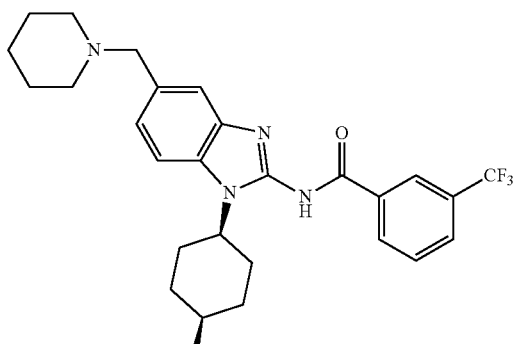
Compound 15
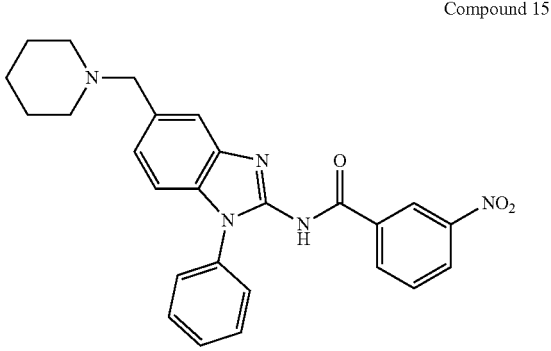
Compound 16
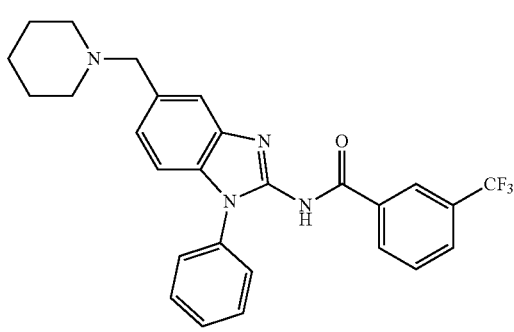
Compound 17
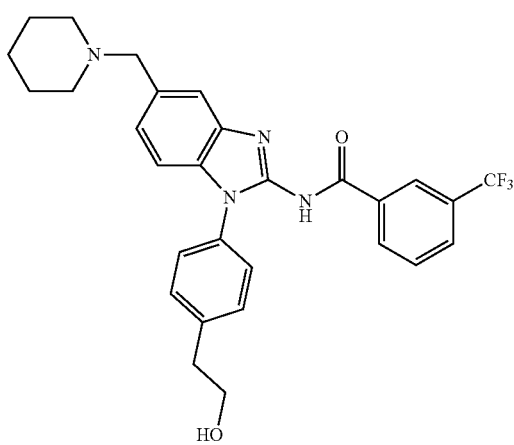

Coumpound 18

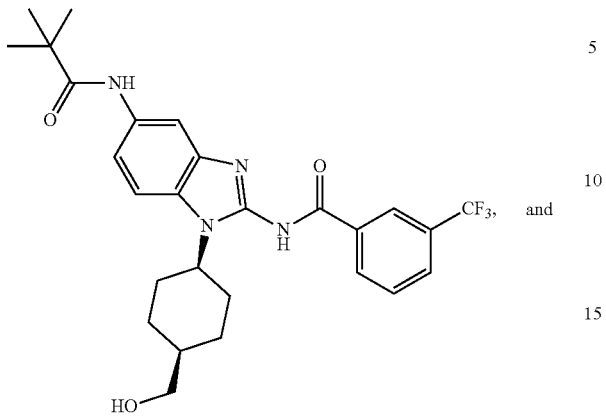

and

Compound 19

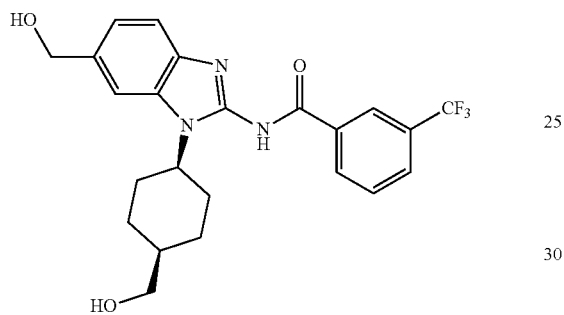

wherein

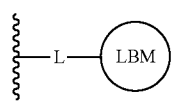

is attached to a modifiable carbon, oxygen, nitrogen or sulfur atom.

In some embodiments, IRAK is selected from a moiety recited in Chaudhary, D. et al., *Recent Advances in the Discovery of Small Molecule Inhibitors of Interleukin-1 Receptor-Associated Kinase 4 (IRAK4) as a Therapeutic Target for Inflammation and Oncology Disorders*, J. Med Chem., 2015, 58 (1): 96-110, such as, for example:

1

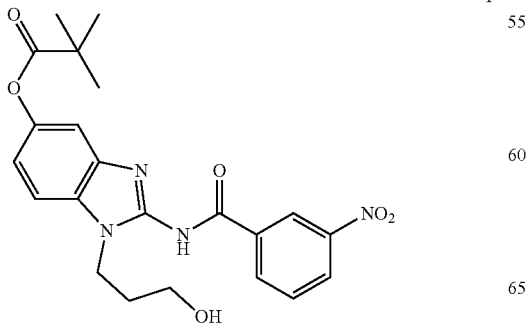

2

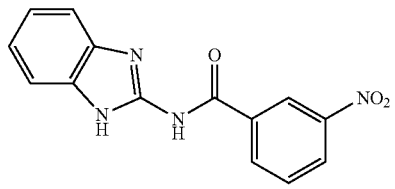

3

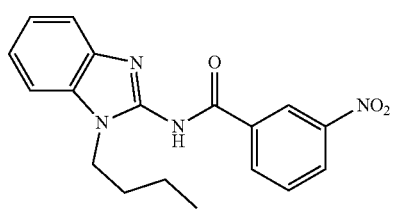

4

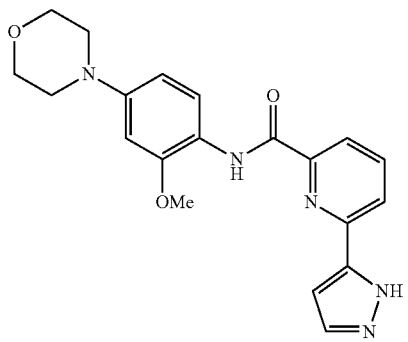

5

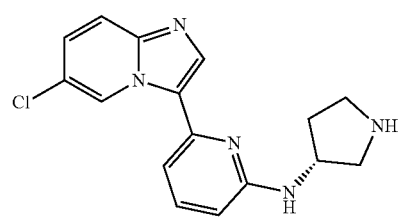

6

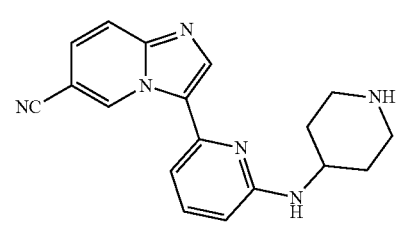

7

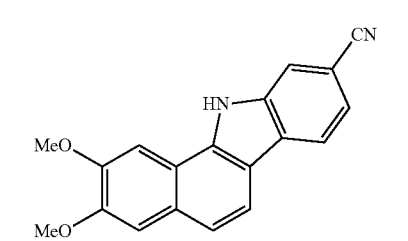

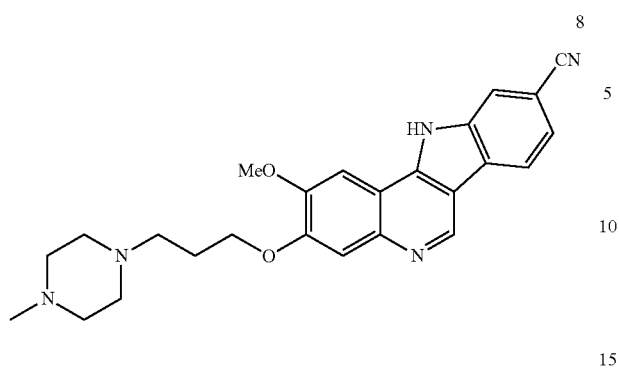
8
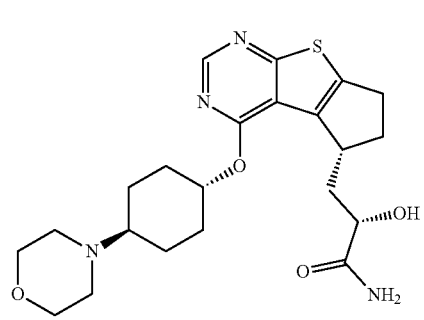
13
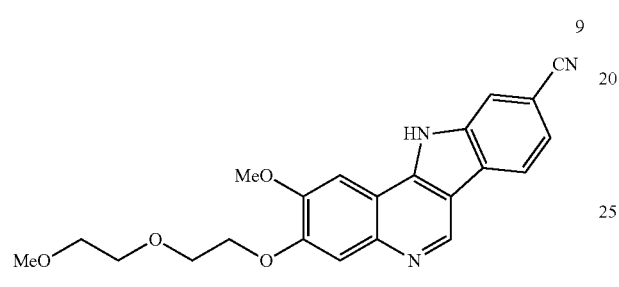
9
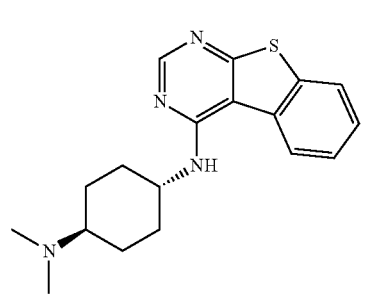
14
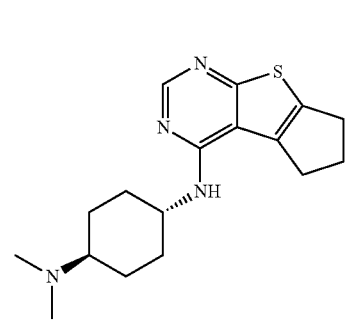
10
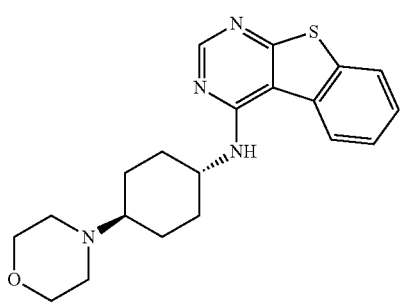
15
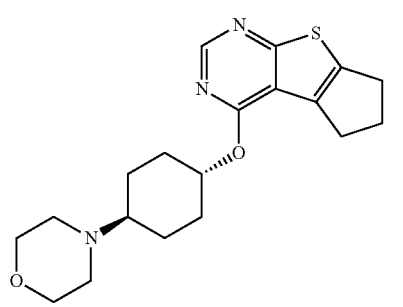
11
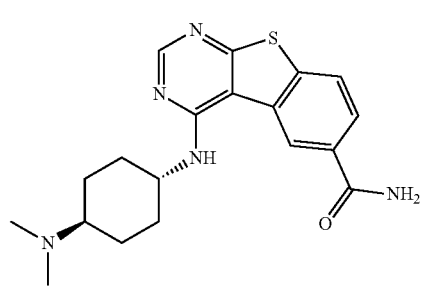
16
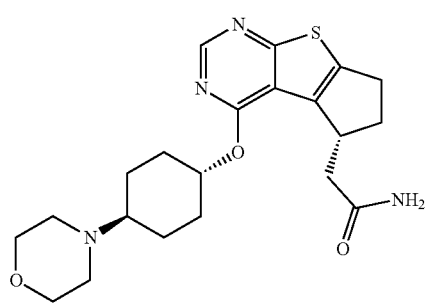
12
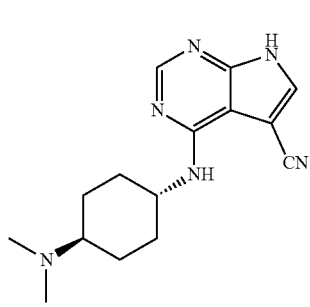
17

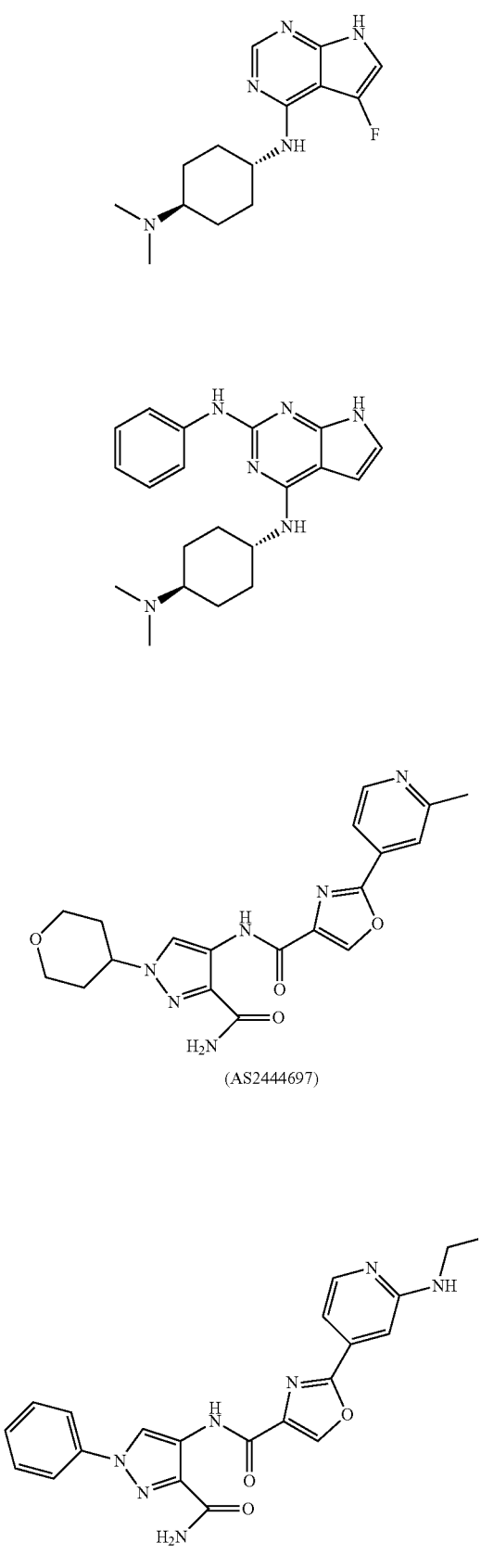
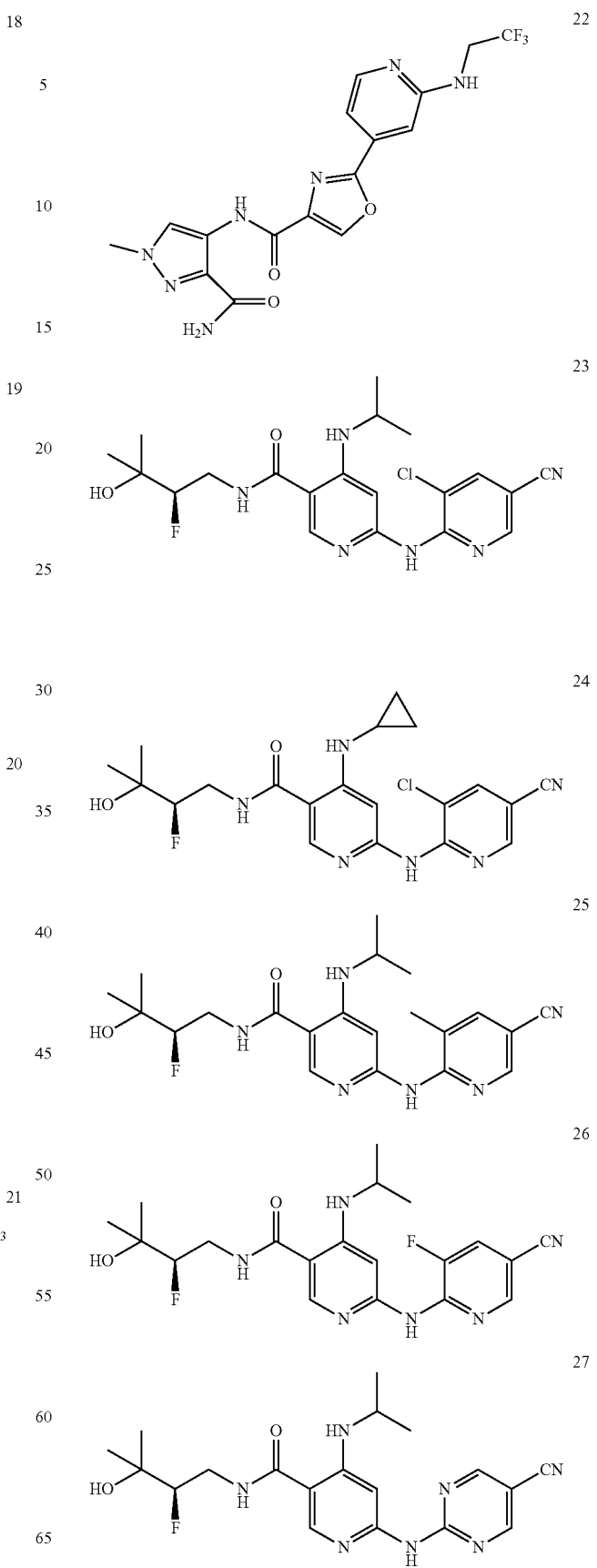

-continued
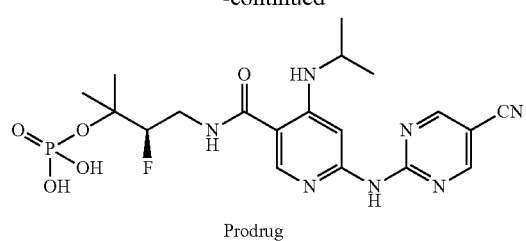
Prodrug
28
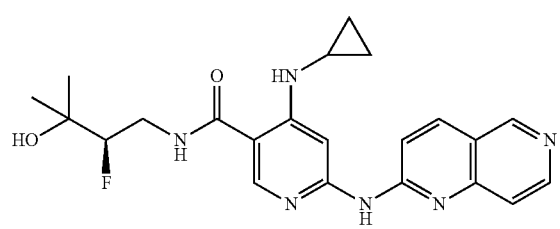
29
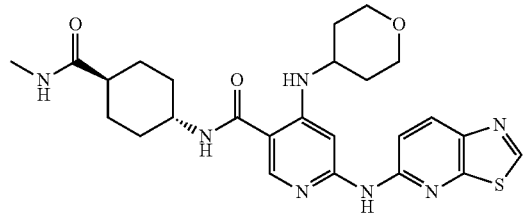
30
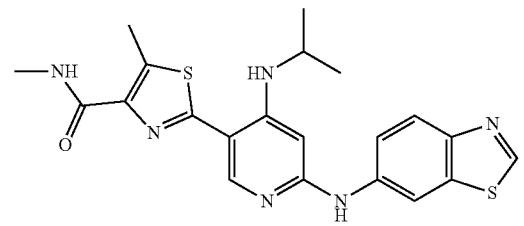
31
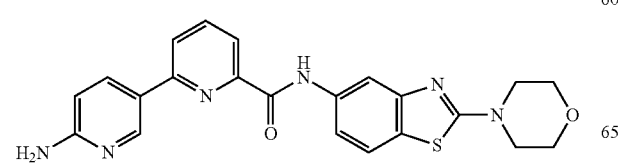
32
-continued
33
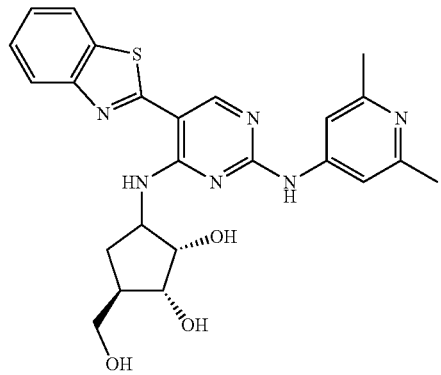
34
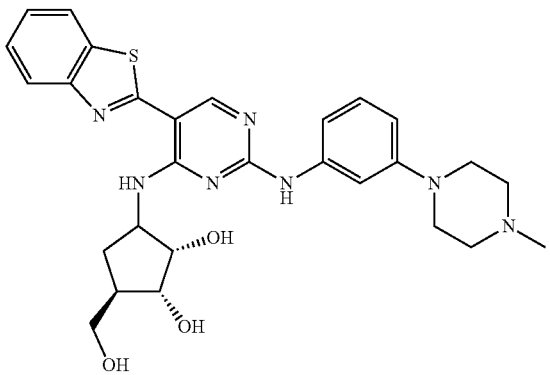
35
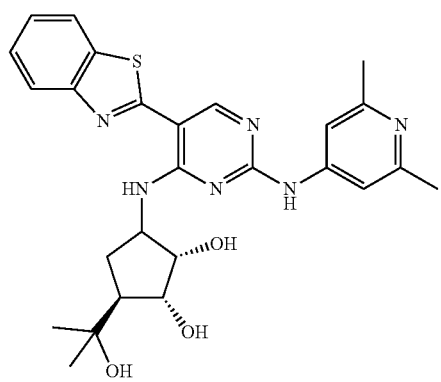
36
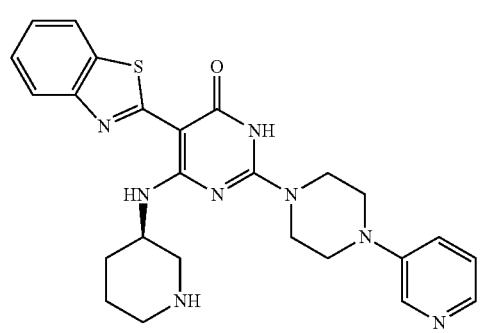

37
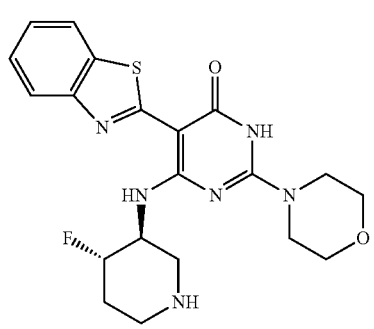
38
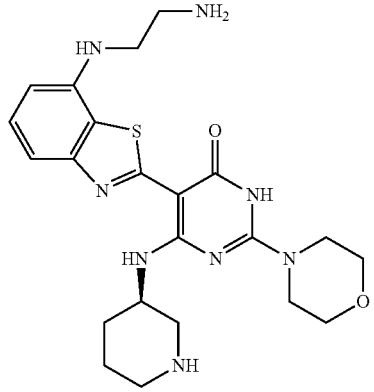
39

40
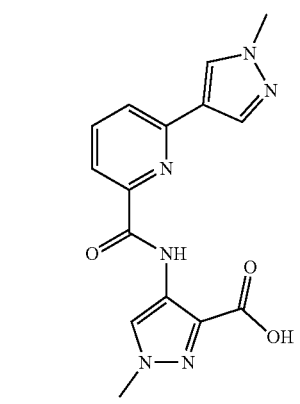
41
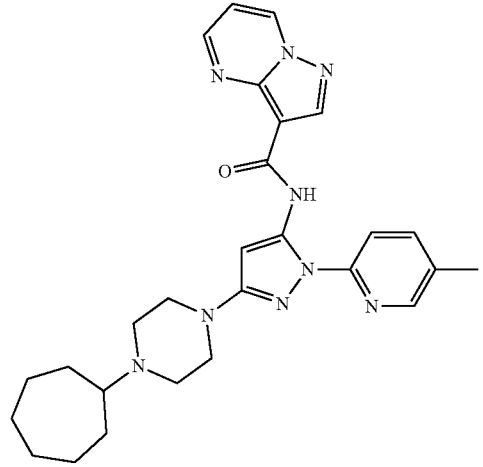
42
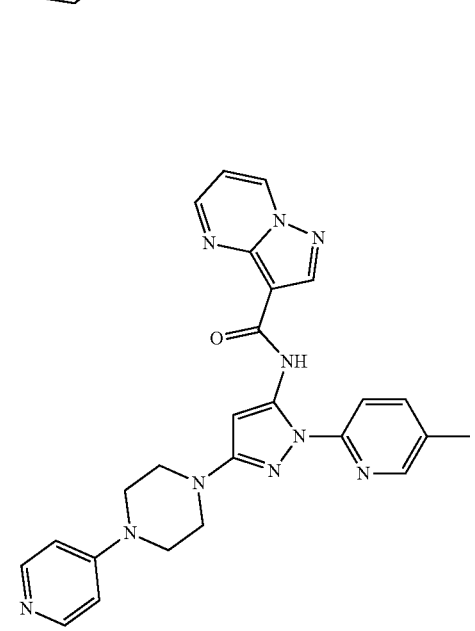
43
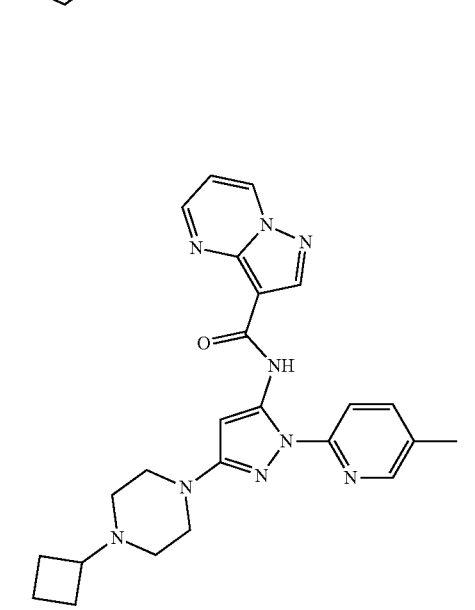

44
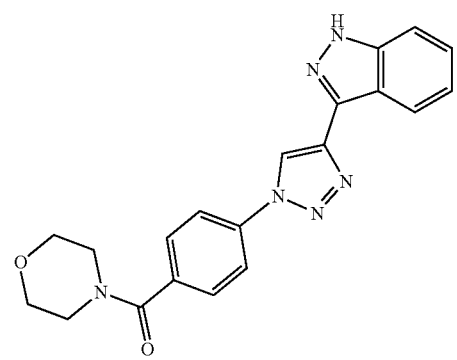
45
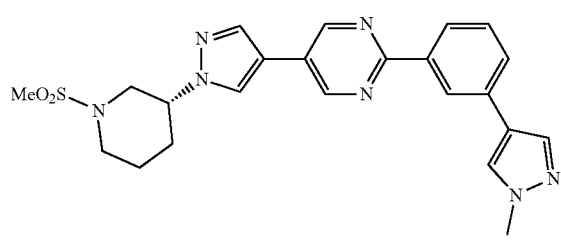
46
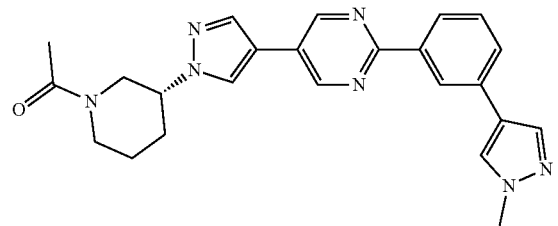
47
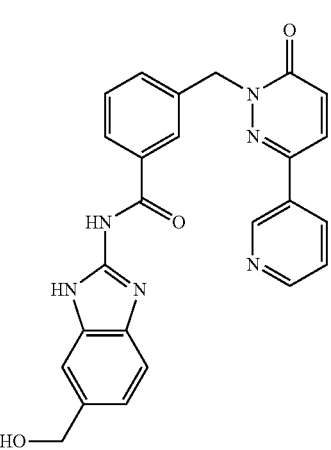
48
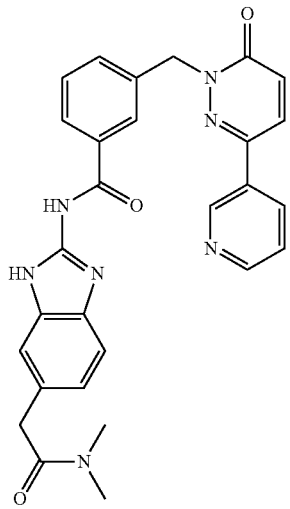
49
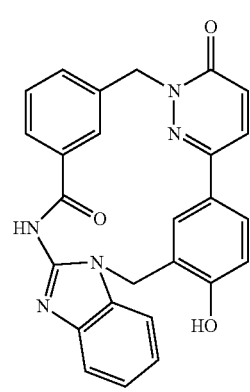
50
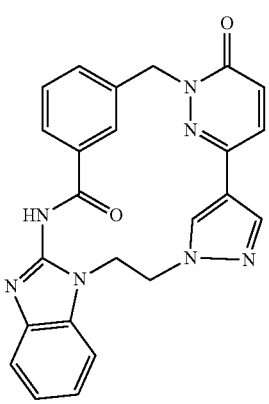
51
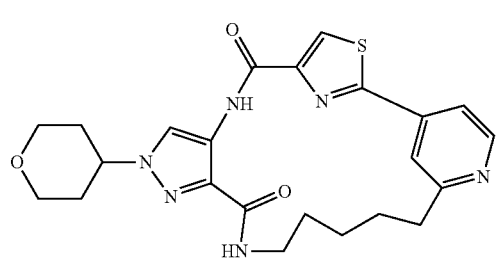

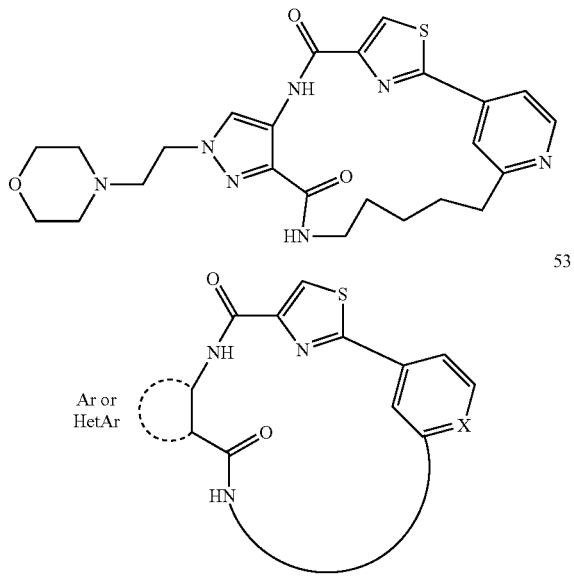

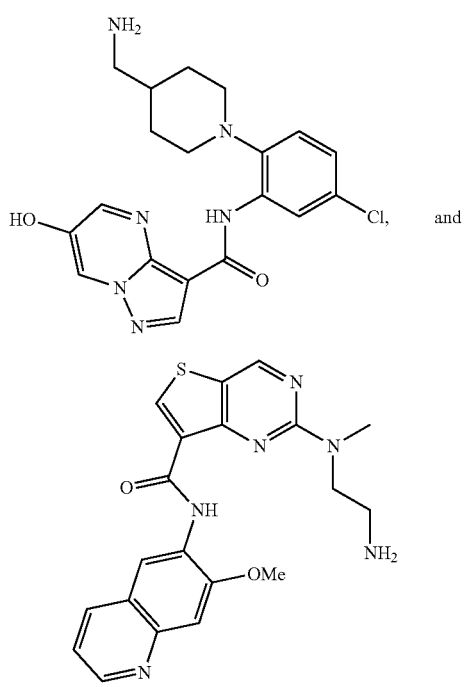 and

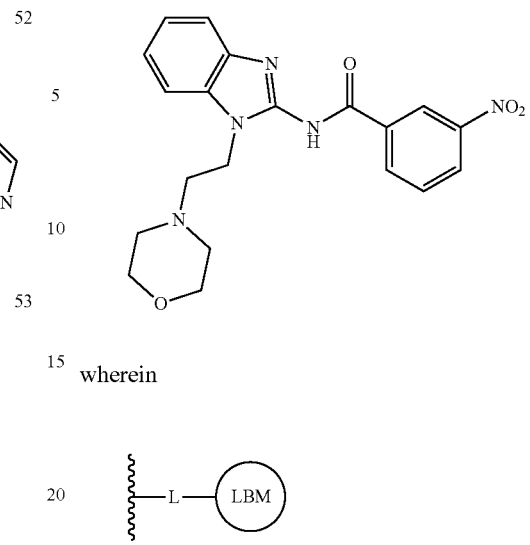

wherein

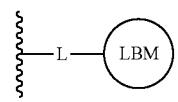

is attached to a modifiable carbon, oxygen, nitrogen or sulfur atom.

In some embodiments, IRAK is selected from a moiety recited in Cushing, L. et al., *IRAK4 kinase controls Toll-like receptor induced inflammation through the transcription factor IRF5 in primary human monocytes*, J. Bio. Chem., 2017, 292 (45): 18689-698, such as, for example:

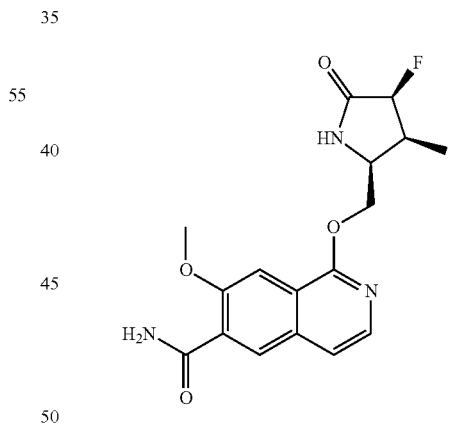

wherein

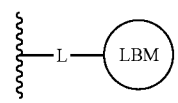

is attached to a modifiable carbon, oxygen, nitrogen or sulfur atom.

In some embodiments, IRAK is selected from a moiety recited in Li, N. et al., *Targeting interleukin-1 receptor-associated kinase for human hepatocellular carcinoma*, J. Ex. Clin. Can. Res., 2016, 35 (1): 140-50, such as, for example:

wherein

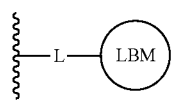

is attached to a modifiable carbon, oxygen, nitrogen or sulfur atom.

In some embodiments, IRAK is selected from a moiety recited in Zhang, D. et al., *Constitutive IRAK4 Activation Underlies Poor Prognosis and Chemoresistance in Pancreatic Ductal Adenocarcinoma*, Clin. Can. Res., 2017, 23 (7): 1748-59, such as, for example:

I-5409

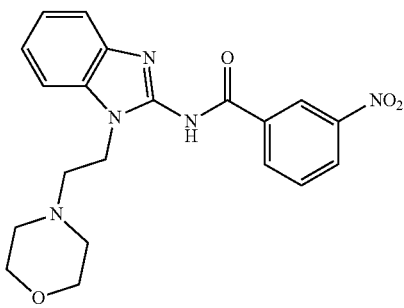 [SMILES: O=C(Nc1nc2ccccc2n1CCN1CCOCC1)c1cccc([N+](=O)[O-])c1]

(Sigma)

wherein

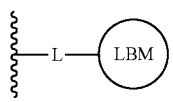

is attached to a modifiable carbon, oxygen, nitrogen or sulfur atom.

In some embodiments, IRAK is selected from a moiety recited in Dudhgaonkar, S. et al., *Selective IRAK4 Inhibition Attenuates Disease in Murine Lupus Models and Demonstrates Steroid Sparing Activity*, J. of Immun., 2017, 198 (3): 1308-19, such as, for example:

wherein

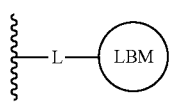

is attached to a modifiable carbon, oxygen, nitrogen or sulfur atom.

In some embodiments, IRAK is selected from a moiety recited in Wang, Z. et al., *IRAK-4 Inhibitors for Inflammation*, Cur. Top. Med. Chem., 2009, 9 (8): 724-37, such as, for example:

1

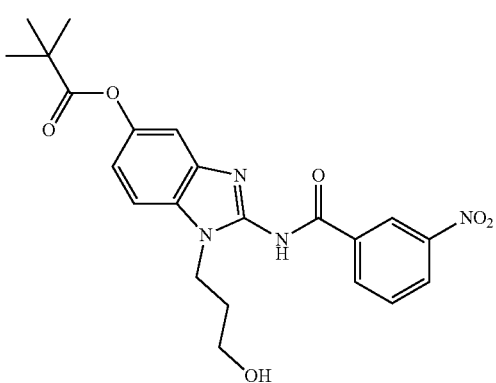

2

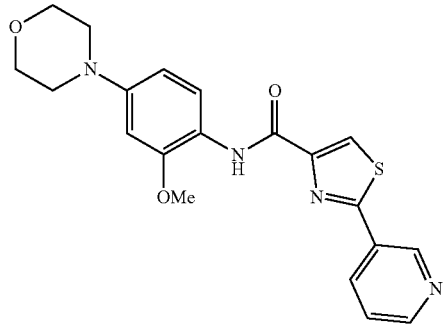

3

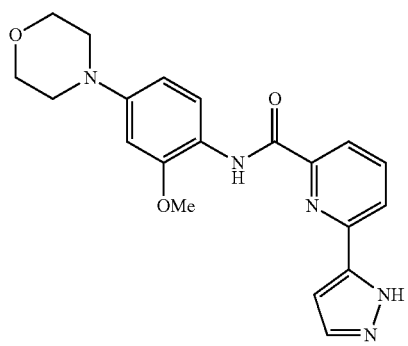

4

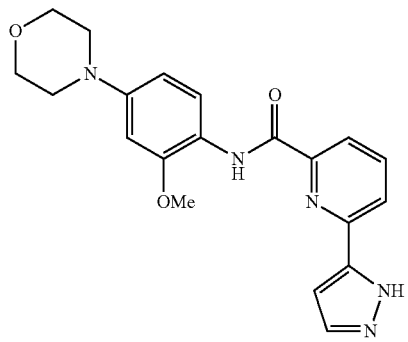

5

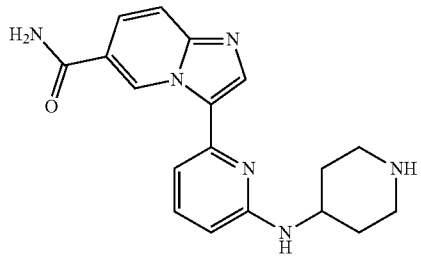

6

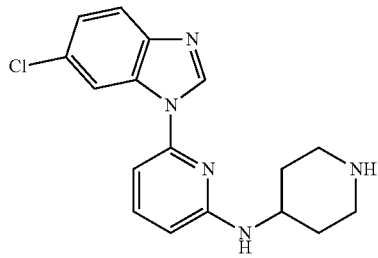

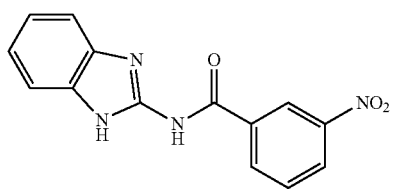
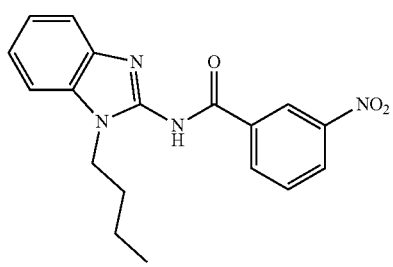
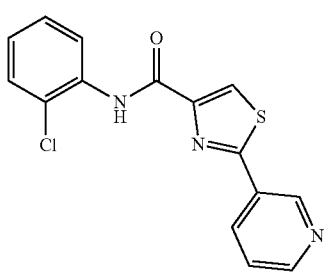
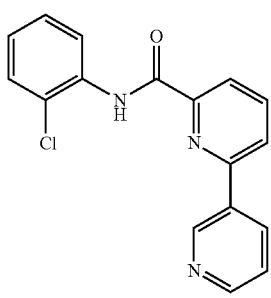
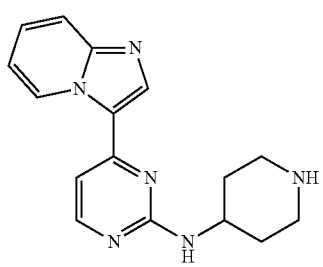
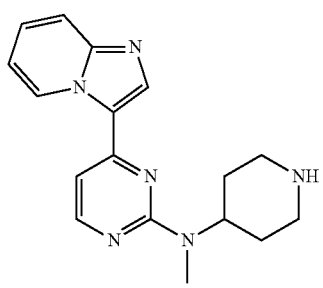
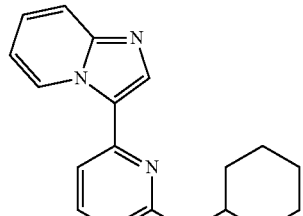
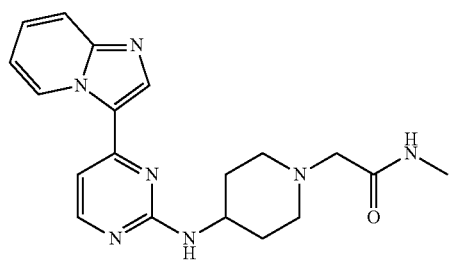
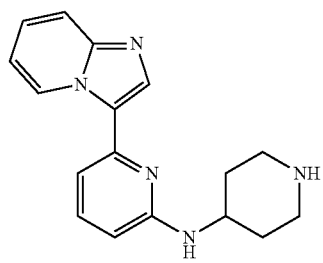
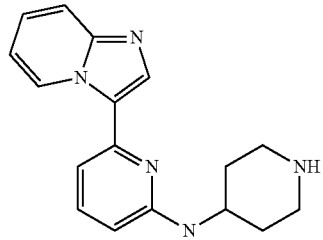
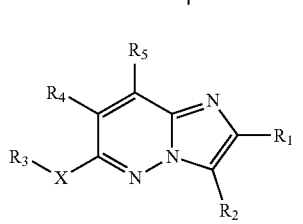
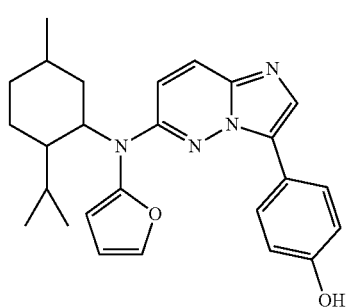

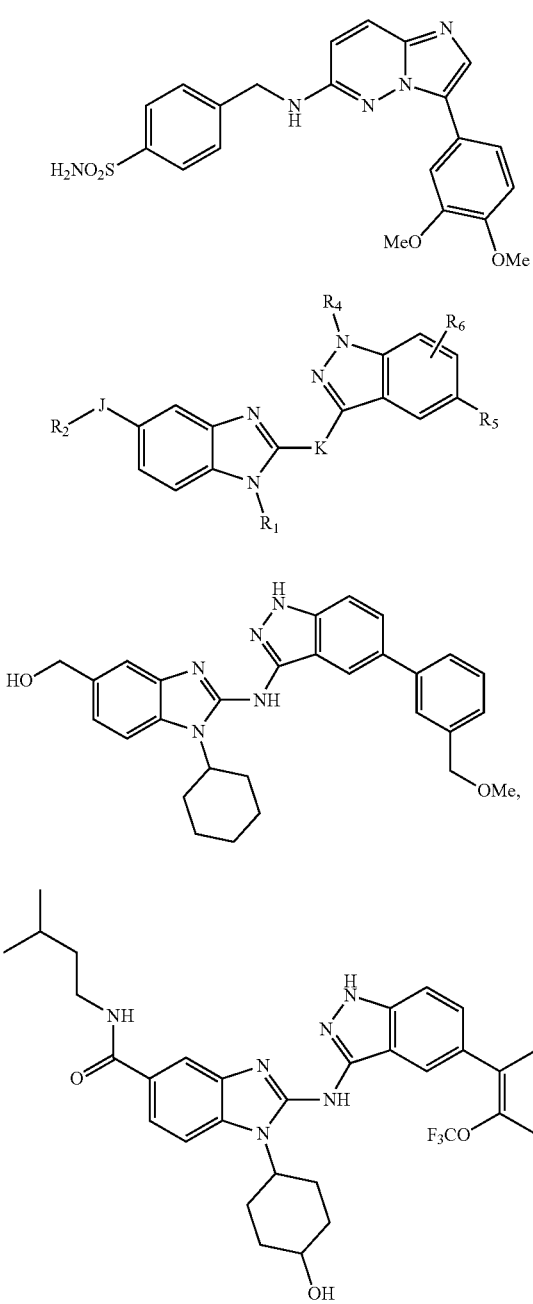

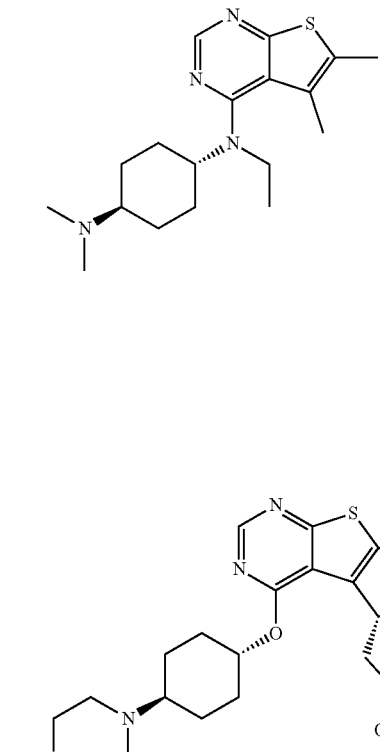

wherein

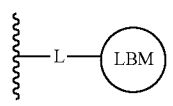

is attached to a modifiable carbon, oxygen, nitrogen or sulfur atom.

In some embodiments, IRAK is selected from a moiety recited in Kelly, P. N. et al., *Selective interleukin-1 receptor-associated kinase 4 inhibitors for the treatment of autoimmune disorders and lymphoid malignancy*, J. Exp. Med., 2015, 212 (13): 2189-201, such as, for example:

wherein

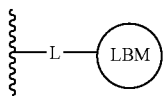

is attached to a modifiable carbon, oxygen, nitrogen or sulfur atom.

In some embodiments, IRAK is selected from a moiety recited in Dunne, A. et al., *IRAK1 and IRAK4 Promote Phosphorylation, Ubiquitation, and Degradation of MyD88 Adaptor-like (Mal)*, J. Bio. Chem., 2010, 285 (24): 18276-82, such as, for example:

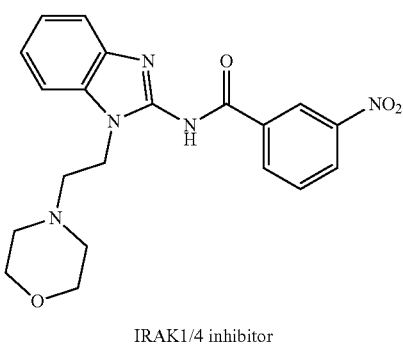 [SMILES: O=C(Nc1nc2ccccc2n1CCN1CCOCC1)c1cccc([N+](=O)[O-])c1]

IRAK1/4 inhibitor wherein

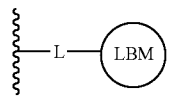

is attached to a modifiable carbon, oxygen, nitrogen or sulfur atom.

In some embodiments, IRAK is selected from a moiety recited in Küppers, R., *IRAK inhibition to shut down TLR signaling in autoimmunity andMyD88-dependent lymphomas*, J. Exp. Med, 2015, 212 (13): 2184, such as, for example:

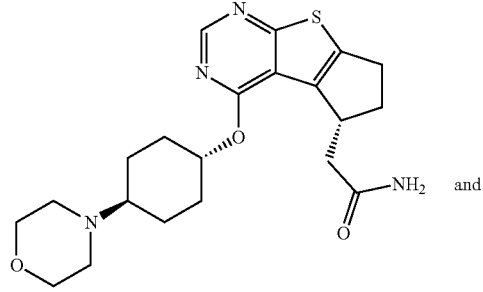

ND-2110

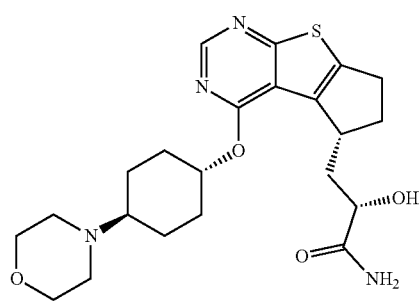

ND-2158 wherein

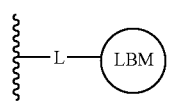

is attached to a modifiable carbon, oxygen, nitrogen or sulfur atom.

In some embodiments, IRAK is selected from a moiety recited in Chiang, E. Y. et al., *Immune Complex-Mediated Cell Activation frJom Systemic Lupus Erythematosus and Rheumatoid Arthritis Patients Elaborate Different Requirements for IRAK1/4 Kinase Activity across human Cell Types*, J. Immunol., 2011, 186 (2): 1279-88, such as, for example:

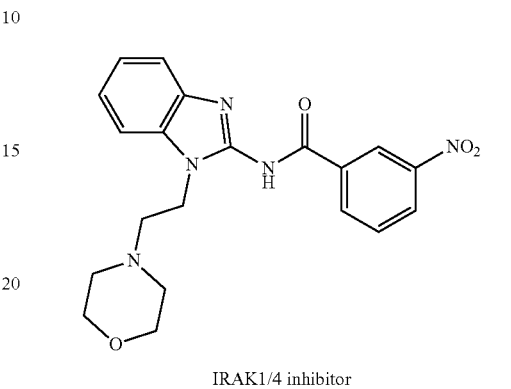

IRAK1/4 inhibitor wherein

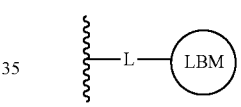

is attached to a modifiable carbon, oxygen, nitrogen or sulfur atom.

In some embodiments, IRAK is selected from a moiety recited in Lee, K. L. et al., *Discovery of Clinical Candidate 1-{[2S,3S,4S)-3-ethyl-4-fluoro-5-oxopyrrolidin-2-yl] methoxy}-7-methoxyisoquinoine-6-carboxamide (PF-06650833), a Potent, Selective Inhibitor of IInterleukin-1 Receptor Associated Kinase 4 9IRAK4), by Fragment-Based Drug Design*, J. Med. Chem., 2017, 60 (13): 5521-42, such as, for example:

Amgen 1

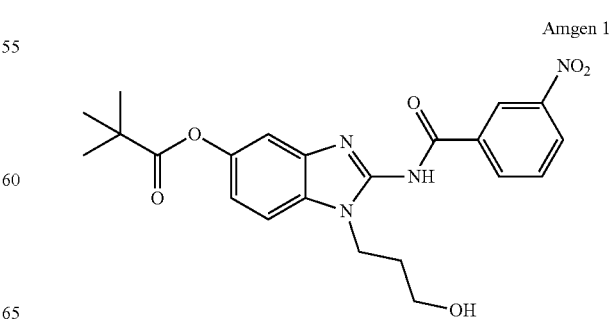

287
-continued
Amgen 2
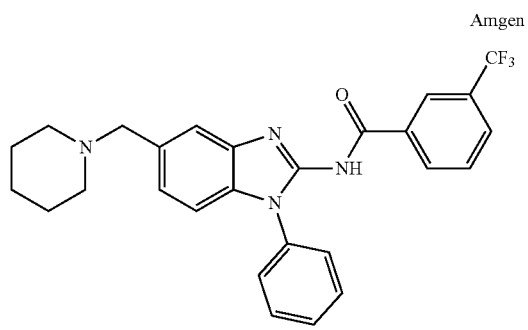
UCB 3
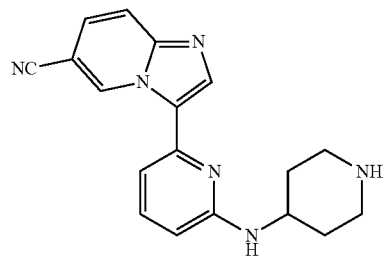
Pfizer 4
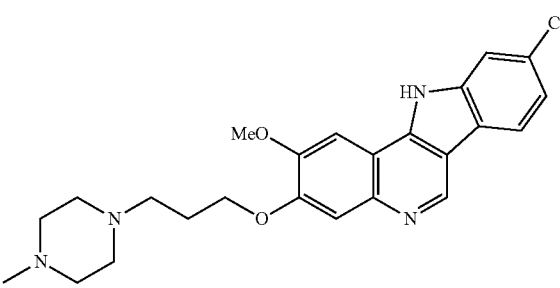
Merck 5
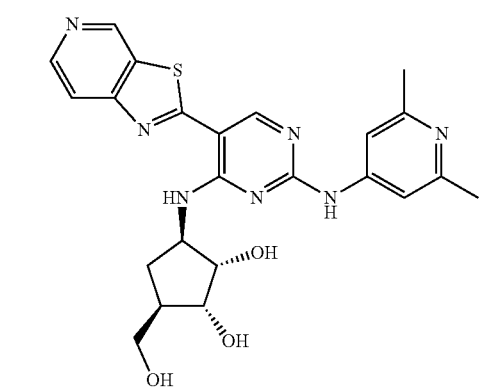
288
-continued
Merck 6
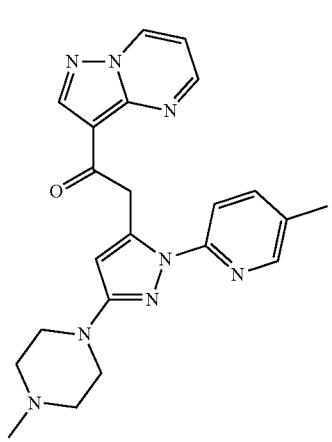
Merck 7
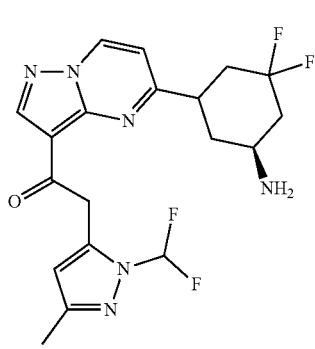
Nimbus 8
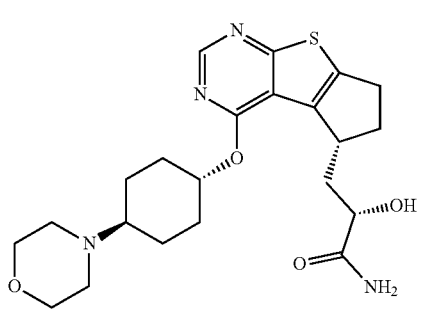
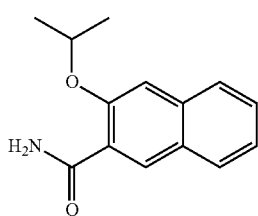
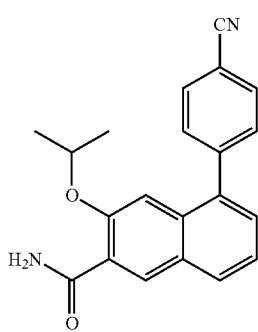

14 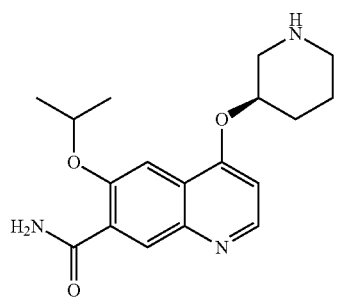
16 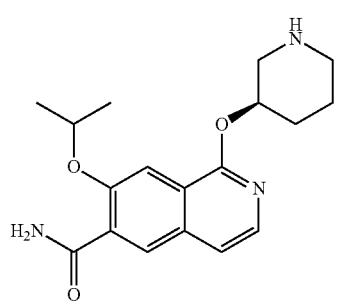
20 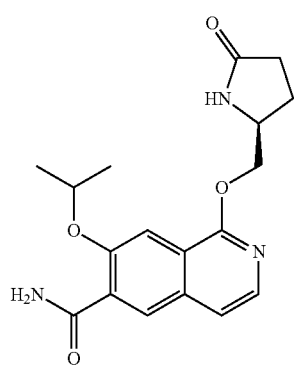
21 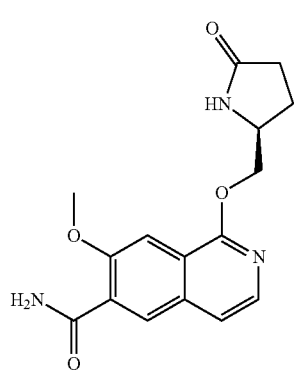
22 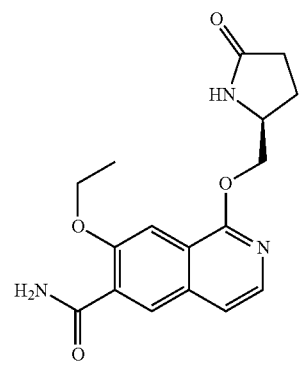
23 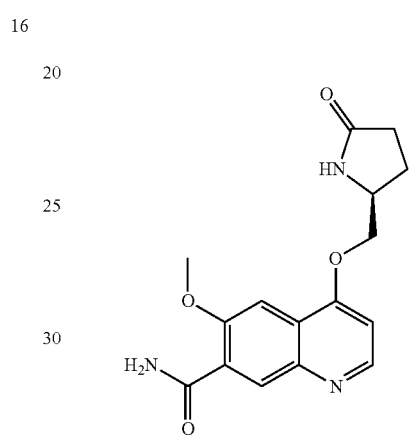
24 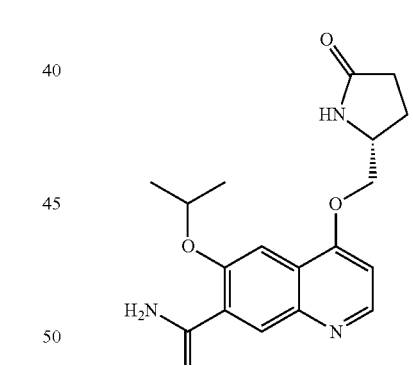
26 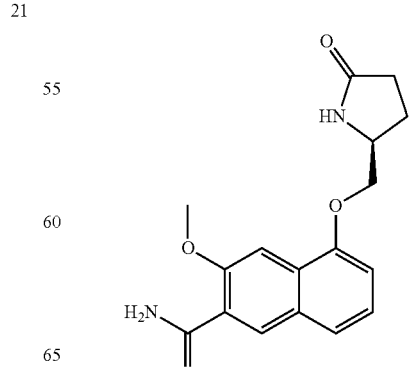

| | |
|---|---|
| 30 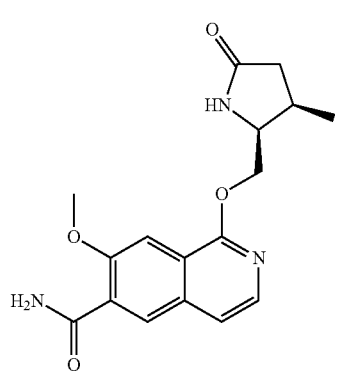 | 36 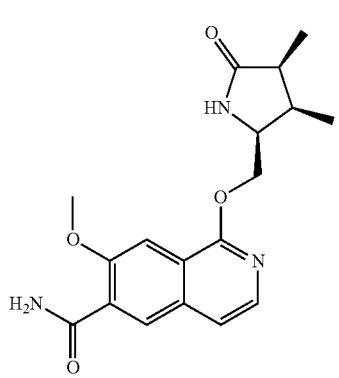 |
| 31 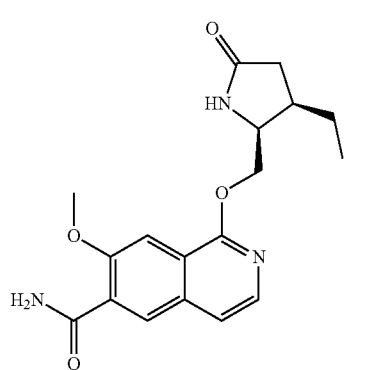 | 37 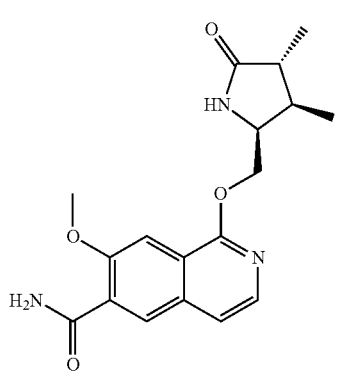 |
| 32 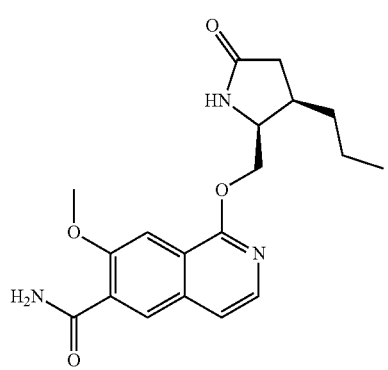 | 38 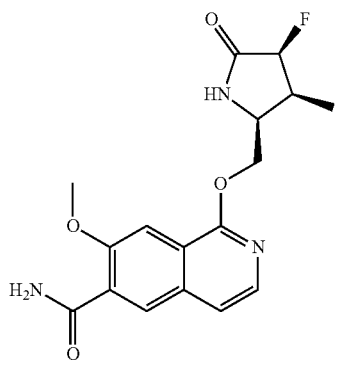 |
| 33 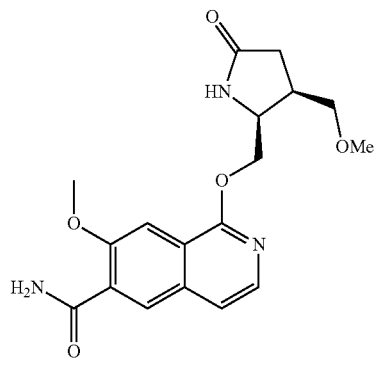 | 39 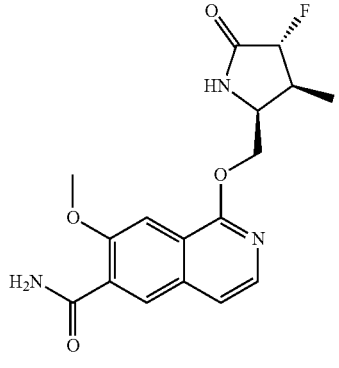 |

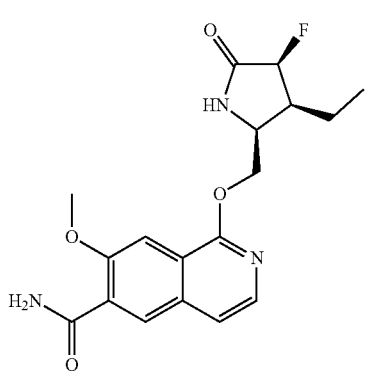

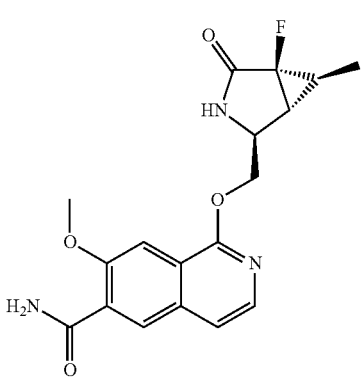

wherein

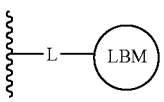

is attached to a modifiable carbon, oxygen, nitrogen or sulfur atom.

In some embodiments, IRAK is selected from a moiety recited in Kondo, M. et al., *Renoprotective effects of novel interleukin-1 receptor-associated kinase 4 inhibitor AS2444697 through anti-inflammatory action in 5/6 nephrectomized rats*, Naunyn-Schmiedeberg's Arch Pharmacol., 2014, 387 (10): 909-19, such as, for example:

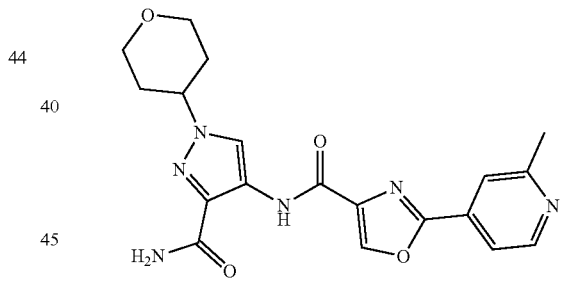

AS2444697 wherein

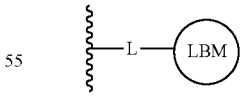

is attached to a modifiable carbon, oxygen, nitrogen or sulfur atom.

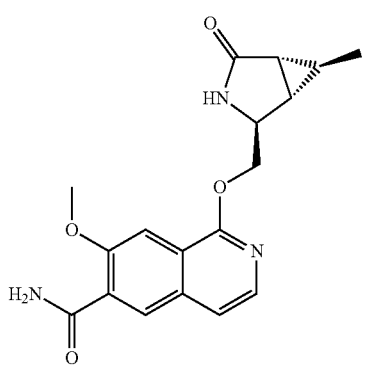

and

In some embodiments, IRAK is selected from a moiety recited in Song, K. W. et al., *The Kinase activities of interleukin-1 receptor associated kinase (IRAK)-1 and 4 are redundant in the control of inflammatory cytokine expression in human cells*, Mol. Immunol., 2009, 46 (7): 1458-66, such as, for example: RO0884, RO1679, or RO6245, wherein

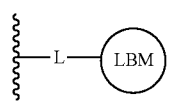

is attached to a modifiable carbon, oxygen, nitrogen or sulfur atom.

In some embodiments, IRAK is selected from a moiety recited in Vollmer, S. et al., *The mechanism of activation of IRAK1 and IRAK4 by interleukin-1 and Toll-like receptor agonists*, Biochem. J., 2017, 474 (12): 2027-38, such as, for example: IRAK-IN-1A, JNK-IN-7, and JNK-IN-8, wherein

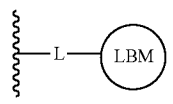

is attached to a modifiable carbon, oxygen, nitrogen or sulfur atom.

In some embodiments, an IRAK ligand is selected from moiety recited in McElroy, W. T., et al., *Potent and Selective Amidopyrazole Inhibitors of IRAK4 That Are Efficacious in a Rodent Model of Inflammation*, Med. Chem. Lett., 2015, 6 (6): 677-82, such as, for example:

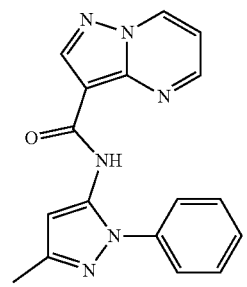

1

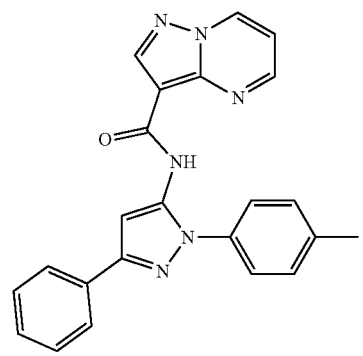

2

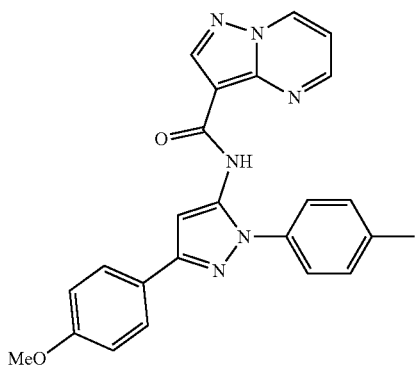

6

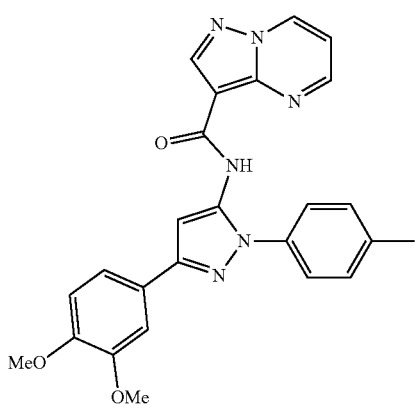

7

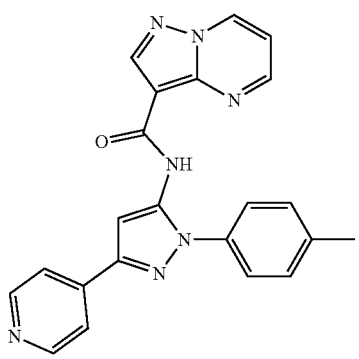

8

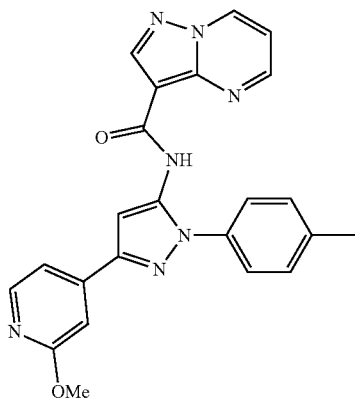

9

10
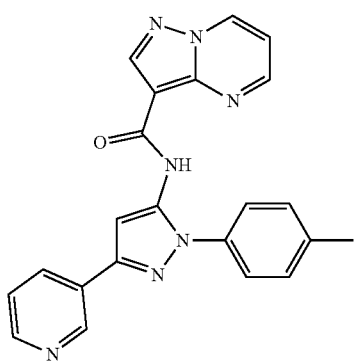
14
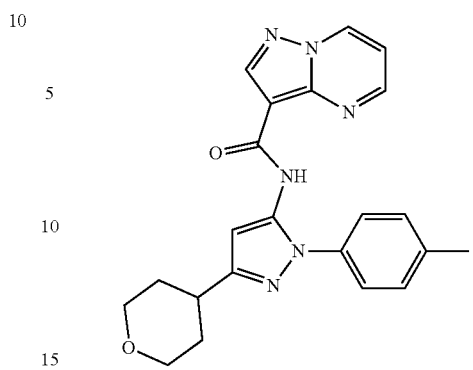
11
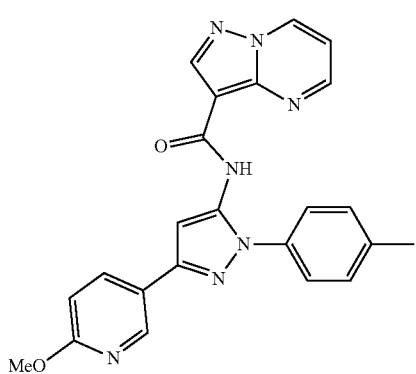
15
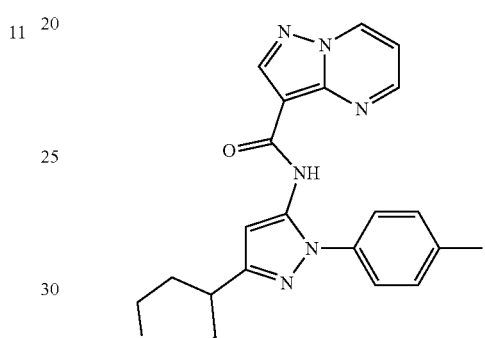
12
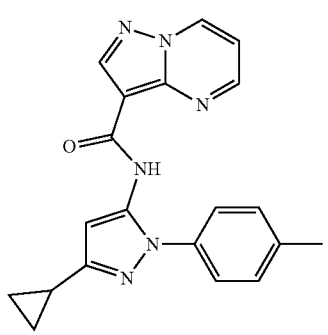
16
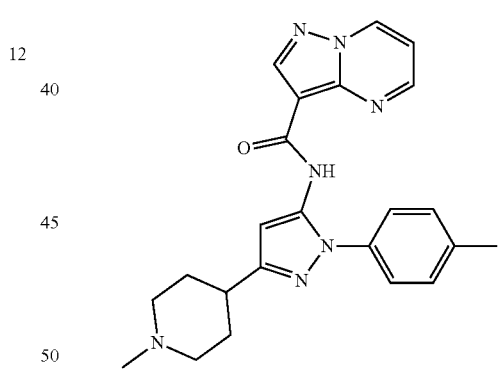
13
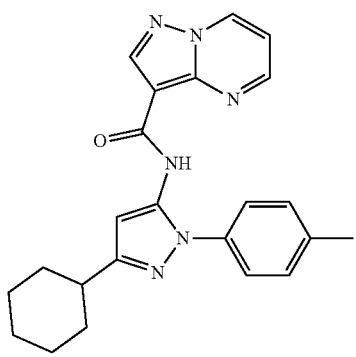
17
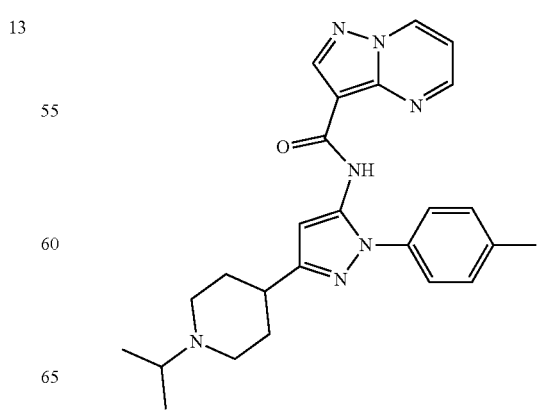

| 18 | 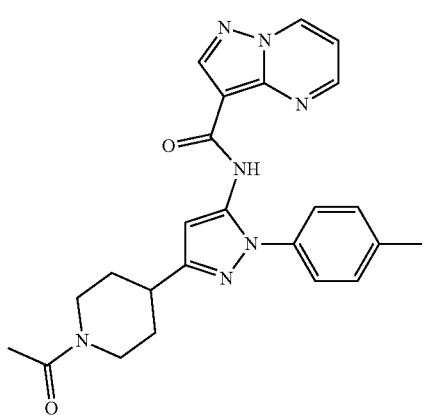 |
|---|---|
| 19 | 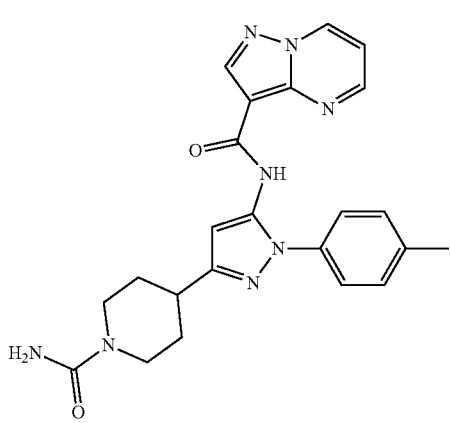 |
| 20 | 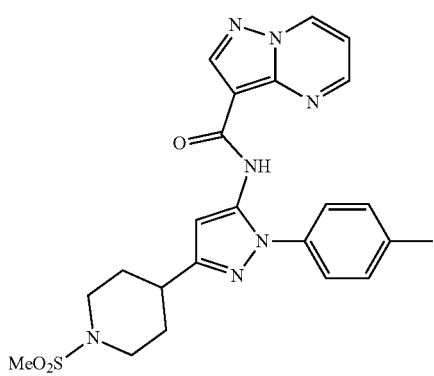 |
| 21 | 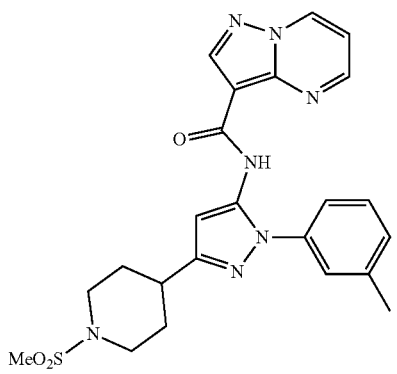 |
| 22 | 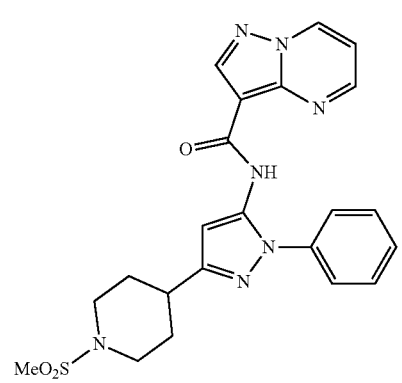 |
| 23 | 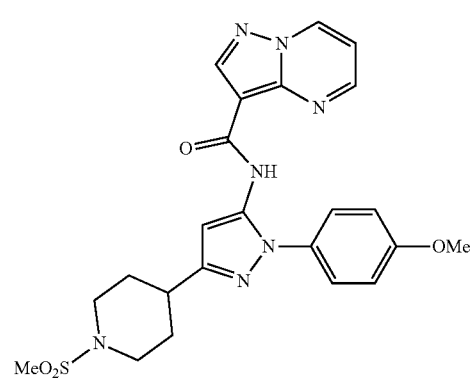 |
| 24 | 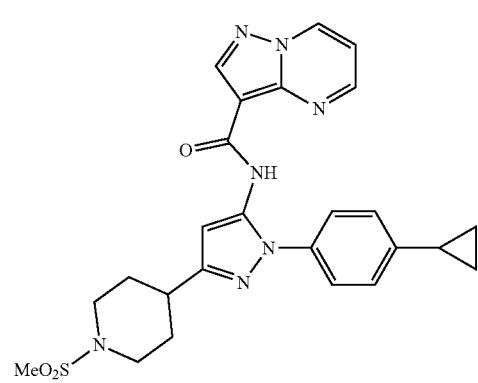 |
| 25 | 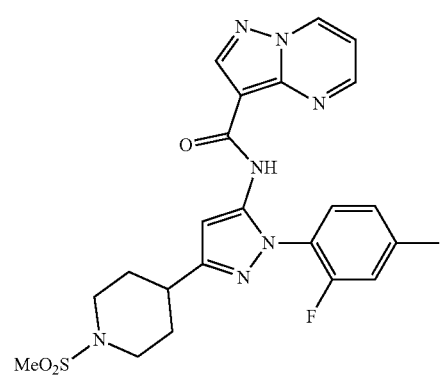 |

-continued
26
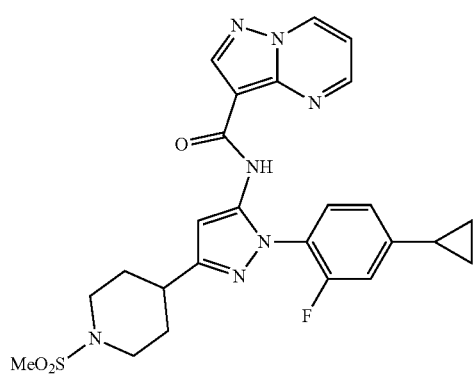
27
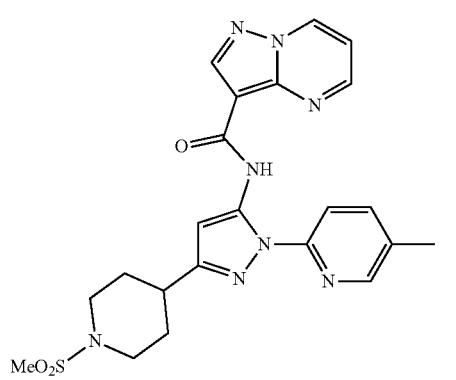
28
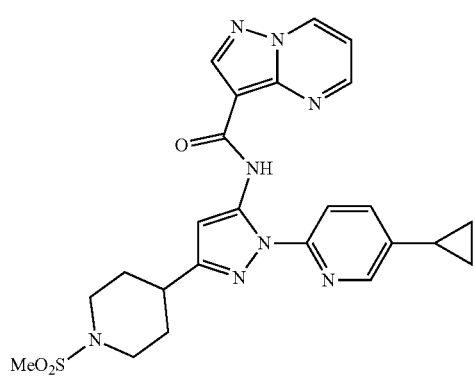
29
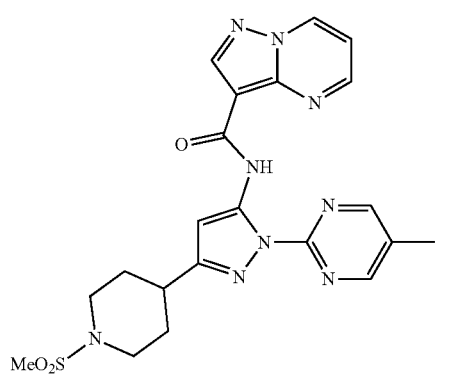
-continued
30
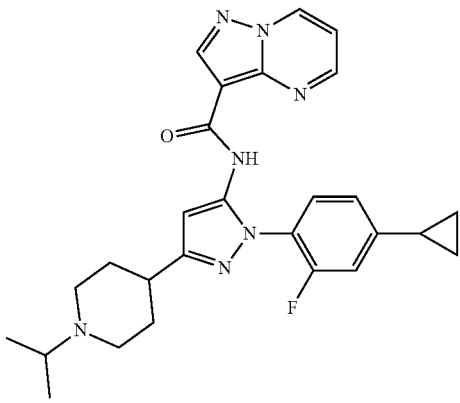
31
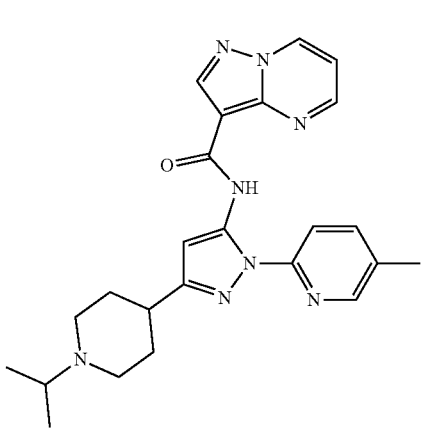
32
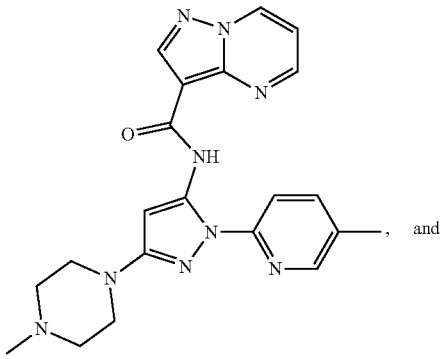
, and
33
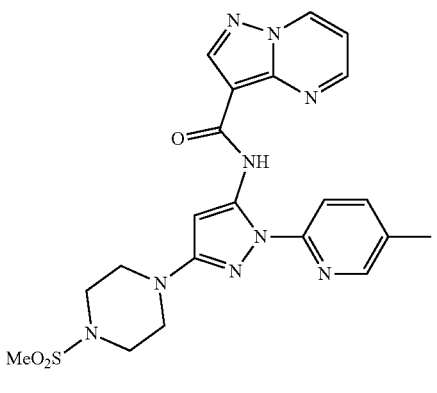

wherein
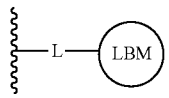
is attached to a modifiable carbon, oxygen, nitrogen or sulfur atom.
In some embodiments, an IRAK ligand is selected from moiety recited in Seganish, W. M., et al., *Discovery and Structure Enabled Synthesis of 2, 6-diaminopyrimidine-4-one IRAK4 Inhibitors*, Med. Chem. Lett., 2015, 6 (8): 942-47, such as, for example:
1
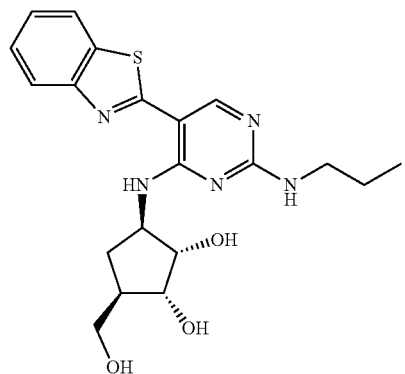
2
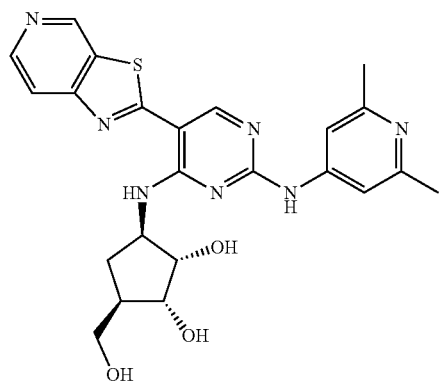
3
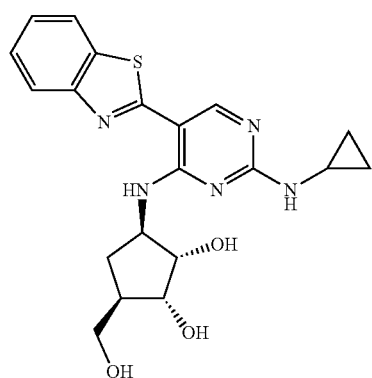
4
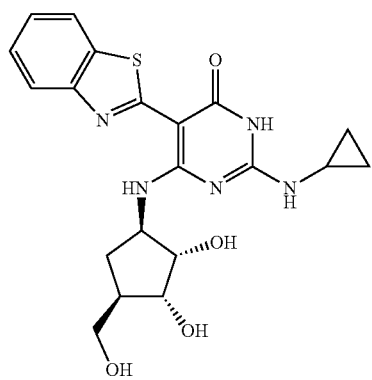
5
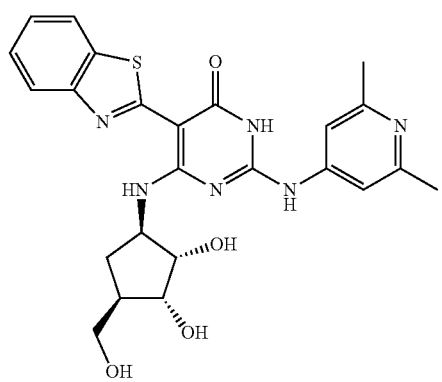
6
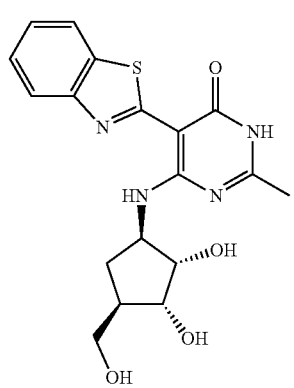
7
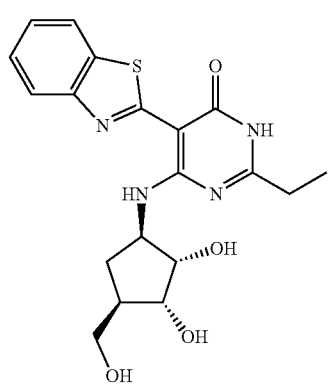

305
-continued
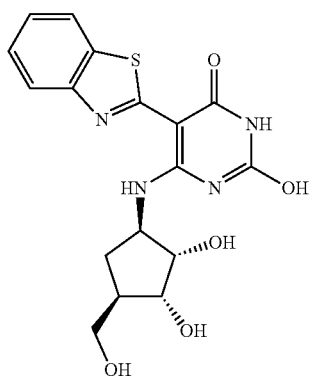
8
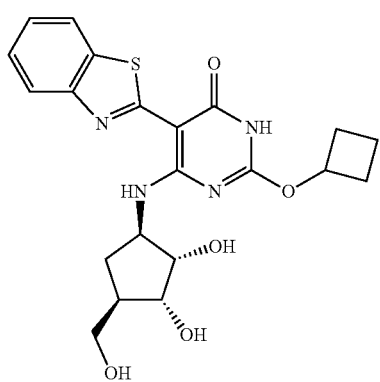
9
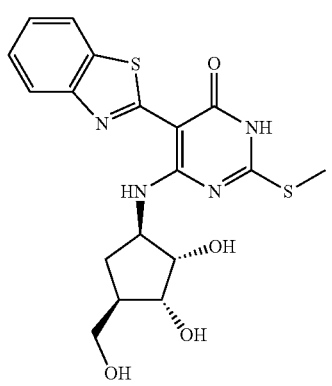
10
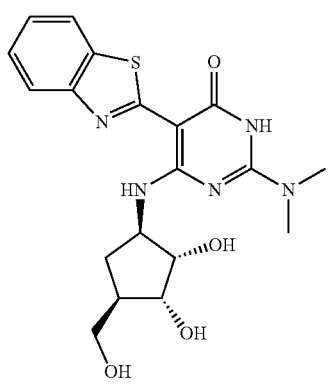
11
306
-continued
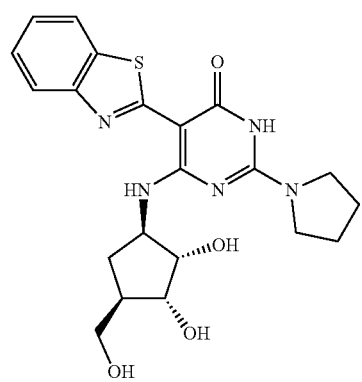
12
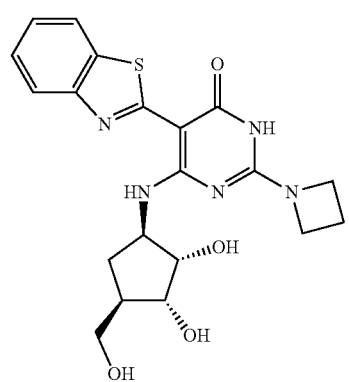
13
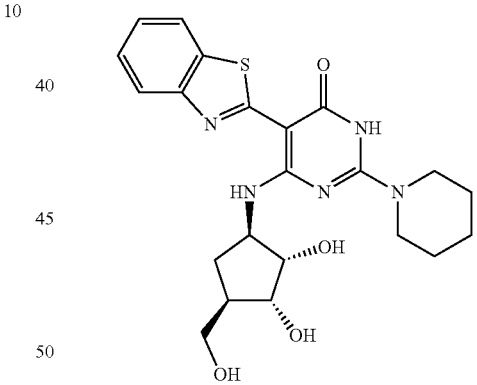
14
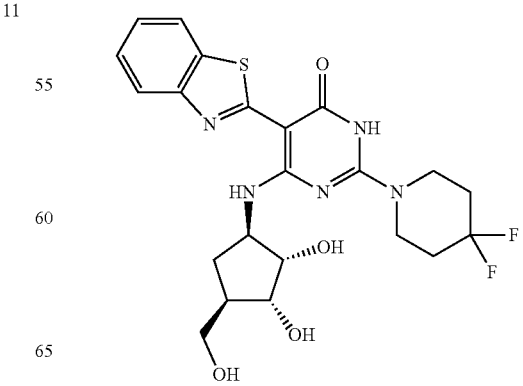
15

16
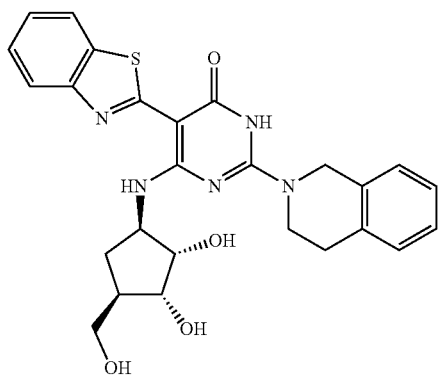
17
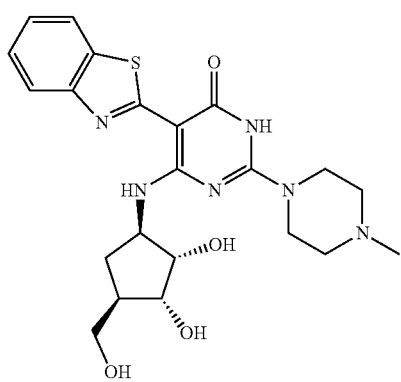
18
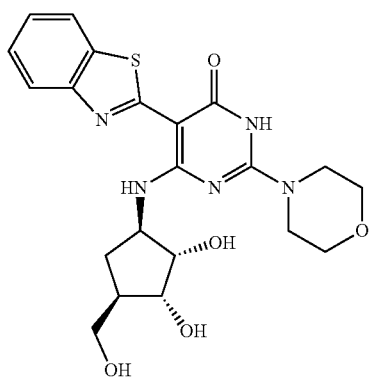
19
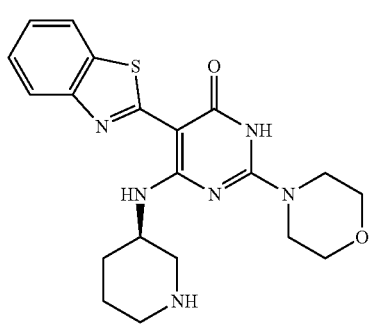
20
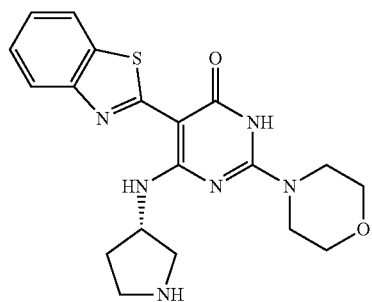
21
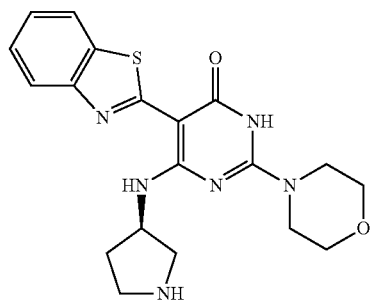
22
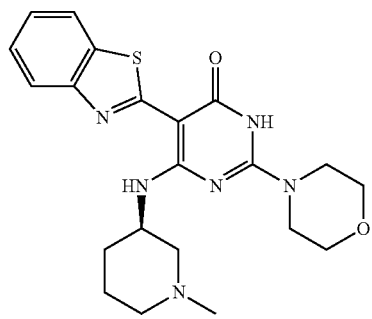
23
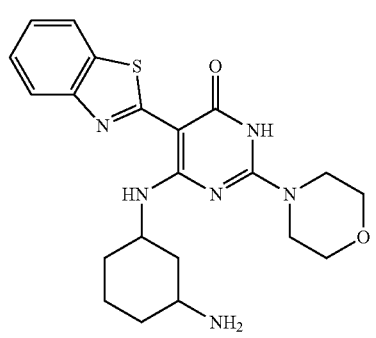
24
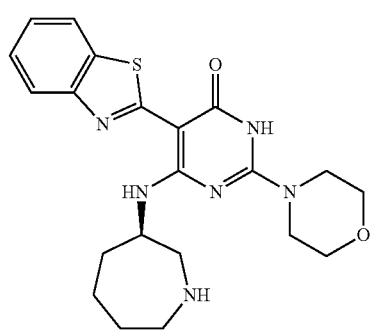

309
-continued
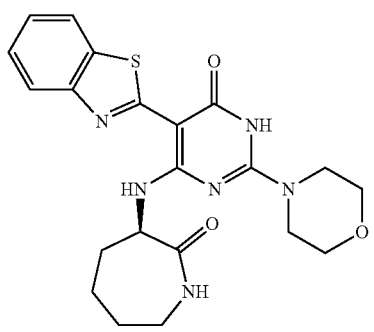
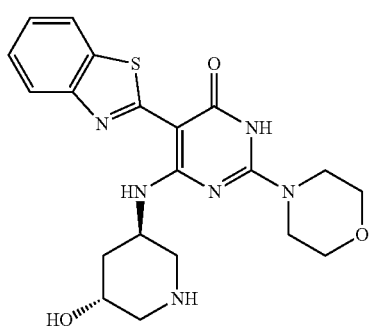
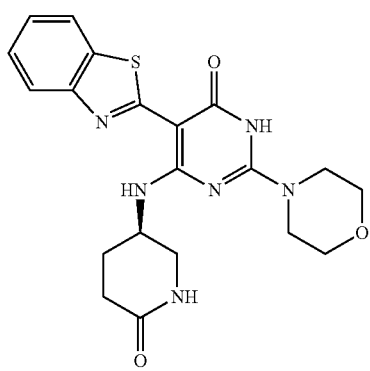
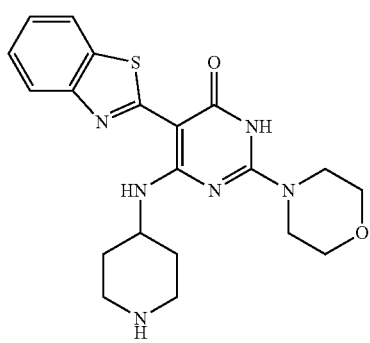
310
-continued
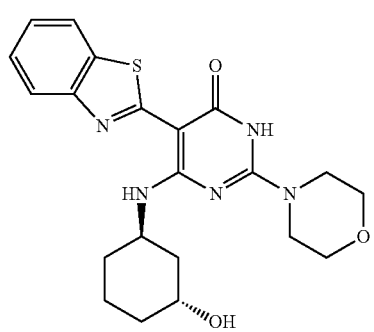

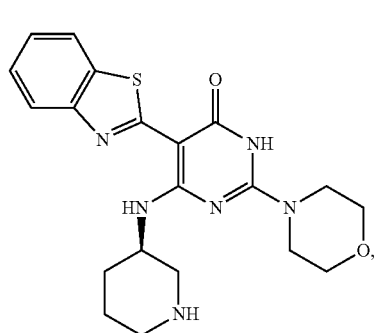
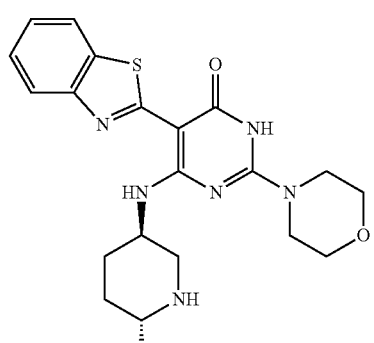, and
wherein
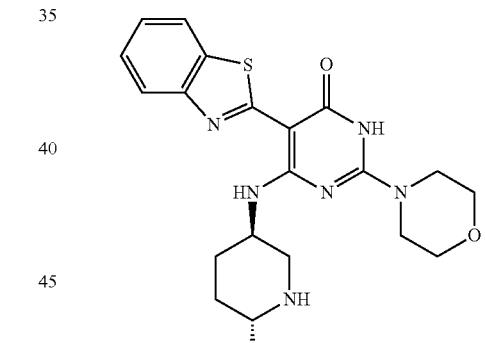
is attached to a modifiable carbon, oxygen, nitrogen or sulfur atom.
In some embodiments, an IRAK ligand is selected from moiety recited in Seganish, W. M., et al., *Initial optimization and series evolution of diaminopyrimidine inhibitors of interleukin-1 receptor associated kinase* 4, Bioorg. Med. Chem. Lett., 2015, 25 (16): 3203-207, such as, for example:

-continued
| 1 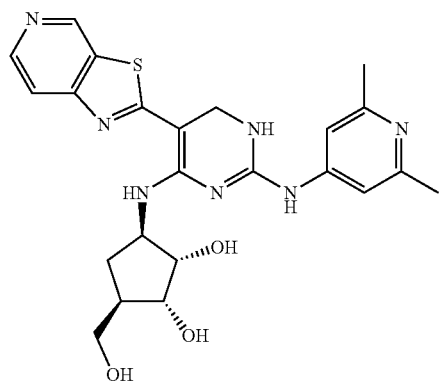 | 5 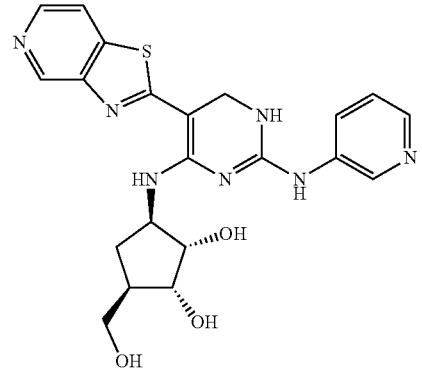 |
| --- | --- |
| 2 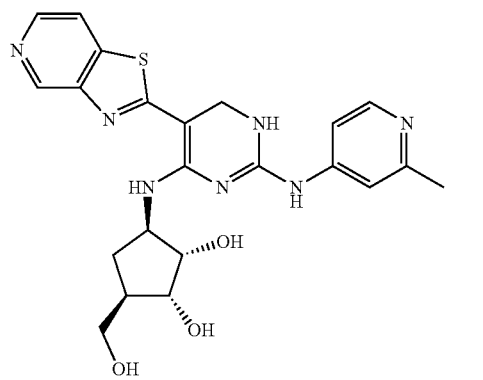 | 6 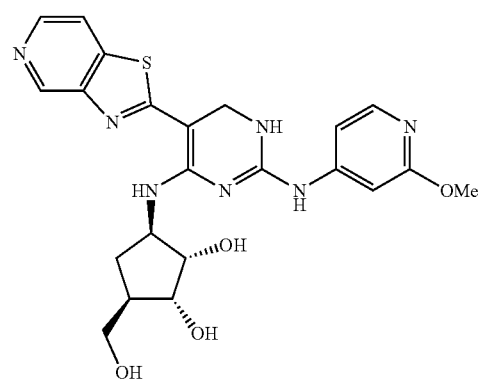 |
| 3 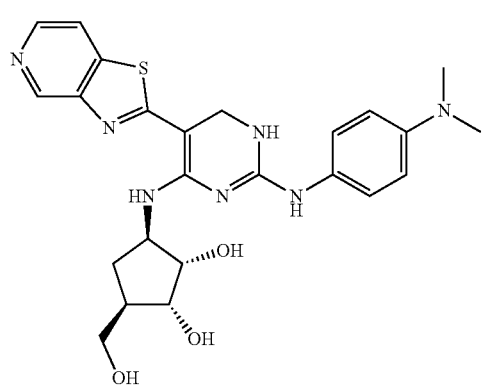 | 7 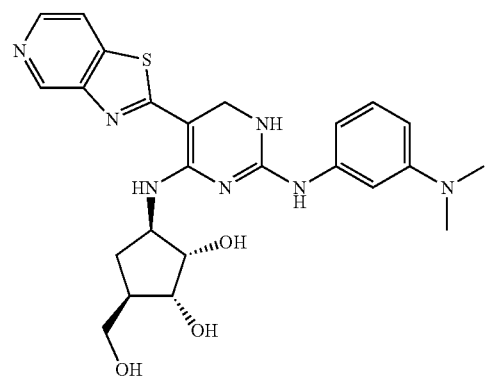 |
| 4 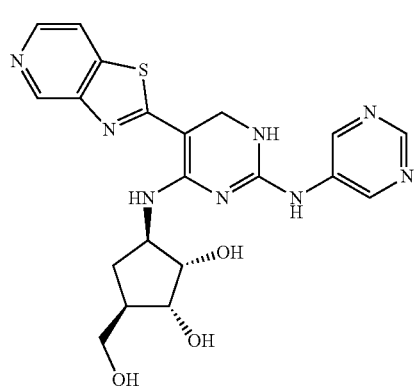 | 8 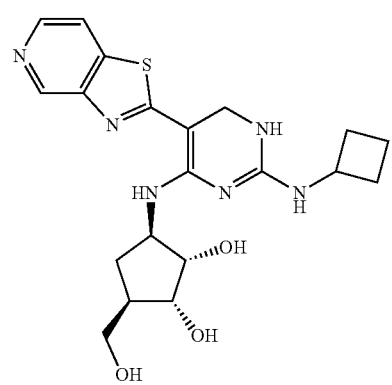 |

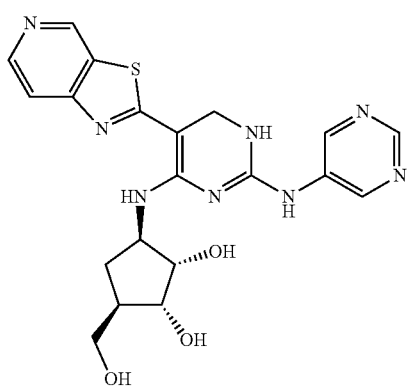
9
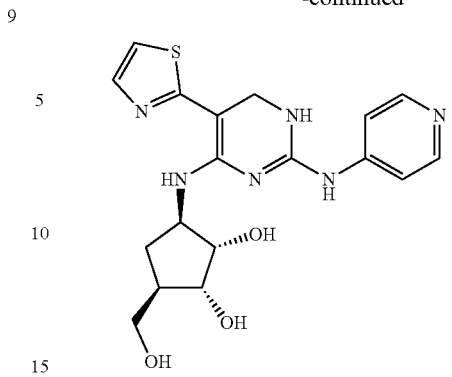
13
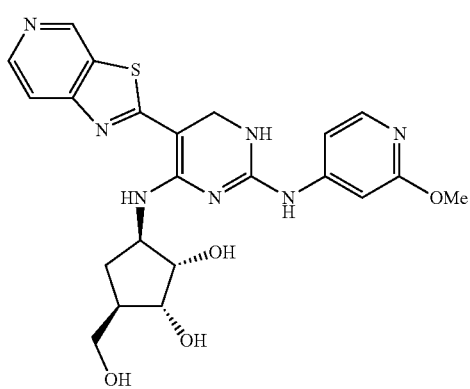
10
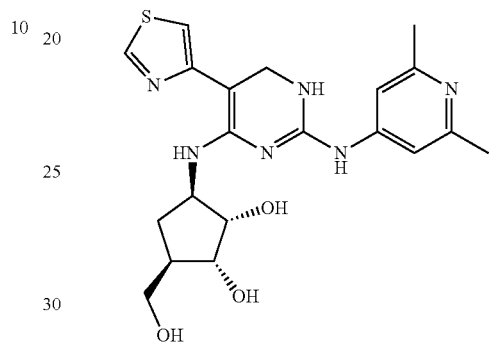
14
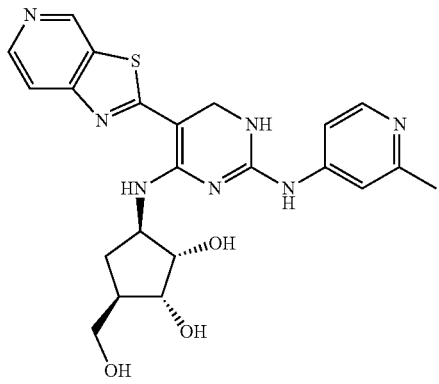
11
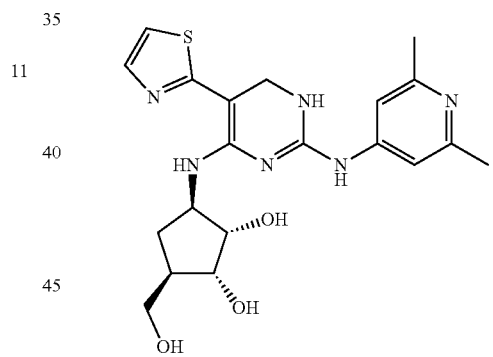
15
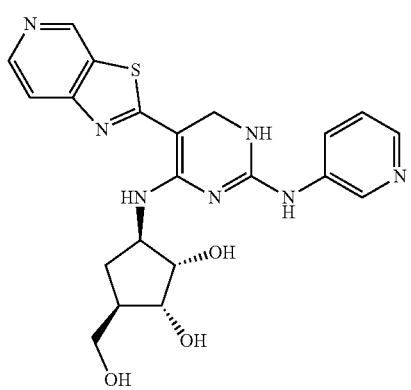
12
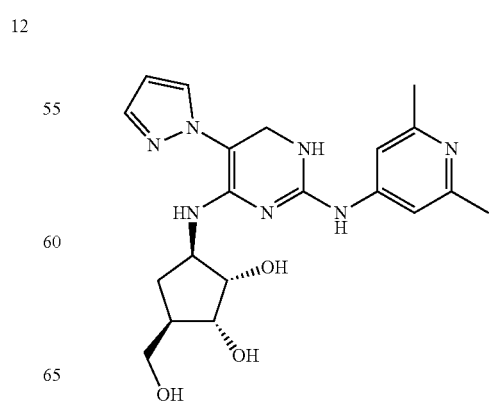
16

17
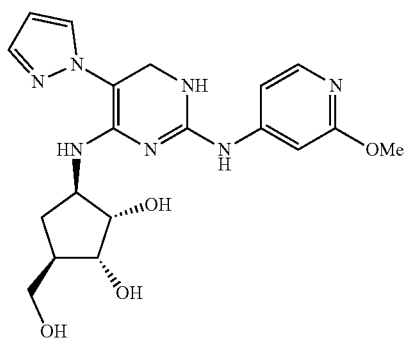
18
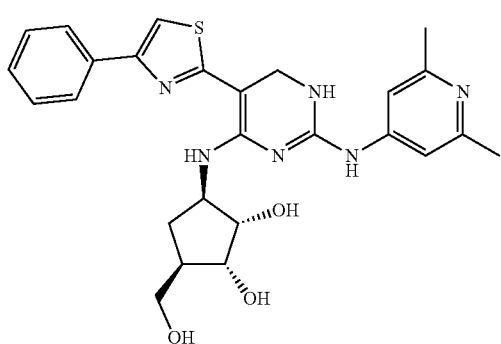
19
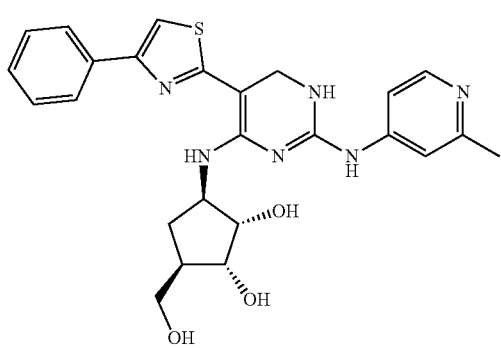
20
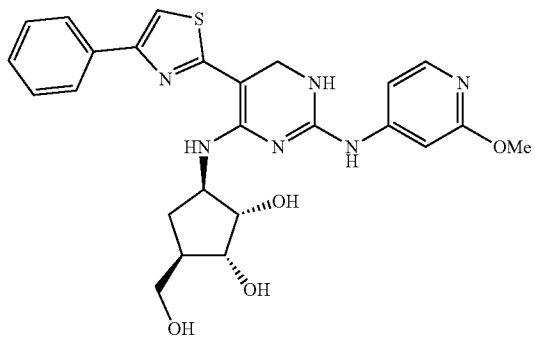
21
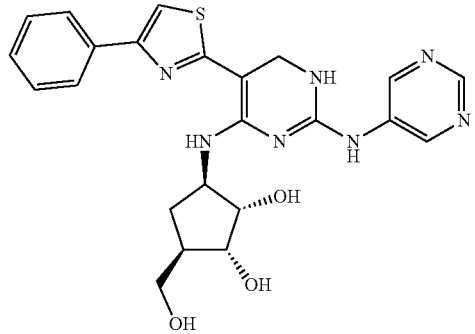
22
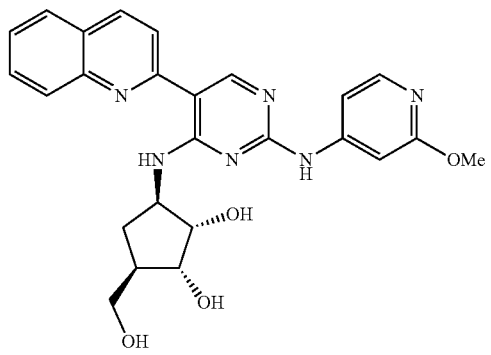
23
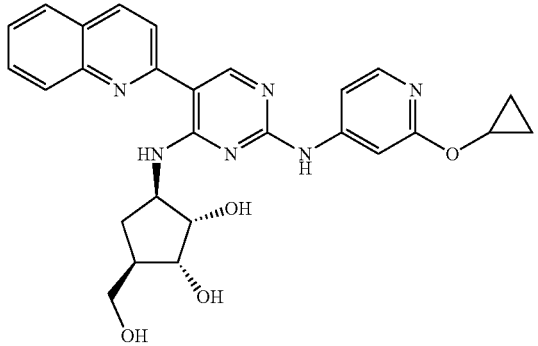
24
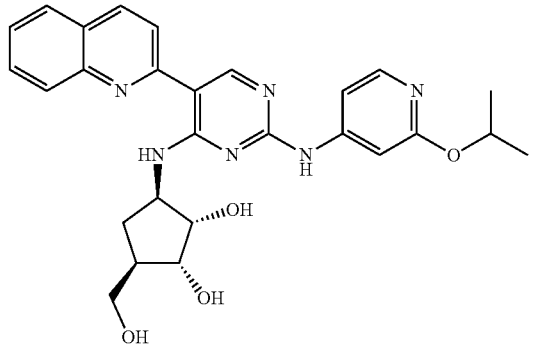

317
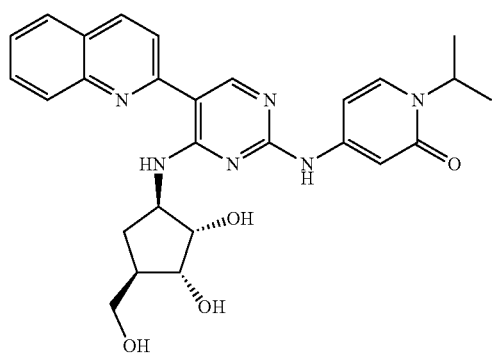  25
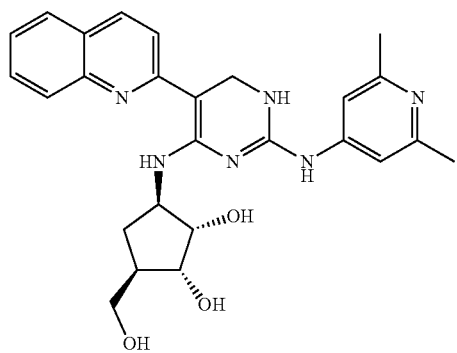  26
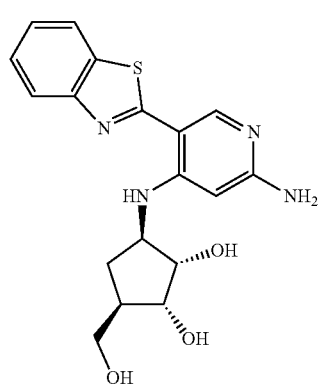  27
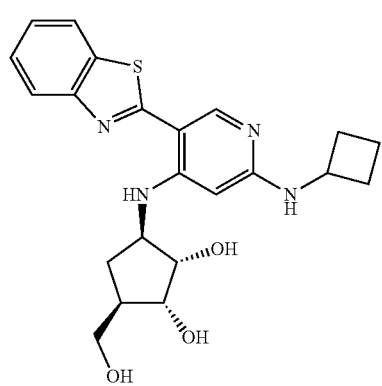  28
318
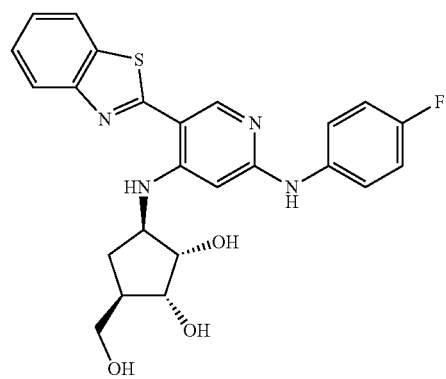  29
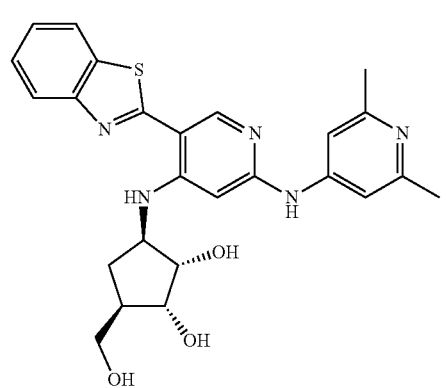  30
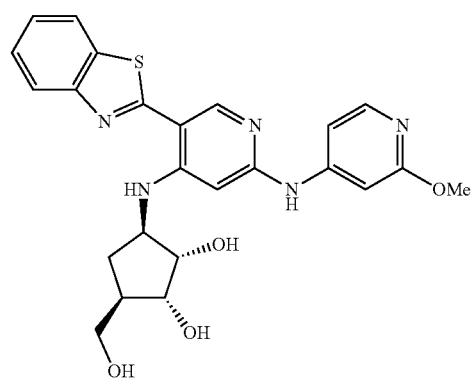  31
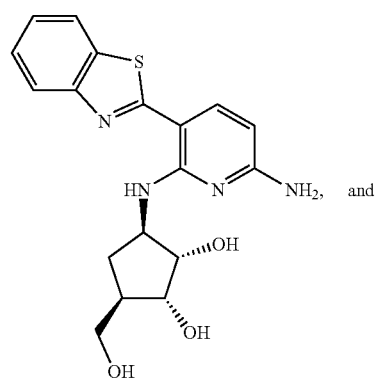  32, and 33
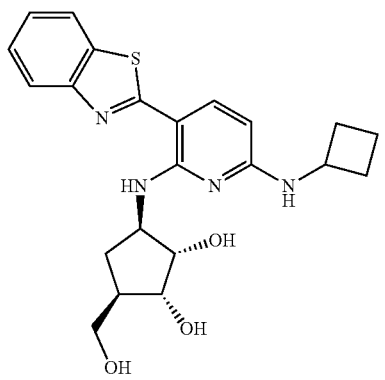
wherein
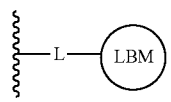
is attached to a modifiable carbon, oxygen, nitrogen or sulfur atom.
In some embodiments, an
In some embodiments, IRAK is
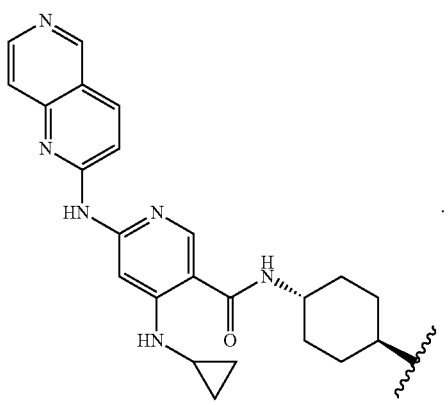 [SMILES: *[C@H]1CC[C@H](NC(=O)c2cnc(Nc3ccc4cnccc4n3)cc2NC2CC2)CC1]
In some IRAK ligand is selected from moiety recited in McElroy, W. T., et al., *Discovery and hit-to-lead optimization of 2, 6-diaminopyrimidine Inhibitors of interleukin-1 receptor-associated kinase 4*, Bioorg. Med. Chem. Lett., 2015, 25 (9): 1836-41, such as, for example:
1
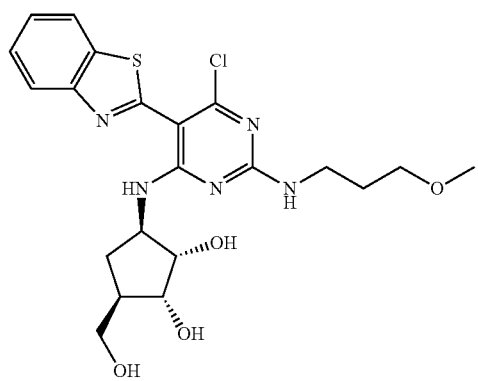
2
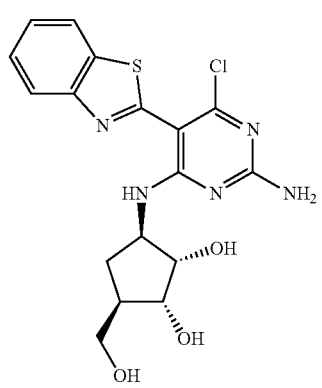
3
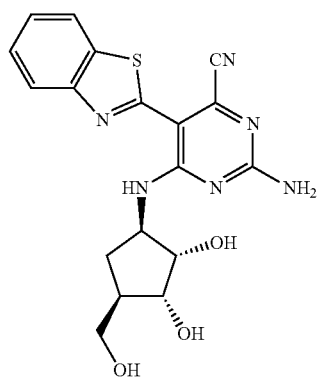
4
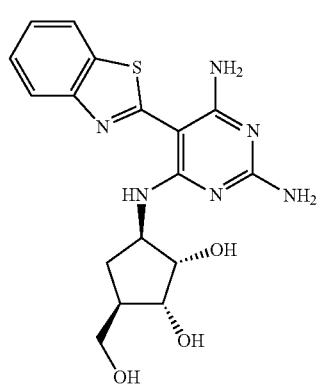

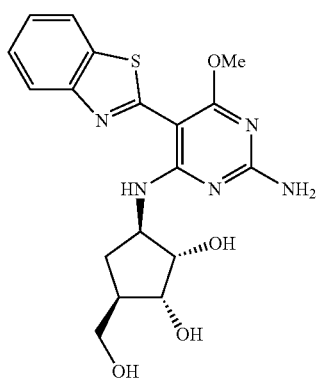
5
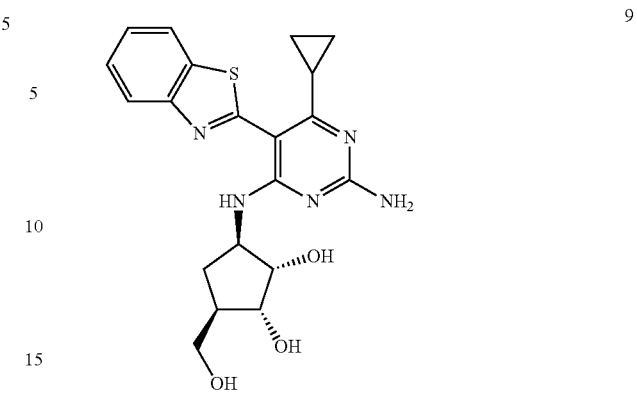
9
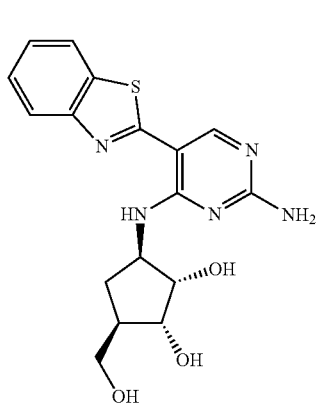
6
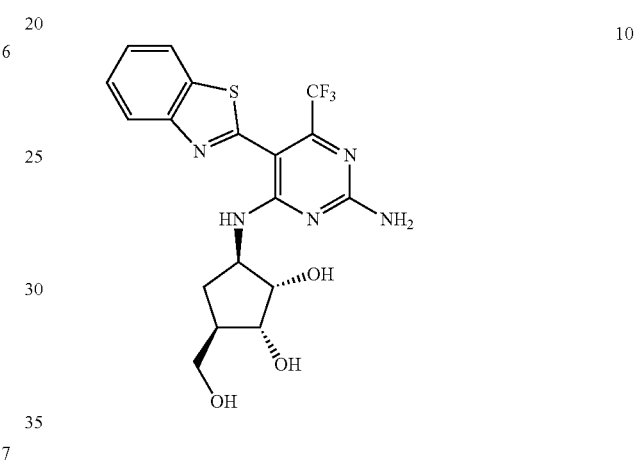
10
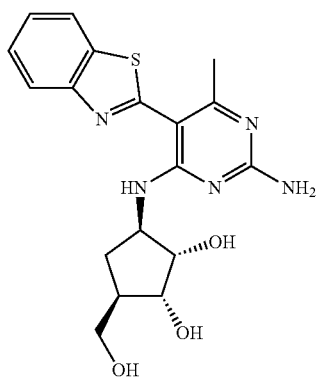
7
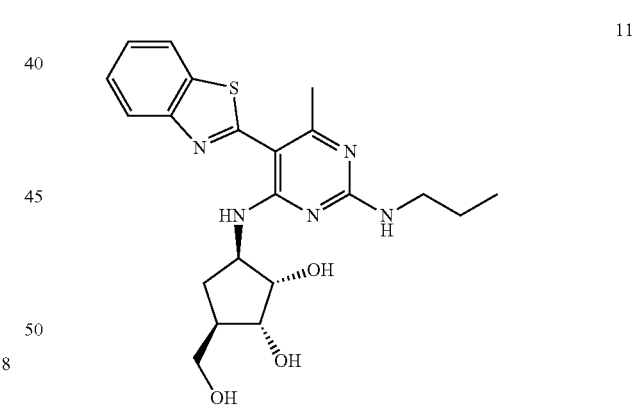
11
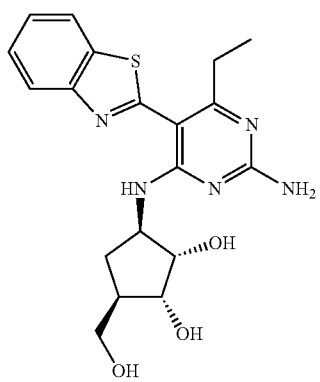
8
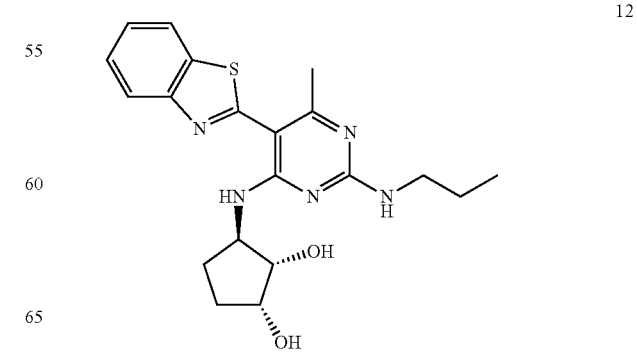
12

323
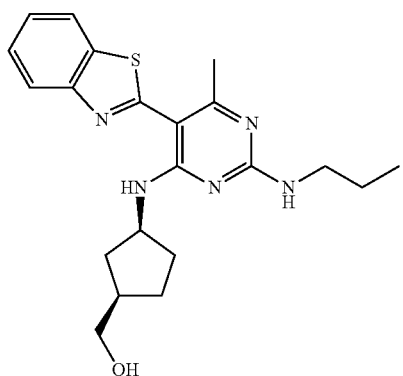
13
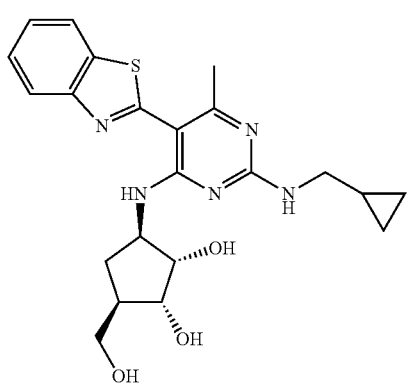
14
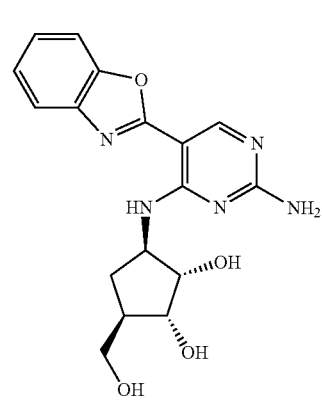
15
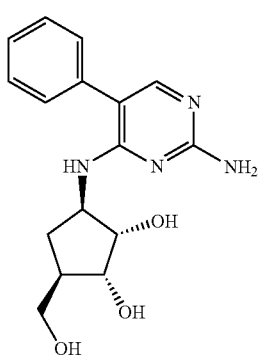
16
324
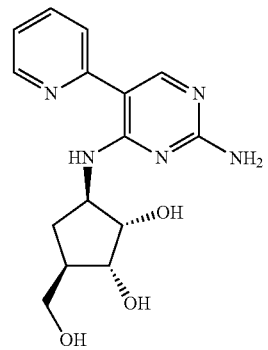
17
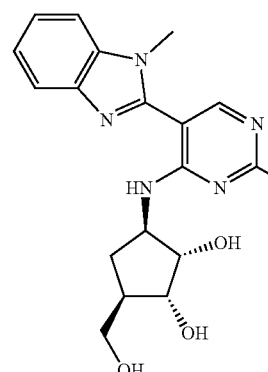
18
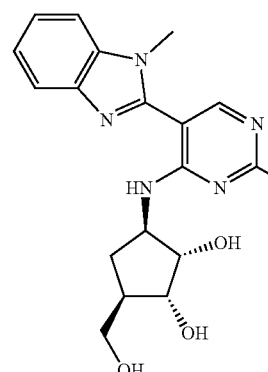
19
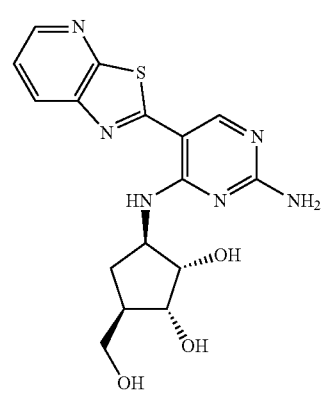
20

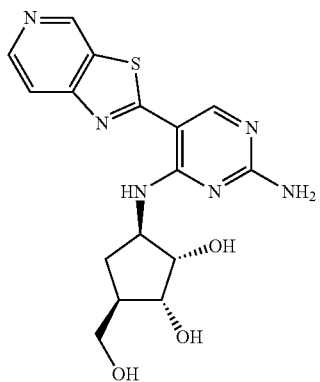
21
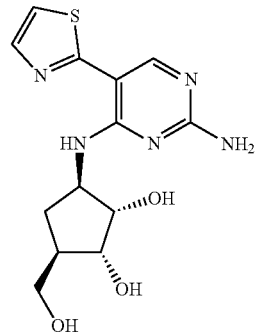
25
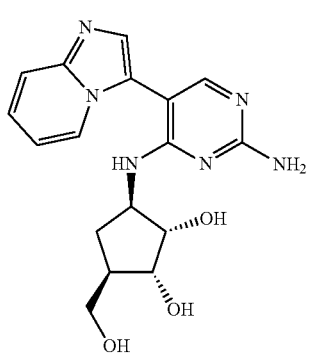
22
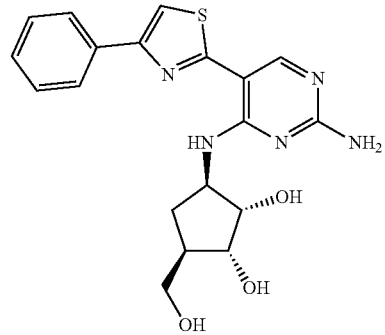
26
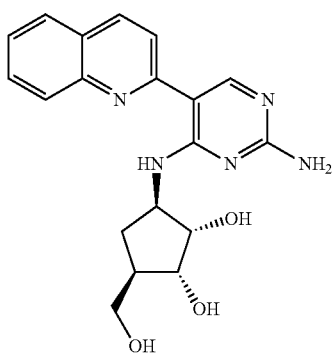
23
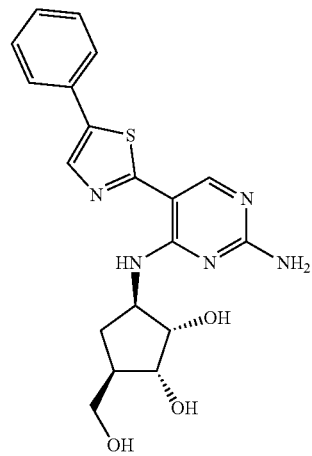
27
24
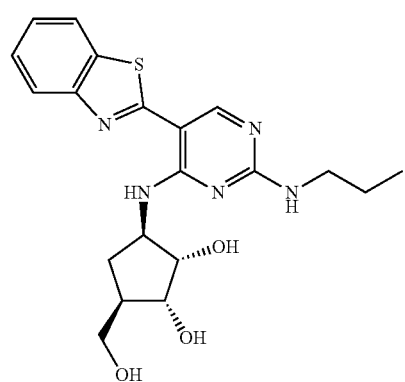
28

| 29 | 33 |
|---|---|
| 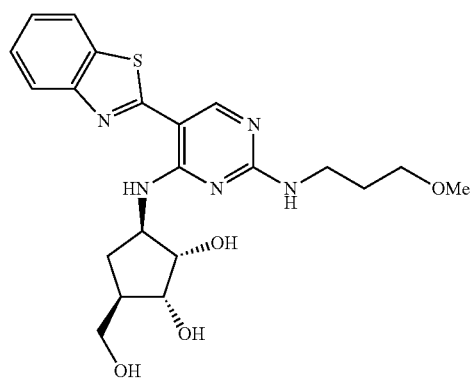 | 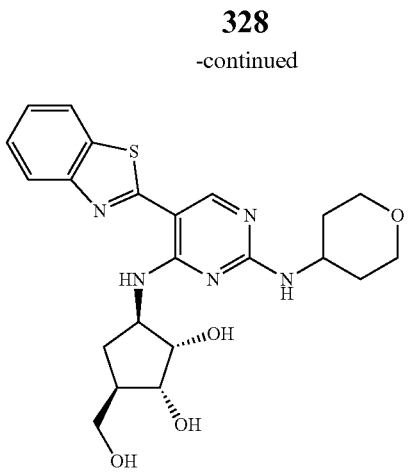 |
| 30 | 34 |
| 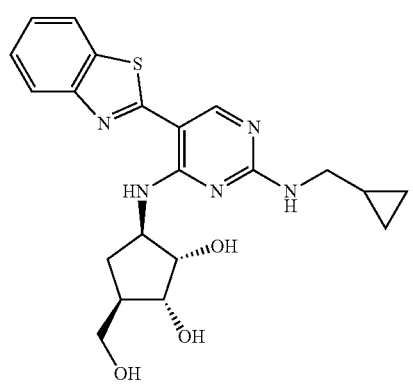 | 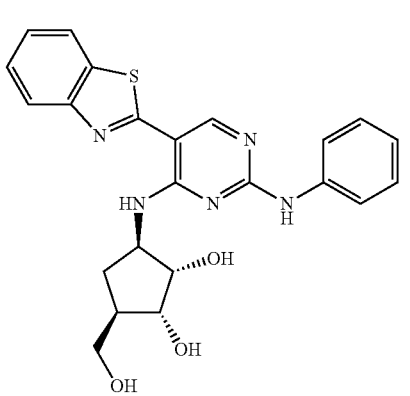 |
| 31 | 35 |
| 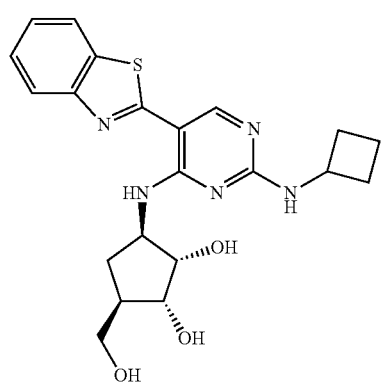 | 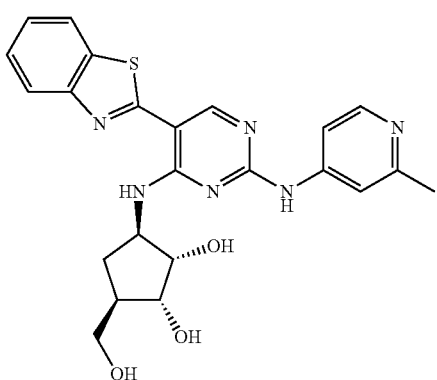 |
| 32 | 36 |
| 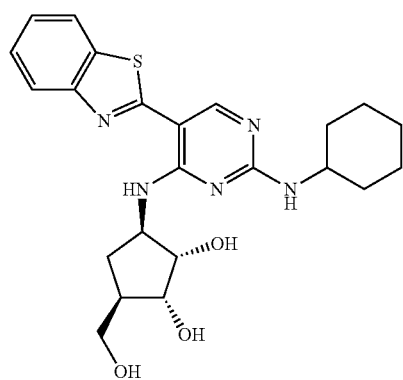 | 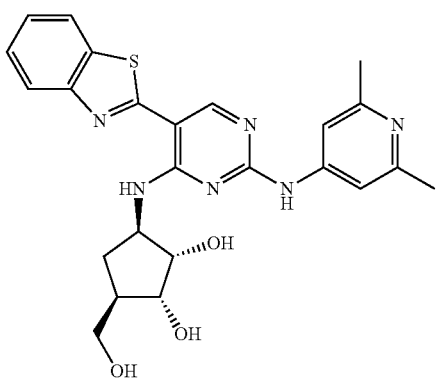 |

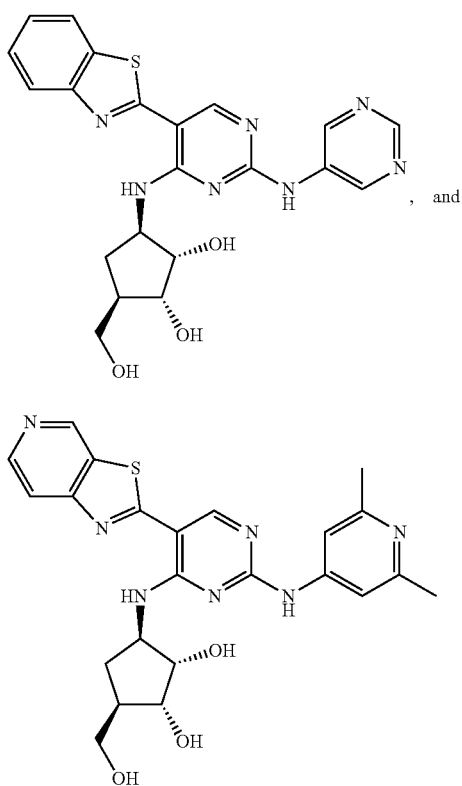
wherein
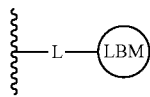
is attached to a modifiable carbon, oxygen, nitrogen or sulfur atom.
In some embodiments, an IRAK ligand is selected from moiety recited in Tumey, L. N., et al., *Identification and optimization of indolo[2,3-c]quinoline inhibitors of IRAK4*, Bioorg. Med. Chem. Lett., 2014, 24 (9): 2066-72, such as, for example:
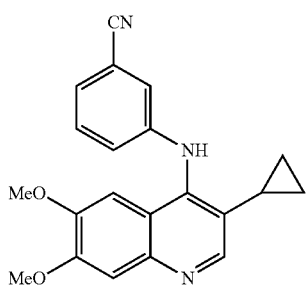
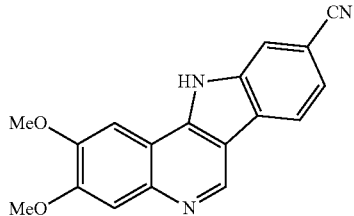

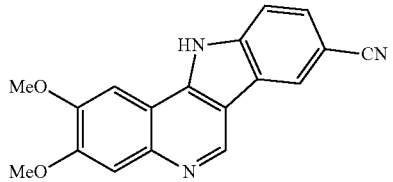
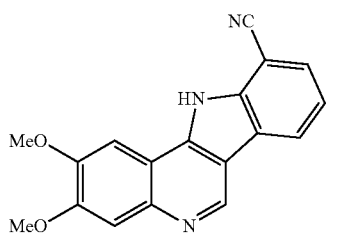
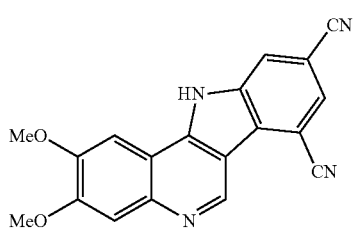
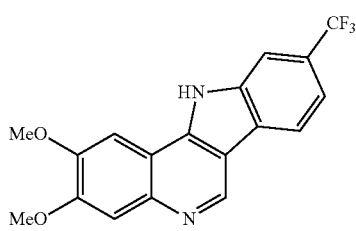
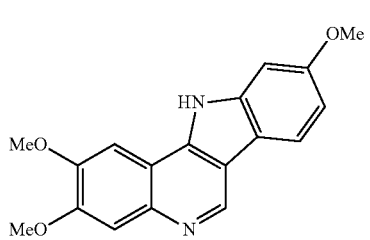

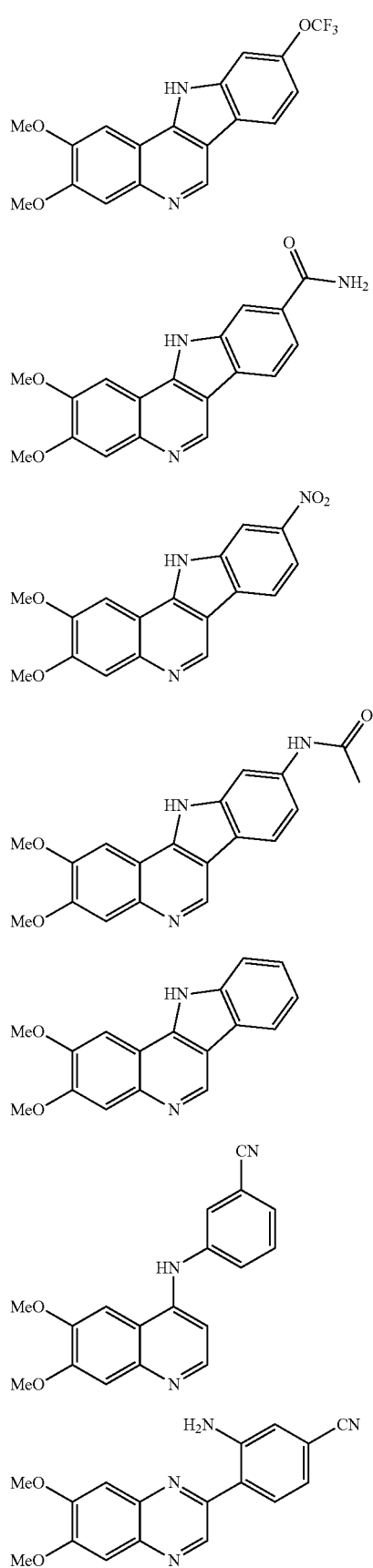
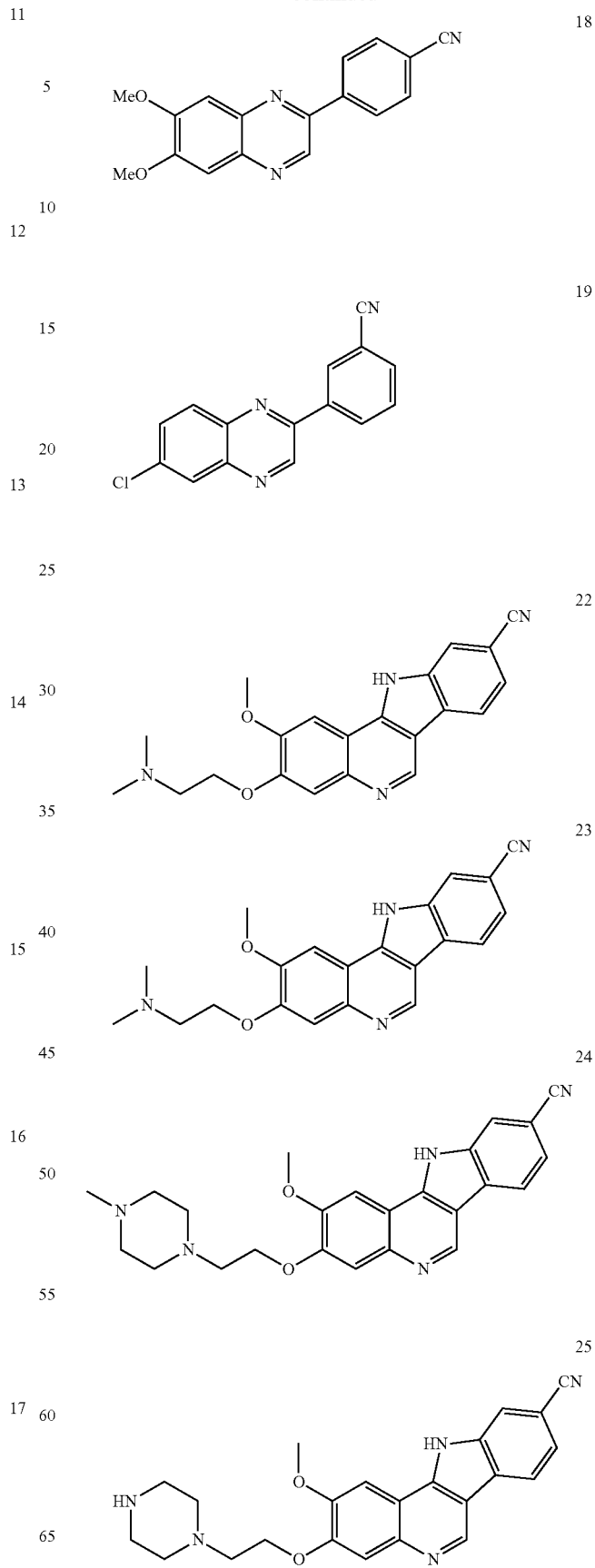

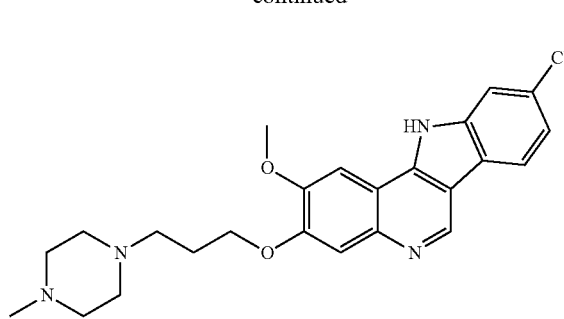
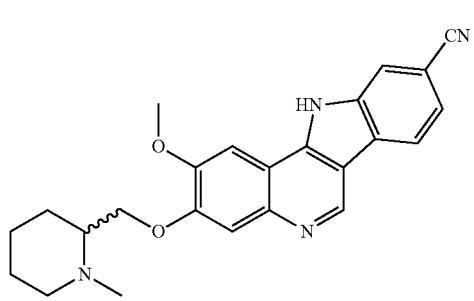
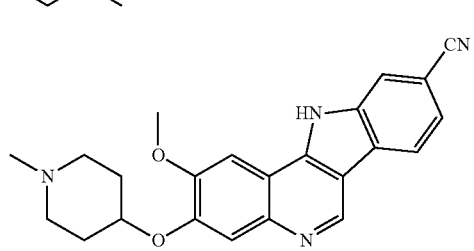
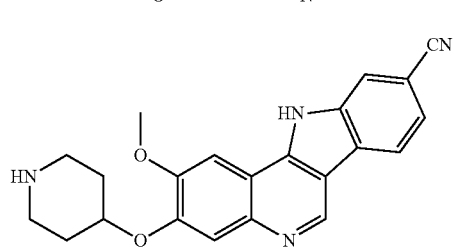
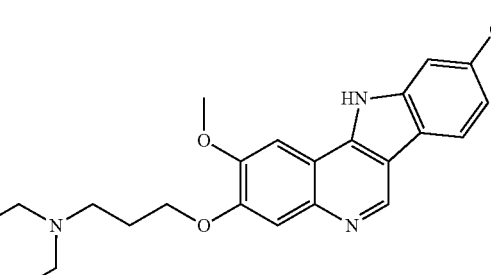
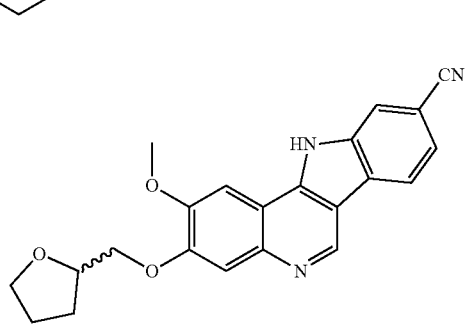
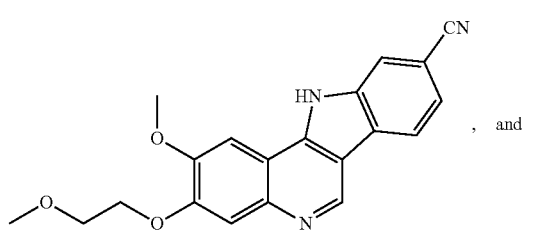
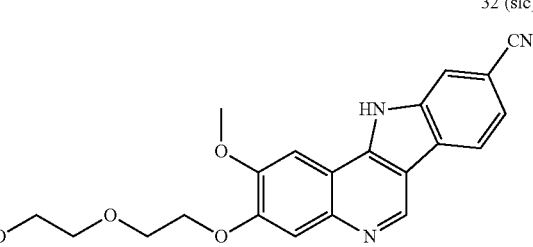
wherein
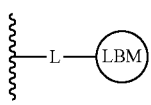
is attached to a modifiable carbon, oxygen, nitrogen or sulfur atom.
In some embodiments, IRAK is
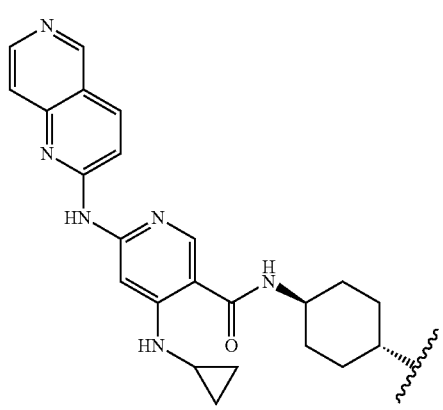

In some embodiments, IRAK is
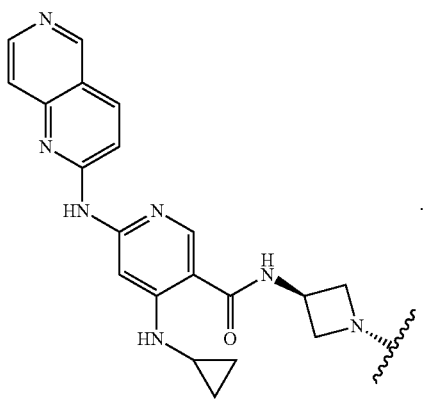
In some embodiments, IRAK is
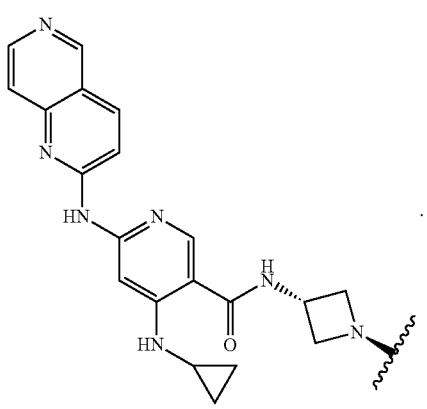
In some embodiments, IRAK is
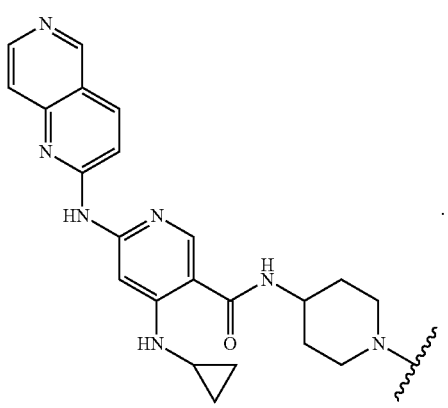 [SMILES: *N1CCC(NC(=O)c2cnc(Nc3ccc4cnccc4n3)cc2NC2CC2)CC1]
In some embodiments, IRAK is
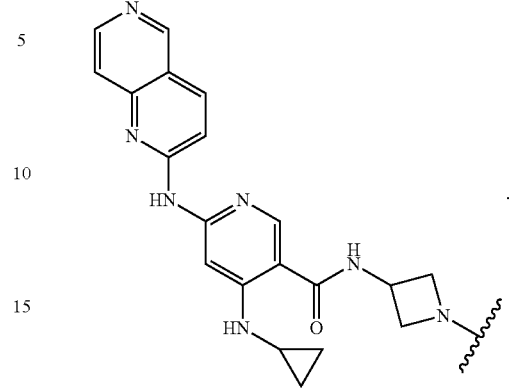
In some embodiments, IRAK is
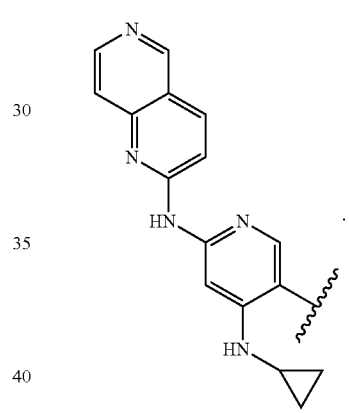
In some embodiments, IRAK is
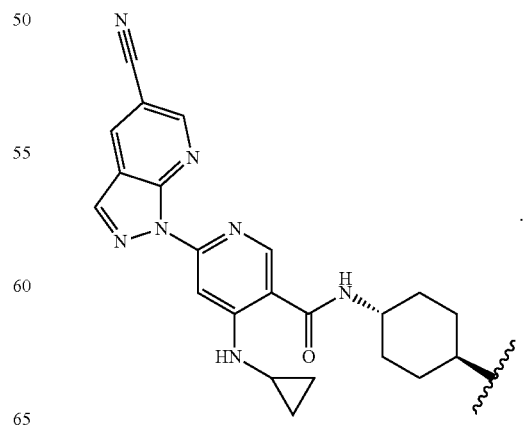

In some embodiments, IRAK is
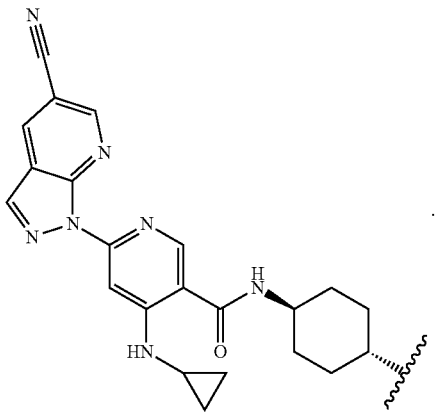 [SMILES: *[C@H]1CC[C@H](NC(=O)c2cnc(-n3ncc4cc(C#N)cnc43)cc2NC2CC2)CC1]
In some embodiments, IRAK is
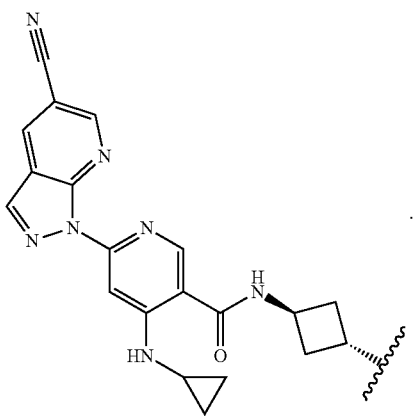 [SMILES: *[C@H]1C[C@H](NC(=O)c2cnc(-n3ncc4cc(C#N)cnc43)cc2NC2CC2)C1]
In some embodiments, IRAK is
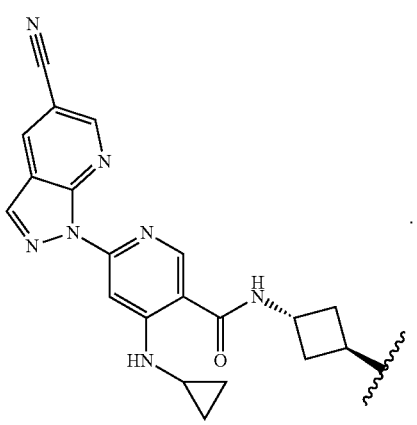 [SMILES: *[C@H]1C[C@H](NC(=O)c2cnc(-n3ncc4cc(C#N)cnc43)cc2NC2CC2)C1]
In some embodiments, IRAK is
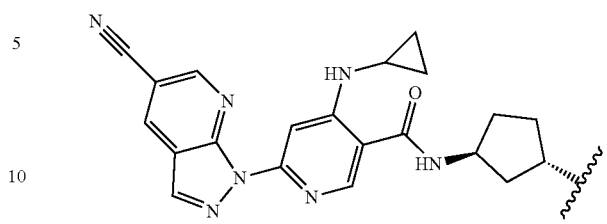
In some embodiments, IRAK is
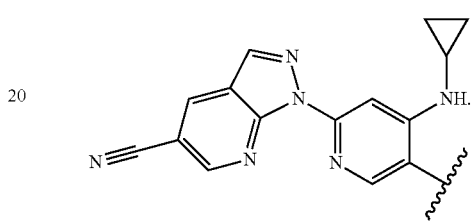
In some embodiments, IRAK is
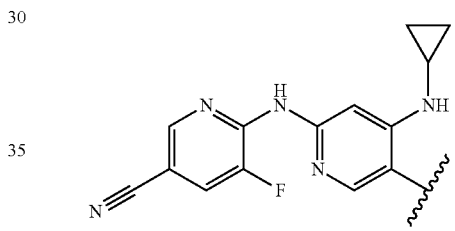
In some embodiments, IRAK is
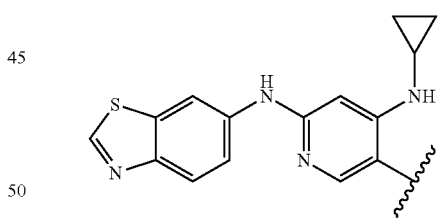
In some embodiments, IRAK is
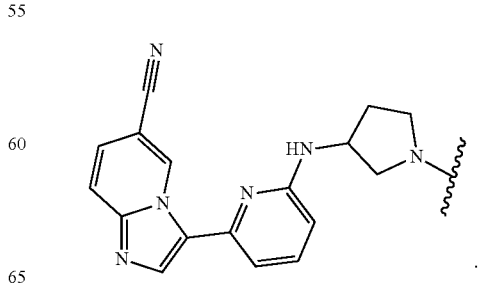

In some embodiments, IRAK is
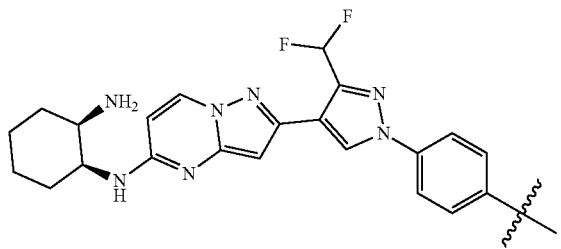
In some embodiments, IRAK is
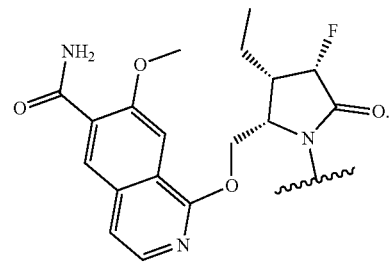 [SMILES: *N1C(=O)[C@@H](F)[C@@H](CC)[C@H]1COc1nccc2cc(C(N)=O)c(OC)cc12]
In some embodiments, IRAK is
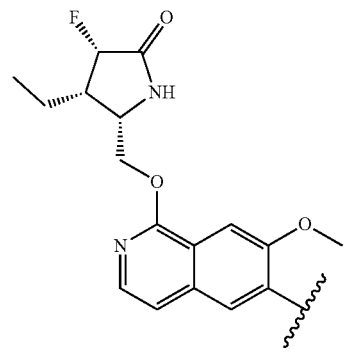
In some embodiments, IRAK is
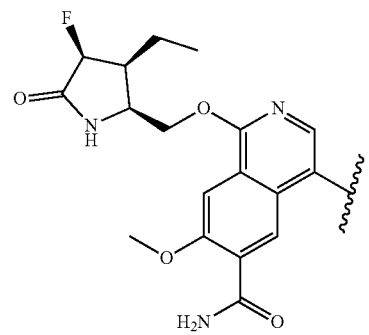
In some embodiments, IRAK is
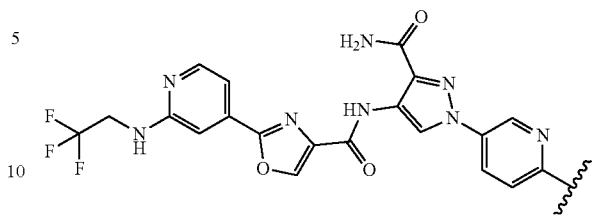
In some embodiments, IRAK is
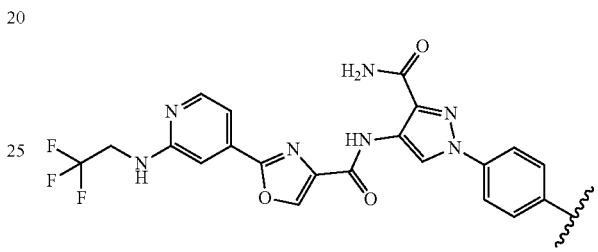
In some embodiments, IRAK is
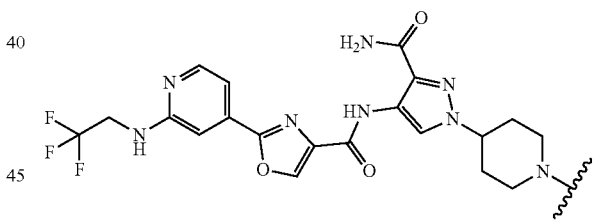
In some embodiments, IRAK is
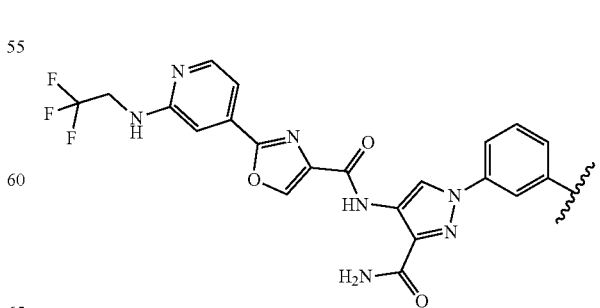

In some embodiments, IRAK is
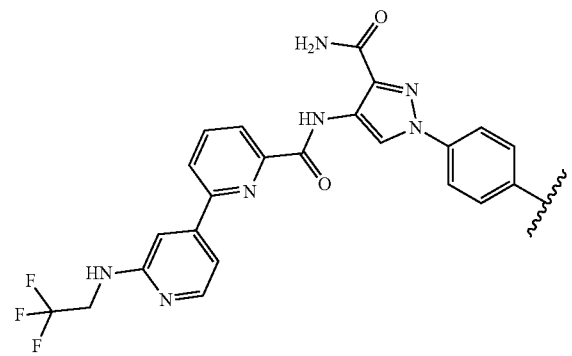
In some embodiments, IRAK is
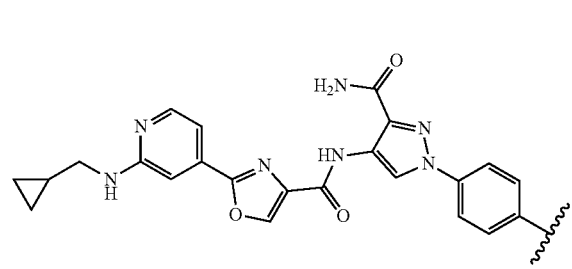
In some embodiments, IRAK is
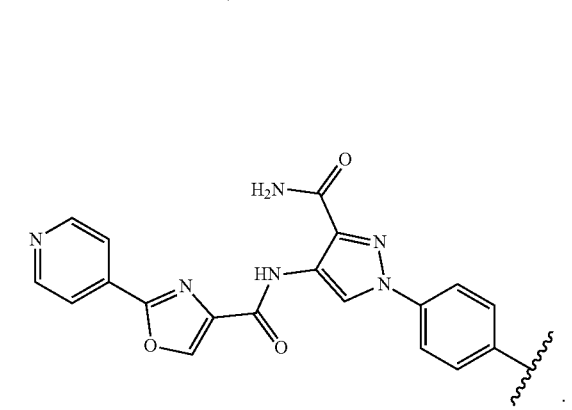
In some embodiments, IRAK is
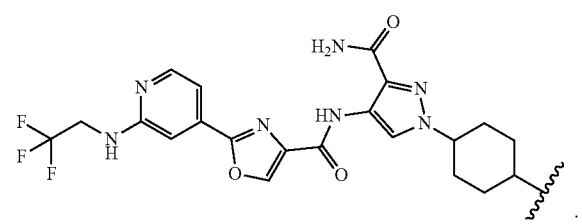 [SMILES: *c1ccc(-n2cc(NC(=O)c3coc(-c4ccnc(NCC(F)(F)F)c4)n3)c(C(N)=O)n2)cn1]
In some embodiments, IRAK is
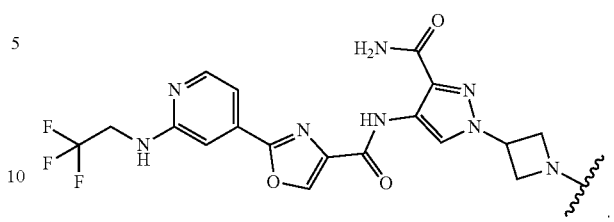
In some embodiments, IRAK is
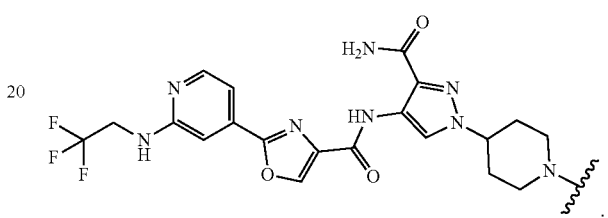
In some embodiments, IRAK is
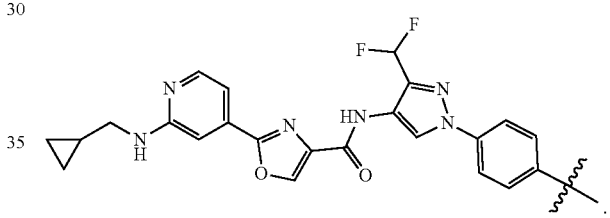
In some embodiments, IRAK is
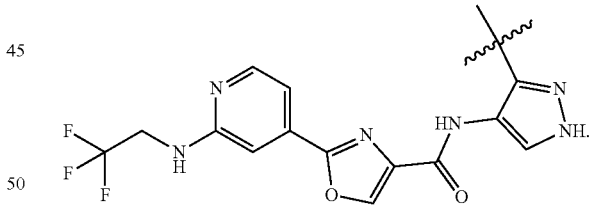
In some embodiments, IRAK is
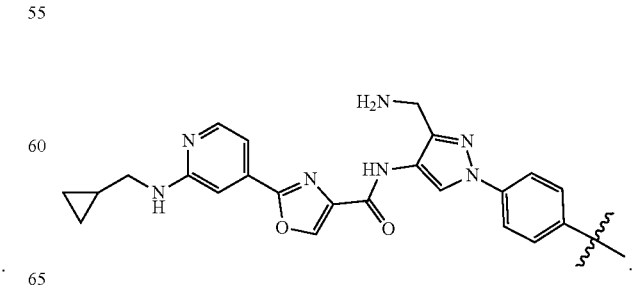

In some embodiments, IRAK is
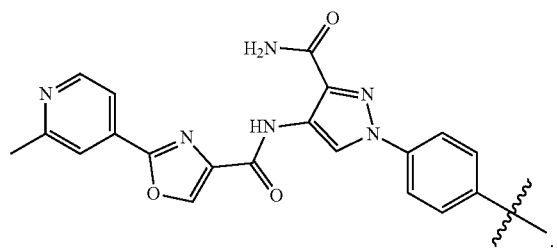 [SMILES: *c1ccc(-n2cc(NC(=O)c3coc(-c4ccnc(C)c4)n3)c(C(N)=O)n2)cc1]
In some embodiments, IRAK is
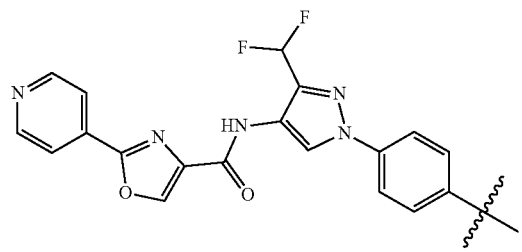 [SMILES: *c1ccc(-n2cc(NC(=O)c3coc(-c4ccncc4)n3)c(C(F)F)n2)cc1]
In some embodiments, IRAK is
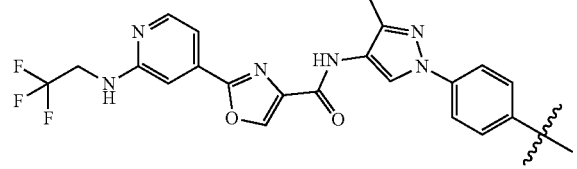
In some embodiments, IRAK is
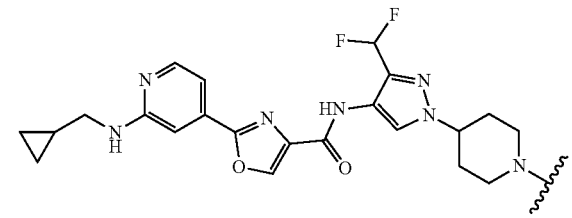
In some embodiments, IRAK is
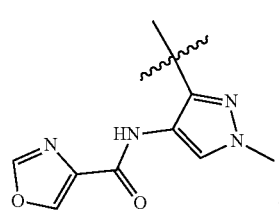
In some embodiments, IRAK is
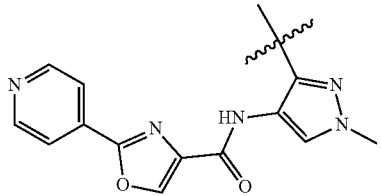
In some embodiments, IRAK is
In some embodiments, IRAK is
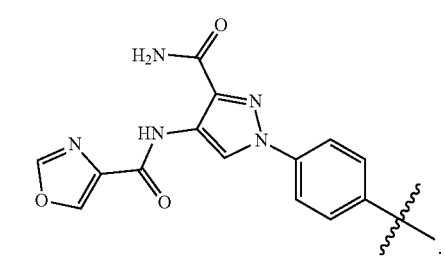 [SMILES: *c1ccc(-n2cc(NC(=O)c3cocn3)c(C(N)=O)n2)cc1]
In some embodiments, IRAK is
In some embodiments, IRAK is
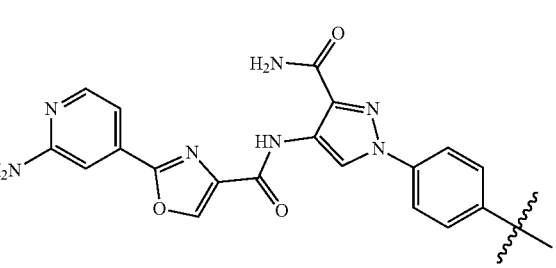

In some embodiments, IRAK is
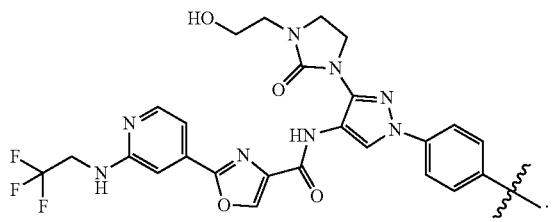 [SMILES: *c1ccc(-n2cc(NC(=O)c3coc(-c4ccnc(NCC(F)(F)F)c4)n3)c(N3CCN(CCO)C3=O)n2)cc1]
In some embodiments, IRAK is
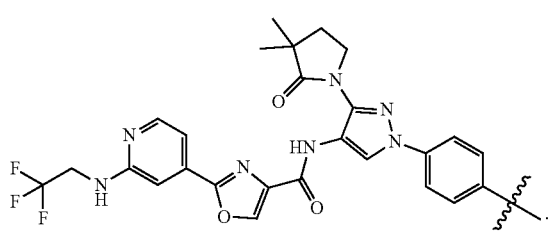 [SMILES: *c1ccc(-n2cc(NC(=O)c3coc(-c4ccnc(NCC(F)(F)F)c4)n3)c(N3CCC(C)(C)C3=O)n2)cc1]
In some embodiments, IRAK is
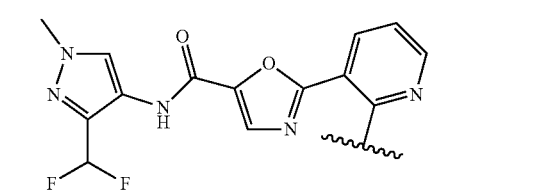 [SMILES: *c1ncccc1-c1ncc(C(=O)Nc2cn(C)nc2C(F)F)o1]
In some embodiments, IRAK is
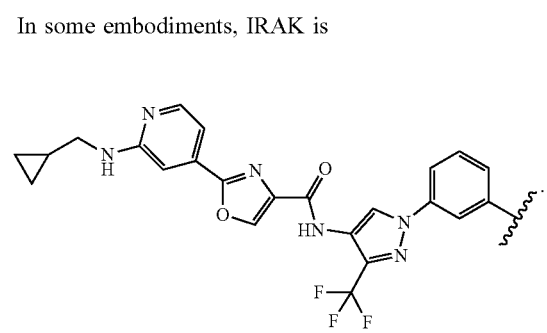
In some embodiments, IRAK is
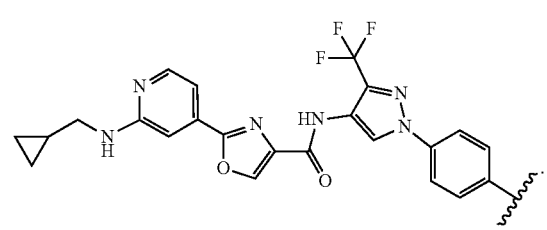 [SMILES: *c1ccc(-n2cc(NC(=O)c3coc(-c4ccnc(NCC5CC5)c4)n3)c(C(F)(F)F)n2)cc1]
In some embodiments, IRAK is
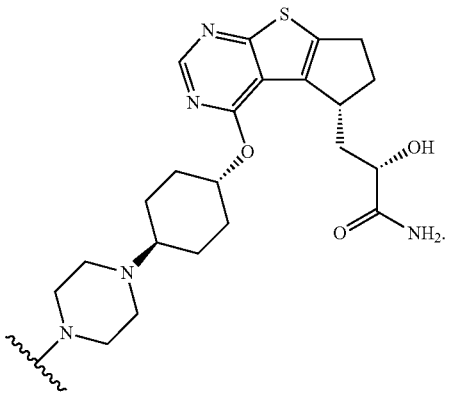 [SMILES: *N1CCN([C@H]2CC[C@H](Oc3ncnc4sc5c(c34)[C@@H](C[C@H](O)C(N)=O)CC5)CC2)CC1]
In some embodiments, IRAK is
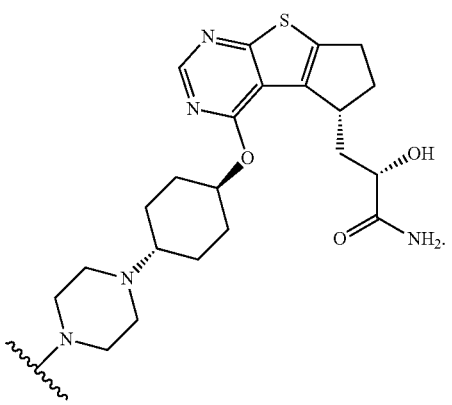 [SMILES: *N1CCN([C@H]2CC[C@H](Oc3ncnc4sc5c(c34)[C@@H](C[C@H](O)C(N)=O)CC5)CC2)CC1]
In some embodiments, IRAK is
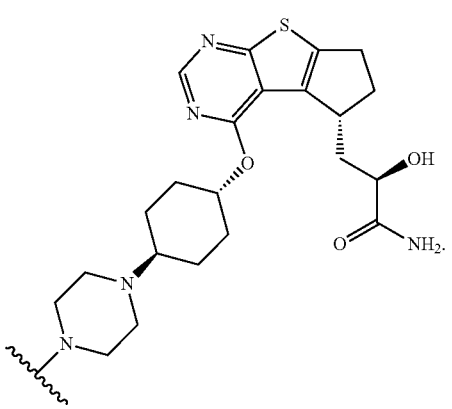 [SMILES: *N1CCN([C@H]2CC[C@H](Oc3ncnc4sc5c(c34)[C@@H](C[C@@H](O)C(N)=O)CC5)CC2)CC1]

In some embodiments, IRAK is
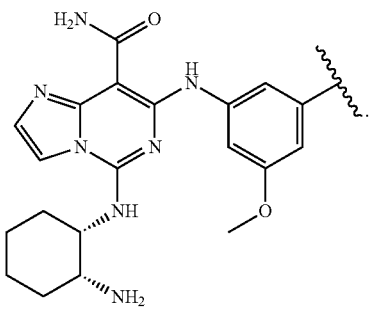 [SMILES: *c1cc(Nc2nc(N[C@H]3CCCC[C@H]3N)n3ccnc3c2C(N)=O)cc(OC)c1]
In some embodiments, IRAK is
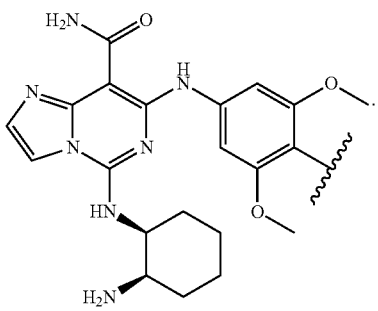 [SMILES: *c1c(OC)cc(Nc2nc(N[C@H]3CCCC[C@H]3N)n3ccnc3c2C(N)=O)cc1OC]
In some embodiments, IRAK is
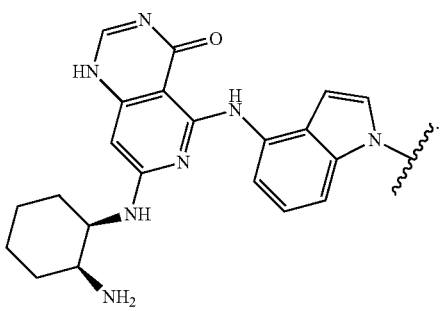 [SMILES: *n1ccc2c(Nc3nc(N[C@@H]4CCCC[C@@H]4N)cc4[nH]cnc(=O)c34)cccc21]
In some embodiments, IRAK is
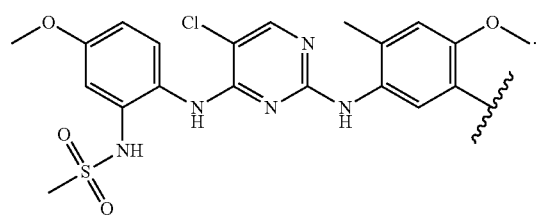
In some embodiments, IRAK is
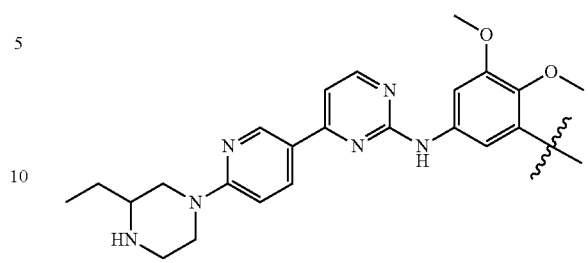
In some embodiments, IRAK is
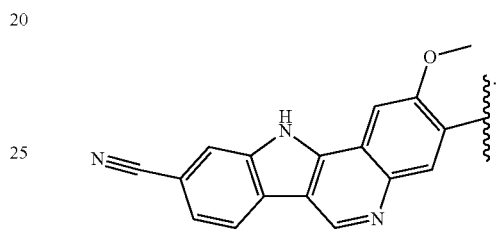
In some embodiments, IRAK is
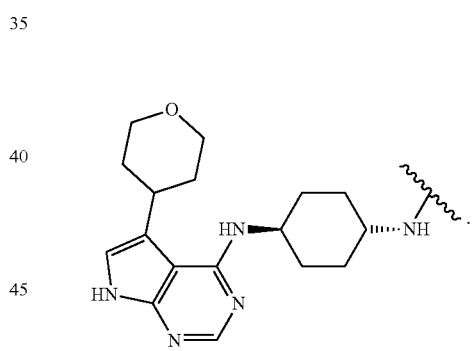
In some embodiments, IRAK is
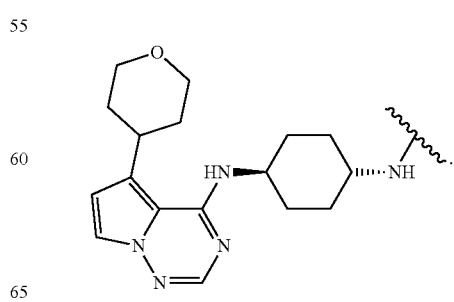

In some embodiments, IRAK is
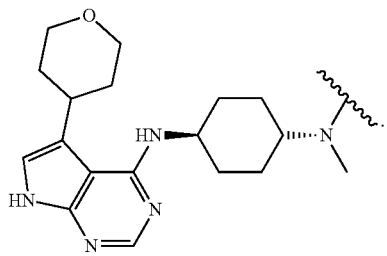
In some embodiments, IRAK is
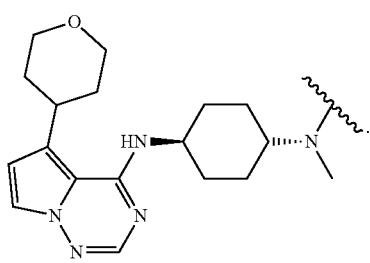
In some embodiments, IRAK is
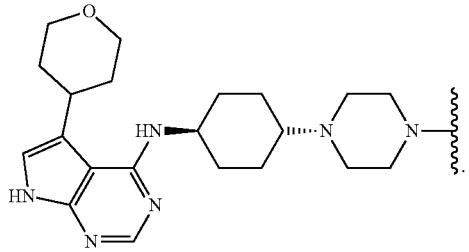
In some embodiments, IRAK is
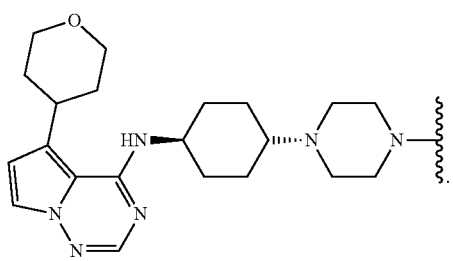
In some embodiments, IRAK is
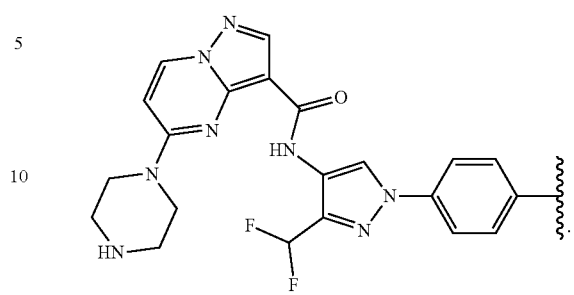
In some embodiments, IRAK is
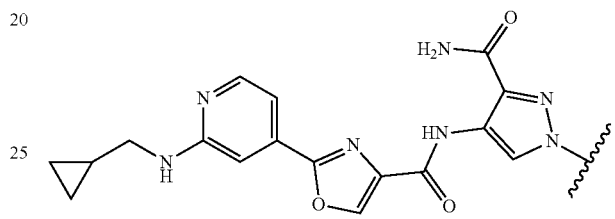
In some embodiments, IRAK is
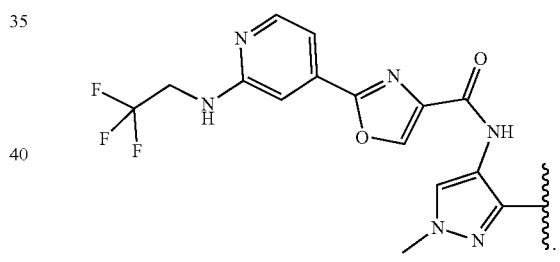
In some embodiments, IRAK is
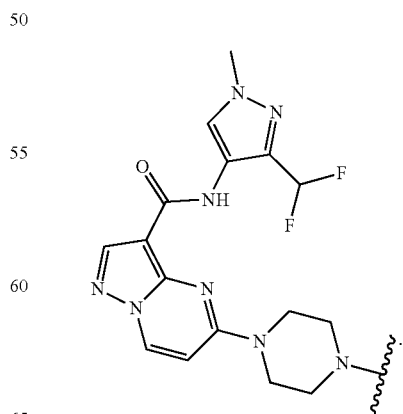

In some embodiments, IRAK is
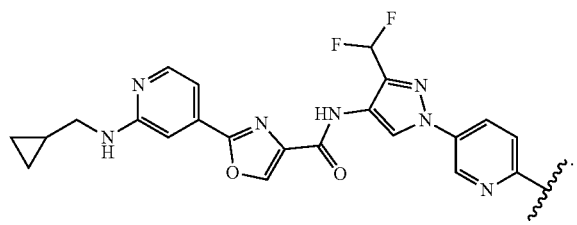 [SMILES: *c1ccc(-n2cc(NC(=O)c3coc(-c4ccnc(NCC5CC5)c4)n3)c(C(F)F)n2)cn1]
In some embodiments, IRAK is
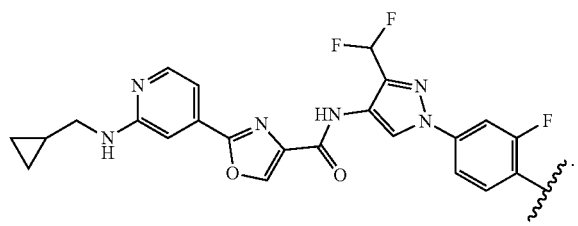 [SMILES: *c1ccc(-n2cc(NC(=O)c3coc(-c4ccnc(NCC5CC5)c4)n3)c(C(F)F)n2)cc1F]
In some embodiments, IRAK is
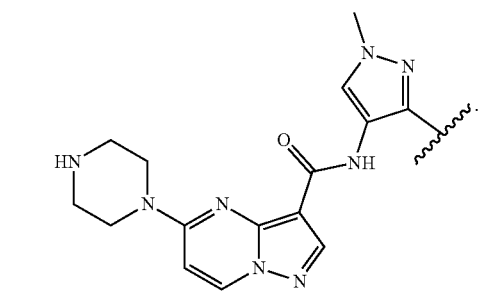 [SMILES: *c1nn(C)cc1NC(=O)c1cnn2ccc(N3CCNCC3)nc12]
In some embodiments, IRAK is
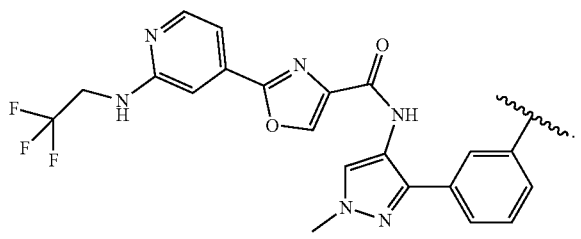 [SMILES: *c1cccc(-c2nn(C)cc2NC(=O)c2coc(-c3ccnc(NCC(F)(F)F)c3)n2)c1]
In some embodiments, IRAK is
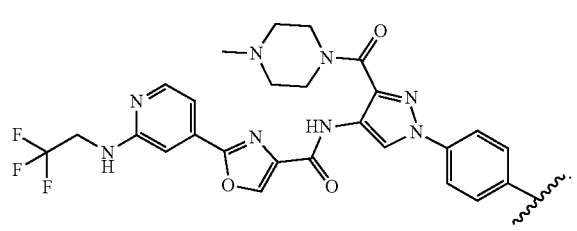 [SMILES: *c1ccc(-n2cc(NC(=O)c3coc(-c4ccnc(NCC(F)(F)F)c4)n3)c(C(=O)N3CCN(C)CC3)n2)cc1]
In some embodiments, IRAK is
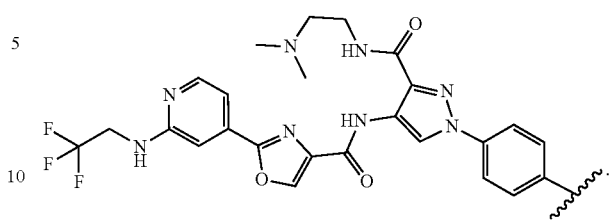
In some embodiments, IRAK is
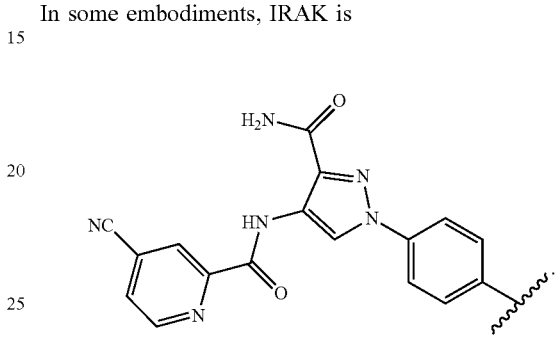
In some embodiments, IRAK is
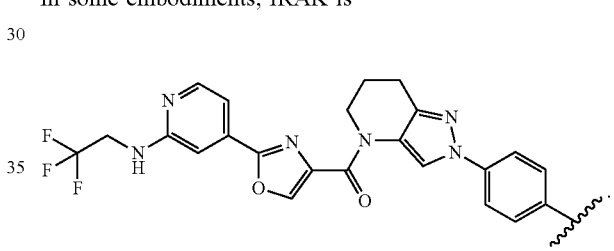
In some embodiments, IRAK is
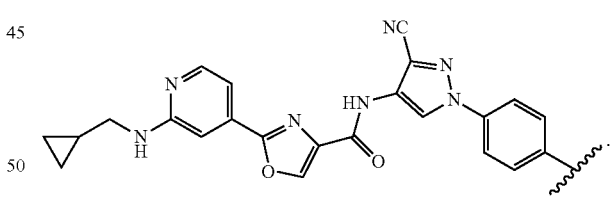
In some embodiments, IRAK is
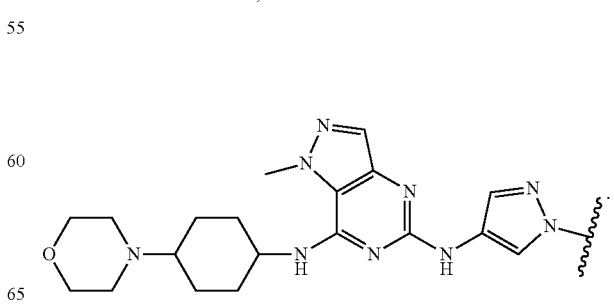

In some embodiments, IRAK is

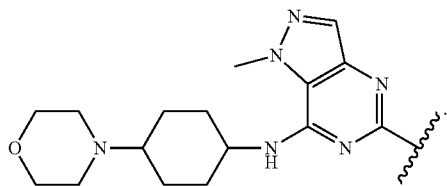 [SMILES: *c1nc(NC2CCC(N3CCOCC3)CC2)c2c(cnn2C)n1]

In some embodiments, IRAK is

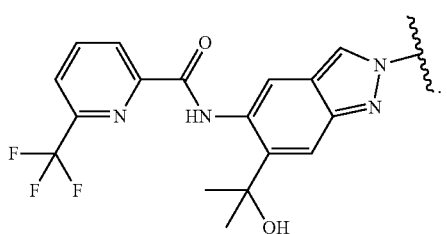 [SMILES: *n1cc2cc(NC(=O)c3cccc(C(F)(F)F)n3)c(C(C)(C)O)cc2n1]

In some embodiments, IRAK is selected from those depicted in Table 1, below.

As defined above and described herein, L is a bivalent moiety that connects IRAK to LBM.

In some embodiments, L is a bivalent moiety that connects IRAK to LBM.

In some embodiments, L is a covalent bond or a bivalent, saturated or unsaturated, straight or branched $C_{1-50}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

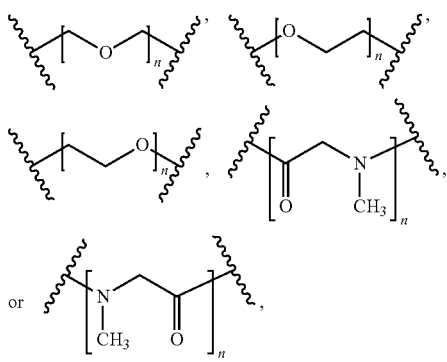

wherein: each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur.

In some embodiments, each -Cy- is independently an optionally substituted bivalent phenylenyl. In some embodiments, each -Cy- is independently an optionally substituted 8-10 membered bicyclic arylenyl. In some embodiments, each -Cy- is independently an optionally substituted 4-7 membered saturated or partially unsaturated carbocyclylenyl. In some embodiments, each -Cy- is independently an optionally substituted 4-7 membered saturated or partially unsaturated spiro carbocyclylenyl. In some embodiments, each -Cy- is independently an optionally substituted 8-10 membered bicyclic saturated or partially unsaturated carbocyclylenyl. In some embodiments, each -Cy- is independently an optionally substituted 4-7 membered saturated or partially unsaturated heterocyclylenyl having 1-2 heteroatoms independently selected from nitrogen, oxygen, and sulfur. In some embodiments, each -Cy- is independently an optionally substituted 4-7 membered saturated or partially unsaturated spiro heterocyclylenyl having 1-2 heteroatoms independently selected from nitrogen, oxygen, and sulfur. In some embodiments, each -Cy- is independently an optionally substituted 8-10 membered bicyclic saturated or partially unsaturated heterocyclylenyl having 1-2 heteroatoms independently selected from nitrogen, oxygen, and sulfur. In some embodiments, each -Cy- is independently an optionally substituted 5-6 membered heteroarylenyl having 1-4 heteroatoms independently selected from nitrogen, oxygen, and sulfur. In some embodiments, each -Cy- is independently an optionally substituted 8-10 membered bicyclic heteroarylenyl having 1-5 heteroatoms independently selected from nitrogen, oxygen, or sulfur.

In some embodiments, -Cy- is

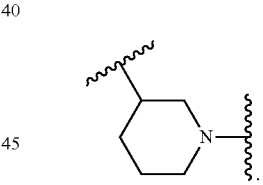

In some embodiments, -Cy- is

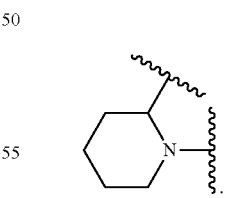

In some embodiments, -Cy- is

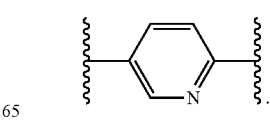

In some embodiments, -Cy- is
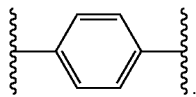
In some embodiments, -Cy- is
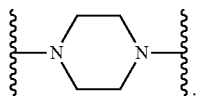
In some embodiments, -Cy- is
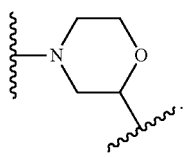 [SMILES: *C1CN(*)CCO1]
In some embodiments, -Cy- is
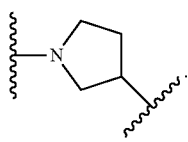 [SMILES: *C1CCN(*)C1]
In some embodiments, -Cy- is
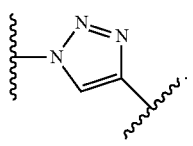 [SMILES: *c1cn(*)nn1]
In some embodiments, -Cy- is
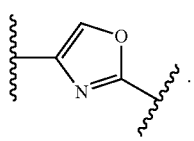 [SMILES: *c1coc(*)n1]
In some embodiments, -Cy- is
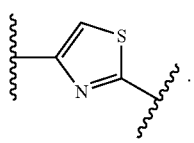 [SMILES: *c1csc(*)n1]
In some embodiments, -Cy- is
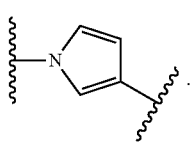 [SMILES: *c1ccn(*)c1]
In some embodiments, -Cy- is
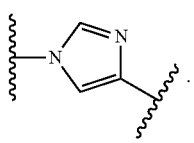 [SMILES: *c1cn(*)cn1]
In some embodiments, -Cy- is
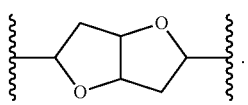 [SMILES: *C1CC2OC(*)CC2O1]
In some embodiments, -Cy- is
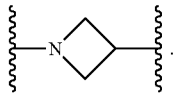 [SMILES: *C1CN(*)C1]
In some embodiments, -Cy- is
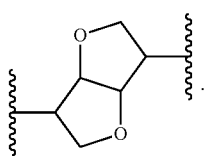 [SMILES: *C1COC2C(*)COC12]
In some embodiments, -Cy- is
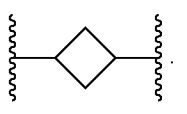 [SMILES: *C1CC(*)C1]
In some embodiments, -Cy- is
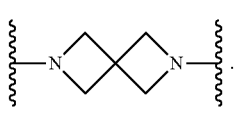 [SMILES: *N1CC2(C1)CN(*)C2]

In some embodiments, -Cy- is
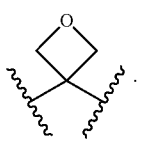 [SMILES: *C1(*)COC1]
In some embodiments, -Cy- is
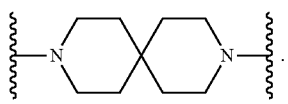
In some embodiments, -Cy- is
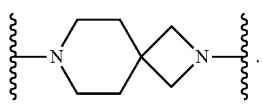
In some embodiments, -Cy- is
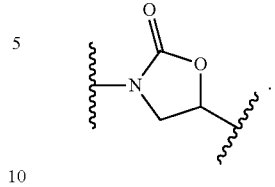
In some embodiments, -Cy- is
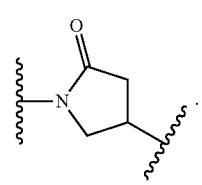 [SMILES: *C1CC(=O)N(*)C1]
In some embodiments, -Cy- is
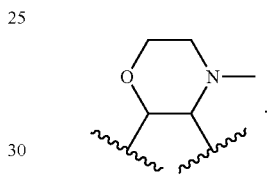
In some embodiments, L is
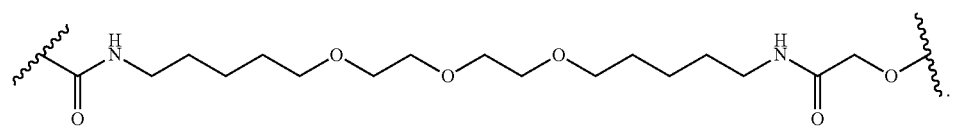 [SMILES: *OCC(=O)NCCCCCOCCOCCOCCCCCNC(*)=O]
In some embodiments, L is
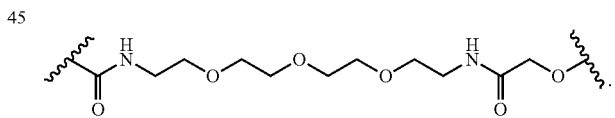
In some embodiments, L is
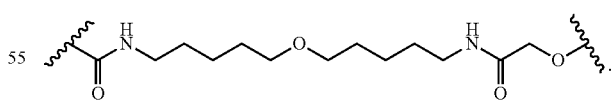
In some embodiments, L is
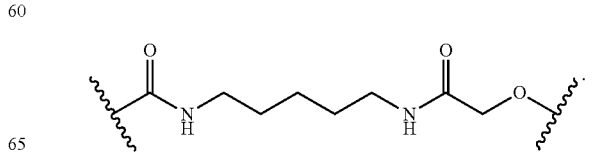

In some embodiments, L is
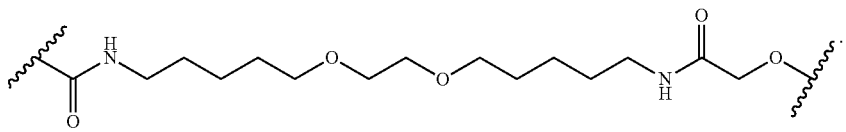
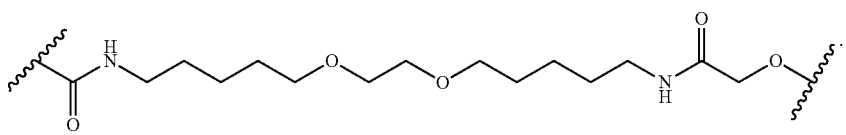
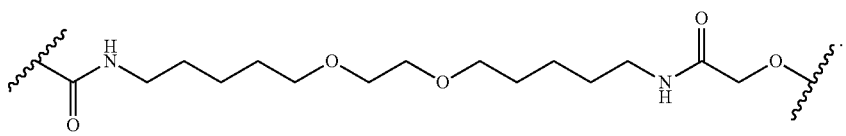
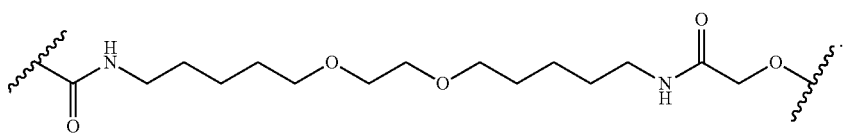
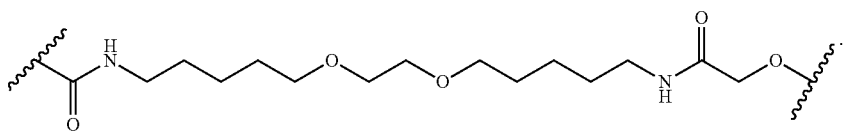 [SMILES: *OCC(=O)NCCCCCOCCOCCCCCNC(*)=O]
In some embodiments, L is
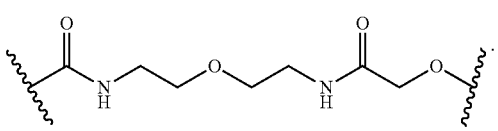 [SMILES: *OCC(=O)NCCOCCNC(*)=O]
In some embodiments, L is
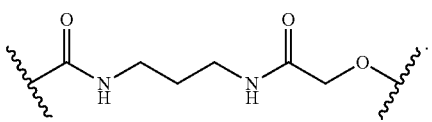 [SMILES: *OCC(=O)NCCCNC(*)=O]
In some embodiments, L is
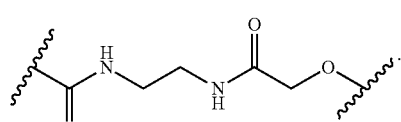
In some embodiments, L is
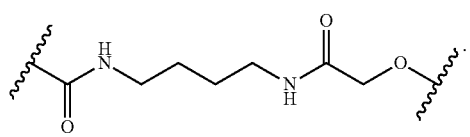 [SMILES: *OCC(=O)NCCCCNC(*)=O]
In some embodiments, L is
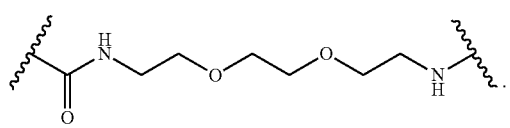 [SMILES: *NCCOCCOCCNC(*)=O]

In some embodiments, L is
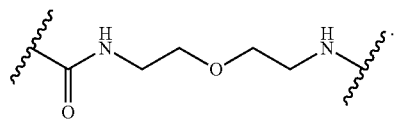 [SMILES: *NCCOCCNC(*)=O]
In some embodiments, L is
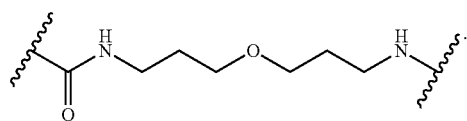 [SMILES: *NCCCOCCCNC(*)=O]
In some embodiments, L is
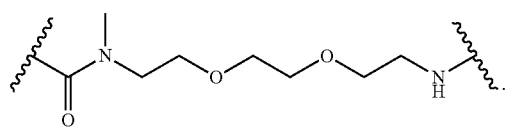 [SMILES: *NCCOCCOCCN(C)C(*)=O]
In some embodiments, L is
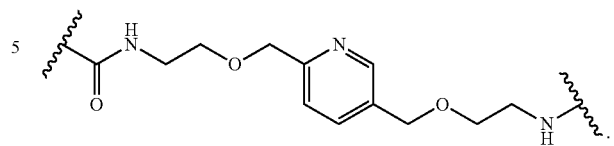
In some embodiments, L is
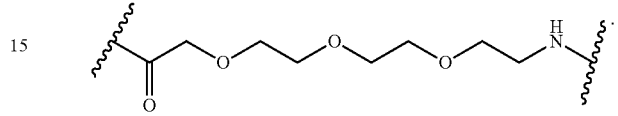
In some embodiments, L is
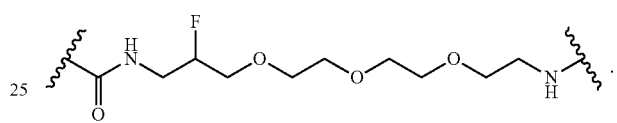
In some embodiments, L is
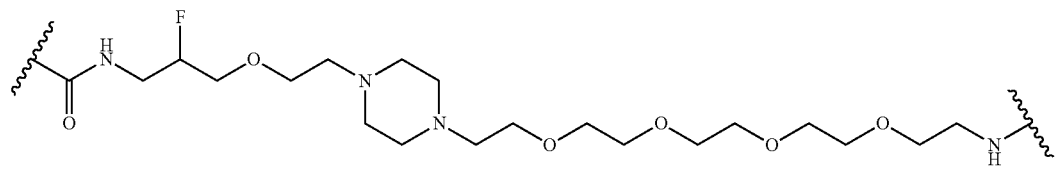
In some embodiments, L is
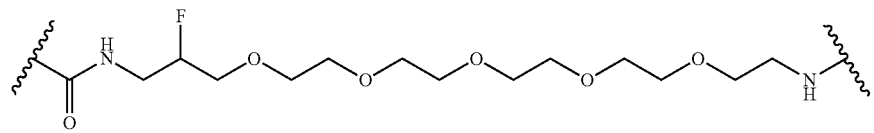
In some embodiments, L is
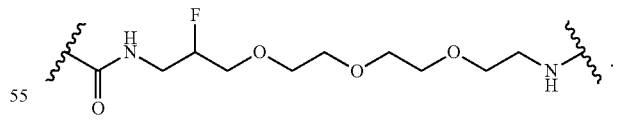
In some embodiments, L is
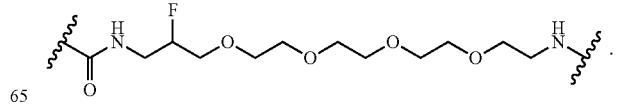

In some embodiments, L is
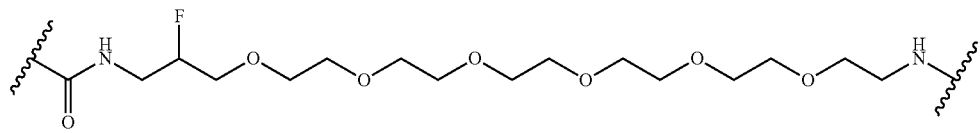
In some embodiments, L is
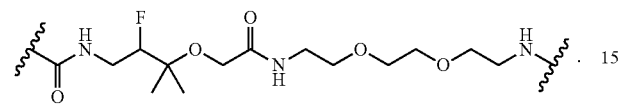
In some embodiments, L is
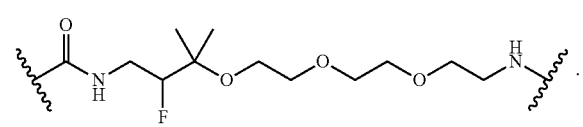 [SMILES: *NCCOCCOCCOC(C)(C)C(F)CNC(*)=O]
In some embodiments, L is
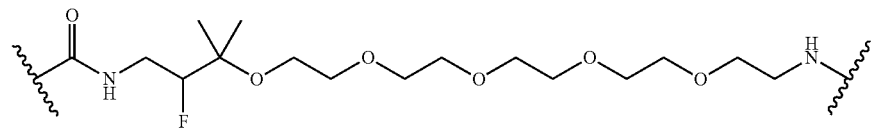
In some embodiments, L is
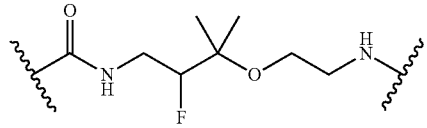
In some embodiments, L is
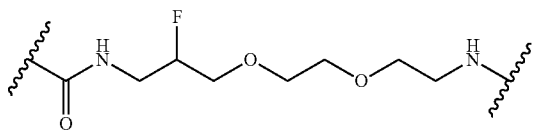
In some embodiments, L is
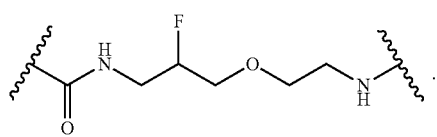 [SMILES: *NCCOCC(F)CNC(*)=O]
In some embodiments, L is
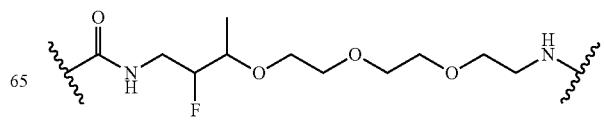

In some embodiments, L is
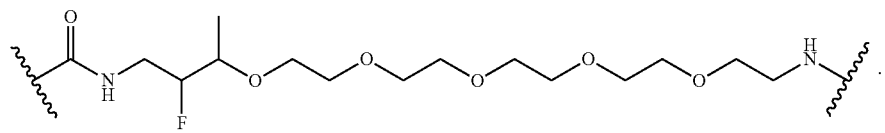 [SMILES: *NCCOCCOCCOCCOCCOC(C)C(F)CNC(*)=O]
In some embodiments, L is
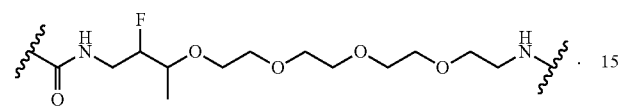
In some embodiments, L is
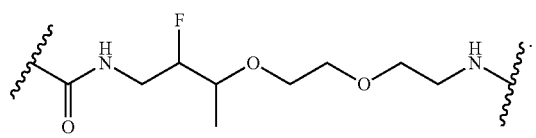 [SMILES: *NCCOCCOC(C)C(F)CNC(*)=O]
In some embodiments, L is
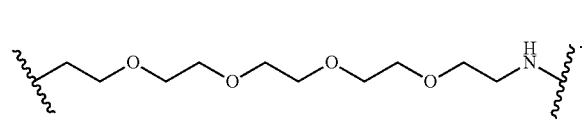 [SMILES: *CCOCCOCCOCCOCCN*]
In some embodiments, L is
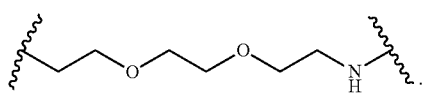 [SMILES: *CCOCCOCCN*]
In some embodiments, L is
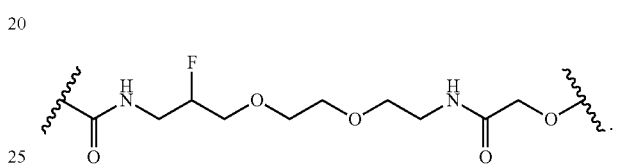
In some embodiments, L is
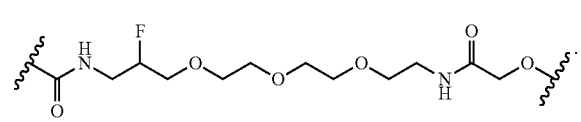 [SMILES: *OCC(=O)NCCOCCOCCOCC(F)CNC(*)=O]
In some embodiments, L is
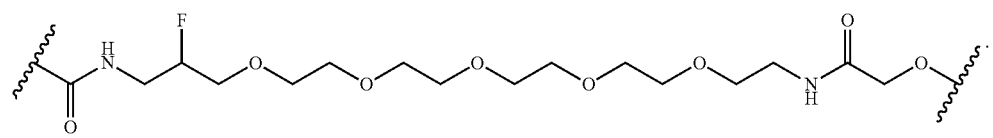 [SMILES: *OCC(=O)NCCOCCOCCOCCOCCOCC(F)CNC(*)=O]
In some embodiments, L is
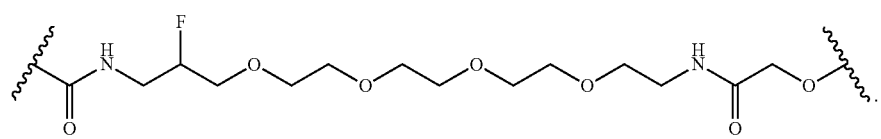 [SMILES: *OCC(=O)NCCOCCOCCOCCOCC(F)CNC(*)=O]
In some embodiments, L is
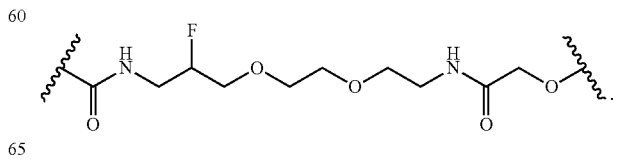

In some embodiments, L is
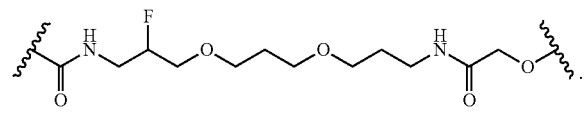 [SMILES: *OCC(=O)NCCCOCCCOCC(F)CNC(*)=O]
In some embodiments, L is
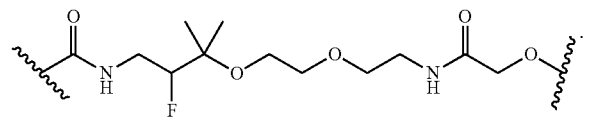 [SMILES: *OCC(=O)NCCOCCOC(C)(C)C(F)CNC(*)=O]
In some embodiments, L is
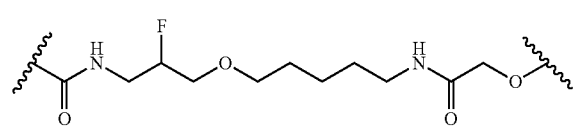
In some embodiments, L is
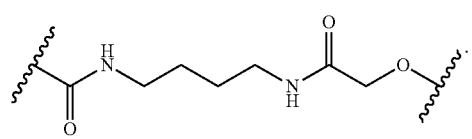 [SMILES: *OCC(=O)NCCCCNC(*)=O]
In some embodiments, L is
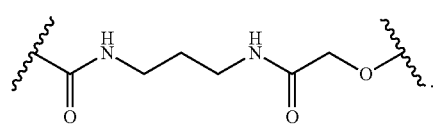 [SMILES: *OCC(=O)NCCCNC(*)=O]
In some embodiments, L is
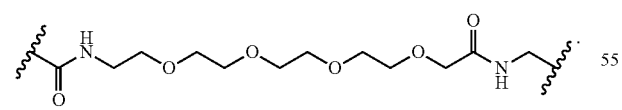
In some embodiments, L is
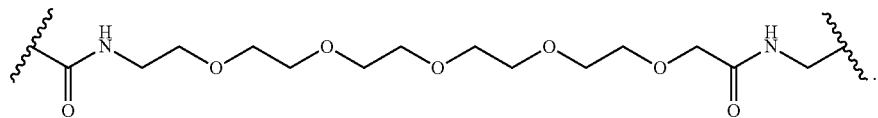 [SMILES: *CNC(=O)COCCOCCOCCOCCOCCNC(*)=O]
In some embodiments, L is
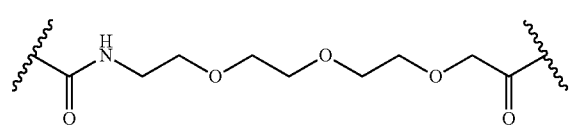
In some embodiments, L is
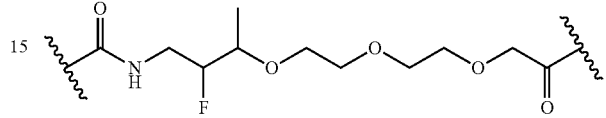
In some embodiments, L is
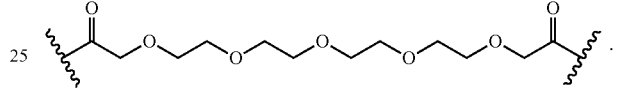
In some embodiments, L is
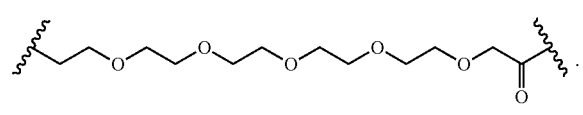 [SMILES: *CCOCCOCCOCCOCCOCC(*)=O]
In some embodiments, L is
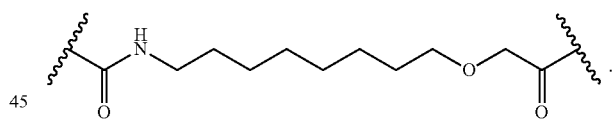
In some embodiments, L is
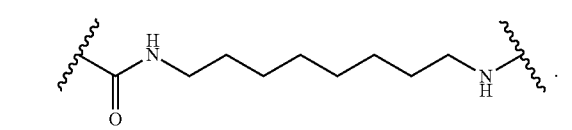 [SMILES: *NCCCCCCCCNC(*)=O]
In some embodiments, L is
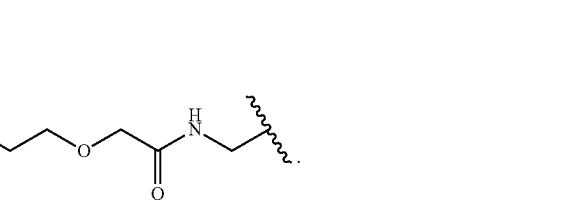

In some embodiments, L is

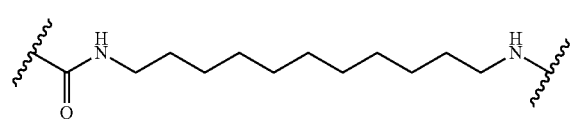

In some embodiments, L is

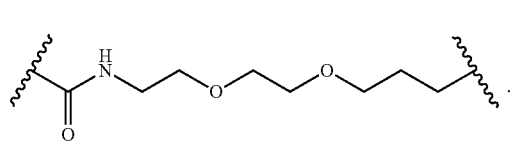 [SMILES: *CCCOCCOCCNC(*)=O]

In some embodiments, L is

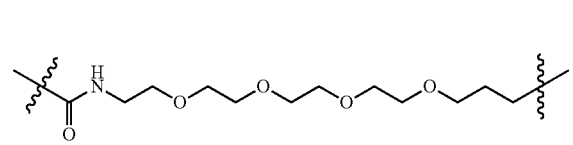

In some embodiments, L is

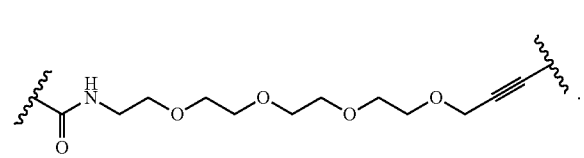 [SMILES: *C#CCOCCOCCOCCOCCNC(*)=O]

In some embodiments, L is

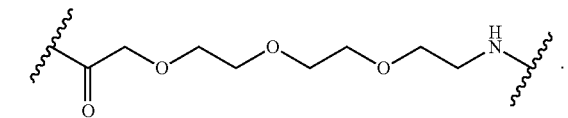 [SMILES: *NCCOCCOCCOCC(*)=O]

In some embodiments, L is

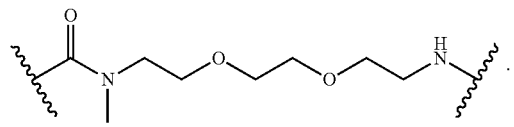 [SMILES: *NCCOCCOCCN(C)C(*)=O]

In some embodiments, L is

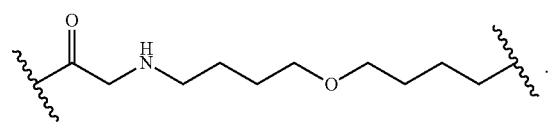 [SMILES: *CCCCOCCCCNCC(*)=O]

In some embodiments, L is

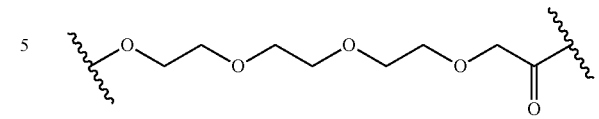

In some embodiments, L is

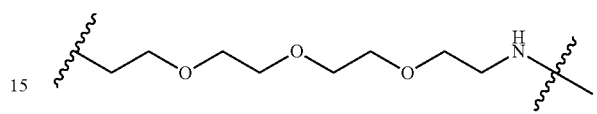

In some embodiments, L is

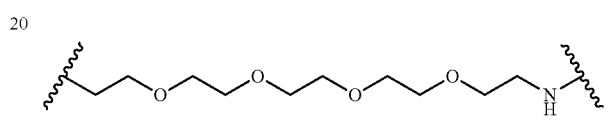

In some embodiments, L is

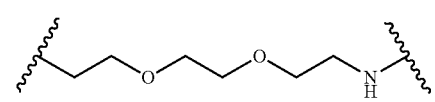

In some embodiments, L is

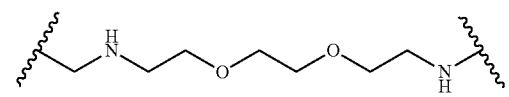

In some embodiments, L is

In some embodiments, L is

In some embodiments, L is

In some embodiments, L is

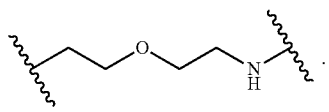 [SMILES: *CCOCCN*]

In some embodiments, L is

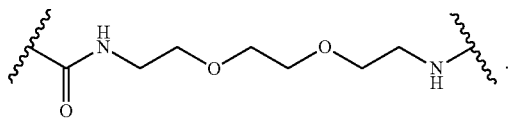 [SMILES: *NCCOCCOCCNC(*)=O]

In some embodiments, L is

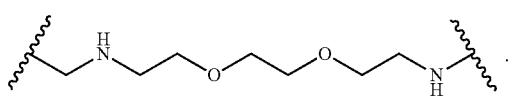 [SMILES: *CNCCOCCOCCN*]

In some embodiments, L is


In some embodiments, L is

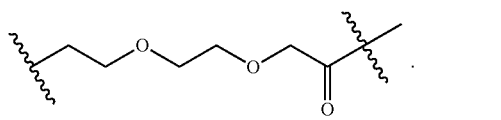 [SMILES: *CCOCCOCC(*)=O]

In some embodiments, L is


In some embodiments, L is

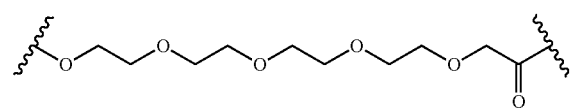

In some embodiments, L is

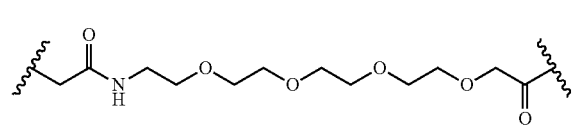

In some embodiments, L is

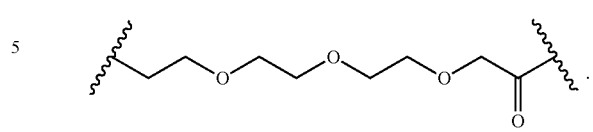

In some embodiments, L is

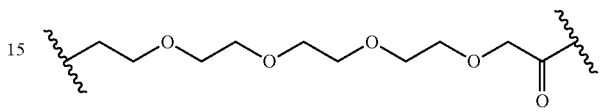

In some embodiments, L is

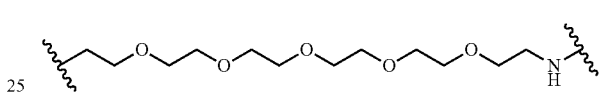

In some embodiments, L is

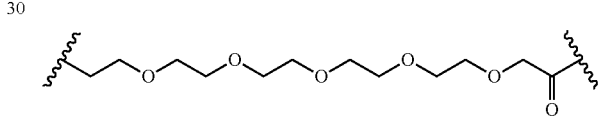

In some embodiments, L is

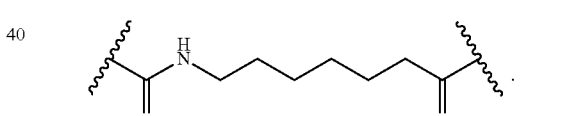

In some embodiments, L is

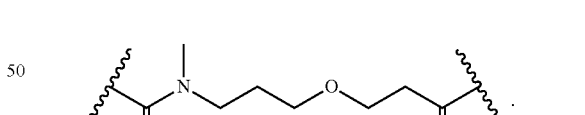

In some embodiments, L is

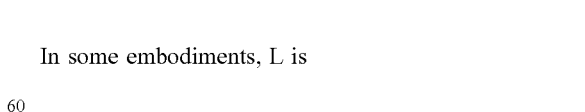

In some embodiments, L is

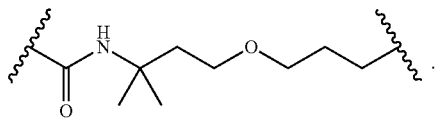 [SMILES: *CCCOCCC(C)(C)NC(*)=O]

In some embodiments, L is

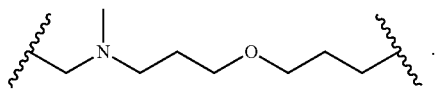 [SMILES: *CCCOCCCN(C)C*]

In some embodiments, L is

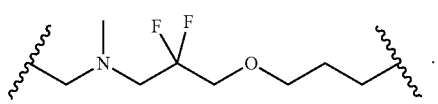 [SMILES: *CCCOCC(F)(F)CN(C)C*]

In some embodiments, L is

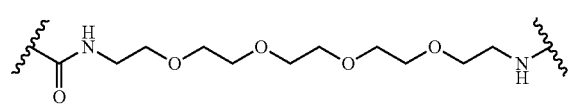

In some embodiments, L is

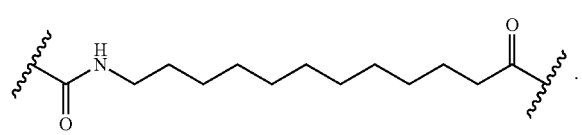 [SMILES: *C(=O)CCCCCCCCCCCNC(*)=O]

In some embodiments, L is

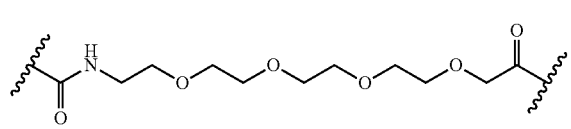

In some embodiments, L is

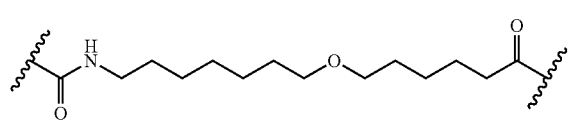

In some embodiments, L is

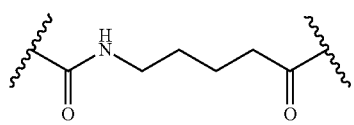

In some embodiments, L is

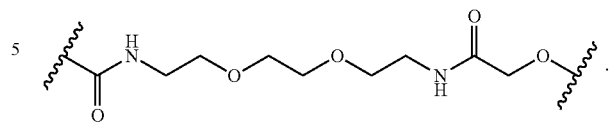

In some embodiments, L is

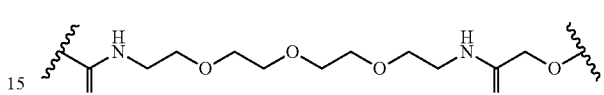

In some embodiments, L is

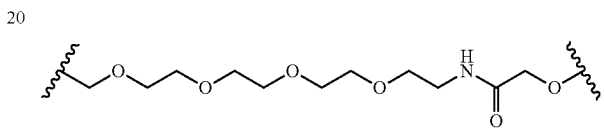

In some embodiments, L is

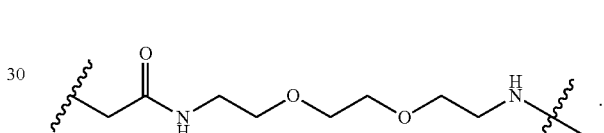

In some embodiments, L is

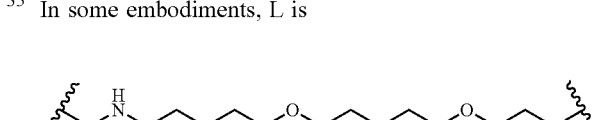

In some embodiments, L is

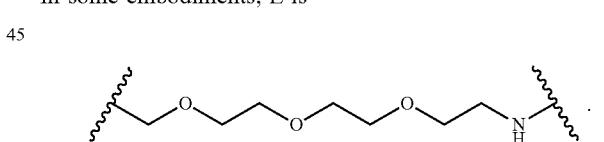

In some embodiments, L is

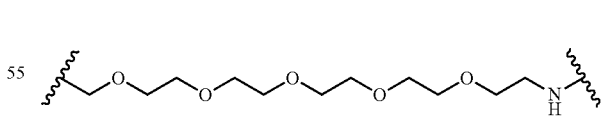

In some embodiments, L is

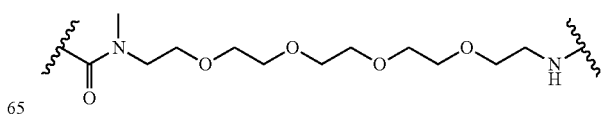

US 10,874,743 B2
In some embodiments, L is
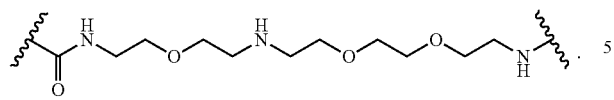
In some embodiments, L is
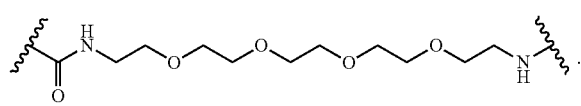 [SMILES: *NCCOCCOCCOCCOCCNC(*)=O]
In some embodiments, L is
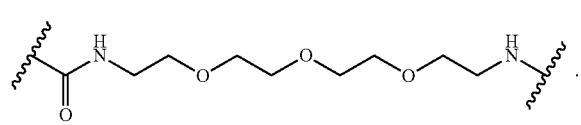 [SMILES: *NCCOCCOCCOCCNC(*)=O]
In some embodiments, L is
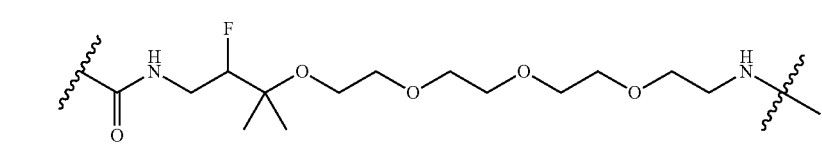
In some embodiments, L is
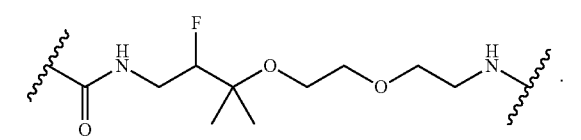 [SMILES: *NCCOCCOC(C)(C)C(F)CNC(*)=O]
In some embodiments, L is
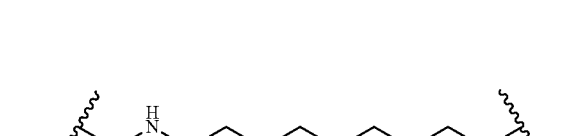
In some embodiments, L is
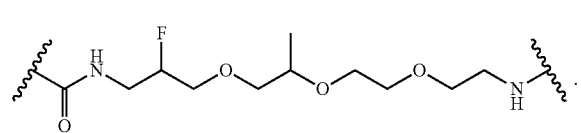 [SMILES: *NCCOCCOC(C)COCC(F)CNC(*)=O]
In some embodiments, L is

In some embodiments, L is

In some embodiments, L is
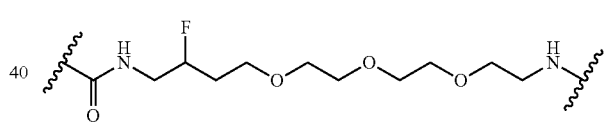
In some embodiments, L is
In some embodiments, L is
In some embodiments, L is
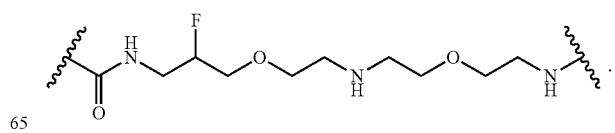

In some embodiments, L is
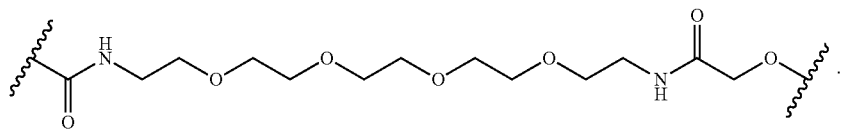 [SMILES: *OCC(=O)NCCOCCOCCOCCOCCNC(*)=O]
In some embodiments, L is
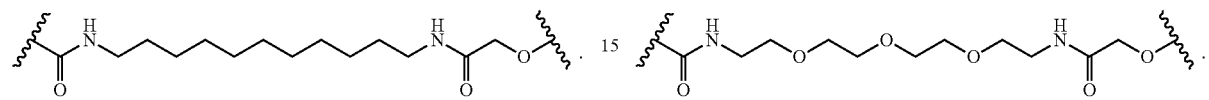
In some embodiments, L is
In some embodiments, L is
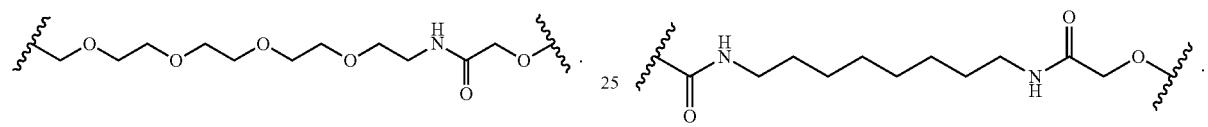
In some embodiments, L is
In some embodiments, L is
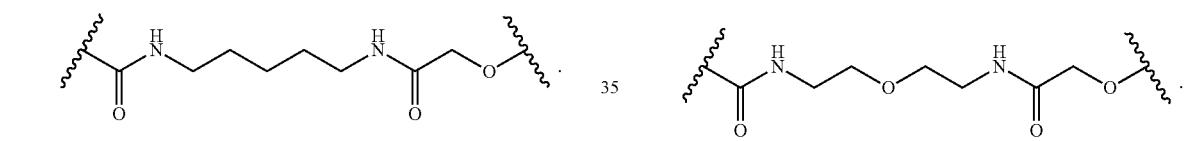
In some embodiments, L is
In some embodiments, L is
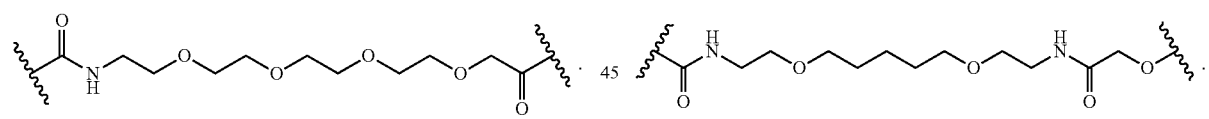
In some embodiments, L is
In embodiments, L is
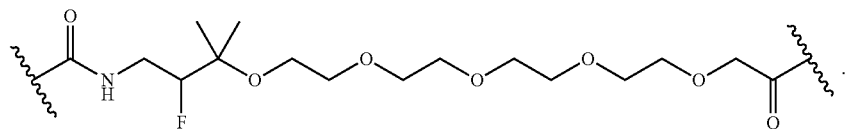 [SMILES: *C(=O)COCCOCCOCCOCCOC(C)(C)C(F)CNC(*)=O]
In some embodiments, L is
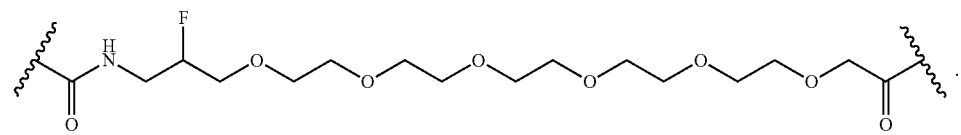 [SMILES: *C(=O)COCCOCCOCCOCCOCCOCC(F)CNC(*)=O]

In some embodiments, L is
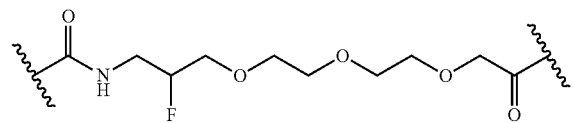
In some embodiments, L is
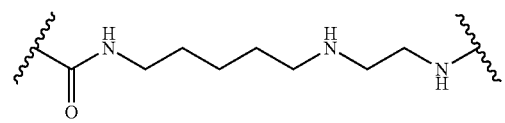
In some embodiments, L is
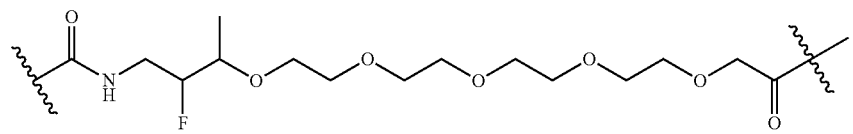
In some embodiments, L is
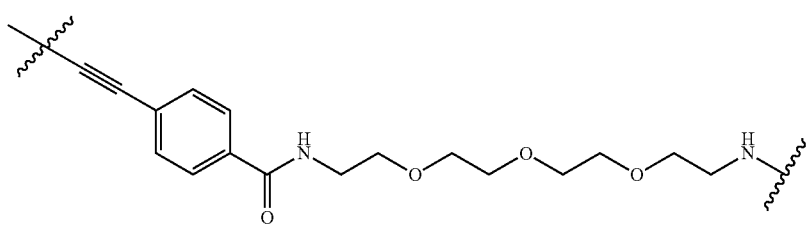
In some embodiments, L is
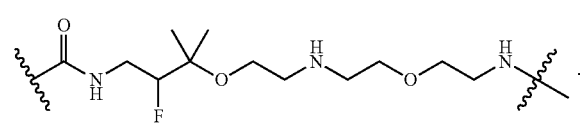 [SMILES: *NCCOCCNCCOC(C)(C)C(F)CNC(*)=O]
In some embodiments, L is
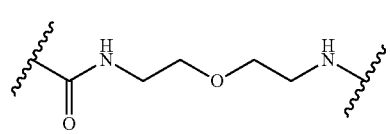
In some embodiments, L is
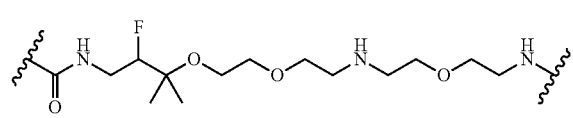
In some embodiments, L is
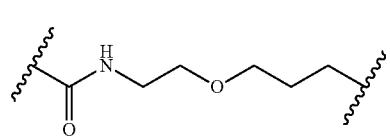
In some embodiments, L is
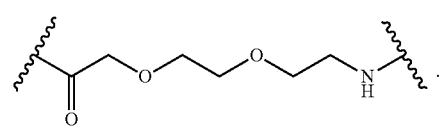 [SMILES: *NCCOCCOCC(*)=O]
In some embodiments, L is In some embodiments, L is
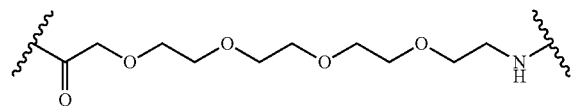
In some embodiments, L is
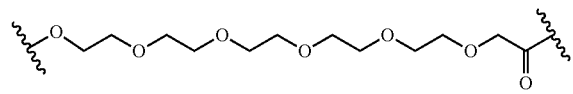
In some embodiments, L is
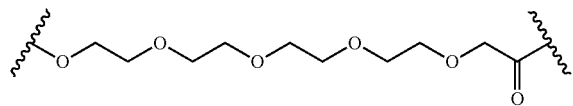
In some embodiments, L is
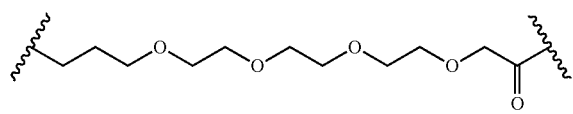
In some embodiments, L is
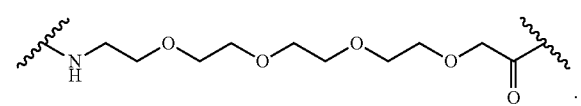 [SMILES: *NCCOCCOCCOCCOCC(*)=O]
In some embodiments, L is
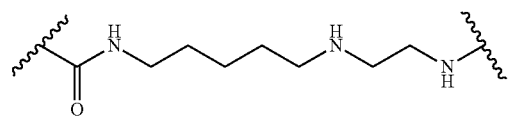
In some embodiments, L is
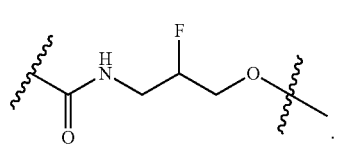 [SMILES: *OCC(F)CNC(*)=O]
In some embodiments, L is
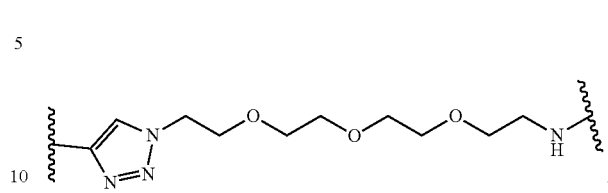
In some embodiments, L is
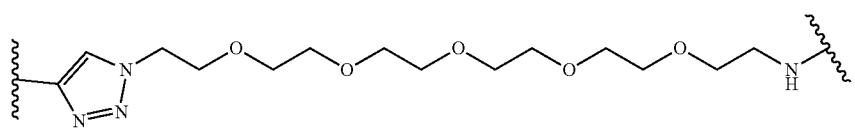 [SMILES: *NCCOCCOCCOCCOCCOCCn1cc(*)nn1]
In some embodiments, L is
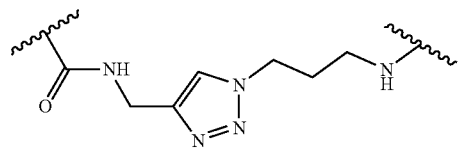
In some embodiments, L is
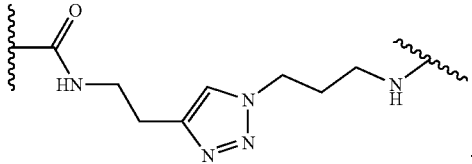 [SMILES: *NCCCn1cc(CCNC(*)=O)nn1]
In some embodiments, L is
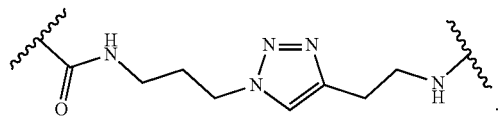 [SMILES: *NCCc1cn(CCCNC(*)=O)nn1]
In some embodiments, L is
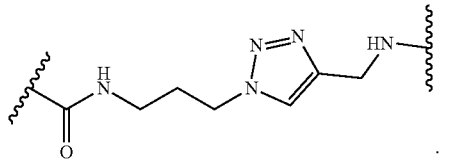 [SMILES: *NCc1cn(CCCNC(*)=O)nn1]

In some embodiments, L is
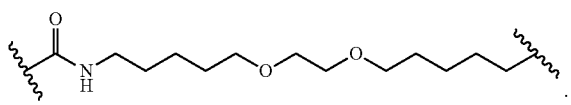 [SMILES: *CCCCCOCCOCCCCCNC(*)=O]
In some embodiments, L is
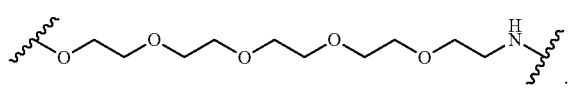 [SMILES: *NCCOCCOCCOCCOCCO*]
In some embodiments, L is
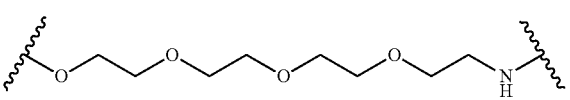
In some embodiments, L is
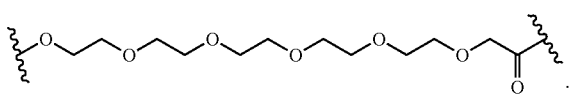 [SMILES: *OCCOCCOCCOCCOCCOCC(*)=O]
In some embodiments, L is
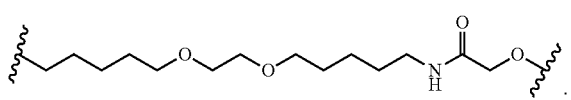 [SMILES: *CCCCCOCCOCCCCCNC(=O)CO*]
In some embodiments, L is
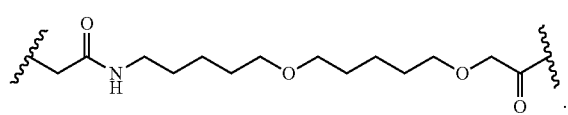 [SMILES: *CC(=O)NCCCCCOCCCCCOCC(*)=O]
In some embodiments, L is
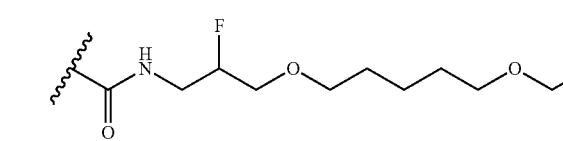
In some embodiments, L is
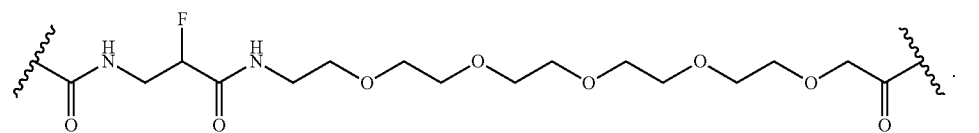 [SMILES: *C(=O)COCCOCCOCCOCCOCCNC(=O)C(F)CNC(*)=O]
In some embodiments, L is
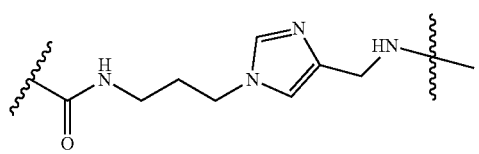
In some embodiments, L is
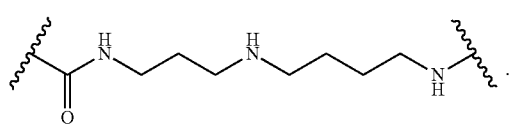 [SMILES: *NCCCCNCCCNC(*)=O]
In some embodiments, L is
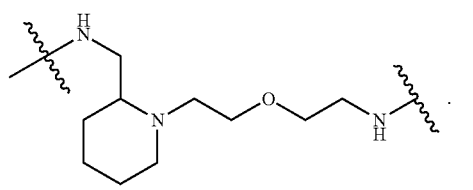 [SMILES: *NCCOCCN1CCCCC1CN*]
In some embodiments, L is
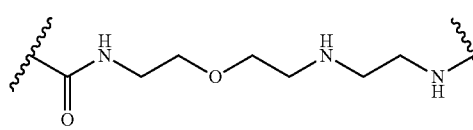
In some embodiments, L is
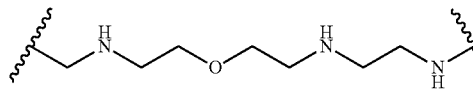

In some embodiment, L is

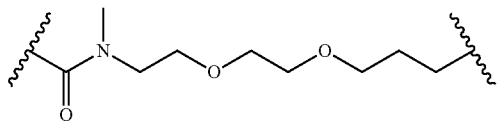

In some embodiment, L is

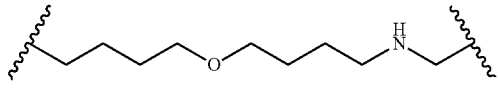

In some embodiment, L is

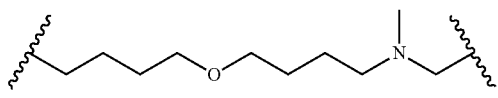

In some embodiments, L is

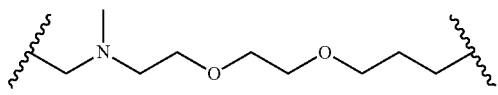

In some embodiments, L is

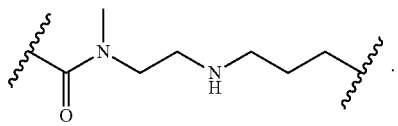

In some embodiments, L is

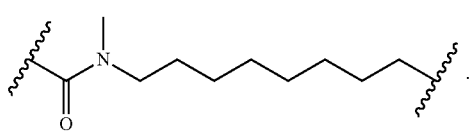 [SMILES: *CCCCCCCCN(C)C(*)=O]

In some embodiments, L is

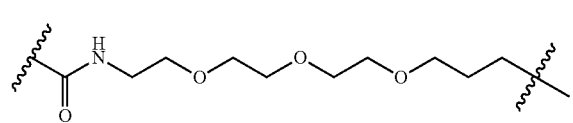

In some embodiments, L is

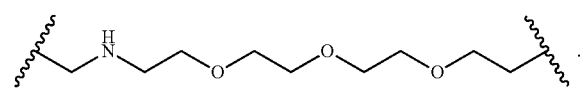 [SMILES: *CCOCCOCCOCCNC*]

In some embodiments, L is

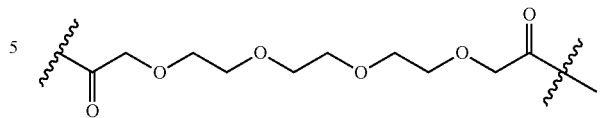

In some embodiments, L is

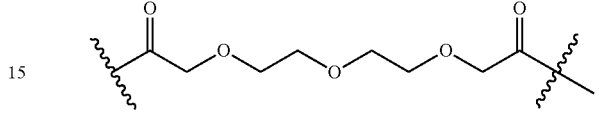

In some embodiments, L is

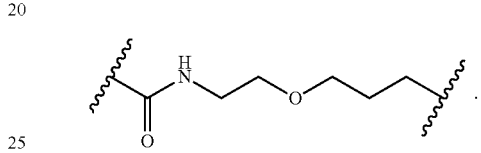

In some embodiments, L is

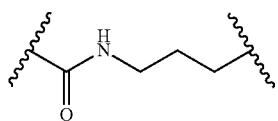

In some embodiments, L is

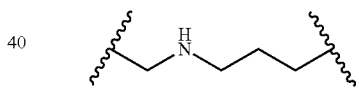

In some embodiments, L is

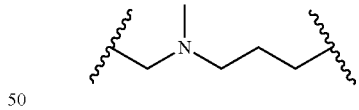

In some embodiments, L is

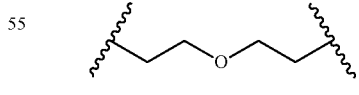

In some embodiments, L is

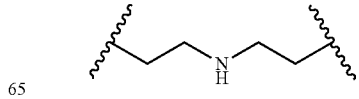

In some embodiments, L is
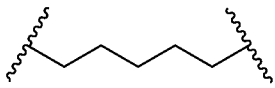
In some embodiments, L is
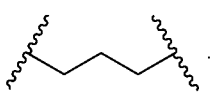 [SMILES: *CCC*]
In some embodiments, L is
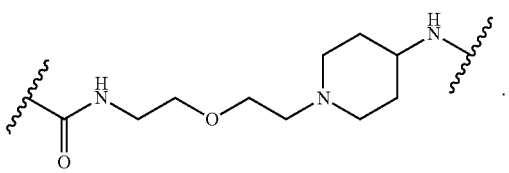 [SMILES: *NC1CCN(CCOCCNC(*)=O)CC1]
In some embodiments, L is
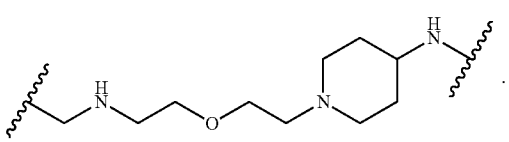 [SMILES: *CNCCOCCN1CCC(N*)CC1]
In some embodiments, L is
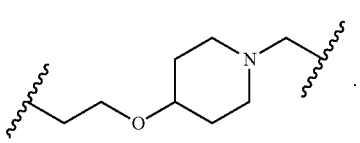 [SMILES: *CCOC1CCN(C*)CC1]
In some embodiments, L is
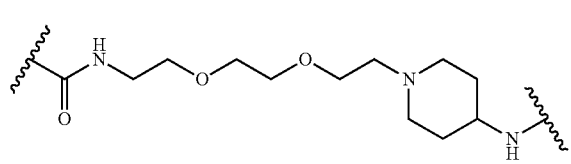
In some embodiments, L is
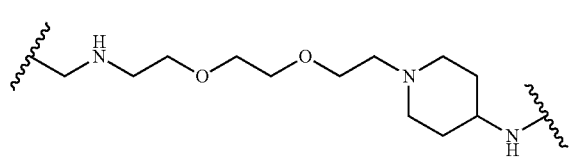
In some embodiments, L is
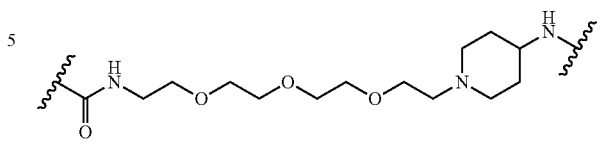
In some embodiments, L is
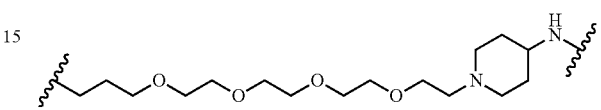
In some embodiments, L is
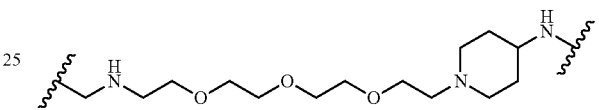
In some embodiments, L is
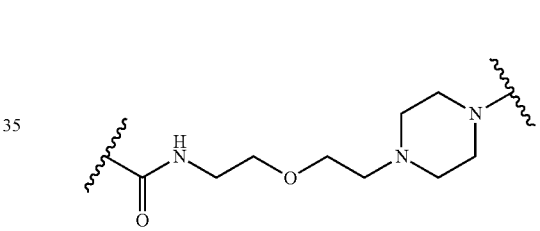
In some embodiments, L is
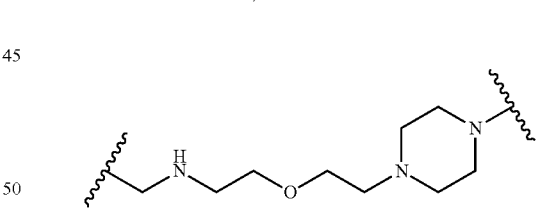
In some embodiments, L is
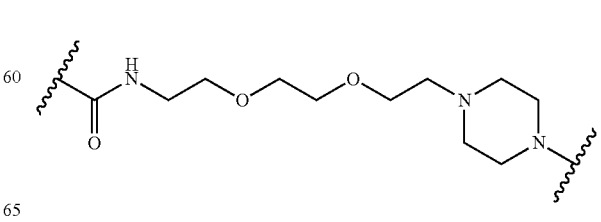

In some embodiments, L is

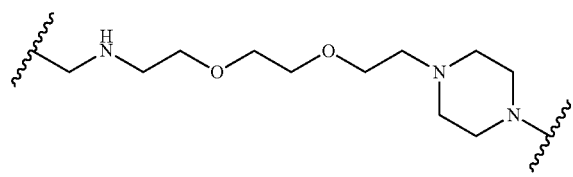

In some embodiments, L is

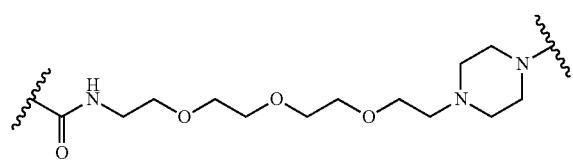

In some embodiments, L is

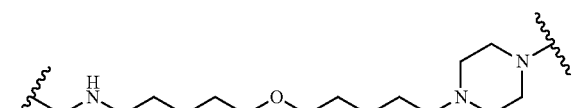

In some embodiments, L is

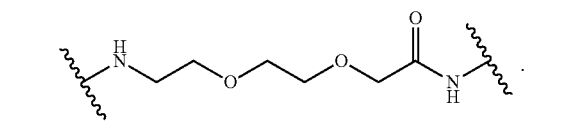 [SMILES: *NCCOCCOCC(=O)N*]

In some embodiments, L is


In some embodiments, L is

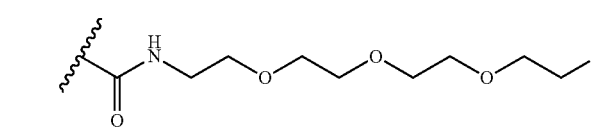

In some embodiments, L is

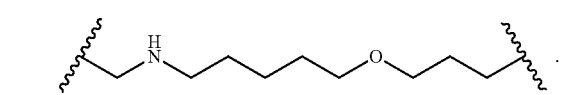 [SMILES: *CCCOCCCCCNC*]

In some embodiments, L is

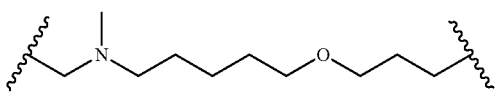

In some embodiments, L is

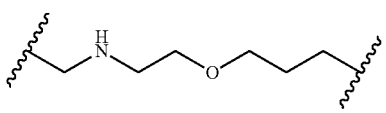

In some embodiments, L is

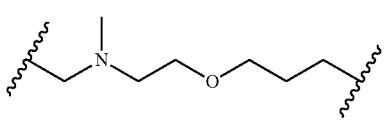

In some embodiments, L is

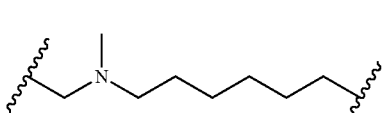

In some embodiments, L is

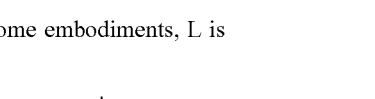

In some embodiments, L is

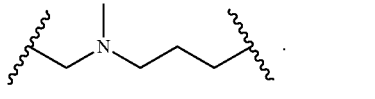 [SMILES: *CCCN(C)C*]

In some embodiments, L is

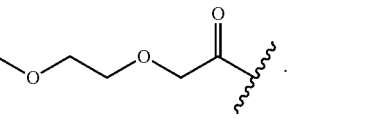

In some embodiments, L is

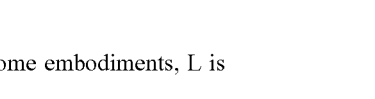

In some embodiments, L is

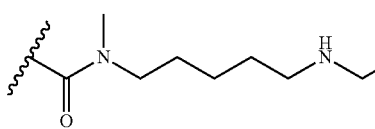

In some embodiments, L is

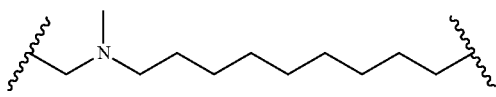

In some embodiments, L is

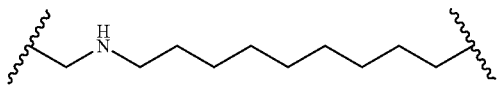

In some embodiments, L is

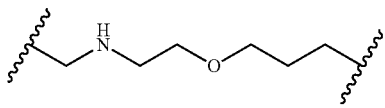

In some embodiments, L is

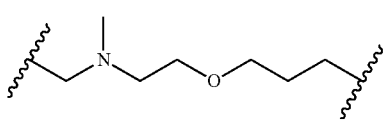

In some embodiments, L is

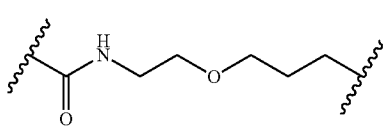

In some embodiments, L is

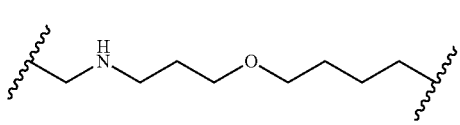

In some embodiments, L is

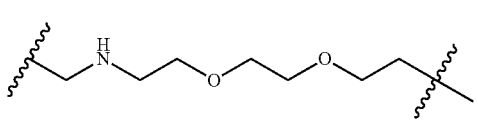

In some embodiments, L is

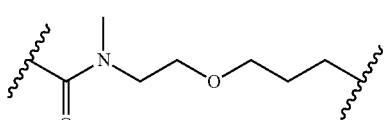

In some embodiments, L is

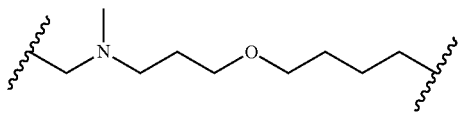

In some embodiments, L is

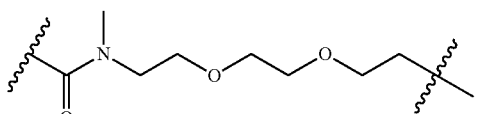

In some embodiments, L is

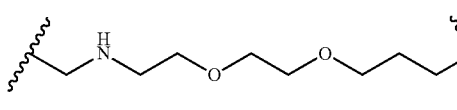

In some embodiments, L is

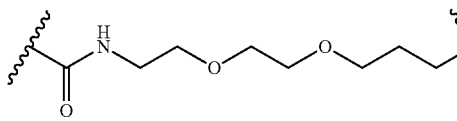

In some embodiments, L is

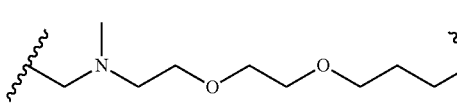

In some embodiments, L is

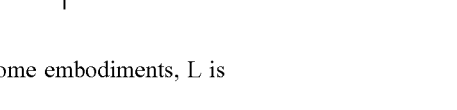

In some embodiments, L is

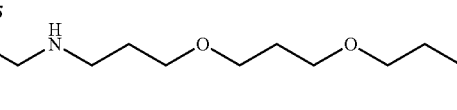

In some embodiment, L is

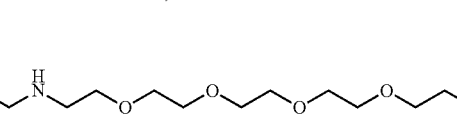

In some embodiment, L is
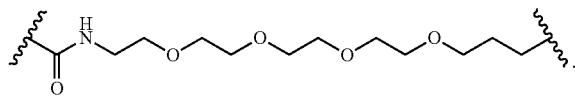 [SMILES: *CCCOCCOCCOCCOCCNC(*)=O]
In some embodiments, L is
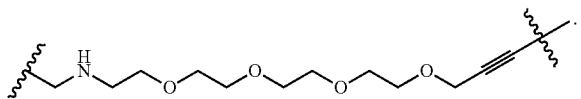 [SMILES: *C#CCOCCOCCOCCOCCNC*]
In some embodiments, L is
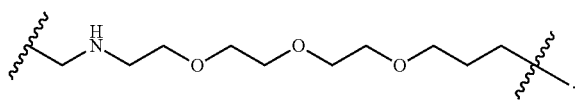 [SMILES: *CCCOCCOCCOCCNC*]
In some embodiments, L is
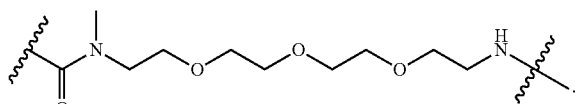
In some embodiments, L is
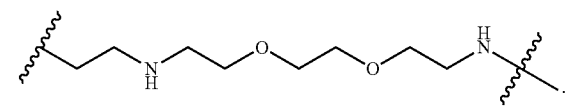 [SMILES: *CCNCCOCCOCCN*]
In some embodiments, L is
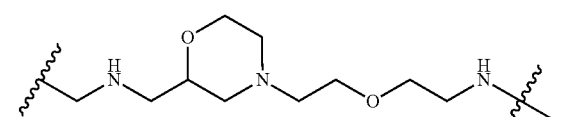
In some embodiments, L is
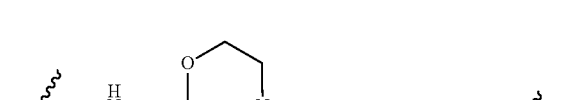
In some embodiments, L is
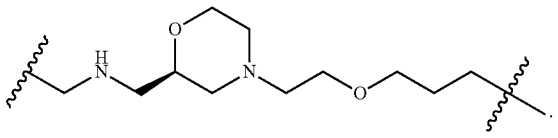 [SMILES: *CCCOCCN1CCO[C@H](CNC*)C1]
In some embodiments, L is
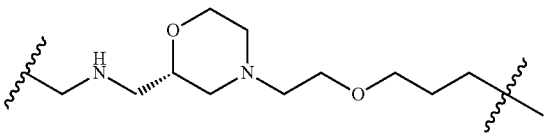
In some embodiments, L is
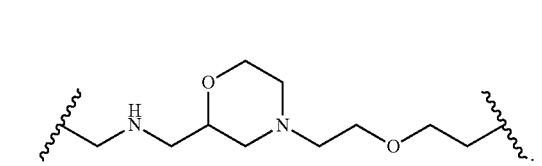 [SMILES: *CCOCCN1CCOC(CNC*)C1]
In some embodiments, L is
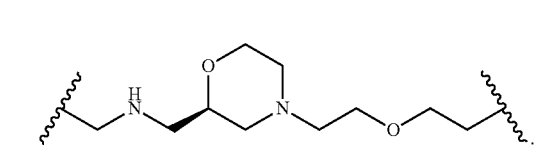 [SMILES: *CCOCCN1CCO[C@H](CNC*)C1]
In some embodiments, L is
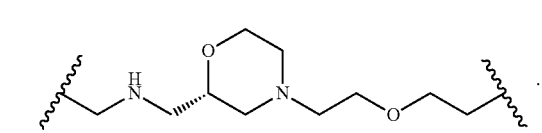 [SMILES: *CCOCCN1CCO[C@@H](CNC*)C1]
In some embodiments, L is
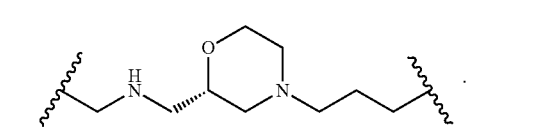 [SMILES: *CCCN1CCO[C@@H](CNC*)C1]
In some embodiments, L is
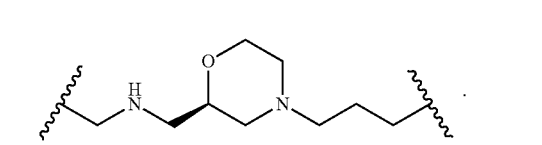 [SMILES: *CCCN1CCO[C@H](CNC*)C1]

In some embodiments, L is
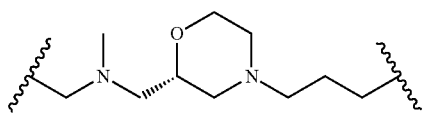
In some embodiments, L is
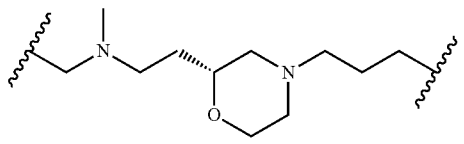
In some embodiments, L is
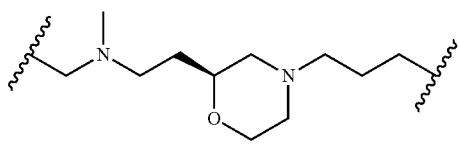
In some embodiments, L is
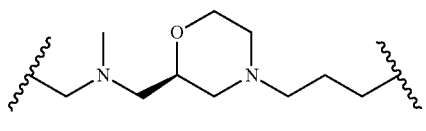
In some embodiments, L is
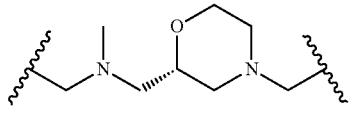
In some embodiments, L is
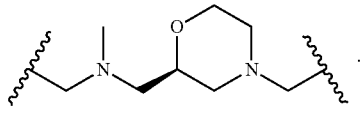 [SMILES: *CN(C)C[C@@H]1CN(C*)CCO1]
In some embodiments, L is
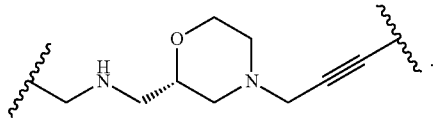 [SMILES: *C#CCN1CCO[C@@H](CNC*)C1]
In some embodiments, L is
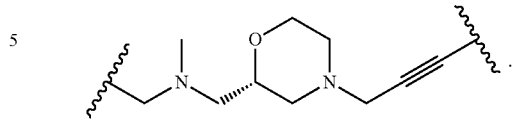
In some embodiments, L is
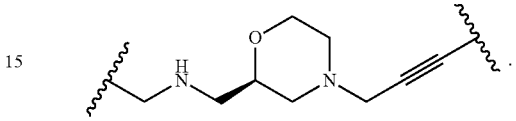
In some embodiments, L is
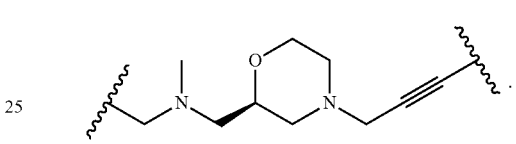
In some embodiments, L is
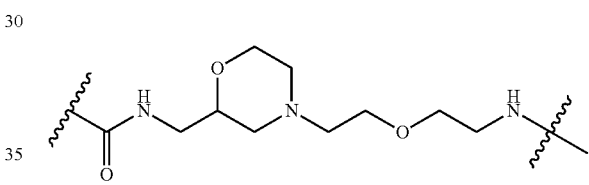
In some embodiments, L is
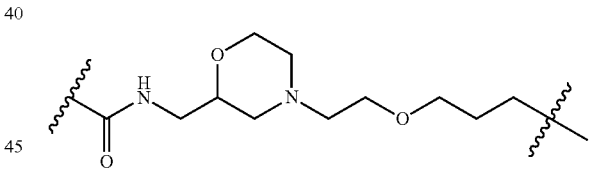
In some embodiments, L is
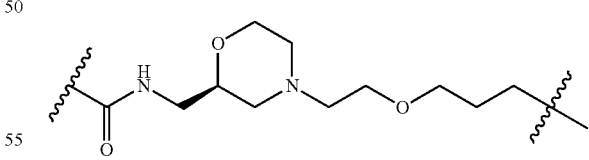
In some embodiments, L is
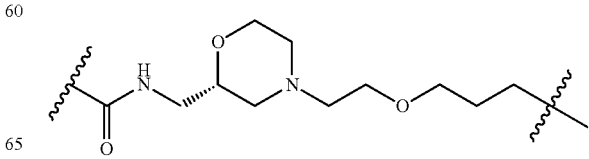

In some embodiments, L is
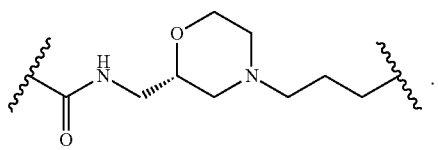 [SMILES: *CCCN1CCO[C@@H](CNC(*)=O)C1]
In some embodiments L is
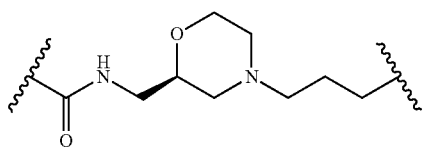
In some embodiments, L is
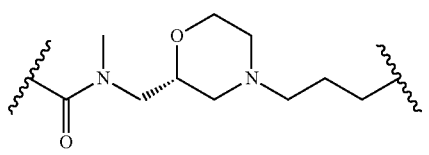
In some embodiments, L is
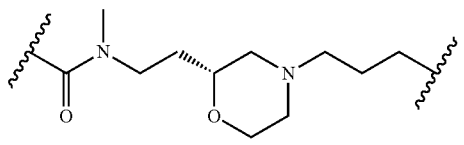
In some embodiments, L is
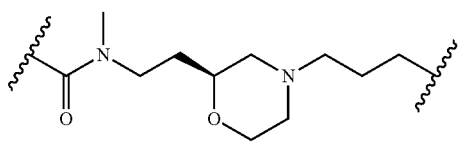
In some embodiments, L is
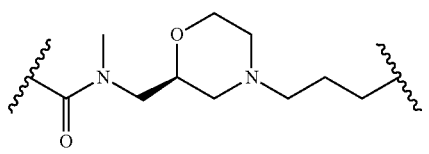
In some embodiments, L is
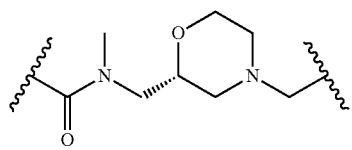
In some embodiments, L is
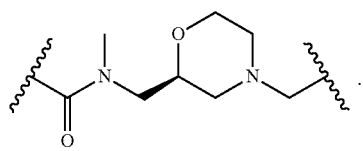 [SMILES: *CN1CCO[C@H](CN(C)C(*)=O)C1]
In some embodiments, L is
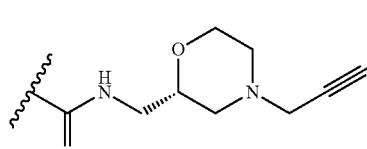
In some embodiments, L is
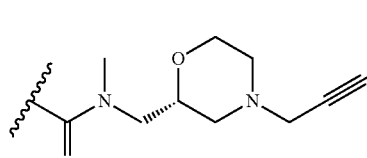
In some embodiments, L is
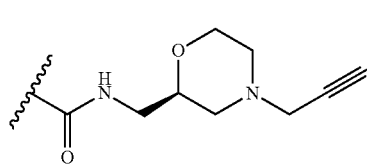
In some embodiments, L is
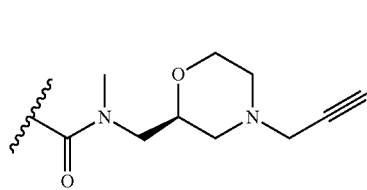

In some embodiments, L is
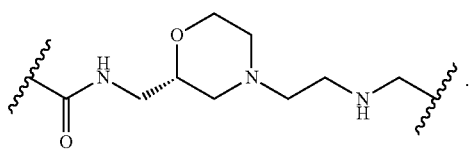 [SMILES: *CNCCN1CCO[C@@H](CNC(*)=O)C1]
In some embodiments, L is
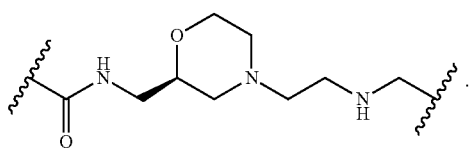 [SMILES: *CNCCN1CCO[C@H](CNC(*)=O)C1]
In some embodiments, L is
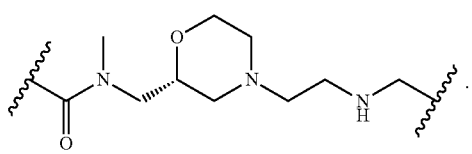 [SMILES: *CNCCN1CCO[C@@H](CN(C)C(*)=O)C1]
In some embodiments, L is
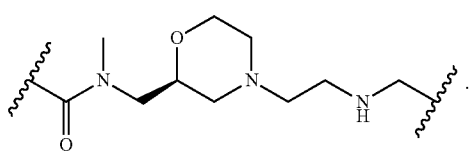 [SMILES: *CNCCN1CCO[C@H](CN(C)C(*)=O)C1]
In some embodiments, L is
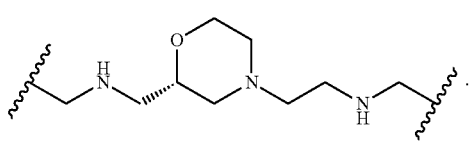 [SMILES: *CNCCN1CCO[C@@H](CNC*)C1]
In some embodiments, L is
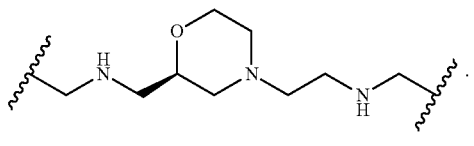 [SMILES: *CNCCN1CCO[C@H](CNC*)C1]
In some embodiments, L is
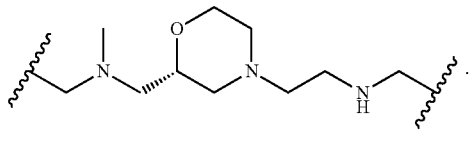 [SMILES: *CNCCN1CCO[C@@H](CN(C)C*)C1]
In some embodiments, L is
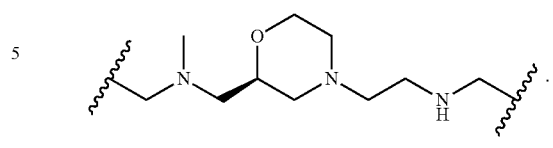
In some embodiments, L is
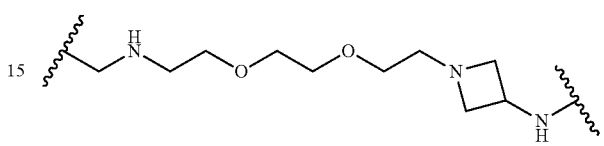
In some embodiments, L is
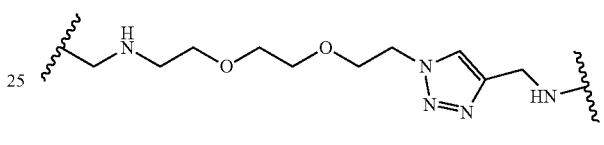
In some embodiments, L is
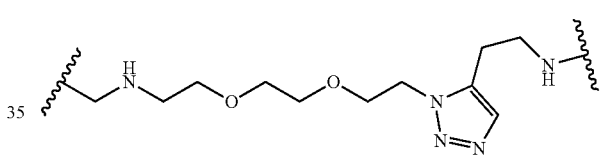
In some embodiments, L is
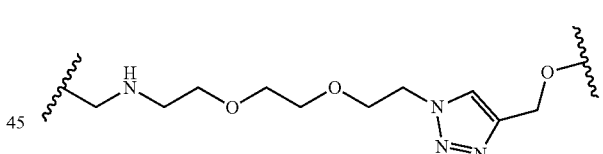
In some embodiments, L is
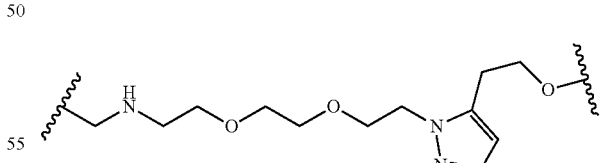
In some embodiments, L is
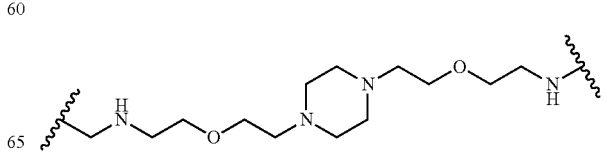

In some embodiments, L is
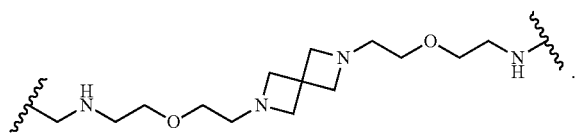 [SMILES: *CNCCOCCN1CC2(CN(CCOCCN*)C2)C1]
In some embodiments, L is
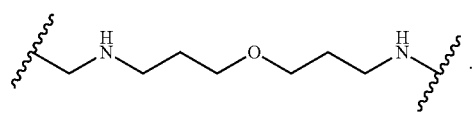 [SMILES: *CNCCCOCCCN*]
In some embodiments, L is
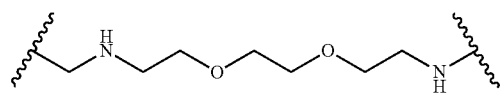
In some embodiments, L is
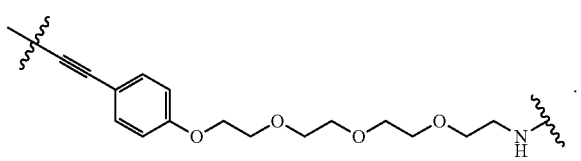 [SMILES: *C#Cc1ccc(OCCOCCOCCOCCN*)cc1]
In some embodiments, L is
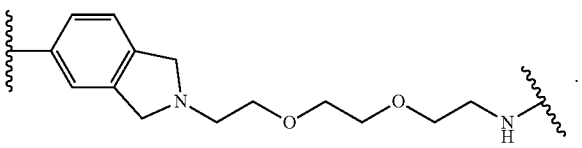 [SMILES: *NCCOCCOCCN1Cc2ccc(*)cc2C1]
In some embodiments, L is
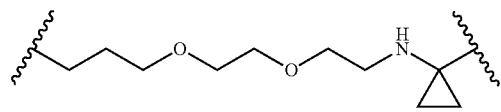
In some embodiments, L is
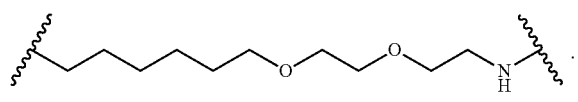 [SMILES: *CCCCCCOCCOCCN*]
In some embodiments, L is
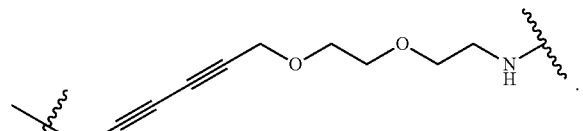
In some embodiments, L is
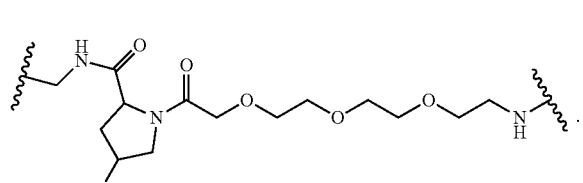
In some embodiments, L is
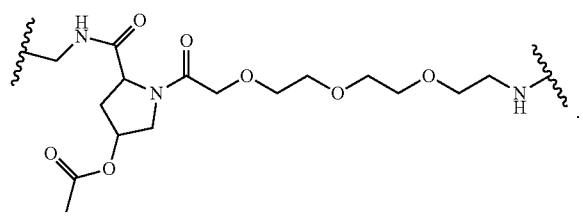 [SMILES: *CNC(=O)C1CC(OC(C)=O)CN1C(=O)COCCOCCOCCN*]
In some embodiments, L is
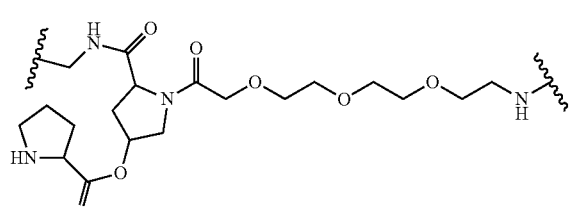
In some embodiments, L is
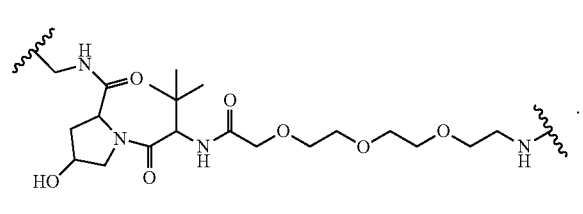 [SMILES: *CNC(=O)C1CC(O)CN1C(=O)C(NC(=O)COCCOCCOCCN*)C(C)(C)C]

In some embodiments, L is
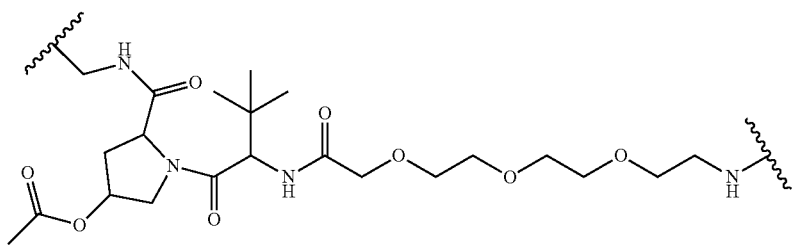
In some embodiments, L is
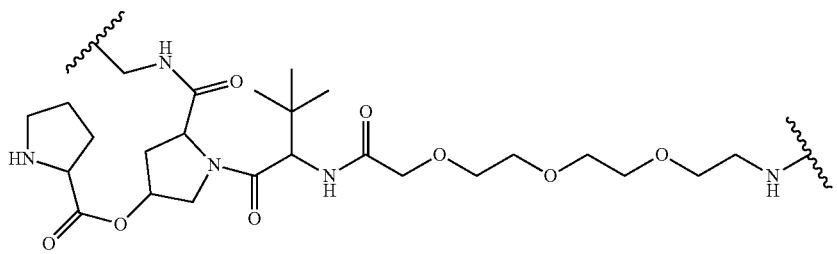
In some embodiments, L is
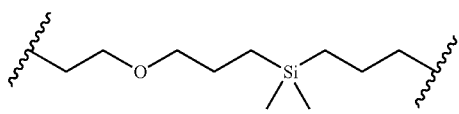
In some embodiments, L is
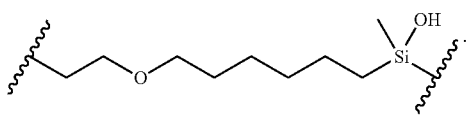 [SMILES: *CCOCCCCCC[Si](*)(C)O]
In some embodiments, L is
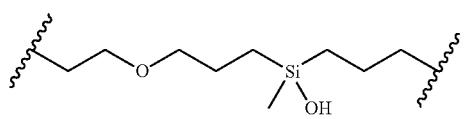
In some embodiments, L is
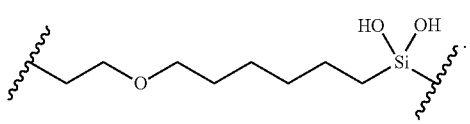 [SMILES: *CCOCCCCCC[Si](*)(O)O]
In some embodiments, L is
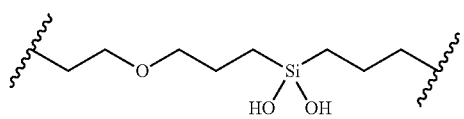
In some embodiments, L is
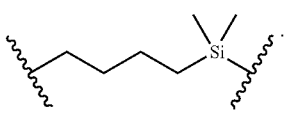 [SMILES: *CCCC[Si](*)(C)C]
In some embodiments, L is
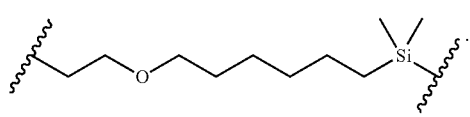
In some embodiments, L is
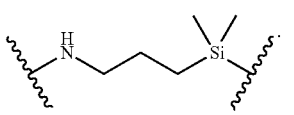 [SMILES: *NCCC[Si](*)(C)C]

In some embodiments, L is
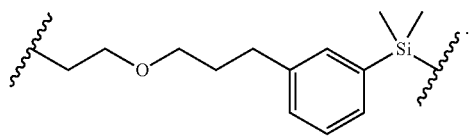 [SMILES: *CCOCCCc1cccc([Si](*)(C)C)c1]
In some embodiments, L is
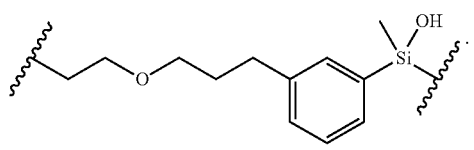 [SMILES: *CCOCCCc1cccc([Si](*)(C)O)c1]
In some embodiments, L is
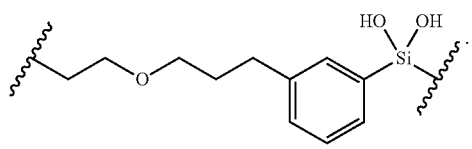 [SMILES: *CCOCCCc1cccc([Si](*)(O)O)c1]
In some embodiments, L is
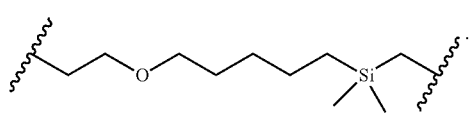 [SMILES: *CCOCCCCC[Si](C)(C)C*]
In some embodiments, L is
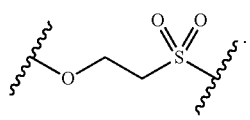 [SMILES: *OCCS(*)(=O)=O]
In some embodiments, L is
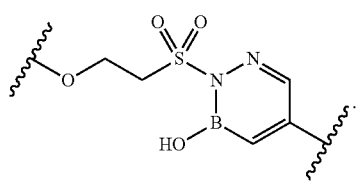 [SMILES: *OCCS(=O)(=O)N1N=CC(*)=CB1O]
In some embodiments, L is
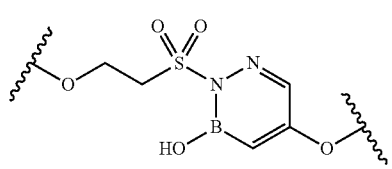
In some embodiments, L is
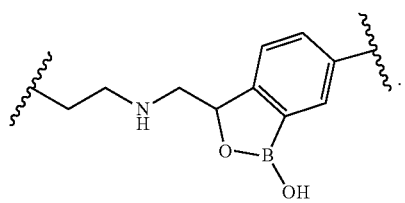 [SMILES: *CCNCC1OB(O)c2cc(*)ccc21]
In some embodiments, L is
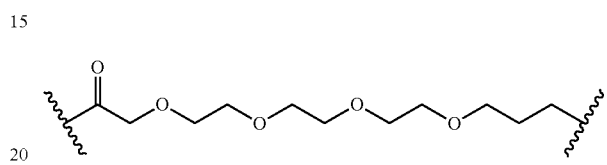
In some embodiments, L is
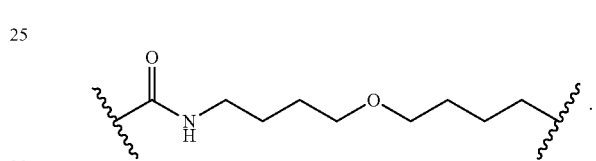
In some embodiments, L is
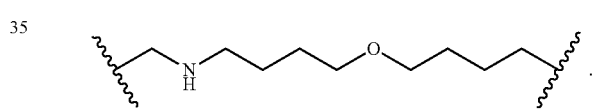
In some embodiments, L is
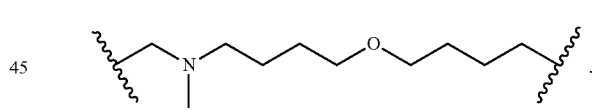
In some embodiments, L is
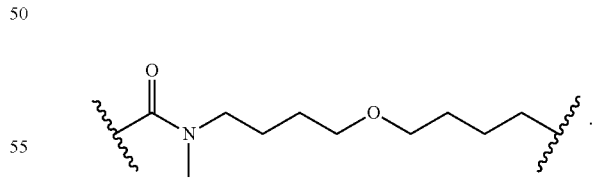
In some embodiments, L is
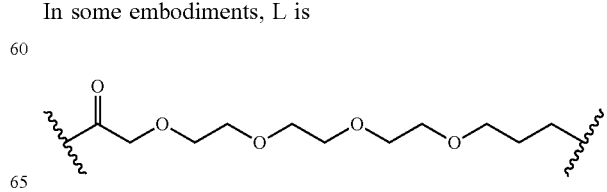

In some embodiments, L is

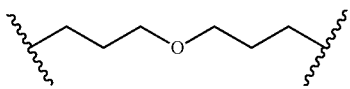

In some embodiments, L is

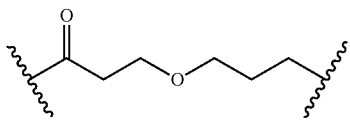

In some embodiments, L is

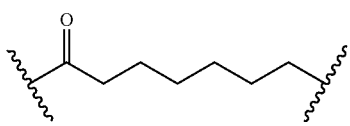

In some embodiments, L is

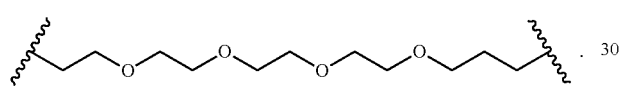

In some embodiments, L is

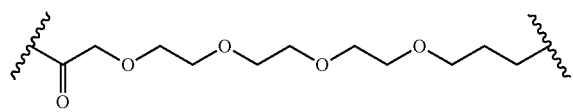

In some embodiments, L is

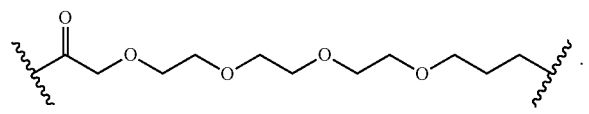 [SMILES: *CCCOCCOCCOCCOCC(*)=O]

In some embodiments, L is

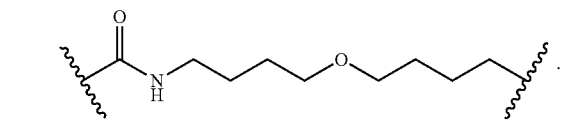 [SMILES: *CCCCOCCCCNC(*)=O]

In some embodiments, L is

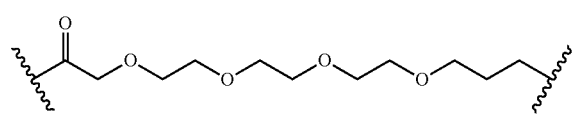

In some embodiments, L is

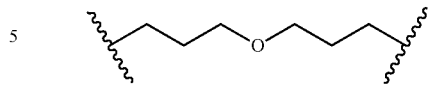

In some embodiments, L is

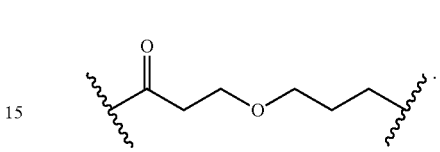

In some embodiments, L is

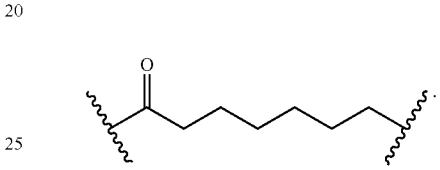

In some embodiments, L is

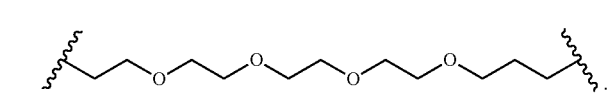 [SMILES: *CCCOCCOCCOCCOCC*]

In some embodiments, L is

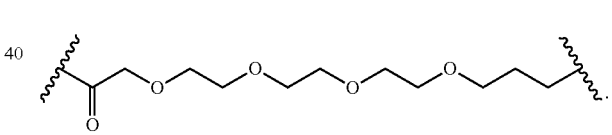

In some embodiments, L is

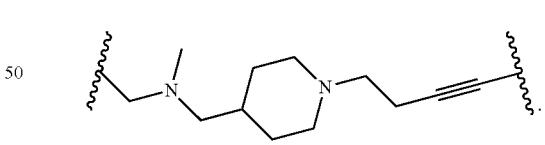

In some embodiments, L is

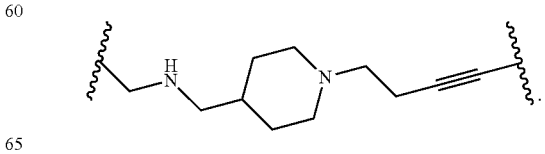

In some embodiments, L is
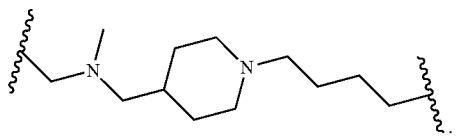 [SMILES: *CCCCN1CCC(CN(C)C*)CC1]
In some embodiments, L is
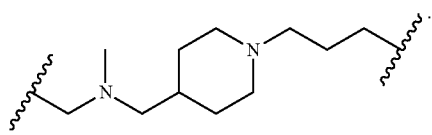 [SMILES: *CCCN1CCC(CN(C)C*)CC1]
In some embodiments, L is
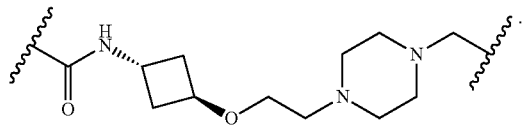 [SMILES: *CN1CCN(CCO[C@H]2C[C@H](NC(*)=O)C2)CC1]
In some embodiments, L is
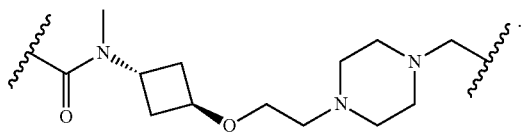 [SMILES: *CN1CCN(CCO[C@H]2C[C@H](N(C)C(*)=O)C2)CC1]
In some embodiments, L is
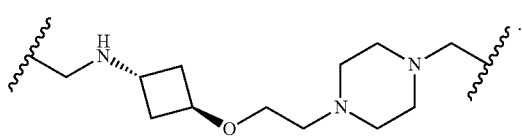 [SMILES: *CN[C@H]1C[C@H](OCCN2CCN(C*)CC2)C1]
In some embodiments, L is
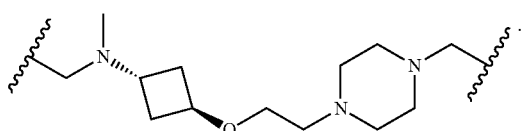
In some embodiments, L is
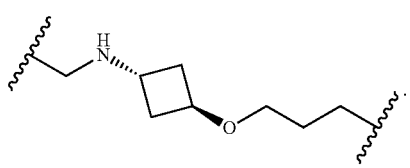 [SMILES: *CCCO[C@H]1C[C@H](NC*)C1]
In some embodiments, L is
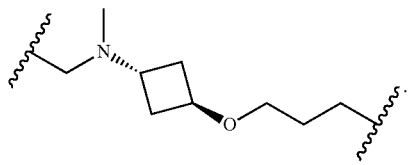 [SMILES: *CCCO[C@H]1C[C@H](N(C)C*)C1]
In some embodiments, L is
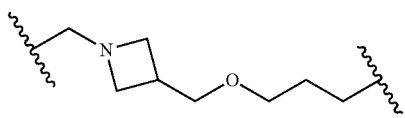
In some embodiments, L is
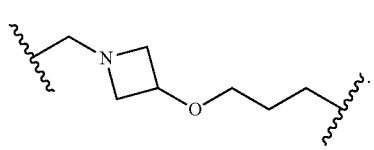 [SMILES: *CCCOC1CN(C*)C1]
In some embodiments, L is
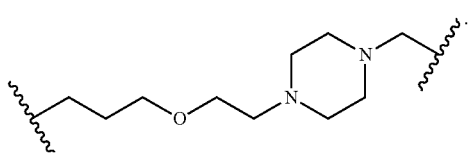 [SMILES: *CCCOCCN1CCN(C*)CC1]
In some embodiments, L is
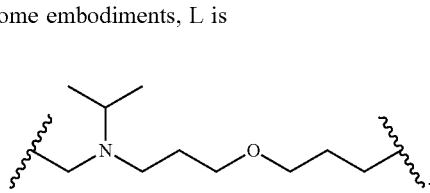
In some embodiments, L is
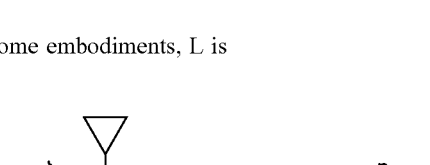
In some embodiments, L is
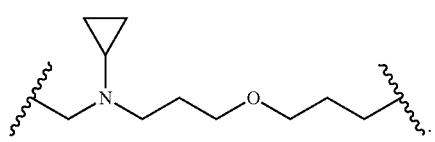 [SMILES: *CCCOCCCN(C*)C1CC1]

In some embodiments, L is
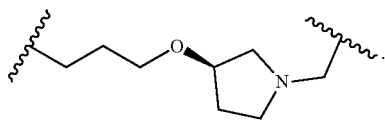 [SMILES: *CCCO[C@@H]1CCN(C*)C1]
In some embodiments, L is
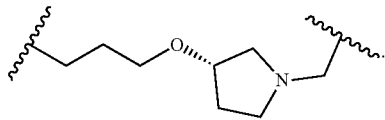 [SMILES: *CCCO[C@H]1CCN(C*)C1]
In some embodiments, L is
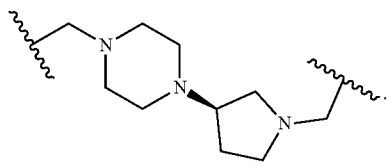 [SMILES: *CN1CCN([C@@H]2CCN(C*)C2)CC1]
In some embodiments, L is
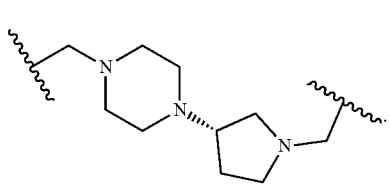 [SMILES: *CN1CCN([C@H]2CCN(C*)C2)CC1]
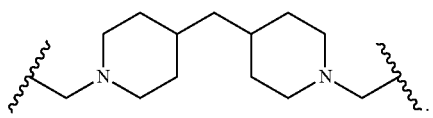 [SMILES: *CN1CCC(CC2CCN(C*)CC2)CC1]
In some embodiments, L is
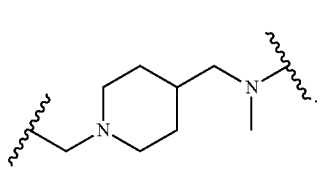 [SMILES: *CN1CCC(CN(*)C)CC1]
In some embodiments, L is
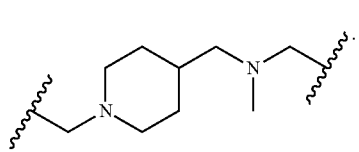 [SMILES: *CN(C)CC1CCN(C*)CC1]
In some embodiments, L is
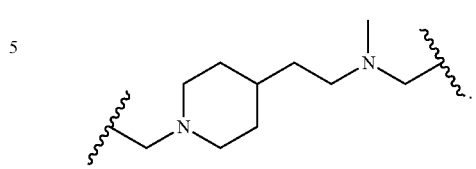
In some embodiments, L is
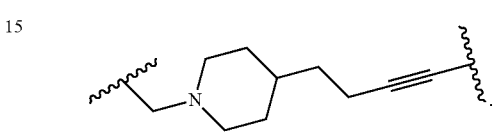
In some embodiments, L is
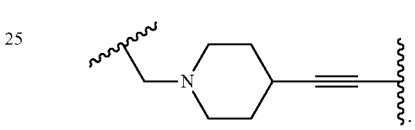
In some embodiments, L is
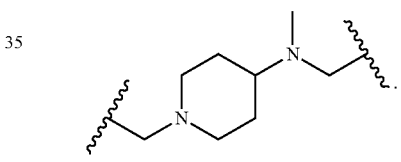
In some embodiments, L is
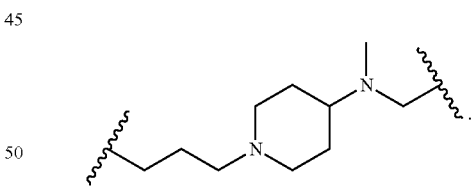
In some embodiments, L is
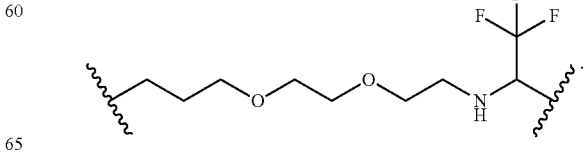

In some embodiments, L is
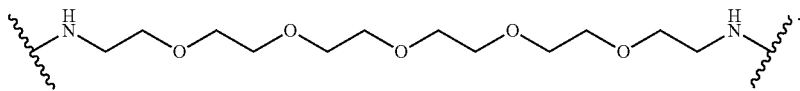 [SMILES: *NCCOCCOCCOCCOCCOCCN*]
In some embodiments, L is
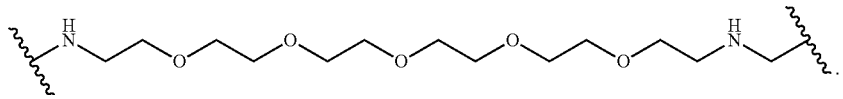 [SMILES: *CNCCOCCOCCOCCOCCOCCN*]
In some embodiments, L is
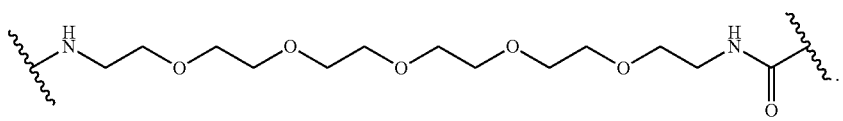 [SMILES: *NCCOCCOCCOCCOCCOCCNC(*)=O]
In some embodiments, L is
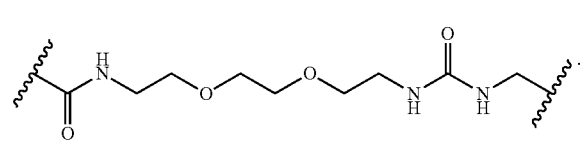 [SMILES: *CNC(=O)NCCOCCOCCNC(*)=O]
In some embodiments, L is
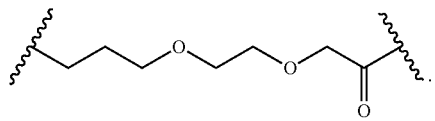 [SMILES: *CCCOCCOCC(*)=O]
In some embodiments, L is
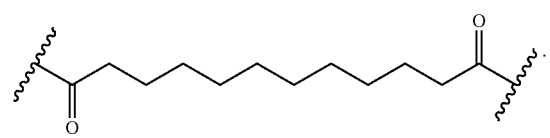 [SMILES: *C(=O)CCCCCCCCCCC(*)=O]
In some embodiments, L is
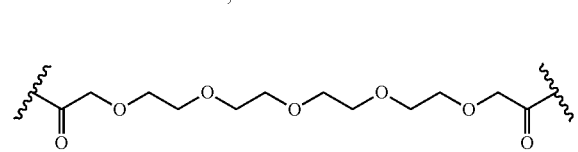
In some embodiments, L is
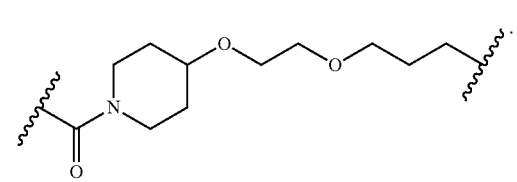 [SMILES: *CCCOCCOC1CCN(C(*)=O)CC1]
In some embodiments, L is
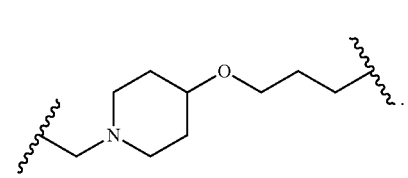 [SMILES: *CCCOC1CCN(C*)CC1]
In some embodiments, L is
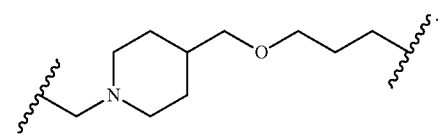 [SMILES: *CCCOCC1CCN(C*)CC1]
In some embodiments, L is
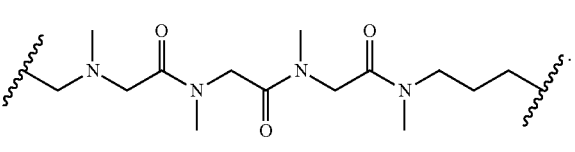 [SMILES: *CCCN(C)C(=O)CN(C)C(=O)CN(C)C(=O)CN(C)C*]

In some embodiments, L is
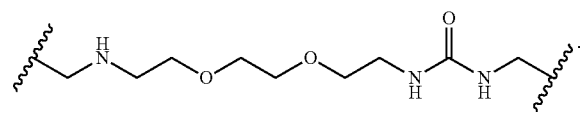 [SMILES: *CNCCOCCOCCNC(=O)NC*]
In some embodiment, L is
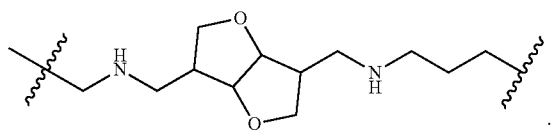 [SMILES: *CCCNCC1COC2C(CNC*)COC12]
In some embodiments, L is
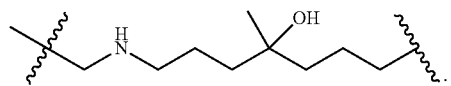 [SMILES: *CCCC(C)(O)CCCNC*]
In some embodiments, L is
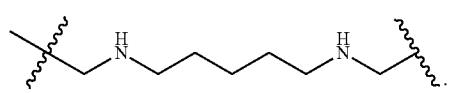 [SMILES: *CNCCCCCNC*]
In some embodiments, L is
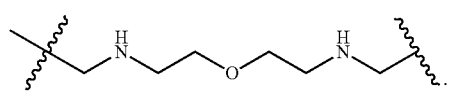 [SMILES: *CNCCOCCNC*]
In some embodiments, L is
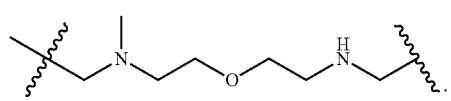 [SMILES: *CNCCOCCN(C)C*]
In some embodiments, L is
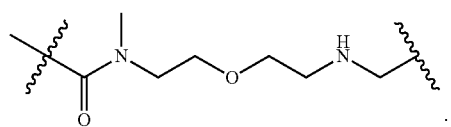 [SMILES: *CNCCOCCN(C)C(*)=O]
In some embodiments, L is
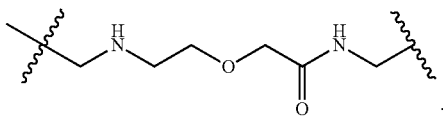 [SMILES: *CNCCOCC(=O)NC*]
In some embodiments, L is
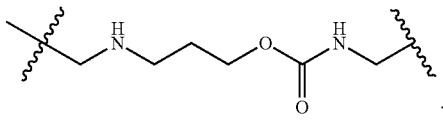 [SMILES: *CNCCCOC(=O)NC*]
In some embodiments, L is
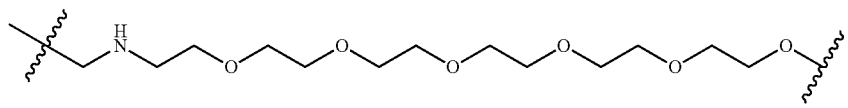 [SMILES: *CNCCOCCOCCOCCOCCOCCO*]
In some embodiments, L is
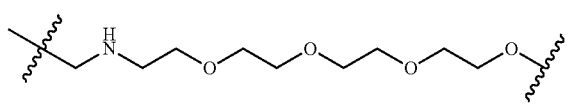
In some embodiments, L is
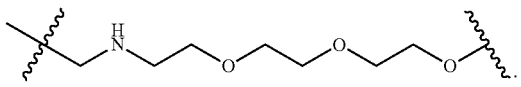 [SMILES: *CNCCOCCOCCO*]
In some embodiments, L is
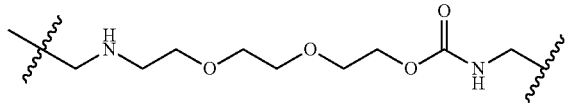
In some embodiments, L is
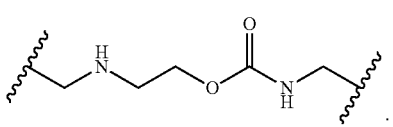 [SMILES: *CNCCOC(=O)NC*]

In some embodiments, L is
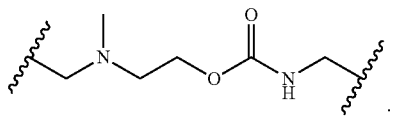 [SMILES: *CNC(=O)OCCN(C)C*]
In some embodiments, L is
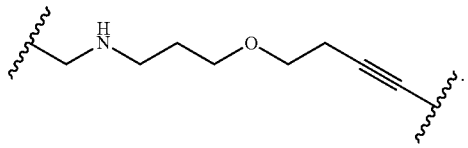 [SMILES: *C#CCCOCCCNC*]
In some embodiments, L is
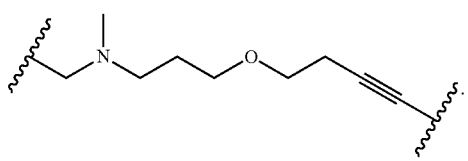 [SMILES: *C#CCCOCCCN(C)C*]
In some embodiments, L is
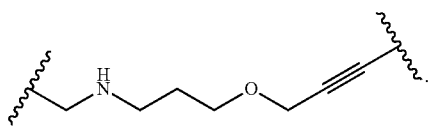 [SMILES: *C#CCOCCCNC*]
In some embodiments, L is
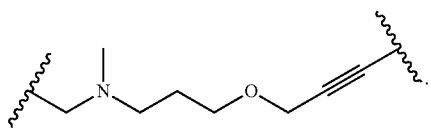 [SMILES: *C#CCOCCCN(C)C*]
In some embodiments, L is
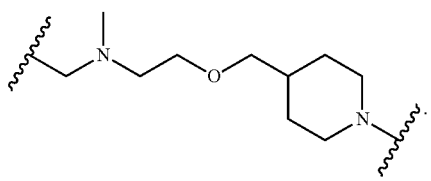 [SMILES: *CN(C)CCOCC1CCN(*)CC1]
In some embodiments, L is
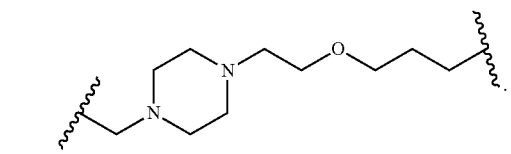 [SMILES: *CCCOCCN1CCN(C*)CC1]
In some embodiments, L is
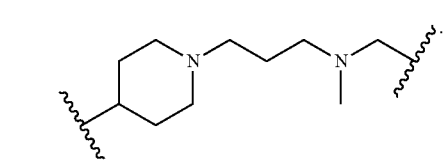 [SMILES: *CN(C)CCCN1CCC(*)CC1]
In some embodiments, L is
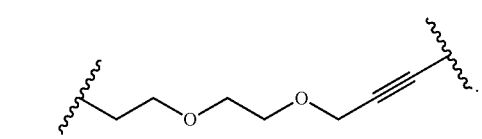 [SMILES: *C#CCOCCOCC*]
In some embodiments, L is
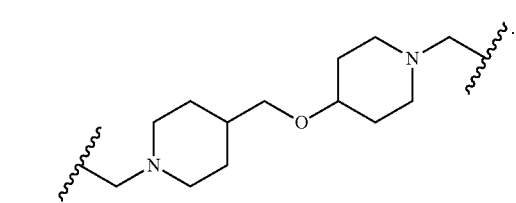 [SMILES: *CN1CCC(COC2CCN(C*)CC2)CC1]
In some embodiments, L is
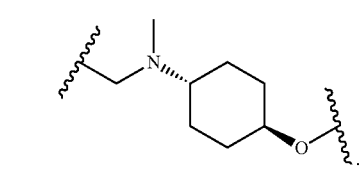 [SMILES: *CN(C)[C@H]1CC[C@H](O*)CC1]
In some embodiments, L is
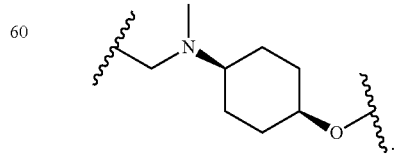

In some embodiments, L is
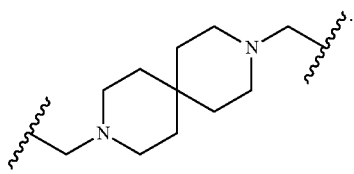 [SMILES: *CN1CCC2(CC1)CCN(C*)CC2]
In some embodiments, L is
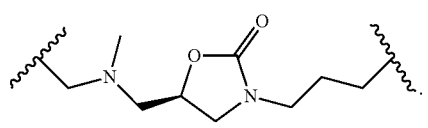 [SMILES: *CCCN1C[C@@H](CN(C)C*)OC1=O]
In some embodiments, L is
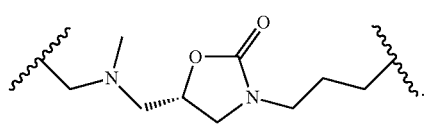 [SMILES: *CCCN1C[C@H](CN(C)C*)OC1=O]
In some embodiments, L is
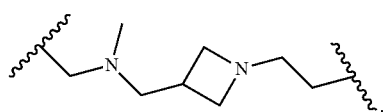 [SMILES: *CCN1CC(CN(C)C*)C1]
In some embodiments, L is
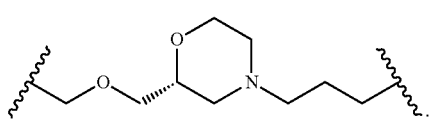 [SMILES: *CCCN1CCO[C@@H](COC*)C1]
In some embodiments, L is
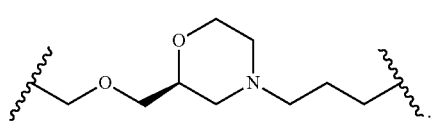 [SMILES: *CCCN1CCO[C@H](COC*)C1]
In some embodiments, L is
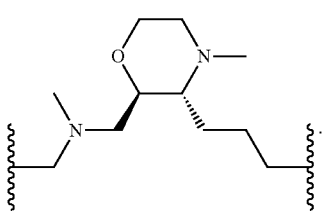 [SMILES: *CCC[C@@H]1[C@@H](CN(C)C*)OCCN1C]
In some embodiments, L is
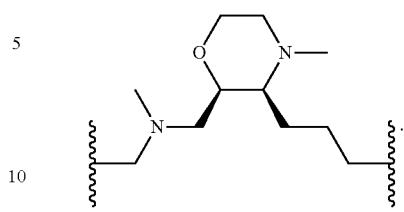
In some embodiments, L is
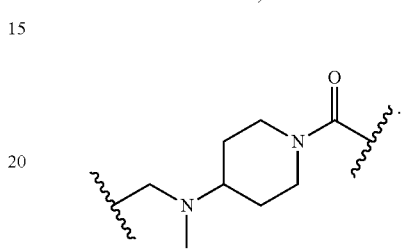
In some embodiments, L is
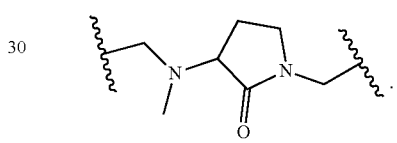
In some embodiments, L is
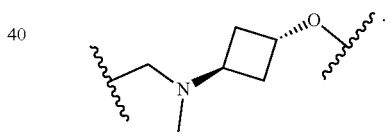
In some embodiments, L is
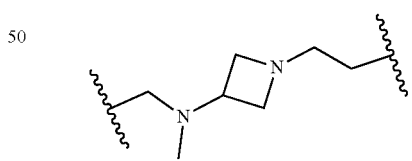
In some embodiments, L is
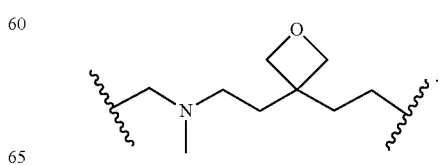

In some embodiments, L is

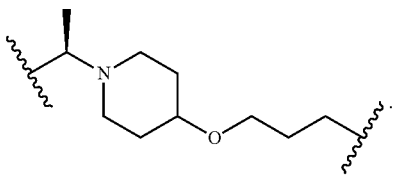 [SMILES: *CCCOC1CCN([C@@H](*)C)CC1]

In some embodiments, L is

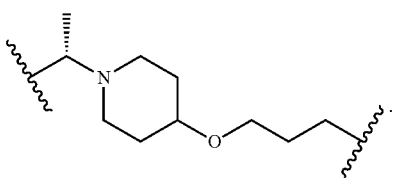 [SMILES: *CCCOC1CCN([C@H](*)C)CC1]

In some embodiments, L is

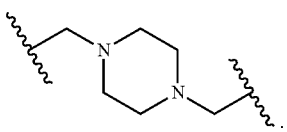 [SMILES: *CN1CCN(C*)CC1]

In some embodiments, L is

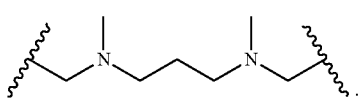 [SMILES: *CN(C)CCCN(C)C*]

In some embodiments, L is

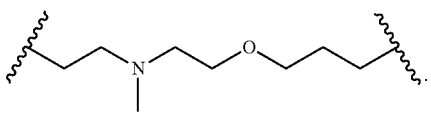 [SMILES: *CCCOCCN(C)CC*]

In some embodiments, L is

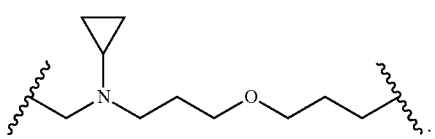 [SMILES: *CCCOCCCN(C*)C1CC1]

In some embodiments, L is

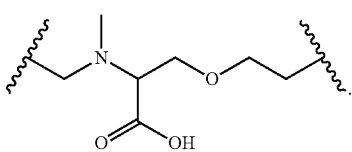 [SMILES: *CCOCC(C(=O)O)N(C)C*]

In some embodiments, L is

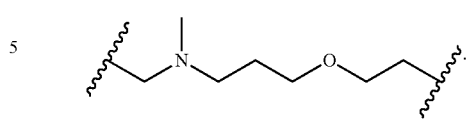

In some embodiments, L is

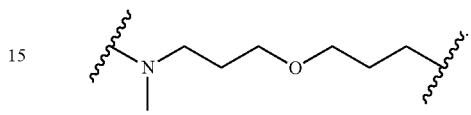

In some embodiments, L is

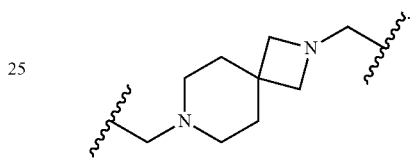

In some embodiments, L is

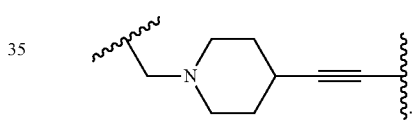

In some embodiments, L is

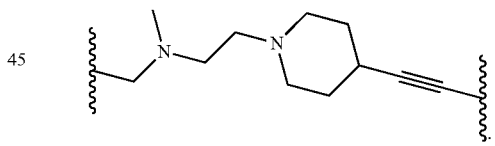

In some embodiments, L is

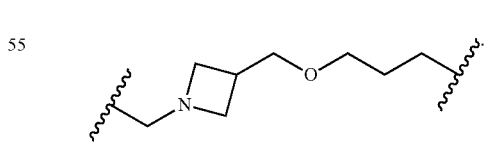

In some embodiments, L is selected from those depicted in Table 1, below.

As defined above and described herein, LBM is a ligase binding moiety.

In some embodiments, LBM is LBM is an E3 ubiquitin ligase (cereblon) binding moiety a DCAF15 E3 ubiquitin ligase binding moiety

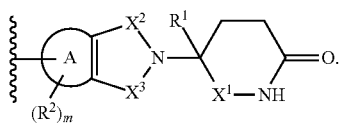

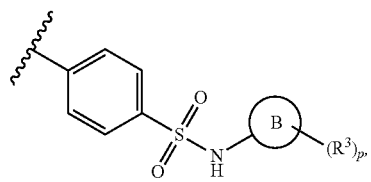

or a VHL E3 ubiquitin ligase binding moiety

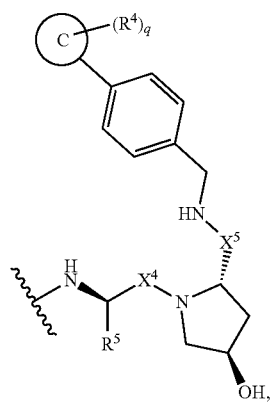

wherein each of $X^1$, $X^2$, and $X^3$ is independently a bivalent moiety selected from a covalent bond, —$CH_2$—, —C(O)—, —C(S)—, or

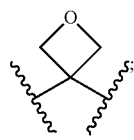 [SMILES: *C1(*)COC1]

each of $X^4$ and $X^5$ is independently a bivalent moiety selected from —$CH_2$—, —C(O)—, —C(S)—, or

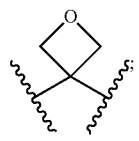 [SMILES: *C1(*)COC1]

$R^1$ is hydrogen, deuterium, halogen, —CN, —OR, —SR, —S(O)R, —S(O)$_2$R, —NR$_2$, or an optionally substituted $C_{1-4}$ aliphatic;

each of $R^2$, $R^3$, and $R^4$ is independently hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^5$ is hydrogen or $C_{1-6}$ aliphatic;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur;

Ring B is selected from 6-membered aryl containing 0-2 nitrogen atoms or a 8-10 membered bicyclic heteroaryl having 1-5 heteroatoms independently selected from nitrogen, oxygen, or sulfur;

Ring C is a selected from 6-membered aryl containing 0-2 nitrogen atoms or a 5-membered heteroaryl with 1-3 heteroatoms independently selected from nitrogen, oxygen or sulfur;

m is 0, 1, 2, 3 or 4;

each of n is independently 1, 2, 3, 4, 5, 6, 7, 8, 9, or 10;

p is 0, 1, 2, 3 or 4;

q is 0, 1, 2, 3 or 4; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, LBM is

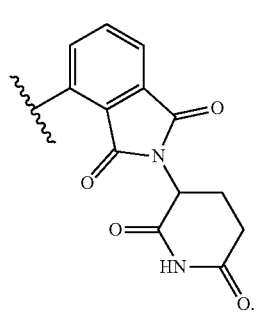

In some embodiments, LBM is
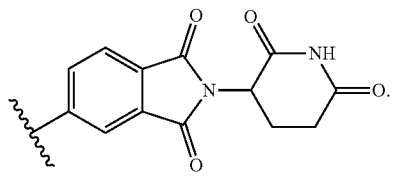 [SMILES: *c1ccc2c(c1)C(=O)N(C1CCC(=O)NC1=O)C2=O]
In some embodiments, LBM is
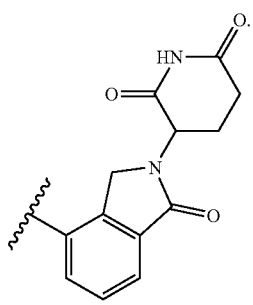 [SMILES: *c1cccc2c1CN(C1CCC(=O)NC1=O)C2=O]
In some embodiments, LBM is
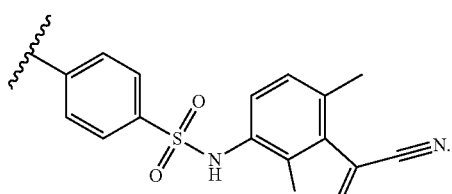
In some embodiments, LBM is
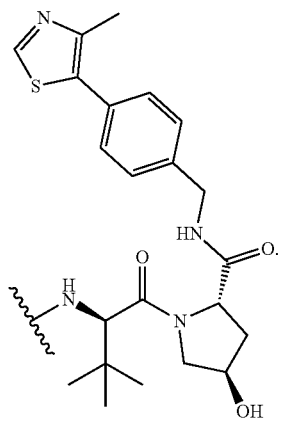 [SMILES: *N[C@@H](C(=O)N1C[C@H](O)C[C@H]1C(=O)NCc1ccc(-c2scnc2C)cc1)C(C)(C)C]
In some embodiments, LBM is
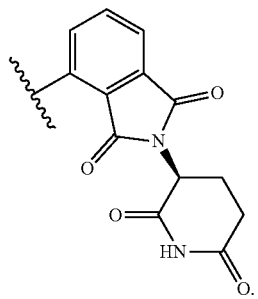 [SMILES: *c1cccc2c1C(=O)N([C@H]1CCC(=O)NC1=O)C2=O]
In some embodiments, LBM is
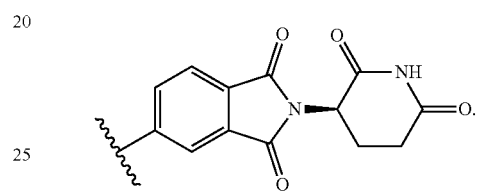
In some embodiments, LBM is
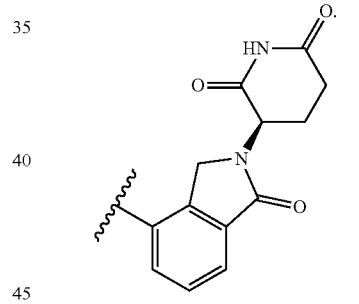
In some embodiments, LBM is
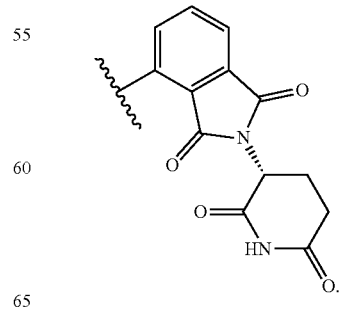

427
In some embodiments, LBM is
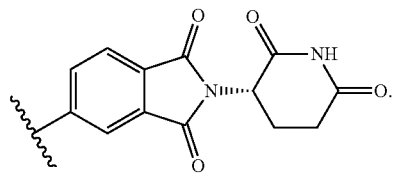 [SMILES: *c1ccc2c(c1)C(=O)N([C@H]1CCC(=O)NC1=O)C2=O]
In some embodiments, LBM is
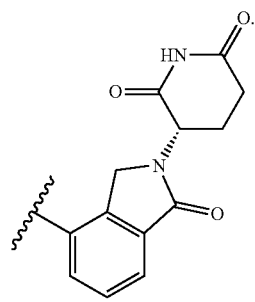 [SMILES: *c1cccc2c1CN([C@H]1CCC(=O)NC1=O)C2=O]
In some embodiments, LBM is
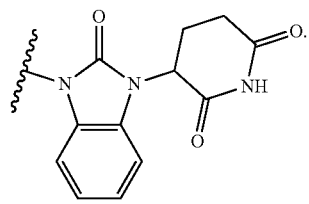 [SMILES: *n1c(=O)n(C2CCC(=O)NC2=O)c2ccccc21]
In some embodiments, LBM is
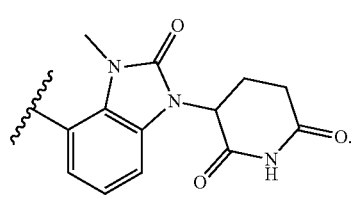 [SMILES: *c1cccc2c1n(C)c(=O)n2C1CCC(=O)NC1=O]
In some embodiments, LBM is
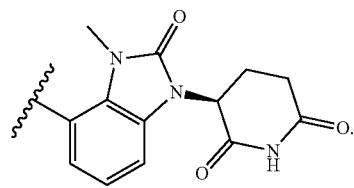 [SMILES: *c1cccc2c1n(C)c(=O)n2[C@H]1CCC(=O)NC1=O]
428
In some embodiments, LBM is
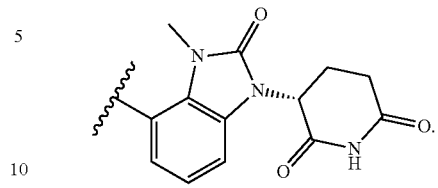
In some embodiments, LBM is
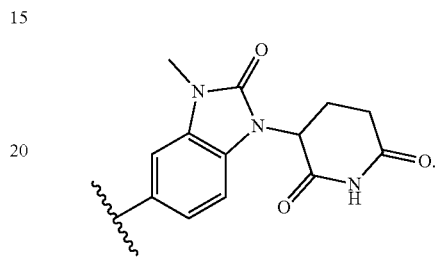
In some embodiments, LBM is
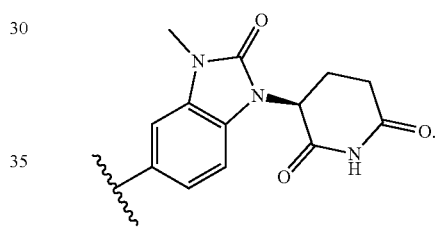
In some embodiments, LBM is
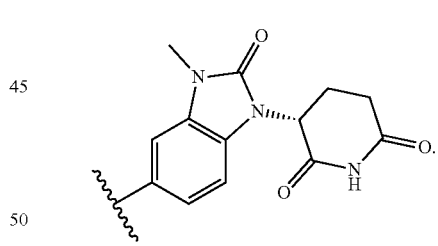
In some embodiments, LBM is
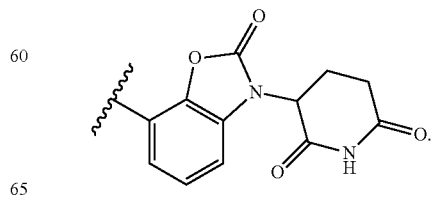

In some embodiments, LBM is
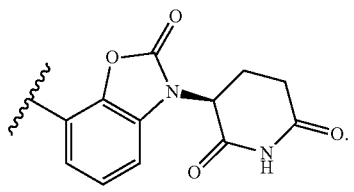 [SMILES: *c1cccc2c1oc(=O)n2[C@H]1CCC(=O)NC1=O]
In some embodiments, LBM is
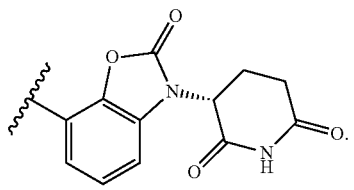 [SMILES: *c1cccc2c1oc(=O)n2[C@@H]1CCC(=O)NC1=O]
In some embodiments, LBM is
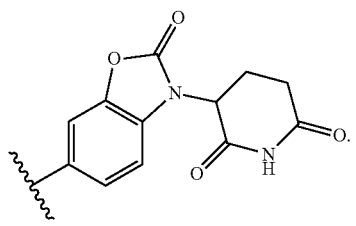 [SMILES: *c1ccc2c(c1)oc(=O)n2C1CCC(=O)NC1=O]
In some embodiments, LBM is
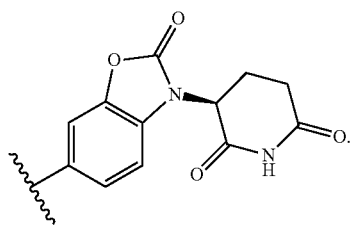 [SMILES: *c1ccc2c(c1)oc(=O)n2[C@H]1CCC(=O)NC1=O]
In some embodiments, LBM is
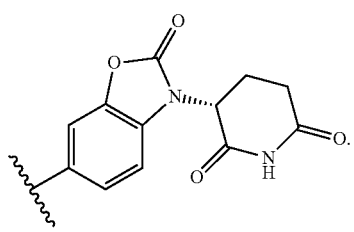 [SMILES: *c1ccc2c(c1)oc(=O)n2[C@@H]1CCC(=O)NC1=O]
In some embodiments, LBM is
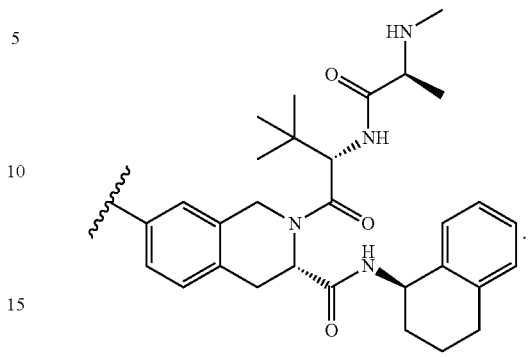
In some embodiments, LBM is
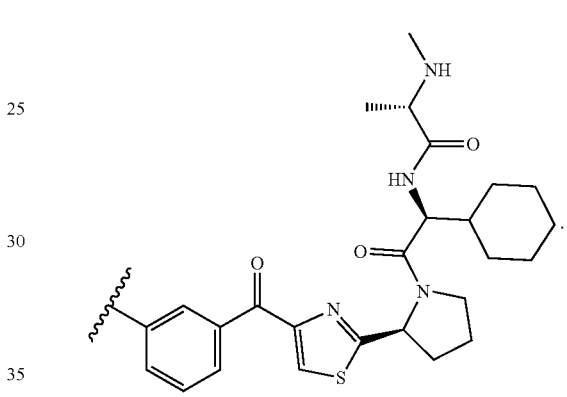
In some embodiments, LBM is
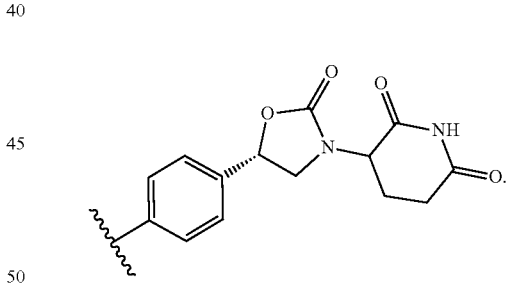
In some embodiments, LBM is
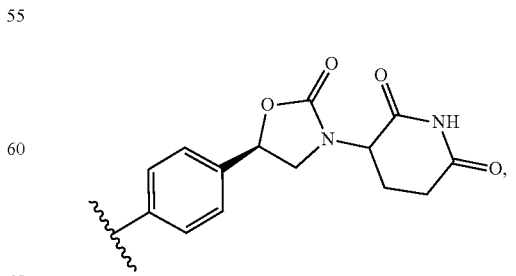

In some embodiments, LBM is

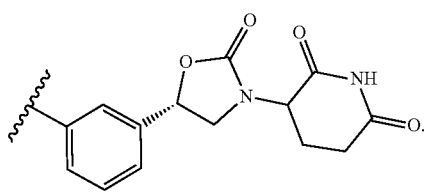 [SMILES: *c1cccc([C@H]2CN(C3CCC(=O)NC3=O)C(=O)O2)c1]

In some embodiments, LBM is

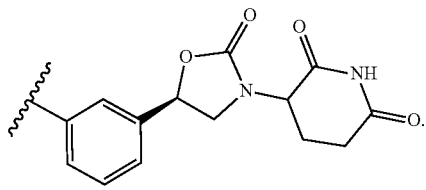 [SMILES: *c1cccc([C@@H]2CN(C3CCC(=O)NC3=O)C(=O)O2)c1]

In some embodiments, LBM is a E3 Ubiquitin ligase (cereblon) binding moiety recited in Varfolomeev, E. et al., *IAP Antagonists Induce Autoubiquitination of c-IAPs, NF-κB activation, and TNFα-Dependent Apoptosis*, Cell, 2007, 131 (4): 669-81, such as, for example:

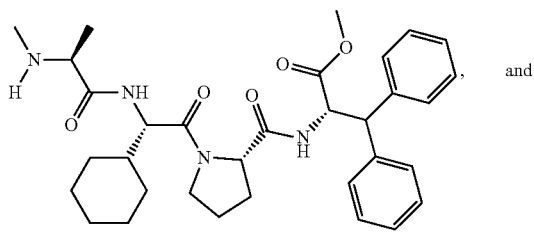

MV1 wherein

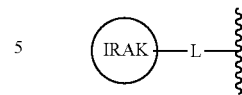

is attached to a modifiable carbon, oxygen, nitrogen or sulfur atom.

In some embodiments, LBM is selected from those depicted in Table 1, below.

As defined above and described herein, each of $X^1$, $X^2$, and $X^3$ is independently a bivalent moiety selected from a covalent bond, —CH$_2$—, —C(O)—, —C(S)—, or

In some embodiments, $X^1$ is a covalent bond, —CH$_2$—, —C(O)—, —C(S)—, or

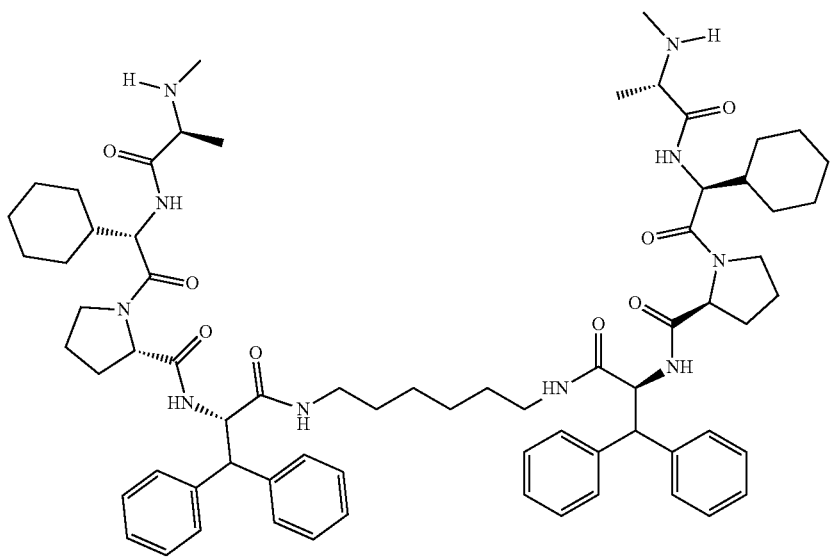

BV6

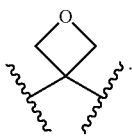 [SMILES: *C1(*)COC1]

In some embodiments, $X^1$ is selected from those depicted in Table 1, below.

In some embodiments, $X^2$ is a covalent bond, —CH$_2$—, —C(O)—, —C(S)—, or

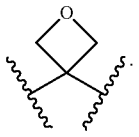 [SMILES: *C1(*)COC1]

In some embodiments, $X^2$ is selected from those depicted in Table 1, below.

In some embodiments, $X^3$ is a covalent bond, —CH$_2$—, —C(O)—, —C(S)—, or

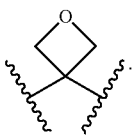

In some embodiments, $X^3$ is selected from those depicted in Table 1, below.

As defined above and described herein, each of $X^4$ and $X^5$ is independently a bivalent moiety selected from —CH$_2$—, —C(O)—, —C(S)—, or

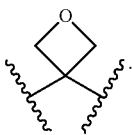 [SMILES: *C1(*)COC1]

In some embodiments, $X^4$ is —CH$_2$—, —C(O)—, —C(S)—, or

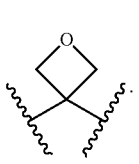

In some embodiments, $X^4$ is selected from those depicted in Table 1, below.

In some embodiments, $X^5$ is —CH$_2$—, —C(O)—, —C(S)—, or

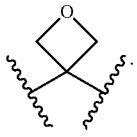

In some embodiments, $X^5$ is selected from those depicted in Table 1, below.

As defined above and described herein, $R^1$ is hydrogen, deuterium, halogen, —CN, —OR, —SR, —S(O)R, —S(O)$_2$R, —NR$_2$, or an optionally substituted C$_{1-4}$ aliphatic.

In some embodiments, $R^1$ is hydrogen, deuterium, halogen, —CN, —OR, —SR, —S(O)R, —S(O)$_2$R, —NR$_2$, or an optionally substituted C$_{1-4}$ aliphatic.

In some embodiments, $R^1$ is selected from those depicted in Table 1, below.

As defined above and described herein, each of $R^2$, $R^3$, and $R^4$ is independently hydrogen, —R$^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R.

In some embodiments, $R^2$ is hydrogen, —R$^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R.

In some embodiments, $R^2$ is selected from those depicted in Table 1, below.

In some embodiments, $R^3$ is hydrogen, —R$^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R.

In some embodiments, $R^3$ is methyl.

In some embodiments, $R^3$ is selected from those depicted in Table 1, below.

In some embodiments, $R^4$ is hydrogen, —R$^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R.

In some embodiments, $R^4$ is methyl.

In some embodiments, $R^4$ is selected from those depicted in Table 1, below.

As defined above and described herein, $R^5$ is hydrogen or C$_{1-6}$ aliphatic.

In some embodiments, $R^5$ is t-butyl.

In some embodiments, $R^5$ is selected from those depicted in Table 1, below.

As defined above and described herein, each $R^6$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, $R^6$ is an optionally substituted C$_{1-6}$ aliphatic group. In some embodiments, $R^6$ is an optionally substituted phenyl. In some embodiments, $R^6$ is an optionally substituted 4-7 membered saturated or partially unsaturated heterocyclic ring having 1-2 heteroatoms independently selected from nitrogen, oxygen, and sulfur. In some embodiments, $R^6$ is an optionally substituted 5-6 membered heteroaryl ring having 1-4 heteroatoms independently selected from nitrogen, oxygen, and sulfur.

In some embodiments, $R^6$ is selected from those depicted in Table 1, below.

As defined above and described herein, Ring A is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur.

In some embodiments Ring A is a fused 6-membered aryl containing 0-2 nitrogen atoms. In some embodiments Ring A is a fused 5 to 7-membered partially saturated carbocyclyl. In some embodiments Ring A is a fused 5 to 7-membered partially saturated heterocyclyl with 1-2 heteroatoms independently selected from nitrogen, oxygen or sulfur. In some embodiments Ring A is a fused 5-membered heteroaryl with 1-3 heteroatoms independently selected from nitrogen, oxygen or sulfur.

In some embodiments, Ring A is a fused phenyl.

In some embodiments, Ring A is selected from those depicted in Table 1, below.

As defined above and described herein, Ring B is selected from 6-membered aryl containing 0-2 nitrogen atoms or a 8-10 membered bicyclic heteroaryl having 1-5 heteroatoms independently selected from nitrogen, oxygen, or sulfur.

In some embodiments, Ring B is a 6-membered aryl containing 0-2 nitrogen atoms. In some embodiments, Ring B is a 8-10 membered bicyclic heteroaryl having 1-5 heteroatoms independently selected from nitrogen, oxygen, or sulfur.

In some embodiments, Ring B is

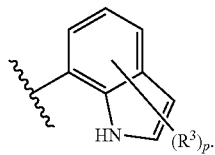

In some embodiments, Ring B is selected from those depicted in Table 1, below.

As defined above and described herein, Ring C is selected from 6-membered aryl containing 0-2 nitrogen atoms or a 5-membered heteroaryl with 1-3 heteroatoms independently selected from nitrogen, oxygen or sulfur.

In some embodiments, Ring C is a 6-membered aryl containing 0-2 nitrogen atoms. In some embodiments, Ring C is a 5-membered heteroaryl with 1-3 heteroatoms independently selected from nitrogen, oxygen or sulfur.

In some embodiments, Ring C is

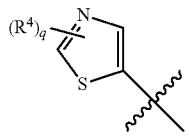

In some embodiments, Ring C is selected from those depicted in Table 1, below.

As defined above and described herein, m is 0, 1, 2, 3 or 4.

In some embodiments, m is 0. In some embodiments, m is 1. In some embodiments, m is 2. In some embodiments, m is 3. In some embodiments, m is 4.

In some embodiments, m is selected from those depicted in Table 1, below.

As defined above and described herein, each of n is independently 1, 2, 3, 4, 5, 6, 7, 8, 9, or 10.

In some embodiments, n is 0. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10.

In some embodiments, n is selected from those depicted in Table 1, below.

As defined above and described herein, p is 0, 1, 2, 3 or 4.

In some embodiments, p is 0. In some embodiments, p is 1. In some embodiments, p is 2. In some embodiments, p is 3. In some embodiments, p is 4.

In some embodiments, p is selected from those depicted in Table 1, below.

As defined above and described herein, q is 0, 1, 2, 3 or 4.

In some embodiments, q is 0. In some embodiments, q is 1. In some embodiments, q is 2. In some embodiments, q is 3. In some embodiments, q is 4.

In some embodiments, q is selected from those depicted in Table 1, below.

As defined above and described herein, each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or: two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is hydrogen. In some embodiments, R is phenyl. In some embodiments, R is a 4-7 membered saturated or partially unsaturated heterocyclic having 1-2 heteroatoms independently selected from nitrogen, oxygen, and sulfur. In some embodiments, R is a 5-6 membered heteroaryl ring having 1-4 heteroatoms independently selected from nitrogen, oxygen, and sulfur. In some embodiments, two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is selected from those depicted in Table 1, below.

As described above, in certain embodiments, the present invention provides a compound of formula I-zzz:

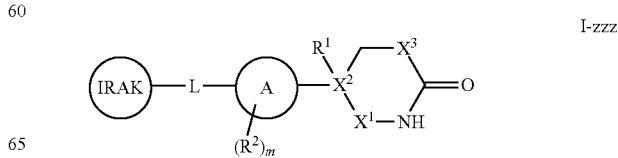

I-zzz or a pharmaceutically acceptable salt thereof, wherein:

$X^1$ is a bivalent moiety selected from a covalent bond, —CH$_2$—, —C(O)—, —C(S)—, or

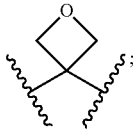 [SMILES: *C1(*)COC1]

$X^2$ is a carbon atom or silicon atom;

$X^3$ is a bivalent moiety selected from —CH$_2$— or —Si(R$_2$)—;

$R^1$ is hydrogen, deuterium, halogen, —CN, —OR, —SR, —S(O)R, —S(O)$_2$R, —N(R)$_2$, —Si(R)$_3$, or an optionally substituted C$_{1-4}$ aliphatic;

each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, —R$^3$, halogen, —CN, —NO$_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —N(R)C(O)OR, —N(R)C(O)R, —N(R)C(O)N(R)$_2$, or —N(R)S(O)$_2$R;

each $R^3$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

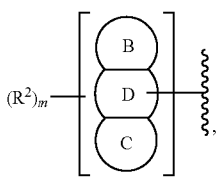

wherein each of Ring B, Ring C, and Ring D is independently a fused ring selected from 6-membered aryl containing 0-3 nitrogens, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-3 heteroatoms independently selected from nitrogen, oxygen or sulfur; and m is 0, 1, 2, 3, 4, 5, 6, 7, 8, 9, 10, 11, 12, 13, 14, 15, or 16; wherein L and IRAK are as described in embodiments herein.

In some embodiments, a compound of formula I-zzz above is provided as a compound of formula I-zzz' or formula I-zzz":

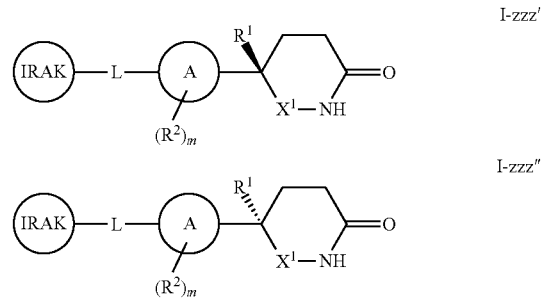

or a pharmaceutically acceptable salt thereof, wherein:
each of IRAK, Ring A, L, R$^1$, R$^2$, X$^1$, and m is as defined above.

As described above, in certain embodiments, the present invention provides a compound of formula I-aaaa:

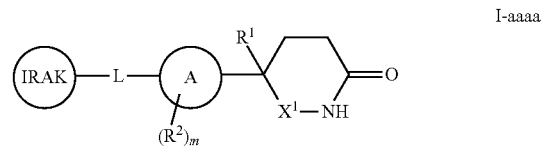

or a pharmaceutically acceptable salt thereof, wherein:

$X^1$ is a bivalent moiety selected from a covalent bond, —CH$_2$—, —C(O)—, —C(S)—, or

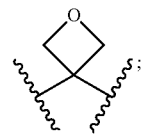 [SMILES: *C1(*)COC1]

$R^1$ is hydrogen, deuterium, halogen, —CN, —OR, —SR, —S(O)R, —S(O)$_2$R, —N(R)$_2$, —Si(R)$_3$, or an optionally substituted C$_{1-4}$ aliphatic;

each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, —R$^3$, halogen, —CN, —NO$_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —N(R)C(O)OR, —N(R)C(O)R, —N(R)C(O)N(R)$_2$, or —N(R)S(O)$_2$R;

each R³ is independently an optionally substituted group selected from C₁₋₆ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

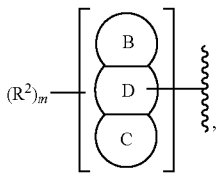

wherein each of Ring B, Ring C, and Ring D is independently a fused ring selected from 6-membered aryl containing 0-3 nitrogens, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-3 heteroatoms independently selected from nitrogen, oxygen or sulfur; and m is 0, 1, 2, 3, 4, 5, 6, 7, 8, 9, 10, 11, 12, 13, 14, 15, or 16;

wherein L and IRAK are as described in embodiments herein.

In some embodiments, a compound of formula I-aaaa above is provided as a compound of formula I-aaaa' or formula I-aaaa":

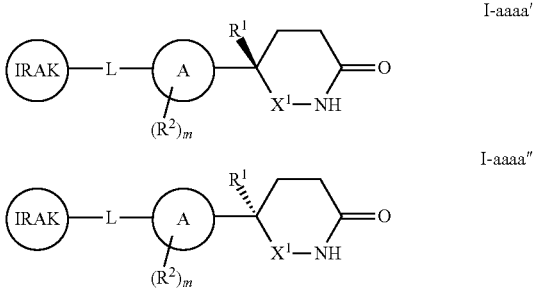

or a pharmaceutically acceptable salt thereof, wherein:
each of IRAK, Ring A, L, R¹, R², X¹, and m is as defined above.

As described above, in certain embodiments, the present invention provides a compound of formula I-bbbb:

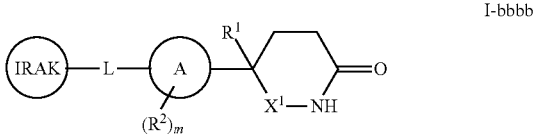

or a pharmaceutically acceptable salt thereof, wherein:
X¹ is a bivalent moiety selected from a covalent bond, —CH₂—, —C(O)—, —C(S)—, or

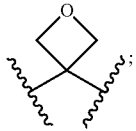

R¹ is hydrogen, deuterium, halogen, —CN, —OR, —SR, —S(O)R, —S(O)₂R, —N(R)₂, —Si(R)₃, or an optionally substituted C₁₋₄ aliphatic;

each R is independently hydrogen, or an optionally substituted group selected from C₁₋₆ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each R² is independently hydrogen, —R³, halogen, —CN, —NO₂, —OR, —SR, —N(R)₂, —Si(R)₃, —S(O)₂R, —S(O)₂N(R)₂, —S(O)R, —C(O)R, —C(O)OR, —C(O)N(R)₂, —C(O)N(R)OR, —C(R)₂N(R)C(O)R, —C(R)₂N(R)C(O)N(R)₂, —OC(O)R, —OC(O)N(R)₂, —N(R)C(O)OR, —N(R)C(O)R, —N(R)C(O)N(R)₂, or —N(R)S(O)₂R;

each R³ is independently an optionally substituted group selected from C₁₋₆ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

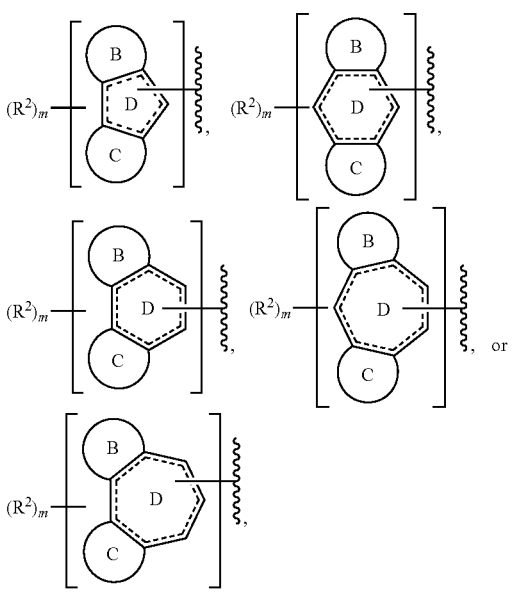

wherein each of Ring B and Ring C is independently a fused ring selected from 6-membered aryl containing 0-3 nitrogens, 5 to 7-membered saturated or partially unsaturated carbocyclyl, 5 to 7-membered saturated or partially unsaturated heterocyclyl ring with 1-3 heteroatoms independently selected from boron, nitrogen, oxygen or sulfur, or 5-membered heteroaryl with 1-3 heteroatoms independently selected from nitrogen, oxygen or sulfur;

Ring D is a fused ring selected from aryl containing 0-3 nitrogens, saturated or partially unsaturated carbocyclyl, saturated or partially unsaturated heterocyclyl ring with 1-2 heteroatoms independently selected from nitrogen, oxygen, silicon, or sulfur, or heteroaryl with 1-3 heteroatoms independently selected from nitrogen, oxygen or sulfur;

=== is a single or double bond;

m is 0, 1, 2, 3, 4, 5, 6, 7, 8, 9, 10, 11, 12, 13, 14, 15, or 16; wherein L and IRAK are as described in embodiments herein.

In some embodiments, a compound of formula I-bbbb above is provided as a compound of formula I-bbbb' or formula I-bbbb":

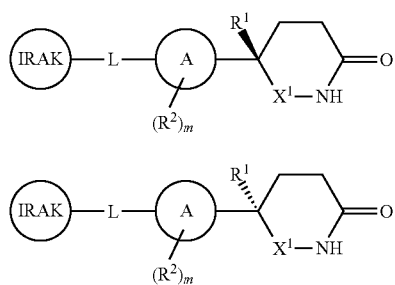

or a pharmaceutically acceptable salt thereof, wherein: each of IRAK, Ring A, L, $R^1$, $R^2$, $X^1$, and m is as defined above.

As described above, in certain embodiments, the present invention provides a compound of formula I-cccc:

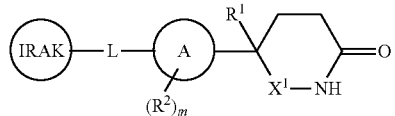

or a pharmaceutically acceptable salt thereof, wherein:

$X^1$ is a bivalent moiety selected from a covalent bond, —$CH_2$—, —C(O)—, —C(S)—, or

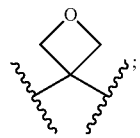 [SMILES: *C1(*)COC1];

$R^1$ is hydrogen, deuterium, halogen, —CN, —OR, —SR, —S(O)R, —S(O)$_2$R, —N(R)$_2$, —Si(R)$_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, —$R^3$, halogen, —CN, —NO$_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —N(R)C(O)OR, —N(R)C(O)R, —N(R)C(O)N(R)$_2$, or —N(R)S(O)$_2$R;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

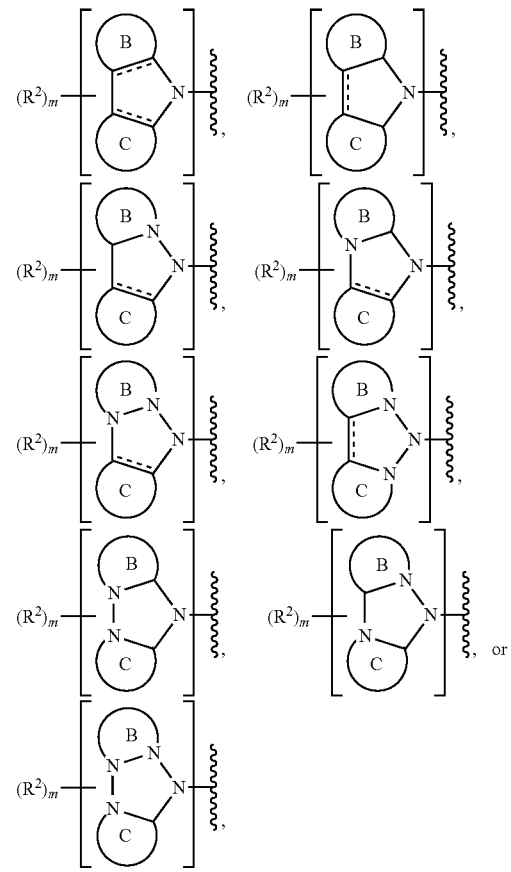

wherein each of Ring B and Ring C is independently a fused ring selected from 6-membered aryl containing 0-2 nitrogens, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-3 heteroatoms independently selected from nitrogen, oxygen or sulfur;

═ is a single or double bond;
m is 0, 1, 2, 3, 4, 5, 6, 7, or 8;
  wherein L and IRAK are as described in embodiments herein.

In some embodiments, a compound of formula I-cccc above is provided as a compound of formula I-cccc' or formula I-cccc":

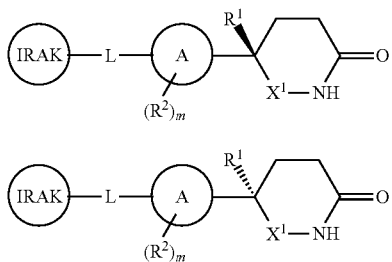

or a pharmaceutically acceptable salt thereof, wherein:
each of IRAK, Ring A, L, $R^1$, $R^2$, $X^1$, and m is as defined above.

As defined above and described herein, $X^1$ is a bivalent moiety selected from a covalent bond, —$CH_2$—, —C(O)—, —C(S)—, or

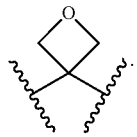 [SMILES: *C1(*)COC1]

In some embodiments, $X^1$ is a covalent bond. In some embodiments, $X^1$ is —$CH_2$—. In some embodiments, $X^1$ is —C(O)—. In some embodiments, $X^1$ is —C(S)—. In some embodiments, $X^1$ is

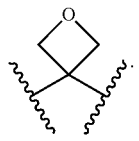 [SMILES: *C1(*)COC1]

In some embodiments, $X^1$ is selected from those depicted in Table 1, below.

As defined above and described herein, $X^2$ is a carbon atom or silicon atom.

In some embodiments, $X^2$ is a carbon atom. In some embodiments, $X^2$ is a silicon atom.

In some embodiments, $X^2$ is selected from those depicted in Table 1, below.

As defined above and described herein, $X^3$ is a bivalent moiety selected from —$CH_2$— or —Si($R_2$)—.

In some embodiments, $X^3$ is —$CH_2$—. In some embodiments, $X^2$ is —Si($R_2$)—.

In some embodiments, $X^3$ is selected from those depicted in Table 1, below.

As defined above and described herein, $R^1$ is hydrogen, deuterium, halogen, —CN, —OR, —SR, —S(O)R, —S(O)$_2$R, —NR$_2$, —Si($R_3$), or an optionally substituted $C_{1-4}$ aliphatic.

In some embodiments, $R^1$ is hydrogen. In some embodiments, $R^1$ is deuterium. In some embodiments, $R^1$ is halogen. In some embodiments, $R^1$ is —CN. In some embodiments, $R^1$ is —OR. In some embodiments, $R^1$ is —SR. In some embodiments, $R^1$ is —S(O)R. In some embodiments, $R^1$ is —S(O)$_2$R. In some embodiments, $R^1$ is —NR$_2$. In some embodiments, $R^1$ is —Si($R_3$). In some embodiments, $R^1$ is an optionally substituted $C_{1-4}$ aliphatic.

In some embodiments, $R^1$ is selected from those depicted in Table 1, below.

As defined above and described herein, each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or: two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is hydrogen. In some embodiments, R is optionally substituted $C_{1-6}$ aliphatic. In some embodiments, R is optionally substituted phenyl. In some embodiments, R is optionally substituted 4-7 membered saturated or partially unsaturated heterocyclic having 1-2 heteroatoms independently selected from nitrogen, oxygen, and sulfur. In some embodiments, R is optionally substituted 5-6 membered heteroaryl ring having 1-4 heteroatoms independently selected from nitrogen, oxygen, and sulfur. In some embodiments, two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is selected from those depicted in Table 1, below.

As defined above and described herein, each $R^2$ is independently hydrogen, —$R^3$, halogen, —CN, —NO$_2$, —OR, —SR, —N(R)$_2$, —Si($R_3$), —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —N(R)C(O)OR, —N(R)C(O)R, —N(R)C(O)N(R)$_2$, or —N(R)S(O)$_2$R.

In some embodiments, $R^2$ is hydrogen. In some embodiments, $R^2$ is —$R^3$. In some embodiments, $R^2$ is halogen. In some embodiments, $R^2$ is —CN. In some embodiments, $R^2$ is —NO$_2$. In some embodiments, $R^2$ is —OR. In some embodiments, $R^2$ is —SR. In some embodiments, $R^2$ is —NR$_2$. In some embodiments, $R^2$ is —Si($R_3$). In some embodiments, $R^2$ is —S(O)$_2$R. In some embodiments, $R^2$ is —S(O)$_2$NR$_2$. In some embodiments, $R^2$ is —S(O)R. In some embodiments, $R^2$ is —C(O)R. In some embodiments, $R^2$ is —C(O)OR. In some embodiments, $R^2$ is —C(O)NR$_2$. In some embodiments, $R^2$ is —C(O)N(R)OR. In some embodiments, $R^2$ is —C(R)$_2$N(R)C(O)R. In some embodiments, $R^2$ is —C(R)$_2$N(R)C(O)N(R)$_2$. In some embodiments, $R^2$ is —OC(O)R. In some embodiments, $R^2$ is —OC(O)NR$_2$. In some embodiments, $R^2$ is —N(R)C(O)OR. In some embodiments, $R^2$ is —N(R)C(O)R. In some embodiments, $R^2$ is —N(R)C(O)NR$_2$. In some embodiments, $R^2$ is —N(R)S(O)$_2$R.

In some embodiments, $R^2$ is selected from those depicted in Table 1, below.

As defined above and described herein, each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, $R^3$ is an optionally substituted $C_{1-6}$ aliphatic. In some embodiments, $R^3$ is an optionally substituted phenyl. In some embodiments, $R^3$ is an optionally substituted 4-7 membered saturated or partially unsaturated heterocyclic ring having 1-2 heteroatoms independently selected from nitrogen, oxygen, and sulfur. In some embodiments, $R^3$ is an optionally substituted 5-6 membered heteroaryl ring having 1-4 heteroatoms independently selected from nitrogen, oxygen, and sulfur.

In some embodiments, $R^3$ is selected from those depicted in Table 1, below.

As defined above and described herein, Ring A is a tricyclic ring selected from

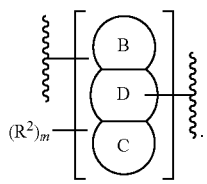

In some embodiments, Ring A is

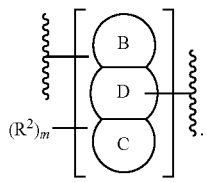

In some embodiments, Ring A is selected from those depicted in Table 1, below.

As defined above and described herein, each of Ring B, Ring C, and Ring D is independently a fused ring selected from 6-membered aryl containing 0-3 nitrogens, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-3 heteroatoms independently selected from nitrogen, oxygen or sulfur.

In some embodiments, each Ring B, Ring C, and Ring D is independently a 6-membered aryl containing 0-2 nitrogen atoms. In some embodiments, each Ring B, Ring C, and Ring D is independently a 5 to 7-membered saturated or partially unsaturated carbocyclyl. In some embodiments, each Ring B, Ring C, and Ring D is independently a 5 to 7-membered saturated or partially unsaturated heterocyclyl with 1-2 heteroatoms independently selected from boron, nitrogen, oxygen, silicon, or sulfur. In some embodiments, each Ring B, Ring C, and Ring D is independently a 5-membered heteroaryl with 1-3 heteroatoms independently selected from nitrogen, oxygen or sulfur.

In some embodiments, Ring B, Ring C, and Ring D is selected from those depicted in Table 1, below.

As defined above and described herein, Ring A is a tricyclic ring selected from

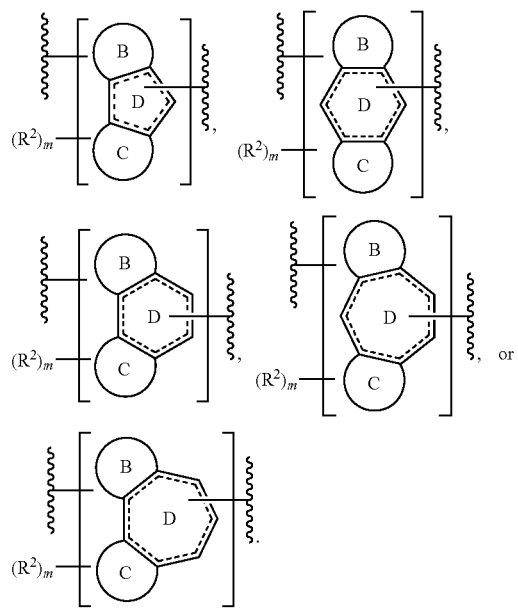

In some embodiments, Ring A is

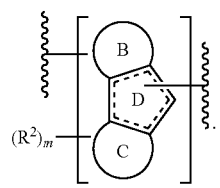

In some embodiments, Ring A is

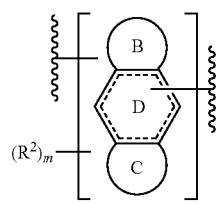

In some embodiment, Ring A is

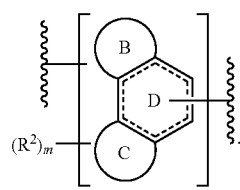

In some embodiments, Ring A is

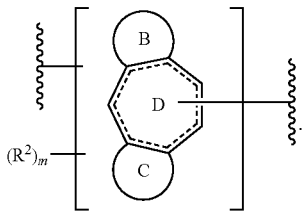

In some embodiments, Ring A is

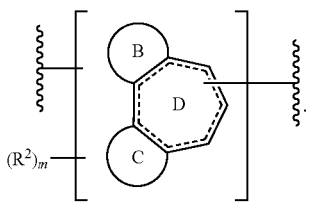

In some embodiments, Ring A is selected from those depicted in Table 1, below.

As defined above and described herein, Ring D is a fused ring selected from aryl containing 0-3 nitrogens, saturated or partially unsaturated carbocyclyl, saturated or partially unsaturated heterocyclyl ring with 1-2 heteroatoms independently selected from nitrogen, oxygen, silicon, or sulfur, or heteroaryl with 1-3 heteroatoms independently selected from nitrogen, oxygen or sulfur.

In some embodiments, Ring D is an aryl containing 0-2 nitrogen atoms. In some embodiments, Ring D is a saturated or partially unsaturated carbocyclyl. In some embodiments, each Ring D is a saturated or partially unsaturated heterocyclyl with 1-2 heteroatoms independently selected from nitrogen, oxygen, silicon, or sulfur. In some embodiments, Ring D is a heteroaryl with 1-3 heteroatoms independently selected from nitrogen, oxygen or sulfur.

In some embodiments, Ring D is

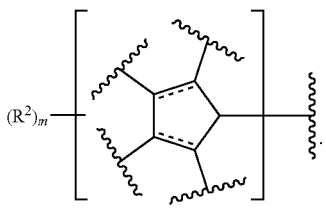

In some embodiments, Ring D is

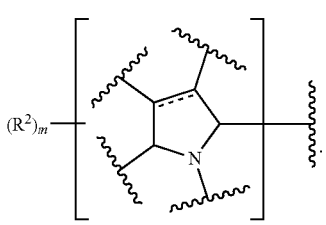

In some embodiments, Ring D is

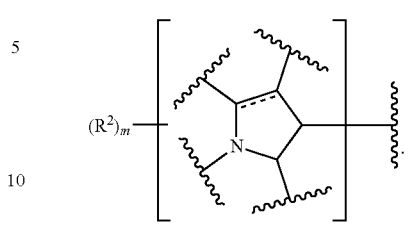

In some embodiments, Ring D is

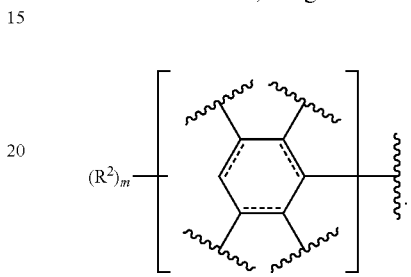

In some embodiments, Ring D is

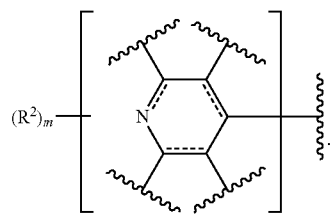

In some embodiments, Ring D is

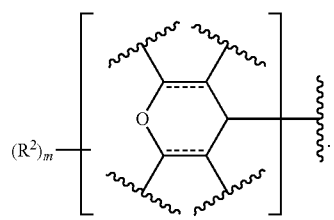

In some embodiments, Ring D is

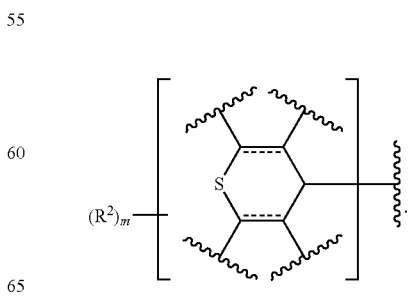

449
In some embodiments, Ring D is
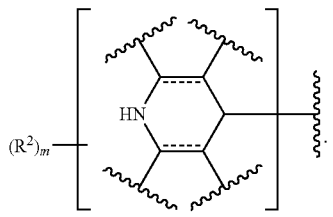
In some embodiments, Ring D is
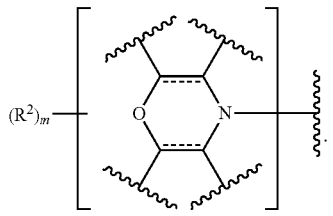
In some embodiments, Ring D is
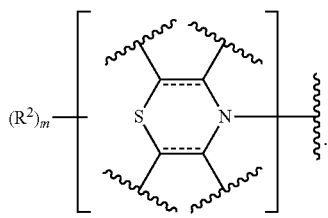
In some embodiments, Ring D is
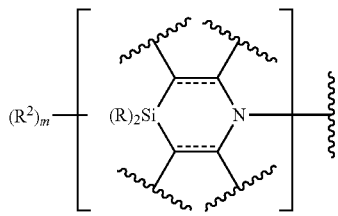
In some embodiments, Ring D is
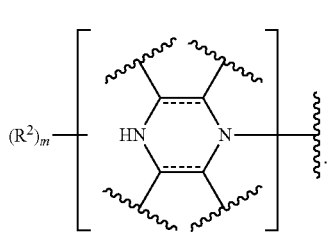
450
In some embodiments, Ring D is
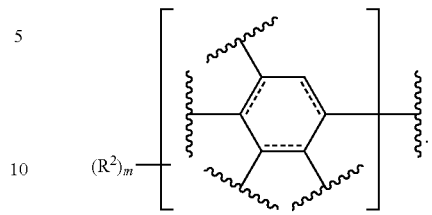
In some embodiments, Ring D is
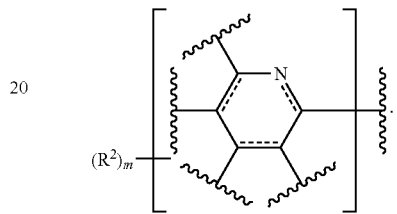
In some embodiments, Ring D is
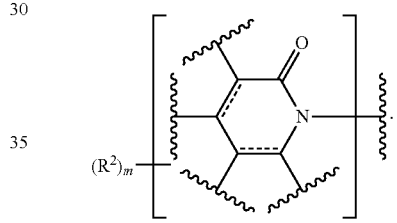
In some embodiments, Ring D is
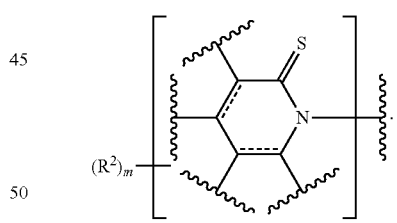
In some embodiments, Ring D is
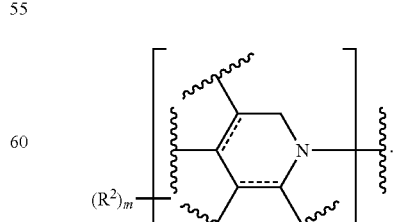

In some embodiments, Ring D is
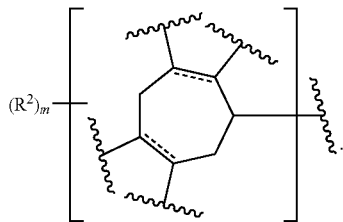
In some embodiments, Ring D is
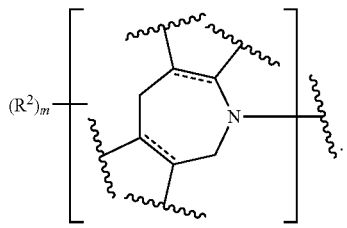
In some embodiments, Ring D is
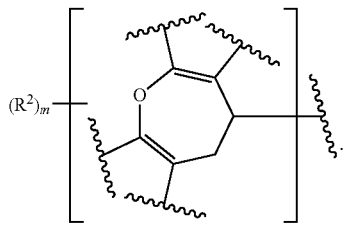
In some embodiments, Ring D is
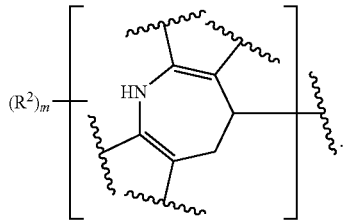
In some embodiments, Ring D is
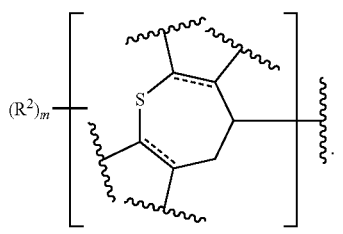
In some embodiments, Ring D is
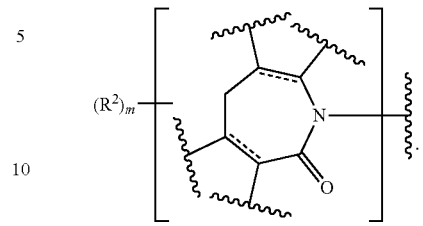
In some embodiments, Ring D is
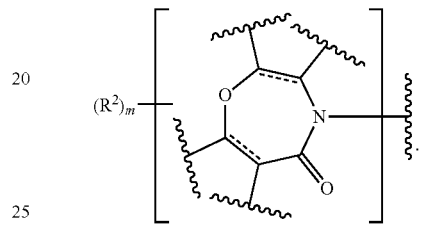
In some embodiments, Ring D is
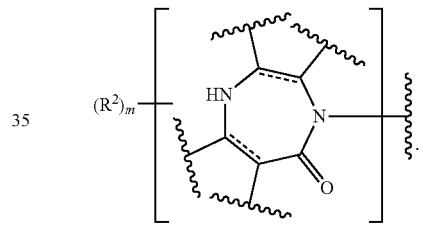
In some embodiments, Ring D is
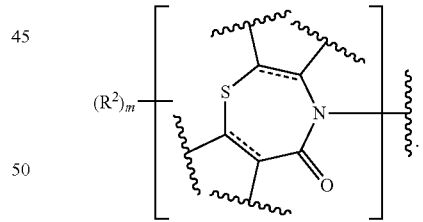
In some embodiments, Ring D is
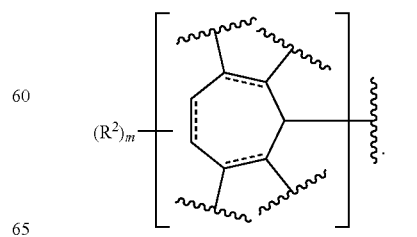

In some embodiments, Ring D is

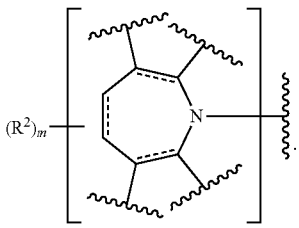

In some embodiments, Ring D is

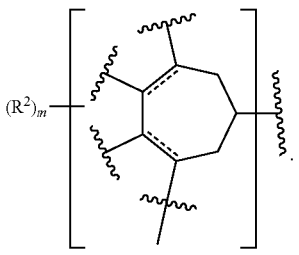

In some embodiments, Ring D is

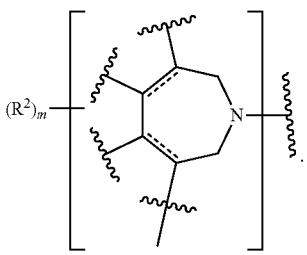

In some embodiments, Ring D is

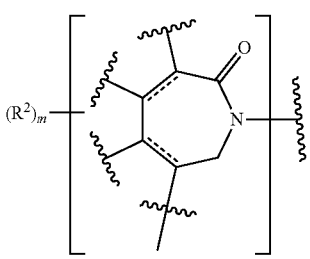

In some embodiments, Ring D is

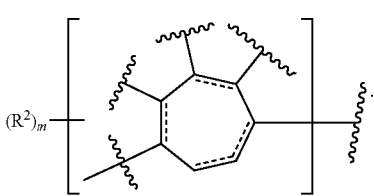

In some embodiments, Ring D is

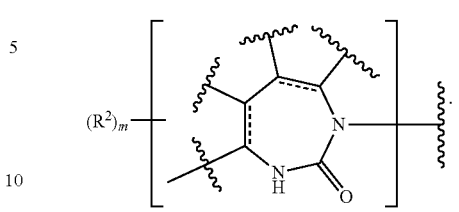

In some embodiments, Ring D is

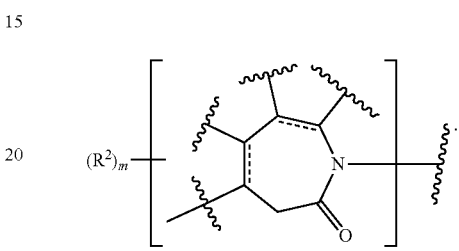

In some embodiments, Ring D is selected from those depicted in Table 1, below.

As defined above and described herein, m is 0, 1, 2, 3, 4, 5, 6, 7, 8, 9, 10, 11, 12, 13, 14, 15, or 16.

In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, m is 12. In some embodiments, m is 13. In some embodiments, m is 14. In some embodiments, m is 15. In some embodiments, m is 16.

In some embodiments, m is selected from those depicted in Table 1, below.

As defined above and described herein, Ring A is a tricyclic ring selected from

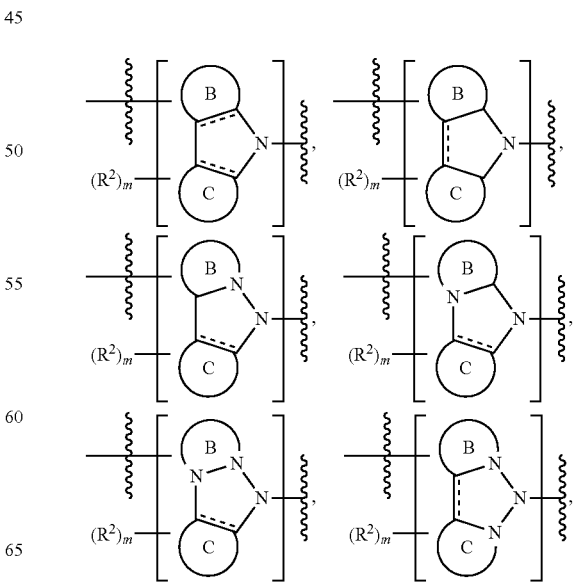

-continued

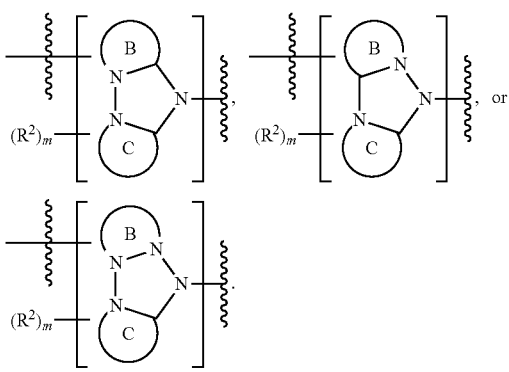

In some embodiments, Ring A is

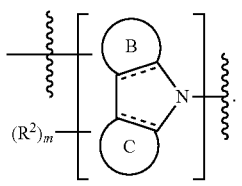

In some embodiments, Ring A is

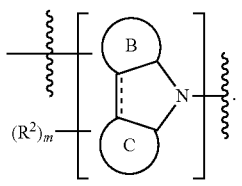

In some embodiment, Ring A is

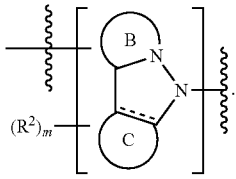

In some embodiments, Ring A is

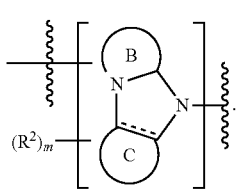

In some embodiments, Ring A is

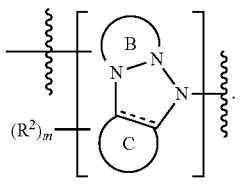

In some embodiments, Ring A is

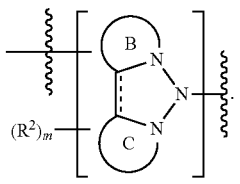

In some embodiments, Ring A is

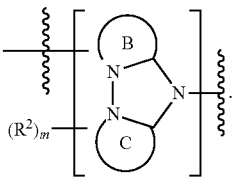

In some embodiments, Ring A is

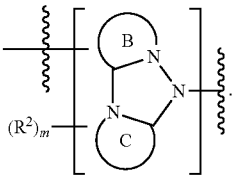

In some embodiments, Ring A is

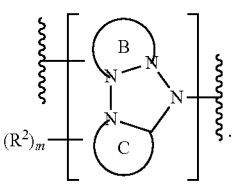

In some embodiments, Ring A is selected from those depicted in Table 1, below.

As defined above and described herein, each Ring B and Ring C is independently a fused ring selected from 6-membered aryl containing 0-2 nitrogen atoms, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-3 heteroatoms independently selected from nitrogen, oxygen or sulfur.

In some embodiments, each Ring B and Ring C is independently a 6-membered aryl containing 0-2 nitrogen atoms. In some embodiments, each Ring B and Ring C is independently a 5 to 7-membered saturated or partially unsaturated carbocyclyl. In some embodiments, each Ring B and Ring C is independently a 5 to 7-membered saturated or partially unsaturated heterocyclyl with 1-3 heteroatoms independently selected from boron, nitrogen, oxygen, silicon, or sulfur. In some embodiments, each Ring B and Ring C is independently a 5-membered heteroaryl with 1-3 heteroatoms independently selected from nitrogen, oxygen or sulfur.

In some embodiments, each Ring B and Ring C is independently

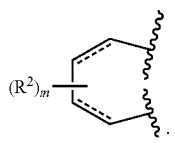

In some embodiments, each Ring B and Ring C is independently

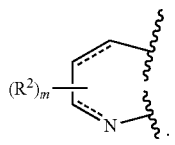

In some embodiments, each Ring B and Ring C is independently

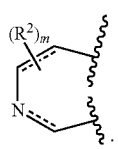

In some embodiments, each Ring B and Ring C is independently

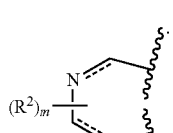

In some embodiments, Ring B and Ring C is independently

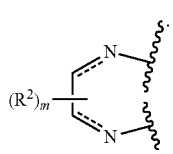

In some embodiments, Ring B and Ring C is independently is

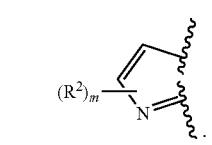

In some embodiments, Ring B and Ring C is independently

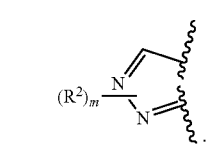

In some embodiments, Ring B and Ring C is independently

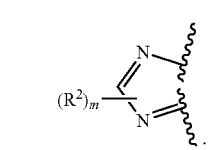

In some embodiments, Ring B and Ring C is independently

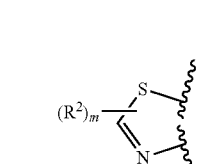

In some embodiments, Ring B and Ring C is independently

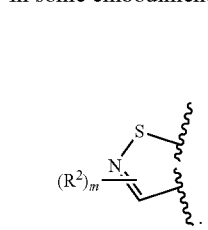

In some embodiments, Ring B and Ring C is independently

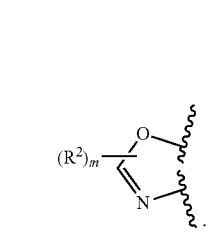

In some embodiments, Ring B and Ring C is independently

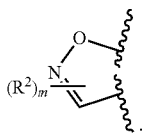

In some embodiments, Ring B and Ring C is independently

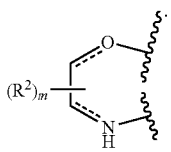

In some embodiments, Ring B and Ring C is independently

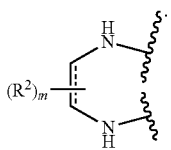

In some embodiments, B and Ring C is independently

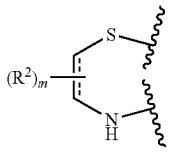

In some embodiments, Ring B and Ring C is independently

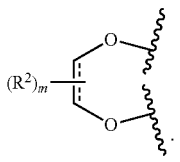

In some embodiments, Ring B and Ring C is independently

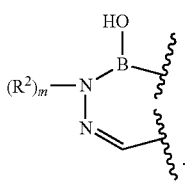

In some embodiments, Ring B and Ring C is independently selected from those depicted in Table 1, below.

As defined above and described herein, === is a single or double bond

In some embodiments, === is a single bond. In some embodiments, === is a double bond.

As defined above and described herein, m is 0, 1, 2, 3, 4, 5, 6, 7, or 8.

In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8.

In some embodiments, m is selected from those depicted in Table 1, below.

In some embodiments, In some embodiments, LBM is

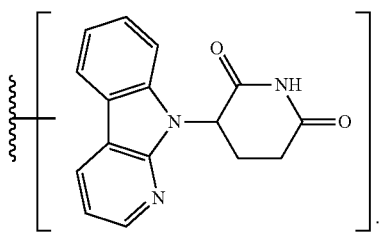

In some embodiments, LBM is

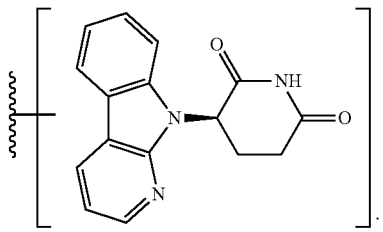

In some embodiments, LBM is

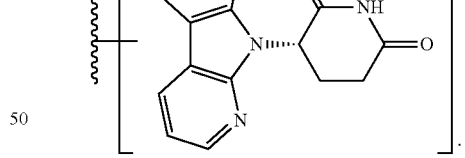

In some embodiments, In some embodiments, LBM is

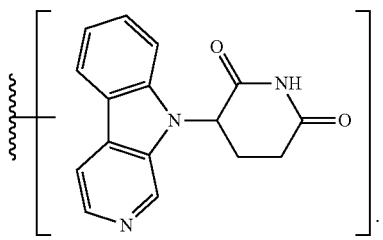

In some embodiments, LBM is

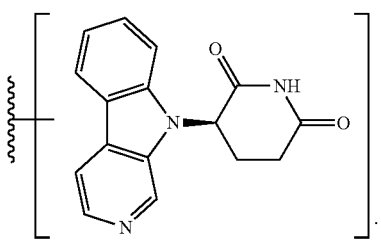

In some embodiments, LBM is

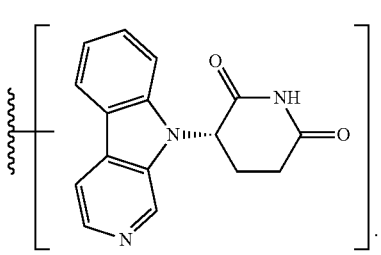

In some embodiments, LBM is

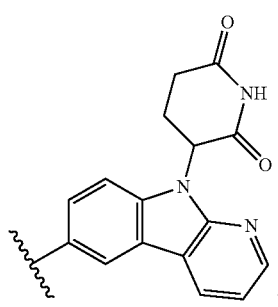

In some embodiments, LBM is

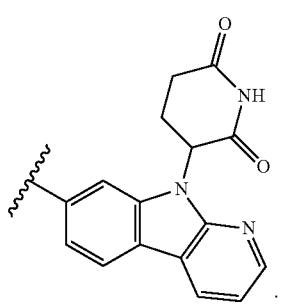 [SMILES: *c1ccc2c3cccnc3n(C3CCC(=O)NC3=O)c2c1]

In some embodiments, LBM is

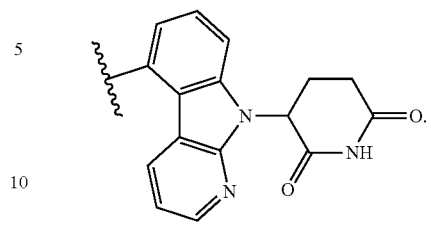

In some embodiments, LBM is

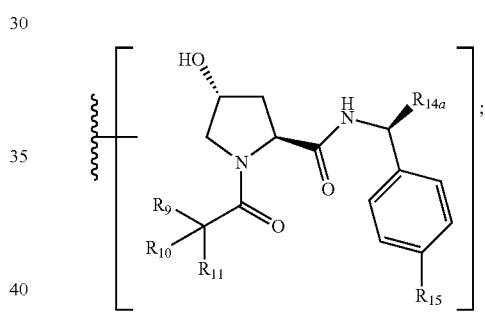

In certain embodiments, the present invention provides a compound of formula I, wherein LBM is a VHL binding moiety

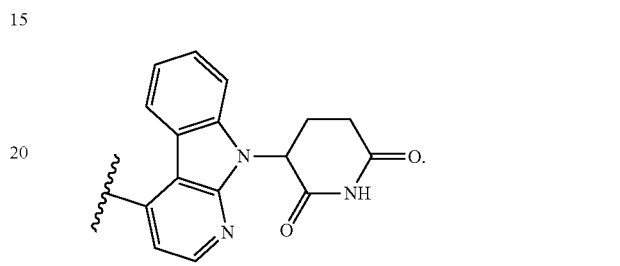

thereby forming a compound of formula I-dddd:

I-dddd

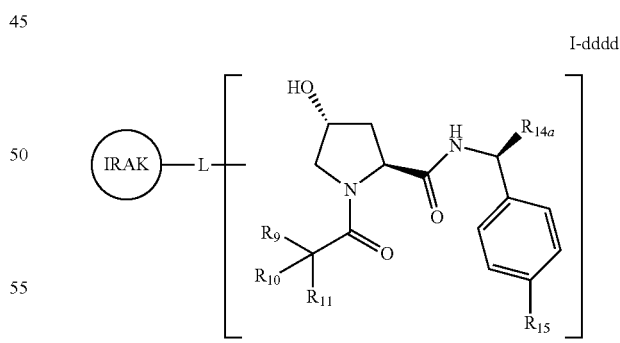

or a pharmaceutically acceptable salt thereof, wherein L and IRAK are as defined above and described in embodiments herein, and wherein each of the variables $R^9$, $R^{10}$, $R^{11}$, $R^{14a}$, and $R^{15}$ is as described and defined in WO 2017/030814, WO 2016/118666, and US 2017/0327469, the entirety of each of which is herein incorporated by reference.

In certain embodiments, the present invention provides a compound of formula I, wherein LBM is a VHL binding moiety

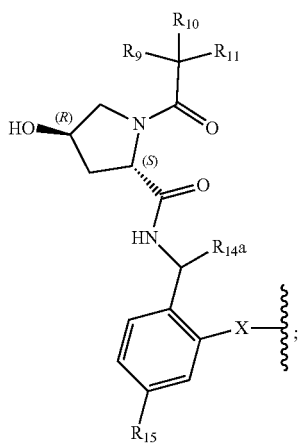

thereby forming a compound of formula I-eeee:

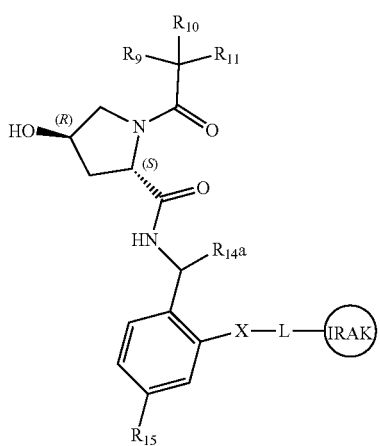

or a pharmaceutically acceptable salt thereof, wherein L and IRAK are as defined above and described in embodiments herein, and wherein each of the variables X, $R^9$, $R^{10}$, $R^{11}$, $R^{14a}$, and $R^{15}$ is as described and defined in WO 2017/030814, WO 2016/118666, and US 2017/0327469, the entirety of each of which is herein incorporated by reference.

In certain embodiments, the present invention provides a compound of formula I, wherein LBM is an IAP binding moiety

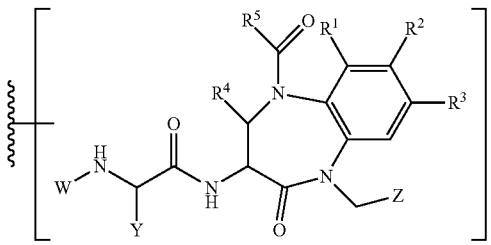

or derivative thereof;

thereby forming a compound of formula I-ffff:

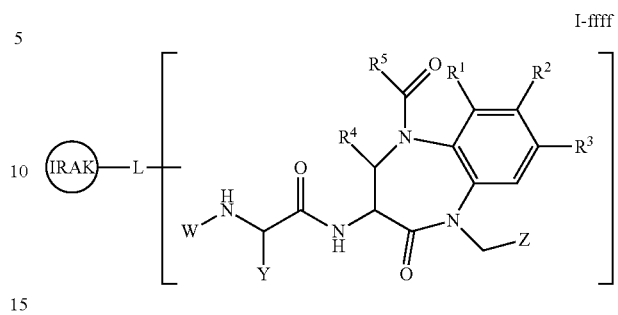

or a pharmaceutically acceptable salt thereof, wherein L and IRAK are as defined above and described in embodiments herein, and wherein each of the variables W, Y, Z, $R^1$, $R^2$, $R^3$, $R^4$, and $R^5$ is as described and defined in WO 2014/044622, US 2015/0225449, WO 2015/071393, and US 2016/0272596, the entirety of each of which is herein incorporated by reference.

In certain embodiments, the present invention provides a compound of formula I, wherein LBM is a MDM2 binding moiety

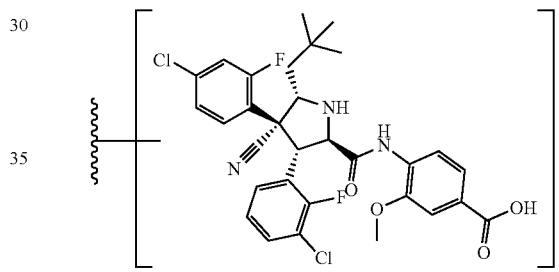

or derivatives thereof, thereby forming a compound of formula I-gggg:

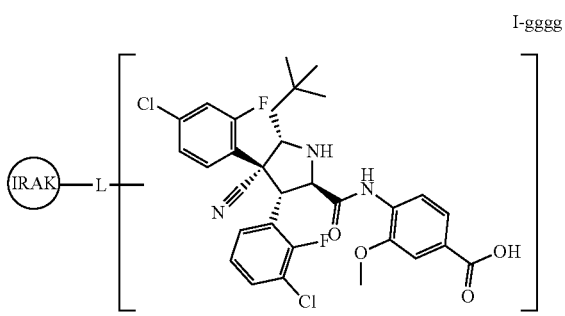

or derivative thereof, or a pharmaceutically acceptable salt thereof, as described and defined in Hines, J. et al., *Cancer Res.* (DOI: 10.1158/0008-5472.CAN-18-2918), the entirety of each of which is herein incorporated by reference.

In certain embodiments, the present invention provides a compound of formula I, wherein LBM is a DCAF16 binding moiety

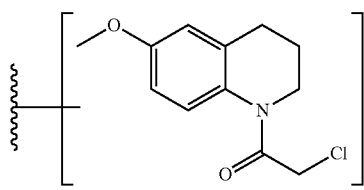

or derivatives thereof;
thereby forming a compound of formula I-hhhh:

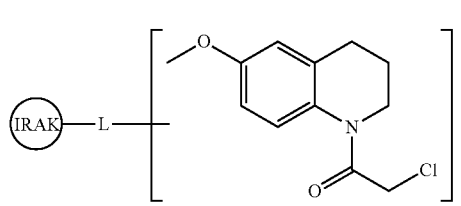

or derivative thereof, or a pharmaceutically acceptable salt thereof, as described and defined in Zhang, X. et al., bioRxiv (doi: https://doi.org/10.1101/443804), the entirety of each of which is herein incorporated by reference.

In certain embodiments, the present invention provides a compound of formula I, wherein LBM is a RNF114 binding moiety

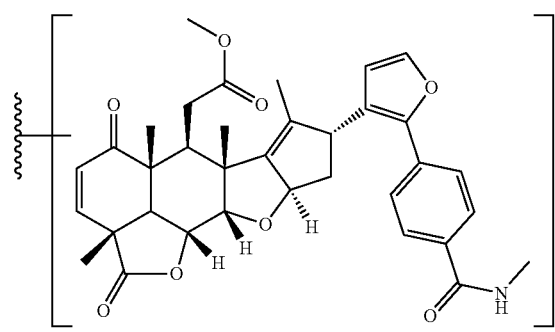

or derivatives thereof;
thereby forming a compound of formula I-iiii:

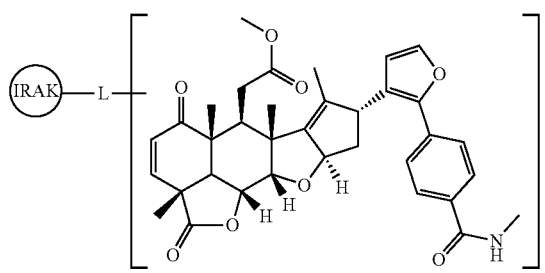

or derivative thereof, or a pharmaceutically acceptable salt thereof, as described and defined in Spradin, J. N. et al., bioRxiv (doi: https://doi.org/10.1101/436998), the entirety of each of which is herein incorporated by reference.

In certain embodiments, the present invention provides a compound of formula I, wherein IRAK is an IRAK4 binding moiety

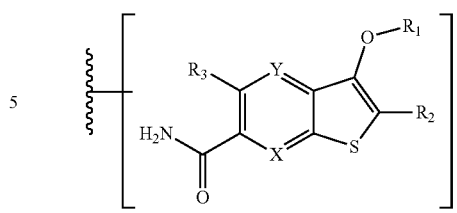

or derivative thereof; thereby forming a compound of formula I-jjjj:

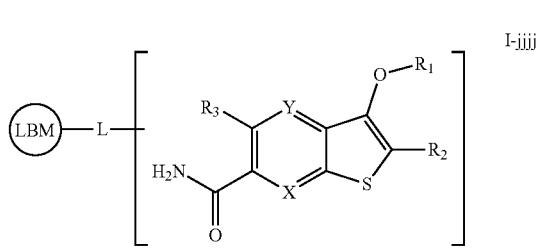

or a pharmaceutically acceptable salt thereof, wherein L and IRAK are as defined above and described in embodiments herein, and wherein X, Y, $R_1$, $R_2$, and $R_3$ are as defined and described in WO 2018/209012, the entirety of which is herein incorporated by reference.

In certain embodiments, the present invention provides a compound of formula I, wherein IRAK is an IRAK4 binding moiety

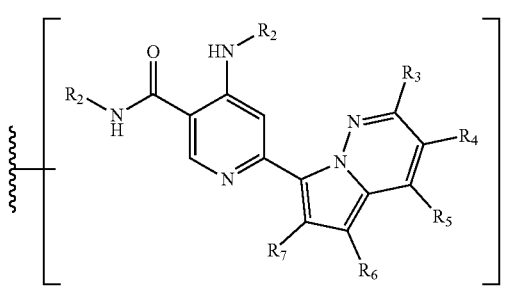

or derivative thereof,
thereby forming a compound of formula I-kkkk:

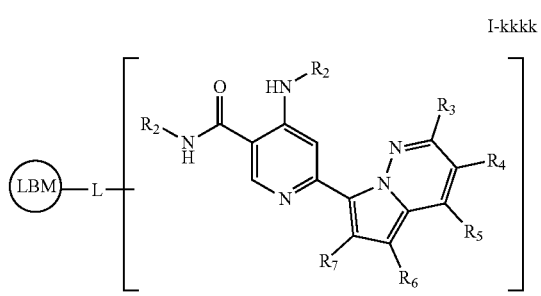

or a pharmaceutically acceptable salt thereof, wherein L and IRAK are as defined above and described in embodiments herein, and wherein $R_1$, $R_2$, $R_3$, $R_4$, $R_5$, $R_6$, and $R_7$ are as defined and described in US 2018/0230157, the entirety of which is herein incorporated by reference.

In certain embodiments, the present invention provides a compound of formula I, wherein IRAK is an IRAK1 and/or IRAK4 binding moiety

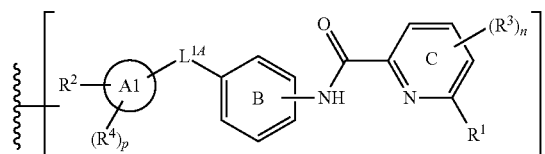

or derivative thereof,
thereby forming a compound of formula I-llll:

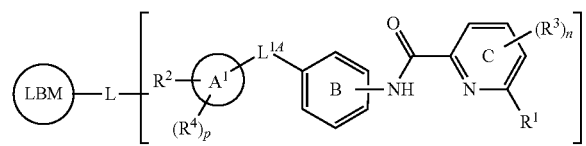

I-llll or a pharmaceutically acceptable salt thereof, wherein L and IRAK are as defined above and described in embodiments herein, and wherein Ring A1, Ring B, Ring C, $L^{1.4}$, $R^1$, $R^2$, $R^3$, $R^4$, n, and p are as defined and described in WO 2018/098367, the entirety of which is herein incorporated by reference.

In certain embodiments, the present invention provides a compound of formula I, wherein IRAK is an IRAK4 binding moiety

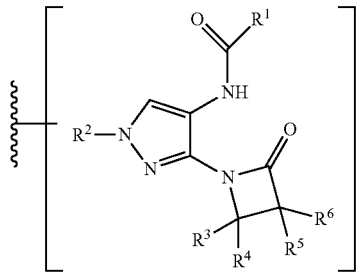

or derivative thereof;
thereby forming a compound of formula I-mmmm:

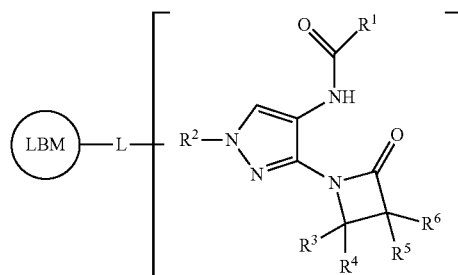

I-mmmm or a pharmaceutically acceptable salt thereof, wherein L and IRAK are as defined above and described in embodiments herein, and wherein $R^1$, $R^2$, $R^3$, $R^4$, $R^5$, and $R^6$ are as defined and described in WO 2018/052058, the entirety of which is herein incorporated by reference.

In certain embodiments, the present invention provides a compound of formula I, wherein IRAK is an IRAK1 and/or IRAK4 binding moiety

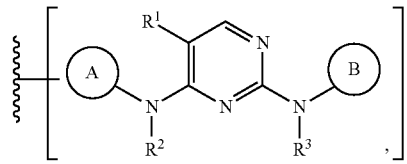

or derivative thereof;
thereby forming a compound of formula I-nnnn:

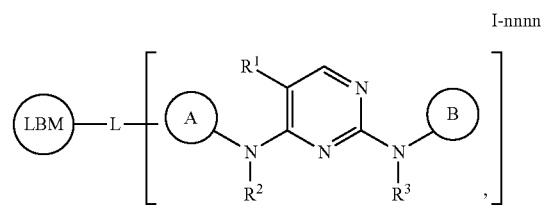

I-nnnn or a pharmaceutically acceptable salt thereof, wherein L and IRAK are as defined above and described in embodiments herein, and wherein Ring A, Ring B, $R^1$, $R^2$, and $R^3$ are as defined and described in US 2017/0369476, the entirety of which is herein incorporated by reference.

In certain embodiments, the present invention provides a compound of formula I, wherein IRAK is an IRAK4 binding moiety

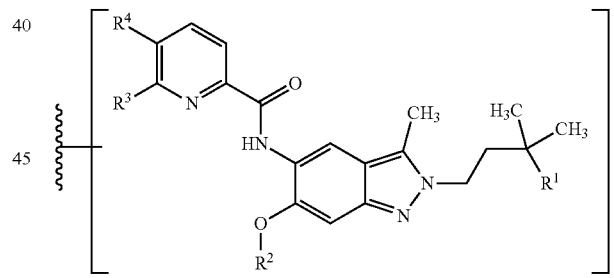

or derivative thereof;
thereby forming a compound of formula I-oooo:

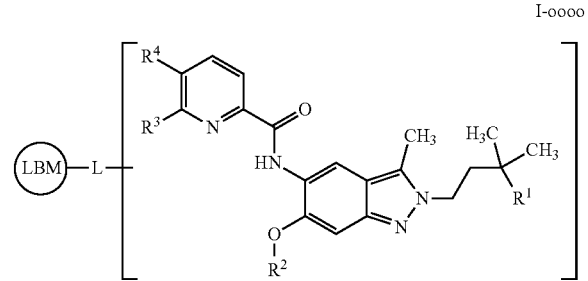

I-oooo or a pharmaceutically acceptable salt thereof, wherein L and IRAK are as defined above and described in embodiments herein, and wherein R¹, R², R³, and R⁴ are as defined and described in WO 2017/207385, the entirety of which is herein incorporated by reference.

In certain embodiments, the present invention provides a compound of formula I, wherein IRAK is an IRAK4 binding moiety

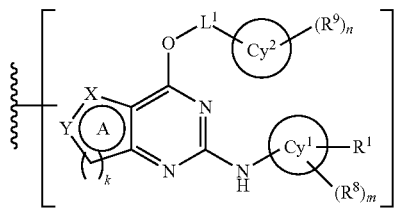

or derivative thereof;
thereby forming a compound of formula I-pppp:

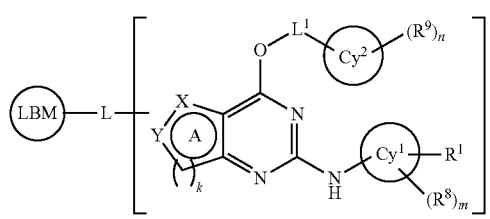

I-pppp or a pharmaceutically acceptable salt thereof, wherein L and IRAK are as defined above and described in embodiments herein, and wherein Ring A, X, Y, L¹, Cy¹, Cy², R¹ R⁸, R⁹, k, m, and n are as defined and described in WO 2017/205766, the entirety of which is herein incorporated by reference.

In certain embodiments, the present invention provides a compound of formula I, wherein IRAK is an IRAK4 binding moiety

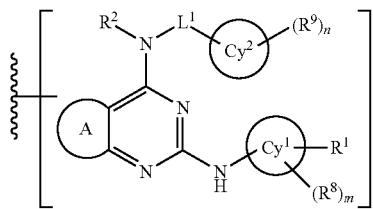

or derivative thereof;
thereby forming a compound of formula I-qqqq:

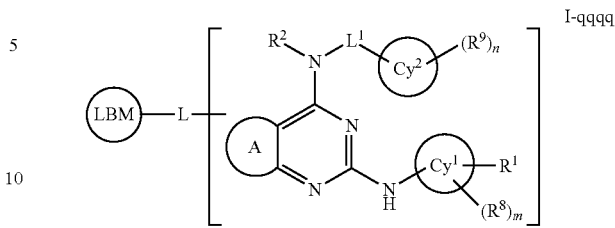

I-qqqq or a pharmaceutically acceptable salt thereof, wherein L and IRAK are as defined above and described in embodiments herein, and wherein Ring A, L¹, Cy¹, Cy², R¹ R⁸, R⁹, m, and n are as defined and described in WO 2017/205762, the entirety of which is herein incorporated by reference.

In certain embodiments, the present invention provides a compound of formula I, wherein IRAK is an IRAK4 binding moiety

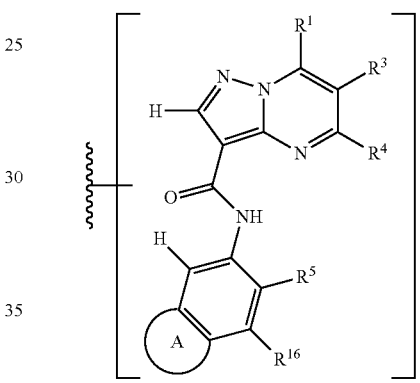

or derivative thereof;
thereby forming a compound of formula I-rrrr:

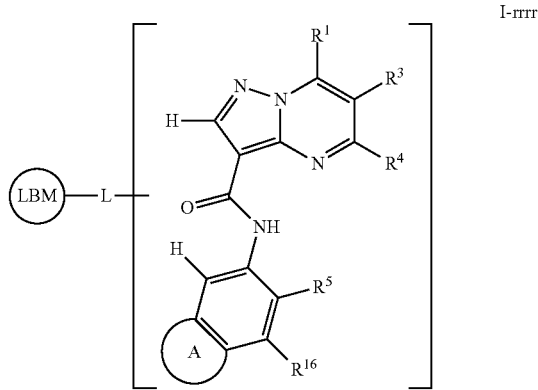

I-rrrr or a pharmaceutically acceptable salt thereof, wherein L and IRAK are as defined above and described in embodiments herein, and wherein Ring A, R¹, R³, R⁴, R⁵, and R¹⁶ are as defined and described in WO 2017/108723, the entirety of which is herein incorporated by reference.

In certain embodiments, the present invention provides a compound of formula I, wherein IRAK is an IRAK1 and/or IRAK4 binding moiety

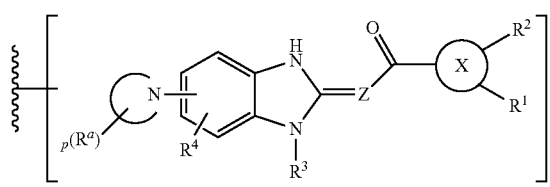

or derivative thereof;

thereby forming a compound of formula I-ssss:

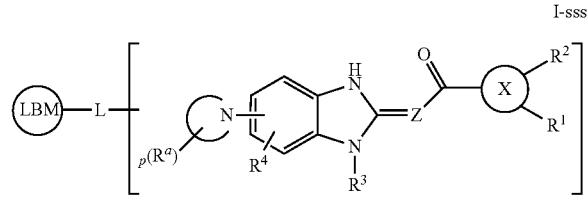

or a pharmaceutically acceptable salt thereof, wherein L and IRAK are as defined above and described in embodiments herein, and wherein Ring X, Z, $R^1$, $R^2$, $R^3$, $R^4$, $R^a$ and p are as defined and described in WO 2017/049068, the entirety of which is herein incorporated by reference.

In certain embodiments, the present invention provides a compound of formula I, wherein IRAK is an IRAK4 binding moiety

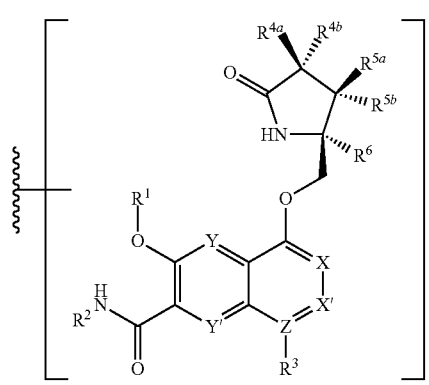

or derivative thereof;

thereby forming a compound of formula I-ssss:

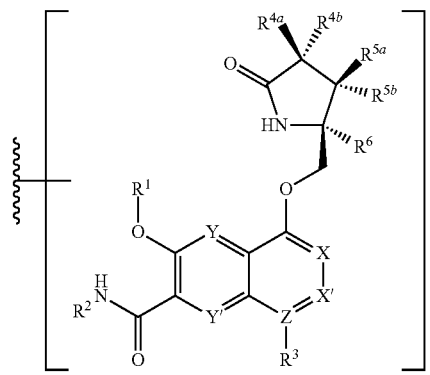

or a pharmaceutically acceptable salt thereof, wherein L and IRAK are as defined above and described in embodiments herein, and wherein X, X', Y, Y', Z, $R^1$, $R^2$, $R^3$, $R^{4a}$, $R^{4b}$, $R^{5a}$, $R^{5b}$ and $R^6$ are as defined and described in WO 2017/033093, the entirety of which is herein incorporated by reference.

In certain embodiments, the present invention provides a compound of formula I, wherein IRAK is an IRAK4 binding moiety or derivative thereof;
thereby forming a compound of formula I-ssss:

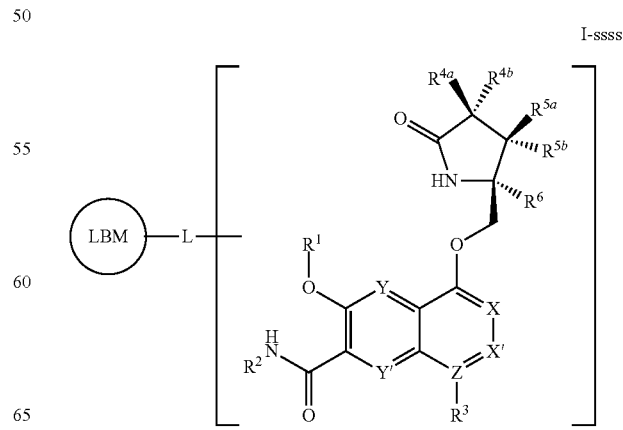

or a pharmaceutically acceptable salt thereof, wherein L and IRAK are as defined above and described in embodiments herein, and wherein X, X', Y, Y', Z, $R^1$, $R^2$, $R^3$, $R^{4a}$, $R^{4b}$, $R^{5a}$, $R^{5b}$ and $R^6$ are as defined and described in WO 2017/033093, the entirety of which is herein incorporated by reference.

In certain embodiments, the present invention provides a compound of formula I, wherein LBM is a RNF114 binding moiety

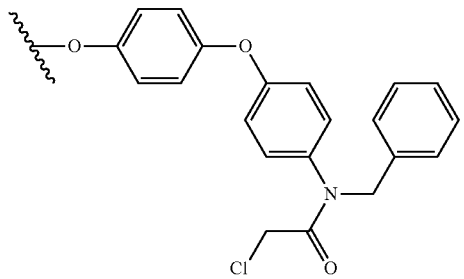 [SMILES: *Oc1ccc(Oc2ccc(N(Cc3ccccc3)C(=O)CCl)cc2)cc1]

or derivatives thereof;
thereby forming a compound of formula I-iiii:

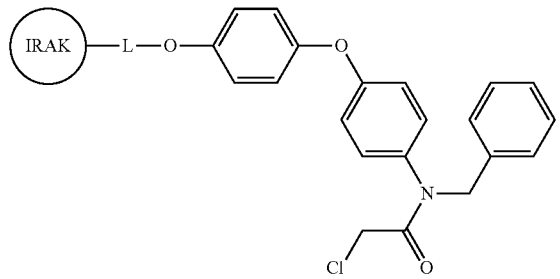

I-iiii or derivative thereof, or a pharmaceutically acceptable salt thereof, as described and defined in Ward, C. C., et al., *bioRxiv* (doi: https://doi.org/10.1101/439125), the entirety of each of which is herein incorporated by reference.

Exemplary compounds of the invention are set forth in Table 1, below.

TABLE 1

Exemplary Compounds

| I # | Structure |
|---|---|
| I-1 | 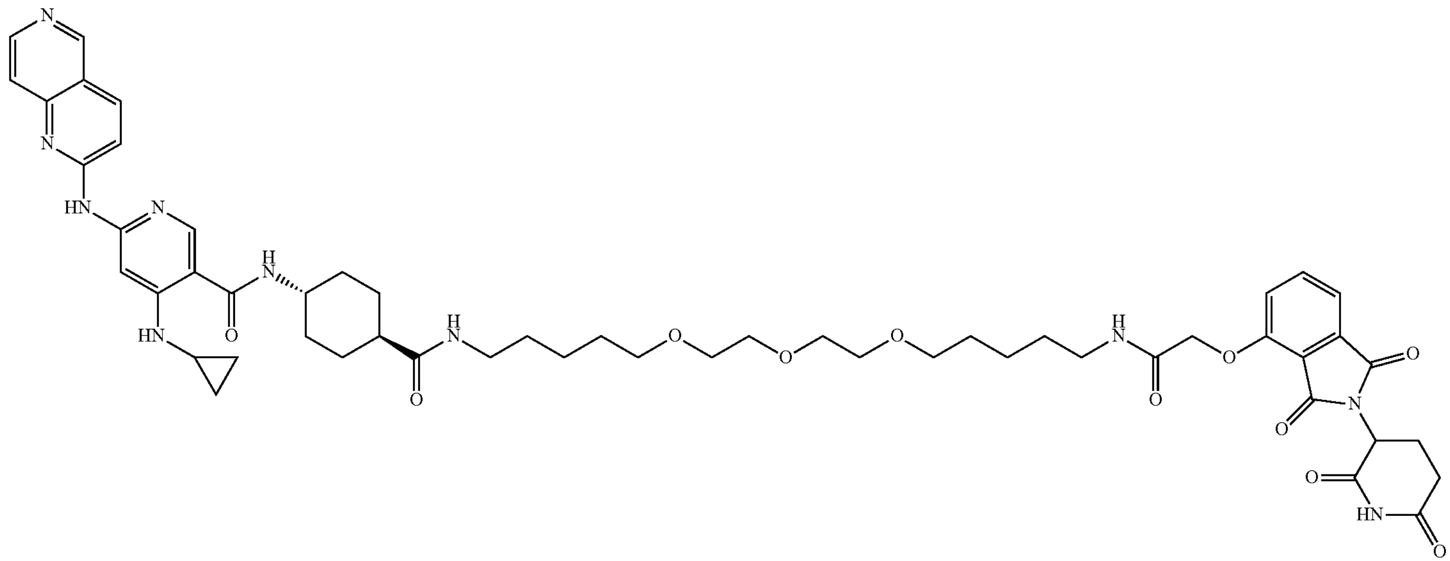 [SMILES: O=C(COc1cccc2c1C(=O)N(C1CCC(=O)NC1=O)C2=O)NCCCCCOCCOCCOCCCCCNC(=O)[C@H]1CC[C@H](NC(=O)c2cnc(Nc3ccc4cnccc4n3)cc2NC2CC2)CC1] |

TABLE 1-continued
Exemplary Compounds
| I-# | Structure |
|---|---|
| I-2 | 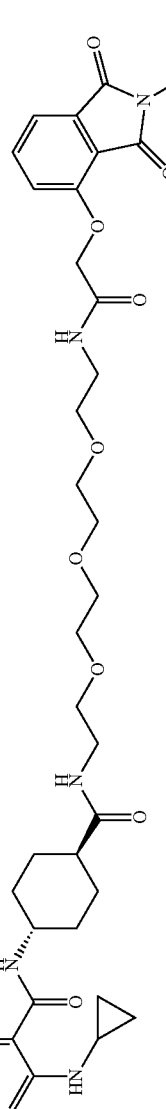 |

TABLE 1-continued
Exemplary Compounds
| I-# | Structure |
|---|---|
| I-3 | 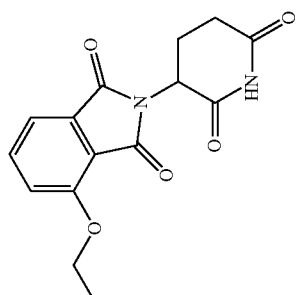 |

TABLE 1-continued
Exemplary Compounds
| I-# | Structure |
|---|---|
| I-4 | 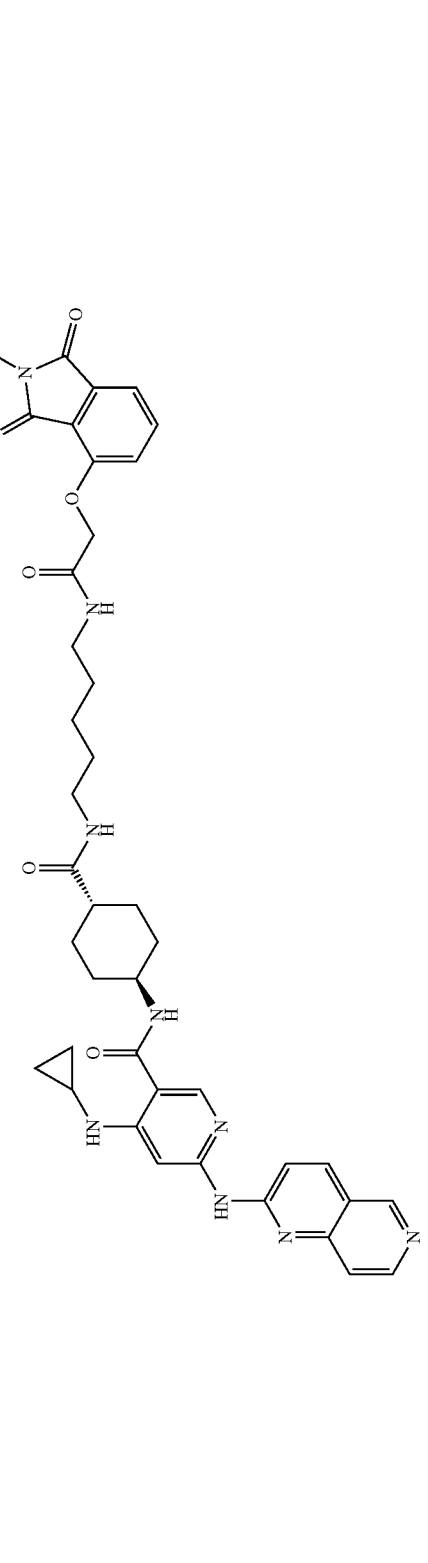 |
| I-5 | 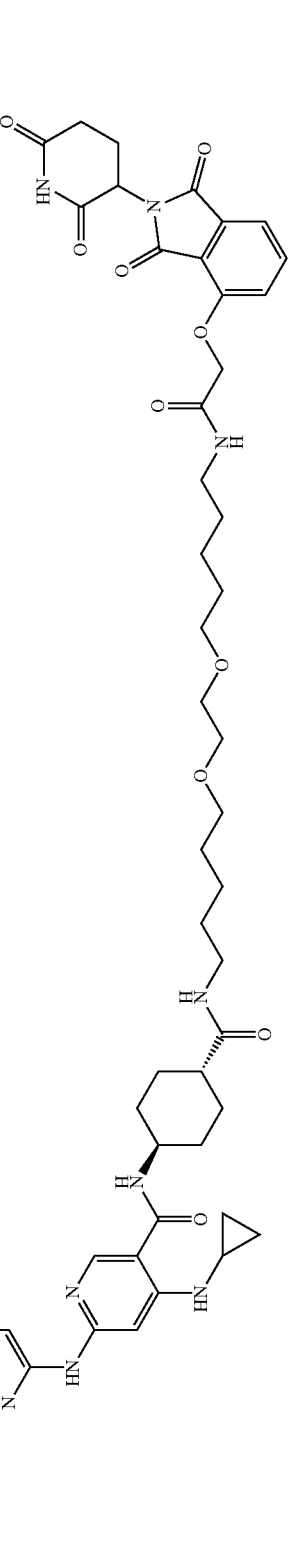 |

TABLE 1-continued
Exemplary Compounds
| I-# | Structure |
|---|---|
| I-6 | 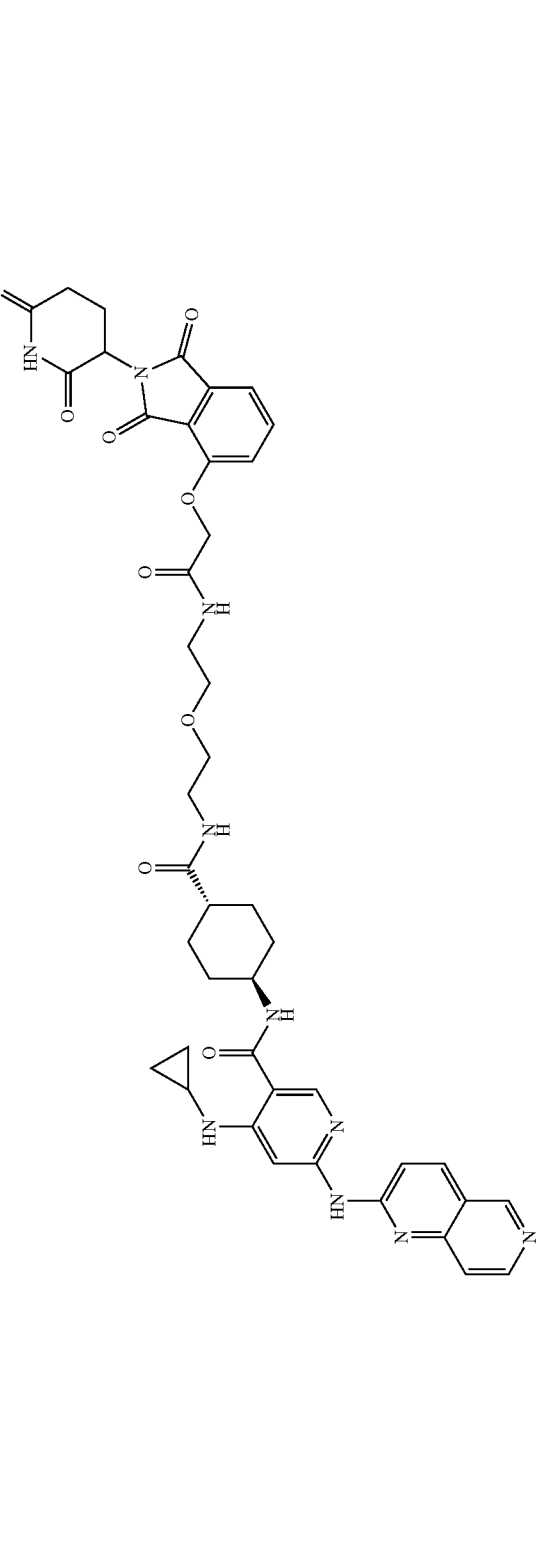 |

TABLE 1-continued
Exemplary Compounds
| I-# | Structure |
|---|---|
| I-7 | 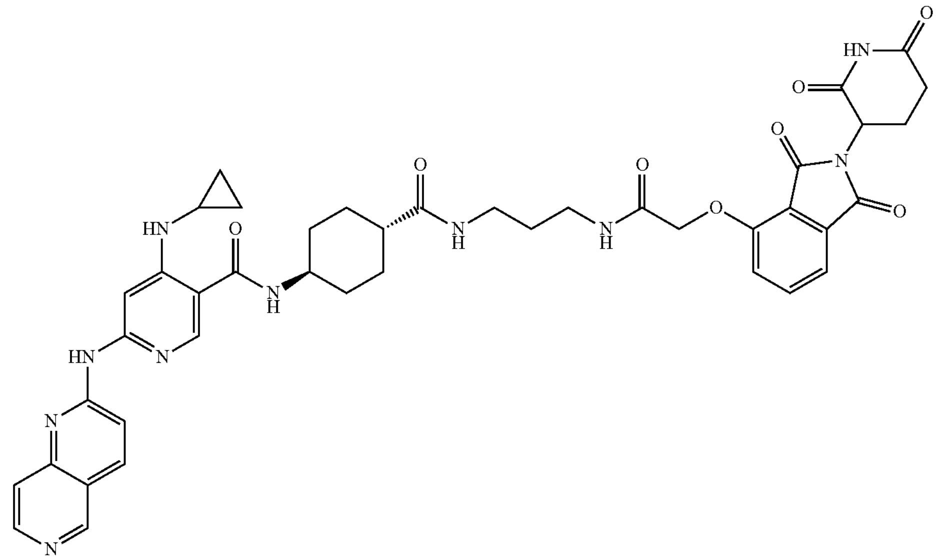 [SMILES: O=C(COc1cccc2c1C(=O)N(C1CCC(=O)NC1=O)C2=O)NCCCNC(=O)[C@H]1CC[C@H](NC(=O)c2cnc(Nc3ccc4cnccc4n3)cc2NC2CC2)CC1] |
| I-8 | 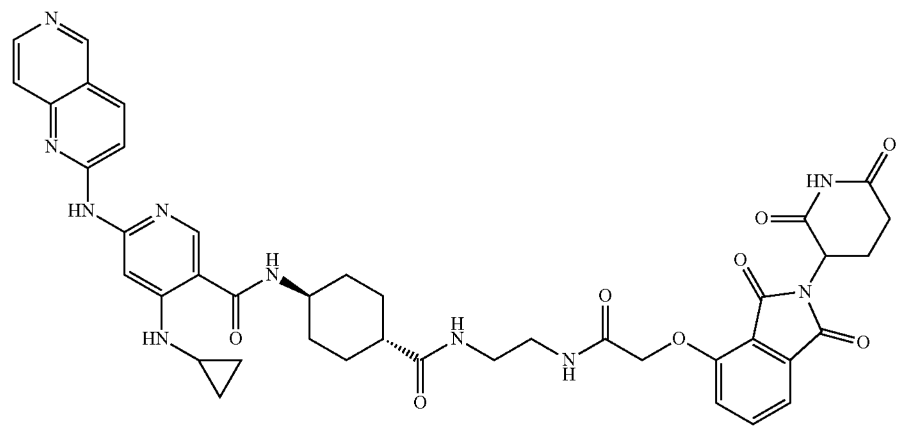 [SMILES: O=C(COc1cccc2c1C(=O)N(C1CCC(=O)NC1=O)C2=O)NCCNC(=O)[C@H]1CC[C@H](NC(=O)c2cnc(Nc3ccc4cnccc4n3)cc2NC2CC2)CC1] |

TABLE 1-continued
Exemplary Compounds
| I-# | Structure |
|---|---|
| I-9 | 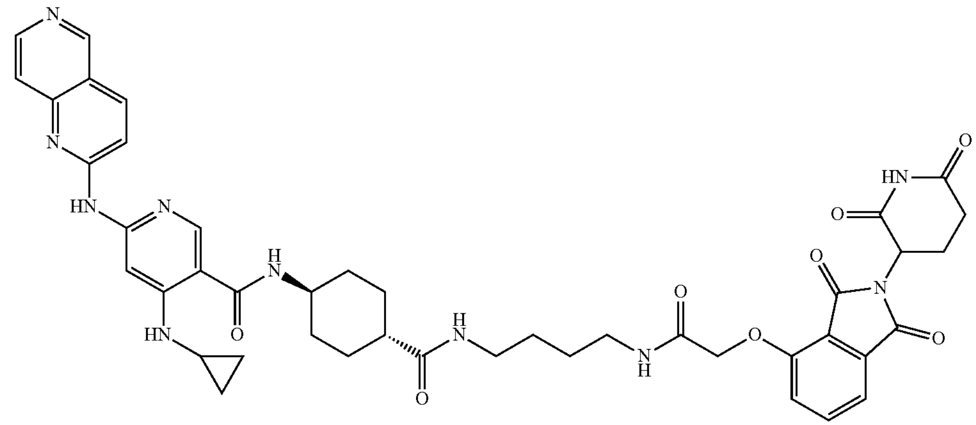 [SMILES: O=C(COc1cccc2c1C(=O)N(C1CCC(=O)NC1=O)C2=O)NCCCCNC(=O)[C@H]1CC[C@H](NC(=O)c2cnc(Nc3ccc4cnccc4n3)cc2NC2CC2)CC1] |
| I-10 | 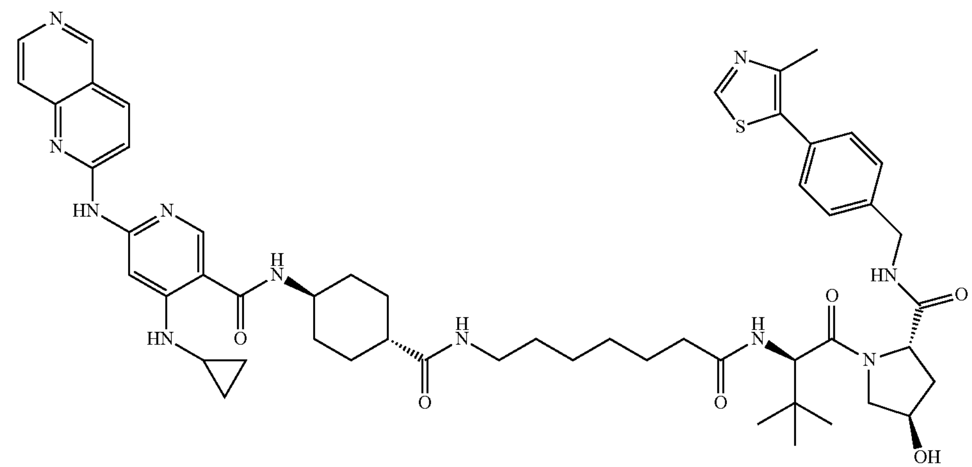 [SMILES: Cc1ncsc1-c1ccc(CNC(=O)[C@@H]2C[C@@H](O)CN2C(=O)[C@H](NC(=O)CCCCCCNC(=O)[C@H]2CC[C@H](NC(=O)c3cnc(Nc4ccc5cnccc5n4)cc3NC3CC3)CC2)C(C)(C)C)cc1] |

TABLE 1-continued
Exemplary Compounds
| I-# | Structure |
|---|---|
| I-11 | 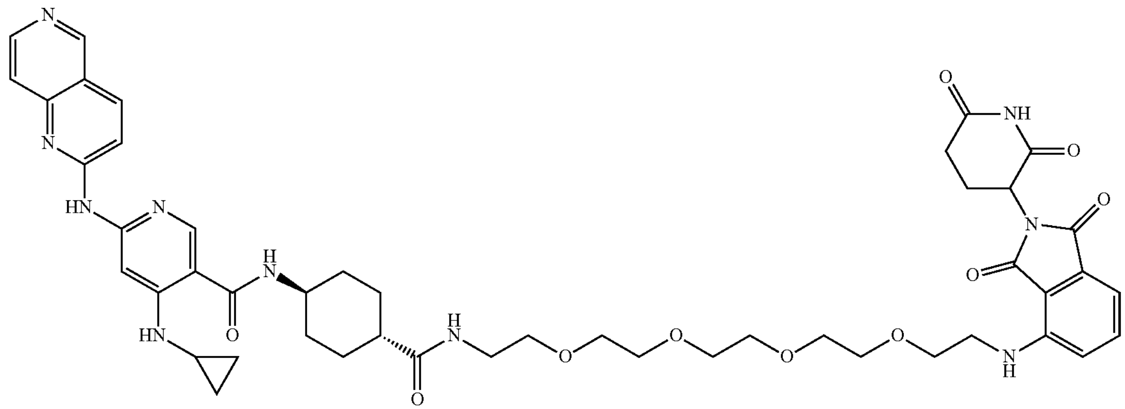 [SMILES: O=C1CCC(N2C(=O)c3cccc(NCCOCCOCCOCCOCCNC(=O)[C@H]4CC[C@H](NC(=O)c5cnc(Nc6ccc7cnccc7n6)cc5NC5CC5)CC4)c3C2=O)C(=O)N1] |

TABLE 1-continued
Exemplary Compounds
| I-# | Structure |
|---|---|
| I-12 | 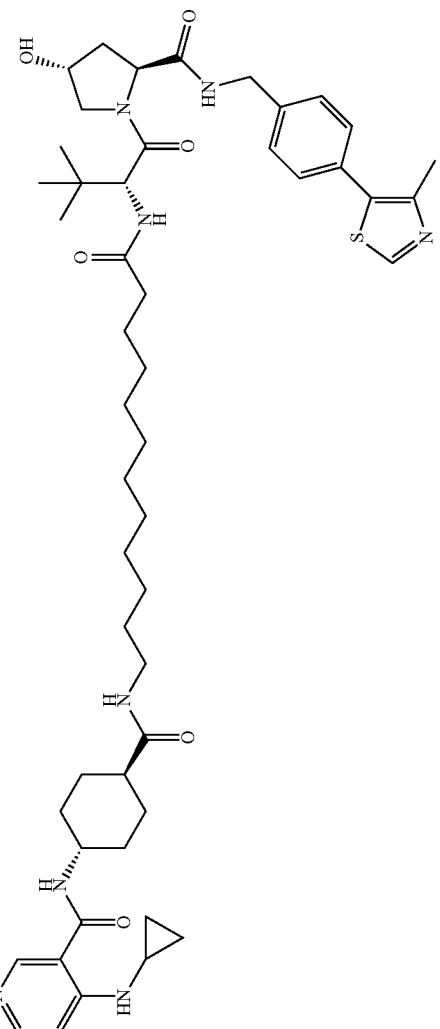 |

TABLE 1-continued
Exemplary Compounds
| I-# | Structure |
|---|---|
| I-13 | 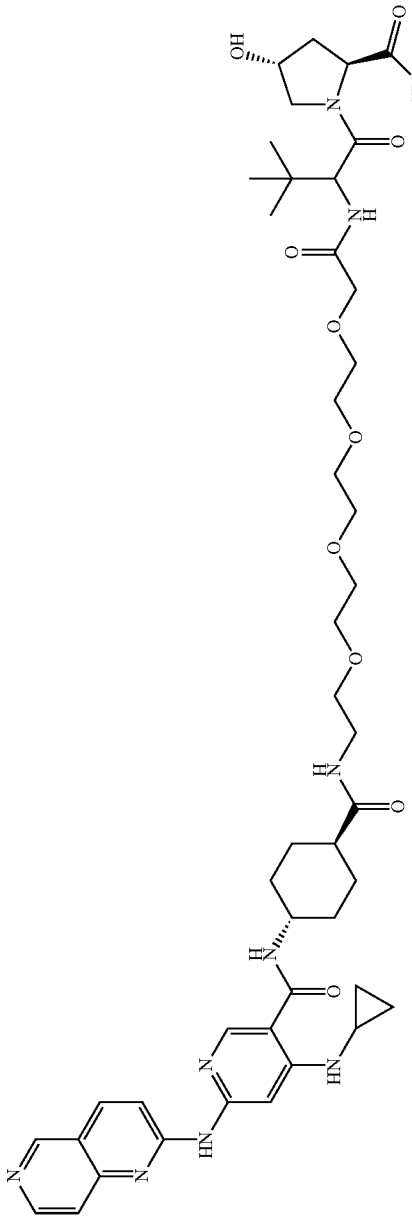 |

TABLE 1-continued
Exemplary Compounds
| I-# | Structure |
|---|---|
| I-14 | 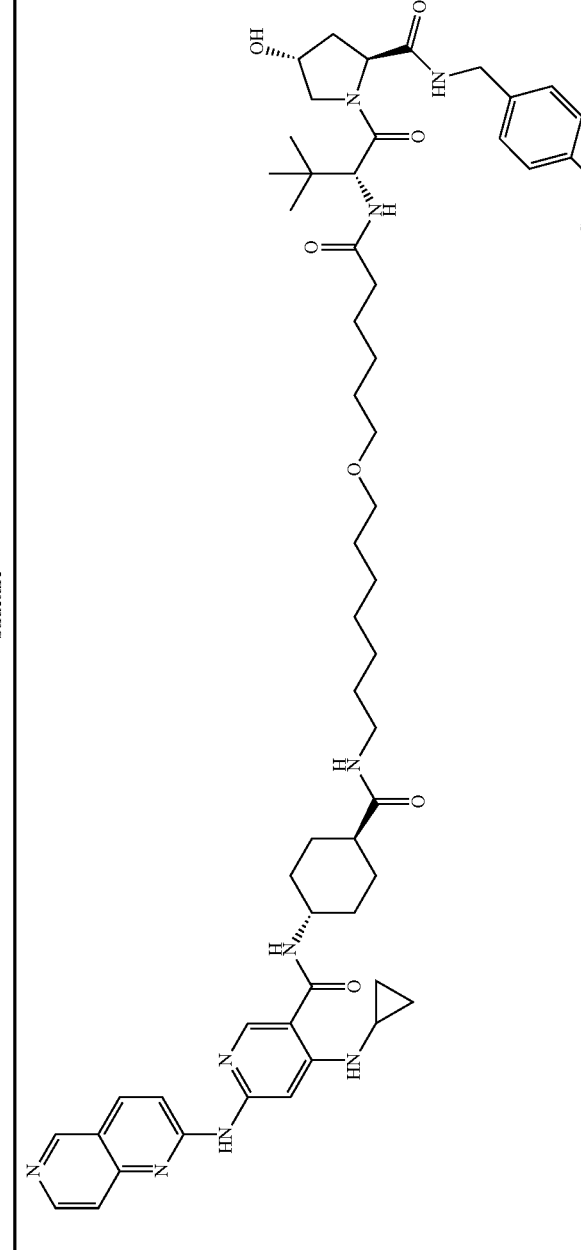 |

TABLE 1-continued
Exemplary Compounds
| I-# | Structure |
|---|---|
| I-15 | 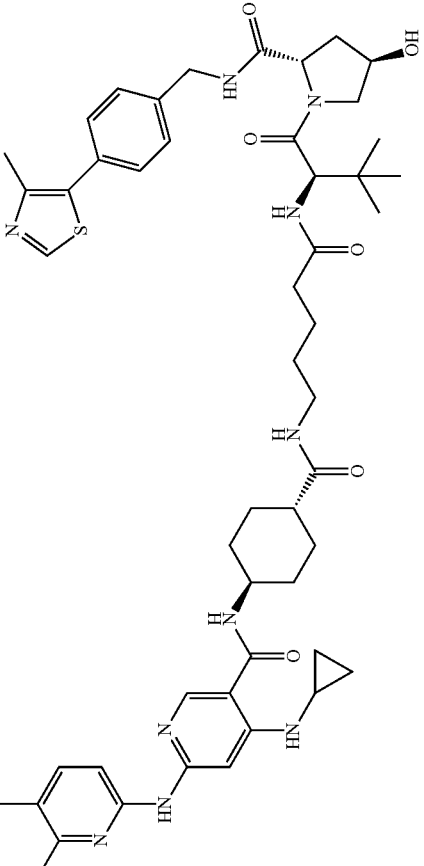 |
| I-16 | 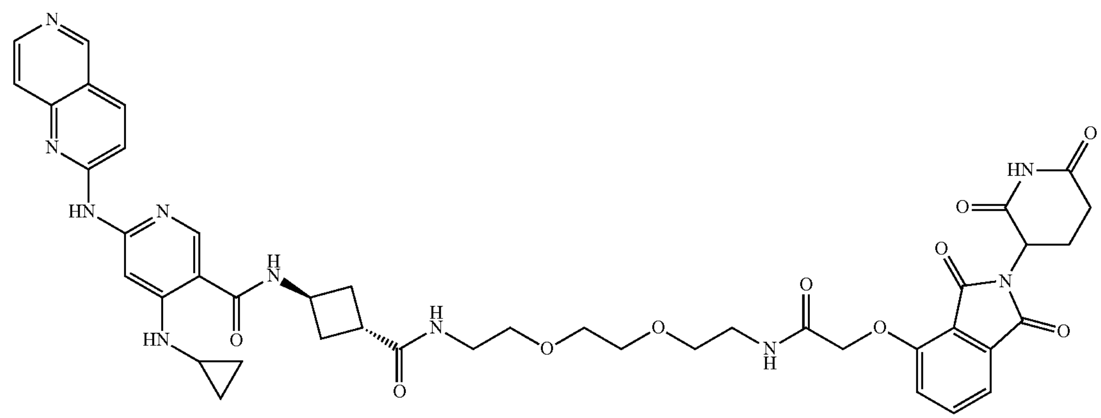 [SMILES: O=C(COc1cccc2c1C(=O)N(C1CCC(=O)NC1=O)C2=O)NCCOCCOCCNC(=O)[C@H]1C[C@H](NC(=O)c2cnc(Nc3ccc4cnccc4n3)cc2NC2CC2)C1] |

TABLE 1-continued
Exemplary Compounds
| I-# | Structure |
|---|---|
| I-17 | 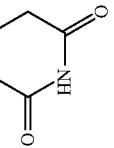 |

TABLE 1-continued
Exemplary Compounds
| I-# | Structure |
|---|---|
| I-18 | 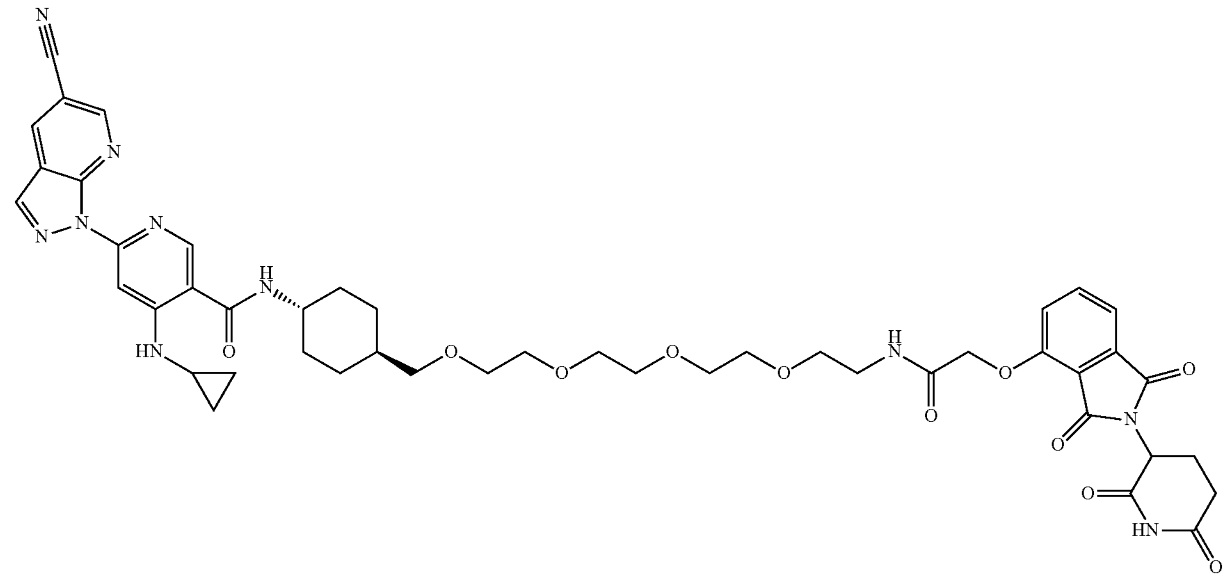 [SMILES: N#Cc1cnc2c(cnn2-c2cc(NC3CC3)c(C(=O)N[C@H]3CC[C@H](COCCOCCOCCOCCNC(=O)COc4cccc5c4C(=O)N(C4CCC(=O)NC4=O)C5=O)CC3)cn2)c1] |
| I-19 | 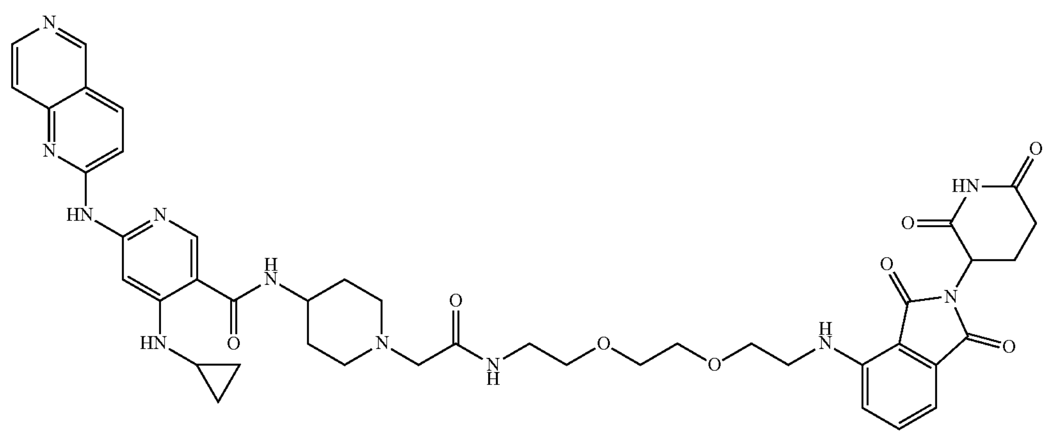 [SMILES: O=C(CN1CCC(NC(=O)c2cnc(Nc3ccc4cnccc4n3)cc2NC2CC2)CC1)NCCOCCOCCNc1cccc2c1C(=O)N(C1CCC(=O)NC1=O)C2=O] |

TABLE 1-continued
Exemplary Compounds
| I-# | Structure |
|---|---|
| I-20 | 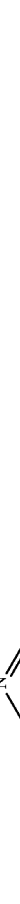 |
| I-21 | 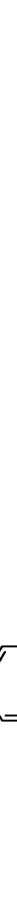 |

TABLE 1-continued
Exemplary Compounds
| I-# | Structure |
|---|---|
| I-22 | 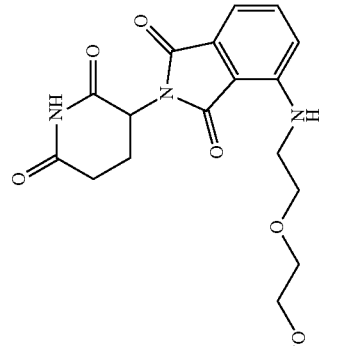 |
| I-23 | 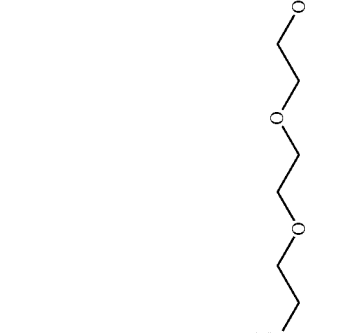 |

TABLE 1-continued
Exemplary Compounds
| I-# | Structure |
|---|---|
| I-24 | 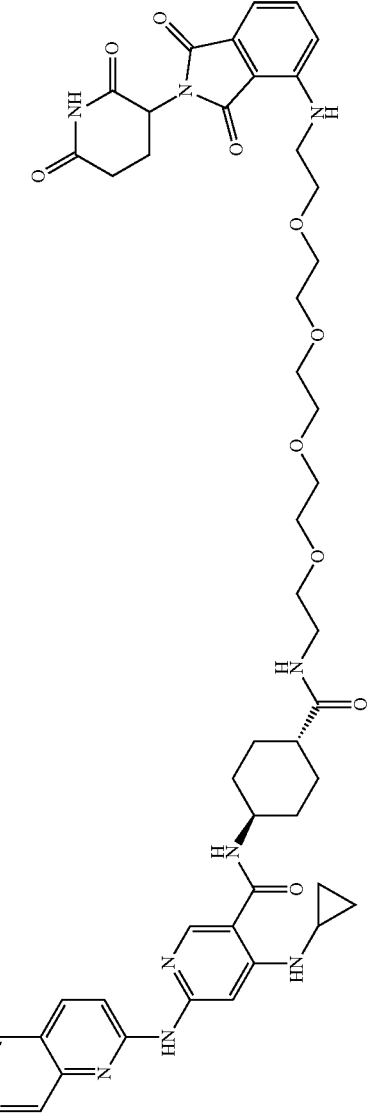 |
| I-25 | 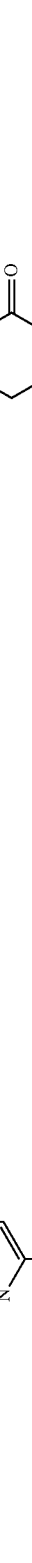 |

TABLE 1-continued
Exemplary Compounds
| I-# | Structure |
|---|---|
| I-26 | 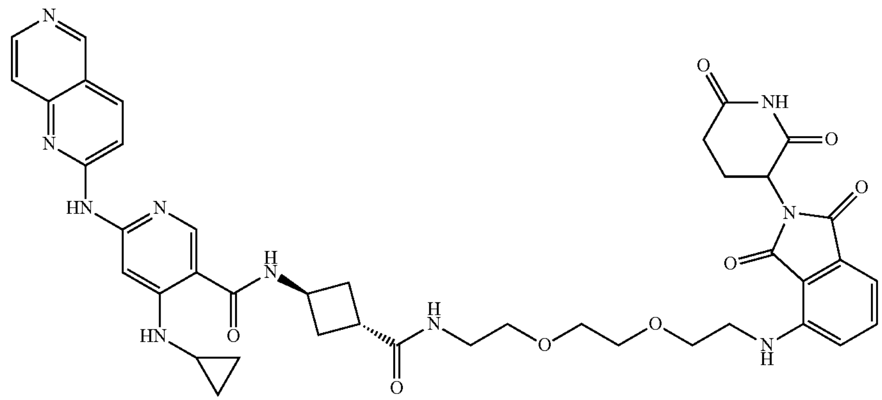 [SMILES: O=C1CCC(N2C(=O)c3cccc(NCCOCCOCCNC(=O)[C@H]4C[C@H](NC(=O)c5cnc(Nc6ccc7cnccc7n6)cc5NC5CC5)C4)c3C2=O)C(=O)N1] |
| I-27 | 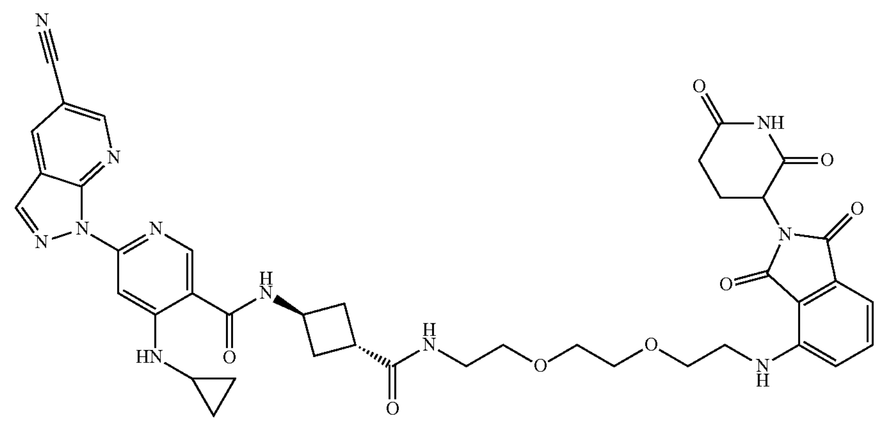 [SMILES: N#Cc1cnc2c(cnn2-c2cc(NC3CC3)c(C(=O)N[C@H]3C[C@H](C(=O)NCCOCCOCCNc4cccc5c4C(=O)N(C4CCC(=O)NC4=O)C5=O)C3)cn2)c1] |

TABLE 1-continued
Exemplary Compounds
| I-# | Structure |
|---|---|
| I-29 | 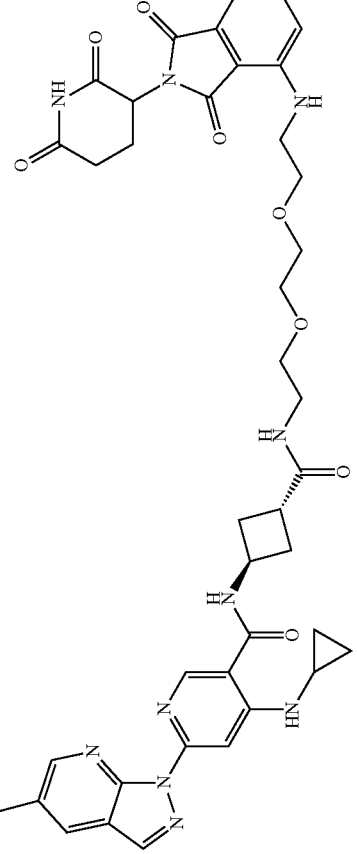 |
| I-30 | 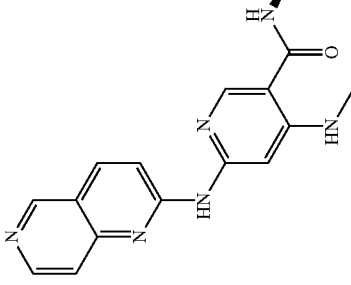 |

TABLE 1-continued
Exemplary Compounds
| I-# | Structure |
|---|---|
| I-31 | 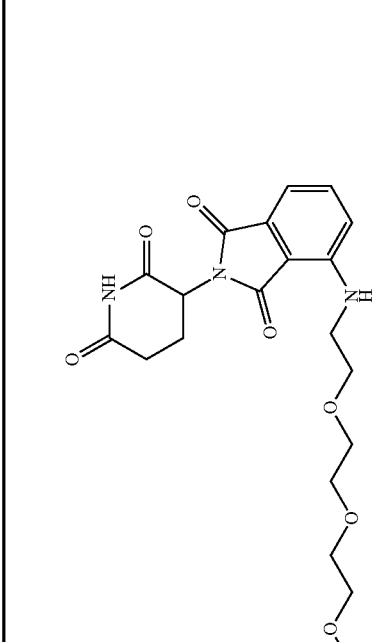 |
| I-32 | 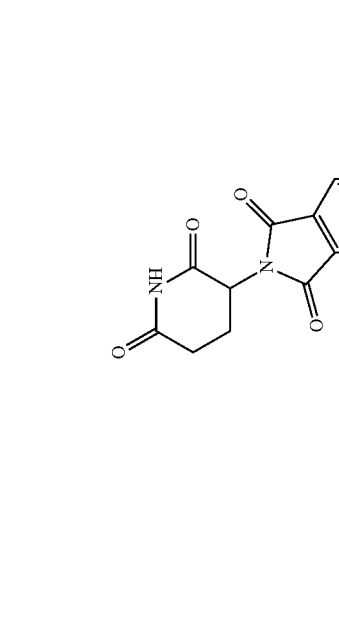 |

TABLE 1-continued
Exemplary Compounds
| I-# | Structure |
|---|---|
| I-33 | 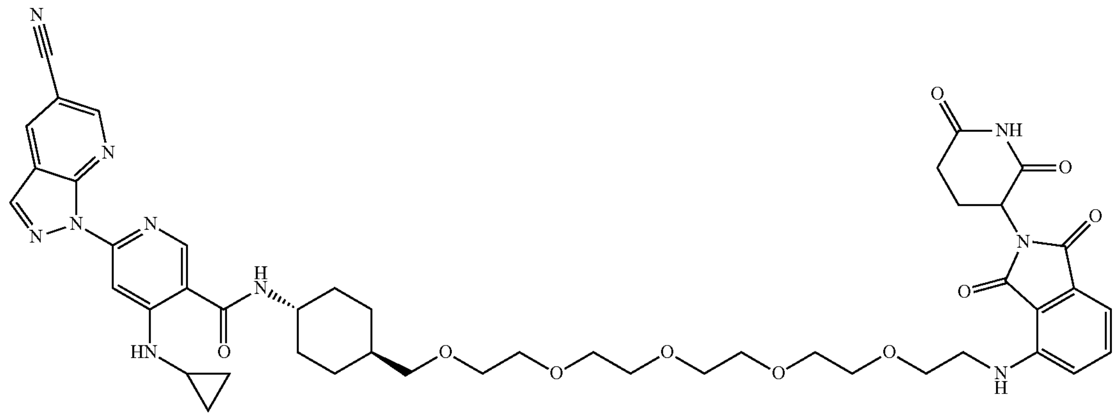 [SMILES: N#Cc1cnc2c(cnn2-c2cc(NC3CC3)c(C(=O)N[C@H]3CC[C@H](COCCOCCOCCOCCOCCNc4cccc5c4C(=O)N(C4CCC(=O)NC4=O)C5=O)CC3)cn2)c1] |
| I-34 | 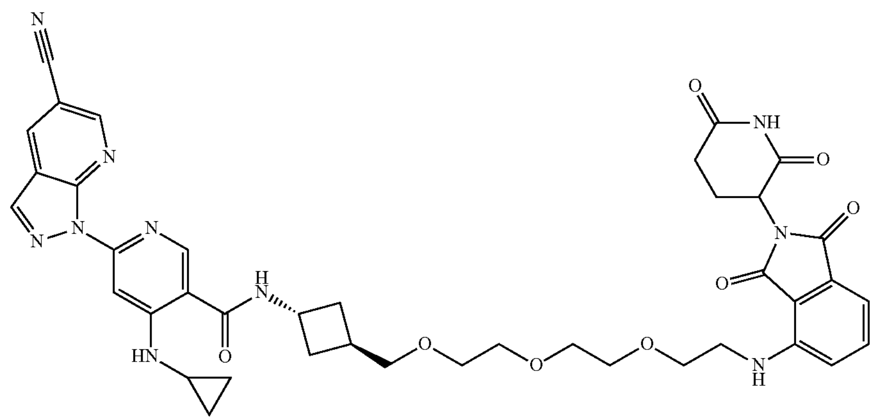 [SMILES: N#Cc1cnc2c(cnn2-c2cc(NC3CC3)c(C(=O)N[C@H]3C[C@H](COCCOCCOCCNc4cccc5c4C(=O)N(C4CCC(=O)NC4=O)C5=O)C3)cn2)c1] |

TABLE 1-continued
Exemplary Compounds
| I-# | Structure |
|---|---|
| I-35 | 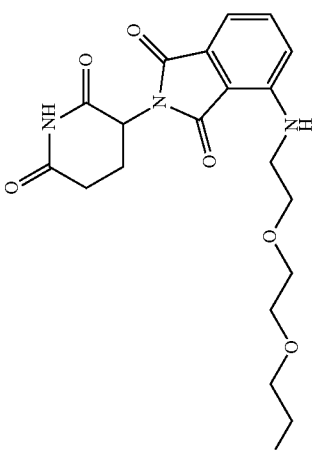 |
| I-36 | 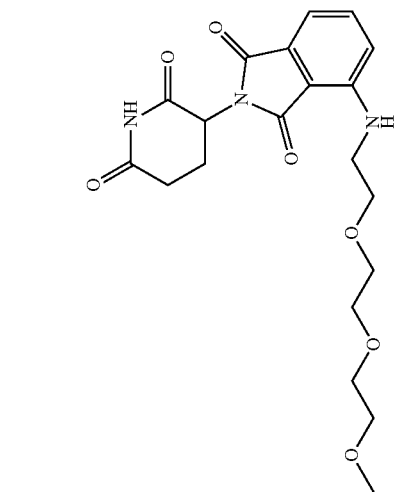 |

TABLE 1-continued
Exemplary Compounds
| I-# | Structure |
|---|---|
| I-37 | 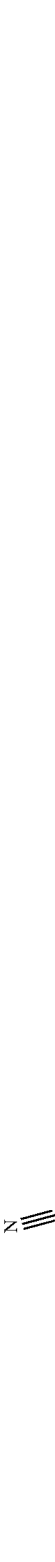 |

TABLE 1-continued
Exemplary Compounds
| I-# | Structure |
|---|---|
| I-38 | 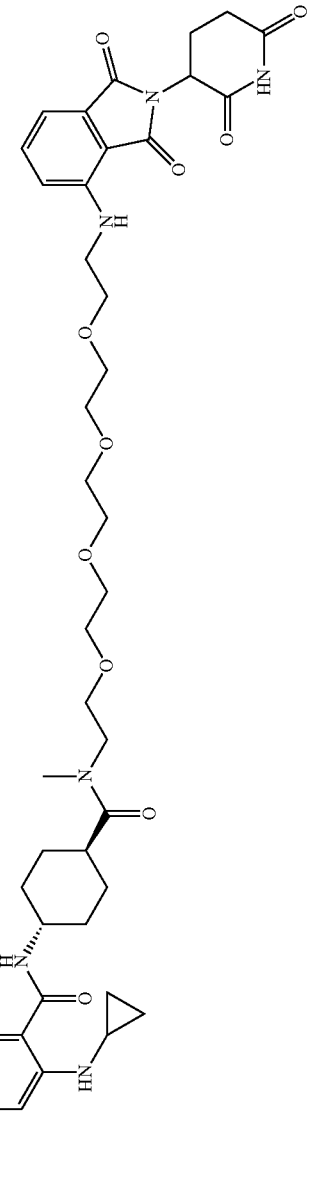 |

TABLE 1-continued
Exemplary Compounds
| I-# | Structure |
|---|---|
| I-39 | 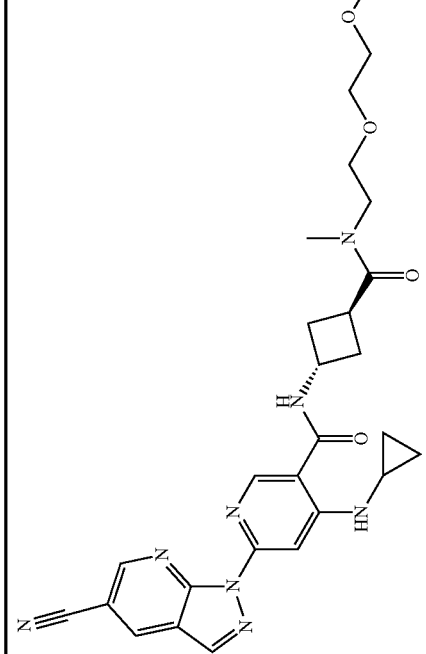 |

TABLE 1-continued
Exemplary Compounds
| I-# | Structure |
|---|---|
| I-40 | 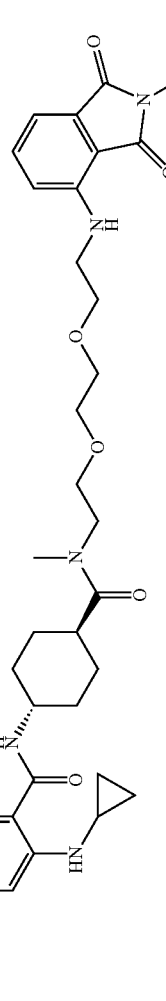 |
| I-41 | 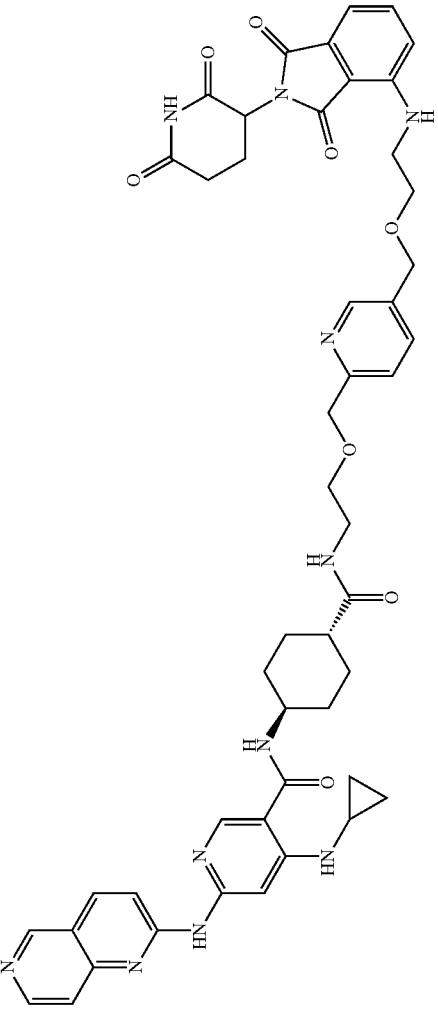 |

TABLE 1-continued
Exemplary Compounds
| I-# | Structure |
|---|---|
| I-42 | 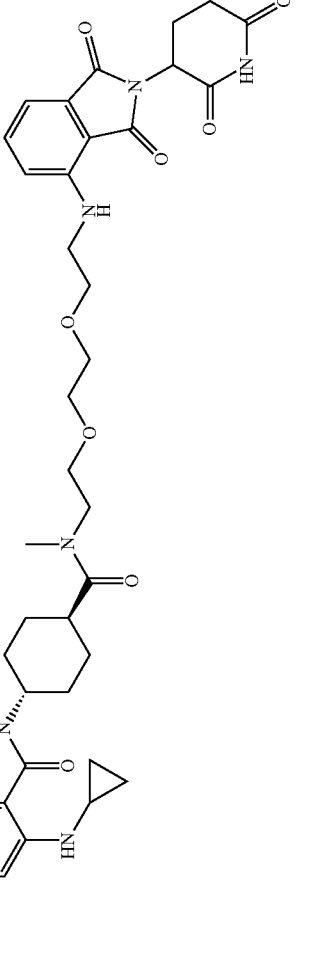 |
| I-43 | 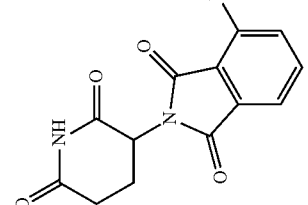 |

TABLE 1-continued
Exemplary Compounds
| I-# | Structure |
|---|---|
| I-44 | 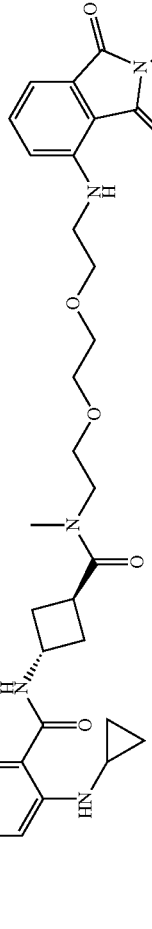 |
| I-45 | 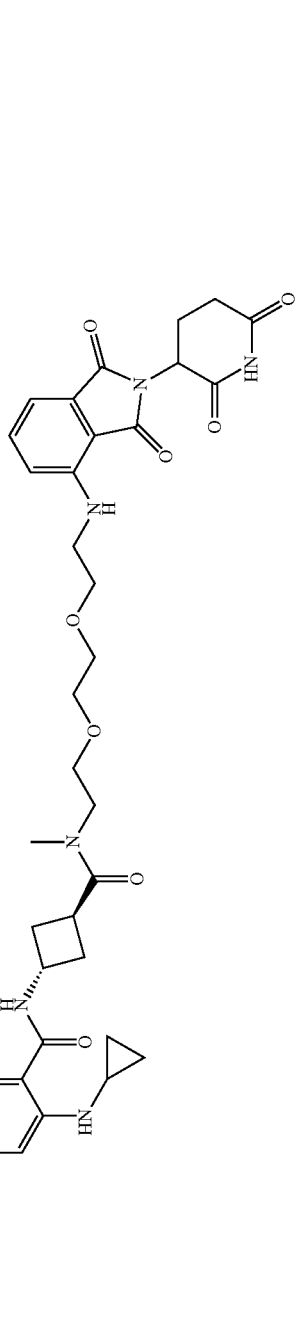 |

TABLE 1-continued
Exemplary Compounds
| I-# | Structure |
|---|---|
| I-46 | 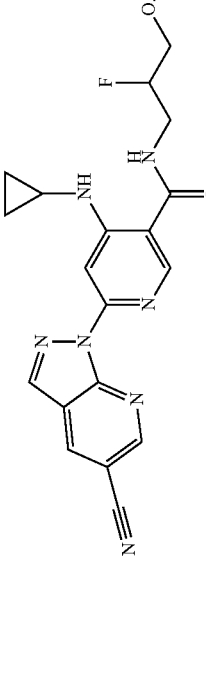 |
| I-47 | 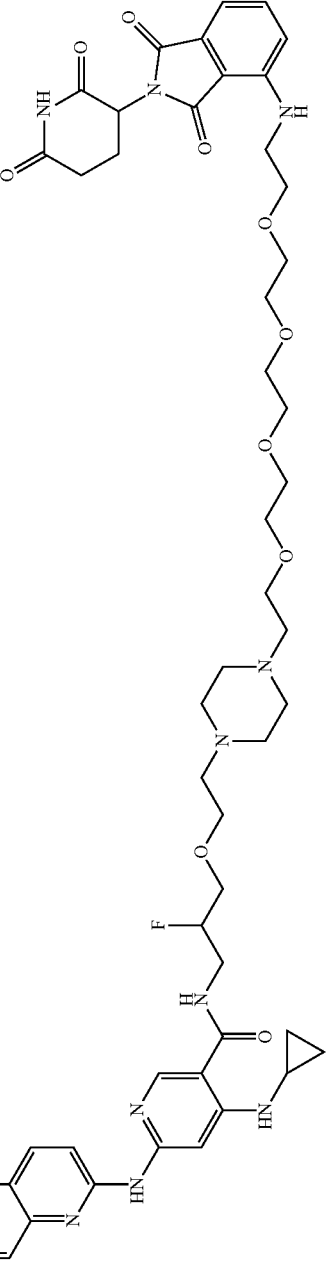 |

TABLE 1-continued
Exemplary Compounds
| I-# | Structure |
|---|---|
| I-48 | 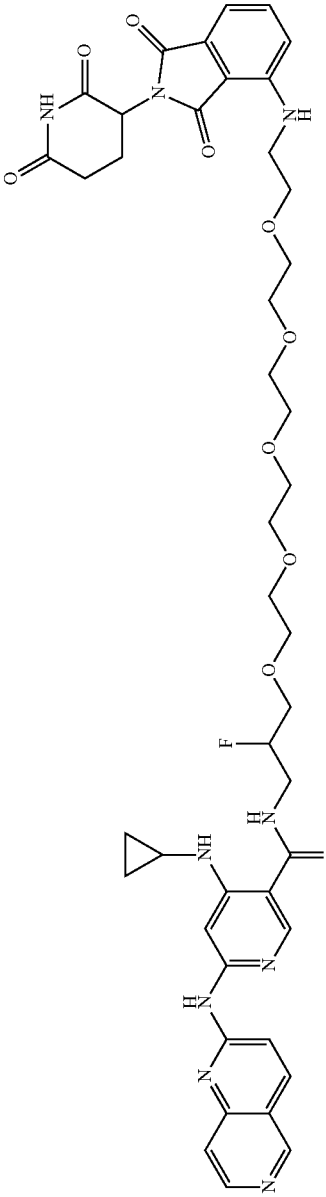 |
| I-49 | 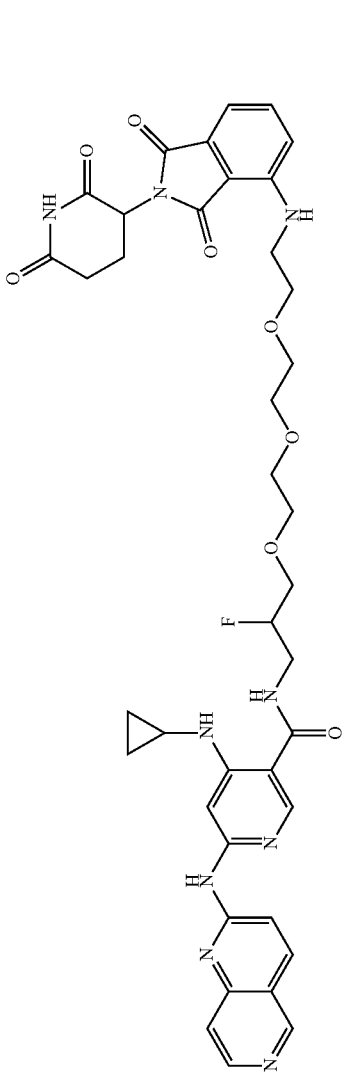 |
| I-50 | 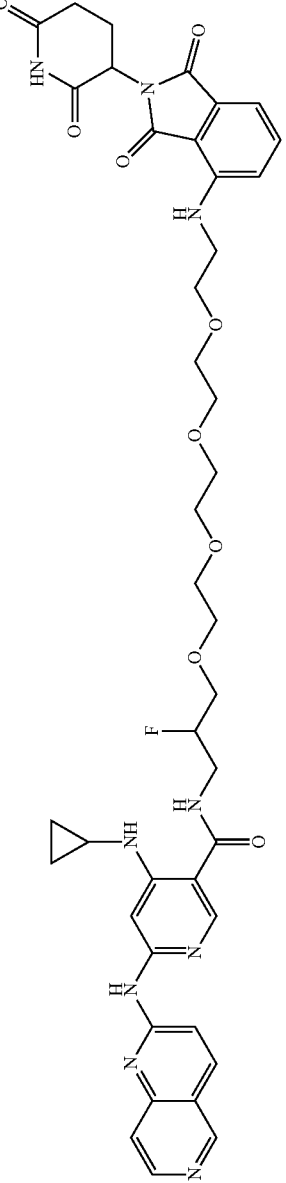 |

TABLE 1-continued

Exemplary Compounds

| I-# | Structure |
|---|---|
| I-51 | 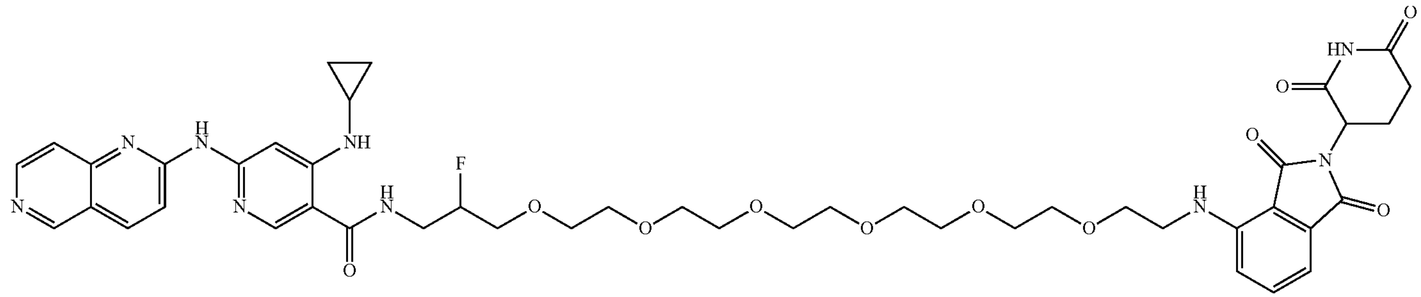 [SMILES: O=C1CCC(N2C(=O)c3cccc(NCCOCCOCCOCCOCCOCCOCC(F)CNC(=O)c4cnc(Nc5ccc6cnccc6n5)cc4NC4CC4)c3C2=O)C(=O)N1] |
| I-52 | 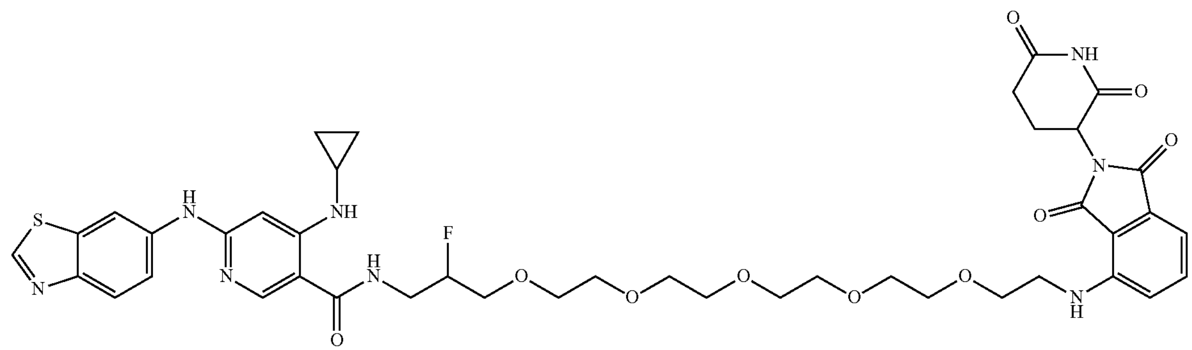 [SMILES: O=C1CCC(N2C(=O)c3cccc(NCCOCCOCCOCCOCCOCC(F)CNC(=O)c4cnc(Nc5ccc6ncsc6c5)cc4NC4CC4)c3C2=O)C(=O)N1] |
| I-53 | 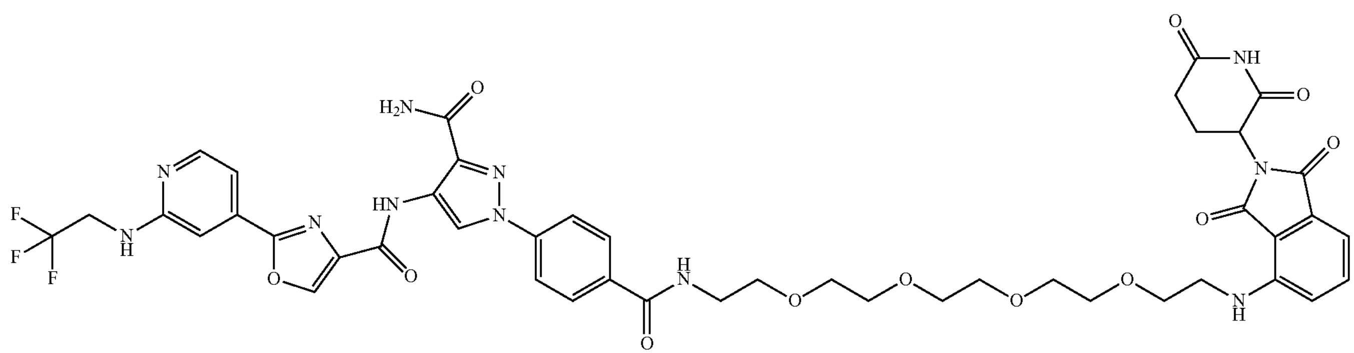 [SMILES: NC(=O)c1nn(-c2ccc(C(=O)NCCOCCOCCOCCOCCNc3cccc4c3C(=O)N(C3CCC(=O)NC3=O)C4=O)cc2)cc1NC(=O)c1coc(-c2ccnc(NCC(F)(F)F)c2)n1] |

TABLE 1-continued

Exemplary Compounds

| I-# | Structure |
|---|---|
| I-54 | 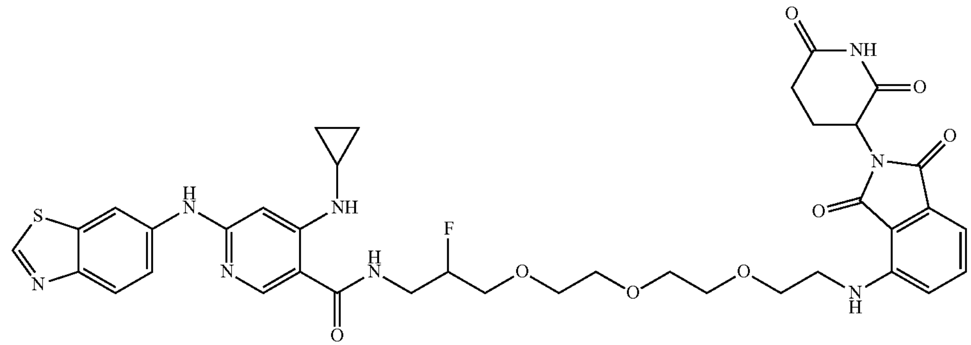 [SMILES: O=C1CCC(N2C(=O)c3cccc(NCCOCCOCCOCC(F)CNC(=O)c4cnc(Nc5ccc6ncsc6c5)cc4NC4CC4)c3C2=O)C(=O)N1] |
| I-55 | 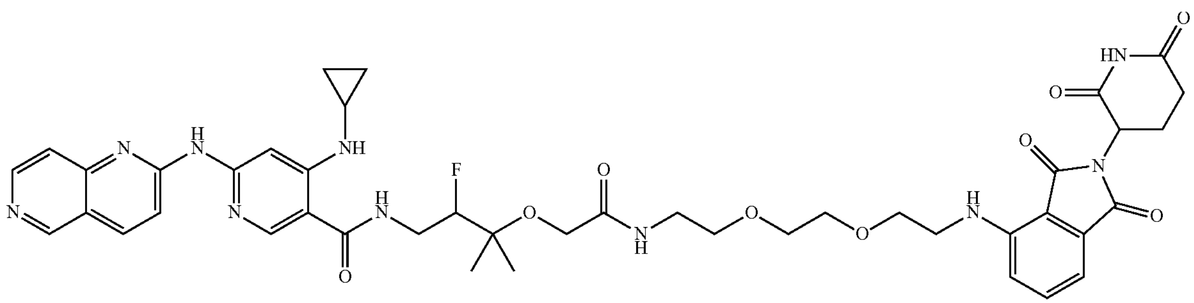 [SMILES: CC(C)(OCC(=O)NCCOCCOCCNc1cccc2c1C(=O)N(C1CCC(=O)NC1=O)C2=O)C(F)CNC(=O)c1cnc(Nc2ccc3cnccc3n2)cc1NC1CC1] |
| I-56 | 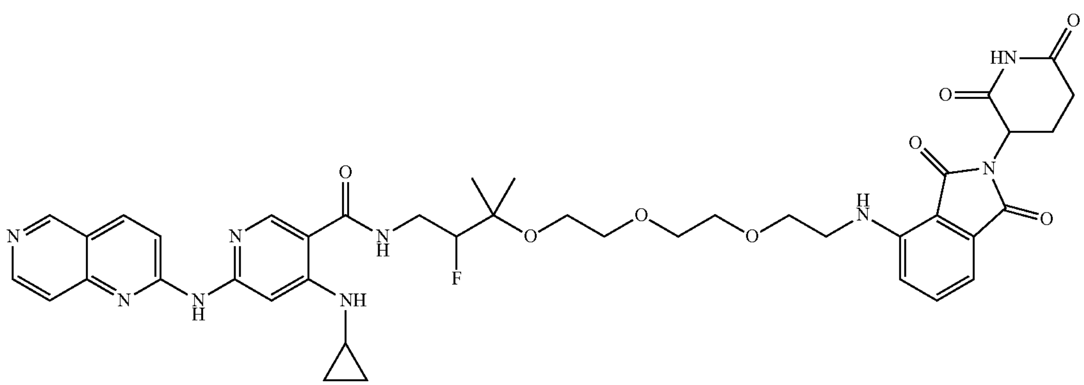 [SMILES: CC(C)(OCCOCCOCCNc1cccc2c1C(=O)N(C1CCC(=O)NC1=O)C2=O)C(F)CNC(=O)c1cnc(Nc2ccc3cnccc3n2)cc1NC1CC1] |

TABLE 1-continued
Exemplary Compounds
| I-# | Structure |
|---|---|
| I-57 | 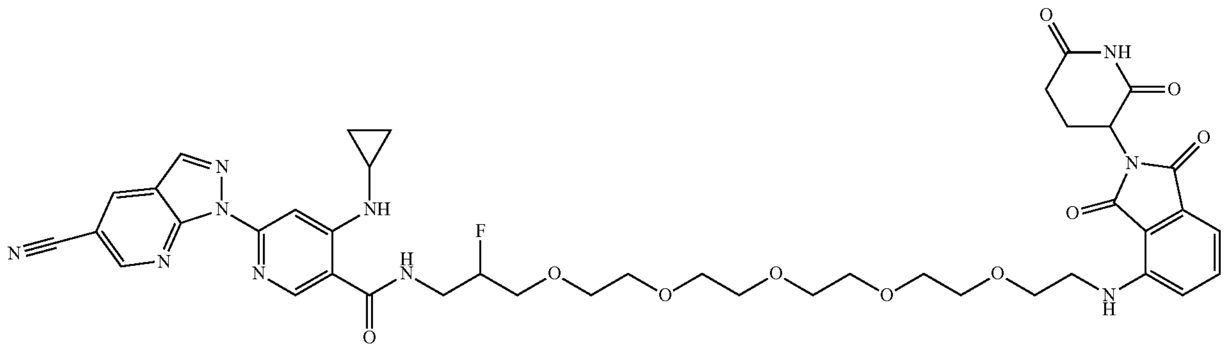 [SMILES: N#Cc1cnc2c(cnn2-c2cc(NC3CC3)c(C(=O)NCC(F)COCCOCCOCCOCCOCCNc3cccc4c3C(=O)N(C3CCC(=O)NC3=O)C4=O)cn2)c1] |
| I-58 | 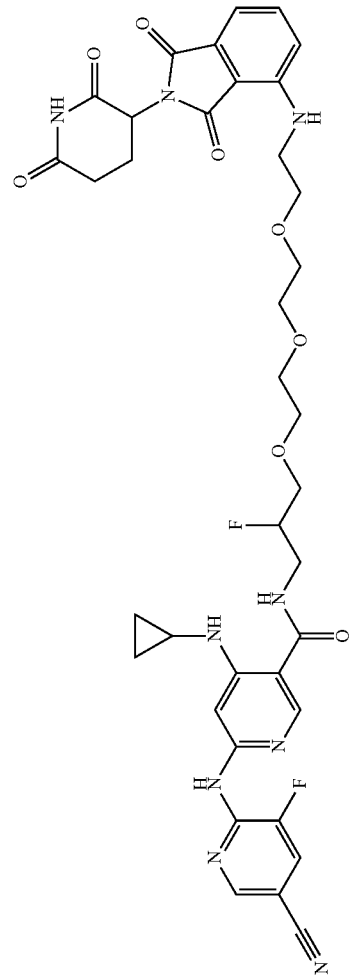 |

TABLE 1-continued
Exemplary Compounds
| I-# | Structure |
|---|---|
| I-59 | 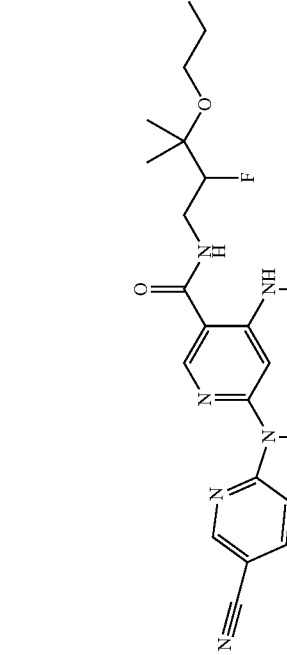 |
| I-60 | 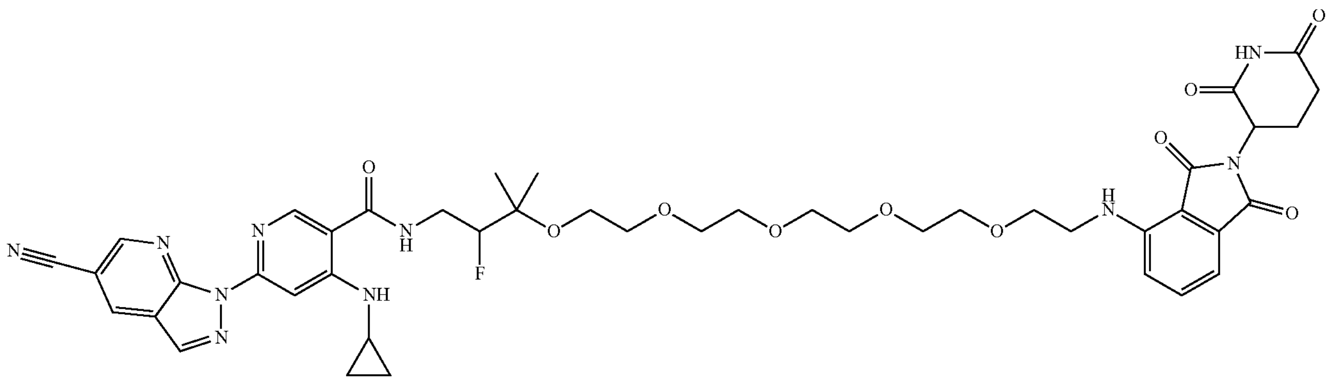 [SMILES: CC(C)(OCCOCCOCCOCCOCCNc1cccc2c1C(=O)N(C1CCC(=O)NC1=O)C2=O)C(F)CNC(=O)c1cnc(-n2ncc3cc(C#N)cnc32)cc1NC1CC1] |

TABLE 1-continued
Exemplary Compounds
| I-# | Structure |
|---|---|
| I-61 | 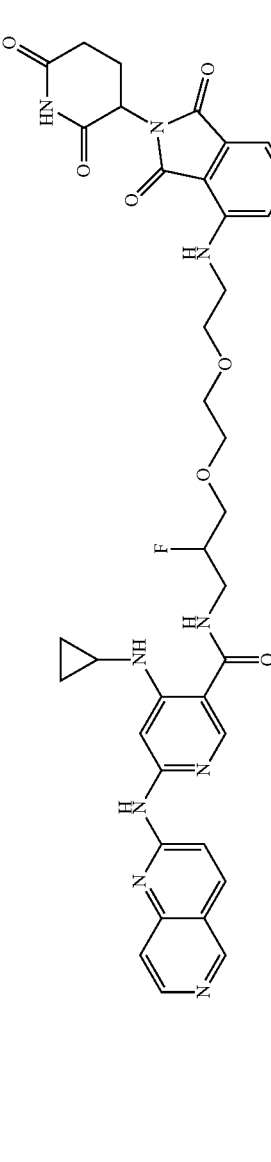 |
| I-62 | 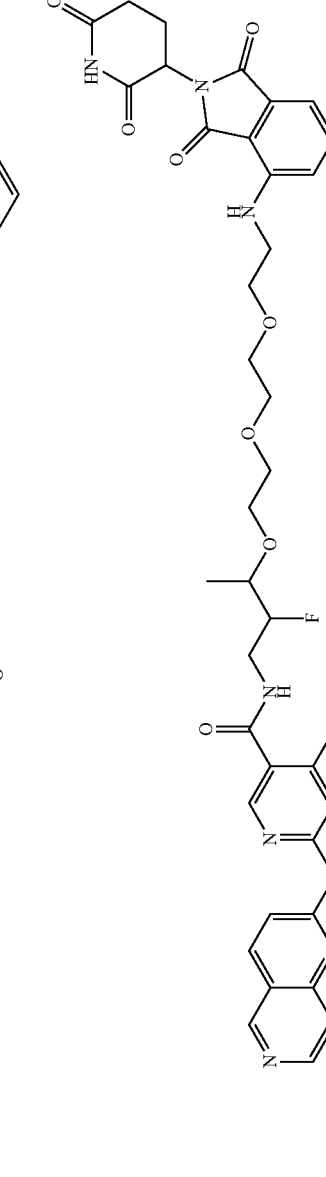 |

TABLE 1-continued
Exemplary Compounds
| I-# | Structure |
|---|---|
| I-63 | 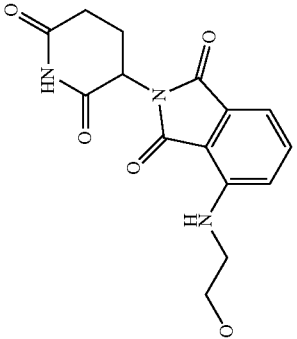 |
| I-64 | 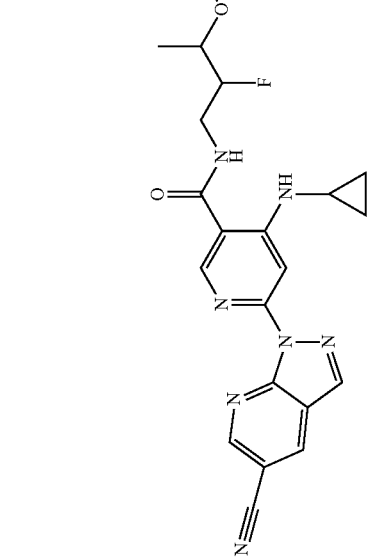 |

TABLE 1-continued
Exemplary Compounds
| I-# | Structure |
|---|---|
| I-65 | 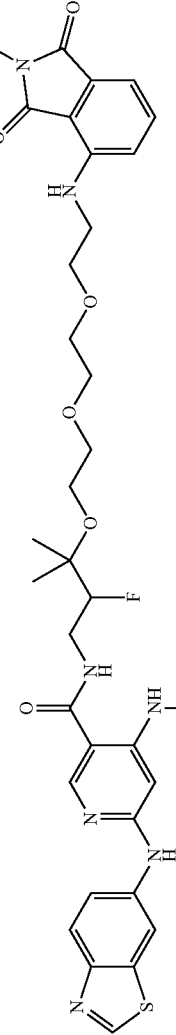 |
| I-66 | 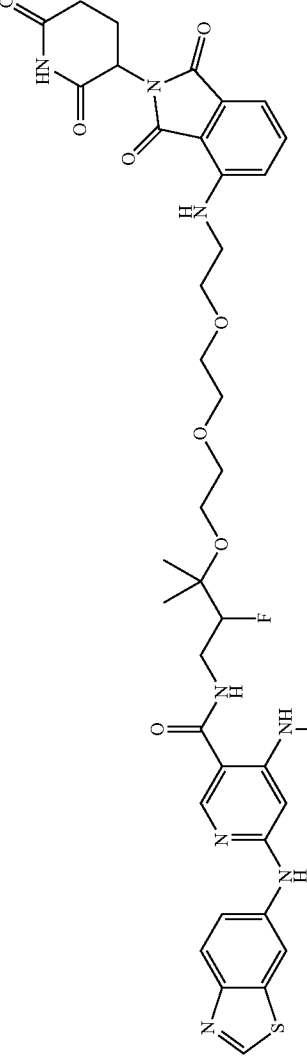 |

TABLE 1-continued
Exemplary Compounds
| I-# | Structure |
|---|---|
| I-67 | 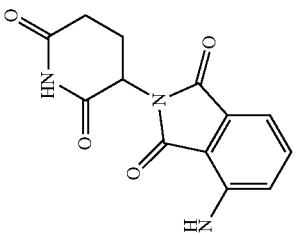 |
| I-68 | 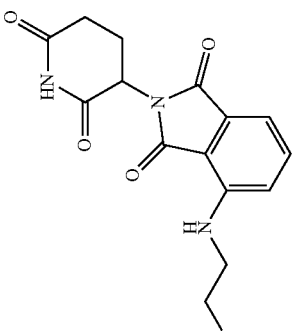 |

TABLE 1-continued
Exemplary Compounds
| I-# | Structure |
|---|---|
| I-69 | 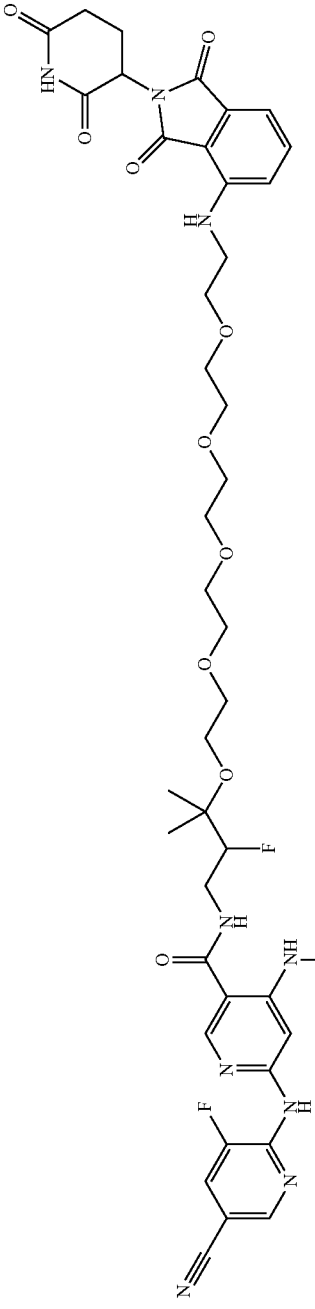 |
| I-70 | 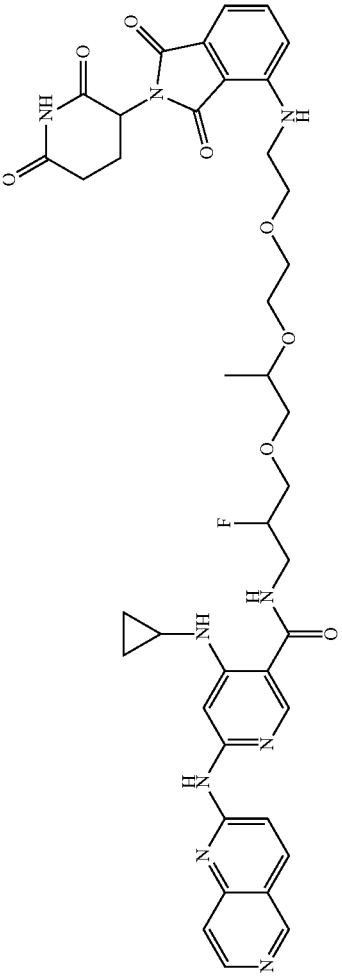 |
| I-71 | 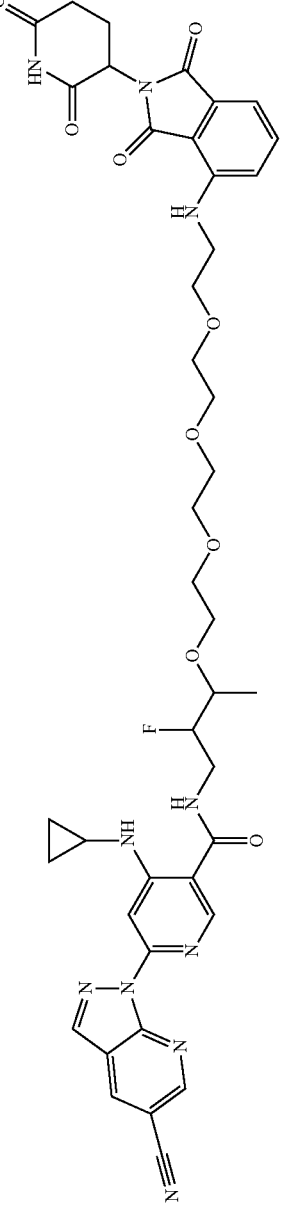 |

TABLE 1-continued

Exemplary Compounds

| I-# | Structure |
|---|---|
| I-72 | 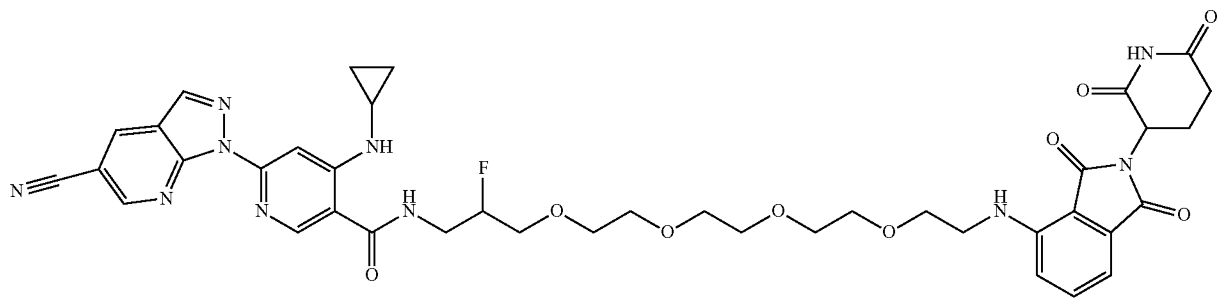 [SMILES: N#Cc1cnc2c(cnn2-c2cc(NC3CC3)c(C(=O)NCC(F)COCCOCCOCCOCCNc3cccc4c3C(=O)N(C3CCC(=O)NC3=O)C4=O)cn2)c1] |
| I-73 | 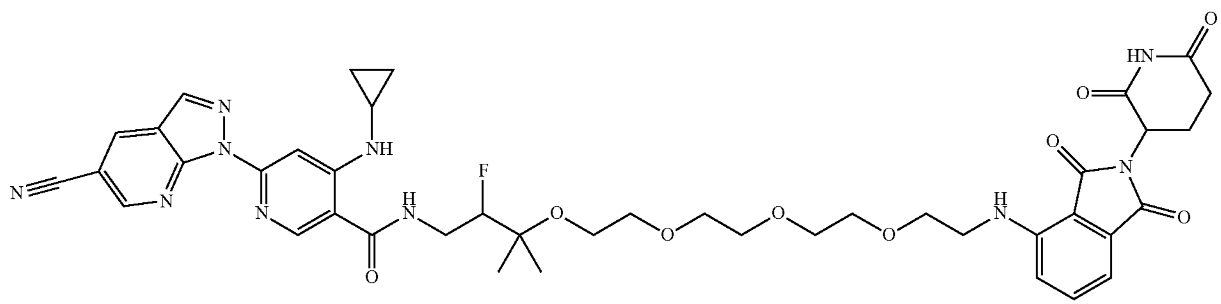 [SMILES: CC(C)(OCCOCCOCCOCCNc1cccc2c1C(=O)N(C1CCC(=O)NC1=O)C2=O)C(F)CNC(=O)c1cnc(-n2ncc3cc(C#N)cnc32)cc1NC1CC1] |
| I-74 | 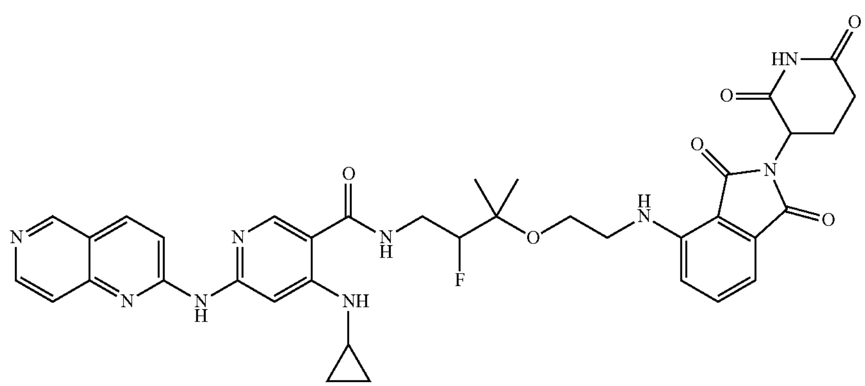 [SMILES: CC(C)(OCCNc1cccc2c1C(=O)N(C1CCC(=O)NC1=O)C2=O)C(F)CNC(=O)c1cnc(Nc2ccc3cnccc3n2)cc1NC1CC1] |

TABLE 1-continued
Exemplary Compounds
| I-# | Structure |
|---|---|
| I-75 | 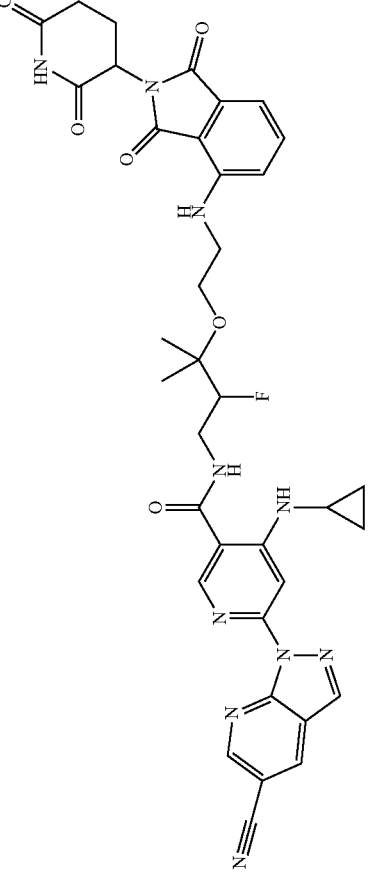 |
| I-76 | 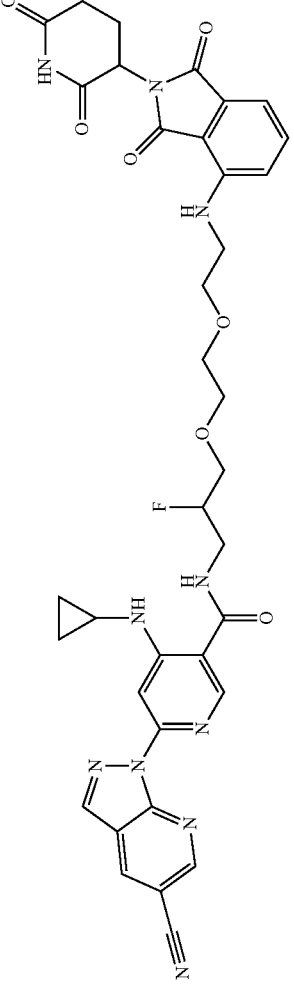 |

TABLE 1-continued
Exemplary Compounds
| I-# | Structure |
|---|---|
| I-77 | 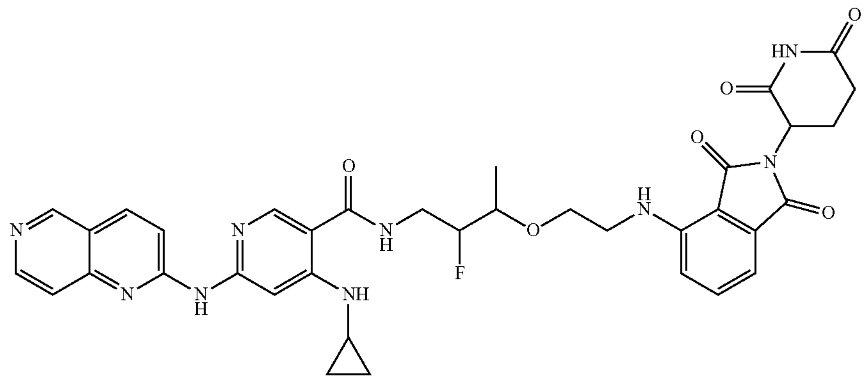 [SMILES: CC(OCCNc1cccc2c1C(=O)N(C1CCC(=O)NC1=O)C2=O)C(F)CNC(=O)c1cnc(Nc2ccc3cnccc3n2)cc1NC1CC1] |
| I-78 | 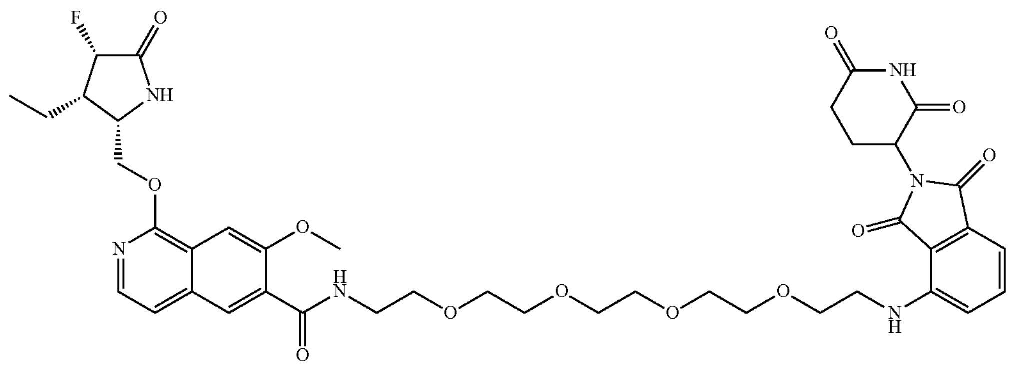 [SMILES: CC[C@@H]1[C@H](F)C(=O)N[C@@H]1COc1nccc2cc(C(=O)NCCOCCOCCOCCOCCNc3cccc4c3C(=O)N(C3CCC(=O)NC3=O)C4=O)c(OC)cc12] |

TABLE 1-continued
Exemplary Compounds
| I-# | Structure |
|---|---|
| I-79 | 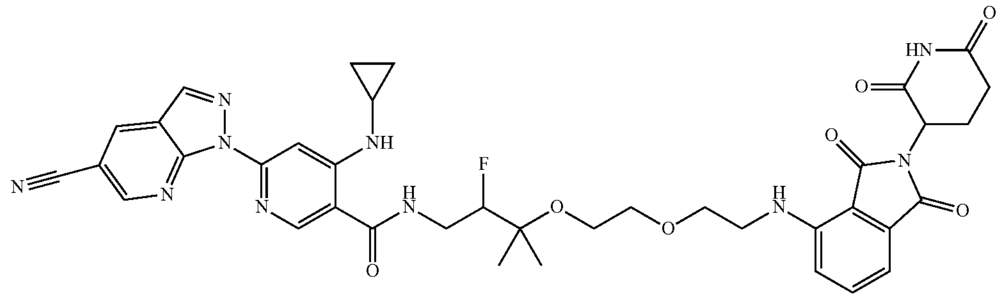 [SMILES: CC(C)(OCCOCCNc1cccc2c1C(=O)N(C1CCC(=O)NC1=O)C2=O)C(F)CNC(=O)c1cnc(-n2ncc3cc(C#N)cnc32)cc1NC1CC1] |
| I-80 | 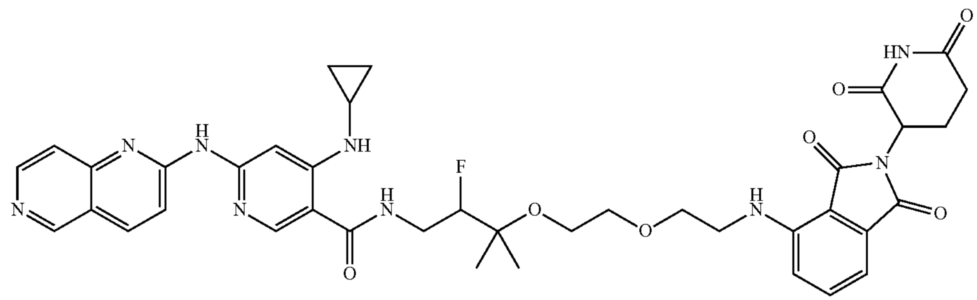 [SMILES: CC(C)(OCCOCCNc1cccc2c1C(=O)N(C1CCC(=O)NC1=O)C2=O)C(F)CNC(=O)c1cnc(Nc2ccc3cnccc3n2)cc1NC1CC1] |
| I-81 | 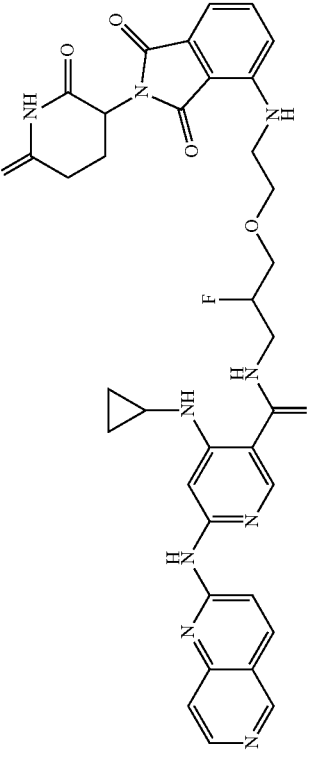 |

TABLE 1-continued
Exemplary Compounds
| I-# | Structure |
|---|---|
| I-82 | 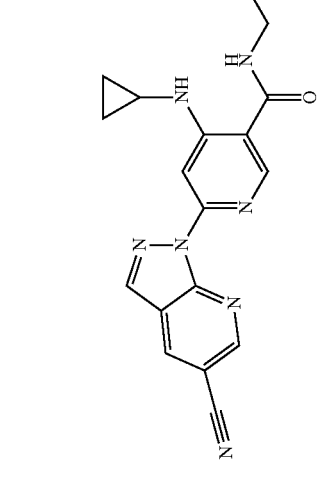 |
| I-83 | 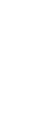 |
| I-84 | 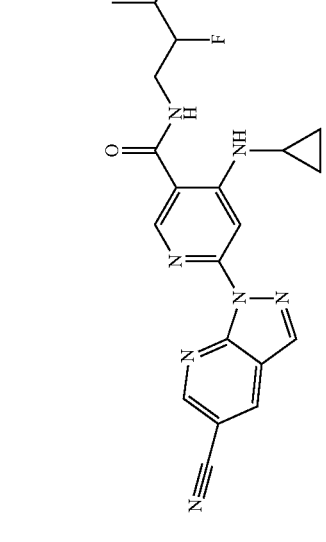 |

TABLE 1-continued
Exemplary Compounds
| I-# | Structure |
|---|---|
| I-85 | 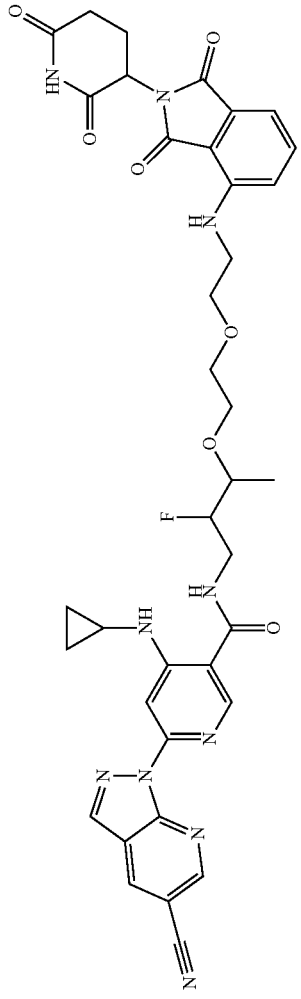 |
| I-86 | 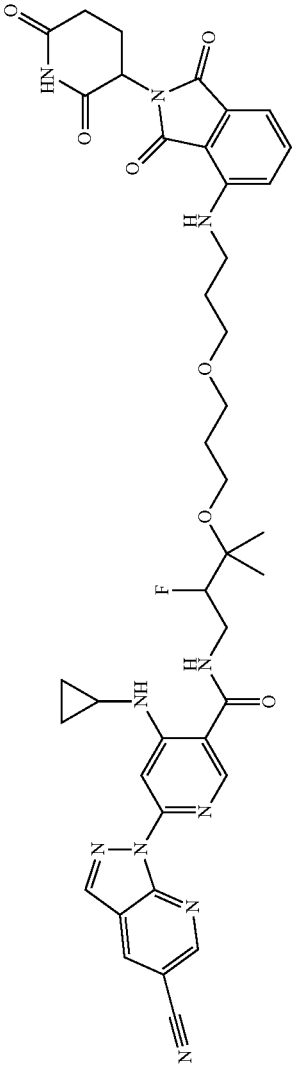 |
| I-87 | 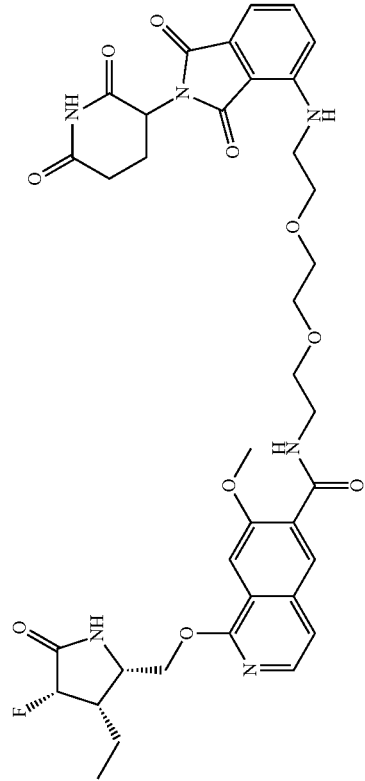 |

TABLE 1-continued
Exemplary Compounds
| I-# | Structure |
|---|---|
| I-88 | 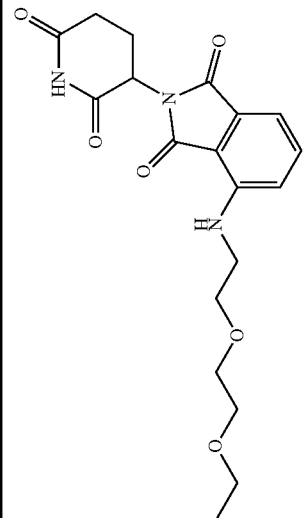 |
| I-89 | 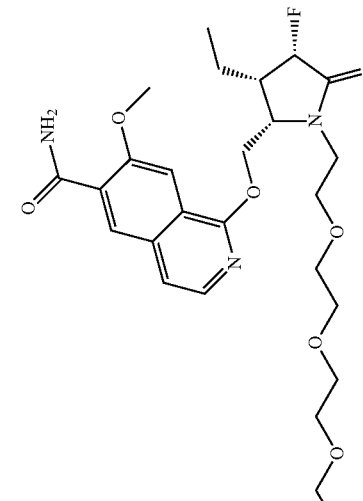 |

TABLE 1-continued
Exemplary Compounds
| I-# | Structure |
|---|---|
| I-90 | 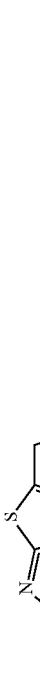 |

TABLE 1-continued
Exemplary Compounds
| I-# | Structure |
|---|---|
| I-91 | 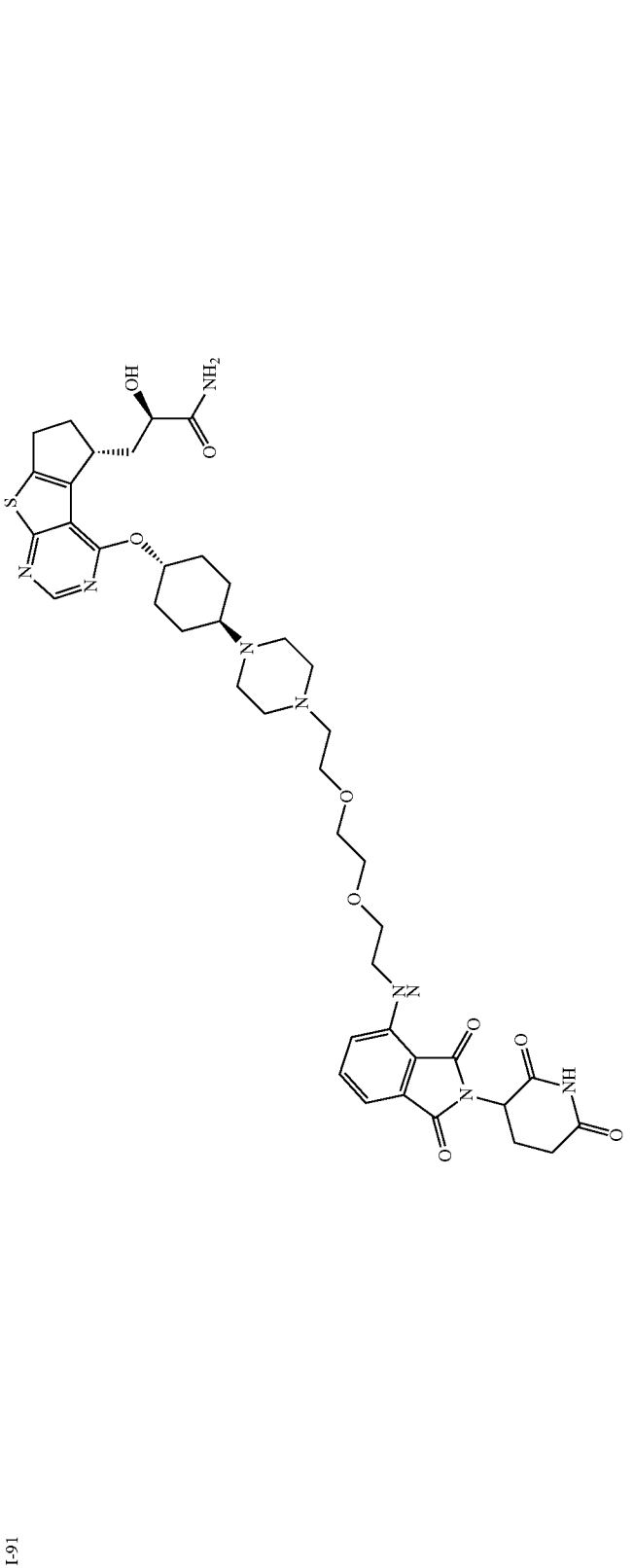 |

TABLE 1-continued
Exemplary Compounds
| I-# | Structure |
|---|---|
| I-92 | 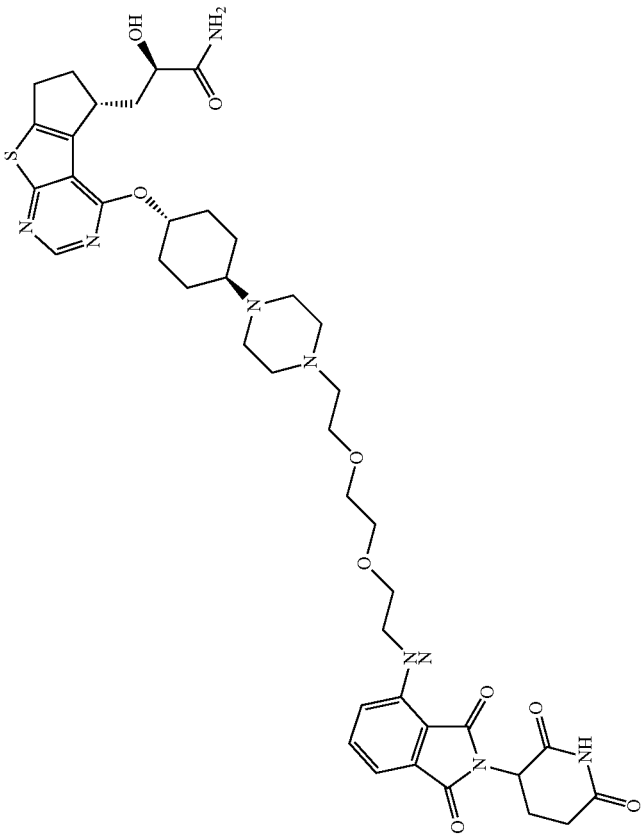 |
| I-93 | 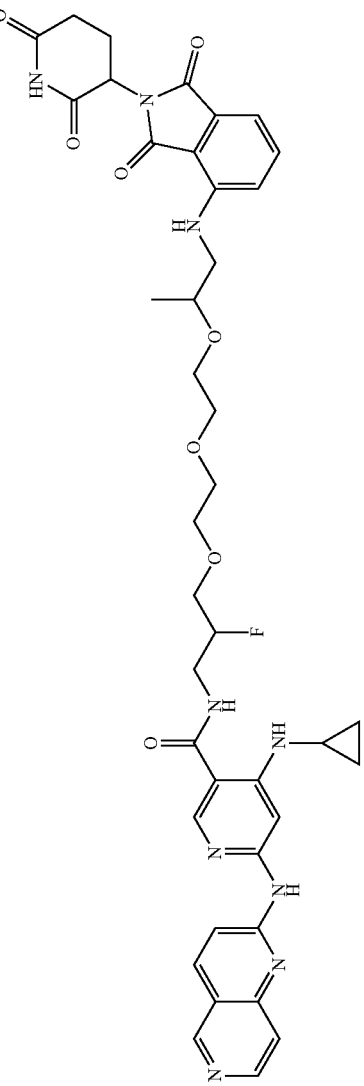 |

TABLE 1-continued
Exemplary Compounds
| I-# | Structure |
|---|---|
| I-94 | 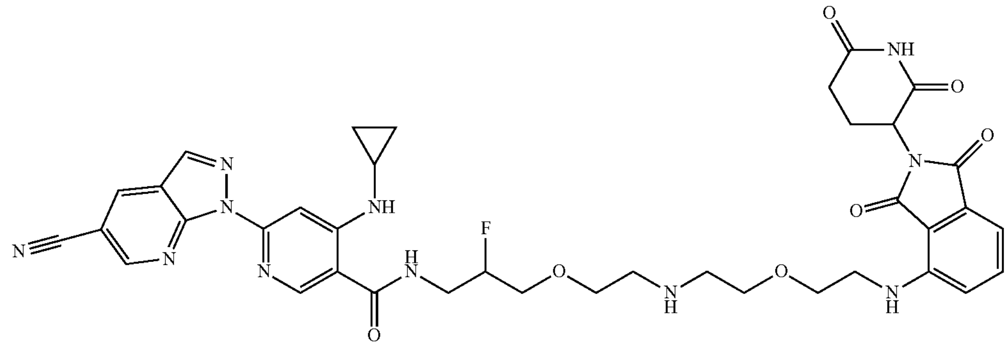 [SMILES: N#Cc1cnc2c(cnn2-c2cc(NC3CC3)c(C(=O)NCC(F)COCCNCCOCCNc3cccc4c3C(=O)N(C3CCC(=O)NC3=O)C4=O)cn2)c1] |
| I-95 | 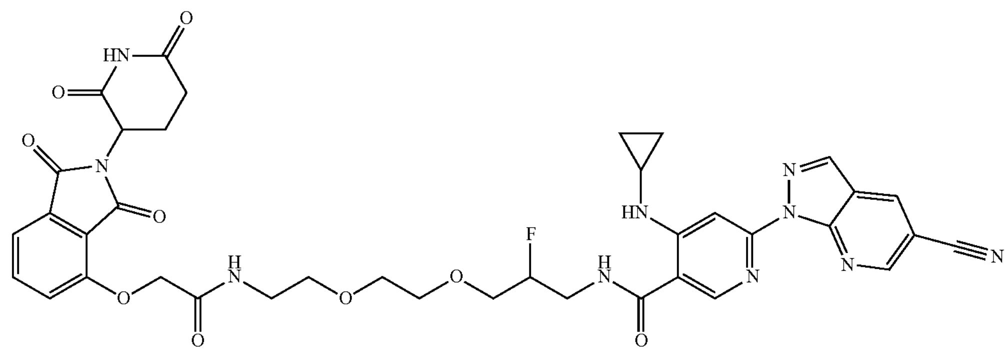 [SMILES: N#Cc1cnc2c(cnn2-c2cc(NC3CC3)c(C(=O)NCC(F)COCCOCCNC(=O)COc3cccc4c3C(=O)N(C3CCC(=O)NC3=O)C4=O)cn2)c1] |
| I-96 | 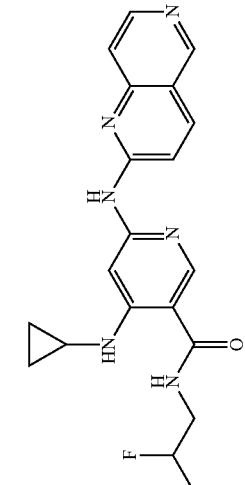 |

TABLE 1-continued

Exemplary Compounds

| I-# | Structure |
|---|---|
| I-97 | 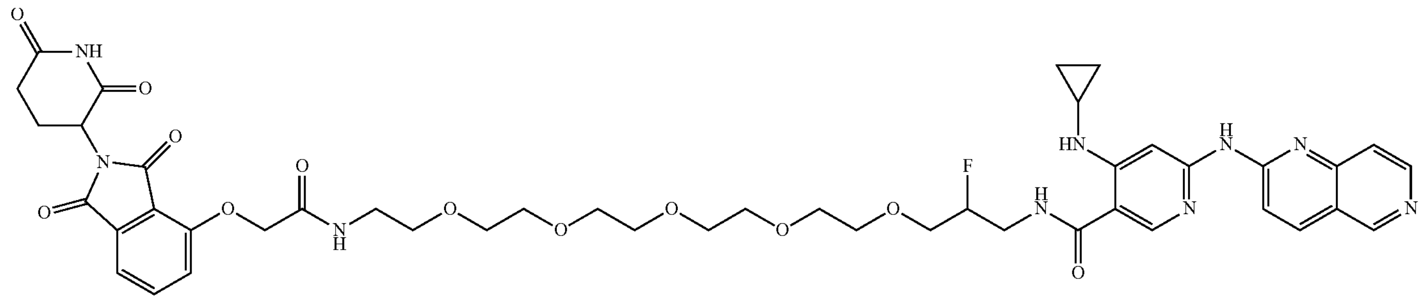 |
| I-98 | 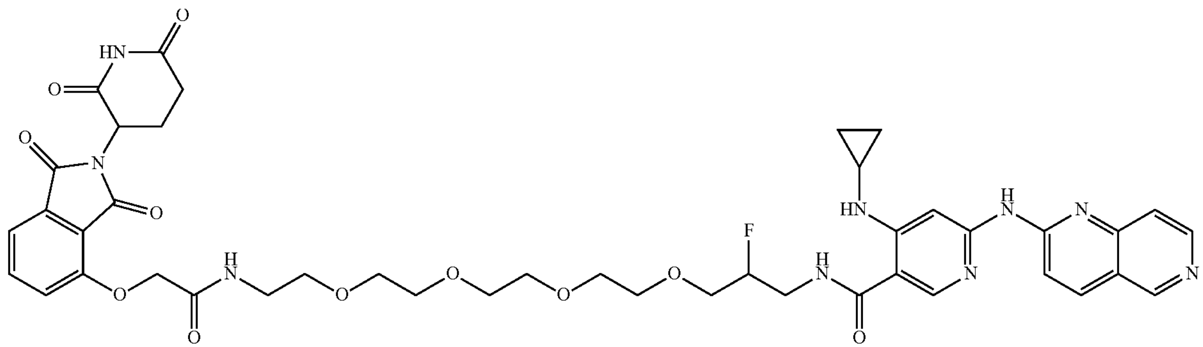 [SMILES: O=C(COc1cccc2c1C(=O)N(C1CCC(=O)NC1=O)C2=O)NCCOCCOCCOCCOCC(F)CNC(=O)c1cnc(Nc2ccc3cnccc3n2)cc1NC1CC1] |
| I-99 | 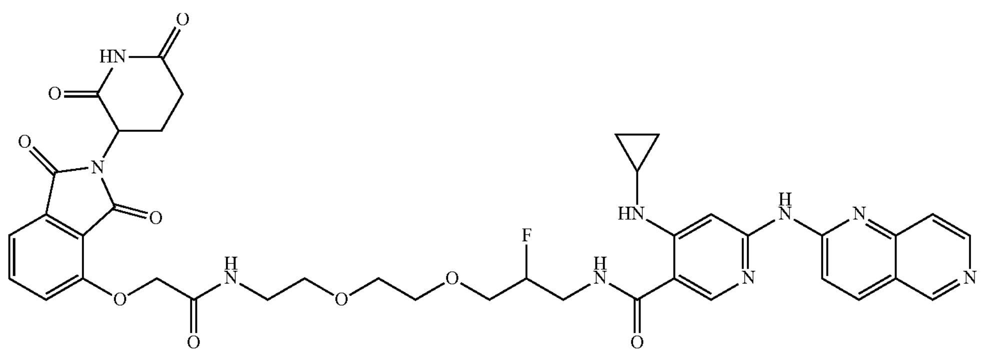 [SMILES: O=C(COc1cccc2c1C(=O)N(C1CCC(=O)NC1=O)C2=O)NCCOCCOCC(F)CNC(=O)c1cnc(Nc2ccc3cnccc3n2)cc1NC1CC1] |

TABLE 1-continued
Exemplary Compounds
| I-# | Structure |
|---|---|
| I-100 | 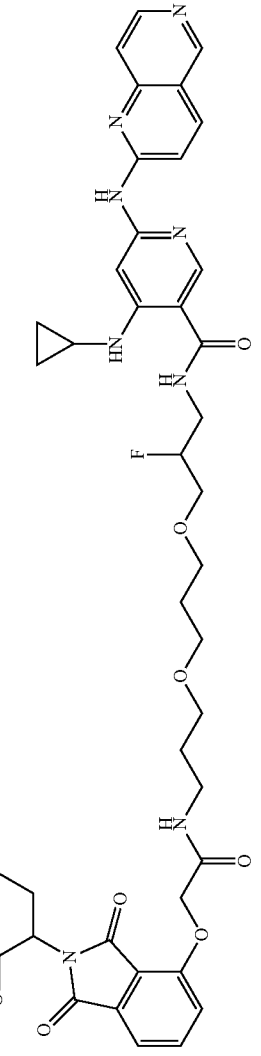 |
| I-101 | 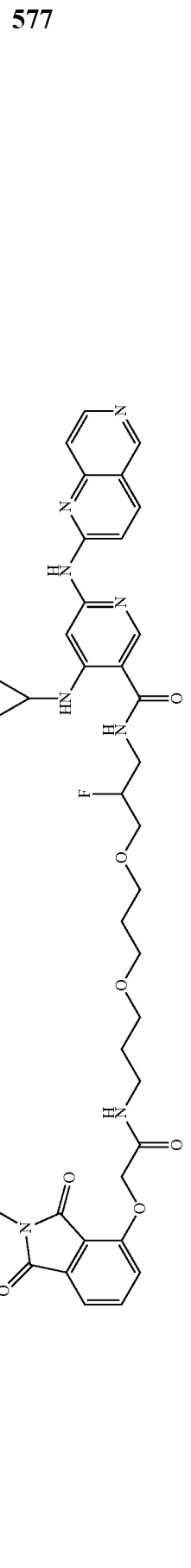 |

TABLE 1-continued
Exemplary Compounds
| I-# | Structure |
|---|---|
| I-102 | 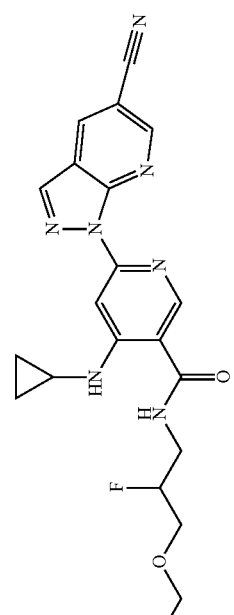 |
| I-103 | 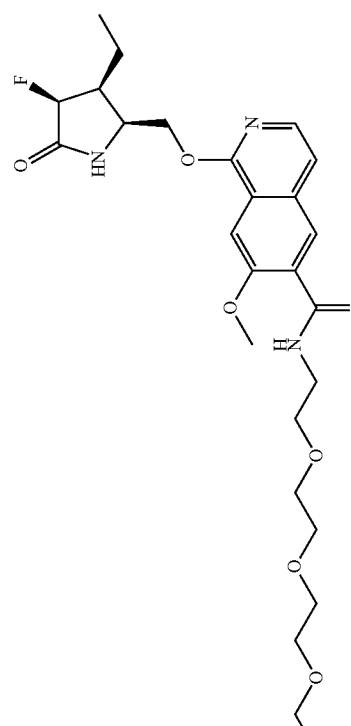 |

TABLE 1-continued
Exemplary Compounds
| I-# | Structure |
|---|---|
| I-104 | 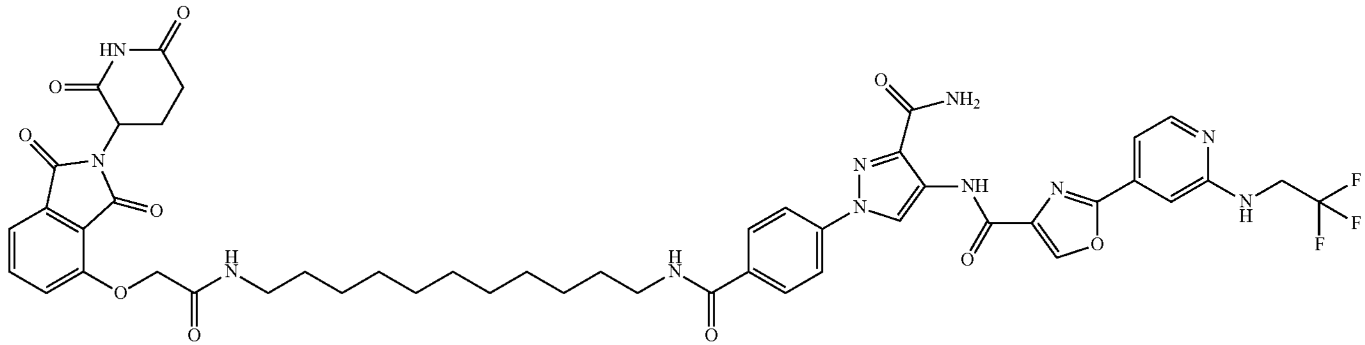 [SMILES: NC(=O)c1nn(-c2ccc(C(=O)NCCCCCCCCCCCNC(=O)COc3cccc4c3C(=O)N(C3CCC(=O)NC3=O)C4=O)cc2)cc1NC(=O)c1coc(-c2ccnc(NCC(F)(F)F)c2)n1] |
| I-105 | 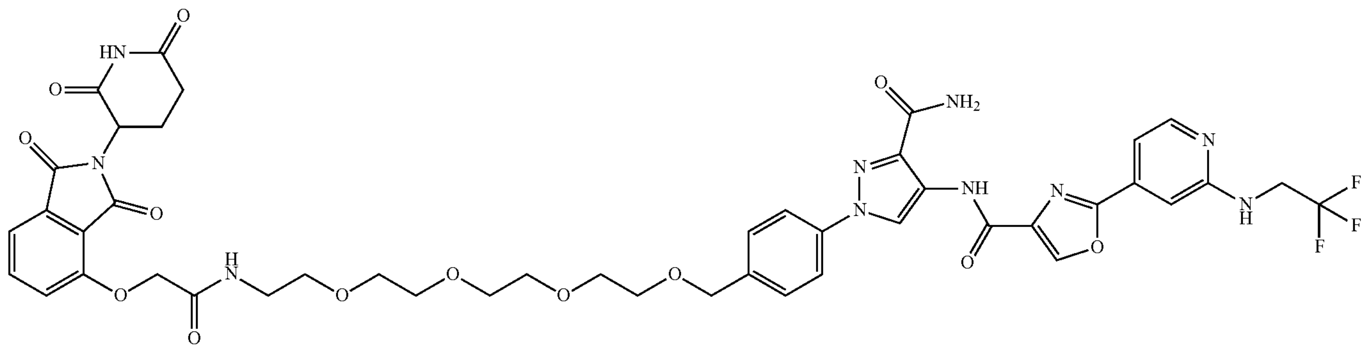 [SMILES: NC(=O)c1nn(-c2ccc(COCCOCCOCCOCCNC(=O)COc3cccc4c3C(=O)N(C3CCC(=O)NC3=O)C4=O)cc2)cc1NC(=O)c1coc(-c2ccnc(NCC(F)(F)F)c2)n1] |

TABLE 1-continued
Exemplary Compounds
| I-# | Structure |
|---|---|
| I-106 | 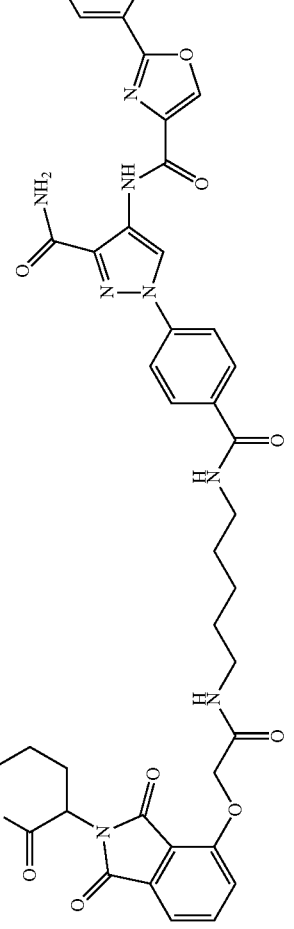 |
| I-107 | 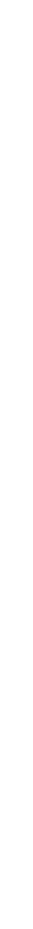 |

TABLE 1-continued

Exemplary Compounds

| I-# | Structure |
|---|---|
| I-108 | 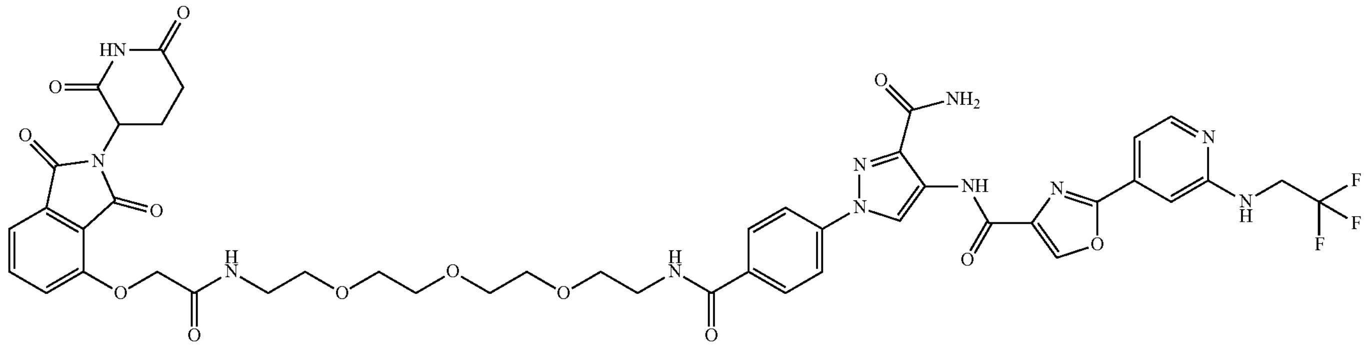 [SMILES: NC(=O)c1nn(-c2ccc(C(=O)NCCOCCOCCOCCNC(=O)COc3cccc4c3C(=O)N(C3CCC(=O)NC3=O)C4=O)cc2)cc1NC(=O)c1coc(-c2ccnc(NCC(F)(F)F)c2)n1] |
| I-109 | 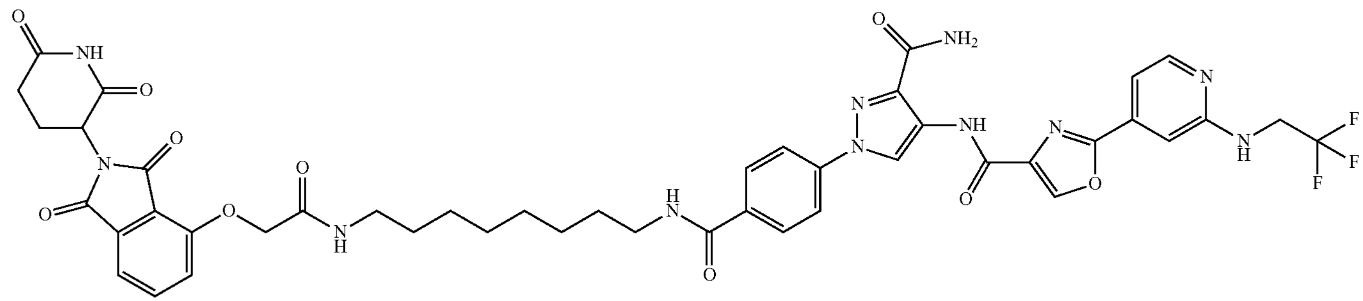 [SMILES: NC(=O)c1nn(-c2ccc(C(=O)NCCCCCCCCNC(=O)COc3cccc4c3C(=O)N(C3CCC(=O)NC3=O)C4=O)cc2)cc1NC(=O)c1coc(-c2ccnc(NCC(F)(F)F)c2)n1] |
| I-110 | 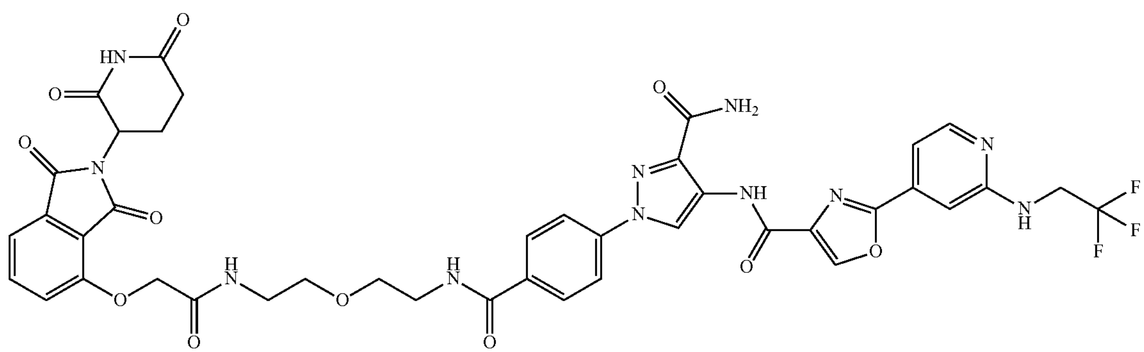 [SMILES: NC(=O)c1nn(-c2ccc(C(=O)NCCOCCNC(=O)COc3cccc4c3C(=O)N(C3CCC(=O)NC3=O)C4=O)cc2)cc1NC(=O)c1coc(-c2ccnc(NCC(F)(F)F)c2)n1] |

TABLE 1-continued
Exemplary Compounds
| I-# | Structure |
|---|---|
| I-111 | 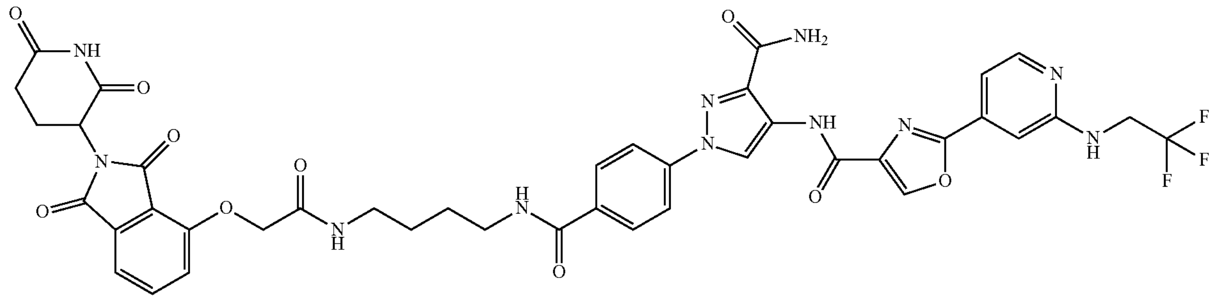 [SMILES: NC(=O)c1nn(-c2ccc(C(=O)NCCCCNC(=O)COc3cccc4c3C(=O)N(C3CCC(=O)NC3=O)C4=O)cc2)cc1NC(=O)c1coc(-c2ccnc(NCC(F)(F)F)c2)n1] |
| I-112 | 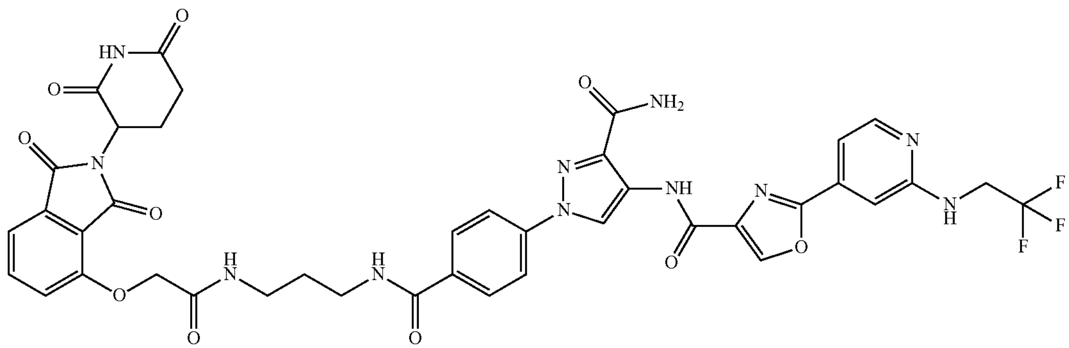 [SMILES: NC(=O)c1nn(-c2ccc(C(=O)NCCCNC(=O)COc3cccc4c3C(=O)N(C3CCC(=O)NC3=O)C4=O)cc2)cc1NC(=O)c1coc(-c2ccnc(NCC(F)(F)F)c2)n1] |
| I-113 | 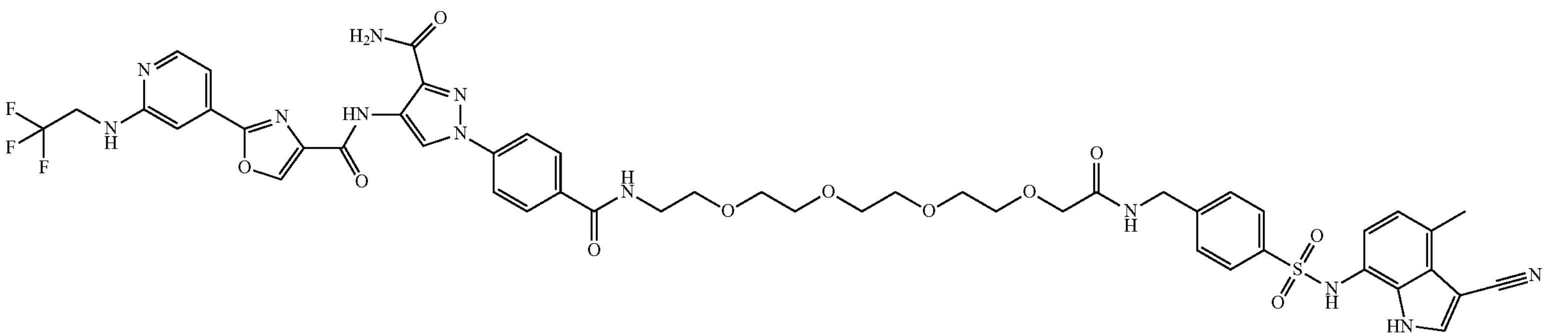 [SMILES: Cc1ccc(NS(=O)(=O)c2ccc(CNC(=O)COCCOCCOCCOCCNC(=O)c3ccc(-n4cc(NC(=O)c5coc(-c6ccnc(NCC(F)(F)F)c6)n5)c(C(N)=O)n4)cc3)cc2)c2[nH]cc(C#N)c12] |

TABLE 1-continued

Exemplary Compounds

| I-# | Structure |
|---|---|
| I-114 | 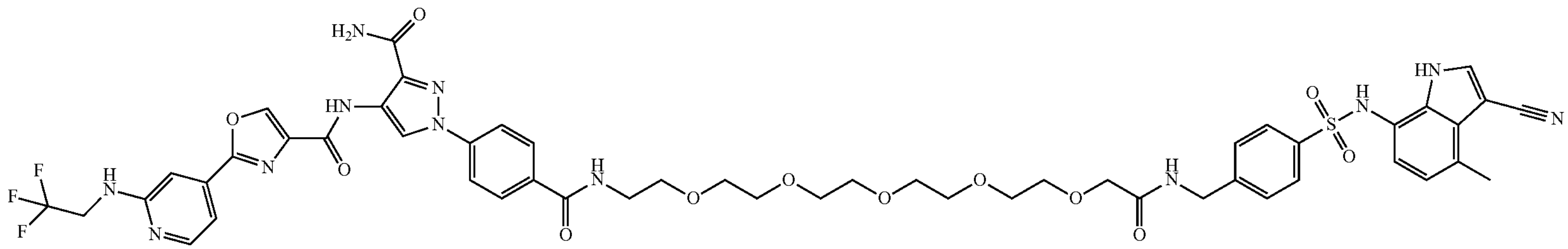 [SMILES: Cc1ccc(NS(=O)(=O)c2ccc(CNC(=O)COCCOCCOCCOCCOCCNC(=O)c3ccc(-n4cc(NC(=O)c5coc(-c6ccnc(NCC(F)(F)F)c6)n5)c(C(N)=O)n4)cc3)cc2)c2[nH]cc(C#N)c12] |
| I-115 | 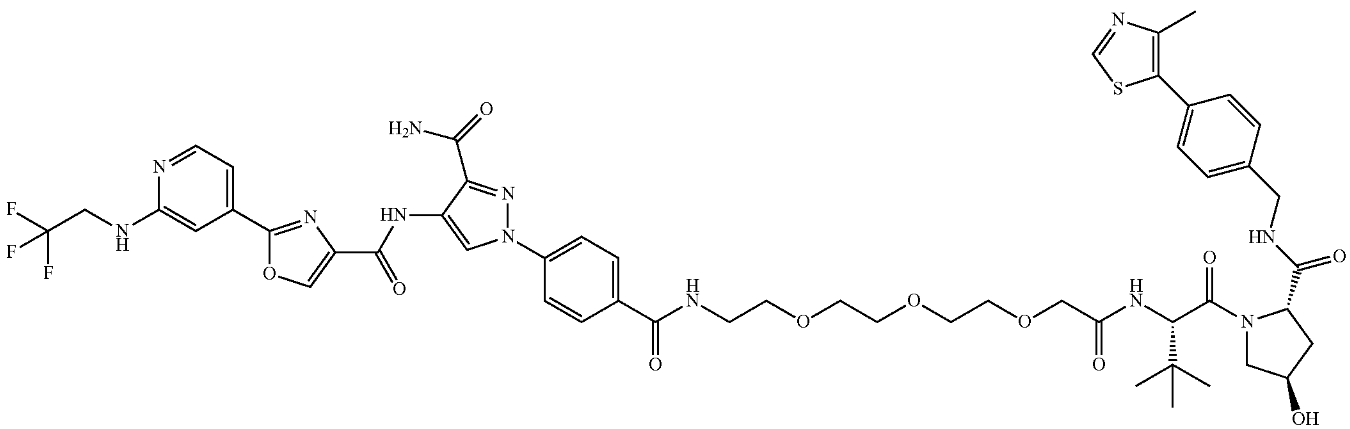 [SMILES: Cc1ncsc1-c1ccc(CNC(=O)[C@@H]2C[C@@H](O)CN2C(=O)[C@@H](NC(=O)COCCOCCOCCNC(=O)c2ccc(-n3cc(NC(=O)c4coc(-c5ccnc(NCC(F)(F)F)c5)n4)c(C(N)=O)n3)cc2)C(C)(C)C)cc1] |
| I-116 | 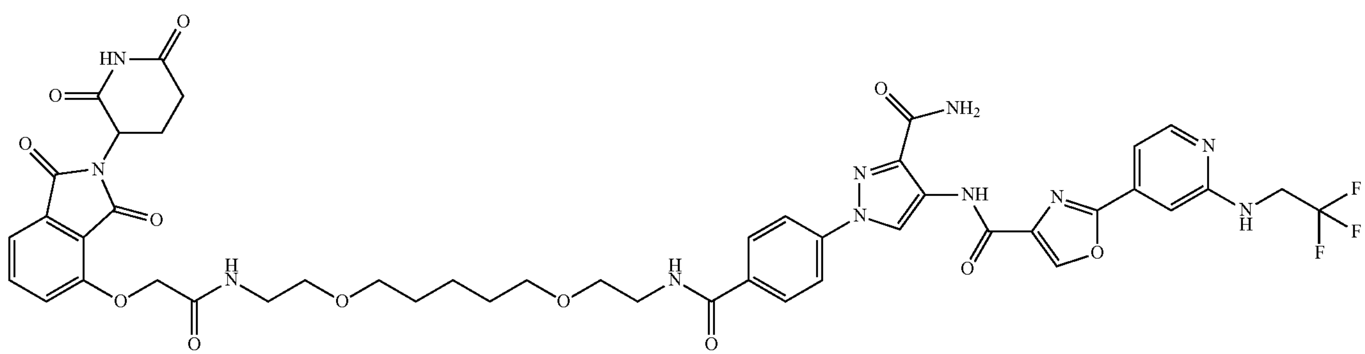 [SMILES: NC(=O)c1nn(-c2ccc(C(=O)NCCOCCCCCOCCNC(=O)COc3cccc4c3C(=O)N(C3CCC(=O)NC3=O)C4=O)cc2)cc1NC(=O)c1coc(-c2ccnc(NCC(F)(F)F)c2)n1] |

TABLE 1-continued

Exemplary Compounds

| I-# | Structure |
|---|---|
| I-117 | 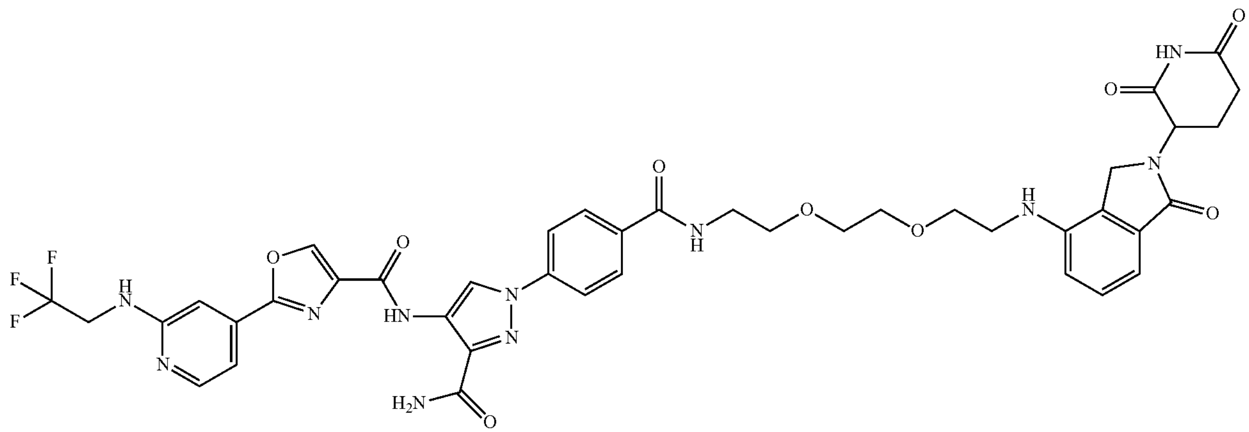 [SMILES: NC(=O)c1nn(-c2ccc(C(=O)NCCOCCOCCNc3cccc4c3CN(C3CCC(=O)NC3=O)C4=O)cc2)cc1NC(=O)c1coc(-c2ccnc(NCC(F)(F)F)c2)n1] |
| I-118 | 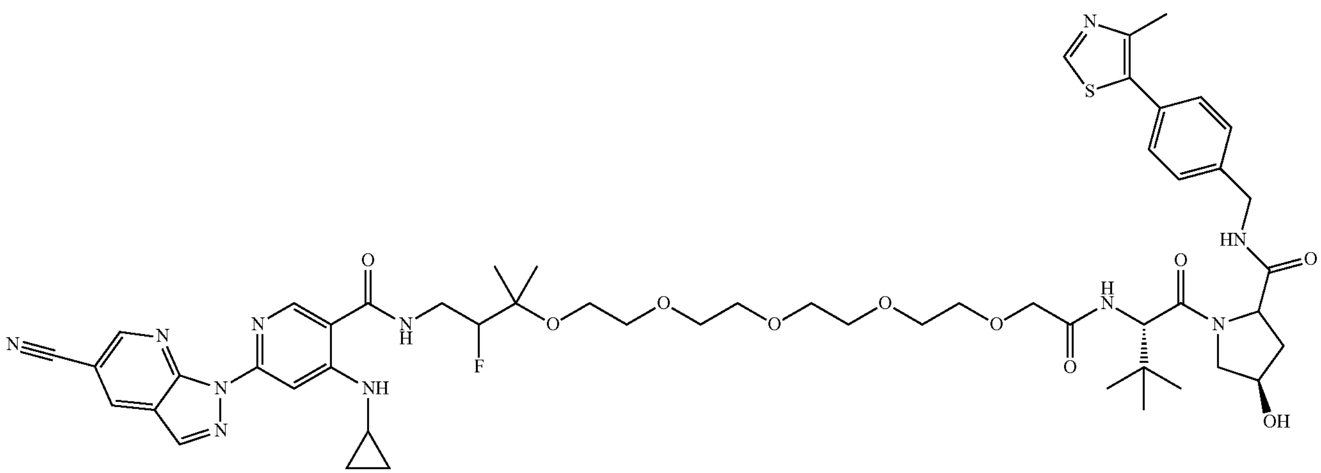 [SMILES: Cc1ncsc1-c1ccc(CNC(=O)C2C[C@@H](O)CN2C(=O)[C@@H](NC(=O)COCCOCCOCCOCCOC(C)(C)C(F)CNC(=O)c2cnc(-n3ncc4cc(C#N)cnc43)cc2NC2CC2)C(C)(C)C)cc1] |

TABLE 1-continued
Exemplary Compounds
| I-# | Structure |
|---|---|
| I-119 | 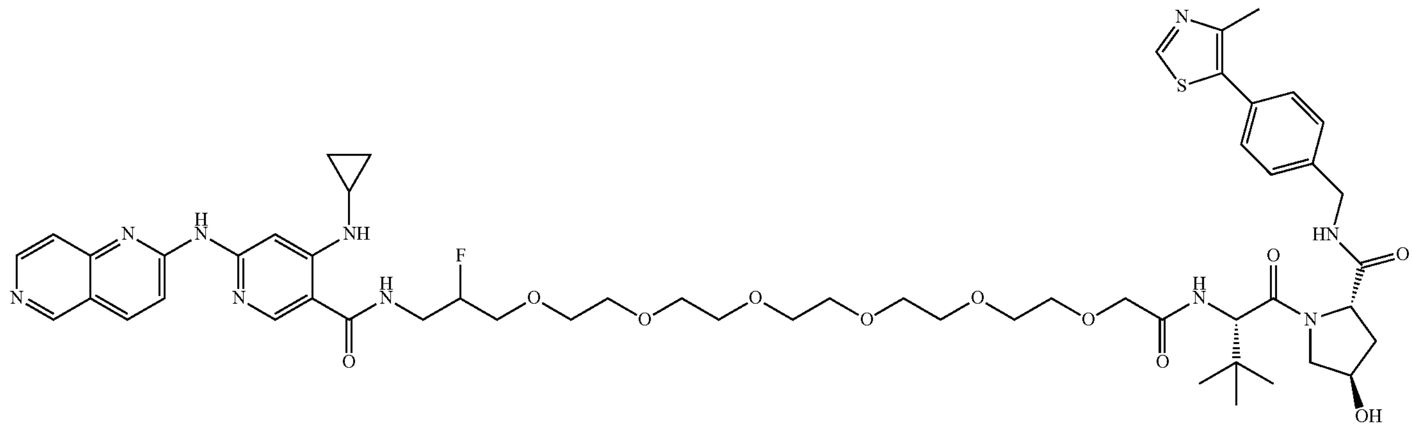 [SMILES: Cc1ncsc1-c1ccc(CNC(=O)[C@@H]2C[C@@H](O)CN2C(=O)[C@@H](NC(=O)COCCOCCOCCOCCOCCOCC(F)CNC(=O)c2cnc(Nc3ccc4cnccc4n3)cc2NC2CC2)C(C)(C)C)cc1] |
| I-120 | 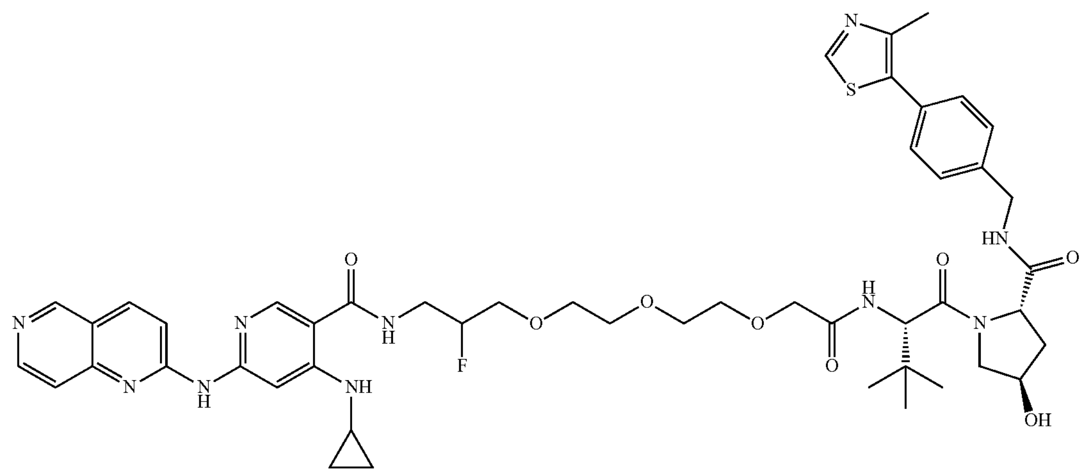 [SMILES: Cc1ncsc1-c1ccc(CNC(=O)[C@@H]2C[C@@H](O)CN2C(=O)[C@@H](NC(=O)COCCOCCOCC(F)CNC(=O)c2cnc(Nc3ccc4cnccc4n3)cc2NC2CC2)C(C)(C)C)cc1] |

TABLE 1-continued
Exemplary Compounds
| I-# | Structure |
|---|---|
| I-121 |  |
| I-122 |  |

TABLE 1-continued
Exemplary Compounds
| I-# | Structure |
|---|---|
| I-123 | 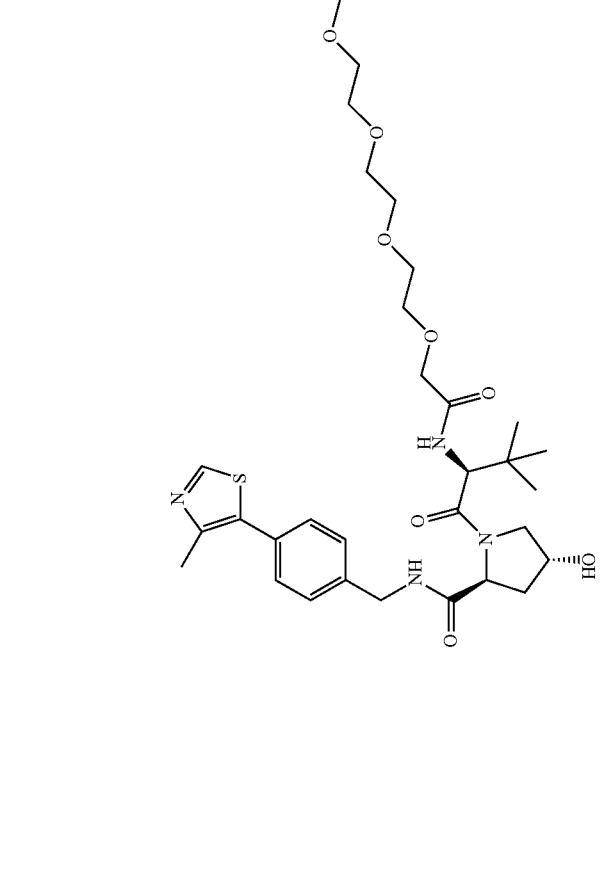 |

TABLE 1-continued
Exemplary Compounds
| I-# | Structure |
|---|---|
| I-124 | 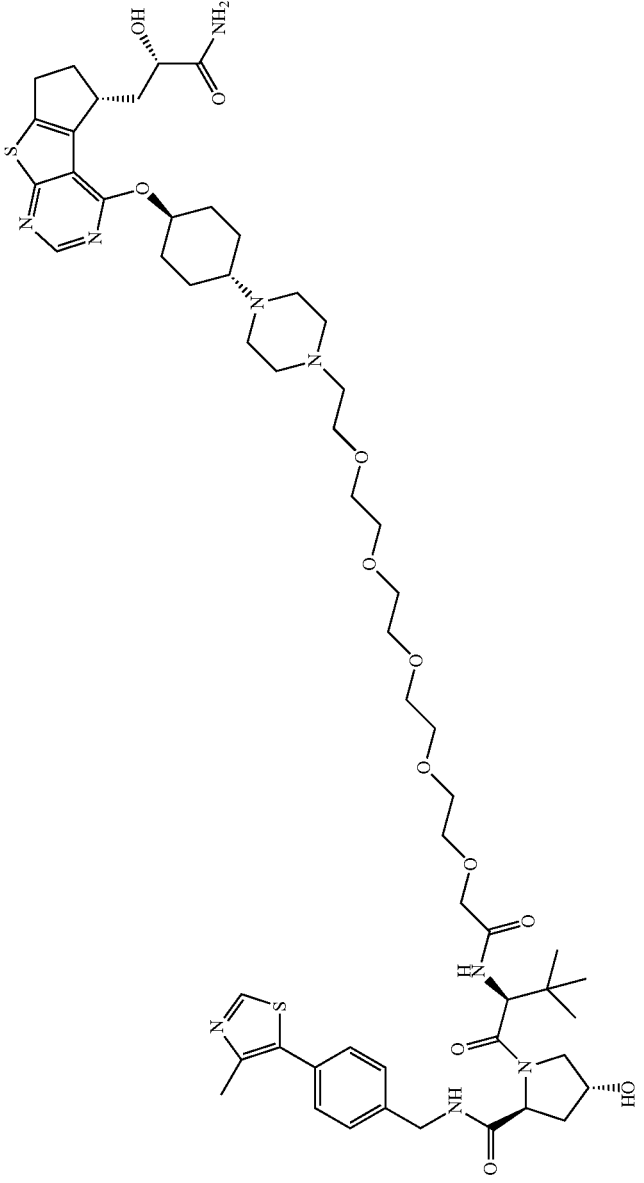 |

TABLE 1-continued
Exemplary Compounds
| I-# | Structure |
|---|---|
| I-125 | 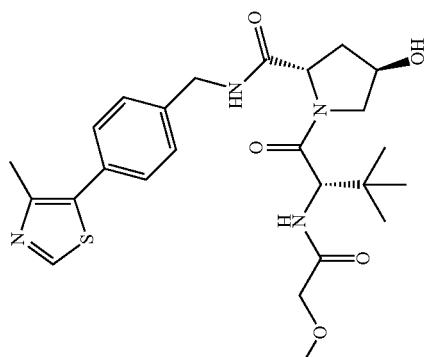 |
| I-126 | 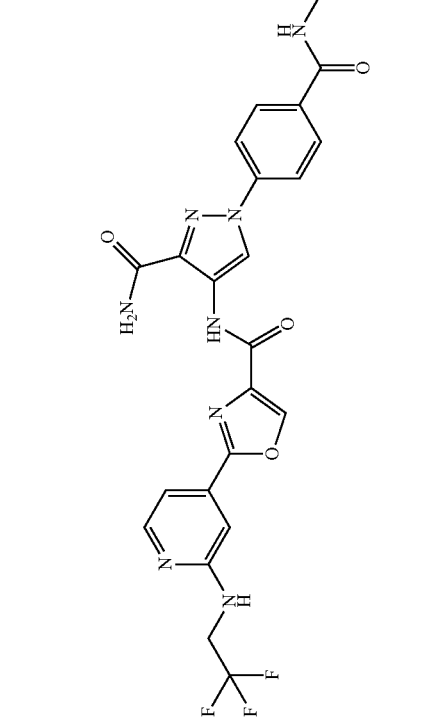 |

TABLE 1-continued

Exemplary Compounds

| I-# | Structure |
|---|---|
| I-127 | 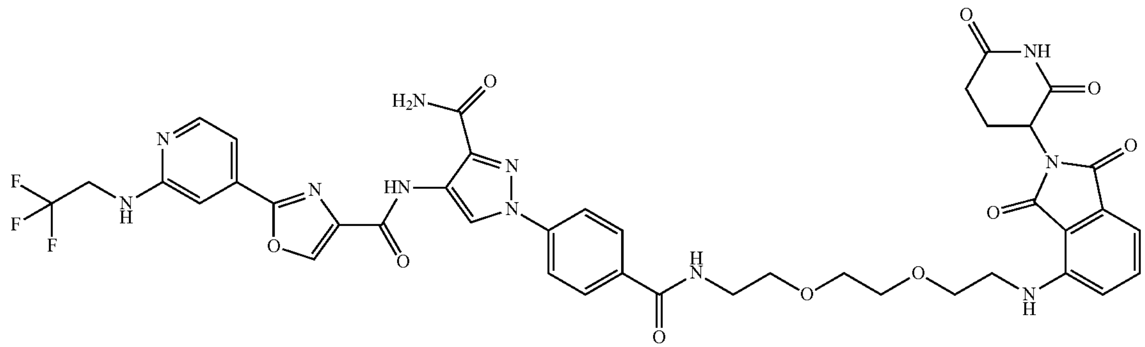 [SMILES: NC(=O)c1nn(-c2ccc(C(=O)NCCOCCOCCNc3cccc4c3C(=O)N(C3CCC(=O)NC3=O)C4=O)cc2)cc1NC(=O)c1coc(-c2ccnc(NCC(F)(F)F)c2)n1] |
| I-128 | 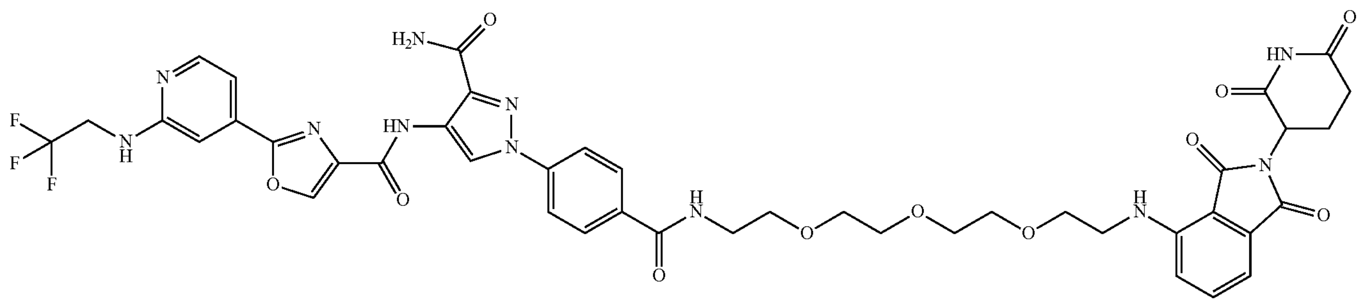 [SMILES: NC(=O)c1nn(-c2ccc(C(=O)NCCOCCOCCOCCNc3cccc4c3C(=O)N(C3CCC(=O)NC3=O)C4=O)cc2)cc1NC(=O)c1coc(-c2ccnc(NCC(F)(F)F)c2)n1] |
| I-129 | 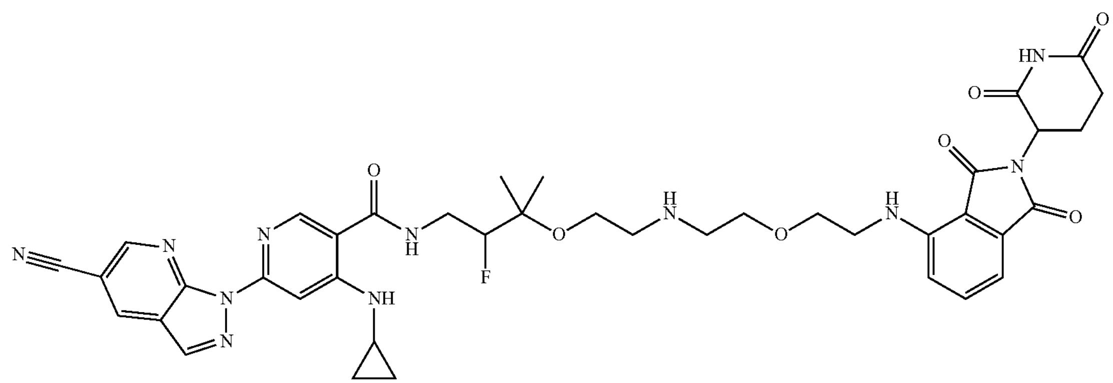 [SMILES: CC(C)(OCCNCCOCCNc1cccc2c1C(=O)N(C1CCC(=O)NC1=O)C2=O)C(F)CNC(=O)c1cnc(-n2ncc3cc(C#N)cnc32)cc1NC1CC1] |

TABLE 1-continued

Exemplary Compounds

| I-# | Structure |
|---|---|
| I-130 | 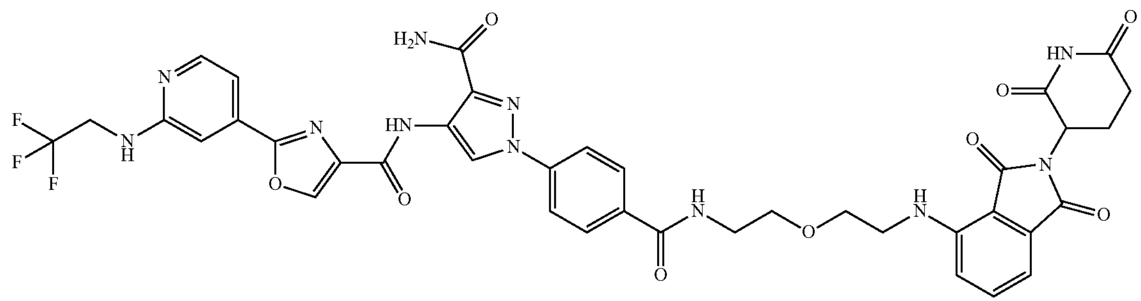 [SMILES: NC(=O)c1nn(-c2ccc(C(=O)NCCOCCNc3cccc4c3C(=O)N(C3CCC(=O)NC3=O)C4=O)cc2)cc1NC(=O)c1coc(-c2ccnc(NCC(F)(F)F)c2)n1] |
| I-131 | 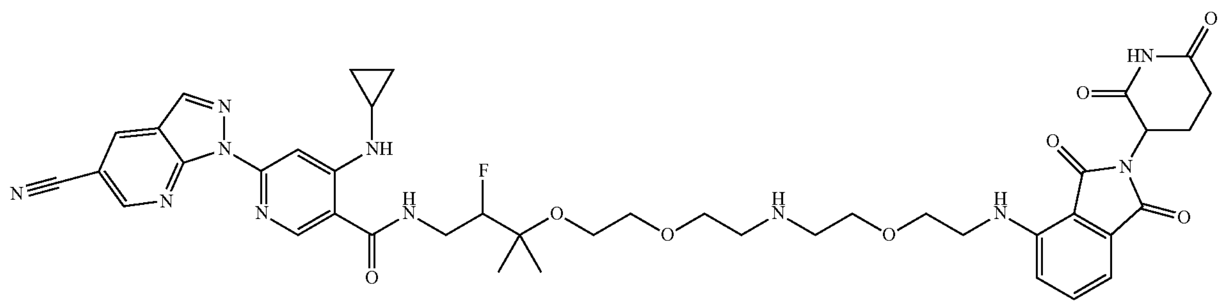 [SMILES: CC(C)(OCCOCCNCCOCCNc1cccc2c1C(=O)N(C1CCC(=O)NC1=O)C2=O)C(F)CNC(=O)c1cnc(-n2ncc3cc(C#N)cnc32)cc1NC1CC1] |
| I-132 | 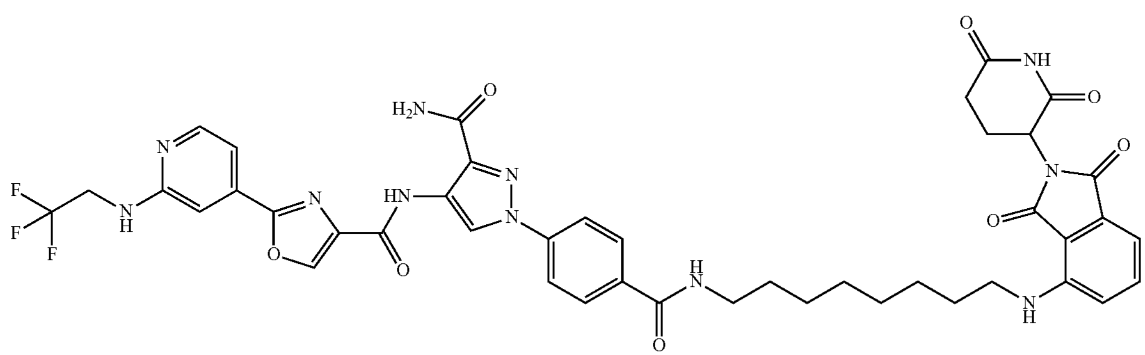 [SMILES: NC(=O)c1nn(-c2ccc(C(=O)NCCCCCCCCNc3cccc4c3C(=O)N(C3CCC(=O)NC3=O)C4=O)cc2)cc1NC(=O)c1coc(-c2ccnc(NCC(F)(F)F)c2)n1] |

TABLE 1-continued
Exemplary Compounds
| I-# | Structure |
|---|---|
| I-133 | 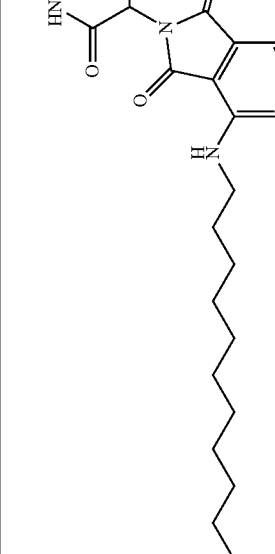 |
| I-134 | 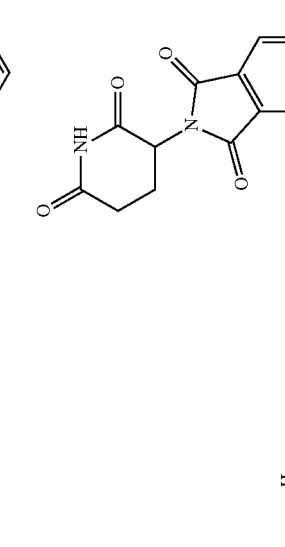 |

TABLE 1-continued

Exemplary Compounds

| I-# | Structure |
|---|---|
| I-135 | 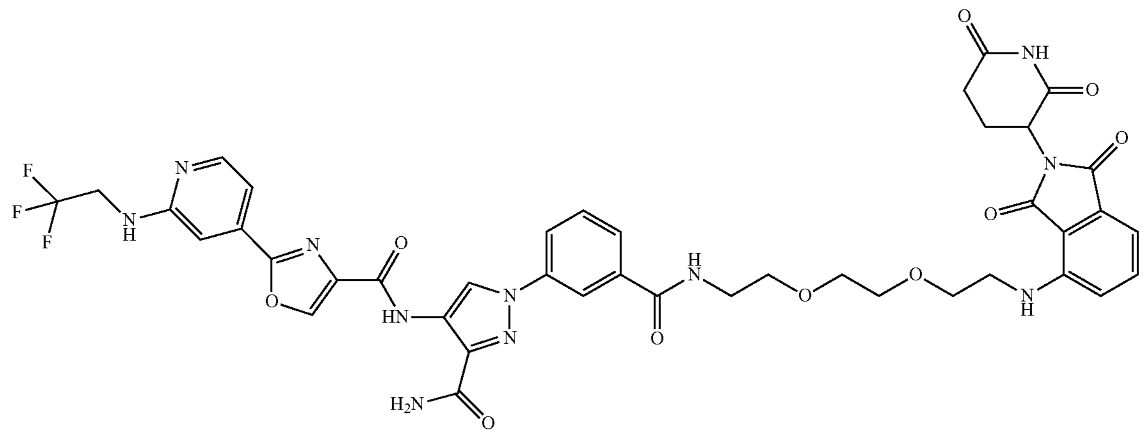 [SMILES: NC(=O)c1nn(-c2cccc(C(=O)NCCOCCOCCNc3cccc4c3C(=O)N(C3CCC(=O)NC3=O)C4=O)c2)cc1NC(=O)c1coc(-c2ccnc(NCC(F)(F)F)c2)n1] |
| I-136 | 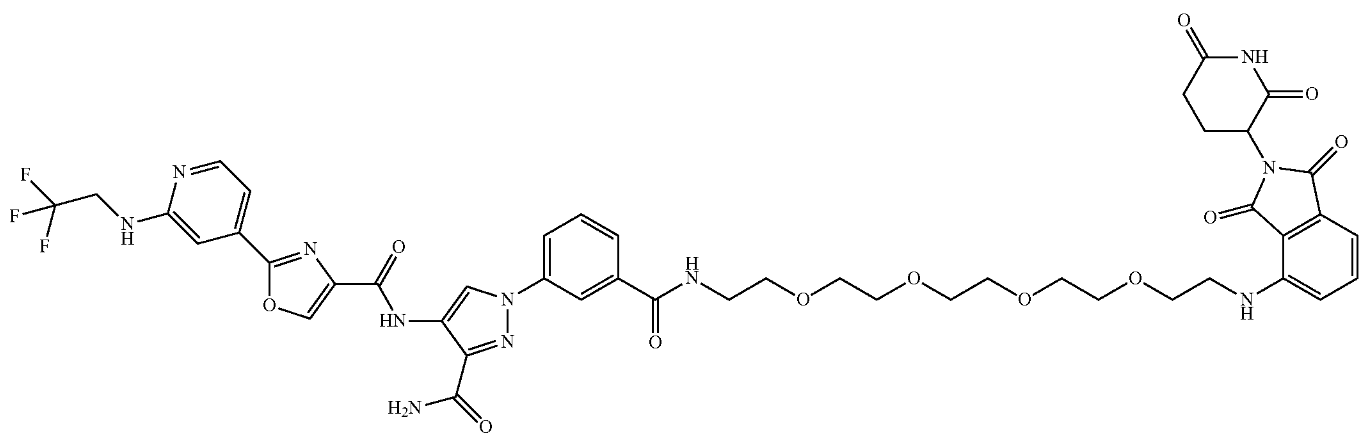 [SMILES: NC(=O)c1nn(-c2cccc(C(=O)NCCOCCOCCOCCOCCNc3cccc4c3C(=O)N(C3CCC(=O)NC3=O)C4=O)c2)cc1NC(=O)c1coc(-c2ccnc(NCC(F)(F)F)c2)n1] |

TABLE 1-continued
Exemplary Compounds
| I-# | Structure |
|---|---|
| I-137 | 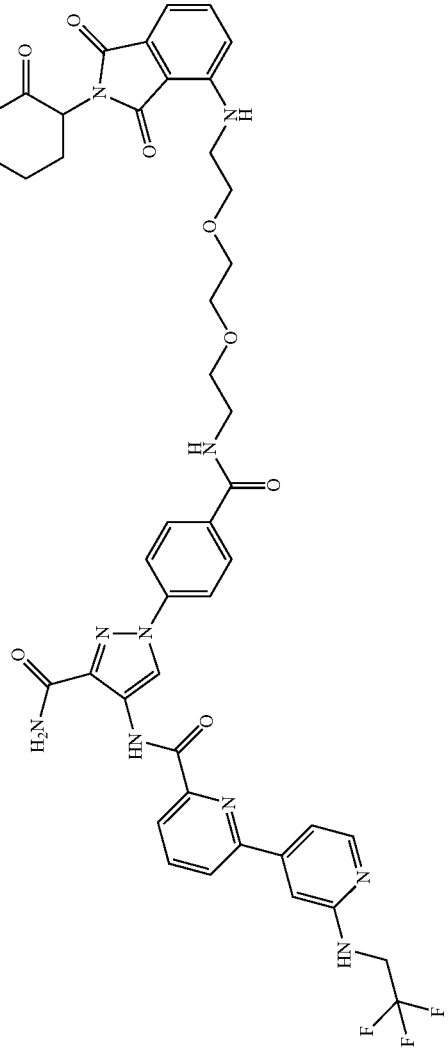 |
| I-138 | 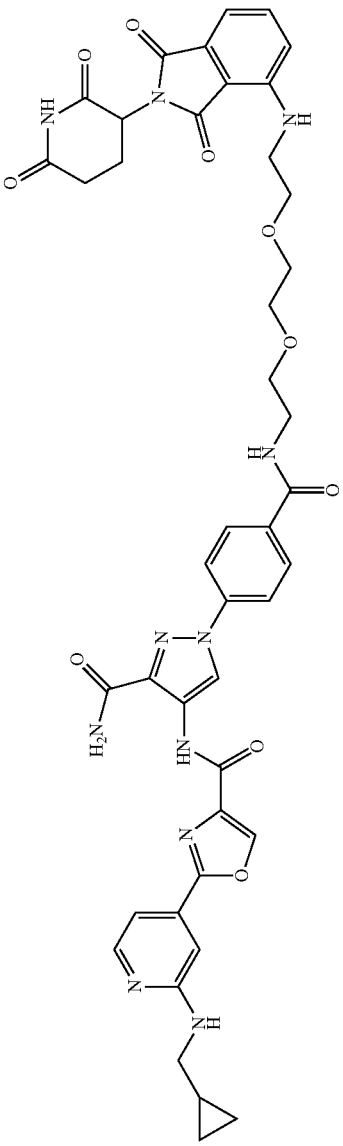 |

TABLE 1-continued

Exemplary Compounds

| I-# | Structure |
|---|---|
| I-139 | 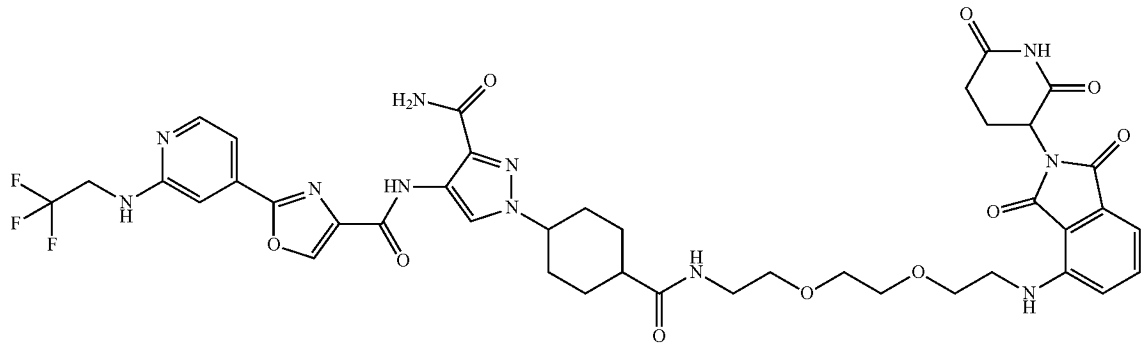 [SMILES: NC(=O)c1nn(C2CCC(C(=O)NCCOCCOCCNc3cccc4c3C(=O)N(C3CCC(=O)NC3=O)C4=O)CC2)cc1NC(=O)c1coc(-c2ccnc(NCC(F)(F)F)c2)n1] |
| I-140 | 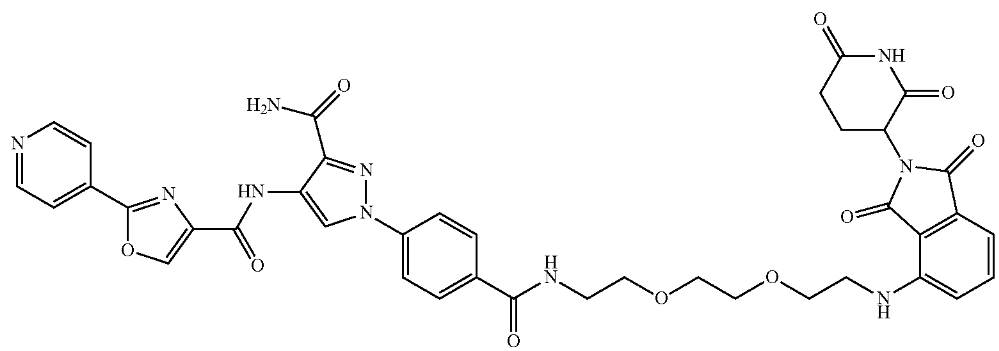 [SMILES: NC(=O)c1nn(-c2ccc(C(=O)NCCOCCOCCNc3cccc4c3C(=O)N(C3CCC(=O)NC3=O)C4=O)cc2)cc1NC(=O)c1coc(-c2ccncc2)n1] |
| I-141 | 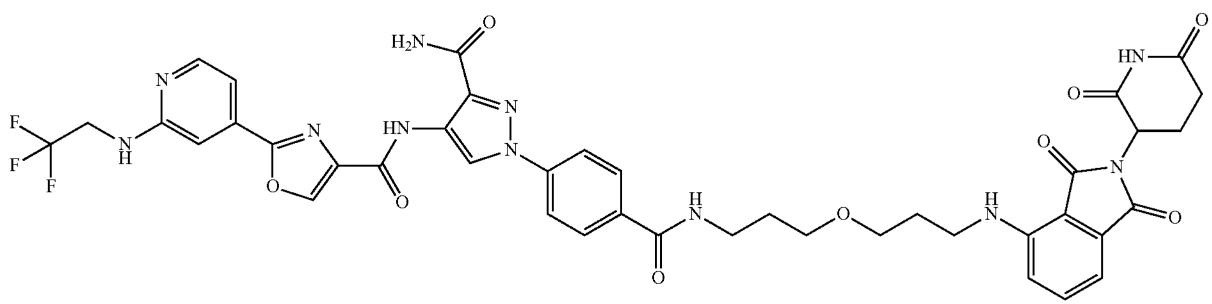 [SMILES: NC(=O)c1nn(-c2ccc(C(=O)NCCCOCCCNc3cccc4c3C(=O)N(C3CCC(=O)NC3=O)C4=O)cc2)cc1NC(=O)c1coc(-c2ccnc(NCC(F)(F)F)c2)n1] |

TABLE 1-continued

Exemplary Compounds

| I-# | Structure |
|---|---|
| I-142 | 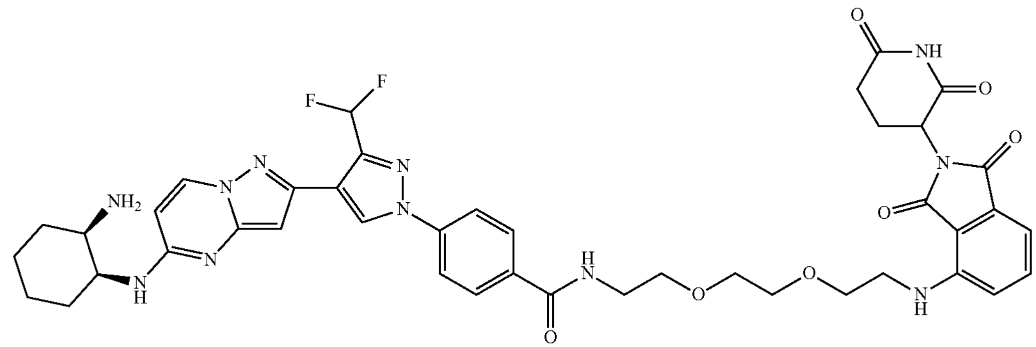 [SMILES: N[C@@H]1CCCC[C@@H]1Nc1ccn2nc(-c3cn(-c4ccc(C(=O)NCCOCCOCCNc5cccc6c5C(=O)N(C5CCC(=O)NC5=O)C6=O)cc4)nc3C(F)F)cc2n1] |
| I-143 | 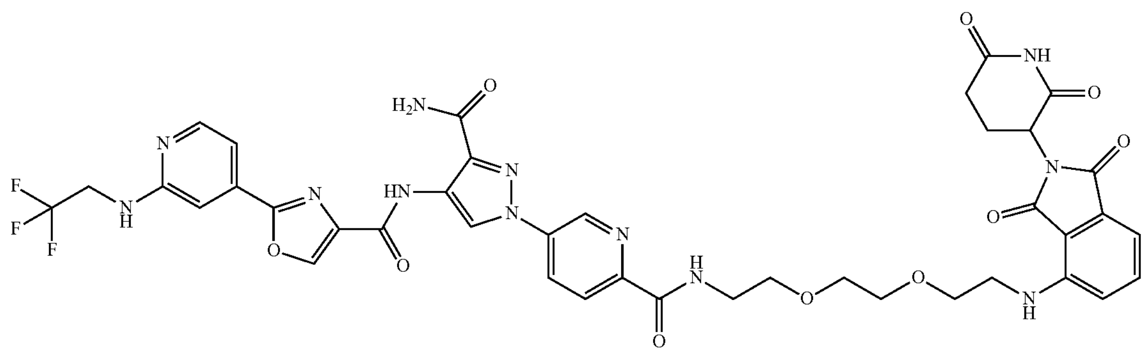 |

TABLE 1-continued

Exemplary Compounds

| I-# | Structure |
|---|---|
| I-144 | 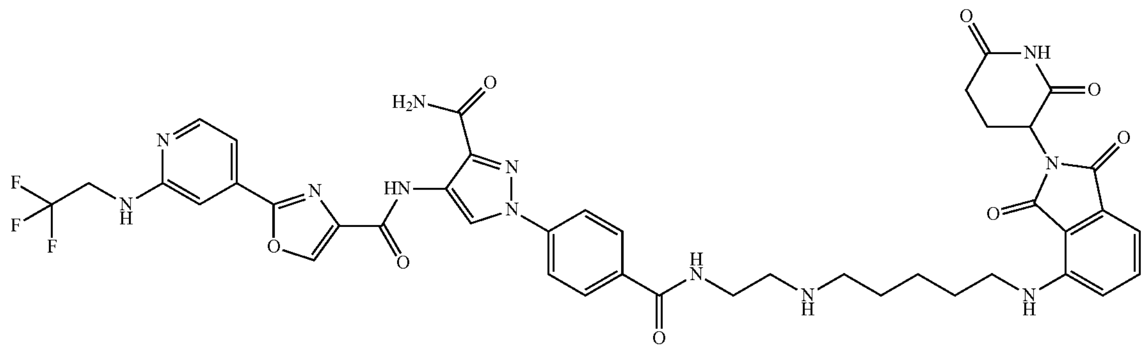 [SMILES: NC(=O)c1nn(-c2ccc(C(=O)NCCNCCCCCNc3cccc4c3C(=O)N(C3CCC(=O)NC3=O)C4=O)cc2)cc1NC(=O)c1coc(-c2ccnc(NCC(F)(F)F)c2)n1] |
| I-145 | 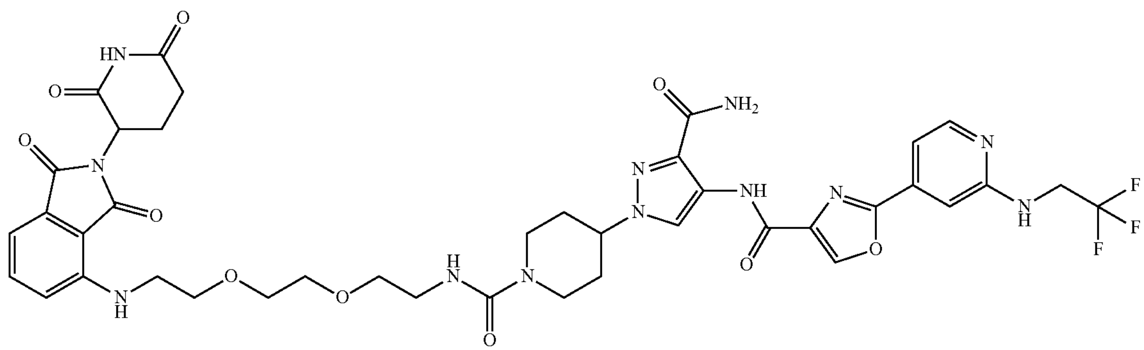 [SMILES: NC(=O)c1nn(C2CCN(C(=O)NCCOCCOCCNc3cccc4c3C(=O)N(C3CCC(=O)NC3=O)C4=O)CC2)cc1NC(=O)c1coc(-c2ccnc(NCC(F)(F)F)c2)n1] |
| I-146 | 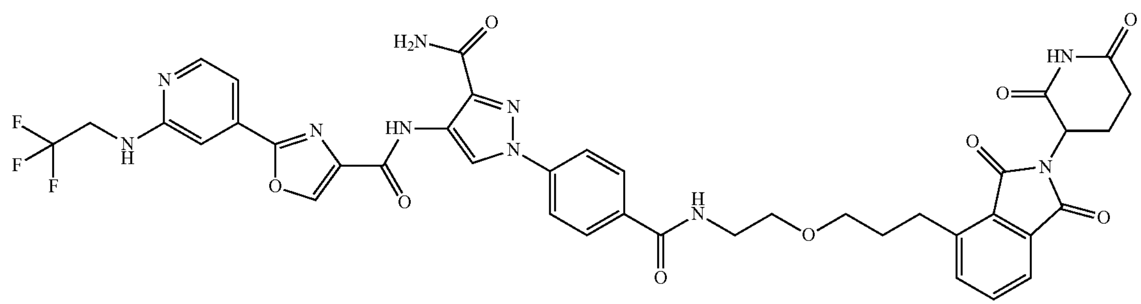 [SMILES: NC(=O)c1nn(-c2ccc(C(=O)NCCOCCCc3cccc4c3C(=O)N(C3CCC(=O)NC3=O)C4=O)cc2)cc1NC(=O)c1coc(-c2ccnc(NCC(F)(F)F)c2)n1] |

TABLE 1-continued

Exemplary Compounds

| I-# | Structure |
|---|---|
| I-147 | 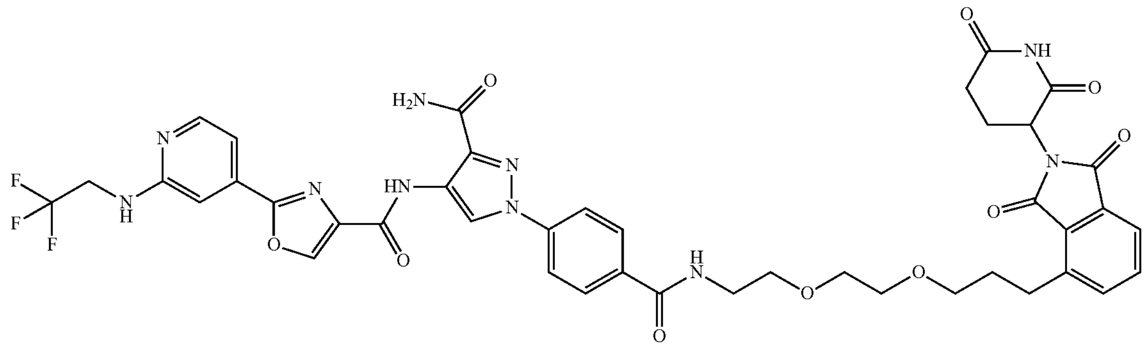 [SMILES: NC(=O)c1nn(-c2ccc(C(=O)NCCOCCOCCCc3cccc4c3C(=O)N(C3CCC(=O)NC3=O)C4=O)cc2)cc1NC(=O)c1coc(-c2ccnc(NCC(F)(F)F)c2)n1] |
| I-148 | 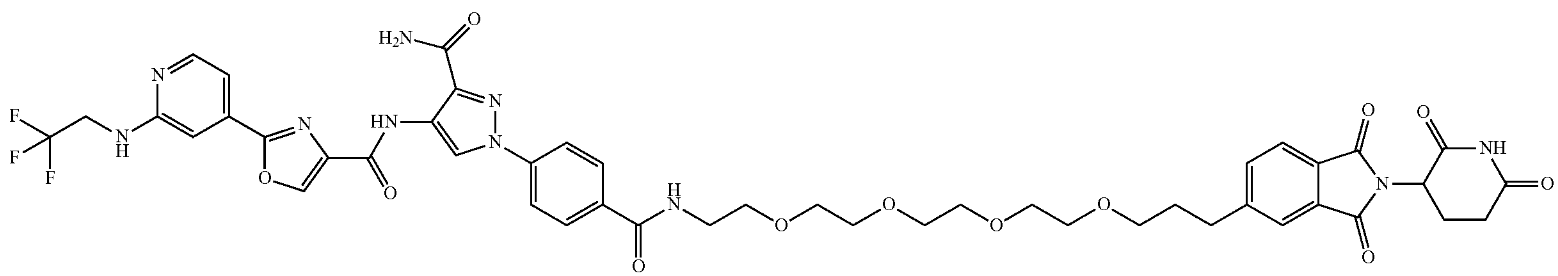 [SMILES: NC(=O)c1nn(-c2ccc(C(=O)NCCOCCOCCOCCOCCCc3ccc4c(c3)C(=O)N(C3CCC(=O)NC3=O)C4=O)cc2)cc1NC(=O)c1coc(-c2ccnc(NCC(F)(F)F)c2)n1] |
| I-149 | 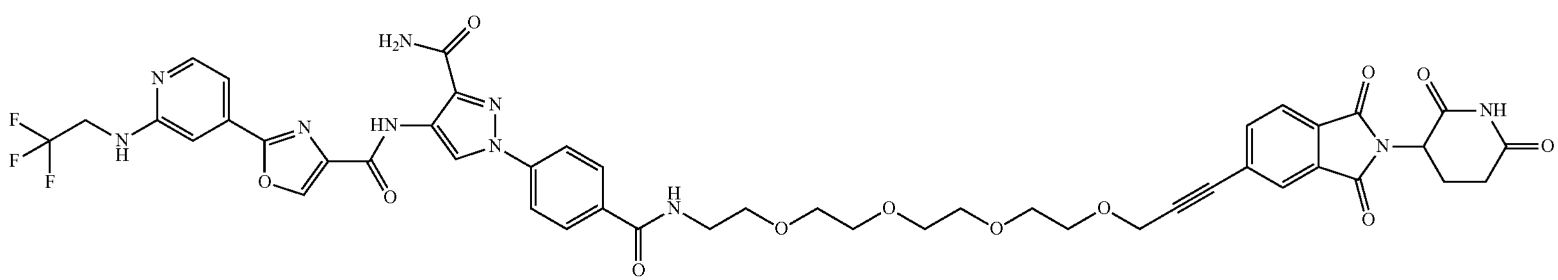 [SMILES: NC(=O)c1nn(-c2ccc(C(=O)NCCOCCOCCOCCOCC#Cc3ccc4c(c3)C(=O)N(C3CCC(=O)NC3=O)C4=O)cc2)cc1NC(=O)c1coc(-c2ccnc(NCC(F)(F)F)c2)n1] |

TABLE 1-continued

Exemplary Compounds

| I-# | Structure |
|---|---|
| I-150 | 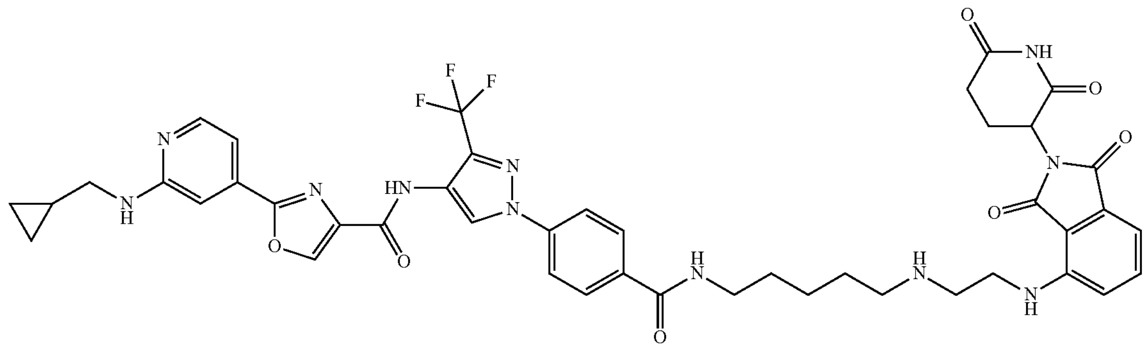 |
| I-151 | 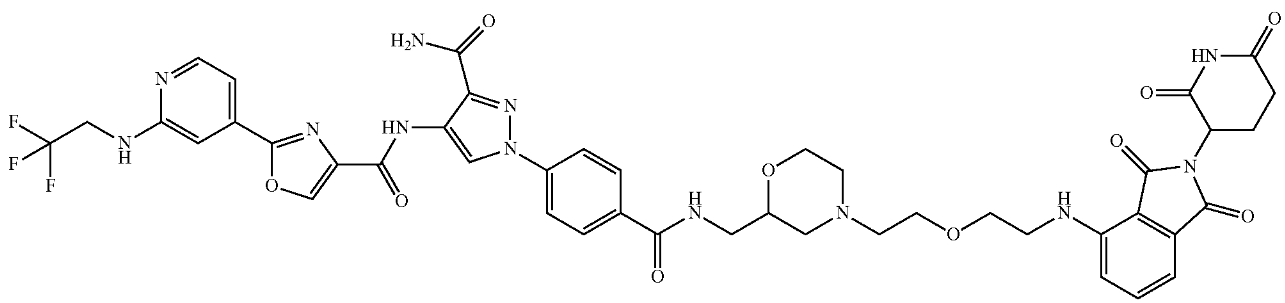 [SMILES: NC(=O)c1nn(-c2ccc(C(=O)NCC3CN(CCOCCNc4cccc5c4C(=O)N(C4CCC(=O)NC4=O)C5=O)CCO3)cc2)cc1NC(=O)c1coc(-c2ccnc(NCC(F)(F)F)c2)n1] |
| I-152 | 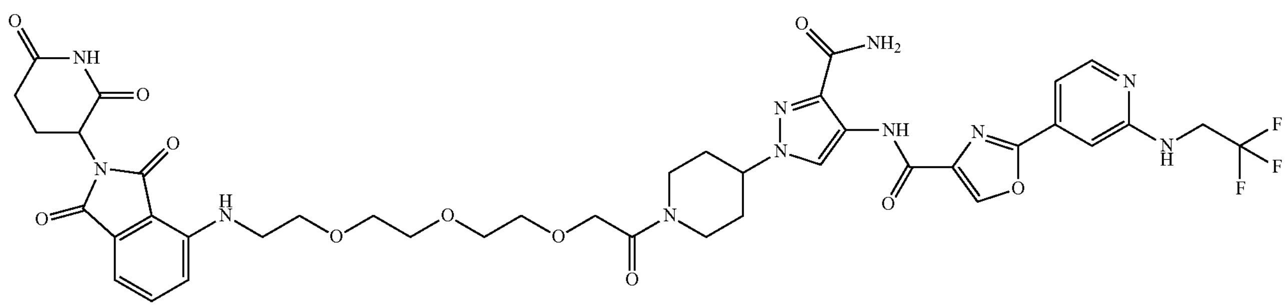 [SMILES: NC(=O)c1nn(C2CCN(C(=O)COCCOCCOCCNc3cccc4c3C(=O)N(C3CCC(=O)NC3=O)C4=O)CC2)cc1NC(=O)c1coc(-c2ccnc(NCC(F)(F)F)c2)n1] |

TABLE 1-continued
Exemplary Compounds
| I-# | Structure |
|---|---|
| I-153 | 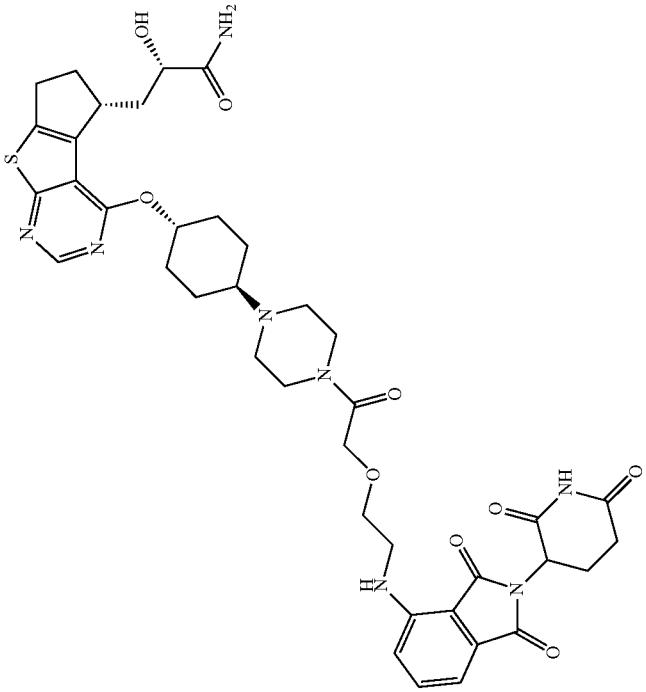 |
| I-154 | 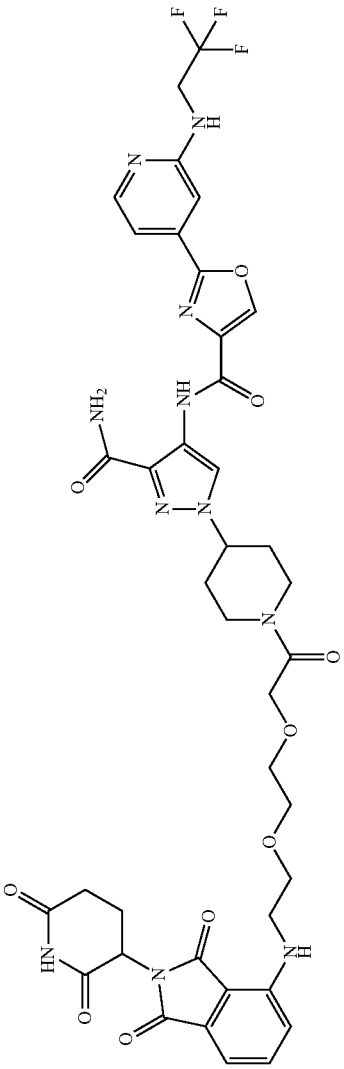 |

TABLE 1-continued
Exemplary Compounds
| I-# | Structure |
|---|---|
| I-155 | 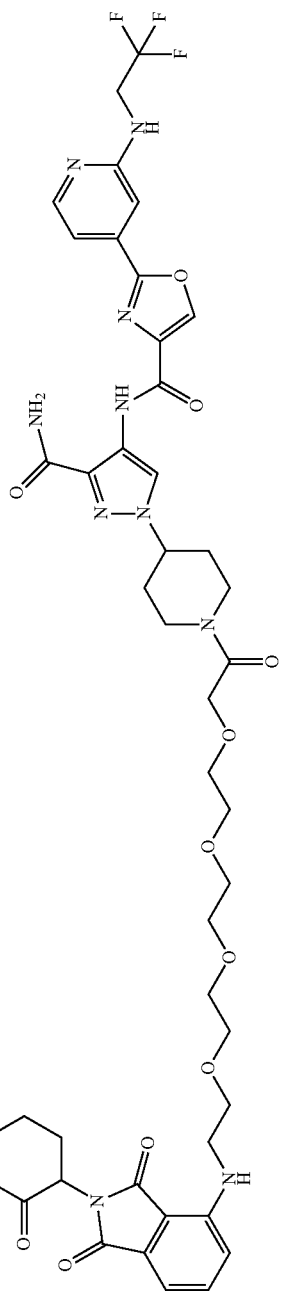 |
| I-156 | 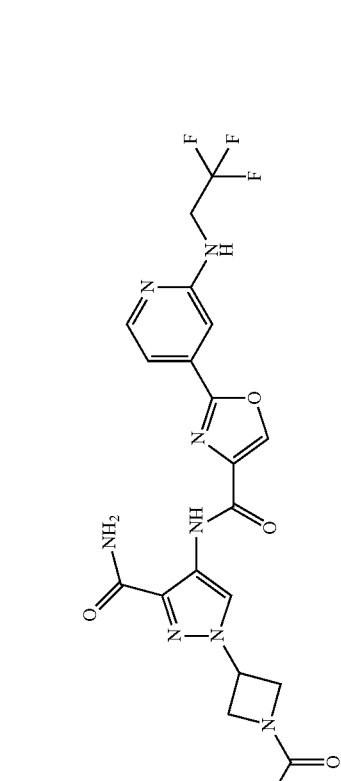 |

TABLE 1-continued
Exemplary Compounds
| I-# | Structure |
|---|---|
| I-157 | 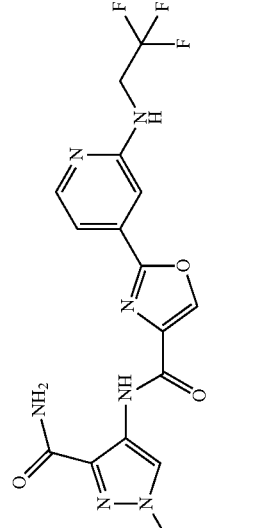 |
| I-158 | 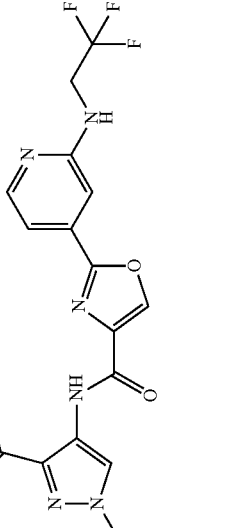 |

TABLE 1-continued
Exemplary Compounds
| I-# | Structure |
|---|---|
| I-159 | 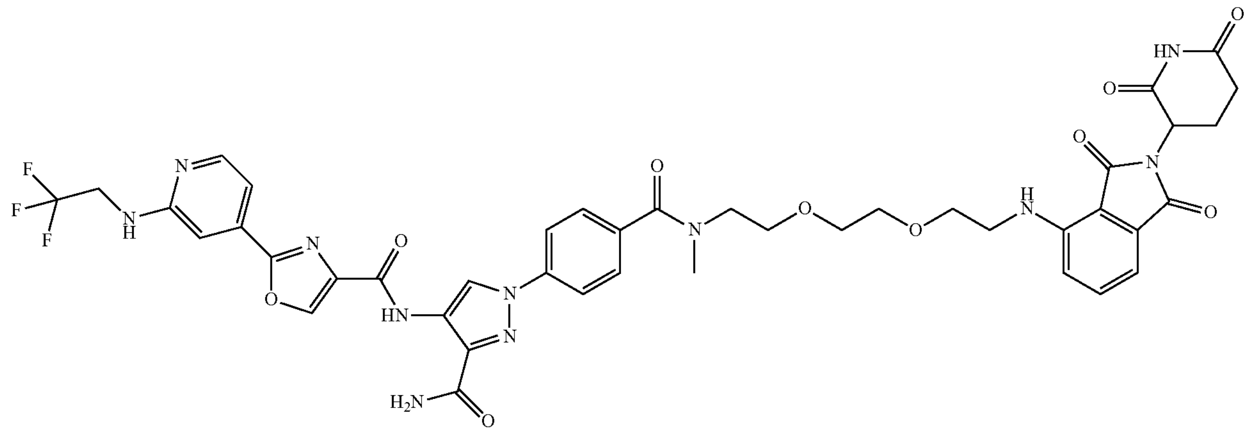 [SMILES: CN(CCOCCOCCNc1cccc2c1C(=O)N(C1CCC(=O)NC1=O)C2=O)C(=O)c1ccc(-n2cc(NC(=O)c3coc(-c4ccnc(NCC(F)(F)F)c4)n3)c(C(N)=O)n2)cc1] |

TABLE 1-continued
Exemplary Compounds
| I-# | Structure |
|---|---|
| I-160 | 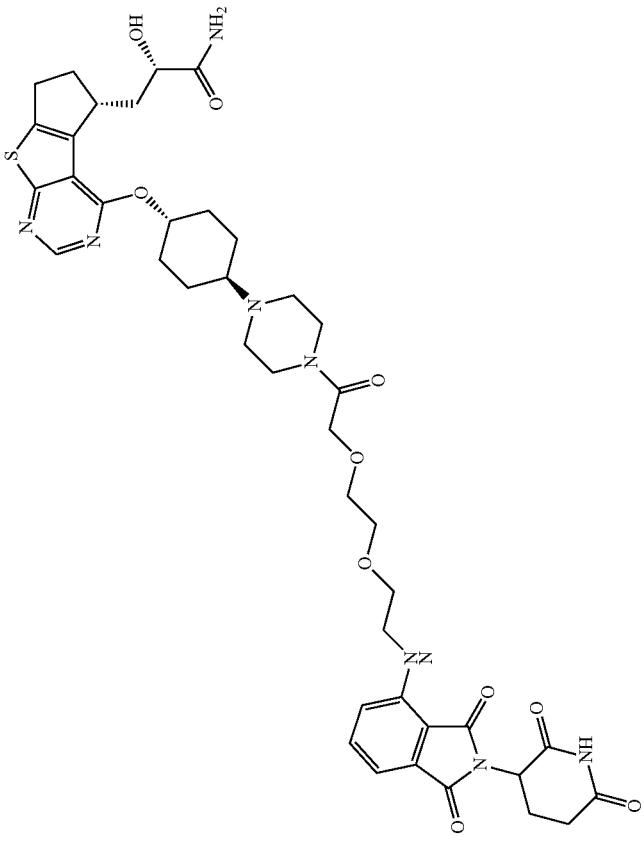 |

TABLE 1-continued
Exemplary Compounds
| I-# | Structure |
|---|---|
| I-161 | 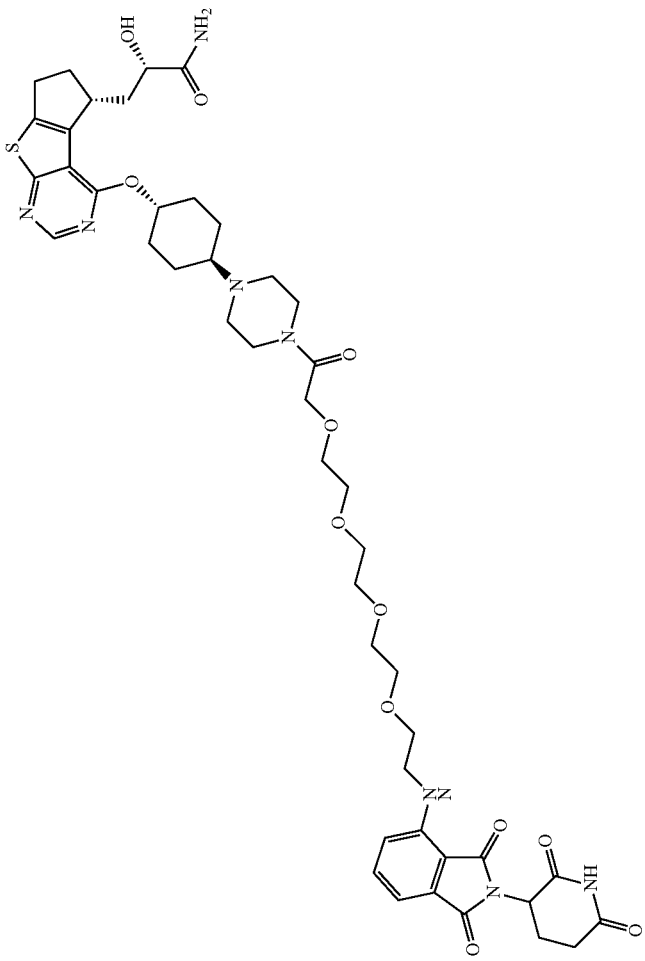 |

TABLE 1-continued
Exemplary Compounds
| I-# | Structure |
|---|---|
| I-162 | 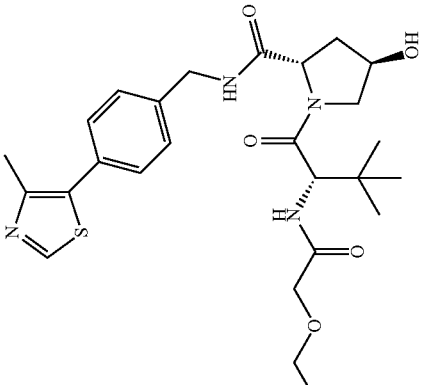 |

TABLE 1-continued
Exemplary Compounds
| I-# | Structure |
|---|---|
| I-163 | 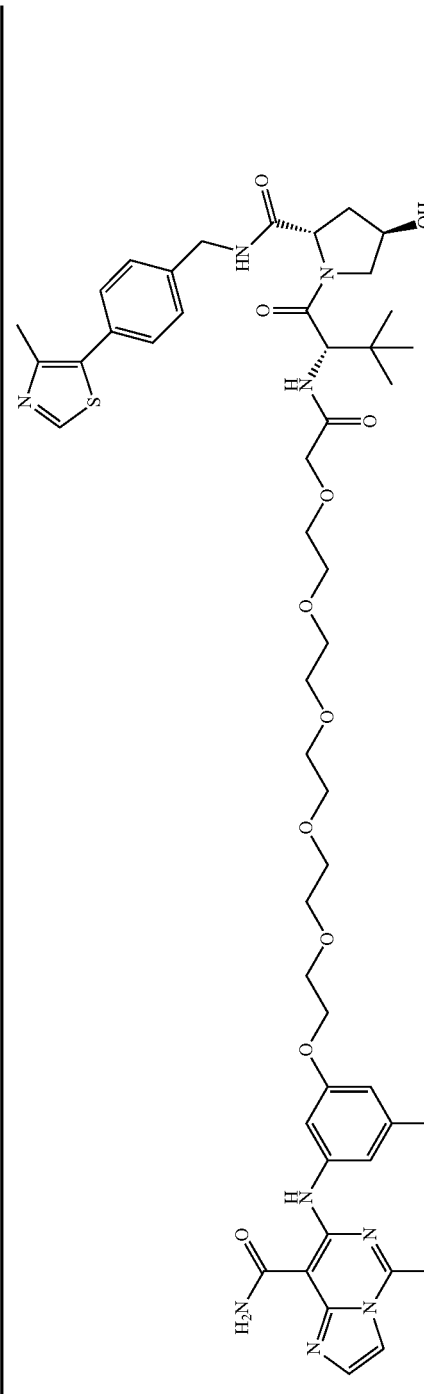 |
| I-164 | 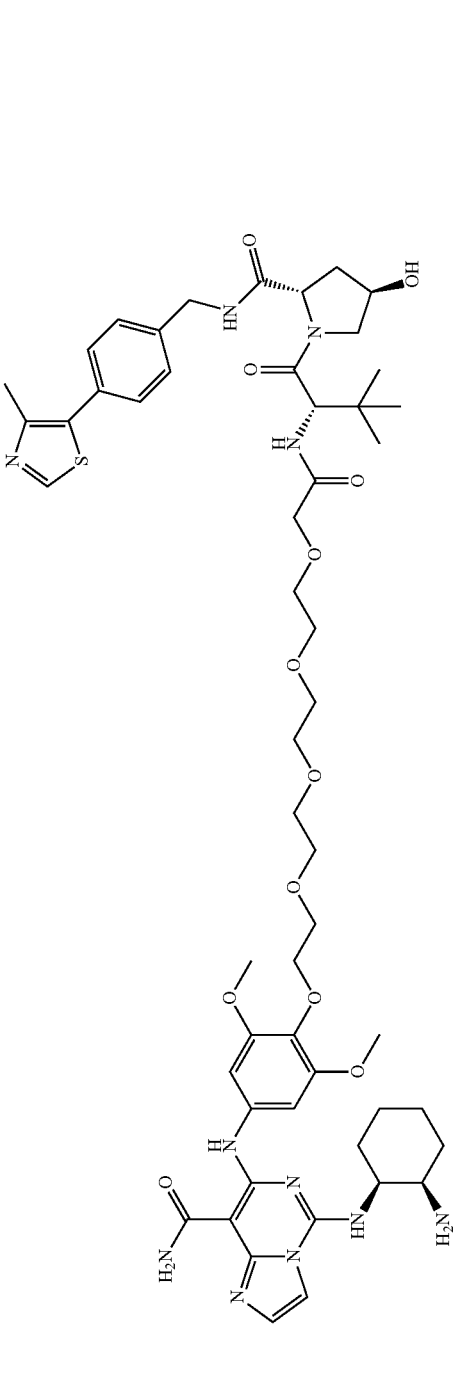 |

TABLE 1-continued
Exemplary Compounds
| I-# | Structure |
|---|---|
| I-165 | 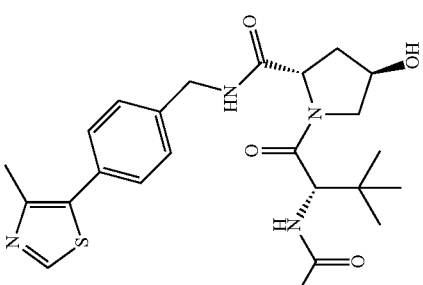 |
| I-166 | 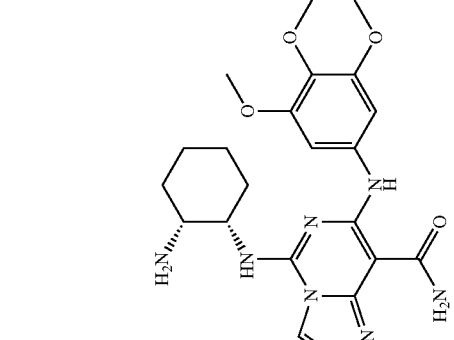 |

TABLE 1-continued
Exemplary Compounds
| I-# | Structure |
|---|---|
| I-167 | 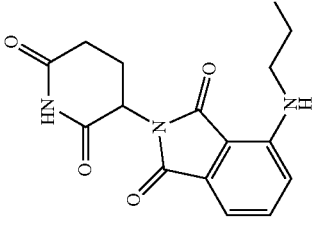 |
| I-168 | 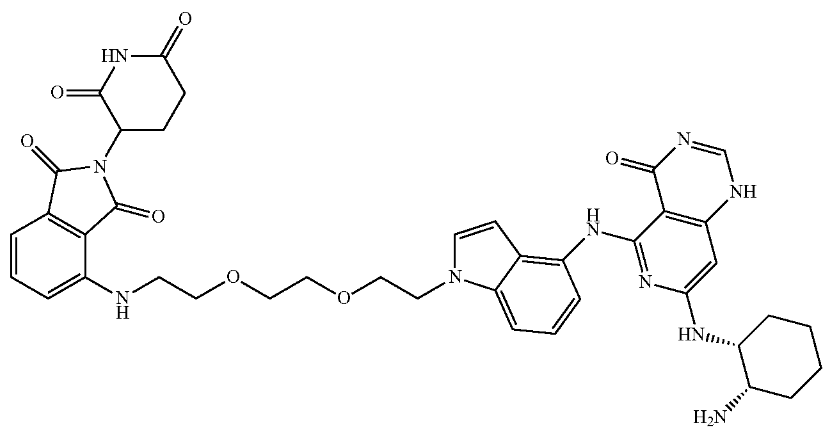 [SMILES: N[C@H]1CCCC[C@H]1Nc1cc2[nH]cnc(=O)c2c(Nc2cccc3c2ccn3CCOCCOCCNc2cccc3c2C(=O)N(C2CCC(=O)NC2=O)C3=O)n1] |

TABLE 1-continued

Exemplary Compounds

| I-# | Structure |
|---|---|
| I-169 | 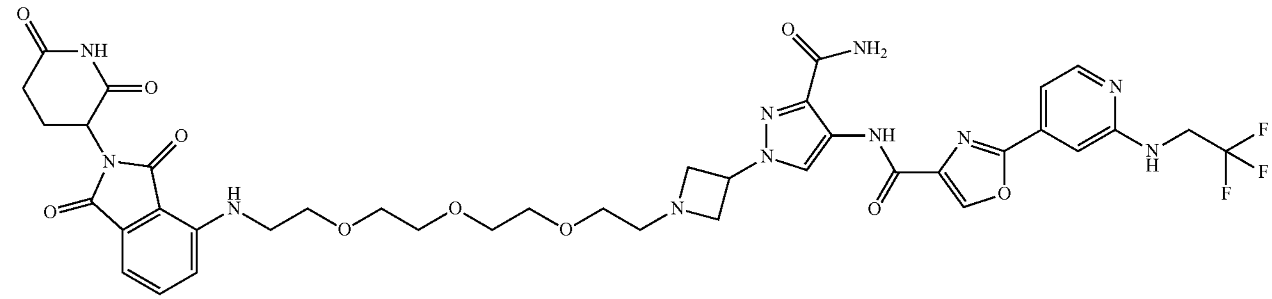 [SMILES: NC(=O)c1nn(C2CN(CCOCCOCCOCCNc3cccc4c3C(=O)N(C3CCC(=O)NC3=O)C4=O)C2)cc1NC(=O)c1coc(-c2ccnc(NCC(F)(F)F)c2)n1] |
| I-170 | 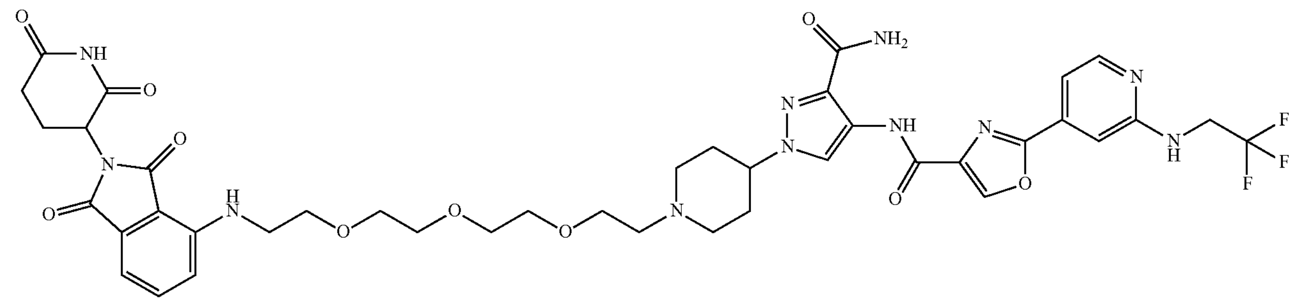 [SMILES: NC(=O)c1nn(C2CCN(CCOCCOCCOCCNc3cccc4c3C(=O)N(C3CCC(=O)NC3=O)C4=O)CC2)cc1NC(=O)c1coc(-c2ccnc(NCC(F)(F)F)c2)n1] |
| I-171 | 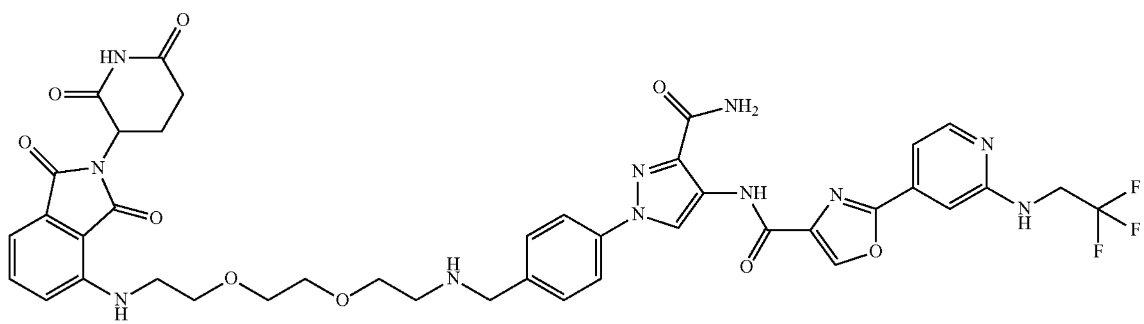 [SMILES: NC(=O)c1nn(-c2ccc(CNCCOCCOCCNc3cccc4c3C(=O)N(C3CCC(=O)NC3=O)C4=O)cc2)cc1NC(=O)c1coc(-c2ccnc(NCC(F)(F)F)c2)n1] |

TABLE 1-continued
Exemplary Compounds
| I-# | Structure |
|---|---|
| I-172 | 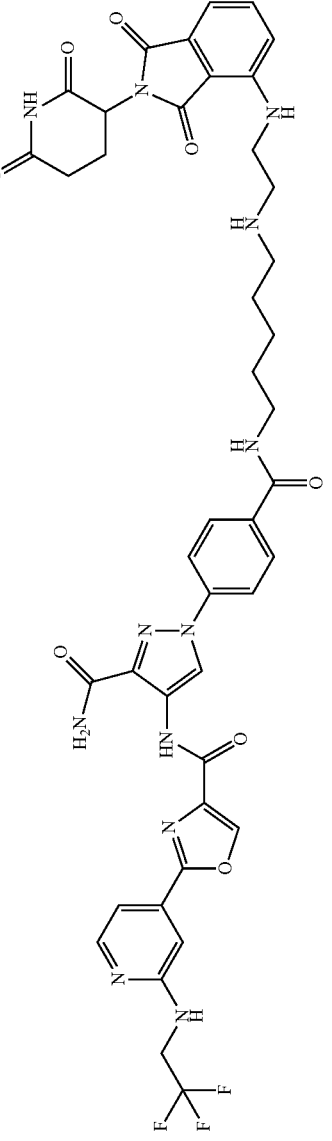 |
| I-173 | 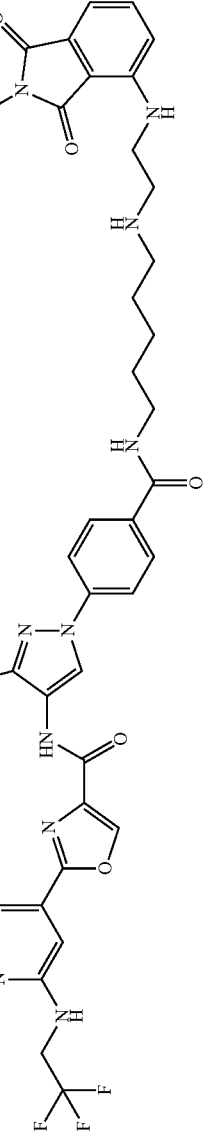 |
| I-174 | 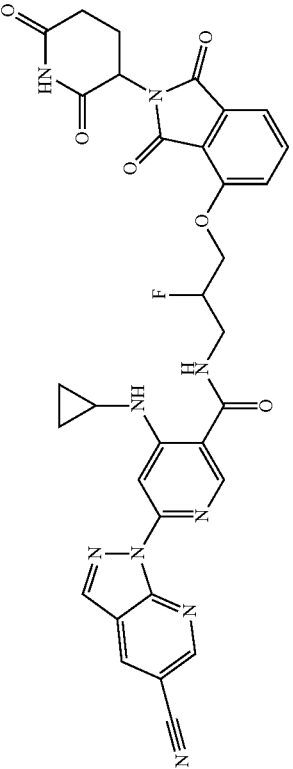 |

TABLE 1-continued
Exemplary Compounds
| I-# | Structure |
|---|---|
| I-175 | 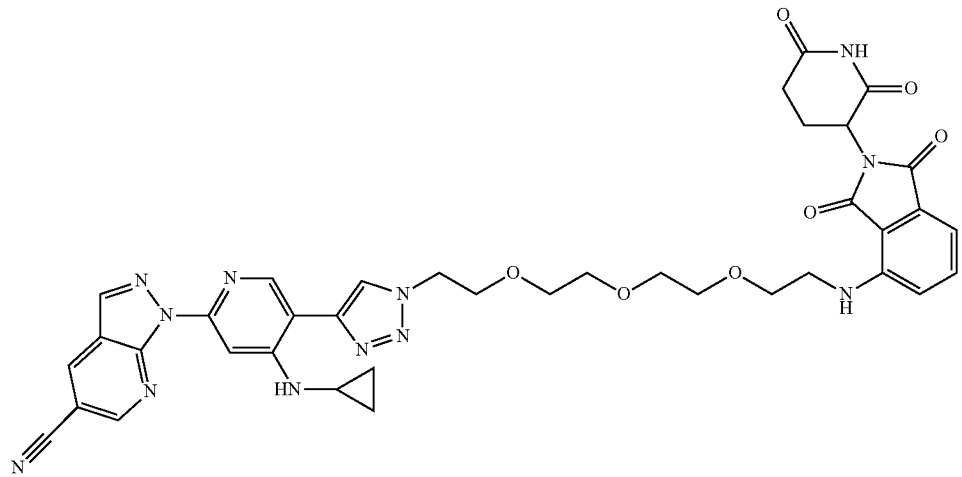 [SMILES: N#Cc1cnc2c(cnn2-c2cc(NC3CC3)c(-c3cn(CCOCCOCCOCCNc4cccc5c4C(=O)N(C4CCC(=O)NC4=O)C5=O)nn3)cn2)c1] |
| I-176 | 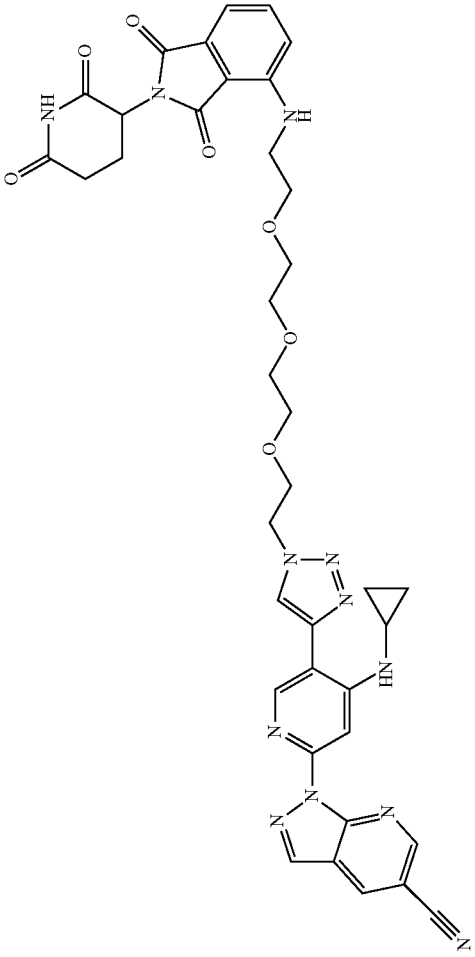 |

TABLE 1-continued
Exemplary Compounds
| I-# | Structure |
|---|---|
| I-177 | 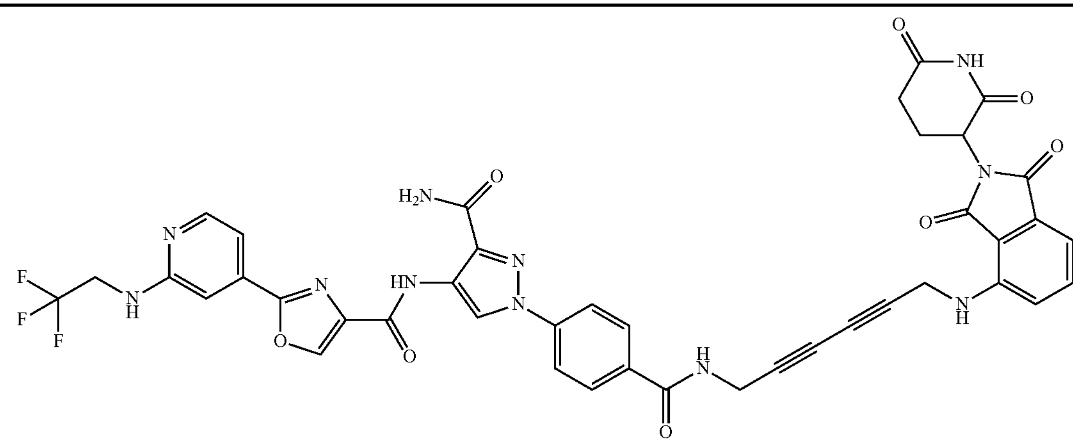 |
| I-178 | 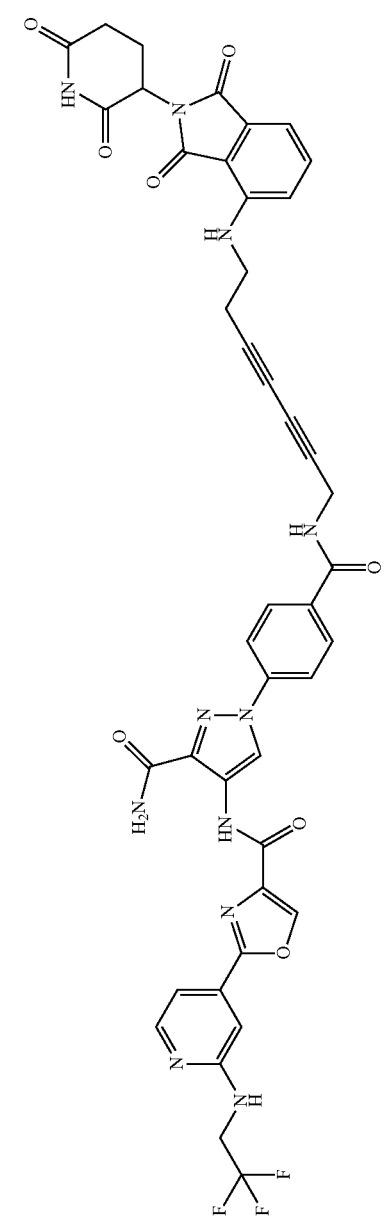 |

TABLE 1-continued

Exemplary Compounds

| I-# | Structure |
|---|---|
| I-179 | 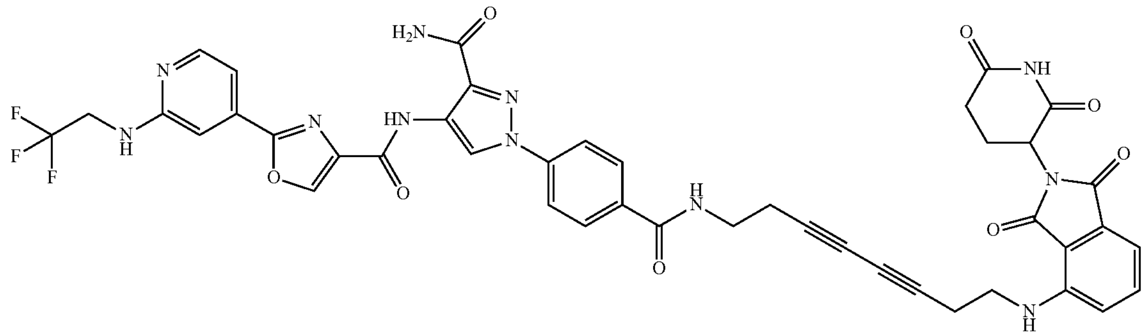 [SMILES: NC(=O)c1nn(-c2ccc(C(=O)NCCC#CC#CCCNc3cccc4c3C(=O)N(C3CCC(=O)NC3=O)C4=O)cc2)cc1NC(=O)c1coc(-c2ccnc(NCC(F)(F)F)c2)n1] |
| I-180 | 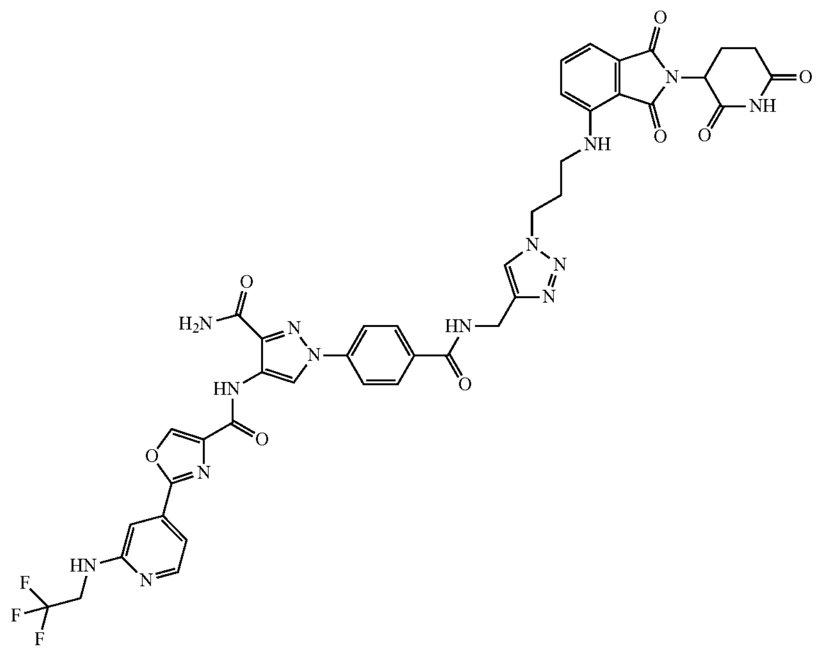 [SMILES: NC(=O)c1nn(-c2ccc(C(=O)NCc3cn(CCCNc4cccc5c4C(=O)N(C4CCC(=O)NC4=O)C5=O)nn3)cc2)cc1NC(=O)c1coc(-c2ccnc(NCC(F)(F)F)c2)n1] |

TABLE 1-continued
Exemplary Compounds
| I-# | Structure |
|---|---|
| I-181 | 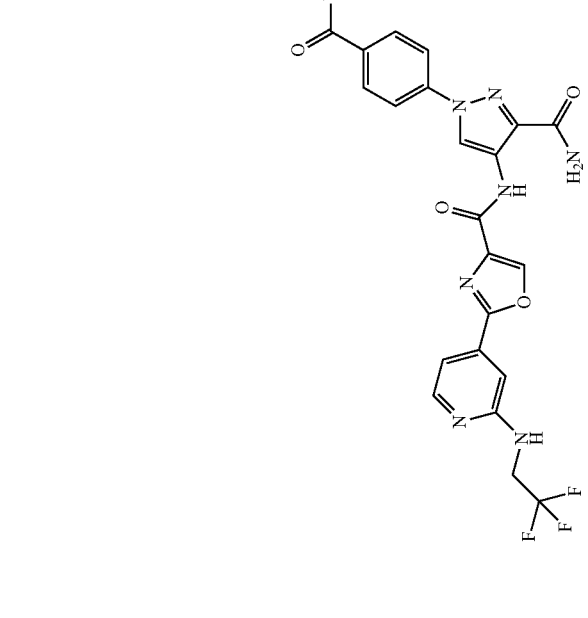 |
| I-182 | 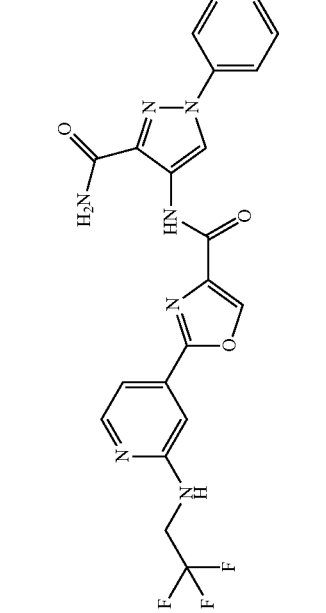 |

TABLE 1-continued
Exemplary Compounds
| I-# | Structure |
|---|---|
| I-183 | 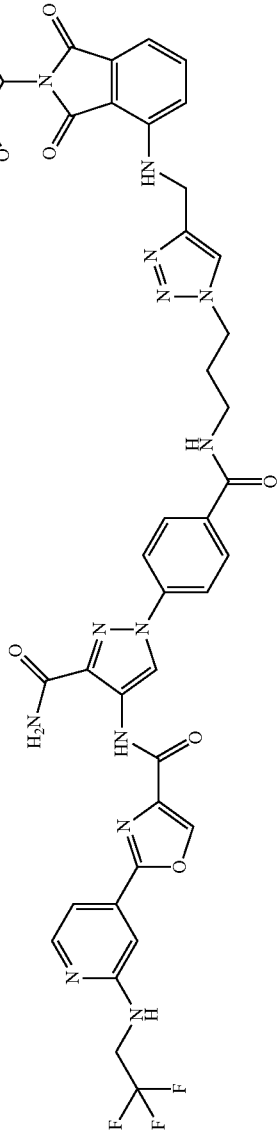 |

TABLE 1-continued
Exemplary Compounds
| I-# | Structure |
|---|---|
| I-184 | 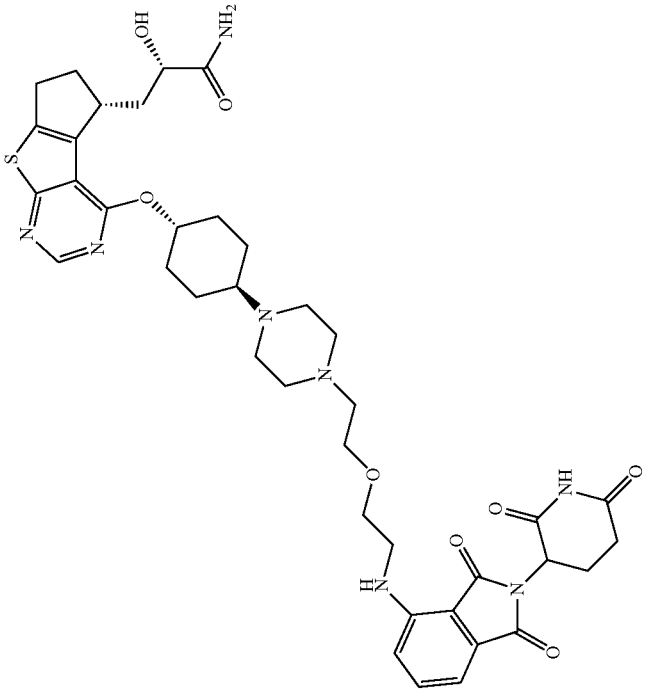 |
| I-185 | 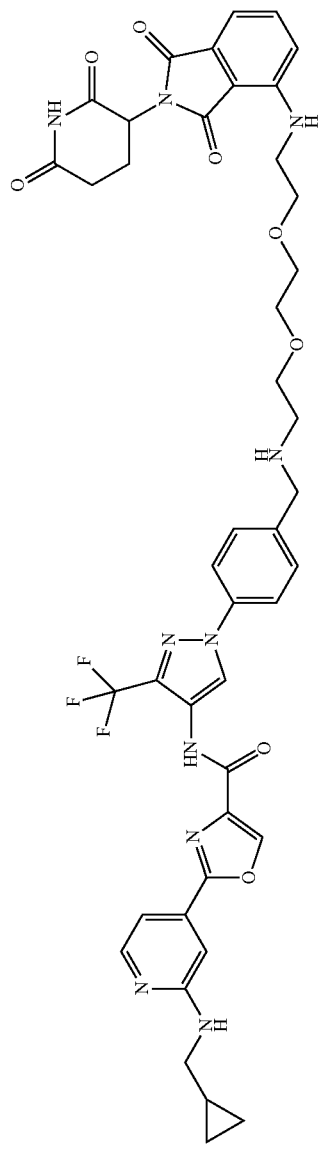 |

TABLE 1-continued
Exemplary Compounds
| I-# | Structure |
|---|---|
| I-186 | 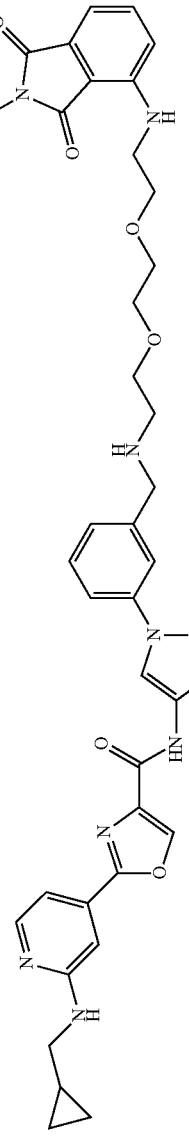 |
| I-187 | 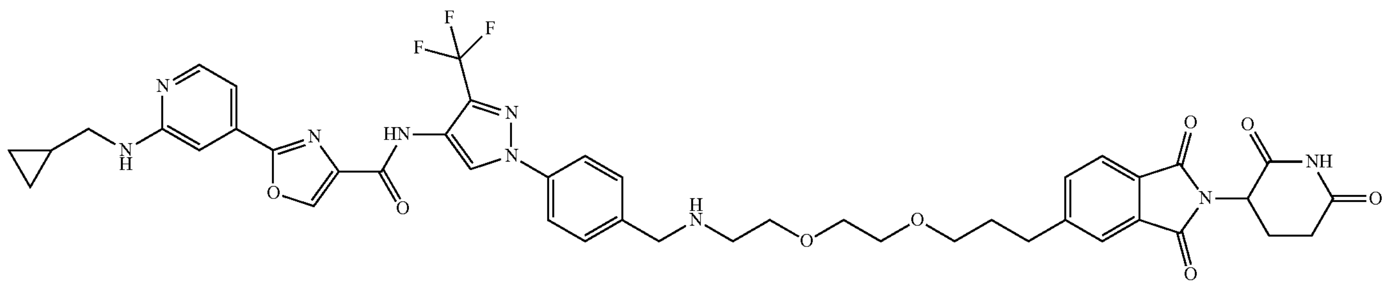 [SMILES: O=C1CCC(N2C(=O)c3ccc(CCCOCCOCCNCc4ccc(-n5cc(NC(=O)c6coc(-c7ccnc(NCC8CC8)c7)n6)c(C(F)(F)F)n5)cc4)cc3C2=O)C(=O)N1] |

TABLE 1-continued
Exemplary Compounds
| I-# | Structure |
|---|---|
| I-188 | 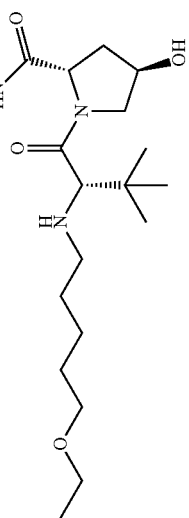 |
| I-189 | 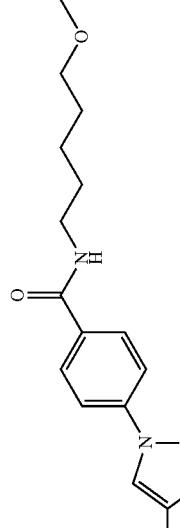 |

TABLE 1-continued
Exemplary Compounds
| I-# | Structure |
|---|---|
| I-190 | 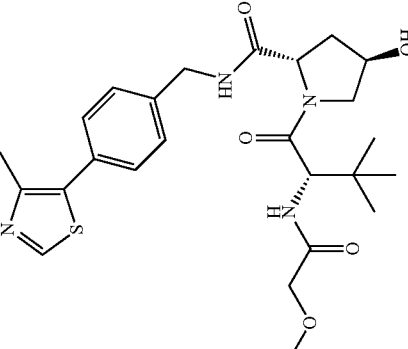 |
| I-191 | 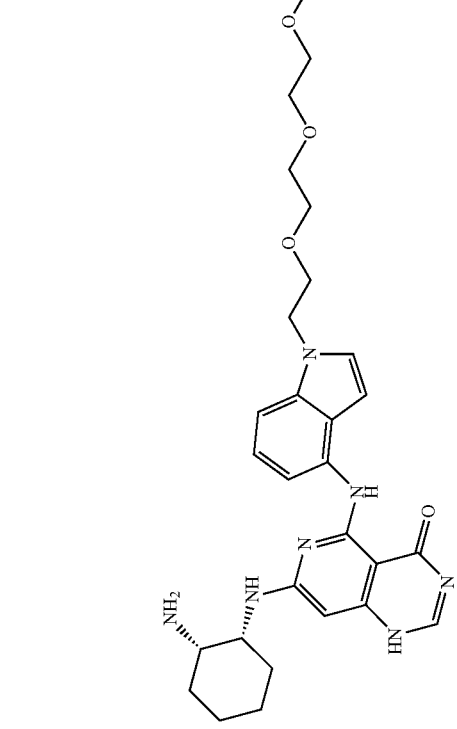 |

TABLE 1-continued
Exemplary Compounds
| I-# | Structure |
|---|---|
| I-192 | 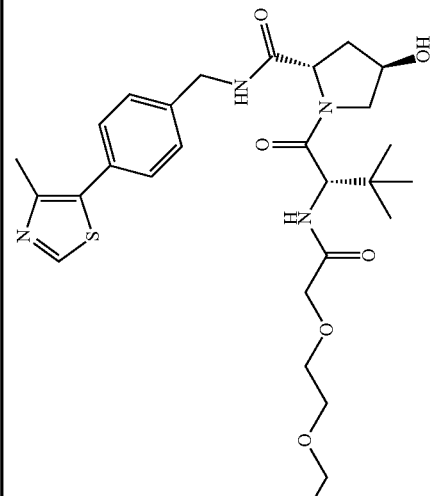 |
| I-193 | 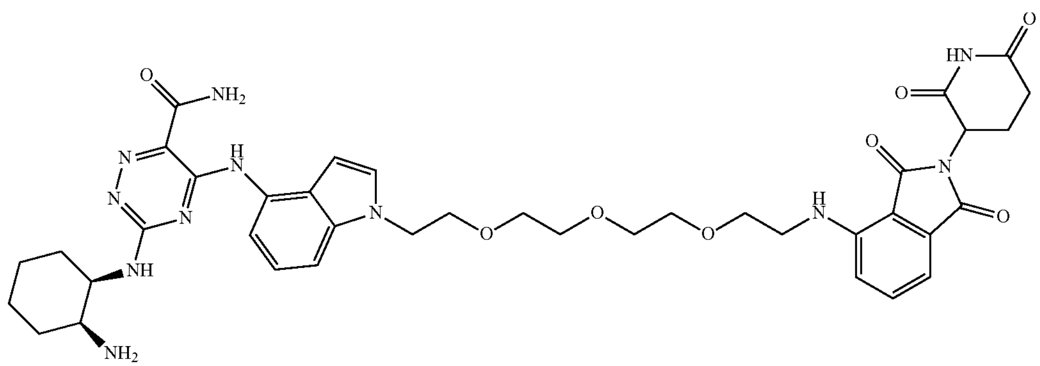 [SMILES: NC(=O)c1nnc(N[C@@H]2CCCC[C@@H]2N)nc1Nc1cccc2c1ccn2CCOCCOCCOCCNc1cccc2c1C(=O)N(C1CCC(=O)NC1=O)C2=O] |

TABLE 1-continued
Exemplary Compounds
| I-# | Structure |
|---|---|
| I-194 | 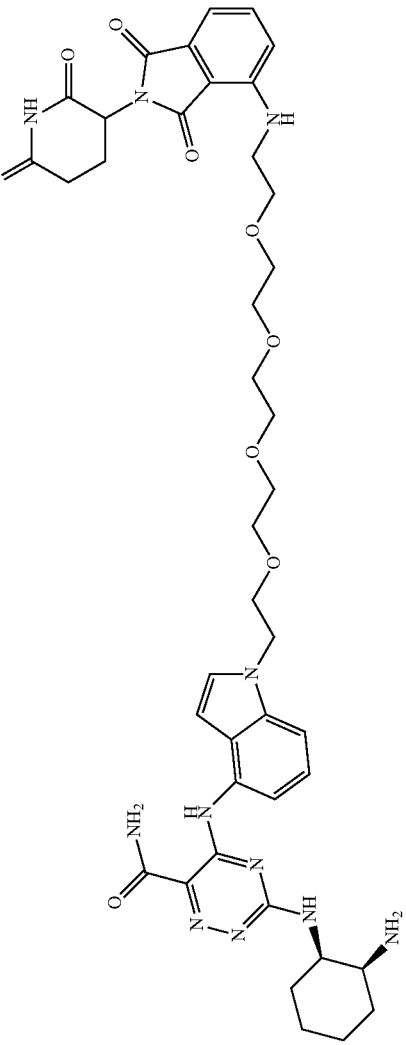 |
| I-195 | 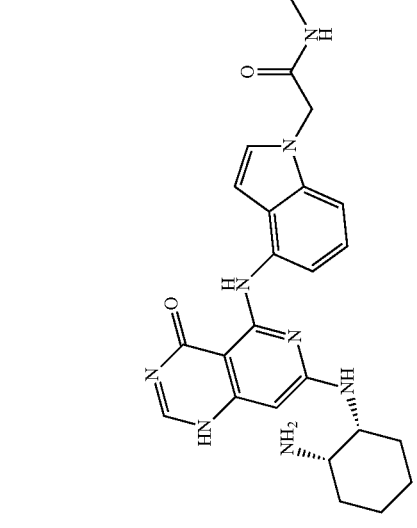 |

TABLE 1-continued
Exemplary Compounds
| I-# | Structure |
|---|---|
| I-196 | 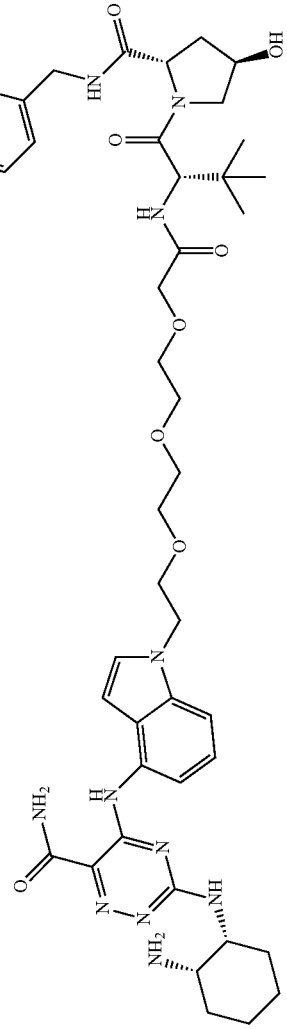 |
| I-197 | 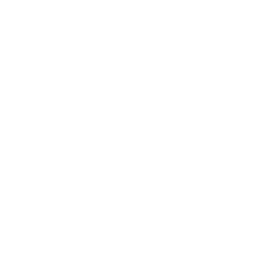 |

TABLE 1-continued
Exemplary Compounds
| I-# | Structure |
|---|---|
| I-198 | 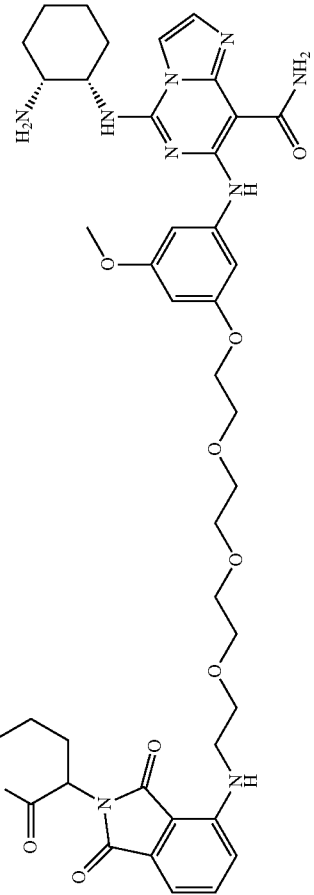 |
| I-199 | 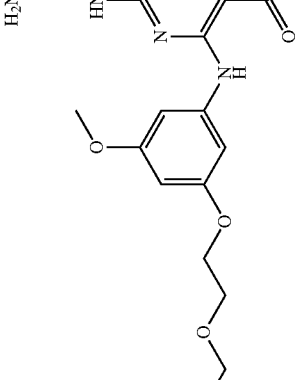 |

TABLE 1-continued
Exemplary Compounds
| I-# | Structure |
|---|---|
| I-200 | 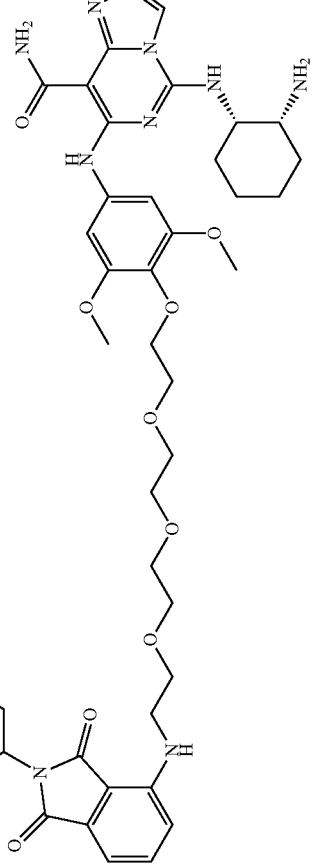 |
| I-201 | 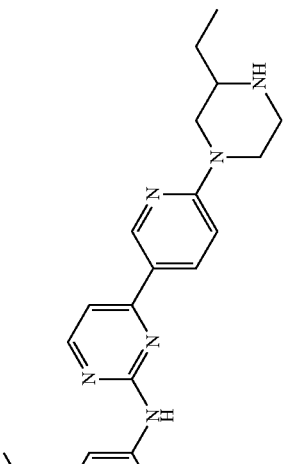 |

TABLE 1-continued
Exemplary Compounds
| I-# | Structure |
|---|---|
| I-202 | 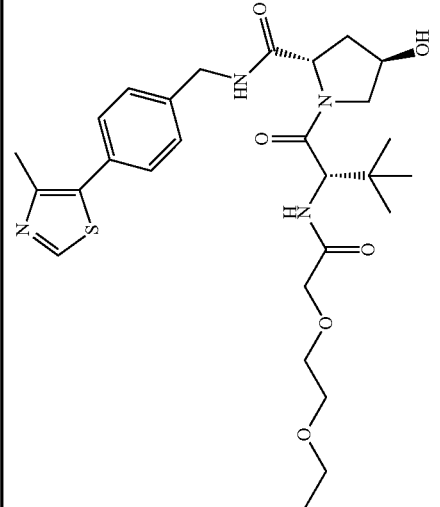 |
| I-203 | 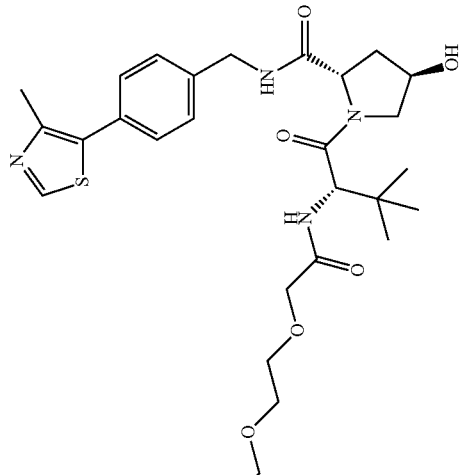 |

TABLE 1-continued
Exemplary Compounds
| I-# | Structure |
|---|---|
| I-204 | 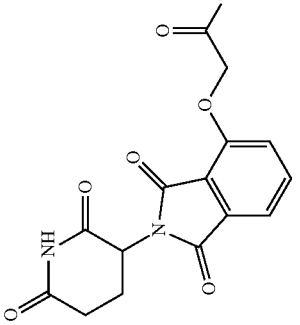 |
| I-205 | 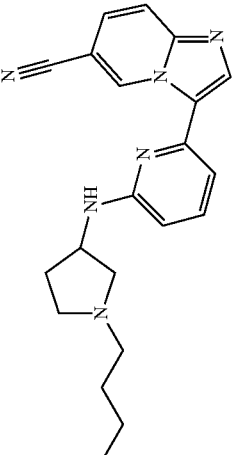 |

TABLE 1-continued
Exemplary Compounds
| I-# | Structure |
|---|---|
| I-206 | 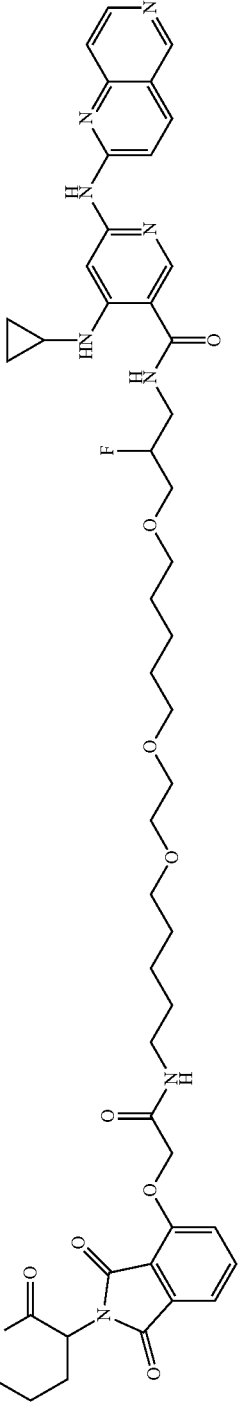 |
| I-207 | 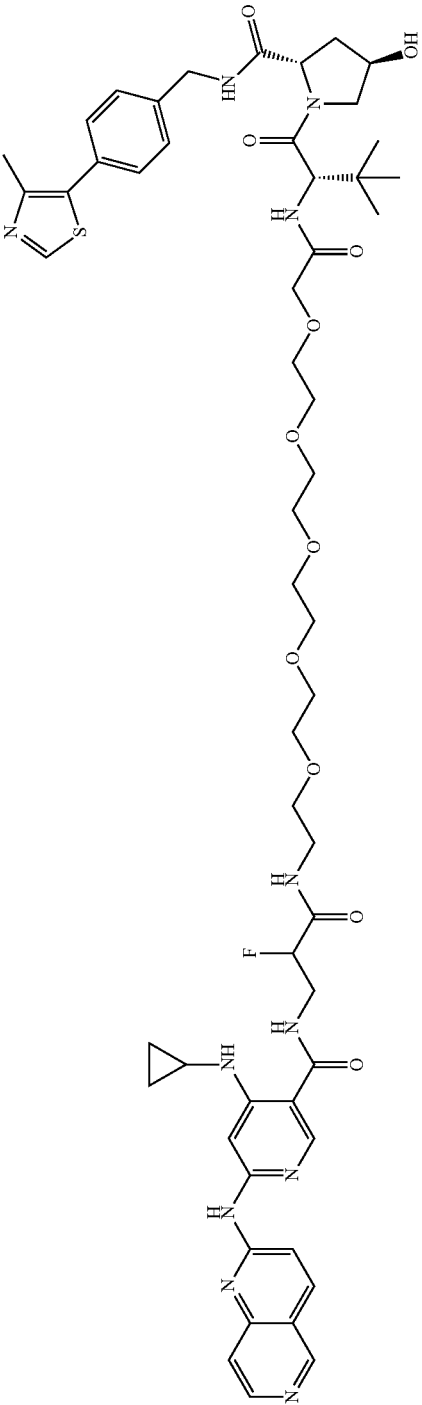 |

TABLE 1-continued
Exemplary Compounds
| I-# | Structure |
|---|---|
| I-208 | 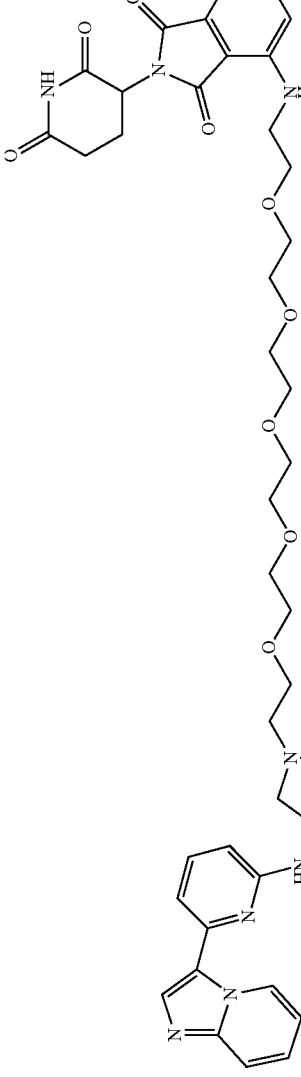 |
| I-209 | 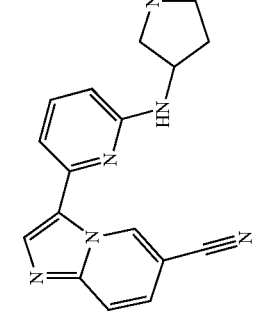 |

TABLE 1-continued

Exemplary Compounds

| I-# | Structure |
|---|---|
| I-210 | 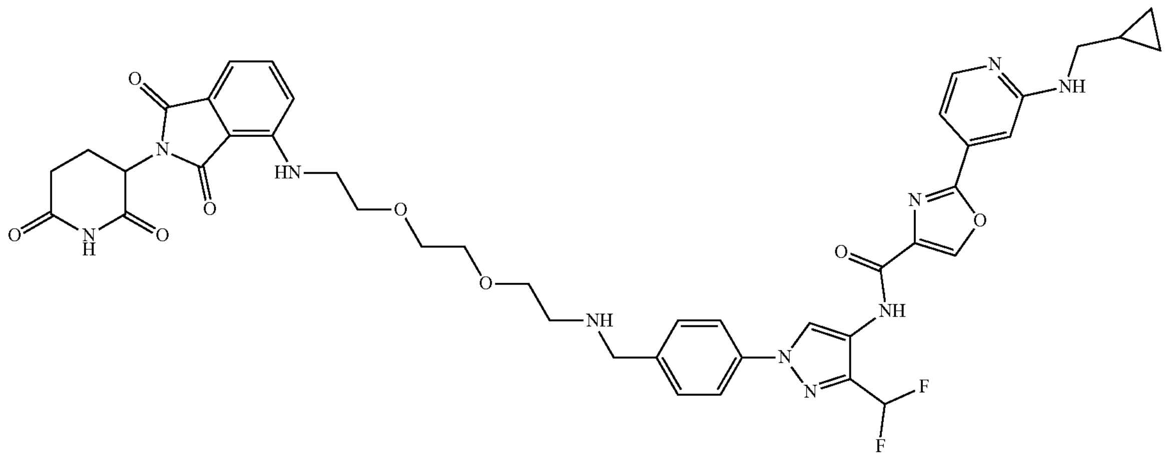 [SMILES: O=C1CCC(N2C(=O)c3cccc(NCCOCCOCCNCc4ccc(-n5cc(NC(=O)c6coc(-c7ccnc(NCC8CC8)c7)n6)c(C(F)F)n5)cc4)c3C2=O)C(=O)N1] |
| I-211 | 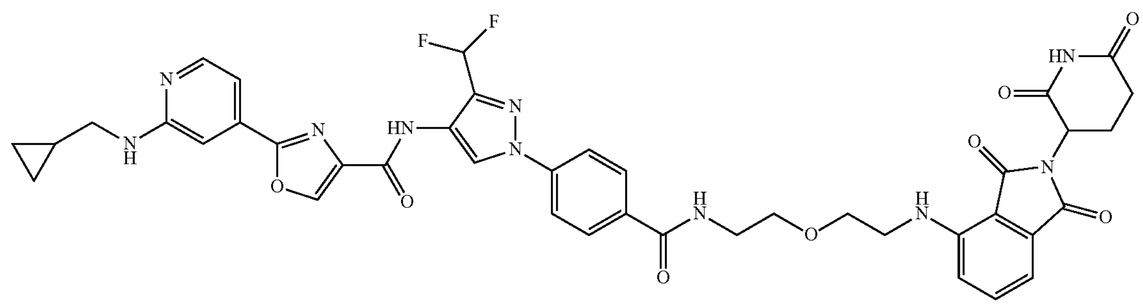 [SMILES: O=C1CCC(N2C(=O)c3cccc(NCCOCCNC(=O)c4ccc(-n5cc(NC(=O)c6coc(-c7ccnc(NCC8CC8)c7)n6)c(C(F)F)n5)cc4)c3C2=O)C(=O)N1] |

TABLE 1-continued
Exemplary Compounds
| I-# | Structure |
|---|---|
| I-212 | 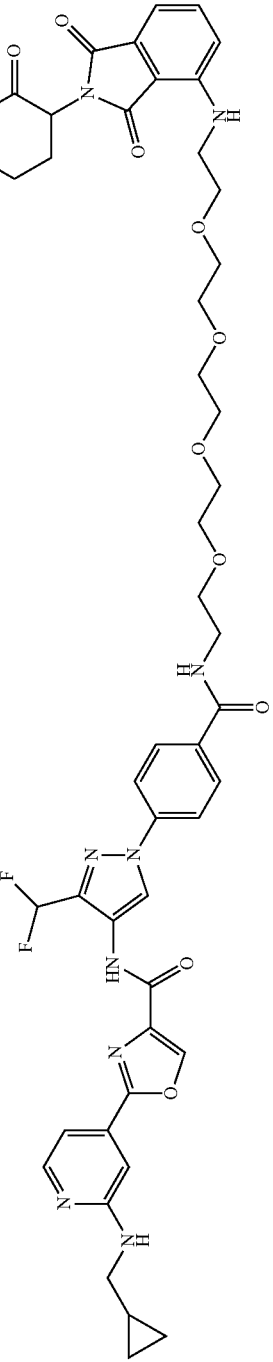 |
| I-213 | 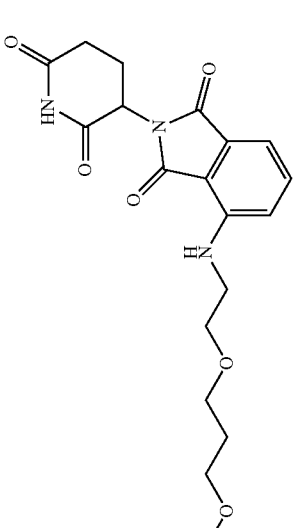 |

TABLE 1-continued

Exemplary Compounds

| I-# | Structure |
|---|---|
| I-214 | 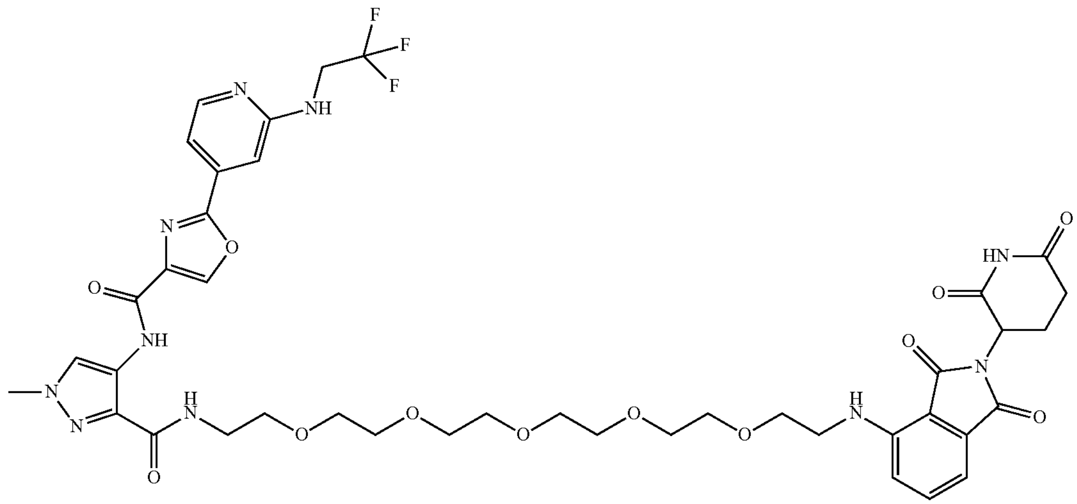 [SMILES: Cn1cc(NC(=O)c2coc(-c3ccnc(NCC(F)(F)F)c3)n2)c(C(=O)NCCOCCOCCOCCOCCOCCNc2cccc3c2C(=O)N(C2CCC(=O)NC2=O)C3=O)n1] |
| I-215 | 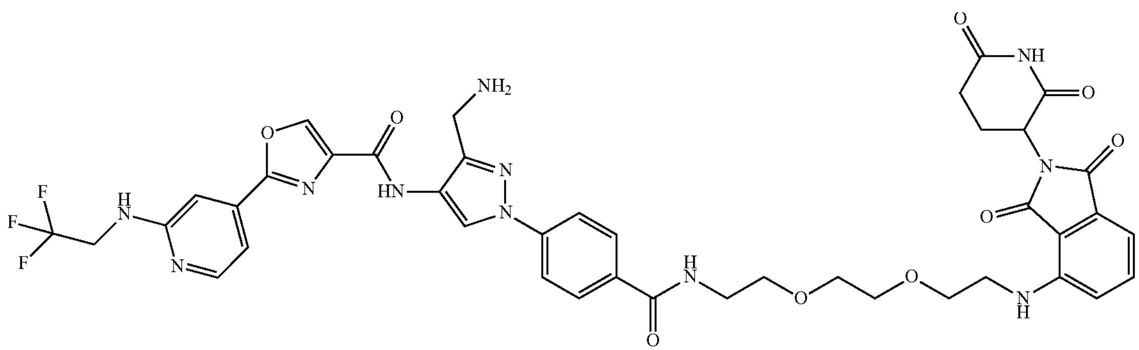 [SMILES: NCc1nn(-c2ccc(C(=O)NCCOCCOCCNc3cccc4c3C(=O)N(C3CCC(=O)NC3=O)C4=O)cc2)cc1NC(=O)c1coc(-c2ccnc(NCC(F)(F)F)c2)n1] |

TABLE 1-continued

Exemplary Compounds

| I-# | Structure |
|---|---|
| I-216 | 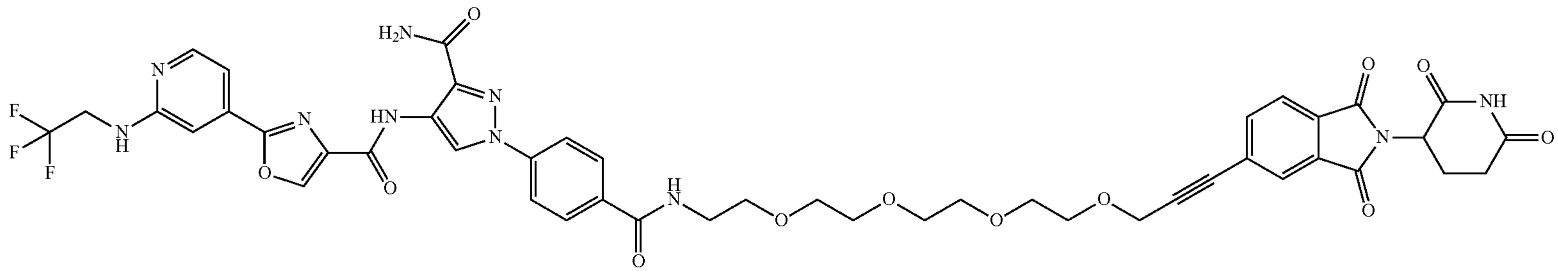 [SMILES: NC(=O)c1nn(-c2ccc(C(=O)NCCOCCOCCOCCOCC#Cc3ccc4c(c3)C(=O)N(C3CCC(=O)NC3=O)C4=O)cc2)cc1NC(=O)c1coc(-c2ccnc(NCC(F)(F)F)c2)n1] |
| I-217 | 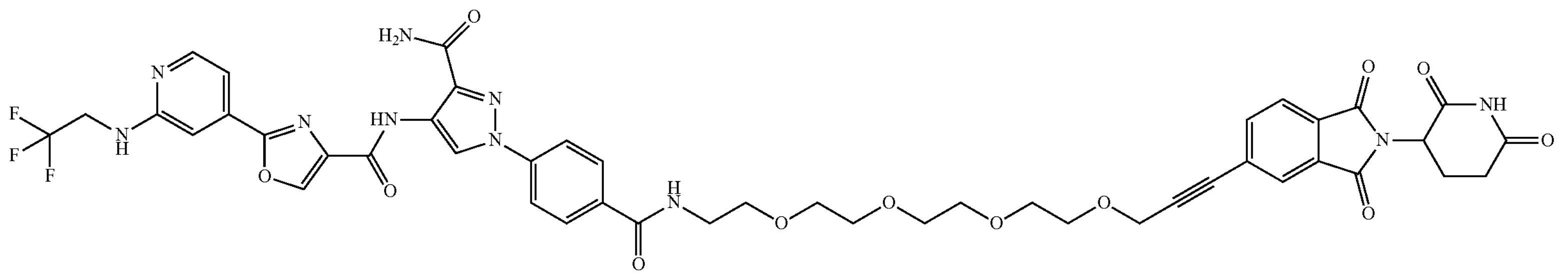 [SMILES: NC(=O)c1nn(-c2ccc(C(=O)NCCOCCOCCOCCOCC#Cc3ccc4c(c3)C(=O)N(C3CCC(=O)NC3=O)C4=O)cc2)cc1NC(=O)c1coc(-c2ccnc(NCC(F)(F)F)c2)n1] |
| I-218 | 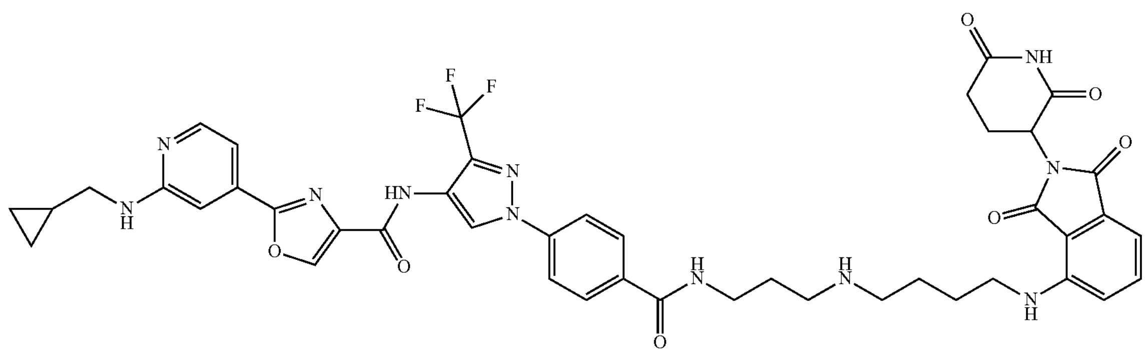 [SMILES: O=C1CCC(N2C(=O)c3cccc(NCCCCNCCCNC(=O)c4ccc(-n5cc(NC(=O)c6coc(-c7ccnc(NCC8CC8)c7)n6)c(C(F)(F)F)n5)cc4)c3C2=O)C(=O)N1] |

TABLE 1-continued
Exemplary Compounds
| I-# | Structure |
|---|---|
| I-219 | 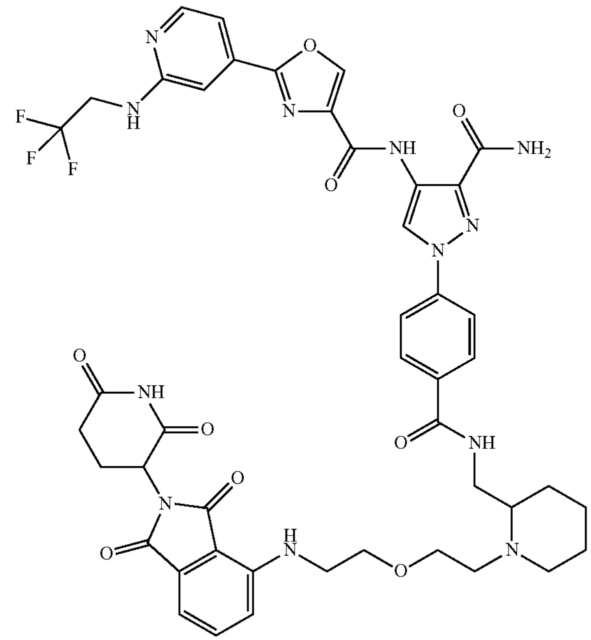 [SMILES: NC(=O)c1nn(-c2ccc(C(=O)NCC3CCCCN3CCOCCNc3cccc4c3C(=O)N(C3CCC(=O)NC3=O)C4=O)cc2)cc1NC(=O)c1coc(-c2ccnc(NCC(F)(F)F)c2)n1] |
| I-220 | 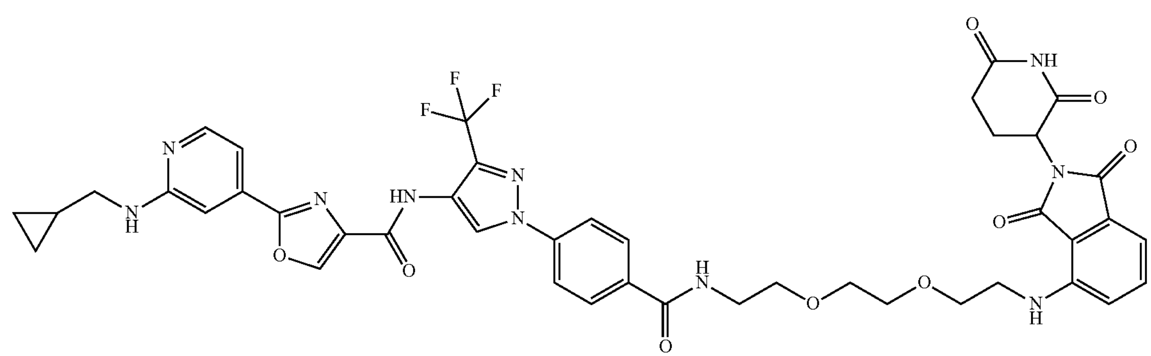 [SMILES: O=C1CCC(N2C(=O)c3cccc(NCCNCCOCCNC(=O)c4ccc(-n5cc(NC(=O)c6coc(-c7ccnc(NCC8CC8)c7)n6)c(C(F)(F)F)n5)cc4)c3C2=O)C(=O)N1] |

TABLE 1-continued
Exemplary Compounds
| I-# | Structure |
|---|---|
| I-221 | 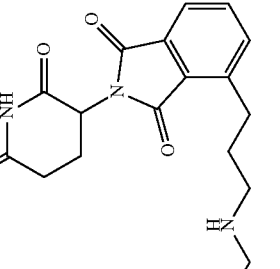 |
| I-222 | 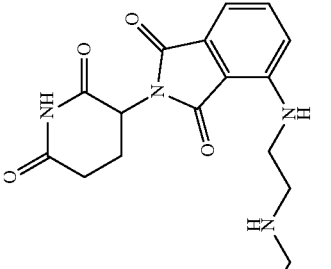 |

TABLE 1-continued
Exemplary Compounds
| I-# | Structure |
|---|---|
| I-223 | 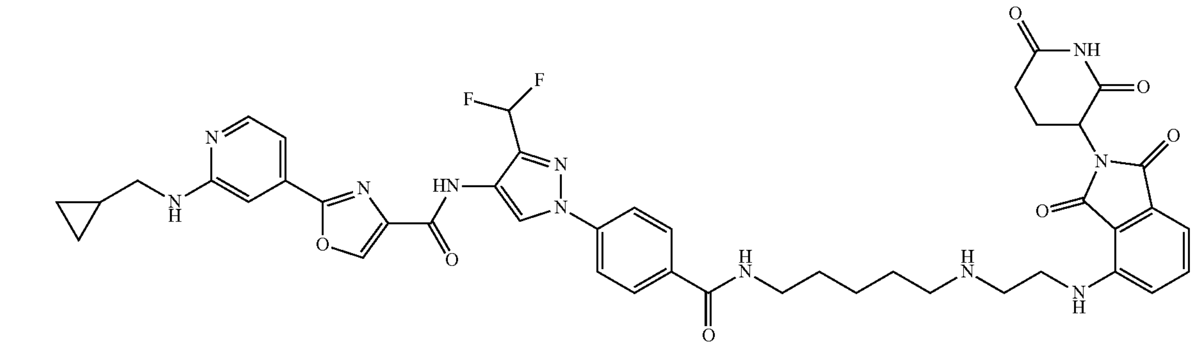 [SMILES: O=C1CCC(N2C(=O)c3cccc(NCCNCCCCCNC(=O)c4ccc(-n5cc(NC(=O)c6coc(-c7ccnc(NCC8CC8)c7)n6)c(C(F)F)n5)cc4)c3C2=O)C(=O)N1] |
| I-224 | 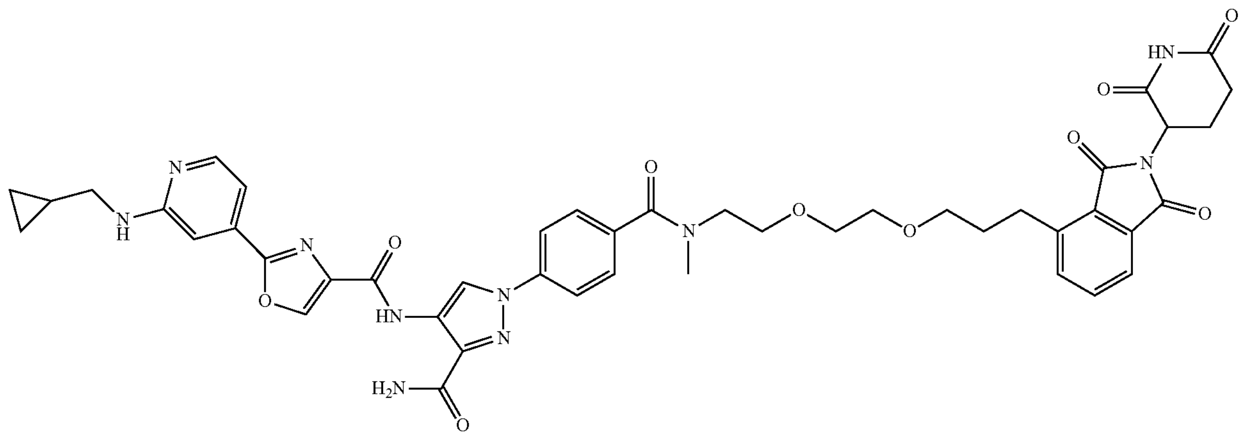 [SMILES: CN(CCOCCOCCCc1cccc2c1C(=O)N(C1CCC(=O)NC1=O)C2=O)C(=O)c1ccc(-n2cc(NC(=O)c3coc(-c4ccnc(NCC5CC5)c4)n3)c(C(N)=O)n2)cc1] |

TABLE 1-continued
Exemplary Compounds
| I-# | Structure |
|---|---|
| I-225 | 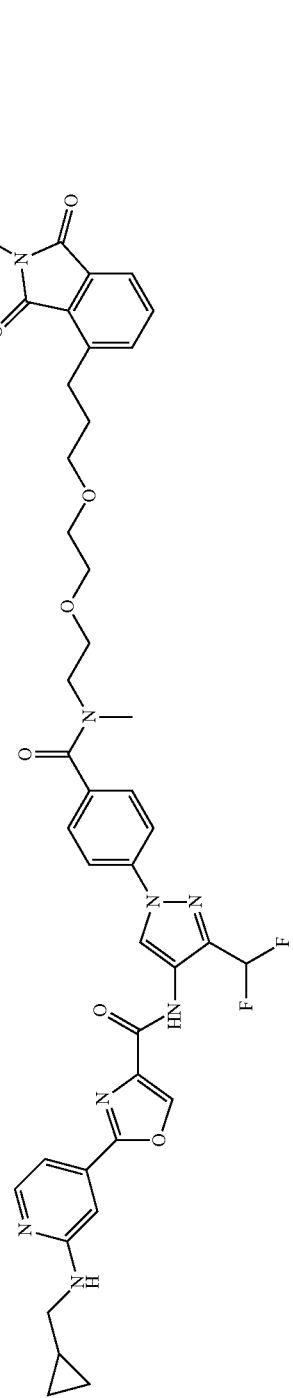 |
| I-226 | 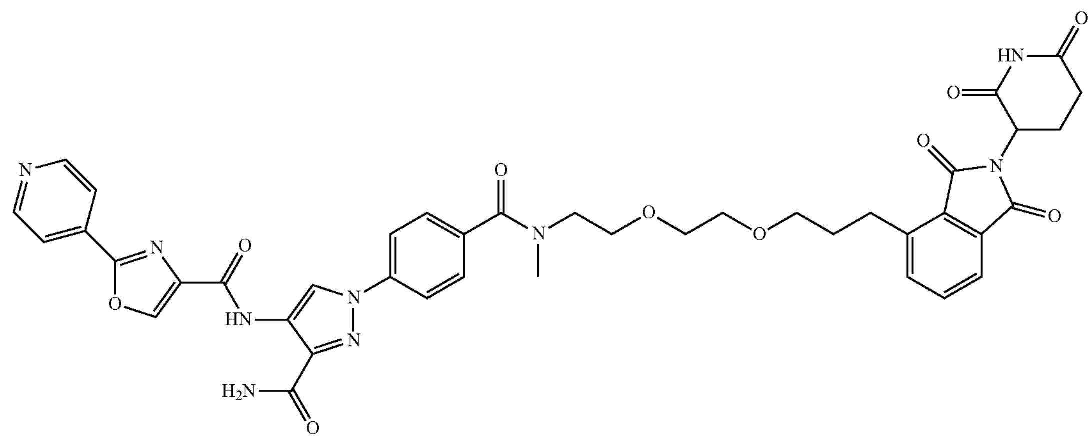 [SMILES: CN(CCOCCOCCCc1cccc2c1C(=O)N(C1CCC(=O)NC1=O)C2=O)C(=O)c1ccc(-n2cc(NC(=O)c3coc(-c4ccncc4)n3)c(C(N)=O)n2)cc1] |

TABLE 1-continued
Exemplary Compounds
| I-# | Structure |
|---|---|
| I-227 | 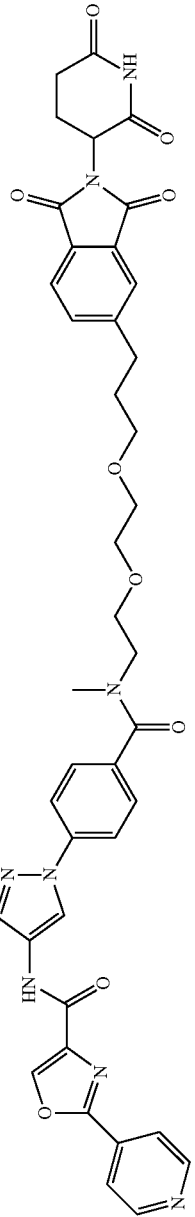 |
| I-228 | 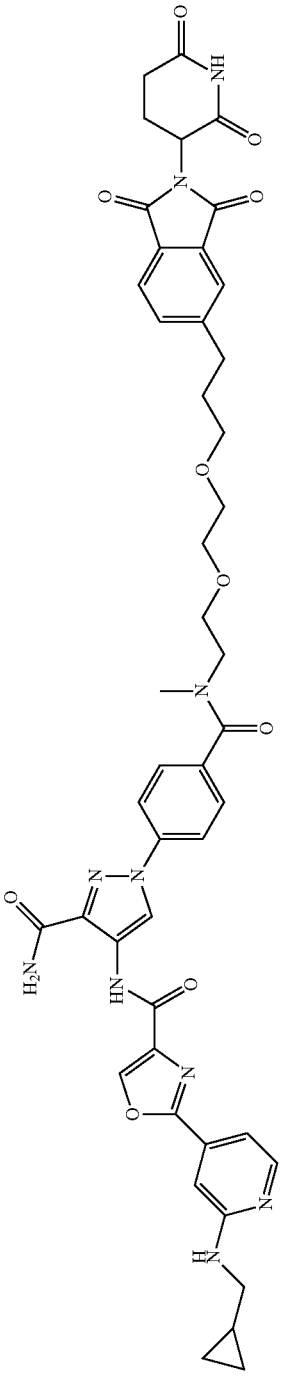 |
| I-229 | 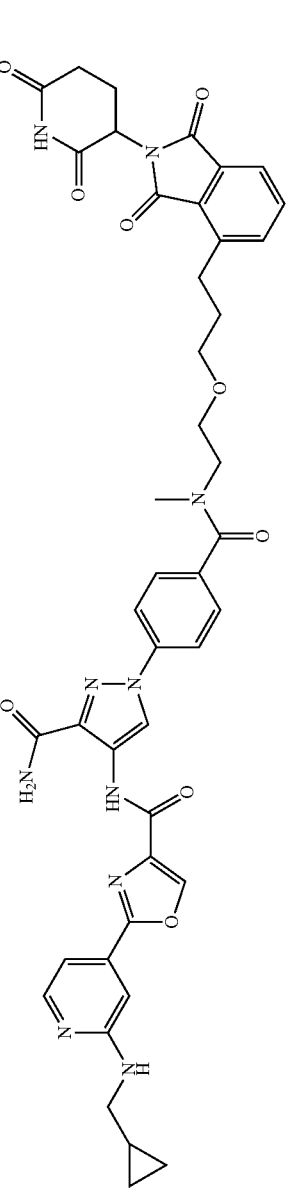 |

TABLE 1-continued

Exemplary Compounds

| I-# | Structure |
|---|---|
| I-230 | (structure) |
| I-231 | (structure) |

TABLE 1-continued

Exemplary Compounds

| I-# | Structure |
|---|---|
| I-232 | 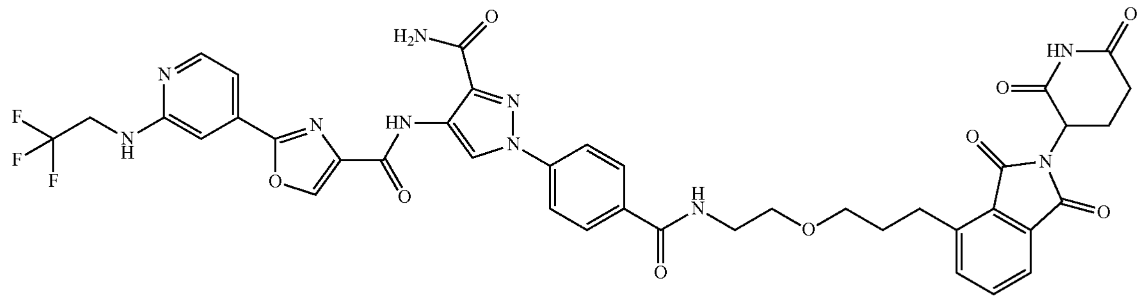 [SMILES: NC(=O)c1nn(-c2ccc(C(=O)NCCOCCCc3cccc4c3C(=O)N(C3CCC(=O)NC3=O)C4=O)cc2)cc1NC(=O)c1coc(-c2ccnc(NCC(F)(F)F)c2)n1] |
| I-233 | 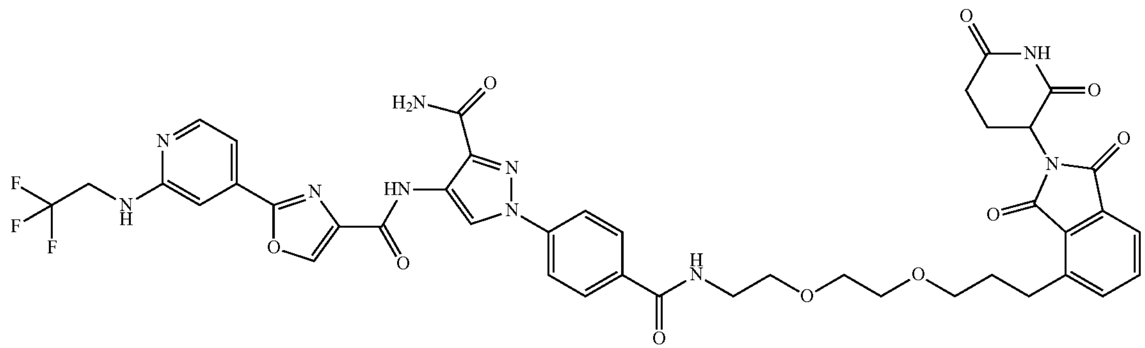 [SMILES: NC(=O)c1nn(-c2ccc(C(=O)NCCOCCOCCCc3cccc4c3C(=O)N(C3CCC(=O)NC3=O)C4=O)cc2)cc1NC(=O)c1coc(-c2ccnc(NCC(F)(F)F)c2)n1] |
| I-234 | 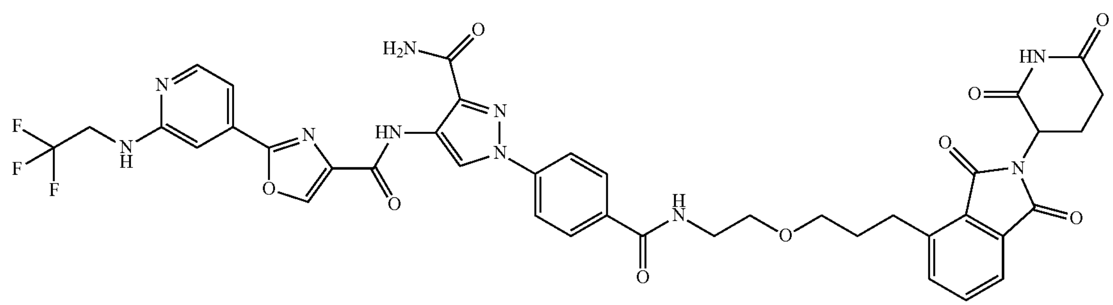 [SMILES: NC(=O)c1nn(-c2ccc(C(=O)NCCOCCCc3cccc4c3C(=O)N(C3CCC(=O)NC3=O)C4=O)cc2)cc1NC(=O)c1coc(-c2ccnc(NCC(F)(F)F)c2)n1] |

TABLE 1-continued
Exemplary Compounds
| I-# | Structure |
|---|---|
| I-235 | 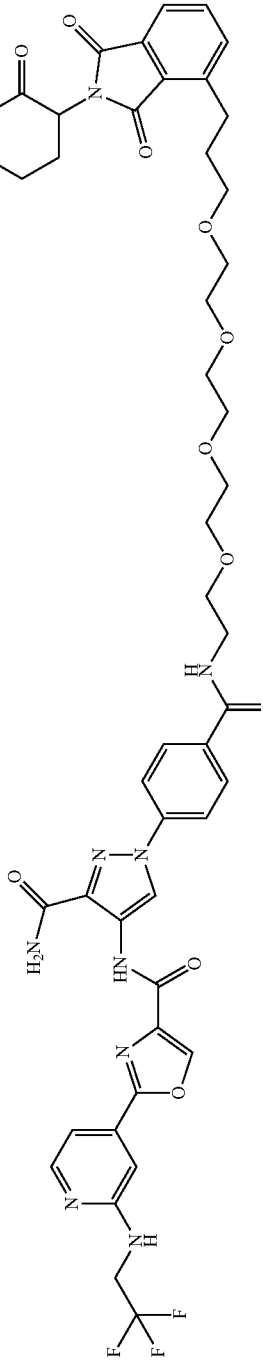 |
| I-236 | 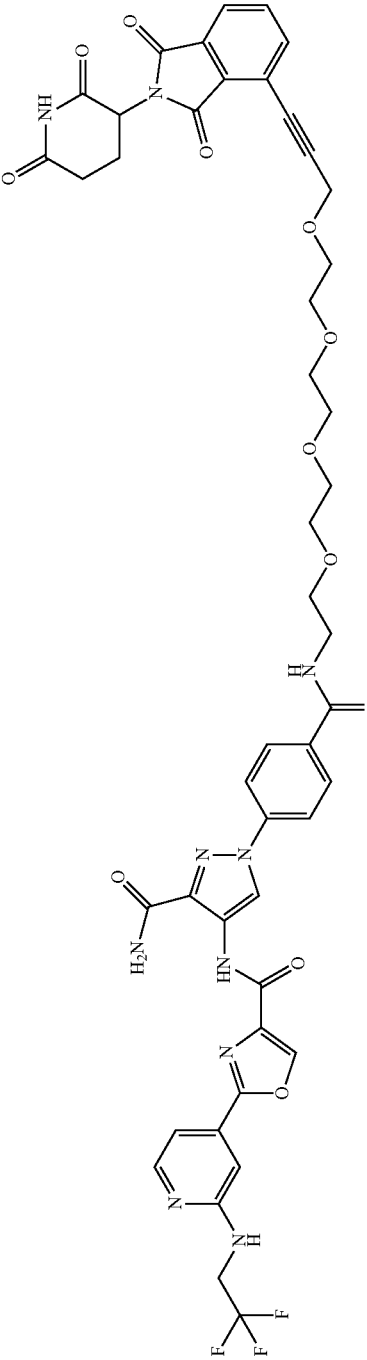 |

TABLE 1-continued
Exemplary Compounds
| I-# | Structure |
|---|---|
| I-237 | 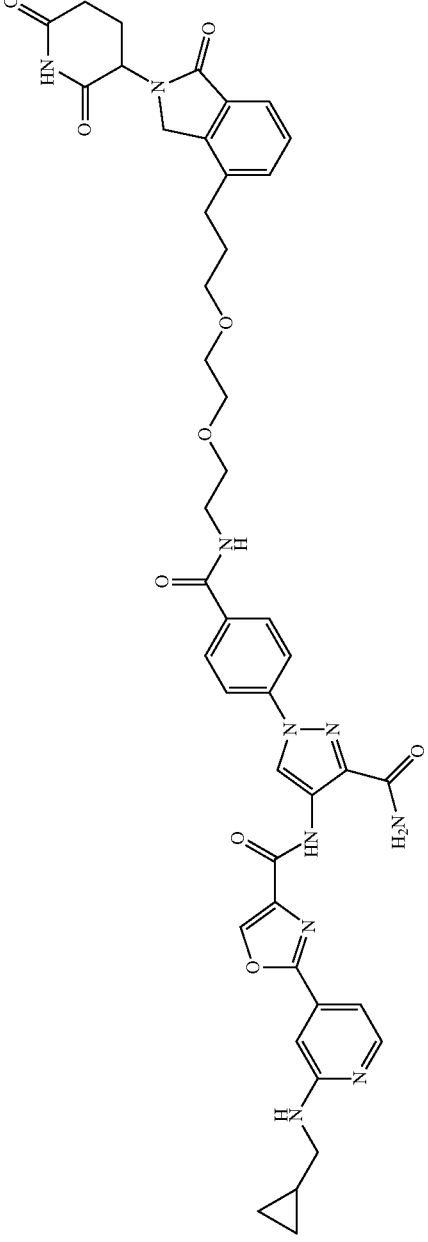 |
| I-238 | 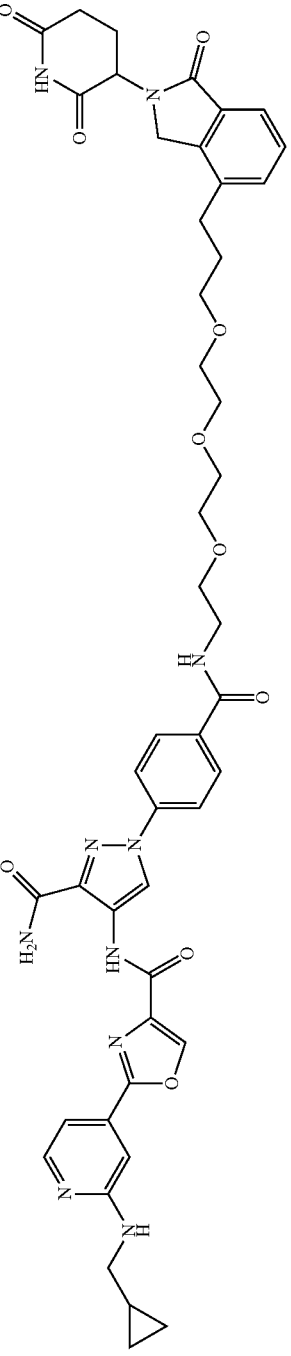 |
| I-239 | 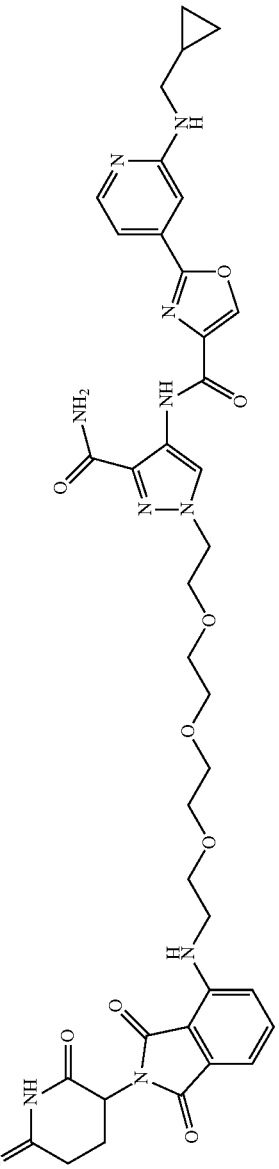 |

TABLE 1-continued
Exemplary Compounds
| I-# | Structure |
|---|---|
| I-240 | 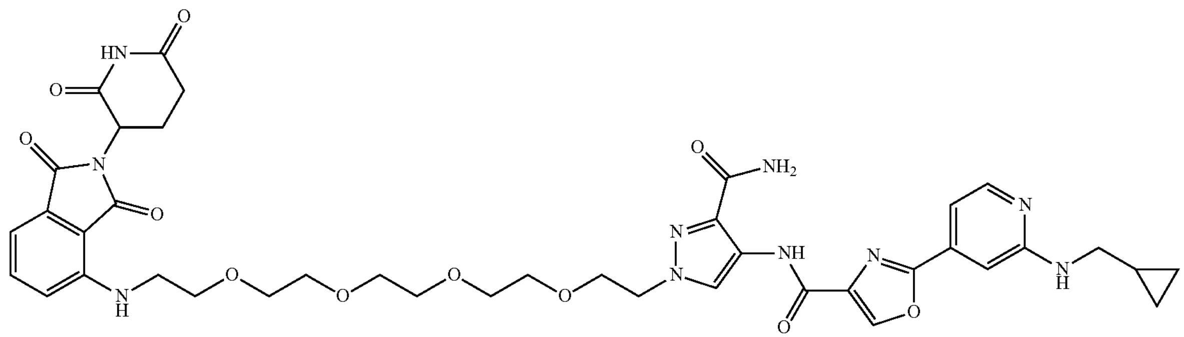 [SMILES: NC(=O)c1nn(CCOCCOCCOCCOCCNc2cccc3c2C(=O)N(C2CCC(=O)NC2=O)C3=O)cc1NC(=O)c1coc(-c2ccnc(NCC3CC3)c2)n1] |
| I-241 | 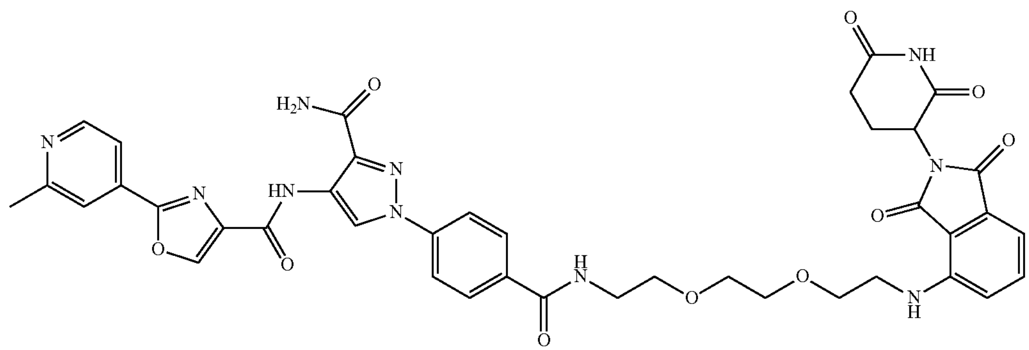 [SMILES: Cc1cc(-c2nc(C(=O)Nc3cn(-c4ccc(C(=O)NCCOCCOCCNc5cccc6c5C(=O)N(C5CCC(=O)NC5=O)C6=O)cc4)nc3C(N)=O)co2)ccn1] |

TABLE 1-continued

Exemplary Compounds

| I-# | Structure |
|---|---|
| I-242 | 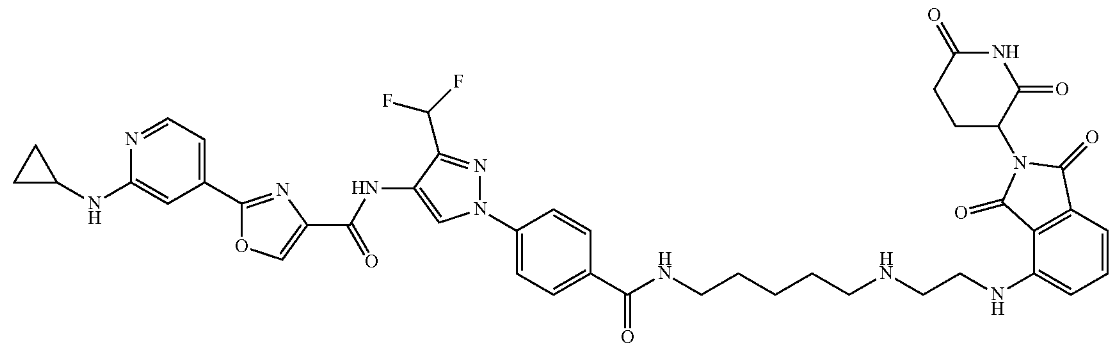 [SMILES: O=C1CCC(N2C(=O)c3cccc(NCCNCCCCCNC(=O)c4ccc(-n5cc(NC(=O)c6coc(-c7ccnc(NC8CC8)c7)n6)c(C(F)F)n5)cc4)c3C2=O)C(=O)N1] |
| I-243 | 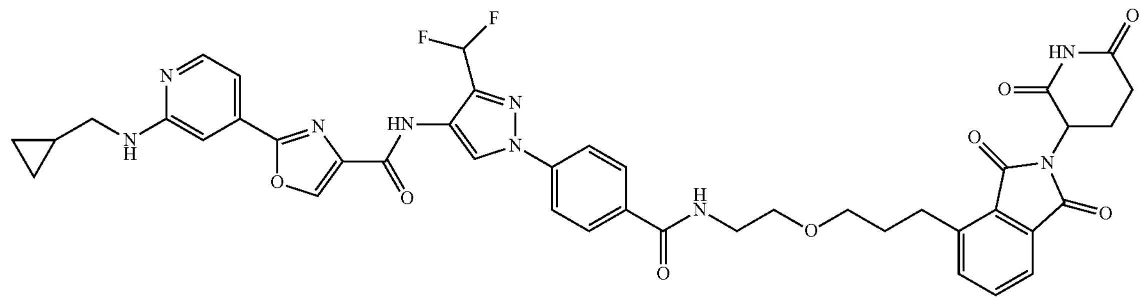 [SMILES: O=C1CCC(N2C(=O)c3cccc(CCCOCCNC(=O)c4ccc(-n5cc(NC(=O)c6coc(-c7ccnc(NCC8CC8)c7)n6)c(C(F)F)n5)cc4)c3C2=O)C(=O)N1] |
| I-244 | 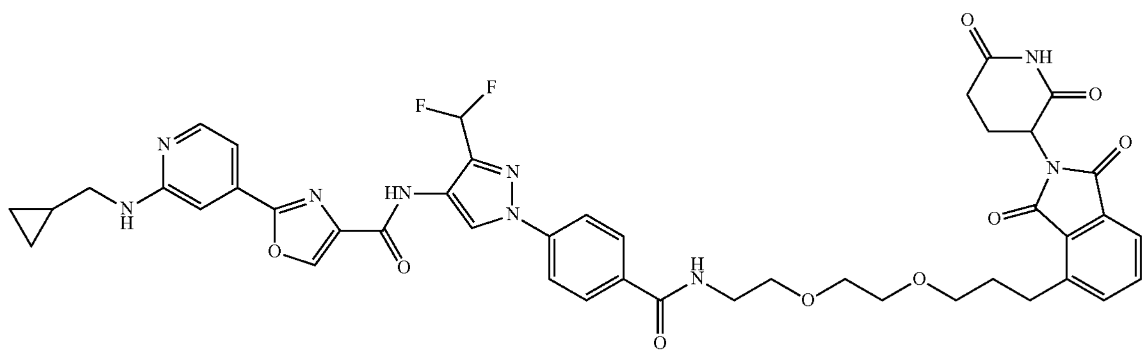 [SMILES: O=C1CCC(N2C(=O)c3cccc(CCCOCCOCCNC(=O)c4ccc(-n5cc(NC(=O)c6coc(-c7ccnc(NCC8CC8)c7)n6)c(C(F)F)n5)cc4)c3C2=O)C(=O)N1] |

TABLE 1-continued

Exemplary Compounds

| I-# | Structure |
|---|---|
| I-245 | 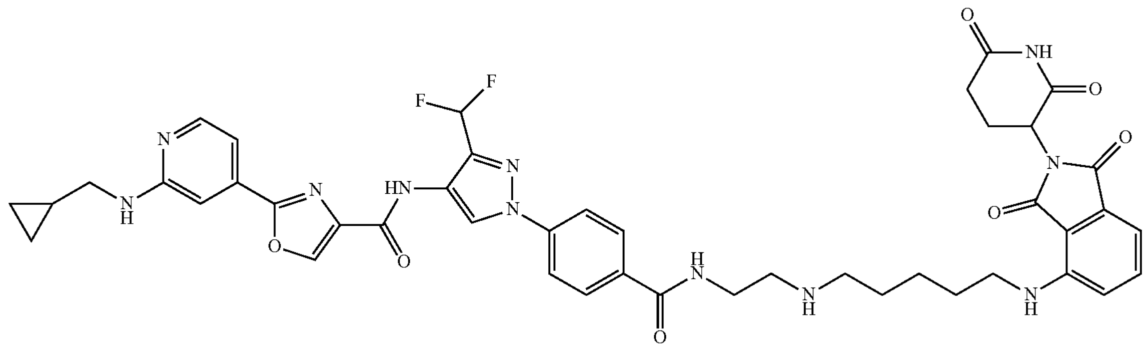 [SMILES: O=C1CCC(N2C(=O)c3cccc(NCCCCCNCCNC(=O)c4ccc(-n5cc(NC(=O)c6coc(-c7ccnc(NCC8CC8)c7)n6)c(C(F)F)n5)cc4)c3C2=O)C(=O)N1] |
| I-246 | 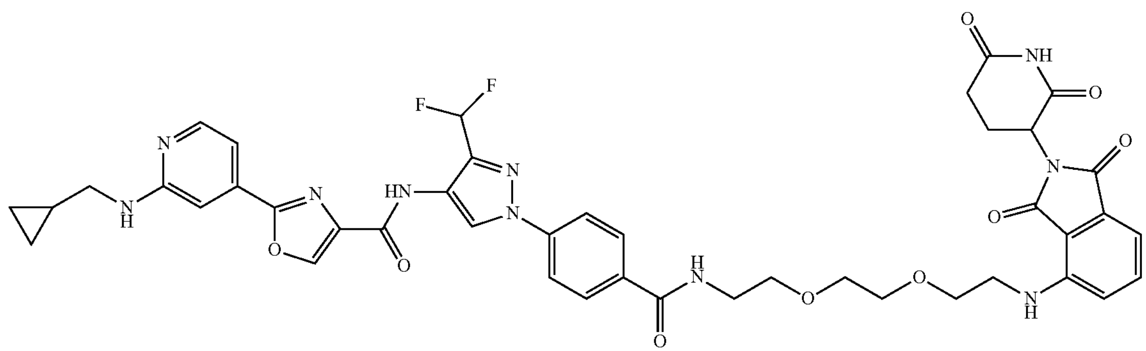 |
| I-247 | 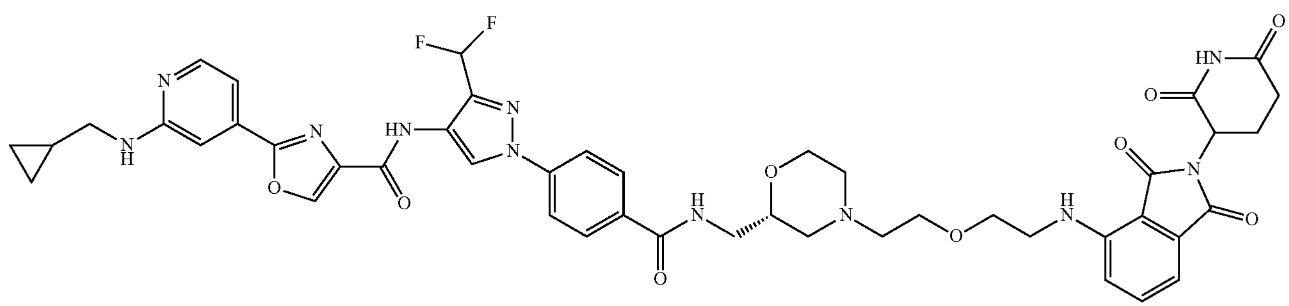 [SMILES: O=C1CCC(N2C(=O)c3cccc(NCCOCCN4CCO[C@@H](CNC(=O)c5ccc(-n6cc(NC(=O)c7coc(-c8ccnc(NCC9CC9)c8)n7)c(C(F)F)n6)cc5)C4)c3C2=O)C(=O)N1] |

TABLE 1-continued

Exemplary Compounds

| I-# | Structure |
|---|---|
| I-248 | 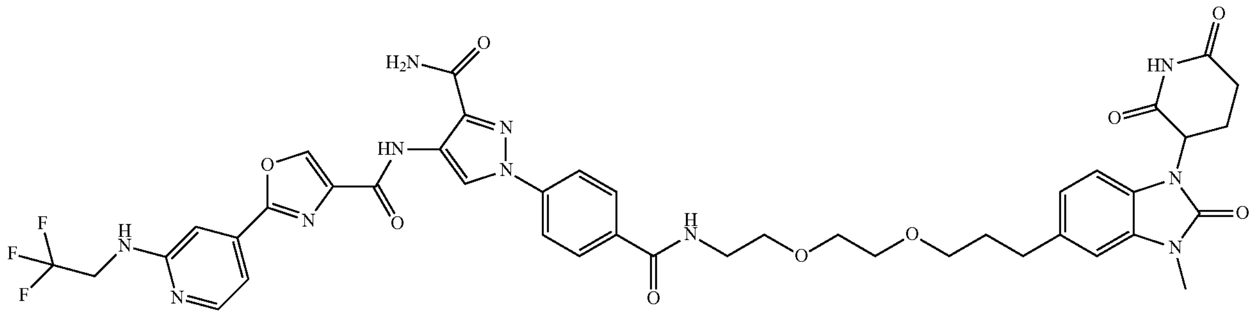 [SMILES: Cn1c(=O)n(C2CCC(=O)NC2=O)c2ccc(CCCOCCOCCNC(=O)c3ccc(-n4cc(NC(=O)c5coc(-c6ccnc(NCC(F)(F)F)c6)n5)c(C(N)=O)n4)cc3)cc21] |
| I-249 | 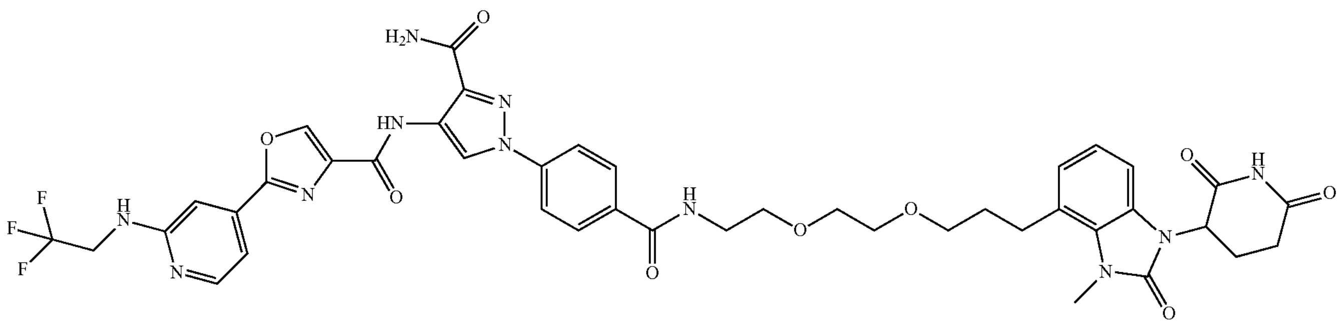 [SMILES: Cn1c(=O)n(C2CCC(=O)NC2=O)c2cccc(CCCOCCOCCNC(=O)c3ccc(-n4cc(NC(=O)c5coc(-c6ccnc(NCC(F)(F)F)c6)n5)c(C(N)=O)n4)cc3)c21] |
| I-250 | 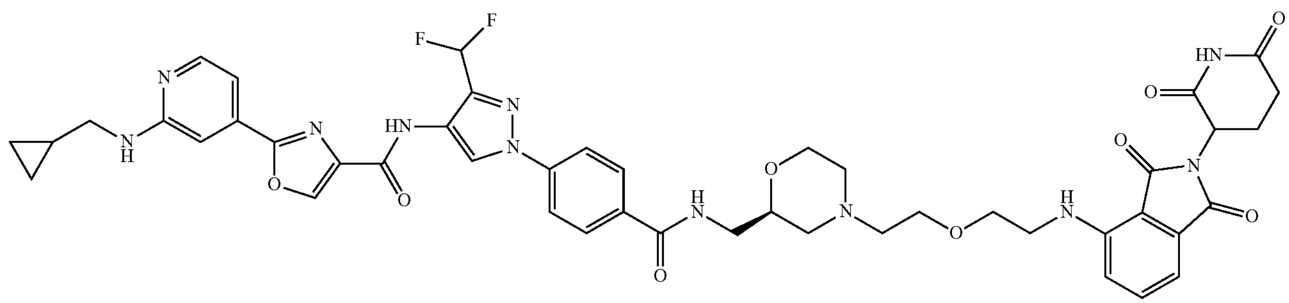 [SMILES: O=C1CCC(N2C(=O)c3cccc(NCCOCCN4CCO[C@H](CNC(=O)c5ccc(-n6cc(NC(=O)c7coc(-c8ccnc(NCC9CC9)c8)n7)c(C(F)F)n6)cc5)C4)c3C2=O)C(=O)N1] |

TABLE 1-continued
Exemplary Compounds
| I-# | Structure |
|---|---|
| I-251 | 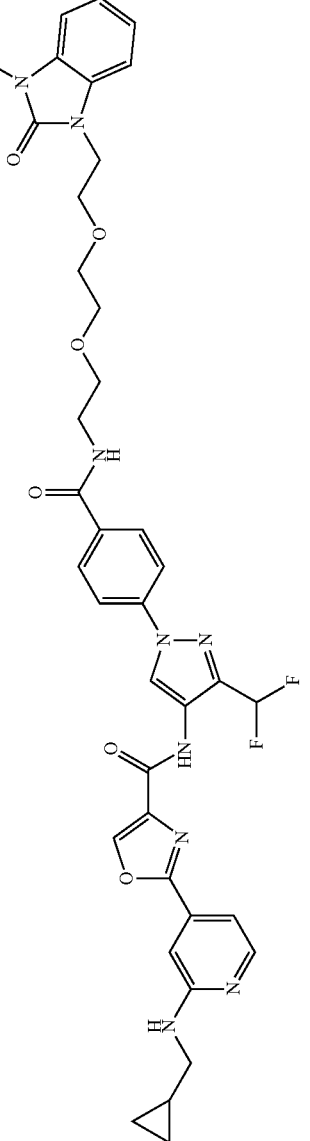 |
| I-252 | 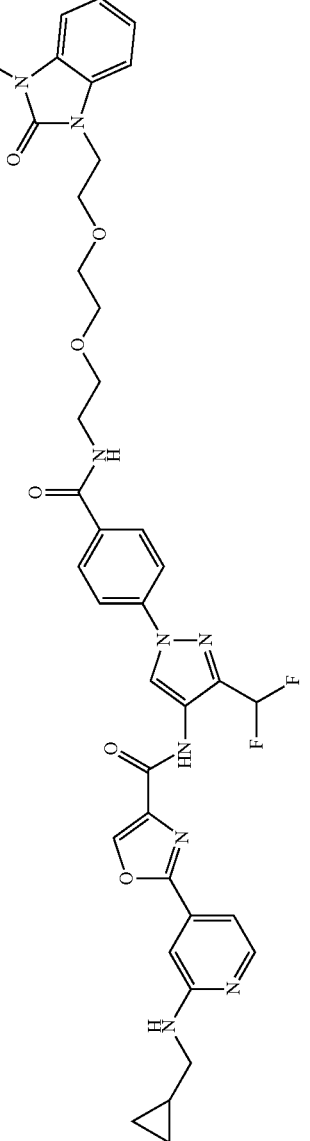 |

TABLE 1-continued

Exemplary Compounds

| I-# | Structure |
|---|---|
| I-253 | 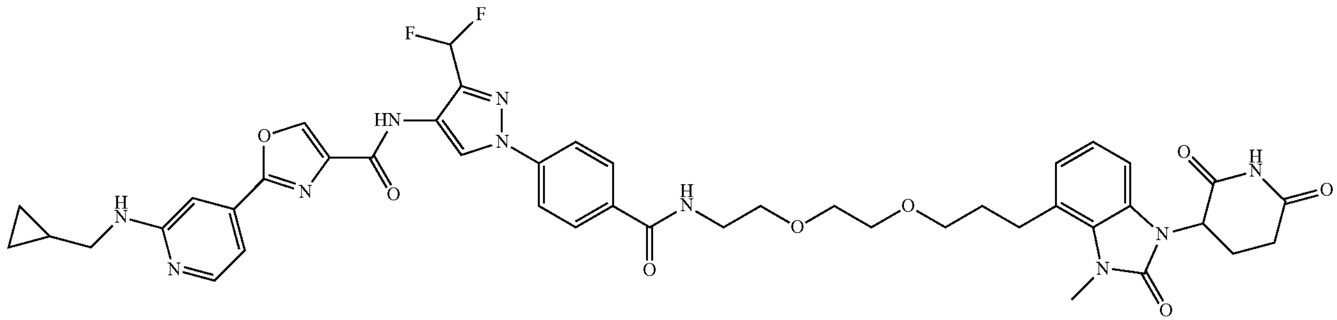 [SMILES: Cn1c(=O)n(C2CCC(=O)NC2=O)c2cccc(CCCOCCOCCNC(=O)c3ccc(-n4cc(NC(=O)c5coc(-c6ccnc(NCC7CC7)c6)n5)c(C(F)F)n4)cc3)c21] |
| I-254 | 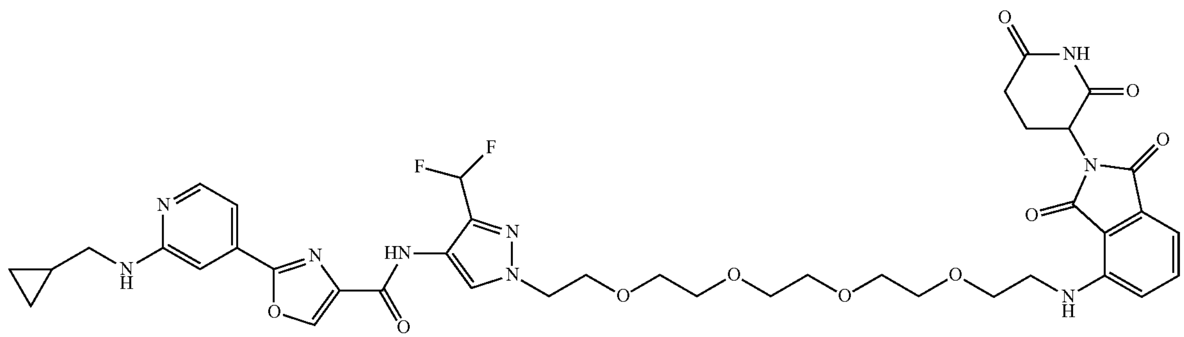 [SMILES: O=C1CCC(N2C(=O)c3cccc(NCCOCCOCCOCCOCCn4cc(NC(=O)c5coc(-c6ccnc(NCC7CC7)c6)n5)c(C(F)F)n4)c3C2=O)C(=O)N1] |
| I-255 | 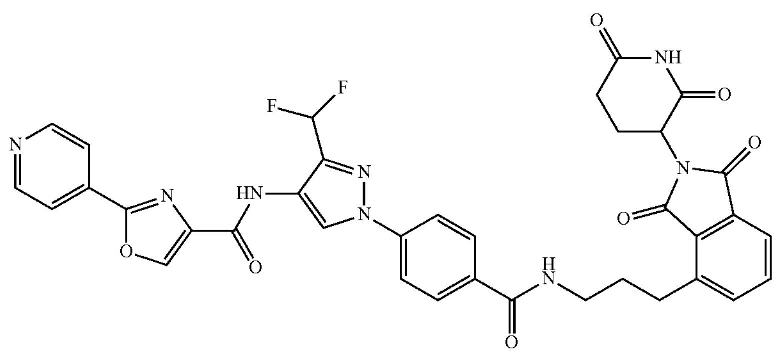 [SMILES: O=C1CCC(N2C(=O)c3cccc(CCCNC(=O)c4ccc(-n5cc(NC(=O)c6coc(-c7ccncc7)n6)c(C(F)F)n5)cc4)c3C2=O)C(=O)N1] |

TABLE 1-continued
Exemplary Compounds
| I-# | Structure |
|---|---|
| I-256 | 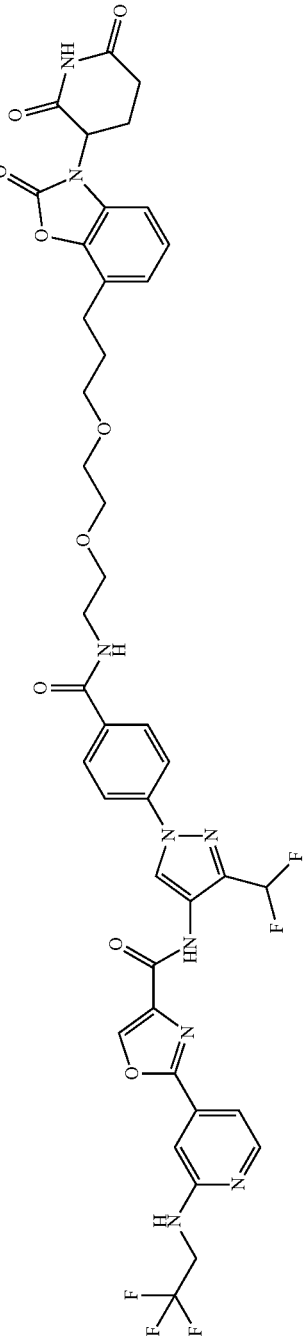 |
| I-257 | 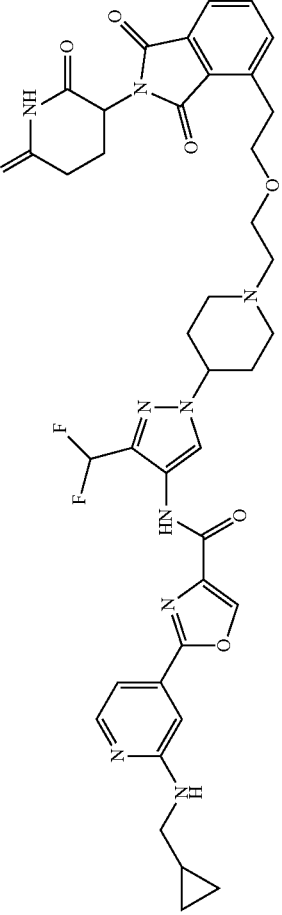 |
| I-258 | 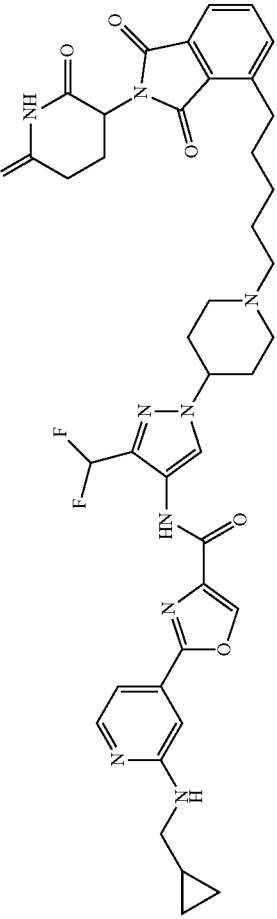 |

TABLE 1-continued
Exemplary Compounds
| I-# | Structure |
|---|---|
| I-259 | 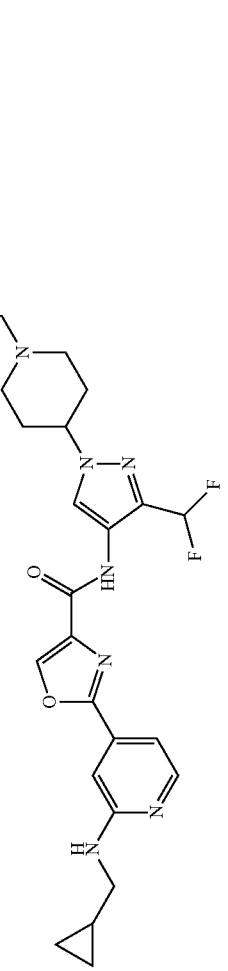 |
| I-260 | 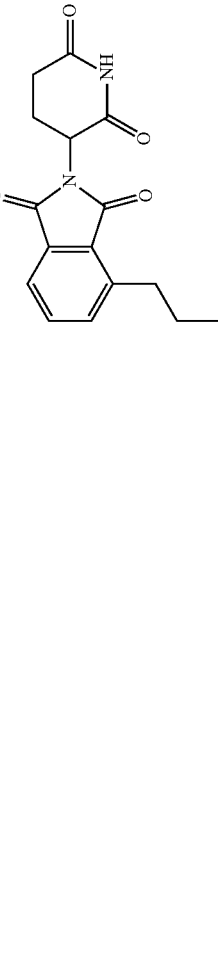 |

TABLE 1-continued
Exemplary Compounds
| I-# | Structure |
|---|---|
| I-261 | 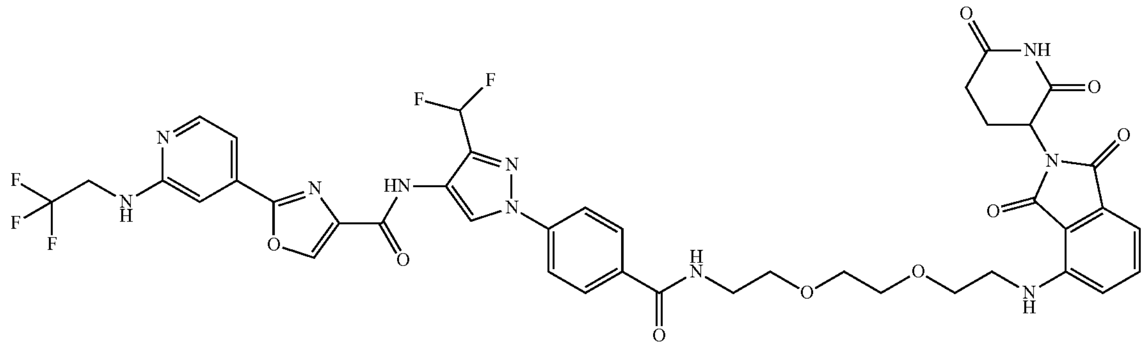 [SMILES: O=C1CCC(N2C(=O)c3cccc(NCCOCCOCCNC(=O)c4ccc(-n5cc(NC(=O)c6coc(-c7ccnc(NCC(F)(F)F)c7)n6)c(C(F)F)n5)cc4)c3C2=O)C(=O)N1] |
| I-262 | 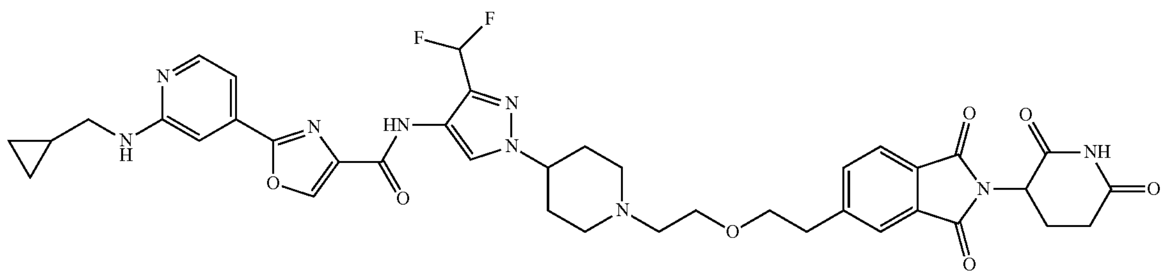 [SMILES: O=C1CCC(N2C(=O)c3ccc(CCOCCN4CCC(n5cc(NC(=O)c6coc(-c7ccnc(NCC8CC8)c7)n6)c(C(F)F)n5)CC4)cc3C2=O)C(=O)N1] |
| I-263 | 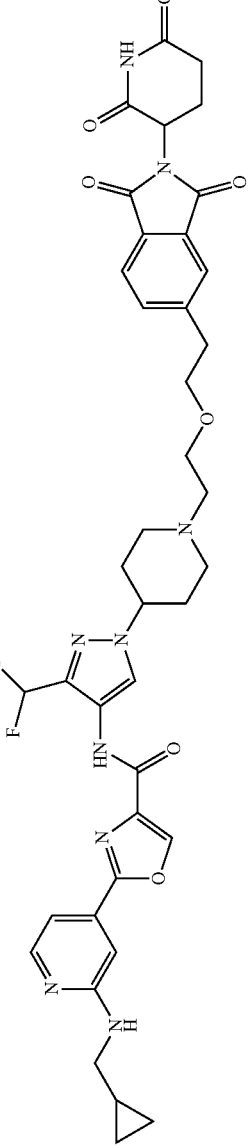 |

TABLE 1-continued

Exemplary Compounds

| I-# | Structure |
|---|---|
| I-264 | 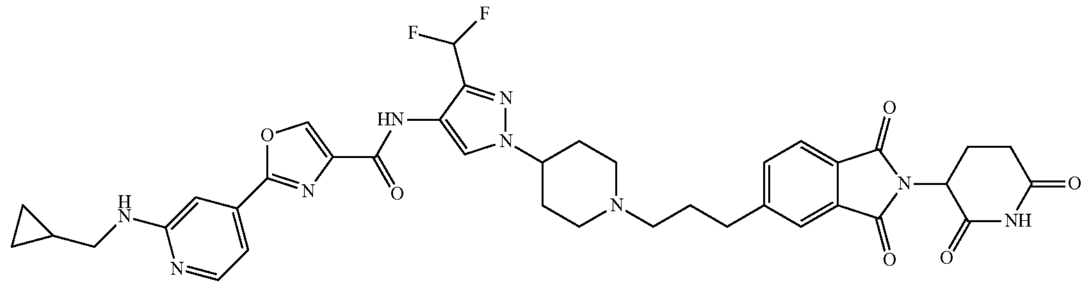 [SMILES: O=C1CCC(N2C(=O)c3ccc(CCCN4CCC(n5cc(NC(=O)c6coc(-c7ccnc(NCC8CC8)c7)n6)c(C(F)F)n5)CC4)cc3C2=O)C(=O)N1] |
| I-265 | 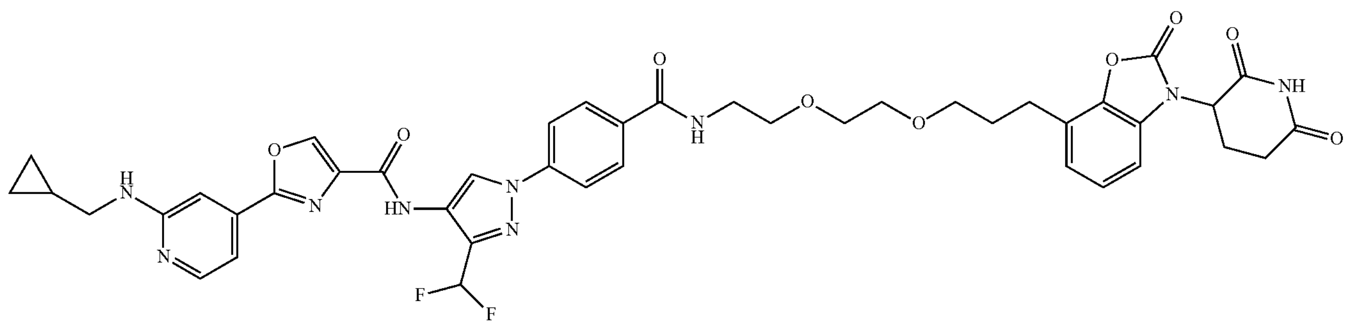 [SMILES: O=C1CCC(n2c(=O)oc3c(CCCOCCOCCNC(=O)c4ccc(-n5cc(NC(=O)c6coc(-c7ccnc(NCC8CC8)c7)n6)c(C(F)F)n5)cc4)cccc32)C(=O)N1] |
| I-266 | 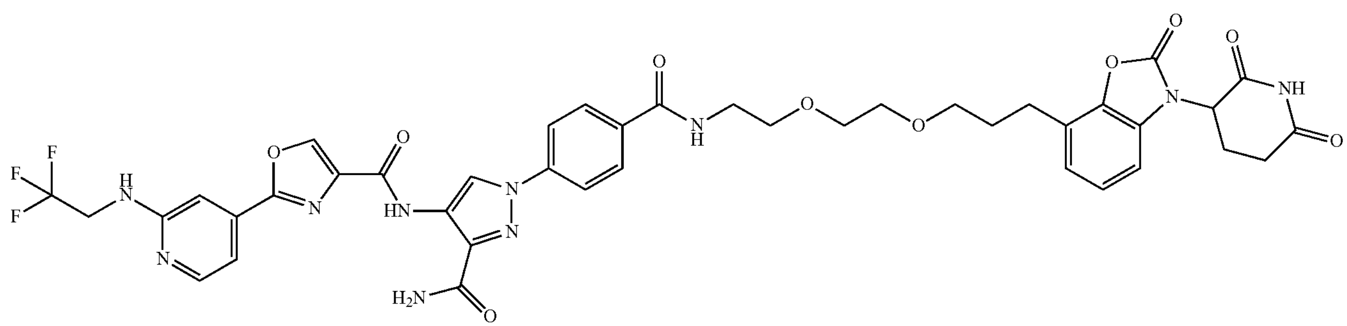 |

TABLE 1-continued
Exemplary Compounds
| I-# | Structure |
|---|---|
| I-267 | 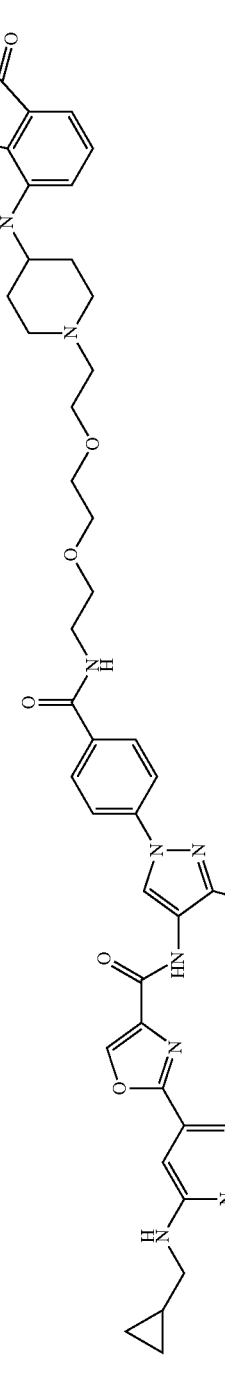 |
| I-268 | 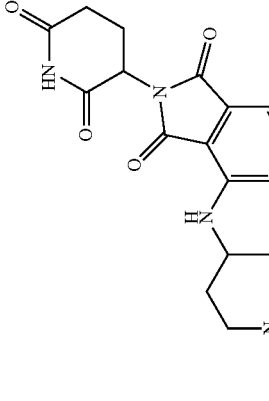 |

TABLE 1-continued

Exemplary Compounds

| I-# | Structure |
|---|---|
| I-269 | 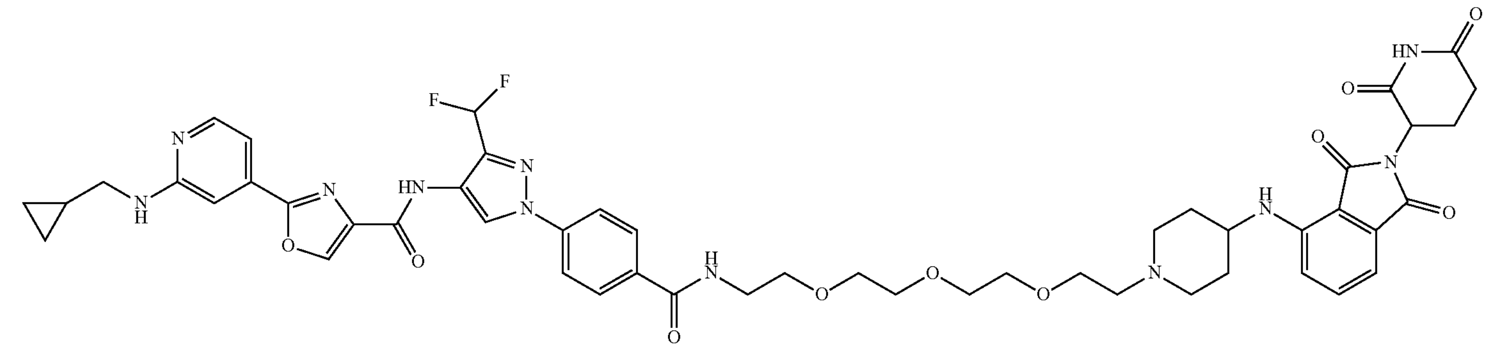 [SMILES: O=C1CCC(N2C(=O)c3cccc(NC4CCN(CCOCCOCCOCCNC(=O)c5ccc(-n6cc(NC(=O)c7coc(-c8ccnc(NCC9CC9)c8)n7)c(C(F)F)n6)cc5)CC4)c3C2=O)C(=O)N1] |
| I-270 | 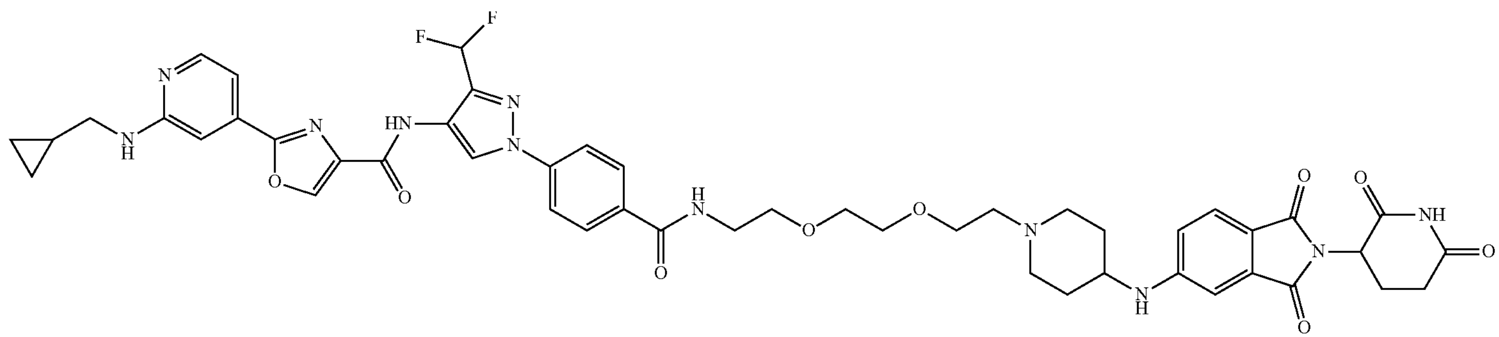 [SMILES: O=C1CCC(N2C(=O)c3ccc(NC4CCN(CCOCCOCCNC(=O)c5ccc(-n6cc(NC(=O)c7coc(-c8ccnc(NCC9CC9)c8)n7)c(C(F)F)n6)cc5)CC4)cc3C2=O)C(=O)N1] |
| I-271 | 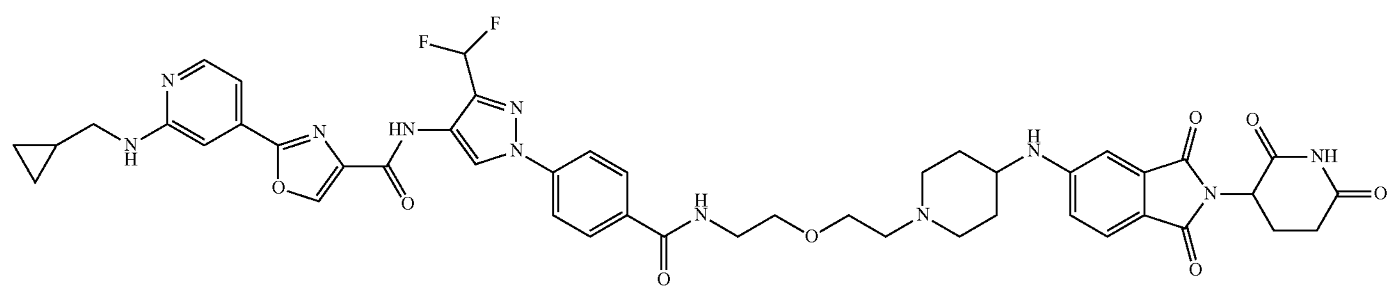 [SMILES: O=C1CCC(N2C(=O)c3ccc(NC4CCN(CCOCCNC(=O)c5ccc(-n6cc(NC(=O)c7coc(-c8ccnc(NCC9CC9)c8)n7)c(C(F)F)n6)cc5)CC4)cc3C2=O)C(=O)N1] |

TABLE 1-continued

Exemplary Compounds

| I-# | Structure |
|---|---|
| I-272 | 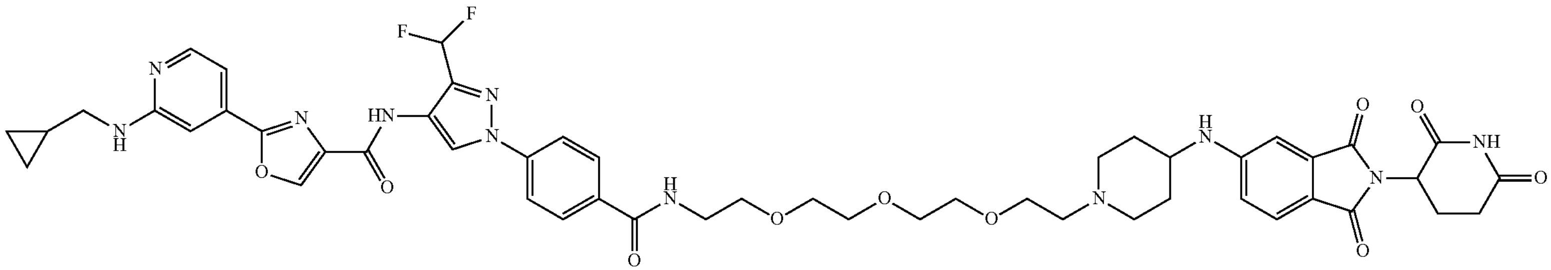 [SMILES: O=C1CCC(N2C(=O)c3ccc(NC4CCN(CCOCCOCCOCCNC(=O)c5ccc(-n6cc(NC(=O)c7coc(-c8ccnc(NCC9CC9)c8)n7)c(C(F)F)n6)cc5)CC4)cc3C2=O)C(=O)N1] |
| I-273 | 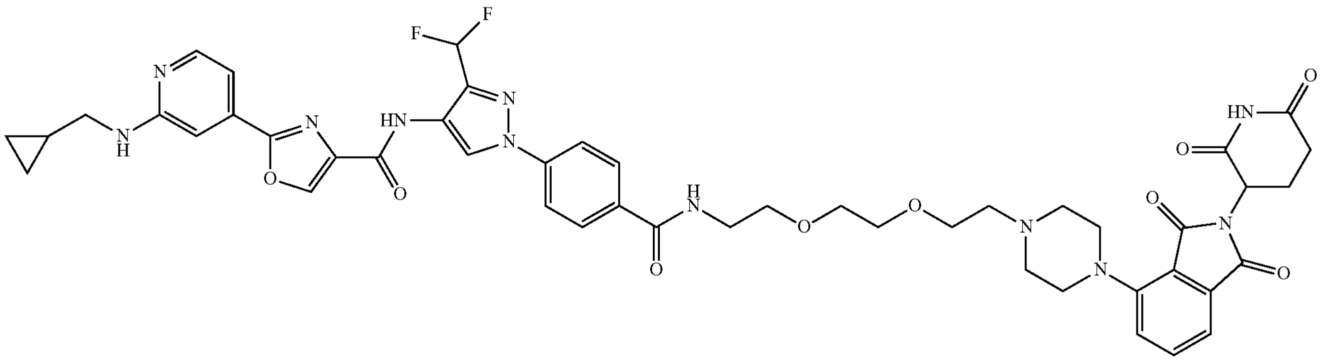 [SMILES: O=C1CCC(N2C(=O)c3cccc(N4CCN(CCOCCOCCNC(=O)c5ccc(-n6cc(NC(=O)c7coc(-c8ccnc(NCC9CC9)c8)n7)c(C(F)F)n6)cc5)CC4)c3C2=O)C(=O)N1] |

TABLE 1-continued
Exemplary Compounds
| I-# | Structure |
|---|---|
| I-274 | 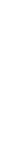 |
| I-275 | 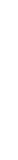 |

TABLE 1-continued

Exemplary Compounds

| I-# | Structure |
|---|---|
| I-276 | 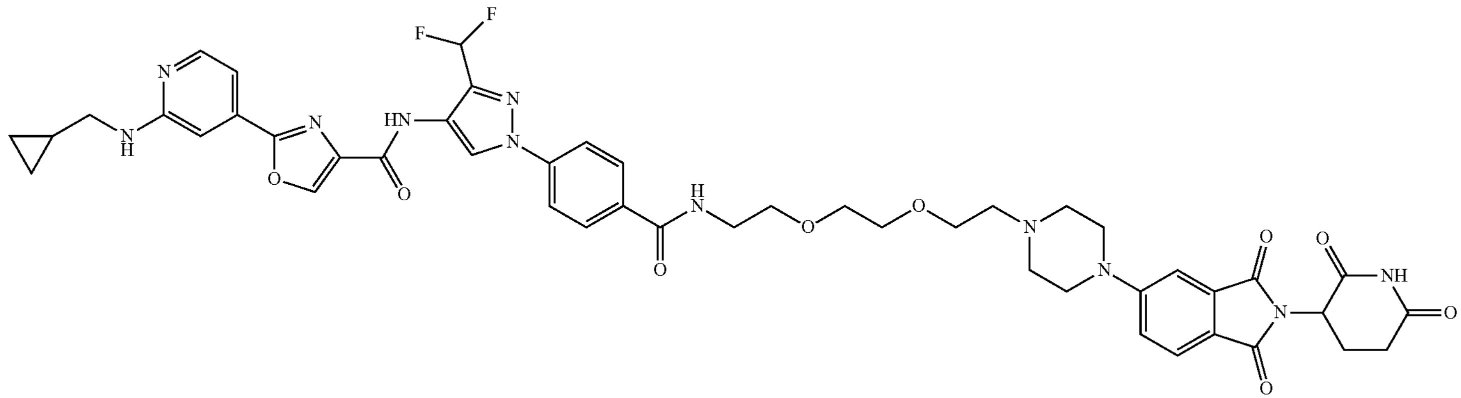 [SMILES: O=C1CCC(N2C(=O)c3ccc(N4CCN(CCOCCOCCNC(=O)c5ccc(-n6cc(NC(=O)c7coc(-c8ccnc(NCC9CC9)c8)n7)c(C(F)F)n6)cc5)CC4)cc3C2=O)C(=O)N1] |
| I-277 | 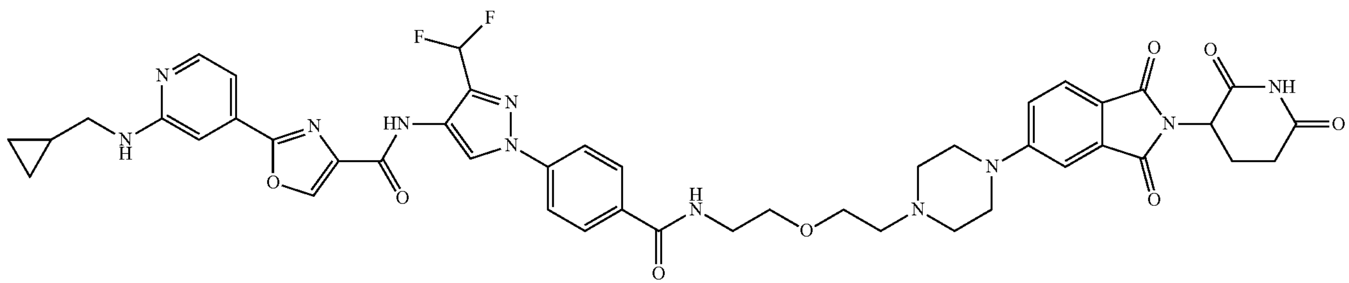 [SMILES: O=C1CCC(N2C(=O)c3ccc(N4CCN(CCOCCNC(=O)c5ccc(-n6cc(NC(=O)c7coc(-c8ccnc(NCC9CC9)c8)n7)c(C(F)F)n6)cc5)CC4)cc3C2=O)C(=O)N1] |
| I-278 | 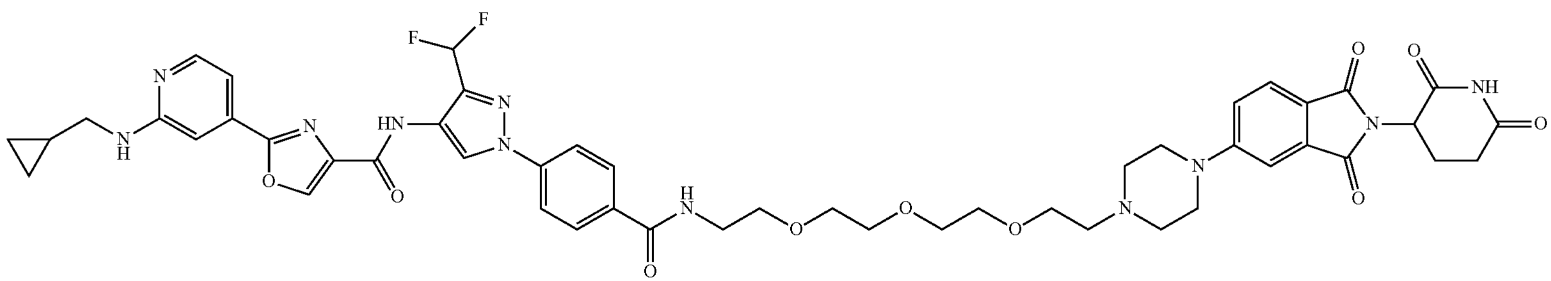 [SMILES: O=C1CCC(N2C(=O)c3ccc(N4CCN(CCOCCOCCOCCNC(=O)c5ccc(-n6cc(NC(=O)c7coc(-c8ccnc(NCC9CC9)c8)n7)c(C(F)F)n6)cc5)CC4)cc3C2=O)C(=O)N1] |

TABLE 1-continued

Exemplary Compounds

| I-# | Structure |
|---|---|
| I-279 | (structure) |
| I-280 | (structure) |
| I-281 | (structure) |

TABLE 1-continued
Exemplary Compounds
| I-# | Structure |
|---|---|
| I-282 | 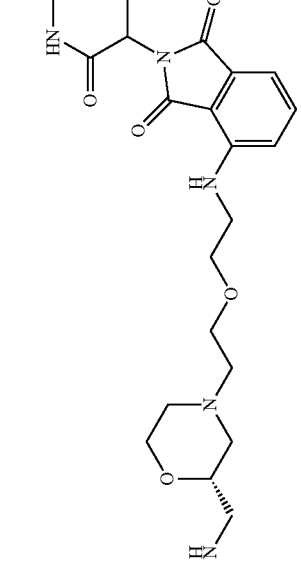 |
| I-283 | 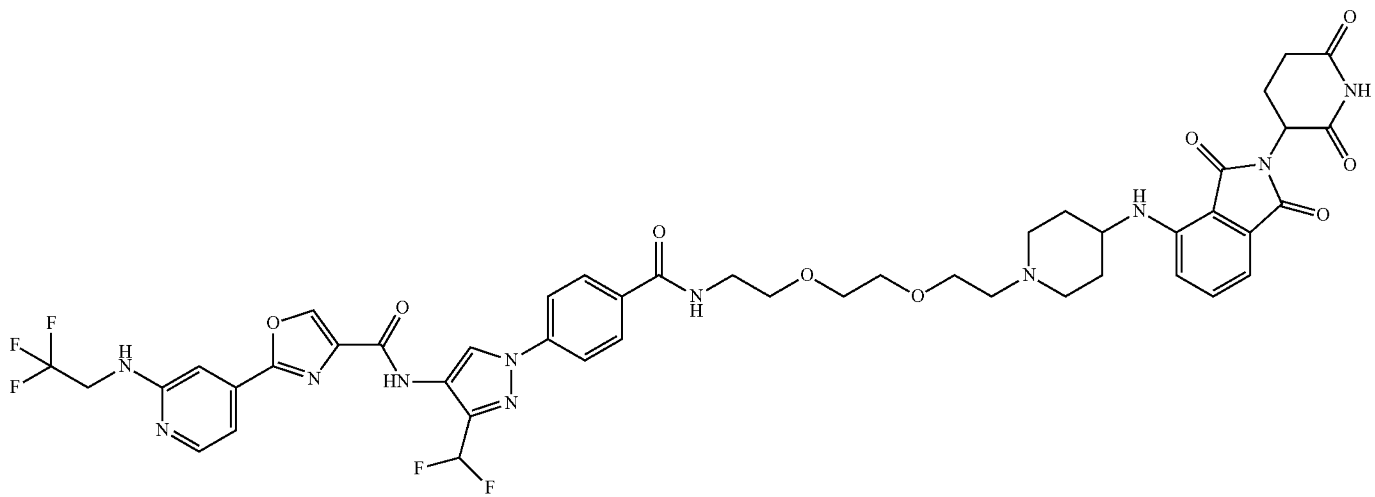 [SMILES: O=C1CCC(N2C(=O)c3cccc(NC4CCN(CCOCCOCCNC(=O)c5ccc(-n6cc(NC(=O)c7coc(-c8ccnc(NCC(F)(F)F)c8)n7)c(C(F)F)n6)cc5)CC4)c3C2=O)C(=O)N1] |

TABLE 1-continued
Exemplary Compounds
| I-# | Structure |
|---|---|
| I-284 | 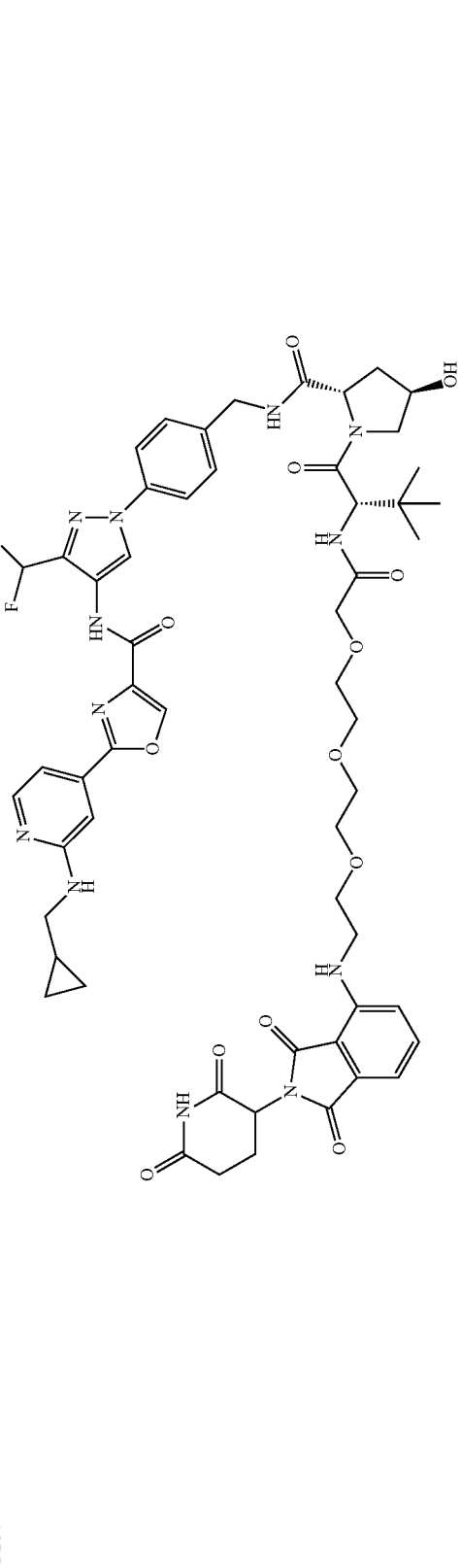 |

TABLE 1-continued
Exemplary Compounds
| I-# | Structure |
|---|---|
| I-285 | 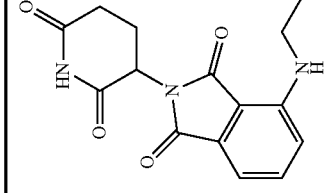 |

TABLE 1-continued

Exemplary Compounds

| I-# | Structure |
|---|---|
| I-286 | 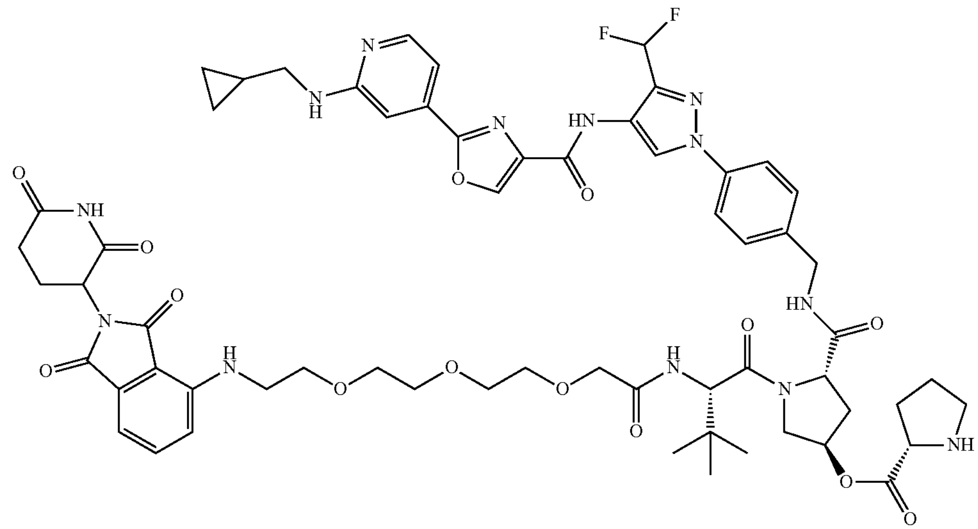 [SMILES: CC(C)(C)[C@H](NC(=O)COCCOCCOCCNc1cccc2c1C(=O)N(C1CCC(=O)NC1=O)C2=O)C(=O)N1C[C@H](OC(=O)[C@@H]2CCCN2)C[C@H]1C(=O)NCc1ccc(-n2cc(NC(=O)c3coc(-c4ccnc(NCC5CC5)c4)n3)c(C(F)F)n2)cc1] |

TABLE 1-continued
Exemplary Compounds
| I-# | Structure |
|---|---|
| I-287 | 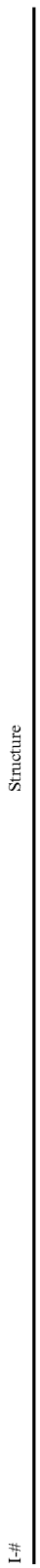 |

TABLE 1-continued
Exemplary Compounds
Structure
| I-# | |
|---|---|
| I-288 | 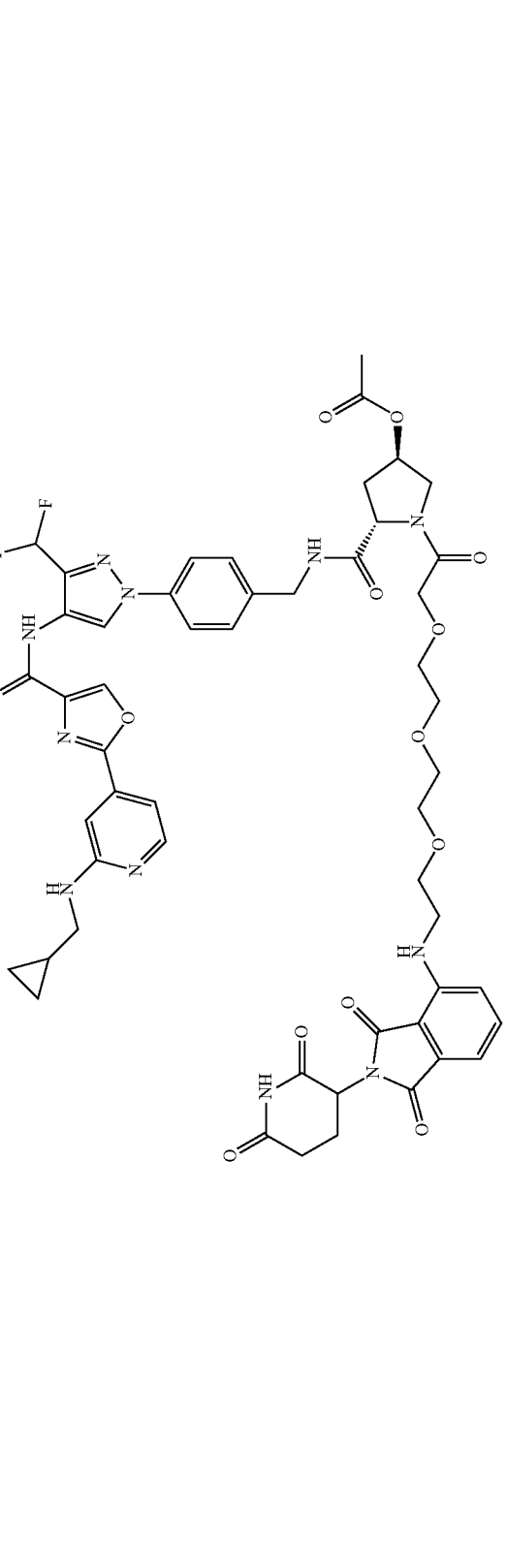 |

TABLE 1-continued
Exemplary Compounds
| I-# | Structure |
|---|---|
| I-289 | 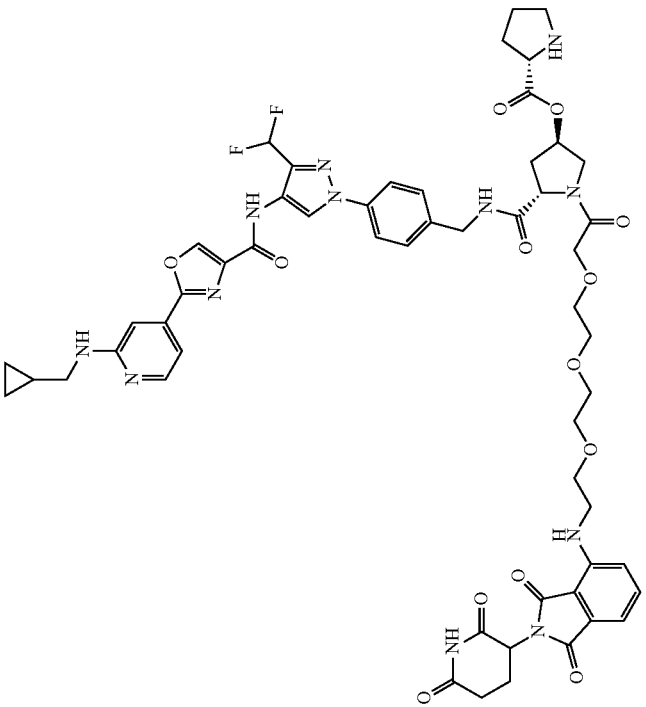 |

TABLE 1-continued
Exemplary Compounds
| I-# | Structure |
|---|---|
| I-290 | 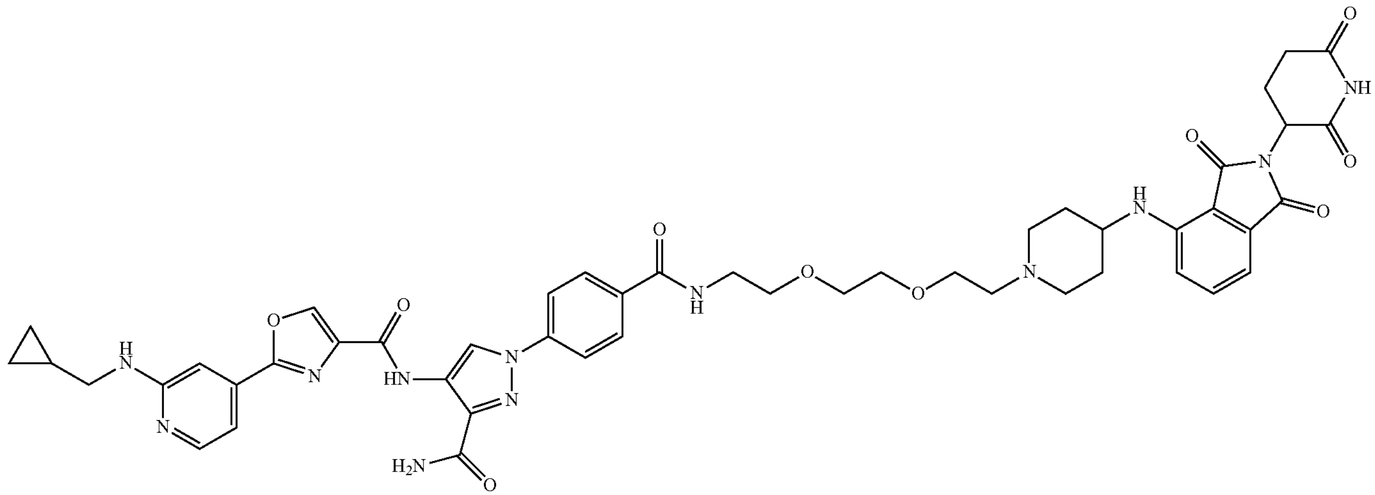 [SMILES: NC(=O)c1nn(-c2ccc(C(=O)NCCOCCOCCN3CCC(Nc4cccc5c4C(=O)N(C4CCC(=O)NC4=O)C5=O)CC3)cc2)cc1NC(=O)c1coc(-c2ccnc(NCC3CC3)c2)n1] |
| I-291 | 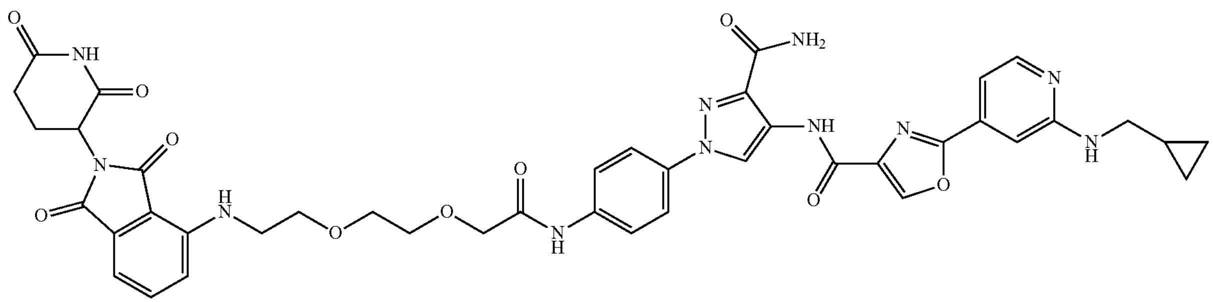 [SMILES: NC(=O)c1nn(-c2ccc(NC(=O)COCCOCCNc3cccc4c3C(=O)N(C3CCC(=O)NC3=O)C4=O)cc2)cc1NC(=O)c1coc(-c2ccnc(NCC3CC3)c2)n1] |

TABLE 1-continued

Exemplary Compounds

| I-# | Structure |
|---|---|
| I-292 | 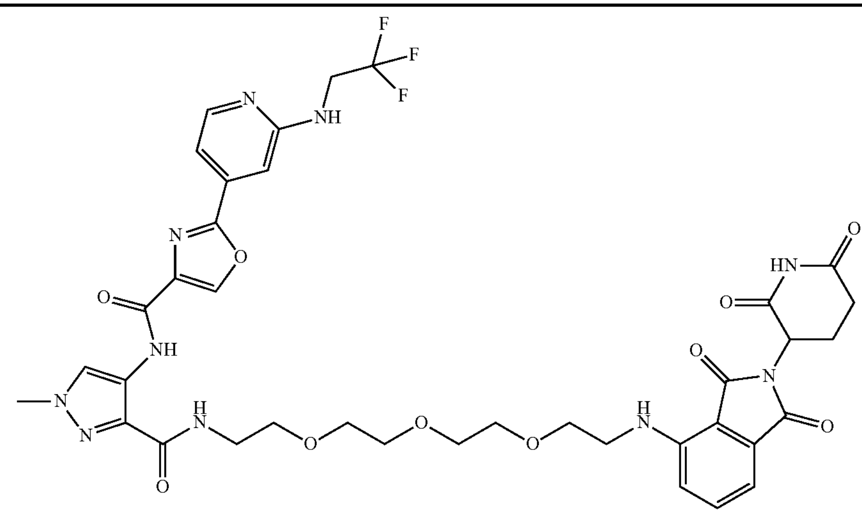 |
| I-293 | 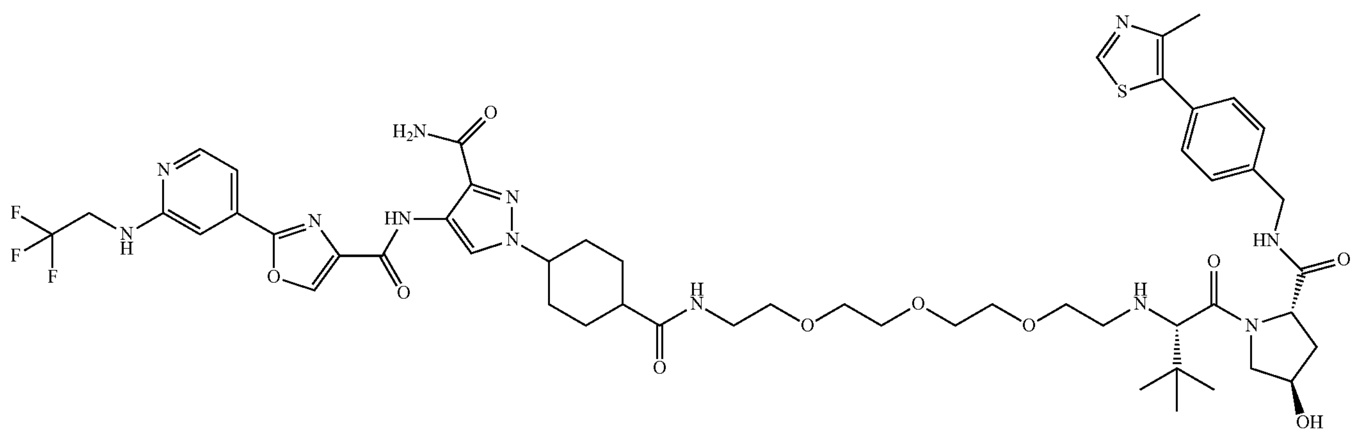 [SMILES: Cc1ncsc1-c1ccc(CNC(=O)[C@@H]2C[C@@H](O)CN2C(=O)[C@@H](NCCOCCOCCOCCNC(=O)C2CCC(n3cc(NC(=O)c4coc(-c5ccnc(NCC(F)(F)F)c5)n4)c(C(N)=O)n3)CC2)C(C)(C)C)cc1] |

TABLE 1-continued
Exemplary Compounds
| I-# | Structure |
|---|---|
| I-294 | 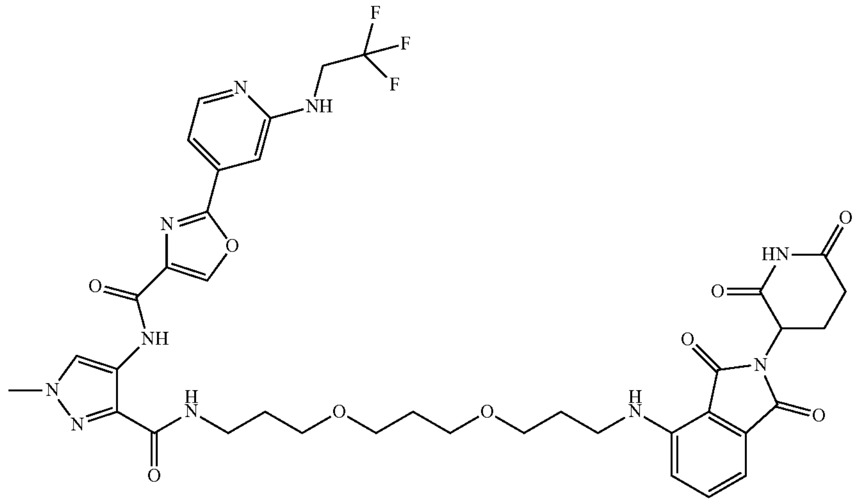 [SMILES: Cn1cc(NC(=O)c2coc(-c3ccnc(NCC(F)(F)F)c3)n2)c(C(=O)NCCCOCCCOCCCNc2cccc3c2C(=O)N(C2CCC(=O)NC2=O)C3=O)n1] |
| I-295 | 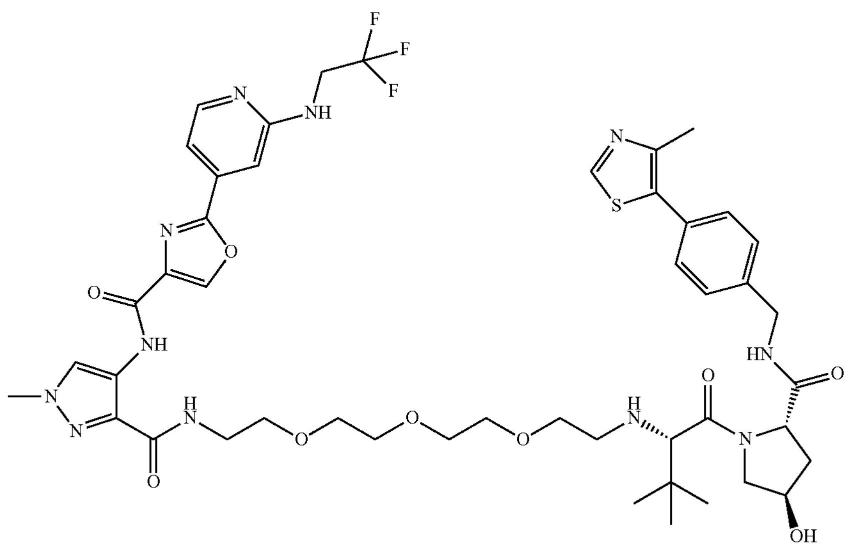 [SMILES: Cc1ncsc1-c1ccc(CNC(=O)[C@@H]2C[C@@H](O)CN2C(=O)[C@@H](NCCOCCOCCOCCNC(=O)c2nn(C)cc2NC(=O)c2coc(-c3ccnc(NCC(F)(F)F)c3)n2)C(C)(C)C)cc1] |

TABLE 1-continued
Exemplary Compounds
| I-# | Structure |
|---|---|
| I-296 | 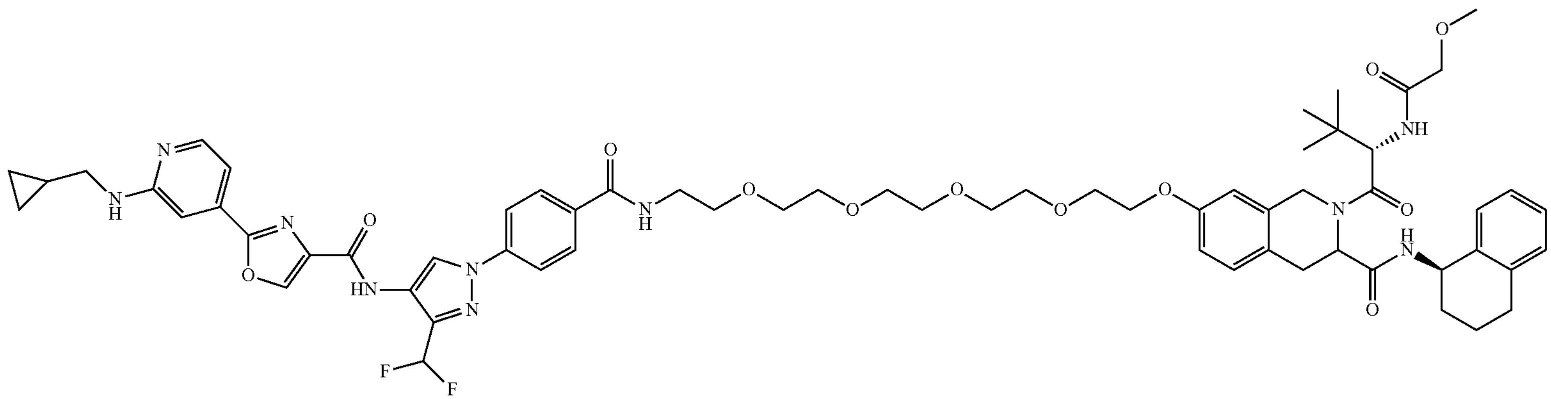 [SMILES: COCC(=O)N[C@H](C(=O)N1Cc2cc(OCCOCCOCCOCCOCCNC(=O)c3ccc(-n4cc(NC(=O)c5coc(-c6ccnc(NCC7CC7)c6)n5)c(C(F)F)n4)cc3)ccc2CC1C(=O)N[C@@H]1CCCc2ccccc21)C(C)(C)C] |
| I-297 | 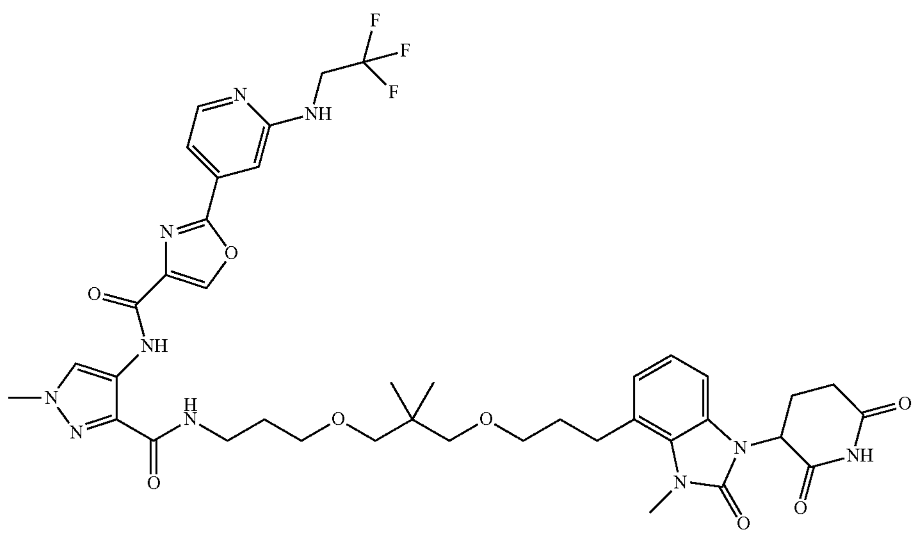 [SMILES: Cn1cc(NC(=O)c2coc(-c3ccnc(NCC(F)(F)F)c3)n2)c(C(=O)NCCCOCC(C)(C)COCCCc2cccc3c2n(C)c(=O)n3C2CCC(=O)NC2=O)n1] |

TABLE 1-continued
Exemplary Compounds
| I-# | Structure |
|---|---|
| I-298 | 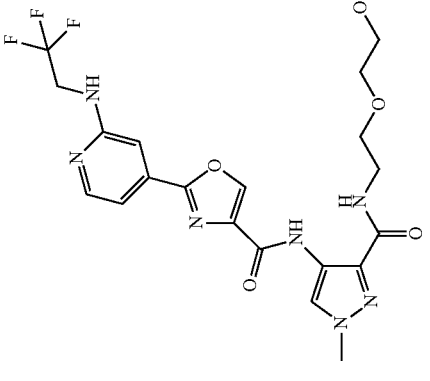 |

TABLE 1-continued
Exemplary Compounds
| I-# | Structure |
|---|---|
| I-299 | 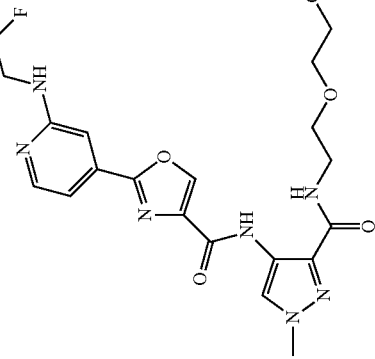 |
| I-300 | 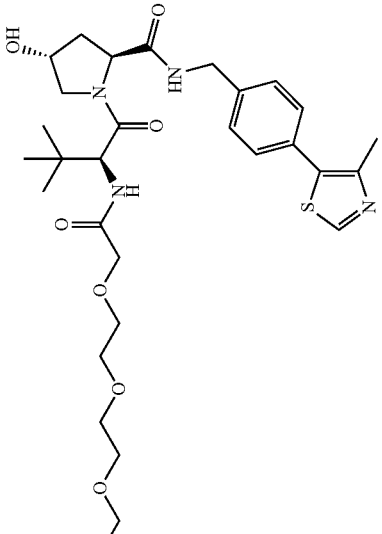 |

TABLE 1-continued
Exemplary Compounds
| I-# | Structure |
|---|---|
| I-301 | 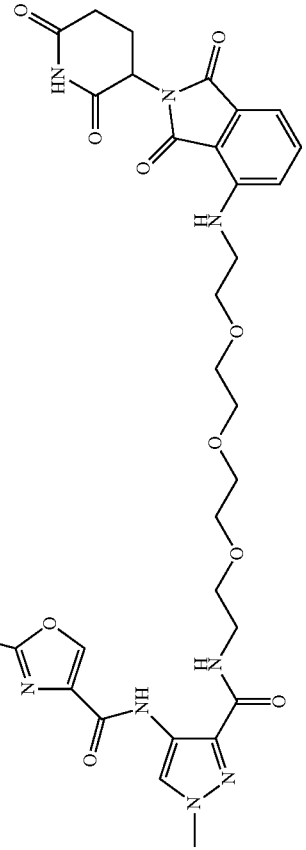 |
| I-302 | 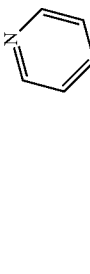 |

TABLE 1-continued
Exemplary Compounds
| I-# | Structure |
|---|---|
| I-303 | 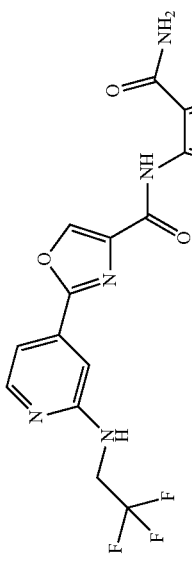 |

TABLE 1-continued
Exemplary Compounds
| I-# | Structure |
|---|---|
| I-304 | 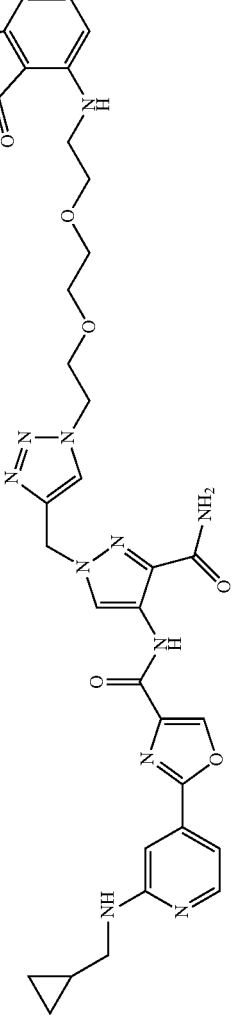 |
| I-305 | 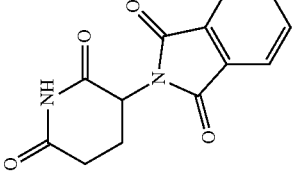 |

TABLE 1-continued

Exemplary Compounds

| I-# | Structure |
|---|---|
| I-306 | 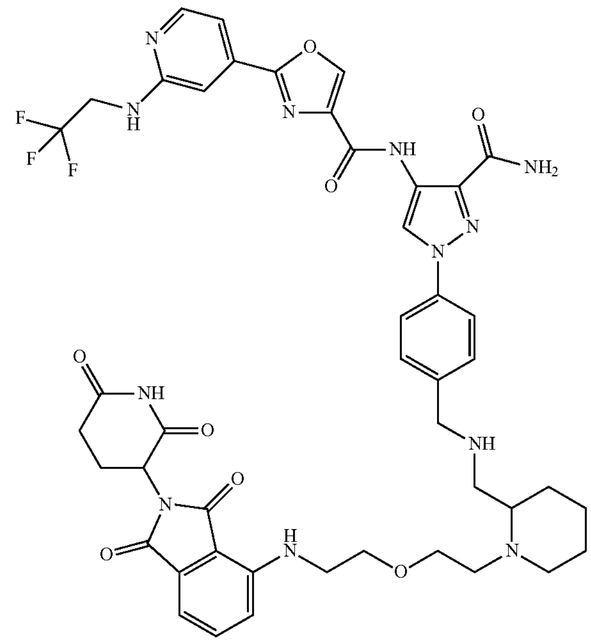 [SMILES: NC(=O)c1nn(-c2ccc(CNCC3CCCCN3CCOCCNc3cccc4c3C(=O)N(C3CCC(=O)NC3=O)C4=O)cc2)cc1NC(=O)c1coc(-c2ccnc(NCC(F)(F)F)c2)n1] |
| I-307 | 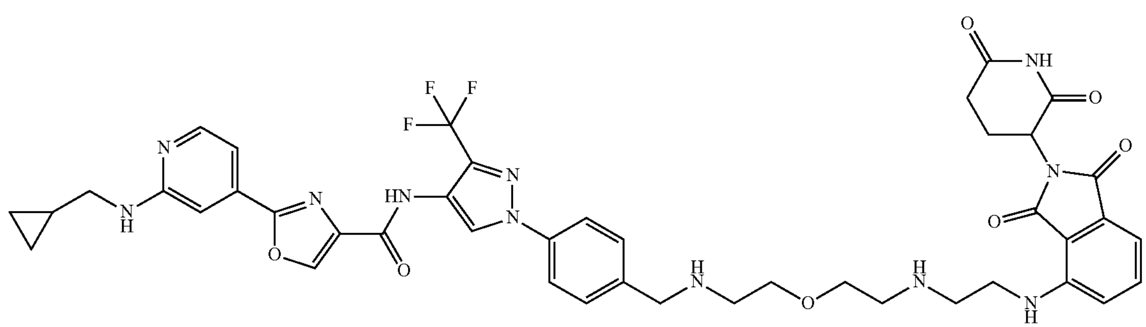 [SMILES: O=C1CCC(N2C(=O)c3cccc(NCCNCCOCCNCc4ccc(-n5cc(NC(=O)c6coc(-c7ccnc(NCC8CC8)c7)n6)c(C(F)(F)F)n5)cc4)c3C2=O)C(=O)N1] |

TABLE 1-continued
Exemplary Compounds
| I-# | Structure |
|---|---|
| I-308 | 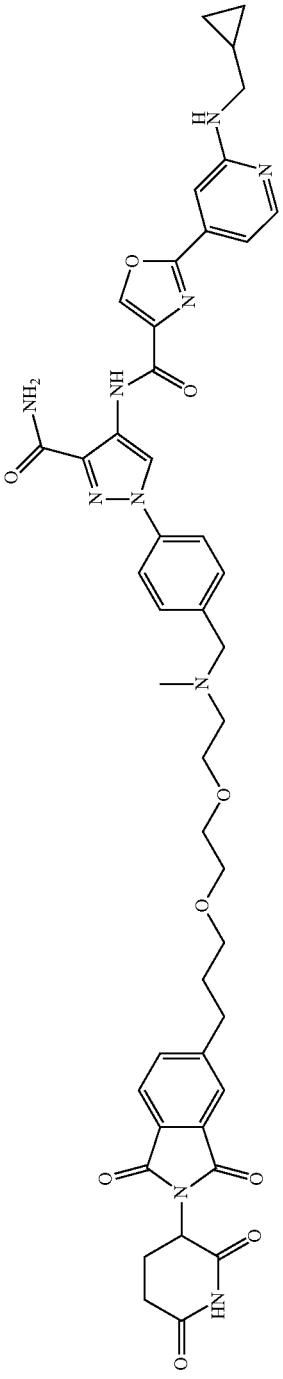 |
| I-309 | 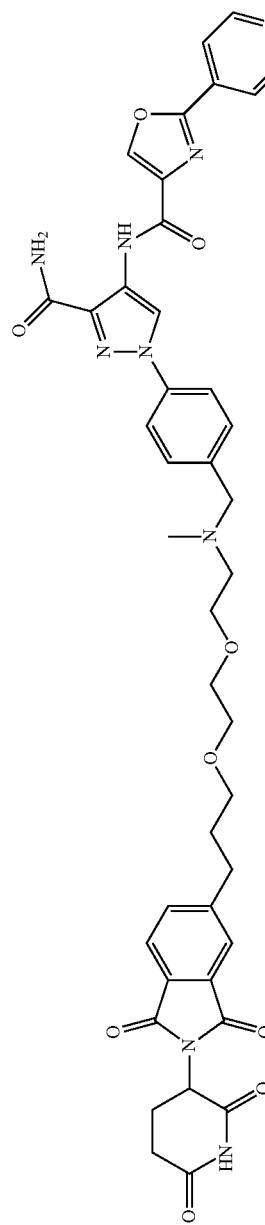 |
| I-310 | 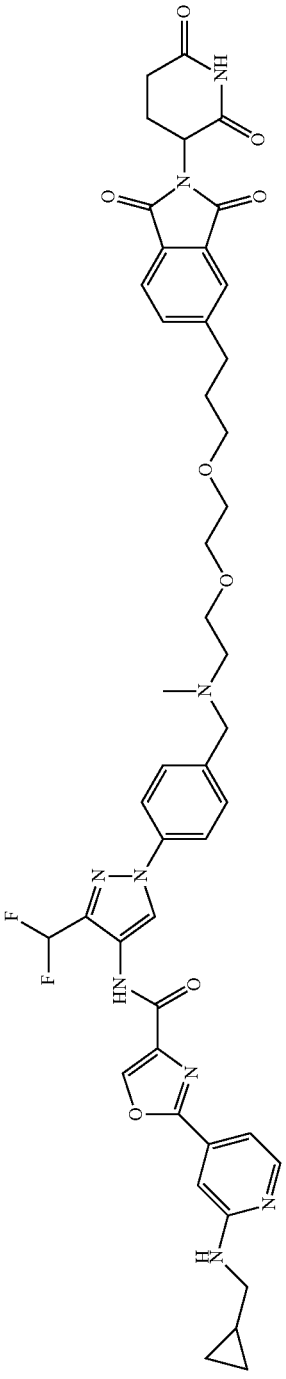 |

TABLE 1-continued

Exemplary Compounds

| I-# | Structure |
|---|---|
| I-311 | 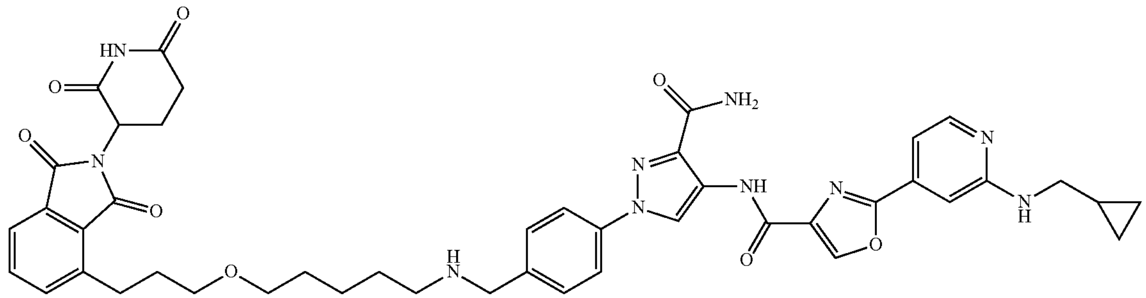 [SMILES: NC(=O)c1nn(-c2ccc(CNCCCCCOCCCc3cccc4c3C(=O)N(C3CCC(=O)NC3=O)C4=O)cc2)cc1NC(=O)c1coc(-c2ccnc(NCC3CC3)c2)n1] |
| I-312 | 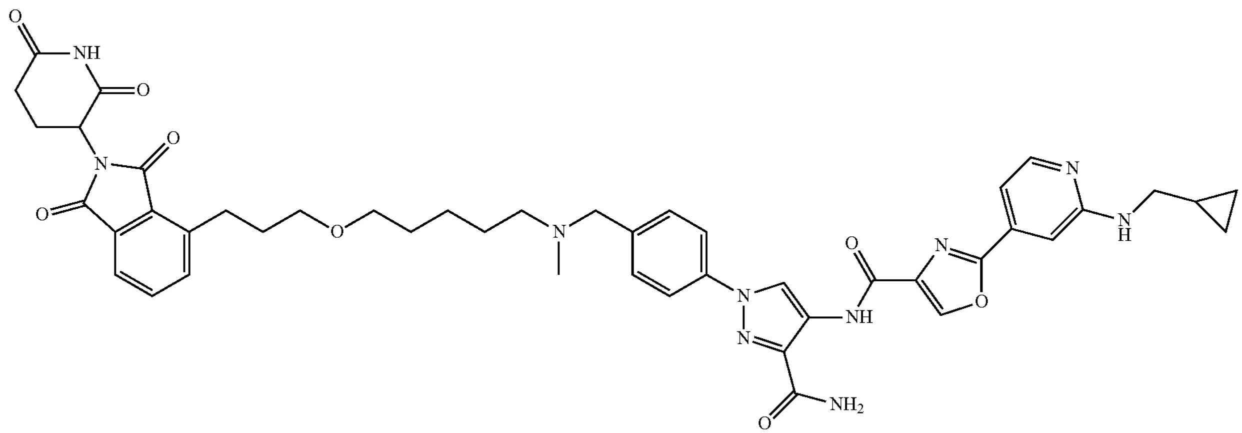 [SMILES: CN(CCCCCOCCCc1cccc2c1C(=O)N(C1CCC(=O)NC1=O)C2=O)Cc1ccc(-n2cc(NC(=O)c3coc(-c4ccnc(NCC5CC5)c4)n3)c(C(N)=O)n2)cc1] |
| I-313 | 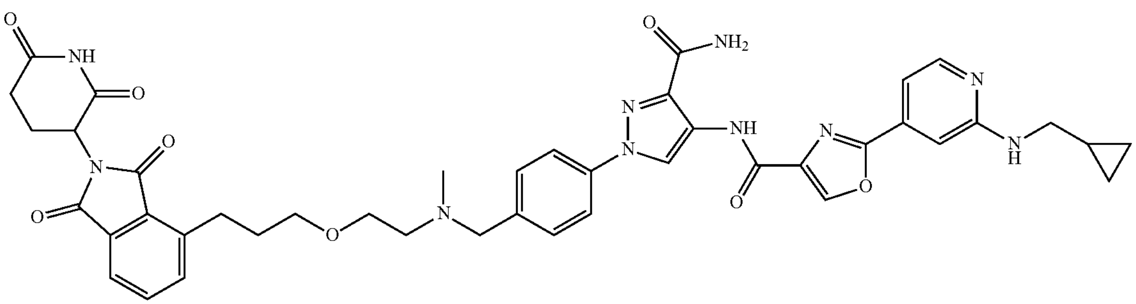 [SMILES: CN(CCOCCCc1cccc2c1C(=O)N(C1CCC(=O)NC1=O)C2=O)Cc1ccc(-n2cc(NC(=O)c3coc(-c4ccnc(NCC5CC5)c4)n3)c(C(N)=O)n2)cc1] |

TABLE 1-continued
Exemplary Compounds
| I-# | Structure |
|---|---|
| I-314 | 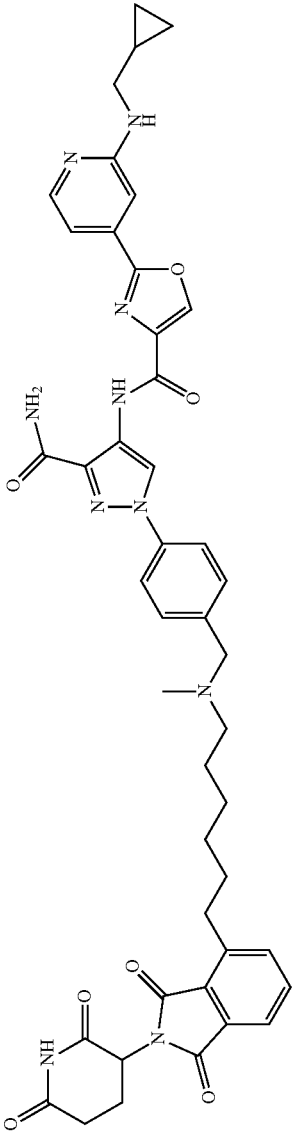 |
| I-315 | 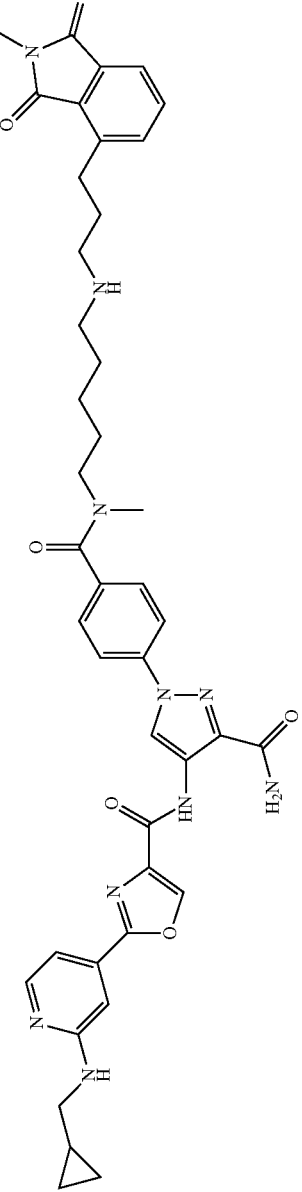 |

TABLE 1-continued
Exemplary Compounds
| I-# | Structure |
|---|---|
| I-316 | 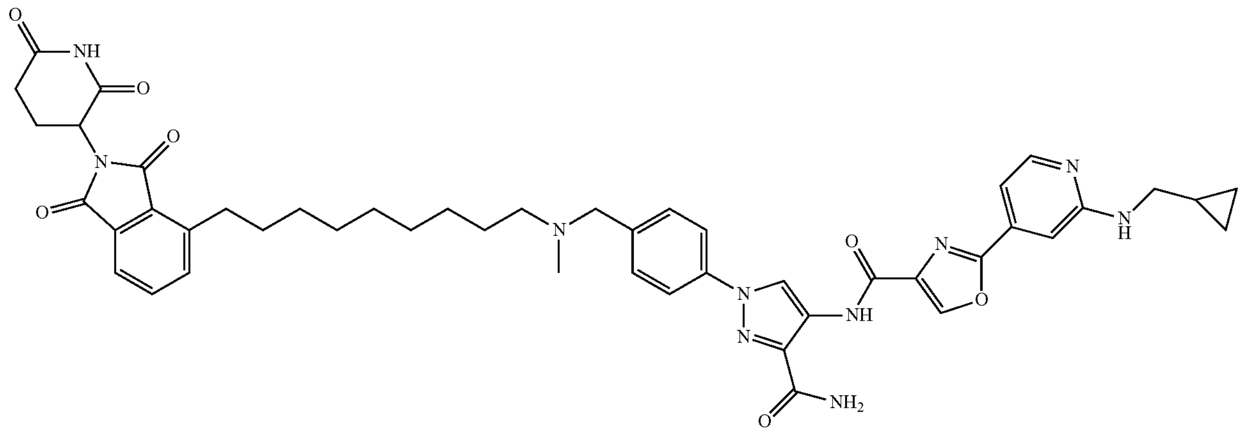 [SMILES: CN(CCCCCCCCCc1cccc2c1C(=O)N(C1CCC(=O)NC1=O)C2=O)Cc1ccc(-n2cc(NC(=O)c3coc(-c4ccnc(NCC5CC5)c4)n3)c(C(N)=O)n2)cc1] |
| I-317 | 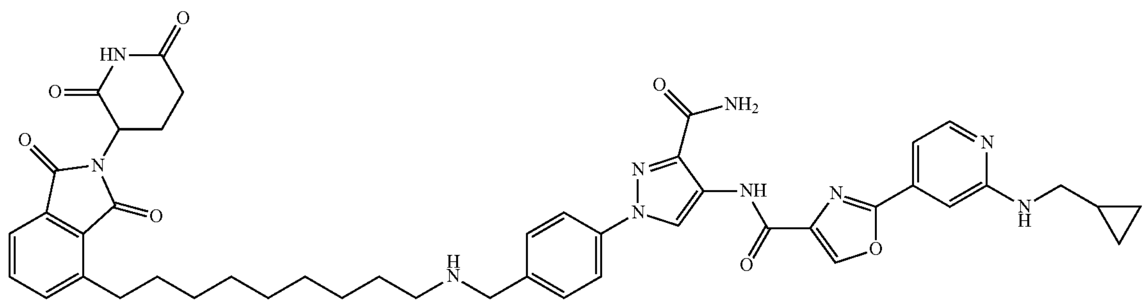 [SMILES: NC(=O)c1nn(-c2ccc(CNCCCCCCCCCc3cccc4c3C(=O)N(C3CCC(=O)NC3=O)C4=O)cc2)cc1NC(=O)c1coc(-c2ccnc(NCC3CC3)c2)n1] |
| I-318 | 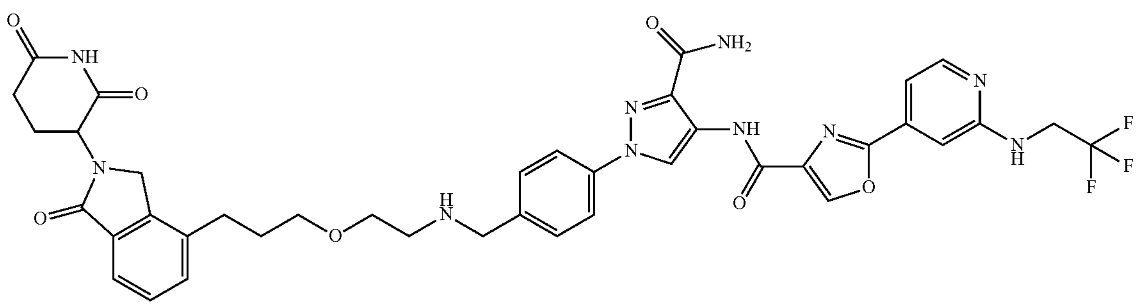 [SMILES: NC(=O)c1nn(-c2ccc(CNCCOCCCc3cccc4c3CN(C3CCC(=O)NC3=O)C4=O)cc2)cc1NC(=O)c1coc(-c2ccnc(NCC(F)(F)F)c2)n1] |

TABLE 1-continued
Exemplary Compounds
| I-# | Structure |
|---|---|
| I-319 | 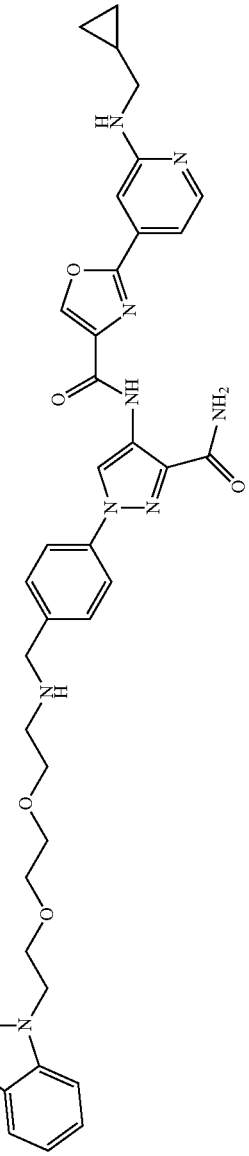 |
| I-320 | 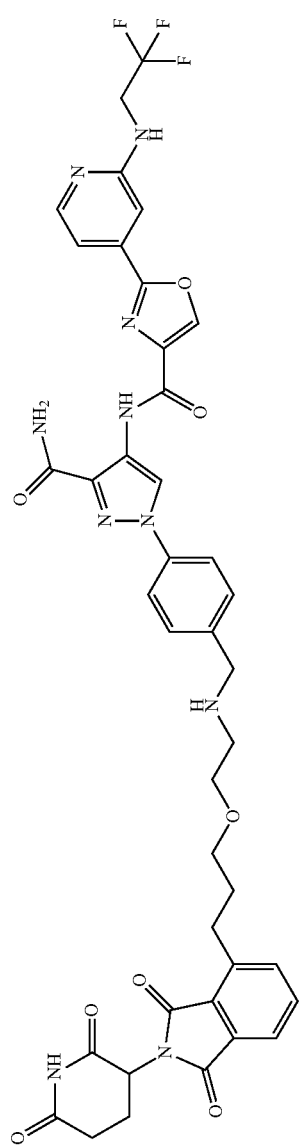 |

TABLE 1-continued

Exemplary Compounds

| I-# | Structure |
|---|---|
| I-321 | 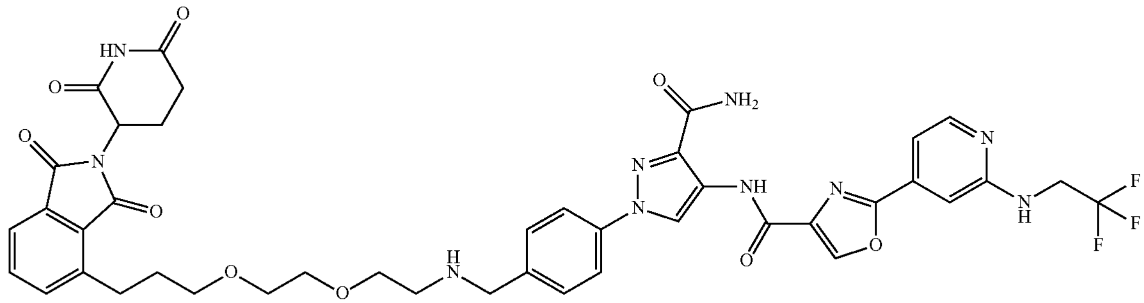 [SMILES: NC(=O)c1nn(-c2ccc(CNCCOCCOCCCc3cccc4c3C(=O)N(C3CCC(=O)NC3=O)C4=O)cc2)cc1NC(=O)c1coc(-c2ccnc(NCC(F)(F)F)c2)n1] |
| I-322 | 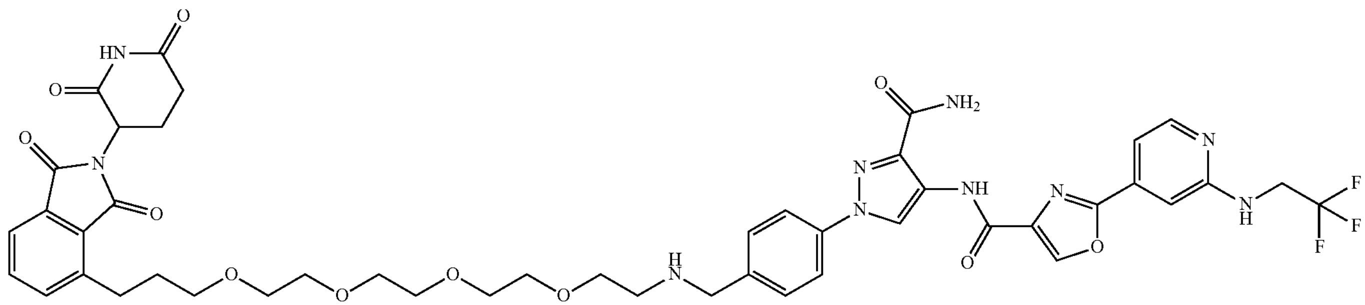 [SMILES: NC(=O)c1nn(-c2ccc(CNCCOCCOCCOCCOCCCc3cccc4c3C(=O)N(C3CCC(=O)NC3=O)C4=O)cc2)cc1NC(=O)c1coc(-c2ccnc(NCC(F)(F)F)c2)n1] |
| I-323 | 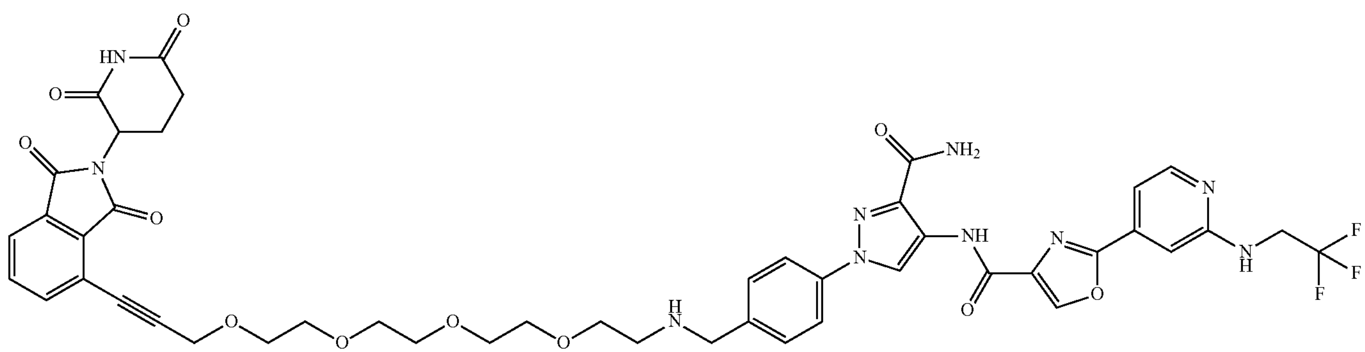 [SMILES: NC(=O)c1nn(-c2ccc(CNCCOCCOCCOCCOCC#Cc3cccc4c3C(=O)N(C3CCC(=O)NC3=O)C4=O)cc2)cc1NC(=O)c1coc(-c2ccnc(NCC(F)(F)F)c2)n1] |

TABLE 1-continued

Exemplary Compounds

| I-# | Structure |
|---|---|
| I-324 | 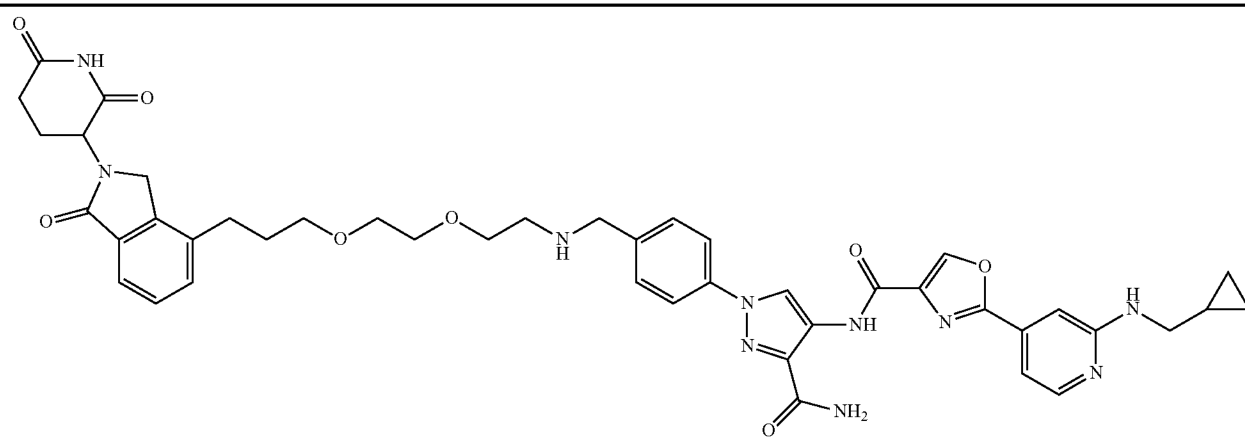 |
| I-325 | 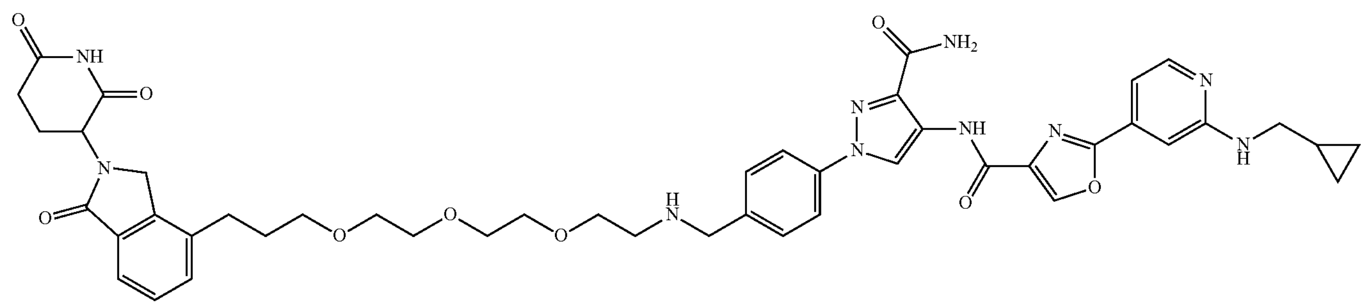 [SMILES: NC(=O)c1nn(-c2ccc(CNCCOCCOCCOCCCc3cccc4c3CN(C3CCC(=O)NC3=O)C4=O)cc2)cc1NC(=O)c1coc(-c2ccnc(NCC3CC3)c2)n1] |
| I-326 | 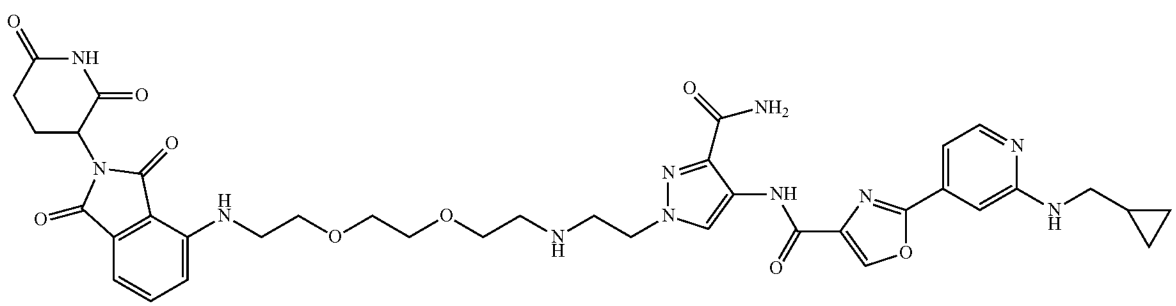 |

TABLE 1-continued

Exemplary Compounds

| I-# | Structure |
|---|---|
| I-327 | 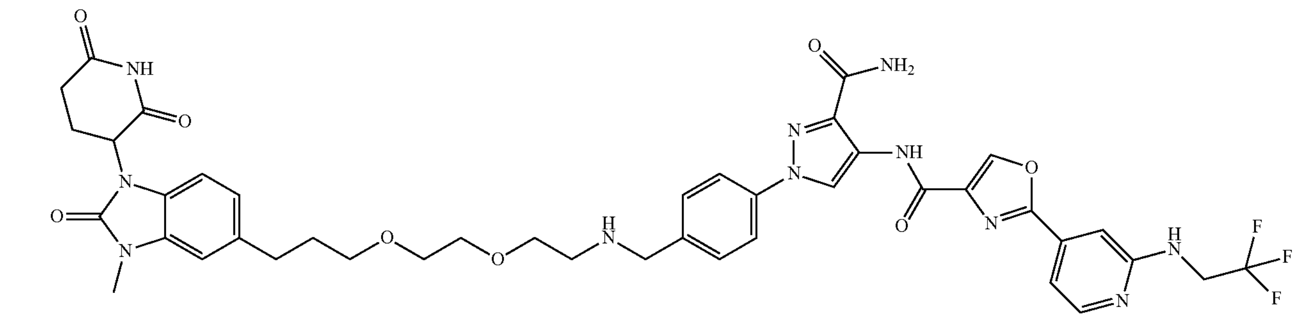 [SMILES: Cn1c(=O)n(C2CCC(=O)NC2=O)c2ccc(CCCOCCOCCNCc3ccc(-n4cc(NC(=O)c5coc(-c6ccnc(NCC(F)(F)F)c6)n5)c(C(N)=O)n4)cc3)cc21] |
| I-328 | 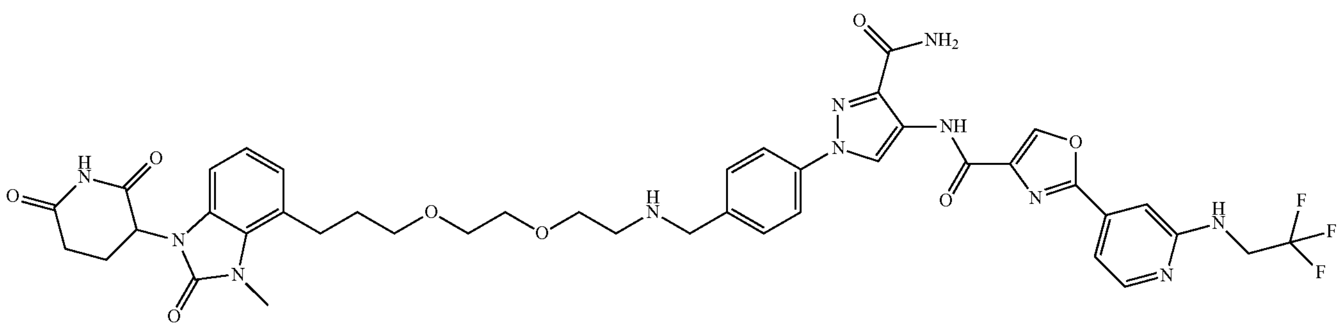 |
| I-329 | 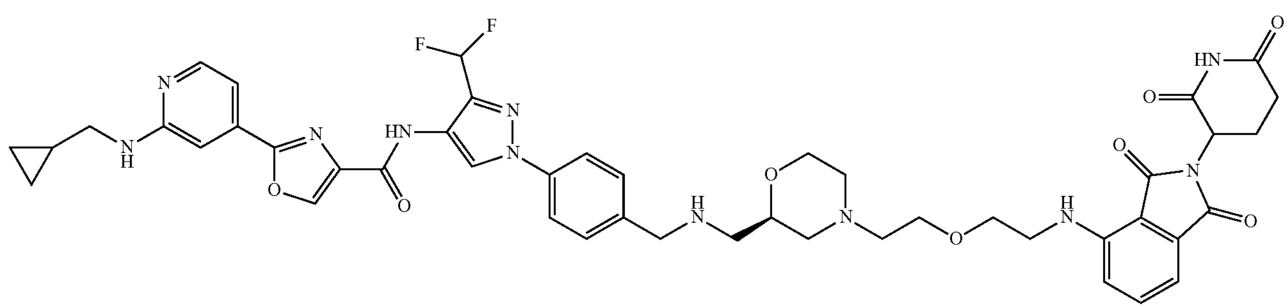 [SMILES: O=C1CCC(N2C(=O)c3cccc(NCCOCCN4CCO[C@H](CNCc5ccc(-n6cc(NC(=O)c7coc(-c8ccnc(NCC9CC9)c8)n7)c(C(F)F)n6)cc5)C4)c3C2=O)C(=O)N1] |

TABLE 1-continued

Exemplary Compounds

| I-# | Structure |
|---|---|
| I-330 | (structure) |
| I-331 | (structure) |
| I-332 | (structure) |

TABLE 1-continued
Exemplary Compounds
| I-# | Structure |
|---|---|
| I-333 | 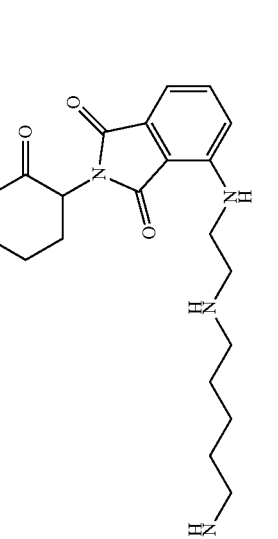 |
| I-334 | 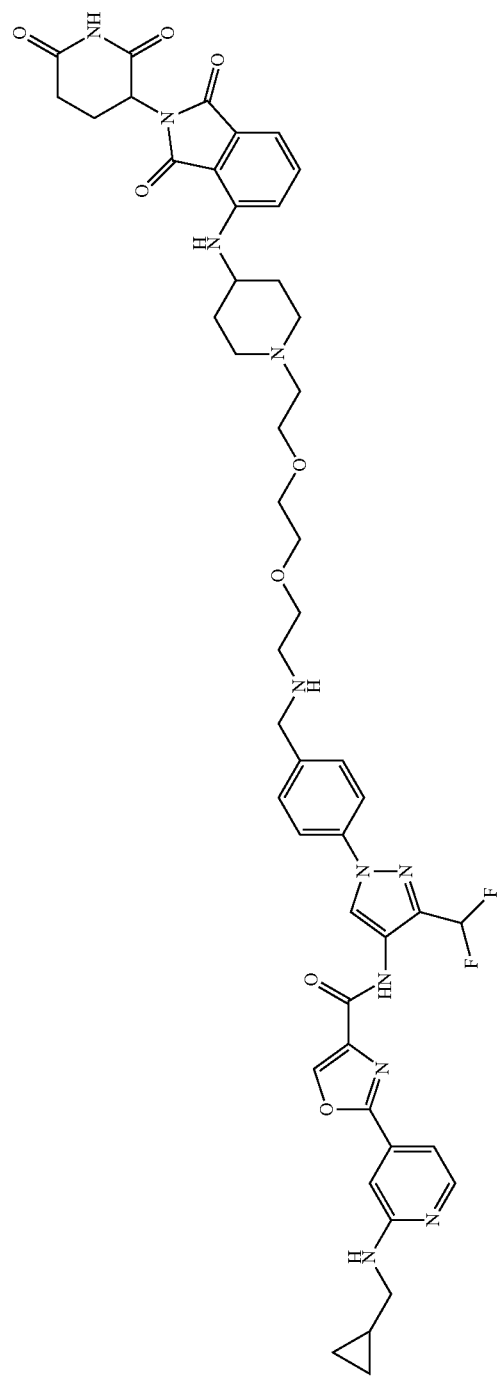 |

TABLE 1-continued

Exemplary Compounds

| I-# | Structure |
|---|---|
| I-335 | 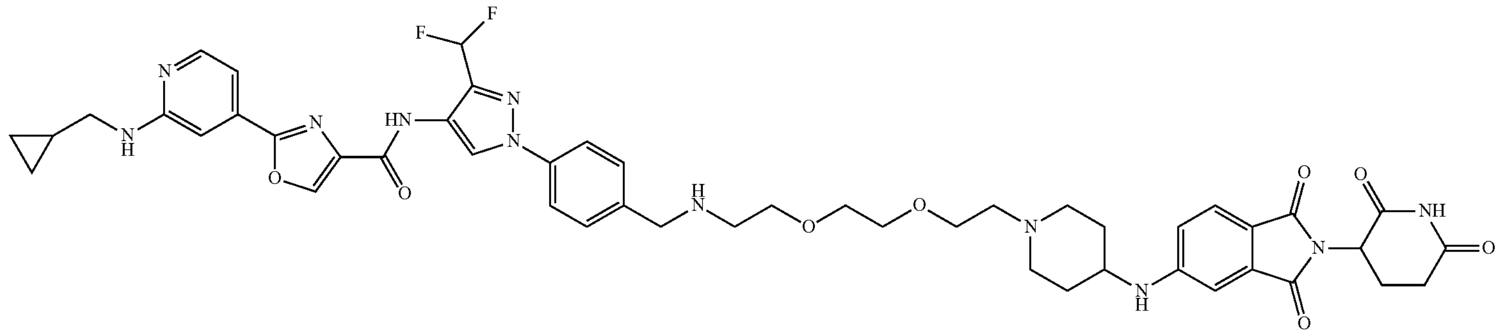 [SMILES: O=C1CCC(N2C(=O)c3ccc(NC4CCN(CCOCCOCCNCc5ccc(-n6cc(NC(=O)c7coc(-c8ccnc(NCC9CC9)c8)n7)c(C(F)F)n6)cc5)CC4)cc3C2=O)C(=O)N1] |
| I-336 | 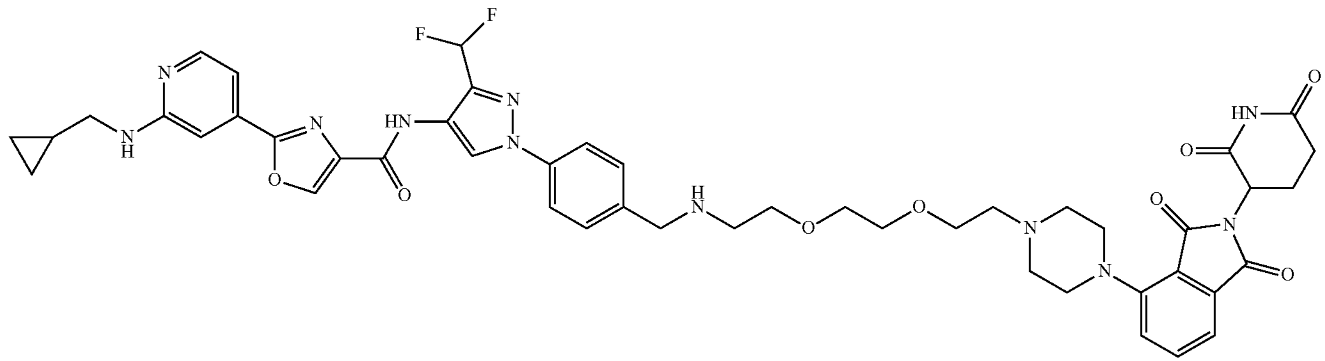 [SMILES: O=C1CCC(N2C(=O)c3cccc(N4CCN(CCOCCOCCNCc5ccc(-n6cc(NC(=O)c7coc(-c8ccnc(NCC9CC9)c8)n7)c(C(F)F)n6)cc5)CC4)c3C2=O)C(=O)N1] |

TABLE 1-continued
Exemplary Compounds
| I-# | Structure |
|---|---|
| I-337 | 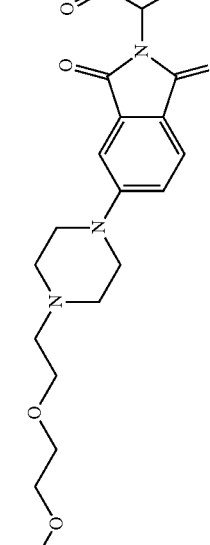 |
| I-338 | 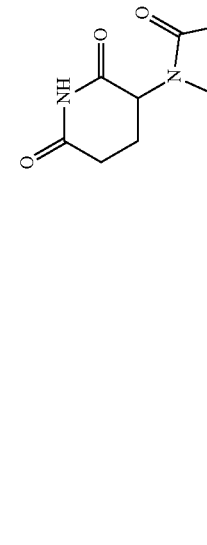 |

TABLE 1-continued

Exemplary Compounds

| I-# | Structure |
|---|---|
| I-339 | (structure) |
| I-340 | (structure) |

TABLE 1-continued
Exemplary Compounds
| I-# | Structure |
|---|---|
| I-341 | 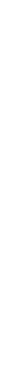 |
| I-342 | 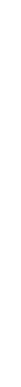 |

TABLE 1-continued
Exemplary Compounds
| I-# | Structure |
|---|---|
| I-343 | 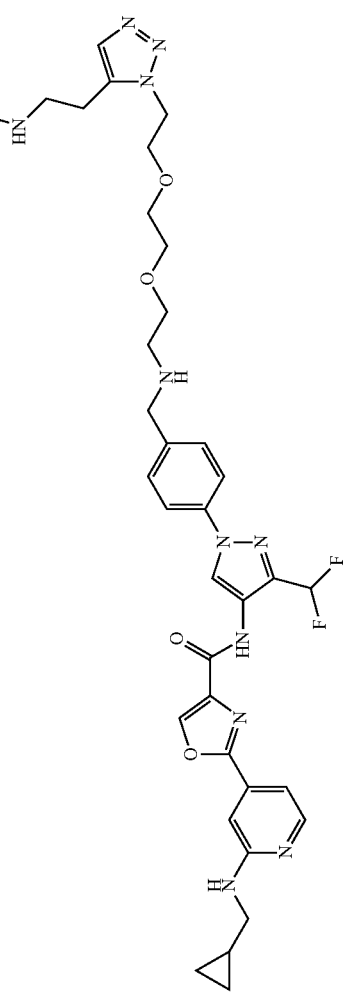 |
| I-344 | 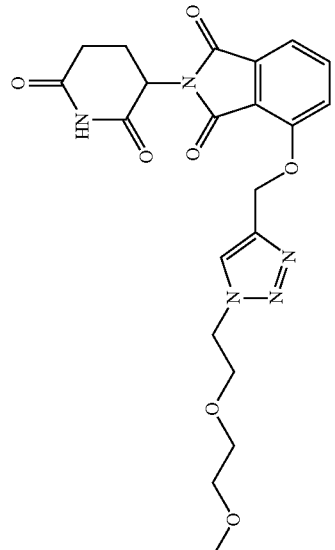 |

TABLE 1-continued

Exemplary Compounds

| I-# | Structure |
|---|---|
| I-345 | 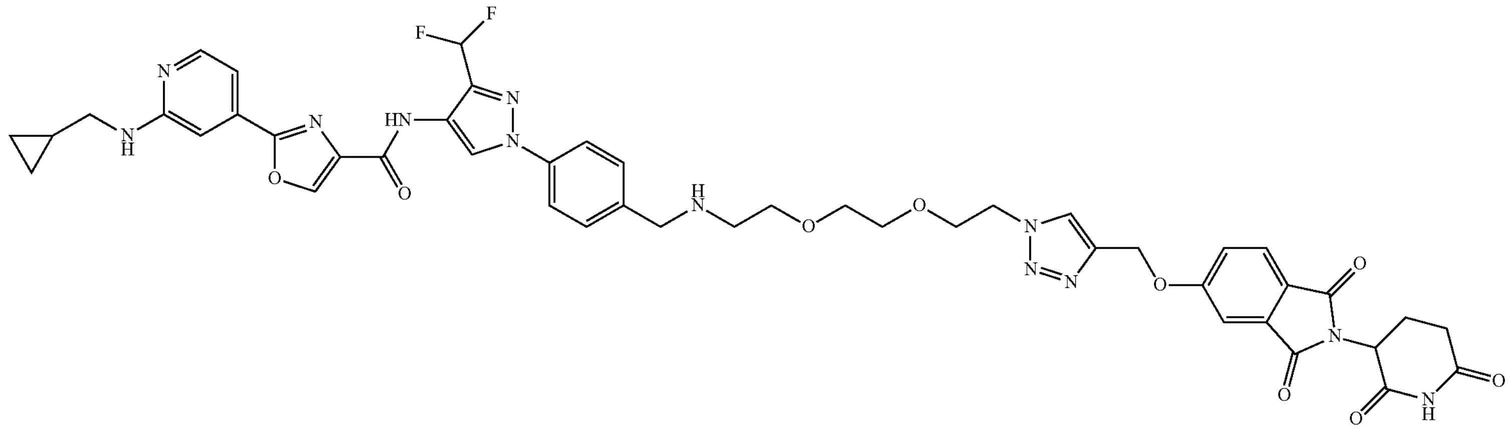 [SMILES: O=C1CCC(N2C(=O)c3ccc(OCc4cn(CCOCCOCCNCc5ccc(-n6cc(NC(=O)c7coc(-c8ccnc(NCC9CC9)c8)n7)c(C(F)F)n6)cc5)nn4)cc3C2=O)C(=O)N1] |
| I-346 | 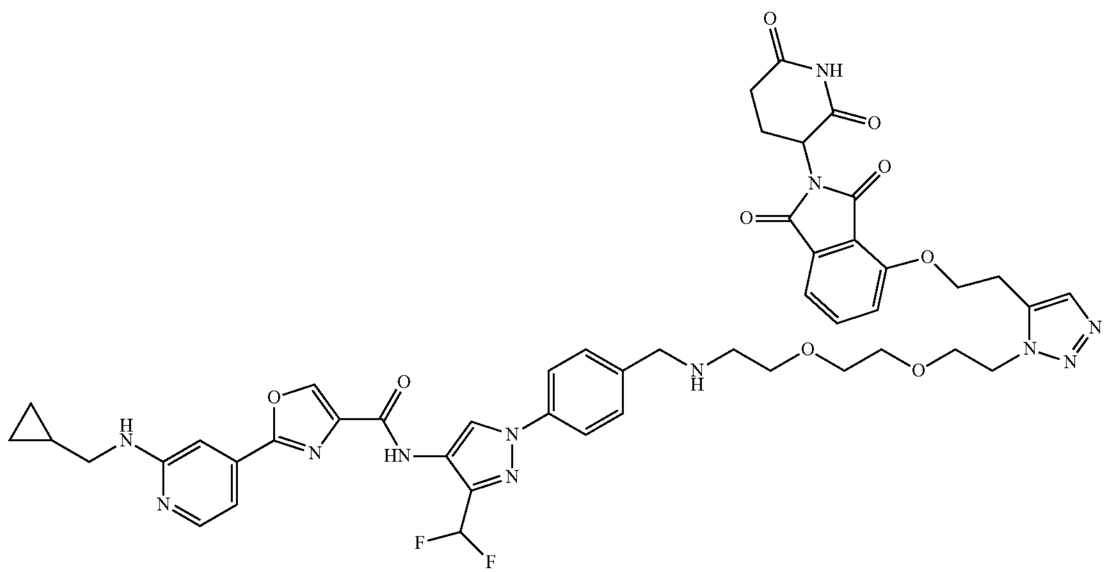 [SMILES: O=C1CCC(N2C(=O)c3cccc(OCCc4cnnn4CCOCCOCCNCc4ccc(-n5cc(NC(=O)c6coc(-c7ccnc(NCC8CC8)c7)n6)c(C(F)F)n5)cc4)c3C2=O)C(=O)N1] |

TABLE 1-continued

Exemplary Compounds

| I-# | Structure |
|---|---|
| I-347 | 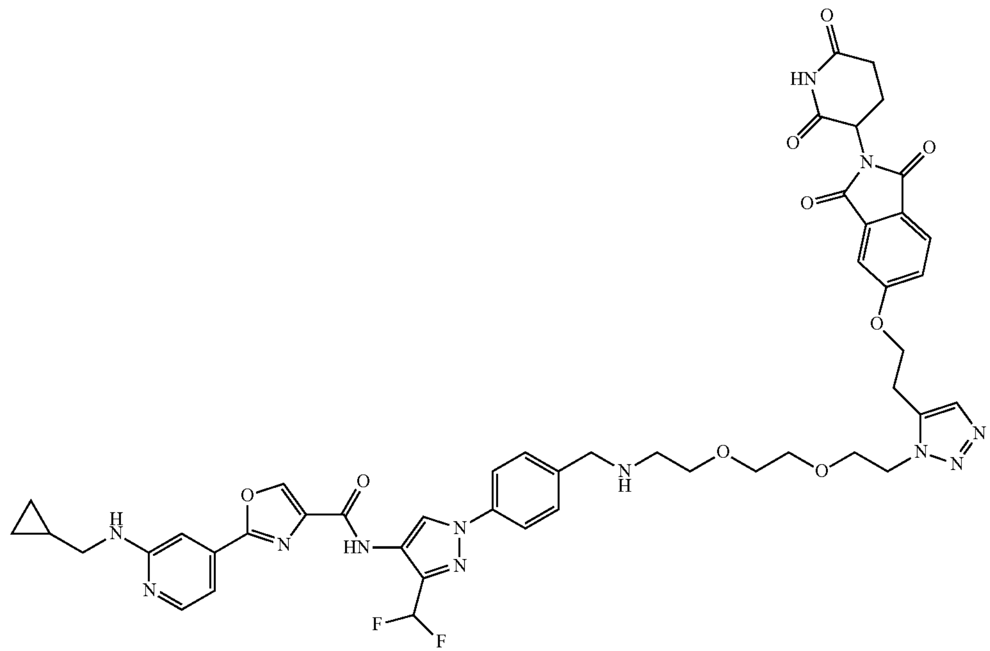 [SMILES: O=C1CCC(N2C(=O)c3ccc(OCCc4cnnn4CCOCCOCCNCc4ccc(-n5cc(NC(=O)c6coc(-c7ccnc(NCC8CC8)c7)n6)c(C(F)F)n5)cc4)cc3C2=O)C(=O)N1] |
| I-348 | 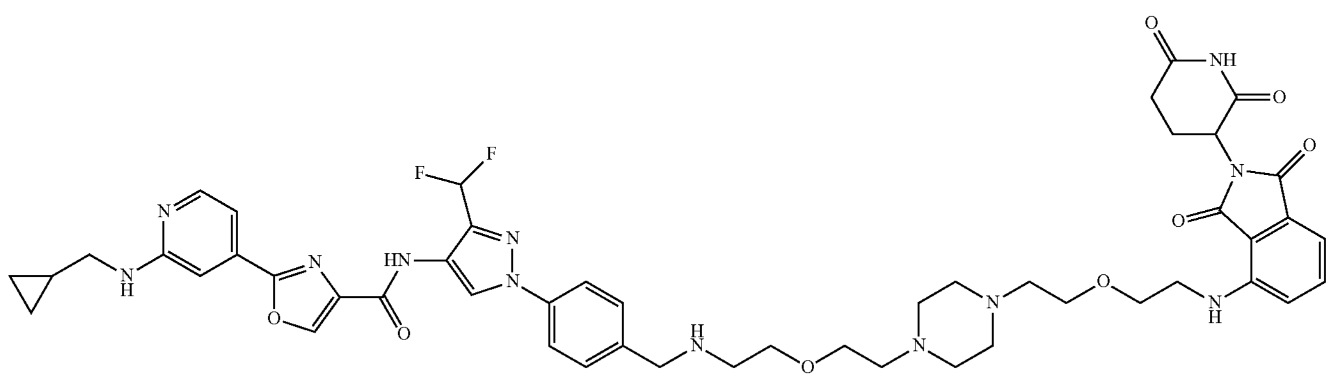 [SMILES: O=C1CCC(N2C(=O)c3cccc(NCCOCCN4CCN(CCOCCNCc5ccc(-n6cc(NC(=O)c7coc(-c8ccnc(NCC9CC9)c8)n7)c(C(F)F)n6)cc5)CC4)c3C2=O)C(=O)N1] |

TABLE 1-continued

Exemplary Compounds

| I-# | Structure |
|---|---|
| I-349 | 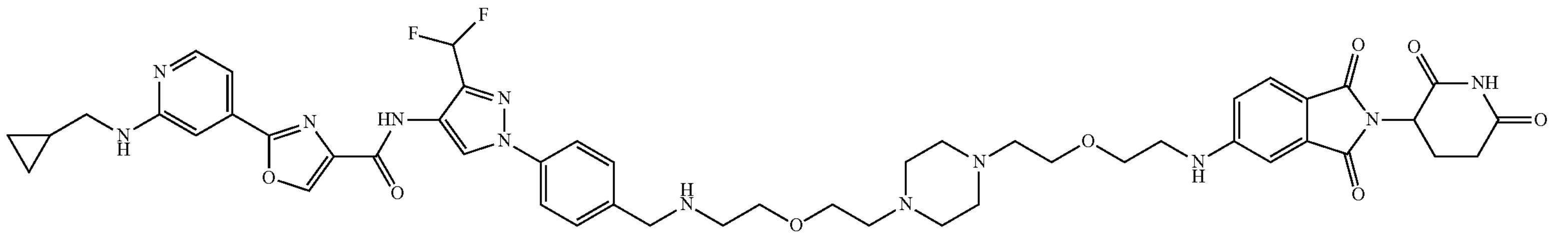 [SMILES: O=C1CCC(N2C(=O)c3ccc(NCCOCCN4CCN(CCOCCNCc5ccc(-n6cc(NC(=O)c7coc(-c8ccnc(NCC9CC9)c8)n7)c(C(F)F)n6)cc5)CC4)cc3C2=O)C(=O)N1] |
| I-350 | 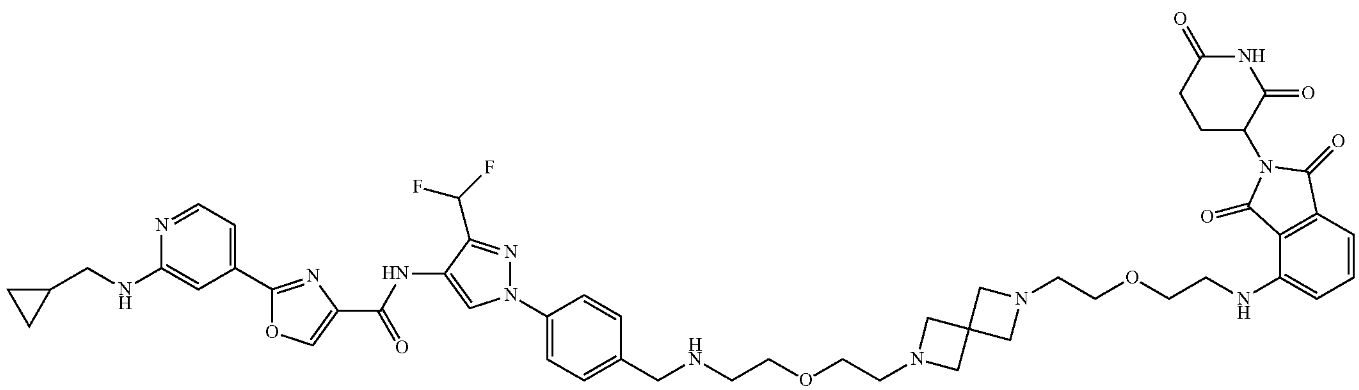 [SMILES: O=C1CCC(N2C(=O)c3cccc(NCCOCCN4CC5(CN(CCOCCNCc6ccc(-n7cc(NC(=O)c8coc(-c9ccnc(NCC%10CC%10)c9)n8)c(C(F)F)n7)cc6)C5)C4)c3C2=O)C(=O)N1] |
| I-351 | 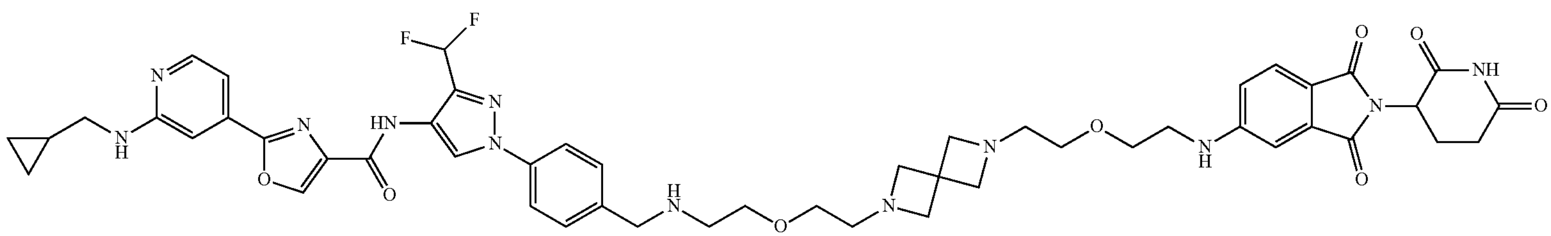 [SMILES: O=C1CCC(N2C(=O)c3ccc(NCCOCCN4CC5(CN(CCOCCNCc6ccc(-n7cc(NC(=O)c8coc(-c9ccnc(NCC%10CC%10)c9)n8)c(C(F)F)n7)cc6)C5)C4)cc3C2=O)C(=O)N1] |

TABLE 1-continued

Exemplary Compounds

| I-# | Structure |
|---|---|
| I-352 | 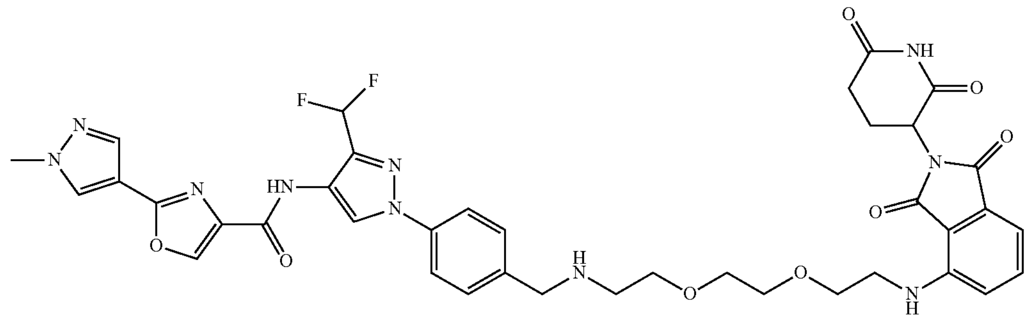 [SMILES: Cn1cc(-c2nc(C(=O)Nc3cn(-c4ccc(CNCCOCCOCCNc5cccc6c5C(=O)N(C5CCC(=O)NC5=O)C6=O)cc4)nc3C(F)F)co2)cn1] |
| I-353 | 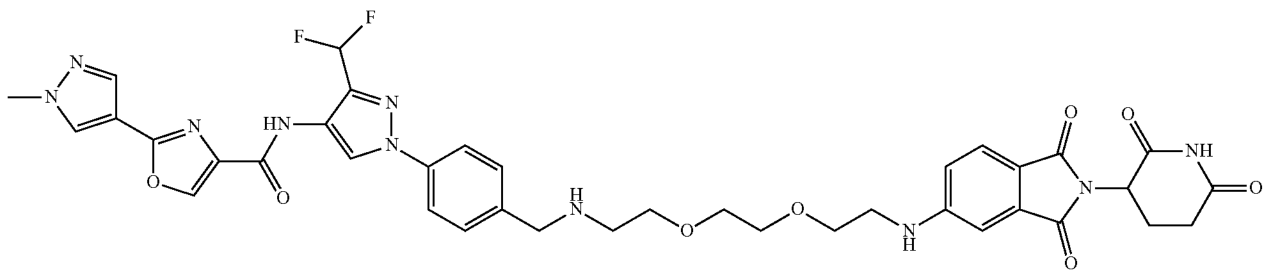 [SMILES: Cn1cc(-c2nc(C(=O)Nc3cn(-c4ccc(CNCCOCCOCCNc5ccc6c(c5)C(=O)N(C5CCC(=O)NC5=O)C6=O)cc4)nc3C(F)F)co2)cn1] |
| I-354 | 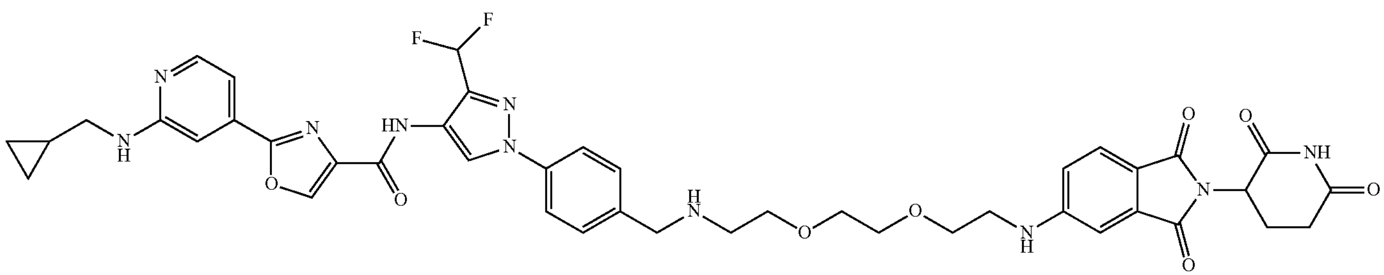 [SMILES: O=C1CCC(N2C(=O)c3ccc(NCCOCCOCCNCc4ccc(-n5cc(NC(=O)c6coc(-c7ccnc(NCC8CC8)c7)n6)c(C(F)F)n5)cc4)cc3C2=O)C(=O)N1] |

TABLE 1-continued
Exemplary Compounds
| I-# | Structure |
|---|---|
| I-355 | 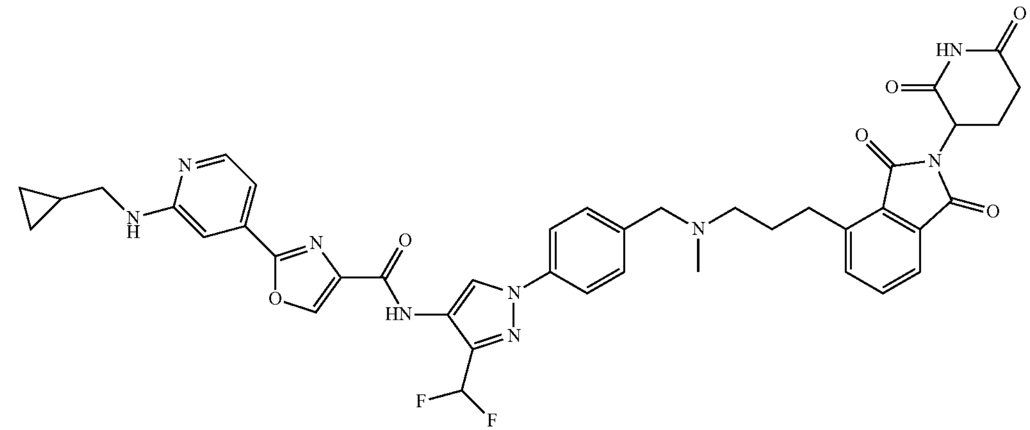 [SMILES: CN(CCCc1cccc2c1C(=O)N(C1CCC(=O)NC1=O)C2=O)Cc1ccc(-n2cc(NC(=O)c3coc(-c4ccnc(NCC5CC5)c4)n3)c(C(F)F)n2)cc1] |
| I-356 | 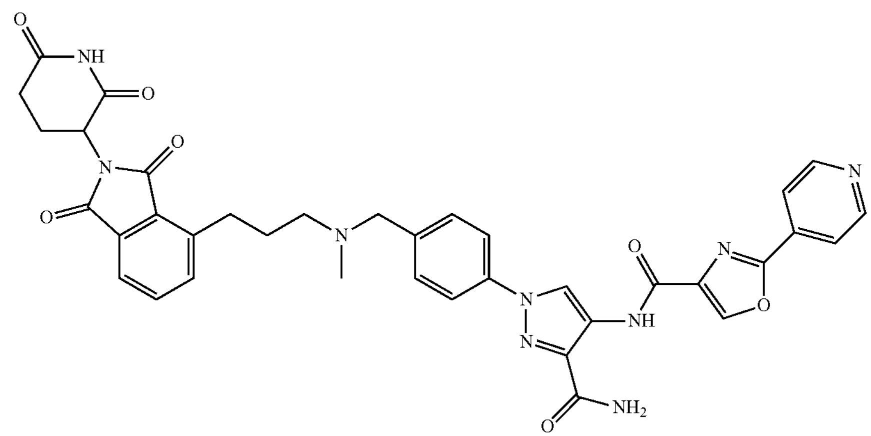 [SMILES: CN(CCCc1cccc2c1C(=O)N(C1CCC(=O)NC1=O)C2=O)Cc1ccc(-n2cc(NC(=O)c3coc(-c4ccncc4)n3)c(C(N)=O)n2)cc1] |

TABLE 1-continued
Exemplary Compounds
| I-# | Structure |
|---|---|
| I-357 | 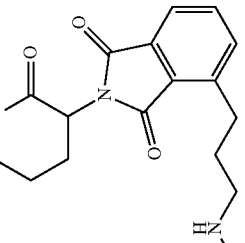 |
| I-358 | 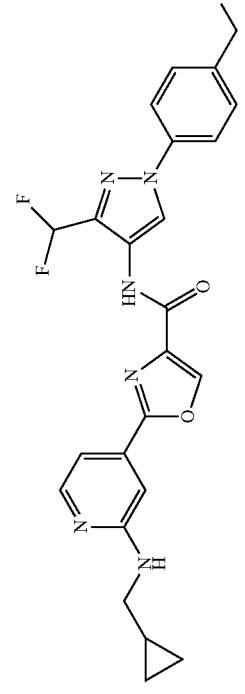 |

TABLE 1-continued
Exemplary Compounds
| I-# | Structure |
|---|---|
| I-359 | 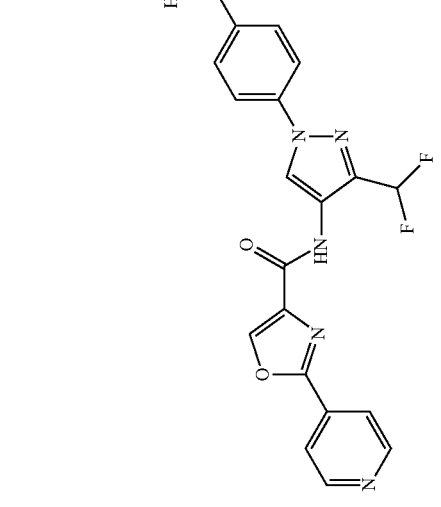 |
| I-360 | 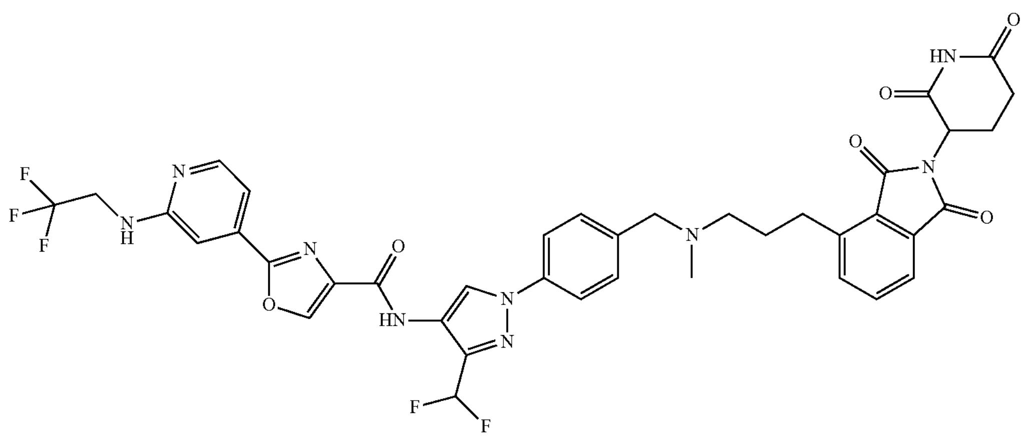 [SMILES: CN(CCCc1cccc2c1C(=O)N(C1CCC(=O)NC1=O)C2=O)Cc1ccc(-n2cc(NC(=O)c3coc(-c4ccnc(NCC(F)(F)F)c4)n3)c(C(F)F)n2)cc1] |

TABLE 1-continued
Exemplary Compounds
| I-# | Structure |
|---|---|
| I-361 | 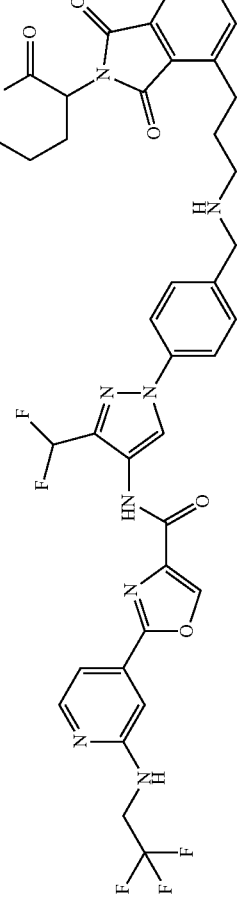 |
| I-362 | 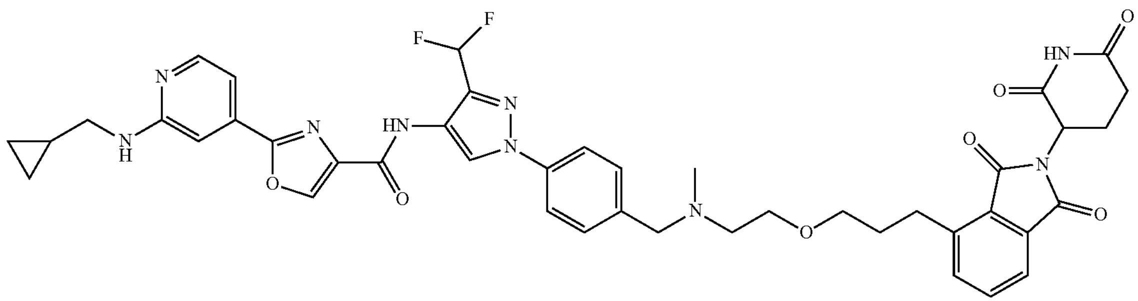 [SMILES: CN(CCOCCCc1cccc2c1C(=O)N(C1CCC(=O)NC1=O)C2=O)Cc1ccc(-n2cc(NC(=O)c3coc(-c4ccnc(NCC5CC5)c4)n3)c(C(F)F)n2)cc1] |
| I-363 | 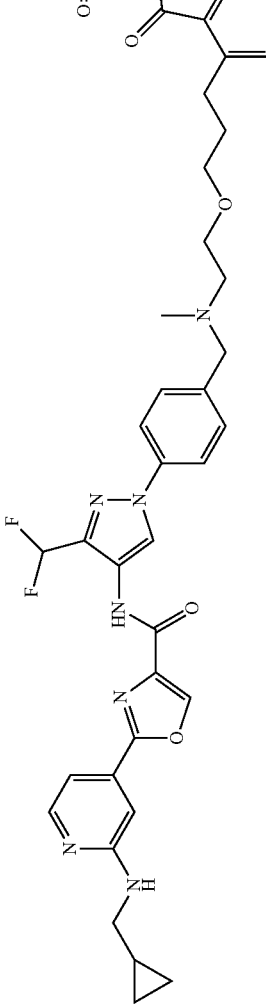 |

TABLE 1-continued
Exemplary Compounds
| I-# | Structure |
|---|---|
| I-364 | 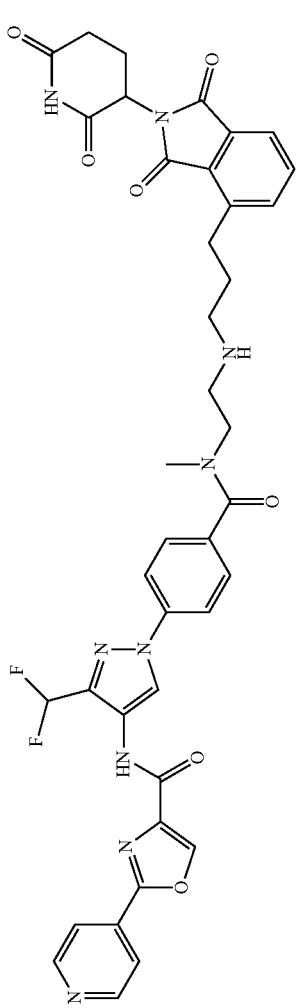 |
| I-365 | 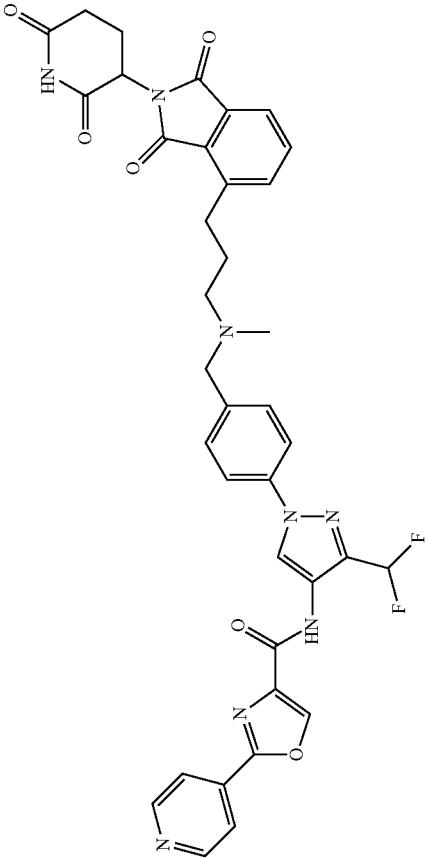 |

TABLE 1-continued

Exemplary Compounds

| I-# | Structure |
|---|---|
| I-366 | 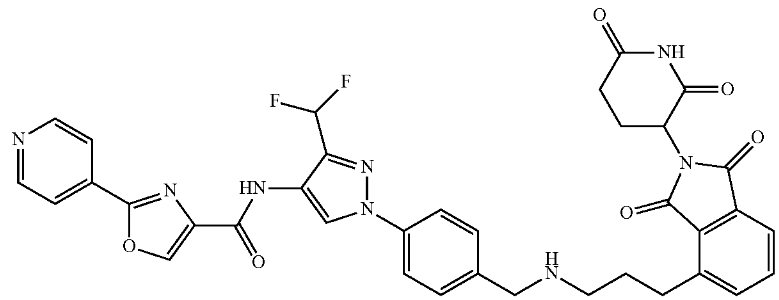 [SMILES: O=C1CCC(N2C(=O)c3cccc(CCCNCc4ccc(-n5cc(NC(=O)c6coc(-c7ccncc7)n6)c(C(F)F)n5)cc4)c3C2=O)C(=O)N1] |
| I-367 | 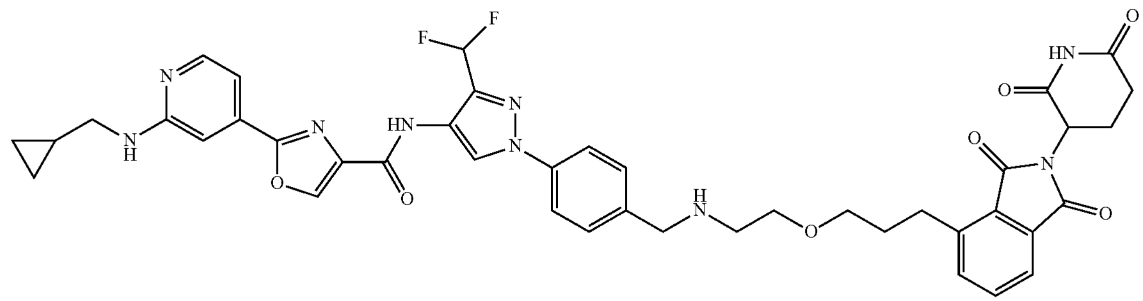 [SMILES: O=C1CCC(N2C(=O)c3cccc(CCCOCCNCc4ccc(-n5cc(NC(=O)c6coc(-c7ccnc(NCC8CC8)c7)n6)c(C(F)F)n5)cc4)c3C2=O)C(=O)N1] |
| I-368 | 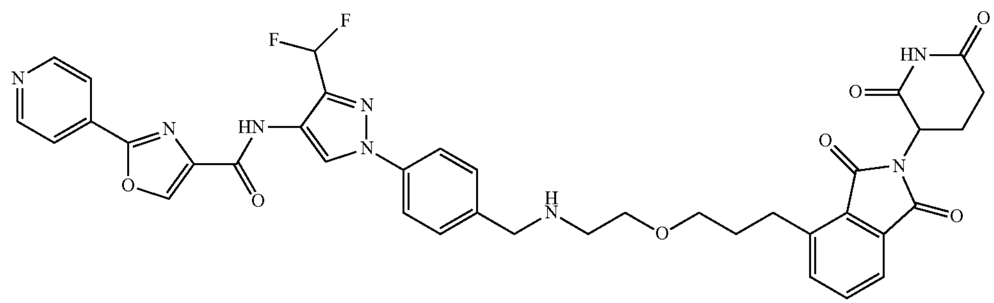 [SMILES: O=C1CCC(N2C(=O)c3cccc(CCCOCCNCc4ccc(-n5cc(NC(=O)c6coc(-c7ccncc7)n6)c(C(F)F)n5)cc4)c3C2=O)C(=O)N1] |

TABLE 1-continued
Exemplary Compounds
| I-# | Structure |
|---|---|
| I-369 | 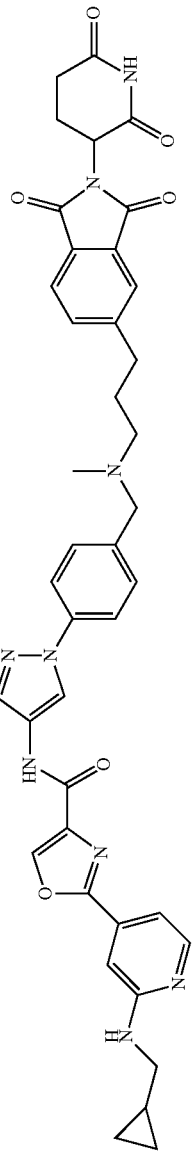 |
| I-370 | 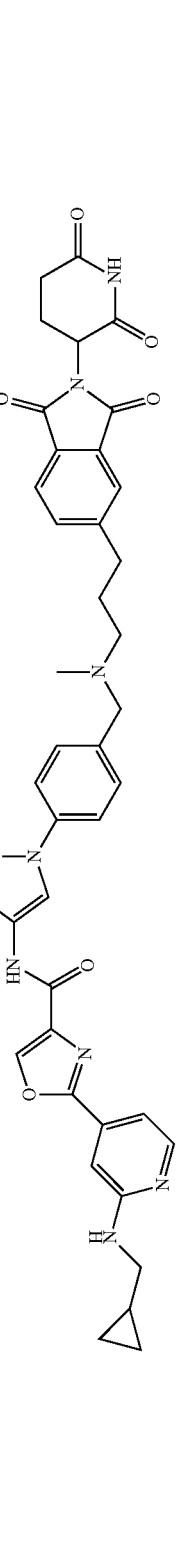 |
| I-371 | 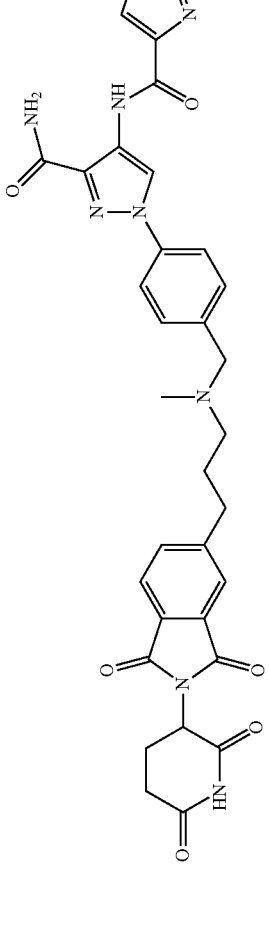 |

TABLE 1-continued

Exemplary Compounds

| I-# | Structure |
|---|---|
| I-372 | 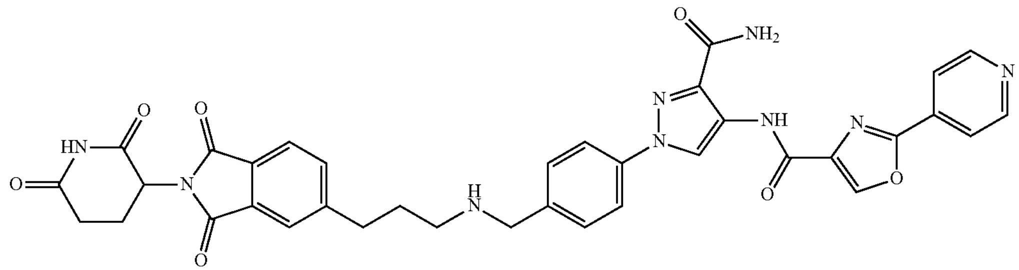 [SMILES: NC(=O)c1nn(-c2ccc(CNCCCc3ccc4c(c3)C(=O)N(C3CCC(=O)NC3=O)C4=O)cc2)cc1NC(=O)c1coc(-c2ccncc2)n1] |
| I-373 | 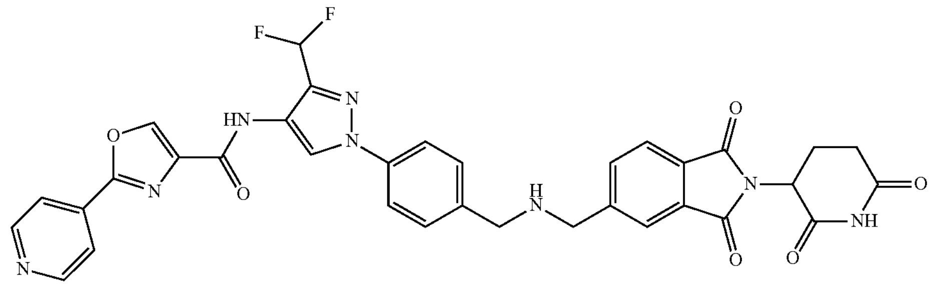 [SMILES: O=C1CCC(N2C(=O)c3ccc(CNCc4ccc(-n5cc(NC(=O)c6coc(-c7ccncc7)n6)c(C(F)F)n5)cc4)cc3C2=O)C(=O)N1] |
| I-374 | 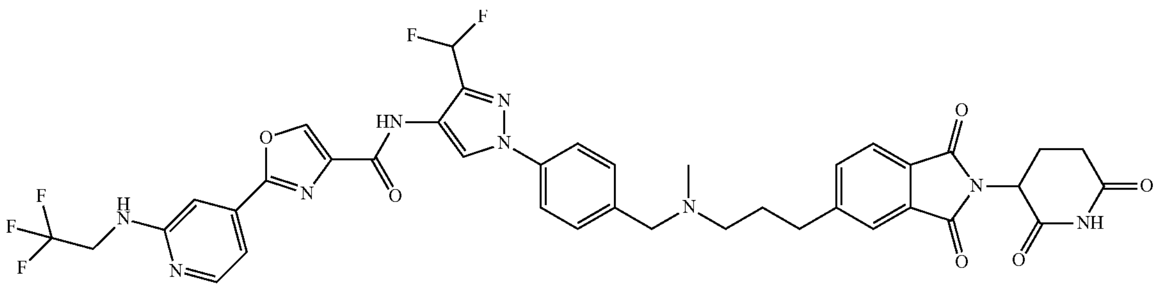 [SMILES: CN(CCCc1ccc2c(c1)C(=O)N(C1CCC(=O)NC1=O)C2=O)Cc1ccc(-n2cc(NC(=O)c3coc(-c4ccnc(NCC(F)(F)F)c4)n3)c(C(F)F)n2)cc1] |

TABLE 1-continued

Exemplary Compounds

| I-# | Structure |
|---|---|
| I-375 | 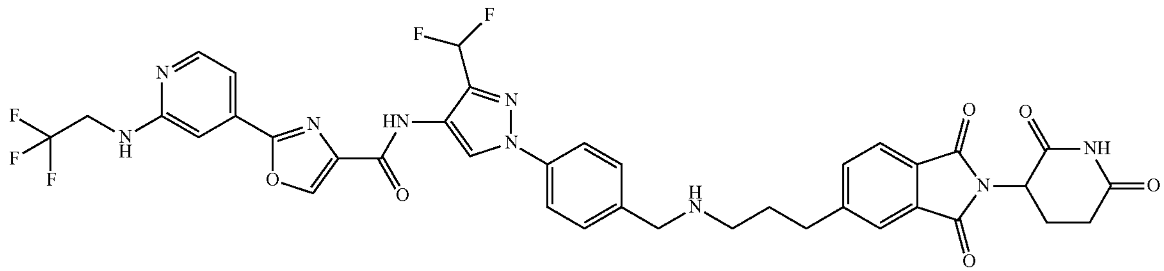 [SMILES: O=C1CCC(N2C(=O)c3ccc(CCCNCc4ccc(-n5cc(NC(=O)c6coc(-c7ccnc(NCC(F)(F)F)c7)n6)c(C(F)F)n5)cc4)cc3C2=O)C(=O)N1] |
| I-376 | 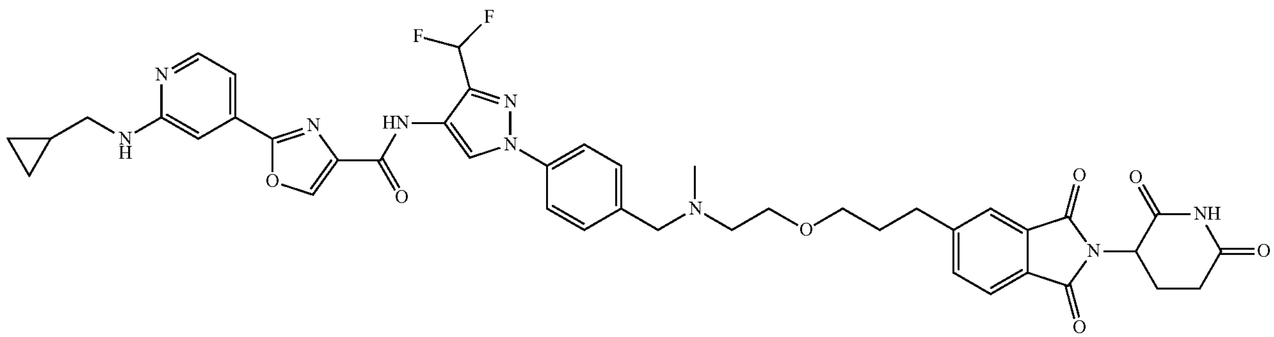 [SMILES: CN(CCOCCCc1ccc2c(c1)C(=O)N(C1CCC(=O)NC1=O)C2=O)Cc1ccc(-n2cc(NC(=O)c3coc(-c4ccnc(NCC5CC5)c4)n3)c(C(F)F)n2)cc1] |
| I-377 | 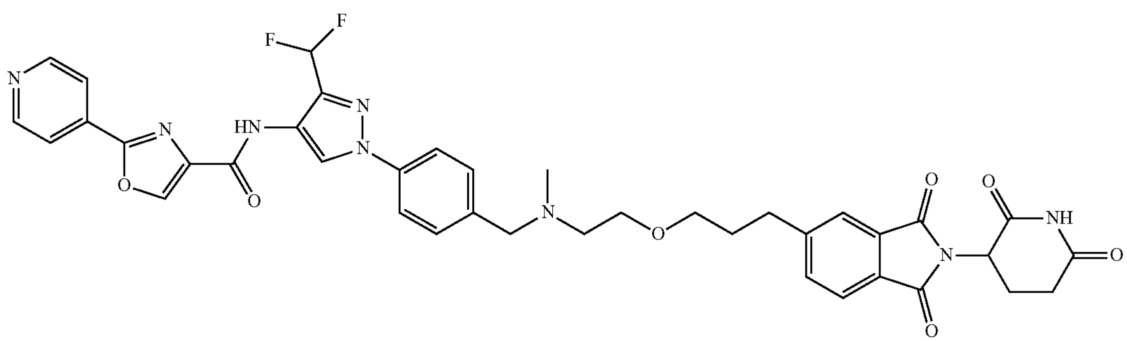 [SMILES: CN(CCOCCCc1ccc2c(c1)C(=O)N(C1CCC(=O)NC1=O)C2=O)Cc1ccc(-n2cc(NC(=O)c3coc(-c4ccncc4)n3)c(C(F)F)n2)cc1] |

TABLE 1-continued
Exemplary Compounds
| I-# | Structure |
|---|---|
| I-378 | 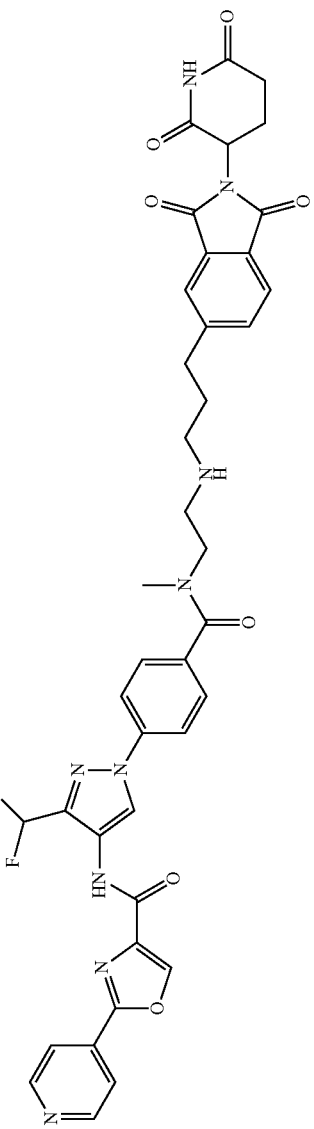 |
| I-379 | 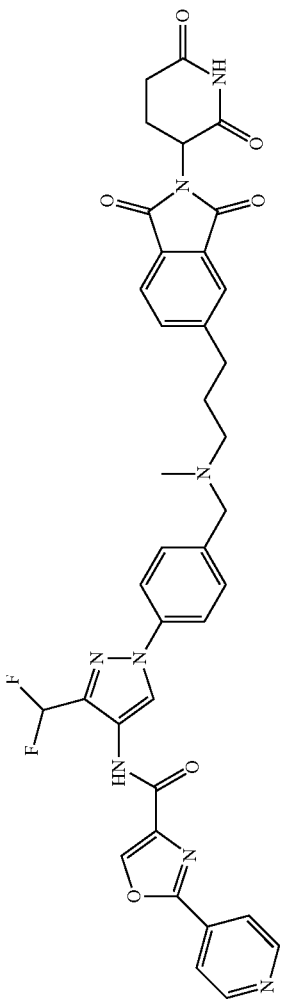 |
| I-380 | 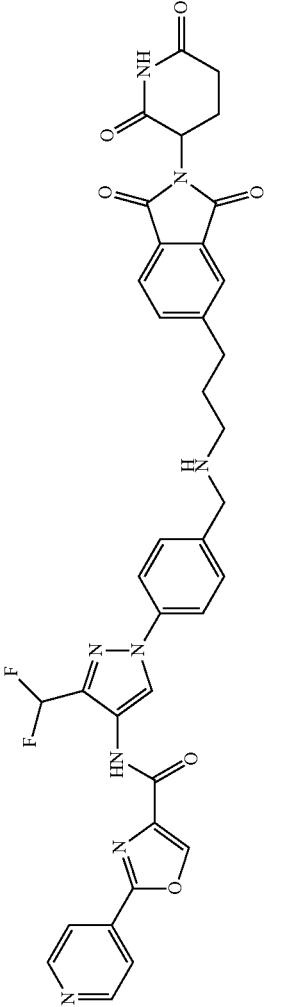 |

TABLE 1-continued
Exemplary Compounds
| I-# | Structure |
|---|---|
| I-381 | 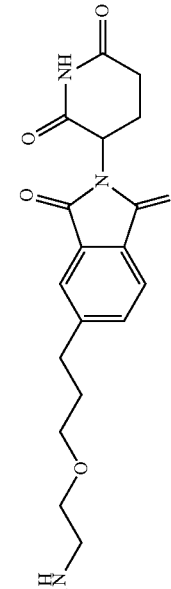 |
| I-382 | 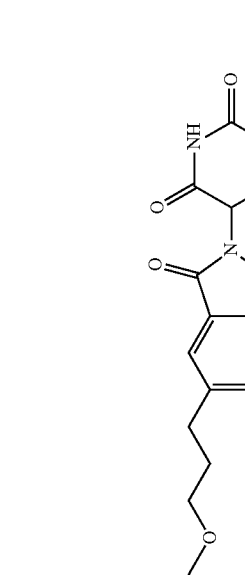 |

TABLE 1-continued
Exemplary Compounds
| I-# | Structure |
|---|---|
| I-383 | 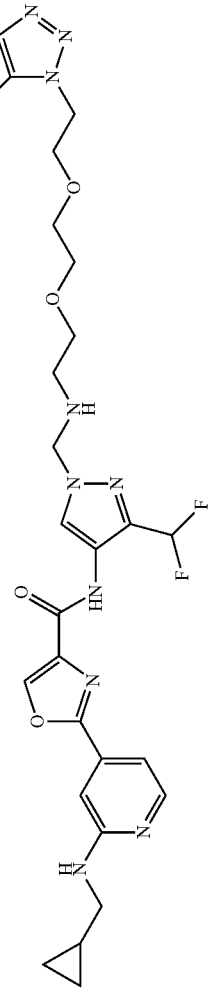 |
| I-384 | 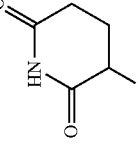 |

TABLE 1-continued

Exemplary Compounds

| I-# | Structure |
|---|---|
| I-385 | 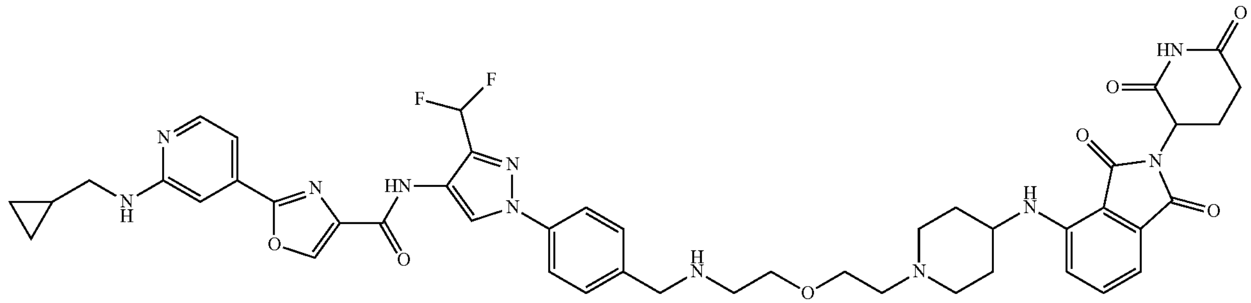 [SMILES: O=C1CCC(N2C(=O)c3cccc(NC4CCN(CCOCCNCc5ccc(-n6cc(NC(=O)c7coc(-c8ccnc(NCC9CC9)c8)n7)c(C(F)F)n6)cc5)CC4)c3C2=O)C(=O)N1] |
| I-386 | 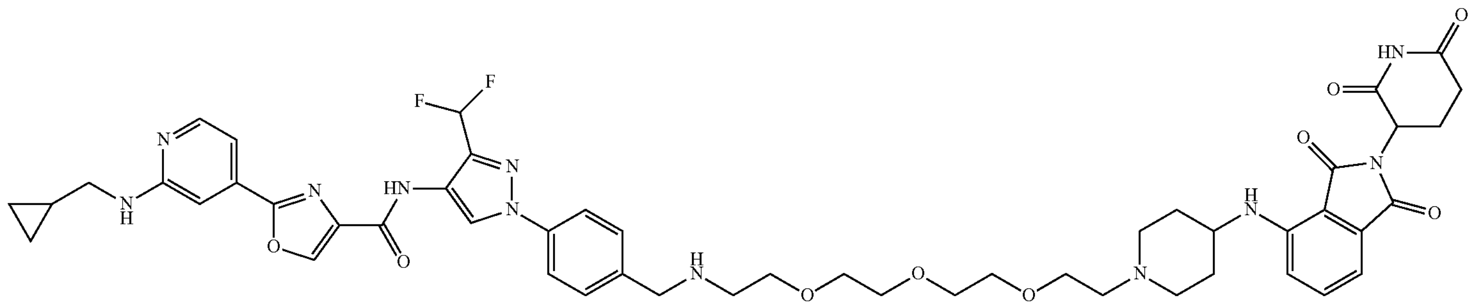 [SMILES: O=C1CCC(N2C(=O)c3cccc(NC4CCN(CCOCCOCCOCCNCc5ccc(-n6cc(NC(=O)c7coc(-c8ccnc(NCC9CC9)c8)n7)c(C(F)F)n6)cc5)CC4)c3C2=O)C(=O)N1] |
| I-387 | 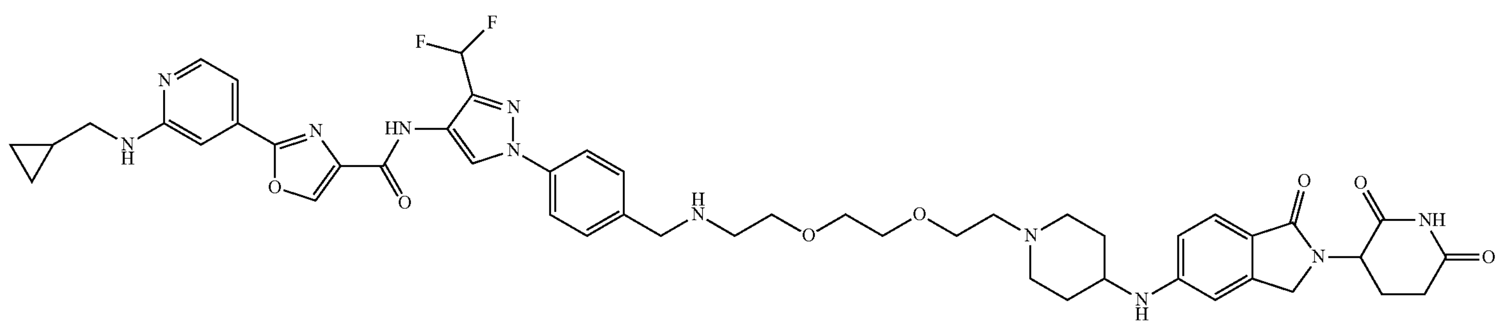 [SMILES: O=C1CCC(N2Cc3cc(NC4CCN(CCOCCOCCNCc5ccc(-n6cc(NC(=O)c7coc(-c8ccnc(NCC9CC9)c8)n7)c(C(F)F)n6)cc5)CC4)ccc3C2=O)C(=O)N1] |

TABLE 1-continued

Exemplary Compounds

| I-# | Structure |
|---|---|
| I-388 | 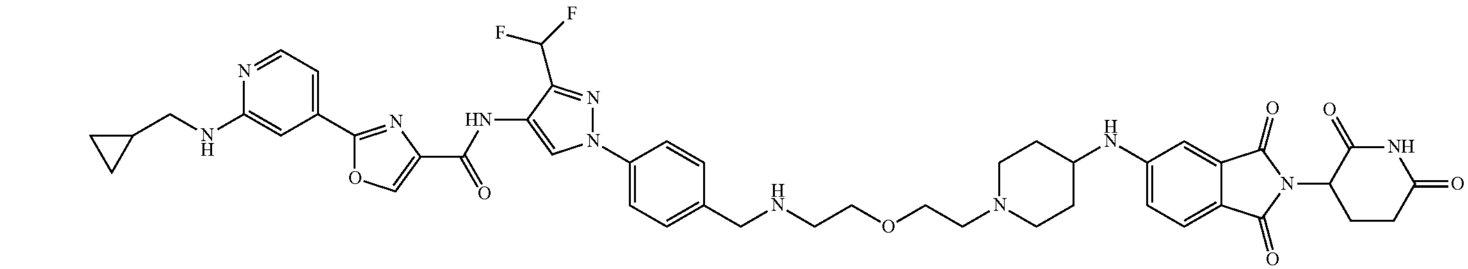 [SMILES: O=C1CCC(N2C(=O)c3ccc(NC4CCN(CCOCCNCc5ccc(-n6cc(NC(=O)c7coc(-c8ccnc(NCC9CC9)c8)n7)c(C(F)F)n6)cc5)CC4)cc3C2=O)C(=O)N1] |
| I-389 | 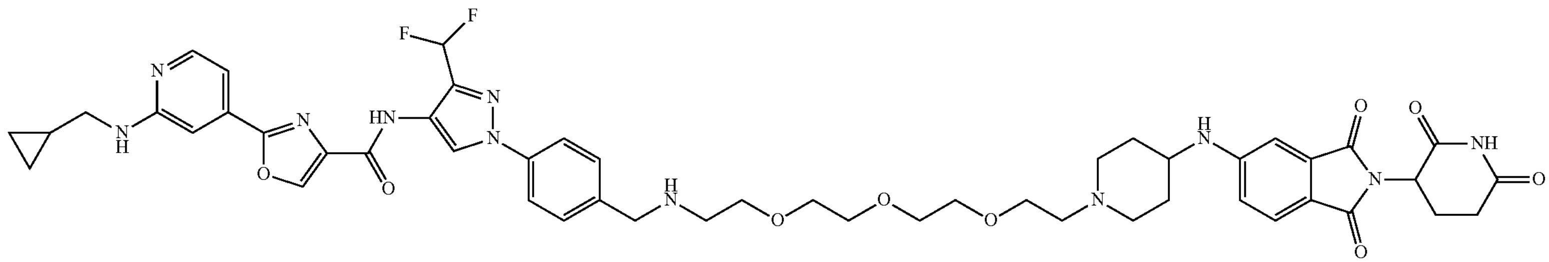 [SMILES: O=C1CCC(N2C(=O)c3ccc(NC4CCN(CCOCCOCCOCCNCc5ccc(-n6cc(NC(=O)c7coc(-c8ccnc(NCC9CC9)c8)n7)c(C(F)F)n6)cc5)CC4)cc3C2=O)C(=O)N1] |
| I-390 | 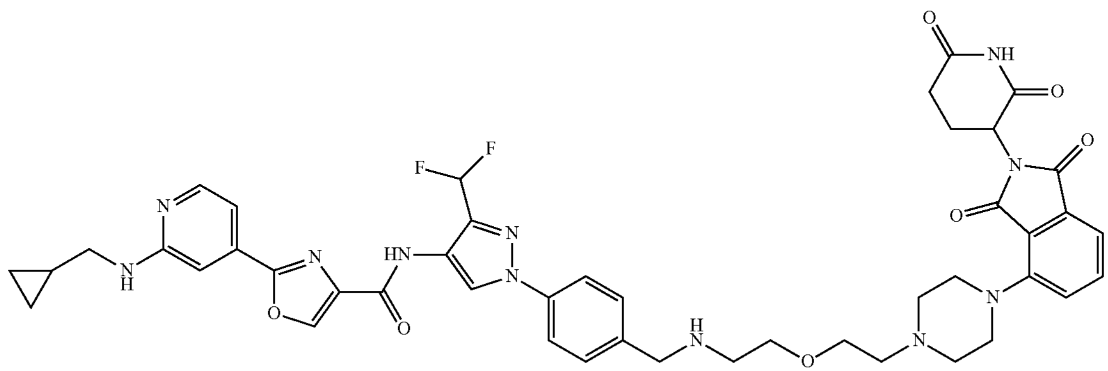 [SMILES: O=C1CCC(N2C(=O)c3cccc(N4CCN(CCOCCNCc5ccc(-n6cc(NC(=O)c7coc(-c8ccnc(NCC9CC9)c8)n7)c(C(F)F)n6)cc5)CC4)c3C2=O)C(=O)N1] |

TABLE 1-continued
Exemplary Compounds
| I-# | Structure |
|---|---|
| I-391 | 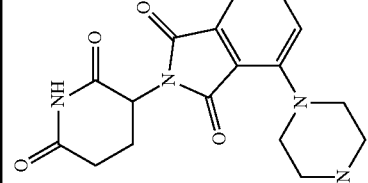 |
| I-392 | 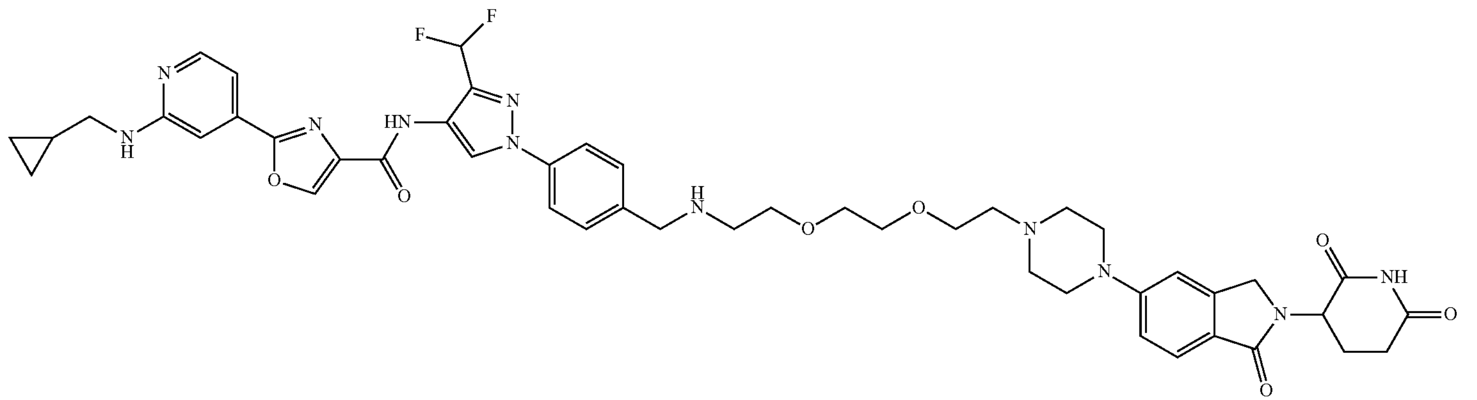 [SMILES: O=C1CCC(N2Cc3cc(N4CCN(CCOCCOCCNCc5ccc(-n6cc(NC(=O)c7coc(-c8ccnc(NCC9CC9)c8)n7)c(C(F)F)n6)cc5)CC4)ccc3C2=O)C(=O)N1] |
| I-393 | 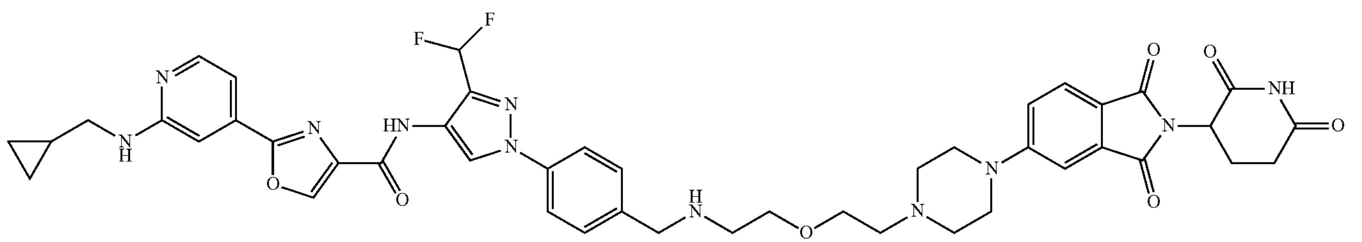 [SMILES: O=C1CCC(N2C(=O)c3ccc(N4CCN(CCOCCNCc5ccc(-n6cc(NC(=O)c7coc(-c8ccnc(NCC9CC9)c8)n7)c(C(F)F)n6)cc5)CC4)cc3C2=O)C(=O)N1] |

TABLE 1-continued
Exemplary Compounds
| I-# | Structure |
|---|---|
| I-394 | 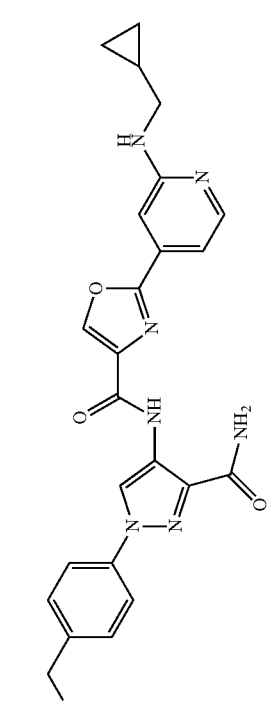 |
| I-395 | 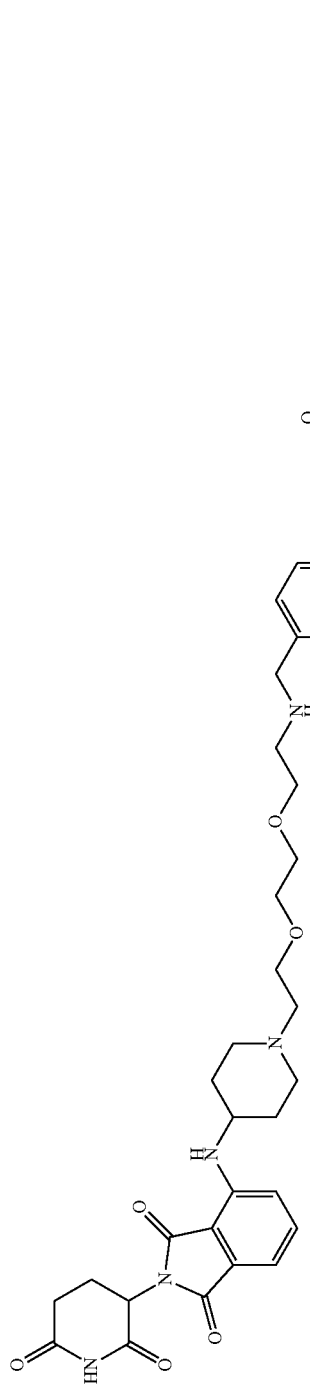 |

TABLE 1-continued

Exemplary Compounds

| I-# | Structure |
|---|---|
| I-396 | 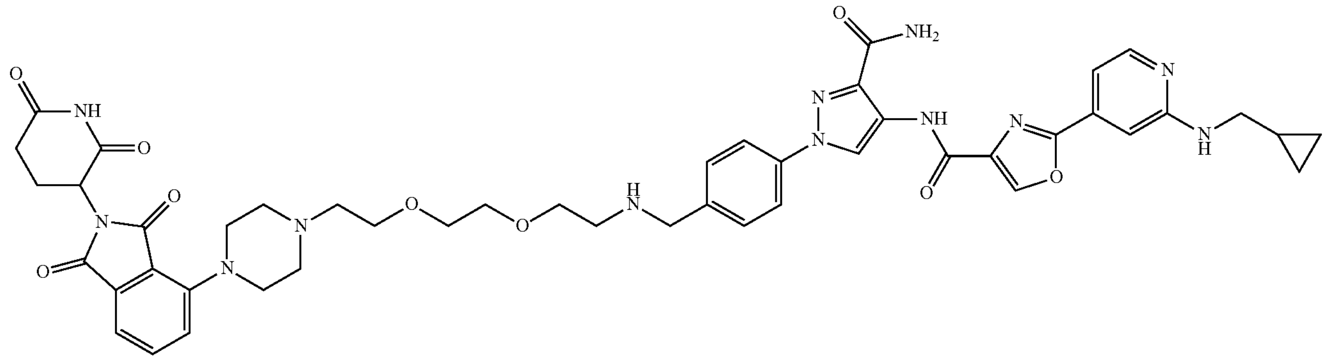 [SMILES: NC(=O)c1nn(-c2ccc(CNCCOCCOCCN3CCN(c4cccc5c4C(=O)N(C4CCC(=O)NC4=O)C5=O)CC3)cc2)cc1NC(=O)c1coc(-c2ccnc(NCC3CC3)c2)n1] |
| I-397 | 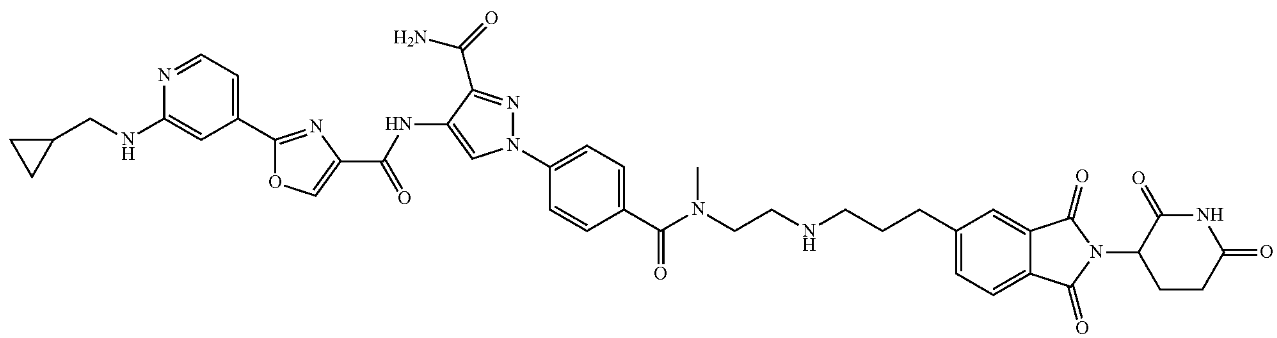 [SMILES: CN(CCNCCCc1ccc2c(c1)C(=O)N(C1CCC(=O)NC1=O)C2=O)C(=O)c1ccc(-n2cc(NC(=O)c3coc(-c4ccnc(NCC5CC5)c4)n3)c(C(N)=O)n2)cc1] |
| I-398 | 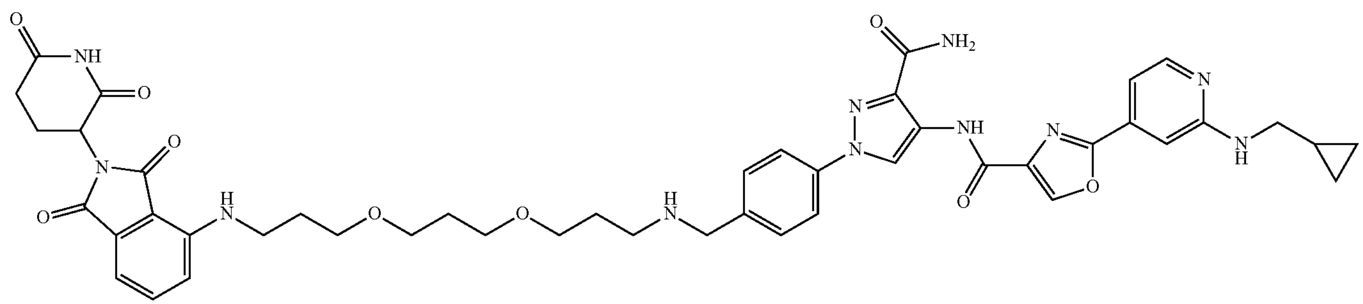 [SMILES: NC(=O)c1nn(-c2ccc(CNCCCOCCCOCCCNc3cccc4c3C(=O)N(C3CCC(=O)NC3=O)C4=O)cc2)cc1NC(=O)c1coc(-c2ccnc(NCC3CC3)c2)n1] |

TABLE 1-continued
Exemplary Compounds
| I-# | Structure |
|---|---|
| I-399 | 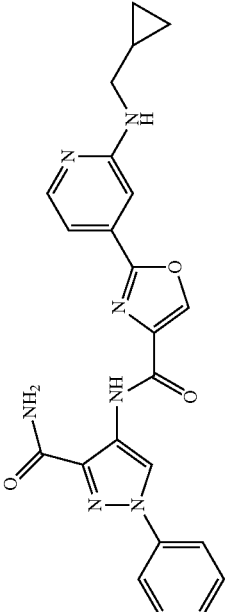 |
| I-400 |  |
| I-401 | 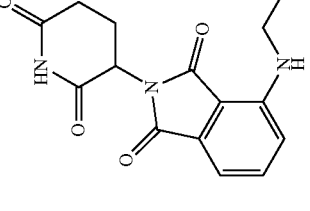 |

TABLE 1-continued
Exemplary Compounds
| I-# | Structure |
|---|---|
| I-402 | 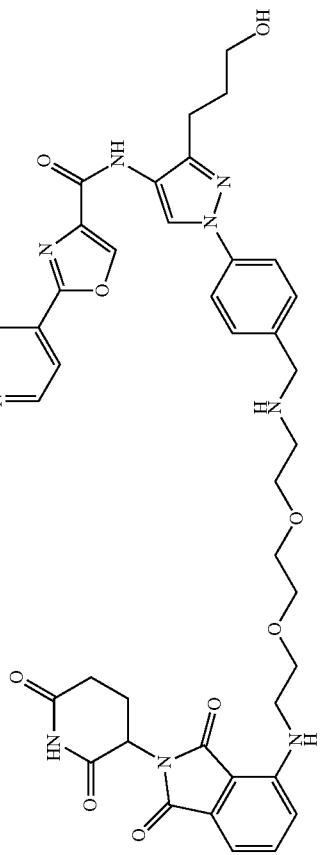 |

TABLE 1-continued
Exemplary Compounds
| I-# | Structure |
|---|---|
| I-403 | 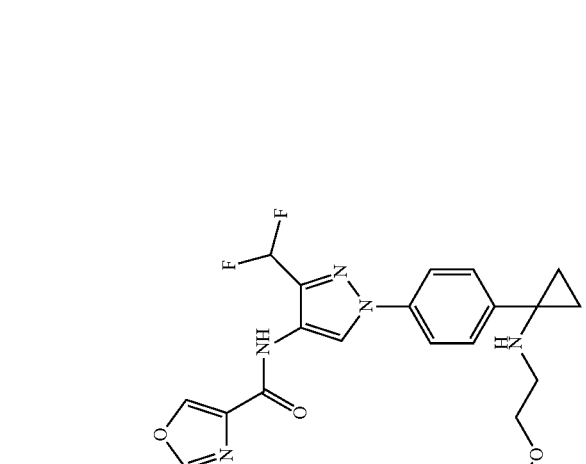 |
| I-404 | 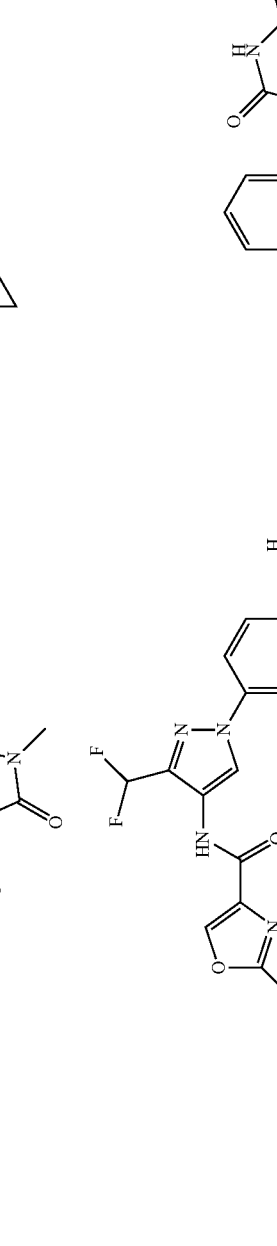 |

TABLE 1-continued

Exemplary Compounds

| I-# | Structure |
|---|---|
| I-405 | 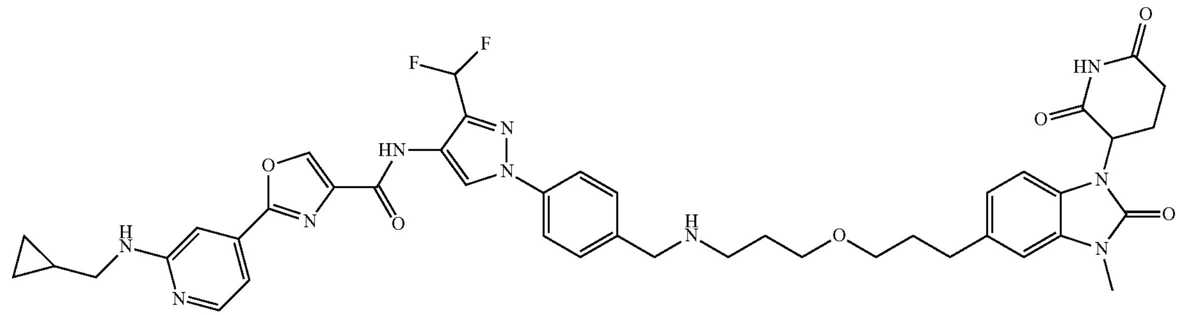 [SMILES: Cn1c(=O)n(C2CCC(=O)NC2=O)c2ccc(CCCOCCCNCc3ccc(-n4cc(NC(=O)c5coc(-c6ccnc(NCC7CC7)c6)n5)c(C(F)F)n4)cc3)cc21] |
| I-406 | 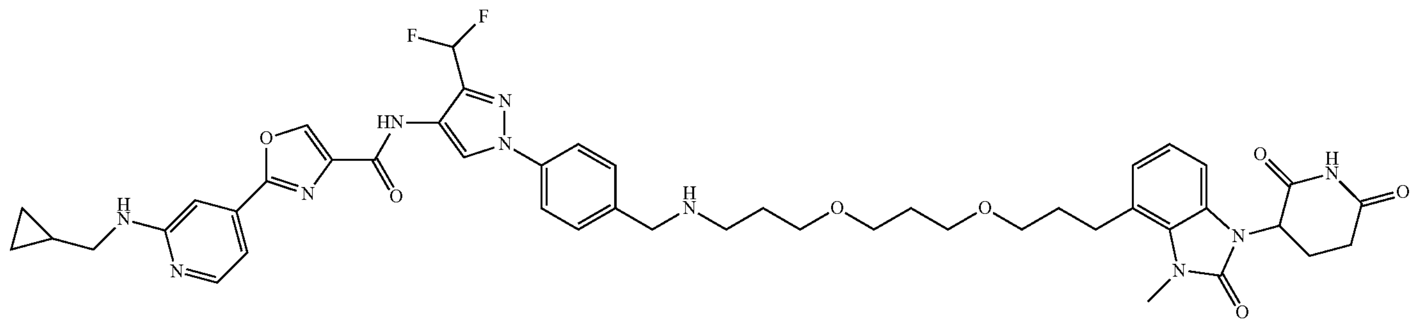 [SMILES: Cn1c(=O)n(C2CCC(=O)NC2=O)c2cccc(CCCOCCCOCCCNCc3ccc(-n4cc(NC(=O)c5coc(-c6ccnc(NCC7CC7)c6)n5)c(C(F)F)n4)cc3)c21] |
| I-407 | 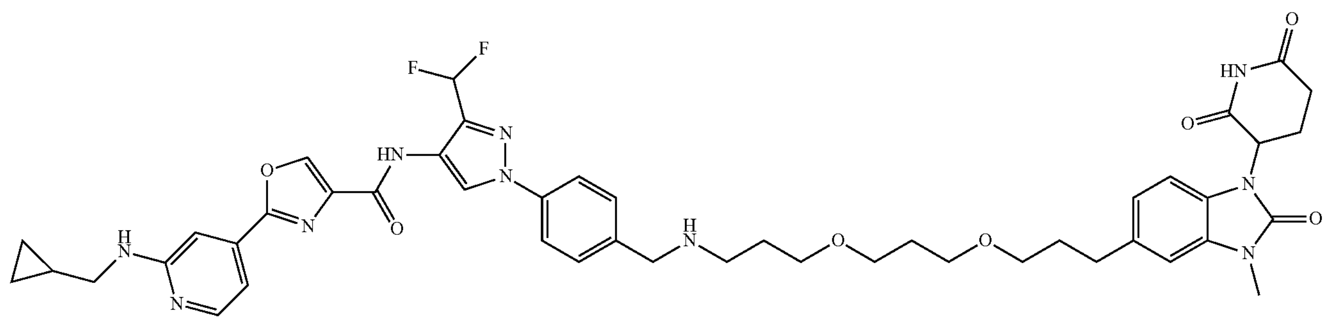 [SMILES: Cn1c(=O)n(C2CCC(=O)NC2=O)c2ccc(CCCOCCCOCCCNCc3ccc(-n4cc(NC(=O)c5coc(-c6ccnc(NCC7CC7)c6)n5)c(C(F)F)n4)cc3)cc21] |

TABLE 1-continued
Exemplary Compounds
| I-# | Structure |
|---|---|
| I-408 | 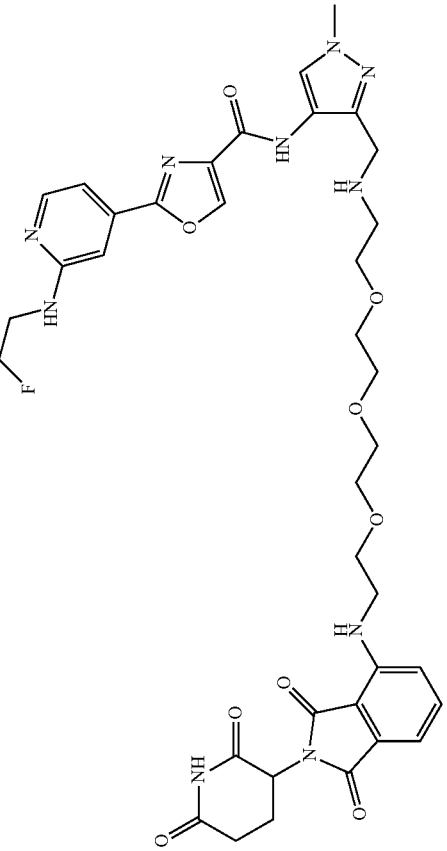 |
| I-409 | 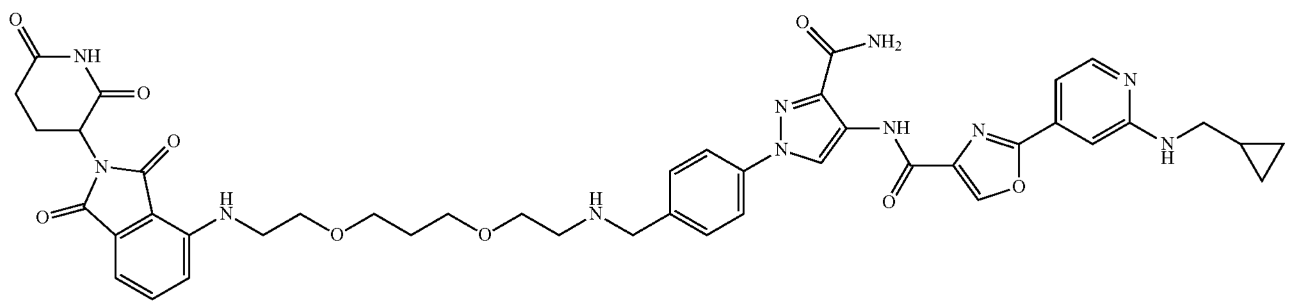 [SMILES: NC(=O)c1nn(-c2ccc(CNCCOCCCOCCNc3cccc4c3C(=O)N(C3CCC(=O)NC3=O)C4=O)cc2)cc1NC(=O)c1coc(-c2ccnc(NCC3CC3)c2)n1] |

TABLE 1-continued
Exemplary Compounds
| I-# | Structure |
|---|---|
| I-410 | 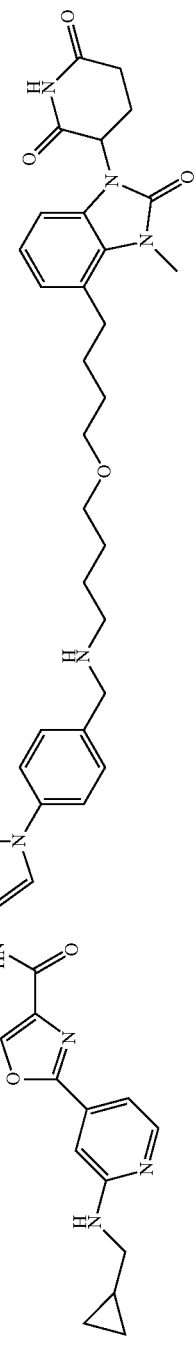 |
| I-411 | 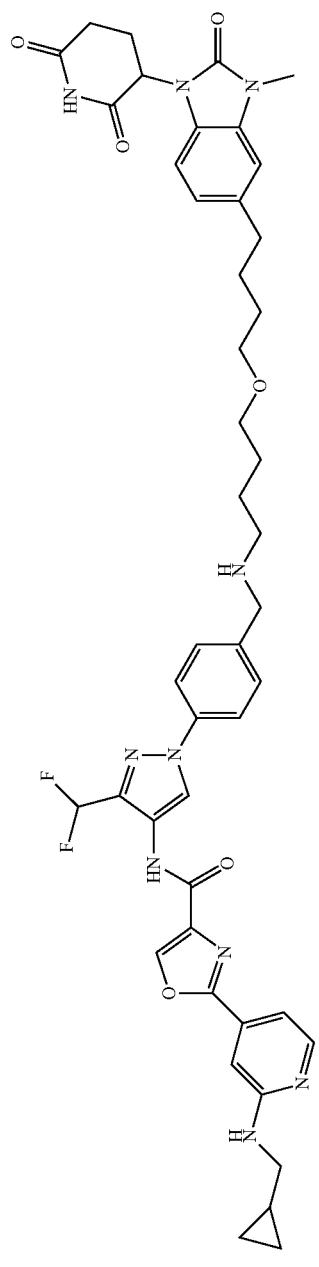 |

TABLE 1-continued
Exemplary Compounds
| I-# | Structure |
|---|---|
| I-412 | 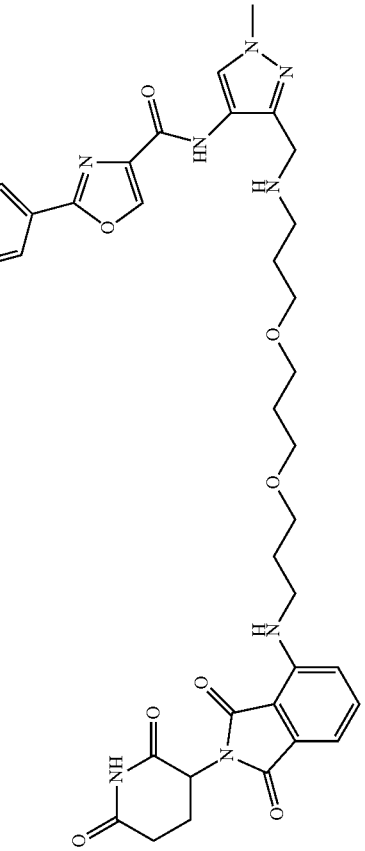 |
| I-413 | 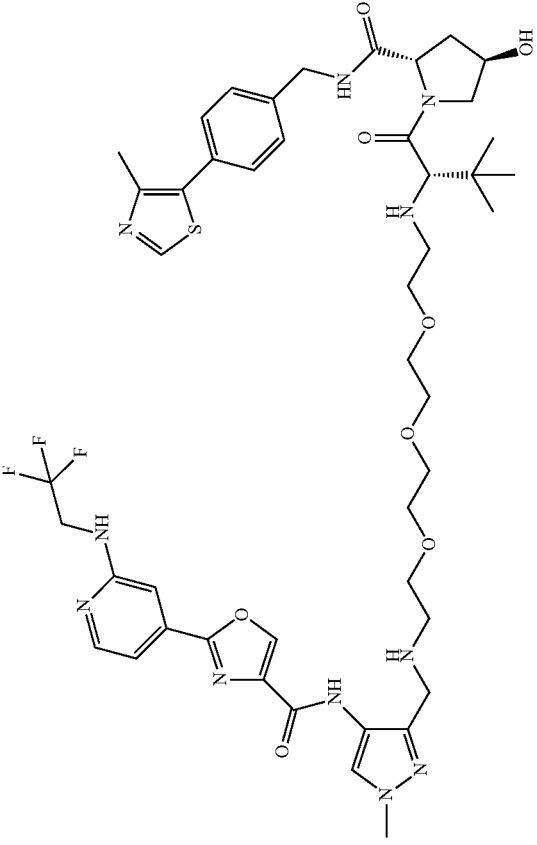 |

TABLE 1-continued
Exemplary Compounds
| I-# | Structure |
|---|---|
| I-414 | 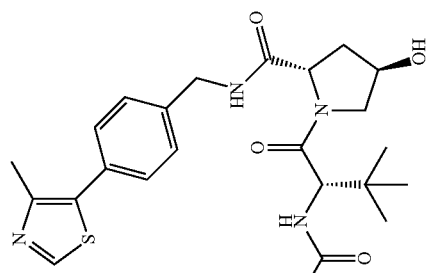 |
| I-415 | 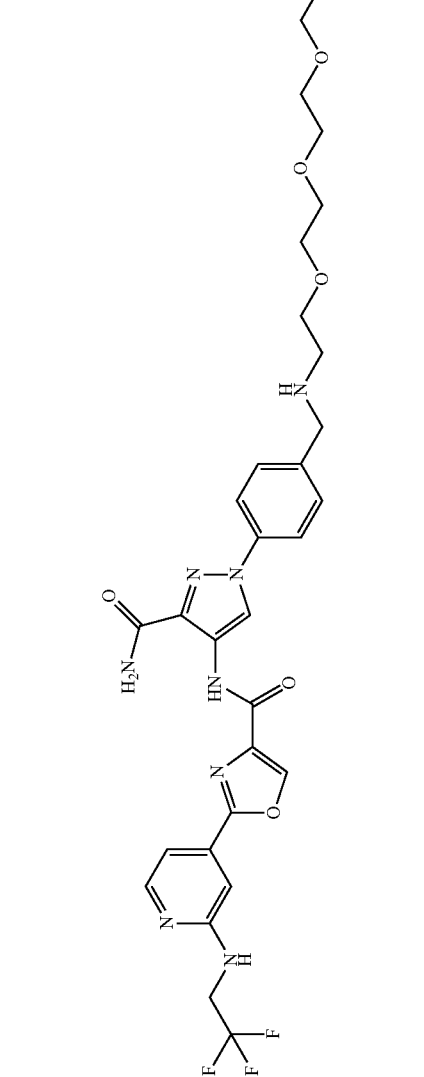 |

TABLE 1-continued

Exemplary Compounds

| I-# | Structure |
|---|---|
| I-416 | 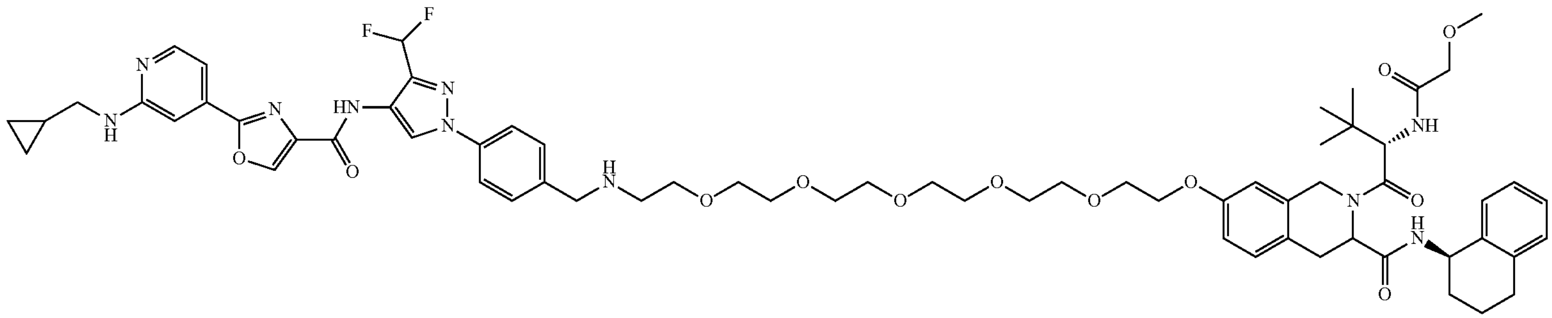 [SMILES: COCC(=O)N[C@H](C(=O)N1Cc2cc(OCCOCCOCCOCCOCCOCCNCc3ccc(-n4cc(NC(=O)c5coc(-c6ccnc(NCC7CC7)c6)n5)c(C(F)F)n4)cc3)ccc2CC1C(=O)N[C@@H]1CCCc2ccccc21)C(C)(C)C] |
| I-417 | 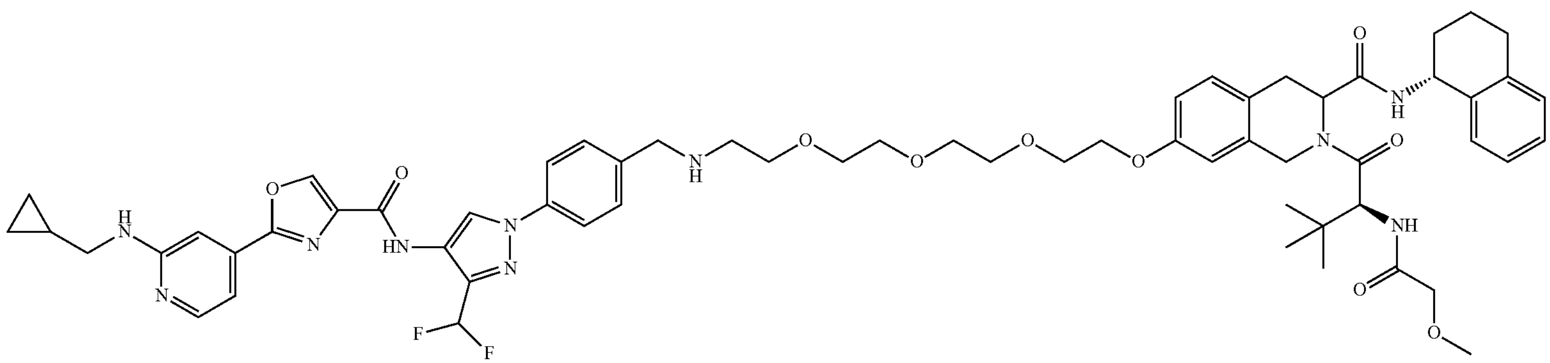 [SMILES: COCC(=O)N[C@H](C(=O)N1Cc2cc(OCCOCCOCCOCCNCc3ccc(-n4cc(NC(=O)c5coc(-c6ccnc(NCC7CC7)c6)n5)c(C(F)F)n4)cc3)ccc2CC1C(=O)N[C@@H]1CCCc2ccccc21)C(C)(C)C] |

TABLE 1-continued
Exemplary Compounds
| I-# | Structure |
|---|---|
| I-418 | 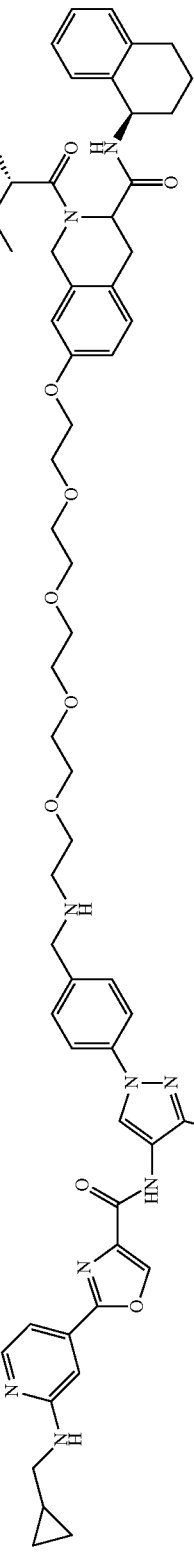 |
| I-419 | 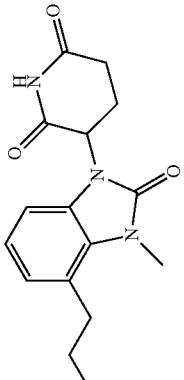 |

TABLE 1-continued

Exemplary Compounds

| I-# | Structure |
|---|---|
| I-420 | 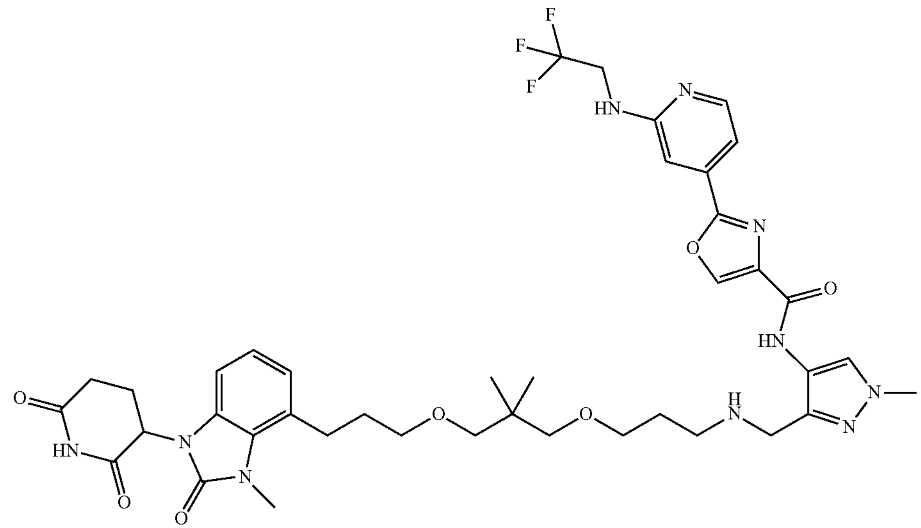 [SMILES: Cn1cc(NC(=O)c2coc(-c3ccnc(NCC(F)(F)F)c3)n2)c(CNCCCOCC(C)(C)COCCCc2cccc3c2n(C)c(=O)n3C2CCC(=O)NC2=O)n1] |
| I-421 | 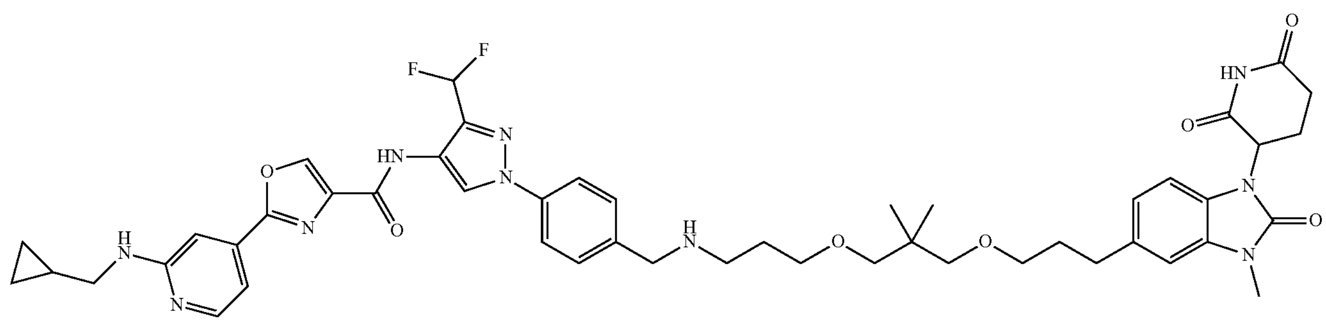 [SMILES: Cn1c(=O)n(C2CCC(=O)NC2=O)c2ccc(CCCOCC(C)(C)COCCCNCc3ccc(-n4cc(NC(=O)c5coc(-c6ccnc(NCC7CC7)c6)n5)c(C(F)F)n4)cc3)cc21] |

TABLE 1-continued
Exemplary Compounds
| I-# | Structure |
|---|---|
| I-422 | 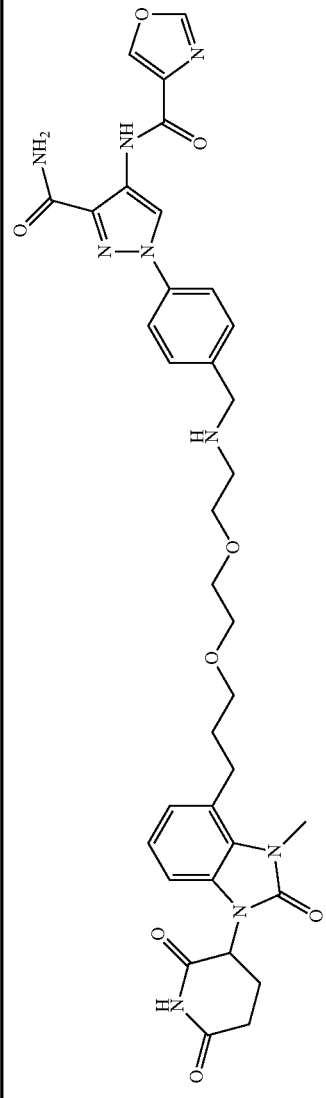 |
| I-423 | 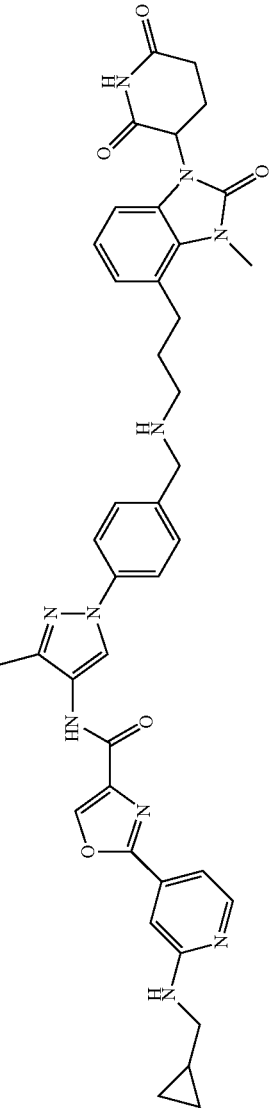 |
| I-424 | 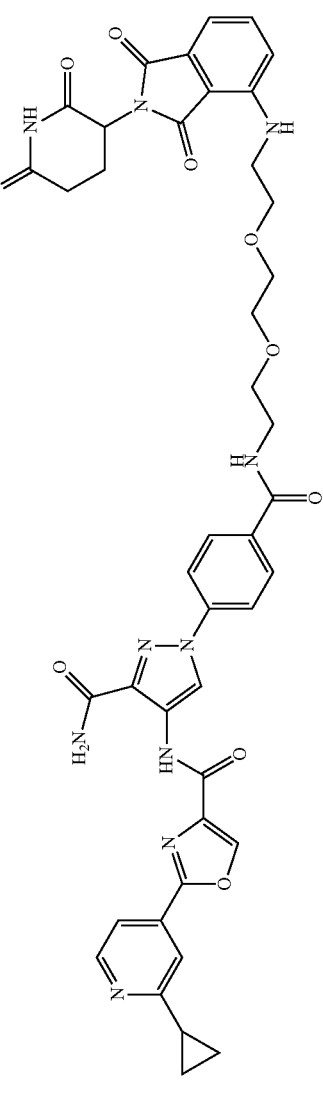 |

TABLE 1-continued
Exemplary Compounds
| I-# | Structure |
|---|---|
| I-425 | 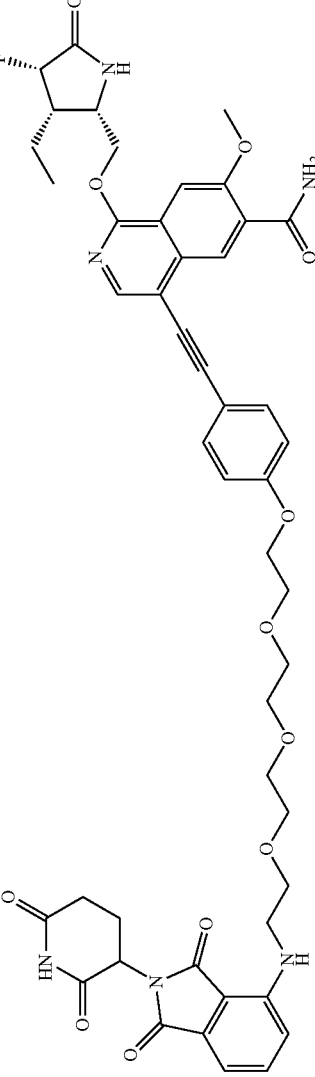 |
| I-426 | 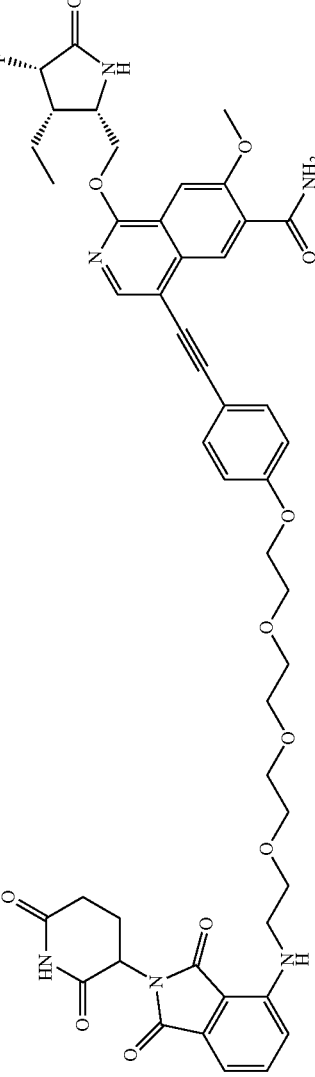 |

TABLE 1-continued
Exemplary Compounds
| I-# | Structure |
|---|---|
| I-427 | 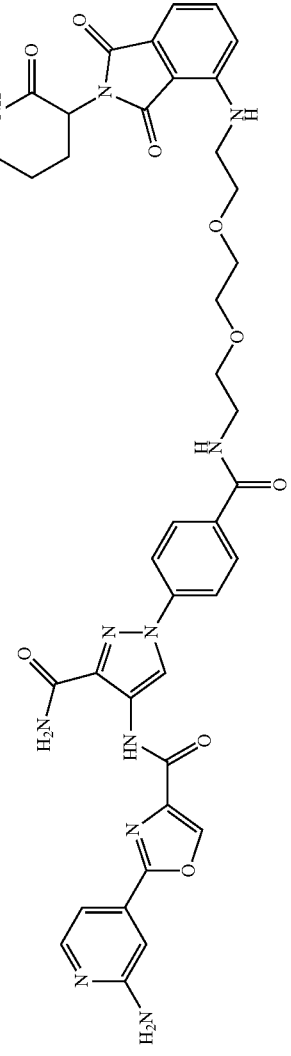 |
| I-428 | 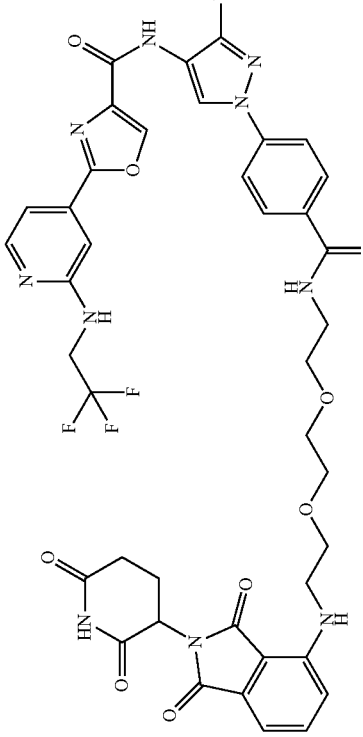 |

TABLE 1-continued
Exemplary Compounds
| I-# | Structure |
|---|---|
| I-429 | 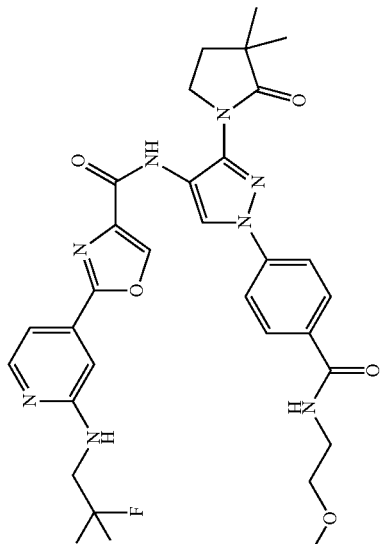 |
| I-432 | 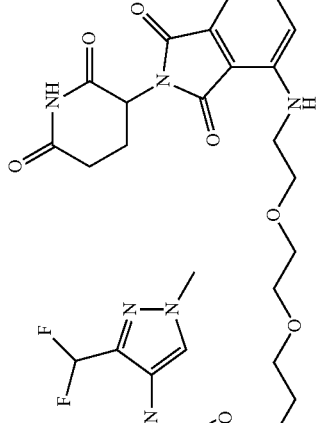 |
| I-434 | 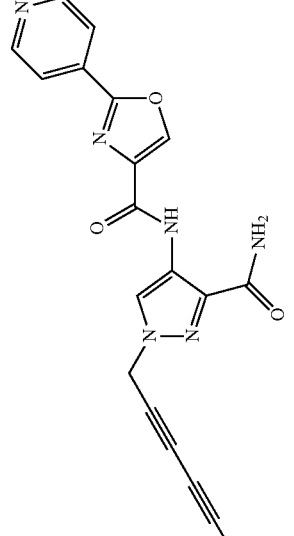 |

TABLE 1-continued
Exemplary Compounds
| I-# | Structure |
|---|---|
| I-435 | 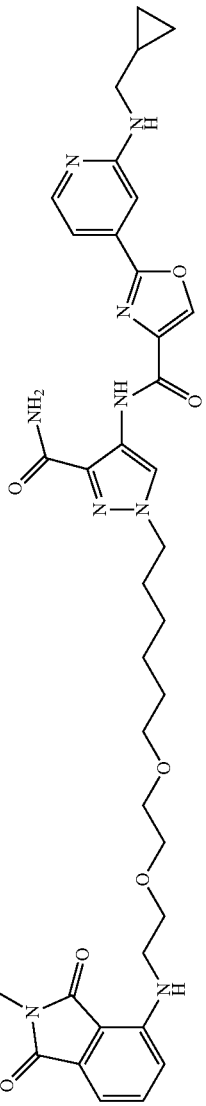 |
| I-436 | 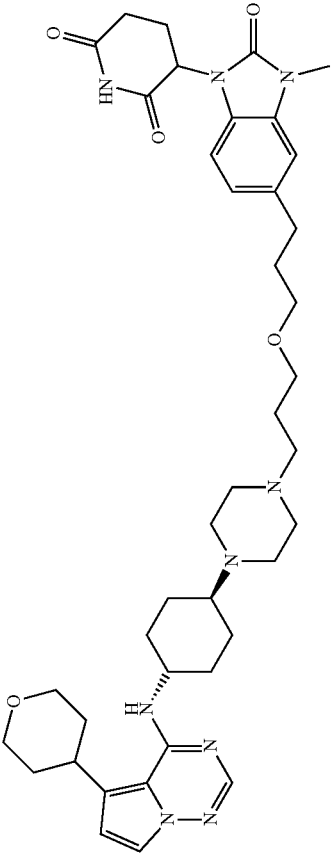 |
| I-437 | 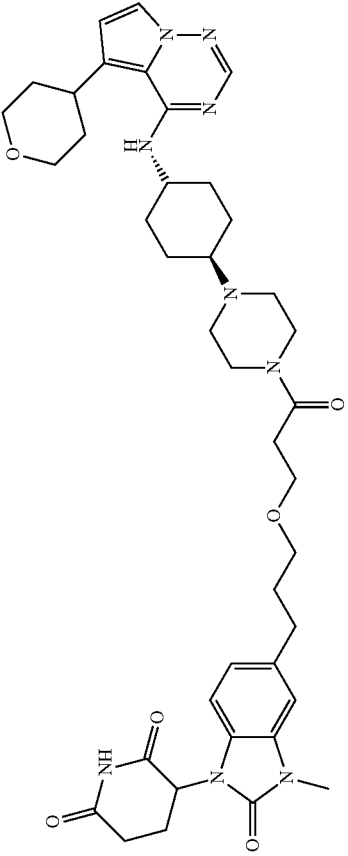 |

TABLE 1-continued
Exemplary Compounds
| I-# | Structure |
|---|---|
| I-438 | 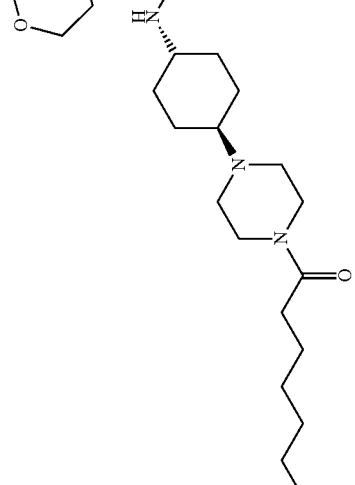 |
| I-439 | 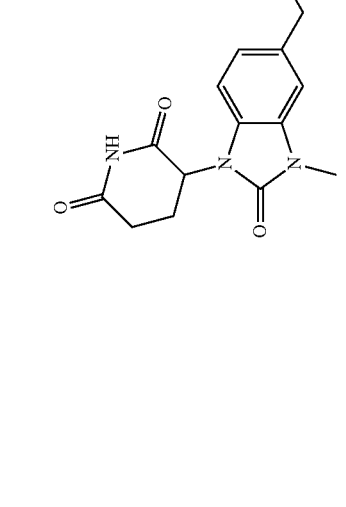 |
| I-440 | 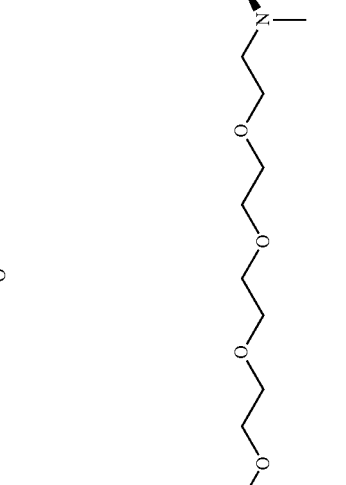 |

TABLE 1-continued
Exemplary Compounds
| I-# | Structure |
|---|---|
| I-441 | 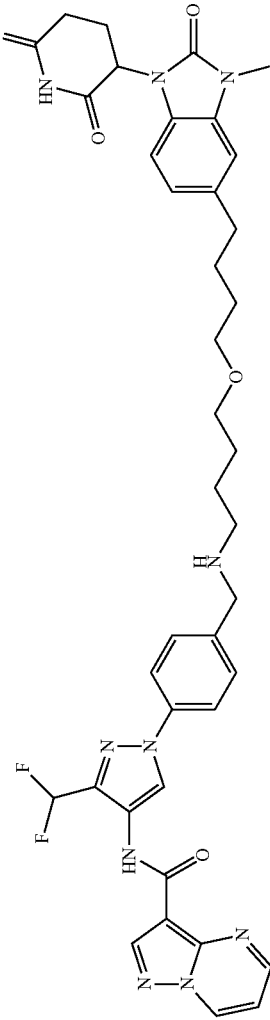 |
| I-442 | 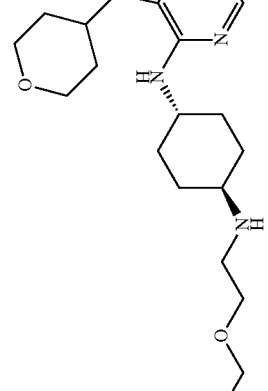 |

TABLE 1-continued
Exemplary Compounds
| I-# | Structure |
|---|---|
| I-444 | 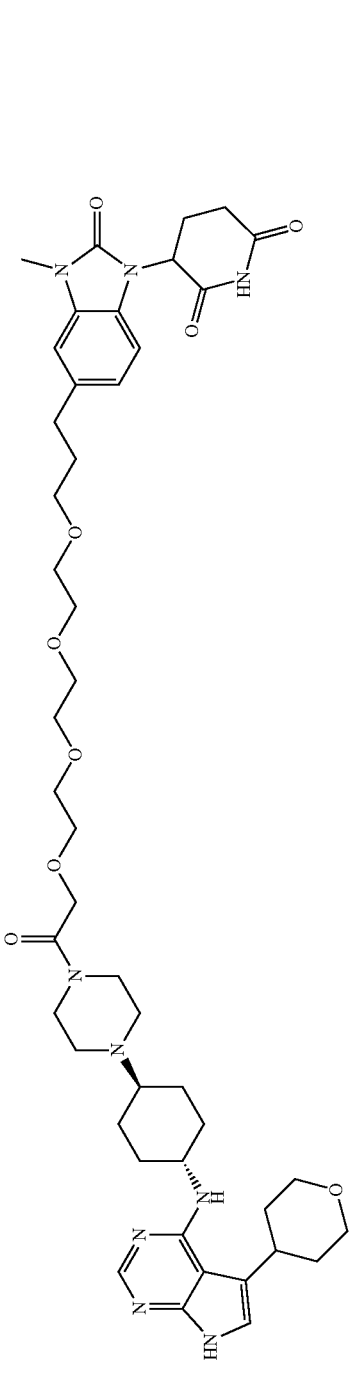 |
| I-445 | 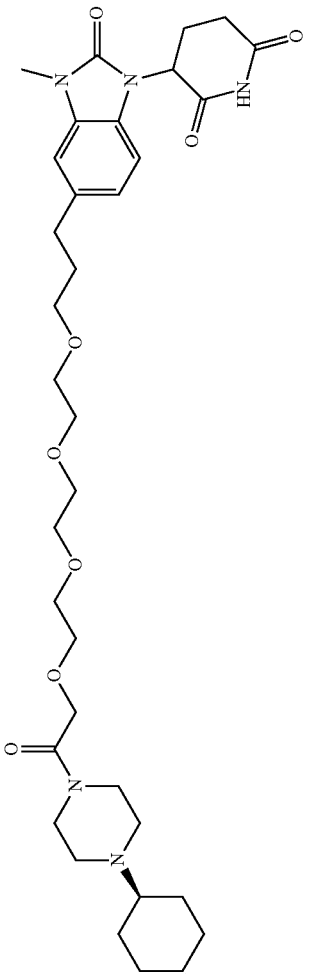 |

TABLE 1-continued
Exemplary Compounds
| I-# | Structure |
|---|---|
| I-446 | 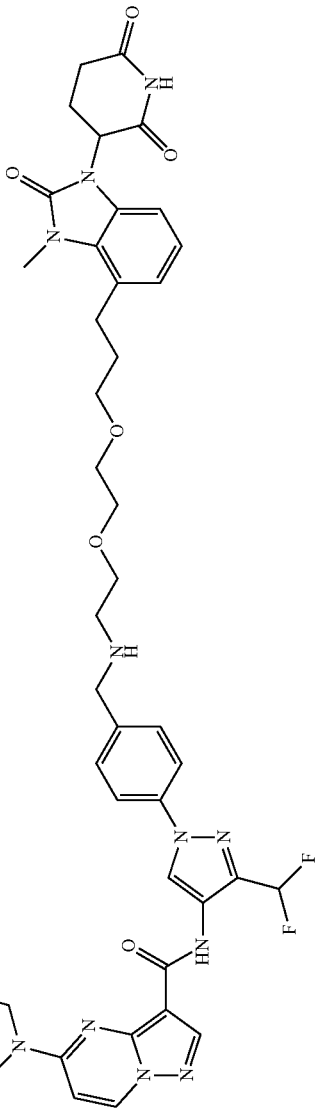 |
| I-447 | 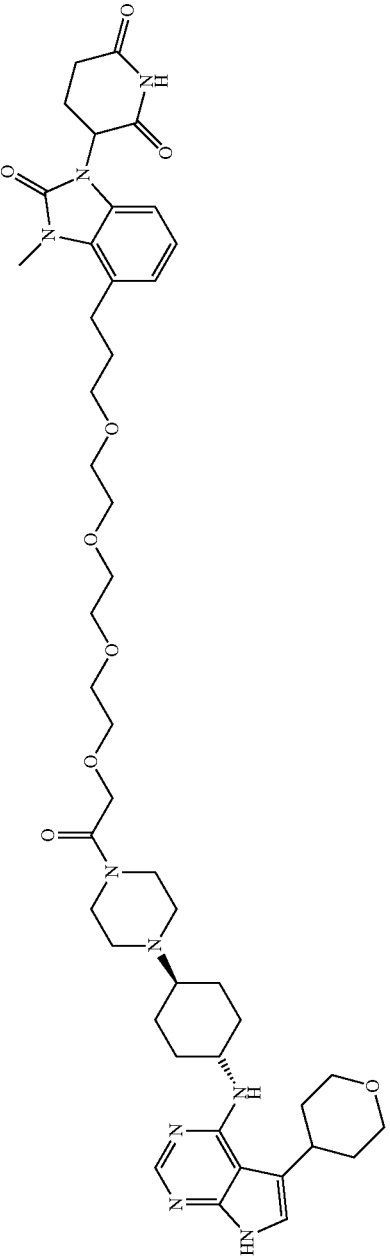 |

TABLE 1-continued
Exemplary Compounds
| I-# | Structure |
|---|---|
| I-448 | 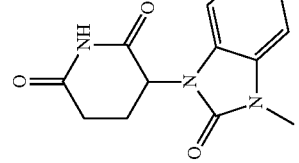 |

TABLE 1-continued
Exemplary Compounds
| I-# | Structure |
|---|---|
| I-449 | 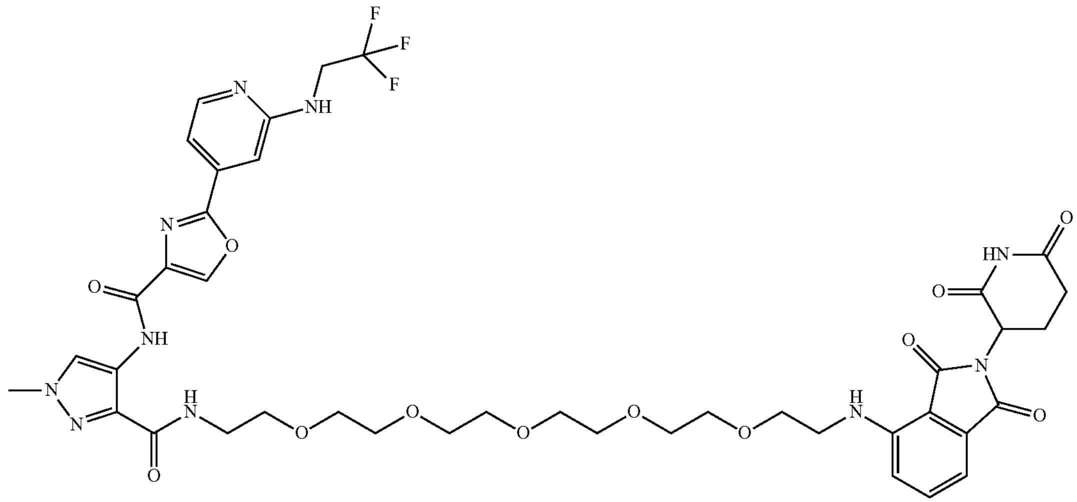 [SMILES: Cn1cc(NC(=O)c2coc(-c3ccnc(NCC(F)(F)F)c3)n2)c(C(=O)NCCOCCOCCOCCOCCOCCNc2cccc3c2C(=O)N(C2CCC(=O)NC2=O)C3=O)n1] |
| I-455 | 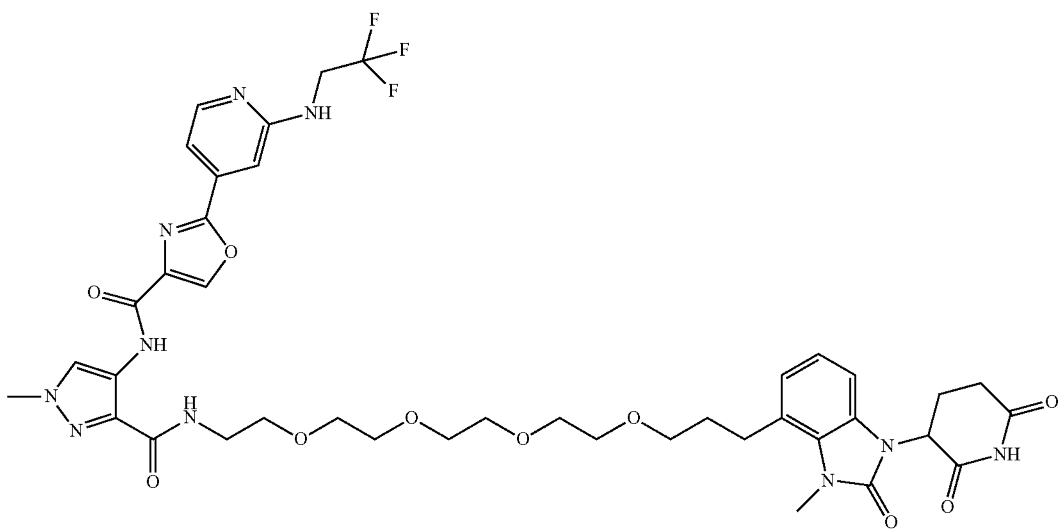 [SMILES: Cn1cc(NC(=O)c2coc(-c3ccnc(NCC(F)(F)F)c3)n2)c(C(=O)NCCOCCOCCOCCOCCCc2cccc3c2n(C)c(=O)n3C2CCC(=O)NC2=O)n1] |

TABLE 1-continued
Exemplary Compounds
| I-# | Structure |
|---|---|
| I-456 | 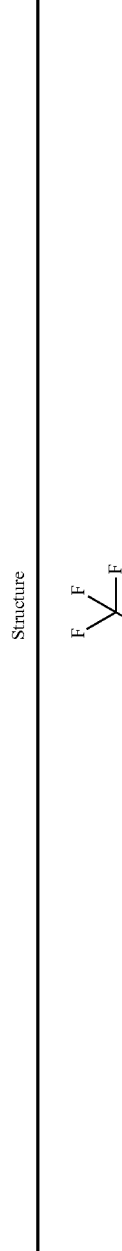 |

TABLE 1-continued

Exemplary Compounds

| I-# | Structure |
|---|---|
| I-457 | 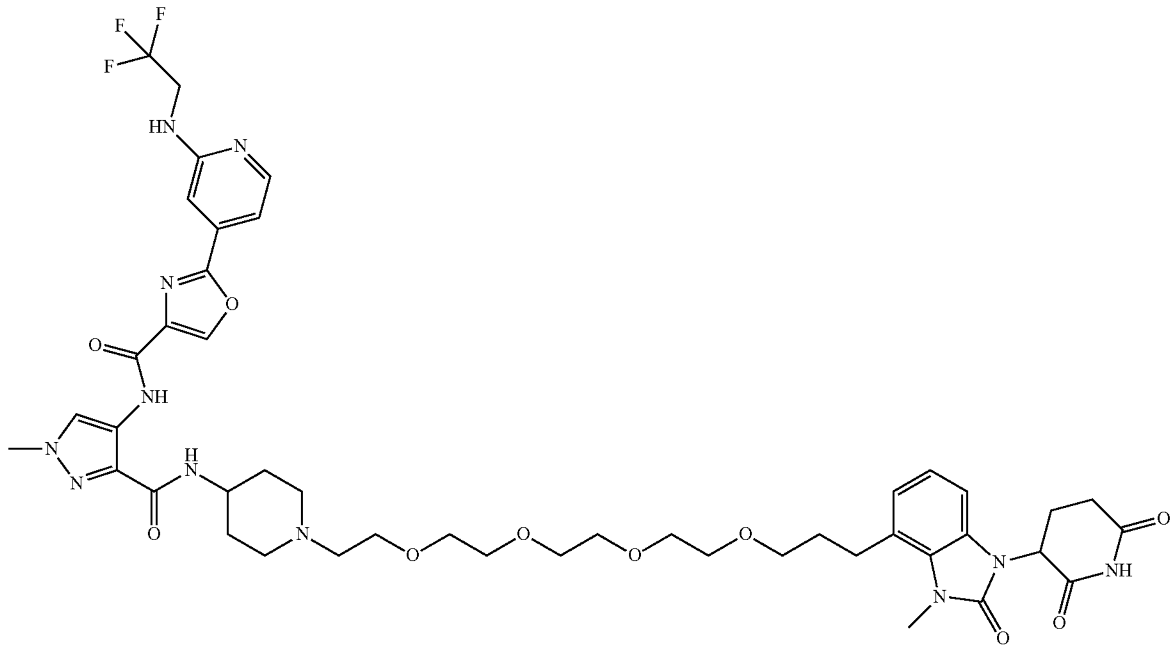 [SMILES: Cn1cc(NC(=O)c2coc(-c3ccnc(NCC(F)(F)F)c3)n2)c(C(=O)NC2CCN(CCOCCOCCOCCOCCCc3cccc4c3n(C)c(=O)n4C3CCC(=O)NC3=O)CC2)n1] |
| I-458 | 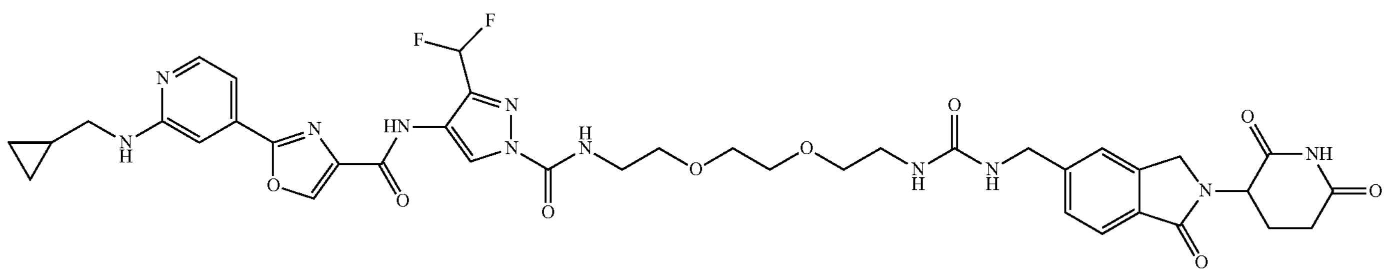 [SMILES: O=C1CCC(N2Cc3cc(CNC(=O)NCCOCCOCCNC(=O)n4cc(NC(=O)c5coc(-c6ccnc(NCC7CC7)c6)n5)c(C(F)F)n4)ccc3C2=O)C(=O)N1] |

TABLE 1-continued
Exemplary Compounds
| I-# | Structure |
|---|---|
| I-459 | 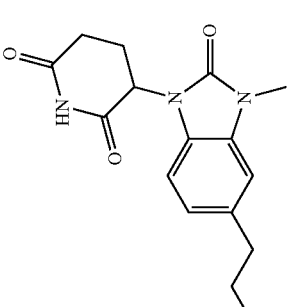 |
| I-460 | 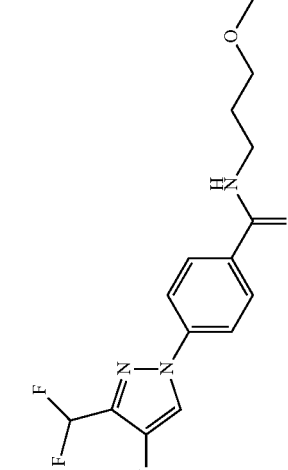 |
| I-461 | 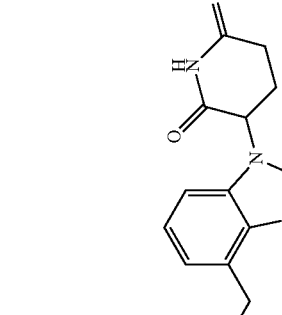 |

TABLE 1-continued
Exemplary Compounds
| I-# | Structure |
|---|---|
| I-462 | 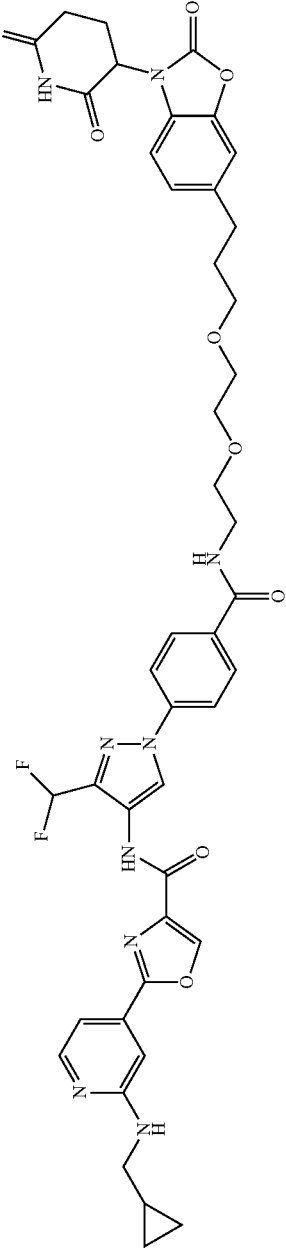 |
| I-463 | 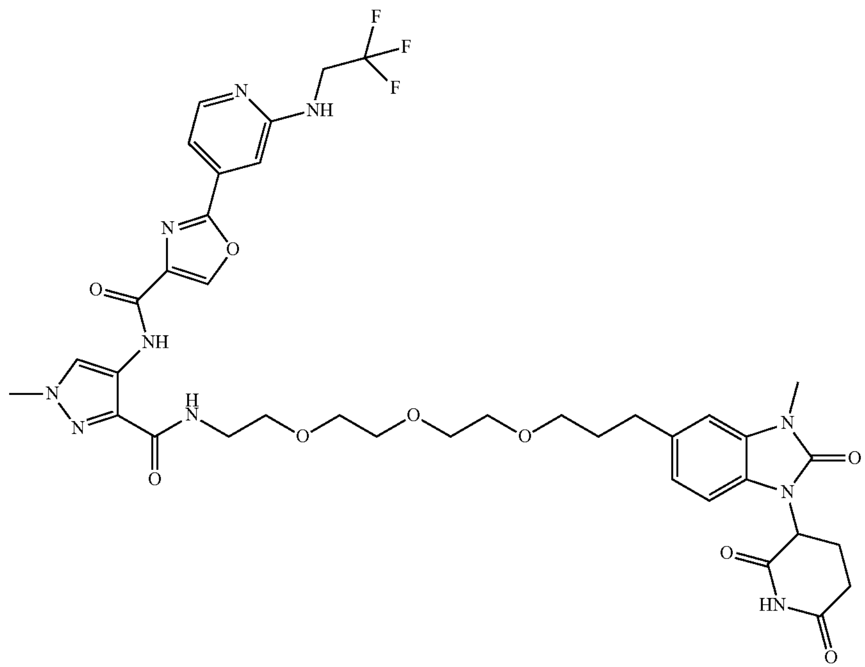 [SMILES: Cn1cc(NC(=O)c2coc(-c3ccnc(NCC(F)(F)F)c3)n2)c(C(=O)NCCOCCOCCOCCCc2ccc3c(c2)n(C)c(=O)n3C2CCC(=O)NC2=O)n1] |

TABLE 1-continued
Exemplary Compounds
| I-# | Structure |
|---|---|
| I-464 | 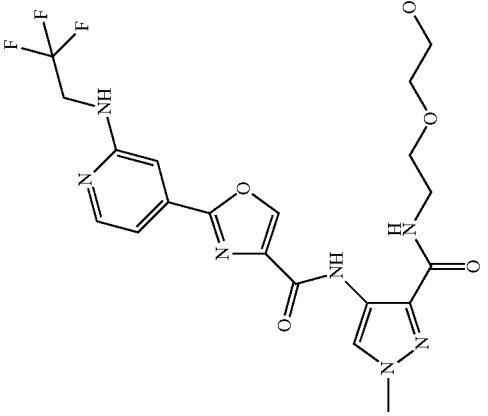 |
| I-465 | 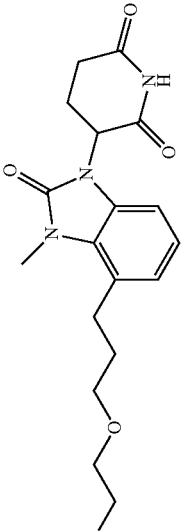 |

TABLE 1-continued
Exemplary Compounds
| I-# | Structure |
|---|---|
| I-466 | 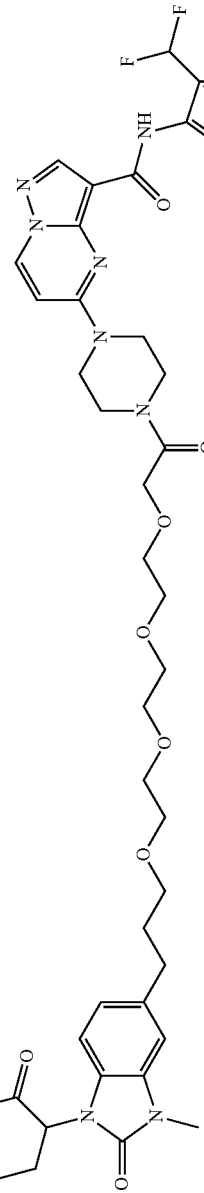 |
| I-467 | 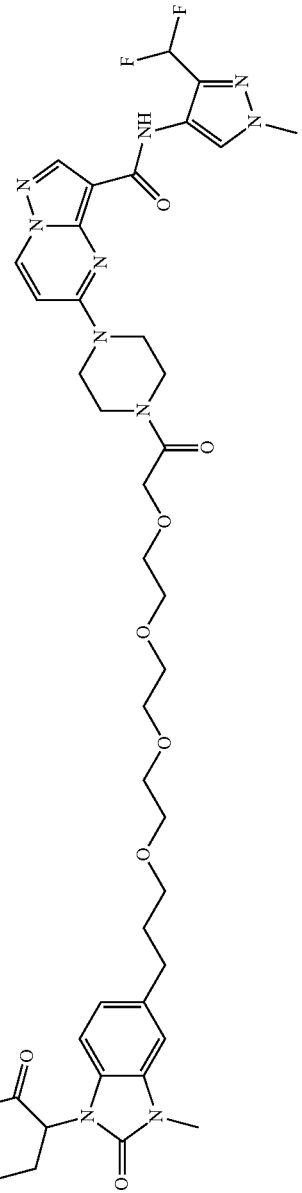 |

TABLE 1-continued
Exemplary Compounds
| I-# | Structure |
|---|---|
| I-468 | 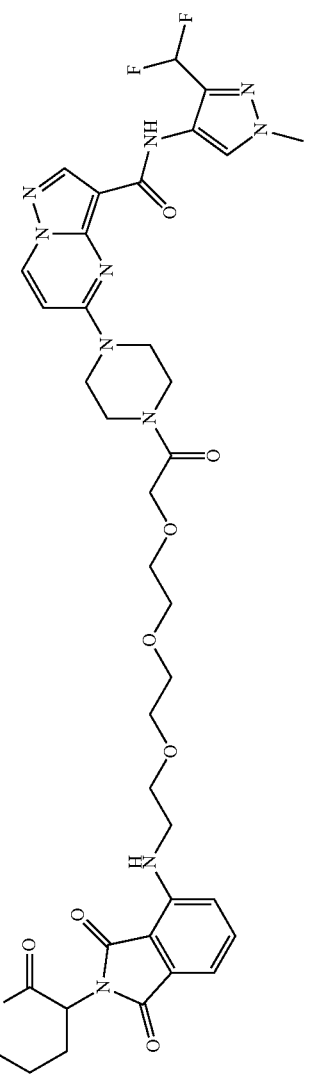 |
| I-469 | 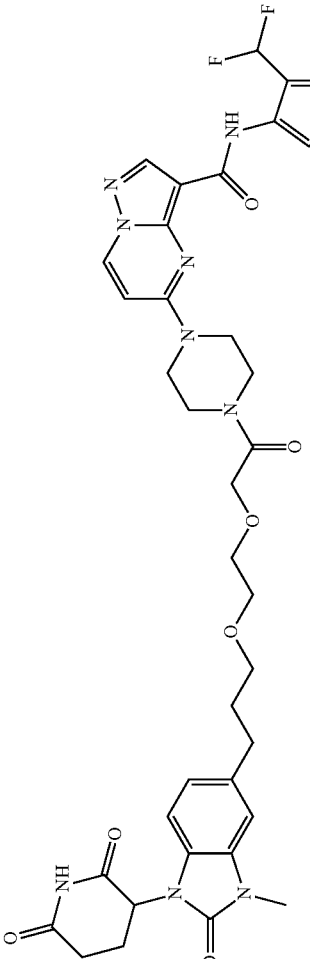 |

TABLE 1-continued
Exemplary Compounds
| I-# | Structure |
|---|---|
| I-470 | 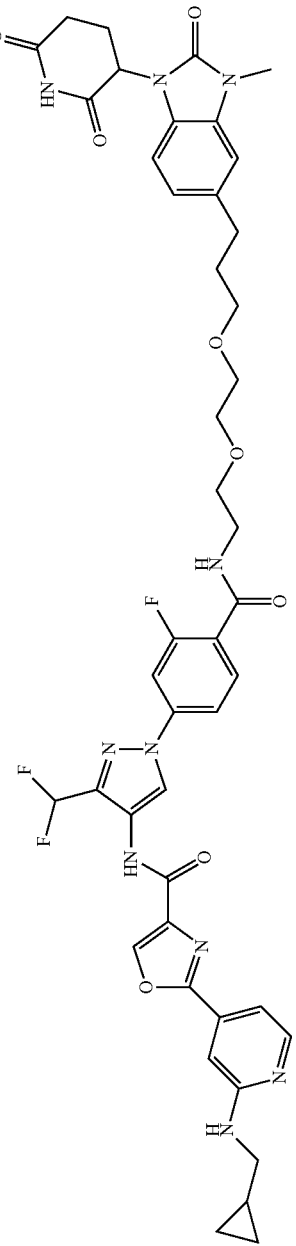 |
| I-471 | 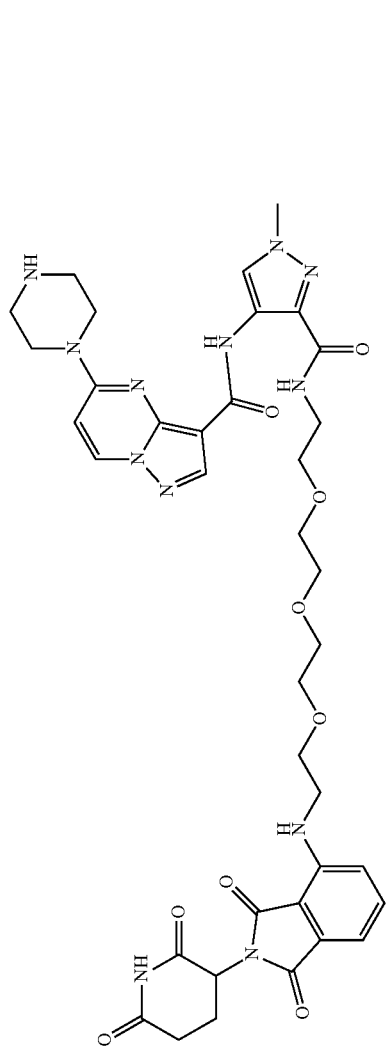 |

TABLE 1-continued

Exemplary Compounds

| I-# | Structure |
|---|---|
| I-472 | 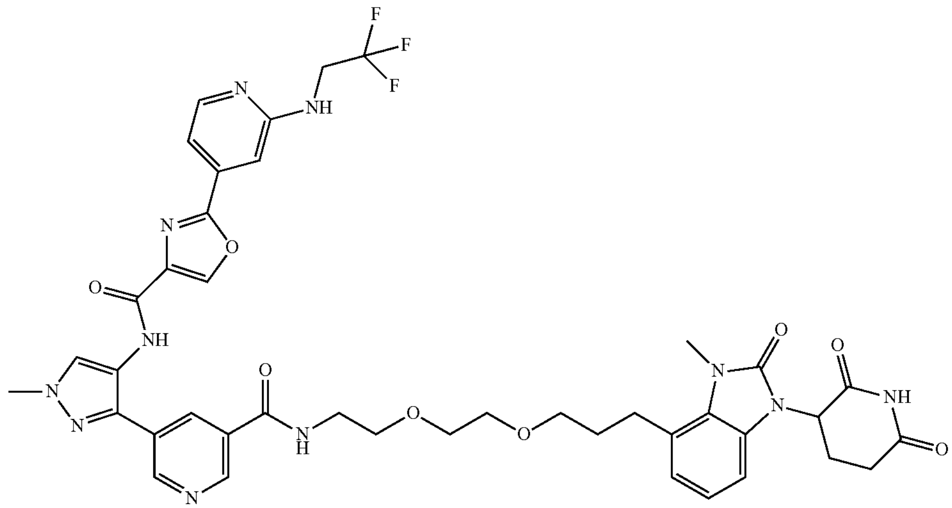 [SMILES: Cn1cc(NC(=O)c2coc(-c3ccnc(NCC(F)(F)F)c3)n2)c(-c2cncc(C(=O)NCCOCCOCCCc3cccc4c3n(C)c(=O)n4C3CCC(=O)NC3=O)c2)n1] |
| I-473 | 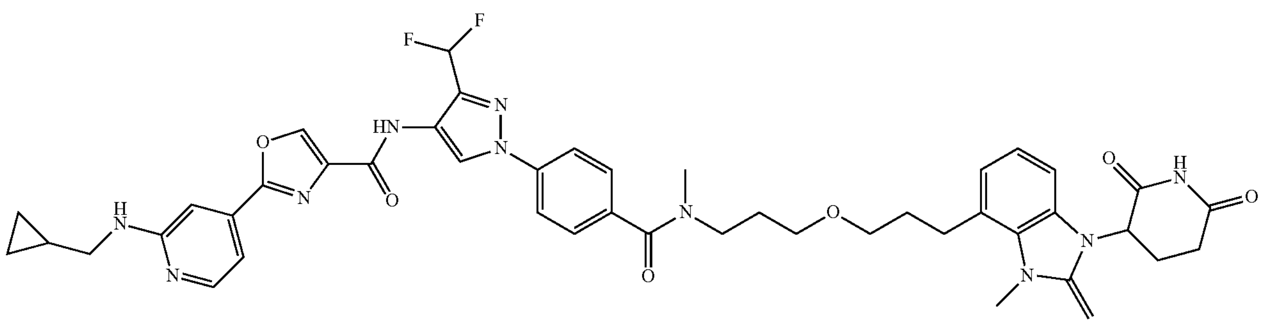 [SMILES: C=C1N(C)c2c(CCCOCCCN(C)C(=O)c3ccc(-n4cc(NC(=O)c5coc(-c6ccnc(NCC7CC7)c6)n5)c(C(F)F)n4)cc3)cccc2N1C1CCC(=O)NC1=O] |

TABLE 1-continued
Exemplary Compounds
| I-# | Structure |
|---|---|
| I-475 | 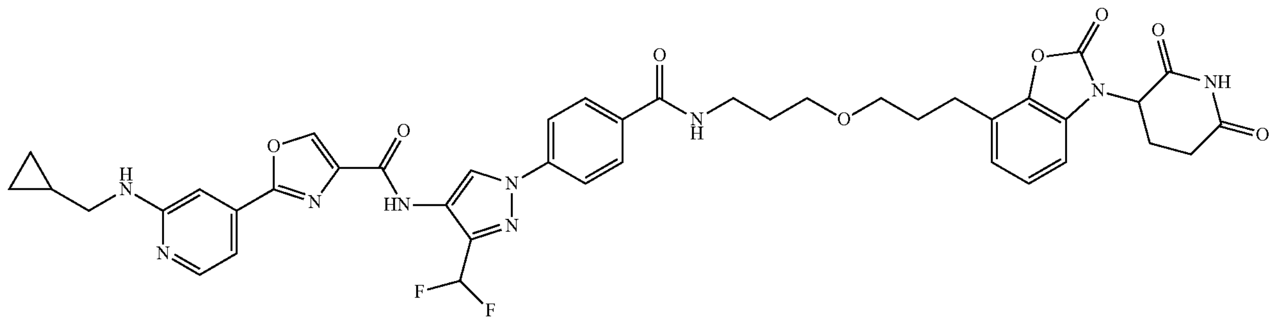 [SMILES: O=C1CCC(n2c(=O)oc3c(CCCOCCCNC(=O)c4ccc(-n5cc(NC(=O)c6coc(-c7ccnc(NCC8CC8)c7)n6)c(C(F)F)n5)cc4)cccc32)C(=O)N1] |
| I-476 | 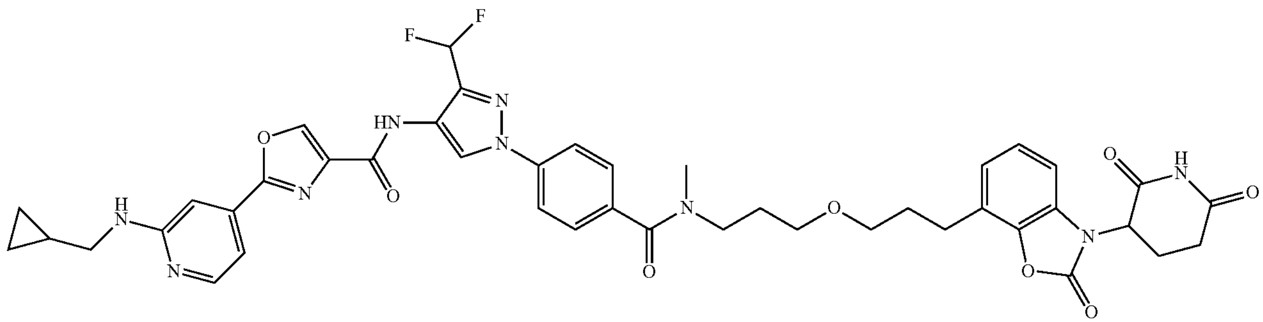 [SMILES: CN(CCCOCCCc1cccc2c1oc(=O)n2C1CCC(=O)NC1=O)C(=O)c1ccc(-n2cc(NC(=O)c3coc(-c4ccnc(NCC5CC5)c4)n3)c(C(F)F)n2)cc1] |
| I-477 | 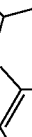 |

TABLE 1-continued
Exemplary Compounds
| I-# | Structure |
|---|---|
| I-478 | 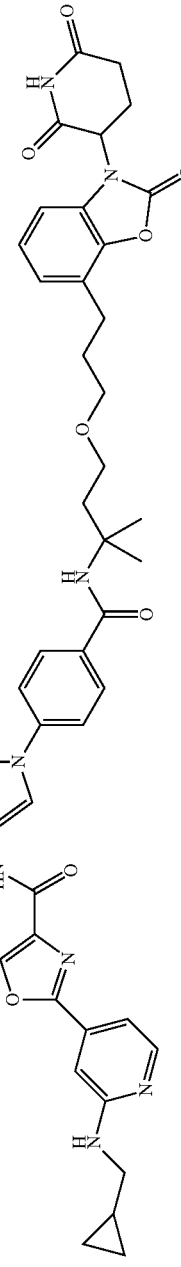 |
| I-479 | 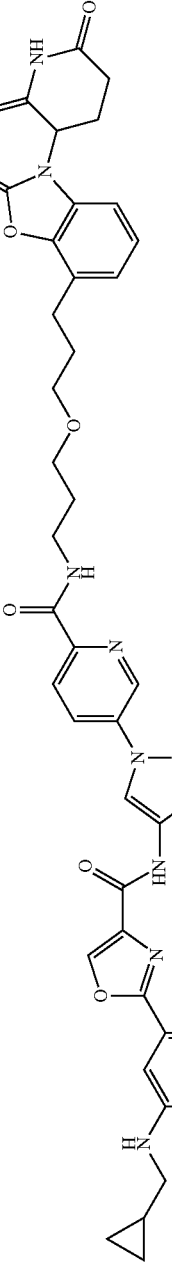 |

TABLE 1-continued

Exemplary Compounds

| I-# | Structure |
|---|---|
| I-481 | 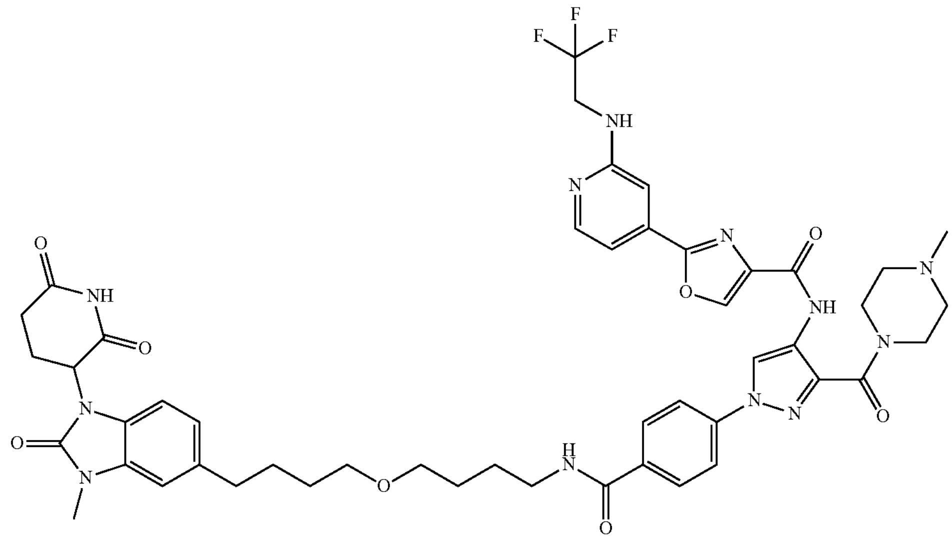 [SMILES: CN1CCN(C(=O)c2nn(-c3ccc(C(=O)NCCCCOCCCCc4ccc5c(c4)n(C)c(=O)n5C4CCC(=O)NC4=O)cc3)cc2NC(=O)c2coc(-c3ccnc(NCC(F)(F)F)c3)n2)CC1] |

TABLE 1-continued
Exemplary Compounds
| I-# | Structure |
|---|---|
| I-482 | 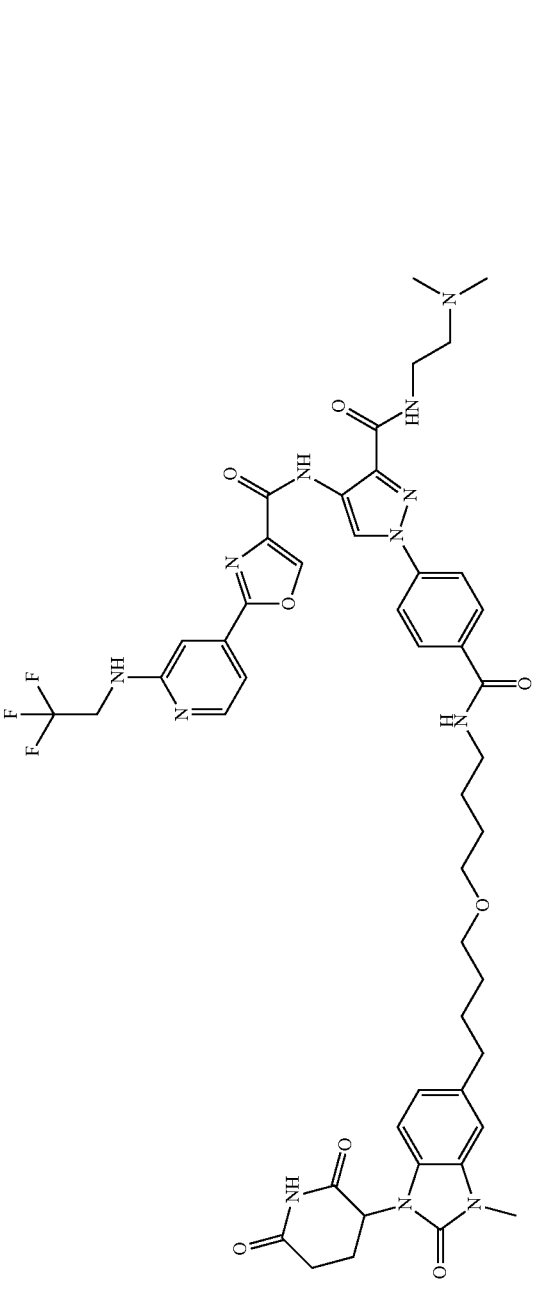 |
| I-483 | 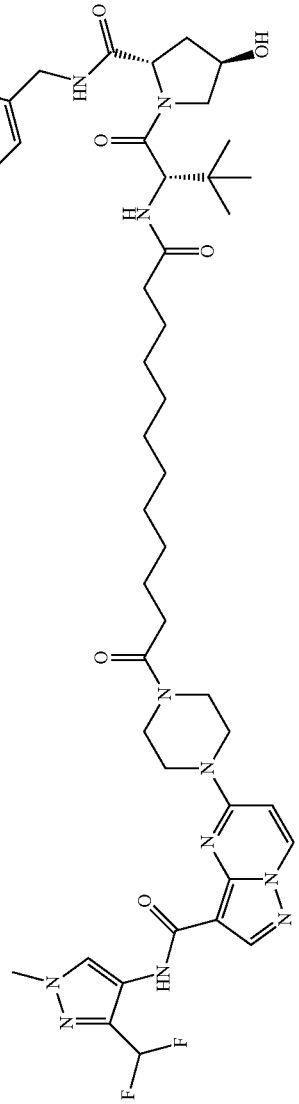 |

TABLE 1-continued

Exemplary Compounds

| I-# | Structure |
|---|---|
| I-484 | 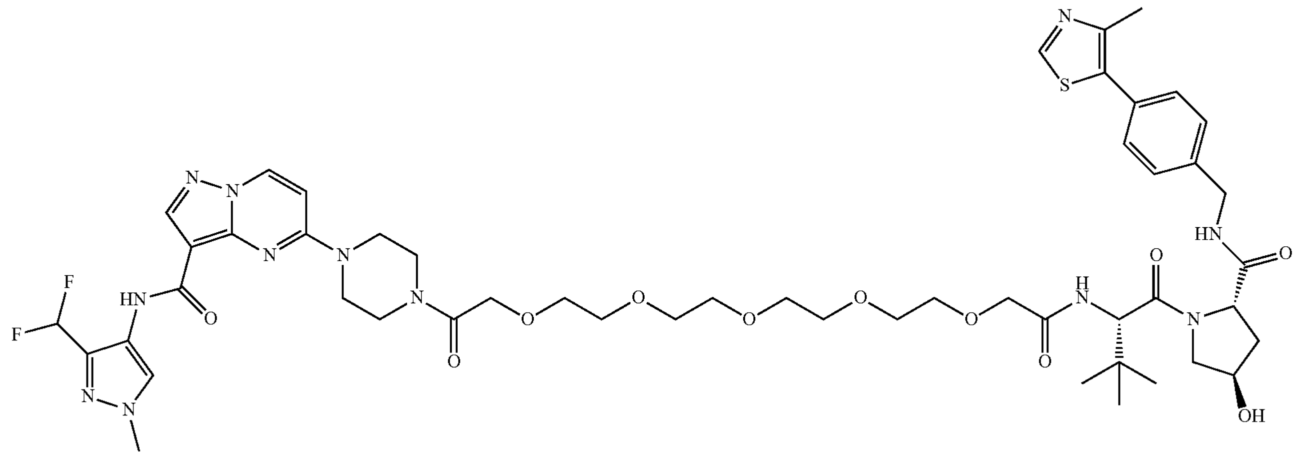 [SMILES: Cc1ncsc1-c1ccc(CNC(=O)[C@@H]2C[C@@H](O)CN2C(=O)[C@@H](NC(=O)COCCOCCOCCOCCOCC(=O)N2CCN(c3ccn4ncc(C(=O)Nc5cn(C)nc5C(F)F)c4n3)CC2)C(C)(C)C)cc1] |
| I-485 | 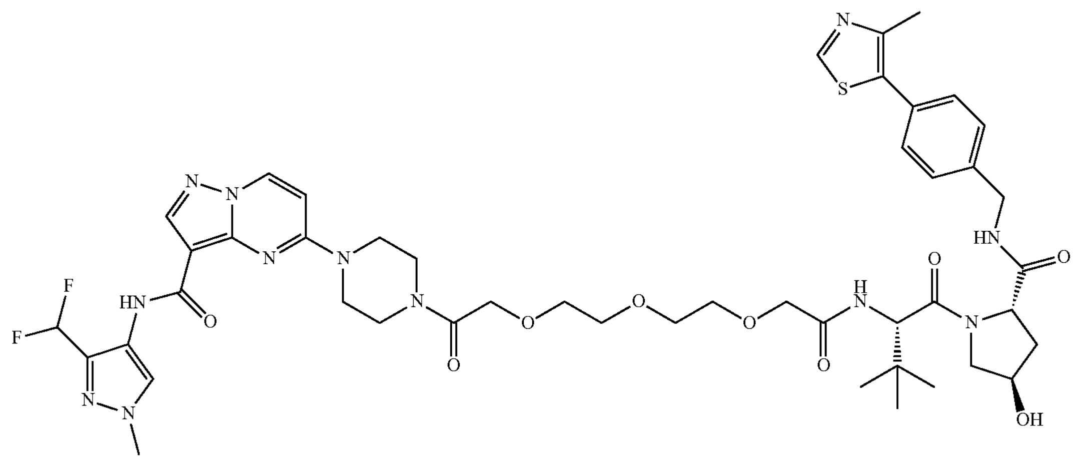 [SMILES: Cc1ncsc1-c1ccc(CNC(=O)[C@@H]2C[C@@H](O)CN2C(=O)[C@@H](NC(=O)COCCOCCOCC(=O)N2CCN(c3ccn4ncc(C(=O)Nc5cn(C)nc5C(F)F)c4n3)CC2)C(C)(C)C)cc1] |

TABLE 1-continued
Exemplary Compounds
| I-# | Structure |
|---|---|
| I-487 | 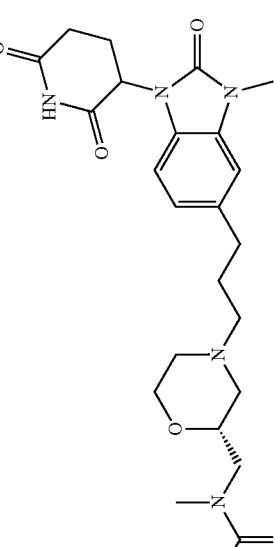 |
| I-488 | 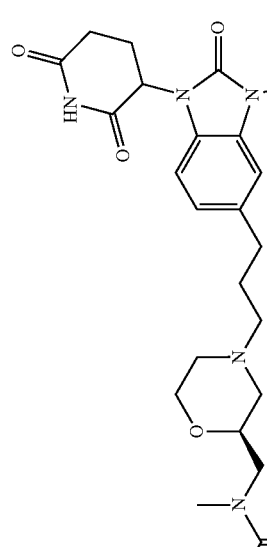 |
| I-489 | 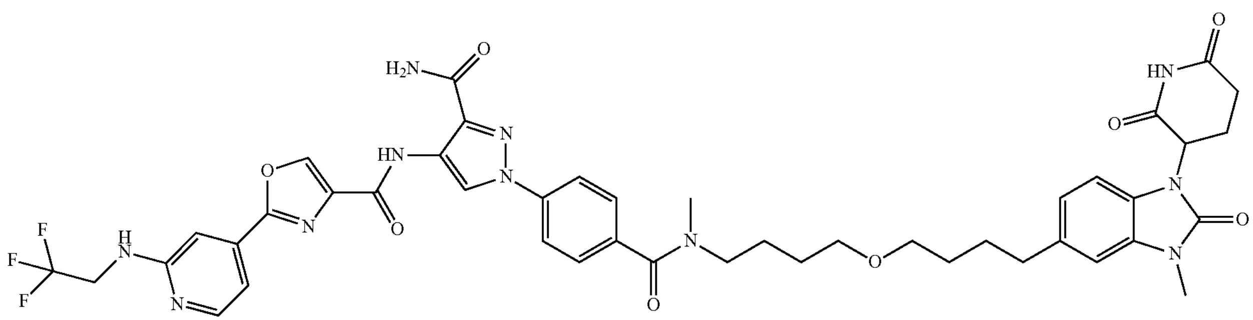 [SMILES: CN(CCCCOCCCCc1ccc2c(c1)n(C)c(=O)n2C1CCC(=O)NC1=O)C(=O)c1ccc(-n2cc(NC(=O)c3coc(-c4ccnc(NCC(F)(F)F)c4)n3)c(C(N)=O)n2)cc1] |

TABLE 1-continued
Exemplary Compounds
| I-# | Structure |
|---|---|
| I-490 | 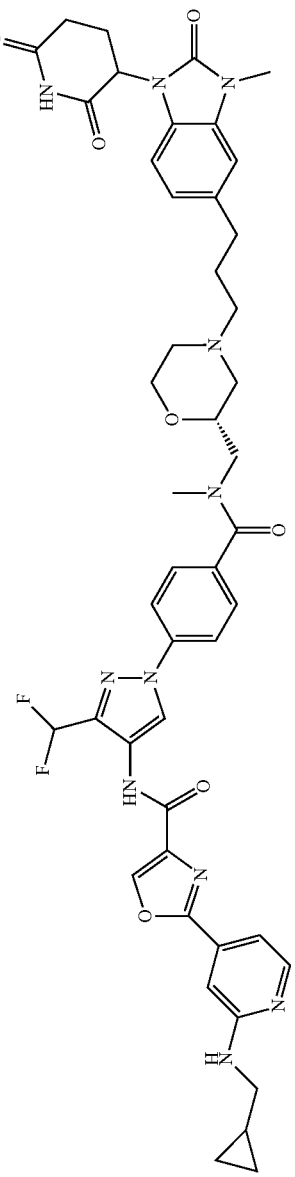 |
| I-491 | 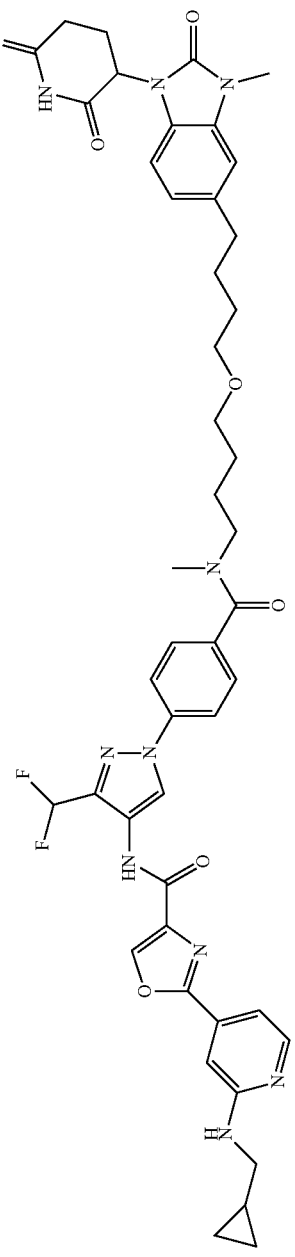 |
| I-494 | 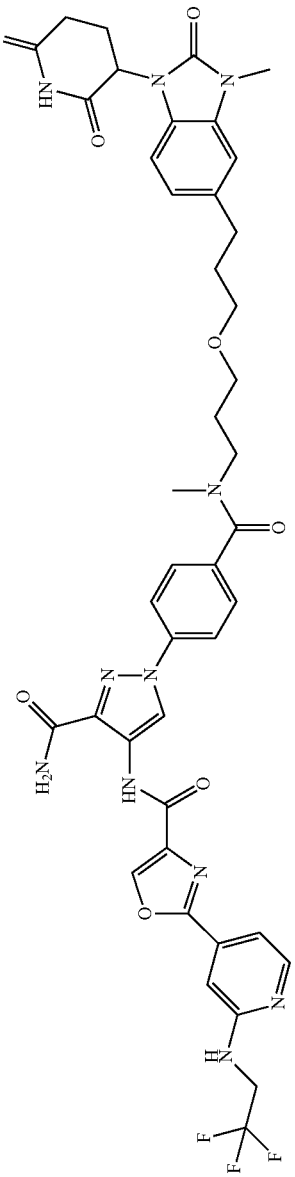 |

TABLE 1-continued
Exemplary Compounds
| I-# | Structure |
|---|---|
| I-495 | 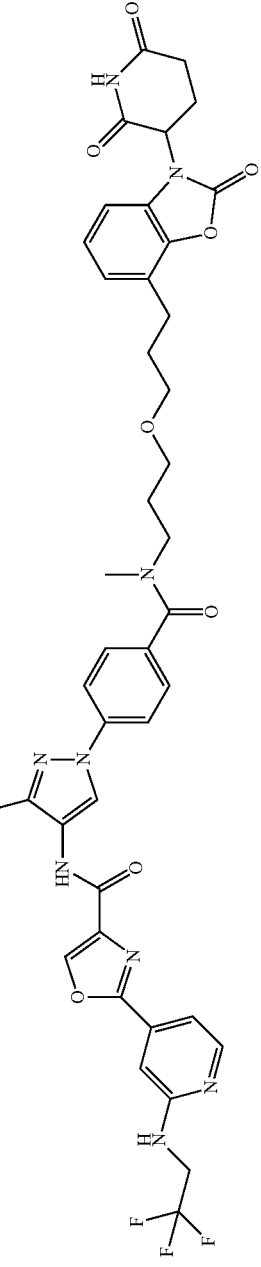 |
| I-504 | 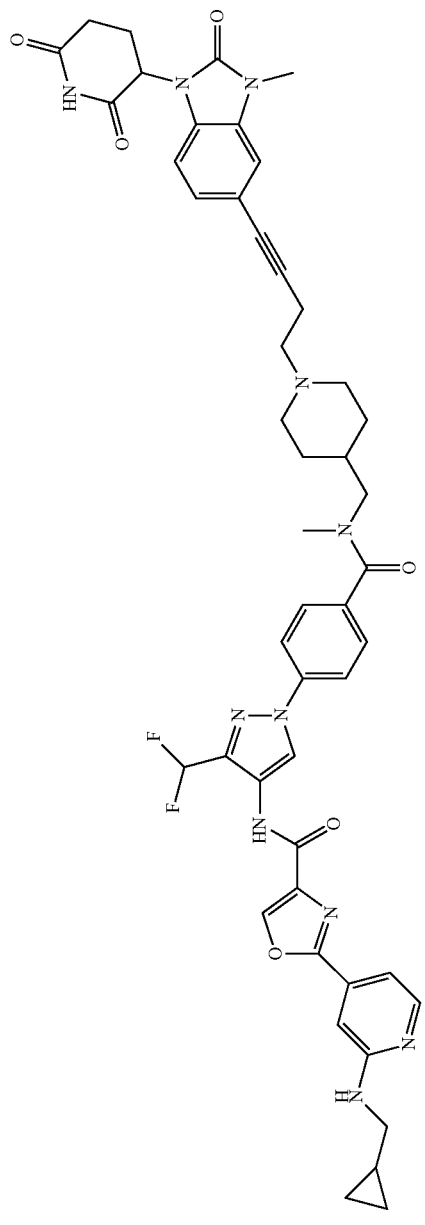 |

TABLE 1-continued
Exemplary Compounds
| I-# | Structure |
|---|---|
| I-506 | 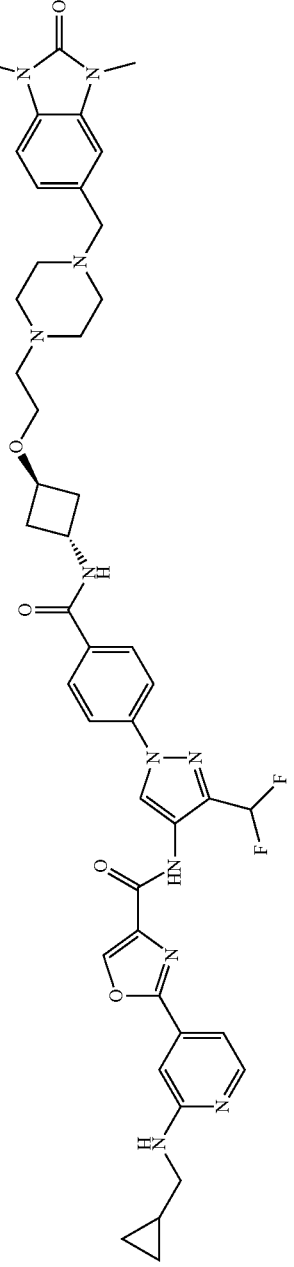 |
| I-508 | 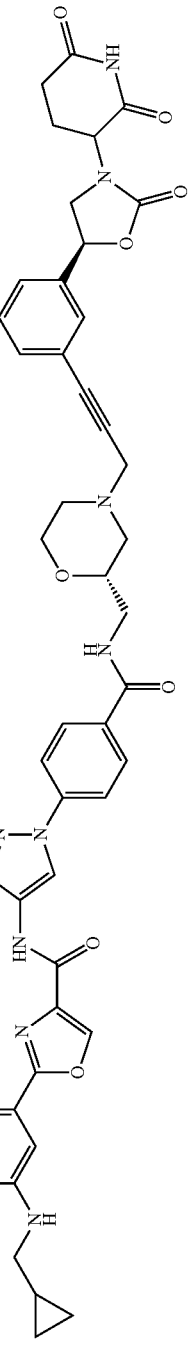 |

TABLE 1-continued
Exemplary Compounds
| I-# | Structure |
|---|---|
| I-509 | 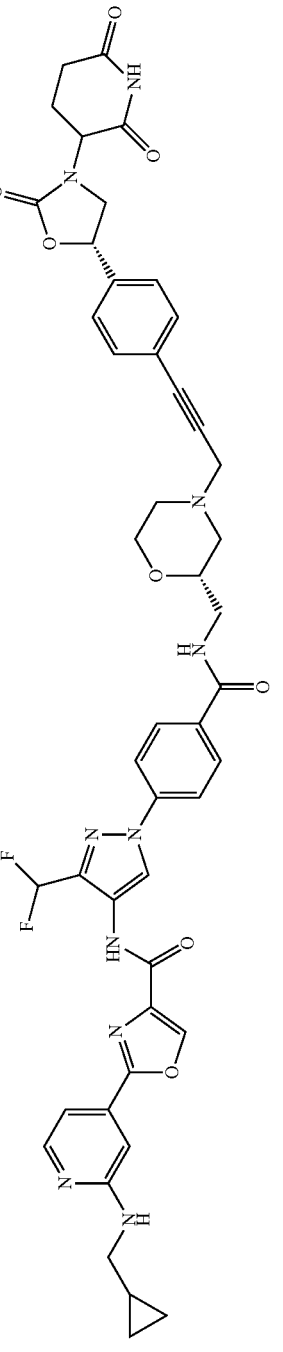 |
| I-513 | 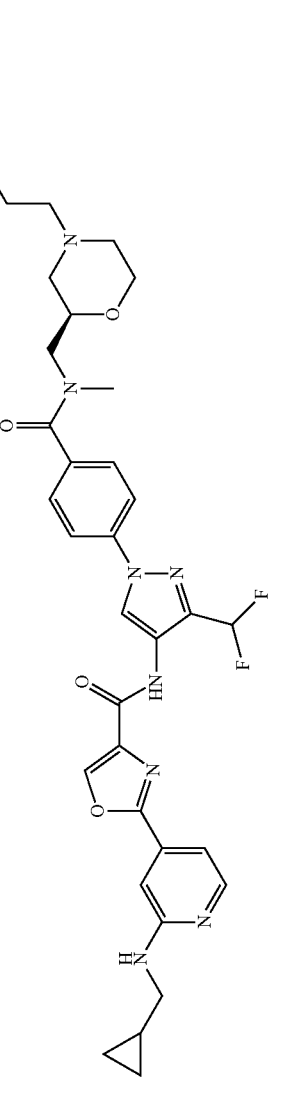 |

TABLE 1-continued
Exemplary Compounds
| I-# | Structure |
|---|---|
| I-514 | 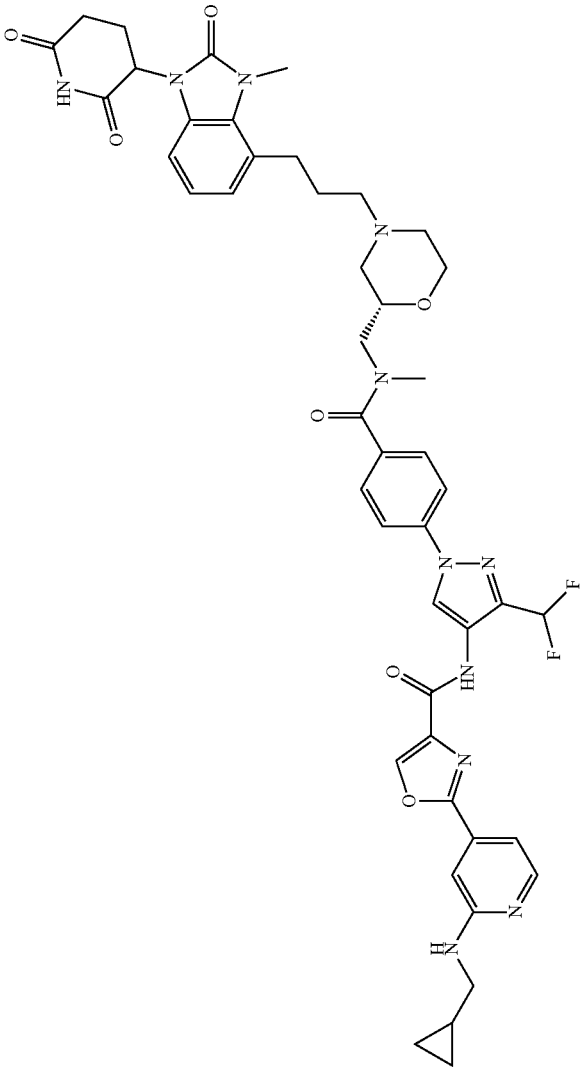 |
| I-515 | 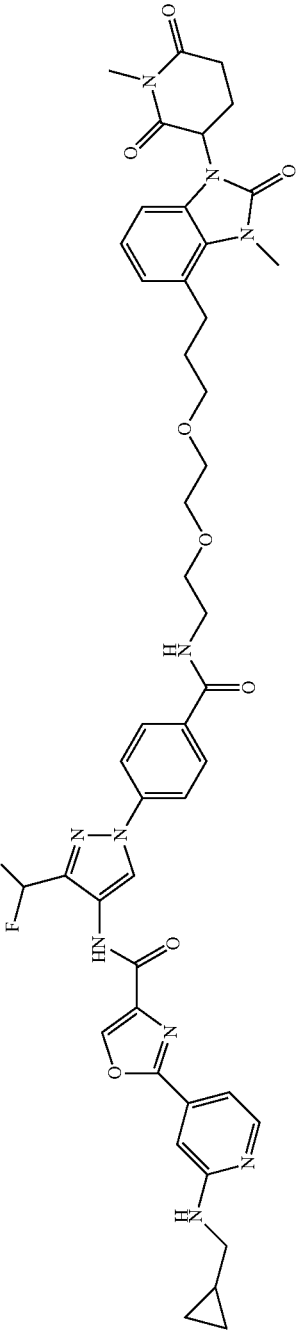 |

TABLE 1-continued
Exemplary Compounds
| I-# | Structure |
|---|---|
| I-517 | 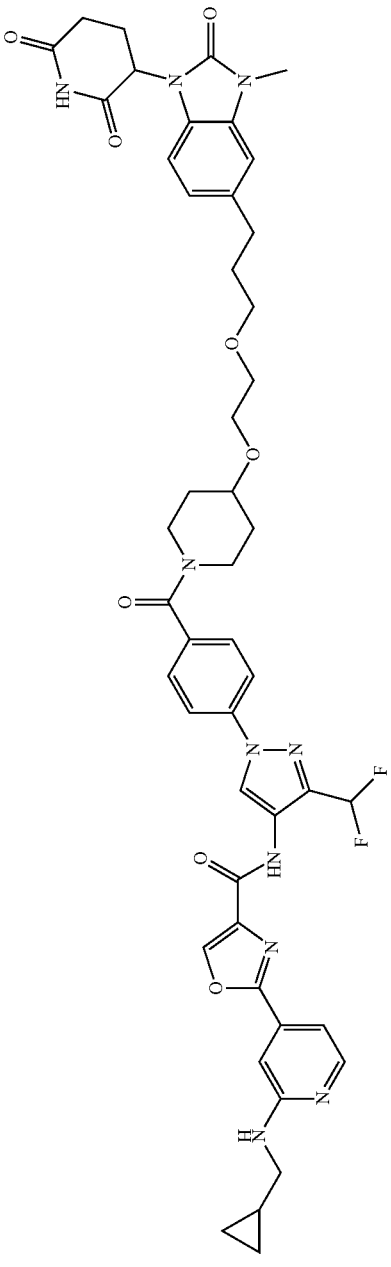 |
| I-522 | 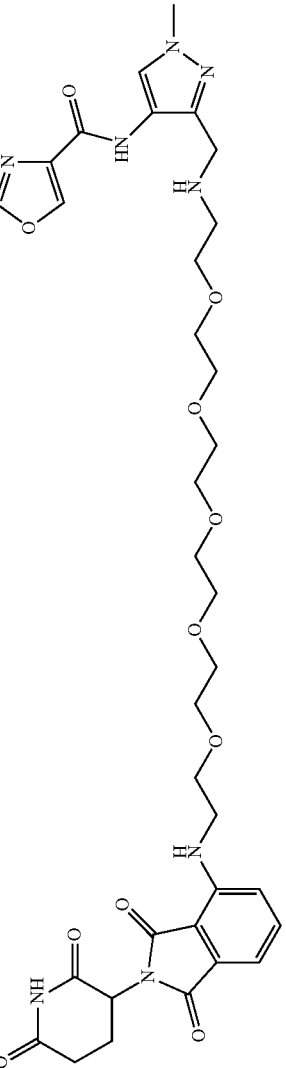 |

TABLE 1-continued
Exemplary Compounds
| I-# | Structure |
|---|---|
| I-523 | 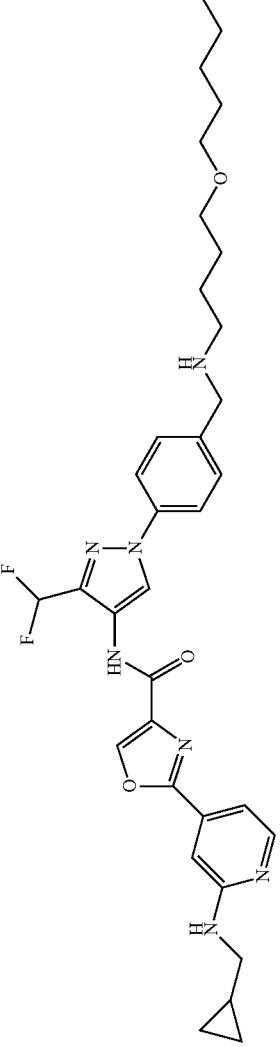 |
| I-524 | 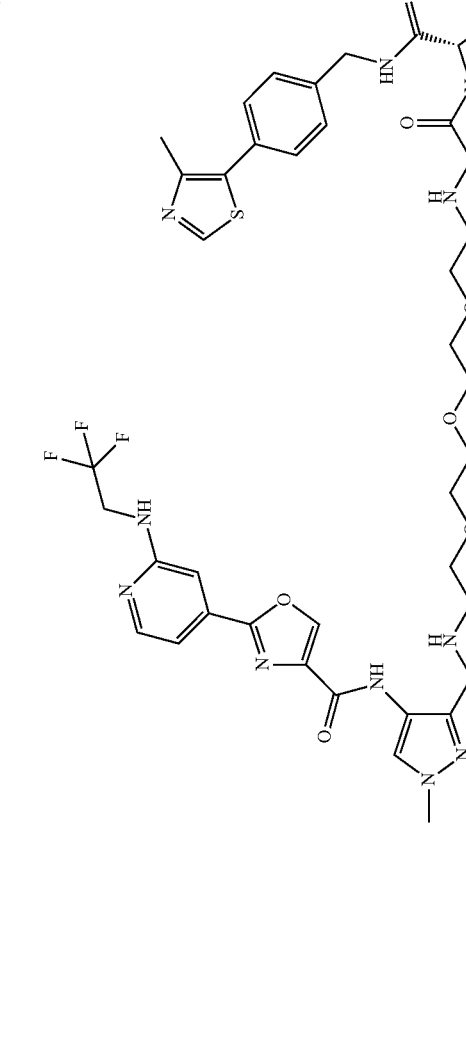 |

TABLE 1-continued

Exemplary Compounds

| I-# | Structure |
|---|---|
| I-525 | 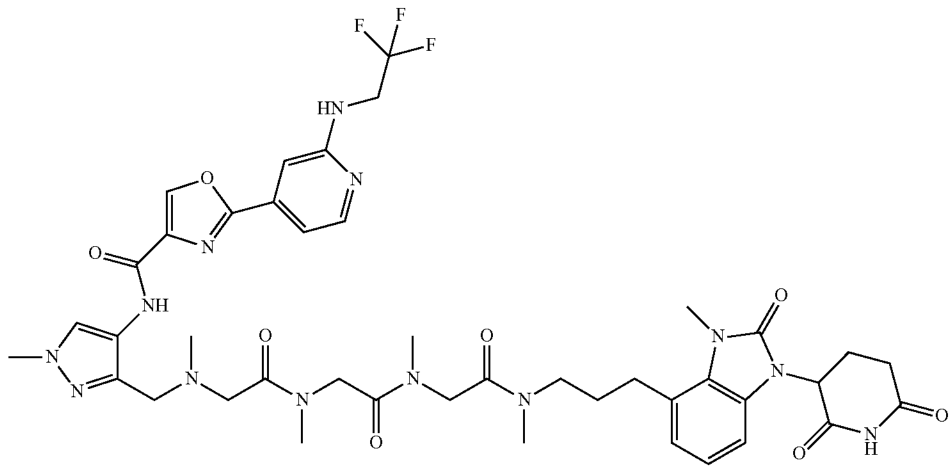 [SMILES: CN(CC(=O)N(C)CC(=O)N(C)CC(=O)N(C)CCCc1cccc2c1n(C)c(=O)n2C1CCC(=O)NC1=O)Cc1nn(C)cc1NC(=O)c1coc(-c2ccnc(NCC(F)(F)F)c2)n1] |
| I-526 | 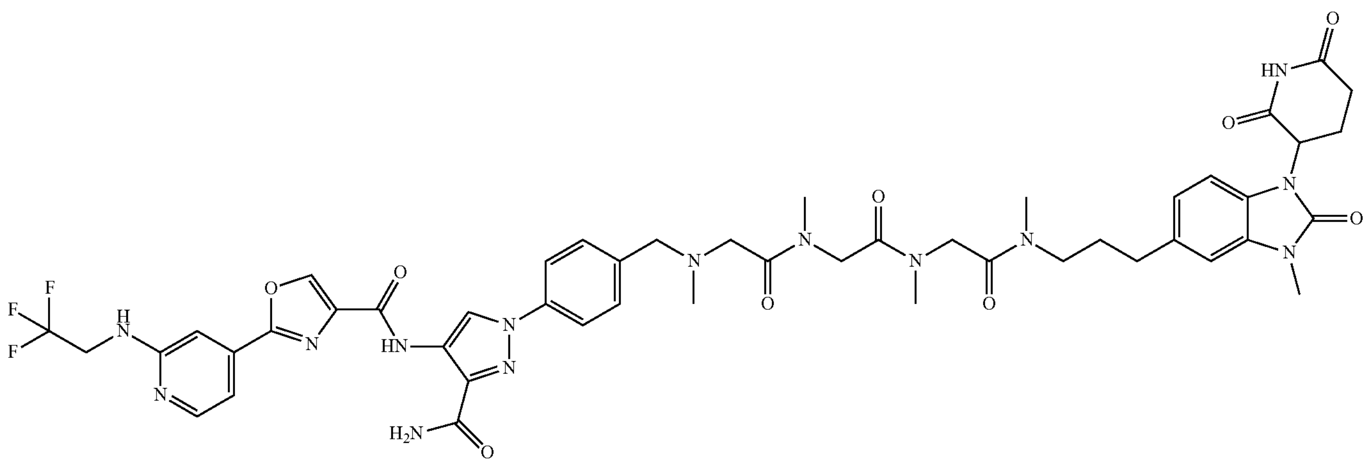 [SMILES: CN(CC(=O)N(C)CC(=O)N(C)CC(=O)N(C)CCCc1ccc2c(c1)n(C)c(=O)n2C1CCC(=O)NC1=O)Cc1ccc(-n2cc(NC(=O)c3coc(-c4ccnc(NCC(F)(F)F)c4)n3)c(C(N)=O)n2)cc1] |

TABLE 1-continued
Exemplary Compounds
| I-# | Structure |
|---|---|
| I-527 | 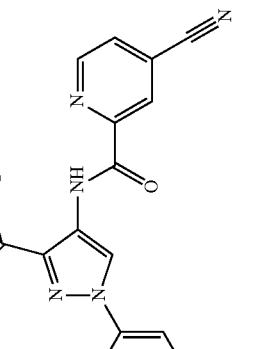 |
| I-528 | 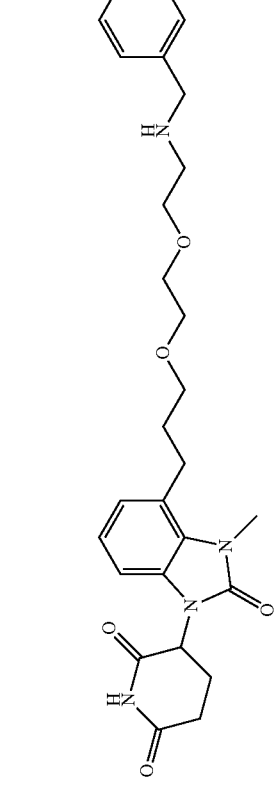 |

TABLE 1-continued
Exemplary Compounds
| I-# | Structure |
|---|---|
| I-529 | 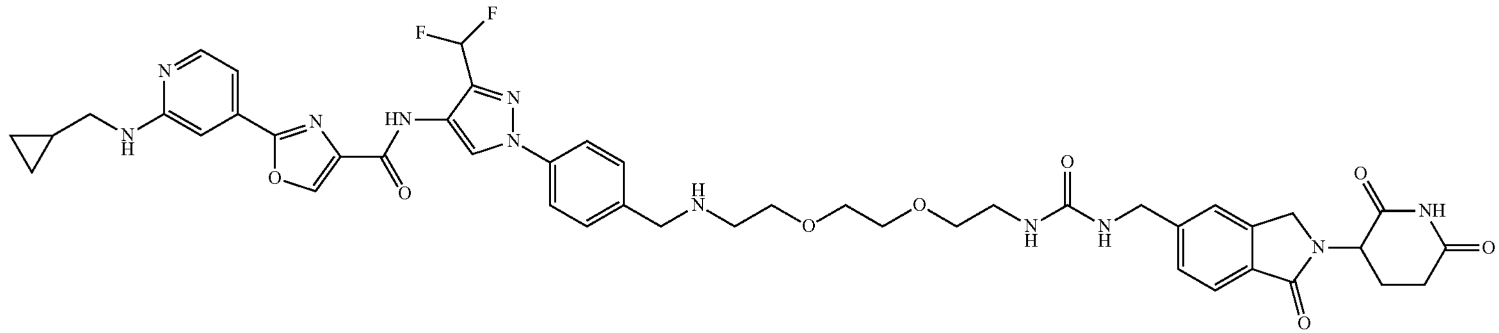 [SMILES: O=C1CCC(N2Cc3cc(CNC(=O)NCCOCCOCCNCc4ccc(-n5cc(NC(=O)c6coc(-c7ccnc(NCC8CC8)c7)n6)c(C(F)F)n5)cc4)ccc3C2=O)C(=O)N1] |
| I-530 | 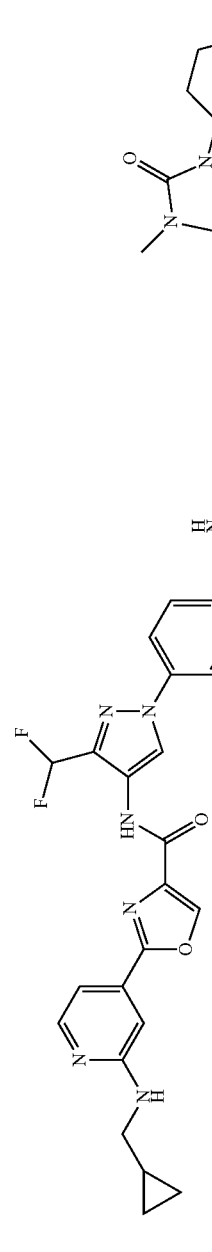 |

TABLE 1-continued
Exemplary Compounds
| I-# | Structure |
|---|---|
| I-531 | 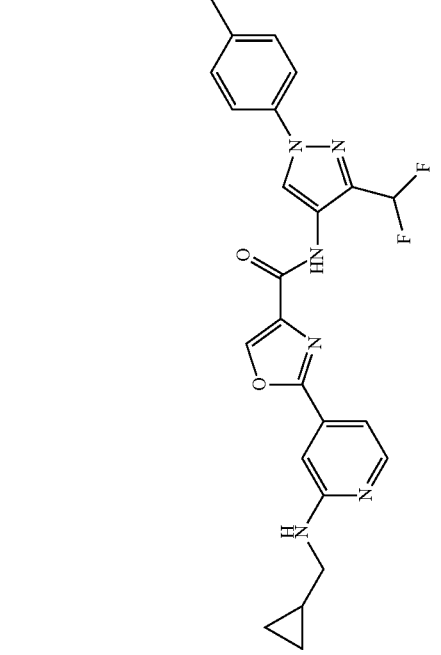 |
| I-532 | 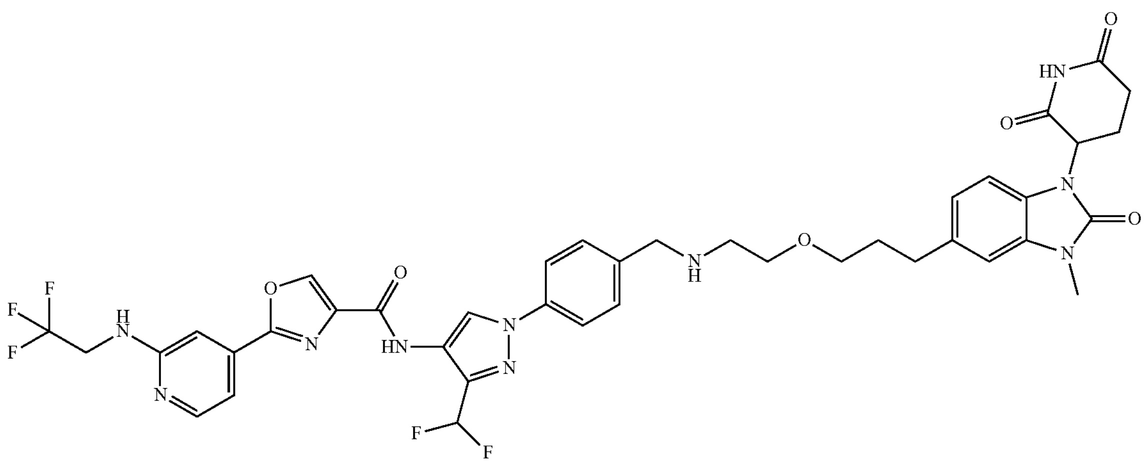 [SMILES: Cn1c(=O)n(C2CCC(=O)NC2=O)c2ccc(CCCOCCNCc3ccc(-n4cc(NC(=O)c5coc(-c6ccnc(NCC(F)(F)F)c6)n5)c(C(F)F)n4)cc3)cc21] |

TABLE 1-continued

Exemplary Compounds

| I-# | Structure |
|---|---|
| I-533 | 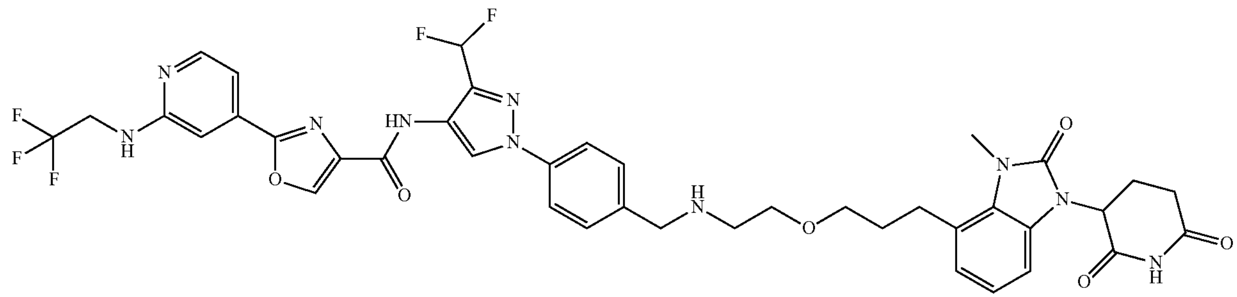 [SMILES: Cn1c(=O)n(C2CCC(=O)NC2=O)c2cccc(CCCOCCNCc3ccc(-n4cc(NC(=O)c5coc(-c6ccnc(NCC(F)(F)F)c6)n5)c(C(F)F)n4)cc3)c21] |
| I-534 | 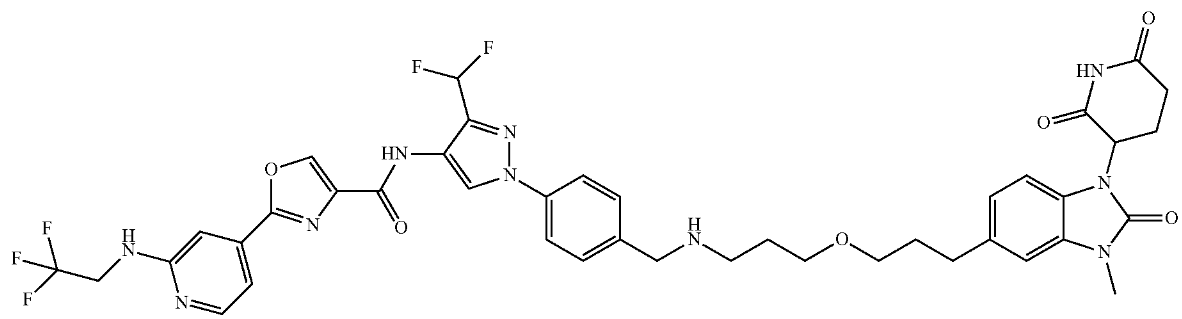 [SMILES: Cn1c(=O)n(C2CCC(=O)NC2=O)c2ccc(CCCOCCCNCc3ccc(-n4cc(NC(=O)c5coc(-c6ccnc(NCC(F)(F)F)c6)n5)c(C(F)F)n4)cc3)cc21] |
| I-535 | 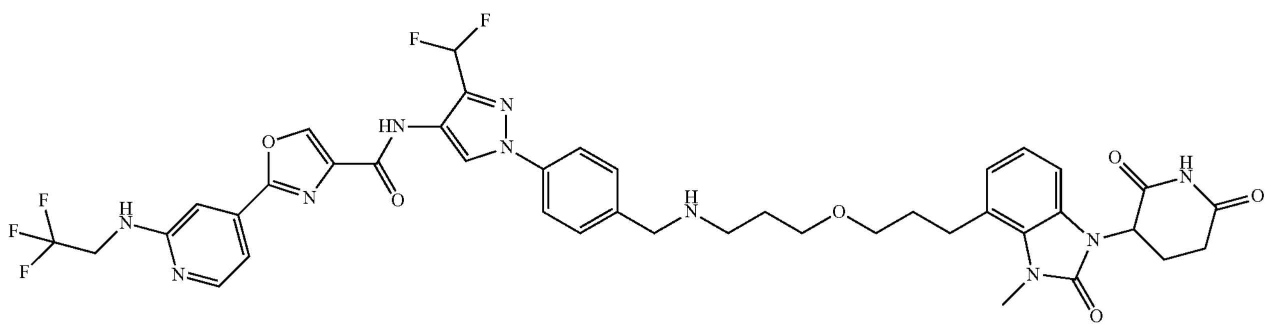 [SMILES: Cn1c(=O)n(C2CCC(=O)NC2=O)c2cccc(CCCOCCCNCc3ccc(-n4cc(NC(=O)c5coc(-c6ccnc(NCC(F)(F)F)c6)n5)c(C(F)F)n4)cc3)c21] |

TABLE 1-continued
Exemplary Compounds
| I-# | Structure |
|---|---|
| I-536 | 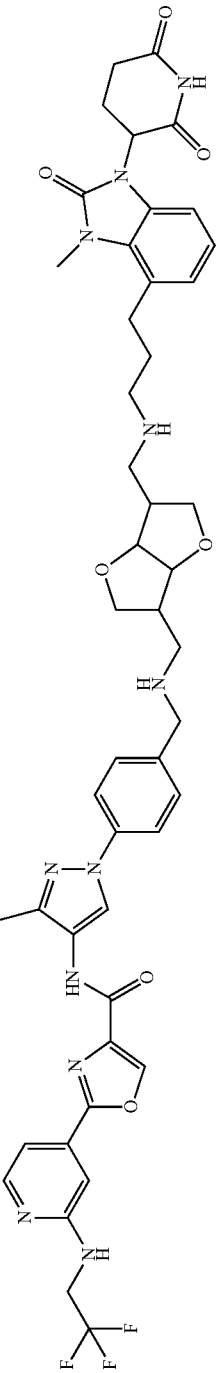 |
| I-537 | 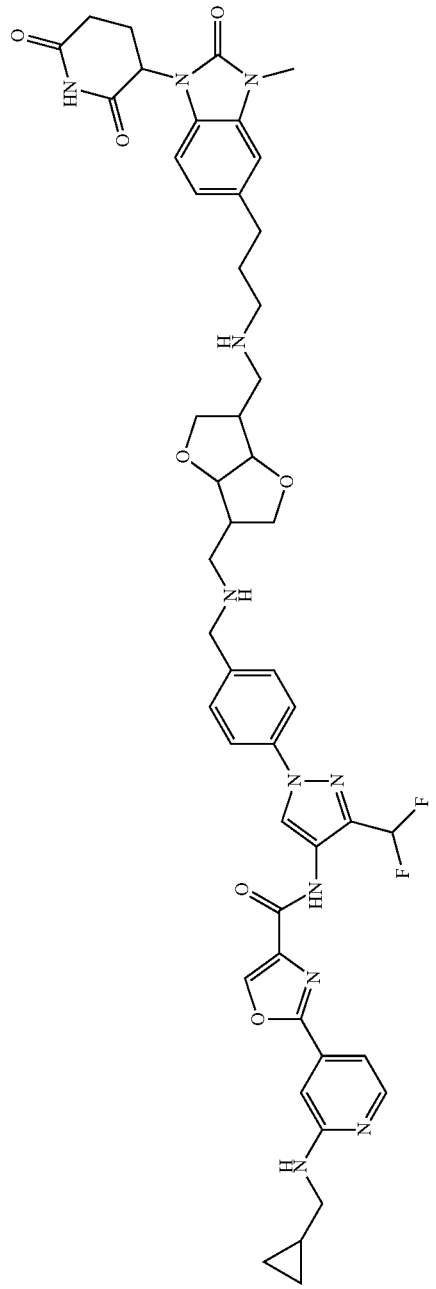 |
| I-538 | 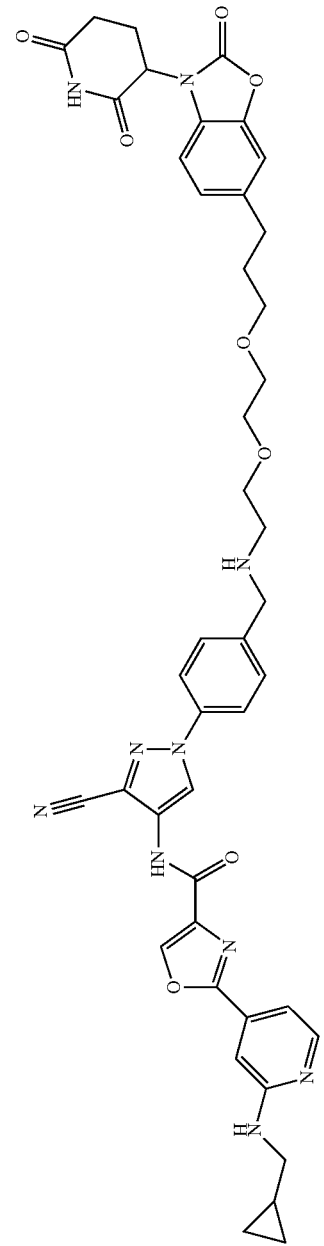 |

TABLE 1-continued
Exemplary Compounds
| I-# | Structure |
|---|---|
| I-539 | 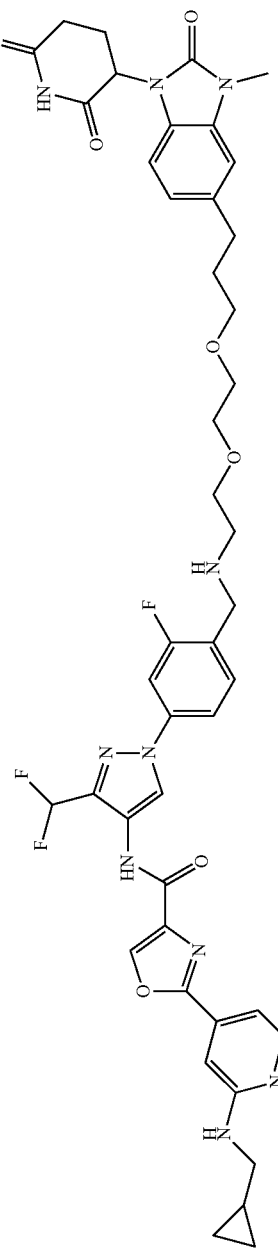 |
| I-540 | 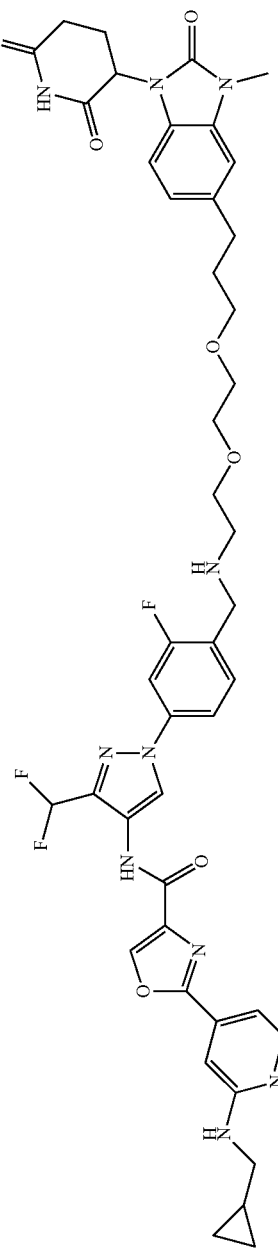 |

TABLE 1-continued

Exemplary Compounds

| I-# | Structure |
|---|---|
| I-541 | 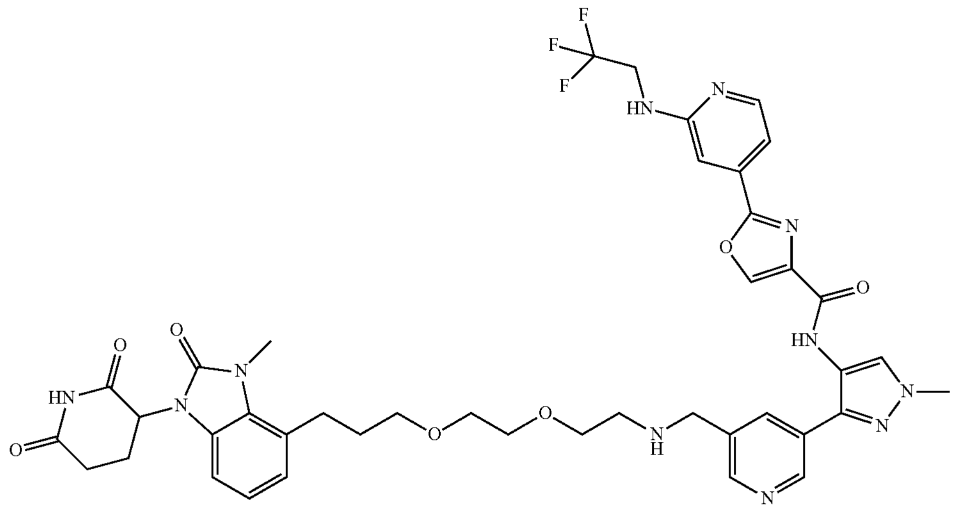 [SMILES: Cn1cc(NC(=O)c2coc(-c3ccnc(NCC(F)(F)F)c3)n2)c(-c2cncc(CNCCOCCOCCCc3cccc4c3n(C)c(=O)n4C3CCC(=O)NC3=O)c2)n1] |
| I-542 | 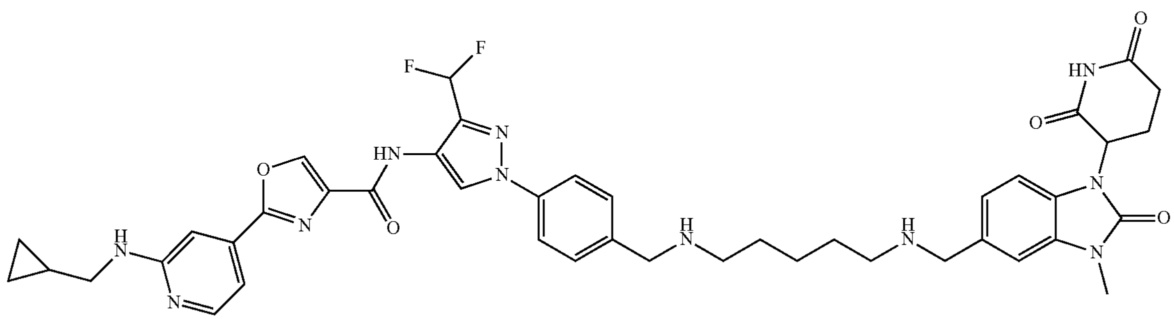 |

TABLE 1-continued

Exemplary Compounds

| I-# | Structure |
|---|---|
| I-543 | 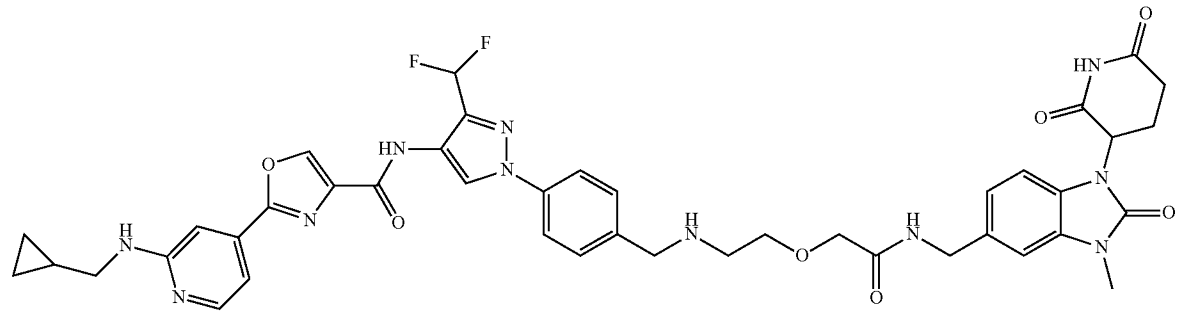 [SMILES: Cn1c(=O)n(C2CCC(=O)NC2=O)c2ccc(CNC(=O)COCCNCc3ccc(-n4cc(NC(=O)c5coc(-c6ccnc(NCC7CC7)c6)n5)c(C(F)F)n4)cc3)cc21] |
| I-544 | 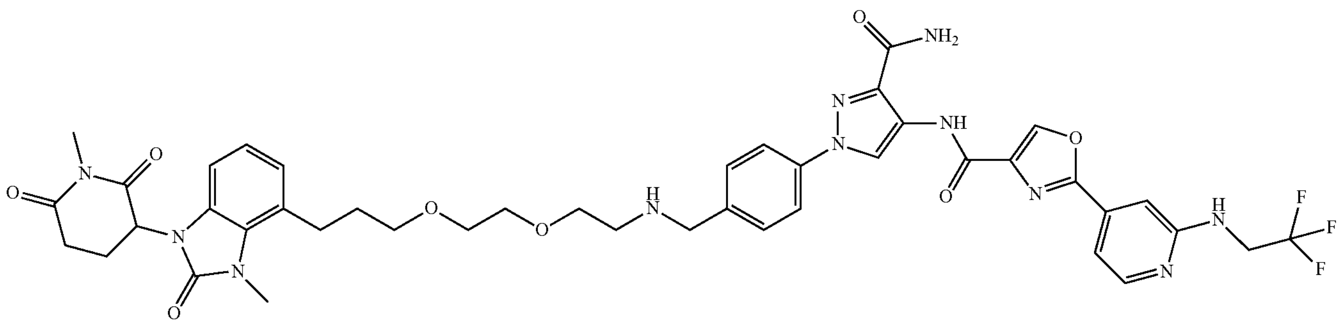 [SMILES: CN1C(=O)CCC(n2c(=O)n(C)c3c(CCCOCCOCCNCc4ccc(-n5cc(NC(=O)c6coc(-c7ccnc(NCC(F)(F)F)c7)n6)c(C(N)=O)n5)cc4)cccc32)C1=O] |
| I-545 | 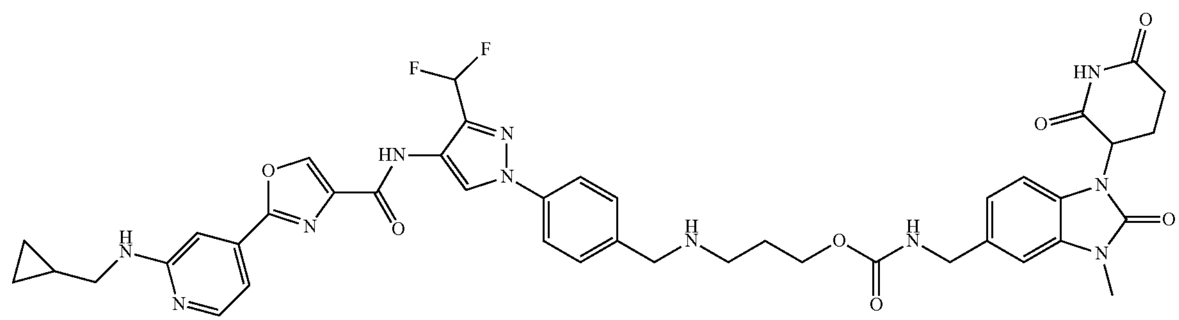 [SMILES: Cn1c(=O)n(C2CCC(=O)NC2=O)c2ccc(CNC(=O)OCCCNCc3ccc(-n4cc(NC(=O)c5coc(-c6ccnc(NCC7CC7)c6)n5)c(C(F)F)n4)cc3)cc21] |

TABLE 1-continued
Exemplary Compounds
| I-# | Structure |
|---|---|
| I-548 | 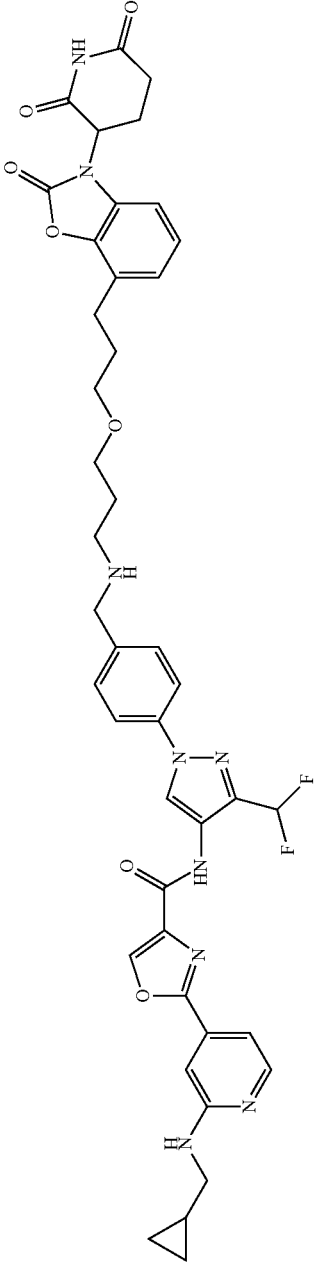 |
| I-549 | 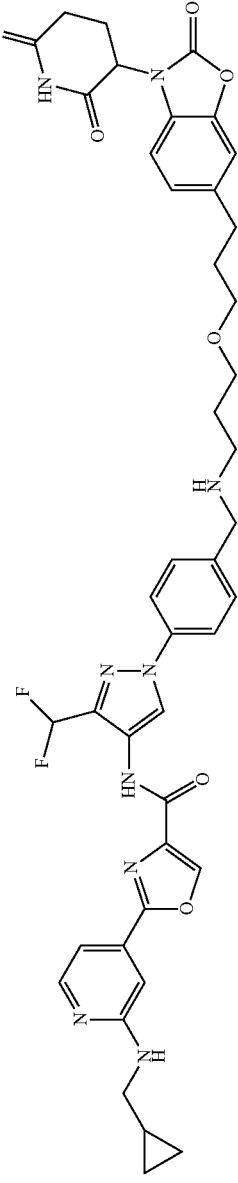 |
| I-550 | 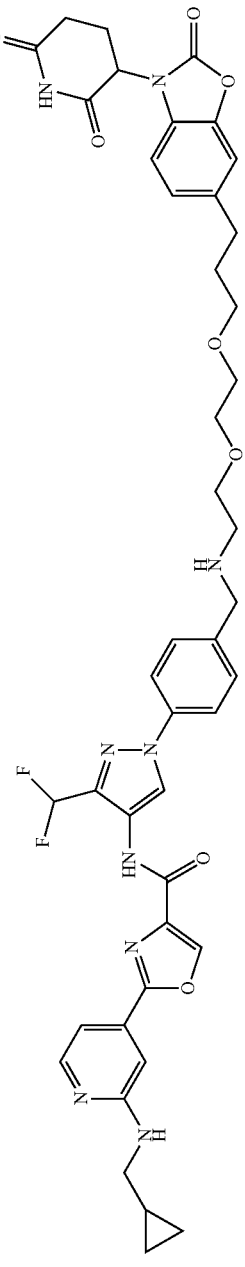 |

TABLE 1-continued
Exemplary Compounds
| I-# | Structure |
|---|---|
| I-551 | 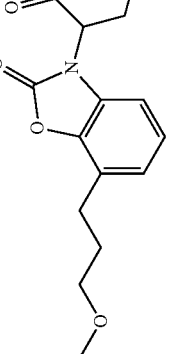 |
| I-552 | 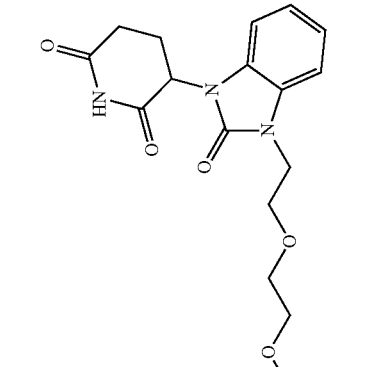 |

TABLE 1-continued
Exemplary Compounds
| I-# | Structure |
|---|---|
| I-553 | 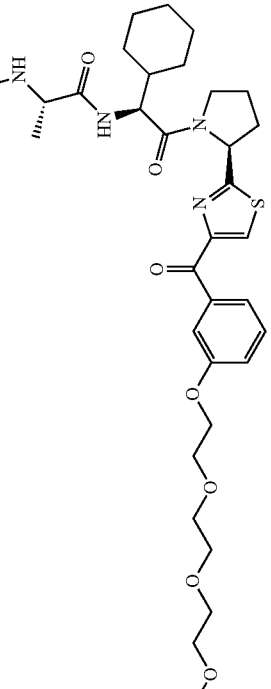 |
| I-554 | 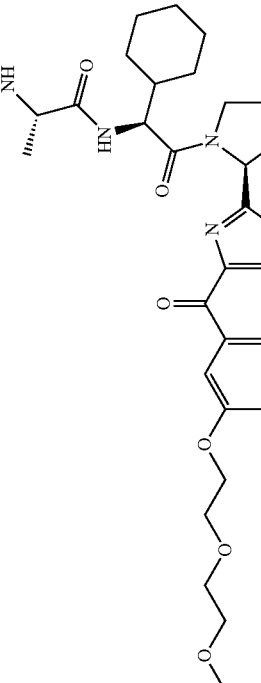 |

TABLE 1-continued
Exemplary Compounds
| I-# | Structure |
|---|---|
| I-555 | 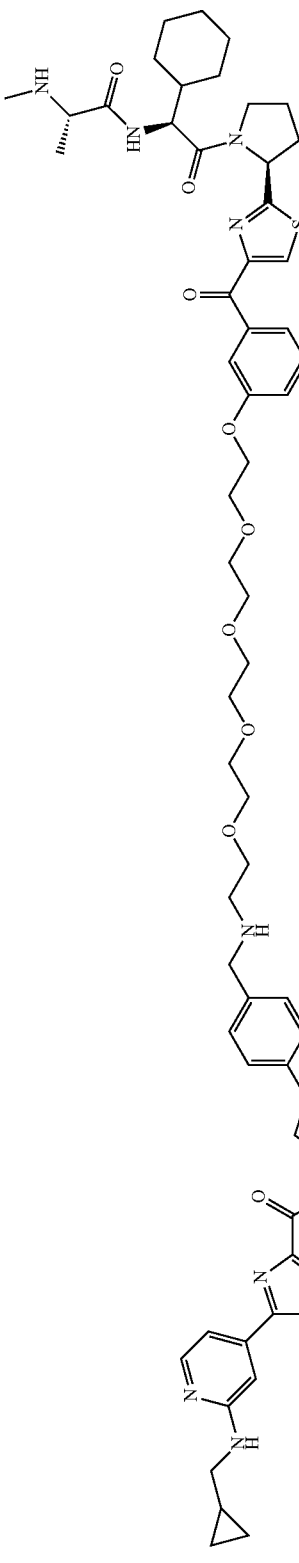 |
| I-556 | 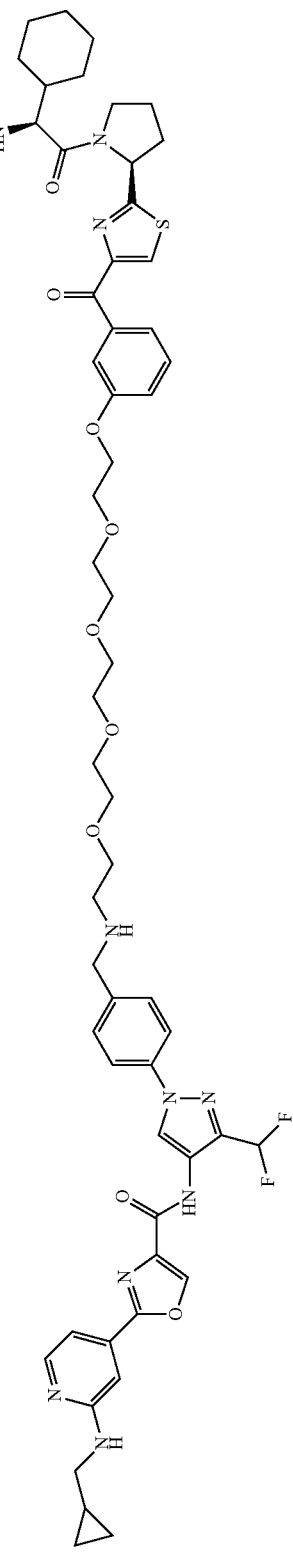 |

TABLE 1-continued
| I-# | Exemplary Compounds Structure |
|---|---|
| I-557 | 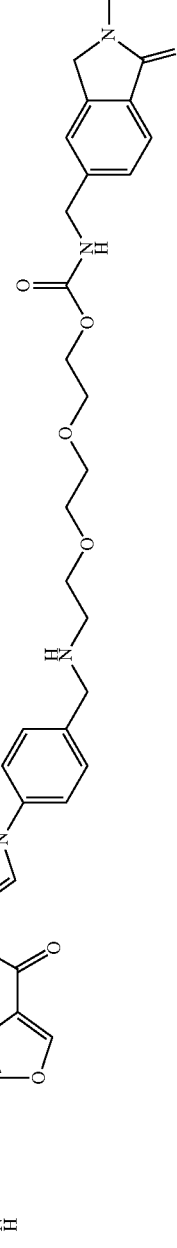 |
| I-558 | 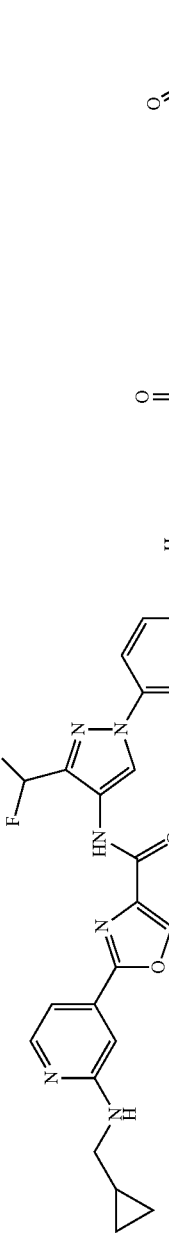 |

TABLE 1-continued
Exemplary Compounds
| I-# | Structure |
|---|---|
| I-559 | 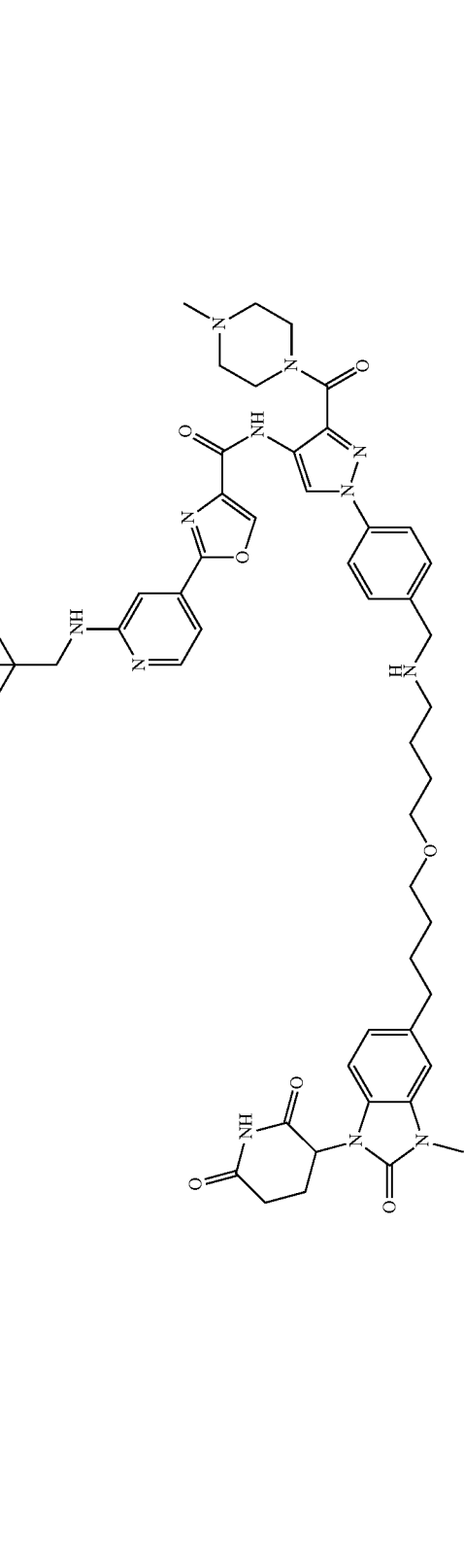 |

TABLE 1-continued

Exemplary Compounds

| I-# | Structure |
|---|---|
| I-560 | 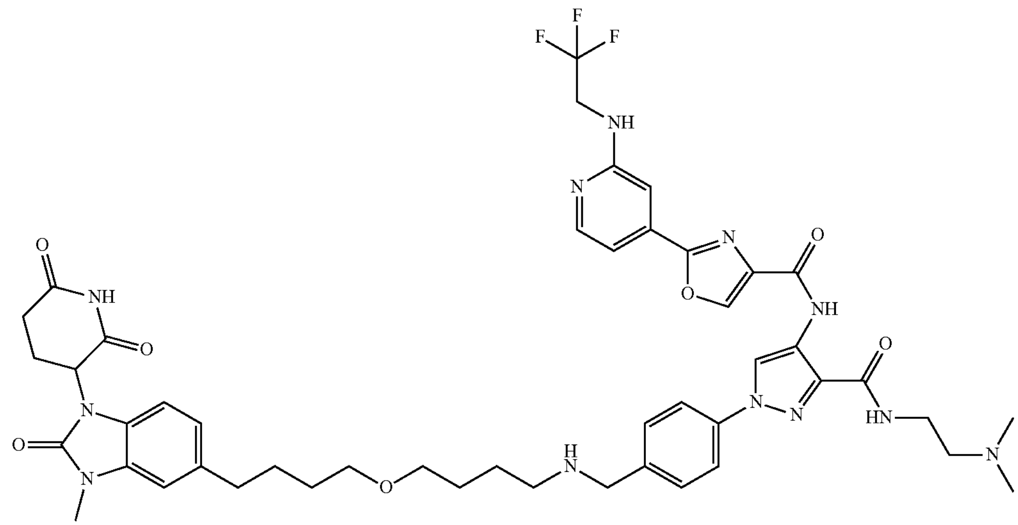 [SMILES: CN(C)CCNC(=O)c1nn(-c2ccc(CNCCCCOCCCCc3ccc4c(c3)n(C)c(=O)n4C3CCC(=O)NC3=O)cc2)cc1NC(=O)c1coc(-c2ccnc(NCC(F)(F)F)c2)n1] |
| I-563 | 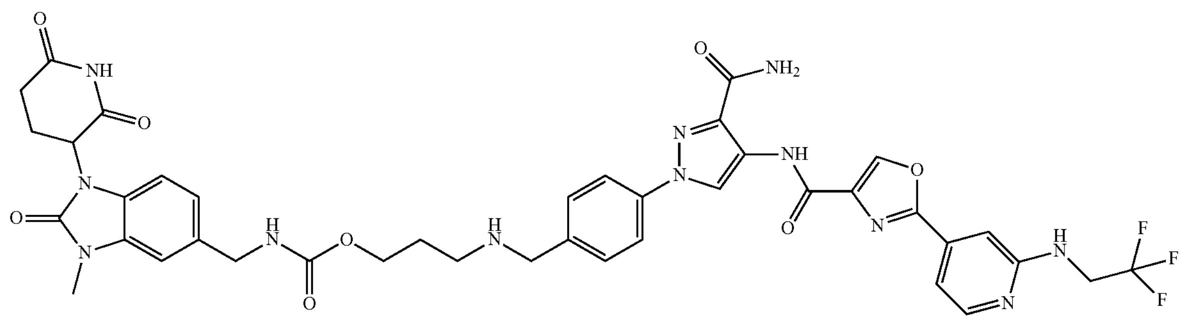 [SMILES: Cn1c(=O)n(C2CCC(=O)NC2=O)c2ccc(CNC(=O)OCCCNCc3ccc(-n4cc(NC(=O)c5coc(-c6ccnc(NCC(F)(F)F)c6)n5)c(C(N)=O)n4)cc3)cc21] |

TABLE 1-continued
Exemplary Compounds
| I-# | Structure |
|---|---|
| I-564 | 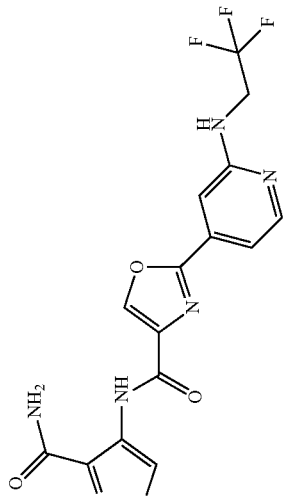 |
| I-567 | 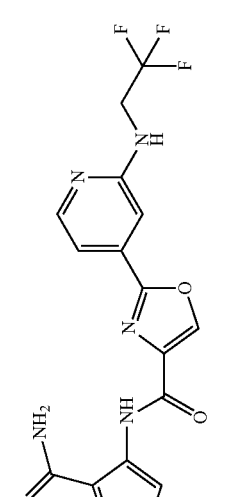 |
| I-568 | 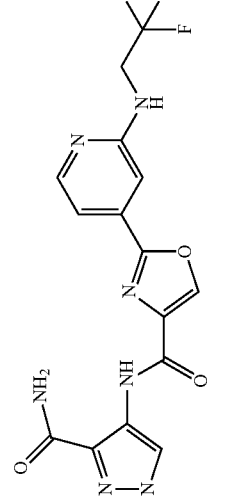 |

TABLE 1-continued

Exemplary Compounds

| I-# | Structure |
|---|---|
| I-572 | 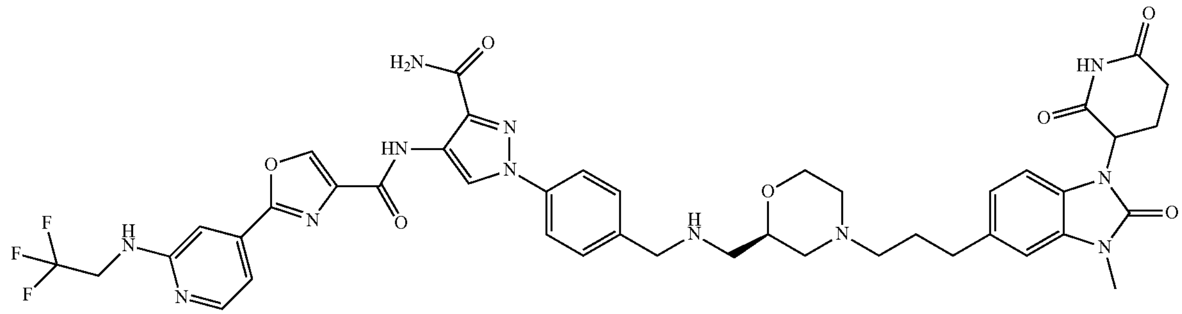 [SMILES: Cn1c(=O)n(C2CCC(=O)NC2=O)c2ccc(CCCN3CCO[C@H](CNCc4ccc(-n5cc(NC(=O)c6coc(-c7ccnc(NCC(F)(F)F)c7)n6)c(C(N)=O)n5)cc4)C3)cc21] |
| I-573 | 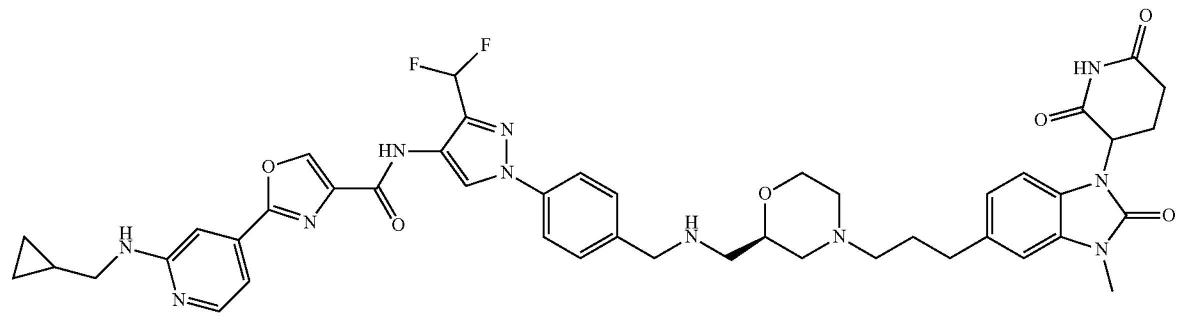 |
| I-574 | 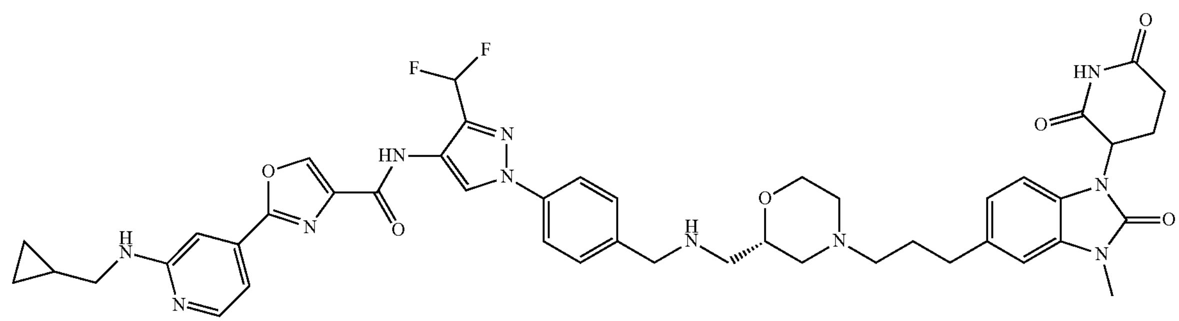 [SMILES: Cn1c(=O)n(C2CCC(=O)NC2=O)c2ccc(CCCN3CCO[C@@H](CNCc4ccc(-n5cc(NC(=O)c6coc(-c7ccnc(NCC8CC8)c7)n6)c(C(F)F)n5)cc4)C3)cc21] |

TABLE 1-continued

Exemplary Compounds

| I-# | Structure |
|---|---|
| I-575 | (structure) |
| I-576 | (structure) |

TABLE 1-continued
Exemplary Compounds
| I-# | Structure |
|---|---|
| I-578 | 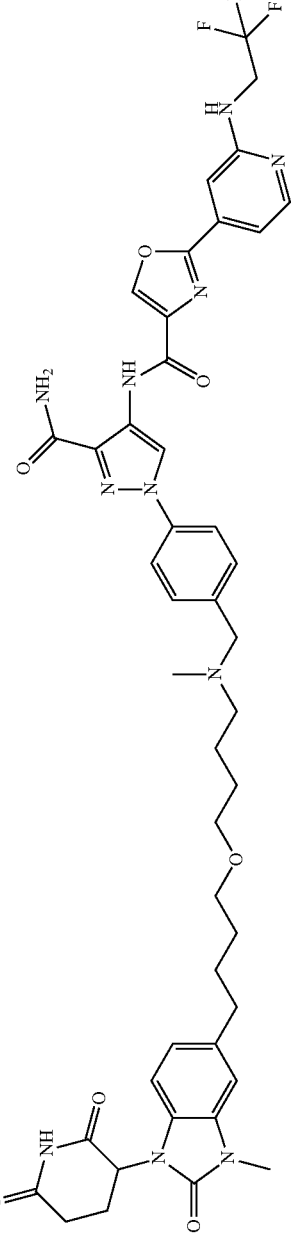 |
| I-579 | 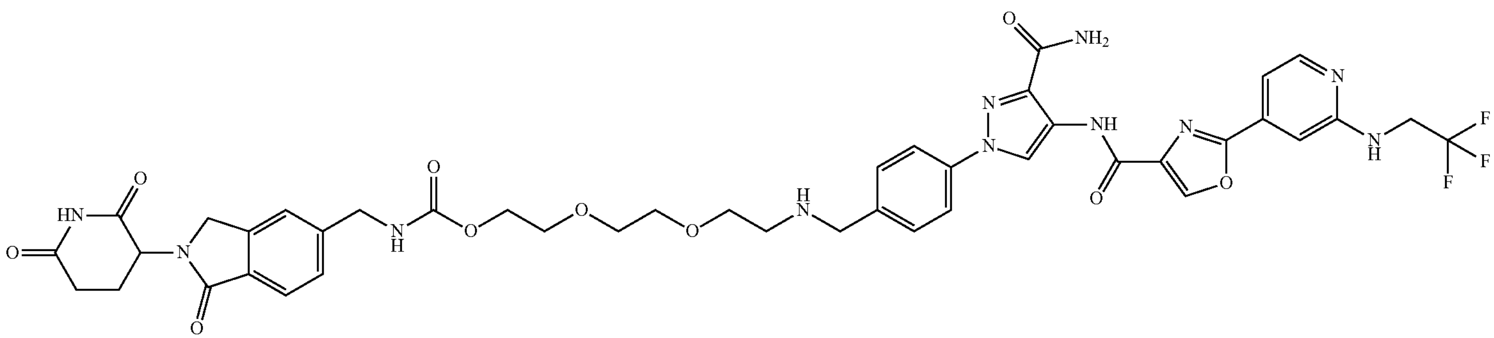 [SMILES: NC(=O)c1nn(-c2ccc(CNCCOCCOCCOC(=O)NCc3ccc4c(c3)CN(C3CCC(=O)NC3=O)C4=O)cc2)cc1NC(=O)c1coc(-c2ccnc(NCC(F)(F)F)c2)n1] |

TABLE 1-continued

Exemplary Compounds

| I-# | Structure |
|---|---|
| I-580 | 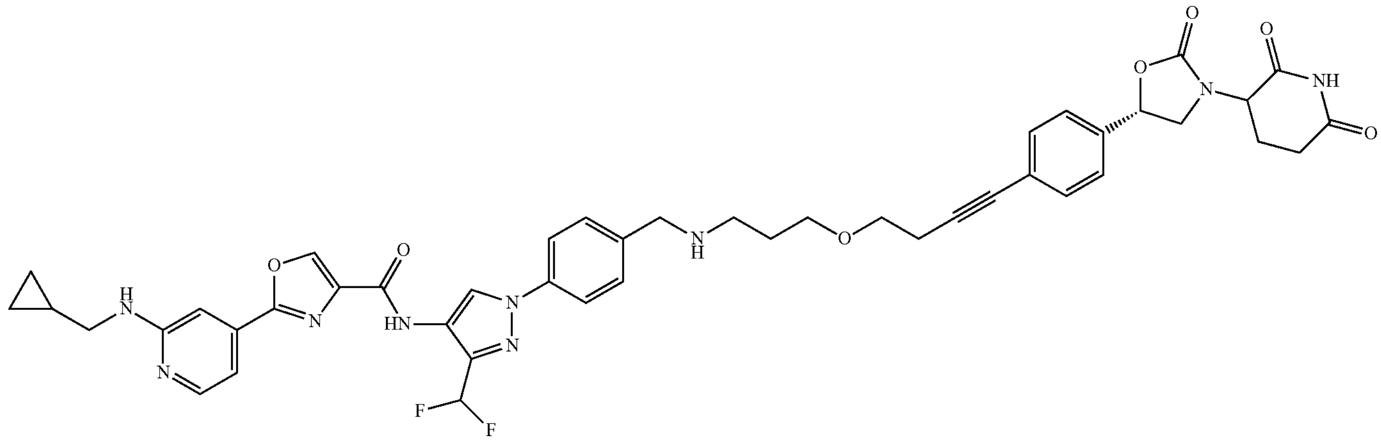 [SMILES: O=C1CCC(N2C[C@H](c3ccc(C#CCCOCCCNCc4ccc(-n5cc(NC(=O)c6coc(-c7ccnc(NCC8CC8)c7)n6)c(C(F)F)n5)cc4)cc3)OC2=O)C(=O)N1] |
| I-581 | 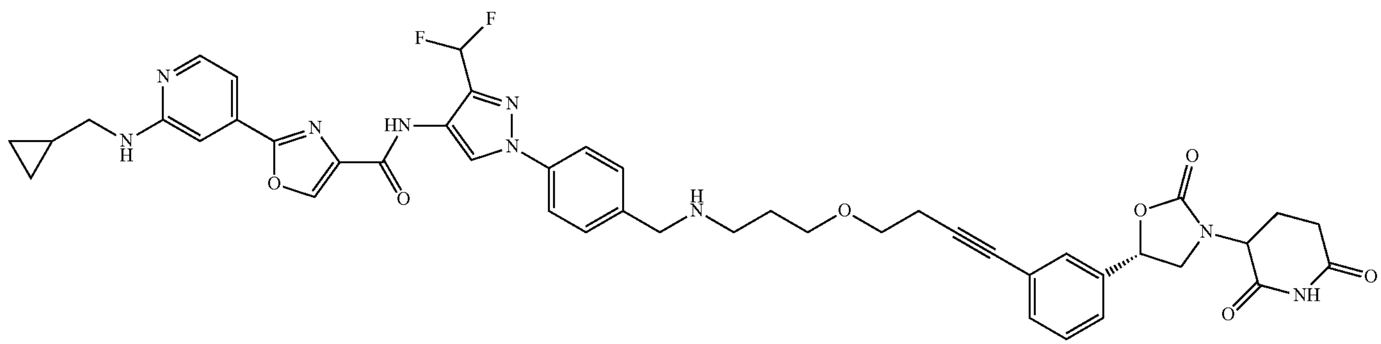 [SMILES: O=C1CCC(N2C[C@H](c3cccc(C#CCCOCCCNCc4ccc(-n5cc(NC(=O)c6coc(-c7ccnc(NCC8CC8)c7)n6)c(C(F)F)n5)cc4)c3)OC2=O)C(=O)N1] |

TABLE 1-continued
Exemplary Compounds
| I-# | Structure |
|---|---|
| I-582 | 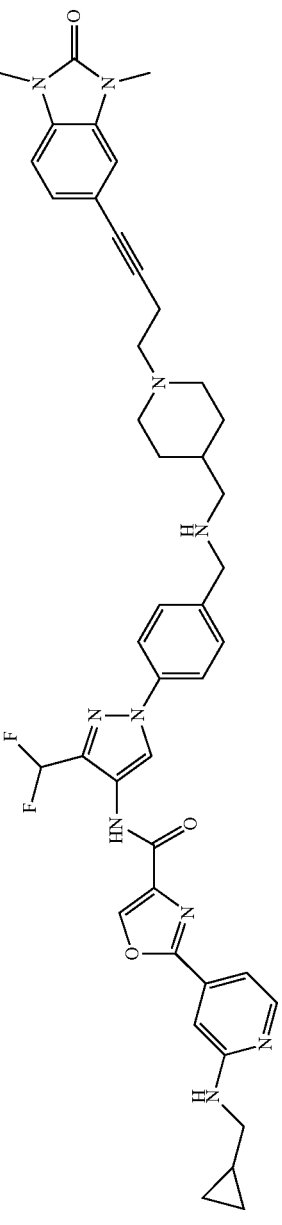 |
| I-583 | 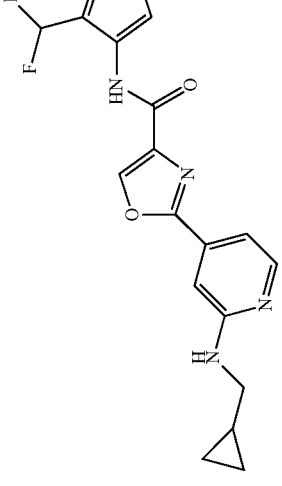 |

TABLE 1-continued

Exemplary Compounds

| I-# | Structure |
|---|---|
| I-584 | 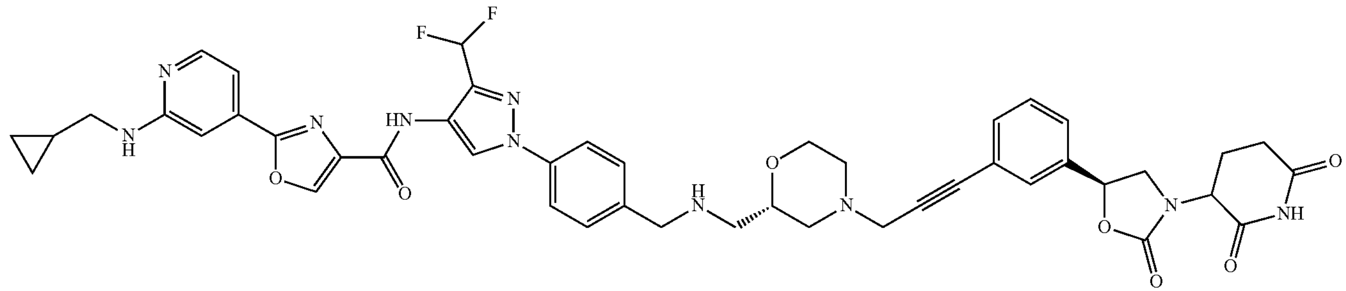 |
| I-585 | 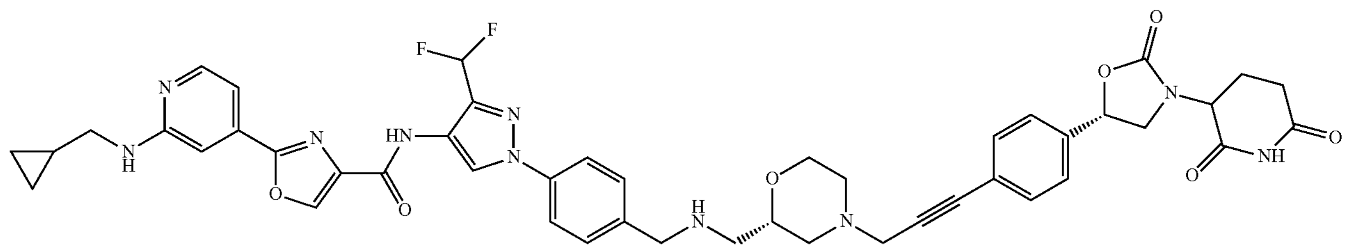 [SMILES: O=C1CCC(N2C[C@H](c3ccc(C#CCN4CCO[C@@H](CNCc5ccc(-n6cc(NC(=O)c7coc(-c8ccnc(NCC9CC9)c8)n7)c(C(F)F)n6)cc5)C4)cc3)OC2=O)C(=O)N1] |
| I-587 | 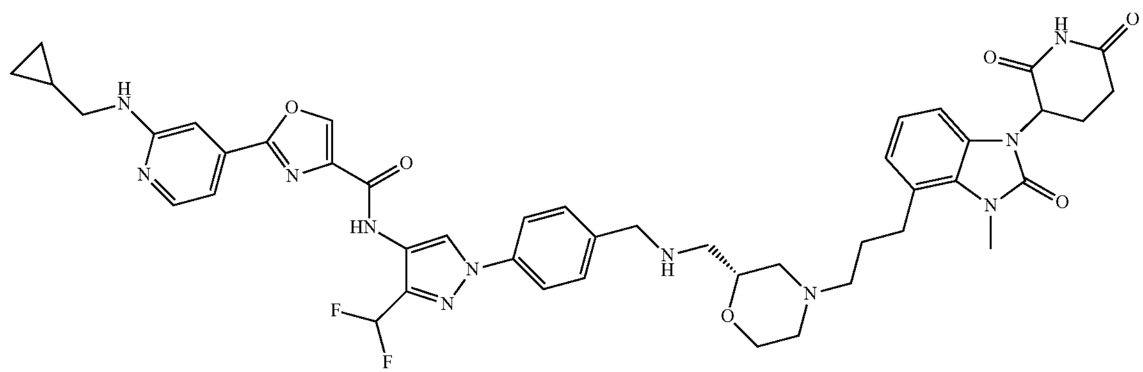 [SMILES: Cn1c(=O)n(C2CCC(=O)NC2=O)c2cccc(CCCN3CCO[C@H](CNCc4ccc(-n5cc(NC(=O)c6coc(-c7ccnc(NCC8CC8)c7)n6)c(C(F)F)n5)cc4)C3)c21] |

TABLE 1-continued
Exemplary Compounds
| I-# | Structure |
|---|---|
| I-588 | 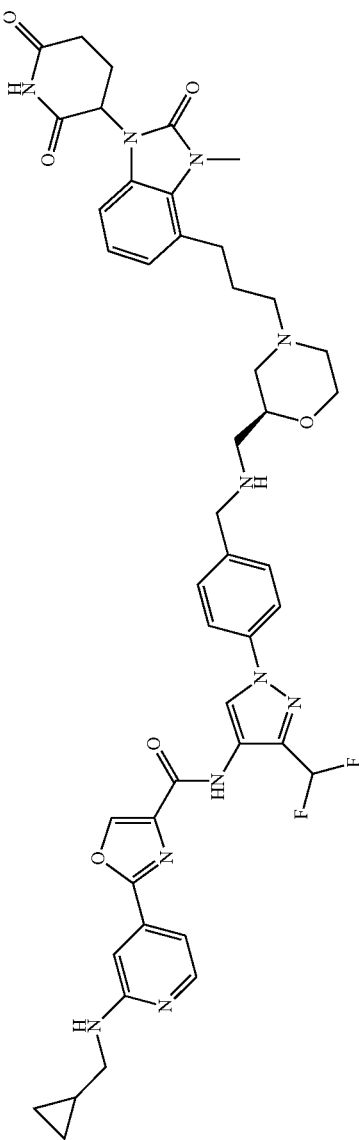 |
| I-589 | 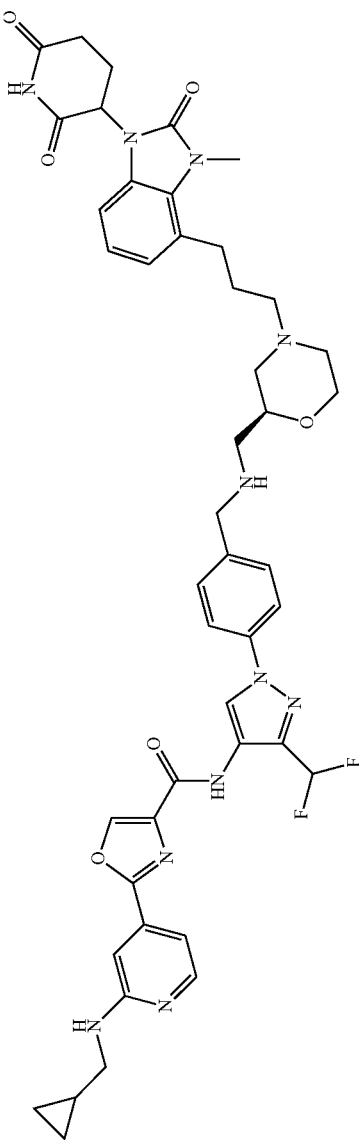 |

TABLE 1-continued

Exemplary Compounds

| I-# | Structure |
|---|---|
| I-590 | 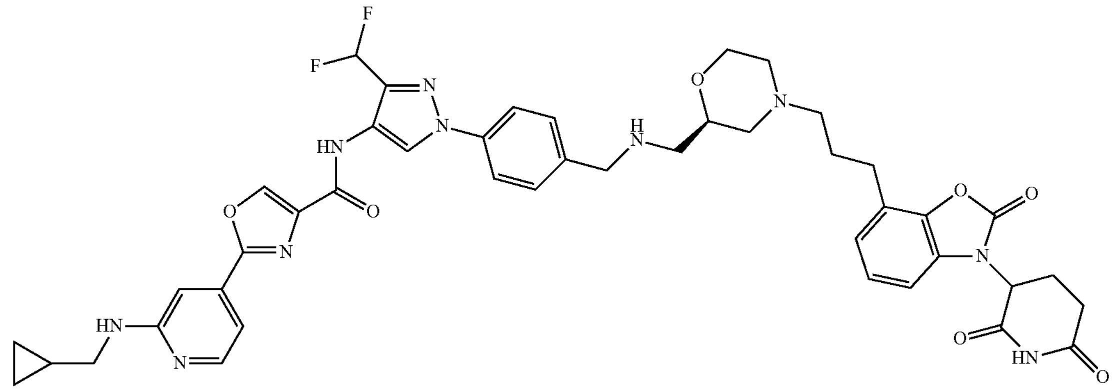 [SMILES: O=C1CCC(n2c(=O)oc3c(CCCN4CCO[C@H](CNCc5ccc(-n6cc(NC(=O)c7coc(-c8ccnc(NCC9CC9)c8)n7)c(C(F)F)n6)cc5)C4)cccc32)C(=O)N1] |
| I-591 | 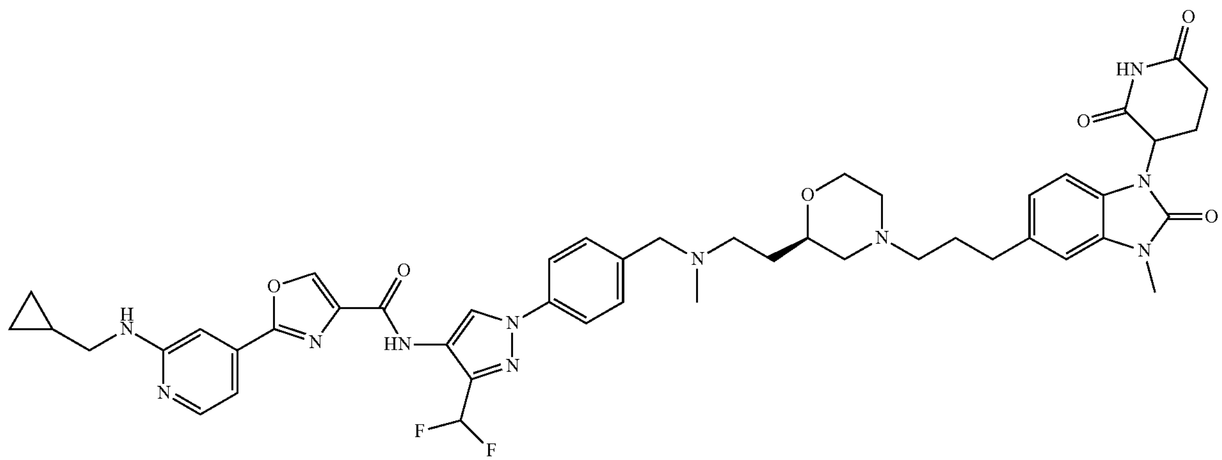 [SMILES: CN(CC[C@@H]1CN(CCCc2ccc3c(c2)n(C)c(=O)n3C2CCC(=O)NC2=O)CCO1)Cc1ccc(-n2cc(NC(=O)c3coc(-c4ccnc(NCC5CC5)c4)n3)c(C(F)F)n2)cc1] |

TABLE 1-continued
Exemplary Compounds
| I-# | Structure |
|---|---|
| I-592 | 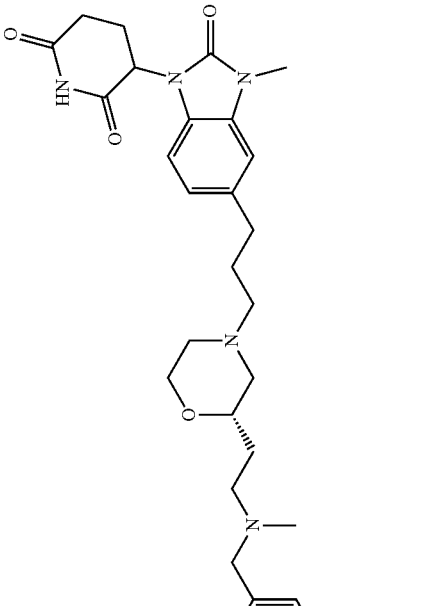 |
| I-593 | 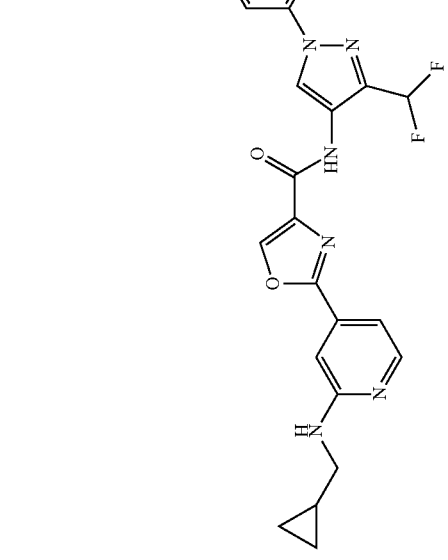 |

TABLE 1-continued
Exemplary Compounds
| I-# | Structure |
|---|---|
| I-595 | 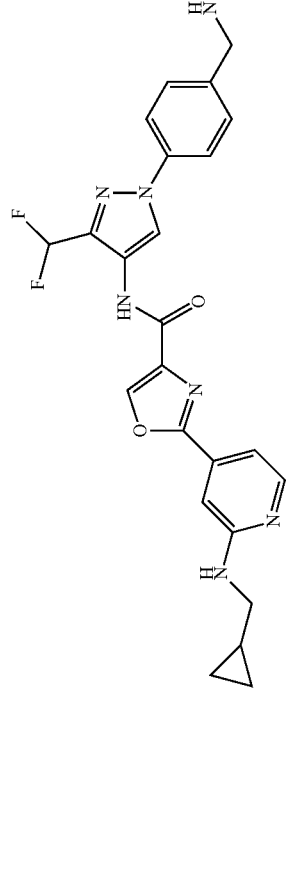 |
| I-596 | 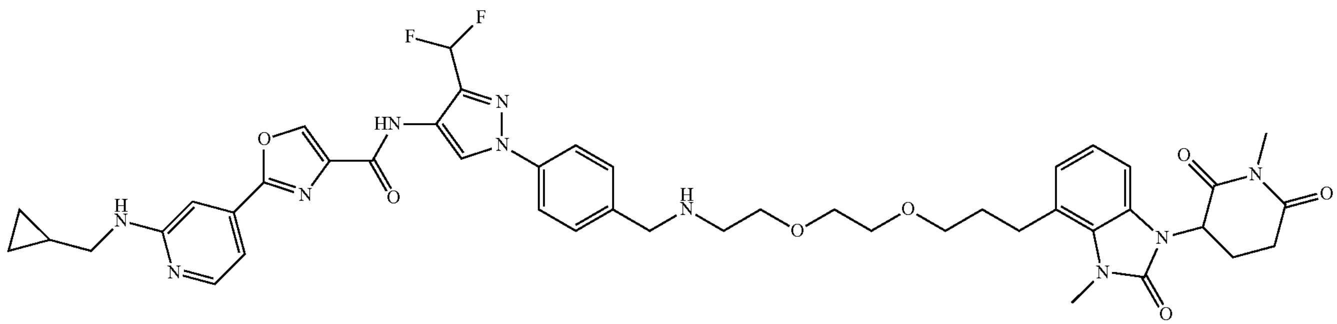 [SMILES: CN1C(=O)CCC(n2c(=O)n(C)c3c(CCCOCCOCCNCc4ccc(-n5cc(NC(=O)c6coc(-c7ccnc(NCC8CC8)c7)n6)c(C(F)F)n5)cc4)cccc32)C1=O] |
| I-597 | 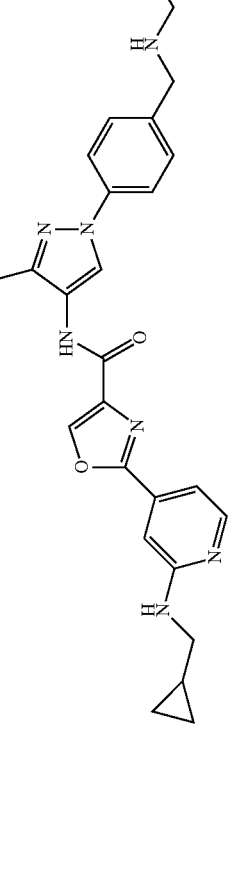 |

TABLE 1-continued

Exemplary Compounds

| I-# | Structure |
|---|---|
| I-598 | 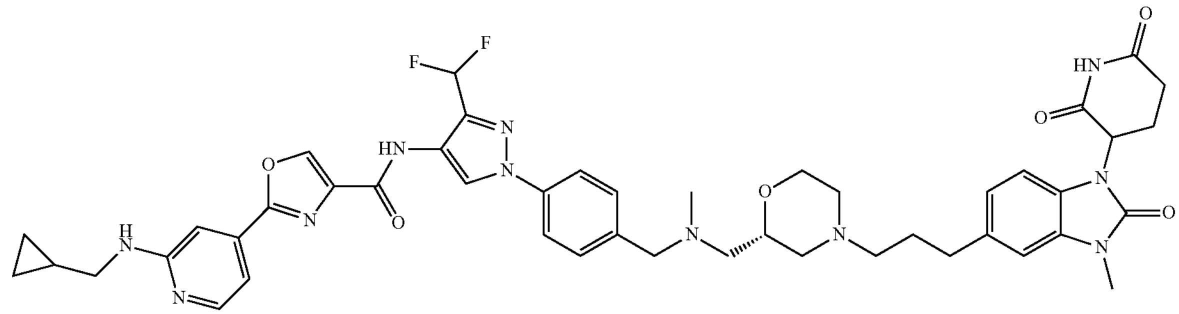 [SMILES: CN(Cc1ccc(-n2cc(NC(=O)c3coc(-c4ccnc(NCC5CC5)c4)n3)c(C(F)F)n2)cc1)C[C@H]1CN(CCCc2ccc3c(c2)n(C)c(=O)n3C2CCC(=O)NC2=O)CCO1] |
| I-599 | 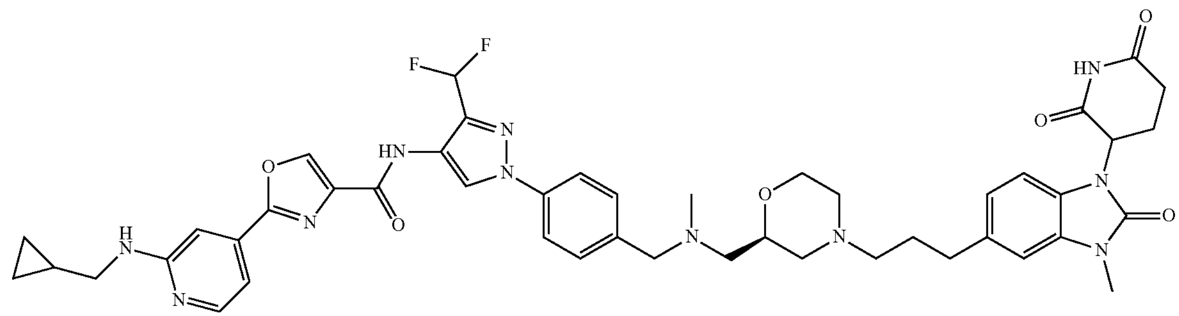 [SMILES: CN(Cc1ccc(-n2cc(NC(=O)c3coc(-c4ccnc(NCC5CC5)c4)n3)c(C(F)F)n2)cc1)C[C@@H]1CN(CCCc2ccc3c(c2)n(C)c(=O)n3C2CCC(=O)NC2=O)CCO1] |
| I-614 | 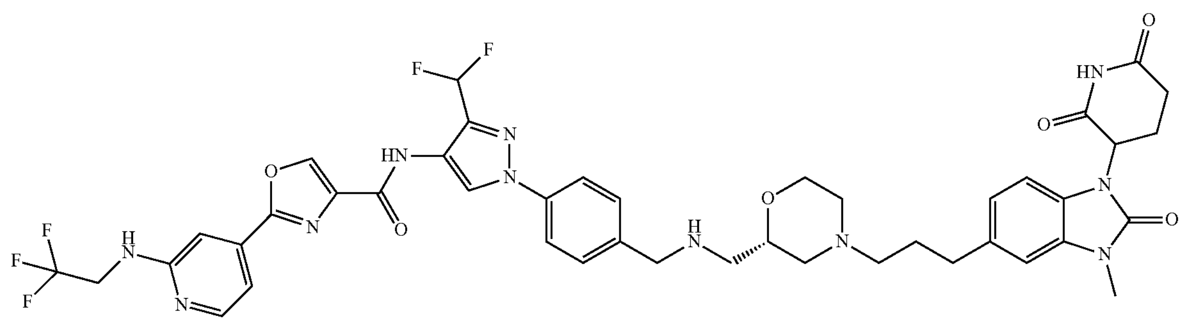 [SMILES: Cn1c(=O)n(C2CCC(=O)NC2=O)c2ccc(CCCN3CCO[C@@H](CNCc4ccc(-n5cc(NC(=O)c6coc(-c7ccnc(NCC(F)(F)F)c7)n6)c(C(F)F)n5)cc4)C3)cc21] |

TABLE 1-continued

Exemplary Compounds

| I-# | Structure |
|---|---|
| I-617 | (structure) |
| I-691 | (structure) |

TABLE 1-continued
Exemplary Compounds
| I-# | Structure |
|---|---|
| I-692 | 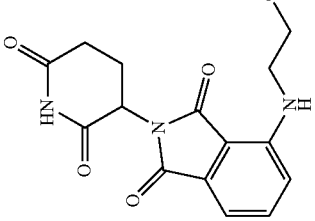 |
| I-693 | 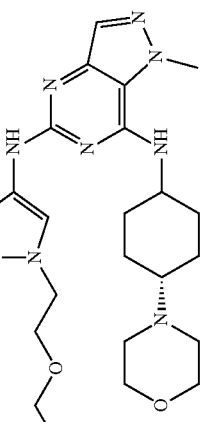 |

TABLE 1-continued
Exemplary Compounds
| I-# | Structure |
|---|---|
| I-694 | 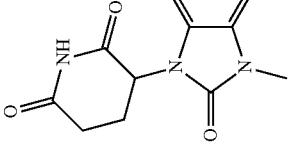 |
| I-684 | 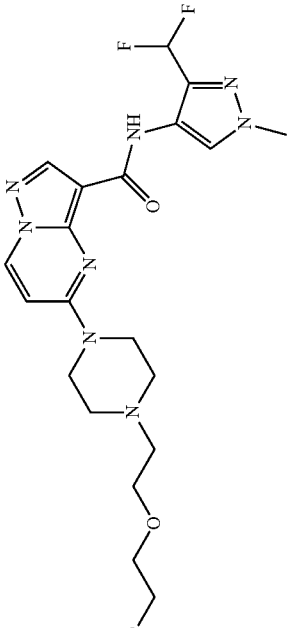 |

TABLE 1-continued

Exemplary Compounds

| I-# | Structure |
| --- | --- |
| I-685 | 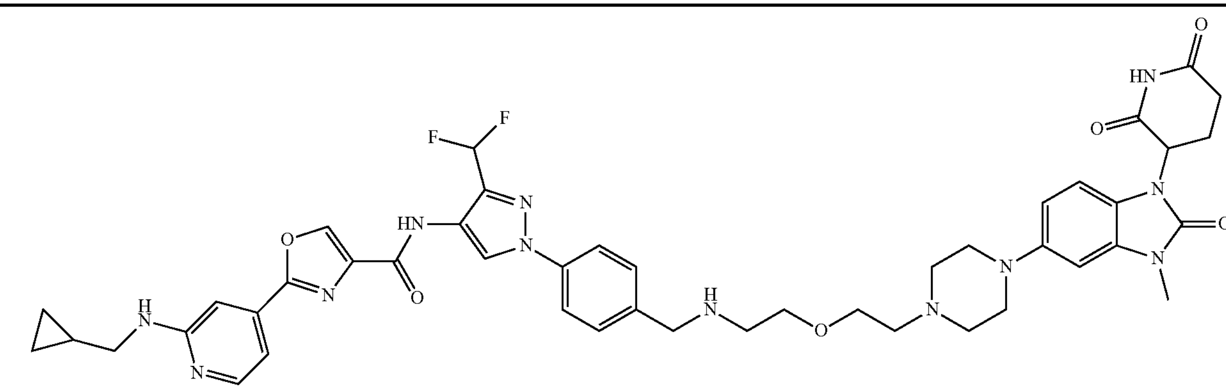 |
| I-699 | 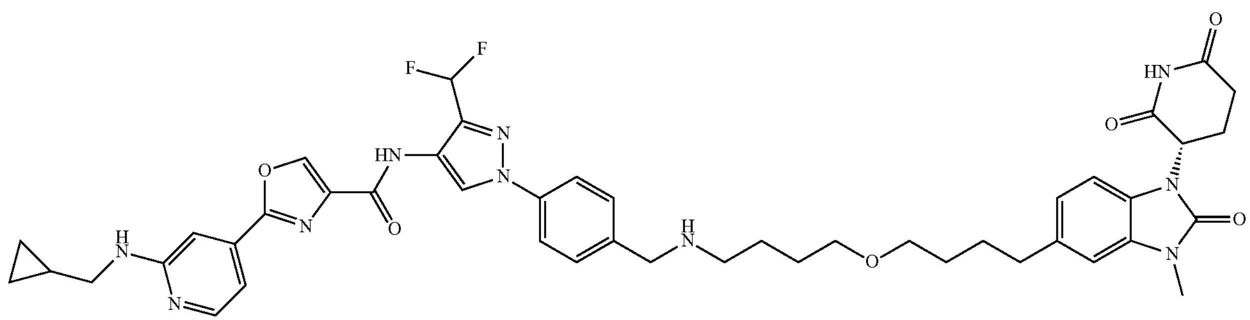 [SMILES: Cn1c(=O)n([C@H]2CCC(=O)NC2=O)c2ccc(CCCCOCCCCNCc3ccc(-n4cc(NC(=O)c5coc(-c6ccnc(NCC7CC7)c6)n5)c(C(F)F)n4)cc3)cc21] |
| I-700 | 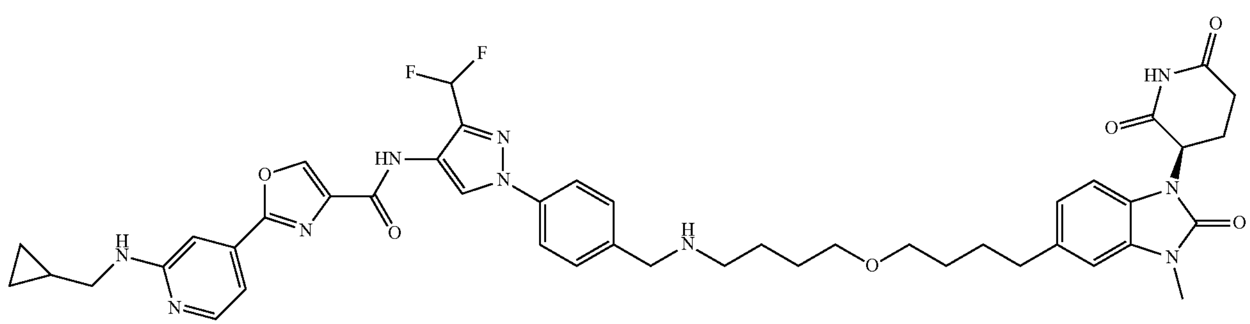 [SMILES: Cn1c(=O)n([C@@H]2CCC(=O)NC2=O)c2ccc(CCCCOCCCCNCc3ccc(-n4cc(NC(=O)c5coc(-c6ccnc(NCC7CC7)c6)n5)c(C(F)F)n4)cc3)cc21] |

TABLE 1-continued

Exemplary Compounds

| I-# | Structure |
|---|---|
| I-688 | 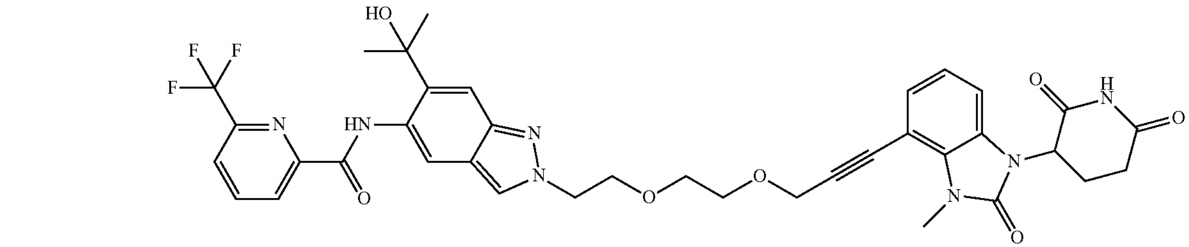 [SMILES: Cn1c(=O)n(C2CCC(=O)NC2=O)c2cccc(C#CCOCCOCCn3cc4cc(NC(=O)c5cccc(C(F)(F)F)n5)c(C(C)(C)O)cc4n3)c21] |
| I-689 | 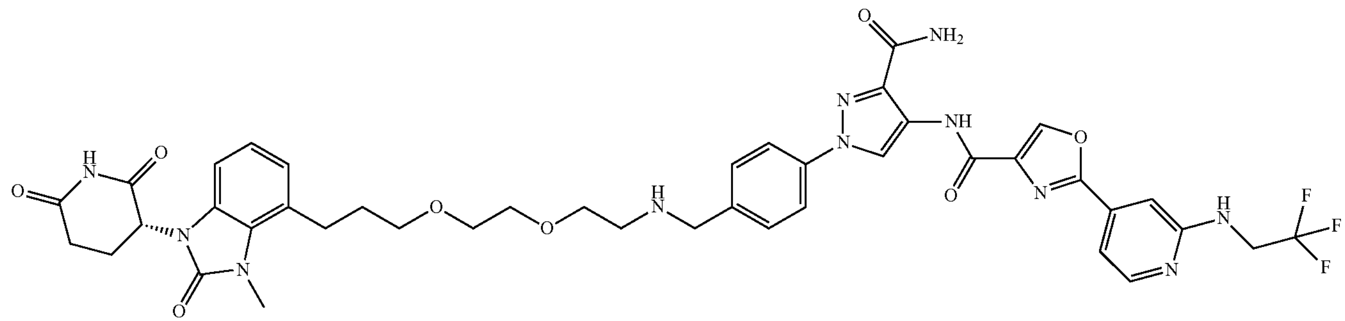 [SMILES: Cn1c(=O)n([C@@H]2CCC(=O)NC2=O)c2cccc(CCCOCCOCCNCc3ccc(-n4cc(NC(=O)c5coc(-c6ccnc(NCC(F)(F)F)c6)n5)c(C(N)=O)n4)cc3)c21] |
| I-690 | 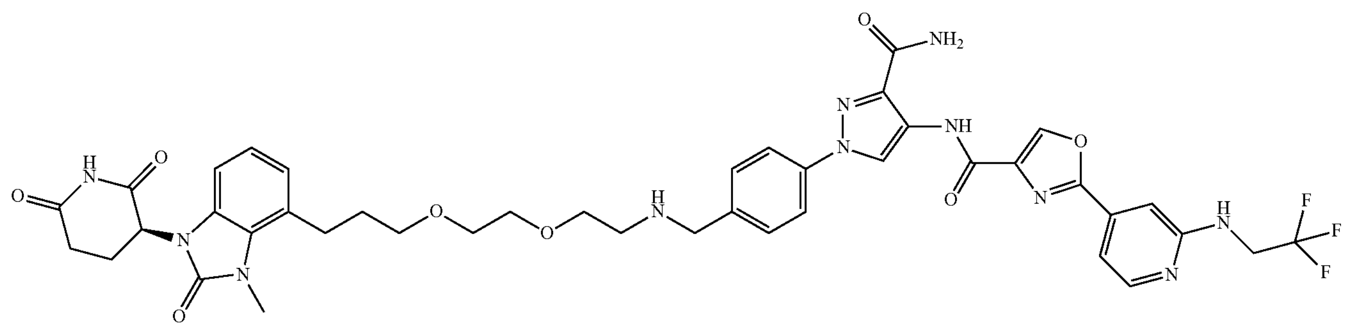 [SMILES: Cn1c(=O)n([C@H]2CCC(=O)NC2=O)c2cccc(CCCOCCOCCNCc3ccc(-n4cc(NC(=O)c5coc(-c6ccnc(NCC(F)(F)F)c6)n5)c(C(N)=O)n4)cc3)c21] |

TABLE 1-continued
Exemplary Compounds
| I-# | Structure |
|---|---|
| I-519 | 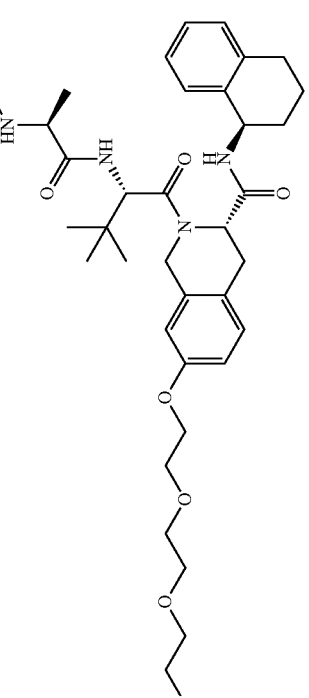 |
| I-520 | 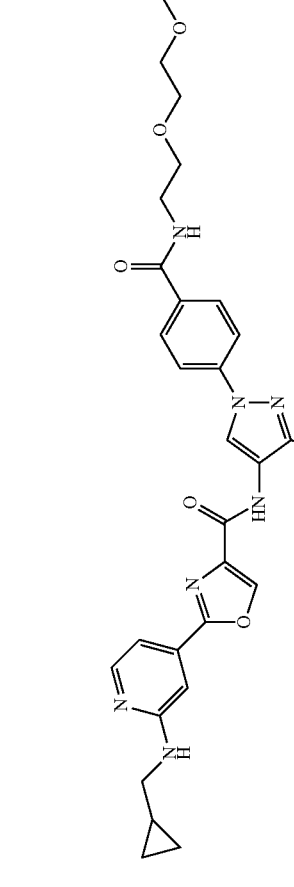 |

TABLE 1-continued

Exemplary Compounds

| I-# | Structure |
|---|---|
| I-521 | 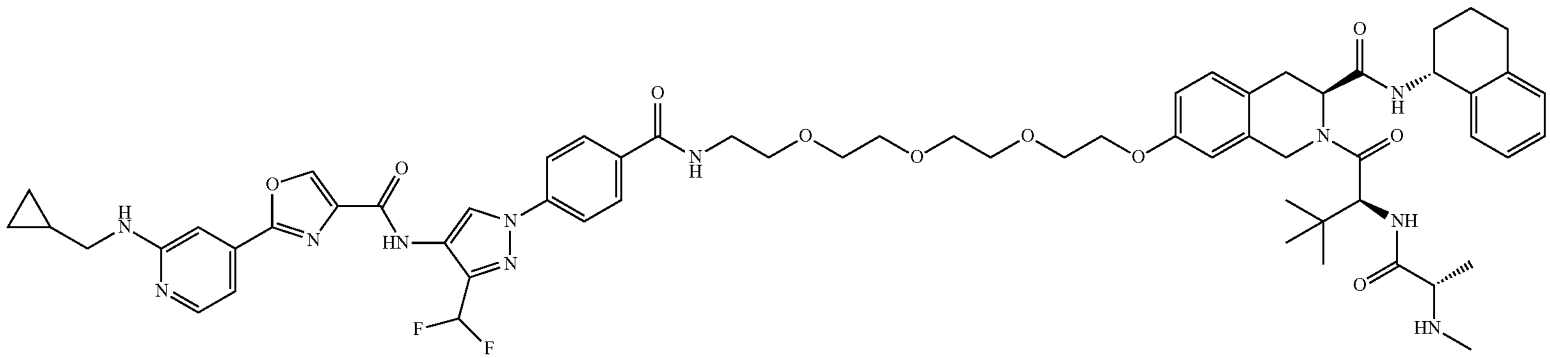 [SMILES: CN[C@@H](C)C(=O)N[C@H](C(=O)N1Cc2cc(OCCOCCOCCOCCNC(=O)c3ccc(-n4cc(NC(=O)c5coc(-c6ccnc(NCC7CC7)c6)n5)c(C(F)F)n4)cc3)ccc2C[C@H]1C(=O)N[C@@H]1CCCc2ccccc21)C(C)(C)C] |
| I-680 | 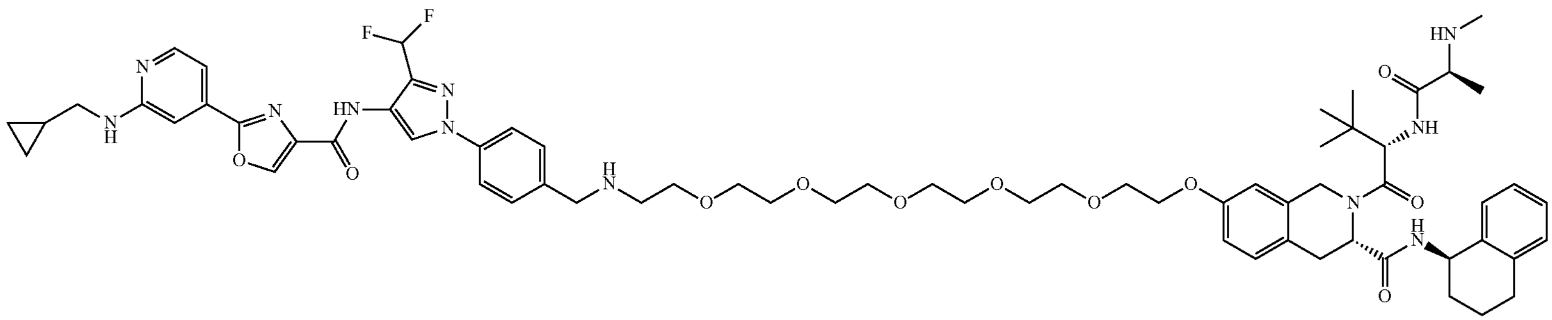 [SMILES: CN[C@@H](C)C(=O)N[C@H](C(=O)N1Cc2cc(OCCOCCOCCOCCOCCOCCNCc3ccc(-n4cc(NC(=O)c5coc(-c6ccnc(NCC7CC7)c6)n5)c(C(F)F)n4)cc3)ccc2C[C@H]1C(=O)N[C@@H]1CCCc2ccccc21)C(C)(C)C] |

TABLE 1-continued

Exemplary Compounds

| I-# | Structure |
|---|---|
| I-681 | 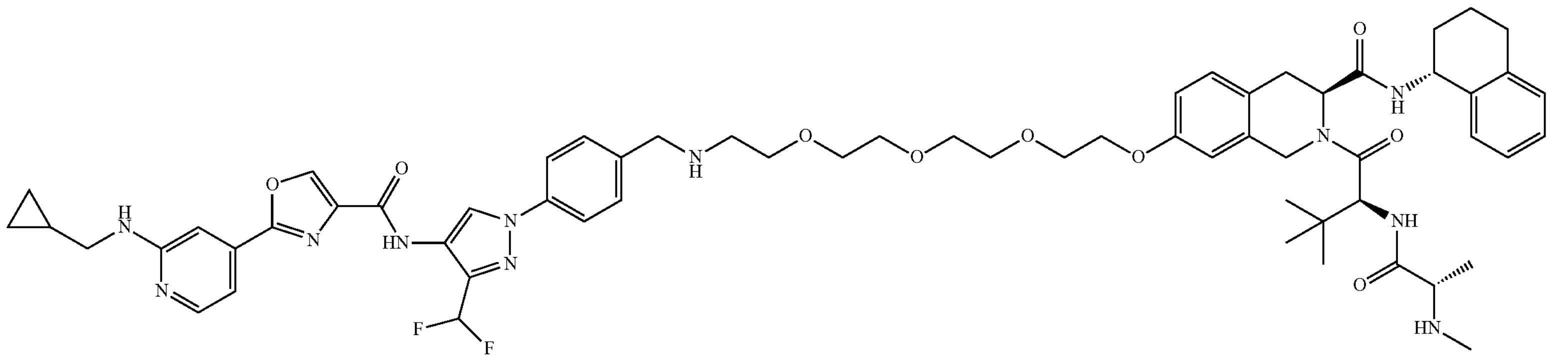 [SMILES: CN[C@@H](C)C(=O)N[C@H](C(=O)N1Cc2cc(OCCOCCOCCOCCNCc3ccc(-n4cc(NC(=O)c5coc(-c6ccnc(NCC7CC7)c6)n5)c(C(F)F)n4)cc3)ccc2C[C@H]1C(=O)N[C@@H]1CCCc2ccccc21)C(C)(C)C] |
| I-682 | 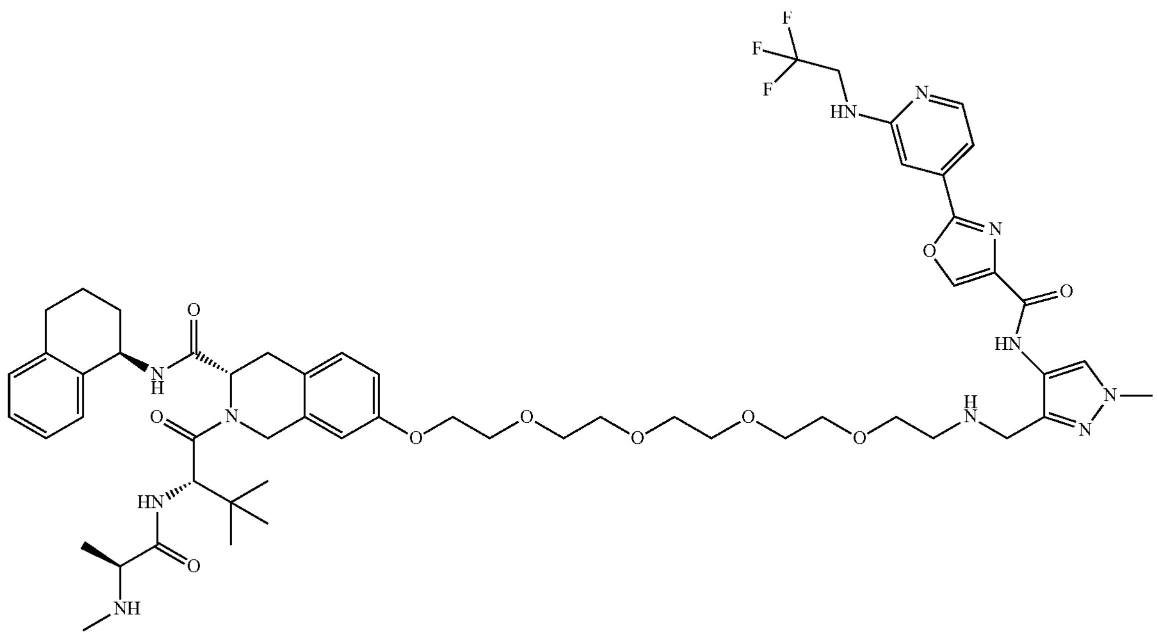 [SMILES: CN[C@@H](C)C(=O)N[C@H](C(=O)N1Cc2cc(OCCOCCOCCOCCOCCNCc3nn(C)cc3NC(=O)c3coc(-c4ccnc(NCC(F)(F)F)c4)n3)ccc2C[C@H]1C(=O)N[C@@H]1CCCc2ccccc21)C(C)(C)C] |

In some embodiments, the present invention provides a compound set forth in Table 1, above, or a pharmaceutically acceptable salt thereof.

4. General Methods of Providing the Present Compounds

The compounds of this invention may be prepared or isolated in general by synthetic and/or semi-synthetic methods known to those skilled in the art for analogous compounds and by methods described in detail in the Examples, herein.

In the Schemes below, where a particular protecting group, leaving group, or transformation condition is depicted, one of ordinary skill in the art will appreciate that other protecting groups, leaving groups, and transformation conditions are also suitable and are contemplated. Such groups and transformations are described in detail in *March's Advanced Organic Chemistry: Reactions, Mechanisms, and Structure*, M. B. Smith and J. March, 5$^{th}$ Edition, John Wiley & Sons, 2001, *Comprehensive Organic Transformations*, R. C. Larock, 2$^{nd}$ Edition, John Wiley & Sons, 1999, and *Protecting Groups in Organic Synthesis*, T. W. Greene and P. G. M. Wuts, 3$^{rd}$ edition, John Wiley & Sons, 1999, the entirety of each of which is hereby incorporated herein by reference.

As used herein, the phrase "oxygen protecting group" includes, for example, carbonyl protecting groups, hydroxyl protecting groups, etc. Hydroxyl protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitable hydroxyl protecting groups include, but are not limited to, esters, allyl ethers, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetyl), crotonate, 4-methoxy-crotonate, benzoate, p-benylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, and 2- and 4-picolyl.

Amino protecting groups are well known in the art and include those described in detail in *Protecting Groups in Organic Synthesis*, T. W. Greene and P. G. M. Wuts, 3$^{d}$ edition, John Wiley & Sons, 1999, the entirety of which is incorporated herein by reference. Suitable amino protecting groups include, but are not limited to, aralkylamines, carbamates, cyclic imides, allyl amines, amides, and the like. Examples of such groups include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like.

In certain embodiments, compounds of the present invention are generally prepared according to Scheme 1 set forth below:

Scheme 1: Synthesis of Compounds of Formula I

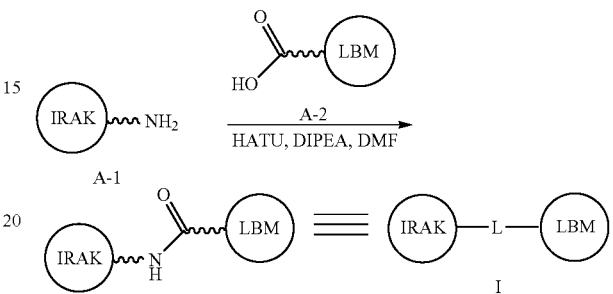

As depicted in Scheme 1, above, amine A-1 is coupled to acid A-2 using the coupling agent HATU in the presence of the base DIPEA in DMF to form a compound of formula I with a linker comprising an amide bond. The squiggly bond, ∼∼∼, represents the portion of the linker between IRAK and the terminal amino group of A-1 or the portion of the linker between LBM and the terminal carboxyl group of A-2, respectively. Additionally, an amide bond can be formed using coupling reagents known in the art such as, but not limited to DCC, DIC, EDC, HBTU, HCTU, PyAOP, PyBrOP, BOP, BOP-Cl, DEPBT, T3P, TATU, TBTU, TNTU, TOTU, TPTU, TSTU, or TDBTU.

In certain embodiments, compounds of the present invention are generally prepared according to Scheme 2 set forth below:

Scheme 2: Synthesis of Compounds of Formula I

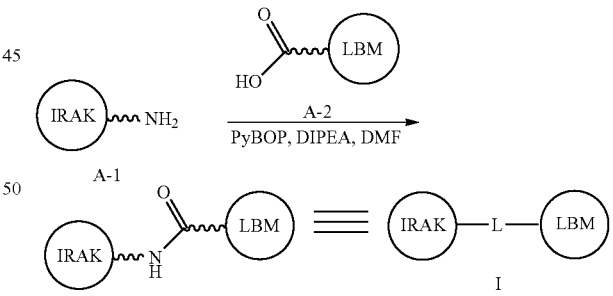

As depicted in Scheme 2, above, amine A-1 is coupled to acid A-2 using the coupling agent PyBOP in the presence of the base DIPEA in DMF to form a compound of formula I with a linker comprising an amide bond. The squiggly bond, ∼∼∼, represents the portion of the linker between IRAK and the terminal amino group of A-1 or the portion of the linker between LBM and the terminal carboxyl group of A-2, respectively. Additionally, an amide bond can be formed using coupling reagents known in the art such as, but not limited to DCC, DIC, EDC, HBTU, HCTU, PyAOP, PyBrOP, BOP, BOP-Cl, DEPBT, T3P, TATU, TBTU, TNTU, TOTU, TPTU, TSTU, or TDBTU.

In certain embodiments, compounds of the present invention are generally prepared according to Scheme 3 set forth below:

Scheme 3: Synthesis of Compounds of Formula I

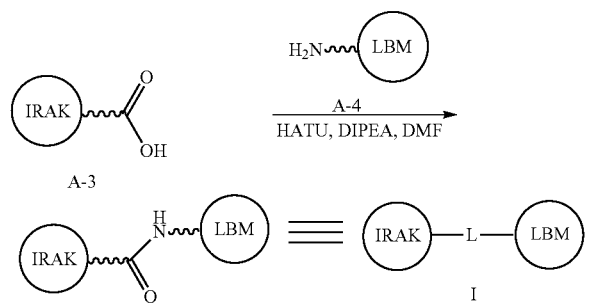

As depicted in Scheme 3, above, acid A-3 is coupled to amine A-4 using the coupling agent HATU in the presence of the base DIPEA in DMF to form a compound of formula I with a linker comprising an amide bond. The squiggly bond, ⁓, represents the portion of the linker between IRAK and the terminal carboxyl group of A-3 or the portion of the linker between LBM and the terminal amino group of A-4, respectively. Additionally, an amide bond can be formed using coupling reagents known in the art such as, but not limited to DCC, DIC, EDC, HBTU, HCTU, PyAOP, PyBrOP, BOP, BOP-Cl, DEPBT, T3P, TATU, TBTU, TNTU, TOTU, TPTU, TSTU, or TDBTU.

In certain embodiments, compounds of the present invention are generally prepared according to Scheme 4 set forth below:

Scheme 4: Synthesis of Compounds of Formula I

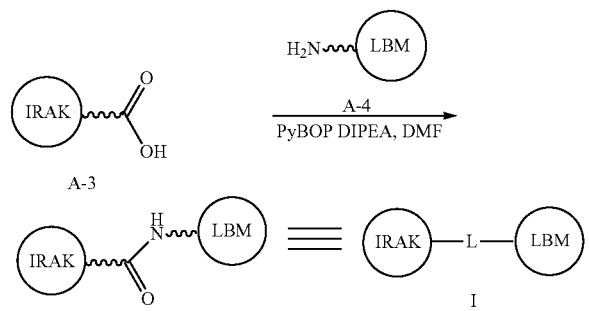

As depicted in Scheme 4, above, acid A-3 is coupled to amine A-4 using the coupling agent PyBOP in the presence of the base DIPEA in DMF to form a compound of formula I with a linker comprising an amide bond. The squiggly bond, ⁓, represents the portion of the linker between IRAK and the terminal carboxyl group of A-3 or the portion of the linker between LBM and the terminal amino group of A-4, respectively. Additionally, an amide bond can be formed using coupling reagents known in the art such as, but not limited to DCC, DIC, EDC, HBTU, HCTU, PyAOP, PyBrOP, BOP, BOP-Cl, DEPBT, T3P, TATU, TBTU, TNTU, TOTU, TPTU, TSTU, or TDBTU.

In certain embodiments, compounds of the present invention are generally prepared according to Scheme 5 set forth below:

Scheme 5: Synthesis of Compounds of Formula I

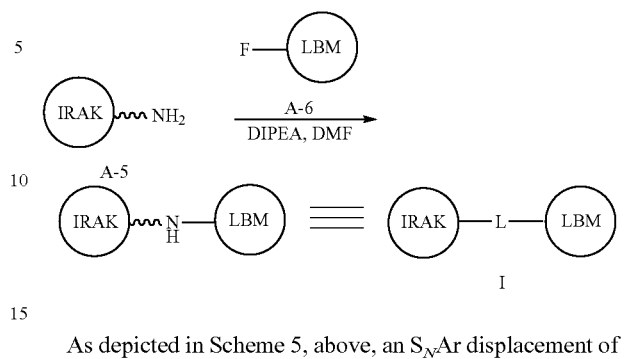

As depicted in Scheme 5, above, an $S_NAr$ displacement of fluoride A-6 by amine A-5 is effected in the presence of the base DIPEA in DMF to form a compound of formula I with a linker comprising a secondary amine. The squiggly bond, ⁓, represents the portion of the linker between IRAK and the terminal amino group of A-5.

In certain embodiments, compounds of the present invention are generally prepared according to Scheme 6 set forth below:

Scheme 6: Synthesis of Compounds of Formula I

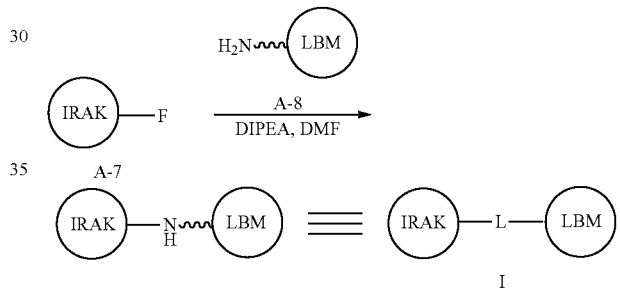

As depicted in Scheme 6, above, an $S_NAr$ displacement of fluoride A-7 by amine A-8 is effected in the presence of the base DIPEA in DMF to form a compound of formula I with a linker comprising a secondary amine. The squiggly bond, ⁓, represents the portion of the linker between LBM and the terminal amino group of A-8.

Scheme 7: Synthesis of Compounds of Formula I

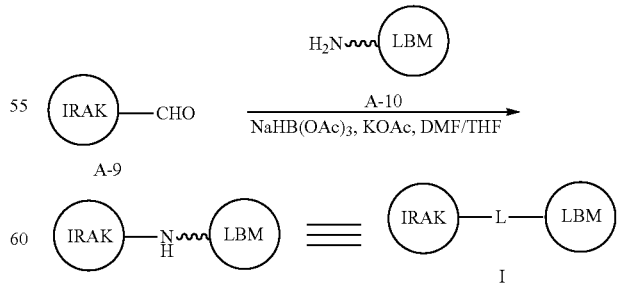

As depicted in Scheme 7, above, reductive amination of the mixture of aldehyde A-9 and amine A-10 is effected in the presence of $NaHB(OAc)_3$ and KOAc in DMF/THF to form a compound of formula I with a linker comprising a secondary amine. The squiggly bond, ⁀⁀⁀ represents the portion of the linker between LBM and the terminal amino group of A-8.

One of skill in the art will appreciate that various functional groups present in compounds of the invention such as aliphatic groups, alcohols, carboxylic acids, esters, amides, aldehydes, halogens and nitriles can be interconverted by techniques well known in the art including, but not limited to reduction, oxidation, esterification, hydrolysis, partial oxidation, partial reduction, halogenation, dehydration, partial hydration, and hydration. "March's Advanced Organic Chemistry", 5$^{th}$ Ed., Ed.: Smith, M. B. and March, J., John Wiley & Sons, New York: 2001, the entirety of which is incorporated herein by reference. Such interconversions may require one or more of the aforementioned techniques, and certain methods for synthesizing compounds of the invention are described below in the Exemplification.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably degrade and/or inhibit an IRAK protein kinase, or a mutant thereof, in a biological sample or in a patient. In certain embodiments, the amount of compound in compositions of this invention is such that is effective to measurably degrade and/or inhibit an IRAK protein kinase, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily or degratorily active metabolite or residue thereof.

As used herein, the term "inhibitorily active metabolite or residue thereof" means that a metabolite or residue thereof is also an inhibitor of an IRAK protein kinase, or a mutant thereof.

As used herein, the term "degratorily active metabolite or residue thereof" means that a metabolite or residue thereof is also a degrader of an IRAK protein kinase, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the degradation and/or inhibition of kinase activity of one or more enzymes.

Examples of kinases that are degraded and/or inhibited by the compounds and compositions described herein and against which the methods described herein are useful include those of the interleukin-1 receptor-associated kinase (IRAK) family of kinases, the members of which include IRAK-1, IRAK-2, and IRAK-4, or a mutant thereof. Li et al., "IRAK-4: A novel member of the IRAK family with the properties of an IRAK-kinase," PNAS 2002, 99 (8), 5567-5572, Flannery et al., "The interleukin-1 receptor-associated kinases: Critical regulators of innate immune signaling" Biochem Pharm 2010, 80 (12), 1981-1991 incorporated by reference in its entirety.

The activity of a compound utilized in this invention as a degrader and/or inhibitor of IRAK-1, IRAK-2, and/or IRAK-4, or a mutant thereof, may be assayed in vitro, in vivo or in a cell line. In vitro assays include assays that determine inhibition of either the phosphorylation activity and/or the subsequent functional consequences, or ATPase activity of activated IRAK-1, IRAK-2, and/or IRAK-4, or a mutant thereof. Alternate in vitro assays quantitate the ability of the inhibitor to bind to IRAK-1, IRAK-2 and/or IRAK-4. Inhibitor binding may be measured by radiolabeling the inhibitor prior to binding, isolating the inhibitor/IRAK-1, inhibitor/IRAK-2, or inhibitor/IRAK-4 complex and determining the amount of radiolabel bound. Alternatively, inhibitor binding may be determined by running a competition experiment where new inhibitors are incubated with IRAK-1, IRAK-2, and/or IRAK-4 bound to known radioligands. Representative in vitro and in vivo assays useful in assaying an IRAK-4 inhibitor include those described and disclosed in, e.g., Kim et al., "A critical role for IRAK4 kinase activity in Toll-like receptor-mediated innate immunity," *J. Exp. Med.* 2007 204 (5), 1025-1036; Lebakken et al., "A Fluorescence Lifetime Based Binding Assay to Characterize Kinase Inhibitors," *J Biomol. Screen.* 2007, 12 (6), 828-841; Maschera et al., "Overexpression of an enzymatically inactive interleukin-1-receptor-associated kinase activates nuclear factor-κB," *Biochem. J.* 1999, 339, 227-231; Song et al., "The kinase activities of interleukin-e receptor associated kinase (IRAK)-1 and 4 are redundant in the control of inflammatory cytokine expression in human cells," *Mol. Immunol.* 2009, 46, 1458-1466, each of, the entirety of each of which is herein incorporated by reference. Detailed conditions for assaying a compound utilized in this invention as a degrader and/or inhibitor of IRAK-1, IRAK-2, and/or IRAK-4, or a mutant thereof, are set forth in the Examples below.

The best characterized member of the IRAK family is the serine/threonine kinase IRAK-4. IRAK-4 is implicated in signaling innate immune responses from Toll-like receptors (TLRs) and Toll/IL-1 receptors (TIRs).

Innate immunity detects pathogens through the recognition of pathogen-associated molecular patterns by TLRs, when then links to the adaptive immune response. TLRs recognize conserved structures of both microbes and endogenous molecules. TLRs which recognize bacterial and fungal components are located on the cell surface, whereas TLRs which recognize viral or microbial nucleic acids are localized to intracellular membranes such as endosomes and phagosomes. Cell surface TLRs can be targeted by small molecules and antibodies, whereas intracellular TLRs require targeting with oligonucleotides.

TLRs mediate the innate immune response by upregulating the expression of inflammatory genes in multiple target cells. See, e.g., Sen et al., "Transcriptional signaling by double-stranded RNA: role of TLR3," *Cytokine & Growth Factor Rev.* 2005, 16, 1-14, incorporated by reference in its entirety. While TLR-mediated inflammatory response is critical for innate immunity and host defense against infections, uncontrolled inflammation is detrimental to the host leading to sepsis and chronic inflammatory diseases, such as chronic arthritis, atherosclerosis, multiple sclerosis, cancers, autoimmune disorders such as rheumatoid arthritis, lupus, asthma, psoriasis, and inflammatory bowel diseases.

Upon binding of a ligand, most TLRs recruit the adaptor molecule MyD88 through the TIR domain, mediating the MyD88-dependent pathway. MyD88 then recruits IRAK-4, which engages with the nuclear factor-κB (NF-κB), mitogen-activated protein (MAP) kinase and interferon-regulatory factor cascades and leads to the induction of pro-inflammatory cytokines. The activation of NF-κB results in the induction of inflammatory cytokines and chemokines, such as TNF-α, IL-1α, IL-6 and IL-8. The kinase activity of IRAK-4 has been shown to play a critical role in the TLR-mediated immune and inflammatory responses. IRAK4 is a key mediator of the innate immune response orchestrated by interleukin-1 receptor (IL-1R), interleukin-18 receptor (IL-18R), IL-33 receptor (IL-33R), and Toll-like receptors (TLRs). Inactivation of IRAK-1 and/or IRAK-4 activity has been shown to result in diminished production of cytokines and chemokines in response to stimulation of IL-1 and TLR ligands. See, e.g., Picard et al., "Clinical features and outcome of patients with IRAK-4 and MyD88 deficiency," *Medicine (Baltimore)*, 2010, 89 (6), 043-25; Li, "IRAK4 in TLR/IL-1R signaling: Possible clinical applications," *Eur. J. Immunology* 2008, 38:614-618; Cohen et al., "Targeting protein kinases for the development of anti-inflammatory drugs," *Curr. Opin. Cell Bio.* 2009, 21:317-324; Flannery et al., "The interleukin-1 receptor-associated kinases: Critical regulators of innate immune signalling," *Biochem. Pharm.* 2010, 80 (12), 1981-1991; Gottipati et al., "IRAK1: A critical signaling mediator of innate immunity," *Cellular Signaling* 2008, 20, 269-276; Kim et al., "A critical role for IRAK4 kinase activity in Toll-like receptor-mediated innate immunity," *J. Exp. Med.* 2007 204 (5), 1025-1036; Koziczak-Holbro et al., "IRAK-4 Kinase Activity Is Required for Interleukin-1 (IL-1) Receptor- and Toll-like Receptor 7-mediated Signaling and Gene Expression," *J. Biol. Chem.* 2007, 282 (18), 13552-13560; Kubo-Murai et al., "IRAK-4-dependent Degradation of IRAK-1 is a Negative Feedback Signal for TLR-mediated NF-κB Activation," *J. Biochem.* 2008, 143, 295-302; Maschera et al., "Overexpression of an enzymatically inactive interleukin-1-receptor-associated kinase activates nuclear factor-κB," *Biochem. J.* 1999, 339, 227-231; Lin et al., "Helical assembly in the MyD88-IRAK4-IRAK2 complex in TLR/IL-1R signalling," *Nature* 2010, 465 (17), 885-891; Suzuki et al., "IRAK-4 as the central TIR signaling mediator in innate immunity," *TRENDS in Immunol.* 2002, 23 (10), 503-506; Suzuki et al., "Severe impairment of interleukin-1 and Toll-like receptor signalling in mice lacking IRAK-4," *Nature* 2002, 416, 750-754; Swantek et al., "IL-1 Receptor-Associated Kinase Modulates Host Responsiveness to Endotoxin," *J. Immunol.* 2000, 164, 4301-4306; Hennessy, E., et al., "Targeting Toll-like receptors: emerging therapeutics?" *Nature Reviews*, vol. 9, pp: 293-307 (2010); Dinarello, C. "Interleukin-18 and the Pathogenesis of Inflammatory Diseases," *Seminars in Nephrology*, vol. 27, no. 1, pp: 98-114 (2007), each of, the entirety of each of which is herein incorporated by reference. In fact, knockdown mice that express a catalytically inactive mutant IRAK-4 protein are completely resistant to septic shock and show impaired IL-1 activity. Moreover, these mice are resistant to joint and bone inflammation/destruction in an arthritis model, suggesting that IRAK-4 may be targeted to treat chronic inflammation. Further, while IRAK-4 appears to be vital for childhood immunity against some pyogenic bacteria, it has been shown to play a redundant role in protective immunity to most infections in adults, as demonstrated by one study in which patients older than 14 lacking IRAK-4 activity exhibited no invasive infections. Cohen et al., "Targeting protein kinases for the development of anti-inflammatory drugs," *Curr. Opin. Cell Bio.* 2009, 21:317-324; Ku et al., "Selective predisposition to bacterial infections in IRAK-4-deficient children: IRAK-4-dependent TLRs are otherwise redundant in protective immunity," *J. Exp. Med.* 2007, 204 (10), 2407-2422; Picard et al., "Inherited human IRAK-4 deficiency: an update," *Immunol. Res.* 2007, 38, 347-352; Song et al., "The kinase activities of interleukin-e receptor associated kinase (IRAK)-1 and 4 are redundant in the control of inflammatory cytokine expression in human cells," *Mol. Immunol.* 2009, 46, 1458-1466; Rokosz, L. et al., "Kinase inhibitors as drugs for chronic inflammatory and immunological diseases: progress and challenges," *Expert Opinions on Therapeutic Targets*, 12 (7), pp: 883-903 (2008); Gearing, A. "Targeting toll-like receptors for drug development: a summary of commercial approaches," *Immunology and Cell Biology*, 85, pp: 490-494 (2007); Dinarello, C. "IL-1: Discoveries, controversies and future directions," *European Journal of Immunology*, 40, pp: 595-653 (2010), each of, the entirety of each of which is herein incorporated by reference. Because TLR activation triggers IRAK-4 kinase activity, IRAK-4 inhibition presents an attractive target for treating the underlying causes of inflammation in countless diseases.

Representative IRAK-4 inhibitors include those described and disclosed in e.g., Buckley et al., *Bioorg. Med. Chem. Lett.* 2008, 18, 3211-3214; Buckley et al., *Bioorg. Med. Chem. Lett.* 2008, 18, 3291-3295; Buckley et al., *Bioorg. Med. Chem. Lett.* 2008, 18, 3656-3660; Powers et al., "Discovery and initial SAR of inhibitors of interleukin-1 receptor-associated kinase-4," *Bioorg. Med. Chem. Lett.* 2006, 16, 2842-2845; Wng et al., "IRAK-4 Inhibitors for Inflammation," *Curr. Topics in Med. Chem.* 2009, 9, 724-737, each of, the entirety of each of which is herein incorporated by reference.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are degraders and/or inhibitors of one of more of IRAK-1, IRAK-2, and/or IRAK-4 and are therefore useful for treating one or more disorders associated with activity of one or more of IRAK-1, IRAK-2, and/or IRAK-4. Thus, in certain embodiments, the present invention provides a method for treating a IRAK-1-mediated, a IRAK-2-mediated, and/or a IRAK-4-mediated disorder comprising the step of administering to a patient in need thereof a compound of the present invention, or pharmaceutically acceptable composition thereof.

As used herein, the terms "IRAK-1-mediated", "IRAK-2-mediated", and/or "IRAK-4-mediated" disorders, diseases, and/or conditions as used herein means any disease or other deleterious condition in which one or more of IRAK-1, IRAK-2, and/or IRAK-4, or a mutant thereof, are known to play a role. Accordingly, another embodiment of the present invention relates to treating or lessening the severity of one or more diseases in which one or more of IRAK-1, IRAK-2, and/or IRAK-4, or a mutant thereof, are known to play a role.

In some embodiments, the present invention provides a method for treating one or more disorders, diseases, and/or conditions wherein the disorder, disease, or condition is a cancer, a neurodegenerative disorder, a viral disease, an autoimmune disease, an inflammatory disorder, a hereditary disorder, a hormone-related disease, a metabolic disorder, conditions associated with organ transplantation, immunodeficiency disorders, a destructive bone disorder, a proliferative disorder, an infectious disease, a condition associated with cell death, thrombin-induced platelet aggregation, liver disease, pathologic immune conditions involving T cell activation, a cardiovascular disorder, or a CNS disorder.

Diseases and conditions treatable according to the methods of this invention include, but are not limited to, cancer (see, e.g., Ngo, V. et al., "Oncogenically active MYD88 mutations in human lymphoma," *Nature*, vol. 000, pp: 1-7 (2010); Lust, J. et al., "Induction of a Chronic Disease State in patients With Smoldering of Indolent Multiple Myeloma by Targeting Interleukin 13-Induced Interleukin 6 Production and the Myeloma Proliferative Component," *Mayo Clinic Proceedings*, 84 (2), pp: 114-122 (2009)), diabetes, cardiovascular disease, viral disease, autoimmune diseases such as lupus (see, e.g., Dinarello, C. "Interleukin-18 and the Pathogenesis of Inflammatory Diseases," *Seminars in Nephrology*, vol. 27, no. 1, pp: 98-114 (2007); Cohen et al., "Targeting protein kinases for the development of antiinflammatory drugs," *Curr Opin. Cell Bio.* 2009, 21:317-324) and rheumatoid arthritis (see, e.g., Geyer, M. et al., "Actual status of antiinterleukin-1 therapies in rheumatic diseases," *Current Opinion in Rheumatology*, 22, pp: 246-251 (2010)), autoinflammatory syndromes (see, e.g., Hoffman, H. et al., "Efficacy and Safety of Rilonacept (Interleukin-1 Trap) in Patients with Cryopyrin-Associated Periodic Syndromes," *Arthritis & Rheumatism*, vol. 58, no. 8, pp: 2443-2452 (2008)), atherosclerosis, psoriasis, allergic disorders, inflammatory bowel disease (see, e.g., Cario, E. "Therapeutic Impact of Toll-like Receptors on Inflammatory Bowel Diseases: A Multiple-edged Sword," *Inflamm. Bowel Dis.*, 14, pp: 411-421 (2008)), inflammation (see, e.g., Dinarello, C. "Interleukin 1 and interleukin 18 as mediators of inflammation and the aging process," *The American Journal of Clinical Nutrition*, 83, pp: 447S-455S (2006)), acute and chronic gout and gouty arthritis (see, e.g., Terkeltaub, R. "Update on gout: new therapeutic strategies and options," *Nature*, vol. 6, pp: 30-38 (2010); Weaver, A. "Epidemiology of gout," *Cleveland Clinic Journal of Medicine*, vol. 75, suppl. 5, pp: S9-S12 (2008); Dalbeth, N. et al., "Hyperuricaemia and gout: state of the art and future perspectives," *Annals of Rheumatic Diseases*, 69, pp: 1738-1743 (2010); Martinon, F. et al., "Gout-associated uric acid crystals activate the NALP3 inflammasome," *Nature*, vol. 440, pp: 237-241 (2006); So, A. et al., "A pilot study of IL-1 inhibition by anakinra in acute gout," *Arthritis Research & Therapy*, vol. 9, no. 2, pp: 1-6 (2007); Terkeltaub, R. et al., "The interleukin 1 inhibitor rilonacept in treatment of chronic gouty arthritis: results of a placebo-controlled, monosequence crossover, non-randomised, single-blind pilot study," *Annals of Rheumatic Diseases*, 68, pp: 1613-1617 (2009); Torres, R. et al., "Hyperalgesia, synovitis and multiple biomarkers of inflammation are suppressed by interleukin 1 inhibition in a novel animal model of gouty arthritis," *Annals of Rheumatic Diseases*, 68, pp: 1602-1608 (2009)), neurological disorders, metabolic syndrome (see, e.g., Troseid, M. "The role of interleukin-18 in the metabolic syndrome," *Cardiovascular Diabetology*, 9:11, pp: 1-8 (2010)), immunodeficiency disorders such as AIDS and HIV (see, e.g., Iannello, A. et al., "Role of Interleukin-18 in the Development and Pathogenesis of AIDS," *AIDS Reviews*, 11, pp: 115-125 (2009)), destructive bone disorders (see, e.g., Hennessy, E., et al., "Targeting Toll-like receptors: emerging therapeutics?" *Nature Reviews*, vol. 9, pp: 293-307 (2010)), osteoarthritis, proliferative disorders, Waldenström's Macroglobulinemia (see, e.g., Treon, et al., "Whole genome sequencing reveals a widely expressed mutation (MYD88 L265P) with oncogenic activity in Waldenström's Macroglobulinemia" $53^{rd}$ ASH Annual Meeting; Xu, et al., "A somatic variant in MYD88 (L256P) revealed by whole genome sequencing differentiates lymphoplasmacytic lymphoma from marginal zone lymphomas" $53^{rd}$ ASH Annual Meeting; Yang et al., "Disruption of MYD88 pathway signaling leads to loss of constitutive IRAK1, NK-kB and JAK/STAT signaling and induces apoptosis of cells expressing the MYD88 L265P mutation in Waldenström's Macroglobulinemia" $53^{rd}$ ASH Annual Meeting; Iriyama et al., "Clinical significance of genetic mutations of CD79B, CARD11, MYD88, and EZH2 genes in diffuse large B-cell lymphoma patients" $53^{rd}$ ASH Annual Meeting; infectious diseases, conditions associated with cell death, pathologic immune conditions involving T cell activation, and CNS disorders in a patient. In one embodiment, a human patient is treated with a compound of the current invention and a pharmaceutically acceptable carrier, adjuvant, or vehicle, wherein said compound is present in an amount to measurably degrade and/or inhibit IRAK-1 only, IRAK-2-only, IRAK-4-only and/or IRAK1 and IRAK4 kinase activity.

Compounds of the current invention are useful in the treatment of a proliferative disease selected from a benign or malignant tumor, solid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, especially colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins and Non-Hodgkins, a mammary carcinoma, follicular carcinoma, undifferentiated carcinoma, papillary carcinoma, seminoma, melanoma, an IL-1 driven disorder, an MyD88 driven disorder, Smoldering of indolent multiple myeloma, or hematological malignancies (including leukemia, diffuse large B-cell lymphoma (DLBCL), ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, Waldenström's macroglobulinemia (WM), splenic marginal zone lymphoma, multiple myeloma, plasmacytoma, intravascular large B-cell lymphoma).

In some embodiments the proliferative disease which can be treated according to the methods of this invention is an MyD88 driven disorder. In some embodiments, the MyD88 driven disorder which can be treated according to the methods of this invention is selected from ABC DLBCL, Waldenström's macroglobulinemia, Hodgkin's lymphoma, primary cutaneous T-cell lymphoma and chronic lymphocytic leukemia.

In some embodiments the proliferative disease which can be treated according to the methods of this invention is an IL-1 driven disorder. In some embodiments the IL-1 driven disorder is Smoldering of indolent multiple myeloma.

Compounds according to the invention are useful in the treatment of inflammatory or obstructive airways diseases, resulting, for example, in reduction of tissue damage, airways inflammation, bronchial hyperreactivity, remodeling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics.

Compounds according to the invention are useful in the treatment of heteroimmune diseases. Examples of such heteroimmune diseases include, but are not limited to, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, such as therapy for or intended to restrict or abort symptomatic attack when it occurs, for example antiinflammatory or bronchodilatory. Prophylactic benefit in asthma may in particular be apparent in subjects prone to "morning dipping". "Morning dipping" is a recognized asthmatic syndrome, common to a substantial percentage of asthmatics and characterised by asthma attack, e.g. between the hours of about 4 to 6 am, i.e. at a time normally substantially distant form any previously administered symptomatic asthma therapy.

Compounds of the current invention can be used for other inflammatory or obstructive airways diseases and conditions to which the present invention is applicable and include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, but not limited to, acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

With regard to their anti-inflammatory activity, in particular in relation to inhibition of eosinophil activation, compounds of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Compounds of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, pemphigus vulgaris, pemphigus foliaceus, paraneoplastic pemphigus, epidermolysis bullosa acquisita, acne vulgaris, and other inflammatory or allergic conditions of the skin.

Compounds of the invention may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments the inflammatory disease which can be treated according to the methods of this invention is an disease of the skin. In some embodiments, the inflammatory disease of the skin is selected from contact dermatitits, atompic dermatitis, alopecia areata, erythema multiforma, dermatitis herpetiformis, scleroderma, vitiligo, hypersensitivity angiitis, urticaria, bullous pemphigoid, pemphigus vulgaris, pemphigus *foliaceus*, paraneoplastic pemphigus, epidermolysis bullosa acquisita, and other inflammatory or allergic conditions of the skin.

In some embodiments the inflammatory disease which can be treated according to the methods of this invention is selected from acute and chronic gout, chronic gouty arthritis, psoriasis, psoriatic arthritis, rheumatoid arthritis, Juvenile rheumatoid arthritis, Systemic jubenile idiopathic arthritis (SJIA), Cryopyrin Associated Periodic Syndrome (CAPS), and osteoarthritis.

In some embodiments the inflammatory disease which can be treated according to the methods of this invention is a TH17 mediated disease. In some embodiments the TH17 mediated disease is selected from Systemic lupus erythematosus, Multiple sclerosis, and inflammatory bowel disease (including Crohn's disease or ulcerative colitis).

In some embodiments the inflammatory disease which can be treated according to the methods of this invention is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis.

Cardiovascular diseases which can be treated according to the methods of this invention include, but are not limited to, restenosis, cardiomegaly, atherosclerosis, myocardial infarction, ischemic stroke, congestive heart failure, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, and deep venous thrombosis.

In some embodiments, the neurodegenerative disease which can be treated according to the methods of this invention include, but are not limited to, Alzheimer's disease, Parkinson's disease, amyotrophic lateral sclerosis, Huntington's disease, cerebral ischemia, and neurodegenerative disease caused by traumatic injury, glutamate neurotoxicity, hypoxia, epilepsy, treatment of diabetes, metabolic syndrome, obesity, organ transplantation and graft versus host disease.

The loss of IRAK4 function results in decreased AP3 levels in an in vivo murine model of Alzheimer's disease and was associated with diminished microgliosis and astrogliosis in aged mice. Analysis of microglia isolated from the adult mouse brain revealed an altered pattern of gene expression associated with changes in microglial phenotype that were associated with expression of IRF transcription factors that govern microglial phenotype. Further, loss of IRAK4 function also promoted amyloid clearance mechanisms, including elevated expression of insulin-degrading enzyme. Finally, blocking IRAK function restored olfactory behavior (Cameron et al. "Loss of Interleukin Receptor-Associated Kinase 4 Signaling Suppresses Amyloid Pathology and Alters Microglial Phenotype in a Mouse Model of Alzheimer's Disease" Journal of Neuroscience (2012) 32 (43), 15112-15123.

In some embodiments the invention provides a method of treating, preventing or lessening the severity of Alzheimer's disease comprising administering to a patient in need thereof a compound of formula I or a pharmaceutically acceptable salt or composition thereof.

In some embodiments the invention provides a method of treating a disease or condition commonly occurring in connection with transplantation. In some embodiments, the disease or condition commonly occurring in connection with transplantation is selected from organ transplantation, organ transplant rejection, and graft versus host disease.

In some embodiments the invention provides a method of treating a metabolic disease. In some embodiments the metabolic disease is selected from Type 1 diabetes, Type 2 diabetes, metabolic syndrome, and obesity.

In some embodiments the invention provides a method of treating a viral disease. In some embodiments, the viral infection is HIV infection.

Furthermore, the invention provides the use of a compound according to the definitions herein, or a pharmaceutically acceptable salt, or a hydrate or solvate thereof for the preparation of a medicament for the treatment of a proliferative disease, an inflammatory disease, an obstructive respiratory disease, a cardiovascular disease, a metabolic disease, a neurological disease, a neurodegenerative disease, a viral disease, or a disorder commonly occurring in connection with transplantation.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

In some embodiments, the present invention provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

One or more other therapeutic agent may be administered separately from a compound or composition of the invention, as part of a multiple dosage regimen. Alternatively, one or more other therapeutic agents agents may be part of a single dosage form, mixed together with a compound of this invention in a single composition. If administered as a multiple dosage regime, one or more other therapeutic agent and a compound or composition of the invention may be administered simultaneously, sequentially or within a period of time from one another, for example within 1, 2, 3, 4, 5, 6, 7, 8, 9, 10, 11, 12, 13, 14, 15, 16, 17, 18, 18, 20, 21, 22, 23, or 24 hours from one another. In some embodiments, one or more other therapeutic agent and a compound or composition of the invention are administered as a multiple dosage regimen within greater than 24 hours apart.

In one embodiment, the present invention provides a composition comprising a compound of formula I and one or more additional therapeutic agents. The therapeutic agent may be administered together with a compound of formula I, or may be administered prior to or following administration of a compound of formula I. Suitable therapeutic agents are described in further detail below. In certain embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a compound of formula I and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®)

and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-Bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating gout comprising administering to a patient in need thereof a compound of formula I and one or more additional therapeutic agents selected from non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol and febuxostat (Uloric®).

In another embodiment, the present invention provides a method of treating rheumatoid arthritis comprising administering to a patient in need thereof a compound of formula I and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating lupus comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating inflammatory bowel disease comprising administering to a patient in need thereof a compound of formula I and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a compound of formula I and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-Bid®, Uniphyl®, Theo-24®) and aminophylline, and IgE antibodies such as omalizumab (Xolair®).

In some embodiments, the present invention provides a method of treating COPD comprising administering to a patient in need thereof a compound of formula I and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-Bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, In some embodiments, the present invention provides a method of treating HIV comprising administering to a patient in need thereof a compound of formula I and one or more additional therapeutic agents selected from nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), and combinations thereof.

In another embodiment, the present invention provides a method of treating a hematological malignancy comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a solid tumor comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a hematological malignancy comprising administering to a patient in need thereof a compound of formula I and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a compound of formula I and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating Waldenström's macroglobulinemia comprising administering to a patient in need thereof a compound of formula I and one or more additional therapeutic agents selected from chlorambucil (Leukeran®), cyclophosphamide (Cytoxan®, Neosar®), fludarabine (Fludara®), cladribine (Leustatin®), rituximab (Rituxan®), a hedgehog signaling inhibitor, a BTK inhibitor, a JAK/pan-JAK inhibitor, a TYK2 inhibitor, a PI3K inhibitor, and a SYK inhibitor.

In some embodiments, one or more other therapeutic agent is an antagonist of the hedgehog pathway. Approved hedgehog pathway inhibitors which may be used in the present invention include sonidegib (Odomzo®, Sun Pharmaceuticals); and vismodegib (Erivedge®, Genentech), both for treatment of basal cell carcinoma.

In some embodiments, one or more other therapeutic agent is a Poly ADP ribose polymerase (PARP) inhibitor. In some embodiments, a PARP inhibitor is selected from olaparib (Lynparza®, AstraZeneca); rucaparib (Rubraca®, Clovis Oncology); niraparib (Zejula®, Tesaro); talazoparib (MDV3800/BMN 673/LT00673, Medivation/Pfizer/Biomarin); veliparib (ABT-888, AbbVie); and BGB-290 (BeiGene, Inc.).

In some embodiments, one or more other therapeutic agent is a histone deacetylase (HDAC) inhibitor. In some embodiments, an HDAC inhibitor is selected from vorinostat (Zolinza®, Merck); romidepsin (Istodax®, Celgene); panobinostat (Farydak®, Novartis); belinostat (Beleodaq®, Spectrum Pharmaceuticals); entinostat (SNDX-275, Syndax Pharmaceuticals) (NCT00866333); and chidamide (Epidaza®, HBI-8000, Chipscreen Biosciences, China).

In some embodiments, one or more other therapeutic agent is a CDK inhibitor, such as a CDK4/CDK6 inhibitor. In some embodiments, a CDK 4/6 inhibitor is selected from palbociclib (Ibrance®, Pfizer); ribociclib (Kisqali®, Novartis); abemaciclib (Ly2835219, Eli Lilly); and trilaciclib (G1T28, G1 Therapeutics).

In some embodiments, one or more other therapeutic agent is a folic acid inhibitor. Approved folic acid inhibitors useful in the present invention include pemetrexed (Alimta®, Eli Lilly).

In some embodiments, one or more other therapeutic agent is a CC chemokine receptor 4 (CCR4) inhibitor. CCR4 inhibitors being studied that may be useful in the present invention include mogamulizumab (Poteligeo®, Kyowa Hakko Kirin, Japan).

In some embodiments, one or more other therapeutic agent is an isocitrate dehydrogenase (IDH) inhibitor. IDH inhibitors being studied which may be used in the present invention include AG120 (Celgene; NCT02677922); AG221 (Celgene, NCT02677922; NCT02577406); BAY1436032 (Bayer, NCT02746081); IDH305 (Novartis, NCT02987010).

In some embodiments, one or more other therapeutic agent is an arginase inhibitor. Arginase inhibitors being studied which may be used in the present invention include AEB1102 (pegylated recombinant arginase, Aeglea Biotherapeutics), which is being studied in Phase 1 clinical trials for acute myeloid leukemia and myelodysplastic syndrome (NCT02732184) and solid tumors (NCT02561234); and CB-1158 (Calithera Biosciences).

In some embodiments, one or more other therapeutic agent is a glutaminase inhibitor. Glutaminase inhibitors being studied which may be used in the present invention include CB-839 (Calithera Biosciences).

In some embodiments, one or more other therapeutic agent is an antibody that binds to tumor antigens, that is, proteins expressed on the cell surface of tumor cells. Approved antibodies that bind to tumor antigens which may be used in the present invention include rituximab (Rituxan®, Genentech/BiogenIdec); ofatumumab (anti-CD20, Arzerra®, GlaxoSmithKline); obinutuzumab (anti-CD20, Gazyva®, Genentech), ibritumomab (anti-CD20 and Yttrium-90, Zevalin®, Spectrum Pharmaceuticals); daratumumab (anti-CD38, Darzalex®, Janssen Biotech), dinutuximab (anti-glycolipid GD2, Unituxin®, United Therapeutics); trastuzumab (anti-HER2, Herceptin®, Genentech); ado-trastuzumab emtansine (anti-HER2, fused to emtansine, Kadcyla®, Genentech); and pertuzumab (anti-HER2, Perjeta®, Genentech); and brentuximab vedotin (anti-CD30-drug conjugate, Adcetris®, Seattle Genetics).

In some embodiments, one or more other therapeutic agent is a topoisomerase inhibitor. Approved topoisomerase inhibitors useful in the present invention include irinotecan (Onivyde®, Merrimack Pharmaceuticals); topotecan (Hycamtin®, GlaxoSmithKline). Topoisomerase inhibitors being studied which may be used in the present invention include pixantrone (Pixuvri®, CTI Biopharma).

In some embodiments, one or more other therapeutic agent is an inhibitor of anti-apoptotic proteins, such as BCL-2. Approved anti-apoptotics which may be used in the present invention include venetoclax (Venclexta®, AbbVie/Genentech); and blinatumomab (Blincyto®, Amgen). Other therapeutic agents targeting apoptotic proteins which have undergone clinical testing and may be used in the present invention include navitoclax (ABT-263, Abbott), a BCL-2 inhibitor (NCT02079740).

In some embodiments, one or more other therapeutic agent is an androgen receptor inhibitor. Approved androgen receptor inhibitors useful in the present invention include enzalutamide (Xtandi®, Astellas/Medivation); approved inhibitors of androgen synthesis include abiraterone (Zytiga®, Centocor/Ortho); approved antagonist of gonadotropin-releasing hormone (GnRH) receptor (degaralix, Firmagon®, Ferring Pharmaceuticals).

In some embodiments, one or more other therapeutic agent is a selective estrogen receptor modulator (SERM), which interferes with the synthesis or activity of estrogens. Approved SERMs useful in the present invention include raloxifene (Evista®, Eli Lilly).

In some embodiments, one or more other therapeutic agent is an inhibitor of bone resorption. An approved therapeutic which inhibits bone resorption is Denosumab (Xgeva®, Amgen), an antibody that binds to RANKL, prevents binding to its receptor RANK, found on the surface of osteoclasts, their precursors, and osteoclast-like giant cells, which mediates bone pathology in solid tumors with osseous metastases. Other approved therapeutics that inhibit bone resorption include bisphosphonates, such as zoledronic acid (Zometa®, Novartis).

In some embodiments, one or more other therapeutic agent is an inhibitor of interaction between the two primary p53 suppressor proteins, MDMX and MDM2. Inhibitors of p53 suppression proteins being studied which may be used in the present invention include ALRN-6924 (Aileron), a stapled peptide that equipotently binds to and disrupts the interaction of MDMX and MDM2 with p53. ALRN-6924 is currently being evaluated in clinical trials for the treatment of AML, advanced myelodysplastic syndrome (MDS) and peripheral T-cell lymphoma (PTCL) (NCT02909972; NCT02264613).

In some embodiments, one or more other therapeutic agent is an inhibitor of transforming growth factor-beta (TGF-beta or TGFβ). Inhibitors of TGF-beta proteins being studied which may be used in the present invention include NIS793 (Novartis), an anti-TGF-beta antibody being tested in the clinic for treatment of various cancers, including breast, lung, hepatocellular, colorectal, pancreatic, prostate and renal cancer (NCT 02947165). In some embodiments, the inhibitor of TGF-beta proteins is fresolimumab (GC1008; Sanofi-Genzyme), which is being studied for melanoma (NCT00923169); renal cell carcinoma (NCT00356460); and non-small cell lung cancer (NCT02581787). Additionally, in some embodiments, the additional therapeutic agent is a TGF-beta trap, such as described in Connolly et al. (2012) Int'l J. Biological Sciences 8:964-978. One therapeutic compound currently in clinical trials for treatment of solid tumors is M7824 (Merck KgaA—formerly MSB0011459X), which is a bispecific, anti-PD-L1/TGFβ trap compound (NCT02699515); and (NCT02517398). M7824 is comprised of a fully human IgG1 antibody against PD-L1 fused to the extracellular domain of human TGF-beta receptor II, which functions as a TGFβ "trap."

In some embodiments, one or more other therapeutic agent is selected from glembatumumab vedotin-monomethyl auristatin E (MMAE) (Celldex), an anti-glycoprotein NMB (gpNMB) antibody (CR011) linked to the cytotoxic MMAE. gpNMB is a protein overexpressed by multiple tumor types associated with cancer cells' ability to metastasize.

In some embodiments, one or more other therapeutic agent is an antiproliferative compound. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF 1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZd$_6$244 from AstraZeneca, PD181461 from Pfizer and leucovorin.

In some embodiments, the present invention provides a method of treating Alzheimer's disease comprising administering to a patient in need thereof a compound of formula I and one or more additional therapeutic agents selected from donepezil (Aricept®), rivastigmine (Excelon®), galantamine (Razadyne®), tacrine (Cognex®), and memantine (Namenda®).

In some embodiments, one or more other therapeutic agent is a taxane compound, which causes disruption of microtubules, which are essential for cell division. In some embodiments, a taxane compound is selected from paclitaxel (Taxol®, Bristol-Myers Squibb), docetaxel (Taxotere®, Sanofi-Aventis; Docefrez®, Sun Pharmaceutical), albumin-bound paclitaxel (Abraxane®; Abraxis/Celgene), cabazitaxel (Jevtana®, Sanofi-Aventis), and SID530 (SK Chemicals, Co.) (NCT00931008).

In some embodiments, one or more other therapeutic agent is a nucleoside inhibitor, or a therapeutic agent that interferes with normal DNA synthesis, protein synthesis, cell replication, or will otherwise inhibit rapidly proliferating cells.

In some embodiments, a nucleoside inhibitor is selected from trabectedin (guanidine alkylating agent, Yondelis®, Janssen Oncology), mechlorethamine (alkylating agent, Valchlor®, Aktelion Pharmaceuticals); vincristine (Oncovin®, Eli Lilly; Vincasar®, Teva Pharmaceuticals; Marqibo®, Talon Therapeutics); temozolomide (prodrug to alkylating agent 5-(3-methyltriazen-1-yl)-imidazole-4-carboxamide (MTIC) Temodar®, Merck); cytarabine injection (ara-C, antimetabolic cytidine analog, Pfizer); lomustine (alkylating agent, CeeNU®, Bristol-Myers Squibb; Gleostine®, NextSource Biotechnology); azacitidine (pyrimidine nucleoside analog of cytidine, Vidaza®, Celgene); omacetaxine mepesuccinate (cephalotaxine ester) (protein synthesis inhibitor, Synribo®; Teva Pharmaceuticals); asparaginase *Erwinia chrysanthemi* (enzyme for depletion of asparagine, Elspar®, Lundbeck; Erwinaze®, EUSA Pharma); eribulin mesylate (microtubule inhibitor, tubulin-based antimitotic, Halaven®, Eisai); cabazitaxel (microtubule inhibitor, tubulin-based antimitotic, Jevtana®, Sanofi-Aventis); capacetrine (thymidylate synthase inhibitor, Xeloda®, Genentech); bendamustine (bifunctional mechlorethamine derivative, believed to form interstrand DNA cross-links, Treanda®, Cephalon/Teva); ixabepilone (semi-synthetic analog of epothilone B, microtubule inhibitor, tubulin-based antimitotic, Ixempra®, Bristol-Myers Squibb); nelarabine (prodrug of deoxyguanosine analog, nucleoside metabolic inhibitor, Arranon®, Novartis); clorafabine (prodrug of ribonucleotide reductase inhibitor, competitive inhibitor of deoxycytidine, Clolar®, Sanofi-Aventis); and trifluridine and tipiracil (thymidine-based nucleoside analog and thymidine phosphorylase inhibitor, Lonsurf®, Taiho Oncology).

In some embodiments, one or more other therapeutic agent is a kinase inhibitor or VEGF-R antagonist. Approved VEGF inhibitors and kinase inhibitors useful in the present invention include: bevacizumab (Avastin®, Genentech/Roche) an anti-VEGF monoclonal antibody; ramucirumab (Cyramza®, Eli Lilly), an anti-VEGFR-2 antibody and ziv-aflibercept, also known as VEGF Trap (Zaltrap®; Regeneron/Sanofi). VEGFR inhibitors, such as regorafenib (Stivarga®, Bayer); vandetanib (Caprelsa®, AstraZeneca); axitinib (Inlyta®, Pfizer); and lenvatinib (Lenvima®, Eisai); Raf inhibitors, such as sorafenib (Nexavar®, Bayer AG and Onyx); dabrafenib (Tafinlar®, Novartis); and vemurafenib (Zelboraf®, Genentech/Roche); MEK inhibitors, such as cobimetanib (Cotellic®, Exelexis/Genentech/Roche); trametinib (Mekinist®, Novartis); Bcr-Abl tyrosine kinase inhibitors, such as imatinib (Gleevec®, Novartis); nilotinib (Tasigna®, Novartis); dasatinib (Sprycel®, BristolMyersS-quibb); bosutinib (Bosulif®, Pfizer); and ponatinib (Inclusig®, Ariad Pharmaceuticals); Her2 and EGFR inhibitors, such as gefitinib (Iressa®, AstraZeneca); erlotinib (Tarceeva®, Genentech/Roche/Astellas); lapatinib (Tykerb®, Novartis); afatinib (Gilotrif®, Boehringer Ingelheim); osimertinib (targeting activated EGFR, Tagrisso®, AstraZeneca); and brigatinib (Alunbrig®, Ariad Pharmaceuticals); c-Met and VEGFR2 inhibitors, such as cabozanitib (Cometriq®, Exelexis); and multikinase inhibitors, such as sunitinib (Sutent®, Pfizer); pazopanib (Votrient®, Novartis); ALK inhibitors, such as crizotinib (Xalkori®, Pfizer); ceritinib (Zykadia®, Novartis); and alectinib (Alecenza®, Genentech/Roche); Bruton's tyrosine kinase inhibitors, such as ibrutinib (Imbruvica®, Pharmacyclics/Janssen); and Flt3 receptor inhibitors, such as midostaurin (Rydapt®, Novartis).

Other kinase inhibitors and VEGF-R antagonists that are in development and may be used in the present invention include tivozanib (Aveo Pharmaecuticals); vatalanib (Bayer/Novartis); lucitanib (Clovis Oncology); dovitinib (TKI258, Novartis); Chiauanib (Chipscreen Biosciences); CEP-11981 (Cephalon); linifanib (Abbott Laboratories); neratinib (HKI-272, Puma Biotechnology); radotinib (Supect®, IY5511, Il-Yang Pharmaceuticals, S. Korea); ruxolitinib (Jakafi®, Incyte Corporation); PTC299 (PTC Therapeutics); CP-547, 632 (Pfizer); foretinib (Exelexis, GlaxoSmithKline); quizartinib (Daiichi Sankyo) and motesanib (Amgen/Takeda).

In another embodiment, the present invention provides a method of treating organ transplant rejection or graft vs. host disease comprising administering to a patient in need thereof a compound of formula I and one or more additional therapeutic agents selected from a steroid, cyclosporin, FK506, rapamycin, a hedgehog signaling inhibitor, a BTK inhibitor, a JAK/pan-JAK inhibitor, a TYK2 inhibitor, a PI3K inhibitor, and a SYK inhibitor.

In another embodiment, the present invention provides a method of treating or lessening the severity of a disease comprising administering to a patient in need thereof a compound of formula I and a BTK inhibitor, wherein the disease is selected from inflammatory bowel disease, arthritis, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenström macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenström macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a compound of formula I and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a compound of formula I and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis *nodosa* (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

In some embodiments, one or more other therapeutic agent is a phosphatidylinositol 3 kinase (PI3K) inhibitor. In some embodiments, a PI3K inhibitor is selected from idelalisib (Zydelig®, Gilead), alpelisib (BYL719, Novartis), taselisib (GDC-0032, Genentech/Roche); pictilisib (GDC-0941, Genentech/Roche); copanlisib (BAY806946, Bayer); duvelisib (formerly IPI-145, Infinity Pharmaceuticals); PQR309 (Piqur Therapeutics, Switzerland); and TGR1202 (formerly RP5230, TG Therapeutics).

The compounds and compositions, according to the method of the present invention, may be administered using any amount and any route of administration effective for treating or lessening the severity of a cancer, an autoimmune disorder, a proliferative disorder, an inflammatory disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity or degading a protein kinase in a biological sample comprising the step of contacting said biological sample with a compound of this invention, or a composition comprising said compound.

According to another embodiment, the invention relates to a method of inhibiting or degrading IRAK-1, IRAK-2, and/or IRAK-4, or a mutant thereof, activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition and/or degradation of a protein kinase, or a protein kinase selected from IRAK-1, IRAK-2, and/or IRAK-4, or a mutant thereof, activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of degrading a protein kinase and/or inhibiting protein kinase activity in a patient comprising the step of administering to said patient a compound of the present invention, or a composition comprising said compound.

According to another embodiment, the invention relates to a method of degrading and/or inhibiting one or more of IRAK-1, IRAK-2, and/or IRAK-4, or a mutant thereof, activity in a patient comprising the step of administering to said patient a compound of the present invention, or a composition comprising said compound. In other embodiments, the present invention provides a method for treating a disorder mediated by one or more of IRAK-1, IRAK-2, and/or IRAK-4, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethyl-amino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin.

The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™ Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

In some embodiments, one or more other therapeutic agent is an mTOR inhibitor, which inhibits cell proliferation, angiogenesis and glucose uptake. In some embodiments, an mTOR inhibitor is everolimus (Afinitor®, Novartis); temsirolimus (Torisel®, Pfizer); and sirolimus (Rapamune®, Pfizer).

In some embodiments, one or more other therapeutic agent is an aromatase inhibitor. In some embodiments, an aromatase inhibitor is selected from exemestane (Aromasin®, Pfizer); anastazole (Arimidex®, AstraZeneca) and letrozole (Femara®, Novartis).

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a P13K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, $C_{1-1033}$, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

Compounds which target, decrease or inhibit the activity of a protein or lipid phosphatase are e.g. inhibitors of phosphatase 1, phosphatase 2A, or CDC25, such as okadaic acid or a derivative thereof.

In some embodiments, one or more other therapeutic agent is a growth factor antagonist, such as an antagonist of platelet-derived growth factor (PDGF), or epidermal growth factor (EGF) or its receptor (EGFR). Approved PDGF antagonists which may be used in the present invention include olaratumab (Lartruvo®; Eli Lilly). Approved EGFR antagonists which may be used in the present invention include cetuximab (Erbitux®, Eli Lilly); necitumumab (Portrazza®, Eli Lilly), panitumumab (Vectibix®, Amgen); and osimertinib (targeting activated EGFR, Tagrisso®, AstraZeneca).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™)); carfilzomib (Kyprolis®, Amgen); and ixazomib (Ninlaro®, Takeda), and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294 Å (Napp), BAY19-8004 (Bayer), SCH-351591 (Schering-Plough), Arofylline (Almirall Prodesfarma), PD189659/PD168787 (ParkeDavis), AWD-12-281 (Asta Medica), CDC-801 (Celgene), SeICID™ CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl] tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of one or more other therapeutic agent present in the compositions of this invention may be no more than the amount that would normally be administered in a composition comprising that therapeutic agent as the only active agent. Preferably the amount of one or more other therapeutic agent in the presently disclosed compositions will range from about 50% to 100% of the amount normally present in a composition comprising that agent as the only therapeutically active agent. In some embodiments, one or more other therapeutic agent is administered at a dosage of about 50%, about 55%, about 60%, about 65%, about 70%, about 75%, about 80%, about 85%, about 90%, or about 95% of the amount normally administered for that agent. As used herein, the phrase "normally administered" means the amount an FDA approved therapeutic agent is approvided for dosing per the FDA label insert.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

Exemplary Immuno-Oncology Agents

In some embodiments, one or more other therapeutic agent is an immuno-oncology agent. As used herein, the term "an immuno-oncology agent" refers to an agent which is effective to enhance, stimulate, and/or up-regulate immune responses in a subject. In some embodiments, the administration of an immuno-oncology agent with a compound of the invention has a synergic effect in treating a cancer.

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD- L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/ Fnl4, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In some embodiments, an immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In some embodiments, a combination of a compound of the invention and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonists of activating receptors on NK cells. In some embodiments, an immuno-oncology agent is an antagonists of KIR, such as lirilumab.

In some embodiments, an immuno-oncology agent is an agent that inhibits or depletes macrophages or monocytes, including but not limited to CSF-1R antagonists such as CSF-1R antagonist antibodies including RG7155 (WO11/ 70024, WO11/107553, WO11/131407, WO13/87699, WO13/119716, WO13/132044) or FPA-008 (WO11/ 140249; WO13169264; WO14/036357).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YER-VOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514; WO2012/145493). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgG1, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is MPDL3280A (RG7446; WO2010/077634), durvalumab (MEDI4736), BMS-936559 (WO2007/005874), and MSB0010718C (WO2013/79174).

In some embodiments, an immuno-oncology agent is a LAG-3 antagonist. In some embodiments, a LAG-3 antagonist is an antagonistic LAG-3 antibody. In some embodiments, a LAG3 antibody is BMS-986016 (WO10/19570, WO14/08218), or IMP-731 or IMP-321 (WO08/132601, WO009/44273).

In some embodiments, an immuno-oncology agent is a CD137 (4-1BB) agonist. In some embodiments, a CD137 (4-1BB) agonist is an agonistic CD137 antibody. In some embodiments, a CD137 antibody is urelumab or PF-05082566 (WO12/32433).

In some embodiments, an immuno-oncology agent is a GITR agonist. In some embodiments, a GITR agonist is an agonistic GITR antibody. In some embodiments, a GITR antibody is BMS-986153, BMS-986156, TRX-518 (WO006/105021, WO009/009116), or MK-4166 (WO11/ 028683).

In some embodiments, an immuno-oncology agent is an indoleamine (2,3)-dioxygenase (IDO) antagonist. In some embodiments, an IDO antagonist is selected from epacadostat (INCB024360, Incyte); indoximod (NLG-8189, NewLink Genetics Corporation); capmanitib (INC280, Novartis); GDC-0919 (Genentech/Roche); PF-06840003 (Pfizer); BMS:F001287 (Bristol-Myers Squibb); Phy906/KD108 (Phytoceutica); an enzyme that breaks down kynurenine (Kynase, Kyn Therapeutics); and NLG-919 (WO09/73620, WO009/1156652, WO11/56652, WO12/142237).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is RG-7888 (WO06/ 029879).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is MGA271 (to B7H3) (WO11/109400).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (Opdivo®, Bristol-Myers Squibb, also known as ONO-4538, MDX1106 and BMS-936558), has shown potential to improve the overall survival in patients with RCC who had experienced disease progression during or after prior anti-angiogenic therapy.

In some embodiments, the immunomodulatory therapeutic specifically induces apoptosis of tumor cells. Approved immunomodulatory therapeutics which may be used in the present invention include pomalidomide (Pomalyst®, Celgene); lenalidomide (Revlimid®, Celgene); ingenol mebutate (Picato®, LEO Pharma).

In some embodiments, an immuno-oncology agent is a cancer vaccine. In some embodiments, the cancer vaccine is selected from sipuleucel-T (Provenge®, Dendreon/Valeant Pharmaceuticals), which has been approved for treatment of asymptomatic, or minimally symptomatic metastatic castrate-resistant (hormone-refractory) prostate cancer; and talimogene laherparepvec (Imlygic®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase- (TK-) deficient vaccinia virus engineered to express GM-CSF, for hepatocellular carcinoma (NCT02562755) and melanoma (NCT00429312); pelareorep (Reolysin®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1h68/GLV-1h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, an immuno-oncology agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFa-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific $CD8^+$ T cell response.

In some embodiments, an immuno-oncology agent is a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682 (June; hereby incorporated by reference in its entirety), which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+(Th17) and CD8+(Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCT02124850) and ovarian cancer (NCT02431559).

Other immuno-oncology agents that may be used in the present invention include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15). rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-IL-12 (Neumedicines, Inc.), NCT02544724, or NCT02542124.

In some embodiments, an immuno-oncology agent is selected from those descripted in Jerry L. Adams ET. AL., "Big opportunities for small molecules in immuno-oncology," Cancer Therapy 2015, Vol. 14, pages 603-622, the content of which is incorporated herein by reference in its entirety. In some embodiments, an immuno-oncology agent is selected from the examples described in Table 1 of Jerry L. Adams ET. AL. In some embodiments, an immuno-oncology agent is a small molecule targeting an immuno-oncology target selected from those listed in Table 2 of Jerry L. Adams ET. AL. In some embodiments, an immuno-oncology agent is a small molecule agent selectd from those listed in Table 2 of Jerry L. Adams ET. AL.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by refenrece in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BiTE®) antibody constructs can mediate bystander tumor cell killing", PLoS ONE 12 (8): e0183390, the conten of which is incorporated herein by reference in its entirety. In some embodiments, an immuno-oncology agent is a bispecific T cell engager (BiTE®) antibody construct. In some embodiments, a bispecific T cell engager (BiTE®) antibody construct is a CD19/CD3 bispecific antibody construct. In some embodiments, a bispecific T cell engager (BiTE®) antibody construct is an EGFR/CD3 bispecific antibody construct. In some embodiments, a bispecific T cell engager (BiTE®) antibody construct activates T cells. In some embodiments, a bispecific T cell engager (BiTE®) antibody construct activates T cells, which release cytokines inducing upregulation of intercellular adhesion molecule 1 (ICAM-1) and FAS on bystander cells. In some embodiments, a bispecific T cell engager (BiTE®) antibody construct activates T cells which result in induced bystander cell lysis. In some embodiments, the bystander cells are in solid tumors. In some embodiments, the bystander cells being lysed are in proximity to the BiTE®-activated T cells. In some embodiment, the bystander cells comprises tumor-associated antigen (TAA) negative cancer cells. In some embodiment, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex-vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

Exemplary Immune Checkpoint Inhibitors

In some embodiments, an immuno-oncology agent is an immune checkpoint inhibitor as described herein.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signaling processes should proceed.

In some embodiments, an immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In one aspect, the checkpoint inhibitor is a biologic therapeutic or a small molecule. In another aspect, the checkpoint inhibitor is a monoclonal antibody, a humanized antibody, a fully human antibody, a fusion protein or a combination thereof. In a further aspect, the checkpoint inhibitor inhibits a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an additional aspect, the checkpoint inhibitor interacts with a ligand of a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an aspect, the checkpoint inhibitor is an immunostimulatory agent, a T cell growth factor, an interleukin, an antibody, a vaccine or a combination thereof. In a further aspect, the interleukin is IL-7 or IL-15. In a specific aspect, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that may be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory $CD8^+$ (αβ) T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (Opdivo®), ipilimumab (Yervoy®), and pembrolizumab (Keytruda®). In some embodiments, the checkpoint inhibitor is selected from nivolumab (anti-PD-1 antibody, Opdivo®, Bristol-Myers Squibb); pembrolizumab (anti-PD-1 antibody, Keytruda®, Merck); ipilimumab (anti-CTLA-4 antibody, Yervoy®, Bristol-Myers Squibb); durvalumab (anti-PD-L1 antibody, Imfinzi®, AstraZeneca); and atezolizumab (anti-PD-L1 antibody, Tecentriq®, Genentech).

In some embodiments, the checkpoint inhibitor is selected from the group consisting of lambrolizumab (MK-3475), nivolumab (BMS-936558), pidilizumab (CT-011), AMP-224, MDX-1105, MEDI4736, MPDL3280A, BMS-936559, ipilimumab, lirlumab, IPH2101, pembrolizumab (Keytruda®), and tremelimumab.

In some embodiments, an immune checkpoint inhibitor is REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (Bavencio®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; or PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

In some embodiments, a checkpoint inhibitor is an inhibitor of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

In some embodiments, a checkpoint inhibitor is an inhibitor of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

In some embodiments, a checkpoint inhibitor is an inhibitor of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IMP321 (Immutep S.A.) is an LAG-3-Ig fusion protein, being studied in melanoma (NCT02676869); adenocarcinoma (NCT02614833); and metastatic breast cancer (NCT00349934).

Checkpoint inhibitors that may be used in the present invention include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MEDI0562 (Medimmune/AstraZeneca), an agonistic anti-OX40 antibody, in advanced solid tumors (NCT02318394 and NCT02705482); MEDI6469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Checkpoint inhibitors that may be used in the present invention include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981).

Checkpoint inhibitors that may be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Checkpoint inhibitors that may be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MEDI1873 (Medimmune/AstraZeneca), an agonistic hexameric GITR-ligand molecule with a human IgG1 Fc domain, in advanced solid tumors (NCT02583165).

Checkpoint inhibitors that may be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck), an agonistic anti-ICOS antibody, in Phase 1 (NCT02723955); JTX-2011 (Jounce Therapeutics), an agonistic anti-ICOS antibody, in Phase 1 (NCT02904226).

Checkpoint inhibitors that may be used in the present invention include killer IgG-like receptor (KIR) inhibitors. KIR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Checkpoint inhibitors that may be used in the present invention include CD47 inhibitors of interaction between CD47 and signal regulatory protein alpha (SIRPa). CD47/SIRPa inhibitors that are being studied in clinical trials include ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, Trillium Therapeutics), a soluble recombinant fusion protein created by linking the N-terminal CD47-binding domain of SIRPa with the Fc domain of human IgG1, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Checkpoint inhibitors that may be used in the present invention include CD73 inhibitors. CD73 inhibitors that are being studied in clinical trials include MEDI9447 (Medimmune), an anti-CD73 antibody, in solid tumors (NCT02503774); and BMS-986179 (Bristol-Myers Squibb), an anti-CD73 antibody, in solid tumors (NCT02754141).

Checkpoint inhibitors that may be used in the present invention include agonists of stimulator of interferon genes protein (STING, also known as transmembrane protein 173, or TMEM173). Agonists of STING that are being studied in clinical trials include MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

Checkpoint inhibitors that may be used in the present invention include CSF1R inhibitors. CSF1R inhibitors that are being studied in clinical trials include pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Checkpoint inhibitors that may be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

EXEMPLIFICATION

Abbreviations

Ac: acetyl
AcOH: acetic acid
ACN: acetonitrile
Ad: adamantly
AIBN: 2,2'-azo bisisobutyronitrile
Anhyd: anhydrous
Aq: aqueous
$B_2Pin_2$: bis (pinacolato)diboron-4,4,4',4',5,5,5',5'-octamethyl-2,2'-bi(1,3,2-dioxaborolane)
BINAP: 2,2'-bis(diphenylphosphino)-1,1'-binaphthyl
$BH_3$: Borane
Bn: benzyl
Boc: tert-butoxycarbonyl
$Boc_2O$: di-tert-butyl dicarbonate
BPO: benzoyl peroxide
$^n$BuOH: n-butanol
CDI: carbonyldiimidazole
COD: cyclooctadiene
d: days DABCO: 1,4-diazobicyclo[2.2.2]octane
DAST: diethylaminosulfur trifluoride
dba: dibenzylideneacetone
DBU: 1,8-diazobicyclo[5.4.0]undec-7-ene
1,2-dichloroethane
DCM: dichloromethane
DEA: diethylamine
DHP: dihydropyran
DIBAL-H: diisobutylaluminum hydride
DIPA: diisopropylamine
DIPEA or DIEA: N,N-diisopropylethylamine
DMA: N,N-dimethylacetamide
DME: 1,2-dimethoxyethane
DMAP: 4-dimethylaminopyridine
DMF: N,N-dimethylformamide
DMP: Dess-Martin periodinane
DMSO-dimethyl sulfoxide
DPPA: diphenylphosphoryl azide
dppf: 1,1'-bis(diphenylphosphino)ferrocene
EDC or EDCI: 1-(3-dimethylaminopropyl)-3-ethylcarbodiimide hydrochloride
ee: enantiomeric excess
ESI: electrospray ionization
EA: ethyl acetate
EtOAc: ethyl acetate
EtOH: ethanol
FA: formic acid
h or hrs: hours
HATU: N,N,N',N'-tetramethyl-O-(7-azabenzotriazol-1-yl)uronium hexafluorophosphate
HCl: hydrochloric acid
HPLC: high performance liquid chromatography
HOAc: acetic acid
IBX: 2-iodoxybenzoic acid
IPA: isopropyl alcohol
KHMDS: potassium hexamethyldisilazide
$K_2CO_3$: potassium carbonate
LAH: lithium aluminum hydride
LDA: lithium diisopropylamide
m-CPBA: meta-chloroperbenzoic acid
M: molar
MeCN: acetonitrile
MeOH: methanol
Me2S: dimethyl sulfide
MeONa: sodium methylate
MeI: iodomethane
min: minutes
mL: milliliters
mM: millimolar
mmol: millimoles
MPa: mega pascal
MOMCl: methyl chloromethyl ether
MsCl: methanesulfonyl chloride
MTBE: methyl tert-butyl ether
nBuLi: n-butyllithium
$NaNO_2$: sodium nitrite
NaOH: sodium hydroxide
$Na_2SO_4$: sodium sulfate
NBS: N-bromosuccinimide
NCS: N-chlorosuccinimide
NFSI: N-Fluorobenzenesulfonimide
NMO: N-rnethylmorph oline N-oxide
NMP: N-methylpyrrolidine
NMR: Nuclear Magnetic Resonance
° C.: degrees Celsius
Pd/C: Palladium on Carbon
Pd(OAc)$_2$: Palladium Acetate
PBS: phosphate buffered saline
PE: petroleum ether
$POCl_3$: phosphorus oxychloride
$PPh_3$: triphenylphosphine
PyBOP: (Benzotriazol-1-yloxy)tripyrrolidinophosphonium hexafluorophosphate
Rel: relative
R.T. or rt: room temperature
sat: saturated
SEMCl: chloromethyl-2-trimethyl silylethyl ether
SFC: supercritical fluid chromatography
$SOCl_2$: sulfur dichloride
tBuOK: potassium tert-butoxide
TBAB: tetrabutylammonium bromide
TBAI: tetrabutylammonium iodide
TEA: triethylamine
Tf: trifluoromethanesulfonate
TfAA, TFMSA or $Tf_2O$: trifluoromethanesulfonic anhydride
TFA: trifluoracetic acid
TIPS: triisopropylsilyl
THF: tetrahydrofuran
THP: tetrahydropyran
TLC: thin layer chromatography
TMEDA: tetramethylethylenediamine
pTSA: para-toluenesulfonic acid
wt: weight
Xantphos: 4,5-bis(diphenylphosphino)-9,9-dimethylxanthene General Synthetic Methods The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

All reactions are carried out under nitrogen or argon unless otherwise stated.

Proton NMR ($^1H$ NMR) is conducted in deuterated solvent. In certain compounds disclosed herein, one or more $^1H$ shifts overlap with residual proteo solvent signals; these signals have not been reported in the experimental provided hereinafter.

TABLE 2

| Analytical instruments | |
| --- | --- |
| LCMS | Shimadzu UFLC MS: LCMS-2020 |
| | Agilent Technologies 1200 series MS: Agilent Technologies 6110 |
| | Agilent Technologies 1200 series MS: LC/MSD VL |

TABLE 2-continued

Analytical instruments

| | |
|---|---|
| NMR | BRUKER AVANCE III/400; Frequency (MHz) 400.13; Nucleus: 1H; Number of Transients: 8 |
| Prep-HPLC | Gilson GX-281 systems: instruments GX-A, GX-B, GX-C, GX-D, GX-E, GX-F, GX-G and GX-H |
| GCMS | SHIMADZU GCMS-QP2010 Ultra |
| Analytical cSFC | Agilent Technologies 1290 Infinity |
| Prep-cSFC | Waters SFC Prep 80 |

For Acidic LCMS Data:

LCMS was recorded on an Agilent 1200 Series LC/MSD or Shimadzu LCMS2020 equipped with electro-spray ionization and quadruple MS detector [ES+ve to give MH$^+$] and equipped with Chromolith Flash RP-18e 25*2.0 mm, eluting with 0.0375 vol % TFA in water (solvent A) and 0.01875 vol % TFA in acetonitrile (solvent B). Other LCMS was recorded on an Agilent 1290 Infinity RRLC attached with Agilent 6120 Mass detector. The column used was BEH C18 50*2.1 mm, 1.7 micron. Column flow was 0.55 ml/min and mobile phase were used (A) 2 mM Ammonium Acetate in 0.1% Formic Acid in Water and (B) 0.1% Formic Acid in Acetonitrile.

For Basic LCMS Data:

LCMS was recorded on an Agilent 1200 Series LC/MSD or Shimadzu LCMS 2020 equipped with electro-spray ionization and quadruple MS detector [ES+ve to give MH$^+$] and equipped with Xbridge C18, 2.1×50 mm columns packed with 5 mm C18-coated silica or Kinetex EVO C18 2.1×30 mm columns packed with 5 mm C18-coated silica, eluting with 0.05 vol % $NH_3.H_2O$ in water (solvent A) and acetonitrile (solvent B).

HPLC Analytical Method:

HPLC was carried out on X Bridge C18 150*4.6 mm, 5 micron. Column flow was 1.0 ml/min and mobile phase were used (A) 0.1% Ammonia in water and (B) 0.1% Ammonia in Acetonitrile.

Prep HPLC Analytical Method:

The compound was purified on Shimadzu LC-20AP and UV detector. The column used was X-BRIDGE C18 (250*19)mm, 5μ. Column flow was 16.0 ml/min. Mobile phase were used (A) 0.1% Formic Acid in Water and (B) Acetonitrile Basic method used (A) 5 mM ammonium bicarbonate and 0.1% $NH_3$ in Water and (B) Acetonitrile or (A) 0.1% Ammonium Hydroxide in Water and (B) Acetonitrile. The UV spectra were recorded at 202 nm & 254 nm.

NMR Method:

The 1H NMR spectra were recorded on a Bruker Ultra Shield Advance 400 MHz/5 mm Probe (BBFO). The chemical shifts are reported in part-per-million.

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Intermediates 1-azido-5-bromopentane (Intermediate A)

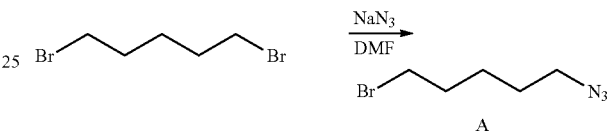

To a stirred solution of sodium azide (2.5 g, 38.5 mmol) in DMF (85 mL) was added 1,5-dibromopentane (8.4 g, 36.7 mmol) at room temperature. The resulting reaction mixture was then stirred at 50° C. for 16 h. The reaction mixture was transferred into ice water and the resulting mixture was extracted using ethyl acetate (3×100 mL). The combined organic layers were dried over anhydrous sodium sulfate and filtered. The filtrate was evaporated under reduced pressure to give 1-azido-5-bromopentane as colorless oil (5.0 g, 71%). $^1$H NMR (400 MHz, DMSO) δ 3.44 (t, J=6.8 Hz, 2H), 3.32 (t, J=4 Hz, 2H), 1.95-1.91 (m, 2H), 1.67-1.62 (m, 2H), 1.56-1.46 (m, 2H).

tert-butyl (5-(2-(2-((5-aminopentyl)oxy)ethoxy) ethoxy)pentyl)carbamate (Intermediate B)

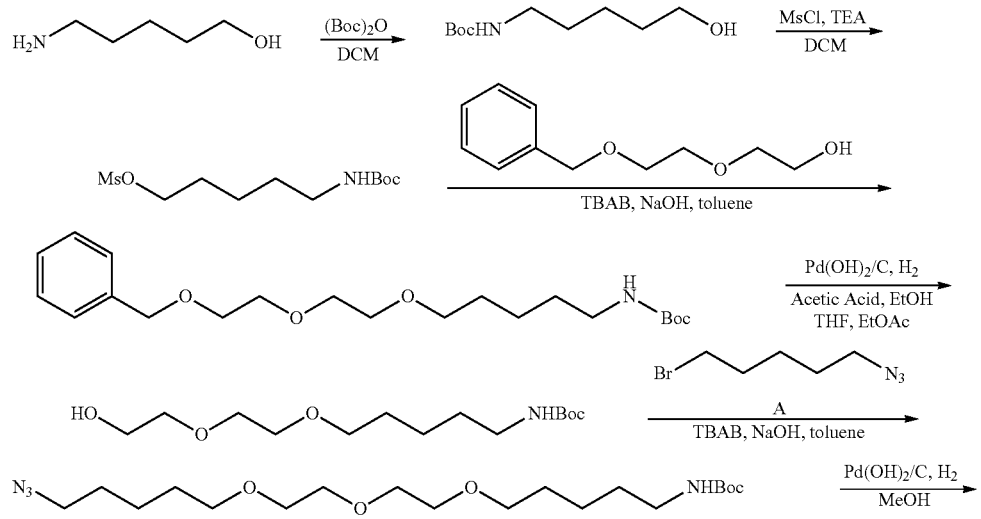

-continued

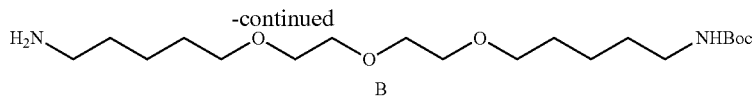

B

Step 1—tert-butyl (5-hydroxypentyl)carbamate

To a stirred solution of 5-aminopentan-1-ol (10.0 g, 96.9 mmol) in DCM (75 mL) was added Boc-anhydride (25.4 g, 116.3 mmol) dropwise at 0° C. The resulting reaction mixture was allowed to warm to room temperature and stirred at rt for 1 h. The reaction mixture was transferred into ice water and the resulting mixture was extracted using DCM (3×100 mL). The combined organic layers were dried over anhydrous sodium sulfate and filtered. The filtrate was evaporated under reduced pressure to give tert-butyl (5-hydroxypentyl)carbamate as colorless oil (16 g, 81%). $^1$H NMR (400 MHz, DMSO) δ 4.56 (bs, 1H), 3.69-3.64 (m, 2H), 3.17-3.12 (m, 2H), 1.64-1.62 (m, 2H), 1.54-1.53 (m, 6H), 1.51-1.49 (m, 1H), 1.46 (s, 9H), 1.43-1.37 (m, 2H).

Step 2—5-((tert-butoxycarbonyl)amino)pentyl methanesulfonate

To a stirred solution of tert-butyl (5-hydroxypentyl)carbamate (6.0 g, 29.5 mmol) and triethylamine (13 mL, 88.5 mmol) in DCM (100 mL) was added mesyl chloride (3.7 mL, 44.3 mmol) dropwise at 0° C. The resulting reaction mixture was allowed to warm to room temperature and stirred at rt for 2 h. The reaction mixture was transferred into water and the resulting mixture was extracted using DCM (3×100 mL). The combined organic layers were dried over anhydrous sodium sulfate and filtered. The filtrate was evaporated under reduced pressure to give 5-((tert-butoxycarbonyl)amino)pentyl methanesulfonate as white solid (7.0 g, 84%). LCMS: (ES$^+$) m/z (M+H)$^+$

Step 3—tert-butyl (5-(2-(2-(benzyloxy)ethoxy)ethoxy)pentyl)carbamate

To a stirred solution of 2-(2-(benzyloxy)ethoxy)ethan-1-ol (3.3 g, 16.8 mmol, CAS #2050-25-1) and 5-((tert-butoxycarbonyl)amino)pentyl methanesulfonate (7.0 g, 25.2 mmol) in toluene (50 mL) and 8 N Aqueous NaOH solution (50 mL) was added TBAB (catalytic amount) at room temperature. The resulting reaction mixture was allowed to stir at 80° C. for 16 h. The reaction mixture was then transferred into ice water and the resulting mixture was extracted using ethyl acetate (3×100 mL). The combined organic layers were dried over anhydrous sodium sulfate and filtered. The filtrate was evaporated under reduced pressure to afford the crude product. The crude product was purified using silica gel column chromatography (25% EtOAc-Hexanes) to give tert-butyl (5-(2-(2-(benzyloxy)ethoxy)ethoxy)pentyl)carbamate as colorless oil (3.5 g, 55%). $^1$H NMR (400 MHz, DMSO) δ 7.36 (d, J=4.4 Hz, 2H), 7.32-7.28 (m, 2H), 4.59 (s, 1H), 3.71-3.70 (m, 2H), 3.69-3.67 (m, 1H), 3.66-3.65 (m, 1H), 3.13-3.11 (m, 1H), 1.65-1.61 (m, 2H), 1.59-1.54 (m, 6H), 1.50-1.48 (m, 1H).

Step 4—tert-butyl (5-(2-(2-hydroxyethoxy)ethoxy)pentyl)carbamate

To a stirred solution of tert-butyl (5-(2-(2-(benzyloxy)ethoxy)ethoxy)pentyl)carbamate (3.5 g, 9.2 mmol) in ethanol (30 mL), THF (30 mL), ethyl acetate (30 mL) and acetic acid (2 mL) was added 20% Pd(OH)$_2$ (2.5 g) at room temperature under nitrogen atmosphere. The resulting reaction mixture was allowed to stir under hydrogen gas (20 kg/cm$^2$ pressure) in an autoclave at 60° C. for 16 h. The reaction mixture was filtered through celite with a vacuum and washed with MeOH (50 mL). The filtrate was evaporated under reduced pressure to give tert-butyl (5-(2-(2-hydroxyethoxy)ethoxy)pentyl)carbamate as colorless oil (2.5 g, 93%). $^1$H NMR (400 MHz, DMSO) δ 4.68 (bs, 1H), 3.77-3.75 (m, 2H), (s, 1H), 3.71-3.69 (m, 2H), 3.69-3.64 (m, 2H), 3.63-3.59 (m, 2H), 3.51-3.48 (m, 2H), 3.14-3.13 (m, 3H), 1.71-1.61 (m, 2H), 1.59-1.55 (m, 2H), 1.45 (s, 9H), 1.42-1.36 (m, 2H).

Step 5—tert-butyl (5-(2-(2-((5-azidopentyl)oxy)ethoxy)ethoxy)pentyl)carbamate To a stirred solution of tert-butyl (5-(2-(2-hydroxyethoxy)ethoxy)pentyl)carbamate (1.4 g, 4.8 mmol) and 1-azido-5-bromopentane (2.8 g, 14.4 mmol, Intermediate A) in toluene (10 mL) and 8 N aqueous NaOH solution (10 mL) was added TBAB (catalytic amount) at rt. The resulting reaction mixture was then heated to 80° C. and stirred for 16 h. The reaction mixture was transferred into ice water and the resulting mixture was extracted using ethyl acetate (3×100 mL). The combined organic layers were dried over anhydrous sodium sulfate and filtered. The filtrate was evaporated under reduced pressure to give tert-butyl (5-(2-(2-((5-azidopentyl)oxy)ethoxy)ethoxy)pentyl)carbamate as colorless oil (0.95 g, 50%). $^1$H NMR (400 MHz, DMSO) δ 4.56 (bs, 1H), 3.69-3.61 (m, 4H), 3.50-3.46 (m, 3H), 3.33-3.27 (m, 1H), 3.14-3.12 (m, 1H), 1.68-1.61 (m, 4H), 1.53-1.42 (m, 7H).

Step 6—tert-butyl (5-(2-(2-hydroxyethoxy)ethoxy)pentyl)carbamate

To a stirred solution of tert-butyl (5-(2-(2-((5-azidopentyl)oxy)ethoxy)ethoxy)pentyl)carbamate (0.45 g, 1.12 mmol) in methanol (30 mL) was added 20% Pd(OH)$_2$ (0.45 g) at room temperature under nitrogen atmosphere. The resulting reaction mixture was stirred under hydrogen gas (20 kg/cm2 pressure) in an auto clave at rt for 3 h. The reaction mixture was filtered through a pad of celite under vacuum and washed with MeOH (50 mL). The filtrate was evaporated under reduced pressure to give tert-butyl (5-(2-(2-((5-aminopentyl)oxy)ethoxy)ethoxy)pentyl)carbamate as colorless oil (0.35 g, 83%).

(1R,4R)-4-(6-((1,6-naphthyridin-2-yl)amino)-4-(cyclopropylamino)nicotinamido)cyclohexane-1-carboxylic acid (Intermediate C)

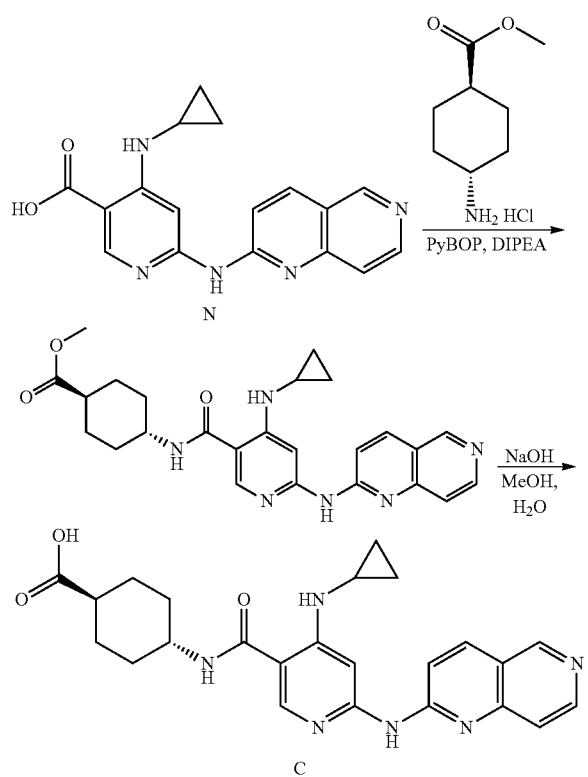

Step 1: Methyl (1R,4R)-4-(6-((1,6-naphthyridin-2-yl)amino)-4-(cyclopropylamino)nicotinamido)cyclohexane-1-carboxylate To a stirred solution of 6-((1,6-naphthyridin-2-yl)amino)-4-(cyclopropylamino)nicotinic acid (1.85 g, 5.76 mmol, Intermediate N) and methyl (1R,4R)-4-aminocyclohexane-1-carboxylate hydrochloride (1.34 g, 6.91 mmol) in DMF (10 mL) was added DIPEA (5 mL, 28.8 mmol) and PyBOP (4.5 g, 8.64 mmol) at rt. The resulting reaction mixture was stirred at rt for 16 h. The reaction mixture was then transferred into ice water and the resulting precipitate was filtered off, and dried reduced pressure. The crude product was purified using silica gel column chromatography (7% MeOH-DCM) to give methyl (1r,4r)-4-(6-((1,6-naphthyridin-2-yl)amino)-4-(cyclopropylamino)nicotinamido)cyclohexane-1-carboxylate as light a green solid (1.3 g, 49%). LC-MS (ESI+) m/z 460.54 (M+H)+

Step 2—(1R,4R)-4-(6-((1,6-naphthyridin-2-yl)amino)-4-(cyclopropylamino)nicotinamido)cyclohexane-1-carboxylic acid To a stirred solution of methyl (1R,4R)-4-(6-((1,6-naphthyridin-2-yl)amino)-4-(cyclopropylamino)nicotinamido)cyclohexane-1-carboxylate (1.2 g, 2.6 mmol) in MeOH (20 mL) was added NaOH (2 g, 50 mmol) in 20 mL water dropwise at rt. The resulting reaction mixture was stirred at rt for 3 h. The reaction mixture was then evaporated under vacuum, water (10 mL) was added and pH was adjusted to 6-7 using 10% citric acid solution. The resulting mixture was stirred for 15 min, the solid precipitate was filtered off and dried under vacuum to give (1R,4R)-4-(6-((1,6-naphthyridin-2-yl)amino)-4-(cyclopropylamino)nicotinamido)cyclohexane-1-carboxylic acid as a brown solid (0.9 g, 77%). LC-MS (ESI+) m/z 446.51 (M+H)+

2-((2-(2,6-dioxopiperidin-3-yl)-1,3-dioxoisoindolin-4-yl)oxy)acetic acid (Intermediate D)

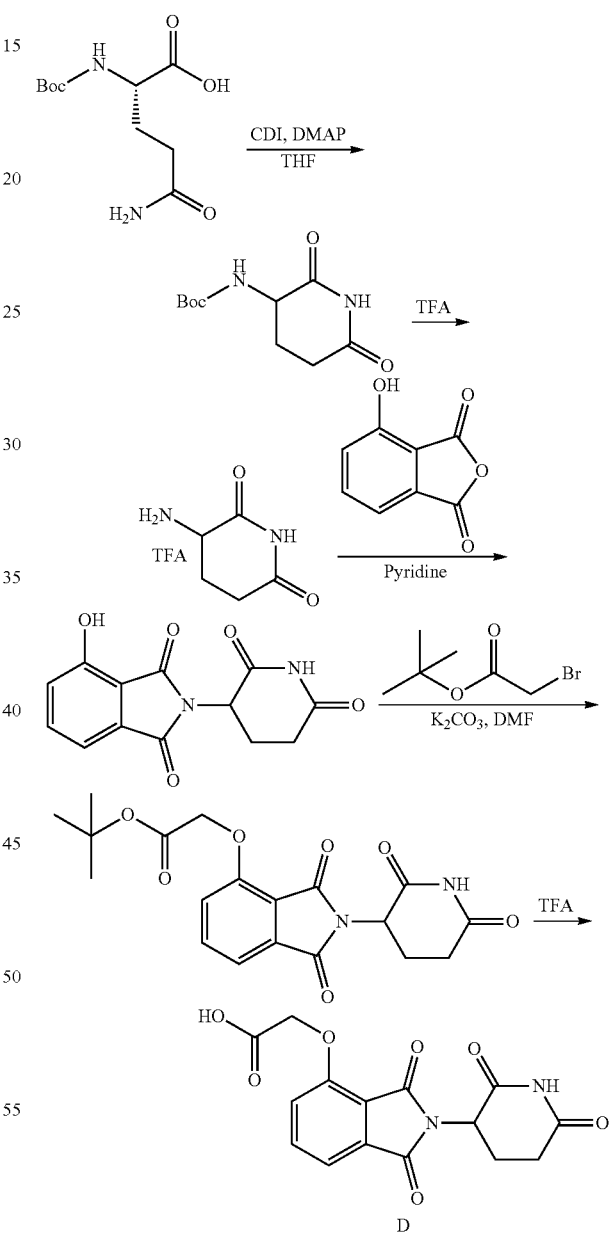

Step 1—tert-butyl (2,6-dioxopiperidin-3-yl)carbamate

To a stirred solution of (tert-butoxycarbonyl)-L-glutamine (6.0 g, 24 mmol) in THF (60 mL) was added CDI (4.2 g, 25.9 mmol) and DMAP (0.012 g, 0.098 mmol) at rt. The resulting reaction mixture heated to 70° C. and stirred for 16 h. The reaction precipitate was filtered and washed with THF (50 mL), and dried under reduced pressure to give tert-butyl (2,6-dioxopiperidin-3-yl)carbamate as white solid (1.8 g, 32%). LCMS (ESI⁻) m/z 227.2 (M−H)⁻.

Step 2—3-aminopiperidine-2,6-dione (TFA salt)

tert-Butyl (2,6-dioxopiperidin-3-yl)carbamate (1.8 g, 7.9 mmol) was dissolved in TFA (10 mL) and stirred at rt for 1 h. The reaction mixture was then evaporated under reduced pressure to give 3-aminopiperidine-2,6-dione as the TFA salt as a brown solid (1.7 g, 96%). LCMS (ESI⁺) m/z 129 (M+H)⁺.

Step 3—2-(2,6-dioxopiperidin-3-yl)-4-hydroxyisoindoline-1,3-dione

To a stirred solution of 4-hydroxyisobenzofuran-1,3-dione (1.2 g, 7.3 mmol) in pyridine (25 mL) was added 3-aminopiperidine-2,6-dione-TFA salt (1.8 g, 7.3 mmol) at room temperature. The resulting reaction mixture was then warmed to 110° C. and stirred for 16 h. The reaction mixture was then evaporated under reduced pressure. The crude product was purified using silica gel column chromatography (4% MeOH-DCM) to give 2-(2,6-dioxopiperidin-3-yl)-4-hydroxyisoindoline-1,3-dione as yellow solid (1 g, 50%). LC-MS (ESI) m/z 273.2 (M−H)⁺.

Step 4—tert-butyl 2-((2-(2,6-dioxopiperidin-3-yl)-1,3-dioxoisoindolin-4-yl)oxy)acetate To a stirred solution of 2-(2,6-dioxopiperidin-3-yl)-4-hydroxyisoindoline-1,3-dione (2.95 g, 10.76 mmol) and K₂CO₃ (2.22 g, 16.14 mmol) in DMF (40 mL) was added tert-butyl 2-bromoacetate (1.6 mL, 10.16 mmol) in DMF (10 mL) dropwise at rt. The resulting reaction mixture was stirred at rt for 2 h. The reaction mixture was then transferred into ice water and the resulting mixture was extracted using ethyl acetate (3×100 mL). The combined organic layers were dried over anhydrous sodium sulfate and filtered. The filtrate was evaporated under reduced pressure and the crude product was purified using silica gel column chromatography (50% EAc-Hexanes) to give tert-butyl 2-((2-(2,6-dioxopiperidin-3-yl)-1,3-dioxoisoindolin-4-yl)oxy)acetate as white solid (3 g, 72%). LC-MS (ESI) m/z 387.2 (M−H)⁺.

Step 5—2-((2-(2,6-dioxopiperidin-3-yl)-1,3-dioxoisoindolin-4-yl)oxy)acetic acid tert-Butyl 2-((2-(2,6-dioxopiperidin-3-yl)-1,3-dioxoisoindolin-4-yl)oxy)acetate (3.0 g, 7.7 mmol) was dissolved in TFA (30 mL) and stirred at rt for 1 h. The reaction mixture was then evaporated under reduced pressure and triturated with MTBE to give 2-((2-(2,6-dioxopiperidin-3-yl)-1,3-dioxoisoindolin-4-yl)oxy)acetic acid as white solid (2 g, 78%). ¹H NMR (400 MHz, DMSO) δ ppm 13.27 (s, 1H), 11.12 (s, 1H), 7.82-7.78 (m, 1H), 7.48 (d, J=7.6 Hz, 1H), 7.40 (d, J=8.4 Hz, 1H), 5.13-5.04 (m, 1H), 4.99 (s, 2H), 2.94-2.85 (m, 1H), 2.73-2.57 (m, 2H), 2.07-2.02 (m, 1H). LCMS (ESI⁺) m/z 333 (M+H)⁺.

tert-butyl (5-((5-aminopentyl)oxy)pentyl)carbamate (Intermediate E)

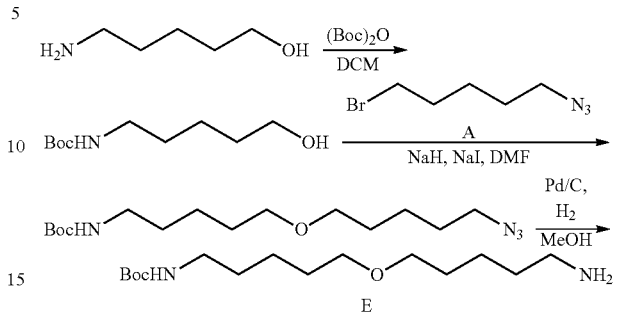

Step 1—tert-butyl (5-hydroxypentyl)carbamate

To a stirred solution of 5-aminopentan-1-ol (10.0 g, 96.9 mmol) in DCM (75 mL) was added Boc-anhydride (25.4 g, 116.3 mmol) dropwise at 0° C. The resulting reaction mixture was stirred at room temperature for 1 h. The reaction mixture was then transferred into ice water and the resulting mixture was extracted using DCM (3×100 mL). The combined organic layers were dried over anhydrous sodium sulfate and filtered. The filtrate was evaporated under reduced pressure to give tert-butyl (5-hydroxypentyl)carbamate as colorless oil (16 g, 81%). ¹H NMR (400 MHz, DMSO) δ 4.56 (bs, 1H), 3.69-3.64 (m, 2H), 3.17-3.12 (m, 2H), 1.64-1.62 (m, 2H), 1.54-1.53 (m, 6H), 1.51-1.49 (m, 1H), 1.46 (s, 9H), 1.43-1.37 (m, 2H).

Step 2—tert-butyl (5-((5-azidopentyl)oxy)pentyl)carbamate

To a stirred solution of tert-butyl (5-hydroxypentyl)carbamate (2.5 g, 12.3 mmol) in DMF (20 mL) was added NaI (catalytic amount) and NaH (0.74 g, 18.4 mmol, 60% dispersion in mineral oil) at room temperature. The resulting reaction mixture was stirred at room temperature for 0.5 h. To this reaction mixture 1-azido-5-bromopentane (3.55 g, 18.4 mmol, Intermediate A) in DMF (5 mL) was added dropwise at room temperature. The resulting reaction mixture was stirred at room temperature for 16 h. The reaction mixture was then transferred into ice water and the resulting mixture was extracted using ethyl acetate (3×100 mL). The combined organic layers were dried over anhydrous sodium sulfate and filtered. The filtrate was evaporated under reduced pressure. The crude product was purified using silica gel column chromatography (6% EAc-Hexanes) to give tert-butyl (5-((5-azidopentyl)oxy)pentyl)carbamate as colorless oil (0.85 g, 22%). LC-MS (ESI⁺) m/z 315.39 (M+H)⁺.

Step 3—tert-butyl (5-((5-aminopentyl)oxy)pentyl)carbamate

To a stirred solution of tert-butyl (5-((5-azidopentyl)oxy)pentyl)carbamate (0.2 g, 0.6 mmol) in methanol (5 mL) was added 10% Pd/C (0.1 g, 50% wet) at room temperature under nitrogen atmosphere. The resulting reaction mixture was stirred under hydrogen gas (5 kg/cm² pressure) in auto clave at rt for 5 h. The reaction mixture was filtered through a pad of celite under vacuum and washed with MeOH (20 mL). The filtrate was evaporated under reduced pressure to give tert-butyl (5-((5-aminopentyl)oxy)pentyl)carbamate as colorless oil (0.15 g, 82%). LC-MS (ESI$^+$) m/z 289.43 (M+H)$^+$.

tert-butyl (5-(2-((5-aminopentyl)oxy)ethoxy)pentyl)carbamate (Intermediate F)

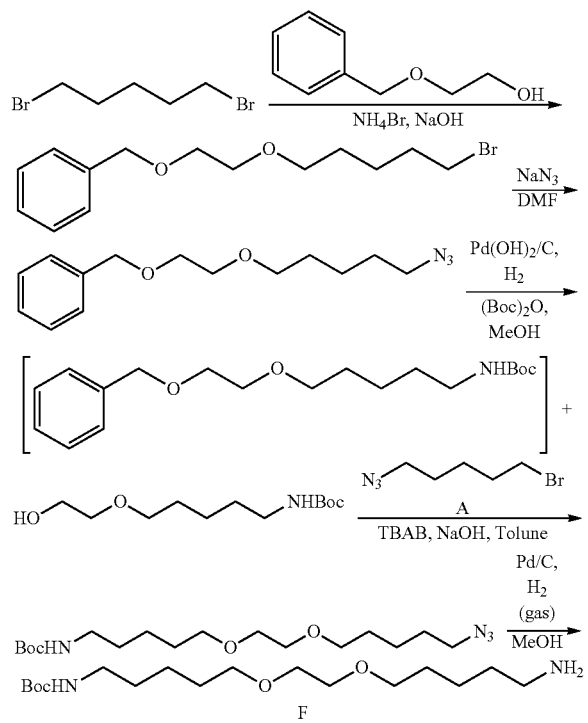

Step 1—((2-((5-bromopentyl)oxy)ethoxy)methyl)benzene

A solution of 2-(benzyloxy) ethan-1-ol (1.67 g, 10.96 mmol), 1,5-dibromopentane (10.0 g, 43.0 mmol), and ammonium bromide (0.5 g) in 8N NaOH (20 mL) was stirred at room temperature for 25 h. The reaction mixture was then transferred into ice water mixture, the pH was adjusted to 6-7, and resulting mixture was extracted using n-hexane (3×100 mL). The combined organic layer was dried over anhydrous sodium sulphate and filtered. The filtrate was evaporated under vacuum to give ((2-((5-bromopentyl)oxy)ethoxy)methyl)benzene as colorless liquid (23 g, 95%). LC-MS (ESI$^+$) m/z 303 (M+H)$^{+2}$.

Step 2—((2-((5-azidopentyl)oxy)ethoxy)methyl)benzene

A solution of ((2-((5-bromopentyl)oxy)ethoxy) methyl)benzene (23.0 g, 76.6 mmol) and sodium azide (7.47 g, 114.93 mmol) in DMF (125 mL) was heated to 60° C. and stirred for 18 h. The reaction mixture was then transferred into ice water and the resulting mixture was extracted using ethyl acetate (3×200 mL). The combined organic layers were dried over anhydrous sodium sulfate and filtered. The filtrate was evaporated under reduced pressure and the crude product was purified using silica gel column chromatography (10% EtOAc-Hexane) to give ((2-((5-azidopentyl)oxy)ethoxy)methyl)benzene as a colorless liquid (10.5 g, 82%). LC-MS (ESI$^+$) m/z 281.2 (M+18)$^+$.

Step 3—tert-butyl (5-(2-hydroxyethoxy)pentyl)carbamate

A solution of ((2-((5-azidopentyl)oxy)ethoxy) methyl) benzene (10.5 g, 39.9 mmol), 10% Pd/(OH)$_2$ (50% wet) (5 g) and Boc anhydride (13.04 g, 59.84 mmol) in MeOH (100 mL) and acetic acid (1 mL) was stirred in an autoclave. The reaction mixture was heated to 60° C. under hydrogen gas (30 kg/cm$^2$ pressure) for 48 h. The reaction mixture was filtered through a pad of celite and washed with methanol (100 mL). The filtrate was evaporated under reduced pressure and the crude product (with tert-butyl (5-(2-(benzyloxy) ethoxy)pentyl)carbamate as a side product) was purified using silica gel column chromatography (20% EtOAc-hexane) to give tert-butyl (5-(2-hydroxyethoxy)pentyl)carbamate as colorless oil (1.6 g, 13%).

Step 4—tert-butyl (5-(2-((5-azidopentyl)oxy)ethoxy)pentyl)carbamate

A solution of tert-butyl (5-(2-hydroxyethoxy)pentyl)carbamate (1.6 g, 6.5 mmol), TBAB (0.3 g, catalytic amount) and 1-azido-5-bromopentane (1.85 g, 9.71 mmol, Intermediate A) were dissolved in a mixture of toluene (30 mL) and 8 N NaOH (20 mL) and heated at 80° C. for 24 h. The reaction mixture was then transferred into ice water and the resulting mixture was extracted using ethyl acetate (3×50 mL). The combined organic layers were dried over anhydrous sodium sulfate and filtered. The filtrate was evaporated under reduced pressure and the crude product was purified using silica gel column chromatography (25% EtOAc-Hexane) to give tert-butyl (5-(2-((5-azidopentyl)oxy)ethoxy)pentyl)carbamate as a colorless oil (0.7 g, 30%). LC-MS (ESI$^+$) m/z 359.3 (M+H)$^+$.

Step 5—tert-butyl (5-(2-((5-aminopentyl)oxy)ethoxy)pentyl)carbamate

A solution of tert-butyl (5-(2-((5-azidopentyl) oxy) ethoxy)pentyl)carbamate (0.7 g, 19.9 mmol) and 10 wt % Pd/C (50% wet) (0.05 g) was dissolved in MeOH (10 mL) in an autoclave. The reaction mixture was heated to 50° C. under hydrogen gas (20 kg/cm$^2$ pressure) for 4 h. Upon completion, the reaction mixture was filtered through a pad of celite and washed with methanol (20 mL). The filtrate was evaporated under reduced pressure to give as tert-butyl (5-(2-((5-aminopentyl)oxy)ethoxy)pentyl)carbamate as a colorless oil (0.55 g) which was used directly in the next step without further purification.

(2S,4R)-1-((S)-2-amino-3,3-dimethylbutanoyl)-4-hydroxy-N-(4-(4-methylthiazol-5-yl)benzyl)pyrrolidine-2-carboxamide hydrochloride (Intermediate G)

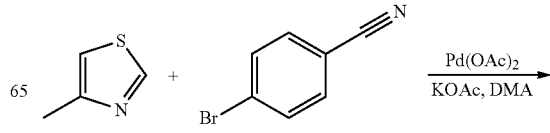

-continued

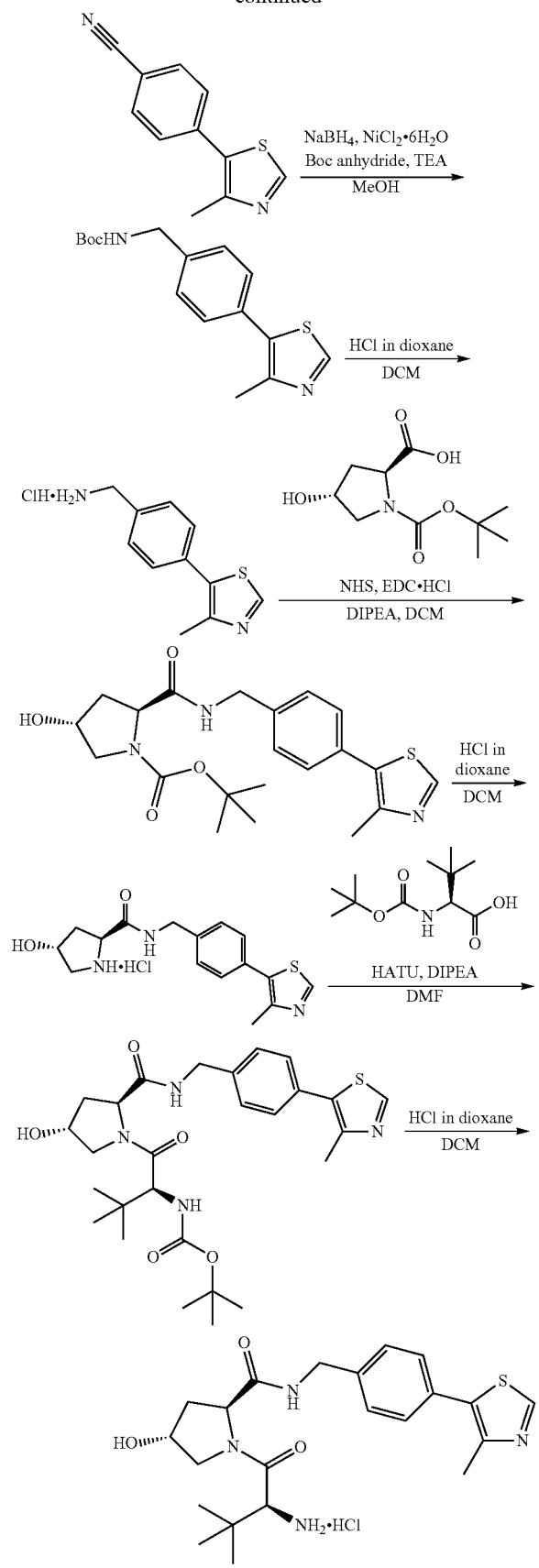

Step 1—4-(4-methylthiazol-5-yl)benzonitrile

To a solution of 4-bromobenzonitrile (1.0 g, 5.5 mmol) and palladium acetate (0.061 g, 2.75 mmol) in dimethyl acetamide (5 mL) was added potassium acetate (1.08 g, 11.0 mmol) and 4-methylthiazole (1 mL, 11.0 mmol) at rt. The reaction mixture was then heated and stirred at 130° C. for 18 h. The reaction mixture was transferred into ice water and the resulting mixture was extracted using DCM (3×20 mL). The combined organic layers were dried over anhydrous sodium sulfate and filtered. The filtrate was evaporated under reduced pressure and the crude product was purified using silica gel column chromatography (10% EtOAc-hexane) to give 4-(4-methylthiazol-5-yl)benzonitrile as yellow solid (0.6 g, 55%). LC-MS (ESI$^+$) m/z 200 (M+H)$^+$.

Step 2—tert-butyl (4-(4-methylthiazol-5-yl)benzyl)carbamate

To a stirred solution of 4-(4-methylthiazol-5-yl)benzonitrile (0.6 g, 3.0 mmol) in methanol (50 mL) was added NiCl$_2$.6H$_2$O (0.07 g, 0.3 mmol) and boc anhydride (1 mL, 4.5 mmol) at 0° C. and stirred for 15 minutes. After 15 minutes, NaBH$_4$ (0.8 g, 21.0 mmol) was added in portions over 30 minutes at 0° C. and stirred additional for 30 minutes. Then triethylamine (0.8 mL, 6.0 mmol) was added and the mixture was stirred for a further 3 h. The reaction mixture was then evaporated under vacuum and diluted with ethyl acetate (50 mL) and filtered through celite. The filtrate was washed using water (50 mL). The combined organic layers were dried over anhydrous sodium sulfate and filtered. The filtrate was evaporated under reduced pressure and the crude product was purified using silica gel column chromatography (15% EtOAc-Hexane) to give tert-butyl (4-(4-methylthiazol-5-yl)benzyl)carbamate as yellow semi-solid (0.5 g, 55%). LC-MS (ESI$^+$) m/z 305.2 (M+H)$^+$.

Step 3—(4-(4-methylthiazol-5-yl)phenyl)methanamine hydrochloride

To a stirred solution of tert-butyl (4-(4-methylthiazol-5-yl)benzyl)carbamate (0.5 g, 1.6 mmol) in DCM (5 mL) was added 4N HCl in dioxane (1 mL) and the reaction mixture was stirred at rt for 3 h. The reaction mixture was then evaporated under vacuum and triturated using diethyl ether to give (4-(4-methylthiazol-5-yl)phenyl)methanamine hydrochloride as yellow solid (0.35 g, 89%). LC-MS (ESI$^+$) m/z 205.2 (M+H)$^+$.

Step 4—tert-butyl (2S,4R)-4-hydroxy-2-((4-(4-methylthiazol-5-yl)benzyl)carbamoyl)pyrrolidine-1-carboxylate To a solution of (2S,4R)-1-(tert-butoxycarbonyl)-4-hydroxypyrrolidine-2-carboxylic acid (0.25 g, 1.08 mmol, CAS #13726-69-7) in DCM (5 mL) was added N-hydroxysuccinimide (0.16 g, 1.40 mmol) and EDC-HCl (0.25 g, 1.30 mmol) and the reaction was stirred at rt for 3 h. After 3 h, (4-(4-methylthiazol-5-yl)phenyl)methanamine hydrochloride (0.31 g, 1.30 mmol) and DIPEA (0.6 mL, 3.24 mmol) was added and the reaction mixture was stirred at room temperature for 18 h. The reaction mixture was diluted with saturated NaHCO$_3$ solution (50 mL) and extracted in DCM (50 mL×3). The combined organic layers were dried over anhydrous sodium sulfate and filtered. The filtrate was evaporated under reduced pressure and the crude product was purified using silica gel column chromatography (2%

MeOH-DCM) to give tert-butyl (2S,4R)-4-hydroxy-2-((4-(4-methylthiazol-5-yl)benzyl)carbamoyl)pyrrolidine-1-carboxylate as yellow solid (0.3 g, 66%). LC-MS (ESI⁺) m/z 418.8 (M+H)⁺.

Step 5—(2S,4R)-4-hydroxy-N-(4-(4-methylthiazol-5-yl)benzyl)pyrrolidine-2-carboxamide hydrochloride To a stirred solution of tert-butyl (2S,4R)-4-hydroxy-2-((4-(4-methylthiazol-5-yl)benzyl)carbamoyl)pyrrolidine-1-carboxylate (0.3 g, 0.7 mmol) in DCM (10 mL) was added 4N HCl in dioxane (1 mL) and the reaction mixture was stirred at rt for 3 h. The reaction mixture was then evaporated under vacuum and triturated using diethyl ether to give (2S,4R)-4-hydroxy-N-(4-(4-methylthiazol-5-yl)benzyl)pyrrolidine-2-carboxamide hydrochloride as yellow solid (0.2 g, 79%). LC-MS (ESI⁺) m/z 318.0 (M+H)⁺.

Step 6—tert-butyl ((S)-1-((2S,4R)-4-hydroxy-2-((4-(4-methylthiazol-5-yl)benzyl)carbamoyl)-pyrrolidin-1-yl)-3,3-dimethyl-1-oxobutan-2-yl)carbamate To a solution of (2S,4R)-4-hydroxy-N-(4-(4-methylthiazol-5-yl)benzyl)pyrrolidine-2-carboxamide hydrochloride (0.2 g, 0.6 mmol), (S)-2-((tert-butoxycarbonyl)amino)-3,3-dimethylbutanoic acid (0.13 g, 0.57 mmol, CAS #62965-35-9) and DIPEA (0.4 mL, 2.28 mmol) in DMF (2 mL), was added HATU (0.3 g, 0.63 mmol) and the reaction mixture was stirred at rt for 1 h. The reaction mixture was then transferred into ice water and the resulting mixture was extracted using ethyl acetate (3×20 mL). The combined organic layer was dried over anhydrous sodium sulfate and filtered. The filtrate was evaporated under reduced pressure and the crude product was purified using silica gel column chromatography (4% MeOH-DCM) to give tert-butyl ((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)carbamate as yellow semisolid (0.15 g, 44%). LC-MS (ESI⁺) m/z 531.81 (M+H)⁺.

Step 7—(2S,4R)-1-((S)-2-amino-3,3-dimethylbutanoyl)-4-hydroxy-N-(4-(4-methylthiazol-5-yl)benzyl)pyrrolidine-2-carboxamide hydrochloride To a stirred solution of tert-butyl ((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)carbamate (0.15 g, 0.28 mmol) in DCM (10 mL) was added 4N HCl in dioxane (1 mL) and the reaction mixture was stirred at rt for 3 h. The reaction mixture was then evaporated under vacuum and solid was triturated using diethyl ether to give (2S,4R)-1-((S)-2-amino-3,3-dimethylbutanoyl)-4-hydroxy-N-(4-(4-methylthiazol-5-yl)benzyl)pyrrolidine-2-carboxamide hydrochloride as yellow solid (0.12 g, 91%). ¹H NMR (400 MHz, DMSO) δ 9.10 (s, 1H), 8.78 (t, J=6 Hz, 1H), 8.27-8.07 (m, 3H), 7.50-7.31 (m, 4H), 4.55 (t, J=8.2 Hz, 1H), 4.50-4.30 (m, 2H), 4.29-4.15 (m, 1H), 4.05-3.85 (m, 1H), 3.84-3.70 (m, 1H), 3.65-3.45 (m, 1H), 2.46 (s, 3H), 2.20-2.05 (m, 1H), 1.95-1.80 (m, 1H), 1.32-1.27 (m, 1H), 1.03 (s, 9H). LC-MS (ESI⁺) m/z 431.85 (M+H)⁺.

tert-butyl ((1R,3R)-3-((2-(2-(2-aminoethoxy)ethoxy)ethoxy)methyl)cyclobutyl) carbamate (Intermediate H)

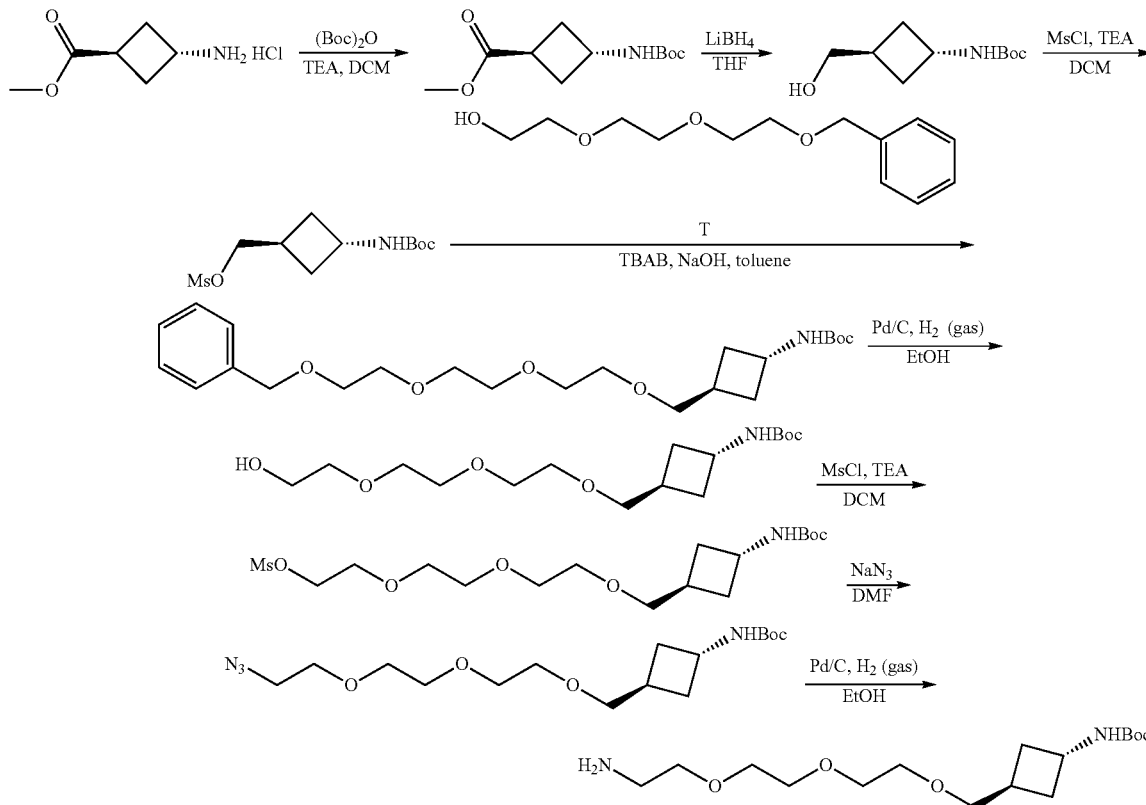

Step 1—methyl (1R,3R)-3-((tert-butoxycarbonyl)amino)cyclobutane-1-carboxylate To a stirred solution of methyl (1R,3R)-3-aminocyclobutane-1-carboxylate hydrochloride (1.0 g, 6.1 mmol), TEA (2 mL, 12 mmol) in DCM (5 mL) was added and Boc anhydride (1.7 g, 7.8 mmol) at 0° C. The reaction mixture was then stirred at rt for 3 h. The reaction mixture was then transferred into ice water and the resulting mixture was extracted using ethyl acetate (3×50 mL). The combined organic layer was dried over anhydrous sodium sulfate and filtered. The filtrate was evaporated under reduced pressure to give methyl (1R,3R)-3-((tert-butoxycarbonyl)amino)cyclobutane-1-carboxylate as a white solid (1.2 g, 72%). $^1$H NMR (400 MHz, DMSO) δ 7.26 (d, J=7.6 Hz, 1H), 4.10 (m, 1H), 3.62 (s, 3H), 2.96-2.91 (m, 1H), 2.36-2.31 (m, 2H), 2.19-2.12 (m, 2H), 1.42 (s, 9H).

Step 2—tert-butyl ((1R,R)-3-(hydroxymethyl)cyclobutyl)carbamate

To a stirred solution of methyl (1R,3R)-3-((tert-butoxycarbonyl)amino)cyclobutane-1-carboxylate (1.0 g, 4.4 mmol) in THF (20 mL) was added 3M lithium borohydride (9 mL, 9 mmol) at 0° C. Then the reaction mixture was heated and stirred at 60° C. for 3 h. The reaction mixture was then transferred into dilute NaOH and the resulting mixture was extracted using ethyl acetate (3×50 mL). The combined organic layer was dried over anhydrous sodium sulfate and filtered. The filtrate was evaporated under reduced pressure and the crude product was purified using silica gel column chromatography (3% MeOH-DCM) to give tert-butyl ((1r3r)-3-(hydroxymethyl)cyclobutyl)carbamate as a white solid (0.8 g, 91%). $^1$H NMR (400 MHz, DMSO) δ 4.77 (bs, 1H), 4.24 (d, J=6.8 Hz, 1H), 3.71 (d, J=6.0 Hz, 3H), 2.39 (s, 1H), 2.25-2.21 (m, 2H), 2.05-1.98 (m, 2H), 1.67-1.29 (m, 13H).

Step 3—((1R,3R)-3-((tert-butoxycarbonyl) amino)cyclobutyl)methyl methane sulfonate To a stirred solution of tert-butyl ((1R,3R)-3-(hydroxymethyl)cyclobutyl)carbamate (0.8 g, 4.0 mmol) in dichloromethane (20 mL) was added triethylamine (1.67 mL, 11.91 mmol) at 0° C. Mesyl chloride (0.82 mL, 5.96 mmol) was then added and the mixture was allowed to warm to rt and stirred for 2 h. The reaction mixture was then transferred into ice water and the resulting mixture was extracted using ethyl acetate (3×50 mL). The combined organic layer was dried over anhydrous sodium sulfate and filtered. The filtrate was evaporated under reduced pressure to give ((1R,3R)-3-((tert-butoxycarbonyl) amino)cyclobutyl)methyl methane sulfonate as yellow solid (0.9 g, 81%).

Step 4—tert-butyl ((1R,3R)-3-(12-phenyl-2,5,8,11-tetraoxadodecyl)cyclobutyl)carbamate A solution of 2-(2-(2-(benzyloxy)ethoxy) ethoxy)ethan-1-ol (0.43 g, 1.79 mmol, Intermediate T), ((1R,3R)-3-((tert-butoxycarbonyl)amino)cyclobutyl)methyl methanesulfonate (2.9 g, 10.39 mmol) and TBAB (20 mg) in toluene:8N NaOH (1:1, 16 mL) was stirred at 90° C. for 16 h. The reaction mixture was then transferred into ice water and the resulting mixture was extracted using ethyl acetate (3×25 mL). The combined organic layer was dried over anhydrous sodium sulfate and filtered. The filtrate was evaporated under reduced pressure and the crude product was purified using silica gel column chromatography (45% EtOAc-Hexane) to give tert-butyl ((1R,3R)-3-(18-phenyl-2,5,8,11,14,17-hexaoxaoctadecyl)cyclobutyl)carbamate as a light yellow liquid (0.7 g, 76%). LC-MS (ESI$^+$) m/z 441.50 (M+H)$^+$.

Step 5—tert-butyl ((1R,3R)-3-((2-(2-(2-hydroxyethoxy)ethoxy)ethoxy)methyl)cyclobutyl)carbamate To a stirred solution of tert-butyl ((1r,3r)-3-(12-phenyl-2,5,8,11-tetraoxadodecyl) cyclobutyl)carbamate (0.7 g, 1.65 mmol) in EtOH (20 mL) was added 10% Pd/C (50% wet) (0.7 g) and the reaction mixture was stirred under hydrogen atmosphere at rt for 6 h. The reaction mixture was then filtered through celite and evaporated under reduced pressure to give tert-butyl ((1R,3R)-3-((2-(2-(2-hydroxyethoxy)ethoxy)methyl)cyclobutyl)carbamate as a colorless liquid (0.5 g). LC-MS (ESI$^+$) m/z 351.45 (M+H)$^+$.

Step 6—2-(2-(2-(((1R,3R)-3-((tert-butoxycarbonyl)amino)cyclobutyl)methoxy)ethoxy)ethoxy)ethyl methanesulfonate To a stirred solution of tert-butyl ((1R,3R)-3-((2-(2-(2-hydroxyethoxy)ethoxy)ethoxy)methyl)cyclobutyl)carbamate (0.5 g, 1.5 mmol) and triethylamine (0.7 mL, 4.5 mmol) in dichloromethane (5 mL) was added mesyl chloride (0.15 mL, 1.8 mmol) at 0° C. The reaction was allowed to warm to rt and stirred for 3 h. The reaction mixture was then transferred into ice water and the resulting mixture was extracted using DCM (3×25 mL). The combined organic layer was dried over anhydrous sodium sulfate and filtered. The filtrate was evaporated under reduced pressure to give 2-(2-(2-(((1R,3R)-3-((tert-butoxycarbonyl)amino)cyclobutyl)methoxy)ethoxy)ethoxy)ethyl methanesulfonate as a light yellow solid (0.53 g, 85%).

Step 7—tert-butyl ((1R,3R)-3-((2-(2-(2-azidoethoxy)ethoxy)ethoxy)methyl) cyclobutyl)carbamate To a stirred solution of 2-(2-(2-(((1R,3R)-3-((tert-butoxycarbonyl)amino)cyclobutyl)methoxy)ethoxy)ethoxy)ethyl methanesulfonate (0.53 g, 1.30 mmol) in DMF (4 mL) was added sodium azide (0.13 g, 1.93 mmol) at rt. Then the reaction mixture was heated at 65° C. for 5 h. The reaction mixture was then transferred into ice water and the resulting mixture was extracted using ethyl acetate (3×25 mL). The combined organic layer was dried over anhydrous sodium sulfate and filtered. The filtrate was evaporated under reduced pressure to afford crude product. The crude product was purified using silica gel column chromatography (2% MeOH-DCM) to give tert-butyl ((1R,3R)-3-((2-(2-(2-azidoethoxy)ethoxy)ethoxy)methyl)cyclobutyl)carbamate as a light yellow liquid (0.45 g, 82%). LC-MS (ESI$^+$) m/z 376 (M+18)$^+$.

Step 8—tert-butyl ((1R,3R)-3-((2-(2-(2-aminoethoxy)ethoxy)ethoxy)methyl)cyclobutyl) carbamate To a stirred solution of tert-butyl ((1R,3R)-3-((2-(2-(2-azidoethoxy)ethoxy)ethoxy)methyl)cyclobutyl)carbamate (0.45 g, 1.25 mmol) in EtOH (20 mL) was added 10% Pd/C (50% wet) (0.45 g) and the reaction mixture was stirred under hydrogen atmosphere for 5 h. The reaction mixture was filtered through celite and concentrated under reduced pressure to give tert-butyl((1r,3 r)-3-((2-(2-(2-aminoethoxy)

ethoxy)ethoxy)methyl)cyclobutyl)carbamate as a colorless liquid (0.35 g). LC-MS (ESI$^+$) m/z 334.45 (M+18)$^+$.

12-((tert-butoxycarbonyl)amino)dodecanoic acid
(Intermediate I)

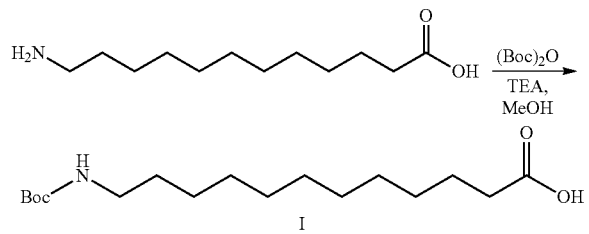

A mixture of 12-aminododecanoic acid (2.0 g, 9.3 mmol, CAS #693-57-2), Boc anhydride (2.4 mL, 10.2 mmol) and triethylamine (1.4 mL, 10.2 mmol) in methanol (50 mL) was refluxed for 18 h. The reaction mixture then cooled to rt and was concentrated under vacuum and diluted with ethyl acetate (200 mL). The organic layer was washed with 5% citric acid (100 mL×2), water (100 mL), dried over anhydrous sodium sulphate, and evaporated to give 12-((tert-butoxycarbonyl)amino)dodecanoic acid as a white solid (2.5 g, 85%). LC-MS (ESI$^+$) m/z 314.2 (M−H)$^+$.

1-phenyl-2,5,8,11-tetraoxatridecan-13-ol
(Intermediate J)

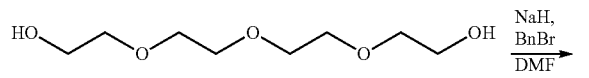

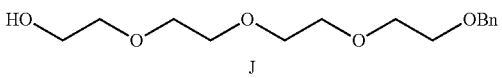

To a stirred solution of 2,2'-((oxybis(ethane-2,1-diyl))bis(oxy))bis(ethan-1-ol) (20.0 g, 103 mmol) in THF (150 mL) was added 60% NaH in paraffin (2.06 g, 51.5 mmol) at 10° C. in an ice water bath and the reaction mixture was stirred 0.5 h. To this reaction mixture benzyl bromide (5.9 mL, 51.49 mmol) in THF (50 mL) was added dropwise at 10° C. over 1.5 h. The resulting reaction mixture was allowed to warm to rt and stirred for 16 h. The reaction mixture was then transferred into ice water and the resulting mixture was extracted using ethyl acetate (3×100 mL). The combined organic layer was dried over anhydrous sodium sulfate and filtered. The filtrate was evaporated under reduced pressure and the crude product was purified using silica gel column chromatography (3% MeOH-DCM) to give 1-phenyl-2,5,8,11-tetraoxatridecan-13-ol as a yellow oil (15 g, 51%). LC-MS (ESI+) m/z 284.35 (M+H$_2$O)$^+$.

tert-butyl ((1R,4R)-4-(13-amino-2,5,8,11-tetraoxatridecyl)cyclohexyl)carbamate (Intermediate K)

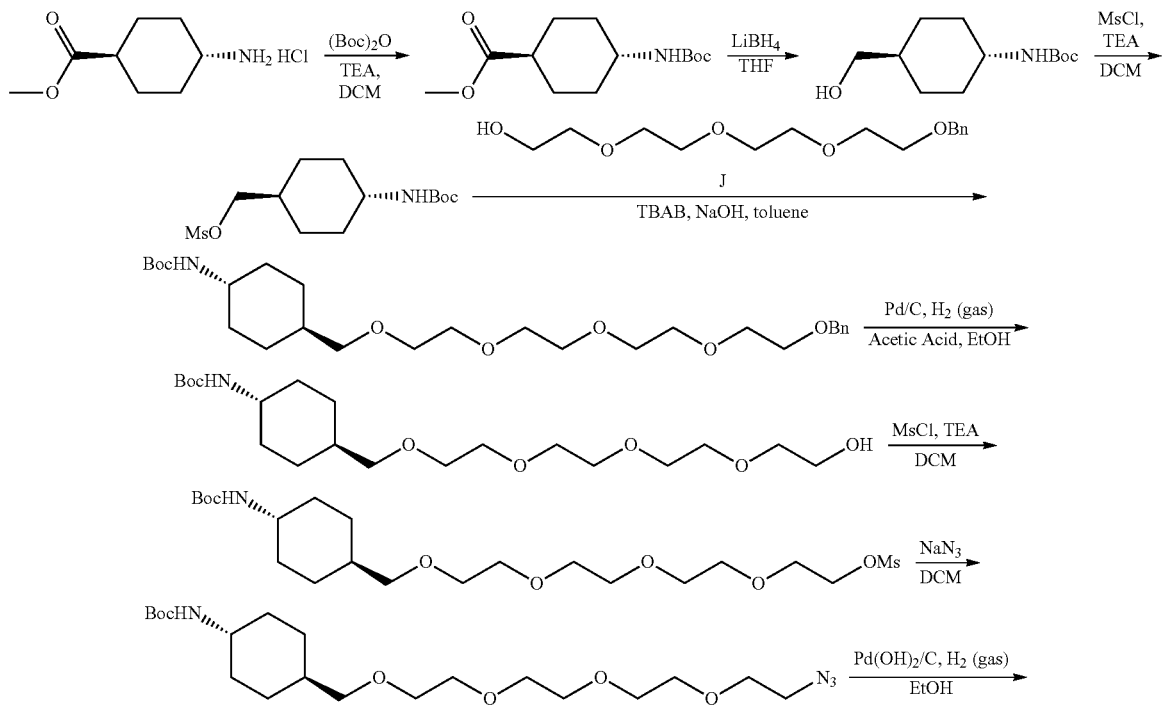

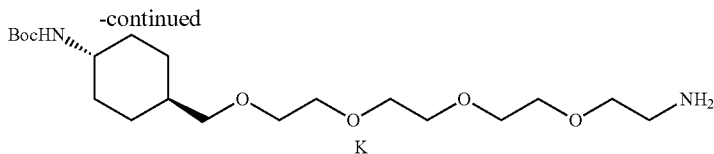

K

Step 1—methyl (1R,4R)-4-((tert-butoxycarbonyl)amino)cyclohexane-1-carboxylate To a stirred solution of methyl (1R,4R)-4-aminocyclohexane-1-carboxylate hydrochloride (6.5 g, 31.0 mmol) and triethylamine (6.8 mL, 92.94 mmol) in DCM (100 mL) was added Boc-anhydride (8.1 g, 37.18 mmol) dropwise at 0° C. The resulting reaction mixture was warmed to rt and stirred for 1.5 h. The reaction mixture was then transferred into ice water and the resulting mixture was extracted using DCM (3×100 mL). The combined organic layer was dried over anhydrous sodium sulfate and filtered. The filtrate was evaporated under reduced pressure to give methyl (1R,4R)-4-((tert-butoxycarbonyl)amino)cyclohexane-1-carboxylate as a white solid (6.6 g, 83%). LC-MS (ESI$^+$) m/z 258.2 (M+H)$^+$.

Step 2—tert-butyl ((1R,4R)-4-(hydroxymethyl)cyclohexyl)carbamate

To a stirred solution of methyl (1R,4R)-4-((tert-butoxycarbonyl)amino)cyclohexane-1-carboxylate (5.5 g, 21.4 mmol) in THF (20 mL) was added 3 M LiBH$_4$ in THF (16 mL, 43 mmol) dropwise at 0° C. The resulting reaction mixture then heated to 75° C. and stirred for 1 h. The reaction mixture was then transferred into 5% citric acid solution. The pH of the reaction mixture was adjusted to pH 8 to 9 with 8 N NaOH solution. The resulting mixture was then extracted using ethyl acetate (3×100 mL). The combined organic layer was dried over anhydrous sodium sulfate and filtered. The filtrate was evaporated under reduced pressure and the crude product was purified using silica gel column chromatography (25% EAc-Hexanes) to give tert-butyl ((1r,4r)-4-(hydroxymethyl)cyclohexyl)carbamate as white solid (1.5 g, 31%). LC-MS (ESI$^+$) m/z 230.2 (M+H)$^+$.

Step 3—((1R,4R)-4-((tert-butoxycarbonyl)amino)cyclohexyl)methyl methanesulfonate To a solution of tert-butyl ((1R,4R)-4-(hydroxymethyl)cyclohexyl)carbamate (1.8 g, 7.8 mmol) in DCM (50 mL) was added triethylamine (2.36 g, 23.4 mmol) and MsCl (0.9 mL, 11.7 mmol) at 0° C. and the reaction was stirred for 90 minutes. The reaction mixture was then diluted with water (50 mL) and product was extracted in DCM (50 mL×3). The organic layer was dried over anhydrous sodium sulphate, filtered and evaporated in vacuum to give ((1R,4R)-4-((tert-butoxycarbonyl)amino)cyclohexyl)methyl methanesulfonate as a light brown solid (1.8 g, 75%); LC-MS (ESI$^+$) m/z 308.2 (M+H)$^+$.

Step 4—tert-butyl ((1R,4R)-4-(15-phenyl-2,5,8,11,14-pentaoxapentadecyl)cyclohexyl)carbamate To a solution of 1-phenyl-2,5,8,11-tetraoxatridecan-13-ol (1.4 g, 4.9 mmol, Intermediate J) in toluene (20 mL) and 8N NaOH (20 mL) was added a catalytic amount of TBAB and the reaction was stirred for 15 minutes at rt. After 15 minutes, ((1R,4R)-4-((tert-butoxycarbonyl)amino)cyclohexyl)methyl methanesulfonate (1.8 g, 5.9 mmol) was added and the reaction mixture was refluxed for 16 h. The reaction mixture was then diluted with water (200 mL) and extracted in ethyl acetate (250 mL×3). The organic layer was dried over anhydrous sodium sulphate, filtered and evaporated in vacuo. The crude product was purified by silica gel column chromatography (45-50% EtOAC-Hexane) to give tert-butyl ((1R,4R)-4-(15-phenyl-2,5,8,11,14-pentaoxapentadecyl)cyclohexyl)carbamate as a yellow semisolid (0.8 g, 33%); LC-MS (ESI$^+$) m/z 496.5 (M+H)$^+$.

Step 5—tert-butyl ((1R,4R)-4-(13-hydroxy-2,5,8,11-tetraoxatridecyl)cyclohexyl)carbamate To a stirred solution of tert-butyl ((1R,4R)-4-(15-phenyl-2,5,8,11,14-pentaoxapentadecyl)cyclohexyl)carbamate (0.8 g, 1.6 mmol) in ethanol (50 mL) was added 10% Pd/C (50% wet) (0.8 g) and acetic acid (0.2 mL) at room temperature with hydrogen gas bubbling through the solution for 2 h. The reaction mixture was then filtered through a pad of celite and the filtrate was evaporated to give tert-butyl ((1R,4R)-4-(13-hydroxy-2,5,8,11-tetraoxatridecyl)cyclohexyl)carbamate as a brown oil (0.7 g, 64%); LC-MS (ESI$^+$) m/z 406.4 (M+H)$^+$.

Step 6 1-((1R,4R)-4-((tert-butoxycarbonyl)amino)cyclohexyl)-2,5,8,11-tetraoxatridecan-13-yl methanesulfonate To a stirred solution of tert-butyl ((1R,4R)-4-(13-hydroxy-2,5,8,11-tetraoxatridecyl)cyclohexyl)carbamate (0.37 g, 0.91 mmol) in DCM (10 mL) was added triethylamine (0.3 mL, 2.7 mmol) at 0° C. followed by mesyl chloride (0.11 g, 1.37 mmol) then the reaction was stirred for 2 h. The reaction was then quenched with water (50 mL) and product was extracted using DCM (50 mL×3). The organic layer was dried over anhydrous sodium sulphate and evaporated in vacuo to give 1-((1R,4R)-4-((tert-butoxycarbonyl)amino)cyclohexyl)-2,5,8,11-tetraoxatridecan-13-yl methanesulfonate as a yellow oil (0.37 g; 82%).

Step 7—tert-butyl ((1r,4r)-4-(13-azido-2,5,8,11-tetraoxatridecyl)cyclohexyl)carbamate To a stirred solution of 1-((1R,4R)-4-((tert-butoxycarbonyl)amino)cyclohexyl)-2,5,8,11-tetraoxatridecan-13-yl methanesulfonate (0.36 g, 0.74 mmol) in DMF (5 mL) was added NaN$_3$ (0.072 g, 1.11 mmol) and the reaction mixture was heated at 70° C. for 2 h. The reaction mixture was then cooled to rt and diluted with water (250 mL) and extracted in ethyl acetate (100 mL×3). The organic layer was dried over anhydrous sodium sulphate and evaporated in vacuo to give and the crude product was purified by silica gel column chromatography (40% EtOAc-Hexane) to give tert-butyl ((1r,4r)-4-(13-azido-2,5,8,11-tetraoxatridecyl)cyclohexyl)carbamate as a yellow semisolid (0.29 g; 90%); LC-MS (ESI$^+$) m/z 448.8 (M+18)$^+$.

Step 8—tert-butyl ((1r,4r)-4-(13-amino-2,5,8,11-tetraoxatridecyl)cyclohexyl)carbamate To a stirred solution of tert-butyl ((1R,4R)-4-(13-azido-2,5,8,11-tetraoxatridecyl)-cyclohexyl)carbamate (0.29 g, 0.67 mmols) in ethanol (20 mL) was added 10% Pd(OH)$_2$/C (50% wet) (0.29 g) at rt and the reaction mixture was stirred in autoclave under hydrogen gas (20 kg/cm$^2$ pressure) for 5 h. The reaction mixture was filtered through a pad of celite and the filtrate was evaporated in vacuo to give tert-butyl ((1R,4R)-4-(13-amino-2,5,8,11-tetraoxatridecyl)cyclohexyl)carbamate as a yellow semisolid (0.17, 62%); LC-MS (ESI$^+$) m/z 405.4 (M+H)$^+$.

6-(5-cyano-1H-pyrazolo[3,4-b]pyridin-1-yl)-4-(cyclopropylamino)nicotinic acid (Intermediate L)

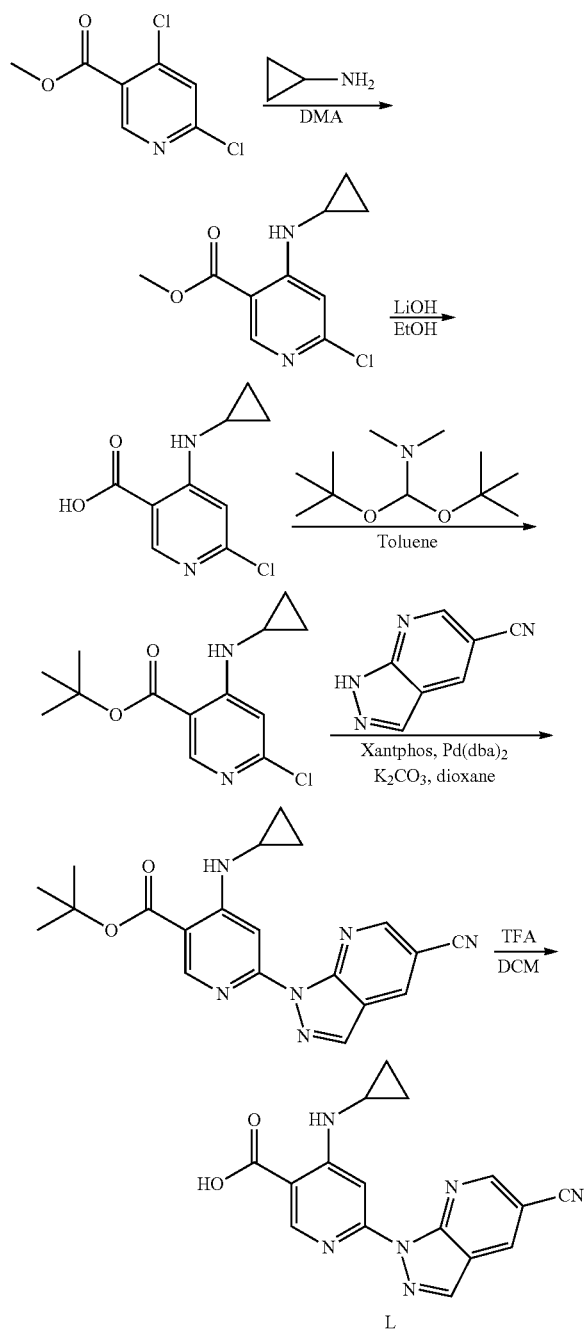

Step 1—methyl 6-chloro-4-(cyclopropylamino)nicotinate

A solution of methyl 4,6-dichloronicotinate (10.0 g, 48.5 mmol), DIPEA (6.26 g, 48.5 mmol, 8.23 mL) and cyclopropylamine (3.04 g, 53.4 mmol) in DMA (80 mL) was stirred at 90° C. for 3 h. The reaction mixture was then transferred into ice water and the resulting mixture was extracted using ethyl acetate (3×25 mL). The combined organic layer was dried over anhydrous sodium sulfate and filtered. The filtrate was evaporated under reduced pressure and the crude product was purified using silica gel column chromatography (10% EtOAc-Hexane) to give methyl 6-chloro-4-(cyclopropylamino)nicotinate as a white solid (8.5 g, 77%). $^1$H NMR (400 MHz, DMSO-d6) δ 8.538 (s, 1H), 8.079 (s, 1H), 7.040 (s, 1H), 3.826 (s, 3H), 2.634-2.594 (m, 1H), 0.892-0.846 (m, 2H), 0.595-0.557 (m, 2H).

Step 2—6-chloro-4-(cyclopropylamino)nicotinic acid

A stirred solution of methyl 6-chloro-4-(cyclopropylamino)nicotinate (6.8 g, 30.0 mmol) in ethanol (70 mL) was cooled to 0-10° C. Then a solution of lithium hydroxide (3.6 g, 85.7 mmol in water (10 mL) was added. The reaction mixture was allowed to warm to rt and was stirred for 3 h. The reaction mixture was then transferred into ice water and the resulting mixture was extracted using ethyl acetate (2×100 mL). The aqueous layer was acidified by addition of saturated citric acid solution until the pH=3-4. The mixture was then extracted with ethyl acetate (3×250 mL). The combined organic layer was dried over anhydrous sodium sulfate and filtered. The filtrate was evaporated under reduced pressure and the crude product was triturated using hexane to give 6-chloro-4-(cyclopropylamino)nicotinic acid as an off-white solid (5 g, 78%). $^1$H NMR (400 MHz, DMSO-d6) δ 13.415 (bs, 1H), 8.525 (s, 1H) 8.318 (s, 1H), 7.007 (s, 1H), 2.616-2.592 (m, 1H), 0.891-0.845 (m, 2H), 0.620-0.564 (m, 2H).

Step 3—tert-butyl 6-chloro-4-(cyclopropylamino)nicotinate

A stirred solution 6-chloro-4-(cyclopropylamino)nicotinic acid (2.5 g, 11.74 mmol) and DMF-DTA (10.2 g, 50.3 mmol) in toluene (50 mL) was heated at 110° C. for 16 h. The reaction mixture was then transferred into ice water and the resulting mixture was extracted using ethyl acetate (3×250 mL). The combined organic layer was dried over anhydrous sodium sulfate and filtered. The filtrate was evaporated under reduced pressure and the crude product was purified using silica gel column chromatography (6% EtOAc-Hexane) to give tert-butyl 6-chloro-4-(cyclopropylamino)nicotinate as a white solid (2.23 g, 70%). LC-MS (ESI$^+$) m/z 269.3 (M+H)$^+$.

Step 4—tert-butyl 6-(5-cyano-1H-pyrazolo[3,4-b]pyridin-1-yl)-4-(cyclopropylamino) nicotinate Under an atmosphere of argon, 1H-pyrazolo[3,4-b]pyridine-5-carbonitrile (1.0 g, 6.94 mmol), tert-butyl 6-chloro-4-(cyclopropylamino)nicotinate (2.05 g, 7.63 mmol), potassium carbonate (2.9 g, 20.83 mmol), Xantphos (1.61 g, 2.77 mmol) and Pd(dba)$_2$ (1.6 g, 2.77 mmol) in 1,4-dioxane (50 mL) was heated at 120° C. for 20 h. The reaction mixture was filtered through celite and washed with ethyl acetate (3×300 mL). The combined organic layer was washed with water (400 mL), dried over anhydrous sodium sulfate and filtered. The filtrate was evaporated under reduced pressure and the crude product was purified using silica gel column chromatography (1% MeOH-DCM) to give tert-butyl 6-(5-cyano-1H-pyrazolo[3,4-b]pyridin-1-yl)-4-(cyclopropylamino) nicotinate as a brown solid (0.6 g, 21%). LC-MS (ESI⁺) m/z 377.3 (M+H)⁺

Step 5—6-(5-cyano-1H-pyrazolo[3,4-b]pyridin-1-yl)-4-(cyclopropylamino)nicotinic acid (as the TFA salt)

A solution of tert-butyl 6-(5-cyano-1H-pyrazolo[3,4-b]pyridin-1-yl)-4-(cyclopropylamino)nicotinate (0.4 g, 1.06 mmol) and TFA (4 mL) in DCM (10 mL) was stirred at rt for 6 h. The organic solvent was evaporated and the residue was triturated with MTBE (20 mL) to give 6-(5-cyano-1H-pyrazolo[3,4-b]pyridin-1-yl)-4-(cyclopropylamino)nicotinic acid as the TFA salt as a white solid (0.3 g, 88%). $^1$H NMR (400 MHz, DMSO-d6) δ 13.38 (bs, 1H), 9.10 (d, J=2 Hz, 1H), 9.04 (d, J=2 Hz, 1H), 8.76 (s, 1H), 8.70 (s, 1H), 8.43 (s, 1H), 7.83 (s, 1H), 2.66-2.60 (m, 1H), 0.93-0.89 (m, 2H), 0.65-0.62 (m, 2H).

1,6-naphthyridin-2-amine (Intermediate M)

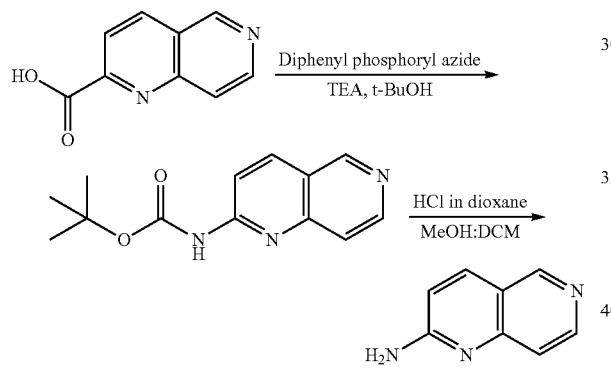

Step 1—tert-butyl (1,6-naphthyridin-2-yl)carbamate

To a stirred solution of 1,6-naphthyridine-2-carboxylic acid (20.0 g, 114 mmol) in t-BuOH (200 mL) was added Et₃N (16 mL, 114 mmol) and diphenyl phosphoryl azide (37.0 g, 137 mmol) respectively at rt. The resulting mixture then heated to 80° C. and stirred for 24 h. The reaction mixture was evaporated carefully under vacuum, diluted with ice water and resulting solid was collected by filtration. The solid was treated with hot ethanol and again filtered and dried under vacuum to give tert-butyl (1,6-naphthyridin-2-yl)carbamate as a light brown solid (13.1 g, 46%). $^1$H NMR (400 MHz, DMSO-d₆) δ 10.49 (s, 1H), 9.20 (s, 1H), 8.61 (d, J=6 Hz, 1H), 8.47 (d, J=9.2 Hz, 1H), 8.18 (d, J=8.8 Hz, 1H), 7.62 (s, 1H), 1.50 (s, 9H). LC-MS (ESI⁺) m/z 246.2 (M+H)⁺

Step 2—1,6-naphthyridin-2-amine

To a stirred solution of tert-butyl (1,6-naphthyridin-2-yl)carbamate (4.37 g, 17.8 mmol) in MeOH:DCM (40 mL, 3:1 ratio) was added 4N HCl in dioxane (15 mL) at 0° C. The resulting reaction mixture was allowed to warm to rt and stirred for 18 h. The reaction mixture was then evaporated under vacuum and diluted with 30 mL of water. Saturated NaHCO₃ solution (15 mL) was added and the resulting mixture was extracted using EtOAc (2×50 mL). The combined organic layers were dried under vacuum to give 1,6-naphthyridin-2-amine as a white solid (2.45 g, 94%). $^1$H NMR (400 MHz, DMSO-d₆) δ 9.03 (s, 1H), 8.43 (d, J=6 Hz, 1H), 8.14 (d, J=8.8 Hz, 1H), 7.72 (bs, 2H), 7.45 (d, J=6 Hz, 1H), 6.96 (d, J=8.8 Hz, 1H); LCMS (ESI⁺) m/z 146.4 (M+H)⁺.

(6-((1,6-naphthyridin-2-yl)amino)-4-(cyclopropylamino)nicotinic acid (Intermediate N)

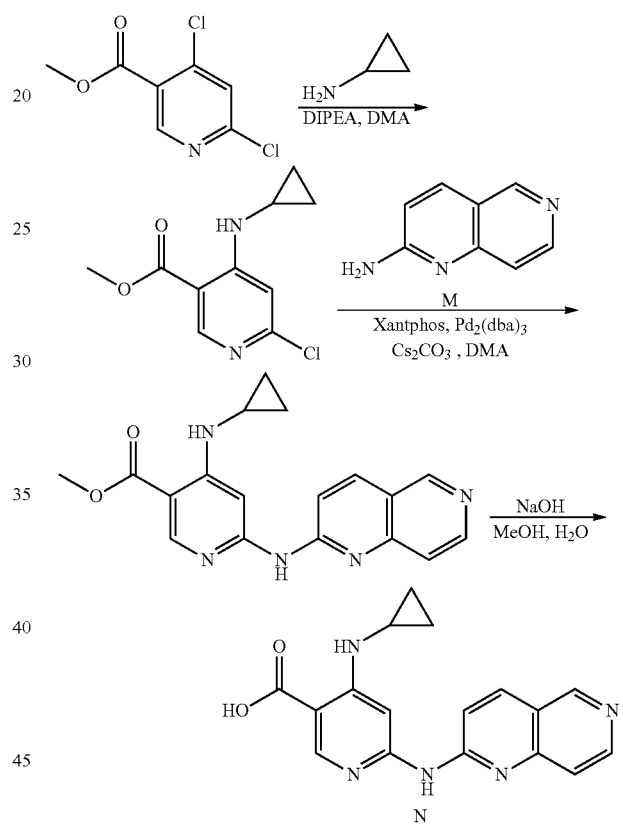

Step 1—methyl 6-chloro-4-(cyclopropylamino)nicotinate

To a stirred solution of methyl 4,6-dichloronicotinate (10.0 g, 48.5 mmol) in DMA (80 mL) was added DIPEA (6.6 mL, 48.5 mmol) and cyclopropylamine (3.7 mL, 53.0 mmol) at rt. The resulting mixture then heated at 90° C. for 3 h. After 3 h, the reaction mixture was cooled to rt and diluted with ice water. The resulting mixture was stirred for 20 min and the solid precipitate was collected by filtration and dried under vacuum. The crude product was purified by silica gel column chromatography (10% EtOAc-hexanes) to give methyl 6-chloro-4-(cyclopropylamino)nicotinate as a white solid (9.5 g, 87%). $^1$H NMR (400 MHz, CDCl₃) δ 8.67 (s, 1H), 8.20 (bs, 1H), 6.98 (s, 1H), 3.89 (s, 3H), 2.51 (m, 1H), 0.91 (q, J=6.8 Hz, 2H), 0.61-0.65 (m, 2H); LC-MS (ESI⁺) m/z 227.2 (M+H)⁺.

Step 2—methyl 6-((1,6-naphthyridin-2-yl)amino)-4-(cyclopropylamino)nicotinate To a stirred solution of methyl 6-chloro-4-(cyclopropylamino)nicotinate (2.5 g, 11.8 mmol) and 1,6-naphthyridin-2-amine (1.6 g, 11.76 mmol, Intermediate M) in DMA (50 mL) was added Xantphos (2.5 g, 4.4 mmol) and $Cs_2CO_3$ (5.76 g, 17.60 mmol) and resulting reaction mixture was degassed using argon for 30 min. Then of $Pd_2(dba)_3$ (2.0 g, 2.2 mmol) was added. The resulting mixture was heated at 120° C. for 18 h. The reaction mixture was cooled to rt and ice water was added. The resulting solid precipitate was collected by filtration and dried under vacuum. The crude product was purified by silica gel column chromatography (5% MeOH-DCM) to give methyl 6-((1,6-naphthyridin-2-yl)amino)-4-(cyclopropylamino)nicotinate as a yellow solid (2.2 g, 59%). $^1$H NMR (400 MHz, DMSO-$d_6$) δ 10.5 (s, 1H), 9.08 (s, 1H), 8.66 (s, 1H), 8.58-8.60 (m, 2H), 8.31 (d, J=8.8 Hz, 1H), 8.03 (s, 1H), 7.61 (d, J=6 Hz, 1H), 7.51 (d, J=8.8 Hz, 1H), 3.80 (s, 3H), 2.67-2.70 (m, 1H), 0.99-1.02 (m, 2H), 0.65-0.67 (m, 2H). LC-MS (ESI$^+$) m/z 336.6 (M+H)$^+$.

Step 3—6-((1,6-naphthyridin-2-yl)amino)-4-(cyclopropylamino)nicotinic acid

To a stirred solution of methyl 6-((1,6-naphthyridin-2-yl)amino)-4-(cyclopropylamino)nicotinate (1.6 g, 1.8 mmol) in methanol:water (30 mL, 1:1 ratio) was added NaOH (0.36 g, 5 mmol) at rt. The resulting reaction mixture was then heated at 70° C. for 16 h. Upon completion, the reaction mixture was in vacuo and the resulting solid was triturated using ethyl acetate and collected by filtration. The solid was taken in water and the pH was adjusted to 6-7 using dilute HCl and the resulting solid was collected by filtration and dried under vacuum to give 6-((1,6-naphthyridin-2-yl)amino)-4-(cyclopropylamino)nicotinic acid as a dark yellow solid (0.45 g, 78%). LC-MS (ESI$^+$) m/z 322.6 (M+H)$^+$

(1R,3R)-3-(6-((1,6-naphthyridin-2-yl)amino)-4-(cyclopropylamino)nicotinamido)cyclobutane-1-carboxylic acid (Intermediate O)

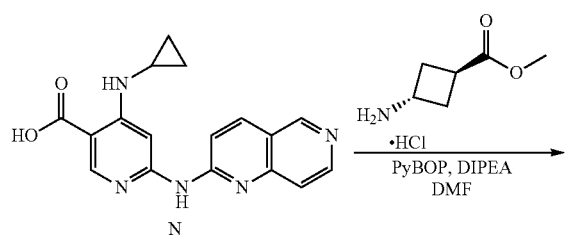

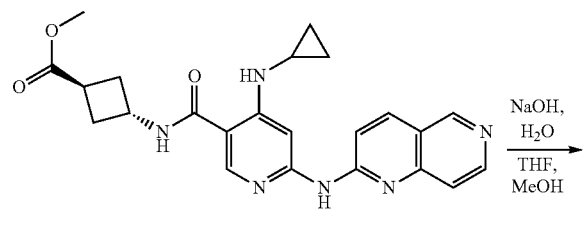

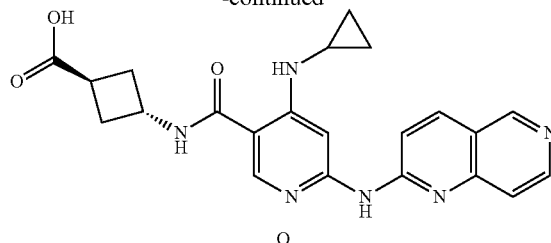

Step 1—methyl (1R,3R)-3-(6-((1,6-naphthyridin-2-yl)amino)-4-(cyclopropylamino) nicotinamido)cyclobutane-1-carboxylate To a stirred solution of methyl (1R,3R)-3-aminocyclobutane-1-carboxylate-HCl (0.2 g, 1.6 mmol) and 6-((1,6-naphthyridin-2-yl)amino)-4-(cyclopropylamino)nicotinic acid (0.5 g, 1.6 mmol, Intermediate N) in DMF (4 mL) was added DIPEA (0.9 mL, 4.7 mmol) and PyBOP (1.2 g, 2.3 mmol) at rt. The resulting reaction mixture was stirred at rt for 2 h. The reaction mixture was then transferred into ice water and the resulting mixture was filtered, dried and dried under reduced pressure. The crude product was triturated with MTBE and dried in vacuo to give methyl (1r,3r)-3-(6-((1,6-naphthyridin-2-yl)amino)-4-(cyclopropylamino)nicotinamido)cyclo butane-1-carboxylate as a yellow solid. (0.55 g, 81%). LC-MS (ESI$^+$) m/z 433.2 (M+H)$^+$.

Step 2—(1R,3R)-3-(6-((1,6-naphthyridin-2-yl)amino)-4-(cyclopropylamino)nicotinamido) cyclobutane-1-carboxylic acid To a stirred solution of methyl (1R,3R)-3-(6-((1,6-naphthyridin-2-yl)amino)-4-(cyclopropylamino)nicotinamido) cyclobutane-1-carboxylate (0.55 g, 1.27 mmol) in THF:MeOH (15 mL, 1:1) was dropwise added NaOH (0.16 g, 3.82 mmol) in 5 mL water at rt. The resulting reaction mixture was stirred at rt for 3 h. The reaction mixture was then evaporated under vacuum, and water (10 mL) was added and the pH was adjusted to 6-7 using 10% citric acid solution. The resulting mixture was then stirred for 15 min, and the solid precipitate was filtered off and dried under vacuo to give (1R,3R)-3-(6-((1,6-naphthyridin-2-yl)amino)-4-(cyclopropylamino)-nicotinamido)cyclobutane-1-carboxylic acid as a yellow solid. (0.4 g, 75%). $^1$H NMR (400 MHz, DMSO) δ 11.18 (s, 1H), 10.36 (s, 1H), 9.05 (d, J=7.2 Hz, 1H), 8.59-8.45 (m, 4H), 8.28-8.23 (m, 1H), 7.58-7.03 (m, 4H), 4.52-4.46 (m, 1H), 2.91 (t, J=8.8 Hz, 1H), 2.58-2.27 (m, 4H), 0.90 (m, 2H), 0.52 (m, 2H).

Ethyl 2-(4-aminopiperidin-1-yl)acetate hydrochloride (Intermediate P)

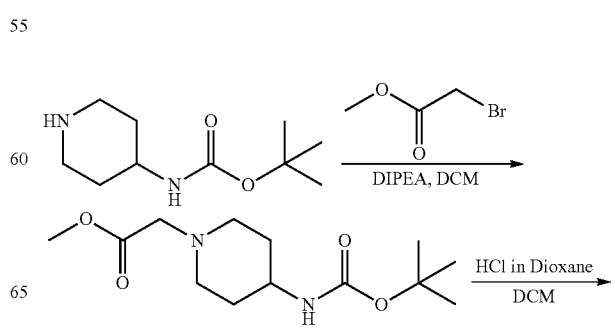

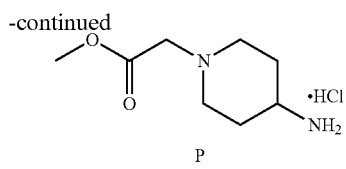

P

Step 1—methyl 2-(4-((tert-butoxycarbonyl)amino) piperidin-1-yl)acetate

A solution of tert-butyl piperidin-4-ylcarbamate (0.5 g, 2.5 mmol), ethyl bromo acetate (0.45 g, 2.75 mmol) and DIPEA (0.65 mL, 3.76 mmol) in DCM (5 mL) was stirred at rt for 3 h. The reaction mixture was then transferred into ice water and the resulting mixture was extracted using DCM (3×20 mL). The combined organic layer was dried over anhydrous sodium sulfate and filtered. The filtrate was evaporated under reduced pressure to give methyl 2-(4-((tert-butoxycarbonyl)amino)piperidin-1-yl)acetate as a colorless oil (0.55 g, 81%). LC-MS (ESI$^+$) m/z 287.2 (M+H)$^+$.

Step 2—ethyl 2-(4-aminopiperidin-1-yl)acetate hydrochloride

To a solution of ethyl 2-(4-((tert-butoxycarbonyl)amino) piperidin-1-yl)acetate (0.55 g, 1.92 mmol) in DCM (10 mL) was added 4N HCl in dioxane (3 mL) at 0° C. and then the reaction was allowed to warm to rt and stirred for 4 h. The reaction mixture was then evaporated under vacuum and the solid was triturated using MTBE (5 mL) to give ethyl 2-(4-aminopiperidin-1-yl)acetate hydrochloride as white solid (0.3 g, 86%). LC-MS (ESI$^+$) m/z 187.2 (M+H)$^+$.

Methyl 2-(3-aminoazetidin-1-yl)acetate 2,2,2-trifluoroacetate (Intermediate Q)

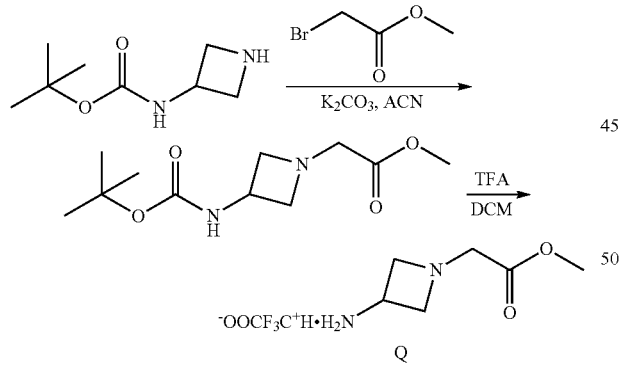

Q

Step 1—methyl 2-(3-((tert-butoxycarbonyl)amino) azetidin-1-yl)acetate

To a mixture of tert-butyl azetidin-3-ylcarbamate (0.5 g, 0.58 mmol) and K$_2$CO$_3$ (0.6 g, 0.87 mmol) in ACN (5 mL) at 0° C. was added a solution of methyl 2-bromoacetate (0.444 g, 0.58 mmol) in ACN (5 mL) at same temperature and the reaction mixture was stirred for 25 minutes. The reaction mixture was then diluted with water (100 mL) and product was extracted in ethyl acetate (50 mL×3). The organic layer was dried over anhydrous sodium sulphate, filtered and evaporated in vacuo. The crude product was purified by silica gel column chromatography (3% MeOH-DCM) to give methyl 2-(3-((tert-butoxycarbonyl)amino) azetidin-1-yl)acetate as a yellow semi-solid (0.15 g, 21%); LC-MS (ESI$^+$) m/z 245.2 (M+H)$^+$.

Step 2—methyl 2-(3-aminoazetidin-1-yl)acetate 2,2,2-trifluoroacetate

To a stirred solution of methyl 2-(3-((tert-butoxycarbonyl)amino)azetidin-1-yl)acetate (0.15 g, 0.61 mmol) in DCM (10 mL) was added TFA (3 mL) at 0° C. and the reaction was stirred for 3 h. The reaction mixture was then evaporated in vacuo and triturated with diethyl ether to give methyl 2-(3-aminoazetidin-1-yl)acetate 2,2,2-trifluoroacetate as a brown semisolid (0.1 g, 63%); LC-MS (ESI$^+$) m/z 145.16 (M+H)$^+$.

2-(2,6-dioxopiperidin-3-yl)-4-fluoroisoindoline-1,3-dione (Intermediate R)

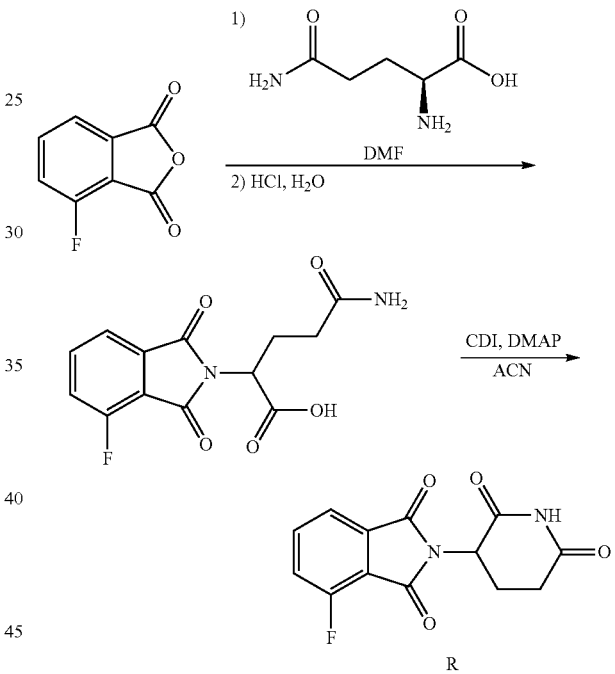

R

Step 1—5-amino-2-(4-fluoro-1,3-dioxoisoindolin-2-yl)-5-oxopentanoic acid

To a stirred solution of 4-fluoroisobenzofuran-1,3-dione (25 g, 150 mmol, CAS #652-39-1) in DMF (100 mL) was added L-glutamine (22 g, 150 mmol) at rt. The resulting reaction mixture was heated to at 90° C. and stirred for 2 h. The reaction mixture was then evaporated under reduced pressure, transferred into 4 N aqueous HCl solution and the resulting mixture was stirred for 36 h at rt. The solid precipitate was then filtered off, washed with cold water and dried under reduced pressure to give 5-amino-2-(4-fluoro-1,3-dioxoisoindolin-2-yl)-5-oxopentanoic acid as a white solid (28 g, 63%). LC-MS (ESI$^+$) m/z 295 (M+H)$^+$.

Step 2—2-(2,6-dioxopiperidin-3-yl)-4-fluoroisoindoline-1,3-dione

To a stirred solution of 5-amino-2-(4-fluoro-1,3-dioxoisoindolin-2-yl)-5-oxopentanoic acid (28 g, 95 mmol) in acetonitrile (200 mL) was added CDI (19 g, 110 mmol) and DMAP (0.14 g, 1.1 mmol) at rt. The resulting reaction mixture then heated to 90° C. and stirred for 5 h. The reaction mixture was then evaporated under reduced pressure. The crude product was purified using silica gel column chromatography (2% MeOH-DCM) to give 2-(2,6-dioxopiperidin-3-yl)-4-fluoroisoindoline-1,3-dione as a yellow solid (12 g, 46%). $^1$H NMR (400 MHz, DMSO) δ ppm 11.16 (s, 1H), 7.98-7.93 (m, 1H), 7.80-7.76 (m, 2H), 5.19-5.14 (m, 1H), 2.94-2.85 (m, 1H), 2.63-2.54 (m, 2H), 2.09-2.04 (m, 1H).

tert-butyl (3-(3-aminopropoxy)propyl)carbamate (Intermediate S)

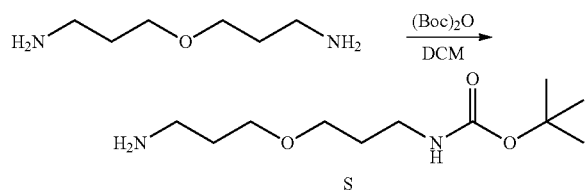

A solution of 3,3'-oxybis(propan-1-amine) (1.0 g, 7.6 mmol, CAS #2157-24-6), and Boc anhydride (0.83 g, 3.78 mmol) in DCM (8 mL) was stirred at rt for 16 h. The reaction mixture was then transferred into ice water and the resulting mixture was extracted using DCM (3×50 mL). The combined organic layer was dried over anhydrous sodium sulfate and filtered. The filtrate was evaporated under reduced pressure. The crude product was purified using silica gel column chromatography (5% MeOH-DCM) to give tert-butyl (3-(3-aminopropoxy)propyl)carbamate as a white solid (0.36 g, 21%). $^1$H NMR (400 MHz, DMSO) δ 10.34 (s, 1H), 9.05 (s, 1H), (d, J=5.2 Hz, 3H), 8.42 (s, 1H), 8.28 (d, J=9.2 Hz, 1H), 8.14 (d, J=7.6 Hz, 1H), 7.70-7.67 (m, 1H), 6.76 (bs, 1H), 3.70 (t, J=2.8 Hz, 1H), 3.00-3.05 (m, 2H), 2.89-2.86 (m, 2H), 2.06 (s, 1H), 1.88 (d, J=12.4 Hz, 2H), 1.77 (d, J=11.6 Hz, 2H), 1.48-1.21 (m, 17H). LC-MS (ESI$^+$) m/z 233.35 (M+H)$^+$ 2-(2-(2-(benzyloxy)ethoxy)ethoxy)ethan-1-ol (Intermediate T)

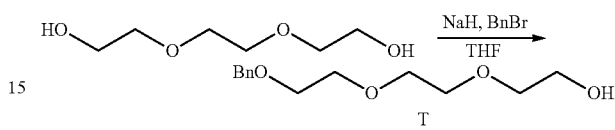

To a stirred solution of 2,2'-(ethane-1,2-diylbis(oxy))bis(ethan-1-ol) (30 g, 200 mmol) in THF (125 mL) was added 60% NaH in paraffin (4 g, 100 mmol) at 10° C. The resulting reaction mixture stirred at the same temperature for 0.5 h. To this reaction mixture was then added benzyl bromide (17 g, 100 mmol) in THF (125) dropwise at 10° C. over 1.5 h. The resulting reaction mixture then stirred at rt for 16 h. The reaction mixture was then transferred into ice water and the resulting mixture was extracted using DCM (3×100 mL). The combined organic layer was dried over anhydrous sodium sulfate and filtered. The filtrate was evaporated under reduced pressure and the crude product was purified using silica gel column chromatography (4% MeOH-DCM) to give 2-(2-(2-(benzyloxy)ethoxy)ethoxy)ethan-1-ol as a yellow oil (20 g, 42%). LC-MS (ESI$^+$) m/z 241.35 (M+H)$^+$ tert-butyl ((1R,3R)-3-((2-(2-(2-aminoethoxy)ethoxy)ethoxy)methyl)cyclopentyl)carbamate (Intermediate U)

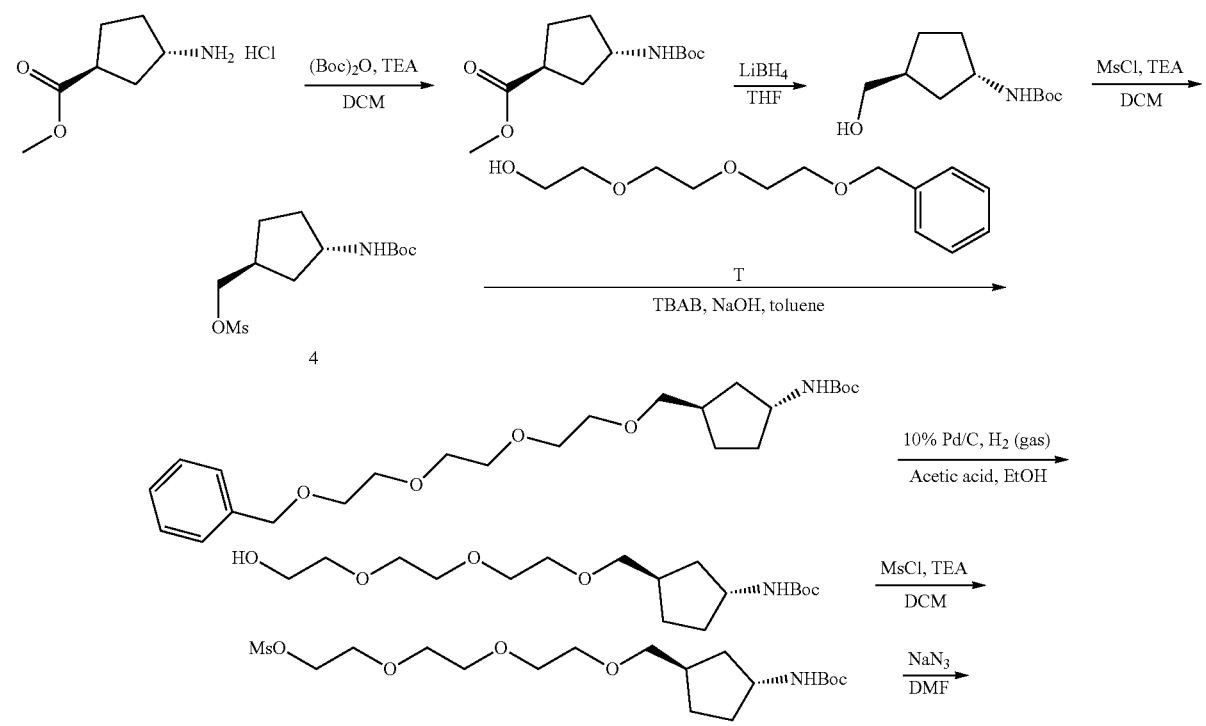

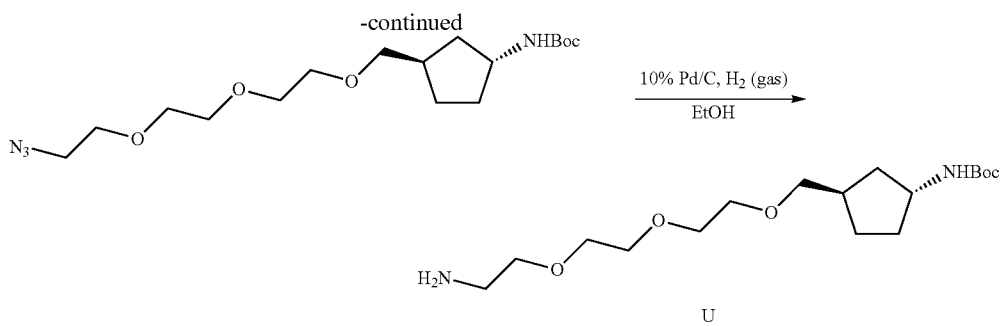

U

Step 1—methyl (1S,3S)-3-((tert-butoxycarbonyl)amino)cyclopentane-1-carboxylate To a stirred solution of methyl (1S,3S)-3-aminocyclopentane-1-carboxylate hydrochloride (4.5 g, 25 mmol) and TEA (10.5 mL, 75 mmol) in DCM (100 mL) was dropwise added Boc-anhydride (6.6 g, 30 mmol) at 0° C. The resulting reaction mixture was then allowed to warm to rt and then stirred for 1.5 h. The reaction mixture was then transferred into ice water and the resulting mixture was extracted using DCM (3×100 mL). The combined organic layer was dried over anhydrous sodium sulfate and filtered. The filtrate was evaporated under reduced pressure and the crude product was purified using silica gel column chromatography (40% EAc-Hexanes) to give methyl (1S,3S)-3-((tert-butoxycarbonyl)amino)cyclopentane-1-carboxylate as a white solid (5.1 g, 84%). LC-MS (ESI$^+$) m/z 261.3 (M+18)$^+$.

Step 2—tert-butyl ((1S,3S)-3-(hydroxymethyl)cyclopentyl)carbamate

To a stirred solution of methyl (1S,3S)-3-((tert-butoxycarbonyl)amino)cyclopentane-1-carboxylate (2.5 g, 10.2 mmol) in THF (50 mL) was added 4 M LiBH$_4$ in THF (5.13 mL, 20.4 mmol) dropwise at 0° C. The resulting reaction mixture then heated to 75° C. and stirred for 1 h. The reaction mixture was then transferred into 5% citric acid solution. The pH of the solution was then adjusted to pH=8 to 9 with 8 N NaOH solution. The resulting mixture was extracted using ethyl acetate (3×100 mL). The combined organic layer was dried over anhydrous sodium sulfate and filtered. The filtrate was evaporated under reduced pressure and crude product was purified using silica gel column chromatography (3% MeOH-DCM) to give tert-butyl ((1S,3S)-3-(hydroxymethyl)cyclopentyl)carbamate as a white solid (1.9 g, 86%). LC-MS (ESI$^+$) m/z 233.15 (M+18)$^+$.

Step 3—((1S,3S)-3-((tert-butoxycarbonyl)amino)cyclopentyl)methyl methanesulfonate To a stirred solution of tert-butyl ((1S,3S)-3-(hydroxymethyl)cyclopentyl)carbamate (1.6 g, 7.4 mmol) and TEA (3.1 mL, 22.3 mmol) in DCM (25 mL) was added Mesyl chloride (0.91 mL, 11.14 mmol) dropwise at 0° C. The resulting reaction mixture was allowed warm to room temperature and then stirred for 1 h. The reaction mixture was then transferred into water and the resulting mixture was extracted using DCM (3×100 mL). The combined organic layer was dried over anhydrous sodium sulfate and filtered. The filtrate was evaporated under reduced pressure to give ((1S,3S)-3-((tert-butoxycarbonyl)amino)cyclopentyl) methyl methanesulfonate as a white solid (1.9 g, 87%). LC-MS (ESI$^+$) m/z 238.3 (M-56)$^+$.

Step 4—tert-butyl ((1R,3R)-3-(12-phenyl-2,5,8,11-tetraoxadodecyl)cyclopentyl)carbamate To a stirred solution of 2-(2-(2-(benzyloxy)ethoxy)ethoxy)ethan-1-ol (1.3 g, 5.4 mmol, Intermediate T) and ((1S,3S)-3-((tert-butoxycarbonyl)amino)cyclopentyl) methyl methanesulfonate (1.9 g, 6.5 mmol) in toluene (20 mL) and 8 N Aqueous NaOH solution (20 mL) was added TBAB (catalytic amount) at rt. The resulting reaction mixture was then heated to 90° C. and stirred for 16 h. The reaction mixture was then transferred into ice water and the resulting mixture was extracted using ethyl acetate (3×100 mL). The combined organic layer was dried over anhydrous sodium sulfate and filtered. The filtrate was evaporated under reduced pressure and the crude product was purified using silica gel column chromatography (2% MeOH-DCM) to give tert-butyl ((1R,3R)-3-(12-phenyl-2,5,8,11-tetraoxadodecyl)cyclopentyl)carbamate as a yellow oil (0.8 g, 41%). LC-MS (ESI$^+$) m/z 338.4 (M-100)$^+$.

Step 5—tert-butyl ((1R,3R)-3-((2-(2-(2-hydroxyethoxy)ethoxy)ethoxy)methyl)cyclopentyl)carbamate To a stirred solution of tert-butyl ((1R,3R)-3-(12-phenyl-2,5,8,11-tetraoxadodecyl)cyclopentyl)carbamate (0.8 g, 1.8 mmol) in ethanol (25 mL) and acetic acid (0.3 mL) was added 10% Pd/C (0.8 g, 50% wet) at rt under nitrogen atmosphere. The resulting reaction mixture was stirred under hydrogen gas (2 kg/cm$^2$ pressure) in an autoclave at rt for 1.5 h. The reaction mixture was then filtered through a pad of celite under vacuum and washed with MeOH (50 mL). The filtrate was evaporated under reduced pressure to give tert-butyl ((1R,3R)-3-((2-(2-(2-hydroxyethoxy)ethoxy)ethoxy)methyl)cyclopentyl)carbamate as a yellow oil (0.6 g, 94%). LC-MS (ESI$^+$) m/z 248.5 (M-100)$^+$.

Step 6—2-(2-(2-(((1R,3R)-3-((tert-butoxycarbonyl)amino)cyclopentyl)methoxy)ethoxy) ethoxy)ethyl methanesulfonate To a stirred solution of tert-butyl ((1R,3R)-3-((2-(2-(2-hydroxyethoxy)ethoxy)ethoxy)methyl)cyclopentyl)carbamate (0.6 g, 1.7 mmol) and TEA (0.75 mL, 5.18 mmol) in DCM (10 mL) was added Mesyl chloride (0.21 mL, 2.59 mmol) dropwise at 0° C. The resulting reaction mixture then warmed to rt and stirred for 1 h. The reaction mixture was then transferred into water and the resulting mixture was extracted using DCM (3×100 mL). The combined organic layer was dried over anhydrous sodium sulfate and filtered. The filtrate was evaporated under reduced pressure to give 2-(2-(2-(((1R,3R)-3-((tert-butoxycarbonyl)amino)cyclopentyl)methoxy)ethoxy)ethoxy)ethyl methanesulfonate as a brown oil (0.72 g, 98%). LC-MS (ESI+) m/z 370.3 (M-56)+.

vacuum and washed with MeOH (50 mL). The filtrate was evaporated under reduced pressure to give tert-butyl ((1R,3R)-3-((2-(2-(2-aminoethoxy)ethoxy)ethoxy)methyl)cyclopentyl)carbamate as a yellow oil (0.48 g, 69%). LC-MS (ESI+) m/z 347.5 (M+H)+.

tert-butyl (14-amino-3,6,9,12-tetraoxatetradecyl)(methyl)carbamate (Intermediate V)

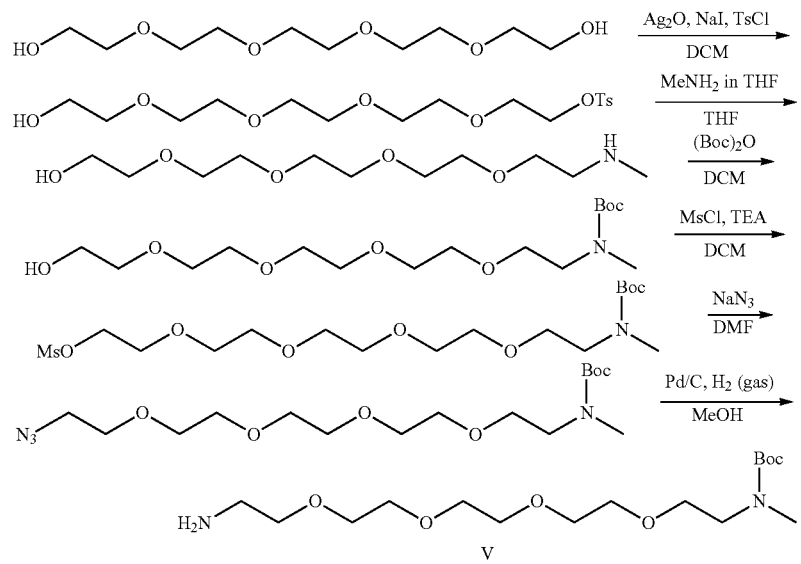

Step 7—tert-butyl ((1R,3R)-3-((2-(2-(2-azidoethoxy)ethoxy)ethoxy)methyl)cyclopentyl)

Carbamate

To a stirred solution of 2-(2-(2-(((1R,3R)-3-((tert-butoxycarbonyl)amino)cyclopentyl)methoxy)ethoxy)ethoxy)ethyl methanesulfonate (0.78 g, 1.83 mmol) in DMF (10 mL) was added NaN₃ (0.18 g, 2.74 mmol) at rt. The resulting reaction mixture was then heated to 65° C. and stirred for 2 h. The reaction mixture was then transferred into water and the resulting mixture was extracted using ethyl acetate (3×100 mL). The combined organic layer was dried over anhydrous sodium sulfate and filtered. The filtrate was evaporated under reduced pressure and the crude product was purified using silica gel column chromatography (3% MeOH-DCM) to give tert-butyl ((1R,3R)-3-((2-(2-(2-azidoethoxy)ethoxy)ethoxy)methyl)cyclopentyl)carbamate as a colorless oil (0.65 g, 95%). LC-MS (ESI+) m/z 390.4 (M+18)+.

Step 8—tert-butyl ((1R,3R)-3-((2-(2-(2-aminoethoxy)ethoxy)ethoxy)methyl)cyclopentyl)carbamate To a stirred solution of tert-butyl ((1R,3R)-3-((2-(2-(2-azidoethoxy)ethoxy)ethoxy)methyl)cyclopentyl)carbamate (0.75 g, 2.01 mmol) in ethanol (20 mL) was added 10% Pd/C (0.75 g, 50% wet) at rt under nitrogen atmosphere. The resulting reaction mixture then stirred under hydrogen gas (15 kg/cm² pressure) in autoclave at rt for 6 h. The reaction mixture was then filtered through a pad of celite under Step 1—14-hydroxy-3,6,9,12-tetraoxatetradecyl 4-methylbenzenesulfonate To a solution of 3,6,9,12-tetraoxatetradecane-1,14-diol (10 g, 41.96 mmol, CAS #4792-15-8), silver oxide (14.6 g, 62.94 mmol) and NaI (7 g, 46.56 mmol) in DCM (250 mL) was added tosyl chloride (8.5 g, 41.96 mmol) at 0° C. The reaction mixture was then allowed to warm to rt and stirred for 1 h. The reaction mixture was then filtered through celite and the filtrate was washed with 10% NaHCO₃ solution (125 mL). The organic layer was dried over anhydrous sodium sulfate and filtered. The filtrate was then evaporated under reduced pressure and the crude product was purified using silica gel column chromatography (3% MeOH-DCM) to give 14-hydroxy-3,6,9,12-tetraoxatetradecyl 4-methylbenzenesulfonate as a yellow oil (13 g, 79%). LC-MS (ESI+) m/z 394.3 (M+H)+.

Step 2—5,8,11,14-tetraoxa-2-azahexadecan-16-ol

To a stirred solution of 14-hydroxy-3,6,9,12-tetraoxatetradecyl 4-methylbenzenesulfonate (3.0 g, 7.7 mmol) in THF (10 mL) was added 2M methyl amine solution in THF (16 mL, 30.6 mmol) dropwise at rt. The resulting reaction mixture then heated to 65° C. and stirred for 16 h. The reaction mixture was filtered and the filter cake was washed with THF (20 mL). The filtrate was then evaporated under reduced pressure to give 5,8,11,14-tetraoxa-2-azahexadecan-16-ol as a yellow oil (1.8 g, 94%). MASS (ESI+) m/z 252 (M+H)+.

Step 3—tert-butyl (14-hydroxy-3,6,9,12-tetraoxatetradecyl)(methyl)carbamate

To a stirred solution of 5,8,11,14-tetraoxa-2-azahexadecan-16-ol (1.8 g, 7.2 mmol) in DCM (50 mL) was added Boc-anhydride (9.36 g, 42.96 mmol) dropwise at 0° C. The resulting reaction mixture then warmed to rt and stirred for 2 h. The reaction mixture was then transferred into ice water and the resulting mixture was extracted using DCM (3×50 mL). The combined organic layer was dried over anhydrous sodium sulfate and filtered. The filtrate was evaporated under reduced pressure and the crude product was purified using silica gel column chromatography (2% MeOH-DCM) to give tert-butyl (14-hydroxy-3,6,9,12-tetraoxatetradecyl)(methyl)carbamate as a light yellow oil (1.5 g, 59%). LC-MS (ESI$^+$) m/z 351.44 (M+H)$^+$.

Step 4—2,2,5-trimethyl-4-oxo-3,8,11,14,17-pentaoxa-5-azanonadecan-19-yl methanesulfonate To a stirred solution of tert-butyl (14-hydroxy-3,6,9,12-tetraoxatetradecyl)(methyl)carbamate (1.5 g, 4.3 mmol) and TEA (1.8 mL, 12.8 mmol) in DCM (30 mL) was added mesyl chloride (0.5 mL, 6.4 mmol) dropwise at 0° C. The resulting reaction mixture then warmed to rt and stirred for 1 h. The reaction mixture was then transferred into water and the resulting mixture was extracted using DCM (3×50 mL). The combined organic layer was dried over anhydrous sodium sulfate and filtered. The filtrate was evaporated under reduced pressure to give 2,2,5-trimethyl-4-oxo-3,8,11,14,17-pentaoxa-5-azanonadecan-19-yl methanesulfonate as a yellow oil (1.5 g, 82%).

Step 5—tert-butyl (14-azido-3,6,9,12-tetraoxatetradecyl)(methyl)carbamate

To a stirred solution of 2,2,5-trimethyl-4-oxo-3,8,11,14,17-pentaoxa-5-azanonadecan-19-yl methanesulfonate (1.5 g, 3.5 mmol) in DMF (15 mL) was added sodium azide (0.34 g, 5.23 mmol) at rt. The resulting reaction mixture was then heated to 65° C. and stirred for 2 h. The reaction mixture was then transferred into ice water and the resulting mixture was extracted using ethyl acetate (3×50 mL). The combined organic layer was dried over anhydrous sodium sulfate and filtered. The filtrate was evaporated under reduced pressure and the crude product was purified using silica gel column chromatography (40% EAc-Hexanes) to give tert-butyl (14-azido-3,6,9,12-tetraoxatetradecyl)(methyl)carbamate as a light yellow oil (1.2 g, 92%). LC-MS (ESI$^+$) m/z 377.2 (M+H)$^+$.

Step 6—tert-butyl (14-amino-3,6,9,12-tetraoxatetradecyl)(methyl)carbamate

To a stirred solution of tert-butyl (14-azido-3,6,9,12-tetraoxatetradecyl)(methyl)carbamate (1.2 g, 3.2 mmol) in MeOH (30 mL) was added 10% Pd/C (1.2 g, 50% wet) at rt under nitrogen atmosphere. The resulting reaction mixture was then stirred under hydrogen gas (15 kg/cm$^2$ pressure) in autoclave at rt for 2 h. The reaction mixture was then filtered through a pad of celite under vacuum and washed with MeOH (30 mL). The filtrate was then evaporated under reduced pressure to give tert-butyl (14-amino-3,6,9,12-tetraoxatetradecyl)(methyl)carbamate as a colorless oil (1 g, 91%). LC-MS (ESI$^+$) m/z 351.7 (M+H)$^+$.

tert-butyl ((1R,4R)-4-((2-(2-(2-aminoethoxy)ethoxy)ethoxy)methyl)cyclohexyl)carbamate (Intermediate W)

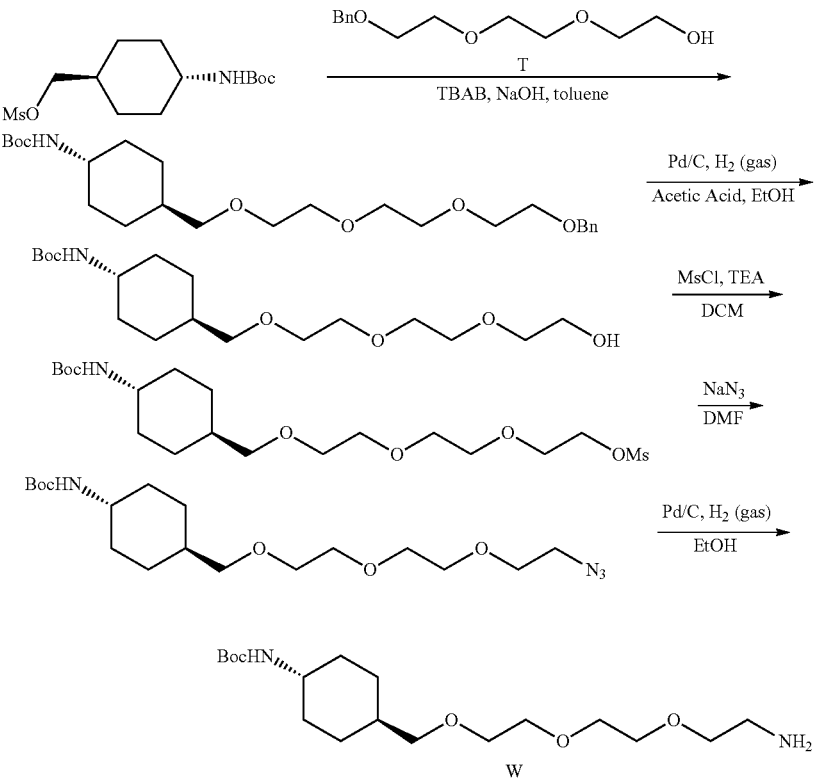

Step 1—tert-butyl ((1R,4R)-4-(12-phenyl-2,5,8,11-tetraoxadodecyl)cyclohexyl)carbamate To a stirred solution of ((1R,4R)-4-((tert-butoxycarbonyl)amino)cyclohexyl)methyl methanesulfonate (1.1 g, 4.6 mmol, synthesized via Steps 1-3 of Intermediate K) and 2-(2-(2-(benzyloxy)ethoxy)ethoxy)ethan-1-ol (1.7 g, 5.5 mmol, Intermediate T) in toluene (20 mL) and 8 N Aqueous NaOH solution (20 mL) was added TBAB (catalytic amount) at rt. The resulting reaction mixture was then heated to 90° C. and stirred for 16 h. The reaction mixture was then transferred into ice water and the resulting mixture was extracted using ethyl acetate (3×100 mL). The combined organic layer was dried over anhydrous sodium sulfate and filtered. The filtrate was evaporated under reduced pressure and the crude product was purified using silica gel column chromatography (2% MeOH-DCM) to give tert-butyl ((1r,4r)-4-(12-phenyl-2,5,8,11-tetraoxadodecyl)cyclohexyl)carbamate as a yellow oil (0.7 g, 28%). LC-MS (ESI$^+$) m/z 452.5 (M+H)$^+$.

Step 2—tert-butyl ((1R,4R)-4-((2-(2-(2-hydroxyethoxy)ethoxy)ethoxy)methyl)cyclohexyl)carbamate To a stirred solution of tert-butyl ((1R,4R)-4-(12-phenyl-2,5,8,11-tetraoxadodecyl)cyclohexyl)carbamate (0.85 g, 1.88 mmol) in ethanol (25 mL) and acetic acid (0.3 mL) was added 10% Pd/C (0.85 g, wet) at rt under nitrogen atmosphere. The resulting reaction mixture was then stirred under hydrogen gas (2 kg/cm$^2$ pressure) in autoclave at rt for 1.5 h. The reaction mixture was filtered through a pad of celite under vacuum and washed with MeOH (50 mL). The filtrate was evaporated under reduced pressure to give tert-butyl ((1R,4R)-4-((2-(2-(2-hydroxyethoxy)ethoxy)ethoxy)methyl)cyclohexyl)carbamate as a yellow oil (0.65 g, 95%). LC-MS (ESI$^+$) m/z 362.4 (M+H)$^-$.

Step 3—2-(2-(2-(((1r,4r)-4-((tert-butoxycarbonyl)amino)cyclohexyl)methoxy)ethoxy)ethoxy)ethyl methanesulfonate To a stirred solution of tert-butyl ((1R,4R)-4-((2-(2-(2-hydroxyethoxy)ethoxy)ethoxy)methyl)cyclohexyl)carbamate (0.65 g, 1.8 mmol) and TEA (0.8 mL, 5.4 mmol) in DCM (10 mL) was added mesyl chloride (0.21 mL, 2.7 mmol) dropwise at 0° C. The resulting reaction mixture was allowed to warm to rt for 1 h. The reaction mixture was then transferred into water and the resulting mixture was extracted using DCM (3×100 mL). The combined organic layer was dried over anhydrous sodium sulfate and filtered. The filtrate was evaporated under reduced pressure to give 2-(2-(2-(((1R,4R)-4-((tert-butoxycarbonyl)amino)cyclohexyl)methoxy)ethoxy)ethoxy)ethyl methanesulfonate as a brown oil (0.75 g, 95%). LC-MS (ESI$^+$) m/z 440.5 (M+H)$^+$.

Step 4—tert-butyl ((1R,4R)-4-((2-(2-(2-azidoethoxy)ethoxy)ethoxy)methyl)cyclohexyl)carbamate To a stirred solution of 2-(2-(2-(((1R,4R)-4-((tert-butoxycarbonyl)amino)cyclohexyl)methoxy)ethoxy)ethoxy)ethyl methanesulfonate (0.75 g, 1.71 mmol) in DMF (10 mL) was added sodium azide (0.17 g, 2.55 mmol) at rt. The resulting reaction mixture was then heated to 65° C. and stirred for 2 h. The reaction mixture was then transferred into water and the resulting mixture was extracted using ethyl acetate (3×100 mL). The combined organic layer was dried over anhydrous sodium sulfate and filtered. The filtrate was then evaporated under reduced pressure and the crude product was purified using silica gel column chromatography (35% EtOAc-Hexanes) to give tert-butyl ((1R,4R)-4-((2-(2-(2-azidoethoxy)ethoxy)ethoxy)methyl)cyclohexyl)carbamate as a colorless oil (0.55 g, 83%). LC-MS (ESI$^+$) m/z 387.4 (M+H)$^+$.

Step 5—tert-butyl ((1R,4R)-4-((2-(2-(2-aminoethoxy)ethoxy)ethoxy)methyl)cyclohexyl)carbamate To a stirred solution of tert-butyl ((1R,4R)-4-((2-(2-(2-azidoethoxy)ethoxy)ethoxy)methyl)cyclohexyl)carbamate (0.55 g, 1.42 mmol) in ethanol (15 mL) was added 10% Pd/C (0.55 g, wet) at rt under nitrogen atmosphere. The resulting reaction mixture was then stirred under hydrogen gas (15 kg/cm$^2$ pressure) in autoclave at rt for 5 h. The reaction mixture was filtered through a pad of celite under vacuum and washed with MeOH (50 mL). The filtrate was evaporated under reduced pressure to give tert-butyl ((1R,4R)-4-((2-(2-(2-aminoethoxy)ethoxy)ethoxy)methyl)cyclohexyl)carbamate as a yellow oil (0.45 g, 88%). LC-MS (ESI$^+$) m/z 361.45 (M+H)$^+$.

1-phenyl-2,5,8,11,14-pentaoxahexadecan-16-yl 4-methylbenzenesulfonate (Intermediate X)

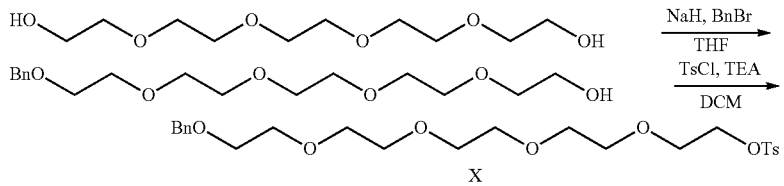

Step 1—1-phenyl-2,5,8,11,14-pentaoxahexadecan-16-ol

To a stirred solution of 3,6,9,12-tetraoxatetradecane-1,14-diol (10 g, 42 mmol, CAS #4792-15-8) in THF (50 mL) was added 60% NaH in paraffin (0.84 g, 21 mmol) at 10° C. The resulting reaction mixture was stirred at the same temperature for 0.5 h. To this reaction mixture benzyl bromide (3.6 g, 21 mmol) in THF (50) was added dropwise at 10° C. over 1.5 h. The resulting reaction mixture was allowed warm to rt and stirred for 16 h. The reaction mixture was then transferred into ice water and the resulting mixture was extracted using ethyl acetate (3×100 mL). The combined organic layer was dried over anhydrous sodium sulfate and filtered. The filtrate was evaporated under reduced pressure and the crude product was purified using silica gel column chromatography (3% MeOH-DCM) to give 1-phenyl-2,5,8,11,14-pentaoxahexadecan-16-ol as a yellow oil (6 g, 43%). LC-MS (ESI$^+$) m/z 347.4 (M+H$_2$O)$^+$.

Step 2—1-phenyl-2,5,8,11,14-pentaoxahexadecan-16-yl 4-methylbenzenesulfonate To a stirred solution of methyl 1-phenyl-2,5,8,11,14-pentaoxahexadecan-16-ol (6.0 g, 18.2 mmol) and TEA (8 mL, 55 mmol) in DCM (150 mL) was added tosyl chloride (5.2 g, 27.3 mmol) at rt. The resulting reaction mixture then stirred at rt for 16 h. The reaction mixture was then transferred into ice water and the resulting mixture was extracted using DCM (3×100 mL). The combined organic layer was dried over anhydrous sodium sulfate and filtered. The filtrate was evaporated under reduced pressure and the crude product was purified using silica gel column chromatography (2% MeOH-DCM) to give 1-phenyl-2,5,8,11,14-pentaoxahexadecan-16-yl 4-methylbenzenesulfonate as a yellow oil (7 g, 79%). LC-MS (ESI$^+$) m/z 484.2 (M+H)$^+$.

tert-butyl ((1R,4R)-4-(16-amino-2,5,8,11,14-pentaoxahexadecyl)cyclohexyl)carbamate (Intermediate Y)

to give tert-butyl ((1R,4R)-4-(18-phenyl-2,5,8,11,14,17-hexaoxaoctadecyl)cyclohexyl)carbamate as a yellow oil (0.92 g, 26%). LC-MS (ESI$^+$) m/z 557.4 (M+18)$^+$.

Step 2—tert-butyl ((1R,4R)-4-(16-hydroxy-2,5,8,11,14-pentaoxahexadecyl)cyclohexyl)carbamate To a stirred solution of tert-butyl ((1R,4R)-4-(18-phenyl-2,5,8,11,14,17-hexaoxaoctadecyl)cyclohexyl)carbamate (0.91 g, 1.68 mmol) in ethanol (15 mL) was added 10% Pd/C (0.9 g, 50% wet) at rt under nitrogen atmosphere. The resulting reaction mixture was stirred under hydrogen gas (2 kg/cm$^2$ pressure) in an autoclave at rt for 6 h. The reaction mixture was filtered through a pad of celite under vacuum and washed with MeOH (50 mL). The filtrate was evaporated under reduced pressure to give tert-butyl ((1R,4R)-4-(16-hydroxy-2,5,8,11,14-pentaoxahexadecyl)cyclohexyl)carbamate as a yellow oil (0.75 g, 99%). LC-MS (ESI$^+$) m/z 450.2 (M+H)$^+$.

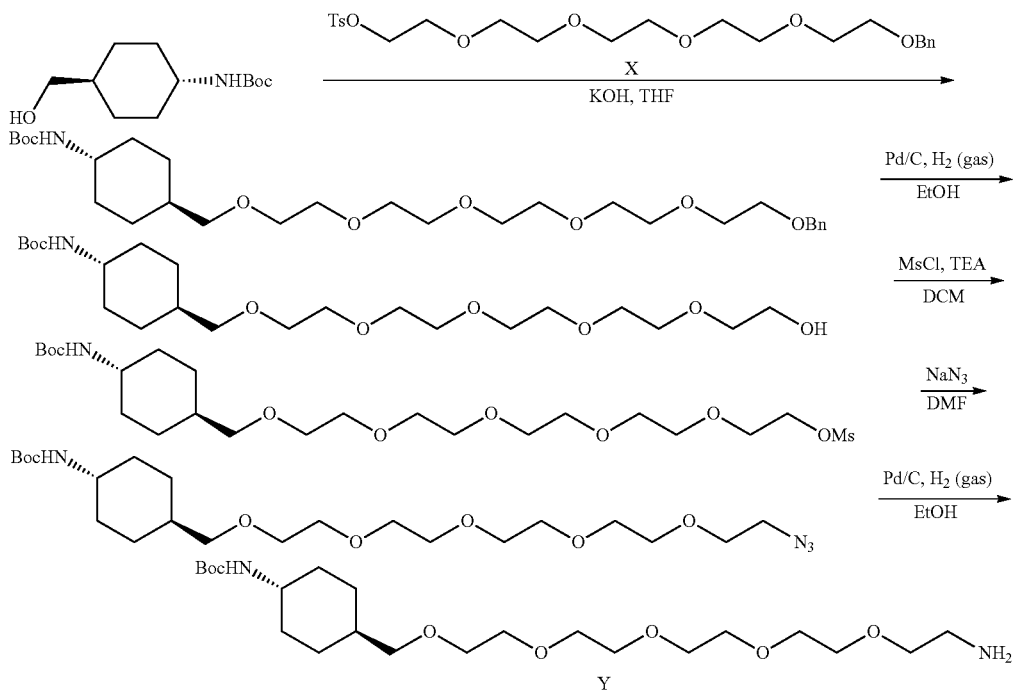

Step 1—tert-butyl ((1R,4R)-4-(18-phenyl-2,5,8,11,14,17-hexaoxaoctadecyl)cyclohexyl)carbamate To a stirred solution of tert-butyl ((1R,4R)-4-(hydroxymethyl)cyclohexyl)carbamate (1.5 g, 0.7 mmol, synthesized via Steps 1-2 of Intermediate K) and 1-phenyl-2,5,8,11,14-pentaoxahexadecan-16-yl 4-methylbenzenesulfonate (4.74 g, 0.98 mmol, Intermediate X) in THF (30 mL) was added KOH (3.67 g, 65.4 mmol) at rt. The resulting reaction mixture then heated to 60° C. and stirred for 16 h. The reaction mixture was then transferred into ice water and the resulting mixture was extracted using ethyl acetate (3×100 mL). The combined organic layer was dried over anhydrous sodium sulfate and filtered. The filtrate was evaporated under reduced pressure and the crude product was purified using silica gel column chromatography (2% MeOH-DCM)

Step 3—1-((1R,4R)-4-((tert-butoxycarbonyl)amino)cyclohexyl)-2,5,8,11,14-pentaoxahexadecan-16-yl methanesulfonate To a stirred solution of tert-butyl ((1R,4R)-4-(16-hydroxy-2,5,8,11,14-pentaoxahexadecyl)cyclohexyl)carbamate (0.8 g, 1.8 mmol) and TEA (0.75 mL, 5.33 mmol) in DCM (10 mL) was added mesyl chloride (0.2 mL, 2.66 mmol) dropwise at 0° C. The resulting reaction mixture was allowed to warm to rt and stirred for 1 h. The reaction mixture was then transferred into water and the resulting mixture was extracted using DCM (3×100 mL). The combined organic layer was dried over anhydrous sodium sulfate and filtered. The filtrate was evaporated under reduced pressure to give 1-((1R,4R)-4-((tert-butoxycarbonyl)amino)

cyclohexyl)-2,5,8,11,14-pentaoxahexadecan-16-yl methanesulfonate as a brown oil (0.9 g, 96%). LC-MS (ESI⁺) m/z 545.6 (M+18)⁺.

Step 4—tert-butyl ((1R,4R)-4-(16-azido-2,5,8,11,14-pentaoxahexadecyl)cyclohexyl)carbamate To a stirred solution of 1-((1R,4R)-4-((tert-butoxycarbonyl)amino)cyclohexyl)-2,5,8,11,14-pentaoxahexadecan-16-yl methanesulfonate (0.9 g, 1.7 mmol) in DMF (10 mL) was added sodium azide (0.17 g, 2.55 mmol) at rt. The resulting reaction mixture was then heated to 65° C. and stirred for 2 h. The reaction mixture was then transferred into water and the resulting mixture was extracted using ethyl acetate (3×100 mL). The combined organic layer was dried over anhydrous sodium sulfate and filtered. The filtrate was evaporated under reduced pressure and the crude product was purified using silica gel column chromatography (45% EAc-Hexanes) to give tert-butyl ((1R,4R)-4-(16-azido-2,5,8,11,14-pentaoxahexadecyl)cyclohexyl)carbamate as a colorless oil (0.72 g, 90%).

Step 5—tert-butyl ((1R,4R)-4-(16-amino-2,5,8,11,14-pentaoxahexadecyl)cyclohexyl)carbamate To a stirred solution of tert-butyl ((1R,4R)-4-(16-azido-2,5,8,11,14-pentaoxahexadecyl)cyclohexyl)carbamate (0.7 g, 1.47 mmol) in ethanol (20 mL) was added 10% Pd/C (0.7 g, 50% wet) at rt under nitrogen atmosphere. The resulting reaction mixture was then stirred under hydrogen gas (15 kg/cm² pressure) in an autoclave at rt for 4 h. The reaction mixture was then filtered through a pad of celite under vacuum and washed with MeOH (50 mL). The filtrate was evaporated under reduced pressure to give tert-butyl ((1R,4R)-4-(16-amino-2,5,8,11,14-pentaoxahexadecyl)cyclohexyl)carbamate as a yellow oil (0.52 g, 78%). LC-MS (ESI⁺) m/z 449.5 (M+H)⁺.

4-((14-amino-3,6,9,12-tetraoxatetradecyl)amino)-2-(2,6-dioxopiperidin-3-yl)isoindoline-1,3-dione hydrochloride (Intermediate Z)

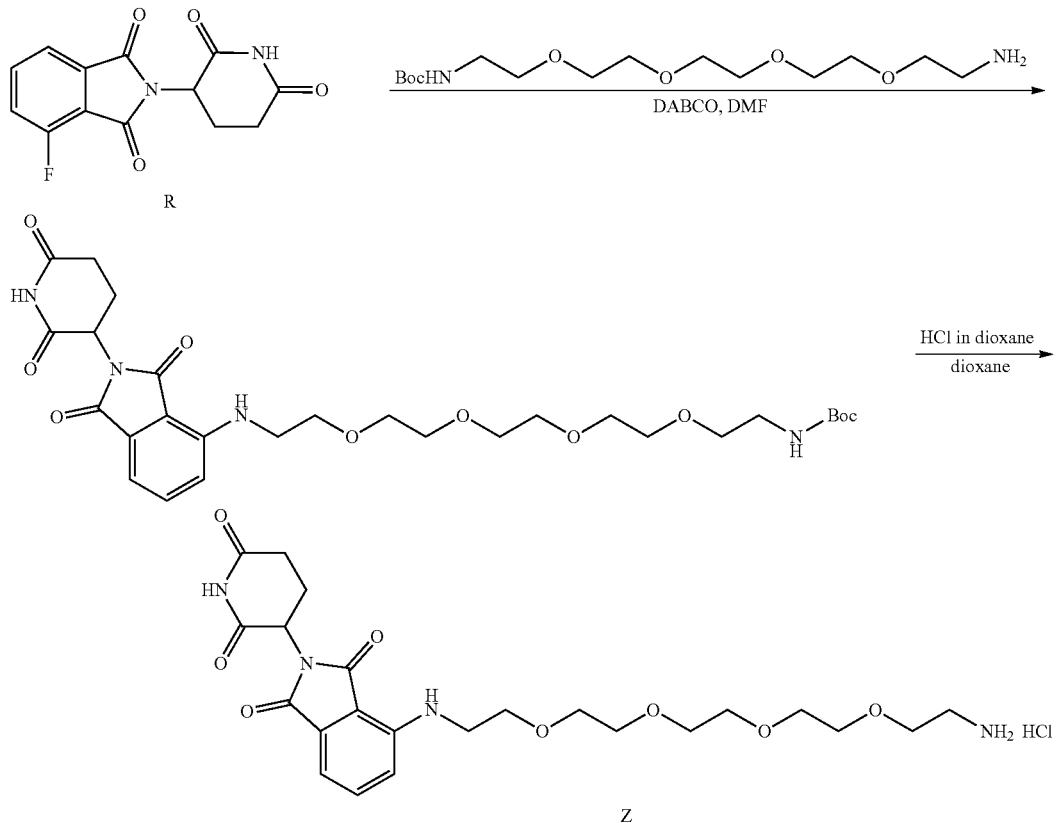

Step 1—tert-butyl (14-((2-(2,6-dioxopiperidin-3-yl)-1,3-dioxoisoindolin-4-yl)amino)-3,6,9,12-tetraoxatetradecyl)carbamate To a stirred solution of 2-(2,6-dioxopiperidin-3-yl)-4-fluoroisoindoline-1,3-dione (0.95 g, 3.44 mmol, Intermediate R) and DABCO (0.5 g, 4.5 mmol) in DMF (25 mL) was added tert-butyl (14-amino-3,6,9,12-tetraoxatetradecyl)carbamate (1.5 g, 4.5 mmol, CAS #811442-84-9) at rt. The resulting reaction mixture then heated at 80° C. for 3 h. The reaction mixture was then transferred into ice water and the resulting mixture was extracted using ethyl acetate (3×50 mL). The combined organic layer was dried over anhydrous sodium sulfate and filtered. The filtrate was evaporated under reduced pressure and the crude product was purified using silica gel column chromatography (2% MeOH-DCM) to give tert-butyl (14-((2-(2,6-dioxopiperidin-3-yl)-1,3-dioxoisoindolin-4-yl)amino)-3,6,9,12-tetraoxatetradecyl)carbamate as a yellow oil (0.35 g, 17%). LCMS (ESI⁺) m/z 593.6 (M+H)⁺.

Step 2—4-((14-amino-3,6,9,12-tetraoxatetradecyl)amino)-2-(2,6-dioxopiperidin-3-yl)isoindoline-1,3-dione hydrochloride To a stirred solution of tert-butyl (14-((2-(2,6-dioxopiperidin-3-yl)-1,3-dioxoisoindolin-4-yl)amino)-3,6,9,12-tetraoxatetradecyl)carbamate (0.35 g, 0.59 mmol) in 1,4 dioxane (10 mL) was added 4 M HCl in dioxane (10 mL) at 0° C. The resulting reaction mixture was allowed to warm to rt and stirred for 16 h. The reaction mixture was then evaporated under vacuum and triturated using MTBE to give 4-((14-amino-3,6,9,12-tetraoxatetradecyl)amino)-2-(2,6-dioxopiperidin-3-yl)isoindoline-1,3-dione hydrochloride as a yellow solid (0.28 g, 90%). LCMS (ESI$^+$) m/z 493.45 (M+H)$^+$.

tert-butyl 6-bromohexanoate (Intermediate AA)

Step 2—tert-butyl 6-bromohexanoate

To a stirred solution of 6-bromohexanoyl chloride (5.5 g, 25.8 mmol) and pyridine (2.55 mL, 30.9 mmol) in DCM (50 mL) was added tert-butanol (3.71 mL g, 38.62 mmol) dropwise at rt. The resulting reaction mixture stirred at rt for 16 h. The reaction mixture was then transferred into ice water and the resulting mixture was extracted using DCM (3×100 mL). The combined organic layer was dried over anhydrous sodium sulfate and filtered. The filtrate was evaporated under reduced pressure and the crude product was purified using silica gel column chromatography (6% EAc-Hexanes) to give tert-butyl 6-bromohexanoate as a colorless oil (4.5 g, 70%). $^1$H NMR (400 MHz, DMSO) δ 3.43 (t, J=8 Hz, 2H), 2.25 (t, J=7.2 Hz, 2H), 1.93-1.86 (m, 2H), 1.67-1.60 (m, 2H), 1.52-1.50 (m, 2H), 1.46 (s, 9H).

tert-butyl 6-((7-aminoheptyl)oxy)hexanoate
(Intermediate AB)

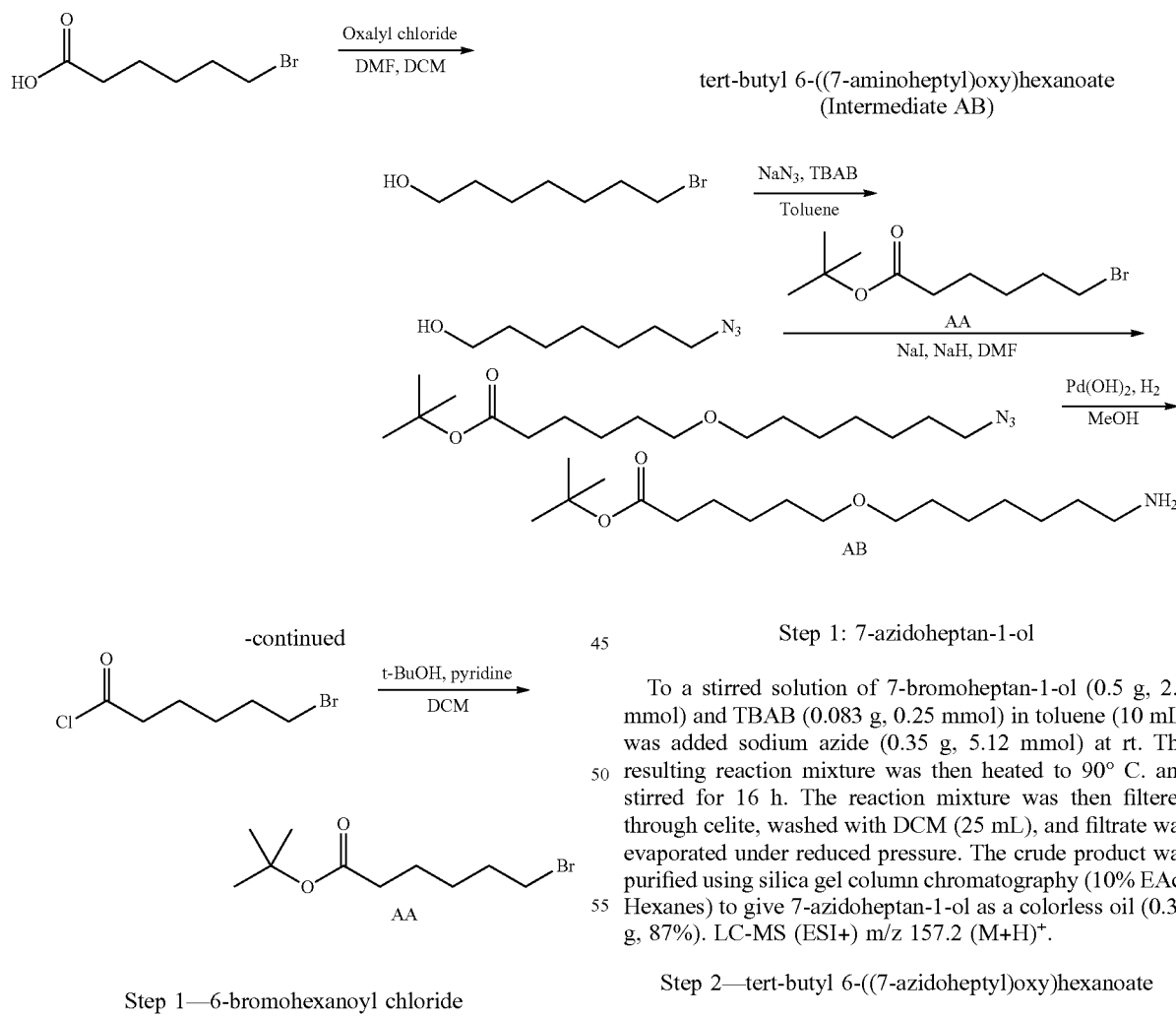

Step 1—6-bromohexanoyl chloride

To a stirred solution of 6-bromohexanoic acid (5.0 g, 25.6 mmol) and DMF (catalytic amount) in DCM (50 mL) was added oxalyl chloride (2.5 mL, 28.16 mmol) dropwise at 0° C. The resulting reaction mixture was then warmed to rt and stirred for 16 h. The reaction mixture was then evaporated under reduced pressure to give 6-bromohexanoyl chloride as a brown oil (5 g, 91%).

Step 1: 7-azidoheptan-1-ol

To a stirred solution of 7-bromoheptan-1-ol (0.5 g, 2.6 mmol) and TBAB (0.083 g, 0.25 mmol) in toluene (10 mL) was added sodium azide (0.35 g, 5.12 mmol) at rt. The resulting reaction mixture was then heated to 90° C. and stirred for 16 h. The reaction mixture was then filtered through celite, washed with DCM (25 mL), and filtrate was evaporated under reduced pressure. The crude product was purified using silica gel column chromatography (10% EAc-Hexanes) to give 7-azidoheptan-1-ol as a colorless oil (0.35 g, 87%). LC-MS (ESI+) m/z 157.2 (M+H)$^+$.

Step 2—tert-butyl 6-((7-azidoheptyl)oxy)hexanoate

To a stirred solution of 7-azidoheptan-1-ol (1.1 g, 7.2 mmol) in DMF (30 mL) was added NaI (0.18 g, 1.19 mmol) and 60% NaH (0.36 g, 8.9 mmol) at rt. The resulting reaction mixture was stirred at rt for 0.5 h then tert-butyl 6-bromohexanoate (1.5 g, 5.97 mmol) in DMF (5 mL) was added dropwise at rt. The resulting reaction mixture then heated to 50° C. and stirred for 16 h. The reaction mixture was then transferred into ice water and the resulting mixture was extracted using ethyl acetate (3×100 mL). The combined organic layer was dried over anhydrous sodium sulfate and filtered. The filtrate was evaporated under reduced pressure and the crude product was purified using silica gel column chromatography (3% EAc-Hexanes) to give tert-butyl 6-((7-azidoheptyl)oxy)hexanoate as a colorless oil (0.3 g, 10%). $^1$H NMR (400 MHz, DMSO) δ 3.43-3.39 (m, 4H), 3.27 (t, J=7.2 Hz, 2H), 2.23 (t, J=7.6 Hz, 2H), 1.66-1.48 (m, 8H), 1.46 (m, 9H), 1.44-1.41 (m, 8H).

Step 3—tert-butyl 6-((7-aminoheptyl)oxy)hexanoate

To a stirred solution of tert-butyl 6-((7-azidoheptyl)oxy) hexanoate (0.3 g, 0.92 mmol) in methanol (30 mL) was added 20% Pd(OH)$_2$ (0.3 g) at rt under nitrogen atmosphere. The resulting reaction mixture then stirred under hydrogen gas (20 kg/cm$^2$ pressure) in an autoclave at rt for 4 h. The reaction mixture was then filtered through a pad of celite under vacuum and washed with MeOH (50 mL). The filtrate was then evaporated under reduced pressure to give tert-butyl 6-((7-aminoheptyl)oxy)hexanoate as a colorless oil (0.25 g, 90%). $^1$H NMR (400 MHz, DMSO) δ 3.42-3.38 (m, 4H), 2.69 (t, J=7.2 Hz, 2H), 2.23 (t, J=7.6 Hz, 2H), 1.65-1.56 (m, 8H), 1.46 (m, 10H), 1.42-1.33 (m, 8H).

tert-butyl(2-(2-(2-(methylamino)ethoxy)ethoxy) ethyl)carbamate (Intermediate AC)

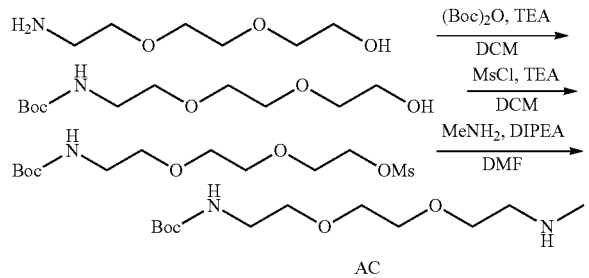

Step 1—tert-butyl (2-(2-(2-hydroxyethoxy)ethoxy)ethyl)carbamate

A solution of 2-(2-(2-aminoethoxy)ethoxy)ethan-1-ol (1.5 g, 10.1 mmol), triethylamine (3.3 mL, 15.1 mmol), and Boc-anhydride (3.3 g, 15.1 mmol) in DCM (10 mL) was stirred at rt for 2 h. The reaction mixture was then transferred into ice water and the resulting mixture was extracted using DCM (3×25 mL). The combined organic layer was dried over anhydrous sodium sulfate and filtered. The filtrate was evaporated under reduced pressure and the crude product was purified using silica gel column chromatography (3% MeOH-DCM) to give tert-butyl (2-(2-(2-hydroxyethoxy) ethoxy)ethyl)carbamate as a colorless oil (1.8 g, 72%). LC-MS (ESI$^+$) m/z 267.35 (M+H)$^+$.

Step 2—2,2-dimethyl-4-oxo-3,8,11-trioxa-5-azatridecan-13-yl methanesulfonate

To a stirred solution of tert-butyl(2-(2-(2-hydroxyethoxy) ethoxy)ethyl)carbamate (1.8 g, 7.2 mmol) and triethylamine (3.0 g, 4.15 mL, 21.7 mmol) in DCM (12 mL) was added of mesyl chloride (0.85 g, 10.8 mmol) and the reaction mixture was stirred at rt for 2 h. The reaction mixture was then transferred into ice water and the resulting mixture was extracted using DCM (3×25 mL). The combined organic layer was dried over anhydrous sodium sulfate and filtered. The filtrate was evaporated under reduced pressure to give 2,2-dimethyl-4-oxo-3,8,11-trioxa-5-azatridecan-13-yl methanesulfonate as a yellow semisolid (2.2 g, 93%).

Step 3—tert-butyl (2-(2-(2-(methylamino)ethoxy) ethoxy)ethyl)carbamate

A stirred solution of tert-butyl(2-(2-(2-(methylamino) ethoxy)ethoxy)ethyl)carbamate (2.0 g, 6.1 mmol), 2M Methyl amine in THF (36.66 mL, 73.32 mmol) and DIPEA (3 mL, 3 eq) in DMF (20 mL) was heated at 90° C. for 10 h. The reaction mixture was then transferred into ice water and the resulting mixture was extracted using ethyl acetate (3×25 mL). The combined organic layer was dried over anhydrous sodium sulfate and filtered. The filtrate was evaporated under reduced pressure to give tert-butyl (2-(2-(2-(methylamino)ethoxy)ethoxy)ethyl)carbamate (1.2 g, 68%).

2-azidoethan-1-ol (Intermediate AD)

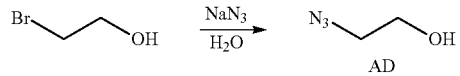

To a stirred solution of 2-bromoethan-1-ol (10 g, 80 mmol) in water (100 mL) was added sodium azide (10.4 g, 160.1 mmol) and the reaction mixture was heated at 80° C. for 16 h. The reaction mixture was then extracted using diethyl ether (250 mL×3), dried over anhydrous sodium sulphate and evaporated in vacuum to give 2-azidoethan-1-ol as a light yellow oil (6.5 g, 93%); $^1$H NMR (400 MHz, DMSO) δ 5.00 (t, J=5.2 Hz, 1H), 3.7-3.5 (m, 2H), 3.3-3.2 (m, 2H).

2-azidoethyl 4-methylbenzenesulfonate (Intermediate AE)

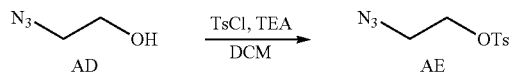

To a stirred mixture of 2-azidoethan-1-ol (0.1 g, 1.2 mmol, Intermediate AD) in DCM (5 mL) was added TEA (0.5 mL, 3.5 mmol) and TsCl (0.286 g, 1.5 mmol) at 0° C. and the reaction mixture was stirred for 3 h. The reaction mixture was then diluted with water (100 mL) and extracted using DCM (50 mL×3). The combined organic layer was dried over anhydrous sodium sulphate, filtered and evaporated in vacuo and the crude product was purified by silica gel column chromatography (10-15% EtOAc-Hexane) to give 2-azidoethyl 4-methylbenzenesulfonate as a colorless semisolid (0.15 g, 54%). $^1$H NMR (400 MHz, DMSO) δ 7.83 (d, J=8.4 Hz, 2H), 7.52 (d, J=8.0 Hz, 2H), 4.17 (t, J=4.8 Hz, 2H), 3.56 (t, J=4.8 Hz, 2H), 2.52 (d, J=1.6 Hz, 2H).

tert-butyl (2-((6-((2-aminoethoxy)methyl)pyridin-3-yl)methoxy)ethyl) carbamate (Intermediate AF)

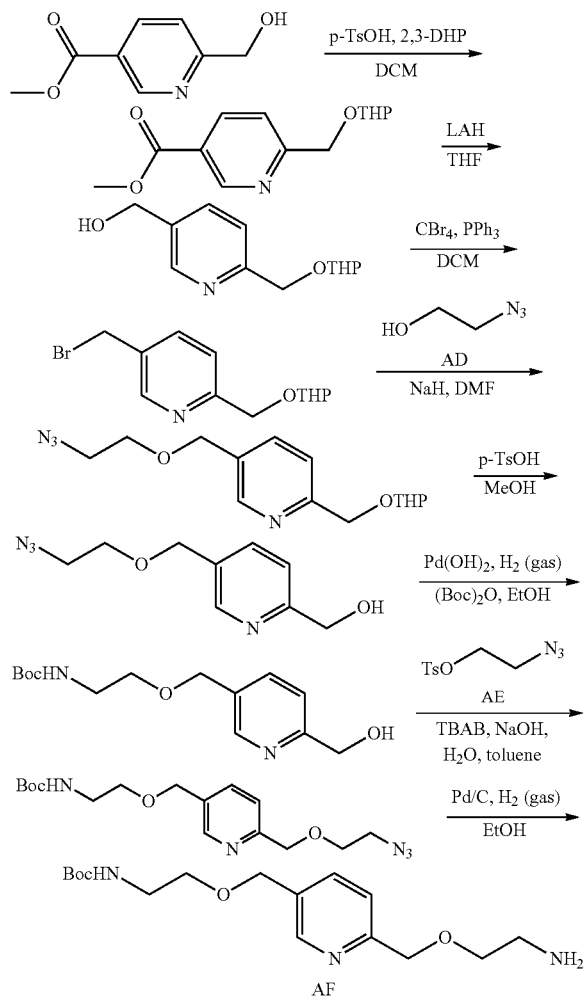

Step 1—methyl 6-(((tetrahydro-2H-pyran-2-yl)oxy)methyl)nicotinate

To a stirred solution of methyl 6-(hydroxymethyl)nicotinate (0.5 g, 3.0 mmol) in DCM (50 mL), was added p-TsOH (0.63 g, 3.3 mmol) at 0° C. followed by 3,4-dihydro-2H-pyran (0.9 mL, 9.0 mmol) at same temperature. The mixture was allowed to warm to rt then stirred for 16 h. The reaction mixture was diluted with water (50 mL) and product was extracted using DCM (50 mL×3). The combined organic layer was dried over anhydrous sodium sulphate and vacuum evaporated and the crude product was purified by silica gel column chromatography (0-1% MeOH-DCM to give methyl 6-(((tetrahydro-2H-pyran-2-yl)oxy)methyl)nicotinate as a yellow semisolid (0.7 g, 90%); LC-MS (ESI$^+$) m/z 252.3 (M+H)$^+$.

Step 2—(6-(((tetrahydro-2H-pyran-2-yl)oxy)methyl)pyridin-3-yl)methanol

To a stirred solution of methyl 6-(((tetrahydro-2H-pyran-2-yl)oxy)methyl)nicotinate (0.7 g, 2.79 mmol) in THF (25 mL) was added 1M lithium aluminum hydride in THF (7 mL, 7 mmol) dropwise at −70° C. and the mixture was stirred for 30 minutes at the same temperature. The reaction mixture was then quenched with water (100 mL), filtered through celite and the filtrate was extracted in ethyl acetate (100 mL×3). The combined organic layer was dried over anhydrous sodium sulphate, filtered and evaporated in vacuo and the crude product was purified by silica gel column chromatography (70-80% EtOAc-Hexane) to give (6-(((tetrahydro-2H-pyran-2-yl)oxy)methyl)pyridin-3-yl)methanol as a yellow semisolid (0.3 g, 48%); LC-MS (ESI$^+$) m/z 224.25 (M+H)$^+$.

Step 3—5-(bromomethyl)-2-(((tetrahydro-2H-pyran-2-yl)oxy)methyl)pyridine

To a stirred solution of (6-(((tetrahydro-2H-pyran-2-yl)oxy)methyl)pyridin-3-yl)methanol (0.3 g, 1.34 mmol) in DCM (10 mL) was added carbon tetrabromide (0.668 g, 2.02 mmol) and triphenylphosphine (0.334 g, 1.47 mmol) at 0° C. and the reaction mixture was stirred for 4 h. The reaction mixture was then diluted with water (50 mL) and product was extracted using DCM (50 mL×3). The combined organic layer was dried over anhydrous sodium sulphate, filtered and evaporated in vacuo. The crude product was purified by silica gel column chromatography (50% EtOAc-Hexane) to give 5-(bromomethyl)-2-(((tetrahydro-2H-pyran-2-yl)oxy)methyl)pyridine as a yellow oil (0.05 g, 13%); LC-MS (ESI$^+$) m/z 288.2 (M+H)$^+$.

Step 4—5-((2-azidoethoxy)methyl)-2-(((tetrahydro-2H-pyran-2-yl)oxy)methyl)pyridine To a stirred solution of 2-azidoethan-1-ol (0.8 g, 9.1 mmol, Intermediate AD) in DMF (10 mL) was added 60% NaH in oil (0.363 g, 9.09 mmol) at 0° C. followed by addition of a solution of 5-(bromomethyl)-2-(((tetrahydro-2H-pyran-2-yl)oxy)methyl)pyridine (1.3 g, 4.54 mmol) in DMF (5 mL) and the reaction was stirred for 15 min. The reaction mixture was then quenched with water (50 mL) and product was extracted in ethyl acetate (250 mL). The organic layer was washed with water (250 mL×3) and dried over anhydrous sodium sulphate, filtered and evaporated in vacuo. The crude product was purified by silica gel column chromatography (50% EtOAc-Hexane) to give 5-((2-azidoethoxy)methyl)-2-(((tetrahydro-2H-pyran-2-yl)oxy)methyl)pyridine as a yellow oil (1.1 g, 83%); LC-MS (ESI$^+$) m/z 293.3 (M+H)$^+$.

Step 5—(5-((2-azidoethoxy)methyl)pyridin-2-yl)methanol

To a stirred solution of 5-((2-azidoethoxy)methyl)-2-(((tetrahydro-2H-pyran-2-yl)oxy)methyl)pyridine (1.1 g, 3.8 mmol) in methanol (25 mL) was added p-TsOH (0.648 g, 3.76 mmol) at 0° C. and the reaction mixture was allowed to warm to rt and stirred for 16 h. The reaction mixture was then concentrated, diluted with water (250 mL) and extracted in ethyl acetate (200 mL×3). The combined organic layer was dried over anhydrous sodium sulphate, filtered and evaporated in vacuo. The crude product was purified by silica gel column chromatography u (10% MeOH-DCM) to give (5-((2-azidoethoxy)methyl)pyridin-2-yl)methanol as a yellow semisolid (0.55 g, 70%); LC-MS (ESI$^+$) m/z 209.2 (M+H)$^+$.

Step 6—tert-butyl (2-((6-(hydroxymethyl)pyridin-3-yl)methoxy)ethyl)carbamate To a stirred solution of (5-((2-azidoethoxy)methyl)pyridin-2-yl)methanol (0.55 g, 2.64 mmol) in ethanol (50 mL) was added Boc anhydride (0.91 mL, 3.96 mmol) and 20% Pd(OH)$_2$/C (50% wet) (0.55 g) in autoclave at rt under hydrogen gas (20 kg/cm$^2$ pressure) and the reaction was stirred for 6 h. The reaction mixture was then filtered through celite and the filtrate was concentrated in vacuo. The crude product was purified by silica gel column chromatography (70-80% EtOAc-Hexane) to give tert-butyl (2-((6-(hydroxymethyl)pyridin-3-yl)methoxy)ethyl)carbamate as a yellow semisolid (0.4 g, 54%); LC-MS (ESI$^+$) m/z 283.3 (M+H)$^+$.

Step 7—tert-butyl (2-((6-((2-azidoethoxy)methyl)pyridin-3-yl)methoxy)ethyl)carbamate To a stirred solution of tert-butyl (2-((6-(hydroxymethyl)pyridin-3-yl)methoxy)ethyl)carbamate (0.15 g, 0.53 mmol), 8N NaOH in water (2 mL) and TBAB in toluene (2 mL) was added 2-azidoethyl 4-methylbenzenesulfonate (3 mL, 18 mmols, Intermediate AE) and the mixture was refluxed for 48 h. The reaction mixture was then diluted with water (100 mL) and extracted using ethyl acetate (50 mL×3). The combined organic layer was dried over anhydrous sodium sulphate, filtered and evaporated in vacuo. The crude product was purified by silica gel column chromatography (2% MeOH-DCM) to give tert-butyl (2-((6-((2-azidoethoxy)methyl)pyridin-3-yl)methoxy)ethyl)carbamate as a colorless oil (0.065 g, 35%); LC-MS (ESI$^+$) m/z 352.3 (M+H)$^+$.

Step 8—tert-butyl (2-((6-((2-aminoethoxy)methyl)pyridin-3-yl)methoxy)ethyl) carbamate To a stirred solution of tert-butyl (2-((6-((2-azidoethoxy)methyl)pyridin-3-yl)methoxy)ethyl)carbamate (0.145 g) in ethanol (10 mL) was added 20% Pd(OH)$_2$/C (50% wet) (0.14 g) in an autoclave at rt and the reaction mixture was stirred under hydrogen gas (20 kg/cm$^2$ pressure) for 4 h. The reaction mixture was then filtered through celite and the filtrate was concentrated and evaporated in vacuo to give tert-butyl (2-((6-((2-aminoethoxy)methyl)pyridin-3-yl)methoxy)ethyl)carbamate as a yellow semisolid (0.1 g, 74%); LC-MS (ESI$^+$) m/z 326.5 (M+H)$^+$.

(1R,4R)-4-(6-(5-cyano-1H-pyrazolo[3,4-b]pyridin-1-yl)-4-(cyclopropylamino)nicotinamido)cyclohexane-1-carboxylic acid (Intermediate AG)

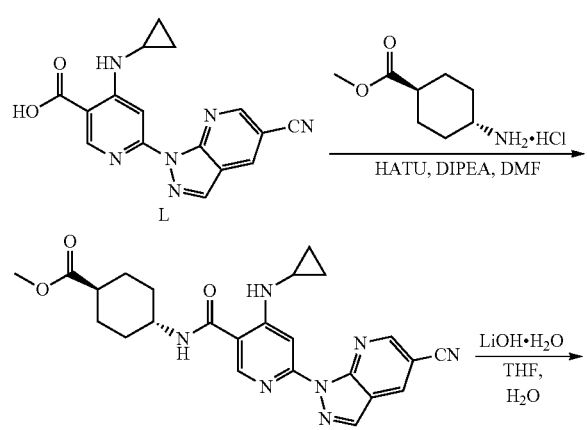

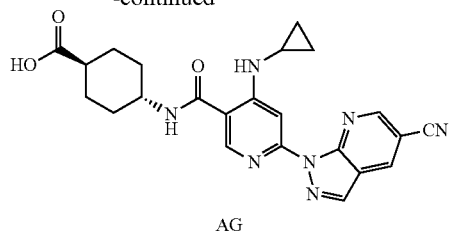

AG

Step 1—methyl (1R,4R)-4-(6-(5-cyano-1H-pyrazolo[3,4-b]pyridin-1-yl)-4-(cyclopropylamino)nicotinamido)cyclohexane-1-carboxylate A stirred solution of 6-(5-cyano-1H-pyrazolo[3,4-b]pyridin-1-yl)-4-(cyclopropylamino)nicotinic acid (0.3 g, 0.94 mmol, Intermediate L), methyl (1R,4R)-4-aminocyclohexane-1-carboxylate hydrochloride (0.18 g, 0.94 mmol), HATU (0.54 g, 1.41 mmol) and DIPEA (0.54 mL, 1.41 mmol) in DMF (5 mL) was stirred at rt for 4 h. The reaction mixture was transferred then into ice water and the resulting precipitate was filtered off and dried under vacuum to give methyl (1R,4R)-4-(6-(5-cyano-1H-pyrazolo[3,4-b]pyridin-1-yl)-4-(cyclopropylamino)nicotinamido)cyclohexane-1-carboxylate as an off white solid (0.38 g, 88%). LC-MS (ESI$^+$) m/z 460.2 (M+H)$^+$.

Step 2—(1R,4R)-4-(6-(5-cyano-1H-pyrazolo[3,4-b]pyridin-1-yl)-4-(cyclopropylamino)nicotinamido)cyclohexane-1-carboxylic acid To a stirred solution of methyl (1r,4r)-4-(6-(5-cyano-1H-pyrazolo[3,4-b]pyridin-1-yl)-4-(cyclopropylamino)nicotinamido)cyclohexane-1-carboxylate (0.38 g, 0.82 mmol) in THF:water (1:1, 10 mL) was added lithium hydroxide monohydrate (0.11 g, 2.48 mmol) at rt and the reaction mixture was stirred for 2 h. The reaction mixture was then transferred into ice water and the pH was adjusted to 5-6 using 10% citric acid solution. The resulting precipitate was filtered off and dried under vacuum to give (1R,4R)-4-(6-(5-cyano-1H-pyrazolo[3,4-b]pyridin-1-yl)-4-(cyclopropylamino)nicotinamido)cyclohexane-1-carboxylic acid as an off-white solid (0.25 g, 76%). LC-MS (ESI$^+$) m/z 446.4 (M+H)$^+$.

3-(dibenzylamino)-2-fluoro-propan-1-ol (Intermediate AH)

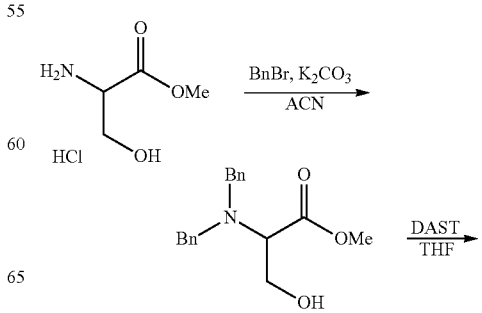

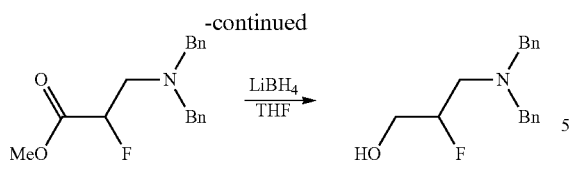

Step 1—Methyl 2-(dibenzylamino)-3-hydroxy-propanoate

To a mixture of methyl 2-amino-3-hydroxy-propanoate (15.0 g, 96.4 mmol, HCl salt) and benzyl bromide (36.3 g, 212 mmol, 25.2 mL) in acetonitrile (200 mL) was added potassium carbonate (66.6 g, 482 mmol). The mixture was stirred at rt for 12 h. On completion, the reaction mixture was filtered and washed with acetonitrile. The combined organic layers were concentrated in vacuo. The residue was purified by column chromatography to give the title compound (16.1 g, 56% yield) as a white solid. $^1$H NMR (400 MHz, DMSO-d$_6$) δ 7.39-7.28 (m, 8H), 7.27-7.20 (m, 2H), 4.80 (dd, J=4.8, 6.0 Hz, 1H), 3.84-3.80 (m, 2H), 3.69 (s, 3H), 3.56 (d, J=14.4 Hz, 2H), 3.40-3.30 (m, 2H); LC-MS (ESI$^+$) m/z 300.1 (M+H)$^+$.

Step 2—Methyl 3-(dibenzylamino)-2-fluoro-propanoate

To a solution of methyl 2-(dibenzylamino)-3-hydroxy-propanoate (5.00 g, 16.7 mmol) in THF (20.0 mL) was added a solution of DAST (3.23 g, 20.0 mmol, 2.65 mL) in 10 mL THF. The reaction mixture was stirred at rt for 1 h. On completion, the reaction mixture was quenched by the addition of ice-water (50 mL) followed by ethyl acetate (200 mL). The mixture was rapidly stirred and solid NaHCO$_3$ was added until effervescence ceased. The layers were then separated and the aqueous layer was extracted with ethyl acetate (2×50 mL). The combined organic phase was washed with water (50 mL), dried over Na$_2$SO$_4$, filtered and concentrated in vacuo to give a residue. The residue was purified by column chromatography to give the title compound (3.63 g, 72% yield) as a yellow oil. $^1$H NMR (400 MHz, CDCl$_3$) δ 7.42-7.25 (m, 10H), 5.19-5.01 (m, 1H), 3.88 (d, J=13.6 Hz, 2H), 3.77-3.71 (s, 3H), 3.57 (d, J=13.6 Hz, 2H), 3.16-2.96 (m, 2H); LC-MS (ESI$^+$) m/z 302.1 (M+H)$^+$.

Step 3—3-(Dibenzylamino)-2-fluoro-propan-1-ol

To a solution of lithium borohydride (50.6 mg, 2.3 mmol) in THF (5 mL) was added a solution of methyl 3-(dibenzylamino)-2-fluoro-propanoate (500 mg, 1.66 mmol) in THF (10 mL) at −15° C. under nitrogen. The reaction was allowed to warm to rt and was stirred for 4 h. On completion, the reaction mixture was quenched with saturated ammonium chloride solution (10 mL) dropwise, and then extracted with ethyl acetate. The combined organic phase was dried over Na$_2$SO$_4$, filtered and concentrated in vacuo to give the title compound (2.70 g, 96% yield) as a white oil. $^1$H NMR (400 MHz, CDCl$_3$) δ 7.44-7.28 (m, 10H), 4.76-4.58 (m, 1H), 3.82-3.67 (m, 4H), 366-3.60 (m, 2H), 3.11-3.08 (m, 1H), 2.90-2.84 (m, 2H) LC-MS (ESI$^+$) m/z 274.1 (M+H)$^+$.

Tert-butyl (2-(2-(2-(3-amino-2-fluoropropoxy)ethoxy)ethoxy)ethyl)carbamate (Intermediate AI)

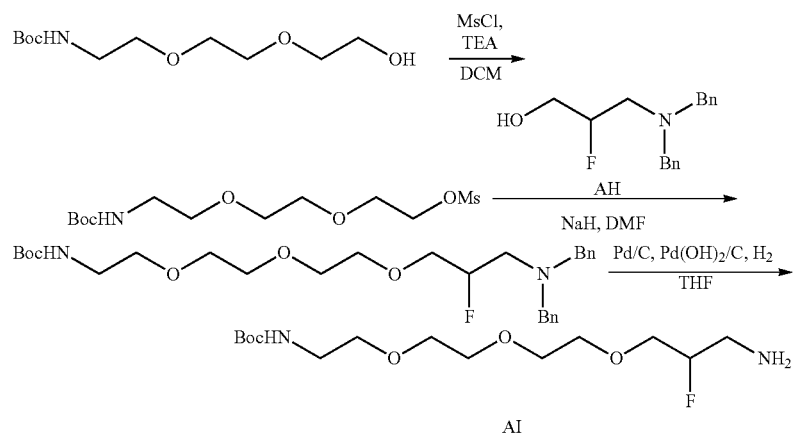

Step 1—2,2-Dimethyl-4-oxo-3,8,11-trioxa-5-azatridecan-13-yl methanesulfonate To a solution of tert-butyl N-[2-[2-(2-hydroxyethoxy)ethoxy]ethyl]carbamate (4.00 g, 16.0 mmol, CAS #139115-92-7) in dichloromethane (5 mL) was added triethylamine (3.25 g, 32.0 mmol) and MsCl (2.21 g, 19.2 mmol) at 0° C. The reaction mixture was then allowed to warm to rt and stirred for 1. On completion, the reaction mixture was quenched with water (10 mL) and extracted with dichloromethane (3×100 mL). The combined organic layer was washed with brine (2×50 mL), dried over anhydrous sodium sulfate, filtered and concentrated in vacuo to give the title compound (5.23 g, 99% yield) as a colorless oil. $^1$H NMR (400 MHz, CDCl$_3$) δ 4.94 (s, 1H), 4.44-4.37 (m, 2H), 3.83-3.75 (m, 2H), 3.69-3.65 (m, 2H), 3.64-3.59 (m, 2H), 3.54 (t, J=5.2 Hz, 2H), 3.36-3.29 (m, 2H), 3.08 (s, 3H), 1.45 (s, 9H).

Step 2—Tert-butyl (2-benzyl-4-fluoro-1-phenyl-6,9,12-trioxa-2-azatetradecan-14-yl)

To a solution of 3-(dibenzylamino)-2-fluoro-propan-1-ol (3.64 g, 13.3 mmol, Intermediate AH) in DMF (5 mL) was added sodium hydride (1.60 g, 39.5 mmol, 60% oil dispersion) at 0° C. under nitrogen atmosphere. The reaction mixture was stirred at 0° C. for 1 h. Then, 2-[2-[2-(tert-butoxycarbonylamino)ethoxy]ethoxy]ethyl methane sulfonate (5.23 g, 15.9 mmol) was added. The resulting reaction mixture was stirred at rt for 3 h. On completion, the reaction mixture was quenched with saturated NH₄Cl (20 mL) and extracted with ethyl acetate (3×100 mL). The combined organic layer was washed with brine (100 mL), dried over anhydrous sodium sulfate, filtered and concentrated in vacuo. The residue was purified by reverse phase flash column (0.1% NH₃.H₂O) to give the title compound (2.95 g, 44% yield) as a colorless oil. $^1$H NMR (400 MHz, CDCl₃) δ 7.40-7.28 (m, 10H), 5.02 (s, 1H), 4.89-4.70 (m, 1H), 3.72-3.61 (m, 12H), 3.60-3.56 (m, 2H), 3.54 (t, J=5.2 Hz, 2H), 3.31-3.18 (m, 2H), 2.82-2.69 (m, 2H), 1.46 (s, 9H); LC-MS (ESI)⁺ m/z 505.2. (M+H)⁺.

Step 3—Tert-butyl (2-(2-(2-(3-amino-2-fluoro-propoxy)ethoxy)ethoxy)ethyl)carbamate To a solution of tert-butyl N-[2-[2-[2-[3-(dibenzylamino)-2-fluoro-propoxy]ethoxy]ethoxy]ethyl]carbamate (2.90 g, 5.75 mmol) in THF (5 mL) was added Pd(OH)₂/C (1.00 g, 10 wt %) and Pd/C (1.00 g, 10 wt %) under nitrogen atmosphere. The suspension was degassed and purged with hydrogen gas 3 times. The mixture was then stirred under hydrogen gas (50 psi pressure) at rt for 24 h. On completion, the reaction mixture was filtered and concentrated in vacuo to give the title compound (1.70 g, 91% yield) as a white gum. LC-MS (ESI)⁺ m/z 325.1. (M+H)⁺.

Benzyl N-[2-[2-[2-[2-(2-hydroxyethoxy)ethoxy]ethoxy]ethyl]carbamate (Intermediate AJ)

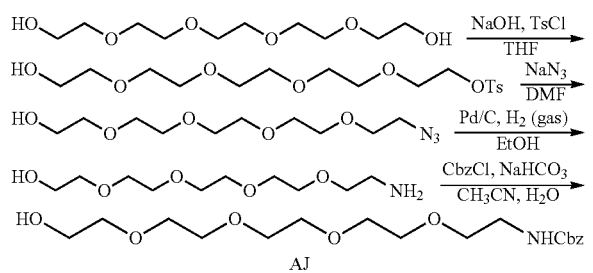

Step 1—2-[2-[2-[2-(2-Hydroxyethoxy)ethoxy]ethoxy]ethyl 4-methylbenzenesulfonate

To a solution of 2-[2-[2-[2-(2-hydroxyethoxy)ethoxy]e thoxy]ethanol (3.50 g, 14.7 mmol, CAS #4792-15-8) in tetrahydrofuran (30 mL) was added a solution of sodium hydroxide (763 mg, 19.1 mmol) in water (30 mL) at 0° C. Then a solution of TsCl (2.80 g, 14.7 mmol) in tetrahydrofuran (90 mL) was added slowly dropwise at 0° C. The reaction mixture was then allowed to warm to rt and stirred for 12 h. On completion, the reaction mixture was diluted with water (100 mL) and extracted with dichloromethane (3×100 mL). The combined organic layer was dried over anhydrous sodium sulfate, filtered and concentrated in vacuo to give the title compound (5.20 g, 87% yield) as a yellowish oil. LC-MS (ESI⁺) m/z 393.0 (M+H)⁺.

Step 2—2-[2-[2-[2-(2-Azidoethoxy)ethoxy]ethoxy]ethoxy]ethanol

To a mixture of 2-[2-[2-[2-(2-hydroxyethoxy)ethoxy]ethoxy]ethoxy]ethyl 4-methylbenzenesulfonate (4.50 g, 11.5 mmol) in DMF (30 mL) was added sodium azide (1.86 g, 28.6 mmol). Then the reaction mixture was stirred at 80° C. for 12 h. On completion, the reaction mixture was diluted with water (30 mL) and extracted with a mixture of dichloromethane and methanol (10:1, 3×30 mL). The organic layer was concentrated in vacuo to give the title compound (3.00 g, 99% yield) as a yellowish oil. LC-MS (ESI⁺) m/z 264.1 (M+H)⁺.

Step 3—2-[2-[2-[2-(2-Aminoethoxy)ethoxy]ethoxy]ethoxy]ethanol

To a mixture of 2-[2-[2-[2-(2-azidoethoxy)ethoxy]ethoxy]ethoxy]ethanol (3.00 g, 11.4 mmol) in ethanol (30 mL) was added Pd/C (1.00 g, 11.4 mmol, 5 wt %). Then the reaction mixture was stirred at rt for 48 hours under hydrogen gas (15 psi pressure). On completion, the reaction mixture was filtered and concentrated in vacuo to give the title compound (2.70 g, 100% yield) as a yellowish oil. LC-MS (ESI⁺) m/z 238.1 (M+H)⁺.

Step 4—Benzyl N-[2-[2-[2-[2-(2-hydroxyethoxy)ethoxy]ethoxy]ethoxy]ethyl]carbamate To a mixture of 2-[2-[2-[2-(2-aminoethoxy)ethoxy]ethoxy]ethoxy]ethanol (1.20 g, 5.06 mmol) in acetonitrile (10 mL) and water (10 mL) was added sodium bicarbonate (1.27 g, 15.1 mmol) and CbzCl (1.04 g, 6.07 mmol). Then the reaction mixture was stirred at 25° C. for 12 h. On completion, the reaction mixture was diluted with water (100 mL) and extracted with ethyl acetate (3×100 mL). Then the organic layer was dried over Na₂SO₄ and concentrated in vacuo. The residue was purified by silica gel column chromatography (petroleum ether:ethyl acetate=1:1) to give the title compound (1.50 g, 70% yield) as white solid. LC-MS (ESI⁺) m/z 372.1 (M+H)⁺.

Tert-butyl N-[2-[2-[2-[2-[2-(3-amino-2-fluoro-propoxy)ethoxy]ethoxy]ethoxy]ethoxy]ethyl]carbamate (Intermediate AK)

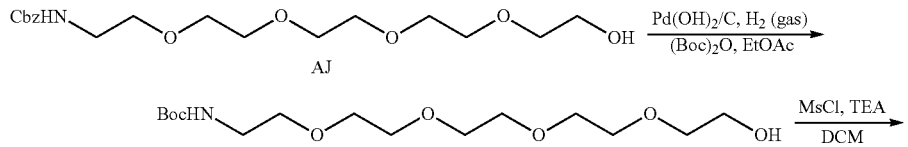

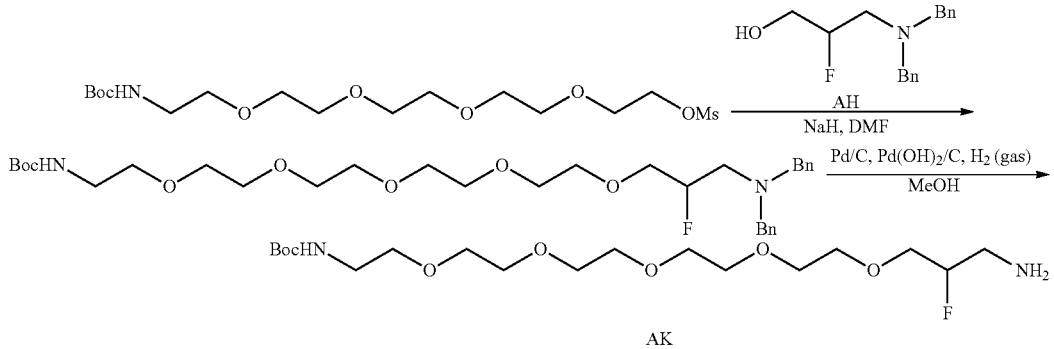

Step 1—Tert-butyl N-[2-[2-[2-[2-(2-hydroxyethoxy)ethoxy]ethoxy]ethoxy]ethyl]carbamate To a solution of benzyl N-[2-[2-[2-[2-(2-hydroxyethoxy)ethoxy]ethoxy]ethoxy]ethyl]carbamate (3.40 g, 9.15 mmol, Intermediate AJ) in ethyl acetate (35.0 mL) was added Pd(OH)$_2$/C (1.00 g, 10 wt %) and (Boc)$_2$O (3.00 g, 13.7 mmol, 3.15 mL). The reaction mixture was stirred under hydrogen gas (15 psi pressure) at rt for 16 h. On completion, the mixture was filtered through a pad of celite and washed with ethyl acetate (2×5 mL). Then the filtrate was concentrated in vacuo to give a residue. The residue was purified by column chromatography (DCM:MeOH=20:1) to give the title compound (2.45 g, 79% yield) as a colorless oil. $^1$H NMR (400 MHz, CDCl$_3$) δ 5.34 (s, 1H), 3.76-3.70 (m, 2H), 3.70-3.58 (m, 14H), 3.57-3.50 (m, 2H), 3.39-3.20 (m, 2H), 1.43 (s, 9H).

Step 2—2-[2-[2-[2-[2-(Tert-butoxycarbonylamino)ethoxy]ethoxy]ethoxy]ethoxy]ethylmethane sulfonate To a solution of tert-butyl N-[2-[2-[2-[2-(2-hydroxyethoxy)ethoxy]ethoxy]ethoxy]ethyl]carbamate (2.45 g, 7.26 mmol) and triethylamine (1.47 g, 14.5 mmol) in DCM (15.0 mL) was added mesyl chloride (998 mg, 8.71 mmol) at 0° C. Then the reaction mixture was allowed to warm to rt and stirred for 1 hr. On completion, the mixture was diluted with water (30 mL), extracted with DCM (3×50 mL). The organic layer was dried over anhydrous Na$_2$SO$_4$, filtered and concentrated in vacuo to give the title compound (2.88 g, 95% yield) as a yellow oil. $^1$H NMR (400 MHz, CDCl$_3$) δ 4.94 (s, 1H), 4.34-4.28 (m, 2H), 3.72-3.67 (m, 2H), 3.61-3.54 (m, 12H), 3.47 (t, J=5.2 Hz, 2H), 3.28-3.20 (m, 2H), 3.01 (s, 3H), 1.38 (s, 9H).

Step 3—Tert-butyl N-[2-[2-[2-[2-[2-[3-(dibenzylamino)-2-fluoro-propoxy]ethoxy]ethoxy]ethoxy]ethoxy]ethyl]carbamate To a solution of 3-(dibenzylamino)-2-fluoro-propan-1-ol (0.50 g, 1.83 mmol, Intermediate AH) in DMF (5.00 mL) was added sodium hydride (219 mg, 5.49 mmol, 60% purity) at 0° C. The mixture was stirred at 0° C. for 1 h, then 2-[2-[2-[2-[2-(tertbutoxycarbonylamino)ethoxy]ethoxy]ethoxy]ethoxy]ethylmethanesulfonate (912 mg, 2.20 mmol) was added to the reaction and the reaction mixture was allowed to warm to rt and stirred for 16 hrs. On completion, the mixture was quenched with water (50 mL) and extracted with ethyl acetate (3×50 mL). The organic layers were dried over anhydrous Na$_2$SO$_4$, filtered and concentrated in vacuo. The mixture was purified by reverse phase chromatography (0.1% NH$_3$.H$_2$O) to give the title compound (0.26 g, 22% yield) as a colorless oil. LC-MS (ESI$^+$) m/z 593.4 (M+H)$^+$.

Step 4—Tert-butyl N-[2-[2-[2-[2-[2-(3-amino-2-fluoro-propoxy)ethoxy]ethoxy]ethoxy]ethoxy]ethyl]carbamate To a solution of tert-butyl N-[2-[2-[2-[2-[2-[3-(dibenzylamino)-2-fluoro-propoxy]ethoxy]ethoxy]ethoxy]ethoxy]ethyl]carbamate (1.66 g, 2.80 mmol) in methanol (8.00 mL) was added Pd(OH)$_2$/C (0.50 g, 10 wt %) and Pd/C (0.50 g, 10 wt %) under nitrogen atmosphere. The suspension was degassed and purged with hydrogen gas 3 times. The mixture was stirred under hydrogen (50 psi pressure) at rt for 16 h. On completion, the reaction mixture was filtered and concentrated in vacuo to give the title compound (0.80 g, 69% yield) as a yellow oil. $^1$H NMR (400 MHz, CDCl$_3$) δ 5.06 (s, 1H), 4.63-4.43 (m, 1H), 3.66-3.54 (m, 18H), 3.47 (t, J=5.2 Hz, 2H), 3.28-3.19 (m, 2H), 2.93-2.83 (m, 2H), 1.37 (s, 9H).

4-(Dibenzylamino)-3-fluoro-butan-2-ol (Intermediate AL)

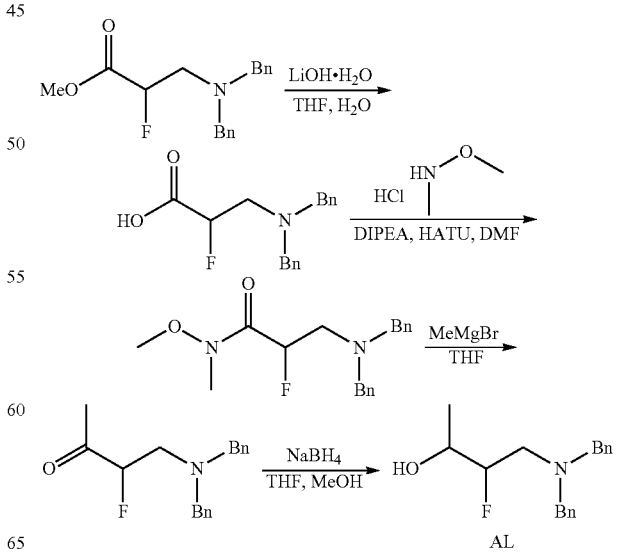

1117

Step 1—3-(Dibenzylamino)-2-fluoro-propanoic acid

To a mixture of methyl 3-(dibenzylamino)-2-fluoro-propanoate (15.0 g, 49.7 mmol, synthesized via Steps 1-2 of Intermediate AH) in THF (150 mL) and water (50 mL) was added LiOH.H₂O (4.18 g, 99.5 mmol). The reaction mixture was stirred at rt for 12 h. On completion, the reaction mixture was acidified with HCl (2 M) until the pH=5-6 and concentrated in vacuo to give a residue. The residue was purified by reverse phase chromatography (0.1% FA condition) to give the title compound (13.4 g, 92% yield) as a light yellow gum. LC-MS (ESI⁺) m/z 288.0 (M+H)⁺.

Step 2—3-(Dibenzylamino)-2-fluoro-N-methoxy-N-methyl-propanamide

To a mixture of N-methoxymethanamine (9.10 g, 93.2 mmol, HCl salt) in DMF (150 mL) was added DIPEA (36.1 g, 279 mmol), then 3-(dibenzylamino)-2-fluoro-propanoic acid (13.4 g, 46.6 mmol) and HATU (35.4 g, 93.2 mmol). The reaction mixture was stirred at rt for 2.5 hrs. On completion, the reaction mixture was concentrated in vacuo. The residue was diluted with water (100 mL) and extracted with ethyl acetate (3×100 mL). The combined organic layers were dried over Na₂SO₄, filtered and concentrated in vacuo to give a residue. The residue was purified by column chromatography to give the title compound (15.0 g, 94% yield) as a light yellow oil. LC-MS (ESI⁺) m/z 331.1 (M+H)⁺.

Step 3—4-(Dibenzylamino)-3-fluoro-butan-2-one

To a mixture of 3-(dibenzylamino)-2-fluoro-N-methoxy-N-methyl-propanamide (7.00 g, 21.1 mmol) in THF (80 mL) was added methyl magnesium bromide (3 M, 21.1 mL, 63.3 mmol) at 0° C. The reaction mixture was then warmed to rt and stirred for 2 h. On completion, the reaction mixture was quenched with slow addition of saturated ammonium chloride solution (30 mL) under stirring. The reaction mixture was then poured into 3 mL of water and extracted with ethyl acetate (3×80 mL). The combined organic layer was dried over Na₂SO₄, filtered and concentrated in vacuo to give a residue. The residue was purified by column chromatography to give the title compound (4.40 g, 72% yield) as a light yellow solid. ¹H NMR (400 MHz, CDCl₃) δ 7.29-7.15 (m, 10H), 4.93-4.77 (m, 1H), 3.72 (d, J=13.6 Hz, 2H), 3.49 (d, J=13.6 Hz, 2H), 2.95-2.84 (m, 2H), 2.02 (d, J=4.0 Hz, 3H); LC-MS (ESI⁺) m/z 286.1 (M+H)⁺.

Step 4—4-(Dibenzylamino)-3-fluoro-butan-2-ol

To a mixture of 4-(dibenzylamino)-3-fluoro-butan-2-one (4.40 g, 15.4 mmol) in THF (40 mL) and methanol (20 mL) was added sodium borohydride (1.17 g, 30.8 mmol) at 0° C. The reaction mixture was then allowed to warm to rt and stirred for 1 hour. On completion, the reaction mixture was quenched with slow addition of sat. NH₄Cl solution (4 mL) under stirring. The reaction mixture was concentrated in vacuo. The residue was then poured into (5 mL) of water and extracted with ethyl acetate (3×10 mL). The combined organic layer was dried over Na₂SO₄, filtered and concentrated in vacuo to give the title compound (4.30 g, 93% yield) as a colorless oil. LC-MS (ESI⁺) m/z 288.1 (M+H)⁺.

1118

Tert-butyl N-[2-[2-[2-(3-amino-2-fluoro-1-methyl-propoxy)ethoxy]ethoxy]ethyl]carbamate (Intermediate AM)

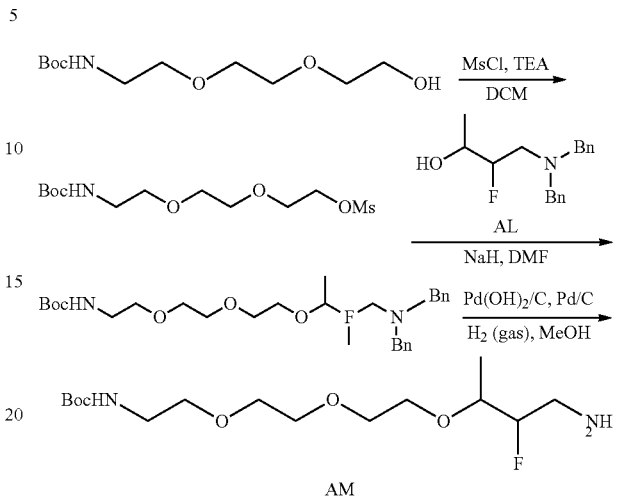

AM

Step 1—2-[2-[2-(Tert-butoxycarbonylamino)ethoxy]ethoxy]ethyl methanesulfonate To a mixture of tert-butyl N-[2-[2-(2-hydroxyethoxy)ethoxy]ethyl]carbamate (2.00 g, 8.02 mmol, CAS #139115-92-7) and triethylamine (2.44 g, 24.0 mmol) in DCM (20 mL) was added mesyl chloride (1.10 g, 9.63 mmol) at 0° C. The reaction mixture was then allowed to warm to rt and stirred for 2 h. On completion, the reaction mixture was poured into water (15 mL) and extracted with DCM (3×20 mL). The combined organic layer was dried over Na₂SO₄, filtered and concentrated in vacuo to give the title compound (2.60 g, 98% yield) as a light yellow oil. ¹H NMR (400 MHz, CDCl₃) δ 4.87 (s, 1H), 4.35-4.29 (m, 2H), 3.73-3.66 (s, 2H), 3.63-3.52 (m, 4H), 3.50-3.43 (m, 2H), 3.30-3.20 (s, 2H), 3.01 (s, 3H), 1.38 (s, 9H).

Step 2—Tert-butyl N-[2-[2-[2-[3-(dibenzylamino)-2-fluoro-1-methyl-propoxy]ethoxy]ethoxy]ethyl]carbamate To a mixture of 4-(dibenzylamino)-3-fluoro-butan-2-ol (1.60 g, 5.57 mmol, Intermediate AL) in DMF (20 mL) was added sodium hydride (668 mg, 16.7 mmol, 60% oil dispersion) at 0° C. and the reaction was stirred for 0.5 h. Then 2-[2-[2-(tert-butoxycarbonylamino)ethoxy]ethoxy]ethyl methanesulfonate (2.60 g, 7.94 mmol) was added. The reaction mixture was allowed to warm to rt and stirred C for 2 h. On completion, the reaction mixture was quenched with slow addition of water (3 mL) under stirring. The reaction mixture was then poured into water (20 mL) and extracted with ethyl acetate (4×20 mL). The combined organic layer was dried over Na₂SO₄, filtered and concentrated in vacuo to give a residue. The residue was purified by reverse phase (0.1% NH₃.H₂O condition) to give the title compound (1.25 g, 41% yield) as a light yellow oil. LC-MS (ESI⁺) m/z 519.3 (M+H)⁺.

Step 3—Tert-butyl N-[2-[2-[2-(3-amino-2-fluoro-1-methyl-propoxy)ethoxy]ethoxy]ethyl]carbamate To a mixture of tert-butyl N-[2-[2-[2-[3-(dibenzylamino)-2-fluoro-1-methyl-propoxy]ethoxy]ethoxy]ethyl]carbamate (1.30 g, 2.51 mmol) in MeOH (10 mL) was added Pd(OH)$_2$/C (470 mg, 10 wt %) and Pd/C (470 mg, 10 wt %) under hydrogen atmosphere (15 psi pressure). The reaction mixture was stirred at rt for 14 h. On completion, the reaction mixture was filtered through a pad of celite and the filtrate was concentrated in vacuo to give the title compound (820 mg, 96% yield) as a colorless oil. LC-MS (ESI$^+$) m/z 339.3 (M+H)$^+$.

2-[3-(dibenzylamino)-2-fluoro-1,1-dimethyl-propoxy]ethanol (Intermediate AN)

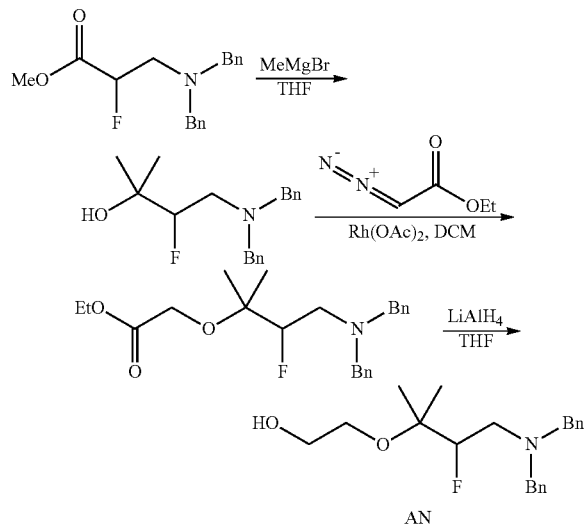

Step 1—4-(Dibenzylamino)-3-fluoro-2-methyl-butan-2-ol

To a mixture of methyl 3-(dibenzylamino)-2-fluoro-propanoate (15.0 g, 49.7 mmol, synthesized via Steps 1-2 of Intermediate AH) in THF (250 mL) was added MeMgBr (3 M, 41.4 mL) dropwise at 0° C. under nitrogen atmosphere. The reaction mixture was stirred at rt for 1 h. On completion, the reaction mixture was quenched with saturated aqueous ammonium chloride (10 mL) at 0° C. and extracted with ethyl acetate (2×50 mL). The organic layers were collected, dried over anhydrous sodium sulfate, filtered and concentrated in vacuo to give the title compound (15.0 g, 89% yield) as a yellow solid. LC-MS (ESI$^+$) m/z 302.1 (M+H)$^+$.

Step 2—Ethyl 2-[3-(dibenzylamino)-2-fluoro-1,1-dimethyl-propoxy]acetate

To a solution of 4-(dibenzylamino)-3-fluoro-2-methyl-butan-2-ol (30.0 g, 99.5 mmol) in DCM (200 mL) was added Rh(OAc)$_2$ (440 mg, 1.99 mmol) then ethyl 2-diazoacetate (34.0 g, 298 mmol) in DCM (100 mL) was added. The reaction mixture was stirred at rt for 12 h. On completion, the reaction mixture was concentrated in vacuo. The residue was purified by silica gel chromatography to give the title compound (11.7 g, 28% yield) as a colorless oil. LC-MS (ESI$^+$) m/z 388.1 (M+H)$^+$ Step 3—2-[3-(Dibenzylamino)-2-fluoro-1,1-dimethyl-propoxy]ethanol To a solution of ethyl 2-[3-(dibenzylamino)-2-fluoro-1,1-dimethyl-propoxy]acetate (8.00 g, 20.6 mmol) in THF (220 mL) was added lithium aluminum hydride (1.20 g, 30.9 mmol, 98% purity) at 0° C., then reaction mixture was allowed to warm to rt and stirred for 3 h. On completion, the reaction mixture was quenched with water (2 mL) and NaOH solution (15%, 6 mL) at 0° C. and the reaction mixture was filtered. The filtrate was dried over Na$_2$SO$_4$, filtered and concentrated in vacuo to give a residue. The residue was purified by silica gel chromatography to give the title compound (5.90 g, 81% yield) as a colorless oil. $^1$H NMR (400 MHz, CDCl$_3$) δ 7.44-7.22 (m, 10H), 4.64-4.46 (dd, J=7.6, 48.8 Hz, 1H), 3.82 (d, J=13.6 Hz, 2H), 3.58 (d, J=13.6 Hz, 2H), 3.53-3.48 (m, 2H), 3.44-3.31 (m, 2H), 2.99-2.82 (m, 1H), 2.75-2.61 (m, 1H), 1.72 (s, 1H), 1.13 (s, 3H), 1.09 (s, 3H).

2-[2-[2-[2-(tert-butoxycarbonylamino)ethoxy]ethoxy]ethoxy]ethyl methanesulfonate (Intermediate AO)

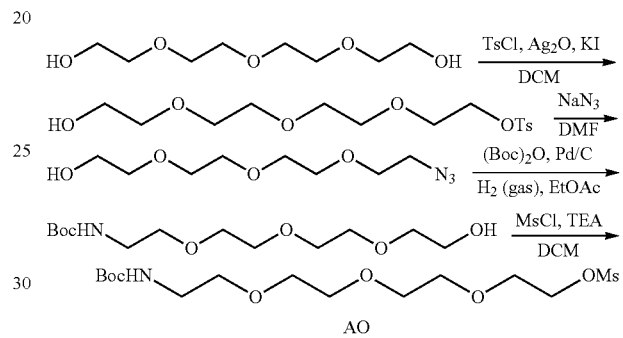

Step 1—2-[2-[2-(2-Hydroxyethoxy)ethoxy]ethoxy]ethyl 4-methylbenzenesulfonate

To a solution of 2-[2-[2-(2-hydroxyethoxy)ethoxy]ethoxy]ethanol (20.0 g, 103 mmol, CAS #112-60-7) and potassium iodide (1.71 g, 10.3 mmol) in DCM (2 L) was added 4-methylbenzenesulfonyl chloride (19.6 g, 103 mmol) and silver oxide (28.6 g, 124 mmol). The reaction mixture was stirred at rt for 17 h. On completion, the reaction mixture was filtered and concentrated in vacuo. The residue was purified by silica gel chromatography to give the title compound (25.1 g, 70% yield) as a yellow oil. $^1$H NMR (400 MHz, CDCl$_3$) δ 7.83-7.78 (m, 2H), 7.37-7.33 (m, 2H), 4.19-4.14 (m, 2H), 3.74-3.60 (m, 14H), 2.45 (s, 3H); LC-MS (ESI$^+$) m/z 349.0 (M+H)$^+$.

Step 2—2-[2-[2-(2-Azidoethoxy)ethoxy]ethoxy]ethanol

To a solution of 2-[2-[2-(2-hydroxyethoxy)ethoxy]ethoxy]ethyl 4-methylbenzenesulfonate (13.5 g, 38.8 mmol) in DMF (100 mL) was added sodium azide (5.04 g, 77.5 mmol) slowly. The reaction mixture was stirred at 80° C. for 18 h. On completion, the reaction mixture was concentrated in vacuo. The residue was diluted with ethyl acetate (200 ml), filtered and the filtrate was concentrated in vacuo to a half volume (50 mL). The crude product ethyl acetate solution was used in next step directly.

Step 3—Tert-butyl N-[2-[2-[2-(2-hydroxyethoxy)ethoxy]ethoxy]ethyl]carbamate

To a solution of 2-[2-[2-(2-azidoethoxy)ethoxy]ethoxy]ethanol (15.0 g, 68.4 mmol) and (Boc)$_2$O (74.7 g, 342 mmol) in ethyl acetate (300 mL) was added Pd/C (5 g, 10 wt %) under nitrogen atmosphere. The suspension was degassed and purged with hydrogen gas three times. The reaction mixture was stirred under hydrogen gas (15 Psi pressure) at rt for 18 h. On completion, the mixture was filtered and the filtrate was concentrated in vacuo. The residue was purified by silica gel chromatography (SiO$_2$, DCM/MeOH=10/1) to give the title compound (5.1 g, 25% yield) as a light yellow oil. $^1$H NMR (400 MHz, CDCl$_3$) δ 5.67 (s, 1H), 3.78-3.72 (m, 4H), 3.69-3.63 (m, 8H), 3.55 (t, J=4.8 Hz, 2H), 3.34 (d, J=4.8 Hz, 2H), 3.07 (s, 1H), 1.46 (s, 9H).

Step 4—2-[2-[2-[2-(tert-butoxycarbonylamino) ethoxy]ethoxy]ethoxy]ethyl methanesulfonate To a solution of tert-butyl N-[2-[2-[2-(2-hydroxyethoxy) ethoxy]ethoxy]ethyl]carbamate (3.0 g, 10.2 mmol) and triethylamine (2.07 g, 2.77 mL, 20.5 mmol) in DCM (30 mL) was added mesyl chloride (1.41 g, 12.3 mmol) at 0° C. The reaction mixture was stirred at rt for 17 h. On completion, the mixture was quenched with water (30 mL) and extracted with DCM (2×30 mL). The organic layer was washed with sat.NaHCO$_3$ (40 mL), then washed with brine (40 mL), dried over Na$_2$SO$_4$, filtered and concentrated in vacuo to give the title compound (3.6 g, 95% yield) as a light yellow oil. $^1$H NMR (400 MHz, CDCl$_3$) δ 5.05 (s, 1H), 4.43-4.39 (m, 2H), 3.82-3.78 (m, 2H), 3.71-3.69 (m, 2H), 3.69-3.67 (m, 2H), 3.67-3.62 (m, 4H), 3.56 (t, J=4.8 Hz, 2H), 3.34 (q, J=4.8 Hz, 2H), 3.10 (s, 3H), 1.46 (s, 9H).

Tert-butyl N-[2-[2-[2-[2-[2-(3-amino-2-fluoro-1,1-dimethyl-propoxy)ethoxy]ethoxy]ethoxy]ethoxy] ethyl]carbamate (Intermediate AP)

Step 1—Tert-butyl N-[2-[2-[2-[2-[2-[3-(dibenzylamino)-2-fluoro-1,1-dimethyl-propoxy]ethoxy] ethoxy]ethoxy]ethyl]carbamate To a mixture of 2-[3-(dibenzylamino)-2-fluoro-1,1-dimethyl-propoxy]ethanol (1.50 g, 4.34 mmol, Intermediate AN) in DMF (10 mL) was added sodium hydride (521 mg, 13.0 mmol, 60% oil dispersion) at 0° C. for 0.5 h. Then the 2-[2-[2-[2-(tert-butoxycarbonylamino)ethoxy]ethoxy] ethoxy]ethyl methanesulfonate (2.42 g, 6.51 mmol, Intermediate AO) was added. The reaction mixture was allowed to warm to rt and stirred for 6 hours. On completion, the reaction mixture was quenched with slow addition of water (10 mL) under stirring. The mixture was extracted with DCM (3×20 mL). The combined organic layer was dried over Na$_2$SO$_4$, filtered and concentrated in vacuo to give a residue. The residue was purified by reverse phase chromatography (0.1% NH$_3$.H$_2$O condition) to give the title compound (1.10 g, 39% yield) as a light yellow oil. LC-MS (ESI$^+$) m/z 621.5 (M+H)$^+$.

Step 2—Tert-butyl N-[2-[2-[2-[2-[2-(3-amino-2-fluoro-1,1-dimethyl-propoxy)ethoxy]ethoxy] ethoxy]ethyl]carbamate To a mixture of tert-butyl N-[2-[2-[2-[2-[2-[3-(dibenzylamino)-2-fluoro-1,1-dimethyl-propoxy]ethoxy]ethoxy] ethoxy]ethoxy]ethyl]carbamate (1.10 g, 1.77 mmol) in methanol (10 mL) was added Pd(OH)$_2$/C (600 mg, 10 wt %), Pd/C (600 mg, 10 wt %) and NH$_3$.H$_2$O (455 mg, 12.9 mmol, 500 uL) under hydrogen atmosphere (15 psi pressure). The reaction mixture was stirred at rt for 15 h. On completion, the reaction mixture was filtered and concentrated in vacuo to give the title compound (750 mg, 96% yield) as a light yellow oil. LC-MS (ESI$^+$) m/z 441.3 (M+H)$^+$.

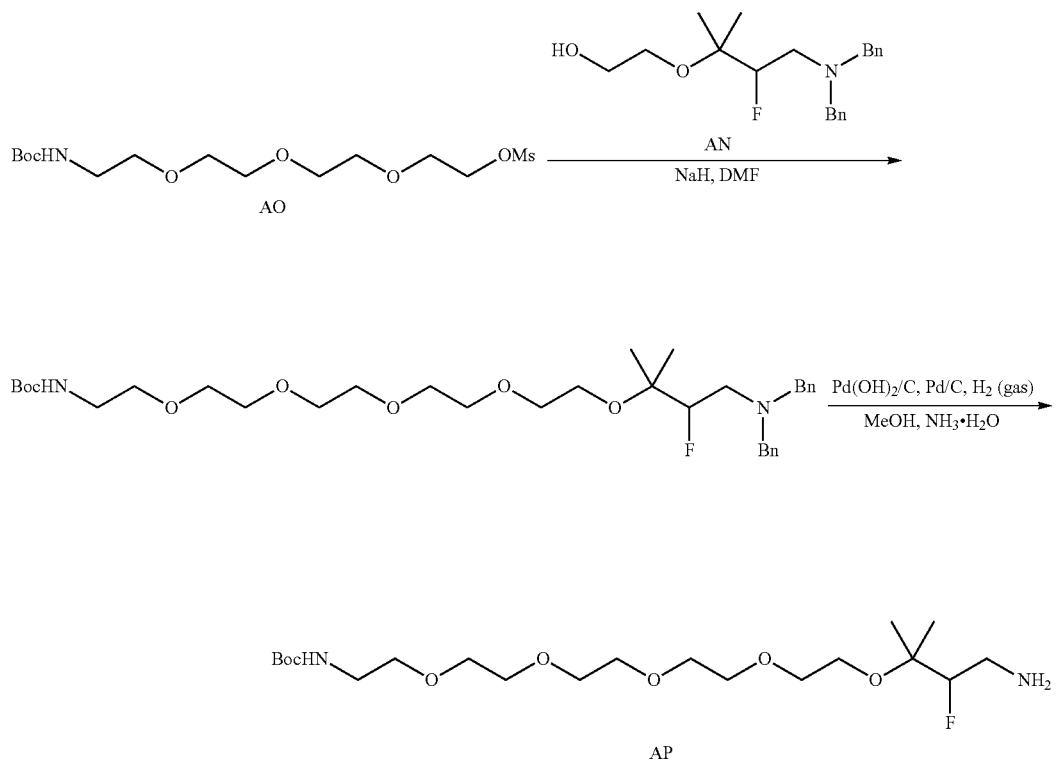

2-[2-(2-Bromoethoxy)ethyl]isoindoline-1,3-dione (Intermediate AQ)

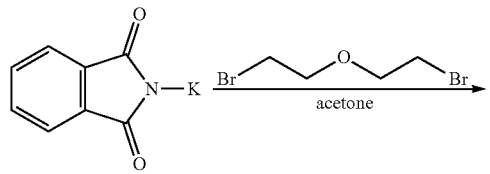

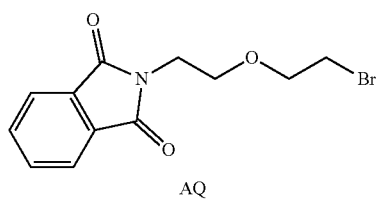

A solution of (1,3-dioxoisoindolin-2-yl)potassium (10.0 g, 53.9 mmol) and 1-bromo-2-(2-bromoethoxy)ethane (37.5 g, 161 mmol) in acetone (250 mL) was stirred at 60° C. for 12 h. On completion, the reaction mixture was filtered and concentrated in vacuo to give a residue. The residue was purified by column chromatography to give the title compound (12.0 g, 74% yield) as a white solid. $^1$H NMR (400 MHz, CDCl$_3$) δ 7.91-7.84 (m, 2H), 7.77-7.72 (m, 2H), 3.96-3.90 (m, 2H), 384-377 (m, 4H), 3.42 (t, J=6.0 Hz, 21-).

Tert-butyl N-[2-[2-[2-(3-amino-2-fluoro-1,1-dimethyl-propoxy)ethoxy]ethoxy]ethyl]carbamate (Intermediate AR)

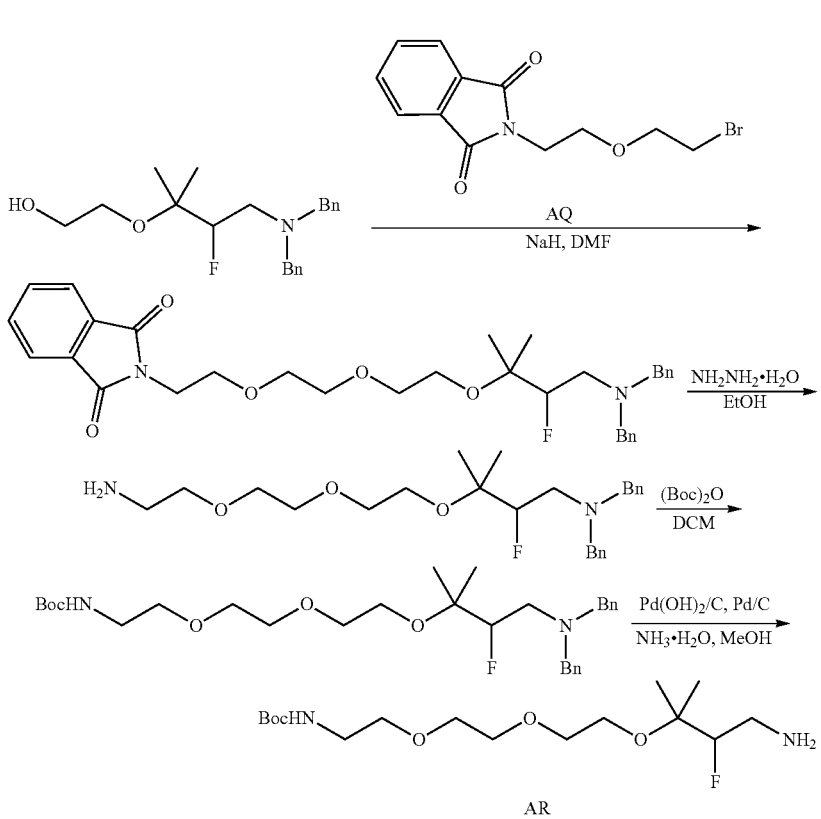

Step 1—2-[2-[2-[2-[3-(Dibenzylamino)-2-fluoro-1,1-dimethyl-propoxy]ethoxy]ethoxy]ethyl]iso indoline-1,3-dione To a solution of 2-[3-(dibenzylamino)-2-fluoro-1,1-dimethyl-propoxy]ethanol (2.00 g, 5.79 mmol, Intermediate AN) in DMF (35 mL) was added sodium hydride (694 mg, 17.3 mmol, 60% oil dispersion) at 0° C. The reaction mixture was stirred at 0° C. for 0.5 h, and then 2-[2-(2-bromoethoxy)ethyl]isoindoline-1,3-dione (2.76 g, 9.26 mmol, Intermediate AQ) was added and the reaction mixture was stirred allowed to warm to rt and stirred for 17 h. On completion, the reaction mixture was quenched with water (1 mL) at 0° C., and then concentrated in vacuo to give the product (5.00 g) as yellow oil. LC-MS (ESI)$^+$ m/z 563.2. (M+H)$^+$.

Step 2—3-[2-[2-(2-Aminoethoxy)ethoxy]ethoxy]-N,N-dibenzyl-2-fluoro-3-methyl-butan-1-amine To a solution of 2-[2-[2-[2-[3-(dibenzylamino)-2-fluoro-1,1-dimethyl-propoxy]ethoxy]ethoxy]ethyl]isoindoline-1,3- dione (5.00 g, 8.89 mmol) in EtOH (40 mL) was added hydrazine (2.27 g, 44.4 mmol, 98% purity) and the reaction mixture was stirred at 80° C. for 38 h. On completion, the reaction mixture was filtered and the filtrate concentrated in vacuo to give the title compound (2.50 g) as a yellow oil. LC-MS (ESI)+ m/z 433.1. (M+H)+.

Step 3—Tert-butyl N-[2-[2-[2-[3-(dibenzylamino)-2-fluoro-1,1-dimethyl-propoxy]ethoxy]ethoxy]ethyl] carbamate To a solution of 3-[2-[2-(2-aminoethoxy)ethoxy]ethoxy]-N,N-dibenzyl-2-fluoro-3-methyl-butan-1-amine (2.50 g, 5.78 mmol, crude) in DCM (30 mL) was added (Boc)$_2$O was filtered and concentrated in vacuo to give the title compound (550 mg, 88% yield) as a colorless oil. $^1$H NMR (400 MHz, CDCl$_3$) δ=5.51 (s, 1H), 4.32-4.15 (m, 1H), 3.67-3.57 (m, 8H), 3.54 (t, J=5.2 Hz, 2H), 3.36-3.28 (m, 2H), 3.07-2.96 (m, 1H), 2.95-2.85 (m, 1H), 1.45 (s, 9H), 1.23 (dd, J=1.6, 10 Hz, 6H); LC-MS (ESI)+ m/z 353.2. (M+H)+.

Tert-butyl N-[2-[2-[2-[2-[2-(3-amino-2-fluoro-1-methyl-propoxy)ethoxy]ethoxy]ethoxy]ethoxy]ethyl] carbamate (Intermediate AS)

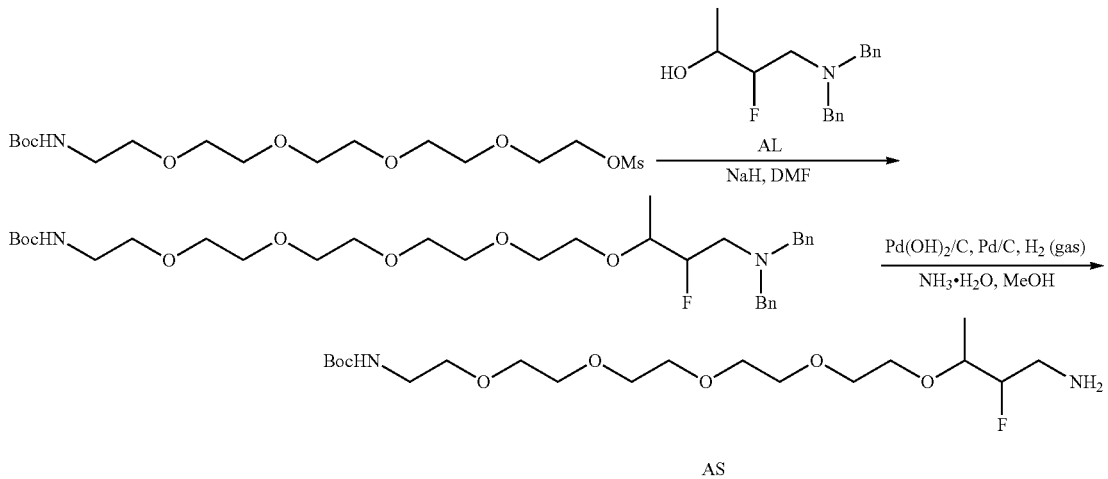

(2.52 g, 11.56 mmol) and the reaction mixture was stirred at rt for 3 h. On completion, the mixture was concentrated in vacuo to give a residue. The residue was purified by reverse phase chromatography (0.1% NH$_3$.H$_2$O) to give the title compound (950 mg, 30% yield) as a colorless oil. $^1$H NMR (400 MHz, CDCl$_3$) δ 7.42 (d, J=7.2 Hz 4H), 7.31 (t, J=7.2 Hz, 4H), 7.26-7.19 (m, 2H), 5.01 (s, 1H), 4.64 (dd, J=8.0, 49.2 Hz, 1H), 3.75 (d, J=13.6 Hz, 2H), 3.60 (d, J=13.6 Hz, 2H), 3.57-3.38 (m, 10H), 3.31 (d, J=3.6 Hz, 2H), 2.98-2.80 (m, 1H), 2.79-2.65 (m, 1H), 1.45 (s, 9H), 1.10 (d, J=8.8 Hz, 6H); LC-MS (ESI)+ m/z 533.4. (M+H)+.

Step 4—Tert-butyl N-[2-[2-[2-(3-amino-2-fluoro-1,1-dimethyl-propoxy)ethoxy]ethoxy]ethyl]carbamate To a solution of tert-butyl N-[2-[2-[2-[3-(dibenzylamino)-2-fluoro-1,1-dimethyl-propoxy]ethoxy]ethoxy]ethyl]carbamate (950 mg, 1.78 mmol) in MeOH (20 mL) was added Pd(OH)$_2$/C (500 mg, 10 wt %), Pd/C (500 mg, 10 wt %) and NH$_3$.H$_2$O (1.92 g, 20.7 mmol, 38 wt %) under nitrogen atmosphere. The suspension was degassed under vacuum and purged with hydrogen gas three times. The reaction mixture was stirred under hydrogen atmosphere (15 psi pressure) at rt for 55 h. On completion, the reaction mixture Step 1-Tert-butyl N-[2-[2-[2-[2-[2-[3-(dibenzylamino)-2-fluoro-1-methyl-propoxy]ethoxy]ethoxy]ethoxy]ethoxy]ethyl]carbamate To a solution of 4-(dibenzylamino)-3-fluoro-butan-2-ol (968 mg, 3.37 mmol, Intermediate AL) in DMF (20 mL) was added NaH (404 mg, 10.1 mmol, 60% dispersion in mineral oil) and the reaction mixture was stirred at rt for 30 min. Then 2-[2-[2-[2-[2-(tert-butoxycarbonylamino)ethoxy]ethoxy]ethoxy]ethyl methanesulfonate (2.10 g, 5.05 mmol, synthesized via Steps 1-2 of Intermediate AK) was added into the mixture and the reaction was stirred at rt for 12 h. On completion, the reaction mixture was quenched by addition H$_2$O (20 mL) and extracted with ethyl acetate (2×30 mL). The combined organic layers were dried over anhydrous Na$_2$SO$_4$, filtered and concentrated in vacuo to give a residue. The residue was purified by prep-HPLC (0.1% NH$_3$.H$_2$O condition) to give the title compound (640 mg, 25% yield) as a yellow oil. LC-MS (ESI+) m/z 607.3 (M+H)+.

Step 2-Tert-butyl N-[2-[2-[2-[2-[2-(3-amino-2-fluoro-1-methyl-propoxy)ethoxy]ethoxy]ethoxy]ethoxy]ethyl]carbamate To a mixture of tert-butyl N-[2-[2-[2-[2-[2-[3-(dibenzylamino)-2-fluoro-1-methyl-propoxy]ethoxy]ethoxy]ethoxy]ethoxy]ethyl]carbamate (840 mg, 1.38 mmol) in MeOH (20 mL) and NH$_3$.H$_2$O (1 mL) was added Pd(OH)$_2$/C (300 mg, 10 wt %) and Pd/C (300 mg, 10 wt %). The reaction mixture was stirred under hydrogen atmosphere (50 psi pressure) at rt for 12 h. On completion, the mixture was filtered, and the filtrate was concentrated in vacuo to give the title compound (540 mg, 91% yield) as a colorless oil. LC-MS (ESI$^+$) m/z 427.2 (M+H)$^+$.

Tert-butyl N-[3-[3-(3-amino-2-fluoro-1,1-dimethyl-propoxy)propoxy]propyl]carbamate (Intermediate AT)

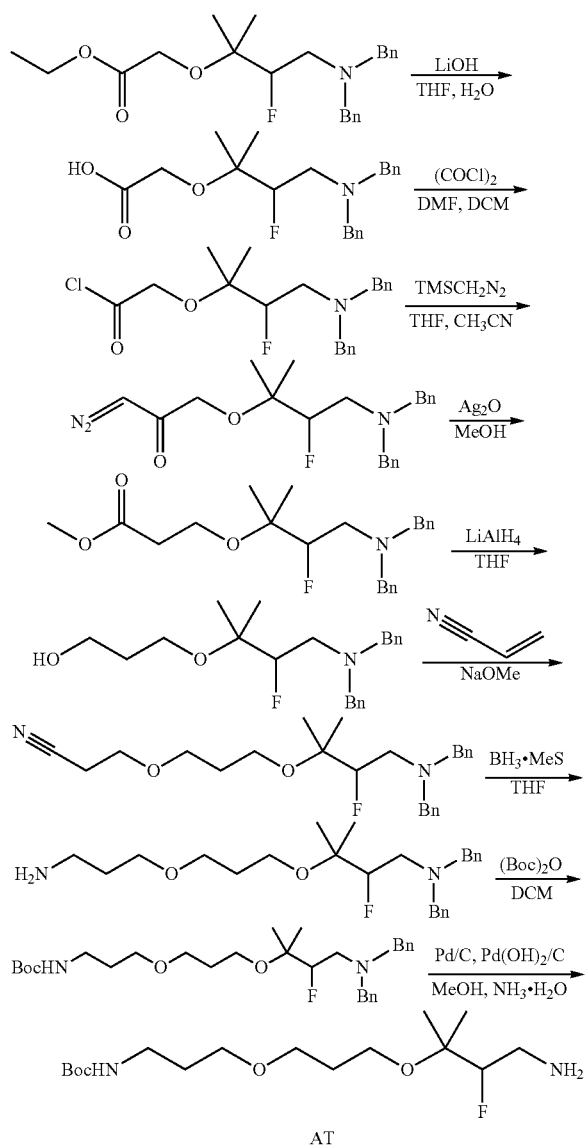

Step 1—2-[3-(dibenzylamino)-2-fluoro-1,1-dimethyl-propoxy]acetic acid

To a solution of ethyl 2-[3-(dibenzylamino)-2-fluoro-1,1-dimethyl-propoxy]acetate (5.00 g, 12.9 mmol, synthesized via Steps 1-2 of Intermediate AN) in THF (50.0 mL) and H$_2$O (30.0 mL) was added LiOH (1.24 g, 51.6 mmol) and the reaction mixture was stirred at rt for 6 h. On completion, the mixture was concentrated and acidified with 5 N HCl (1 mL) until pH=5 and was then concentrated in vacuo again. The residue was purified by reverse phase chromatography (0.1% FA) to give the title compound (3.50 g, 64% yield) as a light yellow oil. $^1$H NMR (400 MHz, CDCl$_3$) δ 7.50-7.31 (m, 10H), 4.64-4.44 (m, 1H), 4.06-3.96 (m, 6H), 3.07-2.77 (m, 2H), 1.10 (s, 3H), 1.07 (s, 3H)

Step 2—2-[3-(dibenzylamino)-2-fluoro-1,1-dimethyl-propoxy]acetyl chloride

To a solution of 2-[3-(dibenzylamino)-2-fluoro-1,1-dimethyl-propoxy]acetic acid (2.00 g, 5.56 mmol) in DCM (40.0 mL) was added DMF (4.07 mg, 55.6 umol, 4.28 uL) and (COCl)$_2$ (2.12 g, 16.6 mmol, 1.46 mL) at 0° C., then reaction mixture was allowed to warm to rt and stirred for 3 h. On completion, the mixture was concentrated in vacuo to give the title compound (2.00 g, 98% yield) as a light yellow oil. LC-MS (ESI$^+$) m/z 388.2 (M+H)$^+$ (+OEt from quench with ethanol).

Step 3—1-diazo-3-[3-(dibenzylamino)-2-fluoro-1,1-dimethyl-propoxy]propan-2-one

To a solution of 2-[3-(dibenzylamino)-2-fluoro-1,1-dimethyl-propoxy]acetyl chloride (3.40 g, 9.00 mmol) in THF (20.0 mL) and ACN (20.0 mL) was dropwise added TMSCHN$_2$ (2 M, 9.00 mL) at 0° C. Then the reaction mixture was allowed to warm to rt and stirred for 19 h. On completion, the mixture was concentrated in vacuo to give a residue. The residue was purified by column chromatography (PE:EA=5:1) to give the title compound (2.30 g, 65% yield) as a yellow solid. $^1$H NMR (400 MHz, CDCl$_3$) δ 7.46-7.21 (m, 10H), 5.08 (s, 1H), 4.61-4.45 (m, 1H), 3.92-3.80 (m, 4H), 3.60-3.50 (m, 2H), 3.00-2.62 (m, 2H), 1.13 (s, 3H), 1.10 (s, 3H)

Step 4—Methyl 3-[3-(dibenzylamino)-2-fluoro-1,1-dimethyl-propoxy]propanoate

To a solution of 1-diazo-3-[3-(dibenzylamino)-2-fluoro-1,1-dimethyl-propoxy]propan-2-one (2.00 g, 5.22 mmol) in MeOH (30 mL) was added Ag$_2$O (120 mg, 521 umol) and the reaction mixture was stirred at 50° C. for 16 h. On completion, the mixture was filtered and concentrated in vacuo to give a residue. The residue was purified by silica gel chromatography (PE:EA=5:1) to give the title compound (1.10 g, 48% yield) as a colorless oil. $^1$H NMR (400 MHz, CDCl$_3$) δ 7.43-7.20 (m, 10H), 4.61-4.42 (m, 1H), 3.81-3.73 (m, 2H), 3.66 (s, 3H), 3.63-3.49 (m, 4H), 2.94-2.63 (m, 2H), 2.40-2.36 (m, 2H), 1.11 (s, 3H), 1.08 (s, 3H)

Step 5—3-[3-(dibenzylamino)-2-fluoro-1,1-dimethyl-propoxy]propan-1-ol

To a solution of methyl 3-[3-(dibenzylamino)-2-fluoro-1,1-dimethyl-propoxy]propanoate (900 mg, 2.32 mmol) in THF (15.0 mL) was added LiAlH$_4$ (116 mg, 3.02 mmol, 98% purity) at 0° C. under nitrogen atmosphere. The reaction mixture was allowed to warm to rt and stirred for 1 hr. On completion, the mixture was quenched with water (1 mL) and 15% NaOH (1.5 mL) at 0° C. The mixture was then filtered, dried over Na$_2$SO$_4$, filtered again and concentrated in vacuo to give the title compound (800 mg, 90% yield) as a colorless oil. $^1$H NMR (400 MHz, CDCl$_3$) δ 7.42-7.21 (m, 10H), 4.64-4.45 (m, 1H), 3.82-3.77 (m, 2H), 3.66-3.56 (m, 4H), 3.55-3.41 (m, 2H), 2.96-2.63 (m, 2H), 2.28 (s, 1H), 1.68-1.62 (m, 2H), 1.11 (s, 3H), 1.09 (s, 3H).

Step 6—3-[3-[3-(dibenzylamino)-2-fluoro-1,1-dimethyl-propoxy]propoxy]propanenitrile To a mixture of 3-[3-(dibenzylamino)-2-fluoro-1,1-dimethyl-propoxy]propan-1-ol (560 mg, 1.56 mmol) and prop-2-enenitrile (1.60 g, 30.1 mmol, 2.00 mL) was added NaOMe (841 ug, 15.5 umol), and the reaction mixture was stirred at rt for 50 h. On completion, the mixture was concentrated in vacuo to give a residue. The residue was purified by silica gel chromatography (PE:EA=5:1) to give the title compound (550 mg, 83% yield) as a colorless oil. $^1$H NMR (400 MHz, CDCl$_3$) δ 7.43-7.20 (m, 10H), 4.64-4.43 (m, 1H), 3.80-3.77 (m, 2H), 3.66-3.52 (m, 4H), 3.44-3.28 (m, 4H), 3.00-2.62 (m, 2H), 2.56-2.53 (m, 2H), 1.70-1.60 (m, 2H), 1.11 (s, 3H), 1.07 (s, 3H).

Step 7—3-[3-(3-aminopropoxy)propoxy]-N,N-dibenzyl-2-fluoro-3-methyl-butan-1-

A solution of BH$_3$-Me$_2$S (10 M, 145 uL) in THF (20.0 mL) was added to a solution of 3-[3-[3-(dibenzylamino)-2-fluoro-1,1-dimethyl-propoxy]propoxy]propanenitrile (300 mg, 727 umol) in THF (5.00 mL) at 0° C. and stirred for 30 min. Then the reaction mixture was heated to 70° C. and stirred for 16 h. On completion, the mixture was quenched with MeOH (3 mL) and concentrated in vacuo to give the title compound (300 mg, 65% yield) as yellow oil. LC-MS (ESI$^+$) m/z 417.4 (M+H)$^+$.

Step 8—Tert-butyl N-[3-[3-[3-(dibenzylamino)-2-fluoro-1,1-dimethyl-propoxy]propoxy]propyl]carbamate To a solution of 3-[3-(3-aminopropoxy)propoxy]-N,N-dibenzyl-2-fluoro-3-methyl-butan-1-amine (300 mg, 720 umol) in DCM (5.00 mL) was added (Boc)$_2$O (314 mg, 1.44 mmol, 330 uL) and the reaction mixture was stirred at rt for 2 h. On completion, the mixture was concentrated in vacuo. The mixture was purified by reverse phase chromatography (0.1% NH$_3$.H$_2$O) to give the title compound (180 mg, 45% yield) as a yellow solid. LCMS (M+1)+: 517.3.

Step 9—Tert-butyl N-[3-[3-(3-amino-2-fluoro-1,1-dimethyl-propoxy)propoxy]propyl]carbamate To a solution of tert-butyl N-[3-[3-[3-(dibenzylamino)-2-fluoro-1,1-dimethyl-propoxy]propoxy]propyl]carbamate (180 mg, 348 umol) and NH$_3$.H$_2$O (151 mg, 1.30 mmol, 166 uL, 30 wt %) in MeOH (5.00 mL) was added Pd/C (90.0 mg, 348 umol, 10 wt %) and Pd(OH)$_2$/C (90.0 mg, 348 umol, 10 wt %) under nitrogen. The suspension was degassed under vacuum and purged with hydrogen gas several times. The reaction mixture was stirred under hydrogen atmosphere (50 psi pressure) at rt for 16 h. On completion, the mixture was filtered and the filtrate concentrated in vacuo to give the title compound (70.0 mg, 59% yield) as a yellow oil. LC-MS (ESI$^+$) m/z 337.2 (M+H)$^+$ Tert-butyl N-[2-[2-(3-amino-2-fluoro-1,1-dimethyl-propoxy)ethoxy]ethyl]carbamate (Intermediate AU)

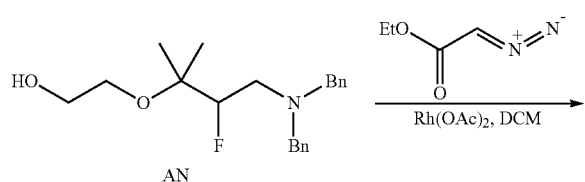

AN

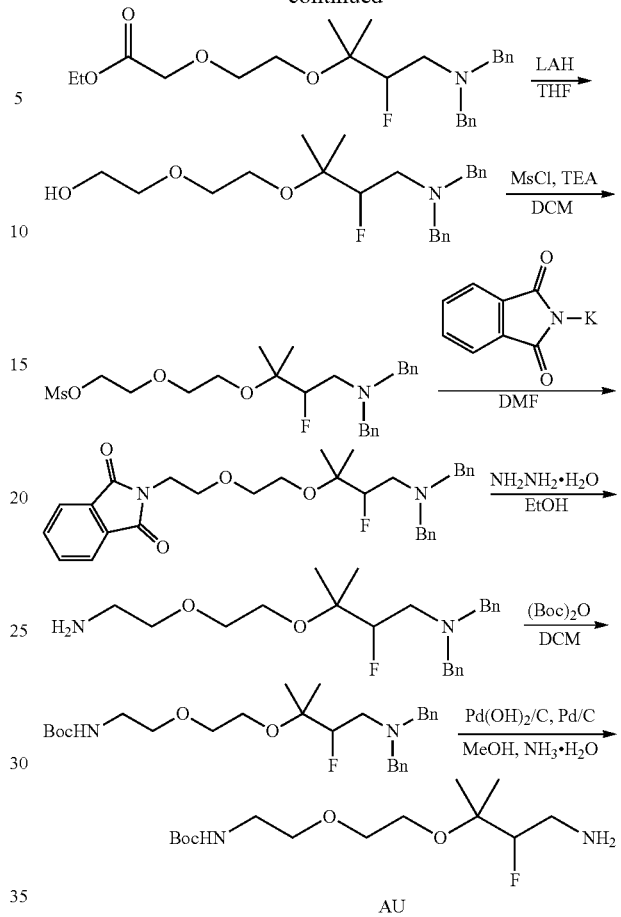

AU

Step 1—Ethyl 2-[2-[3-(dibenzylamino)-2-fluoro-1,1-dimethyl-propoxy]ethoxy]acetate To a solution of 2-[3-(dibenzylamino)-2-fluoro-1,1-dimethyl-propoxy]ethanol (4.00 g, 11.6 mmol, Intermediate AN) and Rh(OAc)$_2$ (128 mg, 579 umol) in DCM (80 mL) was added a solution of ethyl 2-diazoacetate (3.96 g, 34.7 mmol) in DCM (40 mL) dropwise at rt. The reaction mixture was stirred at rt for 20 h. On completion, the reaction mixture was diluted with H$_2$O (60 mL) and extracted with DCM (2×50 mL). The organic layer was dried with anhydrous Na$_2$SO$_4$, filtered and concentrated in vacuo to give the title compound (4.63 g, 93% yield) as a yellow oil. LC-MS (ESI$^+$) m/z 432.2 (M+H)$^+$.

Step 2—2-[2-[3-(Dibenzylamino)-2-fluoro-1,1-dimethyl-propoxy]ethoxy]ethanol

To a mixture of LiAlH$_4$ (611 mg, 16.1 mmol) in THF (20 mL) was added a solution of ethyl 2-[2-[3-(dibenzylamino)-2-fluoro-1,1-dimethyl-propoxy]ethoxy]acetate (4.63 g, 10.7 mmol) in THF (40 mL) dropwise at 0° C. The reaction mixture was stirred at 0° C. for 2 h. On completion, the reaction mixture was quenched with H$_2$O (0.55 mL) at 0° C. Then 15% NaOH solution (1.5 mL) was added to the reaction mixture. The mixture was filtered and the filtrate was concentrated in vacuo to give the title compound (3.53 g, 84% yield) as a yellow oil.

Step 3—2-[2-[3-(Dibenzylamino)-2-fluoro-1,1-dimethyl-propoxy]ethoxy]ethyl methanesulfonate To a solution of 2-[2-[3-(dibenzylamino)-2-fluoro-1,1-dimethyl-propoxy]ethoxy]ethanol (3.53 g, 9.06 mmol) and TEA (2.29 g, 22.7 mmol) in DCM (35 mL) was added MsCl (1.56 g, 13.6 mmol) dropwise at 0° C. The reaction mixture was stirred at rt for 1 hour. On completion, the mixture was quenched with H$_2$O (30 mL) and extracted with DCM (2×30 mL). The organic layer was washed with brine (50 mL), dried with anhydrous Na$_2$SO$_4$, filtered and concentrated in vacuo to give the title compound (4.50 g, 100% yield) as a yellow oil. $^1$H NMR (400 MHz, CDCl$_3$) δ 7.44-7.24 (m, 10H), 4.63-4.46 (m, 1H), 4.35-4.30 (m, 2H), 3.81-3.75 (m, 2H), 3.68-3.64 (m, 2H), 3.63-3.59 (m, 2H), 3.54-3.39 (m, 4H), 3.04 (s, 3H), 2.96-2.67 (m, 2H), 1.11 (s, 6H).

Step 4—2-[2-[2-[3-(Dibenzylamino)-2-fluoro-1,1-dimethyl-propoxy]ethoxy]ethyl]isoindoline-1,3-dione To a solution of 2-[2-[3-(dibenzylamino)-2-fluoro-1,1-dimethyl-propoxy]ethoxy]ethyl methane sulfonate (4.50 g, 9.62 mmol) in DMF (45 mL) was added (1,3-dioxoisoindolin-2-yl)potassium (2.67 g, 14.4 mmol). The reaction mixture was stirred at 80° C. for 3 h. On completion, the mixture was diluted with H$_2$O (30 mL) and extracted with EtOAc (3×40 mL). The organic layer was washed with brine (50 mL), dried over Na$_2$SO$_4$, filtered and concentrated in vacuo to give the title compound (5.90 g, 96% yield) as a yellowish oil. LC-MS (ESI$^+$) m/z 519.3 (M+H)$^+$.

Step 5—3-[2-(2-Aminoethoxy)ethoxy]-N,N-dibenzyl-2-fluoro-3-methyl-butan-1-amine To a solution of 2-[2-[2-[3-(dibenzylamino)-2-fluoro-1,1-dimethyl-propoxy]ethoxy]ethyl]isoindoline-1,3-dione (4.99 g, 9.62 mmol) in EtOH (60 mL) was added NH$_2$NH$_2$·H$_2$O (2.41 g, 48.1 mmol). The reaction mixture was stirred at 80° C. for 15 hours. On completion, the reaction mixture was filtered and the filtrate was concentrated in vacuo to remove solvent. The residue was diluted with DCM (30 mL), filtered and the filtrate was concentrated in vacuo to give the title compound (3.74 g, 100% yield) as a yellow oil. LC-MS (ESI$^+$) m/z 389.2 (M+H)$^+$.

Step 6—Tert-butyl N-[2-[2-[3-(dibenzylamino)-2-fluoro-1,1-dimethyl-propoxy]ethoxy]ethyl]carbamate To a solution of 3-[2-(2-aminoethoxy)ethoxy]-N,N-dibenzyl-2-fluoro-3-methyl-butan-1-amine (3.74 g, 9.63 mmol) in DCM (40 mL) was added (Boc)$_2$O (4.20 g, 19.3 mmol). The reaction mixture was stirred at rt for 3 hours. On completion, the reaction mixture was concentrated in vacuo to remove solvent. The residue was purified by reverse phase chromatography (0.1% NH$_3$·H$_2$O) to give the title compound (3.10 g, 66% yield) as a yellow oil. LC-MS (ESI$^+$) m/z 489.1 (M+H)$^+$.

Step 7—Tert-butyl N-[2-[2-(3-amino-2-fluoro-1,1-dimethyl-propoxy)ethoxy]ethyl]carbamate To a solution of tert-butyl N-[2-[2-[3-(dibenzylamino)-2-fluoro-1,1-dimethyl-propoxy]ethoxy]ethyl]carbamate (3.10 g, 6.34 mmol) in MeOH (30 mL) was added Pd/C (1.5 g, 10 wt %), Pd(OH)$_2$/C (1.5 g, 10 wt %) and NH$_3$·H$_2$O (910 mg, 6.49 mmol, 25 wt %). The reaction mixture was stirred at rt for 17 h under hydrogen atmosphere (15 psi pressure). On completion, the mixture was filtered and the filtrate was concentrated in vacuo to give the title compound (1.82 g, 93% yield) as a yellow oil. LC-MS (ESI$^+$) m/z 309.1 (M+H)$^+$.

Tert-butyl N-[2-[2-(3-amino-2-fluoro-propoxy)ethoxy]ethyl]carbamate (Intermediate AV)

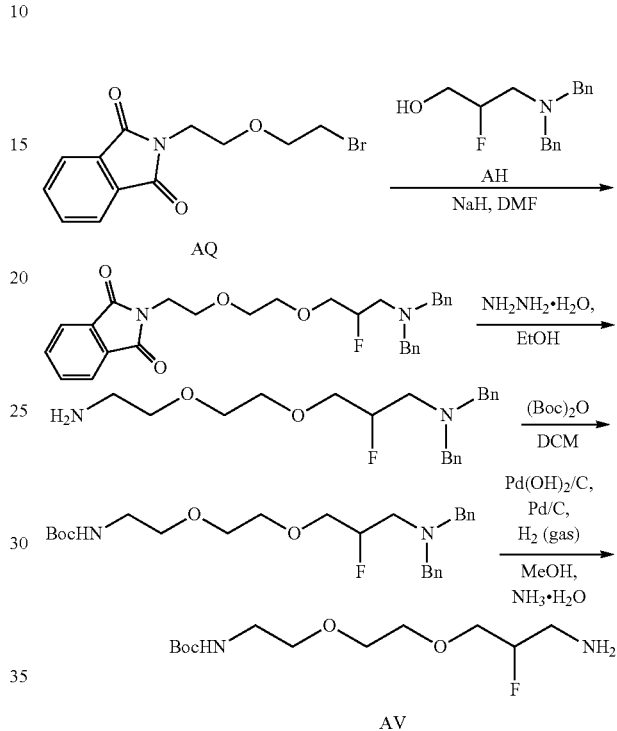

Step 1—2-[2-[2-[3-(Dibenzylamino)-2-fluoro-propoxy]ethoxy]ethyl]isoindoline-1,3-dione To a solution of 3-(dibenzylamino)-2-fluoro-propan-1-ol (1.00 g, 3.66 mmol, Intermediate AH) in DMF (15.0 mL) was added NaH (439 mg, 10.9 mmol, 60% dispersion in mineral oil) under 0° C. and the mixture was stirred at 0° C. for 30 minutes. Then 2-[2-(2-bromoethoxy)ethyl]isoindoline-1,3-dione (1.64 g, 5.49 mmol, Intermediate AQ) was added and the mixture was allowed to warm to rt and stirred 4 h. On completion, the mixture was quenched with H$_2$O (1 mL) and concentrated in vacuo to give the title compound (1.79 g, 80% yield) as yellow solid. LC-MS (ESI$^+$) m/z 491.3 (M+H)$^+$.

Step 2—3-[2-(2-Aminoethoxy)ethoxy]-N,N-dibenzyl-2-fluoro-propan-1-amine

To a solution of 2-[2-[2-[3-(dibenzylamino)-2-fluoro-propoxy]ethoxy]ethyl]isoindoline-1,3-dione (2.68 g, 5.46 mmol) in EtOH (30.0 mL) was added N$_2$H$_4$H$_2$O (5.58 g, 109 mmol, 5.42 mL, 98% purity). The reaction mixture was stirred at 80° C. for 40 hours. On completion, the mixture was filtered, and the filtrate was concentrated in vacuo. The solid was diluted with DCM (50 mL) and stirred for 15 minutes, filtered, and the organic layer was concentrated in vacuo to give the title compound (1.97 g, 80% yield) as a yellow oil. LC-MS (ESI$^+$) m/z 361.2 (M+H)$^+$.

Step 3—Tert-butyl N-[2-[2-[3-(dibenzylamino)-2-fluoro-prop oxy]ethoxy]ethyl]carbamate To a solution of 3-[2-(2-aminoethoxy)ethoxy]-N,N-dibenzyl-2-fluoro-propan-1-amine (1.97 g, 5.47 mmol) in DCM (20.0 mL) was added (Boc)₂O (2.39 g, 10.9 mmol, 2.51 mL) and the reaction mixture was stirred at rt for 16 hours. On completion, the mixture was concentrated in vacuo. The mixture was purified by reverse phase chromatography (0.1% NH₃.H₂O) to give the title compound (930 mg, 36% yield) as a yellow oil. LC-MS (ESI⁺) m/z 461.2 (M+H)⁺.

Step 4—Tert-butyl N-[2-[2-(3-amino-2-fluoro-propoxy)ethoxy]ethyl]carbamate

To a solution of tert-butyl N-[2-[2-[3-(dibenzylamino)-2-fluoro-propoxy]ethoxy]ethyl]carbamate (930 mg, 2.02 mmol) in MeOH (10.0 mL) and NH₃.H₂O (200 uL) was added Pd/C (500 mg, 10 wt %) and Pd(OH)₂/C (500 mg, 10 wt %) under nitrogen atmosphere. The suspension was degassed in vacuo and purged with hydrogen gas several times. The mixture was stirred under hydrogen atmosphere (50 psi pressure) at rt for 16 hours. On completion, the mixture was filtered and concentrated in vacuo to give the title compound (560 mg, 98% yield) as a yellow oil. LC-MS (ESI⁺) m/z 281.1 (M+H)⁺.

Tert-butyl N-[2-(3-amino-2-fluoro-1,1-dimethyl-propoxy)ethyl]carbamate (Intermediate AW)

Step 1—2-[3-(Dibenzyl amino)-2-fluoro-1,1-dimethyl-propoxy]ethyl methanesulfonate To a mixture of 2-[3-(dibenzylamino)-2-fluoro-1,1-dimethyl-propoxy]ethanol (1.50 g, 4.34 mmol, Intermediate AN) and Et₃N (1.32 g, 13.0 mmol, 1.81 mL) in DCM (10 mL) was added MsCl (746 mg, 6.51 mmol). The mixture was stirred at rt for 2 hours. On completion, the mixture was quenched with water (15 mL) and extracted with DCM (2×20 mL). The organic layer was washed with brine (10 mL), dried over anhydrous Na₂SO₄, then filtered and concentrated in vacuo to give the title compound (1.90 g, 98% yield) as a yellow oil. LC-MS (ESI⁺) m/z 424.2 (M+H)⁺.

Step 2—2-[2-[3-(Dibenzylamino)-2-fluoro-1,1-dimethyl-propoxy]ethyl]isoindoline-1,3-

To a solution of 2-[3-(dibenzylamino)-2-fluoro-1,1-dimethyl-propoxy]ethyl methanesulfonate (1.70 g, 4.01 mmol) in DMF (20 mL) was added (1,3-dioxoisoindolin-2-yl) potassium (817 mg, 4.42 mmol). The mixture was heated at 60° C. for 16 hours. On completion, the mixture was diluted with water (10 mL) and extracted with EtOAc (2×50 mL). The organic layer was washed with brine (20 mL), dried over anhydrous Na₂SO₄, then filtered and concentrated in vacuo to give the title compound (1.90 g, 99% yield) as a yellow oil. LC-MS (ESI⁺) m/z 475.2 (M+H)⁺.

Step 3—3-(2-Aminoethoxy)-N,N-dibenzyl-2-fluoro-3-methyl-butan-1-amine

To a solution of 2-[2-[3-(dibenzylamino)-2-fluoro-1,1-dimethyl-propoxy]ethyl]isoindoline-1,3-dione (1.90 g, 4.00 mmol) in EtOH (20 mL) was added NH₂NH₂.H₂O (2.05 g, 40.0 mmol, 1.99 mL, 98% purity). The reaction mixture was stirred at 80° C. for 16 hours. On completion, the mixture was filtered and the filtrate was concentrated in vacuo to give the title compound (2.50 g, crude) as a white solid. LC-MS (ESI⁺) m/z 345.2 (M+H)⁺.

Step 4—Tert-butyl N-[2-[3-(dibenzylamino)-2-fluoro-1,1-dimethyl-propoxy]ethyl]

To a solution of 3-(2-aminoethoxy)-N,N-dibenzyl-2-fluoro-3-methyl-butan-1-amine (1.00 g, 2.90 mmol) in MeOH (10 mL) was added (Boc)₂O (1.27 g, 5.81 mmol). The mixture was stirred at rt for 2 hours. On completion, the mixture was concentrated in vacuo. The residue was purified by silica gel chromatography to give the title compound (1.29 g, 90% yield). ¹H NMR (400 MHz, CDCl₃) δ 7.44-7.22 (m, 10H), 4.66-4.41 (m, 2H), 3.82 (d, J=13.6 Hz, 2H), 3.60 (d, J=13.6 Hz, 2H), 3.41-3.24 (m, 2H), 3.18-3.00 (m, 2H), 2.99-2.81 (m, 1H), 2.77-2.61 (m, 1H), 1.47 (s, 9H), 1.13-1.06 (m, 6H); LC-MS (ESI⁺) m/z 445.3 (M+H)⁺.

Step 5—Tert-butyl N-[2-(3-amino-2-fluoro-1,1-dimethyl-propoxy)ethyl]carbamate To a solution of tert-butyl N-[2-[3-(dibenzylamino)-2-fluoro-1,1-dimethyl-propoxy]ethyl]carbamate (1.3 g, 2.9 mmol) in MeOH (15 mL) was added Pd/C (0.5 g, 10 wt %), Pd(OH)₂/C (0.5 g, 10 wt %) and NH₃.H₂O (100 uL, 30 wt %, catalytic amount). The mixture was degassed and purged with hydrogen gas three times. The mixture was stirred at rt for 24 hours under hydrogen gas (50 psi pressure). On completion, the mixture was filtered and concentrated in vacuo to give the title compound (700 mg, 90% yield) as a

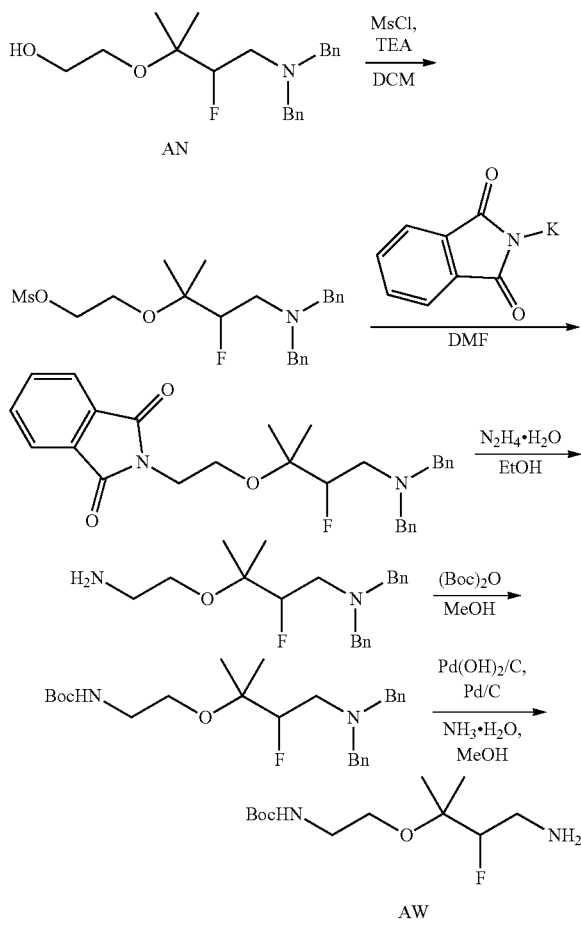

colorless oil. $^1$H NMR (400 MHz, CDCl$_3$) δ 4.93 (s, 1H), 3.57-3.43 (m, 2H), 3.38-3.19 (m, 2H), 3.13-2.91 (m, 2H), 2.38-2.30 (m, 2H), 1.46 (s, 9H), 1.22 (dd, J=1.2, 10.6 Hz, 6H); LC-MS (ESI$^+$) m/z 265.1 (M+H)$^+$.

Tert-butyl N-[2-(3-amino-2-fluoro-propoxy)ethyl]carbamate (Intermediate AX)

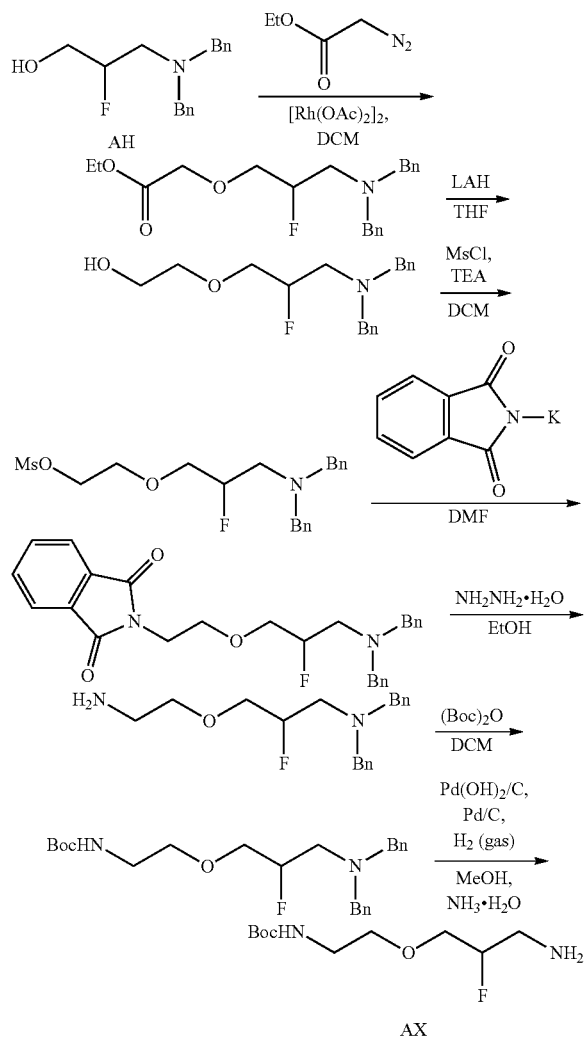

Step 1—Ethyl 2-[3-(dibenzylamino)-2-fluoro-propoxy]acetate

To a solution of 3-(dibenzylamino)-2-fluoro-propan-1-ol (5.00 g, 18.2 mmol, Intermediate AH) in DCM (100 mL) was added [Rh(OAc)$_2$]$_2$ (80.8 mg, 365 umol) in DCM (50.0 mL) then and ethyl 2-diazoacetate (6.26 g, 54.8 mmol, 5.74 mL) was added dropwise. The reaction mixture was stirred at rt for 60 h. On completion, the mixture was concentrated in vacuo. The mixture was purified by reverse phase column (0.1% NH$_3$.H$_2$O) to give the title compound (7.23 g, 78% yield) as a yellow oil. $^1$H NMR (400 MHz, CDCl$_3$) δ 7.42-7.25 (m, 10H), 4.92-4.71 (m, 1H), 4.28-4.18 (m, 2H), 4.13-4.08 (m, 2H), 3.79-3.53 (m, 6H), 2.82-2.71 (m, 2H), 1.30 (t, J=7.2 Hz, 3H).

Step 2—2-[3-(Dibenzylamino)-2-fluoro-propoxy]ethanol

To a solution of LiAlH$_4$ (1.15 g, 30.1 mmol) in THF (70.0 mL) was added a solution of ethyl 2-[3-(dibenzylamino)-2-fluoro-propoxy]acetate (7.23 g, 20.1 mmol) dissolved in THF (30.0 mL) dropwise at 0° C. The reaction mixture was stirred at 0° C. for 2 h. On completion, the mixture was quenched with water (3 mL), then 15% NaOH (3 mL) was added until no precipitate formed. The reaction mixture was then filtered and the filtrate was concentrated in vacuo to give the title compound (5.88 g, 92% yield) as a yellow solid. $^1$H NMR (400 MHz, CDCl$_3$) δ 7.39-7.26 (m, 10H), 4.86-4.64 (m, 1H), 3.71-3.61 (m, 8H), 3.58-3.51 (m, 3H), 2.80-2.70 (m, 2H).

Step 3—2-[3-(Dibenzylamino)-2-fluoro-propoxy]ethyl methanesulfonate

To a solution of 2-[3-(dibenzylamino)-2-fluoro-propoxy]ethanol (2.00 g, 6.30 mmol) and TEA (1.28 g, 12.6 mmol, 1.75 mL) in DCM (20.0 mL) was added MsCl (866 mg, 7.56 mmol, 585 uL) at 0° C. The reaction mixture was then allowed to warm to rt and stirred for 1 hr. On completion, the mixture was diluted with DCM (30 mL), then washed with H$_2$O (3×30 mL). The organic layer was dried over anhydrous Na$_2$SO$_4$, filtered and concentrated in vacuo to give the title compound (2.27 g, 90% yield) as a yellow solid. $^1$H NMR (400 MHz, CDCl$_3$) δ 7.41-7.25 (m, 10H), 4.83-4.63 (m, 1H), 4.33-4.28 (m, 2H), 3.69-3.66 (m, 6H), 3.64-3.55 (m, 2H), 2.99 (s, 3H), 2.81-2.69 (m, 2H)

Step 4—2-[2-[3-(Dibenzyl amino)-2-fluoro-propoxy]ethyl]isoindoline-1,3-dione

To a solution of 2-[3-(dibenzylamino)-2-fluoro-propoxy]ethyl methanesulfonate (2.27 g, 5.74 mmol) in DMF (20.0 mL) was added (1,3-dioxoisoindolin-2-yl)potassium (1.59 g, 8.61 mmol) and the reaction mixture was stirred at 80° C. for 3 h. On completion, the mixture was diluted with water (50 mL) then extracted with EtOAc (3×30 mL). The organic layers were dried over anhydrous Na$_2$SO$_4$, filtered and concentrated in vacuo to give the title compound (2.56 g, 80% yield) as a yellow oil. LC-MS (ESI) m/z 447.2 (M+H)$^+$.

Step 5—3-(2-Aminoethoxy)-N,N-dibenzyl-2-fluoro-propan-1-amine

To a solution of 2-[2-[3-(dibenzylamino)-2-fluoro-propoxy]ethyl]isoindoline-1,3-dione (2.56 g, 5.73 mmol) in EtOH (25.0 mL) was added N$_2$H$_4$.H$_2$O (1.46 g, 28.6 mmol, 1.42 mL, 98% purity) and the reaction mixture was stirred at 80° C. for 16 h. On completion, the mixture was filtered, and the filtrate was concentrated in vacuo. The resulting residue was diluted with DCM (50 mL), stirred for 15 min, filtered, and the filtrate was concentrated in vacuo to give the title compound (1.50 g, 82% yield) as a yellow oil. LC-MS (ESI$^+$) m/z 317.1 (M+H)$^+$.

Step 6—Tert-butyl N-[2-[3-(dibenzylamino)-2-fluoro-propoxy]ethyl]carbamate

To a solution of 3-(2-aminoethoxy)-N,N-dibenzyl-2-fluoro-propan-1-amine (1.50 g, 4.74 mmol) in DCM (15.0 mL) was added (Boc)$_2$O (1.55 g, 7.11 mmol, 1.63 mL) and the reaction mixture was stirred at rt for 16 h. On completion, the mixture was concentrated in vacuo. The mixture was purified by reverse phase chromatography (0.1% NH₃.H₂O) to give the title compound (1.37 g, 67% yield) as a yellow oil. LC-MS (ESI⁺) m/z 417.2 (M+H)⁺.

Step 7—Tert-butyl N-[2-(3-amino-2-fluoro-propoxy)ethyl]carbamate

To a solution of tert-butyl N-[2-[3-(dibenzylamino)-2-fluoro-propoxy]ethyl]carbamate (1.30 g, 3.12 mmol) in a solvent mixed solution of MeOH (15.0 mL) and NH₃.H₂O (300 uL) was added Pd/C (600 mg, 10 wt %) and Pd(OH)₂/C (600 mg, 10 wt %) under nitrogen atmosphere. The suspension was degassed under vacuum and purged with hydrogen gas several times. The mixture was stirred under hydrogen atmosphere (50 psi pressure) at rt for 16 h. On completion, the mixture was filtered and the filtrate was concentrated in vacuo to give the title compound (730 mg, 99% yield) as a yellow oil. LC-MS (ESI⁺) m/z 237.0 (M+H)⁺.

Tert-butyl N-[2-(3-amino-2-fluoro-1-methyl-propoxy)ethyl]carbamate (Intermediate AY)

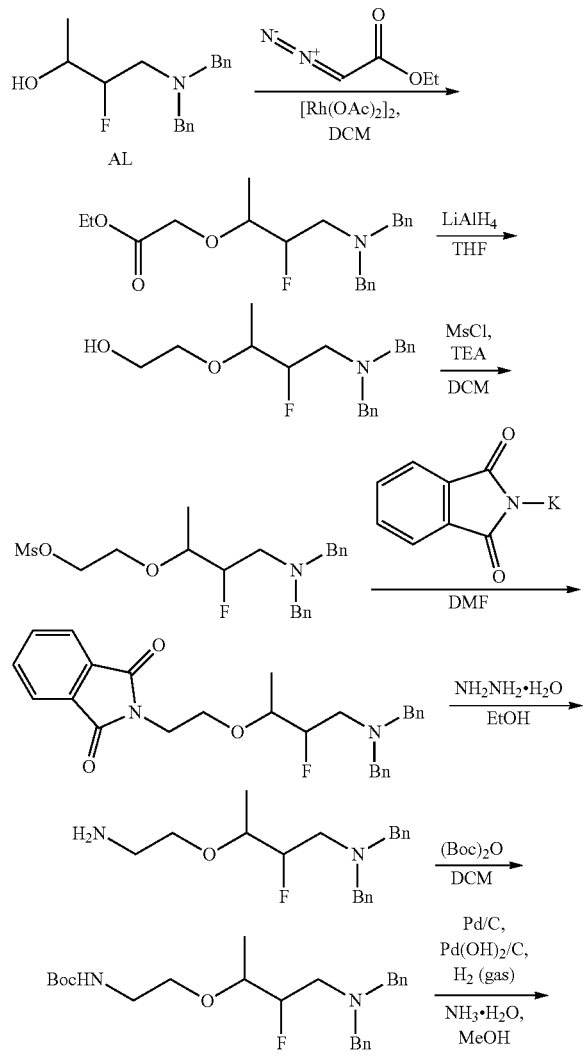

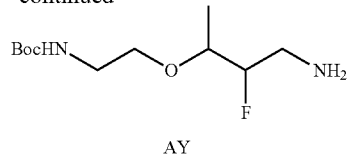

AY

Step 1—Ethyl 2-[3-(dibenzylamino)-2-fluoro-1-methyl-propoxy]acetate

To a mixture of 4-(dibenzylamino)-3-fluoro-butan-2-ol (1.00 g, 3.48 mmol, Intermediate AL) and [Rh(OAc)₂]₂ (15.3 mg, 69.6 umol) in DCM (20 mL) was added a solution of ethyl 2-diazoacetate (1.19 g, 10.4 mmol) in DCM (10 mL) dropwise. The reaction mixture was stirred at rt for 20 h. On completion, the reaction mixture was poured into 30 mL of water and extracted with DCM (3×30 mL). The combined organic layer was dried over Na₂SO₄, filtered and concentrated in vacuo to give a residue. The residue was purified by reverse phase chromatography (0.1% NH₃.H₂O) to give the title compound (890 mg, 67% yield) as a light yellow oil. ¹H NMR (400 MHz, CDCl₃) δ 7.45-7.22 (m, 10H), 4.83-4.50 (m, 1H), 4.25-4.00 (m, 4H), 3.81-3.57 (m, 5H), 2.99-2.75 (m, 2H), 1.31-1.26 (m, 3H), 1.12-1.02 (m, 3H); LC-MS (ESI⁺) m/z 374.1 (M+H)⁺.

Step 2—2-[3-(Dibenzylamino)-2-fluoro-1-methyl-propoxy]ethanol

To a mixture of ethyl 2-[3-(dibenzylamino)-2-fluoro-1-methyl-propoxy]acetate (890 mg, 2.38 mmol) in THF (3 mL) was added LiAlH₄ (138 mg, 3.57 mmol, 98% purity) at 0° C. The reaction mixture was then allowed to warm to rt and stirred 30 min. On completion, the reaction mixture was quenched with water (0.5 mL) and NaOH solution (15%, 0.5 mL) at 0° C. Then the mixture was filtered and the filtrate was concentrated in vacuo to give the title compound (730 mg, 95% yield) as a light yellow oil. LC-MS (ESI⁺) m/z 332.1 (M+H)⁺.

Step 3—2-[3-(Dibenzylamino)-2-fluoro-1-methyl-propoxy]ethyl methanesulfonate

To a mixture of 2-[3-(dibenzylamino)-2-fluoro-1-methyl-propoxy]ethanol (730 mg, 2.20 mmol) and TEA (668 mg, 6.61 mmol) in DCM (10 mL) was added MsCl (378 mg, 3.30 mmol) at 0° C. The reaction mixture was allowed to warm to rt and stirred for 2 h. On completion, the reaction mixture was diluted with water (20 mL) and extracted with DCM (3×50 mL). The combined organic layer was dried over Na₂SO₄, filtered and concentrated in vacuo to give the title compound (900 mg, 100% yield) as a light yellow oil. LC-MS (ESI⁺) m/z 410.1 (M+H)⁺.

Step 4—2-[2-[3-(Dibenzylamino)-2-fluoro-1-methyl-propoxy]ethyl]isoindoline-1,3-dione To a mixture of 2-[3-(dibenzylamino)-2-fluoro-1-methyl-propoxy]ethyl methanesulfonate (900 mg, 2.20 mmol) in DMF (10 mL) was added (1,3-dioxoisoindolin-2-yl)potassium (610 mg, 3.30 mmol). The reaction mixture was stirred at 100° C. for 3 h. On completion, the reaction mixture was concentrated in vacuo to give the title compound (1.00 g, 95% yield) as a light yellow solid. LC-MS (ESI⁺) m/z 461.2 (M+H)⁺.

Step 5—3-(2-Aminoethoxy)-N,N-dibenzyl-2-fluoro-butan-1-amine

To a mixture of 2-[2-[3-(dibenzylamino)-2-fluoro-1-methyl-propoxy]ethyl]isoindoline-1,3-dione (1.00 g, 2.17 mmol) in EtOH (15 mL) was added NH$_2$NH$_2$·H$_2$O (869 mg, 17.3 mmol). The reaction mixture was stirred at 80° C. for 20 h. On completion, the reaction mixture was filtered and concentrated in vacuo. The residue was poured into 30 mL of DCM, filtered and concentrated in vacuo to give the title compound (800 mg, 73% purity, 75% yield) as a light yellow solid. LC-MS (ESI$^+$) m/z 333.1 (M+H)$^+$.

Step 6—Tert-butyl N-[2-[3-(dibenzylamino)-2-fluoro-1-methyl-prop oxy]ethyl]carbamate To a mixture of 3-(2-aminoethoxy)-N,N-dibenzyl-2-fluoro-butan-1-amine (800 mg, 2.42 mmol) in DCM (10 mL) was added (Boc)$_2$O (1.06 g, 4.84 mmol). The reaction mixture was stirred at rt for 2 h. On completion, the reaction mixture was concentrated in vacuo. The residue was purified by reverse phase chromatography (0.1% NH$_3$.H$_2$O) to give the title compound (520 mg, 48% yield) as a light yellow oil. $^1$H NMR (400 MHz, CDCl$_3$) δ 7.42-7.23 (m, 10H), 4.87-4.41 (m, 2H), 3.81-3.68 (m, 2H), 3.68-3.59 (m, 2H), 3.59-3.44 (m, 2H), 3.39-3.24 (m, 1H), 3.19 (d, J=5.2 Hz, 2H), 2.91-2.65 (m, 2H), 1.48-1.45 (m, 9H), 1.07-0.98 (m, 3H); LC-MS (ESI$^+$) m/z 431.2 (M+H)$^+$.

Step 7—Tert-butyl N-[2-(3-amino-2-fluoro-1-methyl-propoxy)ethyl]carbamate

To a mixture of tert-butyl N-[2-[3-(dibenzylamino)-2-fluoro-1-methyl-propoxy]ethyl]carbamate (520 mg, 1.21 mmol), Pd/C (300 mg, 10 wt %) and Pd(OH)$_2$/C (300 mg, 10 wt %) in MeOH (10 mL) was added NH$_3$.H$_2$O (169 mg, 1.21 mmol 25% wt %) under hydrogen atmosphere (15 psi pressure). The reaction mixture was stirred at rt for 16 h. On completion, the reaction mixture was filtered and concentrated in vacuo to give the title compound (280 mg, 100% yield) as a light yellow oil. $^1$H NMR (400 MHz, CDCl$_3$) δ 5.09-4.78 (m, 1H), 4.41-4.07 (m, 1H), 3.63-3.49 (m, 2H), 3.47-3.38 (m, 1H), 3.26-3.16 (m, 2H), 2.96-2.77 (m, 2H), 1.70-1.60 (m, 2H), 1.38 (s, 9H), 1.14-1.10 (m, 3H).

Tert-butyl N-[2-[2-(3-amino-2-fluoro-1-methyl-propoxy)ethoxy]ethyl]carbamate (Intermediate AZ)

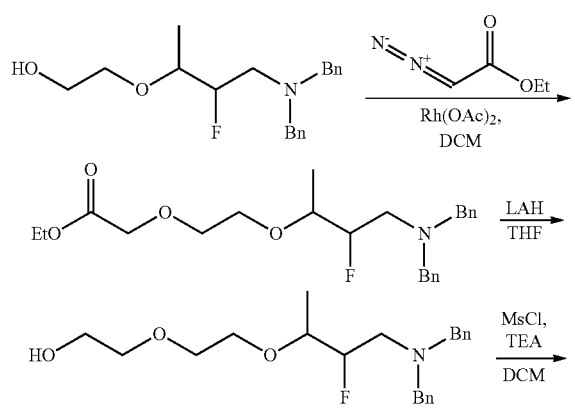

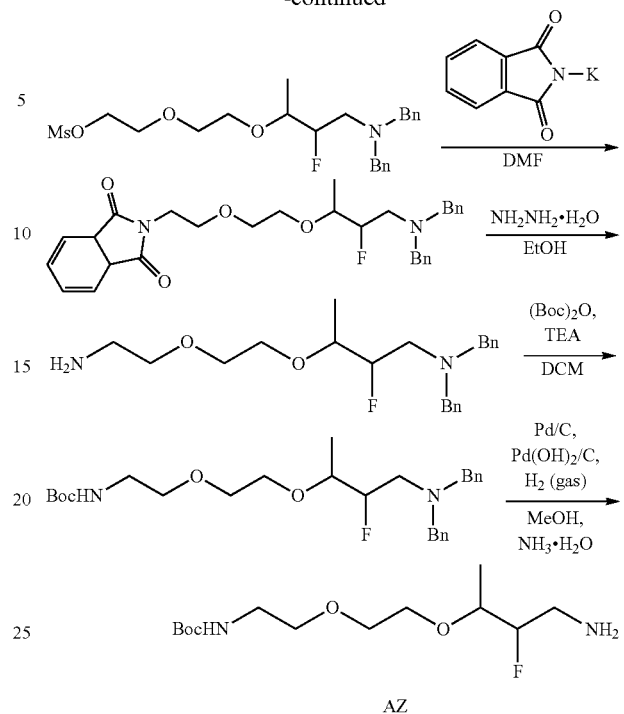

Step 1—Ethyl 2-[2-[3-(dibenzylamino)-2-fluoro-1-methyl-propoxy]ethoxy]acetate To a solution of 2-[3-(dibenzylamino)-2-fluoro-1-methyl-propoxy]ethanol (3.30 g, 9.96 mmol, synthesized via Steps 1-2 of Intermediate AY) in DCM (50 mL) was added Rh(OAc)$_2$ (44 mg, 199 umol), then a solution of ethyl 2-diazoacetate (3.41 g, 29.9 mmol, 3.13 mL) in DCM (50 mL) was added dropwise. The mixture was stirred at rt for 20 h. On completion, the mixture was concentrated in vacuo and the residue was purified by silica gel chromatography to give the title compound (2.70 g, 58% yield) as a colorless oil. LC-MS (ESI$^+$) m/z 418.1 (M+H)$^+$.

Step 2—2-[2-[3-(Dibenzylamino)-2-fluoro-1-methyl-propoxy]ethoxy]ethanol

To a solution of ethyl 2-[2-[3-(dibenzylamino)-2-fluoro-1-methyl-propoxy]ethoxy]acetate (1.00 g, 2.40 mmol) in THF (30 mL) was added LiAlH$_4$ (136 mg, 3.59 mmol). The mixture was stirred at 0° C. for 1 hr. On completion, the mixture was quenched by adding water (1 mL), 15% NaOH (3 mL) then more water (1 mL). A large quantity of white precipitate was formed, the mixture was filtered and the filtrate was concentrated in vacuo to give the title compound (880 mg, 93% yield) as a colorless oil. LC-MS (ESI$^+$) m/z 376.2 (M+H)$^+$.

Step 3—2-[2-[3-(Dibenzylamino)-2-fluoro-1-methyl-propoxy]ethoxy]ethyl methanesulfonate To a solution of 2-[2-[3-(dibenzylamino)-2-fluoro-1-methyl-propoxy]ethoxy]ethanol (2.40 g, 6.39 mmol) in DCM (25 mL) was added Et$_3$N (1.94 g, 19.2 mmol, 2.67 mL) and MsCl (1.10 g, 9.59 mmol, 742 uL). The mixture was stirred at 0° C. for 1 hr. On completion, the reaction was quenched with water (20 mL) and extracted with DCM (2×30 mL). The combined organic layer was washed with brine, dried over anhydrous Na$_2$SO$_4$, filtered and concentrated in vacuo to give the title compound (2.90 g, 98% yield) as a yellow oil. LC-MS (ESI$^+$) m/z 454.1 (M+H)$^+$.

Step 4—2-[2-[2-[3-(Dibenzylamino)-2-fluoro-1-methyl-propoxy]ethoxy]ethyl]isoindoline-1,3-dione To a solution of 2-[2-[2-[3-(dibenzylamino)-2-fluoro-1-methyl-propoxy]ethoxy]ethyl methanesulfonate (2.90 g, 6.39 mmol) in DMF (30 mL) was added (1,3-dioxoisoindolin-2-yl)potassium (1.30 g, 7.03 mmol). The mixture was stirred at 60° C. for 10 h. On completion, the mixture was diluted with water (50 mL) and extracted with EtOAc (2×100 mL). The combined organic layer was washed with brine (50 mL), dried over anhydrous Na$_2$SO$_4$, then filtered and concentrated in vacuo to give the title compound (3.8 g) as a light yellow oil. LC-MS (ESI$^+$) m/z 505.2 (M+H)$^+$.

Step 5—3-[2-(2-Aminoethoxy)ethoxy]-N,N-dibenzyl-2-fluoro-butan-1-amine

To a solution of 2-[2-[2-[3-(dibenzylamino)-2-fluoro-1-methyl-propoxy]ethoxy]ethyl]isoindoline-1,3-dione (3.80 g, 7.53 mmol) in EtOH (50 mL) was added NH$_2$NH$_2$.H$_2$O (3.85 g, 75.3 mmol, 3.73 mL, 98% purity). The mixture was stirred at 90° C. for 3 h. On completion, the mixture was concentrated in vacuo to give the title compound (3.00 g, 100%) as a white solid. LC-MS (ESI$^+$) m/z 375.1 (M+H)$^+$.

Step 6—Tert-butyl N-[2-[2-[3-(dibenzylamino)-2-fluoro-1-methyl-prop oxy]ethoxy]ethyl]carbamate To a solution of 3-[2-(2-aminoethoxy)ethoxy]-N,N-dibenzyl-2-fluoro-butan-1-amine (3.00 g, 8.01 mmol) in MeOH (30 mL) was added (Boc)$_2$O (3.50 g, 16.02 mmol, 3.68 mL). The mixture was stirred at rt for 16 h. On completion, the mixture was concentrated in vacuo and the residue was purified by silica gel chromatography to give the title compound (4.00 g, 100%) as a white solid. LC-MS (ESI$^+$) m/z 475.2 (M+H)$^+$.

Step 7—Tert-butyl N-[2-[2-(3-amino-2-fluoro-1-methyl-propoxy)ethoxy]ethyl]carbamate To a solution of tert-butyl N-[2-[2-[3-(dibenzylamino)-2-fluoro-1-methyl-propoxy]ethoxy]ethyl]carbamate (2.00 g, 4.21 mmol) in MeOH (20 mL) was added Pd/C (400 mg, 10 wt %), Pd(OH)$_2$/C (400 mg, 10 wt %), NH$_3$.H$_2$O (404 mg, 3.46 mmol, 30 wt %). The suspension was degassed and purged with hydrogen gas three times. The mixture was stirred under hydrogen atmosphere (15 psi pressure) at rt for 36 h. On completion, the mixture was filtered and the filtrate was concentrated in vacuo. The residue was purified by silica gel chromatography to give the title compound (400 mg, 32% yield) as a colorless oil. $^1$H NMR (400 MHz, CDCl$_3$) δ 5.36-5.13 (m, 1H), 4.54-4.29 (m, 1H), 3.79-3.46 (m, 7H), 3.33 (s, 2H), 3.08-2.73 (m, 2H), 1.71 (s, 2H), 1.57-1.38 (m, 9H), 1.36-1.14 (m, 3H).

Tert-butyl N-[2-[2-[2-[2-(3-amino-2-fluoro-propoxy)ethoxy]ethoxy]ethoxy]ethyl]carbamate (Intermediate BA)

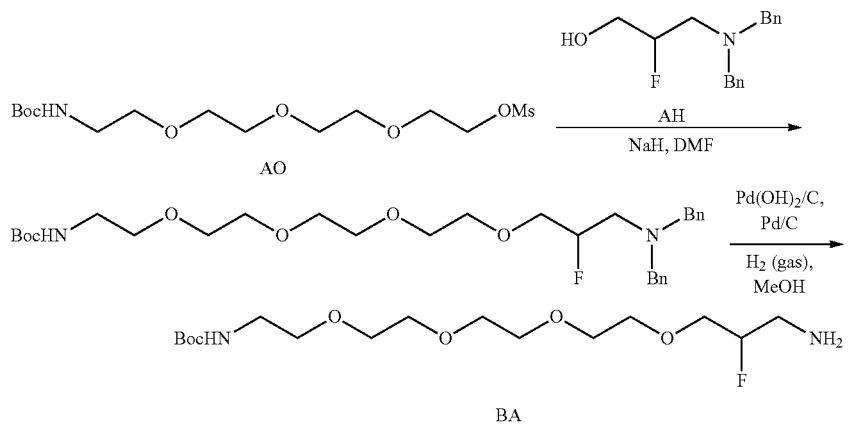

Step 1—Tert-butyl N-[2-[2-[2-[2-[3-(dibenzylamino)-2-fluoro-propoxy]ethoxy]ethoxy]ethoxy]ethyl]-carbamate To a solution of 3-(dibenzylamino)-2-fluoro-propan-1-ol (550 mg, 2.01 mmol, Intermediate AH) in N,N-dimethylformamide (16 mL) was added sodium hydroxide (241 mg, 6.04 mmol, 60% dispersion in mineral oil). The mixture was stirred at 0° C. for 30 minutes then 2-[2-[2-[2-(tert-butoxycarbonyl amino) ethoxy]ethoxy]-ethoxy]ethyl methanesulfonate (747 mg, 2.01 mmol, Intermediate AO) was added. Then, the reaction mixture was allowed to warm to rt and stirred for 4.5 hours under nitrogen atmosphere. On completion, the reaction mixture was quenched by addition of ice water (30 mL) and extracted with ethyl acetate (3×20 mL). The organic phase was collected, dried over anhydrous sodium sulfate, filtered and concentrated in vacuo to get a residue. The residue was purified by reversed phase chromatography (0.1% NH$_3$.H$_2$O) to give the title compound (600 mg, 54% yield) as a colorless gum. $^1$H NMR (400 MHz, CDCl$_3$) δ 7.40-7.23 (m, 10H), 5.08 (m, 1H), 4.89-4.70

(m, 1H), 3.69-3.60 (m, 17H), 3.57-3.52 (m, 3H), 3.36-3.29 (m, 2H), 2.77 (d, J=5.4 Hz, 1H), 2.72 (d, J=5.4 Hz, 1H), 1.46 (s, 9H).

Step 2—Tert-butyl N-[2-[2-[2-[2-(3-amino-2-fluoro-propoxy)ethoxy]ethoxy]ethoxy]ethyl]carbamate To a solution of tert-butyl N-[2-[2-[2-[2-[3-(dibenzylamino)-2-fluoro-propoxy]ethoxy]ethoxy]-ethyl]carbamate (600 mg, 1.09 mmol) in methanol (20 mL) was added Pd/C (300 mg, 10 wt %) and Pd(OH)$_2$/C (300 mg, 10 wt %) under nitrogen gas atmosphere. The suspension was degassed under vacuum and purged with hydrogen gas several times. The mixture was stirred under hydrogen gas (15 psi pressure) at rt for 18 h. On completion, the reaction mixture was filtered through a pad of celite and the filter cake was washed with methanol (3×10 mL). The filtrate was concentrated in vacuo to give the title compound (310 mg, 76% yield) as a colorless oil. LC-MS (ESI$^+$) m/z 369.2 (M+H)$^+$.

Tert-butyl N-[2-[2-[2-[2-(3-amino-2-fluoro-1-methyl-propoxy)ethoxy]ethoxy]ethoxy]ethyl]carbamate (Intermediate BB)

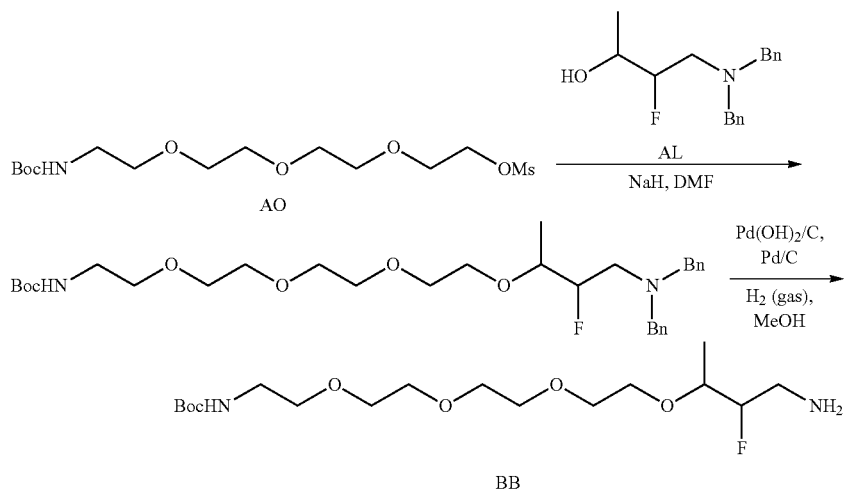

Step 1—Tert-butyl N-[2-[2-[2-[2-[3-(dibenzylamino)-2-fluoro-1-methyl-prop oxy]ethoxy]ethoxy]ethoxy]ethyl]carbamate To a solution of 4-(dibenzylamino)-3-fluoro-butan-2-ol (476 mg, 1.66 mmol, Intermediate AL) in DMF (8 mL) was added NaH (199 mg, 4.97 mmol) at 0° C. for 0.5 h. Then 2-[2-[2-[2-(tert-butoxycarbonylamino)ethoxy]ethoxy]ethoxy]ethyl methanesulfonate (800 mg, 2.15 mmol, Intermediate AO) was added into the above mixture. The reaction mixture allowed to warm to rt and stirred for 17 hrs. On completion, the reaction mixture was quenched with H$_2$O (20 mL) and extracted with EA (3×20 mL). The organic layer was dried with Na$_2$SO$_4$, filtered and the filtrate was concentrated in vacuo. The residue was purified by reverse phase chromatography (0.1% NH$_3$.H$_2$O) to give the title compound (362 mg, 29% yield) as a yellow oil. LC-MS (ESI$^+$) m/z 563.1 (M+H)$^+$.

Step 2—Tert-butyl N-[2-[2-[2-[2-(3-amino-2-fluoro-1-methyl-propoxy)ethoxy]ethoxy]ethoxy]ethyl]carbamate To a solution of tert-butyl N-[2-[2-[2-[2-[3-(dibenzylamino)-2-fluoro-1-methyl-propoxy]ethoxy]ethoxy]ethoxy]ethyl]carbamate (430 mg, 764 umol) in MeOH (10 mL) was added Pd/C (200 mg, wt %), Pd(OH)$_2$/C (200 mg, wt %) and NH$_3$.H$_2$O (182 mg, 30 wt %, 1.30 mmol). The suspension was degassed and purged with hydrogen gas three times. The reaction mixture was stirred at rt for 17 h under hydrogen atmosphere (50 psi pressure). On completion, the reaction mixture was filtered and the filtrate was concentrated in vacuo to give the title compound (250 mg, 86% yield) as a yellow oil. LC-MS (ESI$^+$) m/z 383.1 (M+H)$^+$.

Tert-butyl N-[2-[2-[2-[2-(3-amino-2-fluoro-1,1-dimethyl-propoxy)ethoxy]ethoxy]ethoxy]ethyl]carbamate (Intermediate BC)

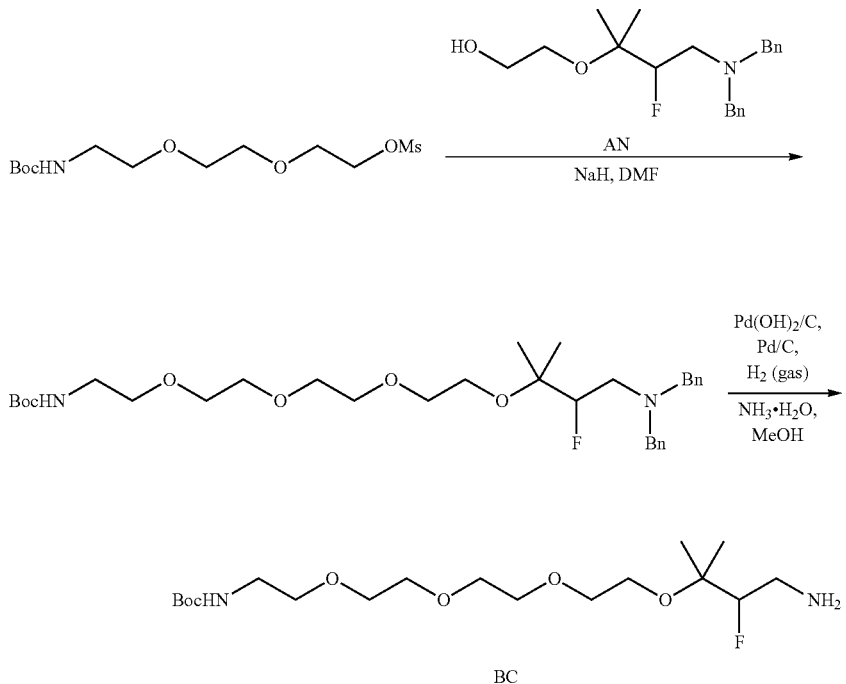

BC

Step 1—Tert-butyl N-[2-[2-[2-[2-[3-(dibenzylamino)-2-fluoro-1,1-dimethyl-propoxy]ethoxy]ethoxy]ethoxy]ethyl]carbamate To a solution of 2-[3-(dibenzylamino)-2-fluoro-1,1-dimethyl-propoxy]ethanol (800 mg, 2.32 mmol, Intermediate AN) in DMF (12 mL) was added NaH (277 mg, 6.95 mmol, 60% oil dispersion) at 0° C. and the mixture was stirred at 0° C. for 0.5 h. Then 2-[2-[2-(tert-butoxycarbonylamino)ethoxy]ethoxy]ethyl methanesulfonate (834 mg, 2.55 mmol, synthesized via Step 1 of Intermediate AM) was added and the mixture was allowed to warm to rt and stirred for 5 hrs. On completion, the reaction mixture was quenched with water (20 mL) and extracted with EtOAc (3×30 mL). The combined organic layer was dried over $Na_2SO_4$, filtered and concentrated in vacuo to give a residue. The residue was purified by reverse phase chromatography (0.1% $NH_3 \cdot H_2O$) to give the title compound (700 mg, 49% yield) as a colorless oil. LC-MS (ESI+) m/z 577.2 (M+H)+.

Step 2—Tert-butyl N-[2-[2-[2-[2-(3-amino-2-fluoro-1,1-dimethyl-propoxy)ethoxy]ethoxy]ethoxy]ethyl]carbamate To a solution of tert-butyl N-[2-[2-[2-[2-[3-(dibenzylamino)-2-fluoro-1,1-dimethyl-propoxy]ethoxy]ethoxy]ethoxy]ethyl]carbamate (450 mg, 780 umol) in MeOH (10 mL) was added $Pd(OH)_2/C$ (150 mg, 10 wt %), Pd/C (150 mg, 10 wt %) and $NH_3 \cdot H_2O$ (455 mg, 4.93 mmol, 38 wt %) under nitrogen atmosphere. The suspension was degassed under vacuum and purged with hydrogen gas three times. The mixture was stirred under hydrogen atmosphere (15 psi pressure) at rt for 62 hours. On completion, the reaction mixture was filtered and concentrated in vacuo to give the title compound (200 mg, 64% yield) as colorless oil. $^1$H NMR (400 MHz, $CDCl_3$) δ 5.24 (s, 1H), 4.33-4.10 (m, 1H), 3.70-3.58 (m, 12H), 3.54 (t, J=4.8 Hz, 2H), 3.38-3.25 (m, 2H), 3.05-2.88 (m, 2H), 1.60 (br. s, 2H), 1.45 (s, 9H), 1.23 (d, J=1.6 Hz, 3H), 1.20 (d, J=1.2 Hz, 3H).

Tert-butyl N-[2-(2-aminoethoxy)ethyl]-N-[2-[2-[3-(benzyloxycarbonylamino)-2-fluoro-1,1-dimethyl-propoxy]ethoxy]ethyl]carbamate (Intermediate BD)

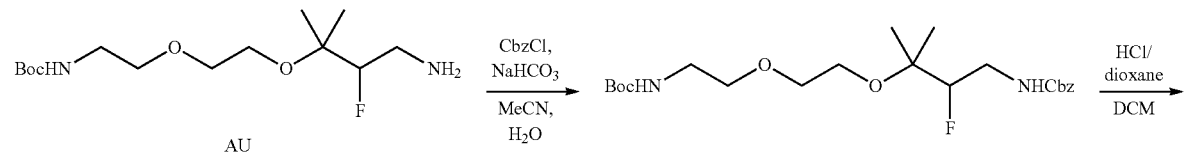

-continued

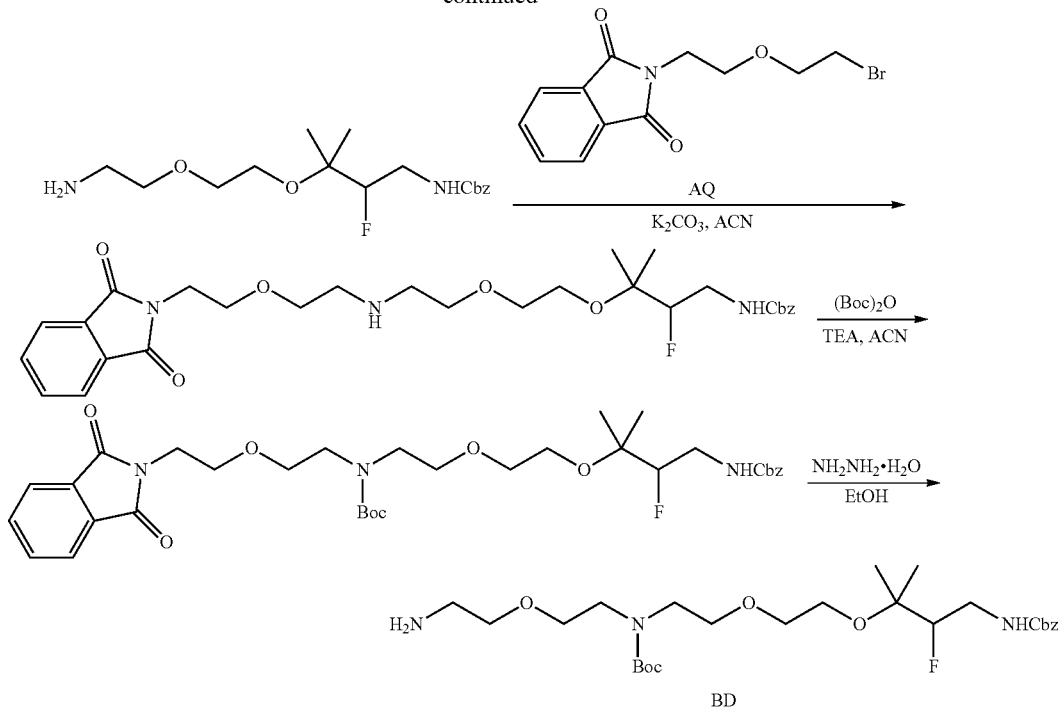

BD

Step 1—Tert-butyl N-[2-[2-[3-(benzyloxycarbonylamino)-2-fluoro-1,1-dimethyl-propoxy]ethoxy]ethyl]carbamate To a solution of tert-butyl N-[2-[2-(3-amino-2-fluoro-1,1-dimethyl-propoxy)ethoxy]ethyl]carbamate (1.1 g, 3.57 mmol, Intermediate AU) in a mixed solvent of ACN (10 mL) and H$_2$O (10 mL) was added NaHCO$_3$ (898 mg, 10.7 mmol, 416 uL) and CbzCl (730 mg, 4.28 mmol, 608 uL). The mixture was stirred at rt for 5 h. On completion, the mixture was extracted with DCM (2×20 mL) and the organic layer was dried over anhydrous Na$_2$SO$_4$, filtered and concentrated in vacuo to give a residue. The residue was purified by silica gel chromatography (PE:EA=3:1) to give the title compound (1.50 g, 95% yield) as a colorless oil. LC-MS (ESI$^+$) m/z 465.2 (M+Na)$^+$.

Step 2—Benzyl N-[3-[2-(2-aminoethoxy)ethoxy]-2-fluoro-3-methyl-butyl]carbamate To a solution of tert-butyl N-[2-[2-[3-(benzyloxycarbonylamino)-2-fluoro-1,1-dimethyl-propoxy]ethoxy]ethyl]carbamate (1.5 g, 3.4 mmol) in DCM (15 mL) was added HCl/dioxane (4 M, 3.00 mL). The mixture was stirred at rt for 1 h. On completion; the reaction mixture was concentrated in vacuo to give the title compound (1.3 g, 93% yield, HCl salt) as a colorless oil. LC-MS (ESI$^+$) m/z 343.1 (M+H)$^+$.

Step 3—Benzyl N-[3-[2-[2-[2-[2-(1,3-dioxoisoindolin-2-yl)ethoxy]ethylamino]ethoxy]ethoxy]-2-fluoro-3-methyl-butyl]carbamate To a solution of benzyl N-[3-[2-(2-aminoethoxy)ethoxy]-2-fluoro-3-methyl-butyl]carbamate (1.3 g, 3.80 mmol) in ACN (10 mL) was added K$_2$CO$_3$ (1.05 g, 7.59 mmol) and 2-[2-(2-bromoethoxy)ethyl]isoindoline 1,3-dione (1.08 g, 3.61 mmol, Intermediate AQ). The mixture was stirred at 60° C. for 16 h. On completion, the reaction mixture was filtered and the filtrate was concentrated in vacuo to give the title compound (2.1 g, crude, 65% yield) as yellow oil. LC-MS (ESI$^+$) m/z 560.3 (M+H)$^+$.

Step 4—Tert-butyl N-[2-[2-[3-(benzyloxycarbonylamino)-2-fluoro-1,1-dimethyl-propoxy]ethoxy]ethyl]-N-[2-[2-(1,3-dioxoisoindolin-2-yl)ethoxy]ethyl]carbamate To a solution of benzyl N-[3-[2-[2-[2-[2-(1,3-dioxoisoindolin-2-yl)ethoxy]ethylamino]ethoxy]ethoxy]-2-fluoro-3-methylbutyl]carbamate (2.1 g, 3.8 mmol) in ACN (20 mL) was added (Boc)$_2$O (1.23 g, 5.63 mmol, 1.29 mL) and TEA (379 mg, 3.75 mmol, 522 uL). The mixture was stirred at rt for 3 h. On completion, the reaction mixture was filtered, and the filtrate was concentrated in vacuo to give a residue. The residue was purified by silica gel chromatography (PE:EA=3:1) to give the title compound (700 mg, 27% yield) as a colorless oil. LC-MS (ESI$^+$) m/z 682.3 (M+Na)$^+$.

Step 5—Tert-butyl N-[2-(2-aminoethoxy)ethyl]-N-[2-[2-[3-(benzyloxycarbonylamino)-2-fluoro-1,1-dimethyl-propoxy]ethoxy]ethyl]carbamate To a solution of tert-butyl N-[2-[2-[3-(benzyloxycarbonylamino)-2-fluoro-1,1-dimethyl-propoxy]ethoxy]ethyl]-N-[2-[2-(1,3-dioxoisoindolin-2-yl)ethoxy]ethyl]carbamate (500 mg, 757 umol) in EtOH (30 mL) was added N$_2$H4.H$_2$O (193 mg, 3.79 mmol, 187 uL, 98% purity) and the reaction mixture was stirred at 80° C. for 16 h. On completion, the filtrate was filtered, and the filtrate was concentrated in vacuo to give a residue. The residue was purified by column chromatography (SiO$_2$, DCM:MeOH=10/1). to give the title compound (340 mg, 84% yield) as a yellow oil. LC-MS (ESI$^+$) m/z 530.3 (M+H)$^+$.

Tert-butyl N-[2-[2-[2-(4-amino-3-fluoro-butoxy)ethoxy]ethoxy]ethyl]carbamate (Intermediate BE)

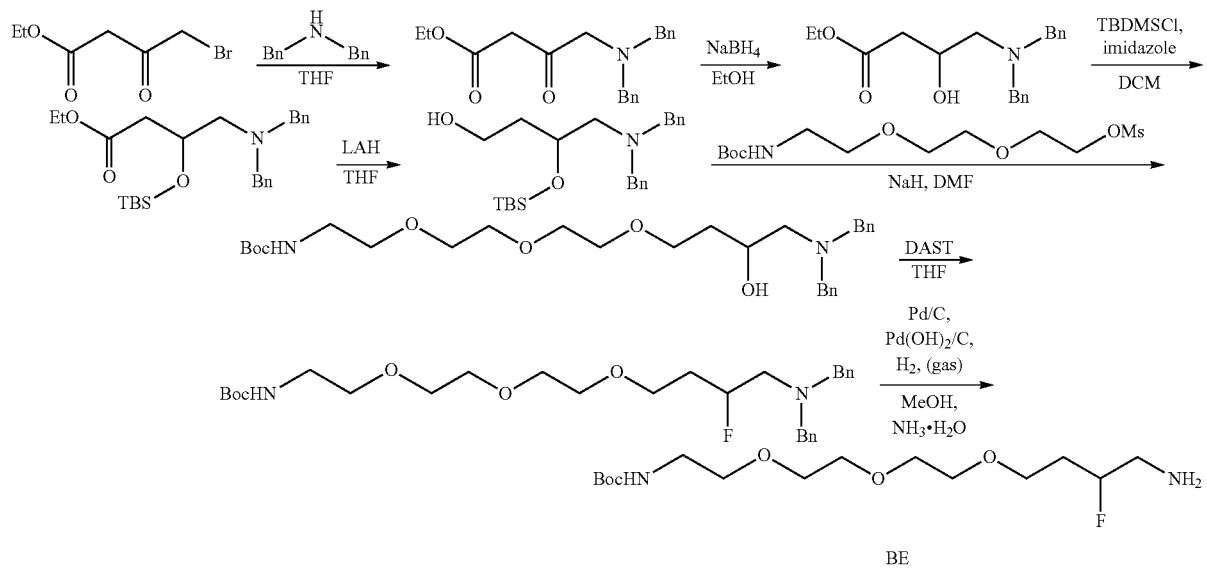

Step 1—Ethyl 4-(dibenzylamino)-3-oxo-butanoate

To a mixture of N-benzyl-1-phenyl-methanamine (49.5 g, 251 mmol, 48.1 mL) ethyl 4-bromo-3-oxo-butanoate (25 g, 119 mmol) in THF (200 mL) was added a solution of ethyl 4-bromo-3-oxo-butanoate (25 g, 119 mmol) in THF (50 mL) dropwise. The reaction mixture was stirred at rt for 1.5 h. On completion, the reaction mixture was concentrated in vacuo to give a residue. The residue was purified by reverse phase chromatography (ACN/H$_2$O) to give the title compound (27 g, 69% yield) as a black brown oil. LC-MS (ESI$^+$) m/z 326.1 (M+H)$^+$.

Step 2—Ethyl 4-(dibenzylamino)-3-hydroxy-butanoate

To a mixture of ethyl 4-(dibenzylamino)-3-oxo-butanoate (4 g, 12.2 mmol) in EtOH (50 mL) was added NaBH$_4$ (930 mg, 24.5 mmol) dropwise at 0° C. The reaction mixture was then allowed to warm to rt and stirred for 2 h. On completion, the reaction mixture was quenched by saturated NH$_4$Cl solution (5 mL) under stirring, the reaction mixture was filtered and the filtrate was concentrated in vacuo to give a residue. The residue was poured into H$_2$O (15 mL) and extracted with EtOAc (3×30 mL). The combined organic layer was dried over Na$_2$SO$_4$, filtered and concentrated in vacuo to give the title compound (3.4 g, 85% yield) as a yellow oil. LC-MS (ESI$^+$) m/z 328.1 (M+H)$^+$.

Step 3—Ethyl 3-[tert-butyl(dimethyl)silyl]oxy-4-(dibenzylamino)butanoate

To a solution of ethyl 4-(dibenzylamino)-3-hydroxy-butanoate (3.0 g, 9.2 mmol) in DCM (30 mL) was added imidazole (2.5 g, 36.7 mmol) and TBDMSCl (4.14 g, 27.4 mmol, 3.37 mL) dropwise at 0° C. The mixture was then stirred at rt for 12 h. On completion, the reaction mixture was filtered, and the filtrate was concentrated in vacuo to give a residue. The residue was purified by column chromatography (SiO$_2$, Petroleum ether/Ethyl acetate=5/1) to give the title compound (3.6 g, 88% yield) as a colorless oil. $^1$H NMR (400 MHz, CDCl$_3$) δ 7.30-7.20 (m, 10H), 4.23-4.13 (m, 1H), 4.11-3.99 (m, 2H), 3.65-3.60 (m, 2H), 3.51-3.47 (m, 2H), 2.78-2.76 (m, 1H), 2.47-2.43 (m, 2H), 2.22-2.18 (m, 1H), 1.21 (t, J=7.2 Hz, 3H), 0.80 (s, 9H), 0.00 (s, 6H).

Step 4—3-[Tert-butyl(dimethyl)silyl]oxy-4-(dibenzylamino)butan-1-ol

To a solution of ethyl 3-[tert-butyl(dimethyl)silyl]oxy-4-(dibenzylamino)butanoate (3.6 g, 8.2 mmol) in THF (40 mL) was added LiBH$_4$ (532 mg, 24.4 mmol) in portions at 0° C. Then the reaction mixture was stirred at rt for 12 h. On completion, the reaction mixture was quenched by sat. NH$_4$Cl (20 mL), and then diluted with H$_2$O (20 mL) and extracted with EtOAc (2×50 mL). The combined organic layers were dried over Na$_2$SO$_4$, filtered and concentrated in vacuo to give a residue. The residue was purified by column chromatography (PE/EA=5/1) to give the title compound (1.8 g, 51% yield) as a yellow oil. $^1$H NMR (400 MHz, CDCl$_3$) δ 7.37-7.26 (m, 10H), 3.97-3.89 (m, 1H), 3.80-3.67 (m, 3H), 3.61-3.48 (m, 4H), 2.70-2.65 (m, 1H), 2.50-2.46 (m, 1H), 1.94-1.86 (m, 1H), 1.79-1.72 (m, 1H), 0.88 (s, 9H), 0.05 (d, J=5.2 Hz, 6H).

Step 5—Tert-butyl N-[2-[2-[2-[4-(dibenzylamino)-3-hydroxybutoxy]ethoxy]ethoxy]ethyl]carbamate To a solution of 3-[tert-butyl(dimethyl)silyl]oxy-4-(dibenzylamino)butan-1-ol (1.8 g, 4.50 mmol) in DMF (30 mL) was added NaH (540 mg, 13.5 mmol) and the mixture was stirred at rt for 30 mins. Then 2-[2-[2-(tert-butoxycarbonylamino)ethoxy]ethoxy]ethyl methanesulfonate (2.21 g, 6.76 mmol, synthesized via Step 1 of Intermediate AM) was added. The reaction mixture was stirred at rt for 3 h. On completion, the reaction mixture was quenched with H$_2$O (20 mL), and then extracted with EtOAc (2×50 mL). The combined organic phase was dried over Na$_2$SO$_4$, filtered and concentrated in vacuo to give a residue. The residue was purified by reverse phase chromatography (0.1% NH$_3$·H$_2$O condition) to give the title compound (250 mg, 11% yield) as a yellow oil. LC-MS (ESI$^+$) m/z 517.2 (M+H)$^+$.

Step 6—Tert-butyl N-[2-[2-[2-[4-(dibenzylamino)-3-fluoro-butoxy]ethoxy]ethoxy]ethyl]carbamate To a solution of tert-butyl N-[2-[2-[2-[4-(dibenzylamino)-3-hydroxybutoxy]ethoxy]ethoxy]ethyl]carbamate (230 mg, 445 umol) in THF (8 mL) was added DAST (86.1 mg, 534 umol, 70.5 uL) dropwise and the mixture was stirred at rt for 1 hr. On completion, the mixture was diluted with H$_2$O (10 mL) and extracted with ethyl acetate (2×20 mL). The combined organic layers were dried over Na$_2$SO$_4$, filtered and concentrated in vacuo to give the title compound (200 mg, 71% yield) as a yellow oil. LC-MS (ESI$^+$) m/z 519.3 (M+H)$^+$.

Step 7—Tert-butyl N-[2-[2-[2-(4-amino-3-fluoro-butoxy)ethoxy]ethoxy]ethyl]carbamate A mixture of tert-butyl N-[2-[2-[2-[4-(dibenzylamino)-3-fluoro-butoxy]ethoxy]ethoxy]ethyl]carbamate (0.28 g, 539.85 umol) in MeOH (10 mL) and NH$_3$.H$_2$O (0.5 mL) was added Pd(OH)$_2$/C (100 mg, 539 umol, 10 wt %) and Pd/C (100 mg, 539 umol, 10 wt %). The reaction mixture was stirred at rt for 24 h under hydrogen atmosphere (50 psi pressure). On completion, the mixture was filtered and concentrated in vacuo to give the title compound (140 mg, 68% yield) as a colorless oil. LC-MS (ESI$^+$) m/z 339.0 (M+H)$^+$.

Tert-butyl N-[2-(2-aminoethoxy)ethyl]-N-[2-[3-(dibenzylamino)-2-fluoro-1,1-dimethyl-propoxy]ethyl]carbamate (Intermediate BF)

Step 1—2-[2-[2-[2-[3-(Dibenzylamino)-2-fluoro-1,1-dimethyl-propoxy]ethylamino]ethoxy]ethyl]isoindoline-1,3-dione To a solution of 2-[2-(2-bromoethoxy)ethyl]isoindoline-1,3-dione (1.95 g, 6.53 mmol, Intermediate AQ) in acetonitrile (150 mL) was added potassium carbonate (3.01 g, 21.7 mmol) and 3-(2-aminoethoxy)-N,N-dibenzyl-2-fluoro-3-methyl-butan-1-amine (2.50 g, 7.26 mmol, synthesized via Steps 1-3 of Intermediate AW). The mixture was stirred at 80° C. for 14 h. On completion, the reaction mixture was filtered and the filtrate was concentrated in vacuo to give the title compound (4.00 g, 51% purity, 50% yield) as a light yellow gum. LC-MS (ESI$^+$) m/z 562.3 (M+H)$^+$.

Step 2—Tert-butyl N-[2-[3-(dibenzylamino)-2-fluoro-1,1-dimethyl-propoxy]ethyl]-N-[2-[2-(1,3-dioxoisoindolin-2-yl)ethoxy]ethyl]carbamate To a solution of 2-[2-[2-[2-[3-(dibenzylamino)-2-fluoro-1,1-dimethyl-propoxy]ethylamino]ethoxy]-ethyl]isoindoline-1,3-dione (4.00 g, 51% purity, 3.63 mmol) in acetonitrile (100 mL) was added Boc$_2$O (2.38 g, 10.9 mmol, 2.50 mL). The mixture was stirred at 60° C. for 1 hour. On completion, the reaction mixture was concentrated in vacuo to get a residue. The residue was purified by column chromatography (petroleum ether:ethyl acetate=8:1 to 5:1) to give the title compound (2.20 g, 91% yield) as a colorless gum. $^1$H NMR (400 MHz, CDCl$_3$) δ 7.88-7.82 (m, 2H), 7.74-7.68 (m, 2H), 7.40-7.38 (m, 4H), 7.32-7.29 (m, 4H), 7.26-7.19 (m, 2H), 4.57-4.40 (m, 1H), 3.92-3.87 (m, 2H), 3.78-3.59 (m, 6H), 3.54-3.15 (m, 8H), 2.93-2.78 (m, 1H), 2.76-2.63 (m, 1H), 1.43 (s, 9H), 1.06 (s, 3H), 1.04 (s, 3H).

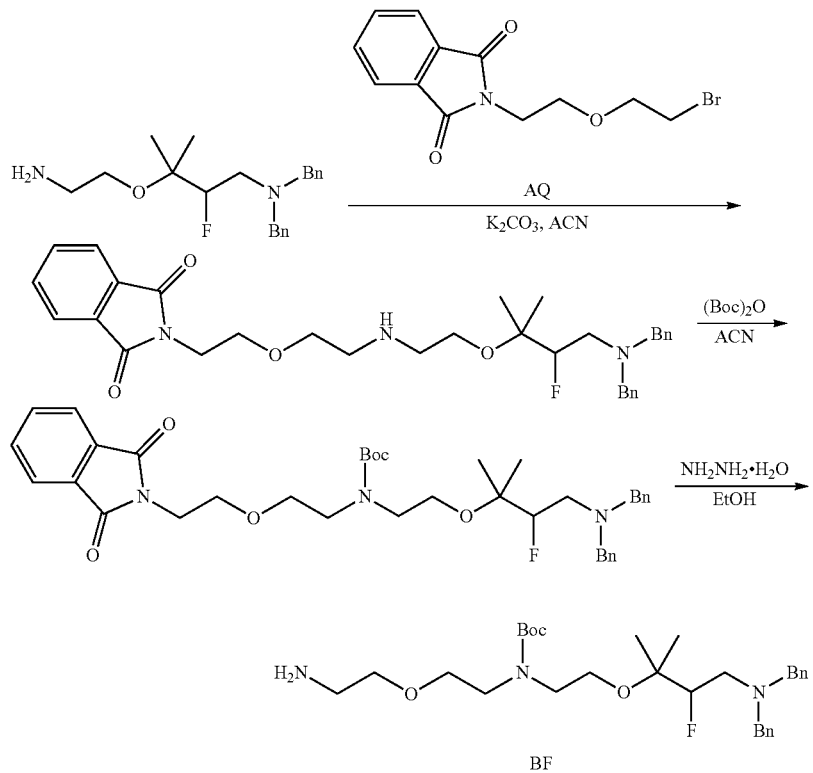

BF

Step 3—Tert-butyl N-[2-(2-aminoethoxy)ethyl]-N-[2-[3-(dibenzylamino)-2-fluoro-1,1-dimethyl-propoxy]ethyl]carbamate To a solution of tert-butyl N-[2-[3-(dibenzylamino)-2-fluoro-1,1-dimethyl-propoxy]ethyl]-N-[2-[2-(1,3-dioxoisoindolin-2-yl)ethoxy]ethyl]carbamate (1.00 g, 1.51 mmol) in ethanol (50 mL) was added hydrazine hydrate (1.51 g, 30.2 mmol, 1.47 mL). The mixture was stirred at 80° C. for 12 h. On completion, the reaction mixture was concentrated in vacuo to get a residue. Then the residue was diluted with (petroleum ether:ethyl acetate=5:1, 25 mL). The insoluble substance was filtered and the filtrate was dried over anhydrous magnesium sulfate, filtered and concentrated in vacuo to give the title compound (780 mg, 97% yield) as a colorless gum. $^1$H NMR (400 MHz, CDCl$_3$) δ 7.34-7.28 (m, 4H), 7.26-7.20 (m, 4H), 7.18-7.11 (m, 2H), 4.50-4.34 (m, 1H), 3.68 (d, J=13.6 Hz, 2H), 3.53 (d, J=13.6 Hz, 2H), 3.44-3.11 (m, 10H), 2.86-2.52 (m, 4H), 1.52 (br, s, 2H), 1.37 (s, 9H), 0.99 (s, 3H), 0.98 (s, 3H).

Tert-butyl N-[5-(3-amino-2-fluoro-propoxy)pentyl]carbamate (Intermediate BG)

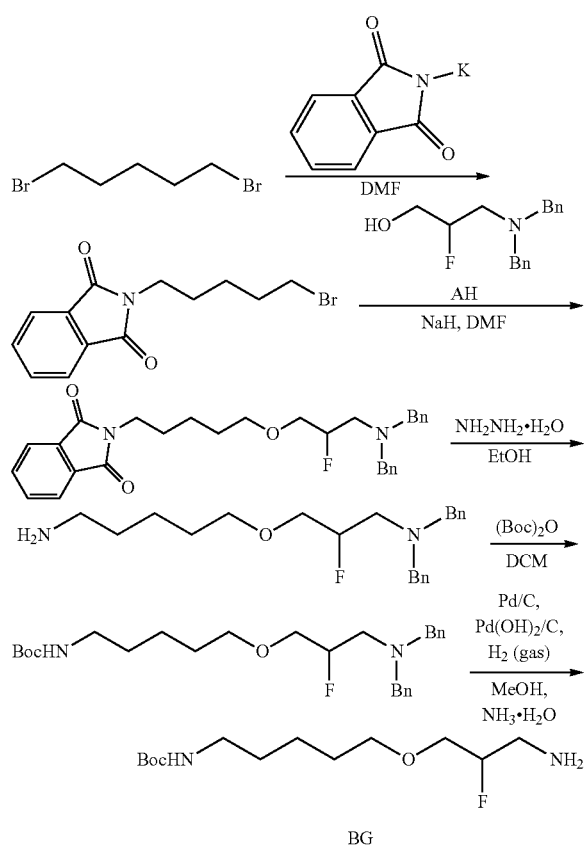

Step 1—2-(5-Bromopentyl)isoindoline-1,3-dione

To a solution of 1,5-dibromopentane (55.9 g, 243 mmol, 32.9 mL) in acetone (250 mL) was added (1,3-dioxoisoindolin-2-yl)potassium (15.0 g, 81.0 mmol) in portions over 30 minutes. The mixture was then stirred at rt for 30 minutes, and then heated to 60° C. and stirred for 15 hrs. On completion, the reaction mixture was filtered and concentrated in vacuo to give a residue. The residue was purified by silica gel chromatography (PE:EA=15:1 to 10:1) to give the title compound (20.0 g, 82% yield) as a white solid. LC-MS (ESI$^+$) m/z 296.0 (M+H)$^+$.

Step 2—2-[5-[3-(Dibenzylamino)-2-fluoro-propoxy]pentl]isoindoline-1,3-dione

To a solution of 3-(dibenzylamino)-2-fluoro-propan-1-ol (2.00 g, 7.32 mmol, Intermediate AH) in DMF (80 mL) was added NaH (878 mg, 22.0 mmol, 60% oil dispersion) and the mixture was stirred at rt for 0.5 h. Then 2-(5-bromopentyl)isoindoline-1,3-dione (5.20 g, 17.6 mmol) was added and the reaction mixture was stirred at 70° C. for a further 34.5 h. On completion, the reaction mixture was quenched by adding H$_2$O (50 mL), and then extracted with ethyl acetate (3×20 mL). The combined organic layers were dried over Na$_2$SO$_4$, filtered and concentrated in vacuo to give a residue. The residue was purified by reverse phase chromatography to give the title compound (560 mg, 16% yield) as colorless oil. LC-MS (ESI$^+$) m/z 489.3 (M+H)$^+$.

Step 3—5-[3-(Dibenzylamino)-2-fluoro-propoxy]pentan-1-amine

To a solution of 2-[5-[3-(dibenzylamino)-2-fluoro-propoxy]pentyl]isoindoline-1,3-dione (560 mg, 1.14 mmol) in EtOH (10 mL) was added NH$_2$NH$_2$.H$_2$O (676 mg, 13.5 mmol). The reaction mixture was stirred at 80° C. for 24 h. On completion, the reaction mixture was filtered and the filtrate was concentrated in vacuo to give the title compound (380 mg, 31% purity, 49% yield) as a light yellow solid. LC-MS (ESI$^+$) m/z 359.1 (M+H)$^+$.

Step 4—Tert-butyl N-[5-[3-(dibenzylamino)-2-fluoro-propoxy]pentyl]carbamate

To a solution of 5-[3-(dibenzylamino)-2-fluoro-propoxy]pentan-1-amine (380 mg, 1.06 mmol) in DCM (10 mL) was added (Boc)$_2$O (462 mg, 2.12 mmol) and the reaction mixture was stirred at rt for 3 h. On completion, the reaction mixture was concentrated in vacuo to give a residue. The residue was purified by column chromatography (SiO$_2$, petroleum ether:ethyl acetate=12:1) to give the title compound (390 mg, 77% yield) as a colorless oil. LC-MS (ESI$^+$) m/z 459.3 (M+H)$^+$.

Step 5—Tert-butyl N-[5-(3-amino-2-fluoro-propoxy)pentyl]carbamate

To a solution of tert-butyl N-[5-[3-(dibenzylamino)-2-fluoro-propoxy]pentyl]carbamate (390 mg, 816 umol) in MeOH (10 mL) was added Pd(OH)$_2$/C (190 mg, 10 wt %), Pd/C (190 mg, 10 wt %) and NH$_3$.H$_2$O (91.0 mg, 779 umol, 30 wt %) under nitrogen atmosphere. The suspension was degassed and purged with hydrogen gas several times. The mixture was stirred at rt for 12 h under hydrogen atmosphere (15 psi pressure). On completion, the reaction mixture was filtered and the filtrate was concentrated in vacuo to give the title compound (206 mg, 61% purity, 55% yield) as a light yellow oil. LC-MS (ESI$^+$) m/z 279.1 (M+H)$^+$.

Tert-butyl (2-(3-amino-2-fluoropropoxy)ethyl)(2-(2-(1,3-dioxoisoindolin-2-yl)ethoxy)ethyl) carbamate
(Intermediate BH)

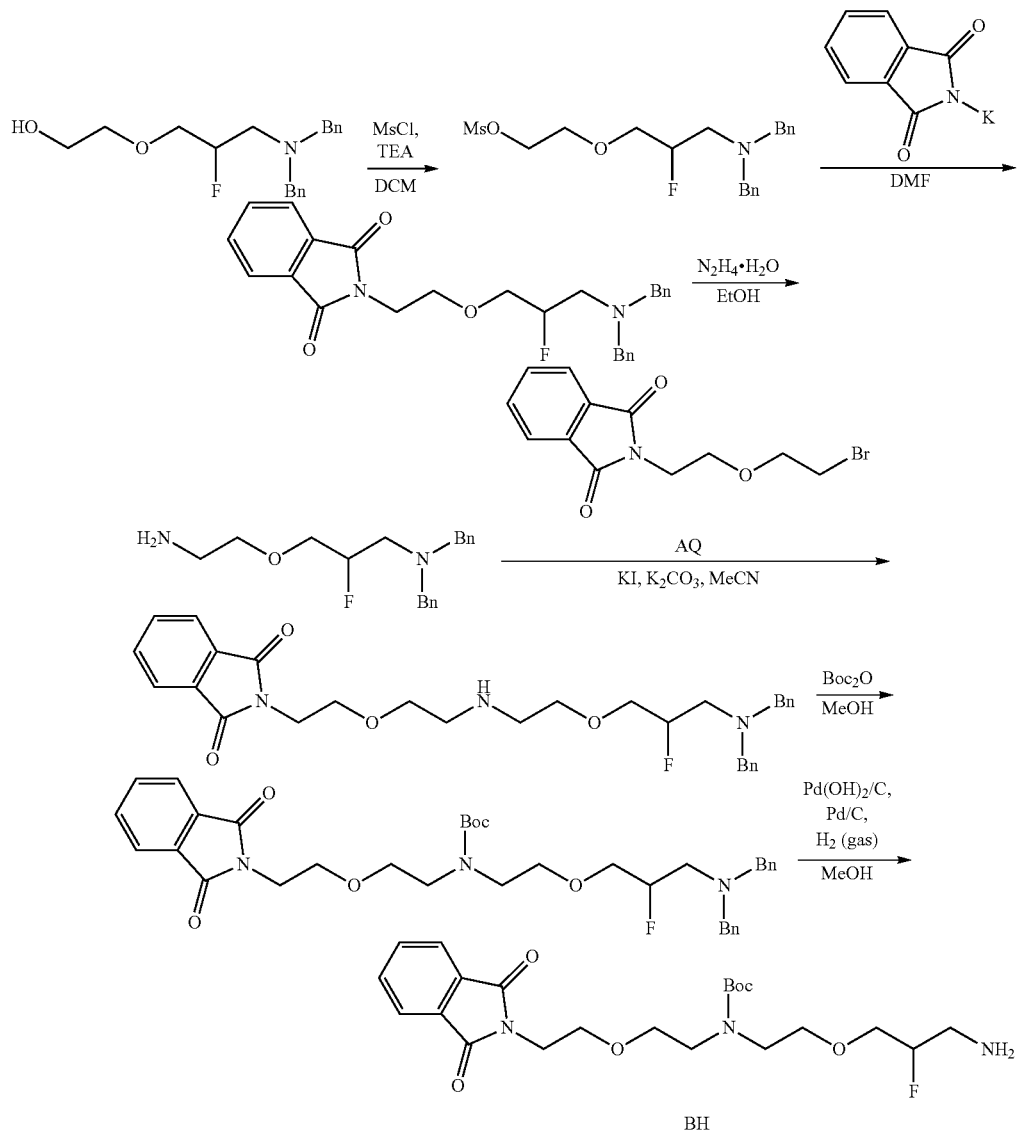

Step 1—2-(3-(Dibenzylamino)-2-fluoropropoxy)ethylmethanesulfonate

To a solution of 2-[3-(dibenzylamino)-2-fluoro-propoxy]ethanol (2.00 g, 6.30 mmol, synthesized via Steps 1-2 of Intermediate AX) and TEA (1.28 g, 12.6 mmol, 1.75 mL) in DCM (20 mL) was added MsCl (866 mg, 7.56 mmol, 585 uL) at 0° C. Then the mixture was allowed to warm to rt and stirred for 3 h. On completion, the reaction mixture was diluted with H$_2$O (50 mL) and extracted with DCM (3×50 mL). The combined organic layers were washed with saturated NH$_4$Cl solution (3×50 mL), dried over anhydrous Na$_2$SO$_4$, filtered and concentrated in vacuo to give the title compound (2.65 g, 90% purity, 96% yield) as a colorless oil.

$^1$H NMR (400 MHz, CDCl$_3$) δ 7.45-7.25 (m, 10H), 4.85-4.65 (m, 1H), 4.38-4.27 (m, 2H), 3.70-3.59 (m, 8H), 2.99 (s, 3H), 2.80-2.70 (m, 2H).

Step 2—2-(2-(3-(Dibenzylamino)-2-fluoropropoxy)ethyl)isoindoline-1,3-dione

A mixture of 2-(3-(dibenzylamino)-2-fluoropropoxy)ethylmethanesulfonate (2.65 g, 6.03 mmol, 90% purity) and potassium 1,3-dioxoisoindolin-2-ide (2.23 g, 12.1 mmol) in DMF (45 mL) was stirred at 85° C. for 12 h. On completion, the reaction mixture was diluted with H$_2$O (50 mL) and extracted with EA (200 mL). The combined organic layer was washed with brine (3×150 mL), dried over anhydrous Na$_2$SO$_4$, filtered and concentrated in vacuo to give the title compound (3.00 g, 90% yield) as a yellow oil. LC-MS (ESI)$^+$ m/z 447.3. (M+H)$^+$.

Step 3—3-(2-Aminoethoxy)-N,N-dibenzyl-2-fluoro-propan-1-amine

To a solution of 2-[2-[3-(dibenzylamino)-2-fluoropropoxy]ethyl]isoindoline-1,3-dione (3.00 g, 1.34 mmol) in EtOH (150 mL) was added N₂H4.H₂O (5 mL, 98% purity) at rt. The mixture was stirred at 85° C. for 12 h. On completion, the reaction mixture was concentrated in vacuo to give a residue. The residue was triturated with DCM (100 mL) and white precipitate was filtered off. The filtrate was concentrated in vacuo to give the title compound (1.93 g, 85% purity, 86% yield) as a colorless oil. LC-MS (ESI)⁺ m/z 317.3. (M+H)⁺.

Step 4—2-(2-Benzyl-4-fluoro-1-phenyl-6,12-dioxa-2,9-diazatetradecan-14-yl)isoindoline-1,3-dione To a mixture of 3-(2-aminoethoxy)-N,N-dibenzyl-2-fluoro-propan-1-amine (1.93 g, 5.19 mmol, 85% purity), K₂CO₃ (2.17 g, 15.6 mmol) and KI (86.2 mg, 519 umol) in MeCN (50 mL) was added dropwise a solution of 2-[2-(2-bromoethoxy)ethyl]isoindoline-1,3-dione (1.39 g, 4.67 mmol, 0.9 eq, Intermediate AQ) in MeCN (10 mL) at rt. The reaction mixture then heated to 80° C. and stirred for 12 h. On completion, the reaction mixture was filtered and concentrated in vacuo to give the title compound (3.33 g, 45% purity, 54% yield) as a colorless oil. LC-MS (ESI)⁺ m/z 534.3. (M+H)⁺.

Step 5—Tert-butyl(2-(3-(dibenzylamino)-2-fluoropropoxy)ethyl)(2-(2-(1,3-dioxoisoindolin-2-yl)ethoxy)ethyl)carbamate A mixture of 2-[2-[2-[2-[3-(dibenzylamino)-2-fluoropropoxy]ethylamino]ethoxy]ethyl]isoindoline-1,3-dione (3.22 g, 45% purity, 2.72 mmol) and Boc₂O (1.19 g, 1.25 mL) in MeOH (30 mL) was stirred at 60° C. for 6 h. On completion, the reaction mixture was concentrated in vacuo to give a residue. The residue was purified by column chromatography (SiO₂, Petroleum ether:Ethyl acetate=1:0 to 5:1) to give the title compound (1.40 g, 79% purity, 65% yield) as a colorless oil. LC-MS (ESI)⁺ m/z 634.4. (M+H)⁺.

Step 6—Tert-butyl (2-(3-amino-2-fluoropropoxy)ethyl)(2-(2-(1,3-dioxoisoindolin-2-yl)ethoxy)ethyl)carbamate A mixture of tert-butyl N-[2-[3-(dibenzylamino)-2-fluoro-propoxy]ethyl]-N-[2-[2-(1,3-dioxoisoindolin-2-yl)ethoxy]ethyl]carbamate (400 mg, 79% purity), Pd/C (200 mg, 10 wt %) and Pd(OH)₂/C (200 mg, 10 wt %) in MeOH (15 mL) was purged with hydrogen gas several times. The reaction mixture was stirred under hydrogen atmosphere (50 psi pressure) at 45° C. for 6 hours. On completion, the reaction mixture was filtered and concentrated in vacuo to give the title compound (273 mg, 71.6% purity) as a colorless oil. LC-MS (ESI)⁺ m/z 454.3. (M+H)⁺.

Ethyl 2-[2-[2-(2-methylsulfonyloxyethoxy)ethoxy]ethoxy]acetate (Intermediate BI)

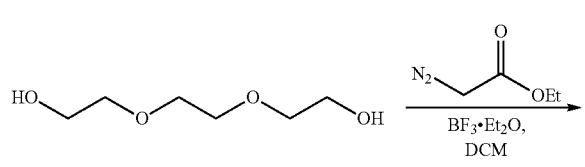

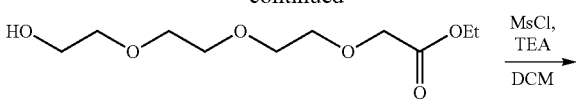

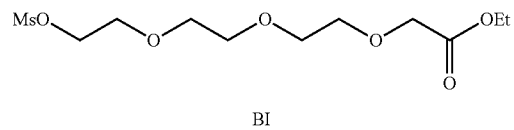

BI

Step 1-Ethyl 2-[2-[2-(2-hydroxyethoxy)ethoxy]ethoxy]acetate

A solution of 2-[2-(2-hydroxyethoxy)ethoxy]ethanol (10.0 g, 66.6 mmol) and BF₃.Et₂O (205 mg, 665 umol) in DCM (150 mL) was cooled to 0° C. Then ethyl 2-diazoacetate (7.60 g, 66.9 mmol) was added to the mixture dropwise. After that, the mixture was stirred at rt for 12 h. On completion, the reaction mixture was quenched with saturated NH₄Cl (5 mL), then diluted with water (100 mL) and extracted with DCM (3×50 mL). The combined organic layers were dried over sodium sulfate, filtered, and concentrated in vacuo to give a residue. The residue was purified by silica gel chromatography (PE:EA=1:3) to give the title compound (5.00 g, 31% yield) as a colorless oil. ¹H NMR (400 MHz, CDCl₃) δ 4.17 (q, J=7.2 Hz, 2H), 4.11 (s, 2H), 3.72-3.60 (m, 10H), 3.59-3.54 (m, 2H), 2.82 (s, 2H), 1.24 (t, J=7.2 Hz, 3H).

Step 2—Ethyl 2-[2-[2-(2-methylsulfonyloxyethoxy)ethoxy]ethoxy]acetate

A solution of ethyl 2-[2-[2-(2-hydroxyethoxy)ethoxy]ethoxy]acetate (900 mg, 3.81 mmol) and TEA (1.16 g, 11.4 mmol) in DCM (10 mL) was cooled to 0° C. Then, MsCl (523 mg, 4.57 mmol) in DCM (2 mL) was added to the reaction mixture dropwise. The mixture was stirred at rt for 1 hour. On completion, the reaction mixture was quenched with water (8 mL) and then extracted with dichloromethane (3×5 mL). The combined organic layer was dried over anhydrous Na₂SO₄, filtered and concentrated in vacuo to give the title compound (1.10 g, 91% yield) as a colorless oil. ¹H NMR (400 MHz, CDCl₃) δ 4.40-4.36 (m, 2H), 4.21 (q, J=7.2 Hz, 2H), 4.13 (s, 2H), 3.79-3.74 (i, 2H), 3.74-3.65 (i, 8H), 3.08 (s, 3H), 1.28 (t, J=7.2 Hz, 3H).

Ethyl 2-[2-[2-[2-[2-(3-amino-2-fluoro-1,1-dimethyl-propoxy)ethoxy]ethoxy]ethoxy]ethoxy]acetate (Intermediate BJ)

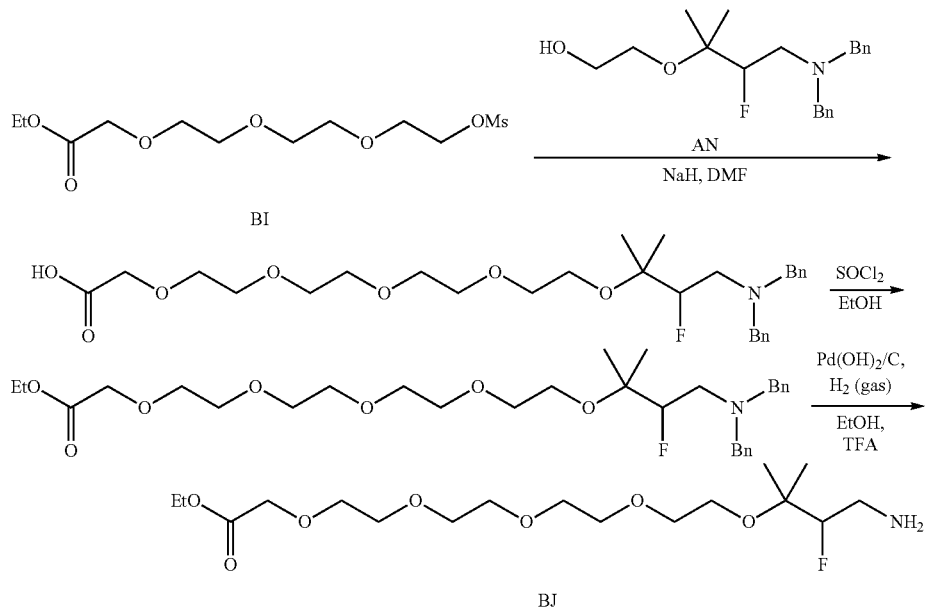

Step 1—2-[2-[2-[2-[2-[3-(Dibenzylamino)-2-fluoro-1,1-dimethyl-propoxy]ethoxy]ethoxy]ethoxy]ethoxy]acetic acid To a mixture of 2-[3-(dibenzylamino)-2-fluoro-1,1-dimethyl-propoxy]ethanol (3.66 g, 10.6 mmol, Intermediate AN) in DMF (40 mL) was added NaH (1.27 g, 31.8 mmol, 60% dispersion in mineral oil) at 0° C. and stirred for 0.5 hour. Then ethyl 2-[2-[2-(2-methylsulfonyloxyethoxy)ethoxy]ethoxy]acetate (4.00 g, 12.7 mmol, Intermediate BI) was added and the reaction was allowed to warm to rt and stirred for 16 hours. On completion, the reaction mixture was quenched with water (1 mL) and concentrated in vacuo to give the title compound (5.00 g, 88% yield) as a yellow oil. LC-MS (ESI$^+$) m/z 536.1 (M+H)$^+$.

Step 2—Ethyl 2-[2-[2-[2-[2-[3-(dibenzylamino)-2-fluoro-1,1-dimethyl-propoxy]ethoxy]ethoxy]ethoxy]ethoxy]acetate To a mixture of 2-[2-[2-[2-[2-[3-(dibenzylamino)-2-fluoro-1,1-dimethyl-propoxy]ethoxy]ethoxy]ethoxy]ethoxy]acetic acid (5.00 g, 9.33 mmol) in EtOH (50 mL) was added SOCl$_2$ (3.33 g, 28.0 mmol). The reaction mixture was stirred at 80° C. for 4 hours. On completion, the reaction mixture was concentrated in vacuo. The residue was diluted with water (10 mL) and basified with NaHCO$_3$ until the pH=7-8, then the mixture was extracted with EA (3×20 mL). The combined organic layers were dried over Na$_2$SO$_4$, filtered and concentrated in vacuo to give a residue. The residue was purified by reverse phase chromatography (0.1% NH$_3$.H$_2$O) to give the title compound (1.80 g, 34% yield) as a light yellow oil. LC-MS (ESI$^+$) m/z 564.4 (M+H)$^+$.

Step 3—Ethyl 2-[2-[2-[2-[2-(3-amino-2-fluoro-1,1-dimethyl-propoxy)ethoxy]ethoxy]ethoxy]ethoxy]acetate To a mixture of ethyl 2-[2-[2-[2-[2-[3-(dibenzylamino)-2-fluoro-1,1-dimethyl-propoxy]ethoxy]ethoxy]ethoxy]ethoxy]acetate (900 mg, 1.60 mmol) and Pd(OH)$_2$/C (600 mg, 10% purity) in EtOH (10 mL) was added TFA (161 mg, 1.60 mmol) under hydrogen atmosphere (15 psi pressure). The reaction mixture was stirred at rt for 16 hours. On completion, the reaction mixture was concentrated in vacuo to give the title compound (610 mg, 90% yield) as a light yellow oil. $^1$H NMR (400 MHz, CDCl$_3$) δ 4.54-4.37 (m, 1H), 4.24 (q, J=7.6 Hz, 2H), 4.15 (s, 2H), 3.80-3.50 (m, 18H), 3.31-3.01 (t, J=7.6 Hz, 3H), 1.31-1.23 (m, 6H).

Ethyl 2-[2-[2-[2-(2-methylsulfonyloxyethoxy)ethoxy]ethoxy]ethoxy]acetate (Intermediate BK)

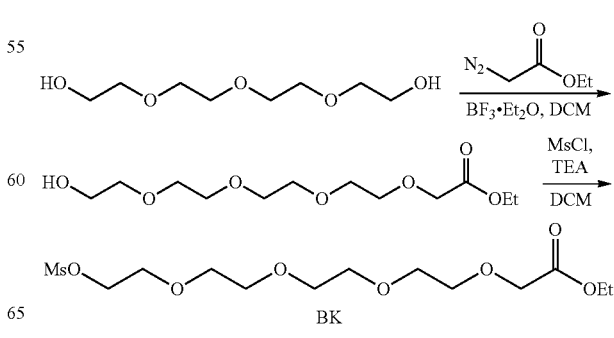

Step 1—Ethyl 2-[2-[2-[2-(2-hydroxyethoxy)ethoxy]ethoxy]ethoxy]acetate

A solution of 2-[2-[2-(2-hydroxyethoxy)ethoxy]ethoxy]ethanol (10.0 g, 51.5 mmol, CAS #112-60-7) and $BF_3 \cdot Et_2O$ (159 mg, 515 umol) in DCM (150 mL) was cooled to 0° C. Then ethyl 2-diazoacetate (5.87 g, 51.5 mmol) was added to the solution dropwise. After that, the mixture was stirred at rt for 12 h. On completion, the reaction mixture was quenched with saturated $NH_4Cl$ aqueous solution (5 mL), diluted with water (100 mL), then extracted with dichloromethane (3×50 mL). The combined organic layer was dried over anhydrous $Na_2SO_4$, filtered and concentrated in vacuo to give a residue. The residue was purified by silica gel chromatography (PE:EA=1:3) to give the title compound (2.90 g, 20% yield) as a colorless oil. $^1H$ NMR (400 MHz, $CDCl_3$) δ 4.19 (q, J=7.2 Hz, 2H), 4.12 (s, 2H), 3.73-3.63 (m, 14H), 3.61-3.56 (m, 2H), 1.26 (t, J=7.2 Hz, 3H)

Step 2—Ethyl 2-[2-[2-[2-(2-methylsulfonyloxyethoxy)ethoxy]ethoxy]ethoxy]acetate A solution of ethyl 2-[2-[2-[2-(2-hydroxyethoxy)ethoxy]ethoxy]ethoxy]acetate (800 mg, 2.85 mmol) and TEA (577 mg, 5.70 mmol) in DCM (30 mL) was cooled to 0° C. Then, a solution of MsCl (392 mg, 3.42 mmol) in DCM (4 mL) was added to the mixture dropwise. The mixture was then allowed to warm to rt and stirred for 1 hour. On completion, the reaction mixture was quenched with water (25 mL), and extracted with dichloromethane (3×10 mL). The combined organic layer was dried over anhydrous $Na_2SO_4$, filtered and concentrated in vacuo to give the title compound (1.90 g, 90% yield) as a yellowish oil.

Methyl 2-[2-[2-[2-[2-(3-amino-2-fluoro-1-methyl-propoxy)ethoxy]ethoxy]ethoxy]ethoxy]acetate (Intermediate BL)

Step 1—2-[2-[2-[2-[2-[3-(Dibenzylamino)-2-fluoro-1-methyl-propoxy]ethoxy]ethoxy]ethoxy]ethoxy] acetic acid To a solution of 4-(dibenzylamino)-3-fluoro-butan-2-ol (600 mg, 2.09 mmol, Intermediate AL) in DMF (10 mL) was added NaH (209 mg, 5.22 mmol) at 0° C. After 0.5 h, ethyl 2-[2-[2-[2-(2-methylsulfonyloxyethoxy)ethoxy]ethoxy]ethoxy]acetate (898 mg, 2.51 mmol, Intermediate BK) was added to the reaction mixture. The reaction mixture was then allowed to warm to rt and stirred for 17 h. On completion, the mixture was acidified with 1N HCl solution until the pH=4-5, then concentrated in vacuo. The residue was purified by reverse phase chromatography (0.1% TFA) to give the title compound (640 mg, 53% yield) as a yellow oil. LC-MS ($ESI^+$) m/z 522.1 $(M+H)^+$.

Step 2—Methyl 2-[2-[2-[2-[2-[3-(dibenzylamino)-2-fluoro-1-methyl-propoxy]ethoxy]ethoxy]ethoxy]ethoxy]acetate To a solution of 2-[2-[2-[2-[2-[3-(dibenzylamino)-2-fluoro-1-methyl-propoxy]ethoxy]ethoxy]ethoxy]ethoxy] acetic acid (640 mg, 1.11 mmol) in MeOH (10 mL) was added $SOCl_2$ (396 mg, 3.33 mmol). The reaction mixture then heated to 65° C. and stirred for 15 h. On completion, the mixture was concentrated in vacuo to remove the solvent MeOH then diluted with $H_2O$ (20 mL). The mixture was then basified with 1N NaOH solution until the pH=8-9, and extracted with DCM (3×20 mL). The combined organic layer was washed with brine (30 mL), dried over $Na_2SO_4$, and concentrated in vacuo. The residue was purified by reverse phase chromatography (0.1% FA) to give the title compound (280 mg, 47% yield) as a yellow oil. LC-MS ($ESI^+$) m/z 536.3 $(M+H)^+$.

Step 3—Methyl 2-[2-[2-[2-[2-(3-amino-2-fluoro-1-methyl-propoxy)ethoxy]ethoxy]ethoxy]ethoxy]acetate To a solution of methyl 2-[2-[2-[2-[2-[3-(dibenzylamino)-2-fluoro-1-methyl-propoxy]ethoxy]ethoxy]ethoxy]ethoxy]

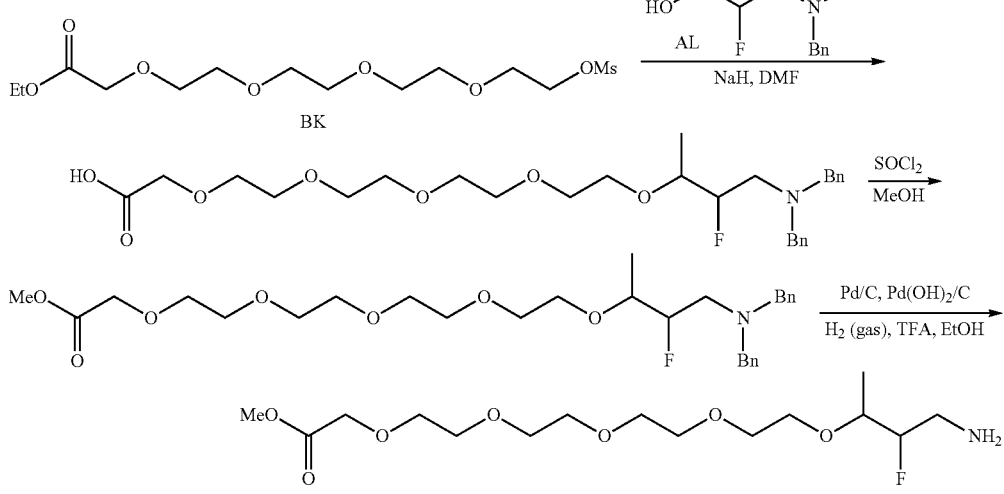

BL acetate (280 mg, 522 umol) in EtOH (4 mL) was added Pd(OH)$_2$/C (0.3 g, 10 wt %), Pd/C (0.3 g, 10 wt %) and TFA (59.6 mg, 523 umol, 0.59 mmol). The suspension was degassed and purged with hydrogen gas three times. The reaction mixture was stirred under hydrogen atmosphere (15 psi pressure) at rt for 17 h. On completion, the mixture was filtered and the filtrate was concentrated in vacuo to give the title compound (200 mg, 100% yield). $^1$H NMR (400 MHz, CDCl$_3$) δ 4.68-4.29 (m, 1H), 4.17-4.11 (m, 1H), 3.75-3.53 (m, 21H), 3.27-3.14 (m, 2H), 1.21-1.18 (m, 3H).

Methyl 2-[2-[2-[3-[[6-(5-cyanopyrazolo[3,4-b]pyridin-1-yl)-4-(cyclopropylamino)pyridine-3-carbonyl]amino]-2-fluoro-1-methyl-propoxy]ethoxy]ethoxy]acetate (Intermediate BM)

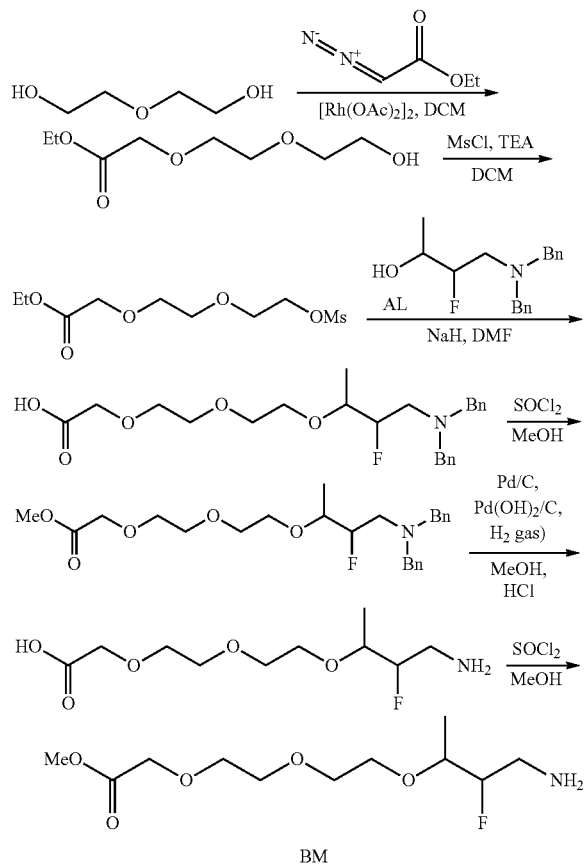

Step 1—Ethyl 2-[2-(2-hydroxyethoxy)ethoxy]acetate

To a mixture of 2-(2-hydroxyethoxy)ethanol (5.00 g, 47.1 mmol, 4.46 mL) and Rh$_2$(OAc)$_4$ (278 mg, 628 umol) in DCM (50 mL) was added a solution of ethyl 2-diazoacetate (3.58 g, 31.4 mmol, 3.29 mL) in DCM (35 mL) dropwise. Then, the reaction mixture was stirred at rt for 16 h. On completion, the reaction mixture was quenched by adding H$_2$O (10 mL), and then extracted with DCM (2×15 mL). The combined organic layers were dried over anhydrous Na$_2$SO$_4$, filtered and concentrated in vacuo to give a residue. The residue was purified by silica gel column chromatography (Petroleum ether:Ethyl acetate=10:1 to 0:1) to give the title compound (1.68 g, 28% yield) as a black-brown oil. $^1$H NMR (400 MHz, CDCl$_3$-d) δ 4.22 (q, J=7.2 Hz, 2H), 4.14 (s, 2H), 3.77-3.68 (m, 6H), 3.64-3.59 (m, 2H), 2.60 (s, 1H), 1.29 (t, J=7.2 Hz, 3H).

Step 2—Ethyl 2-[2-(2-methylsulfonyloxyethoxy)ethoxy]acetate

To a solution of ethyl 2-[2-(2-hydroxyethoxy)ethoxy]acetate (800 mg, 4.16 mmol) in DCM (8 mL) was added TEA (1.26 g, 12.5 mmol, 1.74 mL) and MsCl (715 mg, 6.24 mmol, 483 uL) at 0° C. The reaction mixture was then allowed to warm to rt and stirred for 30 minutes. On completion, the reaction mixture was quenched by adding H$_2$O (10 mL) and then citric acid (5 mL). The mixture was then extracted with DCM (2×10 mL). The combined organic layers were washed with NaHCO$_3$ solution (20 mL), dried over anhydrous Na$_2$SO$_4$, filtered and concentrated in vacuo to give the title compound (1.00 g, 88% yield) as a black-brown oil. $^1$H NMR (400 MHz, CDCl$_3$) δ 4.44-4.37 (m, 2H), 4.24 (q, J=7.2 Hz, 2H), 4.17-4.12 (m, 2H), 3.84-3.78 (m, 2H), 3.77-3.69 (m, 4H), 3.10 (s, 3H), 1.31 (t, J=7.2 Hz, 3H).

Step 3—2-[2-[2-[3-(Dibenzylamino)-2-fluoro-1-methyl-propoxy]ethoxy]ethoxy]acetic acid To a solution of 4-(dibenzylamino)-3-fluoro-butan-2-ol (818 mg, 2.85 mmol, Intermediate AL) in DMF (10 mL) was added NaH (341 mg, 8.54 mmol, 60% dispersion in mineral oil) at 0° C. and the reaction was stirred for 0.5 hour. Then, ethyl 2-[2-(2-methylsulfonyloxyethoxy)ethoxy]acetate (1.00 g, 3.70 mmol) was added, and the reaction mixture was allowed to warm to rt and stirred for a further 16.5 h. On completion, the reaction mixture was adjusted to pH<7 with 10% hydrochloride acid, and then concentrated in vacuo to give the title compound (3.00 g, 31% purity, 76% yield) as a black-brown gum. LC-MS (ESI$^+$) m/z 434.1 (M+H)$^+$.

Step 4—Methyl 2-[2-[2-[3-(dibenzylamino)-2-fluoro-1-methyl-propoxy]ethoxy]ethoxy]acetate To a solution of 2-[2-[2-[3-(dibenzylamino)-2-fluoro-1-methyl-propoxy]ethoxy]ethoxy]acetic acid (3.00 g, 6.92 mmol) in MeOH (30 mL) was added SOCl$_2$ (2.47 g, 20.8 mmol, 1.51 mL). The reaction mixture then heated to 65° C. and stirred for 15 h. On completion, the reaction mixture was concentrated in vacuo. The residue was then adjusted to pH>8 with saturated NaHCO$_3$ solution, and then extracted with ethyl acetate (2×20 mL). The combined organic layers were dried over anhydrous Na$_2$SO$_4$, filtered and concentrated in vacuo to give a residue. The residue was purified by silica gel column chromatography (petroleum ether:ethyl acetate=30:1 to 10:1) first, and then purified by reverse phase column chromatography (0.1% FA) to give the title compound (250 mg, 95% purity, 8% yield) as a brown oil. $^1$H NMR (400 MHz, CDCl$_3$) δ 7.30-7.15 (m, 10H), 4.65-4.36 (m, 1H), 4.07 (d, J=3.2 Hz, 2H), 3.69-3.43 (m, 15H), 3.43-3.35 (m, 1H), 2.77-2.62 (m, 2H), 0.99-0.92 (m, 3H).

Step 5—Methyl 2-[2-[2-(3-amino-2-fluoro-1-methyl-propoxy)ethoxy]ethoxy]acetate

To a solution of methyl 2-[2-[2-[3-(dibenzylamino)-2-fluoro-1-methyl-propoxy]ethoxy]ethoxy]acetate (250 mg, 559 umol) in MeOH (5 mL) was added Pd/C (120 mg, 10 wt %), Pd(OH)$_2$/C (120 mg, 10 wt %) and HCl (1 M, 2.5 mL). The reaction mixture was stirred at rt for 15 h under hydrogen atmosphere (15 psi pressure). On completion, the reaction mixture was filtered and the filtrate concentrated in vacuo to give the title compound (200 mg, 92% purity, 100% yield) as a light yellow oil. LC-MS (ESI$^+$) m/z 254.1 (M+H)$^+$.

EtOAc (50 mL), filtered and the filtrate was removed under nitrogen gas sweep to give the title compound (3.2 g, 90% yield) as a yellow oil. LC-MS (ESI$^+$) m/z 219.1 (M+H–100)$^+$ 2-[2-[2-[2-[2-[2-(Tert-butoxycarbonylamino)ethoxy] ethoxy]ethoxy]ethoxy]ethyl methanesulfonate (Intermediate BO)

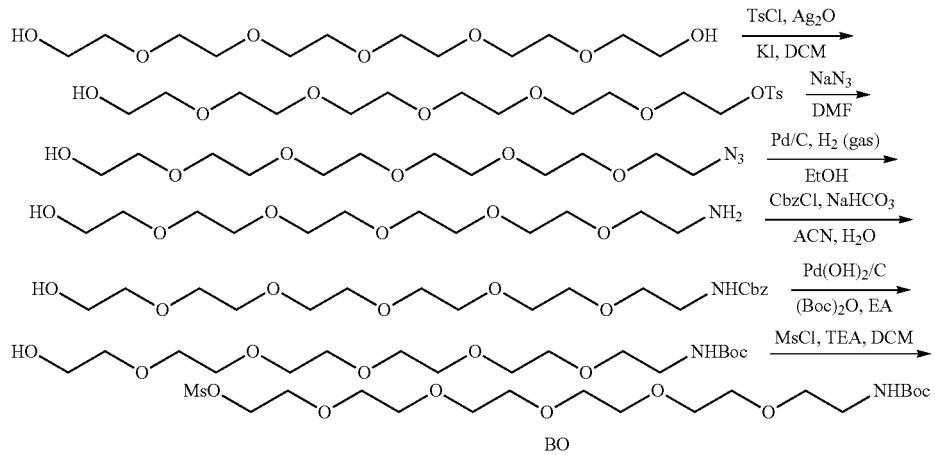

BO

Step 6—Methyl 2-[2-[2-[3-[[6-(5-cyanopyrazolo[3,4-b]pyridin-1-yl)-4-(cyclopropylamino)pyridine-3-carbonyl]amino]-2-fluoro-1-methyl-propoxy]ethoxy] ethoxy]acetate To a solution of 2-[2-[2-(3-amino-2-fluoro-1-methyl-propoxy)ethoxy]ethoxy]acetic acid (140 mg, 553 umol) in MeOH (3 mL) was added SOCl$_2$ (197 mg, 1.66 mmol, 120 uL). The reaction mixture was then heated to 65° C. and stirred for 3 h. On completion, the reaction mixture was concentrated in vacuo to give the title compound (120 mg, 85% purity, 69% yield) as a yellow oil. LC-MS (ESI$^+$) m/z 268.1 (M+H)$^+$.

Tert-butyl N-[2-[2-[2-(2-azidoethoxy)ethoxy] ethoxy]ethyl]carbamate (Intermediate BN)

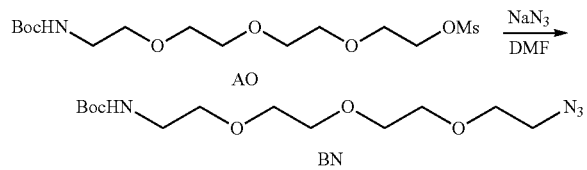

To a solution of 2-[2-[2-[2-(tert-butoxycarbonylamino) ethoxy]ethoxy]ethoxy]ethyl methanesulfonate (3.6 g, 9.7 mmol, Intermediate AO) in DMF (20 mL) was added NaN$_3$ (1.26 g, 19.4 mmol). The reaction mixture was then heated to 80° C. and stirred for 18 h. On completion, the solvent DMF was removed in vacuo. The residue was diluted with

Step 1—2-[2-[2-[2-[2-(2-Hydroxyethoxy)ethoxy] ethoxy]ethoxy]ethoxy]ethyl4-methylbenzene sulfonate To a solution of 2-[2-[2-[2-[2-(2-hydroxyethoxy)ethoxy] ethoxy]ethoxy]ethoxy]ethanol (10.0 g, 35.4 mmol, CAS #2615-15-8) in DCM (1.00 L) was added Ag$_2$O (9.85 g, 42.5 mmol), KI (587 mg, 3.54 mmol) and 4-methylbenzenesulfonylchloride (6.75 g, 35.4 mmol). The reaction mixture was stirred under nitrogen atmosphere at rt for 24 h. On completion, the mixture was filtered through a pad of celite and the filtrate was concentrated in vacuo to give a residue. The residue was purified by silica column chromatography (DCM:MeOH=100:1) to give the title compound (15.0 g, 97% yield) as a yellowish oil. $^1$H NMR (400 MHz, CDCl$_3$) δ 7.73 (d, J=8.4 Hz, 2H), 7.27 (d, J=8.4 Hz, 2H), 4.12-4.06 (m, 2H), 3.68-3.50 (m, 22H), 2.38 (s, 3H).

Step 2—2-[2-[2-[2-[2-(2-Azidoethoxy)ethoxy] ethoxy]ethoxy]ethoxy]ethanol

To a solution of 2-[2-[2-[2-[2-(2-hydroxyethoxy)ethoxy] ethoxy]ethoxy]ethoxy]ethyl 4-methylbenzene sulfonate (15.0 g, 34.3 mmol) in DMF (75.0 mL) was added NaN$_3$ (4.50 g, 69.2 mmol) and the mixture was heated to 80° C. and stirred for 12 h. On completion, the DMF solvent was removed under nitrogen gas sweep. Then the reaction mixture was diluted with water (100 mL) and extracted with DCM:MeOH (10:1) (2×200 mL). The organic layer was purged under nitrogen to give the title compound (10.0 g, 94% yield) as a colorless oil.

Step 3—2-[2-[2-[2-[2-(2-Aminoethoxy)ethoxy] ethoxy]ethoxy]ethoxy]ethanol

To a solution of 2-[2-[2-[2-[2-(2-azidoethoxy)ethoxy] ethoxy]ethoxy]ethoxy]ethanol (10.0 g, 32.5 mmol) in EtOH (80.0 mL) was added Pd/C (4.00 g, 10 wt %). The reaction mixture was stirred under hydrogen atmosphere (15 psi pressure) at rt for 12 h. On completion, the mixture was filtered and concentrated in vacuo to give the title compound (8.50 g, 92% yield) as a light yellow oil. LC-MS (ESI)$^+$ m/z 282.1. (M+H)$^+$.

Step 4—Benzyl N-[2-[2-[2-[2-[2-(2-hydroxyethoxy)ethoxy]ethoxy]ethoxy]ethoxy]ethyl]carbamate To a solution of 2-[2-[2-[2-[2-(2-aminoethoxy)ethoxy]ethoxy]ethoxy]ethoxy]ethanol (4.00 g, 14.2 mmol) in ACN (40.0 mL) and H$_2$O (40.0 mL) was added NaHCO$_3$ (3.58 g, 42.6 mmol) and CbzCl (2.91 g, 17.0 mmol), and the mixture was stirred at rt for 12 h. On completion, the mixture was extracted with DCM (2×100 mL). The organic layer was dried over anhydrous Na$_2$SO$_4$, filtered and concentrated in vacuo. The residue was purified by silica gel column chromatography (DCM:MeOH=10:1) to give the title compound (4.00 g, 67% yield) as a colorless oil. $^1$H NMR (400 MHz, CDCl$_3$) δ 7.38-7.33 (m, 5H), 5.56 (s, 1H), 5.11 (s, 2H), 3.73-3.42 (m, 23H).

Step 5—Tert-butyl N-[2-[2-[2-[2-[2-(2-hydroxyethoxy)ethoxy]ethoxy]ethoxy]ethoxy]ethyl]carbamate To a solution of benzyl N-[2-[2-[2-[2-[2-(2-hydroxyethoxy)ethoxy]ethoxy]ethoxy]ethoxy]ethyl]carbamate (3.00 g, 7.22 mmol) in EtOAc (60.0 mL) was added Pd(OH)$_2$/C (100 mg, 2.41 mmol, 10 wt %) and (Boc)$_2$O (1.89 g, 8.66 mmol), and the mixture was stirred at rt for 12 h. On completion, the mixture was filtered and concentrated in vacuo. The residue was purified by silica column chromatography (DCM:MeOH=10:1) to give the title compound (2.00 g, 72% yield) as a colorless oil. $^1$H NMR (400 MHz, CDCl$_3$) δ 5.19 (s, 1H), 3.84-3.82 (m, 2H), 3.80-3.34 (m, 20H), 3.33 (s, 2H), 1.46 (s, 9H).

Step 6—2-[2-[2-[2-[2-[2-(Tert-butoxycarbonylamino)ethoxy]ethoxy]ethoxy]ethoxy]ethoxy]ethyl methanesulfonate To a solution of tert-butyl N-[2-[2-[2-[2-[2-(2-hydroxyethoxy)ethoxy]ethoxy]ethoxy]ethoxy]ethyl]carbamate (1.70 g, 4.46 mmol) in DCM (5.00 mL) was added MsCl (765 mg, 6.68 mmol) and TEA (1.35 g, 13.3 mmol), and the mixture was stirred at 0° C. for 1 h. On completion, the mixture was quenched with water (20 mL) and extracted with DCM (3×30 mL). The combined organic layer was washed with brine (3×30 mL). The organic layer was dried with anhydrous Na$_2$SO$_4$, filtered and concentrated in vacuo to give the title compound (1.8 g, 87% yield) as a yellow oil. $^1$H NMR (400 MHz, CDCl$_3$) δ 5.07 (s, 1H), 4.44-4.38 (m, 2H), 3.81-3.76 (m, 2H), 3.71-3.62 (m, 16H), 3.56 (t, J=5.2 Hz, 2H), 3.39-3.29 (m, 2H), 3.11 (s, 3H), 1.46 (s, 9H).

Tert-butyl N-[2-[2-[2-[2-[2-[2-(3-amino-2-fluoropropoxy)ethoxy]ethoxy]ethoxy]ethoxy]ethoxy]ethyl]carbamate (Intermediate BP)

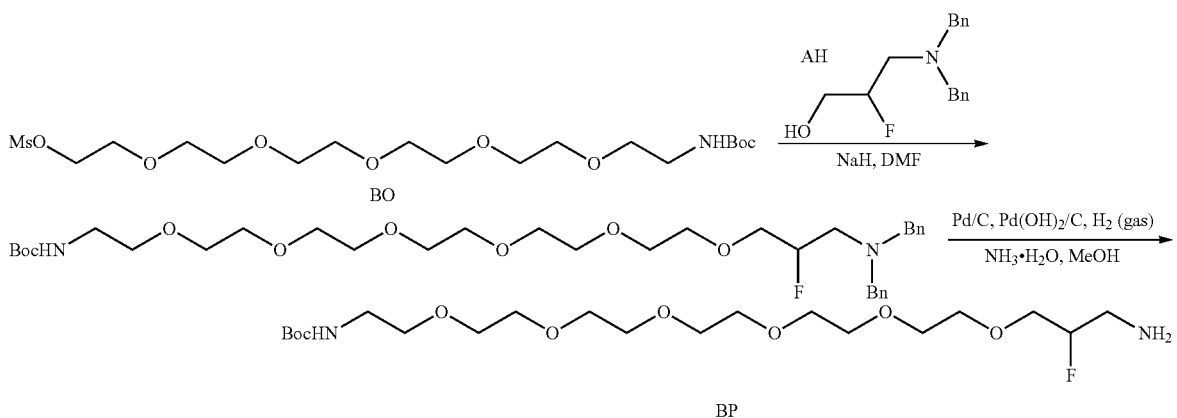

Step 1—Tert-butyl N-[2-[2-[2-[2-[2-[2-[3-(dibenzylamino)-2-fluoro-propoxy]ethoxy]ethoxy]ethoxy]ethoxy]ethoxy]ethyl]carbamate To a solution of 3-(dibenzylamino)-2-fluoro-propan-1-ol (0.50 g, 1.83 mmol, Intermediate AH) in DMF (10.0 mL) was added NaH (219 mg, 5.49 mmol, 60% dispersion in mineral oil), and the mixture was stirred at 0° C. for 1 h. Then 2-[2-[2-[2-[2-[2-(tertbutoxycarbonylamino)ethoxy]ethoxy]ethoxy]ethoxy]ethoxy]ethylmethane sulfonate (1.01 g, 2.20 mmol, Intermediate BO) was added to the reaction mixture and the mixture was allowed to warm to rt and stirred for 16 h. On completion, the mixture was quenched with water (50 mL) and extracted with EA (3×50 mL). The organic layer was dried over anhydrous Na$_2$SO$_4$, filtered and concentrated in vacuo. The mixture was purified by reverse phase flash column chromatography (NH$_3$·H$_2$O, ACN 50%-60%) to give the title compound (300 mg, 21% yield) as a colorless oil. LC-MS (ESI)$^+$ m/z 637.4. (M+H)$^+$.

Step 2—Tert-butyl N-[2-[2-[2-[2-[2-[2-(3-amino-2-fluoro-propoxy)ethoxy]ethoxy]ethoxy]ethoxy]ethoxy]ethyl]carbamate To a solution of tert-butyl N-[2-[2-[2-[2-[2-[2-[3-(dibenzylamino)-2-fluoropropoxy]ethoxy]ethoxy]ethoxy]ethoxy]ethoxy]ethyl]carbamate (0.40 g, 628 umol) in MeOH (5.00 mL) and NH$_3$.H$_2$O (0.2 mL) was added Pd(OH)$_2$/C (0.10 g, 10 wt %) and Pd/C (0.10 g, 10 wt %) under nitrogen atmosphere. The suspension was degassed and purged with hydrogen gas three times. The mixture was stirred under hydrogen atmosphere (50 psi pressure) at rt for 12 h. On completion, the reaction mixture was filtered and the filtrate was concentrated in vacuo to give the title compound (210 mg, 73% yield) as a colorless oil. LC-MS (ESI)$^+$ m/z 457.1. (M+H)$^+$.

Tert-butyl N-[2-[2-[2-[2-[2-(2-azidoethoxy)ethoxy]ethoxy]ethoxy]ethoxy]ethyl]carbamate (Intermediate BQ)

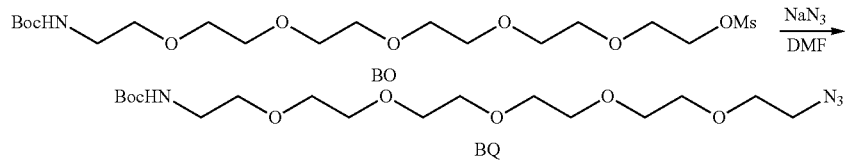

To a solution of 2-[2-[2-[2-[2-[2-(tert-butoxycarbonylamino)ethoxy]ethoxy]ethoxy]ethoxy]ethoxy]ethylmethane sulfonate (4.45 g, 9.68 mmol, Intermediate BO) in DMF (50 mL) was added NaN$_3$ (1.26 g, 19.37 mmol). The reaction mixture then heated to 80° C. and stirred for 16 hours. On completion, the mixture was filtered and the filtrate was concentrated in vacuo to give the title compound (3.90 g, 99% yield) as a yellow oil. LC-MS (ESI$^+$) m/z 424.1 (M+18)$^+$.

Tert-butyl N-[2-[2-[2-[2-[2-[4-[2-(3-amino-2-fluoropropoxy)ethyl]piperazin-1-yl]ethoxy]ethoxy]ethoxy]ethoxy]ethyl]carbamate (Intermediate BR)

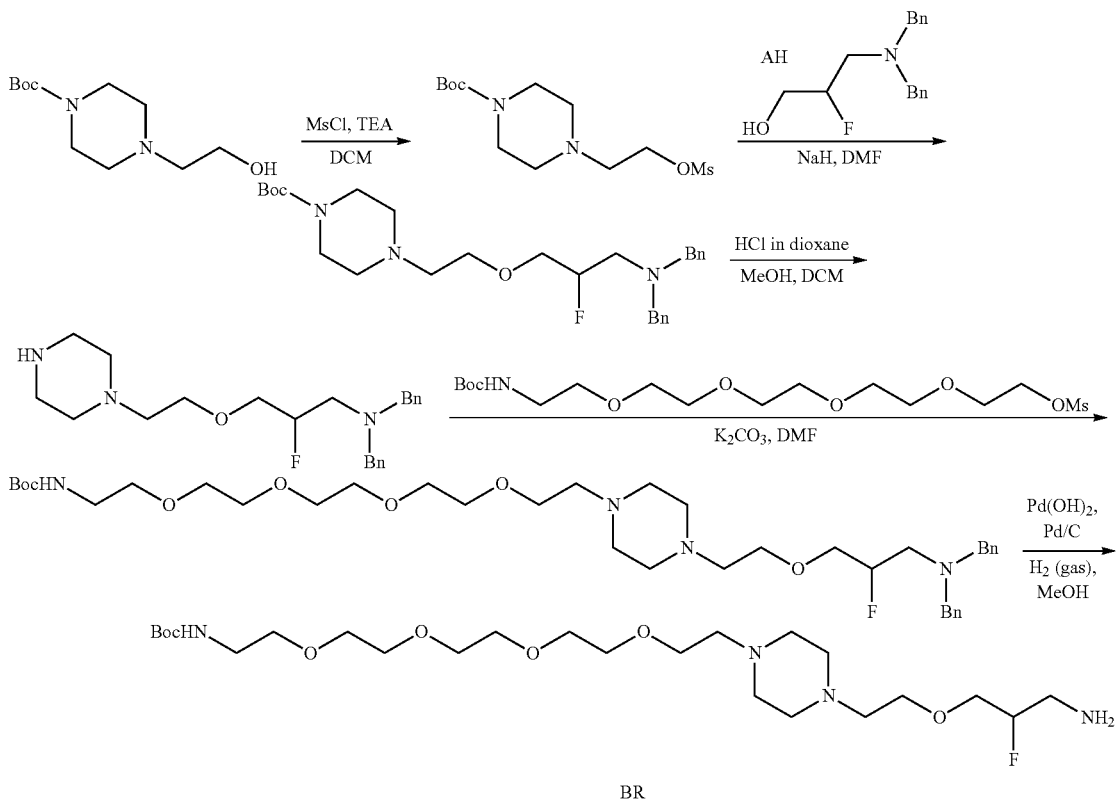

Step 1—Tert-butyl 4-(2-methyl sulfonyloxyethyl)piperazine-1-carboxylate

To a solution of tert-butyl 4-(2-hydroxyethyl)piperazine-1-carboxylate (500 mg, 2.17 mmol, CAS #77279-24-4) in DCM (10 mL) at 0° C. was added TEA (329 mg, 3.26 mmol, 451 uL). After 5 minutes, MsCl (298 mg, 2.60 mmol, 201 uL) was added, and the reaction mixture was allowed to warm to rt and was stirred under nitrogen atmosphere for 3 hours. On completion, the reaction mixture was diluted with H$_2$O (20 mL) and extracted with DCM (2×50 mL). The combined organic layers were dried over Na$_2$SO$_4$, filtered and concentrated in vacuo to give the title compound (620 mg, 93% yield) as a yellowish oil.

Step 2—Tert-butyl 4-[2-[3-(dibenzylamino)-2-fluoro-propoxy]ethyl]piperazine-1-carboxylate To a mixture of tert-butyl 4-(2-methylsulfonyloxyethyl)piperazine-1-carboxylate (620 mg, 2.01 mmol) in DMF (3.00 mL) was added NaH (110 mg, 2.74 mmol, 60% dispersion in mineral oil) at rt under nitrogen atmosphere. The mixture was stirred at rt for 30 minutes, then 3-(dibenzylamino)-2-fluoro-propan-1-ol (500 mg, 1.83 mmol, Intermediate AH) was added to the mixture at rt and the reaction mixture was stirred for 48 hours. On completion, the reaction mixture was quenched with sat. NH$_4$Cl solution (20 mL), then diluted with H$_2$O (20 mL) and extracted with EA (2×50 mL). The combined organic layers were dried over Na$_2$SO$_4$, filtered and concentrated in vacuo to give a residue. The residue was purified by reversed phase flash chromatography (NH$_3$.H$_2$O) to give the title compound (160 mg, 18% yield) as a yellow oil. LC-MS (ESI$^+$) m/z 486.3 (M+H)$^+$.

Step 3—N,N-dibenzyl-2-fluoro-3-(2-piperazin-1-ylethoxy)propan-1-amine

To a mixture of tert-butyl 4-[2-[3-(dibenzylamino)-2-fluoro-propoxy]ethyl]piperazine-1-carboxylate (160 mg, 329 umol) in DCM (5.00 mL) and MeOH (1.00 mL) was added HCl in dioxane (329 umol, 2.00 mL). The mixture was stirred at rt for 1 hour. On completion, the mixture was concentrated in vacuo to give the title compound (200 mg) as a yellow oil. LC-MS (ESI$^+$) m/z 386.2 (M+H)$^+$.

Step 4—Tert-butyl N-[2-[2-[2-[2-[2-[4-[2-[3-(dibenzylamino)-2-fluoro-propoxy]ethyl]piperazin-1-yl]ethoxy]ethoxy]ethoxy]ethoxy]ethyl]carbamate To a mixture of N,N-dibenzyl-2-fluoro-3-(2-piperazin-1-ylethoxy)propan-1-amine (200 mg, 518 umol) and 2-[2-[2-[2-[2-(tert-butoxycarbonylamino)ethoxy]ethoxy]ethoxy]ethyl methanesulfonate (259 mg, 623 umol, synthesized via Steps 1-2 of Intermediate AK) in DMF (1.00 mL) and MeCN (3.00 mL) was added K$_2$CO$_3$ (215 mg, 1.56 mmol). The mixture was then heated to 80° C. and stirred for 12 hours. On completion, the mixture was diluted with H$_2$O (20 mL) and extracted with ethyl acetate (2×40 mL). The combined organic layers were dried over Na$_2$SO$_4$, filtered and concentrated in vacuo to give a residue. The residue was purified by prep-TLC (PE:EA=1:1) to give the title compound (220 mg, 60% yield) as a yellow oil. LC-MS (ESI$^+$) m/z 705.3 (M+H)$^+$.

Step 5—Tert-butyl N-[2-[2-[2-[2-[2-[4-[2-(3-amino-2-fluoro-propoxy)ethyl]piperazin-1-yl]ethoxy]ethoxy]ethoxy]ethyl]carbamate To a solution of tert-butyl N-[2-[2-[2-[2-[2-[4-[2-[3-(dibenzylamino)-2-fluoro-propoxy]ethyl]piperazin-1-yl]ethoxy]ethoxy]ethoxy]ethoxy]ethyl]carbamate (220 mg, 312 umol) in MeOH (7.00 mL) was added Pd(OH)$_2$ (100 mg, 71.2 umol, 10 wt %) and Pd/C (100 mg, 312 umol, 10 wt %). The suspension was degassed under vacuum and purged with hydrogen gas several times. The mixture was then stirred at rt for 192 hours under hydrogen atmosphere (50 psi pressure). On completion, the mixture was filtered and concentrated in vacuo to give the title compound (100 mg, 61% yield) as a white oil.

Tert-butyl (15-amino-14-fluoro-13,13-dimethyl-10-oxo-3,6,12-trioxa-9-azapentadecyl) carbamate (Intermediate BS)

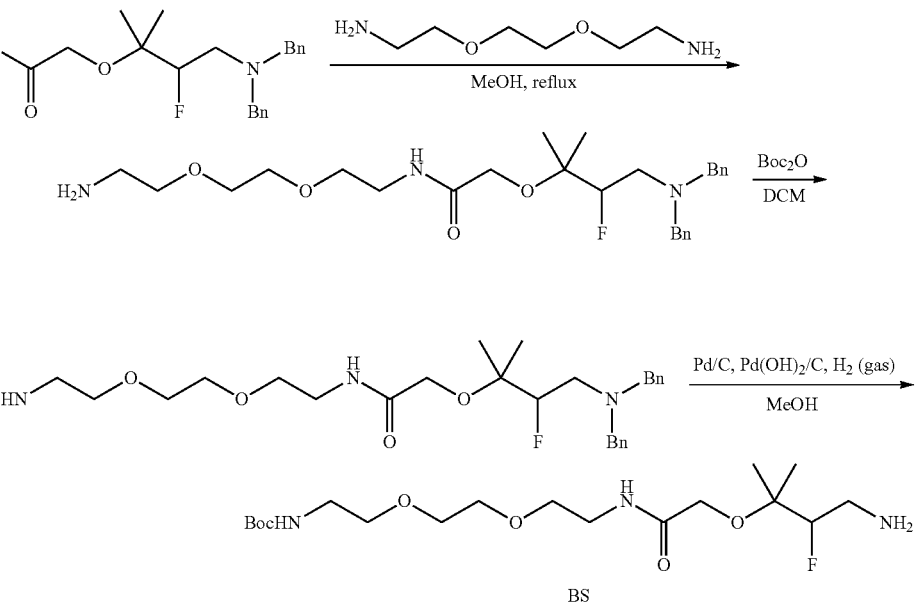

BS

Step 1—N-(2-(2-(2-aminoethoxy)ethoxy)ethyl)-2-((4-(dibenzylamino)-3-fluoro-2-methylbutan-2-yl)oxy)acetamide A solution of ethyl 2-[3-(dibenzylamino)-2-fluoro-1,1-dimethyl-propoxy]acetate (337 mg, 870 umol, synthesized via Steps 1-2 of Intermediate AN) and 2-[2-(2-aminoethoxy)ethoxy]ethanamine (644 mg, 4.35 mmol, CAS #929-59-9) in methanol (2 mL). The reaction mixture was heated to 80° C. for 12 hrs. On completion, the reaction mixture was concentrated in vacuo to give the title compound (850 mg, 40% yield) as a colorless oil. LC-MS (ESI$^+$) m/z 490.3 (M+H)$^+$.

Step 2—Tert-butyl (2-benzyl-4-fluoro-5,5-dimethyl-8-oxo-1-phenyl-6,12,15-trioxa-2,9-diazaheptadecan-17-yl)carbamate To a solution of N-[2-[2-(2-aminoethoxy)ethoxy]ethyl]-2-[3-(dibenzylamino)-2-fluoro-1,1-dimethyl-propoxy]acetamide (920 mg, 1.60 mmol) in DCM (5 mL) was added (Boc)$_2$O (5.23 g, 24.0 mmol). The reaction mixture was stirred at rt for 14 h. On completion, the reaction mixture was concentrated in vacuo. The residue was purified by reversed phase chromatography (NH$_3$.H$_2$O, 0.1%) to give the title compound (440 mg, 44% yield) as a colorless oil. $^1$H NMR (400 MHz, CDCl$_3$) δ=7.42-7.37 (m, 4H), 7.35-7.33 (m, 4H), 7.28-7.23 (m, 2H), 6.80 (s, 1H), 5.01 (s, 1H), 4.66-4.45 (m, 1H), 3.93-3.83 (m, 2H), 3.81-3.70 (m, 2H), 3.63-3.60 (d, J=14.0 Hz, 2H), 3.60-3.44 (m, 10H), 3.32-3.31 (m, 2H), 2.91-2.67 (m, 2H), 1.46 (s, 9H), 1.10 (s, 6H). LC-MS (ESI$^+$) m/z 590.4 (M+H)$^+$.

Step 3—Tert-butyl (15-amino-14-fluoro-13,13-dimethyl-10-oxo-3,6,12-trioxa-9-azapentadecyl)carbamate To a solution of tert-butyl N-[2-[2-[2-[[2-[3-(dibenzylamino)-2-fluoro-1,1-dimethyl-propoxy]acetyl]amino]ethoxy]ethoxy]ethyl]carbamate (440 mg, 746 umol) in MeOH (5 mL) was added Pd(OH)$_2$/C (200 mg, 10 wt %) and Pd/C (200 mg, 10 wt %) under nitrogen atmosphere. The suspension was degassed and purged with hydrogen gas three times. The mixture was stirred under hydrogen atmosphere (55 psi pressure) at rt for 15 h. On completion, the reaction mixture was filtered and the filtrate was concentrated in vacuo to give the title compound (270 mg, 88% yield) as a yellow solid. LC-MS (ESI$^+$) m/z 410.2 (M+H)$^+$.

Tert-butyl N-[2-[2-[2-(3-amino-2-fluoro-propoxy)-1-methyl-ethoxy]ethoxy]ethyl]carbamate (Intermediate BT)

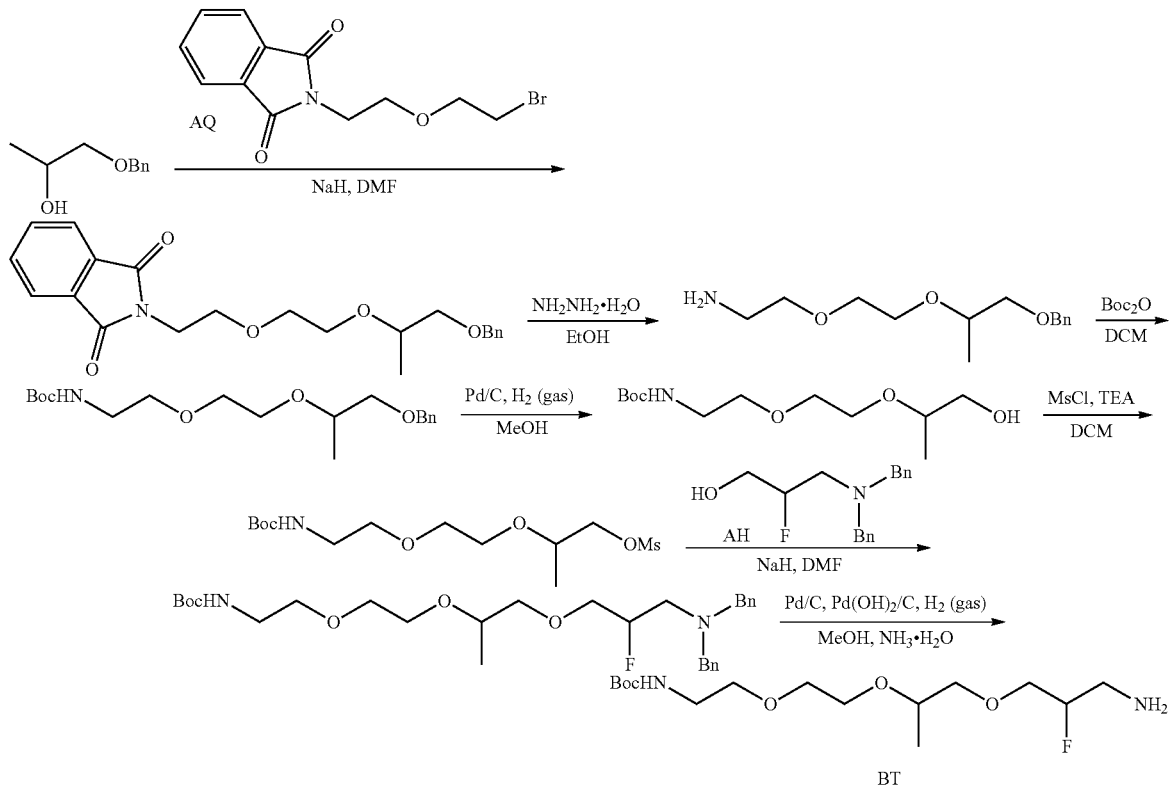

Step 1—2-[2-[2-(2-Benzyloxy-1-methyl-ethoxy)ethoxy]ethyl]isoindoline-1,3-dione To a solution of 1-benzyloxypropan-2-ol (2.5 g, 15.0 mmol, synthesized via Step 1 of Intermediate BU) in DMF (40 mL) was added NaH (1.80 g, 45.12 mmol, 60% dispersion in mineral oil) and the mixture was stirred at rt for 30 min. Then 2-[2-(2-Bromoethoxy)ethyl]isoindoline-1,3-dione (4.48 g, 15.0 mmol, Intermediate AQ) was added to the mixture and the mixture was stirred at rt for an additional 12 h. On completion, the reaction mixture was quenched with H₂O (10 mL) and then concentrated in vacuo to give the title compound (5 g) as yellow solid. LC-MS (ESI⁺) m/z 384.1 (M+H)⁺.

Step 2—2-[2-(2-Benzyloxy-1-methyl-ethoxy)ethoxy]ethanamine

To a solution of 2-[2-[2-(2-benzyloxy-1-methyl-ethoxy)ethoxy]ethyl]isoindoline-1,3-dione (10 g, 26.0 mmol) in EtOH (100 mL) was added N₂H4.H₂O (6.66 g, 130 mmol, 6.47 mL, 98% solution), and the mixture was heated to 80° C. and stirred for 12 h. On completion, the mixture was filtered and the filtrate was concentrated in vacuo to give the title compound (6 g) as a yellow oil. LC-MS (ESI⁺) m/z 254.1 (M+H)⁺.

Step 3—Tert-butyl N-[2-[2-(2-benzyloxy-1-methyl-ethoxy)ethoxy]ethyl]carbamate To a solution of 2-[2-(2-benzyloxy-1-methyl-ethoxy)ethoxy]ethanamine (6 g, 23.6 mmol) in DCM (40 mL) was added Boc₂O (10.3 g, 47.3 mmol, 10.8 mL) and the mixture was stirred at rt for 2 h. On completion, the reaction mixture was concentrated in vacuo to give a residue. The residue was purified by reverse phase chromatography (NH₃.H₂O) to give the title compound (3 g, 32% yield over steps 1-3) as a white solid. LC-MS (ESI⁺) m/z 376.2 (M+Na)⁺.

Step 4—Tert-butyl N-[2-[2-(2-hydroxy-1-methyl-ethoxy)ethoxy]ethyl]carbamate

To a solution of tert-butyl N-[2-[2-(2-benzyloxy-1-methyl-ethoxy)ethoxy]ethyl]carbamate (3 g, 8.49 mmol) in MeOH (30 mL) was added Pd/C (1.5 g, 10 wt %). The mixture was then heated to 40° C. and stirred under hydrogen atmosphere (50 psi pressure) for 18 h. On completion, the reaction mixture was filtered and the filtrate was concentrated in vacuo to give the title compound (2 g, 45% yield) as a colorless oil. $^1$H NMR (400 MHz, CDCl₃) δ 5.14 (s, 1H), 3.84-3.76 (m, 1H), 3.68-3.55 (m, 7H), 3.54-3.45 (m, 1H), 3.34 (J=4.8 Hz, 2H), 1.46 (s, 9H), 1.15 (d, J=6.4 Hz, 3H).

Step 5—2-[2-[2-(Tert-butoxycarbonylamino)ethoxy]ethoxy]propyl methanesulfonate To a solution of tert-butyl N-[2-[2-(2-hydroxy-1-methyl-ethoxy)ethoxy]ethyl]carbamate (0.44 g, 1.67 mmol) in DCM (5 mL) was added TEA (507 mg, 5.01 mmol, 697 uL) and MsCl (287 mg, 2.51 mmol, 193 uL) dropwise at 0° C. The mixture was allowed to warm to rt and stirred for 3 h. On completion, the reaction mixture was diluted with water (10 mL) and extracted with DCM (2×20 mL). The organic phase was dried over Na₂SO₄, filtered and the filtrate was concentrated in vacuo to give the title compound (0.56 g, 90% yield) as a yellow oil.

Step 6—Tert-butyl N-[2-[2-[2-[3-(dibenzylamino)-2-fluoro-propoxy]-1-methyl-ethoxy]ethoxy]ethyl]carbamate To a solution of 3-(dibenzylamino)-2-fluoro-propan-1-ol (298 mg, 1.09 mmol, Intermediate AH) in DMF (8 mL) was added NaH (131 mg, 3.28 mmol, 60% dispersion in mineral oil) and the mixture was stirred at rt for 30 min. Then 2-[2-[2-(tert-butoxycarbonylamino)ethoxy]ethoxy]propyl methanesulfonate (0.56 g, 1.64 mmol) was added to the mixture and the mixture was stirred at rt for an additional 12 h. On completion, the reaction mixture was quenched with water (0.5 mL) and then concentrated in vacuo to give a residue. The residue was purified by reversed phase chromatography (0.1% NH₃.H₂O) to give the title compound (130 mg, 22% yield) as a yellow oil. LC-MS (ESI⁺) m/z 519.4 (M+Na)⁺.

Step 7—Tert-butyl N-[2-[2-[2-(3-amino-2-fluoro-propoxy)-1-methyl-ethoxy]ethoxy]ethyl]carbamate To a solution of tert-butyl N-[2-[2-[2-[3-(dibenzylamino)-2-fluoro-propoxy]-1-methyl-ethoxy]ethoxy]ethyl]carbamate (0.3 g, 578 umol) in MeOH (10 mL) and NH₃.H₂O (1 mL) was added Pd(OH)₂/C (0.2 g, 10 wt %) and Pd/C (0.2 g, 10 wt %), and the mixture was stirred at rt for 12 h under hydrogen atmosphere (15 psi pressure). On completion, the reaction mixture was filtered and the filtrate was concentrated in vacuo to give the title compound (140 mg, 71% yield) as a colorless oil. LC-MS (ESI⁺) m/z 339.2 (M+H)⁺.

2-[2-[2-[2-(3-Amino-2-fluoro-propoxy)ethoxy]ethoxy]propyl]isoindoline-1,3-dione (Intermediate BU)

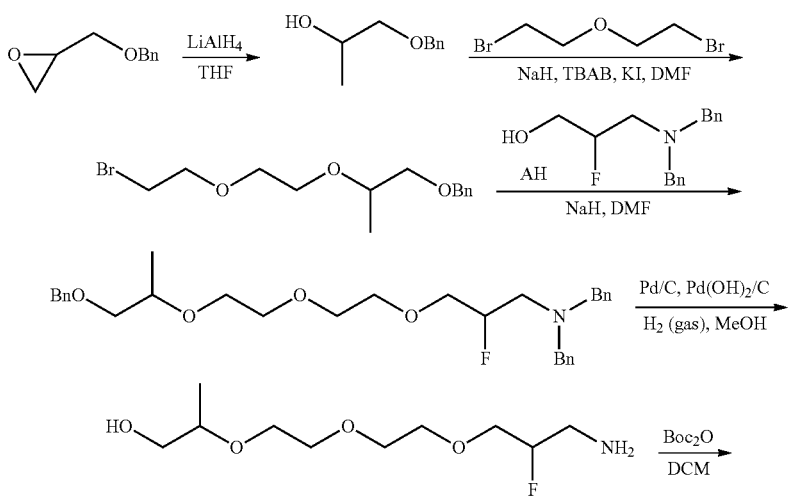

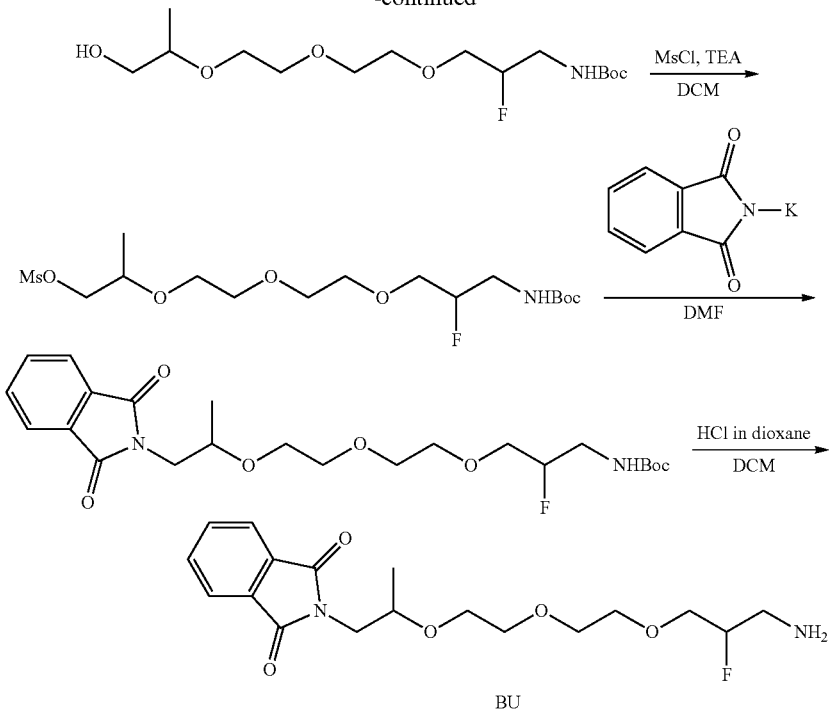

Step 1—1-Benzyloxypropan-2-ol

To a solution of LiAlH$_4$ (7.56 g, 199 mmol) in anhydrous tetrahydrofuran (100 mL) was added a solution of 2-(benzyloxymethyl)oxirane (21.8 g, 132 mmol, 20.1 mL) in anhydrous tetrahydrofuran (300 mL) dropwise at 0° C. under nitrogen atmosphere. The mixture was then stirred for 1 hour. On completion, the reaction mixture was quenched with water (15 mL), then 15% sodium hydroxide solution (15 mL) was added, and the mixture was stirred for a further 15 minutes until no precipitate formed. Next, the inorganic salt precipitate was filtered off and the filter cake was washed with ethyl acetate (2×100 mL). The combine organic phase was dried over anhydrous magnesium sulfate, filtered and concentrated in vacuo to give a residue. The residue was purified by silica gel chromatography (petroleum ether:ethyl acetate=2:1) to give the title compound (21.3 g, 96% yield) as a colorless oil. $^1$H NMR (400 MHz, CDCl$_3$) δ 7.40-7.29 (m, 5H), 4.57 (s, 2H), 4.08-3.94 (m, 1H), 3.49 (dd, J=3.2, 9.2 Hz, 1H), 3.30 (dd, J=8.4, 9.2 Hz, 1H), 2.40 (d, J=2.4 Hz, 1H), 1.16 (d, J=6.4 Hz, 3H).

Step 2—2-[2-(2-Bromoethoxy)ethoxy]propoxymethylbenzene

A mixture of 1-benzyloxypropan-2-ol (4.00 g, 24.0 mmol), 1-bromo-2-(2-bromoethoxy)ethane (27.9 g, 120 mmol, 15.0 mL), tetrabutylammonium bromide (7.76 g, 24.0 mmol), potassium iodide (3.99 g, 24.0 mmol) and sodium hydride (2.89 g, 72.2 mmol, 60% dispersion in mineral oil) in N,N-dimethylformamide (40 mL) was degassed and purged with nitrogen gas three times. Then the mixture was stirred at rt for 20 hours under nitrogen atmosphere. On completion, the reaction mixture was poured into ice water (100 mL) and extracted with ethyl acetate (3×100 mL). The combined organic phase was dried over anhydrous sodium sulfate filtered and concentrated in vacuo to get a residue. The residue was purified by column chromatography (petroleum ether:ethyl acetate=6:1) to give the title compound (4.20 g, 55% yield) as a colorless oil. $^1$H NMR (400 MHz, CDCl$_3$) δ 7.40-7.25 (m, 5H), 4.58 (s, 2H), 3.83 (t, J=6.4 Hz, 2H), 3.75-3.66 (m, 5H), 3.56-3.42 (m, 4H), 1.20 (d, J=6.4 Hz, 3H).

Step 3—N,N-dibenzyl-3-[2-[2-(2-benzyloxy-1-methyl-ethoxy)ethoxy]ethoxy]-2-fluoro-propan-1-amine To a solution of 3-(dibenzylamino)-2-fluoro-propan-1-ol (2.00 g, 7.32 mmol, Intermediate AH) in N,N-dimethylformamide (40 mL) was added sodium hydride (878 mg, 21.9 mmol, 60% dispersion in mineral oil) at 0° C. and the reaction was stirred for 30 minutes. Then 2-[2-(2-bromoethoxy)ethoxy]propoxy-methylbenzene (2.50 g, 7.88 mmol) was added and the reaction mixture was then allowed to warm to rt and stirred for a further 15.5 hours. On completion, the reaction mixture was quenched with ice water (120 mL) and extracted with ethyl acetate (3×50 mL). The organic phase was collected, dried over anhydrous sodium sulfate, filtered and concentrated in vacuo to get a residue. The residue was purified by column chromatography (petroleum ether:ethyl acetate=4:1) to give the title compound (2.60 g, 69% yield) as a colorless oil. $^1$H NMR (400 MHz, CDCl$_3$) δ 7.40-7.34 (m, 15H), 4.91-4.71 (m, 1H), 4.59 (d, J=2.4 Hz, 2H), 3.74-3.60 (m, 16H), 3.48-3.42 (m, 1H), 2.81-2.72 (m, 2H), 1.21 (d, J=6.4 Hz, 3H).

Step 4—2-[2-[2-(3-Amino-2-fluoro-propoxy)ethoxy]ethoxy]propan-1-ol

To a solution of N,N-dibenzyl-3-[2-[2-(2-benzyloxy-1-methyl-ethoxy)ethoxy]ethoxy]-2-fluoro-propan-1-amine (2.30 g, 4.51 mmol) in methanol (30 mL) was added Pd/C (1.00 g, 10 wt %) and Pd(OH)$_2$/C (1.00 g, 10 wt %) under nitrogen gas atmosphere. The suspension was degassed under vacuum and purged with hydrogen gas several times. The mixture was stirred under hydrogen gas (50 psi pressure) at rt for 18 h. On completion, the reaction mixture was filtered through a pad of celite and the pad and the filter cake was washed with methanol (3×10 mL). The filtration was concentrated in vacuo to give the crude product (930 mg, 86% yield) as a colorless oil. LC-MS (ESI)$^+$ m/z 240.0. (M+H)$^+$.

Step 5—Tert-butyl N-[2-fluoro-3-[2-[2-(2-hydroxy-1-methyl-ethoxy)ethoxy]ethoxy]propyl]carbamate To a solution of 2-[2-[2-(3-amino-2-fluoro-propoxy)ethoxy]ethoxy]propan-1-ol (850 mg, 3.55 mmol) in dichloromethane (30 mL) was added Boc$_2$O (852 mg, 3.91 mmol, 897 uL) dropwise. The mixture was stirred at rt for 2 hours. On completion, the reaction mixture was concentrated in vacuo to give a residue. The residue was purified by silica gel column chromatography (petroleum ether:ethyl acetate=0:1) to give the title compound (930 mg, 77% yield) as a colorless gum. $^1$H NMR (400 MHz, CDCl$_3$) δ 5.28 (m, 1H), 4.83-4.60 (m, 1H), 3.87-3.79 (m, 1H), 3.73-3.58 (m, 11H), 3.50-3.36 (m, 3H), 3.13 (br s, 1H), 1.45 (s, 9H), 1.13 (d, J=6.4 Hz, 3H).

Step 6—2-[2-[2-[3-(Tert-butoxycarbonylamino)-2-fluoro-propoxy]ethoxy]ethoxy]propyl methanesulfonate To a solution of tert-butyl N-[2-fluoro-3-[2-[2-(2-hydroxy-1-methyl-ethoxy)ethoxy]ethoxy]propyl]-carbamate (880 mg, 2.59 mmol) in dichloromethane (30 mL) was added triethylamine (787 mg, 7.78 mmol, 1.08 mL) and the reaction mixture was cooled to 0° C. Then methylsulfonyl chloride (445 mg, 3.89 mmol, 301 uL) was added dropwise at 0° C. Then, the mixture was allowed to warm to rt and stirred for 30 minutes. On completion, the reaction mixture was quenched with ice water (30 mL), The organic phase was separated, washed with citric acid (30 mL), then dried over anhydrous magnesium, filtered and concentrated in vacuo to give the title compound (1.00 g, 92% yield) as a colorless gum. $^1$H NMR (400 MHz, CDCl$_3$) δ 4.97 (m, 1H), 4.80-4.60 (m, 1H), 4.24-4.12 (m, 2H), 3.82-3.61 (m, 11H), 3.47-3.28 (m, 2H), 3.08 (s, 3H), 1.45 (s, 9H), 1.22 (d, J=6.4 Hz, 3H).

Step 7—Tert-butyl N-[3-[2-[2-[2-(1,3-dioxoisoindolin-2-yl)-1-methyl-ethoxy]ethoxy]ethoxy]-2-fluoro-propyl]carbamate To a solution of 2-[2-[2-[3-(tert-butoxycarbonylamino)-2-fluoro-propoxy]ethoxy]ethoxy]propyl methanesulfonate (1.00 g, 2.40 mmol) in N,N-dimethylformamide (20 mL) was added (1,3-dioxoiso-indolin-2-yl)potassium (532 mg, 2.87 mmol). The mixture then heated to 80° C. and stirred for 16 h. On completion, the reaction mixture was concentrated in vacuo to get a residue. The residue was diluted in ice water (20 mL) and extracted with ethyl acetate (3×15 mL). The organic phase was collected, dried over anhydrous magnesium sulfate, filtered and concentrated under reduced pressure to give a residue. The residue was purified by silica gel column chromatography (petroleum ether:ethyl acetate=3:1) to give the title compound (730 mg, 65% yield) as a colorless gum. $^1$H NMR (400 MHz, CDCl$_3$) δ 7.78 (m, 2H), 7.65 (m, 2H), 4.91 (m, 1H), 4.70-4.49 (m, 1H), 3.81-3.70 (m, 2H), 3.66-3.42 (m, 12H), 3.30-3.18 (m, 1H), 1.37 (s, 9H), 1.14 (d, J=6.4 Hz, 3H).

Step 8—2-[2-[2-[2-(3-Amino-2-fluoro-propoxy)ethoxy]ethoxy]propyl]isoindoline-1,3-dione To a solution of tert-butyl N-[3-[2-[2-[2-(1,3-dioxoisoindolin-2-yl)-1-methyl-ethoxy]ethoxy]ethoxy]-2-fluoro-propyl]carbamate (350 mg, 747 umol) in dichloromethane (14 mL) was added a solution of hydrochloric acid in dioxane (4 M, 14 mL). The mixture was stirred at rt for 30 minutes. On completion, the reaction mixture was concentrated in vacuo to give the title compound (300 mg, 99% yield, hydrochloride salt) as a colorless gum. LC-MS (ESI)$^+$ m/z 369.1. (M+H)$^+$.

Tert-butyl N-[3-[3-(3-amino-2-fluoro-propoxy)propoxy]propyl]carbamate (Intermediate BV)

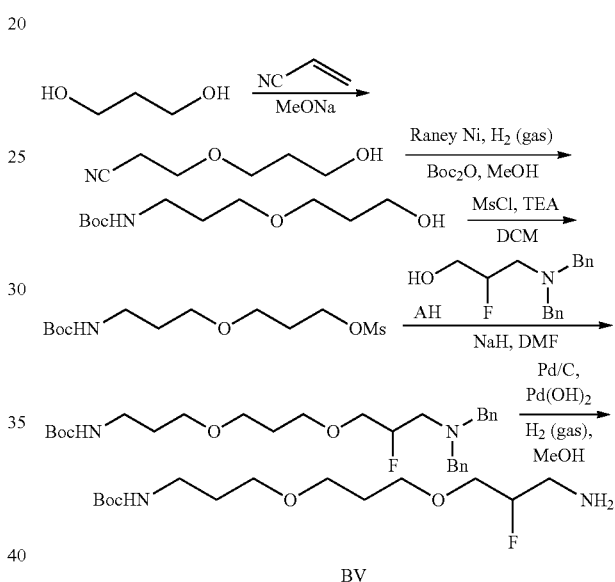

Step 1—3-(3-Hydroxypropoxy)propanenitrile

To a mixture of propane-1,3-diol (28.7 g, 377 mmol, 27.3 mL) and prop-2-enenitrile (20.0 g, 377 mmol, 25.0 mL) was added NaOMe (204 mg, 3.77 mmol). The mixture was stirred at rt for 20 h. On completion, the reaction mixture was concentrated in vacuo to give a residue. The residue was purified by silica column chromatography to give the title compound (20.3 g, 41% yield) as a colorless oil. $^1$H NMR (400 MHz, CDCl$_3$) δ 3.70 (t, J=6.0 Hz, 2H), 3.65-3.57 (m, 4H), 2.55 (t, J=6.4 Hz, 2H), 1.99 (s, 1H), 1.79 (m, 2H).

Step 2—Tert-butyl N-[3-(3-hydroxypropoxy)propyl]carbamate

To a solution of 3-(3-hydroxypropoxy)propanenitrile (5.00 g, 38.7 mmol) in MeOH (50 mL) was added Raney-Ni (1.00 g) and (Boc)$_2$O (12.7 g, 13.3 mL) under nitrogen atmosphere. The suspension was degassed and purged with hydrogen gas three times. The mixture was stirred under hydrogen atmosphere (50 psi pressure) at rt for 72 h. On completion, the mixture was filtered and the filtrate was concentrated in vacuo to give a residue. The residue was purified by silica column chromatography to give the title compound (6.5 g, 72% yield) as a colorless oil. $^1$H NMR (400 MHz, CDCl$_3$) δ 4.86 (s, 1H), 3.79 (t, J=5.6 Hz, 2H), 3.60 (t, J=6.0 Hz, 2H), 3.50 (t, J=6.0 Hz, 2H), 3.30-3.18 (m, 2H), 2.63 (s, 1H), 1.87-1.70 (m, 4H), 1.45 (s, 9H).

Step 3—3-[3-(Tert-butoxycarbonylamino)propoxy]propyl methanesulfonate

To a solution of tert-butyl N-[3-(3-hydroxypropoxy)propyl]carbamate (1.20 g, 5.14 mmol) in DCM (10 mL) was added Et$_3$N (1.56 g, 2.15 mL, 15.4 mmol) and MsCl (884 mg, 7.72 mmol). The mixture was stirred at rt for 2 h. On completion, the reaction was quenched with water (10 mL) and extracted with DCM (2×30 mL). The organic layer was washed with brine (20 mL), dried over anhydrous Na$_2$SO$_4$, filtered and concentrated in vacuo to give the title compound (1.60 g, 99% yield) as a yellow oil. $^1$H NMR (400 MHz, CDCl$_3$) δ 4.88-4.78 (s, 1H), 4.36 (t, J=6.0 Hz, 2H), 3.52 (m, 4H), 3.27-3.19 (m, 2H), 3.03 (s, 3H), 2.01 (t, J=6.0 Hz, 2H), 1.76 (t, J=6.0 Hz, 2H), 1.45 (s, 9H).

Step 4—Tert-butyl N-[3-[3-(3-amino-2-fluoro-propoxy)propoxy]propyl]carbamate

To a solution of 3-(dibenzylamino)-2-fluoro-propan-1-ol (1.00 g, 3.66 mmol, Intermediate AH) in DMF (20 mL) was added NaH (439 mg, 11.0 mmol, 60% dispersion in mineral oil) and the reaction mixture was stirred for 30 minutes at rt. Then, 3-[3-(tert-butoxycarbonylamino) propoxy]propyl methanesulfonate (1.48 g, 4.76 mmol) was added and the mixture was stirred at rt for an additional 12 h. On completion, the reaction was quenched with saturated NH$_4$Cl solution and extracted with EA (3×50 mL). The organic layer was dried over Na$_2$SO$_4$, filtered and concentrated in vacuo. The residue was purified by reversed phase chromatography (0.1% NH$_3$.H2O in water) to give the title compound (800 mg, 45% yield). LC-MS (ESI$^+$) m/z 489.4 (M+H)$^+$.

Step 5—Tert-butyl N-[3-[3-(3-amino-2-fluoro-propoxy)propoxy]propyl]carbamate

To a solution of tert-butyl N-[3-[3-[3-(dibenzylamino)-2-fluoro-propoxy]propoxy]propyl]carbamate (600 mg, 1.23 mmol) in MeOH (10 mL) was added Pd/C (200 mg, 10 wt %) and Pd(OH)$_2$/C (200 mg, 10 wt %) under nitrogen atmosphere. The suspension was degassed and purged with hydrogen gas three times. The mixture was stirred under hydrogen atmosphere (50 psi pressure) at rt for 18 h. On completion, the mixture was filtered and concentrated in vacuo to give the title compound (370 mg, 98% yield) as a white gum. LC-MS (ESI$^+$) m/z 309.0 (M+H)$^+$.

Methyl 2-[2-[2-[2-[2-[2-(3-amino-2-fluoro-propoxy)ethoxy]ethoxy]ethoxy]ethoxy]ethoxy]acetate (Intermediate BW)

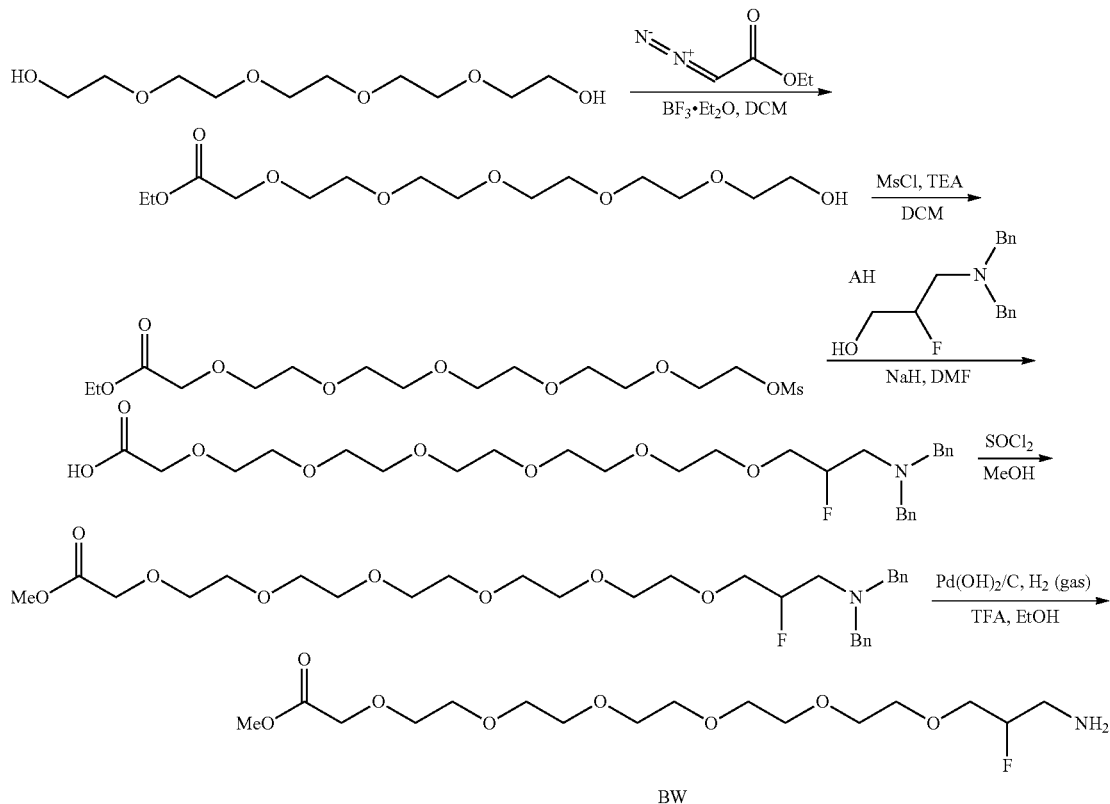

BW

Step 1—Ethyl 2-[2-[2-[2-[2-(2-hydroxyethoxy)ethoxy]ethoxy]ethoxy]ethoxy]acetate

To a mixture 2-[2-[2-[2-(2-hydroxyethoxy)ethoxy]ethoxy]ethoxy]ethanol (14.0 g, 58.7 mmol, CAS #4792-15-8) and BF$_3$.Et$_2$O (833 mg, 5.88 mmol) in DCM (200 mL) was added dropwise ethyl 2-diazoacetate (6.70 g, 58.7 mmol) in DCM (100 mL) at rt under nitrogen atmosphere. The reaction mixture was stirred at rt for 12 hours. On completion, the reaction mixture was concentrated in vacuo. The residue was purified by flash chromatography (DCM/MeOH=100/1) to give the title compound (5.00 g, 26% yield) as a colorless oil. $^1$H NMR (400 MHz, CDCl$_3$) δ 4.20 (q, J=7.2 Hz, 2H), 4.14 (s, 2H), 3.75-3.62 (m, 18H), 3.62-3.58 (m, 2H), 2.69 (s, 1H), 1.27 (t, J=7.2 Hz, 3H).

Step 2—Ethyl 2-[2-[2-[2-[2-(2-methylsulfonyloxyethoxy)ethoxy]ethoxy]ethoxy]ethoxy]acetate To a mixture of ethyl 2-[2-[2-[2-[2-(2-hydroxyethoxy)ethoxy]ethoxy]ethoxy]ethoxy]acetate (5.00 g, 15.4 mmol) in DCM (50 mL) was added TEA (4.68 g, 46.2 mmol) and the reaction was cooled to 0° C. Then MsCl (2.12 g, 18.4 mmol) was added dropwise at 0° C. and the reaction mixture was allowed to warm to rt and stirred for 3 hours. On completion, the reaction mixture was diluted with water (30 mL) and extracted with DCM (3×50 mL). The combined organic layers were dried over Na$_2$SO$_4$, filtered and concentrated in vacuo to give the title compound (6.60 g, 95% yield) as a light yellow oil. $^1$H NMR (400 MHz, CDCl$_3$) δ 4.39-4.35 (m, 2H), 4.20 (q, J=7.2 Hz, 2H), 4.14 (s, 2H), 3.79-3.60 (m, 18H), 3.08 (s, 3H), 1.27 (t, J=7.2 Hz, 3H).

Step 3—2-[2-[2-[2-[2-[2-[3-(Dibenzylamino)-2-fluoro-propoxy]ethoxy]ethoxy]ethoxy]ethoxy]ethoxy]acetic acid To a mixture of 3-(dibenzylamino)-2-fluoro-propan-1-ol (67.9 mg, 248 umol, Intermediate AH) in DMF (4 mL) was added NaH (14.9 mg, 372 umol, 60% dispersion in mineral oil) at 0° C. Then, the reaction mixture was allowed to warm to rt and stirred for 0.5 hour. Then ethyl 2-[2-[2-[2-[2-(2-methylsulfonyloxyethoxy)ethoxy]ethoxy]ethoxy]ethoxy]acetate (100 mg, 248 umol) was added and the reaction mixture was stirred at rt for an additional 12 hours. On completion, the reaction mixture was concentrated in vacuo. The residue was diluted with water (10 mL) and extracted with EA (2×20 mL). The combined organic layers were dried over Na$_2$SO$_4$, filtered and concentrated in vacuo to give a residue. The residue was purified by prep-TLC (DCM/MeOH=10/1) to give the title compound (64.0 mg, 46% yield) as a colorless oil. LC-MS (ESI)$^+$ m/z 552.2. (M+H)$^+$.

Step 4—Methyl 2-[2-[2-[2-[2-[2-[3-(dibenzylamino)-2-fluoro-propoxy]ethoxy]ethoxy]ethoxy]ethoxy]ethoxy]acetate To a mixture of 2-[2-[2-[2-[2-[2-[3-(dibenzylamino)-2-fluoro-propoxy]ethoxy]ethoxy]ethoxy]ethoxy]ethoxy]acetic acid (2.10 g, 3.81 mmol) in MeOH (20 mL) was added SOCl$_2$ (3.28 g, 27.5 mmol). The reaction mixture was stirred at rt for 38 hours. On completion, the reaction mixture was filtered and concentrated in vacuo to give a residue. The residue was diluted with water (10 mL) and extracted with DCM (4×30 mL). The combined organic layers were dried over Na$_2$SO$_4$, filtered and concentrated in vacuo to give a residue. The residue was purified by silica gel column chromatography to give the title compound (550 mg, 25% yield) as a light yellow oil. $^1$H NMR (400 MHz, CDCl$_3$) δ 7.30-7.21 (m, 8H), 7.18-7.13 (m, 2H), 4.10 (s, 2H), 3.69-3.60 (m, 8H), 3.60-3.51 (m, 22H), 2.68 (d, J=5.6 Hz, 1H), 2.63 (d, J=5.2 Hz, 1H).

Step 5—Methyl 2-[2-[2-[2-[2-[2-(3-amino-2-fluoro-propoxy)ethoxy]ethoxy]ethoxy]ethoxy]ethoxy]acetate To a mixture of methyl 2-[2-[2-[2-[2-[2-[3-(dibenzylamino)-2-fluoro-propoxy]ethoxy]ethoxy]ethoxy]ethoxy]ethoxy]acetate (10.0 mg, 17.6 umol) in EtOH (1 mL) was added TFA (15.4 mg, 10.0 uL, 135 umol) and Pd(OH)$_2$/C (20.0 mg, 10 wt %) under hydrogen atmosphere (15 psi pressure). The reaction mixture was stirred at rt for 12 hours. On completion, the reaction mixture was filtered and concentrated in vacuo. The residue was diluted with water (8 mL) and extracted with EA (3×15 mL). The combined organic layers were dried over Na$_2$SO$_4$, filtered and concentrated in vacuo to give the title compound (6.00 mg, 88% yield) as a light yellow oil. LC-MS (ESI)$^+$ m/z 386.2. (M+H)$^+$.

Methyl 2-(2-(2-(3-amino-2-fluoropropoxy)ethoxy)ethoxy)acetate (Intermediate BX)

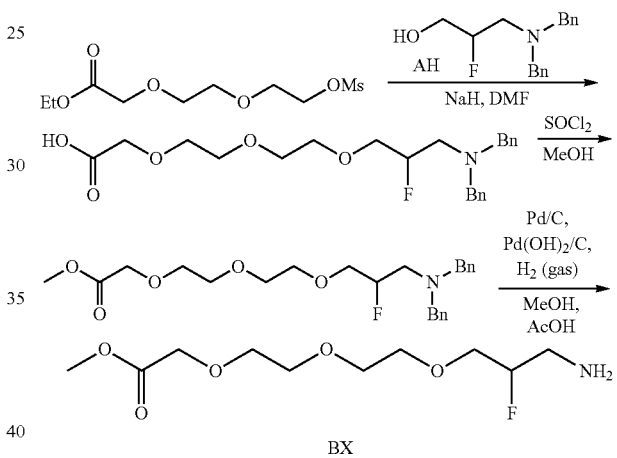

Step 1—2-[2-[2-[3-(Dibenzylamino)-2-fluoropropoxy]ethoxy]ethoxy]acetic acid

To a solution of 3-(dibenzylamino)-2-fluoro-propan-1-ol (1.5 g, 5.49 mmol, Intermediate AH) in DMF (20 mL) was added NaH (658 mg, 60% dispersion in mineral oil) at rt. After stirred for 30 minutes, ethyl 2-[2-(2-methylsulfonyloxyethoxy)ethoxy]acetate (1.93 g, 7.13 mmol, synthesized via Steps 1-2 of Intermediate BM) was added and the mixture was stirred at rt for 12 h. On completion, the mixture was poured into water (60 mL) and extracted with EA (3×50 mL). The organic layer was washed with brine (20 mL), dried over anhydrous Na$_2$SO$_4$, filtered and concentrated in vacuo to give the title compound (2.00 g, 40% yield). LC-MS (ESI$^+$) m/z 420.1 (M+H)$^+$.

Step 2—Methyl 2-[2-[2-[3-(dibenzylamino)-2-fluoro-propoxy]ethoxy]ethoxy]acetate

A mixture of 2-[2-[2-[3-(dibenzylamino)-2-fluoro-propoxy]ethoxy]ethoxy]acetic acid (2.00 g, 4.77 mmol), SOCl$_2$ (24.6 g, 15 mL) and MeOH (20 mL) was stirred at 70° C. for 1 hour under nitrogen atmosphere. On completion, the reaction mixture was concentrated in vacuo. The residue was purified by silica gel chromatography (DCM: MeOH=100:1 to 20:1) to give the title compound (900 mg, 39% yield) as a red oil. LC-MS (ESI+) m/z 434.1 (M+H)+.

Step 3—Methyl 2-(2-(2-(3-amino-2-fluoropropoxy) ethoxy)ethoxy)acetate

To a solution of methyl 2-[2-[2-[3-(dibenzylamino)-2-fluoro-propoxy]ethoxy]ethoxy]acetate (1.00 g, 2.31 mmol) in MeOH (20 mL) was added Pd(OH)$_2$/C (100 mg, 10 wt %), Pd/C (100 mg, 10 wt %) and acetic acid (0.1 mL) under nitrogen atmosphere. The suspension was degassed and purged with hydrogen gas three times. The mixture was stirred under hydrogen atmosphere (50 psi pressure) at rt for 24 hrs. On completion, the mixture was filtered and the filtrate was concentrated in vacuo. The residue was dissolved in DCM (10 mL) and HCl (4M in EA, 5 mL) was added. The mixture was triturated with MTBE (100 mL) and the white solid was collected to give the title compound (400 mg, 60% yield). LC-MS (ESI+) m/z 254.0 (M+H)+.

6-(1,3-Benzothiazol-6-ylamino)-4-(cyclopropylamino)pyridine-3-carboxylic acid (Intermediate BY)

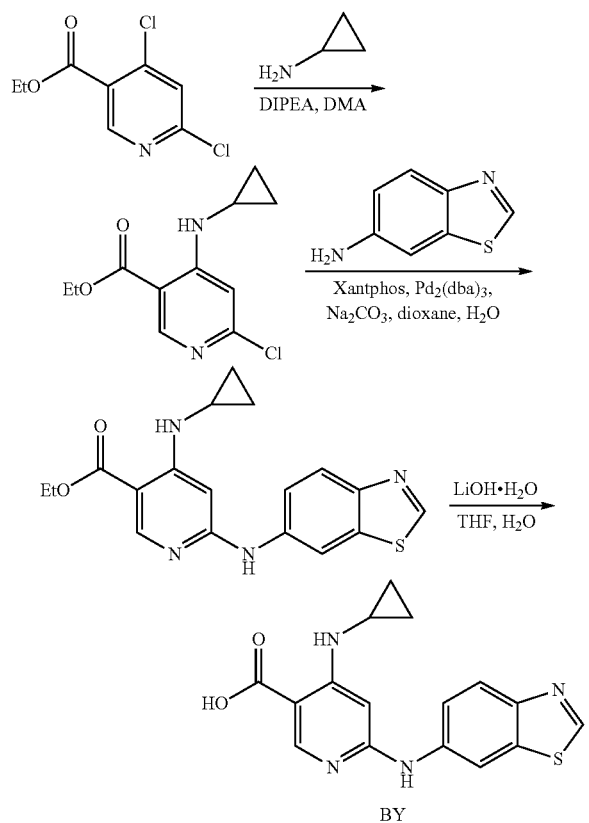

BY

Step 1—Ethyl 6-chloro-4-(cyclopropylamino)pyridine-3-carboxylate

To a mixture of ethyl 4,6-dichloropyridine-3-carboxylate (30.0 g, 136 mmol) in DMA (300 mL) was added DIPEA (17.6 g, 136 mmol) and cyclopropanamine (8.56 g, 149 mmol). The reaction mixture was heated to 90° C. and stirred for 3 h. On completion, the reaction mixture was quenched with crushed ice. The resulting slurry was stirred and filtered. The filter cake was purified by flash chromatography (PE/EA=3/1) to give the title compound (28.4 g, 86% yield) as a white solid. $^1$H NMR (400 MHz, DMSO-d$_6$) δ 8.53 (s, 1H), 8.08 (s, 1H), 7.02 (s, 1H), 4.30 (q, J=7.2 Hz, 2H), 2.63-2.57 (m, 1H), 1.30 (t, J=7.2 Hz, 3H), 0.87-0.84 (m, 2H), 0.58-0.56 (m, 2H).

Step 2—Ethyl 6-(1,3-benzothiazol-6-ylamino)-4-(cyclopropylamino)pyridine-3-carboxylate To a solution of ethyl 6-chloro-4-(cyclopropylamino) pyridine-3-carboxylate (5.00 g, 20.7 mmol) in a mixed solvent of dioxane (30.0 mL) and H$_2$O (5.00 mL) was added 1,3-benzothiazol-6-amine (3.12 g, 20.7 mmol), Xantphos (4.81 g, 8.31 mmol) and Na$_2$CO$_3$ (8.81 g, 83.1 mmol), followed by Pd$_2$(dba)$_3$ (7.61 g, 8.31 mmol) to the reaction mixture under nitrogen. The reaction mixture was then heated at 115° C. for 12 h. On completion, the reaction mixture was diluted with water (100 mL) and extracted with DCM (2×100 mL). The organic layer was dried with Na$_2$SO$_4$, filtered and concentrated in vacuo. The residue was purified by silica gel chromatography (DCM:MeOH=100:1) to give the title compound (0.60 g, 6% yield) as a white solid. $^1$H NMR (400 MHz, CDCl$_3$) δ 8.91 (s, 1H), 8.68 (s, 1H), 8.13 (d, J=2.0 Hz, 1H), 8.09 (d, J=8.8 Hz, 2H), 7.43 (dd, J=2.0, 8.8 Hz, 1H), 6.89-6.84 (m, 1H), 6.46 (s, 1H), 4.30 (q, J=7.2 Hz, 2H), 2.45-2.36 (m, 1H), 1.38 (t, J=7.2 Hz, 3H), 0.80-0.74 (m, 2H), 0.62-0.57 (m, 2H).

Step 3—6-(1,3-Benzothiazol-6-ylamino)-4-(cyclopropylamino)pyridine-3-carboxylic acid To a solution of ethyl 6-(1,3-benzothiazol-6-ylamino)-4-(cyclopropylamino)pyridine-3-carboxylate (0.43 g, 1.21 mmol) in a mixed solvent of H$_2$O (1.00 mL) and THF (3.00 mL) was added LiOH.H$_2$O (152 mg, 3.64 mmol). The reaction mixture was stirred at 40° C. for 24 h. On completion, the reaction was acidified with 2 N HCl until pH=4. The reaction mixture was then concentrated in vacuo and lyophilized to give the title compound (500 mg, 79% yield, HCl salt) as a white solid. LC-MS (ESI+) m/z 327.0 (M+H)+.

6-[(5-Cyano-3-fluoro-2-pyridyl)amino]-4-(cyclopropylamino)pyridine-3-carboxylic acid (Intermediate BZ)

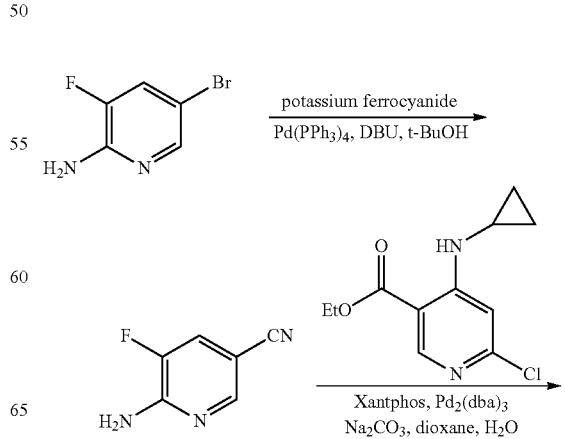

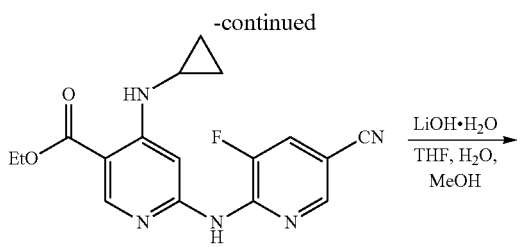

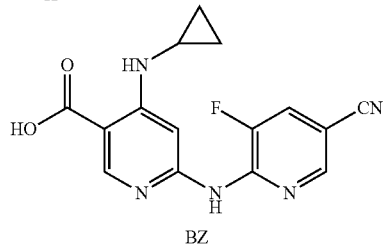

BZ

Step 1—6-Amino-5-fluoro-pyridine-3-carbonitrile

To a solution of 5-bromo-3-fluoro-pyridin-2-amine (5.00 g, 26.1 mmol), potassium ferrocyanide (3.86 g, 10.4 mmol) and Pd(PPh$_3$)$_4$ (1.51 g, 1.31 mmol) in a mixed solvent of t-BuOH (40.0 mL) and H$_2$O (40.0 mL) was added DBU (996 mg, 6.54 mmol, 986 uL) under nitrogen. The reaction mixture was heated to 85° C. and stirred for 16 h. On completion, the mixture was diluted with water (20.0 mL) and extracted with EA (3×20 mL). The combined organic layer was dried over anhydrous Na$_2$SO$_4$, filtered and concentrated in vacuo. The residue was purified by silica gel chromatography (PE:EA=5:1) to give the title compound (2.50 g, 69% yield) as a yellow solid. $^1$H NMR (400 MHz, DMSO-d$_6$) δ 8.23 (s, 1H), 7.85 (dd, J=1.6, 11.6 Hz, 1H), 7.38 (s, 2H).

Step 2—Ethyl 6-[(5-cyano-3-fluoro-2-pyridyl)amino]-4-(cyclopropylamino)pyridine-3-carboxylate To a solution of 6-amino-5-fluoro-pyridine-3-carbonitrile (2.50 g, 18.2 mmol), ethyl 6-chloro-4-(cyclopropylamino)pyridine-3-carboxylate (4.39 g, 18.2 mmol, synthesized via Step 1 of Intermediate BY) and Na$_2$CO$_3$ (7.73 g, 72.9 mmol) in a mixed solvent of dioxane (40.0 mL) and H$_2$O (8.00 mL) was added Xantphos (527 mg, 911 umol) and Pd$_2$(dba)$_3$ (834 mg, 911 umol) under nitrogen. The reaction mixture was then heated to 115° C. and stirred for 16 h. On completion, the mixture was diluted with a mixed solvent of DCM and MeOH (80.0 mL, 10:1), and stirred for 1 h, then filtered. The solid was washed with water (50 mL) and triturated with a mixed solvent of DCM and MeOH (30 mL, 10:1) to give the title compound (2.20 g, 35% yield) as a white solid. $^1$H NMR (400 MHz, DMSO-d$_6$) δ 9.83 (s, 1H), 8.62 (d, J=2.0 Hz, 1H), 8.56 (s, 1H), 8.21 (dd, J=1.6, 11.2 Hz, 1H), 8.05-7.98 (m, 2H), 4.27 (q, J=7.2 Hz, 2H), 2.55-2.54 (m, 1H), 1.31 (t, J=7.2 Hz, 3H), 0.95-0.86 (m, 2H), 0.60-0.55 (m, 2H).

Step 3—6-[(5-Cyano-3-fluoro-2-pyridyl)amino]-4-(cyclopropylamino)pyridine-3-carboxylic acid To a solution of ethyl 6-[(5-cyano-3-fluoro-2-pyridyl)amino]-4-(cyclopropylamino)pyridine-3-carboxylate (500 mg, 1.46 mmol) in a mixed solvent of THF (3.00 mL), MeOH (1.00 mL) and H$_2$O (1.00 mL) was added LiOH.H$_2$O (307 mg, 7.32 mmol). The reaction mixture was stirred at 45° C. for 2 hrs. On completion, the mixture was acidified with 1N HCl until the pH=3. The mixture was lyophilized to give the title compound (800 mg, 80% yield) as a yellow solid. LC-MS (ESI$^+$) m/z 314.0 (M+H)$^+$.

2-[2-(2,6-Dioxo-3-piperidyl)-1,3-dioxo-isoindolin-4-yl]oxyacetic acid (Intermediate CA)

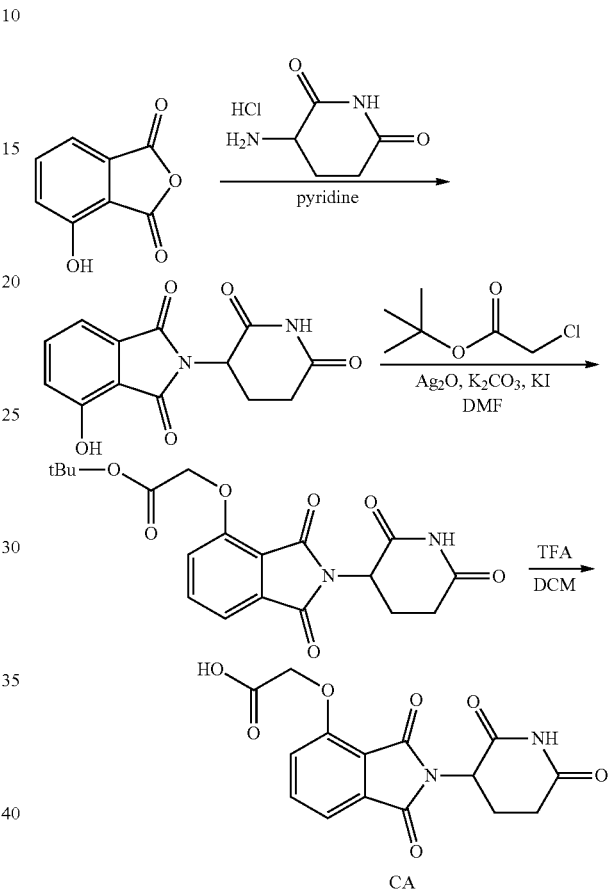

Step 1—2-(2,6-Dioxo-3-piperidyl)-4-hydroxy-isoindoline-1,3-dione

To a solution of 4-hydroxyisobenzofuran-1,3-dione (20.0 g, 122 mmol) in pyridine (100 mL) was added 3-aminopiperidine-2,6-dione (20.0 g, 122 mmol, HCl salt). The reaction mixture was stirred at 110° C. for 16 h. On completion, the mixture was concentrated in vacuo. The residue was diluted with water (500 mL) and stirred for 16 h. The mixture was then filtered and the filter cake was dried in vacuo to give the title compound (24.8 g, 74% yield) as a white solid. LC-MS (ESI$^+$) m/z 297.0 (M+Na)$^+$.

Step 2—Tert-butyl 2-[2-(2,6-dioxo-3-piperidyl)-1,3-dioxo-isoindolin-4-yl]oxyacetate To a mixture of 2-(2,6-dioxo-3-piperidyl)-4-hydroxy-isoindoline-1,3-dione (20 g, 72.9 mmol) and tert-butyl 2-chloroacetate (16.5 g, 109 mmol) in DMF (50 mL) was added Ag$_2$O (16.9 g, 72.9 mmol), K$_2$CO$_3$ (25.2 g, 182 mmol) and KI (1.21 g, 7.29 mmol). The reaction mixture was stirred at rt for 12 h. On completion, the reaction mixture was filtered and the filtrate was diluted with H₂O (40 mL) and extracted with DCM (2×200 mL). The combined organic layer was dried over Na₂SO₄, filtered and concentrated in vacuo. The residue was purified by silica gel chromatography to give the title compound (2.40 g, 8.5% yield) as a white solid. ¹H NMR (400 MHz, DMSO-d₆) δ 11.13 (s, 1H), 7.84-7.78 (m, 1H), 7.49 (d, J=7.2 Hz, 1H), 7.38 (d, J=8.8 Hz, 1H), 5.12 (dd, J=5.2, 12.8 Hz, 1H), 4.98 (s, 2H), 2.60-2.54 (m, 1H), 2.52-2.50 (m, 2H), 2.10-2.01 (m, 1H), 1.43 (s, 9H).

Step 3—2-[2-(2,6-Dioxo-3-piperidyl)-1,3-dioxo-isoindolin-4-yl]oxyacetic acid

To a mixture of tert-butyl 2-[2-(2,6-dioxo-3-piperidyl)-1,3-dioxo-isoindolin-4-yl]oxyacetate (2.40 g, 6.18 mmol) in DCM (10 mL) was added TFA (61.5 g, 539 mmol). Then the reaction mixture was stirred at rt for 12 h. On completion, the reaction mixture was concentrated in vacuo to give the title compound (3.10 g, 90% yield, TFA salt) as a white solid. ¹H NMR (400 MHz, DMSO-d₆) δ 11.13 (s, 1H), 7.80 (dd, J=7.2, 8.4 Hz, 1H), 7.48 (d, J=7.2 Hz, 1H), 7.40 (d, J=8.4 Hz, 1H), 5.11 (dd, J=5.2, 12.8 Hz, 1H), 5.00 (s, 2H), 2.95-2.84 (m, 1H), 2.64-2.53 (m, 2H), 2.11-1.98 (m, 1H); LC-MS (ESI⁺) m/z 332.9 (M+H)⁺.

(3S,4S,5S)-4-Ethyl-3-fluoro-5-(hydroxymethyl)pyrrolidin-2-one (Intermediate CB)

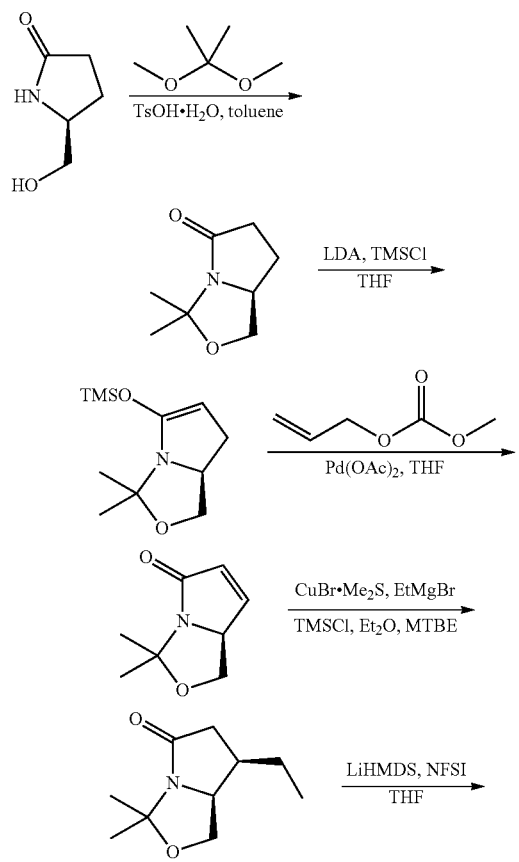

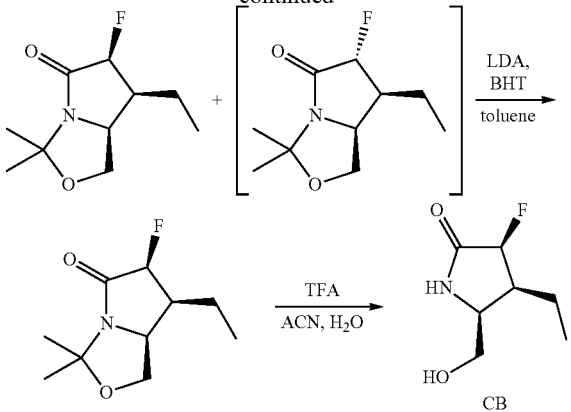

Step 1—(S)-3,3-Dimethyltetrahydropyrrolo[1,2-c]oxazol-5 (3H)-one

To a mixture of (5S)-5-(hydroxymethyl)pyrrolidin-2-one (200 g, 1.74 mol) and 2,2-dimethoxypropane (517 g, 4.97 mol) in toluene (2.4 L) was added TsOH·H₂O (13.2 g, 69.5 mmol). The reaction mixture was then stirred at 120° C. for 16 h. On completion, the reaction mixture was concentrated in vacuo and diluted with EA (5 L). The mixture was washed with 1N NaOH solution (2 L) and extracted with EA (8×1 L). The organic layer was dried over Na₂SO₄, filtered and concentrated in vacuo. The residue was triturated with PE (200 mL) to give the title compound (200 g, 74% yield) as a black brown crystal. ¹H NMR (400 MHz, CDCl₃) δ 4.29-4.19 (m, 1H), 4.05 (dd, J=5.6, 8.4 Hz, 1H), 3.42 (t, J=8.4 Hz, 1H), 2.81-2.71 (m, 1H), 2.58-2.44 (m, 1H), 2.21-2.08 (m, 1H), 1.82-1.66 (m, 1H), 1.68 (s, 3H), 1.47 (s, 3H).

Step 2—(S)-3,3-Dimethyl-5-((trimethylsilyl)oxy)-1,3,7,7a-tetrahydropyrrolo[1,2-c]oxazole To a solution of DIPA (119 g, 1.18 mol) in THF (1.3 mL) was added n-BuLi (2.5 M, 433 mL) at −25° C. The reaction mixture was stirred for 30 min. Then, the reaction mixture was cooled to −70° C. A solution of (S)-3,3-dimethyltetrahydropyrrolo[1,2-c]oxazol-5 (3H)-one (140 g, 902 mmol) in THF (500 mL) was added dropwise. The reaction mixture was stirred at −60° C. for 5 min. Then, TMSCl (127 g, 1.17 mmol) was added dropwise at −60° C. The reaction mixture was allowed to warm to −10° C. and stirred for 25 min. On completion, the reaction mixture was concentrated in vacuo. The residue was triturated with hexane (1 L), filtered and the filtrate was concentrated in vacuo to give the title compound (140 g, 68% yield) as a colorless oil. The product was unstable and was used for the next step directly without purification.

Step 3 (7aS)-3,3-dimethyl-1,7a-dihydropyrrolo[1,2-c]oxazol-5-one

To a mixture of (S)-3,3-dimethyl-5-((trimethylsilyl)oxy)-1,3,7,7a-tetrahydropyrrolo[1,2-c]oxazole (140 g, 616 mmol) and allyl methyl carbonate (107 g, 923 mmol) in THF (1.4 L) was added Pd(OAc)₂ (41.5 g, 185 mmol). The reaction mixture was stirred at 65° C. for 8 h under nitrogen. On completion, the reaction mixture was concentrated in vacuo. The residue was purified by silica gel chromatography (PE:EA=5:1) to give the title compound (30 g, 32% yield) as a colorless oil. $^1$H NMR (400 MHz, CDCl$_3$) δ 7.00 (d, J=5.6 Hz, 1H), 6.04 (d, J=5.6 Hz, 1H), 4.67-4.49 (m, 1H), 4.09-4.04 (m, 1H), 3.27 (t, J=8.8 Hz, 1H), 1.61 (s, 3H), 1.50 (s, 3H).

Step 4—(7R,7aS)-7-Ethyl-3,3-dimethyltetrahydropyrrolo[1,2-c]oxazol-5 (3H)-one To a mixture of bromocopper-methylsulfanylmethane (14.1 g, 68.6 mmol) in THF (200 mL) was added EtMgBr (3 M, 45.7 mL) at −10° C. dropwise. Then, the reaction mixture was cooled to −70° C. and TMSCl (7.45 g, 68.6 mmol) was added dropwise over 15 min. The reaction mixture was then stirred at −70° C. for an additional 15 min. Then a solution of (7aS)-3,3-dimethyl-1,7a-dihydropyrrolo[1,2-c]oxazol-5-one (6.00 g, 27.4 mmol) in THF (20 mL) was added dropwise over 10 min. Then the reaction mixture was stirred at 0° C. for 20 min. On completion, the reaction mixture was poured into cool saturated NH$_4$Cl solution (100 mL) and extracted with EA (3×500 mL). The combined layer was dried over Na$_2$SO$_4$, filtered and concentrated in vacuo. The residue was purified by silica gel chromatography (PE:EA=3:1) to give the title compound (3 g, 60% yield). $^1$H NMR (400 MHz, CDCl$_3$) δ 4.34 (td, J=6.4, 9.6 Hz, 1H), 3.90 (dd, J=6.4, 8.4 Hz, 1H), 3.72 (dd, J=8.4, 9.6 Hz, 1H), 2.91 (dd, J=8.0, 16.8 Hz, 1H), 2.31 (dd, J=1.6, 16.8 Hz, 1H), 2.28-2.18 (m, 1H), 1.64 (s, 3H), 1.55-1.49 (m, 1H), 1.48 (s, 3H), 1.37-1.27 (m, 1H), 0.91 (t, J=7.2 Hz, 3H).

Step 5—(6S,7S,7aS)-7-Ethyl-6-fluoro-3,3-dimethyltetrahydropyrrolo[1,2-c]oxazol-5 (3H)-one A solution of (7R,7aS)-7-ethyl-3,3-dimethyl-1,6,7,7a-tetrahydropyrrolo[1,2-c]oxazol-5-one (2.5 g, 13.6 mmol) in THF (10 mL) was treated at −78° C. with LiHMDS (1 M, 15.0 mL) and the mixture was kept for 0.5 h at −78° C. A solution of NFSI (5.60 g, 17.8 mmol) in THF (10 mL) was added slowly. The mixture was kept at approximately −78° C. for 0.5 h. On completion, the precipitated solid was filtered and washed with THF (20 mL). The filtrate was concentrated in vacuo to an oily residue. The oily residue was purified by silica gel chromatography (PE:EA=10:1). Then, the residue was repurified by reversed phase chromatography (0.1% FA) to give the title compound (575 mg, 21% yield) as a colorless oil. $^1$H NMR (400 MHz, CD$_3$CN) δ 4.89-4.73 (m, 1H), 4.42 (td, J=6.4, 10.4 Hz, 1H), 3.95 (dd, J=5.6, 8.4 Hz, 1H), 3.59 (dd, J=8.4, 10.4 Hz, 1H), 2.49-2.33 (m, 1H), 1.59 (s, 3H), 1.58-1.51 (m, 1H), 1.45 (s, 3H), 1.44-1.37 (m, 1H), 1.00 (t, J=7.2 Hz, 3H).

Step 6—(6S,7S,7aS)-7-Eethyl-6-fluoro-3,3-dimethyltetrahydropyrrolo[1,2-c]oxazol-5 (3H)-

To a solution of diisopropylamine (322 mg, 3.18 mmol) in toluene (5 mL) was added n-BuLi (2.5 M, 1.26 mL) dropwise at −30° C. The mixture was maintained at −30° C. for an additional 30 min, then a solution of (6R,7S,7aS)-7-ethyl-6-fluoro-3,3-dimethyl-1,6,7,7a-tetrahydropyrrolo[1,2-c]oxazol-5-one (575 mg, 2.86 mmol) in toluene (2 mL) was added dropwise at −78° C. over 2 h. After the addition was completed, the mixture was kept at −78° C. for 30 min more before a solution of BHT (1.30 g, 5.91 mmol) in toluene (2 mL) was added dropwise over 0.5 h, keeping the internal temperature below −65° C. After the addition was completed, the mixture was kept at −78° C. for 30 min. The mixture was then warmed to rt and stirred for 2 hrs. On completion, the reaction was quenched with water (5 mL) and extracted with ethyl acetate (3×50 mL). The combined organic layers were washed with brine (20 mL), dried over anhydrous sodium sulfate, filtered and concentrated in vacuo. The residue was purified by silica gel chromatography (PE:EA=10:1) to give the title compound (244 mg, 40% yield) as a white solid. $^1$H NMR (400 MHz, CDCl$_3$) δ 5.36-5.15 (m, 1H), 4.12-4.01 (m, 2H), 3.79-3.68 (m, 1H), 2.78-2.64 (m, 1H), 1.80-1.70 (m, 1H), 1.69 (s, 3H), 1.50 (s, 3H), 1.42-1.32 (m, 1H), 0.98 (t, J=7.2 Hz, 3H). LC-MS (ESI$^+$) m/z 202.1 (M+H)$^+$.

Step 7—(3S,4S,5S)-4-Ethyl-3-fluoro-5-(hydroxymethyl)pyrrolidin-2-one (6S,7S,7aS)-7-ethyl-6-fluoro-3,3-dimethyl-1,6,7,7a-tetrahydropyrrolo[1,2-c]oxazol-5-one (330 mg, 1.64 mmol) in acetonitrile (1.5 mL) and H$_2$O (0.15 mL) was treated with TFA (37.4 mg, 328 umol). The mixture was warmed to −65° C. over 1 h, and held at that temperature for 3 hrs. On completion, the mixture was concentrated in vacuo. The residue was reversed phase chromatography to give the title compound (230 mg, 91% yield). $^1$H NMR (400 MHz, CDCl$_3$) δ 7.59 (s, 1H), 4.80 (dd, 1H), 3.69-3.83 (m, 2H), 3.52-3.64 (m, 1H), 3.48 (br. s, 1H), 2.27-2.52 (m, 1H), 1.57-1.73 (m, 1H), 1.49 (dt, 1H), 1.04 (t, 3H). LC-MS (ESI$^+$) m/z 162.1 (M+H)$^+$

7-Methoxy-1-oxo-1,2-dihydroisoquinoline-6-carbonitrile (Intermediate CC)

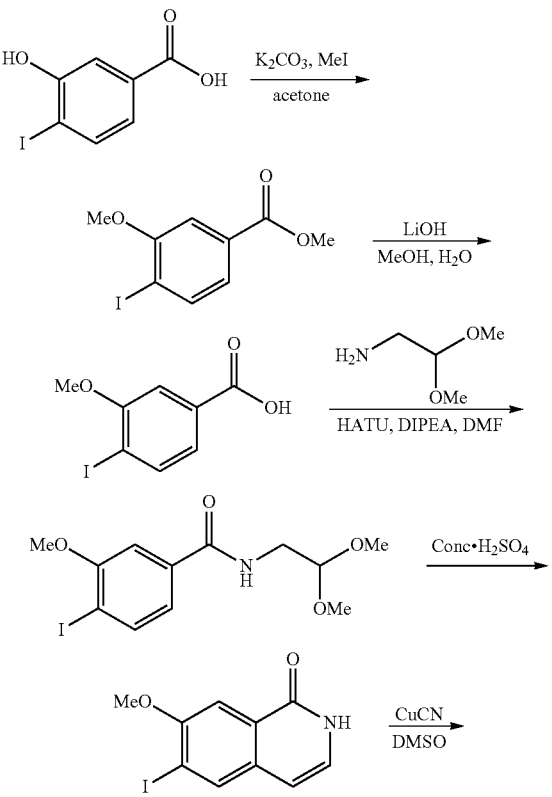

-continued

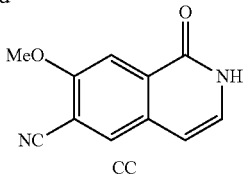

CC

Step 1—Methyl 4-iodo-3-methoxybenzoate

To a solution of 3-hydroxy-4-iodo-benzoic acid (25.0 g, 94.7 mmol) in acetone (350 mL) was added $K_2CO_3$ (52.4 g, 379 mmol) and $CH_3I$ (53.8 g, 379 mmol). The reaction mixture was stirred at 50° C. for 16 hours. On completion, the reaction mixture was concentrated in vacuo. The residue was dissolved with ethyl acetate (150 mL) and washed with water (150 mL). The organic phase was dried over anhydrous sodium sulfate, filtered and concentrated in vacuo to give the title compound (24.5 g, 89% yield) as a yellow oil. $^1$H NMR (400 MHz, $CDCl_3$) δ 7.86 (d, J=8.0 Hz, 1H), 7.46 (d, J=1.6 Hz, 1H), 7.38 (dd, J=1.6, 8.0 Hz, 1H), 3.95 (s, 3H), 3.93 (s, 3H).

Step 2—4-Iodo-3-methoxybenzoic acid

To a solution of methyl 4-iodo-3-methoxy-benzoate (3.00 g, 10.3 mmol) in a mixture of methanol (20 mL) and water (5 mL) was added $LiOH.H_2O$ (1.29 g, 30.8 mmol). The reaction mixture was stirred at rt for 2 h. On completion, the reaction mixture was concentrated in vacuo to remove the methanol. The aqueous phase was acidified with 2N HCl solution until the pH=2, and filtered. The filter cake was dried in vacuo to give the title compound (2.70 g, 95% yield) as a white solid. $^1$H NMR (400 MHz, DMSO-$d_6$) δ 13.21 (s, 1H), 7.91 (d, J=8.0 Hz, 1H), 7.42 (d, J=1.6 Hz, 1H), 7.30 (dd, J=1.6, 8.0 Hz, 1H), 3.89 (s, 3H).

Step 3—N-(2,2-dimethoxyethyl)-4-iodo-3-methoxy-benzamide

To a mixture of 4-iodo-3-methoxy-benzoic acid (2.3 g, 8.3 mmol), HATU (3.77 g, 9.93 mmol) and DIPEA (3.21 g, 24.8 mmol) in DMF (40 mL) was added 2,2-dimethoxy-ethanamine (1.04 g, 9.93 mmol). The reaction mixture was stirred at rt for 1 h. On completion, the reaction mixture was concentrated in vacuo. The residue was diluted with water (40 mL), acidified with citric acid, and extracted with EA (3×100 mL). The organic phase was dried over anhydrous $Na_2SO_4$, filtered and concentrated in vacuo. The crude product was purified by silica gel chromatography (PE/EA=1/2) to give the title compound (2.80 g, 93% yield) as a white solid. $^1$H NMR (400 MHz, $CDCl_3$) δ 7.83 (d, J=8.0 Hz, 1H), 7.34 (d, J=2.0 Hz, 1H), 6.99 (dd, J=2.0, 8.0 Hz, 1H), 6.33 (s, 1H), 4.49 (t, J=5.6 Hz, 1H), 3.95 (s, 3H), 3.61 (t, J=5.6 Hz, 2H), 3.45 (s, 6H).

Step 4—6-Iodo-7-methoxyisoquinolin-1 (2H)-one

A mixture of N-(2,2-dimethoxyethyl)-4-iodo-3-methoxy-benzamide (3.30 g, 9.04 mmol) in concentrated $H_2SO_4$ (15 mL) was stirred at 60° C. for 0.5 h. On completion, the reaction mixture was pour into ice water (200 mL) and extracted with DCM (3×200 mL). The combined organic layer was dried in vacuo to give the title compound (2.50 g, 92% yield) as a white solid. $^1$H NMR (400 MHz, DMSO-$d_6$) δ 11.29 (s, 1H), 8.22 (s, 1H), 7.54 (s, 1H), 7.07 (d, J=7.2 Hz, 1H), 6.48 (d, J=7.2 Hz, 1H), 3.92 (s, 3H).

Step 5—7-Methoxy-1-oxo-1,2-dihydroisoquinoline-6-carbonitrile

A mixture of 6-iodo-7-methoxy-2H-isoquinolin-1-one (2.4 g, 7.97 mmol) and CuCN (2.14 g, 23.9 mmol) in DMF (50 mL) was stirred at 125° C. for 1 h under nitrogen. On completion, the reaction mixture was concentrated in vacuo. The residue was dissolved in DCM:MeOH=10:1 (100 mL), filtered and concentrated in vacuo to give the title compound (1.40 g, 88% yield) as a yellow solid. $^1$H NMR (400 MHz, DMSO-$d_6$) δ 11.52 (s, 1H), 8.24 (s, 1H), 7.78 (s, 1H), 7.17 (dd, J=5.6, 7.2 Hz, 1H), 6.57 (d, J=7.2 Hz, 1H), 4.02 (s, 3H).

1-(((2S,3S,4S)-3-Ethyl-4-fluoro-5-oxopyrrolidin-2-yl)methoxy)-7-methoxyisoquinoline-6-carbonitrile (Intermediate CD)

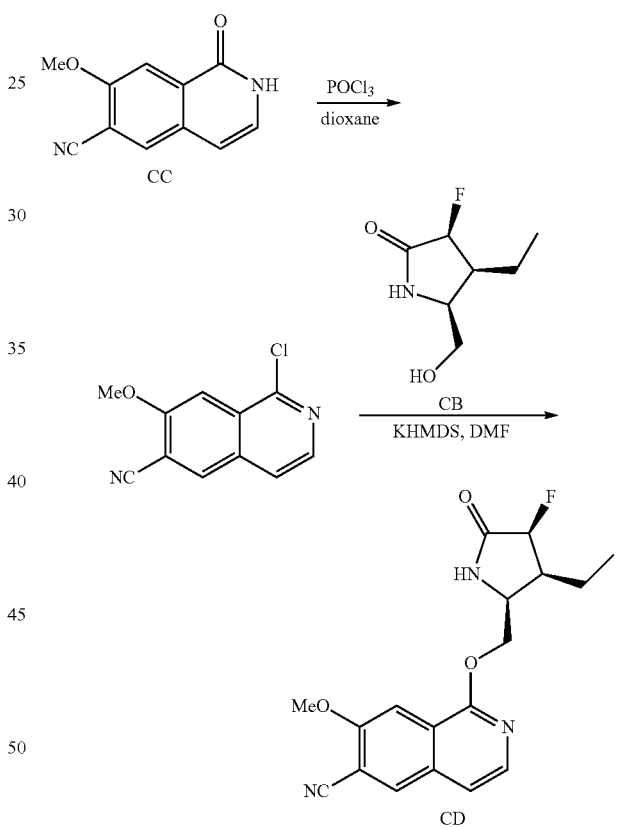

Step 1—1-Chloro-7-methoxyisoquinoline-6-carbonitrile

To a mixture of 7-methoxy-1-oxo-2H-isoquinoline-6-carbonitrile (1.25 g, 6.24 mmol, Intermediate CC) in dioxane (50 mL) was added $POCl_3$ (3.83 g, 25.0 mmol). The reaction mixture was stirred at 110° C. for 2 h. On completion, the reaction mixture was concentrated to remove the solvent. The residue was dissolved in DCM (20 mL) and washed with $NaHCO_3$ solution until the pH=8. The reaction mixture was then extracted with DCM (3×100 mL). The combined layer was dried over $Na_2SO_4$, filtered, and the filtrate was concentrated in vacuo. The residue was purified by silica gel chromatography (PE:DCM=1:5) to give the title compound (1.00 g, 60% yield) as an off-white solid. LC-MS (ESI$^+$) m/z 219.0 (M+H)$^+$.

Step 2—1-(((2S,3S,4S)-3-Ethyl-4-fluoro-5-oxopyrrolidin-2-yl)methoxy)-7-methoxyisoquinoline-6-carbonitrile A mixture of 1-chloro-7-methoxy-isoquinoline-6-carbonitrile (50.0 mg, 229 umol) and (3S,4S,5S)-4-ethyl-3-fluoro-5-(hydroxymethyl)pyrrolidin-2-one (36.9 mg, 229 umol, Intermediate CB) were stirred in DMF (1 mL) and cooled to approximately −10° C. A solution of KHMDS (1 M, 503.11 uL) in THF was then added into the reaction mixture over −15 minutes, maintaining the internal reaction temperature at approximately −10° C. After, the reaction was stirred at −10° C. for approximately an additional 30 minutes. On completion, the reaction mixture was quenched with saturated NaH$_2$PO$_4$ (20 mL) and extracted with ethyl acetate (3×100 mL). The combined organic layers were washed with brine (20 mL), dried over anhydrous sodium sulfate, filtered and concentrated in vacuo. The residue was purified by prep-TLC (EA) to give the title compound (50.0 mg, 49% yield) as a white solid. LC-MS (ESI$^+$) m/z 344.0 (M+H)$^+$ 1-[[(2S,3S,4S)-3-ethyl-4-fluoro-5-oxo-pyrrolidin-2-yl]methoxy]-7-methoxy-isoquinoline-6-carboxylic acid (Intermediate CE)

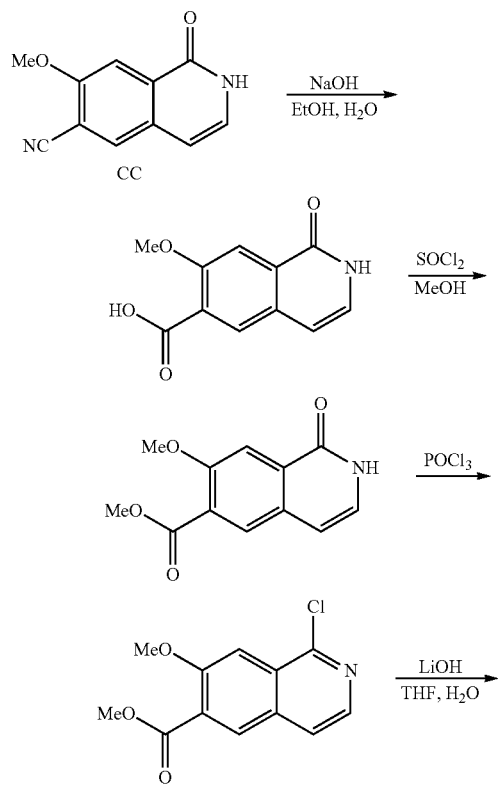

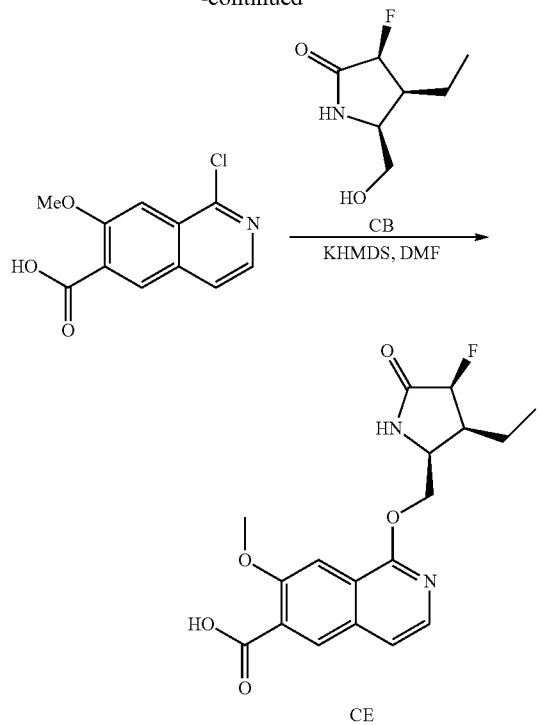

Step 1—7-Methoxy-1-oxo-2H-isoquinoline-6-carboxylic acid

To a solution of 7-methoxy-1-oxo-2H-isoquinoline-6-carbonitrile (1.50 g, 7.49 mmol, Intermediate CC) in ethanol (30 mL) was added aqueous sodium hydroxide (10 M, 15.0 mL). The mixture was stirred at 80° C. for 15 h. On completion, the reaction mixture was concentrated in vacuo to remove the ethanol. The residue was acidified with saturated citric acid aqueous until the pH<6. A fine light yellow precipitate formed and the precipitate was filtered and dried in vacuo to give the title product (1.20 g, 73% yield) as a light yellow solid. $^1$H NMR (400 MHz, DMSO-d$_6$) δ 13.16 (br s, 1H), 11.35 (br s, 1H), 7.91 (s, 1H), 7.70 (s, 1H), 7.10 (dd, J=5.6, 6.8 Hz, 1H), 6.59 (d, J=7.2 Hz, 1H), 3.91 (s, 3H).

Step 2—Methyl 7-methoxy-1-oxo-2H-isoquinoline-6-carboxylate

To a solution of 7-methoxy-1-oxo-2H-isoquinoline-6-carboxylic acid (1.10 g, 5.02 mmol) in methanol (50 mL) was added sulfonyl chloride (3.58 g, 30.1 mmol, 2.18 mL). The mixture was stirred at 70° C. for 15 h. On completion, the reaction mixture was concentrated in vacuo to give a residue. The residue was dissolved in ice water (30 mL) and basified with saturated sodium bicarbonate aqueous until the pH>7 and a fine light yellow precipitate was formed. The precipitate was filtered and dried in vacuo to give the title compound (1.10 g, 93% yield) as a light yellow solid. $^1$H NMR (400 MHz, CDCl$_3$) δ 10.79 (br s, 1H), 7.89 (s, 1H), 7.83 (s, 1H), 7.03 (d, J=6.8 Hz, 1H), 6.49 (d, J=7.2 Hz, 1H), 3.96 (s, 3H), 3.89 (s, 3H).

Step 3—Methyl 1-chloro-7-methoxy-isoquinoline-6-carboxylate

Methyl 7-methoxy-1-oxo-2H-isoquinoline-6-carboxylate (1.00 g, 4.29 mmol) was dissolved in POCl$_3$ (30 mL) and the mixture was stirred at 105° C. for 14 h. On completion, the reaction mixture was concentrated in vacuo to give a residue. The residue was dissolved in ice water (50 mL) and basified with saturated sodium bicarbonate aqueous until the pH>7, and a fine light yellow precipitate was formed. The precipitate was filtered and dried in vacuo to give the title compound (1.00 g, 92% yield) as a light yellow solid. $^1$H NMR (400 MHz, CDCl$_3$) δ 8.25 (d, J=5.6 Hz, 1H), 8.23 (s, 1H), 7.65 (s, 1H), 7.60 (d, J=5.6 Hz, 1H), 4.09 (s, 3H), 4.00 (s, 3H).

Step 4—1-Chloro-7-methoxy-isoquinoline-6-carboxylic acid

To a solution of methyl 1-chloro-7-methoxy-isoquinoline-6-carboxylate (1.00 g, 3.97 mmol) in a mixed solution of tetrahydrofuran (20 mL) and water (10 mL) was added lithium hydroxide (380 mg, 15.8 mmol). The mixture was stirred at rt or 14 h. On completion, the reaction mixture was concentrated in vacuo to remove the tetrahydrofuran. The resulting residue was acidified with 1 N hydrochloride acid until the pH=6 and a white precipitate was formed. The precipitate was filtered and the filter cake was dried in vacuo to give the title compound (900 mg, 95% yield) as a white solid. $^1$H NMR (400 MHz, DMSO-d$_6$) δ 8.22 (d, J=5.6 Hz, 1H), 8.18 (s, 1H), 7.89 (d, J=5.6 Hz, 1H), 7.53 (s, 1H), 3.98 (s, 3H).

Step 5—1-[[(2S,3S,4S)-3-ethyl-4-fluoro-5-oxo-pyrrolidin-2-yl]methoxy]-7-methoxy-isoquinoline-6-carboxylic acid A mixture of 1-chloro-7-methoxy-isoquinoline-6-carboxylic acid (200 mg, 841 umol), (3S,4S,5S)-4-ethyl-3-fluoro-5-(hydroxymethyl)pyrrolidin-2-one (135 mg, 841 umol, Intermediate CB) in N,N-dimethylformamide (8 mL) was cooled to −10° C., and KHMDS (1 M, 3.53 mL) was added dropwise under nitrogen gas atmosphere to keep the temperature at −10° C. over 0.25 h. The mixture was stirred at 0° C. for 15 h. On completion, the reaction mixture was quenched with ice water (30 mL) and acidified with 1 N hydrochloride acid until the pH=5, and then extracted with dichloromethane (3×15 mL). The combine organic phase was dried over anhydrous magnesium sulfate, filtered and concentrated in vacuo to give a residue. The residue was purified by prep-HPLC (column: Phenomenex Synergi C18 150*25*10 um; mobile phase: [water (0.05% HCl)-ACN]) to give the title compound (95.0 mg, 28% yield, hydrochloride salt) as a yellow solid. $^1$H NMR (400 MHz, DMSO-d$_6$) δ 8.91 (s, 1H), 8.13 (s, 1H), 7.92 (d, J=5.6 Hz, 1H), 7.74 (s, 1H), 7.43 (d, J=5.6 Hz, 1H), 4.99-4.82 (m, 1H), 4.55 (dd, J=3.2, 11.2 Hz, 1H), 4.26 (dd, J=6.4, 11.2 Hz, 1H), 4.10-4.09 (m, 1H), 3.94 (s, 3H), 2.69-2.55 (m, 1H), 1.66-1.56 (m, 2H), 1.02 (t, J=7.2 Hz, 3H).

2,2'-(Pentane-1,5-diylbis(oxy))diethanamine (Intermediate CF)

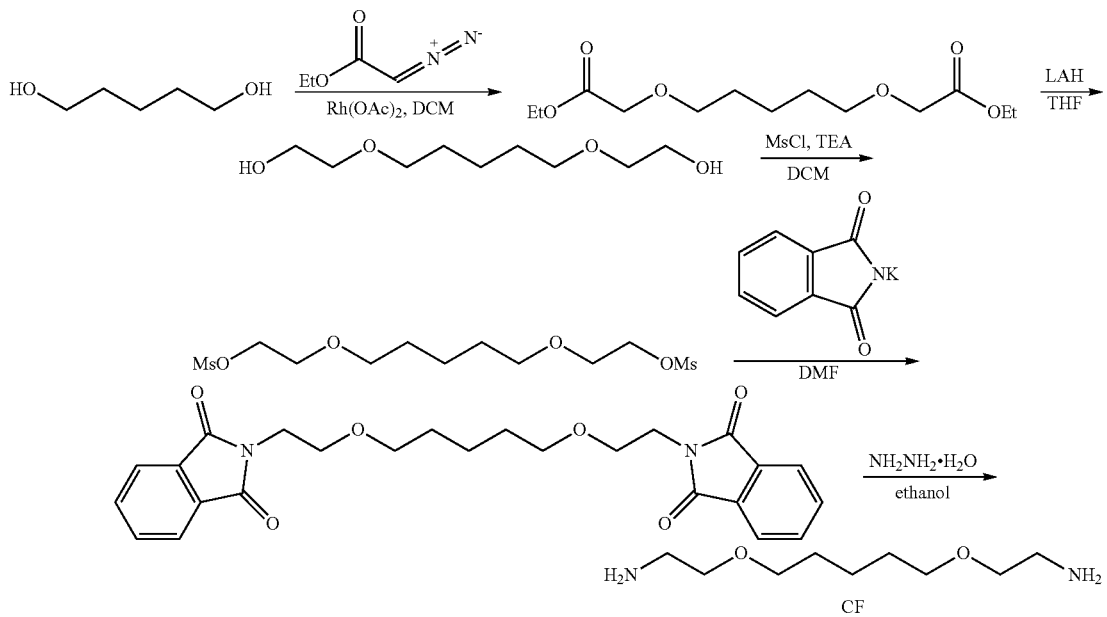

Step 1—Diethyl 2,2'-(pentane-1,5-diylbis(oxy))diacetate

To a solution of pentane-1,5-diol (20 g, 192 mmol, 20.2 mL) and Rh(OAc)$_2$ (1.70 g, 7.68 mmol) in DCM (50 mL) was added a solution of ethyl 2-diazoacetate (21.9 g, 192 mmol) in DCM (200 mL), and the reaction mixture was stirred at rt for 12 h. On completion, the reaction mixture was diluted with water (100 mL) and extracted with DCM (2×200 mL). The combined organic phase was dried over Na$_2$SO$_4$, filtered and concentrated in vacuo to give a residue. The residue was purified by silica gel chromatography (PE/EA=5/1) to give the title compound (10 g, 19% yield)

as a yellow oil. $^1$H NMR (400 MHz, CDCl$_3$) δ 4.24-4.20 (m, 4H), 4.05 (s, 4H), 3.55-3.51 (m, 4H), 1.67-1.64 (m, 4H), 1.48-1.46 (m, 2H), 1.30-1.26 (m, 6H).

Step 2—2,2'-(Pentane-1,5-diylbis(oxy))diethanol

To a solution of LAH (3.43 g, 90.5 mmol) in THF (100 mL) was added slowly dropwise a solution of ethyl 2-[5-(2-ethoxy-2-oxo-ethoxy)pentoxy]acetate (10.0 g, 36.2 mmol) in THF (100 mL) at 0° C. The reaction mixture was then allowed to warm to rt and stirred for 1 h under nitrogen. On completion, the reaction mixture was quenched with water (6 mL) and 15% sodium hydroxide solution (10 mL). Then, the mixture was filtered. The filtrate was concentrated in vacuo to give the title compound (5.7 g, 83% yield) as a colorless oil. $^1$H NMR (400 MHz, CDCl$_3$) δ 3.69-3.62 (m, 4H), 3.49-3.45 (m, 4H), 3.42 (t, J=6.0 Hz, 4H), 2.33 (t, J=6.0 Hz, 2H), 1.60-1.52 (m, 4H), 1.44-1.35 (m, 2H).

Step 3-(Pentane-1,5-diylbis(oxy))bis(ethane-2,1-diyl) dimethanesulfonate

To a solution of 2-[5-(2-hydroxyethoxy)pentoxy]ethanol (5.7 g, 29.7 mmol) in DCM (60 mL) was added TEA (9.00 g, 89.0 mmol) and MsCl (8.49 g, 74.1 mmol). The reaction mixture was stirred at rt for 1 hr. On completion, the reaction mixture was quenched with water (10 mL). Then, the mixture was washed with 1N citric aqueous (20 mL). The organic layer was dried over anhydrous sodium sulfate, filtered and concentrated in vacuo to give the title compound (10 g, 97% yield) as a colorless oil. $^1$H NMR (400 MHz, CDCl$_3$) δ 4.45-4.33 (m, 4H), 3.76-3.68 (m, 4H), 3.51 (t, J=6.4 Hz, 4H), 3.08 (s, 6H), 1.67-1.60 (m, 4H), 1.48-1.41 (m, 2H).

Step 4—2,2'-((Pentane-1,5-diylbis(oxy))bis(ethane-2,1-diyl))bis(isoindoline-1,3-dione)

A solution of 2-[5-(2-methylsulfonyloxyethoxy)pentoxy] ethyl methanesulfonate (10 g, 28.7 mmol) and (1,3-dioxoisoindolin-2-yl)potassium (11.7 g, 63.1 mmol) in DMF (100 mL) was heated to 100° C. for 12 h. On completion, the reaction mixture was concentrated in vacuo. The residue was dissolved ethyl acetate (300 mL) and filtered. The filtrate was concentrated in vacuo. The residue was purified by silica gel chromatography (PE:EA=5:1) to give the title compound (11 g, 77% yield). $^1$H NMR (400 MHz, CDCl$_3$) δ 7.92-7.82 (m, 4H), 7.77-7.72 (m, 4H), 3.88 (t, J=6.0 Hz, 4H), 3.64 (t, J=6.0 Hz, 4H), 3.39 (t, J=6.4 Hz, 4H), 1.54-1.44 (m, 4H), 1.30-1.23 (m, 2H).

Step 5—2,2'-(Pentane-1,5-diylbis(oxy))di-ethanamine

To a solution of 2-[2-[5-[2-(1,3-dioxoisoindolin-2-yl)ethoxy]pentoxy]ethyl]isoindoline-1,3-dione (1.10 g, 2.44 mmol) in ethanol (20 mL) was added NH$_2$NH$_2$H$_2$O (624 mg, 12.2 mmol). The reaction mixture was stirred at 80° C. for 2 h. On completion, the reaction mixture was cooled to rt and filtered. The filtrate was concentrated in vacuo. Then, the residue was diluted with DCM (20 mL) and filtered again. The filtrate was concentrated in vacuo to give the title compound (460 mg, 99% yield) as a colorless oil. $^1$H NMR (400 MHz, CDCl$_3$) δ 3.51-3.43 (m, 8H), 2.87 (t, J=5.2 Hz, 4H), 1.68-1.57 (m, 4H), 1.50-1.39 (m, 2H).

Tert-butyl N-(11-aminoundecyl)carbamate
(Intermediate CG)

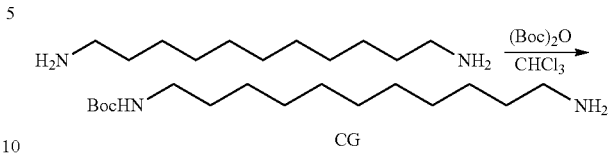

To a mixture of undecane-1,11-diamine (512 mg, 2.75 mmol) in CHCl$_3$ (25 mL) was added a solution of tert-butoxycarbonyl tert-butyl carbonate (120 mg, 549 umol) in CHCl$_3$ (5 mL) dropwise. The reaction mixture was stirred at it for 20 hours. On completion, the reaction mixture was concentrated in vacuo. The residue was purified by column chromatography to give the title compound (120 mg, 76% yield) as a light yellow oil. $^1$H NMR (400 MHz, CDCl$_3$) 4.54 (s, 1H), 3.12 (d, J=6.0 Hz, 2H), 2.70 (t, J=7.0 Hz, 2H), 1.70-1.55 (m, 4H), 1.46 (s, 9H), 1.32-1.25 (m, 14H).

Ethyl 2-[2-[2-[2-[2-(tert-butoxycarbonylamino)ethoxy]ethoxy]ethoxy]ethoxy]acetate (Intermediate CH)

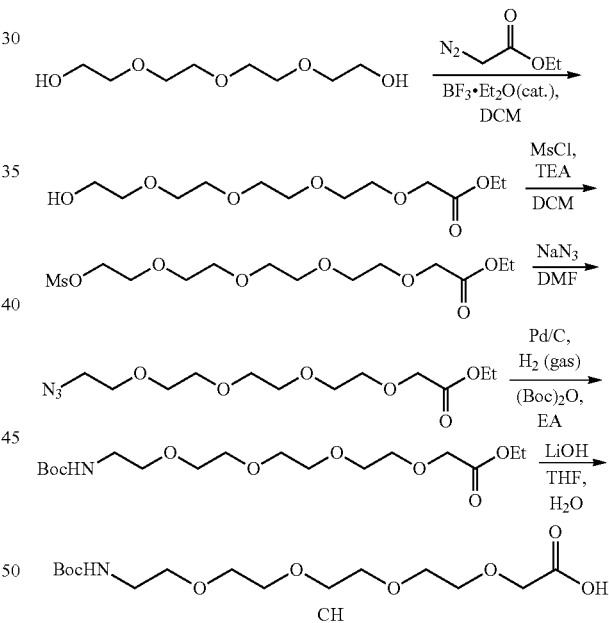

Step 1—Ethyl 14-hydroxy-3,6,9,12-tetraoxatetradecan-1-oate

To a solution of 2-[2-[2-(2-hydroxyethoxy)ethoxy]ethoxy]ethanol (10.0 g, 51.5 mmol, CAS #112-60-7) in DCM (150 mL) was added BF$_3$.Et$_2$O (159 mg, 515 umol) at 0° C. Then, ethyl 2-diazoacetate (5.87 g, 51.5 mmol) was added to the reaction mixture dropwise. After that, the mixture was allowed to warm to rt and stirred for 12 hours. On completion, the reaction mixture was quenched by ammonium chloride (5 mL), then diluted with water (100 mL), and extracted with DCM (3×50 mL). The combined organic layers were dried over sodium sulfate and concentrated in vacuo to give a residue. The residue was purified by silica gel chromatography to give the title compound (2.60 g, 18% yield) as a colorless oil. $^1$H NMR (400 MHz, CDCl$_3$) δ 4.16 (q, J=7.2 Hz, 2H), 4.10 (s, 2H), 3.71-3.59 (m, 14H), 3.58-3.54 (m, 2H), 1.24 (t, J=7.2 Hz, 3H).

Step 2—Ethyl 2-[2-[2-[2-(2-methylsulfonyloxyethoxy)ethoxy]ethoxy]ethoxy]acetate

To a solution of ethyl 2-[2-[2-[2-(2-hydroxyethoxy)ethoxy]ethoxy]ethoxy]acetate (6.86 g, 24.5 mmol) in DCM (50 mL) was added TEA (4.95 g, 48.9 mmol). The reaction mixture was cooled to 0° C. Then MsCl (3.36 g, 29.4 mmol) was added into the solution slowly. The reaction mixture was stirred at rt for 0.5 hour. On completion, the reaction mixture was quenched with H$_2$O (20 mL) and saturated citric acid solution (20 mL) was added until the pH=5-6, then they organic layer was separated. The organic layer was washed with brine (4×50 mL), dried over Na$_2$SO$_4$, filtered and concentrated in vacuo to give the title compound (8.00 g, 91% yield) as a brown oil. $^1$H NMR (400 MHz, CDCl$_3$) δ 4.43-4.37 (m, 2H), 4.23 (q, J=7.2 Hz, 2H), 4.16 (s, 2H), 3.82-3.62 (m, 14H), 3.10 (s, 3H), 1.30 (t, J=7.2 Hz, 3H).

Step 3—Ethyl 2-[2-[2-[2-(2-azidoethoxy)ethoxy]ethoxy]ethoxy]acetate

To a solution of ethyl 2-[2-[2-[2-(2-methylsulfonyloxyethoxy)ethoxy]ethoxy]ethoxy]acetate (8.00 g, 22.3 mmol) in DMF (30 mL) was added NaN$_3$ (2.90 g, 44.6 mmol). The reaction mixture was stirred at 80° C. for 15 h. On completion, the solvent DMF was removed in vacuo. Then the residue was diluted with EA (150 mL) and filtered. The filtrate was used for the next step directly without further purification or concentration. LC-MS (ESI$^+$) m/z 278.1 (M+H−28)$^+$.

Step 4—Ethyl 2-[2-[2-[2-[2-(tert-butoxycarbonylamino)ethoxy]ethoxy]ethoxy]ethoxy]acetate To a solution of ethyl 2-[2-[2-[2-(2-azidoethoxy)ethoxy]ethoxy]ethoxy]acetate (6.81 g, 22.3 mmol) in EA (150 mL) was added Pd/C (700 mg, 10 wt %) and (Boc)$_2$O (24.3 g, 112 mmol). The mixture was degassed and purged with hydrogen gas three times. Then the reaction mixture was stirred at rt for 15 hours. On completion, the mixture was filtered and the filtrate was concentrated in vacuo to give a residue. The residue was purified by silica gel chromatography (DCM/MeOH=10/1) to give the title compound (5.15 g, 61% yield) as a colorless oil. $^1$H NMR (400 MHz, CDCl$_3$) δ 5.05 (s, 1H), 4.27 (q, J=7.2 Hz, 2H), 4.17 (s, 2H), 3.79-3.60 (m, 12H), 3.56 (t, J=5.2 Hz, 2H), 3.37-3.27 (m, 2H), 1.45 (s, 9H), 1.31 (t, J=7.2 Hz, 3H).

Step 5—Ethyl 2-[2-[2-[2-[2-(tert-butoxycarbonylamino)ethoxy]ethoxy]ethoxy]ethoxy]acetate To a solution of ethyl 2-[2-[2-[2-[2-(tert-butoxycarbonylamino)ethoxy]ethoxy]ethoxy]ethoxy]acetate (0.40 g, 1.05 mmol) in THF (10 mL) and H$_2$O (4 mL) was added LiOH (50.5 mg, 2.11 mmol). The reaction mixture was stirred at rt for 16 hours. On completion, the mixture was concentrated in vacuo to give a residue, then diluted with H$_2$O. The aqueous phase was acidified with conc. HCl until the pH=6 and concentrated in vacuo to give the title compound (350 mg, 996 umol) as a yellow solid. $^1$H NMR (400 MHz, CDCl$_3$) δ 4.18 (m, 2H), 3.80-3.63 (m, 14H), 3.46-3.17 (m, 2H), 1.46-1.41 (s, 9H).

(2S,4R)-1-[(2S)-2-amino-3,3-dimethyl-butanoyl]-4-hydroxy-N-[[4-(4-methylthiazol-5-yl)-phenyl]methyl]pyrrolidine-2-carboxamide (Intermediate CI)

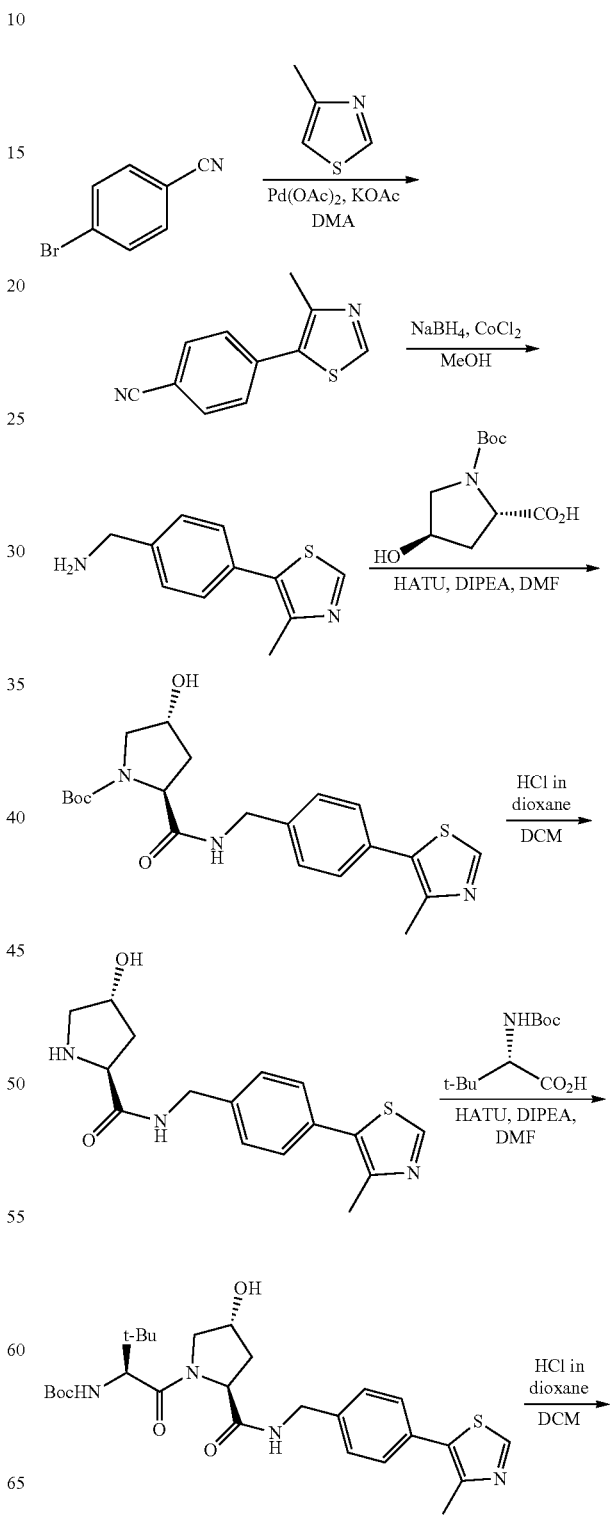

-continued

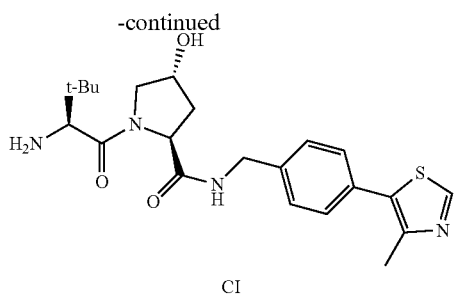

Step 1—4-(4-Methylthiazol-5-yl)benzonitrile

To a mixture of 4-bromobenzonitrile (32.0 g, 176 mmol), 4-methylthiazole (34.86 g, 352 mmol) and KOAc (34.5 g, 352 mmol) in DMA (100 mL) was added Pd(OAc)$_2$ (820 mg, 3.65 mmol). The mixture was stirred at 150° C. under nitrogen atmosphere for 2 hours. On completion, the mixture was diluted with water (200 mL) and extracted with ethyl acetate (3×200 mL). The combined organic layer was dried over anhydrous Na$_2$SO$_4$, filtered and concentrated in vacuo to give the crude product. The crude product was triturated with PE (100 mL) and filtered to give the title compound (28.8 g, 82% yield) as a yellow solid. $^1$H NMR (400 MHz, MeOD-d$_4$) δ 8.98 (s, 1H), 7.85-7.81 (m, 2H), 7.71-7.66 (m, 2H), 2.53 (s, 3H); LC-MS (ESI$^+$) m/z 201.0 (M+H)$^+$.

Step 2—[4-(4-Methylthiazol-5-yl)phenyl]methanamine

To a solution of 4-(4-methylthiazol-5-yl)benzonitrile (14.7 g, 73.4 mmol) in MeOH (460 mL) was added dichlorocobalt (14.3 g, 110 mmol) and the mixture was cooled to 0° C. Then, NaBH$_4$ (13.9 g, 367 mmol) was added in portions over 0.5 hour. Finally, the mixture was allowed to warm to rt and stirred for 12 hours. On completion, the reaction mixture was quenched with NH$_3$.H$_2$O (20 mL, 30 wt %), then diluted with water (100 mL) and extracted with DCM (3×80 mL). The combined organic layer was dried over anhydrous Na$_2$SO$_4$, filtered and concentrated in vacuo to give a residue. The residue was purified by reverse phase flash column (0.1% NH$_3$—H$_2$O in water) to give the title compound (3.50 g, 23.3% yield) as a yellowish oil. LC-MS (ESI$^+$) m/z 205.1 (M+H)$^+$.

Step 3—Tert-butyl (2S,4R)-4-hydroxy-2-[[4-(4-methylthiazol-5-yl)phenyl]methylcarbamoyl]-pyrrolidine-1-carboxylate A solution of (2S,4R)-1-tert-butoxycarbonyl-4-hydroxy-pyrrolidine-2-carboxylic acid (3.36 g, 14.5 mmol, CAS #13726-69-7) in DMF (50 mL) was cooled to 0° C. Then, DIPEA (5.13 g, 39.7 mmol), [4-(4-methylthiazol-5-yl) phenyl]methanamine (2.70 g, 13.2 mmol) and HATU (6.03 g, 15.9 mmol) were added. Finally, the mixture was allowed to warm to rt and stirred for 12 hours. On completion, the reaction mixture was concentrated under reduced pressure to remove the DMF. The residue was diluted with water (50 mL) and extracted with DCM (3×60 mL). The combined organic layer was dried over anhydrous Na$_2$SO$_4$, filtered and concentrated in vacuo to give a residue. The residue was purified by reverse phase flash (0.1% NH$_3$—H$_2$O in water) column to give the title compound (1.70 g, 30% yield) as a yellowish solid. $^1$H NMR (400 MHz, MeOD-d$_4$) δ 8.91 (s, 1H), 7.48-7.40 (m, 4H), 4.74-4.25 (m, 4H), 3.66-3.56 (m, 1H), 3.54-3.43 (m, 1H), 2.48 (s, 3H), 2.31-2.20 (m, 1H), 2.08-1.98 (m, 1H), 1.54-1.25 (m, 9H); LC-MS (ESI$^+$) m/z 418.0 (M+H)$^+$.

Step 4—(2S,4R)-4-hydroxy-N-[[4-(4-methylthiazol-5-yl)phenyl]methyl]pyrrolidine-2-carboxamide To a solution of tert-butyl (2S,4R)-4-hydroxy-2-[[4-(4-methylthiazol-5-yl)phenyl]methylcarbamoyl]-pyrrolidine-1-carboxylate (1.70 g, 4.07 mmol) in DCM (10 mL) was added HCl in dioxane (4 M, 10 mL) and the mixture was stirred at rt for 6 hours. On completion, the mixture was concentrated under reduced pressure to give the product (1.60 g, HCl salt, 96% yield) as a yellowish solid. LC-MS (ESI$^+$) m/z 318.0 (M+H)$^+$.

Step 5—Tert-butyl N-[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]carbamate A solution of (2S,4R)-4-hydroxy-N-[[4-(4-methylthiazol-5-yl)phenyl]methyl]pyrrolidine-2-carboxamide (1.60 g, 4.52 mmol, HCl salt) in DMF (25.00 mL) was cooled to 0° C. Then, DIPEA (1.75 g, 13.6 mmol), (2S)-2-(tert-butoxycarbonylamino)-3,3-dimethyl-butanoic acid (1.31 g, 5.65 mmol) and HATU (2.06 g, 5.43 mmol) were added. Finally, the mixture was allowed to warm to rt and stirred for 12 hours. On completion, the reaction mixture was concentrated under reduced pressure to remove the DMF. The residue was diluted with water (40 mL) and extracted with DCM (3×40 mL). The combined organic layer was dried over anhydrous Na$_2$SO$_4$, filtered and concentrated in vacuo to give a residue. The residue was purified by reverse phase flash column (0.1% NH$_3$—H$_2$O in water) to give the title compound (1.70 g, 70% yield) as a light yellow solid. $^1$H NMR (400 MHz, CDCl$_3$-d$_1$) δ 8.71 (s, 1H), 7.43 (s, 1H), 7.39-7.30 (m, 4H), 5.20 (d, J=8.0 Hz, 1H), 4.78 (t, J=1.6 Hz, 1H), 4.59 (m, 1H), 4.33 (m, 1H), 4.18-4.09 (m, 2H), 3.58 (m, 1H), 2.60 (m, 1H), 2.52 (s, 3H), 2.14 (m, 1H), 1.41 (s, 9H), 0.92 (s, 9H); LC-MS (ESI$^+$) m/z 531.1 (M+H)$^+$.

Step 6—(2S,4R)-1-[(2S)-2-amino-3,3-dimethyl-butanoyl]-4-hydroxy-N-[[4-(4-methylthiazol-5-yl)-phenyl]methyl]pyrrolidine-2-carboxamide To a solution of tert-butyl N-[(1S)-1-[(2S,4R)-4-hydroxy-2-[[4-(4-methylthiazol-5-yl)phenyl]-methyl carbamoyl]pyrrolidine-1-carbonyl]-2,2-dimethyl-propyl]carbamate (1.60 g, 3.01 mmol) in DCM (20 mL) was added HCl in dioxane (4 M, 20 mL). Then, the mixture was stirred at rt for 6 hours. On completion, the mixture was concentrated under reduced pressure to give the title compound as a light yellow solid (1.90 g, HCl salt, 95% yield). $^1$H NMR (400 MHz, MeOD-d$_4$) δ 9.98 (s, 1H), 7.58-7.52 (m, 4H), 4.72-4.65 (m, 1H), 4.60-4.50 (m, 2H), 4.46-4.38 (m, 1H), 4.07 (s, 1H), 3.86-3.83 (m, 1H), 3.75-3.68 (m, 1H), 3.60 (s, 1H), 2.61 (s, 3H), 2.33-2.28 (m, 1H), 2.11-2.05 (m, 1H), 1.14 (s, 9H); LC-MS (ESI$^+$) m/z 431.1 (M+H)$^+$.

4-Nitro-1H-pyrazole-5-carboxamide (Intermediate CJ)

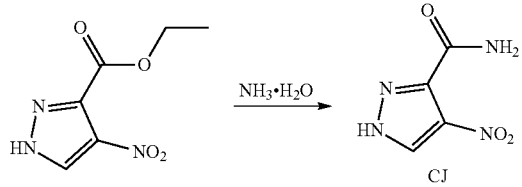

A solution of ethyl 4-nitro-1H-pyrazole-5-carboxylate (6.00 g, 32.4 mmol, CAS #55864-87-4) in NH$_3$.H$_2$O (60 mL) was stirred at 100° C. for 16 hours. On completion, the reaction mixture was concentrated in vacuo to give the title compound (5.10 g, 98% yield) as a light yellow solid. H NMR (400 MHz, DMSO-d$_6$) δ 8.71 (s, 1H), 8.09 (s, 1-H), 7.85 (s, 1H).

(E)-N,N-dimethyl-2-nitro-ethenamine (Intermediate CK)

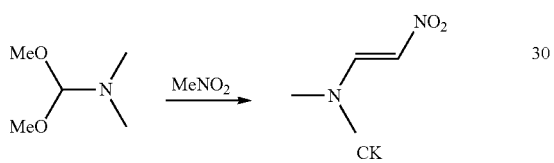

A mixture of 1,1-dimethoxy-N,N-dimethyl-methanamine (20.0 g, 167 mmol, 22.30 mL) in MeNO$_2$ (12.8 mL) was stirred at 80° C. for 30 minutes. On completion, the mixture was concentrated in vacuo. The residue was purified by column chromatography to give the title compound (14.0 g, 72% yield) as a red brown solid. $^1$H NMR (400 MHz, DMSO-d$_6$) δ 8.13 (d, J=10.8 Hz 1H), 6.62 (d, J=10.8 Hz, 1H), 3.21 (s, 3H), 2.88 (s, 3H).

Methyl 4-(4-amino-3-carbamoyl-pyrazol-1-yl)benzoate (Intermediate CL)

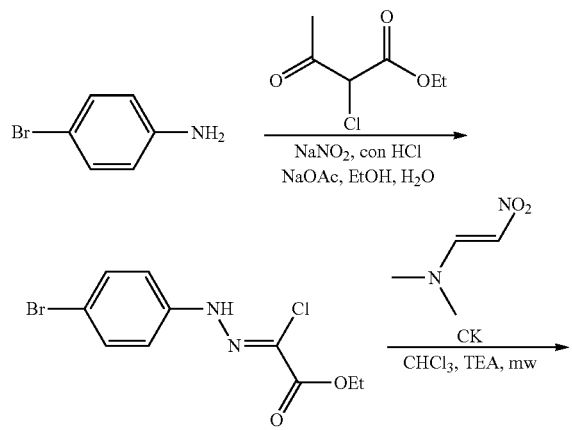

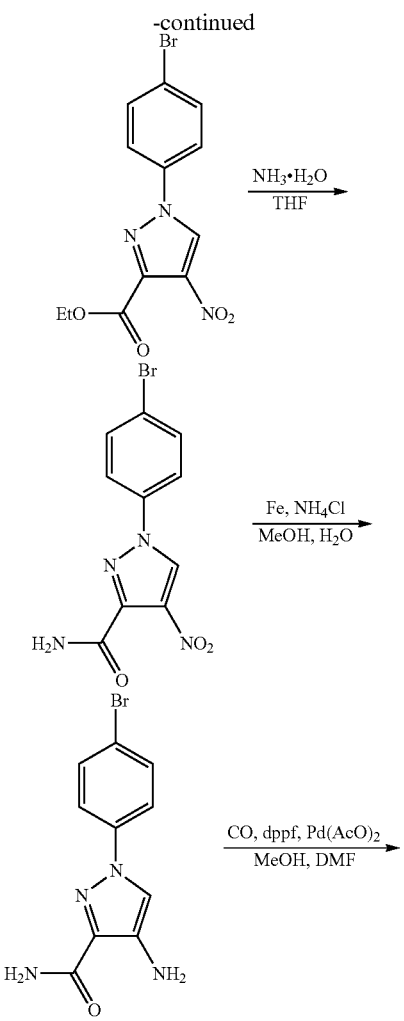

Step 1—Ethyl (2E)-2-[(4-bromophenyl)hydrazono]-2-chloro-acetate

To a mixture of 4-bromoaniline (50.0 g, 291 mmol) in a mixed solvent of HCl (12 N, 72.6 mL) and H$_2$O (150 mL) was added a solution of NaNO$_2$ (22.1 g, 319 mmol) in H$_2$O (50 mL) dropwise at −5° C. The mixture was stirred at 0° C. for 0.5 hour. Then ethyl 2-chloro-3-oxo-butanoate (50.2 g, 305 mmol, 42.2 mL) and NaOAc (71.53 g, 872 mmol) were added to the solution at 0° C. and the mixture was stirred for 30 minutes. The reaction mixture was then allowed to warm to rt and stirred for an additional for 2 hours. On completion, the reaction mixture was filtered and the filter cake was dried in vacuo. The residue was triturated with MeOH (500 mL) to give the title compound (50.0 g, 56% yield) as a yellow solid. $^1$H NMR (400 MHz, DMSO-$d_6$) δ 8.32 (s, 1H), 7.45-7.20 (m, 2H), 7.14-7.11 (m, 2H), 4.40 (q, J=7.2 Hz, 2H), 1.41 (t, J=7.2 Hz, 3H).

Step 2—Ethyl 1-(4-bromophenyl)-4-nitro-pyrazole-3-carboxylate

Ethyl (2Z)-2-[(4-bromophenyl)hydrazono]-2-chloro-acetate (1.00 g, 3.27 mmol), (E)-N,N-dimethyl-2-nitro-ethenamine (380 mg, 3.27 mmol, Intermediate CK) and Et$_3$N (331 mg, 3.27 mmol) were taken up into a microwave tube in CHCl$_3$ (3 mL). The sealed tube was heated at 140° C. for 1 hour under microwave. On completion, the mixture was concentrated in vacuo. The residue was purified by reverse phase flash (0.1% FA in water) to give the title compound (350 mg, 28% yield) as a yellow solid. $^1$H NMR (400 MHz, DMSO-$d_6$) δ 9.76 (s, 1H), 7.97-7.90 (m, 2H), 7.85-7.78 (m, 2H), 4.43 (q, J=7.2 Hz, 2H), 1.34 (t, J=7.2 Hz, 3H).

Step 3—1-(4-Bromophenyl)-4-nitro-pyrazole-3-carboxamide

To a solution of ethyl 1-(4-bromophenyl)-4-nitro-pyrazole-3-carboxylate (0.50 g, 1.47 mmol) in THF (10 mL) was added NH$_3$.H$_2$O (15.1 g, 129 mmol, 16.6 mL, 30 wt %). The mixture was stirred at 110° C. for 3 hours in a seal tube. On completion, the reaction mixture was concentrated in vacuo to give the title compound (500 mg, 98% yield) as pale solid. LC-MS (ESI$^+$) m/z 310.9 (M+H)$^+$.

Step 4—4-Amino-1-(4-bromophenyl)pyrazole-3-carboxamide

To a solution of 1-(4-bromophenyl)-4-nitro-pyrazole-3-carboxamide (500 mg, 1.61 mmol) in MeOH (10 mL) and H$_2$O (4 mL) was added Fe (898 mg, 16.0 mmol) and NH$_4$Cl (860 mg, 16.0 mmol). The mixture was stirred at 75° C. for 5 hours. On completion, the mixture was filtered and the filtrate was concentrated in vacuo. The residue was dissolved in EA (30 mL) and washed with water (10 mL). The organic layer was separated and concentrated in vacuo. The residue was purified by silica gel chromatography to give the title compound (230 mg, 49% yield) as a yellow solid. LC-MS (ESI$^+$) m/z 304.9 (M+Na+2)$^+$.

Step 5—Methyl 4-(4-amino-3-carbamoyl-pyrazol-1-yl)benzoate

A mixture of 4-amino-1-(4-bromophenyl)pyrazole-3-carboxamide (0.23 g, 818 umol), dppf (18.2 mg, 32.0 umol), Pd(OAc)$_2$ (7.35 mg, 32.0 umol) in DMF (5 mL) and MeOH (5 mL) was degassed and purged with nitrogen gas three times. Then the mixture was stirred at 80° C. for 16 h under CO atmosphere (50 psi pressure). On completion, the mixture was filtered and the filtrate was concentrated to remove MeOH. Then the residue was diluted with EA (200 mL) and washed with water (2×50 mL). The organic layer was dried over anhydrous Na$_2$SO$_4$, filtered and concentrated in vacuo. The residue was purified by silica gel chromatography to give the title compound (140 mg, 61% yield) as a light yellow solid. $^1$H NMR (400 MHz, DMSO-$d_6$) δ 8.12-7.96 (m, 4H), 7.89 (s, 1H), 7.62 (s, 1H), 7.33 (s, 1H), 4.95 (s, 2H), 3.87 (s, 3H); LC-MS (ESI$^+$) m/z 261.0 (M+H)$^+$.

2-[2-[tert-butoxycarbonyl(2,2,2-trifluoroethyl)amino]-4-pyridyl]oxazole-4-carboxylic acid (Intermediate CM)

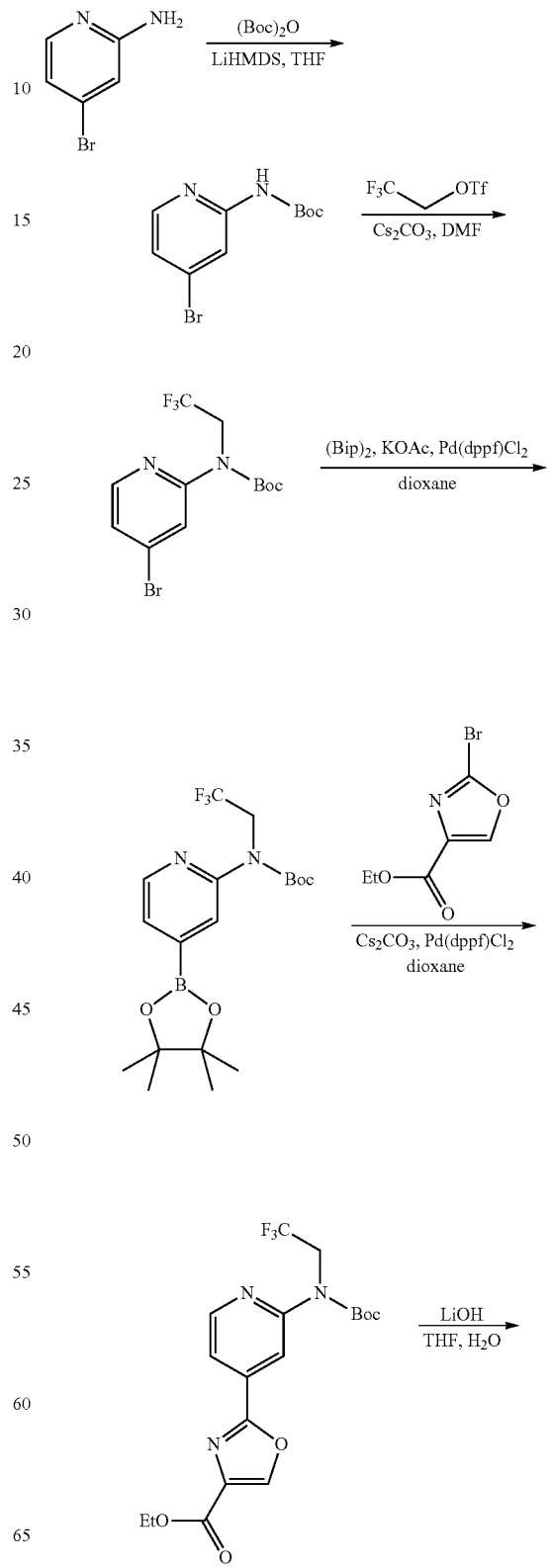

-continued

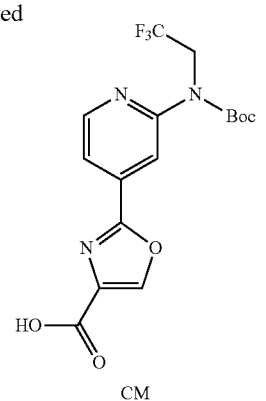

CM

Step 1—Tert-butyl N-(4-bromo-2-pyridyl)carbamate

A solution of 4-bromopyridin-2-amine (5.00 g, 28.9 mmol) in dry THF (100 mL) was treated with LiHMDS (1 M, 57.8 mL) at −5 OC and the solution was stirred at −5 OC for 10 minutes. Then (Boc)$_2$O (6.31 g, 28.9 mmol) was added and the mixture was allowed to warm to rt and stirred for 1 h. On completion, the reaction mixture was quenched with saturated ammonium chloride solution (20 mL) and extracted with EtOAc (3×100 mL). The combined organic layers were washed with brine (20 mL), dried with Na$_2$SO$_4$, filtered and concentrated in vacuo. The residue was purified by silica gel column chromatography to give the title compound (6.50 g, 82% yield) as a white solid. $^1$H NMR (400 MHz, CDCl$_3$) δ=8.92 (s, 1H), 8.27 (d, J=0.8 Hz, 1H), 8.13 (d, J=5.2 Hz, 1H), 7.12 (dd, J=1.6, 5.2 Hz, 1H), 1.55 (s, 9H).

Step 2—Tert-butyl N-(4-bromo-2-pyridyl)-N-(2,2,2-trifluoroethyl)carbamate

To a mixture of tert-butyl N-(4-bromo-2-pyridyl)carbamate (6.10 g, 22.3 mmol), cesium carbonate (11.0 g, 33.7 mmol) and DMF (60 mL) was added 2,2,2-trifluoroethyl trifluoromethanesulfonate (5.18 g, 22.3 mmol). The reaction mixture was stirred at rt for 15 h. On completion, the reaction mixture was quenched with saturated aqueous ammonium chloride solution (50 mL) and extracted with ethyl acetate (3×100 mL). The organic layer was washed with saturated brine (20 mL), dried over anhydrous sodium sulfate, filtered and concentrated in vacuo. The residue was purified by silica gel column chromatography to give the title compound (5.70 g, 72% yield) as a colorless oil. $^1$H NMR (400 MHz, CDCl$_3$) δ=8.18 (d, J=5.2 Hz, 1H), 8.01-7.94 (m, 1H), 7.24 (dd, J=1.6, 5.2 Hz, 1H), 4.81 (q, J=8.8 Hz, 2H), 1.55 (s, 9H).

Step 3—Tert-butyl N-[4-(4,4,5,5-tetramethyl-1,3,2-dioxaborolan-2-yl)-2-pyridyl]-N-(2,2,2-trifluoroethyl)carbamate To a solution of tert-butyl N-(4-bromo-2-pyridyl)-N-(2,2,2-trifluoroethyl)carbamate (3.00 g, 8.45 mmol) in dioxane (60 mL) was added 4,4,5,5-tetramethyl-2-(4,4,5,5-tetramethyl-1,3,2-dioxaborolan-2-yl)-1,3,2-dioxaborolane (10.7 g, 42.2 mmol), KOAc (1.66 g, 16.9 mmol) and Pd(dppf)Cl$_2$.CH$_2$Cl$_2$ (345 mg, 423 umol) under nitrogen atmosphere. The reaction mixture was then heated to 65° C. and stirred for 2 h. On completion, the reaction mixture was diluted with ethyl acetate (100 mL) and filtered. The filtrate was concentrated in vacuo. The residue was purified by silica gel column chromatography to give the title compound (3.00 g, 96% yield) as a white solid. $^1$H NMR (400 MHz, CDCl$_3$) δ=8.38 (dd, J=0.8, 4.8 Hz, 1H), 7.91 (s, 1H), 7.42 (d, J=4.8 Hz, 1H), 4.76 (q, J=8.8 Hz, 2H), 1.52 (s, 9H), 1.35 (s, 12H).

Step 4—Ethyl 2-[2-[tert-butoxycarbonyl(2,2,2-trifluoroethyl)amino]-4-pyridyl]oxazole-4-carboxylate To a solution of tert-butyl N-[4-(4,4,5,5-tetramethyl-1,3,2-dioxaborolan-2-yl)-2-pyridyl]-N-(2,2,2-trifluoroethyl)carbamate (4.00 g, 9.94 mmol), ethyl 2-bromooxazole-4-carboxylate (2.19 g, 9.94 mmol) in dioxane (40 mL) and H$_2$O (8 mL) was added Cs$_2$CO$_3$ (6.48 g, 19.9 mmol) and Pd(dppf)Cl$_2$—CH$_2$Cl$_2$ (406 mg, 497 umol) and the mixture was stirred at 80° C. for 16 h. On completion, the reaction mixture was diluted with ethyl acetate (200 mL) and filtered. The filtrate was concentrated in vacuo. The residue was purified by silica gel column chromatography to give the title compound (2.10 g, 51% yield) as a yellow solid. $^1$H NMR (400 MHz, CDCl$_3$) δ=8.50 (d, J=5.2 Hz, 1H), 8.38 (s, 1H), 8.34 (s, 1H), 7.79 (d, J=5.2 Hz, 1H), 4.85 (q, J=8.8 Hz, 2H), 4.45 (q, J=7.2 Hz, 2H), 1.56 (s, 9H), 1.43 (t, J=7.2 Hz, 3H); LC-MS (ESI$^+$) m/z 416.1 (M+H)$^+$.

Step 5—2-[2-[Tert-butoxycarbonyl(2,2,2-trifluoroethyl)amino]-4-pyridyl]oxazole-4-carboxylic acid To a solution of ethyl 2-[2-[tert-butoxycarbonyl(2,2,2-trifluoroethyl)amino]-4-pyridyl]oxazole-4-carboxylate (100 mg, 241 umol) in THF (1 mL) and H$_2$O (200 uL) was added LiOH (11.5 mg, 482 umol). The mixture was stirred at rt for 0.5 h. On completion, the reaction mixture was acidified with 1N HCl (3 mL) to pH=5, then extracted with ethyl acetate (5×20 mL). The combined organic layers were washed with brine (20 mL), dried over anhydrous sodium sulfate, filtered and concentrated in vacuo to give the title compound (90.0 mg, 97% yield) as a white solid. $^1$H NMR (400 MHz, CDCl$_3$) δ=8.53 (dd, J=0.8, 5.2 Hz, 1H), 8.46 (s, 1H), 8.40 (s, 1H), 7.79 (dd, J=1.2, 5.2 Hz, 1H), 7.81-7.77 (m, 1H), 4.86 (q, J=8.8 Hz, 2H), 1.57 (s, 9H); LC-MS (ESI$^+$) m/z 388.1 (M+H)$^+$

4-[4-[[2-[2-[Tert-butoxycarbonyl(2,2,2-trifluoro-ethyl)amino]-4-pyridyl]oxazole-4-carbonyl]amino]-3-carbamoyl-pyrazol-1-yl]benzoic acid (Intermediate CN)

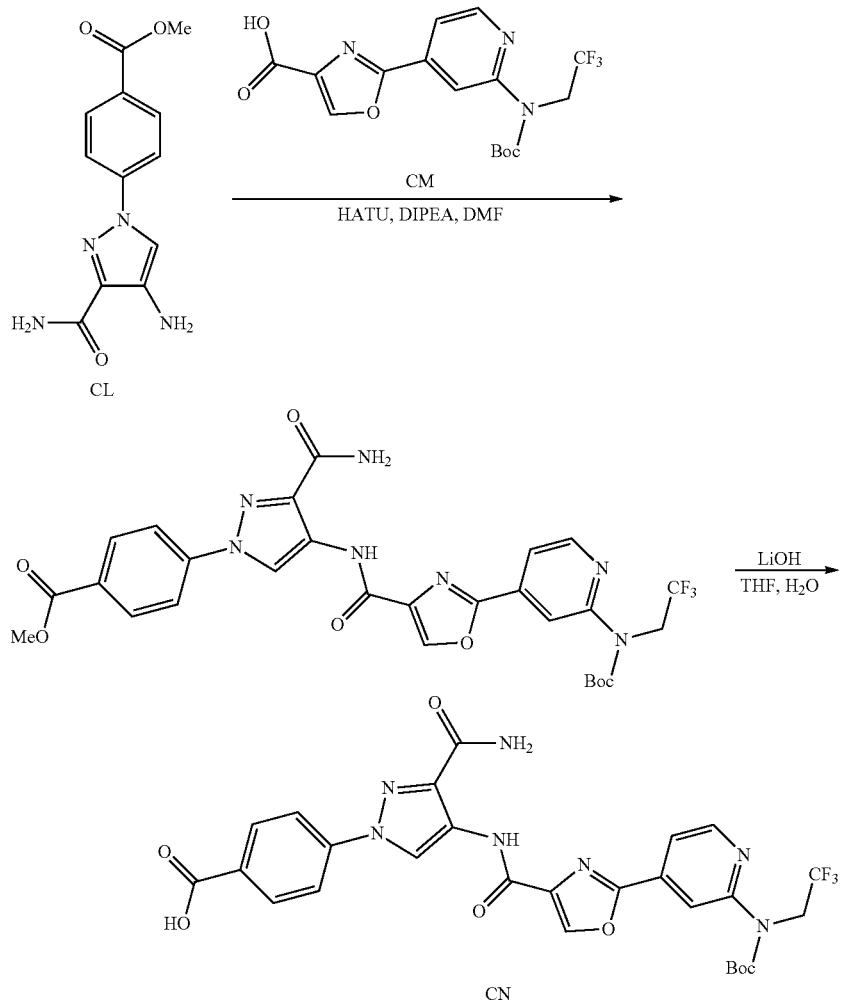

Step 1—Methyl 4-[4-[[2-[2-[tert-butoxycarbonyl(2,2,2-trifluoroethyl)amino]-4-pyridyl]oxazole-4-carbonyl]amino]-3-carbamoyl-pyrazol-1-yl]benzoate To a mixture of methyl 4-(4-amino-3-carbamoyl-pyrazol-1-yl)benzoate (120 mg, 461 umol, Intermediate CL) and 2-[2-[tert-butoxycarbonyl(2,2,2-trifluoroethyl)amino]-4-pyridyl]oxazole-4-carboxylic acid (179 mg, 461, Intermediate CM) in DMF (5 mL) was added DIPEA (179 mg, 1.38 mmol) and HATU (210 mg, 553 umol) and the mixture was stirred at rt for 2 h. On completion, the mixture was diluted with water (20 mL), extracted with EA (2×50 mL), and the organic layer was concentrated in vacuo. The residue was purified by silica gel chromatography to give the title compound (223 mg, 72% yield) as a white solid. $^1$H NMR (400 MHz, DMSO-$d_6$) δ 11.07 (s, 1H), 9.11 (s, 1H), 9.06 (s, 1H), 8.74-8.61 (m, 1H), 8.26 (s, 1H), 8.16-8.05 (m, 5H), 7.86-7.75 (m, 2H), 4.91 (m, 2H), 3.89 (s, 3H), 1.54 (s, 9H); LC-MS (ESI$^+$) m/z 630.2 (M+H)$^+$.

Step 2—4-[4-[[2-[2-[Tert-butoxycarbonyl(2,2,2-trifluoroethyl)amino]-4-pyridyl]oxazole-4-carbonyl]amino]-3-carbamoyl-pyrazol-1-yl]benzoic acid To a solution of methyl 4-[4-[[2-[2-[tert-butoxycarbonyl(2,2,2-trifluoroethyl)amino]-4-pyridyl]oxazole-4-carbonyl]amino]-3-carbamoyl-pyrazol-1-yl]benzoate (210 mg, 333 umol) in THF (5 mL) and H$_2$O (5 mL) was added LiOH (40.0 mg, 1.67 mmol). The mixture was stirred at rt for 16 h. On completion, the mixture was adjusted to pH=6 with 1N HCl, then extracted with EA (2×100 mL). The organic layer was concentrated in vacuo to give the title compound (150 mg, 68% yield) as a white solid. $^1$H NMR (400 MHz, DMSO-$d_6$) δ 11.08 (s, 1H), 9.12 (s, 1H), 8.99 (s, 1H), 8.67 (d, J=5.2 Hz, 1H), 8.26 (s, 1H), 8.13-7.97 (m, 5H), 7.79-7.76 (m, 2H), 7.76 (s, 1H), 4.91 (m, 2H), 1.54 (s, 9H); LC-MS (ESI$^+$) m/z 616.2 (M+H)$^+$.

1213

5-bromo-2-(2,6-dioxopiperidin-3-yl)isoindoline-1,3-dione (Intermediate CO)

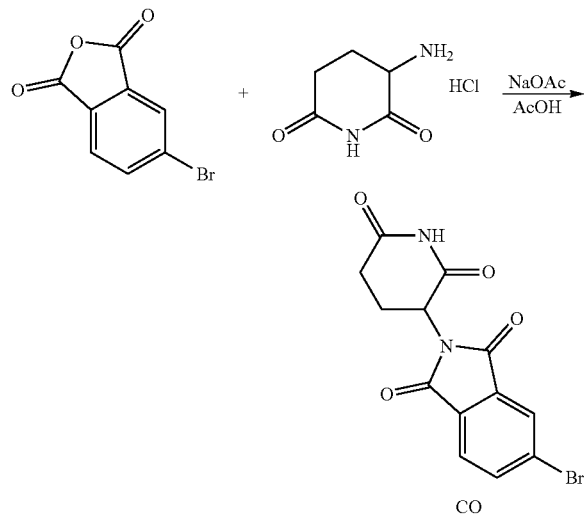

To a solution of 4-bromophthalic anhydride (15.0 g, 66.1 mmol, CAS #86-90-8) in acetic acid (225 mL) was added 2,6-dioxopiperidin-3-amine hydrochloride (10.87 g, 66.1 mmol, CAS #24666-56-6) and sodium acetate (5.42 g, 66.07 mmol) at rt. The reaction mixture was heated to 80° C. and stirred for 16 h. The resulting reaction mixture was cooled to rt and concentrated on a rotary evaporator. The obtained residue was suspended in water (255 mL) and the resulting mixture was cooled to 0° C. The resulting slurry was stirred at 0° C. for 1 h. The resulting precipitate was filtered, washed with water (60 mL) and dried under vacuum to give the title compound (20.44 g, 92%) as a purple solid. LC-MS (ESI$^+$) m/z 336.9 (M+H)$^+$.

5-(3-(2-aminoethoxy)propyl)-2-(2,6-dioxopiperidin-3-yl)isoindoline-1,3-dione (Intermediate CP)

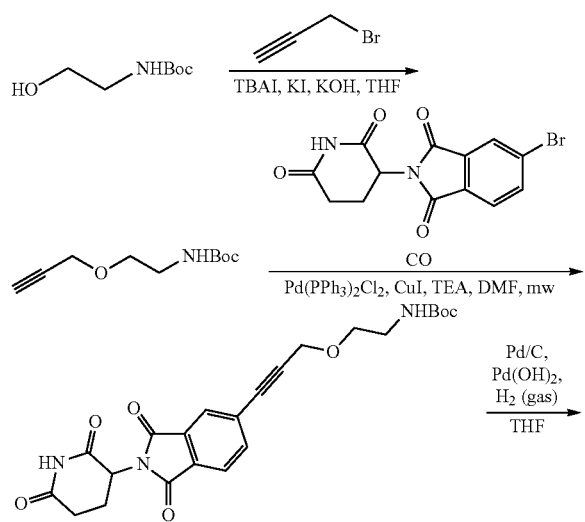

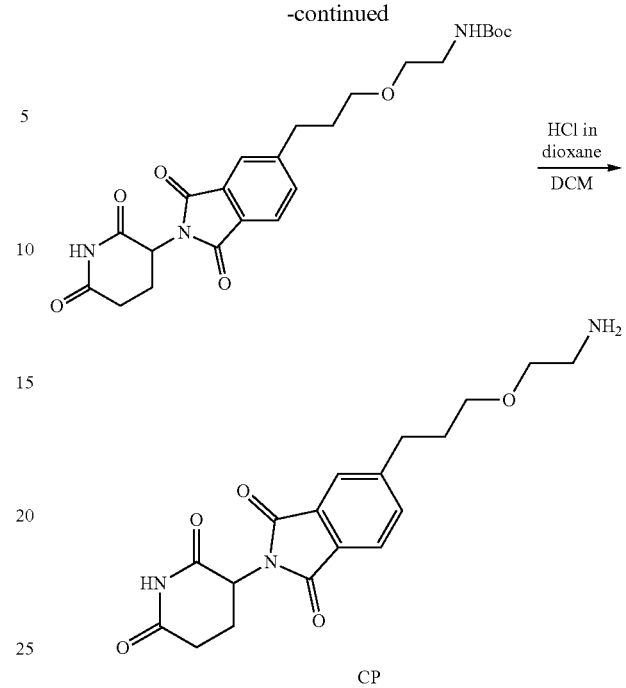

Step 1—Tert-butyl N-(2-prop-2-ynoxyethyl)carbamate

To a solution of tert-butyl N-(2-hydroxyethyl)carbamate (1 g, 6.20 mmol) and 3-bromoprop-1-yne (775 mg, 6.51 mmol) in THF (30 mL) was added TBAI (137 mg, 372 umol) and KI (154 mg, 931 umol). Then KOH (409 mg, 6.20 mmol) was added into the above mixture and the reaction mixture was stirred at rt for 20 h. On completion, the mixture was concentrated in vacuo to remove the solvent. The residue was diluted with water (40 mL) and extracted with EA (3×30 mL). The organic phase was dried over Na$_2$SO$_4$, filtered and concentrated in vacuo. The residue was purified by silica gel chromatography (SiO$_2$) to give the title compound (0.84 g, 68% yield) as a colorless oil. $^1$H NMR (400 MHz, CDCl$_3$) δ 4.84 (s, 1H), 4.09 (d, J=2.4 Hz, 2H), 3.52 (t, J=5.2 Hz, 2H), 3.28-3.26 (m, 2H), 2.38 (t, J=2.4 Hz, 1H), 1.38 (s, 9H).

Step 2—Tert-butyl (2-((3-(2-(2,6-dioxopiperidin-3-yl)-1,3-dioxoisoindolin-5-yl)prop-2-yn-1-yl)oxy)ethyl)carbamate 5-bromo-2-(2,6-dioxopiperidin-3-yl)isoindoline-1,3-dione (0.4 g, 1.19 mmol, Intermediate CO), CuI (22.6 mg, 119 umol) and Pd(PPh$_3$)$_2$Cl$_2$ (83.3 mg, 119 umol) were put into a microwave tube. Then tert-butyl N-(2-prop-2-ynoxyethyl) carbamate (473 mg, 2.37 mmol), TEA (2.16 g, 2.98 mL, 21.4 mmol) and DMF (3 mL) were added into the tube. The mixture was degassed with nitrogen for 5 minutes. The sealed tube was then heated at 80° C. for 30 minutes under microwave. On completion, the reaction mixture was filtered and the filtrate was concentrated in vacuo. The residue was purified by silica gel chromatography (SiO$_2$) to give the title compound (510 mg, 94% yield) as a yellow oil. $^1$H NMR (400 MHz, CDCl$_3$) δ 8.16 (s, 1H), 7.92 (s, 1H), 7.87-7.78 (m, 2H), 5.03-4.96 (m, 1H), 4.94 (s, 1H), 4.43 (s, 2H), 3.67

(t, J=5.2 Hz, 2H), 3.39 (d, J=5.2 Hz, 2H), 2.96-2.90 (m, 1H), 2.88-2.80 (m, 1H), 2.79-2.71 (m, 1H), 2.21-2.13 (m, 1H), 1.45 (s, 9H).

Step 3—Tert-butyl (2-(3-(2-(2,6-dioxopiperidin-3-yl)-1,3-dioxoisoindolin-5-yl)propoxy)ethyl)carbamate To a solution of tert-butyl N-[2-[3-[2-(2,6-dioxo-3-piperidyl)-1,3-dioxo-isoindolin-4-yl]prop-2-ynoxy]ethyl]carbamate (490 mg, 1.08 mmol) in THF (5 mL) was added Pd/C (0.2 g, 329 umol, 10 wt %) and Pd(OH)$_2$/C (0.2 g, 329 umol, 10 wt %). The reaction mixture was stirred at rt for 18 h under hydrogen atmosphere (15 Psi pressure). On completion, the mixture was filtered and the filtrate was concentrated in vacuo to give the title compound (370 mg, 75% yield) as a yellow oil. LC-MS (ESI$^+$) m/z 360.0 (M+H–100)$^+$.

Step 4—5-(3-(2-aminoethoxy)propyl)-2-(2,6-dioxopiperidin-3-yl)isoindoline-1,3-dione To a solution of tert-butyl N-[2-[3-[2-(2,6-dioxo-3-piperidyl)-1,3-dioxo-isoindolin-4-yl]propoxy]ethyl]carbamate (120 mg, 26 umol) in DCM (1 mL) was added HCl/dioxane (4 M, 1 mL). The reaction mixture was stirred at rt for 0.5 hr. On completion, the mixture was concentrated in vacuo to give the title compound (90 mg, 96% yield) as a yellow oil. LC-MS (ESI$^+$) m/z 360.0 (M+H)$^+$.

5-(3-(2-(2-aminoethoxy)ethoxy)propyl)-2-(2,6-dioxopiperidin-3-yl)isoindoline-1,3-dione (Intermediate CO)

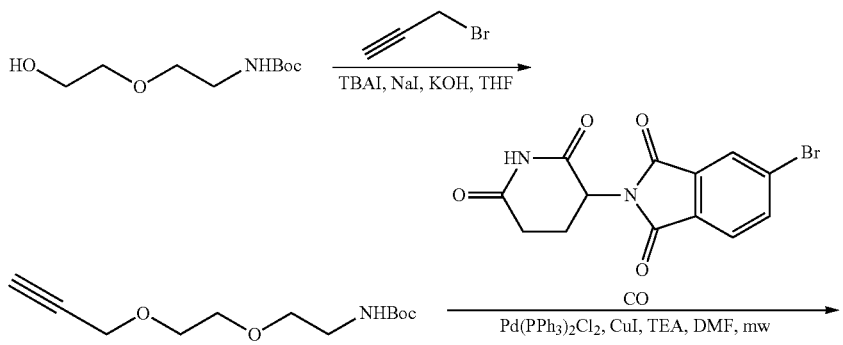

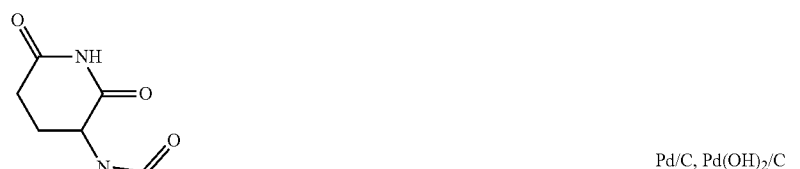

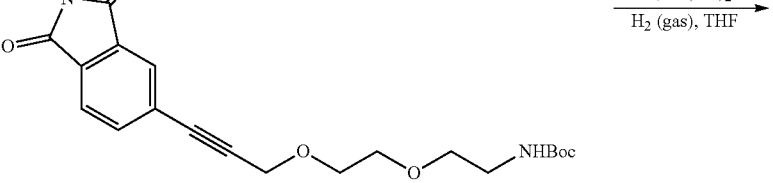

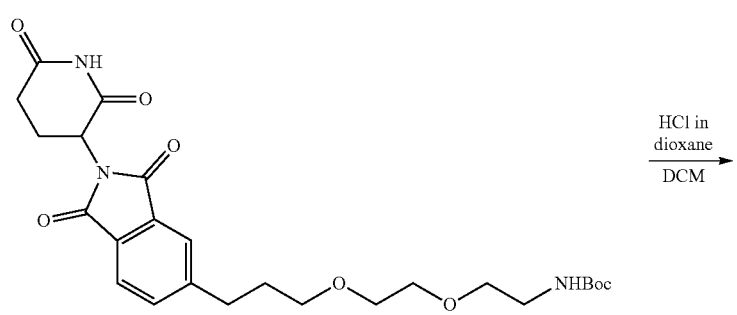

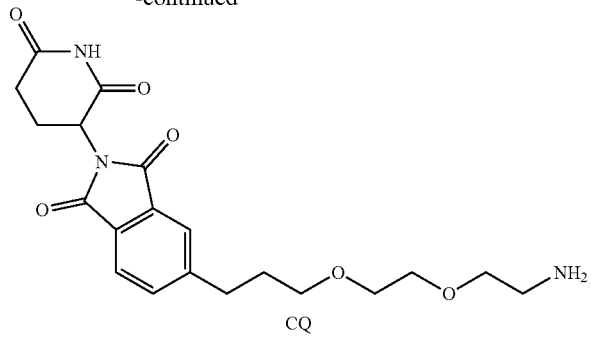

CQ

Step 1—Tert-butyl N-[2-(2-prop-2-ynoxyethoxy)ethyl]carbamate

To a solution of tert-butyl N-[2-(2-hydroxyethoxy)ethyl]carbamate (5.00 g, 24.4 mmol, CAS #139115-91-6) and 3-bromoprop-1-yne (2.90 g, 24.4 mmol, 2.10 mL) in THF (40 mL) was added TBAI (540 mg, 1.46 mmol), KI (606 mg, 3.65 mmol) and KOH (1.61 g, 24.4 mmol, 85% wt %). The reaction mixture was stirred at rt for 16 h. On completion, the mixture was filtered, and the filtrate was concentrated in vacuo to give a residue. The residue was diluted with H$_2$O (20 mL) and extracted with EA (2×50 mL). The organic phase was concentrated in vacuo to give a residue. The residue was purified by column chromatography (SiO$_2$, Petroleum ether:Ethyl acetate=5:1) to give the title compound (4.00 g, 67% yield) as a yellow oil. $^1$H NMR (400 MHz, CDCl$_3$) δ 5.02 (s, 1H), 4.17 (d, J=2.4 Hz, 2H), 3.68-3.63 (m, 2H), 3.62-3.58 (m, 2H), 3.51 (t, J=5.2 Hz, 2H), 3.28 (q, J=5.2 Hz, 2H), 2.43 (t, J=2.4 Hz, 1H), 1.43 (s, 9H).

Step 2-Tert-butyl (2-(2-((3-(2-(2,6-dioxopiperidin-3-yl)-1,3-dioxoisoindolin-5-yl)prop-2-yn-1-yl)oxy)ethoxy)ethyl)carbamate To a solution of 5-bromo-2-(2,6-dioxopiperidin-3-yl)isoindoline-1,3-dione (300 mg, 890 umol, Intermediate CO) and tert-butyl N-[2-(2-prop-2-ynoxyethoxy)ethyl]carbamate (433 mg, 1.78 mmol) in DMF (8 mL) was added Pd(PPh$_3$)$_2$Cl$_2$ (62.5 mg, 88.9 umol), TEA (1.62 g, 16.0 mmol, 2.23 mL) and CuI (16.9 mg, 88.9 umol). The reaction mixture was heated at 80° C. for 30 minutes under microwave. On completion, the mixture was concentrated in vacuo to give a residue. The residue was purified by column chromatography (SiO$_2$, Petroleum ether:Ethyl acetate=5:1 to 1:0) to give the title compound (440 mg, 89% yield) as a yellow solid. LC-MS (ESI$^+$) m/z 400.1 (M+H-100)$^+$.

Step 3—Tert-butyl (2-(2-(3-(2-(2,6-dioxopiperidin-3-yl)-1,3-dioxoisoindolin-5-yl)propoxy)ethoxy)ethyl)carbamate To a solution of tert-butyl N-[2-[2-[3-[2-(2,6-dioxo-3-piperidyl)-1,3-dioxo-isoindolin-4-yl]prop-2-ynoxy]ethoxy]ethyl]carbamate (580 mg, 1.16 mmol) in THF (10 mL) was added Pd/C (300 mg, 10 wt %) and Pd(OH)$_2$/C (300 mg, 10 wt %). The reaction mixture was stirred at rt under hydrogen atmosphere (15 psi pressure) for 12 h. On completion, the residue was filtered and the filter was concentrated in vacuo to give the title compound (500 mg, 85% yield) as a yellow oil. LC-MS (ESI$^+$) m/z 526.1 (M+Na)$^+$.

Step 4—5-(3-(2-(2-amino ethoxy)propyl)-2-(2,6-dioxopiperidin-3-yl)isoindoline-1,3-dione To a solution of tert-butyl N-[2-[2-[3-[2-(2,6-dioxo-3-piperidyl)-1,3-dioxo-isoindolin-4-yl]propoxy]ethoxy]ethyl]carbamate (200 mg, 397 umol) in DCM (2 mL) was added HCl in dioxane (4 M, 2.00 mL), and the reaction mixture was stirred at rt for 20 minutes. On completion, the mixture was concentrated in vacuo to give the title compound (160 mg, 99% yield) as a yellow solid. LC-MS (ESI$^+$) m/z 404.0 (M+H)$^+$.

2-[2-[2-[(4-Methoxyphenyl)methyl-methyl-amino]ethoxy]ethoxy]ethanamine (Intermediate CR)

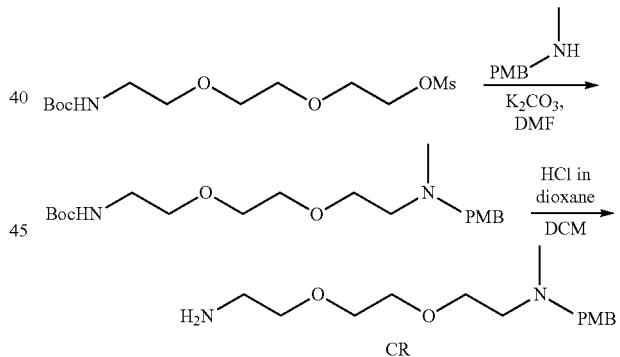

CR

Step 1—Tert-butyl N-[2-[2-[2-[(4-methoxyphenyl)methyl-methyl-amino]ethoxy]ethoxy]ethyl]carbamate To a mixture of 2-[2-[2-(tert-butoxycarbonylamino)ethoxy]ethoxy]ethyl methanesulfonate (1.30 g, 3.97 mmol, synthesized via Step 1 of Intermediate AM) and 1-(4-methoxyphenyl)-N-methyl-methanamine (600 mg, 3.97 mmol) in DMF (15 mL) was added K$_2$CO$_3$ (1.10 g, 7.94 mmol). The reaction mixture was stirred at rt for 16 hours. On completion, the mixture was diluted with water (10 mL) and extracted with DCM (3×20 mL). The organic layers were dried over anhydrous Na$_2$SO$_4$, filtered and the filtrate was concentrated in vacuo to give a residue. The residue was purified by reverse phase chromatography (0.1% NH$_3$.H$_2$O)

to give the title compound (670 mg, 44% yield) as a light yellow oil. LC-MS (ESI+) m/z 383.2 (M+H)+.

Step 2—2-[2-[2-[(4-Methoxyphenyl)methyl-methyl-amino]ethoxy]ethoxy]ethanamine

To a mixture of tert-butyl N-[2-[2-[2-[(4-methoxyphenyl)methyl-methyl-amino]ethoxy]ethoxy]ethyl]carbamate (470 mg, 1.23 mmol) in DCM (4 mL) was added HCl in dioxane (4 M, 1.5 mL). The reaction mixture was stirred at rt for 2 hours. On completion, the mixture was concentrated in vacuo to give the title compound (350 mg, 95% yield) as a light yellow oil. LC-MS (ESI+) m/z 283.1 (M+H)+.

5-(1-amino-3,6,9,12-tetraoxapentadec-14-yn-15-yl)-2-(2,6-dioxopiperidin-3-yl)isoindoline-1,3-dione hydrochloride (Intermediate CS)

degassed with argon for 10-15 min. Then Pd(PPh3)2Cl2 (0.02 g, 0.029 mmol) was added to the reaction mixture and argon purging was continued for 5-10 min. The reaction mixture was then heated at 70° C. and stirred for 0.5 h under argon atmosphere. The resulting reaction mixture was then cooled to rt and concentrated on a rotary evaporator. The obtained crude product was purified by gradient column chromatography using neutral alumina as stationary phase and DCM/IPA as a mobile phase. The title compound (1.1 g, 63%) was isolated as a light yellow viscous oil which solidified upon standing overnight at 0-5° C. temperature. LC-MS (ESI+) m/z 488.0 (M-100+H)+.

Step 2—5-(1-amino-3,6,9,12-tetraoxapentadec-14-yn-15-yl)-2-(2,6-dioxopiperidin-3-yl)isoindoline-1,3-dione hydrochloride To a solution of tert-butyl (15-(2-(2,6-dioxopiperidin-3-yl)-1,3-dioxoisoindolin-5-yl)-3,6,9,12-tetraoxapentadec-14-

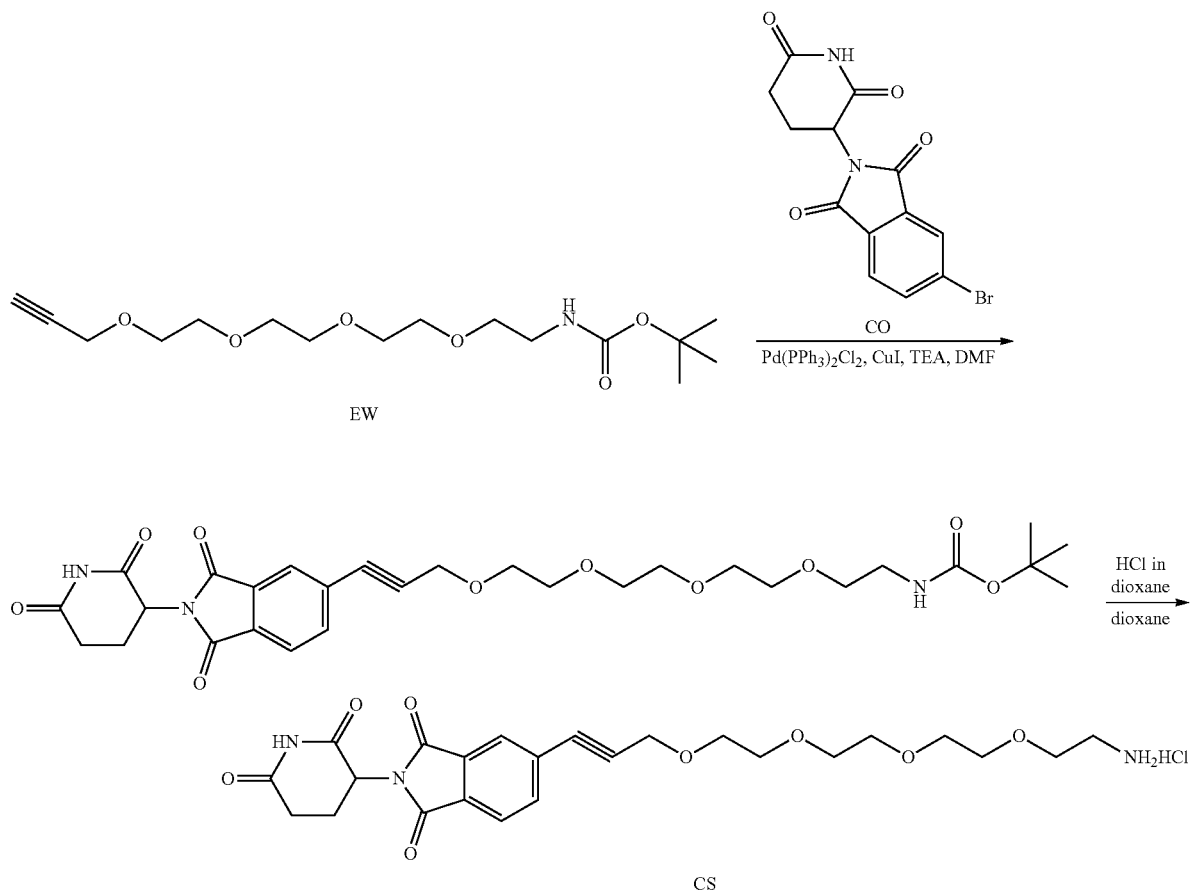

Step 1—tert-butyl (15-(2-(2,6-dioxopiperidin-3-yl)-1,3-dioxoisoindolin-5-yl)-3,6,9,12-tetraoxapentadec-14-yn-1-yl)carbamate In a flame dried reaction assembly equipped with nitrogen bubbler was prepared a solution of 5-bromo-2-(2,6-dioxopiperidin-3-yl)isoindoline-1,3-dione (1.0 g, 3.0 mmol, Intermediate CO) and tert-butyl (3,6,9,12-tetraoxapentadec-14-yn-1-yl)carbamate (1.18 g, 3.56 mmol, Intermediate EW) in DMF (20 mL) at rt. Cuprous iodide (0.11 g, 0.59 mmol) and TEA (5.0 mL, 36.0 mmol) were sequentially added to the reaction mixture at rt. The resulting reaction mixture was yn-1-yl)carbamate (2.1 g, 35.8 mmol) in 1,4-dioxane (5 mL) was added 4N HCl in Dioxane (20 mL) at rt. The reaction mixture was stirred at rt for 5 h. The resulting reaction mixture was concentrated under vacuum to get a brown color viscous liquid which was further triturated with diethyl ether (20 mL) followed by n-pentanes (30 mL) to give the title compound (1.9 g, 99%) as a yellowish hygroscopic solid. LC-MS (ESI+) m/z 488.0 (M+H)+.

5-(1-amino-3,6,9,12-tetraoxapentadecan-15-yl)-2-(2,6-dioxopiperidin-3-yl)isoindoline-1,3-dione hydrochloride (Intermediate CT)

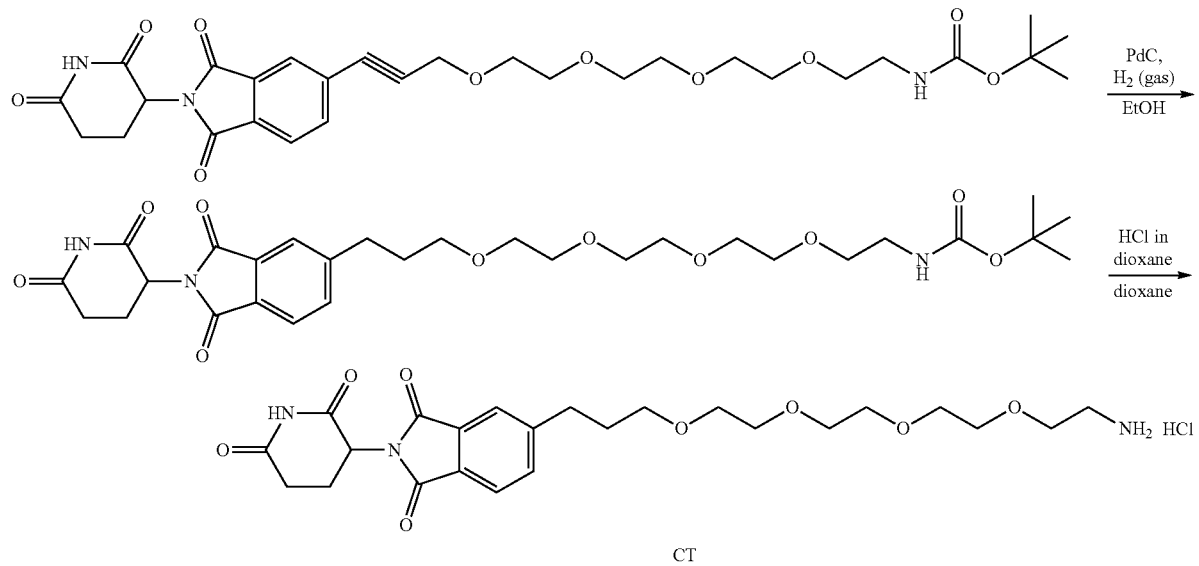

Step-1 tert-butyl (15-(2-(2,6-dioxopiperidin-3-yl)-1,3-dioxoisoindolin-5-yl)-3,6,9,12-tetraoxapentadecyl)carbamate To a solution of tert-butyl (15-(2-(2,6-dioxopiperidin-3-yl)-1,3-dioxoisoindolin-5-yl)-3,6,9,12-tetraoxapentadec-14-yn-1-yl)carbamate (3.0 g, 51.0 mmol, synthesized via Step 1 of Intermediate CS) in ethanol (100 mL) was added Pd/C (1.5 g, 10 wt %) under nitrogen atmosphere. Hydrogen gas was purged into the reaction mixture and the reaction was stirred for 6 h at rt. The resulting reaction mixture was filtered through a pad of celite and washed with ethanol (30 mL). The resulting filtrate was concentrated under vacuum to give the title compound (3.0 g, 96%) as a green viscous oil. LC-MS (ESI$^+$) m/z 492.0 (M-100+H)$^+$.

Step-2 5-(1-amino-3,6,9,12-tetraoxapentadecan-15-yl)-2-(2,6-dioxopiperidin-3-yl)isoindoline-1,3-dione hydrochloride To a solution of tert-butyl (15-(2-(2,6-dioxopiperidin-3-yl)-1,3-dioxoisoindolin-5-yl)-3,6,9,12-tetraoxapentadecyl)carbamate (3.0 g, 50.7 mmol) in 1,4-dioxane (20 mL) was added 4N HCl in dioxane (25 mL) at rt. The reaction mixture was stirred at rt for 5 h. The resulting reaction mixture was concentrated under vacuum to get a brown color viscous liquid which was further triturated with diethyl ether (30 mL) followed by n-pentanes (30 mL) to give the title compound (2.5 g, 93%) as a brown liquid. LC-MS (ESI$^+$) m/z 492.4 (M+H)$^+$.

4-[4-[[6-[2-[Tert-butoxycarbonyl(2,2,2-trifluoroethyl)amino]-4-pyridyl]pyridine-2-carbonyl]amino]-3-carbamoyl-pyrazol-1-yl]benzoic acid (Intermediate CU)

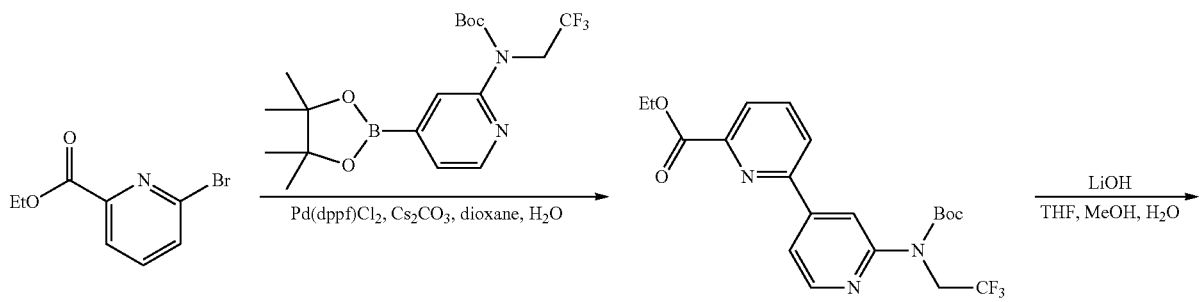

-continued

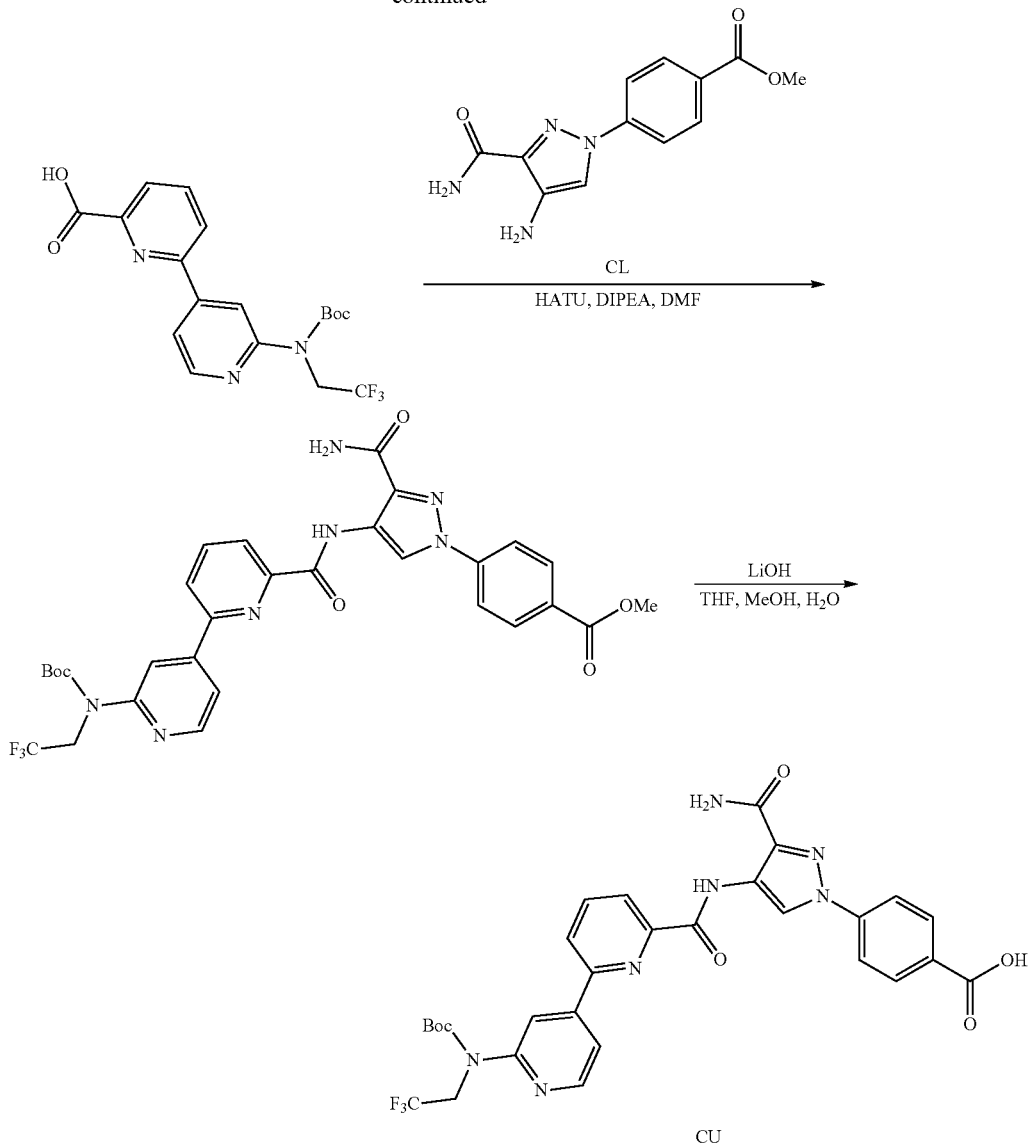

Step 1—Ethyl 6-[2-[tert-butoxycarbonyl(2,2,2-trifluoroethyl)amino]-4-pyridyl]pyridine-2-carboxylate To a mixture of ethyl 6-bromopyridine-2-carboxylate (1.50 g, 6.52 mmol) and tert-butyl N-[4-(4,4,5,5-tetramethyl-1,3,2-dioxaborolan-2-yl)-2-pyridyl]-N-(2,2,2-trifluoroethyl)carbamate (5.46 g, 6.52 mmol, synthesized via Steps 1-3 of Intermediate CM) in a mixed solvent of dioxane (40 mL) and H$_2$O (8 mL) was added Cs$_2$CO$_3$ (6.37 g, 19.5 mmol) and Pd(dppf)Cl$_2$ (238 mg, 326 umol). The reaction mixture was stirred at 80° C. for 16 hours. On completion, the reaction mixture was filtered and concentrated in vacuo. The residue was purified by column chromatography to give the title compound (1.90 g, 68% yield) as a light yellow oil. LC-MS (ESI$^+$) m/z 448.0 (M+Na)$^+$.

Step 2—6-[2-[Tert-butoxycarbonyl(2,2,2-trifluoroethyl)amino]-4-pyridyl]pyridine-2-carboxylic acid To a mixture of methyl 6-[2-[tert-butoxycarbonyl(2,2,2-trifluoroethyl)amino]-4-pyridyl]pyridine-2-carboxylate (800 mg, 1.94 mmol) in a mixed solvent of THF (6 mL), H$_2$O (1 mL) and MeOH (1 mL) was added LiOH (93.1 mg, 3.89 mmol). The reaction mixture was stirred at rt for 0.5 hour. On completion, the reaction mixture was acidified with HCl (1 N) until the pH=5-6 and concentrated in vacuo to give the title compound (700 mg, 95% yield) as a white solid. LC-MS (ESI$^+$) m/z 420.1 (M+Na)$^+$.

Step 3—Methyl 4-[4-[[6-[2-[tert-butoxycarbonyl(2,2,2-trifluoroethyl)amino]-4-pyridyl]pyridine-2-carbonyl]amino]-3-carbamoyl-pyrazol-1-yl]benzoate To a mixture of methyl 4-(4-amino-3-carbamoyl-pyrazol-1-yl)benzoate (550 mg, 2.11 mmol, Intermediate CL) and DIPEA (975 mg, 7.55 mmol in DMF (8 mL) was added 6-[2-[tert-butoxycarbonyl (2,2,2-trifluoroethyl)amino]-4-pyridyl]pyridine-2-carboxylic acid (600 mg, 1.51 mmol) and HATU (688 mg, 1.81 mmol). The reaction mixture was stirred at rt for 0.5 hour. On completion, the reaction mixture was diluted with water (10 mL) and extracted with EA (4×10 mL). The combined organic layers were dried over Na₂SO₄, filtered and concentrated in vacuo to give a residue. The residue was purified by prep-HPLC (0.1% FA) to give the title compound (140 mg, 14% yield) as a white solid. LC-MS (ESI⁺) m/z 640.2 (M+H)⁺.

Step 4—4-[4-[[6-[2-[Tert-butoxycarbonyl(2,2,2-trifluoroethyl)amino]-4-pyridyl]pyridine-2-carbonyl]amino]-3-carbamoyl-pyrazol-1-yl]benzoic acid To a mixture of methyl 4-[4-[[6-[2-[tert-butoxycarbonyl(2,2,2-trifluoroethyl)amino]-4-pyridyl]pyridine-2-carbonyl]amino]-3-carbamoyl-pyrazol-1-yl]benzoate (80.0 mg, 125 umol) in a mixed solvent of THF (4 mL), MeOH (1 mL) and H₂O (1 mL) was added LiOH (14.9 mg, 625 umol). The reaction mixture was stirred at rt for 4 hours. On completion, the reaction mixture was acidified with HCl (1 N) until the pH=5-6 and concentrated in vacuo to give the title compound (120 mg, 100% yield) as a brown solid. LC-MS (ESI⁺) m/z 626.2 (M+H)⁺.

N-[1-[4-(bromomethyl)phenyl]-3-carbamoyl-pyrazol-4-yl]-2-[2-(2,2,2-trifluoroethylamino)-4-pyridyl]oxazole-4-carboxamide (Intermediate CV Step 1—Tert-butyl N-[4-[4-[[3-carbamoyl-1-[4-(hydroxymethyl)phenyl]pyrazol-4-yl]carbamoyl]oxazol-2-yl]-2-pyridyl]-N-(2,2,2-trifluoroethyl)carbamate To a solution of 4-[4-[[2-[2-[tert-butoxycarbonyl(2,2,2-trifluoroethyl)amino]-4-pyridyl]oxazole-4-carbonyl]amino]-3-carbamoyl-pyrazol-1-yl]benzoic acid (1.00 g, 1.62 mmol, Intermediate CN) in THF (30 mL) was added TEA (329 mg, 3.25 mmol) and isopropyl carbonochloridate (398 mg, 3.25 mmol). The mixture was stirred at −10° C. for 2 hours, then the mixture was filtered and washed with THF (30 mL). To the filtrate was then added NaBH₄ (246 mg, 6.50 mmol) and H₂O (5 mL) at 0° C. and the mixture was stirred at 0° C. for 1 hour. On completion, the mixture was extracted with DCM (200 mL). The organic layer was concentrated in vacuo and the residue was triturated in DCM to give the title compound (420 mg, 43% yield) as a white solid. LC-MS (ESI⁺) m/z 602.2 (M+H)⁺.

Step 2—N-[1-[4-(bromomethyl)phenyl]-3-carbamoyl-pyrazol-4-yl]-2-[2-(2,2,2-trifluoroethylamino)-4-pyridyl]oxazole-4-carboxamide To a mixture of tert-butyl N-[4-[4-[[3-carbamoyl-1-[4-(hydroxymethyl)phenyl]pyrazol-4-yl]carbamoyl]oxazol-2-

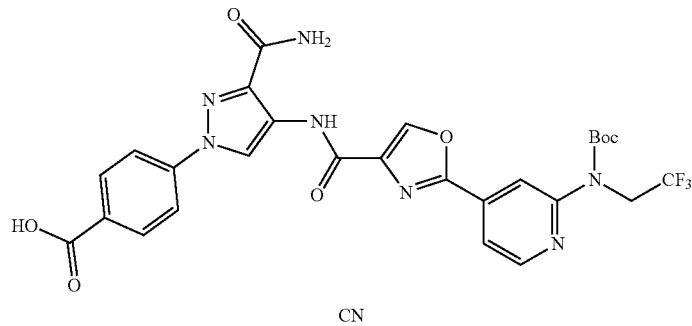

CN

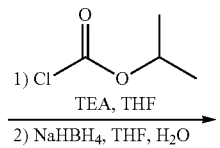

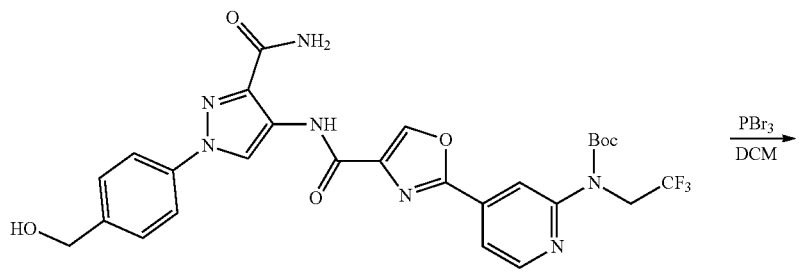

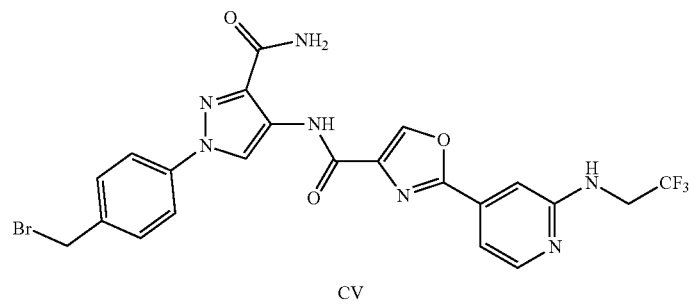

CV yl]-2-pyridyl]-N-(2,2,2-trifluoroethyl)carbamate (0.25 g, 416 umol) in DCM (5 mL) was added PBr₃ (169 mg, 623 umol). Then the reaction mixture was stirred at rt for 3 hours. On completion, the reaction mixture was quenched with water (20 mL), washed with saturated NaHCO₃ (30 mL), and extracted with DCM (3×30 mL). The organic layer was dried with Na₂SO₄, filtered and concentrated in vacuo to give the title compound (0.10 g, 34% yield) as a pale solid. LC-MS (ESI⁺) m/z 565.9 (M+H)⁺.

4-[4-[[2-[2-[Tert-butoxycarbonyl(2,2,2-trifluoro-ethyl)amino]-4-pyridyl]oxazole-4-carbonyl]amino]-3-carbamoyl-pyrazol-1-yl]cyclohexanecarboxylic acid (Intermediate CW)

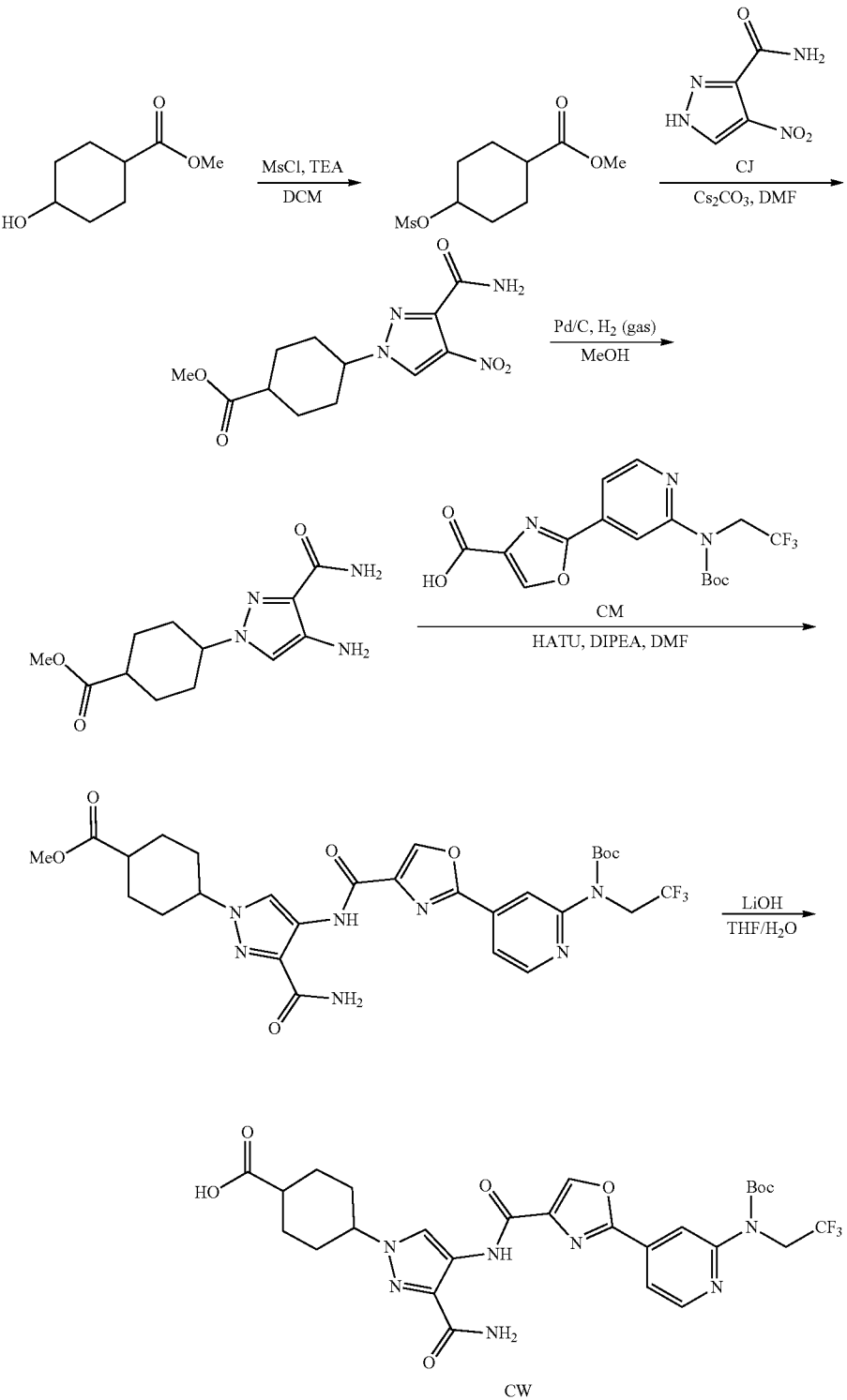

Step 1—Methyl 4-methyl sulfonyloxycyclohexanecarboxylate

To a solution of methyl 4-hydroxycyclohexanecarboxylate (5.00 g, 31.6 mmol) and TEA (6.40 g, 63.2 mmol, 8.80 mL) in DCM (50 mL) was added MsCl (4.34 g, 37.9 mmol, 2.94 mL) dropwise at 0° C. Then the reaction mixture was allowed to warm to rt and stirred for 3 hours. On completion, the mixture was diluted with $H_2O$ (20 mL), then extracted with DCM (2×40 mL). The combined organic phase was dried over by $Na_2SO_4$ and concentrated in vacuo to give the title compound (7.00 g, 93% yield) as a white solid.

Step 2—Methyl 4-(3-carbamoyl-4-nitro-pyrazol-1-yl)cyclohexanecarboxylate

To a solution of 4-nitro-1H-pyrazole-3-carboxamide (4.62 g, 29.6 mmol, Intermediate CJ) and methyl 4-methylsulfonyloxycyclohexanecarboxylate (7.00 g, 29.6 mmol) in DMF (100 mL) was added $Cs_2CO_3$ (19.3 g, 59.2 mmol). The reaction mixture was stirred at 130° C. for 12 hours. On completion, the mixture was filtered, and concentrated in vacuo to give a residue. The residue was purified by reverse phase chromatography (0.1% $NH_3.H_2O$) to give the title compound (2.20 g, 25% yield) as a yellow oil. LC-MS (ESI$^+$) m/z 297.2 (M+H)$^+$.

Step 3—Methyl 4-(4-amino-3-carbamoyl-pyrazol-1-yl)cyclohexanecarboxylate

To a solution of methyl 4-(3-carbamoyl-4-nitro-pyrazol-1-yl)cyclohexanecarboxylate (0.60 g, 2.03 mmol) in MeOH (10 mL) was added Pd/C (400 mg, 10 wt %). The reaction mixture was stirred under hydrogen atmosphere (15 psi pressure) at rt for 16 hours. On completion, the mixture was filtered and the filtrate was concentrated in vacuo to give the title compound (490 mg, 90% yield) as a purple oil. LC-MS (ESI$^+$) m/z 267.1 (M+H)$^+$.

Step 4—methyl 4-[4-[[2-[2-[tert-butoxycarbonyl(2,2,2-trifluoroethyl)amino]-4-pyridyl]oxazole-4-carbonyl]amino]-3-carbamoyl-pyrazol-1-yl]cyclohexanecarboxylate To a solution of methyl 4-(4-amino-3-carbamoyl-pyrazol-1-yl)cyclohexanecarboxylate (150 mg, 563 umol) and 2-[2-[tert-butoxycarbonyl(2,2,2-trifluoroethyl)amino]-4-pyridyl]oxazole-4-carboxylic acid (218 mg, 563 umol, Intermediate CM) in DMF (5 mL) was added DIPEA (363 mg, 2.82 mmol, 490 uL). The mixture was stirred at rt for 12 minutes, then HATU (257 mg, 675 umol) was added and the reaction mixture was stirred at rt for 12 hours. On completion, the mixture was diluted with $H_2O$ (10 mL) and then extracted with EtOAc (2×20 mL). The organic phase was dried over $Na_2SO_4$, filtrated and concentrated in vacuo to give the title compound (400 mg, 83% purity, 92% yield) as a white solid. LC-MS (ESI$^+$) m/z 636.2 (M+H)$^+$.

Step 5—4-[4-[[2-[2-[Tert-butoxycarbonyl(2,2,2-trifluoroethyl)amino]-4-pyridyl]oxazole-4-carbonyl]amino]-3-carbamoyl-pyrazol-1-yl]cyclohexanecarboxylic acid To a solution of methyl 4-[4-[[2-[2-[tert-butoxycarbonyl(2,2,2-trifluoroethyl)amino]-4-pyridyl]oxazole-4-carbonyl]amino]-3-carbamoyl-pyrazol-1-yl]cyclohexanecarboxylate (400 mg, 629 umol) in THF (10 mL) and $H_2O$ (2 mL) was added LiOH (22.6 mg, 944 umol). The reaction mixture was stirred at rt for 12 hours. On completion, the mixture was concentrated in vacuo to remove THF, then diluted with $H_2O$ (20 mL). The mixture was adjusted to pH=5 with 1N HCl, then extracted with EA (2×40 mL). The combined organic phase was dried with $Na_2SO_4$, filtered and concentrated in vacuo to give the title compound (330 mg, 84%) as a yellow solid. LC-MS (ESI$^+$) m/z 644.2 (M+Na)$^+$.

N-[3-carbamoyl-1-(4-piperidyl)pyrazol-4-yl]-2-[2-(2,2,2-trifluoroethylamino)-4-pyridyl]oxazole-4-carboxamide (Intermediate CX)

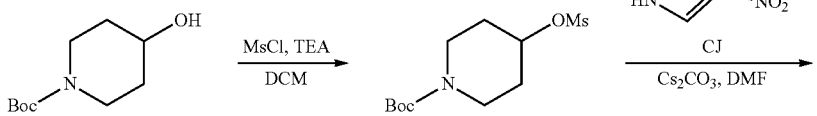

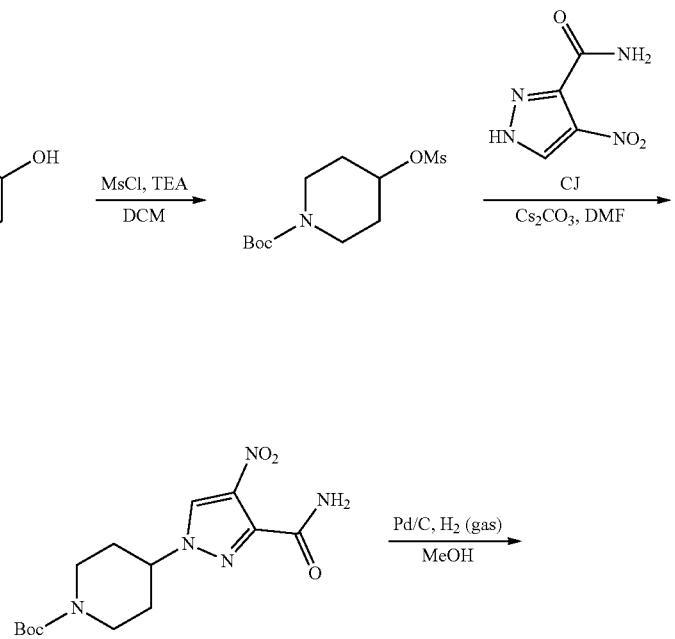

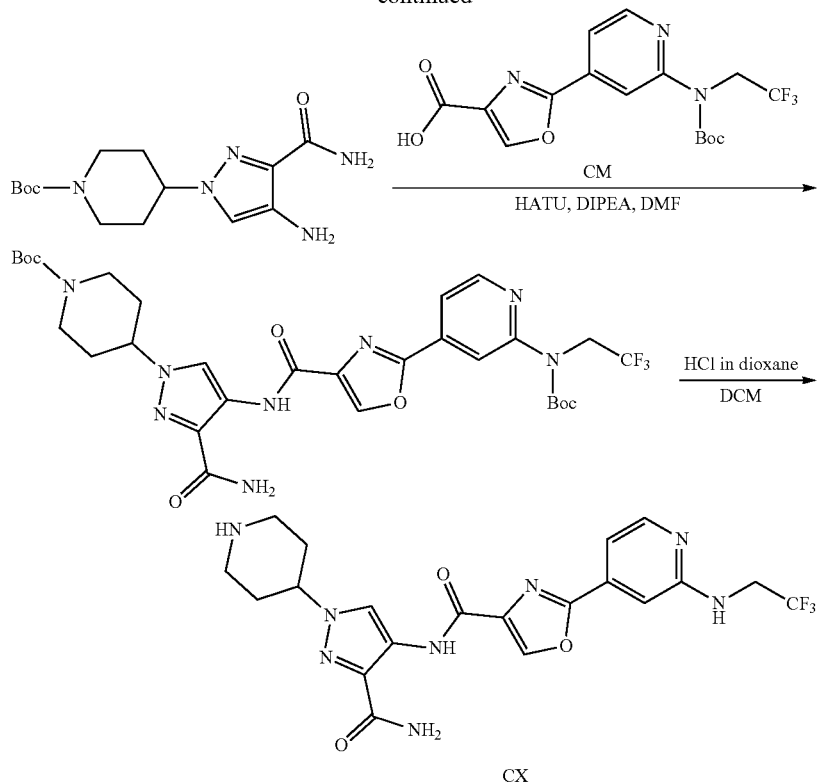

CX

Step 1—Tert-butyl 4-methylsulfonyloxypiperidine-1-carboxylate

To a mixture of tert-butyl 4-hydroxypiperidine-1-carboxylate (5.00 g, 24.8 mmol) and TEA (5.03 g, 49.6 mmol) in DCM (50 mL) was added MsCl (4.27 g, 37.2 mmol). The reaction mixture was stirred at rt for 0.5 hour. On completion, the reaction mixture was diluted with water (10 mL) and acidified with citric acid solution until the pH=5-6. Then the mixture was extracted with DCM (3×15 mL). The combined organic layers were diluted with water (10 mL) and basified with NaHCO$_3$ solution until the pH=7-8. Then the mixture was extracted with DCM (3×15 mL). The combined organic layers were dried over Na$_2$SO$_4$, filtered and concentrated in vacuo to give the title compound (7.00 g, 90% yield) as a white solid. $^1$H NMR (400 MHz, CDCl$_3$) δ 4.84 m 4.78 (m, 1H), 3.68-3.59 (m, 2H), 3.26-3.20 (m, 2H), 2.97 (s, 3H), 1.94-1.84 (m, 2H), 1.80-1.69 (m, 2H), 1.39 (s, 9H).

Step 2—Tert-butyl 4-(3-carbamoyl-4-nitro-pyrazol-1-yl)piperidine-1-carboxylate To a mixture of 4-nitro-1H-pyrazole-3-carboxamide (3.91 g, 25.0 mmol, Intermediate CJ) and tert-butyl 4-methylsulfonyloxypiperidine-1-carboxylate (7.00 g, 25.0 mmol) in DMF (70 mL) was added Cs$_2$CO$_3$ (16.3 g, 50.1 mmol). The reaction mixture was stirred at 130° C. for 16 hours. On completion, the reaction mixture was concentrated in vacuo. The residue was purified by prep-HPLC (0.1% NH$_3$.H$_2$O) to give the title compound (1.80 g, 21% yield) as a brown solid. $^1$H NMR (400 MHz, DMSO-d$_6$) δ=8.95 (s, 1H), 8.00 (s, 1H), 7.76 (s, 1H), 4.49-4.43 (m, 1H), 4.06 (d, J=11.6 Hz, 2H), 3.01-2.70 (m, 2H), 2.04 (d, J=9.6 Hz, 2H), 1.87-1.70 (m, 2H), 1.42 (s, 9H).

Step 3—Tert-butyl 4-(4-amino-3-carbamoyl-pyrazol-1-yl)piperidine-1-carboxylate To a mixture of tert-butyl 4-(3-carbamoyl-4-nitro-pyrazol-1-yl)piperidine-1-carboxylate (1.80 g, 5.30 mmol) in MeOH (30 mL) was added Pd/C (1.00 g, 10 wt %) under hydrogen atmosphere (15 psi pressure). The reaction mixture was stirred at rt for 16 hours. On completion, the reaction mixture was filtered and concentrated in vacuo to give the title compound (610 mg, 100% yield) as a light yellow solid. $^1$H NMR (400 MHz, DMSO-d$_6$) δ 7.17 (s, 1H), 7.08 (s, 1H), 6.98 (s, 1H), 4.70-4.53 (m, 2H), 4.25-4.17 (m, 1H), 4.03 (d, J=11.2 Hz, 2H), 2.99-2.80 (m, 2H), 1.94 (d, J=10.0 Hz, 2H), 1.80-1.70 (m, 2H), 1.42 (s, 9H).

Step 4—Tert-butyl4-[4-[[2-[2-[tert-butoxycarbonyl (2,2,2-trifluoroethyl)amino]-4-pyridyl]oxazole-4-carbonyl]amino]-3-carbamoyl-pyrazol-1-yl]piperidine-1-carboxylate To a mixture of tert-butyl 4-(4-amino-3-carbamoyl-pyrazol-1-yl)piperidine-1-carboxylate (159 mg, 516 umol) and DIPEA (200 mg, 1.55 mmol) in DMF (5 mL) was added 2-[2-[tert-butoxycarbonyl (2,2,2-trifluoroethyl)amino]-4-pyridyl]oxazole-4-carboxylic acid (200 mg, 516 umol, Intermediate CM) and HATU (235 mg, 619 umol). The reaction mixture was stirred at rt for 0.5 hour. On completion, the reaction mixture was diluted with water (10 mL) and extracted with EA (3×10 mL). The combined organic layers were dried over Na$_2$SO$_4$, filtered and concentrated in vacuo to give the title compound (400 mg, 80% purity, 91% yield) as a light yellow solid. LC-MS (ESI+) m/z 679.3 (M+H)+.

Step 5—N-[3-carbamoyl-1-(4-piperidyl)pyrazol-4-yl]-2-[2-(2,2,2-trifluoroethylamino)-4-pyridyl]oxazole-4-carboxamide To a mixture of tert-butyl 4-[4-[[2-[2-[tert-butoxycarbonyl(2,2,2-trifluoroethyl)amino]-4-pyridyl]oxazole-4-carbonyl]amino]-3-carbamoyl-pyrazol-1-yl]piperidine-1-carboxylate (400 mg, 589 umol) in DCM (4 mL) was added HCl in dioxane (4 M, 2 mL). The reaction mixture was stirred at rt for 1 hour. On completion, the reaction mixture was concentrated in vacuo to give the title compound (280 mg, HCl salt) as a light yellow solid. LC-MS (ESI+) m/z 479.2 (M+H)+.

Tert-butyl 2-(2-(2-(2-aminoethoxy)ethoxy)ethoxy) acetate (Intermediate CY)

mL) was added (1,3-dioxoisoindolin-2-yl)potassium (12.8 g, 69.0 mmol). The resulting reaction mixture was stirred at 80° C. for 12 hours. On completion, the reaction mixture was concentrated in vacuo. The residue was purified by silica gel chromatography to give the title compound (14.6 g, 80% yield) as a colorless oil. $^1$H NMR (400 MHz, CDCl$_3$) δ 7.89-7.83 (m, 2H), 7.75-7.69 (m, 2H), 3.95-3.90 (m, 2H), 3.79-3.74 (m, 2H), 3.69-3.64 (m, 4H), 3.63-3.59 (m, 2H), 3.56-3.52 (m, 2H).

Step 3—Tert-butyl 2-(2-(2-(2-(1,3-dioxoisoindolin-2-yl)ethoxy)ethoxy)ethoxy)acetate To a solution of 2-[2-[2-(2-hydroxyethoxy)ethoxy]ethyl] isoindoline-1,3-dione (10.0 g, 35.8 mmol) and Rh(OAc)$_2$ (396 mg, 1.79 mmol) in DCM (50 mL) was added a solution of tert-butyl 2-diazoacetate (7.63 g, 53.7 mmol) in DCM (200 mL) dropwise. The reaction mixture was stirred at rt for 18 hours. On completion, the reaction mixture was concentrated in vacuo. The residue was purified by silica gel

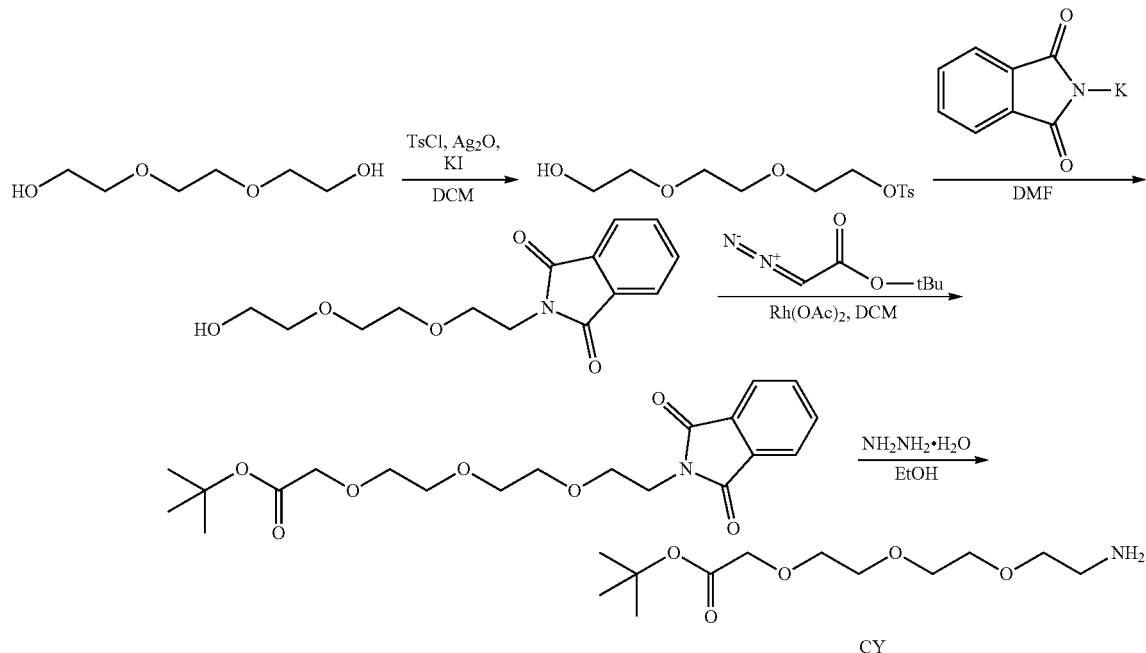

Step 1—2-(2-(2-Hydroxyethoxy)ethoxy)ethyl 4-methylbenzenesulfonate

To a solution of 2-[2-(2-hydroxyethoxy)ethoxy]ethanol (50.0 g, 333 mmol, 44.6 mL) in DCM (1 L) was added Ag$_2$O (84.9 g, 366 mmol) and KI (5.53 g, 33.3 mmol) and TsCl (63.5 g, 333 mmol). The reaction mixture was stirred at rt for 18 hours. On completion, the reaction mixture was filtered and the filtrate was concentrated in vacuo. The residue was purified by silica gel chromatography to give the title compound (76.0 g, 74% yield) as a colorless oil. $^1$H NMR (400 MHz, CDCl$_3$) δ 7.81 (d, J=8.0 Hz, 2H), 7.35 (d, J=8.0 Hz, 2H), 4.20-4.15 (m, 2H), 3.74-3.69 (m, 4H), 3.64-3.56 (m, 6H), 2.45 (s, 3H); LC-MS (ESI+) m/z 305.0 (M+H)+.

Step 2—2-(2-(2-(2-Hydroxyethoxy)ethoxy)ethyl) isoindoline-1,3-dione

To a solution of 2-[2-(2-hydroxyethoxy)ethoxy]ethyl 4-methylbenzenesulfonate (20.0 g, 65.7 mmol) in DMF (200 chromatography to give the title compound (11.0 g, 78% yield) as a colorless oil. $^1$H NMR (400 MHz, CDCl$_3$) δ 7.88-7.82 (m, 2H), 7.75-7.69 (m, 2H), 3.99 (s, 2H), 3.94-3.88 (m, 2H), 3.77-3.72 (m, 2H), 3.68-3.58 (m, 8H), 1.47 (s, 9H).

Step 4—Tert-butyl 2-(2-(2-(2-aminoethoxy)ethoxy) ethoxy)acetate

To a solution of tert-butyl 2-[2-[2-[2-(1,3-dioxoisoindolin-2-yl)ethoxy]ethoxy]ethoxy]acetate (11.0 g, 28.0 mmol) in ethanol (200 mL) was added NH$_2$NH$_2$.H$_2$O (7.00 g, 140 mmol). The reaction mixture was stirred at 80° C. for 2 hours. On completion, the reaction mixture was filtered. The filtrate was concentrated in vacuo. The residue was diluted with DCM (200 mL) and filtered. The filtrate was concentrated in vacuo to give the title compound (6.40 g, 87% yield) as a colorless oil. $^1$H NMR (400 MHz, CDCl$_3$) δ 4.02

(s, 2H), 3.72-3.63 (m, 10H), 3.53-3.50 (m, 2H), 1.47 (s, 9H); LC-MS (ESI+) m/z 264.0 (M+H)+.

Ethyl 2-[2-(2-aminoethoxy)ethoxy]acetate (Intermediate CZ)

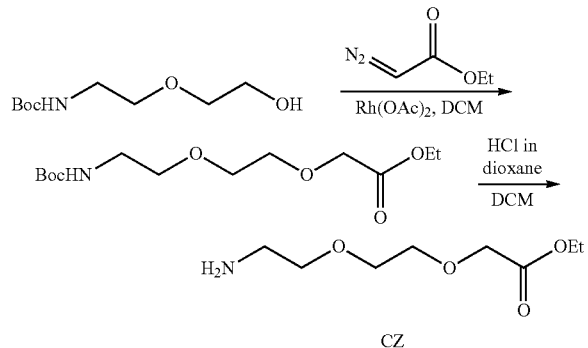

Step 1—Ethyl 2-[2-[2-(tert-butoxycarbonylamino)ethoxy]ethoxy]acetate

To a mixture of tert-butyl N-[2-(2-hydroxyethoxy)ethyl]carbamate (10.0 g, 48.7 mmol, CAS #139115-91-6) and Rh(OAc)₂ (215 mg, 974 umol) in DCM (150 mL) was added a solution of ethyl 2-diazoacetate (16.6 g, 146 mmol) in DCM (100 mL) dropwise. The reaction mixture was stirred at rt for 20 hours. On completion, the reaction mixture was diluted with water (50 mL) and extracted with DCM (2×100 mL). The combined organic layers were dried over Na₂SO₄, filtered and concentrated in vacuo to give a residue. The residue was purified by column chromatography to give the title compound (12.0 g, 84% yield) as a colorless oil. ¹H NMR (400 MHz, CDCl₃) δ 4.23-4.16 (m, 4H), 4.11 (s, 1H), 4.05-3.97 (m, 2H), 3.67-3.58 (m, 3H), 3.51-3.41 (m, 2H), 1.47-1.37 (m, 9H), 1.28-1.26 (m, 3H).

Step 2—Ethyl 2-[2-(2-aminoethoxy)ethoxy]acetate

To a mixture of ethyl 2-[2-[2-(tert-butoxycarbonylamino)ethoxy]ethoxy]acetate (3.00 g, 10.3 mmol) in DCM (20 mL) was added HCl in dioxane (4 M, 10 mL). The reaction mixture was stirred at rt for 2 hours. On completion, the reaction mixture was concentrated in vacuo to give the title compound (2.00 g, 100% yield) as a red brown oil. ¹H NMR (400 MHz, CDCl₃) δ 4.27-4.14 (m, 3H), 4.12 (s, 1H), 4.07-3.93 (m, 2H), 3.75-3.69 (m, 3H), 3.67 (s, 2H), 3.45-3.36 (m, 1H), 1.29 (t, J=7.6 Hz, 3H).

Tert-butyl 2-[2-[2-[2-(2-aminoethoxy)ethoxy]ethoxy]ethoxy]acetate (Intermediate DA)

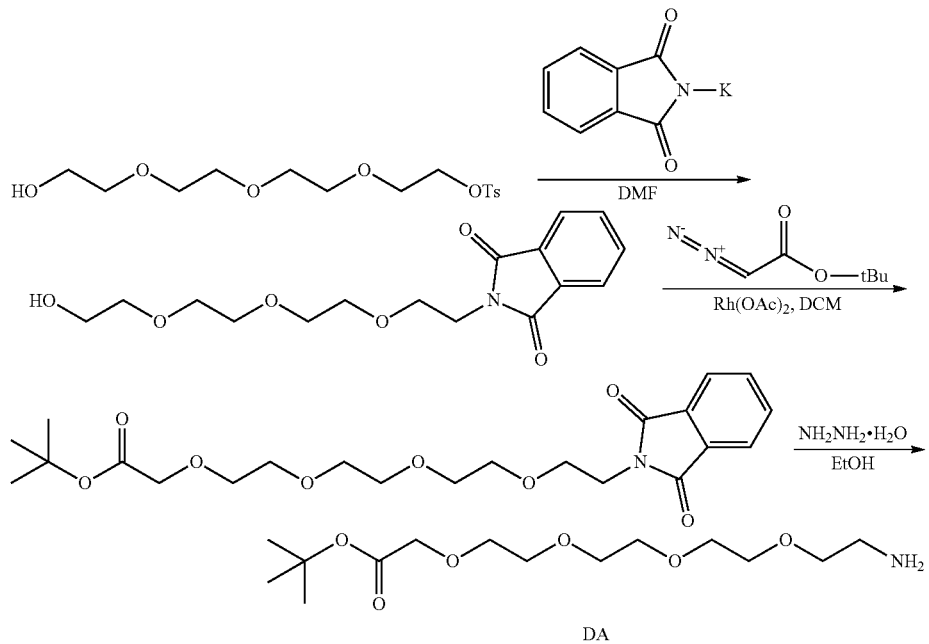

Step 1—2-[2-[2-[2-(2-Hydroxyethoxy)ethoxy]ethoxy]ethyl]isoindoline-1,3-dione

To a solution of 2-[2-[2-(2-hydroxyethoxy)ethoxy]ethyl 4-methylbenzenesulfonate (20.0 g, 57.4 mmol, synthesized via Step 1 of Intermediate AO) in DMF (200 mL) was added (1,3-dioxoisoindolin-2-yl)potassium (12.7 g, 68.8 mmol) and the mixture was stirred at 80° C. for 2 h. On completion, the mixture was concentrated in vacuo. The residue was then diluted with EA (200 mL) and stirred for 30 min, filtered, and the organic layer was concentrated in vacuo. The mixture was purified by silica gel chromatography (petroleum ether:ethyl acetate=1:2) to give the title compound (9.00 g, 48% yield) as a yellow solid. ¹H NMR (400 MHz, CDCl₃) δ 7.90-7.84 (m, 2H), 7.78-7.70 (m, 2H), 3.97-3.89 (m, 2H), 3.81-3.74 (m, 2H), 3.73-3.69 (m, 2H), 3.69-3.65 (m, 2H), 3.65-3.61 (m, 6H), 3.61-3.57 (m, 2H).

Step 2—Tert-butyl 2-[2-[2-[2-[2-(1,3-dioxoisoindolin-2-yl)ethoxy]ethoxy]ethoxy]ethoxy]acetate To a solution of 2-[2-[2-[2-(2-hydroxyethoxy)ethoxy]ethoxy]ethyl]isoindoline-1,3-dione (1.00 g, 3.09 mmol) and Rh(OAc)₂ (27.3 mg, 123 umol) in DCM (10.0 mL) was added a solution of tert-butyl 2-diazoacetate (1.32 g, 9.28 mmol) in DCM (20 mL) dropwise at rt for 1 hr. The reaction mixture was stirred at rt for 20 h. On completion, the mixture was extracted with H₂O (3×30 mL), the organic layer was dried over anhydrous Na₂SO₄, filtered and concentrated in vacuo. The mixture was purified by silica gel chromatography (petroleum ether:ethyl acetate=3:1) to give the title compound (1.00 g, 73% yield) as a yellow oil. ¹H NMR (400 MHz, CDCl3) δ 7.81-7.76 (m, 2H), 7.68-7.63 (m, 2H), 3.95 (s, 2H), 3.87-3.82 (m, 2H), 3.70-3.66 (m, 2H), 3.66-3.61 (m, 2H), 3.61-3.57 (m, 4H), 3.56-3.52 (m, 6H), 1.42 (s, 9H).

Step 3—Tert-butyl 2-[2-[2-[2-(2-aminoethoxy)ethoxy]ethoxy]ethoxy]acetate

To a solution of tert-butyl 2-[2-[2-[2-[2-(1,3-dioxoisoindolin-2-yl)ethoxy]ethoxy]ethoxy]ethoxy]acetate (1.00 g, 2.29 mmol) in EtOH (15.0 mL) was added NH₂NH₂.H₂O (233 mg, 4.57 mmol, 226 uL, 98% purity), and the mixture was stirred at 80° C. for 12 h. On completion, the mixture was concentrated in vacuo. The residue was diluted with DCM (30 mL), filtered and the organic layer was concentrated in vacuo to give the title compound (700 mg, 99% yield) as a yellow oil. ¹H NMR (400 MHz, CDCl3) δ 4.04 (s, 2H), 3.75-3.64 (m, 12H), 3.57-3.51 (m, 2H), 2.94-2.84 (m, 2H), 2.08-1.95 (m, 2H), 1.52-1.45 (m, 9H).

N-[1-(azetidin-3-yl)-3-carbamoyl-pyrazol-4-yl]-2-[2-(2,2,2-trifluoroethylamino)-4-pyridyl]oxazole-4-carboxamide (Intermediate DB)

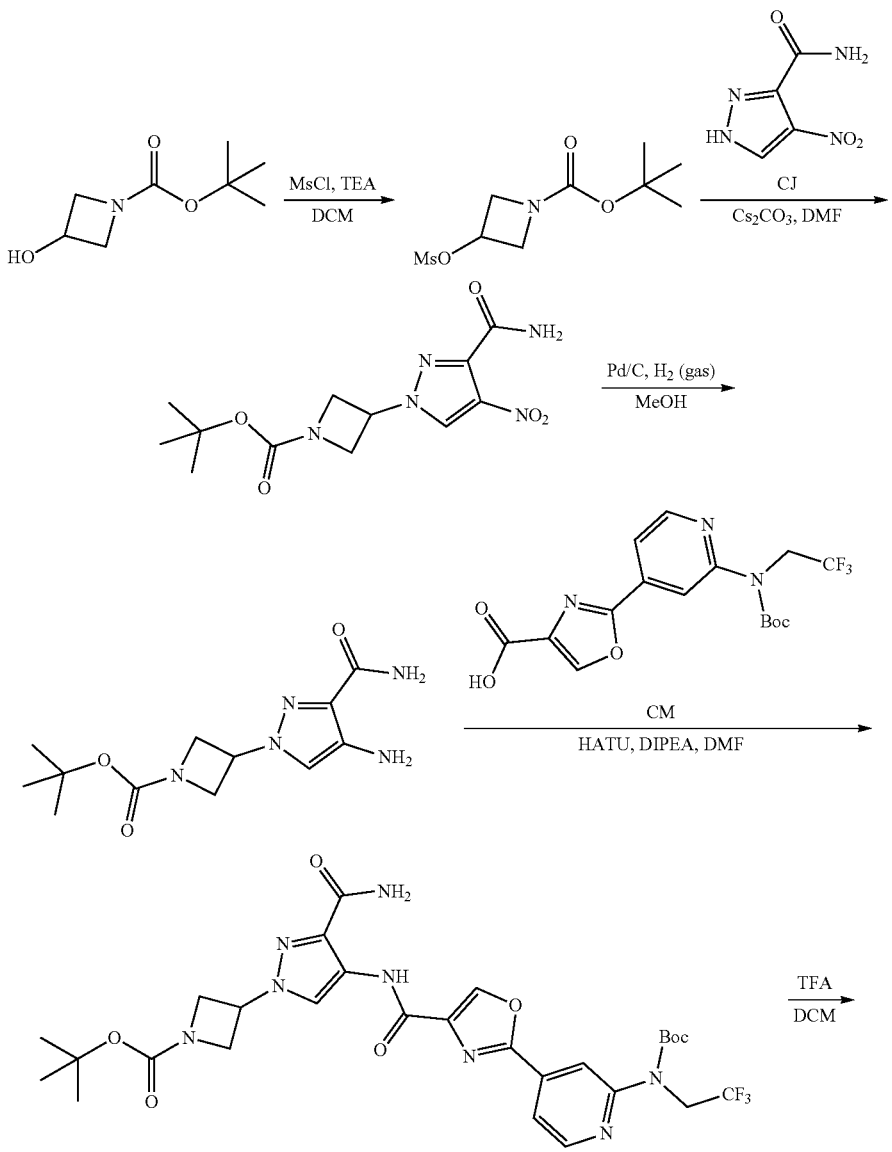

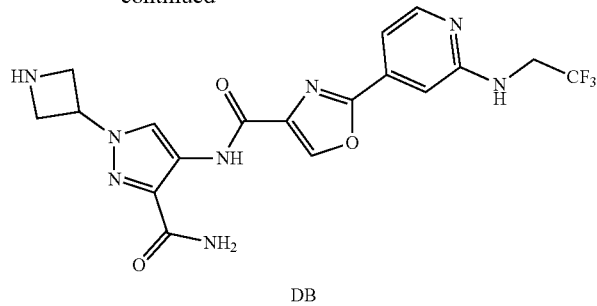

DB

Step 1—Tert-butyl 3-methylsulfonyloxyazetidine-1-carboxylate

To a solution of tert-butyl 3-hydroxyazetidine-1-carboxylate (10.0 g, 57.7 mmol) and TEA (17.5 g, 24.1 mL, 173 mmol) in DCM (80.0 mL) was added MsCl (9.92 g, 86.6 mmol) at 0° C. The mixture was then allowed to warm to rt and stirred for 30 min. On completion, the mixture was washed with $H_2O$ (3×50 mL). The organic layer was washed with brine (3×30 mL), dried over anhydrous $Na_2SO_4$, filtered and concentrated in vacuo to give the title compound (14.2 g, 97% yield) as a yellow oil. $^1$H NMR (400 MHz, $CDCl_3$) δ 5.25-5.17 (m, 1H), 4.33-4.25 (m, 2H), 4.15-4.09 (m, 2H), 3.08 (s, 3H), 1.46 (s, 9H).

Step 2—Tert-butyl 3-(3-carbamoyl-4-nitro-pyrazol-1-yl)azetidine-1-carboxylate To a solution of tert-butyl 3-methylsulfonyloxyazetidine-1-carboxylate (8.85 g, 35.2 mmol) and 4-nitro-1H-pyrazole-3-carboxamide (5.00 g, 32.0 mmol, Intermediate CJ) in DMF (110 mL) was added $Cs_2CO_3$ (20.8 g, 64.0 mmol), and the mixture was stirred at 130° C. for 16 h. On completion, the mixture was filtered and the filtrate was concentrated in vacuo. The mixture was purified by reverse phase chromatography (0.1% FA) to give the title compound (3.50 g, 35% yield) as a yellow solid. $^1$H NMR (400 MHz, $CDCl_3$) δ 9.04 (s, 1H), 8.06 (s, 1H), 7.83 (s, 1H), 5.36-5.22 (m, 1H), 4.38-4.27 (m, 2H), 4.22-4.08 (m, 2H), 1.41 (s, 9H).

Step 3—Tert-butyl 3-(4-amino-3-carbamoyl-pyrazol-1-yl)azetidine-1-carboxylate To a solution of tert-butyl 3-(3-carbamoyl-4-nitro-pyrazol-1-yl)azetidine-1-carboxylate (500 mg, 1.61 mmol) in MeOH (5.00 mL) was added Pd/C (50.0 mg, 10 wt %) under nitrogen. The suspension was degassed under vacuum and purged with hydrogen gas several times. The mixture was stirred under hydrogen atmosphere (15 psi pressure) at rt for 14 hours. On completion, the mixture was concentrated in vacuo to give the title compound (335 mg, 74% yield) as a purple oil. LC-MS (ESI$^+$) m/z 304.0 (M+Na)$^+$

Step 4—Tert-butyl 3-[4-[[2-[2-[tert-butoxycarbonyl(2,2,2-trifluoroethyl)amino]-4-pyridyl]oxazole-4-carbonyl]amino]-3-carbamoylpyrazol-1-yl]azetidine-1-carboxylate To a solution of tert-butyl 3-(4-amino-3-carbamoyl-pyrazol-1-yl)azetidine-1-carboxylate (145 mg, 516 umol), 2-[2-[tert-butoxycarbonyl(2,2,2-trifluoroethyl)amino]-4-pyridyl]oxazole-4-carboxylic acid (200 mg, 516 umol, Intermediate CM) in DMF (3.00 mL) was added HATU (235 mg, 619 umol) and DIPEA (333 mg, 2.58 mmol, 449 uL), and the mixture was stirred at rt for 30 min. On completion, the mixture was diluted with $H_2O$ (20 mL) and stirred for 20 min. The mixture was filtered and the solid was dried in vacuo to give the title compound (250 mg, 74% yield) as a white solid. $^1$H NMR (400 MHz, DMSO-$d_6$) δ 11.01 (s, 1H), 9.07 (s, 1H), 8.66 (d, J=5.2 Hz, 1H), 8.49 (s, 1H), 8.25 (s, 1H), 7.83 (s, 1H), 7.77 (d, J=5.2 Hz, 1H), 7.59 (s, 1H), 5.42-5.32 (m, 1H), 4.96-4.87 (m, 2H), 4.36-4.28 (m, 2H), 4.27-4.17 (m, 2H), 1.53 (s, 9H), 1.43 (s, 9H)

Step 5—N-[1-(azetidin-3-yl)-3-carbamoyl-pyrazol-4-yl]-2-[2-(2,2,2-trifluoroethylamino)-4-pyridyl]oxazole-4-carboxamide To a solution of tert-butyl 3-[4-[[2-[2-[tert-butoxycarbonyl(2,2,2-trifluoroethyl)amino]-4-pyridyl]oxazole-4-carbonyl]amino]-3-carbamoyl-pyrazol-1-yl]azetidine-1-carboxylate (220 mg, 338 umol) in DCM (5.00 mL) was added TFA (7.70 g, 67.5 mmol), and the mixture was stirred at rt for 30 min. On completion, the mixture was concentrated in vacuo to give the title compound (190 mg, 99% yield, TFA salt) as a white solid. LC-MS (ESI$^+$) m/z 451.2 (M+H)$^+$.

2-[2-[2-(2-Aminoethoxy)ethoxy]ethoxy]ethanol (Intermediate DC)

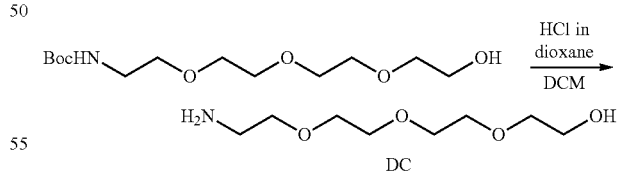

DC

To a solution of tert-butyl N-[2-[2-[2-(2-hydroxyethoxy)ethoxy]ethoxy]ethyl]carbamate (2.00 g, 6.82 mmol, synthesized via Steps 1-3 of Intermediate AO) in DCM (30 mL) was added HCl in dioxane (4 M, 10.2 mL), and the mixture was stirred rt for 1 hour. On completion, the reaction mixture was concentrated in vacuo to give the title compound (1.30 g, 82% yield, HCl salt) as a brown oil. $^1$H NMR (400 MHz, DMSO-$d_6$) δ 8.03 (s, 2H), 3.57-3.50 (m, 13H), 3.43-3.41 (m, 2H), 2.97-2.90 (m, 2H).

1241

3-[4-[[2-[2-[tert-butoxycarbonyl(2,2,2-trifluoroethyl)amino]-4-pyridyl]oxazole-4-carbonyl]amino]-3-carbamoyl-pyrazol-1-yl]benzoic acid (Intermediate DD)

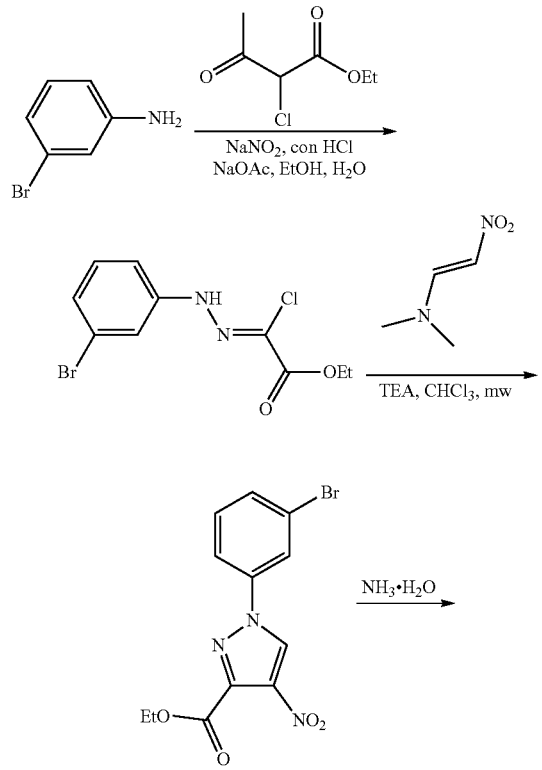

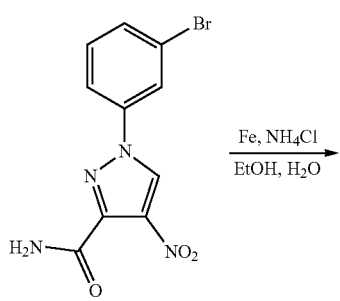

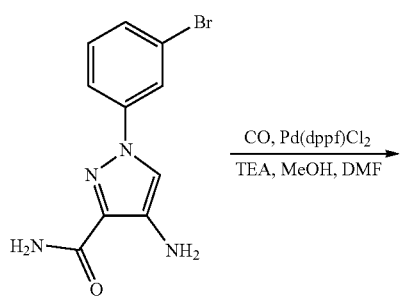

1242

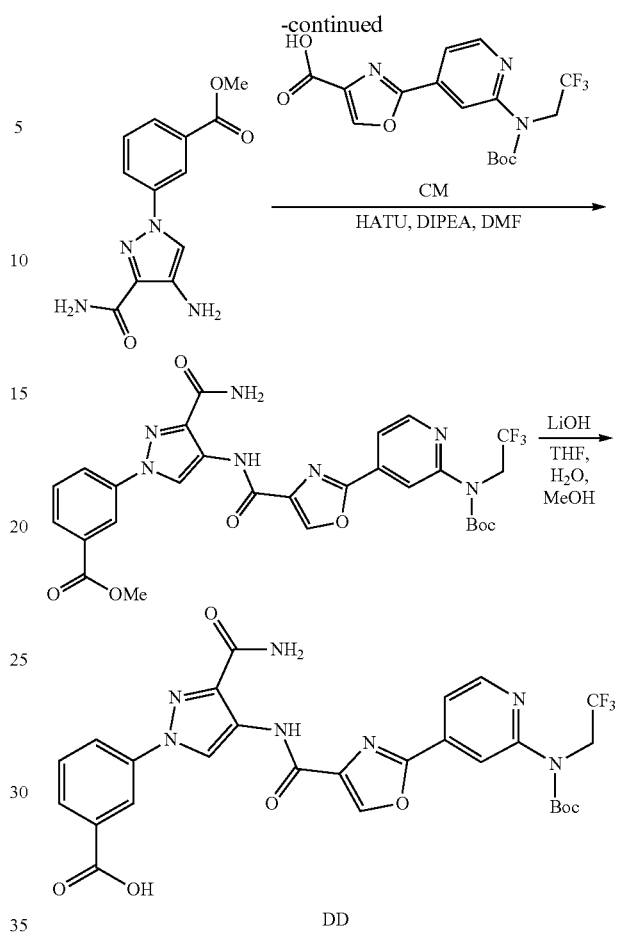

Step 1—Ethyl (2Z)-2-[(3-bromophenyl)hydrazono]-2-chloro-acetate

To a mixture of 3-bromoaniline (30.0 g, 174 mmol) in a mixed solvent of HCl (12 M, 43.6 mL) and H₂O (30.0 mL) was added a solution of NaNO₂ (13.2 g, 191 mmol) in H₂O (10 mL) at −5° C. dropwise. Then the mixture was stirred at 0° C. for 0.5 hr. Ethyl 2-chloro-3-oxo-butanoate (30.1 g, 183 mmol) and NaOAc (42.9 g, 523 mmol) were added to the solution and the mixture was stirred for 30 min. The reaction mixture was then allowed to warm to rt and stirred for an additional for 2 h. On completion, the mixture was filtered and the filter cake was dried in vacuo to give the title compound (46.6 g, 87% yield) as a yellow solid. ¹H NMR (400 MHz, DMSO-d₆) δ 10.68 (s, 1H), 7.53 (t, J=2.0 Hz, 1H), 7.38-7.33 (m, 1H), 7.29 (t, J=8.0 Hz, 1H), 7.19-7.14 (m, 1H), 4.30 (q, J=7.2 Hz, 2H), 1.30 (t, J=7.2 Hz, 3H).

Step 2—Ethyl 1-(3-bromophenyl)-4-nitro-pyrazole-3-carboxylate

Ethyl (2Z)-2-[(3-bromophenyl)hydrazono]-2-chloro-acetate (2.50 g, 8.18 mmol), (E)-N,N-dimethyl-2-nitro-ethenamine (950 mg, 8.18 mmol) and TEA (827 mg, 8.18 mmol) were taken up into a microwave tube in CHCl₃ (20 mL). The sealed tube was heated at 140° C. for 30 min under microwave. On completion, the mixture was concentrated in vacuo. The mixture was purified by silica column chromatography (PE:EA=10:1) to give the title compound (0.42 g, 15% yield) as a yellow solid. 1H NMR (400 MHz, CDCl$_3$) δ 8.63 (s, 1H), 7.98 (t, J=2.0 Hz, 1H), 7.71-7.66 (m, 1H), 7.64-7.61 (m, 1H), 7.46-7.40 (m, 1H), 4.54 (q, J=7.2 Hz, 2H), 1.46 (t, J=7.2 Hz, 3H).

Step 3—1-(3-bromophenyl)-4-nitro-pyrazole-3-carboxamide

To a solution of ethyl 1-(3-bromophenyl)-4-nitro-pyrazole-3-carboxylate (3.00 g, 8.82 mmol) in THF (20.0 mL) was added NH$_3$.H$_2$O (13.4 g, 115 mmol, 14.7 mL, 30 wt %), and the mixture was stirred at 110° C. for 16 h. On completion, the mixture was concentrated in vacuo to give the title compound (2.70 g, 90% yield) as a yellow solid. LC-MS (ESI$^+$) m/z 312.9 (M+H)$^+$.

Step 4—4-amino-1-(3-bromophenyl)pyrazole-3-carboxamide

To a solution of 1-(3-bromophenyl)-4-nitro-pyrazole-3-carboxamide (2.70 g, 8.68 mmol) in MeOH (50.0 mL) and H$_2$O (25.0 mL) was added Fe (4.85 g, 86.7 mmol) and NH$_4$Cl (4.64 g, 86.7 mmol). The mixture was stirred at 80° C. for 3 h. On completion, the mixture was filtered and the filtrated was concentrated in vacuo to remove MeOH. The residue was extracted with EA (2×200 ml). The combined organic layer was then washed with water (200 ml) and concentrated in vacuo to give the title compound (1.90 g, 77% yield) as a yellow solid. LC-MS (ESI$^+$) m/z 281.0 and 283.0 (M+H)$^+$.

Step 5—Methyl 3-(4-amino-3-carbamoyl-pyrazol-1-yl)benzoate

To a solution of 4-amino-1-(3-bromophenyl)pyrazole-3-carboxamide (1.90 g, 6.76 mmol) in DMF (20 mL) and MeOH (20 mL) was added TEA (683 mg, 6.76 mmol) and Pd(dppf)Cl$_2$ (494 mg, 675 umol). The mixture was stirred at 80° C. for 16 h under CO atmosphere (50 psi pressure). On completion, the mixture was concentrated in vacuo. The mixture was purified by silica gel column chromatography (PE:EA=1:1) to give the title compound (1.10 g, 62% yield) as a yellow solid. $^1$H NMR (400 MHz, DMSO-d$_6$) δ 8.38 (t, J=2.0 Hz, 1H), 8.12-8.06 (m, 1H), 7.89 (s, 1H), 7.88-7.84 (m, 1H), 7.67-7.58 (m, 2H), 7.28 (s, 1H), 4.91 (s, 2H), 3.90 (s, 3H).

Step 6—Methyl 3-[4-[[2-[2-[tert-butoxycarbonyl(2,2,2-trifluoroethyl)amino]-4-pyridyl]oxazole-4-carbonyl]amino]-3-carbamoyl-pyrazol-1-yl]benzoate To a solution of methyl 3-(4-amino-3-carbamoyl-pyrazol-1-yl)benzoate (300 mg, 1.15 mmol), 2-[2-[tertbutoxycarbonyl(2,2,2-trifluoroethyl)amino]-4-pyridyl]oxazole-4-carboxylic acid (446 mg, 1.15 mmol, Intermediate CM) in DMF (5.00 mL) was added HATU (525 mg, 1.38 mmol) and DIPEA (446 mg, 3.46 mmol), and the mixture was stirred at 25° C. for 30 min. On completion, the mixture was diluted with H$_2$O (40 mL) and stirred for 30 min. The mixture was then filtered and the solid was dried in vacuo to give the title compound (660 mg, 90% yield) as off-white solid. $^1$H NMR (400 MHz, DMSO-d$_6$) δ 11.10 (s, 1H), 9.11 (s, 1H), 9.04 (s, 1H), 8.67 (d, J=5.2 Hz, 1H), 8.50 (s, 1H), 8.31-8.25 (m, 2H), 8.18 (s, 1H), 7.97 (d, J=7.6 Hz, 1H), 7.81-7.75 (m, 2H), 7.75-7.69 (m, 1H), 4.95-4.87 (m, 2H), 3.93 (s, 3H), 1.54 (s, 9H).

Step 7—3-[4-[[2-[2-[tert-butoxycarbonyl(2,2,2-trifluoroethyl)amino]-4-pyridyl]oxazole-4-carbonyl]amino]-3-carbamoyl-pyrazol-1-yl]benzoic acid To methyl 3-[4-[[2-[2-[tert-butoxycarbonyl(2,2,2-trifluoroethyl)amino]-4-pyridyl]oxazole-4-carbonyl]amino]-3-carbamoyl-pyrazol-1-yl]benzoate (660 mg, 1.05 mmol) in a solution of THF (10.0 mL), H$_2$O (1.00 mL) and MeOH (1.00 mL) was added LiOH (125 mg, 5.24 mmol), and the mixture was stirred at rt for 7 h. On completion, the mixture was diluted with H$_2$O (50 mL) and then acidified with 1N HCl solution until the pH=5. The mixture was then extracted with EA (3×40 mL). The combined organic layers were dried over anhydrous Na$_2$SO$_4$, filtered and concentrated in vacuo to give the title compound (620 mg, 96% yield) as an off-white solid. $^1$H NMR (400 MHz, DMSO-d$_6$) δ 13.33 (s, 1H), 11.10 (s, 1H), 9.11 (s, 1H), 9.02 (s, 1H), 8.66 (d, J 5.2 Hz, 1H), 8.49 (s, 1H), 8.27-8.21 (m, 2H), 8.17 (s, 1H), 7.95 (d, J=7.6 Hz, 1H), 7.80-7.74 (m, 2H), 7.71-7.65 (m, 1H), 4.95-4.85 (m, 2H), 1.53 (s, 9H).

4-(4-(2-(2-((Tert-butoxycarbonyl)(2,2,2-trifluoroethyl)amino)pyridin-4-yl)oxazole-4-carboxamido)-3-(trifluoromethyl)-1H-pyrazol-1-yl)benzoic acid (Intermediate DE)

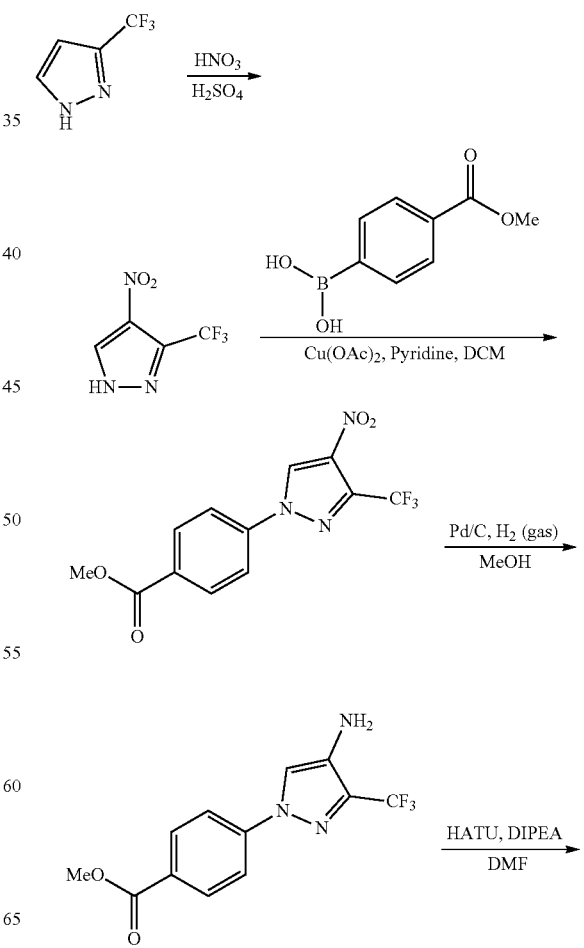

-continued

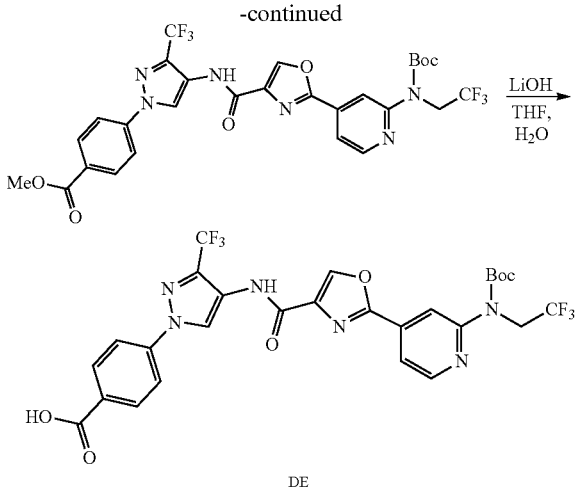

DE

Step 1—4-Nitro-3-(trifluoromethyl)-1H-pyrazole

To a solution of 3-(trifluoromethyl)-1H-pyrazole (5.0 g, 36.7 mmol) in concentrated sulfuric acid (75 mL) was carefully added dropwise at 0° C. 65% HNO₃ (8.91 g, 91.86 mmol, 6.36 mL). After stirring for 10 min the reaction mixture was heated to 115° C., and stirring was continued at 115° C. for 4 h. On completion, the reaction mixture was cooled to rt. Then, the reaction mixture was poured onto the 200 mL ice, and extracted with ethyl acetate (3×150 mL). The combined organic layers were washed with brine (2×100 mL), dried over with anhydrous sodium sulfate, filtered and concentrated in vacuo. The residue was purified by silica gel chromatography (PE:EA=10:1) to give the title compound (5.9 g, 89% yield) as a white solid. ¹H NMR (400 MHz, DMSO-d₆) δ 14.72 (s, 1H), 9.15 (s, 1H).

Step 2—Methyl 4-(4-nitro-3-(trifluoromethyl)-1H-pyrazol-1-yl)benzoate

A mixture of 4-nitro-3-(trifluoromethyl)-1H-pyrazole (5.70 g, 31.5 mmol), (4-methoxycarbonylphenyl) boronic acid (7.00 g, 38.9 mmol), pyridine (9.96 g, 125.9 mmol) and Cu(OAc)₂ (8.58 g, 47.2 mmol) in DCM (150 mL) was stirred at rt for 5 h. On completion, the reaction mixture was concentrated in vacuo. The residue was purified by silica gel chromatography (PE:EA=10:1) to give the title compound (4.5 g, 45% yield) as a white solid. ¹H NMR (400 MHz, CDCl₃) δ 8.74 (d, J=0.6 Hz, 1H), 8.22-8.12 (m, 2H), 7.82-7.74 (m, 2H), 3.90 (s, 3H).

Step 3—Methyl 4-(4-amino-3-(trifluoromethyl)-1H-pyrazol-1-yl)benzoate

To a solution of methyl 4-[4-nitro-3-(trifluoromethyl)pyrazol-1-yl]benzoate (500 mg, 1.59 mmol) in a mixed solvent of DCM (20 mL) and MeOH (20 mL) was added Pd/C (100 mg, 10 wt %) under nitrogen. The suspension was degassed under vacuum and purged with hydrogen gas several times. The mixture was stirred under hydrogen atmosphere (15 psi pressure) at rt for 14 hours. On completion, the reaction mixture was filtered and the filtrate was concentrated in vacuo to give the title compound (450 mg, 97% yield) as a white solid. LC-MS (ESI⁺) m/z 286.0 (M+H)⁺

Step 4—Methyl 4-(4-(2-(2-(((tert-butoxycarbonyl)(2,2,2-trifluoroethyl)amino)pyridin-4-yl)oxazole-4-carboxamido)-3-(trifluoromethyl)-1H-pyrazol-1-yl)benzoate To a solution of methyl 4-[4-amino-3-(trifluoromethyl)pyrazol-1-yl]benzoate (150 mg, 526 umol) and 2-[2-[tert-butoxycarbonyl(2,2,2-trifluoroethyl)amino]-4-pyridyl]oxazole-4-carboxylic acid (204 mg, 526 umol, Intermediate CM) in DMF (5 mL) was added HATU (240 mg, 631 umol) and DIPEA (136 mg, 1.05 mmol, 183 uL). The mixture was stirred at rt for 1 hr. On completion, the reaction mixture was quenched with water 50 mL. A white precipitate formed which was filtered. The filter cake was dried over in vacuo to give the title compound (300 mg, 88% yield) as a white solid. ¹H NMR (400 MHz, CDCl₃) δ 9.07 (s, 1H), 8.98 (s, 1H), 8.55 (d, J=4.8 Hz, 1H), 8.45 (s, 1H), 8.37 (s, 1H), 8.19 (d, J=8.0 Hz, 2H), 7.87 (d, J=8.0 Hz, 2H), 7.73 (d, J=4.0 Hz, 1H), 4.98-4.81 (m, 2H), 3.97 (s, 3H).

Step 5—4-(4-(2-(2-((Tert-butoxycarbonyl)(2,2,2-trifluoroethyl)amino)pyridin-4-yl)oxazole-4-carboxamido)-3-(trifluoromethyl)-1H-pyrazol-1-yl)benzoic acid To a solution of methyl 4-[4-[[2-[2-[tert-butoxycarbonyl(2,2,2-trifluoroethyl)amino]-4-pyridyl]oxazole-4-carbonyl]amino]-3-(trifluoromethyl)pyrazol-1-yl]benzoate (300 mg, 458 umol) in THF (6 mL) and H₂O (2 mL) was added LiOH.H₂O (38.5 mg, 917 umol). The mixture was stirred at rt for 12 h. On completion, the reaction mixture was concentrated in vacuo to remove THF. The residue was acidified with 1N HCl until the pH=4, then filtered. The filter cake was collected to give the title compound (460 mg, 99% yield) as a white solid. LC-MS (ESI⁺) m/z 641.0 (M+H)⁺.

4-[4-[[2-[2-Tert-butoxycarbonyl(cyclopropylmethyl)amino]-4-pyridyl oxazole-4-carbonyl]amino]-3-carbamoyl-pyrazol-1-yl]benzoic acid (Intermediate DF)

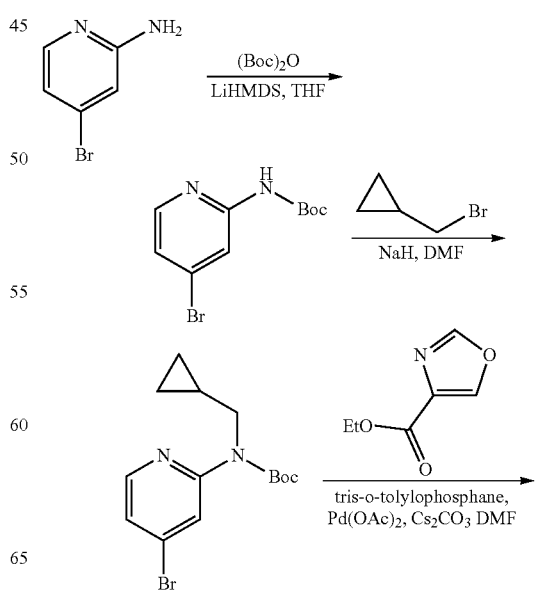

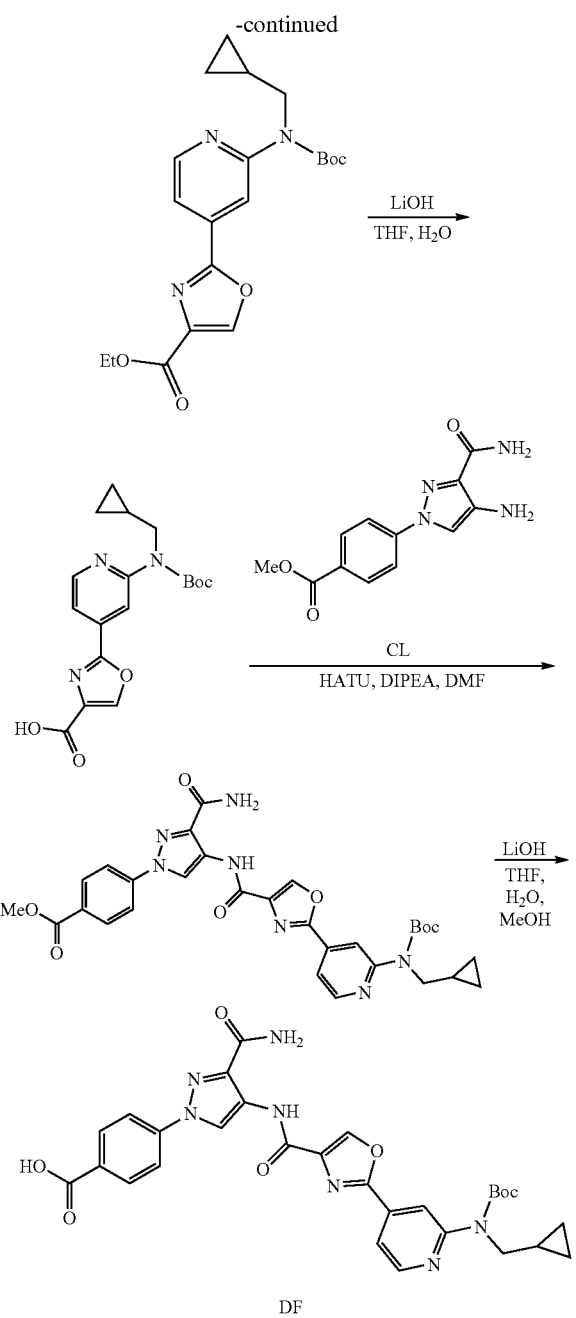

Step 1—Tert-butyl N-(4-bromo-2-pyridyl)-N-(cyclopropylmethyl)carbamate

To a solution of tert-butyl N-(4-bromo-2-pyridyl)carbamate (5.0 g, 18.3 mmol, synthesized via Step 1 of Intermediate CM) in DMF (50 mL) was added NaH (1.10 g, 27.5 mmol) at 0° C. for 30 minutes. Then bromomethylcyclopropane (2.97 g, 22.0 mmol) was added into the mixture. The reaction mixture was stirred at rt for 17 h. On completion, the mixture was quenched with water (40 mL) and extracted with EA (2×50 mL). The organic phase was washed with brine (60 mL), dried over $Na_2SO_4$, and concentrated in vacuo. The residue was purified by silica gel chromatography to give the title compound (2.7 g, 45% yield) as a white solid. $^1$H NMR (400 MHz, CDCl$_3$) δ 8.18 (d, J=5.2 Hz, 1H), 7.98 (d, J=1.6 Hz, 1H), 7.17 (dd, J=1.6, 5.2 Hz, 1H), 3.88 (d, J=7.2 Hz, 2H), 1.55 (s, 9H), 1.22-1.15 (m, 1H), 0.47-0.40 (m, 2H), 0.28-0.23 (m, 2H).

Step 2—Ethyl 2-[2-[tert-butoxycarbonyl(cyclopropylmethyl)amino]-4-pyridyl]oxazole-4-carboxylate To a solution of ethyl oxazole-4-carboxylate (1.16 g, 8.25 mmol) and tert-butyl N-(4-bromo-2-pyridyl)-N-(cyclopropylmethyl)carbamate (2.7 g, 8.25 mmol) in DMF (30 mL) was added tris-o-tolylphosphane (502 mg, 1.65 mmol), Pd(OAc)$_2$ (185 mg, 825 umol) and Cs$_2$CO$_3$ (5.38 g, 16.5 mmol). The reaction mixture was stirred at 80° C. under nitrogen for 17 h. On completion, the mixture was diluted with water (50 mL) and extracted with EA (3×50 mL). The organic layer was washed with water (100 ml), dried over Na$_2$SO$_4$, and concentrated in vacuo. The residue was purified by silica gel chromatography to give the title compound (1.8 g, 56% yield) as a white oil. $^1$H NMR (400 MHz, CDCl$_3$) δ 8.50 (dd, J=1.6, 5.2 Hz, 1H), 8.38 (s, 1H), 8.35 (s, 1H), 7.71 (dd, J=1.6, 5.2 Hz, 1H), 4.46 (q, J=7.2 Hz, 2H), 3.93 (d, J=7.2 Hz, 2H), 1.57 (s, 9H), 1.44 (t, J=7.2 Hz, 3H), 1.24-1.16 (m, 1H), 0.46-0.40 (m, 2H), 0.28-0.24 (m, 2H).

Step 3—2-[2-Tert-butoxycarbonyl(cyclopropylmethyl)amino]-4-pyridyl]oxazole-4-carboxylic acid To a solution of ethyl 2-[2-[tert-butoxycarbonyl(cyclopropylmethyl)amino]-4-pyridyl]oxazole-4-carboxylate (0.5 g, 1.29 mmol) in a mixed solvent of THF (5 mL) and H$_2$O (1 mL) was added LiOH (92.7 mg, 3.87 mmol). The reaction mixture was stirred at rt for 2 h. On completion, the mixture was acidified with 1N HCl solution until the pH=3-5, then extracted with EA (2×30 mL). The combined organic phase was dried over Na$_2$SO$_4$, filtered and concentrated in vacuo to give the title compound (460 mg, 99% yield) as a white solid. LC-MS (ESI$^+$) m/z 304.0 (M-56)$^+$.

Step 4—Methyl 4-[4-[[2-[2-[tert-butoxycarbonyl(cyclopropylmethyl)amino]-4-pyridyl]oxazole-4-carbonyl]amino]-3-carbamoyl-pyrazol-1-yl]benzoate To a solution of 2-[2-[tert-butoxycarbonyl(cyclopropylmethyl)amino]-4-pyridyl]oxazole-4-carboxylic acid (360 mg, 1.00 mmol) and methyl 4-(4-amino-3-carbamoyl-pyrazol-1-yl)benzoate (443 mg, 1.70 mmol, Intermediate CL) in DMF (5 mL) was added DIPEA (647 mg, 5.01 mmol) and HATU (457 mg, 1.20 mmol). The reaction mixture was stirred at rt for 0.5 hr. On completion, the mixture was diluted with water (40 mL) and extracted with EA (2×30 mL). The combined organic layer was washed with brine (40 mL) and concentrated in vacuo. The residue was purified by silica gel chromatography to give the title compound (190 mg, 32% yield) as a white solid. LC-MS (ESI$^+$) m/z 602.3 (M+H)$^+$.

Step 5—4-[4-[[2-[2-[Tert-butoxycarbonyl(cyclopropylmethyl)amino]-4-pyridyl]oxazole-4-carbonyl]amino]-3-carbamoyl-pyrazol-1-yl]benzoic acid To a solution of methyl 4-[4-[[2-[2-[tert-butoxycarbonyl(cyclopropylmethyl)amino]-4-pyridyl]oxazole-4-carbonyl]amino]-3-carbamoyl-pyrazol-1-yl]benzoate (190 mg, 316 umol) in a mixed solvent of THF (3 mL), MeOH (2 mL) and H$_2$O (1 mL) was added LiOH (37.8 mg, 1.58 mmol). The reaction mixture was stirred at rt for 17 h. On completion, the mixture was acidified with 1N HCl solution until the pH=5-7, concentrated in vacuo to give the title compound (180 mg, 97% yield) as a yellow solid. LC-MS (ESI⁺) m/z 588.3 (M+H)⁺.

4-[(1,3-Dioxoisoindolin-2-yl)methyl]benzenesulfonyl chloride (Intermediate DG)

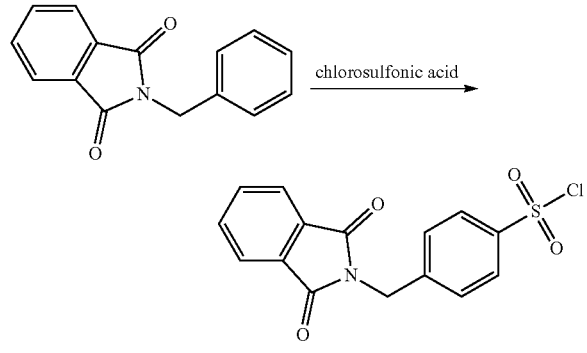

A mixture of 2-benzylisoindoline-1,3-dione (5.00 g, 21.0 mmol) and sulfurochloridic acid (17.1 g, 147 mmol, 9.82 mL) was stirred at 60° C. for 1.5 h until the evolution of hydrochloric gas ceased. On completion, the mixture was poured in a mixture of water and ice (100 mL), and a fine white precipitate was formed. The precipitate was filtered and washed with cold water. The precipitate was purified by column chromatography (dichloromethane:petroleum ether=1:1) to give the title compound (5.20 g, 73% yield) as a white solid. ¹H NMR (400 MHz, DMSO-d₆) δ 7.91-7.85 (m, 4H), 7.57-7.55 (m, 2H), 7.30-7.25 (m, 2H), 4.77 (s, 2H).

4-(Aminomethyl)-N-(3-cyano-4-methyl-1H-indol-7-yl)benzenesulfonamide (Intermediate DH)

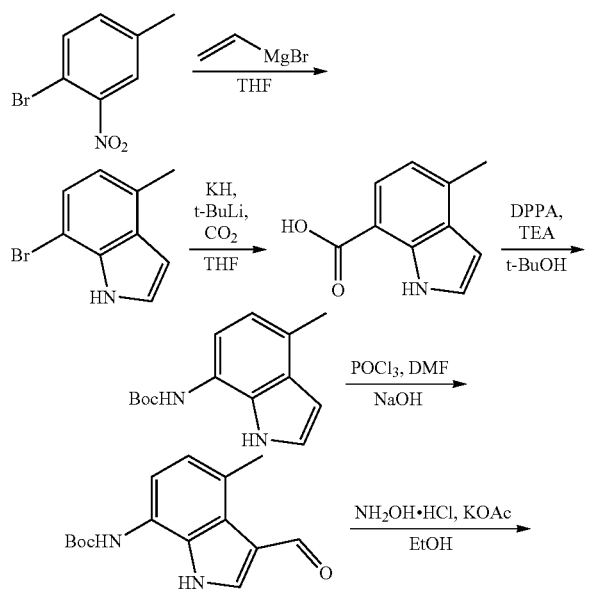

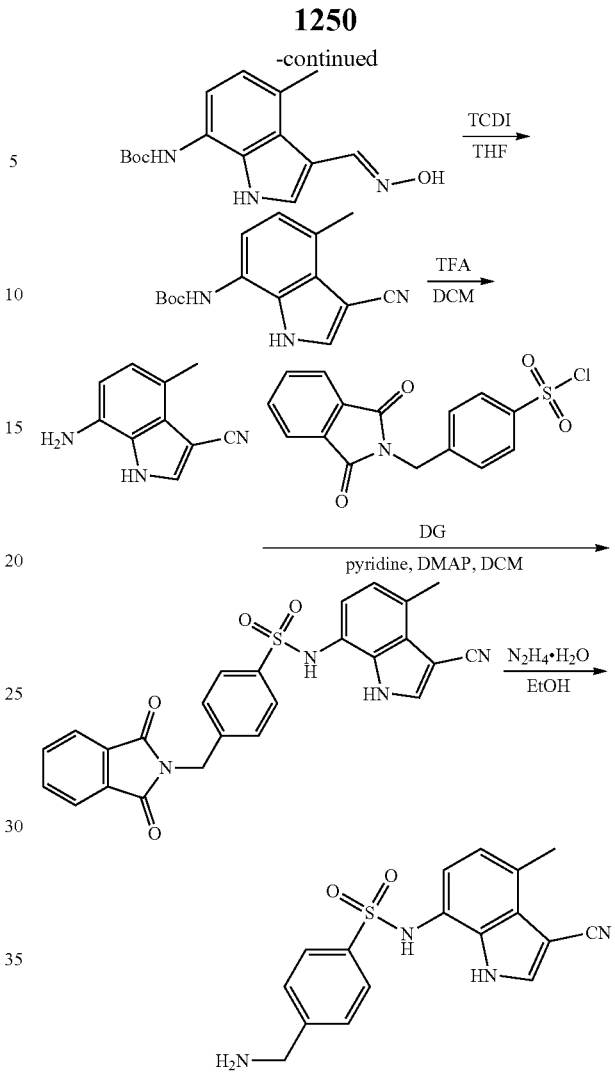

Step 1—7-Bromo-4-methyl-1H-indole

To a solution of 1-bromo-4-methyl-2-nitro-benzene (40.0 g, 185 mmol, 25.3 mL) in tetrahydrofuran (400 mL) was added bromo(vinyl)magnesium (1 M, 611 mL) at −60° C. under nitrogen gas atmosphere. The reaction mixture was then stirred at −30° C. for 1 hour. On completion, the reaction mixture was quenched with saturated ammonium chloride solution (150 mL), followed with water (100 mL). The mixture was concentrated in vacuo to remove the tetrahydrofuran. The residue was extracted with ethyl acetate (2×500 mL). The organic layer was dried over anhydrous sodium sulfate, filtered and concentrated in vacuo. The residue was then purified by column chromatography (petroleum ether:ethyl acetate=100:1) to give the title compound (18.0 g, 42% yield) as a yellow oil. ¹H NMR (400 MHz, DMSO-d₆) δ 11.27 (br s, 1H), 7.37 (t, J=2.8 Hz, 1H), 7.18 (d, J=7.6 Hz, 1H), 6.75 (dd, J=0.8, 7.6 Hz, 1H), 6.57 (dd, J=1.6, 3.2 Hz, 1H), 2.44 (s, 3H).

Step 2—4-Methyl-1H-indole-7-carboxylic acid

To a mixture of potassium hydride (4.47 g, 34.27 mmol, 30 wt %) suspended in anhydrous tetrahydrofuran (80 mL)

was added 7-bromo-4-methyl-1H-indole (6.00 g, 28.56 mmol) dissolved in tetrahydrofuran (30 mL) at 0° C. After 15 minutes, the mixture was cooled to −70° C. and t-BuLi (1.3 M, 54.9 mL) was added dropwise, keeping the temperature below −65° C. After further 15 minutes, carbon dioxide gas (15 psi pressure) was bubbled into the reaction and the reaction was slowly warmed to rt over 30 minutes. On completion, the reaction mixture was quenched with ice water (120 mL), and washed with ethyl acetate (3×60 mL). The aqueous phase was collected and acidified with 1 N hydrochloride acid solution until the pH<7. Then, the mixture was extracted with ethyl acetate (3×60 mL). The organic phase was collected, dried over anhydrous sodium sulfate, filtered and concentrated in vacuo to give the crude product as a brown solid. The crude product was triturated with petroleum ether:dichloromethane (10:1, 100 mL) to give the product (3.50 g, 69% yield) as a white solid. $^1$H NMR (400 MHz, DMSO-$d_6$) δ 12.82 (br s, 1H), 11.02 (br s, 1H), 7.67 (d, J=7.6 Hz, 1H), 7.35 (t, J=2.8 Hz, 1H), 6.92 (d, J=7.6 Hz, 1H), 6.56 (dd, J=2.0, 3.2 Hz, 1H), 2.54 (s, 3H).

Step 3—Tert-butyl N-(4-methyl-1H-indol-7-yl)carbamate

To a solution of 4-methyl-1H-indole-7-carboxylic acid (2.20 g, 12.5 mmol) in t-BuOH (36 mL) was added triethylamine (3.81 g, 37.6 mmol, 5.24 mL) and DPPA (4.49 g, 16.3 mmol, 3.54 mL). The mixture was stirred at 80° C. for 3 h. On completion, the reaction mixture was poured into ice water (150 mL) and extracted with ethyl acetate (3×80 mL). The organic phase was collected, dried over anhydrous sodium sulfate, filtered and concentrated in vacuo to get a residue. The residue was purified by column chromatography (petroleum ether:ethyl acetate=10:1 to 5:1) to give the title compound (2.00 g, 64% yield) as a white solid. $^1$H NMR (400 MHz, CDCl$_3$) δ 9.80 (br s, 1H), 7.14 (t, J=2.8 Hz, 1H), 6.70 (d, J=7.6 Hz, 1H), 6.60 (br s, 1H), 6.52 (br s, 1H), 6.45 (dd, J=2.0, 2.8 Hz, 1H), 2.44 (s, 3H), 1.48 (s, 9H).

Step 4—Tert-butyl N-(3-formyl-4-methyl-1H-indol-7-yl)carbamate

Phosphorus oxychloride (2.61 g, 17.0 mmol, 1.58 mL) was added to anhydrous N,N-dimethyl-formamide (20 mL) at 0° C. under nitrogen atmosphere and the reaction mixture was stirred for 30 minutes. Tert-butyl N-(4-methyl-1H-indol-7-yl)carbamate (2.80 g, 11.3 mmol) dissolved in N,N-dimethylformamide (8 mL) was then added dropwise and the reaction mixture was allowed to warm to rt and then stirred for 1.5 hrs. Next, to the reaction mixture was added 30% sodium hydroxide (100 mL) and the mixture was heated to reflux for 30 minutes. On completion, the mixture was extracted with ethyl acetate (3×150 mL). The organic phase was collected, dried over anhydrous sodium sulfate, filtered and concentrated in vacuo to give a residue. The residue was purified by column chromatography (Petroleum ether:Ethyl acetate=3:1 to 0:1) to give the title compound (2.70 g, 86% yield) as a white solid. $^1$H NMR (400 MHz, DMSO-$d_6$) δ 11.93 (br s, 1H), 9.99 (s, 1H), 9.04 (br s, 1H), 8.27 (s, 1H), 7.43 (br d, J=6.0 Hz, 1H), 6.96 (d, J=8.0 Hz, 1H), 2.76 (s, 3H), 1.55 (s, 9H).

Step 5—Tert-butyl N-[3-(hydroxyiminomethyl)-4-methyl-1H-indol-7-yl]carbamate

To a solution of tert-butyl N-(3-formyl-4-methyl-1H-indol-7-yl)carbamate (2.70 g, 9.84 mmol) in ethanol (80 mL) was added NH$_2$OH.HCl (1.03 g, 14.7 mmol) and anhydrous potassium acetate (2.90 g, 29.5 mmol). The mixture was stirred at 80° C. for 30 minutes. On completion, the reaction mixture was concentrated in vacuo to get a residue. The residue was diluted with water (60 mL) and extracted with ethyl acetate (3×60 mL). The organic phase was collected, dried over anhydrous magnesium sulfate, filtered and concentrated in vacuo to give the title compound (2.80 g, 98% yield) as a white solid. LC-MS (ESI$^+$) m/z 290.2 (M+H)$^+$.

Step 6—Tert-butyl N-(3-cyano-4-methyl-1H-indol-7-yl)carbamate

To a solution of tert-butyl N-[3-(hydroxyiminomethyl)-4-methyl-1H-indol-7-yl]carbamate (2.60 g, 8.99 mmol) in anhydrous tetrahydrofuran (70 mL) was added di(imidazol-1-yl)methanthione (3.20 g, 17.9 mmol) and the mixture was stirred at rt for 2 h. The reaction mixture was then concentrated in vacuo to get a residue. The residue was diluted with ice water (60 mL) and extracted with ethyl acetate (3×40 mL). The combined organic phase was collected, dried over anhydrous magnesium sulfate, filtered and concentrated in vacuo to get a residue. The residue was purified by column chromatography (Petroleum ether:Ethyl acetate=5:1 to 2:1) to give the title compound (2.40 g, 98% yield) as a gray solid. $^1$H NMR (400 MHz, CDCl$_3$) δ 10.98 (br s, 1H), 7.74 (d, J=3.2 Hz, 1H), 6.89 (d, J=7.6 Hz, 1H), 6.81 (br s, 1H), 6.66 (br d, J=6.8 Hz, 1H), 2.75 (s, 3H), 1.57 (s, 9H).

Step 7—7-Amino-4-methyl-1H-indole-3-carbonitrile

To a solution of tert-butyl N-(3-cyano-4-methyl-1H-indol-7-yl)carbamate (2.30 g, 8.48 mmol) in anhydrous dichloromethane (23 mL) was added trifluoroacetic acid (17.7 g, 155 mmol, 11.50 mL). The mixture was stirred at rt for 30 minutes. On completion, the reaction mixture was concentrated in vacuo to give a residue. The residue was diluted with saturated sodium bicarbonate solution (50 mL) and extracted with ethyl acetate (3×30 mL). The combined organic phase was collected, dried over anhydrous sodium sulfate, filtered and concentrated in vacuo to give the crude product. The crude product was triturated with petroleum ether:dichloromethane (30:1, 50 mL) to give the title compound (1.40 g, 96% yield) as a white solid. $^1$H NMR (400 MHz, DMSO-$d_6$) δ 11.73 (br s, 1H), 8.12 (d, J=3.2 Hz, 1H), 6.67 (d, J=7.6 Hz, 1H), 6.37 (d, J=7.6 Hz, 1H), 5.09 (br s, 2H), 2.50 (br s, 3H).

Step 8—N-(3-cyano-4-methyl-1H-indol-7-yl)-4-[(1,3-dioxoisoindolin-2-yl)methyl]benzenesulfonamide To a solution of 4-[(1,3-dioxoisoindolin-2-yl)methyl]benzenesulfonyl chloride (1.51 g, 4.50 mmol, Intermediate DG) in dichloromethane (30 mL) was added pyridine (646 mg, 8.18 mmol, 660 uL) and DMAP (49.9 mg, 408 umol) and 7-amino-4-methyl-1H-indole-3-carbonitrile (700 mg, 4.09 mmol). The mixture was stirred at rt for 3 h. On completion, the reaction mixture was concentrated in vacuo to get a residue. The residue was triturated with (dichloromethane:methanol=10:1, 50 mL) to give the title compound (1.00 g, 51% yield) as a white solid. $^1$H NMR (400 MHz, DMSO-$d_6$) δ 11.92 (d, J=2.4 Hz, 1H), 9.97 (s, 1H), 8.15 (d, J=3.2 Hz, 1H), 7.93-7.84 (m, 4H), 7.67 (d, J=8.4 Hz, 2H), 7.46 (d, J=8.4 Hz, 2H), 6.76 (d, J=8.4 Hz, 1H), 6.59 (d, J=8.0 Hz, 1H), 4.83 (s, 2H), 2.55 (s, 3H).

Step 9—4-(Aminomethyl)-N-(3-cyano-4-methyl-1H-indol-7-yl)benzenesulfonamide

To a solution of N-(3-cyano-4-methyl-1H-indol-7-yl)-4-[(1,3-dioxoisoindolin-2-yl)methyl]-benzene sulfonamide (1.00 g, 2.13 mmol) in ethanol (30 mL) was added hydrazine hydrate (2.13 g, 2.07 mL). The mixture was stirred at 80° C. for 2 h. On completion, the reaction mixture was concentrated in vacuo to give the title compound (1.05 g, 92% yield) as a white solid. LC-MS (ESI$^+$) m/z 341.1 (M+H)$^+$.

2-[2-[2-[2-[2-[2-(Tert-butoxycarbonylamino)ethoxy]ethoxy]ethoxy]ethoxy]acetic acid (Intermediate DI)

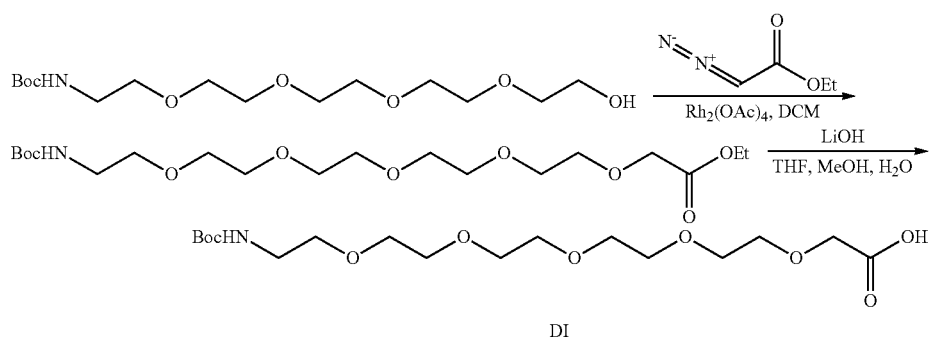

DI

Step 1—Ethyl 2-[2-[2-[2-[2-[2-(tert-butoxycarbonylamino)ethoxy]ethoxy]ethoxy]ethoxy]ethoxy]acetate To a mixture of tert-butyl N-[2-[2-[2-[2-(2-hydroxyethoxy)ethoxy]ethoxy]ethoxy]ethyl]carbamate (2.00 g, 5.93 mmol, synthesized via Step 1 of Intermediate AK) and Rh$_2$(OAc)$_4$ (52.4 mg, 119 umol) in dichloromethane (10 mL) was added a solution of ethyl 2-diazoacetate (1.01 g, 8.89 mmol, 931 uL) dissolved in dichloromethane (10 mL) dropwise at rt. Then the reaction mixture was stirred at rt for 17 h. On completion, the reaction mixture was quenched by adding water (15 mL) and was then extracted with dichloromethane (2×10 mL). The combined organic layers were dried over anhydrous sodium sulfate, filtered and concentrated in vacuo to give a residue. The residue was purified by silica gel column chromatography (Petroleum ether:Ethyl acetate=5:1 to 1:1) to give the title compound (370 mg, 15% yield) as a colorless oil. $^1$H NMR (400 MHz, CDCl$_3$) δ 5.12 (s, 1H), 4.23 (q, J=7.2 Hz, 2H), 4.16 (s, 2H), 3.76-3.64 (m, 16H), 3.56 (t, J=5.2 Hz, 2H), 3.33 (d, J=4.8 Hz, 2H), 1.46 (s, 9H), 1.30 (t, J=7.2 Hz, 3H).

Step 2—2-[2-[2-[2-[2-[2-(Tert-butoxycarbonylamino)ethoxy]ethoxy]ethoxy]ethoxy]ethoxy]acetic acid To a mixed solution of ethyl 2-[2-[2-[2-[2-[2-(tert-butoxycarbonylamino)ethoxy]ethoxy]ethoxy]-ethoxy]ethoxy]acetate (370 mg, 877 umol) in tetrahydrofuran (4 mL), methanol (1 mL) and H$_2$O (1 mL) was added lithium hydroxide (41.8 mg, 1.75 mmol). The reaction mixture was stirred at rt for 0.5 hr. On completion, the reaction mixture was adjusted pH<7 with 1 N hydrochloride acid solution, and then concentrated in vacuo to give the title compound (520 mg, 70% purity, 87% yield) as a light yellow oil. $^1$H NMR (400 MHz, CDCl$_3$) δ 5.33 (s, 1H), 4.67 (s, 1H), 3.88 (s, 2H), 3.61-3.55 (m, 16H), 3.47 (t, J=5.2 Hz, 2H), 3.23 (d, J=5.2 Hz, 2H), 1.37 (s, 9H).

4-(2-Aminoethylamino)-2-(2,6-dioxo-3-piperidyl)isoindoline-1,3-dione (Intermediate DJ)

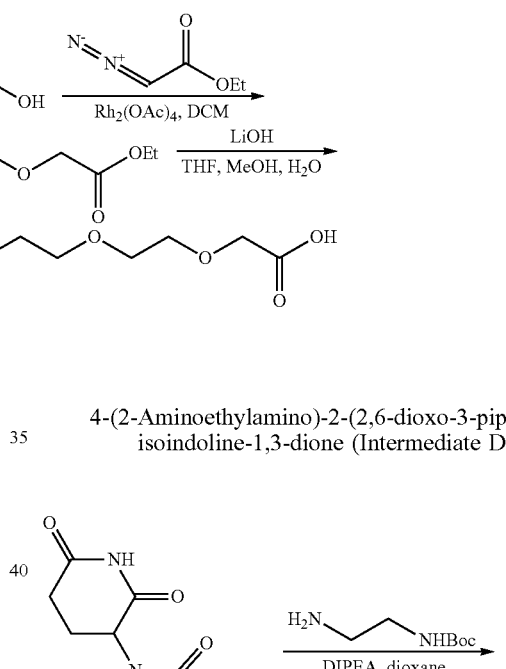

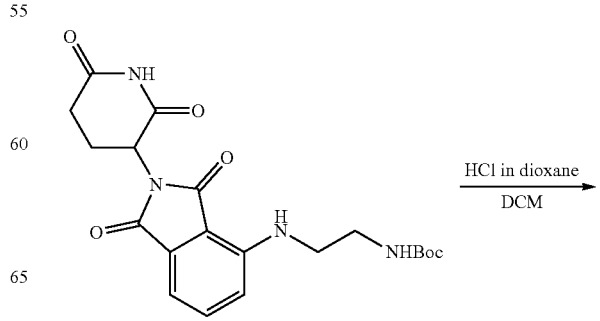

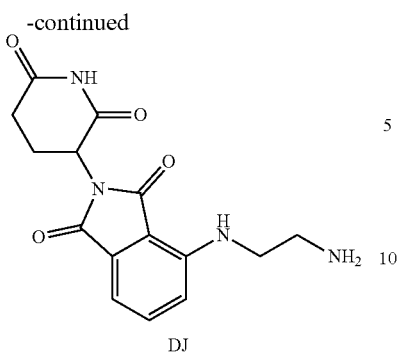

DJ

Step 1—Tert-butyl N-[2-[[2-(2,6-dioxo-3-piperidyl)-1,3-dioxo-isoindolin-4-yl]amino]ethyl]carbamate A mixture of 2-(2,6-dioxo-3-piperidyl)-4-fluoro-isoindoline-1,3-dione (2.07 g, 7.49 mmol, Intermediate R), tert-butyl N-(2-aminoethyl)carbamate (1.00 g, 6.24 mmol) and DIPEA (1.61 g, 12.5 mmol, 2.17 mL) in dioxane (10 mL) was stirred at 115° C. for 12 hours. On completion, the mixture was concentrated in vacuo. The residue was purified by column chromatography to give the title compound (0.90 g, 28% yield) as a yellow solid. $^1$H NMR (400 MHz, DMSO-$d_6$) δ 11.09 (s, 1H), 7.58 (t, J=7.6 Hz, 1H), 7.15 (d, J=8.8 Hz, 1H), 7.08-6.96 (m, 2H), 6.71 (t, J=5.6 Hz, 1H), 5.05 (dd, J=5.6, 12.8 Hz, 1H), 3.41-3.35 (m, 2H), 3.13 (m, 2H), 2.97-2.82 (m, 1H), 2.65-2.53 (m, 2H), 2.07-1.96 (m, 1H), 1.37 (s, 9H).

Step 2—4-(2-Aminoethyl amino)-2-(2,6-dioxo-3-piperidyl)isoindoline-1,3-dione To a solution of tert-butyl N-[2-[[2-(2,6-dioxo-3-piperidyl)-1,3-dioxo-isoindolin-4-yl]amino]ethyl]carbamate (0.30 g, 720 umol) in DCM (10 mL) was added HCl in dioxane (4 N, 3 mL). The reaction mixture was stirred at rt for 0.5 hr. On completion, the mixture was concentrated in vacuo to give the title compound (0.25 g, 98% yield) as a yellow solid. $^1$H NMR (400 MHz, DMSO-$d_6$) δ 11.12 (s, 1H), 7.63 (t, J=7.8 Hz, 1H), 7.20 (d, J=8.4 Hz, 1H), 7.10 (d, J=6.8 Hz, 1H), 6.84 (t, J=6.4 Hz, 1H), 5.05 (dd, J=5.6, 12.8 Hz, 1H), 3.62-3.57 (m, 2H), 3.01-2.89 (m, 2H), 2.90-2.89 (m, 1H), 2.62-2.55 (m, 2H), 2.05-2.03 (m, 1H).

2-Chloro-N-cyclopropyl-5-ethynyl-pyridin-4-amine (Intermediate DL)

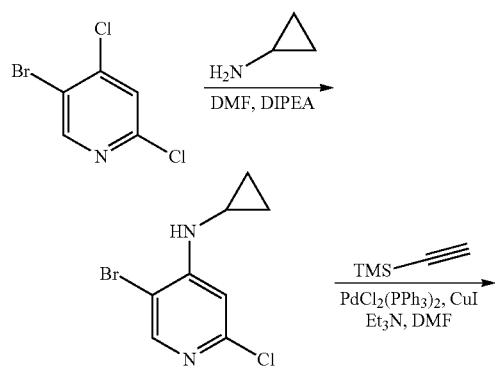

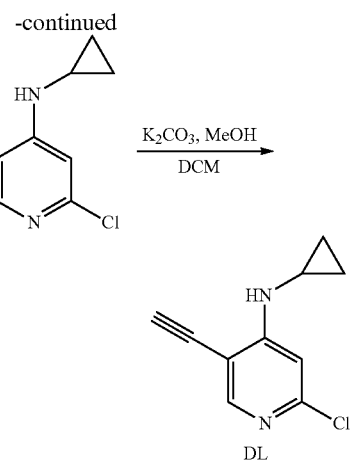

DL

Step 1—5-Bromo-2-chloro-N-cyclopropyl-pyridin-4-amine

To a solution of 5-bromo-2,4-dichloro-pyridine (5 g, 22.0 mmol) and cyclopropanamine (1.32 g, 23.1 mmol) in DMF (50 mL) was added DIPEA (8.54 g, 66.1 mmol). The reaction mixture was stirred at 100° C. for 17 h. On completion, the mixture was diluted with H$_2$O (40 mL) and extracted with EA (2×40 mL). The organic layer was washed with brine (50 mL), dried with anhydrous Na$_2$SO$_4$, filtered and concentrated in vacuo. The residue was purified by silica gel chromatography to give the title compound (2.10 g, 39% yield) as a white solid. $^1$H NMR (400 MHz, CDCl$_3$) δ 8.14 (s, 1H), 6.90 (s, 1H), 5.22 (s, 1H), 2.56-2.49 (m, 1H), 0.96-0.90 (m, 2H), 0.69-0.64 (m, 2H); LC-MS (ESI$^+$) m/z 248.9 and 246.9 (M+H)$^+$.

Step 2—2-Chloro-N-cyclopropyl-5-(2-trimethylsilylethynyl)pyridin-4-amine

5-Bromo-2-chloro-N-cyclopropyl-pyridin-4-amine (1.0 g, 4.0 mmol), CuI (46.2 mg, 242 umol) and Pd(PPh$_3$)$_2$Cl$_2$ (170 mg, 242 umol) was taken up into a microwave tube. Then ethynyl(trimethyl)silane (794 mg, 8.08 mmol), TEA (7.36 g, 72.7 mmol) and DMF (5 mL) were added into the above tube. The mixture was degassed with nitrogen gas for 5 minutes. The sealed tube was then heated to 120° C. for 1 h under microwave. On completion, the reaction mixture was filtered and the filtrate was concentrated in vacuo to give the title compound (900 mg, 45% yield) as a brown solid. LC-MS (ESI$^+$) m/z 265.0 (M+H)$^+$.

Step 3—2-Chloro-N-cyclopropyl-5-ethynyl-pyridin-4-amine

To a solution of 2-chloro-N-cyclopropyl-5-(2-trimethylsilylethynyl)pyridin-4-amine (1.0 g, 3.8 mmol) in a mixed solvent of MeOH (10 mL) and DCM (10 mL) was added K$_2$CO$_3$ (2.09 g, 15.1 mmol). The reaction mixture was stirred at rt for 15 h. On completion, the mixture was filtered and concentrated in vacuo. The residue was purified by silica gel chromatography to give the title compound (268 mg, 35% yield) as a yellow solid. $^1$H NMR (300 MHz, CDCl$_3$) δ 8.13 (s, 1H), 6.88 (s, 1H), 5.42 (s, 1H), 3.50 (s, 1H), 2.57-2.46 (m, 1H), 0.96-0.84 (m, 2H), 0.70-0.58 (m, 2H); LC-MS (ESI$^+$) m/z 193.0 (M+H)$^+$.

2-[2-[2-[2-(Tert-butoxycarbonylamino)ethoxy]ethoxy]ethoxy]acetic acid (Intermediate DM)

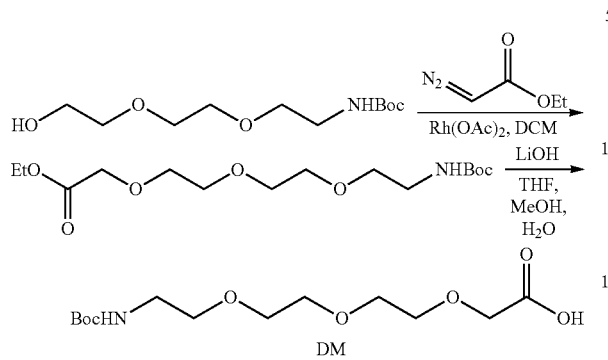

Step 1—Ethyl 2-[2-[2-[2-(tert-butoxycarbonylamino)ethoxy]ethoxy]ethoxy]

To a mixture of tert-butyl N-[2-[2-(2-hydroxyethoxy)ethoxy]ethyl]carbamate (3.00 g, 12.0 mmol, CAS #139115-92-7) and Rh(OAc)$_2$ (106 mg, 481 umol) in DCM (70 mL) was added a solution of ethyl 2-diazoacetate (4.12 g, 36.1 mmol) in DCM (40 mL) dropwise. The reaction mixture was stirred at rt for 16 h. On completion, the reaction mixture was diluted with water (100 mL) and extracted with DCM (3×100 mL). The combined organic layer was dried over anhydrous sodium sulfate, filtered and concentrated in vacuo. The residue was purified by column chromatography to give the title compound (600 mg, 14% yield) as a colorless oil. $^1$H NMR (400 MHz, CDCl$_3$) δ 5.15-5.13 (m, 1H), 4.23 (q, J=7.2 Hz, 2H), 4.16 (s, 2H), 3.77-3.69 (m, 41-), 3.68-361 (m, 4H), 3.55 (t, J=5.2 Hz, 2H), 3.32 (d, J=4.8 Hz, 2-1), 1.45 (s, 9-1), 1.29 (t, J=7.2 Hz, 3H).

Step 2—2-[2-[2-[2-(Tert-butoxycarbonylamino)ethoxy]ethoxy]ethoxy]acetic acid To a solution of ethyl 2-[2-[2-[2-(tert-butoxycarbonylamino)ethoxy]ethoxy]ethoxy]acetate (300 mg, 894 umol) in a mixed solvent of MeOH (5 mL) and H$_2$O (5 mL) was added LiOH.H$_2$O (75.0 mg, 1.79 mmol). The reaction mixture was stirred at rt for 1 hour. On completion, the reaction mixture was concentrated in vacuo. The residue was acidified with 1N HCl solution until the pH=7. The mixture was lyophilized to give the title compound (300 mg, 100% yield) as a white solid.

2-(2,6-Dioxo-3-piperidyl)-4-(prop-2-ynylamino)isoindoline-1,3-dione (Intermediate DN)

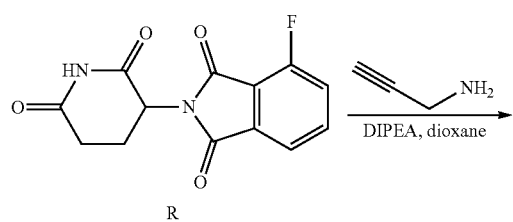

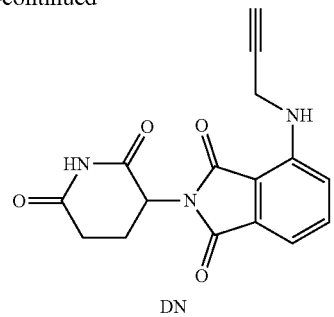

To a solution of prop-2-yn-1-amine (332 mg, 6.03 mmol, 386 uL) and DIPEA (3.90 g, 30.1 mmol, 5.25 mL) in dioxane (20.0 mL) was added 2-(2,6-dioxo-3-piperidyl)-4-fluoro-isoindoline-1,3-dione (2.00 g, 7.24 mmol, Intermediate R), and the mixture was stirred at 115° C. for 16 h. On completion, the mixture was concentrated in vacuo. The mixture was purified by reverse phase chromatography (0.1% FA) to give the title compound (550 mg, 29% yield) as a yellow solid. $^1$H NMR (400 MHz, CDCl3) δ 8.00 (s, 1H), 7.65-7.57 (m, 1H), 7.23 (d, J=7.2 Hz, 1H), 7.06 (d, J=8.4 Hz, 1H), 6.50-6.48 (m, 1H), 4.99-4.91 (m, 1H), 4.14-4.10 (m, 2H), 2.91-2.77 (m, 2H), 2.31-2.28 (m, 1H), 2.20-2.11 (m, 1H), 2.07 (s, 1H).

4-(But-3-ynylamino)-2-(2,6-dioxo-3-piperidyl)isoindoline-1,3-dione (Intermediate DO)

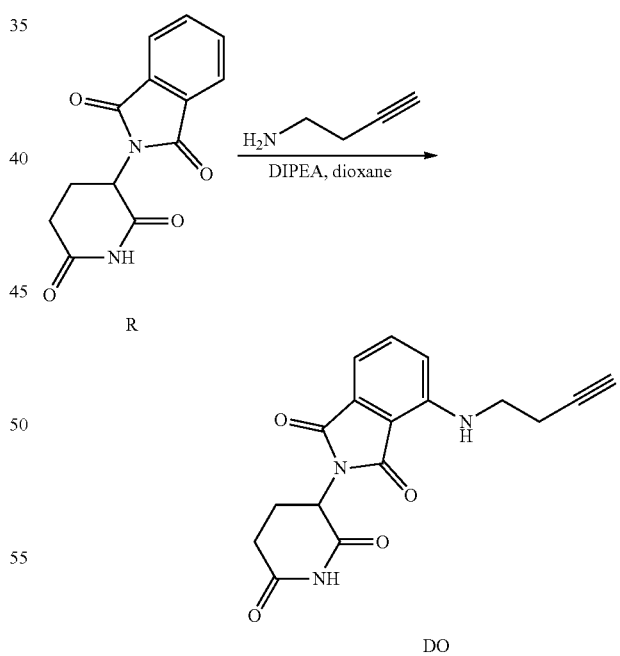

To a mixture of 2-(2,6-dioxo-3-piperidyl)-4-fluoro-isoindoline-1,3-dione (2.04 g, 7.39 mmol, Intermediate R) and but-3-yn-1-amine (650 mg, 6.16 mmol, hydrochloride) in dioxane (20 mL) was added DIPEA (7.96 g, 61.5 mmol). The reaction mixture was stirred at 115° C. for 16 hours. On completion, the reaction mixture was concentrated in vacuo. The residue was purified by prep-HPLC (0.1% FA) to give 4-(3-Azidopropylamino)-2-(2,6-dioxo-3-piperidyl)isoindoline-1,3-dione (Intermediate DP)

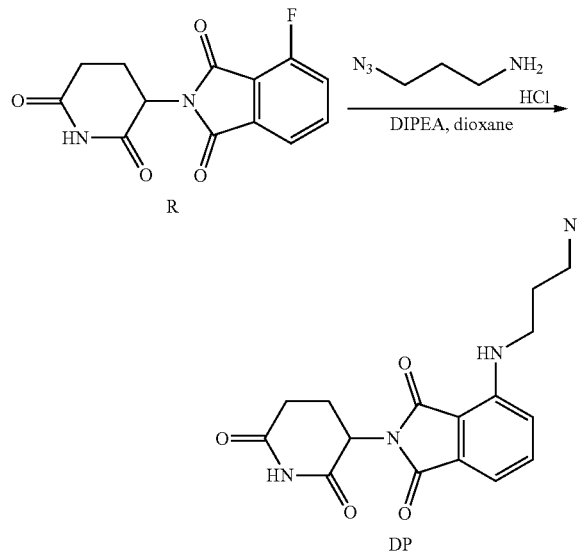

To a solution of 3-azidopropan-1-amine (198 mg, 1.45 mmol, HCl, CAS #88192-19-2) and 2-(2,6-dioxo-3-piperidyl)-4-fluoro-isoindoline-1,3-dione (0.40 g, 1.45 mmol, Intermediate R) in DMF (10 mL) was added DIPEA (936 mg, 7.24 mmol, 1.26 mL). The reaction mixture was stirred at 115° C. for 12 hours. On completion, the reaction mixture was concentrated in vacuo to give a residue. The residue was purified by reverse phase chromatography (NH$_3$.H$_2$O) to give the title compound (200 mg, 38.4% yield) as a yellow solid. LC-MS (ESI$^+$) m/z 357.0 (M+H)$^+$.

Tert-butyl 4-(4-hydroxycyclohexyl)piperazine-1-carboxylate (Intermediate DQ)

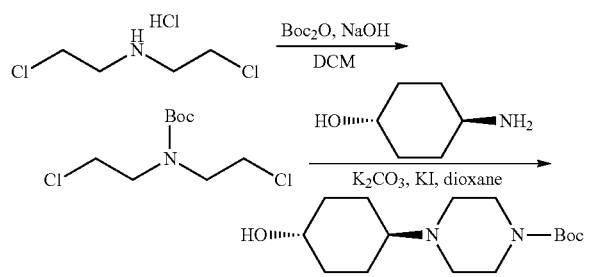

Step 1—Tert-butyl N,N-bis(2-chloroethyl)carbamate

To a mixture of 2-chloro-N-(2-chloroethyl)ethanamine (20.0 g, 112 mmol, HCl salt) in a mixed solution of DCM (150 mL) and NaOH (13.5 g, 3 M, 110 mL) was added a solution of (Boc)$_2$O (24.5 g, 112 mmol) in DCM (80 mL) dropwise. The reaction mixture was stirred at rt for 18 h. On completion, the mixture was separated and the organic layer was washed with brine (300 mL), dried over anhydrous Na$_2$SO$_4$, filtered and concentrated in vacuo. The residue was purified by silica gel chromatography to give the title compound (24.5 g, 90% yield) as a colorless oil. $^1$H NMR (400 MHz, CDCl$_3$) δ 3.71-3.58 (m, 8H), 1.49 (s, 9H).

Step 2—Tert-butyl 4-(4-hydroxycyclohexyl)piperazine-1-carboxylate

To a solution of tert-butyl N,N-bis(2-chloroethyl)carbamate (10.0 g, 41.3 mmol) and 4-aminocyclohexanol (5.04 g, 43.8 mmol) in dioxane (200 mL) was added K$_2$CO$_3$ (17.1 g, 124 mmol) and KI (20.6 g, 124 mmol). The reaction mixture was stirred at 115° C. for 17 h. On completion, the reaction mixture was filtered and the filtrate was concentrated in vacuo. The residue was purified by silica gel chromatography to give the title compound (3.50 g, 30% yield) as a red solid. $^1$H NMR (400 MHz, MeOH-d$_4$) δ 3.54-3.47 (m, 1H), 3.47-3.39 (m, 4H), 2.60-2.51 (m, 4H), 2.37-2.27 (m, 1H), 2.03-1.97 (m, 2H), 1.96-1.90 (m, 2H), 1.47 (s, 9H), 1.38-1.27 (m, 4H).

(2S)-2-Hydroxy-3-[(8R)-1-(4-piperazin-1-ylcyclohexoxy)-7,8-dihydro-6H-cyclopenta[4,5]thieno[1,2-c]pyrimidin-8-yl]propenamide (Intermediate DR)

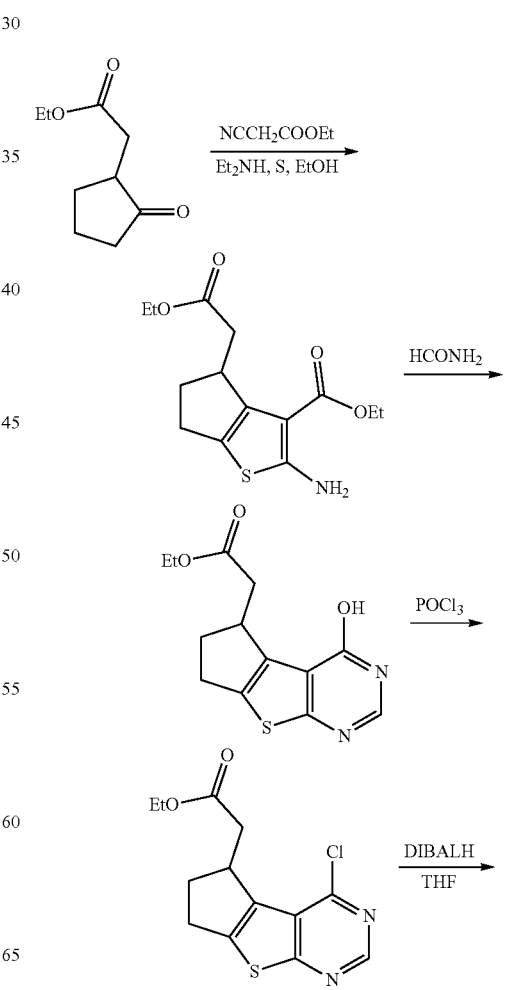

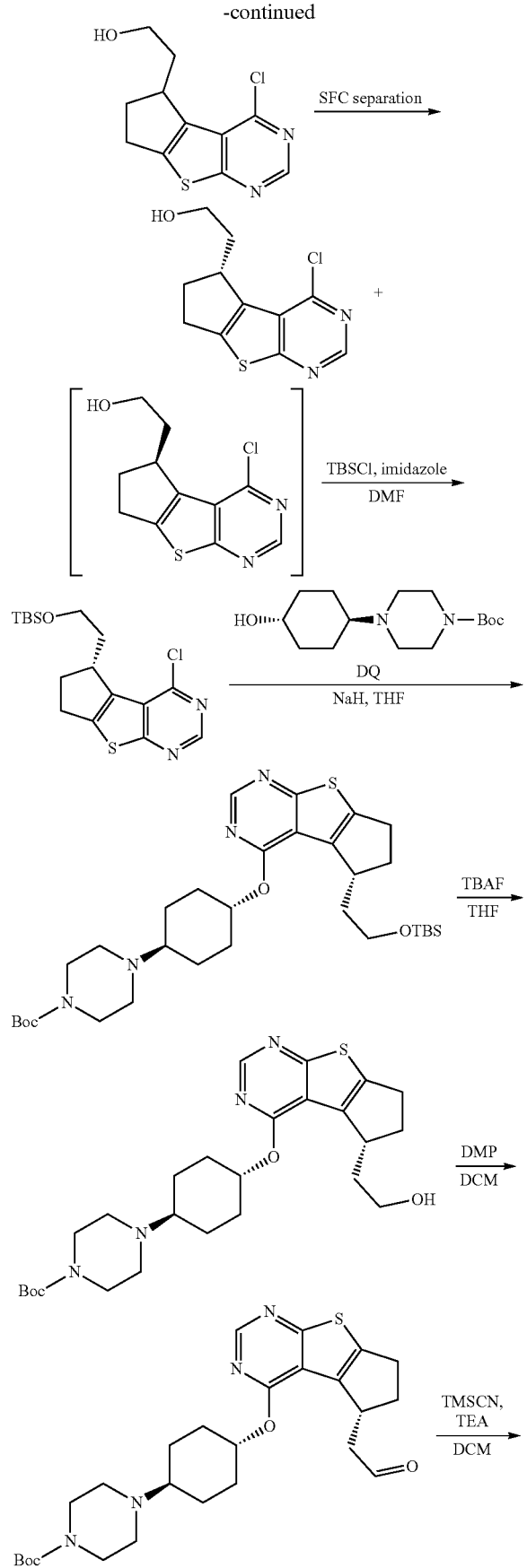
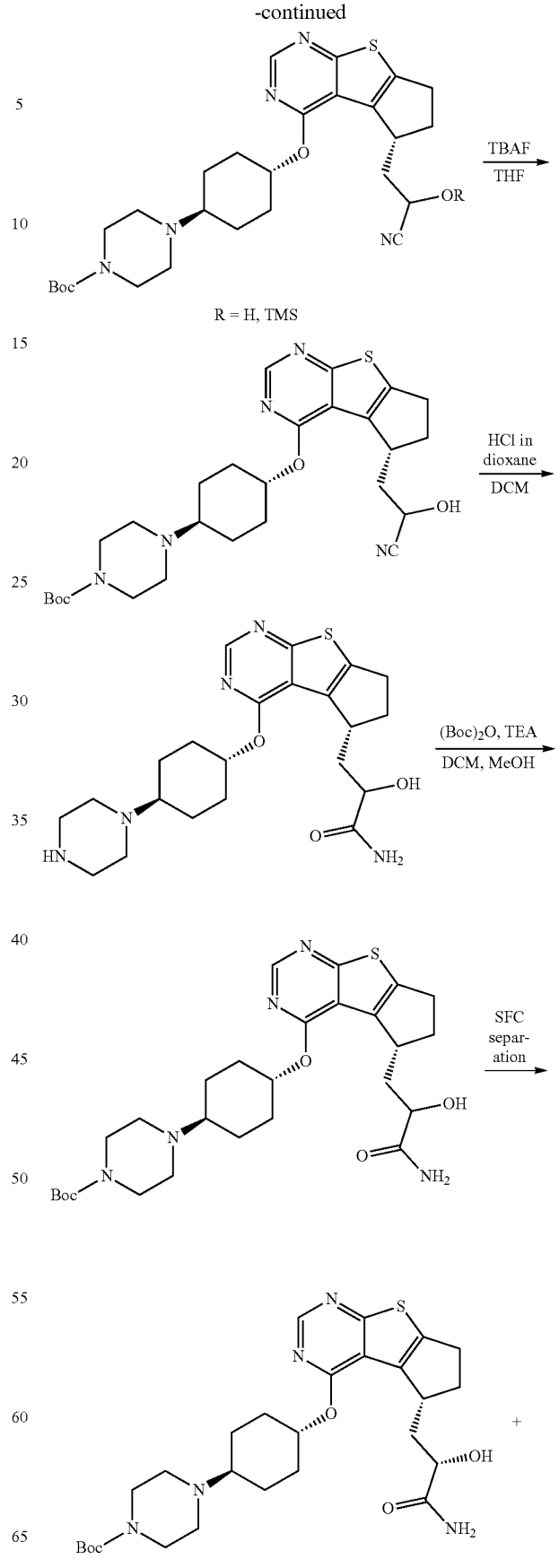

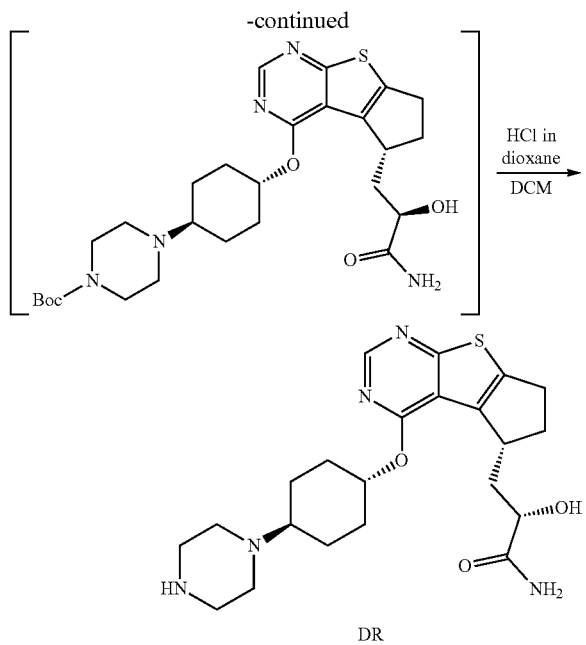

DR

Step 1-Ethyl 2-amino-4-(2-ethoxy-2-oxo-ethyl)-5,6-dihydro-4H-cyclopenta[b]thiophene-3-carboxylate To a solution of ethyl 2-(2-oxocyclopentyl)acetate (30.0 g, 169 mmol) in EtOH (300 mL) was added ethyl 2-cyanoacetate (17.2 g, 152 mmol), Et$_2$NH (15.2 g, 208 mmol) and sulphur (6.62 g, 206 mmol) at rt and the mixture was stirred for 90 h. On completion, the reaction mixture was concentrated in vacuo to give a residue. The residue was diluted with EA (300 mL) and washed with brine (3×40 mL). The organic layer was dried over Na$_2$SO$_4$, filtered and concentrated in vacuo to give a residue. The residue was purified by column chromatography (SiO$_2$, PE:EA=10:1) to give the title compound (25.0 g, 47% yield) as a yellow oil. $^1$H NMR (400 MHz, CDCl$_3$) δ 5.95 (s, 2H), 4.27 (q, J=7.2 Hz, 2H), 4.15 (q, J=7.2 Hz, 2H), 3.64-3.55 (m, 1H), 2.87-2.11 (m, 6H), 1.35 (t, J=7.2 Hz, 3H), 1.25 (t, J=7.2 Hz, 3H); LC-MS (ESI$^+$) m/z 298.0 (M+H)$^+$.

Step 2—Ethyl 2-(1-hydroxy-7,8-dihydro-6H-cyclopenta[3,4]thieno[1,3-c]pyrimidin-8-yl)acetate A mixture of ethyl 2-amino-4-(2-ethoxy-2-oxo-ethyl)-5,6-dihydro-4H-cyclopenta[b]thiophene-3-carboxylate (28.0 g, 94.1 mmol) and formamide (158 g, 3.51 mol) was stirred at 180° C. for 8 h. On completion, the reaction mixture was cooled to room temperature and then quenched with water/ice (200 mL). The mixture was extracted with ethyl acetate (3×100 mL) and the combined organic layer was dried over anhydrous Na$_2$SO$_4$, filtered and concentrated in vacuo to give the title compound (15.0 g, 57% yield) as a yellow brown solid. $^1$H NMR (400 MHz, DMSO-d$_6$) δ 12.49 (s, 1H), 8.03 (s, 1H), 4.05 (q, J=7.2 Hz, 2H), 3.66-3.52 (m, 1H), 3.28 (dd, J=3.6, 16 Hz, 1H), 3.08-2.81 (m, 2H), 2.74-2.59 (m, 1H), 2.40-2.30 (m, 1H), 2.18-1.99 (m, 1H), 1.15 (t, J=7.2 Hz, 3H); LC-MS (ESI$^+$) m/z 279.0 (M+H)$^+$.

Step 3—Ethyl 2-(1-chloro-7,8-dihydro-6H-cyclopenta[3,4]thieno[1,3-d]pyrimidin-8-yl)acetate A mixture of ethyl 2-(1-hydroxy-7,8-dihydro-6H-cyclopenta[3,4]thieno[1,3-c]pyrimidin-8-yl)acetate (14.0 g, 50.3 mmol) in POCl$_3$ (165 g, 1.08 mol) was stirred at 85° C. for 16 h. On completion, the reaction mixture was concentrated in vacuo to give a residue. The residue was purified by column chromatography (SiO$_2$, PE:EA=5:1) to give the title compound (12.0 g, 80% yield) as a light yellow oil. $^1$H NMR (400 MHz, CDCl$_3$) δ 8.71-8.63 (m, 1H), 4.07 (q, J=7.2 Hz, 2H), 3.93-3.83 (m, 1H), 3.16-3.04 (m, 1H), 3.00-2.90 (m, 1H), 2.85 (dd, J=2.8, 12.8 Hz, 1H), 2.73-2.67 (m, 1H), 2.42 (dd, J=10.4, 15.2 Hz, 1H), 2.34-2.28 (m, 1H), 1.15 (t, J=7.2 Hz, 3H); LC-MS (ESI$^+$) m/z 297.0 (M+H)$^+$.

Step 4—2-(1-Chloro-7,8-dihydro-6H-cyclopenta[3,4]thieno[1,3-d]pyrimidin-8-yl)ethanol To a solution of ethyl 2-(1-chloro-7,8-dihydro-6H-cyclopenta[3,4]thieno[1,3-d]pyrimidin-8-yl)acetate (18.0 g, 60.6 mmol) in THF (200 mL) was added DIBAL-H (1 M, 196 mL) at −50° C. dropwise. Then the mixture was stirred at −30° C. for 1 hour. On completion, the mixture was added to water (10 mL) and NaOH solution (15%, 20 mL) at 0° C. The mixture was then filtered and dried over Na$_2$SO$_4$, then filtered again and concentrated in vacuo to give a residue. The residue was purified by column chromatography (SiO$_2$, PE:EA=5:1) to give the title compound (12.0 g, 68% yield) as a light yellow solid. $^1$H NMR (400 MHz, CDCl$_3$) δ 8.76 (s, 1H), 3.85-3.71 (m, 2H), 3.62 (t, J=8.8 Hz, 1H), 3.21-3.07 (m, 1H), 3.06-2.93 (m, 1H), 2.70-2.60 (m, 1H), 2.44-2.33 (m, 1H), 2.20-2.08 (m, 1H), 1.78-1.68 (m, 1H); LC-MS (ESI$^+$) m/z 254.9 (M+H)$^+$.

Step 5—2-[(8R)-1-chloro-7,8-dihydro-6H-cyclopenta[3,4]thieno[1,3-d]pyrimidin-8-yl]ethanol The racemic 2-(1-chloro-7,8-dihydro-6H-cyclopenta[3,4]thieno[1,3-d]pyrimidin-8-yl)ethanol (23.0 g, 90.2 mmol) was separated by SFC (column: AD (250 mm*30 mm, 10 um); mobile phase: [0.1% NH$_3$H$_2$O MEOH]) to give to give two isomers. The first fraction was the desired product: 2-[(8R)-1-chloro-7,8-dihydro-6H-cyclopenta[3,4]thieno[1,3-d]pyrimidin-8-yl]ethanol (10.9 g, 47% yield, tR=2.562) which was isolated as a yellow solid. The second fraction is 2-[(8S)-1-chloro-7,8-dihydro-6H-cyclopenta[3,4]thieno[1,3-d]pyrimidin-8-yl]ethanol (11.5 g, 49% yield, tR=3.522) was also isolated as a yellow solid. $^1$H NMR (400 MHz, CDCl$_3$) δ 8.72 (s, 1H), 3.87-3.72 (m, 2H), 3.70-3.59 (m, 1H), 3.21-3.09 (m, 1H), 3.06-2.95 (m, 1H), 2.71-2.61 (m, 1H), 2.41-2.35 (m, 1H), 2.19-2.09 (m, 1H), 1.78-1.69 (m, 1H); LC-MS (ESI$^+$) m/z 255.0 (M+H)$^+$.

Step 6—Tert-butyl-[2-[(8R)-1-chloro-7,8-dihydro-6H-cyclopenta[3,4]thieno[1,3-d]pyrimidin-8-yl]ethoxy]-dimethyl-silane To a solution of 2-[(8R)-1-chloro-7,8-dihydro-6H-cyclopenta[3,4]thieno[1,3-d]pyrimidin-8-yl]ethanol (5.9 g, 23.1 mmol) in DMF (60 mL) was added imidazole (2.21 g, 32.4 mmol) and TBSCl (4.19 g, 27.7 mmol). The reaction mixture was stirred at rt for 13 h under nitrogen atmosphere. On completion, the reaction mixture was diluted with water (30 mL) and extracted with EA (3×30 mL). The combined organic layers were dried over Na$_2$SO$_4$, filtered and concentrated in vacuo to give a residue. The residue was purified by silica gel chromatography (PE:EA=5:1) to give the title compound (7.80 g, 87% yield) as a light yellow oil. $^1$H NMR (400 MHz, CDCl$_3$) δ 8.74 (s, 1H), 3.82-3.70 (m, 2H), 3.68-3.58 (m, 1H), 3.20-3.09 (m, 1H), 3.05-2.95 (m, 1H), 2.68-2.58 (m, 1H), 2.48-2.37 (m, 1H), 2.17-2.05 (m, 1H), 1.70-1.63 (m, 1H), 0.89 (s, 9H), 0.06 (d, J=0.8 Hz, 6H); LC-MS (ESI⁺) m/z 369.0 (M+H)⁺.

Step 7—Tert-butyl 4-[4-[[(8R)-8-[2-[tert-butyl(dimethyl)silyl]oxyethyl]-7,8-dihydro-6H-cyclopenta[4,5]thieno[1,2-c]pyrimidin-1-yl]oxy]cyclohexyl]piperazine-1-carboxylate To a solution of tert-butyl 4-(4-hydroxycyclohexyl)piperazine-1-carboxylate (4.32 g, 15.1 mmol, Intermediate DQ) in THF (80 mL) was added NaH (1.73 g, 43.3 mmol, 60% dispersion in mineral oil) at 0° C. The reaction mixture was stirred at 0° C. for 1 hour, then a solution of tert-butyl-[2-[(8R)-1-chloro-7,8-dihydro-6H-cyclopenta[3,4]thieno[1,3-d]pyrimidin-8-yl]ethoxy]-dimethyl-silane (4.00 g, 10.8 mmol) in THF (40 mL) was added at 0° C. dropwise. The reaction mixture was then heated to 60° C. and stirred for 14 h. On completion, the reaction mixture was quenched with water (50 mL) and the mixture was extracted with EA (3×80 mL). The combined organic layer was dried over Na₂SO₄, filtered and concentrated in vacuo to give a residue. The residue was purified by silica gel chromatography (PE:EA=3:1) to give the title compound (4.00 g, 42% yield) as a light yellow solid. ¹H NMR (400 MHz, CDCl₃) δ 8.49 (s, 1H), 5.27-5.14 (m, 1H), 3.77-3.63 (m, 2H), 3.50-3.40 (m, 5H), 3.14-3.01 (m, 1H), 2.99-2.87 (m, 1H), 2.68-2.57 (m, 1H), 2.56-2.47 (m, 4H), 2.43-2.37 (m, 1H), 2.36-2.19 (m, 4H), 1.97 (d, J=10.4 Hz, 2H), 1.64-1.51 (m, 5H), 1.47 (s, 9H), 0.90 (s, 9H), 0.05 (s, 6H); LC-MS (ESI⁺) m/z 617.2 (M+H)⁺.

Step 8—Tert-butyl 4-[4-[[(8R)-8-(2-hydroxyethyl)-7,8-dihydro-6H-cyclopenta[4,5]thieno[1,2-c]pyrimidin-1-yl]oxy]cyclohexyl]piperazine-1-carboxylate To a solution of tert-butyl 4-[4-[[(8R)-8-[2-[tert-butyl(dimethyl)silyl]oxyethyl]-7,8-dihydro-6H-cyclopenta[4,5]thieno[1,2-c]pyrimidin-1-yl]oxy]cyclohexyl]piperazine-1-carboxylate (12.0 g, 19.4 mmol) in THF (120 mL) was added TBAF (1 M, 29.1 mL), and the mixture was stirred at rt for 14 h. On completion, the reaction mixture was quenched by addition of water (100 mL), and then extracted with EA (3×200 mL). The combined organic layers were dried over Na₂SO₄, filtered and concentrated in vacuo to give a residue. The residue was purified by silica gel chromatography (PE:EA=1:1) to give the title compound (9.7 g, 93% yield) as a light yellow oil. ¹H NMR (400 MHz, CDCl₃) δ 8.50 (s, 1H), 5.29-5.16 (m, 1H), 3.79-3.67 (m, 2H), 3.52-3.40 (m, 5H), 3.14-3.02 (m, 1H), 2.96-2.90 (m, 1H), 2.71-2.62 (m, 1H), 2.58-2.48 (m, 4H), 2.47-2.39 (m, 1H), 2.38-2.25 (m, 3H), 2.21-2.12 (m, 1H), 2.03-1.92 (m, 2H), 1.81-1.70 (m, 2H), 1.65-1.49 (m, 4H), 1.47 (s, 9H). LC-MS (ESI⁺) m/z 503.2 (M+H)⁺.

Step 9—Tert-butyl 4-[4-[[(8R)-8-(2-oxoethyl)-7,8-dihydro-6H-cyclopenta[4,5]thieno[1,2-c]pyrimidin-1-yl]oxy]cyclohexyl]piperazine-1-carboxylate To a solution of tert-butyl 4-[4-[[(8R)-8-(2-hydroxyethyl)-7,8-dihydro-6H-cyclopenta[4,5]thieno[1,2-c]pyrimidin-1-yl]oxy]cyclohexyl]piperazine-1-carboxylate (9.70 g, 19.3 mmol) in DCM (160 mL) was added DMP (16.3 g, 38.5 mmol) at 0° C. Then the mixture was allowed to warm to rt and stirred for 16 h. On completion, the reaction mixture was quenched by saturated NaHCO₃ (200 mL) and then extracted with DCM (3×200 mL). The combined organic layers were dried over Na₂SO₄, filtered and concentrated in vacuo to give a residue. The residue was purified by silica gel chromatography (PE:EA=1:1) to give the title compound (9.00 g, 72% yield) as a yellow oil. ¹H NMR (400 MHz, CDCl₃) δ 9.84 (s, 1H), 8.52 (s, 1H), 5.28-5.17 (m, 1H), 3.48 (t, J=5.2 Hz, 1H), 3.58-3.48 (m, 4H), 3.16-2.98 (m, 3H), 2.88-2.76 (m, 1H), 2.74-2.52 (m, 6H), 2.38-2.27 (m, 2H), 2.18-2.11 (m, 1H), 2.05-1.98 (m, 2H), 1.60-1.50 (m, 4H), 1.47 (s, 9H); LC-MS (ESI⁺) m/z 501.2 (M+H)⁺.

Step 10—Tert-butyl 4-[4-[[(8R)-8-(2-cyano-2-trimethylsilyloxy-ethyl)-7,8-dihydro-6H-cyclopenta[4,5]thieno[1,2-c]pyrimidin-1-yl]oxy]cyclohexyl]piperazine-1-carboxylate and tert-butyl 4-[4-[[(8R)-8-(2-cyano-2-hydroxy-ethyl)-7,8-dihydro-6H-cyclopenta[4,5]thieno[1,2-c]pyrimidin-1-yl]oxy]cyclohexyl]piperazine-1-carboxylate To a solution of tert-butyl 4-[4-[[(8R)-8-(2-oxoethyl)-7,8-dihydro-6H-cyclopenta[4,5]thieno[1,2-c]pyrimidin-1-yl]oxy]cyclohexyl]piperazine-1-carboxylate (6.00 g, 11.98 mmol) and TEA (1.21 g, 11.9 mmol) in DCM (80 mL) was added TMSCN (3.57 g, 35.9 mmol), and the mixture was stirred at rt for 4 h. On completion, the reaction mixture was diluted with water (60 mL) and extracted with DCM (3×80 mL). The combined organic layers were dried over Na₂SO₄, filtered and concentrated under reduced pressure to give tert-butyl 4-[4-[[(8R)-8-(2-cyano-2-trimethylsilyloxy-ethyl)-7,8-dihydro-6H-cyclopenta[4,5]thieno[1,2-c]pyrimidin-1-yl]oxy]cyclohexyl]piperazine-1-carboxylate (5.5 g) and tert-butyl 4-[4-[[(8R)-8-(2-cyano-2-hydroxy-ethyl)-7,8-dihydro-6H-cyclopenta[4,5]thieno[1,2-c]pyrimidin-1-yl]oxy]cyclohexyl]piperazine-1-carboxylate (0.5 g) as a yellow oil, which were brought on to the next step as a mixture. LC-MS (ESI⁺) m/z 600.3 (M+H)⁺.

Step 11—Tert-butyl 4-[4-[[(8R)-8-(2-cyano-2-hydroxy-ethyl)-7,8-dihydro-6H-cyclopenta[4,5]thieno[1,2-c]pyrimidin-1-yl]oxy]cyclohexyl]piperazine-1-carboxylate To a solution of tert-butyl 4-[4-[[(8R)-8-(2-cyano-2-trimethylsilyloxy-ethyl)-7,8-dihydro-6H-cyclopenta[4,5]thieno[1,2-c]pyrimidin-1-yl]oxy]cyclohexyl]piperazine-1-carboxylate (5.50 g, 9.17 mmol) and tert-butyl 4-[4-[[(8R)-8-(2-cyano-2-hydroxy-ethyl)-7,8-dihydro-6H-cyclopenta[4,5]thieno[1,2-c]pyrimidin-1-yl]oxy]cyclohexyl]piperazine-1-carboxylate (500 mg, 947 umol) in THF (80 mL) was added TBAF (1 M, 13.75 mL), and the mixture was stirred at rt for 3 h. On completion, the reaction mixture was quenched with water (80 mL), and then extracted with EA (3×100 mL). The combined organic layers were dried over Na₂SO₄, filtered and concentrated in vacuo to give a residue. The residue was purified by silica gel chromatography (PE:EA=1:1) to give the title compound (4.20 g, 69% yield) as a light yellow oil. ¹H NMR (400 MHz, CDCl₃) δ 8.51 (d, J=1.6 Hz, 1H), 5.32-5.18 (m, 1H), 4.58-4.50 (m, 1H), 3.69-3.37 (m, 5H), 3.17-2.92 (m, 2H), 2.80-2.66 (m, 1H), 2.65-2.46 (m, 6H), 2.43-2.23 (m, 3H), 2.04-1.85 (m, 3H), 1.76-1.49 (m, 4H), 1.46 (s, 9H). LC-MS (ESI⁺) m/z 528.1 (M+H)⁺.

Step 12—2-Hydroxy-3-[(8R)-1-(4-piperazin-1-ylcyclohexoxy)-7,8-dihydro-6H-cyclopenta[4,5]thieno[1,2-c]pyrimidin-8-yl]propanamide To a solution of tert-butyl 4-[4-[[(8R)-8-(2-cyano-2-hydroxy-ethyl)-7,8-dihydro-6H-cyclopenta[4,5]thieno[1,2-c]pyrimidin-1-yl]oxy]cyclohexyl]piperazine-1-carboxylate (4.20 g, 7.96 mmol) in DCM (80 mL) was added HCl in dioxane (4 M, 33.6 mL), and the mixture was stirred at rt for 3 h. On completion, the reaction mixture was quenched with saturated sodium bicarbonate (30 mL). The mixture was concentrated in vacuo to give the title compound (4.00 g, 100% yield) as a light yellow solid. LC-MS (ESI$^+$) m/z 446.2 (M+H)$^+$.

Step 13—Tert-butyl 4-[4-[[(8R)-8-(3-amino-2-hydroxy-3-oxo-propyl)-7,8-dihydro-6H-cyclopenta[4,5]thieno[1,2-c]pyrimidin-1-yl]oxy]cyclohexyl]piperazine-1-carboxylate To a solution of 2-hydroxy-3-[(8R)-1-(4-piperazin-1-ylcyclohexoxy)-7,8-dihydro-6H-cyclopenta[4,5]thieno[1,2-c]pyrimidin-8-yl]propanamide (2.50 g, 5.61 mmol) in a mixed solvent of DCM (25 mL) and MeOH (25 mL) was added TEA (1.70 g, 16.8 mmol) and Boc$_2$O (2.45 g, 11.2 mmol), and the mixture was stirred at rt for 16 h. On completion, the reaction mixture was concentrated in vacuo to give a residue. The residue was purified by reverse phase chromatography (0.1% NH$_3$.H$_2$O) to give the title compound (1.50 g, 47% yield) as a colorless oil. $^1$H NMR (400 MHz, CDCl$_3$) δ 8.49 (d, J=5.2 Hz, 1H), 6.70-6.50 (m, 1H), 6.01-5.87 (m, 1H), 5.29-5.13 (m, 1H), 4.20-4.13 (m, 1H), 3.72-3.53 (m, 1H), 3.42 (t, J=4.4 Hz, 4H), 3.15-3.04 (m, 1H), 3.01-2.88 (m, 1H), 2.78-2.60 (m, 1H), 2.58-2.49 (m, 4H), 2.49-2.12 (m, 6H), 1.99-1.83 (m, 3H), 1.63-1.43 (m, 13H). LC-MS (ESI$^+$) m/z 546.2 (M+H)$^+$.

Step 14—Tert-butyl 4-[4-[[(8R)-8-[(2S)-3-amino-2-hydroxy-3-oxo-propyl]-7,8-dihydro-6H-cyclopenta[4,5]thieno[1,2-c]pyrimidin-1-yl]oxy]cyclohexyl]piperazine-1-carboxylate The racemic tert-butyl 4-[4-[[(8R)-8-(3-amino-2-hydroxy-3-oxo-propyl)-7,8-dihydro-6H-cyclopenta[4,5]thieno[1,2-c]pyrimidin-1-yl]oxy]cyclohexyl]piperazine-1-carboxylate (1.50 g, 2.66 mmol) was separated by SFC (column: AD (250 mm*30 mm, 10 um); mobile phase: [0.1% NH$_3$H$_2$O ETOH]) to give the two isomers. The first fraction is tert-butyl 4-[4-[[(8R)-8-[(2R)-3-amino-2-hydroxy-3-oxo-propyl]-7,8-dihydro-6H-cyclopenta[4,5]thieno[1,2-c]pyrimidin-1-yl]oxy]cyclohexyl]piperazine-1-carboxylate (700 mg, 46% yield, tR=1.034) which was isolated as a light yellow solid. $^1$H NMR (400 MHz, CDCl$_3$) δ 8.46 (s, 1H), 6.66 (d, J=2.8 Hz, 1H), 5.99 (d, J=2.8 Hz, 1H), 5.25-5.11 (m, 1H), 4.21-4.10 (m, 1H), 3.67-3.56 (m, 1H), 3.47-3.29 (m, 4H), 3.13-3.01 (m, 1H), 2.98-2.86 (m, 1H), 2.70-2.57 (m, 1H), 2.54-2.43 (m, 4H), 2.40-2.04 (m, 6H), 1.97-1.79 (m, 3H), 1.75-1.26 (m, 13H); LC-MS (ESI$^+$) m/z 546.2 (M+H)$^+$.

The second fraction was the desired 4-[4-[[(8R)-8-[(2S)-3-amino-2-hydroxy-3-oxo-propyl]-7,8-dihydro-6H-cyclopenta[4,5]thieno[1,2-c]pyrimidin-1-yl]oxy]cyclohexyl]piperazine-1-carboxylate (560 mg, 37% yield, tR=1.238) was also isolated as a light yellow solid. $^1$H NMR (400 MHz, CDCl$_3$) δ 8.50 (s, 1H), 6.60 (d, J=2.8 Hz, 1H), 5.72 (d, J=2.8 Hz, 1H), 5.30-5.23 (m, 1H), 4.18-4.10 (m, 1H), 3.63-3.51 (m, 1H), 3.48-3.36 (m, 4H), 3.18-3.05 (m, 1H), 3.00-2.88 (m, 1H), 2.81-2.66 (m, 1H), 2.55-2.59 (m, 4H), 2.45-2.23 (m, 6H), 2.05-1.81 (m, 3H), 1.66-1.44 (m, 13H); LC-MS (ESI$^+$) m/z 546.3 (M+H)$^+$.

Step 15—(2S)-2-Hydroxy-3-[(8R)-1-(4-piperazin-1-ylcyclohexoxy)-7,8-dihydro-6H-cyclopenta[4,5]thieno[1,2-c]pyrimidin-8-yl]propanamide To a solution of tert-butyl 4-[4-[[(8R)-8-[(2S)-3-amino-2-hydroxy-3-oxo-propyl]-7,8-dihydro-6H-cyclopenta[4,5]thieno[1,2-c]pyrimidin-1-yl]oxy]cyclohexyl]piperazine-1-carboxylate (80.0 mg, 143 umol) in DCM (2 mL) was added HCl in dioxane (4 M, 1.37 mL), and the mixture was stirred at rt for 1 hour. On completion, the reaction mixture was concentrated in vacuo to give the title compound (80 mg, 100% yield, HCl salt) as a white solid; LC-MS (ESI$^+$) m/z 446.1 (M+H)$^+$.

Tert-butyl 2-(2-aminoethoxy)acetate (Intermediate DS)

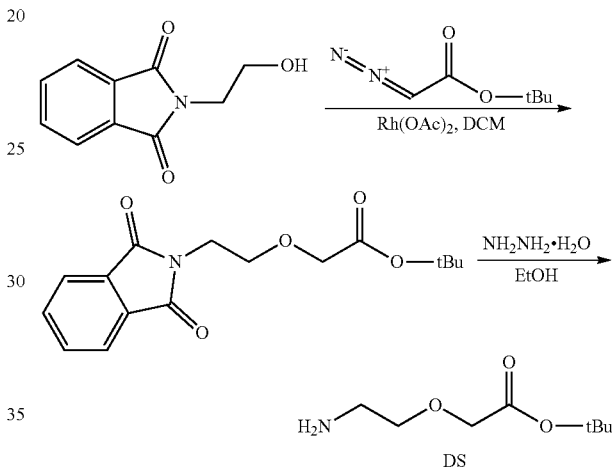

Step 1—Tert-butyl 2-[2-(1,3-dioxoisoindolin-2-yl)ethoxy]acetate

To a solution of 2-(2-hydroxyethyl)isoindoline-1,3-dione (1.00 g, 5.23 mmol, CAS #3891-07-4) and Rh(OAc)$_2$ (46.2 mg, 209 umol) in DCM (20 mL) was added tert-butyl 2-diazoacetate (1.64 g, 11.5 mmol) in DCM (20 mL) dropwise at rt over 1 hour. The reaction mixture was then stirred at rt for 20 hours. On completion, the mixture was concentrated in vacuo. The residue was purified by silica gel chromatography to give the title compound (0.76 g, 48% yield) as a yellow oil. $^1$H NMR (400 MHz, CDCl$_3$) δ 7.90-7.84 (m, 2H), 7.77-7.70 (m, 2H), 3.99 (s, 2H), 3.97-3.93 (m, 2H), 3.85-3.80 (m, 2H), 1.45 (s, 9H); LC-MS (ESI$^+$) m/z 328.0 (M+Na)$^+$.

Step 2—Tert-butyl 2-(2-aminoethoxy)acetate

To a solution of tert-butyl 2-[2-(1,3-dioxoisoindolin-2-yl)ethoxy]acetate (0.76 g, 2.49 mmol) in EtOH (20 mL) was added NH$_2$NH$_2$.H$_2$O (623 mg, 12.5 mmol). The reaction mixture was stirred at 80° C. for 2 hours. On completion, the mixture was filtered and the filtrate was concentrated in vacuo. The residue was diluted with DCM (20 mL), filtered and the filtrate was concentrated in vacuo to give the title compound (340 mg, 78% yield) as a yellow oil. LC-MS (ESI$^+$) m/z 176.0 (M+H)$^+$.

2-[2-[2-[2-[2-(2-ethoxy-2-oxo-ethoxy)ethoxy]ethoxy]ethoxy]ethoxy]acetic acid (Intermediate DT)

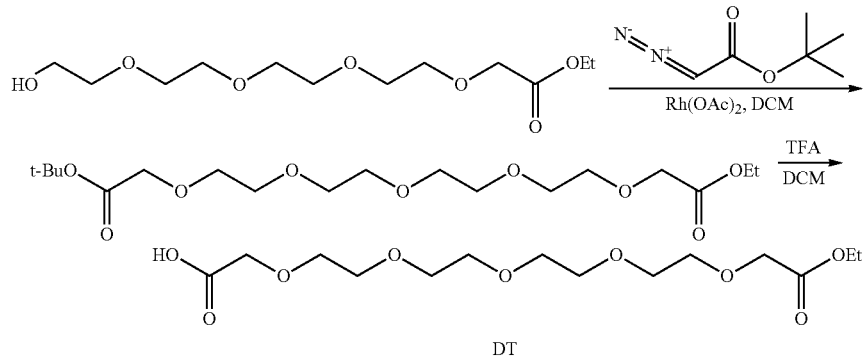

Step 1—Ethyl 2-[2-[2-[2-[2-(2-tert-butoxy-2-oxo-ethoxy)ethoxy]ethoxy]ethoxy]ethoxy]acetate To a solution of ethyl 2-[2-[2-[2-(2-hydroxyethoxy)ethoxy]ethoxy]ethoxy]acetate (1.00 g, 3.57 mmol, synthesized via Step 1 of Intermediate BK) and Rh(OAc)$_2$ (39.5 mg, 178 umol) in DCM (20 mL) was added a solution of tert-butyl 2-diazoacetate (1.01 g, 7.14 mmol) in DCM (30 mL) dropwise at rt over 30 minutes. The reaction mixture was then stirred at rt for an additional 17 hours. On completion, the mixture was washed with water (3×30 mL). The organic phase was separated and was dried over Na$_2$SO$_4$, filtered and concentrated in vacuo. The residue was purified by silica gel chromatography to give the title compound (0.64 g, 45% yield) as a yellow oil. $^1$H NMR (400 MHz, CDCl$_3$) δ 4.23 (q, J=7.2 Hz, 2H), 4.17 (s, 2H), 4.04 (s, 2H), 3.78-3.66 (m, 16H), 1.49 (s, 9H), 1.30 (t, J=7.2 Hz, 3H).

Step 2—2-[2-[2-[2-[2-(2-ethoxy-2-oxo-ethoxy)ethoxy]ethoxy]ethoxy]ethoxy]acetic acid To a solution of ethyl 2-[2-[2-[2-[2-(2-tert-butoxy-2-oxo-ethoxy)ethoxy]ethoxy]ethoxy]ethoxy]acetate (200 mg, 507 umol) in DCM (1.5 mL) was added TFA (1.5 mL). The reaction mixture was stirred at rt for 30 minutes. On completion, the mixture was concentrated in vacuo to give the title compound (170 mg, 99% yield) as a yellow oil.

(4-Hydroxycyclohexyl) 4-methylbenzenesulfonate (Intermediate DU)

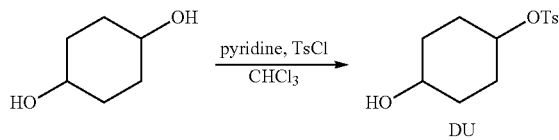

To a solution of pyridine (12.3 g, 155 mmol) in CHCl$_3$ (150 mL) was added cyclohexane-1,4-diol (15.0 g, 129 mmol) at rt. Then the mixture was then cooled to 0° C. and 4-methylbenzenesulfonyl chloride (24.6 g, 129 mmol) was added into the mixture. The reaction mixture was then allowed to warm to rt and stirred for 18 hrs. On completion, the reaction mixture was acidified with 1N HCl solution until the pH=5-6, and extracted with EA (3×30 mL). The organic layer was washed with brine (50 mL), dried over Na$_2$SO$_4$, and concentrated in vacuo. The residue was purified by silica gel chromatography to give the title compound (16.0 g, 46% yield) as a white solid. $^1$H NMR (400 MHz, CDCl$_3$) δ 7.85-7.76 (m, 2H), 7.36 (d, J=8.0 Hz, 2H), 4.66-4.49 (m, 1H), 3.80-3.70 (m, 1H), 2.47 (s, 3H), 1.97-1.91 (m, 2H), 1.72-1.65 (m, 2H), 1.64-1.50 (m, 4H).

Tert-butyl 4-((4-(4,4,5,5-tetramethyl-1,3,2-dioxaborolan-2-yl)phenyl)sulfonyl) piperazine-1-carboxylate

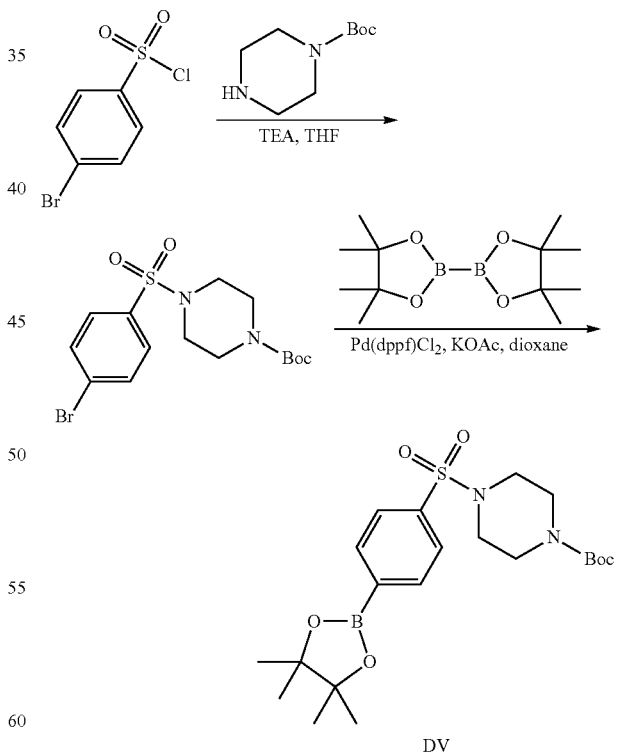

Step 1—Tert-butyl 4-((4-bromophenyl)sulfonyl) piperazine-1-carboxylate

To a solution of tert-butyl piperazine-1-carboxylate (20.1 g, 108 mmol) in THF (250 mL) was added TEA (19.8 g, 196 mmol) at 0° C. The mixture was stirred at 0° C. for 10 minutes, then 4-bromobenzene sulfonylchloride (25.0 g, 97.8 mmol) was added to the reaction mixture. The reaction mixture was then allowed to warm to rt and stirred for 50 minutes. On completion, the reaction mixture was filtered and concentrated in vacuo. The residue was washed with water (100 mL) and 10% HCl (50 mL), and then extracted with DCM (2×50 mL). The organic layer was washed with NaHCO$_3$ (50 mL) until the pH=8. The combined organic layers were dried over Na$_2$SO$_4$, filtered and concentrated in vacuo to give a residue. The residue was purified by column chromatography (petroleum ether/ethyl acetate=0:1) to give the title compound (33 g, 83% yield)) as a white solid. $^1$H NMR (400 MHz, CDCl$_3$) δ 7.72-7.70 (m, 2H), 7.64-7.62 (m, 2H), 3.54 (t, J=4.8 Hz, 4H), 3.00 (t, J=4.8 Hz, 4H), 1.43 (s, 9H).

Step 2—Tert-butyl 4-((4-(4,4,5,5-tetramethyl-1,3,2-dioxaborolan-2-yl)phenyl)sulfonyl) piperazine-1-carboxylate To a solution of tert-butyl 4-(4-bromophenyl)sulfonylpiperazine-1-carboxylate (10.0 g, 24.7 mmol) and 4,4,5,5-tetramethyl-2-(4,4,5,5-tetramethyl-1,3,2-dioxaborolan-2-yl)-1,3,2-dioxaborolane (18.8 g, 74.0 mmol) in dioxane (100 mL) was added Pd(dppf)Cl$_2$ (1.81 g, 2.47 mmol) and KOAc (4.84 g, 49.4 mmol). The reaction mixture was stirred at 80° C. for 3 hours. On completion, the mixture was filtered, and the filter was concentrated in vacuo to give a residue. The residue was purified by flash silica gel chromatography (Ethyl acetate:Petroleum ether=1/1) to give the title compound (8.00 g, 63% yield) as a gray solid. $^1$H NMR (400 MHz, CDCl$_3$) δ 7.98 (d, J=8.0 Hz, 2H), 7.74 (d, J=8.0 Hz, 2H), 3.52 (t, J=4.8 Hz, 4H), 2.98 (t, J=4.8 Hz, 4H), 1.42 (s, 9H), 1.37 (s, 12H), LC-MS (ESI$^+$) m/z 397.0 (M+H−56)$^+$.

Ethyl 2-[2-[2-[2-(2-aminoethoxy)ethoxy]ethoxy]ethoxy]acetate (Intermediate DW)

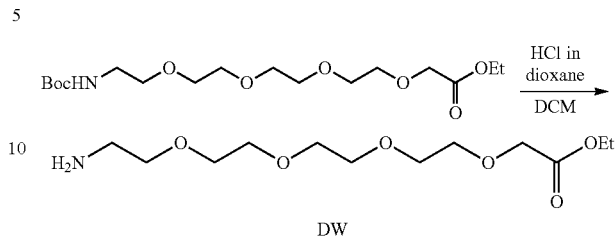

To a solution of ethyl 2-[2-[2-[2-[2-(tert-butoxycarbonylamino)ethoxy]ethoxy]ethoxy]ethoxy]acetate (0.80 g, 2.11 mmol, synthesized via Steps 1-4 of Intermediate CH) in DCM (10 mL) was added HCl in dioxane (4 M, 2.67 mL). The reaction mixture was stirred at rt for 15 minutes. On completion, the reaction mixture was concentrated in vacuo to give the title compound (0.55 g, 83% yield, HCl) as a yellow oil.

Tert-butyl 2-(8-aminooctoxy)acetate (Intermediate DX)

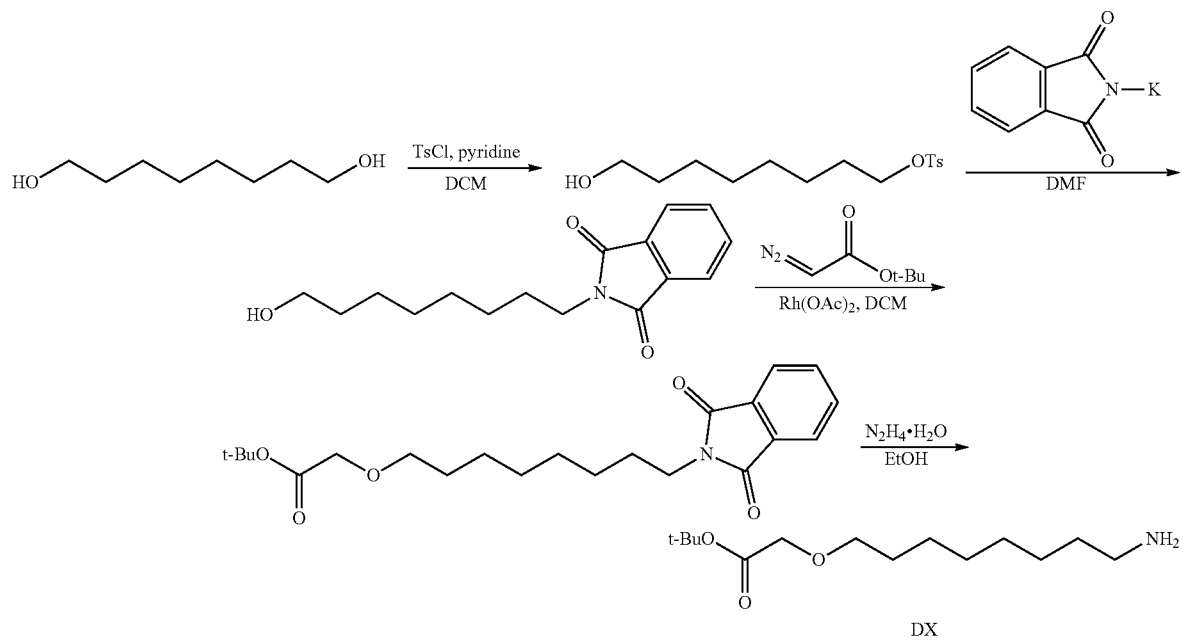

Step 1—8-Hydroxyoctyl 4-methylbenzenesulfonate

To a mixture of octane-1,8-diol (23.5 g, 160 mmol, CAS #629-41-4) and pyridine (10.1 g, 128 mmol) in DCM (360 mL) was added a solution of TsCl (24.5 g, 128 mmol) in DCM (240 mL) dropwise. The mixture was then stirred at rt for 16 hours. On completion, the mixture was washed with 1N HCl (2×50 mL). The organic layer was dried with Na$_2$SO$_4$, filtered and concentrated in vacuo to give a residue. The residue was purified by silica gel chromatography (petroleum ether:ethyl acetate=3:1) to give the title compound (10.0 g, 20% yield) as a colorless oil. $^1$H NMR (400 MHz, CDCl$_3$) δ 7.80 (d, J=8.0 Hz, 2H), 7.35 (d, J=8.0 Hz, 2H), 4.02 (t, J=6.4 Hz, 2H), 3.63 (t, J=6.4 Hz, 2H), 2.45 (s, 3H), 1.69-1.60 (m, 2H), 1.56-1.53 (m, 2H), 1.36-1.23 (m, 8H); LC-MS (ESI$^+$) m/z 323.0 (M+Na)$^+$.

Step 2—2-(8-Hydroxyoctyl)isoindoline-1,3-dione

To a solution of 8-hydroxyoctyl 4-methylbenzenesulfonate (5.00 g, 16.6 mmol) in DMF (80 mL) was added (1,3-dioxoisoindolin-2-yl)potassium (4.01 g, 21.6 mmol). The mixture was stirred at 100° C. for 16 hours. On completion, the reaction mixture was concentrated in vacuo to give a residue. The residue was diluted with DCM (50 mL), filtered and the filtrate was concentrated in vacuo to give a residue. The residue was purified by silica gel chromatography (PE/EA=3/1) to give the title compound (4.50 g, 98% yield) as a white solid. $^1$H NMR (400 MHz, CDCl$_3$) δ 7.86-7.79 (m, 2H), 7.74-7.66 (m, 2H), 3.69-3.59 (m, 4H), 1.76-1.46 (m, 6H), 1.32-1.29 (m, 6H).

Step 3—Tert-butyl 2-[8-(1,3-dioxoisoindolin-2-yl)octoxy]acetate

To a solution of 2-(8-hydroxyoctyl)isoindoline-1,3-dione (3.00 g, 10.9 mmol) and Rh(OAc)$_2$ (120 mg, 544 umol) in DCM (20 mL) was added a solution of tert-butyl 2-diazoacetate (2.32 g, 16.3 mmol) in DCM (80 mL) dropwise. The reaction mixture was stirred at rt for 48 hours. On completion, the reaction mixture was concentrated in vacuo to give a residue. The residue was purified by silica gel chromatography (PE/EA=2/1) to give the title compound (1.40 g, 26% yield) as a light yellow oil. LC-MS (ESI$^+$) m/z 412.2 (M+Na)$^+$.

Step 4—Tert-butyl 2-(8-aminooctoxy)acetate

To a solution of tert-butyl 2-[8-(1,3-dioxoisoindolin-2-yl)octoxy]acetate (1.4 g, 2.91 mmol) in EtOH (25 mL) was added N$_2$H$_4$.H$_2$O (1.49 g, 29.1 mmol). Then the reaction mixture was stirred at 80° C. for 16 hours. On completion, the reaction mixture was filtered. The filtrate was concentrated in vacuo to give the title compound (750 mg, 99% yield) as a light yellow oil. LC-MS (ESI$^+$) m/z 260.2 (M+H)$^+$.

Methyl 5-(4-amino-3-carbamoyl-pyrazol-1-yl)pyridine-2-carboxylate Intermediate DY)

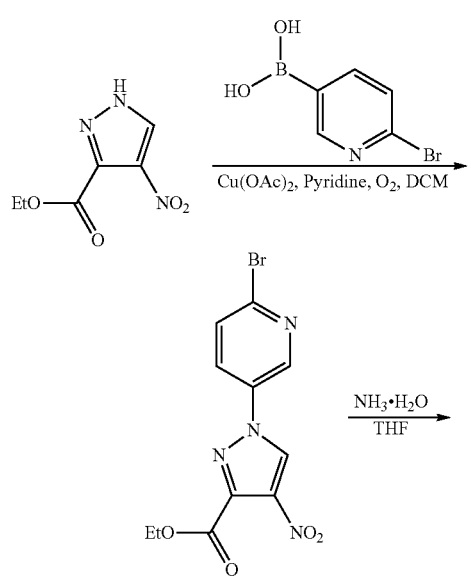

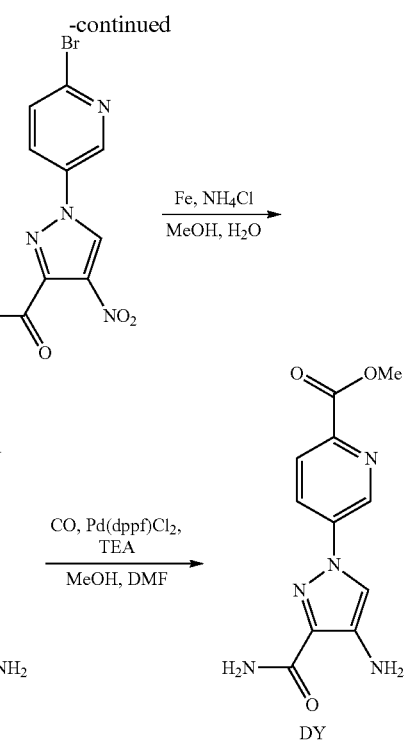

Step 1—Ethyl 1-(6-bromo-3-pyridyl)-4-nitro-pyrazole-3-carboxylate

To a solution of ethyl 4-nitro-1H-pyrazole-3-carboxylate (5.8 g, 31.3 mmol, CAS #55864-87-4), pyridine (9.91 g, 125 mmol) and Cu(OAc)$_2$ (8.54 g, 46.9 mmol) in DCM (120 mL) was added (6-bromo-3-pyridyl)boronic acid (7.59 g, 37.5 mmol, CAS #223463-14-7). The mixture was stirred at rt for 16 hours under an oxygen atmosphere (15 psi pressure). On completion, the reaction mixture was quenched by adding saturated NH$_3$.H$_2$O solution (40 mL). The organic layer was separated and dried over Na$_2$SO$_4$, filtered and concentrated in vacuo to give a residue. The residue was purified by silica gel chromatography (PE/EA=3/1) to give the title compound (2.30 g, 21% yield) as a white solid. $^1$H NMR (400 MHz, DMSO-d$_6$) δ 9.83 (s, 1H), 9.00 (d, J=2.8 Hz, 1H), 8.31 (dd, J=3.2, 8.8 Hz, 1H), 7.91 (d, J=8.8 Hz, 1H), 4.42 (q, J=7.2 Hz, 2H), 1.33 (t, J=7.2 Hz, 3H).

Step 2—1-(6-Bromo-3-pyridyl)-4-nitro-pyrazole-3-carboxamide

To a solution of ethyl 1-(6-bromo-3-pyridyl)-4-nitro-pyrazole-3-carboxylate (2.30 g, 6.74 mmol) in THF (15 mL) was added NH$_3$—H$_2$O (1.03 mmol, 25 mL, 30% solution) in a sealed tube, and the mixture was stirred at 80° C. for 16 hours. On completion, the reaction mixture was concentrated in vacuo to give the title compound (1.80 g, 72% yield) as a yellow solid. $^1$H NMR (400 MHz, DMSO-d$_6$) δ 9.74 (s, 1H), 9.03 (d, J=3.2 Hz, 1H), 8.32 (dd, J=2.8, 8.8 Hz, 1H), 8.23 (s, 1H), 7.96 (s, 1H), 7.91 (d, J=8.8 Hz, 1H); LC-MS (ESI$^+$) m/z 311.9 (M+H)$^+$.

Step 3—4-Amino-1-(6-bromo-3-pyridyl)pyrazole-3-carboxamide

To a solution of 1-(6-bromo-3-pyridyl)-4-nitro-pyrazole-3-carboxamide (1.80 g, 4.90 mmol) in a mixed solvent of MeOH (45 mL) and H₂O (10 mL) was added Fe (2.74 g, 49.0 mmol) and NH₄Cl (2.62 g, 49.0 mmol). The mixture was stirred at 70° C. for 36 hours. On completion, the reaction mixture was filtered and the filtrate was concentrated in vacuo to give a residue. The residue was triturated with water (20 mL), filtered and the filter cake was dried in vacuo to give the title compound (0.90 g, 65% yield) as a brown solid. LC-MS (ESI⁺) m/z 282.0 (M+H)⁺.

Step 4—Methyl 5-(4-amino-3-carbamoyl-pyrazol-1-yl)pyridine-2-carboxylate

To a solution of 4-amino-1-(6-bromo-3-pyridyl)pyrazole-3-carboxamide (450 mg, 1.60 mmol) in a mixed solvent of DMF (15 mL) and MeOH (15 mL) was added Pd(dppf)Cl₂ (46.6 mg, 63.8 umol) and TEA (161 mg, 1.60 mmol). The suspension was degassed under vacuum and purged with CO three times. The mixture was stirred at 80° C. for 16 hours under CO (50 psi pressure). On completion, the reaction mixture was concentrated in vacuo to give a residue. The residue was purified by silica gel column chromatography (Petroleum ether/Ethyl acetate=1/1) to give the title compound (400 mg, 94% yield) as a brown solid. LC-MS (ESI⁺) m/z 262.0 (M+H)⁺.

5-[4-[[2-[2-Tert-butoxycarbonyl(2,2,2-trifluoroethyl)amino]-4-pyridyl]oxazole-4-carbonyl]amino]-3-carbamoylpyrazol-1-yl pyridine-2-carboxylic acid (Intermediate DZ)

Step 1—Methyl 5-[4-[[2-[2-[tert-butoxycarbonyl(2,2,2-trifluoroethyl)amino]-4-pyridyl]oxazole-4-carbonyl]amino]-3-carbamoyl-pyrazol-1-yl]pyridine-2-carboxylate To a solution of 2-[2-[tert-butoxycarbonyl(2,2,2-trifluoroethyl)amino]-4-pyridyl]oxazole-4-carboxylic acid (494 mg, 1.28 mmol, Intermediate CM) in DMF (6 mL) was added HATU (630 mg, 1.66 mmol) and DIPEA (494.54 mg, 3.83 mmol). The mixture was stirred at rt for 12 minutes, then methyl 5-(4-amino-3-carbamoyl-pyrazol-1-yl)pyridine-2-carboxylate (340 mg, 1.28 mmol, Intermediate DY) was added, and the mixture was stirred at rt for 2 hours. On completion, the reaction mixture was concentrated in vacuo to give a residue. The residue was purified by silica gel chromatography to give the title compound (500 mg, 49% yield) as a yellow solid. LC-MS (ESI⁺) m/z 631.2 (M+H)⁺.

Step 2—5-[4-[[2-[2-[Tert-butoxycarbonyl(2,2,2-trifluoroethyl)amino]-4-pyridyl]oxazole-4-carbonyl]amino]-3-carbamoylpyrazol-1-yl]pyridine-2-carboxylic acid To a mixture of methyl 5-[4-[[2-[2-[tert-butoxycarbonyl(2,2,2-trifluoroethyl)amino]-4-pyridyl]oxazole-4-carbonyl]amino]-3-carbamoyl-pyrazol-1-yl]pyridine-2-carboxylate (500 mg, 792 umol) in a mixed solvent of THF (5 mL), MeOH (1 mL) and H₂O (1 mL) was added LiOH (94.9 mg, 3.96 mmol). The reaction mixture was stirred at rt for 2 hours. On completion, the reaction mixture was concentrated in vacuo to give the title compound (500 mg, 90% yield) as a brown solid. LC-MS (ESI⁺) m/z 617.2 (M+H)⁺.

Tert-butyl N-[(1S,2R)-2-[(2-bromopyrazolo[1,5-a]pyrimidin-5-yl)amino]cyclohexyl]carbamate (Intermediate EA)

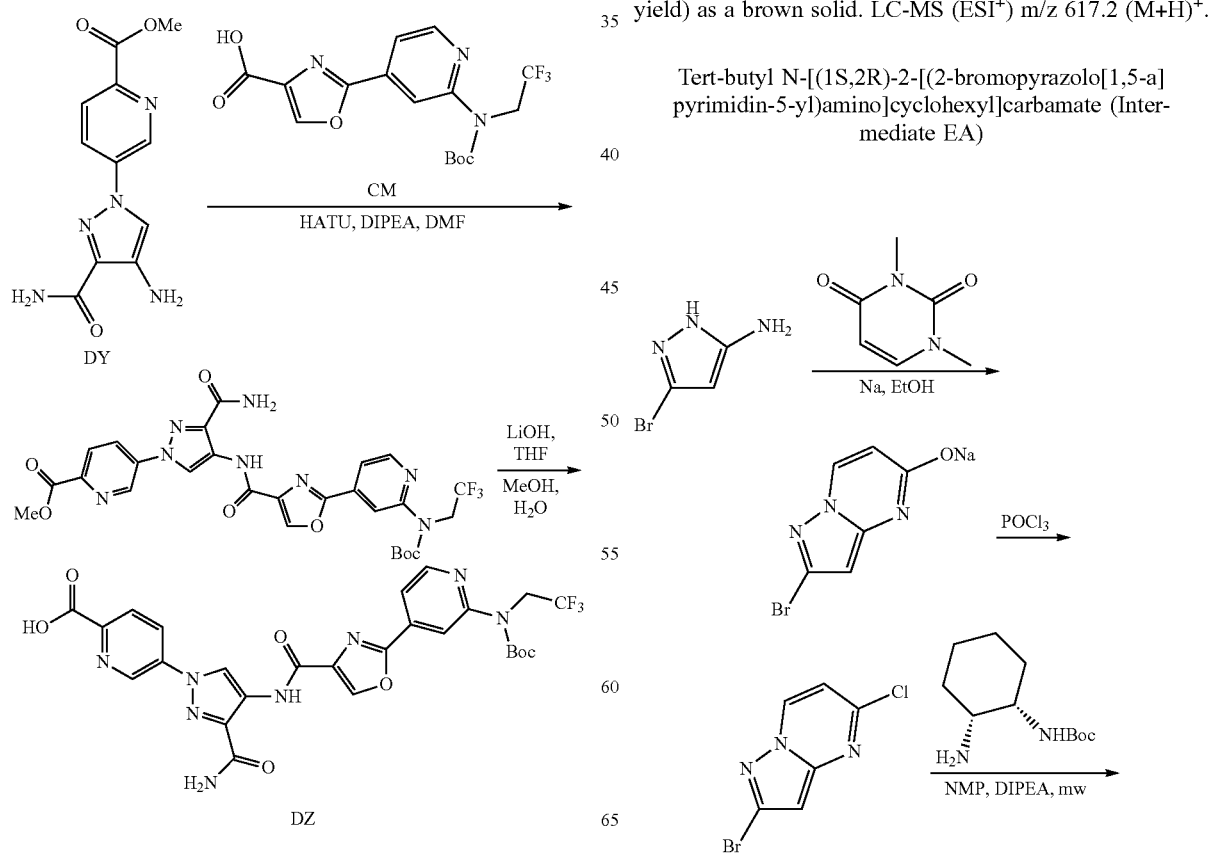

1277

-continued

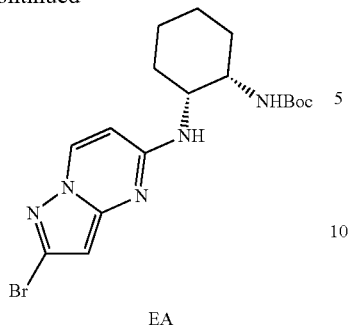

EA

Step 1—(2-Bromopyrazolo[1,5-a]pyrimidin-5-yl) oxysodium

To a solution of Na (7.10 g, 309 mmol) in EtOH (125 mL) was added 3-bromo-1H-pyrazol-5-amine (5.00 g, 30.9 mmol, CAS #1203705-55-8) and 1,3-dimethylpyrimidine-2,4-dione (4.33 g, 30.9 mmol, CAS #874-14-6). The reaction mixture was stirred at 80° C. for 3 hours. On completion, the mixture was cooled to 0-5° C., then filtered. The filter cake was washed with cold EtOH, and dried in vacuo to give the title compound (2.80 g, 38% yield) as a yellow solid. $^1$H NMR (400 MHz, D$_2$O) δ 8.02 (d, J=7.6 Hz, 1H), 5.98 (d, J=7.6 Hz, 1H), 5.85 (s, 1H).

Step 2—2-Bromo-5-chloro-pyrazolo[1,5-a]pyrimidine

A mixture of (2-bromopyrazolo[1,5-a]pyrimidin-5-yl) oxysodium (1.00 g, 4.24 mmol) in POCl$_3$ (10 mL) was stirred at 110° C. for 3 hours. On completion, the mixture was concentrated in vacuo. The residue was diluted with EA (20 mL), washed with NaHCO$_3$ (10 ml), and concentrated in vacuo. The residue was purified by silica gel chromatography to give the title compound (0.67 g, 68% yield) as a white solid. $^1$H NMR (400 MHz, CDCl$_3$) δ 8.51 (d, J=7.2 Hz, 1H), 6.84 (d, J=7.2 Hz, 1H), 6.69 (s, 1H).

Step 3—Tert-butyl N-[(1S,2R)-2-[(2-bromopyrazolo[1,5-a]pyrimidin-5-yl)amino]cyclohexyl]carbamate 2-bromo-5-chloro-pyrazolo[1,5-a]pyrimidine (620 mg, 2.67 mmol), tert-butyl N-[(1S,2R)-2-amino cyclohexyl]carbamate (686 mg, 3.20 mmol, CAS #184954-75-4) and DIPEA (379 mg, 2.93 mmol) were taken up into a microwave tube in NMP (6 mL). The sealed tube was heated at 130° C. for 3 hours under microwave. On completion, the mixture was concentrated in vacuo to remove the solvent. Then the residue was purified by silica gel chromatography to give the title compound (1.00 g, 91% yield) as a white solid. $^1$H NMR (400 MHz, CDCl$_3$) δ 8.08 (d, J=7.6 Hz, 1H), 6.10 (s, 1H), 5.98 (d, J=7.6 Hz, 1H), 5.76 (s, 1H), 4.94 (br s, 1H), 4.20-4.11 (m, 1H), 4.01-3.92 (m, 1H), 2.00-1.83 (m, 1H), 1.75-1.49 (m, 6H), 1.45 (s, 9H), 1.39-1.22 (m, 1H).

1278

Methyl 4-[3-(difluoromethyl)-4-(4,4,5,5-tetramethyl-1,3,2-dioxaborolan-2-yl)pyrazol-1-yl]benzoate (Intermediate EB)

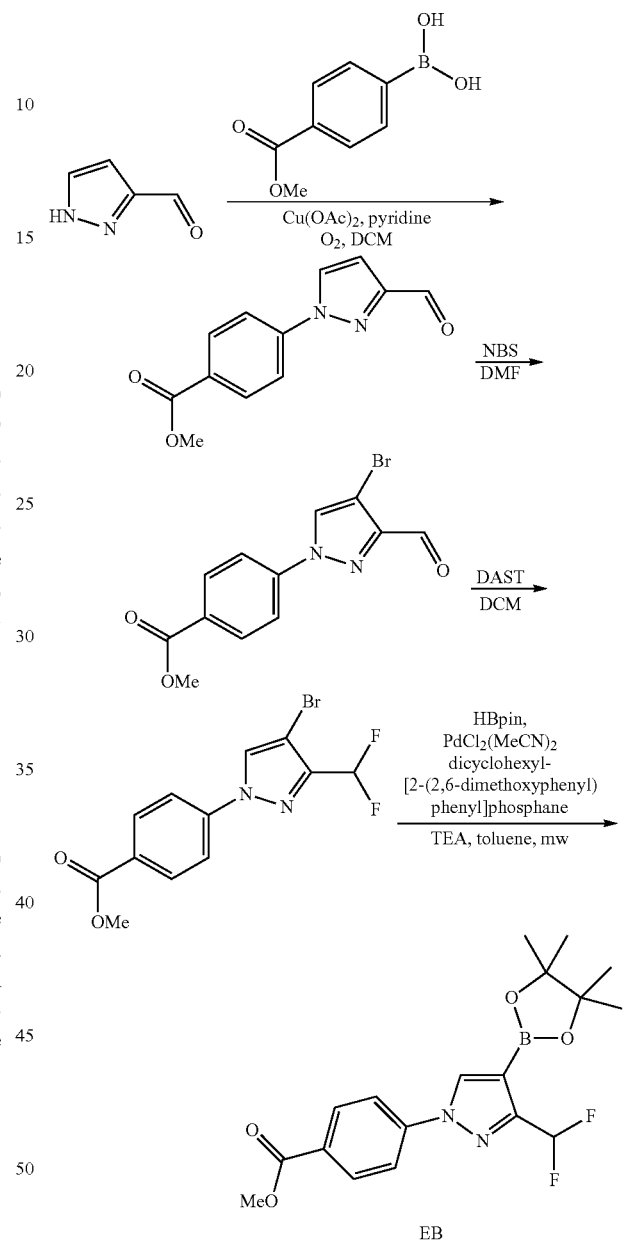

EB

Step 1—Methyl 4-(3-formyl-1H-pyrazol-1-yl)benzoate

To a solution of 1H-pyrazole-3-carbaldehyde (10.0 g, 104 mmol, CAS #3920-20-1) and (4-methoxy carbonyl-phenyl) boronic acid (22.5 g, 125 mmol, CAS #99768-12-4) in DCM (50 mL) was added Cu(OAc)$_2$ (22.7 g, 125 mmol) and pyridine (32.9 g, 416 mmol). The reaction mixture was stirred at rt for 18 hours under oxygen gas (balloon). On completion, the mixture was concentrated in vacuo. The residue was purified by silica gel chromatography to give the title compound (12.0 g, 50% yield) as a white solid. $^1$H NMR (400 MHz, CDCl$_3$) δ 10.10 (s, 1H), 8.24-8.14 (m, 2H), 8.06 (d, J=2.4 Hz, 1H), 7.90-7.82 (m, 2H), 7.02 (d, J=2.4 Hz, 1H), 3.95 (s, 3H).

Step 2—Methyl 4-(4-bromo-3-formyl-1H-pyrazol-1-yl)benzoate

To a solution of methyl 4-(3-formylpyrazol-1-yl)benzoate (4.00 g, 17.4 mmol) in DMF (40 mL) was added NBS (6.18 g, 34.8 mmol). The reaction mixture was stirred at rt for 1 hour. Then, the reaction mixture was heated to 50° C. and stirred for 12 hours. On completion, the mixture was concentrated in vacuo. The residue was purified by prep-HPLC (0.1% FA) to give the title compound (4.50 g, 82% yield) as a white solid. $^1$H NMR (400 MHz, CDCl$_3$) δ 10.02 (s, 1H), 8.12 (d, J=8.4 Hz, 2H) 8.04 (s, 1H), 7.75 (d, J=8.4 Hz, 2H), 3.89 (s, 3H); LC-MS (ESI$^+$) m/z 308.9, 310.9 (M+1)$^+$.

Step 3—Methyl 4-(4-bromo-3-(difluoromethyl)-1H-pyrazol-1-yl)benzoate

To a solution of methyl 4-(4-bromo-3-formyl-pyrazol-1-yl)benzoate (1.70 g, 5.50 mmol) in DCM (100 mL) was added DAST (7.98 g, 49.5 mmol) at 0° C. The reaction mixture was then allowed to warm to rt and stirred for 5 hours. On completion, the mixture was quenched with methanol (30 mL) at 0° C. then mixture was concentrated in vacuo. The residue was purified by prep-HPLC (0.1% HCl) to give the title compound (1.44 g, 78% yield) as a white solid. $^1$H NMR (400 MHz, CDCl$_3$) δ 8.17 (d, J=8.8 Hz, 2H), 8.07 (s, 1H), 7.76 (d, J=8.8 Hz, 2H), 6.80 (t, J=53.2 Hz, 1H), 3.96 (s, 3H); LC-MS (ESI$^+$) m/z 330.9 (M+H)$^+$.

Step 4—Methyl 4-[3-(difluoromethyl)-4-(4,4,5,5-tetramethyl-1,3,2-dioxaborolan-2-yl)pyrazol-1-yl] benzoate Methyl 4-[4-bromo-3-(difluoromethyl)pyrazol-1-yl]benzoate (500 mg, 1.51 mmol), TEA (382 mg, 3.78 mmol), acetonitrile-dichloropalladium (58.8 mg, 227 umol), dicyclohexyl-[2-(2,6-dimethoxy phenyl)phenyl]phosphane (93.0 mg, 227 umol) and HBPin (1.93 g, 15.1 mmol) were taken up into a microwave tube in toluene (10 mL). The sealed tube was heated at 90° C. for 60 minutes under microwave. On completion, the mixture was filtered and the filtrate was concentrated in vacuo. The residue was purified by silica gel chromatography to give the title compound (440 mg, 54% yield) as a yellow solid. LC-MS (ESI$^+$) m/z 379.2 (M+H)$^+$.

4-[4-[5-[[(1R,2S)-2-(tert-butoxycarbonylamino)cyclohexyl]amino]pyrazolo[1,5-a]pyrimidin-2-yl]-3-(difluoromethyl)pyrazol-1-yl]benzoic acid (Intermediate EC)

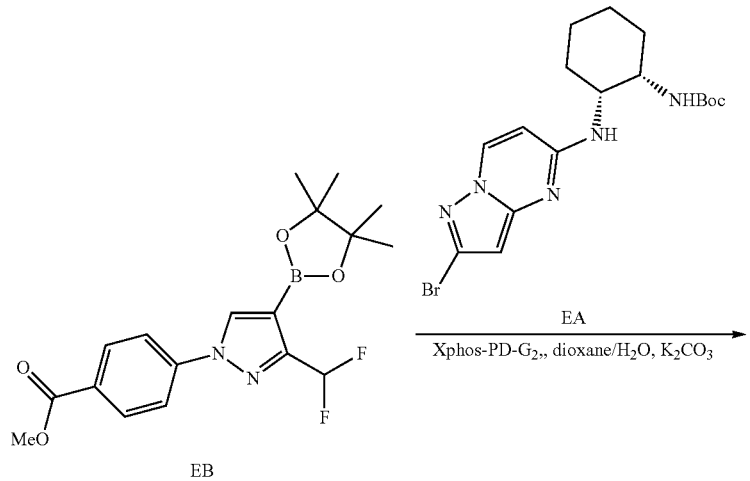

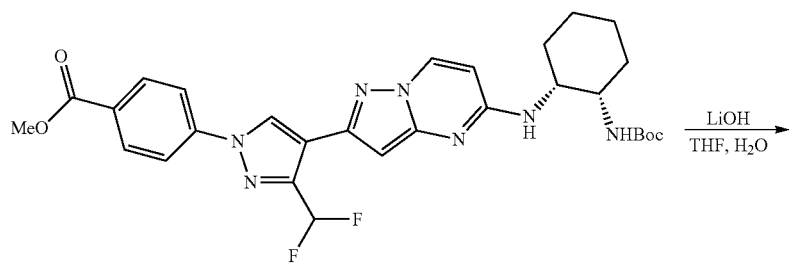

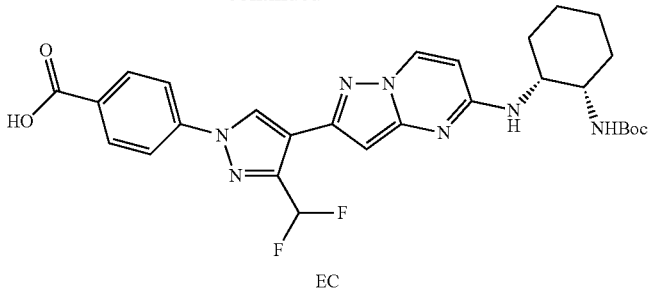

EC

Step 1—Methyl 4-[4-[5-[[(1R,2S)-2-(tert-butoxycarbonylamino)cyclohexyl]amino]pyrazolo[1,5-a]pyrimidin-2-yl]-3-(difluoromethyl)pyrazol-1-yl]benzoate To a solution of methyl 4-[3-(difluoromethyl)-4-(4,4,5,5-tetramethyl-1,3,2-dioxaborolan-2-yl)pyrazol-1-yl]benzoate (379 mg, 702 umol, Intermediate EB) and tert-butyl N-[(1S,2R)-2-[(2-bromopyrazolo[1,5-a]pyrimidin-5-yl)amino]cyclohexyl]carbamate (160 mg, 390 umol, Intermediate EA) in a mixed solvent of H$_2$O (0.6 mL) and dioxane (3 mL) was added K$_2$CO$_3$ (162 mg, 1.17 mmol) and XPHOS-PD-G$_2$ (30.7 mg, 39.0 umol). The reaction mixture was stirred at 90° C. for 17 hours. On completion, the mixture was concentrated in vacuo to remove the solvent dioxane. The residue was purified by reverse phase chromatography (0.1% HCl) to give the title compound (80.0 mg, 35% yield) as a yellow solid. LC-MS (ESI$^+$) m/z 582.1 (M+H)$^+$.

Step 2—4-[4-[5-[[(1R,2S)-2-(tert-butoxycarbonylamino)cyclohexyl]amino]pyrazolo[1,5-a]pyrimidin-2-yl]-3-(difluoromethyl)pyrazol-1-yl]benzoic acid To a solution of methyl 4-[4-[5-[[(1R,2S)-2-(tert-butoxycarbonylamino)cyclohexyl]amino]pyrazolo[1,5-a]pyrimidin-2-yl]-3-(difluoromethyl)pyrazol-1-yl]benzoate (80.0 mg, 138 umol) in a mixed solvent of THF (2 mL) and H$_2$O (0.4 mL) was added LiOH (16.5 mg, 688 umol). The reaction mixture was stirred at rt for 17 hours. On completion, the mixture was acidified with 1N HCl solution until the pH=6-7, then concentrated in vacuo to give the title compound (75.0 mg, 96% yield) as a yellow solid. LC-MS (ESI$^+$) m/z 568.3 (M+H)$^+$.

2-(4-Pyridyl)oxazole-4-carboxylic acid (Intermediate ED)

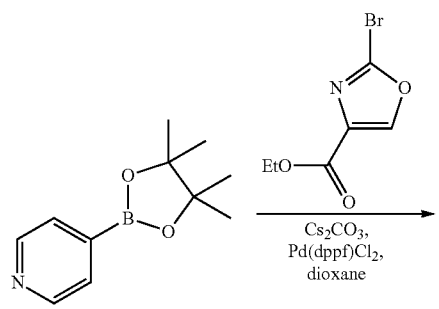

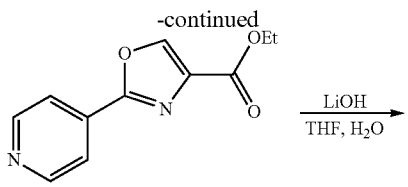

Step 1—Ethyl 2-(4-pyridyl)oxazole-4-carboxylate

To a solution of 4-(4,4,5,5-tetramethyl-1,3,2-dioxaborolan-2-yl)pyridine (1.50 g, 7.31 mmol) and ethyl 2-bromooxazole-4-carboxylate (1.61 g, 7.31 mmol, CAS #460081-20-3) in a mixed solvent of dioxane (20 mL) and H$_2$O (4 mL) was added Cs$_2$CO$_3$ (7.15 g, 21.9 mmol) and Pd(dppf)Cl$_2$ (267 mg, 365 umol) under nitrogen atmosphere. The reaction mixture was stirred at 80° C. for 16 hours. On completion, the reaction mixture was filtered and the filtrate was concentrated in vacuo to give a residue. The residue was purified by column chromatography (Petroleum ether/Ethyl acetate=1/1, PE/EA=1/1) to give the title compound (200 mg, 12% yield) as a yellow solid. $^1$H NMR (400 MHz, CDCl$_3$) δ 8.82-8.77 (m, 2H), 8.37 (s, 1H), 8.01-7.97 (m, 2H), 4.47 (q, J=7.2 Hz, 2H), 1.44 (t, J=7.2 Hz, 3H).

Step 2—2-(4-Pyridyl)oxazole-4-carboxylic acid

To a solution of ethyl 2-(4-pyridyl)oxazole-4-carboxylate (0.2 g, 916 umol) in THF (5 mL), MeOH (1 mL) and H$_2$O (1 mL) was added LiOH (26.34 mg, 1.10 mmol). The reaction mixture was stirred at rt for 12 hours. On completion, the mixture was concentrated in vacuo to give a residue. The residue was then diluted with H$_2$O and the aqueous phase was acidified with conc. HCl until the pH=6. The mixture was concentrated in vacuo to give the title compound (220 mg) as a yellow solid.

4-[3-Carbamoyl-4-[[2-(4-pyridyl)oxazole-4-carbonyl]amino]pyrazol-1-yl]benzoic acid (Intermediate EE)

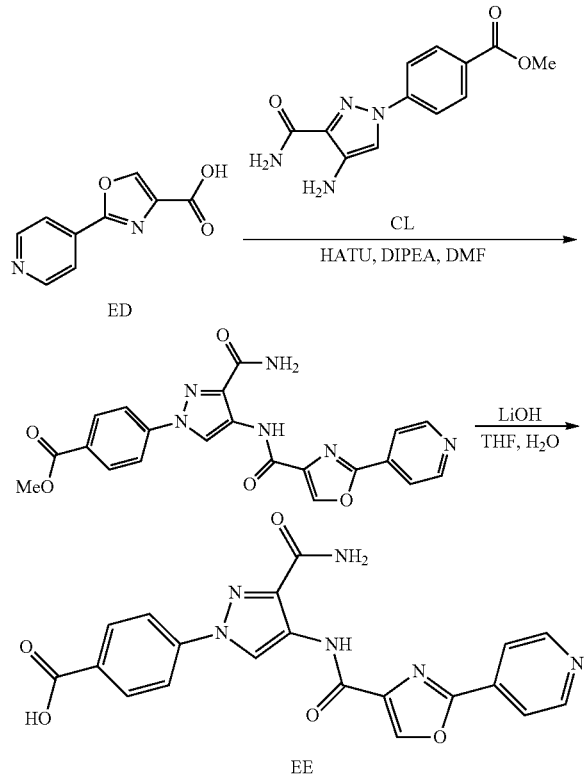

Step 1—Methyl 4-r[3-carbamoyl-4-[[2-(4-pyridyl)oxazole-4-carbonyl]amino]pyrazol-1-yl]benzoate To a solution of 2-(4-pyridyl)oxazole-4-carboxylic acid (200 mg, 1.05 mmol, Intermediate ED) and methyl 4-(4-amino-3-carbamoyl-pyrazol-1-yl)benzoate (328 mg, 1.26 mmol, Intermediate CL) in DMF (5 mL) was added DIPEA (679 mg, 5.26 mmol, 915 uL). The mixture was stirred at rt for 12 minutes, and then HATU (479 mg, 1.26 mmol) was added. The reaction mixture was stirred at rt for 12 hours. On completion, the mixture was diluted with H₂O (10 mL) and extracted with EA (2×20 mL). The combined organic layers were concentrated in vacuo to give the title compound (60.0 mg, 13% yield) as a brown solid. LC-MS (ESI⁺) m/z 433.2 (M+H)⁺.

Step 2—4-[3-Carbamoyl-4-[[2-(4-pyridyl)oxazole-4-carbonyl]amino]pyrazol-1-yl]benzoic acid To a solution of methyl 4-[3-carbamoyl-4-[[2-(4-pyridyl)oxazole-4-carbonyl]amino]pyrazol-1-yl]benzoate (60.0 mg, 138 umol) in THF (8 mL) and H₂O (2 mL) was added LiOH (4.99 mg, 208 umol). The reaction mixture was stirred at rt for 12 hours. On completion, the mixture was concentrated in vacuo to give a residue. The residue was then diluted with H₂O and the aqueous phase was acidified with conc. HCl until the pH=6. The reaction mixture was concentrated in vacuo to give a residue. The residue was purified by reverse phase chromatography (0.1% HCl) to give the title compound (25.0 mg, 43% yield) as a white solid. LC-MS (ESI⁺) m/z 419.1 (M+H)⁺.

Tert-butyl N-[3-(3-aminopropoxy)propyl]carbamate (Intermediate EF)

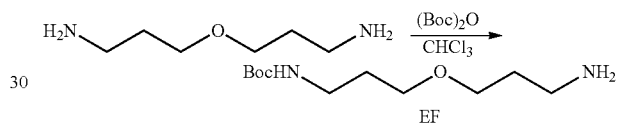

To a mixture of 3-(3-aminopropoxy)propan-1-amine (499 mg, 3.78 mmol, CAS #2157-24-6) in CHCl₃ (25 mL) was added a solution of tert-butoxycarbonyl tert-butyl carbonate (165 mg, 756 umol) in CHCl₃ (5 mL) dropwise. Then the reaction mixture was stirred at rt for 16 hours. On completion, the reaction mixture was concentrated in vacuo to give a residue. The residue was purified by column chromatography (DCM:MeOH=10:1) to give the title compound (140 mg, 79% yield) as a light yellow oil. ¹H NMR (400 MHz, CDCl₃) δ 4.87 (s, 1H), 3.42 (q, J=6.4 Hz, 4H), 3.15 (q, J=5.6 Hz, 2H), 2.76 (t, J=6.4 Hz, 2H), 1.70-1.63 (m, 4H), 1.37 (s, 9H).

4-(4-(2-(2-((Tert-butoxycarbonyl)(cyclopropylmethyl)amino)pyridin-4-yl)oxazole-4-carboxamido)-3-(trifluoromethyl)-1H-pyrazol-1-yl)benzoic acid (Intermediate EG)

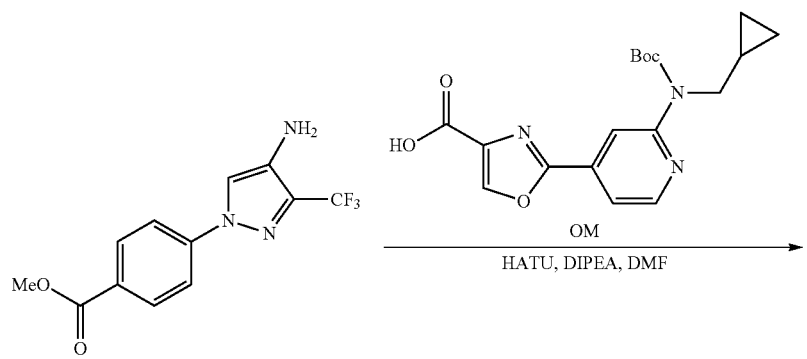

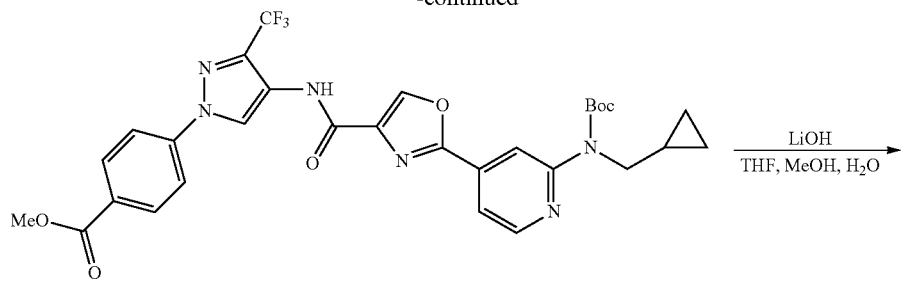

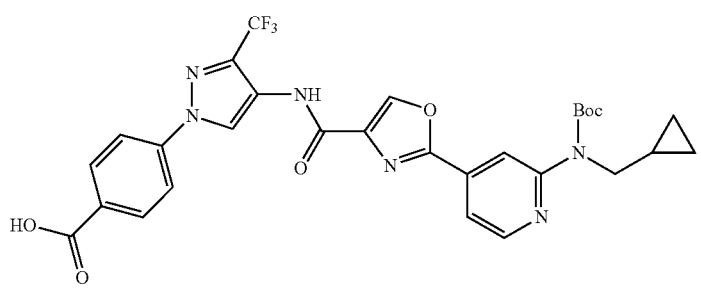

EG

Step 1—Methyl 4-(4-(2-(2-((tert-butoxycarbonyl)(cyclopropylmethyl)amino)pyridin-4-yl)oxazole-4-carboxamido)-3-(trifluoromethyl)-1H-pyrazol-1-yl)benzoate To a solution of methyl 4-[4-amino-3-(trifluoromethyl)pyrazol-1-yl]benzoate (300 mg, 1.05 mmol, synthesized via Steps 1-3 of Intermediate DE) and 2-[2-[tert-butoxycarbonyl(cyclopropylmethyl)amino]-4-pyridyl]oxazole-4-carboxylic acid (378 mg, 1.05 mmol, synthesized via Steps 1-4 of Intermediate DF) in DMF (5 mL) was added DIPEA (408 mg, 3.16 mmol). Then, HATU (478 mg, 1.26 mmol) was added and the reaction mixture was stirred at rt for 0.5 hour. On completion, the reaction mixture was quenched with water (20 mL) and filtered. The filtered cake was collected and dried in vacuo to give the title compound (659 mg, 100% yield) as a white solid. $^1$H NMR (400 MHz, CDCl$_3$) δ 9.09 (s, 1H), 8.99 (s, 1H), 8.55 (d, J=5.2 Hz, 1H), 8.44 (s, 1H), 8.38 (s, 1H), 8.21 (d, J=8.8 Hz, 2H), 7.89 (d, J=8.8 Hz, 2H), 7.65 (dd, J=1.2, 5.2 Hz, 1H), 4.01-3.95 (m, 5H), 1.60 (s, 9H), 1.30-1.20 (m, 1H), 0.50-0.43 (m, 2H), 0.30 (m, 2H); LC-MS (ESI$^+$) m/z 627.1 (M+H)$^+$.

Step 2—4-(4-(2-(2-((Tert-butoxycarbonyl)(cyclopropylmethyl)amino)pyridin-4-yl)oxazole-4-carboxamido)-3-(trifluoromethyl)-1H-pyrazol-1-yl)benzoic acid To a solution of methyl 4-[4-[[2-[2-[tert-butoxycarbonyl(cyclopropylmethyl)amino]-4-pyridyl]-oxazole-4-carbonyl]amino]-3-(trifluoromethyl)pyrazol-1-yl]benzoate (659 mg, 1.05 mmol) in a mixed of solvent THF (30 mL), H$_2$O (10 mL) and methanol (10 mL) was added LiOH (126 mg, 5.26 mmol). The reaction mixture was stirred at rt for 12 hours. On completion, the reaction mixture was concentrated in vacuo. The residue was diluted with water (20 mL) and acidified with 1N HCl until the pH=4, then the mixture was filtered. The filtered cake was collected and dried in vacuo to give the title compound (700 mg, 91% yield) as a white solid. LC-MS (ESI$^+$) m/z 613.0 (M+H)$^+$.

[3-[4-Amino-3-(trifluoromethyl)pyrazol-1-yl]phenyl]methanol (Intermediate EH)

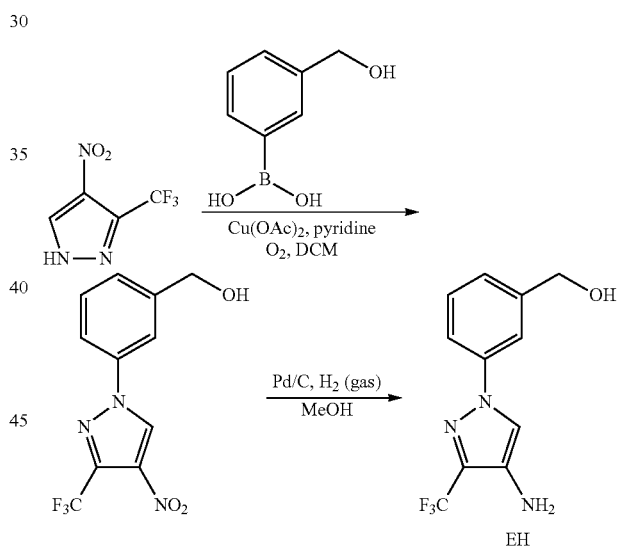

Step 1—[3-[4-Nitro-3-(trifluoromethyl)pyrazol-1-yl]phenyl]methanol

To a solution of 4-nitro-3-(trifluoromethyl)-1H-pyrazole (10.0 g, 55.2 mmol, synthesized via Step 1 of Intermediate DE) and [3-(hydroxymethyl) phenyl]boronic acid (12.9 g, 85.3 mmol) in DCM (200 mL) was added Cu(OAc)$_2$ (15.0 g, 82.8 mmol) and pyridine (17.4 g, 220 mmol). The mixture was stirred at rt for 16 hours under oxygen (15 psi pressure). On completion, the mixture was concentrated in vacuo. The mixture was purified by silica gel column (PE:EA=1:1) to give the title compound (8.00 g, 50% yield) as a white solid. $^1$H NMR (400 MHz, DMSO-d$_6$) δ 9.90 (s, 1H), 7.93 (s, 1H), 7.85 (d, J=8.0 Hz, 1H), 7.58 (t, J=7.6 Hz, 1H), 7.48 (d, J 7.6 Hz, 1H), 5.45 (t, J=6.0 Hz, 1H), 4.62 (d, J=6.0 Hz, 2H).

Step 2—[3-[4-Amino-3-(trifluoromethyl)pyrazol-1-yl]phenyl]methanol

To a solution of [3-[4-nitro-3-(trifluoromethyl)pyrazol-1-yl]phenyl]methanol (1.00 g, 3.48 mmol) in MeOH (20.0 mL) was added Pd/C (200 mg, 10 wt %) under hydrogen (15 psi pressure). The mixture was stirred at rt for 3 hours. On completion, the mixture was filtered and concentrated in vacuo. The mixture was purified by silica gel column (PE:EA=1:1) to give the title compound (700 mg, 78% yield) as a yellow oil. $^1$H NMR (400 MHz, CDCl$_3$) δ 7.60 (s, 1H), 7.47 (s, 1H), 7.45 (s, 1H), 7.36 (t, J=8.0 Hz, 1H), 7.24 (d, J=7.2 Hz, 1H), 4.70 (d, J=3.2 Hz, 2H), 3.28 (s, 2H), 1.76 (s, 1H).

Tert-butyl N-(cyclopropylmethyl)-N-[4-[4-[[1-[3-(hydroxymethyl)phenyl]-3-(trifluoromethyl) pyrazol-4-yl]carbamoyl]oxazol-2-yl]-2-pyridyl]carbamate (Intermediate EI)

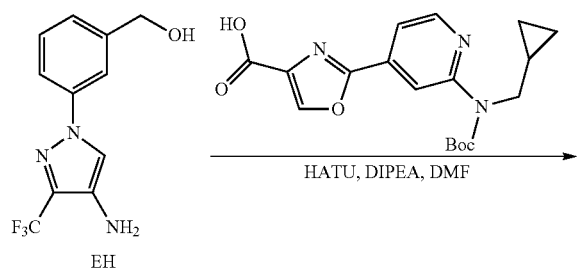

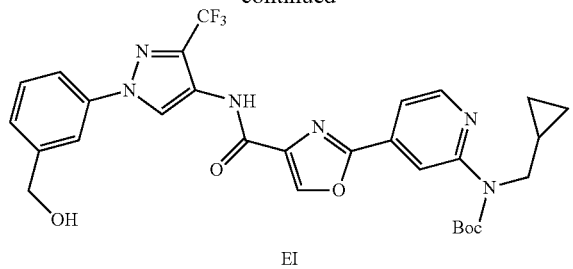

To a solution of [3-[4-amino-3-(trifluoromethyl)pyrazol-1-yl]phenyl]methanol (400 mg, 1.56 mmol, Intermediate EH) and 2-[2-[tertbutoxycarbonyl(cyclopropylmethyl)amino]-4-pyridyl]oxazole-4-carboxylic acid (558 mg, 1.56 mmol, Intermediate OM) in DMF (5.00 mL) was added HATU (709 mg, 1.87 mmol) and DIPEA (602 mg, 4.67 mmol). The mixture was stirred at rt for 30 minutes. On completion, the mixture was quenched with H$_2$O (1 mL) and concentrated in vacuo. The mixture was purified by reverse phase prep-HPLC (0.1% FA) to give the title compound (320 mg, 34% yield) as a white solid. $^1$H NMR (400 MHz, CDCl$_3$) δ 9.08 (s, 1H), 8.92 (s, 1H), 8.55 (d, J=5.2 Hz, 1H), 8.44 (s, 1H), 8.38 (s, 1H), 7.83 (s, 1H), 7.70 (d, J=8.0 Hz, 1H), 7.66 (dd, J=1.2, 5.2 Hz, 1H), 7.52 (t, J=7.6 Hz, 1H), 7.41 (d, J=7.6 Hz, 1H), 4.83 (d, J=5.2 Hz, 2H), 3.97 (d, J=7.2 Hz, 2H), 1.90-1.82 (m, 1H), 1.59 (s, 9H), 1.28-1.25 (m, 1H), 0.49-0.43 (m, 2H), 0.33-0.29 (m, 2H).

4-[2-[2-[2-(Aminomethyl)morpholin-4-yl]ethoxy]ethylamino]-2-(2,6-dioxo-3-piperidyl) isoindoline-1,3-dione (Intermediate EJ)

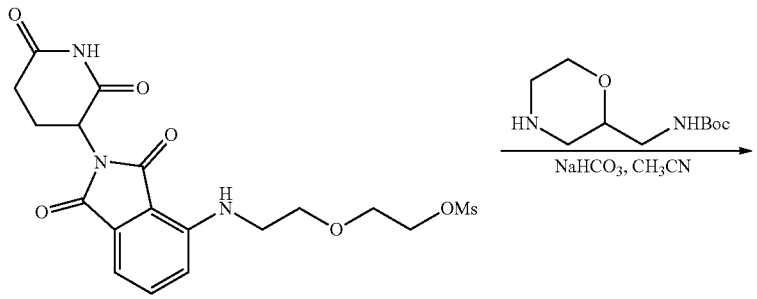

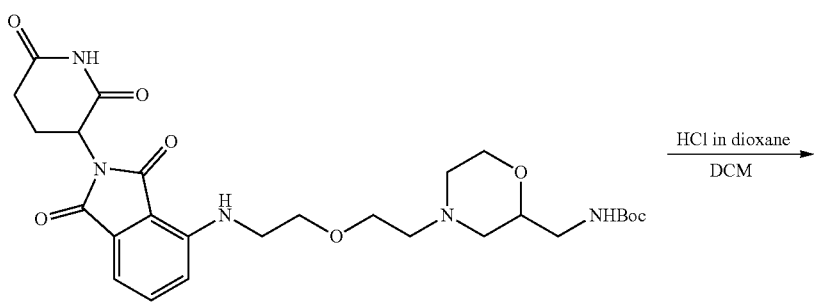

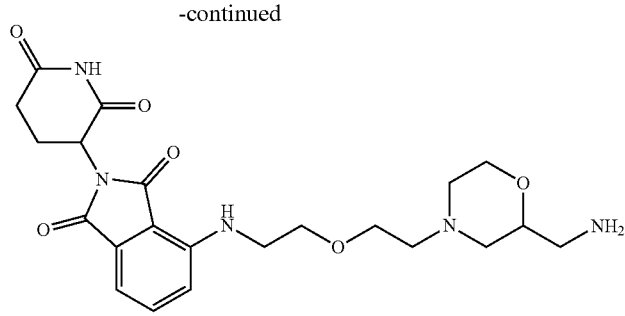

EJ

Step 1—Tert-butyl N-[[4-[2-[2-[[2-(2,6-dioxo-3-piperidyl)-1,3-dioxo-isoindolin-4-yl]amino]ethoxy]ethyl]morpholin-2-yl]methyl]carbamate To a solution of 2-[2-[[2-(2,6-dioxo-3-piperidyl)-1,3-dioxo-isoindolin-4-yl]amino]ethoxy]ethyl methanesulfonate (195 mg, 443 umol, synthesized via Steps 1-2 of Example 184) and tert-butyl N-(morpholin-2-ylmethyl)carbamate (287.92 mg, 1.33 mmol, CAS #173341-02-1) in CH$_3$CN (30 mL) was added NaHCO$_3$ (111 mg, 1.33 mmol, 51.7 uL). The mixture was stirred at 80° C. for 6 hours. On completion the mixture was concentrated and extracted with EA (3×30 mL). The combined organic layers were washed with brine (50 mL, dried over Na$_2$SO$_4$, filtered and concentrated in vacuo to give a residue. The mixture was purified by column chromatography (TLC; PE:EA 1:1) to give the title compound (100 mg, 35% yield) as a yellow oil. LC-MS (ESI$^+$) m/z 560.2 (M+H)$^+$.

Step 2—4-[2-[2-[2-(Aminomethyl)morpholin-4-yl]ethoxy]ethylamino]-2-(2,6-dioxo-3-piperidyl) isoindoline-1,3-dione To a solution of tert-butyl N-[[4-[2-[2-[[2-(2,6-dioxo-3-piperidyl)-1,3-dioxo-isoindolin-4-yl]amino]ethoxy]ethyl]morpholin-2-yl]methyl]carbamate (50.0 mg, 89.3 umol) in DCM (2 mL) was added HCl in dioxane (4 M, 1 mL). The mixture was stirred at rt for 0.5 hr. On completion, the mixture was concentrated in vacuo to give the title compound (44.3 mg, HCl salt, 90% yield) as a yellow oil. LC-MS (ESI$^+$) m/z 460.2 (M+H)$^+$.

Tert-butyl N-(5-oxopentyl)carbamate (Intermediate EK)

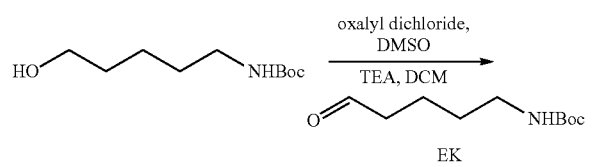

To a solution of oxalyl dichloride (312 mg, 2.46 mmol, 215 uL) in dichloromethane (5 mL) at −78° C. was added dimethyl sulfoxide (384 mg, 4.92 mmol, 384 uL) dissolved in dichloromethane (0.5 mL) dropwise, while keeping the temperature below −65° C. Five minutes later, tert-butyl N-(5-hydroxypentyl)carbamate (500 mg, 2.46 mmol, 500 uL, CAS #: 75178-90-4) dissolved in dichloromethane (0.5 mL) was added slowly to the solution and the mixture was stirred at −78° C. for 15 min. Finally, triethylamine (1.24 g, 12.3 mmol, 1.71 mL) was added dropwise and stirred the reaction was stirred for 15 min. The mixture was allowed to warm to rt and stirred for 1 hour. The reaction mixture was quenched with water (10 mL), and extracted with dichloromethane (3×5 mL). The combined organic layers were washed with brine (2×10 mL), dried over sodium sulfate, filtered and concentrated in vacuo to give title compound (450 mg, crude) as a brown oil. $^1$H NMR (400 MHz, DMSO-d$_6$) δ 6.76-6.60 (m, 1H), 4.96-4.74 (m, 1H), 3.13-3.02 (m, 1H), 2.00-1.93 (m, 2H), 1.76-1.68 (m, 2H), 1.43 (s, 9H), 1.20 (t, J=7.2 Hz, 1H).

4-[2-(5-Aminopentylamino)ethylamino]-2-(2,6-dioxo-3-piperidyl)isoindoline-1,3-dione (Intermediate EL)

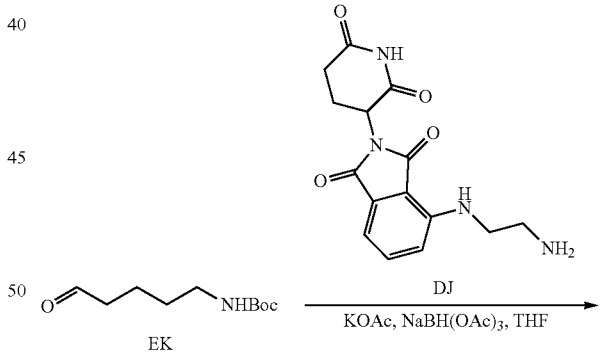

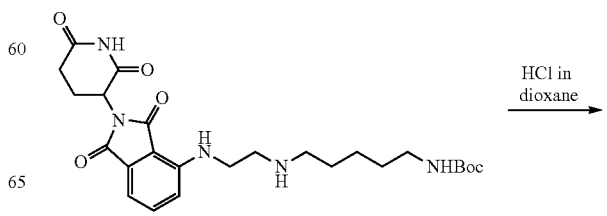

1291

-continued

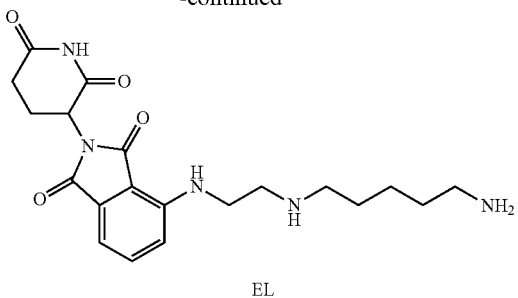

EL

Step 1—Tert-butyl N-[5-[2-[[2-(2,6-dioxo-3-piperidyl)-1,3-dioxo-isoindolin-4-yl]amino]ethylamino]pentyl]carbamate To a solution of 4-(2-aminoethylamino)-2-(2,6-dioxo-3-piperidyl)isoindoline-1,3-dione (100 mg, 283 umol, HCl, Intermediate DJ) and tert-butyl N-(5-oxopentyl)carbamate (68.5 mg, 340 umol, Intermediate EK) in THF (20 mL) was added KOAc (55.6 mg, 567 umol). The mixture was stirred at rt for 30 minutes, then NaBH(OAc)$_3$ (150 mg, 709 umol) was added in portions. The mixture was stirred at rt for 11.5 hours. The reaction mixture was quenched with water (1 mL) and concentrated in vacuo. The residue was purified by silica gel column chromatography (Petroleum ether/Ethyl acetate=5/1 to dichloromethane:methanol=10/1) to give title compound (60.0 mg, 39% yield) as a yellow oil. $^1$H NMR (400 MHz, DMSO-d$_6$) δ 11.11 (s, 1H), 9.07 (s, 2H), 7.65-7.60 (m, 1H), 7.31 (d, J=8.8 Hz, 1H), 7.10 (d, J=6.8 Hz, 1H), 6.87 (t, J=6.8 Hz, 1H), 5.08 (dd, J=5.2, 12.8 Hz, 1H), 3.77-3.67 (m, 2H), 3.14-3.04 (m, 2H), 2.97-2.85 (m, 3H), 2.81-2.72 (m, 2H), 2.64-2.56 (m, 2H), 2.10-1.98 (m, 1H), 1.68-1.61 (m, 2H), 1.59-1.53 (m, 2H), 1.45-1.34 (m, 2H).

Step 2—4-[2-(5-Aminopentylamino)ethylamino]-2-(2,6-dioxo-3-piperidyl)isoindoline-1,3-dione Tert-butyl N-[5-[2-[[2-(2,6-dioxo-3-piperidyl)-1,3-dioxo-isoindolin-4-yl]amino]ethyl amino]pentyl]carbamate (60.0 mg, 119 umol, HCl) was dissolved in 4 M HCl in dioxane (5 mL). The mixture was stirred at rt for 1 hour. The reaction mixture was then concentrated in vacuo to give title compound (60.0 mg, 95% yield) as a brown oil. $^1$H NMR (400 MHz, DMSO-d$_6$) δ 11.10 (s, 1H), 9.10 (s, 2H), 7.62 (t, J=7.6 Hz, 1H), 7.31 (d, J=8.4 Hz, 1H), 7.10 (d, J=7.2 Hz, 1H), 6.86 (s, 1H), 5.07 (dd, J=5.2, 12.4 Hz, 1H), 3.98-3.86 (m, 1H), 3.51-3.41 (m, 4H), 3.36-3.29 (m, 1H), 3.11-3.03 (m, 2H), 2.96-2.86 (m, 3H), 2.76-2.73 (m, 2H), 2.69-2.59 (m, 2H), 2.07-1.99 (m, 1H), 1.70-1.53 (m, 4H), 1.43-1.33 (m, 2H).

(2R)-2-hydroxy-3-[(8R)-1-(4-piperazin-1-ylcyclohexoxy)-7,8-dihydro-6H-cyclopenta[4,5]thieno[1,2-c]pyrimidin-8-yl]propanamide (Intermediate EM)

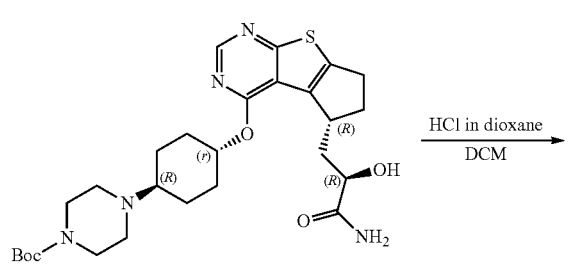

1292

-continued

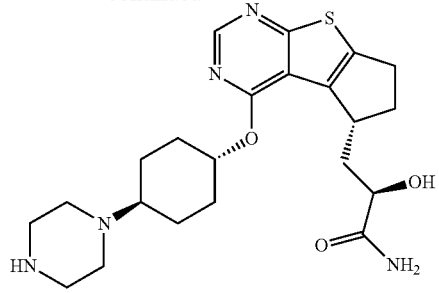

EM

To a mixture of tert-butyl 4-[4-[[(8R)-8-[(2R)-3-amino-2-hydroxy-3-oxo-propyl]-7,8-dihydro-6H-cyclopenta[4,5]thieno[1,2-c]pyrimidin-1-yl]oxy]cyclohexyl]piperazine-1-carboxylate (0.09 g, 164 umol, synthesized via Steps 1-14 of Intermediate DR) in DCM (2 mL) was added HCl in dioxane (4.0 M, 6.43 mL). Then the reaction mixture was stirred at rt for 20 minutes. On completion, the reaction mixture was concentrated in vacuo to give the title compound (79.5 mg, 100% yield) as white solid. LC-MS (ESI$^+$) m/z 446.1 (M+H)$^+$.

2,2-dimethyl-4-oxo-3,8,11,14,17-pentaoxa-5-azanonadecan-19-oic acid (Intermediate EN)

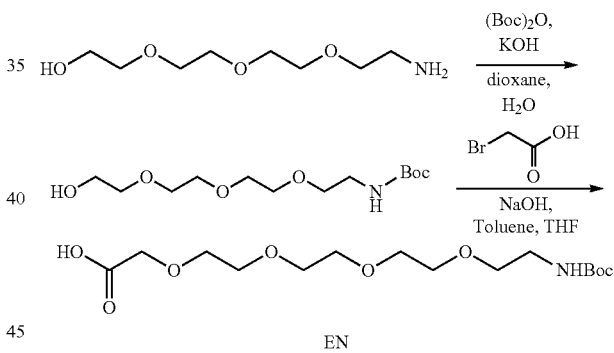

EN

Step 1—tert-butyl (2-(2-(2-(2-hydroxyethoxy)ethoxy)ethoxy)ethyl)carbamate

To a stirred solution of 2-(2-(2-(2-aminoethoxy)ethoxy)ethoxy)ethan-1-ol (1.0 g, 5.2 mmol, CAS #86770-74-3) and KOH (0.32 g, 5.6 mmol) in 1,4 dioxane (4 mL) and water (8 mL) was added Boc-anhydride (1.24 g, 5.6 mmol) dropwise at 10° C. The resulting reaction mixture was allowed to warm to rt and stirred for 16 h. The reaction mixture was transferred into ice water and the resulting mixture was extracted using ethyl acetate (3×100 mL). The combined organic layers were dried over anhydrous sodium sulfate and filtered. The filtrate was evaporated under reduced pressure to afford crude product. The crude product was purified using silica gel column chromatography (8% MeOH-DCM) to give tert-butyl (2-(2-(2-(2-hydroxyethoxy)ethoxy)ethoxy)ethyl)carbamate as a colorless oil (1.2 g, 79%). LC-MS (ESI$^+$) m/z 293.13 (M+H)$^+$.

Step 2—2,2-dimethyl-4-oxo-3,8,11,14,17-pentaoxa-5-azanonadecan-19-oic acid

To a stirred solution of tert-butyl (2-(2-(2-(2-hydroxyethoxy)ethoxy)ethoxy)ethyl)carbamate (0.38 g, 1.29 mmol) and 2-bromoacetic acid (0.54 g, 3.8 mmol) in toluene:THF (1:1, 4 mL) was added NaOH (0.31 g, 7.7 mmol) at 45° C. The resulting reaction mixture stirred at 45° C. for 16 h. The reaction mixture was then evaporated, water (10 mL) was added and aqueous layer was acidified with 1 N HCl solution. The resulting mixture was extracted using DCM (3×50 mL) and the combined organic layer was dried over anhydrous sodium sulfate and filtered. The filtrate was evaporated under reduced pressure to give 2,2-dimethyl-4-oxo-3,8,11,14,17-pentaoxa-5-azanonadecan-19-oic acid as a colorless oil (0.24 g, 53%). LC-MS (ESI$^+$) m/z 351.4 (M+H)$^+$.

6-((1,6-naphthyridin-2-yl)amino)-4-(cyclopropylamino)-N-(piperidin-4-yl)nicotinamide hydrochloride (Intermediate EO)

Step 1—tert-butyl 4-(6-((1,6-naphthyridin-2-yl)amino)-4-(cyclopropylamino)nicotinamido)piperidine-1-carboxylate A solution of 6-((1,6-naphthyridin-2-yl)amino)-4-(cyclopropylamino)nicotinic acid (0.5 g, 1.56 mmol, Intermediate N), tert-butyl 4-aminopiperidine-1-carboxylate (0.32 g, 1.56 mmol, CAS #87120-72-7), PyBOP (1.22 g, 2.34 mmol) and DIPEA (0.4 mL, 2.34 mmol) in DMF (3 mL) was stirred at rt for 2 h. On completion, the reaction mixture was transferred into ice water and the resulting mixture was extracted using ethyl acetate (3×30 mL). The combined organic layers were dried over anhydrous sodium sulfate and filtered. The filtrate was evaporated under reduced pressure to afford crude product. The crude product was purified using silica gel column chromatography (5% MeOH-DCM) to give tert-butyl 4-(6-((1,6-naphthyridin-2-yl)amino)-4-(cyclopropylamino)nicotinamido)piperidine-1-carboxylate as a yellow solid (0.6 g, 76%). LC-MS (ESI$^+$) m/z 504.50 (M+H)$^+$.

Step 2—6-((1,6-naphthyridin-2-yl)amino)-4-(cyclopropylamino)-N-(piperidin-4-yl)nicotinamide hydrochloride To the solution tert-butyl 4-(6-((1,6-naphthyridin-2-yl)amino)-4-(cyclopropylamino)nicotinamido)piperidine-1-carboxylate (0.6 g, 1.19 mmol) in DCM (10 mL) was added 4N HCl in dioxane (3 mL) at 0° C. Then the reaction mixture was allowed to warm to rt and stirred for 3 h. The reaction mixture was evaporated under reduced pressure to afford the crude product. The crude product was triturated using MTBE to give 6-((1,6-naphthyridin-2-yl)amino)-4-(cyclopropylamino)-N-(piperidin-4-yl)nicotinamide hydrochloride as a white solid (0.45 g, 85%). LC-MS (ESI$^+$) m/z 404.40 (M+H)$^+$.

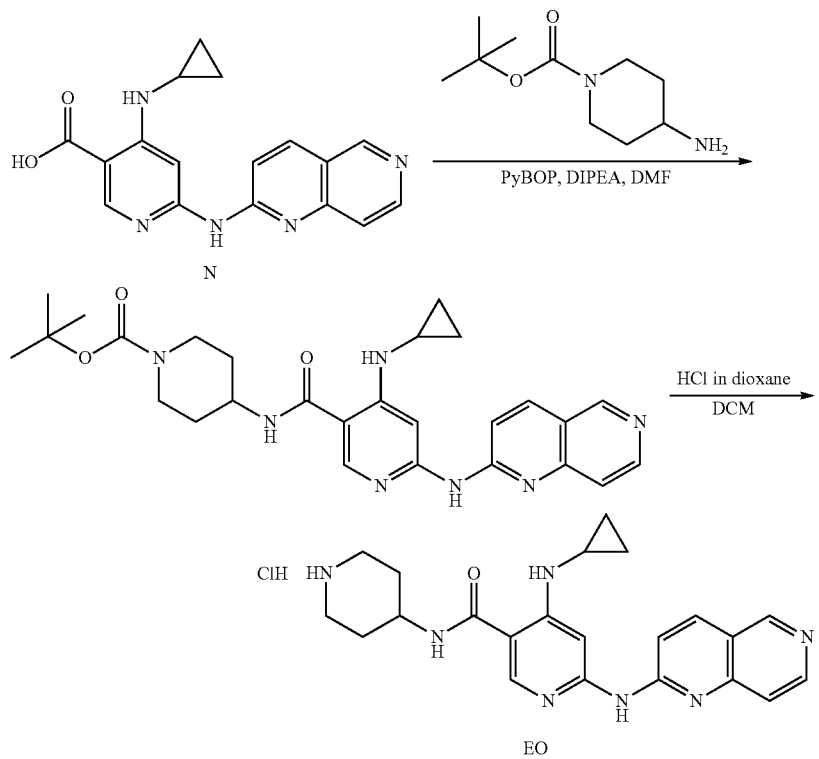

tert-butyl (2-(2-(2-aminoethoxy)ethoxy)ethyl)(methyl)carbamate (Intermediate EP)

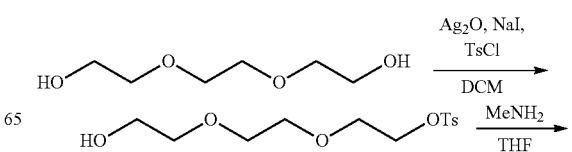

-continued

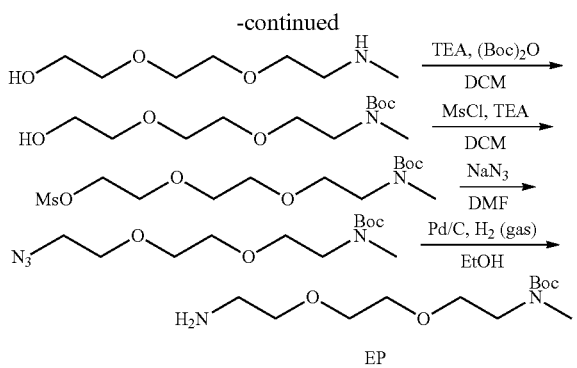

EP

Step 1—2-(2-(2-hydroxyethoxy)ethoxy)ethyl 4-methylbenzenesulfonate

To a stirred solution of 2,2'-(ethane-1,2-diylbis(oxy))bis (ethan-1-ol) (15.0 g, 0.10 mmol, CAS #112-27-6), silver oxide (34.65 g, 34.65 mmol), and sodium iodide (16.5 g, 1.1 mmol) in DCM (200 mL) was added tosyl chloride (19.06 g, 0.10 mmol) portion-wise at 0° C., and the reaction mixture was stirred for 3 h. On completion, the reaction mixture was filtered through a pad of celite and the filtrate was extracted using DCM (3×20 mL). The combined organic layer was washed with water, dried over anhydrous sodium sulfate and filtered. The filtrate was evaporated under reduced pressure to get the crude product. The crude product was purified using silica gel column chromatography (3% MeOH:DCM) to give 2-(2-(2-hydroxyethoxy)ethoxy)ethyl 4-methylbenzenesulfonate as a yellow liquid (18 g, 59%). LC-MS (ESI$^+$) m/z 305.34 (M+H)$^+$.

Step 2—2-(2-(2-(methylamino)ethoxy)ethoxy)ethan-1-ol

To a stirred solution of 2-(2-(2-hydroxyethoxy)ethoxy) ethyl 4-methylbenzenesulfonate (5.0 g, 16.4 mmol) in THF (15 mL) was added 2M Methylamine in THF (34 mL, 66 mmol) at rt, then the reaction mixture was heated to 90° C. and stirred for 8 h. The reaction mixture was then filtered and filtrate was evaporated under reduce pressure to give 2-(2-(2-(methylamino)ethoxy)ethoxy)ethan-1-ol as a yellow oil (2.5 g, 93% yield). LC-MS (ESI$^+$) m/z 164.21 (M+H)$^+$.

Step 3—tert-butyl (2-(2-(2-hydroxyethoxy)ethoxy) ethyl)(methyl)carbamate

To a stirred solution of 2-(2-(2-(methylamino)ethoxy) ethoxy)ethan-1l-ol (2.5 g, 15.3 mmol) in DCM (40 mL) was added boc anhydride (20 g, 92 mmol) and TEA (4.0 mL, 30.6 mmol) at 0° C. and the reaction mixture was stirred for 2 h. The reaction mixture was then transferred into ice water and the resulting mixture was extracted with DCM (3×100 mL). The combined organic layer was dried over anhydrous sodium sulfate and filtered. The filtrate was evaporated under reduced pressure to afford crude product. The crude product was purified using silica gel column chromatography (40% EtOAc-Hexane) to give tert-butyl (2-(2-(2-hydroxyethoxy)ethoxy)ethyl)(methyl)carbamate as a yellow semisolid (2.2 g, 54%). LC-MS (ESI$^+$) m/z 264.32 (M+H)$^+$.

Step 4—2,2,5-trimethyl-4-oxo-3,8,11-trioxa-5-azatridecan-13-yl methanesulfonate To a stirred solution of tert-butyl(2-(2-(2-hydroxyethoxy) ethoxy)ethyl)(methyl)carbamate (2.2 g, 8.4 mmol) and tri- ethylamine (3.5 g, 25.08 mmol) in DCM (15 mL) was added mesyl chloride (1.2 mL, 12.54 mmol) at 0° C., then the reaction mixture was stirred for 2 h. The reaction mixture was then transferred into ice water and the resulting mixture was extracted with DCM (3×25 mL). The combined organic layer was dried over anhydrous sodium sulfate and filtered. The filtrate was evaporated under reduced pressure to give 2,2,5-trimethyl-4-oxo-3,8,11-trioxa-5-azatridecan-13-yl methanesulfonate as a yellow semisolid (2.8 g, 78%).

Step 5—tert-butyl (2-(2-(2-azidoethoxy)ethoxy) ethyl)(methyl)carbamate

To a stirred solution of 2,2,5-trimethyl-4-oxo-3,8,11-tri- oxa-5-azatridecan-13-yl methanesulfonate (2.8 g, 8.2 mmol) in DMF (10 mL) was added sodium azide (0.8 g, 12.3 mmol) at rt. Then the reaction mixture was heated to 60° C. and stirred for 3 h. The reaction mixture was then transferred into ice water and the resulting mixture was extracted with ethyl acetate (3×100 mL). The combined organic layer was dried over anhydrous sodium sulfate and filtered. The filtrate was evaporated under reduced pressure to afford crude product. The crude product was purified using silica gel column chromatography (30% EtOAc-Hexane) to give tert-butyl (2-(2-(2-azidoethoxy)ethoxy)ethyl)(methyl)carbamate as a yellow semisolid (1.6 g, 98%). LC-MS (ESI$^+$) m/z 355.33 (M+FA adduct)$^+$.

Step 6—tert-butyl (2-(2-(2-aminoethoxy)ethoxy) ethyl)(methyl)carbamate

To a stirred solution of tert-butyl(2-(2-(2-azidoethoxy) ethoxy)ethyl)(methyl)carbamate (1.6 g, 5.6 mmol) in EtOH (15 mL) in an autoclave was added 10% Pd/C (50% wet) (1.6 g) under hydrogen gas (5 kg/cm$^2$ pressure) at rt for 3 h. The reaction mixture was filtered through celite and concentrated under reduced pressure to give tert-butyl (2-(2-(2-aminoethoxy)ethoxy)ethyl)(methyl)carbamate a as colorless oil (1 g, 68% yield). LC-MS (ESI$^+$) m/z 263.32 (M+H)$^+$

2-(2-(benzyloxy)ethoxy)ethyl methanesulfonate (Intermediate EQ)

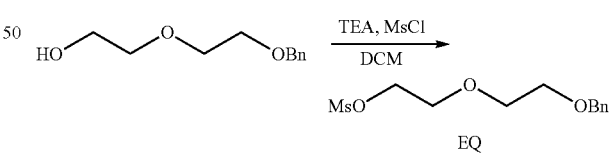

EQ

To a stirred solution of 2-(2-(benzyloxy)ethoxy)ethan-1-ol (0.5 g, 2.5 mmol, CAS #2050-25-1) and TEA (1.1 mL, 7.6 mmol) in DCM (10 mL) was added mesyl chloride (0.3 mL, 3.8 mmol) dropwise at 0° C. The resulting reaction mixture stirred at 0° C. for 2 h. The reaction mixture was transferred into ice water and the resulting mixture was extracted with DCM (3×50 mL). The combined organic layer was dried over anhydrous sodium sulfate and filtered. The filtrate was evaporated under reduced pressure to give 2-(2-(benzyloxy) ethoxy)ethyl methanesulfonate as a colorless oil (0.45 g, 64%).

tert-butyl (2-(2-aminoethoxy)ethyl)(2,2-dimethyl-4-oxo-3,8,11-trioxa-5-azatridecan-13-yl)carbamate
(Intermediate ER)

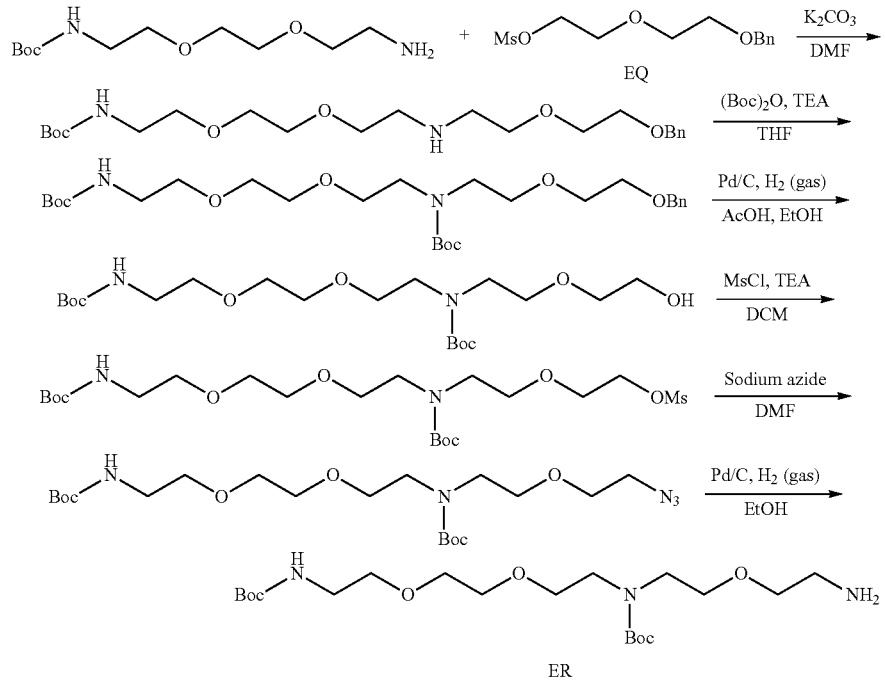

Step 1—tert-butyl (1-phenyl-2,5,11,14-tetraoxa-8-azahexadecan-16-yl)carbamate To a stirred solution of tert-butyl (2-(2-(2-aminoethoxy)ethoxy)ethyl)carbamate (3.0 g, 12.1 mmol, CAS #153086-78-3, Supplier: Chem-Impex) and 2-(2-(benzyloxy)ethoxy)ethyl methanesulfonate (5.0 g, 18.2 mmol, Intermediate EQ) in DMF (45 mL) was added $K_2CO_3$ (5 g, 36.2 mmol) at rt. The resulting reaction mixture heated to 80° C. and stirred for 5 h. The reaction mixture was transferred into ice water and the resulting mixture was extracted using ethyl acetate (3×100 mL). The combined organic layer was dried over anhydrous sodium sulfate and filtered. The filtrate was evaporated under reduced pressure to afford crude product. The crude product was purified using silica gel column chromatography (5% MeOH-DCM) to give tert-butyl (1-phenyl-2,5,11,14-tetraoxa-8-azahexadecan-16-yl)carbamate as a yellow oil (2.4 g, 47%). LCMS (ESI$^+$) m/z 426.55 (M+H)$^+$.

Step 2—tert-butyl (2-(2-(benzyloxy)ethoxy)ethyl)(2,2-dimethyl-4-oxo-3,8,11-trioxa-5-azatridecan-13-yl)carbamate To a stirred solution of tert-butyl (1-phenyl-2,5,11,14-tetraoxa-8-azahexadecan-16-yl)carbamate (2.4 g, 5.6 mmol) and TEA (1.6 mL, 11.2 mmol) in THF (40 mL) was added Boc anhydride (1.47 g, 6.7 mmol) dropwise at 0° C. The resulting reaction mixture stirred at rt for 1 h. The reaction mixture was transferred into ice water and the resulting mixture was extracted using ethyl acetate (3×50 mL). The combined organic layer was dried over anhydrous sodium sulfate and filtered. The filtrate was evaporated under reduced pressure to give tert-butyl (2-(2-(benzyloxy)ethoxy)ethyl)(2,2-dimethyl-4-oxo-3,8,8,11-trioxa-5-azatridecan-13-yl)carbamate as a colorless oil (2.9 g, 98%). LCMS (ESI$^+$) m/z 526.67 (M+H)$^+$.

Step 3—tert-butyl (2,2-dimethyl-4-oxo-3,8,11-trioxa-5-azatridecan-13-yl)(2-(2-hydroxyethoxy)ethyl)carbamate To a stirred solution of tert-butyl (2-(2-(benzyloxy)ethoxy)ethyl)(2,2-dimethyl-4-oxo-3,8,11-trioxa-5-azatridecan-13-yl)carbamate (3.2 g, 6.1 mmol) in ethanol (60 mL) and acetic acid (0.1 mL) in autoclave was added 10% Pd/C (50% wet) (3.2 g) at rt under nitrogen atmosphere. The resulting reaction mixture stirred under hydrogen gas (2 kg/cm$^2$ pressure) in autoclave at rt for 4 h. The reaction mixture was filtered through a pad of celite and washed with MeOH (50 mL). The filtrate was evaporated under reduced pressure to give tert-butyl (2,2-dimethyl-4-oxo-3,8,11-trioxa-5-azatridecan-13-yl)(2-(2-hydroxyethoxy)ethyl)carbamate as a yellow oil (2.4 g, 81%). LC-MS (ESI$^+$) m/z 436.55 (M+H)$^+$.

Step 4—14-(tert-butoxycarbonyl)-2,2-dimethyl-4-oxo-3,8,11,17-tetraoxa-5,14-diazanonadecan-19-yl methanesulfonate To a stirred solution of tert-butyl (2,2-dimethyl-4-oxo-3,8,11-trioxa-5-azatridecan-13-yl)(2-(2-hydroxyethoxy)ethyl)carbamate (2.2 g, 5.0 mmol) and TEA (2.1 mL, 15.1 mmol) in dichloromethane (50 mL) was added mesyl chloride (0.6 mL, 7.7 mmol) dropwise at 0° C. The resulting reaction mixture allowed to warm to rt and stirred for 4 h. The reaction mixture was transferred into ice water and the resulting mixture was extracted with DCM (3×100 mL). The combined organic layer was dried over anhydrous sodium sulfate and filtered. The filtrate was evaporated under reduced pressure to give 14-(tert-butoxycarbonyl)-2,2-dimethyl-4-oxo-3,8,11,17-tetraoxa-5,14-diazanonadecan-19-yl methanesulfonate as a brown oil (2.5 g, 96%). LCMS (ESI⁺) m/z 514.63 (M+H)⁺.

Step 5—tert-butyl (2-(2-azidoethoxy)ethyl)(2,2-dimethyl-4-oxo-3,8,11-trioxa-5-azatridecan-13-yl) carbamate To a stirred solution of 14-(tert-butoxycarbonyl)-2,2-dimethyl-4-oxo-3,8,11,17-tetraoxa-5,14-diazanonadecan-19-yl methanesulfonate (2.5 g, 4.8 mmol) in DMF (25 mL) was added sodium azide (0.48 g, 7.2 mmol) at rt. The resulting reaction mixture was heated to 65° C. and stirred for 4 h. The reaction mixture was transferred into ice water and the resulting mixture was extracted with ethyl acetate (3×100 mL). The combined organic layer was dried over anhydrous sodium sulfate and filtered. The filtrate was evaporated under reduced pressure to afford crude product. The crude product was purified using silica gel column chromatography (1% MeOH-DCM) to give tert-butyl (2-(2-azidoethoxy) ethyl)(2,2-dimethyl-4-oxo-3,8,11-trioxa-5-azatridecan-13-yl)carbamate as a yellow liquid (2 g, 89%). LCMS (ESI⁺) m/z 461.56 (M+H)⁺.

Step 6—tert-butyl (2-(2-aminoethoxy)ethyl)(2,2-dimethyl-4-oxo-3,8,11-trioxa-5-azatridecan-13-yl) carbamate To a stirred solution of tert-butyl (2-(2-azidoethoxy)ethyl) (2,2-dimethyl-4-oxo-3,8,11-trioxa-5-azatridecan-13-yl)carbamate (1.8 g, 3.9 mmol) in ethanol (100 mL) was added 10% Pd/C (50% wet) (1.8 g) at rt under nitrogen atmosphere. The resulting reaction mixture was stirred under hydrogen gas (2 kg/cm² pressure) in an autoclave at rt for 4 h. The reaction mixture was filtered through a pad of celite and washed with MeOH (50 mL). The filtrate was evaporated under reduced pressure to give tert-butyl (2-(2-aminoethoxy)ethyl)(2,2-dimethyl-4-oxo-3,8,11-trioxa-5-azatridecan-13-yl)carbamate as a colorless oil (1.4 g, 82%). LC-MS (ESI⁺) m/z 435.56 (M+H)⁺.

Tert-butyl ((1R,3R)-3-(16-amino-2,5,8,11,14-pentaoxahexadecyl)cyclobutyl)carbamate (Intermediate ES)

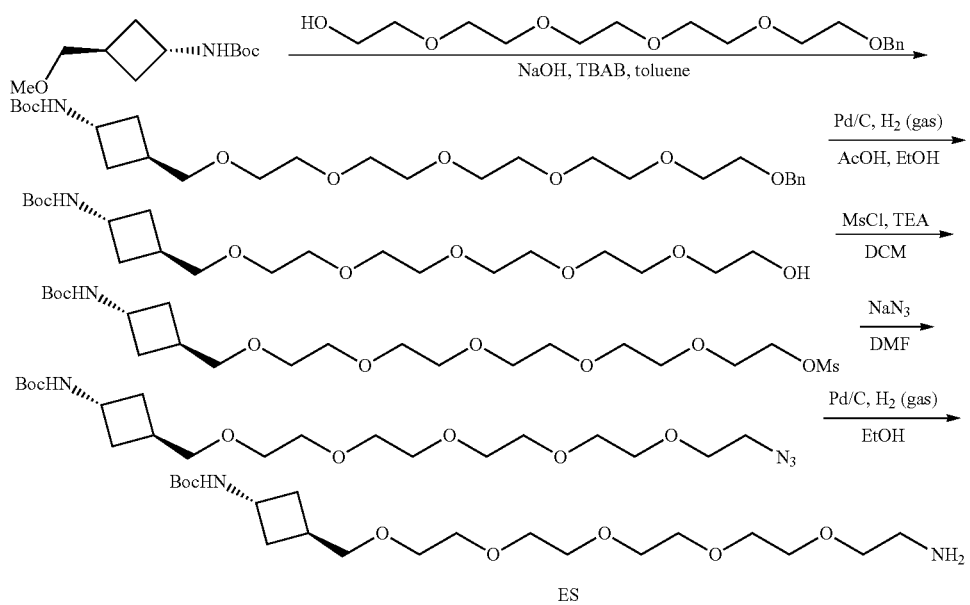

Step 1—tert-butyl ((1R,3R)-3-(18-phenyl-2,5,8,11,14,17-hexaoxaoctadecyl)cyclobutyl) carbamate To a stirred solution of ((1R,3R)-3-((tert-butoxycarbonyl) amino)cyclobutyl)methyl methanesulfonate (2.9 g, 10.4 mmol, synthesized via Steps 1-3 of Intermediate H) and 1-phenyl-2,5,8,11,14-pentaoxahexadecan-16-ol (6.8 g, 20.78 mmol, synthesized via Step 1 of Intermediate X) in toluene (30 mL) and 8 N NaOH solution (30 mL) was added TBAB (500 mg, 2.1 mmol) at rt. The resulting reaction mixture then heated to 90° C. and stirred for 16 h. The reaction mixture was then transferred into ice water and the resulting mixture was extracted with ethyl acetate (3×100 mL). The combined organic layer was dried over anhydrous sodium sulfate and filtered. The filtrate was evaporated under reduced pressure to afford crude product. The crude product was purified using silica gel column chromatography (1% MeOH-DCM) to give tert-butyl ((1R,3R)-3-(18-phenyl-2,5,8,11,14,17-hexaoxaoctadecyl)cyclobutyl)carbamate as a colorless oil (2.4 g, 46%). LCMS (ESI⁺) m/z 511.66 (M+H₂O)⁺.

Step 2—tert-butyl ((1R,3R)-3-(16-hydroxy-2,5,8,11,14-pentaoxahexadecyl)cyclobutyl)carbamate To a stirred solution of tert-butyl ((1r,3r)-3-(18-phenyl-2,5,8,11,14,17-hexaoxaoctadecyl)cyclobutyl) carbamate (3.15 g, 6.16 mmol) in ethanol (40 mL) and acetic acid (0.3 mL) was added 10% Pd/C (50% wet) (3.15 g) at rt under nitrogen atmosphere. The resulting reaction mixture was stirred under hydrogen gas (2 kg/cm² pressure) in autoclave at rt for 4 h. The reaction mixture was filtered through a pad of celite and washed with MeOH (50 mL). The filtrate was evaporated under reduced pressure to give tert-butyl ((1R,3R)-3-(16-hydroxy-2,5,8,11,14-pentaoxahexadecyl)cyclobutyl) carbamate as a brown oil (2.1 g, 81%). LC-MS (ESI⁺) m/z 421.53 (M+H)⁺.

Step 3—1-((1R,3R)-3-((tert-butoxycarbonyl)amino)cyclobutyl)-2,5,8,11,14-pentaoxahexadecan-16-yl methanesulfonate To a stirred solution of tert-butyl ((1R,3R)-3-(16-hydroxy-2,5,8,11,14-pentaoxahexadecyl)cyclobutyl) carbamate (2.1 g, 5.0 mmol) and TEA (2.1 mL, 15.0 mmol) in dichloromethane (50 mL) was added mesyl chloride (0.58 mL, 7.5 mmol) dropwise at 0° C. The resulting reaction mixture stirred at rt for 3 h. The reaction mixture was then transferred into ice water and the resulting mixture was extracted with DCM (3×100 mL). The combined organic layer was dried over anhydrous sodium sulfate and filtered. The filtrate was evaporated under reduced pressure to give 1-((1R,3R)-3-((tert-butoxycarbonyl)amino)cyclobutyl)-2,5,8,11,14-pentaoxahexadecan-16-yl methanesulfonate as a brown oil (2.3 g, 92%). LCMS (ESI⁺) m/z 499.62 (M+H)⁺.

Step 4—tert-butyl ((1R,3R)-3-(16-azido-2,5,8,11,14-pentaoxahexadecyl)cyclobutyl)carbamate To a stirred solution of 1-((1R,3R)-3-((tert-butoxycarbonyl)amino)cyclobutyl)-2,5,8,11,14-pentaoxahexadecan-16-yl methanesulfonate (2.0 g, 4.0 mmol) in DMF (20 mL) was added sodium azide (390 mg, 6.0 mmol) at rt. The resulting reaction mixture then heated to 65° C. and stirred for 2 h. The reaction mixture was then transferred into ice water and the resulting mixture was extracted with ethyl acetate (3×100 mL). The combined organic layer was dried over anhydrous sodium sulfate and filtered. The filtrate was evaporated under reduced pressure to afford crude product which was purified by silica gel column chromatography (2% MeOH-DCM) to give tert-butyl ((1R,3R)-3-(16-azido-2,5,8,11,14-pentaoxahexadecyl)cyclobutyl) carbamate as a colorless liquid (1.75 g, 98%). LCMS (ESI⁺) m/z 446.55 (M+H)⁺.

Step 5—tert-butyl ((1R,3R)-3-(16-amino-2,5,8,11,14-pentaoxahexadecyl)cyclobutyl)carbamate To a stirred solution of tert-butyl ((1R,3R)-3-(16-azido-2,5,8,11,14-pentaoxahexadecyl)cyclobutyl) carbamate (1.8 g, 4.0 mmol) in ethanol (40 mL) was added 10% Pd/C (50% wet) (1.8 g) at rt under nitrogen atmosphere. The resulting reaction mixture was then stirred under hydrogen gas (2 kg/cm² pressure) in autoclave at rt for 2 h. The reaction mixture was filtered through a pad of celite and washed with MeOH (50 mL). The filtrate was evaporated under reduced pressure to give tert-butyl ((1r,3r)-3-(16-amino-2,5,8,11,14-pentaoxahexadecyl)cyclobutyl)carbamate as a brown oil (1.41 g, 83%). LC-MS (ESI⁺) m/z 420.55 (M+H)⁺

4-(3-carbamoyl-4-(2-(2-((2,2,2-trifluoroethyl)amino)pyridin-4-yl)oxazole-4-carboxamido)-1H-pyrazol-1-yl)benzoic acid (Intermediate ET)

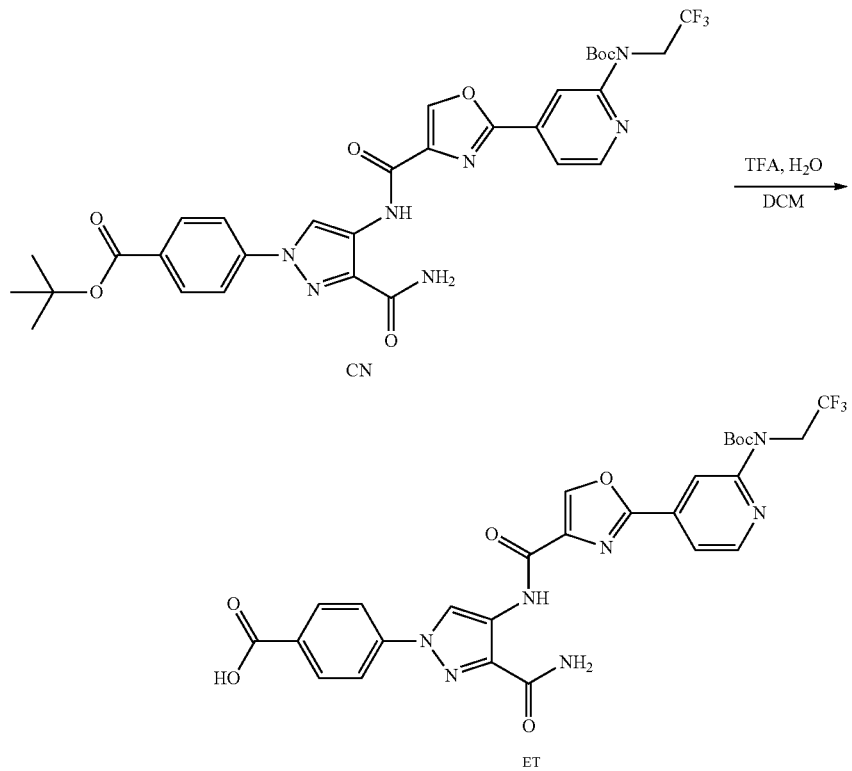

Prepared a 5:4:1 mixture of DCM:TFA:H₂O by combining DCM (5.6 mL), trifluoroacetic acid (4.5 mL), and water (1.1 mL). To this solution was added Intermediate CN (870 mg, 1.69 mmol) and the reaction mixture was stirred for 2.5 h at rt. On completion, the solvent was removed and the residue was placed under high vacuum to yield 1.07 g (quantitative yield) of the title compound as a brown solid. LC-MS (ESI⁺) m/z 516.1 (M+H)⁺.

2-(4-iodobutyl)isoindoline-1,3-dione (Intermediate EU)

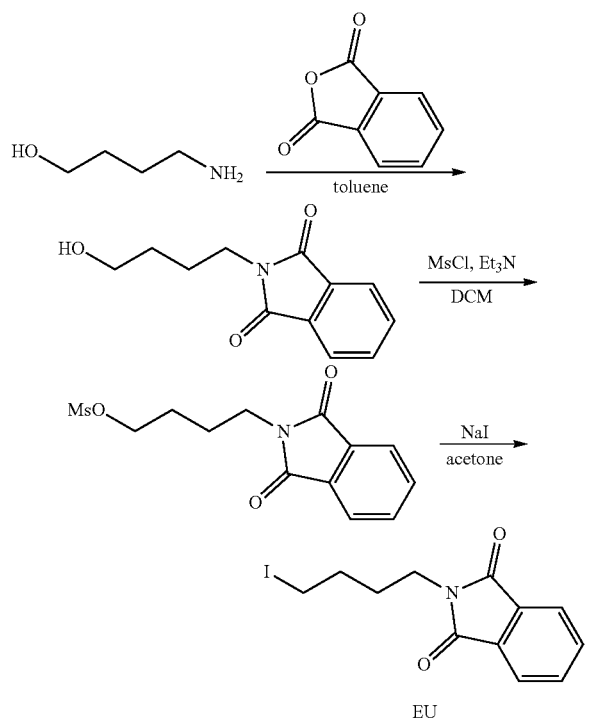

Step 1—2-(4-hydroxybutyl)isoindoline-1,3-dione

To a suspension of 4-aminobutan-1-ol (5.05 g, 48.95 mmol) in toluene (200 mL) was added phthalic anhydride (7.25 g, 48.95 mmol). The reaction mixture was stirred under a Dean-Stark apparatus at 110° C. for 16 h at. The reaction mixture was then cooled to rt and washed with a 1N aqueous solution of HCl. The organics were washed with brine, dried over magnesium sulfate, filtered and concentrated in vacuo. The residue was purified by flash column chromatography (gradient of 25-75% Ethyl Acetate in Hexanes) to yield the title compound (8.62 g, 76%) as a colorless oil.

Step 2—4-(1,3-dioxoisoindolin-2-yl)butyl methanesulfonate 2-(4-hydroxybutyl)isoindoline-1,3-dione (7.6 g, 32.6 mmol) was dissolved in dichloromethane (200 mL) and cooled to 0° C. Triethylamine (5.9 mL, 42.4 mmol) and methane sulfonyl chloride (2.77 mL, 35.83 mmol) were added and the reaction was stirred for 1.5 hours. The reaction mixture was then quenched with a saturated aqueous solution of NaHCO₃, and the layers were partitioned. The organic layer was washed with a saturated aqueous solution of NaHCO₃ (3 times), dried over magnesium sulfate, filtered and concentrated in vacuo to give the title compound (9.9 g, 97%) as an off-white powder.

Step 3—2-(4-iodobutyl)isoindoline-1,3-dione 4-(1,3-dioxoisoindolin-2-yl)butyl methanesulfonate (9.90 g, 31.82 mmol) was dissolved in acetone (200 mL). Then sodium iodide (14.4 g, 95.5 mmol) was added and the reaction mixture was heated to 58° C. for 2 hours. The reaction mixture was then concentrated in vacuo, then the residue was diluted with water and the aqueous layer was extracted with Ethyl Acetate (3 times). The combined organic layer was washed with water, dried over magnesium sulfate, filtered and concentrated in vacuo. The title compound was isolated as a yellow powder (10.22 g, 93%). LC-MS (ESI⁺) m/z 344.0 (M+H)⁺.

5-(2-(4-((tetrahydro-2H-pyran-2-yl)oxy)butoxy)ethoxy)pentan-1-amine (Intermediate EV)

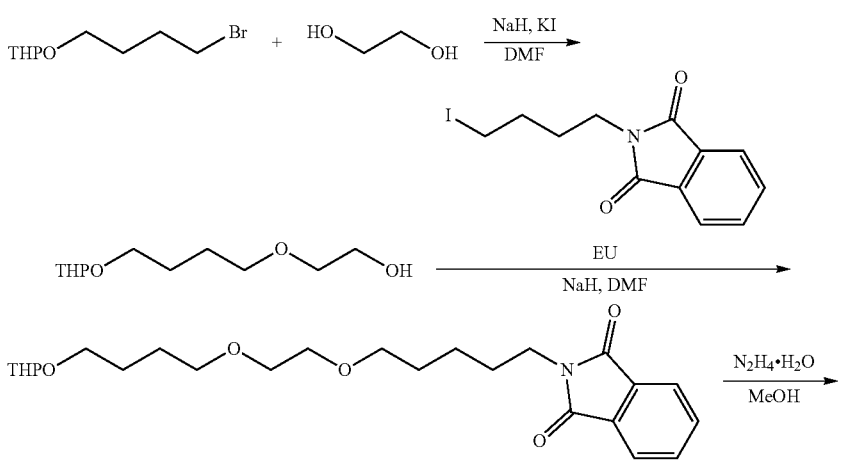

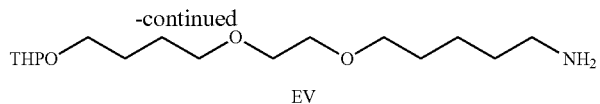

EV

Step 1—2-(4-((tetrahydro-2H-pyran-2-yl)oxy)butoxy)ethan-1-ol

To a suspension of NaH (2.9 g, 73.42 mmol, 60% dispersion in mineral oil) in dry DMF (150 mL) was added ethylene glycol (17.2 mL, 306 mmol) dropwise. The reaction mixture was stirred for 30 minutes at rt before the addition of potassium iodide (10.15 g, 61.19 mmol) and 2-(4-bromobutoxy)tetrahydro-2H-pyran (15.37 g, 61.19 mmol, CAS #31608-22-7). The reaction was stirred at rt for 16 h. The reaction mixture was then quenched with a saturated aqueous solution of NH$_4$Cl. The aqueous layer was extracted with Ethyl Acetate (3 times). The combined organic layer was dried over magnesium sulfate, filtered and concentrated in vacuo. The residue was purified by silica gel column chromatography (gradient of 20-100% Ethyl Acetate in Hexanes). The title compound was isolated as a yellow powder (4.33 g, 30% yield).

Step 2—2-(5-(2-(4-((tetrahydro-2H-pyran-2-yl)oxy)butoxy)ethoxy)pentyl)isoindoline-1,3-dione 2-(4-((tetrahydro-2H-pyran-2-yl)oxy)butoxy)ethan-1-ol (2.2 g, 9.5 mmol) was dissolved in dry DMF (40 mL). Then NaH (0.41 g, 10.4 mmol, 60% dispersion in mineral oil) was carefully added. After stirring for 30 minutes at rt, 2-(4-iodobutyl)isoindoline-1,3-dione (3.9 g, 11.3 mmol, Intermediate EU) was added and the reaction mixture was stirred at rt for 16 h. The reaction mixture was then was quenched with water and the aqueous layer was extracted with Ethyl Acetate (3 times). The combined organic layer was washed with water, dried over magnesium sulfate, filtered and concentrated. The resulting residue was purified by silica gel chromatography (gradient of 0-100% Ethyl Acetate in Hexanes) to give the title compound (956 mg, 22% yield) as a colorless oil. LC-MS (ESI$^+$) m/z 449.2 (M+H)$^+$.

Step 3—5-(2-(4-((tetrahydro-2H-pyran-2-yl)oxy)butoxy)ethoxy)pentan-1-amine 2-(5-(2-(4-((tetrahydro-2H-pyran-2-yl)oxy)butoxy)ethoxy)pentyl)isoindoline-1,3-dione (200 mg, 0.44 mmol) was dissolved in methanol (3 mL) and hydrazine hydrate (64 µL, 1.32 mmol) was added. The reaction mixture was heated to 70° C. and stirred for 3 hours. The reaction mixture was then cooled to rt and concentrated in vacuo. The residue was triturated in diethyl ether, and the white precipitate was filtered off. The filtrate was then concentrated in vacuo to give the title compound as a colorless oil (120 mg, 87% yield).

Tert-butyl (3,6,9,12-tetraoxapentadec-14-yn-1-yl)carbamate (Intermediate EW)

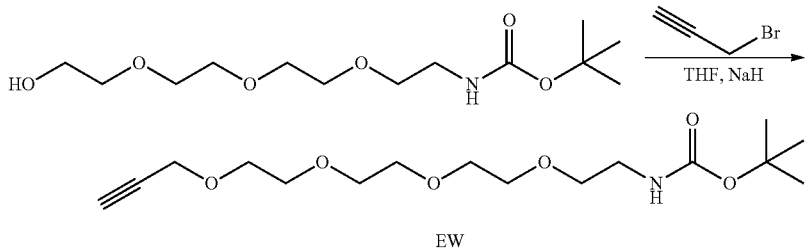

EW

To a solution of tert-butyl (2-(2-(2-(2-hydroxyethoxy)ethoxy)ethoxy)ethyl)carbamate (10.0 g, 34.1 mmol, Step 1 of Intermediate EN) in anhydrous THF (250 mL) was added sodium hydride (1.63 g, 40.94 mmol, 60% dispersion in mineral oil) in one portion under nitrogen atmosphere. The reaction mixture was stirred at rt for 0.5 h and thereafter it was cooled to 0° C. An 80% solution of 3-bromoprop-1-yne in toluene (5.7 mL, 51.2 mmol) was added dropwise to the reaction mixture at 0° C. over a period of 10 min. The resulting reaction mixture was stirred at 0° C. for 1 h and thereafter it was allowed to warm to rt. The resulting reaction mixture was stirred overnight at rt. Then the reaction mixture was quenched with a small aliquot of methanol (1.6 mL) and concentrated on a rotary evaporator. The obtained crude material was suspended in DCM (100 mL) and was washed with water (2×30 mL) and brine (50 mL). The resulting organic layer was dried over anhydrous sodium sulphate, filtered and concentrated on a rotary evaporator. The obtained crude product was purified by silica gel chromatography (gradient Ethyl acetate/Hexanes) to give the title compound (6.25 g, 55%) as a light yellow viscous liquid.

3-Benzyloxy-5-methoxy-aniline (Intermediate EX)

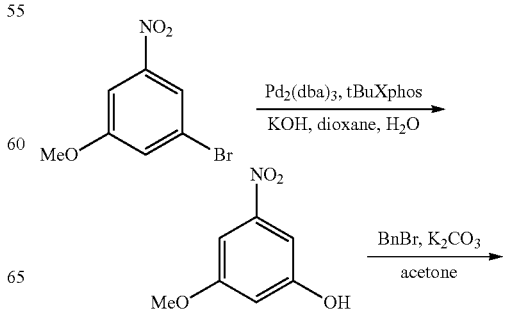

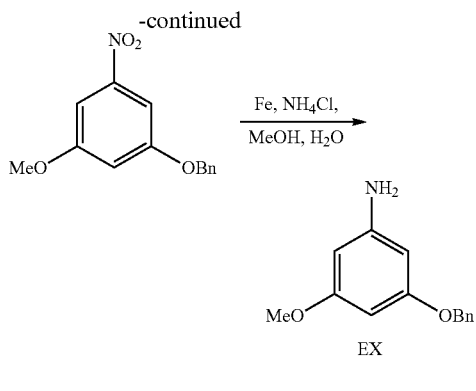

Step 1—3-Methoxy-5-nitro-phenol

A mixture of KOH (11.6 g, 206 mmol) and 1-bromo-3-methoxy-5-nitro-benzene (12.0 g, 51.7 mmol) in a mixed solvent of dioxane (80 mL) and H$_2$O (80 mL) was degassed for 5 minutes. Then Pd$_2$(dba)$_3$ (473 mg, 517 umol) and tBuXphos (439 mg, 1.03 mmol) were added to the reaction mixture. The resulting reaction mixture was degassed for a further 0.5 hour, and then the reaction mixture was heated at 100° C. for 12 hours under a nitrogen atmosphere. On completion, the mixture was cooled, then acidified with 5 M HCl until the pH=1.0 and extracted with EtOAc (2×200 mL). The combined organic layer was washed with saturated brine (200 mL), dried over anhydrous Na$_2$SO$_4$, filtered and concentrated in vacuo. The residue was purified by silica gel chromatography (PE:EA=3:1) to give the title compound (8.60 g, 98% yield) as a yellow solid. $^1$H NMR (400 MHz, DMSO-d$_6$) δ 10.46 (s, 1H), 7.18 (d, J=2.4 Hz, 2H), 6.75 (t, J=2.4 Hz, 1H), 3.81 (s, 3H).

Step 2—1-Benzyloxy-3-methoxy-5-nitro-benzene

To a mixture of 3-methoxy-5-nitro-phenol (4.00 g, 23.6 mmol) in acetone (150 mL) was added K$_2$CO$_3$ (8.17 g, 59.1 mmol) and BnBr (6.07 g, 35.4 mmol, 4.21 mL). Then the reaction mixture was stirred at 50° C. for 12 hours. On completion, the reaction mixture was filtered, and the filtrate was concentrated in vacuo to remove acetone. The residue was washed with water (100 mL) and extracted with EA (2×200 mL). The combined organic layers were dried over Na$_2$SO$_4$, filtered and concentrated in vacuo to give a residue. The residue was purified by silica gel chromatography (PE:EA=8:1) to give the title compound (6.00 g, 97% yield) as a yellow solid. $^1$H NMR (400 MHz, CDCl$_3$) δ 7.52-7.34 (m, 7H), 6.84 (t, J=2.4 Hz, 1H), 5.13 (s, 2H), 3.87 (s, 3H).

Step 3—3-Benzyloxy-5-methoxy-aniline

To a solution of 1-benzyloxy-3-methoxy-5-nitro-benzene (2.00 g, 7.71 mmol) in MeOH (45 mL) and H$_2$O (10 mL) was added Fe (4.31 g, 77.1 mmol) followed by NH$_4$Cl (4.12 g, 77.1 mmol). Then, the reaction mixture was stirred at 75° C. for 14 hours. On completion, the reaction mixture was filtered and the filtrate was concentrated in vacuo to remove MeOH. The residue was washed with water (100 mL) and extracted with EA (2×200 mL). The combined organic layers were dried over Na$_2$SO$_4$, filtered and concentrated in vacuo to give the title compound (1.14 g, 64% yield) as black brown oil. $^1$H NMR (400 MHz, CDCl$_3$) δ 7.47-7.28 (m, 5H), 6.04 (t, J=2.0 Hz, 1H), 5.98 (t, J=2.0 Hz, 1H), 5.92 (t, J=2.0. Hz, 1H), 5.03 (s, 2H), 3.76 (s, 3H); LC-MS (ESI$^+$) m/z 230.1 (M+H)$^+$.

2-[2-[2-[2-(Benzyloxycarbonylamino)ethoxy]ethoxy]ethoxy]ethyl methanesulfonate (Intermediate EY)

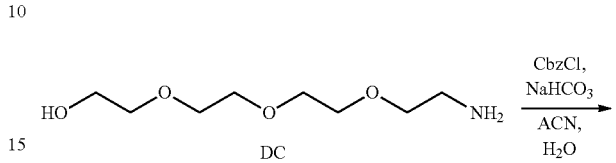

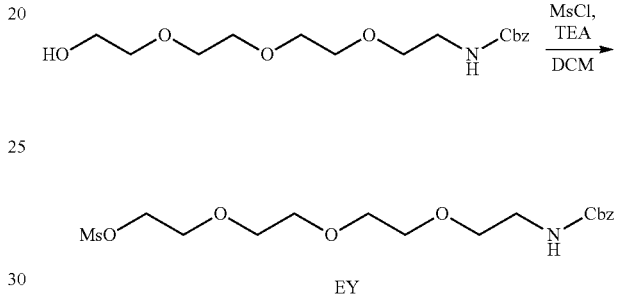

Step 1—Benzyl N-[2-[2-[2-(2-hydroxyethoxy)ethoxy]ethoxy]ethyl]carbamate

To a solution of 2-[2-[2-(2-aminoethoxy)ethoxy]ethoxy]ethanol (6.00 g, 31.0 mmol, Intermediate DC) in ACN (50 mL) and H$_2$O (50 mL) was added CbzCl (6.36 g, 37.2 mmol) and NaHCO$_3$ (7.83 g, 93.1 mmol). The reaction mixture was stirred at rt for 12 hours. On completion, the reaction mixture was diluted with water (30 mL) and extracted with EA (3×30 mL). The combined organic layers were dried over anhydrous sodium sulfate, filtered and concentrated in vacuo to give a residue. The residue was purified by column chromatography to give the title compound (9.20 g, 90% yield) as a colorless oil. LC-MS (ESI$^+$) m/z 350.0 (M+Na)$^+$.

Step 2—2-[2-[2-[2-(Benzyloxycarbonylamino)ethoxy]ethoxy]ethoxy]ethyl methanesulfonate To a mixture of benzyl N-[2-[2-[2-(2-hydroxyethoxy)ethoxy]ethoxy]ethyl]carbamate (1.00 g, 3.05 mmol) in dichloromethane (10 mL) was added TEA (617 mg, 0.85 mL, 6.10 mmol) and MsCl (524 mg, 0.354 mL, 4.57 mmol) dropwise at 0° C. under nitrogen atmosphere. The reaction mixture then allowed to warm to rt and stirred for 1 hour. On completion, the reaction mixture was poured into 5 mL of water and acidified with citric acid until the pH=5-6. The mixture was extracted with dichloromethane (2×10 mL). The combined organic layers were dried over Na$_2$SO$_4$, filtered and concentrated in vacuo to give the title compound (1.10 g, 88% yield) as a light yellow oil. LC-MS (ESI$^+$) m/z 406.0 (M+H)$^+$.

1309

7-((3-Hydroxy-5-methoxyphenyl)amino)-5-(methyl-thio)imidazo[1,2-c]pyrimidine-8-carboxamide (Intermediate EZ)

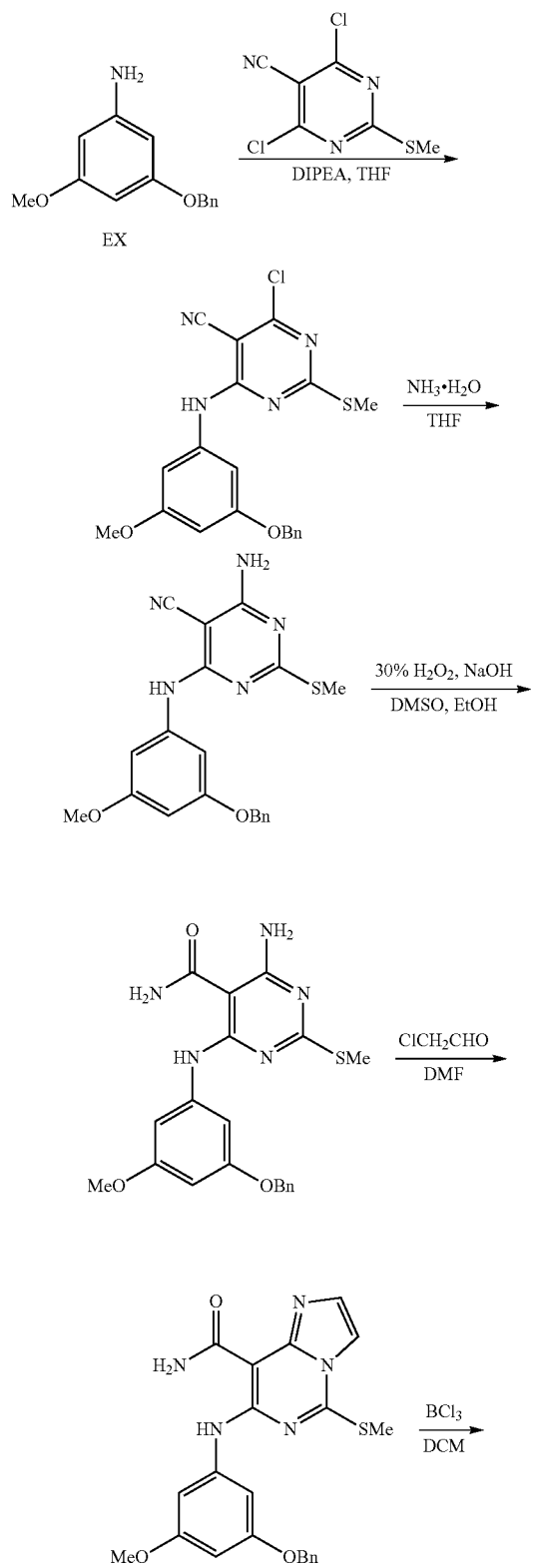

1310

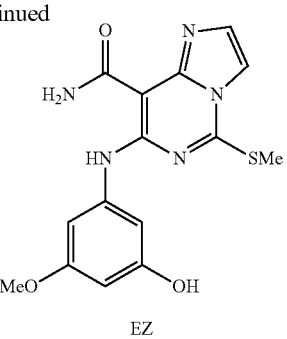

EZ

Step 1—4-(3-Benzyloxy-5-methoxy-anilino)-6-chloro-2-methylsulfanyl-pyrimidine-5-carbonitrile To a mixture of 3-benzyloxy-5-methoxy-aniline (6.90 g, 30.1 mmol, Intermediate EX) and 4,6-dichloro-2-methylsulfanyl-pyrimidine-5-carbonitrile (6.62 g, 30.1 mmol, CAS #33097-13-1) in THF (20 mL) was added DIPEA (5.83 g, 45.1 mmol, 7.88 mL) dropwise at 0° C. The reaction mixture was then allowed to warm to rt and stirred for 12 hours. On completion, the reaction mixture was concentrated in vacuo to remove THF. The residue was washed with water (100 mL) and extracted with EA (2×200 mL). The combined organic layers were dried over $Na_2SO_4$, filtered and concentrated in vacuo to give the title compound (9.00 g, 72% yield) as a light yellow solid. $^1$H NMR (400 MHz, DMSO-$d_6$) δ 7.51-7.29 (m, 5H), 6.93 (t, J=2.0 Hz, 1H), 6.85 (t, J=2.0 Hz, 1H), 6.45 (t, J=2.4 Hz, 1H), 5.08 (s, 2H), 3.73 (s, 3H), 2.46 (s, 3H); LC-MS (ESI$^+$) m/z 412.9 (M+H)$^+$.

Step 2—4-Amino-6-(3-benzyloxy-5-methoxy-anilino)-2-methylsulfanyl-pyrimidine-5-carbonitrile To a solution 4-(3-benzyloxy-5-methoxy-anilino)-6-chloro-2-methylsulfanylpyrimidine-5-carbonitrile (10.2 g, 24.7 mmol) in THF (50 mL) was added $NH_3·H_2O$ (30 mL). The reaction mixture was stirred at 70° C. for 12 hours. On completion, the reaction mixture was concentrated in vacuo to give a residue. The residue was triturated with DCM (100 mL) and filtered. The filter cake was collected to afford a white solid. Then, the white solid was triturated with acetone (50 mL) to give the title compound (7.79 g, 80% yield) as an off-white solid. LC-MS (ESI$^+$) m/z 394.0 (M+H)$^+$.

Step 3—4-Amino-6-(3-benzyloxy-5-methoxy-anilino)-2-methylsulfanyl-pyrimidine-5-carboxamide To a mixture 4-amino-6-(3-benzyloxy-5-methoxy-anilino)-2-methylsulfanylpyrimidine-5-carbonitrile (7.79 g, 19.8 mmol) in DMSO (80 mL) and EtOH (80 mL) was added NaOH (5 M, 19.8 mL) and $H_2O_2$ (11.2 g, 99.0 mmol, 9.51 mL, 30% solution) dropwise. The reaction mixture was stirred at rt of 2.5 hours. On completion, the reaction mixture was quenched by slow addition of saturated $Na_2S_2O_3$ solution (50 mL) under stirring. The reaction mixture was concentrated in vacuo to remove the EtOH. The residue was poured into 100 mL of water and acidified with 1M HCl until the pH=7. The mixture was extracted with EA (2×200 mL). The combined organic layer was dried over $Na_2SO_4$, filtered and concentrated in vacuo to give the title compound (10.0 g, 91% yield) as a white solid. $^1$H NMR (400 MHz, DMSO-$d_6$) δ 9.89 (s, 1H), 7.56 (s, 2H), 7.47-7.31 (m, 5H), 6.91 (t, J=2.0 Hz, 1H), 6.88 (t, J=2.0 Hz, 1H), 6.85 (s, 2H), 6.25 (t, J=2.0 Hz, 1H), 5.07 (s, 2H), 3.72 (s, 3H), 2.46 (s, 3H); LC-MS (ESI$^+$) m/z 412.0 (M+H)$^+$.

Step 4—7-(3-Benzyloxy-5-methoxy-anilino)-5-methylsulfanyl-imidazo[1,2-c]pyrimidine-8-carboxamide To a mixture of 4-amino-6-(3-benzyloxy-5-methoxy-anilino)-2-methylsulfanylpyrimidine-5-carboxamide (8.00 g, 19.4 mmol) in DMF (50 mL) was added a solution of 2-chloroacetaldehyde (11.4 g, 58.3 mmol, 9.39 mL, 40% solution in water). The reaction mixture was stirred at 60° C. for 8 hours. On completion, the reaction mixture was concentrated in vacuo to remove the DMF. The residue was purified by silica gel chromatography (DCM:MeOH=80:1) to give the title compound (2.30 g, 27% yield) as a yellow solid. $^1$H NMR (400 MHz, CDCl$_3$) δ 12.04 (s, 1H), 10.04 (s, 1H), 7.48-7.33 (m, 7H), 6.94-6.92 (m, 1H), 6.88-6.85 (m, 1H), 6.34 (t, J=2.0 Hz, 1H), 5.74 (s, 1H), 5.07 (s, 2H), 3.81 (s, 3H), 2.80 (s, 3H); LC-MS (ESI$^+$) m/z 436.0 (M+H)$^+$.

Step 5—7-((3-Hydroxy-5-methoxyphenyl)amino)-5-(methylthio)imidazo[1,2-c]pyrimidine-8-carboxamide To a solution of 7-(3-benzyloxy-5-methoxy-anilino)-5-methylsulfanyl-imidazo[1,2-c]pyrimidine-8-carboxamide (2.30 g, 5.28 mmol) in DCM (150 mL) was added a solution of BCl$_3$ in DCM (1 M, 42.2 mL) under nitrogen atmosphere. The reaction mixture was stirred at rt for 12 h. On completion, the reaction mixture was concentrated in vacuo. The residue was purified by silica gel chromatography (dichloromethane:methanol=20:1) to give the title compound (1.42 g, 70% yield) as a yellow solid. $^1$H NMR (400 MHz, DMSO-d$_6$) δ 11.98 (s, 1H), 7.76 (d, J=1.6 Hz, 1H), 7.55 (d, J=1.6 Hz, 1H), 6.67 (d, J=2.0 Hz, 1H), 6.64 (d, J=2.0 Hz, 1H), 6.10 (d, J=2.0 Hz, 1H), 3.71 (s, 3H), 2.80 (s, 3H).

7-(4-Hydroxy-3,5-dimethoxy-anilino)-5-methylsulfanyl-imidazo[1,2-c]pyrimidine-8-carboxamide (Intermediate FA)

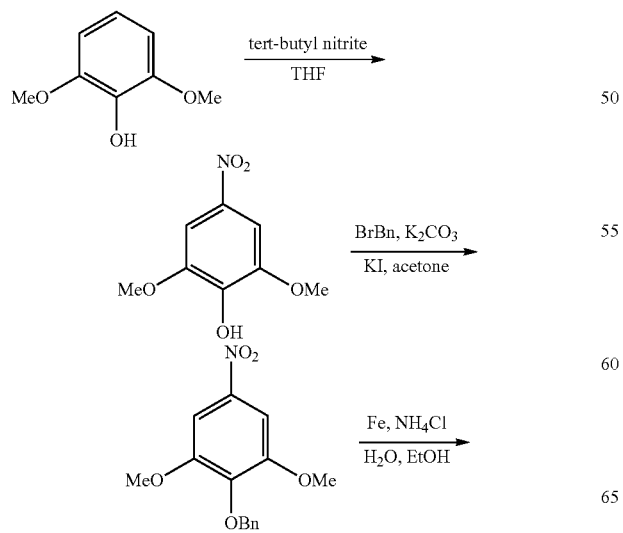

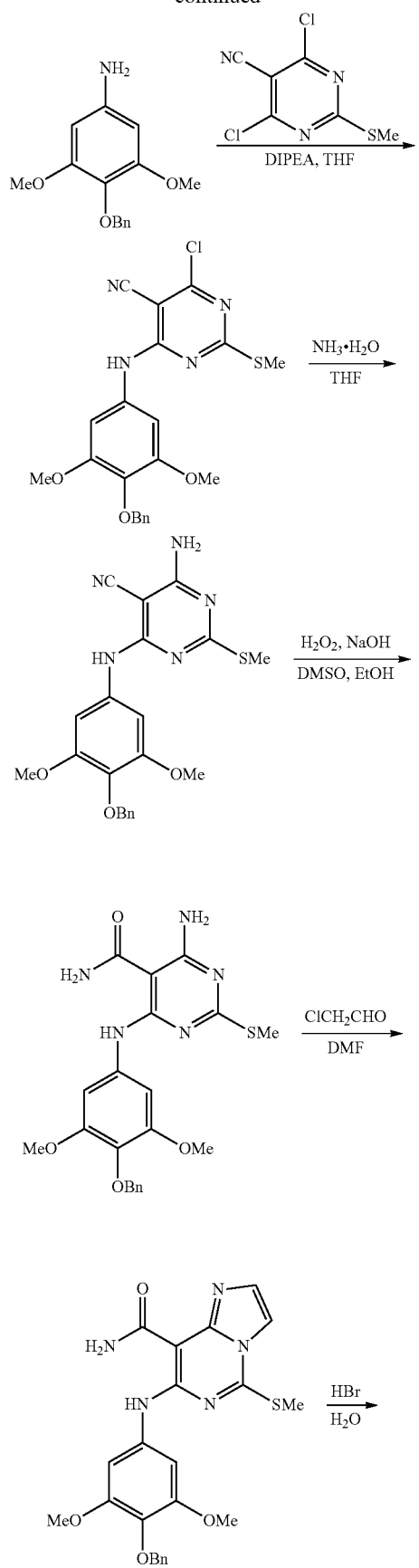

-continued

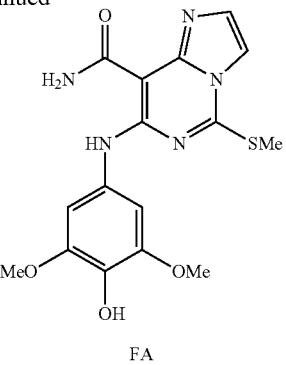

FA

Step 1—2,6-dimethoxy-4-nitro-phenol

To a solution of 2,6-dimethoxyphenol (5.00 g, 32.4 mmol) in THF (50 mL) was added dropwise tert-butyl nitrite (10.0 g, 97.3 mmol). Then, the reaction mixture was stirred at rt for 0.5 hr. On completion, the reaction mixture was concentrated in vacuo. The residue was purified by column chromatography to give the title compound (3.73 g, 58% yield) as a yellow solid. $^1$H NMR (400 MHz, CDCl$_3$) δ 7.57 (s, 2H), 6.06 (s, 1H), 3.91 (s, 6H).

Step 2—2-Benzyloxy-1,3-dimethoxy-5-nitro-benzene

To a solution of 2,6-dimethoxy-4-nitro-phenol (8.00 g, 40.2 mmol) in acetone (100 mL) was added K$_2$CO$_3$ (11.1 g, 80.3 mmol) and KI (667 mg, 4.02 mmol) at rt. The suspension was stirred at rt for 1 hr. Then, bromomethylbenzene (10.3 g, 60.3 mmol) was added to the mixture dropwise. The reaction mixture was then heated to 60° C. and stirred for 12 hours. On completion, the reaction mixture was concentrated in vacuo to remove the acetone. The residue was diluted with water (100 mL) and extracted with EA (3×150 mL). The combined organic layers were dried over anhydrous Na$_2$SO$_4$, filtered and concentrated in vacuo to give a residue. The residue was purified by column chromatography to give the title compound (8.62 g, 74% yield) as a white solid. $^1$H NMR (400 MHz, CDCl$_3$) δ 7.51 (s, 2H), 7.45 (d, J=6.8 Hz, 2H), 7.39-7.27 (m, 3H), 5.14 (s, 2H), 3.91 (s, 6H).

Step 3—4-Benzyloxy-3,5-dimethoxy-aniline

To a solution of 2-benzyloxy-1,3-dimethoxy-5-nitro-benzene (8.62 g, 29.8 mmol) in a mixed solvent of H$_2$O (50 mL) and EtOH (170 mL) was added Fe (16.6 g, 298 mmol) followed by NH$_4$Cl (15.9 g, 298 mmol). Then, the reaction mixture was stirred at 75° C. under nitrogen for 1.5 hrs. On completion, the mixture was diluted with MeOH (150 mL), filtered through a pad of Celite and washed with MeOH (80 mL). The filtrate was concentrated, and the residue was washed with H$_2$O (100 mL) and extracted with EA (2×150 mL). The organic layer was dried over anhydrous Na$_2$SO$_4$ and concentrated in vacuo to give a residue. The residue was purified by column chromatography to give the title compound (7.27 g, 94% yield) as a black brown oil. LC-MS (ESI$^+$) m/z 260.0 (M+H)$^+$.

Step 4—4-(4-Benzyloxy-3,5-dimethoxy-anilino)-6-chloro-2-methylsulfanyl-pyrimidine-5-carbonitrile To a solution of 4,6-dichloro-2-methylsulfanyl-pyrimidine-5-carbonitrile (6.17 g, 28.0 mmol) and 4-benzyloxy-3,5-dimethoxy-aniline (7.27 g, 28.0 mmol) in THF (150 mL) was added DIPEA (5.44 g, 42.1 mmol) dropwise. The reaction mixture was stirred at rt for 15 hours. On completion, the reaction mixture was diluted with water (150 mL) and filtered. Then, the filter cake was dried in vacuo to give the title compound (9.49 g, 76% yield) as a yellow solid. LC-MS (ESI$^+$) m/z 464.9 (M+Na)$^+$.

Step 5—4-Amino-6-(4-benzyloxy-3,5-dimethoxy-anilino)-2-methylsulfanyl-pyrimidine-5-carbonitrile To a mixture of 4-(4-benzyloxy-3,5-dimethoxy-anilino)-6-chloro-2-methylsulfanyl-pyrimidine-5-carbonitrile (4.49 g, 10.1 mmol) in THF (50 mL) was added NH$_3$.H$_2$O (7.11 g, 203 mmol). Then, the reaction mixture heated to 70° C. and stirred for 17 hours at autoclave. On completion, the reaction mixture was concentrated in vacuo to give a residue. The residue was triturated with DCM to give the title compound (3.74 g, 87% yield) as a yellow solid. $^1$H NMR (400 MHz, CDCl$_3$) δ 7.54-7.48 (m, 2H), 7.41-7.30 (m, 3H), 6.88 (s, 1H), 6.84 (s, 2H), 5.35 (s, 2H), 5.02 (s, 2H), 3.85 (s, 6H), 2.50 (s, 3H); LC-MS (ESI$^+$) m/z 424.0 (M+H)$^+$.

Step 6—4-Amino-6-(4-benzyloxy-3,5-dimethoxy-anilino)-2-methylsulfanyl-pyrimidine-5-carboxamide To a solution of 4-amino-6-(4-benzyloxy-3,5-dimethoxy-anilino)-2-methylsulfanyl-pyrimidine-5-carbonitrile (5.60 g, 13.2 mmol) in DMSO (30 mL) and EtOH (30 mL) at 0° C. was added H$_2$O$_2$ (7.50 g, 66.1 mmol, 30% solution) and NaOH (5 M, 13.2 mL, 20% solution). The reaction mixture was stirred at rt for 3 hours. On completion, the mixture was quenched with sat.Na$_2$SO$_3$. Then the mixture was filtered through a pad of celite. After that, the filter cake was washed with H$_2$O (3×50 mL) and dried to give the title compound (5.70 g, 98% yield) as a yellow solid. $^1$H NMR (400 MHz, DMSO-d$_6$) δ 9.82 (s, 1H), 7.54 (s, 2H), 7.46 (d, J=6.8 Hz, 2H), 7.41-7.28 (m, 3H), 6.95 (s, 2H), 6.83 (s, 2H), 4.85 (s, 2H), 3.76 (s, 6H), 2.45 (s, 3H); LC-MS (ESI$^+$) m/z 442.1 (M+H)$^+$.

Step 7—7-(4-Benzyloxy-3,5-dimethoxy-anilino)-5-methylsulfanyl-imidazo[1,2-c]pyrimidine-8-carboxamide A mixture of 4-amino-6-(4-benzyloxy-3,5-dimethoxy-anilino)-2-methylsulfanyl-pyrimidine-5-carboxamide (5.00 g, 11.3 mmol) and 2-chloroacetaldehyde (3.33 g, 17.0 mmol) in DMF (20 mL) was heated at 60° C. for 6 hours under nitrogen atmosphere. On completion, the reaction mixture was concentrated in vacuo to give a residue. The residue was purified by column chromatography to give the title compound (5.07 g, 96% yield) as a yellow solid. $^1$H NMR (400 MHz, CDCl$_3$) δ 11.88 (s, 1H), 10.00 (s, 1H), 7.42 (d, J=7.2 Hz, 2H), 7.32-7.22 (m, 5H), 6.70 (s, 2H), 5.64 (m, 1H), 4.94 (s, 2H), 3.75 (s, 6H), 2.64 (s, 3H); LC-MS (ESI$^+$) m/z 466.0 (M+H)$^+$.

Step 8—7-(4-Hydroxy-3,5-dimethoxy-anilino)-5-methylsulfanyl-imidazo[1,2-c]pyrimidine-8-carboxamide To 7-(4-benzyloxy-3,5-dimethoxy-anilino)-5-methylsulfanyl-imidazo[1,2-c]pyrimidine-8-carboxamide (1.55 g, 3.33 mmol) was added HBr (22.4 g, 15 mL, 110 mmol, 40% solution). The reaction mixture was stirred at 50° C. for 3 hours under nitrogen atmosphere. On completion, the reaction mixture was concentrated in vacuo to give a residue. The residue was triturated with dichloromethane:methanol=10:1 to give the title compound (1.20 g, 96% yield) as a yellow solid. LC-MS (ESI+) m/z 376.0 (M+H)+.

5,7-Dichloropyrido[4,3-d]pyrimidin-4 (3H)-one (Intermediate FB)

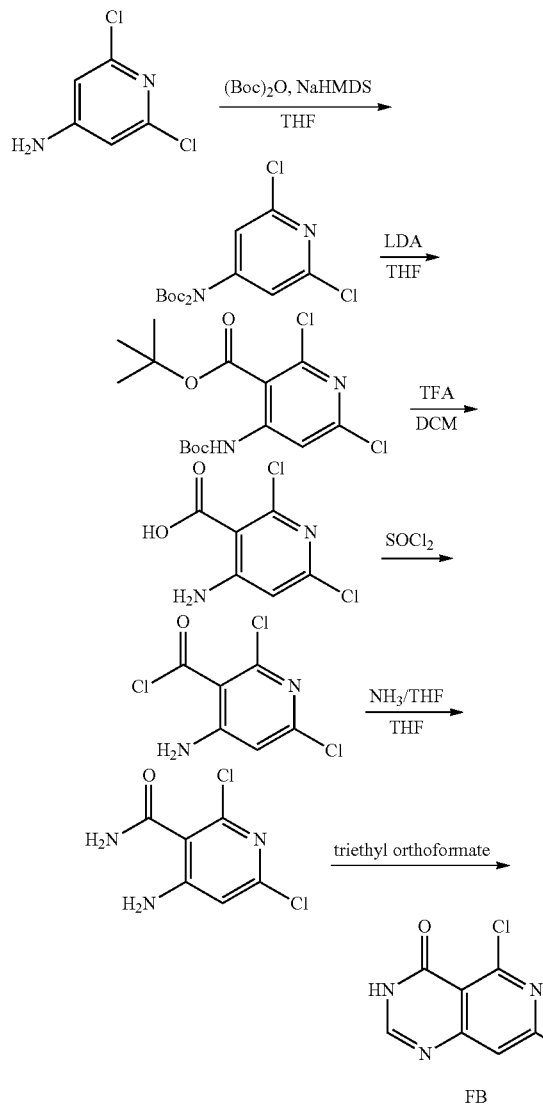

Step 1—Tert-butyl N-tert-butoxycarbonyl-N-(2,6-dichloro-4-pyridyl)carbamate

A solution of 2,6-dichloropyridin-4-amine (28.0 g, 172 mmol, CAS #2587-02-2) in THF (400 mL) under nitrogen was cooled to 0° C. with an ice-water bath. To this mixture was added a solution of NaHMDS (1 M, 412 mL) in THF. After the reaction mixture was stirred at 0° C. for 0.5 h, a solution of (Boc)$_2$O (82.5 g, 378 mmol, 86.8 mL) in THF (1.2 L) was added and the ice-water bath was then removed. The reaction mixture was then stirred at rt for 16 hrs. On completion, the reaction mixture was quenched with saturated NH$_4$Cl (1000 mL) and extracted with ethyl acetate (3×500 mL). The combined organic layer was washed with brine (100 mL), dried over anhydrous sodium sulfate, filtered and concentrated in vacuo to give the title compound (42.0 g, 96% yield) as a white solid. $^1$H NMR (400 MHz, CDCl$_3$) δ 8.98 (s, 1H), 8.34 (s, 1H), 1.63 (s, 9H), 1.53 (s, 9H).

Step 2—Tert-butyl 4-(tert-butoxycarbonylamino)-2,6-dichloro-pyridine-3-carboxylate To a solution of LDA (2 M, 169 mL) was added a solution of tert-butyl N-tert-butoxycarbonyl-N-(2,6-dichloro-4-pyridyl)carbamate (35.0 g, 96.4 mmol) in THF (600 mL) under nitrogen at −78° C. The reaction mixture was stirred at −78° C. for 0.5 hr. On completion, the reaction mixture was quenched with saturated NH$_4$Cl, and extracted with ethyl acetate (3×100 mL). The combined organic layer was washed with brine (100 mL), dried over anhydrous sodium sulfate, filtered and concentrated in vacuo. The residue was purified by silica gel chromatography (PE:EA=200:1) to give the title compound (35.0 g, 100% yield) as a white solid. $^1$H NMR (400 MHz, CDCl$_3$) δ 8.99 (s, 1H), 8.35 (s, 1H), 1.64 (s, 9H), 1.54 (s, 9H).

Step 3—4-Amino-2,6-dichloro-pyridine-3-carboxylic acid

To a solution of tert-butyl 4-(tert-butoxycarbonylamino)-2,6-dichloro-pyridine-3-carboxylate (35 g, 96.4 mmol) in DCM (100 mL) was added TFA (139 g, 1.22 mol, 90 mL). The reaction mixture was stirred at 65° C. for 12 h. On completion, the reaction was mixture was concentrated in vacuo to give the title compound (31.0 g, 82% yield, TFA salt) as yellow solid. LCMS (ESI+) m/z 206.9 (M+H)+.

Step 4—4-amino-2,6-dichloro-pyridine-3-carbonyl chloride

A solution of 4-amino-2,6-dichloro-pyridine-3-carboxylic acid (26.0 g, 81.0 mmol, TFA) and SOCl$_2$ (164 g, 1.38 mol, 100 mL) was heated at 80° C. for 15 min. On completion, the reaction mixture was concentrated in vacuo and the title compound was used directly in the next step. LCMS (M+1)+: 221.0

Step 5—4-Amino-2,6-dichloro-pyridine-3-carboxamide

To a solution of NH$_3$/THF (7 M, 50.1 mL) was added a solution of 4-amino-2,6-dichloro-pyridine-3-carbonyl chloride (5.30 g, 15.6 mmol, TFA salt) in THF (100 mL) at 0° C. The reaction mixture was then allowed to warm to rt and stirred for 12 h. On completion, the reaction mixture was concentrated in vacuo. The crude product was purified by silica gel chromatography (DCM:MeOH=50:1 to 10:1) to give the title compound (2.00 g, 58% yield) as a yellow solid. $^1$H NMR (400 MHz, DMSO-d$_6$) δ=7.99 (s, 1H), 7.72 (s, 1H), 6.61 (s, 1H), 6.59 (s, 2H); LC-MS (ESI+) m/z 205.9 (M+H)+.

Step 6—5,7-Dichloropyrido[4,3-d]pyrimidin-4 (3H)-one

A mixture of 4-amino-2,6-dichloro-pyridine-3-carboxamide (3.00 g, 14.6 mmol) and triethyl orthoformate (53.4 g, 360 mmol, 60 mL) was heated to 150° C. for 3 hrs. On completion, the reaction mixture was concentrated in vacuo and the residue was triturated with PE/EA=1:1 (5 mL) to give the title compound (2.0 g, 64% yield) as a yellow solid. $^1$H NMR (400 MHz, DMSO-d$_6$) δ 12.83 (s, 1H), 8.33 (s, 1H), 7.72 (s, 1H).

2-[2-[2-[2-[2-(Benzyloxycarbonylamino)ethoxy]ethoxy]ethoxy]ethoxy]ethyl methane sulfonate (Intermediate FC)

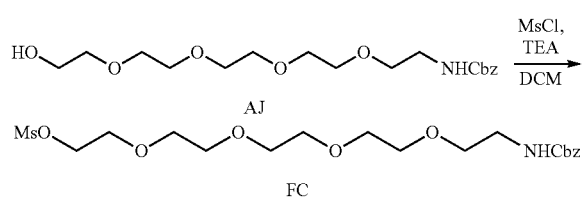

To a solution of benzyl N-[2-[2-[2-[2-(2-hydroxyethoxy)ethoxy]ethoxy]ethoxy]ethyl]carbamate (500 mg, 1.35 mmol, Intermediate AJ) in dichloromethane (6 mL) was added triethylamine (273 mg, 2.70 mmol, 374 uL) and MsCl (185 mg, 1.62 mmol, 125 uL) at 0° C. The reaction mixture was stirred at rt for 1 hour. On completion, the reaction mixture was diluted with water (100 mL), and extracted with ethyl acetate (3×100 mL). Then the combined organic layer was dried over Na$_2$SO$_4$ and concentrated in vacuo to give the title compound (600 mg, 98% yield) as a yellowish oil.

3-Oxo-1-phenyl-2,7,10-trioxa-4-azadodecan-12-yl methanesulfonate (Intermediate FD)

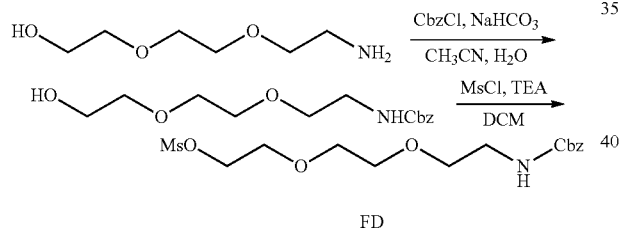

Step 1—Benzyl N-[2-[2-(2-hydroxyethoxy)ethoxy]ethyl]carbamate

To a solution of 2-[2-(2-aminoethoxy)ethoxy]ethanol (3.50 g, 23.5 mmol, CAS #6338-55-2) in CH$_3$CN (30 mL) and H$_2$O (30 mL) was added CbzCl (4.80 g, 28.1 mmol) and NaHCO$_3$ (5.91 g, 70.4 mmol). The reaction mixture was stirred at rt for 12 hours. On completion, the reaction mixture was diluted with water (20 mL) and extracted with ethyl acetate (3×20 mL). The combined organic layer was washed with brine, dried over Na$_2$SO$_4$, filtered and concentrated in vacuo to give a residue. The residue was purified by column chromatography (petroleum ether:ethyl acetate=5:1 to 1:1) to give the title compound (5.00 g, 75% yield) as a colorless oil. $^1$H NMR (400 MHz, CDCl$_3$) δ 7.38-7.29 (m, 5H), 5.47 (s, 1H), 5.11 (s, 2H), 3.71 (s, 2H), 3.65-3.56 (m, 8H), 3.43-3.37 (m, 2H).

Step 2—3-Oxo-1-phenyl-2,7,10-trioxa-4-azadodecan-12-yl methanesulfonate

To a solution of benzyl N-[2-[2-(2-hydroxyethoxy)ethoxy]ethyl]carbamate (2.00 g, 7.06 mmol) in DCM (30 mL) was added TEA (2.14 g, 21.2 mmol, 2.94 mL) and MsCl (1.05 g, 9.18 mmol, 710 uL) at 0° C. The reaction mixture was then allowed to warm to rt and stirred for 0.5 hr. On completion, the reaction mixture was quenched with saturated citric acid (5 mL), and extracted with dichloromethane (3×50 mL). The combined organic layer was washed with brine (20 mL), dried over anhydrous sodium sulfate, filtered and concentrated in vacuo to give the title compound (2.4 g, 94% yield) as a colorless oil. $^1$H NMR (400 MHz, CDCl$_3$) δ 7.39-7.31 (m, 5H), 5.24 (s, 1H), 5.11 (s, 2H), 4.38-4.34 (m, 1H), 4.38-4.34 (m, 1H), 3.76 (dd, J=3.6, 5.2 Hz, 2H), 3.67-3.64 (m, 2H), 3.64-3.60 (m, 2H), 3.59-3.54 (m, 2H), 3.40 (q, J=5.2 Hz, 2H), 3.02 (s, 3H).

N-[2-[(2,5-dichloropyrimidin-4-yl)amino]-5-methoxy-phenyl]methanesulfonamide (Intermediate FE)

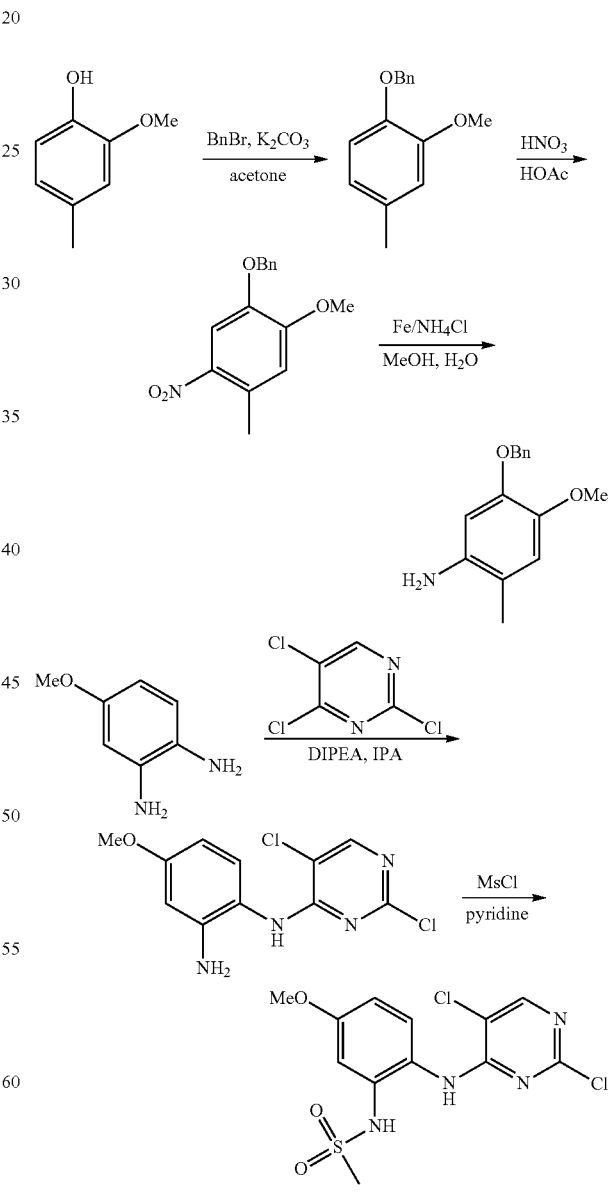

Step 1—1-Benzyloxy-2-methoxy-4-methyl-benzene

To a mixture of 2-methoxy-4-methyl-phenol (25.0 g, 180 mmol) in acetone (460 mL) was added $K_2CO_3$ (62.5 g, 452 mmol) and BnBr (46.4 g, 271 mmol) under nitrogen atmosphere. The reaction mixture was stirred at 50° C. for 12 hours. On completion, the reaction mixture was filtered and concentrated in vacuo to remove the acetone. The residue was diluted with water (100 mL) and extracted with EA (2×200 mL). The combined organic layers was dried over $Na_2SO_4$, filtered and concentrated in vacuo to give a residue. The residue was purified by column chromatography to give the title compound (40.0 g, 96% yield) as white solid. $^1H$ NMR (400 MHz, $CDCl_3$) δ 7.49-7.43 (m, 2H), 7.42-7.27 (m, 3H), 6.83-6.73 (m, 2H), 6.69-6.63 (m, 1H), 5.15 (s, 2H), 3.90 (s, 3H), 2.32 (s, 3H).

Step 2—1-Benzyloxy-2-methoxy-4-methyl-5-nitro-benzene

A stirred mixture of 1-benzyloxy-2-methoxy-4-methyl-benzene (17.5 g, 76.6 mmol) in HOAc (60 mL) was cooled to 4-6° C. and a mixture of concentrated $HNO_3$ (49.0 g, 778 mmol) in HOAc (17 mL) was added dropwise. The reaction mixture was stirred at 4-6° C. for 3 hours. On completion, the reaction mixture was poured into 100 mL of an ice-$H_2O$ mixture. The mixture was filtered and the solid precipitate was washed with water. The solid was dried in vacuo to give the title compound (20.0 g, 95% yield) as a yellow solid. $^1H$ NMR (400 MHz, DMSO-$d_6$) δ 7.73 (s, 1H), 7.49-7.33 (m, 5H), 7.09 (s, 1H), 5.17 (s, 2H), 3.90 (s, 3H), 2.54 (s, 3H).

Step 3—5-Benzyloxy-4-methoxy-2-methyl-aniline

To a mixture of 1-benzyloxy-2-methoxy-4-methyl-5-nitro-benzene (10.0 g, 36.5 mmol) in MeOH (100 mL) and $H_2O$ (60 mL) was added Fe (26.5 g, 475 mmol) and $NH_4Cl$ (25.4 g, 475 mmol). The reaction mixture was stirred at 65° C. for 12 hours. On completion, the reaction mixture was filtered and concentrated in vacuo to remove the MeOH. The residue was diluted with water (50 mL), and neutralized with sat. $NaHCO_3$ (20 mL) until the pH=8-9. The residue was diluted with water (30 mL) and extracted with EA (2×100 mL). The combined organic layer was dried over $Na_2SO_4$, filtered and concentrated in vacuo to give a residue. The residue was purified by column chromatography to give the title compound (1.60 g, 17% yield) as a white solid. LC-MS ($ESI^+$) m/z 244.1 $(M+H)^+$.

Step 4—N1-(2,5-dichloropyrimidin-4-yl)-4-methoxy-benzene-1,2-diamine

A mixture of 4-methoxybenzene-1,2-diamine (25.0 g, 180 mmol) and DIPEA (28.0 g, 217 mmol) in IPA (150 mL) was stirred at 0° C. 2,4,5-trichloropyrimidine (33.1 g, 180 mmol) was then added dropwise and the mixture was allowed to warm to rt and stirred for 1 hour. On completion, the reaction mixture was concentrated in vacuo to remove the IPA. The residue was diluted with water (50 mL) and extracted with EA (2×100 mL). The combined organic layer was dried over $Na_2SO_4$, filtered and concentrated in vacuo to give the title compound (44.0 g, 85% yield) as a pale solid. LC-MS ($ESI^+$) m/z 284.9 $(M+H)^+$.

Step 5—N-[2-[(2,5-dichloropyrimidin-4-yl)amino]-5-methoxy-phenyl]methanesulfonamide To a mixture of N1-(2,5-dichloropyrimidin-4-yl)-4-methoxy-benzene-1,2-diamine (8.00 g, 28.0 mmol) in pyridine (20 mL) was added MsCl (3.54 g, 30.8 mmol) at 0° C. Then the reaction mixture was then allowed to warm to rt and stirred for 4 hours. On completion, the reaction mixture was concentrated in vacuo. The residue was purified by column chromatography to give the title compound (7.00 g, 68% yield) as a pale solid. LC-MS ($ESI^+$) m/z 362.9 $(M+H)^+$.

2-Methoxy-4-methyl-5-nitro-phenol (Intermediate FF)

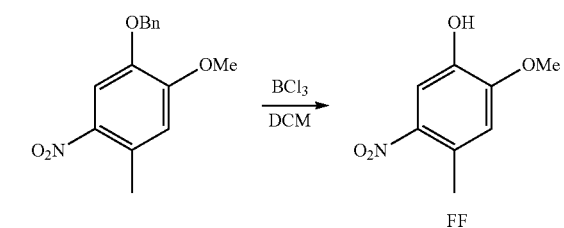

To a mixture of 1-benzyloxy-2-methoxy-4-methyl-5-nitro-benzene (5.00 g, 18.3 mmol, synthesized via Steps 1-2 of Intermediate FE) in DCM (60 mL) was added $BCl_3$.DCM (1.0 M, 91 mL). Then the reaction mixture was stirred at rt for 8 hours. On completion, the reaction mixture was concentrated in vacuo. The reaction mixture was washed with sat.$NaHCO_3$ (150 mL) and extracted with DCM (3×100 mL). The organic layer was dried with $Na_2SO_4$, filtrated and concentrated in vacuo. The residue was purified by column chromatography to give the title compound (2.80 g, 83% yield) as yellowish solid. LC-MS ($ESI^+$) m/z 184.1 $(M+H)^+$.

2,3-Dimethoxy-5-nitrophenol (Intermediate FG)

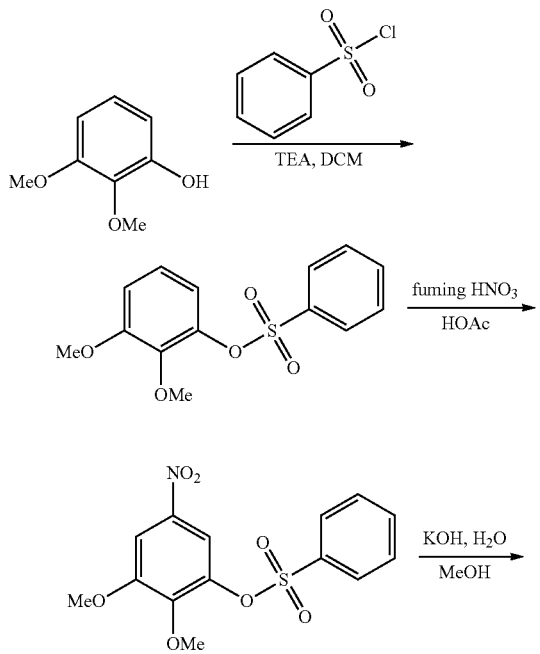

-continued

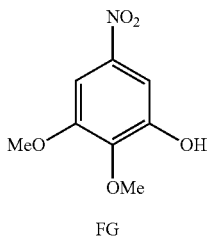

FG

Step 1—2,3-Dimethoxyphenyl benzenesulfonate

To a solution of 2,3-dimethoxyphenol (10.0 g, 64.8 mmol, 8.47 mL) in dichloromethane (200 mL) was added triethylamine (13.1 g, 129 mmol, 17.9 mL) at 0° C. Then benzenesulfonyl chloride (13.7 g, 77.8 mmol, 9.96 mL) was added dropwise over 1 hour at 0° C. The mixture was then allowed to warm to rt and stirred for 15 hours. On completion, the reaction mixture was diluted with water (700 mL), and then extracted with dichloromethane (4×250 mL). The combined organic layers were washed with brine (2×250 mL), dried over anhydrous sodium sulfate, filtered and concentrated in vacuo to give a residue. The residue was purified by silica gel chromatography (petroleum ether:ethyl acetate=10:1) to give the title compound (17.0 g, 89% yield) as a light yellow oil. $^1$H NMR (400 MHz, CDCl$_3$) δ 7.85 (t, J=7.2 Hz, 2H), 7.57 (d, J=7.6 Hz, 1H), 7.45 (t, J=8.0 Hz, 2H), 6.89-6.87 (m, 1H), 6.78-6.75 (m, 2H), 3.75 (s, 3H), 3.61 (s, 3H).

Step 2—2,3-Dimethoxy-5-nitrophenyl benzenesulfonate

To a solution of (2,3-dimethoxyphenyl)benzenesulfonate (17.0 g, 57.7 mmol) in acetic acid (340 mL) was added nitrosoaphyllinic acid (17.0 g, 57.7 mmol, 61.2 mL) dropwise over 1 hour at 0° C. The mixture was then allowed to warm to rt and was stirred for 15 hours. On completion, the reaction mixture was diluted with water 50 mL and extracted with ethyl acetate (3×300 mL). The combined organic layers were washed with brine (2×300 mL), dried over anhydrous sodium sulfate, filtered and concentrated in vacuo to give a residue. The residue was purified by column chromatography (petroleum ether:ethyl acetate=50:1 to 20:1) to give the title compound (17.0 g, 86% yield) as a white solid. $^1$H NMR (400 MHz, CDCl$_3$) δ 7.96 (t, J=5.2 Hz, 1H), 7.74 (d, J=4.8 Hz, 1H), 7.63-7.61 (m, 5H), 3.96 (s, 3H), 3.88 (s, 3H).

Step 3—2,3-Dimethoxy-5-nitrophenol

To a solution of (2,3-dimethoxy-5-nitro-phenyl)benzenesulfonate (2.80 g, 8.25 mmol) in methanol (28.2 mL) was added 20% potassium hydroxide solution (16.89 mL). The mixture was stirred at 50° C. for 4 hours. On completion, the reaction mixture was concentrated in vacuo to remove methanol. The residue was diluted with water (50 mL), and acidified with HCl until the pH=5-6. The mixture was then filtered, and the solid precipitate was collected and dried in vacuo to give the title compound (1.40 g, 85% yield) as a white solid. $^1$H NMR (400 MHz, CDCl$_3$) δ 7.45 (d, J=2.8 Hz, 1H), 7.34 (d, J=2.8 Hz, 1H), 5.94 (s, 1H), 3.95 (s, 3H), 3.83 (s, 3H).

(±)-Tert-butyl 2-ethyl-4-[5-(2-methylsulfonylpyrimidin-4-yl)-2-pyridyl]piperazine-1-carboxylate (Intermediate FH)

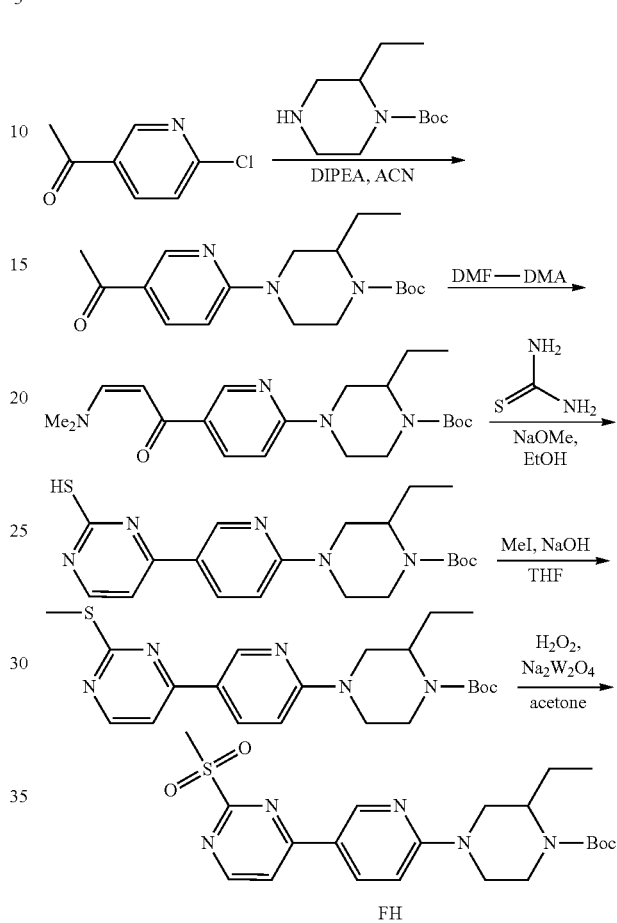

FH

Step 1—(±)-Tert-butyl 4-(5-acetyl-2-pyridyl)-2-ethyl-piperazine-1-carboxylate To a solution of 1-(6-chloro-3-pyridyl)ethanone (4.00 g, 24.9 mmol; CAS #36357-38-7) in ACN (8 mL) was added DIPEA (9.67 g, 74.8 mmol) and (±)-tert-butyl 2-ethylpiperazine-1-carboxylate (6.41 g, 29.9 mmol; CAS #393781-71-0). The reaction mixture was stirred at 85° C. for 12 hours. On completion, the reaction mixture was concentrated in vacuo to give a residue. The residue was purified by column chromatography (petroleum ether:ethyl acetate=30:1 to 5:1) to give the title compound (8.30 g, 100% yield) as a yellow oil. $^1$H NMR (400 MHz, CDCl$_3$) δ 8.75 (d, J=2.0 Hz, 1H), 8.03 (dd, J=2.4, 9.2 Hz, 1H), 6.58 (d, J=8.8 Hz, 1H), 4.34 (d, J=13.2 Hz, 1H), 4.27 (d, J=10.4 Hz, 1H), 4.13 (q, J=7.2 Hz, 1H), 4.02 (s, 1H), 3.27 (dd, J=4.0, 13.2 Hz, 1H), 3.20-3.04 (m, 2H), 2.51 (s, 3H), 1.63-1.50 (m, 2H), 1.49 (s, 9H), 0.90 (t, J=7.2 Hz, 3H).

Step 2—(±)-Ethyl 1-(4-bromo-3,5-dimethyl-phenyl)-5-phenyl-pyrazole-4-carboxylate A mixture of (±)-tert-butyl 4-(5-acetyl-2-pyridyl)-2-ethyl-piperazine-1-carboxylate (8.30 g, 24.9 mmol) and 1,1-dimethoxy-N,N-dimethyl-methanamine (29.7 g, 249 mmol) was heated to 110° C. for 14 hours. LCMS showed that the starting material remained, thus the reaction was then heated to 120° C. for another 22 hours. On completion, the reaction mixture was concentrated in vacuo to give the residue. The residue was purified by column chromatography (petroleum ether:ethyl acetate=5:1 to ethyl acetate) to give the title compound (7.70 g, 80% yield) as a yellow oil. $^1$H NMR (400 MHz, CDCl$_3$) δ 8.73 (d, J=2.4 Hz, 1H), 8.07 (dd, J=2.4, 8.8 Hz, 1H), 7.79 (d, J=12.4 Hz, 1H), 6.59 (d, J=8.8 Hz, 1H), 5.66 (d, J=12.4 Hz, 1H), 4.31-4.21 (m, 2H), 4.12 (q, J=7.2 Hz, 1H), 3.99 (d, J=10.4 Hz, 1H), 3.49 (s, 1H), 3.24-2.97 (m, 8H), 1.67-1.52 (m, 2H), 1.49 (s, 9H), 0.90 (t, J=7.2 Hz, 3H).

Step 3—(±)-Tert-butyl 2-ethyl-4-[5-(2-sulfanylpyrimidin-4-yl)-2-pyridyl]piperazine-1-carboxylate To a solution of (±)-tert-butyl 4-[5-[(Z)-3-(dimethylamino)prop-2-enoyl]-2-pyridyl]-2-ethyl-piperazine-1-carboxylate (7.70 g, 19.8 mmol) in ethanol (80 mL) was added thiourea (3.02 g, 39.6 mmol) and NaOMe (2.68 g, 49.6 mmol). The reaction mixture was stirred at 78° C. for 12 hours. On completion, the reaction mixture was concentrated in vacuo to give the title compound (7.90 g, 99% yield) as a white solid. LC-MS (ESI$^+$) m/z 401.9 (M+H)$^+$.

Step 4—(±)-Tert-butyl 2-ethyl-4-[5-(2-methylsulfanylpyrimidin-4-yl)-2-pyridyl]piperazine-1-carboxylate To a solution of (±)-tert-butyl 2-ethyl-4-[5-(2-sulfanylpyrimidin-4-yl)-2-pyridyl]piperazine-1-carboxylate (7.90 g, 19.7 mmol) and iodomethane (11.2 g, 78.7 mmol) in THF (80 mL) was added NaOH (1 M, 29.5 mL). The reaction mixture was stirred at rt for 5 hours. On completion, the reaction mixture was diluted with water (20 mL) and extracted with ethyl acetate (3×20 mL). The combined organic layers were washed with brine (10 mL), dried over anhydrous Na$_2$SO$_4$, filtered and concentrated in vacuo to give a residue. The residue was purified by column chromatography (petroleum ether:ethyl acetate=5:1 to dichloromethane:methanol=100:1) to give the title compound (7.70 g, 94% yield) as a yellow solid. $^1$H NMR (400 MHz, CDCl$_3$) δ 8.90 (d, J=2.0 Hz, 1H), 8.45 (d, J=5.2 Hz, 1H), 8.22 (dd, J=2.4, 8.8 Hz, 1H), 7.24 (d, J=5.2 Hz, 1H), 6.66 (d, J=8.8 Hz, 1H), 4.31 (d, J=13.2 Hz, 1H), 4.25 (d, J=11.6 Hz, 1H), 4.18-4.08 (m, 1H), 4.03 (s, 1H), 3.25 (dd, J=4.0, 13.2 Hz, 1H), 3.21-3.02 (m, 2H), 2.63 (s, 3H), 1.70-1.64 (m, 1H), 1.55 (dd, J=7.2, 14.4 Hz, 1H), 1.50 (s, 9H), 0.91 (t, J=7.2 Hz, 3H).

Step 5—(+)-Tert-butyl 2-ethyl-4-[5-(2-methylsulfonylpyrimidin-4-yl)-2-pyridyl]piperazine-1-carboxylate To a solution of (±)-tert-butyl 2-ethyl-4-[5-(2-methylsulfanylpyrimidin-4-yl)-2-pyridyl]piperazine-1-carboxylate (3.85 g, 9.26 mmol) in acetone (15.0 mL) was added H$_2$O$_2$ (5.90 g, 52.0 mmol) and disodium dioxide (dioxo) tungstendihydrate (306 mg, 926 umol). The reaction mixture was stirred at 40° C. for 12 hours. On completion, the reaction mixture was quenched with saturated Na$_2$SO$_4$ (20 mL) and extracted with dichloromethane (3×100 mL). The combined organic layer was washed with brine (50 mL), dried over anhydrous sodium sulfate, filtered and concentrated in vacuo. The residue was purified by silica gel chromatography (dichloromethane:methanol=100:1) to give the title compound (4.00 g, 97% yield) as a white solid. $^1$H NMR (400 MHz, CDCl$_3$) δ 8.93 (d, J=2.0 Hz, 1H), 8.78 (d, J=5.6 Hz, 1H), 8.31 (dd, J=2.4, 9.2 Hz, 1H), 7.74 (d, J=5.6 Hz, 1H), 6.69 (d, J=8.8 Hz, 1H), 4.37 (d, J=13.4 Hz, 1H), 4.29 (d, J=8.8 Hz, 1H), 4.19-3.99 (m, 2H), 3.41 (s, 3H), 3.30 (dd, J=3.6, 13.2 Hz, 1H), 3.21-3.08 (m, 2H), 1.69-1.61 (m, 1H), 1.53 (d, J=7.2 Hz, 1H), 1.50 (s, 9H), 0.92 (t, J=7.2 Hz, 3H).

4-[3-(Tert-butoxycarbonylamino)methyl-4-[[2-[2-[tert-butoxycarbonyl(2,2,2-trifluoroethyl)amino]-4-pyridyl]oxazole-4-carbonyl]amino]pyrazol-1-yl]benzoic acid (Intermediate FI)

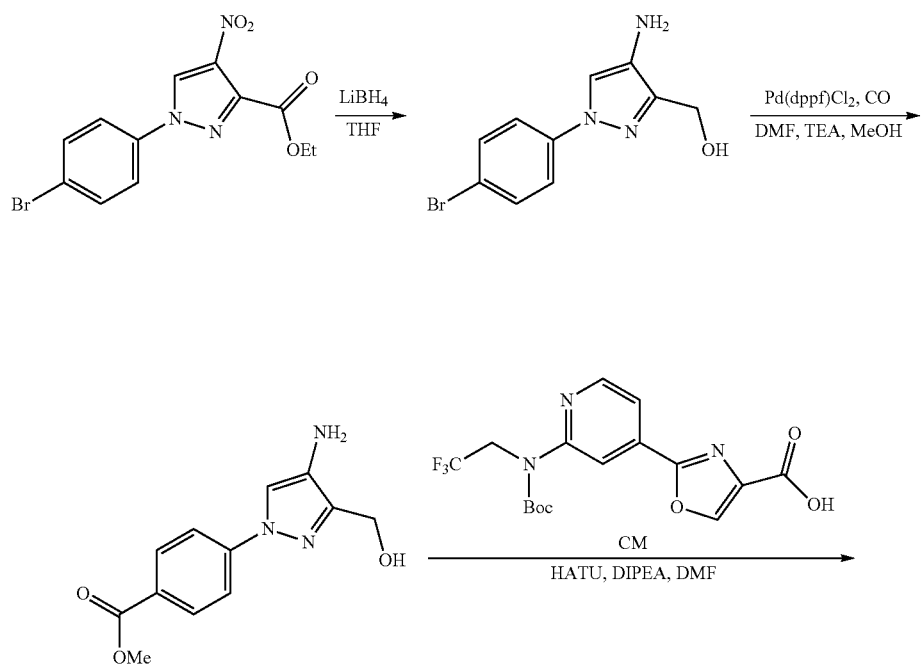

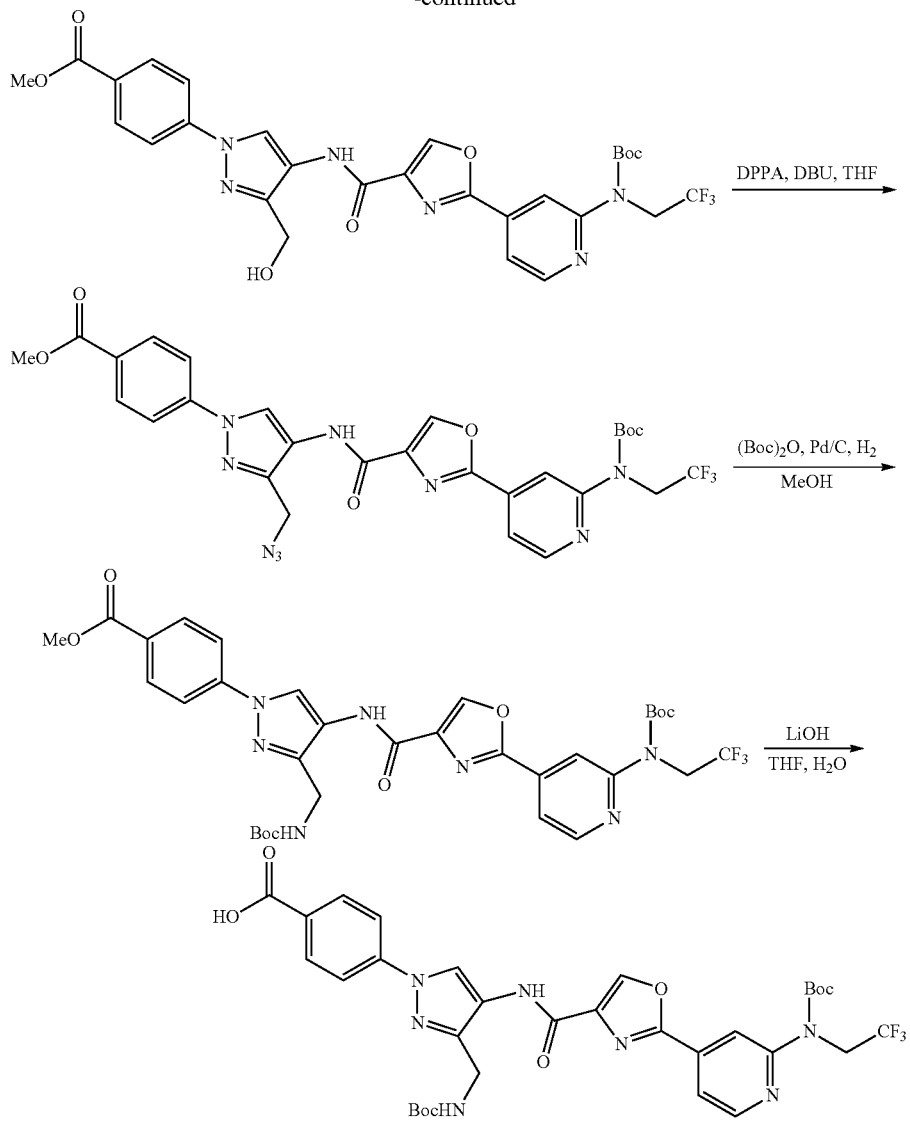

FI

Step 1—[4-Amino-1-(4-bromophenyl)pyrazol-3-yl]methanol

To a solution of ethyl 1-(4-bromophenyl)-4-nitro-pyrazole-3-carboxylate (3.70 g, 10.8 mmol, synthesized via Steps 1-2 of Intermediate CL) in THF (30.0 mL) was added LiBH₄ (1.18 g, 54.3 mmol). The reaction mixture was stirred at 50° C. for 3 hrs under N₂. On completion, the reaction mixture was quenched with water (100 mL), concentrated in vacuo to removed the THF, and filtered. The filtered cake was collected and dried under vaccuum to give the title compound (1.80 g, 61% yield) as yellow solid. ¹H NMR (400 MHz, DMSO-d₆) δ 7.72 (s, 1H), 7.69-7.62 (m, 4H), 5.07-5.03 (m, 1H), 4.51 (d, J=5.6 Hz, 2H), 4.16 (s, 2H).

Step 2—Methyl 4-[4-amino-3-(hydroxymethyl)pyrazol-1-yl]benzoate

To a solution of [4-amino-1-(4-bromophenyl)pyrazol-3-yl]methanol (1.60 g, 5.97 mmol) in a mixed solvent of DMF (30.0 mL) and MeOH (30.0 mL) was added Pd(dppf)Cl₂.CH₂Cl₂ (487 mg, 596 umol) and TEA (1.81 g, 17.9 mmol, 2.49 mL) under N₂. The suspension was degassed in vacuo and purged with CO several times. The mixture was stirred under CO (50 psi) at 80° C. for 36 hours. On completion, the reaction mixture was concentrated in vacuo to give the residue. The residue was purified by prep-HPLC (0.1%, HCl) to give the title compound (800 mg, 54% yield) as white solid. ¹H NMR (400 MHz, DMSO-d₆) δ 8.62 (s, 1H), 8.08 (d, J=8.8 Hz, 2H), 8.03-7.93 (m, 2H), 4.63 (s, 2H), 3.87 (s, 3H).

Step 3—Methyl 4-[4-[[2-[2-[tert-butoxycarbonyl(2,2,2-trifluoroethyl)amino]-4-pyridyl]oxazole-4-carbonyl]amino]-3-(hydroxymethyl)pyrazol-1-yl]benzoate To a solution of methyl 4-[4-amino-3-(hydroxymethyl)pyrazol-1-yl]benzoate (400 mg, 1.62 mmol) and 2-[2-[tert-butoxycarbonyl(2,2,2-trifluoroethyl)amino]-4-pyridyl]oxazole-4-carboxylic acid (626 mg, 1.62 mmol, Intermediate CM) in DMF (3.00 mL) was added DIPEA (418 mg, 3.24 mmol). The reaction mixture was stirred at 25° C. for 0.5 hr. Then, HATU (676 mg, 1.78 mmol) was added. The resulting reaction mixture was stirred at 25° C. for 0.5 hr. On completion, the reaction mixture was quenched with water (15 mL), and a white solid precipitation formed, which was filtered. The filter cake was dried in vacuo to give the title compound (920 mg, 92% yield) as white solid. $^1$H NMR (400 MHz, DMSO-$d_6$) δ 9.08 (s, 1H), 8.90 (s, 1H), 8.66 (d, J=5.2 Hz, 1H), 8.10-8.04 (m, 2H), 8.02-7.96 (m, 2H), 7.73-7.70 (m, 2H), 7.83-7.75 (m, 1H), 4.91-4.87 (m, 2H), 4.80 (d, J=5.2 Hz, 2H), 3.87 (s, 3H), 1.53 (s, 9H).

Step 4—Methyl 4-[3-(azidomethyl)-4-[[2-[2-[tert-butoxycarbonyl(2,2,2-trifluoroethyl)amino]-4-pyridyl]oxazole-4-carbonyl]amino]pyrazol-1-yl]benzoate To a solution of methyl 4-[4-[[2-[2-[tert-butoxycarbonyl (2,2,2-trifluoroethyl)amino]-4-pyridyl]oxazole-4-carbonyl] amino]-3-(hydroxymethyl)pyrazol-1-yl]benzoate (500 mg, 810 umol) in THF (15.0 mL) was added DPPA (334 mg, 1.22 mmol) and DBU (308 mg, 2.03 mmol) at 0° C. The mixture was stirred at 25° C. for 3 hr. On completion, the mixture was diluted with H$_2$O (50 mL), then extracted with DCM (3×30 mL). The organic layers were dried over anhydrous Na$_2$SO$_4$, filtered and concentrated in vacuo to give the title compound (520 mg, 70% yield) as yellow solid. LC-MS (ESI$^+$) m/z 642.3 (M+H)$^+$.

Step 5—Methyl 4-[3-[(tert-butoxycarbonylamino)methyl]-4-[[2-[2-[tert-butoxycarbonyl(2,2,2-trifluoroethyl)amino]-4-pyridyl]oxazole-4-carbonyl]amino]pyrazol-1-yl]benzoate To a solution of methyl 4-[3-(azidomethyl)-4-[[2-[2-[tert-butoxycarbonyl(2,2,2-trifluoroethyl)amino]-4-pyridyl]oxazole-4-carbonyl]amino]pyrazol-1-yl]benzoate (520 mg, 810 umol) and (Boc)$_2$O (265 mg, 1.22 mmol) in MeOH (10.0 mL) was added Pd/C (100 mg, 810 umol). The mixture was stirred at 25° C. for 3 hrs under H$_2$ (15 psi). On completion, the mixture was filtered and concentrated in vacuo. The mixture was purified by reverse phase (0.1% FA) to give the title compound (500 mg, 86% yield) as white solid. $^1$H NMR (400 MHz, DMSO-$d_6$) δ 10.64 (s, 1H), 9.05 (s, 1H), 8.95 (s, 1H), 8.64 (d, J=5.2 Hz, 1H), 8.35 (s, 1H), 8.09 (s, 1H), 8.07 (s, 1H), 8.00 (s, 1H), 7.98 (s, 1H), 7.86 (d, J=5.2 Hz, 1H), 7.79 (s, 1H), 4.91 (d, J=8.8 Hz, 2H), 4.29 (d, J 6.8 Hz, 2H), 3.88 (s, 3H), 1.52 (s, 9H), 1.36 (s, 9H).

Step 6—4-[3-[(Tert-butoxycarbonylamino)methyl]-4-[[2-[2-[tert-butoxycarbonyl(2,2,2-trifluoroethyl)amino]-4-pyridyl]oxazole-4-carbonyl]amino]pyrazol-1-yl]benzoic acid (8)—Notebook Page: EW7002-283

To a solution of methyl 4-[3-[(tert-butoxycarbonylamino) methyl]-4-[[2-[2-[tert-butoxycarbonyl (2,2,2-trifluoroethyl) amino]-4-pyridyl]oxazole-4-carbonyl]amino]pyrazol-1-yl] benzoate (160 mg, 223 umol) in a mixed solvent of THF (20.0 mL), H$_2$O (5.00 mL) and MeOH (5.00 mL) was added LiOH (26.7 mg, 1.12 mmol). The mixture was stirred at 25° C. for 16 hrs. On completion, the mixture was acidified with 1N HCl solution until the pH=5. The mixture was diluted with H$_2$O (50 mL), and extracted with EA (3×30 mL). The organic layers were dried over anhydrous Na$_2$SO$_4$, filtered and concentrated in vacuo to give the title compound (70.0 mg, 44% yield) as white solid. LC-MS (ESI$^+$) m/z 702.4 (M+H)$^+$.

2-[2-[2-[2-(4-Iodophenoxy)ethoxy]ethoxy]ethoxy]ethanamine (Intermediate FJ)

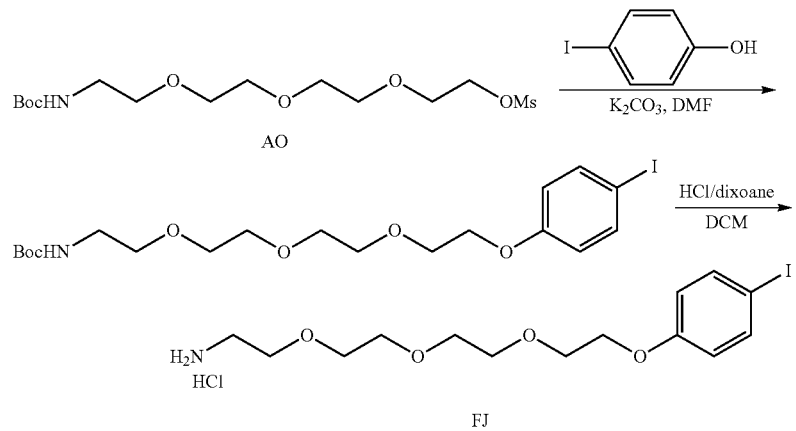

Step 1—Tert-butyl N-[2-[2-[2-[2-(4-iodophenoxy)ethoxy]ethoxy]ethoxy]ethyl]carbamate To a solution of 4-iodophenol (1 g, 4.55 mmol) and 2-[2-[2-[2-(tert-butoxycarbonylamino)ethoxy]ethoxy] ethoxy]ethyl methanesulfonate (1.69 g, 4.55 mmol, Intermediate AO) in DMF (15 mL) was added K$_2$CO$_3$ (1.57 g, 11.3 mmol), and the reaction mixture was stirred at 100° C. for 12 hr. On completion, the mixture was diluted with H$_2$O (30 mL), then extracted with EA (2×40 mL), and the organic phase was concentrated in vacuo to give a residue. The residue was purified by reverse phase (0.1% FA condition) to give the title compound (1.00 g, 44% yield) as yellow oil. LC-MS (ESI$^+$) m/z 496.2 (M+H)$^+$.

Step 2—2-[2-[2-[2-(4-Iodophenoxy)ethoxy]ethoxy]ethoxy]ethanamine

To a solution of tert-butyl N-[2-[2-[2-[2-(4-iodophenoxy) ethoxy]ethoxy]ethoxy]ethyl]carbamate (0.9 g, 1.82 mmol)

in DCM (2 mL) was added HCl/dixoane (4 M, 2.00 mL), and the reaction mixture was stirred at 20° C. for 20 mins. On completion, the residue was concentrated in vacuo to give the title compound (800 mg, 99% yield) as yellow oil. LC-MS (ESI+) m/z 396.1 (M+1)+.

2-[2-[2-[[2-(2,6-Dioxo-3-piperidyl)-1,3-dioxo-isoindolin-4-yl]amino]ethoxy]ethoxy]acetaldehyde (Intermediate FK)

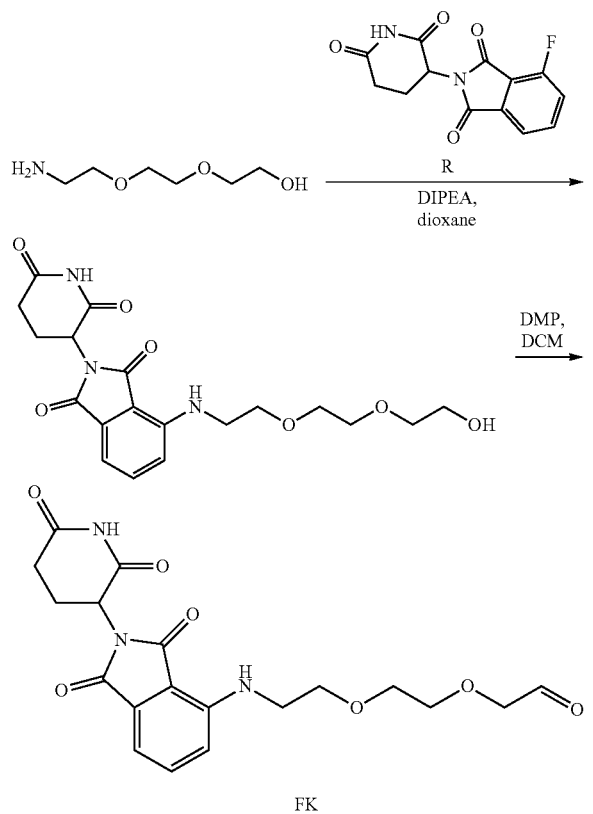

FK

Step 1—2-(2,6-Dioxo-3-piperidyl)-4-[2-[2-(2-hydroxyethoxy)ethoxy]ethylamino]isoindoline-1,3-dione To a solution of 2-[2-(2-aminoethoxy)ethoxy]ethanol (1.80 g, 12.0 mmol, CAS #6338-55-2) and 2-(2,6-dioxo-3-piperidyl)-4-fluoroisoindoline-1,3-dione (4.00 g, 14.4 mmol, Intermediate R) in dioxane (35.0 mL) was added DIPEA (9.36 g, 72.3 mmol). The reaction mixture was stirred at 115° C. for 20 hrs. On completion, the mixture was concentrated in vacuo to remove the solvent. The residue was purified by silica gel chromatography (PE:EA=1:1) to give the title compound (2.90 g, 59% yield) as yellow solid. $^1$H NMR (400 MHz, CDCl$_3$) δ 8.28 (s, 1H), 7.50 (dd, J=7.2, 8.4 Hz, 1H), 7.11 (d, J=7.2 Hz, 1H), 6.91 (d, J=8.4 Hz, 1H), 6.57 (t, J=5.2 Hz, 1H), 4.96-4.85 (m, 1H), 3.77-3.67 (m, 8H), 3.64-3.59 (m, 2H), 3.48 (q, J=5.2 Hz, 2H), 2.92-2.70 (m, 3H), 2.62 (s, 1H), 2.17-2.08 (m, 1H).

Step 2—2-[2-[2-[[2-(2,6-Dioxo-3-piperidyl)-1,3-dioxo-isoindolin-4-yl]amino]ethoxy]ethoxy]acetaldehyde (11)—Notebook Page: EW7002-288

To a solution of 2-(2,6-dioxo-3-piperidyl)-4-[2-[2-(2-hydroxyethoxy)ethoxy]ethylamino]isoindoline-1,3-dione (200 mg, 493 umol) in DCM (10.0 mL) was added DMP (209 mg, 493 umol). The mixture was stirred at 25° C. for 16 hrs. On completion, the mixture was diluted with DCM (30 mL), and extracted with saturated Na$_2$S$_2$O$_3$ (2×30 mL) and saturated NaHCO$_3$ (2×30 mL). The organic layer was dried over anhydrous Na$_2$SO$_4$, filtered and concentrated in vacuo to give the title compound (140 mg, 70% yield) as yellow solid. $^1$H NMR (400 MHz, CDCl$_3$) δ 9.74 (s, 1H), 8.15 (s, 1H), 7.52 (t, J=7.6 Hz, 1H), 7.14 (d, J=7.2 Hz, 1H), 6.97-6.90 (m, 1H), 6.57-6.49 (m, 1H), 4.97-4.89 (m, 1H), 3.83-3.65 (m, 10H), 2.17-2.11 (m, 1H), 1.91-1.87 (m, 1H), 1.87-1.83 (m, 1H), 1.31-1.03 (m, 1H).

Tert-butyl 5-(4,4,5,5-tetramethyl-1,3,2-dioxaborolan-2-yl)isoindoline-2-carboxylate (Intermediate FL)

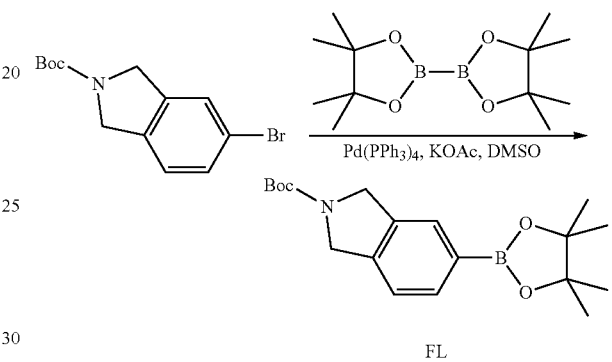

FL

To a solution of tert-butyl 5-bromoisoindoline-2-carboxylate (1.20 g, 4.02 mmol, CAS #201940-08-1), 4,4,5,5-tetramethyl-2-(4,4,5,5-tetramethyl-1,3,2-dioxaborolan-2-yl)-1,3,2-dioxaborolane (1.12 g, 4.43 mmol) in DMSO (20.0 mL) was added KOAc (1.18 g, 12.0 mmol) and Pd(PPh$_3$)$_4$ (139 mg, 120 umol). The mixture was stirred at 80° C. for 16 hours under N$_2$. On completion, the mixture was diluted with H$_2$O (50 mL), and extracted with EA (3×30 mL). The organic layers were washed with brine (3×30 mL), dried over anhydrous Na$_2$SO$_4$, filtered and concentrated in vacuo. The mixture was purified by prep-HPLC (reserve phase (0.1% FA)) to give the title compound (500 mg, 36% yield) as yellow solid. $^1$H NMR (400 MHz, CDCl$_3$) δ 7.75 (s, 1H), 7.32-7.29 (m, 1H), 7.25 (d, J=7.6 Hz, 1H), 4.74-4.66 (m, 4H), 1.54 (s, 9H), 1.37 (s, 12H).

Tert-butyl 5-[4-amino-3-(trifluoromethyl)pyrazol-1-yl]isoindoline-2-carboxylate (Intermediate FM)

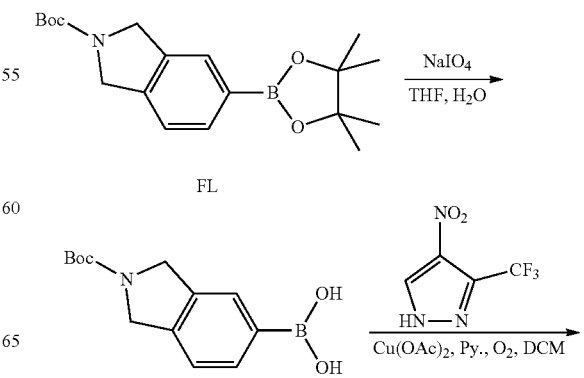

1331

-continued

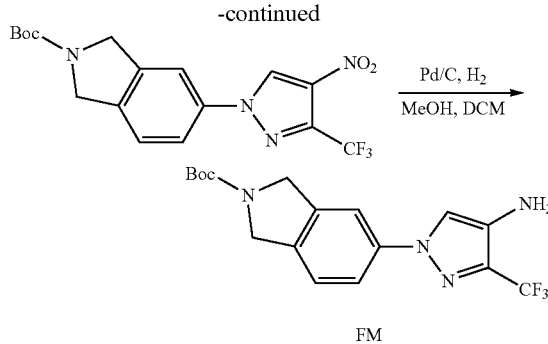

Step 1—(2-Tert-butoxycarbonylisoindolin-5-yl)boronic acid

To a solution of tert-butyl 5-(4,4,5,5-tetramethyl-1,3,2-dioxaborolan-2-yl)isoindoline-2-carboxylate (500 mg, 1.45 mmol, Intermediate FL) in a mixed solvent of THF (20.0 mL) and H$_2$O (4.00 mL) was added NaIO$_4$ (929 mg, 4.34 mmol). The mixture was stirred at 25° C. for 0.5 hr. HCl (3 M, 965 uL) was added to the mixture; and the mixture was stirred at 25° C. for 1.5 hrs. On completion, the mixture was diluted with H$_2$O (30 mL), and extracted with EA (3×30 mL). The organic layers were washed with brine (3×20 mL), the organic layers were dried over anhydrous Na$_2$SO$_4$, filtered and concentrated in vacuo. The mixture was purified by prep-HPLC (reverse phase (0.1% FA)) to give the title compound (260 mg, 68% yield) as a white solid. $^1$H NMR (400 MHz, DMSO-d$_6$) δ 8.05 (s, 2H), 7.72 (s, 1H), 7.70 (s, 1H), 7.29 (t, J=6.4 Hz, 1H), 4.64-4.53 (m, 4H), 1.46 (s, 9H).

Step 2—Tert-butyl 5-[4-nitro-3-(trifluoromethyl)pyrazol-1-yl]isoindoline-2-carboxylate To a solution of 4-nitro-3-(trifluoromethyl)-1H-pyrazole (378 mg, 2.09 mmol, synthesized via Step 1 of Intermediate DE), (2-tert-butoxycarbonyl isoindolin-5-yl)boronic acid (660 mg, 2.51 mmol) in DCM (20.0 mL) was added Cu(OAc)$_2$ (569 mg, 3.14 mmol) and pyridine (661 mg, 8.36 mmol). The mixture was stirred at 25° C. for 12 hrs under O$_2$ (15 psi). On completion, the mixture was concentrated in vacuo then washed with NH$_3$.H$_2$O (5 mL), filtered and the solid was dried in vacuo. The mixture was triturated again with MeOH (5 mL), then filtered and the solid was dried in vacuo to give the title compound (400 mg, 48% yield) as white solid. $^1$H NMR (400 MHz, DMSO-d$_6$) δ 9.86 (d, J=6.8 Hz, 1H), 7.93 (d, J=12.8 Hz, 1H), 7.90-7.85 (m, 1H), 7.59-7.52 (m, 1H), 4.71-4.60 (m, 4H), 1.47 (s, 9H).

Step 3—Tert-butyl 5-[4-amino-3-(trifluoromethyl)pyrazol-1-yl]isoindoline-2-carboxylate (7)—Notebook Page: EW7002-281

To a solution of tert-butyl 5-[4-nitro-3-(trifluoromethyl)pyrazol-1-yl]isoindoline-2-carboxylate (260 mg, 652 umol) in a mixed solvent of DCM (10.0 mL) and MeOH (10.0 mL) was added Pd/C (50.0 mg). Then the reaction mixture was stirred at 25° C. for 16 hrs under H$_2$ (15 psi). On completion, the mixture was filtered and concentrated in vacuo to give the title compound (240 mg, 80% yield) as white solid. LC-MS (ESI$^+$) m/z 369.2 (M+H)$^+$.

1332

4-(4-Aminobutylamino)-2-(2,6-dioxo-3-piperidyl)isoindoline-1,3-dione (Intermediate FN)

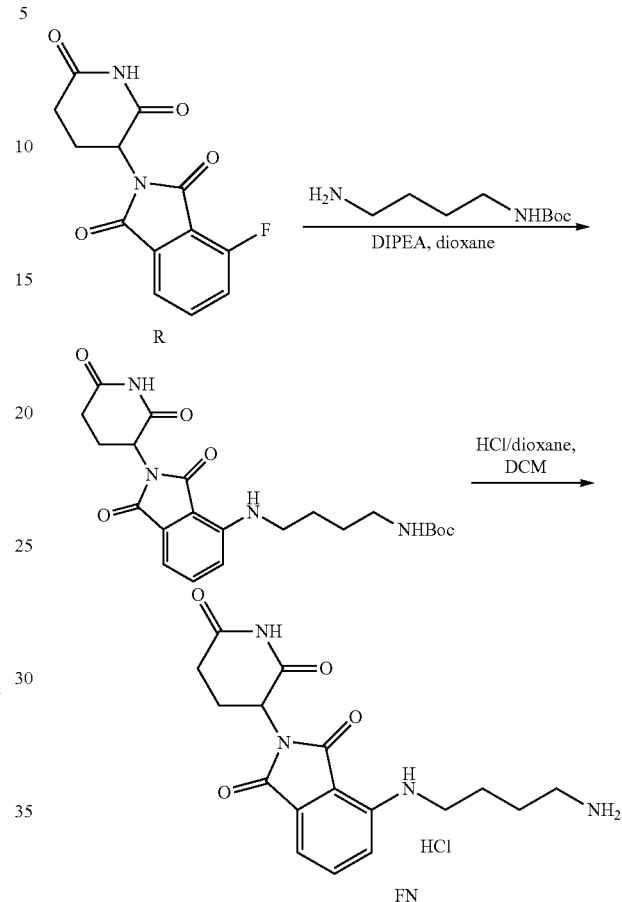

Step 1—Tert-butyl N-[4-[[2-(2,6-dioxo-3-piperidyl)-1,3-dioxo-isoindolin-4-yl]amino]butyl]carbamate To a solution of 2-(2,6-dioxo-3-piperidyl)-4-fluoro-isoindoline-1,3-dione (1.50 g, 5.43 mmol, Intermediate R) and tert-butyl N-(4-aminobutyl)carbamate (1.02 g, 5.43 mmol, CAS #33545-98-1) in dioxane (15 mL) was added DIPEA (2.81 g, 23 mmol). The reaction mixture was stirred at 115° C. for 24 hours. On completion, the mixture was concentrated in vacuo to remove the solvent. The residue was purified by silica gel chromatography to give the title compound (0.96 g, 40% yield) as a yellow solid. LC-MS (ESI$^+$) m/z 445.2 (M+H)$^+$.

Step 2—4-(4-Aminobutylamino)-2-(2,6-dioxo-3-piperidyl)isoindoline-1,3-dione

To a solution of tert-butyl N-[4-[[2-(2,6-dioxo-3-piperidyl)-1,3-dioxo-isoindolin-4-yl]amino]butyl]carbamate (0.96 g, 2.16 mmol) in DCM (5 mL) was added HCl/dioxane (4 M, 10 mL). The reaction mixture was stirred at 25° C. for 3 hours. On completion, the mixture was concentrated in vacuo to give the title compound (0.82 g, 100% yield, HCl) as a yellow solid. The crude product was used for the next step directly without further purification. LC-MS (ESI$^+$) m/z 345.1 (M+H)$^+$.

Tert-butyl N-(3-oxopropyl)carbamate (Intermediate FO)

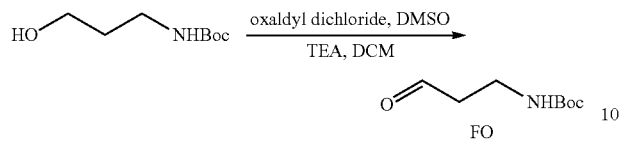

To a solution of DMSO (2.23 g, 28.53 mmol, 2.23 mL, 2.5 eq) in DCM (15 mL) was added a solution of (COCl)$_2$ (2.90 g, 22.8 mmol) in DCM (10 mL) dropwise at −70° C. The mixture was stirred at −70° C. for 10 minutes. Then a solution of tert-butyl N-(3-hydroxypropyl)carbamate (2.00 g, 11.4 mmol, CAS #58885-58-8) in DCM (15 mL) was added into the above mixture slowly. After stirred at −70° C. for 50 minutes, TEA (6.93 g, 68.5 mmol) was added and the reaction mixture was stirred at −70° C. for 0.5 hour. On completion, the mixture was quenched with water (30 mL) and separated. The aqueous phase was extracted with DCM (2×30 mL). Then the organic phase was combined and washed with brine (100 mL), dried over Na$_2$SO$_4$ and concentrated in vacuo to give the title compound (1.70 g, 86% yield) as yellow oil. The residue was used for the next step directly without further purification. $^1$H NMR (400 MHz, CDCl$_3$) δ 9.80 (s, 1H), 5.01-4.87 (m, 1H), 3.41 (q, J=6.0 Hz, 2H), 2.70 (t, J=6.0 Hz, 2H), 1.42 (s, 9H).

4-[4-(3-Aminopropylamino)butylamino]-2-(2,6-dioxo-3-piperidyl)isoindoline-1,3-dione (Intermediate FP)

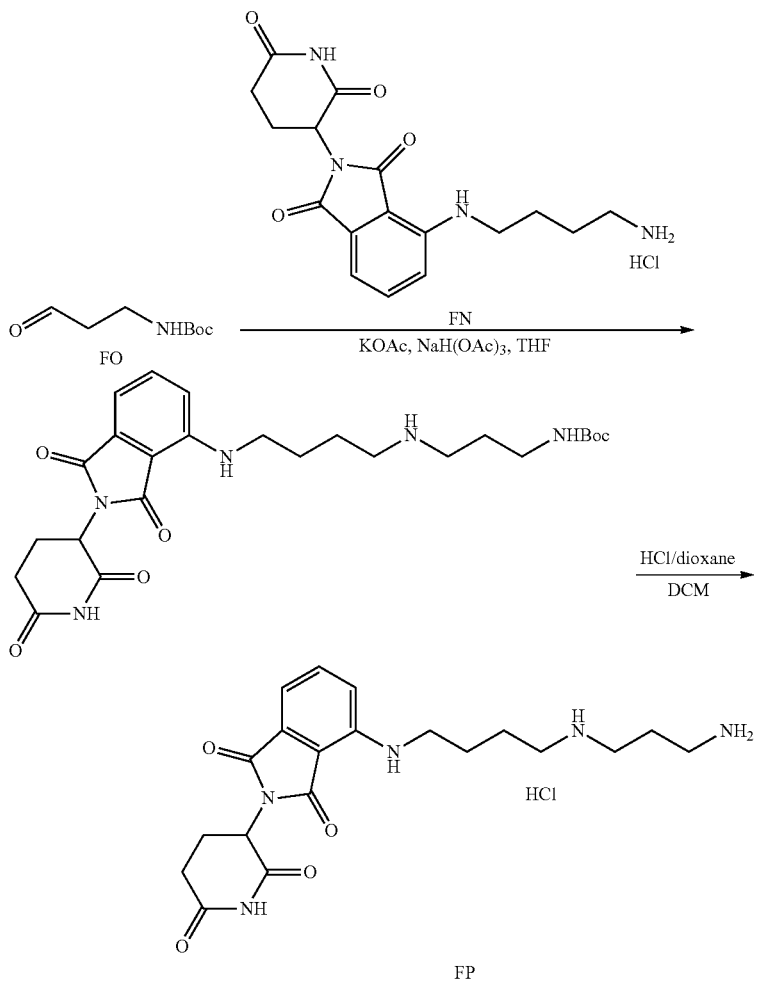

Step 1—Tert-butyl N-[3-[4-[[2-(2,6-dioxo-3-piperidyl)-1,3-dioxo-isoindolin-4-yl]amino]butylamino]propyl]carbamate To a solution of tert-butyl N-(3-oxopropyl)carbamate (0.10 g, 577 umol, Intermediate FO) and 4-(4-aminobutylamino)-2-(2,6-dioxo-3-piperidyl)isoindoline-1,3-dione (264 mg, 693 umol, HCl, Intermediate FN) in THF (20 mL) was added KOAc (113 mg, 1.15 mmol). One hour later, NaBH(OAc)$_3$ (245 mg, 1.15 mmol) was added into the above mixture. The reaction mixture was stirred at 25° C. for 72 hours. On completion, the mixture was concentrated in vacuo. The residue was purified by reverse phase (0.1% HCl condition) to give the title compound (60.0 mg, 21% yield) as a yellow solid. LC-MS (ESI⁺) m/z 502.1 (M+H)⁺.

Step 2—4-[4-(3-Aminopropylamino)butylamino]-2-(2,6-dioxo-3-piperidyl)isoindoline-1,3-dione To a solution of tert-butyl N-[3-[4-[[2-(2,6-dioxo-3-piperidyl)-1,3-dioxo-isoindolin-4-yl]amino]butylamino]propyl]carbamate (60.0 mg, 120 umol) in DCM (2 mL) was added HCl/dioxane (4 mL). The reaction mixture was stirred at 25° C. for 0.5 hour. On completion, the mixture was concentrated in vacuo to give the title compound (50.0 mg, 95% yield, HCl) as a yellow solid. The residue was used for the next step directly without further purification. LC-MS (ESI⁺) m/z 402.1 (M+H)⁺.

Tert-butyl N-[3-[4-(aminomethyl)imidazol-1-yl]propyl]carbamate (Intermediate FQ)

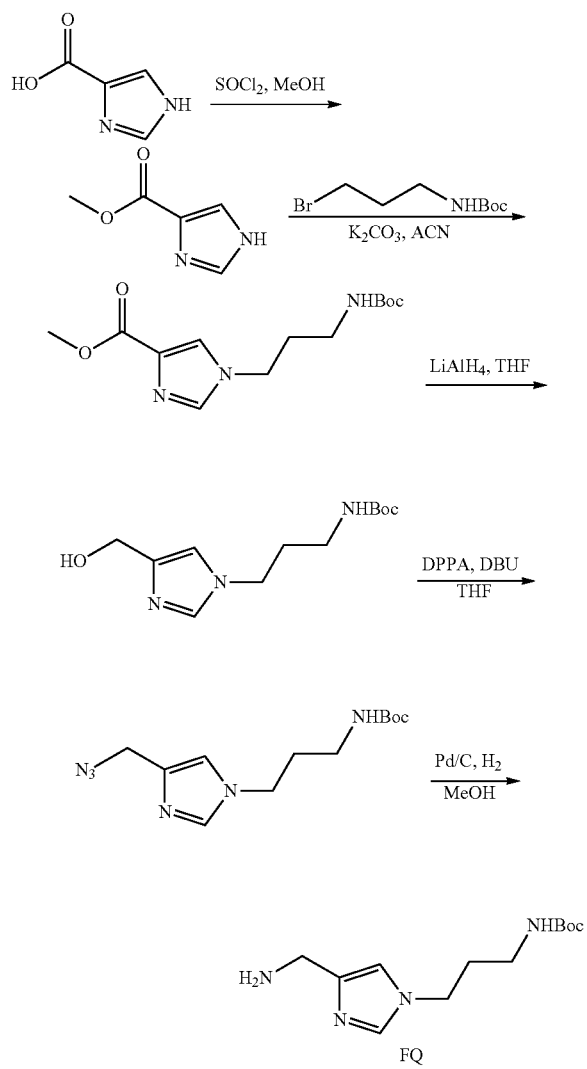

Step 1—Methyl 1H-imidazole-4-carboxylate

To a mixture of 1H-imidazole-4-carboxylic acid (5.00 g, 44.6 mmol, CAS #1072-84-0) in MeOH (50 mL) was added SOCl₂ (10.6 g, 89.2 mmol, 6.47 mL). The reaction mixture was stirred at 70° C. for 16 hours. On completion, the reaction mixture was concentrated in vacuo to give the title compound (5.60 g, 99% yield) as white solid. The residue was used to the next step directly without further purification. ¹H NMR (400 MHz, DMSO-d₆) δ 9.29-9.25 (m, 1H), 8.37 (s, 1H), 3.87 (s, 3H).

Step 2—Methyl 1-[3-(tert-butoxycarbonylamino)propyl]imidazole-4-carboxylate

To a mixture of methyl 1H-imidazole-4-carboxylate (3.10 g, 24.5 mmol) in ACN (50 mL) was added K₂CO₃ (11.2 g, 81.1 mmol) and tert-butyl N-(3-bromopropyl)carbamate (11.7 g, 49.1 mmol, CAS #83948-53-2). The reaction mixture was stirred at 25° C. for 16 hours. On completion, the reaction mixture was concentrated in vacuo. The residue was purified by column chromatography (SiO₂, PE:EA=5:1) to give the title compound (4.00 g, 57% yield) as colourless oil. ¹H NMR (400 MHz, DMSO-d₆) δ 8.02 (s, 1H), 7.83 (s, 1H), 7.00 (s, 1H), 4.10-4.08 (m, 2H), 3.80 (s, 3H), 2.99-2.88 (m, 2H), 1.90-1.88 (m, 2H), 1.45 (s, 9H).

Step 3—Tert-butyl N-[3-[4-(hydroxymethyl)imidazol-1-yl]propyl]carbamate

To a mixture of methyl 1-[3-(tert-butoxycarbonylamino)propyl]imidazole-4-carboxylate (3.00 g, 10.5 mmol) in THF (50 mL) was added LiAlH₄ (602 mg, 15.8 mmol) at 0° C. The reaction mixture was stirred at 20° C. for 2 hours. On completion, the reaction mixture was quenched with water (3 mL) and NaOH solution (15%, 5 mL) at 0° C., then Na₂SO₄ (20 g) was added. Then the mixture was filtered and the filtrate was concentrated in vacuo to give the title compound (2.50 g, 92% yield) as colourless oil. The residue was used to the next step directly without further purification. LC-MS (ESI⁺) m/z 256.2 (M+H)⁺.

Step 4—Tert-butyl N-[3-[4-(azidomethyl)imidazol-1-yl]propyl]carbamate (6)—Notebook Page: EW5435-653

To a mixture of tert-butyl N-[3-[4-(hydroxymethyl)imidazol-1-yl]propyl]carbamate (1.00 g, 3.92 mmol) and DPPA (1.62 g, 5.88 mmol, 1.27 mL) in THF (20 mL) was added DBU (1.49 g, 9.79 mmol, 1.48 mL) at 0° C. The reaction mixture was stirred at 25° C. for 12 hours. On completion, the reaction mixture was concentrated in vacuo. The residue was diluted with water (10 mL) and extracted with EA (3×10 mL). The combined organic layers were dried over Na₂SO₄, filtered and concentrated in vacuo to give the title compound (1.10 g, 100% yield) as light yellow oil. The residue was used to the next step directly without further purification. LC-MS (ESI⁺) m/z 281.3 (M+H)⁺

Step 5—Tert-butyl N-[3-[4-(aminomethyl)imidazol-1-yl]propyl]carbamate

To a mixture of tert-butyl N-[3-[4-(azidomethyl)imidazol-1-yl]propyl]carbamate (1.10 g, 3.92 mmol) in MeOH (50 mL) was added Pd/C (500 mg, 10 wt %). The reaction mixture was stirred at 25° C. for 3 hours under H₂ (15 Psi) atmosphere. On completion, the reaction mixture was filtered and concentrated in vacuo to give the title compound (950 mg, 95% yield) as light yellow oil. The residue was used in the next step directly without further purification. LC-MS (ESI⁺) m/z 255.3 (M+H)⁺.

4-[2-[2-[2-(Aminomethyl)-1-piperidyl]ethoxy]ethyl-amino]-2-(2,6-dioxo-3-piperidyl)iso indoline-1,3-dione (Intermediate FR)

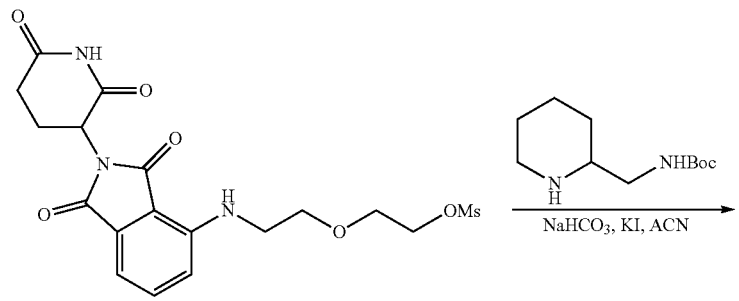

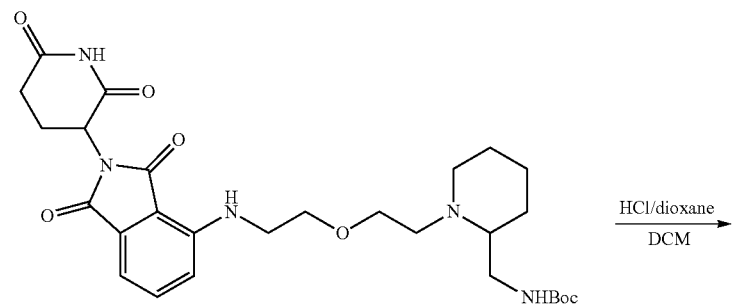

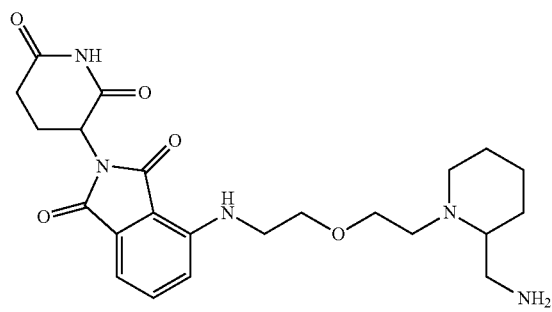

FR

Step 1-Tert-butyl N-[[1-[2-[2-[[2-(2,6-dioxo-3-piperidyl)-1,3-dioxo-isoindolin-4-yl]amino]ethoxy]ethyl]-2-piperidyl]methyl]carbamate To a solution of 2-[2-[[2-(2,6-dioxo-3-piperidyl)-1,3-dioxo-isoindolin-4-yl]amino]ethoxy]ethyl methanesulfonate (500 mg, 1.14 mmol, synthesized via Steps 1-2 of Example 184) in CH$_3$CN (20 mL) was added tert-butyl N-(2-piperidylmethyl) carbamate (488 mg, 2.28 mmol, CAS #141774-61-0), NaHCO$_3$ (287 mg, 3.41 mmol) and KI (18.9 mg, 114 umol). The mixture was stirred at 80° C. for 16 hours. On completion, the mixture was concentrated in vacuo. The residue was purified by reversed phase flash to give the title compound (450 mg, 71% yield) as yellow solid. LC-MS (ESI$^+$) m/z 558.4 (M+H)$^+$.

Step 2—4-[2-[2-[2-(Aminomethyl)-1-piperidyl]ethoxy]ethylamino]-2-(2,6-dioxo-3-piperidyl)isoindoline-1,3-dione To a solution of tert-butyl N-[[1-[2-[2-[[2-(2,6-dioxo-3-piperidyl)-1,3-dioxo-isoindolin-4-yl]amino]ethoxy]ethyl]-2-piperidyl]methyl]carbamate (450 mg, 807 umol) in DCM (5 mL) was added HCl/dioxane (4 M, 4 mL). The mixture was stirred at 20° C. for 2 hours. On completion, the mixture was concentrated in vacuo to give the title compound (360 mg, 91% yield) as yellow solid. LC-MS (ESI$^+$) m/z 458.3 (M+H)$^+$.

4-[2-[2-(2-Aminoethoxy)ethylamino]ethylamino]-2-(2,6-dioxo-3-piperidyl)isoindoline-1,3-dione (Intermediate FS)

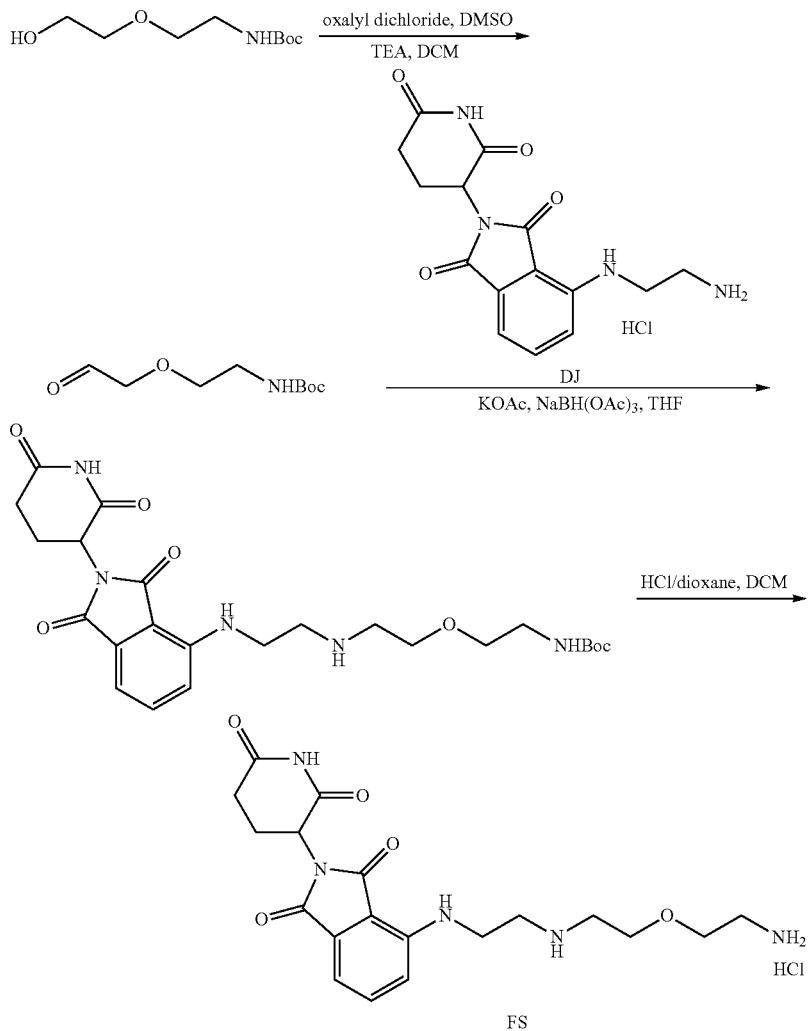

Step 1—Tert-butyl N-[2-(2-oxoethoxy)ethyl]carbamate

To a solution of DMSO (1.90 g, 24.4 mmol) in DCM (10 mL) was added a solution of (COCl)$_2$ (2.47 g, 19.5 mmol) in DCM (10 mL) dropwise at −70° C. The mixture was stirred at this temperature for 10 minutes. Then a solution of tert-butyl N-[2-(2-hydroxyethoxy)ethyl]carbamate (2 g, 9.74 mmol, CAS #139115-91-6) in DCM (15 mL) was added into the above mixture slowly. After stirring at −70° C. for 50 minutes, TEA (7.89 g, 78.0 mmol) was added and the reaction mixture was stirred at −70° C. for 0.5 hour. On completion, the mixture was quenched with water (30 mL) and separated. The aqueous phase was extracted with DCM (2×30 mL). Then the organic phase was combined and washed with brine (100 mL), dried over Na$_2$SO$_4$ and concentrated in vacuo to give the title compound (1.30 g, crude) as yellow oil.

Step 2—Tert-butyl N-[2-[2-[2-[[2-(2,6-dioxo-3-piperidyl)-1,3-dioxo-isoindolin-4-yl]amino]ethyl amino]ethoxy]ethyl]carbamate To a solution of 4-(2-aminoethylamino)-2-(2,6-dioxo-3-piperidyl)isoindoline-1,3-dione (202 mg, 572 umol, HCl, Intermediate DJ) and tert-butyl N-[2-(2-oxoethoxy)ethyl]carbamate (90.0 mg, 443 umol) in THF (20 mL) was added KOAc (102 mg, 1.04 mmol). One hour later, NaBH(OAc)$_3$ (220 mg, 1.04 mmol) was added into the above mixture. The reaction mixture was stirred at 25° C. for 17 hours. On completion, the reaction mixture was concentrated in vacuo.

1341

The residue was purified by reverse phase (0.1% HCl condition) to give the title compound (80.0 mg, 31% yield) as a yellow solid. LC-MS (ESI⁺) m/z 504.1 (M+H)⁺.

Step 3—4-[2-[2-(2-Aminoethoxy)ethylamino]ethyl-amino]-2-(2,6-dioxo-3-piperidyl)isoindoline-1,3-dione To a solution of tert-butyl N-[2-[2-[2-[[2-(2,6-dioxo-3-piperidyl)-1,3-dioxo-isoindolin-4-yl]amino]ethylamino] ethoxy]ethyl]carbamate (75.0 mg, 149 umol) in DCM (2 mL) was added HCl/dioxane (2 mL). The reaction mixture was stirred at 25° C. for 0.5 hour. On completion, the mixture was concentrated in vacuo to give the title compound (65.0 mg, 99% yield, HCl) as a yellow solid. LC-MS (ESI⁺) m/z 404.1 (M+H)⁺.

4-Bromo-2-(2,6-dioxo-3-piperidyl)isoindoline-1,3-dione (Intermediate FT)

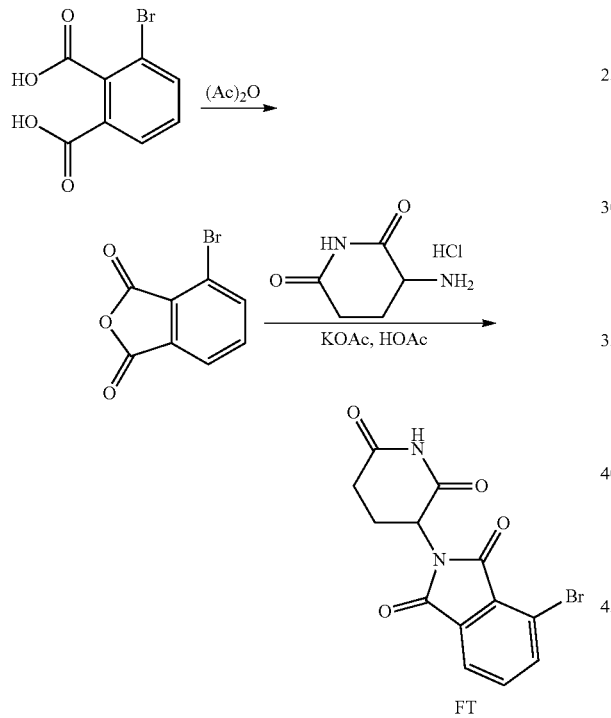

Step 1—4-Bromoisobenzofuran-1,3-dione

A solution of 3-bromophthalic acid (5.00 g, 20.4 mmol, CAS #116-69-8) in (Ac)₂O (20.4 mmol, 20 mL) was stirred at 120° C. for 12 hours. The reaction mixture was then stirred at 25° C. for 16 hours. On completion, the mixture was concentrated in vacuo to give the title compound (4.60 g, 99% yield) as yellow solid. LC-MS (ESI⁺) m/z 227.1 (M+H)⁺.

Step 2—4-Bromo-2-(2,6-dioxo-3-piperidyl)isoindoline-1,3-dione

To a solution of 4-bromoisobenzofuran-1,3-dione (4.60 g, 20.2 mmol) and 3-aminopiperidine-2,6-dione (3.67 g, 22.2 mmol, HCl, CAS #24666-56-6) in HOAc (40 mL) was added KOAc (6.16 g, 62.8 mmol), the reaction mixture was stirred at 90° C. for 16 hr. On completion, the mixture was cooled to 25° C. and diluted with ice water (800 mL), and then stirred at 0° C. for 0.5 hr. The reaction mixture was filtered and the filter cake was dried in vacuo to give the title compound (6.8 g, 99% yield) as gray solid. ¹H NMR (400 MHz, DMSO-d₆) δ 11.17 (s, 1H), 8.19-7.65 (m, 3H), 5.41-4.91 (m, 1H), 3.35 (s, 1H), 3.05-2.85 (m, 1H), 2.72-2.54 (m, 2H), 2.09 (s, 1H).

4-(3-Aminopropyl)-2-(2,6-dioxo-3-piperidyl)isoindoline-1,3-dione (Intermediate FU)

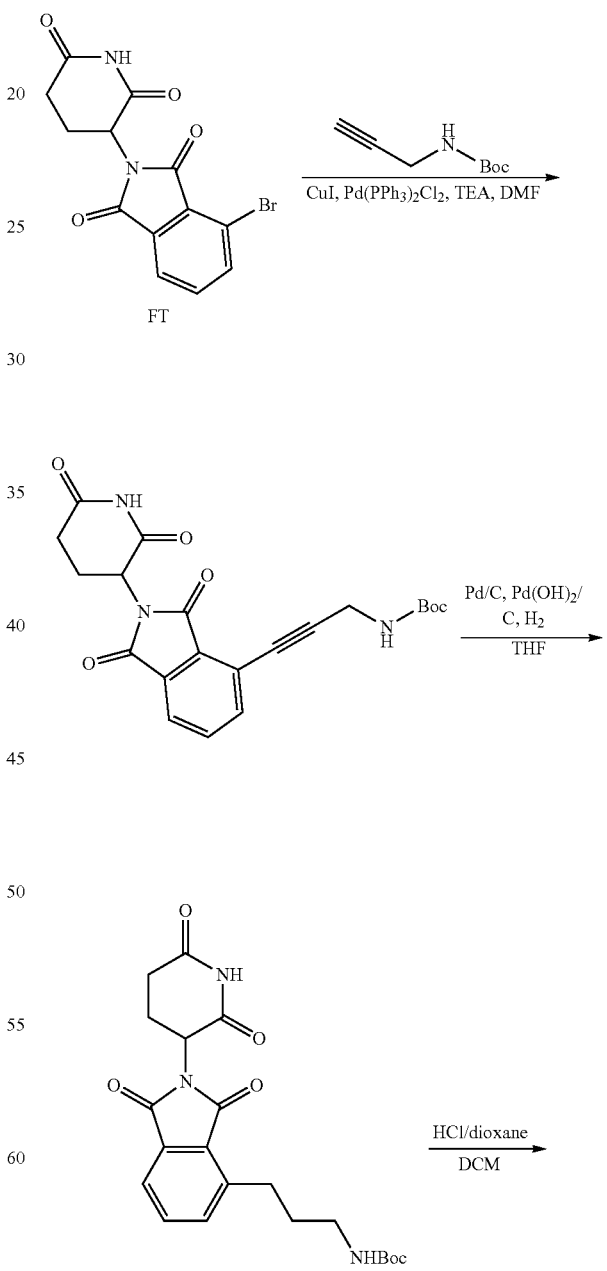

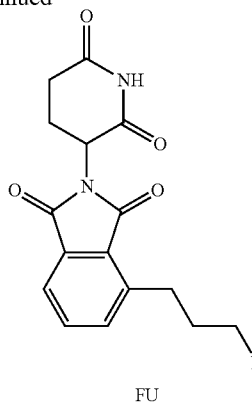

FU

Step 1—Tert-butyl N-[3-[2-(2,6-dioxo-3-piperidyl)-1,3-dioxo-isoindolin-4-yl]prop-2-ynyl]carbamate To a solution of 4-bromo-2-(2,6-dioxo-3-piperidyl)isoindoline-1,3-dione (1.00 g, 2.97 mmol, Intermediate FT) and tert-butyl N-prop-2-ynylcarbamate (598 mg, 3.86 mmol, CAS #92136-39-5) in DMF (6 mL) was added TEA (5.40 g, 53.3 mmol, 7.43 mL), CuI (56.4 mg, 296 umol) and Pd(PPh$_3$)$_2$Cl$_2$ (208 mg, 296 umol). The reaction mixture was heated at 80° C. for 30 minutes under microwave. On completion, the reaction mixture was concentrated in vacuo. The residue was purified by column chromatography to give the title compound (1.20 g, 98% yield) as yellow solid. LC-MS (ESI$^+$) m/z 434.0 (M+Na)$^+$.

Step 2—Tert-butyl N-[3-[2-(2,6-dioxo-3-piperidyl)-1,3-dioxo-isoindolin-4-yl]propyl]carbamate To a mixture of tert-butyl N-[3-[2-(2,6-dioxo-3-piperidyl)-1,3-dioxo-isoindolin-4-yl]prop-2-ynyl]carbamate (520 mg, 1.26 mmol) in THF (20 mL) was added Pd(OH)$_2$/C (150 g, 10 wt %) and Pd/C (130 mg, 10 wt %). The reaction mixture was stirred at 25° C. for 12 hours under H$_2$ (15 Psi) atmosphere. On completion, the reaction mixture was filtered and concentrated in vacuo to give the title compound (0.52 g, 99% yield) as light yellow solid. LC-MS (ESI$^+$) m/z 438.3 (M+Na)$^+$.

Step 3—4-(3-Aminopropyl)-2-(2,6-dioxo-3-piperidyl)isoindoline-1,3-dione

To a mixture of tert-butyl N-[3-[2-(2,6-dioxo-3-piperidyl)-1,3-dioxo-isoindolin-4-yl]propyl]carbamate (520 mg, 1.25 mmol) in DCM (3 mL) was added HCl/dioxane (4 M, 3 mL). The reaction mixture was stirred at 25° C. for 2 hours. On completion, the reaction mixture was concentrated in vacuo to give the title compound (520 mg, 99% yield, HCl) as light yellow solid. LC-MS (ESI$^+$) m/z 316.1 (M+H)$^+$ 4-[3-(5-Aminopentylamino)propyl]-2-(2,6-dioxo-3-piperidyl)isoindoline-1,3-dione (Intermediate FV)

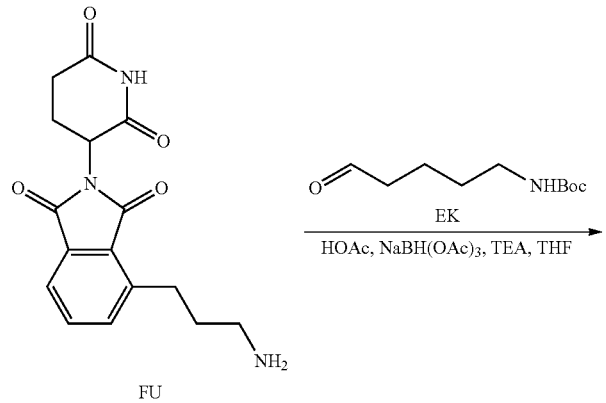

FU

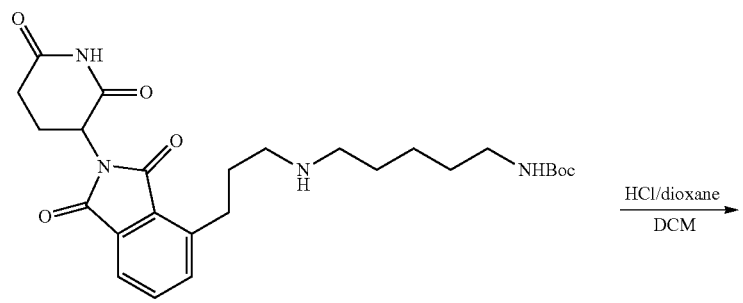

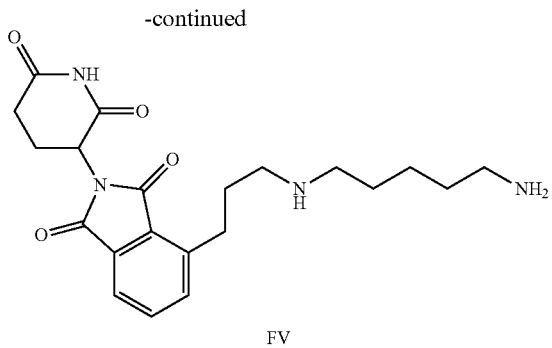

FV

Step 1—Tert-butyl N-[5-[3-[2-(2,6-dioxo-3-piperidyl)-1,3-dioxo-isoindolin-4-yl]propylamino]pentyl]carbamate To a mixture of 4-(3-aminopropyl)-2-(2,6-dioxo-3-piperidyl)isoindoline-1,3-dione (445 mg, 1.27 mmol, HCl, Intermediate FU) in THF (5 mL) was added TEA (85.4 mg, 844 umol, 117 uL) and tert-butyl N-(5-oxopentyl)carbamate (170 mg, 844 umol, Intermediate EK) and HOAc (76.0 mg, 1.27 mmol, 72.4 uL), then NaBH(OAc)$_3$ (358 mg, 1.69 mmol) was added. The reaction mixture was stirred at 25° C. for 5 hours under N$_2$ atmosphere. On completion, the reaction mixture was concentrated in vacuo. The residue was purified by prep-HPLC (0.1% FA condition) to give the title compound (200 mg, 47% yield) as light yellow oil. LC-MS (ESI$^+$) m/z 501.4 (M+H)$^+$.

Step 2—4-[3-(5-Aminopentylamino)propyl]-2-(2,6-dioxo-3-piperidyl)isoindoline-1,3-dione To a mixture of tert-butyl N-[5-[3-[2-(2,6-dioxo-3-piperidyl)-1,3-dioxo-isoindolin-4-yl]propylamino]pentyl]carbamate (170 mg, 339 umol) in DCM (5 mL) was added HCl/dioxane (4 M, 8 mL). The reaction mixture was stirred at 25° C. for 1 hour. On completion, the reaction mixture was concentrated in vacuo to give the title compound (170 mg, 99% yield) as light yellow solid. LC-MS (ESI$^+$) m/z 401.2 (M+H)$^+$.

Methyl 4-[4-amino-3-(difluoromethyl)pyrazol-1-yl]benzoate (Intermediate FW)

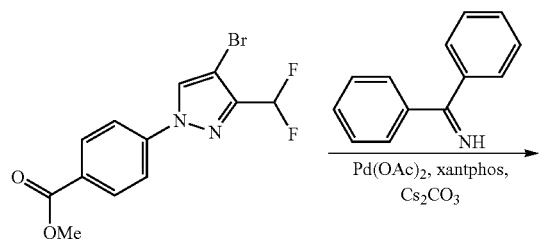

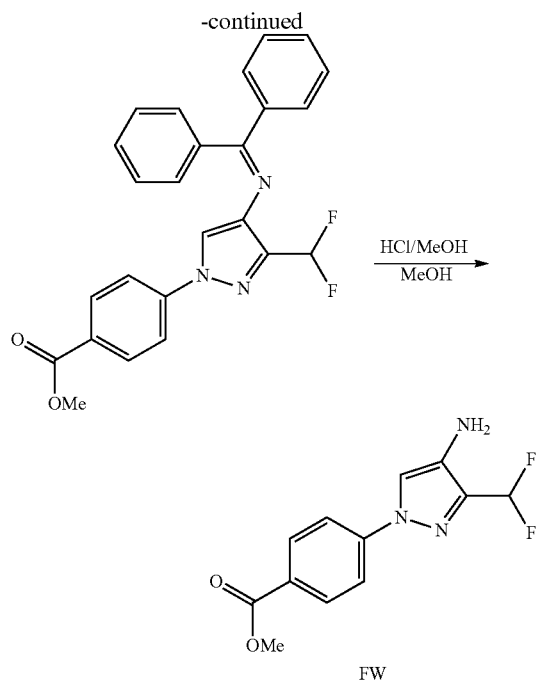

FW

Step 1—Methyl 4-[4-(benzhydrylideneamino)-3-(difluoromethyl)pyrazol-1-yl]benzoate A mixture of methyl 4-[4-bromo-3-(difluoromethyl)pyrazol-1-yl]benzoate (0.15 g, 453 umol, synthesized via Steps 1-2 of Intermediate EB), diphenylmethanimine (205 mg, 1.13 mmol), Pd(OAc)$_2$ (20.8 mg, 92.4 umol), Xantphos (26.2 mg, 45.3 umol) and Cs$_2$CO$_3$ (448 mg, 1.38 mmol) in dioxane (3 mL) was degassed and purged with N$_2$ 3 times, and then the mixture was stirred at 120° C. for 3 hrs under N$_2$ atmosphere. On completion, the mixture was concentrated, then H$_2$O (30 mL) was added and the mixture was extracted with EtOAc (3×30 mL). The organic phase was dried with Na$_2$SO$_4$, filtrated and concentrated in vacuo. The residue was purified by flash silica gel chromatography to give the title compound (0.24 g, 50% yield) as a yellow solid. $^1$H NMR (400 MHz, CDCl$_3$) δ 8.02-7.95 (m, 2H), 7.80-7.73 (m, 2H), 7.51-7.45 (m, 3H), 7.43-7.31 (m, 5H), 7.22-7.19 (m, 2H), 7.12-6.82 (m, 1H), 6.37 (s, 1H), 3.85 (s, 3H); LC-MS (ESI$^+$) m/z 432.1 (M+H)$^+$.

Step 2—Methyl 4-[4-amino-3-(difluoromethyl)pyrazol-1-yl]benzoate

To a solution of methyl 4-[4-(benzhydrylideneamino)-3-(difluoromethyl)pyrazol-1-yl]benzoate (215 mg, 498 umol) in THF (2 mL) and MeOH (20 mL) was added HCl/MeOH (4 M, 124 uL). The mixture was stirred at 25° C. for 30 min. On completion, the mixture was concentrated to give the title compound (0.20 g, 90% yield) as a yellow solid. LC-MS (ESI$^+$) m/z 268.1 (M+H)$^+$.

4-[4-[[2-[2-(Cyclopropylmethylamino)-4-pyridyl]oxazole-4-carbonyl]amino]-3-(difluoro methyl)pyrazol-1-yl]benzoic acid (Intermediate FX)

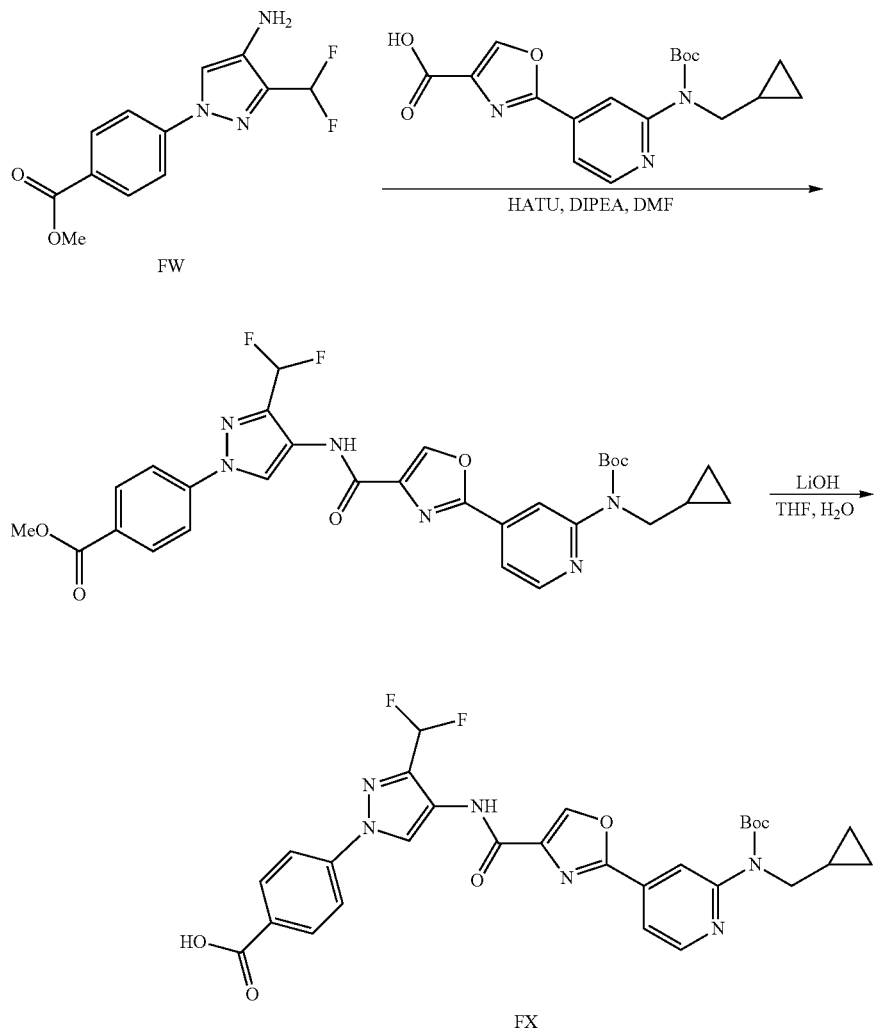

Step 1—Methyl 4-[4-[[2-[2-[tert-butoxycarbonyl(cyclopropylmethyl)amino]-4-pyridyl]oxazole-4-carbonyl]amino]-3-(difluoromethyl)pyrazol-1-yl]benzoate A mixture of methyl 4-[4-amino-3-(difluoromethyl)pyrazol-1-yl]benzoate (340 mg, 1.27 mmol, Intermediate FW), 2-[2-[tert-butoxycarbonyl(cyclopropylmethyl)amino]-4-pyridyl]oxazole-4-carboxylic acid (412 mg, 1.15 mmol, from Steps 1-4 of Intermediate DF), HATU (484 mg, 1.27 mmol), DIPEA (411 mg, 3.18 mmol, 554 uL) in DMF (10 mL) was degassed and purged with N$_2$ 3 times. Then the mixture was stirred at 25° C. for 6 hrs. On completion, the mixture was diluted with 50 mL H$_2$O and then filtered. The filter cake was dried in vacuo to give the title compound (260 mg, 27% yield) as a yellow solid. LC-MS (ESI$^+$) m/z 609.2 (M+H)$^+$.

Step 2—4-[4-[[2-[2-(Cyclopropylmethylamino)-4-pyridyl]oxazole-4-carbonyl]amino]-3-(difluoro methyl)pyrazol-1-yl]benzoic acid To a solution of methyl 4-[4-[[2-[2-[tert-butoxycarbonyl(cyclopropylmethyl)amino]-4-pyridyl]oxazole-4-carbonyl]amino]-3-(difluoromethyl)pyrazol-1-yl]benzoate (200 mg, 329 umol) in THF (5 mL) and H$_2$O (5 mL) and MeOH (1 mL) was added LiOH (39.4 mg, 1.64 mmol). The mixture was stirred at 25° C. for 6 hrs. On completion, the mixture was concentrated, the residue was diluted with H$_2$O (50 mL) and added 1M HCl to pH=5-6, extracted with EA (3×30 mL). The combined organic layers were washed with brine (50 mL), dried over Na$_2$SO$_4$, filtered and concentrated in vacuo to give the title compound (0.13 g, 95% yield) as a yellow solid. LC-MS (ESI$^+$) m/z 595.4 (M+H)$^+$.

Tert-butyl N-methyl-N-[2-(2-prop-2-ynoxyethoxy)ethyl]carbamate (Intermediate FY)

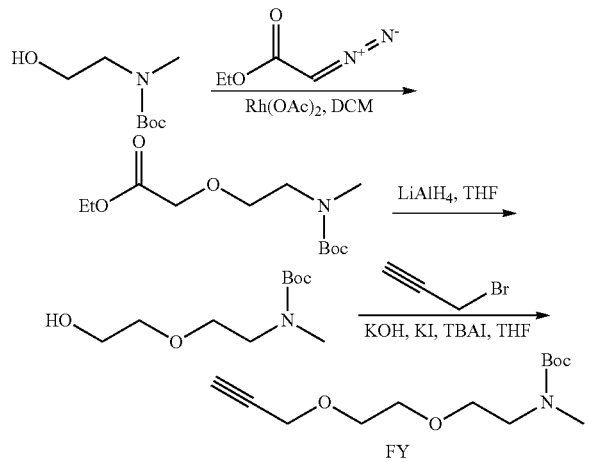

Step 1—Ethyl 2-[2-[tert-butoxycarbonyl(methyl)amino]ethoxy]acetate

To a solution of tert-butyl N-(2-hydroxyethyl)-N-methyl-carbamate (10 g, 57.0 mmol) and Rh(OAc)$_2$ (630 mg, 2.85 mmol) in DCM (100 mL) was added a solution of ethyl 2-diazoacetate (13.0 g, 114 mmol, CAS #623-73-4) in DCM (200 mL) dropwise, and the mixture was stirred at 25° C. for 16 hours. On completion, the reaction mixture was washed with water (50 mL×4), dried over Na$_2$SO$_4$, filtered and concentrated in vacuo to give the title compound (14.5 g, 97% yield) as light yellow liquid. $^1$H NMR (400 MHz, CDCl$_3$) δ 4.21 (q, J=7.2 Hz, 2H), 4.09-4.04 (m, 2H), 3.71-3.59 (m, 2H), 3.46-3.38 (m, 2H), 2.92 (s, 3H), 1.44 (s, 9H), 1.27 (t, J=7.2 Hz, 3H).

Step 2—Tert-butyl N-[2-(2-hydroxyethoxy)ethyl]-N-methyl-carbamate

To a solution of ethyl 2-[2-[tert-butoxycarbonyl(methyl)amino]ethoxy]acetate (12.4 g, 47.4 mmol) in THF (200 mL) was added LiAlH$_4$ (2.76 g, 71.1 mmol, 98% purity) at 0° C. under N$_2$ atmosphere. The reaction mixture was stirred at 20° C. for 1 hour. On completion, the mixture was quenched with water (4 mL) and NaOH aqueous solution (15%, 4 mL) at 0° C., filtered and dried over Na$_2$SO$_4$, filtered and concentrated in vacuo to give the title compound (9.40 g, 90% yield) as colorless liquid. $^1$H NMR (400 MHz, CDCl$_3$) δ 3.72-3.67 (m, 2H), 3.66-3.54 (m, 4H), 3.50-3.42 (m, 2H), 2.91 (s, 3H), 1.46 (s, 9H).

Step 3—Tert-butyl N-methyl-N-[2-(2-prop-2-ynoxyethoxy)ethyl]carbamate

To a solution of tert-butyl N-[2-(2-hydroxyethoxy)ethyl]-N-methyl-carbamate (8.70 g, 39.6 mmol) and 3-bromoprop-1-yne (5.19 g, 43.6 mmol) in THF (100 mL) was added TBAI (879 mg, 2.38 mmol), KI (987 mg, 5.95 mmol) and KOH (2.62 g, 39.6 mmol, 85%). The mixture was stirred at 20° C. for 16 hours. On completion, the reaction mixture was filtered and concentrated in vacuo to give a residue. The residue was purified by silica gel chromatography (PE:EA=3:1) to give the title compound (4.20 g, 41% yield) as colorless oil. $^1$H NMR (400 MHz, CDCl$_3$) δ 4.21 (d, J=2.4 Hz, 2H), 3.72-3.67 (m, 2H), 3.67-3.62 (m, 2H), 3.61-3.55 (m, 2H), 3.45-3.35 (m, 2H), 2.92 (s, 3H), 2.43 (t, J=2.4 Hz, 1H), 1.46 (s, 9H).

2-(2,6-Dioxo-3-piperidyl)-4-[3-[2-[2-(methylamino)ethoxy]ethoxy]propyl]isoindoline-1,3-dione (Intermediate FZ)

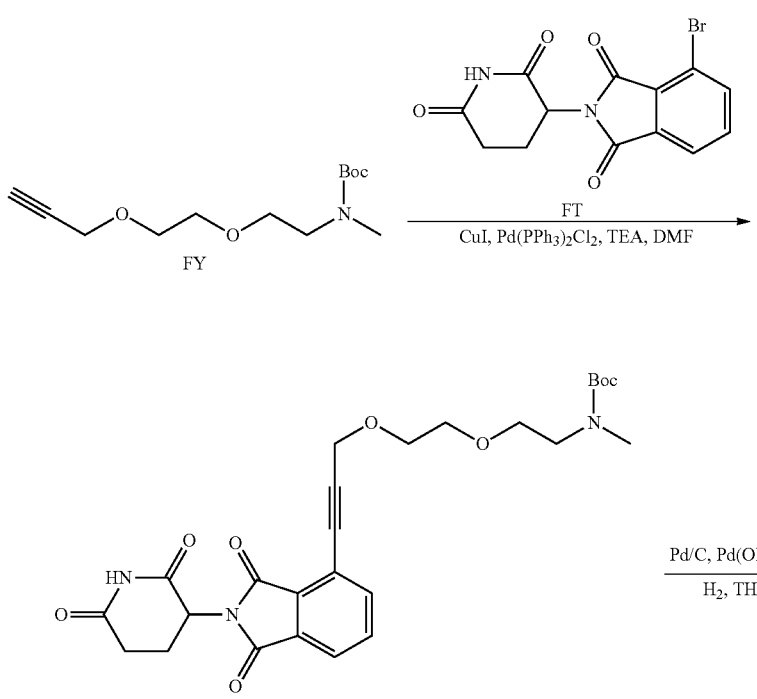

-continued

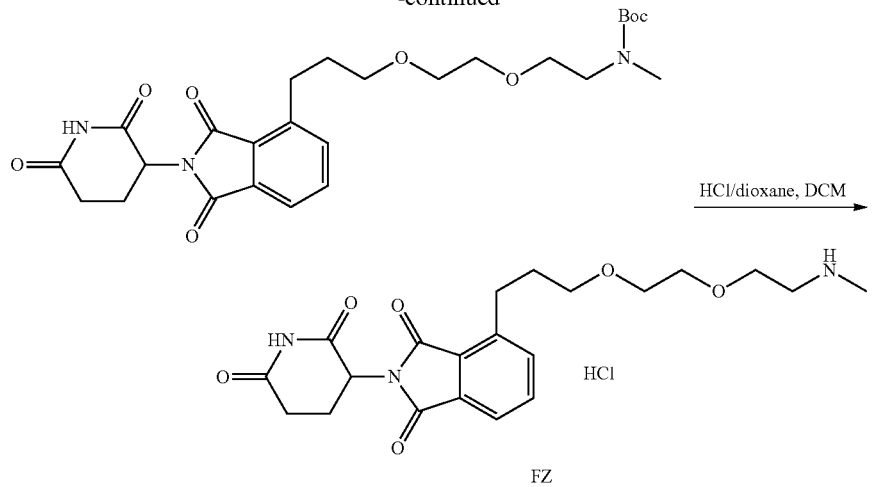

Step 1—Tert-butyl N-[2-[2-[3-[2-(2,6-dioxo-3-piperidyl)-1,3-dioxo-isoindolin-4-yl]prop-2-ynoxy]ethoxy]ethyl]-N-methyl-carbamate 4-Bromo-2-(2,6-dioxo-3-piperidyl)isoindoline-1,3-dione (0.60 g, 1.78 mmol, Intermediate FT), CuI (33.9 mg, 178 umol) and Pd(PPh$_3$)$_2$Cl$_2$ (125 mg, 178 umol) was taken up into a microwave tube. Then tert-butyl N-methyl-N-[2-(2-prop-2-ynoxyethoxy)ethyl]carbamate (458 mg, 1.78 mmol, Intermediate FY), TEA (3.24 g, 32.0 mmol) and DMF (5 mL) were added into the above tube. The mixture was degassed with N$_2$ for 5 minutes. The sealed tube was heated at 80° C. for 30 minutes under microwave. On completion, the reaction mixture was filtered and the filtrate was concentrated in vacuo. The residue was purified by silica gel chromatography to give the title compound (460 mg, 43% yield, 85% purity) as yellow oil. LC-MS (ESI$^+$) m/z 536.3 (M+Na)$^+$.

Step 2—Tert-butyl N-[2-[2-[3-[2-(2,6-dioxo-3-piperidyl)-1,3-dioxo-isoindolin-4-yl]propoxy]ethoxy]ethyl]-N-methyl-carbamate To a solution of tert-butyl N-[2-[2-[3-[2-(2,6-dioxo-3-piperidyl)-1,3-dioxo-isoindolin-4-yl]prop-2-ynoxy]ethoxy]ethyl]-N-methyl-carbamate (460 mg, 761 umol) in THF (5 mL) was added Pd/C (0.2 g, 10% wt) and Pd(OH)$_2$/C (0.2 g, 10% wt). The reaction mixture was stirred at 25° C. for 18 hrs under H$_2$ (15 Psi). On completion, the mixture was filtered and the filtrate was concentrated in vacuo to give the title compound (450 mg, 100% yield) as yellow oil. LC-MS (ESI$^+$) m/z 540.1 (M+Na)$^+$.

Step 3—2-(2,6-Dioxo-3-piperidyl)-4-[3-[2-[2-(methylamino)ethoxy]ethoxy]propyl]isoindoline-1,3-dione To a solution of tert-butyl N-[2-[2-[3-[2-(2,6-dioxo-3-piperidyl)-1,3-dioxo-isoindolin-4-yl]propoxy]ethoxy]ethyl]-N-methyl-carbamate (450 mg, 869 umol) in DCM (3 mL) was added HCl/dioxane (4 M, 4 mL). The reaction mixture was stirred at 25° C. for 0.5 hr. On completion, the residue was concentrated in vacuo to give the title compound (330 mg, 84% yield, HCl) as yellow oil. LC-MS (ESI$^+$) m/z 418.1 (M+H)$^+$.

5-Bromo-2-(2,6-dioxo-3-piperidyl)isoindoline-1,3-dione (Intermediate GA)

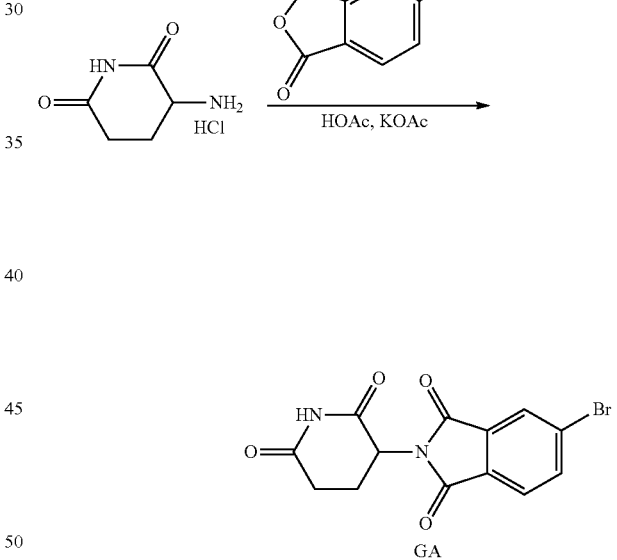

To a solution of 3-aminopiperidine-2,6-dione (7.98 g, 48.4 mmol, HCl salt, CAS #24666-56-6), KOAc (13.4 g, 136 mmol) in HOAc (200 mL) was added 5-bromoisobenzofuran-1,3-dione (10.0 g, 44.0 mmol, CAS #282-73-5). The mixture was then heated to 90° C. and stirred for 12 hours. On completion, the mixture was cooled down to 25° C. and diluted with water (800 mL), and then filtered to give a filter cake. The filter cake was stirred in DCM (20 mL) for 1 hour and filtered to give a filter cake. The filter cake was dried in vacuo to give the title compound (9.00 g, 60% yield) as a blue solid. $^1$H NMR (400 MHz, DMSO-d$_6$) δ 11.15 (s, 1H), 8.15 (d, J=1.2 Hz, 1H), 8.10 (dd, J=1.6, 8.0 Hz, 1H), 7.87 (d, J=8.0 Hz, 1H), 5.17 (dd, J=5.6, 12.8 Hz, 1H), 2.95-2.83 (m, 1H), 2.65-2.52 (m, 2H), 2.11-2.00 (m, 1H).

4-Amino-1-[4-(hydroxymethyl)phenyl]pyrazole-3-carboxamide (Intermediate GB)

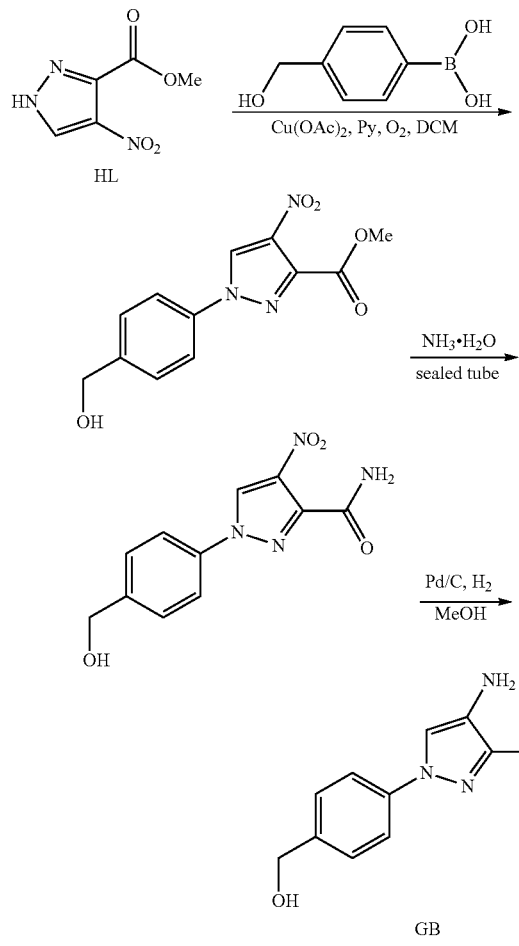

Step 1—Methyl 1-[4-(hydroxymethyl)phenyl]-4-nitro-pyrazole-3-carboxylate

To a mixture of methyl 4-nitro-1H-pyrazole-3-carboxylate (8.00 g, 38.5 mmol, HCl salt, Intermediate HL), [4-(hydroxymethyl)phenyl]boronic acid (7.03 g, 46.2 mmol, CAS #59016-93-2) and pyridine (18.2 g, 231 mmol) in DCM (130 mL) was added Cu(OAc)$_2$ (8.40 g, 46.2 mmol). The mixture was stirred at 25° C. under O$_2$ (15 psi) for 16 hours. On completion, the mixture was concentrated in vacuo to give a residue. The residue was purified by silica gel chromatography (PE:EA=1:1) to give the title compound (4.00 g, 36% yield) as white solid. $^1$H NMR (400 MHz, DMSO-d$_6$) δ 9.68 (s, 1H), 7.89 (d, J=8.8 Hz, 2H), 7.51 (d, J=8.8 Hz, 2H), 5.37 (t, J=5.6 Hz, 1H), 4.57 (d, J=5.6 Hz, 2H), 3.94 (s, 3H); LC-MS (ESI$^+$) m/z 300.0 (M+Na)$^+$.

Step 2—1-[4-(Hydroxymethyl)phenyl]-4-nitro-pyrazole-3-carboxamide

To a solution of methyl 1-[4-(hydroxymethyl)phenyl]-4-nitro-pyrazole-3-carboxylate (2.30 g, 7.72 mmol) in THF (15 mL) was added NH$_3$·H$_2$O (22.7 g, 194 mmol, 30% w/w) in a sealed tube. The mixture was stirred at 80° C. for 16 hours. On completion, the reaction mixture was concentrated in vacuo to give the title compound (2.20 g, 97% yield) as yellow solid. $^1$H NMR (400 MHz, DMSO-d$_6$) δ 9.60 (s, 1H), 8.19 (s, 1H), 7.90 (d, J=8.4 Hz, 3H), 7.50 (d, J=8.4 Hz, 2H), 5.37 (s, 1H), 4.56 (d, J=2.4 Hz, 2H).

Step 3—4-Amino-1-[4-(hydroxymethyl)phenyl]pyrazole-3-carboxamide

To a solution of 1-[4-(hydroxymethyl)phenyl]-4-nitro-pyrazole-3-carboxamide (1.60 g, 6.10 mmol) in MeOH (120 mL) was added Pd/C (0.8 g, 10% w/w) under N$_2$. The suspension was degassed in vacuo and purged with H$_2$ three times. The mixture was stirred under H$_2$ (15 psi) at 20° C. for 40 minutes. On completion, the reaction mixture was filtered and the filtrate was concentrated in vacuo to give the title compound (1.40 g, 91% yield) as yellow solid; LC-MS (ESI$^+$) m/z 233.1 (M+H)$^+$.

Tert-butyl N-[4-[4-[3-carbamoyl-1-(4-formylphenyl)pyrazol-4-yl]carbamoyl]oxazol-2-yl-2-pyridyl]-N-(cyclopropylmethyl)carbamate (Intermediate GC)

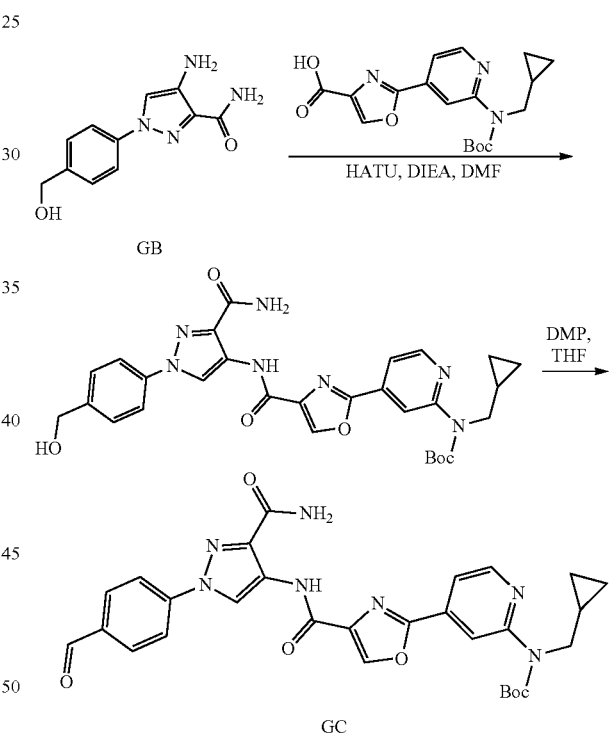

Step 1—Tert-butyl N-[4-[4-[[3-carbamoyl-1-[4-(hydroxymethyl)phenyl]pyrazol-4-yl]carbamoyl]oxazol-2-yl]-2-pyridyl]-N-(cyclopropylmethyl)carbamate To a solution of 2-[2-[tert-butoxycarbonyl(cyclopropylmethyl)amino]-4-pyridyl]oxazole-4-carboxylic acid (1.24 g, 3.44 mmol, from Steps 1-4 of Intermediate DF) in DMF (25 mL) was added DIPEA (1.67 g, 12.9 mmol), HATU (1.96 g, 5.17 mmol) and 4-amino-1-[4-(hydroxymethyl)phenyl]pyrazole-3-carboxamide (1.00 g, 4.31 mmol, Intermediate GB). The mixture was stirred at 20° C. for 2 hours. On completion, the reaction mixture was diluted with water (80 mL), filtered to give a filter cake which was dried in vacuo to give the title compound (1.50 g, 60% yield) as brown solid. LC-MS (ESI+) m/z 574.1 (M+H)+.

Step 2—Tert-butyl N-[4-[4-[[3-carbamoyl-1-(4-formylphenyl)pyrazol-4-yl]carbamoyl]oxazol-2-yl]-2-pyridyl]-N-(cyclopropylmethyl)carbamate To a solution of tert-butyl N-[4-[4-[[3-carbamoyl-1-[4-(hydroxymethyl)phenyl]pyrazol-4-yl]carbamoyl]oxazol-2-yl]-2-pyridyl]-N-(cyclopropylmethyl)carbamate (1.5 g, 2.62 mmol) in a THF (300 mL) was added DMP (1.22 g, 2.88 mmol), and the mixture was stirred at 20° C. for 16 hours. On completion, the reaction mixture was quenched with saturated Na$_2$S$_2$O$_3$ (20 mL) and saturated NaHCO$_3$ (20 mL) at 25° C. This reaction mixture was then stirred for 30 minutes, then extracted with CH$_2$Cl$_2$ (80 mL×3). The combined organic layers were filtered and concentrated in vacuo to give the title compound (1 g, 67% yield) as gray solid. $^1$H NMR (400 MHz, DMSO-d$_6$) δ 11.04 (s, 1H), 10.04 (s, 1H), 9.09 (s, 2H), 8.60 (d, J=5.2 Hz, 1H), 8.25-8.23 (m, 3H), 8.17 (s, 1H), 8.07 (d, J=8.4 Hz, 2H), 7.81 (br s, 1H), 7.67 (d, J=4.8 Hz, 1H), 3.86 (br d, J=7.2 Hz, 2H), 1.52 (s, 9H), 1.20-1.16 (m, 1H), 0.46-0.35 (m, 2H), 0.25-0.22 (m, 2H); LC-MS (ESI+) m/z 572.1 (M+H)+.

2-(2,6-Dioxo-3-piperidyl)-5-[3-[2-[2-(methylamino)ethoxy]ethoxy]propyl]isoindoline-1,3-dione (Intermediate GD)

Step 1—Tert-butyl N-[2-[2-[3-[2-(2,6-dioxo-3-piperidyl)-1,3-dioxo-isoindolin-5-yl]prop-2-ynoxy]ethoxy]ethyl]-N-methyl-carbamate To a solution of 5-bromo-2-(2,6-dioxo-3-piperidyl)isoindoline-1,3-dione (3.73 g, 11.0 mmol, Intermediate GA) and tert-butyl N-methyl-N-[2-(2-prop-2-ynoxyethoxy)ethyl]carbamate (3.70 g, 14.3 mmol, Intermediate FY) in DMF (30 mL) was added Pd(PPh$_3$)$_2$Cl$_2$ (776 mg, 1.11 mmol), TEA (20.1 g, 199 mmol) and CuI (210 mg, 1.11 mmol). The mixture was heated at 80° C. for 30 minutes under microwave. On completion, the reaction mixture was concentrated in vacuo to give a residue. The residue was purified by silica gel chromatography (PE:EA=1:1) to give the title compound (5.50 g, 96% yield) as brown oil. $^1$H NMR (400 MHz, CDCl$_3$) δ 8.09 (s, 1H), 7.91 (s, 1H), 7.87-7.78 (m, 2H), 4.99 (dd, J=5.6, 12.4 Hz, 1H), 4.48 (s, 2H), 3.80-3.73 (m, 2H), 3.71-3.66 (m, 2H), 3.65-3.58 (m, 2H), 3.45-3.35 (m, 2H), 2.98-2.94 (m, 1H), 2.93 (s, 3H), 2.88-2.70 (m, 2H), 2.21-2.13 (m, 1H), 1.46 (s, 9H).

Step 2—Tert-butyl N-[2-[2-[3-[2-(2,6-dioxo-3-piperidyl)-1,3-dioxo-isoindolin-5-yl]propoxy]ethoxy]ethyl]-N-methyl-carbamate (19)—Notebook Page: EW5417-733

To a solution of tert-butyl N-[2-[2-[3-[2-(2,6-dioxo-3-piperidyl)-1,3-dioxo-isoindolin-5-yl]prop-2-ynoxy]ethoxy]ethyl]-N-methyl-carbamate (1.00 g, 1.95 mmol) in THF (20

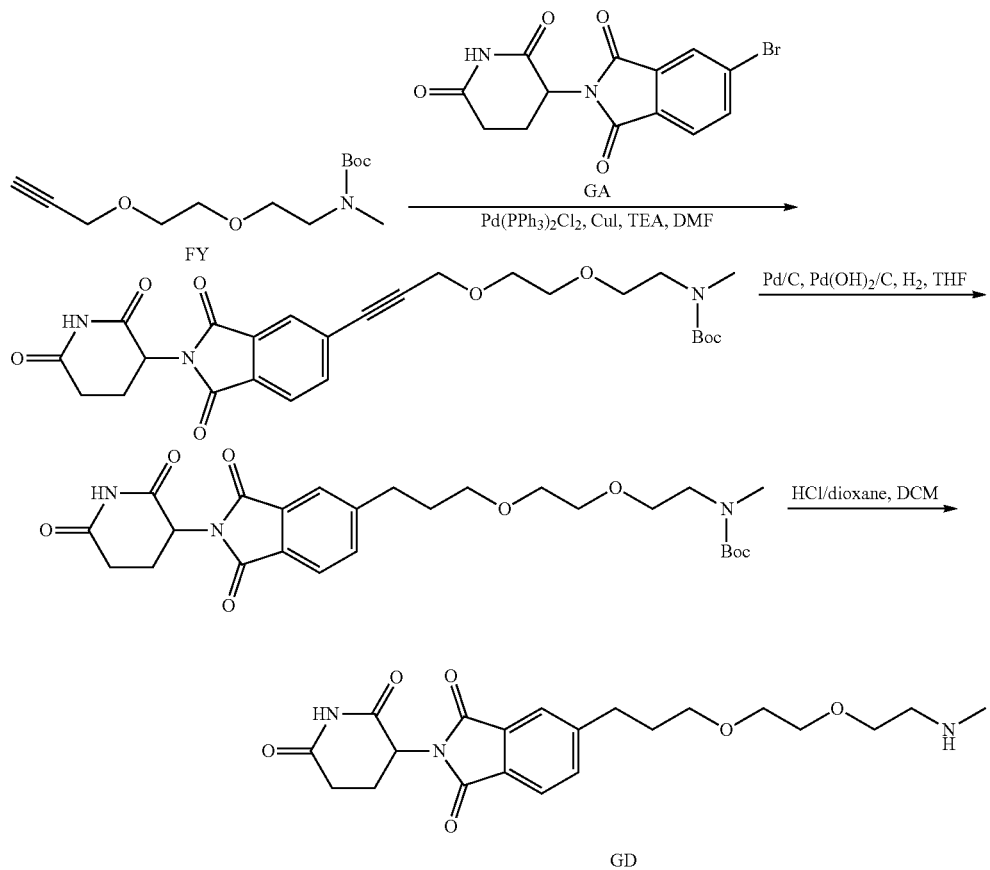

mL) was added Pd/C (0.30 g, 10% w/w) and Pd(OH)₂/C (0.30 g, 10% w/w) under N₂ atmosphere. The suspension was degassed under vacuum and purged with H₂ three times. The mixture was stirred under H₂ (15 Psi) at 20° C. for 1 hour. On completion, the reaction mixture was filtered and the filterate was concentrated in vacuo to give the title compound (0.95 g, 95% yield) as brown oil. ¹H NMR (400 MHz, CDCl₃) δ 8.08 (s, 1H), 7.79 (d, J=8.0 Hz, 1H), 7.72 (s, 1H), 7.59 (dd, J=1.2, 7.6 Hz, 1H), 5.02 (dd, J=5.2, 13.6 Hz, 1H), 3.67-3.55 (m, 6H), 3.48 (t, J=6.0 Hz, 2H), 3.44-3.36 (m, 2H), 2.92 (s, 3H), 2.91-2.89 (m, 1H), 2.88-2.85 (m, 2H), 2.84-2.68 (m, 2H), 2.19-2.11 (m, 1H), 2.00-1.91 (m, 2H), 1.46 (s, 9H); LC-MS (ESI⁺) m/z 540.3 (M+Na)⁺.

Step 3—2-(2,6-Dioxo-3-piperidyl)-5-[3-[2-[2-(methylamino)ethoxy]ethoxy]propyl]isoindoline-1,3-dione To a solution of tert-butyl N-[2-[2-[3-[2-(2,6-dioxo-3-piperidyl)-1,3-dioxo-isoindolin-5-yl]propoxy]ethoxy]ethyl]-N-methyl-carbamate (0.95 g, 1.84 mmol) in DCM (20 mL) was added HCl/dioxane (4 M, 12 mL). The mixture was stirred at 20° C. for 1 hour. On completion, the mixture was concentrated in vacuo to give the title compound (0.83 g, 99% yield, HCl salt) as light yellow solid. LC-MS (ESI⁺) m/z 418.3 (M+H)⁺.

N-[3-carbamoyl-1-(4-formylphenyl)pyrazol-4-yl]-2-(4-pyridyl)oxazole-4-carboxamide (Intermediate GE)

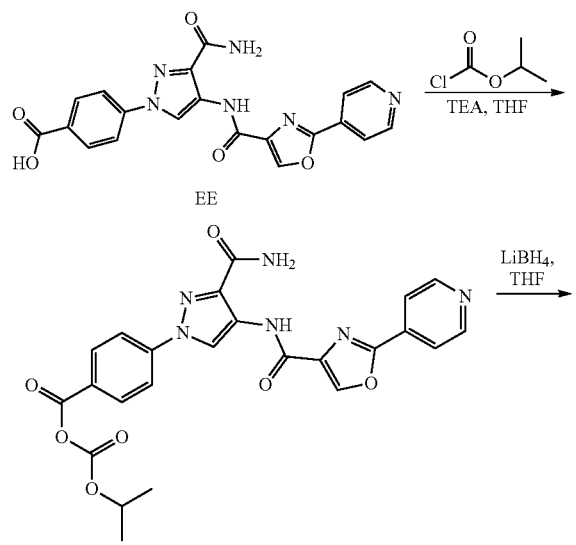

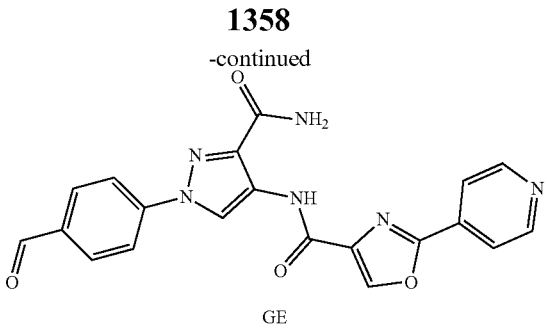

GE

Step 1—Isopropoxycarbonyl 4-[3-carbamoyl-4-[[2-(4-pyridyl)oxazole-4-carbonyl]amino]pyrazol-1-yl] benzoate To a mixture of 4-[3-carbamoyl-4-[[2-(4-pyridyl)oxazole-4-carbonyl]amino]pyrazol-1-yl]benzoic acid (500 mg, 1.20 mmol, Intermediate EE) in THF (20 mL) was added TEA (483 mg, 4.78 mmol, 665 uL) and isopropyl carbonochloridate (366 mg, 2.99 mmol, 414 uL). The reaction mixture was stirred at −10° C. for 2 hours. On completion, the reaction mixture was filtered. The filtrate was used to the next step directly without further purification to give the title compound (600 mg, 99% yield) as light yellow oil. LC-MS (ESI⁺) m/z 505.0 (M+H)⁺.

Step 2—N-[3-carbamoyl-1-[4-(hydroxymethyl)phenyl]pyrazol-4-yl]-2-(4-pyridyl)oxazole-4-carboxamide To a mixture of isopropoxycarbonyl 4-[3-carbamoyl-4-[[2-(4-pyridyl)oxazole-4-carbonyl]amino]pyrazol-1-yl]benzoate (600 mg, 1.19 mmol) in H₂O (5 mL) and THF (50 mL) was added LiBH₄ (155 mg, 7.14 mmol) at 0° C. The reaction mixture was stirred at 0° C. for 2 hours. On completion, the reaction mixture was quenched with water (30 mL) under stirring. Then the mixture was extracted with EA (3×50 mL). The combined organic layer was dried over Na₂SO₄, filtered and concentrated in vacuo to give a residue. The residue was triturated with DCM/PE (5 mL/30 mL) and filtered to give the title compound (250 mg, 51% yield) as light yellow solid. LC-MS (ESI⁺) m/z 405.2 (M+H)⁺.

Step 3—N-[3-carbamoyl-1-(4-formylphenyl)pyrazol-4-yl]-2-(4-pyridyl)oxazole-4-carboxamide To a mixture of N-[3-carbamoyl-1-[4-(hydroxymethyl)phenyl]pyrazol-4-yl]-2-(4-pyridyl)oxazole-4-carboxamide (250 mg, 618 umol) in DCM (10 mL) and THF (10 mL) was added DMP (524 mg, 1.24 mmol) at 0° C. The reaction mixture was stirred at 0° C. for 2 hours. On completion, the reaction mixture was diluted with Na₂S₂O₃ (10 mL), NaHCO₃ (10 mL) and stirred for 30 min. Then the mixture was extracted with DCM (3×10 mL) and the combined organic layers was dried over Na₂SO₄, filtered and concentrated in vacuo to give the title compound (230 mg, 92% yield) as light yellow solid. LC-MS (ESI⁺) m/z 403.2 (M+H)⁺.

Tert-butyl N-(cyclopropylmethyl)-N-[4-[4-[[3-(difluoromethyl)-1-(4-formylphenyl)pyrazol-4-yl]carbamoyl]oxazol-2-yl]-2-pyridyl]carbamate (Intermediate GF)

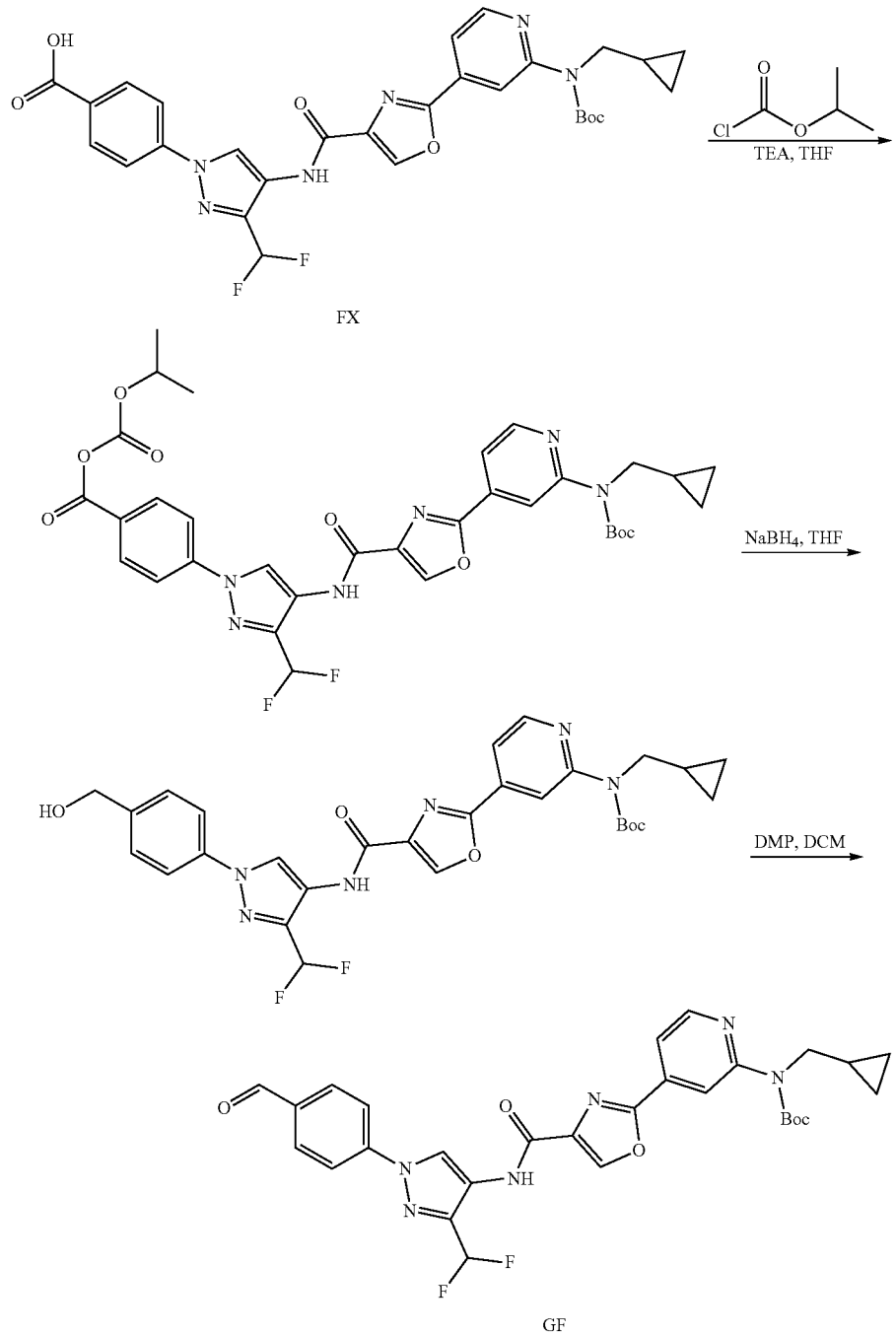

Step 1—Isopropoxycarbonyl 4-[4-[[2-[2-[tert-butoxycarbonyl(cyclopropylmethyl)amino]-4-pyridyl]oxazole-4-carbonyl]amino]-3-(difluoromethyl)pyrazol-1-yl]benzoate To a solution of 4-[4-[[2-[2-[tert-butoxycarbonyl(cyclopropylmethyl)amino]-4-pyridyl]oxazole-4-carbonyl]amino]-3-(difluoromethyl)pyrazol-1-yl]benzoic acid (250 mg, 420 umol, Intermediate FX) in THF (10 mL) was added TEA (170 mg, 1.68 mmol) and isopropyl carbonochloridate (128 mg, 1.05 mmol). The mixture was stirred at −10° C. for 1 hour. On completion, the mixture was filtered and the filtrate was concentrated in vacuo to give the title compound (280 mg, 90% yield) as yellow solid. LC-MS (ESI$^+$) m/z 681.3 (M+H)$^+$.

Step 2—Tert-butyl N-(cyclopropylmethyl)-N-[4-[4-[[3-(difluoromethyl)-1-[4-(hydroxymethyl)phenyl]pyrazol-4-yl]carbamoyl]oxazol-2-yl]-2-pyridyl]carbamate To a solution of isopropoxycarbonyl 4-[4-[[2-[2-[tert-butoxycarbonyl(cyclopropylmethyl)amino]-4-pyridyl]oxazole-4-carbonyl]amino]-3-(difluoromethyl)pyrazol-1-yl]benzoate (280 mg, 411 umol) in THF (30.0 mL) and H₂O (4.00 mL) was added NaBH₄ (62.2 mg, 1.65 mmol). The mixture was stirred at 0° C. for 1 hour. On completion, the mixture was diluted with H₂O (50 mL) and extracted with EtOAc (3×30 mL). The organic layers were dried over anhydrous Na₂SO₄, filtered and concentrated in vacuo. The mixture was triturated with DCM:PE=1:5 (30 mL), and filtered. The filter cake was dried in vacuo to give the title compound (200 mg, 83% yield) as white solid. LC-MS (ESI⁺) m/z 581.3 (M+H)⁺.

Step 3—Tert-butyl N-(cyclopropylmethyl)-N-[4-[4-[[3-(difluoromethyl)-1-(4-formylphenyl)pyrazol-4-yl]carbamoyl]oxazol-2-yl]-2-pyridyl]carbamate To a solution of tert-butyl N-(cyclopropylmethyl)-N-[4-[4-[[3-(difluoromethyl)-1-[4-(hydroxymethyl)phenyl]pyrazol-4-yl]carbamoyl]oxazol-2-yl]-2-pyridyl]carbamate (140 mg, 241 umol) in DCM (10.0 mL) was added DMP (204 mg, 482 umol). The mixture was stirred at 15° C. for 2 hours. On completion, the mixture was diluted with DCM (30 mL), and washed with saturated Na₂S2O3 (2×30 mL) and saturated NaHCO₃ (2×30 mL). The organic layer was dried over anhydrous Na₂SO₄, filtered and concentrated in vacuo to give the title compound (80.0 mg, 57% yield) as white solid. LC-MS (ESI⁺) m/z 579.1 (M+H)⁺.

Tert-butyl N-(5-prop-2-ynoxypentyl)carbamate (Intermediate GG)

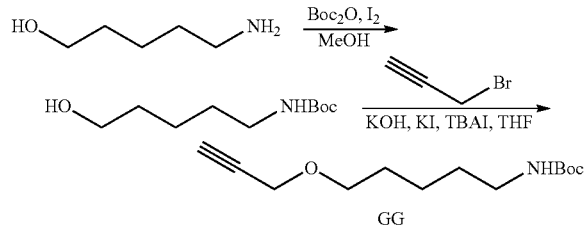

Step 1—Tert-butyl N-(5-hydroxypentyl)carbamate

To a solution of 5-aminopentan-1-ol (21.3 g, 206 mmol) in MeOH (200 mL) was added I₂ (2.63 g, 10.3 mmol) and tert-butoxycarbonyl tert-butyl carbonate (54.2 g, 248 mmol). The mixture was stirred at 25° C. for 12 hours. On completion, the mixture was concentrated to give a residue. The residue was purified by silica gel chromatography to give the title compound (40.0 g, 95% yield) as yellow oil. ¹H NMR (400 MHz, CDCl₃) δ 4.60 (s, 1H), 3.69-3.59 (m, 2H), 3.12 (d, J=5.6 Hz, 2H), 1.9-1.7 (m, 1H), 1.61-1.36 (m, 15H).

Step 2—Tert-butyl N-(5-prop-2-ynoxypentyl)carbamate

To a solution of tert-butyl N-(5-hydroxypentyl)carbamate (5.00 g, 24.6 mmol) and 3-bromoprop-1-yne (3.07 g, 25.8 mmol) in THF (100 mL) was added TBAI (545 mg, 1.48 mmol) and KI (612 mg, 3.69 mmol). Then KOH (1.38 g, 24.6 mmol) was added into the above mixture. The reaction mixture was stirred at 25° C. for 12 hours. On completion, the mixture was filtered and the filtrate was concentrated in vacuo to give a residue. The residue was purified by silica gel chromatograph (PE:EA=5/1) to give the title compound (3.00 g, 50% yield) as a light yellow oil. ¹H NMR (400 MHz, DMSO-d₆) δ 4.12 (d, J=2.4 Hz, 2H), 3.50 (t, J=6.4 Hz, 2H), 3.11 (q, J=6.4 Hz, 2H), 2.41 (t, J=2.4 Hz, 1H), 1.65-1.55 (m, 2H), 1.53-1.33 (m, 13H).

4-[3-(5-Aminopentoxy)propyl]-2-(2,6-dioxo-3-piperidyl)isoindoline-1,3-dione (Intermediate GH)

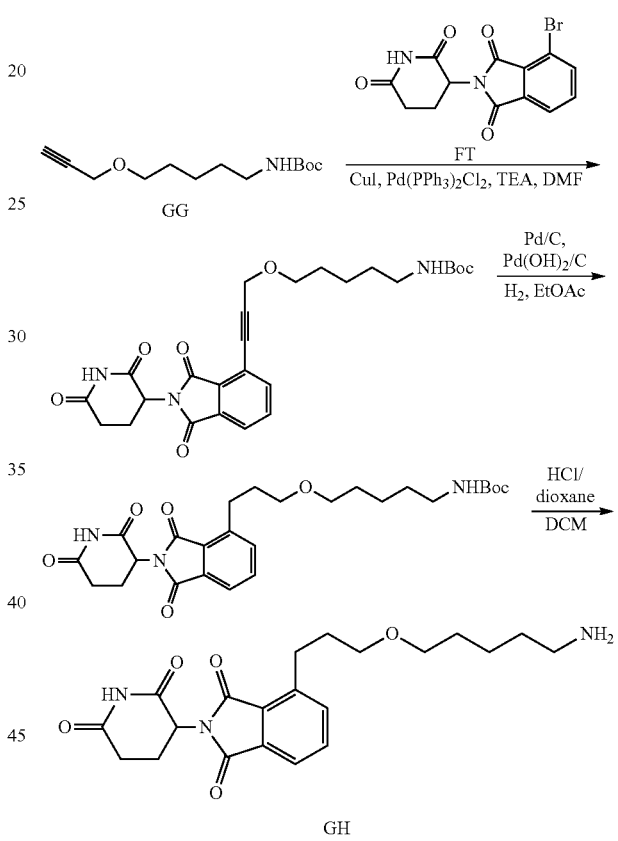

Step 1—Tert-butyl N-[5-[3-[2-(2,6-dioxo-3-piperidyl)-1,3-dioxo-isoindolin-4-yl]prop-2-ynoxy]pentyl]carbamate 4-bromo-2-(2,6-dioxo-3-piperidyl)isoindoline-1,3-dione (500 mg, 1.48 mmol, Intermediate FT), CuI (28.2 mg, 148 umol) and Pd(PPh₃)₂Cl₂ (104 mg, 148 umol) was taking up into a microwave tube. Then DMF (10 mL), TEA (2.70 g, 26.7 mmol) and tert-butyl N-(5-prop-2-ynoxypentyl)carbamate (715 mg, 2.97 mmol, Intermediate GG) were added to the tube. The sealed tube was heated to 80° C. and stirred for 0.5 hours. On completion, the reaction mixture was diluted with water (100 mL) and extracted with EA (5×10 mL). The organic phase was dried over Na₂SO₄, filtered and concentrated in vacuo to give a residue. The residue was purified by silica gel chromatograph (EA/PE=1/1) to give the title compound (1.10 g, 74% yield) as a white solid. LC-MS (ESI+) m/z 498.1 (M+H)+.

Step 2—Tert-butyl N-[5-[3-[2-(2,6-dioxo-3-piperidyl)-1,3-dioxo-isoindolin-4-yl]propoxy]pentyl]carbamate To a solution of tert-butyl N-[5-[3-[2-(2,6-dioxo-3-piperidyl)-1,3-dioxo-isoindolin-4-yl]prop-2-ynoxy]pentyl]carbamate (0.50 g, 1.00 mmol) in THF (5 mL) was added Pd/C (50.0 mg, 10 wt %) and Pd(OH)$_2$ (50 mg, 10 wt %). The mixture was purged with H$_2$ gas several times. The mixture was stirred under H$_2$ (15 psi) at 25° C. for 12 minutes. On completion, the reaction mixture was filtered and the filtrate was concentrated in vacuo to give a residue. The residue was purified by silica gel chromatograph to give the title compound (380 mg, 75% yield) as a yellow gum; LC-MS (ESI+) m/z 502.1 (M+H)+.

Step 3—4-[3-(5-Aminopentoxy)propyl]-2-(2,6-dioxo-3-piperidyl)isoindoline-1,3-dione To a solution of tert-butyl N-[5-[3-[2-(2,6-dioxo-3-piperidyl)-1,3-dioxo-isoindolin-4-yl]propoxy]pentyl]carbamate (380 mg, 757 umol) in DCM (4 mL) was added HCl/dioxane (4 M, 4 mL). The mixture was stirred at 20° C. for 0.5 hour. On completion, the reaction mixture was concentrated in vacuo to give the product (330 mg, 65% yield) as light yellow solid; LC-MS (ESI+) m/z 402.3 (M+H)+.

Tert-butyl methyl(5-(prop-2-yn-1-yloxy)pentyl)carbamate (Intermediate GI)

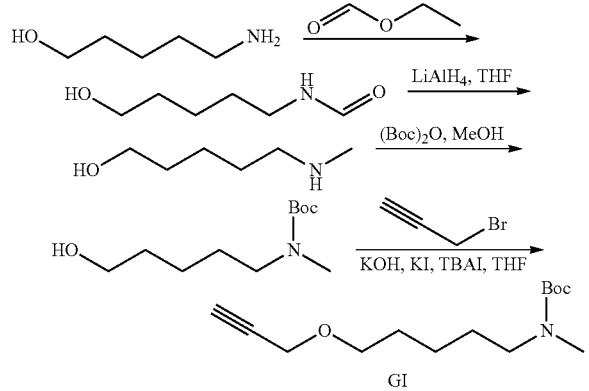

Step 1—N-(5-hydroxypentyl)formamide

A solution of 5-aminopentan-1-ol (CAS #2508-29-4) (7 g, 67.9 mmol) in ethyl formate (20.1 g, 271 mmol) was heated to 90° C. for 6 hrs. On completion, the reaction mixture was concentrated in vacuo to give the title compound (8.9 g, 97% yield) as colorless oil. The residue was used for the next step without purification. LC-MS (ESI+) m/z 132.1 (M+H)+.

Step 2—5-(Methylamino)pentan-1-ol

To a solution of LiAlH$_4$ (3.09 g, 81.4 mmol) in THF (100 mL) was added N-(5-hydroxypentyl)formamide (8.9 g, 67.8 mmol) slowly at 0° C. Then, the reaction mixture was heated to 80° C. for 2 hrs. On completion, the reaction mixture was quenched with a solution of 15% NaOH (20 mL). Thereafter, 50 g anhydrous sodium sulfate was added, and the mixture was filtered. The filtrate was concentrated in vacuo to give the title compound (7.95 g, 100% yield, crude) as colorless oil.

Step 3—Tert-butyl (5-hydroxypentyl)(methyl)carbamate

To a solution of 5-(methylamino)pentan-1-ol (7.95 g, 67.8 mmol) in methanol (100 mL) was added tert-butoxycarbonyl tert-butyl carbonate (14.8 g, 67.8 mmol, 15.6 mL). The reaction mixture was stirred at 25° C. for 12 hrs. On completion, the reaction mixture was concentrated in vacuo. The residue was purified by silica gel chromatography (PE:EA=2:1) to give the title compound (9.6 g, 65% yield) as a colorless oil. $^1$H NMR (400 MHz, CDCl$_3$) δ 3.66 (t, J=6.4 Hz, 2H), 3.25-3.21 (m, 2H), 2.85 (s, 3H), 1.65-1.59 (m, 2H), 1.58-1.51 (m, 2H), 1.47 (s, 9H), 1.42-1.33 (m, 2H).

Step 4—Tert-butyl methyl(5-(prop-2-yn-1-yloxy)pentyl)carbamate

To a solution of tert-butyl N-(5-hydroxypentyl)-N-methyl-carbamate (1.00 g, 4.60 mmol) and 3-bromoprop-1-yne (575 mg, 4.83 mmol) in THF (10 mL) was added KOH (334 mg, 5.06 mmol, 85% purity), KI (153 mg, 920 umol) and TBAI (340 mg, 920 umol). The reaction mixture was stirred at 20° C. for 12 hrs. On completion, the reaction mixture was extracted with ethyl acetate (3×50 mL). The combined organic layers was washed with brine (20 mL), dried over anhydrous sodium sulfate, filtered and concentrated in vacuo. The residue was purified by silica gel chromatography (PE:EA=50:1) to give the title compound (530 mg, 45% yield) as a colorless oil. $^1$H NMR (400 MHz, CDCl$_3$) δ 4.15 (d, J=2.4 Hz, 2H), 3.53 (t, J=6.4 Hz, 2H), 3.24-3.22 (m, 2H), 2.85 (s, 3H), 2.43 (t, J=2.4 Hz, 1H), 1.68-1.63 (m, 2H), 1.57-1.53 (m, 2H), 1.47 (s, 9H), 1.41-1.34 (m, 2H).

2-(2,6-Dioxopiperidin-3-yl)-4-(3-((5-(methylamino)pentyl)oxy)propyl)isoindoline-1,3-dione (Intermediate GJ)

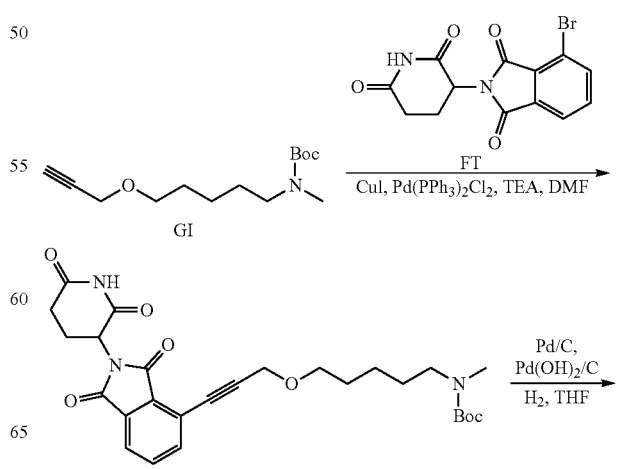

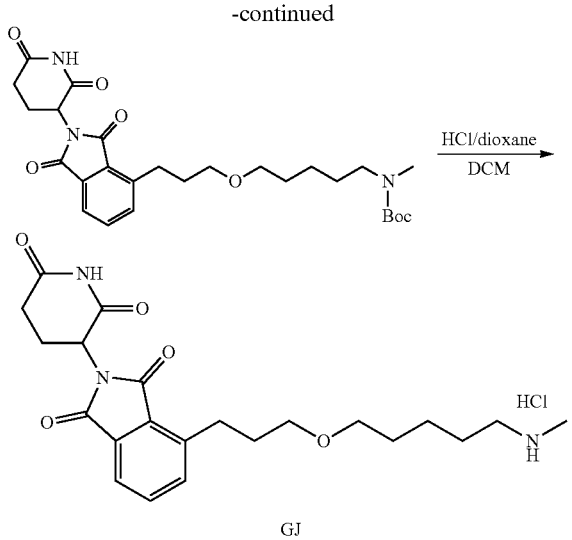

GJ

Step 1—Tert-butyl (5-((3-(2-(2,6-dioxopiperidin-3-yl)-1,3-dioxoisoindolin-4-yl)prop-2-yn-1-yl)oxy)pentyl)(methyl)carbamate 4-Bromo-2-(2,6-dioxo-3-piperidyl)isoindoline-1,3-dione (200 mg, 593 umol, Intermediate FT), tert-butyl N-methyl-N-(5-prop-2-ynoxypentyl)carbamate (152 mg, 593 umol, Intermediate GI), $Pd(PPh_3)_2Cl_2$ (41.6 mg, 59.3 umol), CuI (11.3 mg, 59.3 umol) and TEA (1.08 g, 10.7 mmol, 1.49 mL) were taken up into a microwave tube in DMF (3 mL) under $N_2$. The reaction mixture was de-gassed with $N_2$ and then the seal tube was heated to 80° C. for 0.5 hour. On completion, the reaction mixture was concentrated in vacuo. The residue was purified by silica gel chromatography (PE:EA=2:1) to give the title compound (260 mg, 66% yield) as a yellow oil. $^1$H NMR (400 MHz, $CDCl_3$) δ 8.47 (s, 1H), 7.76 (d, J=7.2 Hz, 1H), 7.71-7.67 (m, 1H), 7.65-7.60 (m, 1H), 4.95-4.91 (m, 1H), 4.38 (s, 2H), 3.60 (t, J=6.8 Hz, 2H), 3.14 (t, J=6.8 Hz, 2H), 2.83-2.66 (m, 7H), 1.66-1.56 (m, 2H), 1.49-1.43 (m, 2H), 1.38 (s, 9H), 1.36-1.30 (m, 2H); LC-MS (ESI$^+$) m/z 512.1 (M+H)$^+$.

Step 2—Tert-butyl (5-(3-(2-(2,6-dioxopiperidin-3-yl)-1,3-dioxoisoindolin-4-yl)propoxy)pentyl)(methyl) carbamate To a solution of tert-butyl N-[5-[3-[2-(2,6-dioxo-3-piperidyl)-1,3-dioxo-isoindolin-4-yl]prop-2-ynoxy]pentyl]-N-methyl-carbamate (260 mg, 391 umol) in THF (20 mL) was added $Pd(OH)_2$/C (26 mg, 10% wt) and Pd/C (26 mg, 10% wt) under $N_2$. The suspension was degassed under vacuum and purged with $H_2$ several times. The mixture was stirred under $H_2$ (15 Psi) at 25° C. for 12 hours. On completion, the reaction mixture was filtered and concentrated in vacuo to give the title compound (260 mg, 99% yield) as a white solid. LC-MS (ESI$^+$) m/z 538.1 (M+Na)$^+$.

Step 3—2-(2,6-Dioxopiperidin-3-yl)-4-(3-((5-(methylamino)pentyl)oxy)propyl)isoindoline-1,3-dione To a solution of tert-butyl N-[5-[3-[2-(2,6-dioxo-3-piperidyl)-1,3-dioxo-isoindolin-4-yl]propoxy]pentyl]-N-methyl-carbamate (260 mg, 388 umol) in DCM (5 mL) was added HCl/dioxane (4 M, 5 mL) under $N_2$. The mixture was stirred at 25° C. for 1 hour. On completion, the reaction mixture was concentrated in vacuo to give the title compound (175 mg, 99% yield) as a white solid which was used for the next step without purification. LC-MS (ESI$^+$) m/z 416.1 (M+H)$^+$.

Tert-butyl N-methyl-N-(2-prop-2-ynoxyethyl)carbamate (Intermediate GK)

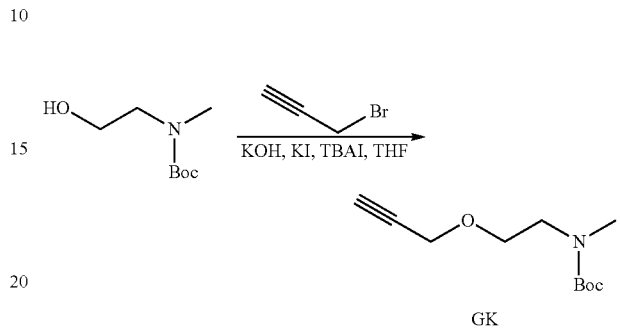

To a solution of tert-butyl N-(2-hydroxyethyl)-N-methyl-carbamate (4 g, 22.8 mmol, CAS #57561-39-4) and 3-bromoprop-1-yne (2.72 g, 22.8 mmol, 1.97 mL) in THF (40 mL) was added TBAI (505 mg, 1.37 mmol), KI (568 mg, 3.42 mmol), and KOH (1.28 g, 22.8 mmol), and the reaction mixture was stirred at 25° C. for 16 hr. On completion, the mixture was filtered, and the filtrate was concentrated in vacuo to give a residue. The residue was purified by flash silica gel chromatography (PE/EA=5/1, Rf=0.6) to give the title compound (2.9 g, 59% yield) as yellow oil. $^1$H NMR (400 MHz, $CDCl_3$) δ 4.15 (d, J=2.4 Hz, 2H), 3.64 (s, 2H), 3.41 (s, 2H), 2.92 (s, 3H), 2.53-2.35 (m, 1H), 1.46 (s, 9H)

2-(2,6-Dioxo-3-piperidyl)-4-[3-[2-(methylamino)ethoxy]propyl]isoindoline-1,3-dione (Intermediate GL)

1367

-continued

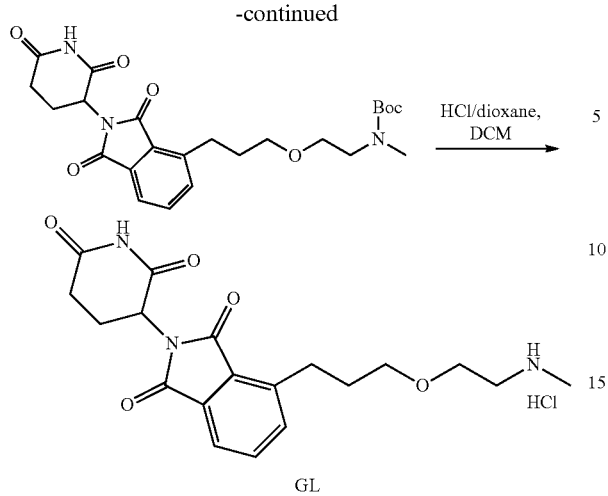

GL

Step 1—Tert-butyl N-[2-[3-[2-(2,6-dioxo-3-piperidyl)-1,3-dioxo-isoindolin-4-yl]prop-2-ynoxy]ethyl]-N-methyl-carbamate To a solution of tert-butyl N-methyl-N-(2-prop-2-ynoxyethyl)carbamate (379 mg, 1.78 mmol, Intermediate GK) and 4-bromo-2-(2,6-dioxo-3-piperidyl)isoindoline-1,3-dione (300 mg, 889 umol, Intermediate FT) in DMF (4 mL) was added TEA (1.62 g, 16.0 mmol, 2.23 mL), CuI (16.9 mg, 88.9 umol) and Pd(PPh$_3$)$_2$Cl$_2$ (62.4 mg, 88.9 umol), the reaction mixture was heated at 80° C. for 30 min under microwave. On completion, the mixture was concentrated in vacuo to give a residue. The residue was purified by column chromatography (SiO$_2$, Petroleum ether/Ethyl acetate=5/1 to I/O, Rf=0.29) to give the title compound (430 mg, 100% yield) as yellow oil. LC-MS (ESI$^+$) m/z 370.2 (M+H–100)$^+$.

Step 2—Tert-butyl N-[2-[3-[2-(2,6-dioxo-3-piperidyl)-1,3-dioxo-isoindolin-4-yl]propoxy]ethyl]-N-methyl-carbamate To a solution of tert-butyl N-[2-[3-[2-(2,6-dioxo-3-piperidyl)-1,3-dioxo-isoindolin-4-yl]prop-2-ynoxy]ethyl]-N-methyl-carbamate (430 mg, 915 umol) in THF (10 mL) was added Pd(OH)$_2$/C (250 mg, 10 wt %) and Pd/C (250 mg, 10 wt %), and the reaction mixture was stirred at 25° C. under H$_2$ (15 psi) for 16 hr. On completion, the residue was filtered and the filtrate was concentrated in vacuo to give the title compound (350 mg, 80% yield) as brown solid. LC-MS (ESI$^+$) m/z 496.2 (M+Na)$^+$.

Step 3—2-(2,6-Dioxo-3-piperidyl)-4-[3-[2-(methylamino)ethoxy]propyl]isoindoline-1,3-dione To a solution of tert-butyl N-[2-[3-[2-(2,6-dioxo-3-piperidyl)-1,3-dioxo-isoindolin-4-yl]propoxy]ethyl]-N-methyl-carbamate (350 mg, 739 umol) in DCM (4 mL) was added HCl/dioxane (4 M, 4 mL), and the reaction mixture was stirred at 25° C. for 20 mins. On completion, the mixture was concentrated in vacuo to give the title compound (300 mg, 99% yield) as yellow oil. LC-MS (ESI$^+$) m/z 374.2 (M+H)$^+$.

1368

Tert-butyl N-hex-5-ynyl-N-methyl-carbamate (Intermediate GM)

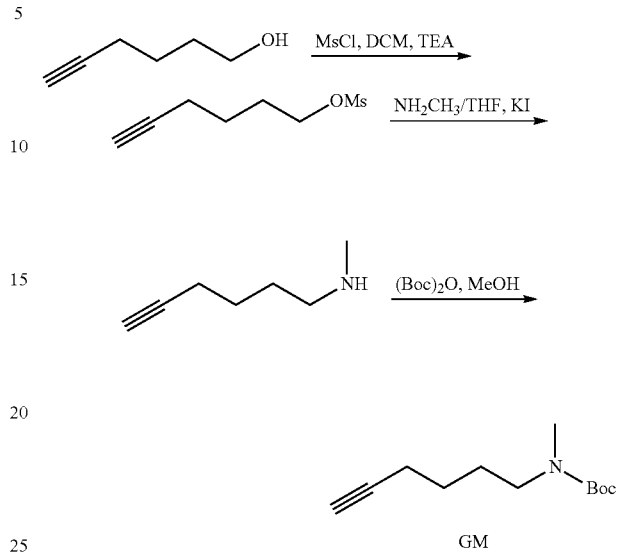

Step 1—Hex-5-ynyl methanesulfonate

To a solution of hex-5-yn-1-ol (2.00 g, 20.4 mmol, CAS #928-90-5) and TEA (5.16 g, 51.0 mmol) in DCM (20 mL) was added MsCl (2.80 g, 24.5 mmol) at 0° C. The reaction mixture was stirred at 0° C. for 3 hrs. On completion, the mixture was quenched with water (20 mL), and extracted with DCM (2×20 mL). The organic layer was washed with brine (50 mL), dried with Na$_2$SO$_4$, filtered and the filtrate was concentrated in vacuo to give the title compound (3.20 g, 89% yield) as yellow oil. $^1$H NMR (400 MHz, CDCl$_3$) δ 4.27 (t, J=6.4 Hz, 2H), 3.02 (s, 3H), 2.30-2.24 (m, 2H), 1.98 (t, J=2.8 Hz, 1H), 1.93-1.84 (m, 2H), 1.70-1.64 (m, 2H).

Step 2—N-methylhex-5-yn-1-amine

A solution of hex-5-ynyl methanesulfonate (0.60 g, 3.40 mmol) and KI (28.3 mg, 170 umol) in a solution of methanamine (2 M, 8.51 mL) was stirred at 55° C. for 15 hrs. On completion, the mixture was concentrated in vacuo to give the title compound (0.25 g, 66% yield) as yellow oil. $^1$H NMR (400 MHz, CDCl$_3$) δ 2.63 (t, J=7.2 Hz, 2H), 2.45 (s, 3H), 2.23-2.19 (m, 2H), 1.94 (t, J=2.4 Hz, 1H), 1.68-1.56 (m, 4H).

Step 3—Tert-butyl N-hex-5-ynyl-N-methyl-carbamate

To a solution of N-methylhex-5-yn-1-amine (500 mg, 4.50 mmol) in MeOH (10 mL) was added (Boc)$_2$O (1.18 g, 5.40 mmol). The reaction mixture was stirred at 25° C. for 17 hrs. On completion, the mixture was concentrated in vacuo. The residue was purified by silica gel chromatography to give the title compound (670 mg, 70% yield) as colorless oil. $^1$H NMR (400 MHz, CDCl$_3$) δ 3.22-3.11 (m, 2H), 2.77 (s, 3H), 2.20-2.12 (m, 2H), 1.88 (t, J=2.4 Hz, 1H), 1.60-1.53 (m, 2H), 1.46-1.41 (m, 2H), 1.39 (s, 9H).

1369

2-(2,6-Dioxo-3-piperidyl)-4-[6-(methylamino)hexyl]isoindoline-1,3-dione (Intermediate GN)

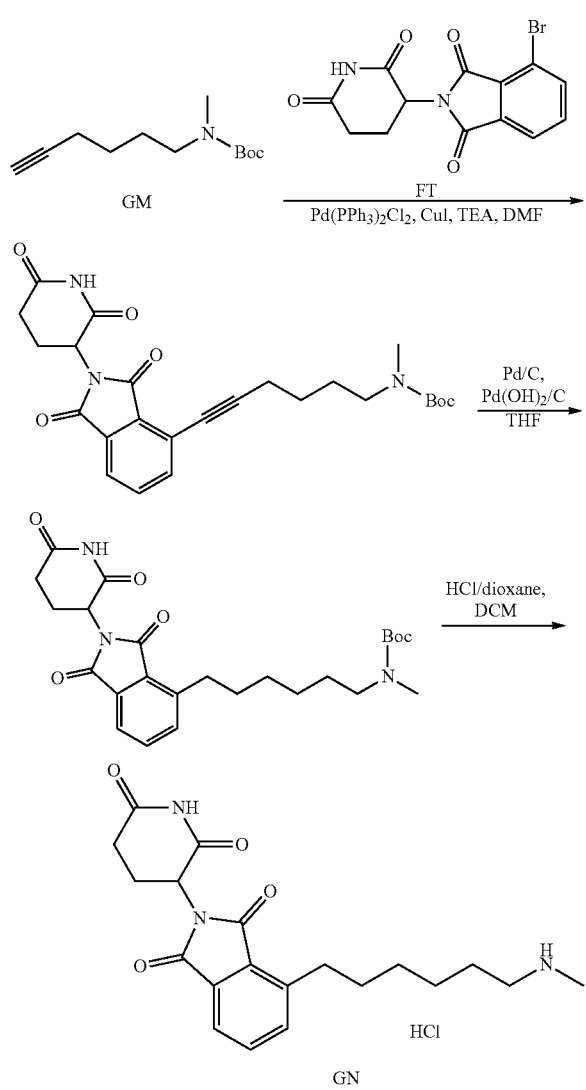

Step 1—Tert-butyl N-[6-[2-(2,6-dioxo-3-piperidyl)-1,3-dioxo-isoindolin-4-yl]hex-5-ynyl]-N-methyl-carbamate 4-Bromo-2-(2,6-dioxo-3-piperidyl)isoindoline-1,3-dione (0.60 g, 1.78 mmol, Intermediate FT), CuI (33.9 mg, 178 umol) and Pd(PPh$_3$)$_2$Cl$_2$ (125 mg, 178 umol) was taken up into a microwave tube. Then tert-butyl N-hex-5-ynyl-N-methyl-carbamate (602 mg, 2.85 mmol, Intermediate GM), TEA (3.24 g, 32.0 mmol) and DMF (5 mL) were added into the above tube. The mixture was degassed with N$_2$ gas for 5 minutes. The sealed tube was heated at 80° C. for 30 minutes under microwave. On completion, the mixture was filtered and the filtrate was concentrated in vacuo. The residue was purified by reverse phase (0.1% HCl condition) to give the title compound (720 mg, 78% yield) as a yellow gum. LC-MS (ESI$^+$) m/z 490.1 (M+Na)$^+$.

1370

Step 2—Tert-butyl N-[6-[2-(2,6-dioxo-3-piperidyl)-1,3-dioxo-isoindolin-4-yl]hexyl]-N-methyl-carbamate To a solution of tert-butyl N-[6-[2-(2,6-dioxo-3-piperidyl)-1,3-dioxo-isoindolin-4-yl]hex-5-ynyl]-N-methyl-carbamate (720 mg, 1.39 mmol) in THF (8 mL) was added Pd/C (0.2 g, 10 wt %) and Pd(OH)$_2$/C (0.2 g, 10 wt %). The reaction mixture was stirred at 25° C. for 18 hrs under H$_2$ (15 Psi). On completion, the mixture was filtered and the filtrate was concentrated in vacuo to give the title compound (620 mg, 95% yield) as a light yellow solid. LC-MS (ESI$^+$) m/z 494.1 (M+Na)$^+$.

Step 3—2-(2,6-Dioxo-3-piperidyl)-4-[6-(methylamino)hexyl]isoindoline-1,3-dione To a solution of tert-butyl N-[6-[2-(2,6-dioxo-3-piperidyl)-1,3-dioxo-isoindolin-4-yl]hexyl]-N-methyl-carbamate (620 mg, 1.31 mmol) in DCM (4 mL) was added HCl/dioxane (6 mL). The reaction mixture was stirred at 25° C. for 0.5 hr. On completion, the mixture was concentrated in vacuo to give the title compound (530 mg, 94% yield) as a yellow solid. LC-MS (ESI$^+$) m/z 372.2 (M+H)$^+$.

4-(3-Aminopropyl)-2-(2,6-dioxopiperidin-3-yl)isoindoline-1,3-dione (Intermediate GO)

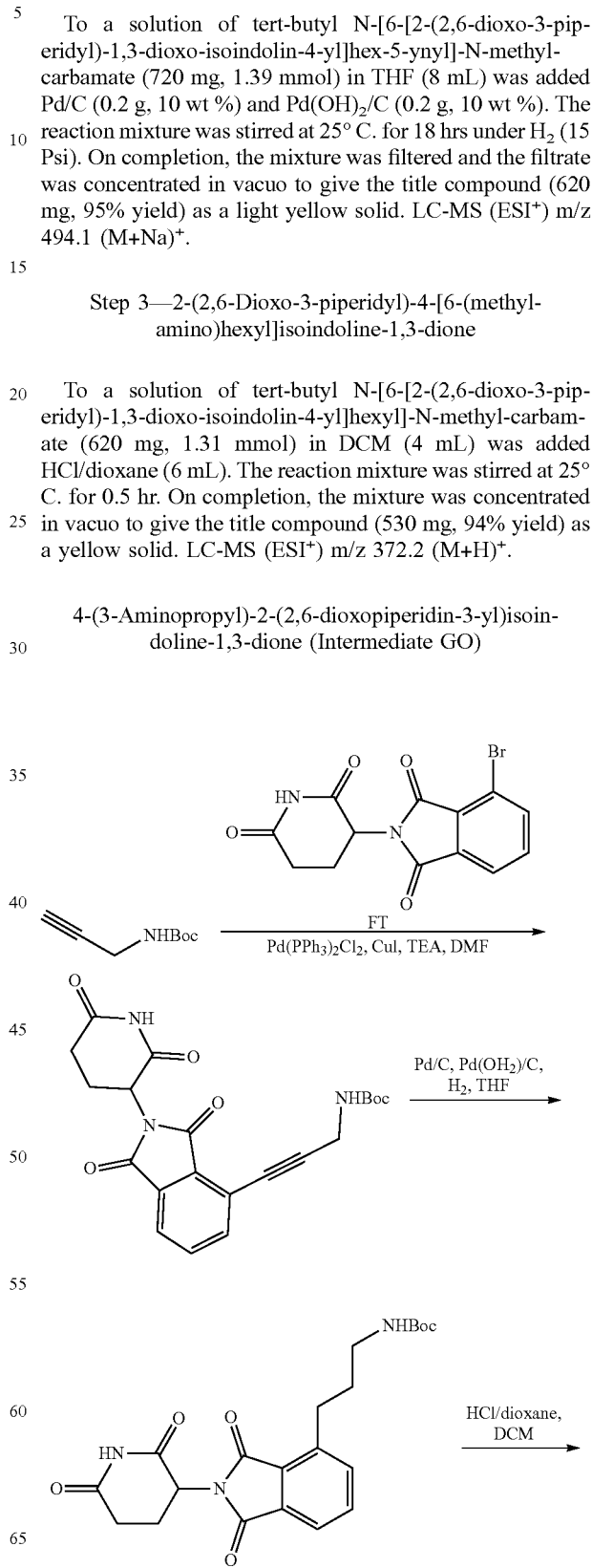

-continued

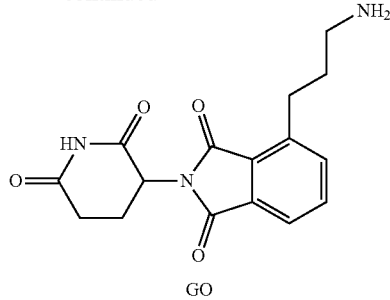

GO

Step 1—Tert-butyl (3-(2-(2,6-dioxopiperidin-3-yl)-1,3-dioxoisoindolin-4-yl)prop-2-yn-1-yl)carbamate 4-Bromo-2-(2,6-dioxo-3-piperidyl)isoindoline-1,3-dione (200 mg, 593 umol, Intermediate FT), tert-butyl N-prop-2-ynylcarbamate (CAS #: 92136-39-5) (92.0 mg, 593 umol), Pd(PPh$_3$)$_2$Cl$_2$ (41.6 mg, 59.3 umol) and TEA (1.08 g, 10.7 mmol, 1.49 mL), CuI (11.3 mg, 59.3 umol) were taken up into a microwave tube in DMF (3 mL) under N$_2$. The reaction mixture was de-gassed with N$_2$ and then the seal tube was heated to 80° C. for 0.5 hour. On completion, the reaction mixture was concentrated in vacuo. The residue was purified by silica gel chromatography (PE:EA=2:1) to give the title compound (200 mg, 73% yield) as a white solid. $^1$H NMR (400 MHz, CDCl$_3$) δ 8.07 (s, 1H), 7.85 (dd, J=1.2, 7.2 Hz, 1H), 7.78-7.69 (m, 2H), 5.01 (dd, J=5.2, 12.4 Hz, 1H), 4.94 (s, 1H), 4.28 (d, J=5.2 Hz, 2H), 2.94-2.74 (m, 3H), 2.21-2.14 (m, 1H), 1.50 (s, 9H); LC-MS (ESI$^+$) m/z 434.0 (M+Na)$^+$.

Step 2—Tert-butyl (3-(2-(2,6-dioxopiperidin-3-yl)-1,3-dioxoisoindolin-4-yl)propyl)carbamate To a solution of tert-butyl N-[3-[2-(2,6-dioxo-3-piperidyl)-1,3-dioxo-isoindolin-4-yl]prop-2-ynyl]carbamate (200 mg, 433 umol) in THF (20 mL) was added Pd/C (20 mg, 10% wt) and Pd(OH)$_2$/C (20 mg, 10% wt) under N$_2$. The suspension was degassed under vacuum and purged with H$_2$ gas several times. The mixture was stirred under H$_2$ (15 Psi) at 25° C. for 12 hours. On completion, the reaction mixture was filtered and concentrated in vacuo to give the title compound (200 mg, 95% yield) as a white solid. LC-MS (ESI$^+$) m/z 438.0 (M+Na)$^+$.

Step 3—4-(3-Aminopropyl)-2-(2,6-dioxopiperidin-3-yl)isoindoline-1,3-dione

To a solution of tert-butyl N-[3-[2-(2,6-dioxo-3-piperidyl)-1,3-dioxo-isoindolin-4-yl]propyl]carbamate (200 mg, 404 umol) in DCM (5 mL) was added HCl/dioxane (4 M, 5 mL). The mixture was stirred at 25° C. for 1 hour. On completion, the reaction mixture was concentrated in vacuo to give the title compound (142 mg, 100% yield) as a white solid.

Tert-butyl (4-(4-((3-carbamoyl-1-(4-(methyl(5-oxopentyl)carbamoyl)phenyl)-1H-pyrazol-4-yl)carbamoyl)oxazol-2-yl)pyridin-2-yl)(cyclopropylmethyl)carbamate (Intermediate GP)

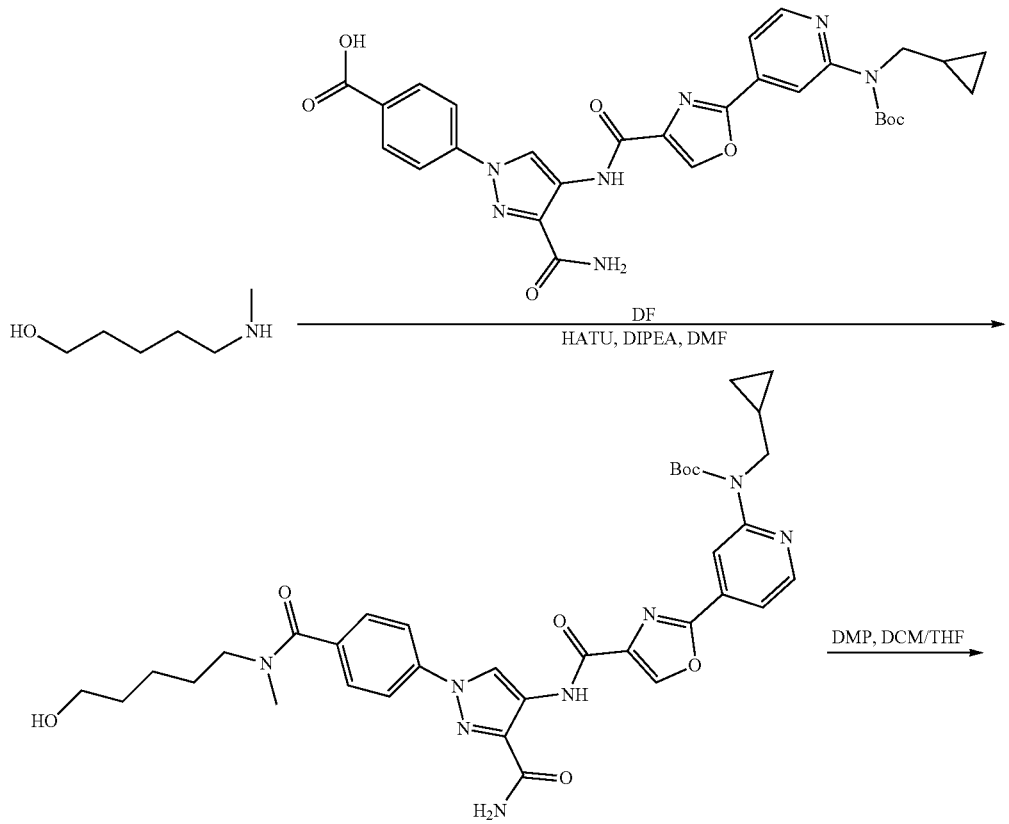

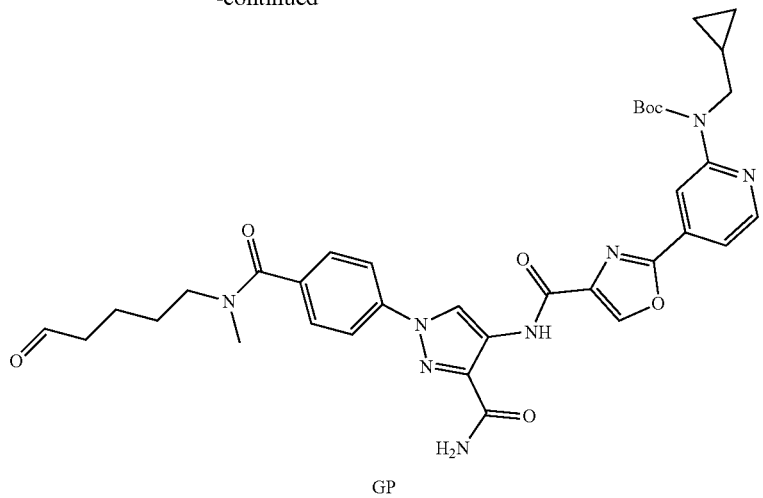

GP

Step 1—Tert-butyl (4-(4-((3-carbamoyl-1-(4-((5-hydroxypentyl)(methyl)carbamoyl)phenyl)-1H-pyrazol-4-yl)carbamoyl)oxazol-2-yl)pyridin-2-yl)(cyclopropylmethyl)carbamate To a solution of 5-(methylamino)pentan-1-ol (141 mg, 918 umol, HCl, synthesized via Steps 1-2 of Intermediate GI) and 4-[4-[[2-[2-[tert-butoxycarbonyl(cyclopropylmethyl)amino]-4-pyridyl]oxazole-4-carbonyl]amino]-3-carbamoyl-pyrazol-1-yl]benzoic acid (539 mg, 918 umol, Intermediate DF) in DMF (25 mL) was added DIPEA (593 mg, 4.59 mmol, 799 uL). The reaction mixture was stirred at 0.5 hour. Then HATU (384 mg, 1.01 mmol) was added to the reaction mixture. The resulting reaction mixture was stirred at 25° C. for 0.5 hr. On completion, the reaction mixture was concentrated in vacuo to give the residue. The residue was purified by prep-HPLC (acidified condition: 0.1%, HCl) to give the title compound (300 mg, 48% yield) as a white solid. $^1$H NMR (400 MHz, CDCl$_3$) δ 10.97 (s, 1H), 8.91 (s, 1H), 8.58-8.49 (m, 1H), 8.42 (s, 1H), 8.36 (s, 1H), 7.84 (d, J=8.8 Hz, 2H), 7.79 (dd, J=1.2, 5.2 Hz, 1H), 7.62-7.54 (m, 2H), 6.91 (s, 1H), 5.58 (s, 1H), 3.95 (d, J=7.2 Hz, 2H), 3.73-3.71 (m, 1H), 3.63-3.61 (m, 2H), 3.33-3.31 (m, 1H), 1.75-1.59 (m, 2H), 1.59 (s, 9H), 1.54-1.50 (m, 2H), 1.31-1.18 (m, 3H), 0.50-0.40 (m, 2H), 0.34-0.25 (m, 2H).

Step 2—Tert-butyl (4-(4-((3-carbamoyl-1-(4-(methyl(5-oxopentyl)carbamoyl)phenyl)-1H-pyrazol-4-yl)carbamoyl)oxazol-2-yl)pyridin-2-yl)(cyclopropylmethyl)carbamate (9)—Notebook Page: EW5356-822

To a solution of tert-butyl N-[4-[4-[[3-carbamoyl-1-[4-[5-hydroxypentyl(methyl)carbamoyl]phenyl]pyrazol-4-yl]carbamoyl]oxazol-2-yl]-2-pyridyl]-N-(cyclopropylmethyl)carbamate (300 mg, 437 umol) in DCM (10 mL) was added DMP (371 mg, 874 umol, 270 uL). The reaction mixture was stirred at 25° C. for 5 hrs. On completion, the reaction mixture was quenched with saturated NaS$_2$O$_3$ (30 mL), and extracted with DCM (3×100 mL). The combined organic layer was washed with saturated NaHCO$_3$ (50 mL), then washed with brine (50 mL), dried over anhydrous sodium sulfate, filtered and concentrated in vacuo to give the title compound (299 mg, 100% yield) as a white solid. LC-MS (ESI$^+$) m/z 685.1 (M+H)$^+$.

Tert-butyl N-tert-butoxycarbonyl-N-non-8-ynyl-carbamate (Intermediate GO)

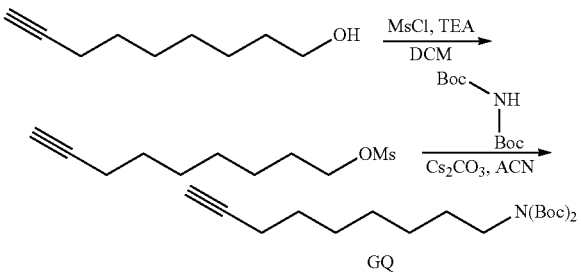

GQ

Step 1—Non-8-ynyl methanesulfonate

To a mixture of non-8-yn-1-ol (5.00 g, 35.6 mmol, CAS #10160-28-8) and TEA (10.8 g, 106 mmol, 14.8 mL) in DCM (100 mL) was added MsCl (6.13 g, 53.4 mmol, 4.14 mL). The reaction mixture was stirred at 25° C. for 2 hours. On completion, the reaction mixture was concentrated in vacuo. The residue was diluted with water (10 mL) and extracted with DCM (3×10 mL). The combined organic layers was dried over Na$_2$SO$_4$, filtered and concentrated in vacuo to give the title compound (7.70 g, 98% yield) as light yellow oil. $^1$H NMR (400 MHz, CDCl$_3$) δ 4.23 (t, J=6.4 Hz, 2H), 3.01 (s, 3H), 2.22-2.18 (m, 2H), 1.95 (t, J=2.4 Hz, 1H), 1.80-1.73 (m, 2H), 1.58-1.50 (m, 2H), 1.47-1.36 (m, 6H).

Step 2—Tert-butyl N-tert-butoxycarbonyl-N-non-8-ynyl-carbamate

To a mixture of non-8-ynyl methanesulfonate (1.00 g, 4.58 mmol) and tert-butyl N-tert-butoxycarbonylcarbamate (1.49 g, 6.87 mmol, CAS #51779-32-9) in ACN (10 mL) was added Cs$_2$CO$_3$ (4.48 g, 13.7 mmol). The reaction mixture was stirred at 80° C. for 2 hours. On completion, the reaction mixture was filtered and concentrated in vacuo. The residue was purified by column chromatography to give the title compound (650 mg, 41% yield) as colorless oil. $^1$H NMR (400 MHz, CDCl$_3$) δ 3.59-3.53 (m, 2H), 2.22-2.12 (m, 2H), 1.94 (t, J=2.4 Hz, 1H), 1.62-1.53 (m, 4H), 1.52 (s, 18H), 1.45-1.29 (m, 6H).

Tert-butyl N-methyl-N-non-8-ynyl-carbamate (Intermediate GR)

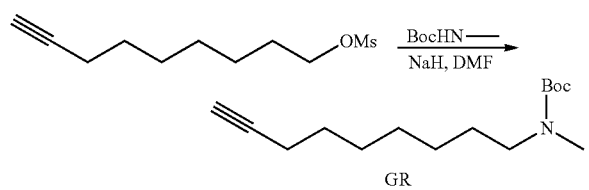

To a solution of tert-butyl N-methylcarbamate (300 mg, 2.29 mmol, CAS #16066-84-5) in DMF (10 mL) was added NaH (183 mg, 4.58 mmol, 60% purity) at 0° C. The mixture was stirred at 25° C. for 2 hours. Then non-8-ynyl methanesulfonate (0.5 g, 2.29 mmol, synthesized via Step 1 of Intermediate GQ) in dry DMF (2 mL) was added at 0° C., and then the mixture was stirred at 25° C. for 5 hours. On completion, the mixture was quenched by addtion H$_2$O (30 mL), then extracted with EA (3×50 mL), and the organic phase was concentrated in vacuo to give a residue. The residue was purified by flash silica gel chromatography to give the title compound (410 mg, 70% yield) as colorless oil. $^1$H NMR (400 MHz, DMSO-d$_6$) δ 3.14 (t, J=7.6 Hz, 2H), 2.75 (s, 3H), 2.74-2.72 (m, 1H), 2.17-2.11 (m, 2H), 1.48-1.42 (m, 4H), 1.39 (s, 9H), 1.35-1.18 (m, 6H).

2-(2,6-Dioxo-3-piperidyl)-4-[9-(methylamino)nonyl]isoindoline-1,3-dione (Intermediate GS)

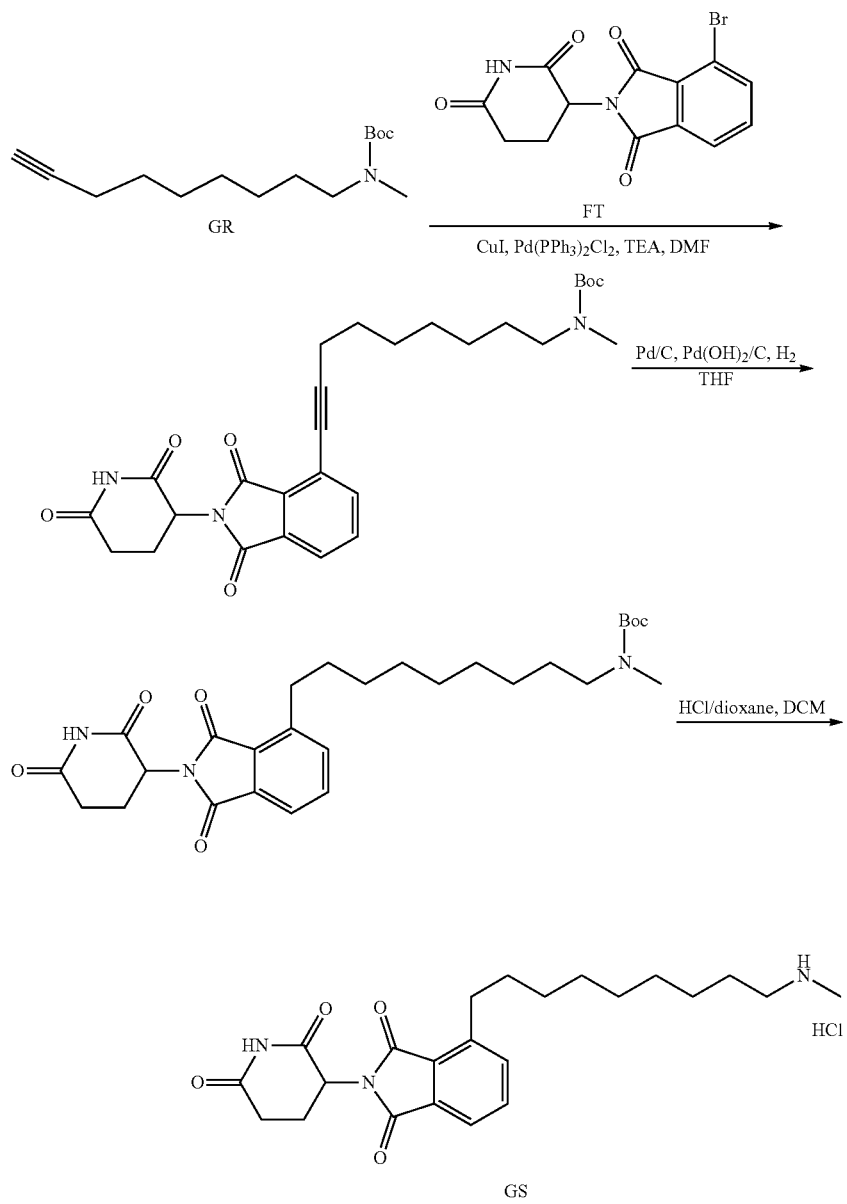

Step 1—Tert-butyl N-[9-[2-(2,6-dioxo-3-piperidyl)-1,3-dioxo-isoindolin-4-yl]non-8-ynyl]-N-methyl-carbamate 4-Bromo-2-(2,6-dioxo-3-piperidyl)isoindoline-1,3-dione (300 mg, 889 umol, Intermediate FT), CuI (16.9 mg, 88.9 umol) and Pd(PPh₃)₂Cl₂ (62.4 mg, 88.9 umol) were taken up into a microwave tube. Then tert-butyl N-methyl-N-non-8-ynyl-carbamate (405 mg, 1.60 mmol, Intermediate GR), TEA (1.62 g, 16.0 mmol, 2.23 mL) and DMF (3 mL) were added into the above tube. The mixture was degassed with N₂ for 5 minutes. The sealed tube was heated at 80° C. for 30 minutes under microwave. On completion, the mixture was concentrated in vacuo to give a residue. The residue was purified by reverse phase (0.1% FA condition) to give the title compound (380 mg, 77% yield) as a white solid. LC-MS (ESI⁺) m/z 532.4 (M+Na)⁺.

Step 2—Tert-butyl N-[9-[2-(2,6-dioxo-3-piperidyl)-1,3-dioxo-isoindolin-4-yl]nonyl]-N-methyl-carbamate To a solution of tert-butyl N-[9-[2-(2,6-dioxo-3-piperidyl)-1,3-dioxo-isoindolin-4-yl]non-8-ynyl]-N-methyl-carbamate (380 mg, 745 umol) in THF (10 mL) was added Pd(OH)₂/C (100 mg, 10 wt %) and Pd/C (100 mg, 10 wt %). The reaction mixture was stirred under H₂ (15 psi) at 25° C. for 12 hours. On completion, the residue was filtered and the filtrate was concentrated in vacuo to give the title compound (380 mg, 99% yield) as yellow oil. LC-MS (ESI⁺) m/z 536.2 (M+Na)⁺.

Step 3—2-(2,6-Dioxo-3-piperidyl)-4-[9-(methylamino)nonyl]isoindoline-1,3-dione

To a solution of tert-butyl N-[9-[2-(2,6-dioxo-3-piperidyl)-1,3-dioxo-isoindolin-4-yl]nonyl]-N-methyl-carbamate (380 mg, 739 umol) in DCM (3 mL) was added HCl/dioxane (4 M, 4 mL), and the reaction mixture was stirred at 25° C. for 20 min. On completion, the mixture was concentrated in vacuo to give the title compound (330 mg, 99% yield, HCl) as yellow solid. LC-MS (ESI⁺) m/z 414.3 (M+H)⁺.

4-(9-Aminononyl)-2-(2,6-dioxo-3-piperidyl)isoindoline-1,3-dione (Intermediate GT)

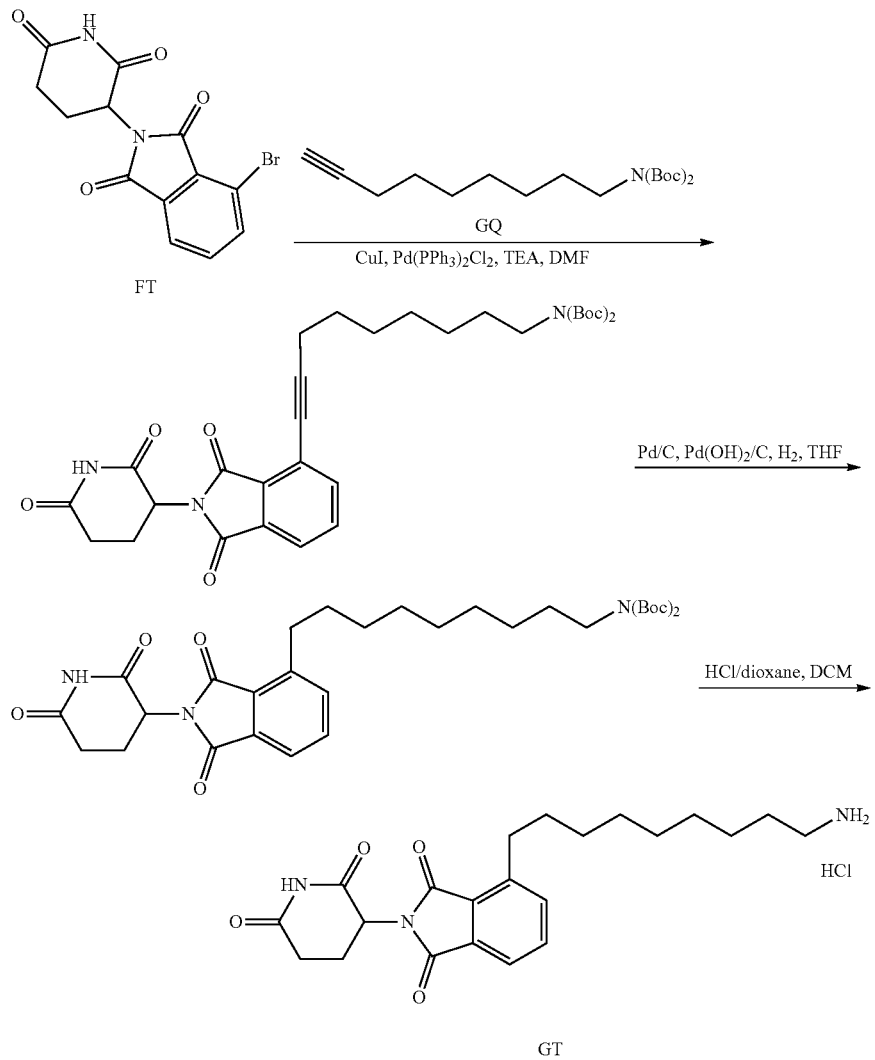

Step 1—Tert-butyl N-tert-butoxycarbonyl-N-[9-[2-(2,6-dioxo-3-piperidyl)-1,3-dioxo-isoindolin-4-yl]non-8-ynyl]carbamate To a mixture of 4-bromo-2-(2,6-dioxo-3-piperidyl)isoindoline-1,3-dione (300 mg, 889 umol, Intermediate FT) and tert-butyl N-tert-butoxycarbonyl-N-non-8-ynyl-carbamate (453 mg, 1.33 mmol, Intermediate GQ) in DMF (5 mL) was added Pd(PPh$_3$)$_2$Cl$_2$ (62.4 mg, 88.9 umol), CuI (16.9 mg, 88.9 umol) and TEA (1.62 g, 16.0 mmol, 2.23 mL). The reaction mixture was heated at 80° C. for 30 mins under microwave. On completion, the reaction mixture was concentrated in vacuo. The residue was purified by prep-HPLC (0.1% FA condition) compound (340 mg, 64% yield) as brown oil. LC-MS (ESI$^+$) m/z 618.4 (M+Na)$^+$

Step 2—Tert-butyl N-tert-butoxycarbonyl-N-[9-[2-(2,6-dioxo-3-piperidyl)-1,3-dioxo-isoindolin-4-yl]nonyl]carbamate To a mixture of tert-butyl N-tert-butoxycarbonyl-N-[9-[2-(2,6-dioxo-3-piperidyl)-1,3-dioxo-isoindolin-4-yl]non-8-ynyl]carbamate (440 mg, 738 umol) in THF (5 mL) was added Pd/C (150 mg, 10 wt %) and Pd(OH)$_2$/C (150 mg, 10 wt %). The reaction mixture was stirred at 25° C. for 1 hour under H$_2$ (15 Psi) atmosphere. On completion, the reaction mixture was filtered and concentrated in vacuo to give the title compound (442 mg, 99% yield) as white solid. LC-MS (ESI$^+$) m/z 622.5 (M+Na)$^+$.

Step 3—4-(9-Aminononyl)-2-(2,6-dioxo-3-piperidyl)isoindoline-1,3-dione

To a mixture of tert-butyl N-tert-butoxycarbonyl-N-[9-[2-(2,6-dioxo-3-piperidyl)-1,3-dioxo-isoindolin-4-yl]nonyl]carbamate (442 mg, 737 umol) in DCM (3 mL) was added HCl/dioxane (4 M, 5 mL). The reaction mixture was stirred at 25° C. for 1 hour. On completion, the reaction mixture was concentrated in vacuo to give the title compound (320 mg, 99% yield, HCl) as colourless oil. LC-MS (ESI$^+$) m/z 400.3 (M+H)$^+$.

3-[4-[3-(2-aminoethoxy)propyl]-1-oxo-isoindolin-2-yl]piperidine-2,6-dione (Intermediate GU)

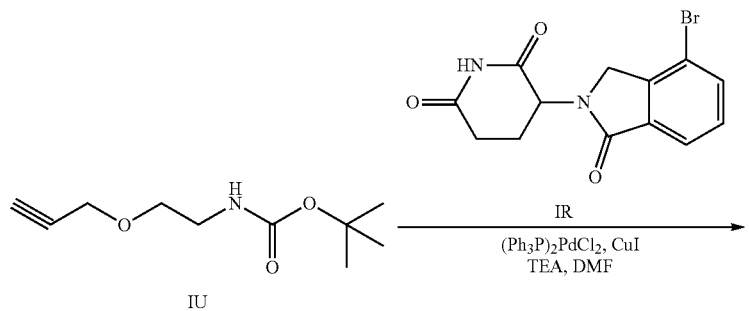

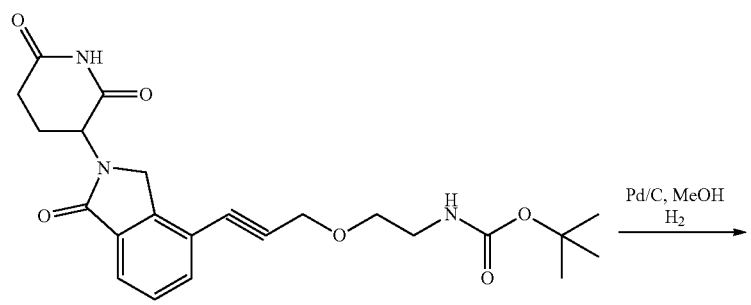

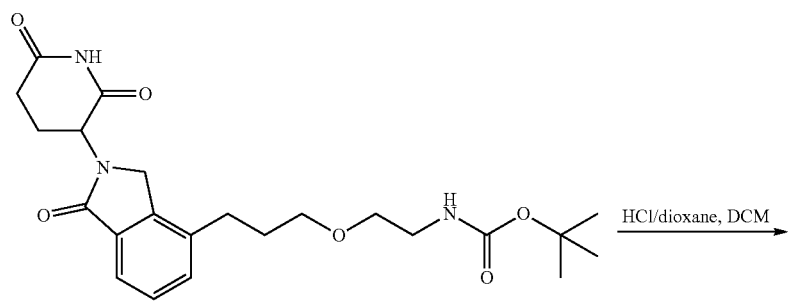

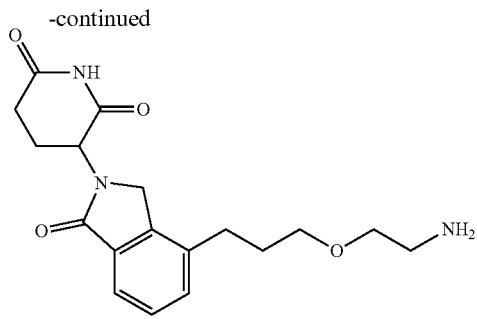

GU

Step 1-tert-butyl (2-((3-(2-(2,6-dioxopiperidin-3-yl)-1-oxoisoindolin-4-yl)prop-2-vn-1-yl)oxy)ethyl)carbamate To a stirred solution of 3-(4-bromo-1-oxoisoindolin-2-yl)piperidine-2,6-dione (0.5 g, 1.551 mmol, Intermediate IR) in DMF (6.0 ml) was added tert-butyl (2-(prop-2-yn-1-yloxy)ethyl)carbamate (0.46 g, 2.32 mmol, Intermediate IU) at rt. The reaction mixture was purged with $N_2$ gas for 20 min. To this stirred reaction mixture were added CuI (0.014 g, 0.077 mmol), TEA (6.0 ml, 36.09 mmol), $PdCl_2(PPh_3)_2$ (0.054 g, 0.0776 mmol) and the mixture was further purged with $N_2$ gas for 20 min. The reaction mixture was heated at 80° C. for 3 h. The reaction mixture was then poured into water (100 ml) and the product was extracted with ethyl acetate (3×100 ml). The combined organic layer dried over anhydrous $Na_2SO_4$, filtered and concentrated under vacuum to afford tert-butyl (2-((3-(2-(2,6-dioxopiperidin-3-yl)-1-oxoisoindolin-4-yl)prop-2-yn-1-yl)oxy)ethyl)carbamate (0.28 g, 0.64 mmol). LCMS m/z: ES+386.17 (M-55)+.

Step 2—tert-butyl (2-(3-(2-(2,6-dioxopiperidin-3-yl)-1-oxoisoindolin-4-yl)propoxy)ethyl)carbamate To a solution of tert-butyl (2-((3-(2-(2,6-dioxopiperidin-3-yl)-1-oxoisoindolin-4-yl)prop-2-yn-1-yl)oxy)ethyl)carbamate (1.5 g, 3.40 mmol) in methanol (50 ml) was added 10 wt % Pd/C (0.2 g) at rt. Hydrogen gas was purged in to the reaction mixture at rt for 4 h. The resulting reaction mixture was filtered over a bed of celite and washed with methanol (50 ml). The obtained filtrate was concentrated under vacuum. The crude material was purified by silica gel flash chromatography (eluting at 4% MeOH in MDC) to afford tert-butyl (2-(3-(2-(2,6-dioxopiperidin-3-yl)-1-oxoisoindolin-4-yl)propoxy)ethyl)carbamate (0.6 g, 1.34 mmol). LCMS m/z: ES+346.2 (M-99)+. $^1H$ NMR (400 MHz, DMSO-d6) δ 11.01 (s, 1H), 7.58 (dd, J=5.0, 3.6 Hz, 1H), 7.49-7.45 (m, 2H), 6.80 (t, J=5.7 Hz, 1H), 5.15 (dd, J=13.2, 5.1 Hz, 1H), 4.47 (d, J=17.2 Hz, 1H), 4.31 (d, J=17.1 Hz, 1H), 3.38 (dd, J=12.9, 6.4 Hz, 7H), 3.08 (q, J=6.0 Hz, 2H), 2.94 (ddd, J=17.3, 13.7, 5.4 Hz, 1H), 2.69 (dd, J=8.9, 6.5 Hz, 2H), 2.66-2.56 (m, 1H), 2.42 (td, J=13.2, 4.5 Hz, 1H), 2.02 (dtd, J=12.6, 5.3, 2.3 Hz, 1H), 1.83 (p, J=6.8 Hz, 2H), 1.37 (s, 9H).

Step 3—3-(4-(3-(2-aminoethoxy)propyl)-1-oxoisoindolin-2-yl)piperidine-2,6-dione To a solution of tert-butyl N-[2-[3-[2-(2,6-dioxo-3-piperidyl)-1-oxo-isoindolin-4-yl]propoxy]ethyl]carbamate (200 mg, 448 umol) in DCM (2.00 mL) was added HCl/dioxane (4 M, 2.00 mL). The mixture was stirred at 20° C. for 0.5 hour. On completion, the mixture was concentrated in vacuo to give the title compound (170 mg, 80% yield, HCl) as yellow solid. LC-MS (ESI+) m/z 346.3 (M+H)+.

3-[3-[2-[2-(2-aminoethoxy)ethoxy]ethyl]-2-oxobenzimidazol-1-yl]piperidine-2,6-dione (Intermediate GV)

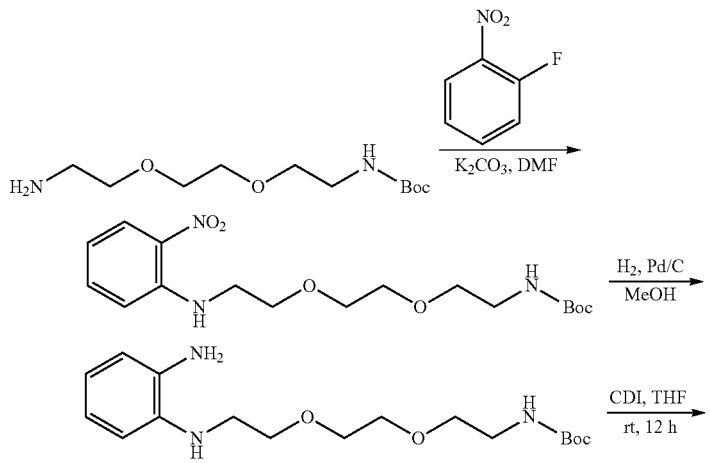

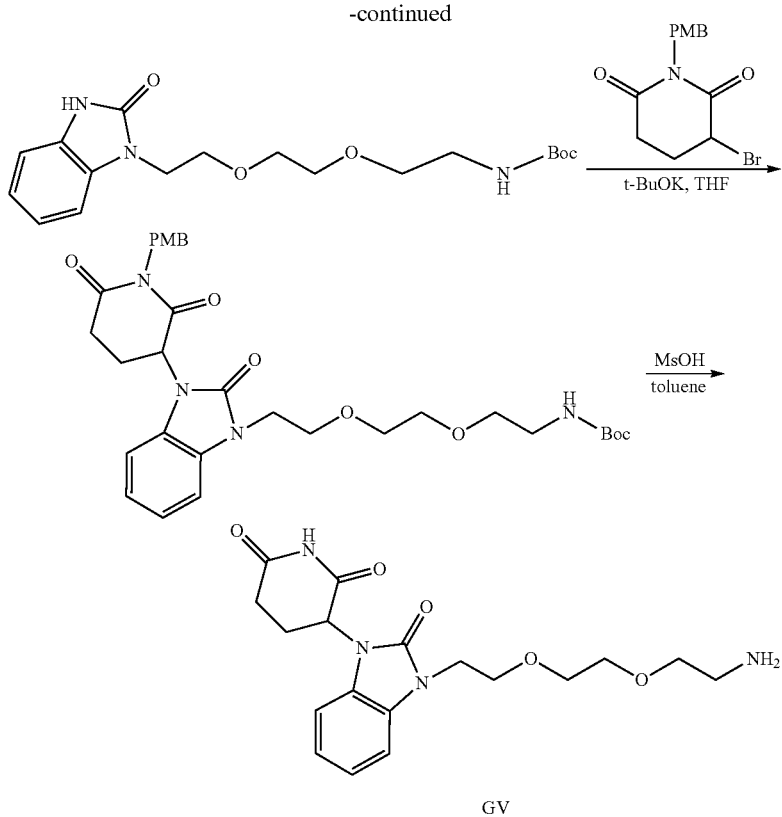

GV

Step 1: tert-butyl (2-(2-(2-((2-nitrophenyl)amino)ethoxy)ethoxy)ethyl)carbamate

To a solution of tert-butyl (2-(2-(2-aminoethoxy)ethoxy)ethyl)carbamate (15.0 g, 0.060 mol, CAS #153086-78-3) in DMF (30 mL) was added 1-fluoro-2-nitrobenzene (10.2 g, 0.072 mmol), and K$_2$CO$_3$ (25.1 g, 0.182 mmol) at r.t. The reaction was heated at 60° C. for 3 h. The mixture was quenched with water and extracted with EtOAc (100 ml×2). The combined organic layer was washed with brine, dried and concentrated in vacuo. The residue was purified via column chromatography (petroleum ether/EtOAc=5%-80%) to give the desired compound (12.8 g, 57% yield) as a yellow oil. LC-MS (ESI$^+$): m/z 370.2 (M+H)$^+$.

Step 2: tert-butyl (2-(2-(2-((2-aminophenyl)amino)ethoxy)ethoxy)ethyl)carbamate

To a solution of tert-butyl (2-(2-(2-((2-nitrophenyl)amino)ethoxy)ethoxy)ethyl)carbamate (12.8 g, 34.7 mmol) in MeOH (200 mL) was added Pd/C (720 mg) at r.t. The reaction mixture was degassed and purged with hydrogen three times. The reaction was stirred at r.t. for 12 hs under hydrogen. On completion, the mixture was filtered and the filtrate was concentrated in vacuo to give the desired compound (11.2 g, 95% yield) as a yellow oil. LC-MS (ESI$^+$): m/z 340.2 (M+H)$^+$.

Step 3: tert-butyl (2-(2-(2-(2-oxo-2,3-dihydro-1H-benzo[d]imidazol-1-yl)ethoxy)ethoxy)ethyl)carbamate To a solution of tert-butyl (2-(2-(2-((2-aminophenyl)amino)ethoxy)ethoxy)ethyl)carbamate (11.2 g, 33.04 mmol) in THF (100 mL) was added CDI (6.5 g, 40.37 mmol) at r.t. The reaction was stirred at r.t. overnight. The mixture was quenched with water and extracted with EtOAc (100 ml×2). The combined organic layer was washed with brine, dried and concentrated in vacuo. The residue was purified via column chromatography (petroleum ether/EtOAc=5%-80%) to give the desired compound (3.7 g, 31% yield) as a yellow oil. $^1$H NMR (400 MHz, DMSO-d$_6$) δ ppm: 10.84 (s, 1H), 7.20-7.13 (m, 1H), 7.03-6.94 (m, 3H), 6.75 (t, J=5.5 Hz, 1H), 3.94 (t, J=5.7 Hz, 2H), 3.66 (t, J=5.7 Hz, 2H), 3.51 (d, J=5.3 Hz, 2H), 3.44 (d, J=5.2 Hz, 2H), 3.32 (t, J=6.1 Hz, 2H), 3.02 (q, J=5.9 Hz, 2H), 1.37 (s, 9H).

Step 4: tert-butyl (2-(2-(2-(3-(1-(4-methoxybenzyl)-2,6-dioxopiperidin-3-yl)-2-oxo-2,3-dihydro-1H-benzo[d]imidazol-1-yl)ethoxy)ethoxy)ethyl)carbamate To a stirred solution of tert-butyl (2-(2-(2-(2-oxo-2,3-dihydro-1H-benzo[d]imidazol-1-yl)ethoxy)ethoxy)ethyl)carbamate (1.5 g, 4.12 mmol) in THF (300 ml) was added t-BuOK (370 mg, 3.3 mol) at room temperature portion-wise. After addition, the mixture was stirred at room temperature for 2 h. Then the 3-bromo-1-(4-methoxybenzyl)piperidine-2,6-dione (1.9 g, 6.16 mmol) in THF (20 ml) was added dropwise. The mixture was stirred at room temperature for 2 h. Then a second batch of t-BuOK (370 mg, 3.3 mmol) was added portion-wise, and the mixture was stirred for an additional 30 min. Then the mixture was poured into water, and extracted with EtOAc (3×200 ml). The combined organic layers were concentrated under reduced pressure, and the residue was purified by column on silica gel eluting with EtOAc:DCM=2:1 to get the title compound (600 mg, 24% yield) as a white solid. $^1$H NMR (400 MHz, CDCl$_3$) δ ppm: 7.36 (m, J=8.50 Hz, 2H), 7.17 (d, J=7.75 Hz, 1H), 7.08 (t, J=7.75 Hz, 1H), 6.94 (t, J=7.75 Hz, 1H), 6.83 (m, J=8.38 Hz, 2H), 6.50 (d, J=7.88 Hz, 1H), 5.23 (dd, J=13.13, 5.38 Hz, 1H), 4.96 (d, J=2.00 Hz, 2H), 4.09 (t, J=5.63 Hz, 2H), 3.74-3.86 (m, 5H), 3.57-3.62 (m, 2H), 3.51-3.56 (m, 2H), 3.41-3.49 (m, 2H), 3.21-3.29 (m, 2H), 2.95-3.07 (m, 1H), 2.77-2.89 (m, 1H), 2.54-2.68 (m, 1H), 2.13-2.22 (m, 1H), 1.46 (s, 9H). LC-MS (ESI$^+$): m/z 597.0 (M+H)$^+$.

Step 5: 3-(3-(2-(2-(2-aminoethoxy)ethoxy)ethyl)-2-oxo-2,3-dihydro-1H-benzo[d]imidazol-1-yl)piperidine-2,6-dione To a solution of tert-butyl (2-(2-(2-(3-(1-(4-methoxybenzyl)-2,6-dioxopiperidin-3-yl)-2-oxo-2,3-dihydro-1H-benzo[d]imidazol-1-yl)ethoxy)ethoxy)ethyl)carbamate (640 mg, 1.074 mmol) in toluene (5 mL) was added MsOH (2.1 g, 21 mmol). The reaction was heated at 110° C. for 3 h. The reaction mixture was cooled to room temperature, then concentrated under reduced pressure. The residue was poured into ice water, then basified with sat. NaHCO$_3$ to pH=7-8. Then the mixture was purified by prep HPLC eluting with ACN/H$_2$O (0.1% HCOOH)=0%-10% to give the desired formic acid salt compound as a colorless oil (62 mg, 15% yield). $^1$H NMR (400 MHz, DMSO-d$_6$) δ ppm: 7.33 (d, J=7.38 Hz, 1H), 7.01-7.24 (m, 3H), 5.45 (dd, J=12.57, 5.07 Hz, 1H), 4.27-4.54 (m, 2H), 4.04-4.13 (m, 2H), 3.68-3.86 (m, 2H), 3.61 (br. s., 2H) 3.34-3.58 (m, 4H), 2.89-3.03 (m, 1H), 2.63-2.84 (m, 2H), 1.98-2.18 (m, 1H) LC-MS (ESI$^+$): m/z 377.0 (M+H)$^+$.

4-[3-(2-Aminoethoxy)propyl]-2-(2,6-dioxo-3-piperidyl)isoindoline-1,3-dione (Intermediate GW)

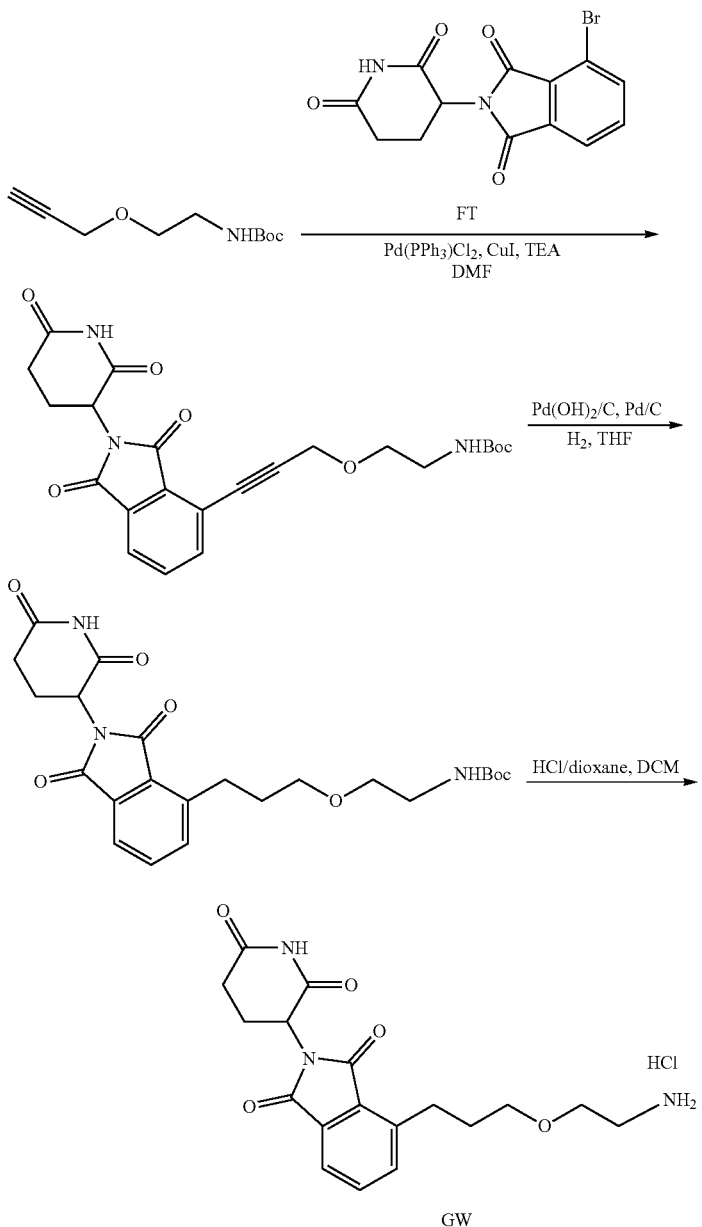

Step 1—Tert-butyl N-[2-[3-[2-(2,6-dioxo-3-piperidyl)-1,3-dioxo-isoindolin-4-yl]prop-2-ynoxy]ethyl]carbamate To a solution of 4-bromo-2-(2,6-dioxo-3-piperidyl)isoindoline-1,3-dione (1.95 g, 5.79 mmol, Intermediate FT) and tert-butyl N-(2-prop-2-ynoxyethyl)carbamate (1.50 g, 7.53 mmol, synthesized via Step 1 on Intermediate CP) in DMF (10 mL) was added Pd(PPh$_3$)$_2$Cl$_2$ (406 mg, 579 umol), TEA (10.5 g, 104 mmol) and CuI (110 mg, 579 umol). The mixture was heated at 80° C. for 30 minutes under microwave. On completion, the reaction mixture was concentrated in vacuo to give a residue. The residue was purified by silica gel chromatography (PE:EA=1:1) to give the title compound (1.80 g, 68% yield) as light yellow oil; LC-MS (ESI$^+$) m/z 478.0 (M+Na)$^+$.

Step 2—Tert-butyl N-[2-[3-[2-(2,6-dioxo-3-piperidyl)-1,3-dioxo-isoindolin-4-yl]propoxy]ethyl]carbamate To a solution of tert-butyl N-[2-[3-[2-(2,6-dioxo-3-piperidyl)-1,3-dioxo-isoindolin-4-yl]prop-2-ynoxy]ethyl]carbamate (1.00 g, 2.20 mmol) in THF (30 mL) was added Pd/C (0.2 g, 10% w/w) and Pd(OH)$_2$/C (0.2 g, 10% w/w) under N$_2$. The suspension was degassed under vacuum and purged with H$_2$ gas three times. The mixture was stirred under H$_2$ (15 Psi) at 20° C. for 1 hour. On completion, the reaction mixture was filtered and the filtrate was concentrated in vacuo to give title compound (600 mg, 60% yield) as white solid; LC-MS (ESI$^+$) m/z 482.2 (M+Na)$^+$.

Step 3—4-[3-(2-Aminoethoxy)propyl]-2-(2,6-dioxo-3-piperidyl)isoindoline-1,3-dione (7)—Notebook Page: EW5417-748

To a solution of tert-butyl N-[2-[3-[2-(2,6-dioxo-3-piperidyl)-1,3-dioxo-isoindolin-4-yl]propoxy]ethyl]carbamate (200 mg, 435 umol) in DCM (2 mL) was added HCl/dioxane (4 M, 0.8 mL). The mixture was stirred at 20° C. for 2 hours. On completion, the reaction mixture was concentrated in vacuo to give the title compound (156 mg, 90% yield, HCl salt) as white solid; LC-MS (ESI$^+$) m/z 360.1 (M+H)$^+$.

4-[3-[2-(2-aminoethoxy)ethoxy]propyl]-2-(2,6-dioxo-3-piperidyl)isoindoline-1,3-dione (Intermediate GX)

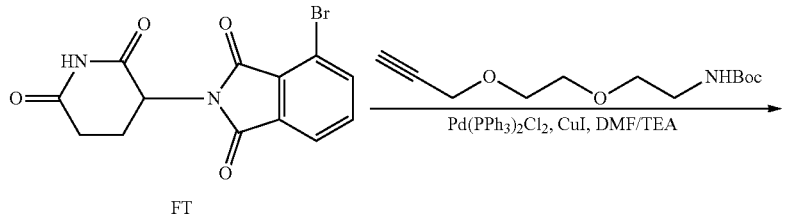

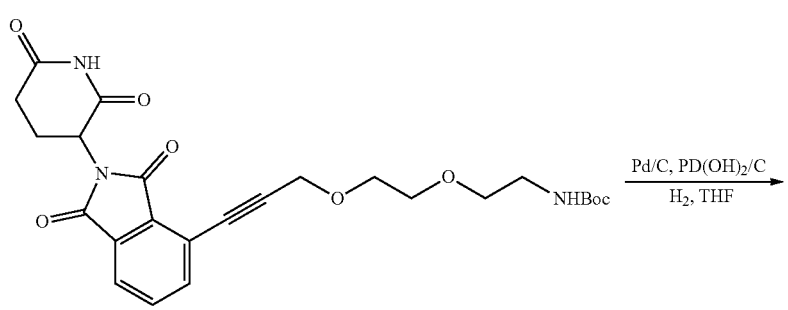

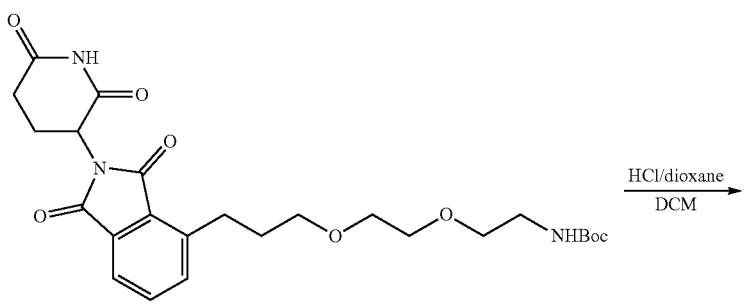

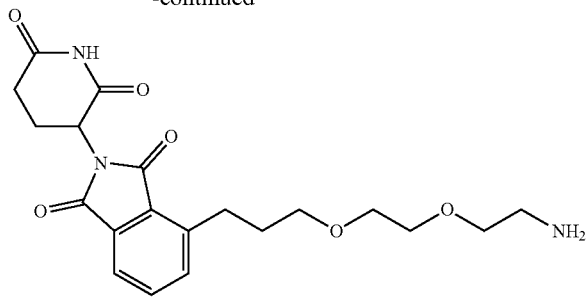

GX

Step 1—Tert-butyl N-[2-[2-[3-[2-(2,6-dioxo-3-piperidyl)-1,3-dioxo-isoindolin-4-yl]prop-2-ynoxy]ethoxy]ethyl]carbamate To a solution of 4-bromo-2-(2,6-dioxo-3-piperidyl)isoindoline-1,3-dione (1 g, 2.97 mmol, Intermediate FT) and tert-butyl N-[2-(2-prop-2-ynoxyethoxy)ethyl]carbamate (1.44 g, 5.93 mmol, synthesized via Step 1 of Intermediate CQ) in DMF (8 mL) was added Pd(PPh$_3$)$_2$Cl$_2$ (208 mg, 296 umol), TEA (5.4 g, 53.3 mmol, 7.43 mL) and CuI (56.4 mg, 296 umol). The reaction mixture was heated at 80° C. for 30 min under microwave. On completion, the mixture was concentrated in vacuo to give a residue. The residue was purified by column chromatography (SiO2, Petroleum ether/Ethyl acetate=5/1 to I/O, Rf=0.73) to give the title compound (1.20 g, 72% yield) as yellow solid. LC-MS (ESI$^+$) m/z 500.1 (M+H)$^+$.

Step 2—Tert-butyl N-[2-[2-[3-[2-(2,6-dioxo-3-piperidyl)-1,3-dioxo-isoindolin-4-yl]propoxy]ethoxy]ethyl]carbamate To a solution of tert-butyl N-[2-[2-[3-[2-(2,6-dioxo-3-piperidyl)-1,3-dioxo-isoindolin-4-yl]prop-2-ynoxy]ethoxy]ethyl]carbamate (600 mg, 1.20 mmol) in THF (10 mL) was added Pd/C (300 mg, 1.20 mmol, 10 wt %) and Pd(OH)$_2$/C (300 mg, 1.20 mmol, 10 wt %). The reaction mixture was stirred at 25° C. under H$_2$ (15 psi) for 12 hours. On completion, the residue was filtered and the filtrate was concentrated in vacuo to give the title compound (600 mg, 99% yield) as yellow oil. LC-MS (ESI$^+$) m/z 526.4 (M+Na)$^+$.

Step 3—4-[3-[2-(2-aminoethoxy)ethoxy]propyl]-2-(2,6-dioxo-3-piperidyl)isoindoline-1,3-dione To a solution of tert-butyl N-[2-[2-[3-[2-(2,6-dioxo-3-piperidyl)-1,3-dioxo-isoindolin-4-yl]propoxy]ethoxy]ethyl]carbamate (600 mg, 1.19 mmol) in DCM (2 mL) was added HCl/dioxane (4 M, 2.00 mL), and the reaction mixture was stirred at 25° C. for 20 minutes. On completion, the mixture was concentrated in vacuo to give the title compound (500 mg, 95% yield) as yellow solid. LC-MS (ESI$^+$) m/z 404.3 (M+H)$^+$.

tert-butyl N-[4-[4-[[3-carbamoyl-1-(4-formylphenyl)pyrazol-4-yl]carbamoyl]oxazol-2-yl]-2-pyridyl]-N-(2,2,2-trifluoroethyl)carbamate (Intermediate GY)

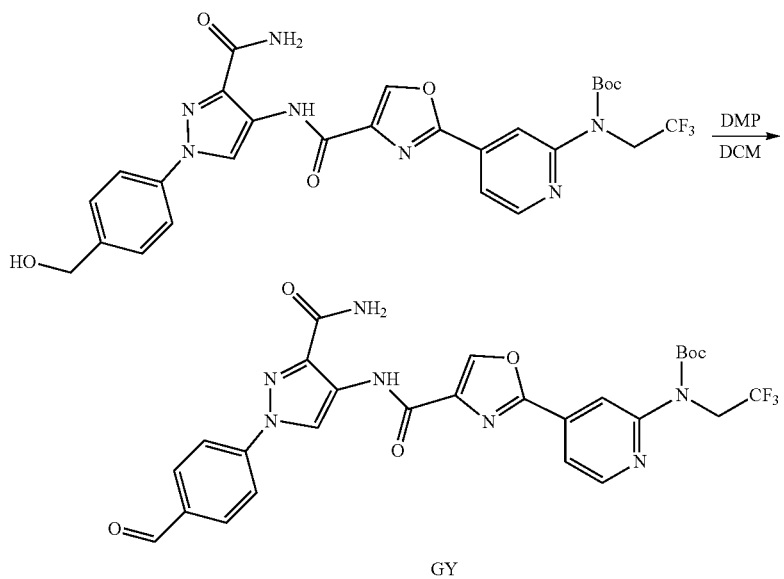

GY

Tert-butyl N-[4-[4-[[3-carbamoyl-1-(4-formylphenyl) pyrazol-4-yl]carbamoyl]oxazol-2-yl]-2-pyridyl]-N-(2,2,2-trifluoroethyl)carbamate was synthesized as described below in Step 1 of Example 171.

Tert-butyl N-[2-[2-[2-(2-prop-2-ynoxyethoxy) ethoxy]ethoxy]ethyl]carbamate (Intermediate GZ)

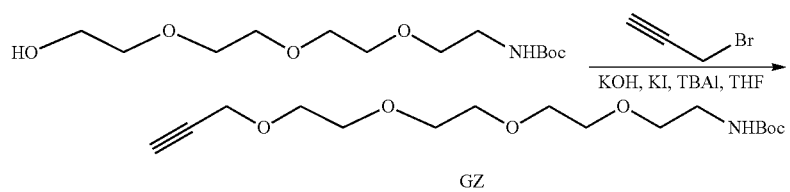

To a solution of tert-butyl N-[2-[2-[2-(2-hydroxyethoxy) ethoxy]ethoxy]ethyl]carbamate (2.00 g, 6.82 mmol, synthesized via Steps 1-3 of Intermediate AO) and 3-bromoprop-1-yne (973 mg, 8.18 mmol, 705 uL) in THF (30 mL) was added TBAI (151 mg, 409 umol), KI (169 mg, 1.02 mmol), KOH (382 mg, 6.82 mmol). The reaction mixture was stirred at 25° C. for 16 hours. On completion, the mixture was filtered, and the filtrate was concentrated in vacuo to give a residue. The residue was purified by flash silica gel chromatography to give the title compound (0.85 g, 37% yield) as yellow oil. $^1$H NMR (400 MHz, CDCl$_3$) δ 5.06 (s, 1H), 4.21 (d, J=2.4 Hz, 2H), 3.72-3.61 (m, 14H), 3.54 (t, J=5.2 Hz, 2H), 2.46-2.43 (m, 1H), 1.45 (s, 9H).

4-[3-[2-[2-[2-(2-Aminoethoxy)ethoxy]ethoxy]propyl]-2-(2,6-dioxo-3-piperidyl) isoindoline-1,3-dione (Intermediate HA)

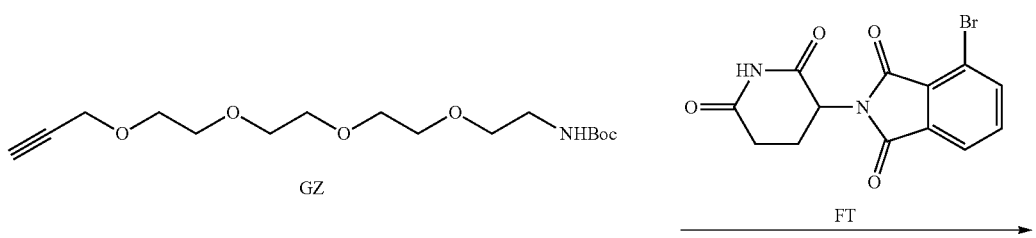

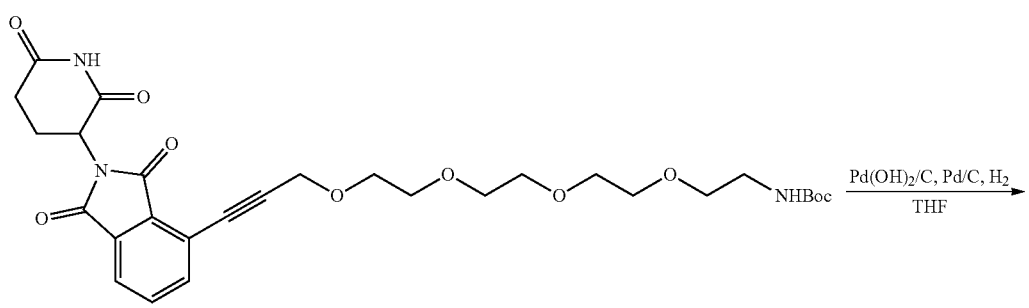

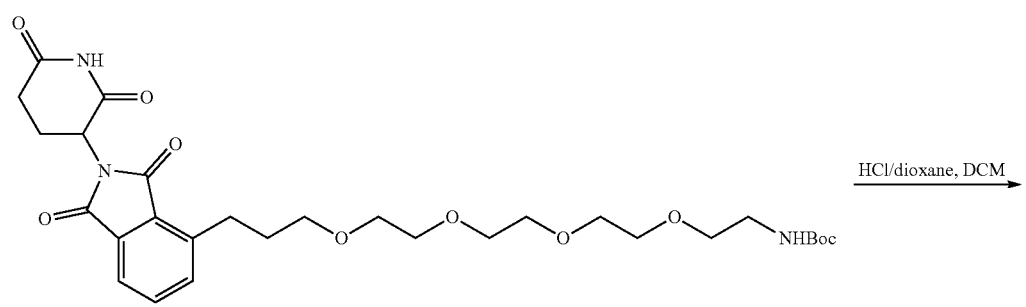

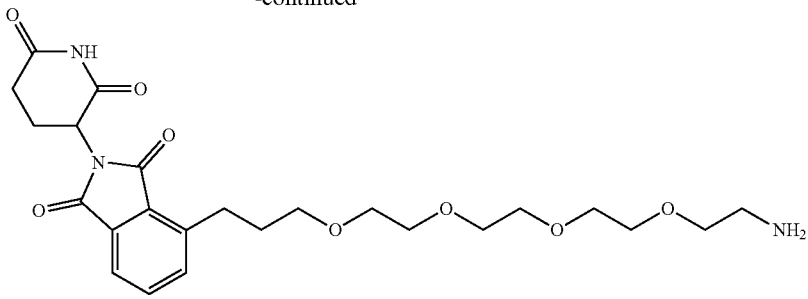

HA

Step 1—Tert-butyl N-[2-[2-[2-[2-[3-[2-(2,6-dioxo-3-piperidyl)-1,3-dioxo-isoindolin-4-yl]prop-2-ynoxy]ethoxy]ethoxy]ethoxy]ethyl]carbamate To a mixture of tert-butyl N-[2-[2-[2-(2-prop-2-ynoxy-ethoxy)ethoxy]ethoxy]ethyl]carbamate (690 mg, 2.08 mmol, Intermediate GZ) and 4-bromo-2-(2,6-dioxo-3-piperidyl)isoindoline-1,3-dione (540 mg, 1.60 mmol, Intermediate FT) in DMF (6 mL) was added Pd(PPh$_3$)$_2$Cl$_2$ (112 mg, 160 umol), CuI (30.5 mg, 160 umol) and TEA (2.92 g, 28.8 mmol, 4.01 mL). The reaction mixture was heated at 80° C. for 30 minutes under microwave. On completion, the reaction mixture was concentrated in vacuo. The residue was purified by prep-HPLC (0.1% FA condition) to give the title compound (580 mg, 61% yield) as light yellow oil. LC-MS (ESI$^+$) m/z 610.4 (M+Na)$^+$.

Step 2—Tert-butyl N-[2-[2-[2-[2-[3-[2-(2,6-dioxo-3-piperidyl)-1,3-dioxo-isoindolin-4-yl]propoxy]ethoxy]ethoxy]ethoxy]ethyl]carbamate To a mixture of tert-butyl N-[2-[2-[2-[2-[3-[2-(2,6-dioxo-3-piperidyl)-1,3-dioxo-isoindolin-4-yl]prop-2-ynoxy]ethoxy]ethoxy]ethoxy]ethyl]carbamate (380 mg, 646 umol) in THF (10 mL) was added Pd(OH)$_2$/C (150 mg, 10 wt %) and Pd/C (150 mg, 10 wt %). The reaction mixture was stirred at 25° C. for 0.5 hour under H$_2$ (15 Psi) atmosphere. On completion, the reaction mixture was filtered and concentrated in vacuo to give the title compound (382 mg, 99% yield) as light yellow oil. LC-MS (ESI$^+$) m/z 592.3 (M+H)$^+$.

Step 3—4-[3-[2-[2-[2-(2-Aminoethoxy)ethoxy]ethoxy]ethoxy]propyl]-2-(2,6-dioxo-3-piperidyl)isoindoline-1,3-dione To a mixture of tert-butyl N-[2-[2-[2-[2-[3-[2-(2,6-dioxo-3-piperidyl)-1,3-dioxo-isoindolin-4-yl]propoxy]ethoxy]ethoxy]ethoxy]ethyl]carbamate (382 mg, 645 umol) in DCM (3 mL) was added HCl/dioxane (4 M, 5 mL). The reaction mixture was stirred at 25° C. for 1 hour. On completion, the reaction mixture was concentrated in vacuo to give the title compound (340 mg, 99% yield, HCl) as light yellow oil. LC-MS (ESI$^+$) m/z 492.3 (M+H)$^+$

3-[4-[3-[2-(2-aminoethoxy)ethoxy]propyl]-1-oxo-isoindolin-2-yl]piperidine-2,6-dione (Intermediate HB)

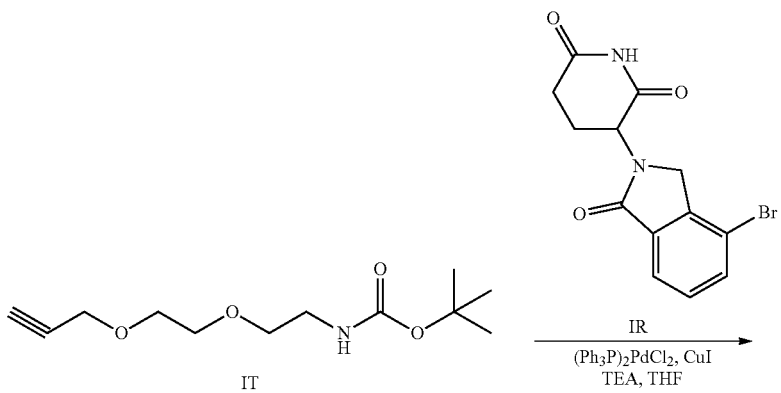

-continued

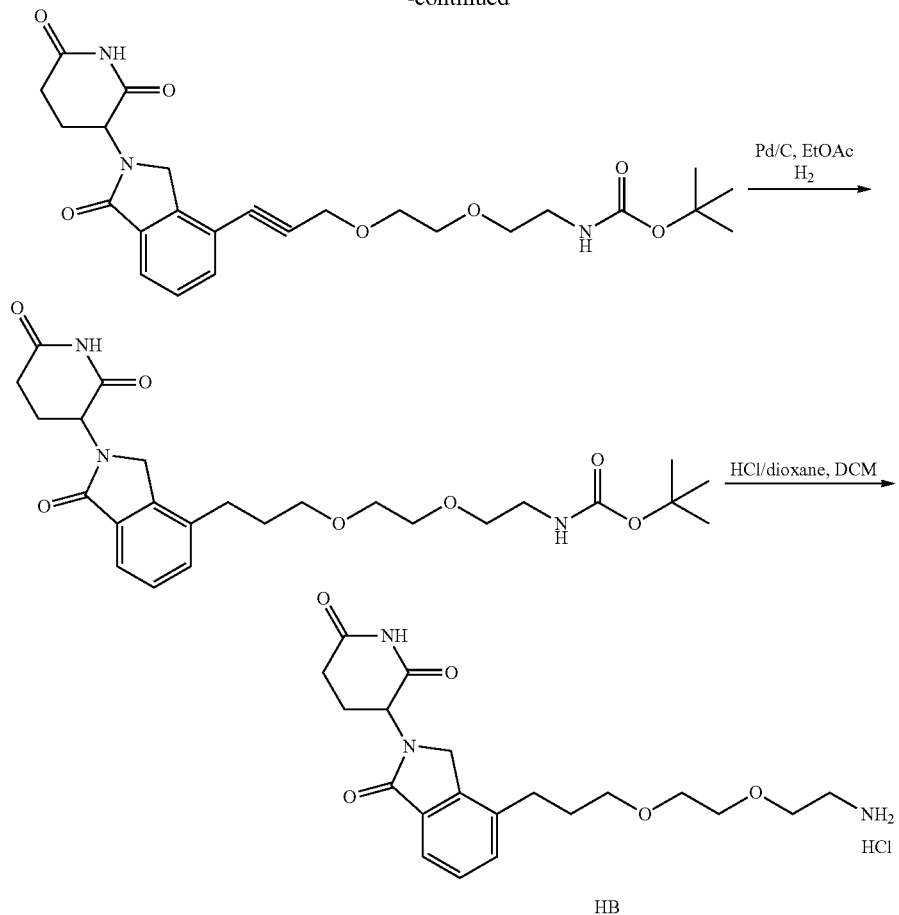

Step 1—(2-(2-((3-(2-(2,6-dioxopiperidin-3-yl)-1-oxoisoindolin-4-yl)prop-2-yn-1-yl)oxy)ethoxy)ethyl) carbamate To a stirred solution of 3-(4-bromo-1-oxoisoindolin-2-yl)piperidine-2,6-dione (0.3 g, 0.93 mmol, Intermediate IR) in DMF (6.0 ml) was added tert-butyl (2-(2-(prop-2-yn-1-yloxy)ethoxy)ethyl)carbamate (0.34 g, 1.39 mmol, Intermediate IT) at rt. The reaction mixture was purged with $N_2$ gas for 20 min. To this stirred reaction mixture were added CuI (0.008 g, 0.0465 mmol), TEA (3.2 ml, 22.35 mmol), $PdCl_2(PPh_3)_2$ (0.032 g, 0.0465 mmol) and the reaction was further purged with $N_2$ gas for 20 min. Then the reaction mixture was heated at 80° C. for 3 h. On completion, the reaction mixture was poured into water (100 ml) and product was extracted with ethyl acetate (3×100 ml). The combined organic layer was dried over anhydrous $Na_2SO_4$, filtered and concentrated under vacuum. The crude material was purified by silica gel flash chromatography (eluting at 3% MeOH in MDC) to afford tert-butyl (2-(2-((3-(2-(2,6-dioxopiperidin-3-yl)-1-oxoisoindolin-4-yl)prop-2-yn-1-yl)oxy)ethoxy)ethyl)carbamate (0.2 g, 0.412 mmol). LCMS m/z: (ES+) 508.2 (M+23)$^+$.

Step 2—tert-butyl (2-(2-(3-(2-(2,6-dioxopiperidin-3-yl)-1-oxoisoindolin-4-yl)propoxy)ethoxy)ethyl) carbamate To a solution of tert-butyl (2-(2-((3-(2-(2,6-dioxopiperidin-3-yl)-1-oxoisoindolin-4-yl)prop-2-yn-1-yl)oxy)ethoxy)ethyl)carbamate (1.4 g, 2.88 mmol) in methanol (50 ml) was added 10 wt % Pd/C (0.2 g) at rt. Hydrogen gas was purged in to the reaction mixture at rt for 4 h. The resulting reaction mixture was filtered over a bed of celite and washed with methanol (50 ml). The obtained filtrate was concentrated under vacuum. The obtained crude material was purified by silica gel chromatography (eluting at 4% MeOH in MDC) to afford tert-butyl (2-(2-(3-(2-(2,6-dioxopiperidin-3-yl)-1-oxoisoindolin-4-yl)propoxy)ethoxy)ethyl) carbamate (0.8 g, 1.63 mmol). LCMS m/z: ES+390.3 (M-99)$^+$. $^1$H NMR (400 MHz, DMSO-d6) δ 11.02 (s, 1H), 7.58 (dd, J=5.3, 3.3 Hz, 1H), 7.51-7.42 (m, 2H), 5.15 (dd, J=13.3, 5.0 Hz, 1H), 4.47 (d, J=17.2 Hz, 1H), 4.30 (d, J=17.1 Hz, 1H), 3.49 (td, J=5.2, 2.9 Hz, 3H), 3.38 (dd, J=7.0, 4.4 Hz, 6H), 3.06 (q, J=6.1 Hz, 2H), 3.00-2.86 (m, 1H), 2.70 (d, J=7.8 Hz, 2H), 2.61 (d, J=17.6 Hz, 2H), 2.42 (d, J=4.5 Hz, 1H), 2.01 (dd, J=9.4, 3.7 Hz, 1H), 1.84 (t, J=7.5 Hz, 2H), 1.36 (d, J=4.6 Hz, 9H).

Step 3—3-(4-(3-(2-(2-aminoethoxy)ethoxy)propyl)-1-oxoisoindolin-2-yl)piperidine-2,6-dione To a solution of tert-butyl N-[2-[2-[3-[2-(2,6-dioxo-3-piperidyl)-1-oxo-isoindolin-4-yl]propoxy]ethoxy]ethyl]carbamate (200 mg, 408 umol) in DCM (3 mL) was added HCl/dioxane (4 M, 4 mL). The mixture was stirred at 20° C. for 2 hours. On completion, the reaction mixture was concentrated in vacuo to give the title compound (155 mg, 89% yield) as yellow solid. LC-MS (ESI$^+$) m/z 390.1 (M+H)$^+$.

3-[4-[3-[2-[2-(2-Aminoethoxy)ethoxy]ethoxy]propyl]-1-oxo-isoindolin-2-yl]piperidine-2,6-dione (Intermediate HC)

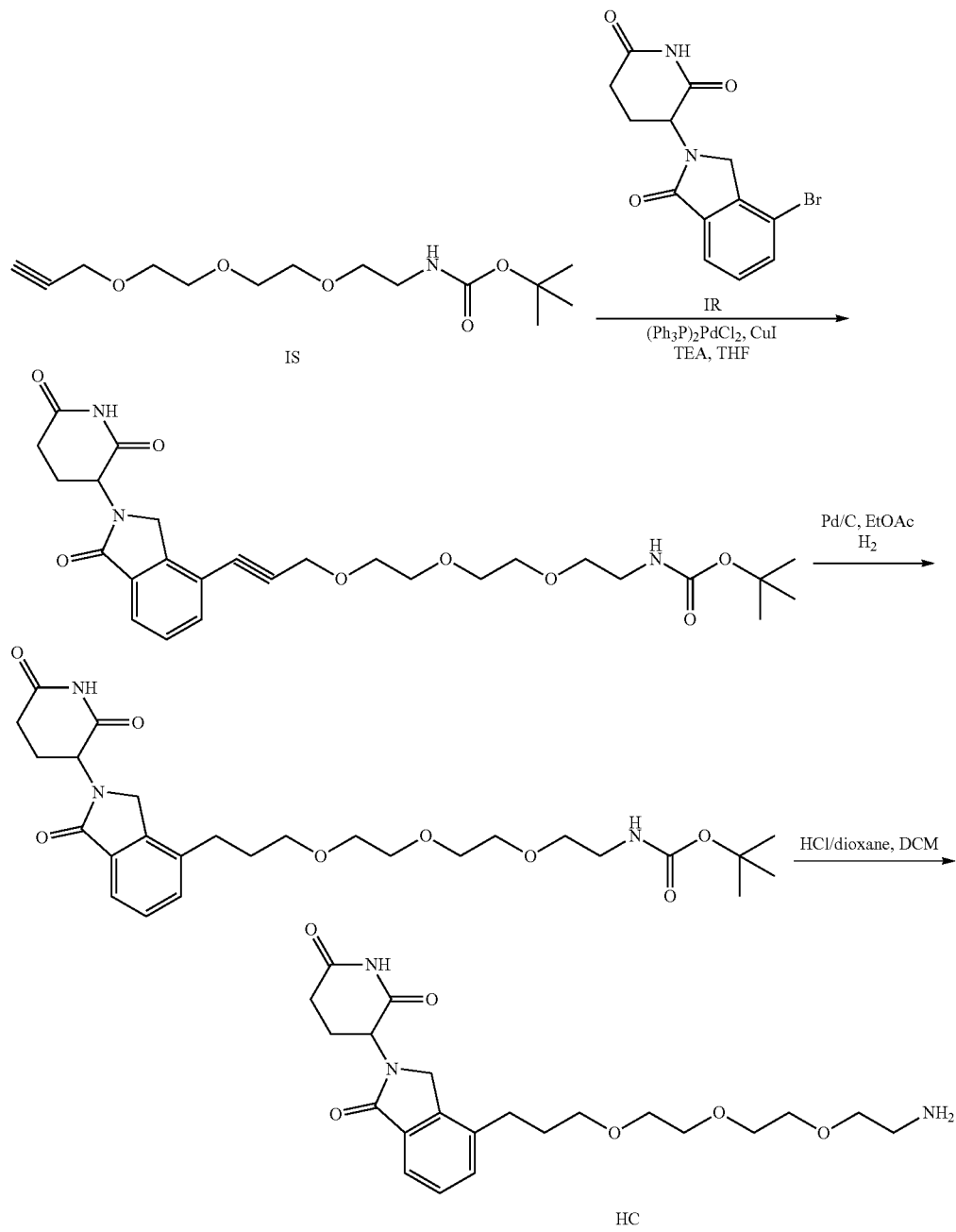

Step 1—tert-butyl (2-(2-(2-((3-(2-(2,6-dioxopiperidin-3-yl)-1-oxoisoindolin-4-yl)prop-2-yn-1-yl)oxy)ethoxy)ethoxy)ethyl)carbamate To a stirred solution of 3-(4-bromo-1-oxoisoindolin-2-yl) piperidine-2,6-dione (0.5 g, 1.55 mmol, Intermediate IR) in DMF (6.0 ml) was added tert-butyl (2-(2-(2-(prop-2-yn-1-yloxy)ethoxy)ethoxy)ethyl)carbamate (0.6 g, 2.32 mmol, Intermediate IS) at rt. The reaction mixture was purged with $N_2$ gas for 20 min. To the stirred reaction mixture were added CuI (0.014 g, 0.0776 mmol), TEA (5.5 ml, 37.26 mmol), PdCl$_2$(PPh$_3$)$_2$ (0.054 g, 0.0776 mmol) and further purged with $N_2$ gas for 20 min. The reaction mixture was heated at 80° C. for 3 h. On completion, the reaction mixture was poured into water (200 ml) and product was extracted with ethyl acetate (3×200 ml). The combined organic layer was dried over anhydrous Na$_2$SO$_4$, filtered and concentrated under vacuum. The crude material was purified by silica gel flash chromatography (eluting at 4% MeOH in MDC) to afford tert-butyl (2-(2-(2-((3-(2-(2,6-dioxopiperidin-3-yl)-1-oxoisoindolin-4-yl)prop-2-yn-1-yl)oxy)ethoxy)ethoxy) ethyl)carbamate (0.5 g, 1.0 mmol). LCMs m/z: (ES+) 528.4 (M-1)$^+$.

Step 2—tert-butyl (2-(2-(3-(2-(2,6-dioxopiperidin-3-yl)-1-oxoisoindolin-4-yl)propoxy)ethoxy)ethyl) carbamate To a solution of tert-butyl (2-(2-(2-((3-(2-(2,6-dioxopiperidin-3-yl)-1-oxoisoindolin-4-yl)prop-2-yn-1-yl)oxy)ethoxy)ethoxy)ethyl)carbamate (1.5 g, 2.83 mmol) in methanol (50 ml) was added 10 wt % Pd/C (0.15 g) at rt. Hydrogen gas was purged into the reaction mixture at rt for 4 h. The resulting reaction mixture was filtered over a bed of celite and washed with methanol (50 ml). The obtained filtrate was concentrated under vacuum. The crude material was purified by combi flash chromatography (eluting at 4% MeOH in MDC) to afford tert-butyl (2-(2-(3-(2-(2,6-dioxopiperidin-3-yl)-1-oxoisoindolin-4-yl)propoxy)ethoxy)ethyl) carbamate (0.3 g, 0.56 mmol). LCMS m/z: (ES+) 390.3 (M-99)$^+$. $^1$H NMR (400 MHz, DMSO-d6) δ 11.03 (s, 1H), 7.58 (dd, J=5.6, 3.0 Hz, 1H), 7.49-7.44 (m, 2H), 6.78 (t, J=5.8 Hz, 1H), 5.15 (dd, J=13.3, 5.1 Hz, 1H), 4.47 (d, J=17.1 Hz, 1H), 4.30 (d, J=17.2 Hz, 1H), 3.50 (tq, J=8.2, 2.8 Hz, 8H), 3.05 (q, J=6.0 Hz, 3H), 2.94 (ddd, J=17.2, 13.6, 5.4 Hz, 1H), 2.74-2.63 (m, 3H), 2.59 (s, 3H), 2.41 (td, J=13.2, 4.5 Hz, 1H), 2.05-1.92 (m, 1H), 1.91-1.77 (m, 2H), 1.37 (d, J=4.5 Hz, 9H).

Step 3—3-[4-[3-[2-[2-(2-Aminoethoxy)ethoxy]ethoxy]propyl]-1-oxo-isoindolin-2-yl]piperidine-2,6-dione To a solution of tert-butyl N-[2-[2-[2-[3-[2-(2,6-dioxo-3-piperidyl)-1-oxo-isoindolin-4-yl]propoxy]ethoxy]ethoxy]ethyl]carbamate (200 mg, 374 umol) in DCM (2.00 mL) was added HCl/dioxane (4 M, 4.00 mL). The mixture was stirred at 15° C. for 0.5 hr. On completion, the mixture was concentrated in vacuo to give the title compound (170 mg, 80% yield) as yellow solid. LC-MS (ESI$^+$) m/z 434.3 (M+H)$^+$.

1-[2-[2-[2-(2-Aminoethoxy)ethoxy]ethoxy]ethyl]-4-nitro-pyrazole-3-carboxamide (Intermediate HD)

Step 1—Tert-butyl N-[2-[2-[2-[2-(3-carbamoyl-4-nitro-pyrazol-1-yl)ethoxy]ethoxy]ethoxy]ethyl]carbamate To a solution of 2-[2-[2-[2-(tert-butoxycarbonylamino)ethoxy]ethoxy]ethoxy]ethyl methanesulfonate (6.50 g, 17.5 mmol, Intermediate AO), 4-nitro-1H-pyrazole-3-carboxamide (2.48 g, 15.9 mmol, Intermediate CJ) in DMF (80.0 mL) was added Cs$_2$CO$_3$ (10.3 g, 31.8 mmol). The mixture was stirred at 130° C. for 16 hours. On completion, the mixture was filtered and the organic layer was concentrated in vacuo. The mixture was purified by reverse phase (0.1% FA) to give the title compound (2.00 g, 29% yield) as yellow solid. LC-MS (ESI$^+$) m/z 454.3 (M+Na)$^+$.

Step 2—1-[2-[2-[2-(2-Aminoethoxy)ethoxy]ethoxy]ethyl]-4-nitro-pyrazole-3-carboxamide To a solution of tert-butyl N-[2-[2-[2-[2-(3-carbamoyl-4-nitro-pyrazol-1-yl)ethoxy]ethoxy]ethoxy]ethyl]carbamate (1.00 g, 2.32 mmol) in DCM (3.00 mL) was added HCl/dioxane (4 M, 5.00 mL). The mixture was stirred at 15° C. for 0.5 hour. On completion, the mixture was concentrated in vacuo to give the title compound (500 mg, 80% yield, HCl) as yellow oil. $^1$H NMR (400 MHz, MeOD-d$_4$) δ 8.64 (s, 1H), 4.41-4.38 (m, 2H), 3.90-3.87 (m, 2H), 3.68-3.65 (m, 4H), 3.62-3.60 (m, 6H), 3.13-3.09 (m, 2H).

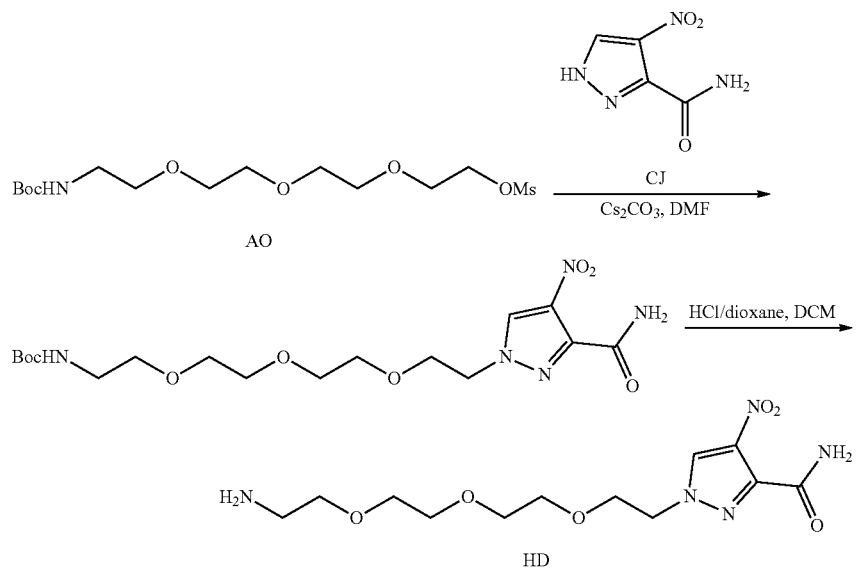

1401

4-Amino-1-[2-[2-[2-[2-[[2-(2,6-dioxo-3-piperidyl)-1,3-dioxo-isoindolin-4-yl]amino]ethoxy]ethoxy]ethoxy]ethyl]pyrazole-3-carboxamide (Intermediate HE)

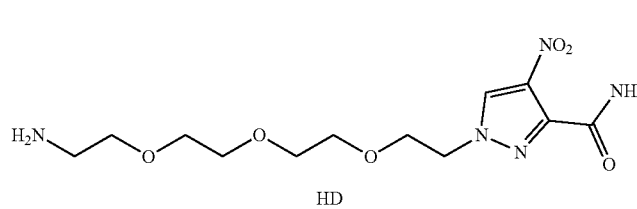

HD

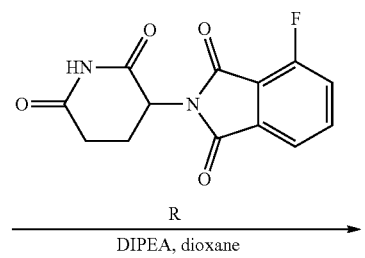

R

DIPEA, dioxane

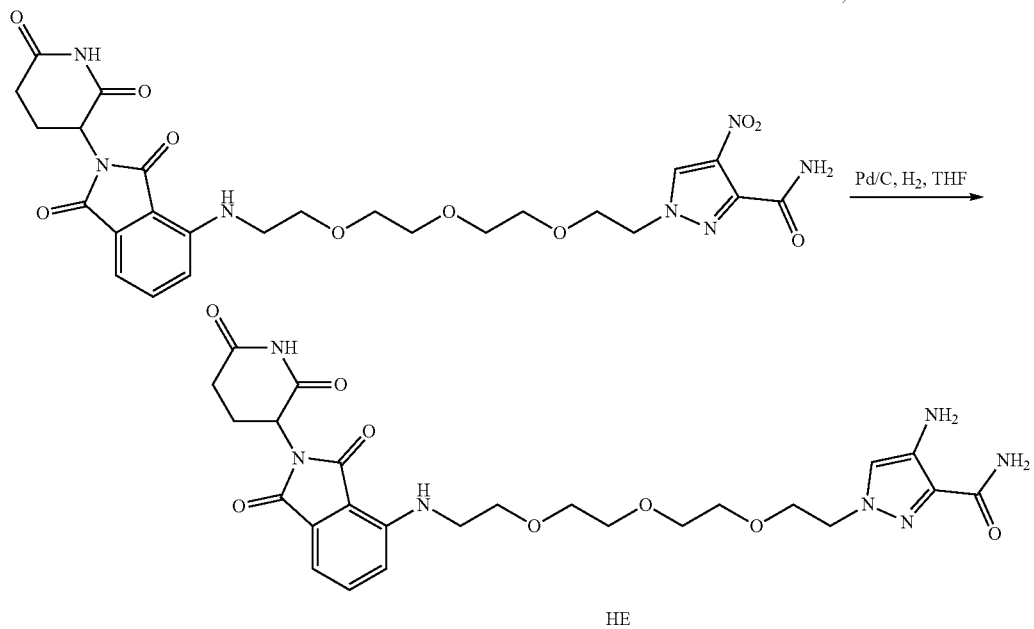

HE

Step 1—1-[2-[2-[2-[2-[[2-(2,6-Dioxo-3-piperidyl)-1,3-dioxo-isoindolin-4-yl]amino]ethoxy]ethoxy]ethoxy]ethyl]-4-nitro-pyrazole-3-carboxamide To a solution of 1-[2-[2-[2-(2-aminoethoxy)ethoxy]ethoxy]ethyl]-4-nitro-pyrazole-3-carboxamide (300 mg, 815 umol, HCl, Intermediate HD), 2-(2,6-dioxo-3-piperidyl)-4-fluoro-isoindoline-1,3-dione (247 mg, 897 umol, Intermediate R) in dioxane (5.00 mL) was added DIPEA (1.05 g, 8.16 mmol), and the mixture was stirred at 115° C. for 16 hours. On completion, the mixture was concentrated in vacuo. The mixture was purified by silica gel column (DCM:MeOH=30:1) to give the title compound (100 mg, 20% yield) as yellow oil. LC-MS (ESI$^+$) m/z 588.3 (M+H)$^+$.

Step 2—4-Amino-1-[2-[2-[2-[2-[[2-(2,6-dioxo-3-piperidyl)-1,3-dioxo-isoindolin-4-yl]amino]ethoxy]ethoxy]ethoxy]ethyl]pyrazole-3-carboxamide To a solution of 1-[2-[2-[2-[2-[[2-(2,6-dioxo-3-piperidyl)-1,3-dioxo-isoindolin-4-yl]amino]ethoxy]ethoxy]ethoxy]ethyl]-4-nitropyrazole-3-carboxamide (70.0 mg, 119 umol) in THF (5.00 mL) was added Pd/C (25.0 mg), and the mixture was stirred at 15° C. for 15 min under H$_2$ (15 psi). On completion, the mixture was filtered. The filtrate was concentrated in vacuo to give the title compound (60.0 mg, 90% yield) as yellow solid. LC-MS (ESI$^+$) m/z 558.2 (M+H)$^+$.

1402

4-Amino-1-(2-hydroxyethyl)pyrazole-3-carboxamide (Intermediate HF)

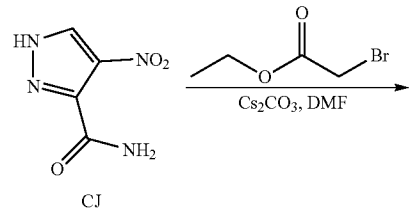

CJ

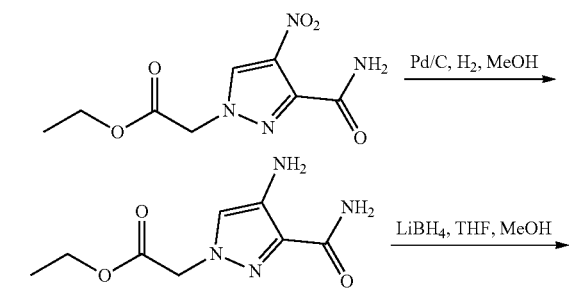

1403

-continued

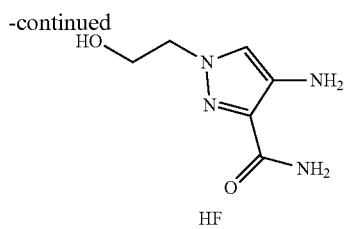

HF

Step 1—Ethyl 2-(3-carbamoyl-4-nitro-pyrazol-1-yl)acetate

To a solution of 4-nitro-1H-pyrazole-3-carboxamide (1.5 g, 9.61 mmol, Intermediate CJ) and ethyl 2-bromoacetate (1.68 g, 10.0 mmol) in DMF (20 mL) was added $Cs_2CO_3$ (3.13 g, 9.61 mmol), the mixture was stirred at 20° C. for 16 hours. On completion, the mixture was filtered to give the filtrate and concentrated in vacuo to give a residue. The residue was purified by silica gel chromatography to give the title compound (1.60 g, 68% yield) as white solid. $^1$H NMR (400 MHz, DMSO-$d_6$) δ 8.87 (s, 1H), 8.05 (s, 1H), 7.78 (s, 1H), 5.19 (s, 2H), 4.20 (q, J=7.2 Hz, 2H), 1.23 (t, J=7.2 Hz, 3H).

Step 2—Ethyl 2-(4-amino-3-carbamoyl-pyrazol-1-yl)acetate

To a solution of ethyl 2-(3-carbamoyl-4-nitro-pyrazol-1-yl)acetate (1 g, 4.13 mmol) in MeOH (40 mL) was added Pd/C (0.3 g, 10% w/w) under $N_2$. The suspension was degassed under vacuum and purged with $H_2$ three times. The mixture was stirred under $H_2$ (15 Psi) at 20° C. for 12 hours. On completion, the reaction mixture was filtered and concentrated in vacuo to give the title compound (780 mg, 89% yield) as white solid. $^1$H NMR (400 MHz, DMSO-$d_6$) δ 7.13 (s, 2H), 7.00 (s, 1H), 4.93 (s, 2H), 4.68 (s, 2H), 4.14 (q, J=7.2 Hz, 2H), 1.20 (t, J=7.2 Hz, 3H).

Step 3—4-Amino-1-(2-hydroxyethyl)pyrazole-3-carboxamide

To a solution of ethyl 2-(4-amino-3-carbamoyl-pyrazol-1-yl)acetate (770 mg, 3.59 mmol) in a mixed solvent of THF (120 mL) and MeOH (15 mL) was added $LiBH_4$ (156 mg, 7.18 mmol) at 0° C., and the mixture was stirred at 0° C. for 1 hour. On completion, the reaction mixture was quenched with water (0.5 mL), and then concentrated in vacuo to give a residue. The residue was diluted with water 20 mL, and then extracted with DCM (100 mL×3). The combined organic layers were dried over $Na_2SO_4$, filtered and concentrated in vacuo to give the title compound (600 mg, 98% yield) as white solid. $^1$H NMR (400 MHz, DMSO-d6) δ 7.10 (s, 2H), 6.93 (s, 1H), 4.97 (t, J=5.6 Hz, 1H), 4.61 (s, 2H), 4.01 (t, J=5.6 Hz, 2H), 3.69 (q, J=5.6 Hz, 2H).

1404

Tert-butyl N-[4-[4-[[3-carbamoyl-1-(2-oxoethyl)pyrazol-4-yl]carbamoyl]oxazol-2-yl]-2-pyridyl]-N-(cyclopropylmethyl)carbamate (Intermediate HG)

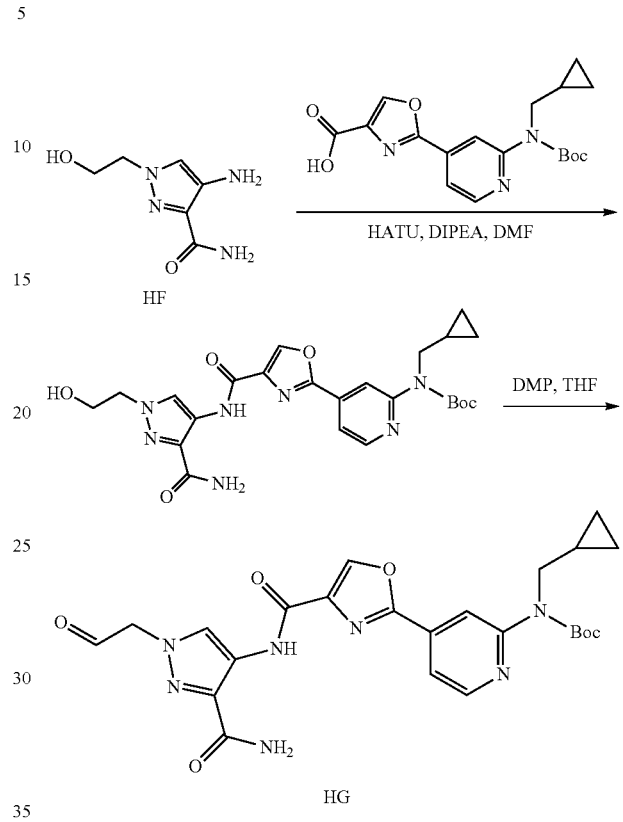

Step 1—Tert-butyl N-[4-[4-[[3-carbamoyl-1-(2-hydroxyethyl)pyrazol-4-yl]carbamoyl]oxazol-2-yl]-2-pyridyl]-N-(cyclopropylmethyl)carbamate To a solution of 4-amino-1-(2-hydroxyethyl)pyrazole-3-carboxamide (500 mg, 2.94 mmol, Intermediate HF) in DMF (15 mL) was added 2-[2-[tert-butoxycarbonyl(cyclopropylmethyl)amino]-4-pyridyl]oxazole-4-carboxylic acid (844 mg, 2.35 mmol, synthesized via Steps 1-4 of Intermediate DF), DIPEA (1.14 g, 8.81 mmol) and HATU (1.23 g, 3.23 mmol). The mixture was stirred at 25° C. for 0.5 hour. On completion, the reaction mixture was diluted with water 80 mL, filtered to give the filter cake which was dried in vacuo to give the title compound (1.00 g, 67% yield) as light yellow solid; LC-MS (ESI$^+$) m/z 512.4 (M+H)$^+$.

Step 2—Tert-butyl N-[4-[4-[[3-carbamoyl-1-(2-oxoethyl)pyrazol-4-yl]carbamoyl]oxazol-2-yl]-2-pyridyl]-N-(cyclopropylmethyl)carbamate To a solution of tert-butyl N-[4-[4-[[3-carbamoyl-1-(2-hydroxyethyl)pyrazol-4-yl]carbamoyl]oxazol-2-yl]-2-pyridyl]-N-(cyclopropylmethyl)carbamate (300 mg, 486 umol) in THF (50 mL) was added DMP (412 mg, 973 umol), and the mixture was stirred at 10° C. for 16 hours. On completion, the reaction mixture was filtered to give the filtrate, which was then concentrated in vacuo to give a residue. The residue was purified by prep-HPLC (FA condition) to give the title compound (90.0 mg, 33% yield) as light yellow solid; LC-MS (ESI$^+$) m/z 528.3 (M+H+$H_2O$)$^+$.

1-[2-[2-[2-[3-(2-Aminoethoxy)propoxy]ethoxy]ethoxy]ethyl]-4-nitro-pyrazole-3-carboxamide (Intermediate HH)

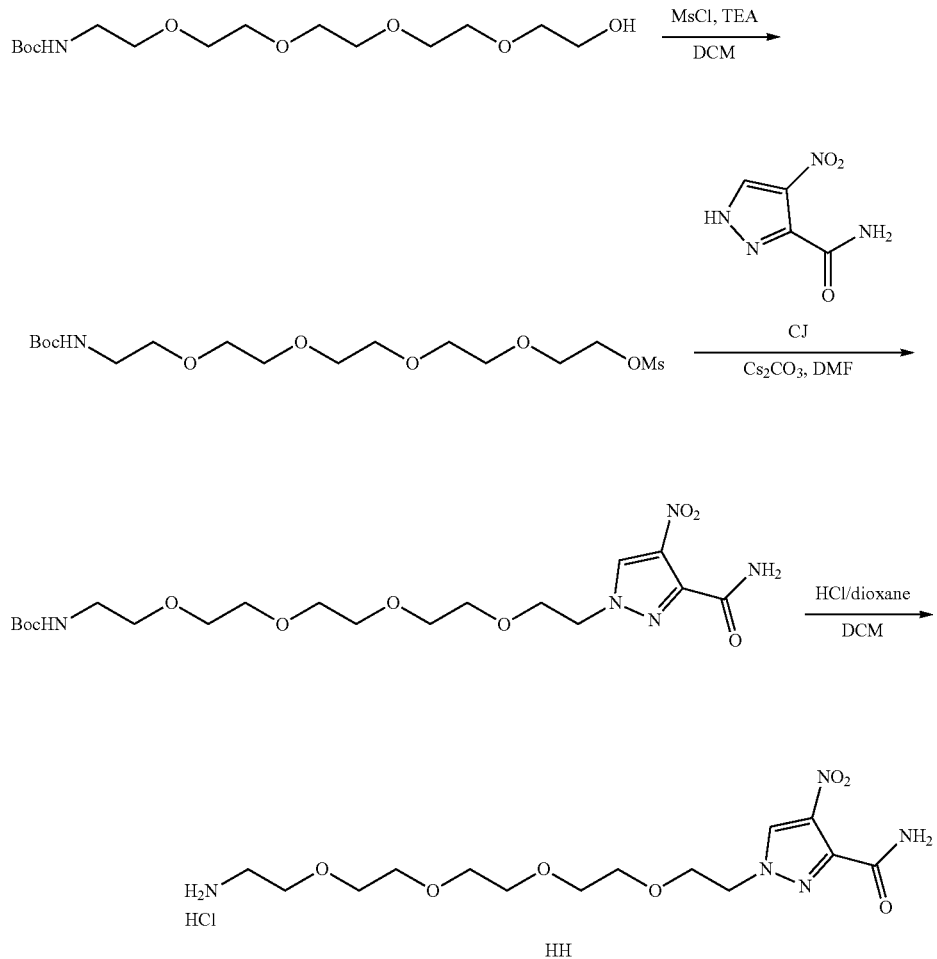

Step 1—2-[2-[2-[2-[2-(Tert-butoxycarbonylamino)ethoxy]ethoxy]ethoxy]ethyl methane sulfonate To a solution of tert-butyl N-[2-[2-[2-[2-(2-hydroxyethoxy)ethoxy]ethoxy]ethoxy]ethyl]carbamate (4.00 g, 11.9 mmol, CAS #1404111-67-6) and TEA (3.00 g, 29.6 mmol) in DCM (40 mL) was added MsCl (1.77 g, 15.4 mmol) at 0° C. The reaction mixture was stirred at 25° C. for 2 hours. On completion, the mixture was quenched with water (20 mL), and extracted with DCM. The organic layer was washed with water (50 mL) and brine (50 mL), dried with $Na_2SO_4$, and filtered. The filtrate was concentrated in vacuo to give the title compound (4.65 g, 94% yield) as a yellow solid. $^1$H NMR (400 MHz, $CDCl_3$) δ 5.05 (s, 1H), 4.41-4.31 (m, 2H), 3.79-3.74 (m, 2H), 3.69-3.58 (m, 12H), 3.56-3.51 (m, 2H), 3.34-3.27 (m, 2H), 3.08 (s, 3H), 1.44 (s, 9H).

Step 2—Tert-butyl N-[2-[2-[2-[2-[2-(3-carbamoyl-4-nitro-pyrazol-1-yl)ethoxy]ethoxy]ethoxy]ethoxy]ethyl]carbamate To a solution of 2-[2-[2-[2-[2-(tert-butoxycarbonylamino)ethoxy]ethoxy]ethoxy]ethoxy]ethyl methanesulfonate (4.59 g, 11.1 mmol) and 4-nitro-1H-pyrazole-3-carboxamide (1.50 g, 9.61 mmol, Intermediate CJ) in DMF (25 mL) was added $Cs_2CO_3$ (7.20 g, 22.1 mmol). The reaction mixture was stirred at 125° C. for 15 hours. On completion, the mixture was filtered and the filtrate was concentrated in vacuo, and the residue was purified by reverse phase (0.1% HCl condition) to give the title compound (1.45 g, 31% yield) as yellow oil. LC-MS ($ESI^+$) m/z 498.3 $(M+Na)^+$.

Step 3—1-[2-[2-[2-[3-(2-Aminoethoxy)propoxy]ethoxy]ethoxy]ethyl]-4-nitro-pyrazole-3-carboxamide To a solution of tert-butyl N-[2-[2-[2-[2-[2-(3-carbamoyl-4-nitro-pyrazol-1-yl)ethoxy]ethoxy]ethoxy]ethoxy]ethyl]carbamate (1.45 g, 2.99 mmol) in DCM (6 mL) was added HCl/dioxane (10 mL). The reaction mixture was stirred at 25° C. for 20 minutes. On completion, the mixture was concentrated in vacuo to give the title compound (1.19 g, 94% yield) as yellow oil. $^1$H NMR (400 MHz, DMSO-$d_6$) δ 8.83 (s, 1H), 8.02 (s, 1H), 7.77 (s, 1H), 4.40-4.30 (m, 2H), 3.81 (t, J=5.2 Hz, 2H), 3.60 (t, J=5.2 Hz, 2H), 3.56-3.53 (m, 8H), 3.49-3.46 (m, 4H), 2.98-2.91 (m, 2H); LC-MS ($ESI^+$) m/z 376.2 $(M+H)^+$.

4-Amino-1-[2-[2-[2-[2-[2-[[2-(2,6-dioxo-3-piperidyl)-1,3-dioxo-isoindolin-4-yl]amino]ethoxy]ethoxy]ethoxy]ethoxy]ethyl]pyrazole-3-carboxamide (Intermediate HI)

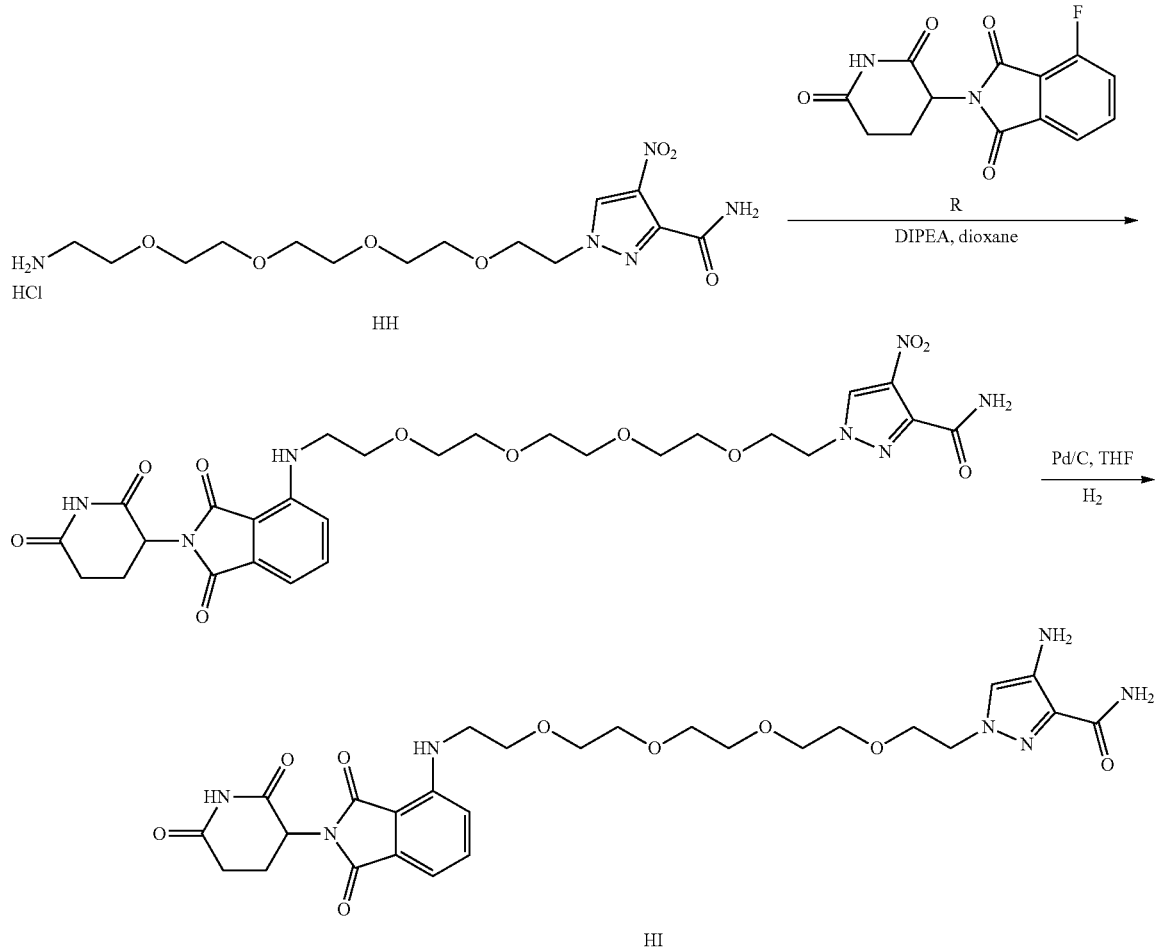

Step 1—1-[2-[2-[2-[2-[2-[[2-(2,6-Dioxo-3-piperidyl)-1,3-dioxo-isoindolin-4-yl]amino]ethoxy]ethoxy]ethoxy]ethoxy]ethyl]-4-nitro-pyrazole-3-carboxamide To a solution of 1-[2-[2-[2-[2-(2-aminoethoxy)ethoxy]ethoxy]ethoxy]ethyl]-4-nitro-pyrazole-3-carboxamide (0.50 g, 1.21 mmol, HCl, Intermediate HH) and 2-(2,6-dioxo-3-piperidyl)-4-fluoro-isoindoline-1,3-dione (352 mg, 1.27 mmol, Intermediate R) in dioxane (8 mL) was added DIPEA (785 mg, 6.07 mmol). The reaction mixture was stirred at 115° C. for 12 hours. On completion, the mixture was concentrated in vacuo. The residue was purified by silica gel chromatography to give the title compound (280 mg, 37% yield) as yellow oil. LC-MS (ESI⁺) m/z 632.3 (M+H)⁺.

Step 2—4-Amino-1-[2-[2-[2-[2-[2-[[2-(2,6-dioxo-3-piperidyl)-1,3-dioxo-isoindolin-4-yl]amino]ethoxy]ethoxy]ethoxy]ethoxy]ethyl]pyrazole-3-carboxamide To a solution of 1-[2-[2-[2-[2-[2-[[2-(2,6-dioxo-3-piperidyl)-1,3-dioxo-isoindolin-4-yl]amino]ethoxy]ethoxy]ethoxy]ethoxy]ethyl]-4-nitro-pyrazole-3-carboxamide (140 mg, 222 umol) in THF (5 mL) was added Pd/C (0.3 g, 20% wt). The reaction mixture was stirred at 25° C. for 0.4 hour under H₂ (15 Psi). On completion, the mixture was filtered and the filtrate was concentrated in vacuo to give the title compound (100 mg, 75% yield) as yellow oil. LC-MS (ESI⁺) m/z 602.1 (M+H)⁺.

2-[2-(Tert-butoxycarbonylamino)-4-pyridyl]oxazole-4-carboxylic acid (Intermediate HJ)

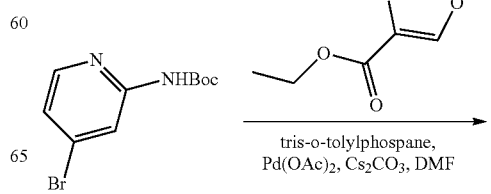

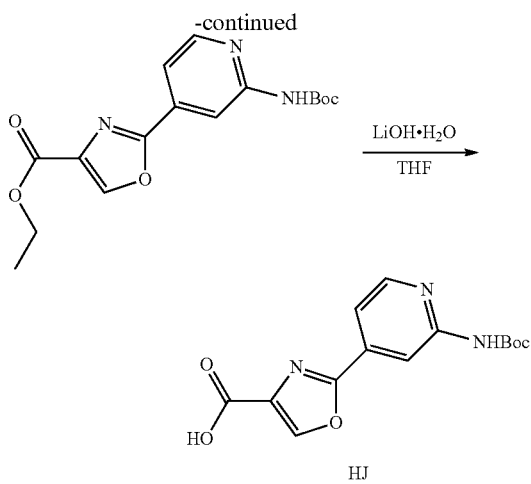

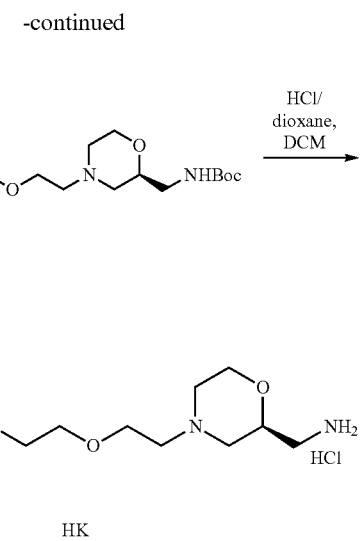

Step 1—Ethyl 2-[2-(tert-butoxycarbonylamino)-4-pyridyl]oxazole-4-carboxylate A mixture of tert-butyl N-(4-bromo-2-pyridyl)carbamate (1.00 g, 3.66 mmol, CAS #207799-10-8), ethyl oxazole-4-carboxylate (517 mg, 3.66 mmol, CAS #170487-38-4), tris-o-tolylphosphane (223 mg, 732 umol), Pd(OAc)$_2$ (82.2 mg, 366 umol) and Cs$_2$CO$_3$ (2.39 g, 7.32 mmol) in DMF (10 mL) was degassed and purged with N$_2$ 3 times, and then the mixture was stirred at 70° C. for 17 hrs under N$_2$ atmosphere. On completion, the mixture was diluted with water (300 mL), and extracted with EA (3×200 mL). The organic layer was washed with water (400 mL), dried over Na$_2$SO$_4$, filtered and concentrated in vacuo to give the title compound (1.22 g, 50% yield) as a yellow solid. LC-MS (ESI$^+$) m/z 278.2 (M+H−56)$^+$.

Step 2—2-[2-(Tert-butoxycarbonylamino)-4-pyridyl]oxazole-4-carboxylic acid

To a solution of methyl 2-[2-(tert-butoxycarbonylamino)-4-pyridyl]oxazole-4-carboxylate (1.17 g, 3.66 mmol) in MeOH (5 mL) and H$_2$O (5 mL) was added LiOH.H$_2$O (439 mg, 18.3 mmol). The mixture was stirred at 15° C. for 6 hours. On completion, the mixture was concentrated, then 1M HCl was added to the residue until the pH=5-6, and then filtered. The filter cake was dried in vacuo to give the title compound (400 mg, 28% yield) as a yellow solid. $^1$H NMR (400 MHz, DMSO-d$_6$) δ 13.37 (br s, 1H), 10.31-10.12 (m, 1H), 9.13-8.95 (m, 1H), 8.52 (s, 1H), 8.50 (d, J=5.4 Hz, 1H), 7.63-7.58 (m, 1H), 1.69-1.53 (m, 9H); LC-MS (ESI$^+$) m/z 250.2 (M+H−56)$^+$.

4-[2-[2-[(2S)-2-(aminomethyl)morpholin-4-yl]ethoxy]ethylamino]-2-(2,6-dioxo-3-piperidyl) isoindoline-1,3-dione (Intermediate HK)

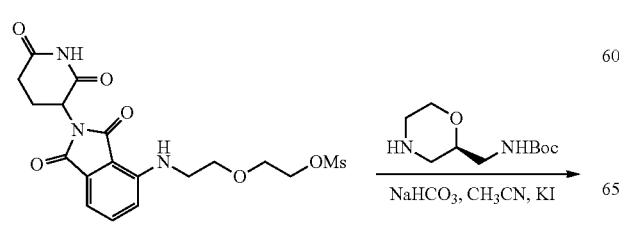

Step 1—Tert-butyl N-[[(2S)-4-[2-[2-[[2-(2,6-dioxo-3-piperidyl)-1,3-dioxo-isoindolin-4-yl]amino]ethoxy]ethyl]morpholin-2-yl]methyl]carbamate To a solution of 2-[2-[[2-(2,6-dioxo-3-piperidyl)-1,3-dioxo-isoindolin-4-yl]amino]ethoxy]ethyl methanesulfonate (460 mg, 1.05 mmol, synthesized via Steps 1-2 of Example 184) and tert-butyl N-[[(2R)-morpholin-2-yl]methyl]carbamate (453 mg, 2.09 mmol, CAS #186202-57-3) in ACN (15 mL) was added KI (17.4 mg, 105 umol) and NaHCO$_3$ (264 mg, 3.14 mmol). The reaction mixture was stirred at 80° C. for 17 hrs. On completion, the mixture was concentrated in vacuo. The residue was purified by silica gel chromatography to give the title compound (530 mg, 91% yield) as a yellow solid. LC-MS (ESI$^+$) m/z 560.2 (M+H)$^+$.

Step 2—4-[2-[2-[(2S)-2-(aminomethyl)morpholin-4-yl]ethoxy]ethylamino]-2-(2,6-dioxo-3-piperidyl) isoindoline-1,3-dione To a solution of tert-butyl N-[[(2S)-4-[2-[2-[[2-(2,6-dioxo-3-piperidyl)-1,3-dioxo-isoindolin-4-yl]amino]ethoxy]ethyl]morpholin-2-yl]methyl]carbamate (630 mg, 1.13 mmol) in DCM (6 mL) was added HCl/dioxane (10 mL). The reaction mixture was stirred at 15° C. for 1 hr. On completion, the mixture was concentrated in vacuo to give the title compound (550 mg, 99% yield) as a yellow solid. LC-MS (ESI$^+$) m/z 460.4 (M+H)$^+$.

Methyl 4-nitro-1H-pyrazole-3-carboxylate (Intermediate HL)

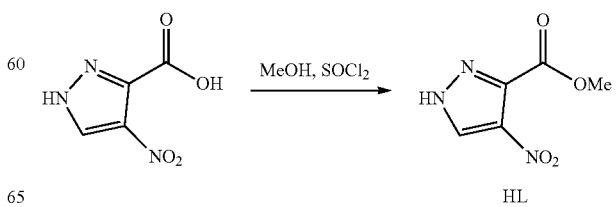

1411

To a solution of 4-nitro-1H-pyrazole-3-carboxylic acid (50.0 g, 318 mmol, CAS #5334-40-7) in MeOH (250 mL) was added SOCl$_2$ (56.8 g, 477 mmol). The mixture was stirred at 70° C. for 5 hrs. On completion, the mixture was concentrated in vacuo to give the title compound (54.0 g, 99% yield) as white solid. $^1$H NMR (400 MHz, DMSO-d$_6$) δ 14.40 (s, 1H), 9.98 (s, 1H), 3.89 (s, 3H).

Tert-butyl (cyclopropylmethyl)(4-(4-((1-(4-formylphenyl)-3-(trifluoromethyl)-1H-pyrazol-4-yl)carbamoyl)oxazol-2-yl)pyridin-2-yl)carbamate (Intermediate HM)

1412

Step 1—4-(4-(2-(2-((Tert-butoxycarbonyl)(cyclopropylmethyl)amino)pyridin-4-yl)oxazole-4-carboxamido)-3-(trifluoromethyl)-1H-pyrazol-1-yl)benzoic (isopropylcarbonic)anhydride To a solution of 4-[4-[[2-[2-[tert-butoxycarbonyl(cyclopropylmethyl)amino]-4-pyridyl]oxazole-4-carbonyl]amino]-3-(trifluoromethyl)pyrazol-1-yl]benzoic acid (700 mg, 960 umol, Intermediate EG) in THF (10 mL) was added TEA (194 mg, 1.92 mmol). Then, the reaction mixture was cooled to −10° C. After, isopropyl carbonochloridate (235 mg, 1.92 mmol) was added and the reaction mixture was stirred at −10° C. for 2 hours. On completion, the reaction mixture was filtered. The filtrate was concentrated in vacuo

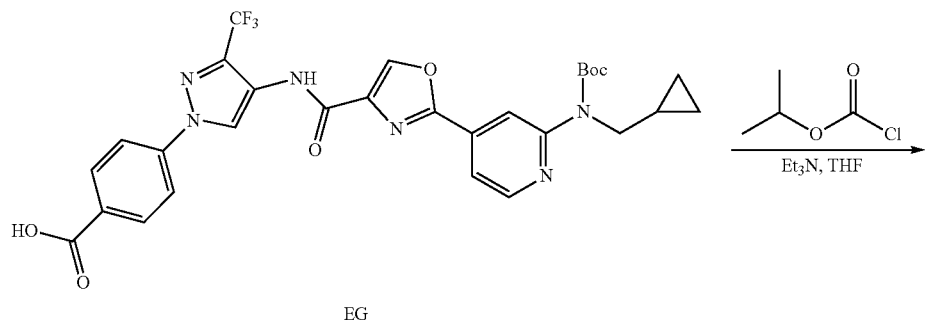

EG

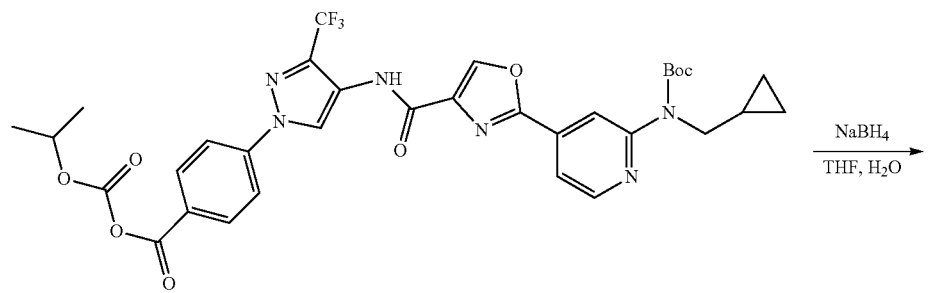

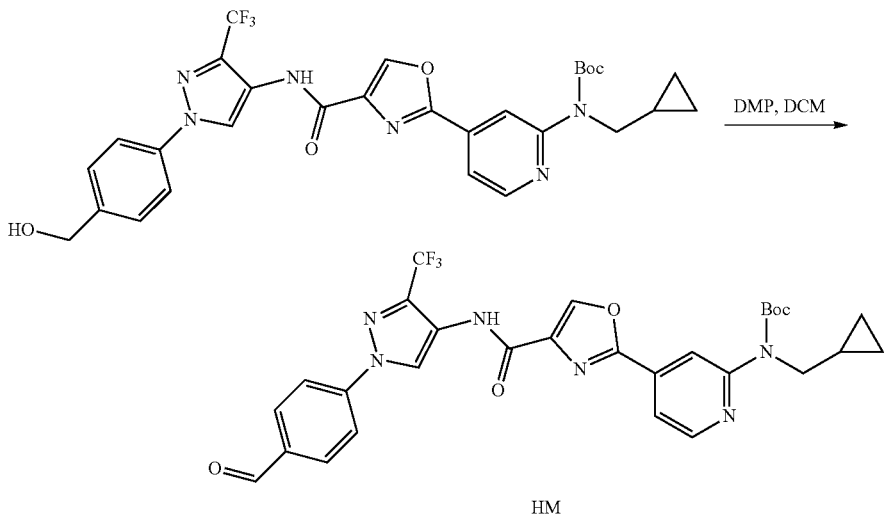

HM to give the title compound (720 mg, 91% yield) as white solid. LC-MS (ESI⁺) m/z 699.0 (M+H)⁺.

Step 2—Tert-butyl (cyclopropylmethyl)(4-(4-((1-(4-(hydroxymethyl)phenyl)-3-(trifluoromethyl)-1H-pyrazol-4-yl)carbamoyl)oxazol-2-yl)pyridin-2-yl)carbamate To a solution of isopropoxycarbonyl 4-[4-[[2-[2-[tert-butoxycarbonyl(cyclopropylmethyl)amino]-4-pyridyl]oxazole-4-carbonyl]amino]-3-(trifluoromethyl)pyrazol-1-yl]benzoate (720 mg, 876 umol) in THF (20 mL) was added NaBH₄ (66.3 mg, 1.75 mmol) and water (63.1 mg, 3.50 mmol). The residue was mixture was stirred at 0° C. for 1 hour. On completion, the reaction mixture was quenched with water (5 mL) and the mixture was extracted with DCM (3×50 mL). The combined organic layer was washed with brine (20 mL), dried over anhydrous sodium sulfate, filtered and concentrated in vacuo to give the title compound (520 mg, 99% yield) as a white solid. ¹H NMR (400 MHz, CDCl₃) δ 9.06 (s, 1H), 8.88 (s, 1H), 8.54 (d, J=5.2 Hz, 1H), 8.42 (s, 1H), 8.36 (s, 1H), 7.76 (d, J=8.4 Hz, 2H), 7.64 (d, J=4.8 Hz, 1H), 7.51 (d, J=8.4 Hz, 2H), 4.78 (s, 2H), 3.96 (d, J=7.2 Hz, 2H), 1.59 (s, 9H), 0.93-0.81 (m, 1H), 0.47-0.42 (m, 2H), 0.30-0.26 (m, 2H); LC-MS (ESI⁺) m/z 599.2 (M+H)⁺.

Step 3—Tert-butyl (cyclopropylmethyl)(4-(4-((1-(4-formylphenyl)-3-(trifluoromethyl)-1H-pyrazol-4-yl)carbamoyl)oxazol-2-yl)pyridin-2-yl)carbamate To a solution of tert-butyl N-(cyclopropylmethyl)-N-[4-[4-[[1-[4-(hydroxymethyl)phenyl]-3-(trifluoromethyl)pyrazol-4-yl]carbamoyl]oxazol-2-yl]-2-pyridyl]carbamate (320 mg, 535 umol) in DCM (10 mL) was added DMP (454 mg, 1.07 mmol). The reaction mixture was stirred at 25° C. for 5 hours. On completion, the reaction mixture was quenched with saturated Na₂S₂O₃ (20 mL), and extracted with DCM (3×30 mL). The combined organic layers was washed with saturated NaHCO₃ (2×20 mL), then washed with brine (30 mL), dried over with anhydrous sodium sulfate, filtered and concentrated in vacuo. The residue was purified by prep-HPLC (0.1% HCl) to give the title compound (123 mg, 39% yield) as a white solid. ¹H NMR (400 MHz, CDCl₃) δ 10.08 (s, 1H), 9.08 (s, 1H), 9.01 (d, J=5.2 Hz, 1H), 8.98 (s, 1H), 8.57 (s, 1H), 8.06 (d, J=8.4 Hz, 2H), 7.95 (d, J=8.8 Hz, 2H), 7.45 (s, 1H), 7.39 (s, 1H), 3.35 (s, 2H), 1.67 (s, 9H), 1.15-1.05 (m, 1H), 0.78-0.76 (m, 2H), 0.45-0.44 (m, 2H).

3-(5-bromo-3-methyl-2-oxo-benzimidazol-1-yl)piperidine-2,6-dione (3-(5-bromo-3-methyl-2-oxo-2,3-dihydro-1H-1,3-benzodiazol-1-yl)piperidine-2,6-dione)

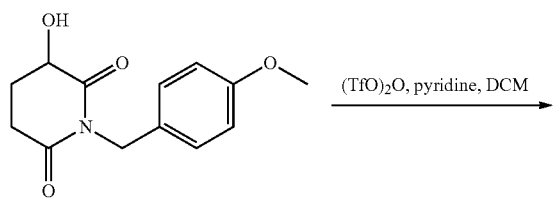

(TfO)₂O, pyridine, DCM

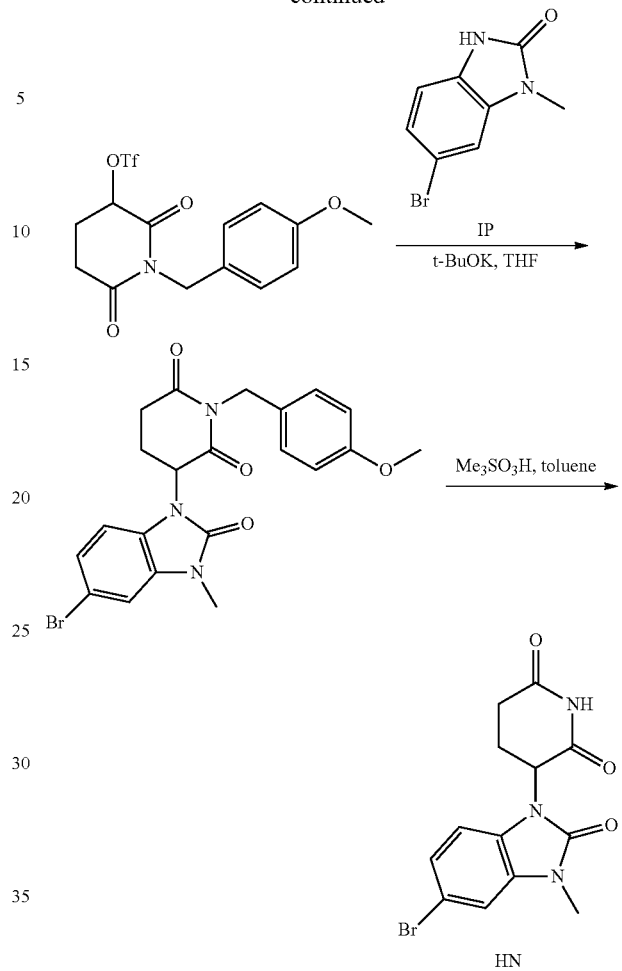

Step 1—[1-[(4-Methoxyphenyl)methyl]-2,6-dioxo-3-piperidyl]trifluoromethanesulfonate To a solution of 3-hydroxy-1-[(4-methoxyphenyl)methyl]piperidine-2,6-dione (43.0 g, 173 mmol, Intermediate IQ) and pyridine (27.3 g, 345 mmol) in DCM (500 mL) was added trifluoromethylsulfonyl trifluoromethanesulfonate (73.0 g, 258.74 mmol) dropwise at 0° C. The mixture was stirred at 0-10° C. for 1.5 hours under N₂. On completion, the mixture was concentrated in vacuo. The residue was purified by column chromatography on silica gel to give the title compound (45.0 g, 68% yield) as light yellow gum. ¹H NMR (400 MHz, CDCl₃) δ 7.36 (d, J=8.4 Hz, 2H), 6.85-6.82 (m, 2H), 5.32-5.28 (m, 1H), 4.91 (s, 2H), 3.79 (s, 3H), 3.02-2.97 (m, 1H), 2.79-2.74 (m, 1H), 2.41-2.35 (m, 2H).

Step 2—3-(5-Bromo-3-methyl-2-oxo-benzimidazol-1-yl)-1-[(4-methoxyphenyl)methyl]piperidine-2,6-dione To a solution of 5-bromo-3-methyl-1H-benzimidazol-2-one (4.90 g, 21.6 mmol, Intermediate IP) in THF (300 mL) was added t-BuOK (3.63 g, 32.3 mmol) at 0° C. The mixture was stirred at 0-10° C. for 1 hour under N₂. Then a solution of [1-[(4-methoxyphenyl)methyl]-2,6-dioxo-3-piperidyl]trifluoromethanesulfonate (9.87 g, 25.9 mmol) in THF (100 mL) was added to the reaction mixture at 0-10° C. during 30 minutes. The mixture was stirred at 0-10° C. for 30 minutes under N₂. An additional solution of [1-[(4-methoxyphenyl) methyl]-2,6-dioxo-3-piperidyl]trifluoromethanesulfonate (2.47 g, 6.47 mmol) in THF (20 mL) was added to the reaction mixture at 0-10° C. dropwise. The mixture was then stirred at 0-10° C. for another 30 minutes under N₂. On completion, the reaction was quenched water (400 mL) and extracted with EA (3×200 mL). The combined organic layer was concentrated in vacuo. The residue was triturated with EA (80 mL) and filtered. The filter cake was collected and dried in vacuo to give the title compound (6.70 g, 67% yield) as light yellow solid. The filtrate was also concentrated in vacuo and the residue was purified by column chromatography to give another batch title compound (1.80 g, 18% yield) as light yellow solid. ¹H NMR (400 MHz, DMSO-d₆) δ 7.47 (d, J=1.6 Hz, 1H), 7.21-7.16 (m, 3H), 7.01 (d, J=8.0 Hz, 1H), 6.85 (d, J=8.8 Hz, 2H), 5.55-5.51 (m, 1H), 4.84-4.73 (m, 2H), 3.72 (s, 3H), 3.33 (s, 3H), 3.04-3.00 (m, 1H), 2.83-2.67 (m, 2H), 2.07-2.05 (m, 1H).

Step 3—3-(5-Bromo-3-methyl-2-oxo-benzimidazol-1-yl)piperidine-2,6-dione

To a mixture of 3-(5-bromo-3-methyl-2-oxo-benzimidazol-1-yl)-1-[(4-methoxyphenyl)methyl]piperidine-2,6-dione (8.50 g, 18.6 mmol) in toluene (50 mL) was added methanesulfonic acid (33.8 g, 351 mmol, 25 mL) at room temperature (15° C.). The mixture was stirred at 120° C. for 2 hours. On completion, the reaction mixture was cooled to room temperature and concentrated in vacuo. The residue was poured into ice/water (200 mL), and extracted with EA (3×100 mL). The combined organic layer was washed with brine (50 mL), dried over Na₂SO₄, filtered and concentrated in vacuo. The residue was triturated with EA (80 mL) and filtered. The filtrate cake was collected and dried in vacuo to give the title compound (4.20 g, 67% yield) as off-white solid. ¹H NMR (400 MHz, DMSO-d₆) δ 11.12 (s, 1H), 7.47 (d, J=2.0 Hz, 1H), 7.22 (d, J=8.4 Hz, 1H), 7.10 (d, J=8.4 Hz, 1H), 5.40-5.35 (m, 1H), 2.34 (s, 3H), 2.92-2.88 (m, 1H), 2.71-2.60 (m, 2H), 2.03-1.99 (m, 1H).

3-[5-[3-[2-(2-Aminoethoxy)ethoxy]propyl]-3-methyl-2-oxo-benzimidazol-1-yl]piperidine-2,6-dione (Intermediate HO)

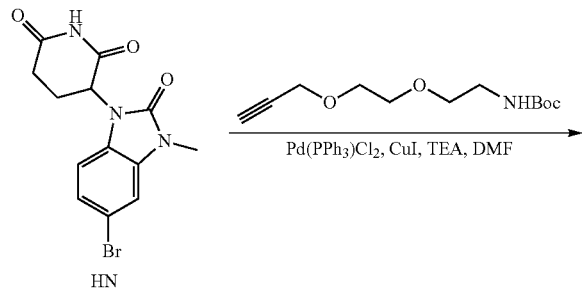

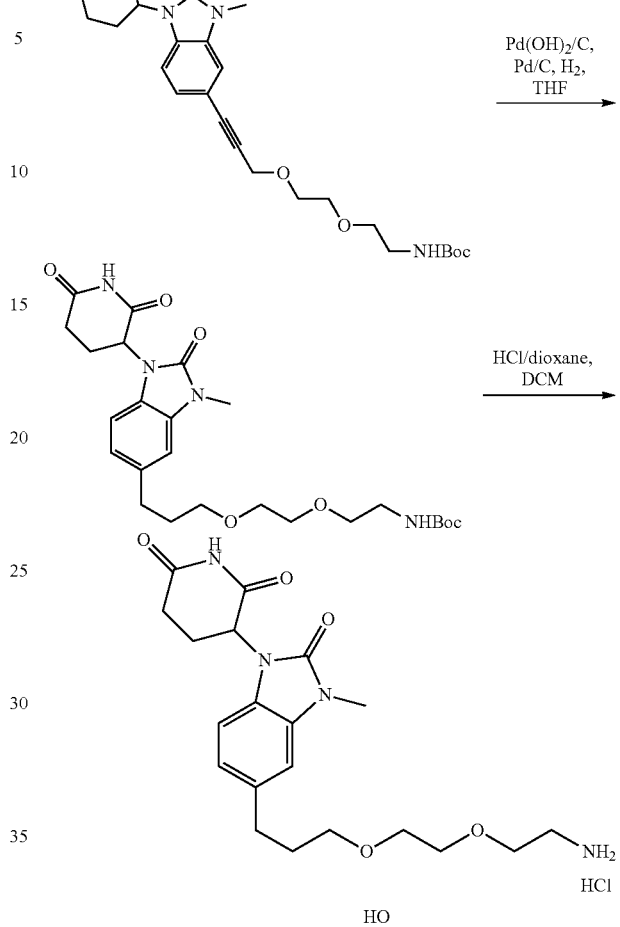

Step 1—Tert-butyl N-[2-[2-[3-[1-(2,6-dioxo-3-piperidyl)-3-methyl-2-oxo-benzimidazol-5-yl]prop-2-ynoxy]ethoxy]ethyl]carbamate To a solution of 3-(5-bromo-3-methyl-2-oxo-benzimidazol-1-yl)piperidine-2,6-dione (350 mg, 1.04 mmol, Intermediate HN) and tert-butyl N-[2-(2-prop-2-ynoxyethoxy)ethyl]carbamate (629 mg, 2.59 mmol, synthesized via Step 1 of Intermediate CQ) in DMF (10 mL) was added TEA (2.62 g, 25.8 mmol, 3.60 mL), CuI (98.5 mg, 517 umol) and Pd(PPh₃)₂Cl₂ (363 mg, 517 umol). The reaction mixture was stirred at 80° C. for 1.5 hours under N₂. On completion, the mixture was filtered, and the filtrate was concentrated in vacuo to give a residue. The residue was dissolved in DCM (20 mL) and thiourea (resin) (300 mg) was added. The mixture was stirred at 20° C. for 12 hours. Then the reaction mixture was filtered and the filtrate was concentrated in vacuo to give a residue. The residue was purified by reverse phase (0.1% FA condition) to give the title compound (208 mg, 40% yield) as yellow solid. LC-MS (ESI⁺) m/z 523.3 (M+Na)⁺. ¹H NMR (400 MHz, DMSO-d₆) δ 11.13 (s, 1H), 7.34 (d, J=0.8 Hz, 1H), 7.22-7.12 (m, 2H), 6.83-6.70 (m, 1H), 5.40 (dd, J=5.6, 12.8 Hz, 1H), 4.40 (s, 2H), 3.67-3.61 (m, 2H), 3.60-3.54 (m, 2H), 3.40 (t, J=6.0 Hz, 2H), 3.35 (s, 3H), 3.08 (q, J=6.0 Hz, 2H), 2.96-2.84 (m, 1H), 2.73-2.60 (m, 2H), 2.09-2.00 (m, 1H), 1.38 (s, 9H).

Step 2—Tert-butyl N-[2-[2-[3-[1-(2,6-dioxo-3-piperidyl)-3-methyl-2-oxo-benzimidazol-5-yl]propoxy]ethoxy]ethyl]carbamate To a solution of tert-butyl N-[2-[2-[3-[1-(2,6-dioxo-3-piperidyl)-3-methyl-2-oxo-benzimidazol-5-yl]prop-2-ynoxy]ethoxy]ethyl]carbamate (100 mg, 199 umol) in THF (10 mL) was added Pd(OH)$_2$/C (50 mg, 10 wt %) and Pd/C (50 mg, 10 wt %), and the reaction mixture was stirred under H$_2$ (15 psi) for 1 hr. On completion, the residue was filtered and the filtrate was concentrated in vacuo to give the title compound (100 mg, 99.2% yield) as yellow oil. LC-MS (ESI$^+$) m/z 527.4 (M+Na)$^+$.

Step 3—3-[5-[3-[2-(2-Aminoethoxy)ethoxy]propyl]-3-methyl-2-oxo-benzimidazol-1-yl]piperidine-2,6-dione To a solution of tert-butyl N-[2-[2-[3-[1-(2,6-dioxo-3-piperidyl)-3-methyl-2-oxo-benzimidazol-5-yl]propoxy]ethoxy]ethyl]carbamate (100 mg, 198.19 umol) in DCM (2 mL) was added HCl/dioxane (4 M, 2 mL), and the reaction mixture was stirred at 20° C. for 1 hr. On completion, the mixture was concentrated in vacuo to give the title compound (85.0 mg, 97% yield) as yellow oil. LC-MS (ESI$^+$) m/z 405.2 (M+H)$^+$. $^1$H NMR (400 MHz, DMSO-d$_6$) δ 7.09-6.96 (m, 2H), 6.88 (d, J=7.6 Hz, 1H), 5.34 (dd, J=5.2, 12.8 Hz, 1H), 3.57-3.49 (m, 6H), 3.41 (t, J=6.4 Hz, 2H), 3.33 (s, 3H), 2.98-2.83 (m, 2H), 2.76-2.68 (m, 1H), 2.64-2.68 (m, 2H), 2.63-2.54 (m, 1H), 2.46-2.44 (m, 1H), 2.04-1.97 (m, 1H), 1.87-1.78 (m, 2H).

3-(4-bromo-3-methyl-2-oxo-2,3-dihydro-1H-benzo[d]imidazol-1-yl)piperidine-2,6-dione (Intermediate HP)

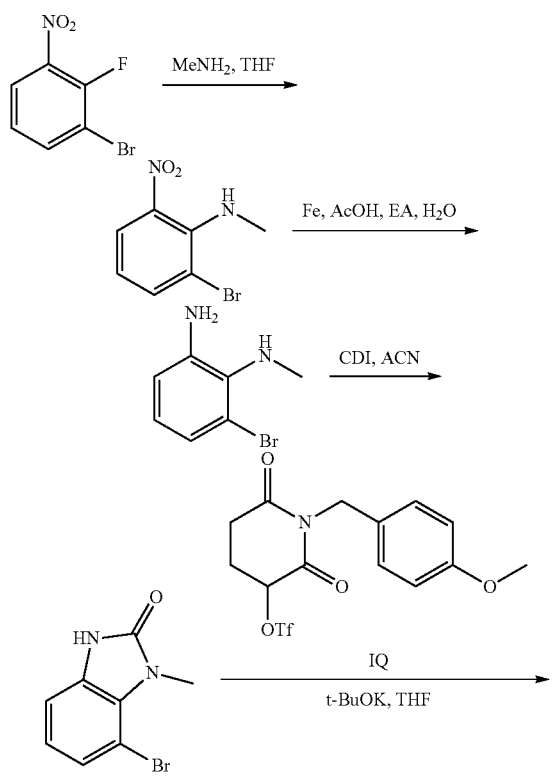

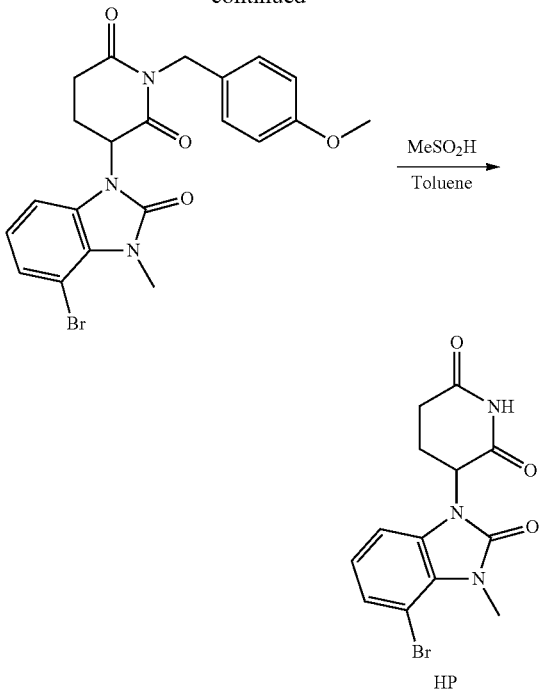

Step 1—2-Bromo-N-methyl-6-nitro-aniline

To a solution of 1-bromo-2-fluoro-3-nitro-benzene (40.0 g, 181 mmol, CAS #58534-94-4) in THF (40 mL) was added MeNH$_2$ (2 M, 400 mL). The reaction mixture was stirred at 60° C. for 12 hours. On completion, the reaction mixture was poured into sat.NaHCO$_3$ (30 mL) and extracted with EA (3×200 mL). The combined organic layers were washed with brine (2×200 mL), dried with anhydrous Na$_2$SO$_4$, filtered and concentrated in vacuo to give the title compound (40.0 g, 95% yield) as red oil. LC-MS (ESI$^+$) m/z 230.9 (M+H)$^+$

Step 2—3-Bromo-N2-methyl-benzene-1,2-diamine

To a mixture of 2-bromo-N-methyl-6-nitro-aniline (23.0 g, 99.5 mmol) in EA (300 mL) and H$_2$O (10 mL) was added AcOH (100 mL). The mixture was warmed to 50° C. Then Fe (22.2 g, 398 mmol) was added to the reaction mixture and the mixture was heated to 80° C. about 4 hours. On completion, the reaction mixture was filtered and concentrated in vacuo. The residue was diluted with water (100 mL) and extracted with EA (3×200 mL). The combined organic layers was dried over Na$_2$SO$_4$, filtered and concentrated in vacuo to give the title compound (20.0 g, 99% yield) as red oil. $^1$H NMR (400 MHz, DMSO-d$_6$) δ 6.73-6.70 (m, 1H), 6.68-6.60 (m, 2H), 5.02 (s, 2H), 3.67 (s, 1H), 2.58 (s, 3H).

Step 3—4-Bromo-3-methyl-1H-benzimidazol-2-one

To a mixture of 3-bromo-N2-methyl-benzene-1,2-diamine (20.0 g, 99.4 mmol) in ACN (300 mL) was added CDI (32.2 g, 198 mmol). The reaction mixture was stirred at 85° C. for 12 hours under N$_2$ atmosphere. On completion, the reaction mixture was concentrated in vacuo. The reaction mixture was diluted with water (200 mL), where a solid precipitate was formed, which was filtered off. The solid was washed with water (1 L) and dried in vacuo to give the title compound (20.0 g, 88% yield) as white solid. $^1$H NMR (400 MHz, DMSO-d$_6$) δ 11.17 (s, 1H), 7.14 (dd, J=1.2, 8.0 Hz, 1H), 7.00-6.95 (m, 1H), 6.93-6.87 (m, 1H), 3.55 (s, 3H).

Step 4—3-(4-Bromo-3-methyl-2-oxo-benzimidazol-1-yl)-1-[(4-methoxyphenyl)methyl]piperidine-2,6-dione To a solution of 4-bromo-3-methyl-1H-benzimidazol-2-one (12.0 g, 52.8 mmol) in THF (300 mL) was added t-BuOK (7.12 g, 63.4 mmol). The reaction mixture was stirred at 0° C. for 0.5 hr. Subsequently, [1-[(4-methoxyphenyl)methyl]-2,6-dioxo-3-piperidyl]trifluoromethanesulfonate (20.1 g, 52.8 mmol, Intermediate IQ) in a solution of THF (100 mL) was added dropwise. The resulting reaction mixture was stirred at 20° C. for 0.5 hr under N$_2$. On completion, the reaction mixture was quenched with saturated NH$_4$Cl (100 mL), and extracted with ethyl acetate (200 mL). The combined organic layers were washed with brine (2×100 mL), dried over anhydrous sodium sulfate, filtered, the filtrate was concentrated in vacuo. The crude product was purified by reversed-phase HPLC (0.1% FA condition) to give the title compound (13.3 g, 55% yield) as a yellow solid. $^1$H NMR (400 MHz, CDCl$_3$) δ 7.38 (d, J=8.8 Hz, 2H), 7.22 (d, J=8.0 Hz, 1H), 6.84 (d, J=8.8 Hz, 2H), 6.80 (t, J=8.0 Hz, 1H), 6.48-6.40 (d, J=8.0 Hz, 1H), 5.22 (dd, J=5.2, 12.8 Hz, 1H), 5.04-4.93 (m, 2H), 3.81 (s, 3H), 3.80 (s, 3H), 3.12-2.98 (m, 1H), 2.93-2.77 (m, 1H), 2.62 (dq, J=4.4, 13.2 Hz, 1H), 2.20-2.17 (m, 1H).

Step 5—3-(4-bromo-3-methyl-2-oxo-2,3-dihydro-1H-benzo[d]imidazol-1-yl)piperidine-2,6-dione A mixture of 3-(4-bromo-3-methyl-2-oxo-benzimidazol-1-yl)-1-[(4-methoxyphenyl)methyl]piperidine-2,6-dione (13.3 g, 29.0 mmol) in a mixed solvent of Tol. (80 mL) and methane sulfonic acid (40 mL) was degassed and purged with N$_2$ for 3 times, and then the mixture was stirred at 120° C. for 2 hrs under N$_2$ atmosphere. On completion, the reaction mixture was concentrated in vacuo to remove toluene. The residue was added 200 mL of ice water, and then white solid precipitate formed. The mixture was filtered and the filtered cake was collected and dried over in vacuo to give the title compound (7.30 g, 74% yield) as white solid. $^1$H NMR (400 MHz, DMSO-d$_6$) δ 11.13 (s, 1H), 7.25 (d, J=8.0 Hz, 1H), 7.17 (d, J=8.0 Hz, 1H), 7.05-6.93 (m, 1H), 5.41 (dd, J=5.2, 12.8 Hz, 1H), 3.64 (s, 3H), 2.96-2.83 (m, 1H), 2.78-2.59 (m, 2H), 2.08-2.00 (m, 1H).

3-[4-[3-[2-(2-Aminoethoxy)ethoxy]propyl]-3-methyl-2-oxo-benzimidazol-1-yl]piperidine-2,6-dione (Intermediate HQ)

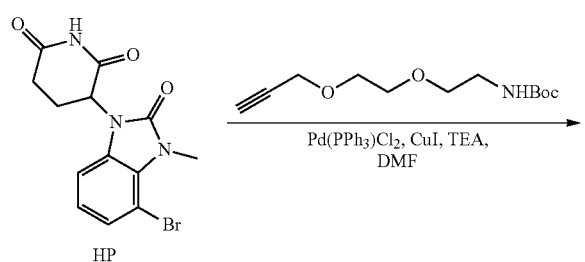

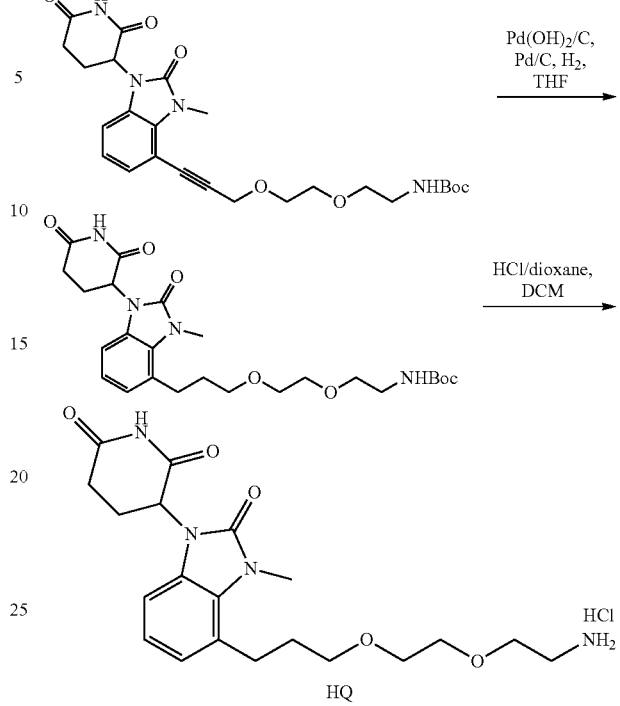

Step 1—Tert-butyl N-[2-[2-[3-[1-(2,6-dioxo-3-piperidyl)-3-methyl-2-oxo-benzimidazol-4-yl]prop-2-ynoxy]ethoxy]ethyl]carbamate To a mixture of 3-(4-bromo-3-methyl-2-oxo-benzimidazol-1-yl)piperidine-2,6-dione (100 mg, 295 umol, Intermediate HP) and tert-butyl N-[2-(2-prop-2-ynoxyethoxy)ethyl]carbamate (93.5 mg, 384 umol, synthesized via Step 1 of Intermediate CQ) in DMF (5 mL) was added CuI (5.63 mg, 29.5 umol), Pd(PPh$_3$)$_2$Cl$_2$ (20.7 mg, 29.5 umol) and TEA (538 mg, 5.32 mmol, 740 uL). The reaction mixture was heated at 80° C. for 30 minutes under microwave. On completion, the reaction mixture was concentrated in vacuo. The residue was purified by prep-HPLC (column: Kromasil 150*25 mm*10 um; mobile phase: [water (0.225% FA)-ACN]) to give the title compound (55.0 mg, 34% yield, FA) as brown solid. $^1$H NMR (400 MHz, DMSO-d$_6$) δ 11.12 (s, 1H), 7.18 (d, J=7.6 Hz, 1H), 7.13 (d, J=7.6 Hz, 1H), 7.08-7.00 (m, 1H), 6.76 (s, 1H), 5.41 (dd, J=4.4, 12.4 Hz, 1H), 4.47 (s, 2H), 3.69-3.65 (m, 2H), 3.65 (s, 3H), 3.57 (d, J=4.4 Hz, 2H), 3.40 (t, J=6.0 Hz, 2H), 3.08 (d, J=5.6 Hz, 2H), 2.96-2.84 (m, 1H), 2.77-2.63 (m, 2H), 2.09-1.97 (m, 1H), 1.37 (s, 9H). LC-MS (ESI$^+$) m/z 501.4 (M+H)$^+$.

Step 2—Tert-butyl N-[2-[2-[3-[1-(2,6-dioxo-3-piperidyl)-3-methyl-2-oxo-benzimidazol-4-yl]propoxy]ethoxy]ethyl]carbamate To a mixture of tert-butyl N-[2-[2-[3-[1-(2,6-dioxo-3-piperidyl)-3-methyl-2-oxo-benzimidazol-4-yl]prop-2-ynoxy]ethoxy]ethyl]carbamate (50.0 mg, 99.8 umol) in THF (4 mL) was added Pd/C (15 mg, 10 wt %) and Pd(OH)$_2$/C (15 mg, 10 wt %). The reaction mixture was stirred at 25° C. for 1 hour under H$_2$ (15 Psi) atmosphere. On completion, the reaction mixture was filtered and concentrated in vacuo to give the title compound (50.0 mg, 99% yield) as brown oil. LC-MS (ESI⁺) m/z 505.4 (M+H)⁺

Step 3—3-[4-[3-[2-(2-Aminoethoxy)ethoxy]propyl]-3-methyl-2-oxo-benzimidazol-1-yl]piperidine-2,6-dione To a mixture of tert-butyl N-[2-[2-[3-[1-(2,6-dioxo-3-piperidyl)-3-methyl-2-oxo-benzimidazol-4-yl]propoxy]ethoxy]ethyl]carbamate (50.0 mg, 99.0 umol) in DCM (5 mL) was added HCl/dioxane (4 M, 5 mL). The reaction mixture was stirred at 25° C. for 1 hour. On completion, the reaction mixture was concentrated in vacuo to give the title compound (43.0 mg, 98% yield, HCl) as colourless oil. LC-MS (ESI⁺) m/z 405.3 (M+H)⁺.

4-[2-[2-[(2R)-2-(aminomethyl)morpholin-4-yl]ethoxy]ethylamino]-2-(2,6-dioxo-3-piperidyl) isoindoline-1,3-dione (Intermediate HR)

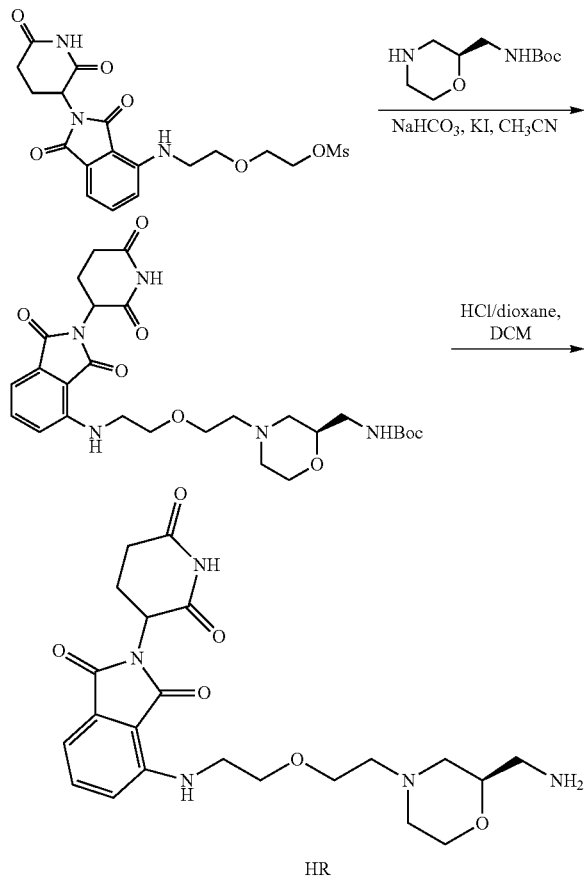

HR

Step 1—Tert-butyl N-[[(2R)-4-[2-[2-[[2-(2,6-dioxo-3-piperidyl)-1,3-dioxo-isoindolin-4-yl]amino]ethoxy]ethyl]morpholin-2-yl]methyl]carbamate To a solution of 2-[2-[[2-(2,6-dioxo-3-piperidyl)-1,3-dioxo-isoindolin-4-yl]amino]ethoxy]ethyl methanesulfonate (500 mg, 1.14 mmol, synthesized via Steps 1-2 of Example 184), tert-butyl N-[[(2S)-morpholin-2-yl]methyl]carbamate (492 mg, 2.28 mmol, CAS #875551-59-0) in ACN (20.0 mL) was added KI (18.8 mg, 113 umol) and NaHCO₃ (286 mg, 3.41 mmol). The mixture was stirred at 80° C. for 16 hrs. On completion, the mixture was concentrated in vacuo. The mixture was purified by silica gel column (DCM:MeOH=50:1) to give the title compound (400 mg, 62% yield) as yellow solid. ¹H NMR (400 MHz, CDCl₃) δ 8.38-8.13 (m, 1H), 7.46-7.40 (m, 1H), 7.04 (d, J=7.2 Hz, 1H), 6.83 (d, J=8.8 Hz, 1H), 6.43 (s, 1H), 4.94-4.81 (m, 2H), 3.80-3.72 (m, 1H), 3.67-3.54 (m, 6H), 3.41-3.34 (m, 2H), 3.34-3.18 (m, 1H), 3.07-2.94 (m, 1H), 2.84-2.75 (m, 2H), 2.73-2.66 (m, 2H), 2.61-2.49 (m, 2H), 2.21-2.09 (m, 1H), 2.08-2.01 (m, 1H), 1.95-1.85 (m, 1H), 1.69-1.55 (m, 1H), 1.36 (s, 9H).

Step 2—4-[2-[2-[(2R)-2-(aminomethyl)morpholin-4-yl]ethoxy]ethylamino]-2-(2,6-dioxo-3-piperidyl) isoindoline-1,3-dione To a solution of tert-butyl N-[[(2R)-4-[2-[2-[[2-(2,6-dioxo-3-piperidyl)-1,3-dioxo-isoindolin-4-yl]amino]ethoxy]ethyl]morpholin-2-yl]methyl]carbamate (380 mg, 679 umol) in DCM (3.00 mL) was added HCl/dioxane (4 M, 5.00 mL). The mixture was stirred at 15° C. for 1 hr. On completion, the mixture was concentrated in vacuo to give the title compound (330 mg, 95% yield) as yellow solid. LC-MS (ESI⁺) m/z 460.1 (M+H)⁺.

3-(Difluoromethyl)-4-nitro-1H-pyrazole (Intermediate HS)

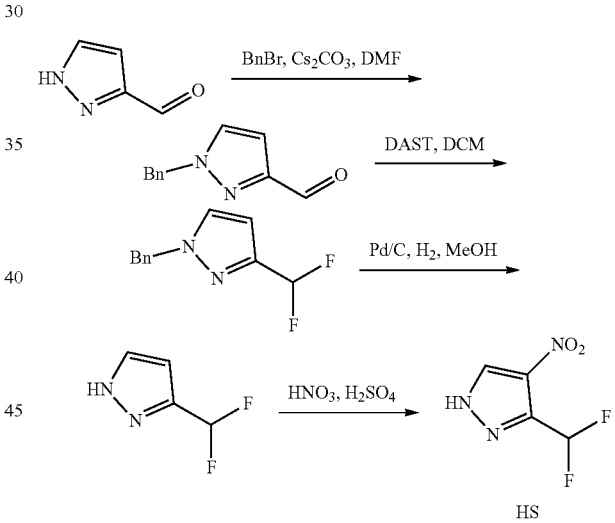

HS

Step 1—1-Benzyl-1H-pyrazole-3-carbaldehyde

To a solution of 1H-pyrazole-3-carbaldehyde (5.00 g, 52.0 mmol, CAS #: 3920-50-1) and BnBr (9.34 g, 54.6 mmol) in DMF (50 mL) was added Cs₂CO₃ (42.4 g, 130 mmol). The reaction mixture was stirred at 25° C. for 1 hour. On completion, the reaction mixture was diluted with water, extracted with ethyl acetate (3×100 mL). The combined organic layers was washed with brine (50 mL), dried over anhydrous sodium sulfate, filtered and concentrated in vacuo. The crude product was purified by silica gel chromatography (Petroleum ether:Ethyl acetate=20:1) to give the title compound (8.00 g, 83% yield) as a colorless oil. ¹H NMR (400 MHz, CDCl₃) δ 10.02 (s, 1H), 7.44 (d, J=2.4 Hz, 1H), 7.43-7.33 (m, 3H), 7.29-7.24 (m, 2H), 6.85 (d, J=2.4 Hz, 1H), 5.42 (s, 2H).

Step 2—1-Benzyl-3-(difluoromethyl)-1H-pyrazole

To a solution of 1-benzylpyrazole-3-carbaldehyde (5.00 g, 26.9 mmol) in DCM (30 mL) was added DAST (17.3 g, 107 mmol) at 0° C. The reaction mixture was stirred at 25° C. for 5 hours. On completion, the reaction mixture was quenched with methanol (30 mL) at 0° C. After, the mixture was concentrated in vacuo. The crude product was purified by silica gel chromatography (petroleum ether:ethyl acetate=20:1) to give the title compound (3.30 g, 59% yield) as a white solid. $^1$H NMR (400 MHz, CDCl$_3$) δ 7.43-7.36 (m, 3H), 7.27-7.21 (m, 2H), 6.91-6.57 (m, 1H), 6.55-6.51 (m, 1H), 5.35 (s, 2H); LC-MS (ESI$^+$) m/z 209.1 (M+H)$^+$.

Step 3—3-(Difluoromethyl)-1H-pyrazole

To a solution of 1-benzyl-3-(difluoromethyl)pyrazole (1.00 g, 4.80 mmol) in methanol (20 mL) was added Pd(OH)$_2$/C (0.1 g, 10% purity) under N$_2$ atmosphere. The suspension was degassed and purged with H$_2$ for 3 times. The mixture was stirred at 40° C. for 12 hrs under H$_2$ (50 Psi). On completion, the reaction mixture was filtered and concentrated in vacuo to give the title compound (470 mg, 83% yield) as colorless oil. $^1$H NMR (400 MHz, DMSO-d$_6$) δ 13.16 (s, 1H), 7.85 (s, 1H), 7.14-6.82 (m, 1H), 6.52 (s, 1H).

Step 4—3-(Difluoromethyl)-4-nitro-1H-pyrazole

To a solution of 3-(difluoromethyl)-1H-pyrazole (470 mg, 3.98 mmol) in H$_2$SO$_4$ (5 mL) was carefully added a 65% solution of HNO$_3$ (965 mg, 9.95 mmol) dropwise at 0° C. After stirring for 10 minutes, the reaction mixture was heated to 115° C., and stirred for 12 hrs. On completion, the reaction mixture was cooled to 25° C. Then, the reaction mixture was poured onto the (100 mL) ice, extracted with ethyl acetate (3×50 mL). The combined organic layers was washed with brine (2×50 mL), dried over with anhydrous sodium sulfate, filtered and concentrated in vacuo to give the title compound (530 mg, 82% yield). $^1$H NMR (400 MHz, DMSO-d$_6$) δ 14.41 (s, 1H), 9.04 (s, 1H), 7.50-7.17 (m, 1H), 7.50-7.17 (m, 1H).

14-(3-(Difluoromethyl)-4-nitro-1H-pyrazol-1-yl)-3,6,9,12-tetraoxatetradecan-1-amine (Intermediate HT)

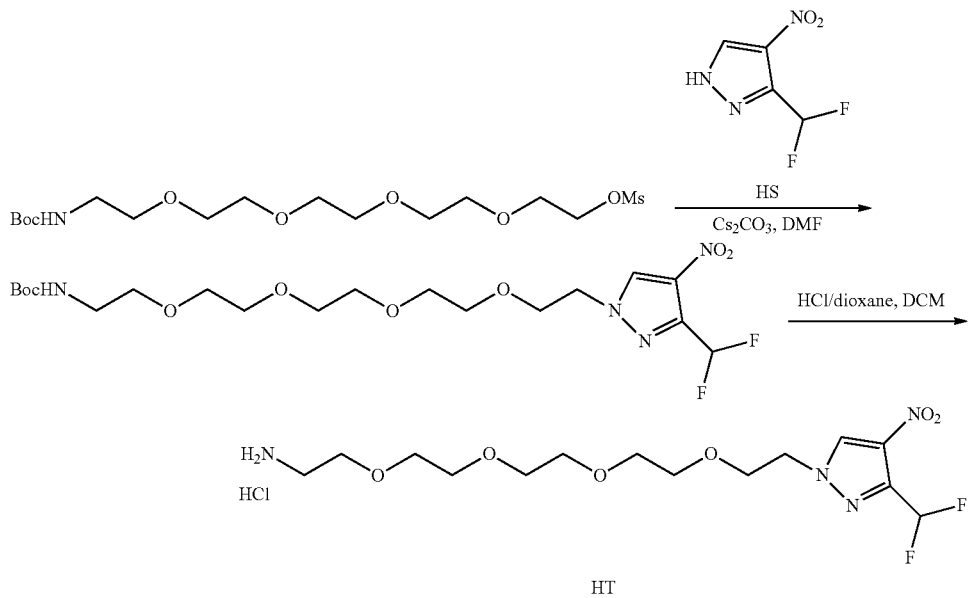

Step 1—Tert-butyl N-[2-[2-[2-[2-[2-[3-(difluoromethyl)-4-nitro-pyrazol-1-yl]ethoxy]ethoxy]ethoxy]ethoxy]ethyl]carbamate To a solution of 3-(difluoromethyl)-4-nitro-1H-pyrazole (200 mg, 1.23 mmol, Intermediate HS) and 2-[2-[2-[2-(tert-butoxycarbonylamino)ethoxy]ethoxy]ethoxy]ethoxy]ethyl methanesulfonate (560 mg, 1.35 mmol, synthesized via Step 1 of Intermediate HH) in DMF (5 mL) was added Cs$_2$CO$_3$ (799 mg, 2.45 mmol). The reaction mixture was stirred at 130° C. for 12 hrs. On completion, the reaction mixture was filtered and the filtrate was concentrated in vacuo. The residue was purified by prep-HPLC (condition: 0.1% HCl) to give the title compound (220 mg, 36% yield) as a yellow oil. $^1$H NMR (400 MHz, DMSO-d$_6$) δ 8.99 (s, 1H), 7.51-7.16 (m, 1H), 6.76 (s, 1H), 4.41 (t, J=5.2 Hz, 2H), 3.83 (t, J=5.2 Hz, 2H), 3.61-3.44 (m, 13H), 3.61-3.44 (m, 1H), 3.05 (q, J=5.6 Hz, 2H), 1.37 (s, 8H); LC-MS (ESI$^+$) m/z 505.4 (M+Na)$^+$.

Step 2—14-(3-(Difluoromethyl)-4-nitro-1H-pyrazol-1-yl)-3,6,9,12-tetraoxatetradecan-1-amine To a solution of tert-butyl N-[2-[2-[2-[2-[2-[3-(difluoromethyl)-4-nitro-pyrazol-1-yl]ethoxy]ethoxy]ethoxy]ethoxy]ethyl]carbamate (220 mg, 456 umol) in DCM (5 mL) was added HCl/dioxane (4 M, 114 uL). The reaction mixture was stirred at 20° C. for 15 min. On completion, the reaction mixture was concentrated in vacuo to give the title compound (191 mg, 100% yield) as yellow oil. LC-MS (ESI$^+$) m/z 383.0 (M+H)$^+$.

4-((14-(4-Amino-3-(difluoromethyl)-1H-pyrazol-1-yl)-3,6,9,12-tetraoxatetradecyl)amino)-2-(2,6-dioxopiperidin-3-yl)isoindoline-1,3-dione (Intermediate HU)

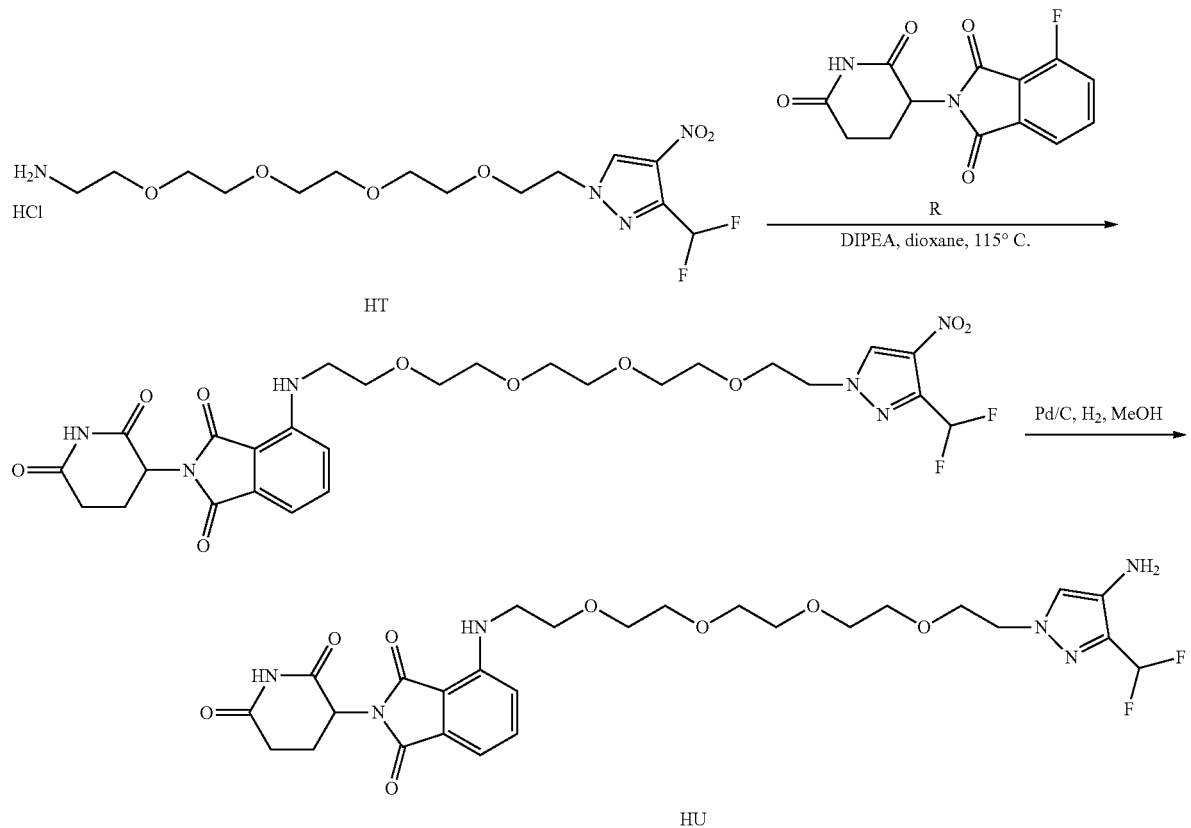

Step 1—4-((14-(3-(Difluoromethyl)-4-nitro-1H-pyrazol-1-yl)-3,6,9,12-tetraoxatetradecyl)amino)-2-(2,6-dioxopiperidin-3-yl)isoindoline-1,3-dione To a solution of 2-[2-[2-[2-[2-[3-(difluoromethyl)-4-nitro-pyrazol-1-yl]ethoxy]ethoxy]ethoxy]ethoxy]ethanamine (191 mg, 456 umol, Intermediate HT) and 2-(2,6-dioxo-3-piperidyl)-4-fluoro-isoindoline-1,3-dione (139 mg, 502 umol, Intermediate R) in dioxane (10 mL) was added DIPEA (295 mg, 2.28 mmol). The reaction mixture was stirred at 115° C. for 12 hours. On completion, the mixture was concentrated in vacuo. The crude product was purified by prep-HPLC (condition: 0.1% HCl) to give the title compound (170 mg, 58% yield) as a yellow oil. $^1$H NMR (400 MHz, DMSO-$d_6$) δ 11.10 (s, 1H), 8.98 (s, 1H), 7.58 (t, J=7.6 Hz, 1H), 7.45-7.18 (m, 1H), 7.14 (d, J=8.4 Hz, 1H), 7.04 (d, J=6.8 Hz, 1H), 6.60 (s, 1H), 5.06 (dd, J=4.8, 13.2 Hz, 1H), 4.43-4.37 (m, 2H), 3.82 (t, J=4.8 Hz, 2H), 3.64-3.59 (m, 1H), 3.61 (d, J=4.8 Hz, 1H), 3.56-3.46 (m, 14H), 2.97-2.80 (m, 1H), 2.65-2.55 (m, 2H), 2.09-1.98 (m, 1H); LC-MS (ESI$^+$) m/z 639.1 (M+H)$^+$.

Step 2—4-((14-(4-Amino-3-(difluoromethyl)-1H-pyrazol-1-yl)-3,6,9,12-tetraoxatetradecyl)amino)-2-(2,6-dioxopiperidin-3-yl)isoindoline-1,3-dione To a solution of 4-[2-[2-[2-[2-[2-[3-(difluoromethyl)-4-nitro-pyrazol-1-yl]ethoxy]ethoxy]ethoxy]ethoxy]ethyl-amino]-2-(2,6-dioxo-3-piperidyl)isoindoline-1,3-dione (170 mg, 266 umol) in methanol (20 mL) was added Pd/C (0.05 g, 10% wt) under N$_2$ atmosphere. The suspension was degassed and purged with H$_2$ for 3 times. The mixture was stirred at 20° C. for 0.5 hr under H$_2$ (15 Psi). On completion, the reaction mixture was filtered and concentrated in vacuo to give the title compound (130 mg, 80% yield) as yellow oil. LC-MS (ESI$^+$) m/z 609.1 (M+H)$^+$.

4-Fluoro-2-(2-oxo-3-piperidyl)isoindoline-1,3-dione (Intermediate HV

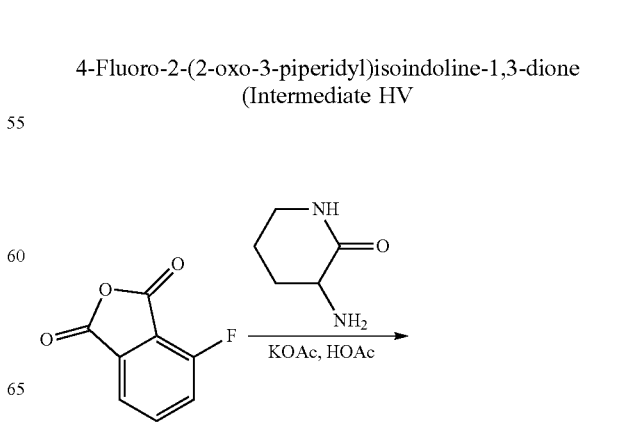

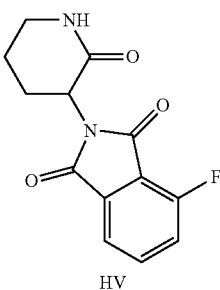

To a solution of 4-fluoroisobenzofuran-1,3-dione (661 mg, 3.98 mmol, CAS #652-39-1), KOAc (1.21 g, 12.3 mmol) in HOAc (30 mL) was added 3-aminopiperidin-2-one (0.50 g, 4.38 mmol CAS #1892-22-4). Then the mixture was stirred at 90° C. for 16 hours. On completion, the mixture was concentrated in vacuo to give a residue, which was then diluted with water 60 mL, and filtered to give the filter cake (0.60 g, 57% yield) as yellow solid. $^1$H NMR (400 MHz, DMSO-$d_6$) δ 7.97-7.86 (m, 2H), 7.79-7.66 (m, 2H), 4.60 (dd, J=6.4, 12.0 Hz, 1H), 3.26-3.14 (m, 2H), 2.27-2.13 (m, 1H), 2.06-1.96 (m, 1H), 1.95-1.86 (m, 2H).

4-(2-Aminoethylamino)-2-(2-oxo-3-piperidyl)isoindoline-1,3-dione (Intermediate HW)

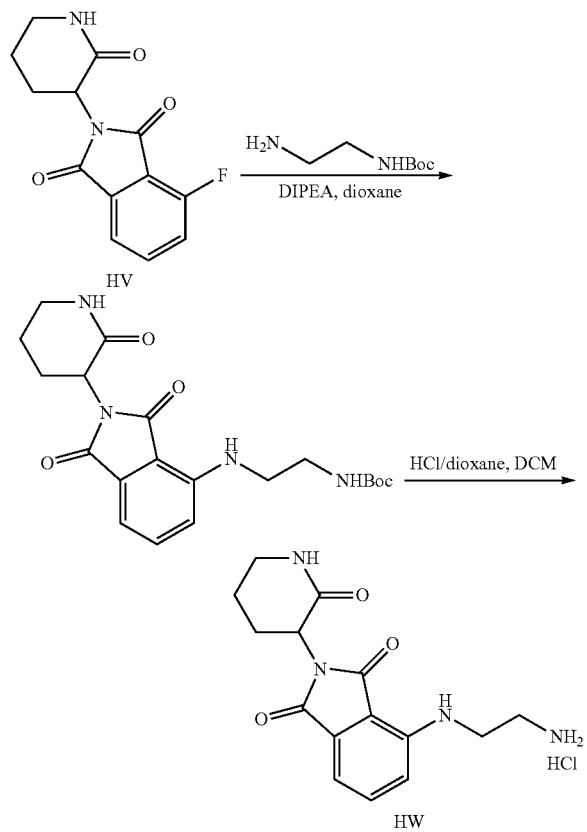

Step 1—Tert-butyl N-[2-[[1,3-dioxo-2-(2-oxo-3-piperidyl)isoindolin-4-yl]amino]ethyl]carbamate To a solution of tert-butyl N-(2-aminoethyl)carbamate (366 mg, 2.29 mmol) in dioxane (20 mL) was added 4-fluoro-2-(2-oxo-3-piperidyl)isoindoline-1,3-dione (0.6 g, 2.29 mmol, Intermediate HV) and DIPEA (1.48 g, 11.4 mmol), and the mixture was stirred at 115° C. for 16 hours. On completion, the reaction mixture was concentrated in vacuo to give a residue. The residue was purified by column chromatography to give the title compound (360 mg, 39.06% yield) as light yellow oil. $^1$H NMR (400 MHz, DMSO-$d_6$) δ 7.81 (s, 1H), 7.55 (t, J=8.0 Hz, 1H), 7.11 (d, J=8.4 Hz, 1H), 7.07-6.95 (m, 2H), 6.68 (t, J=5.6 Hz, 1H), 4.50 (dd, J=6.0, 12.6 Hz, 1H), 3.44-3.34 (m, 2H), 3.24-3.16 (m, 2H), 3.14-3.09 (m, 2H), 2.25-2.14 (m, 2H), 1.98-1.81 (m, 3H), 1.37 (s, 9H).

Step 2—4-(2-Aminoethyl amino)-2-(2-oxo-3-piperidyl)isoindoline-1,3-dione

To a solution of tert-butyl N-[2-[[1,3-dioxo-2-(2-oxo-3-piperidyl)isoindolin-4-yl]amino]ethyl]carbamate (350 mg, 869 umol) in DCM (4 mL) was added HCl/dioxane (4 M, 3 mL). The mixture was stirred at 5° C. for 0.5 hour. On completion, the reaction mixture was concentrated in vacuo to give the title compound (280 mg, 91% yield) as yellow solid; LC-MS (ESI$^+$) m/z 303.2 (M+H)$^+$.

2-(2,6-dioxo-3-piperidyl)-5-fluoro-isoindoline-1,3-dione (Intermediate HX)

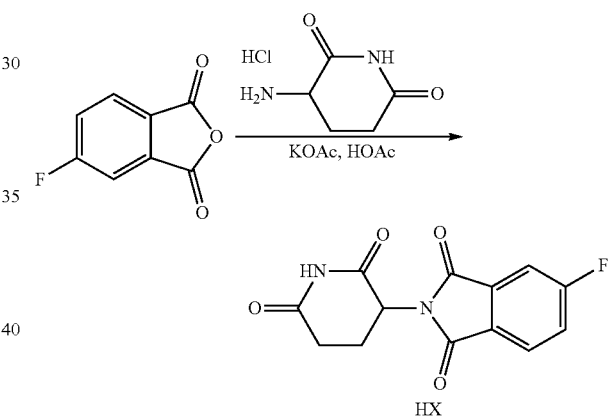

To a mixture of 3-aminopiperidine-2,6-dione (10.8 g, 65.8 mmol, HCl) and KOAc (18.2 g, 185 mmol) in HOAc (160 mL) was added 5-fluoroisobenzofuran-1,3-dione (9.95 g, 59.9 mmol, CAS #319-03-9). Then the mixture was stirred at 90° C. for 16 hours. On completion, the reaction mixture was cooled to 25° C. and diluted with water (600 mL), and then stirred at 0° C. for 0.5 hour then filtered. The filter cake was dried in vacuo to give the title compound (14.0 g, 84% yield) as black brown solid. $^1$H NMR (400 MHz, DMSO-$d_6$) δ 11.15 (s, 1H), 8.01 (dd, J=4.4, 8.0 Hz, 1H), 7.84 (dd, J=2.4, 7.6 Hz, 1H), 7.76-7.67 (m, 1H), 5.17 (dd, J=5.6, 12.8 Hz, 1H), 2.97-2.83 (m, 1H), 2.65-2.51 (m, 2H), 2.13-2.03 (m, 1H).

Tert-butyl N-[2-[2-(2-oxoethoxy)ethoxy]ethyl]carbamate (Intermediate HY)

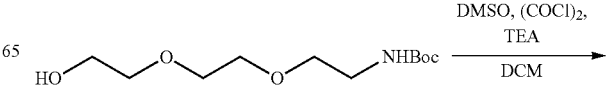

-continued

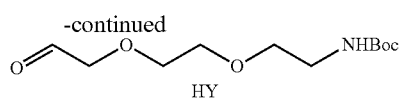

To a solution of DMSO (1.57 g, 20.0 mmol) in DCM (20 mL) was added a solution of (COCl)$_2$ (2.04 g, 16.0 mmol) in DCM (15 mL) dropwise at −70° C. The mixture was stirred at this temperature for 10 minutes. Then a solution of tert-butyl N-[2-[2-(2-hydroxyethoxy)ethoxy]ethyl]carbamate (2 g, 8.02 mmol, CAS #139115-92-7) in DCM (15 mL) was added into the above mixture slowly. After stirred at −70° C. for 50 minutes, TEA (6.49 g, 64.2 mmol) was added and the reaction mixture was stirred at −70° C. for 0.5 hr. On completion, the mixture was quenched with water (30 mL) and separated. The aqueous phase was extracted with DCM (2×30 mL). Then the organic phase was combined and washed with brine (2×50 mL), dried over Na$_2$SO$_4$, and concentrated in vacuo to give the title compound (1.36 g, 69% yield) as yellow oil. $^1$H NMR (400 MHz, DMSO-d$_6$) δ 9.57 (s, 1H), 6.80-6.74 (m, 1H), 4.18 (s, 2H), 3.63-3.53 (m, 4H), 3.39-3.34 (m, 2H), 3.08-3.04 (m, 2H), 1.37 (s, 9H).

5-[[1-[2-[2-(2-Aminoethoxy)ethoxy]ethyl]-4-piperidyl]amino]-2-(2,6-dioxo-3-piperidyl) isoindoline-1,3-dione (Intermediate HZ)

Step 1—Tert-butyl 4-[[2-(2,6-dioxo-3-piperidyl)-1,3-dioxo-isoindolin-5-yl]amino]piperidine-1-carboxylate To a solution of 2-(2,6-dioxo-3-piperidyl)-5-fluoro-isoindoline-1,3-dione (600 mg, 2.17 mmol, Intermediate HX) and tert-butyl 4-aminopiperidine-1-carboxylate (522 mg, 2.61 mmol, CAS #502482-34-0) in DMSO (7 mL) was added DIPEA (1.40 g, 10.8 mmol, 1.89 mL). The reaction mixture was stirred at 130° C. for 1.5 hours. On completion, the mixture was diluted with H$_2$O (10 mL), then filtered and the filtrate was concentrated in vacuo to give the title compound (250 mg, 25% yield) as a yellow solid. LC-MS (ESI$^+$) m/z 479.2 (M+Na)$^+$.

Step 2—2-(2,6-Dioxo-3-piperidyl)-5-(4-piperidylamino)isoindoline-1,3-dione

To a solution of tert-butyl 4-[[2-(2,6-dioxo-3-piperidyl)-1,3-dioxo-isoindolin-5-yl]amino]piperidine-1-carboxylate (350 mg, 766 umol) in DCM (4 mL) was added HCl/dixoane (4 M, 4 mL). The reaction mixture was stirred at 25° C. for 1 hour. On completion, the mixture was concentrated in vacuo to give the title compound (300 m g, 99% yield) as a yellow solid. LC-MS (ESI$^+$) m/z 357.3 (M+H)$^+$.

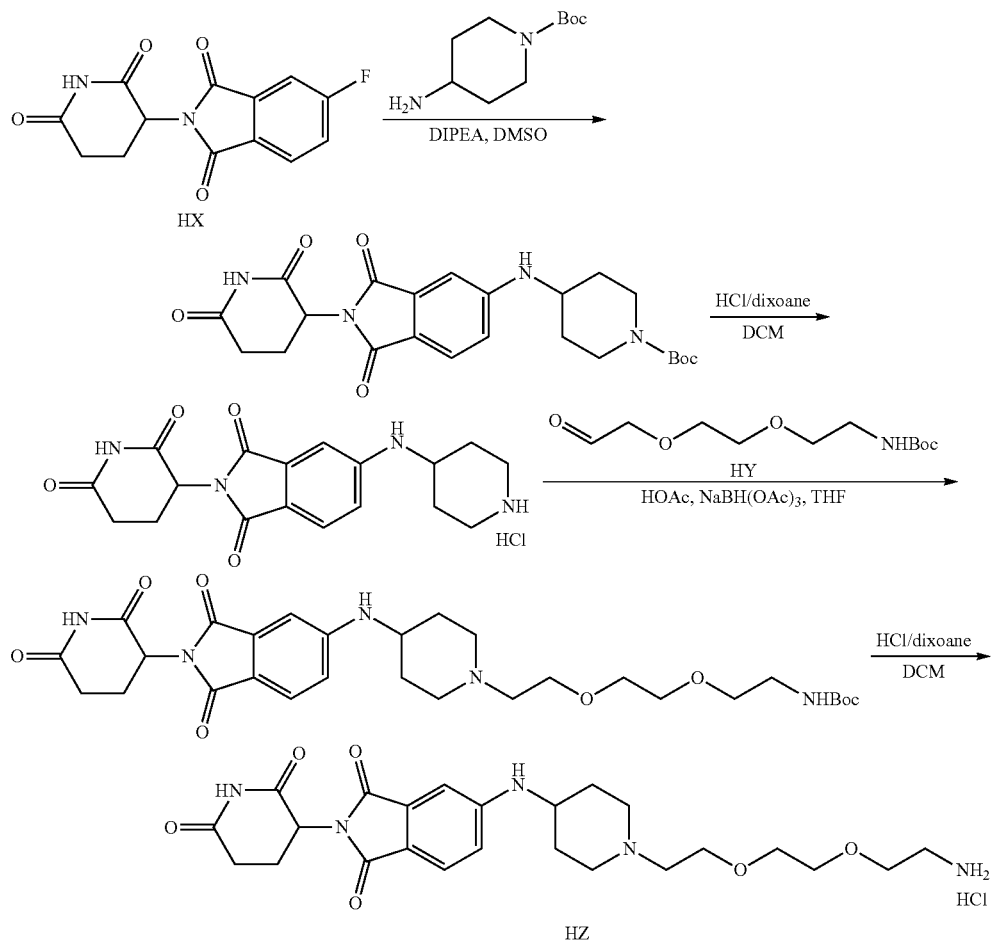

1431

Step 3—Tert-butyl N-[2-[3-[2-(2,6-dioxo-3-piperidyl)-1,3-dioxo-isoindolin-4-yl]propoxy]ethyl]carbamate To a solution of 2-(2,6-dioxo-3-piperidyl)-5-(4-piperidylamino)isoindoline-1,3-dione (200 mg, 509 umol, HCl) in THF (20 mL) was added TEA (103 mg, 1.02 mmol, 141 uL), the mixture was stirred at 20° C. for 10 mins, then tert-butyl N-[2-[2-(2-oxoethoxy)ethoxy]ethyl]carbamate (163 mg, 661 umol, Intermediate HY), HOAc (91.7 mg, 1.53 mmol, 87.3 uL) and NaBH(OAc)₃ (215 mg, 1.02 mmol) was added to the mixture, and the reaction mixture was stirred at 20° C. for 16 hr. On completion, the mixture was filtered, and the filtrate was concentrated in vacuo to give a residue. The residue was purified by reverse phase (0.1% FA condition) to give the title compound (110 mg, 37% yield) as a yellow solid. LC-MS (ESI⁺) m/z 588.1 (M+H)⁺.

1432

Step 4—5-[[1-[2-[2-(2-Aminoethoxy)ethoxy]ethyl]-4-piperidyl]amino]-2-(2,6-dioxo-3-piperidyl) isoindoline-1,3-dione To a solution of tert-butyl N-[2-[2-[2-[4-[[2-(2,6-dioxo-3-piperidyl)-1,3-dioxo-isoindolin-5-yl]amino]-1-piperidyl]ethoxy]ethoxy]ethyl]carbamate (110 mg, 187 umol) in DCM (4 mL) was added HCl/dioxane (4 M, 4 mL). The reaction mixture was stirred at 25° C. for 1 hour. On completion, the mixture was concentrated in vacuo to give the title compound (95.0 mg, 97% yield) as a yellow solid. LC-MS (ESI⁺) m/z 488.3 (M+H)⁺.

4-[4-[2-[2-(2-Aminoethoxy)ethoxy]ethyl]piperazin-1-yl]-2-(2,6-dioxo-3-piperidyl)isoindoline-1,3-dione
(Intermediate IA)

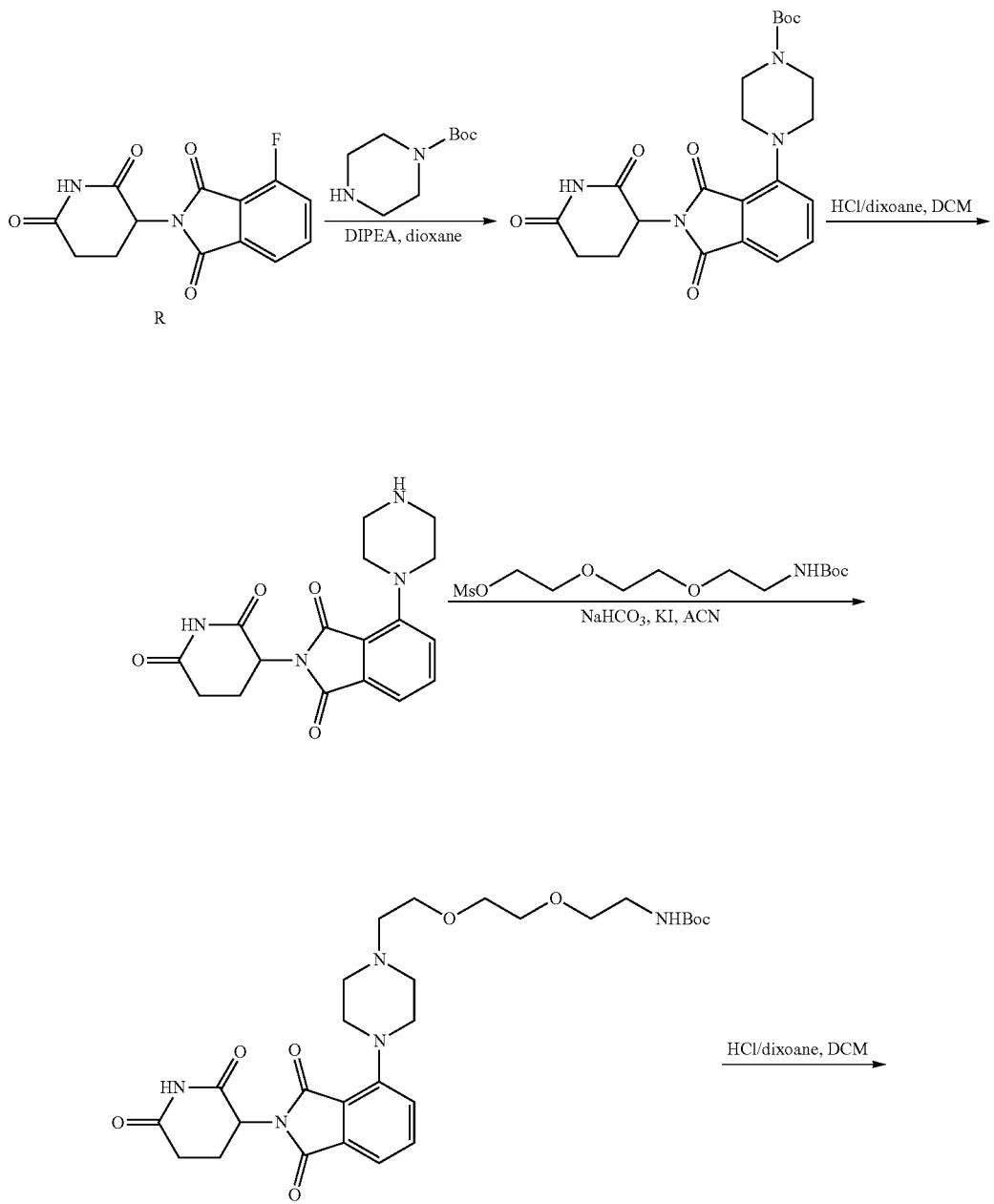

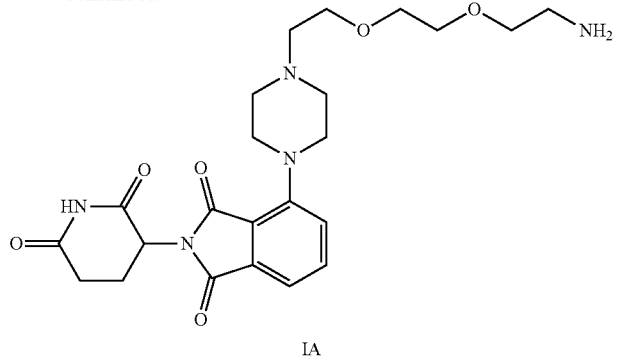

IA

Step 1—Tert-butyl 4-[2-(2,6-dioxo-3-piperidyl)-1,3-dioxo-isoindolin-4-yl]piperazine-1-carboxylate To a solution of 2-(2,6-dioxo-3-piperidyl)-4-fluoro-isoindoline-1,3-dione (500 mg, 1.81 mmol, Intermediate R), and tert-butyl piperazine-1-carboxylate (404 mg, 2.17 mmol, CAS #143238-38-4) in dioxane (5.00 mL) was added DIPEA (1.17 g, 9.05 mmol). The mixture was stirred at 115° C. for 16 hrs. On completion, the mixture was concentrated in vacuo. The mixture was purified by reverse phase chromatography (0.1% HCl) to give the title compound (270 mg, 33% yield) as yellow solid. LC-MS (ESI$^+$) m/z 465.2 (M+Na)$^+$.

Step 2—2-(2,6-Dioxo-3-piperidyl)-4-piperazin-1-yl-isoindoline-1,3-dione

To a solution of tert-butyl 4-[2-(2,6-dioxo-3-piperidyl)-1,3-dioxo-isoindolin-4-yl]piperazine-1-carboxylate (270 mg, 610 umol) in DCM (2.00 mL) was added HCl/dioxane (4.00 M, 3.00 mL). The mixture was stirred at 15° C. for 0.5 hour. On completion, the mixture was concentrated in vacuo to give the title compound (230 mg, 95% yield, HCl) as a yellow solid. $^1$H NMR (400 MHz, DMSO-d$_6$) δ 11.12 (s, 1H), 9.22 (s, 1H), 7.80-7.74 (m, 1H), 7.49-7.39 (m, 2H), 5.16-5.08 (m, 1H), 3.53-3.48 (m, 4H), 3.33-3.19 (m, 4H), 2.95-2.83 (m, 1H), 2.70-2.61 (m, 1H), 2.59-2.53 (m, 1H), 2.10-1.97 (m, 1H).

Step 3—Tert-butyl N-[2-[2-[2-[4-[2-(2,6-dioxo-3-piperidyl)-1,3-dioxo-isoindolin-4-yl]piperazin-1-yl]ethoxy]ethoxy]ethyl]carbamate To a solution of 2-(2,6-dioxo-3-piperidyl)-4-piperazin-1-yl-isoindoline-1,3-dione (100 mg, 263 umol, HCl), 2-[2-[2-(tert-butoxycarbonylamino)ethoxy]ethoxy]ethyl methanesulfonate (86.4 mg, 263 umol, synthesized via Step 1 of Intermediate AM) in ACN (5.00 mL) was added KI (4.38 mg, 26.4 umol) and NaHCO$_3$ (66.5 mg, 791 umol). The mixture was stirred at 80° C. for 16 hours. On completion, the mixture was concentrated in vacuo to give the title compound (100 mg, 60% yield) as yellow solid. LC-MS (ESI$^+$) m/z 574.4 (M+H)$^+$.

Step 4—4-[4-[2-[2-(2-Aminoethoxy)ethoxy]ethyl]piperazin-1-yl]-2-(2,6-dioxo-3-piperidyl)isoindoline-1,3-dione To a solution of tert-butyl N-[2-[2-[2-[4-[2-(2,6-dioxo-3-piperidyl)-1,3-dioxo-isoindolin-4-yl]piperazin-1-yl]ethoxy]ethoxy]ethyl]carbamate (70.0 mg, 122 umol) in DCM (2.00 mL) was added HCl/dioxane (4.00 M, 4.00 mL). The mixture was stirred at 15° C. for 0.5 hour. On completion, the mixture was concentrated in vacuo to give the title compound (60.0 mg, 80% yield, HCl) as yellow solid. LC-MS (ESI$^+$) m/z 474.3 (M+H)$^+$.

5-[4-[2-[2-(2-Aminoethoxy)ethoxy]ethyl]piperazin-1-yl]-2-(2,6-dioxo-3-piperidyl)isoindoline-1,3-dione (Intermediate IB)

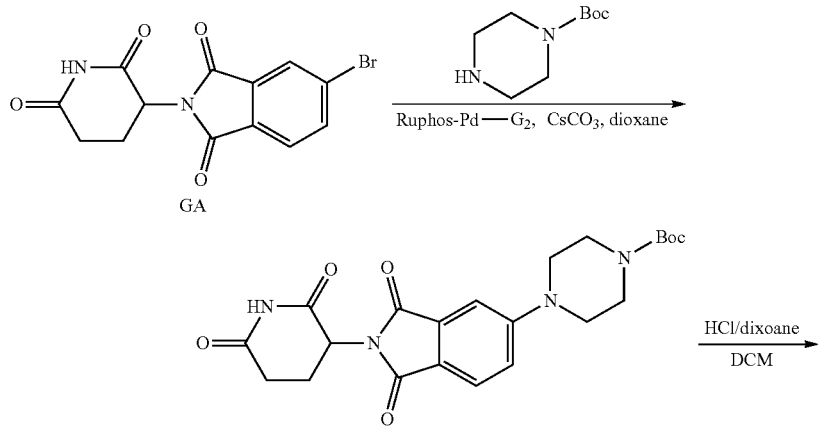

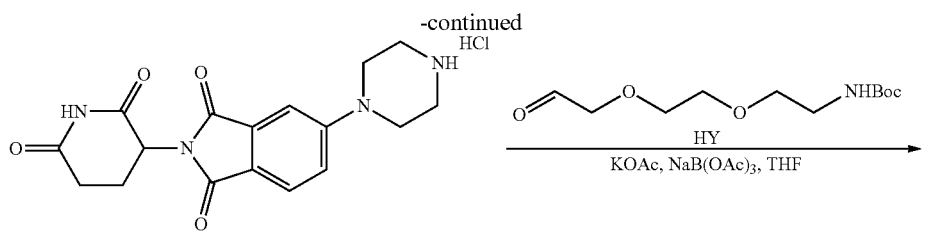

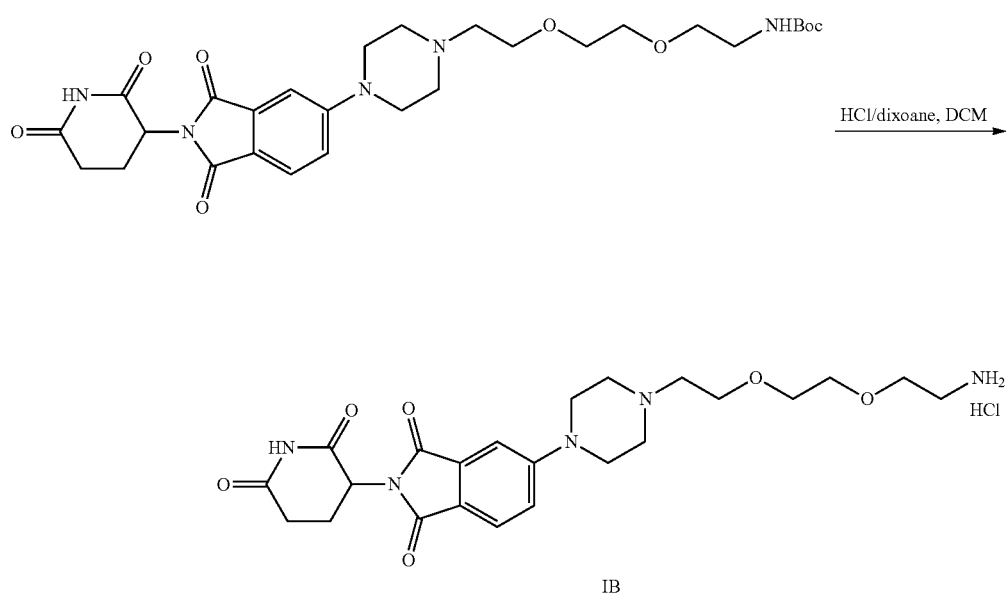

Step 1—Tert-butyl 4-[2-(2,6-dioxo-3-piperidyl)-1,3-dioxo-isoindolin-5-yl]piperazine-1-carboxylate 5-Bromo-2-(2,6-dioxo-3-piperidyl)isoindoline-1,3-dione (0.5 g, 1.48 mmol, Intermediate GA), tert-butyl piperazine-1-carboxylate (552 mg, 2.97 mmol), $Cs_2CO_3$ (966 mg, 2.97 mmol) and [2-(2-aminophenyl)phenyl]-chloro-palladium; dicyclohexyl-[2-(2,6-diisopropoxyphenyl)phenyl]-phosphane (115 mg, 148 umol, CAS #1375325-68-0) in dioxane (10 mL) was degassed and then heated to 80° C. for 15 hours under $N_2$. On completion, the mixture was filtered and the filtrate was concentrated in vacuo. The residue was purified by silica gel chromatography to give the title compound (100 mg, 14% yield) as a yellow solid. LC-MS ($ESI^+$) m/z 465.1 $(M+Na)^+$.

Step 2—2-(2,6-Dioxo-3-piperidyl)-5-piperazin-1-yl-isoindoline-1,3-dione

To a solution of tert-butyl 4-[2-(2,6-dioxo-3-piperidyl)-1,3-dioxo-isoindolin-5-yl]piperazine-1-carboxylate (70 mg, 142 umol) in DCM (1 mL) was added HCl/dioxane (2 mL). The reaction mixture was stirred at 20° C. for 1 hr. On completion, the mixture was concentrated in vacuo to give the title compound (53.0 mg, 98% yield, HCl) as a yellow solid. LC-MS ($ESI^+$) m/z 343.1 $(M+H)^+$.

Step 3—Tert-butyl N-[2-[2-[2-[4-[2-(2,6-dioxo-3-piperidyl)-1,3-dioxo-isoindolin-5-yl]piperazin-1-yl]ethoxy]ethoxy]ethyl]carbamate To a solution of 2-(2,6-dioxo-3-piperidyl)-5-piperazin-1-yl-isoindoline-1,3-dione (53 mg, 140 umol, HCl) and tert-butyl N-[2-[2-(2-oxoethoxy)ethoxy]ethyl]carbamate (45 mg, 182 umol, Intermediate HY) in THF (10 mL) was added KOAc (27.5 mg, 280 umol). One hour later, $NaBH(OAc)_3$ (59.3 mg, 280 umol) was added and the reaction mixture was stirred at 20° C. for 14 hrs. On completion, the mixture was concentrated in vacuo. The residue was purified by silica gel chromatography ($SiO_2$) to give the title compound (70 mg, 87% yield) as yellow oil. LC-MS ($ESI^+$) m/z 574.3 $(M+H)^+$.

Step 4—5-[4-[2-[2-(2-Aminoethoxy)ethoxy]ethyl]piperazin-1-yl]-2-(2,6-dioxo-3-piperidyl)isoindoline-1,3-dione To a solution of tert-butyl N-[2-[2-[2-[4-[2-(2,6-dioxo-3-piperidyl)-1,3-dioxo-isoindolin-5-yl]piperazin-1-yl]ethoxy]ethoxy]ethyl]carbamate (90.0 mg, 157 umol) in DCM (2 mL) was added HCl/dioxane (4 mL). The reaction mixture was stirred at 20° C. for 3 hrs. On completion, the mixture was concentrated in vacuo to give the title compound (80 mg, 100% yield, HCl) as a yellow solid. LC-MS ($ESI^+$) m/z 474.2 $(M+H)^+$.

5-[[1-[2-[2-(2-Aminoethoxy)ethoxy]ethyl]azetidin-3-yl]amino]-2-(2,6-dioxo-3-piperidyl) isoindoline-1,3-dione (Intermediate IC)

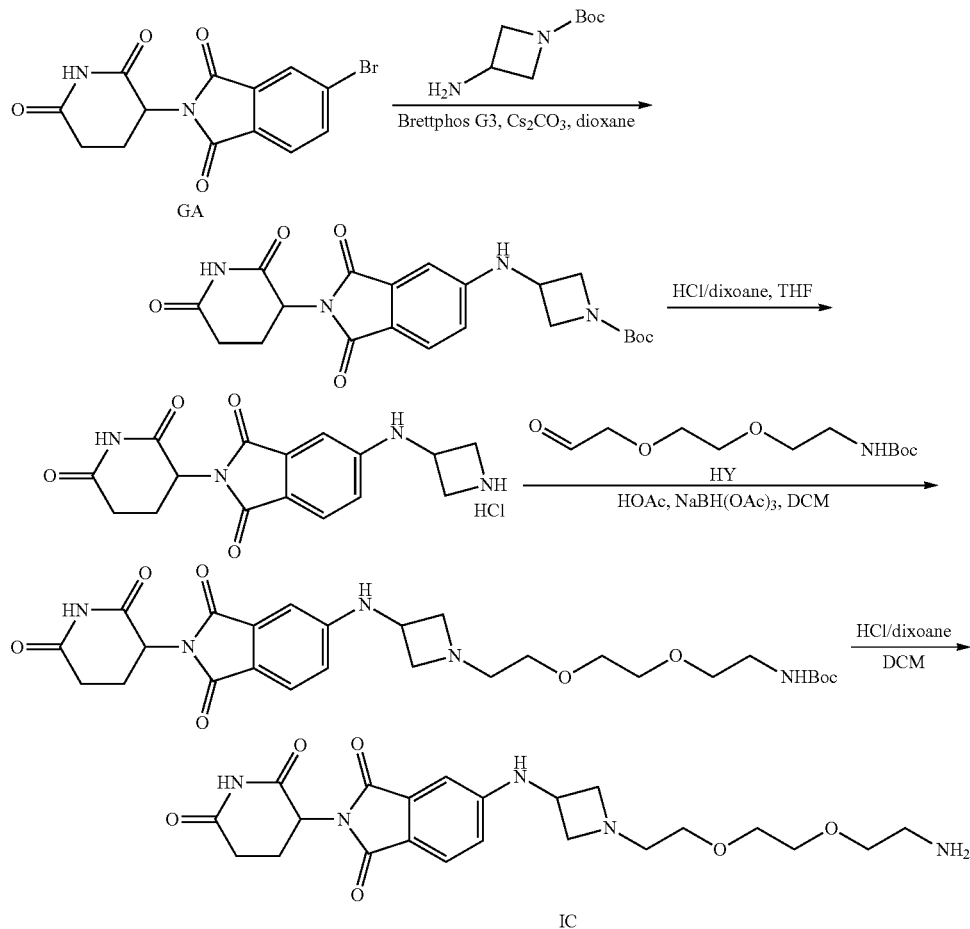

Step 1—Tert-butyl 3-[[2-(2,6-dioxo-3-piperidyl)-1,3-dioxo-isoindolin-5-yl]amino]azetidine-1-carboxylate A mixture of 5-bromo-2-(2,6-dioxo-3-piperidyl)isoindoline-1,3-dione (500 mg, 1.48 mmol, Intermediate GA), tert-butyl 3-aminoazetidine-1-carboxylate (383 mg, 2.22 mmol, CAS #193269-78-2), Brettphos-G3 (134 mg, 148 umol), and $Cs_2CO_3$ (1.45 g, 4.45 mmol) in dioxane (50 mL) was degassed and purged with $N_2$ 3 times. Then the mixture was stirred at 90° C. for 2 hours under $N_2$ atmosphere. On completion, the mixture was concentrated in vacuo. The residue was purified by pre-HPLC to give the title compound (90.0 mg, 13% yield) as yellow solid. LC-MS (ESI$^+$) m/z 451.1 (M+Na)$^+$.

Step 2—5-(Azetidin-3-ylamino)-2-(2,6-dioxo-3-piperidyl)isoindoline-1,3-dione To a solution of tert-butyl 3-[[2-(2,6-dioxo-3-piperidyl)-1,3-dioxo-isoindolin-5-yl]amino]azetidine-1-carboxylate (100 mg, 233 umol) in THF (5 mL) was added HCl/dioxane (4 M, 5 mL). The mixture was stirred at 20° C. for 2 hours. On completion, the mixture was concentrated in vacuo to give the title compound (85.0 mg, 99% yield) as yellow solid. LC-MS (ESI$^+$) m/z 329.0 (M+H)$^+$.

Step 3—Tert-butyl N-[2-[2-[2-[3-[[2-(2,6-dioxo-3-piperidyl)-1,3-dioxo-isoindolin-5-yl]amino]azetidin-1-yl]ethoxy]ethoxy]ethyl]carbamate To a mixture of 5-(azetidin-3-ylamino)-2-(2,6-dioxo-3-piperidyl)isoindoline-1,3-dione (85.0 mg, 233 umol), tert-butyl N-[2-[2-(2-oxoethoxy)ethoxy]ethyl]carbamate (57.6 mg, 233 umol, Intermediate HY) in THF (10 mL) and DMF (10 mL) was added TEA (23.5 mg, 233 umol, 32.4 uL). The reaction mixture was stirred for 0.5 hour. Then HOAc (13.9 mg, 233 umol) and NaBH(OAc)$_3$ (98.7 mg, 466 umol) was added to the reaction mixture, and the mixture was stirred at 20° C. for 48 hours under $N_2$ atmosphere. On completion, the mixture was concentrated in vacuo. The residue was purified by prep-HPLC to give the title compound (60.0 mg, 40% yield) as yellow oil. LC-MS (ESI$^+$) m/z 560.4 (M+H)$^+$.

Step 4—5-[[1-[2-[2-(2-Aminoethoxy)ethoxy]ethyl] azetidin-3-yl]amino]-2-(2,6-dioxo-3-piperidyl) isoindoline-1,3-dione To a solution of tert-butyl N-[2-[2-[2-[3-[[2-(2,6-dioxo-3-piperidyl)-1,3-dioxo-isoindolin-5-yl]amino]azetidin-1-yl]

ethoxy]ethoxy]ethyl]carbamate (60.0 mg, 107 umol) in THF (5 mL) was added HCl/dioxane (4 M, 4 mL). The mixture was stirred at 25° C. for 2 hrs. On completion, the mixture was concentrated in vacuo to give the title compound (50.0 mg, 95% yield) as yellow solid. LC-MS (ESI$^+$) m/z 460.3 (M+H)$^+$.

Tert-butyl N-[2-[2-(2-azidoethoxy)ethoxy]ethyl] carbamate (Intermediate ID)

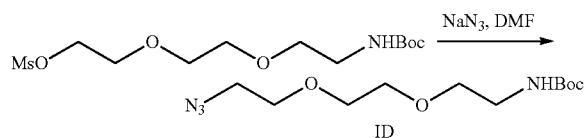

To a solution of 2-[2-[2-(tert-butoxycarbonylamino) ethoxy]ethoxy]ethyl methanesulfonate (2.30 g, 7.03 mmol, synthesized via Step 1 of Intermediate AM) in DMF (20 mL) was added NaN$_3$ (913 mg, 14.1 mmol). The reaction mixture was stirred at 80° C. for 12 hrs. On completion, the mixture was diluted with water (50 mL), and extracted with DCM (2×30 mL). The organic layer was washed with brine (50 mL), dried under N$_2$ to give the title compound (1.60 g, 83% yield) as yellow oil. LC-MS (ESI$^+$) m/z 297.1 (M+Na)$^+$.

4-[[1-[2-[2-(2-Aminoethoxy)ethoxy]ethyl]triazol-4-yl]methylamino]-2-(2,6-dioxo-3-piperidyl)isoindoline-1,3-dione (Intermediate IE)

ID), CuSO$_4$ (507 ug, 3.18 umol) and sodium; (2R)-2-[(1S)-1,2-dihydroxyethyl]-4-hydroxy-5-oxo-2H-furan-3-olate (1.26 mg, 6.36 umol) in a mixed solvent of H$_2$O (2 mL) and t-BuOH (2 mL) was added 2-(2,6-dioxo-3-piperidyl)-4-(prop-2-ynylamino)isoindoline-1,3-dione (200 mg, 636 umol, Intermediate DN). The reaction mixture was stirred at 60° C. for 2 hours. On completion, the reaction mixture was diluted with water (10 mL) and extracted with EA (20 mL×3). The combined organic layers dried over Na$_2$SO$_4$, filtered and concentrated in vacuo to give a residue. The residue was purified by silica gel chromatography (PE/EA=1/1) to give the title compound (0.30 g, 78% yield) as yellow solid. $^1$H NMR (400 MHz, DMSO-d$_6$) δ 11.11 (s, 1H), 7.99 (s, 1H), 7.57 (t, J=7.8 Hz, 1H), 7.18 (d, J=8.8 Hz, 1H), 7.12-7.02 (m, 2H), 6.76 (t, J=5.2 Hz, 1H), 5.06 (dd, J=5.2, 12.8 Hz, 1H), 4.60 (d, J=6.0 Hz, 2H), 4.48 (t, J=5.2 Hz, 2H), 3.78 (t, J=5.2 Hz, 2H), 3.52-3.38 (m, 4H), 3.33-3.28 (m, 2H), 3.03 (q, J=5.6 Hz, 2H), 2.95-2.82 (m, 1H), 2.63-2.52 (m, 2H), 2.08-1.99 (m, 1H), 1.36 (s, 9H); LC-MS (ESI$^+$) m/z 586.4 (M+H)$^+$.

Step 2—4-[[1-[2-[2-(2-Aminoethoxy)ethoxy]ethyl] triazol-4-yl]methylamino]-2-(2,6-dioxo-3-piperidyl) isoindoline-1,3-dione To a solution of tert-butyl N-[2-[2-[2-[4-[[[2-(2,6-dioxo-3-piperidyl)-1,3-dioxo-isoindolin-4-yl]amino]methyl]tri-

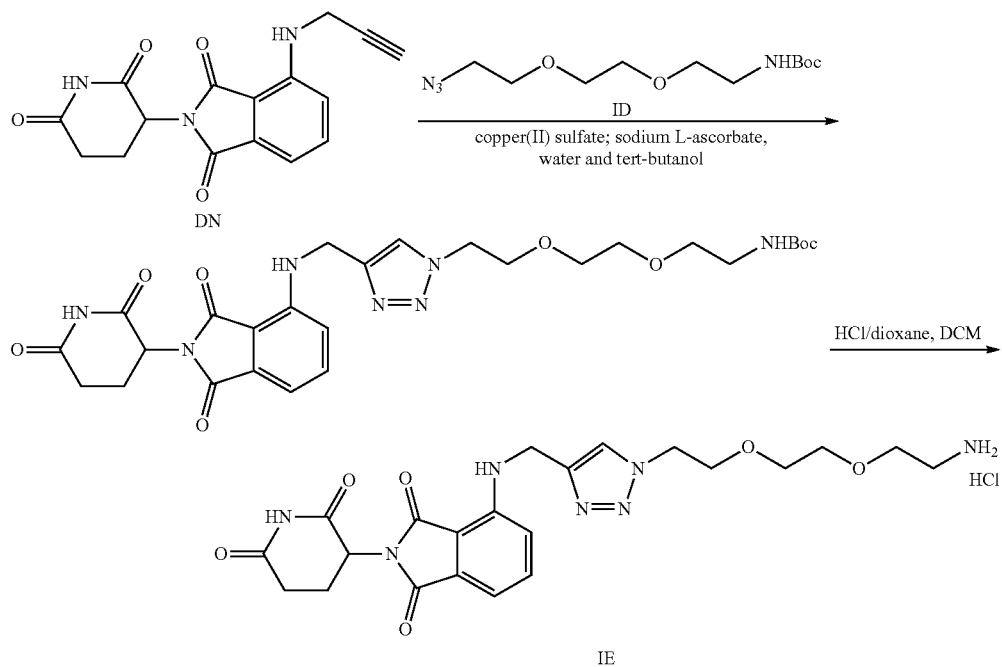

Step 1—Tert-butyl N-[2-[2-[2-[4-[[[2-(2,6-dioxo-3-piperidyl)-1,3-dioxo-isoindolin-4-yl]amino]methyl] triazol-1-yl]ethoxy]ethoxy]ethyl]carbamate To a solution of tert-butyl N-[2-[2-(2-azidoethoxy) ethoxy]ethyl]carbamate (348 mg, 1.27 mmol, Intermediate azol-1-yl]ethoxy]ethoxy]ethyl]carbamate (0.30 g, 502 umol) in DCM (6 mL) was added HCl/dioxane (4 M, 2.94 mL). The mixture was stirred at 5° C. for 0.5 hour. On completion, the reaction mixture was concentrated in vacuo to give the title compound (0.22 g, 84% yield) as yellow solid. LC-MS (ESI$^+$) m/z 486.3 (M+H)$^+$.

2-(2,6-Dioxo-3-piperidyl)-5-(prop-2-ynylamino) isoindoline-1,3-dione (Intermediate IF)

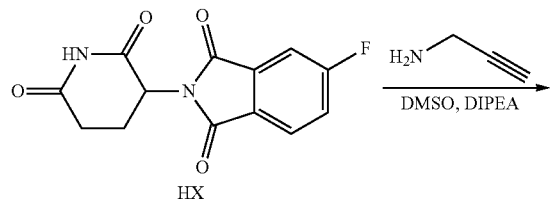

mixture was stirred at 130° C. for 1.5 hours. On completion, the mixture was diluted with water (40 mL), and extracted with DCM (2×30 mL). The organic layers were washed with brine (40 mL), and concentrated in vacuo. The residue was purified by silica gel chromatography to give the title compound (0.25 g, 27% yield) as a yellow solid. LC-MS (ESI$^+$) m/z 312.2 (M+H)$^+$.

5-[[1-[2-[2-(2-Aminoethoxy)ethoxy]ethyl]triazol-4-yl]methylamino]-2-(2,6-dioxo-3-piperidyl) isoindoline-1,3-dione (Intermediate IG)

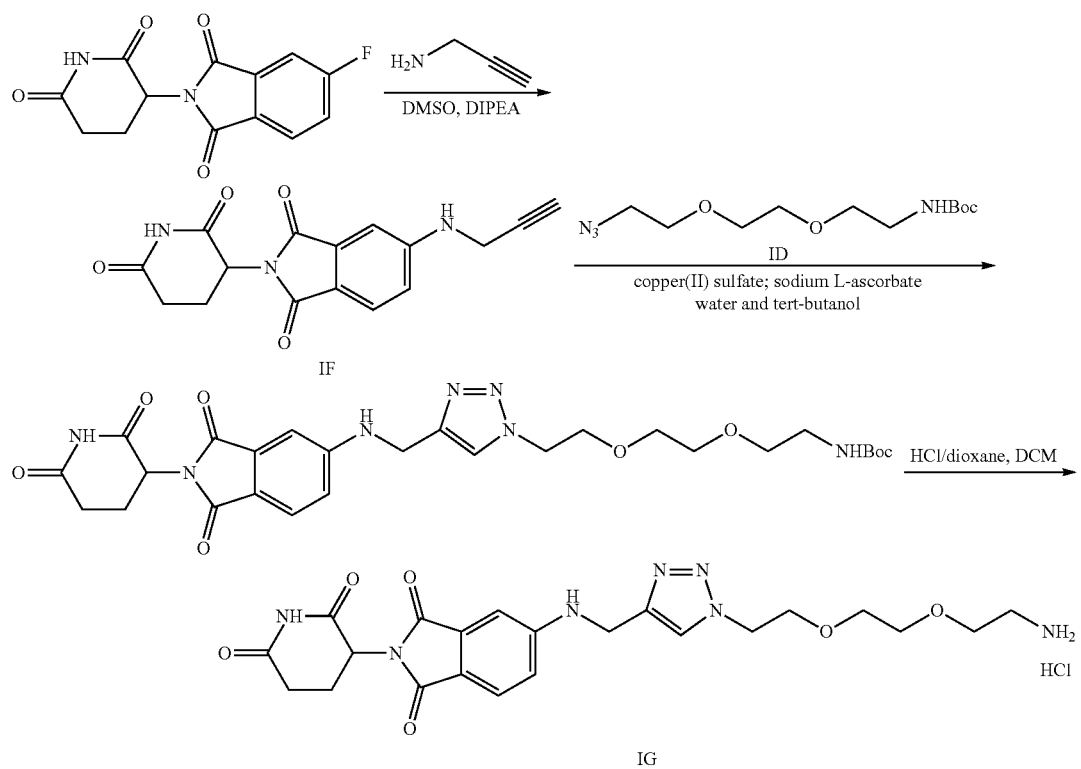

-continued

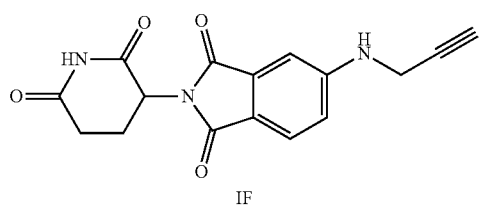

To a solution of 2-(2,6-dioxo-3-piperidyl)-5-fluoro-isoindoline-1,3-dione (700 mg, 2.53 mmol, Intermediate HX) and prop-2-yn-1-amine (209 mg, 3.80 mmol) in DMSO (10 mL) was added DIPEA (983 mg, 7.60 mmol). The reaction Step 1—Tert-butyl N-[2-[2-[2-[4-[[[2-(2,6-dioxo-3-piperidyl)-1,3-dioxo-isoindolin-5-yl]amino]methyl]triazol-1-yl]ethoxy]ethoxy]ethyl]carbamate To a solution of 2-(2,6-dioxo-3-piperidyl)-5-(prop-2-ynylamino)isoindoline-1,3-dione (200 mg, 546 umol, Intermediate IF) and tert-butyl N-[2-[2-(2-azidoethoxy)ethoxy] ethyl]carbamate (300 mg, 1.09 mmol, Intermediate ID) in a mixed solvent of H$_2$O (3 mL) and t-BuOH (3 mL) was added CuSO$_4$ (872 ug, 5.46 umol) and sodium; (2R)-2-[(1S)-1,2-dihydroxyethyl]-4-hydroxy-5-oxo-2H-furan-3-olate (2.16 mg, 10.9 umol). The reaction mixture was stirred at 60° C. for 2 hrs. On completion, the mixture was diluted with water (30 mL), and extracted with DCM (30 mL). The organic layers were concentrated in vacuo. The residue was purified by silica gel chromatography to give the title compound (240 mg, 75% yield) as a yellow solid. LC-MS (ESI$^+$) m/z 586.1 (M+H)$^+$.

Step 2—5-[[1-[2-[2-(2-Aminoethoxy)ethoxy]ethyl]triazol-4-yl]methylamino]-2-(2,6-dioxo-3-piperidyl)isoindoline-1,3-dione To a solution of tert-butyl N-[2-[2-[2-[4-[[[2-(2,6-dioxo-3-piperidyl)-1,3-dioxo-isoindolin-5-yl]amino]methyl]triazol-1-yl]ethoxy]ethoxy]ethyl]carbamate (240 mg, 410 umol) in DCM (2 mL) was added HCl/dioxane (4 mL). The reaction mixture was stirred at 20° C. for 12 hrs. On completion, the mixture was concentrated in vacuo to give the title compound (210 mg, 98% yield, HCl) as a yellow solid. LC-MS (ESI$^+$) m/z 486.1 (M+H)$^+$.

4-[2-[3-[2-[2-(2-Aminoethoxy)ethoxy]ethyl]triazol-4-yl]ethylamino]-2-(2,6-dioxo-3-piperidyl) isoindoline-1,3-dione (Intermediate IH tion) to give the title compound (230 mg, 49% yield) as a yellow solid. $^1$H NMR (400 MHz, DMSO-d$_6$) δ 11.11 (s, 1H), 7.63-7.56 (m, 1H), 7.17 (d, J=8.8 Hz, 1H), 7.06 (d, J=7.2 Hz, 1H), 6.72 (t, J=6.0 Hz, 1H), 5.07 (dd, J=5.2, 12.8 Hz, 1H), 3.70 (t, J=7.0 Hz, 1H), 3.48 (q, J=6.8 Hz, 2H), 2.96-2.83 (m, 3H), 2.57-2.53 (m, 2H), 2.09-1.99 (m, 1H); LC-MS (ESI$^+$) m/z 326.1 (M+H)$^+$.

Step 2—Tert-butyl (2-(2-(2-(5-(2-((2-(2,6-dioxopiperidin-3-yl)-1,3-dioxoisoindolin-4-yl)amino)ethyl)-1H-1,2,3-triazol-1-yl)ethoxy)ethoxy)ethyl)carbamate To a solution of 4-(but-3-ynylamino)-2-(2,6-dioxo-3-piperidyl)isoindoline-1,3-dione (280 mg, 861 umol) and tert-butyl N-[2-[2-(2-azidoethoxy)ethoxy]ethyl]carbamate (472 mg, 1.72 mmol, Intermediate ID) in THF (5 mL) was added chlororuthenium (1+); 1,2,3,4,5-pentamethylcyclopenta-1,

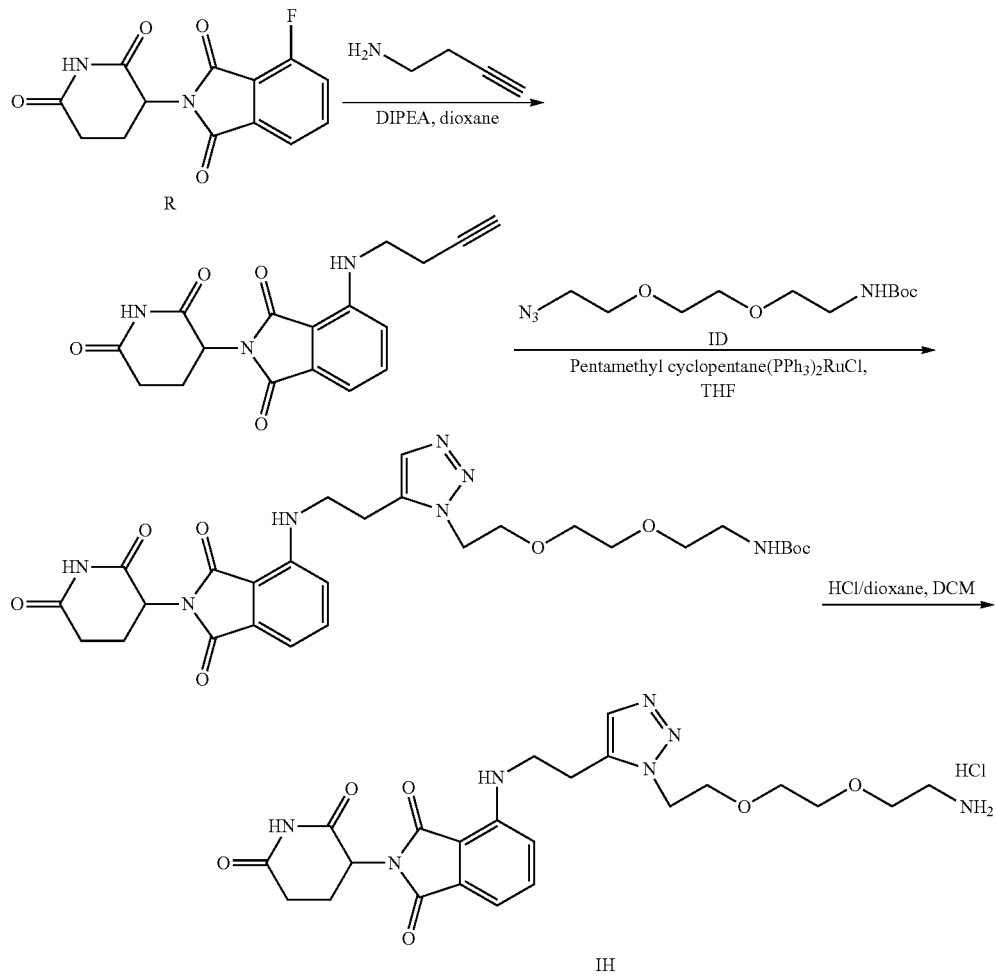

Step 1—4-(But-3-yn-1-yl amino)-2-(2,6-dioxopiperidin-3-yl)isoindoline-1,3-dione To a solution of 2-(2,6-dioxo-3-piperidyl)-4-fluoro-isoindoline-1,3-dione (400 mg, 1.45 mmol, Intermediate R) and but-3-yn-1-amine (120 mg, 1.74 mmol) in dioxane (10 mL) was added DIPEA (561 mg, 4.34 mmol). The reaction mixture was stirred at 115° C. for 12 hrs. On completion, the reaction mixture was concentrated in vacuo. The crude product was purified by reversed phase (0.1% HCl condi- 3-diene; triphenylphosphane (13.7 mg, 17.2 umol, CAS: 92361-49-4). The reaction mixture was stirred at 65° C. for 12 hrs under N$_2$. On completion, the reaction mixture was filtered and concentrated in vacuo. The crude product was purified by silica gel chromatography (EA:ACN=1:1) to give the title compound (300 mg, 57% yield) as a yellow solid. $^1$H NMR (400 MHz, CDCl$_3$) δ 8.40 (s, 1H), 7.57-7.52 (m, 1H), 7.57-7.52 (m, 1H), 7.28 (s, 1H), 7.16 (d, J=7.2 Hz, 1H), 6.93 (d, J=8.8 Hz, 1H), 6.40 (t, J=5.6 Hz, 1H), 4.92 (d, J=5.6 Hz, 1H), 4.49 (t, J=5.6 Hz, 2H), 3.93 (t, J=5.6 Hz, 2H), 3.65 (q, J=7.2 Hz, 2H), 3.55-3.51 (m, 4H), 3.44 (t, J=5.2 Hz, 2H), 3.27 (d, J=4.8 Hz, 2H), 3.11 (t, J=7.2 Hz, 2H), 2.93-2.74 (m, 3H), 2.22-2.11 (m, 1H), 1.45 (s, 9H); LC-MS (ESI$^+$) m/z 600.1 (M+H)$^+$.

Step 3—4-[2-[3-[2-[2-(2-Aminoethoxy)ethoxy]ethyl]triazol-4-yl]ethylamino]-2-(2,6-dioxo-3-piperidyl) isoindoline-1,3-dione To a solution of tert-butyl N-[2-[2-[2-[5-[2-[[2-(2,6-dioxo-3-piperidyl)-1,3-dioxo-isoindolin-4-yl]amino]ethyl]triazol-1-yl]ethoxy]ethoxy]ethyl]carbamate (300 mg, 500 umol) in DCM (5 mL) was added HCl/dioxane (4 M, 7.50 mL). The reaction mixture was stirred at 20° C. for 0.5 hr. On completion, the reaction mixture was concentrated in vacuo to give the title compound (268 mg, 100% yield, HCl salt) as yellow solid. LC-MS (ESI$^+$) m/z 500.1 (M+H)$^+$.

4-[[1-[2-[2-(2-Aminoethoxy)ethoxy]ethyl]triazol-4-yl]methoxy]-2-(2,6-dioxo-3-piperidyl) isoindoline-1,3-dione (Intermediate II)

Step 1—2-(2,6-Dioxo-3-piperidyl)-4-prop-2-ynoxy-isoindoline-1,3-dione

To a solution of 2-(2,6-dioxo-3-piperidyl)-4-hydroxy-isoindoline-1,3-dione (3.00 g, 10.9 mmol, synthesized via Step 1 of Intermediate CA) in DMF (30 mL) was added K$_2$CO$_3$ (1.66 g, 12.0 mmol). Then 3-bromoprop-1-yne (1.43 g, 12.0 mmol) was added and the mixture was stirred at 20° C. for 12 hrs. On completion, the mixture was diluted with water (200 mL), stirred and filtered. The filter cake was purified by reverse phase (0.1% HCl condition) to give the title compound (0.90 g, 26% yield) as a light yellow solid. LC-MS (ESI$^+$) m/z 313.1 (M+H)$^+$.

Step 2—Tert-butyl N-[2-[2-[2-[4-[[2-(2,6-dioxo-3-piperidyl)-1,3-dioxo-isoindolin-4-yl]oxymethyl]triazol-1-yl]ethoxy]ethoxy]ethyl]carbamate To a solution of tert-butyl N-[2-[2-(2-azidoethoxy)ethoxy]ethyl]carbamate (527 mg, 1.92 mmol, Intermediate ID), CuSO$_4$ (1.53 mg, 9.61 umol) and sodium; (2R)-2-[(1S)-1,2-dihydroxyethyl]-4-hydroxy-5-oxo-2H-furan-3-olate (3.81 mg, 19.2 umol) in a mixed solvent of H$_2$O (3 mL) and t-BuOH (3 mL) was added 2-(2,6-dioxo-3-piperidyl)-4-prop-2-ynoxy-isoindoline-1,3-dione (300 mg, 961 umol). The reaction mixture was stirred at 60° C. for 2 hrs. On completion, the mixture was diluted with H$_2$O (20 mL), and extracted with EA (2×30 mL). The organic layer was washed with brine (50 mL), dried over Na$_2$SO$_4$, filtered and concentrated in vacuo. The residue was purified by silica gel chromatography to give the title compound (460 mg, 82% yield) as a white solid. LC-MS (ESI$^+$) m/z 587.3 (M+H)$^+$.

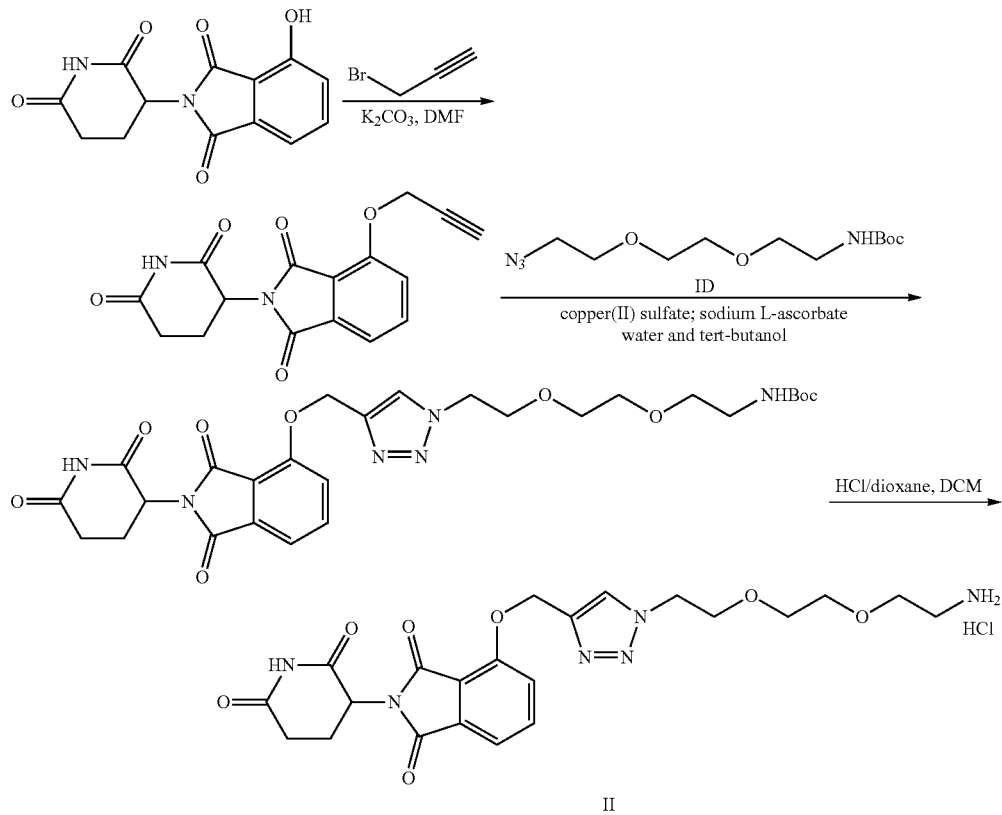

Step 3—4-[[1-[2-[2-(2-Aminoethoxy)ethoxy]ethyl]triazol-4-yl]methoxy]-2-(2,6-dioxo-3-piperidyl) isoindoline-1,3-dione To a solution of tert-butyl N-[2-[2-[2-[4-[[2-(2,6-dioxo-3-piperidyl)-1,3-dioxo-isoindolin-4-yl]oxymethyl]triazol-1-yl]ethoxy]ethoxy]ethyl]carbamate (105 mg, 179 umol) in DCM (2 mL) was added HCl/dioxane (3 mL). The reaction mixture was stirred at 20° C. for 1 hr. On completion, the mixture was concentrated in vacuo to give the title compound (93.0 mg, 99% yield, HCl) as a white solid. LC-MS (ESI$^+$) m/z 487.2 (M+H)$^+$.

4-[2-[3-[2-[2-(2-Aminoethoxy)ethoxy]ethyl]triazol-4-yl]ethoxy]-2-(2,6-dioxo-3-piperidyl) isoindoline-1,3-dione (Intermediate IJ)

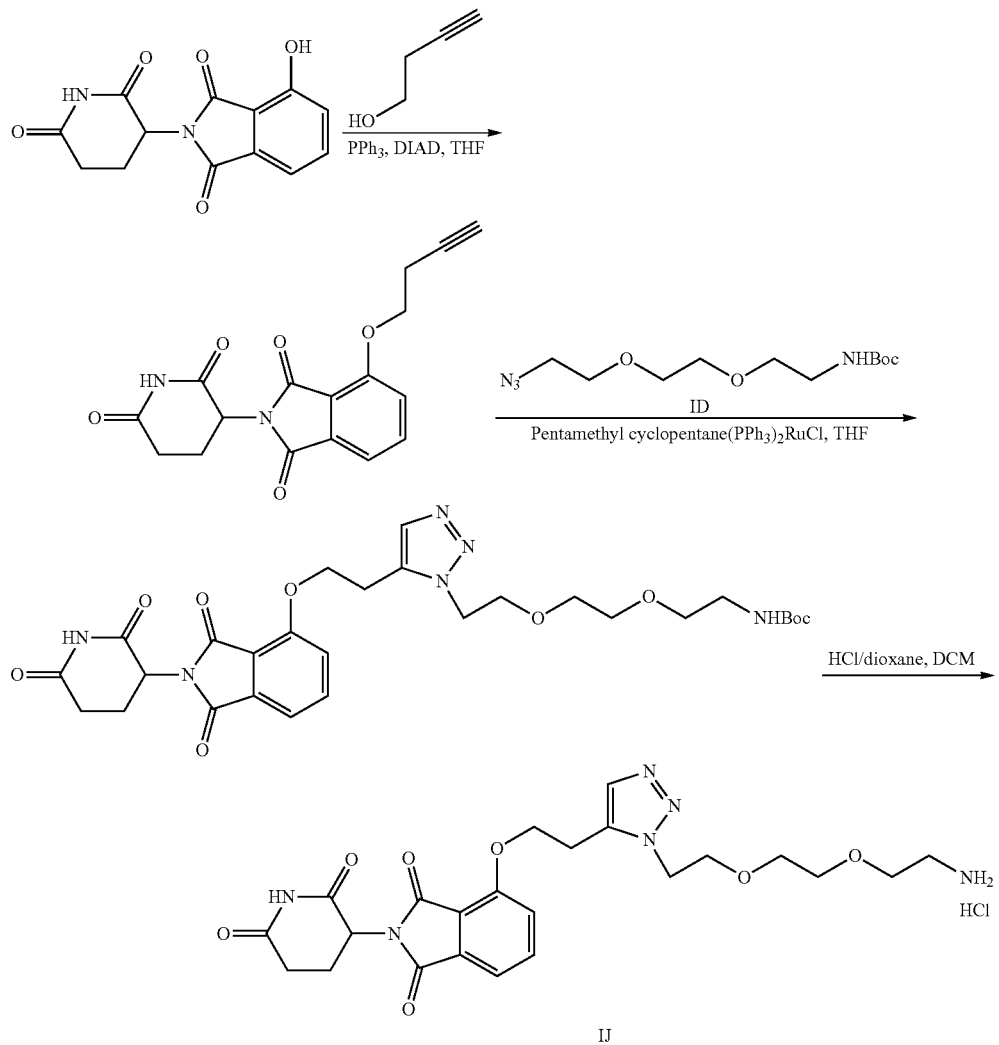

Step 1—4-But-3-ynoxy-2-(2,6-dioxo-3-piperidyl) isoindoline-1,3-dione

To a solution of 2-(2,6-dioxo-3-piperidyl)-4-hydroxy-isoindoline-1,3-dione (1 g, 3.65 mmol, synthesized via Step 1 of Intermediate CA) and but-3-yn-1-ol (307 mg, 4.38 mmol, CAS #927-74-2) in THF (10 mL) was added PPh$_3$ (1.43 g, 5.47 mmol). Then a solution of DIAD (1.47 g, 7.29 mmol, 1.42 mL, 2.0 eq) in THF (10 mL) was added into the above mixture dropwise at 0° C. The reaction mixture was stirred at 20° C. for 12 hrs. On completion, the mixture was concentrated in vacuo. The residue was purified by reverse phase (0.1% HCl condition) to give the title compound (0.7 g, 59% yield) as an off-white solid. $^1$H NMR (300 MHz, DMSO-d$_6$) δ 11.12 (s, 1H), 7.86-7.76 (m, 1H), 7.54 (d, J=8.4 Hz, 1H), 7.47 (d, J=7.2 Hz, 1H), 5.08 (dd, J=5.2, 12.8 Hz, 1H), 4.31 (t, J=6.8 Hz, 2H), 2.92 (t, J=2.8 Hz, 1H), 2.90-2.80 (m, 1H), 2.75-2.66 (m, 2H), 2.64-2.52 (m, 2H), 2.09-1.97 (m, 1H).

Step 2—Tert-butyl N-[2-[2-[2-[5-[2-[2-(2,6-dioxo-3-piperidyl)-1,3-dioxo-isoindolin-4-yl]oxyethyl]triazol-1-yl]ethoxy]ethoxy]ethyl]carbamate To a solution of 4-but-3-ynoxy-2-(2,6-dioxo-3-piperidyl) isoindoline-1,3-dione (0.25 g, 766 umol) and tert-butyl N-[2-[2-(2-azidoethoxy)ethoxy]ethyl]carbamate (420 mg, 1.53 mmol, Intermediate ID) in THF (8 mL) was added chlororuthenium (1+); 1,2,3,4,5-pentamethylcyclopenta-1,3-diene; triphenylphosphane (30.5 mg, 38.3 umol, CAS #92361-49-4). The reaction mixture was stirred at 65° C. for 15 hrs. On completion, the mixture was concentrated in vacuo. The residue was purified by silica gel chromatography (SiO$_2$) to give the title compound (330 mg, 68% yield) as a white solid. LC-MS (ESI$^+$) m/z 601.2 (M+H)$^+$.

Step 3—4-[2-[3-[2-[2-(2-Aminoethoxy)ethoxy]ethyl]triazol-4-yl]ethoxy]-2-(2,6-dioxo-3-piperidyl)isoindoline-1,3-dione To a solution of tert-butyl N-[2-[2-[2-[5-[2-[2-(2,6-dioxo-3-piperidyl)-1,3-dioxo-isoindolin-4-yl]oxyethyl]triazol-1-yl]ethoxy]ethoxy]ethyl]carbamate (330 mg, 522 umol) in DCM (2 mL) was added HCl/dioxane (4 mL). The reaction mixture was stirred at 20° C. for 12 hrs. On completion, the mixture was concentrated in vacuo to give the title compound (280 mg, 100% yield, HCl) as an off-white solid. LC-MS (ESI⁺) m/z 501.1 (M+H)⁺.

2-(2-(((benzyloxy)carbonyl)amino)ethoxy)ethyl methanesulfonate (Intermediate IK)

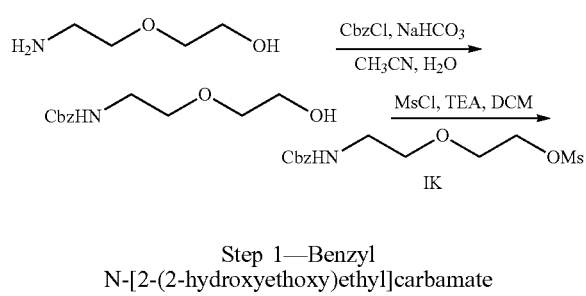

Step 1—Benzyl N-[2-(2-hydroxyethoxy)ethyl]carbamate

To a solution of 2-(2-aminoethoxy)ethanol (5.00 g, 47.5 mmol, 4.76 mL, CAS #929-06-6) and NaHCO₃ (11.9 g, 142 mmol, 5.55 mL) in MeCN (50 mL) and H₂O (50 mL) was added CbzCl (9.74 g, 57.07 mmol, 8.11 mL) dropwise at 0° C. The reaction mixture was stirred at 20° C. for 12 hours. On completion, the mixture was filtered, the filtrate was extracted with EA (2×100 mL), and the organic phase was concentrated in vacuo to give a residue. The residue was purified by flash silica gel chromatography to give the title compound (10.0 g, 87.9% yield) as yellow oil. ¹H NMR (400 MHz, CDCl₃) δ 7.38-7.29 (m, 5H), 5.55 (s, 1H), 5.10 (s, 2H), 3.73-3.69 (m, 2H), 3.57-3.51 (m, 4H), 3.40 (q, J=5.2 Hz, 2H), 2.84 (s, 1H).

Step 2—2-(2-(((benzyloxy)carbonyl)amino)ethoxy)ethyl methanesulfonate (3)—Notebook Page: EW5765-602, EW5765-605

To a solution of benzyl N-[2-(2-hydroxyethoxy)ethyl]carbamate (1 g, 4.18 mmol) and TEA (1.27 g, 12.5 mmol, 1.75 mL) in DCM (10 mL) was added MsCl (574 mg, 5.02 mmol, 388 uL) at 0° C. The reaction mixture was stirred at 20° C. for 1 hour. On completion, the mixture was quenched with the addition of H₂O (30 mL), then exacted with DCM (2×50 mL). The organic phase was concentrated in vacuo to give a title compound (1.30 g, 98% yield) as yellow oil. LC-MS (ESI⁺) m/z 318.2 (M+H)⁺.

Benzyl N-[2-(2-piperazin-1-ylethoxy)ethyl]carbamate (Intermediate IL)

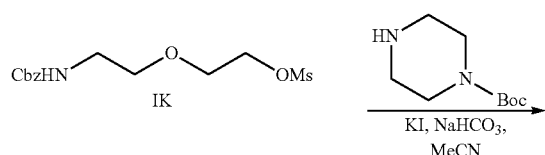

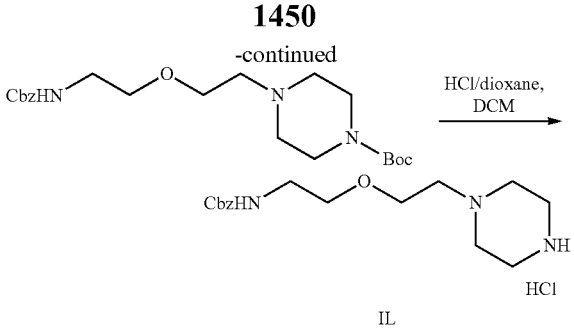

Step 1—tert-butyl 4-(2-(2-(((benzyloxy)carbonyl)amino)ethoxy)ethyl)piperazine-1-carboxylate To a solution of 2-[2-(benzyloxycarbonylamino)ethoxy]ethyl methanesulfonate (6.6 g, 20.8 mmol) and tert-butyl piperazine-1-carboxylate; hydrochloride (4.49 g, 17.3 mmol, HCl, CAS #57260-71-6) in MeCN (100 mL) was added KI (287 mg, 1.73 mmol) and NaHCO₃ (4.37 g, 51.9 mmol, 2.02 mL). The reaction mixture was stirred at 80° C. for 16 hours. On completion, the mixture was filtered, and the filtrate was concentrated in vacuo to give a residue. The residue was purified by column chromatography to give the title compound (5.00 g, 71% yield) as yellow oil. ¹H NMR (400 MHz, CDCl₃) δ 7.39-7.28 (m, 5H), 5.58 (s, 1H), 5.30 (s, 1H), 5.10 (s, 2H), 3.58 (t, J=5.6 Hz, 2H), 3.56-3.50 (m, 2H), 3.47-3.33 (m, 6H), 2.55 (t, J=5.6 Hz, 2H), 2.42 (m, J=4.8 Hz, 4H), 1.46 (s, 9H).

Step 2—Benzyl N-[2-(2-piperazin-1-ylethoxy)ethyl]carbamate

To a solution of tert-butyl 4-[2-[2-(benzyloxycarbonylamino)ethoxy]ethyl]piperazine-1-carboxylate (5.00 g, 12.2 mmol) in DCM (10 mL) was added HCl/dioxane (4 M, 25 mL). The reaction mixture was stirred at 25° C. for 3 hours. On completion, the mixture was concentrated in vacuo to give the title compound (3.80 g, 90% yield) as a yellow solid. LC-MS (ESI⁺) m/z 308.3 (M+H)⁺.

Tert-butyl N-[2-[2-[4-[2-(2-aminoethoxy)ethyl]piperazin-1-yl]ethoxy]ethyl]carbamate (Intermediate IM)

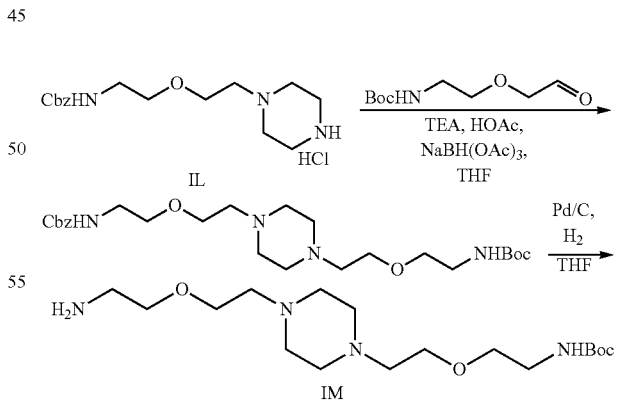

Step 1—Tert-butyl N-[2-[2-[4-[2-[2-(benzyloxycarbonylamino)ethoxy]ethyl]piperazin-1-yl]ethoxy]ethyl]carbamate To a solution of benzyl N-[2-(2-piperazin-1-ylethoxy)ethyl]carbamate (2.00 g, 6.51 mmol, Intermediate IL) in THF (50 mL) was added TEA (1.32 g, 13.0 mmol, 1.81 mL). The mixture was stirred at 25° C. for 30 min, then tert-butyl N-[2-(2-oxoethoxy)ethyl]carbamate (1.85 g, 9.11 mmol, synthesized via Step 1 of Intermediate FS), HOAc (1.17 g, 19.5 mmol, 1.12 mL) and NaBH(OAc)$_3$ (2.76 g, 13.0 mmol) was added in the mixture. The reaction mixture was stirred at 25° C. for 24 hours. On completion, the reaction mixture was concentrated in vacuo to give a residue. The residue was purified by reverse phase (0.1% FA condition) to give the title compound (2.00 g, 62% yield) as yellow oil. LC-MS (ESI$^+$) m/z 495.4 (M+1)$^+$.

Step 2—Tert-butyl N-[2-[2-[4-[2-(2-aminoethoxy)ethyl]piperazin-1-yl]ethoxy]ethyl]carbamate To a solution of tert-butyl N-[2-[2-[4-[2-[2-(benzyloxycarbonylamino)ethoxy]ethyl]piperazin-1-yl]ethoxy]ethyl]carbamate (1.00 g, 2.02 mmol) in THF (5 mL) was added Pd/C (500 mg, 202 umol, 10 wt %). The reaction mixture was stirred at 20° C. under H$_2$ (15 psi) for 24 hours. On completion, the residue was filtered and the filtrate was concentrated in vacuo to give the title compound (600 mg, 82% yield) as colorless oil. LC-MS (ESI$^+$) m/z 361.3 (M+H)$^+$.

4-[2-[2-[4-[2-(2-Aminoethoxy)ethyl]piperazin-1-yl]ethoxy]ethylamino]-2-(2,6-dioxo-3-piperidyl)isoindoline-1,3-dione (Intermediate IN ate R) in DMSO (10 mL) was added DIPEA (537 mg, 4.16 mmol, 724 uL). The reaction mixture was stirred at 90° C. for 2 hours. On completion, the mixture was diluted with H$_2$O (30 mL), then extracted with DCM (2×60 mL). The combined organic phase was washed with brine, and then concentrated in vacuo to give a residue. The residue was purified by reverse phase (0.1% FA condition) to give the title compound (200 mg, 39% yield) as a yellow solid. LC-MS (ESI+) m/z 617.4 (M+H)$^+$.

Step 2—4-[2-[2-[4-[2-(2-Aminoethoxy)ethyl]piperazin-1-yl]ethoxy]ethylamino]-2-(2,6-dioxo-3-piperidyl)isoindoline-1,3-dione To a solution of tert-butyl N-[2-[2-[4-[2-[2-[[2-(2,6-dioxo-3-piperidyl)-1,3-dioxo-isoindolin-4-yl]amino]ethoxy]ethyl]piperazin-1-yl]ethoxy]ethyl]carbamate (200 mg, 324 umol) in DCM (4 mL) was added HCl/dioxane (4 M, 4 mL), and the reaction mixture was stirred at 25° C. for 1 hour. On completion, the mixture was concentrated in vacuo to give the title compound (150 mg, 83% yield) as a yellow solid. LC-MS (ESI$^+$) m/z 517.3 (M+H)$^+$.

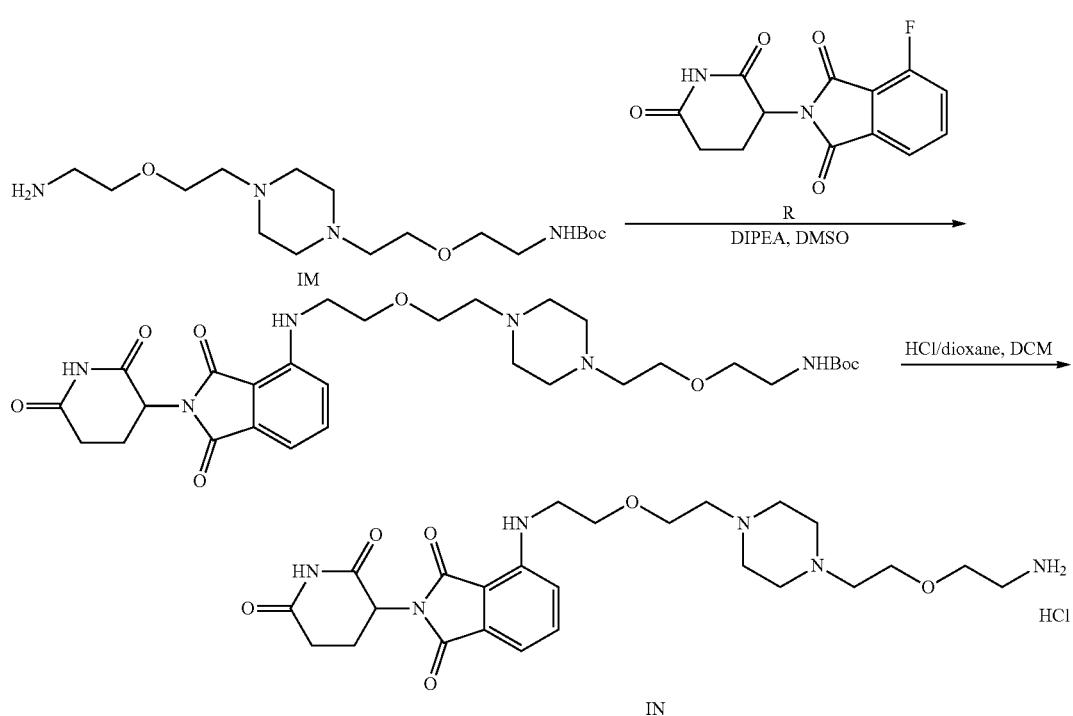

Step 1—Tert-butyl N-[2-[2-[4-[2-[2-[[2-(2,6-dioxo-3-piperidyl)-1,3-dioxo-isoindolin-4-yl]amino]ethoxy]ethyl]piperazin-1-yl]ethoxy]ethyl]carbamate To a solution of tert-butyl N-[2-[2-[4-[2-(2-aminoethoxy)ethyl]piperazin-1-yl]ethoxy]ethyl]carbamate (300 mg, 832 umol, Intermediate IM) and 2-(2,6-dioxo-3-piperidyl)-4-fluoro-isoindoline-1,3-dione (229 mg, 832 umol, Intermedi-

4-[2-[2-[6-[2-(2-Aminoethoxy)ethyl]-2,6-diazaspiro 13.31 heptan-2-yl]ethoxy]ethylamino]-2-(2,6-dioxo-3-piperidyl)isoindoline-1,3-dione (Intermediate IO)

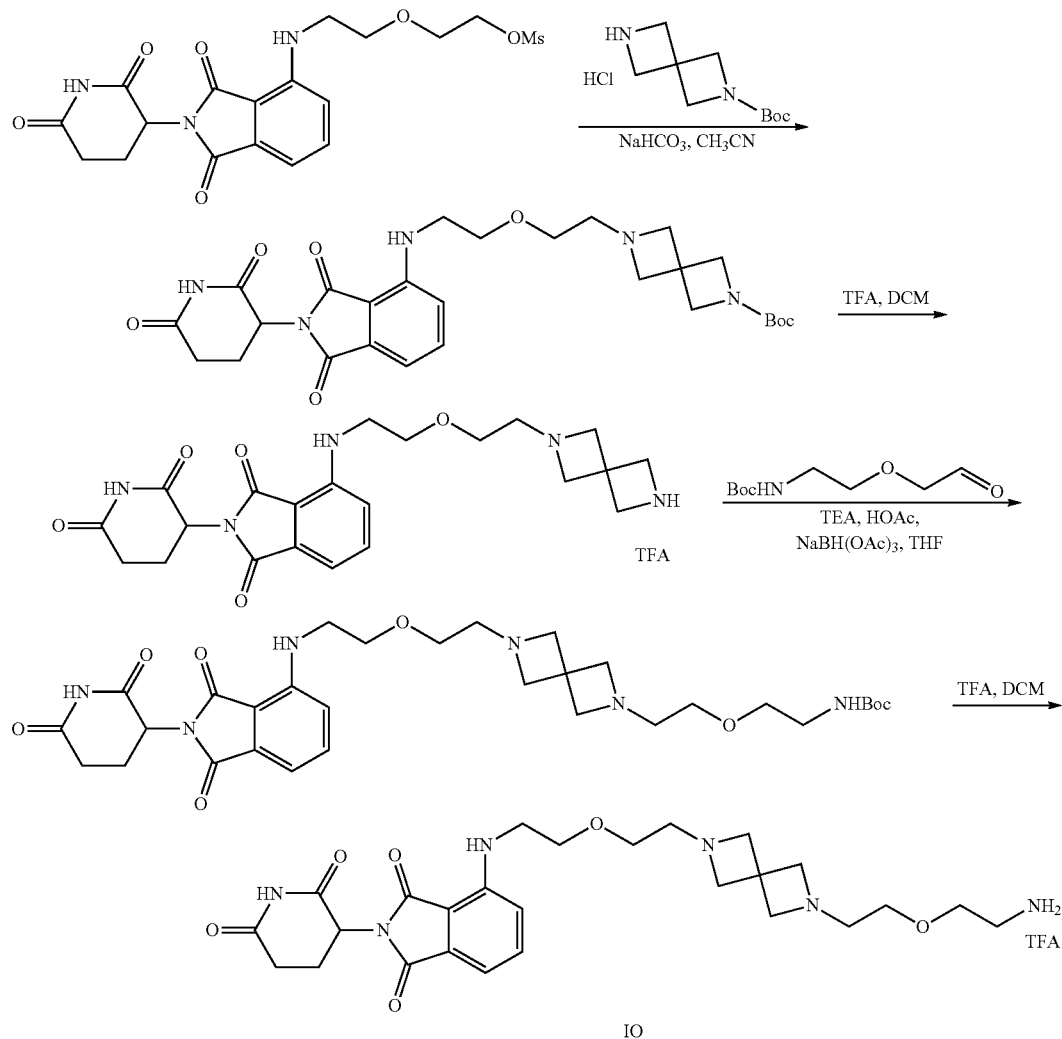

IO

Step 1—Tert-butyl 6-[2-[2-[[2-(2,6-dioxo-3-piperidyl)-1,3-dioxo-isoindolin-4-yl]amino]ethoxy]ethyl]-2,6-diazaspiro[3.3]heptane-2-carboxylate To a solution of tert-butyl 2,6-diazaspiro[3.3]heptane-2-carboxylate (0.40 g, 1.70 mmol, HCl, CAS #1041026-70-3) and 2-[2-[[2-(2,6-dioxo-3-piperidyl)-1,3-dioxo-isoindolin-4-yl]amino]ethoxy]ethyl methanesulfonate (899 mg, 2.04 mmol, synthesized via Steps 1-2 of Example 184) in CH$_3$CN (80 mL) was added NaHCO$_3$ (429 mg, 5.11 mmol). The mixture was stirred at 80° C. for 6 hr. On completion, the mixture was concentrated. The residue was purified by flash silica gel chromatography (DCM:MeOH=10:1) to give the title compound (0.80 g, 69% yield, 80% purity) as a yellow solid. LC-MS (ESI$^+$) m/z 542.4 (M+H)$^+$.

Step 2—4-[2-[2-(2,6-Diazaspiro[3.3]heptan-2-yl)ethoxy]ethylamino]-2-(2,6-dioxo-3-piperidyl) isoindoline-1,3-dione To a solution of tert-butyl 6-[2-[2-[[2-(2,6-dioxo-3-piperidyl)-1,3-dioxo-isoindolin-4-yl]amino]ethoxy]ethyl]-2,6-diazaspiro[3.3]heptane-2-carboxylate (0.80 g, 1.48 mmol) in DCM (50 mL) was added TFA (6.16 g, 54.0 mmol). The mixture was stirred at 15° C. for 5 min. On completion, the mixture was concentrated. The crude product was purified by reversed-phase chromatography (0.1% FA condition) to give the title compound (0.34 g, 47% yield, FA salt) as a yellow solid. LC-MS (ESI$^+$) m/z 442.3 (M+H)$^+$.

Step 3—Tert-butyl N-[2-[2-[6-[2-[2-[[2-(2,6-dioxo-3-piperidyl)-1,3-dioxo-isoindolin-4-yl]amino]ethoxy]ethyl]-2,6-diazaspiro[3.3]heptan-2-yl]ethoxy]ethyl]carbamate To a solution of 4-[2-[2-(2,6-diazaspiro[3.3]heptan-2-yl)ethoxy]ethylamino]-2-(2,6-dioxo-3-piperidyl) isoindoline- 1,3-dione (0.29 g, 595 umol, FA) and tert-butyl N-[2-(2-oxoethoxy)ethyl]carbamate (363 mg, 1.78 mmol, synthesized via Step 1 of Intermediate FS) in DCM (1 mL) and THF (1 mL) was added Et₃N (181 mg, 1.78 mmol) and AcOH (71.5 mg, 1.19 mmol) and then added NaBH(OAc)₃ (252 mg, 1.19 mmol). The mixture was stirred at 15° C. for 6 hrs. On completion, the mixture was concentrated. The crude product was purified by reversed-phase chromatography (0.1% FA condition) to give the title compound (0.32 g, 68% yield, 80% purity) as a yellow solid. LC-MS (ESI⁺) m/z 629.4 (M+H)⁺.

Step 4—4-[2-[2-[6-[2-(2-Aminoethoxy)ethyl]-2,6-diazaspiro[3.3]heptan-2-yl]ethoxy]ethylamino]-2-(2,6-dioxo-3-piperidyl)isoindoline-1,3-dione To a solution of tert-butyl N-[2-[2-[6-[2-[2-[[2-(2,6-dioxo-3-piperidyl)-1,3-dioxo-isoindolin-4-yl]amino]ethoxy]ethyl]-2,6-diazaspiro[3.3]heptan-2-yl]ethoxy]ethyl]carbamate (0.22 g, 350 umol) in DCM (2 mL) was added TFA (39.9 mg, 350 umol). The mixture was stirred at 15° C. for 0.5 hr. On completion, the mixture was concentrated to give the title compound (0.10 g, 31% yield, 70% purity, TFA) as yellow oil. LC-MS (ESI⁺) m/z 529.4 (M+H)⁺.

5-Bromo-3-methyl-1H-benzimidazol-2-one (Intermediate IP)

then Fe (174 g, 3.11 mol) was added to the reaction mixture. After that, the reaction mixture was stirred at 80° C. for 6 hours. On completion, the mixture was filtered through celite. The filtrate was concentrated in vacuo and the residue was diluted with H₂O (250 mL) and extracted with EtOAc (3×300 mL). The combined organic layers were washed with aq.NaHCO₃ and brine (300 mL), dried over Na₂SO₄, filtered and concentrated in vacuo. The residue was purified by flash silica gel chromatography to give the title compound (130 g, 75% yield) as black oil. ¹H NMR (400 MHz, DMSO-d₆) δ 6.55-6.52 (m, 1H), 6.48-6.45 (m, 1H), 6.43-6.42 (m, 1H), 4.89-4.88 (m, 1H), 4.61 (s, 2H), 2.70 (d, J=4.0 Hz, 3H).

Step 3—5-Bromo-3-methyl-1H-benzimidazol-2-one

To a solution of 4-bromo-N2-methyl-benzene-1,2-diamine (110 g, 547 mmol) in CH₃CN (1.3 L) was added CDI (177 g, 1.09 mol). The mixture was stirred at 80° C. for 6 hours under N₂. On completion, the mixture was concentrated in vacuo. The mixture was diluted with H₂O (1.0 L) and filtered. The filter cake was washed with water (3×200 mL) and dried in vacuo to give the title compound (106 g, 85% yield) as a white solid. ¹H NMR (400 MHz, DMSO-d₆) δ 11.00 (s, 1H), 7.33 (s, 1H), 7.13 (d, J=8.0 Hz, 1H), 6.92 (d, J=8.0 Hz, 1H), 3.27 (s, 3H).

[1-[(4-Methoxyphenyl)methyl]-2,6-dioxo-3-piperidyl]trifluoromethanesulfonate (Intermediate IQ)

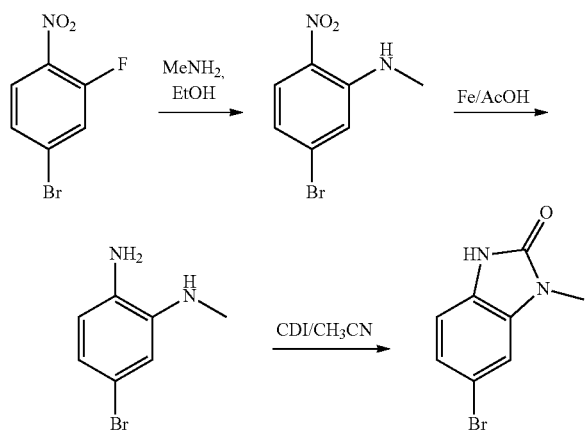

Step 1—5-Bromo-N-methyl-2-nitro-aniline 4-bromo-2-fluoro-1-nitro-benzene (230 g, 1.05 mol, CAS #321-23-3) was added to a solution of methylamine in tetrahydrofuran (2 M, 1.51 L). The mixture was stirred at 15° C. for 10 minutes. On completion, the mixture was diluted with H₂O (250 mL) and extracted with EtOAc (3×300 mL). The combined organic layers were washed with brine (300 mL), dried over Na₂SO₄, filtered and concentrated in vacuo to give the title compound (200 g, 83% yield) as a yellow solid. ¹H NMR (400 MHz, DMSO-d₆) δ 8.22 (s, 1H), 7.98 (d, J=9.2 Hz, 1H), 7.16 (d, J=1.6 Hz, 1H), 6.82 (dd, J=8.4, 1.6 Hz, 1H), 2.95 (d, J=4.8 Hz, 3H).

Step 2—4-Bromo-N2-methyl-benzene-1,2-diamine

To a mixture of 5-bromo-N-methyl-2-nitro-aniline (200 g, 865 mmol) in EtOAc (1 L) and H₂O (500 mL) was added AcOH (1.00 L). The mixture was warmed to 50° C., and

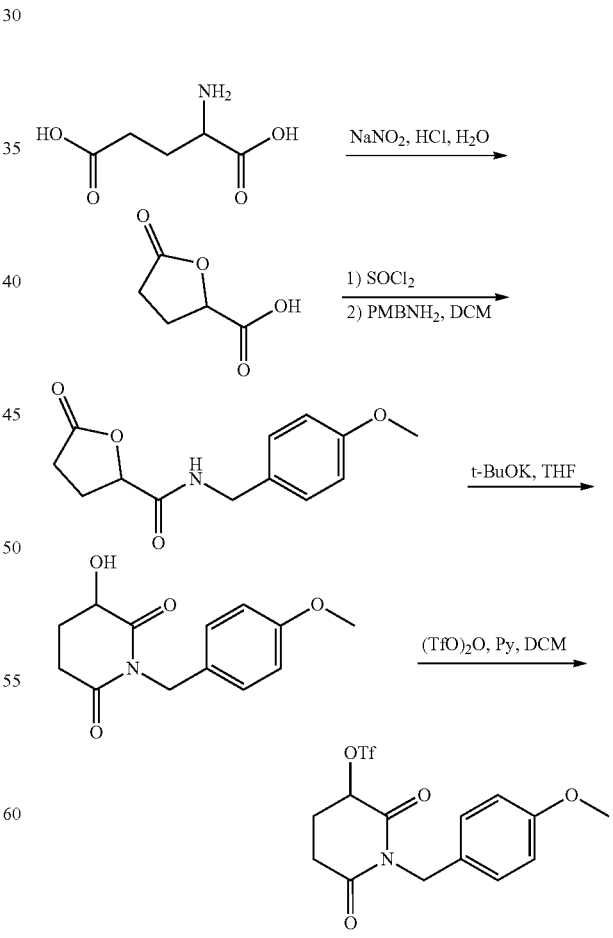

Step 1—5-Oxotetrahydrofuran-2-carboxylic acid

To a solution of 2-aminopentanedioic acid (210 g, 1.43 mol, CAS #617-65-2) in H$_2$O (800 mL) and HCl (12 M, 210 mL) was added a solution of NaNO$_2$ (147 g, 2.13 mol) in H$_2$O (400 mL) at −5° C. The mixture was stirred at 15° C. for 12 hrs. On completion, the mixture was concentrated and then dissolved in EA (500 mL) and filtered and washed with EA (3×100 mL). The filtrate and washed solution were dried over Na$_2$SO$_4$, filtered and concentrated in vacuo to give the title compound (200 g, crude) as yellow oil. $^1$H NMR (400 MHz, CDCl$_3$) δ 6.43 (s, 1H), 5.02-4.95 (m, 1H), 2.67-2.38 (m, 4H)

Step 2—N-[(4-methoxyphenyl)methyl]-5-oxo-tetrahydrofuran-2-carboxamide

To 5-oxotetrahydrofuran-2-carboxylic acid (120 g, 922 mmol) was added SOCl$_2$ (246 g, 2.07 mol) at 0° C. slowly. The mixture was stirred at 85° C. for 3 hrs, and then the mixture was stirred at 15° C. for 6 hrs. The mixture was concentrated in vacuo. The residue was dissolved in dry DCM (1 L) at 0° C. under N$_2$. After that a solution of Et$_3$N (187 g, 1.84 mol) and 4-methoxybenzylamine (101 g, 738 mmol) in DCM (400 mL) was added, then the mixture was stirred at 15° C. for 3 hrs. On completion, water (600 mL) was added and the mixture was extracted with DCM (3×300 mL). The combined organic phase was washed with 0.5 M HCl (500 mL), brine (500 mL), dried over with anhydrous sodium sulfate and filtered. The filtrate was concentrated in vacuo and the residue was purified by flash silica gel chromatography (PE:EA=1:1) to give the title compound (138 g, 60% yield) as a yellow solid. $^1$H NMR (400 MHz, CDCl$_3$) δ 7.22-7.20 (d, J=8.0, 1H), 6.89-6.87 (d, J=8.0, 1H), 4.90-4.86 (m, 1H), 4.47-4.4.36 (m, 2H) 3.81 (s, 3H), 2.67-2.64 (m, 1H), 2.59-2.54 (m, 2H), 2.40-2.38 (m, 1H); LC-MS (ESI$^+$) m/z 272.0 (M+Na)$^+$.

Step 3—3-Hydroxy-1-[(4-methoxyphenyl)methyl]piperidine-2,6-dione

A solution of N-[(4-methoxyphenyl)methyl]-5-oxo-tetrahydrofuran-2-carboxamide (138 g, 553 mmol) in anhydrous THF (1500 mL) was cooled to −78° C. Then, t-BuOK (62.7 g, 559 mmol) in a solution of anhydrous THF (1000 mL) was added dropwise slowly at −78° C. under nitrogen atmosphere. The resulting reaction mixture was stirred at −40° C. for 1 hr. On completion, the reaction mixture was quenched with saturated NH$_4$Cl solution (100 mL). The mixture was extracted with ethyl acetate (3×1500 mL). The combined organic layer was washed with brine (300 mL), dried over anhydrous sodium sulfate, filtered and the filtrate was concentrated in vacuo. The residue was purified by silica gel chromatography (PE:EA=1:1) to give the title compound (128 g, 92% yield) as a white solid. $^1$H NMR (400 MHz, CDCl$_3$) δ 7.39-7.32 (m, 2H), 6.89-6.81 (m, 2H), 4.91 (s, 2H), 4.17-4.11 (m, 1H), 3.80 (s, 3H), 3.54 (s, 1H), 2.98-2.87 (m, 1H), 2.73-2.60 (m, 2H), 2.26-2.20 (m, 1H), 1.80 (dq, J=4.8, 13.1 Hz, 1H).

Step 4—[1-[(4-Methoxyphenyl)methyl]-2,6-dioxo-3-piperidyl]trifluoromethanesulfonate To a solution of 3-hydroxy-1-[(4-methoxyphenyl)methyl]piperidine-2,6-dione (43.0 g, 173 mmol) and pyridine (27.3 g, 345 mmol) in DCM (500 mL) was added trifluoromethylsulfonyl trifluoromethanesulfonate (73.0 g, 258 mmol) dropwise at 0° C. The mixture was stirred at −10° C. for 1.5 hours under N$_2$. On completion, the mixture was concentrated in vacuo. The residue was purified by column chromatography on silica gel (PE:EA=20:1/8:1) to give the title compound (45.0 g, 68% yield) as light yellow gum. $^1$H NMR (400 MHz, CDCl$_3$) δ 7.36 (d, J=8.4 Hz, 2H), 6.85-6.82 (m, 2H), 5.32-5.28 (m, 1H), 4.91 (s, 2H), 3.79 (s, 3H), 3.02-2.97 (m, 1H), 2.79-2.74 (m, 1H), 2.41-2.35 (m, 2H).

3-(4-bromo-1-oxoisoindolin-2-yl)piperidine-2,6-dione (Intermediate IR)

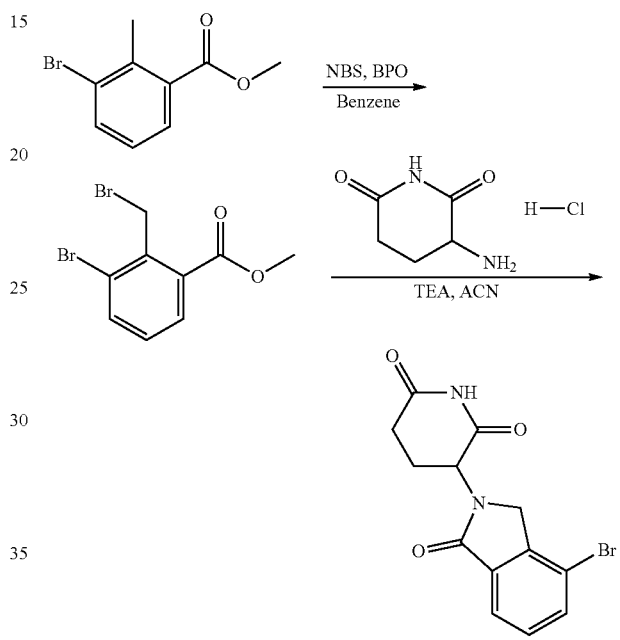

IR

Step 1: 3-bromo-2-(bromomethyl)benzoate

To a solution of methyl 3-bromo-2-methylbenzoate (10.0 g, 43.64 mmol, CAS #: 99548-54-6) in benzene (60 ml) were added N-bromosuccinimide (6.1 g, 52.37 mmol) and benzoyl peroxide (1.05 g, 4.36 mmol) at rt. The reaction mixture was stirred at 80° C. for 12 h. The resulting reaction mixture was poured into EtOAc (260 mL) and the organic layer was washed with water (200 ml), separated, dried over anhydrous Na$_2$SO$_4$ and concentrated under reduced pressure to give the residue. The crude was purified by flash chromatography (eluting at 0-2% ethyl acetate in hexane) to afford 3-bromo-2-(bromomethyl)benzoate (12.0 g, 39.33 mmol). $^1$H NMR (400 MHz, DMSO-d6) δ 7.92 (dd, J=8.0, 1.3 Hz, 1H), 7.85 (dd, J=7.8, 1.3 Hz, 1H), 7.41 (t, J=7.9 Hz, 1H), 5.02 (s, 2H), 3.87 (s, 3H).

Step 2: 3-(4-bromo-1-oxoisoindolin-2-yl)piperidine-2,6-dione

To a solution of 3-bromo-2-(bromomethyl)benzoate (12.0 g, 39.33 mmol) in ACN (100 ml) were added 3-aminopiperidine-2,6-dione hydrochloride (7.76 g, 47.20 mmol, CAS #: 24666-56-6), TEA (11.95 g, 117.9 mmol) at rt. The reaction mixture was heated 80° C. for 12 h then cooled to rt. EtOAc (250 ml) was added and the organic layer was washed with water (500 ml), separated, dried over anhydrous Na₂SO₄ and concentrated under vacuum. The obtained crude material was purified by flash chromatography (eluting at 4-6% Methanol in DCM) to give 3-(4-bromo-1-oxoisoindolin-2-yl)piperidine-2,6-dione (5.60 g, 17.33 mmol). LCMS m/z: (ES+) 323.0 (M+1)⁺. ¹H NMR (400 MHz, DMSO-d6) δ 11.04 (s, 1H), 7.88 (dd, J=7.9, 0.9 Hz, 1H), 7.78 (dd, J=7.5, 0.9 Hz, 1H), 7.52 (t, J=7.7 Hz, 1H), 5.16 (dd, J=13.3, 5.1 Hz, 1H), 4.43 (d, J=17.6 Hz, 1H), 4.27 (d, J=17.7 Hz, 1H), 2.92 (ddd, J=17.2, 13.7, 5.4 Hz, 1H), 2.61 (dd, J=17.5, 4.3 Hz, 1H), 2.02 (dtd, J=12.8, 5.4, 2.3 Hz, 1H).

tert-butyl (2-(2-(2-(prop-2-yn-1-yloxy)ethoxy)ethoxy)ethyl)carbamate (Intermediate IS)

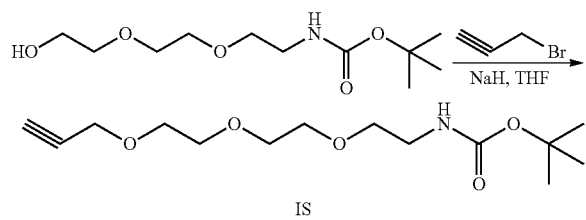

To a stirred solution of tert-butyl (2-(2-(2-hydroxyethoxy)ethoxy)ethyl)carbamate (1.0 g, 4.01 mmol, synthesized via Step 1 on Intermediate AC) in THF (50 ml) was added NaH (0.2 g, 4.81 mmol) at 0-5° C. 3-bromoprop-1-yne (0.9 ml, 6.02 mmol, CAS #: 106-96-7) was added dropwise at 0-5° C. The reaction mixture was stirred at rt for 5 h. The resulting reaction mixture was poured into ice cold water (200 ml) and extracted with ethyl acetate (3×200 ml). The combined organic layer was dried over anhydrous Na₂SO₄, filtered and concentrated under vacuum to afford tert-butyl (2-(2-(2-(prop-2-yn-1-yloxy)ethoxy)ethoxy)ethyl)carbamate (1.1 g, 3.83 mmol). LCMS m/z (ES+): 188.2 (M-99)⁺.

tert-butyl (2-(2-(prop-2-yn-1-yloxy)ethoxy)ethyl)carbamate (Intermediate IT)

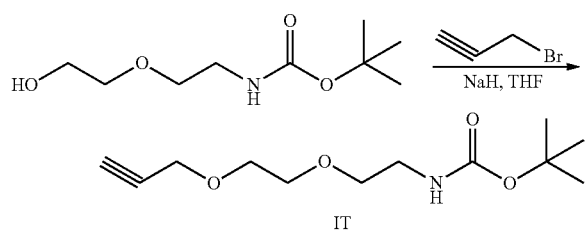

To a stirred solution of tert-butyl (2-(2-hydroxyethoxy)ethyl)carbamate (2.0 g, 9.74 mmol, CAS #: 139115-91-6) in THF (50 ml) was added NaH (0.47 g, 11.70 mmol) at 0-5° C. 3-bromoprop-1-yne (2.1 ml, 14.62 mmol) was added dropwise at 0-5° C. The reaction mixture was stirred at rt for 5 h. The resulting reaction mixture was poured into ice cold water (200 ml) and extracted with ethyl acetate (3×200 ml). The combined organic layer was dried over anhydrous Na₂SO₄, filtered and concentrated under vacuum to afford tert-butyl (2-(2-(prop-2-yn-1-yloxy)ethoxy)ethyl)carbamate (2.1 g, 8.97 mmol). LCMS m/z: (ES+) 144.1 (M-99)⁺.

tert-butyl (2-(prop-2-yn-1-yloxy)ethyl)carbamate (Intermediate IU)

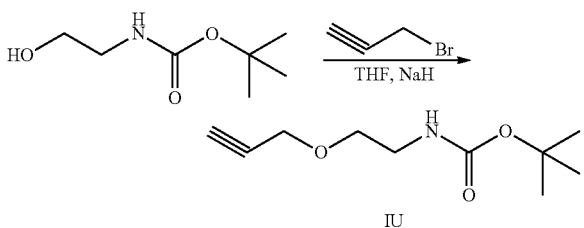

To a stirred solution of tert-butyl (2-hydroxyethyl)carbamate (3.70 g, 22.96 mmol, CAS #: 26690-80-) in THF (150 ml) was added NaH (1.1 g, 27.55 mmol) at 0-5° C. Then 3-bromoprop-1-yne (3.3 ml, 34.44 mmol) was added dropwise at 0-5° C. The reaction mixture was stirred at rt for 3 h. The resulting reaction mixture was poured into ice cold water (200 ml) and extracted with ethyl acetate (3×100 ml). The combined organic layer was dried over anhydrous Na₂SO₄, filtered and concentrated under vacuum to afford crude material. The isolated crude material was further purified by column chromatography (eluting at 15% ethyl acetate in hexane) to afford tert-butyl (2-(prop-2-yn-1-yloxy)ethyl)carbamate (4.12 g, 20.69 mmol). ¹H NMR (400 MHz, DMSO-d6) δ 6.83 (t, J=5.8 Hz, 1H), 4.12 (d, J=2.4 Hz, 2H), 3.42 (s, 2H), 3.08 (q, J=6.0 Hz, 2H), 1.38 (s, 9H).

2-(1-Methylpyrazol-4-yl)oxazole-4-carboxylic acid (Intermediate IV)

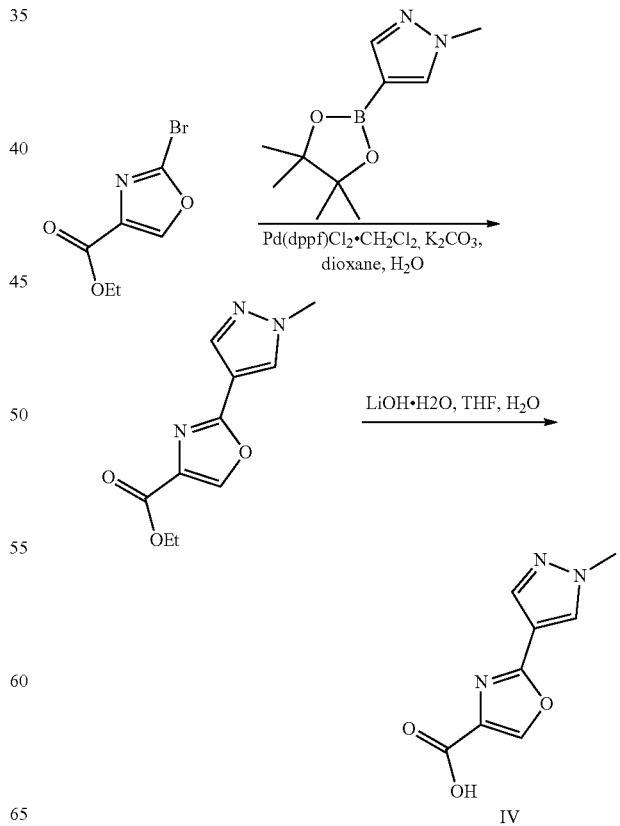

Step 1—Ethyl 2-(1-methylpyrazol-4-yl)oxazole-4-carboxylate

To a solution of ethyl 2-chlorooxazole-4-carboxylate (1.87 g, 10.7 mmol, CAS #4600081-18-9) and 1-methyl-4-(4,4,5,5-tetramethyl-1,3,2-dioxaborolan-2-yl)pyrazole (2.22 g, 10.7 mmol, CAS #761446-44-0) in a mixed solvent of $H_2O$ (6 mL) and dioxane (30 mL) was added $K_2CO_3$ (2.94 g, 21.3 mmol) and $Pd(dppf)Cl_2 \cdot CH_2Cl_2$ (870 mg, 1.07 mmol). The reaction mixture was stirred at 80° C. for 4 hours under nitrogen. On completion, the reaction mixture was diluted with EA (100 mL) and filtered. The organic layers were dried with anhydrous $Na_2SO_4$, and concentrated in vacuo. The residue was purified by silica column chromatography ($SiO_2$) to give the title compound (1.50 g, 64% yield) as a white solid. LC-MS (ESI$^+$) m/z 222.1 (M+H)$^+$.

Step 2—2-(1-Methylpyrazol-4-yl)oxazole-4-carboxylic acid

To a solution of ethyl 2-(1-methylpyrazol-4-yl)oxazole-4-carboxylate (1.20 g, 5.42 mmol) in THF (30 mL) was added a solution of $LiOH \cdot H_2O$ (683 mg, 16.3 mmol) in $H_2O$ (6 mL). The reaction mixture was stirred at 25° C. for 12 hours. On completion, the reaction mixture was diluted with water (50 mL), acidified with HCl (1N, 10 mL), and filtered. The filter cake was washed with water (2×10 mL) and dried in vacuo to give the title compound (1.10 g, 80% purity) as a white solid.

N-[3-(difluoromethyl)-1-(4-formylphenyl)pyrazol-4-yl]-2-(1-methylpyrazol-4-yl)oxazole-4-carboxamide (Intermediate IW)

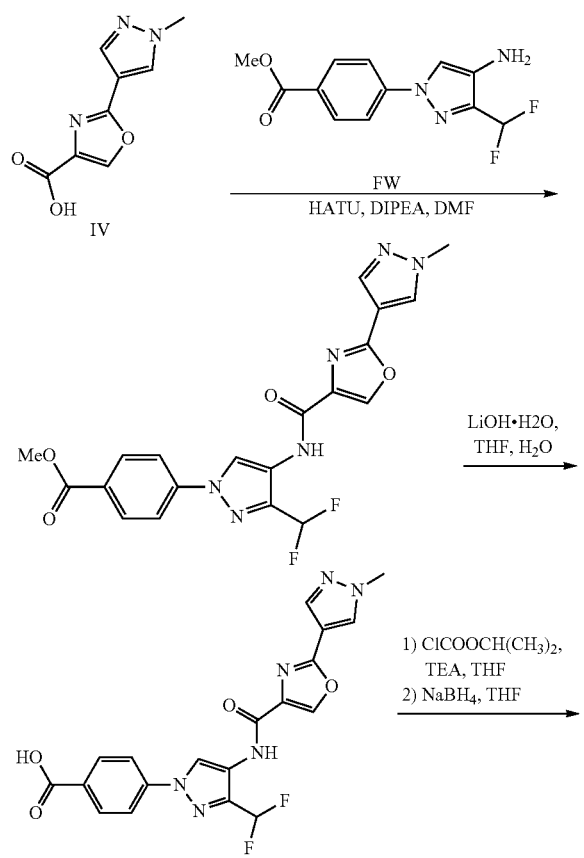

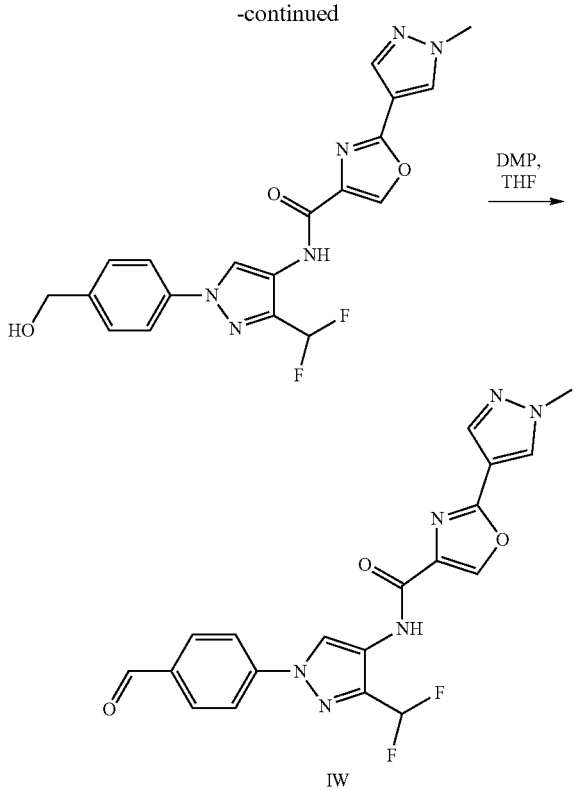

Step 1—Methyl 4-[3-(difluoromethyl)-4-[[2-(1-methylpyrazol-4-yl)oxazole-4-carbonyl]amino]pyrazol-1-yl]benzoate To a solution of 2-(1-methylpyrazol-4-yl)oxazole-4-carboxylic acid (860 mg, 4.45 mmol, Intermediate IV) and methyl 4-[4-amino-3-(difluoromethyl)pyrazol-1-yl]benzoate (833 mg, 3.12 mmol, Intermediate FW) in DMF (30 mL) was added DIPEA (2.30 g, 17.8 mmol) and HATU (1.86 g, 4.90 mmol). The reaction mixture was stirred at 25° C. for 1 hour. On completion, the reaction mixture was poured into water (50 mL), and filtered to give the filter cake. The cake was washed with water (2×20 mL) and dried in vacuo to give the title compound (1.40 g, 68% yield) as a white solid. LC-MS (ESI$^+$) m/z 443.2 (M+H)$^+$.

Step 2—4-[3-(Difluoromethyl)-4-[[2-(1-methylpyrazol-4-yl)oxazole-4-carbonyl]amino]pyrazol-1-yl]benzoic acid To a solution of methyl 4-[3-(difluoromethyl)-4-[[2-(1-methylpyrazol-4-yl)oxazole-4-carbonyl]amino]pyrazol-1-yl]benzoate (800 mg, 1.81 mmol) in THF (10 mL) was added a solution of $LiOH \cdot H_2O$ (228 mg, 5.43 mmol) in $H_2O$ (2 mL). The reaction mixture was stirred at 40° C. for 12 hours. On completion, the reaction mixture was quenched with HCl (1N, 3 mL) and concentrated in vacuo to give the title compound (900 mg, 59% purity) as a white solid. LC-MS (ESI$^+$) m/z 429.0 (M+H)$^+$.

Step 3—N-[3-(difluoromethyl)-1-[4-(hydroxymethyl)phenyl]pyrazol-4-yl]-2-(1-methylpyrazol-4-yl)oxazole-4-carboxamide To a solution of 4-[3-(difluoromethyl)-4-[[2-(1-methylpyrazol-4-yl)oxazole-4-carbonyl]amino]pyrazol-1-yl]

benzoic acid (775 mg, 1.81 mmol) and TEA (732 mg, 7.24 mmol) in THF (30 mL) was added isopropyl carbonochloridate (443 mg, 3.62 mmol) at −10° C. The reaction mixture was stirred at −10° C. for 2 hours. After that, H$_2$O (3 mL) was added. The reaction mixture was warmed to 0° C. Then LiBH$_4$ (158 mg, 7.24 mmol) was added slowly. The reaction mixture was stirred at 0° C. for 2 hours. On completion, the reaction mixture was diluted with THF (50 mL) and filtered. The filtrate was concentrated in vacuo and the residue was purified by silica column chromatography (SiO$_2$) to give the title compound (200 mg, 27% yield) as a white solid. LC-MS (ESI$^+$) m/z 415.2 (M+H)$^+$.

Step 4—N-[3-(difluoromethyl)-1-(4-formylphenyl)pyrazol-4-yl]-2-(1-methylpyrazol-4-yl)oxazole-4-carboxamide To a solution of N-[3-(difluoromethyl)-1-[4-(hydroxymethyl)phenyl]pyrazol-4-yl]-2-(1-methylpyrazol-4-yl)oxazole-4-carboxamide (180 mg, 434 umol) in THF (20 mL) was added DMP (184 mg, 434 umol). The reaction mixture was stirred at 25° C. for 12 hours. On completion, the reaction mixture was quenched with water (5 mL) and concentrated in vacuo. The residue was dissolved in EA (200 mL), washed with water (50 mL), sat.NaHCO$_3$ (50 mL), and brine (50 mL). The organic layer was dried with anhydrous Na$_2$SO$_4$, filtered and concentrated in vacuo to give the title compound (200 mg, 71% yield) as a white solid. LC-MS (ESI$^+$) m/z 413.1 (M+H)$^+$.

5-[2-[2-(2-Aminoethoxy)ethoxy]ethylamino]-2-(2,6-dioxo-3-piperidyl)isoindoline-1,3-dione (Intermediate IX)

was added DIPEA (233 mg, 1.81 mmol, 315 uL). The reaction mixture was stirred at 130° C. for 1 hour. On completion, the reaction mixture was diluted with water (20 mL) and extracted with EA (3×30 mL). The combined organic layers was dried over Na$_2$SO$_4$, filtered and concentrated in vacuo to give a residue. The residue was purified by prep-HPLC (0.1% FA condition) to give the title compound (90.0 mg, 49% yield) as light yellow solid. LC-MS (ESI$^+$) m/z 505.1 (M+H)$^+$ Step 2—5-[2-[2-(2-Aminoethoxy)ethoxy]ethyl amino]-2-(2,6-dioxo-3-piperidyl)isoindoline-1,3-dione To a mixture of tert-butyl N-[2-[2-[2-[[2-(2,6-dioxo-3-piperidyl)-1,3-dioxo-isoindolin-5-yl]amino]ethoxy]ethoxy]ethyl]carbamate (90.0 mg, 178 umol) in DCM (5 mL) was added HCl/dioxane (4 M, 5 mL). The reaction mixture was stirred at 20° C. for 1 hour. On completion, the reaction mixture was concentrated in vacuo to give the title compound (72.0 mg, 91% yield, HCl) as light yellow solid. LC-MS (ESI$^+$) m/z 405.3 (M+H)$^+$.

Tert-butyl N-methyl-N-prop-2-ynyl-carbamate (Intermediate IY)

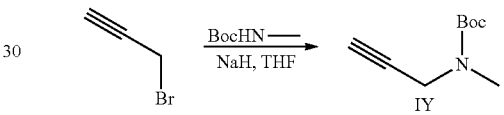

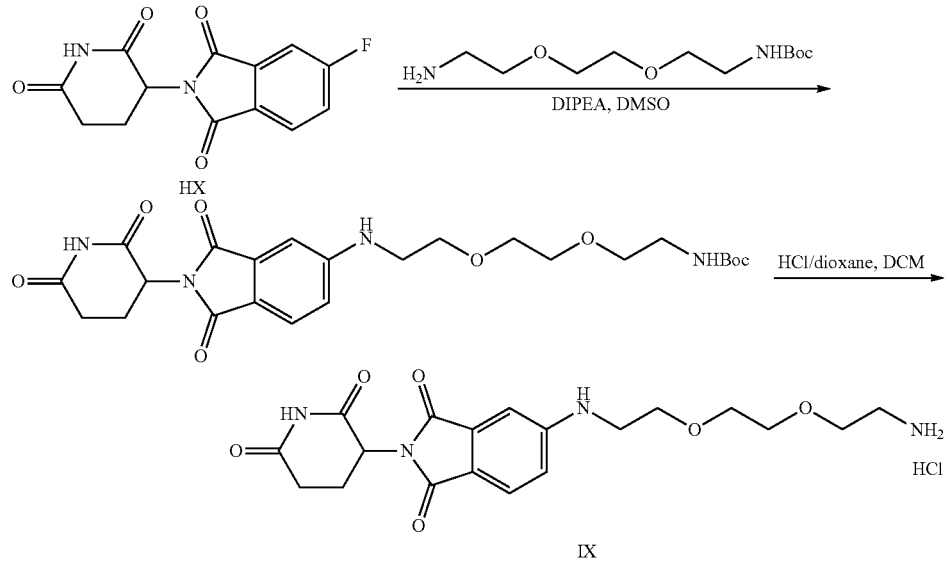

Step 1—Tert-butyl N-[2-[2-[2-[[2-(2,6-dioxo-3-piperidyl)-1,3-dioxo-isoindolin-5-yl]amino]ethoxy]ethoxy]ethyl]carbamate To a mixture of 2-(2,6-dioxo-3-piperidyl)-5-fluoro-isoindoline-1,3-dione (100 mg, 362 umol, Intermediate HX) and tert-butyl N-[2-[2-(2-aminoethoxy)ethoxy]ethyl]carbamate (107 mg, 434 umol, CAS #153086-78-3) in DMSO (5 mL)

To a solution of tert-butyl N-methylcarbamate (10.4 g, 79.2 mmol) in THF (120 mL) was added NaH (4.12 g, 103 mmol, 60% purity) under 0° C. The mixture was stirred at 0° C. for 0.5 hour, then 3-bromoprop-1-yne (13.2 g, 111 mmol) was added dropwise. The mixture was stirred at rt for 16 hours. On completion, the reaction mixture was quenched with water (10 mL) at 0° C., and then concentrated in vacuo to give a residue. The residue was diluted with water (80 mL) and extracted with DCM (4×60 mL). The combined organic layers were dried over Na₂SO₄, filtered and concentrated in vacuo to give a residue. The residue was purified by column chromatography to give the title compound (4.50 g, 33% yield) as light yellow oil. $^1$H NMR (400 MHz, DMSO-d₆) δ 4.05 (s, 2H), 2.92 (s, 3H), 2.22 (t, J=2.4 Hz, 1H), 1.47 (s, 9H).

2-(2,6-Dioxo-3-piperidyl)-4-[3-(methylamino)propyl]isoindoline-1,3-dione (Intermediate IZ)

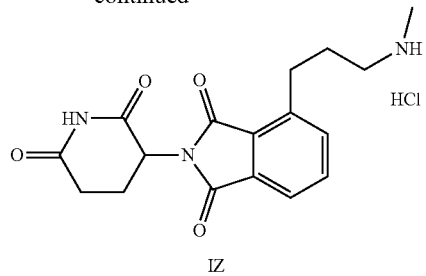

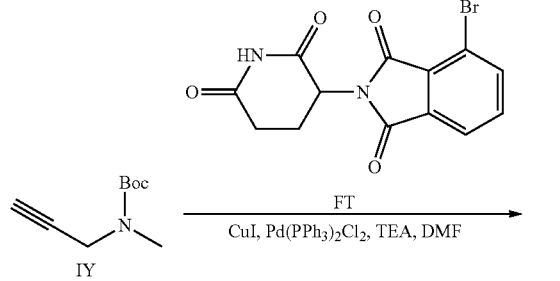

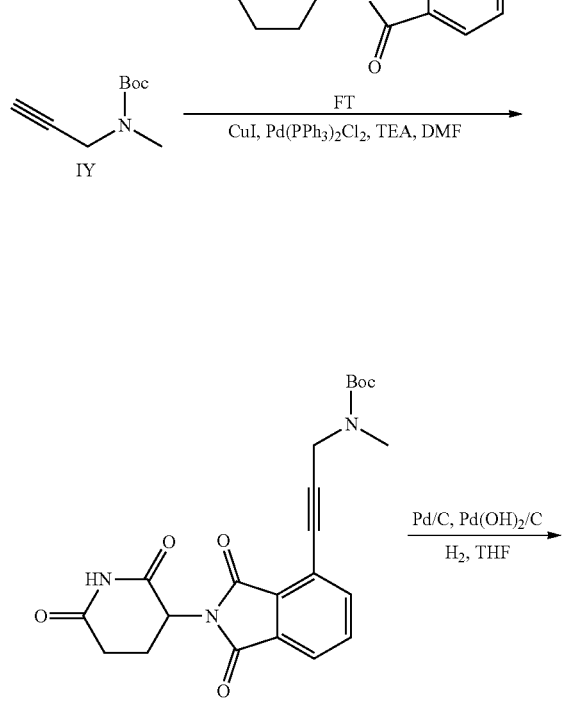

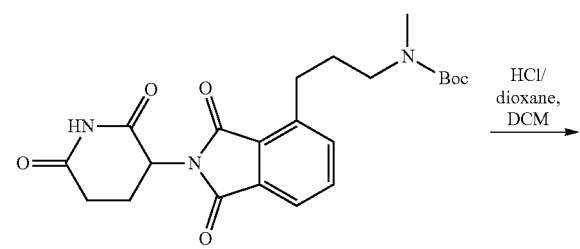

Step 1—Tert-butyl N-[3-[2-(2,6-dioxo-3-piperidyl)-1,3-dioxo-isoindolin-4-yl]prop-2-ynyl]-N-methyl-carbamate To a solution of 4-bromo-2-(2,6-dioxo-3-piperidyl)isoindoline-1,3-dione (1.87 g, 5.54 mmol, Intermediate FT) and tert-butyl N-methyl-N-prop-2-ynyl-carbamate (1.5 g, 8.86 mmol, Intermediate IY) in DMF (5 mL) was added Pd(PPh₃)₂Cl₂ (388 mg, 554 umol), TEA (10.0 g, 99.7 mmol) and CuI (105 mg, 554 umol). The mixture was heated at 80° C. for 30 minutes under microwave. On completion, the reaction mixture was concentrated in vacuo to give a residue. The residue was purified by silica gel chromatography (PE:EA=1:1) to give the title compound (1.90 g, 71% yield) as light yellow solid. $^1$H NMR (400 MHz, DMSO-d₆) δ 11.13 (s, 1H), 7.93-7.89 (m, 1H), 7.89-7.84 (m, 2H), 5.15 (dd, J=5.4, 12.8 Hz, 1H), 4.37 (s, 2H), 3.32 (s, 3H), 3.01-2.90 (m, 3H), 2.90-2.82 (m, 1H), 2.64-2.51 (m, 2H), 2.11-2.00 (m, 1H), 1.47-1.36 (m, 9H); LC-MS (ESI⁺) m/z 448.2 (M+Na)⁺.

Step 2—Tert-butyl N-[3-[2-(2,6-dioxo-3-piperidyl)-1,3-dioxo-isoindolin-4-yl]propyl]-N-methyl-carbamate To a solution of tert-butyl N-[3-[2-(2,6-dioxo-3-piperidyl)-1,3-dioxo-isoindolin-4-yl]prop-2-ynyl]-N-methyl-carbamate (0.50 g, 1.05 mmol) in THF (20 mL) was added Pd/C (0.2 g, 1.05 mmol, 10 wt %) and Pd(OH)₂/C (0.2 g, 1.05 mmol, 10% purity) under N₂. The suspension was degassed under vacuum and purged with H₂ three times. The mixture was stirred under H₂ (15 Psi) at 20° C. for 2 hours. On completion, the reaction mixture was filtered and the filtrate was concentrated in vacuo to give the title compound (0.4 g, 89% yield) as black brown solid. LC-MS (ESI⁺) m/z 452.3 (M+Na)⁺.

Step 3—2-(2,6-Dioxo-3-piperidyl)-4-[3-(methylamino)propyl]isoindoline-1,3-dione To a solution of tert-butyl N-[3-[2-(2,6-dioxo-3-piperidyl)-1,3-dioxo-isoindolin-4-yl]propyl]-N-methyl-carbamate (0.40 g, 828 umol) in DCM (4 mL) was added HCl/dioxane (4 M, 4 mL). The mixture was stirred at 5° C. for 20 minutes. On completion, the reaction mixture was concentrated in vacuo to give the title compound (0.28 g, 92% yield) as black brown solid. LC-MS (ESI⁺) m/z 330.2 (M+H)⁺.

N-[3-carbamoyl-1-(4-formylphenyl)pyrazol-4-yl]-2-(4-pyridyl)oxazole-4-carboxamide (Intermediate JA)

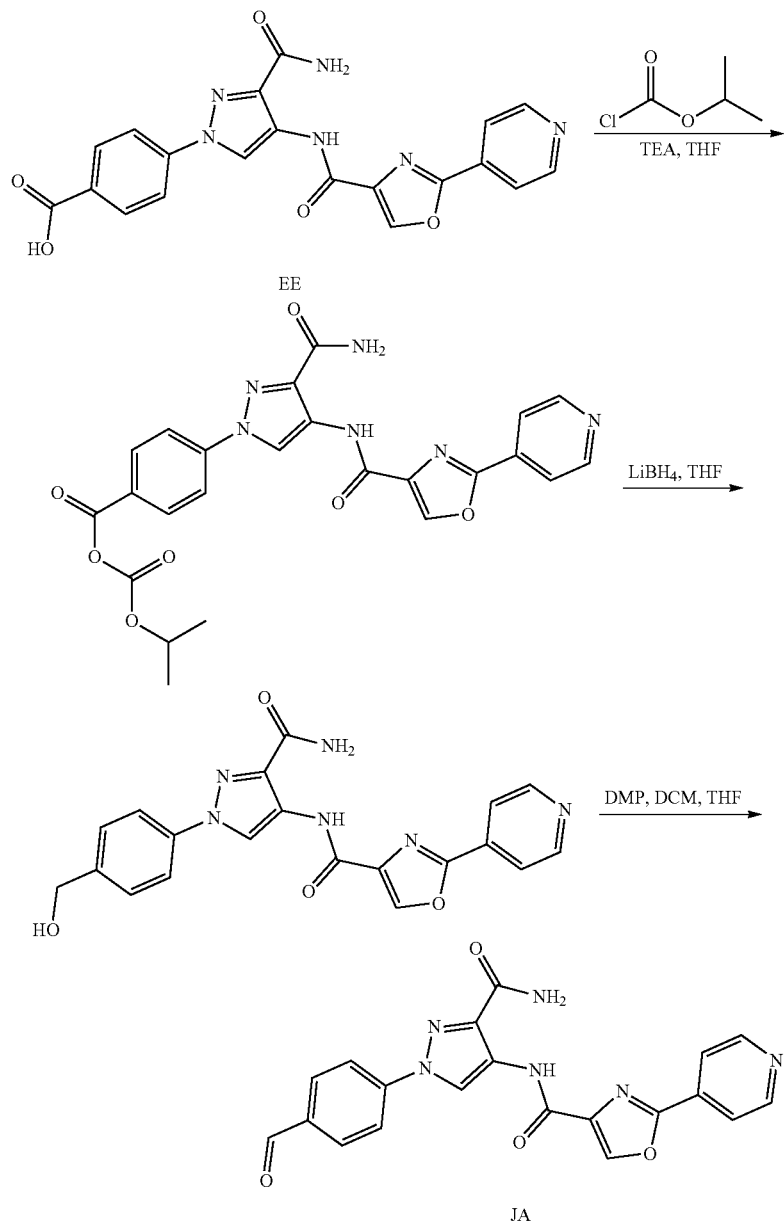

Step 1—Isopropoxycarbonyl 4-[3-carbamoyl-4-[[2-(4-pyridyl)oxazole-4-carbonyl]amino]pyrazol-1-yl]benzoate To a mixture of 4-[3-carbamoyl-4-[[2-(4-pyridyl)oxazole-4-carbonyl]amino]pyrazol-1-yl]benzoic acid (500 mg, 1.20 mmol, Intermediate EE) in THF (20 mL) was added TEA (483 mg, 4.78 mmol, 665 uL) and isopropyl carbonochloridate (366 mg, 2.99 mmol, 414 uL). The reaction mixture was stirred at −10° C. for 2 hours. On completion, the reaction mixture was filtered. The filtrate was concentrated to give the title compound (600 mg, 99% yield)

Step 2—N-[3-carbamoyl-1-[4-(hydroxymethyl)phenyl]pyrazol-4-yl]-2-(4-pyridyl)oxazole-4-carboxamide To a mixture of isopropoxycarbonyl 4-[3-carbamoyl-4-[[2-(4-pyridyl)oxazole-4-carbonyl]amino]pyrazol-1-yl]benzoate (600 mg, 1.19 mmol) in H$_2$O (5 mL) and THF (50 mL) was added LiBH$_4$ (155 mg, 7.14 mmol) at 0° C. The reaction mixture was stirred at 0° C. for 2 hours. On completion, the reaction mixture was quenched with water (30 mc) under stirring. Then the mixture was extracted with EA (3×50 mL). The combined organic layers was dried over Na$_2$SO$_4$, filtered and concentrated in vacuo to give a residue. The residue was triturated with DCM/PE (5 mL/3 mL) and filtered to give the title compound (250 mg, 51% yield) as light yellow solid. LC-MS (ESI⁺) m/z 405.2 (M+H)⁺.

Step 3—N-[3-carbamoyl-1-(4-formylphenyl)pyrazol-4-yl]-2-(4-pyridyl)oxazole-4-carboxamide To a mixture of N-[3-carbamoyl-1-[4-(hydroxymethyl)phenyl]pyrazol-4-yl]-2-(4-pyridyl)oxazole-4-carboxamide (250 mg, 618 umol) in DCM (10 mL) and THF (10 mL) was added DMP (524 mg, 1.24 mmol) at 0° C. The reaction mixture was stirred at 0° C. for 2 hours. On completion, the reaction mixture was diluted with Na$_2$S$_2$O$_3$ (10 mL), NaHCO$_3$ (10 mL) and stirred for 30 min. Then the mixture was extracted with DCM (3×10 mL) and the combined organic layers was dried over Na$_2$SO$_4$, filtered and concentrated in vacuo to give the title compound (230 mg, 92% yield) as light yellow solid. LC-MS (ESI⁺) m/z 403.2 (M+H)⁺.

[4-[4-Amino-3-(difluoromethyl)pyrazol-1-yl]phenyl]methanol (Intermediate JB)

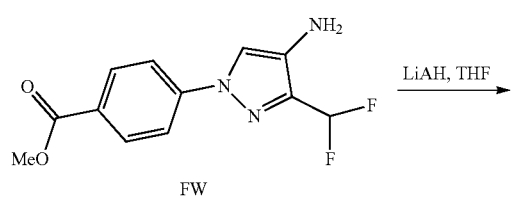

FW

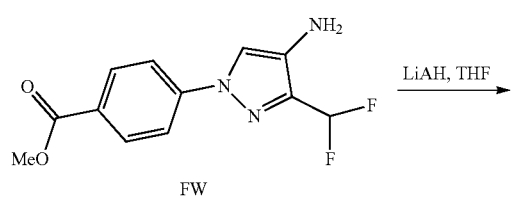

JB

To a solution of methyl 4-[4-amino-3-(difluoromethyl)pyrazol-1-yl]benzoate (1.30 g, 4.86 mmol, Intermediate FW) in a mixed solvent of THF (40 mL) was added LiAlH$_4$ (369 mg, 9.73 mmol) at 0° C. The mixture was stirred at 0° C. for 1 hour. The mixture was quenched with water (0.8 mL) and NaOH aqueus solution (15%, 0.8 mL) at 0° C., then filtered and dried over Na$_2$SO$_4$, filtered again and concentrated in vacuo to give the title compound (1.10 g, 94% yield) as light yellow solid. $^1$H NMR (400 MHz, DMSO-d$_6$) δ 7.78 (s, 1H), 7.67 (d, J=8.8 Hz, 2H), 7.40 (d, J=8.8 Hz, 2H), 7.05 (t, J=13.6 Hz, 1H), 5.25 (t, J=5.6 Hz, 1H), 4.51 (d, J=5.6 Hz, 2H), 4.39 (s, 2H).

Tert-butyl N-[4-[4-[[3-(difluoromethyl)-1-(4-formylphenyl)pyrazol-4-yl]carbamoyl]oxazol-2-yl]-2-pyridyl]-N-(2,2,2-trifluoroethyl)carbamate (Intermediate JC)

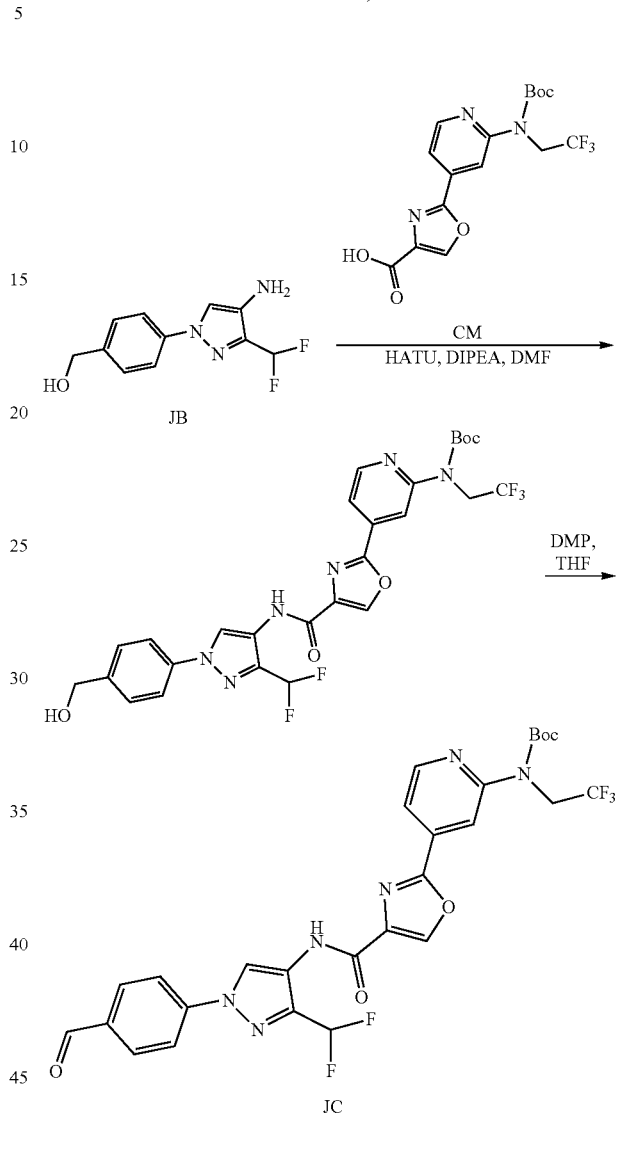

Step 1—Tert-butyl N-[4-[4-[[3-(difluoromethyl)-1-[4-(hydroxymethyl)phenyl]pyrazol-4-yl]carbamoyl]oxazol-2-yl]-2-pyridyl]-N-(2,2,2-trifluoroethyl)carbamate To a solution of 2-[2-[tert-butoxycarbonyl(2,2,2-trifluoroethyl)amino]-4-pyridyl]oxazole-4-carboxylic acid (1.42 g, 3.68 mmol, Intermediate CM) and HATU (1.92 g, 5.06 mmol) in DMF (20 mL) was added DIPEA (1.78 g, 13.7 mmol) and [4-[4-amino-3-(difluoromethyl)pyrazol-1-yl]phenyl]methanol (1.1 g, 4.60 mmol, Intermediate JB). The mixture was stirred at 25° C. for 2 hours. On completion, the reaction mixture was diluted with 80 mL water, filtered to give the filter cake and was dried in vacuo to give the product (1.90 g, 67% yield) as gray solid. $^1$H NMR (400 MHz, DMSO-d$_6$) δ 10.06 (s, 1H), 9.07 (s, 1H), 8.80 (s, 1H), 8.65 (d, J=5.2 Hz, 1H), 8.31 (s, 1H), 7.87-7.77 (m, 3H), 7.48

(d, J=8.4 Hz, 2H), 7.28 (d, J=14.4 Hz, 1H), 5.30 (t, J=5.6 Hz, 1H), 4.90 (q, J=9.2 Hz, 2H), 4.56 (d, J=5.6 Hz, 2H), 1.52 (s, 9H).

Step 2—Tert-butyl N-[4-[4-[[3-(difluoromethyl)-1-(4-formylphenyl)pyrazol-4-yl]carbamoyl]oxazol-2-yl]-2-pyridyl]-N-(2,2,2-trifluoroethyl)carbamate To a solution of tert-butyl N-[4-[4-[[3-(difluoromethyl)-1-[4-(hydroxymethyl)phenyl]pyrazol-4-yl]carbamoyl]oxazol-2-yl]-2-pyridyl]-N-(2,2,2-trifluoroethyl)carbamate (1.90 g, 3.12 mmol) in a THF (60 mL) was added DMP (1.59 g, 3.75 mmol). The mixture was stirred at 20° C. for 12 hours. On completion, the reaction mixture was quenched by saturated Na$_2$S$_2$O$_3$ (20 mL) and saturated NaHCO$_3$ (20 mL) at 25° C. The mixture was stirred for 30 minutes, then extracted with CH$_2$Cl$_2$ (3×100 mL). The combined organic layers dried over Na$_2$SO$_4$, filtered and concentrated in vacuo to give the title compound (1.30 g, 68% yield) as gray solid. $^1$H NMR (400 MHz, DMSO-d$_6$) δ 10.17 (s, 1H), 10.05 (s, 1H), 9.09 (s, 1H), 8.99 (s, 1H), 8.65 (d, J=5.2 Hz, 1H), 8.31 (s, 1H), 8.12 (d, J=8.4 Hz, 2H), 8.04 (d, J=8.4 Hz, 2H), 7.80 (dd, J=0.8, 5.2 Hz, 1H), 7.33 (t, J=14.0 Hz, 1H), 4.90 (q, J=8.8 Hz, 2H), 1.52 (s, 9H); LC-MS (ESI$^+$) m/z 607.1 (M+H)$^+$.

N-[3-(difluoromethyl)-1-(4-formylphenyl)pyrazol-4-yl]-2-(4-pyridyl)oxazole-4-carboxamide (Intermediate JD)

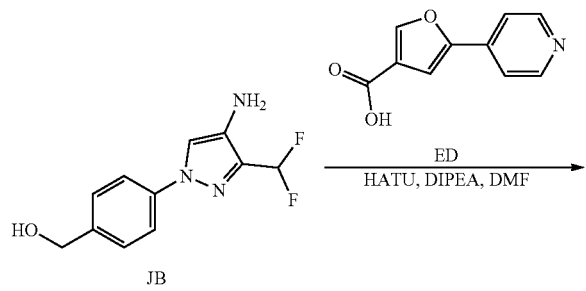

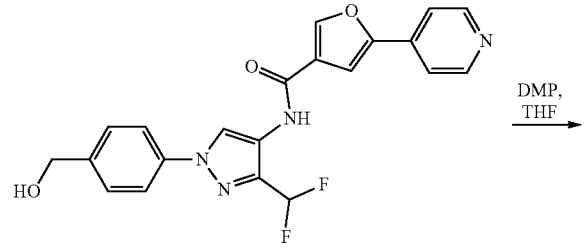

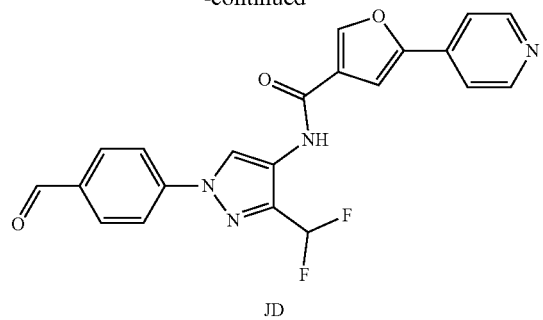

Step 1—N-[3-(difluoromethyl)-1-[4-(hydroxymethyl)phenyl]pyrazol-4-yl]-2-(4-pyridyl)oxazole-4-carboxamide To a solution of 2-(4-pyridyl)oxazole-4-carboxylic acid (1.27 g, 6.69 mmol, Intermediate ED) and HATU (3.18 g, 8.36 mmol) in DMF (60 mL) was added DIPEA (3.24 g, 25.0 mmol) and [4-[4-amino-3-(difluoromethyl) pyrazol-1-yl]phenyl]methanol (2 g, 8.36 mmol, Intermediate JB). The mixture was stirred at 25° C. for 2 hours. On completion, the reaction mixture was diluted with water (80 mL), filtered to give the filter cake and dried in vacuo to give the title compound (3.00 g, 87% yield) as gray solid. $^1$H NMR (400 MHz, DMSO-d$_6$) δ 10.05 (s, 1H), 9.04 (s, 1H), 8.83 (d, J=6.0 Hz, 2H), 8.78 (s, 1H), 7.97 (d, J=6.0 Hz, 2H), 7.82 (d, J=8.8 Hz, 2H), 7.48 (d, J=8.8 Hz, 2H), 7.29 (t, J=54 Hz, 1H), 5.30 (t, J=5.2 Hz, 1H), 4.56 (d, J=4.8 Hz, 2H).

Step 2—N-[3-(difluoromethyl)-1-(4-formylphenyl)pyrazol-4-yl]-2-(4-pyridyl)oxazole-4-carboxamide To a solution of N-[3-(difluoromethyl)-1-[4-(hydroxymethyl)phenyl]pyrazol-4-yl]-2-(4-pyridyl) oxazole-4-carboxamide (2.50 g, 6.08 mmol) in THF (160 mL) was added DMP (3.09 g, 7.29 mmol). The mixture was stirred at 20° C. for 12 hours. On completion, the reaction mixture was quenched with saturated Na$_2$S$_2$O$_3$ (20 mL) and saturated NaHCO$_3$ (20 mL) at 25° C., and then stirred for 30 minutes. The mixture was then extracted with CH$_2$Cl$_2$ (3×100 mL). The combined organic layers dried over Na$_2$SO$_4$, filtered and concentrated in vacuo to give the title compound (1.80 g, 73% yield) as gray solid. LC-MS (ESI$^+$) m/z 410.2 (M+H)$^+$.

4-[4-[[2-[2-[Tert-butoxycarbonyl(2,2,2-trifluoroethyl)amino]-4-pyridyl]oxazole-4-carbonyl]amino]-3-(difluoromethyl)pyrazol-1-yl]benzoic acid (Intermediate JE)

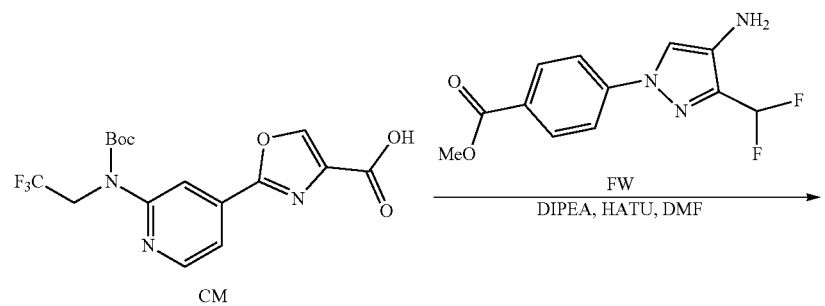

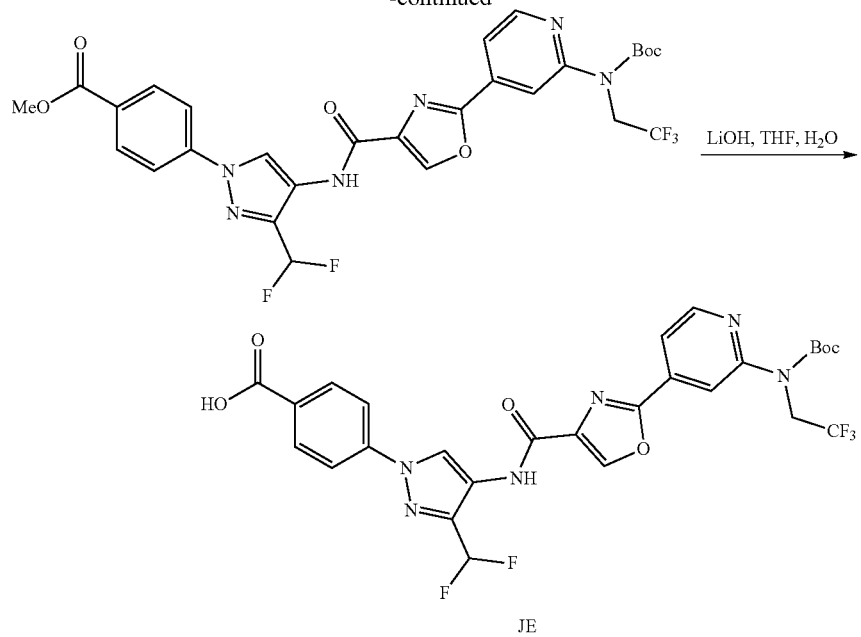

Step 1—Methyl 4-[4-[[2-[2-[tert-butoxycarbonyl(2,2,2-trifluoroethyl)amino]-4-pyridyl]oxazole-4-carbonyl]amino]-3-(difluoromethyl)pyrazol-1-yl]benzoate To a solution of methyl 4-[4-amino-3-(difluoromethyl)pyrazol-1-yl]benzoate (340 mg, 1.27 mmol, Intermediate FW) and 2-[2-[tert-butoxycarbonyl(2,2,2-trifluoroethyl)amino]-4-pyridyl]oxazole-4-carboxylic acid (493 mg, 1.27 mmol, Intermediate CM) in DMF (8 mL) was added DIPEA (658 mg, 5.09 mmol) and HATU (581 mg, 1.53 mmol). The reaction mixture was stirred at 20° C. for 1 hour. On completion, the mixture was quenched with water (80 mL), stirred and filtered. The filter cake was dried in vacuo to give the title compound (0.7 g, 86% yield) as an off-white solid. LC-MS (ESI$^+$) m/z 637.3 (M+H)$^+$.

Step 2—4-[4-[[2-[2-[Tert-butoxycarbonyl(2,2,2-trifluoroethyl)amino]-4-pyridyl]oxazole-4-carbonyl]amino]-3-(difluoromethyl)pyrazol-1-yl]benzoic acid To a solution of methyl 4-[4-[[2-[2-[tert-butoxycarbonyl(2,2,2-trifluoroethyl)amino]-4-pyridyl]oxazole-4-carbonyl]amino]-3-(difluoromethyl)pyrazol-1-yl]benzoate (0.70 g, 1.10 mmol) in a mixed solvent of THF (10 mL) and H$_2$O (2 mL) was added LiOH (132 mg, 5.50 mmol). The reaction mixture was stirred at 20° C. for 2 days. On completion, the mixture was acidified with 0.5 N HCl solution until the pH=3-4, then stirred and filtered. The filter cake was dried in vacuo to give the title compound (0.68 g, 99% yield) as a white solid. LC-MS (ESI$^+$) m/z 623.2 (M+H)$^+$.

3-(7-bromo-2-oxo-1,3-benzoxazol-3-yl)piperidine-2,6-dione (Intermediate JF

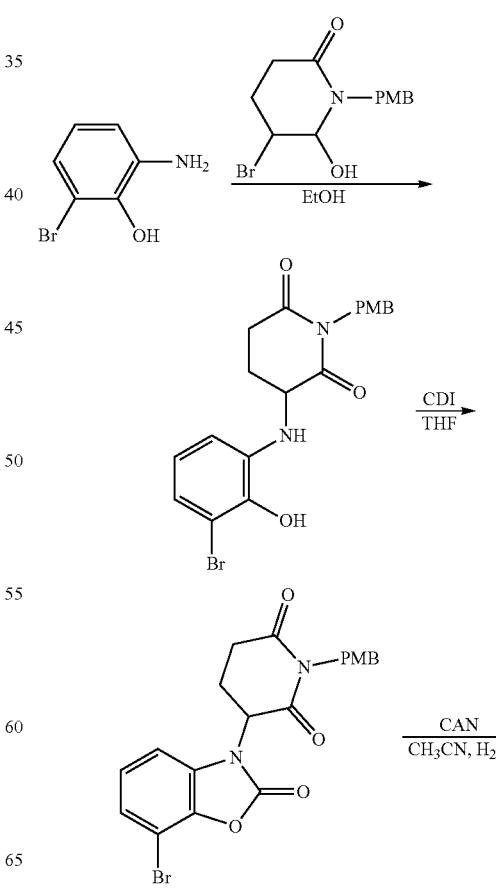

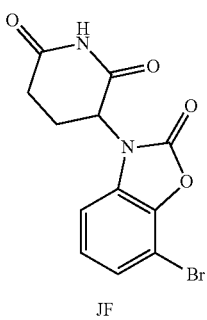

JF

Step 1—3-(3-bromo-2-hydroxyphenylamino)-1-(4-methoxybenzyl)piperidine-2,6-dione To a solution of 3-bromo-1-(4-methoxybenzyl)piperidine-2,6-dione (145 mg, 0.77 mmol, Intermediate LJ) in EtOH (10 mL) was added 2-amino-6-bromophenol (200 mg, 0.64 mmol) and at r.t. The reaction mixture was heated and stirred under microwave irradiation at 140° C. for 25 mins. The reaction mixture was concentrated under reduced pressure. The residue was purified via reverse phase column chromatography (ACN/H$_2$O with 0.1% TFA) to give title compound (80 mg, 30% yield) as a colorless oil. $^1$H NMR (400 MHz, DMSO-d$_6$) δ 8.94 (s, 1H), 7.18 (d, J=8.6 Hz, 2H), 6.85 (d, J=8.7 Hz, 2H), 6.75 (dd, J=6.9, 2.6 Hz, 1H), 6.67-6.59 (m, 2H), 5.48 (d, J=7.1 Hz, 1H), 4.76 (q, J=14.3 Hz, 2H), 4.58-4.40 (m, 1H), 3.71 (s, 3H), 3.05-2.89 (m, 1H), 2.83-2.61 (m, 1H), 2.25-2.10 (m, 1H), 2.02-1.97 (m, 1H). LC-MS (ESI$^+$): m/z 421.1 (M+H)$^+$.

Step 2—3-(7-bromo-2-oxobenzo[d]oxazol-3 (2H)-yl)-1-(4-methoxybenzyl)piperidine-2,6-dione To a solution of 3-(3-bromo-2-hydroxyphenyl amino)-1-(4-methoxybenzyl)piperidine-2,6-dione (80 mg, 0.19 mmol) in THF (5 mL) was added a solution of CDI (46 mg, 0.284 mmol) in THF (5 mL) at r.t. under N$_2$. The reaction mixture was stirred at 35° C. for 12 h. The reaction mixture was then concentrated under reduced pressure and the residue was purified via column chromatography (Petroleum ether/EtOAc=2/1) to give title compound (70 mg, 74% yield) as a white solid. $^1$H NMR (400 MHz, DMSO-d$_6$) δ 7.39 (dd, J=8.0, 1.1 Hz, 1H), 7.23-7.16 (m, 4H), 6.86 (d, J=8.7 Hz, 2H), 5.56 (dd, J=13.3, 5.3 Hz, 1H), 4.89-4.70 (m, 2H), 3.72 (s, 3H), 3.04-3.01 (m, 1H), 2.87-2.83 (m, 1H), 2.71-2.65 (m, 1H), 2.27-2.18 (m, 1H). LC-MS (ESI$^+$): m/z 445.1 (M+H)$^+$.

Step 3—3-(7-bromo-2-oxobenzo[d]oxazol-3 (2H)-yl)piperidine-2,6-dione

To a solution of 3-(7-bromo-2-oxobenzo[d]oxazol-3 (2H)-yl)-1-(4-methoxybenzyl)piperidine-2,6-dione (80 mg, 0.180 mmol) in CH$_3$CN (2 mL) was added a solution of CAN (690 mg, 1.26 mmol) in 0.5 mL of water dropwise at r.t. The reaction mixture was stirred at r.t. for 2 hours. The reaction mixture was then extracted with EtOAc (15 mL×2), the organic layer washed with brine, dried over anhydrous Na$_2$SO$_4$ and concentrated under reduced pressure. The residue was purified via Pre-TLC (Petroleum ether/EtOAc=1/1) to give the title compound (9.7 mg, 17% yield) as a pale yellow solid. $^1$H NMR (400 MHz, DMSO-d$_6$) δ 11.26 (s, 1H), 7.39 (dd, J=8.2, 0.8 Hz, 1H), 7.33-7.27 (m, 1H), 7.19 (t, J=8.1 Hz, 1H), 5.42-5.38 (m, 1H), 2.97-2.79 (m, 1H), 2.75-2.60 (m, 2H), 2.27-2.12 (m, 1H). LC-MS (ESI$^+$): m/z 325.1 (M+H)$^+$.

3-[7-[3-[2-(2-Aminoethoxy)ethoxy]propyl]-2-oxo-1,3-benzoxazol-3-yl]piperidine-2,6-dione (Intermediate JG)

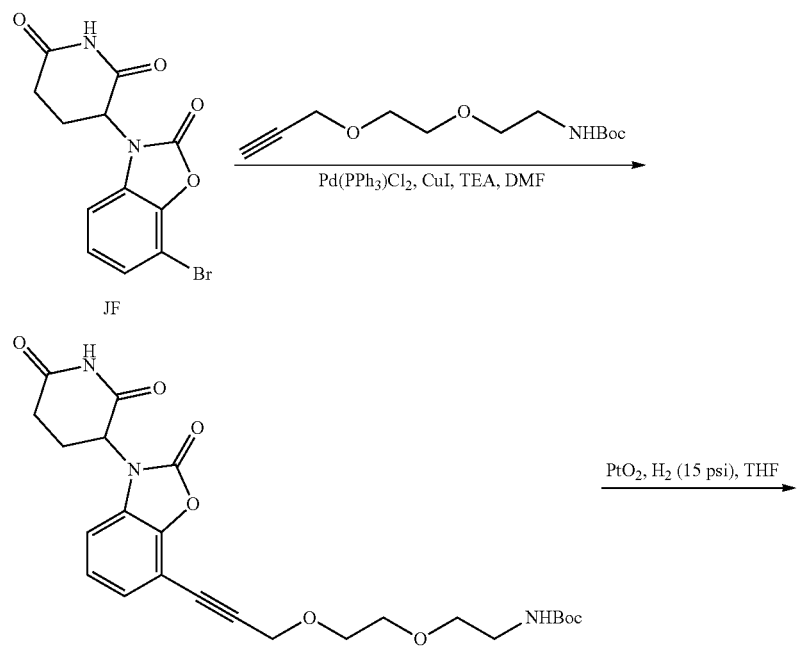

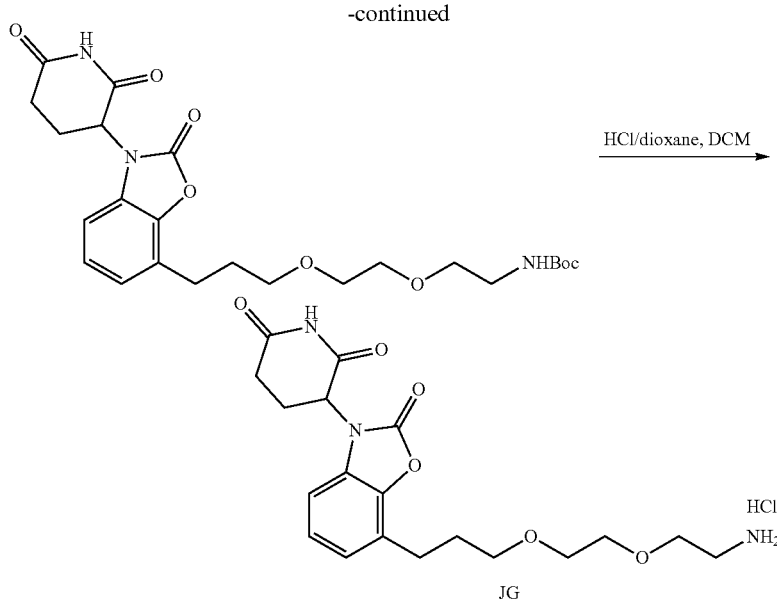

Step 1—Tert-butyl N-[2-[2-[3-[3-(2,6-dioxo-3-piperidyl)-2-oxo-1,3-benzoxazol-7-yl]prop-2-ynoxy]ethoxy]ethyl]carbamate To a solution of 3-(7-bromo-2-oxo-1,3-benzoxazol-3-yl)piperidine-2,6-dione (220 mg, 676 umol, Intermediate JF) and tert-butyl N-[2-(2-prop-2-ynoxyethoxy)ethyl]carbamate (411 mg, 1.69 mmol, synthesized via Step 1 of Intermediate CQ) in DMF (10 mL) was added TEA (1.23 g, 12.1 mmol, 1.70 mL), CuI (64.4 mg, 338 umol) and Pd(PPh$_3$)$_2$Cl$_2$ (237 mg, 338 umol). The reaction mixture was stirred at 80° C. for 1.5 hours under N$_2$. On completion, the mixture was filtered; and the filtrate was concentrated in vacuo to give a residue. The residue was dissolved in DCM (20 mL) and thiourea (resin) (300 mg) was added. The mixture was stirred at 20° C. for 2 hours. Then the reaction mixture was filtered and the filtrate was concentrated in vacuo to give a residue. The residue was purified by column chromatography to give the title compound (250 mg, 76% yield) as a yellow solid. LC-MS (ESI$^+$) m/z 510.2 (M+Na)$^+$.

Step 2—Tert-butyl N-[2-[2-[3-[3-(2,6-dioxo-3-piperidyl)-2-oxo-1,3-benzoxazol-7-yl]propoxy]ethoxy]ethyl]carbamate To a solution of tert-butyl N-[2-[2-[3-[3-(2,6-dioxo-3-piperidyl)-2-oxo-1,3-benzoxazol-7-yl]prop-2-ynoxy]ethoxy]ethyl]carbamate (250 mg, 512 umol) in THF (10 mL) was added PtO$_2$ (58.2 mg, 256 umol). The reaction mixture was stirred at 20° C. under H$_2$ (15 psi) for 1 hour. On completion, the residue was filtered and the filtrate was concentrated in vacuo to give the title compound (250 mg, 99%) as yellow oil. LC-MS (ESI$^+$) m/z 514.2 (M+Na)$^+$.

Step 3—3-[7-[3-[2-(2-Aminoethoxy)ethoxy]propyl]-2-oxo-1,3-benzoxazol-3-yl]piperidine-2,6-dione To a solution of tert-butyl N-[2-[2-[3-[3-(2,6-dioxo-3-piperidyl)-2-oxo-1,3-benzoxazol-7-yl]propoxy]ethoxy]ethyl]carbamate (250 mg, 508 umol) in DCM (4 mL) was added HCl/dioxane (4 M, 4 mL). The reaction mixture was stirred at 25° C. for 1 hour. On completion, the mixture was concentrated in vacuo to give the title compound (190 mg, 87% yield) as yellow oil. LC-MS (ESI$^+$) m/z 392.3 (M+H)$^+$.

2-(2,6-Dioxo-3-piperidyl)-5-[3-(methylamino)propyl]isoindoline-1,3-dione (Intermediate JH)

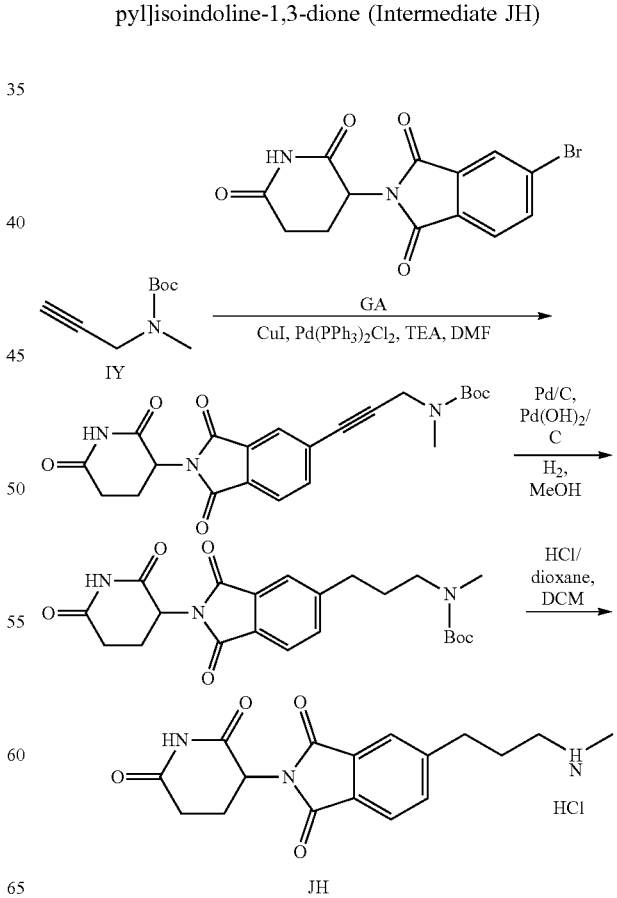

Step 1—Tert-butyl N-[3-[2-(2,6-dioxo-3-piperidyl)-1,3-dioxo-isoindolin-5-yl]prop-2-ynyl]-N-methyl-carbamate To a mixture of tert-butyl N-methyl-N-prop-2-ynyl-carbamate (1.00 g, 5.93 mmol, Intermediate IY) and 5-bromo-2-(2,6-dioxo-3-piperidyl)isoindoline-1,3-dione (1.00 g, 2.97 mmol, Intermediate GA) in DMF (4 mL) was added CuI (56.4 mg, 296 umol), TEA (5.40 g, 53.3 mmol, 7.43 mL) and Pd(PPh$_3$)$_2$Cl$_2$ (208 mg, 296 umol). The reaction mixture was heated at 80° C. for 0.5 hour under microwave. On completion, the reaction mixture was diluted with water (30 mL) and extracted with EA (3×50 mL). The combined organic layer was dried over Na$_2$SO$_4$, filtered and concentrated in vacuo to give a residue. The residue was purified by column chromatography to give the title compound (1.20 g, 95% yield) as yellow solid. $^1$H NMR (400 MHz, DMSO-d$_6$) δ 11.14 (s, 1H), 7.96-7.88 (m, 3H), 5.16 (dd, J=5.6, 12.8 Hz, 1H), 4.33 (s, 2H), 3.33 (s, 3H), 2.89-2.83 (m, 1H), 2.64-2.51 (m, 2H), 2.10-2.02 (m, 1H), 1.42 (s, 9H).

Step 2—Tert-butyl N-[3-[2-(2,6-dioxo-3-piperidyl)-1,3-dioxo-isoindolin-5-yl]propyl]-N-methyl-carbamate To a mixture of tert-butyl N-[3-[2-(2,6-dioxo-3-piperidyl)-1,3-dioxo-isoindolin-5-yl]prop-2-ynyl]-N-methyl-carbamate (2.40 g, 5.64 mmol) in MeOH (50 mL) was added Pd/C (500 mg, 10 wt %) and Pd(OH)$_2$/C (500 mg, 10 wt %). The reaction mixture was stirred at 20° C. for 1 hour under H$_2$ (15 Psi) atmosphere. On completion, the reaction mixture was filtered and concentrated in vacuo to give the title compound (2.40 g, 99% yield) as light yellow solid. LC-MS (ESI$^+$) m/z 452.3 (M+Na)$^+$.

Step 3—2-(2,6-Dioxo-3-piperidyl)-5-[3-(methylamino)propyl]isoindoline-1,3-dione To a mixture of tert-butyl N-[3-[2-(2,6-dioxo-3-piperidyl)-1,3-dioxo-isoindolin-5-yl]propyl]-N-methyl-carbamate (2.40 g, 5.59 mmol) in DCM (10 mL) was added HCl/dioxane (4 M, 19.2 mL). The reaction mixture was stirred at 20° C. for 1 hour. On completion, the reaction mixture was concentrated in vacuo to give the title compound (2.00 g, 97% yield) as light yellow solid. LC-MS (ESI$^+$) m/z 330.2 (M+H)$^+$.

5-(3-Aminopropyl)-2-(2,6-dioxo-3-piperidyl)isoindoline-1,3-dione (Intermediate JI)

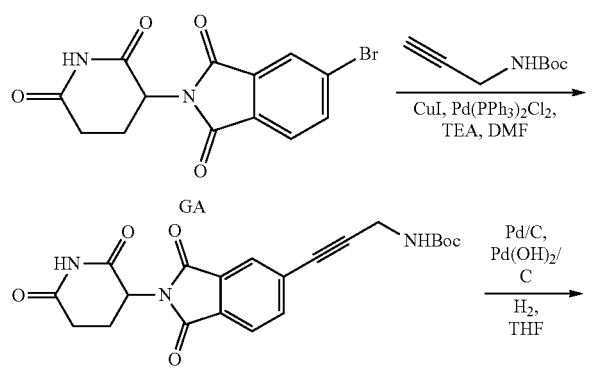

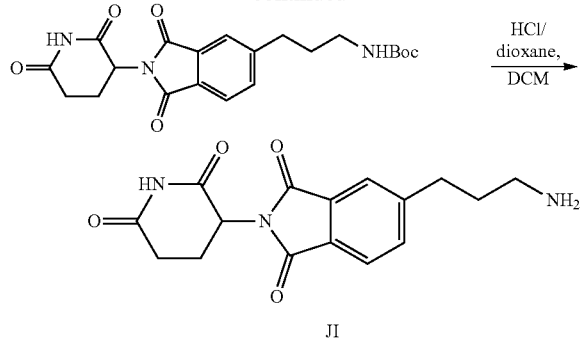

Step 1—Tert-butyl N-[3-[2-(2,6-dioxo-3-piperidyl)-1,3-dioxo-isoindolin-5-yl]prop-2-ynyl]carbamate To a solution of 5-bromo-2-(2,6-dioxo-3-piperidyl)isoindoline-1,3-dione (1 g, 2.97 mmol Intermediate GA) and tert-butyl N-prop-2-ynylcarbamate (920 mg, 5.93 mmol) in DMF (4 mL) was added Pd(PPh$_3$)$_2$Cl$_2$ (208 mg, 296 umol) TEA (5.40 g, 53 mmol, 7.43 mL) and CuI (57 mg, 296 umol). The mixture was stirred at 80° C. for 0.5 hr under microwave. On completion, the mixture was concentrated in vacuo, the residue was purified by silica gel chromatography to give the title compound (1.3 g, 95% yield) as yellow solid. $^1$H NMR (400 MHz, DMSO-d$_6$) δ 11.15 (s, 1H), 8.01-7.81 (m, 3H), 5.17 (dd, J=5.2, 12.8 Hz, 1H), 4.10-4.03 (m, 2H), 3.33 (s, 1H), 2.94-2.84 (m, 1H), 2.73-2.53 (m, 2H), 2.13-2.02 (m, 1H), 1.47-1.36 (m, 9H); LC-MS (ESI$^+$) m/z 434.0 (M+Na)$^+$.

Step 2—Tert-butyl N-[3-[2-(2,6-dioxo-3-piperidyl)-1,3-dioxo-isoindolin-5-yl]propyl]carbamate A mixture of tert-butyl N-[3-[2-(2,6-dioxo-3-piperidyl)-1,3-dioxo-isoindolin-5-yl]prop-2-ynyl]carbamate (2.5 g, 6.08 mmol), Pd/C (400 mg), Pd(OH)$_2$/C (400 mg) in THF (40 mL) was degassed and purged with H$_2$ gas 3 times. The mixture was then stirred at 20° C. for 16 hrs under H$_2$ atmosphere at 15 psi. On completion, the mixture was filtered and the filtrate was concentrated in vacuo to give the title compound (2.4 g, 95% yield) as brown solid. $^1$H NMR (400 MHz, DMSO-d$_6$) δ 11.12 (s, 1H), 7.84 (d, J=7.6 Hz, 1H), 7.80 (s, 1H), 7.72 (dd, J=1.2, 7.6 Hz, 1H), 6.94-6.85 (m, 1H), 5.14 (dd, J=5.2, 12.8 Hz, 1H), 2.99-2.84 (m, 3H), 2.82-2.72 (m, 2H), 2.65-2.54 (m, 2H), 2.11-2.01 (m, 1H), 1.80-1.68 (m, 2H), 1.38 (s, 9H) LC-MS (ESI$^+$) m/z 438.1 (M+Na)$^+$.

Step 3—5-(3-Aminopropyl)-2-(2,6-dioxo-3-piperidyl)isoindoline-1,3-dione

To a solution of tert-butyl N-[3-[2-(2,6-dioxo-3-piperidyl)-1,3-dioxo-isoindolin-5-yl]propyl]carbamate (2.4 g, 5.78 mmol) in DCM (25 mL) was added HCl/dioxane (4 M, 10 mL). The mixture was stirred at 20° C. for 2 hrs. On completion, the mixture was concentrated in vacuo to give the title compound (1.2 g, 65% yield) as light yellow solid. $^1$H NMR (400 MHz, DMSO-d$_6$) δ 11.14 (s, 1H), 8.01 (s, 3H), 7.88 (d, J=7.6 Hz, 1H), 7.84 (s, 1H), 7.76 (d, J=8.0 Hz, 1H), 5.15 (dd, J=5.2, 12.8 Hz, 1H), 2.95-2.84 (m, 3H), 2.83-2.72 (m, 2H), 2.69-2.52 (m, 2H), 2.11-2.01 (m, 1H), 1.97-1.89 (m, 2H); LC-MS (ESI$^+$) m/z 316.2 (M+H)$^+$.

5-(Aminomethyl)-2-(2,6-dioxo-3-piperidyl)isoindoline-1,3-dione (Intermediate JJ)

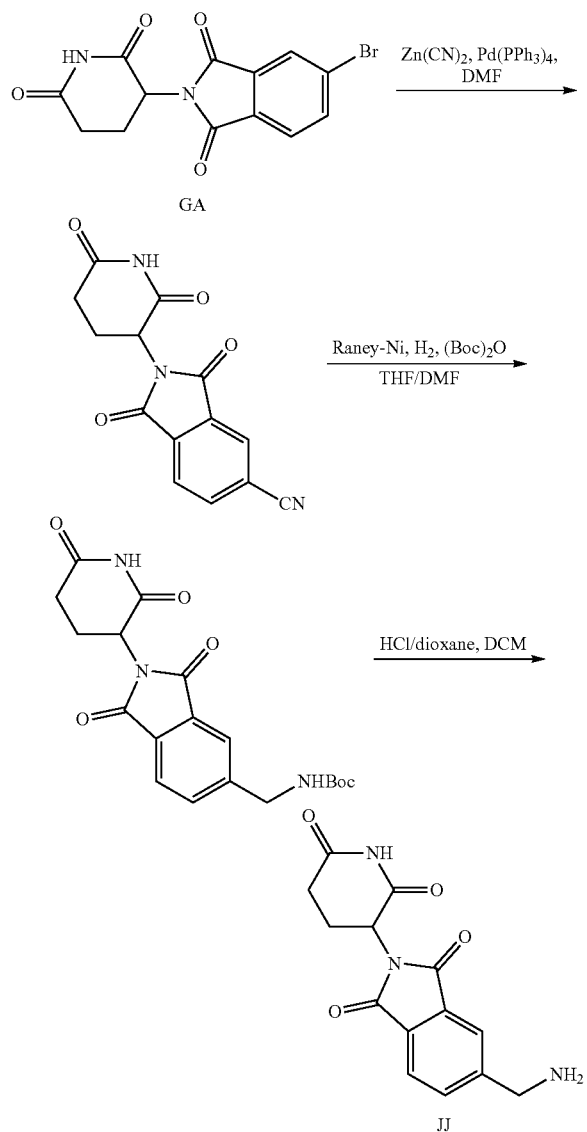

Step 1—2-(2,6-Dioxo-3-piperidyl)-1,3-dioxo-isoindoline-5-carbonitrile

To a solution of 5-bromo-2-(2,6-dioxo-3-piperidyl)isoindoline-1,3-dione (450 mg, 1.33 mmol, Intermediate GA), Zn(CN)$_2$ (94.0 mg, 800 umol) in DMF (15.0 mL) was added Pd(PPh$_3$)$_4$ (154 mg, 133 umol). The mixture was stirred at 100° C. for 3 hours under N$_2$. On completion, the mixture was diluted with H$_2$O (50 mL), filtered and the solid was dried in vacuo. The solid was triturated with PE:EA=5:1 (30 mL), filtered and the solid was dried in vacuo to give the title compound (200 mg, 52% yield) as purple solid. $^1$H NMR (400 MHz, DMSO-d$_6$) δ 11.16 (s, 1H), 8.49 (s, 1H), 8.38 (dd, J=1.2, 7.6 Hz, 1H), 8.12 (d, J=7.6 Hz, 1H), 5.26-5.17 (m, 1H), 2.97-2.89 (m, 1H), 2.65-2.58 (m, 1H), 2.57-2.52 (m, 1H), 2.12-2.05 (m, 1H).

Step 2—Tert-butyl N-[[2-(2,6-dioxo-3-piperidyl)-1,3-dioxo-isoindolin-5-yl]methyl]carbamate To a solution of 2-(2,6-dioxo-3-piperidyl)-1,3-dioxo-isoindoline-5-carbonitrile (200 mg, 706 umol) in THF (10.0 mL) and DMF (10.0 mL) was added (Boc)$_2$O (169 mg, 776 umol) and Raney-Ni (50.0 mg, 583 umol). The mixture was stirred at 30° C. for 3 hours under H$_2$ (50 psi). On completion, the mixture was filtered and concentrated in vacuo. The mixture was purified by silica gel column (PE:EA=1:1) to give the title compound (250 mg, 91% yield) as white solid. $^1$H NMR (400 MHz, DMSO-d$_6$) δ 11.10 (s, 1H), 7.88 (d, J=7.6 Hz, 1H), 7.76 (s, 1H), 7.72 (d, J=7.6 Hz, 1H), 7.63-7.55 (m, 1H), 5.18-5.04 (m, 1H), 4.33-4.24 (m, 2H), 2.95-2.88 (m, 1H), 2.84-2.83 (m, 1H), 2.64-2.57 (m, 1H), 2.57-2.52 (m, 1H), 2.11-2.01 (m, 1H), 1.39 (s, 9H).

Step 3—5-(Aminomethyl)-2-(2,6-dioxo-3-piperidyl)isoindoline-1,3-dione

To a solution of tert-butyl N-[[2-(2,6-dioxo-3-piperidyl)-1,3-dioxo-isoindolin-5-yl]methyl]carbamate (250 mg, 645 umol) in DCM (3.00 mL) was added HCl/dioxane (4.00 M, 4.00 mL), and the mixture was stirred at 15° C. for 0.5 hr. On completion, the mixture was concentrated in vacuo to give the title compound (200 mg, 90% yield, HCl) as white solid. LC-MS (ESI$^+$) m/z 288.1 (M+H)$^+$.

2-(2,6-Dioxo-3-piperidyl)-5-[3-[2-(methylamino)ethoxy]propyl]isoindoline-1,3-dione (Intermediate JK)

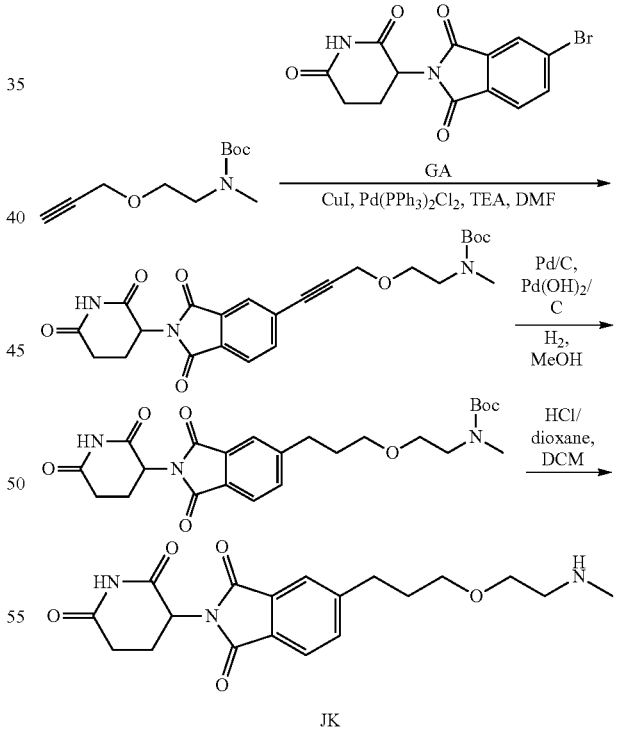

Step 1—Tert-butyl N-[2-[3-[2-(2,6-dioxo-3-piperidyl)-1,3-dioxo-isoindolin-5-yl]prop-2-ynoxy]ethyl]-N-methyl-carbamate To a solution of tert-butyl N-methyl-N-(2-prop-2-ynoxyethyl)carbamate (2.53 g, 11.8 mmol, Intermediate GK) and 5-bromo-2-(2,6-dioxo-3-piperidyl)isoindoline-1,3-dione (2.00 g, 5.93 mmol, Intermediate GA) in DMF (4.00 mL) was added TEA (10.8 g, 106 mmol), CuI (112 mg, 593 umol) and Pd(PPh$_3$)$_2$Cl$_2$ (416 mg, 593 umol), and the reaction mixture was heated at 80° C. for 30 min under microwave. On completion, the mixture was concentrated in vacuo. The mixture was purified by silica gel column (PE:EA=1:1) to give the title compound (2.7 g, 96% yield) as yellow solid. 1H NMR (400 MHz, CDCl$_3$) δ 8.00 (s, 1H), 7.93 (s, 1H), 7.89-7.79 (m, 2H), 5.02-4.96 (m, 1H), 4.44 (s, 2H), 3.73 (s, 2H), 3.48 (s, 2H), 2.97 (s, 3H), 2.96-2.91 (m, 1H), 2.89-2.82 (m, 1H), 2.82-2.73 (m, 1H), 2.22-2.15 (m, 1H), 1.48 (s, 9H).

Step 2—Tert-butyl N-[2-[3-[2-(2,6-dioxo-3-piperidyl)-1,3-dioxo-isoindolin-5-yl]propoxy]ethyl]-N-methyl-carbamate To a solution of tert-butyl N-[2-[3-[2-(2,6-dioxo-3-piperidyl)-1,3-dioxo-isoindolin-5-yl]prop-2-ynoxy]ethyl]-N-methylcarbamate (2.70 g, 5.75 mmol) in THF (30.0 mL) was added Pd/C (400 mg) and Pd(OH)$_2$/C (400 mg), and the mixture was stirred at 15° C. for 16 hr under H$_2$ (15 psi). On completion, the mixture was concentrated in vacuo to give the title compound (2.70 g, 95% yield) as black solid. LC-MS (ESI$^+$) m/z 496.1 (M+Na)$^+$.

Step 3—2-(2,6-Dioxo-3-piperidyl)-5-[3-[2-(methylamino)ethoxy]propyl]isoindoline-1,3-dione To a solution of tert-butyl N-[2-[3-[2-(2,6-dioxo-3-piperidyl)-1,3-dioxo-isoindolin-5-yl]propoxy]ethyl]-N-methyl-carbamate (2.70 g, 5.70 mmol) in DCM (20.0 mL) was added HCl/dioxane (4.00 M, 20.0 mL). The mixture was stirred at 15° C. for 0.5 hr. On completion, the mixture was concentrated in vacuo to give the title compound (2.37 g, 90% yield, HCl) as yellow solid. $^1$H NMR (400 MHz, DMSO-d$_6$) δ 11.14 (s, 1H), 9.02 (s, 1H), 7.87-7.74 (m, 3H), 5.19-5.10 (m, 1H), 3.67-3.63 (m, 2H), 3.57 (s, 3H), 3.46-3.42 (m, 2H), 3.12-3.03 (m, 2H), 2.91-2.86 (m, 2H), 2.64-2.58 (m, 1H), 2.57-2.55 (m, 1H), 2.55-2.54 (m, 1H), 2.10-2.01 (m, 1H), 1.94-1.83 (m, 2H).

4-[3-(Difluoromethyl)-4-[[2-(4-pyridyl)oxazole-4-carbonyl]amino]pyrazol-1-yl]benzoic acid (Intermediate JL)

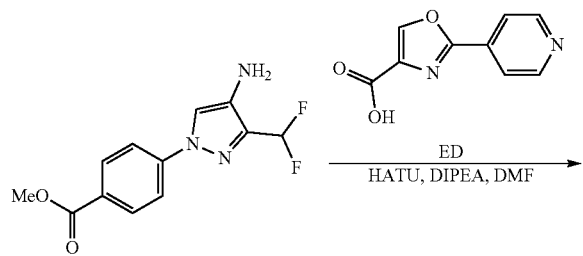


Step 1—Difluoromethyl)-4-[[2-(4-pyridyl)oxazole-4-carbonyl]amino]pyrazol-1-yl]benzoate A mixture of methyl 4-[4-amino-3-(difluoromethyl)pyrazol-1-yl]benzoate (900 mg, 3.37 mmol, Intermediate FW), 2-(4-pyridyl)oxazole-4-carboxylic acid (640 mg, 3.37 mmol, Intermediate ED), DIPEA (1.31 g, 10 mmol, 1.76 mL), and HATU (1.54 g, 4.04 mmol) in DMF (20 mL) was degassed and purged with N$_2$ gas 3 times, and then the mixture was stirred at 20° C. for 1 hr under N$_2$ atmosphere. On completion, the mixture was concentrated in vacuo. The residue was purified by prep-HPLC (basic condition) to give the title compound (1.45 g, 67% yield) as white solid. LC-MS (ESI$^+$) m/z 440.2 (M+1)$^+$.

Step 2—4-[3-(Difluoromethyl)-4-[[2-(4-pyridyl)oxazole-4-carbonyl]amino]pyrazol-1-yl]benzoic acid To a solution of methyl 4-[3-(difluoromethyl)-4-[[2-(4-pyridyl)oxazole-4-carbonyl]amino]pyrazol-1-yl]benzoate (1.60 g, 3.64 mmol) in a mixed of THF (160 mL), MeOH (20 mL) and H$_2$O (30 mL) was added LiOH (436 mg, 18.2 mmol). The mixture was stirred at 20° C. for 16 hrs. On completion, the mixture was adjusted to pH=6 with 1N HCl, and then filtered and the filter cake was dried in vacuo to give the title compound (1.5 g, 96% yield) as white solid. LC-MS (ESI$^+$) m/z 426.1 (M+1)$^+$.

N-[3-(difluoromethyl)-1-[4-[methyl(2-oxoethyl)carbamoyl]phenyl]pyrazol-4-yl]-2-(4-pyridyl) oxazole-4-carboxamide (Intermediate JM)

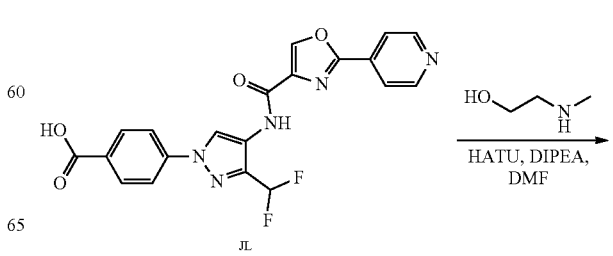

1485

-continued

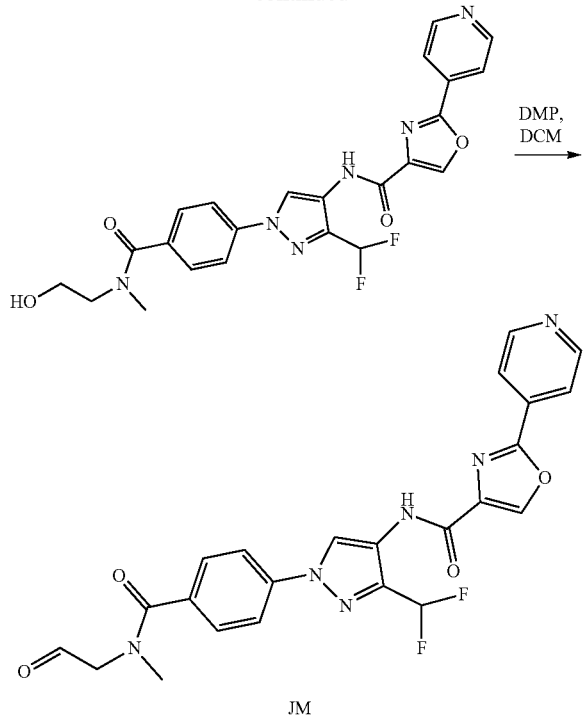

Step 1—N-[3-(difluoromethyl)-1-[4-[2-hydroxyethyl(methyl)carbamoyl]phenyl]pyrazol-4-yl]-2-(4-pyridyl)oxazole-4-carboxamide A mixture of 4-[3-(difluoromethyl)-4-[[2-(4-pyridyl)oxazole-4-carbonyl]amino]pyrazol-1-yl]benzoic acid (500 mg, 1.18 mmol, Intermediate JL), 2-(methylamino)ethanol (88.3 mg, 1.18 mmol, CAS #109-83-1), DIPEA (456 mg, 3.53 mmol, 614 uL), and HATU (537 mg, 1.41 mmol) in DMF (20 mL) was degassed and purged with $N_2$ gas 3 times, and then the mixture was stirred at 25° C. for 3 hrs under $N_2$ atmosphere. On completion, the mixture was concentrated in vacuo. The residue was purified by prep-HPLC (acid condition) to give the title compound (500 mg, 85% yield) as light yellow solid. $^1$H NMR (400 MHz, DMSO-$d_6$) δ 10.16 (s, 1H), 9.07 (s, 1H), 8.91-8.74 (m, 3H), 8.03-7.84 (m, 4H), 7.59 (d, J=8.4 Hz, 2H), 7.48-7.10 (m, 1H), 4.83 (s, 1H), 3.64-3.38 (m, 4H), 3.00 (s, 3H); LC-MS (ESI$^+$) m/z 483.2 (M+1)$^+$.

Step 2—N-[3-(difluoromethyl)-1-[4-[methyl(2-oxoethyl)carbamoyl]phenyl]pyrazol-4-yl]-2-(4-pyridyl)oxazole-4-carboxamide To a solution of N-[3-(difluoromethyl)-1-[4-[2-hydroxyethyl(methyl)carbamoyl]phenyl]pyrazol-4-yl]-2-(4-pyridyl)oxazole-4-carboxamide (500 mg, 1.04 mmol) in THF (10 mL) was added Dess-Martin (528 mg, 1.24 mmol). The mixture was stirred at 25° C. for 3 hrs. On completion, the mixture was quenched with saturated $Na_2S_2O_3$ (10 mL), then extracted with DCM (2×150 mL). The organic layer was concentrated in vacuo to give the title compound (490 mg, 98% yield) as yellow solid. LC-MS (ESI$^+$) m/z 481.2 (M+1)$^+$.

1486

2-(2,6-Dioxo-3-piperidyl)-5-[2-(2-hydroxyethoxy)ethyl]isoindoline-1,3-dione (Intermediate JN)

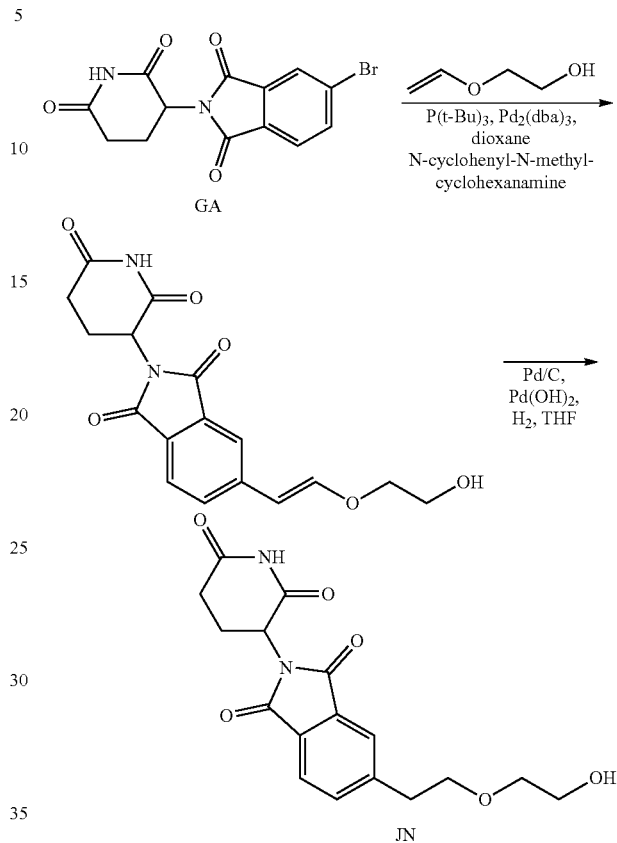

Step 1—2-(2,6-Dioxo-3-piperidyl)-5-[(E)-2-(2-hydroxyethoxy)vinyl]isoindoline-1,3-dione To a solution of 5-bromo-2-(2,6-dioxo-3-piperidyl)isoindoline-1,3-dione (2.00 g, 5.93 mmol Intermediate GA), 2-vinyloxyethanol (1.05 g, 11.8 mmol) in dioxane (15.0 mL) was added P(t-Bu)$_3$ (2.40 g, 1.19 mmol, 10 wt %), Pd$_2$(dba)$_3$ (543 mg, 593 umol) and N-cyclohexyl-N-methyl-cyclohexanamine (1.51 g, 7.71 mmol), and the mixture was stirred at 25° C. for 16 hrs. On completion, the mixture was concentrated in vacuo. The mixture was purified by silica gel column (EA) to give the title compound (2.00 g, 97% yield) as yellow solid. $^1$H NMR (400 MHz, DMSO-$d_6$) δ 11.13 (s, 1H), 7.91 (s, 1H), 7.79-7.76 (m, 1H), 7.72 (s, 1H), 7.71-7.67 (m, 1H), 6.08 (d, J 12.8 Hz, 1H), 5.17-5.10 (m, 1H), 4.91-4.86 (m, 1H), 3.96 (t, J=4.8 Hz, 2H), 3.70-3.63 (m, 2H), 2.95-2.84 (m, 1H), 2.65-2.57 (m, 1H), 2.57-2.53 (m, 1H), 2.11-2.01 (m, 1H).

Step 2—2-(2,6-Dioxo-3-piperidyl)-5-[2-(2-hydroxyethoxy)ethyl]isoindoline-1,3-dione To a solution of 2-(2,6-dioxo-3-piperidyl)-5-[(E)-2-(2-hydroxyethoxy)vinyl]isoindoline-1,3-dione (1.00 g, 2.90 mmol) in THF (40.0 mL) was added Pd/C (300 mg, 10 wt %) and Pd(OH)$_2$/C (300 mg, 10 wt %). The mixture was stirred at 15° C. for 12 hours under $H_2$ (15 psi). On completion, the mixture was filtered and concentrated in vacuo to give the title compound (1.00 g, 95% yield) as yellow solid. LC-MS (ESI⁺) m/z 347.2 (M+H)⁺.

2-[2-[2-(2,6-Dioxo-3-piperidyl)-1,3-dioxo-isoindolin-5-yl]ethoxy]ethyl methanesulfonate (Intermediate JO)

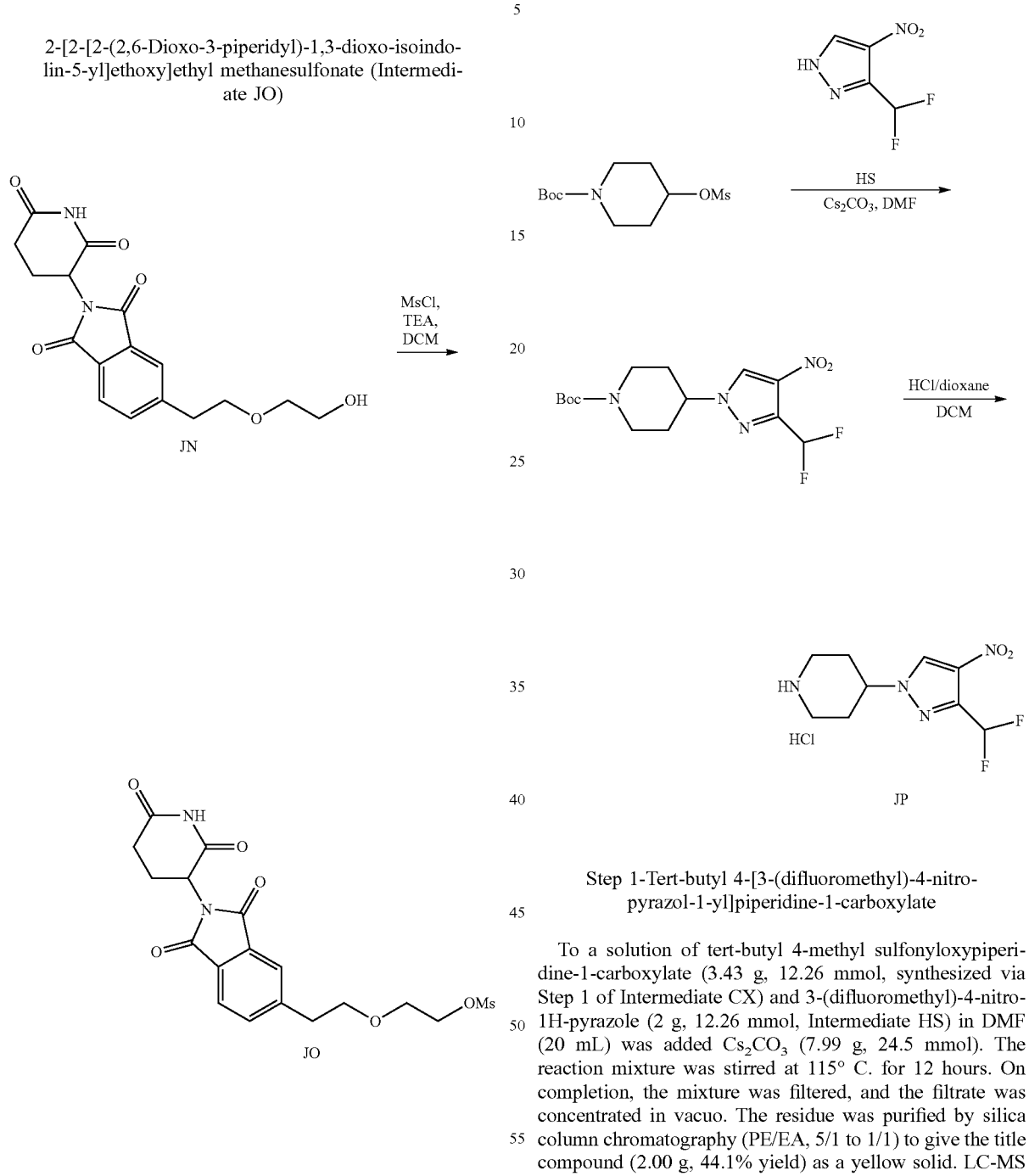

To a solution of 2-(2,6-dioxo-3-piperidyl)-5-[2-(2-hydroxyethoxy)ethyl]isoindoline-1,3-dione (300 mg, 866 umol, Intermediate JN) in DCM (30.0 mL) was added MsCl (148 mg, 1.30 mmol) and TEA (262 mg, 2.60 mmol), and the mixture was stirred at 15° C. for 0.5 hr. On completion, the mixture was diluted with DCM (20 mL), and extracted with H₂O (3×20 mL). The organic layer was dried over anhydrous Na₂SO₄, filtered and concentrated in vacuo to give the title compound (350 mg, 95% yield) as yellow oil. LC-MS (ESI⁺) m/z 425.2 (M+H)⁺.

4-[3-(difluoromethyl)-4-nitro-pyrazol-1-yl]piperidine (Intermediate JP)

Step 1-Tert-butyl 4-[3-(difluoromethyl)-4-nitro-pyrazol-1-yl]piperidine-1-carboxylate To a solution of tert-butyl 4-methyl sulfonyloxypiperidine-1-carboxylate (3.43 g, 12.26 mmol, synthesized via Step 1 of Intermediate CX) and 3-(difluoromethyl)-4-nitro-1H-pyrazole (2 g, 12.26 mmol, Intermediate HS) in DMF (20 mL) was added Cs₂CO₃ (7.99 g, 24.5 mmol). The reaction mixture was stirred at 115° C. for 12 hours. On completion, the mixture was filtered, and the filtrate was concentrated in vacuo. The residue was purified by silica column chromatography (PE/EA, 5/1 to 1/1) to give the title compound (2.00 g, 44.1% yield) as a yellow solid. LC-MS (ESI⁺) m/z 291.0 (M+H−56)⁺.

Step 2—4-[3-(difluoromethyl)-4-nitro-pyrazol-1-yl]piperidine

To a solution of tert-butyl 4-[3-(difluoromethyl)-4-nitro-pyrazol-1-yl]piperidine-1-carboxylate (1 g, 2.89 mmol) in DCM (10 mL) was added HCl (4 M, 20 mL). The reaction mixture was concentrated in vacuo to give the title compound (830 mg, HCl, 85% purity) as a white solid. LC-MS (ESI⁺) m/z 247.0 (M+H)⁺.

5-[2-[2-[4-[4-Amino-3-(difluoromethyl)pyrazol-1-yl]-1-piperidyl]ethoxy]ethyl]-2-(2,6-dioxo-3-piperidyl)isoindoline-1,3-dione (Intermediate JQ)

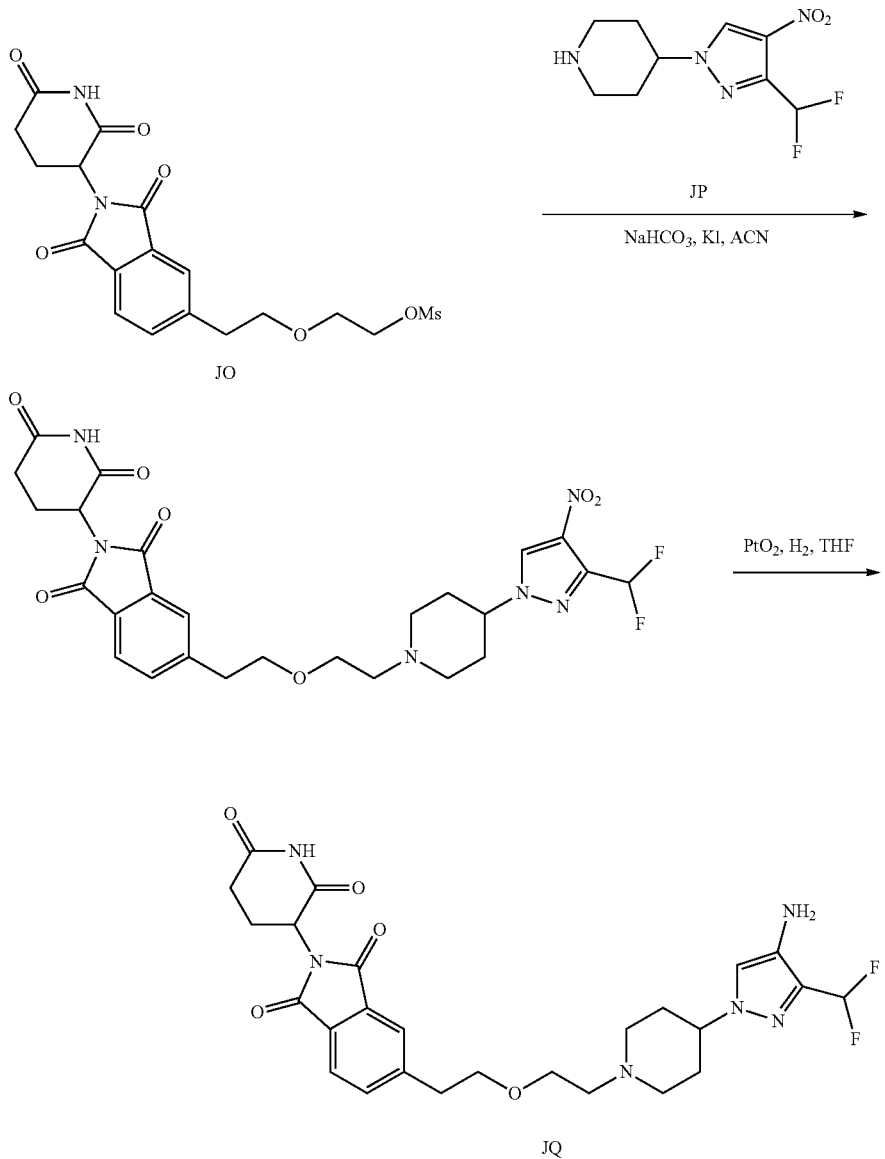

Step 1—5-[2-[2-[4-[3-(Difluoromethyl)-4-nitro-pyrazol-1-yl]-1-piperidyl]ethoxy]ethyl]-2-(2,6-dioxo-3-piperidyl)isoindoline-1,3-dione To a solution of 2-[2-[2-(2,6-dioxo-3-piperidyl)-1,3-dioxo-isoindolin-5-yl]ethoxy]ethyl methanesulfonate (225 mg, 530 umol, Intermediate JO), 4-[3-(difluoromethyl)-4-nitro-pyrazol-1-yl]piperidine (100 mg, 353 umol, HCl, Intermediate JP) in ACN (2.00 mL) was added KI (5.87 mg, 35.3 umol) and NaHCO₃ (89.1 mg, 1.06 mmol). The mixture was stirred at 80° C. for 16 hrs. On completion, the mixture was concentrated in vacuo. The mixture was purified by silica gel column (DCM:MeOH=50:1) to give the title compound (100 mg, 49% yield) as white solid. LC-MS (ESI⁺) m/z 575.1 (M+H)⁺.

Step 2—5-[2-[2-[4-[4-Amino-3-(difluoromethyl)pyrazol-1-yl]-1-piperidyl]ethoxy]ethyl]-2-(2,6-dioxo-3-piperidyl)isoindoline-1,3-dione To a solution of 5-[2-[2-[4-[3-(difluoromethyl)-4-nitro-pyrazol-1-yl]-1-piperidyl]ethoxy]ethyl]-2-(2,6-dioxo-3-piperidyl)isoindoline-1,3-dione (90.0 mg, 156 umol) in THF (5.00 mL) was added PtO₂ (3.56 mg, 15.6 umol), the mixture was stirred at 15° C. for 16 hrs under H₂ (15 psi). On completion, the mixture was filtered and the filtrate was concentrated in vacuo to give the title compound (85.0 mg, 90% yield) as yellow solid. LC-MS (ESI⁺) m/z 545.3 (M+H)⁺.

5-[3-(2-Aminoethoxy)propyl]-2-(2,6-dioxo-3-piperidyl)isoindoline-1,3-dione (Intermediate JR)

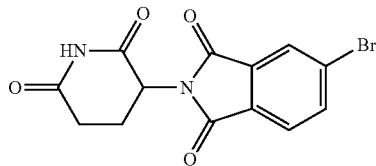

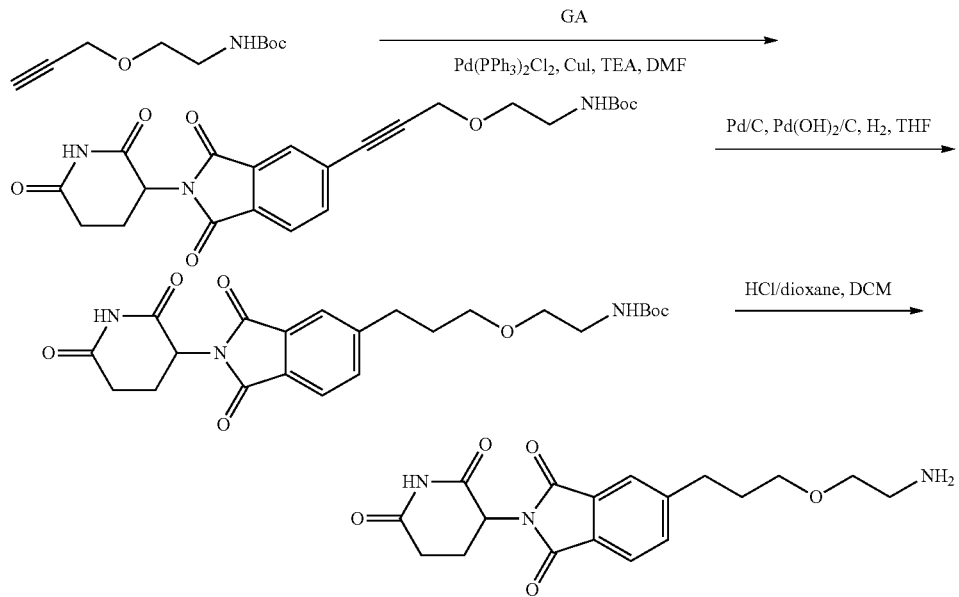

Step 1—Tert-butyl N-[2-[3-[2-(2,6-dioxo-3-piperidyl)-1,3-dioxo-isoindolin-5-yl]prop-2-ynoxy]ethyl]carbamate To a solution of tert-butyl N-(2-prop-2-ynoxyethyl)carbamate (2.36 g, 11.8 mmol synthesized via Step 1 on Intermediate CP), 5-bromo-2-(2,6-dioxo-3-piperidyl)isoindoline-1,3-dione (2.00 g, 5.93 mmol, Intermediate GA) in DMF (4.00 mL) was added CuI (112 mg, 593 umol), Pd(PPh$_3$)$_2$Cl$_2$ (416 mg, 593 umol), and TEA (10.8 g, 106 mmol). The mixture was stirred at 80° C. for 0.5 hr. On completion, the mixture was concentrated in vacuo. The mixture was purified by silica gel column (PE:EA=1:1) to give the title compound (2.60 g, 96% yield) as yellow solid. $^1$H NMR (400 MHz, DMSO-d$_6$) δ 11.2 (s, 1H), 8.01 (s, 1H), 8.00 (s, 2H), 6.97-6.87 (m, 1H), 5.28-5.17 (m, 1H), 4.52 (s, 2H), 3.66-3.55 (m, 2H), 3.25-3.17 (m, 2H), 2.95-2.89 (m, 1H), 2.71-2.63 (m, 1H), 2.62-2.58 (m, 1H), 2.17-2.09 (m, 1H), 1.43 (s, 9H).

Step 2—Tert-butyl N-[2-[3-[2-(2,6-dioxo-3-piperidyl)-1,3-dioxo-isoindolin-5-yl]propoxy]ethyl]carbamate To a solution of tert-butyl N-[2-[3-[2-(2,6-dioxo-3-piperidyl)-1,3-dioxo-isoindolin-5-yl]prop-2-ynoxy]ethyl]carbamate (2.60 g, 5.71 mmol) in THF (30.0 mL) was added Pd/C (500 mg, 10 wt %), and Pd(OH)$_2$/C (500 mg, 10 wt %). The mixture was stirred at 15° C. for 16 hours under H$_2$ (15 psi). On completion, the mixture was filtered and concentrated in vacuo to give the title compound (2.40 g, 91% yield) as yellow solid. LC-MS (ESI$^+$) m/z 482.3 (M+Na)$^+$.

Step 3—5-[3-(2-Aminoethoxy)propyl]-2-(2,6-dioxo-3-piperidyl)isoindoline-1,3-dione To a solution of tert-butyl N-[2-[3-[2-(2,6-dioxo-3-piperidyl)-1,3-dioxo-isoindolin-5-yl]propoxy]ethyl]carbamate (2.40 g, 5.22 mmol) in DCM (15.0 mL) was added HCl/dioxane (4.00 M, 15.0 mL). The mixture was stirred at 15° C. for 0.5 hour. On completion, the mixture was concentrated in vacuo to give the title compound (2.00 g, 90% yield, HCl) as yellow solid. $^1$H NMR (400 MHz, DMSO-d$_6$) δ 11.18 (s, 1H), 8.14 (s, 2H), 7.91 (d, J=7.6 Hz, 1H), 7.87 (s, 1H), 7.81 (d, J=7.6 Hz, 1H), 5.25-5.15 (m, 1H), 3.66-3.63 (m, 2H), 3.52-3.47 (m, 2H), 3.07-2.98 (m, 2H), 2.97-2.94 (m, 1H), 2.93-2.88 (m, 2H), 2.70-2.64 (m, 1H), 2.62-2.58 (m, 1H), 2.15-2.08 (m, 1H), 1.99-1.90 (m, 2H).

1493

Methyl 4-(3-bromo-4-nitro-pyrazol-1-yl)benzoate (Intermediate JS)

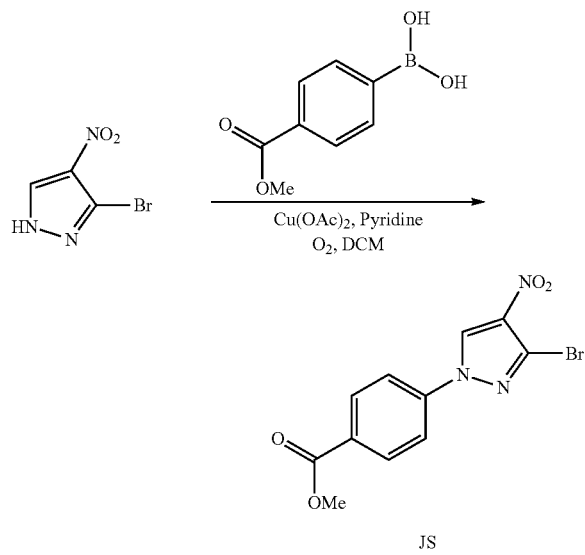

To a solution of 3-bromo-4-nitro-1H-pyrazole (4.8 g, 25.0 mmol, CAS #784193-37-9) and (4-methoxycarbonylphenyl) boronic acid (6.75 g, 37.5 mmol, CAS #99768-12-4) in DCM (100 mL) was added Cu(OAc)$_2$ (4.54 g, 25.0 mmol), and pyridine (7.91 g, 100 mmol) under O$_2$ (15 Psi). The reaction mixture was stirred at 20° C. for 12 hours under O$_2$ (15 Psi) atmosphere. On completion, the mixture was washed with NH$_3$.H$_2$O (50 mL), filtered and extracted with ethyl acetate (3×100 mL). The combined organic layers were washed with 2 N aq.HCl (60 mL) and brine (2×100 mL), dried over anhydrous sulfate sodium, filtered and concentrated in vacuo. The crude product was triturated with PE:EA=10:1 (100 mL) to give the title compound (5.00 g, 61% yield) as a white solid. $^1$H NMR (400 MHz, DMSO-d$_6$) δ 9.82 (s, 1H), 8.11-8.06 (m, 4H), 3.88 (s, 3H).

Methyl 4-[4-amino-3-[3-(2-hydroxyethyl)-2-oxo-imidazolidin-1-yl]pyrazol-1-yl]benzoate (Intermediate JT)

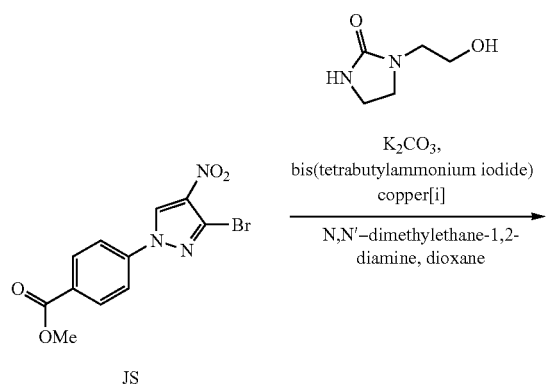

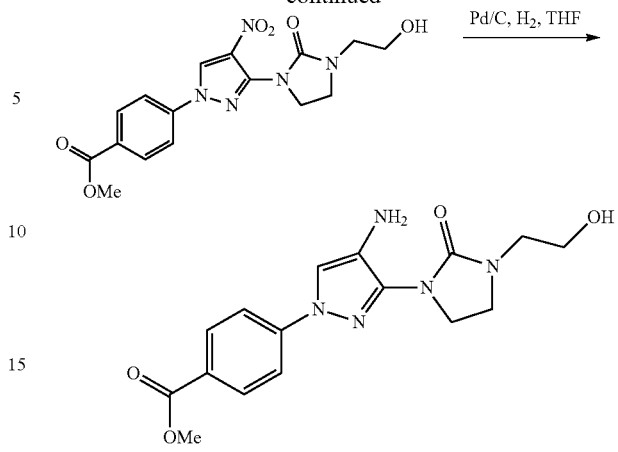

Step 1—Methyl 4-[3-[3-(2-hydroxyethyl)-2-oxo-imidazolidin-1-yl]-4-nitro-pyrazol-1-yl]benzoate A mixture of methyl 4-(3-bromo-4-nitro-pyrazol-1-yl) benzoate (500 mg, 1.53 mmol, 1 eq, Intermediate JS), 1-(2-hydroxyethyl)imidazolidin-2-one (239 mg, 1.84 mmol, CAS #3699-54-5), bis (tetrabutylammonium iodide) copper [I] (132 mg, 306 umol), K$_2$CO$_3$ (423 mg, 3.07 mmol) and N1,N2-dimethylethane-1,2-diamine (27.0 mg, 306 umol) in dioxane (25 mL) was degassed and purged with N$_2$ 3 times. Then the mixture was stirred at 110° C. for 16 hours under N$_2$ atmosphere. The mixture was filtered and the filtrate was concentrated in vacuo. The residue was purified by Pre-HPLC (acid condition) give the title compound (110 mg, 17% yield) as yellow solid; LC-MS (ESI$^+$) m/z 376.0 (M+H)$^+$.

Step 2—Methyl 4-[4-amino-3-[3-(2-hydroxyethyl)-2-oxo-imidazolidin-1-yl]pyrazol-1-yl]benzoate To a solution of methyl 4-[3-[3-(2-hydroxyethyl)-2-oxo-imidazolidin-1-yl]-4-nitro-pyrazol-1-yl]benzoate (110 mg, 293 umol) in THF (10 mL) was added Pd/C (20 mg, 10 wt %). The mixture was stirred at 20° C. for 3 hours under H$_2$ (15 Psi). On completion, the reaction mixture was filtered and the filtrate was concentrated in vacuo to give the title compound (100 mg, 98% yield) as yellow solid; LC-MS (ESI$^+$) m/z 346.2 (M+H)$^+$.

3,3-Dimethylpyrrolidin-2-one (Intermediate JU)

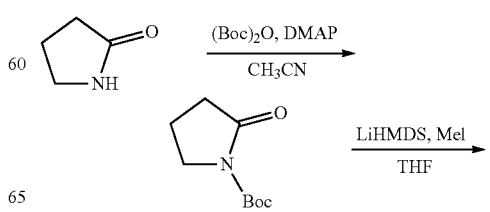

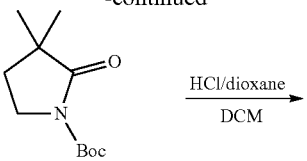

Step 1—Tert-butyl 2-oxopyrrolidine-1-carboxylate

To a solution of pyrrolidin-2-one (20 g, 235 mmol) in ACN (450 mL) was added (Boc)$_2$O (61.5 g, 282 mmol) and DMAP (2.87 g, 23.50 mmol) at 0° C. The mixture was stirred at 10° C. for 16 hours. On completion, the mixture was concentrated in vacuo. The residue was purified by column chromatography (SiO$_2$, PE/EA=3/1) to give the title compound (38 g, 87% yield) as light yellow solid. $^1$H NMR (400 MHz, CDCl$_3$) δ 3.74 (t, J=7.2 Hz, 2H), 2.50 (t, J=8.2 Hz, 2H), 2.06-1.93 (m, 2H), 1.52 (s, 9H).

Step 2—Tert-butyl 3,3-dimethyl-2-oxo-pyrrolidine-1-carboxylate

To a mixture of tert-butyl 2-oxopyrrolidine-1-carboxylate (4.5 g, 24.3 mmol) in THF (50 mL) was added LiHMDS (1.0 M, 25.5 mL) at −70° C. Then the reaction mixture was stirred at −30° C. for 0.5 hour. MeI (8.62 g, 60.7 mmol) was added to the mixture. The reaction mixture was stirred at 25° C. for 1 hour. On completion, the mixture was concentrated in vacuo. The residue was quenched with water (30 mL) and extracted with EtOAc (3×30 mL). The organic layer was dried with Na$_2$SO$_4$, filtrated and concentrated in vacuo. The residue was purified by column chromatography (SiO$_2$, PE:EA=5:1) to give the title product (2.80 g, 54% yield) as colorless solid. $^1$H NMR (400 MHz, CDCl$_3$) δ 3.67 (t, J=7.2 Hz, 2H), 1.85 (t, J=7.2 Hz, 2H), 1.55 (s, 9H), 1.20 (s, 6H).

Step 3—3,3-Dimethylpyrrolidin-2-one

To a mixture of tert-butyl 3,3-dimethyl-2-oxo-pyrrolidine-1-carboxylate (2.0 g, 9.38 mmol) in DCM (3 mL) was added HCl/dioxane (4 M, 2.00 mL). Then the reaction mixture was stirred at 25° C. for 12 hours. On completion, the reaction mixture was concentrated in vacuo to give the title compound (1.00 g, 94% yield) as yellowish solid. $^1$H NMR (400 MHz, DMSO-d$_6$) δ 3.06 (t, J=6.8 Hz, 2H), 1.76 (t, J=6.8 Hz, 2H), 0.93 (s, 6H).

Methyl 4-[4-amino-3-(3,3-dimethyl-2-oxo-pyrrolidin-1-yl)pyrazol-1-yl]benzoate (Intermediate JV)

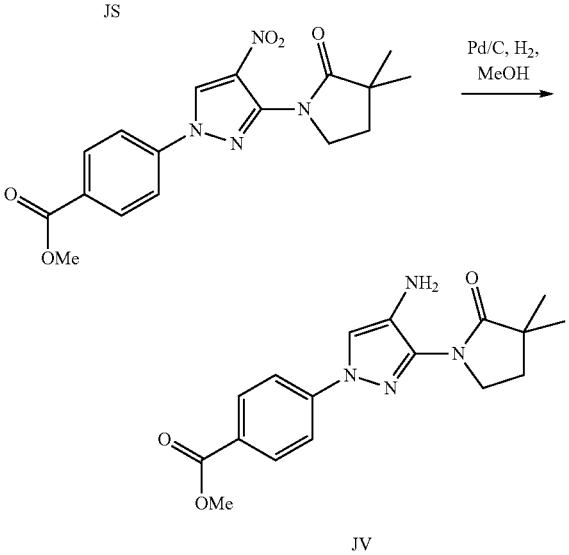

Step 1—Methyl 4-[3-(3,3-dimethyl-2-oxo-pyrrolidin-1-yl)-4-nitro-pyrazol-1-yl]benzoate A mixture of methyl 4-(3-bromo-4-nitro-pyrazol-1-yl)benzoate (500 mg, 1.53 mmol, Intermediate JS), 3,3-dimethylpyrrolidin-2-one (208 mg, 1.84 mmol, Intermediate JU), bis(tetrabutylammonium iodide) copper[I] (132 mg, 306 umol), K$_2$CO$_3$ (423 mg, 3.07 mmol) and N,N'-dimethylethane-1,2-diamine (27.0 mg, 306 umol) in dioxane (20 mL) was degassed and purged with N$_2$ gas 3 times, and then the mixture was stirred at 110° C. for 16 hours under N$_2$ atmosphere. On completion, the reaction mixture was filtered and the filtrate was concentrated in vacuo. The residue was purified by Pre-HPLC (acid condition) to give the title compound (200 mg, 18% yield) as yellow solid, LC-MS (ESI$^+$) m/z 359.2 (M+H)$^+$.

Step 2—Methyl 4-[4-amino-3-(3,3-dimethyl-2-oxo-pyrrolidin-1-yl)pyrazol-1-yl]benzoate To a solution of methyl 4-[3-(3,3-dimethyl-2-oxo-pyrrolidin-1-yl)-4-nitro-pyrazol-1-yl]benzoate (50 mg, 139 umol) in MeOH (5 mL) was added Pd/C (30 mg, 10 wt %) under N$_2$. The suspension was degassed under vacuum and purged with H₂ gas three times. The mixture was stirred at 20° C. for 3 hours under H₂ (15 Psi). On completion, the reaction mixture was concentrated in vacuo to give the title compound (45 mg, 97% yield) as light yellow solid; LC-MS (ESI⁺) m/z 329.2 (M+H)⁺.

2-(2,6-Dioxo-3-piperidyl)-4-(4-piperidylamino) isoindoline-1,3-dione (Intermediate JW)

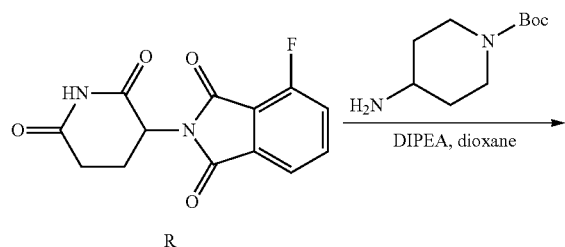

Step 1—Tert-butyl 4-[[2-(2,6-dioxo-3-piperidyl)-1,3-dioxo-isoindolin-4-yl]amino]piperidine-1-carboxylate To a solution of 2-(2,6-dioxo-3-piperidyl)-4-fluoro-isoindoline-1,3-dione (2.5 g, 9.05 mmol, Intermediate R) and tert-butyl 4-aminopiperidine-1-carboxylate (1.81 g, 9.05 mmol, CAS #502482-34-0) in dioxane (25 mL) was added DIPEA (4.68 g, 36.2 mmol). The reaction mixture was stirred at 115° C. for 15 hrs. On completion, the mixture was concentrated in vacuo. The residue was purified by silica gel chromatography to give the title compound (2.16 g, 52% yield) as a yellow solid. LC-MS (ESI⁺) m/z 479.1 (M+Na)⁺.

Step 2—2-(2,6-Dioxo-3-piperidyl)-4-(4-piperidylamino)isoindoline-1,3-dione

To a solution of tert-butyl 4-[[2-(2,6-dioxo-3-piperidyl)-1,3-dioxo-isoindolin-4-yl]amino]piperidine-1-carboxylate (2.16 g, 4.73 mmol) in DCM (5 mL) was added HCl/dioxane (10 mL). The reaction mixture was stirred at 20° C. for 2 hrs. On completion, the mixture was concentrated in vacuo. The residue was triturated with DCM (50 mL), stirred and filtered. The filter cake was dried in vacuo to give the title compound (1.20 g, 65% yield, HCl) as a yellow green solid. LC-MS (ESI⁺) m/z 357.1 (M+H)⁺.

Tert-butyl N-[2-[2-[2-(2-oxoethoxy)ethoxy]ethoxy]ethyl]carbamate (Intermediate JX)

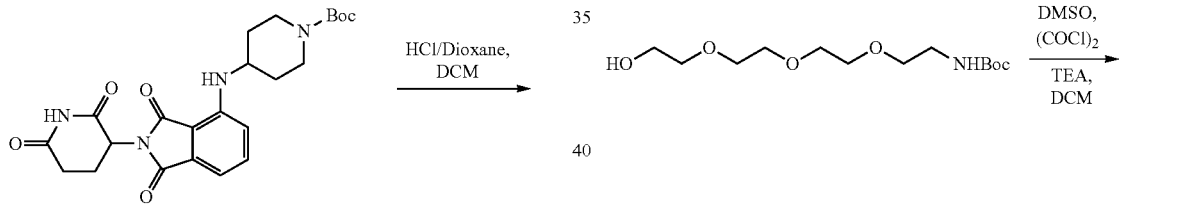

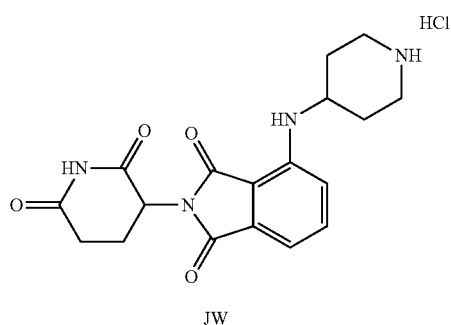

To a solution of DMSO (1.33 g, 17.0 mmol) in DCM (10 mL) was added a solution of (COCl)₂ (1.73 g, 13.6 mmol) in DCM (15 mL) dropwise at −70° C. The mixture was stirred at this temperature for 10 minutes. Then a solution of tert-butyl N-[2-[2-[2-(2-hydroxyethoxy)ethoxy]ethoxy]ethyl]carbamate (2.00 g, 6.82 mmol, synthesized via Steps 1-3 of Intermediate AO) in DCM (15 mL) was added into the above mixture slowly. After stirred at −70° C. for 50 minutes, TEA (5.52 g, 54.5 mmol) was added and the reaction mixture was stirred at −70° C. for 0.5 hr. On completion, the mixture was quenched with water (30 mL), and then separated. The aqueous phase was extracted with DCM (2×30 mL). Then the organic phase was combined and washed with brine (2×30 mL), dried over Na₂SO₄, filtered and the filtrate was concentrated in vacuo to give the title compound (1.50 g, 76% yield) as yellow oil, which was used directly in the next step without further purification.

4-[[1-[2-[2-[2-(2-Aminoethoxy)ethoxy]ethoxy]ethyl]-4-piperidyl]amino]-2-(2,6-dioxo-3-piperidyl)isoindoline-1,3-dione (Intermediate JY)

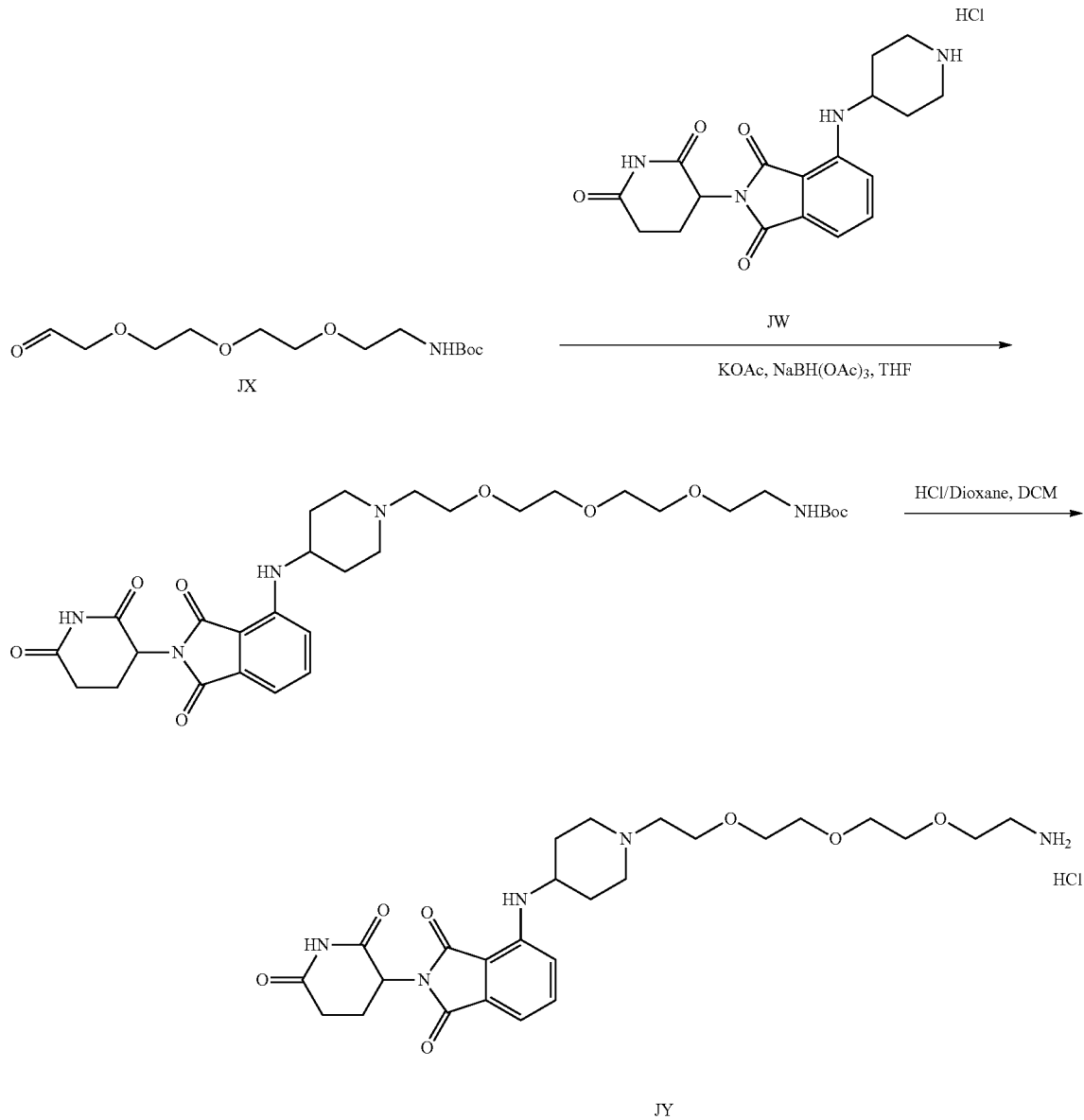

Step 1—Tert-butyl N-[2-[2-[2-[2-[4-[[2-(2,6-dioxo-3-piperidyl)-1,3-dioxo-isoindolin-4-yl]amino]-1-piperidyl]ethoxy]ethoxy]ethoxy]ethyl]carbamate To a mixture of tert-butyl N-[2-[2-[2-(2-oxoethoxy)ethoxy]ethoxy]ethyl]carbamate (386 mg, 1.32 mmol, Intermediate JX) and 2-(2,6-dioxo-3-piperidyl)-4-(4-piperidylamino)isoindoline-1,3-dione (400 mg, 1.02 mmol, HCl, Intermediate JW) in THF (20 mL) was added KOAc (200 mg, 2.04 mmol). One hour later, NaBH(OAc)₃ (432 mg, 2.04 mmol) was added and the reaction mixture was stirred at 20° C. for 16 hrs. On completion, the mixture was concentrated in vacuo. The residue was purified by reverse phase (0.1% HCl condition) to give the title compound (550 mg, 86% yield) as a yellow solid. LC-MS (ESI⁺) m/z 632.4 (M+H)⁺

Step 2—4-[[1-[2-[2-[2-(2-Aminoethoxy)ethoxy]ethoxy]ethyl]-4-piperidyl]amino]-2-(2,6-dioxo-3-piperidyl)isoindoline-1,3-dione To a solution of tert-butyl N-[2-[2-[2-[2-[4-[[2-(2,6-dioxo-3-piperidyl)-1,3-dioxo-isoindolin-4-yl]amino]-1-piperidyl]ethoxy]ethoxy]ethoxy]ethyl]carbamate (550 mg, 871 umol) in DCM (5 mL) was added HCl/dioxane (10 mL). The reaction mixture was stirred at 20° C. for 10 hrs. On completion, the mixture was concentrated in vacuo to give the title compound (460 mg, 93% yield, HCl) as a yellow solid. LC-MS (ESI⁺) m/z 532.2 (M+H)⁺.

5-[[1-[2-(2-Aminoethoxy)ethyl]-4-piperidyl]amino]-2-(2,6-dioxo-3-piperidyl)isoindoline-1,3-dione (Intermediate JZ)

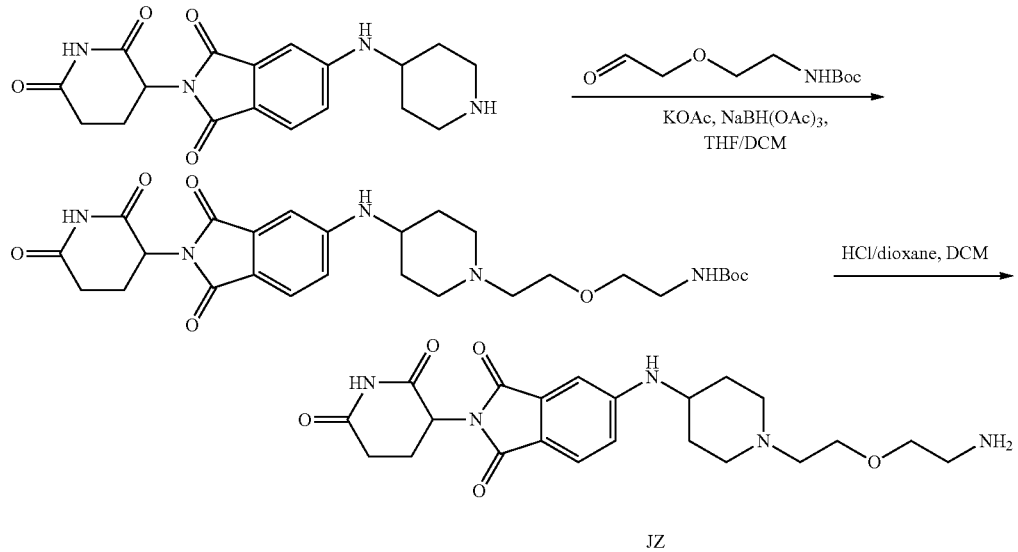

Step 1—Tert-butyl N-[2-[2-[4-[[2-(2,6-dioxo-3-piperidyl)-1,3-dioxo-isoindolin-5-yl]amino]-1-piperidyl]ethoxy]ethyl]carbamate To a solution of 2-(2,6-dioxo-3-piperidyl)-5-(4-piperidylamino)isoindoline-1,3-dione (400 mg, 1.02 mmol, HCl, synthesized via Steps 1-2 of Intermediate HZ), tert-butyl N-[2-(2-oxoethoxy)ethyl]carbamate (310 mg, 1.53 mmol, synthesized via Step 1 of Intermediate FS) in a mixed solvent of THF (10.0 mL) and DCM (10.0 mL) was added KOAc (199 mg, 2.04 mmol), the mixture was stirred at 15° C. for 0.5 hr, then NaBH(OAc)$_3$ (431 mg, 2.04 mmol) was added, and the mixture was stirred at 15° C. for 16 hrs. On completion, the mixture was quenched with H$_2$O (2.00 mL) and concentrated in vacuo. The crude product was purified by reverse phase: (0.1% HCl condition) to give the title compound (380 mg, 68% yield) as yellow solid. LC-MS (ESI$^+$) m/z 544.4 (M+H)$^+$.

Step 2—5-[[1-[2-(2-Aminoethoxy)ethyl]-4-piperidyl]amino]-2-(2,6-dioxo-3-piperidyl)isoindoline-1,3-dione To a solution of tert-butyl N-[2-[2-[4-[[2-(2,6-dioxo-3-piperidyl)-1,3-dioxo-isoindolin-5-yl]amino]-1-piperidyl]ethoxy]ethyl]carbamate (380 mg, 699 umol) in DCM (3.00 mL) was added HCl/dioxane (4.00 M, 5.00 mL), the mixture was stirred at 15° C. for 0.5 hr. On completion, the mixture was concentrated in vacuo to give the title compound (300 mg, 90% yield, HCl) as yellow solid. LC-MS (ESI$^+$) m/z 444.1 (M+H)$^+$.

5-[[1-[2-[2-[2-(2-Aminoethoxy)ethoxy]ethoxy]ethyl]-4-piperidyl]amino]-2-(2,6-dioxo-3-piperidyl)isoindoline-1,3-dione (Intermediate KA)

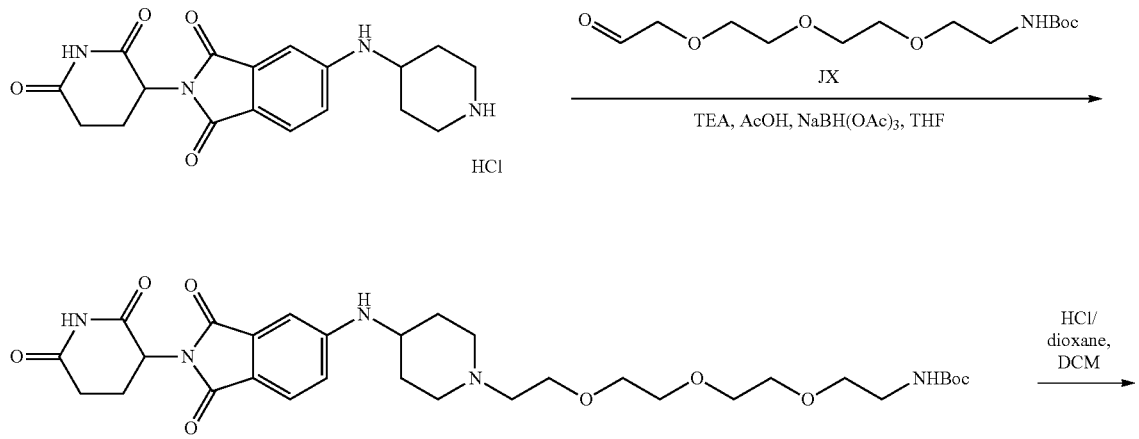

-continued

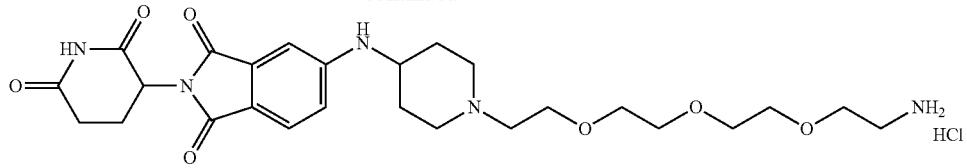

KA

Step 1—Tert-butyl N-[2-[2-[2-[2-[4-[[2-(2,6-dioxo-3-piperidyl)-1,3-dioxo-isoindolin-5-yl]amino]-1-piperidyl]ethoxy]ethoxy]ethoxy]ethyl]carbamate To a solution of 2-(2,6-dioxo-3-piperidyl)-5-(4-piperidylamino)isoindoline-1,3-dione (400 mg, 1.02 mmol, HCl, synthesized via Steps 1-2 of Intermediate HZ) in THF (20 mL) was added TEA (206 mg, 2.04 mmol, 283 uL). The mixture was stirred at 20° C. for 30 minutes, then tert-butyl N-[2-[2-[2-(2-oxoethoxy)ethoxy]ethoxy]ethyl]carbamate (385 mg, 1.32 mmol, Intermediate JX), HOAc (183 mg, 3.05 mmol, 174 uL) and NaBH(OAc)$_3$ (431 mg, 2.04 mmol) was added to the mixture. The reaction mixture was stirred at 20° C. for 16 hours. On completion, the mixture was filtered, and the filtrate was concentrated in vacuo to give a residue. The residue was purified by reverse phase (0.1% FA condition) to give the title compound (400 mg, 62% yield) as a yellow solid. LC-MS (ESI$^+$) m/z 632.4 (M+H)$^+$.

Step 2—5-[[1-[2-[2-[2-(2-Aminoethoxy)ethoxy]ethoxy]ethyl]-4-piperidyl]amino]-2-(2,6-dioxo-3-piperidyl)isoindoline-1,3-dione To a solution of tert-butyl N-[2-[2-[2-[2-[4-[[2-(2,6-dioxo-3-piperidyl)-1,3-dioxo-isoindolin-5-yl]amino]-1-piperidyl]ethoxy]ethoxy]ethoxy]ethyl]carbamate (400 mg, 633 umol) in DCM (5 mL) was added HCl/dioxane (4 M, 6.20 mL). The reaction mixture was stirred at 25° C. for 1 hour. On completion, the mixture was concentrated in vacuo to give the title compound (350 mg, 97% yield) as a yellow solid. LC-MS (ESI$^+$) m/z 532.4 (M+H)$^+$.

4-[4-[2-[2-[2-(2-Aminoethoxy)ethoxy]ethoxy]ethyl]piperazin-1-yl]-2-(2,6-dioxo-3-piperidyl) isoindoline-1,3-dione (Intermediate KB)

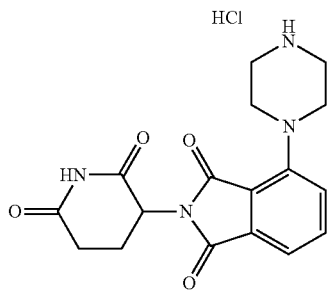
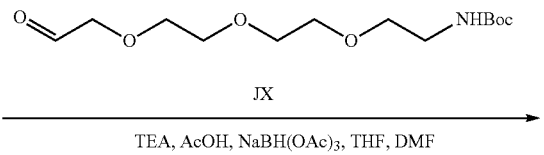

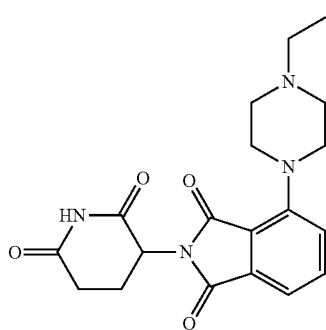

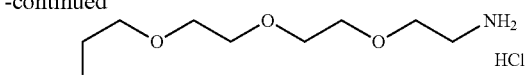
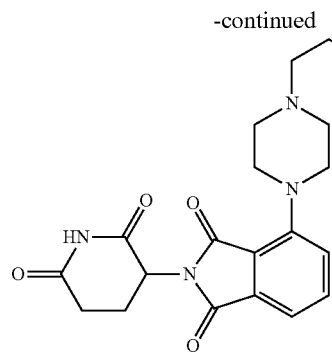

KB

Step 1—Tert-butyl N-[2-[2-[2-[2-[4-[2-(2,6-dioxo-3-piperidyl)-1,3-dioxo-isoindolin-4-yl]piperazin-1-yl]ethoxy]ethoxy]ethoxy]ethyl]carbamate To a mixture of 2-(2,6-dioxo-3-piperidyl)-4-piperazin-1-yl-isoindoline-1,3-dione (250 mg, 659 umol, HCl, synthesized via Steps 1-2 Intermediate IA) and TEA (66.7 mg, 659 umol, 91.8 uL) in THF (10 mL) and DMF (5 mL) was added tert-butyl N-[2-[2-[2-(2-oxoethoxy)ethoxy]ethoxy]ethyl]carbamate (249 mg, 857 umol, Intermediate JX), HOAc (39.6 mg, 659 umol, 37.7 uL) and NaBH(OAc)$_3$ (279 mg, 1.32 mmol). The reaction mixture was stirred at 20° C. for 20 hours. On completion, the reaction mixture was concentrated in vacuo. The residue was purified by prep-HPLC (FA condition) to give the title compound (200 mg, 49% yield) as yellow solid. LC-MS (ESI$^+$) m/z 618.4 (M+H)$^+$

Step 2—4-[4-[2-[2-[2-(2-Aminoethoxy)ethoxy]ethoxy]ethyl]piperazin-1-yl]-2-(2,6-dioxo-3-piperidyl) isoindoline-1,3-dione To a mixture of tert-butyl N-[2-[2-[2-[2-[4-[2-(2,6-dioxo-3-piperidyl)-1,3-dioxo-isoindolin-4-yl]piperazin-1-yl]ethoxy]ethoxy]ethoxy]ethyl]carbamate (200 mg, 323 umol) in DCM (5 mL) was added HCl/dioxane (4 M, 10 mL). The reaction mixture was stirred at 20° C. for 3 hours. On completion, the reaction mixture was concentrated in vacuo to give the title compound (179 mg, 99% yield, HCl) light yellow gum. LC-MS (ESI$^+$) m/z 518.3 (M+H)$^+$.

3-(5-Bromo-1-oxo-isoindolin-2-yl)piperidine-2,6-dione (Intermediate KC)

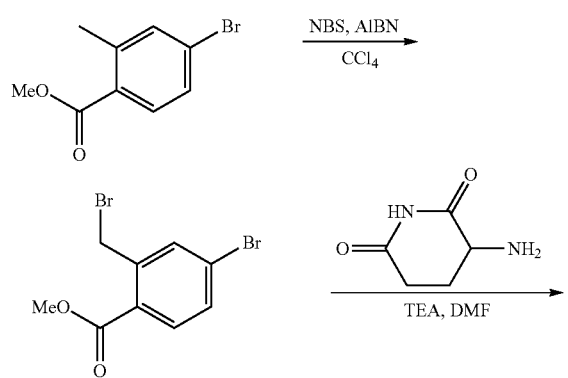

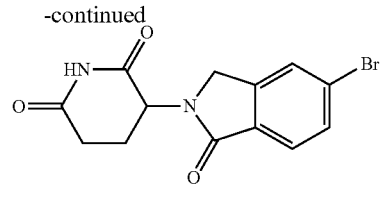

KC

Step 1—Methyl 4-bromo-2-(bromomethyl)benzoate

To a solution of methyl 4-bromo-2-methyl-benzoate (5.00 g, 21.8 mmol, CAS #99548-55-7) in CCl$_4$ (50.0 mL), NBS (4.66 g, 26.1 mmol) and AIBN (358 mg, 2.18 mmol) were added. The reaction mixture was stirred at 80° C. for 24 hrs. On completion, the reaction was filtered and concentrated in vacuo. The residue was purified by silica gel chromatography (PE:EA=20:1) to give the title compound (5.1 g, 76% yield) as colorless liquid. $^1$H NMR (400 MHz, DMSO-d$_6$) δ 7.86 (d, J=8.4 Hz, 1H), 7.59 (s, 1H), 7.54-7.52 (m, 1H), 4.92 (s, 2H), 3.96 (s, 3H).

Step 2—3-(5-bromo-1-oxo-isoindolin-2-yl)piperidine-2,6-dione

To a solution of 3-aminopiperidine-2,6-dione (2.00 g, 12.1 mmol, HCl) and methyl 4-bromo-2-(bromomethyl)benzoate (5.10 g, 16.5 mmol) in DMF (50.0 mL) was added TEA (4.92 g, 48.6 mmol). The reaction mixture was stirred at 75° C. for 12 hrs. On completion, the reaction mixture was diluted with water (200 mL) and filtered. The filtered cake was collected. The reaction mixture was concentrated in vacuo. The residue was triturated with EA:H$_2$O=1:1 (50 mL) to give the title compound (1.70 g, 39% yield) as blue solid. $^1$H NMR (400 MHz, DMSO-d$_6$) δ 10.99 (s, 1H), 7.90 (s, 1H), 7.74-7.66 (m, 2H), 5.14-5.09 (m, 1H), 4.50-4.33 (m, 2H), 2.95-2.86 (m, 1H), 2.70-2.61 (m, 1H), 2.42-2.36 (m, 1H), 2.04-2.01 (m, 1H).

3-(1-Oxo-5-piperazin-1-yl-isoindolin-2-yl)piperidine-2,6-dione (Intermediate KD)

Step 1—Tert-butyl 4-[2-(2,6-dioxo-3-piperidyl)-1-oxo-isoindolin-5-yl]piperazine-1-carboxylate To a solution of 3-(5-bromo-1-oxo-isoindolin-2-yl)piperidine-2,6-dione (500 mg, 1.55 mmol, Intermediate KC), and tert-butyl piperazine-1-carboxylate (413 mg, 1.86 mmol, HCl) in dioxane (40.0 mL) was added $Cs_2CO_3$ (1.01 g, 3.09 mmol), RuPhos (144 mg, 309 umol), [2-(2-aminophenyl)phenyl]-chloro-palladium; dicyclohexyl-[2-(2,6-diisopropoxyphenyl)phenyl]phosphane (240 mg, 309 umol) and 4 Å molecular sieves (30.0 mg), and the mixture was stirred at 100° C. for 16 hr under $N_2$. On completion, the mixture was filtered and the filtrate was concentrated in vacuo. The mixture was purified by reverse phase: (0.1% HCl) to give the title compound (350 mg, 95% yield) as yellow oil, LC-MS (ESI$^+$) m/z 429.3 (M+H)$^+$.

Step 2—3-(1-Oxo-5-piperazin-1-yl-isoindolin-2-yl)piperidine-2,6-dione

To a solution of tert-butyl 4-[2-(2,6-dioxo-3-piperidyl)-1-oxo-isoindolin-5-yl]piperazine-1-carboxylate (160 mg, 373 umol) in DCM (2.00 mL) was added HCl/dioxane (4.00 M, 4.00 mL), the mixture was stirred at 15° C. for 0.5 hr. On completion, the mixture was concentrated in vacuo to give the title compound (130 mg, 90% yield, HCl) as yellow solid. LC-MS (ESI$^+$) m/z 329.2 (M+H)$^+$.

3-[5-[4-[2-[2-(2-Aminoethoxy)ethoxy]ethyl]piperazin-1-yl]-1-oxo-isoindolin-2-yl]piperidine-2,6-dione (Intermediate KE)

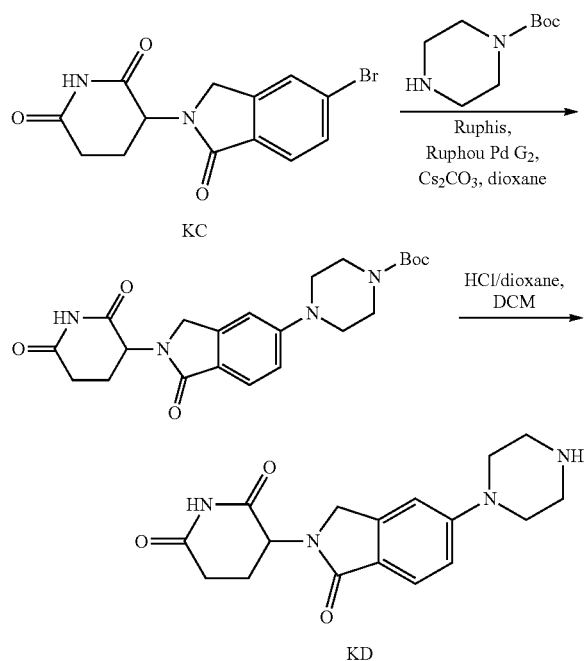

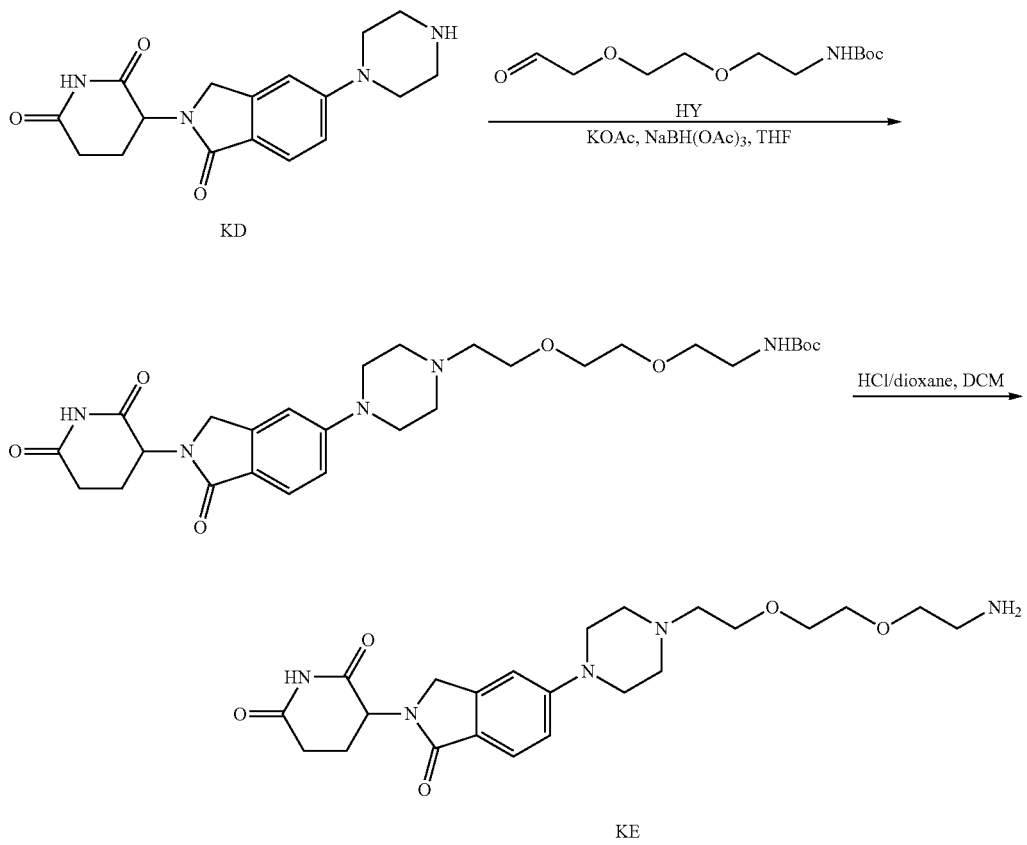

1509

Step 1—Tert-butyl N-[2-[2-[2-[4-[2-(2,6-dioxo-3-piperidyl)-1-oxo-isoindolin-5-yl]piperazin-1-yl]ethoxy]ethoxy]ethyl]carbamate To a solution of 3-(1-oxo-5-piperazin-1-yl-isoindolin-2-yl)piperidine-2,6-dione (130 mg, 356 umol, HCl, Intermediate KE), tert-butyl N-[2-[2-(2-oxoethoxy)ethoxy]ethyl]carbamate (105 mg, 427 umol, Intermediate HY) in THF (10.0 mL) was added KOAc (69.9 mg, 712 umol). The mixture was stirred at 15° C. for 0.5 hr, then NaBH(OAc)$_3$ (151 mg, 712 umol) was added, and the mixture was stirred at 15° C. for 16 hrs. On completion, the mixture was diluted with H$_2$O (1.00 mL) and concentrated in vacuo. The crude product was purified by reverse phase: (0.1% HCl) to give the title compound (130 mg, 65% yield) as yellow solid. LC-MS (ESI$^+$) m/z 560.4 (M+H)$^+$

Step 2—3-[5-[4-[2-[2-(2-Aminoethoxy)ethoxy]ethyl]piperazin-1-yl]-1-oxo-isoindolin-2-yl]piperidine-2,6-dione To a solution of tert-butyl N-[2-[2-[2-[4-[2-(2,6-dioxo-3-piperidyl)-1-oxo-isoindolin-5-yl]piperazin-1-yl]ethoxy]ethoxy]ethyl]carbamate (130 mg, 232 umol) in DCM (3.00 mL) was added HCl/dioxane (4.00 M, 4.00 mL), and the mixture was stirred at 15° C. for 0.5 hr. On completion, the mixture was concentrated in vacuo to give the title compound (110 mg, 90% yield, HCl) as yellow solid. LC-MS (ESI$^+$) m/z 460.4 (M+H)$^+$.

5-[4-[2-(2-Aminoethoxy)ethyl]piperazin-1-yl]-2-(2,6-dioxo-3-piperidyl)isoindoline-1,3-dione (Intermediate KF)

1510

Step 1—Tert-butyl N-[2-[2-[4-[2-(2,6-dioxo-3-piperidyl)-1,3-dioxo-isoindolin-5-yl]piperazin-1-yl]ethoxy]ethyl]carbamate To a solution of 2-(2,6-dioxo-3-piperidyl)-5-piperazin-1-yl-isoindoline-1,3-dione (500 mg, 1.32 mmol, HCl, synthesized via Steps 1-2 of Intermediate IB) in a mixed solvent of DCM (20 mL) and DMF (6 mL) was added TEA (200 mg, 1.98 mmol), HOAc (158 mg, 2.64 mmol) and tert-butyl N-[2-(2-oxoethoxy)ethyl]carbamate (804 mg, 3.96 mmol, synthesized via Step 1 of Intermediate FS) at 5° C. The mixture was stirred at 5° C. for 30 minutes, and then NaBH(OAc)$_3$ (559 mg, 2.64 mmol) was added at 0° C., the mixture was stirred at 10° C. for 72 hours. On completion, the reaction mixture was quenched by water (0.1 mL), and then concentrated in vacuo. The residue was purified by prep-HPLC (FA condition) to give the title compound (0.40 g, 53% yield) as yellow solid. LC-MS (ESI$^+$) m/z 530.2 (M+H)$^+$.

Step 2—5-[4-[2-(2-Aminoethoxy)ethyl]piperazin-1-yl]-2-(2,6-dioxo-3-piperidyl)isoindoline-1,3-dione To a solution of tert-butyl N-[2-[2-[4-[2-(2,6-dioxo-3-piperidyl)-1,3-dioxo-isoindolin-5-yl]piperazin-1-yl]ethoxy]ethyl]carbamate (0.37 g, 649 umol) in DCM (5 mL) was added HCl/dioxane (4 M, 3 mL). The mixture was stirred at rt for 1.5 hours. On completion, the reaction mixture was concentrated in vacuo to give the title compound (0.28 g, 91% yield, HCl) as yellow solid. LC-MS (ESI$^+$) m/z 430.1 (M+H)$^+$.

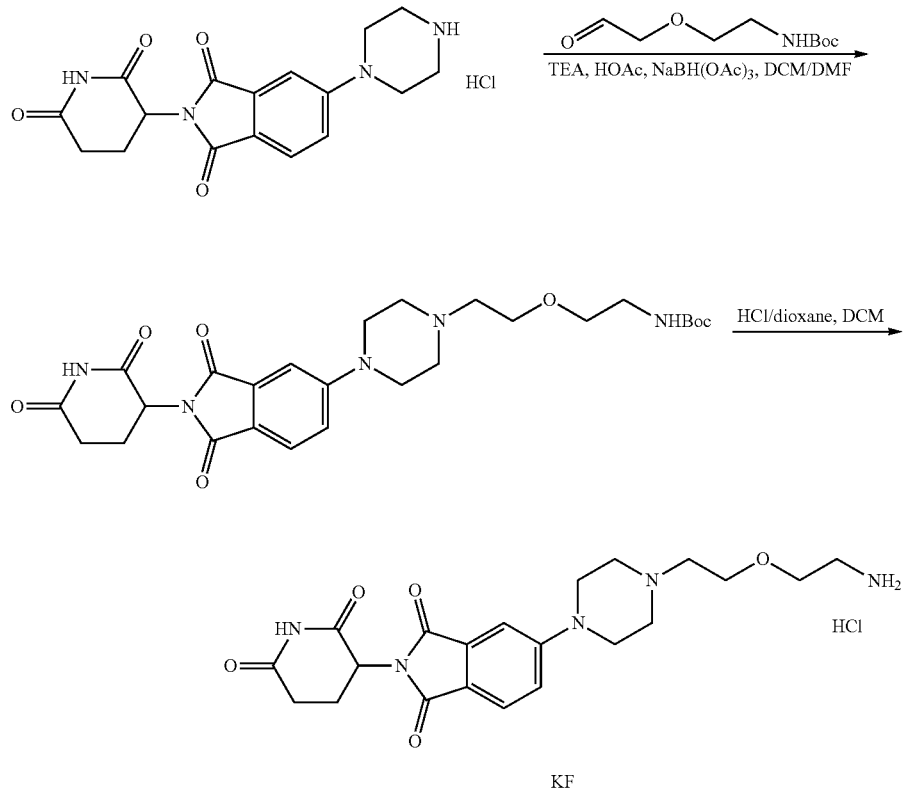

KF

2-[2-(Cyclopropylmethylamino)-4-pyridyl]-N-[3-(difluoromethyl)-1-[4-[[[(2S,4R)-4-hydroxy pyrrolidine-2-carbonyl]amino]methyl]phenyl]pyrazol-4-yl] oxazole-4-carboxamide (Intermediate KG)
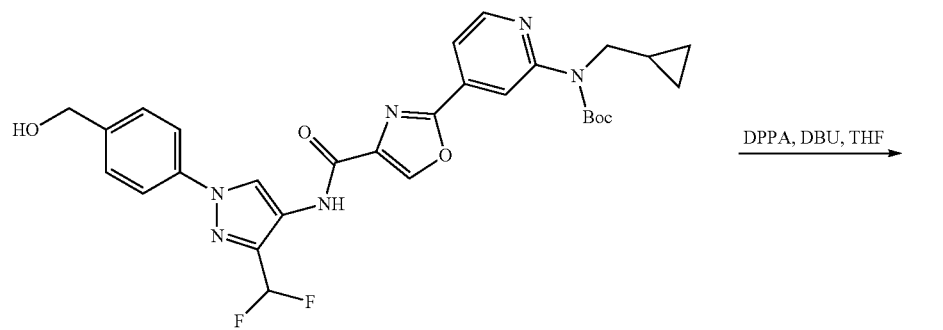
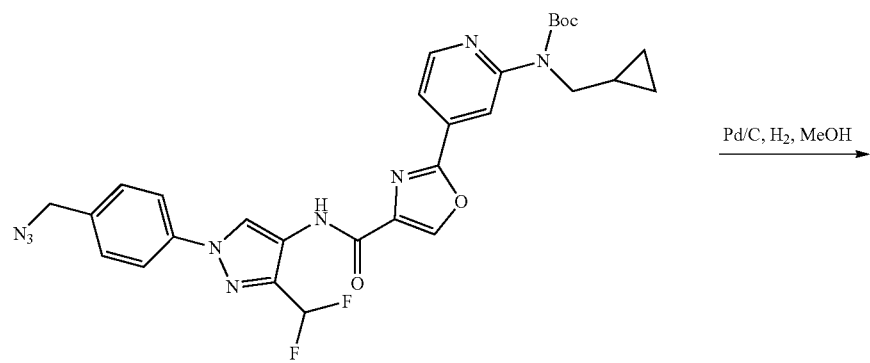
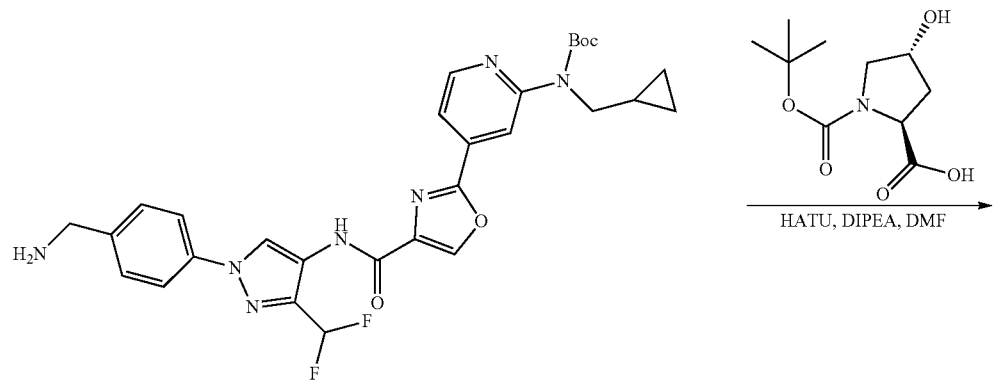

-continued

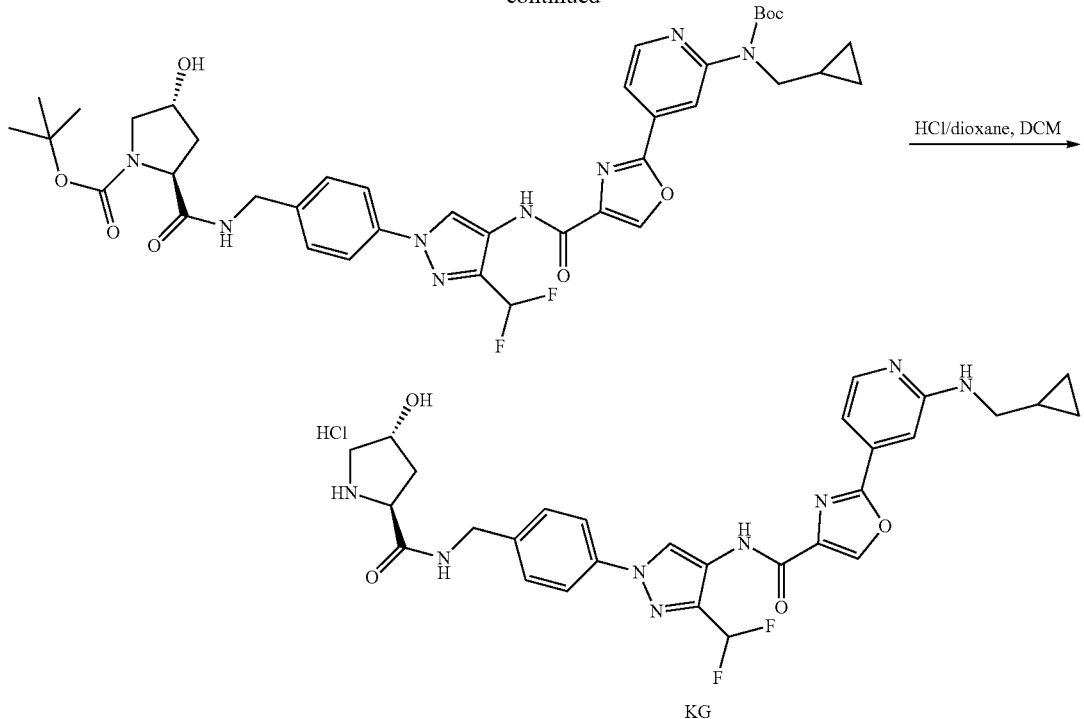

Step 1—Tert-butyl N-[4-[4-[[1-[4-(azidomethyl)phenyl]-3-(difluoromethyl)pyrazol-4-yl]carbamoyl]oxazol-2-yl]-2-pyridyl]-N-(cyclopropylmethyl)carbamate To a mixture of tert-butyl N-(cyclopropylmethyl)-N-[4-[4-[[3-(difluoromethyl)-1-[4-(hydroxymethyl)phenyl]pyrazol-4-yl]carbamoyl]oxazol-2-yl]-2-pyridyl]carbamate (1 g, 1.72 mmol, synthesized via Step 1-2 of Intermediate GF) in THF (20 mL) was added DPPA (2.37 g, 8.61 mmol) at 0° C., then DBU (1.31 g, 8.61 mmol) was added. The mixture was stirred at 20° C. for 16 hrs. On completion, the mixture was quenched with water (10 mL), then extracted with EA (2×50 mL). The organic layer was concentrated in vacuo to give a residue, which was purified by silica gel chromatography to give the title compound (700 mg, 67% yield) as white solid. LC-MS (ESI$^+$) m/z 606.3 (M+1)$^+$.

Step 2—Tert-butyl N-[4-[4-[[1-[4-(aminomethyl)phenyl]-3-(difluoromethyl)pyrazol-4-yl]carbamoyl]oxazol-2-yl]-2-pyridyl]-N-(cyclopropylmethyl)carbamate To a solution of tert-butyl N-[4-[4-[[1-[4-(azidomethyl)phenyl]-3-(difluoromethyl)pyrazol-4-yl]carbamoyl]oxazol-2-yl]-2-pyridyl]-N-(cyclopropylmethyl)carbamate (700 mg, 1.16 mmol) in THF (100 mL) was added Pd/C (50 mg, 10 wt %). The suspension was degassed and purged with H$_2$ for 3 times. The mixture was stirred under H$_2$ (15 Psi) at rt for 16 hrs. On completion, the mixture was filtered and the filtrate was concentrated in vacuo to give the title compound (500 mg, 74% yield) as white solid. LC-MS (ESI$^+$) m/z 580.3 (M+1)$^+$.

Step 3—Tert-butyl (2S,4R)-2-[[4-[4-[[2-[2-[tert-butoxycarbonyl(cyclopropylmethyl)amino]-4-pyridyl]oxazole-4-carbonyl]amino]-3-(difluoromethyl)pyrazol-1-yl]phenyl]methylcarbamoyl]-4-hydroxy-pyrrolidine-1-carboxylate A mixture of (2S,4R)-1-tert-butoxycarbonyl-4-hydroxy-pyrrolidine-2-carboxylic acid (199 mg, 862 umol, CAS #13726-69-7), tert-butyl N-[4-[4-[[1-[4-(aminomethyl)phenyl]-3-(difluoromethyl) pyrazol-4-yl]carbamoyl]oxazol-2-yl]-2-pyridyl]-N-(cyclopropylmethyl)carbamate (500 mg, 862 umol), HATU (393 mg, 1.04 mmol), and DIPEA (334 mg, 2.59 mmol) in DMF (3 mL) was degassed and purged with N$_2$ gas 3 times, and then the mixture was stirred at rt for 2 hrs under N$_2$ atmosphere. On completion, the reaction mixture was quenched with water 20 mL, and then extracted with EA (2×100 mL). The combined organic layer was washed with brine (20 mL), dried over Na$_2$SO$_4$, filtered and concentrated in vacuo to give a residue. The residue was purified by prep-HPLC to give the title compound (460 mg, 67% yield) as white solid. LC-MS (ESI$^+$) m/z 793.2 (M+1)$^+$.

Step 4—2-[2-(Cyclopropylmethylamino)-4-pyridyl]-N-[3-(difluoromethyl)-1-[4-[[[(2S,4R)-4-hydroxy pyrrolidine-2-carbonyl]amino]methyl]phenyl]pyrazol-4-yl]oxazole-4-carboxamide To a solution of tert-butyl (2S,4R)-2-[[4-[4-[[2-[2-[tert-butoxycarbonyl(cyclopropylmethyl)amino]-4-pyridyl]oxazole-4-carbonyl]amino]-3-(difluoromethyl)pyrazol-1-yl]phenyl]methylcarbamoyl]-4-hydroxy-pyrrolidine-1-carboxylate (200 mg, 252 umol) in DCM (10 mL) was added HCl/dioxane (4 M, 3 mL). The mixture was stirred at rt for 16 hrs. On completion, the mixture was concentrated in vacuo to give the title compound (150 mg, 94% yield) as white solid. LC-MS (ESI$^+$) m/z 593.4 (M+1)$^+$.

N-[1-[4-[[[(2S,4R)-1-[(2S)-2-amino-3,3-dimethyl-butanoyl]-4-hydroxy-pyrrolidine-2-carbonyl]amino]methyl]phenyl]-3-(difluoromethyl)pyrazol-4-yl]-2-[2-(cyclopropylmethylamino)-4-pyridyl]oxazole-4-carboxamide (Intermediate KH)

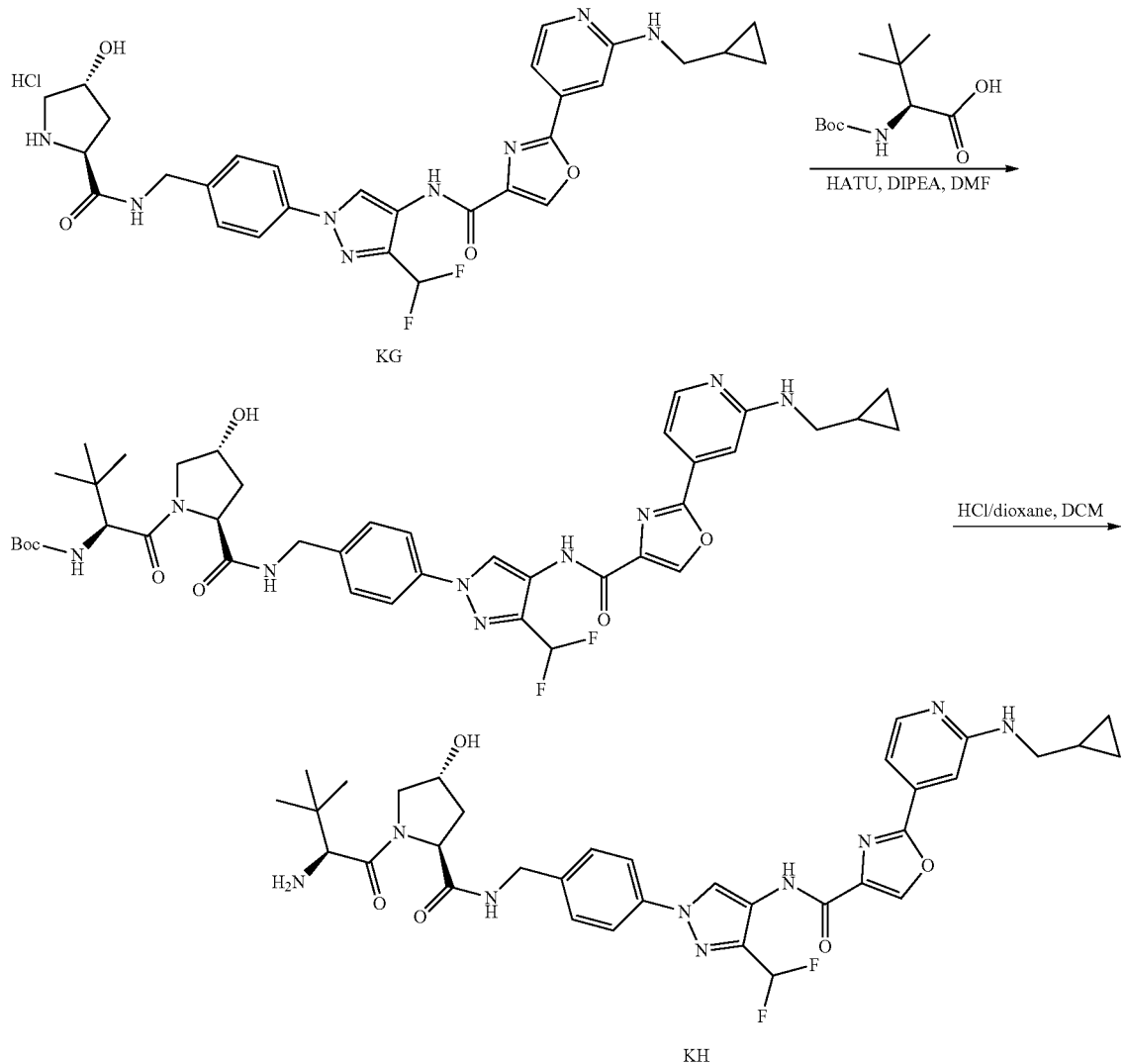

Step 1—Tert-butyl N-[(1S)-1-[(2S,4R)-2-[[4-[4-[[2-[2-(cyclopropylmethylamino)-4-pyridyl]oxazole-4-carbonyl]amino]-3-(difluoromethyl)pyrazol-1-yl]phenyl]methylcarbamoyl]-4-hydroxy-pyrrolidine-1-carbonyl]-2,2-dimethyl-propyl]

A mixture of 2-[2-(cyclopropylmethylamino)-4-pyridyl]-N-[3-(difluoromethyl)-1-[4-[[[(2S,4R)-4-hydroxypyrrolidine-2-carbonyl]amino]methyl]phenyl]pyrazol-4-yl]oxazole-4-carboxamide (70 mg, 111 umol, HCl, Intermediate KG), (2S)-2-(tert-butoxycarbonylamino)-3,3-dimethyl-butanoic acid (26 mg, 111 umol, CAS #62965-35-9), HATU (51 mg, 133 umol), and DIPEA (43. mg, 334 umol) in DMF (5 mL) was degassed and purged with $N_2$ gas 3 times, and then the mixture was stirred at rt for 2 hrs under $N_2$ atmosphere. On completion, the mixture was concentrated in vacuo, the residue was purified by prep-HPLC to give the title compound (65 mg, 65% yield) as white solid. LC-MS (ESI$^+$) m/z 806.5 (M+1)$^+$.

Step 2—N-[1-[4-[[[(2S,4R)-1-[(2S)-2-amino-3,3-dimethyl-butanoyl]-4-hydroxy-pyrrolidine-2-carbonyl]amino]methyl]phenyl]-3-(difluoromethyl)pyrazol-4-yl]-2-[2-(cyclopropylmethylamino)-4-pyridyl]oxazole-4-carboxamide To a solution of tert-butyl N-[(1S)-1-[(2S,4R)-2-[[4-[4-[[2-[2-(cyclopropylmethylamino)-4-pyridyl]oxazole-4-carbonyl]amino]-3-(difluoromethyl)pyrazol-1-yl]phenyl]methylcarbamoyl]-4-hydroxy-pyrrolidine-1-carbonyl]-2,2-dimethyl-propyl]carbamate (100 mg, 124 umol) in DCM (6 mL) was added HCl/dioxane (4 M, 2 mL). The mixture was stirred at rt for 2 hrs. On completion, the mixture was concentrated in vacuo to give the title compound (95 mg, 100% yield) as white solid. LC-MS (ESI$^+$) m/z 706.2 (M+1)$^+$ O1-Benzyl O2-[(3R,5S)-5-[[4-[4-[[2-[2-(cyclopropylmethylamino)-4-pyridyl]oxazole-4-carbonyl]amino]-3-(difluoromethyl)pyrazol-1-yl]phenyl]methylcarbamoyl]pyrrolidin-3-yl](2S)-pyrrolidine-1,2-dicarboxylate (Intermediate KI)

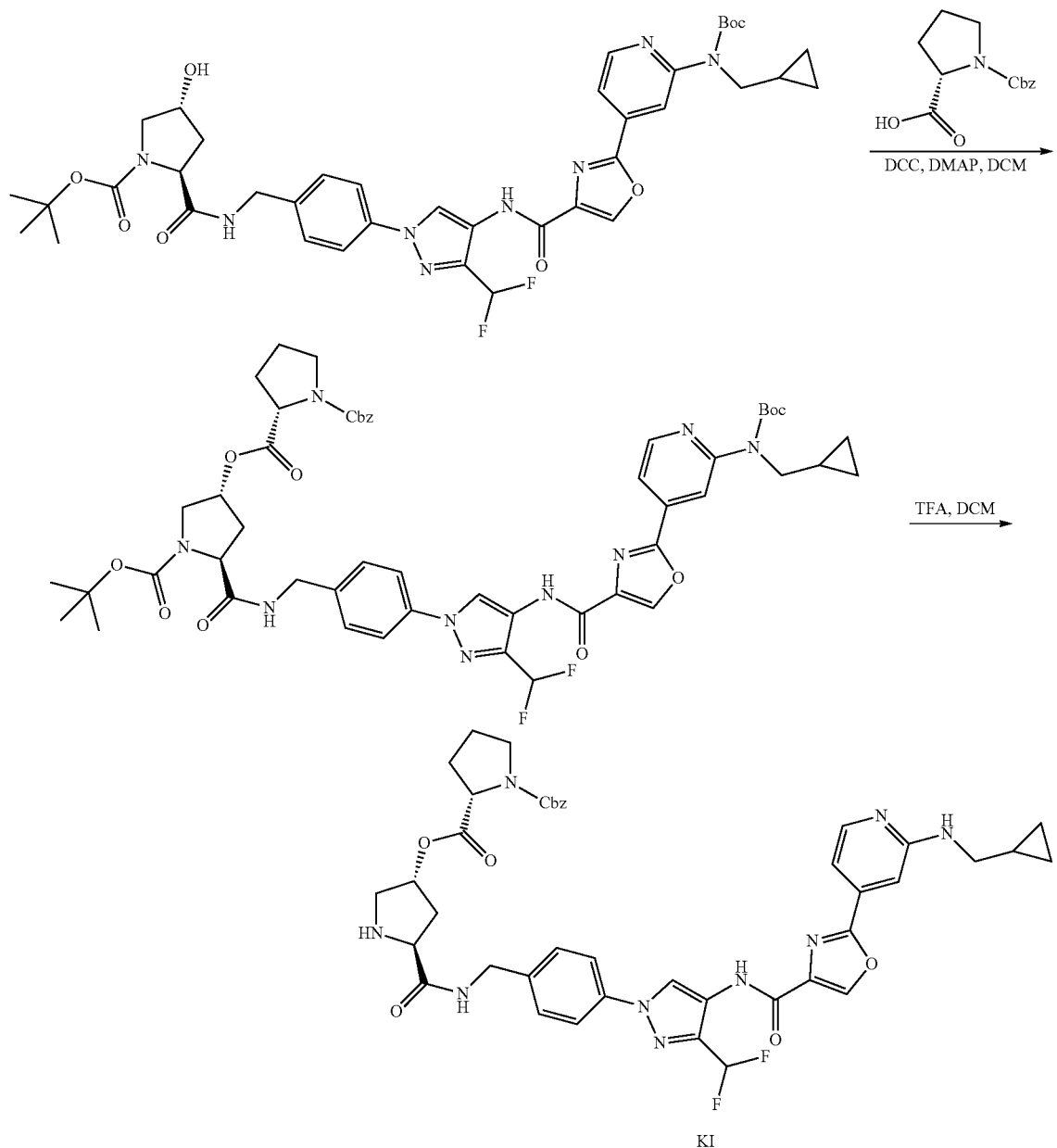

Step 1—O1-benzyl O2-[(3R,5S)-1-tert-butoxycarbonyl-5-[[4-[4-[[2-[2-[tert-butoxycarbonyl(cyclopropylmethyl)amino]-4-pyridyl]oxazole-4-carbonyl]amino]-3-(difluoromethyl)pyrazol-1-yl]phenyl]methylcarbamoyl]pyrrolidin-3-yl] (2S)-pyrrolidine-1,2-dicarboxylate To a solution of (2S)-1-benzyloxycarbonylpyrrolidine-2-carboxylic acid (72.3 mg, 290 umol) in DCM (10 mL) was added EDCI (83.4 mg, 435 umol) and DMAP (3.54 mg, 29.0 umol) at 0° C., then tert-butyl(2S,4R)-2-[[4-[4-[[2-[2-[tert-butoxycarbonyl(cyclopropylmethyl)amino]-4-pyridyl]oxazole-4-carbonyl]amino]-3-(difluoromethyl)pyrazol-1-yl]phenyl]methylcarbamoyl]-4-hydroxy-pyrrolidine-1-carboxylate (230 mg, 290 umol, synthesized via Steps 1-3 of Intermediate KG) was added to the mixture, and the reaction mixture was stirred at rt for 12 hr. On completion, the mixture was diluted with $H_2O$ (5 mL), then concentrated in vacuo to give a residue. The residue was purified by reverse phase (0.1% FA condition) to give the title compound (280 mg, 94% yield) as a white solid. LC-MS (ESI$^+$) m/z 1024.6 (M+H)$^+$.

Step 2-O1-benzyl O2-[(3R,5S)-5-[[4-[4-[[2-[2-(cy-clopropylmethylamino)-4-pyridyl]oxazole-4-carbonyl]amino]-3-(difluoromethyl)pyrazol-1-yl]phenyl]methylcarbamoyl]pyrrolidin-3-yl](2S)-pyrrolidine-1,2-dicarboxylate To a solution of O1-benzyl O2-[(3R,5S)-1-tert-butoxycarbonyl-5-[[4-[4-[[2-[2-[tert-butoxycarbonyl (cyclopropylmethyl)amino]-4-pyridyl]oxazole-4-carbonyl]amino]-3-(difluoromethyl)pyrazol-1-yl]phenyl]methylcarbamoyl] pyrrolidin-3-yl] (2S)-pyrrolidine-1,2-dicarboxylate (260 mg, 253 umol) in DCM (2 mL) was added TFA (1.54 g, 13.5 mmol, 1 mL), and the reaction mixture was stirred at rt for 12 hr. On completion, the mixture was concentrated in vacuo to give the title compound (200 mg, 96% yield) as a white solid. LC-MS (ESI$^+$) m/z 824.4 (M+H)$^+$.

O2-[(3R,5S)-1-[(2S)-2-amino-3,3-dimethyl-butanoyl]-5-[[4-[4-[[2-[2-(cyclopropylmethylamino)-4-pyridyl]oxazole-4-carbonyl]amino]-3-(difluoromethyl)pyrazol-1-yl]phenyl]methylcarbamoyl] pyrrolidin-3-yl] O1-benzyl (2S)-pyrrolidine-1,2-dicarboxylate (Intermediate KJ)

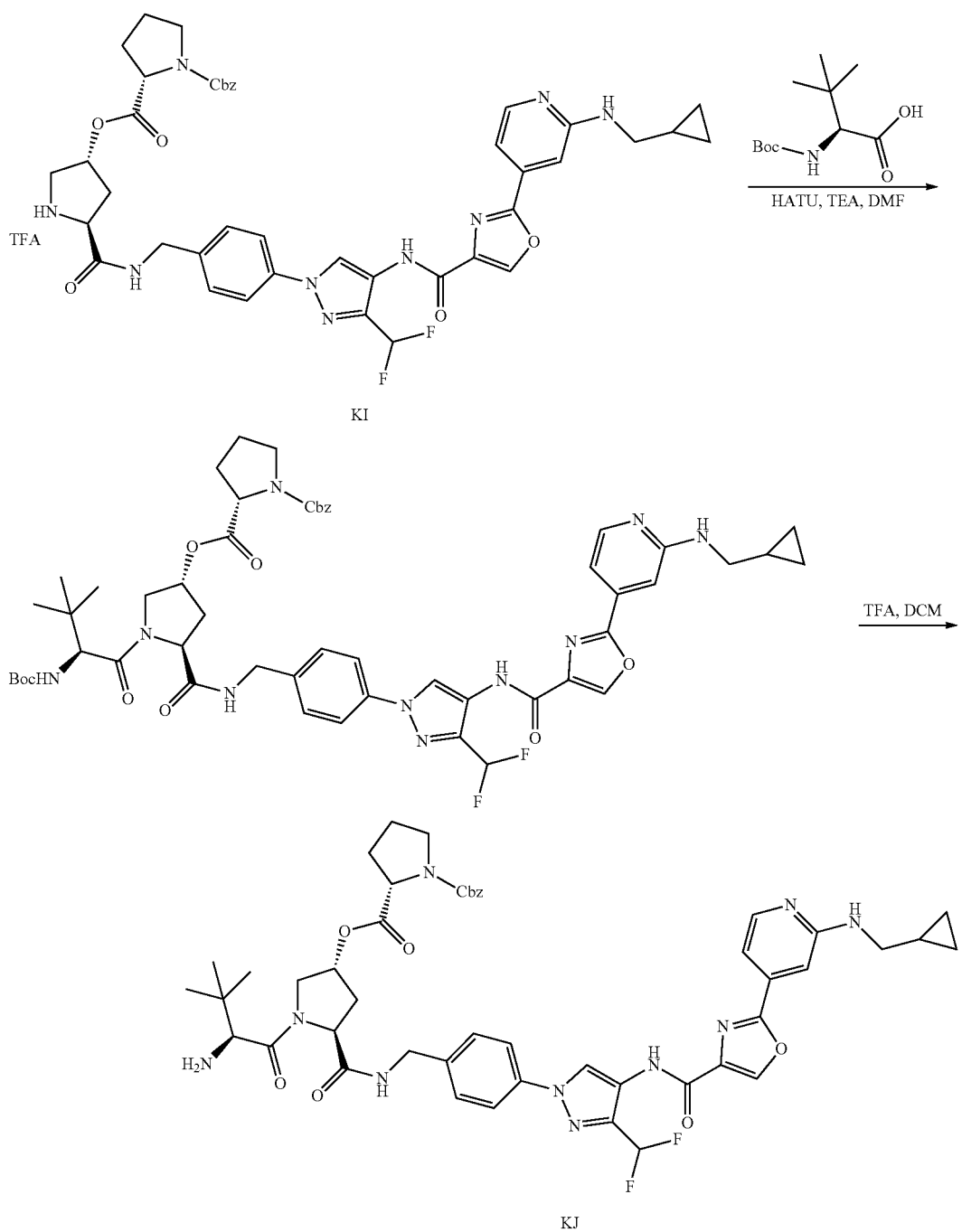

Step 1—(S)-1-Benzyl 2-((3R,5S)-1-((S)-2-((tert-butoxycarbonyl)amino)-3,3-dimethylbutanoyl)-5-((4-(4-(2-(2-((cyclopropylmethyl)amino)pyridin-4-yl)oxazole-4-carboxamido)-3-(difluoromethyl)-1H-pyrazol-1-yl)benzyl)carbamoyl)pyrrolidin-3-yl) pyrrolidine-1,2-dicarboxylate To a solution of O1-benzyl O2-[(3R,5S)-5-[[4-[4-[[2-[2-(cyclopropylmethylamino)-4-pyridyl]oxazole-4-carbonyl]amino]-3-(difluoromethyl)pyrazol-1-yl]phenyl]methylcarbamoyl]pyrrolidin-3-yl](2S)-pyrrolidine-1,2-dicarboxylate (140 mg, 169 umol, Intermediate KI) and (2S)-2-(tert-butoxycarbonylamino)-3,3-dimethyl-butanoic acid (39.3 mg, 169 umol, CAS #62965-35-9) in DMF (10 mL) was added DIPEA (21.9 mg, 169 umol, 29.6 uL) and HATU (77.5 mg, 203 umol), and the mixture was stirred at rt for 12 hr. On completion, the mixture was quenched by addition of H$_2$O (5 mL), and then concentrated in vacuo to give a residue. The residue was purified by reverse phase (0.1% FA condition) to give the title compound (160 mg, 91% yield) as a white solid. LC-MS (ESI$^+$) m/z 1037.3 (M+H)$^+$.

Step 2—O2-[(3R,5S)-1-[(2S)-2-amino-33-dimethyl-butanoyl]-5-[[4-[4-[[2-[2-(cyclopropylmethyl-amino)-4-pyridyl]oxazole-4-carbonyl]amino]-3-(difluoromethyl)pyrazol-1-yl]phenyl]methylcarbamoyl]pyrrolidin-3-yl] O1-benzyl (2S)-pyrrolidine-1,2-dicarboxylate To a solution of O1-benzyl O2-[(3R,5S)-1-[(2S)-2-(tert-butoxycarbonylamino)-3,3-dimethyl-butanoyl]-5-[[4-[4-

[[2-[2-(cyclopropylmethylamino)-4-pyridyl]oxazole-4-carbonyl]amino]-3-(difluoromethyl)pyrazol-1-yl]phenyl]methylcarbamoyl]pyrrolidin-3-yl] (2S)-pyrrolidine-1,2-dicarboxylate (150 mg, 144 umol) in DCM (4 mL) was added TFA (3.08 g, 27.0 mmol, 2.0 mL), and the reaction mixture was stirred at rt for 3 hr. On completion, the reaction mixture was concentrated in vacuo to give the title compound (130 mg, 96% yield) as a yellow solid. LC-MS (ESI$^+$) m/z 937.5 (M+H)$^+$.

4-[[1-[2-[2-(2-Aminoethoxy)ethoxy]ethyl]-4-piperidyl]amino]-2-(2,6-dioxo-3-piperidyl)isoindoline-1,3-dione (Intermediate KK)

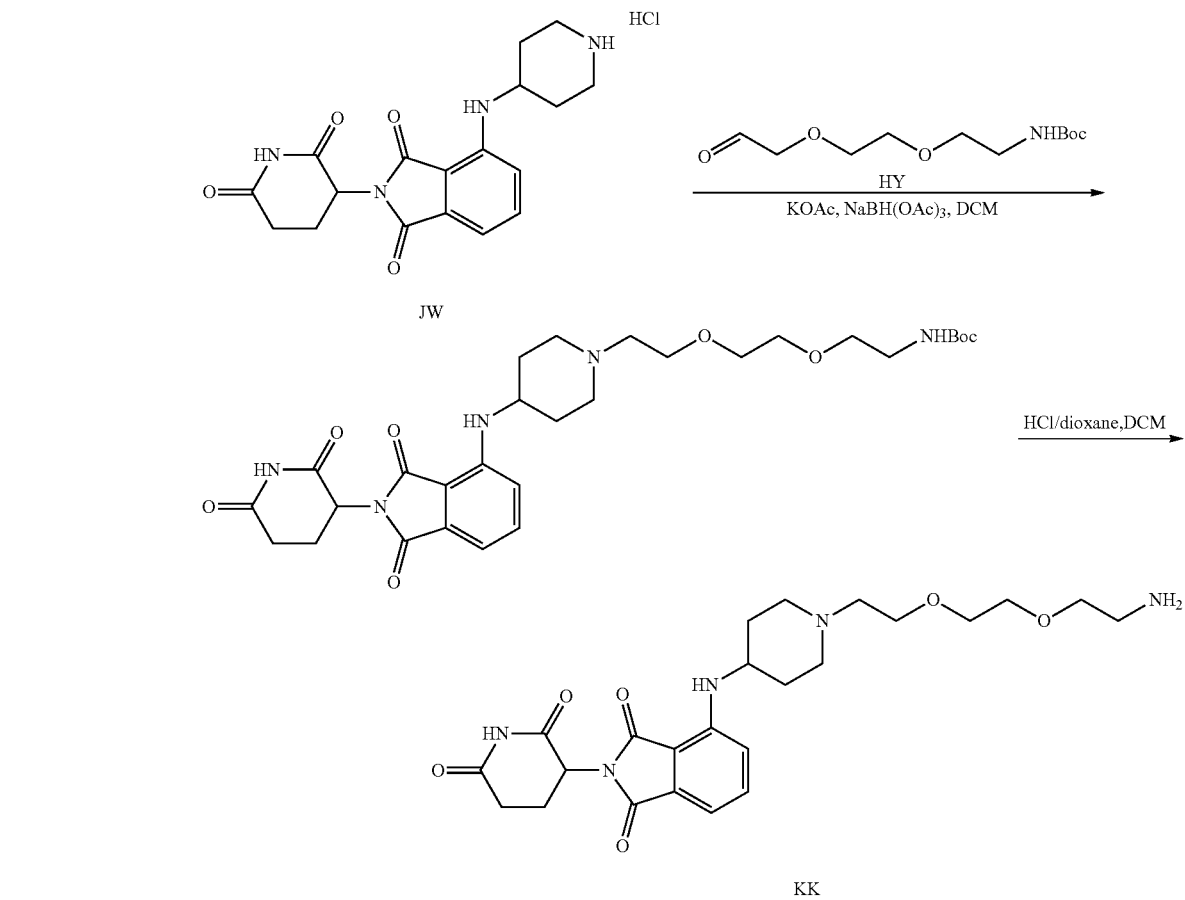

Step 1—Tert-butyl N-[2-[2-[2-[4-[[2-(2,6-dioxo-3-piperidyl)-1,3-dioxo-isoindolin-4-yl]amino]-1-piperidyl]ethoxy]ethoxy]ethyl]carbamate To a mixture of 2-(2,6-dioxo-3-piperidyl)-4-(4-piperidylamino)isoindoline-1,3-dione (200 mg, 509 umol, HCl, Intermediate JW) in DCM (10 mL) was added KOAc (99.9 mg, 1.02 mmol) and stirred at 1 hr. Tert-butyl N-[2-[2-(3-oxopropoxy)ethoxy]ethyl]carbamate (133 mg, 509 umol, Intermediate HY) and NaBH(OAc)$_3$ (216 mg, 1.02 mmol) was added into the mixture. The reaction mixture was stirred at rt for 11 hrs. On completion, the reaction mixture was concentrated in vacuo. The residue was purified by reverse phase (0.1%

FA) to give the title compound (165 mg, 55% yield) as a yellow solid. LC-MS (ESI⁺) m/z 588.2 (M+H)⁺.

Step 2—4-[[1-[2-[2-(2-Aminoethoxy)ethoxy]ethyl]-4-piperidyl]amino]-2-(2,6-dioxo-3-piperidyl)isoindoline-1,3-dione To a mixture of tert-butyl N-[2-[2-[2-[4-[[2-(2,6-dioxo-3-piperidyl)-1,3-dioxo-isoindolin-4-yl]amino]-1-piperidyl]ethoxy]ethoxy]ethyl]carbamate (165 mg, 281 umol) in DCM (2 mL) was added HCl/dioxane (4 M, 0.7 mL). The reaction mixture was stirred at rt for 0.5 hr. On completion, the mixture was concentrated in vacuo to give the title compound (136 mg, 92% yield, HCl) as brown oil. LC-MS (ESI⁺) m/z 488.2 (M+H)⁺.

4-[4-[2-[2-(2-Aminoethoxy)ethoxy]ethyl]piperazin-1-yl]-2-(2,6-dioxo-3-piperidyl)isoindoline-1,3-dione (Intermediate KL)

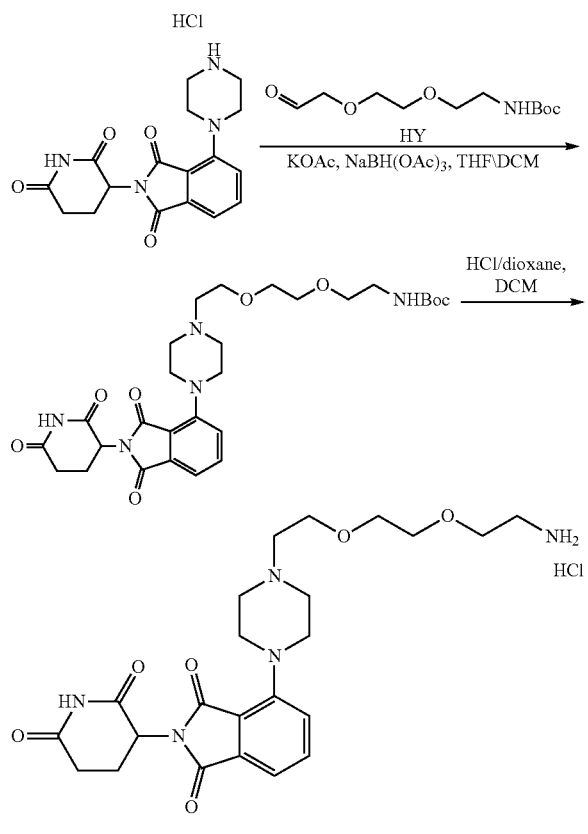

KL

Step 1—Tert-butyl N-[2-[2-[2-[4-[2-(2,6-dioxo-3-piperidyl)-1,3-dioxo-isoindolin-4-yl]piperazin-1-yl]ethoxy]ethoxy]ethyl]carbamate To a solution of 2-(2,6-dioxo-3-piperidyl)-4-piperazin-1-yl-isoindoline-1,3-dione (250 mg, 660 umol, HCl, synthesized via Steps 1-2 Intermediate IA) and tert-butyl N-[2-[2-(2-oxoethoxy)ethoxy]ethyl]carbamate (212 mg, 858 umol, Intermediate HY) in a mixed solvent of THF (15 mL) and DCM (5 mL) was added KOAc (130 mg, 1.32 mmol). Then one hour later, NaBH(OAc)₃ (280 mg, 1.32 mmol) was added and the reaction mixture was stirred at rt for 17 hrs. On completion, the mixture was concentrated in vacuo. The residue was purified by reverse phase (0.1% HCl condition) to give the title compound (110 mg, 29% yield) as a yellow solid. LC-MS (ESI⁺) m/z 574.2 (M+H)⁺.

Step 2—4-[4-[2-[2-(2-Aminoethoxy)ethoxy]ethyl]piperazin-1-yl]-2-(2,6-dioxo-3-piperidyl)isoindoline-1,3-dione To a solution of tert-butyl N-[2-[2-[2-[4-[2-(2,6-dioxo-3-piperidyl)-1,3-dioxo-isoindolin-4-yl]piperazin-1-yl]ethoxy]ethoxy]ethyl]carbamate (110 mg, 192 umol) in DCM (4 mL) was added HCl/dioxane (4 mL). The reaction mixture was stirred at rt for 1 hr. On completion, the mixture was concentrated in vacuo to give the title compound (90 mg, 92% yield, HCl) as a yellow solid. LC-MS (ESI⁺) m/z 474.2 (M+H)⁺.

Tert-butyl N-[4-[4-[[3-carbamoyl-1-[4-[methyl(2-oxoethyl)carbamoyl]phenyl]pyrazol-4-yl]carbamoyl]oxazol-2-yl]-2-pyridyl]-N-(cyclopropylmethyl)carbamate (Intermediate KM)

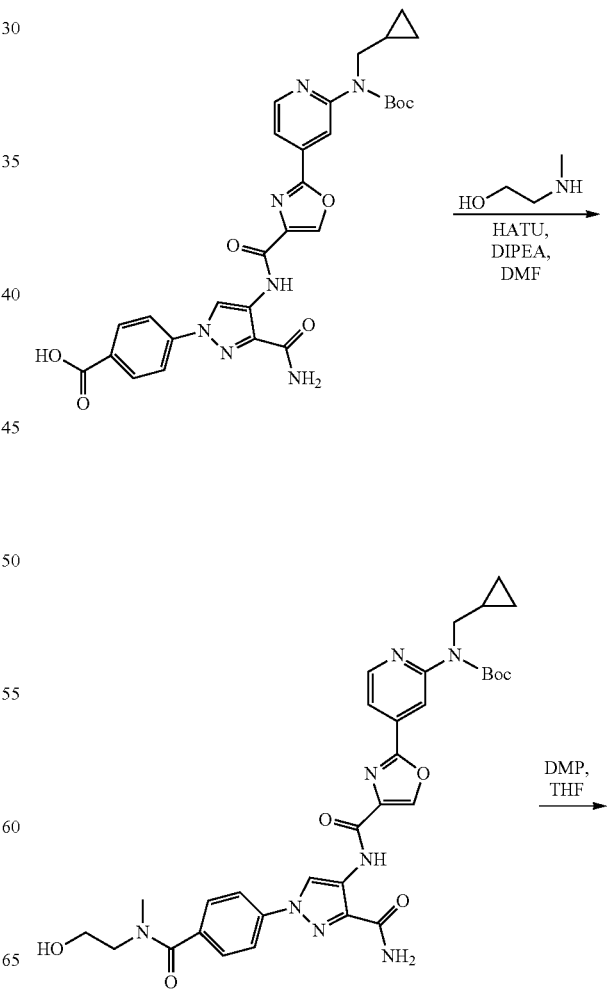

-continued

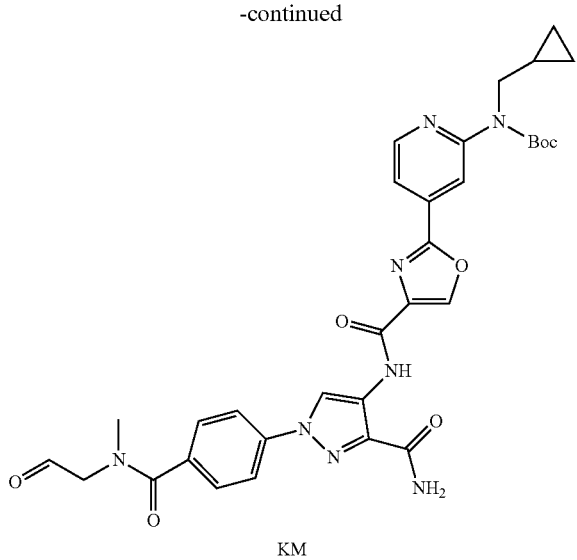

KM

Step 1—Tert-butyl N-[4-[4-[[3-carbamoyl-1-[4-[2-hydroxyethyl(methyl)carbamoyl]phenyl]pyrazol-4-yl]carbamoyl]oxazol-2-yl]-2-pyridyl]-N-(cyclopropylmethyl)carbamate To a solution of 4-[4-[[2-[2-[tert-butoxycarbonyl(cyclopropylmethyl)amino]-4-pyridyl]oxazole-4-carbonyl]amino]-3-carbamoyl-pyrazol-1-yl]benzoic acid (300 mg, 510 umol, Intermediate DF) and 2-(methylamino) ethanol (38.3 mg, 510 umol, 41.0 Ul, CAS #109-83-1) in DMF (2 mL) was added HATU (232 mg, 612 umol) and DIPEA (329 mg, 2.55 mmol, 444 uL), and the reaction mixture was stirred at rt for 12 hrs. On completion, the mixture was filtered, and the filter cake was dried in vacuo to give the title compound (210 mg, 64% yield) as a yellow solid. LC-MS (ESI$^+$) m/z 645.4 (M+H)$^+$.

Step 2—Tert-butyl N-[4-[4-[[3-carbamoyl-1-[4-[methyl(2-oxoethyl)carbamoyl]phenyl]pyrazol-4-yl]carbamoyl]oxazol-2-yl]-2-pyridyl]-N-(cyclopropylmethyl)carbamate To a solution of tert-butyl N-[4-[4-[[3-carbamoyl-1-[4-[2-hydroxyethyl(methyl)carbamoyl]phenyl]pyrazol-4-yl]carbamoyl]oxazol-2-yl]-2-pyridyl]-N-(cyclopropylmethyl)carbamate (160 mg, 248 umol) in THF (5 mL) was added DMP (126 mg, 297 umol, 92.2 uL). The reaction mixture was stirred at rt for 2 hours. On completion, the mixture was diluted with H$_2$O (20 mL), then extracted with DCM (2×30 mL). The combined organic layer was then washed with Na$_2$S$_2$O$_3$ (30 mL), NaHCO$_3$ (30 mL), and concentrated in vacuo to give the title compound (150 mg, 94% yield) as a yellow solid. LC-MS (ESI$^+$) m/z 643.4 (M+H)$^+$.

Tert-butyl N-[2-[3-(2-aminoethoxy)propoxy]ethyl] carbamate (Intermediate KN)

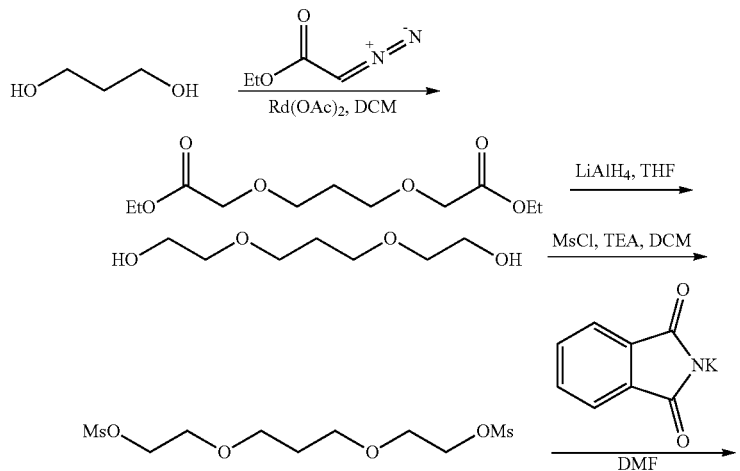

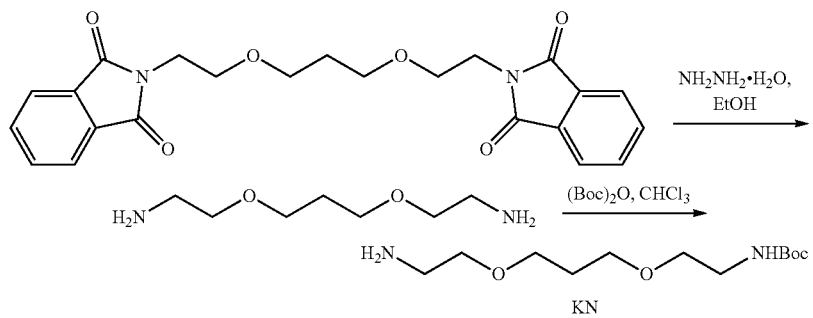

Step 1—Ethyl 2-[3-(2-ethoxy-2-oxo-ethoxy) propoxy]acetate

To a solution of propane-1,3-diol (15.0 g, 197 mmol, CAS #126-30-7) and Rh(OAc)$_2$ (435 mg, 1.97 mmol) in DCM (200 mL) was added a solution of ethyl 2-diazoacetate (67.4 g, 591 mmol) in DCM (100 mL) dropwise. The mixture was stirred at 10° C. for 16 hours. On completion, the mixture was diluted with H$_2$O (150 mL) and extracted with DCM (3×150 mL). The combined organic layers were dried over Na$_2$SO$_4$, filtered and concentrated in vacuo to give a residue. The residue was purified by column chromatography (SiO$_2$) to give the title compound (30.0 g, 61% yield) as colorless liquid. $^1$H NMR (400 MHz, CDCl$_3$) δ 4.21 (q, J=7.2 Hz, 4H), 4.07 (s, 4H), 3.65 (t, J=6.4 Hz, 4H), 1.99-1.89 (m, 2H), 1.28 (t, J=7.2 Hz, 6H).

Step 2—2-[3-(2-Hydroxyethoxy)propoxy]ethanol

To a solution of ethyl 2-[3-(2-ethoxy-2-oxo-ethoxy) propoxy]acetate (20.0 g, 80.5 mmol) in THF (300 mL) was added LiAlH$_4$ (6.24 g, 161 mmol, 98% purity) at 0° C. The mixture was then stirred at 10° C. for 1 hour. On completion, the mixture was quenched with water (10 mL) and NaOH aqueous solution (15%, 10 mL) at 0° C., and the reaction was filtered. The filtrate was dried over Na$_2$SO$_4$, filtered and concentrated in vacuo to give the title compound (12 g, 90% yield) as colourless oil. $^1$H NMR (400 MHz, DMSO-d$_6$) δ 4.53 (t, J=5.2 Hz, 2H), 3.50-3.45 (m, 4H), 3.43 (t, J=6.4 Hz, 4H), 3.37 (t, J=5.2 Hz 4H), 1.75-1.68 (m, 2H)

Step 3—2-[3-(2-Methylsulfonyloxyethoxy)propoxy] ethyl methanesulfonate

To a solution of 2-[3-(2-hydroxyethoxy)propoxy]ethanol (12.0 g, 73.0 mmol) and TEA (44.3 g, 438 mmol) in DCM (160 mL) was added MsCl (25.1 g, 219 mmol) dropwise at 0° C., then the mixture was stirred at 10° C. for 1 hour. On completion, the reaction mixture was quenched by water (50 mL) at 0° C., and then extracted with DCM (3×150 mL). The combined organic layers were washed with saturated citric acid (2×30 mL), dried over Na$_2$SO$_4$, filtered and concentrated in vacuo to give title compound (23 g, 98% yield) as light yellow oil. $^1$H NMR (400 MHz, CDCl$_3$) δ 3.67 (t, J=4.4 Hz, 4H), 3.71 (t, J=4.4 Hz, 4H), 3.58 (t, J=6.0 Hz, 4H), 3.06 (s, 6H), 1.93-1.79 (m, 2H).

Step 4—2-[2-[3-[2-(1,3-Dioxoisoindolin-2-yl) ethoxy]propoxy]ethyl]isoindoline-1,3-dione To a solution of 2-[3-(2-methylsulfonyloxyethoxy) propoxy]ethyl methanesulfonate (16.0 g, 49.9 mmol) in DMF (280 mL) was added (1,3-dioxoisoindolin-2-yl)potassium (27.7 g, 149 mmol). The mixture was stirred at 85° C. for 16 hours. On completion, the reaction mixture was filtered and concentrated in vacuo to give a residue. The residue was triturated with EA (30 mL) and filtered to give a filter cake. The filter cake was triturated with water (150 mL) and filtered again to give the filter cake as the title compound (19 g, 90% yield) as white solid. $^1$H NMR (400 MHz, DMSO-d$_6$) δ 7.87-7.78 (m, 8H), 3.67 (t, J=6.0 Hz, 4H), 3.47 (t, J=6.0 Hz, 4H), 3.32 (t, J=6.0 Hz, 4H), 1.59-1.52 (m, 2H).

Step 5—2-[3-(2-Aminoethoxy)propoxy]ethanamine

To a solution of 2-[2-[3-[2-(1,3-dioxoisoindolin-2-yl) ethoxy]propoxy]ethyl]isoindoline-1,3-dione (18.0 g, 42.6 mmol) in EtOH (250 mL) was added NH$_2$NH$_2$.H$_2$O (21.7 g, 426 mmol, 98% purity). The mixture was stirred at 80° C. for 16 hours. On completion, the reaction mixture was filtered to give the filtrate which was concentrated in vacuo to give the title compound (7.2 g, 100% yield) as colorless oil. $^1$H NMR (400 MHz, DMSO-d$_6$) δ 3.42 (t, J=6.4 Hz, 4H), 3.31 (t, J=5.6 Hz, 4H), 2.63 (t, J=5.6 Hz, 4H), 2.46-2.09 (m, 4H), 1.75-1.68 (m, 2H).

Step 6—Tert-butyl N-[2-[3-(2-aminoethoxy) propoxy]ethyl]carbamate

To a solution of 2-[3-(2-aminoethoxy)propoxy] ethanamine (7.20 g, 44.3 mmol) in CHCl$_3$ (250 mL) was added a solution of (Boc)$_2$O (3.23 g, 14.7 mmol) in CHCl$_3$ (80 mL) dropwise. The mixture was stirred at rt for 16 hours. On completion, the reaction mixture was concentrated in vacuo to give a residue. The residue was purified by column chromatography (SiO$_2$) to give the title compound (2.50 g, 64% yield) as colorless oil. $^1$H NMR (400 MHz, CDCl$_3$) δ 4.98 (s, 1H), 3.54 (t, J=6.0 Hz, 4H), 3.51-3.42 (m, 4H), 3.34-3.25 (m, 2H), 2.86 (t, J=5.2 Hz, 2H), 1.88-1.82 (m, 2H), 1.45 (s, 9H).

Benzyl N-[4-(4-amino-3-carbamoyl-pyrazol-1-yl) phenyl]carbamate (Intermediate KO)

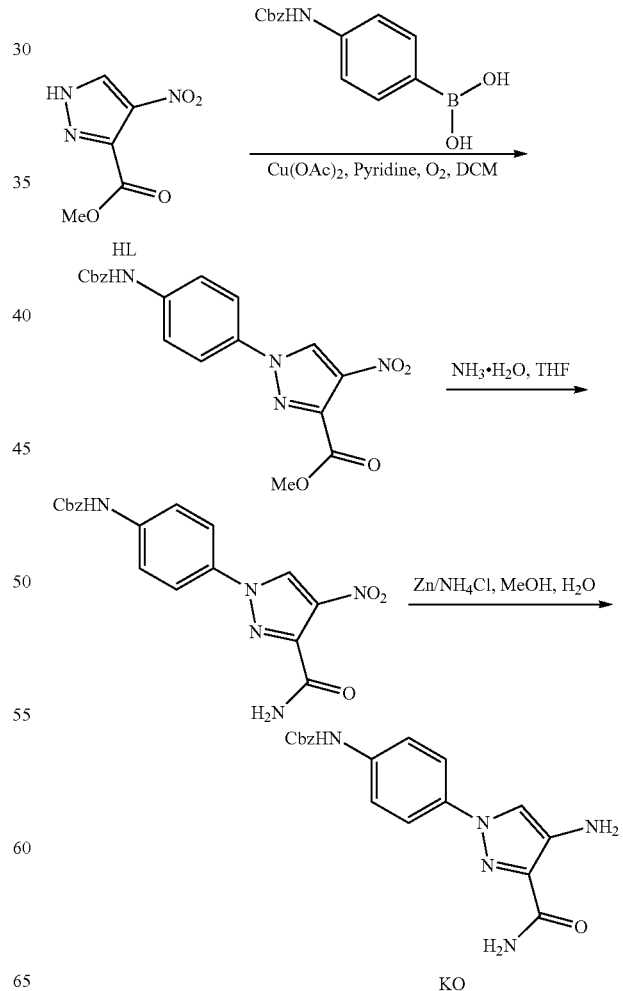

Step 1—Methyl 1-[4-(benzyloxycarbonylamino)phenyl]-4-nitro-pyrazole-3-carboxylate To a solution of methyl 4-nitro-1H-pyrazole-3-carboxylate (841 mg, 4.92 mmol, CAS #1345513-95-2, Intermediate HL), [4-(benzyloxycarbonylamino)phenyl]boronic acid (2.00 g, 7.38 mmol, CAS #192804-36-7) in DCM (70.0 mL) was added pyridine (1.56 g, 19.6 mmol) and $Cu(OAc)_2$ (1.34 g, 7.38 mmol), and the mixture was stirred at rt for 16 hrs under $O_2$ (15 psi). On completion, the mixture was concentrated in vacuo. The mixture was purified by silica gel column (PE:EA=1:1) to give the title compound (400 mg, 20% yield) as white solid. $^1H$ NMR (400 MHz, $CDCl_3$) δ 8.14 (s, 1H), 7.50-7.45 (m, 2H), 7.40-7.36 (m, 2H), 7.35-7.30 (m, 5H), 6.79 (s, 1H), 5.16 (s, 2H), 3.87 (s, 3H).

Step 2-Benzyl N-[4-(3-carbamoyl-4-nitro-pyrazol-1-yl)phenyl]carbamate

To a solution of methyl 1-[4-(benzyloxycarbonylamino)phenyl]-4-nitro-pyrazole-3-carboxylate (200 mg, 504 umol) in THF (10.0 mL) was added $NH_3.H_2O$ (4.55 g, 38.9 mmol, 30 wt %), and the mixture was stirred at 110° C. for 16 hrs. On completion, the mixture was concentrated in vacuo. The mixture was purified by reverse phase: (0.1% FA) to give the title compound (70.0 mg, 36% yield) as yellow solid. $^1H$ NMR (400 MHz, DMSO-$d_6$) δ 10.07 (s, 1H), 9.54 (s, 1H), 8.53 (s, 1H), 7.88 (d, J=8.8 Hz, 2H), 7.64 (d, J=8.8 Hz, 2H), 7.48-7.36 (m, 5H), 5.19 (s, 2H).

Step 3—Benzyl N-[4-(4-amino-3-carbamoyl-pyrazol-1-yl)phenyl]carbamate

To a solution of benzyl N-[4-(3-carbamoyl-4-nitro-pyrazol-1-yl)phenyl]carbamate (70.0 mg, 183 umol) in MeOH (10.0 mL) and $H_2O$ (5.00 mL) was added $NH_4Cl$ (98.1 mg, 1.84 mmol) and Zn (60.0 mg, 917 umol), and the mixture was stirred at rt for 1 hr. On completion, the mixture was concentrated in vacuo. The mixture was diluted with $H_2O$ (10.0 mL) then extracted with EA (3×10 mL). The organic layers were dried with anhydrous $Na_2SO_4$, filtered and concentrated in vacuo to give the title compound (60.0 mg, 93% yield) as yellow solid, LC-MS (ESI$^+$) m/z 352.1 $(M+H)^+$ Tert-butyl N-[4-[4-[[1-(4-aminophenyl)-3-carbamoyl-pyrazol-4-yl]carbamoyl]oxazol-2-yl]-2-pyridyl]-N-(cyclopropylmethyl)carbamate (Intermediate KP)

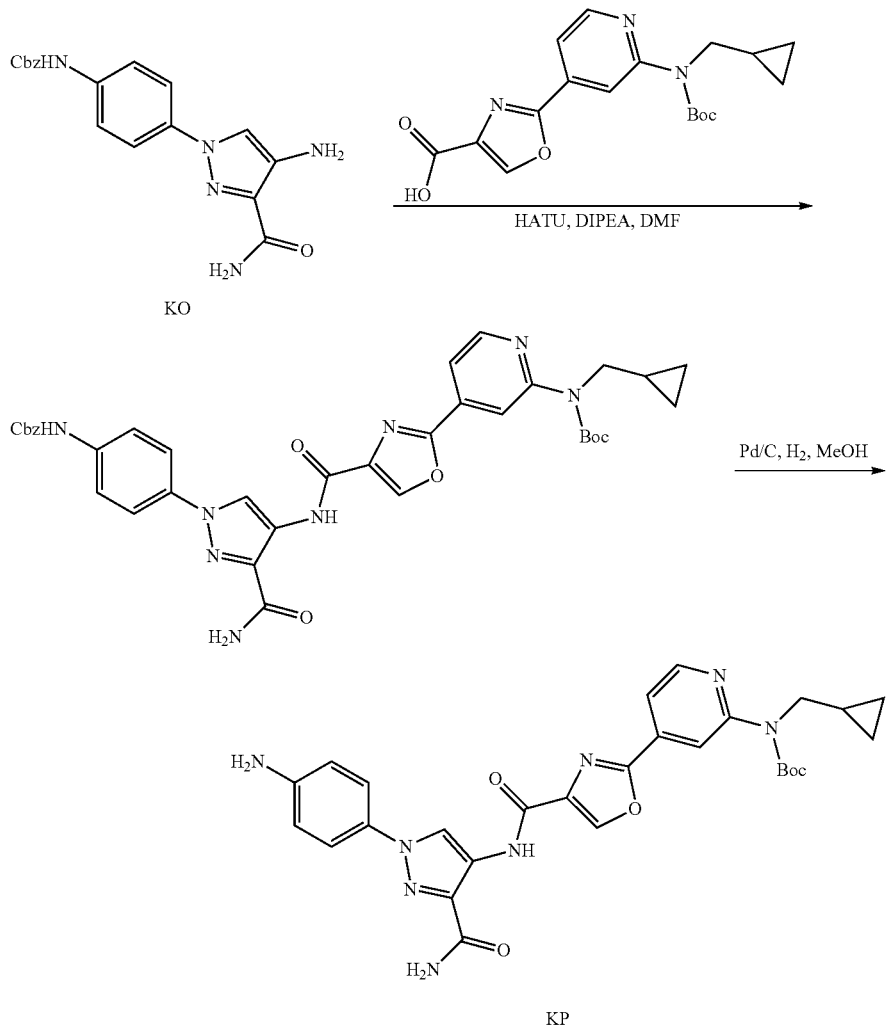

1531

Step 1—Tert-butyl N-[4-[4-[[1-[4-(benzyloxycarbonylamino)phenyl]-3-carbamoyl-pyrazol-4-yl]carbamoyl]oxazol-2-yl]-2-pyridyl]-N-(cyclopropylmethyl)carbamate To a solution of benzyl N-[4-(4-amino-3-carbamoyl-pyrazol-1-yl)phenyl]carbamate (60.0 mg, 170 umol, Intermediate KO), and 2-[2-[tertbutoxycarbonyl(cyclopropylmethyl)amino]-4-pyridyl]oxazole-4-carboxylic acid (92.0 mg, 256 umol, synthesized via Steps 1-4 of Intermediate DF) in DMF (3.00 mL) was added DIPEA (66.2 mg, 512 umol) and HATU (97.4 mg, 256 umol), and the mixture was stirred at rt for 0.5 hr. On completion, the mixture was diluted with H$_2$O (15 mL) and extracted with EA (3×15 mL). The organic layers were dried over anhydrous Na$_2$SO$_4$, filtered and concentrated in vacuo. The mixture was purified by reverse phase: (0.1% FA) to give the title compound (70.0 mg, 59% yield) as yellow solid. LC-MS (ESI$^+$) m/z 693.2 (M+H)$^+$.

Step 2—Tert-butyl N-[4-[4-[[1-(4-aminophenyl)-3-carbamoyl-pyrazol-4-yl]carbamoyl]oxazol-2-yl]-2-pyridyl]-N-(cyclopropylmethyl)carbamate To a solution of tert-butyl N-[4-[4-[[1-[4-(benzyloxycarbonylamino)phenyl]-3-carbamoyl-pyrazol-4-yl]carbamoyl]oxazol-2-yl]-2-pyridyl]-N-(cyclopropylmethyl)carbamate (70.0 mg, 101 umol) in THF (10.0 mL) was added Pd/C (30.0 mg), the mixture was stirred at rt for 1 hr under H$_2$ (15 Psi). On completion, the mixture was filtered and concentrated in vacuo to give the title compound (55.0 mg, 90% yield) as yellow solid. LC-MS (ESI$^+$) m/z 559.4 (M+H)$^+$.

Methyl 4-amino-1-methyl-pyrazole-3-carboxylate (Intermediate KQ)

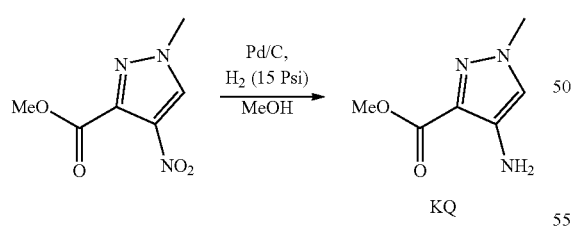

To a solution of methyl 1-methyl-4-nitro-pyrazole-3-carboxylate (2 g, 10.8 mmol, CAS #400877-57-8) in MeOH (20 mL) was added Pd/C (200 mg, 10% wt) under N$_2$ atmosphere. The suspension was degassed and purged with H$_2$ gas 3 times. The mixture was stirred under H$_2$ (15 Psi) at rt for 12 hr. On completion, the reaction mixture was filtered and concentrated in vacuo to give the title compound (1.68 g, 100% yield) as a white solid. $^1$H NMR (400 MHz, CDCl$_3$) δ 6.95 (s, 1H), 3.92 (s, 3H), 3.86 (s, 3H).

1532

4-[[2-[2-[Tert-butoxycarbonyl(2,2,2-trifluoroethyl)amino]-4-pyridyl]oxazole-4-carbonyl]amino]-1-methyl-pyrazole-3-carboxylic acid (Intermediate KR)

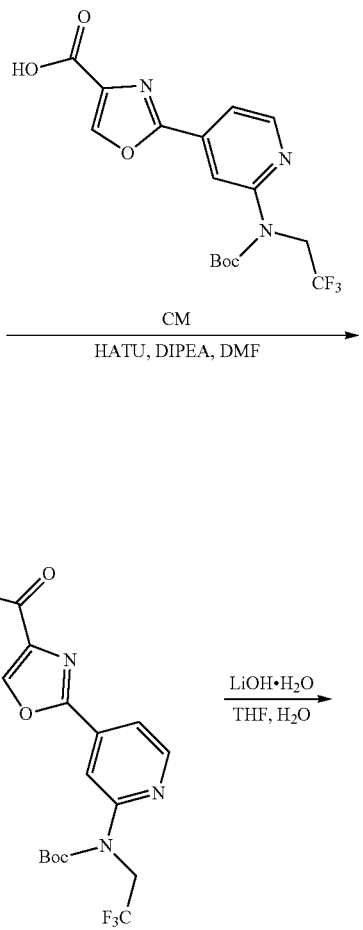

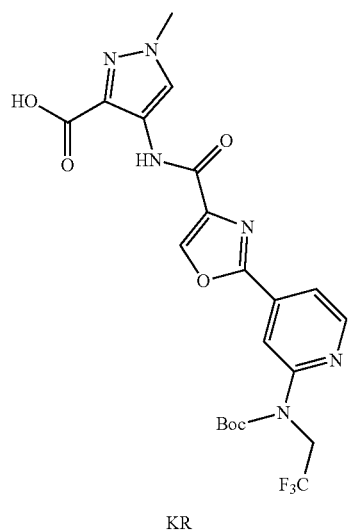

Step 1—Methyl 4-[[2-[2-[tert-butoxycarbonyl(2,2,2-trifluoroethyl)amino]-4-pyridyl]oxazole-4-carbonyl]amino]-1-methyl-pyrazole-3-carboxylate To a solution of methyl 4-amino-1-methyl-pyrazole-3-carboxylate (1.68 g, 10.8 mmol, Intermediate KQ) and 2-[2-[tert-butoxycarbonyl(2,2,2-trifluoroethyl)amino]-4-pyridyl]oxazole-4-carboxylic acid (4.19 g, 10.8 mmol, Intermediate CM) in DMF (20 mL) was added DIPEA (2.80 g, 21.7 mmol), The reaction mixture was stirred at rt for 0.5 hr. After, HATU (4.94 g, 13.0 mmol) was added and the resulting reaction mixture was stirred at rt for 0.5 hr. On completion, the reaction mixture was quenched with water (200 mL). White precipitate formed after the reaction was added to water, which was filtered and the filtered cake was dried in vacuo to give the title compound (5.1 g, 90% yield) as a white solid; $^1$H NMR (400 MHz, DMSO-$d_6$) δ 10.30 (s, 1H), 9.09 (s, 1H), 8.65 (s, 1H), 8.43 (s, 1H), 8.31 (s, 1H), 7.76 (s, 1H), 4.93-4.86 (m, 2H), 3.95 (s, 3H), 3.93 (s, 3H), 1.53 (s, 9H). LC-MS (ESI$^+$) m/z 547.1 (M+Na)$^+$.

Step 2—4-[[2-[2-[Tert-butoxycarbonyl(2,2,2-trifluoroethyl)amino]-4-pyridyl]oxazole-4-carbonyl]amino]-1-methyl-pyrazole-3-carboxylic acid To a solution of methyl 4-[[2-[2-[tert-butoxycarbonyl(2,2,2-trifluoroethyl)amino]-4-pyridyl]oxazole-4-carbonyl]amino]-1-methyl-pyrazole-3-carboxylate (500 mg, 953 umol) in a mixed solvent of THF (10 mL) and H$_2$O (2 mL) was added LiOH.H$_2$O (120 mg, 2.86 mmol). The reaction mixture was stirred at rt for 12 hrs. On completion, the reaction mixture was concentrated in vacuo. The residue was diluted with water (50 mL) and acidified with HCl (2 N) to pH=5, then filtered. The filtered cake was collected, ground up, and dried for 2 hours at 105-110° C. in the drying oven. This was then ground again to a fine powder to give the title compound (480 mg, 99% yield) as a white solid. $^1$H NMR (400 MHz, DMSO-$d_6$) δ 10.65 (s, 1H), 9.07 (s, 1H), 8.64 (d, J=4.8 Hz, 1H), 8.38 (s, 1H), 8.24 (s, 1H), 7.77 (dd, J=1.2, 5.2 Hz, 1H), 4.89 (q, J=8.8 Hz, 2H), 3.95 (s, 3H), 1.52 (s, 9H).

4-[3-(3-Aminopropoxy)propylamino]-2-(2,6-dioxo-3-piperidyl)isoindoline-1,3-dione (Intermediate KS)

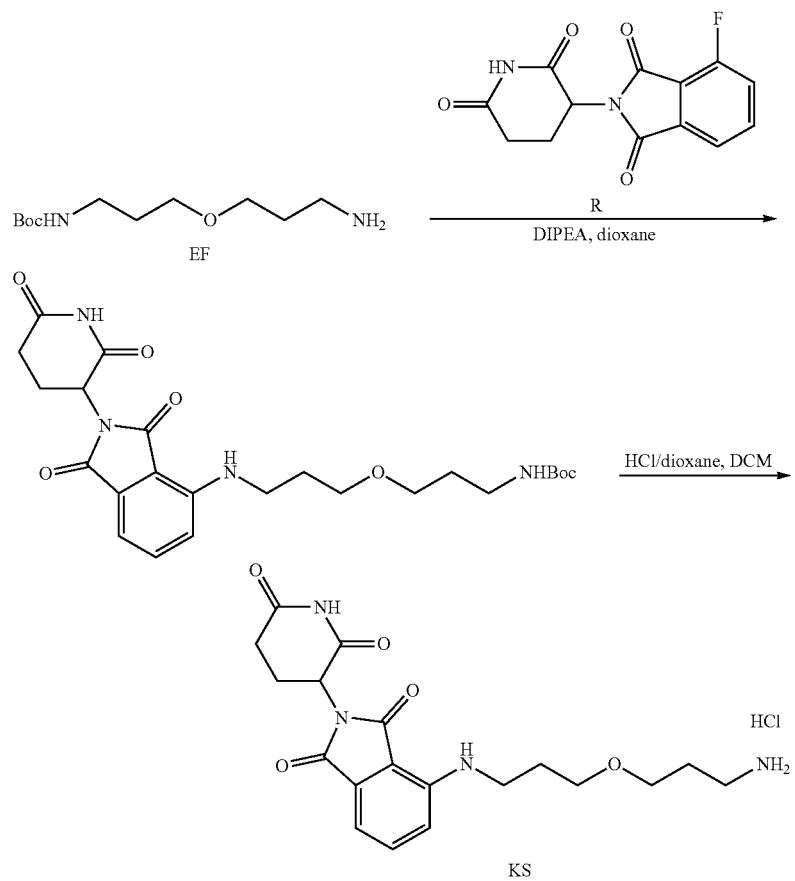

Step 1—Tert-butyl N-[3-[3-[[2-(2,6-dioxo-3-piperidyl)-1,3-dioxo-isoindolin-4-yl]amino]propoxy]propyl]carbamate To a mixture of tert-butyl N-[3-(3-aminopropoxy)propyl]carbamate (1.20 g, 5.17 mmol, Intermediate EF) and 2-(2,6-dioxo-3-piperidyl)-4-fluoro-isoindoline-1,3-dione (1.43 g, 5.17 mmol, Intermediate R) in dioxane (50 mL) was added DIPEA (6.68 g, 51.6 mmol, 9.00 mL). The reaction mixture was stirred at 115° C. for 12 hours. On completion, the reaction mixture was concentrated in vacuo. The residue was purified by column chromatography (SiO2, PE:EA=1:1 PE:EA=1:1, P1: Rf=0.08) to give the title compound (1.00 g, 39% yield) as yellow solid. LC-MS (ESI$^+$) m/z 511.3 (M+Na)$^+$ Step 2—4-[3-(3-Aminopropoxy)propylamino]-2-(2,6-dioxo-3-piperidyl)isoindoline-1,3-dione To a mixture of tert-butyl N-[3-[3-[[2-(2,6-dioxo-3-piperidyl)-1,3-dioxo-isoindolin-4-yl]amino]propoxy]propyl]

carbamate (1.20 g, 2.46 mmol) in DCM (10 mL) was added HCl/dioxane (4 M, 20 mL). The reaction mixture was stirred at rt for 1 hour. On completion, the reaction mixture was concentrated in vacuo to give the title compound (1.00 g, 95% yield, HCl) as yellow solid. LC-MS (ESI$^+$) m/z 389.1 (M+H)$^+$.

Tert-butyl N-[4-[4-[[1-(4-formylphenyl)-3-(methylcarbamoyl)pyrazol-4-yl]carbamoyl]oxazol-2-yl]-2-pyridyl]-N-(2,2,2-trifluoroethyl)carbamate (Intermediate KT)

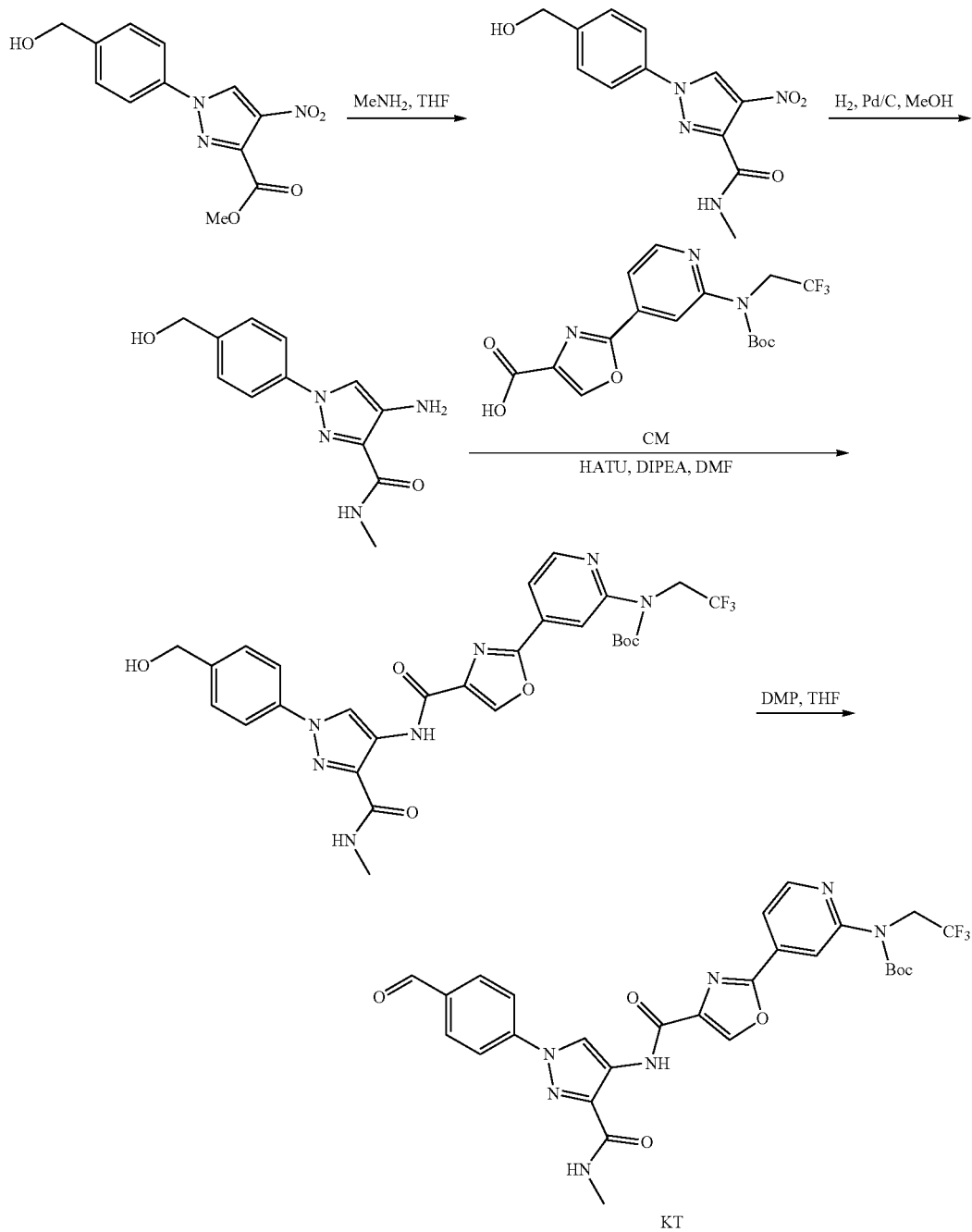

22Step 1—1-[4-(Hydroxymethyl)phenyl]-N-methyl-4-nitro-pyrazole-3-carboxamide To a solution of methyl 1-[4-(hydroxymethyl)phenyl]-4-nitro-pyrazole-3-carboxylate (200 mg, 721 umol, synthesized via Step 1 of Intermediate GB) in THF (5.00 mL) was added MeNH$_2$ (2.00 M, 5.00 mL), and the mixture was stirred at 70° C. for 16 hrs in a sealed tube. On completion, the mixture was concentrated in vacuo. The mixture was diluted with H$_2$O (30 mL), then extracted with EA (3×30 mL). The organic layers were dried over anhydrous Na$_2$SO$_4$, filtered and concentrated in vacuo to give the title compound (195 mg, 97% yield) as yellow solid. 1H NMR (400 MHz, DMSO-d$_6$) δ 9.68 (s, 1H), 8.81-8.68 (m, 1H), 7.97 (d, J=8.8 Hz, 2H), 7.57 (d, J=8.8 Hz, 2H), 5.39 (t, J=5.6 Hz, 1H), 4.63 (d, J=5.6 Hz, 2H), 2.87 (d, J 4.8 Hz, 3H)

Step 2—4-Amino-1-[4-(hydroxymethyl)phenyl]-N-methyl-pyrazole-3-carboxamide

To a solution of 1-[4-(hydroxymethyl)phenyl]-N-methyl-4-nitro-pyrazole-3-carboxamide (195 mg, 705 umol) in MeOH (100 mL) was added Pd/C (10 wt %, 100 mg), and the mixture was purged with H$_2$ several times and stirred at 15° C. for 0.5 hr under H$_2$ (15 psi). On completion, the mixture was filtered and concentrated in vacuo to give the title compound (160 mg, 90% yield) as yellow solid. LC-MS (ESI$^+$) m/z 247.1 (M+H)$^+$.

Step 3—Tert-butyl N-[4-[4-[[1-[4-(hydroxymethyl)phenyl]-3-(methylcarbamoyl)pyrazol-4-yl]carbamoyl]oxazol-2-yl]-2-pyridyl]-N-(2,2,2-trifluoroethyl)carbamate To a solution of 4-amino-1-[4-(hydroxymethyl)phenyl]-N-methyl-pyrazole-3-carboxamide (160 mg, 649 umol), 2-[2-[tert-butoxycarbonyl(2,2,2-trifluoroethyl)amino]-4-pyridyl]oxazole-4-carboxylic acid (251 mg, 649 umol, Intermediate CM) in DMF (3.00 mL) was added DIPEA (251 mg, 1.95 mmol) and HATU (296 mg, 779 umol), and the mixture was stirred at rt for 0.5 hr. On completion, the mixture was diluted with H$_2$O (1.00 mL) and concentrated in vacuo. The mixture was purified by reverse phase chromatography (0.1% NH$_3$.H$_2$O) to give the title compound (200 mg, 50% yield) as yellow solid. $^1$H NMR (400 MHz, DMSO-d$_6$) δ 11.08 (s, 1H), 9.10 (s, 1H), 8.93 (s, 1H), 8.67 (d, J=5.2 Hz, 1H), 8.62-8.56 (m, 1H), 8.29 (s, 1H), 7.93 (d, J=8.8 Hz, 2H), 7.82-7.77 (m, 1H), 7.50 (d, J=8.8 Hz, 2H), 5.30 (t, J=5.6 Hz, 1H), 4.96-4.86 (m, 2H), 4.57 (d, J=5.6 Hz, 2H), 2.87 (d, J=4.8 Hz, 3H), 1.56 (s, 9H).

Step 4—Tert-butyl N-[4-[4-[[1-(4-formylphenyl)-3-(methylcarbamoyl)pyrazol-4-yl]carbamoyl]oxazol-2-yl]-2-pyridyl]-N-(2,2,2-trifluoroethyl)carbamate To a solution of tert-butyl N-[4-[4-[[1-[4-(hydroxymethyl)phenyl]-3-(methylcarbamoyl)pyrazol-4-yl]carbamoyl]oxazol-2-yl]-2-pyridyl]-N-(2,2,2-trifluoroethyl)carbamate (110 mg, 178 umol) in THF (20.0 mL) was added DMP (90.9 mg, 214 umol), and the mixture was stirred at rt for 1 hr. On completion, the mixture was quenched with saturated Na$_2$S203 (30 mL) and washed with saturated NaHCO$_3$ (2×30 mL). The organic layer was dried over anhydrous Na$_2$SO$_4$, filtered and concentrated in vacuo to give the title compound (105 mg, 90% yield) as yellow solid. LC-MS (ESI$^+$) m/z 614.3 (M+H)$^+$.

1-[4-[4-Amino-3-(difluoromethyl)pyrazol-1-yl]phenyl]ethenone (Intermediate KU)

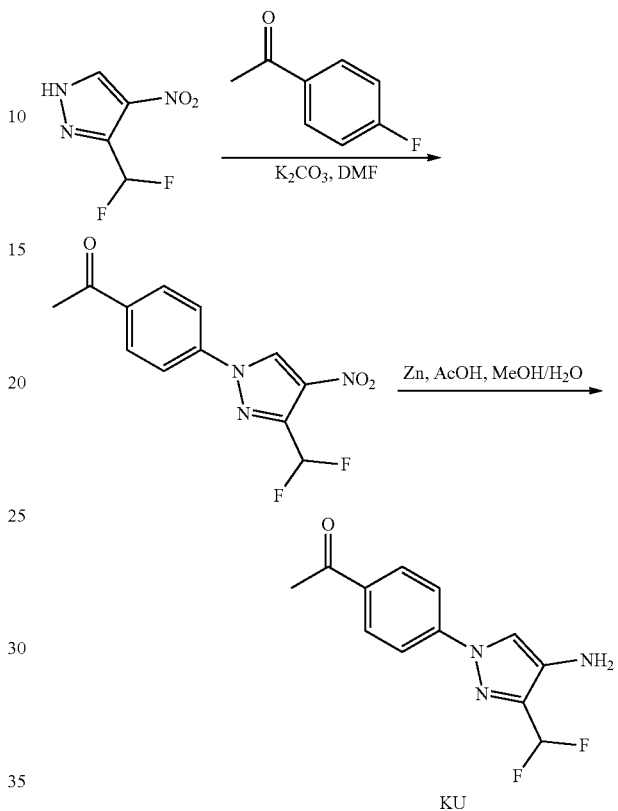

Step 1—1-[4-[3-(difluoromethyl)-4-nitro-pyrazol-1-yl]phenyl]ethanone

To a mixture of 3-(difluoromethyl)-4-nitro-1H-pyrazole (1.42 g, 8.69 mmol, Intermediate HS), 1-(4-fluorophenyl)ethanone (1.0 g, 7.24 mmol) in DMF (10 mL) was added K$_2$CO$_3$ (1.50 g, 10.8 mmol). The reaction mixture was stirred at 120° C. for 12 hours. On completion, the mixture was concentrated in vacuo. The residue was purified by column chromatography (SiO$_2$) to give the title compound (435 mg, 21% yield) as brown oil. $^1$H NMR (400 MHz, DMSO-d$_6$) δ 9.93 (s, 1H), 8.17-8.13 (m, 4H), 7.59-7.32 (m, 1H), 2.64 (s, 3H).

Step 2—1-[4-[4-Amino-3-(difluoromethyl)pyrazol-1-yl]phenyl]ethanone

To a mixture of 1-[4-[3-(difluoromethyl)-4-nitro-pyrazol-1-yl]phenyl]ethanone (360 mg, 1.28 mmol) in MeOH (20 mL) and H$_2$O (10 mL) was added Zn (837 mg, 12.8 mmol) and AcOH (769 mg, 12.8 mmol). The reaction mixture was stirred at rt for 1 hour. On completion, the mixture was concentrated in vacuo to give the title compound (186 mg, 58% yield) as a yellow solid. LC-MS (ESI$^+$) m/z 252.2 (M+H)$^+$.

Tert-butyl N-[4-[4-[[1-(4-acetylphenyl)-3-(difluoromethyl)pyrazol-4-yl]carbamoyl]oxazol-2-yl]-2-pyridyl]-N-(cyclopropylmethyl)carbamate (Intermediate KV)

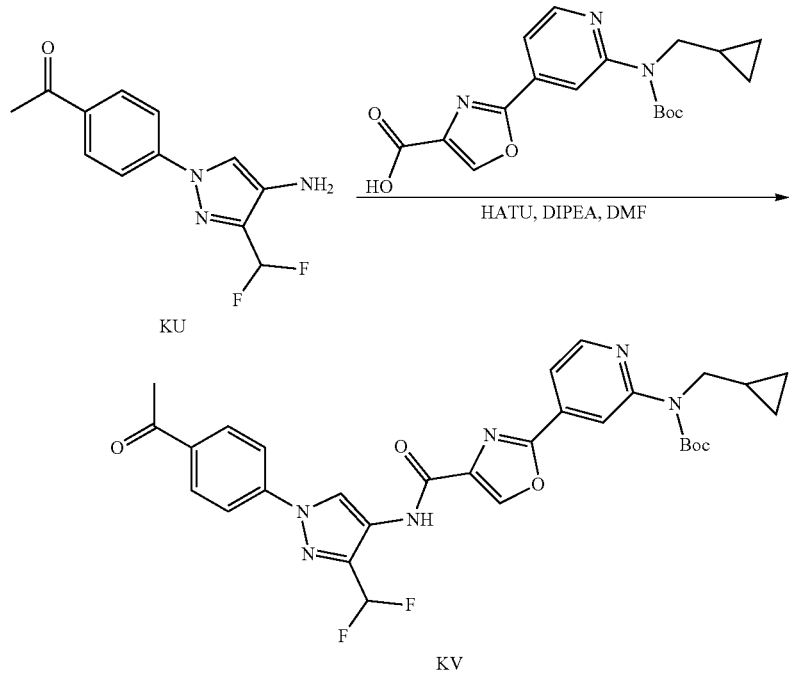

To a mixture of 1-[4-[4-amino-3-(difluoromethyl)pyrazol-1-yl]phenyl]ethanone (90 mg, 358 umol, Intermediate KU), 2-[2-[tert-butoxycarbonyl(cyclopropylmethyl)amino]-4-pyridyl]oxazole-4-carboxylic acid (154 mg, 429 umol, synthesized via Steps 1-4 of Intermediate DF) in DMF (10 mL) was added DIPEA (139 mg, 1.07 mmol) and HATU (163 mg, 430 umol). The mixture and stirred at rt for 2 hours. On completion, the mixture was concentrated in vacuo. The residue was purified by reversed-phase HPLC (0.1% FA condition) to give the title compound (165 mg, 75% yield) as a white solid. LC-MS (ESI⁺) m/z 593.2 (M+H)⁺

Methyl 4-(4-amino-3-(3-((tetrahydro-2H-pyran-2-yl)oxy)propyl)-1H-pyrazol-1-yl)benzoate (Intermediate KW)

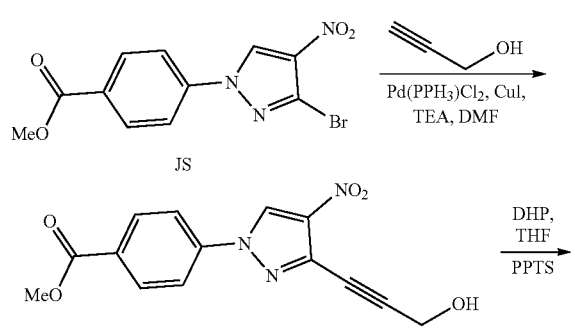

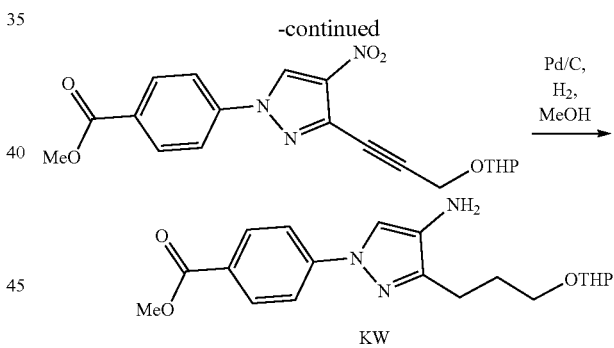

Step 1—Methyl 4-(3-(3-hydroxyprop-1-yn-1-yl)-4-nitro-1H-pyrazol-1-yl)benzoate

Methyl 4-(3-bromo-4-nitro-pyrazol-1-yl)benzoate (1 g, 3.07 mmol, Intermediate JS), prop-2-yn-1-ol (500 mg, 8.92 mmol), Pd(PPh₃)₂Cl₂ (215 mg, 307 umol), TEA (3.10 g, 30.7 mmol), and CuI (58.4 mg, 307 umol) were taken up into a microwave tube in DMF (10 mL) under N₂. The reaction mixture was de-gassed with N₂ and then the sealed tube was heated to 80° C. for 0.5 hour. On completion, the reaction mixture was concentrated in vacuo. The crude product was purified by silica gel chromatography (PE:EA=2:1) to give the title compound (920 mg, 100% yield) as a yellow solid. ¹H NMR (400 MHz, DMSO-d₆) δ9.87 (s, 1H), 8.18 (s, 4H), 5.62 (t, J=6.0 Hz, 1H), 5.49-5.43 (m, 1H), 4.47 (d, J=6.0 Hz, 2H), 3.94 (s, 3H).

Step 2—Methyl 4-(4-nitro-3-(3-((tetrahydro-2H-pyran-2-yl)oxy)prop-1-yn-1-yl)-1H-pyrazol-1-yl)benzoate To a solution of methyl 4-[3-(3-hydroxyprop-1-ynyl)-4-nitro-pyrazol-1-yl]benzoate (600 mg, 1.99 mmol) and DHP (251 mg, 2.99 mmol) in a mixed solvent of DCM (100 mL) and THF (20 mL) was added PPTS (50.1 mg, 199 umol). The reaction mixture was stirred at rt for 12 hours under $N_2$. On completion, the reaction mixture was concentrated in vacuo. The crude product purified by column chromatography ($SiO_2$, Petroleum ether/Ethyl acetate=5/1) to give the title compound (700 mg, 91% yield) as a white solid. $^1$H NMR (400 MHz, DMSO-$d_6$) δ 9.83 (s, 1H), 8.13 (s, 4H), 4.94-4.86 (m, 1H), 4.66-4.50 (m, 2H), 3.90 (s, 3H), 3.79 (ddd, J=3.2, 8.4, 11.2 Hz, 1H), 3.57-3.47 (m, 1H), 1.75-1.65 (m, 2H), 1.59-1.49 (m, 4H). LC-MS (ESI$^+$) m/z 408.1 (M+Na)$^+$.

Step 3—Methyl 4-(4-amino-3-(3-((tetrahydro-2H-pyran-2-yl)oxy)propyl)-1H-pyrazol-1-yl)benzoate To a solution of methyl 4-[4-nitro-3-(3-tetrahydropyran-2-yloxyprop-1-ynyl)pyrazol-1-yl]benzoate (930 mg, 2.41 mmol) in MeOH (10 mL) was added Pd/C (50 mg, 10 wt %) and Pd(OH)$_2$/C (50 mg, 10 wt %) under $N_2$ atmosphere. The suspension was degassed and purged with $H_2$ gas 3 times. The mixture was stirred under $H_2$ (15 Psi) at rt for 24 hours. On completion, the reaction mixture was filtered and concentrated in vacuo to give the title compound (760 mg, 88% yield) as a yellow solid. LC-MS (ESI$^+$) m/z 360.2 (M+H)$^+$.

4-(4-(2-(2-((Tert-butoxycarbonyl)(2,2,2-trifluoroethyl)amino)pyridin-4-yl)oxazole-4-carboxamido)-3-(3-((tetrahydro-2H-pyran-2-yl)oxy)propyl)-1H-pyrazol-1-yl)benzoic acid (Intermediate KX)

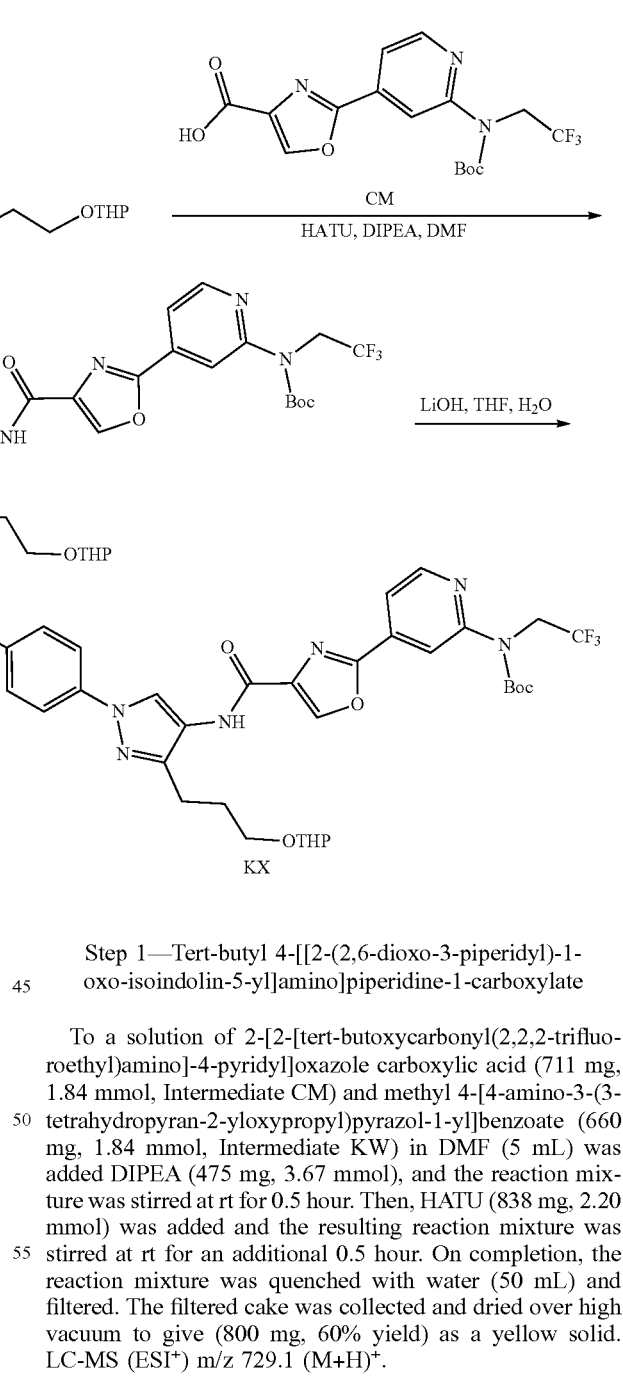

Step 1—Tert-butyl 4-[[2-(2,6-dioxo-3-piperidyl)-1-oxo-isoindolin-5-yl]amino]piperidine-1-carboxylate To a solution of 2-[2-[tert-butoxycarbonyl(2,2,2-trifluoroethyl)amino]-4-pyridyl]oxazole carboxylic acid (711 mg, 1.84 mmol, Intermediate CM) and methyl 4-[4-amino-3-(3-tetrahydropyran-2-yloxypropyl)pyrazol-1-yl]benzoate (660 mg, 1.84 mmol, Intermediate KW) in DMF (5 mL) was added DIPEA (475 mg, 3.67 mmol), and the reaction mixture was stirred at rt for 0.5 hour. Then, HATU (838 mg, 2.20 mmol) was added and the resulting reaction mixture was stirred at rt for an additional 0.5 hour. On completion, the reaction mixture was quenched with water (50 mL) and filtered. The filtered cake was collected and dried over high vacuum to give (800 mg, 60% yield) as a yellow solid. LC-MS (ESI$^+$) m/z 729.1 (M+H)$^+$.

Step 2—4-(4-(2-(2-((Tert-butoxycarbonyl)(2,2,2-trifluoroethyl)amino)pyridin-4-yl)oxazole-4-carboxamido)-3-(3-((tetrahydro-2H-pyran-2-yl)oxy)propyl)-1H-pyrazol-1-yl)benzoic acid To a solution of methyl 4-[4-[[2-[2-[tert-butoxycarbonyl(2,2,2-trifluoroethyl)amino]-4-pyridyl]oxazole-4-carbonyl]

1543 amino]-3-(3-tetrahydropyran-2-yloxypropyl)pyrazol-1-yl]benzoate (800 mg, 1.10 mmol) in a mixed solvent of THF (9 mL) and H$_2$O (3 mL) was added LiOH.H$_2$O (138 mg, 3.29 mmol). The reaction mixture was stirred at rt for 12 hours. On completion, the reaction mixture was concentrated in vacuo to removed THF then diluted with water (10 mL) and acidified with 2 N aq.HCl to pH=5, then extracted with ethyl acetate (3×50 mL). The combined organic layer was washed with brine, dried over anhydrous sodium sulfate, filtered and concentrated in vacuo to give the title compound (740 mg, 94% yield) as a yellow solid. LC-MS (ESI$^+$) m/z 715.1 (M+H)$^+$.

Tert-butyl (4-(4-((1-(4-formylphenyl)-3-(3-((tetrahydro-2H-pyran-2-yl)oxy)propyl)-1H-pyrazol-4-yl)carbamoyl)oxazol-2-yl)pyridin-2-yl)(2,2,2-trifluoroethyl)carbamate (Intermediate KY)

1544

Step 1—4-(4-(2-(2-((Tert-butoxycarbonyl)(2,2,2-trifluoroethyl)amino)pyridin-4-yl)oxazole-4-carboxamido)-3-(3-((tetrahydro-2H-pyran-2-yl)oxy)propyl)-1H-pyrazol-1-yl)benzoic (isopropyl carbonic) anhydride To a solution of 4-[4-[[2-[2-[tert-butoxycarbonyl(2,2,2-trifluoroethyl)amino]-4-pyridyl]oxazole-4-carbonyl]amino]-3-(3-tetrahydropyran-2-yloxypropyl)pyrazol-1-yl]benzoic acid (740 mg, 1.04 mmol, Intermediate KX) in THF (20 mL) was added TEA (419 mg, 4.14 mmol). Then, the reaction mixture was cooled to −10° C. and isopropyl carbonochloridate (254 mg, 2.07 mmol) was added. The resulting reaction mixture was stirred at −10° C. for 2 hours. On completion, the reaction mixture was filtered. The filtrate

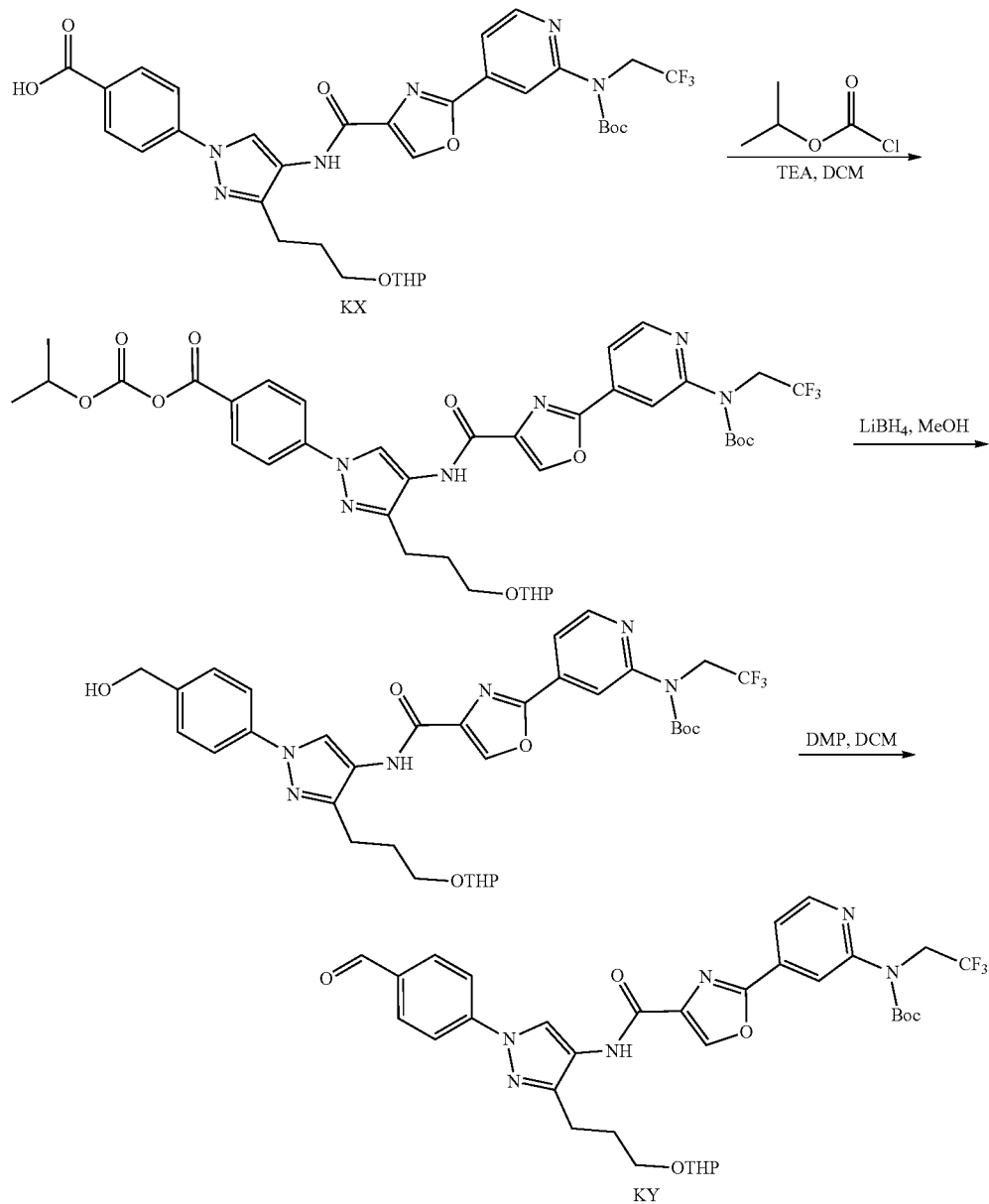

was concentrated in vacuo to give the title compound (800 mg, 96% yield) as a white solid. LC-MS (ESI$^+$) m/z 801.1 (M+H)$^+$.

Step 2—Tert-butyl (4-(4-((1-(4-(hydroxymethyl) phenyl)-3-(3-((tetrahydro-2H-pyran-2-yl)oxy) propyl)-1H-pyrazol-4-yl)carbamoyl)oxazol-2-yl)pyridin-2-yl)(2,2,2-trifluoroethyl)carbamate To a solution of isopropoxycarbonyl 4-[4-[[2-[2-[tert-butoxycarbonyl(2,2,2-trifluoroethyl)amino]-4-pyridyl]oxazole-4-carbonyl]amino]-3-(3-tetrahydropyran-2-yloxypropyl)pyrazol-1-yl]benzoate (800 mg, 999 umol) in THF (50 mL) was added H$_2$O (180 mg, 9.99 mmol) and LiBH$_4$ (109 mg, 5.00 mmol). The reaction mixture was stirred at 0° C. for 10 minutes. On completion, the mixture was quenched with water (5 mL) and was extracted with DCM (3×50 mL). The combined organic layer was washed with brine (20 mL), dried over anhydrous sodium sulfate, filtered and concentrated in vacuo to give the title compound (700 mg, 100% yield) as a white solid. LC-MS (ESI$^+$) m/z 701.1 (M+H)$^+$.

Step 3—Tert-butyl (4-(4-((1-(4-formylphenyl)-3-(3-((tetrahydro-2H-pyran-2-yl)oxy)propyl)-1H-pyrazol-4-yl)carbamoyl)oxazol-2-yl)pyridin-2-yl)(2,2,2-trifluoroethyl)carbamate To a solution of tert-butyl N-[4-[4-[[1-[4-(hydroxymethyl)phenyl]-3-(3-tetrahydropyran-2-yloxypropyl) pyrazol-4-yl]carbamoyl]oxazol-2-yl]-2-pyridyl]-N-(2,2,2-trifluoroethyl)carbamate (700 mg, 999 umol) in DCM (20 mL) was added DMP (847 mg, 2.00 mmol). The reaction mixture was stirred at rt for 2 hours. On completion, the reaction mixture was quenched with water (1 mL) and was concentrated in vacuo. The crude product was purified by prep-HPLC (condition: 0.1% FA) to give the title compound (270 mg, 30% yield) as colorless solid. LC-MS (ESI$^+$) m/z 699.1 (M+H)$^+$.

4-[1-(Tert-butoxycarbonylamino)cyclopropyl phenyl]boronic acid (Intermediate KZ)

Step 1—Tert-butyl N-[1-[4-(4,4,5,5-tetramethyl-1,3,2-dioxaborolan-2-yl)phenyl]cyclopropyl]carbamate A mixture of tert-butyl N-[1-(4-bromophenyl)cyclopropyl]carbamate (3 g, 9.61 mmol, CAS #360773-84-8), Pin$_2$B$_2$ (4.88 g, 19.2 mmol), KOAc (2.83 g, 28.8 mmol) and cyclopentyl(diphenyl)phosphane; dichloromethane; dichloropalladium; iron (392 mg, 480 umol) in DMSO (30 mL) was degassed and then heated to 70° C. for 12 hours under N$_2$. On completion, the mixture was quenched with water (200 mL) and filtered. The filter cake was purified by silica gel chromatography (SiO$_2$) to give the title compound (3.0 g, 87% yield) as a white solid. LC-MS (ESI+) m/z 398.2 (M+K)$^+$.

Step 2—[4-[1-(Tert-butoxycarbonylamino)cyclopropyl]phenyl]boronic acid

To a solution of tert-butyl N-[1-[4-(4,4,5,5-tetramethyl-1,3,2-dioxaborolan-2-yl)phenyl]cyclopropyl]carbamate (1.2 g, 3.34 mmol) in a mixed solvent of THF (30 mL) and H$_2$O (6 mL) was added NaIO$_4$ (2.14 g, 10.0 mmol). The reaction mixture was stirred at rt for 0.5 hour. Then, HCl (3 M, 2.23 mL) was added and the mixture was stirred at rt for 4 hrs. On completion, the mixture was diluted with water, then extracted with EA (30 mL×2). The organic layer was washed with water and concentrated in vacuo. The residue was purified by reverse phase (0.1% FA condition) to give the title compound (0.76 g, 82% yield) as a white solid. LC-MS (ESI$^+$) m/z 278.1 (M+H)$^+$.

Tert-butyl N-[1-[4-[4-amino-3-(difluoromethyl)pyrazol-1-yl]phenyl]cyclopropyl]carbamate (Intermediate LA)

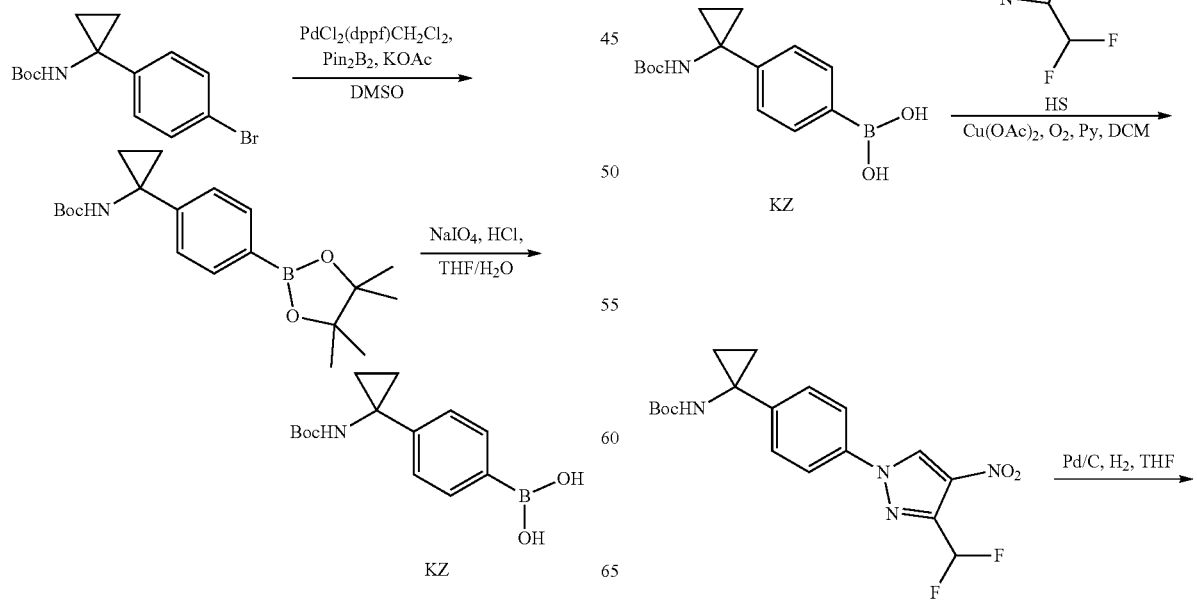

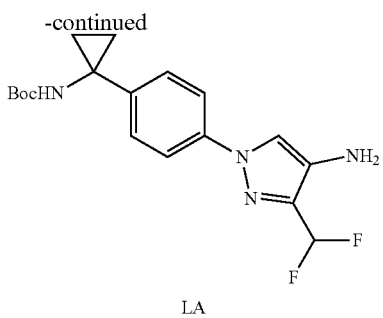

LA

Step 1—Tert-butyl N-[1-[4-[3-(difluoromethyl)-4-nitro-pyrazol-1-yl]phenyl]cyclopropyl]carbamate To a solution of [4-[1-(tert-butoxycarbonylamino)cyclopropyl]phenyl]boronic acid (0.76 g, 2.74 mmol, Intermediate KZ) and 3-(difluoromethyl)-4-nitro-1H-pyrazole (447 mg, 2.74 mmol, Intermediate HS) in DCM (10 mL) was added Cu(OAc)₂ (747 mg, 4.11 mmol) and pyridine (4.34 g, 54.9 mmol). The reaction mixture was stirred at rt for 10 hours under oxygen (15 Psi) atmosphere. On completion, the mixture was concentrated in vacuo. The residue was purified by silica gel chromatography (SiO₂), then the residue was repurified by reverse phase (0.1% FA condition) to give the title compound (550 mg, 51% yield) as a white solid. ¹H NMR (400 MHz, DMSO-d₆) δ 9.71 (s, 1H), 7.86 (d, J=8.4 Hz, 2H), 7.78 (s, 1H), 7.56-7.27 (m, 3H), 1.43-1.25 (m, 9H), 1.22-1.17 (m, 4H); LC-MS (ESI⁺) m/z 339.0 (M-56+H)⁺.

Step 2—Tert-butyl N-[1-[4-[4-amino-3-(difluoromethyl)pyrazol-1-yl]phenyl]cyclopropyl]carbamate To a solution of tert-butyl N-[1-[4-[3-(difluoromethyl)-4-nitro-pyrazol-1-yl]phenyl]cyclopropyl]carbamate (0.55 g, 1.39 mmol) in THF (10 mL) was added Pd/C (0.2 g, 10 wt %). The reaction mixture was stirred at rt for 4 hours under H₂ (15 Psi) atmosphere. On completion, the mixture was filtered and the filtrate was concentrated in vacuo to give the title compound (0.42 g, 83% yield) as a yellow solid. LC-MS (ESI⁺) m/z 365.1 (M+H)⁺.

N-[1-[4-(1-aminocyclopropyl)phenyl]-3-(difluoromethyl)pyrazol-4-yl]-2-[2-(cyclopropylmethylamino)-4-pyridyl]oxazole-4-carboxamide (Intermediate LB)

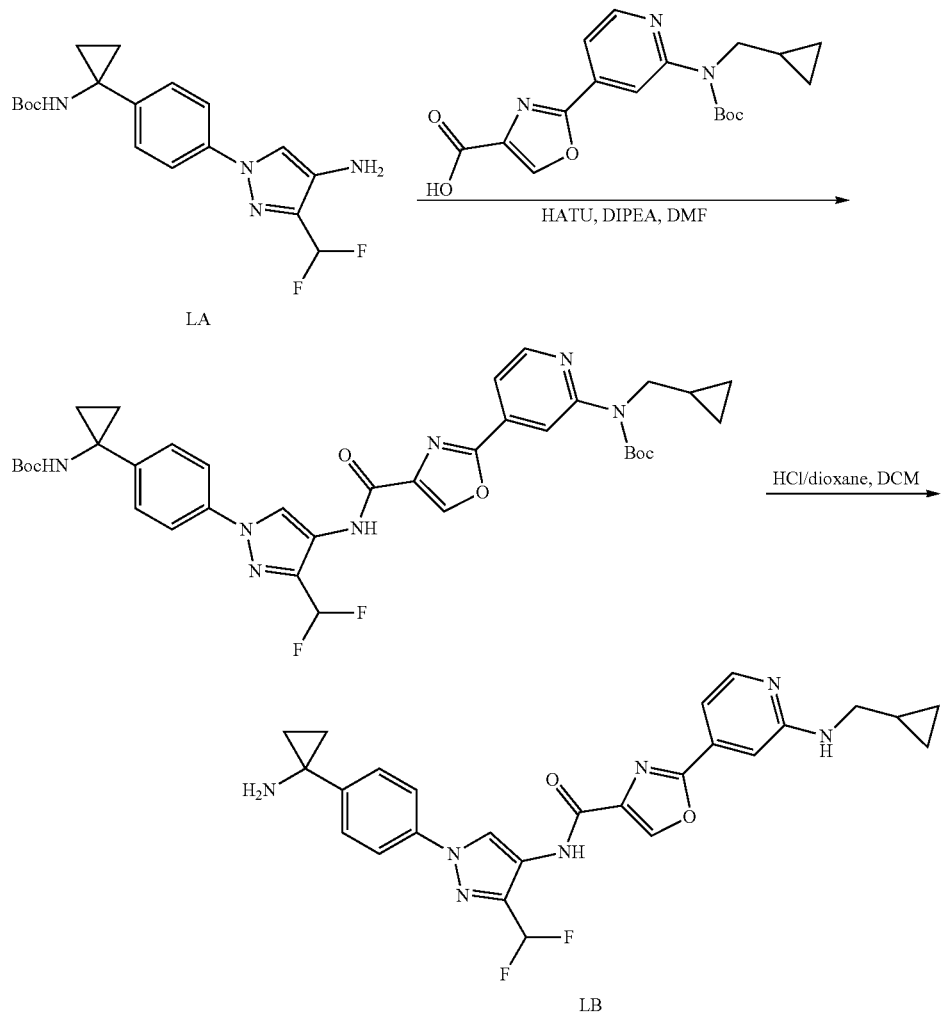

LB

Step 1—Tert-butyl N-[4-[4-[[1-[4-[1-(tert-butoxy-carbonylamino)cyclopropyl]phenyl]-3-(difluoromethyl)pyrazol-4-yl]carbamoyl]oxazol-2-yl]-2-pyridyl]-N-(cyclopropylmethyl)carbamate To a solution of tert-butyl N-[1-[4-[4-amino-3-(difluoromethyl)pyrazol-1-yl]phenyl]cyclopropyl]carbamate (220 mg, 604 umol, Intermediate LA) and 2-[2-[tert-butoxycarbonyl(cyclopropylmethyl)amino]-4-pyridyl]oxazole-4-carboxylic acid (217 mg, 604 umol, synthesized via Steps 1-4 of Intermediate DF) in DMF (5 mL) was added DIPEA (234 mg, 1.81 mmol) and HATU (276 mg, 725 umol). The reaction mixture was stirred at rt for 0.5 hour. On completion, the mixture was quenched with water (50 mL), filtered and the filter cake was dried in vacuo to give the title compound (0.27 g, 63% yield) as a brown solid. LC-MS (ESI$^+$) m/z 706.4 (M+H)$^+$.

Step 2—N-[1-[4-(1-aminocyclopropyl)phenyl]-3-(difluoromethyl)pyrazol-4-yl]-2-[2-(cyclopropylmethylamino)-4-pyridyl]oxazole-4-carboxamide To a solution of tert-butyl N-[4-[4-[[1-[4-[1-(tert-butoxycarbonylamino)cyclopropyl]phenyl]-3-(difluoromethyl)pyrazol-4-yl]carbamoyl]oxazol-2-yl]-2-pyridyl]-N-(cyclopropylmethyl)carbamate (250 mg, 354 umol) in DCM (1 mL) was added 4.0 M HCl/dioxane (1 mL). The reaction mixture was stirred at rt for 10 hours. On completion, the mixture was concentrated in vacuo to give the title compound (0.19 g, 99% yield, HCl) as a light yellow solid. LC-MS (ESI$^+$) m/z 506.2 (M+H)$^+$.

2-(2-Prop-2-ynoxyethoxy)ethanol (Intermediate LC)

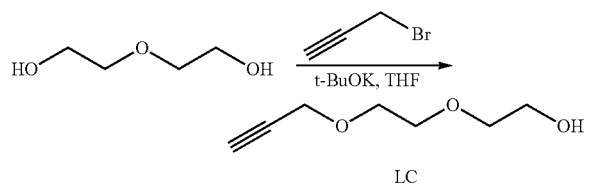

To a mixture of t-BuOK (4.76 g, 42.5 mmol) in THF (120 mL) was added 2-(2-hydroxyethoxy)ethanol (8.92 g, 84.0 mmol, CAS #111-46-4) at 0° C. The reaction mixture was stirred at rt for 30 minutes and then 3-bromoprop-1-yne (5 g, 42.0 mmol) in THF (25 mL) was added dropwise. The reaction mixture was stirred at rt for 12 hours. On completion, the mixture was filtered and the filtrate was concentrated in vacuo. The residue was purified by silica gel chromatography (SiO$_2$) to give the title compound (3 g, 50% yield) as yellow oil. $^1$H NMR (400 MHz, CDCl$_3$) δ 4.20 (d, J=2.4 Hz, 2H), 3.76-3.65 (m, 6H), 3.63-3.56 (m, 2H), 2.44 (t, J=2.4 Hz, 1H), 2.41 (s, 1H).

2,2-Dimethyl-4-oxo-3,8,11,14-tetraoxa-5-azahexadecan-16-yl 4-methylbenzenesulfonate (Intermediate LD)

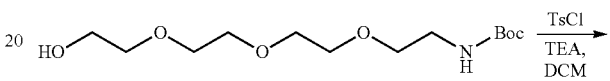

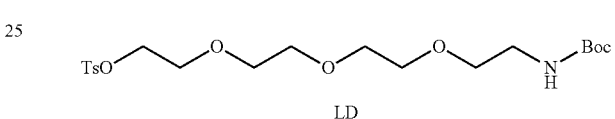

LD

To a stirred solution of tert-butyl (2-(2-(2-(2-hydroxyethoxy)ethoxy)ethoxy)ethyl)carbamate (8 g, 27.30 mmol, synthesized via Step 1 of Intermediate EN) in DCM (100 mL) was added TEA (5.52 g, 54.60 mmol) at rt. To the above reaction mixture was added dropwise TsCl (10.41 g, 54.60 mmol) in DCM (5 mL) at 0° C. After the addition, the reaction mixture was stirred at rt overnight. The mixture was concentrated in vacuo and the residue was purified via column chromatography (Petroleum ether/EtOAc=5%-80%) to give the title compound (10.9 g, 73%) as a yellow oil. LC-MS (ESI$^+$): m/z 448.3 (M+H)$^+$.

2-[2-[3-[1-(2,6-Dioxo-3-piperidyl)-3-methyl-2-oxobenzimidazol-4-yl]propoxy]ethoxy]acetaldehyde (Intermediate LE)

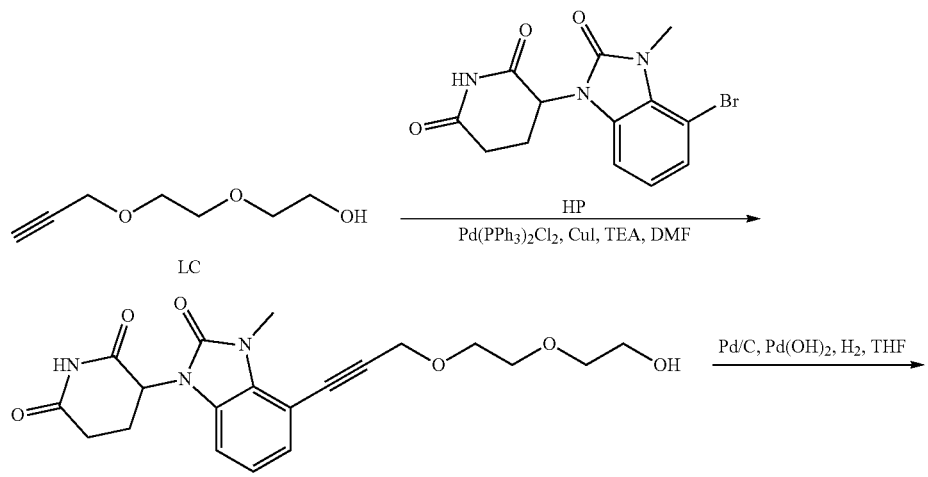

-continued

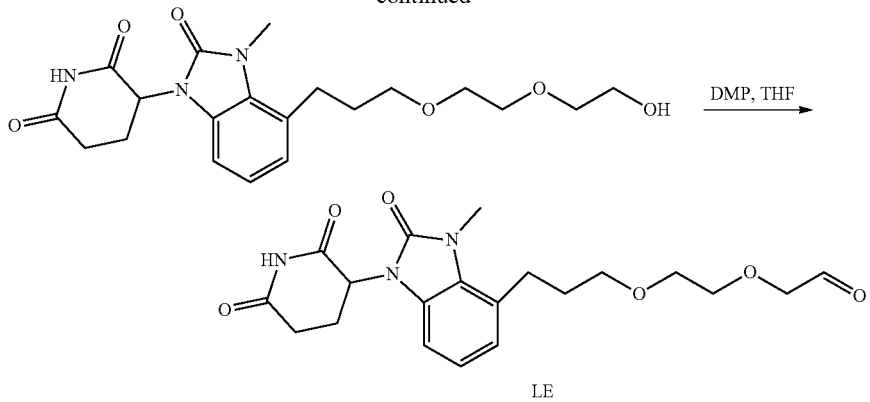

LE

Step 1—3-[4-[3-[2-(2-hydroxyethoxy)ethoxy]prop-1-ynyl]-3-methyl-2-oxo-benzimidazol-1-yl]piperidine-2,6-dione 2-(2-prop-2-ynoxyethoxy)ethanol (384 mg, 2.66 mmol, Intermediate LC), CuI (84.5 mg, 444 umol) and Pd(PPh$_3$)$_2$Cl$_2$ (311 mg, 444 umol) was taken up into a tube. Then 3-(4-bromo-3-methyl-2-oxo-benzimidazol-1-yl) piperidine-2,6-dione (300 mg, 887 umol, Intermediate HP), TEA (1.62 g, 16 mmol) and DMF (5 mL) were added into the above tube. The mixture was degassed with N$_2$ and the sealed tube was heated at 80° C. for 2 hours. On completion, the mixture was concentrated in vacuo. The residue was purified by reverse phase (0.1% FA condition) to give the title compound (0.12 g, 34% yield) as a brown solid. LC-MS (ESI$^+$) m/z 402.1 (M+H)$^+$.

Step 2—3-[4-[3-[2-(2-hydroxyethoxy)ethoxy]propyl]-3-methyl-2-oxo-benzimidazol-1-yl]piperidine-2,6-dione To a solution of 3-[4-[3-[2-(2-hydroxyethoxy)ethoxy]prop-1-ynyl]-3-methyl-2-oxo-benzimidazol-1-yl]piperidine-2,6-dione (50 mg, 125 umol) in THF (4 mL) was added Pd/C (0.1 g, 10 wt %) and Pd(OH)$_2$/C (0.1 g, 10 wt %). The reaction mixture was stirred at rt for 10 hours under H$_2$ (15 Psi) atmosphere. On completion, the mixture was filtered and filtrate was concentrated in vacuo to give the title compound (50 mg, 99% yield) as yellow oil. LC-MS (ESI$^+$) m/z 406.1 (M+H)$^+$.

Step 3—2-[2-[3-[1-(2,6-Dioxo-3-piperidyl)-3-methyl-2-oxo-benzimidazol-4-yl]propoxy]ethoxy]acetaldehyde To a solution of 3-[4-[3-[2-(2-hydroxyethoxy)ethoxy]propyl]-3-methyl-2-oxo-benzimidazol-1-yl]piperidine-2,6-dione (50 mg, 123 umol) in THF (3 mL) was added DMP (78.5 mg, 185 umol). The reaction mixture was stirred at rt for 2 hours. On completion, the mixture was quenched with sat. Na$_2$S$_2$O$_3$ (20 mL) and sat. NaHCO$_3$ (20 mL) and stirred for 0.5 hour. The reaction mixture was then extracted with DCM (2×30 mL). The organic layer was washed with brine (40 mL), dried over Na$_2$SO$_4$, filtered and the filtrate was concentrated in vacuo to give the title compound (30 mg, 60% yield) as yellow oil. LC-MS (ESI$^+$) m/z 404.2 (M+H)$^+$.

3-[4-[3-(3-aminopropoxy)propyl]-3-methyl-2-oxo-benzimidazol-1-yl]piperidine-2,6-dione (Intermediate LF)

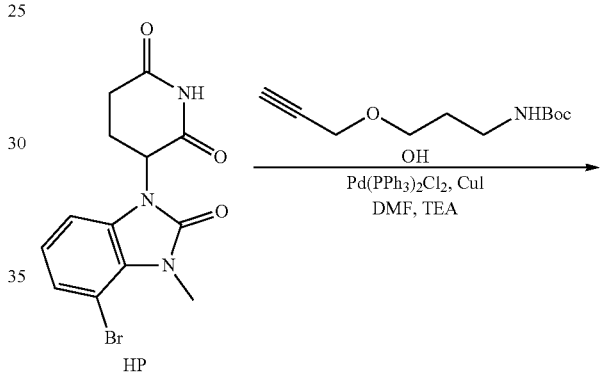

HP

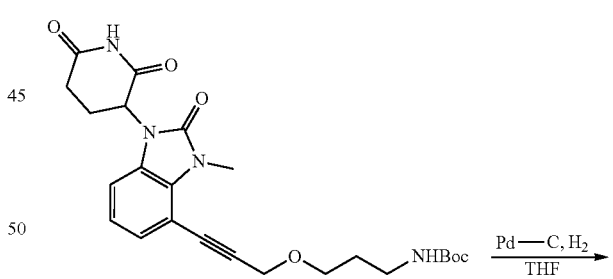

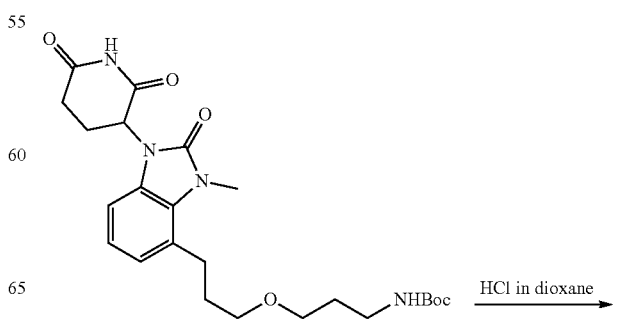

-continued

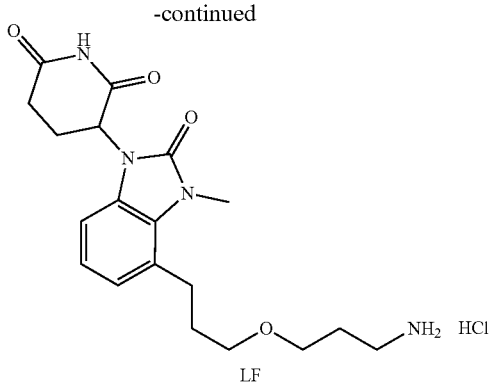

LF

Step 1—Tert-butyl N-[3-([3-[1-(2,6-dioxopiperidin-3-yl)-3-methyl-2-oxo-2,3-dihydro-1H-1,3-benzodiazol-4-yl]prop-2-yn-1-yl]oxy)propyl]carbamate To a stirred solution of 3-(4-bromo-3-methyl-2-oxo-2,3-dihydro-1H-1,3-benzodiazol-1-yl)piperidine-2,6-dione (221 mg, 0.65 mmol), tert-butyl N-[3-(prop-2-yn-1-yloxy)propyl]carbamate (209 mg, 0.98 mmol, Intermediate OH) and TEA (1 mL) in DMA (3 mL) were added CuI (12.4 mg, 0.07 mmol) and Pd(PPh$_3$)$_2$Cl$_2$ (45.9 mg, 0.07 mmol) at room temperature under nitrogen atmosphere. The resulting mixture was stirred for 2 h at 90° C. The mixture was cooled down to room temperature and concentrated under reduced pressure to remove TEA. The residue was purified by reverse phase flash chromatography with the following conditions: Column: WelFlash™ C18-I, 20-40 µm, 80 g; Eluent A: Water (plus 10 mmol/L FA); Eluent B: ACN; Gradient: 35%-55% B in 15 min; Flow rate: 50 mL/min; Detector: 220/254 nm; desired fractions were collected at 50% B and concentrated under reduced pressure to afford tert-butyl N-[3-([3-[1-(2,6-dioxopiperidin-3-yl)-3-methyl-2-oxo-2,3-dihydro-1H-1,3-benzodiazol-4-yl]prop-2-yn-1-yl]oxy)propyl]carbamate (90 mg, 29%) as a light pink solid. $^1$H NMR (400 MHz, CDCl$_3$) δ 8.12 (s, 1H), 7.20 (d, J=7.9 Hz, 1H), 7.01 (t, J=7.9 Hz, 1H), 6.78 (d, J=7.9 Hz, 1H), 5.22 (dd, J=12.5, 5.3 Hz, 1H), 4.80 (s, 1H), 4.42 (s, 2H), 3.80 (s, 3H), 3.68 (t, J=6.0 Hz, 2H), 3.30-3.24 (m, 2H), 3.02-2.95 (m, 1H), 2.91-2.69 (m, 2H), 2.28-2.26 (m, 1H), 1.85 (q, J=6.2 Hz, 2H), 1.46 (s, 9H); LC/MS (ESI, m/z): [(M−1)]=469.5.

Step 2—Tert-butyl N-(3-[3-[1-(2,6-dioxopiperidin-3-yl)-3-methyl-2-oxo-2,3-dihydro-1H-1,3-benzodiazol-4-yl]propoxy]propyl)carbamate To a stirred solution of tert-butyl N-[3-([3-[1-(2,6-dioxopiperidin-3-yl)-3-methyl-2-oxo-2,3-dihydro-1H-1,3-benzodiazol-4-yl]prop-2-yn-1-yl]oxy)propyl]carbamate (0.5 g, 1.06 mmol) in THF (10 mL) was added palladium on charcoal (100 mg, 10% w/w) at room temperature under nitrogen atmosphere. The resulting mixture was purged with H$_2$ gas 3 times and stirred for 16 h at room temperature under hydrogen atmosphere. The reaction mixture was filtered through a Celite pad. The filtrate was concentrated under reduced pressure to afford tert-butyl N-(3-[3-[1-(2,6-dioxopiperidin-3-yl)-3-methyl-2-oxo-2,3-dihydro-1H-1,3-benzodiazol-4-yl]propoxy]propyl)carbamate (430 mg, 85%) as a light green oil. $^1$H NMR (400 MHz, CDCl$_3$) δ 8.07 (s, 1H), 7.01 (t, J=7.8 Hz, 1H), 6.92 (d, J=7.8 Hz, 1H), 6.69 (d, I=7.7 Hz, 1H), 5.22 (dd, J=12.3, 5.5 Hz, 1H), 4.88 (s, 1H), 3.77 (s, 1H), 3.71 (s, 3H), 3.50 (m, 3H), 3.26 (d, J=6.3 Hz, 2H), 3.08-3.00 (m, 2H), 3.00-2.91 (m, 1H), 2.91-2.71 (m, 2H), 2.32-2.19 (m, 1H), 2.00-1.74 (m, 4H), 1.46 (s, 9H); LC/MS (ESI, m/z): [(M−1)]=473.3.

Step 3—3-[4-[3-(3-Aminopropoxy)propyl]-3-methyl-2-oxo-2,3-dihydro-1H-1,3-benzodiazol-1-yl]piperidine-2,6-dione hydrochloride To a stirred solution of tert-butyl N-(3-[3-[1-(2,6-dioxopiperidin-3-yl)-3-methyl-2-oxo-2,3-dihydro-1H-1,3-benzodiazol-4-yl]propoxy]propyl)carbamate (430 mg, 0.91 mmol) in 1,4-dioxane (5 mL) was added a solution of HCl in 1,4-dioxane (4 M, 5 mL) dropwise at 0° C. under nitrogen atmosphere. The resulting mixture was stirred for 3 h at room temperature. The resulting mixture was concentrated under reduced pressure and the residue was dissolved in 1,4-dioxane (15 mL) and re-concentrated under reduced pressure to afford 3-[4-[3-(3-aminopropoxy)propyl]-3-methyl-2-oxo-2,3-dihydro-1H-1,3-benzodiazol-1-yl]piperidine-2,6-dione hydrochloride (310 mg, 91%) as a brown yellow solid. $^1$H NMR (400 MHz, DMSO-d$_6$) δ 11.10 (s, 1H), 7.94 (s, 3H), 7.02-6.92 (m, 2H), 6.88 (dd, J=6.4, 2.5 Hz, 1H), 5.39 (dd, J=12.6, 5.4 Hz, 1H), 3.60-3.54 (s, 3H), 3.51-3.43 (m, 4H), 3.02-2.82 (m, 5H), 2.79-2.58 (m, 2H), 2.09-1.93 (m, 1H), 1.90-1.80 (m, 4H); LC/MS (ESI, m/z): [(M+1)]$^+$=375.3.

3-[5-[3-(3-aminopropoxy)propyl]-3-methyl-2-oxo-benzimidazol-1-yl]piperidine-2,6-dione (Intermediate LG)

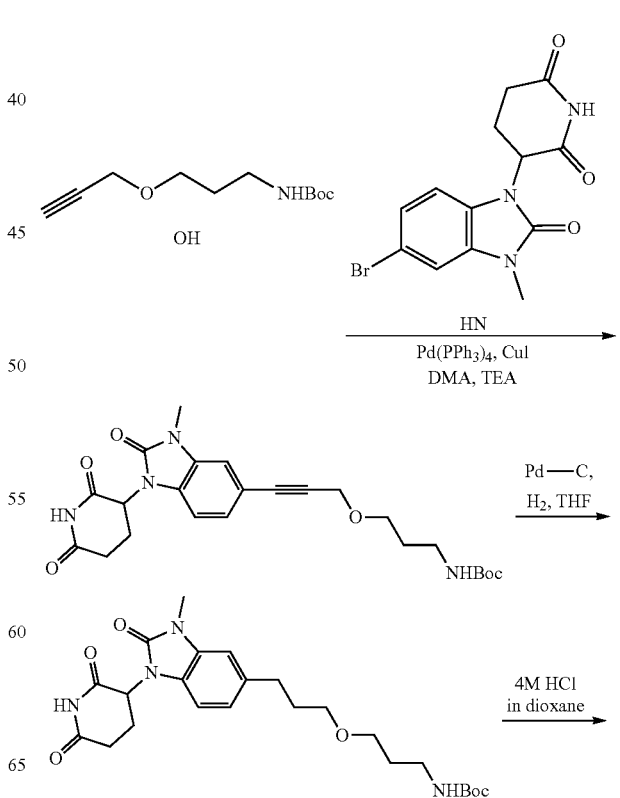

-continued

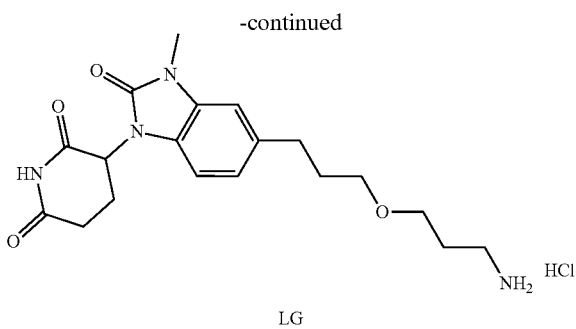

LG

Step 1—Tert-butyl N-[3-([3-[1-(2,6-dioxopiperidin-3-yl)-3-methyl-2-oxo-2,3-dihydro-1H-1,3-benzodiazol-5-yl]prop-2-yn-1-yl]oxy)propyl]carbamate To a stirred mixture of 3-(5-bromo-3-methyl-2-oxo-2,3-dihydro-1H-1,3-benzodiazol-1-yl)piperidine-2,6-dione (2 g, 6 mmol, Intermediate HN), Pd(PPh$_3$)$_4$ (683.4 mg, 0.59 mmol) and CuI (225.3 mg, 1.18 mmol) in DMSO (10 mL) and TEA (5 mL) was added tert-butyl N-[3-(prop-2-yn-1-yloxy)propyl]carbamate (3.8 g, 18 mmol, Intermediate OH) at room temperature under nitrogen atmosphere. The resulting mixture was purged with nitrogen three times and stirred for 16 h at 90° C. under nitrogen atmosphere. The resulting mixture was concentrated under reduced pressure to remove TEA. The resulting mixture was diluted with a solution of AcOH (3 mL) in ice water (50 mL) and extracted with EtOAc (2×50 mL). The combined organic layers was washed with brine (30 mL) and dried over anhydrous Na$_2$SO$_4$. After filtration, the filtrate was concentrated under reduced pressure. The residue was purified by reverse phase flash chromatography with the following conditions: Column: WelFlash™ C18-I, 20-40 μm, 330 g; Eluent A: Water (plus 10 mmol/L FA); Eluent B: ACN; Gradient: 50%-60% B in 20 min; Flow rate: 80 mL/min; Detector: 220/254 nm; desired fractions were collected at 57% B and concentrated under reduced pressure to afford tert-butyl N-[3-([3-[1-(2,6-dioxopiperidin-3-yl)-3-methyl-2-oxo-2,3-dihydro-1H-1,3-benzodiazol-5-yl]prop-2-yn-1-yl]oxy)propyl]carbamate (1.5 g, 54%) as a light yellow solid: $^1$H NMR (400 MHz, DMSO-d$_6$) δ 11.12 (s, 1H), 7.34 (s, 1H), 7.23-7.11 (m, 2H), 6.80 (s, 1H), 5.40 (dd, J=12.7, 5.4 Hz, 1H), 4.35 (s, 2H), 3.51 (t, J=6.4 Hz, 2H), 3.35 (s, 3H), 3.00 (q, J=6.7 Hz, 2H), 2.95-2.83 (m, 1H), 2.79-2.58 (m, 2H), 2.03 (dd, J=9.3, 4.3 Hz, 1H), 1.66 (p, J=6.6 Hz, 2H), 1.37 (s, 9H); LC/MS (ESI, m/z): [(M+1)]$^+$=469.20.

Step 2—Tert-butyl N-(3-[3-[1-(2,6-dioxopiperidin-3-yl)-3-methyl-2-oxo-2,3-dihydro-1H-1,3-benzodiazol-5-yl]propoxy]propyl)carbamate To a stirred solution of tert-butyl N-[3-([3-[1-(2,6-dioxopiperidin-3-yl)-3-methyl-2-oxo-2,3-dihydro-1H-1,3-benzodiazol-5-yl]prop-2-yn-1-yl]oxy)propyl]carbamate (800 mg, 1.70 mmol) in THF (20 mL) was added palladium on charcoal (200 mg, 10% w/w) at rt under nitrogen atmosphere. The resulting mixture was purged with H$_2$ gas 3 times and stirred for 4 h at room temperature under hydrogen atmosphere. The reaction mixture was filtered through a Celite pad. The filtrate was concentrated under reduced pressure to afford tert-butyl N-(3-[3-[1-(2,6-dioxopiperidin-3-yl)-3-methyl-2-oxo-2,3-dihydro-1H-1,3-benzodiazol-5-yl]propoxy]propyl)carbamate (730 mg, 90%) as a white solid. $^1$H NMR (400 MHz, DMSO-d$_6$) δ 11.08 (s, 1H), 7.06-6.97 (m, 2H), 6.87 (d, J=7.8 Hz, 1H), 6.77 (s, 1H), 5.34 (dd, J=12.7, 5.3 Hz, 1H), 3.61 (s, 1H), 3.40-3.31 (m, 6H), 2.99 (q, J=6.6 Hz, 2H), 2.90 (t, J=15.0 Hz, 1H), 2.73-2.58 (m, 4H), 2.01 (d, J=12.7 Hz, 1H), 1.83-1.73 (m, 2H), 1.66-1.58 (m, 2H), 1.38 (s, 9H); LC/MS (ESI, m/z): [(M−1)]$^-$=473.3.

Step 3—3-[5-[3-(3-Aminopropoxy)propyl]-3-methyl-2-oxo-2,3-dihydro-1H-1,3-benzodiazol-1-yl]piperidine-2,6-dione hydrochloride To a stirred solution of tert-butyl N-(3-[3-[1-(2,6-dioxopiperidin-3-yl)-3-methyl-2-oxo-2,3-dihydro-1H-1,3-benzodiazol-5-yl]propoxy]propyl)carbamate (730 mg, 1.54 mmol) in 1,4-dioxane (10 mL) was added a solution of HCl in dioxane (4 M, 10 mL) dropwise at 0° C. under nitrogen atmosphere. The resulting mixture was stirred for 16 h at rt under nitrogen atmosphere. The resulting mixture was concentrated under reduced pressure. The residue was dissolved in 1,4-dioxane (20 mL) and re-concentrated under reduced pressure to afford 3-[5-[3-(3-aminopropoxy)propyl]-3-methyl-2-oxo-2,3-dihydro-1H-1,3-benzodiazol-1-yl]piperidine-2,6-dione hydrochloride (600 mg, 99%) as a light brown solid. $^1$H NMR (400 MHz, DMSO-d$_6$) δ 11.09 (s, 1H), 7.74 (br s, 3H), 7.11-6.95 (m, 2H), 6.87 (d, J=8.0 Hz, 1H), 5.35 (dd, J=12.8, 5.4 Hz, 1H), 3.58 (s, 3H), 3.44 (t, J=6.1 Hz, 2H), 3.39 (t, J=6.5 Hz, 2H), 2.94-2.80 (m, 3H), 2.77-2.56 (m, 4H), 2.10-1.95 (m, 1H), 1.90-1.76 (m, 4H); LC/MS (ESI, m/z): [(M+1)]$^+$=375.10.

3-(4-(3-(3-(3-Aminopropoxy)propoxy)propyl)-3-methyl-2-oxo-2,3-dihydro-1H-benzo[d]imidazol-1-yl)piperidine-2,6-dione (Intermediate LH)

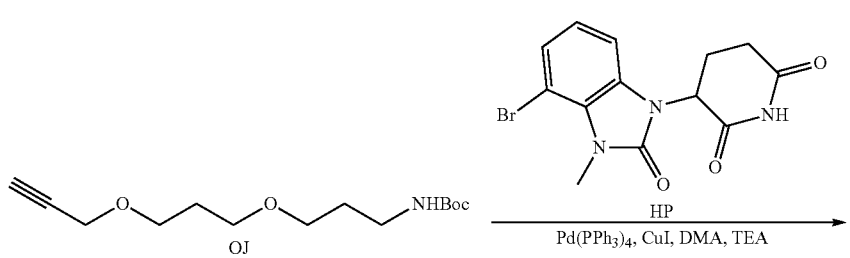

-continued

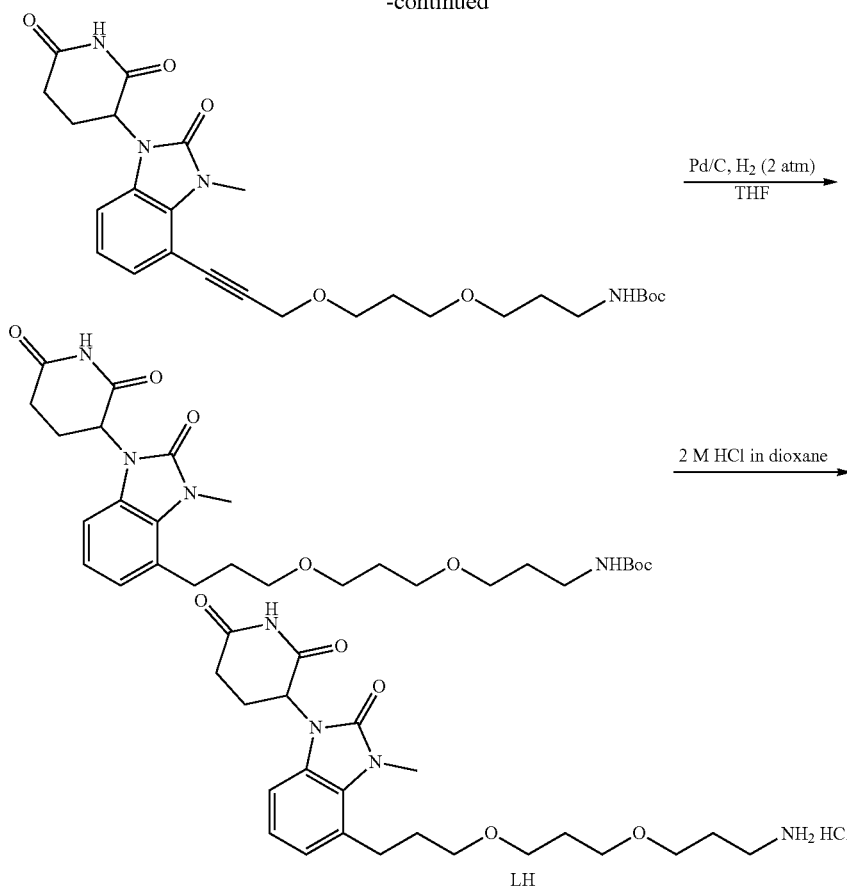

Step 1—tert-butyl N-[3-[3-([3-[1-(2,6-dioxopiperidin-3-yl)-3-methyl-2-oxo-2,3-dihydro-1H-1,3-benzodiazol-4-yl]prop-2-yn-1-yl]oxy)propoxy]propyl]carbamate To a solution of 3-(4-bromo-3-methyl-2-oxo-2,3-dihydro-1H-1,3-benzodiazol-1-yl)piperidine-2,6-dione (2 g, 5.91 mmol, Intermediate HP) in DMA (30 mL) were added tert-butyl N-[3-[3-(prop-2-yn-1-yloxy)propoxy]propyl]carbamate (3 g, 11.06 mmol, Intermediate OJ), TEA (15 mL), CuI (113 mg, 0.59 mmol) and Pd(PPh$_3$)$_4$ (0.68 g, 0.59 mmol) at rt under nitrogen atmosphere. The resulting mixture was stirred for 5 h at 90° C. under nitrogen atmosphere. The resulting mixture was cooled down to rt and concentrated under reduced pressure. The residue was purified by reverse phase flash chromatography with the following conditions: Column: WelFlash™ C18-I, 20-40 μm, 330 g; Eluent A: Water (plus 10 mmol/L HCOOH); Eluent B: ACN; Gradient: 35%-60% B in 15 min; Flow rate: 80 mL/min; Detector: 220/254 nm; desired fractions were collected at 55% B and concentrated under reduced pressure to afford tert-butyl N-[3-[3-([3-[1-(2,6-dioxopiperidin-3-yl)-3-methyl-2-oxo-2,3-dihydro-1H-1,3-benzodiazol-4-yl]prop-2-yn-1-yl]oxy)propoxy]propyl]carbamate (1.4 g, 45%) as a light brown solid. $^1$H NMR (400 MHz, DMSO-d$_6$) δ 11.12 (br s, 1H), 7.19-7.12 (m, 2H), 7.08-6.95 (m, 1H), 6.75 (br s, 1H), 5.41 (dd, J=12.7, 5.4 Hz, 1H), 4.43 (s, 2H), 3.64 (s, 3H), 3.63-3.55 (m, 4H), 3.42 (t, J=6.4 Hz, 2H), 3.35 (d, J=12.6 Hz, 2H), 3.00-2.83 (m, 3H), 2.71 (m, 2H), 2.10-1.97 (m, 2H), 1.78 (p, J=6.4 Hz, 2H), 1.59 (p, J=6.6 Hz, 2H), 1.37 (s, 9H); LC/MS (ESI, m/z): [(M+1)]$^+$=529.35.

Step 2—tert-butyl N-[3-(3-[3-[1-(2,6-dioxopiperidin-3-yl)-3-methyl-2-oxo-2,3-dihydro-1H-1,3-benzodiazol-4-yl]propoxy]propoxy)propyl]carbamate To a stirred solution of tert-butyl N-[3-[3-([3-[1-(2,6-dioxopiperidin-3-yl)-3-methyl-2-oxo-2,3-dihydro-1H-1,3-benzodiazol-4-yl]prop-2-yn-1-yl]oxy)propoxy]propyl]carbamate (900 mg, 1.71 mmol) in THF (20 mL) was added palladium on charcoal (300 mg, 10% w/w) at rt under nitrogen atmosphere. The resulting mixture was purged with hydrogen for 3 times and was stirred for 4 h at rt under hydrogen atmosphere. The reaction mixture was filtered through a Celite pad. The filtrate was concentrated under reduced pressure to afford tert-butyl N-[3-(3-[3-[1-(2,6-dioxopiperidin-3-yl)-3-methyl-2-oxo-2,3-dihydro-1H-1,3-benzodiazol-4-yl]propoxy]propoxy)propyl]carbamate (800 mg, 88%) as a light brown solid. $^1$H NMR (400 MHz, DMSO-d$_6$) δ 11.10 (br s, 1H), 7.02-6.98 (m, 2H), 6.90-6.83 (m, 1H), 6.76 (t, J=5.7 Hz, 1H), 5.37 (dd, J=12.6, 5.4 Hz, 1H), 3.56 (s, 3H), 3.52-3.33 (m, 6H), 3.01-2.83 (m, 5H), 2.72-2.58 (m, 2H), 2.00 (ddd, J=11.1, 5.9, 3.6 Hz, 1H), 1.89-1.68 (m, 6H), 1.60 (p, J=6.6 Hz, 2H), 1.37 (s, 9H); LC/MS (ESI, m/z): [(M+1)]$^+$=533.40.

Step 3—3-(4-[3-[3-(3-Aminopropoxy)propoxy]propyl]-3-methyl-2-oxo-2,3-dihydro-1H-1,3-benzodiazol-1-yl)piperidine-2,6-dione hydrochloride To a stirred solution of tert-butyl N-[3-(3-[3-[1-(2,6-dioxopiperidin-3-yl)-3-methyl-2-oxo-2,3-dihydro-1H-1,3-benzodiazol-4-yl]propoxy]propoxy)propyl]carbamate (800 mg, 1.50 mmol) in 1,4-dioxane (10 mL) was added a solution of hydrochloride in dioxane (4 M, 10 mL) dropwise at 0° C. The resulting mixture was stirred for 2 h at rt. The resulting mixture was concentrated under reduced pressure to afford 3-(4-[3-[3-(3-aminopropoxy)propoxy]propyl]-3-methyl-2-oxo-2,3-dihydro-1H-1,3-benzodiazol-1-yl)piperidine-2,6-dione hydrochloride (640 mg, 91%) as a white solid. $^1$H NMR (400 MHz, DMSO-$d_6$) δ 11.11 (br s, 1H), 7.83 (br s, 3H), 7.05-6.93 (m, 2H), 6.88 (td, J=6.8, 5.9, 3.1 Hz, 1H), 5.38 (dd, J=12.5, 5.4 Hz, 1H), 3.57 (s, 3H), 3.45-3.31 (m, 8H), 3.04-2.77 (m, 5H), 2.77-2.57 (m, 2H), 1.99 (dd, J=9.8, 4.9 Hz, 1H), 1.90-1.70 (m, 6H); LC/MS (ESI, m/z): [(M+1)]$^+$=433.30.

3-(5-[3-[3-(3-Aminopropoxy)propoxy]propyl]-3-methyl-2-oxo-2,3-dihydro-1H-1,3-benzodiazol-1-yl)piperidine-2,6-dione (Intermediate LI)

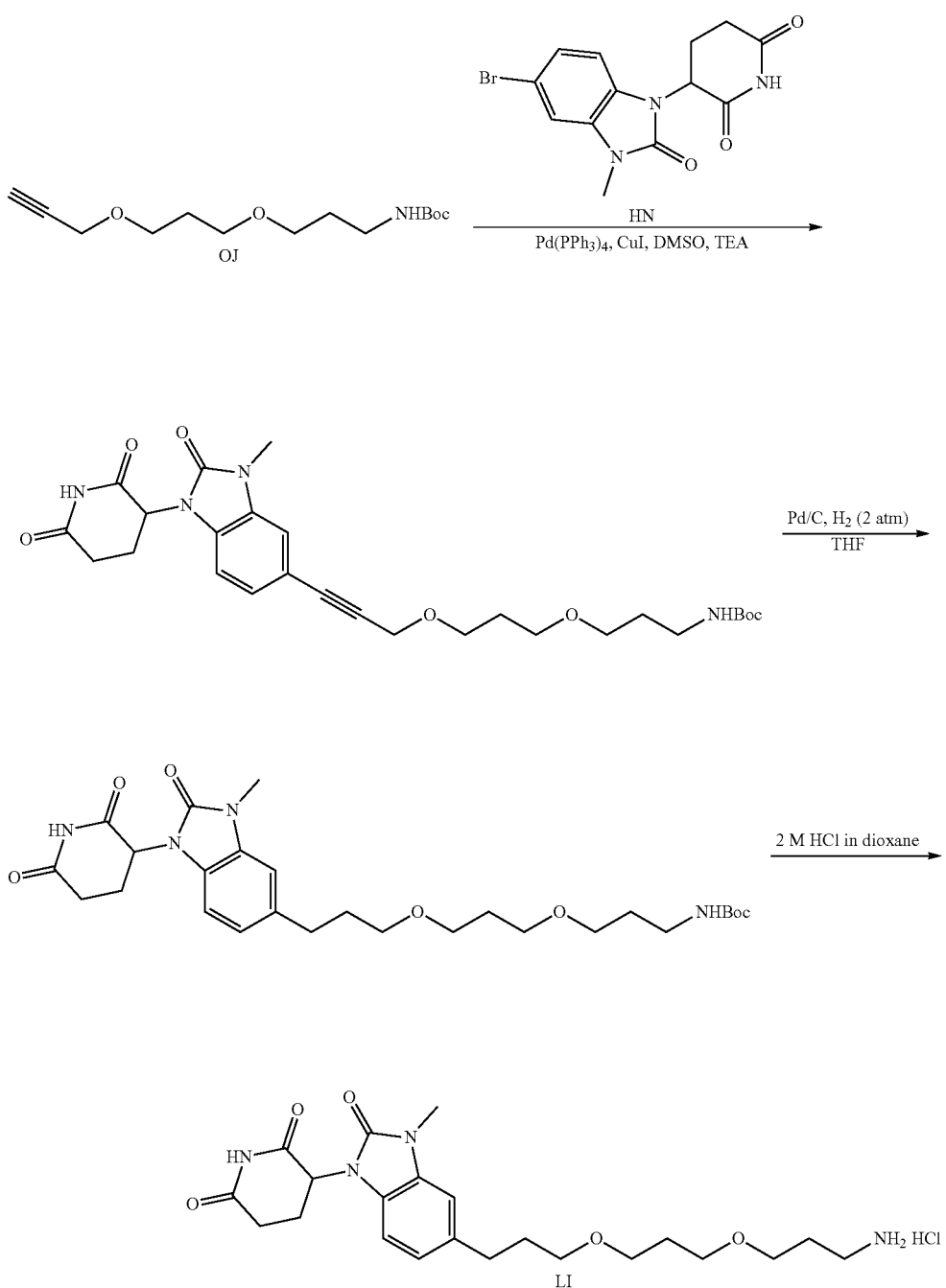

Step 1—tert-Butyl N-[3-[3-([3-[1-(2,6-dioxopiperidin-3-yl)-3-methyl-2-oxo-2,3-dihydro-1H-1,3-benzodiazol-5-yl]prop-2-yn-1-yl]oxy)propoxy]propyl]carbamate To a stirred solution of 3-(5-bromo-3-methyl-2-oxo-2,3-dihydro-1H-1,3-benzodiazol-1-yl)piperidine-2,6-dione (2.0 g, 5.91 mmol, Intermediate HN) in DMSO (20 mL) were added tert-butyl N-[3-[3-(prop-2-yn-1-yloxy)propoxy]propyl]carbamate (5.8 g, 21.4 mmol, Intermediate OJ), TEA (10 mL), CuI (0.2 g, 1 mmol) and Pd(PPh$_3$)$_4$ (0.7 g, 0.59 mmol) at rt under nitrogen atmosphere. The resulting mixture was stirred for 3 h at 90° C. The resulting mixture was cooled to rt and concentrated under reduced pressure. The resulting mixture was diluted with 1% aqueous solution of AcOH (100 mL) and extracted with EtOAc (2×100 mL). The combined organic layers was washed with brine (100 mL) and dried over anhydrous Na$_2$SO$_4$. After filtration, the filtrate was concentrated under reduced pressure. The residue was purified by reverse phase flash chromatography with the following conditions: Column: WelFlash™ C18-I, 20-40 μm, 330 g; Eluent A: Water (plus 10 mmol/L AcOH); Eluent B: ACN; Gradient: 45%-55% B in 10 min; Flow rate: 80 mL/min; Detector: 220/254 nm; desired fractions were collected at 51% B and concentrated under reduced pressure to afford tert-butyl N-[3-[3-([3-[1-(2,6-dioxopiperidin-3-yl)-3-methyl-2-oxo-2,3-dihydro-1H-1,3-benzodiazol-5-yl]prop-2-yn-1-yl]oxy)propoxy]propyl]carbamate (1.5 g, 48%) as a yellow solid. $^1$H NMR (400 MHz, CDCl$_3$) δ 8.21 (br s, 1H), 7.22 (dd, J=8.2, 1.5 Hz, 1H), 7.14 (d, J=1.4 Hz, 1H), 6.77 (d, J=8.1 Hz, 1H), 5.22 (dd, J=12.7, 5.3 Hz, 1H), 4.89 (br s, 1H), 4.39 (s, 2H), 3.69 (t, J=6.3 Hz, 2H), 3.55 (t, J=6.3 Hz, 2H), 3.51 (t, J=5.9 Hz, 2H), 3.44 (s, 3H), 3.23 (q, J=6.1 Hz, 2H), 3.03-2.64 (m, 3H), 2.34-2.24 (m, 1H), 1.92 (p, J=6.3 Hz, 2H), 1.76 (p, J=6.3 Hz, 2H), 1.46 (s, 9H); LC/MS (ESI, m/z): [(M+1)]$^+$=529.25.

Step 2—tert-Butyl N-[3-(3-[3-[1-(2,6-dioxopiperidin-3-yl)-3-methyl-2-oxo-2,3-dihydro-1H-1,3-benzodiazol-5-yl]propoxy]propoxy)propyl]carbamate To a solution of tert-butyl N-[3-[3-([3-[1-(2,6-dioxopiperidin-3-yl)-3-methyl-2-oxo-2,3-dihydro-1H-1,3-benzodiazol-5-yl]prop-2-yn-1-yl]oxy)propoxy]propyl]carbamate (200 mg, 0.38 mmol) in THF (10 mL) was added palladium on charcoal (402 mg, 10% w/w) under nitrogen atmosphere. The mixture was purged with hydrogenated for three times and was stirred at rt for 6 h under hydrogen atmosphere. The resulting mixture was filtered through a Celite pad and the filtrate was concentrated under reduced pressure to afford tert-butyl N-[3-(3-[3-[1-(2,6-dioxopiperidin-3-yl)-3-methyl-2-oxo-2,3-dihydro-1H-1,3-benzodiazol-5-yl]propoxy]propoxy)propyl]carbamate (150 mg, 74%) as a white solid. $^1$H NMR (400 MHz, DMSO-d$_6$) δ 11.09 (br s, 1H), 7.93 (br s, 1H), 7.06-6.98 (m, 2H), 6.87 (d, J=8.0 Hz, 1H), 5.36 (dt, J=12.6, 6.0 Hz, 1H), 3.57 (s, 5H), 3.47-3.34 (m, 8H), 3.04-2.84 (m, 2H), 2.82-2.66 (m, 1H), 2.66-2.58 (m, 3H), 2.04-1.96 (m, 1H), 1.86-1.68 (m, 4H), 1.65-1.53 (m, 1H), 1.37 (s, 9H); LC/MS (ESI, m/z): [(M+1)]$^+$=533.25.

Step 3—3-(5-[3-[3-(3-Aminopropoxy)propoxy]propyl]-3-methyl-2-oxo-2,3-dihydro-1H-1,3-benzodiazol-1-yl)piperidine-2,6-dione hydrochloride To a solution of tert-butyl N-[3-(3-[3-[1-(2,6-dioxopiperidin-3-yl)-3-methyl-2-oxo-2,3-dihydro-1H-1,3-benzodiazol-5-yl]propoxy]propoxy)propyl]carbamate (300 mg, 0.56 mmol) in dioxane (10 mL) was added a solution of hydrochloride in 1,4-dioxane (4 M, 10 mL). The resulting solution was stirred for 4 h at rt under nitrogen atmosphere. The resulting mixture was concentrated under vacuum to afford 3-(5-[3-[3-(3-aminopropoxy)propoxy]propyl]-3-methyl-2-oxo-2,3-dihydro-1H-1,3-benzodiazol-1-yl)piperidine-2,6-dione hydrochloride (200 mg, 76%) as a yellow solid. $^1$H NMR (400 MHz, DMSO-d$_6$) δ 11.09 (br s, 1H), 7.93 (br s, 3H), 7.06-6.99 (m, 2H), 6.87 (d, J=8.0 Hz, 1H), 5.36 (dd, J=12.7, 5.5 Hz, 1H), 3.58 (s, 3H), 3.48-3.34 (m, 8H), 3.02-2.54 (m, 7H), 2.00 (dd, J=11.4, 6.2 Hz, 1H), 1.87-1.68 (m, 6H); LC/MS (ESI, m/z): [(M+1)]$^+$=433.15.

3-Bromo-1-(4-methoxybenzyl)piperidine-2,6-dione (Intermediate LJ)

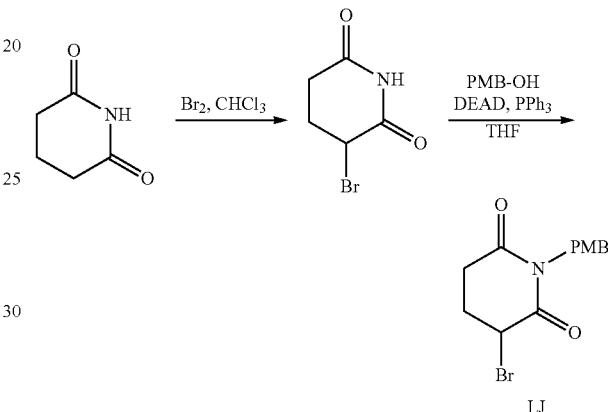

Step 1—3-bromopiperidine-2,6-dione

To a stirred solution of piperidine-2,6-dione (30 g, 0.266 mol) in CHCl$_3$ (60 mL) was added Br$_2$ (13.5 mL, 0.265 mol) in a sealed glass tube, then the reaction mixture was heated to 113° C. for 1.5 h. The mixture was cooled to r.t. and transferred to a round bottom flask and concentrated. To the residue was added 100 mL ice water, and the solution was basified to pH=~8 with saturated NaHCO$_3$ aqueous, then extracted with DCM (100 mL×5). The organic layer was dried with Na$_2$SO$_4$, filtered, and concentrated to give crude product, which was dissolved in a solution of DCM:EtOAc=1:1 (~90 mL), then heated to 80° C. After the solid was completely dissolved, the heating was stopped and the solution was cooled to r.t. for overnight. The solution was filtered, the solid was collected, and dried under vacuum to give desired compound (15.7 g) as a white solid. The filtrate was also concentrated to dry to give crude product, which was purified by column chromatography on silica gel eluting with DCM:Petroleum ether:EtOAc=5:5:1 to DCM:Petroleum ether:EtOAc=5:5:2 to obtain desired the second batch pure product (12 g) as a white solid (total yield: 54.5%). $^1$H NMR (400 MHz, DMSO-d$_6$) δ 11.06 (s, 1H), 5.00-4.78 (m, 1H), 2.69-2.54 (m, 2H), 2.45 (dd, J=10.0, 5.1 Hz, 1H), 2.17-2.12 (m, 1H).

Step 2—3-bromo-1-(4-methoxybenzyl)piperidine-2,6-dione

To a solution of 3-bromopiperidine-2,6-dione (30 g, 156.3 mmol), (4-methoxyphenyl)methanol (23.3 g, 168 mmol) and PPh₃ (40.5 g, 154.5 mmol) in dry THF (450 mL) was added dropwise DEAD (26.9 g, 154.5 mmol) at 0° C. under N₂ for 30 min. The mixture was stirred for another 1.5 hour at 0° C. under N₂. The mixture was quenched with H₂O (300 mL) at 0° C., and extracted with EA (400 mL×3). The organic layer was concentrated to give a residue, which was purified by column chromatography on silica gel eluting with PE:EA=5:1 to PE:EA=4:1 to give crude product. The crude product was further purified by column chromatography on silica gel eluting with DCM to give 3-bromo-1-(4-methoxybenzyl) piperidine-2,6-dione (26.8 g, 55% yield) as a pale yellow solid. ¹H NMR (400 MHz, CDCl₃) δ 7.32-7.29 (d, J=8.8 Hz, 2H), 6.83-6.81 (d, J=8.8 Hz, 2H), 4.96-4.83 (dd, J=13.6 Hz, J=38 Hz, 2H), 4.72-4.70 (m, 1H), 3.78 (s, 3H), 3.06-2.99 (m, 1H), 2.76-2.72 (m, 1H), 2.36-2.32 (m, 1H), 2.25-2.21 (m, 1H).

5-Chloro-1-methyl-N-(4-morpholinocyclohexyl) pyrazolo[4,3-d]pyrimidin-7-amine (Intermediate LK)

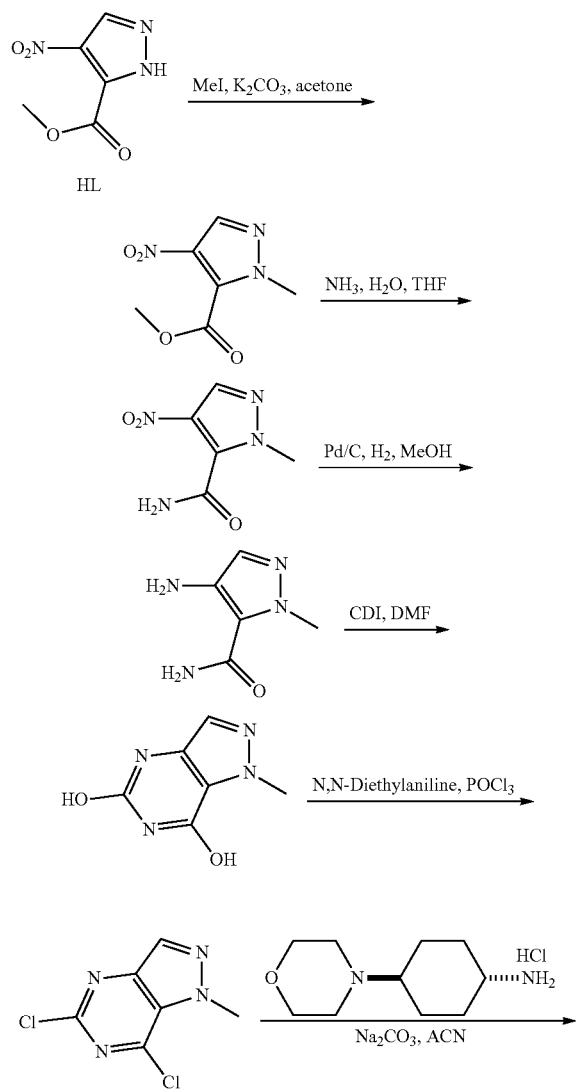

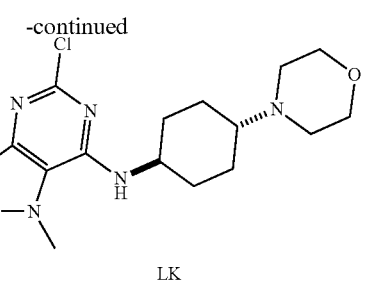

LK

Step 1—Methyl 2-methyl-4-nitro-pyrazole-3-carboxylate

To a mixture of methyl 4-nitro-1H-pyrazole-5-carboxylate (30.0 g, 175 mmol, Intermediate HL) and K₂CO₃ (48.4 g, 350 mmol) in acetone (600 mL) was added MeI (49.7 g, 350 mmol, 21.8 mL). The reaction mixture was stirred at 70° C. for 2 hours. On completion, the reaction mixture was filtered and concentrated in vacuo. The residue was purified by column chromatography to give the title compound (10.0 g, 30% yield) as light yellow solid. ¹H NMR (400 MHz, CDCl₃) δ 7.99 (s, 1H), 4.01 (s, 3H), 4.01 (s, 3H).

Step 2—2-Methyl-4-nitro-pyrazole-3-carboxamide

To a mixture of methyl 2-methyl-4-nitro-pyrazole-3-carboxylate (10.0 g, 54.0 mmol) in THF (20 mL) was added NH₃.H₂O (27.3 g, 740 mmol, 30 mL, 95%). The reaction mixture was stirred at 100° C. for 16 hours. On completion, the reaction mixture was concentrated in vacuo to give the title compound (8.80 g, 95% yield) as white solid. ¹H NMR (400 MHz, DMSO-d₆) δ 8.46 (s, 1H), 8.29 (s, 1H), 8.26 (s, 1H), 3.86 (s, 3H).

Step 3—4-Amino-2-methyl-pyrazole-3-carboxamide

To a mixture of 2-methyl-4-nitro-pyrazole-3-carboxamide (8.80 g, 51.7 mmol) in MeOH (100 mL) was added Pd/C (6.00 g, 10 wt %). The reaction mixture was stirred at rt for 12 hours under H₂ (15 psi) atmosphere. On completion, the reaction mixture was filtered and concentrated in vacuo to give the title compound (7.10 g, 97% yield) as red solid. ¹H NMR (400 MHz, DMSO-d₆) δ 7.37 (s, 2H), 7.02 (s, 1H), 4.41 (s, 2H), 3.89 (s, 3H).

Step 4—1-Methylpyrazolo[4,3-d]pyrimidine-5,7-diol

To a mixture of 4-amino-2-methyl-pyrazole-3-carboxamide (11.3 g, 80.6 mmol) in DMF (120 mL) was added CDI (26.1 g, 161 mmol). The reaction mixture was stirred at 90° C. for 24 hours. On completion, the reaction mixture was diluted with water (400 mL) then the solid was formed, and filtered to afford solid. The solid was washed with water (1 L) to give the title compound (13.0 g, 97% yield) as off-white solid. ¹H NMR (400 MHz, DMSO-d₆) δ 11.08 (s, 1H), 10.92 (s, 1H), 7.33 (s, 1H), 4.04 (s, 3H).

Step 5—5,7-Dichloro-1-methyl-pyrazolo[4,3-d]pyrimidine

To a mixture of 1-methylpyrazolo[4,3-d]pyrimidine-5,7-diol (5.00 g, 30.1 mmol) in POCl₃ (50.0 g, 326 mmol, 30.3 mL) was added N,N-diethylaniline (4.46 g, 29.8 mmol, 4.78 mL). The reaction mixture was stirred at 110° C. for 4 hours. On completion, the reaction mixture was concentrated in vacuo. The residue was purified by column chromatography to give the title compound (3.70 g, 60% yield) as white solid. $^1$H NMR (400 MHz, DMSO-$d_6$) δ 8.48 (s, 1H), 4.33 (s, 3H).

Step 6—5-Chloro-1-methyl-N-(4-morpholinocyclohexyl)pyrazolo[4,3-d]pyrimidin-7-amine To a solution of 5,7-dichloro-1-methyl-pyrazolo[4,3-d]pyrimidine (1.00 g, 4.93 mmol) and 4-morpholinocyclohexanamine (1.27 g, 4.93 mmol, 2HCl, CAS #558442-97-0) in ACN (30 mL) was added Na$_2$CO$_3$ (2.09 g, 19.70 mmol). The reaction mixture was stirred at 80° C. for 12 hours. The reaction mixture was concentrated in vacuo, diluted with DCM (30 mL), and filtered. The filtrate was concentrated in vacuo. The crude product was triturated with ACN/DCM/PE=1:0.2:10 (30 mL) to give the title compound (1.30 g, 75% yield) as a yellow solid. H NMR (400 MHz, CDCl$_3$) δ 7.85 (s, 1H), 5.18 (d, J=6.8 Hz, 1H), 4.30 (s, 3H), 4.28-4.17 (m, 1H), 3.86 (s, 4H), 2.74 (s, 4H), 2.56-2.50 (m, 1H), 2.36 (d, J=11.6 Hz, 2H), 2.13 (d, J=11.6 Hz, 2H), 1.69-1.53 (m, 2H), 1.47-1.32 (m, 2H).

Tert-butyl N-[2-[2-[2-[2-[2-(4-aminopyrazol-1-yl)ethoxy]ethoxy]ethoxy]ethoxy]ethyl]carbamate (Intermediate LL)

Step 2—Tert-butyl N-[2-[2-[2-[2-[2-(4-aminopyrazol-1-yl)ethoxy]ethoxy]ethoxy]ethoxy]ethyl]carbamate To a mixture of tert-butyl N-[2-[2-[2-[2-[2-(4-nitropyrazol-1-yl)ethoxy]ethoxy]ethoxy]ethoxy]ethyl]carbamate (1.20 g, 2.77 mmol) in MeOH (20 mL) was added Pd/C (800 mg, 10 wt %). The reaction mixture was stirred at rt for 12 hours under H$_2$ (15 Psi) atmosphere. On completion, the reaction mixture was filtered and concentrated in vacuo to give the title compound (1.00 g, 89% yield) as red oil. $^1$H NMR (400 MHz, CDCl$_3$) δ 7.16 (d, J=5.2 Hz, 2H), 5.23 (s, 1H), 4.17 (t, J=5.2 Hz, 2H), 3.78 (t, J=5.2 Hz, 2H), 3.65-3.51 (m, 14H), 3.30 (d, J=4.8 Hz, 2H), 2.67 (s, 2H), 1.43 (s, 9H).

1-[2-[2-[2-(4-Aminopyrazol-1-yl)ethoxy]ethoxy]ethoxy]pentan-2-one (Intermediate LM)

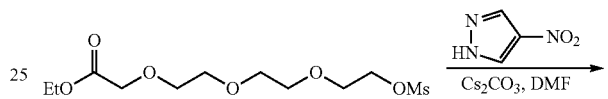

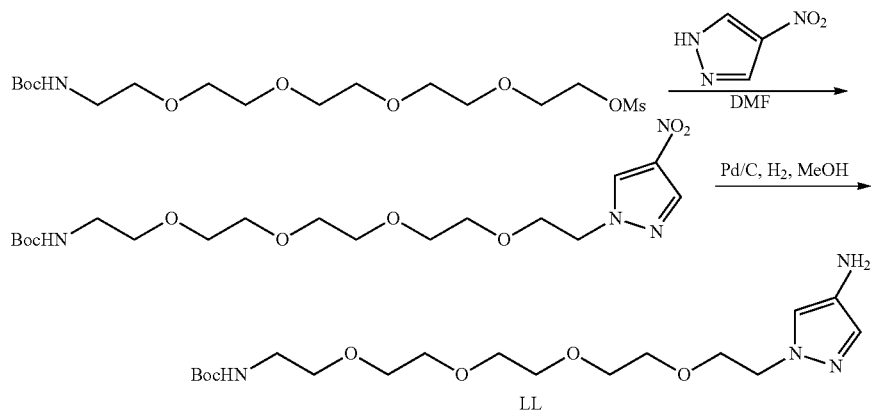

Step 1—Tert-butyl N-[2-[2-[2-[2-[2-(4-nitropyrazol-1-yl)ethoxy]ethoxy]ethoxy]ethoxy]ethyl]carbamate To a solution of 2-[2-[2-[2-[2-(tert-butoxycarbonylamino)ethoxy]ethoxy]ethoxy]ethoxy]ethyl methanesulfonate (1.76 g, 4.24 mmol, synthesized via Step 1 of Intermediate HH) and 4-nitro-1H-pyrazole (0.40 g, 3.54 mmol, CAS #2075-46-9) in DMF (15 mL) was added Cs$_2$CO$_3$ (2.31 g, 7.07 mmol). The reaction mixture was stirred at 130° C. for 3 hours. On completion, the mixture was diluted with H$_2$O (50 mL), then extracted with EA (2×100 mL). The combined organic phase was concentrated in vacuo. The residue was purified by reverse phase (0.1% FA condition) to give the title compound (1.20 g, 78% yield) as yellow oil. LC-MS (ESI$^+$) m/z 455.2 (M+Na)$^+$.

-continued

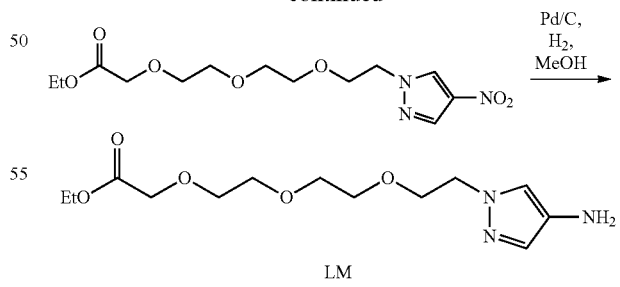

Step 1—Ethyl 2-[2-[2-[2-(4-nitropyrazol-1-yl)ethoxy]ethoxy]ethoxy]acetate

To a mixture of ethyl 2-[2-[2-(2-methylsulfonyloxyethoxy)ethoxy]ethoxy]acetate (0.5 g, 1.59 mmol, Intermediate BI) and 4-nitro-1H-pyrazole (270 mg, 2.38 mmol) in DMF (10 mL) was added Cs$_2$CO$_3$ (1.04 g, 3.18 mmol). The reaction mixture was stirred at rt for 24 hours under N$_2$ atmosphere. On completion, the reaction mixture was diluted with H$_2$O (20 mL) and extracted with EtOAc (3×20 mL). The combined organic layers were washed with brine (50 ml), dried over Na$_2$SO$_4$, filtered and concentrated in vacuo. The residue was purified by flash silica gel chromatography to give the title compound (0.5 g, 1.43 mmol, 90% yield, 95% purity) as a yellow solid. $^1$H NMR (400 MHz, DMSO-d$_6$) δ=8.84 (s, 1H), 8.27 (s, 1H), 4.35 (t, J=5.2 Hz, 2H), 4.19-4.04 (m, 4H), 3.82 (t, J=5.2 Hz, 2H), 3.62-3.46 (m, 8H), 1.19 (t, J=7.2 Hz, 3H) LC-MS (ESI+) m/z 332.2 (M+H)$^+$.

Step 2—1-[2-[2-[2-(4-Aminopyrazol-1-yl)ethoxy]ethoxy]ethoxy]pentan-2-one

To a solution of ethyl 2-[2-[2-[2-(4-nitropyrazol-1-yl)ethoxy]ethoxy]ethoxy]acetate (0.5 g, 1.51 mmol) in EtOH (10 mL) was added Pd/C (0.05 g, 50 wt %) under N$_2$. The suspension was degassed under vacuum and purged with H$_2$ several times. The mixture was stirred under H2 (15 psi) at rt for 2 hours. On completion, the mixture was filtered with celite. The filtrate was concentrated in vacuo to give the title compound (0.34 g, 75% yield) as black red oil. $^1$H NMR (400 MHz, DMSO-d$_6$) δ 7.14-7.01 (m, 1H), 6.96-6.83 (m, 1H), 4.17-4.09 (m, 4H), 4.08-4.03 (m, 2H), 3.72-3.66 (m, 2H), 3.63-3.57 (m, 2H), 3.55-3.51 (m, 2H), 3.49 (s, 4H), 1.25-1.17 (m, 3H).

3-[4-[4-(4-aminobutoxy)butyl]-3-methyl-2-oxo-benzimidazol-1-yl]piperidine-2,6-dione (Intermediate LN)

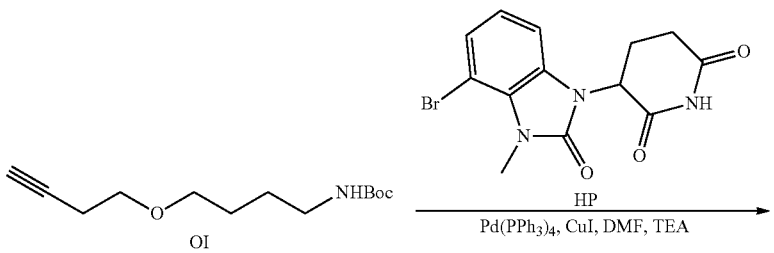

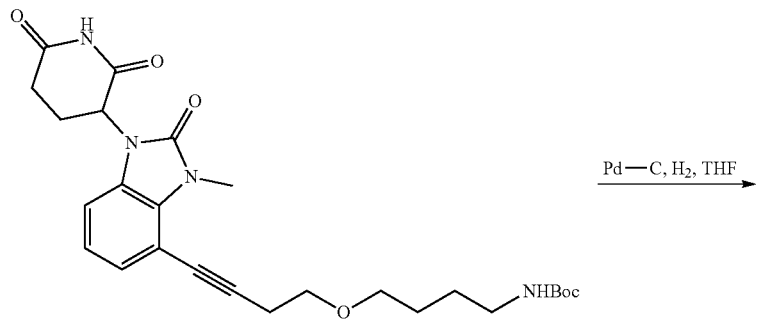

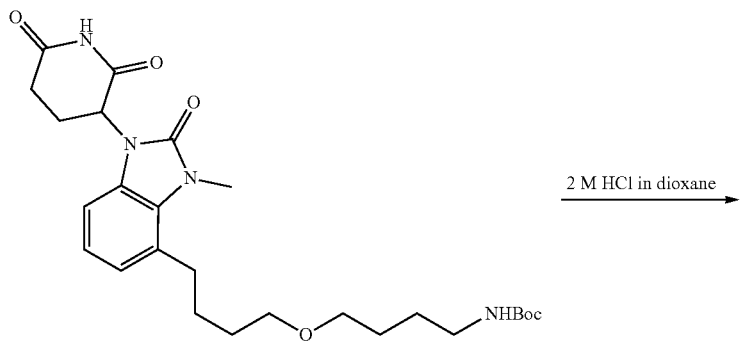

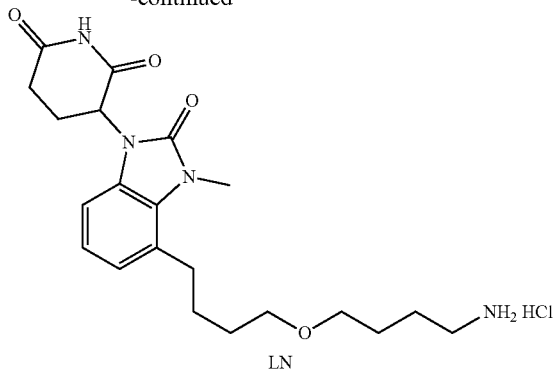

Step 1—Tert-butyl N-[4-([4-[1-(2,6-dioxopiperidin-3-yl)-3-methyl-2-oxo-2,3-dihydro-1H-1,3-benzodiazol-4-yl]but-3-yn-1-yl]oxy)butyl]carbamate To a stirred mixture of 3-(4-bromo-3-methyl-2-oxo-2,3-dihydro-1H-1,3-benzodiazol-1-yl)piperidine-2,6-dione (1.5 g, 4.4 mmol, Intermediate HP), Pd(PPh$_3$)$_2$Cl$_2$ (311.3 mg, 0.44 mmol) and CuI (84.5 mg, 0.44 mmol) in DMA (22 mL) and TEA (7 mL) was added tert-butyl N-[4-(but-3-yn-1-yloxy)butyl]carbamate (5.4 g, 22.2 mmol, Intermediate OI) at rt under nitrogen atmosphere. The resulting mixture was purged with nitrogen three times and stirred for 16 h at 85° C. under nitrogen atmosphere. The resulting mixture was cooled and concentrated under reduced pressure to remove TEA. The resulting mixture was diluted with a solution of AcOH (3 mL) in ice water (50 mL). The resulting mixture was extracted with EtOAc (2×50 mL). The combined organic layers was washed with brine (30 mL) and dried over anhydrous Na$_2$SO$_4$. After filtration, the filtrate was concentrated under reduced pressure. The residue was purified by reverse phase flash chromatography with the following conditions: Column: WelFlash™ C18-I, 20-40 m, 120 g; Eluent A: Water (plus 10 mmol/L FA); Eluent B: ACN; Gradient: 50%-60% B in 20 min; Flow rate: 60 mL/min; Detector: 220/254 nm; desired fractions were collected at 57% B and concentrated under reduced pressure to afford tert-butyl N-[4-([4-[1-(2,6-dioxopiperidin-3-yl)-3-methyl-2-oxo-2,3-dihydro-1H-1,3-benzodiazol-4-yl]but-3-yn-1-yl]oxy)butyl]carbamate (1.4 g, 63%) as a light yellow solid. $^1$H NMR (400 MHz, DMSO-d$_6$) δ 11.11 (s, 1H), 7.12 (d, J=7.7 Hz, 1H), 7.05 (d, J=7.7 Hz, 1H), 7.00 (d, J=7.8 Hz, 1H), 6.79 (t, J=5.7 Hz, 1H), 5.39 (dd, J=12.6, 5.4 Hz, 1H), 3.65 (s, 3H), 3.63-3.54 (m, 2H), 3.43 (t, J=6.3 Hz, 2H), 2.98-2.83 (m, 3H), 2.79-2.58 (m, 4H), 2.03 (dt, J=10.8, 5.1 Hz, 1H), 1.56-1.39 (m, 4H), 1.37 (s, 9H); LC/MS (ESI, m/z): [(M−1)]$^-$=497.15.

Step 2—Tert-butyl N-(4-[4-[1-(2,6-dioxopiperidin-3-yl)-3-methyl-2-oxo-2,3-dihydro-1H-1,3-benzodiazol-4-yl]butoxy]butyl)carbamate To a stirred solution of tert-butyl N-[4-([4-[1-(2,6-dioxopiperidin-3-yl)-3-methyl-2-oxo-2,3-dihydro-1H-1,3-benzodiazol-4-yl]but-3-yn-1-yl]oxy)butyl]carbamate (800 mg, 1.60 mmol) in THF (20 mL) was added palladium on charcoal (80 mg, 10% w/w) at room temperature. The resulting mixture was stirred for 3 h at rt under hydrogen atmosphere. After filtration, the filter cake was washed with EtOAc (2×10 mL). The filtrate was concentrated under reduced pressure to afford tert-butyl N-(4-[4-[1-(2,6-dioxopiperidin-3-yl)-3-methyl-2-oxo-2,3-dihydro-1H-1,3-benzodiazol-4-yl]butoxy]butyl)carbamate (500 mg, 62%) as a white solid; $^1$H NMR (400 MHz, DMSO-d$_6$) δ 11.09 (s, 1H), 6.96 (d, J=5.0 Hz, 2H), 6.87 (q, J=4.6 Hz, 1H), 6.77 (t, J=6.2 Hz, 1H), 5.37 (dd, J=12.5, 5.4 Hz, 1H), 3.56 (s, 3H), 3.40 (t, J=5.8 Hz, 2H), 3.37-3.29 (m, 2H), 3.00-2.82 (m, 5H), 2.78-2.57 (m, 2H), 2.06-1.95 (m, 1H), 1.71-1.55 (m, 4H), 1.53-1.37 (m, 4H), 1.37 (s, 9H); LC/MS (ESI, m/z): [(M+1)]$^+$=503.20.

Step 3—3-[4-[4-(4-Aminobutoxy)butyl]-3-methyl-2-oxo-2,3-dihydro-1H-1,3-benzodiazol-1-yl]piperidine-2,6-dione hydrochloride To a stirred solution of tert-butyl N-(4-[4-[1-(2,6-dioxopiperidin-3-yl)-3-methyl-2-oxo-2,3-dihydro-1H-1,3-benzodiazol-4-yl]butoxy]butyl)carbamate (500 mg, 0.99 mmol) in dioxane (4 mL) was added a solution of hydrochloride in 1,4-dioxane (4 M, 4 mL) dropwise at rt under nitrogen atmosphere. The resulting solution was stirred for 2 h at rt under nitrogen atmosphere. The resulting mixture was concentrated under reduced pressure to afford 3-[4-[4-(4-aminobutoxy)butyl]-3-methyl-2-oxo-2,3-dihydro-1H-1,3-benzodiazol-1-yl]piperidine-2,6-dione hydrochloride (420 mg, 96%) as a white solid. $^1$H NMR (400 MHz, DMSO-d$_6$) δ 11.08 (s, 1H), 7.88 (br s, 3H), 7.02-6.92 (m, 2H), 6.87 (dd, J=6.2, 2.6 Hz, 1H), 5.38 (dd, J=12.6, 5.4 Hz, 1H), 3.57 (s, 3H), 3.47-3.28 (m, 4H), 2.99-2.84 (m, 3H), 2.79-2.58 (m, 4H), 2.00 (dt, J=11.1, 5.2 Hz, 1H), 1.69-1.50 (m, 8H); LC/MS (ESI, m/z): [(M+1)]$^+$=403.25.

(2S,4R)-1-[(2S)-2-[[2-[2-[2-(2-aminoethoxy)ethoxy]ethoxy]acetyl]amino]-3,3-dimethyl-butanoyl]-4-hydroxy-N-[[4-(4-methylthiazol-5-yl)phenyl]methyl]pyrrolidine-2-carboxamide (Intermediate LO)

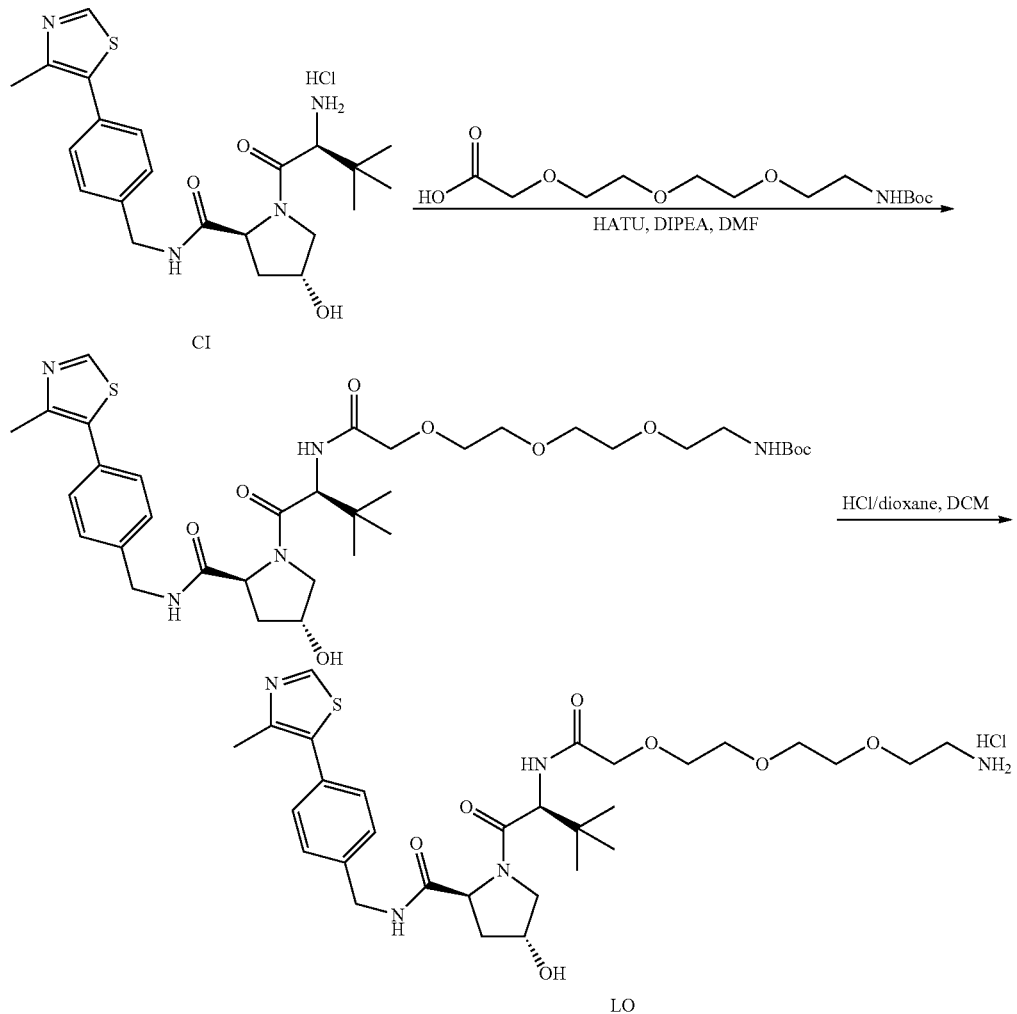

Step 1—Tert-butyl N-[2-[2-[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethoxy]ethyl]carbamate To a solution of (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide (250 mg, 535 umol, HCl, Intermediate CI) and 2-[2-[2-[2-(tert-butoxycarbonylamino)ethoxy]ethoxy]ethoxy]acetic acid (164 mg, 535 umol, CAS #462100-06-7) in DMF (5 mL) was added DIPEA (207 mg, 1.61 mmol) and HATU (244 mg, 642 umol). The mixture was stirred at rt for 1 hour. On completion, the reaction mixture was quenched with water 20 mL, and then extracted with EA (3×30 mL). The combined organic layers were dried over Na$_2$SO$_4$, filtered and concentrated in vacuo to give a residue. The residue was purified by prep-HPLC (FA condition) to give the title compound (300 mg, 77% yield) as brown solid. LC-MS (ESI$^+$) m/z 720.4 (M+H)$^+$.

Step 2 (2S,4R)-1-[(2S)-2-[[2-[2-[2-(2-aminoethoxy)ethoxy]ethoxy]acetyl]amino]-3,3-dimethyl-butanoyl]-4-hydroxy-N-[[4-(4-methylthiazol-5-yl)phenyl]methyl]pyrrolidine-2-carboxamide To a solution of tert-butyl N-[2-[2-[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethoxy]ethyl]carbamate (240 mg, 333 umol) in DCM (12 mL) was added HCl/dioxane (4 M, 2.5 mL). The mixture was stirred at rt for 0.5 hour. On completion, the reaction mixture was concentrated in vacuo to give the title compound (0.21 g, 96% yield, HCl) as light yellow solid. LC-MS (ESI$^+$) m/z 620.2 (M+H)$^+$.

(2S,4R)-1-[(2S)-2-[2-[2-[2-(2-aminoethoxy)ethoxy]ethoxy]ethylamino]-3,3-dimethyl-butanoyl]-4-hydroxy-N-[[4-(4-methylthiazol-5-yl)phenyl]methyl]pyrrolidine-2-carboxamide (Intermediate LP)

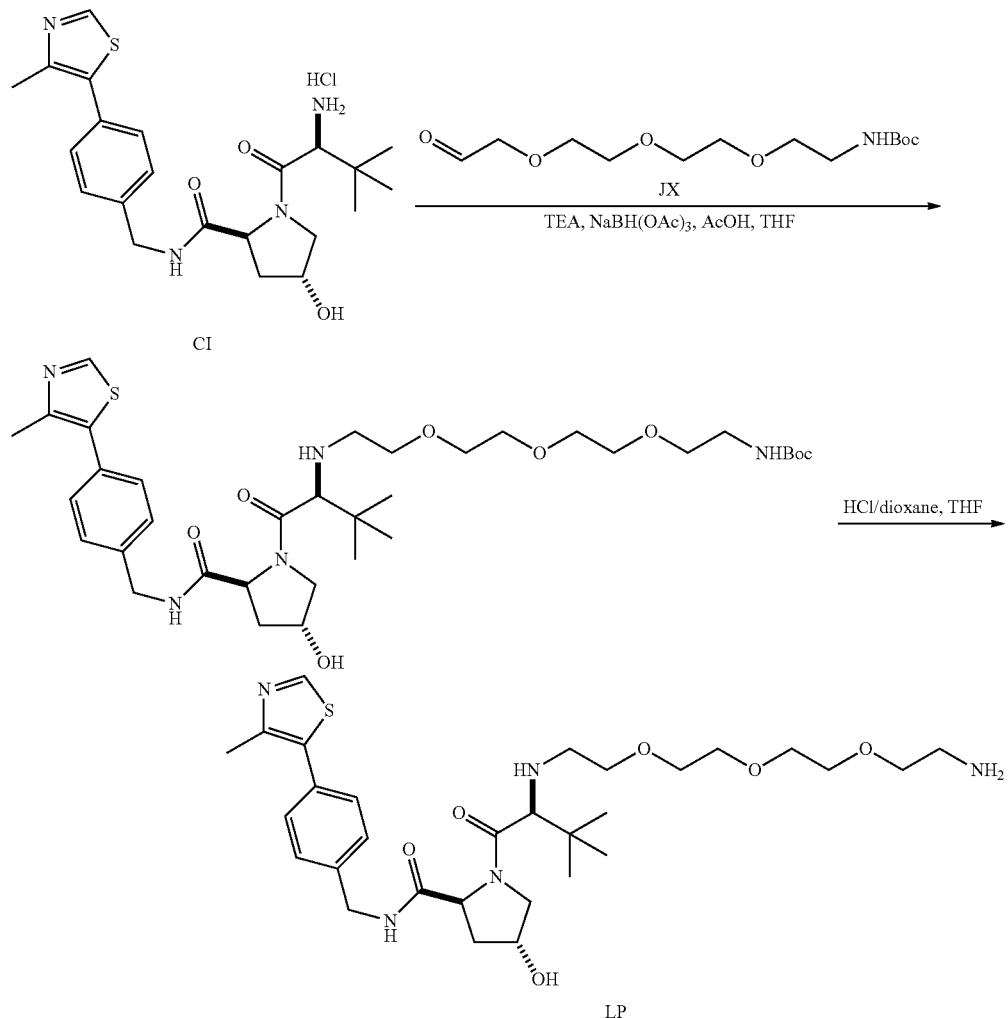

Step 1—Tert-butyl N-[2-[2-[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]ethoxy]ethoxy]ethoxy]ethyl]carbamate To a mixture of tert-butyl N-[2-[2-[2-(2-oxoethoxy)ethoxy]ethoxy]ethyl]carbamate (500 mg, 1.72 mmol, Intermediate JX), (2S,4R)-1-[(2S)-2-amino-3,3-dimethyl-butanoyl]-4-hydroxy-N-[[4-(4-methyl thiazol-5-yl)phenyl]methyl]pyrrolidine-2-carboxamide (801 mg, 1.72 mmol, HCl, Intermediate CI), and TEA (174 mg, 1.72 mmol) in THF (20 mL) was added AcOH (103 mg, 1.72 mmol) and NaBH(OAc)₃ (727 mg, 3.43 mmol). Then the mixture was stirred at rt for 72 hrs under N₂ atmosphere. On completion, the mixture was concentrated in vacuo to give a residue. The residue was purified by Pre-HPLC (acid condition) to give the title compound (480 mg, 38% yield) as colorless solid. LC-MS (ESI⁺) m/z 706.5 (M+H)⁺.

Step 2—(2S,4R)-1-[(2S)-2-[2-[2-[2-(2-aminoethoxy)ethoxy]ethoxy]ethylamino]-3,3-dimethyl-butanoyl]-4-hydroxy-N-[[4-(4-methylthiazol-5-yl)phenyl]methyl]pyrrolidine-2-carboxamide To a solution of tert-butyl N-[2-[2-[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]ethoxy]ethoxy]ethoxy]ethyl]carbamate (380 mg, 538 umol) in THF (10 mL) was added HCl/dioxane (4 M, 12 mL). The mixture was stirred at rt for 6 hrs. On completion, the mixture was concentrated in vacuo to give the title compound (325 mg, 94% yield) as white solid. LC-MS (ESI⁺) m/z 606.4 (M+H)⁺.

1575

Tert-butyl N-[3-[3-(3-aminopropoxy)propoxy]propyl]carbamate (Intermediate LQ)

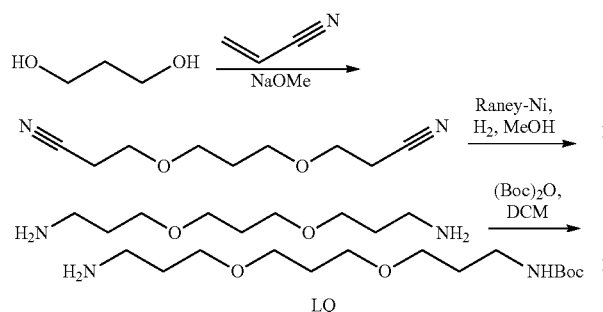

Step 1—3-[3-(2-Cyanoethoxy)propoxy]propanenitrile

NaOMe (71.00 mg, 1.31 mmol) was dissolved in a solution of propane-1,3-diol (10 g, 131 mmol, CAS #126-30-7). Then prop-2-enenitrile (27.9 g, 525 mmol, CAS #107-13-1) was added into the mixture. The reaction mixture was stirred at rt for 48 hrs. On completion, the mixture was concentrated in vacuo. The residue was purified by column chromatography to give the title compound (21.6 g, 90% yield) as a brown solid. $^1$H NMR (400 MHz, DMSO-$d_6$) δ 3.57 (t, J=6.4 Hz, 4H), 3.50 (t, J=6.4 Hz, 4H), 2.74 (t, J=6.4 Hz, 4H), 1.79-1.73 (m, 2H).

Step 2—3-[3-(3-Aminopropoxy)propoxy]propan-1-amine

To a mixture of 3-[3-(2-cyanoethoxy)propoxy]propanenitrile (10 g, 54.9 mmol) in MeOH (10 mL) was added Raney-Ni (9.40 g, 109 mmol), and the reaction mixture was stirred at 25° C. for 12 hrs under $H_2$ (50 psi). On completion, the mixture was concentrated in vacuo. The residue was purified by column chromatography to give the title compound (8.40 g, 80% yield) as brown oil. $^1$H NMR (400 MHz, CDCl$_3$) δ 3.74-3.30 (m, 9H), 2.79-2.38 (m, 4H), 1.85-1.56 (m, 4H), 1.91-1.48 (m, 1H).

Step 3—Tert-butyl N-[3-[3-(3-aminopropoxy)propoxy]propyl]carbamate

To a solution of 3-[3-(3-aminopropoxy)propoxy]propan-1-amine (4.00 g, 21.0 mmol) in DCM (40 mL) was dropwise added (Boc)$_2$O (5.51 g, 25.2 mmol). The reaction mixture was stirred at rt for 12 hrs. On completion, the mixture was concentrated in vacuo. The residue was purified by column chromatography to give the title compound (2.20 g, 36% yield) brown oil. $^1$H NMR (400 MHz, CDCl$_3$) δ 3.66-3.60 (m, 3H), 3.66-3.60 (m, 3H), 3.49-3.45 (m, 4H), 2.61-2.53 (m, 4H), 1.88-1.68 (m, 6H), 1.41 (s, 9H).

4-[3-[3-(3-Aminopropoxy)propoxy]propylamino]-2-(2,6-dioxo-3-piperidyl)isoindoline-1,3-dione (Intermediate LR)

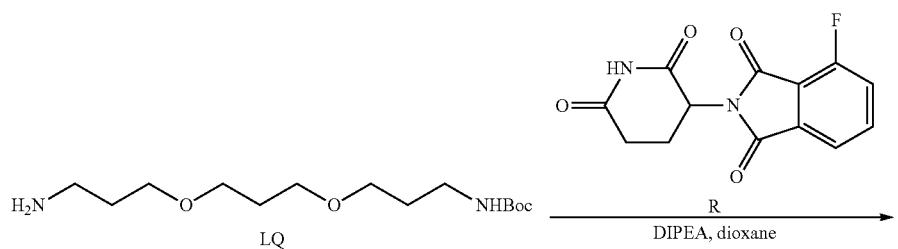

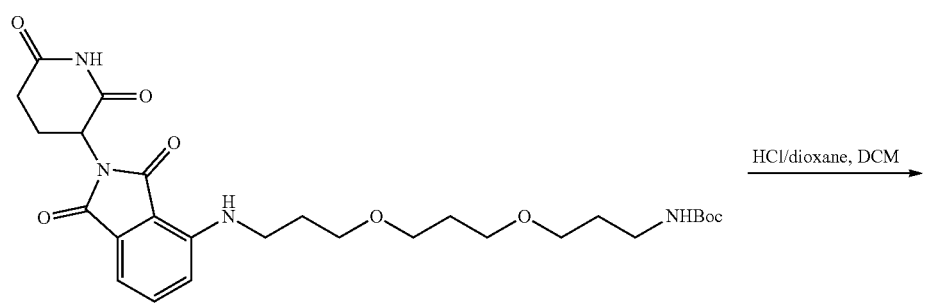

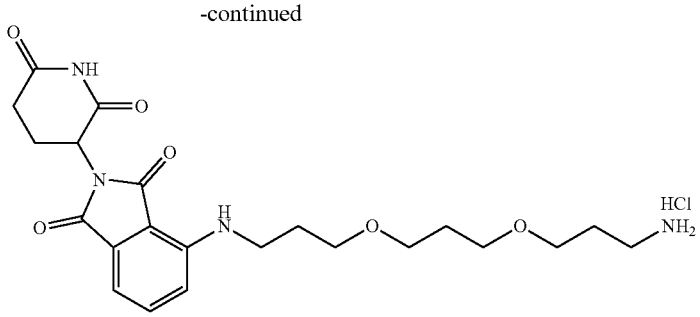

LR

Step 1—Tert-butyl N-[3-[3-[3-[[2-(2,6-dioxo-3-piperidyl)-1,3-dioxo-isoindolin-4-yl]amino]propoxy]propoxy]propyl]carbamate To a mixture of 2-(2,6-dioxo-3-piperidyl)-4-fluoro-isoindoline-1,3-dione (476 mg, 1.72 mmol, Intermediate R), tert-butyl N-[3-[3-(3-aminopropoxy)propoxy]propyl]carbamate (500 mg, 1.72 mmol, Intermediate LQ) in dioxane (10 mL) was added DIPEA (2.23 g, 17.2 mmol). The reaction mixture was stirred at 115° C. for 12 hrs. On completion, the mixture was concentrated in vacuo. The residue was purified by reverse phase (0.1% FA) to give the title compound (820 mg, 87% yield) as brown oil. LC-MS (ESI$^+$) m/z 547.4 (M+H)$^+$.

Step 2—4-[3-[3-(3-Aminopropoxy)propoxy]propylamino]-2-(2,6-dioxo-3-piperidyl)isoindoline-1,3-dione To a mixture of tert-butyl N-[3-[3-[3-[[2-(2,6-dioxo-3-piperidyl)-1,3-dioxo-isoindolin-4-yl]amino]propoxy]propoxy]propyl]carbamate (820 mg, 1.50 mmol) in DCM (5 mL) was added HCl/dioxane (4 M, 750 uL) and the reaction was stirred at rt for 1 hr. On completion, the mixture was concentrated in vacuo to give the title compound (695 mg, 96% yield, HCl) as yellow oil LC-MS (ESI$^+$) m/z 447.1 (M+H)$^+$.

Tert-butyl N-[4-[4-[(3-formyl-1-methyl-pyrazol-4-yl)carbamoyl]oxazol-2-yl]-2-pyridyl]-N-(2,2,2-trifluoroethyl)carbamate (Intermediate LS)

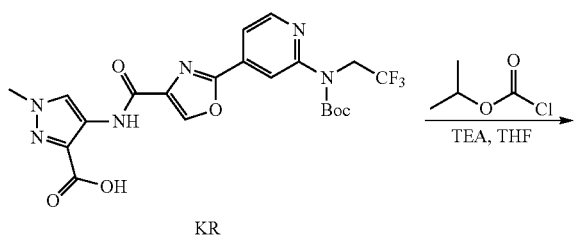

KR

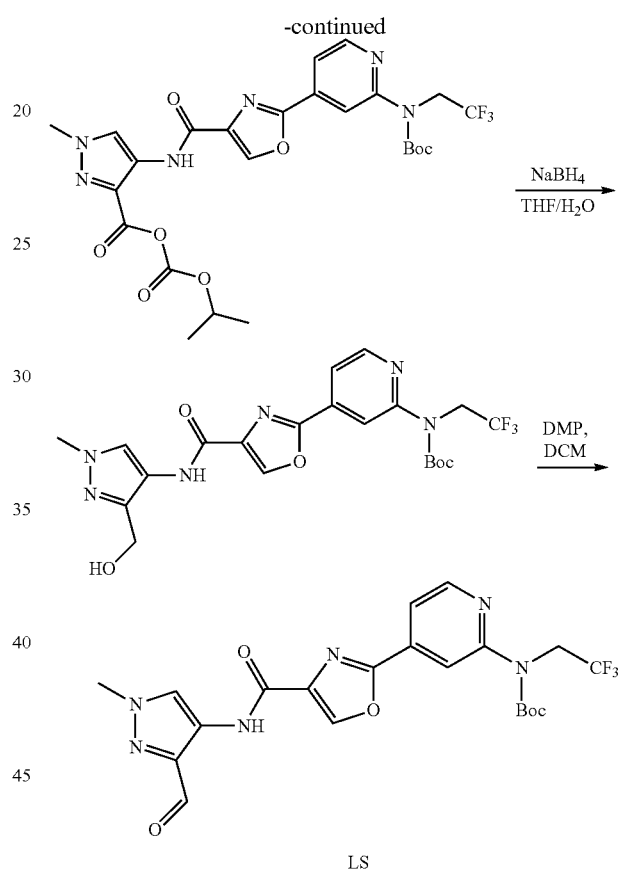

LS

Step 1—Isopropoxycarbonyl 4-[[2-[2-[tert-butoxycarbonyl(2,2,2-trifluoroethyl)amino]-4-pyridyl]oxazole-4-carbonyl]amino]-1-methyl-pyrazole-3-carboxylate To a solution of 4-[[2-[2-[tert-butoxycarbonyl(2,2,2-trifluoroethyl)amino]-4-pyridyl]oxazole-4-carbonyl]amino]-1-methyl-pyrazole-3-carboxylic acid (3 g, 5.88 mmol, Intermediate KR) in THF (50 mL) was added TEA (595 mg, 5.88 mmol). Then, the reaction mixture was cooled to −10° C. To the mixture was added isopropyl carbonochloridate (1.44 g, 11.8 mmol). The resulting reaction mixture was stirred at −10° C. for 2 hours. On completion, the reaction mixture was filtered. The filtrate was concentrated in vacuo to give the title compound (3.51 g, 82% yield) as a white solid. LC-MS (ESI$^+$) m/z 597.1 (M+H)$^+$.

Step 2—Tert-butyl N-[4-[4-[[3-(hydroxymethyl)-1-methyl-pyrazol-4-yl]carbamoyl]oxazol-2-yl]-2-pyridyl]-N-(2,2,2-trifluoroethyl)carbamate To a solution of isopropoxycarbonyl 4-[[2-[2-[tert-butoxycarbonyl(2,2,2-trifluoroethyl)amino]-4-pyridyl]oxazole-4-carbonyl]amino]-1-methyl-pyrazole-3-carboxylate (3.51 g, 4.83 mmol) in THF (60 mL) was added LiBH$_4$ (315 mg, 14.5 mmol) and H$_2$O (1.37 g, 76.0 mmol). The reaction mixture was stirred at 0° C. for 1 hr. On completion, the reaction mixture was quenched with water (5 mL) and the mixture was extracted with DCM (3×50 mL). The combined organic layer was washed with brine (20 mL), dried over anhydrous sodium sulfate, filtered and concentrated in vacuo to give the title compound (2.92 g, 73% yield) as a white solid. LC-MS (ESI$^+$) m/z 497.1 (M+H)$^+$.

Step 3—Tert-butyl N-[4-[4-[(3-formyl-1-methyl-pyrazol-4-yl)carbamoyl]oxazol-2-yl]-2-pyridyl]-N-(2,2,2-trifluoroethyl)carbamate To a solution of tert-butyl N-[4-[4-[[3-(hydroxymethyl)-1-methyl-pyrazol-4-yl]carbamoyl]oxazol-2-yl]-2-pyridyl]-N-(2,2,2-trifluoroethyl)carbamate (2.42 g, 4.19 mmol) in DCM (30 mL) was added DMP (3.56 g, 8.38 mmol). The reaction mixture was stirred at rt for 5 hrs. On completion, the reaction mixture was quenched with saturated Na$_2$S$_2$O$_3$ (20 mL), and extracted with DCM (3×30 mL). The combined organic layer was washed with saturated NaHCO$_3$ (2×20 mL) and brine (30 mL), dried over with anhydrous sodium sulfate, filtered and concentrated in vacuo. The residue was triturated with methanol (10 mL) to give the title compound (1.60 g, 77% yield) as a white solid. $^1$H NMR (400 MHz, DMSO-d$_6$) δ 10.32 (s, 1H), 10.00 (s, 1H), 9.11 (s, 1H), 8.67 (d, J=5.2 Hz, 1H), 8.44 (s, 1H), 8.29 (s, 1H), 7.79 (dd, J=1.2, 5.2 Hz, 1H), 4.91 (q, J=8.8 Hz, 2H), 4.02 (s, 3H), 1.54 (s, 9H). LC-MS (ESI$^+$) m/z 495.1 (M+H)$^+$.

2-(2-Chloro-3-pyridyl)oxazole-4-carboxylic acid (Intermediate LT)

Step 1—Methyl 2-(2-chloro-3-pyridyl)oxazole-4-carboxylate

To a solution of methyl 2-amino-3-hydroxy-propanoate; hydrochloride (1.10 g, 7.06 mmol, CAS #2104-89-4) in DMA (20 mL) was added NaHCO$_3$ (1.19 g, 14.1 mmol). The mixture was stirred at rt for 2 hours. Then, to the mixture was added 2-chloropyridine-3-carbaldehyde (1 g, 7.06 mmol, CAS #36404-88-3) in one portion. The mixture was stirred for 12 hours. Then, to the mixture was added bromo(trichloro)methane (4.20 g, 21.2 mmol) and DBU (3.23 g, 21.2 mmol) at 0° C. Then, the mixture was stirred at rt for an additional 12 hours. On completion, the mixture was quenched with water (20 mL) and extracted with EA (2×100 mL). The organic layer was washed with brine (30 mL) and concentrated in vacuo. The residue was purified by silica gel chromatography (SiO$_2$) to give the title compound (1.2 g, 71% yield) as a white solid. LC-MS (ESI+) m/z 238.9 (M+H)$^+$.

Step 2—2-(2-Chloro-3-pyridyl)oxazole-4-carboxylic acid

To a solution of methyl 2-(2-chloro-3-pyridyl) oxazole-4-carboxylate (1.2 g, 5.03 mmol) in a mixed solvent of H$_2$O (4 mL) and THF (20 mL) was added LiOH.H$_2$O (602 mg, 25.1 mmol). The mixture was stirred at rt for 5 hours. On completion, the mixture was adjusted to pH=7 with 1N aq.HCl, and filtered. The filter cake was dried in vacuo to give the title compound (0.7 g, 62% yield) as a white solid. LC-MS (ESI+) m/z 225.0 (M+H)$^+$.

3-(Difluoromethyl)-1-methyl-pyrazol-4-amine (Intermediate LU)

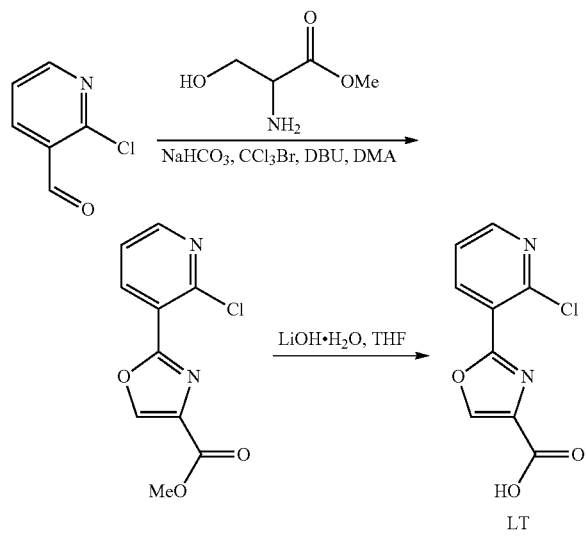

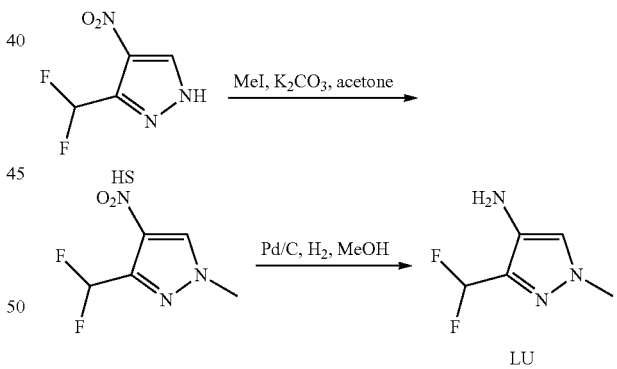

Step 1—3-Difluoromethyl)-1-methyl-4-nitro-pyrazole

A mixture of 3-(difluoromethyl)-4-nitro-1H-pyrazole (1 g, 6.13 mmol, Intermediate HS), K$_2$CO$_3$ (1.69 g, 12.3 mmol), and MeI (1.74 g, 12.3 mmol) in acetone (20 mL) was degassed and purged with N$_2$ gas 3 times. Then the mixture was stirred at 70° C. for 2 hours under N$_2$ atmosphere. On completion, the mixture was filtered and the filtrate was concentrated in vacuo. The residue was purified by silica gel chromatography (SiO$_2$) to give the title compound (0.5 g, 46% yield) as yellow oil.

Step 2—3-(Difluoromethyl)-1-methyl-pyrazol-4-amine

To a solution of 3-(difluoromethyl)-1-methyl-4-nitro-pyrazole (200 mg, 1.13 mmol) in MeOH (10 mL) was added Pd/C (200 mg, 10 wt %). The mixture was stirred at rt for 3 hours under H$_2$ atmosphere (15 Psi). On completion, the mixture was filtered and the filtrate was concentrated in vacuo to give the title compound (0.2 g, crude) as red oil. $^1$H NMR (400 MHz, CDCl$_3$) δ 6.89 (s, 1H), 6.76-6.45 (m, 1H), 3.72 (s, 3H), 2.86 (s, 2H).

2-(2-Chloro-3-pyridyl)-N-[3-(difluoromethyl)-1-methyl-pyrazol-4-yl]oxazole-4-carboxamide (Intermediate LV)

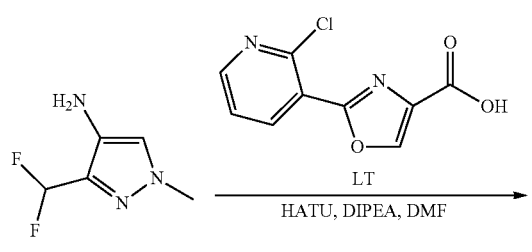

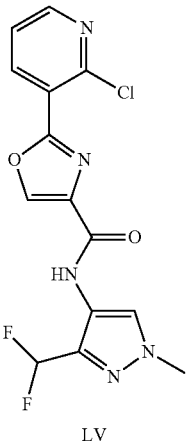

A mixture of 3-(difluoromethyl)-1-methyl-pyrazol-4-amine (350 mg, 2.38 mmol, Intermediate LU), 2-(2-chloro-3-pyridyl)oxazole-4-carboxylic acid (534 mg, 2.38 mmol, Intermediate LT), DIPEA (922 mg, 7.14 mmol), and HATU (1.09 g, 2.85 mmol) in DMF (3 mL) was degassed and purged with N$_2$ gas 3 times, and then the mixture was stirred at rt for 3 hours under N$_2$ atmosphere. On completion, the mixture was quenched with water (20 ml) and extracted with EA (2×20 mL). The organic layer was washed with brine (20 mL), then concentrated in vacuo to give the title compound (0.6 g, 96% yield) as a white solid. LC-MS (ESI+) m/z 354.1 (M+H)$^+$.

2-[2-[2-[2-[2-(2-Aminoethoxy)ethoxy]ethoxy]ethylamino]-3-pyridyl]-N-[3-(difluoromethyl)-1-methyl-pyrazol-4-yl]oxazole-4-carboxamide (Intermediate LW)

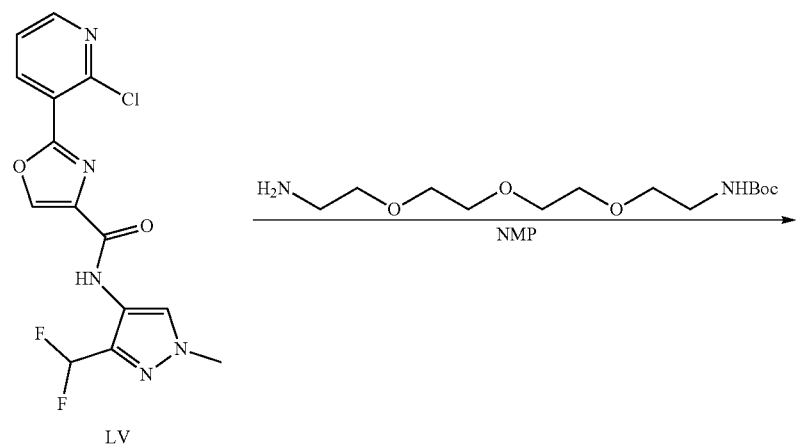

-continued

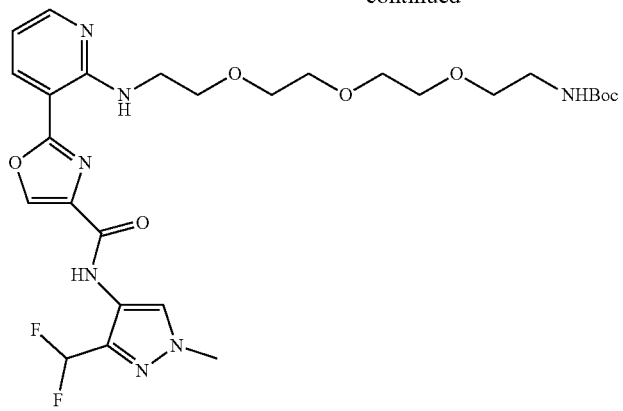

HCl/dioxane, THF →

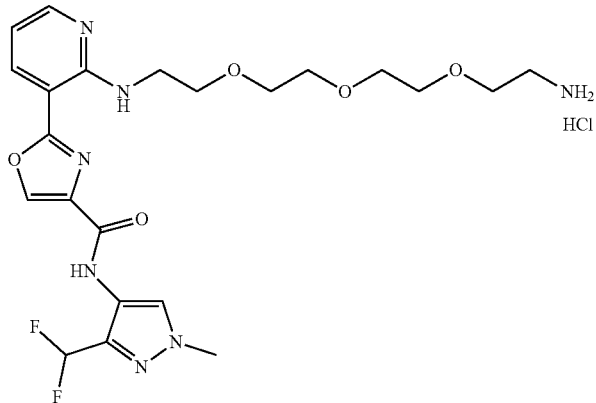

LW

Step 1—Tert-butyl N-[2-[2-[2-[2-[[3-[4-[[3-(difluoromethyl)-1-methyl-pyrazol-4-yl]carbamoyl]oxazol-2-yl]-2-pyridyl]amino]ethoxy]ethoxy]ethoxy]ethyl]carbamate To a solution of 2-(2-chloro-3-pyridyl)-N-[3-(difluoromethyl)-1-methyl-pyrazol-4-yl]oxazole-4-carboxamide (200 mg, 565 umol, Intermediate LV) in NMP (2 mL) was added tert-butyl N-[2-[2-[2-(2-aminoethoxy) ethoxy]ethoxy]ethyl] carbamate (827 mg, 2.83 mmol, CAS #101187-40-0). The mixture was stirred at 150° C. for 1 hour under microwave. On completion, the mixture was concentrated in vacuo. The residue was purified by prep-HPLC (acid condition) to give the title compound (0.2 g, 55% yield) as a white solid. LC-MS (ESI$^+$) m/z 610.4 (M+H)$^+$.

Step 2—2-[2-[2-[2-[2-(2-Aminoethoxy)ethoxy]ethoxy]ethylamino]-3-pyridyl]-N-[3-(difluoromethyl)-1-methyl-pyrazol-4-yl]oxazole-4-carboxamide To a solution of tert-butyl N-[2-[2-[2-[2-[[3-[4-[[3-(difluoromethyl)-1-methyl-pyrazol-4-yl]carbamoyl]oxazol-2-yl]-2-pyridyl]amino]ethoxy]ethoxy]ethoxy]ethyl]carbamate (200 mg, 328 umol) in THF (5 mL) was added HCl/dioxane (4 M, 4 mL). The mixture was stirred at rt for 16 hours. On completion, the mixture was concentrated in vacuo to give the title compound (180 mg, 93% yield, HCl) as a yellow solid. LC-MS (ESI$^+$) m/z 510.3 (M+H)$^+$.

7-[2-[2-[2-[2-(2-aminoethoxy)ethoxy]ethoxy]ethoxy]ethoxy]-2-[(2S)-2-[(2-methoxyacetyl)amino]-3,3-dimethyl-butanoyl]-N-[(1R)-tetralin-1-yl]-3,4-dihydro-1H-isoquinoline-3-carboxamide (Intermediate LX)

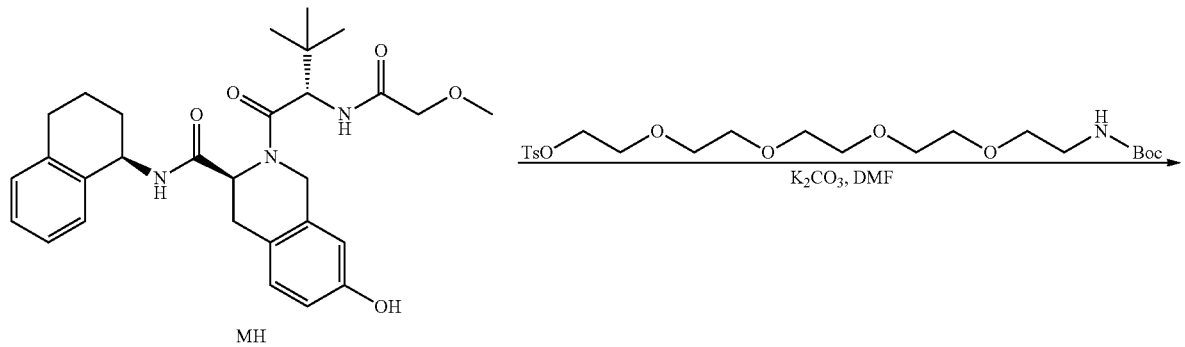

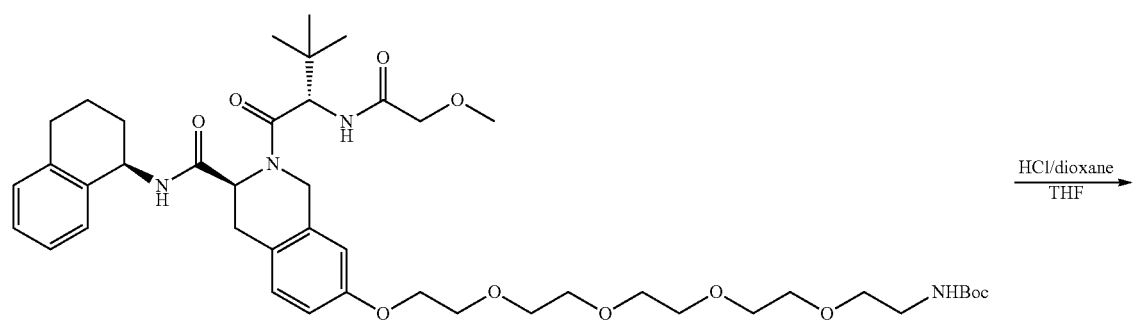

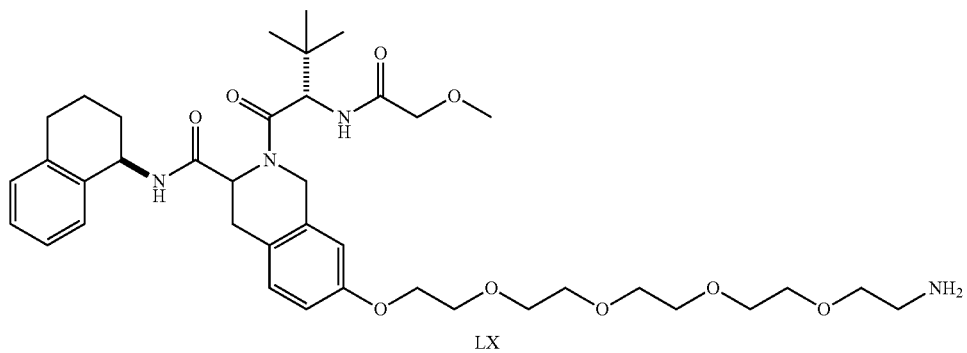

7-[2-[2-[2-[2-(2-aminoethoxy)ethoxy]ethoxy]ethoxy]ethoxy]-2-[(2S)-2-[(2-methoxyacetyl)amino]-3,3-dimethyl-butanoyl]-N-[(1R)-tetralin-1-yl]-3,4-dihydro-1H-isoquinoline-3-carboxamide was synthesized as described for Intermediate LY, using 2,2-dimethyl-4-oxo-3,8,11,14,17-pentaoxa-5-azanonadecan-19-yl 4-methylbenzenesulfonate, Intermediate ON, as the tosylate in Step 1 to couple with alcohol Intermediate MH. $^1$H NMR (400 MHz, DMSO-d$_6$) δ 8.21-8.15 (m, 1H), 7.45-7.30 (m, 1H), 7.14-6.77 (m, 7H), 5.11-4.40 (m, 5H), 4.07-4.02 (m, 2H), 3.90-3.72 (m, 4H), 3.60-3.41 (m, 12H), 3.36-3.20 (m, 7H), 3.05-2.93 (m, 2H), 2.76-2.61 (m, 4H), 1.87-1.52 (m, 4H), 1.03-0.93 (m, 9H). LC-MS (ESI$^+$): m/z 727.2 (M+H)$^+$ 7-[2-[2-[2-(2-aminoethoxy)ethoxy]ethoxy]ethoxy]-2-[(2S)-2-[(2-methoxyacetyl)amino]-3,3-dimethylbutanoyl]-N-[(1R)-tetralin-1-yl]-3,4-dihydro-1H-isoquinoline-3-carboxamide (Intermediate LY)

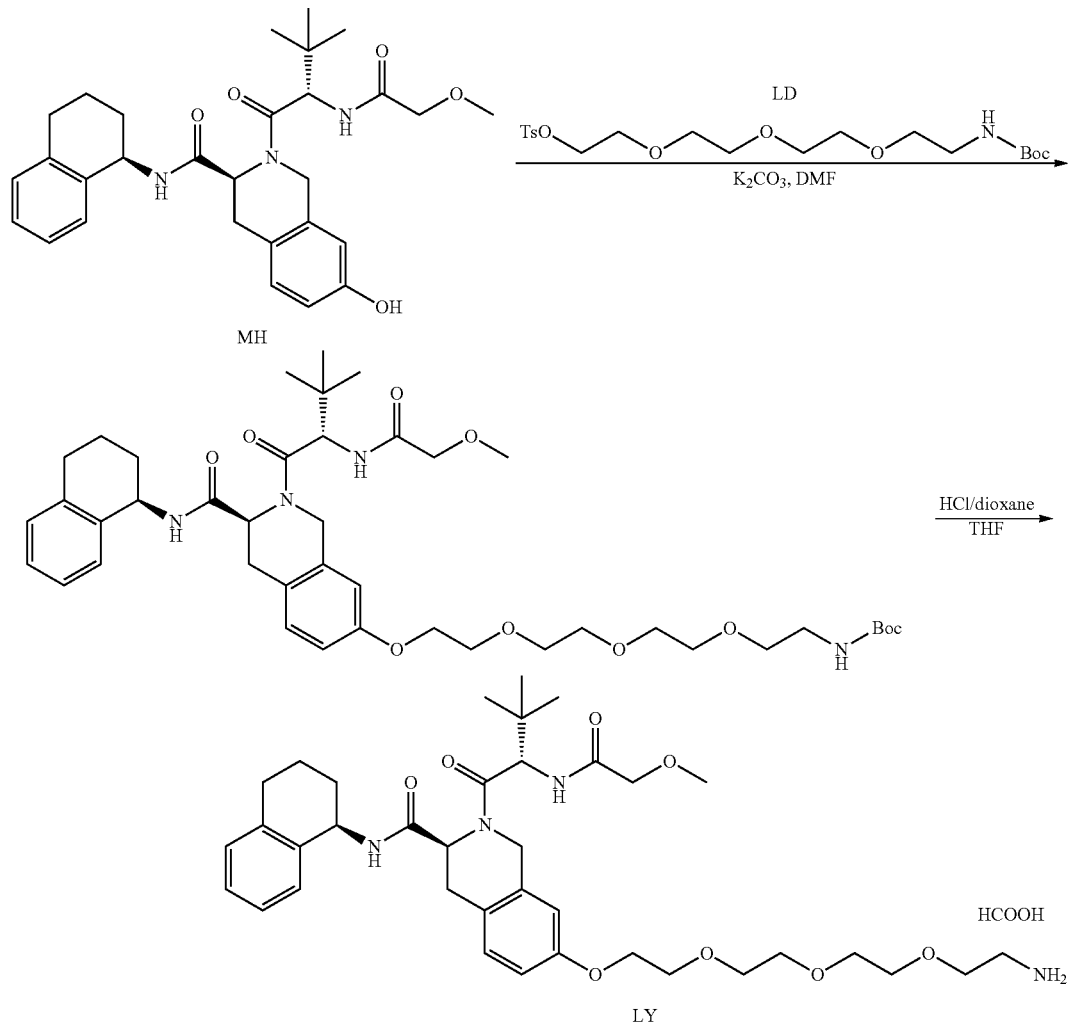

Step 1—tert-butyl (2-(2-(2-(2-(((S)-2-((S)-2-(2-methoxyacetamido)-3,3-dimethylbutanoyl)-3-(((R)-1,2,3,4-tetrahydronaphthalen-1-yl)carbamoyl)-1,2,3,4-tetrahydroisoquinolin-7-yl)oxy)ethoxy)ethoxy)ethoxy)ethyl)carbamate To a mixture of (S)-7-hydroxy-2-((S)-2-(2-methoxyacetamido)-3,3-dimethylbutanoyl)-N—((R)-1,2,3,4-tetrahydronaphthalen-1-yl)-1,2,3,4-tetrahydroisoquinoline-3-carboxamide (1.75 g, 3.45 mmol, Intermediate MH) and 2,2-dimethyl-4-oxo-3,8,11,14-tetraoxa-5-azahexadecan-16-yl 4-methyl benzenesulfonate (1.7 g, 3.8 mmol, Intermediate LD) in DMF (25 mL) was added $K_2CO_3$ (714 mg, 5.2 mmol), and the mixture was stirred at 110° C. for overnight. The solution was then poured into water (150 mL) and the mixture was extracted with EtOAc (20 mL×2). The combined organic layer was washed with brine (50 mL×3), dried over $Na_2SO_4$, filtered, concentrated in vacuo and purified via column chromatography (Petroleum ether/EtOAc=1/1) to give the title compound (1.38 g, 51.1% yield) as a colorless oil. LC-MS (ESI+): m/z 683.2 (M-99)+.

Step 2—(S)-7-(2-(2-(2-(2-aminoethoxy)ethoxy)ethoxy)-2-((S)-2-(2-methoxyacetamido)-3,3-dimethylbutanoyl)-N—((R)-1,2,3,4-tetrahydronaphthalen-1-yl)-1,2,3,4-tetrahydroisoquinoline-3-carboxamide To a mixture of tert-butyl (2-(2-(2-(2-(((S)-2-((S)-2-(2-methoxyacetamido)-3,3-dimethyl butanoyl)-3-(((R)-1,2,3,4-tetrahydronaphthalen-1-yl)carbamoyl)-1,2,3,4-tetrahydroisoquinolin-7-yl)oxy)ethoxy)ethoxy)ethoxy)ethyl) carbamate (1.38 g, 1.76 mmol) in THF (15 mL) was added 4 M HCl/dioxane (10 mL), and the mixture was stirred at rt for overnight. Then the solution was poured into aq.NaHCO$_3$ (100 mL), and the mixture was extracted with EtOAc (20 mL×2). The combined organic layer was washed with brine (50 mL×3), dried over $Na_2SO_4$, filtered, concentrated in vacuo and purified via column chromatography (DCM/MeOH=10/1) to give the title compound (600 mg, 50% yield) as a white solid. $^1$H NMR (400 MHz, DMSO-d$_6$) δ (s, 1H), 8.23-8.17 (m, 1H), 7.46-7.30 (m, 1H), 7.14-6.77

(m, 7H), 5.12-4.41 (m, 5H), 4.07-4.03 (m, 2H), 3.90-3.73 (m, 4H), 3.60-3.47 (m, 10H), 3.32-3.29 (m, 3H), 3.06-2.93 (m, 2H), 2.81-2.64 (m, 4H), 1.87-1.52 (m, 4H), 1.03-0.94 (m, 9H). LC-MS (ESI$^+$): m/z 683.2 (M+H)$^+$.

3-[4-[3-[3-(3-aminopropoxy)-2,2-dimethyl-propoxy]propyl]-3-methyl-2-oxo-benzimidazol-1-yl]piperidine-2,6-dione (Intermediate LZ)

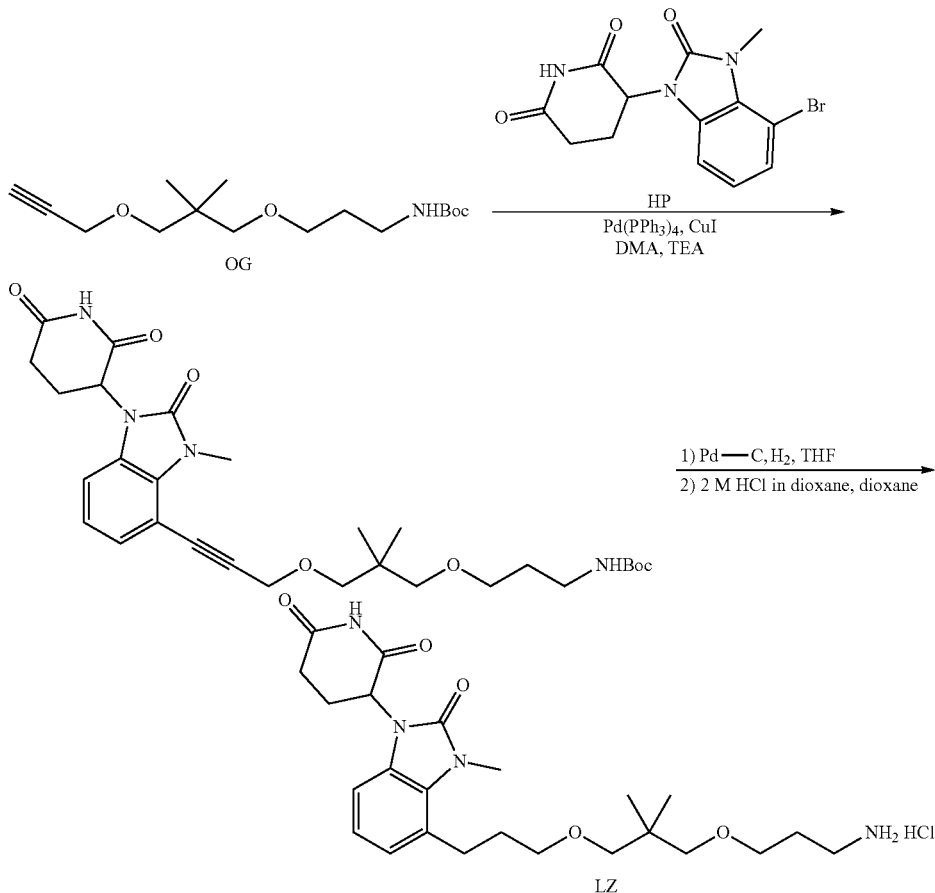

Step 1—Tert-butyl N-[3-[3-([3-[1-(2,6-dioxopiperidin-3-yl)-3-methyl-2-oxo-2,3-dihydro-1H-1,3-benzodiazol-4-yl]prop-2-yn-1-yl]oxy)-2,2-dimethylpropoxy]propyl]carbamate To a stirred solution of 3-(4-bromo-3-methyl-2-oxo-2,3-dihydro-1H-1,3-benzodiazol-1-yl)piperidine-2,6-dione (2.45 g, 7.25 mmol, Intermediate HP) and tert-butyl N-[3-[2,2-dimethyl-3-(prop-2-yn-1-yloxy)propoxy]propyl]carbamate (1.5 g, 4.85 mmol, Intermediate OG) in DMA (25 mL) were added CuI (138.0 mg, 0.72 mmol), TEA (10 mL) and Pd(PPh$_3$)$_4$ (837.2 mg, 0.72 mmol) at rt under nitrogen atmosphere. The resulting mixture was stirred for 5 h at 90° C. under nitrogen atmosphere. The resulting mixture was cooled and concentrated under reduced pressure to remove TEA. The residue was purified by reverse phase flash chromatography with the following conditions: Column: WelFlash™ C18-I, 20-40 μm, 300 g; Eluent A: Water (plus 10 mmol/L FA); Eluent B: ACN; Gradient: 48%-68% B in 25 min; Flow rate: 80 mL/min; Detector: 220/254 nm; desired fractions were collected at 60% B and concentrated under reduced pressure to afford tert-butyl N-[3-[3-([3-[1-(2,6-dioxopiperidin-3-yl)-3-methyl-2-oxo-2,3-dihydro-1H-1,3-benzodiazol-4-yl]prop-2-yn-1-yl]oxy)-2,2-dimethylpropoxy]propyl]carbamate (1.4 g, 33%) as a light brown solid: $^1$H NMR (400 MHz, DMSO-d$_6$) δ 11.12 (s, 1H), 7.20-7.16 (m, 1H), 7.12 (dd, J=8.0, 1.1 Hz, 1H), 7.03 (t, J=7.9 Hz, 1H), 6.71 (s, 1H), 5.41 (dd, J=12.6, 5.4 Hz, 1H), 4.44 (s, 2H), 3.65 (s, 3H), 3.36 (t, J=6.2 Hz, 2H), 3.32-3.30 (m, 2H), 3.13 (s, 2H), 2.97 (q, J=6.6 Hz, 2H), 2.94-2.84 (m, 1H), 2.79-2.58 (m, 2H), 2.09-1.99 (m, 1H), 1.59 (p, J=6.5 Hz, 2H), 1.36 (s, 9H), 0.88 (s, 6H); LC/MS (ESI, m/z): [(M–100+1)]$^+$=457.4.

Step 2—3-(4-[3-[3-(3-Aminopropoxy)-2,2-dimethylpropoxy]propyl]-3-methyl-2-oxo-2,3-dihydro-1H-1,3-benzodiazol-1-yl)piperidine-2,6-dione hydrochloride To a solution of tert-butyl N-[3-[3-([3-[1-(2,6-dioxopiperidin-3-yl)-3-methyl-2-oxo-2,3-dihydro-1H-1,3-benzodiazol-4-yl]prop-2-yn-1-yl]oxy)-2,2-dimethylpropoxy]propyl]carbamate (800 mg, 1.44 mmol) in THF (15 mL) was added palladium on charcoal (152.9 mg, 10% w/w) in a pressure tank. The mixture was purged with hydrogen gas 3 times at rt and the mixture was hydrogenated at rt under 1 psi for 16 h. After filtration, the filter cake was concentrated under reduced pressure. The residue was dissolved in dioxane (8 mL). To it was added a solution of HCl in 1,4-dioxane (4 M, 8 mL) dropwise at rt under nitrogen atmosphere. The resulting solution was stirred for 2 hours at rt under nitrogen atmosphere. The resulting solution was concentrated under reduced pressure. The residue was purified by reverse phase flash chromatography with the following conditions: Column: WelFlash™ C18-I, 20-40 μm, 80 g; Eluent A: Water (plus 10 mmol/L FA); Eluent B: ACN; Gradient: 45%-70% B in 25 min; Flow rate: 50 mL/min; Detector: 220/254 nm; desired fractions were collected at 63% B and concentrated under reduced pressure to afford 3-(4-[3-[3-(3-aminopropoxy)-2,2-dimethylpropoxy]propyl]-3-methyl-2-oxo-2,3-dihydro-1H-1,3-benzodiazol-1-yl)piperidine-2,6-dione hydrochloride (72.8 mg, 10%) as a light yellow solid: $^1$H NMR (400 MHz, CDCl$_3$) δ 8.51 (br s, 1H), 7.48 (br s, 3H), 6.99 (t, J=7.8 Hz, 1H), 6.90 (d, J=7.8 Hz, 1H), 6.74 (d, J=7.8 Hz, 1H), 5.22 (dd, J=12.4, 5.5 Hz, 1H), 3.69 (s, 3H), 3.51-3.38 (m, 4H), 3.20-3.08 (m, 4H), 3.06-2.93 (m, 4H), 2.89-2.66 (m, 3H), 2.22-2.13 (m, 1H), 1.99-1.83 (m, 4H), 0.87 (s, 6H); LC/MS (ESI, m/z): [(M+1)]$^+$=461.35.

3-[5-[3-[3-(3-aminopropoxy)-2,2-dimethyl-propoxy]propyl]-3-methyl-2-oxo-benzimidazol-1-yl]piperidine-2,6-dione (Intermediate MA)

perature under nitrogen atmosphere. The mixture was purged with nitrogen gas 3 times, and the resulting mixture was stirred for 5 h at 90° C. under nitrogen atmosphere. After cooling to rt, the mixture was purified by reverse phase flash chromatography with the following conditions: Column: WelFlash™ C18-I, 20-40 μm, 300 g; Eluent A: Water (plus 10 mmol/L FA); Eluent B: ACN; Gradient: 48%-68% B in 20 min; Flow rate: 80 mL/min; Detector: 220/254 nm; desired fractions were collected at 60% B and concentrated under reduced pressure to afford tert-butyl N-[3-[3-([3-[1-(2,6-dioxopiperidin-3-yl)-3-methyl-2-oxo-2,3-dihydro-1H-1,3-benzodiazol-5-yl]prop-2-yn-1-yl]oxy)-2,2-dimethylpropoxy]propyl]carbamate (600 mg, 22%) as a light brown solid. $^1$H NMR (400 MHz, DMSO-d$_6$) δ 11.12 (br s, 1H), 7.32 (d, J=1.4 Hz, 1H), 7.22-7.07 (m, 2H), 6.84-6.64 (m, 1H), 5.40 (dd, J=12.8, 5.4 Hz, 1H), 4.37 (s, 2H), 3.40-3.32 (m, 5H), 3.29 (s, 2H), 3.13 (s, 2H), 2.98 (q, J=6.6 Hz, 2H), 2.95-2.83 (m, 1H), 2.76-2.59 (m, 2H), 2.04 (ddd, J=10.8, 6.0, 3.9 Hz, 1H), 1.61 (t, J=6.7 Hz, 2H), 1.37 (s, 9H), 0.88 (s, 6H); LC/MS (ESI, m/z): [(M+1)]$^+$=557.25.

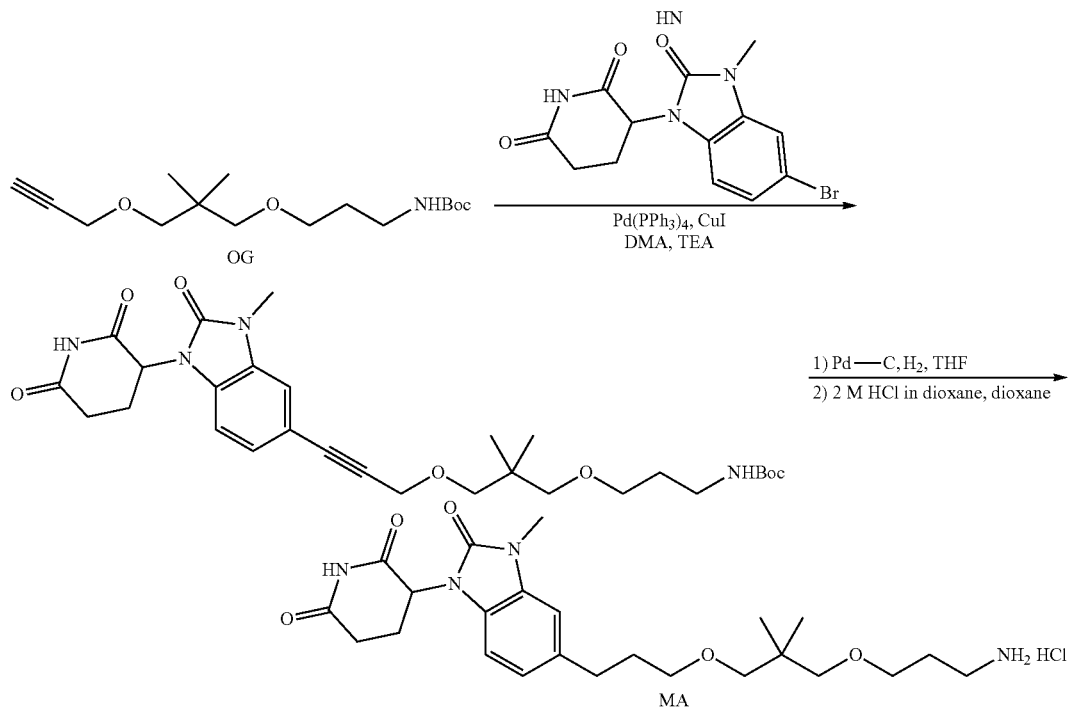

Step 1—Tert-butyl N-[3-[3-([3-[1-(2,6-dioxopiperidin-3-yl)-3-methyl-2-oxo-2,3-dihydro-1H-1,3-benzodiazol-5-yl]prop-2-yn-1-yl]oxy)-2,2-dimethylpropoxy]propyl]carbamate To a stirred solution of 3-(5-bromo-3-methyl-2-oxo-2,3-dihydro-1H-1,3-benzodiazol-1-yl)piperidine-2,6-dione (1.68 g, 4.97 mmol, Intermediate HN) and tert-butyl N-[3-[2,2-dimethyl-3-(prop-2-yn-1-yloxy)propoxy]propyl]carbamate (996.6 mg, 3.33 mmol, Intermediate OG) in DMA (15 mL) were added CuI (94.6 mg, 0.50 mmol), TEA (10 mL) and Pd(PPh$_3$)$_4$ (574.1 mg, 0.50 mmol) at room tem- Step 2—3-(5-[3-[3-(3-Aminopropoxy)-2,2-dimethylpropoxy]propyl]-3-methyl-2-oxo-2,3-dihydro-1H-1,3-benzodiazol-1-yl)piperidine-2,6-dione hydrochloride To a solution of tert-butyl N-[3-[3-([3-[1-(2,6-dioxopiperidin-3-yl)-3-methyl-2-oxo-2,3-dihydro-1H-1,3-benzodiazol-5-yl]prop-2-yn-1-yl]oxy)-2,2-dimethylpropoxy]propyl]carbamate (600 mg, 1.08 mmol) in THF (10 mL) was added palladium on charcoal (114.7 mg, 10% w/w) in a pressure tank. The mixture was purged with hydrogen gas 3 times and was hydrogenated at rt under 1 psi of hydrogen for 16 h. After filtration, the filtrate was concentrated under reduced pressure. The residue was dissolved in dioxane (5 mL). To it was added a solution of HCl in 1,4-dioxane (4 M, 5 mL) dropwise at rt under nitrogen atmosphere. The resulting solution was stirred for 2 hours at rt under nitrogen atmosphere, then was concentrated under reduced pressure. The residue was purified by reverse phase flash chromatography with the following conditions: Column: WelFlash™ C18-I, 20-40 μm, 80 g; Eluent A: Water (plus 10 mmol/L FA); Eluent B: ACN; Gradient: 45%-70% B in 25 min; Flow rate: 50 mL/min; Detector: 220/254 nm; desired fractions were collected at 63% B and concentrated under reduced pressure to afford 3-(5-[3-[3-(3-aminopropoxy)-2,2-dimethylpropoxy]propyl]-3-methyl-2-oxo-2,3-dihydro-1H-1,3-benzodiazol-1-yl)piperidine-2,6-dione hydrochloride (58.1 mg, 10%) as a light yellow solid. $^1$H NMR (400 MHz, CDCl$_3$) δ 8.47 (s, 1H), 8.21 (br, 3H), 6.96-6.76 (m, 3H), 5.28 (dd, J=12.7, 5.4 Hz, 1H), 3.47-3.39 (m, 5H), 3.39-3.32 (m, 2H), 3.19-3.08 (m, 4H), 2.96 (t, J=6.9 Hz, 2H), 2.88-2.79 (m, 2H), 2.72 (q, J=11.8, 9.5 Hz, 3H), 2.22-2.12 (m, 1H), 1.87 (q, J=6.4, 5.6 Hz, 4H), 0.87 (s, 3H), 0.86 (s, 3H); LC/MS (ESI, m/z): [(M+1)]$^+$=461.40.

N-[3-carbamoyl-1-(4-formylphenyl)pyrazol-4-yl]oxazole-4-carboxamide (Intermediate MB)

mixture was stirred at rt for 0.5 hour. On completion, the mixture was diluted with H$_2$O (15 mL), the mixture was filtered and the solid was dried in vacuo to give the title compound (270 mg, 75% yield) as white solid. LC-MS (ESI+) m/z 350.2 (M+Na)$^+$.

Step 2—N-[3-carbamoyl-1-(4-formylphenyl)pyrazol-4-yl]oxazole-4-carboxamide

To a solution of N-[3-carbamoyl-1-[4-(hydroxymethyl)phenyl]pyrazol-4-yl]oxazole-4-carboxamide (270 mg, 824 umol) in DCM (30 mL) was added DMP (419 mg, 989 umol). The mixture was stirred at rt for 2 hours. On completion, the mixture was quenched with saturated aq. Na$_2$S$_2$O$_3$ (30 mL) and washed with saturated aq. NaHCO$_3$ (2×30 mL). The organic layer was dried over anhydrous Na$_2$SO$_4$, filtered and concentrated in vacuo to give the title compound (100 mg, 40% yield) as yellow solid. LC-MS (ESI$^+$) m/z 326.1 (M+H)$^+$.

1-Methyl-4-[[2-[2-(2,2,2-trifluoroethylamino)-4-pyridyl]oxazole-4-carbonyl]amino]pyrazole-3-carboxylic acid (Intermediate MC)

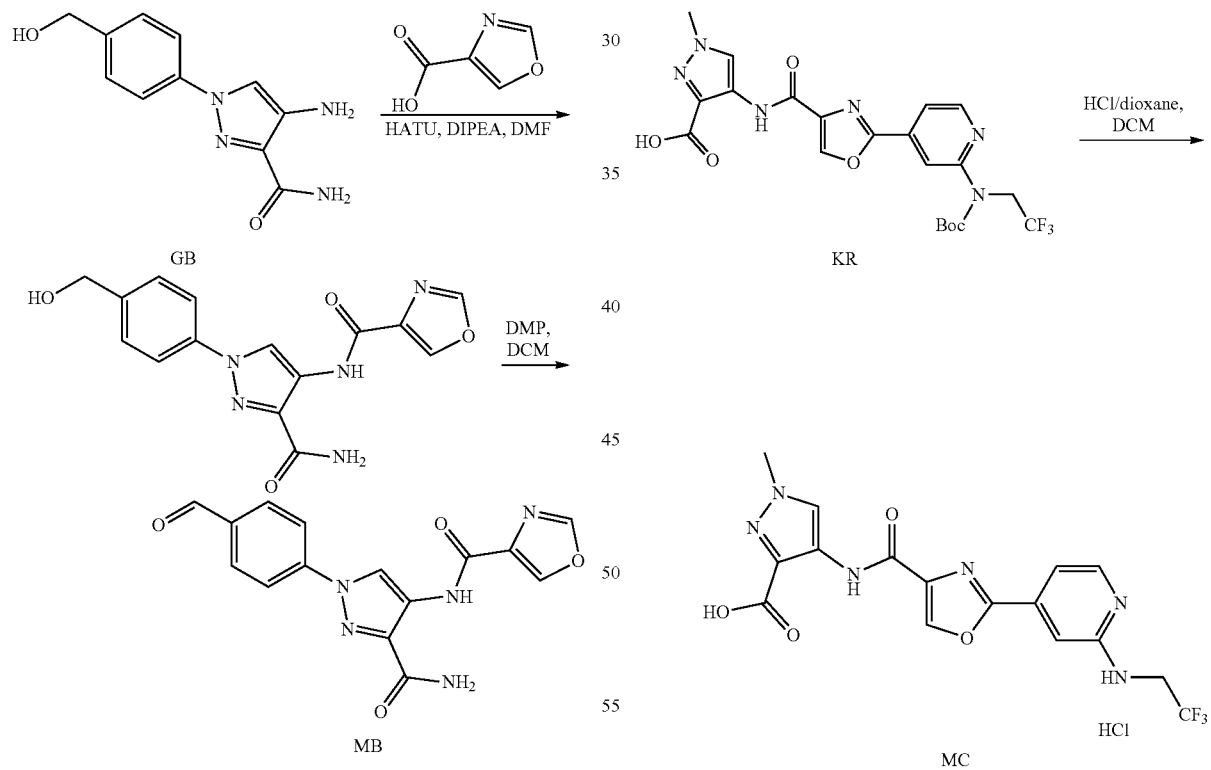

Step 1—N-[3-carbamoyl-1-[4-(hydroxymethyl)phenyl]pyrazol-4-yl]oxazole-4-carboxamide To a solution of 4-amino-1-[4-(hydroxymethyl)phenyl]pyrazole-3-carboxamide (200 mg, 861 umol, Intermediate GB) and oxazole-4-carboxylic acid (97.3 mg, 861 umol, CAS #23012-13-7) in DMF (3 mL) was added DIPEA (333 mg, 2.58 mmol) and HATU (392 mg, 1.03 mmol). The To a solution of 4-[[2-[2-[tert-butoxycarbonyl(2,2,2-trifluoroethyl)amino]-4-pyridyl]oxazole-4-carbonyl]amino]-1-methyl-pyrazole-3-carboxylic acid (35 mg, 68.6 umol, Intermediate KR) in DCM (2 mL) was added 4.0 M HCl/dioxane (2 mL). The reaction mixture was stirred at rt for 2 hours. On completion, the mixture was concentrated in vacuo to give the title compound (30 mg, 98% yield, HCl) as a yellow solid. LC-MS (ESI$^+$) m/z 411.5 (M+H)$^+$.

(2S,4R)-1-[(2S)-2-[[2-[2-[2-[2-[2-[2-(2-aminoethoxy)ethoxy]ethoxy]ethoxy]ethoxy]ethoxy]acetyl]amino]-3,3-dimethyl-butanoyl]-4-hydroxy-N-[[4-(4-methylthiazol-5-yl)phenyl]methyl]pyrrolidine-2-carboxamide (Intermediate MD)

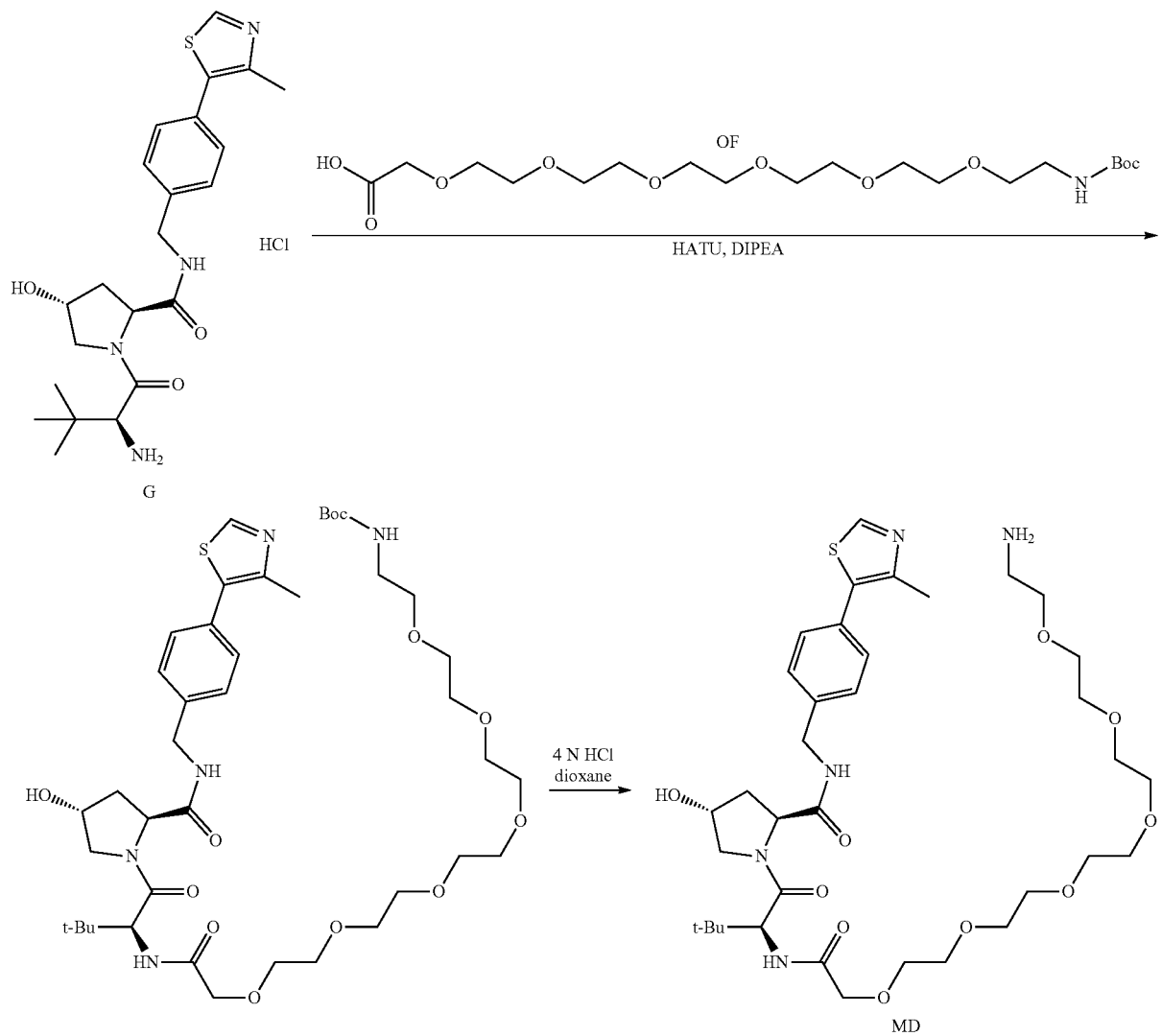

Step 1—tert-butyl ((S)-22-((2S,4R)-4-hydroxy-2-((4-(4-methylthiazol-5-yl)benzyl)carbamoyl)pyrrolidine-1-carbonyl)-23,23-dimethyl-20-oxo-3,6,9,12,15,18-hexaoxa-21-azatetracosyl)carbamate To a solution of (2S,4R)-1-((S)-2-amino-3,3-dimethylbutanoyl)-4-hydroxy-N-(4-(4-methylthiazol-5-yl)benzyl)pyrrolidine-2-carboxamide (1.0 g, 2.15 mmol, Intermediate G) in DMF (100 mL) was added 2,2-dimethyl-4-oxo-3,8,11,14,17,20,23-heptaoxa-5-azapentacosan-25-oic acid (1.083 g, 2.47 mmol, Intermediate OF), HATU (939.1 mg, 2.47 mmol), and DIPEA (693.4 mg, 5.4 mmol) at rt. The reaction mixture was stirred rt for 1 h. The reaction mixture was diluted with water, then extracted with EA (100 mL×2). The combined organic layer was washed with brine (50 mL×3), dried over anhydrous $Na_2SO_4$, filtered, and concentrated in vacuo. The residue was purified by column chromatography (DCM/MeOH=0%-10%) to give the desired compound (1.4 g, 76.5%) as a colorless oil. LC-MS (ESI$^+$): m/z 852.6 (M+H)$^+$.

Step 2—(2S,4R)-1-((S)-23-amino-2-(tert-butyl)-4-oxo-6,9,12,15,18,21-hexaoxa-3-azatricosan-1-oyl)-4-hydroxy-N-(4-(4-methylthiazol-5-yl)benzyl)pyrrolidine-2-carboxamide A solution of tert-butyl ((S)-22-((2S,4R)-4-hydroxy-2-((4-(4-methylthiazol-5-yl)benzyl)carbamoyl)pyrrolidine-1-carbonyl)-23,23-dimethyl-20-oxo-3,6,9,12,15,18-hexaoxa-21-azatetracosyl)carbamate (1.4 g, 1.65 mmol) in dioxane (4 N HCl in dioxane, 20 mL) was stirred rt for 2 h. The reaction mixture was concentrated in vacuo and the residue was purified via reverse phase column chromatography ($H_2O$ (0.1% formic acid)/$CH_3CN$=0%-100%) to give the desired FA salt compound (545.1 g, 43.99%) as a colorless oil. $^1$H NMR (400 MHz, DMSO-$d_6$) δ 8.88 (s, 1H), 7.49-7.38 (m, 4H), 4.70 (s, 1H), 4.59-4.48 (m, 3H), 4.36 (dd, J=15.2, 3.4 Hz, 1H), 4.09 (s, 2H), 3.83 (dt, J=11.0, 7.4 Hz, 2H), 3.74 (dd, J=6.4, 3.8 Hz, 2H), 3.72-3.60 (m, 20H), 3.13 (dd, J=6.4, 3.9 Hz, 2H), 2.47 (s, 3H), 2.30-2.20 (m, 1H), 2.09 (ddd, J=13.3, 9.2, 4.4 Hz, 1H), 1.05 (s, 9H). LC-MS (ESI$^+$): m/z 752.4 (M+H)$^+$.

(2S,4R)-1-[(2S)-2-[[2-[2-[2-[2-(2-aminoethoxy)ethoxy]ethoxy]ethoxy]acetyl]amino]-3,3-dimethyl-butanoyl]-4-hydroxy-N-[[4-(4-methylthiazol-5-yl)phenyl]methyl]pyrrolidine-2-carboxamide (Intermediate ME)

(2S,4R)-1-[(2S)-2-[[2-[2-[2-[2-(2-aminoethoxy)ethoxy]ethoxy]ethoxy]acetyl]amino]-3,3-dimethyl-butanoyl]-4-hydroxy-N-[[4-(4-methylthiazol-5-yl)phenyl]methyl]pyrrolidine-2-carboxamide was synthesized as described for Intermediate MD, using 2,2-dimethyl-4-oxo-3,8,11,14,17-pentaoxa-5-azanonadecan-19-oic acid (Intermediate EN) as the acid which coupled with Intermediate G in the first step. $^1$H NMR (400 MHz, DMSO-d$_6$) δ 8.99 (s, 1H), 8.61-8.58 (t, J=6.0 Hz, 1H), 7.79 (s, 3H), 7.51-7.38 (m, 5H), 4.58-4.55 (d, J=9.6 Hz, 1H), 4.45-4.23 (m, 4H), 3.98 (s, 2H), 3.69-3.51 (m, 16H), 2.99-2.95 (m, 2H), 2.44 (s, 3H), 2.09-2.04 (m, 1H), 1.93-1.87 (m, 1H), 0.95 (s, 9H). LC-MS (ESI$^+$): m/z 664.2 (M+H)$^+$.

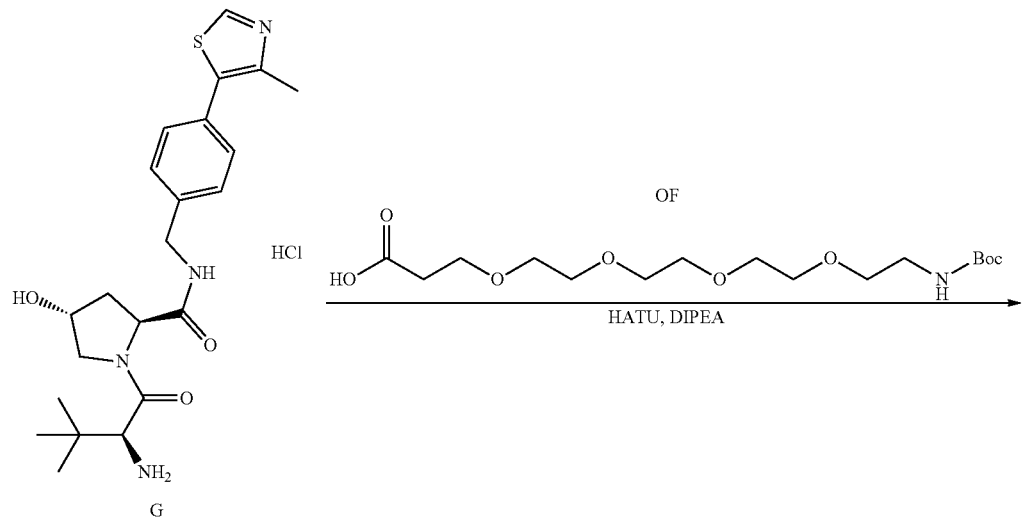

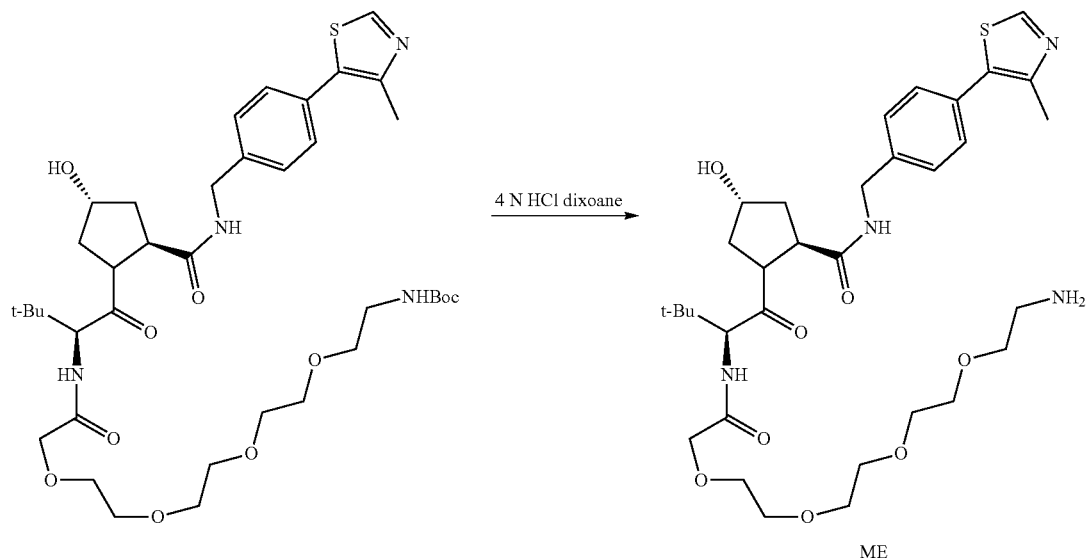

1599
1-Methyl-4-(oxazole-4-carbonylamino)pyrazole-3-carboxylic acid (Intermediate MF)

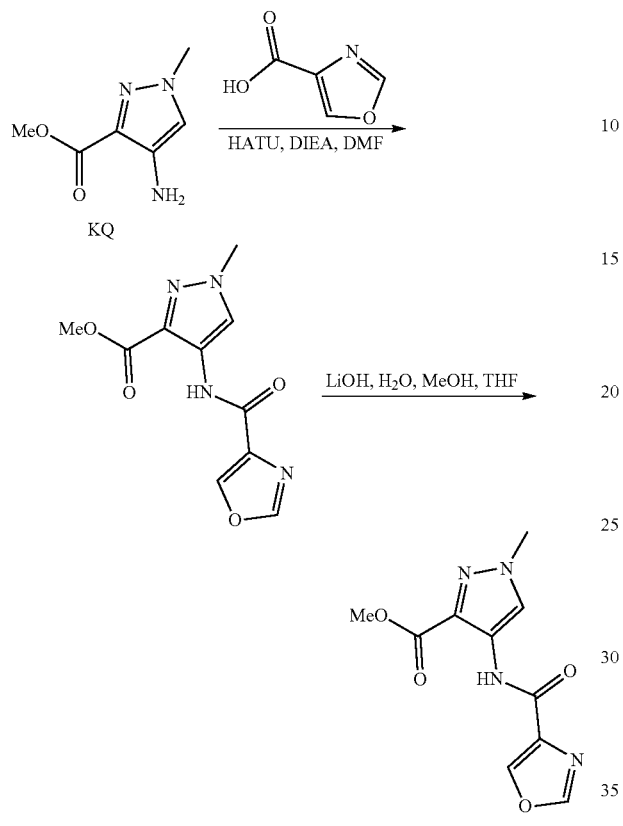

Step 1—Methyl 1-methyl-4-(oxazole-4-carbonylamino)pyrazole-3-carboxylate

To a solution of methyl 4-amino-1-methyl-pyrazole-3-carboxylate (100 mg, 645 umol, Intermediate KQ) and oxazole-4-carboxylic acid (72.9 mg, 645 umol, CAS #23012-13-7) in DMF (2 mL) was added DIPEA (333 mg, 2.58 mmol) and HATU (294 mg, 773 umol). The reaction mixture was stirred at rt for 0.5 hour. On completion, the mixture was quenched with water (30 mL), filtered and the filter cake was dried in vacuo to give the title compound (100 mg, 62% yield) as a white solid. LC-MS (ESI$^+$) m/z 251.2 (M+H)$^+$.

Step 2—1-Methyl-4-(oxazole-4-carbonylamino)pyrazole-3-carboxylic acid

To a solution of methyl 1-methyl-4-(oxazole-4-carbonylamino) pyrazole-3-carboxylate (100 mg, 400 umol) in a mixed solvent of THF (2 mL), MeOH (1 mL) and H$_2$O (0.4 mL) was added LiOH (47.9 mg, 2.00 mmol). The reaction mixture was stirred at rt for 12 hours. On completion, the mixture was acidified with 1N aq.HCl to pH=4-6, then stirred and filtered. The filter cake was dried in vacuo to give the title compound (50 mg, 53% yield) as a white solid. LC-MS (ESI$^+$) m/z 237.1 (M+H)$^+$.

1600
3-[4-(3-Aminopropyl)-3-methyl-2-oxo-benzimidazol-1-yl]piperidine-2,6-dione (Intermediate MG)

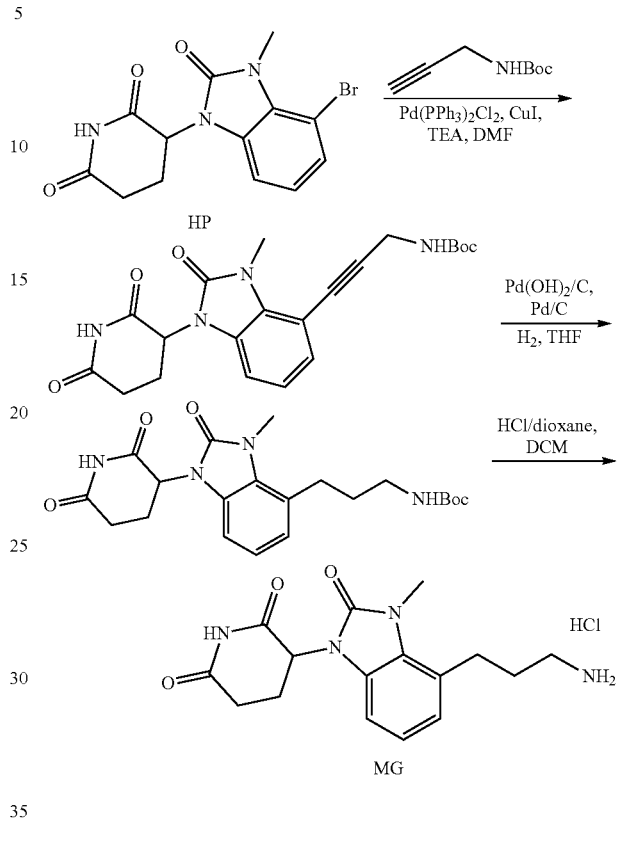

Step 1—Tert-butyl N-[3-[1-(2,6-dioxo-3-piperidyl)-3-methyl-2-oxo-benzimidazol-4-yl]prop-2-ynyl]carbamate To a mixture of 3-(4-bromo-3-methyl-2-oxo-benzimidazol-1-yl)piperidine-2,6-dione (150 mg, 444 umol, Intermediate HP), tert-butyl N-prop-2-ynylcarbamate (172 mg, 1.11 mmol) in DMF (2.5 mL) was added TEA (808 mg, 7.98 mmol), CuI (25.3 mg, 133 umol), Pd(PPh$_3$)$_2$Cl$_2$ (93.4 mg, 133 umol) under N$_2$. The reaction mixture was stirred at 80° C. for 12 hrs. On completion, the reaction mixture was poured into water (10 mL). The aqueous phase was then extracted with ethyl acetate (2×20 mL). The combined organic phase was washed with brine (2×25 mL), dried with anhydrous Na$_2$SO$_4$, filtered and concentrated in vacuo. The residue was purified by column chromatography (SiO$_2$, Petroleum ether/Ethyl acetate=3:1) to give the title compound (96 mg, 52% yield) as brown oil. LC-MS (ESI$^+$) m/z 357.2 (M-55)$^+$.

Step 2-Tert-butyl N-[3-[1-(2,6-dioxo-3-piperidyl)-3-methyl-2-oxo-benzimidazol-4-yl]propyl]carbamate To a solution of tert-butyl N-[3-[1-(2,6-dioxo-3-piperidyl)-3-methyl-2-oxo-benzimidazol-4-yl]prop-2-ynyl]carbamate (112 mg, 272 umol) in THF (5 mL) was added Pd/C (543 umol, 20 wt %) and Pd(OH)$_2$/C (543 umol, 20 wt %) under N$_2$. The suspension was degassed under vacuum and purged with H$_2$ gas 3 times. The mixture was stirred (15 Psi) at rt for 12 hours under H$_2$. On completion, the mixture was filtered and concentrated in vacuo to give the title compound (112 mg, 91% yield) as a white solid. LC-MS (ESI+) m/z 439.3 (M+Na)+

Step 3—3-[4-(3-Aminopropyl)-3-methyl-2-oxo-benzimidazol-1-yl]piperidine-2,6-dione To a solution of tert-butyl N-[3-[1-(2,6-dioxo-3-piperidyl)-3-methyl-2-oxo-benzimidazol-4-yl]propyl]carbamate (112 mg, 269 umol) in DCM (5 mL) was added HCl/dioxane (4 M, 134 uL). The mixture was stirred at rt for 1 hr. On completion, the mixture was concentrated in vacuo to get the title compound (92 mg, 97% yield, HCl) as a white solid. LC-MS (ESI+) m/z 217.2 (M+Na)+.

(S)-7-hydroxy-2-((S)-2-(2-methoxyacetamido)-3,3-dimethylbutanoyl)-N—((R)-1,2,3,4-tetrahydronaphthalen-1-yl)-1,2,3,4-tetrahydroisoquinoline-3-carboxamide (Intermediate MH)

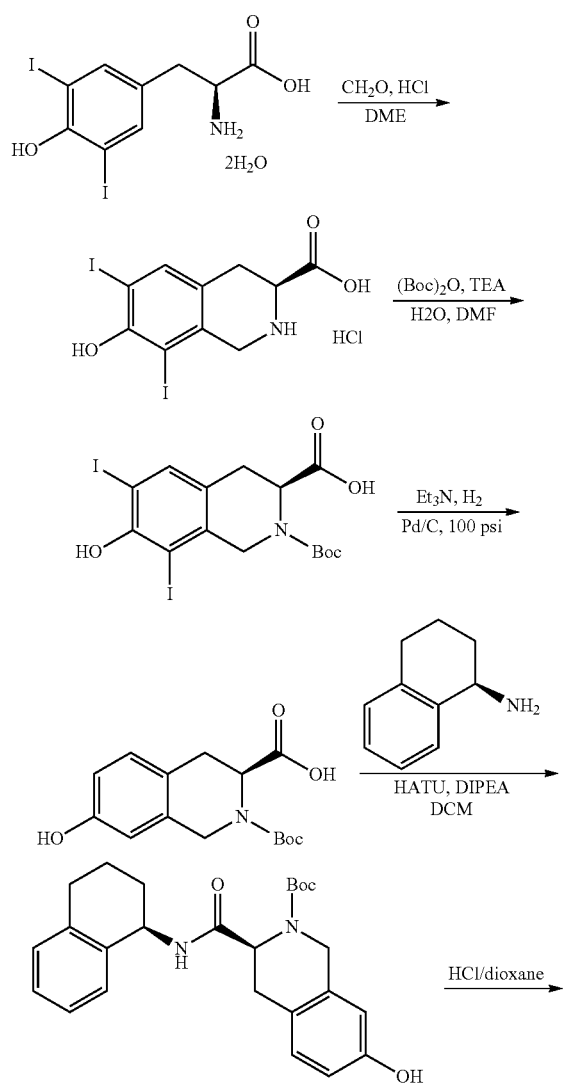

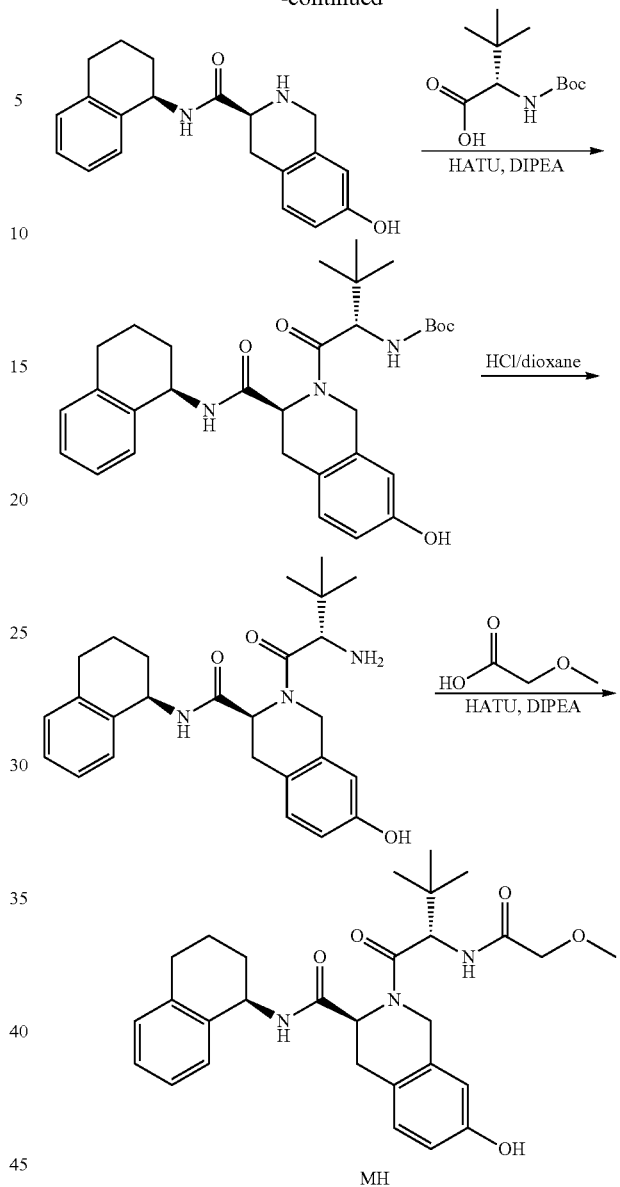

MH

Step 1—(S)-7-hydroxy-6,8-diiodo-1,2,3,4-tetrahydroisoquinoline-3-carboxylic acid hydrochloride To concentrate HCl (780 mL) was added (S)-2-amino-3-(4-hydroxy-3,5-diiodophenyl)propanoic acid (65 g, 150 mmol, CAS #18835-59-1), CH$_2$O (37% in H$_2$O) and DME (65 mL). The mixture was heated to 72° C. slowly, and then stirred overnight. To the mixture was added another 20 mL of CH$_2$O (37% in H$_2$O), and the reaction was stirred for another 4 h at 72° C. The mixture was cooled to 0° C. and filtered. The filter cake was washed with DME (50 mL) give (S)-7-hydroxy-6,8-diiodo-1,2,3,4-tetrahydroisoquinoline-3-carboxylic acid hydrochloride HCl salt (32 g, 72% yield) as a yellow solid. $^1$H NMR (400 MHz, DMSO-d$_6$) δ 9.89 (s, 1H), 9.69 (s, 1H), 7.73 (s, 1H), 4.34-4.30 (dd, J=4.8 Hz, J=11.2 Hz, 1H), 4.14-4.00 (dd, J=16.4 Hz, J=40 Hz, 2H), 3.24-3.18 (m, 1H), 3.09-3.02 (m, 1H). LC-MS (ESI+): m/z 482.5 (M+H)+.

Step 2—(S)-2-(tert-butoxycarbonyl)-7-hydroxy-6,8-diiodo-1,2,3,4-tetrahydroisoquinoline-3-carboxylic acid A mixture of (S)-7-hydroxy-6,8-diiodo-1,2,3,4-tetrahydroisoquinoline-3-carboxylic acid hydrochloride (20 g, 41.6 mmol), (Boc)$_2$O (13.6 g, 62.4 mmol), TEA (16.8 g, 166 mmol), H$_2$O (40 mL) and DMF (300 mL) was stirred overnight at rt. To the mixture was added H$_2$O (200 mL), and the solution was washed with EA (200 mL). The aqueous layer adjusted with 1 N HCl to pH<7, then extracted with EA (300 mL). The organic layer was washed with brine (100 mL), dried over Na$_2$SO$_4$, filtered, concentrated, and purified by column to give (S)-2-(tert-butoxycarbonyl)-7-hydroxy-6,8-diiodo-1,2,3,4-tetrahydroisoquinoline-3-carboxylic acid (15.5 g, 68% yield) as a yellow solid. $^1$H NMR (400 MHz, DMSO-d$_6$) δ 12.77 (s, 1H), 9.46 (s, 1H), 7.64 (s, 1H), 4.83-4.67 (m, 1H), 4.49-4.39 (m, 1H), 4.21-4.17 (d, J=16.8 Hz, 1H), 3.05-3.04 (d, J=4 Hz, 2H), 1.47-1.40 (d, J=24.4 Hz, 9H).

Step 3: (S)-2-(tert-butoxycarbonyl)-7-hydroxy-1,2,3,4-tetrahydroisoquinoline-3-carboxylic acid A mixture of (S)-2-(tert-butoxycarbonyl)-7-hydroxy-6,8-diiodo-1,2,3,4-tetrahydroisoquinoline-3-carboxylic acid (7 g, 12.8 mmol), Pd/C (10 wt %, 1.4 g), TEA (2.9 g, 28.3 mmol) and MeOH (100 mL) was stirred for overnight at rt under N$_2$. The mixture was filtered to remove Pd/C, concentrated to dry, then H$_2$O (100 mL) was added and the mixture was washed with EA (100 mL). The aqueous layer was adjusted with 1N HCl to pH<7, then extracted with EA (300 mL). The organic layer was dried over Na$_2$SO$_4$, filtered and concentrated to give (S)-2-(tert-butoxycarbonyl)-7-hydroxy-1,2,3,4-tetrahydroisoquinoline-3-carboxylic acid (3 g, 80% yield) as a yellow solid. $^1$H NMR (400 MHz, DMSO-d$_6$) δ 12.58 (s, 1H), 9.26 (s, 1H), 6.97 (t, J=8.4 Hz, 1H), 6.58-6.52 (m, 2H), 4.83-4.25 (m, 3H), 3.01-2.96 (m, 2H), 1.45-1.39 (d, J=26.4 Hz, 9H). LC-MS (ESI$^+$): m/z 294.4 (M+H)$^+$.

Step 4—(S)-tert-butyl7-hydroxy-3-(((R)-1,2,3,4-tetrahydronaphthalen-1-yl)carbamoyl)-3,4-dihydroisoquinoline-2 (1H)-carboxylate To a mixture of (S)-2-(tert-butoxycarbonyl)-7-hydroxy-1,2,3,4-tetrahydroisoquinoline-3-carboxylic acid (32 g, 109 mmol) and (R)-1,2,3,4-tetrahydronaphthalen-1-amine (19.3 g, 131 mmol, CAS #23357-46-2) in DMF (150 mL) was added HATU (54 g, 142 mmol) and DIPEA (42 g, 328 mmol), and the mixture was stirred at rt for 15 min. The solution was then poured into water (1500 mL) and extracted with EtOAc (200 mL×2). The combined organic layer was washed with brine (500 mL×3), dried over Na$_2$SO$_4$, filtered, concentrated in vacuo and purified via column chromatography (Petroleum ether/EtOAc=4/1) to give the title compound (40.2 g, 86.9% yield) as a white solid. LC-MS (ESI$^+$): m/z 423.1 (M+H)$^+$

Step 5—(S)-7-hydroxy-N—((R)-1,2,3,4-tetrahydronaphthalen-1-yl)-1,2,3,4-tetrahydroisoquino line-3-carboxamide hydrochloride To a mixture of (S)-tert-butyl7-hydroxy-3-(((R)-1,2,3,4-tetrahydronaphthalen-1-yl) carbamoyl)-3,4-dihydroisoqui-noline-2 (1H)-carboxylate (44 g, 104 mmol) in THF (300 mL) was added 4N HCl in dioxane (300 mL), and the mixture was stirred at rt overnight. The solution was concentrated under reduced pressure to give the crude product, which was recrystallized by EA to give the title compound (33.3 g, 82.0% yield) as a white solid. LC-MS (ESI$^+$): m/z 323.1 (M+H)$^+$.

Step 6—tert-butyl ((S)-1-((S)-7-hydroxy-3-(((R)-1,2,3,4-tetrahydronaphthalen-1-yl) carbamoyl)-3,4-dihydroisoquinolin-2 (1H)-yl)-3,3-dimethyl-1-oxobutan-2-yl)carbamate To a mixture of (S)-7-hydroxy-N—((R)-1,2,3,4-tetrahydronaphthalen-1-yl)-1,2,3,4-tetrahydroisoquinoline-3-carboxamidehydrochloride (33.3 g, 92.8 mmol) and (S)-2-((tert-butoxy carbonyl)amino)-3,3-dimethylbutanoic acid (22.5, 97.4 mmol, CAS #62963-35-9) in DMF (400 mL) was added HATU (42.3 g, 111.3 mmol) and DIPEA (48 g, 371 mmol), and the mixture was stirred at rt for 1.5 h. The solution was then poured into water (2500 mL) and the mixture was extracted with EtOAc (200 mL×2). The combined organic layer was washed with brine (500 mL×3), dried over Na$_2$SO$_4$, filtered, concentrated in vacuo and purified via column chromatography (Petroleum ether/EtOAc=2/1) to give the title compound (21.5 g, 43.9% yield) as a white solid. LC-MS (ESI$^+$): m/z 536.2 (M+H)$^+$.

Step 7—(S)-2-((S)-2-amino-3,3-dimethylbutanoyl)-7-hydroxy-N—((R)-1,2,3,4-tetrahydronaphthalen-1-yl)-1,2,3,4-tetrahydroisoquinoline-3-carboxamide hydrochloride To a mixture of tert-butyl ((S)-1-((S)-7-hydroxy-3-(((R)-1,2,3,4-tetrahydronaphthalen-1-yl) carbamoyl)-3,4-dihydroisoquinolin-2 (1H)-yl)-3,3-dimethyl-1-oxobutan-2-yl)carbamate (21.5 g, 40 mmol) in THF (200 mL) was added 4N HCl in dioxane (200 mL), and the mixture was stirred at rt overnight. The solution was then poured into aq.NaHCO$_3$ (1000 mL), and the mixture was extracted with EtOAc (200 mL×2). The combined organic layer was washed with brine (500 mL×3), dried over Na$_2$SO$_4$, filtered, and concentrated in vacuo to give the title compound as the HCl salt (17 g, 97% yield) as a white solid. LC-MS (ESI$^+$): m/z 436.1 (M+H)$^+$.

Step 8—(S)-7-hydroxy-2-((S)-2-(2-methoxyacetamido)-3,3-dimethylbutanoyl)-N—((R)-1,2,3,4-tetrahydronaphthalen-1-yl)-1,2,3,4-tetrahydroisoquinoline-3-carboxamide To a mixture of (S)-2-((S)-2-amino-3,3-dimethylbutanoyl)-7-hydroxy-N—((R)-1,2,3,4-tetrahydronaphthalen-1-yl)-1,2,3,4-tetrahydroisoquinoline-3-carboxamide hydrochloride (14.4 g, 33 mmol) and 2-methoxyacetic acid (2.97 g, 131 mmol) in DMF (120 mL) was added HATU (15 g, 39.6 mmol) and DIPEA (6.4 g, 49.5 mmol), and the mixture was stirred at rt for 1 h. The solution was then poured into water (1500 mL), and the mixture was extracted with EtOAc (200 mL×2). The combined organic layer was washed with brine (500 mL×3), dried over Na$_2$SO$_4$, filtered, concentrated in vacuo and purified via column chromatography (Petroleum ether/EtOAc=1/1) to give the title compound (14 g, 83.8% yield) as a white solid. LC-MS (ESI$^+$): m/z 508.2 (M+H)$^+$.

1-methyl-4-[[2-(4-pyridyl)oxazole-4-carbonyl]amino]pyrazole-3-carboxylic acid (Intermediate MI)

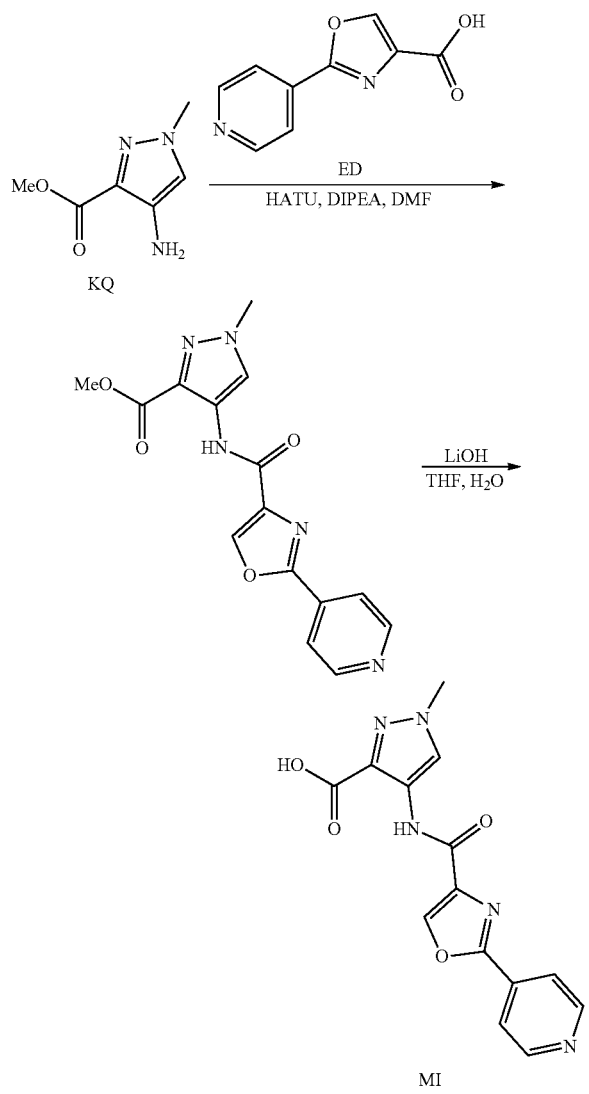

Step 1—Methyl 1-methyl-4-[[2-(4-pyridyl)oxazole-4-carbonyl]amino]pyrazole-3-carboxylate A mixture of methyl 4-amino-1-methyl-pyrazole-3-carboxylate (500 mg, 3.22 mmol, Intermediate KQ), 2-(4-pyridyl)oxazole-4-carboxylic acid (612 mg, 3.22 mmol, Intermediate ED), HATU (1.47 g, 3.87 mmol), and DIPEA (1.25 g, 9.67 mmol) in DMF (10 mL) was degassed and purged with $N_2$ gas 3 times, and then the mixture was stirred at rt for 2 hours under $N_2$ atmosphere. On completion, the mixture was quenched with water (50 mL), filtered and the filter cake was dried in vacuo to give the title compound (900 mg, 85% yield) as white solid. LC-MS (ESI⁺) m/z 328.2 (M+H)⁺.

Step 2—1-methyl-4-[[2-(4-pyridyl)oxazole-4-carbonyl]amino]pyrazole-3-carboxylic acid To a solution of methyl 1-methyl-4-[[2-(4-pyridyl)oxazole-4-carbonyl]amino]pyrazole-3-carboxylate (900 mg, 2.75 mmol) in $H_2O$ (4 mL) and THF (20 mL) was added LiOH (32 mg, 13.7 mmol). The mixture was stirred at rt for 4 hours. On completion, the mixture was adjusted to pH=6 with 1N aq.HCl, filtered and the filter cake was dried in vacuo to give the title compound (600 mg, 69% yield) as white solid. LC-MS (ESI⁺) m/z 314.1 (M+H)⁺.

[4-[(4-Tert-butoxycarbonylmorpholin-2-yl)methoxymethyl]phenyl]boronic acid (Intermediate MJ)

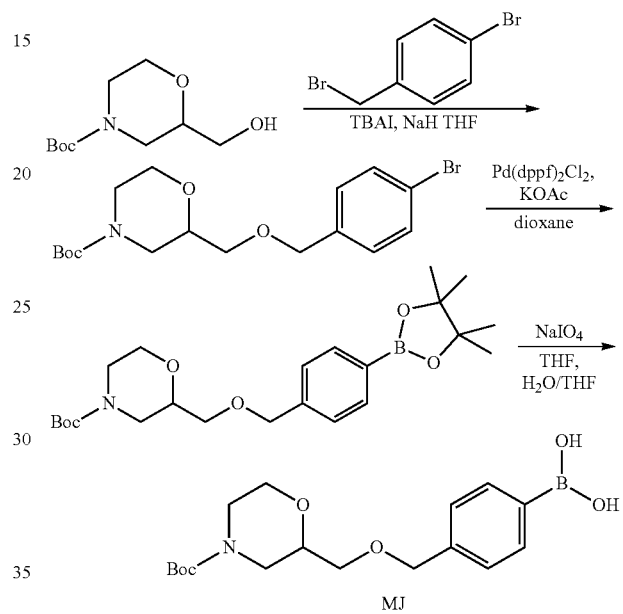

Step 1—Tert-butyl 2-[(4-bromophenyl)methoxymethyl]morpholine-4-carboxylate

To a mixture of 1-bromo-4-(bromomethyl)benzene (10.3 g, 41.4 mmol, CAS #3433-80-5), tert-butyl 2-(hydroxymethyl)morpholine-4-carboxylate (4.50 g, 20.7 mmol, CAS #135065-69-9), TBAI (0.80 g, 2.07 mmol) in DMF (80 mL) was added NaH (1.70 g, 41.4 mmol, 60% oil dispersion) at 0° C. The mixture was then stirred at rt for 12 hrs. On completion, the mixture was concentrated in vacuo. The mixture was poured into a solution of saturated sodium bicarbonate (60 mL) and extracted with ethyl acetate (2×80 mL). The combined organic phase was washed with brine (2×80 mL), dried with anhydrous $Na_2SO_4$, filtered and concentrated in vacuo at 45° C. The residue was purified by silica gel chromatography (petroleum ether:ethyl acetate=20:1) to give the title compound (4.80 g, 61% yield) as a brown oil. ¹H NMR (400 MHz, CDCl₃) δ 7.47 (d, J=8.4 Hz, 2H), 7.23-7.18 (m, 1H), 7.21 (d, J=8.4 Hz, 1H), 4.51 (s, 2H), 3.90 (d, J=10.4 Hz, 3H), 3.64-3.43 (m, 4H), 2.94 (s, 1H), 2.74 (s, 1H), 1.47 (s, 9H).

Step 2—Tert-butyl 2-[[4-(4,4,5,5-tetramethyl-1,3,2-dioxaborolan-2-yl)phenyl]methoxymethyl]morpholine-4-carboxylate To a mixture of tert-butyl 2-[(4-bromophenyl)methoxymethyl]morpholine-4-carboxylate (460 mg, 11.9 mmol), 4,4, 5,5-tetramethyl-2-(4,4,5,5-tetramethyl-1,3,2-dioxaborolan-2-yl)-1,3,2-dioxaborolane (363 mg, 14.3 mmol) in dioxane (50 mL) was added Pd(dppf)Cl2 (972 mg, 1.19 mmol) and KOAc (234 mg, 23.8 mmol). The reaction mixture was stirred at 100° C. for 12 hrs. On completion, the mixture was concentrated in vacuo. The residue was purified by column chromatography to give the title compound (480 mg, 93% yield) as brown oil. $^1$H NMR (400 MHz, CDCl$_3$) δ 7.72 (d, J=7.8 Hz, 2H), 7.26 (d, J=7.8 Hz, 2H), 4.51 (s, 2H), 3.83 (d, J=8.8 Hz, 3H), 3.52-3.36 (m, 4H), 2.86 (s, 1H), 2.66 (t, J=12.0 Hz, 1H), 1.39 (s, 9H), 1.27 (s, 12H).

Step 3—[4-[(4-Tert-butoxycarbonylmorpholin-2-yl)methoxymethyl]phenyl]boronic acid To a mixture of tert-butyl 2-[[4-(4,4,5,5-tetramethyl-1,3,2-dioxaborolan-2-yl)phenyl]methoxymethyl]morpholine-4-carboxylate (4.80 g, 11.1 mmol) in THF (40 mL) and H$_2$O (8 mL) was added NaIO$_4$ (7.10 g, 33.3 mmol). After that, to the reaction mixture was added 4M HCl (7.4 mL) and the mixture was stirred at rt for 12 hrs. On completion, the mixture was concentrated in vacuo. The residue was purified by column chromatography to give the title compound (1.50 g, 38% yield) as brown oil. $^1$H NMR (400 MHz, DMSO-d$_6$) δ 8.02 (s, 2H), 7.77 (d, J=8.0 Hz, 2H), 7.28 (d, J=7.9 Hz, 2H), 4.50 (s, 2H), 3.90-3.74 (m, 2H), 3.73-3.64 (m, 1H), 3.53-3.37 (m, 7H), 1.41 (s, 9H).

Tert-butyl 2-[[4-(4-amino-3-carbamoyl-pyrazol-1-yl)phenyl]methoxymethyl]morpholine-4-carboxylate (Intermediate MK)

Step 1—Tert-butyl 2-[[4-(3-methoxycarbonyl-4-nitro-pyrazol-1-yl)phenyl]methoxymethyl]morpholine-4-carboxylate To a mixture of methyl 4-nitro-1H-pyrazole-3-carboxylate (0.80 g, 4.70 mmol, CAS #170487-38-4), [4-[(4-tert-butoxycarbonylmorpholin-2-yl)methoxymethyl]phenyl]boronic acid (1.50 g, 4.27 mmol, Intermediate MJ) in DCM (20 mL) was added pyridine (1.35 g, 17.1 mmol) and Cu(OAc)$_2$ (1.16 g, 6.41 mmol) under oxygen, and the mixture was stirred at rt for 12 hrs. On completion, the mixture was concentrated in vacuo. The residue was purified by column chromatography to give the title compound (1.10 g, 54% yield) as brown oil. $^1$H NMR (400 MHz, DMSO-d$_6$) δ 9.74 (s, 1H), 7.93 (s, 1H), 7.52 (s, 1H), 7.10 (s, 1H), 6.73 (d, J=8.4 Hz, 1H), 4.60-4.57 (m, 1H), 4.58 (s, 1H), 4.35 (s, 1H), 4.03 (q, J=7.2 Hz, 1H), 3.95 (s, 3H), 3.82 (d, J=8.8 Hz, 2H), 3.70 (d, J=12.4 Hz, 1H), 3.48-3.36 (m, 4H), 1.41 (s, 9H).

Step 2—Tert-butyl 2-[[4-(3-carbamoyl-4-nitro-pyrazol-1-yl)phenyl]methoxymethyl]morpholine-4-carboxylate To a sealed tube was added a solution of tert-butyl 2-[[4-(3-methoxycarbonyl-4-nitro-pyrazol-1-yl)phenyl]methoxymethyl]morpholine-4-carboxylate (1.10 g, 2.31 mmol), NH$_3$.H$_2$O (971 mg, 6.93 mmol, 25% solution) in THF (10 mL). The mixture was stirred at 80° C. for 12 hrs. On completion, the mixture was concentrated in vacuo to give the title compound (840 mg, 79% yield) as brown oil. LC-MS (ESI$^+$) m/z 484.1 (M+Na)$^+$ Step 3—Tert-butyl 2-[[4-(4-amino-3-carbamoyl-pyrazol-1-yl)phenyl]methoxymethyl]morpholine-4-carboxylate To a mixture of tert-butyl 2-[[4-(3-carbamoyl-4-nitro-pyrazol-1-yl)phenyl]Methoxymethyl]morpholine-4-carboxylate (300 mg, 650 umol) in MeOH (3 mL) was added Pd/C (150 mg, 1.30 mmol) under H$_2$ (15 Psi), and the mixture was stirred at rt for 0.2 hr. On completion, the reaction mixture was filtered and concentrated in vacuo to give the title compound (275 mg, 98% yield) as brown oil. LC-MS (ESI$^+$) m/z 454.1 (M+Na)$^+$.

[4-[(1-Tert-butoxycarbonyl-2-piperidyl)methoxymethyl]phenyl]boronic acid (Intermediate ML)

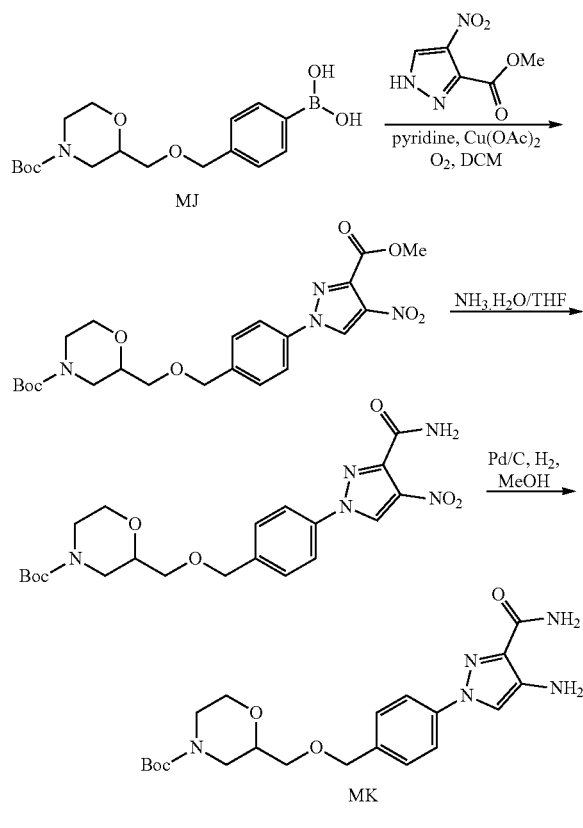

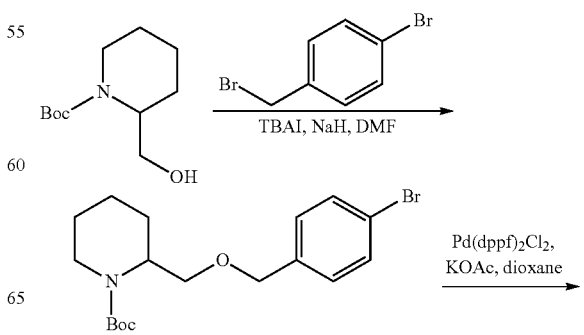

1609

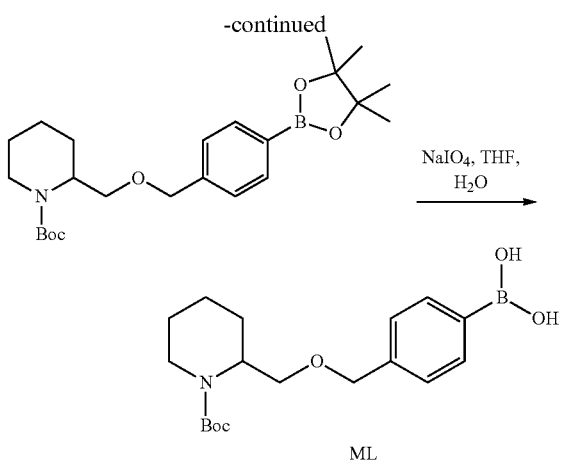

Step 1—Tert-butyl 2-[(4-bromophenyl)methoxymethyl]morpholine-4-carboxylate

To a mixture of 1-bromo-4-(bromomethyl)benzene (1.15 g, 4.60 mmol, CAS #3433-80-5), tert-butyl 2-(hydroxymethyl)morpholine-4-carboxylate (0.50 g, 2.30 mmol, CAS #157634-00-9) and TBAI (85.0 mg, 0.23 mmol) in DMF (10 mL) was added NaH (184 mg, 4.60 mmol, 60% oil dispersion) at 0° C. The mixture was stirred at rt for 12 hrs. On completion, the reaction mixture was concentrated in vacuo. The mixture was poured into a solution of saturated sodium bicarbonate (20 mL) and extracted with ethyl acetate (2×20 mL). The combined organic phase was washed with brine (2×30 mL), dried with anhydrous $Na_2SO_4$, filtered and concentrated in vacuo at 45° C. The residue was purified by silica gel chromatography to give the title compound (554 mg, 62% yield) as brown oil. $^1$H NMR (400 MHz, $CDCl_3$) δ 7.39 (d, J=8.4 Hz, 2H), 7.13 (d, J=8.4 Hz, 2H), 4.43 (s, 2H), 3.96-3.63 (m, 3H), 3.41 (dd, J=4.8, 8.0 Hz, 4H), 2.94-2.59 (m, 2H), 1.39 (s, 9H).

Step 2—Tert-butyl2-[[4-(4,4,5,5-tetramethyl-1,3,2-dioxaborolan-2-yl)phenyl]methoxymethyl]piperidine-1-carboxylate To a mixture of tert-butyl 2-[(4-bromophenyl)methoxymethyl]piperidine-1-carboxylate (5.00 g, 13.0 mmol), 4,4,5,5-tetramethyl-2-(4,4,5,5-tetramethyl-1,3,2-dioxaborolan-2-yl)-1,3,2-dioxaborolane (3.30 g, 13.0 mmol) in dioxane (50 mL) was added dioxane (50 mL) and KOAc (2.55 g, 26.0 mmol) and $Pd(dppf)Cl_2.CH_2Cl_2$ (1.06 g, 1.30 mmol). The reaction mixture was stirred at 100° C. for 12 hrs. On completion, the mixture was concentrated in vacuo. The residue was purified by column chromatography to give the title compound (3.20 g, 57% yield) as brown oil. $^1$H NMR (400 MHz, $CDCl_3$) δ 7.88-7.77 (m, 2H), 7.41-7.33 (m, 2H), 4.65-4.53 (m, 3H), 3.99 (d, J=10.8 Hz, 1H), 3.61-3.52 (m, 1H), 3.63-3.47 (m, 1H), 2.85-2.65 (m, 1H), 1.90-1.72 (m, 1H), 1.88-1.71 (m, 1H), 1.66-1.53 (m, 3H), 1.47 (s, 9H), 1.37 (s, 12H).

Step 3—[4-[(1-Tert-butoxycarbonyl-2-piperidyl)methoxymethyl]phenyl]boronic acid

To a mixture of tert-butyl 2-[[4-(4,4,5,5-tetramethyl-1,3,2-dioxaborolan-2-yl)phenyl]methoxymethyl]piperidine-1-carboxylate (3.20 g, 7.42 mmol) in THF (60 mL) and $H_2O$ (12 mL) was added $NaIO_4$ (4.76 g, 22.2 mmol, 1.2 mL). Then HCl (3 M, 4.95 mL) was added to the mixture. The reaction mixture was stirred at rt for 12 hrs. On completion, the mixture was diluted with $H_2O$ (30 mL), and extracted with EA (3×30 mL). The organic layers were washed with brine (3×20 mL), dried over anhydrous $Na_2SO_4$, filtered and concentrated in vacuo. The residue was purified by column chromatography to give the title compound (1.50 g, 58% yield) as brown oil. $^1$H NMR (400 MHz, DMSO-$d_6$) δ 8.02 (s, 2H), 7.76 (d, J=8.0 Hz, 2H), 7.27 (d, J=8.0 Hz, 2H), 4.58-4.44 (m, 2H), 4.30 (s, 1H), 3.82 (d, J=12.4 Hz, 1H), 3.58-3.47 (m, 2H), 3.35 (s, 3H), 2.79-2.63 (m, 1H), 1.70 (d, J=7.2 Hz, 1H), 1.59-1.41 (m, 4H), 1.37 (s, 9H), 1.32-1.21 (m, 1H).

Tert-butyl 2-[[4-(4-amino-3-carbamoyl-pyrazol-1-yl)phenyl]methoxymethyl]piperidine-1-carboxylate
(Intermediate MM)

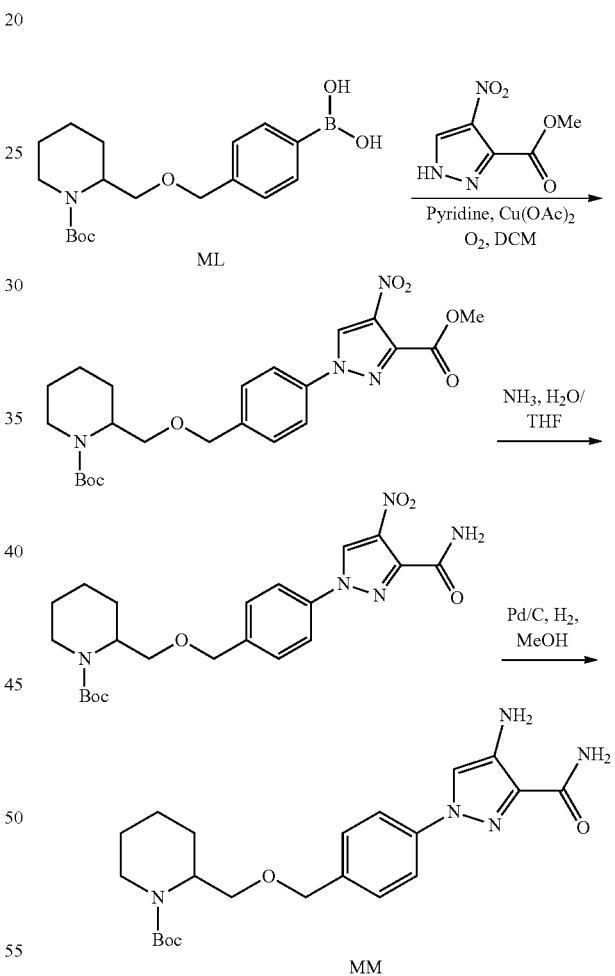

Step 1—Tert-butyl 2-[[4-(3-methoxycarbonyl-4-nitro-pyrazol-1-yl)phenyl]methoxymethyl]piperidine-1-carboxylate To a mixture of [4-[(1-tert-butoxycarbonyl-2-piperidyl)methoxymethyl]phenyl]boronic acid (1.50 g, 4.30 mmol, Intermediate ML), and methyl 4-nitro-1H-pyrazole-3-carboxylate (0.70 g, 4.08 mmol, CAS #170487-38-4) in DCM (20 mL) was added pyridine (1.36 g, 17.2 mmol) and Cu(OAc)$_2$ (1.17 g, 6.44 mmol) under oxygen. The reaction mixture was stirred at rt for 12 hrs. On completion, the mixture was concentrated in vacuo. The residue was purified by column chromatography to give the title compound (1.50 g, 73% yield)) as a brown oil. $^1$H NMR (400 MHz, DMSO-d$_6$) δ 9.75 (s, 1H), 7.94 (d, J=8.8 Hz, 2H), 7.55-7.50 (m, 2H), 4.64-4.51 (m, 2H), 4.41-4.29 (m, 2H), 3.95 (s, 3H), 3.63-3.50 (m, 2H), 3.45 (d, J=7.6 Hz, 1H), 1.61-1.42 (m, 6H), 1.38 (s, 9H).

Step 2—Tert-butyl 2-[[4-(3-carbamoyl-4-nitro-pyrazol-1-yl)phenyl]methoxymethyl]piperidine-1-carboxylate To a sealed tube was added a mixture of tert-butyl 2-[[4-(3-methoxycarbonyl-4-nitro-pyrazol-1-yl)phenyl] methoxymethyl]piperidine-1-carboxylate (1.50 g, 3.16 mmol) in MeOH (10 mL). Then NH$_3$.H$_2$O (1.33 g, 9.48 mmol, 1.46 mL) was added and the mixture was stirred at 80° C. for 12 hrs. On completion, the mixture was concentrated in vacuo to give the title compound (850 mg, 58% yield) as brown oil. LC-MS (ESI$^+$) m/z 482.2 (M+Na)$^+$.

Step 3—Tert-butyl 2-[[4-(4-amino-3-carbamoyl-pyrazol-1-yl)phenyl]methoxymethyl]piperidine-1-carboxylate To a mixture of tert-butyl 2-[[4-(3-carbamoyl-4-nitro-pyrazol-1-yl)phenyl]methoxymethyl]piperidine-1-carboxylate (300 mg, 653 umol) in MeOH (3 mL) was added Pd/C (120 mg, 652.89 umol) under H$_2$ (15 Psi). The mixture was stirred at rt for 0.3 hour. On completion, the reaction mixture was filtered and concentrated in vacuo to give the title compound (265 mg, 94% yield) as brown oil. LC-MS (ESI$^+$) m/z 452.1 (M+Na)$^+$.

4-[3-[2-[2-[2-(2-Aminoethoxy)ethoxy]ethoxy] ethoxy]prop-1-ynyl]-2-(2,6-dioxo-3-piperidyl) isoindoline-1,3-dione (Intermediate MN)

To a mixture of tert-butyl N-[2-[2-[2-[2-[3-[2-(2,6-dioxo-3-piperidyl)-1,3-dioxo-isoindolin-4-yl]prop-2-ynoxy] ethoxy]ethoxy]ethoxy]ethyl]carbamate (300 mg, 510 umol, synthesized via Step 1 of Intermediate HA) in DCM (3 mL) was added HCl/dioxane (4 M, 0.3 mL). The reaction mixture was stirred at rt for 0.5 hr. On completion, the mixture was concentrated in vacuo to give the title compound (245 mg, 91% yield) as a brown solid. LC-MS (ESI$^+$) m/z 488.3 (M+H)$^+$.

2-(2-Methyl-4-pyridyl)oxazole-4-carboxylic acid (Intermediate MO)

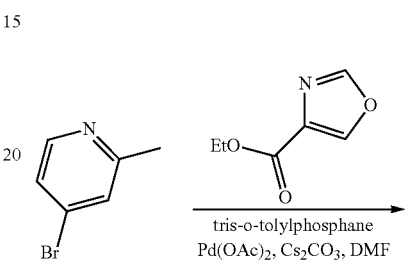

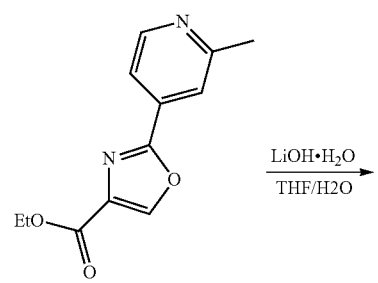

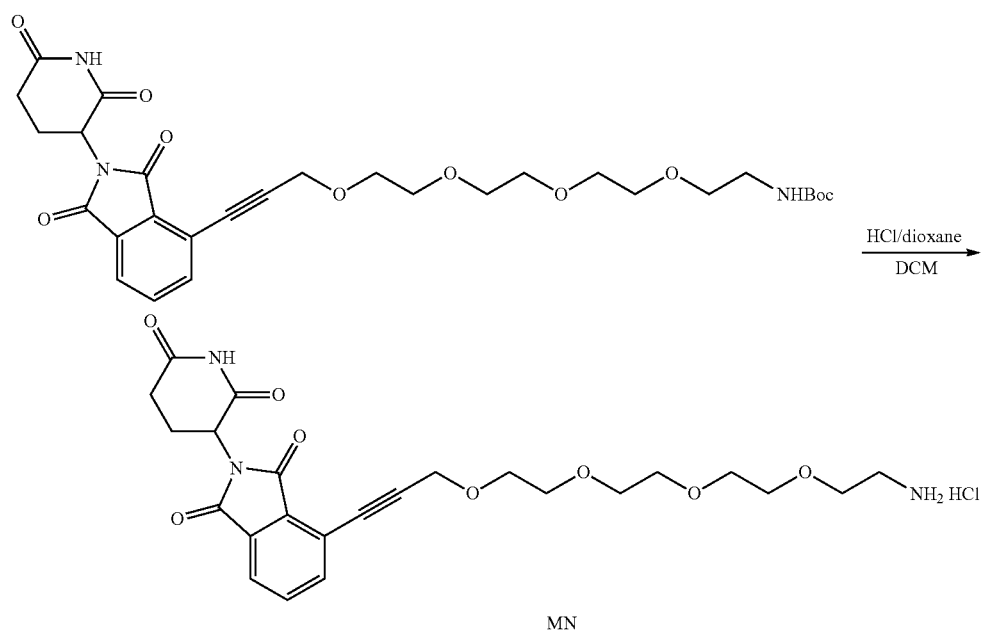

MN

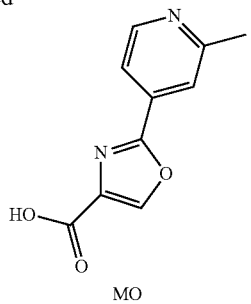

MO

Step 1—Ethyl 2-(2-methylpyridin-4-yl)oxazole-4-carboxylate

To a solution of 4-bromo-2-methyl-pyridine (1.50 g, 8.72 mmol, from CAS #22282-99-1) and ethyl oxazole-4-carboxylate (1.23 g, 8.72 mmol, from CAS #170487-38-4) in DMF (40 mL) was added tris-o-tolylphosphane (531 mg, 1.74 mmol), Pd(OAc)$_2$ (196 mg, 872 umol) and Cs$_2$CO$_3$ (5.68 g, 17.4 mmol). The reaction mixture was stirred at 70° C. for 12 hours under nitrogen. On completion, the reaction mixture was filtered and concentrated. The residue was purified by silica gel column chromatography to give the title compound (1.10 g, 44% yield) as a yellow solid. $^1$H NMR (400 MHz, CDCl$_3$) δ 8.65 (d, J=5.2 Hz, 1H), 8.31-8.36 (m, 1H), 7.86 (s, 1H), 7.75 (d, J=5.2 Hz, 1H), 4.44 (q, J=7.2 Hz, 2H), 2.64 (s, 3H), 1.41 (t, J=7.2 Hz, 3H); LC-MS (ESI$^+$) m/z 233.1 (M+H)$^+$.

Step 2—2-(2-Methyl-4-pyridyl)oxazole-4-carboxylic acid

To a solution of ethyl 2-(2-methyl-4-pyridyl)oxazole-4-carboxylate (1.10 g, 4.74 mmol) in THF (20 mL) was added LiOH·H$_2$O (795 mg, 19.0 mmol) in H$_2$O (4 mL). The reaction mixture was stirred at rt for 12 hours. On completion, the reaction mixture was filtered and the filter cake was dissolved in water (20 mL). The solution was acidified to pH=4 and filtered. The filter cake was washed with water (2×5 mL) and dried in vacuo. The residue was purified by prep-HPLC to give the title compound (600 mg, 52% yield) as a white solid.

4-[3-Carbamoyl-4-[[2-(2-methyl-4-pyridyl)oxazole-4-carbonyl]amino]pyrazol-1-yl]benzoic acid (Intermediate MP)

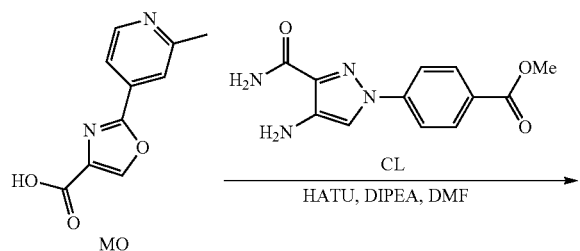

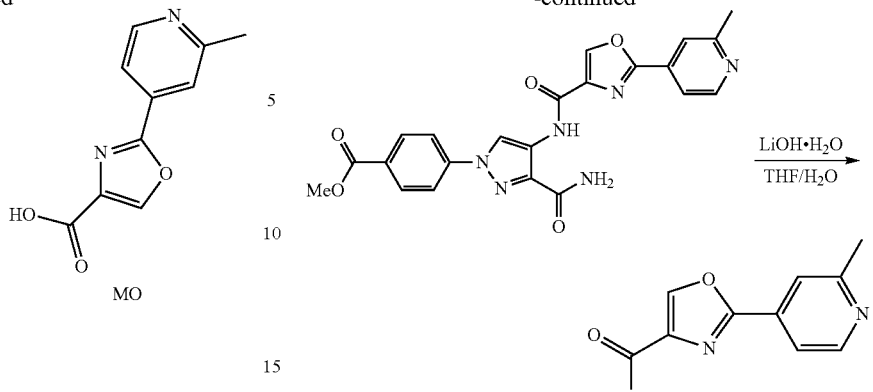

MP

Step 1—Methyl 4-[3-carbamoyl-4-[[2-(2-methyl-4-pyridyl)oxazole-4-carbonyl]amino]pyrazol-1-yl]benzoate To a solution of 2-(2-methyl-4-pyridyl)oxazole-4-carboxylic acid (200 mg, 831.11 umol, HCl, Intermediate MO) and methyl 4-(4-amino-3-carbamoyl-pyrazol-1-yl)benzoate (173 mg, 665 umol, Intermediate CL) in DMF (20 mL) was added DIPEA (322 mg, 2.49 mmol) and HATU (379 mg, 997 umol). The reaction mixture was stirred at rt for 0.5 hour. On completion, the reaction mixture was quenched with water (5 mL) and filtered. The filter cake was washed with water (3×3 mL) and dried in vacuo to give the title compound (200 mg, 53% yield) as a white solid. LC-MS (ESI$^+$) m/z 447.3 (M+H)$^+$.

Step 2—4-[3-Carbamoyl-4-[[2-(2-methyl-4-pyridyl)oxazole-4-carbonyl]amino]pyrazol-1-yl]benzoic acid To a solution of methyl 4-[3-carbamoyl-4-[[2-(2-methyl-4-pyridyl)oxazole-4-carbonyl]amino]pyrazol-1-yl]benzoate (150 mg, 336 umol) in THF (20 mL) and MeOH (4 mL) was added LiOH·H$_2$O (42.3 mg, 1.01 mmol) in H$_2$O (4 mL). The reaction mixture was stirred at rt for 12 hours. On completion, the reaction mixture was poured into HCl (1N, 2 mL) and concentrated in vacuo to give the title compound (200 mg, 100% yield) as a white solid. LC-MS (ESI+) m/z 433.2 (M+H)$^+$.

2-(2-Cyclopropyl-4-pyridyl)oxazole-4-carboxylic acid (Intermediate MQ)

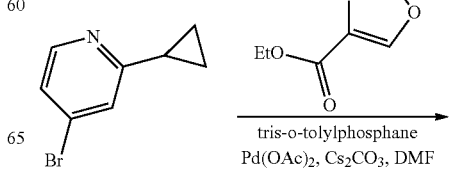

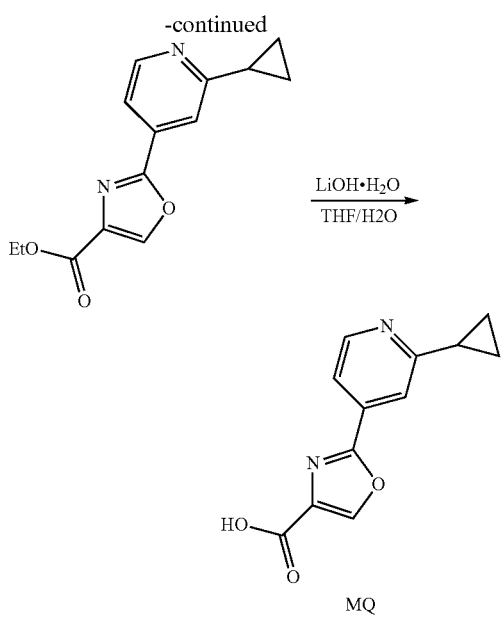

Step 1—Ethyl 2-(2-cyclopropyl-4-pyridyl)oxazole-4-carboxylate

To a solution of 4-bromo-2-cyclopropyl-pyridine (512 mg, 2.59 mmol, CAS #1086381-28-3) and ethyl oxazole-4-carboxylate (365 mg, 2.59 mmol, CAS #170487-38-4) in DMF (5 mL) was added tris-o-tolylphosphane (157 mg, 517 umol), Pd(OAc)$_2$ (58.0 mg, 259 umol) and Cs$_2$CO$_3$ (1.68 g, 5.17 mmol). The reaction mixture was stirred at 70° C. for 12 hours under nitrogen. On completion, the reaction mixture was diluted with EA (100 mL), poured into sat.NH$_4$Cl (50 mL) and extracted with EA (3×50 mL). The combined organic layers were washed with brine (50 mL), dried with anhydrous Na$_2$SO$_4$, filtered and concentrated in vacuo. The residue was purified by silica column chromatography (PE/EA, 10/1 to 5/1) to give the title compound (380 mg, 55% yield) as a white solid. $^1$H NMR (400 MHz, DMSO-d$_6$) δ 8.57 (d, J=4.8 Hz, 1H), 8.33 (s, 1H), 7.82 (s, 1H), 7.67 (dd, J=1.6, 5.2 Hz, 1H), 4.44 (q, J=7.2 Hz, 2H), 2.16-2.07 (m, 1H), 1.42 (t, J=7.2 Hz, 3H), 1.12-1.02 (m, 4H). LC-MS (ESI$^+$) m/z 259.1 (M+H)$^+$.

Step 2—2-(2-Cyclopropyl-4-pyridyl)oxazole-4-carboxylic acid

To a solution of ethyl 2-(2-cyclopropyl-4-pyridyl)oxazole-4-carboxylate (370 mg, 1.43 mmol) in THF (20 mL) was added a solution of LiOH.H$_2$O (150 mg, 3.57 mmol) in H$_2$O (4 mL). The reaction mixture was stirred at rt for 12 hours. On completion, the reaction mixture was quenched with 4 mL of HCl (1N) and concentrated in vacuo to give the title compound (450 mg, 100% yield) as a white solid. LC-MS (ESI$^+$) m/z 231.1 (M+H)$^+$.

2-(2-(2-Aminoethoxy)ethoxy)ethanol (Intermediate MR)

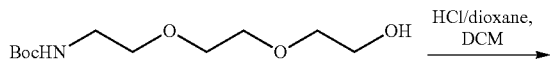

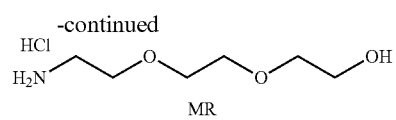

To a solution of tert-butyl N-[2-[2-(2-hydroxyethoxy)ethoxy]ethyl]carbamate (1.60 g, 6.42 mmol, from CAS #139115-92-7) in DCM (10 mL) was added HCl/dioxane (4 M, 1.60 mL). The reaction mixture was stirred at rt for 1 hour. On completion, the reaction mixture was concentrated in vacuo to give the title compound (1.19 g, 100% yield) as colorless oil.

4-[2-[2-(2-Azidoethoxy)ethoxy]ethylamino]-2-(2,6-dioxo-3-piperidyl)isoindoline-1,3-dione (Intermediate MS)

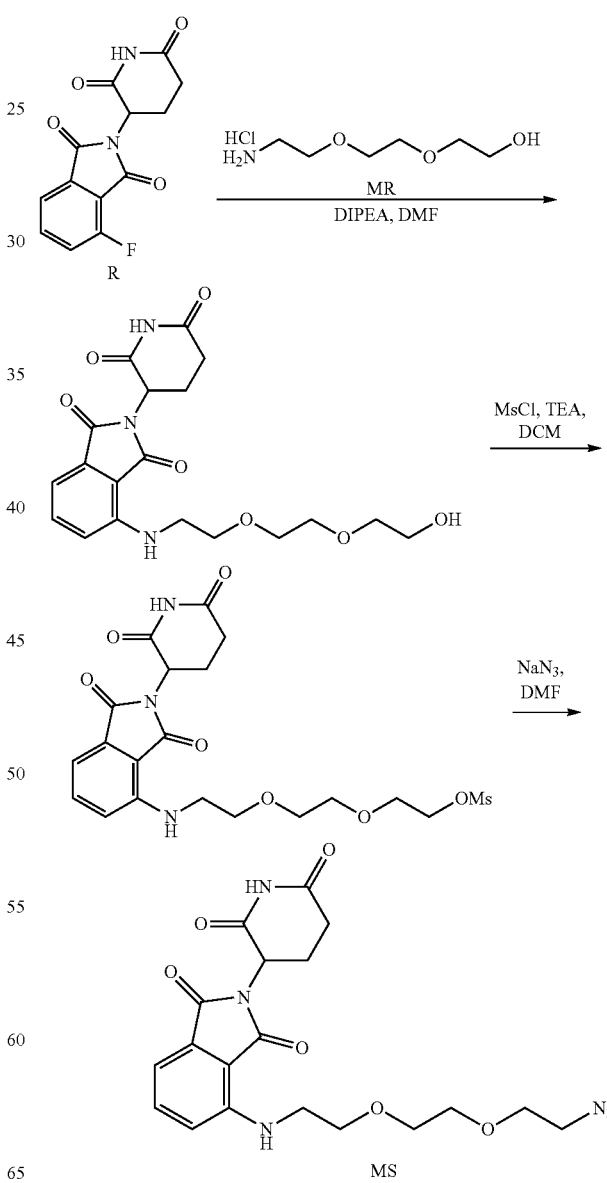

Step 1—2-(2,6-Dioxopiperidin-3-yl)-4-((2-(2-(2-hydroxyethoxy)ethoxy)ethyl)amino)isoindoline-1,3-dione To a solution of 2-(2,6-dioxo-3-piperidyl)-4-fluoro-isoindoline-1,3-dione (1.50 g, 5.43 mmol, Intermediate R) and 2-[2-(2-aminoethoxy)ethoxy]ethanol (1.01 g, 5.43 mmol, HCl, Intermediate MR) in DMF (5 mL) was added DIPEA (2.81 g, 21.7 mmol). The reaction mixture was stirred at 115° C. for 12 hours. On completion, the reaction mixture was poured into sat.NaHCO$_3$ (30 mL) and extracted with EA (3×100 mL). The combined organic layers were washed with brine (100 mL), dried with anhydrous Na$_2$SO$_4$, filtered and concentrated in vacuo. The residue was purified by silica column chromatography (PE/EA, 1/1 to 0/1) to give the title compound (600 mg, 27% yield) as a yellow solid. LC-MS (ESI$^+$) m/z 406.2 (M+H)$^+$.

Step 2—(2-(2-((2-(2,6-dioxopiperidin-3-yl)-1,3-dioxoisoindolin-4-yl)amino)ethoxy)ethoxy)ethyl methanesulfonate To a solution of 2-(2,6-dioxo-3-piperidyl)-4-[2-[2-(2-hydroxyethoxy)ethoxy]ethylamino]isoindoline-1,3-dione (100 mg, 247 umol) in DCM (5 mL) was added TEA (49.9 mg, 493 umol) and MsCl (37.0 mg, 323 umol) at 0° C. The reaction mixture was then stirred at rt for 0.5 hour. On completion, the reaction mixture was concentrated in vacuo to give title compound (130 mg, 100% yield) as a yellow solid. LC-MS (ESI$^+$) m/z 484.2 (M+H)$^+$.

Step 3—4-[2-[2-(2-Azidoethoxy)ethoxy]ethyl amino]-2-(2,6-dioxo-3-piperidyl)isoindoline-1,3-dione To a solution of 2-[2-[2-[[2-(2,6-dioxo-3-piperidyl)-1,3-dioxo-isoindolin-4-yl]amino]ethoxy]ethoxy]ethyl methanesulfonate (60.0 mg, 124 umol) in DMF (3 mL) was added NaN$_3$ (16.1 mg, 248 umol). The reaction mixture was stirred at 65° C. for 2 hours. On completion, the reaction mixture was poured into sat. NaHCO$_3$ (30 mL) and extracted with DCM (2×50 mL). The combined organic layers were washed with brine (50 mL), dried with anhydrous Na$_2$SO$_4$, filtered and concentrated in vacuo to give the title compound (60.0 mg, 100% yield) as a yellow solid. LC-MS (ESI$^+$) m/z 453.2 (M+Na)$^+$.

4-Amino-1-prop-2-ynyl-pyrazole-3-carboxamide (Intermediate MT)

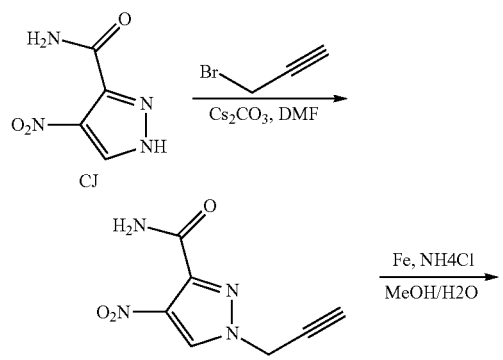

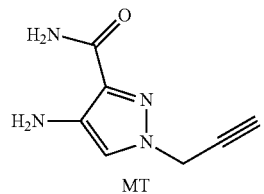

Step 1—4-Nitro-1-(prop-2-yn-1-yl)-1H-pyrazole-3-carboxamide

To a solution of 4-nitro-1H-pyrazole-3-carboxamide (2.00 g, 12.8 mmol, Intermediate CJ) and 3-bromoprop-1-yne (3.05 g, 25.6 mmol, 2.21 mL) in DMF (30 mL) was added K$_2$CO$_3$ (3.54 g, 25.6 mmol). The reaction mixture was stirred at 60° C. for 1 hour. On completion, the reaction mixture was diluted with EA (50 mL) and filtered, then the filtrate was concentrated in vacuo. The residue was purified by silica column chromatography (PE/EA, 1/1 to 0/1) to give the title compound (1.30 g, 52% yield) as an off-white solid. $^1$H NMR (300 MHz, DMSO-d$_6$) δ 8.90 (s, 1H), 8.07 (s, 1H), 7.82 (s, 1H), 5.14 (d, J=2.4 Hz, 2H), 3.67 (t, J=2.4 Hz, 1H), 2.73 (s, 1H).

Step 2—4-Amino-1-prop-2-ynyl-pyrazole-3-carboxamide

To a solution of 4-nitro-1-prop-2-ynyl-pyrazole-3-carboxamide (1.20 g, 6.18 mmol) in MeOH (30 mL) was added a solution of NH$_4$Cl (1.65 g, 30.9 mmol) in H$_2$O (10 mL) and Fe (1.73 g, 30.9 mmol). The reaction mixture was stirred at 80° C. for 12 hours under nitrogen. On completion, the reaction mixture was diluted with DCM (400 mL), stirred at rt for 10 min, then washed with brine (2×50 mL). The organic layer was dried with anhydrous Na$_2$SO$_4$, filtered and concentrated in vacuo to give the title compound (800 mg, 79% yield) as a light yellow solid.

2-(2-Prop-2-ynoxyethoxy)ethanamine (Intermediate MU)

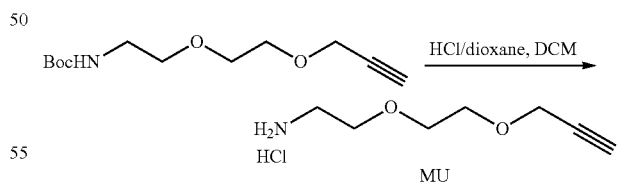

To a mixture of tert-butyl N-[2-(2-prop-2-ynoxyethoxy)ethyl]carbamate (2.50 g, 10.3 mmol, synthesized via Step 1 of Intermediate CQ) in DCM (20 mL) was added HCl/dioxane (4 M, 5.14 mL) and the reaction was stirred at rt for 0.5 hr. On completion, the mixture was concentrated in vacuo to give the title compound (1.80 g, 97% yield, HCl) as a brown solid. $^1$H NMR (400 MHz, DMSO-d$_6$) δ 8.27 (s, 2H), 4.14 (d, J=2.4 Hz, 2H), 3.62 (t, J=5.6 Hz, 2H), 3.59-3.54 (m, 4H), 3.45 (t, J=2.4 Hz, 1H), 2.91 (s, 2H).

1619

2-(2,6-Dioxo-3-piperidyl)-4-[2-(2-prop-2-ynoxy-ethoxy)ethylamino]isoindoline-1,3-dione (Intermediate MV)

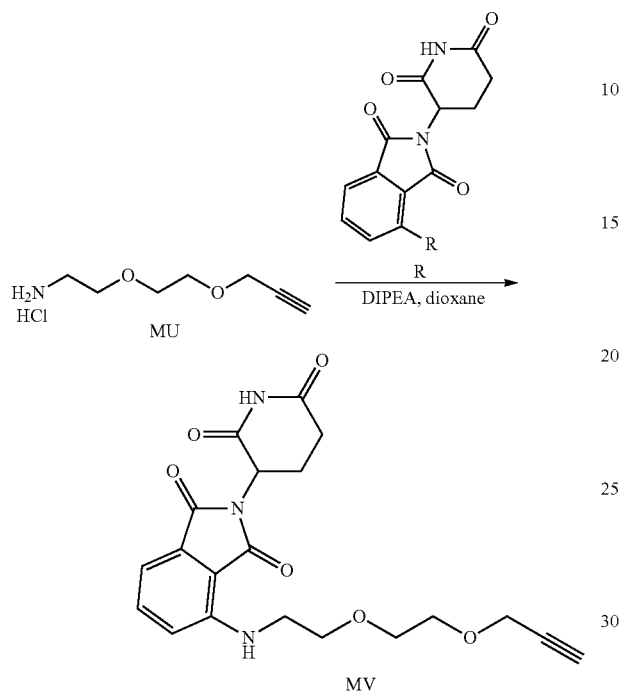

To a mixture of 2-(2-prop-2-ynoxyethoxy)ethanamine (1.80 g, 10.0 mmol, HCl, Intermediate MU) in dioxane (30 mL) was added DIPEA (3.88 g, 30.0 mmol, 5.24 mL), and 2-(2,6-dioxo-3-piperidyl)-4-fluoro-isoindoline-1,3-dione (2.77 g, 10.0 mmol, Intermediate R) into the mixture. The reaction mixture was stirred at 115° C. for 12 hrs. On completion, the mixture was concentrated in vacuo. The residue was purified by column chromatography to give the title compound (1.10 g, 27% yield) as a brown solid. $^1$H NMR (400 MHz, CDCl$_3$) δ 8.61 (s, 1H), 7.49 (t, J=7.6 Hz, 1H), 7.10 (d, J=7.2 Hz, 1H), 6.93 (d, J=8.8 Hz, 1H), 6.49 (t, J=5.6 Hz, 1H), 4.98-4.89 (m, 1H), 4.21 (d, J=2.4 Hz, 2H), 3.75-3.70 (m, 6H), 3.49 (q, J=5.6 Hz, 2H), 2.90-2.73 (m, 3H), 2.46 (t, J=2.4 Hz, 1H), 2.18-2.06 (m, 1H).

4-(Azetidin-3-ylamino)-2-(2,6-dioxo-3-piperidyl)isoindoline-1,3-dione (Intermediate MW)

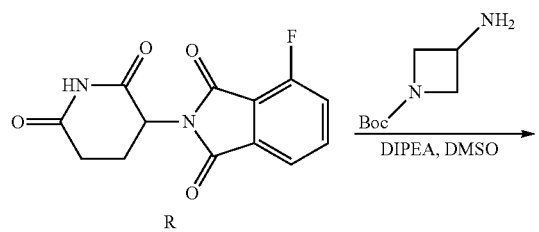

1620

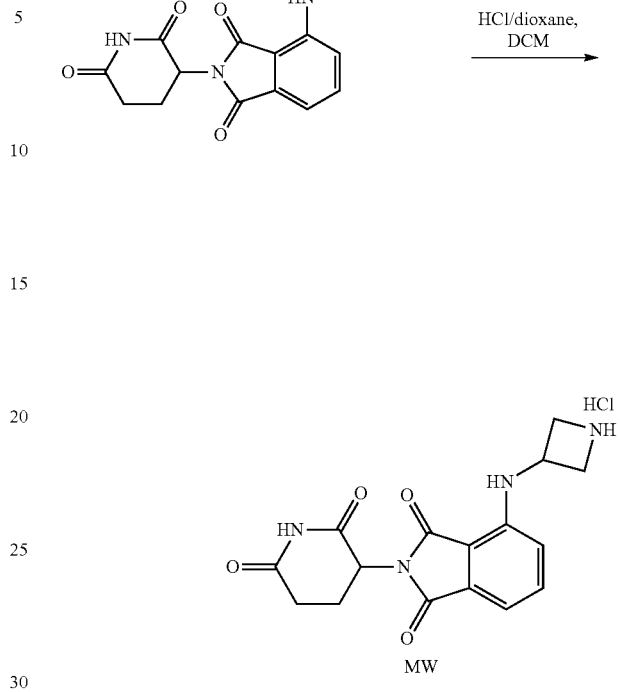

Step 1—Tert-butyl 3-[[2-(2,6-dioxo-3-piperidyl)-1,3-dioxo-isoindolin-4-yl]amino]azetidine-1-carboxylate To a solution of 2-(2,6-dioxo-3-piperidyl)-4-fluoro-isoindoline-1,3-dione (500 mg, 1.81 mmol, Intermediate R) and tert-butyl 3-aminoazetidine-1-carboxylate (374 mg, 2.17 mmol, CAS #193269-78-2) in DMSO (20 mL) was added DIPEA (702 mg, 5.43 mmol). The reaction mixture was stirred at 90° C. for 15 hrs. On completion, the reaction mixture was filtered and acidified to pH=5. The crude product was purified by reversed phase (0.1% HCl condition) to give the title compound (350 mg, 44% yield) as a yellow solid. $^1$H NMR (400 MHz, DMSO-d$_6$) δ 11.12 (s, 1H), 7.61 (t, J=8.0 Hz, 1H), 7.13 (d, J=7.2 Hz, 1H), 6.96 (d, J=8.4 Hz, 1H), 6.89 (d, J=6.4 Hz, 1H), 5.08 (dd, J=5.2, 12.8 Hz, 1H), 4.49-4.41 (m, 1H), 4.19-4.23 (m, 2H), 3.80-3.84 (m, 2H), 2.95-2.84 (m, 1H), 2.95-2.84 (m, 1H), 2.65-2.60 (m, 1H), 2.54-2.52 (m, 1H), 2.09-1.99 (m, 1H), 1.39 (s, 9H).

Step 2—4-(Azetidin-3-ylamino)-2-(2,6-dioxo-3-piperidyl)isoindoline-1,3-dione To a solution of tert-butyl 3-[[2-(2,6-dioxo-3-piperidyl)-1,3-dioxo-isoindolin-4-yl]amino]azetidine-1-carboxylate (430 mg, 1.00 mmol) in DCM (5 mL) was added HCl/dioxane (4 M, 5.12 mL). The reaction mixture was stirred at rt for 1 hr. On completion, the reaction mixture was concentrated in vacuo to give the title compound (430 mg, 100% yield, HCl) as a yellow solid. LC-MS (ESI$^+$) m/z 329.0 (M+H)$^+$.

4-[[1-[2-[2-(2-aminoethoxy)ethoxy]ethyl]azetidin-3-yl]amino]-2-(2,6-dioxo-3-piperidyl) isoindoline-1,3-dione (Intermediate MX)

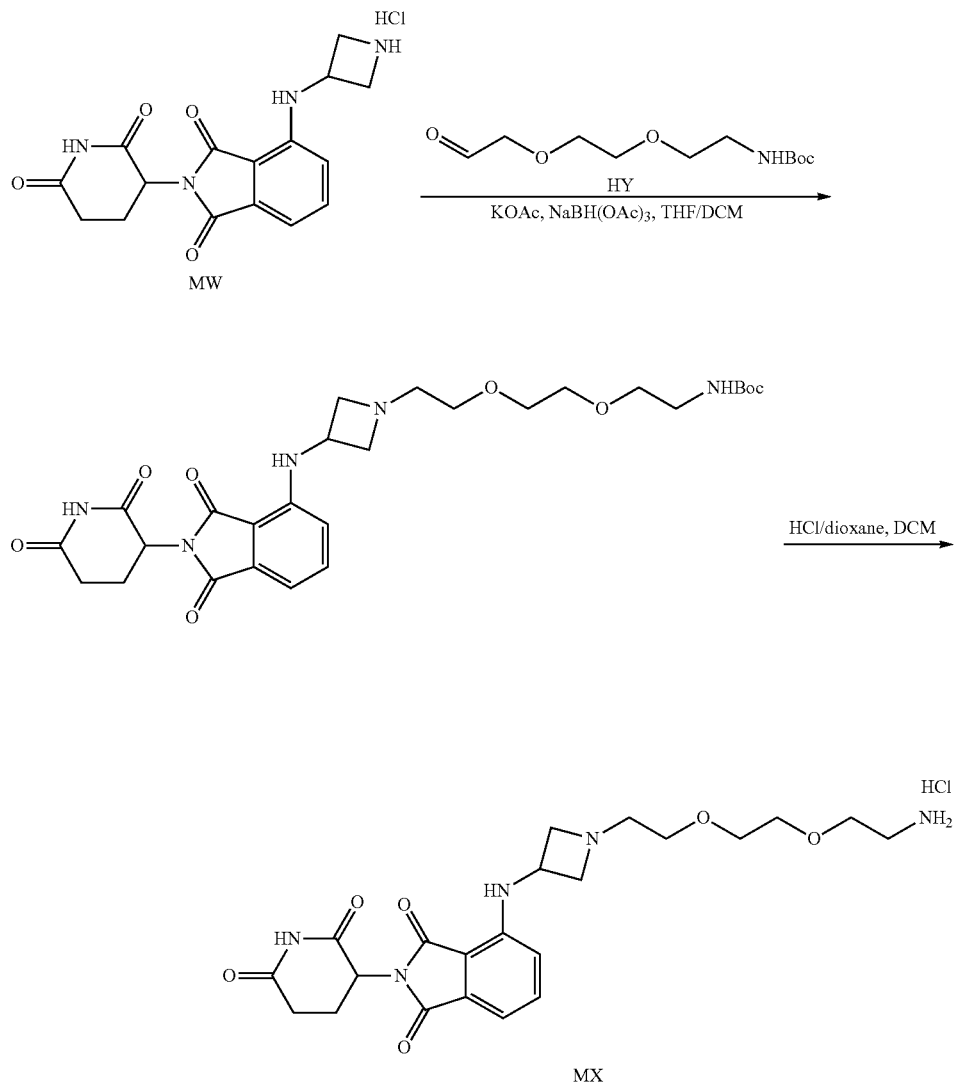

Step 1—Tert-butyl N-[2-[2-[2-[3-[[2-(2,6-dioxo-3-piperidyl)-1,3-dioxo-isoindolin-4-yl]amino]azetidin-1-yl]ethoxy]ethoxy]ethyl]carbamate To a solution of 4-(azetidin-3-ylamino)-2-(2,6-dioxo-3-piperidyl)isoindoline-1,3-dione (250 mg, 685 umol, Intermediate MW) and tert-butyl N-[2-[2-(2-oxoethoxy)ethoxy]ethyl]carbamate (220 mg, 891 umol, Intermediate HY) in DCM (10 mL) and THF (20 mL) was added KOAc (135 mg, 1.37 mmol) and NaBH(OAc)$_3$ (218 mg, 1.03 mmol). The reaction mixture was stirred at rt for 2 hrs. On completion, the reaction mixture was quenched with water (2 mL), and concentrated in vacuo. The crude product was purified by reversed phase (acidified condition: 0.1% FA) to give the title compound (270 mg, 66% yield) as yellow oil. $^1$H NMR (400 MHz, DMSO-d$_6$) δ 11.09 (s, 1H), 7.72-7.54 (m, 1H), 7.09 (d, J=8.8 Hz, 1H), 7.01 (d, J=8.8 Hz, 1H), 6.76-6.74 (m, 1H), 6.61 (d, J=6.8 Hz, 1H), 5.07 (dd, J=5.2, 12.8 Hz, 1H), 4.34-4.19 (m, 1H), 3.70 (t, J=6.8 Hz, 2H), 3.50-3.36 (m, 10H), 3.06 (q, J=6.0 Hz, 2H), 3.00-2.96 (m, 2H), 2.92-2.84 (m, 1H), 2.65-2.61 (m, 2H), 2.09-2.01 (m, 1H), 1.37 (s, 9H); LC-MS (ESI$^+$) m/z 560.1 (M+H)$^+$.

Step 2—4-[[1-[2-[2-(2-aminoethoxy)ethoxy]ethyl]azetidin-3-yl]amino]-2-(2,6-dioxo-3-piperidyl)isoindoline-1,3-dione To a solution of tert-butyl N-[2-[2-[2-[3-[[2-(2,6-dioxo-3-piperidyl)-1,3-dioxo-isoindolin-4-yl]amino]azetidin-1-yl]ethoxy]ethoxy]ethyl]carbamate (270 mg, 483 umol) in DCM (5 mL) was added HCl/dioxane (4 M, 121 uL). The reaction mixture was stirred at 20° C. for 1 hr. On completion, the reaction mixture was concentrated in vacuo to give the title compound (239 mg, 100% yield, HCl salt) as a yellow solid. LC-MS (ESI$^+$) m/z 460.3 (M+H)$^+$.

5-[2-[3-[2-[2-(2-Aminoethoxy)ethoxy]ethyl]triazol-4-yl]ethylamino]-2-(2,6-dioxo-3-piperidyl) isoindoline-1,3-dione (Intermediate MY)

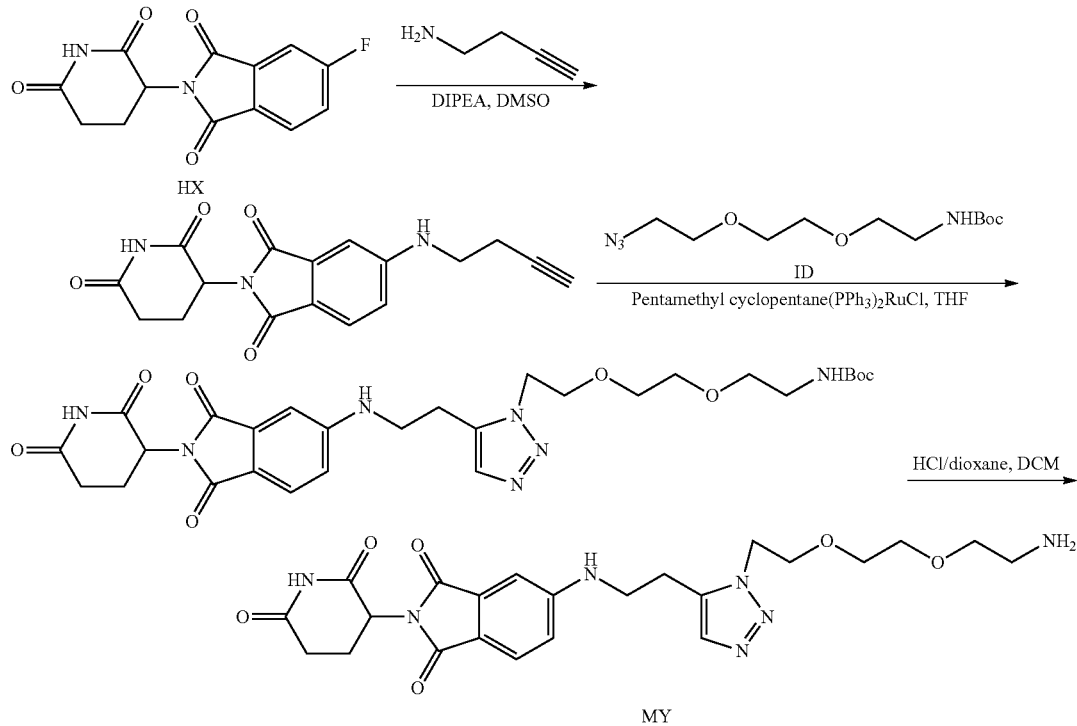

Step 1—5-(But-3-ynylamino)-2-(2,6-dioxo-3-piperidyl)isoindoline-1,3-dione

To a mixture of 2-(2,6-dioxo-3-piperidyl)-5-fluoro-isoindoline-1,3-dione (650 mg, 2.35 mmol, Intermediate HX), but-3-yn-1-amine (373 mg, HCl, CAS #14044-63-4) in DMSO (10 mL) was added DIPEA (3.04 g, 23.5 mmol) and stirred at 130° C. for 1hr. On completion, the mixture was poured into water (20 mL). The aqueous phase was extracted with ethyl acetate (2×20 mL). The combined organic phase was washed with brine (2×30 mL), dried with anhydrous $Na_2SO_4$, filtered and concentrated in vacuo. The residue was purified by column chromatography ($SiO_2$, Petroleum ether/Ethyl acetate=1:1) to give the title compound (386 mg, 50% yield) as a brown solid; LC-MS ($ESI^+$) m/z 326.0 $(M+H)^+$.

Step 2—Tert-butyl N-[2-[2-[2-[5-[2-[[2-(2,6-dioxo-3-piperidyl)-1,3-dioxo-isoindolin-5-yl]amino]ethyl]triazol-1-yl]ethoxy]ethoxy]ethyl]carbamate To a mixture of 5-(but-3-ynylamino)-2-(2,6-dioxo-3-piperidyl)isoindoline-1,3-dione (200 mg, 0.615 mmol), tert-butyl N-[2-[2-(2-azidoethoxy)ethoxy]ethyl]carbamate (506 mg, 1.84 mmol, Intermediate ID) in THF (5 mL) was added chlororuthenium (1+); 1,2,3,4,5-pentamethylcyclopenta-1,3-diene; triphenylphosphane (24.4 mg, 0.030 mmol). The mixture was stirred at 65° C. for 12 hrs. On completion, the mixture was concentrated in vacuo. The residue was purified by column chromatography ($SiO_2$, Petroleum ether/Ethyl acetate=1:1) to give the title compound (210 mg, 54% yield) as a brown oil; LC-MS ($ESI^+$) m/z 600.2 $(M+H)^+$.

Step 3—5-[2-[3-[2-[2-(2-Aminoethoxy)ethoxy]ethyl]triazol-4-yl]ethylamino]-2-(2,6-dioxo-3-piperidyl) isoindoline-1,3-dione To a mixture of tert-butyl N-[2-[2-[2-[5-[2-[[2-(2,6-dioxo-3-piperidyl)-1,3-dioxo-isoindolin-5-yl]amino]ethyl]triazol-1-yl]ethoxy]ethoxy]ethyl]carbamate (210 mg, 350 umol) in DCM (5 mL) was added HCl/dioxane (4 M, 87.5 uL) and stirred at 15° C. for 0.5 hr. On completion, the mixture was concentrated in vacuo to give the title compound (185 mg, 98% yield, HCl) brown oil. LC-MS ($ESI^+$) m/z 500.2 $(M+H)^+$.

2-(2,6-Dioxo-3-piperidyl)-5-hydroxy-isoindoline-1,3-dione (Intermediate MZ)

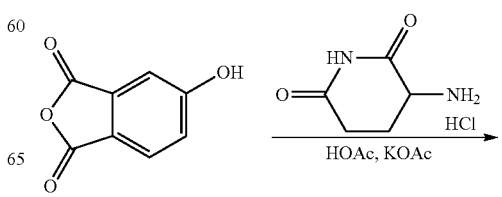

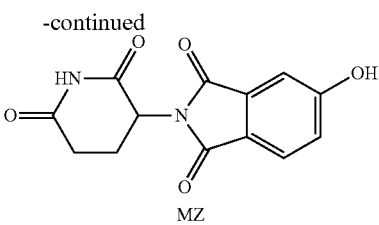

MZ

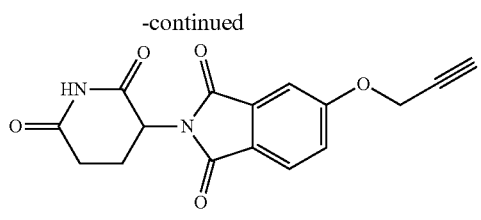

NA

To a solution of 5-hydroxyisobenzofuran-1,3-dione (1.00 g, 6.09 mmol, CAS #27550-59-0) and 3-aminopiperidine-2,6-dione (1.05 g, 6.40 mmol, HCl) in HOAc (20 mL) was added KOAc (1.79 g, 18.3 mmol). The mixture was stirred at 90° C. for 6 hrs. On completion, the mixture was poured into ice water (100 mL), and solid was obtained and then filtered. The residue was washed with H$_2$O (3×50 mL), dried in vacuo to give the title compound (1.40 g, 83% yield) as a light white solid. $^1$H NMR (400 MHz, DMSO-d$_6$) δ 11.29-10.90 (m, 2H), 7.75 (d, J=8.2 Hz, 1H), 7.39-6.87 (m, 2H), 5.09 (dd, J=5.4, 12.8 Hz, 1H), 3.34 (s, 1H), 2.96-2.82 (m, 1H), 2.69-2.58 (m, 1H), 2.08-1.99 (m, 1H).

2-(2,6-Dioxo-3-piperidyl)-5-prop-2-ynoxy-isoindoline-1,3-dione (Intermediate NA)

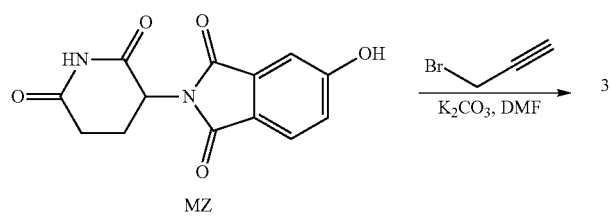

To a solution of 2-(2,6-dioxo-3-piperidyl)-5-hydroxy-isoindoline-1,3-dione (1.40 g, 5.11 mmol, Intermediate MZ) in DMF (20 mL) was added K$_2$CO$_3$ (847 mg, 6.13 mmol) and 3-bromoprop-1-yne (668 mg, 5.62 mmol, 484 uL). The mixture was stirred at 15° C. for 6 hrs. On completion, the residue was diluted with H$_2$O (50 mL) and extracted with EA (3×50 mL). The combined organic layers were washed with brine (100 mL), dried over Na$_2$SO$_4$, filtered and concentrated to give a residue. The residue was purified by reversed phase (FA condition) to give the title compound (0.700 g, 43% yield) as a light yellow solid. $^1$H NMR (400 MHz, DMSO-d$_6$) δ 11.11 (s, 1H), 7.89 (d, J=8.4 Hz, 1H), 7.53 (d, J=2.4 Hz, 1H), 7.41 (dd, J=2.4, 8.4 Hz, 1H), 5.14 (dd, J=5.4, 12.8 Hz, 1H), 5.07 (d, J=2.0 Hz, 2H), 3.70 (t, J=2.4 Hz, 1H), 3.41-3.35 (m, 1H), 2.97-2.83 (m, 1H), 2.65-2.52 (m, 2H), 2.11-2.01 (m, 1H); LC-MS (ESI$^+$) m/z 313.2 (M+H)$^+$.

5-[[1-[2-[2-(2-Aminoethoxy)ethoxy]ethyl]triazol-4-yl]methoxy]-2-(2,6-dioxo-3-piperidyl) isoindoline-1,3-dione (Intermediate NB)

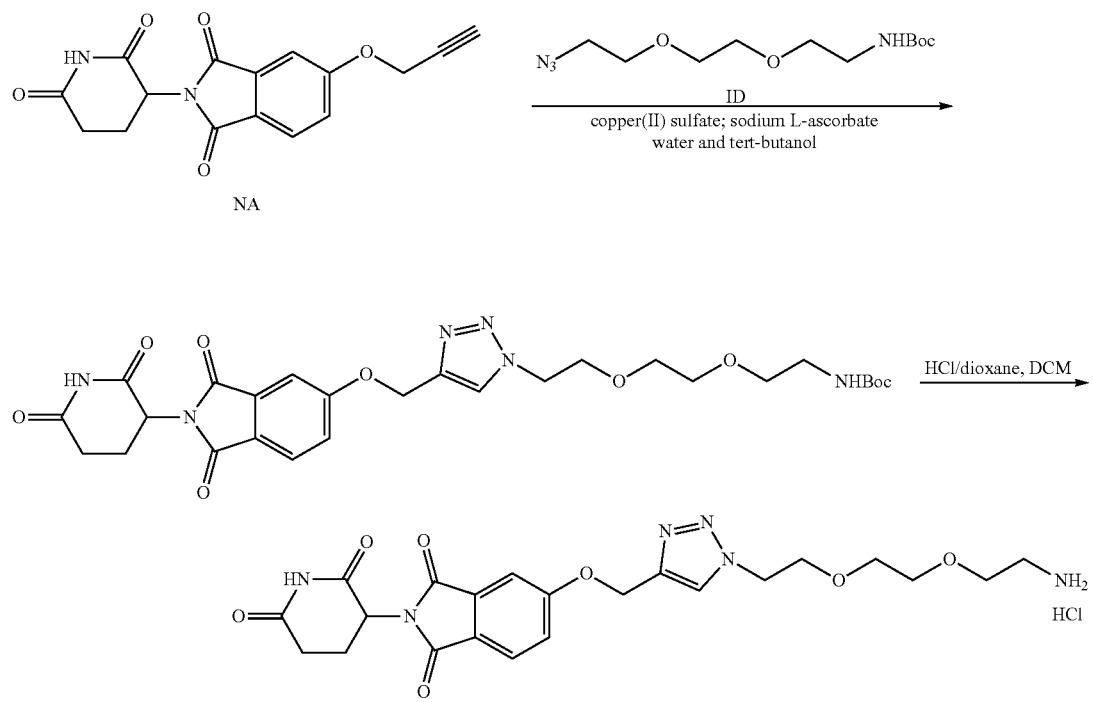

Step 1—Tert-butyl N-[2-[2-[2-[4-[[2-(2,6-dioxo-3-piperidyl)-1,3-dioxo-isoindolin-5-yl]oxymethyl]triazol-1-yl]ethoxy]ethoxy]ethyl]carbamate To a solution of 2-(2,6-dioxo-3-piperidyl)-5-prop-2-ynoxy-isoindoline-1,3-dione (0.6 g, 1.92 mmol, Intermediate NA), CuSO$_4$ (3.07 mg, 19.2 umol) and sodium; (2R)-2-[(1S)-1,2-dihydroxyethyl]-4-hydroxy-5-oxo-2H-furan-3-olate (7.61 mg, 38.4 umol) in H$_2$O (3 mL) and t-BuOH (3 mL) was added tert-butyl N-[2-[2-(2-azidoethoxy)ethoxy]ethyl]carbamate (527.06 mg, 1.92 mmol, Intermediate ID). The mixture was stirred at 60° C. for 2 hrs. On completion, the mixture was diluted with H$_2$O (20 ml), extracted with EA (2×30 ml), washed with brine (50 ml), dried over Na$_2$SO$_4$, filtered and concentrated in vacuo. The residue was purified by reversed phase (FA condition) to give the title compound (0.800 g, 71% yield) as a yellow solid. $^1$H NMR (400 MHz, DMSO-d$_6$) δ 11.10 (s, 1H), 8.25 (s, 1H), 7.85 (d, J=8.2 Hz, 1H), 7.61 (s, 1H), 7.45 (d, J=8.2 Hz, 1H), 6.72 (s, 2H), 5.38 (s, 2H), 5.17-5.09 (m, 1H), 4.55 (s, 2H), 4.10-3.97 (m, 4H), 3.83 (s, 2H), 3.65-3.51 (m, 13H), 3.07 (d, J=6.0 Hz, 4H), 2.88 (d, J=13.6 Hz, 1H), 2.70-2.57 (m, 4H), 1.38 (s, 9H).

Step 2—5-[[1-[2-[2-(2-Aminoethoxy)ethoxy]ethyl]triazol-4-yl]methoxy]-2-(2,6-dioxo-3-piperidyl)isoindoline-1,3-dione To a solution of tert-butyl N-[2-[2-[2-[4-[[2-(2,6-dioxo-3-piperidyl)-1,3-dioxo-isoindolin-5-yl]oxymethyl]triazol-1-yl]ethoxy]ethoxy]ethyl]carbamate (0.800 g, 1.36 mmol) in DCM (10 mL) was added HCl/dioxane (4 M, 1 mL). The mixture was stirred at rt for 30 minutes. On completion, the mixture was concentrated, to give the title compound (500 mg 70% yield, HCl) as a yellow solid. LC-MS (ESI$^+$) m/z 487.3 (M+H)$^+$.

5-But-3-ynoxy-2-(2,6-dioxo-3-piperidyl)isoindoline-1,3-dione (Intermediate NC)

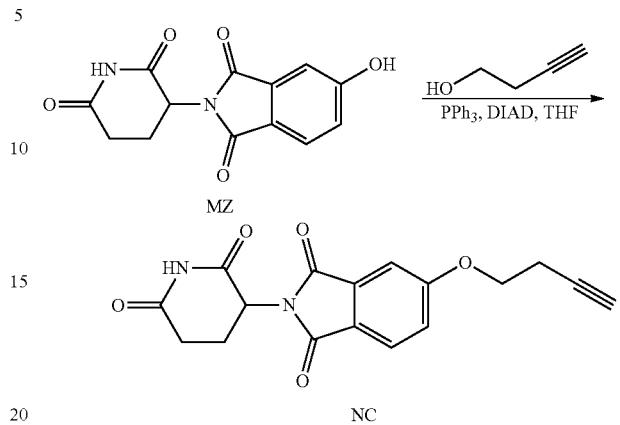

To a mixture of 2-(2,6-dioxo-3-piperidyl)-5-hydroxy-isoindoline-1,3-dione (1.00 g, 3.65 mmol, Intermediate MZ) and but-3-yn-1-ol (307 mg, 4.38 mmol, CAS #927-74-2) in THF (10 mL) was added PPh$_3$ (1.43 g, 5.47 mmol). Then DIAD (1.47 g, 7.29 mmol) was added into the mixture at 0° C. and the mixture was stirred at rt for 12 hrs. On completion, the mixture was concentrated in vacuo. The residue was purified by column chromatography (SiO$_2$) to give the title compound (568 mg, 48% yield) as a brown solid. LC-MS (ESI$^+$) m/z 327.0 (M+H)$^+$.

5-[2-[3-[2-[2-(2-aminoethoxy)ethoxy]ethyl]triazol-4-yl]ethoxy]-2-(2,6-dioxo-3-piperidyl) isoindoline-1,3-dione (Intermediate ND)

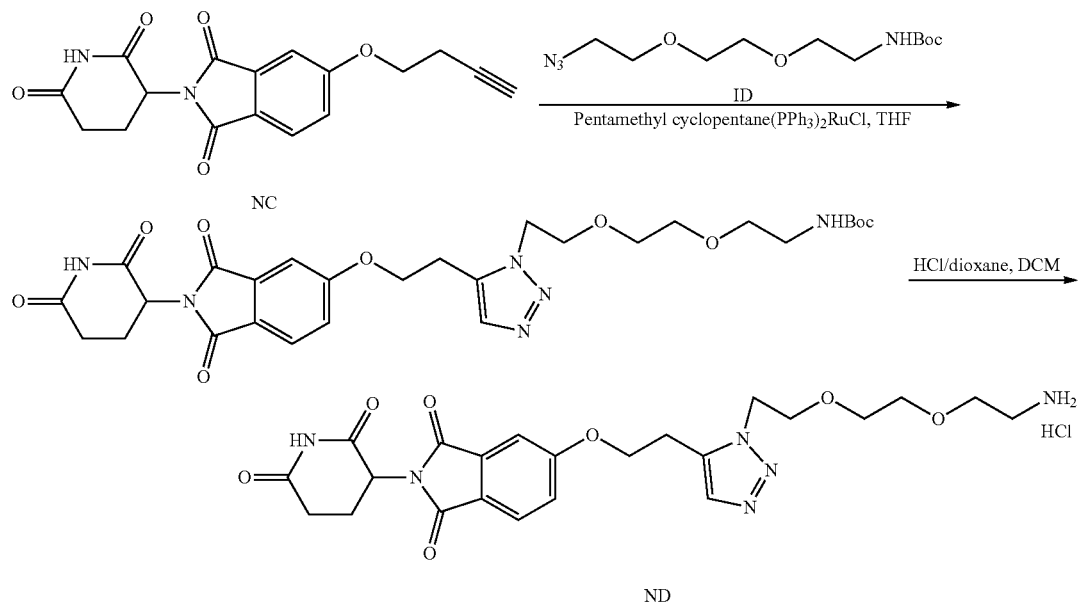

Step 1—Tert-butyl N-[2-[2-[2-[5-[2-[2-(2,6-dioxo-3-piperidyl)-1,3-dioxo-isoindolin-5-yl]oxyethyl]triazol-1-yl]ethoxy]ethoxy]ethyl]carbamate To a mixture of 5-but-3-ynoxy-2-(2,6-dioxo-3-piperidyl)isoindoline-1,3-dione (115 mg, 352 umol, Intermediate NC), tert-butyl N-[2-[2-(2-azidoethoxy)ethoxy]ethyl]carbamate (290 mg, 1.06 mmol, Intermediate ID) in THF (3 mL) was added chlororuthenium (1+); 1,2,3,4,5-pentamethylcyclopenta-1,3-diene; triphenylphosphane (14.0 mg, 17.6 umol). The mixture was stirred at 65° C. for 12 hrs. On completion, the mixture was concentrated in vacuo. The residue was purified by column chromatography (SiO$_2$) to give the title compound (156 mg, 73% yield) as brown oil. LC-MS (ESI$^+$) m/z 601.1 (M+H)$^+$.

Step 2—5-[2-[3-[2-[2-(2-aminoethoxy)ethoxy]ethyl]triazol-4-yl]ethoxy]-2-(2,6-dioxo-3-piperidyl) isoindoline-1,3-dione To a mixture of tert-butyl N-[2-[2-[2-[5-[2-[2-(2,6-dioxo-3-piperidyl)-1,3-dioxo-isoindolin-5-yl]oxyethyl]triazol-1-yl]ethoxy]ethoxy]ethyl]carbamate (156 mg, 259 umol) in DCM (2 mL) was added HCl/dioxane (4 M, 129 uL). The reaction mixture was stirred at rt for 0.5 hr. On completion, the mixture was concentrated in vacuo. The residue was purified by reverse phase (0.1% FA condition) to give the title compound (135 mg, 96% yield, HCl) as brown oil. LC-MS (ESI$^+$) m/z 501.1 (M+H)$^+$.

5-[2-[2-[4-[2-(2-Aminoethoxy)ethyl]piperazin-1-yl]ethoxy]ethylamino]-2-(2,6-dioxo-3-piperidyl)isoindoline-1,3-dione (Intermediate NE)

Step 1—Tert-butyl N-[2-[2-[4-[2-[2-[[2-(2,6-dioxo-3-piperidyl)-1,3-dioxo-isoindolin-5-yl]amino]ethoxy]ethyl]piperazin-1-yl]ethoxy]ethyl]carbamate To a solution of 2-(2,6-dioxo-3-piperidyl)-5-fluoro-isoindoline-1,3-dione (250 mg, 905 umol, Intermediate HX) and tert-butyl N-[2-[2-[4-[2-(2-aminoethoxy)ethyl]piperazin-1-yl]ethoxy]ethyl]carbamate (343 mg, 950 umol, Intermediate IM) in DMSO (8 mL) was added DIPEA (351 mg, 2.72 mmol). The reaction mixture was stirred at 130° C. for 13 hours. On completion, the reaction mixture was quenched with water (2 mL), concentrated in vacuo. The crude product was purified by reversed phase (acidified condition: 0.1% FA) to give the title compound (324 mg, 55% yield) as a yellow oil. LC-MS (ESI$^+$) m/z 517.2 (M+H−100)$^+$.

Step 2—5-[2-[2-[4-[2-(2-Aminoethoxy)ethyl]piperazin-1-yl]ethoxy]ethylamino]-2-(2,6-dioxo-3-piperidyl)isoindoline-1,3-dione To a solution of tert-butyl N-[2-[2-[4-[2-[2-[[2-(2,6-dioxo-3-piperidyl)-1,3-dioxo-isoindolin-5-yl]amino]ethoxy]ethyl]piperazin-1-yl]ethoxy]ethyl]carbamate (350 mg, 534 umol) in DCM (5 mL) was added HCl/dioxane (4 M, 133 uL). The reaction mixture was stirred at rt for 1 hr. On completion, the reaction mixture was concentrated in vacuo to give the title compound (290 mg, 98% yield) as a yellow solid. LC-MS (ESI$^+$) m/z 517.2 (M+H)$^+$.

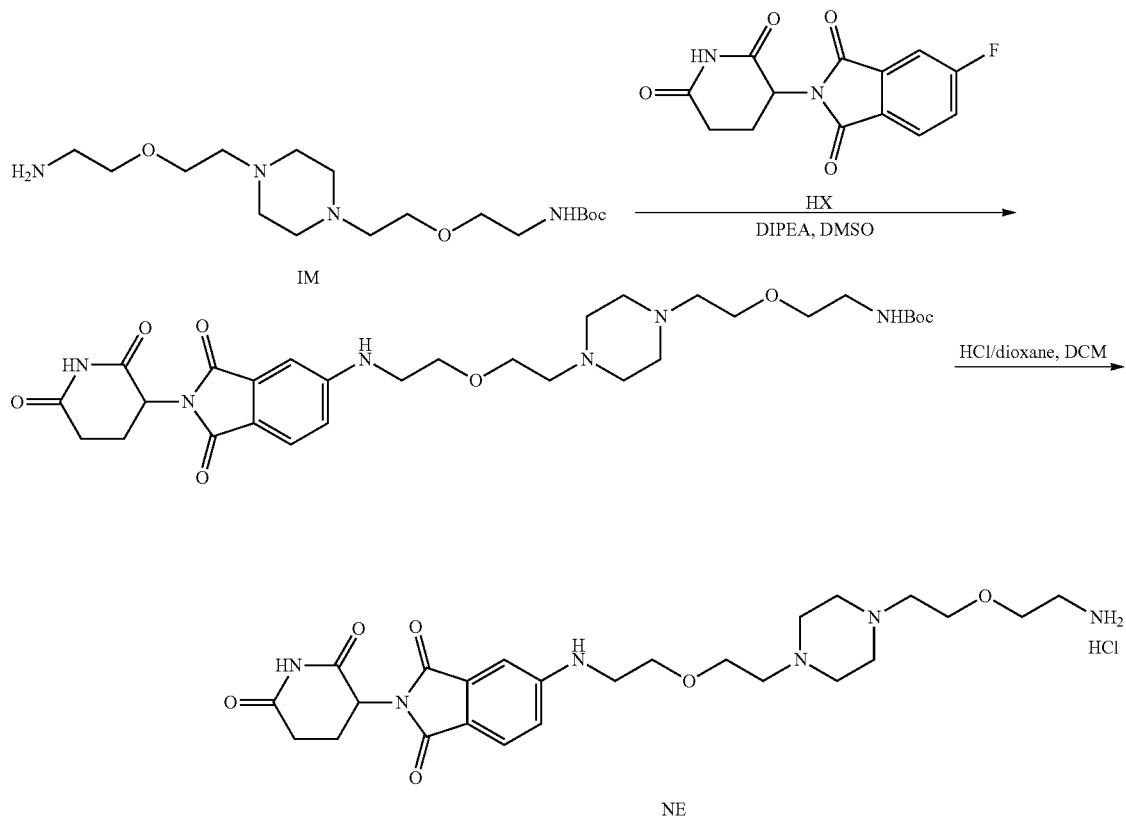

2-[2-1 [[12-(2,6-Dioxo-3-piperidyl)-1,3-dioxo-isoindolin-5-yl]amino]ethoxy]ethyl methanesulfonate (Intermediate NF)

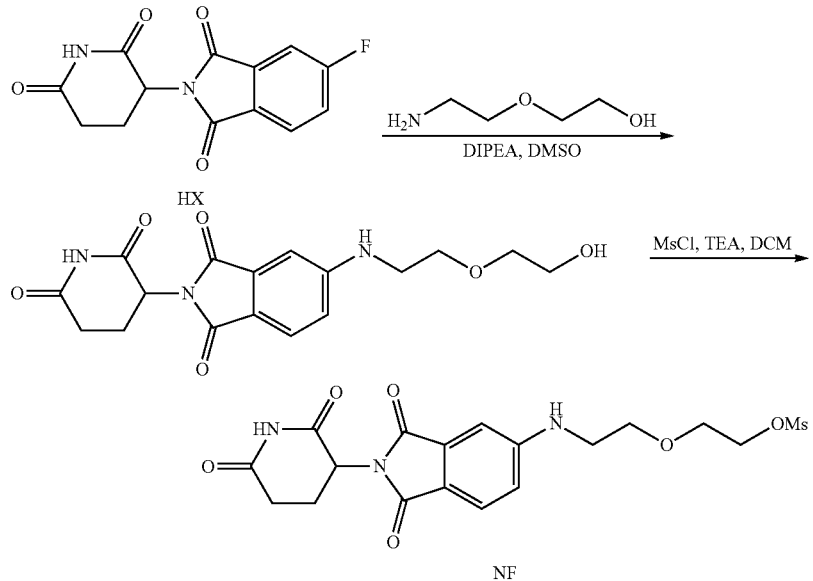

Step 1—2-(2,6-Dioxopiperidin-3-yl)-5-((2-(2-hydroxyethoxy)ethyl)amino)isoindoline-1,3-dione To a solution of 2-(2,6-dioxo-3-piperidyl)-5-fluoro-isoindoline-1,3-dione (500 mg, 1.81 mmol, Intermediate HX) and 2-(2-aminoethoxy)ethanol (210 mg, 2.00 mmol) in DMSO (10.0 mL) was added DIPEA (702 mg, 5.43 mmol). The reaction mixture was stirred at 130° C. for 15 hrs. On completion, the mixture was added $H_2O$ (10.0 mL) and extracted with DCM (3×100 mL). The combined organic layers were washed with brine (50 mL), dried over $Na_2SO_4$, filtered and concentrated to give the title compound (250 mg, 38% yield) as a yellow solid. $^1H$ NMR (400 MHz, $CDCl_3$) δ 8.14 (s, 1H), 7.62 (d, J=8.4 Hz, 1H), 7.01 (d, J=2.0 Hz, 1H), 6.79 (dd, J=2.0, 8.4 Hz, 1H), 5.05 (s, 1H), 4.95 (dd, J=5.2, 12.8 Hz, 1H), 3.81 (d, J=4.2 Hz, 2H), 3.78 (t, J=5.2 Hz, 2H), 3.68-3.63 (m, 2H), 3.45 (t, J=5.2 Hz, 2H), 2.95-2.70 (m, 3H), 2.19-2.11 (m, 1H). LC-MS ($ESI^+$) m/z 362.1 $(M+H)^+$.

Step 2—2-[2-[[2-(2,6-Dioxo-3-piperidyl)-1,3-dioxo-isoindolin-5-yl]amino]ethoxy]ethyl methanesulfonate To a solution of 2-(2,6-dioxo-3-piperidyl)-5-[2-(2-hydroxyethoxy)ethylamino]isoindoline-1,3-dione (300 mg, 830 umol) in DCM (20.0 mL) was added TEA (168 mg, 1.66 mmol) and MsCl (105 mg, 913 umol). The reaction mixture was stirred at rt for 2 hrs. On completion, the mixture was diluted with water (50 mL) and extracted with DCM (2×100 mL). The organic layer was washed with brine (20 mL), dried over anhydrous sodium sulfate, filtered and concentrated in vacuo to give the title compound (360 mg, 98% yield) as a yellow solid. $^1H$ NMR (400 MHz, $CDCl_3$) δ 7.99 (s, 1H), 7.64 (d, J=8.4 Hz, 1H), 7.02 (d, J=2.0 Hz, 1H), 6.83 (dd, J=2.0, 8.4 Hz, 1H), 5.03-4.89 (m, 1H), 4.52-4.39 (m, 2H), 3.85-3.76 (m, 4H), 3.44 (t, J=5.2 Hz, 2H), 3.10 (s, 3H), 2.96-2.72 (m, 3H), 2.24-2.10 (m, 1H).

5-[2-[2-[6-[2-(2-Aminoethoxy)ethyl]-2,6-diazaspiro[3.3]heptan-2-yl]ethoxy]ethylamino]-2-(2,6-dioxo-3-piperidyl)isoindoline-1,3-dione (Intermediate NG)

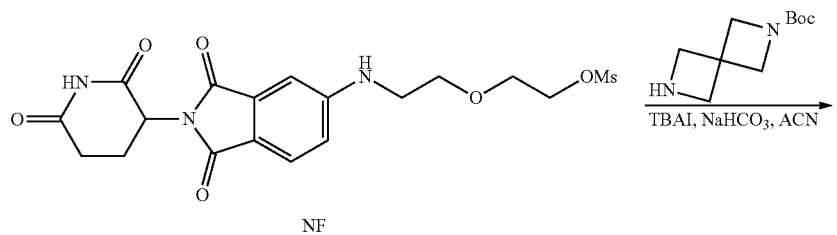

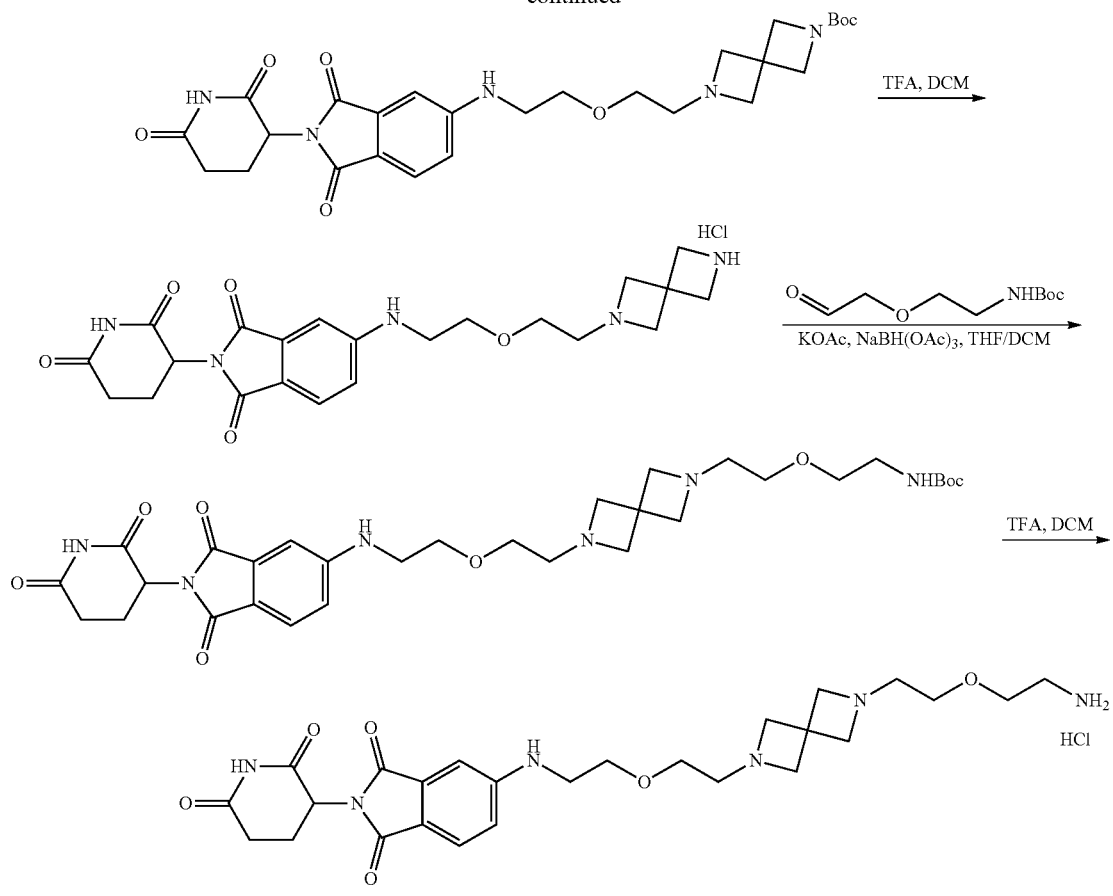

NG

Step 1-Tert-butyl 6-[2-[2-[[2-(2,6-dioxo-3-piperidyl)-1,3-dioxo-isoindolin-5-yl]amino]ethoxy]ethyl]-2,6-diazaspiro[3.3]heptane-2-carboxylate To a solution of 2-[2-[[2-(2,6-dioxo-3-piperidyl)-1,3-dioxo-isoindolin-5-yl]amino]ethoxy]ethyl methanesulfonate (260 mg, 592 umol, Intermediate NF) and tert-butyl 2,6-diazaspiro[3.3]heptane-2-carboxylate (139 mg, 592 umol, HCl, CAS #1041026-70-3) in ACN (15.0 mL) was added NaHCO₃ (149 mg, 1.77 mmol) and TBAI (21.9 mg, 59.2 umol). The reaction mixture was stirred at 80° C. for 16 hrs. On completion, the mixture was concentrated in vacuo. The crude product was purified by silica gel chromatography (DCM:MeOH=20:1) to give the title compound (159 mg, 45% yield) as a yellow solid. ¹H NMR (400 MHz, DMSO-d₆) δ 11.07 (s, 1H), 7.57 (d, J=8.4 Hz, 1H), 7.16 (s, 1H), 7.01 (s, 1H), 6.90 (d, J=8.4 Hz, 1H), 5.04 (dd, J=5.2, 12.8 Hz, 1H), 3.86 (s, 4H), 3.54 (t, J=5.2 Hz, 2H), 3.44-3.35 (m, 10H), 2.96-2.80 (m, 1H), 2.63-2.59 (m, 2H), 2.00 (d, J=10.8 Hz, 1H), 1.36 (s, 9H). LC-MS (ESI⁺) m/z 542.3 (M+H)⁺.

Step 2—5-[2-[2-(2,6-Diazaspiro[3.3]heptan-2-yl)ethoxy]ethylamino]-2-(2,6-dioxo-3-piperidyl) isoindoline-1,3-dione To a solution of tert-butyl 6-[2-[2-[[2-(2,6-dioxo-3-piperidyl)-1,3-dioxo-isoindolin-5-yl]amino]ethoxy]ethyl]-2,6-diazaspiro[3.3]heptane-2-carboxylate (177 mg, 327 umol) in DCM (5.00 mL) was added TFA (2.48 g, 21.7 mmol). The reaction mixture was stirred at rt for 1 hr. On completion, the mixture was concentrated in vacuo. Then, the residue was diluted with anhydrous toluene (30.0 mL). Then the mixture was concentrated in vacuo to give the title compound (181 mg, 100% yield, TFA) as a yellow solid. LC-MS (ESI⁺) m/z 442.3 (M+H)⁺.

Step 3—Tert-butyl N-[2-[2-[6-[2-[2-[[2-(2,6-dioxo-3-piperidyl)-1,3-dioxo-isoindolin-5-yl]amino]ethoxy]ethyl]-2,6-diazaspiro[3.3]heptan-2-yl]ethoxy]ethyl]carbamate To a solution of 5-[2-[2-(2,6-diazaspiro[3.3]heptan-2-yl)ethoxy]ethylamino]-2-(2,6-dioxo-3-piperidyl) isoindoline-1,3-dione (181 mg, 327 umol, TFA) and tert-butyl N-[2-(2-oxoethoxy)ethyl]carbamate (230 mg, 1.13 mmol, synthesized via Step 1 of Intermediate FS) in a mixed solvent of THF (15.0 mL) and DMF (5.00 mL) was added TEA (66.1 mg, 654 umol) and HOAc (78.5 mg, 1.31 mmol). The reaction mixture was stirred at rt for 12 hrs. After, NaBH(OAc)₃ (83.1 mg, 392 umol) was added and the resulting reaction mixture was stirred at rt for 24 hrs. On completion, the mixture was quenched with water (1.00 mL). The mixture was concentrated in vacuo. The crude product was purified by reversed phase (condition: 0.1% FA) to give the title compound (77 mg, 34% yield) as yellow solid. LC-MS (ESI⁺) m/z 629.4 (M+H)⁺.

Step 4—5-[2-[2-[6-[2-(2-Aminoethoxy)ethyl]-2,6-diazaspiro[3.3]heptan-2-yl]ethoxy]ethylamino]-2-(2,6-dioxo-3-piperidyl)isoindoline-1,3-dione To a solution of tert-butyl N-[2-[2-[6-[2-[2-[[2-(2,6-dioxo-3-piperidyl)-1,3-dioxo-isoindolin-5-yl]amino]ethoxy]ethyl]-2,6-diazaspiro[3.3]heptan-2-yl]ethoxy]ethyl]carbamate (100 mg, 151 umol) in DCM (5.00 mL) was added TFA (86.2 mg, 756 umol). The reaction mixture was stirred at rt for 1 hr. On completion, the reaction mixture was concentrated in vacuo to give the title compound (97 mg, 100% yield, TFA) as a yellow solid. LC-MS (ESI$^+$) m/z 529.4 (M+H)$^+$.

4-(Aminomethyl)-2-(2,6-dioxo-3-piperidyl)isoindoline-1,3-dione (Intermediate NH)

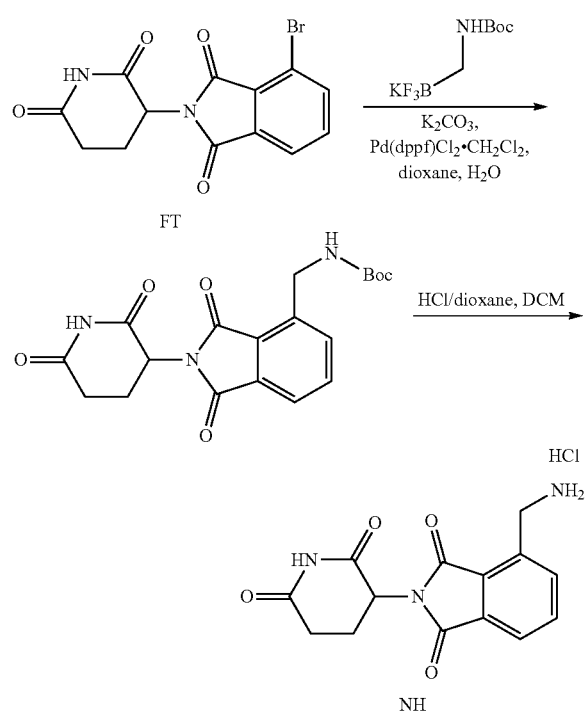

Step 1—Tert-butyl N-[[2-(2,6-dioxo-3-piperidyl)-1,3-dioxo-isoindolin-4-yl]methyl]carbamate To a solution of 4-bromo-2-(2,6-dioxo-3-piperidyl)isoindoline-1,3-dione (700 mg, 2.08 mmol, Intermediate FT) and potassium N-Boc-amino methyltrifluoroborate (738 mg, 3.11 mmol, CAS #1314538-55-0) in dioxane (10 mL) and H$_2$O (2 mL) was added K$_2$CO$_3$ (861 mg, 6.23 mmol) and Pd(dppf)Cl$_2$·CH$_2$Cl$_2$ (170 mg, 208 umol). The reaction mixture was stirred at 85° C. for 6 hours under nitrogen. On completion, the reaction mixture was poured into brine (30 mL) and extracted with EA (3×80 mL). The combined organic layers were washed with brine (80 mL), dried with anhydrous Na$_2$SO$_4$, filtered, concentrated in vacuo. The residue was purified by silica column chromatography (PE/EA, 3/1 to 1/1) to give the title compound (270 mg, 34% yield) as a yellow solid. $^1$H NMR (400 MHz, DMSO-d$_6$) δ 11.11 (s, 1H), 7.88-7.77 (m, 2H), 7.74-7.64 (m, 1H), 5.20-5.09 (m, 1H), 4.69-4.54 (m, 2H), 3.02-2.79 (m, 1H), 2.69-2.56 (m, 2H), 2.17-2.01 (m, 1H), 1.41 (s, 9H).

Step 2—4-(Aminomethyl)-2-(2,6-dioxo-3-piperidyl)isoindoline-1,3-dione

To a solution of tert-butyl N-[[2-(2,6-dioxo-3-piperidyl)-1,3-dioxo-isoindolin-4-yl]methyl]carbamate (80.0 mg, 207 umol) in DCM (10 mL) was added HCl/dioxane (4 M, 12.3 mL). The reaction mixture was stirred at rt for 1 hour. On completion, the reaction mixture was concentrated in vacuo to give the title compound (60.0 mg, 90% yield) as yellow oil.

5-[2-(2,6-Dioxo-3-piperidyl)-1,3-dioxo-isoindolin-4-yl]pentyl methanesulfonate (Intermediate NI)

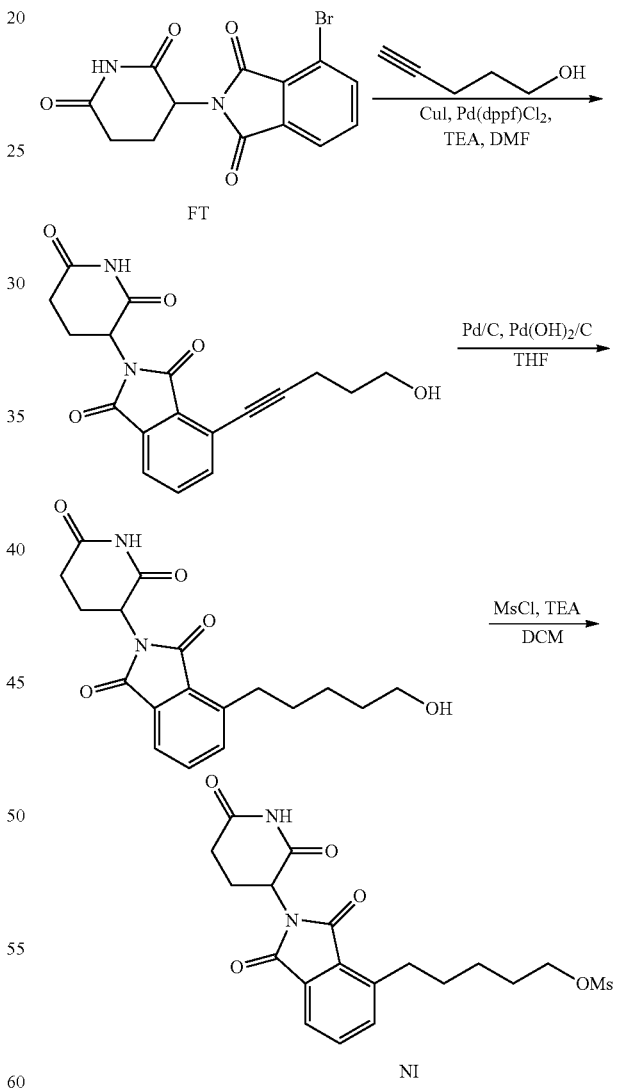

Step 1—2-(2,6-Dioxo-3-piperidyl)-4-(5-hydroxypent-1-ynyl)isoindoline-1,3-dione To a solution of 4-bromo-2-(2,6-dioxo-3-piperidyl)isoindoline-1,3-dione (1.00 g, 2.97 mmol, Intermediate FT) and pent-4-yn-1-ol (499 mg, 5.93 mmol, CAS #5390-04-5) in DMF (10 mL) was added Pd(PPh$_3$)$_2$Cl$_2$ (208 mg, 296 umol), TEA (5.40 g, 53.3 mmol, 7.43 mL), and CuI (56.4 mg, 296 umol) under N$_2$. The reaction mixture was stirred at 80° C. for 30 min under microwave. On completion, the reaction mixture was diluted with EA (20 mL), filtered and concentrated in vacuo. The residue was purified by column chromatography (SiO$_2$, Petroleum ether/Ethyl acetate=5:1 to 1:1) to give the title compound (800 mg, 76% yield) as a light yellow solid. LC-MS (ESI$^+$) m/z 341.1 (M+H)$^+$.

Step 2—2-(2,6-Dioxo-3-piperidyl)-4-(5-hydroxypentyl)isoindoline-1,3-dione

To a solution of 2-(2,6-dioxo-3-piperidyl)-4-(5-hydroxypent-1-ynyl)isoindoline-1,3-dione (800 mg, 2.35 mmol) in THF (25 mL) was added Pd/C (100 mg, 2.35 mmol, 10 wt %) and Pd(OH)$_2$/C (100 mg, 71.2 umol, 10 wt %). The reaction mixture was stirred at rt for 12 hours under H$_2$ (15 psi). On completion, the residue was filtered and the filtrate was concentrated in vacuo to give the title compound (810 mg, 95% yield) as a black brown solid. LC-MS (ESI$^+$) m/z 345.3 (M+H)$^+$.

Step 3—5-[2-(2,6-Dioxo-3-piperidyl)-1,3-dioxoisoindolin-4-yl]pentyl methanesulfonate To a solution of 2-(2,6-dioxo-3-piperidyl)-4-(5-hydroxypentyl)isoindoline-1,3-dione (300 mg, 871 umol) and TEA (264 mg, 2.61 mmol, 363 uL) in DCM (5 mL) was added MsCl (119 mg, 1.05 mmol, 80.9 uL). The reaction mixture was stirred at rt for 0.5 hour. The mixture was quenched by addition of H$_2$O (50 mL), then extracted with DCM (2×100 mL). The organic phase was concentrated in vacuo to give the title compound (370 mg, 90% yield) as a yellow solid. LC-MS (ESI$^+$) m/z 423.2 (M+H)$^+$.

2-[2-[2-(2,6-Dioxo-3-piperidyl)-1,3-dioxo-isoindolin-4-yl]ethoxy]ethyl methanesulfonate (Intermediate NJ)

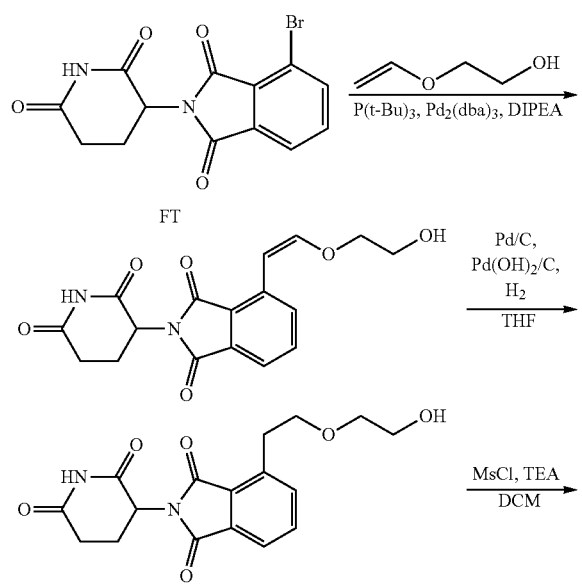

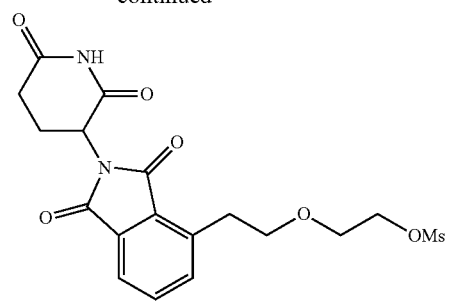

NJ

Step 1—2-(2,6-Dioxo-3-piperidyl)-4-[(Z)-2-(2-hydroxyethoxy)vinyl]isoindoline-1,3-dione To a solution of 4-bromo-2-(2,6-dioxo-3-piperidyl)isoindoline-1,3-dione (1.5 g, 4.45 mmol, Intermediate FT) and 2-vinyloxyethanol (784 mg, 8.90 mmol, CAS #764-48-7) in dioxane (100 mL) was added P(t-Bu)$_3$ (1.80 g, 889 umol, 2.09 mL, 10% purity), DIPEA (690 mg, 5.34 mmol, 930 uL) and Pd$_2$(dba)$_3$ (407 mg, 444 umol). The reaction mixture was stirred at rt for 12 hours under N$_2$. On completion, the reaction mixture was poured into sat.NH$_4$Cl (30 mL) and extracted with EA (3×100 mL). The combined organic layers were washed with brine (50 mL), dried with anhydrous Na$_2$SO$_4$, filtered and concentrated in vacuo. The residue was purified by column chromatography (SiO$_2$, Petroleum ether/Ethyl acetate=2:1 to 0:1) to give the title compound (600 mg, 33% yield) as a light yellow solid. LC-MS (ESI$^+$) m/z 345.1 (M+H)$^+$.

Step 2—2-(2,6-Dioxo-3-piperidyl)-4-[2-(2-hydroxyethoxy)ethyl]isoindoline-1,3-dione To a solution of 2-(2,6-dioxo-3-piperidyl)-4-[(Z)-2-(2-hydroxyethoxy)vinyl]isoindoline-1,3-dione (500 mg, 1.45 mmol) in THF (20 mL) was added Pd/C (50 mg, 1.45 mmol, 10 wt %). The reaction mixture was stirred at rt for 24 hours under H$_2$ (15 Psi). Then Pd(OH)$_2$/C (50 mg, 35.6 umol, 10 wt %) was added. The reaction mixture was stirred at rt for 12 hours under H$_2$ (15 Psi). On completion, the residue was filtered and the filtrate was concentrated in vacuo to give the title compound (600 mg, 85% purity) as a light yellow solid. LC-MS (ESI$^+$) m/z 347.2 (M+H)$^+$.

Step 3—2-[2-[2-(2,6-Dioxo-3-piperidyl)-1,3-dioxoisoindolin-4-yl]ethoxy]ethyl methanesulfonate To a solution of 2-(2,6-dioxo-3-piperidyl)-4-[2-(2-hydroxyethoxy)ethyl]isoindoline-1,3-dione (250 mg, 721.85 umol) in DCM (10 mL) was added TEA (219 mg, 2.17 mmol, 301 uL) and MsCl (124 mg, 1.08 mmol, 83.8 uL) at 0° C. The reaction mixture was stirred at rt for 30 min. The mixture was quenched by addition H$_2$O (50 mL), then extracted with DCM (2×100 mL). The organic phase was concentrated in vacuo to give the title compound (310 mg, 63% purity) as a yellow solid. LC-MS (ESI$^+$) m/z 425.0 (M+H)$^+$.

4-[2-[2-[4-[4-Amino-3-(difluoromethyl)pyrazol-1-yl]-1-piperidyl]ethoxy]ethyl]-2-(2,6-dioxo-3-piperidyl)isoindoline-1,3-dione (Intermediate NK)

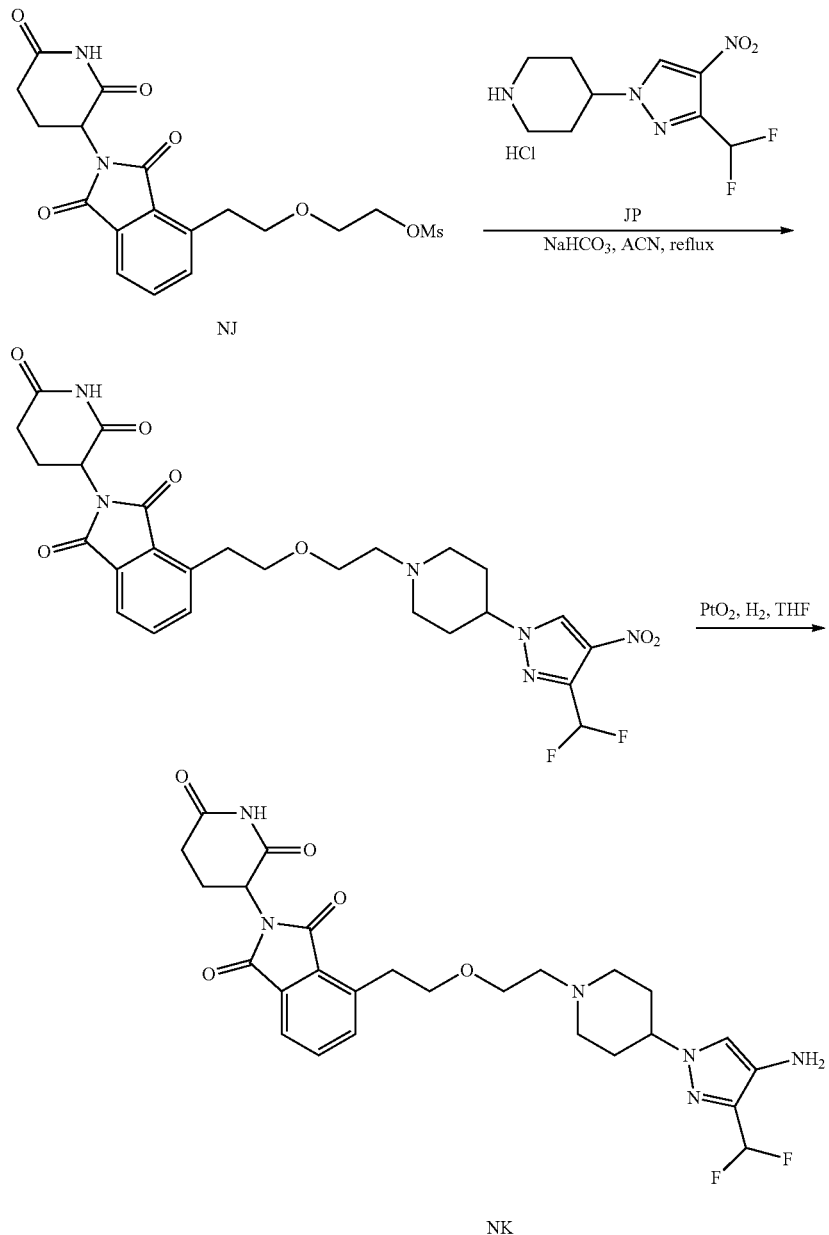

Step 1—4-[2-[2-[4-[3-(Difluoromethyl)-4-nitro-pyrazol-1-yl]-1-piperidyl]ethoxy]ethyl]-2-(2,6-dioxo-3-piperidyl)isoindoline-1,3-dione To a solution of 2-[2-[2-(2,6-dioxo-3-piperidyl)-1,3-dioxo-isoindolin-4-yl]ethoxy]ethyl methanesulfonate (300 mg, 706 umol, Intermediate NJ) and 4-[3-(difluoromethyl)-4-nitro-pyrazol-1-yl]piperidine (199 mg, 706 umol, HCl, Intermediate JP) in CH$_3$CN (20 mL) was added NaHCO$_3$ (178 mg, 2.12 mmol) and KI (11.7 mg, 70.6 umol). The reaction mixture was stirred at 80° C. for 12 hours. On completion, the mixture was filtered, and the filtrate was concentrated in vacuo to give the title compound (410 mg, 85% purity) as a yellow solid. LC-MS (ESI$^+$) m/z 575.2 (M+H)$^+$.

Step 2—4-[2-[2-[4-[4-Amino-3-(difluoromethyl) pyrazol-1-yl]-1-piperidyl]ethoxy]ethyl]-2-(2,6-dioxo-3-piperidyl)isoindoline-1,3-dione To a solution of 4-[2-[2-[4-[3-(difluoromethyl)-4-nitro-pyrazol-1-yl]-1-piperidyl]ethoxy]ethyl]-2-(2,6-dioxo-3-piperidyl)isoindoline-1,3-dione (260 mg, 452 umol) in THF (10 mL) was added PtO$_2$ (41.1 mg, 181 umol), the reaction mixture was stirred at rt under H$_2$ (15 psi) for 16 hrs. On completion, the mixture was filtered, the filtrate was concentrated was concentrated in vacuo to give the title compound (40 mg, 16% yield) as a white solid. LC-MS (ESI⁺) m/z 545.3 (M+H)⁺.

4-[5-[4-[4-Amino-3-(difluoromethyl)pyrazol-1-yl]-1-piperidyl]pentyl]-2-(2,6-dioxo-3-piperidyl)isoindoline-1,3-dione (Intermediate NL)

55.2 uL) and KI (7.86 mg, 47.3 umol), the reaction mixture was stirred at 80° C. for 16 hr. On completion, the mixture was filtered, and the filtrate was concentrated in vacuo. The residue was purified by column chromatography (SiO₂, DCM/MeOH=100/1 to 50/1) to give the title compound (140 mg, 51% yield) as a white solid. LC-MS (ESI⁺) m/z 573.3 (M+H)⁺.

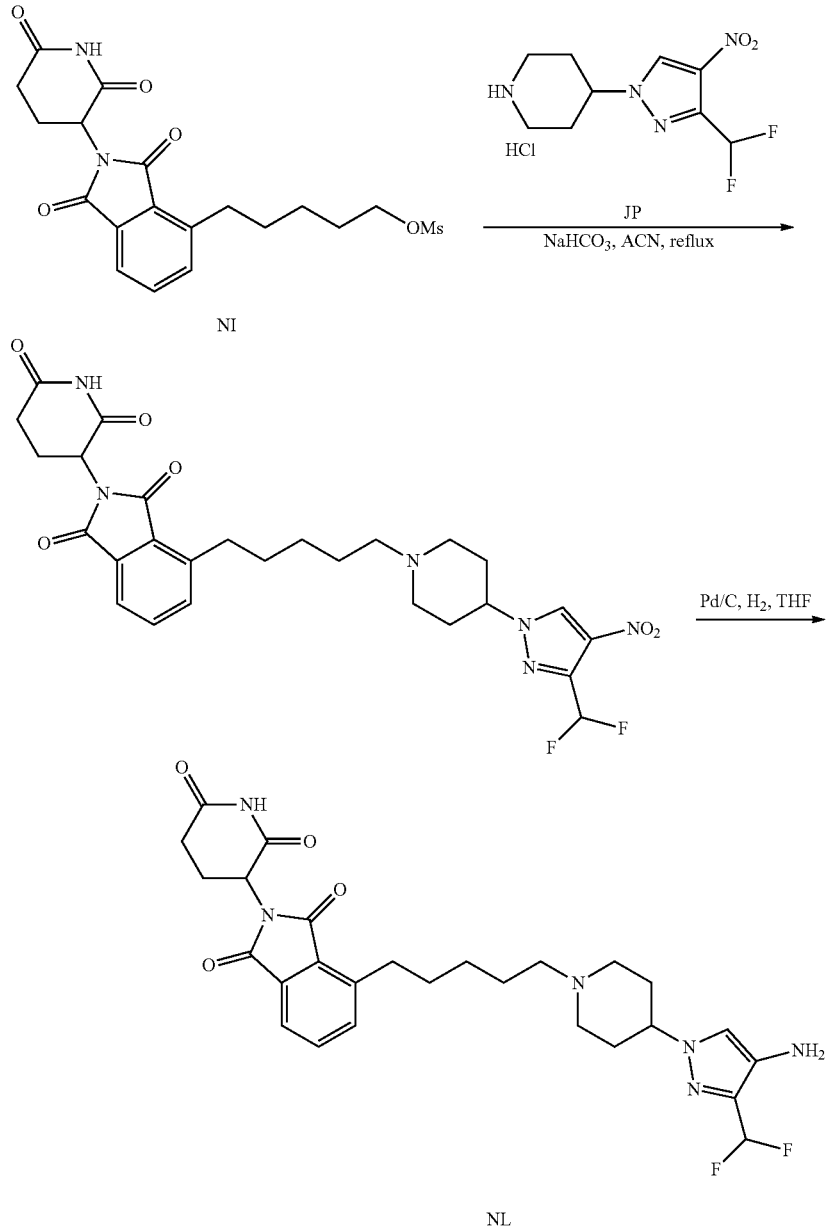

Step 1—4-[5-[4-[3-(Difluoromethyl)-4-nitro-pyrazol-1-yl]-1-piperidyl]pentyl]-2-(2,6-dioxo-3-piperidyl) isoindoline-1,3-dione To a solution of 5-[2-(2,6-dioxo-3-piperidyl)-1,3-dioxoisoindolin-4-yl]pentyl methanesulfonate (260 mg, 615 umol, Intermediate NI) and 4-[3-(difluoromethyl)-4-nitro-pyrazol-1-yl]piperidine (133 mg, 473 umol, HCl, Intermediate JP) in ACN (15 mL) was added NaHCO₃ (119 mg, 1.42 mmol, Step 2—4-[5-[4-[4-Amino-3-(difluoromethyl)pyrazol-1-yl]-1-piperidyl]pentyl]-2-(2,6-dioxo-3-piperidyl)isoindoline-1,3-dione To a solution of 4-[5-[4-[3-(difluoromethyl)-4-nitro-pyrazol-1-yl]-1-piperidyl]pentyl]-2-(2,6-dioxo-3-piperidyl) isoindoline-1,3-dione (190 mg, 331 umol) in THF (5 mL) was added PtO₂ (37.6 mg, 165 umol), and the reaction mixture was stirred at rt under H₂ (15 psi) for 3 hrs. On completion, the mixture was filtered, the filtrate was concentrated in vacuo to give the title compound (180 mg, 99% yield) as a white solid. LC-MS (ESI⁺) m/z 543.4 (M+H)⁺.

3-[2-(2,6-Dioxo-3-piperidyl)-1,3-dioxo-isoindolin-4-yl]propyl methanesulfonate (Intermediate NM)

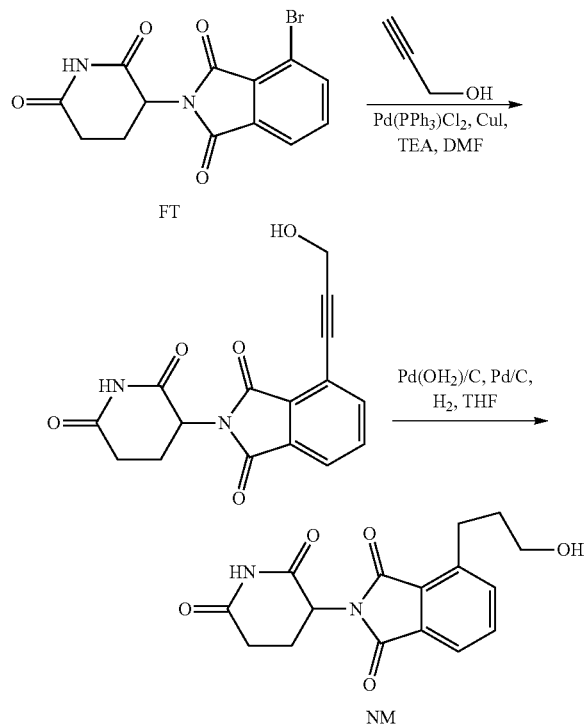

Step 1—2-(2,6-Dioxo-3-piperidyl)-4-(3-hydroxyprop-1-ynyl)isoindoline-1,3-dione

4-Bromo-2-(2,6-dioxo-3-piperidyl)isoindoline-1,3-dione (1.00 g, 2.97 mmol, Intermediate FT), prop-2-yn-1-ol (332 mg, 5.93 mmol, CAS #107-19-7), Pd(PPh₃)₂Cl₂ (208 mg, 296 umol), CuI (113 mg, 593 umol), and TEA (5.40 g, 53.4 mmol) were taken up into a microwave tube in DMF (20 mL). The sealed tube was heated at 80° C. for 0.5 hr under microwave. On completion, the mixture was poured into water (100 mL). The aqueous phase was extracted with ethyl acetate (2×50 mL). The combined organic phase was washed with brine (2×40 mL), dried with anhydrous Na₂SO₄, filtered and concentrated in vacuo. The residue was purified by column chromatography (SiO₂, Petroleum ether/Ethyl acetate=0:1) to give the title compound (185 mg, 9% yield) as white solid. LC-MS (ESI⁺) m/z 335.0 (M+Na)⁺.

Step 2—2-(2,6-Dioxo-3-piperidyl)-4-(3-hydroxypropyl)isoindoline-1,3-dione

To a mixture of 2-(2,6-dioxo-3-piperidyl)-4-(3-hydroxyprop-1-ynyl)isoindoline-1,3-dione (320 mg, 1.02 mmol) in THF (10 mL) was added Pd/C (2.05 mmol, 10 wt %), and Pd(OH)₂ (288 mg, 2.05 mmol) under H₂ (15 Psi), and the reaction mixture was stirred at rt for 5 hrs. On completion, the mixture was concentrated in vacuo to give the title compound (296 mg, 91% yield) as brown oil. LC-MS (ESI⁺) m/z 339.0 (M+Na)⁺.

Step 3—3-[2-(2,6-Dioxo-3-piperidyl)-1,3-dioxo-isoindolin-4-yl]propyl methanesulfonate To a mixture of 2-(2,6-dioxo-3-piperidyl)-4-(3-hydroxypropyl)isoindoline-1,3-dione (296 mg, 935 umol) in DCM (10 mL) was added DIPEA (362 mg, 2.81 mmol) and the mixture was cooled to 0° C. MsCl (161 mg, 1.40 mmol) was added into the mixture. The reaction mixture was stirred at rt for 1 hr. On completion, the mixture was poured into water (15 mL). The aqueous phase was extracted with ethyl acetate (2×20 mL). The combined organic phase was washed with brine (2×20 mL), then dried with anhydrous Na₂SO₄, filtered and concentrated in vacuo to give title compound (348 mg, 94% yield) as brown oil. LC-MS (ESI⁺) m/z 395.0 (M+H)⁺.

4-[3-[4-[3-(Difluoromethyl)-4-nitro-pyrazol-1-yl]-1-piperidyl]propyl]-2-(2,6-dioxo-3-piperidyl)isoindoline-1,3-dione (Intermediate NN)

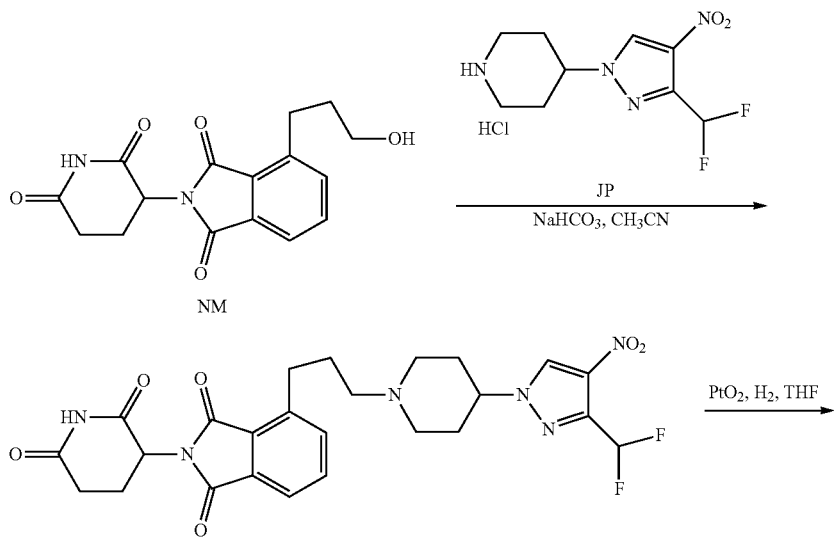

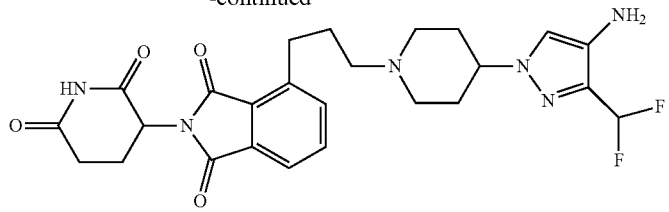

NN

Step 1—4-[3-[4-[3-(Difluoromethyl)-4-nitro-pyrazol-1-yl]-1-piperidyl]propyl]-2-(2,6-dioxo-3-piperidyl)isoindoline-1,3-dione To a mixture of 3-[2-(2,6-dioxo-3-piperidyl)-1,3-dioxo-isoindolin-4-yl]propyl methanesulfonate (348 mg, 882 umol, Intermediate NM), 4-[3-(difluoromethyl)-4-nitro-pyrazol-1-yl]piperidine (274.36 mg, 970 umol, HCl, Intermediate JP) in CH$_3$CN (10 mL) was added NaHCO$_3$ (296 mg, 3.53 mmol) and the mixture was stirred at 80° C. for 12 hrs. On completion, the mixture was concentrated in vacuo. The crude product was purified by column chromatography (SiO2, Petroleum ether/Ethyl acetate=0:1) to give title compound (190 mg, 30% yield) as a yellow solid. LC-MS (ESI$^+$) m/z 545.3 (M+H)$^+$.

Step 2—4-[3-[4-[3-(Difluoromethyl)-4-nitro-pyrazol-1-yl]-1-piperidyl]propyl]-2-(2,6-dioxo-3-piperidyl)isoindoline-1,3-dione To a mixture of 4-[3-[4-[3-(difluoromethyl)-4-nitro-pyrazol-1-yl]-1-piperidyl]propyl]-2-(2,6-dioxo-3-piperidyl)isoindoline-1,3-dione (20.0 mg, 36.7 umol) in THF (2 mL) was added PtO$_2$ (1.67 mg, 7.35 umol) under H$_2$ (15 Psi) and the reaction mixture was stirred at rt for 12 hrs. On completion, the mixture was concentrated in vacuo to give title compound (15 mg, 80% yield) as brown oil. LC-MS (ESI$^+$) m/z 515.2 (M+H)$^+$.

5-[2-(2,6-Dioxo-3-piperidyl)-1,3-dioxo-isoindolin-5-yl]pentyl methanesulfonate (Intermediate NO)

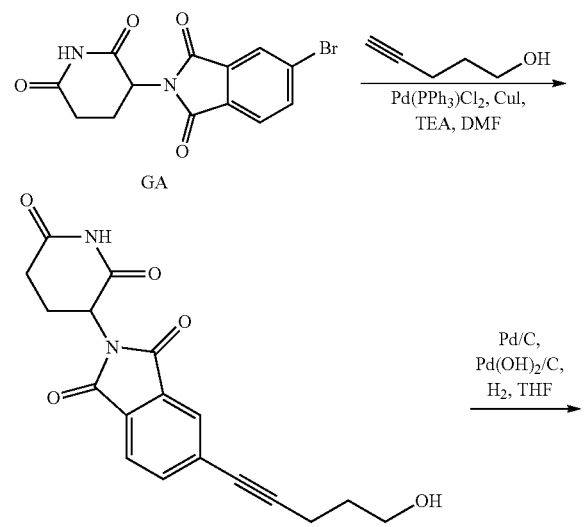

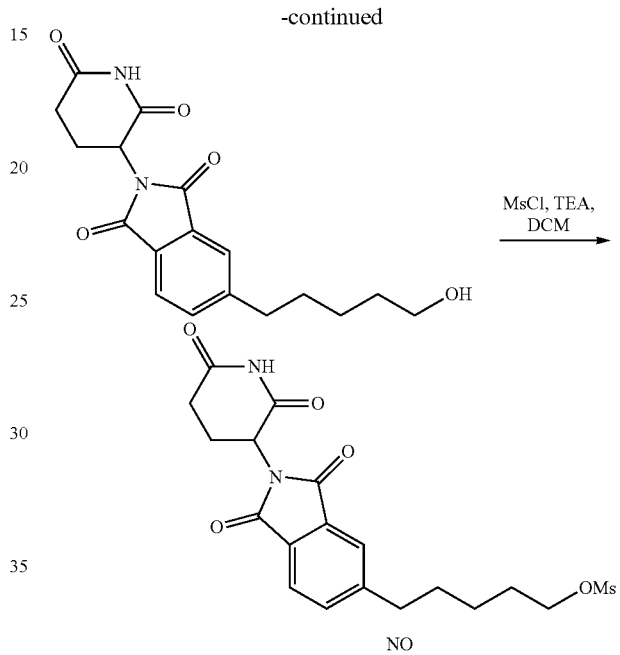

NO

Step 1—2-(2,6-Dioxo-3-piperidyl)-5-(5-hydroxypent-1-ynyl)isoindoline-1,3-dione A mixture of 5-bromo-2-(2,6-dioxo-3-piperidyl)isoindoline-1,3-dione (1.00 g, 2.97 mmol, Intermediate GA), pent-4-yn-1-ol (499 mg, 5.93 mmol), Pd(PPh$_3$)$_2$Cl$_2$ (208 mg, 296 umol), CuI (56.0 mg, 296 umol) and TEA (5.40 g, 53.3 mmol, 7.43 mL) in DMF (4 mL) was degassed and purged with N$_2$ gas 3 times. The mixture was stirred at 80° C. for 0.5 hr under microwave. On completion, the mixture was extracted with EA (2×100 mL). The organic layer was washed with brine (100 mL), dried over anhydrous Na$_2$SO$_4$, then filtered and concentrated in vacuo. The residue was purified by silica gel chromatography to give the title compound (900 mg, 89% yield) as light yellow solid. $^1$H NMR (400 MHz, DMSO-d$_6$) δ 11.14 (s, 1H), 7.94-7.78 (m, 3H), 5.17 (dd, J=5.6, 12.8 Hz, 1H), 4.57 (t, J=5.2 Hz, 1H), 3.55 (q, J=6.0 Hz, 2H), 2.97-2.84 (m, 1H), 2.67-2.55 (m, 4H), 2.15-2.02 (m, 1H), 1.77-1.70 (m, 2H).

Step 2—2-(2,6-Dioxo-3-piperidyl)-5-(5-hydroxypentyl)isoindoline-1,3-dione

To a solution of 2-(2,6-dioxo-3-piperidyl)-5-(5-hydroxypent-1-ynyl)isoindoline-1,3-dione (900 mg, 2.64 mmol) in THF (20 mL) was added Pd/C (100 mg, 10 wt %) and Pd(OH)$_2$/C (100 mg, 10 wt %) under H$_2$ atmosphere (15 psi). The mixture was stirred at rt for 2 hrs. On completion, the mixture was filtered and the filtrate was concentrated in vacuo to give the title compound (800 mg, 87% yield) as light yellow solid. $^1$H NMR (400 MHz, DMSO-d$_6$) δ 11.12 (s, 1H), 7.89-7.65 (m, 3H), 5.14 (dd, J=5.2, 12.8 Hz, 1H), 4.38-4.33 (m, 1H), 3.43-3.34 (m, 2H), 2.89 (s, 1H), 2.78 (t, J=7.6 Hz, 2H), 2.65-2.52 (m, 2H), 2.12-2.00 (m, 1H), 1.80-1.72 (m, 1H), 1.68-1.60 (m, 2H), 1.48-1.41 (m, 2H), 1.35-1.24 (m, 2H).

Step 3—5-[2-(2,6-Dioxo-3-piperidyl)-1,3-dioxo-isoindolin-5-yl]pentyl methanesulfonate To a solution of 2-(2,6-dioxo-3-piperidyl)-5-(5-hydroxypentyl)isoindoline-1,3-dione (200 mg, 580 umol) in DCM (20 mL) was added TEA (176 mg, 1.74 mmol) and MsCl (133 mg, 1.16 mmol, 89.9 uL). The mixture was stirred at rt for 3 hrs. On completion, the mixture was washed with citric acid (10 mL), and brine (20 mL). The organic layer was dried over anhydrous Na$_2$SO$_4$, filtered and the filtrate was concentrated in vacuo to give the title compound (240 mg, 97% yield) as yellow oil. LC-MS (ESI$^+$) m/z 423.3 (M+1)$^+$.

5-[3-[4-[4-Amino-3-(difluoromethyl)pyrazol-1-yl]-1-piperidyl]propyl]-2-(2,6-dioxo-3-piperidyl)isoindoline-1,3-dione (Intermediate NP)

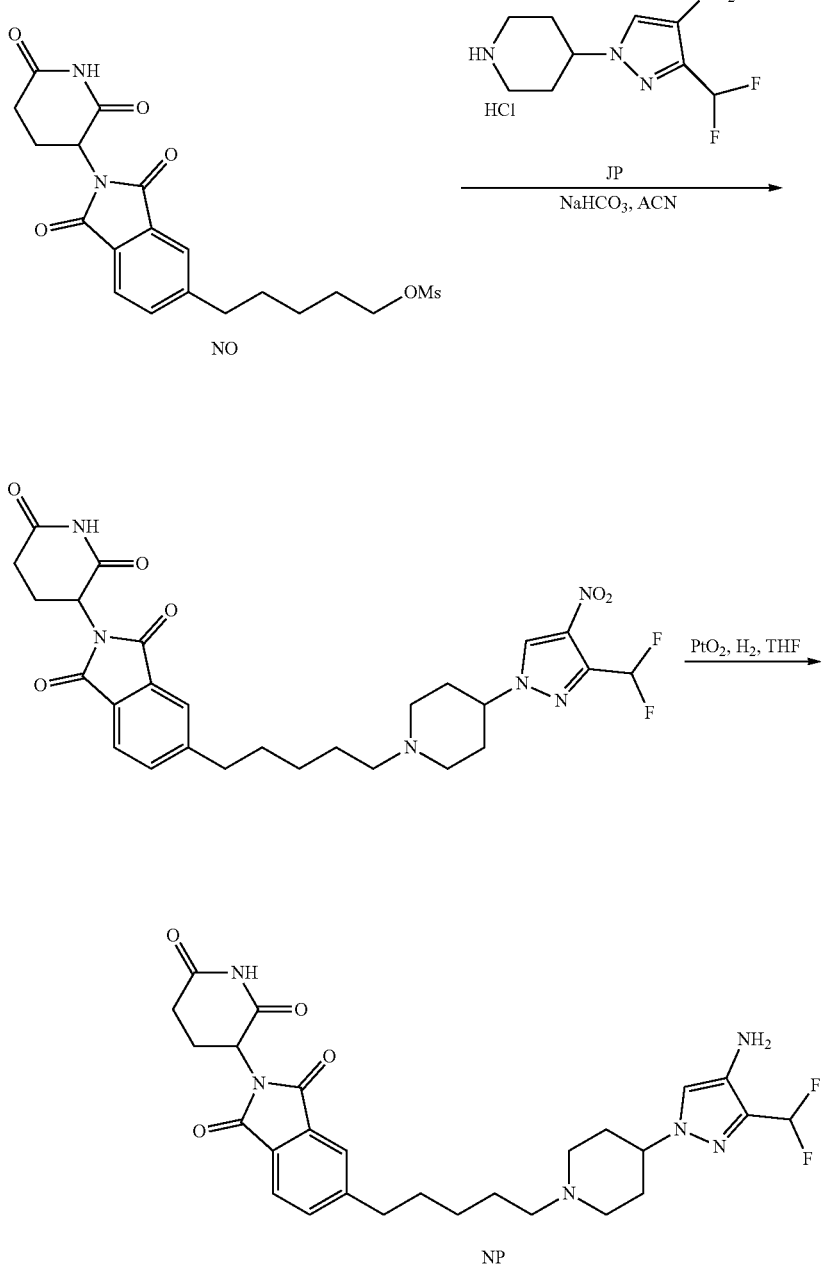

Step 1—5-[5-[4-[3-(Difluoromethyl)-4-nitro-pyrazol-1-yl]-1-piperidyl]pentyl]-2-(2,6-dioxo-3-piperidyl) isoindoline-1,3-dione To a mixture of 5-[2-(2,6-dioxo-3-piperidyl)-1,3-dioxo-isoindolin-5-yl]pentyl methanesulfonate (179 mg, 424 umol, Intermediate NO) and 4-[3-(difluoromethyl)-4-nitro-pyrazol-1-yl]piperidine (100 mg, 354 umol, HCl, Intermediate JP) in ACN (8 mL) was added NaHCO$_3$ (89.2 mg, 1.06 mmol) and KI (5.87 mg, 35.4 umol). The mixture was stirred at 80° C. for 16 hrs. On completion, the mixture was filtered and the filtrate was concentrated in vacuo, the residue was purified by Pre-HPLC (acid condition) to give the title compound (140 mg, 69% yield) as white solid. $^1$H NMR (400 MHz, DMSO-d$_6$) δ 11.11 (s, 1H), 9.08 (s, 1H), 7.85 (d, J=7.6 Hz, 1H), 7.79 (s, 1H), 7.73 (d, J=7.2 Hz, 1H), 7.46-7.17 (m, 1H), 5.14 (dd, J=5.2, 12.8 Hz, 1H), 4.38-4.27 (m, 1H), 3.03-2.95 (m, 2H), 2.94-2.85 (m, 1H), 2.83-2.77 (m, 2H), 2.71-2.53 (m, 2H), 2.38-2.31 (m, 2H), 2.16-1.95 (m, 7H), 1.73-1.62 (m, 2H), 1.55-1.44 (m, 2H), 1.37-1.28 (m, 2H).

Step 2—5-[3-[4-[4-Amino-3-(difluoromethyl)pyrazol-1-yl]-1-piperidyl]propyl]-2-(2,6-dioxo-3-piperidyl)isoindoline-1,3-dione To a solution of 5-[5-[4-[3-(difluoromethyl)-4-nitro-pyrazol-1-yl]-1-piperidyl]pentyl]-2-(2,6-dioxo-3-piperidyl) isoindoline-1,3-dione (140 mg, 244 umol) in THF (20 mL) was added PtO$_2$ (11.1 mg, 48.9 umol). The mixture was stirred at rt for 16 hrs under H$_2$ (15 psi). On completion, the mixture was filtered and the filtrate was concentrated in vacuo to give the title compound (130 mg, 98% yield) as white solid. $^1$H NMR (400 MHz, DMSO-d$_6$) δ 11.11 (s, 1H), 7.85-7.83 (m, 2H), 7.78 (s, 1H), 7.74-7.71 (m, 2H), 7.17 (s, 1H), 7.03-6.61 (m, 3H), 5.14 (dd, J=5.6, 12.8 Hz, 1H), 3.99-3.94 (m, 1H), 2.96-2.88 (m, 3H), 2.84-2.76 (m, 2H), 2.67-2.58 (m, 2H), 2.30-2.24 (m, 2H), 1.98-1.74 (m, 7H), 1.72-1.60 (m, 2H), 1.53-1.41 (m, 2H), 1.33-1.22 (m, 2H).

3-[2-(2,6-Dioxo-3-piperidyl)-1,3-dioxo-isoindolin-5-yl]propyl methanesulfonate (Intermediate NO)

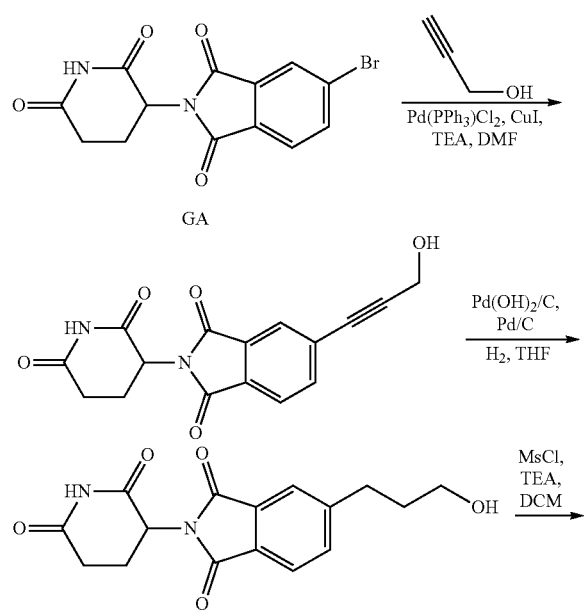

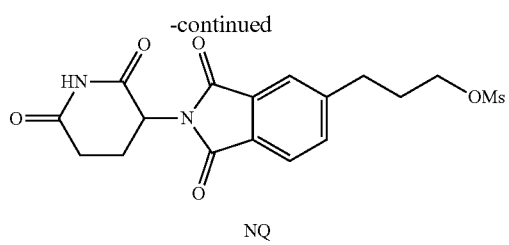

NQ

Step 1—2-(2,6-Dioxo-3-piperidyl)-5-(3-hydroxy-prop-1-ynyl)isoindoline-1,3-dione A mixture of 5-bromo-2-(2,6-dioxo-3-piperidyl)isoindoline-1,3-dione (1.00 g, 2.97 mmol, Intermediate GA), prop-2-yn-1-ol (333 mg, 5.93 mmol, CAS #107-19-7), Pd(PPh$_3$)$_2$Cl$_2$ (208 mg, 297 umol), CuI (56.5 mg, 297 umol) and TEA (5.40 g, 53.4 mmol, 7.43 mL) in DMF (4 mL) was degassed and purged with N$_2$ gas 3 times, and then the mixture was stirred at 80° C. for 0.5 hr under microwave. On completion, the mixture was extracted with EA (2×100 mL), the organic layer was washed with brine (100 mL), dried over anhydrous Na$_2$SO$_4$, then filtered and concentrated in vacuo. The residue was purified by silica gel chromatography to give the title compound (800 mg, 86% yield) as light white solid. $^1$H NMR (400 MHz, DMSO-d$_6$) δ 11.15 (s, 1H), 7.96-7.90 (m, 3H), 5.48 (t, J=6.0 Hz, 1H), 5.17 (dd, J=5.2, 12.8 Hz, 1H), 4.38 (d, J=6.0 Hz, 2H), 2.96-2.84 (m, 1H), 2.70-2.54 (m, 2H), 2.13-2.03 (m, 1H).

Step 2—2-(2,6-Dioxo-3-piperidyl)-5-(3-hydroxypropyl)isoindoline-1,3-dione

To a solution of 2-(2,6-dioxo-3-piperidyl)-5-(3-hydroxy-prop-1-ynyl)isoindoline-1,3-dione (800 mg, 2.56 mmol) in THF (20 mL) was added Pd/C (200 mg, 10 wt %) and Pd(OH)$_2$/C (200 mg, 10 wt %). The mixture was stirred at rt for 3 hrs under H$_2$ (15 psi) atmosphere. On completion, the mixture was filtered and the filtrate was concentrated in vacuo to give the title compound (800 mg, 98% yield) as light brown solid. $^1$H NMR (400 MHz, DMSO-d$_6$) δ 11.12 (s, 1H), 7.86-7.69 (m, 3H), 5.14 (dd, J=5.2, 12.8 Hz, 1H), 4.54 (t, J=5.2 Hz, 1H), 3.45-3.38 (m, 2H), 2.96-2.90 (m, 1H), 2.87-2.79 (m, 2H), 2.69-2.53 (m, 2H), 2.11-2.01 (m, 1H), 1.83-1.72 (m, 2H).

Step 3—3-[2-(2,6-Dioxo-3-piperidyl)-1,3-dioxo-isoindolin-5-yl]propyl methanesulfonate To a solution of 2-(2,6-dioxo-3-piperidyl)-5-(3-hydroxypropyl)isoindoline-1,3-dione (300 mg, 948 umol) in DCM (10 mL) was added MsCl (217 mg, 1.90 mmol) and TEA (288 mg, 2.85 mmol). The mixture was stirred at rt for 3 hrs. On completion, the mixture was washed with citric acid (10 mL), and brine (20 mL). The organic layer was dried over anhydrous Na$_2$SO$_4$, filtered and the filtrate was concentrated in vacuo to give the title compound (350 mg, 93% yield) as yellow solid. LC-MS (ESI$^+$) m/z 412.2 (M+18)$^+$.

5-[3-[4-[4-Amino-3-(difluoromethyl)pyrazol-1-yl]-1-piperidyl]propyl]-2-(2,6-dioxo-3-piperidyl)isoindoline-1,3-dione (Intermediate NR)

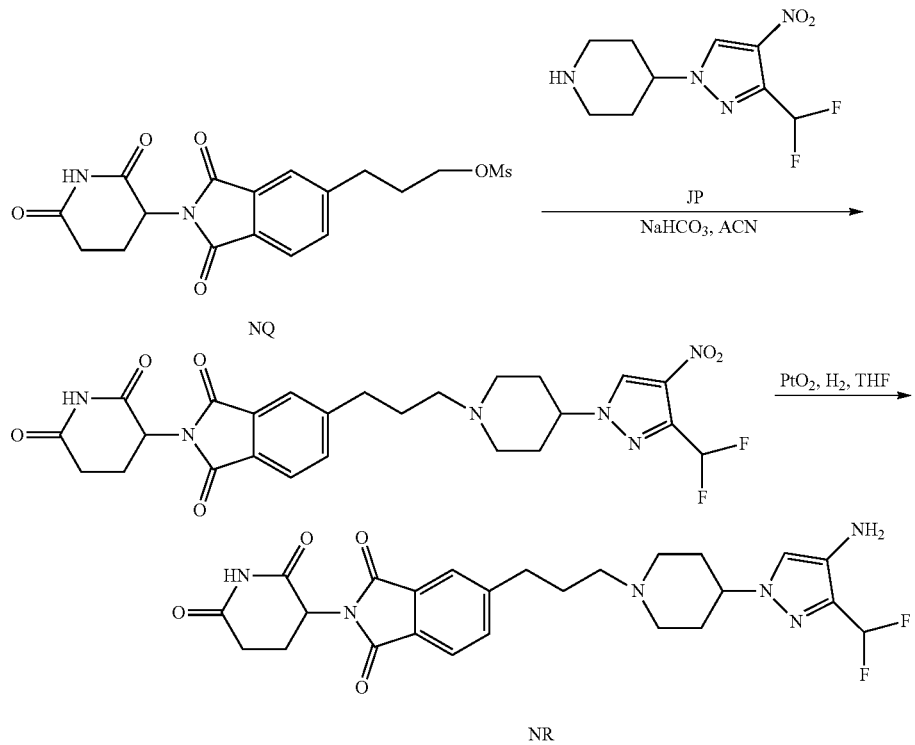

Step 1—5-[3-[4-[4-Amino-3-(difluoromethyl)pyrazol-1-yl]-1-piperidyl]propyl]-2-(2,6-dioxo-3-piperidyl)isoindoline-1,3-dione To a mixture of 3-[2-(2,6-dioxo-3-piperidyl)-1,3-dioxoisoindolin-5-yl]propyl methanesulfonate (167 mg, 424 umol, Intermediate NQ) and 4-[3-(difluoromethyl)-4-nitropyrazol-1-yl]piperidine (100 mg, 354 umol, HCl, Intermediate JP) in ACN (10 mL) was added NaHCO$_3$ (89.0 mg, 1.06 mmol) and KI (5.87 mg, 35.4 umol). The mixture was stirred at 80° C. for 16 hrs. On completion, the mixture was filtered and the filtrate was concentrated in vacuo, the residue was purified by Pre-HPLC (acid condition) to give the title compound (100 mg, 52% yield) as white solid. $^1$H NMR (400 MHz, DMSO-d$_6$) δ 11.11 (s, 1H), 9.09 (s, 1H), 7.87-7.80 (m, 1H), 7.78-7.71 (m, 1H), 7.46-7.17 (m, 1H), 5.14 (dd, J=5.2, 12.8 Hz, 1H), 4.38-4.28 (m, 1H), 3.00-2.93 (m, 2H), 2.91-2.79 (m, 3H), 2.65-2.53 (m, 2H), 2.39-2.29 (m, 2H), 2.12-2.00 (m, 7H), 1.88-1.76 (m, 2H).

Step 2—5-[3-[4-[4-Amino-3-(difluoromethyl)pyrazol-1-yl]-1-piperidyl]propyl]-2-(2,6-dioxo-3-piperidyl)isoindoline-1,3-dione To a solution of 5-[3-[4-[3-(difluoromethyl)-4-nitro-pyrazol-1-yl]-1-piperidyl]propyl]-2-(2,6-dioxo-3-piperidyl)isoindoline-1,3-dione (100 mg, 184 umol) in THF (15 mL) was added PtO$_2$ (41.7 mg, 184 umol). The mixture was stirred at rt for 16 hrs under H$_2$ (15 psi) atmosphere. On completion, the mixture was filtered and the filtrate was concentrated in vacuo to give the title compound (80 mg, 85% yield) as white solid. LC-MS (ESI$^+$) m/z 515.3 (M+1)$^+$.

3-[1-Oxo-4-(4-piperidylamino)isoindolin-2-yl]piperidine-2,6-dione (Intermediate NS)

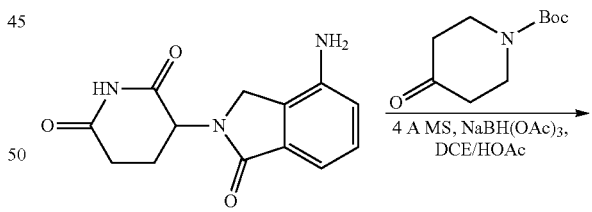

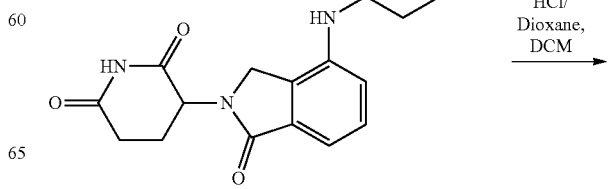

-continued

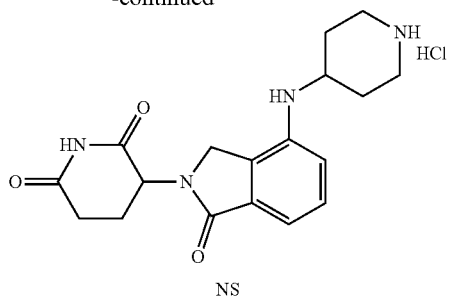

NS

Step 1—Tert-butyl 4-[[2-(2,6-dioxo-3-piperidyl)-1-oxo-isoindolin-4-yl]amino]piperidine-1-carboxylate To a solution of 3-(4-amino-1-oxo-isoindolin-2-yl)piperidine-2,6-dione (400 mg, 1.54 mmol, CAS #191732-72-6) and tert-butyl 4-oxopiperidine-1-carboxylate (615 mg, 3.09 mmol) in a mixed solvent of DCE (10 mL) and HOAc (1.05 g, 17.5 mmol) was added molecular sieves (200 mg, 386 umol, 4 Å). The reaction mixture was stirred at 30° C. for 4 hrs. Then, NaBH(OAc)$_3$ (327 mg, 1.54 mmol) was added. The resulting reaction mixture was stirred at 30° C. for 12 hrs. On completion, the reaction mixture was concentrated in vacuo to give the crude product which was purified by reversed-phase chromatography (0.1% FA condition) to give the title compound (168 mg, 22% yield) as a white solid. $^1$H NMR (400 MHz, DMSO-d$_6$) δ 11.00 (s, 1H), 7.29 (t, J=7.6 Hz, 1H), 6.95 (d, J=7.6 Hz, 1H), 6.86 (d, J=8.4 Hz, 1H), 5.35 (d, J=8.4 Hz, 1H), 5.12 (dd, J=5.2, 12.8 Hz, 1H), 4.31-4.10 (m, 2H), 3.92 (d, J=12.6 Hz, 2H), 3.02-2.85 (m, 3H), 2.71-2.59 (m, 1H), 2.38-2.23 (m, 1H), 2.09-2.00 (m, 1H), 1.92-1.90 (m, 2H), 1.41 (s, 9H), 1.33-1.29 (m, 2H) LC-MS (ESI$^+$) m/z 387.1 (M-56)$^+$.

Step 2—3-[1-Oxo-4-(4-piperidylamino)isoindolin-2-yl]piperidine-2,6-dione

To a solution of tert-butyl 4-[[2-(2,6-dioxo-3-piperidyl)-1-oxo-isoindolin-4-yl]amino]piperidine-1-carboxylate (210 mg, 475 umol) in dichloromethane (10 mL) was added HCl/dioxane (4 M, 5 mL). The reaction mixture was stirred at 20° C. for 1 hr. On completion, the reaction mixture was concentrated in vacuo to give the title compound (180 mg, 100% yield, HCl salt) as a white solid which was used for the next step without purification. LC-MS (ESE) m/z 343.1 (M+H)$^+$.

3-[4-[[1-[2-[2-(2-Aminoethoxy)ethoxy]ethyl]-4-piperidyl]amino]-1-oxo-isoindolin-2-yl]piperidine-2,6-dione (Intermediate NT)

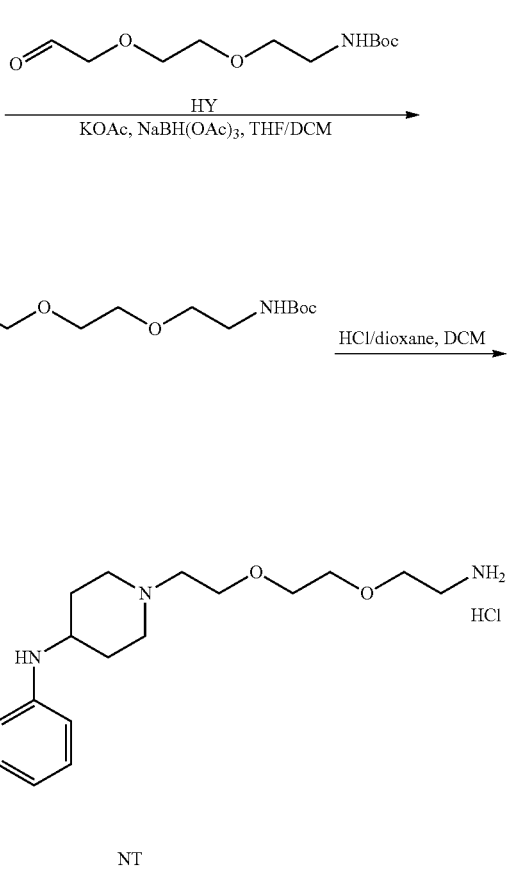

Step 1—Tert-butyl N-[2-[2-[2-[4-[[2-(2,6-dioxo-3-piperidyl)-1-oxo-isoindolin-4-yl]amino]-1-piperidyl]ethoxy]ethoxy]ethyl]carbamate To a solution of 3-[1-oxo-4-(4-piperidylamino)isoindolin-2-yl]piperidine-2,6-dione (180 mg, 475 umol, HCl, Intermediate NS) and tert-butyl N-[2-[2-(2-oxoethoxy)ethoxy]ethyl]carbamate (176.0 mg, 712 umol, Intermediate HY) in THF (20 mL) was added KOAc (93.2 mg, 949 umol) and NaBH(OAc)₃ (111 mg, 522 umol). The reaction mixture was stirred at rt for 36 hrs. On completion, the reaction mixture was quenched with water (1 mL) and the mixture was concentrated in vacuo. The residue was purified by prep-HPLC (condition: 0.1% FA) to give the title compound (130 mg, 45% yield) as a colorless oil. LC-MS (ESI⁺) m/z 574.2 (M+H)⁺. 1H NMR (400 MHz, DMSO-d₆) δ 11.03 (s, 1H), 7.30-7.25 (m, 1H), 6.93 (d, J=7.6 Hz, 1H), 6.82-6.75 (m, 2H), 5.33 (d, J=7.6 Hz, 1H), 5.13 (dd, J=5.2, 13.2 Hz, 1H), 4.26-4.11 (m, 2H), 4.26-4.10 (m, 1H), 3.06 (d, J=6.0 Hz, 2H), 2.99-2.89 (m, 3H), 2.68-2.59 (m, 1H), 2.30-2.26 (m, 1H), 2.20-2.14 (m, 2H), 2.06-2.00 (m, 1H), 1.92-1.88 (m, 2H), 1.48-1.42 (m, 2H), 1.37 (s, 9H).

Step 2—3-[4-[[1-[2-[2-(2-Aminoethoxy)ethoxy]ethyl]-4-piperidyl]amino]-1-oxo-isoindolin-2-yl]piperidine-2,6-dione To a solution of tert-butyl N-[2-[2-[2-[4-[[2-(2,6-dioxo-3-piperidyl)-1-oxo-isoindolin-4-yl]amino]-1-piperidyl]ethoxy]ethoxy]ethyl]carbamate (130 mg, 227 umol) in DCM (5 mL) was added HCl/dioxane (4 M, 5 mL). The reaction mixture was stirred at rt for 1 hr. On completion, the mixture was concentrated in vacuo to give the title compound (116 mg, 99% yield, HCl salt) as a white solid. LC-MS (ESI⁺) m/z 474.2 (M+H)⁺.

4-[[1-[2-(2-Aminoethoxy)ethyl]-4-piperidyl]amino]-2-(2,6-dioxo-3-piperidyl)isoindoline-1,3-dione (Intermediate NU)

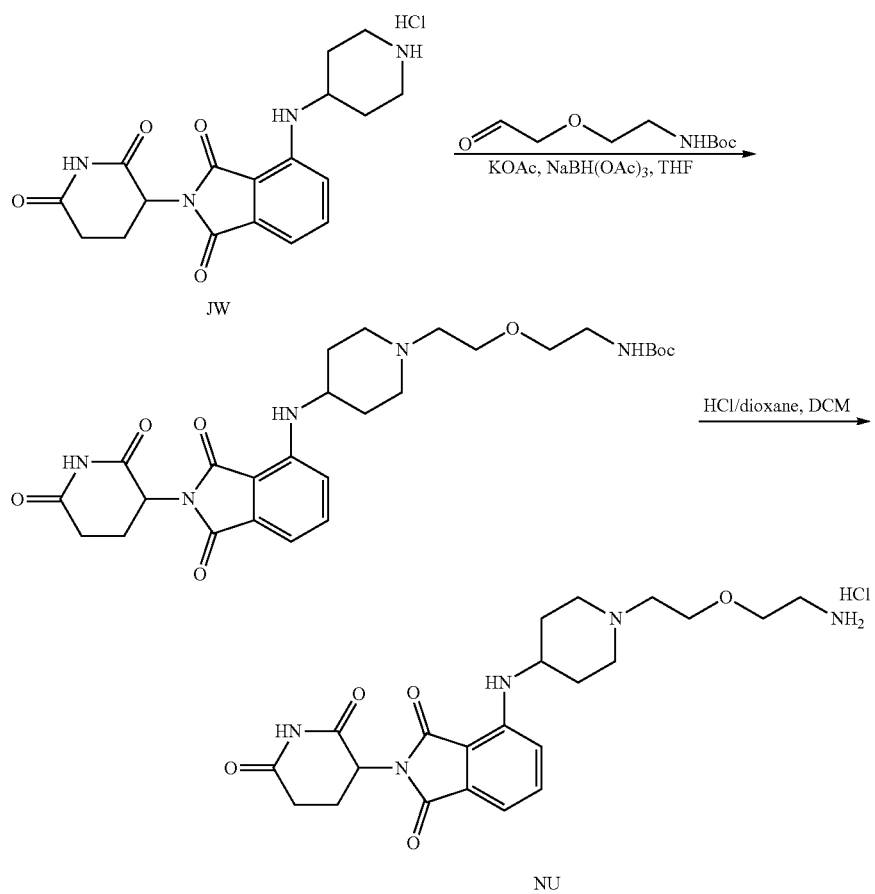

Step 1—Tert-butyl N-[2-[2-[4-[[2-(2,6-dioxo-3-piperidyl)-1,3-dioxo-isoindolin-4-yl]amino]-1-piperidyl]ethoxy]ethyl]carbamate To a solution of 2-(2,6-dioxo-3-piperidyl)-4-(4-piperidylamino)isoindoline-1,3-dione (300 mg, 764 umol, HCl, Intermediate JW) and tert-butyl N-[2-(2-oxoethoxy)ethyl]carbamate (233 mg, 1.15 mmol, synthesized via Step 1 of Intermediate FS) in THF (10 mL) was added KOAc (150 mg, 1.53 mmol). One hour later, NaBH(OAc)₃ (324 mg, 1.53 mmol) was added. The reaction mixture was stirred at rt for 16 hrs. On completion, the mixture was concentrated in vacuo. The residue was purified reverse phase (0.1% HCl condition) to give the title compound (300 mg, 72% yield) as a white solid. LC-MS (ESI+) m/z 544.4 (M+H)+.

Step 2—4-[[1-[2-(2-Aminoethoxy)ethyl]-4-piperidyl]amino]-2-(2,6-dioxo-3-piperidyl)isoindoline-1,3-dione To a solution of tert-butyl N-[2-[2-[4-[[2-(2,6-dioxo-3-piperidyl)-1,3-dioxo-isoindolin-4-yl]amino]-1-piperidyl]ethoxy]ethyl]carbamate (300 mg, 552 umol) in DCM (5 mL) was added HCl/dioxane (10 mL). The reaction mixture was stirred at rt for 10 hrs. On completion, the mixture was concentrated in vacuo to give the title compound (240 mg, 91% yield, HCl) as a yellow solid. LC-MS (ESI+) m/z 444.1 (M+H)+.

3-(5-Amino-1-oxo-isoindolin-2-yl)piperidine-2,6-dione (Intermediate NV)

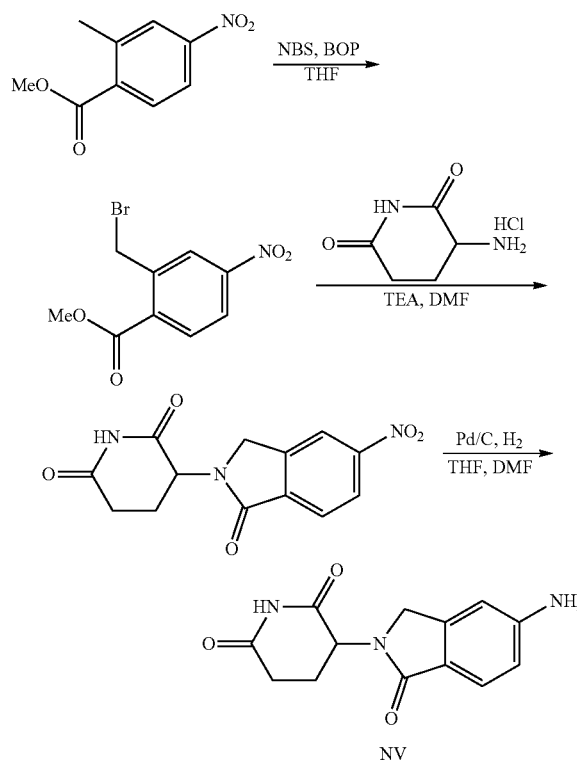

Step 1—Methyl 2-(bromomethyl)-4-nitro-benzoate

To a solution of methyl 2-methyl-4-nitro-benzoate (3.00 g, 15.4 mmol) in CCl4 (60.0 mL) was added NBS (3.28 g, 18.4 mmol) and BOP (68.0 mg, 154 umol). The reaction mixture was stirred at 85° C. for 12 hrs. On completion, the mixture was washed with saturated NaHCO3 (20.0 mL) and brine (50.0 mL), dried over anhydrous MgSO4, filtered and concentrated in vacuo. The residue was purified by silica gel column chromatography (PE:AcOEt=3:1) to give the title compound (4.21 g, 100% yield) as a colorless oil. 1H NMR (400 MHz, CDCl3) δ 8.30 (d, J=2.0 Hz, 1H), 8.20 (dd, J=2.0, 6.4 Hz, 1H), 8.10 (d, J=6.4 Hz, 1H), 4.96 (s, 2H), 4.00 (s, 3H).

Step 2—3-(5-Nitro-1-oxo-isoindolin-2-yl)piperidine-2,6-dione

To a solution of 3-aminopiperidine-2,6-dione (2.00 g, 12.2 mmol, HCl) and methyl 2-(bromomethyl)-4-nitro-benzoate (4.21 g, 15.4 mmol) in DMF (10.0 mL) was added TEA (3.07 g, 30.4 mmol). The reaction mixture was stirred at 75° C. for 12 hrs. On completion, the reaction mixture was diluted with water (200 mL), filtered. The filtered cake was collected. The reaction mixture was concentrated in vacuo. The residue was triturated EA:H2O=1:1 (50 mL) to give the title compound (1.7 g, 48% yield) as a blue solid. 1H NMR (400 MHz, DMSO-d6) δ 11.04 (s, 1H), 8.53 (d, J=1.2 Hz, 1H), 8.36 (dd, J=2.0, 8.4 Hz, 1H), 7.98 (d, J=8.4 Hz, 1H), 5.17 (dd, J=5.2, 13.2 Hz, 1H), 4.69-4.45 (m, 1H), 3.01-2.86 (m, 1H), 2.68-2.59 (m, 1H), 2.48-2.35 (m, 1H), 2.13-2.02 (m, 1H).

Step 3—3-(5-Amino-1-oxo-isoindolin-2-yl)piperidine-2,6-dione

To a solution of 3-(5-nitro-1-oxo-isoindolin-2-yl)piperidine-2,6-dione (500 mg, 1.73 mmol) in a mixed of solvent DMF (5.00 mL) and THF (10.0 mL) was added Pd/C (50.0 mg, 1.73 mmol, 10% wt) under N2. The suspension was degassed under vacuum and purged with H2 several times. The mixture was stirred under H2 (15 psi) at rt for 12 hours. On completion, the reaction mixture was filtered and the filter cake was collected and dried in vacuo to give the title compound (530 mg, 82% yield) as a brown solid. LC-MS (ESI+) m/z 260.2 (M+H)+.

3-[1-Oxo-5-(4-piperidylamino)isoindolin-2-yl]piperidine-2,6-dione (Intermediate NW)

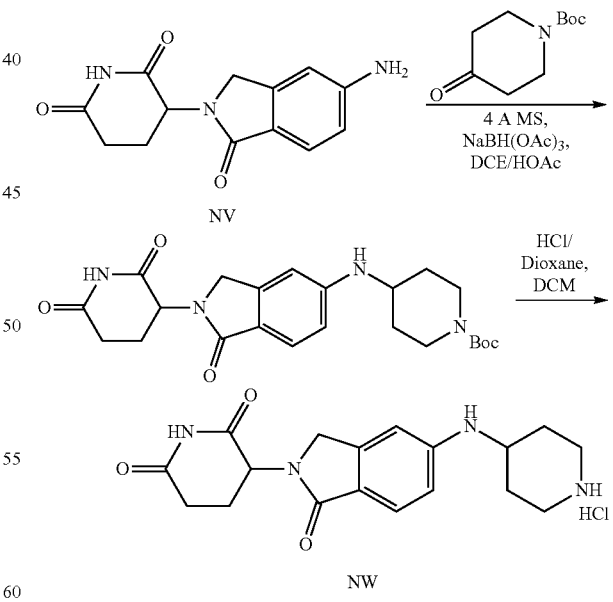

Step 1—Tert-butyl 4-[[2-(2,6-dioxo-3-piperidyl)-1-oxo-isoindolin-5-yl]amino]piperidine-1-carboxylate To a solution of 3-(5-amino-1-oxo-isoindolin-2-yl)piperidine-2,6-dione (448 mg, 1.73 mmol, Intermediate NV) and tert-butyl 4-oxopiperidine-1-carboxylate (689 mg, 3.46 mmol) in a mixed solvent of DCE (10 mL) and HOAc (1.18 g, 19.6 mmol) was added molecular sieves (200 mg, 386 umol, 4 Å). The reaction mixture was stirred at 30° C. for 4 hrs. Then, NaBH(OAc)$_3$ (366 mg, 1.73 mmol) was added. The resulting reaction mixture was stirred at 30° C. for 12 hrs. On completion, the reaction mixture was concentrated in vacuo to give the crude product, which was purified by reversed-phase chromatography (0.1% FA condition) to give the title compound (120 mg, 15% yield) as a white solid. $^1$H NMR (400 MHz, DMSO-d$_6$) δ 10.93 (s, 1H), 7.39 (d, J=8.8 Hz, 1H), 7.26-7.17 (m, 1H), 6.69 (s, 1H), 6.28 (d, J=8.8 Hz, 1H), 5.02 (dd, J=5.2, 13.2 Hz, 1H), 4.34-4.10 (m, 2H), 3.89 (d, J=12.4 Hz, 2H), 3.06-2.82 (m, 3H), 2.71-2.55 (m, 1H), 2.41-2.29 (m, 1H), 1.95-1.93 (m, 1H), 1.92-1.89 (m, 2H), 1.41 (s, 9H), 1.27-1.24 (m, 2H); LC-MS (ESI$^+$) m/z 443.1 (M+H)$^+$.

Step 2—3-[1-Oxo-5-(4-piperidylamino)isoindolin-2-yl]piperidine-2,6-dione

To a solution of tert-butyl 4-[[2-(2,6-dioxo-3-piperidyl)-1-oxo-isoindolin-5-yl]amino]piperidine-1-carboxylate (120 mg, 257.6 umol) in DCM (5.00 mL) was added HCl/dioxane (4.00 M, 2.83 mL). The reaction mixture was stirred at rt for 1 hr. On completion, the reaction mixture was concentrated in vacuo to give the title compound (97.6 mg, 100% yield, HCl) as a white solid. LC-MS (ESI$^+$) m/z 343.1 (M+H)$^+$.

3-[5-[[1-[2-[2-(2-Aminoethoxy)ethoxy]ethyl]-4-piperidyl]amino]-1-oxo-isoindolin-2-yl]piperidine-2,6-dione (Intermediate NX)

Step 1—Tert-butyl N-[2-[2-[2-[4-[[2-(2,6-dioxo-3-piperidyl)-1-oxo-isoindolin-5-yl]amino]-1-piperidyl]ethoxy]ethoxy]ethyl]carbamate To a solution of 3-[1-oxo-5-(4-piperidylamino)isoindolin-2-yl]piperidine-2,6-dione (97.0 mg, 256 umol, HCl, Intermediate NW) and 2-(2,6-dioxo-3-piperidyl)-5-piperazin-1-yl-isoindoline-1,3-dione (82.3 mg, 333 umol, synthesized via Steps 1-2 of Intermediate IB) in a mixed of solvent DMF (3.00 mL) and DCM (20.0 mL) was added KOAc (50.3 mg, 512 umol) and NaBH(OAc)$_3$ (81.4 mg, 384 umol). The reaction mixture was stirred at rt for 12 hrs. On completion, the reaction mixture was quenched with water (1.00 mL) and the mixture was concentrated in vacuo. The residue was purified by prep-HPLC (condition: 0.1% FA) to give the title compound (60 mg, 33% yield) as a colorless oil. LC-MS (ESI$^+$) m/z 574.2 (M+H)$^+$.

Step 2—3-[5-[[1-[2-[2-(2-Aminoethoxy)ethoxy]ethyl]-4-piperidyl]amino]-1-oxo-isoindolin-2-yl]piperidine-2,6-dione To a solution of tert-butyl N-[2-[2-[2-[4-[[2-(2,6-dioxo-3-piperidyl)-1-oxo-isoindolin-5-yl]amino]-1-piperidyl]ethoxy]ethoxy]ethyl]carbamate (60 mg, 105 umol) in DCM (10.0 mL) was added HCl/dioxane (4.00 M, 5.00 mL). The reaction mixture was stirred at rt for 1 hr. On completion, the mixture was concentrated in vacuo to give the title compound (53 mg, 99% yield, HCl) as a white solid. LC-MS (ESI$^+$) m/z 474.2 (M+H)$^+$.

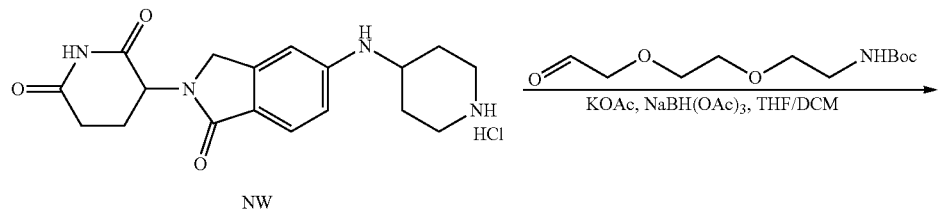

NW

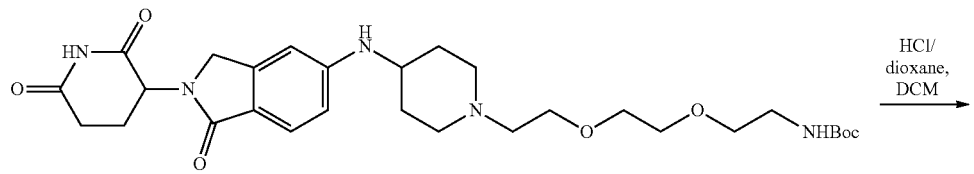

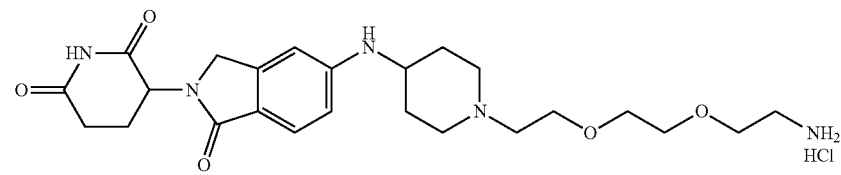

NX

1661

Tert-butyl N-[2-[2-[4-[2-(2,6-dioxo-3-piperidyl)-1,3-dioxo-isoindolin-4-yl]piperazin-1-yl]ethoxy]ethyl]carbamate (Intermediate NY)

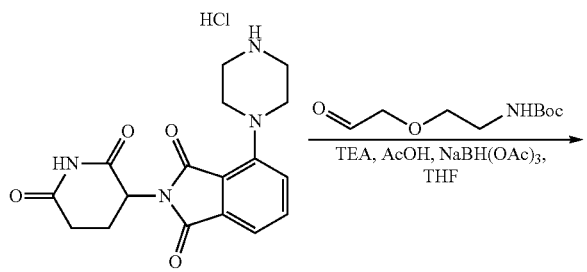

1662

To a solution of 2-(2,6-dioxo-3-piperidyl)-4-piperazin-1-yl-isoindoline-1,3-dione (0.5 g, 1.46 mmol, HCl, synthesized via Steps 1-2 Intermediate IA) and tert-butyl N-[2-(2-oxoethoxy)ethyl]carbamate (445 mg, 2.19 mmol, synthesized via Step 1 of Intermediate FS) in THF (10 mL) was added Et$_3$N (296 mg, 2.92 mmol, 407 uL) and AcOH (263 mg, 4.38 mmol, 251 uL) and then was added NaBH(OAc)$_3$ (619 mg, 2.92 mmol). The mixture was stirred at rt for 6 hr. On completion, the mixture was concentrated in vacuo. The crude product was purified by reversed-phase chromatography (0.1% HCl condition) to give the title compound (0.3 g, crude) as a yellow solid. LC-MS (ESI$^+$) m/z 530.4 (M+H)$^+$.

5-[4-[2-[2-[2-(2-Aminoethoxy)ethoxy]ethoxy]ethyl]piperazin-1-yl]-2-(2,6-dioxo-3-piperidyl)isoindoline-1,3-dione (Intermediate NZ)

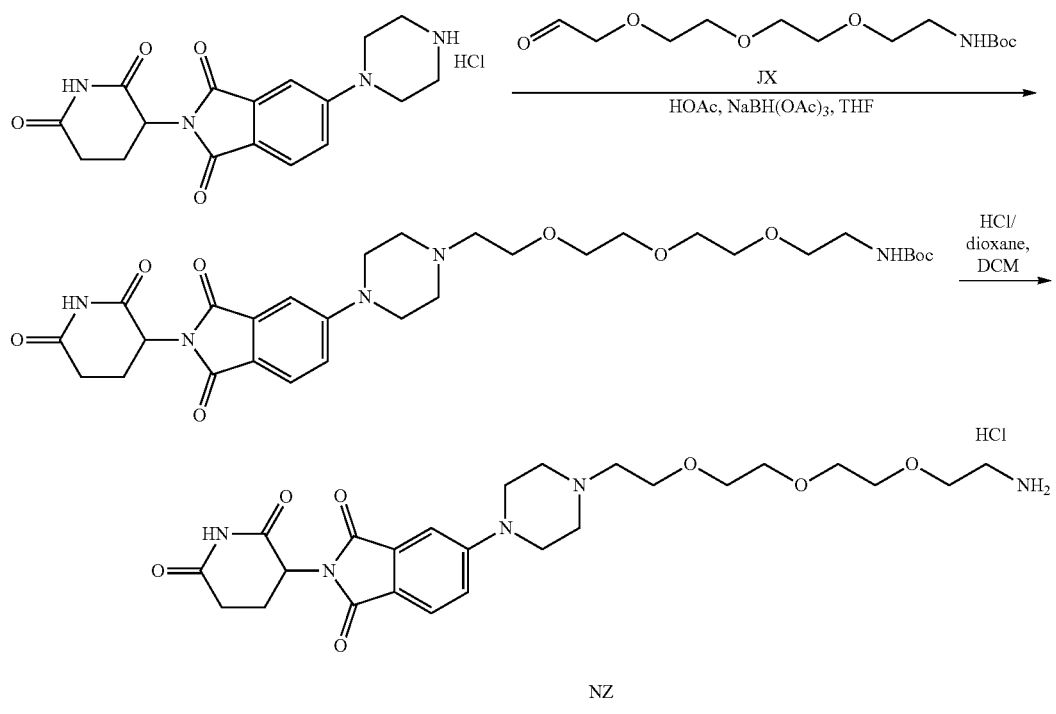

NZ

-continued

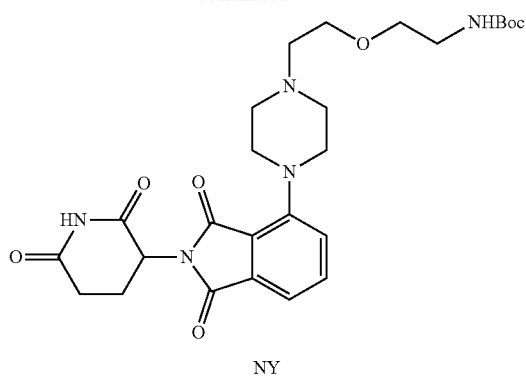

NY

Step 1—Tert-butyl N-[2-[2-[2-[2-[4-[2-(2,6-dioxo-3-piperidyl)-1,3-dioxo-isoindolin-5-yl]piperazin-1-yl]ethoxy]ethoxy]ethoxy]ethyl]carbamate A mixture of 2-(2,6-dioxo-3-piperidyl)-5-piperazin-1-yl-isoindoline-1,3-dione (390 mg, 1.03 mmol, HCl, synthesized via Steps 1-2 of Intermediate IB), tert-butyl N-[2-[2-[2-(2-oxoethoxy)ethoxy]ethoxy]ethyl]carbamate (250 mg, 858 umol, Intermediate JX), TEA (86.8 mg, 858 umol) in THF (10 mL) was added HOAc (51.5 mg, 858 umol, 49.0 uL) and NaBH(OAc)$_3$ (363 mg, 1.72 mmol), the mixture was stirred at rt for 72 hrs under N$_2$ atmosphere. On completion, the mixture was concentrated in vacuo. The residue was purified by Pre-HPLC (0.1% FA condition) to give the title compound (220 mg, 41% yield) as yellow solid. LC-MS (ESI$^+$) m/z 618.4 (M+H)$^+$.

Step 2—5-[4-[2-[2-[2-(2-Aminoethoxy)ethoxy]ethoxy]ethyl]piperazin-1-yl]-2-(2,6-dioxo-3-piperidyl)isoindoline-1,3-dione To a solution of tert-butyl N-[2-[2-[2-[2-[4-[2-(2,6-dioxo-3-piperidyl)-1,3-dioxo-isoindolin-5-yl]piperazin-1-yl]ethoxy]ethoxy]ethoxy]ethyl]carbamate (220 mg, 356 umol) in THF (10 mL) was added HCl/dioxane (4 M, 5 mL). The mixture was stirred at rt for 3 hrs. On completion, the mixture was concentrated in vacuo to give the title compound (190 mg, 96% yield) as yellow solid. LC-MS (ESI$^+$) m/z 518.3 (M+H)$^+$.

5-[4-[2-[2-(2-Aminoethoxy)ethoxy]ethyl]piperazin-1-yl]-2-(2,6-dioxo-3-piperidyl)isoindoline-1,3-dione (Intermediate OA)

Intermediate HY) in THF (20.0 mL) was added KOAc (143 mg, 1.46 mmol) and NaBH(OAc)$_3$ (170 mg, 803 umol). The reaction mixture was stirred at rt for 3 hrs. On completion, the reaction mixture was quenched with water (1.00 mL). The mixture was concentrated in vacuo. The residue was purified by prep-HPLC (condition: 0.1% FA) to give the title compound (275 mg, 62% yield) as a yellow solid. LC-MS (ESI$^+$) m/z 574.2 (M+H)$^+$.

Step 2—5-[4-[2-[2-(2-Aminoethoxy)ethoxy]ethyl]piperazin-1-yl]-2-(2,6-dioxo-3-piperidyl)isoindoline-1,3-dione To a solution of tert-butyl N-[2-[2-[2-[4-[2-(2,6-dioxo-3-piperidyl)-1,3-dioxo-isoindolin-5-yl]piperazin-1-yl]ethoxy]

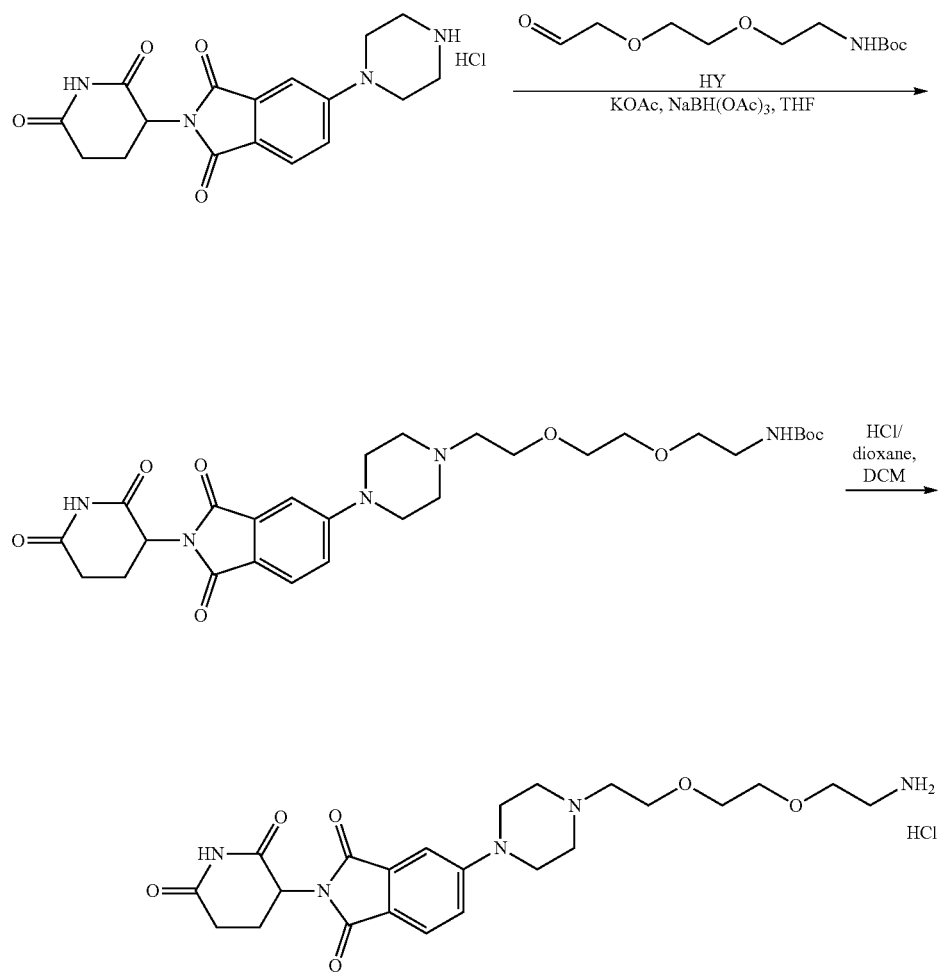

Step 1—Tert-butyl N-[2-[2-[2-[4-[2-(2,6-dioxo-3-piperidyl)-1,3-dioxo-isoindolin-5-yl]piperazin-1-yl]ethoxy]ethoxy]ethyl]carbamate To a solution of 2-(2,6-dioxo-3-piperidyl)-5-piperazin-1-yl-isoindoline-1,3-dione (250 mg, 730 umol, HCl, synthesized via Steps 1-2 of Intermediate IB) and tert-butyl (2-(2-(2-oxoethoxy)ethoxy)ethyl)carbamate (271 mg, 1.10 mmol, ethoxy]ethyl]carbamate (275 mg, 455 umol) in DCM (10.0 mL) was added HCl/dioxane (4.00 M, 7.60 mL). The reaction mixture was stirred at rt for 1 hr. On completion, the mixture was concentrated in vacuo to give the title compound (232 mg, 99% yield, HCl) as a yellow solid. LC-MS (ESI$^+$) m/z 474.3 (M+H)$^+$.

[(3R,5S)-5-[[4-[4-[[2-[2-(Cyclopropylmethylamino)-4-pyridyl]oxazole-4-carbonyl]amino]-3-(difluoromethyl)pyrazol-1-yl]phenyl]methylcarbamoyl]pyrrolidin-3-yl]acetate (Intermediate OB)

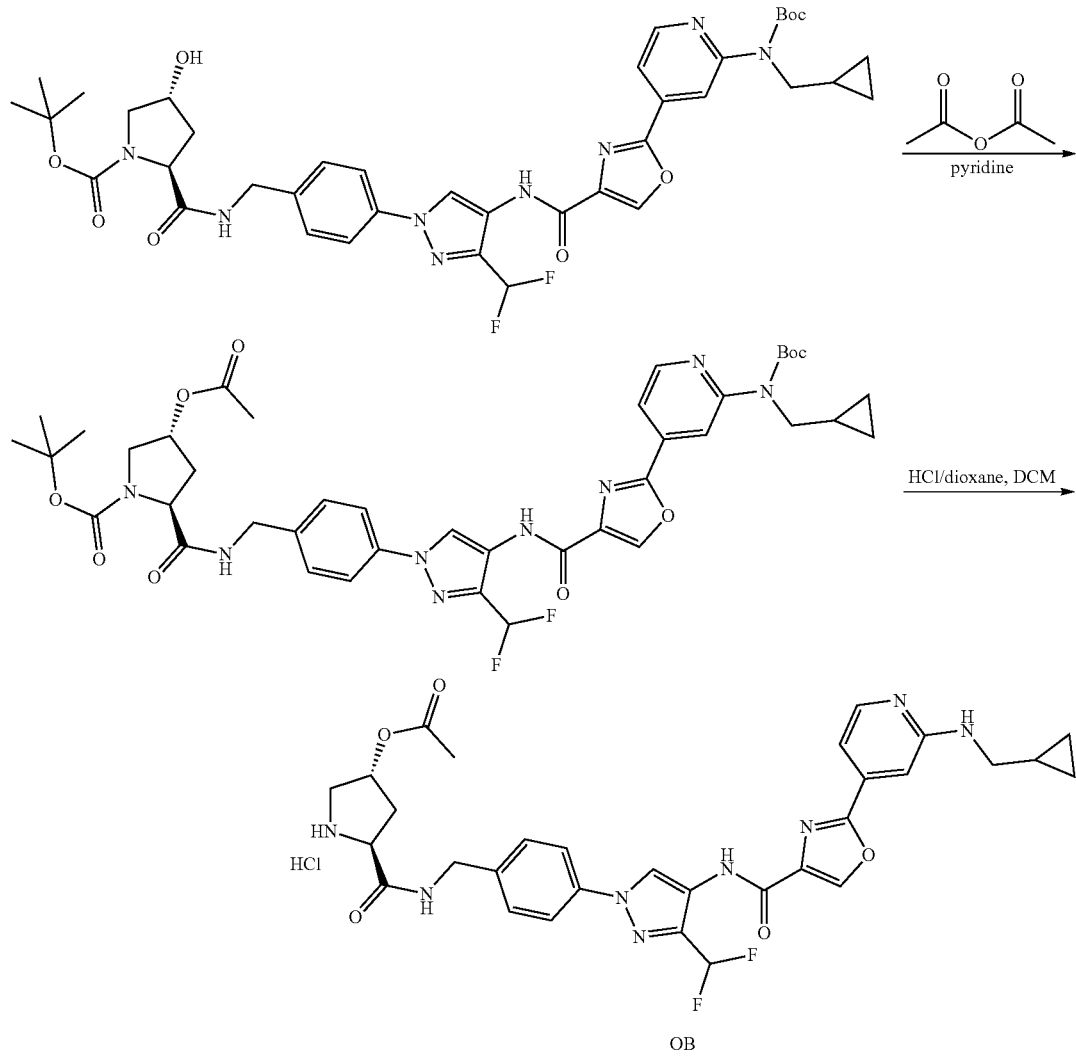

Step 1—Tert-butyl (2S,4R)-4-acetoxy-2-[[4-[4-[[2-[2-[tert-butoxycarbonyl(cyclopropylmethyl)amino]-4-pyridyl]oxazole-4-carbonyl]amino]-3-(difluoromethyl)pyrazol-1-yl]phenyl]methylcarbamoyl]pyrrolidine-1-carboxylate To a solution of tert-butyl (2S,4R)-2-[[4-[4-[[2-[2-[tert-butoxycarbonyl(cyclopropylmethyl)amino]-4-pyridyl]oxazole-4-carbonyl]amino]-3-(difluoromethyl)pyrazol-1-yl]phenyl]methylcarbamoyl]-4-hydroxy-pyrrolidine-1-carboxylate (180 mg, 227 umol, synthesized via Steps 1-3 of Intermediate KG) in pyridine (5.00 mL) was added acetyl acetate (545 mg, 5.34 mmol). The reaction mixture was stirred at rt for 12 hrs. On completion, the reaction mixture was concentrated in vacuo. The crude product was purified by prep-HPLC (0.1%, HCl) to give the title compound (180 mg, 95% yield) as colorless oil. LC-MS (ESI$^+$) m/z 835.1 (M+H)$^+$.

Step 2—[(3R,5S)-5-[[4-[4-[[2-[2-(Cyclopropylmethylamino)-4-pyridyl]oxazole-4-carbonyl]amino]-3-(difluoromethyl)pyrazol-1-yl]phenyl]methylcarbamoyl]pyrrolidin-3-yl]acetate To a solution of tert-butyl (2S,4R)-4-acetoxy-2-[[4-[4-[[2-[2-[tert-butoxycarbonyl(cyclopropylmethyl)amino]-4-pyridyl]oxazole-4-carbonyl]amino]-3-(difluoromethyl)pyrazol-1-yl]phenyl]methylcarbamoyl]pyrrolidine-1-carboxylate (110 mg, 132 umol) in DCM (3.00 mL) was added HCl/dioxane (4.00 M, 7.33 mL). The reaction mixture was stirred at rt for 1 hr. On completion, the reaction mixture was concentrated in vacuo to give the title compound (88.4 mg, 100% yield) as a white solid. LC-MS (ESI$^+$) m/z 635.2 (M+H)$^+$.

[(3R,5S)-1-[(2S)-2-Amino-3,3-dimethyl-butanoyl]-5-[[4-[4-[[2-[2-(cyclopropylmethylamino)-4-pyridyl]oxazole-4-carbonyl]amino]-3-(difluoromethyl)pyrazol-1-yl]phenyl]methylcarbamoyl]pyrrolidin-3-yl] acetate (Intermediate OC)

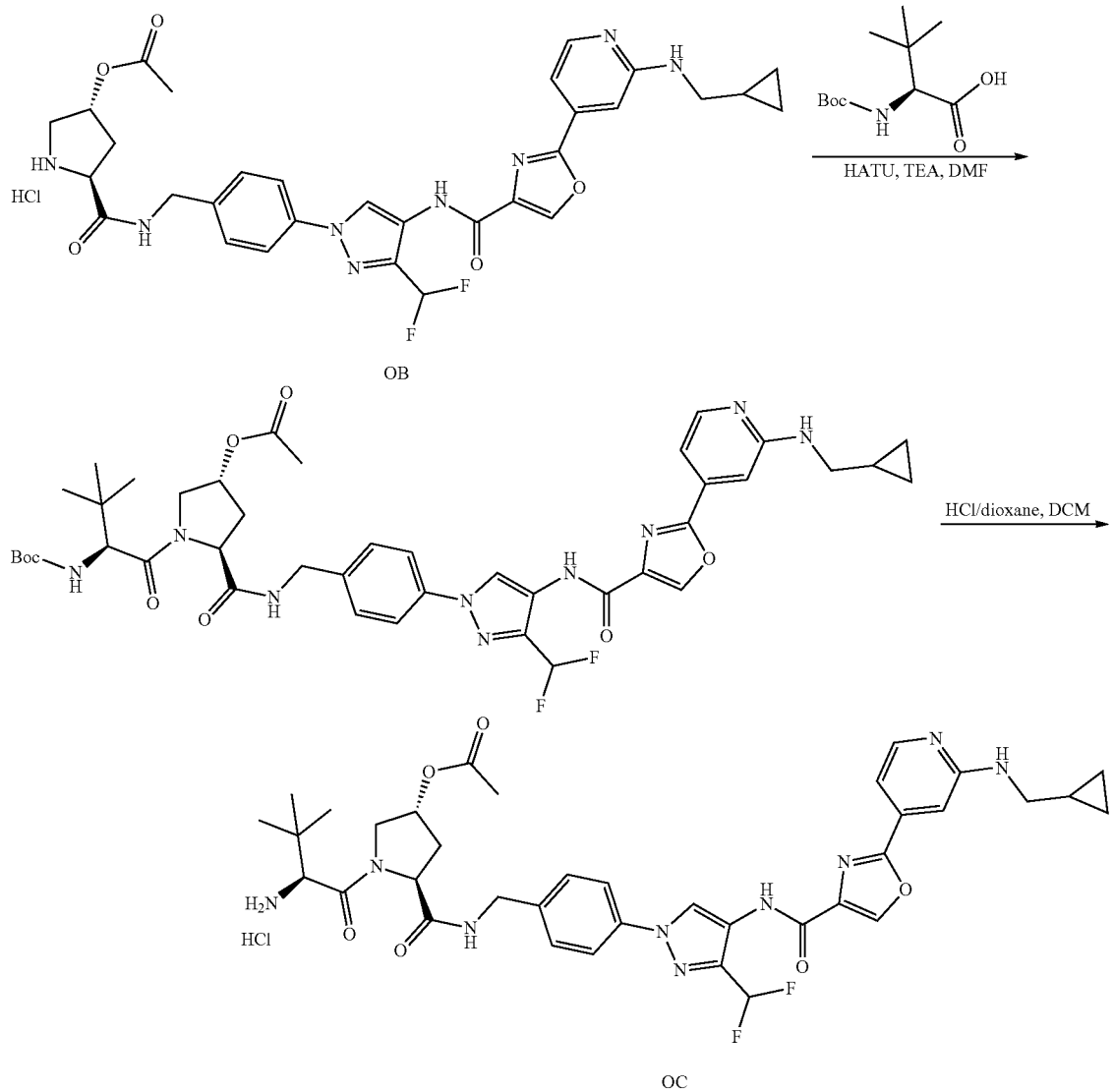

Step 1-[(3R,5S)-1-[(2S)-2-(Tert-butoxycarbonylamino)-3,3-dimethyl-butanoyl]-5-[[4-[4-[[2-[2-(cyclopropylmethylamino)-4-pyridyl]oxazole-4-carbonyl]amino]-3-(difluoromethyl)pyrazol-1-yl]phenyl]methylcarbamoyl]pyrrolidin-3-yl]acetate To a solution of [(3R,5S)-5-[[4-[4-[[2-[2-(cyclopropylmethylamino)-4-pyridyl]oxazole-4-carbonyl]amino]-3-(difluoromethyl)pyrazol-1-yl]phenyl]methylcarbamoyl]pyrrolidin-3-yl]acetate (88.4 mg, 132 umol, Intermediate OB) and (2S)-2-(tert-butoxycarbonylamino)-3,3-dimethyl-butanoic acid (36.6 mg, 158 umol, CAS #62965-35-9) in DMF (3.00 mL) was added DIPEA (85.1 mg, 659 umol), The reaction mixture was stirred at rt for 0.5 hr. After, HATU (60.10 mg, 158.07 umol) was added. The resulting reaction mixture was stirred at rt for 0.5 hr. On completion, the reaction mixture was quenched with water (15.0 mL), and extracted with ethyl acetate (3×30 mL). The combined organic layer was washed with brine (20 mL), dried over anhydrous sulfate sodium, filtered and concentrated in vacuo to give the title compound (110 mg, 99% yield) as a white solid. $^1$H NMR (400 MHz, DMSO-$d_6$) δ 9.07 (s, 1H), 8.74 (s, 1H), 8.30 (s, 1H), 8.17 (d, J=5.2 Hz, 1H), 7.58 (d, J=8.4 Hz, 2H), 7.33 (d, J=8.4 Hz, 2H), 7.24 (s, 1H), 7.13 (d, J=5.2 Hz, 1H), 7.05-6.73 (m, 2H), 5.28 (s, 1H), 5.06 (d, J=10.0 Hz, 1H), 4.68 (t, J=7.6 Hz, 1H), 4.51 (dd, J=6.4, 16 Hz, 1H), 4.28 (dd, J=5.2, 14.9 Hz, 1H), 4.11 (d, J=10.0 Hz, 1H), 4.00-3.98 (m, 1H), 3.68-3.61 (m, 1H), 3.17 (dd, J=5.2, 6.8 Hz, 2H), 2.76-2.68 (m, 1H), 1.98 (s, 3H), 1.34 (s, 9H), 1.08 (s, 1H), 0.83 (s, 9H), 0.57-0.50 (m, 2H), 0.28-0.22 (m, 2H). LC-MS (ESI$^+$) m/z 848.3 (M+H)$^+$.

Step 2—[(3R,5S)-1-[(2S)-2-Amino-3,3-dimethyl-butanoyl]-5-[[4-[4-[[2-[2-(cyclopropylmethyl-amino)-4-pyridyl]oxazole-4-carbonyl]amino]-3-(difluoromethyl)pyrazol-1-yl]phenyl]methylcarbamoyl]pyrrolidin-3-yl]acetate To a solution of [(3R,5S)-1-[(2S)-2-(tert-butoxycarbonylamino)-3,3-dimethyl-butanoyl]-5-[[4-[4-[[2-[2-(cyclopropylmethylamino)-4-pyridyl]oxazole-4-carbonyl]amino]-3-(difluoromethyl)pyrazol-1-yl]phenyl]methylcarbamoyl]pyrrolidin-3-yl]acetate (110 mg, 130 umol) in DCM (5.00 mL) was added HCl/dioxane (4.00 M, 5.45 mL). The reaction mixture was stirred at rt for 1 hr. On completion, the reaction mixture was concentrated in vacuo to give the title compound (100 mg, 98% yield) as a white solid. LC-MS (ESI$^+$) m/z 748.2 (M+H)$^+$.

3-[5-[4-(4-aminobutoxy)butyl]-3-methyl-2-oxo-benzimidazol-1-yl]piperidine-2,6-dione (Intermediate OD)

Step 1-Tert-butyl N-[4-([4-[1-(2,6-dioxopiperidin-3-yl)-3-methyl-2-oxo-2,3-dihydro-1H-1,3-benzodiazol-5-yl]but-3-yn-1-yl]oxy)butyl]carbamate To a solution of 3-(5-bromo-3-methyl-2-oxo-2,3-dihydro-1H-1,3-benzodiazol-1-yl)piperidine-2,6-dione (2 g, 6 mmol, Intermediate HN) in DMSO (20 mL) were added tert-butyl N-[4-(but-3-yn-1-yloxy)butyl]carbamate (4.3 g, 18 mmol, Intermediate OI), Pd(PPh$_3$)$_4$ (683.4 mg, 0.59 mmol), CuI (225.3 mg, 1.18 mmol) and TEA (10 mL) at rt under nitrogen atmosphere. The resulting mixture was stirred for 16 h at 85° C. under nitrogen atmosphere. The reaction mixture was cooled to rt and concentrated under reduced pressure to remove the TEA. The resulting mixture was diluted with ice/water (50 ml, plus 3 ml AcOH) and extracted with EtOAc (2×50 mL). The combined organic layer was washed with brine (30 mL) and dried over anhydrous Na$_2$SO$_4$. After filtration, the filtrate was concentrated under reduced pressure. The residue was purified by reverse phase flash chromatography with the following

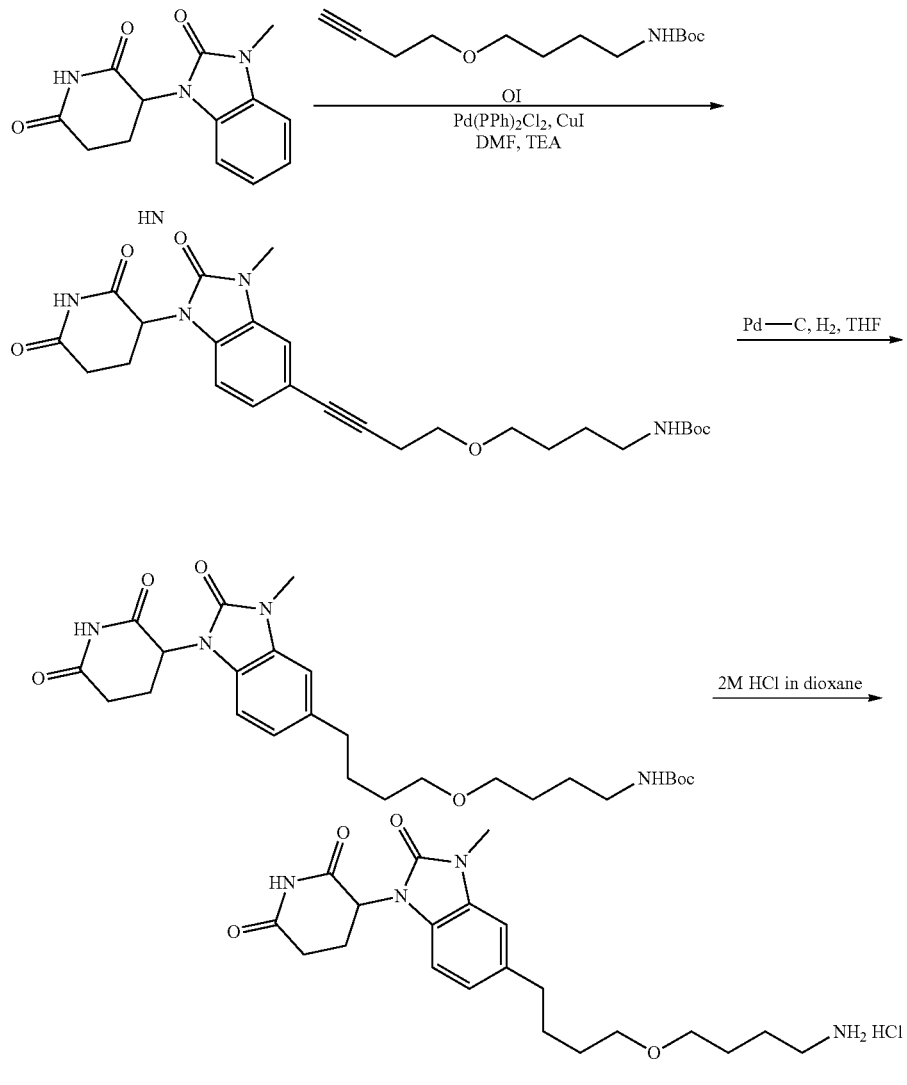

OD conditions: Column: WelFlash™ C18-I, 20-40 μm, 330 g; Eluent A: Water (plus 10 mmol/L FA); Eluent B: ACN; Gradient: 5% B-5% B in 10 min; 50% B-60% B in 25 min; Flow rate: 80 mL/min; Detector: 220/254 nm; desired fractions were collected at 57% B and concentrated under reduced pressure to afford tert-butyl N-[4-([4-[1-(2,6-dioxopiperidin-3-yl)-3-methyl-2-oxo-2,3-dihydro-1H-1,3-benzodiazol-5-yl]but-3-yn-1-yl]oxy)butyl]carbamate (1.5 g, 51%) as a yellow solid. $^1$H NMR (400 MHz, DMSO-d$_6$) δ 11.12 (s, 1H), 7.24 (s, 1H), 7.10 (s, 2H), 6.79 (s, 1H), 5.41-5.34 (m, 1H), 3.55 (t, J=6.8 Hz, 2H), 3.44 (t, J=6.3 Hz, 2H), 3.32 (s, 3H), 2.96-2.88 (m, 3H), 2.71-2.65 (m, 4H), 2.11-2.00 (m, 1H), 1.49 (s, 2H), 1.48-1.40 (m, 2H), 1.37 (s, 9H); LC/MS (ESI, m/z): [M−1]⁻=497.2.

Step 2—Tert-butyl N-(4-[4-[1-(2,6-dioxopiperidin-3-yl)-3-methyl-2-oxo-2,3-dihydro-1H-1,3-benzodiazol-5-yl]butoxy]butyl)carbamate To a solution of tert-butyl N-[4-([4-[1-(2,6-dioxopiperidin-3-yl)-3-methyl-2-oxo-2,3-dihydro-1H-1,3-benzodiazol-5-yl]but-3-yn-1-yl]oxy)butyl]carbamate (1.5 g, 3.01 mmol) in THF (50 mL) was added palladium on charcoal (0.15 g, 10% w/w) under nitrogen atmosphere. The mixture was hydrogenated at rt for 4 h using a hydrogen balloon. The resulting mixture was filtered through a celite pad and concentrated under reduced pressure to afford tert-butyl N-(4-[4-[1-(2,6-dioxopiperidin-3-yl)-3-methyl-2-oxo-2,3-dihydro-1H-1,3-benzodiazol-5-yl]butoxy]butyl)carbamate (1.2 g, 79%) as a white solid. $^1$H NMR (400 MHz, CDCl$_3$) δ 8.12 (br s, 1H), 6.94-6.89 (m, 1H), 6.87 (d, J=1.5 Hz, 1H), 6.73 (d, J=8.0 Hz, 1H), 5.23 (dd, J=12.5, 5.4 Hz, 1H), 4.73-4.60 (m, 1H), 3.49-3.36 (m, 7H), 3.15 (d, J=6.1 Hz, 2H), 2.97 (d, J=16.7 Hz, 1H), 2.87 (dd, J=13.3, 5.0 Hz, 1H), 2.70 (t, J=7.6 Hz, 2H), 2.32-2.19 (m, 1H), 1.76-1.50 (m, 9H), 1.46 (s, 9H); LC/MS (ESI, m/z): [M+1]⁺=503.4.

Step 3—3-[5-[4-(4-Aminobutoxy)butyl]-3-methyl-2-oxo-2,3-dihydro-1H-1,3-benzodiazol-1-yl]piperidine-2,6-dione hydrochloride A solution of tert-butyl N-(4-[4-[1-(2,6-dioxopiperidin-3-yl)-3-methyl-2-oxo-2,3-dihydro-1H-1,3-benzodiazol-5-yl]butoxy]butyl)carbamate (150 mg, 0.29 mmol) in dioxane (2 mL) was treated with a solution of HCl (gas) in 1,4-dioxane (4 M, 2 mL) for 16 h at rt under nitrogen atmosphere. The resulting mixture was concentrated under reduced pressure to afford 3-[5-[4-(4-aminobutoxy)butyl]-3-methyl-2-oxo-2,3-dihydro-1H-1,3-benzodiazol-1-yl]piperidine-2,6-dione hydrochloride (100 mg, 77%) as a light yellow solid. $^1$H NMR (400 MHz, DMSO-d$_6$) δ 11.08 (s, 1H), 7.86 (br s, 3H), 7.05-6.98 (m, 2H), 6.87 (d, J=8.0 Hz, 1H), 5.35 (dd, J=12.7, 5.3 Hz, 1H), 3.74-3.63 (m, 1H), 3.57 (s, 1H), 3.49 (dd, J=11.6, 4.4 Hz, 1H), 3.42-3.33 (m, 4H), 2.97-2.85 (m, 1H), 2.82-2.59 (m, 6H), 2.06-1.96 (m, 1H), 1.67-1.48 (m, 8H); LC/MS (ESI, m/z): [(M+1)]⁺=403.2.

(S)-7-(2-(2-(2-(2-aminoethoxy)ethoxy)ethoxy)ethoxy)-2-((S)-2-(2-methoxyacetamido)-3,3-dimethylbutanoyl)-N—((R)-1,2,3,4-tetrahydronaphthalen-1-yl)-1,2,3,4-tetrahydroisoquinoline-3-carboxamide (Intermediate OE)

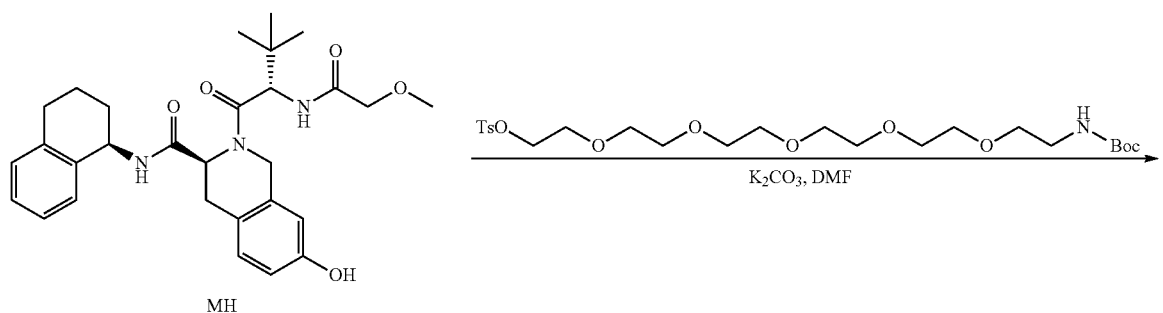

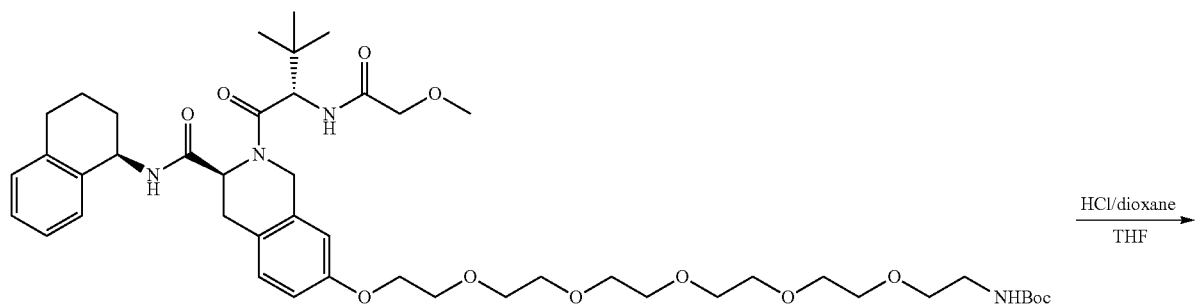

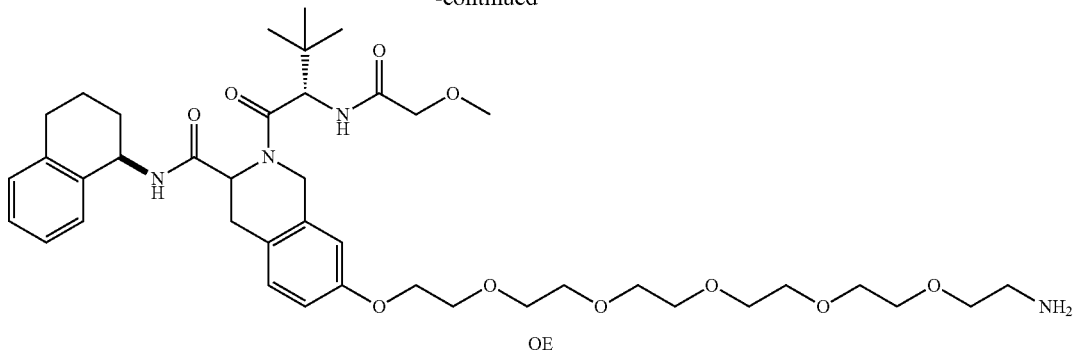

OE (S)-7-(2-(2-(2-(2-aminoethoxy)ethoxy)ethoxy)ethoxy)-2-((S)-2-(2-methoxyacetamido)-3,3-dimethylbutanoyl)-N—((R)-1,2,3,4-tetrahydronaphthalen-1-yl)-1,2,3,4-tetrahydroisoquinoline-3-carboxamide was synthesized as described for Intermediate LY, using 2,2-dimethyl-4-oxo-3,8,11,14,17,20-hexaoxa-5-azadocosan-22-yl 4-methylbenzenesulfonate, Intermediate OO, as the tosylate in Step 1 to couple with alcohol Intermediate MH. $^1$H NMR (400 MHz, DMSO-$d_6$) δ 8.37 (br. s., 1H), 8.17-8.23 (m, 1H), 7.30-7.46 (m, 1H), 6.77-7.14 (m, 7H), 4.63-5.11 (m, 5H), 4.03-4.10 (m, 2H), 3.70-3.92 (m, 4H), 3.40-3.63 (m, 18H), 3.28-3.35 (m, 3H), 2.91-3.08 (m, 2H), 2.78-2.88 (m, 2H), 2.61-2.76 (m, 2H), 1.52-1.88 (m, 4H), 0.84-1.04 (m, 9H). LC-MS (ESI$^+$): m/z 771.2 (M+H)$^+$.

2,2-dimethyl-4-oxo-3,8,11,14,17,20,23-heptaoxa-5-azapentacosan-25-oic acid (Intermediate OF)

Step 1—2-(17-hydroxy-3,6,9,12,15-pentaoxaheptadecyl)isoindoline-1,3-dione

To a stirred solution of 3,6,9,12,15-pentaoxaheptadecane-1,17-diol (10 g, 35.4 mmol, CAS #2615-15-8) in THF (200 ml) was added phthalimide (6.253 g, 42.51 mmol), and PPh$_3$ (12.06 g, 46.02 mmol) at room temperature. The reaction mixture was degassed and purged with nitrogen several times. The reaction mixture was cooled to 0° C. then DEAD (8.02 g, 46.02 mmol) was added dropwise to the reaction mixture at 0° C. After the addition, the mixture was stirred at room temperature for 12 h. The mixture was concentrated in vacuo and the residue was purified via column chromatography (DCM/MeOH=0%-10%) to give the desired compound (6.4 g, 44.0%) as a colorless oil. $^1$H NMR (400 MHz, DMSO-$d_6$) δ 7.93-7.81 (m, 4H), 4.57 (t, J=5.5 Hz, 1H), 3.75

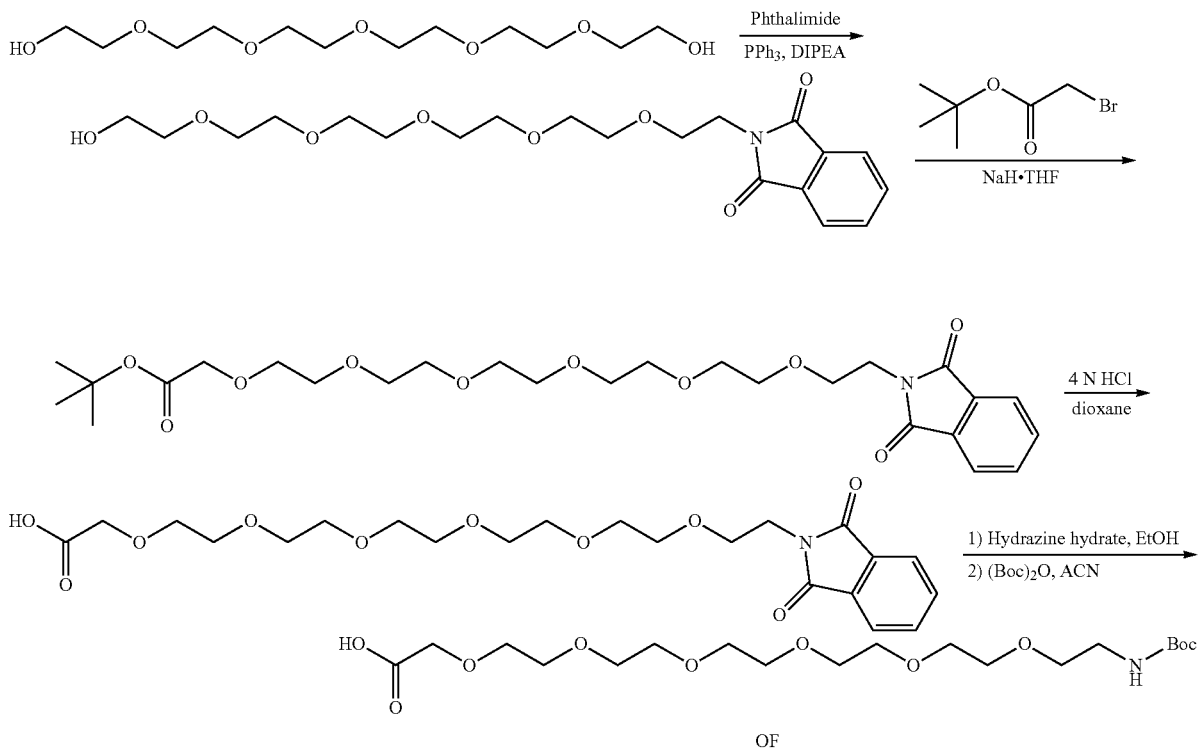

OF (t, J=5.8 Hz, 2H), 3.63 (t, J=5.8 Hz, 2H), 3.54-3.48 (m, 7H), 3.46 (ddd, J=7.0, 4.7, 1.9 Hz, 7H), 3.43-3.38 (m, 6H).

Step 2—tert-butyl 20-(1,3-dioxoisoindolin-2-yl)-3,6,9,12,15,18-hexaoxaicosan-1-oate To a solution of 2-(17-hydroxy-3,6,9,12,15-pentaoxaheptadecyl)isoindoline-1,3-dione (7.0 g, 17.03 mmol) in THF (200 mL) was added 60% NaH (885.6 mg, 22.14 mmol) at 0° C. After stirring for 0.5 h at 0° C., tert-butyl 2-bromoacetate (4.65 g, 23.84 mmol) was added dropwise to the reaction mixture at 0° C. The reaction mixture was stirred at 0° C. for 2 hrs, then warmed to rt with stirring on for another 2 hrs. The reaction mixture was quenched with water at 0° C., and extracted with EtOAc (100 mL×2). The combined organic layer was washed with brine (50 mL×3), dried over anhydrous $Na_2SO_4$, filtered, and concentrated in vacuo. The residue was purified by column chromatography (DCM/MeOH=0%-10%) to give the desired compound (4.5 g, 50.3%) as a pale yellow solid. LC-MS (ESI$^+$): m/z 526.3 (M+H)$^+$.

Step 3—20-(1,3-dioxoisoindolin-2-yl)-3,6,9,12,15,18-hexaoxaicosan-1-oic acid

To a solution of tert-butyl 20-(1,3-dioxoisoindolin-2-yl)-3,6,9,12,15,18-hexaoxaicosan-1-oate (4.5 g, 8.571 mmol) in DCM (100 mL) was added TFA (50 mL) at rt. The reaction mixture was stirred at rt for 2 hs, then concentrated in vacuo to give the desired compound (3.5 g, 87.1%) as a yellow solid. LC-MS (ESI$^+$): m/z 470.2 (M+H)$^+$.

Step 4: 2,2-dimethyl-4-oxo-3,8,11,14,17,20,23-heptaoxa-5-azapentacosan-25-oic acid To a solution of 20-(1,3-dioxoisoindolin-2-yl)-3,6,9,12,15,18-hexaoxaicosan-1-oic acid (3.5 g, 7.463 mmol) in EtOH (50 mL) was added hydrazinium (716.8 mg, 22.4 mmol, 99%) at r.t. The reaction mixture was heated to reflux for 3 hs. A white solid formed, then the reaction mixture was filtered and the filtrate was concentrated in vacuo. The residue was dissolved in $CH_3CN$ (100 mL). (Boc)$_2$O (9.8 g, 44.8 mmol) was added to the reaction mixture at rt and the mixture was stirred at room temperature for 2 hr. The reaction mixture was then concentrated in vacuo to give a residue which was purified by column chromatography (DCM/MeOH=0%-10%) to give the desired compound (1.4 g, 42.7%) as a colorless oil. LC-MS (ESI$^+$): m/z 440.5 (M+H)$^+$.

Tert-butyl N-[3-[2,2-dimethyl-3-(prop-2-yn-1-yloxy)propoxy]propyl]carbamate (Intermediate OG)

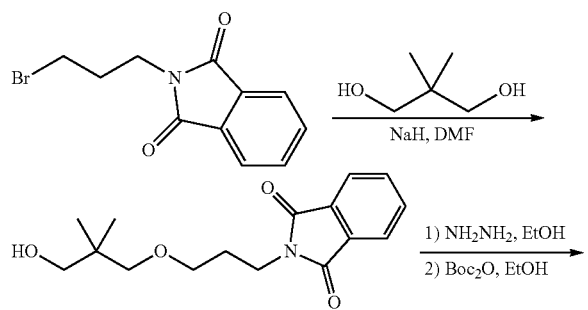

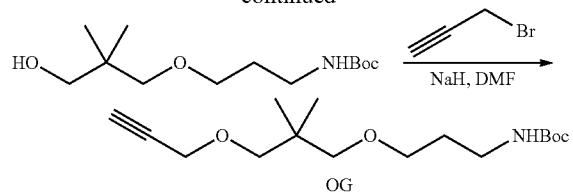

Step 1—2-[3-(3-Hydroxy-2,2-dimethylpropoxy)propyl]-2,3-dihydro-1H-isoindole-1,3-dione To a solution of 2,2-dimethylpropane-1,3-diol (38.8 g, 373 mmol, CAS #126-30-7) in DMF (400 mL) was added sodium hydride (60% dispersion in mineral oil, 15.0 g, 375 mmol) at 0° C. The mixture was stirred for 15 min at the same temperature. Then a solution of 2-(3-bromopropyl)-2,3-dihydro-1H-isoindole-1,3-dione (50 g, 187 mmol, CAS #5460-29-7) in DMF (50 mL) was added dropwise and the mixture was allowed to warm to room temperature and stirred for 16 hours. The reaction was quenched by the addition of a solution of HOAc (60 g) in water (1 L) at it. The resulting mixture was extracted with EtOAc (3×500 mL). The combined organic layer was washed with brine (500 mL) and dried over anhydrous $Na_2SO_4$, filtered and the filtrate was concentrated under reduced pressure. The residue was purified by silica gel column chromatography, eluted with 50% ethyl acetate in petroleum ether to afford 2-[3-(3-hydroxy-2,2-dimethylpropoxy)propyl]-2,3-dihydro-1H-isoindole-1,3-dione (7.4 g, 11%) as a light yellow solid. $^1$H NMR (400 MHz, CDCl$_3$) δ 7.81 (dd, J=5.5, 3.1 Hz, 2H), 7.69 (dd, J=5.5, 3.1 Hz, 2H), 3.77 (t, J=6.6 Hz, 2H), 3.44-3.37 (m, 4H), 3.20 (s, 2H), 1.92 (p, J=6.2 Hz, 2H), 0.86 (s, 6H); LC/MS (ESI, m/z): [(M+18)]$^+$=292.30.

Step 2—Tert-butyl N-[3-(3-hydroxy-2,2-dimethylpropoxy)propyl]carbamate

To a stirred solution of 2-[3-(3-hydroxy-2,2-dimethylpropoxy)propyl]-2,3-dihydro-1H-isoindole-1,3-dione (6.1 g, 20.9 mmol) in EtOH (400 mL) was added hydrazine hydrate (2.1 g, 41.9 mmol, 98%) at rt under nitrogen atmosphere. The resulting solution was stirred for 2 h at 70° C. The mixture was cooled down to room temperature. To the above mixture was added di-tert-butyl dicarbonate (27.4 g, 125.6 mmol) at rt and the resulting mixture was stirred for additional 16 hours at rt. After filtration, the filter cake was washed with EtOH (50 mL) and the filtrate was concentrated under reduced pressure. The residue was purified by silica gel column chromatography, eluted with 25% ethyl acetate in petroleum ether, to afford tert-butyl N-[3-(3-hydroxy-2,2-dimethylpropoxy)propyl]carbamate (5.6 g, 82%) as a light yellow oil. $^1$H NMR (400 MHz, CDCl$_3$) δ 5.00 (br s, 1H), 3.45 (td, J=5.8, 1.3 Hz, 2H), 3.40 (t, J=2.0 Hz, 2H), 3.25-3.14 (m, 4H), 1.71 (p, J=6.6, 6.1 Hz, 2H), 1.41 (s, 9H), 0.87 (s, 6H); LC/MS (ESI, m/z): [(M−100+1)]$^+$=162.35.

Step 3—Tert-butyl N-[3-[2,2-dimethyl-3-(prop-2-yn-1-yloxy)propoxy]propyl]carbamate To a solution of tert-butyl N-[3-(3-hydroxy-2,2-dimethylpropoxy)propyl]carbamate (5.6 g, 21.4 mmol) in DMF (60 mL) was added sodium hydride (60% dispersion in mineral oil, 1.7 g, 42.5 mmol) at 0° C. The mixture was stirred for 15 min at the same temperature. Then a solution of 3-bromoprop-1-yne (2.5 g, 21.43 mmol) in DMF (20 mL) was added dropwise and the mixture was allowed to warm to rt and stirred for 16 hours. The reaction was quenched by the addition of saturated aqueous NH$_4$Cl (300 mL) at room temperature. The resulting mixture was diluted with water (200 mL) and extracted with EtOAc (3×200 mL). The combined organic layers was washed with brine (500 mL) and dried over anhydrous Na$_2$SO$_4$, filtered and the filtrate was concentrated under reduced pressure. The residue was purified by silica gel column chromatography, eluted with 10% ethyl acetate in petroleum ether, to afford tert-butyl N-[3-[2,2-dimethyl-3-(prop-2-yn-1-yloxy)propoxy]propyl] carbamate (2.9 g, 45%) as a light yellow oil: $^1$H NMR (400 MHz, DMSO-d$_6$) δ 6.71 (t, J=5.7 Hz, 1H), 4.10 (d, J=2.4 Hz, 2H), 3.41-3.31 (m, 3H), 3.20 (s, 2H), 3.10 (s, 2H), 2.98 (q, J=6.6 Hz, 2H), 1.61 (p, J=6.6 Hz, 2H), 1.38 (s, 9H), 0.84 (s, 6H); LC/MS (ESI, m/z): [(M+1)]$^+$=300.20.

Tert-butyl N-[3-(prop-2-yn-1-yloxy)propyl]carbamate (Intermediate OH)

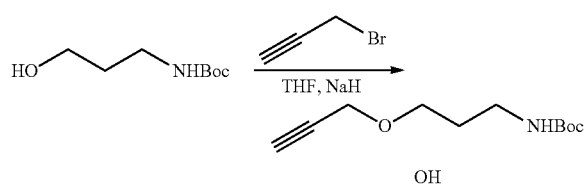

A solution of tert-butyl N-(3-hydroxypropyl)carbamate (1 g, 6 mmol, CAS #58885-58-8) in THF (40 mL) was treated with NaH (60% dispersion in mineral oil, 0.3 g, 14 mmol) for 30 min at 0° C. under nitrogen atmosphere. Next, a solution of 3-bromoprop-1-yne (0.7 g, 6.28 mmol) in THF (5 mL) was added dropwise at 0° C. The resulting mixture was stirred for 16 h at rt. The reaction was quenched with saturated aqueous NH$_4$HCO$_3$ (100 mL) and extracted with EtOAc (3×50 mL). The combined organic layer was washed with brine (50 mL) and dried over anhydrous Na$_2$SO$_4$. After filtration, the filtrate was concentrated under reduced pressure. The residue was purified by silica gel column chromatography, eluted with 5%-20% ethyl acetate in petroleum ether, to afford tert-butyl N-[3-(prop-2-yn-1-yloxy)propyl] carbamate (0.6 g, 49%) as a yellow oil: $^1$H NMR (400 MHz, DMSO-d$_6$) δ 6.77 (t, J=5.7 Hz, 1H), 4.10 (t, J=2.0 Hz, 2H), 3.44-3.39 (m, 3H), 2.99-2.91 (m, 2H), 1.64-1.59 (m, 2H), 1.38 (s, 9H); LC/MS (ESI, m/z): [(M−1)]$^-$=212.2.

Tert-butyl N-[4-(but-3-yn-1-yloxy)butyl]carbamate (Intermediate OI)

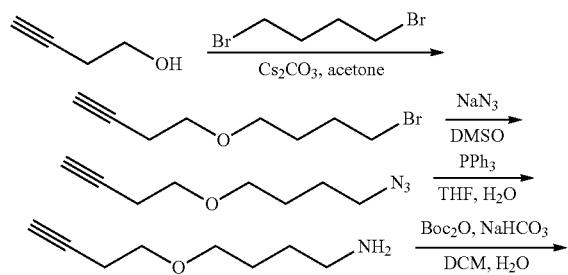

Step 1—4-(4-Bromobutoxy)but-1-yne

To a stirred solution of 1,4-dibromobutane (201 g, 933 mmol) in acetone (1 L) were added Cs$_2$CO$_3$ (223 g, 685 mmol) and but-3-yn-1-ol (43.6 g, 622.05 mmol) at rt. The resulting mixture was stirred for 16 h at rt under nitrogen atmosphere. After filtration, the filter cake was washed with acetone (2×50 mL). The filtrate was concentrated under reduced pressure. The residue was purified by silica gel column chromatography, eluted with 1% ethyl acetate in petroleum ether to afford 4-(4-bromobutoxy)but-1-yne (29 g, 23%) as a light yellow oil. $^1$H NMR (400 MHz, CDCl$_3$) δ 3.54 (t, J=6.9 Hz, 2H), 3.49 (t, J=6.2 Hz, 2H), 3.44 (t, J=6.6 Hz, 2H), 2.45 (td, J=7.0, 2.6 Hz, 2H), 2.02-1.88 (m, 3H), 1.80-1.65 (m, 2H).

Step 2—4-(4-Azidobutoxy)but-1-yne

A mixture of 4-(4-bromobutoxy)but-1-yne (29 g, 141 mmol) and NaN$_3$ (14 g, 212 mmol) in DMSO (300 mL) was stirred for 4 h at rt under nitrogen atmosphere. The resulting mixture was diluted with ice water (1 L) and extracted with petroleum ether/EtOAc (5/1, v/v, 2×500 mL). The combined organic layers was washed with brine (500 mL) and dried over anhydrous Na$_2$SO$_4$. After filtration, the filtrate was concentrated under reduced pressure to afford 4-(4-azidobutoxy)but-1-yne (22.2 g, 94%) as a light yellow oil: $^1$H NMR (400 MHz, CDCl$_3$) δ 3.53 (td, J=6.9, 1.6 Hz, 2H), 3.47 (td, J=6.0, 1.7 Hz, 2H), 3.29 (t, J=6.2 Hz, 2H), 2.44 (tt, J=7.0, 2.2 Hz, 2H), 1.97 (t, J=2.7 Hz, 1H), 1.73-1.57 (m, 4H); LC/MS (ESI, m/z): [(2M+1)]$^+$=335.25.

Step 3—4-(But-3-yn-1-yloxy)butan-1-amine

A solution of 4-(4-azidobutoxy)but-1-yne (22.2 g, 132.8 mmol) and Ph$_3$P (52.2 g, 199.2 mmol) in THF (400 mL) and H$_2$O (80 mL) was stirred for 4 h at 50° C. under nitrogen atmosphere. The resulting mixture was cooled and concentrated under reduced pressure to remove THF. The residue was acidified to pH=1 with 4 M aqueous HCl. The resulting mixture was extracted with EtOAc (2×500 mL). The water layer was neutralized to pH=7 with 2 M aqueous NaOH, and extracted with DCM (2×500 mL). The combined organic layers was washed with brine (500 mL) and dried over anhydrous Na$_2$SO$_4$. After filtration, the filtrate was concentrated under reduced pressure to afford crude product (18 g). LC/MS (ESI, m/z): [(M+1)]$^+$=142.1.

Step 4—Tert-butyl N-[4-(but-3-yn-1-yloxy)butyl] carbamate

To a stirred solution of 4-(but-3-yn-1-yloxy)butan-1-amine (18 g, 127.5 mmol) in DCM (500 mL) and H$_2$O (500 mL) were added NaHCO$_3$ (21.4 g, 254.9 mmol) and Boc$_2$O (33.4 g, 152.9 mmol) at rt. The resulting mixture was stirred for 16 h at rt under nitrogen atmosphere. The resulting mixture was extracted with CH$_2$Cl$_2$ (2×500 mL). The combined organic layers was washed with brine (500 mL) and dried over anhydrous Na$_2$SO$_4$. After filtration, the filtrate was concentrated under reduced pressure. The residue was purified by silica gel column chromatography, eluted with 20% ethyl acetate in petroleum ether to afford tert-butyl N-[4-(but-3-yn-1-yloxy)butyl]carbamate (30 g, 98%) as a light yellow oil. ¹H NMR (400 MHz, CDCl₃) δ 4.67 (s, 1H), 3.54 (td, J=6.9, 3.6 Hz, 2H), 3.51-3.42 (m, 2H), 3.13 (q, J=5.6, 4.7 Hz, 2H), 2.45 (dh, J=7.2, 4.0, 3.5 Hz, 2H), 1.98 (q, J=2.8 Hz, 1H), 1.58 (td, J=8.7, 7.7, 4.4 Hz, 4H), 1.42 (s, 9H); LC/MS (ESI, m/z): [(M+1)]⁺=242.3.

tert-butyl N-[3-[3-(prop-2-yn-1-yloxy)propoxy]propyl]carbamate (Intermediate OJ)

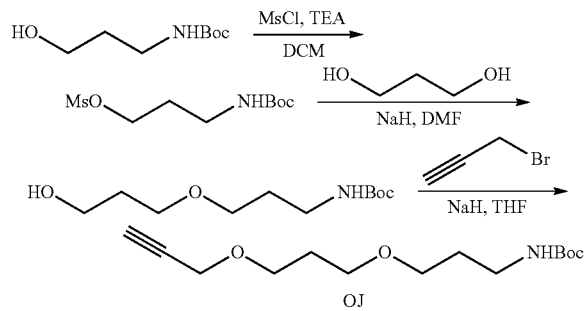

Step 1—tert-butyl N-[3-(methanesulfonyloxy)propyl]carbamate

To a stirred solution of tert-butyl N-(3-hydroxypropyl)carbamate (92.6 g, 528.4 mmol, CAS #58885-58-8) in DCM (800 mL) were added TEA (80.2 g, 792.7 mmol) and a solution of MsCl (60.5 g, 528.5 mmol) in DCM (200 mL) dropwise at 0° C. over 30 min under nitrogen atmosphere. The resulting mixture was stirred for 30 min at rt under nitrogen atmosphere. The resulting mixture was diluted with water (2 L) and extracted with CH₂Cl₂ (3×800 mL). The combined organic layers was washed with brine (1 L) and dried over anhydrous Na₂SO₄. After filtration, the filtrate was concentrated under reduced pressure. The residue was purified by silica gel column chromatography, eluted with 40% ethyl acetate in petroleum ether to afford tert-butyl N-[3-(methanesulfonyloxy)propyl]carbamate (112 g, 84%) as a light brown solid. ¹H NMR (400 MHz, CDCl₃) δ 4.91 (br s, 1H), 4.24 (td, J=6.9, 6.4, 2.9 Hz, 2H), 3.21 (d, J=7.9 Hz, 2H), 3.06-2.92 (m, 3H), 1.89 (pd, J=6.3, 2.6 Hz, 2H), 1.39 (d, J=3.0 Hz, 9H).

Step 2—tert-butyl N-[3-(3-hydroxypropoxy)propyl]carbamate

To a solution of propane-1,3-diol (50 g, 657 mmol) in DMF (500 mL) was added sodium hydride (4.79 g, 200 mmol, 60% dispersed in mineral oil) at 0° C. The mixture was stirred for 15 min at rt. To the above mixture was added a solution of tert-butyl N-[3-(methanesulfonyloxy)propyl]carbamate (25.3 g, 100 mmol) in DMF (150 mL) dropwise rt and the mixture was stirred for 16 hours at rt. The reaction was quenched with sat. NH₄Cl (200 mL) at 0° C. The resulting mixture was concentrated under reduced pressure. The residue was diluted with brine (1.5 L) and extracted with EtOAc (3×500 mL). The combined organic layers was washed with brine (500 mL) and dried over anhydrous Na₂SO₄. After filtration, the filtrate was concentrated under reduced pressure. The residue was purified by silica gel column chromatography, eluted with 30% ethyl acetate in petroleum ether to afford tert-butyl N-[3-(3-hydroxypropoxy)propyl]carbamate (13.7 g, 59%) as a light yellow oil. ¹H NMR (400 MHz, CDCl₃) δ 4.11 (s, 1H), 3.57 (td, J=6.3, 1.9 Hz, 2H), 3.50-3.42 (m, 4H), 3.19 (q, J=6.5 Hz, 2H), 1.88-1.78 (m, 2H), 1.71 (p, J=6.5 Hz, 2H), 1.41 (s, 9H); LC/MS (ESI, m/z): [(M+1)]⁺=234.15.

Step 3—tert-butyl N-[3-[3-(prop-2-yn-1-yloxy)propoxy]propyl]carbamate

To a solution of tert-butyl N-[3-(3-hydroxypropoxy)propyl]carbamate (12.5 g, 53.6 mmol) in THF (300 mL) was added sodium hydride (2.6 g, 108.3 mmol, 60% dispersion in mineral oil) at 0° C. The mixture was stirred for 15 min. To the mixture was added a solution of 3-bromoprop-1-yne (6.4 g, 53.8 mmol) in THF (50 mL) dropwise and the mixture was warmed to rt and stirred for 16 hours. The reaction was quenched with sat. NH₄Cl (200 mL) at 0° C., diluted with brine (500 mL) and extracted with EtOAc (3×300 mL). The combined organic layers was washed with brine (500 mL) and dried over anhydrous Na₂SO₄. After filtration, the filtrate was concentrated under reduced pressure. The residue was purified by silica gel column chromatography, eluted with 25% ethyl acetate in petroleum ether to afford tert-butyl N-[3-[3-(prop-2-yn-1-yloxy)propoxy]propyl]carbamate (9.2 g, 60%) as a light yellow solid. ¹H NMR (400 MHz, CDCl₃) δ 4.90 (br s, 1H), 4.11 (d, J=2.4 Hz, 2H), 3.57 (t, J=6.3 Hz, 2H), 3.50-3.40 (m, 4H), 3.18 (t, J=7.2 Hz, 2H), 2.42 (t, J=2.4 Hz, 1H), 1.83 (p, J=6.2 Hz, 2H), 1.71 (p, J=6.2 Hz, 2H), 1.41 (s, 9H).

4-[2-[2-(2-aminoethoxy)ethoxy]ethylamino]-2-(2,6-dioxo-3-piperidyl)isoindoline-1,3-dione (Intermediate OK)

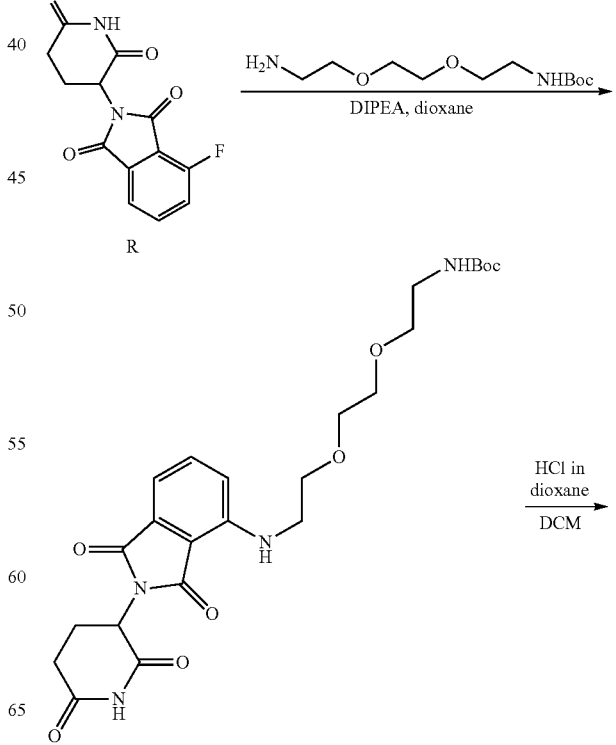

1681
-continued

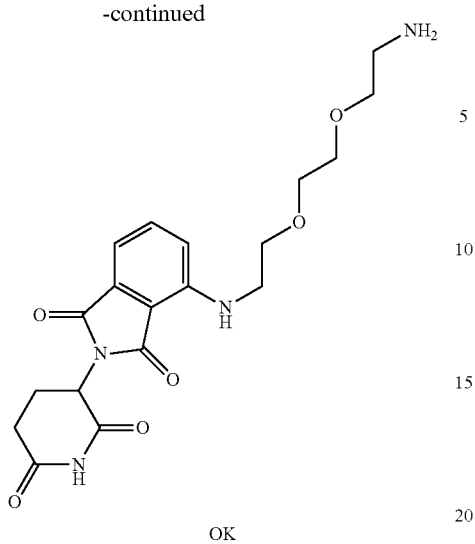

OK

4-[2-[2-(2-aminoethoxy)ethoxy]ethylamino]-2-(2,6-dioxo-3-piperidyl)isoindoline-1,3-dione was synthesized as described in Steps 1-2 of Example 127.

2-[2-[2-[2-[[2-(2,6-dioxo-3-piperidyl)-1,3-dioxo-isoindolin-4-yl]amino]ethoxy]ethoxy]ethoxy]acetic acid (Intermediate OL)

1682

2-[2-[2-[2-[[2-(2,6-dioxo-3-piperidyl)-1,3-dioxo-isoindolin-4-yl]amino]ethoxy]ethoxy]ethoxy]acetic acid was synthesized via Steps 1-2 of Example 152.

2-[2-[tert-butoxycarbonyl(cyclopropylmethyl)amino]-4-pyridyl]oxazole-4-carboxylic acid (Intermediate OM)

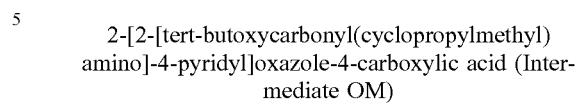

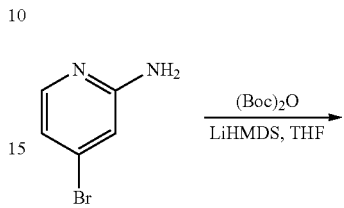

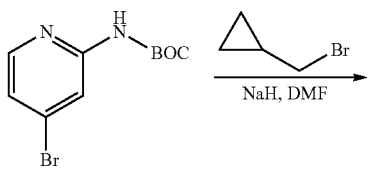

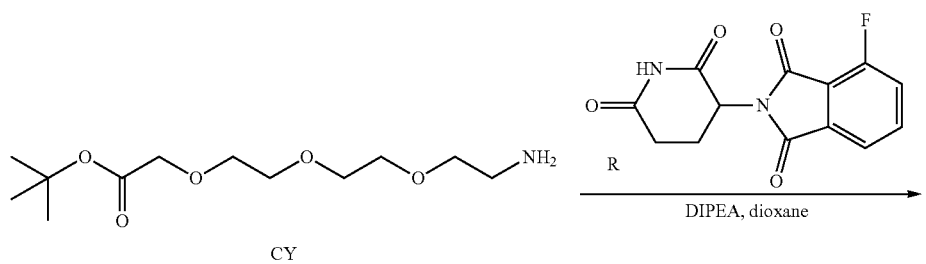

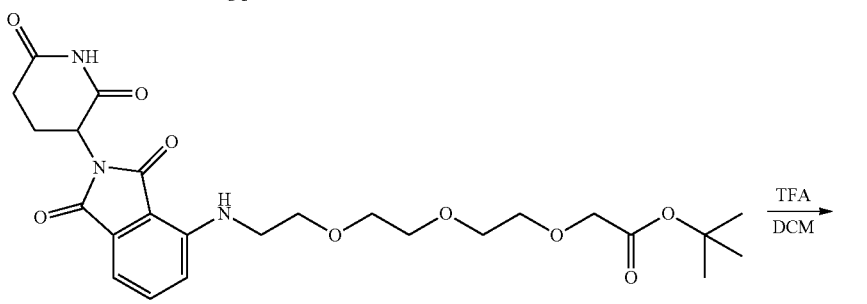

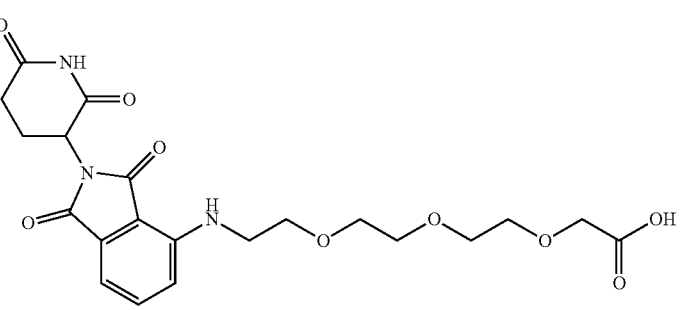

OL

1683
-continued

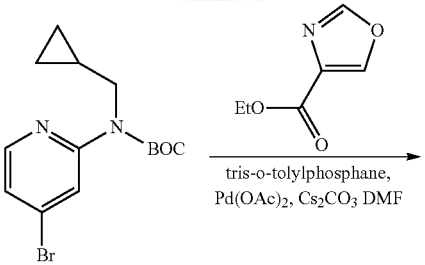

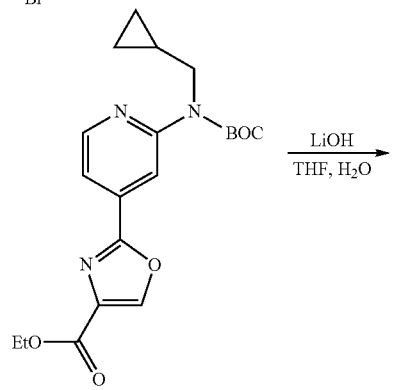

2-[2-[tert-butoxycarbonyl(cyclopropylmethyl)amino]-4-pyridyl]oxazole-4-carboxylic acid was synthesized via Steps 1-4 of Intermediate DF.

2,2-dimethyl-4-oxo-3,8,11,14,17-pentaoxa-5-azanonadecan-19-yl 4-methylbenzenesulfonate (Intermediate ON)

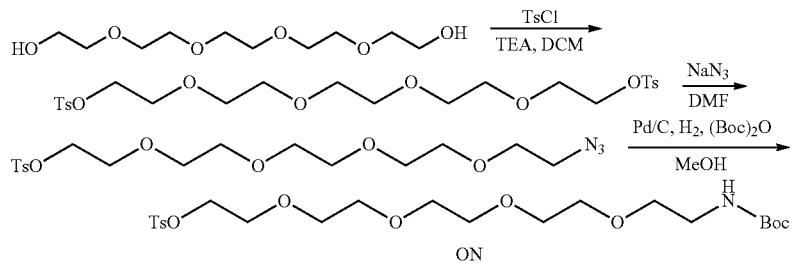

Step 1—3,6,9,12-tetraoxatetradecane-1,14-diyl bis(4-methylbenzenesulfonate)

To a mixture of 3,6,9,12-tetraoxatetradecane-1,14-diol (10 g, 42 mmol, CAS #75506-78-4) and TsCl (17.56 g, 92.4 mmol) in DCM (200 ml) was added TEA (17 g, 168 mmol) dropwise at rt and the mixture was stirred at rt overnight. Then the reaction mixture was concentrated in vacuo, the residue was dissolved in EtOAc (100 ml) and washed with water (100 ml×2), brine (100 ml), dried with Na$_2$SO$_4$, and filtered. The organic phase was evaporated and the residue was purified by silica gel chromatography (PE:EA=1:1) to give the title compound (19.17 g, 83.35 yield) as a yellow solid LC-MS (ESI$^+$): m/z 547.1 (M+H)$^+$.

Step 2—3,6,9,12-tetraoxatetradecane-1,14-diyl bis(4-methylbenzenesulfonate)

To a solution of 3,6,9,12-tetraoxatetradecane-1,14-diyl bis(4-methylbenzenesulfonate) (19.17 g, 35.1 mmol) in DMF (100 ml) was added NaN$_3$ (2.51 g, 38.62 mmol). The mixture was stirred rt for 2 days. The mixture was poured into water (300 ml) and extracted with EtOAc (3×300 ml). The combined organic layers were washed with water (300 ml×3) and brine (300 ml), dried with Na$_2$SO$_4$, and filtered. The organic phase was evaporated and the residue was purified by silica gel chromatography (PE:EA) to give the title compound as a colorless oil (6.5 g, 44% yield). LC-MS (ESI$^+$): m/z 418.2 (M+H)$^+$.

Step 3—2,2-dimethyl-4-oxo-3,8,11,14,17-pentaoxa-5-azanonadecan-19-yl 4-methylbenzenesulfonate A mixture of 14-azido-3,6,9,12-tetraoxatetradecyl 4-methylbenzenesulfonate (10 g, 20.4 mmol), Pd/C (20%, 1 g), (Boc)$_2$O (6.7 g, 30.6 mmol) and MeOH (200 mL) was stirred for overnight at rt under H$_2$. The mixture was filtered and concentrated in vacuo. To the mixture was added H$_2$O (200 mL) then it was extracted with EA (300 mL). The organic layer was concentrated and purified by column chromatography (PE/EA=2/1 to 1/1 to EA) to give 2,2-dimethyl-4-oxo-3,8,11,14,17-pentaoxa-5-azanonadecan-19-yl 4-methylbenzenesulfonate (8.2 g, 69% yield) as a yellow oil. $^1$H NMR (400 MHz, CDCl$_3$) δ 7.81-7.79 (d, J=8 Hz, 2H), 7.35-7.33 (d, J=8 Hz, 2H), 4.17-4.13 (t, J=4.8 Hz, 2H), 3.70-3.47 (m, 16H), 3.31-3.29 (t, J=5.2 Hz, 2H), 2.45 (s, 3H), 1.44 (s, 9H). LC-MS (ESI$^+$): m/z 492.7 (M+H)$^+$.

2,2-dimethyl-4-oxo-3,8,11,14,17,20-hexaoxa-5-azadocosan-22-yl 4-methylbenzenesulfonate (Intermediate OO)

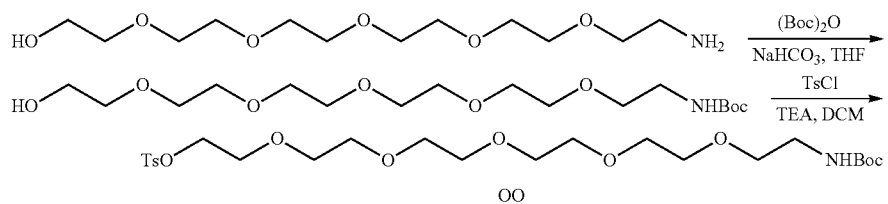

Step 1-tert-butyl tert-butyl (17-hydroxy-3,6,9,12,15-pentaoxaheptadecyl)carbamate To a stirred solution of 17-amino-3,6,9,12,15-pentaoxaheptadecan-1-ol (4.0 g, 14.22 mmol, CAS #39160-70-8) in THF (50 mL) was added (Boc)$_2$O (3.72 g, 17.06 mmol) and NaHCO$_3$ (saturated solution, 2 mL) at rt. The reaction mixture was stirred at rt for 3 h. The mixture was concentrated in vacuo and the residue was purified by column to give the desired compound (4.96 g, yield, 73%) as a yellow oil. LC-MS (ESI$^+$): m/z 382.43 (M+H)$^+$.

Step 2—2,2-dimethyl-4-oxo-3,8,11,14,17,20-hexaoxa-5-azadocosan-22-yl 4-methylbenzenesulfonate To a stirred solution of tert-butyl (17-hydroxy-3,6,9,12,15-pentaoxaheptadecyl)carbamate (2.0 g, 5.25 mmol) in DCM (10 mL) was added TEA (1.06 g, 10.5 mmol) at rt. To the above reaction mixture was added dropwise TsCl (2.0 g, 10.5 mmol) in DCM (5 mL) at 0° C. After the addition, the reaction was stirred at rt overnight. The mixture was concentrated in vacuo and the residue was purified via column chromatography (Petroleum ether/EtOAc=5%-80%) to give the desired compound (1.85 g, 66%) as a yellow oil. LC-MS (ESI$^+$): m/z 536.50 (M+H)$^+$.

N-(4-piperazin-1-ylcyclohexyl)-5-tetrahydropyran-4-yl-pyrrolo[2,1-f][1,2,4]triazin-4-amine (Intermediate OP)

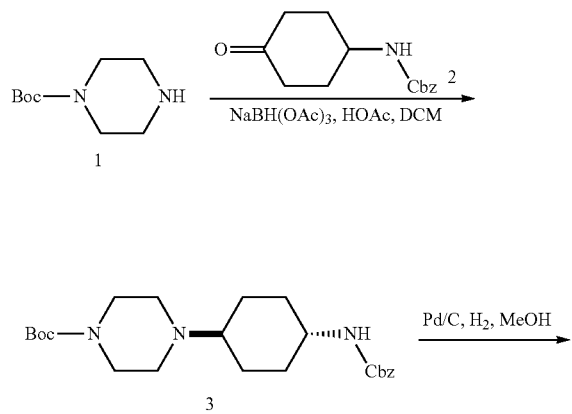

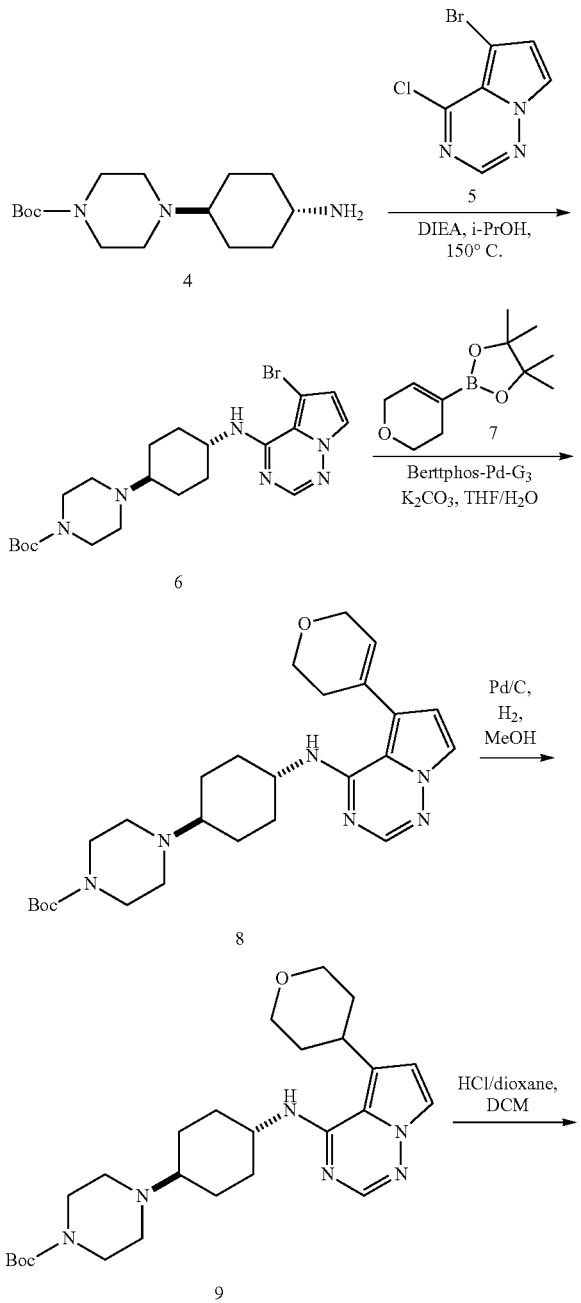

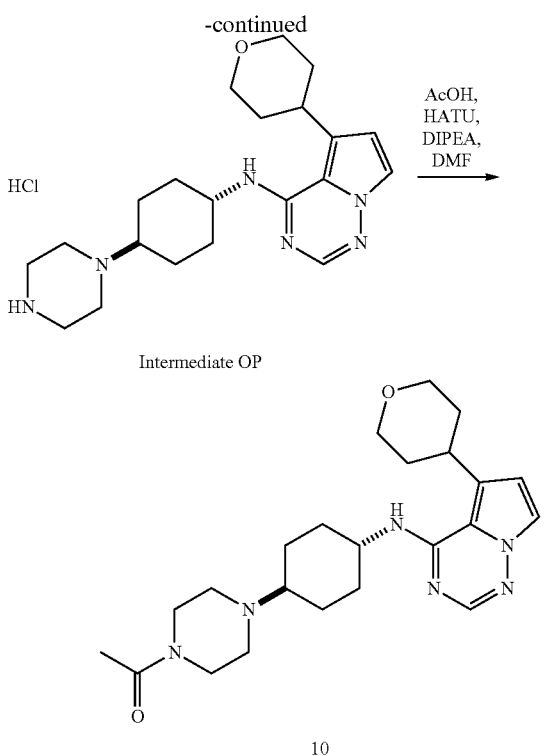

Intermediate OP

10

Step 1—Tert-butyl 4-(trans-4-(((benzyloxy)carbonyl)amino)cyclohexyl)piperazine-1-carboxylate (3)

The reaction was performed in parallel for two batches: to a solution of tert-butyl piperazine-1-carboxylate (24.0 g, 129 mmol) in DCM (400 mL) was added benzyl N-(4-oxocyclohexyl)carbamate (31.9 g, 129 mmol, CAS #16801-63-1), HOAc (3.15 g, 52.5 mmo) and NaBH(OAc)$_3$ (81.9 g, 387 mmol) successively at 0-10° C., and the mixture was stirred at 15° C. for 16 hours under N$_2$. On completion, the mixture of two bathces was combined, basified to pH=8 with sat.aq-.NaHCO$_3$, and partitioned. The aqueous phase was extracted with DCM (2×200 mL). The combined organic layer was washed with brine (300 mL), dried over Na$_2$SO$_4$, filtered and concentrated in vacuum. The residue was purified by prep-HPLC (column: Phenomenex Gemini C18 250*50 mm*10 um; mobile phase: [water (0.05% ammonia hydroxide v/v)-ACN]; B %: 50%-75%, 26MIN, 40% min) to give two fractions. The first fraction is the title compound (20.0 g, 18% yield) as white solid. $^1$H NMR (400 MHz, CDCl$_3$) δ ppm 7.46-7.29 (m, 5H), 5.09 (s, 2H), 4.57 (s, 1H), 3.43 (m, 5H), 2.50 (m, 4H), 2.28 (m, 1H), 2.10 (d, J=12.0 Hz, 2H), 1.90 (d, J=11.6 Hz, 2H), 1.46 (s, 9H), 1.40-1.27 (m, 2H), 1.22-1.08 (m, 2H). The second fraction is undesired cis-isomer (12.7 g, 11% yield).

Step 2—Tert-butyl 4-(trans-4-aminocyclohexyl)piperazine-1-carboxylate (4)

A mixture of tert-butyl 4-[4-(benzyloxycarbonylamino)cyclohexyl]piperazine-1-carboxylate (8.00 g, 16.4 mmol) and Pd/C (800 mg, 10% purity) in MeOH (80 mL) was stirred at 25° C. for 2 hours under H$_2$ (15 Psi). On completion, the mixture was filtered, and the cake was washed with MeOH (50 mL). The filtrate and washings were combined and concentrated in vacuum to give the title compound (5.3 g, crude) as white solid. $^1$H NMR (400 MHz, CDCl$_3$) δ ppm 3.49-3.21 (m, 4H), 2.64-2.58 (m, 1H), 2.54 (m, 4H), 2.31-2.20 (m, 1H), 1.88 (t, J=15.2 Hz, 4H), 1.45 (s, 9H), 1.34-1.22 (m, 2H), 1.17-1.05 (m, 2H).

Step 3—Tert-butyl 4-[4-[(5-bromopyrrolo[2,1-f][1,2,4]triazin-4-yl)amino]cyclohexyl]piperazine-1-carboxylate (6)

5-bromo-4-chloro-pyrrolo[2,1-f][1,2,4]triazine (250 mg, 1.08 mmol, CAS #1403767-33-8), DIPEA (555 mg, 4.30 mmol) and tert-butyl 4-(4-aminocyclohexyl)piperazine-1-carboxylate (350 mg, 1.23 mmol) were suspended in IPA (5 mL) under nitrogen and sealed into a microwave tube. The resulting suspension was heated to 150° C. for 3 hours under microwave irradiation. On completed, the mixture was concentrated in vacuo. The crude product was triturated with methanol (5 mL) to give the title compound (300 mg, 58% yield) as a white solid. $^1$H NMR (400 MHz, DMSO-d$_6$) δ 7.92 (s, 1H), 7.72 (d, J=2.8 Hz, 1H), 6.80 (d, J=2.8 Hz, 1H), 6.61 (d, J=6.8 Hz, 1H), 4.08-4.00 (m, 1H), 3.32-3.20 (m, 4H), 2.93-2.91 (m, 1H), 2.45-2.41 (m, 2H), 2.11-2.07 (m, 2H), 1.84-1.80 (m, 1H), 1.57-1.16 (m, 16H); LC-MS (ESI$^+$) m/z 481.2 & 479.2 (M+H)$^+$.

Step 4—Tert-butyl 4-[4-[[5-(3,6-dihydro-2H-pyran-4-yl)pyrrolo[2,1-f][1,2,4]triazin-4-yl]amino]cyclohexyl]piperazine-1-carboxylate (8)

A mixture of tert-butyl 4-[4-[(5-bromopyrrolo[2,1-f][1,2,4]triazin-4-yl)amino]cyclohexyl]piperazine-1-carboxylate (300 mg, 625 umol), 2-(3,6-dihydro-2H-pyran-4-yl)-4,4,5,5-tetramethyl-1,3,2-dioxaborolane (394 mg, 1.88 mmol, CAS #287944-16-5), Brettphos-Pd-G$_3$ (56.7 mg, 62.5 umol) and K$_2$CO$_3$ (173 mg, 1.25 mmol) in a mixed solvent of THF (20 mL) and H$_2$O (4 mL) was degassed and purged with N$_2$ for 3 times, and then the mixture was stirred at 55° C. for 12 hrs under N$_2$ atmosphere. On completion, the reaction mixture was concentrated in vacuo. The residue was washed with water (60 mL), extracted with ethyl acetate (3×50 mL). The organic layer was dried with Na$_2$SO$_4$, filtrated and concentrated in vacuo. The crude product was purified by reversed-phase HPLC (0.1% FA condition) to give the title compound (220 mg, 73% yield) as yellow oil. $^1$H NMR (400 MHz, DMSO-d$_6$) δ 7.89 (s, 1H), 7.62 (d, J=2.8 Hz, 1H), 6.66 (d, J=2.8 Hz, 1H), 6.20 (d, J=8.0 Hz, 1H), 5.82 (s, 1H), 4.22-4.19 (m, 2H), 3.98-3.94 (m, 1H), 3.84 (t, J=5.2 Hz, 2H), 3.28-3.26 (m, 4H), 2.46-2.44 (m, 4H), 2.36 (t, J=10.8 Hz, 1H), 2.10-2.07 (m, 2H), 1.83-1.80 (m, 2H), 1.39 (s, 9H), 1.37-1.23 (m, 4H); LC-MS (ESI$^+$) m/z 483.4 (M+H)$^+$.

Step 5—Tert-butyl 4-[4-[(5-tetrahydropyran-4-ylpyrrolo[2,1-f][1,2,4]triazin-4-yl)amino]cyclohexyl]piperazine-1-carboxylate (9)

To a solution of tert-butyl 4-[4-[[5-(3,6-dihydro-2H-pyran-4-yl)pyrrolo[2,1-f][1,2,4]triazin-4-yl]amino]cyclohexyl]piperazine-1-carboxylate (220 mg, 455 umol) in methanol (30 mL) was added Pd/C (100 mg, 10%, wt) under N$_2$. The suspension was degassed under vacuum and purged with H$_2$ several times. The mixture was stirred under H$_2$ (15 psi) at 25° C. for 16 hours. On completion, the reaction mixture was filtered. The filtrate was concentrated in vacuo to give the title compound (190 mg, 86% yield) as a white solid. $^1$H NMR (400 MHz, DMSO-d$_6$) δ 7.78 (s, 1H), 7.54 (d, J=2.8 Hz, 1H), 6.53 (d, J=2.8 Hz, 1H), 6.21 (d, J=8.0 Hz, 1H), 4.17-3.97 (m, 1H), 3.92-3.88 (m, 2H), 3.57-3.51 (m, 2H), 3.44-3.38 (m, 1H), 3.29-3.27 (m, 4H), 2.45-2.43 (m, 4H), 2.35-2.29 (m, 1H), 2.01-1.98 (m, 2H), 1.84-1.81 (m, 2H), 1.79-1.72 (m, 2H), 1.66-1.63 (m, 2H), 1.57-1.47 (m, 2H), 1.39 (s, 9H), 1.37-1.28 (m, 2H); LC-MS (ESI$^+$) m/z 485.4 (M+H)$^+$.

Step 6—N-(4-piperazin-1-ylcyclohexyl)-5-tetrahydropyran-4-yl-pyrrolo[2,1-f][1,2,4]triazin-4-amine (Intermediate OP)

To a solution of tert-butyl 4-[4-[(5-tetrahydropyran-4-ylpyrrolo[2,1-f][1,2,4]triazin-4-yl)amino]cyclohexyl]piperazine-1-carboxylate (180 mg, 345 umol) in DCM (3 mL) was added HCl/dioxane (4 M, 50 mL). The reaction mixture was stirred at 20° C. for 20 minutes. On completion, the mixture was filtered and concentrated in vacuo to give the title compound (145 mg, 99% yield) as a white solid. LC-MS (ESI$^+$) m/z 385.3 (M+H)$^+$.

Step 7—1-[4-[4-[(5-Tetrahydropyran-4-ylpyrrolo[2,1-f][1,2,4]triazin-4-yl)amino]cyclohexyl]piperazin-1-yl]ethanone (10)

To a solution of N-(4-piperazin-1-ylcyclohexyl)-5-tetrahydropyran-4-yl-pyrrolo[2,1-f][1,2,4]triazin-4-amine (153 mg, 363 umol, HCl salt) and AcOH (24.0 mg, 399 umol) in DMF (3 mL) was added HATU (165 mg, 436 umol). Then, DIPEA (187 mg, 1.45 mmol) was added. The reaction mixture was stirred at 20° C. for 0.5 hr. On completion, the reaction mixture was concentrated in vacuo. The crude product was purified by prep-HPLC (column: Phenomenex Synergi C18 150*25*10 um; mobile phase: [water (0.225% FA)-ACN]; B %: 3%-33%, 10 min) to give the title compound (94.0 mg, 61% yield) as white solid. $^1$H NMR (400 MHz, DMSO-d$_6$) δ 7.79 (s, 1H), 7.54 (d, J=2.8 Hz, 1H), 6.54 (d, J=2.8 Hz, 1H), 6.20 (d, J=8.0 Hz, 1H), 4.14-4.01 (m, 1H), 3.91 (dd, J=3.2, 10.8 Hz, 2H), 3.55 (t, J=10.8 Hz, 2H), 3.44-3.40 (m, 6H), 2.58-2.54 (m, 2H), 2.43-2.39 (m, 1H), 2.04-2.00 (m, 2H), 1.98 (s, 3H), 1.87-1.85 (m, 2H), 1.78-1.72 (m, 2H), 1.71-1.59 (m, 2H), 1.58-1.47 (m, 2H), 1.44-1.31 (m, 2H); LC-MS (ESI$^+$) m/z 427.3 (M+H)$^+$.

N1-methyl-N4-(5-tetrahydropyran-4-yl-7H-pyrrolo[2,3-d]pyrimidin-4-yl)cyclohexane-1,4-diamine (Intermediate OQ)

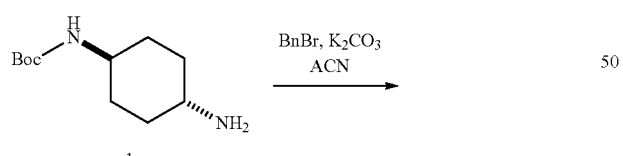

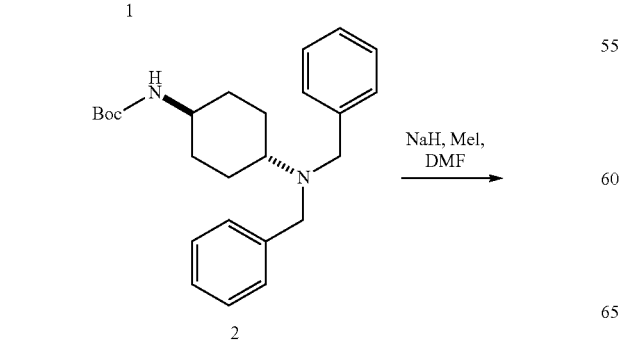

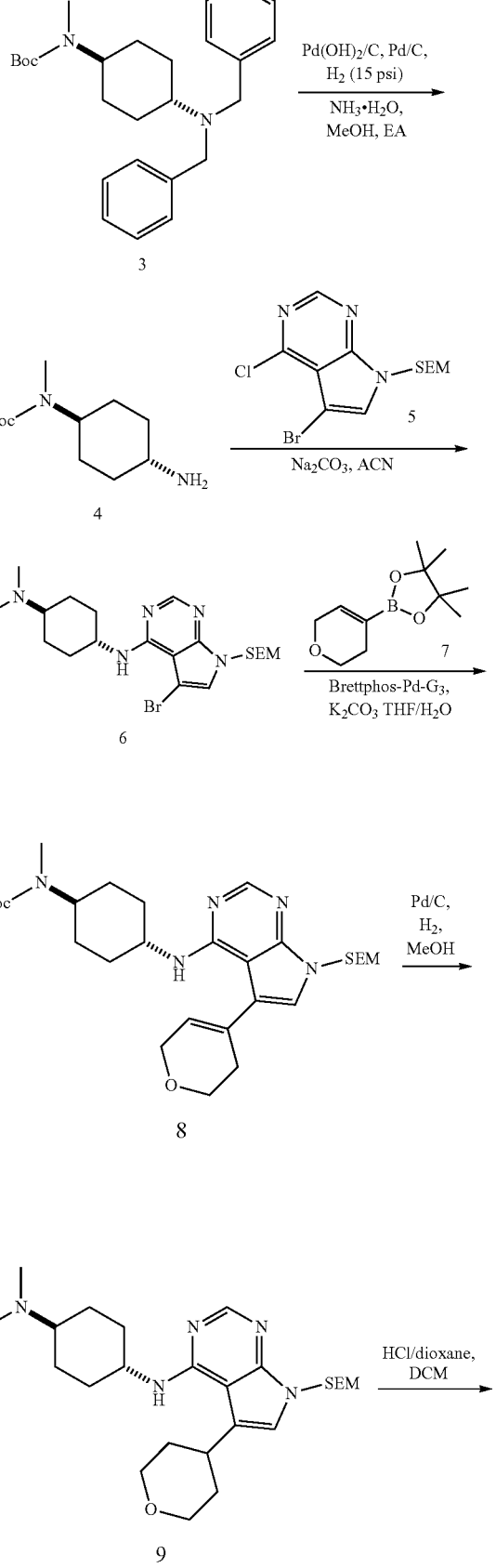

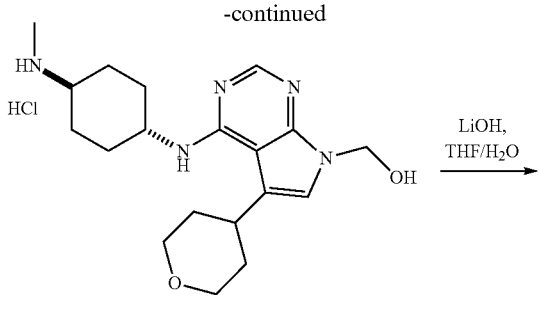

-continued

10

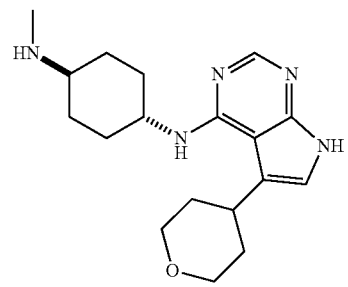

Intermediate OQ

Step 1—Tert-butyl
N-[4-(dibenzylamino)cyclohexyl]carbamate (2)

To a solution of tert-butyl N-(4-aminocyclohexyl)carbamate (3.00 g, 14.0 mmol, CAS #177906-48-8) in ACN (50 mL) was added K$_2$CO$_3$ (5.80 g, 42.0 mmol) and BnBr (7.18 g, 42.0 mmol). The mixture was stirred at 60° C. for 16 hours. On completion, the reaction mixture was filtered and concentrated in vacuo to give a residue. The residue was purified by column chromatography to give the title compound (4.60 g, 83% yield) as white solid. $^1$H NMR (400 MHz, DMSO-d$_6$) δ 7.38-7.26 (m, 8H), 7.24-7.14 (m, 2H), 6.58 (d, J=8.0 Hz, 1H), 3.56 (s, 4H), 3.16 (d, J=8.4 Hz, 1H), 2.32 (t, J=12.0 Hz, 1H), 1.78 (d, J=10.4 Hz, 4H), 1.49-1.38 (m, 2H), 1.35 (s, 9H), 1.08-0.91 (m, 2H); LC-MS (ESI$^+$) m/z 395.3 (M+H)$^+$.

Step 2—Tert-butyl N-[4-(dibenzylamino)cyclohexyl]-N-methyl-carbamate (3)

To a solution of tert-butyl N-[4-(dibenzylamino)cyclohexyl]carbamate (4.00 g, 10.1 mmol) in DMF (80 mL) was added NaH (810 mg, 20.2 mmol, 60% purity) at 0° C. The mixture was stirred at 0° C. for 0.5 hour, and then MeI (2.88 g, 20.2 mmol) was added. The mixture was stirred at 20° C. for 16 hours. On completion, the reaction mixture was quenched by water (60 mL) at 0° C., and then extracted with EA (3×100 mL). The combined organic layers were dried over Na$_2$SO$_4$, filtered and concentrated in vacuo to give a residue. The residue was triturated with DMF (8 mL) to give the title compound (3.70 g, 89% yield) as white solid. $^1$H NMR (400 MHz, CDCl$_3$) δ 7.38 (d, J=7.2 Hz, 4H), 7.30 (t, J=7.2 Hz, 4H), 7.25-7.18 (m, 2H), 3.63 (s, 4H), 2.66 (s, 3H), 2.52-2.39 (m, 1H), 1.96 (d, J=11.6 Hz, 2H), 1.72 (d, J=11.2 Hz, 2H), 1.58-1.30 (m, 14H); LC-MS (ESI$^+$) m/z 409.2 (M+H)$^+$.

Step 3—Tert-butyl
N-(4-aminocyclohexyl)-N-methyl-carbamate (4)

To a solution of tert-butyl N-[4-(dibenzylamino)cyclohexyl]-N-methyl-carbamate (2.60 g, 6.36 mmol) in a mixed solvent of MeOH (10 mL) and EA (50 mL) was added Pd(OH)$_2$/C (200 mg, 10% purity), Pd/C (200 mg, 10% purity) and NH$_3$.H$_2$O (182 mg, 0.2 mL, 38% purity) under N$_2$ atmosphere. The suspension was degassed under vacuum and purged with H$_2$ three times. The mixture was stirred at 20° C. for 16 hours under H$_2$ (15 psi). On completion, the reaction mixture was filtered and concentrated in vacuo to give the title compound (1.40 g, 96% yield) as colorless oil. $^1$H NMR (400 MHz, CDCl$_3$) δ 2.70 (s, 3H), 2.64-2.57 (m, 1H), 1.91 (d, J=12.0 Hz, 2H), 1.67 (d, J=12.0 Hz, 2H), 1.58-1.48 (m, 2H), 1.45 (s, 9H), 1.32-1.17 (m, 3H).

Step 4—Tert-butyl N-[4-[[5-bromo-7-(2-trimethylsilylethoxymethyl)pyrrolo[2,3-d]pyrimidin-4-yl]amino]cyclohexyl]-N-methyl-carbamate (6)

To a solution of tert-butyl N-(4-aminocyclohexyl)-N-methyl-carbamate (1.25 g, 5.47 mmol) and 2-[(5-bromo-4-chloro-pyrrolo[2,3-d]pyrimidin-7-yl)methoxy]ethyl-trimethyl-silane (2.18 g, 6.02 mmol, from I-442) in ACN (50 mL) was added Na$_2$CO$_3$ (1.16 g, 10.9 mmol). The mixture was stirred at 85° C. for 16 hours. On completion, the reaction mixture was filtered and concentrated in vacuo to give a residue. The residue was purified by silica gel chromatography to give the title compound (2.40 g, 79% yield) as light yellow oil. $^1$H NMR (400 MHz, DMSO-d$_6$) δ 8.21 (s, 1H), 7.55 (s, 1H), 6.06 (d, J=8.0 Hz, 1H), 5.46 (s, 2H), 4.06 (s, 1H), 3.49 (t, J=8.0 Hz, 2H), 3.32-3.29 (m, 1H), 2.69 (s, 3H), 2.08 (d, J=10.0 Hz, 2H), 1.73-1.54 (m, 4H), 1.54-1.44 (m, 2H), 1.40 (s, 9H), 0.81 (t, J=8.0 Hz, 2H), −0.09 (s, 9H); LC-MS (ESI$^+$) m/z 554.2 (M+H)$^+$.

Step 5—Tert-butyl N-[4-[[5-(3,6-dihydro-2H-pyran-4-yl)-7-(2-trimethylsilylethoxymethyl)pyrrolo[2,3-d]pyrimidin-4-yl]amino]cyclohexyl]-N-methyl-carbamate (8)

To a mixture of tert-butyl N-[4-[[5-bromo-7-(2-trimethylsilylethoxymethyl)pyrrolo[2,3-d]pyrimidin-4-yl]amino]cyclohexyl]-N-methyl-carbamate (1.20 g, 2.16 mmol) and 2-(3,6-dihydro-2H-pyran-4-yl)-4,4,5,5-tetramethyl-1,3,2-dioxaborolane (1.36 g, 6.49 mmol, CAS #287944-16-5) in a mixed solvent of THF (20 mL) and H$_2$O (4 mL) was added BrettPhos-Pd-G$_3$ (196 mg, 216 umol) and K$_2$CO$_3$ (598 mg, 4.33 mmol). The mixture was degassed and purged with N$_2$ for 3 times, and then the mixture was stirred at 55° C. for 16 hours under N$_2$ atmosphere. On completion, the reaction mixture was filtered and concentrated in vacuo to give a residue. The residue was washed with water (30 mL) and extracted with EA (6×30 mL). The combined organic layers were dried over Na$_2$SO$_4$, filtered and concentrated in vacuo to give a residue. The residue was purified by silica gel chromatography to give the title compound (0.92 g, 76% yield) as light yellow solid. $^1$H NMR (400 MHz, DMSO-d$_6$) δ 8.20 (s, 1H), 7.36 (s, 1H), 5.81 (s, 1H), 5.62 (d, J=8.0 Hz, 1H), 5.47 (s, 2H), 4.24 (d, J=2.4 Hz, 2H), 4.07-3.94 (m, 1H), 3.84 (t, J=5.6 Hz, 2H), 3.49 (t, J=8.0 Hz, 2H), 2.69 (s, 3H), 2.44 (s, 2H), 2.09 (d, J=10.4 Hz, 2H), 1.73-1.55 (m, 4H), 1.45-1.35 (m, 11H), 0.81 (t, J=8.0 Hz, 2H), −0.08 (s, 9H); LC-MS (ESI$^+$) m/z 558.4 (M+H)$^+$.

Step 6—Tert-butyl N-methyl-N-[4-1 [[5-tetrahydropyran-4-yl-7-(2-trimethylsilylethoxymethyl)pyrrolo[2,3-d]pyrimidin-4-yl]amino]cyclohexyl]carbamate (9)

To a solution of tert-butyl N-[4-[[5-(3,6-dihydro-2H-pyran-4-yl)-7-(2-trimethyl silylethoxymethyl) pyrrolo[2,3- d]pyrimidin-4-yl]amino]cyclohexyl]-N-methyl-carbamate (200 mg, 358 umol) in MeOH (10 mL) was added Pd/C (60.0 mg, 10% purity) under $N_2$. The suspension was degassed in vacuo and purged with $H_2$ three times. The mixture was stirred under $H_2$ (15 psi) at 25° C. for 16 hours. On completion, the reaction mixture was filtered and concentrated in vacuo to give the title compound (195 mg, 88% yield) as light yellow solid. LC-MS (ESI$^+$) m/z 560.3 (M+H)$^+$.

Step 7—[4-[[4-(Methylamino)cyclohexyl]amino]-5-tetrahydropyran-4-yl-pyrrolo[2,3-d]pyrimidin-7-yl] methanol (10)

To a solution of tert-butyl N-methyl-N-[4-[[5-tetrahydropyran-4-yl-7-(2-trimethylsilylethoxymethyl) pyrrolo[2,3-d]pyrimidin-4-yl]amino]cyclohexyl]carbamate (190 mg, 339 umol) in DCM (5 mL) was added HCl/dioxane (4 M, 2 mL). The reaction mixture was stirred at 45° C. for 16 hours. On completion, the reaction mixture was concentrated in vacuo to give the title compound (120 mg, 63% yield) as light yellow solid. LC-MS (ESI$^+$) m/z 360.1 (M+H)$^+$.

Step 8—N1-methyl-N4-(5-tetrahydropyran-4-yl-7H-pyrrolo[2,3-d]pyrimidin-4-yl)cyclohexane-1,4-diamine (Intermediate OQ)

To a solution of [4-[[4-(methylamino)cyclohexyl]amino]-5-tetrahydropyran-4-yl-pyrrolo[2,3-d]pyrimidin-7-yl] methanol (120 mg, 303 umol) in a mixed solvent of THF (6 mL) and $H_2O$ (1.5 mL) was added LiOH.$H_2O$ (50.8 mg, 1.21 mmol). The mixture was stirred at 25° C. for 16 hours. On completion, the reaction mixture was acidified with 1N HCl solution till pH=7, and then concentrated in vacuo give a residue. The residue was purified by prep-HPLC (column: Phenomenex Gemini 150*25 mm*10 um; mobile phase: [water (0.04% $NH_3H_2O$+10 mM $NH_4HCO_3$) to give the title compound (12.1 mg, 12% yield) as white solid. $^1$H NMR (400 MHz, DMSO-$d_6$) δ 11.31 (s, 1H), 8.07 (s, 1H), 6.83 (s, 1H), 5.53 (d, J=8.0 Hz, 1H), 4.13-3.99 (m, 1H), 3.90 (dd, J=3.2, 11.2 Hz, 2H), 3.54 (t, J=11.6 Hz, 2H), 3.28-3.19 (m, 2H), 2.32-2.21 (m, 4H), 2.01-1.80 (m, 6H), 1.60-1.49 (m, 2H), 1.47-1.32 (m, 2H), 1.20-1.01 (m, 2H); LC-MS (ESI$^+$) m/z 330.3 (M+H)$^+$.

3-(1-(2,6-Dioxopiperidin-3-yl)-3-methyl-2-oxo-2,3-dihydro-1H-benzo[d]imidazol-4-yl) propanal (Intermediate OR)

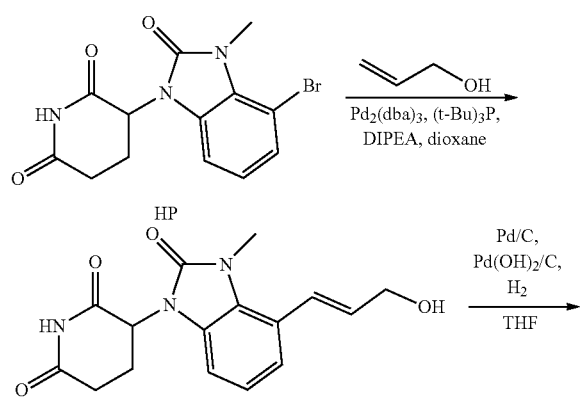

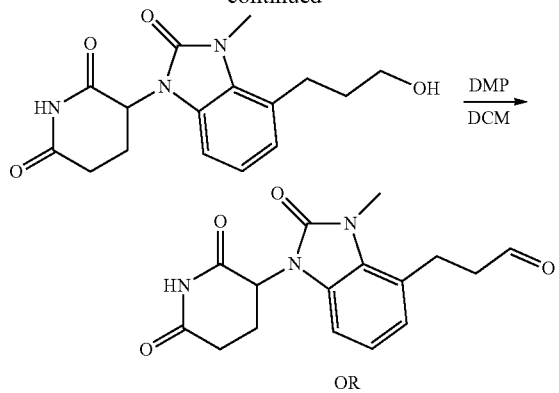

Step 1—(E)-3-(4-(3-hydroxyprop-1-en-1-yl)-3-methyl-2-oxo-2,3-dihydro-1H-benzo[d]imidazol-1-yl) piperidine-2,6-dione A mixture of 3-(4-bromo-3-methyl-2-oxo-benzimidazol-1-yl)piperidine-2,6-dione (1.00 g, 2.96 mmol, Intermediate HP), prop-2-en-1-ol (0.500 g, 8.61 mmol), DIPEA (764. mg, 5.91 mmol), $Pd_2(dba)_3$ (271 mg, 296 umol) and P(t-Bu)$_3$ (1.20 g, 591 umol, 10% purity in hexane solution) in dioxane (50 mL) was de-gassed and then heated to 30° C. for 24 hours under $N_2$. On completion, the reaction mixture was concentrated in vacuo. The residue was purified by reverse phase chromatography (0.1% FA condition) to give the title compound (860 mg, 88% yield) as a yellow solid. LC-MS (ESI$^+$) m/z 316.1 (M+H).

Step 2—3-(4-(3-Hydroxypropyl)-3-methyl-2-oxo-2,3-dihydro-1H-benzo[d]imidazol-1-yl)piperidine-2,6-dione To a solution of 3-[4-[(E)-3-hydroxyprop-1-enyl]-3-methyl-2-oxo-benzimidazol-1-yl]piperidine-2,6-dione (860 mg, 2.73 mmol) in THF (10 mL) was added Pd/C (100 mg, 163 umol) (10%, wt) under $N_2$. The suspension was degassed under vacuum and purged with $H_2$ several times. The mixture was stirred under $H_2$ (15 psi) at 20° C. for 48 hours. On completion, the reaction mixture was filtered and concentrated in vacuo. The residue was purified by reversed-phase chromatography (0.1% FA condition) to give the title compound (450 mg, 44% yield) as a yellow solid. LC-MS (ESI$^+$) m/z 318.1 (M+H).

Step 3—3-(1-(2,6-Dioxopiperidin-3-yl)-3-methyl-2-oxo-2,3-dihydro-1H-benzo[d]imidazol-4-yl) propanal To a solution of 3-[4-(3-hydroxypropyl)-3-methyl-2-oxo-benzimidazol-1-yl]piperidine-2,6-dione (250 mg, 788 umol) in DCM (10 mL) was added DMP (400 mg, 945 umol). The reaction mixture was stirred at 25° C. for 12 hours. On completion, the reaction mixture was quenched with saturated sodium thiosulfate (50 mL) and saturated aq.$NaHCO_3$, then extracted with DCM (3×150 mL). The combined organic layers were washed with brine (50 mL), dried over anhydrous sodium sulfate, and filtered. The filtrate was concentrated in vacuo to give the title compound (240 mg, 96% yield) as a white solid. $^1$H NMR (400 MHz, CDCl$_3$) δ 9.80 (s, 1H), 8.33-8.04 (m, 1H), 6.96-6.91 (m, 1H), 6.82 (d, J=8.0 Hz, 1H), 6.62 (d, J=8.0 Hz, 1H), 5.13 (dd, J=5.6, 12.4 Hz, 1H), 3.61 (s, 3H), 3.21 (t, J=7.6 Hz, 2H), 2.81 (t, J=7.6 Hz, 2H).

3-(4-(3-(((6-(Aminomethyl)hexahydrofuro[3,2-b]furan-3-yl)methyl)amino)propyl)-3-methyl-2-oxo-2,3-dihydro-1H-benzo[d]imidazol-1-yl)piperidine-2,6-dione (Intermediate OS)

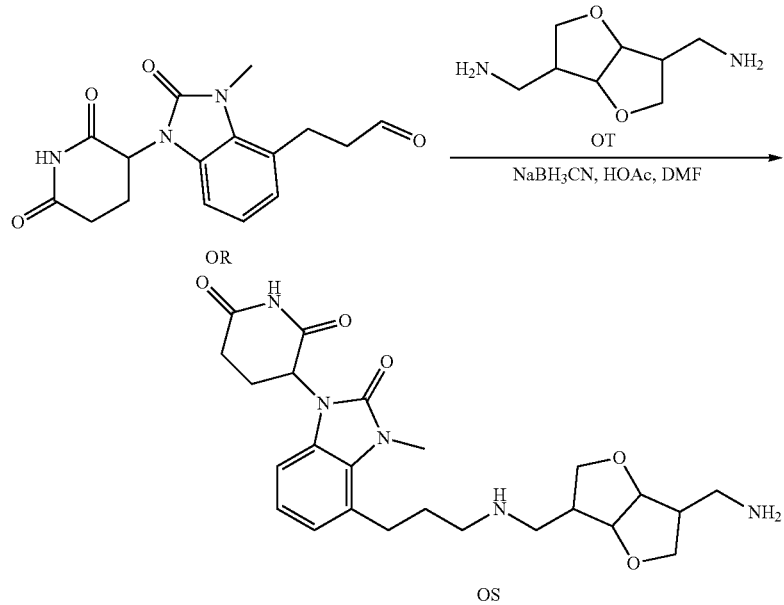

To a solution of 3-[1-(2,6-dioxo-3-piperidyl)-3-methyl-2-oxo-benzimidazol-4-yl]propanal (120 mg, 380 umol, Intermediate OR) and [6-(aminomethyl)-2,3,3a,5,6,6a-hexahydrofuro[3,2-b]furan-3-yl]methanamine (328 mg, 1.90 mmol, Intermediate OT) in DMF (5 mL) was added 4 Å MS (100 mg) and HOAc (45.7 mg, 761 umol). The reaction mixture was stirred at 80° C. for 1 hour. Then, NaBH₃CN (47.8 mg, 761 umol) was added. The resulting reaction mixture was stirred at 25° C. for 1 hour. On completion, the reaction mixture was concentrated in vacuo. The residue was purified by prep-HPLC (column: Shim-pack C18 150*25*10 um; mobile phase: [water (0.225% FA)-ACN]; B %: 1%-25%, 10 min) to give the title compound (50.0 mg, 23% yield) as a white solid. LC-MS (ESI$^+$) m/z 472.3 (M+H).

[6-(Aminomethyl)-2,3,3a,5,6,6a-hexahydrofuro[3,2-b]furan-3-yl]methanamine (Intermediate OT)

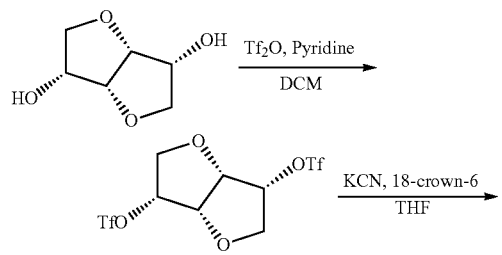

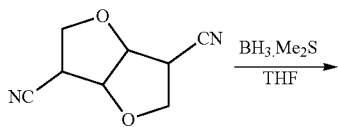

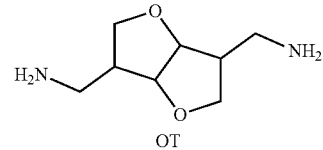

Step 1—[(3R,3aS,6R,6aS)-6-(Trifluoromethylsulfonyloxy)-2,3,3a,5,6,6a-hexahydrofuro[3,2-b]furan-3-yl]trifluoromethanesulfonate To a solution of (3R,3aR,6R,6aR)-2,3,3a,5,6,6a-hexahydrofuro[3,2-b]furan-3,6-diol (25.0 g, 171 mmol, CAS #641-74-7) and pyridine (32.4 g, 410 mmol) in DCM (250 mL) at 0° C. was added Tf₂O (115 g, 410 mmol, 67.74 mL) dropwise. Then the mixture was stirred at rt for 3 hours. On completion, the reaction mixture was acidified with 1N aq.HCl until the pH=3. The mixture was washed with H₂O (3×50 mL). The organic layer was basified with saturated NaHCO₃ solution until the pH=8. The organic layer was then washed with brine (2×30 mL) and dried over Na₂SO₄, then filtered. The filtrate was concentrated in vacuo to give the title compound (70.0 g, 99% yield) as yellow solid. ¹H NMR (400 MHz, CDCl₃) δ 5.28-5.19 (m, 2H), 4.82-4.75 (m, 2H), 4.22-4.12 (m, 4H).

Step 2—2,3,3A,5,6,6a-Hexahydrofuro[3,2-b]furan-3,6-dicarbonitrile

To a mixture of 18-crown-6 (58.9 g, 223 mmol) and KCN (48.4 g, 743 mmol) in THF (400 mL) was added a solution of [(3R,3aS,6R,6aS)-6-(trifluoromethylsulfonyloxy)-2,3,3a,5,6,6a-hexahydrofuro[3,2-b]furan-3-yl]trifluoromethanesulfonate (61.0 g, 148 mmol) in THF (400 mL). Then the reaction mixture was stirred at 0° C. for 3 hours. On completion, the reaction was warmed to room temperature, then the mixture was poured into cold water (200 mL) and extracted with chloroform (5×100 mL). The combined organic layers were dried over Mg$_2$SO$_4$, then filtered. The filtrate was decolorized with activated carbon. After filtration through celite, the filtrate was concentrated in vacuo. The residue was purified by Prep-TLC (SiO$_2$, PE:EA=1:1) to give the title compound (5.00 g, 20% yield) as yellowish solid. $^1$H NMR (400 MHz, CDCl$_3$) δ 5.03 (s, 2H), 4.14-4.07 (m, 4H), 3.22-3.19 (m, 2H).

Step 3—[6-(Aminomethyl)-2,3,3a,5,6,6a-hexahydrofuro[3,2-b]furan-3-yl]methanamine To a solution of 2,3,3a,5,6,6a-hexahydrofuro[3,2-b]furan-3,6-dicarbonitrile (2.50 g, 15.2 mmol) in THF (25.0 mL) was added BH$_3$-Me$_2$S (10.0 M, 25.0 mL) dropwise. The mixture was stirred at 20° C. for 16 hours under N$_2$. On completion, the reaction mixture was quenched with MeOH (50 mL). The mixture was concentrated in vacuo to give the title compound (2.62 g, 100% yield) as white solid. $^1$H NMR (400 MHz, D$_2$O) δ 4.30-3.86 (m, 1H), 3.71-3.47 (m, 4H), 3.12-2.91 (m, 3H), 2.68-2.50 (m, 2H), 1.68-1.40 (m, 2H).

3-[1-(2,6-Dioxo-3-piperidyl)-3-methyl-2-oxo-benzimidazol-5-yl]propanal (Intermediate OU)

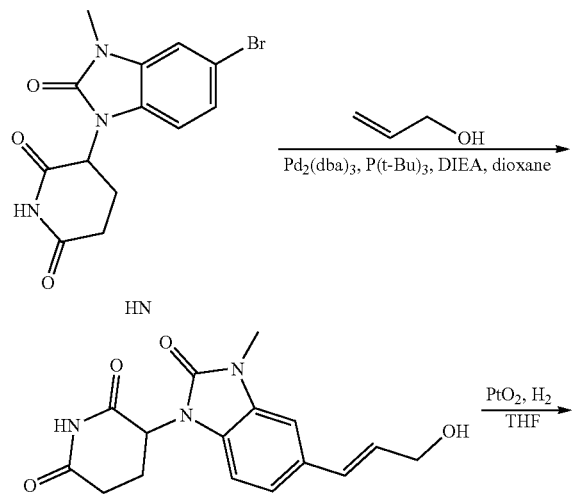

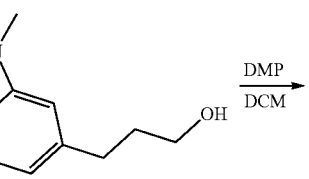

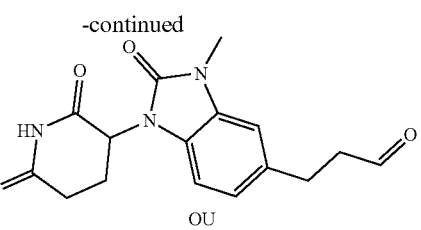

Step 1—3-[5-(3-Hydroxyprop-1-enyl)-3-methyl-2-oxo-benzimidazol-1-yl]piperidine-2,6-dione To a solution of 3-(5-bromo-3-methyl-2-oxo-benzimidazol-1-yl)piperidine-2,6-dione (1.00 g, 2.96 mmol, Intermediate HN) and prop-2-en-1-ol (350 mg, 6.03 mmol) in dioxane (10.0 mL) was added P(t-Bu)$_3$ (1.20 g, 591 umol, 10 wt %), Pd$_2$(dba)$_3$ (270 mg, 295 umol) and DIPEA (496 mg, 3.84 mmol). The mixture was stirred at 20° C. for 16 hours under N$_2$. On completion, the mixture was concentrated in vacuo. The residue was purified by reverse phase chromatography (0.1% FA) to give the title compound (750 mg, 80% yield) as yellow solid. $^1$H NMR (400 MHz, DMSO-d$_6$) δ 12.74 (s, 1H), 11.08 (s, 1H), 9.80-9.62 (m, 1H), 7.11-7.07 (m, 1H), 7.01 (d, J=8.0 Hz, 1H), 6.95-6.93 (m, 1H), 6.96-6.83 (m, 1H), 5.41-5.25 (m, 1H), 3.31 (s, 3H), 2.94-2.89 (m, 2H), 2.81-2.76 (m, 1H), 2.75-2.65 (m, 1H), 2.65-2.54 (m, 1H), 2.04-1.94 (m, 1H).

Step 2—3-[5-(3-Hydroxypropyl)-3-methyl-2-oxo-benzimidazol-1-yl]piperidine-2,6-dione To a solution of 3-[5-[(E)-3-hydroxyprop-1-enyl]-3-methyl-2-oxo-benzimidazol-1-yl]piperidine-2,6-dione (750 mg, 2.38 mmol) in THF (30.0 mL) was added PtO$_2$ (54.0 mg, 237 umol). The mixture was stirred at 20° C. for 16 hours under H$_2$ (15 psi). On completion, the mixture was filtered and the filtrate was concentrated in vacuo. The residue was purified by reverse phase chromatography (0.1% FA) to give the title compound (220 mg, 29% yield) as white solid. $^1$H NMR (400 MHz, DMSO-d$_6$) δ 11.08 (s, 1H), 7.06-6.96 (m, 2H), 6.90-6.82 (m, 1H), 5.38-5.27 (m, 1H), 3.45-3.42 (m, 2H), 3.33 (s, 3H), 2.98-2.78 (m, 2H), 2.76-2.68 (m, 1H), 2.64-2.60 (m, 1H), 2.59-2.52 (m, 1H), 2.05-1.93 (m, 1H), 1.83-1.66 (m, 2H).

Step 3—3-[1-(2,6-Dioxo-3-piperidyl)-3-methyl-2-oxo-benzimidazol-5-yl]propanal To a solution of 3-[5-(3-hydroxypropyl)-3-methyl-2-oxo-benzimidazol-1-yl]piperidine-2,6-dione (220 mg, 693 umol) in DCM (10.0 mL) was added DMP (352 mg, 831 umol). The mixture was stirred at 25° C. for 1 hour. On completion, the mixture was quenched with saturated Na$_2$S$_2$O$_3$ (30 mL) and washed with saturated NaHCO$_3$ (2×30 mL). The organic layer was dried over anhydrous Na$_2$SO$_4$, filtered and concentrated in vacuo to give the title compound (200 mg, 91% yield) as yellow solid. LC-MS (ESI$^+$) m/z 316.1 (M+H)$^+$.

3-[5-[3-[[3-(Aminomethyl)-2,3,3a,5,6,6a-hexahydro-furo[3,2-b]furan-6-yl]methylamino]propyl]-3-methyl-2-oxo-benzimidazol-1-yl]piperidine-2,6-dione (Intermediate OV)

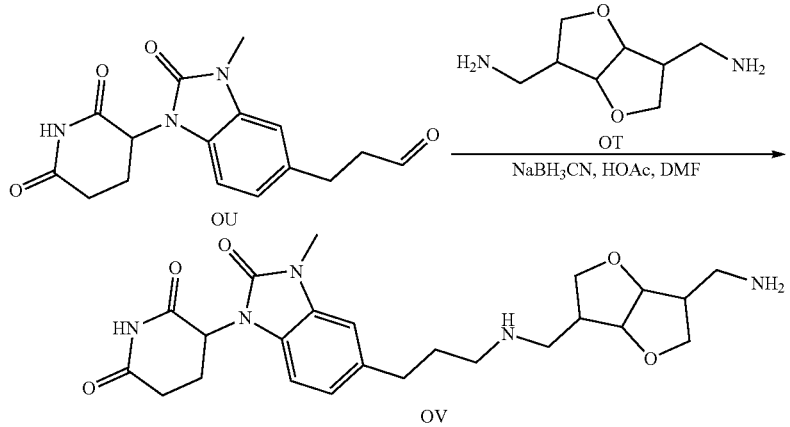

To a solution of 3-[1-(2,6-dioxo-3-piperidyl)-3-methyl-2-oxo-benzimidazol-5-yl]propanal (190 mg, 602 umol, Intermediate OU), [6-(aminomethyl)-2,3,3a,5,6,6a-hexahydro-furo[3,2-b]furan-3-yl]methanamine (518 mg, 3.01 mmol, Intermediate OT) in DMF (6.00 mL) was added HOAc (72.3 mg, 1.21 mmol) and 4 Å molecular sieves (10.0 mg). The mixture was stirred at 80° C. for 1 hour. The mixture was cooled to 25° C., then NaBH$_3$CN (75.7 mg, 1.21 mmol) was added, and the mixture was stirred at 25° C. for 16 hours. On completion, the mixture was quenched with H$_2$O (1 mL), filtered and the filtrate was concentrated in vacuo. The residue was purified by prep-HPLC (column: Shim-pack C18 150*25*10 um; mobile phase: [water (0.225% FA)-ACN]; B %: 1%-30%, 10 min) to give the title compound (120 mg, 42% yield) as yellow solid. $^1$H NMR (400 MHz, DMSO-d$_6$) δ 8.19 (s, 1H), 8.04 (s, 1H), 7.07-6.98 (m, 2H), 6.87 (d, J=7.2 Hz, 1H), 5.42-5.28 (m, 1H), 4.42-4.35 (m, 2H), 4.31-4.22 (m, 2H), 3.85-3.78 (m, 2H), 3.33 (s, 3H), 3.12-3.06 (m, 2H), 3.02-2.94 (m, 2H), 2.79-2.73 (m, 1H), 2.66-2.64 (m, 1H), 2.47-2.46 (m, 1H), 2.32-2.24 (m, 6H), 2.07-1.94 (m, 1H), 1.79-1.70 (m, 2H).

4-Amino-1-[4-(hydroxymethyl)phenyl]pyrazole-3-carbonitrile (Intermediate OW) (IRW-598)

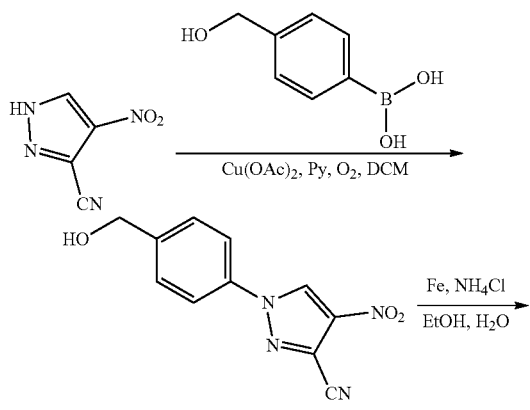

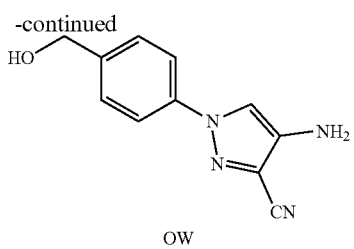

Step 1—1-[4-(Hydroxymethyl)phenyl]-4-nitro-pyrazole-3-carbonitrile

To a mixture of 4-nitro-1H-pyrazole-3-carbonitrile (3.00 g, 21.7 mmol, CAS #61241-07-4) and [4-(hydroxylmethyl)phenyl]boronic acid (2.20 g, 14.4 mmol, CAS #59012-93-2) in mixed solvents of pyridine (25 mL) and DCM (75 mL) was added Cu(OAc)$_2$ (3.94 g, 21.7 mmol) under O$_2$ (15 psi), then the mixture was stirred at 20° C. for 12 hours. On completion, the reaction mixture was concentrated in vacuo to give a residue. The residue was purified by column chromatography (SiO$_2$) to give the title compound (3.00 g, 78% yield) as a yellow solid. $^1$H NMR (400 MHz, DMSO-d$_6$) δ 9.90 (s, 1H), 7.95 (d, J=8.8 Hz, 2H), 7.56 (d, J=8.4 Hz, 2H), 4.62 (s, 2H), 4.39 (s, 1H).

Step 2—4-Amino-1-[4-(hydroxymethyl)phenyl]pyrazole-3-carbonitrile

To a mixture of 1-[4-(hydroxymethyl)phenyl]-4-nitro-pyrazole-3-carbonitrile (3.00 g, 12.3 mmol) in a mixed solvents of EtOH (120 mL) and H$_2$O (30 mL) was added NH$_4$Cl (6.57 g, 123 mmol). The mixture was heated to 65° C. Then Fe (6.86 g, 123 mmol) was added in portions. The reaction mixture was stirred at 65° C. for 1 hour. On completion, the reaction mixture was cooled to 25° C., filtered and concentrated in vacuo to give a residue. The residue was purified by column chromatography (SiO$_2$) to give the title compound (1.20 g, 42% yield) as a yellow solid. $^1$H NMR (400 MHz, DMSO-d$_6$) δ 7.84 (s, 1H), 7.70

(d, J=8.8 Hz, 2H), 7.41 (d, J=8.8 Hz, 2H), 5.25 (t, J=5.6 Hz, 1H), 5.00 (s, 2H), 4.50 (d, J=5.6 Hz, 2H).

Tert-butyl N-[4-[4-[[3-cyano-1-(4-formylphenyl)pyrazol-4-yl]carbamoyl]oxazol-2-yl]-2-pyridyl]-N-(cyclopropylmethyl)carbamate (Intermediate OX)

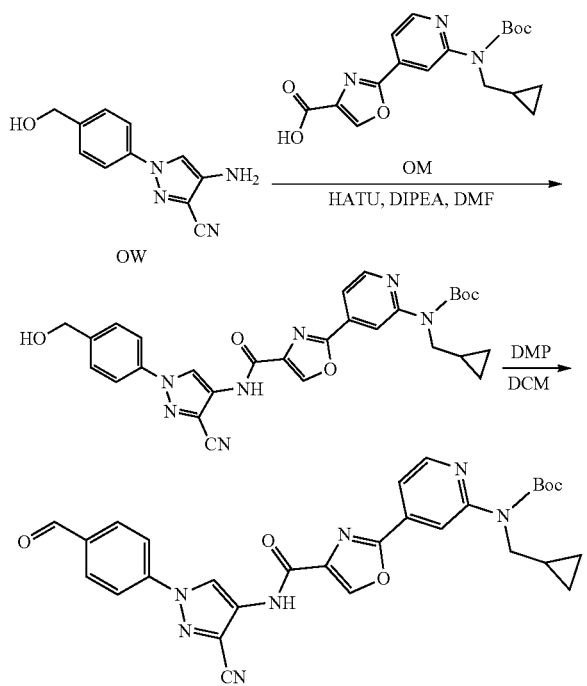

Step 1-Tert-butyl N-[4-[4-[[3-cyano-1-[4-(hydroxymethyl)phenyl]pyrazol-4-yl]carbamoyl]oxazol-2-yl]-2-pyridyl]-N-(cyclopropylmethyl)carbamate To a mixture of 4-amino-1-[4-(hydroxymethyl)phenyl]pyrazole-3-carbonitrile (300 mg, 1.40 mmol, Intermediate OW) and 2-[2-[tert-butoxycarbonyl(cyclopropylmethyl)amino]-4-pyridyl]oxazole-4-carboxylic acid (503 mg, 1.40 mmol, Intermediate OM) in DMF (10 mL) was added DIPEA (543 mg, 4.20 mmol) and HATU (639 mg, 1.68 mmol). The reaction mixture was stirred at 20° C. for 1 hour. On completion, the reaction mixture was concentrated in vacuo to give a residue. The residue was purified by reverse phase (0.1% FA condition) to give the title compound (453 mg, 52% yield) as a yellow solid. $^1$H NMR (400 MHz, DMSO-d$_6$) δ 10.73 (s, 1H), 9.08 (s, 1H), 8.85 (s, 1H), 8.61 (d, J=5.2 Hz, 1H), 8.36 (s, 1H), 7.86 (d, J=8.8 Hz, 2H), 7.72 (d, J=1.2, 4.0 Hz, 1H), 7.51 (d, J=8.4 Hz, 2H), 5.34 (t, J=5.6 Hz, 1H), 4.58 (d, J=5.6 Hz, 2H), 3.88 (d, J=6.8 Hz, 2H), 1.52 (s, 9H), 1.20-1.15 (m, 1H), 0.46-0.37 (m, 2H), 0.30-0.20 (m, 2H).

Step 2-Tert-butyl N-[4-[4-[[3-cyano-1-(4-formylphenyl)pyrazol-4-yl]carbamoyl]oxazol-2-yl]-2-pyridyl]-N-(cyclopropylmethyl)carbamate To a mixture of tert-butyl N-[4-[4-[[3-cyano-1-[4-(hydroxymethyl)phenyl]pyrazol-4-yl]carbamoyl]oxazol-2-yl]-2-pyridyl]-N-(cyclopropylmethyl)carbamate (350 mg, 630 umol) in DCM (15 mL) was added DMP (294 mg, 693 umol). The reaction was stirred at 20° C. for 1 hour. On completion, a solution of sodium thiosulfate aqueous solution (20 mL) and saturated sodium bicarbonate (20 mL) was added into the mixture and stirred for 10 minutes. Then the mixture was extracted with DCM (2×20 mL). The combined organic layer was washed with brine (2×30 mL), dried over anhydrous Na$_2$SO$_4$, filtered and concentrated in vacuo to give title compound (320 mg, 91% yield) as a yellow solid. $^1$H NMR (400 MHz, DMSO-d$_6$) δ 10.85 (s, 1H), 10.07 (s, 1H), 9.14-9.02 (m, 2H), 8.61 (d, J=5.2 Hz, 1H), 8.36 (s, 1H), 8.23-8.15 (m, 2H), 8.14-8.08 (m, 2H), 7.72 (d, J=5.2 Hz, 1H), 3.88 (d, J=7.2 Hz, 2H), 1.52 (s, 9H), 1.26-1.11 (m, 1H), 0.49-0.37 (m, 2H), 0.30-0.21 (m, 2H).

6-Bromo-3H-1,3-benzoxazol-2-one (Intermediate OY)

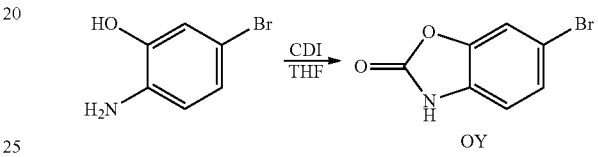

To a solution of 2-amino-5-bromo-phenol (4.50 g, 23.9 mmol, CAS #38191-34-3) in THF (120 mL) was added CDI (4.66 g, 28.7 mmol). The reaction mixture was stirred at 70° C. for 2 hours. On completion, the reaction mixture was added to water (240 mL) and the mixture was adjusted pH=6-7 with 2.0 M aq.HCl, then ethyl acetate (150 mL) was added. The organic layer was separated and washed with a saturated sodium chloride solution (20 mL), dried over anhydrous sodium sulfate, filtered, and concentrated in vacuo. The residue was recrystallized in toluene (60 mL) to give the title compound (3.75 g, 90% yield) as an off-white solid. $^1$H NMR (400 MHz, DMSO-d$_6$) δ 7.58 (d, J=1.6 Hz, 1H), 7.32 (dd, J=1.8, 8.4 Hz, 1H), 7.06 (s, 1H), 7.04-7.01 (m, 1H). LC-MS (ESI$^+$) m/z 216.0 & 214.0 (M+Na)$^+$.

3-(6-Bromo-2-oxo-1,3-benzoxazol-3-yl)piperidine-2,6-dione (Intermediate OZ)

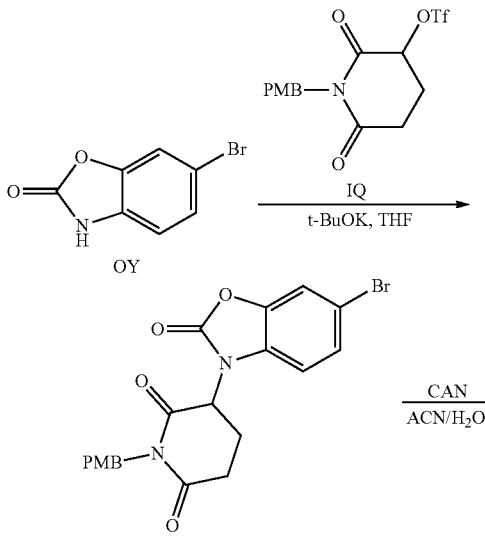

Step 1—3-(6-Bromo-2-oxo-1,3-benzoxazol-3-yl)-1-[(4-methoxyphenyl)methyl]piperidine-2,6-dione

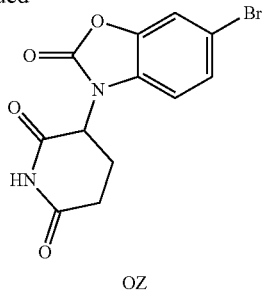

OZ

To a solution of 6-bromo-3H-1,3-benzoxazol-2-one (2.00 g, 9.35 mmol, Intermediate OY) in THF (50 mL) was added t-BuOK (1.26 g, 11.2 mmol). The reaction mixture was stirred at 0° C. for 0.5 hour. Subsequently, [1-[(4-methoxyphenyl)methyl]-2,6-dioxo-3-piperidyl]trifluoromethanesulfonate (4.81 g, 12.6 mmol, Intermediate IQ) in a solution of THF (30 mL) was added dropwise. The resulting reaction mixture was stirred at 20° C. for 0.5 hour under $N_2$. On completion, the reaction mixture was quenched with saturated $NH_4Cl$ (100 mL), and extracted with ethyl acetate (100 mL). The combined organic layer was washed with brine (2×100 mL), dried over anhydrous sodium sulfate and filtered. The filtrate was concentrated in vacuo. The residue was purified by silica gel chromatography (PE:EA:DCM=5:1:2) to give the title compound (3.75 g, 90% yield) as a yellow solid. $^1$H NMR (400 MHz, CDCl$_3$) δ 7.22-7.20 (d, J=8.0 Hz, 1H), 6.89-6.87 (d, J=8.0 Hz, 1H), 4.90-4.86 (m, 1H), 4.47-4.36 (m, 2H) 3.81 (s, 3H), 2.67-2.64 (m, 1H), 2.59-2.54 (m, 2H), 2.40-2.38 (m, 1H). LC-MS (ESI$^+$) m/z 466.9 & 468.9 (M+Na)$^+$.

Step 2—3-(6-Bromo-2-oxo-1,3-benzoxazol-3-yl)piperidine-2,6-dione

To a mixture of 3-(6-bromo-2-oxo-1,3-benzoxazol-3-yl)-1-[(4-methoxyphenyl)methyl]piperidine-2,6-dione (2.00 g, 4.49 mmol) in ACN (60 mL) was added CAN (7.39 g, 13.4 mmol) in solution of $H_2O$ (20 mL), and the reaction mixture was degassed and purged with $N_2$ for 3 times. Then the mixture was stirred at 20° C. for 3 hours under $N_2$ atmosphere. On completion, the reaction mixture was filtered. The filtered cake was collected and dried in vacuo to give the title compound (900 mg, 61% yield) as a white solid. $^1$H NMR (400 MHz, DMSO-d$_6$) δ 11.24 (s, 1H), 7.74 (d, J=1.6 Hz, 1H), 7.48-7.41 (m, 1H), 7.27 (d, J=8.4 Hz, 1H), 5.39 (dd, J=5.2, 12.8 Hz, 1H), 3.00-2.80 (m, 1H), 2.76-2.60 (m, 2H), 2.18-2.15 (m Hz, 1H). LC-MS (ESI$^+$) m/z 325.0 &327.0 (M+H)$^+$.

2-3-[6-[3-[2-(2-Aminoethoxy)ethoxy]propyl]-2-oxo-1,3-benzoxazol-3-yl]piperidine-2,6-dione (Intermediate PA)

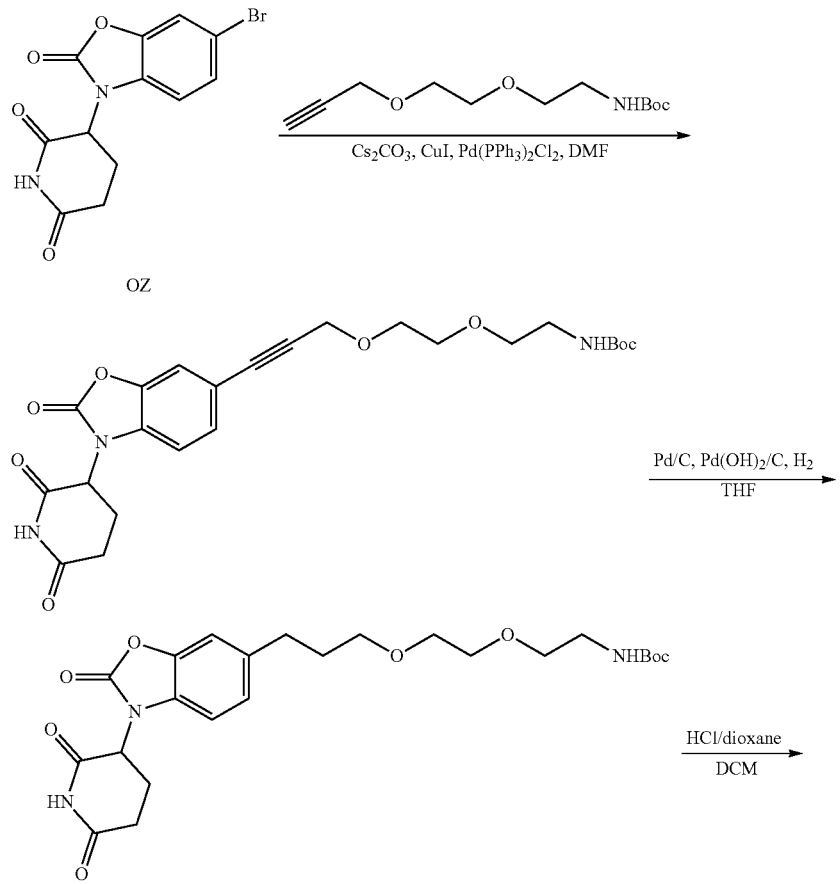

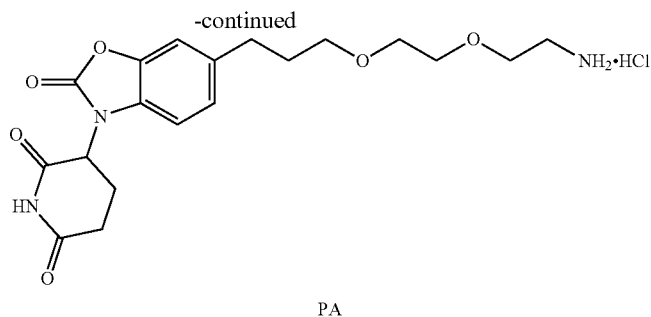

PA

Step 1—Tert-butyl N-[2-[2-[3-[3-(2,6-dioxo-3-piperidyl)-2-oxo-1,3-benzoxazol-6-yl]propoxy]ethoxy]ethyl]carbamate 3-(6-bromo-2-oxo-1,3-benzoxazol-3-yl)piperidine-2,6-dione (400 mg, 1.23 mmol, Intermediate OZ), tert-butyl N-[2-(2-prop-2-ynoxyethoxy)ethyl]carbamate (898 mg, 3.69 mmol, synthesized via Step 1 of Intermediate CQ), Pd(PPh$_3$)$_2$Cl$_2$ (86.3 mg, 123 umol), CuI (23.4 mg, 123 umol), 4 Å MS (400 mg, 307 umol) and Cs$_2$CO$_3$ (2.00 g, 6.15 mmol) in DMF (6 mL) was stirred at 80° C. for 2 hours under N$_2$. On completion, the reaction mixture was filtered and the filtrate was concentrated in vacuo. The residue was purified by column chromatography (ACN) to give an impure product. The impure product was re-purified by reverse phase (0.1% FA condition) to give the title compound (340 mg, 54% yield) as yellow oil. $^1$H NMR (400 MHz, DMSO-d$_6$) δ 11.23 (s, 1H), 7.53 (s, 1H), 7.37-7.33 (m, 1H), 7.31-7.27 (m, 1H), 6.82-6.75 (m, 1H), 5.40 (dd, J=5.2, 12.8 Hz, 1H), 4.39 (s, 2H), 3.65-3.60 (m, 2H), 3.57-3.53 (m, 2H), 3.41-3.38 (m, 2H), 3.07-3.02 (m, 2H), 2.93-2.81 (m, 1H), 2.72-2.61 (m, 2H), 2.18-2.16 (m, 1H), 1.37 (s, 9H), 1.37-1.36 (m, 1H). LC-MS (ESI$^+$) m/z 510.2 (M+Na)$^+$.

Step 2—Tert-butyl N-[2-[2-[3-[3-(2,6-dioxo-3-piperidyl)-2-oxo-1,3-benzoxazol-6-yl]propoxy]ethoxy]ethyl]carbamate To a solution of tert-butyl N-[2-[2-[3-[3-(2,6-dioxo-3-piperidyl)-2-oxo-1,3-benzoxazol-6-yl]prop-2-ynoxy]ethoxy]ethyl]carbamate (420 mg, 861 umol) in THF (30 mL) was added Pd/C (0.1 g, 10% wt) and Pd(OH)$_2$/C (0.1 g, 10% wt) under N$_2$. The suspension was degassed under vacuum and purged with H$_2$ gas several times. The mixture was stirred under H$_2$ (15 psi) at 20° C. for 12 hours. On completion, the reaction mixture was filtered and the filtrate was concentrated in vacuo to give the title compound (440 mg, 93% yield) as yellow oil. $^1$H NMR (400 MHz, DMSO-d$_6$) δ 11.25 (s, 1H), 7.32 (s, 1H), 7.22 (d, J=8.0 Hz, 1H), 7.11 (d, J=8.0 Hz, 1H), 6.79 (s, 1H), 5.40 (dd, J=5.2, 12.8 Hz, 1H), 3.57-3.53 (m, 4H), 3.46-3.43 (m, 4H), 3.13 (d, J=6.0 Hz, 2H), 3.00-2.89 (m, 1H), 3.00-2.89 (m, 1H), 2.80-2.67 (m, 4H), 2.25-2.20 (m, 1H), 1.88-1.83 (m, 2H), 1.43-1.42 (m, 9H). LC-MS (ESI$^+$) m/z 514.2 (M+Na)$^+$.

Step 3—2-3-[6-[3-[2-(2-Aminoethoxy)ethoxy]propyl]-2-oxo-1,3-benzoxazol-3-yl]piperidine-2,6-dione To a solution of tert-butyl N-[2-[2-[3-[3-(2,6-dioxo-3-piperidyl)-2-oxo-1,3-benzoxazol-6-yl]propoxy]ethoxy]ethyl]carbamate (150 mg, 305 umol) in DCM (5 mL) was added HCl/dioxane (4 M, 7.50 mL). The reaction mixture was stirred at 20° C. for 1 hour. On completion, the reaction mixture was concentrated in vacuo to give the title compound (130 mg, 99% yield, HCl salt) as a white solid. LC-MS (ESI$^+$) m/z 392.2 (M+H)$^+$.

2-[2-(Cyclopropylmethylamino)-4-pyridyl]-N-[3-(difluoromethyl)-1-(4-formylphenyl)pyrazol-4-yl]oxazole-4-carboxamide (Intermediate PB)

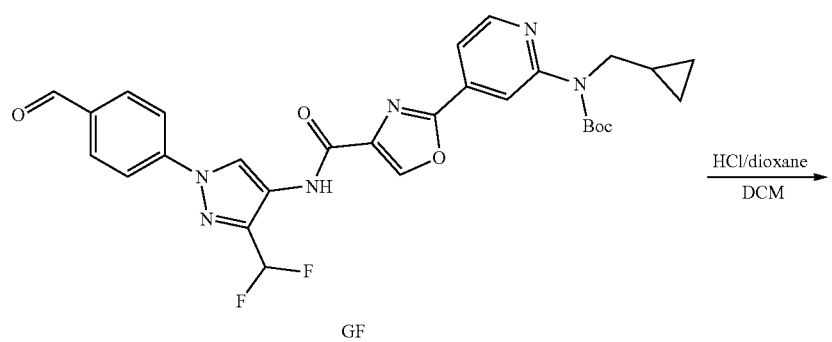

GF

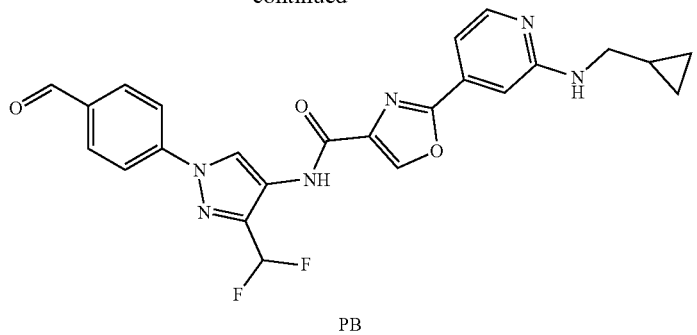

PB

To a solution of tert-butyl N-(cyclopropylmethyl)-N-[4-[4-[[3-(difluoromethyl)-1-(4-formylphenyl) pyrazol-4-yl]carbamoyl]oxazol-2-yl]-2-pyridyl]carbamate (100 mg, 172 umol, Intermediate GF) in DCM (3.00 mL) was added HCl/dioxane (4.00 M, 3.00 mL), and the mixture was stirred at 25° C. for 0.5 hr. On completion, the mixture was concentrated in vacuo to give the title compound (80.0 mg, 96% yield) as yellow solid. LC-MS (ESI$^+$) m/z 479.2 (M+H)$^+$.

Tert-butyl N-(4-hydroxy-4-methyl-hept-6-enyl)carbamate (Intermediate PC)

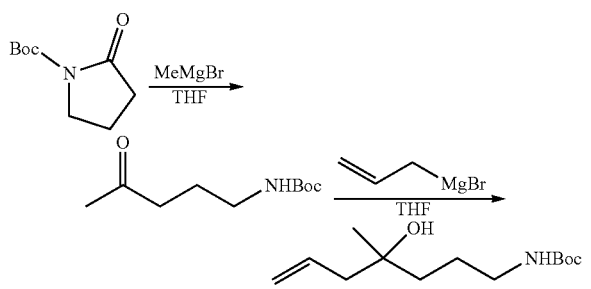

Step 1—Tert-butyl N-(4-oxopentyl)carbamate

To a solution of tert-butyl 2-oxopyrrolidine-1-carboxylate (5.00 g, 26.9 mmol) in THF (50.0 mL) was added MeMgBr (3.00 M, 10.8 mL) dropwise at −78° C. under N$_2$, and the mixture was stirred at −78° C. for 3 hrs. On completion, the mixture was poured into cool water (50 mL) and then extracted with MTBE (2×50 mL). The organic layers were dried over anhydrous Na$_2$SO$_4$, filtered and concentrated in vacuo. The mixture was purified by silica gel column (PE:EA=5:1) to give the title compound (4.45 g, 81% yield) as yellow solid. $^1$H NMR (400 MHz, CDCl$_3$) δ 4.67 (s, 1H), 3.19-3.02 (m, 2H), 2.51-2.47 (m, 2H), 2.14 (s, 3H), 1.80-1.70 (m, 2H), 1.42 (s, 9H).

Step 2—Tert-butyl N-(4-hydroxy-4-methyl-hept-6-enyl)carbamate

To a solution of tert-butyl N-(4-oxopentyl)carbamate (2.00 g, 9.94 mmol) in THF (20.0 mL) was added allyl(bromo)magnesium (1.00 M, 12.9 mL) dropwise at −78° C., and the mixture was stirred at 0° C. for 3 hrs under N$_2$. On completion, the mixture was quenched with saturated NH$_4$Cl (30 mL), then extracted with MTBE (3×30 mL). The organic layers were dried over anhydrous Na$_2$SO$_4$, filtered and concentrated in vacuo. The mixture was purified by silica gel column (PE:EA=5:1) to give the title compound (770 mg, 31% yield) as yellow oil. $^1$H NMR (400 MHz, DMSO-d$_6$) δ 6.74 (s, 1H), 5.91-5.74 (m, 1H), 5.03 (s, 1H), 4.99 (d, J=3.6 Hz, 1H), 4.15 (s, 1H), 2.91-2.83 (m, 2H), 2.15-2.05 (m, 2H), 1.46-1.39 (m, 2H), 1.38 (s, 9H), 1.31-1.24 (m, 2H), 1.00 (s, 3H).

3-[5-(7-Amino-4-hydroxy-4-methyl-heptyl)-3-methyl-2-oxo-benzimidazol-1-yl]piperidine-2,6-dione (Intermediate PD)

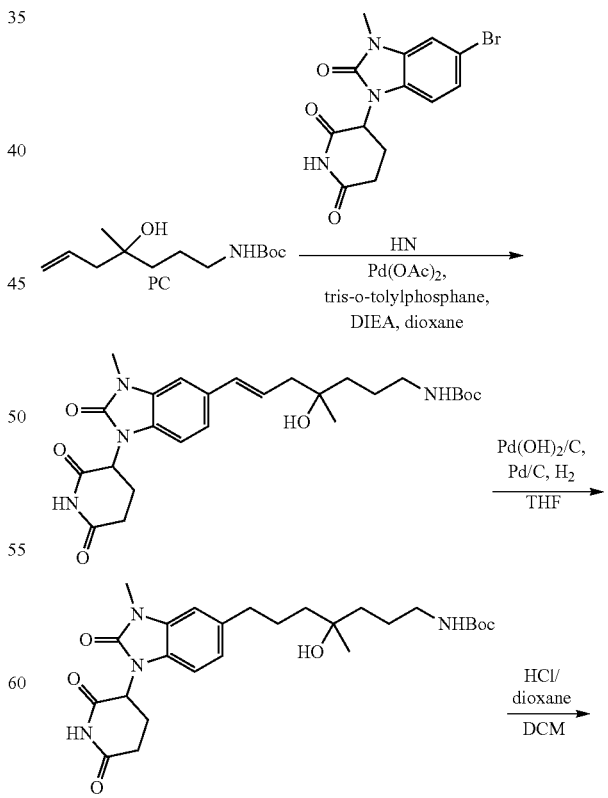

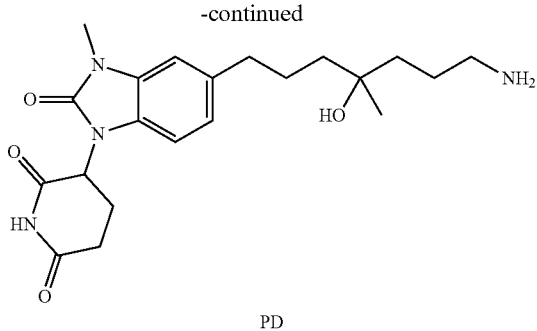

PD

Step 1—Tert-butyl N-[(E)-7-[1-(2,6-dioxo-3-piperidyl)-3-methyl-2-oxo-benzimidazol-5-yl]-4-hydroxy-4-methyl-hept-6-enyl]carbamate To a solution of 3-(5-bromo-3-methyl-2-oxo-benzimidazol-1-yl)piperidine-2,6-dione (200 mg, 591 umol, Intermediate HN), tert-butyl N-(4-hydroxy-4-methyl-hept-6-enyl)carbamate (287 mg, 1.18 mmol, Intermediate PC) in dioxane (12.0 mL) was added tris-o-tolylphosphane (36.0 mg, 118 umol), Pd(OAc)$_2$ (13.2 mg, 59.1 umol) and DIPEA (1.53 g, 11.8 mmol) under N$_2$. The mixture was stirred at 120° C. for 16 hrs. On completion, the mixture was concentrated in vacuo. The mixture was purified by reverse phase chromatography (0.1% FA) to give the title compound (180 mg, 60% yield) as yellow solid. $^1$H NMR (400 MHz, DMSO-d$_6$) δ 11.10 (s, 1H), 7.27 (s, 1H), 7.04 (s, 2H), 6.76 (s, 1H), 6.45-6.34 (m, 1H), 6.33-6.21 (m, 1H), 5.40-5.30 (m, 1H), 4.26 (s, 1H), 2.92-2.89 (m, 1H), 2.89-2.84 (m, 2H), 2.71-2.67 (m, 1H), 2.64-2.56 (m, 1H), 2.30-2.20 (m, 2H), 2.08 (s, 3H), 2.05-1.96 (m, 1H), 1.52-1.41 (m, 2H), 1.36 (s, 9H), 1.35-1.31 (m, 2H), 1.07 (s, 3H).

Step 2—Tert-butyl N-[7-[1-(2,6-dioxo-3-piperidyl)-3-methyl-2-oxo-benzimidazol-5-yl]-4-hydroxy-4-methyl-heptyl]carbamate To a solution of tert-butyl N-[(E)-7-[1-(2,6-dioxo-3-piperidyl)-3-methyl-2-oxo-benzimidazol-5-yl]-4-hydroxy-4-methyl-hept-6-enyl]carbamate (160 mg, 319 umol) in THF (8.00 mL) was added Pd(OH)$_2$/C (50.0 mg, 10% wt) and Pd/C (50 mg, 10% wt), and the mixture was stirred at 25° C. for 3 hrs under H$_2$ gas (15 psi). On completion, the mixture was filtered and the filtrate was concentrated in vacuo to give the title compound (160 mg, 99% yield) as white solid. $^1$H NMR (400 MHz, DMSO-d$_6$) δ 11.13 (s, 1H), 7.08 (s, 1H), 7.05 (d, J=8.0 Hz, 1H), 6.92 (s, 2H), 6.79 (s, 1H), 5.44-5.34 (m, 1H), 4.03 (s, 1H), 3.38 (s, 3H), 3.01-2.95 (m, 1H), 2.94-2.87 (m, 2H), 2.80-2.69 (m, 2H), 2.68-2.64 (m, 1H), 2.64-2.60 (m, 1H), 2.11-2.01 (m, 1H), 1.69-1.59 (m, 2H), 1.48-1.43 (m, 2H), 1.42 (s, 9H), 1.40-1.36 (m, 2H), 1.40-1.35 (m, 2H), 1.05 (s, 3H).

Step 3—3-[5-(7-Amino-4-hydroxy-4-methyl-heptyl)-3-methyl-2-oxo-benzimidazol-1-yl]piperidine-2,6-dione To a solution of tert-butyl N-[7-[1-(2,6-dioxo-3-piperidyl)-3-methyl-2-oxo-benzimidazol-5-yl]-4-hydroxy-4-methylheptyl]carbamate (150 mg, 298 umol) in DCM (10.0 mL) was added HCl/dioxane (4.00 M, 1.00 mL) at 0° C., and the mixture was stirred at 0° C. for 3 hrs. On completion, the mixture was concentrated in vacuo. The mixture was purified by reverse phase chromatography (0.1% FA) to give the title compound (50.0 mg, 41% yield) as yellow solid. $^1$H NMR (400 MHz, DMSO-d$_6$) δ 8.43 (s, 1H), 7.05-6.98 (m, 2H), 6.87 (d, J=7.6 Hz, 1H), 5.40-5.28 (m, 1H), 3.33 (s, 3H), 2.96-2.87 (m, 1H), 2.74-2.68 (m, 2H), 2.69-2.63 (m, 2H), 2.62-2.56 (m, 2H), 2.06-1.98 (m, 1H), 1.67-1.46 (m, 4H), 1.40-1.28 (m, 4H), 1.02 (s, 3H).

Benzyl ((S)-1-(((S)-1-((S)-7-hydroxy-3-(((R)-1,2,3,4-tetrahydronaphthalen-1-yl)carbamoyl)-3,4-dihydroisoquinolin-2 (1H)-yl)-3,3-dimethyl-1-oxobutan-2-yl)amino)-1-oxopropan-2-yl)(methyl)carbamate (Intermediate PE)

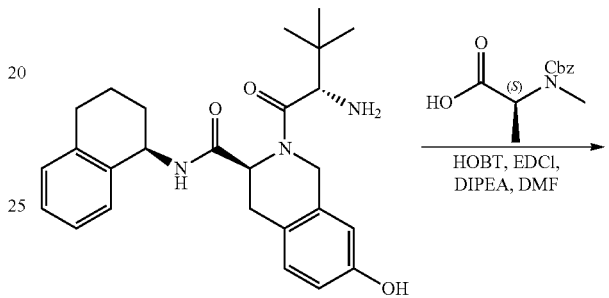

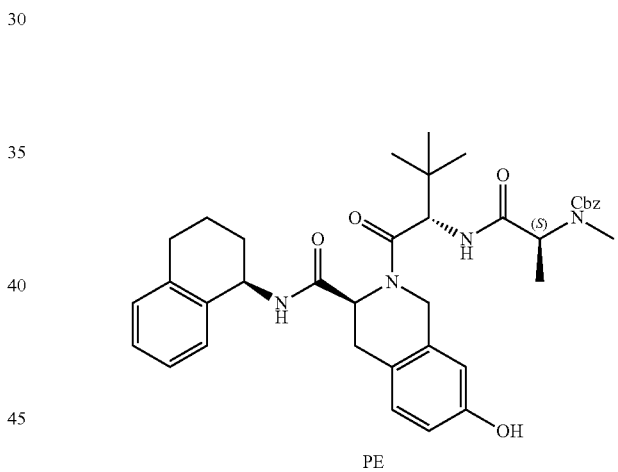

PE

To a solution of (S)-2-((S)-2-amino-3,3-dimethylbutanoyl)-7-hydroxy-N—((R)-1,2,3,4-tetrahydronaphthalen-1-yl)-1,2,3,4-tetrahydroisoquinoline-3-carboxamide (13.45 g, 30.92 mmol, synthesized via Steps 1-7 of Intermediate MH), (S)-2-(((benzyloxy)carbonyl)(methyl)amino)propanoic acid (7.70 g, 32.47 mmol, CAS #21691-41-8) in DMF (150 mL) was added HOBT (4.59 g, 34.01 mmoL), EDCI (6.53 g, 34.01 mmoL), and DIPEA (9.97 g, 77.30 mmoL) at rt. The reaction mixture was stirred at r.t. for 4 h. The mixture was then concentrated under reduce pressure. Then the mixture was poured into H$_2$O (200 mL), extracted with EA (3×100 mL), and the combined organic layers were dried over anhydrous Na$_2$SO$_4$. The solid was filtered and the filtrate was concentrated under reduced pressure. The crude product was purified by silica gel chromatography eluted with DCM/MEOH=10:1 to give the title compound (13.7 g, 63% yield) as a white solid. LC/MS (ESI, m/z): [M+1]$^+$= 655.4.

Benzyl N-[(1S)-2-[[(1S)-1-[(3S)-7-[2-[2-[2-(2-aminoethoxy)ethoxy]ethoxy]ethoxy]-3-[[(1R)-tetralin-1-yl]carbamoyl]-3,4-dihydro-1H-isoquinoline-2-carbonyl]-2,2-dimethyl-propyl]amino]-1-methyl-2-oxoethyl]-N-methyl-carbamate (Intermediate PF)

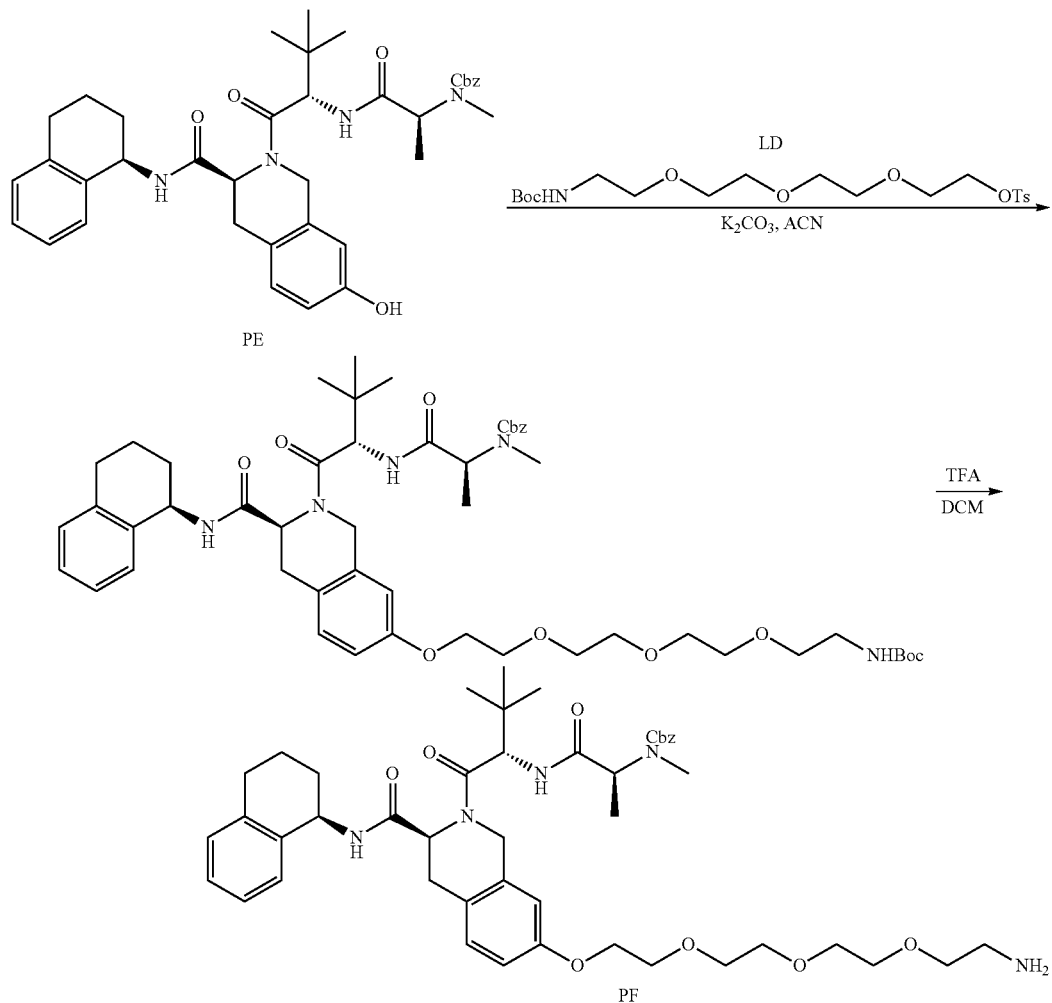

Step 1—benzyl ((S)-1-(((S)-1-((S)-7-((2,2-dimethyl-4-oxo-3,8,11,14-tetraoxa-5-azahexadecan-16-yl)oxy)-3-(((R)-1,2,3,4-tetrahydronaphthalen-1-yl)carbamoyl)-3,4-dihydroisoquinolin-2 (1H)-yl)-3,3-dimethyl-1-oxobutan-2-yl)amino)-1-oxopropan-2-yl)(methyl)carbamate To a solution of benzyl ((S)-1-(((S)-1-((S)-7-hydroxy-3-(((R)-1,2,3,4-tetrahydronaphthalen-1-yl)carbamoyl)-3,4-dihydroisoquinolin-2 (1H)-yl)-3,3-dimethyl-1-oxobutan-2-yl)amino)-1-oxopropan-2-yl)(methyl)carbamate (1.50 g, 2.29 mmol, Intermediate PE) in $CH_3CN$ (20 mL) was added 2,2-dimethyl-4-oxo-3,8,11,14-tetraoxa-5-azahexadecan-16-yl 4-methylbenzenesulfonate (1.23 g, 2.75 mmoL, Intermediate LD), and $K_2CO_3$ (475 mg, 3.44 mmoL). The mixture was stirred at 82° C. overnight. The reaction mixture was then concentrated under reduced pressure and purified by silica gel chromatography eluted with DCM/EA=1:1 to give the title compound (1.64 g, 77% yield) as a yellow oil. LC/MS (ESI, m/z): $[M+1]^+$=931.4.

Step 2—benzyl ((S)-1-(S)-1-((S)-7-(2-aminoethoxy)ethoxy)ethoxy)-3-(((R)-1,2,3,4-tetrahydronaphthalen-1-yl)carbamoyl)-3,4-dihydroisoquinolin-2 (1H)-yl)-3,3-dimethyl-1-oxobutan-2-yl)amino)-1-oxopropan-2-yl)(methyl)carbamate A solution of benzyl ((S)-1-(((S)-1-((S)-7-((2,2-dimethyl-4-oxo-3,8,11,14-tetraoxa-5-azahexadecan-16-yl)oxy)-3-(((R)-1,2,3,4-tetrahydronaphthalen-1-yl)carbamoyl)-3,4-dihydroisoquinolin-2 (1H)-yl)-3,3-dimethyl-1-oxobutan-2-yl)amino)-1-oxopropan-2-yl)(methyl)carbamate (1.37 g, 1.47 mmoL) in TFA/DCM=10 mL/5 mL was stirred at rt for 1 h. The mixture was then concentrated under reduced pressure to give the title compound (900 mg, 74% yield) as a white solid. LC/MS (ESI, m/z): $[M+1]^+$=830.7. $^1$H NMR (400 MHz, DMSO-$d_6$) δ 8.23 (dd, J=49.6, 8.8 Hz, 1H), 7.81-7.56 (m, 4H), 7.35 (s, 5H), 7.16-6.71 (m, 7H), 5.29-4.58 (m, 8H), 4.06 (d, J=3.2 Hz, 2H), 3.76-3.73 (m, 2H), 3.64-3.52 (m, 10H), 3.05-2.91 (m, 3H), 2.87-2.80 (m, 2H), 2.78-2.61 (m, 3H), 1.91-1.50 (m, 4H), 1.20 (d, J=7.2 Hz, 2H), 1.12 (d, J=7.2 Hz, 1H), 0.99 (s, 6H), 0.92 (s, 3H).

1713

Tert-butyl N-[[4-[4-[[2-[2-[tert-butoxycarbonyl(cyclopropylmethyl)amino]-4-pyridyl]oxazole-4-carbonyl]amino]-3-(difluoromethyl)pyrazol-1-yl]phenyl]methyl]-N-(5-oxopentyl)carbamate (Intermediate PG)

1714

1.81 mmol, CAS #2508-29-4) in DMF (4 mL) and dioxane (20 mL) was stirred at 100° C. for 30 min. Then the reaction mixture was cooled to 25° C., and AcOH (217 mg, 3.63 mmol, 207 uL) and NaBH(OAc)₃ (769 mg, 3.63 mmol) were added. The reaction mixture was stirred at 25° C. for 1 hour. Then another batch NaBH(OAc)₃ (256 mg, 1.21 mmol) was

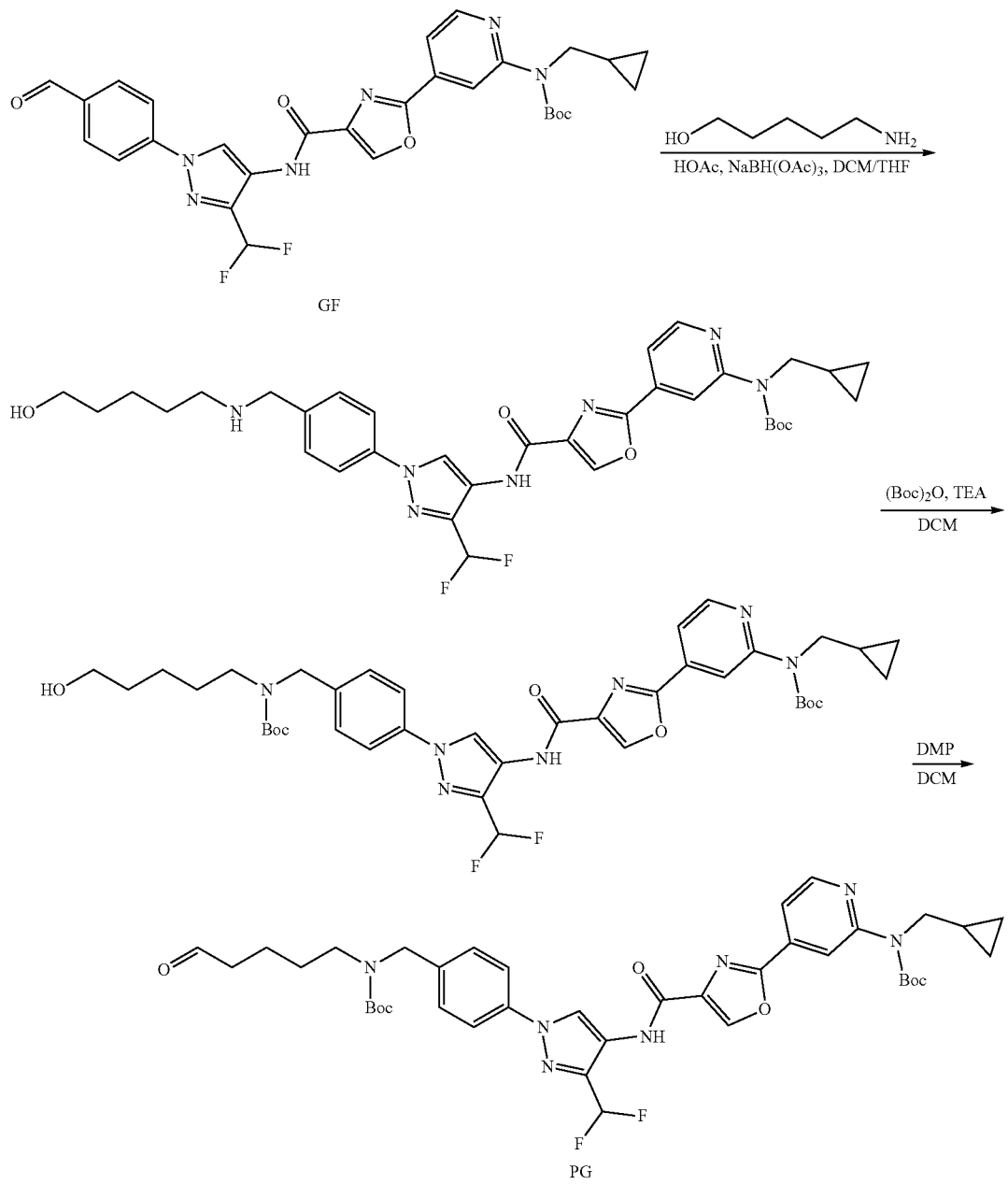

Step 1—Tert-butyl N-(cyclopropylmethyl)-N-[4-[4-[[3-(difluoromethyl)-1-[4-[(5-hydroxypentyl amino)methyl]phenyl]pyrazol-4-yl]carbamoyl]oxazol-2-yl]-2-pyridyl]

A solution of tert-butyl N-(cyclopropylmethyl)-N-[4-[4-[[3-(difluoromethyl)-1-(4-formylphenyl) pyrazol-4-yl]carbamoyl]oxazol-2-yl]-2-pyridyl]carbamate (700 mg, 1.21 mmol, Intermediate GF) and 5-aminopentan-1-ol (187 mg, added to the reaction mixture. The reaction mixture was stirred at 25° C. for another 2 hours. On completion, the reaction was quenched with sat.NaHCO₃ (50 mL) and extracted with EA (2×300 mL). The organic layers were washed with brine (2×70 mL), dried with anhydrous Na₂SO₄ and filtered. The filtrate was concentrated in vacuo to give the title compound (500 mg, 62% yield) as a white solid. ¹H NMR (400 MHz, DMSO-d₆) δ 10.09 (s, 1H), 9.06 (s, 1H), 8.82 (s, 1H), 8.60 (d, J=4.8 Hz, 1H), 8.32 (s, 1H), 8.28 (s, 1H), 7.85 (d, J=8.8 Hz, 2H), 7.55 (d, J=8.8 Hz, 2H), 7.44-7.15 (m, 1H), 3.91-3.78 (m, 4H), 3.38 (t, J=6.4 Hz, 2H), 2.63 (t, J=6.4 Hz, 2H), 1.54-1.28 (m, 13H), 1.25-1.13 (m, 1H), 0.48-0.39 (m, 2H), 0.27-0.20 (m, 2H).

Step 2—Tert-butyl N-[[4-[4-[[2-[2-[tert-butoxycarbonyl(cyclopropylmethyl)amino]-4-pyridyl]oxazole-4-carbonyl]amino]-3-(difluoromethyl)pyrazol-1-yl]phenyl]methyl]-N-(5-hydroxypentyl)carbamate To a solution of tert-butyl N-(cyclopropylmethyl)-N-[4-[4-[[3-(difluoromethyl)-1-[4-[(5-hydroxypentylamino)methyl]phenyl]pyrazol-4-yl]carbamoyl]oxazol-2-yl]-2-pyridyl]carbamate (450 mg, 675 umol) in DCM (5 mL) was added (Boc)$_2$O (147 mg, 675 umol) and TEA (136 mg, 1.35 mmol). The reaction mixture was stirred at 25° C. for 0.5 hour. On completion, the reaction mixture was poured into sat.NaHCO$_3$ (60 mL) and extracted with EA (2×150 mL). The combined organic layers were washed with brine (70 mL), dried with anhydrous Na$_2$SO$_4$, filtered and concentrated in vacuo. The residue was purified by silica column chromatography (PE/EA, 4/1 to 1/1) to give the title compound (370 mg, 483 umol, 71% yield) as a white solid. $^1$H NMR (400 MHz, DMSO-d$_6$) δ 10.06 (s, 1H), 9.05 (s, 1H), 8.80 (s, 1H), 8.60 (d, J=5.2 Hz, 1H), 8.32 (s, 1H), 7.84 (d, J=8.4 Hz, 2H), 7.70 (dd, J=1.2, 5.2 Hz, 1H), 7.45-7.11 (m, 2H), 4.42 (s, 2H), 3.87 (d, J=6.8 Hz, 2H), 3.33 (s, 9H), 2.59-2.52 (m, 3H), 1.52 (s, 9H), 1.48-1.40 (m, 8H), 1.27-1.23 (m, 1H), 0.49-0.32 (m, 2H), 0.32-0.16 (m, 2H).

Step 3—Tert-butyl N-[[4-[4-[[2-[2-[tert-butoxycarbonyl(cyclopropylmethyl)amino]-4-pyridyl]oxazole-4-carbonyl]amino]-3-(difluoromethyl)pyrazol-1-yl]phenyl]methyl]-N-(5-oxopentyl)carbamate To a solution of tert-butyl N-[[4-[4-[[2-[2-[tert-butoxycarbonyl(cyclopropylmethyl)amino]-4-pyridyl]oxazole-4-carbonyl]amino]-3-(difluoromethyl)pyrazol-1-yl]phenyl]methyl]-N-(5-hydroxypentyl)carbamate (370 mg, 483 umol) in DCM (20 mL) was added DMP (225 mg, 531 umol). The reaction mixture was stirred at 25° C. for 2 hours. On completion, the reaction mixture was quenched sat.Na$_2$S$_2$O$_3$ (10 mL) and extracted with EA (2×100). The combined organic layers were washed with brine (70 mL), dried with anhydrous Na$_2$SO$_4$ and filtered. The filtrate was concentrated in vacuo to give the title compound (350 mg, 458 umol, 94% yield) as a light yellow solid. $^1$H NMR (400 MHz, DMSO-d$_6$) δ 10.06 (s, 1H), 9.08-8.99 (m, 1H), 8.83-8.74 (m, 1H), 8.65-8.52 (m, 1H), 8.36-8.27 (m, 1H), 8.02-7.93 (m, 1H), 7.87-7.77 (m, 2H), 7.73-7.69 (m, 1H), 7.50-7.44 (m, 1H), 7.42-7.37 (m, 1H), 7.30-7.20 (m, 1H), 4.42 (s, 2H), 3.91-3.82 (m, 2H), 3.33 (s, 9H), 2.56-2.52 (m, 2H), 2.47-2.34 (m, 1H), 1.55-1.41 (m, 15H), 0.92-0.70 (m, 1H), 0.45-0.36 (m, 2H), 0.30-0.18 (m, 2H).

3-[5-(Aminomethyl)-3-methyl-2-oxo-benzimidazol-1-yl]piperidine-2,6-dione (Intermediate PH)

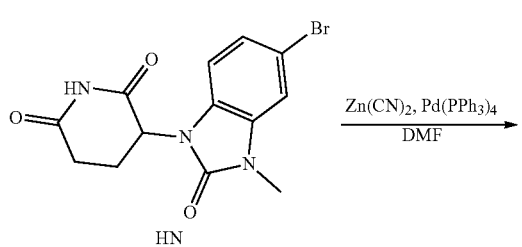

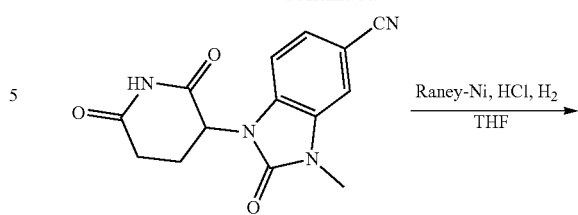

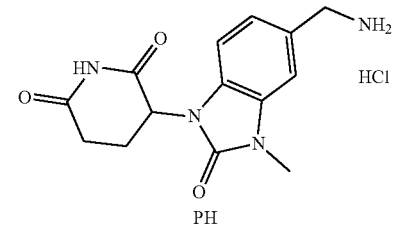

Step 1—1-(2,6-Dioxo-3-piperidyl)-3-methyl-2-oxo-benzimidazole-5-carbonitrile

To a mixture of 3-(5-bromo-3-methyl-2-oxo-benzimidazol-1-yl)piperidine-2,6-dione (3.00 g, 8.87 mmol, Intermediate HN) in DMF (30 mL) was added Zn(CN)$_2$ (1.04 g, 8.87 mmol) and Pd(PPh$_3$)$_4$ (1.03 g, 887 umol). The reaction mixture was stirred at 100° C. for 3 hours under N$_2$. On completion, the reaction mixture was filtered and the filtrate was concentrated in vacuo. The residue was diluted with water (50 mL) and extracted with EA (3×100 mL). The combined organic layers were dried over Na$_2$SO$_4$, filtered and the filtrate concentrated in vacuo. The residue was purified by prep-HPLC (0.1% FA condition) to give the title compound (1.50 g, 59% yield) as a white solid. $^1$H NMR (400 MHz, DMSO-d$_6$) δ 11.31-11.00 (m, 1H), 11.15 (s, 1H), 7.75 (d, J=1.2 Hz, 1H), 7.57-7.52 (m, 1H), 7.34 (d, J=8.4 Hz, 1H), 5.49-5.42 (m, 1H), 3.38 (s, 3H), 2.95-2.83 (m, 1H), 2.79-2.59 (m, 2H), 2.10-2.01 (m, 1H).

Step 2—3-[5-(Aminomethyl)-3-methyl-2-oxo-benzimidazol-1-yl]piperidine-2,6-dione

To a solution of 1-(2,6-dioxo-3-piperidyl)-3-methyl-2-oxo-benzimidazole-5-carbonitrile (1.40 g, 4.92 mmol) in THF (150 mL) was added Raney-Ni (421 mg, 4.92 mmol) and HCl/dioxane (4 M, 4.92 mL). The reaction mixture was stirred at 25° C. for 36 hours under H$_2$ (50 Psi). On completion, the reaction mixture was filtered. The filter cake was washed with DMF (3×10 mL). The combined organic layers were concentrated in vacuo to give the title compound (1.40 g, 98% yield) as a green solid. LC-MS (ESI$^+$) m/z 289.0 (M+H)$^+$.

2-[2-[Tert-butoxycarbonyl-[[4-[4-[[2-[2-[tert-butoxy-carbonyl(cyclopropylmethyl)amino]-4-pyridyl]oxazole-4-carbonyl]amino]-3-(difluoromethyl)pyrazol-1-yl]phenyl]methyl]amino]ethoxy]ethyl methanesulfonate (Intermediate PI)

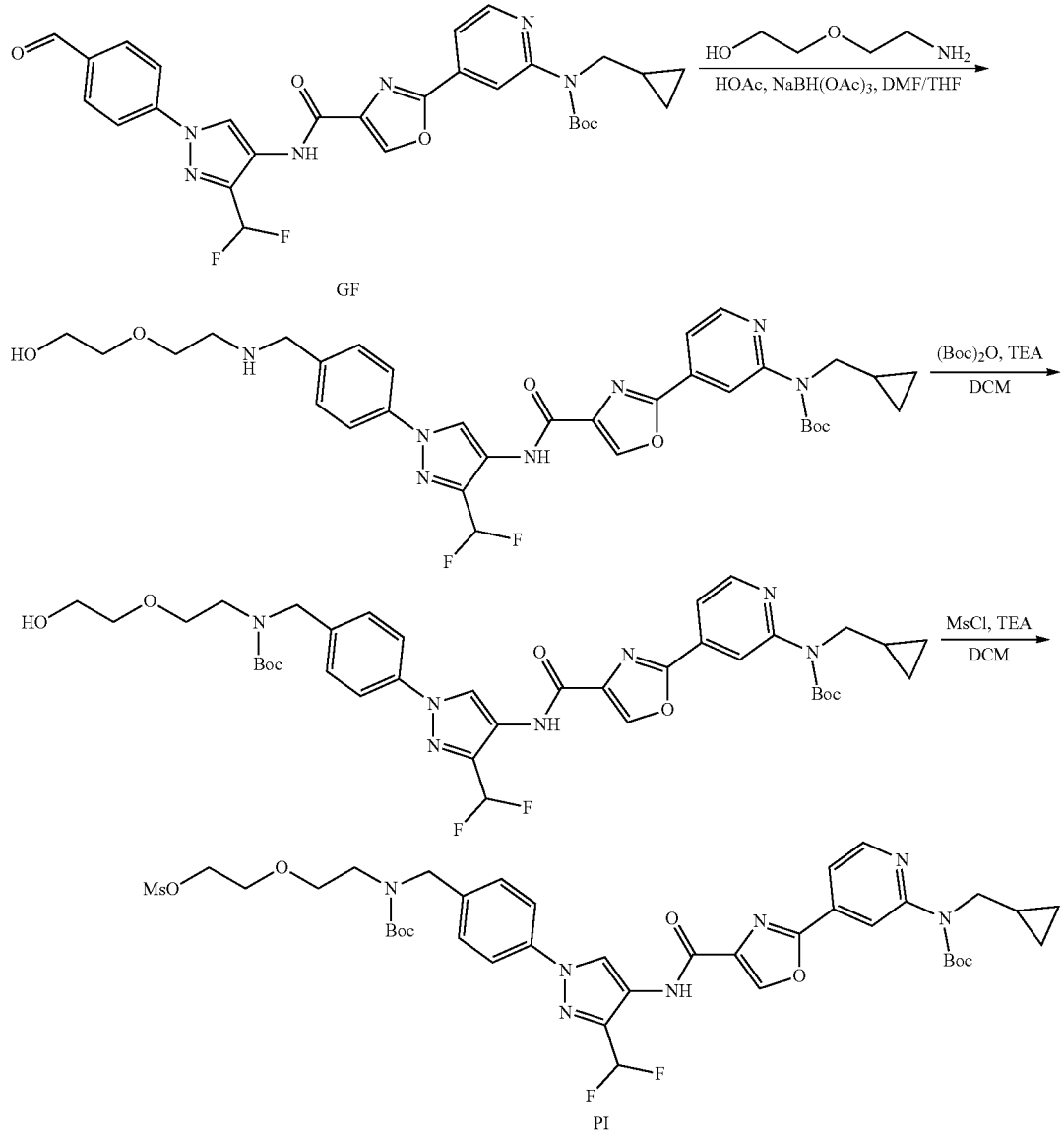

Step 1—Tert-butyl N-(cyclopropylmethyl)-N-[4-[4-[[3-(difluoromethyl)-1-[4-[[2-(2-hydroxyethoxy)ethylamino]methyl]phenyl]pyrazol-4-yl]carbamoyl]oxazol-2-yl]-2-pyridyl]carbamate To a solution of tert-butyl N-(cyclopropylmethyl)-N-[4-[4-[[3-(difluoromethyl)-1-(4-formylphenyl) pyrazol-4-yl]carbamoyl]oxazol-2-yl]-2-pyridyl]carbamate (600 mg, 1.04 mmol, Intermediate GF) in a mixed solvent of DMF (10 mL) and THF (100 mL) was added 2-(2-aminoethoxy)ethanol (141 mg, 1.35 mmol, CAS #929-06-6) and HOAc (124 mg, 2.07 mmol). The reaction mixture was stirred at 25° C. for 0.5 hr. Then, NaBH(OAc)₃ (659 mg, 3.11 mmol) was added. The resulting reaction mixture was stirred at 25° C. for 16 hours. On completion, the reaction mixture was quenched with water (1 mL) and concentrated in vacuo. The residue was purified by reversed-phase flash chromatography (FA, 0.1%) to give the title compound (400 mg, 57% yield) as a yellow solid. ¹H NMR (400 MHz, DMSO-d₆) δ 10.06 (s, 1H), 9.05 (s, 1H), 8.82 (s, 1H), 8.60 (d, J=5.2 Hz, 1H), 8.32 (s, 1H), 7.86 (d, J=8.8 Hz, 2H), 7.70 (dd, J=1.6, 5.2 Hz, 1H), 7.55 (d, J=8.8 Hz, 2H), 7.43-7.15 (m, 1H), 5.75 (s, 1H), 3.92 (s, 2H), 3.87 (d, J=6.8 Hz, 2H), 3.56 (t, J=5.6 Hz, 2H), 3.53-3.50 (m, 2H), 3.45-3.42 (m, 2H), 2.81 (t, J=5.6 Hz, 2H), 1.52 (s, 9H), 1.24-1.12 (t, J=7.8 Hz, 1H), 0.45-0.38 (m, 2H), 0.27-0.22 (m, 2H).

Step 2—Tert-butyl N-[[4-[4-[[2-[2-[tert-butoxycarbonyl(cyclopropylmethyl)amino]-4-pyridyl]oxazole-4-carbonyl]amino]-3-(difluoromethyl)pyrazol-1-yl] phenyl]methyl]-N-[2-(2-hydroxyethoxy)ethyl] carbamate To a solution of tert-butyl N-(cyclopropylmethyl)-N-[4-[4-[[3-(difluoromethyl)-1-[4-[[2-(2-hydroxyethoxy)ethylamino]methyl]phenyl]pyrazol-4-yl]carbamoyl]oxazol-2-yl]-2-pyridyl]carbamate (400 mg, 599 umol) in DCM (20 mL) was added TEA (181 mg, 1.80 mmol) and Boc$_2$O (156 mg, 718 umol). The reaction mixture was stirred at 25° C. for 0.5 hour. On completion, the reaction mixture was poured into sat. NaHCO$_3$ (30 mL) and extracted with EA (3×100 mL). The combined organic layers were washed with brine (100 mL), dried over anhydrous Na$_2$SO$_4$, and filtered. The filtrate was concentrated in vacuo to give the title compound (450 mg, 100% yield) as a white solid. LC-MS (ESI$^+$) m/z 768.1 (M+H)$^+$.

Step 3—2-[2-[Tert-butoxycarbonyl-[[4-[4-[[2-[2-[tert-butoxycarbonyl(cyclopropylmethyl)amino]-4-pyridyl]oxazole-4-carbonyl]amino]-3-(difluoromethyl)pyrazol-1-yl]phenyl]methyl]amino]ethoxy]ethyl methanesulfonate To a solution of tert-butyl N-[[4-[4-[[2-[2-[tert-butoxycarbonyl(cyclopropylmethyl)amino]-4-pyridyl]oxazole-4-carbonyl]amino]-3-(difluoromethyl)pyrazol-1-yl]phenyl]methyl]-N-[2-(2-hydroxyethoxy)ethyl]carbamate (400 mg, 520 umol) in DCM (20 mL) was added TEA (158 mg, 1.56 mmol). The reaction mixture was cooled to 0° C. Then, MsCl (119 mg, 1.04 mmol) was dropwise into the mixture slowly. The reaction mixture was stirred at 25° C. for 1 hour. On completion, the reaction mixture was poured into sat-.NaHCO$_3$ (30 mL) and extracted with EA (3×50 mL). The combined organic layers were washed with brine (50 mL), dried with anhydrous Na$_2$SO$_4$ and filtered. The filtrate was concentrated in vacuo to give the title compound (400 mg, 100% yield) as a yellow solid. LC-MS (ESI$^+$) m/z 846.2 (M+H)$^+$.

Benzyl N-[(1S)-2-[[(1S)-1-[(3S)-7-[2-[2-[2-[2-(2-aminoethoxy)ethoxy]ethoxy]ethoxy]ethoxy]-3-[[(1R)-tetralin-1-yl]carbamoyl]-3,4-dihydro-1H-isoquinoline-2-carbonyl]-2,2-dimethyl-propyl]amino]-1-methyl-2-oxo-ethyl]-N-methyl-carbamate (Intermediate PJ)

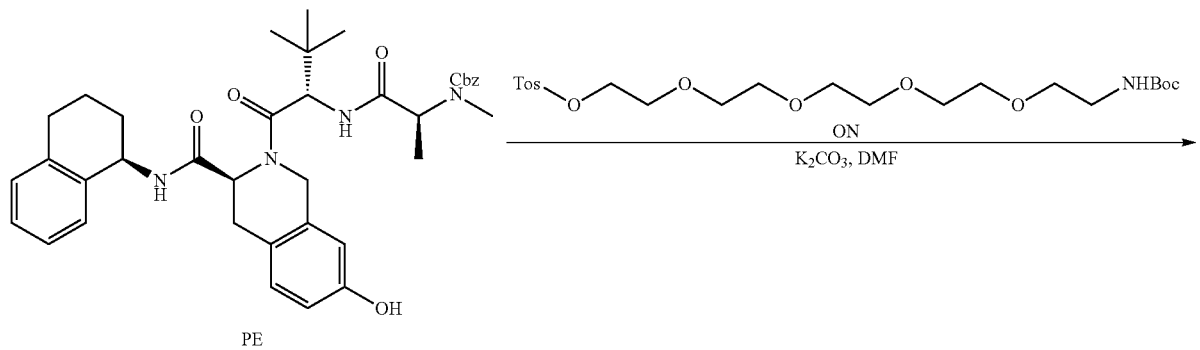

PE

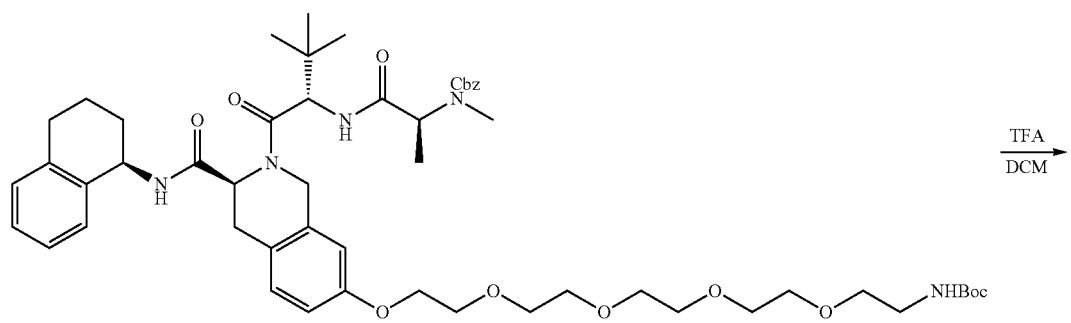

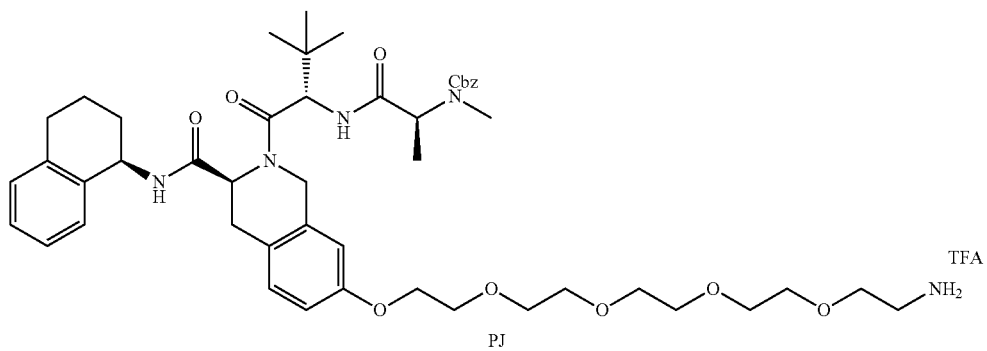

PJ

Step 1—benzyl ((S)-1-(((S)-1-((S)-7-((2,2-dimethyl-4-oxo-3,8,11,14,17-pentaoxa-5-azanonadecan-9-yl)oxy)-3-(((R)-1,2,3,4-tetrahydronaphthalen-1-yl)carbamoyl)-3,4-dihydroisoquinolin-2 (1H)-yl)-3,3-dimethyl-1-oxobutan-2-yl)amino)-1-oxopropan-2-yl)(methyl)carbamate To a solution of benzyl ((S)-1-(((S)-1-((S)-7-hydroxy-3-(((R)-1,2,3,4-tetrahydronaphthalen-1-yl)carbamoyl)-3,4-dihydroisoquinolin-2 (1H)-yl)-3,3-dimethyl-1-oxobutan-2-yl)amino)-1-oxopropan-2-yl)(methyl)carbamate (1.0 g, 1.53 mmol, Intermediate PE) in CH₃CN (50 mL) was added 2,2-dimethyl-4-oxo-3,8,11,14,17-pentaoxa-5-azanonadecan-9-yl 4-methylbenzenesulfonate (901 mg, 1.84 mmol, Intermediate ON) and K₂CO₃ (317 mg, 2.3 mmol) at rt. The reaction mixture was then stirred at 80° C. for 12 h. The reaction mixture was cooled to rt and filtered. The filtrate was concentrated under reduced pressure. The residue was purified via column chromatography (EtOAc/petroleum ether) to give the title compound (1.08 g, 73% yield) as a pale yellow oil. LC/MS (ESI, m/z): [M+1]⁺=974.68.

Step 2—benzyl ((S)-1-(((S)-1-((S)-7-((14-amino-3,6,9,12-tetraoxatetradecyl)oxy)-3-(((R)-1,2,3,4-tetrahydronaphthalen-1-yl)carbamoyl)-3,4-dihydroisoquinolin-2 (1H)-yl)-3,3-dimethyl-1-oxobutan-2-yl)amino)-1-oxopropan-2-yl)(methyl)carbamate 2,2,2-trifluoroacetate To a solution of benzyl ((S)-1-(((S)-1-((S)-7-((2,2-dimethyl-4-oxo-3,8,11,14,17-pentaoxa-5-azanonadecan-19-yl)oxy)-3-(((R)-1,2,3,4-tetrahydronaphthalen-1-yl)carbamoyl)-3,4-dihydroisoquinolin-2 (1H)-yl)-3,3-dimethyl-1-oxobutan-2-yl)amino)-1-oxopropan-2-yl)(methyl)carbamate (1.4 g, 1.43 mmol) in DCM (20 mL) was added TFA (20 mL) and the reaction mixture was stirred at rt for 3 h. The reaction mixture was concentrated under reduced pressure and the residue was purified via reverse phase column chromatography (ACN/H₂O) to give the title compound (1.341 g, 94.8% yield) as as a white solid. ¹H NMR (400 MHz, DMSO-d₆): 8.30-8.15 (m, 1H), 7.77-7.56 (m, 4H), 7.40-7.35 (m, 5H), 7.18-6.70 (m, 7H), 5.28-4.23 (m, 9H), 4.13-4.00 (m, 2H), 3.74 (t, J=4.5 Hz, 2H), 3.69-3.23 (m, 14H), 3.02-2.64 (m, 8H), 1.95-1.45 (m, 4H), 1.21-1.11 (m, J3H), 0.99-0.91 (m, 9H). LC/MS (ESI, m/z): [M+1]= 874.55.

3-(Tert-butoxycarbonylamino)propyl (4-nitrophenyl) carbonate (Intermediate PK)

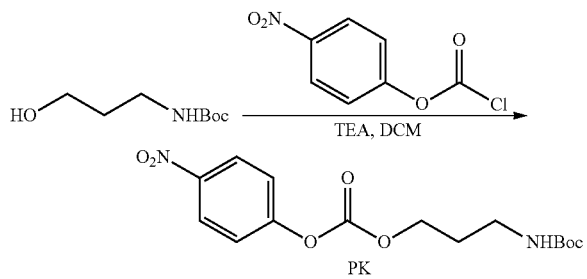

To a solution of tert-butyl N-(3-hydroxypropyl)carbamate (0.600 g, 3.42 mmol, CAS #58885-58-8) and (4-nitrophenyl) carbonochloridate (759 mg, 3.77 mmol, CAS #7693-46-1) in DCM (25 mL) was added TEA (866 mg, 8.56 mmol) at 0° C. The reaction mixture was stirred at this temperature for 1 hr. On completion, the mixture was quenched with water (10 mL), then concentrated in vacuo. The residue was purified by silica gel chromatography (SiO₂) to give the title compound (520 mg, 45% yield) as colorless oil. ¹H NMR (300 MHz, CDCl₃) δ 8.34-8.25 (m, 2H), 7.44-7.35 (m, 2H), 4.77 (s, 1H), 4.36 (t, J=6.4 Hz, 2H), 3.29 (q, J=6.4 Hz, 2H), 2.03-1.90 (m, 2H), 1.45 (s, 9H).

3-Aminopropyl N-[[1-(2,6-dioxo-3-piperidyl)-3-methyl-2-oxo-benzimidazol-5-yl]methyl]carbamate (Intermediate PL)

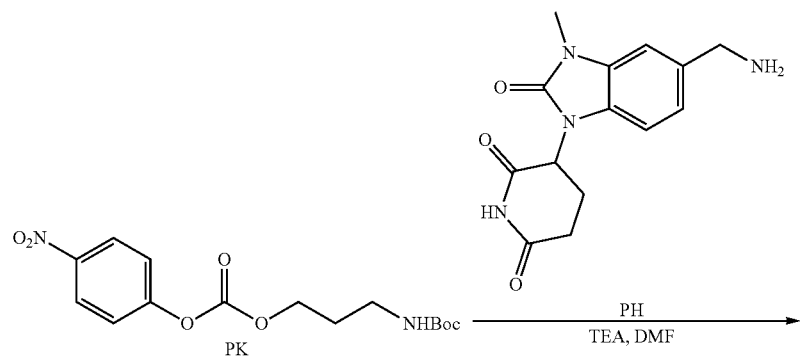

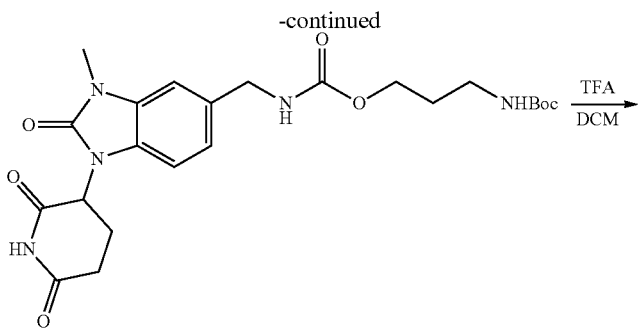

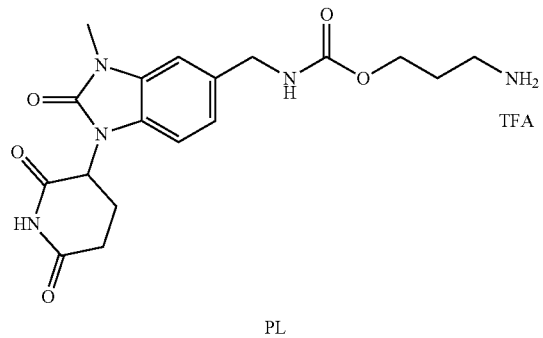

PL

Step 1—3-(Tert-butoxycarbonylamino)propyl N-[[1-(2,6-dioxo-3-piperidyl)-3-methyl-2-oxo-benzimidazol-5-yl]methyl]carbamate To a solution of 3-[5-(aminomethyl)-3-methyl-2-oxo-benzimidazol-1-yl]piperidine-2,6-dione (120 mg, 416 umol, Intermediate PH) and 3-(tert-butoxycarbonylamino)propyl (4-nitrophenyl) carbonate (170 mg, 500 umol, Intermediate PK) in DMF (2 mL) was added TEA (84.2 mg, 832 umol). The reaction mixture was stirred at 25° C. for 3 hrs. On completion, the mixture was concentrated in vacuo. The residue was purified by reverse phase (0.1% FA condition) to give the title compound (110 mg, 54% yield) as a white solid. $^1$H NMR (400 MHz, DMSO-$d_6$) δ 11.05 (s, 1H), 7.64 (s, 1H), 7.10-7.01 (m, 2H), 6.98-6.91 (m, 1H), 6.86-6.78 (m, 1H), 5.43-5.29 (m, 1H), 4.19 (d, J=6.0 Hz, 2H), 3.95 (t, J=6.4 Hz, 2H), 3.30 (s, 3H), 3.02-2.94 (m, 2H), 2.94-2.84 (m, 1H), 2.69-2.56 (m, 2H), 2.09-1.94 (m, 1H), 1.73-1.58 (m, 2H), 1.37 (s, 9H); LC-MS (ESI$^+$) m/z 512.3 (M+Na)$^+$.

Step 2—3-Aminopropyl N-[[1-(2,6-dioxo-3-piperidyl)-3-methyl-2-oxo-benzimidazol-5-yl]methyl]carbamate To a solution of 3-(tert-butoxycarbonylamino)propyl N-[[1-(2,6-dioxo-3-piperidyl)-3-methyl-2-oxo-benzimidazol-5-yl]methyl]carbamate (140 mg, 286 umol) in DCM (5 mL) was added TFA (5 mL). The reaction mixture was stirred at 25° C. for 1 hr. On completion, the mixture was concentrated in vacuo to give the title compound (140 mg, 97% yield, TFA) as a white solid. LC-MS (ESI$^+$) m/z 390.2 (M+H)$^+$

Tert-butyl 4-(3-methyl-2-oxo-1H-benzimidazol-5-yl)piperazine-1-carboxylate (Intermediate PM)

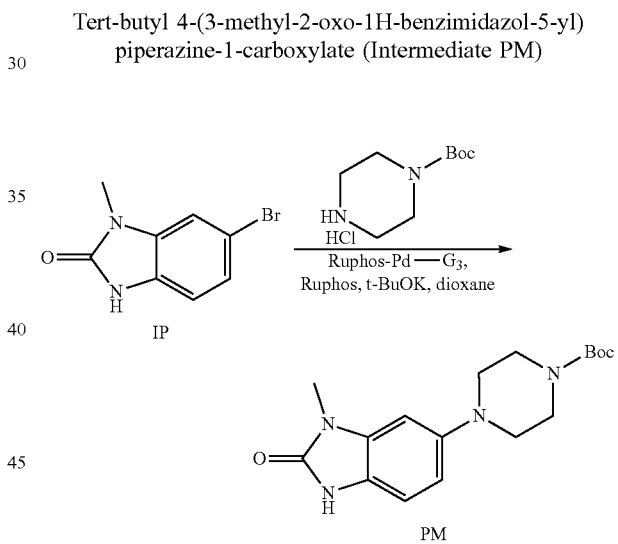

To a solution of 5-bromo-3-methyl-1H-benzimidazol-2-one (4.00 g, 17.6 mmol, Intermediate IP), tert-butyl piperazine-1-carboxylate (4.92 g, 26.4 mmol, CAS #1433238-38-4) and t-BuOK (4.35 g, 38.8 mmol), was added RuPhos (822 mg, 1.76 mmol) and [2-(2-aminophenyl)phenyl]-chloro-palladium; dicyclohexyl-[2-(2,6-diisopropoxyphenyl)phenyl]phosphane (1.37 g, 1.76 mmol) in dioxane (100 mL), and the mixture was stirred at 90° C. for 1 hr at N$_2$. On completion, the residue was diluted with H$_2$O (50 mL) and extracted with EtOAc (3×100 mL). The combined organic layers were washed with brine (150 mL), dried over Na$_2$SO$_4$, filtered and concentrated under reduced pressure to give a residue. The residue was triturated with PE:EA (10:1, 50 mL), filtered and filtered caked was dried under reduced pressure to give the title compound (3.80 g, 65% yield) as a yellow solid. $^1$H NMR (400 MHz, DMSO-$d_6$) δ 10.54 (s, 1H), 6.83 (d, J=8.4 Hz, 1H), 6.78 (d, J=2.20 Hz, 1H), 6.60 (dd, J=8.4, Hz, 1H), 3.43-3.50 (m, 4H), 3.24 (s, 3H), 2.98-3.03 (m, 4H), 1.42 (s, 9H), LC-MS (ESI+) m/z 333.1 (M+H)⁺.

3-(3-Methyl-2-oxo-5-piperazin-1-yl-benzimidazol-1-yl)piperidine-2,6-dione (Intermediate PN)

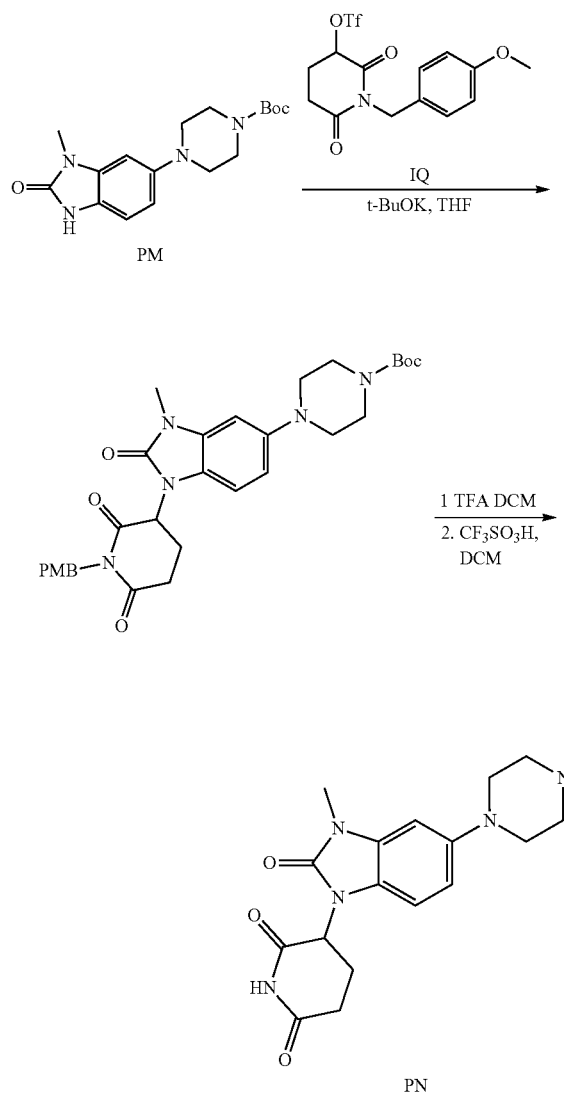

Step 1—Tert-butyl 4-[1-[1-[(4-methoxyphenyl)methyl]-2,6-dioxo-3-piperidyl]-3-methyl-2-oxo-benzimidazol-5-yl]piperazine-1-carboxylate To a solution of tert-butyl 4-(3-methyl-2-oxo-1H-benzimidazol-5-yl)piperazine-1-carboxylate (3.80 g, 11.4 mmol, Intermediate PM) in THF (100 mL) was added t-BuOK (2.57 g, 22.9 mmol); then [1-[(4-methoxyphenyl)methyl]-2,6-dioxo-3-piperidyl]trifluoromethanesulfonate (8.72 g, 22.86 mmol, Intermediate IQ) in THF (20 mL) was added at 0° C. The mixture was stirred at 0° C. for 2 hrs. On completion, the residue was diluted with H₂O (50 mL) and extracted with EtOAc (3×50 mL). The combined organic layers were washed with brine (100 mL), dried over Na₂SO₄, filtered and concentrated under reduced pressure to give a residue. The residue was triturated with PE:EA (10:1, 50 mL), filtered and the filtered cake was dried in vacuo to give the title compound (3.00 g, 37% yield, 80% purity) as a blue solid. LC-MS (ESI+) m/z 564.3 (M+H)⁺.

Step 2—3-(3-Methyl-2-oxo-5-piperazin-1-yl-benzimidazol-1-yl)piperidine-2,6-dione To a solution of tert-butyl 4-[1-[1-[(4-methoxyphenyl)methyl]-2,6-dioxo-3-piperidyl]-3-methyl-2-oxo-benzimidazol-5-yl]piperazine-1-carboxylate (2.50 g, 4.44 mmol) in DCM (40 mL) was added TFA (38.5 g, 338 mmol, 25.0 mL), and the mixture was stirred at 15° C. for 1 hr. Then methanesulfonic acid (33.8 g, 351 mmol, 25 mL) was added and the mixture was stirred at 15° C. for 25 hrs. On completion, the mixture was concentrated in vacuo. The residue was purified by reversed-phase HPLC (0.1% FA condition) to give the title compound (700 mg, 40% yield) as a blue solid. ¹H NMR (400 MHz, DMSO-d₆) δ 10.89-11.20 (m, 1H), 6.98 (d, J=8.4 Hz, 1H), 6.89 (d, J=1.6 Hz, 1H), 6.67 (dd, J=8.4, 1.6 Hz, 1H), 5.31 (dd, J=12.8, 5.6 Hz, 1H), 3.21 (d, J=3.6 Hz, 4H), 3.15 (s, 4H), 2.85-2.95 (m, 1H), 2.63-2.75 (m, 2H), 1.96-2.04 (m, 1H), LC-MS (ESI+) m/z 344.1 (M+H)⁺.

Tert-butyl N-methyl-N-(3-prop-2-ynoxypropyl)carbamate (Intermediate PO)

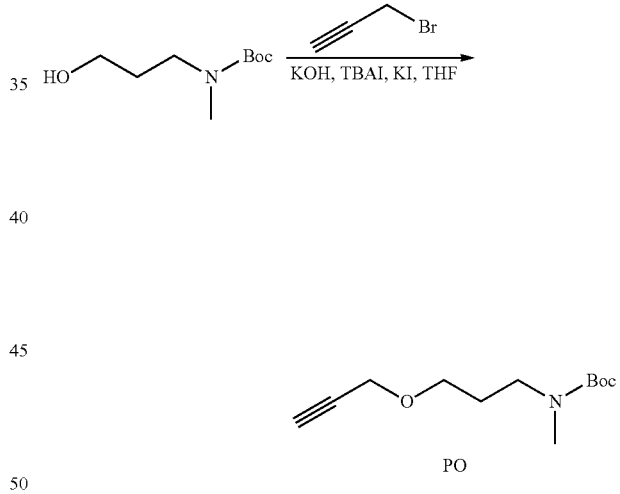

To a solution of 3-bromoprop-1-yne (1.32 g, 11.1 mmol, CAS #106-96-7) and tert-butyl N-(3-hydroxypropyl)-N-methyl-carbamate (2.00 g, 10.6 mmol, CAS #98642-44-5) in THF (20 mL) was added TBAI (234 mg, 634 umol) and KI (263 mg, 1.59 mmol). Then KOH (698 mg, 10.6 mmol, 85% purity) was added into the above mixture. The reaction mixture was stirred at 25° C. for 12 hrs. On completion, the mixture was concentrated in vacuo to remove the solvent, the residue was diluted with water (30 mL), then extracted with EA (3×40 mL). The organic phase was dried over Na₂SO₄, filtered and the filtrate was concentrated in vacuo. The residue was purified by silica gel chromatography (SiO₂) to give the title compound (1.15 g, 48% yield) as colorless oil. ¹H NMR (400 MHz, CDCl₃) δ 4.15-4.11 (m, 2H), 3.57-3.49 (m, 2H), 3.29 (t, J=6.8 Hz, 2H), 2.86 (s, 3H), 2.42 (t, J=2.4 Hz, 1H), 1.85-1.76 (m, 2H), 1.46 (s, 9H).

3-[3-Methyl-4-[3-[3-(methylamino)propoxy]propyl-2-oxo-benzimidazol-1-yl]piperidine-2,6-dione (Intermediate PP)

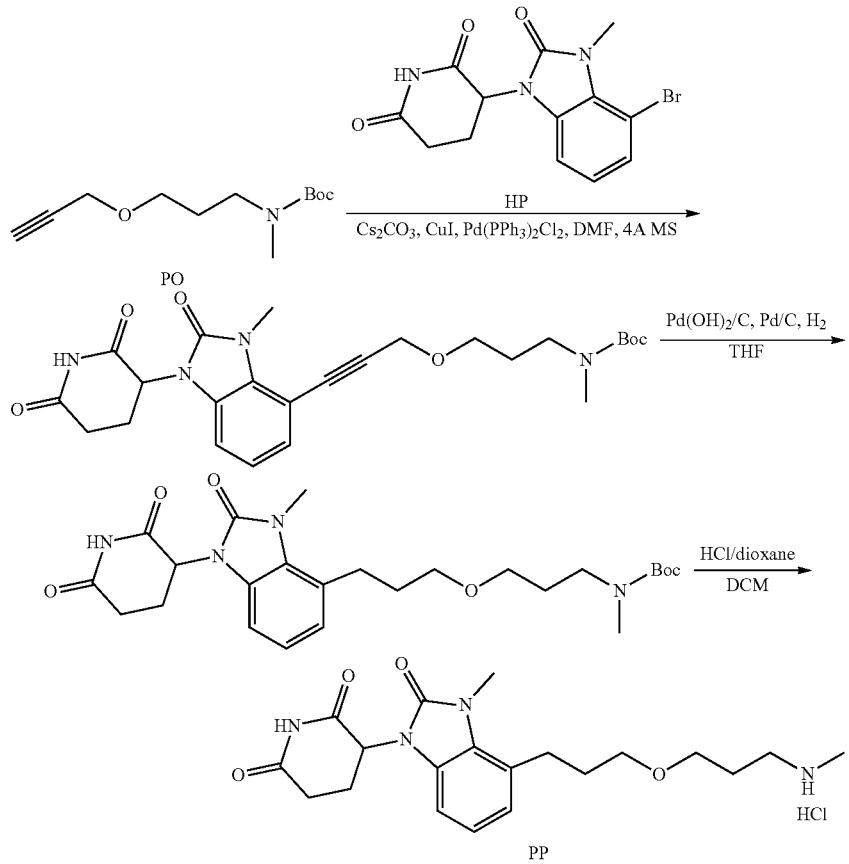

Step 1—Tert-butyl N-[3-[3-[1-(2,6-dioxo-3-piperidyl)-3-methyl-2-oxo-benzimidazol-4-yl]prop-2-ynoxy]propyl]-N-methyl-carbamate 3-(4-bromo-3-methyl-2-oxo-benzimidazol-1-yl)piperidine-2,6-dione (300 mg, 887 umol, Intermediate HP), tert-butyl N-methyl-N-(3-prop-2-ynoxypropyl)carbamate (504 mg, 2.22 mmol, Intermediate PO), Pd(PPh$_3$)$_2$Cl$_2$ (125 mg, 177 umol), Cs$_2$CO$_3$ (1.45 g, 4.44 mmol), CuI (33.8 mg, 177 umol) and 4 Å molecular sieves (150 mg) in DMF (8 mL) was heated at 80° C. for 2 hrs under N$_2$. On completion, the mixture was concentrated in vacuo. The residue was purified by reverse phase (0.1% FA condition) to give the title compound (200 mg, 40% yield) as a yellow solid. LC-MS (ESI$^+$) m/z 507.3 (M+Na)$^+$.

Step 2—Tert-butyl N-[3-[3-[1-(2,6-dioxo-3-piperidyl)-3-methyl-2-oxo-benzimidazol-4-yl]propoxy]propyl-N-methyl-carbamate To a solution of tert-butyl N-[3-[3-[1-(2,6-dioxo-3-piperidyl)-3-methyl-2-oxo-benzimidazol-4-yl]prop-2-ynoxy]propyl]-N-methyl-carbamate (200 mg, 351 umol) in THF (6 mL) was added Pd/C (0.100 g, 10% wt) and Pd(OH)$_2$/C (0.100 g, 10% wt). The reaction mixture was stirred at 25° C. for 10 hrs under H$_2$ (15 Psi) atmosphere. On completion, the mixture was filtered and the filtrate was concentrated in vacuo to give the title compound (200 mg, 93% yield) as a yellow solid. $^1$H NMR (400 MHz, DMSO-d$_6$) δ 11.10 (s, 1H), 7.00-6.92 (m, 2H), 6.90-6.84 (m, 1H), 5.44-5.24 (m, 1H), 3.56 (s, 3H), 3.44-3.40 (m, 4H), 3.22 (t, J=7.2 Hz, 2H), 2.99-2.92 (m, 2H), 2.76 (s, 3H), 2.74-2.69 (m, 1H), 2.65-2.58 (m, 2H), 2.04-1.96 (m, 1H), 1.87-1.79 (m, 2H), 1.74-1.65 (m, 2H), 1.38 (s, 9H); LC-MS (ESI$^+$) m/z 511.3 (M+Na)$^+$.

Step 3—3-[3-Methyl-4-[3-[3-(methylamino)propoxy]propyl-2-oxo-benzimidazol-1-yl]piperidine-2,6-dione To a solution of tert-butyl N-[3-[3-[1-(2,6-dioxo-3-piperidyl)-3-methyl-2-oxo-benzimidazol-4-yl]propoxy]propyl]-N-methyl-carbamate (200 mg, 327 umol) in DCM (4 mL) was added HCl/dioxane (4 M, 3.20 mL). The reaction mixture was stirred at 25° C. for 2 hrs. On completion, the mixture was concentrated in vacuo to give the title compound (160 mg, 100% yield, HCl) as a white solid. $^1$H NMR (400 MHz, DMSO-d$_6$) δ 11.08 (s, 1H), 7.02-6.92 (m, 2H), 6.90-6.83 (m, 1H), 5.44-5.24 (dd, J=5.6, 12.4 Hz, 1H), 3.57 (s, 3H), 3.49-3.43 (m, 4H), 3.00-2.91 (m, 4H), 2.74-2.53 (m, 6H), 2.04-1.94 (m, 1H), 1.90-1.81 (m, 4H); LC-MS (ESI$^+$) m/z 389.2 (M+H)$^+$.

1729

Tert-butyl N-(3-prop-2-ynoxypropyl)carbamate (Intermediate PX)

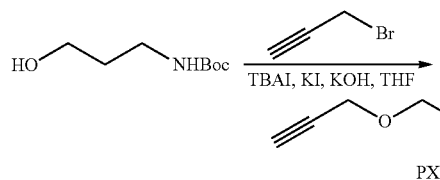

To a mixture of tert-butyl N-(3-hydroxypropyl)carbamate (10.0 g, 57.1 mmol, CAS #58885-58-8), 3-bromoprop-1-yne (8.15 g, 68.5 mmol, CAS #106-96-7) in THF (150 mL) was added TBAI (1.26 g, 3.42 mmol) KOH (3.20 g, 57.07 mmol) and KI (1.42 g, 8.56 mmol). The mixture was stirred at 20° C. for 12 hours. On completion, the reaction mixture was concentrated in vacuo to give residue. The residue was purified by column chromatography to give the title compound (6.80 g, 55% yield) as yellow solid. $^1$H NMR (400 MHz, CDCl$_3$) δ 4.76 (s, 1H), 4.10-4.05 (m, 2H), 3.51 (t, J=6.0 Hz, 2H), 3.16 (q, J=6.0 Hz, 2H), 2.37 (t, J=2.4 Hz, 1H), 1.74-1.65 (m, 2H), 1.37 (s, 9H).

3-[7-[3-(3-Aminopropoxy)propyl]-2-oxo-1,3-benzoxazol-3-yl]piperidine-2,6-dione (Intermediate PY)

1730

Step 1—Tert-butyl N-[3-[3-[3-(2,6-dioxo-3-piperidyl)-2-oxo-1,3-benzoxazol-7-yl]prop-2-ynoxy]propyl]carbamate To a mixture of 3-(7-bromo-2-oxo-1,3-benzoxazol-3-yl)piperidine-2,6-dione (3.00 g, 9.23 mmol, Intermediate JF) and tert-butyl N-(3-prop-2-ynoxypropyl)carbamate (4.92 g, 23.0 mmol, Intermediate PX) in DMF (30 mL) was added Cs$_2$CO$_3$ (15.0 g, 46.1 mmol), CuI (175 mg, 922 umol) and Pd(PPh$_3$)$_2$Cl$_2$ (647 mg, 922 umol). The reaction mixture was stirred at 80° C. for 2 hours. On completion, the reaction mixture was filtered and concentrated in vacuo. The residue was diluted with water (50 mL) and extracted with EA (3×100 mL). The combined organic layers was dried over Na$_2$SO$_4$, filtered and concentrated in vacuo to give a residue. The residue was purified by reverse phase (0.1% FA condition) to give the title compound (2.70 g, 63% yield) as light yellow solid. $^1$H NMR (400 MHz, DMSO-d$_6$) δ 11.23 (s, 1H), 7.32 (dd, J=2.0, 7.2 Hz, 1H), 7.27-7.19 (m, 2H), 6.81-6.77 (m, 1H), 5.39 (dd, J=5.6, 13.2 Hz, 1H), 4.43 (s, 2H), 3.53 (t, J=6.4 Hz, 2H), 3.02-2.97 (m, 2H), 2.92-2.81 (m, 1H), 2.73-2.58 (m, 2H), 2.22-2.13 (m, 1H), 1.70-1.64 (m, 2H), 1.36 (s, 9H); LC-MS (ESI$^+$) m/z 480.2 (M+Na)$^+$.

Step 2—Tert-butyl N-[3-[3-[3-(2,6-dioxo-3-piperidyl)-2-oxo-1,3-benzoxazol-7-yl]propoxy]propyl]carbamate To a mixture was tert-butyl N-[3-[3-[3-(2,6-dioxo-3-piperidyl)-2-oxo-1,3-benzoxazol-7-yl]prop-2-ynoxy]propyl]

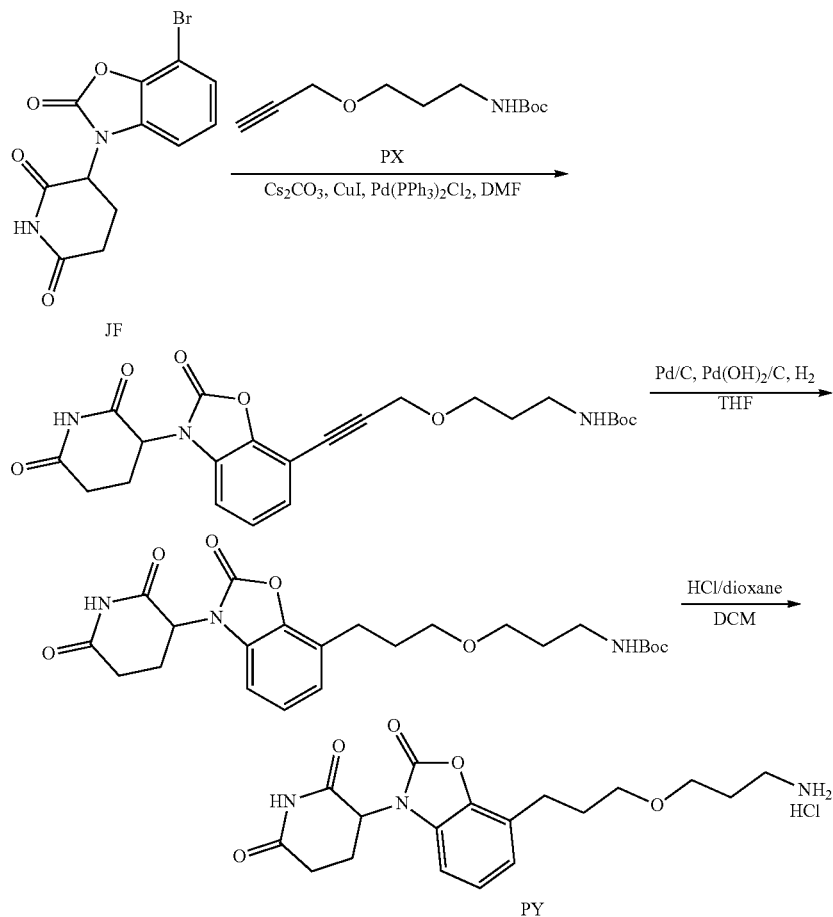

carbamate (2.30 g, 5.03 mmol) in THF (200 mL) was added Pd/C (0.6 g, 10% wt) and Pd(OH)$_2$/C (0.6 g, 10% wt). The reaction mixture was stirred at 25° C. for 12 hours under H$_2$ (15 Psi) atmosphere. On completion, the reaction mixture was filtered and concentrated in vacuo to give the title compound (2.30 g, 99% yield) as off-white solid. LC-MS (ESI$^+$) m/z 484.2 (M+Na)$^+$.

Step 3—3-[7-[3-(3-Aminopropoxy)propyl]-2-oxo-1,3-benzoxazol-3-yl]piperidine-2,6-dione To a mixture of tert-butyl N-[3-[3-[3-(2,6-dioxo-3-piperidyl)-2-oxo-1,3-benzoxazol-7-yl]propoxy]propyl]carbamate (2.30 g, 4.98 mmol) in DCM (10 mL) was added HCl/dioxane (4 M, 10 mL). The reaction mixture was stirred at 25° C. for 1 hour. On completion, the reaction mixture was concentrated in vacuo to give the title compound (1.80 g, 90% yield, HCl salt) as off-white solid. $^1$H NMR (400 MHz, DMSO-d$_6$) δ 11.20 (s, 1H), 7.86 (s, 2H), 7.17-7.09 (m, 2H), 7.04-7.00 (m, 1H), 5.37 (dd, J=5.2, 13.2 Hz, 1H), 3.47-3.43 (m, 2H), 3.43-3.41 (m, 2H), 2.90-2.84 (m, 2H), 2.83-2.79 (m, 1H), 2.78-2.72 (m, 2H), 2.70-2.61 (m, 2H), 2.20-2.10 (m, 1H), 1.91-1.84 (m, 2H), 1.83-1.78 (m, 2H).

3-[6-[3-(3-Aminopropoxy)propyl]-2-oxo-1,3-benzoxazol-3-yl]piperidine-2,6-dione (Intermediate PZ)

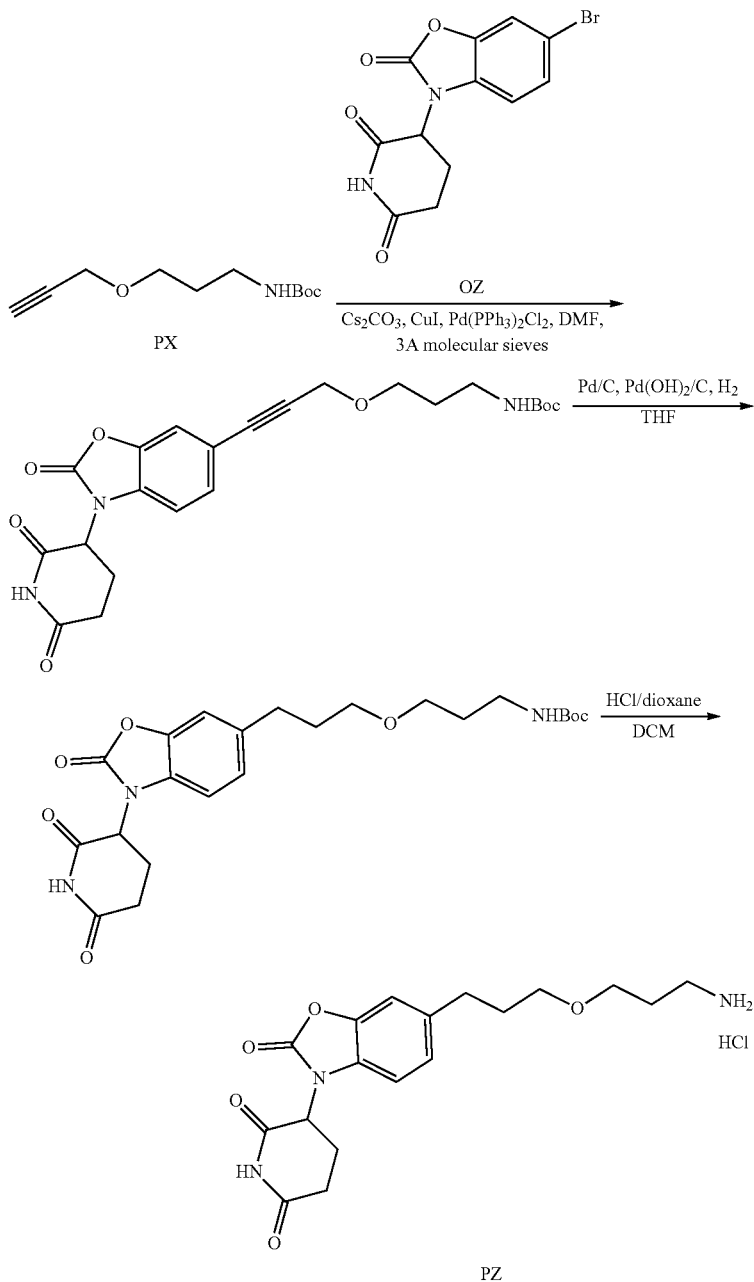

Step 1—Tert-butyl N-[3-[3-[3-(2,6-dioxo-3-piperidyl)-2-oxo-1,3-benzoxazol-6-yl]prop-2-ynoxy]propyl]carbamate To a mixture of 3-(6-bromo-2-oxo-1,3-benzoxazol-3-yl)piperidine-2,6-dione (1.20 g, 3.69 mmol, Intermediate OZ) and tert-butyl N-(3-prop-2-ynoxypropyl)carbamate (1.57 g, 7.38 mmol, Intermediate PX) in DMF (30 mL) was added CuI (210 mg, 1.11 mmol), Pd(PPh$_3$)$_2$Cl$_2$ (777 mg, 1.11 mmol), Cs$_2$CO$_3$ (6.01 g, 18.5 mmol) and 3 Å molecular sieves (100 mg, 3.69 mmol) under N$_2$. The reaction mixture was stirred at 80° C. for 2 hours. On completion, the reaction mixture was cooled to 25° C. Then the mixture was filtered and concentrated in vacuo to give a residue. The residue was purified by reverse phase (0.1% FA condition) to give the title compound (868 mg, 42% yield) as brown solid. $^1$H NMR (400 MHz, CDCl$_3$) δ 8.49 (s, 1H), 7.74-7.65 (m, 1H), 7.61-7.54 (m, 1H), 7.36 (d, J=1.0 Hz, 1H), 7.30-7.27 (m, 1H), 6.79 (d, J=8.4 Hz, 1H), 5.07 (d, J=5.6, 13.2 Hz, 1H), 4.37 (s, 2H), 3.66 (t, J=6.0 Hz, 2H), 3.27 (d, J=6.0 Hz, 2H), 3.05-2.95 (m, 1H), 2.92-2.80 (m, 1H), 2.79-2.65 (m, 1H), 2.40-2.26 (m, 1H), 1.85-1.80 (m, 2H), 1.45 (s, 9H).

Step 2—Tert-butyl N-[3-[3-[3-(2,6-dioxo-3-piperidyl)-2-oxo-1,3-benzoxazol-6-yl]propoxy]propyl]carbamate To a mixture of tert-butyl N-[3-[3-[3-(2,6-dioxo-3-piperidyl)-2-oxo-1,3-benzoxazol-6-yl]prop-2-ynoxy]propyl]carbamate (868 mg, 1.90 mmol) in THF (30 mL) was added Pd/C (200 mg, 10 wt %) and Pd(OH)$_2$/C (200 mg, 10 wt %). The suspension was degassed under vacuum and purged with H$_2$ gas 3 times. The mixture was stirred under H$_2$ (15 psi) at 20° C. for 12 hours. On completion, the reaction mixture was filtered and the filtrate was concentrated in vacuo to give the title compound (835 mg, 95% yield) as brown solid. $^1$H NMR (400 MHz, DMSO-d$_6$) δ 11.22 (s, 1H), 7.66-7.59 (m, 1H), 7.27 (s, 1H), 7.16 (s, 1H), 7.05 (s, 1H), 5.37-5.32 (m, 1H), 2.98 (d, J=6.4 Hz, 2H), 2.71-2.64 (m, 5H), 2.34 (d, J=1.6 Hz, 3H), 2.16-2.15 (m, 2H), 1.88-1.72 (m, 2H), 1.66-1.54 (m, 2H), 1.37 (s, 9H).

Step 3—3-[6-[3-(3-Aminopropoxy)propyl]-2-oxo-1,3-benzoxazol-3-yl]piperidine-2,6-dione To a mixture of tert-butyl N-[3-[3-[3-(2,6-dioxo-3-piperidyl)-2-oxo-1,3-benzoxazol-6-yl]propoxy]propyl]carbamate (680 mg, 1.47 mmol) in DCM (20 mL) was added HCl/dioxane (4 M, 0.7 mL). The reaction mixture was stirred at 20° C. for 2 hours. On completion, the reaction mixture was concentrated in vacuo to give title compound (580 mg, 98% yield) as a white solid. LC-MS (ESI$^+$) m/z 362.1 (M+H)$^+$.

3-[7-[3-[3-(Methylamino)propoxy]propyl]-2-oxo-1,3-benzoxazol-3-yl]piperidine-2,6-dione (Intermediate QA)

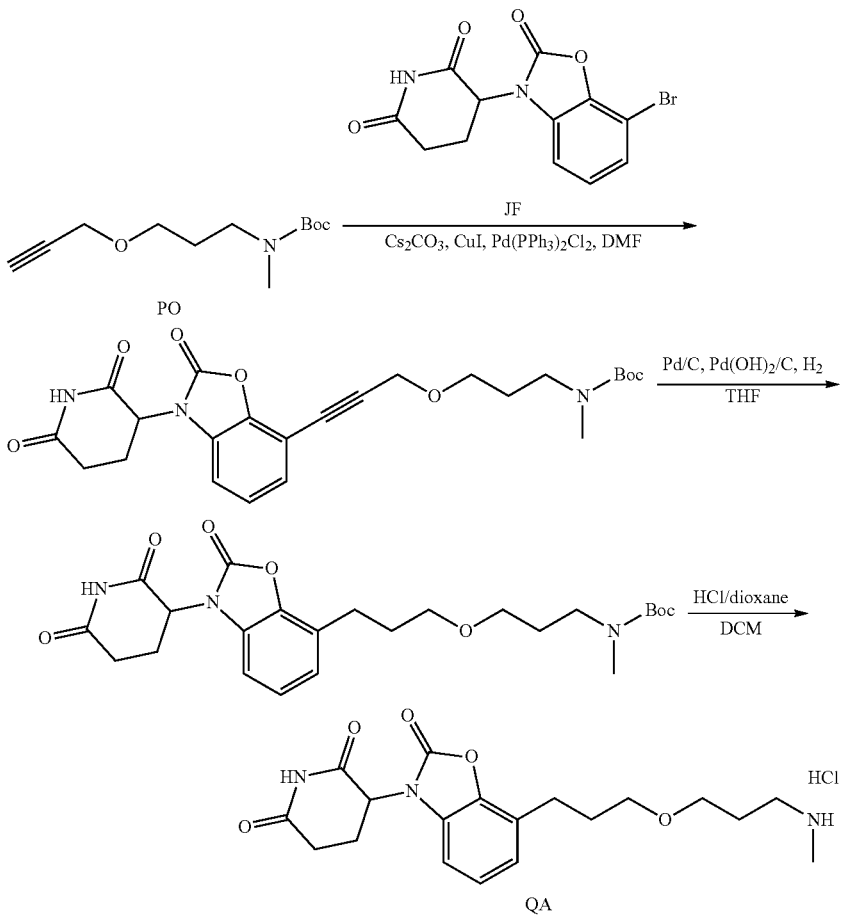

Step 1—Tert-butyl N-[3-[3-[3-(2,6-dioxo-3-piperidyl)-2-oxo-1,3-benzoxazol-7-yl]prop-2-ynoxy]propyl]-N-methyl-carbamate To a solution of tert-butyl N-methyl-N-(3-prop-2-ynoxypropyl)carbamate (1.05 g, 4.61 mmol, Intermediate PO) and 3-(7-bromo-2-oxo-1,3-benzoxazol-3-yl)piperidine-2,6-dione (500 mg, 1.54 mmol, Intermediate JF) in DMF (10 mL) was added Pd(PPh$_3$)$_2$Cl$_2$ (215 mg, 307 umol), CuI (58.5 mg, 307 umol) and Cs$_2$CO$_3$ (2.51 g, 7.69 mmol). The reaction mixture was stirred at 80° C. for 2 hr under N$_2$. On completion, the mixture was filtered, and the filtrate was concentrated in vacuo to give a residue. The residue was purified by reverse phase (0.1% FA condition) to give the title compound (440 mg, 60% yield) as a yellow solid. $^1$H NMR (400 MHz, DMSO-d$_6$) δ 11.21 (s, 1H), 7.35-7.28 (m, 1H), 7.28-7.19 (m, 2H), 5.39 (dd, J=5.2, 12.8 Hz, 1H), 4.45 (s, 2H), 3.53 (t, J=6.4 Hz, 2H), 3.23 (t, J=6.8 Hz, 2H), 2.94-2.82 (m, 1H), 2.77 (s, 3H), 2.71-2.60 (m, 2H), 2.22-2.13 (m, 1H), 1.81-1.68 (m, 2H), 1.37 (s, 9H); LC-MS (ESI$^+$) m/z 372.1 (M+H−100)$^+$.

Step 2—Tert-butyl N-[3-[3-[3-(2,6-dioxo-3-piperidyl)-2-oxo-1,3-benzoxazol-7-yl]propoxy]propyl]-N-methyl-carbamate To a solution of tert-butyl N-[3-[3-[3-(2,6-dioxo-3-piperidyl)-2-oxo-1,3-benzoxazol-7-yl]prop-2-ynoxy]propyl]-N-methyl-carbamate (440 mg, 933 umol) in THF (10 mL) was added Pd(OH)$_2$/C (150 mg, 10 wt %) and Pd/C (150 mg, 10 wt %). The reaction mixture was stirred at 25° C. under H$_2$ (15 psi) for 12 hours. On completion, the residue was filtered and the filtrate was concentrated in vacuo to give the title compound (400 mg, 90% yield) as a white solid. $^1$H NMR (400 MHz, DMSO-d$_6$) δ $^1$H NMR (400 MHz, DMSO-d$_6$) δ 11.21 (s, 1H), 7.18-7.06 (m, 2H), 7.01 (d, J=7.2 Hz, 1H), 5.35 (dd, J=5.2, 12.8 Hz, 1H), 3.42-3.38 (m, 2H), 3.35-3.30 (m, 2H), 3.21 (t, J=7.2 Hz, 2H), 2.93-2.83 (m, 1H), 2.78-2.71 (m, 5H), 2.70-2.61 (m, 2H), 2.19-2.10 (m, 1H), 1.91-1.79 (m, 2H), 1.74-1.63 (m, 2H), 1.37 (s, 9H); LC-MS (ESI$^+$) m/z 489.2 (M+Na)$^+$.

Step 3—3-[7-[3-[3-(Methylamino)propoxy]propyl]-2-oxo-1,3-benzoxazol-3-yl]piperidine-2,6-dione To a solution of tert-butyl N-[3-[3-[3-(2,6-dioxo-3-piperidyl)-2-oxo-1,3-benzoxazol-7-yl]propoxy]propyl]-N-methyl-carbamate (400 mg, 841 umol) in DCM (5 mL) was added HCl/dioxane (4 M, 5 mL). The reaction mixture was stirred at 20° C. for 1 hr. On completion, the mixture was concentrated in vacuo to give the title compound (340 mg, 98% yield, HCl) as a white solid. LC-MS (ESI$^+$) m/z 376.2 (M+H)$^+$.

2-Tert-butyl N-[2-[2-[2-(2-oxo-3H-benzimidazol-1-yl)ethoxy]ethoxy]ethyl]carbamate (Intermediate QB)

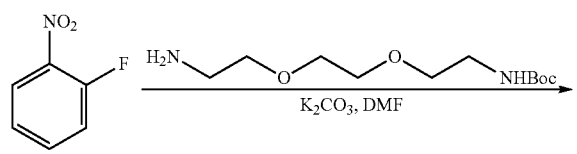

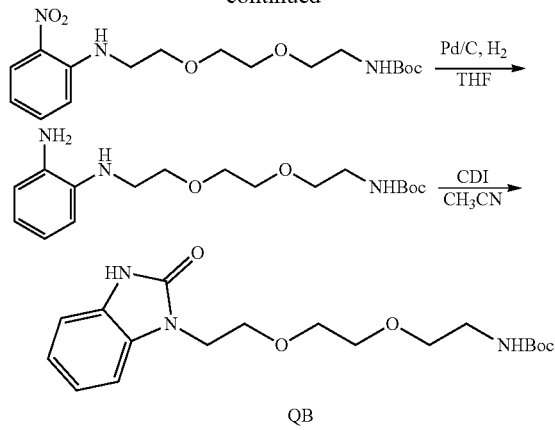

Step 1—Tert-butyl N-[2-[2-[2-(2-nitroanilino)ethoxy]ethoxy]ethyl]carbamate

To a mixture of 1-fluoro-2-nitro-benzene (2.84 g, 20.1 mmol, 2.12 mL, CAS #127723-77-7) and tert-butyl N-[2-[2-(2-aminoethoxy)ethoxy]ethyl]carbamate (5.00 g, 20.1 mmol, CAS #153086-78-3) in DMF (50 mL) was added K$_2$CO$_3$ (8.35 g, 60.4 mmol). The reaction mixture was stirred at 80° C. for 2 hours. On completion, the reaction mixture was diluted with water (50 mL) and extracted with EA (2×100 mL). The combined organic layers was dried over Na$_2$SO$_4$, filtered and concentrated in vacuo to give the title compound (7.40 g, 99% yield) as red oil. $^1$H NMR (400 MHz, CDCl$_3$) δ 8.25 (s, 1H), 8.20-8.14 (m, 1H), 7.48-7.40 (m, 1H), 6.86 (d, J=8.4 Hz, 1H), 6.71-6.61 (m, 1H), 5.07 (s, 1H), 3.80 (t, J=5.2 Hz, 2H), 3.71-3.62 (m, 4H), 3.59-3.49 (m, 4H), 3.88-3.27 (m, 2H), 1.43 (s, 9H).

Step 2—Tert-butyl N-[2-[2-[2-(2-aminoanilino)ethoxy]ethoxy]ethyl]carbamate

To a mixture of tert-butyl N-[2-[2-[2-(2-nitroanilino)ethoxy]ethoxy]ethyl]carbamate (7.00 g, 18.9 mmol) in THF (100 mL) was added Pd/C (3.00 g, 10 wt %). The reaction mixture was stirred at 25° C. for 12 hours under H$_2$ (15 Psi) atmosphere. On completion, the reaction mixture was filtered and concentrated in vacuo to give the title compound (6.40 g, 99% yield) as red oil. $^1$H NMR (400 MHz, CDCl$_3$) δ 6.84-6.78 (m, 1H), 6.74-6.64 (m, 3H), 5.32 (s, 1H), 3.76 (t, J=5.2 Hz, 2H), 3.67-3.60 (m, 4H), 3.54 (t, J=5.2 Hz, 2H), 3.35-3.27 (m, 4H), 1.45 (s, 9H).

Step 3—2-Tert-butyl N-[2-[2-[2-(2-oxo-3H-benzimidazol-1-yl)ethoxy]ethoxy]ethyl]carbamate To a mixture of tert-butyl N-[2-[2-[2-(2-aminoanilino)ethoxy]ethoxy]ethyl]carbamate (6.70 g, 19.7 mmol) in THF (100 mL) was added CDI (11.8 g, 73.0 mmol) and DIPEA (9.44 g, 73.0 mmol, 12.7 mL). The mixture was stirred at 25° C. for 3 hours. On completion, the reaction mixture was diluted with water (50 mL) and extracted with EA (2×100 mL). The combined organic layers was dried over Na$_2$SO$_4$, filtered and concentrated in vacuo to give a residue. The residue was purified by column chromatography to give the title compound (7.20 g, 99% yield) as red oil. $^1$H NMR (400 MHz, DMSO-d$_6$) δ 10.86 (s, 1H), 7.02-6.94 (m, 4H), 6.74

(s, 1H), 3.93 (t, J=5.6 Hz, 2H), 3.65 (t, J=5.6 Hz, 2H), 3.52-3.41 (m, 4H), 3.32 (t, J=6.0 Hz, 2H), 3.10-2.94 (m, 2H), 1.36 (s, 9H).

3-[3-[2-[2-(2-Aminoethoxy)ethoxy]ethyl]-2-oxo-benzimidazol-1-yl]piperidine-2,6-dione (Intermediate QC)

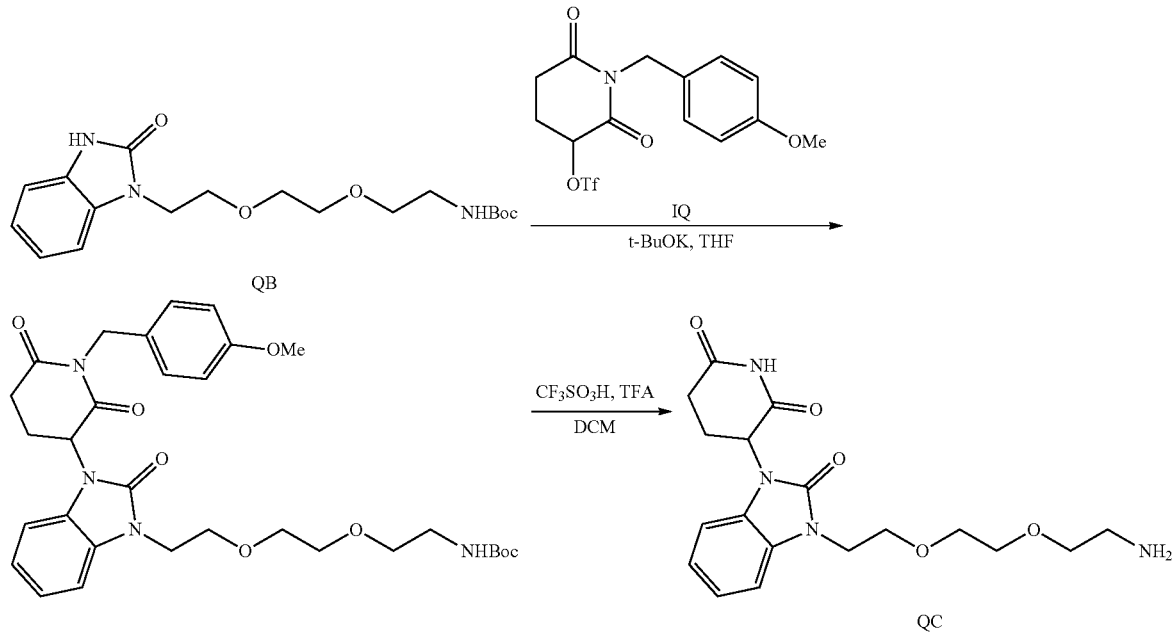

Step 1—Tert-butyl N-[2-[2-[2-[3-[1-[(4-methoxyphenyl)methyl]-2,6-dioxo-3-piperidyl]-2-oxo-benzimidazol-1-yl]ethoxy]ethoxy]ethyl]carbamate To a mixture of tert-butyl N-[2-[2-[2-(2-oxo-3H-benzimidazol-1-yl)ethoxy]ethoxy]ethyl]carbamate (3.00 g, 8.21 mmol, Intermediate QB) in THF (50 mL) was added t-BuOK (1.38 g, 12.3 mmol), the mixture was stirred at 0° C. for 0.5 hour. Then [1-[(4-methoxyphenyl)methyl]-2,6-dioxo-3-piperidyl]trifluoromethane sulfonate (4.70 g, 12.3 mmol, Intermediate IQ) in THF (20 mL) was added to the mixture. The reaction mixture was stirred at 0° C. for 2 hours under N₂ atmosphere. On completion, the reaction mixture was diluted with water (30 mL) and extracted with EA (2×200 mL). The combined organic layers was dried over Na₂SO₄, filtered and concentrated in vacuo to give a residue. The residue was purified by prep-HPLC (0.1% FA condition) to give the title compound (4.00 g, 81% yield) as brown oil. ¹H NMR (400 MHz, DMSO-d₆) δ 7.26 (d, J=7.6 Hz, 1H), 7.21 (d, J=8.8 Hz, 2H), 7.09-7.04 (m, 1H), 7.02-6.95 (m, 2H), 6.85 (d, J=8.8 Hz, 2H), 6.70 (s, 1H), 5.57-5.48 (m, 1H), 4.87-4.73 (m, 2H), 4.02-3.98 (m, 2H), 3.72 (s, 3H), 3.68 (d, J=5.2 Hz, 2H), 3.54-3.49 (m, 2H), 3.46-3.41 (m, 2H), 3.33 (s, 2H), 3.12-3.05 (m, 1H), 3.04-2.97 (m, 2H), 2.86-2.69 (m, 2H), 2.10-2.01 (m, 1H), 1.36 (s, 9H).

Step 2—3-[3-[2-[2-(2-Aminoethoxy)ethoxy]ethyl]-2-oxo-benzimidazol-1-yl]piperidine-2,6-dione To a mixture of tert-butyl N-[2-[2-[2-[3-[1-[(4-methoxyphenyl)methyl]-2,6-dioxo-3-piperidyl]-2-oxo-enzimidazol-1-yl]ethoxy]ethoxy]ethyl]carbamate (1.00 1.68 mmol) in DCM (10 mL) was added TFA (7.70 g, 67.5 mmol, 5.00 mL). The mixture was stirred at 25° C. for 0.5 hour. Then CF₃SO₃H (4.25 g, 28.3 mmol, 2.50 mL) was added to the mixture. The mixture was stirred at 25° C. for 30 hours. On completion, the reaction mixture was diluted with water (20 mL) and basified with saturated aqueous K₂CO₃ till pH=8-9, then the solution was extracted with DCM (3×50 mL). The aqueous phase was concentrated in vacuo to give a residue. The residue was purified by prep-HPLC (0.1% HCl condition) to give the title compound (330 mg, 52% yield) as brown oil. ¹H NMR (400 MHz, DMSO-d₆) δ 11.10 (s, 1H), 7.74 (s, 2H), 7.25 (d, J=7.2 Hz, 1H), 7.15-7.09 (m, 1H), 7.09-7.00 (m, 2H), 5.41-5.33 (m, 1H), 4.01 (t, J=5.4 Hz, 2H), 3.70 (t, J=5.4 Hz, 2H), 3.58-3.55 (m, 2H), 3.53-3.50 (m, 4H), 2.94-2.85 (m, 3H), 2.78-2.63 (m, 2H), 2.06-1.97 (m, 1H).

Benzyl ((S)-1-(((S)-1-cyclohexyl-2-((S)-2-(4-(3-hydroxybenzoyl)thiazol-2-yl)pyrrolidin-1-yl)-2-oxoethyl)amino)-1-oxopropan-2-yl)(methyl)carbamate (Intermediate

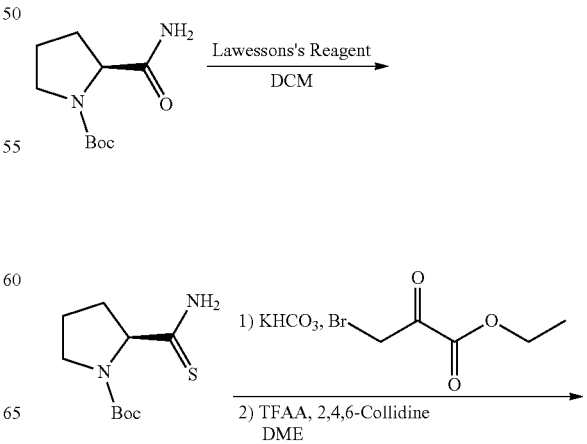

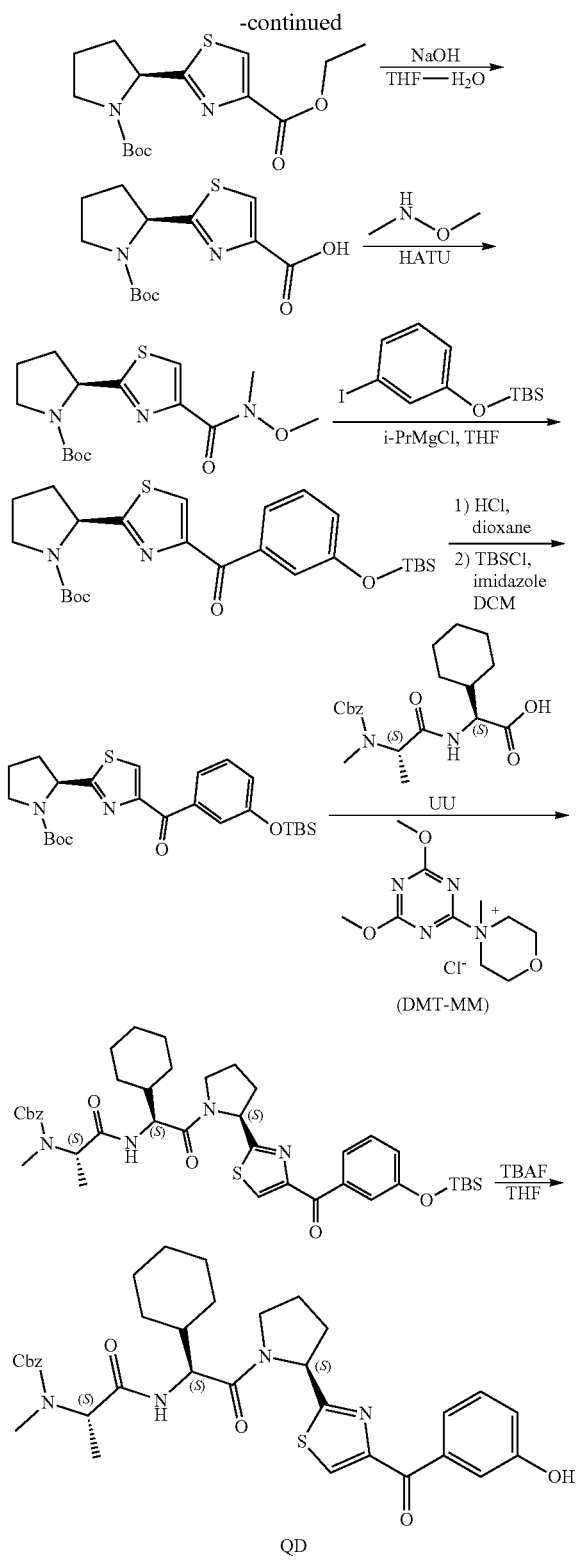

Step 1—(S)-tert-butyl 2-carbamothioylpyrrolidine-1-carboxylate

To a stirred solution Boc-D-prolinamide (50.0 g, 234.0 mmol) in CH$_2$Cl$_2$ (25 mL) at rt was added Lawesson's reagent (62.2 g, 140.0 mmol). The mixture was stirred overnight, then washed with NaHCO$_3$ (sat., 500 mL). The organic layer was washed with brine, and dried over anhydrous Na$_2$SO$_4$. The oily residue was purified by column chromatography on silica gel, eluted with a 0-10 percent MeOH in CH$_2$Cl$_2$ gradient, to afford the title compound (42 g, 78% yield) as a white solid. $^1$H NMR (400 MHz, DMSO-d$_6$) δ 9.51 (s, 1H), 9.08 (m, 1H), 4.41 (dd, J=8.4, 3.3 Hz, 1H), 3.47-3.46 (m, 1H), 3.27 (s, 1H), 2.27-2.09 (m, 1H), 1.92-1.65 (m, 3H), 1.37 (m, 9H).

Step 2—ethyl (S)-2-(1-(tert-butoxycarbonyl)pyrrolidin-2-yl)thiazole-4-carboxylate Ethyl bromopyruvate (4.15 g, 21.3 mmol) was added dropwise via syringe to a mixture of (S)-tert-butyl 2-carbamothioylpyrrolidine-1-carboxylate (3.5 g, 15.2 mmol) and potassium bicarbonate (50.5 g, 504 mmol) in 35 mL of dimethoxyethane at 23° C. The resulting mixture was stirred vigorously for 25 minutes, and then the mixture was cooled to 0° C. A mixture of trifluoroacetic anhydride (TFAA) (3.19 g, 15.2 mmol, 1 equiv.) and 2,4,6-collidine (2.94 g, 24.3 mmol, 1.6 equiv.) was then added dropwise via canula to the yellow mixture prepared above at 0° C. Following this addition, an additional three portions of neat TFAA (3.19 g, 15.2 mmol, 1 equiv.) and 2,4,6-collidine (2.94 g, 24.3 mmol, 1.6 equiv.) were prepared and added in sequence dropwise via canula to the yellow reaction mixture at 0° C. The resulting yellow mixture was stirred vigorously at 0° C. for 3 h. Then water (1,000 mL) was added and the solution was extracted with dichloromethane (2×50 mL). The organic phases were combined, washed with 0.5 N aqueous HCl (100 mL), washed with brine (100 mL), and dried over anhydrous sodium sulfate. The solution was filtered and concentrated to afford a light yellow solid. This solid was purified by flash column chromatography on silica gel (1:9 to 2:3 ethyl acetate:hexanes) providing a light yellow solid. This solid was triturated with ether (20 mL) to afford the title compound as a white solid (2.2 g, 44% yield). $^1$H NMR (400 MHz, DMSO-d$_6$) δ 8.41 (d, J=9.8 Hz, 1H), 5.08 (d, J=7.3 Hz, 1H), 4.33-4.25 (m, 2H), 3.53-3.34 (m, 2H), 2.38-2.27 (m, 1H), 2.04-1.99 (m, 1H), 1.93-1.79 (m, 2H), 1.43 (s, 6H), 1.30 (t, J=7.1 Hz, 3H), 1.24 (s, 3H). LC/MS (ESI, m/z): [M+1]$^+$=327.3.

Step 3—(S)-2-(1-(tert-butoxycarbonyl)pyrrolidin-2-yl)thiazole-4-carboxylic acid

A solution of (S)-ethyl 2-(1-(tert-butoxycarbonyl)pyrrolidin-2-yl)thiazole-4-carboxylate (14.5 g, 44.5 mmol, 1 equiv.) in tetrahydrofuran (60 mL) was added to a solution of sodium hydroxide (5.33 g, 134.5 mmol, 3 equiv.) in water (40 mL) at 23° C. The resulting mixture was stirred vigorously at 23° C. for 3 h. Then the mixture was concentrated to 20 mL. The concentrated mixture was cooled to 0° C. and the pH was adjusted to 3 by the addition of concentrated HCl solution dropwise. A lot of white solid was formed and the solid was collected by filtration to provide the title compound as a white solid (10.4 g, 74% yield). LC/MS (ESI, m/z): [M+1]$^+$=299.4.

Step 4—tert-butyl (S)-2-(4-(methoxy(methyl)carbamoyl)thiazol-2-yl)pyrrolidine-1-carboxylate (S)-2-(1-(tert-butoxycarbonyl)pyrrolidin-2-yl)thiazole-4-carboxylic acid (22.6 g, 75.8 mmol), O,N-dimethylhydroxylamine hydrochloride (11.9 g, 122.7 mmol), diisopropyl ethyl amine (45.0 mL, 243 mmol) and HATU (46.2 g, 122.0 mmol) in DMF (200 mL) were stirred at rt for 12 hours. The reaction mixture was quenched with water, and the layers were separated. The aqueous layer was extracted with EtOAc (100 mL×3), and the combined organic layers were dried, filtered and concentrated. The crude product was purified via column chromatography on silica gel, eluting with hexanes/ethyl acetate (1:1) to give the title compound as an oil (23.0 g, 89% yield). LC/MS (ESI, m/z): [M+1]$^+$=342.2. $^1$H NMR (400 MHz, DMSO-d$_6$) δ 8.11 (s, 1H), 5.08 (m, 1H), 3.72 (s, 3H), 3.52-3.35 (m, 2H), 3.29 (s, 3H), 2.32 (m, 1H), 2.06 (m, 1H), 1.96-1.77 (m, 2H), 1.50-1.20 (d, 9H).

Step 5—(S)-tert-butyl 2-(4-(3-((tert-butyldimethylsilyl)oxy)benzoyl)thiazol-2-yl)pyrrolidine-1-carboxylate To a solution of tert-butyl(3-iodophenoxy)dimethylsilane (6.9 g, 20.6 mmol) in THF (50 mL) was added isopropylmagnesium chloride solution (9.27 mL, 2.0 M in THF) dropwise at −10° C. under N$_2$. The reaction mixture was stirred at 0° C. for 30 min. Then this resulting mixture, which formed (3-((tert-butyldimethylsilyl)oxy)phenyl)magnesium iodide, was added dropwise via syringe to a solution of the weinreb amide tert-butyl (S)-2-(4-(methoxy(methyl) carbamoyl)thiazol-2-yl)pyrrolidine-1-carboxylate (3.9 g, 11.4 mmol) in THF (10 mL) at 0° C. The mixture was stirred at 0° C. for 30 min then warmed up to rt and stirred for 4 h. The mixture was then cooled to −5° C. and quenched with saturated ammonium chloride solution (20 mL). The mixture was partitioned between water (30 mL) and ethyl acetate (100 mL). The organic phase was separated and the aqueous phase was further extracted with ethyl acetate (3×100 mL). The organic phases were combined, washed with brine (50 mL) and dried over anhydrous sodium sulfate. The dried solution was filtered and concentrated to give a light yellow oil. This oil was purified by flash column chromatography on silica gel (1:30 to 1:10 ethyl acetate: hexanes) providing the title compound as a colorless oil (5.13 g, 92.1%). $^1$H NMR (400 MHz, CDCl$_3$) δ 8.10 (s, 1H), 7.76 (d, J=7.7 Hz, 1H), 7.71-7.66 (m, 1H), 7.34 (t, J=7.9 Hz, 1H), 7.07 (d, J=7.0 Hz, 1H), 5.30-5.19 (m, 1H), 3.66-3.41 (m, 2H), 2.42-2.19 (m, 2H), 2.01-1.90 (m, 2H), 1.50 (s, 3H), 1.35 (s, 6H), 1.02-0.98 (m, 9H), 0.28-0.14 (m, 6H); LC/MS (ESI, m/z): [M+1]$^+$=489.5.

Step 6—(S)-(3-((tert-butyldimethylsilyl)oxy)phenyl) (2-(pyrrolidin-2-yl)thiazol-4-yl)methanone To a solution of (S)-tert-butyl 2-(4-(3-((tert-butyldimethylsilyl)oxy)benzoyl)thiazol-2-yl)pyrrolidine-1-carboxylate (12.0 g, 20.5 mmol) in 1,4-dioxane (60 mL) was added HCl-dioxane (40 mL) (4 M in dioxane) dropwise. The reaction mixture was stirred at rt for 3 h. The reaction mixture concentrated in vacuo and used directly without further purification to afford (S)-(3-hydroxyphenyl)(2-(pyrrolidin-2-yl)thiazol-4-yl)methanone HCl salt (8.0 g). To a solution of (S)-(3-hydroxyphenyl)(2-(pyrrolidin-2-yl)thiazol-4-yl)methanone HCl salt (8.00 g, 25.7 mmol) in DCM (80 mL) was added imidazole (5.2 g, 57.2 mmol) slowly at 0° C. Then TBSCl (3.89 g, 34.3 mmol, in 20 mL DCM) was added slowly at 0° C. The resulting mixture was stirred at rt for 130 min. The reaction mixture was quenched with water, extracted with ethyl acetate (3×100 mL), washed with brine (50 mL) and dried over anhydrous sodium sulfate. The solution was filtered, concentrated, and purified by flash column chromatography on silica gel (1:100 to 1:40 methanol/DCM) to give the title compound as a yellow oil (8.0 g, 84% yield). $^1$H NMR (400 MHz, DMSO-d$_6$) δ 8.38 (s, 1H), 7.71-7.64 (m, 2H), 7.43 (t, J=8.0 Hz, 1H), 7.14 (ddd, J=8.0, 2.4, 1.1 Hz, 1H), 4.51 (dd, J=8.3, 4.9 Hz, 1H), 3.56 (s, 1H), 3.00-2.89 (m, 2H), 2.27-2.10 (m, 1H), 1.75-1.70 (m, 1H), 1.77-1.65 (m, 2H), 0.97 (s, 9H), 0.22 (s, 6H).

Step 7—benzyl ((S)-1-(((S)-2-((S)-2-(4-(3-((tert-butyldimethylsilyl)oxy)benzoyl)thiazol-2-yl)pyrrolidin-1-yl)-1-cyclohexyl-2-oxoethyl)amino)-1-oxopropan-2-yl)(methyl)carbamate In a 250-mL round-bottom flask, was placed (S)-(3-((tert-butyldimethyl silyl)oxy)phenyl)(2-(pyrrolidin-2-yl)thiazol-4-yl)methanone (7.5 g, 19.3 mmol), (S)-2-((S)-2-(((benzyloxy)carbonyl)(methyl)amino)propanamido)-2-cyclohexylacetic acid (9.5 g, 25.1 mmol, Intermediate UU), and 4-methylmorpholine (3.90 g, 38.60 mmol) in EtOAc (100 mL) at 0° C. DMT-MM (6.94 g, 25.1 mmol) was then added and the resulting solution was stirred for 3 h at 0° C. Then H$_2$O (40 mL) was added, and the resulting solution was extracted with EtOAC (3×50 mL). The combined organic layers were washed with 50 mL of brine, dried over anhydrous sodium sulfate and concentrated under vacuum. The residue was applied onto a silica gel column eluting with ethyl acetate/petroleum ether (1:2) to give the title compound as a yellow solid. (7.3 g, 60% yield). $^1$H NMR (400 MHz, DMSO-d$_6$) δ 8.49 (s, 1H), 7.95 (d, J=39.4 Hz, 1H), 7.74-7.63 (m, 2H), 7.43 (t, J=7.9 Hz, 1H), 7.35-7.31 (m, 5H), 7.16 (dd, J=8.0, 2.5 Hz, 1H), 5.37 (dd, J=7.6, 2.2 Hz, 1H), 5.08-5.01 (m, 1H), 4.66 (d, J=6.6 Hz, 1H), 4.37 (t, J=7.5 Hz, 1H), 3.83-3.75 (m, 2H), 2.83 (s, 3H), 2.33-2.14 (m, 2H), 2.07-1.98 (m, 2H), 1.67-1.48 (m, 6H), 1.25 (s, 3H), 1.07-0.89 (m, 14H), 0.22 (s, 6H). LC/MS (ESI, m/z): [M+1]$^+$=747.6.

Step 8—benzyl ((S)-1-(((S)-1-cyclohexyl-2-((S)-2-(4-(3-hydroxybenzoyl)thiazol-2-yl)pyrrolidin-1-yl)-2-oxoethyl)amino)-1-oxopropan-2-yl)(methyl)carbamate To a stirred solution of benzyl ((S)-1-(((S)-2-((S)-2-(4-(3-((tert-butyldimethylsilyl)oxy)benzoyl)thiazol-2-yl)pyrrolidin-1-yl)-1-cyclohexyl-2-oxoethyl)amino)-1-oxopropan-2-yl)(methyl)carbamate (5.0 g, 6.68 mmol) in THF (20 mL) was added TBAF (8.0 mL, 8.0 mmol) a rt. The reaction mixture was stirred at rt for 4 h. Then H$_2$O (20 mL) was added and the mixture was extracted with EtOAc (50 mL×2). The combined organic layer was washed with brine, dried and concentrated in vacuo. The mixture was purified via column chromatography (DCM/EtOAc=5%-80%) to give the title compound (3.2 g, 76% yield) as a yellow solid. $^1$H NMR (400 MHz, MeOD-d$_4$) δ 8.26 (s, 1H), 7.59-7.53 (m, 1H), 7.51 (dd, J=2.3, 1.7 Hz, 1H), 7.37-7.28 (m, 6H), 7.05 (ddd, J=8.1, 2.6, 0.9 Hz, 1H), 5.50-5.39 (m, 1H), 5.13 (s, 2H), 4.69 (s, 1H), 4.54-4.38 (m, 1H), 4.02-3.93 (m, 1H), 3.90-3.86 (m, 1H), 2.94 (s, 3H), 2.23-2.10 (m, 4H), 1.72-1.56 (m, 6H), 1.37 (d, J=5.2 Hz, 3H), 1.16-0.88 (m, 5H); LC-MS (ESI$^+$): m/z 633.5 (M+H)$^+$.

Benzyl N-[(1S)-2-[[(1S)-2-[(2S)-2-[4-[3-[2-[2-[2-[2-[2-(2-aminoethoxy)ethoxy]ethoxy]ethoxy]ethoxy]benzoyl]thiazol-2-yl]pyrrolidin-1-yl]-1-cyclohexyl-2-oxo-ethyl]amino]-1-methyl-2-oxo-ethyl]-N-methyl-carbamate (Intermediate QE)

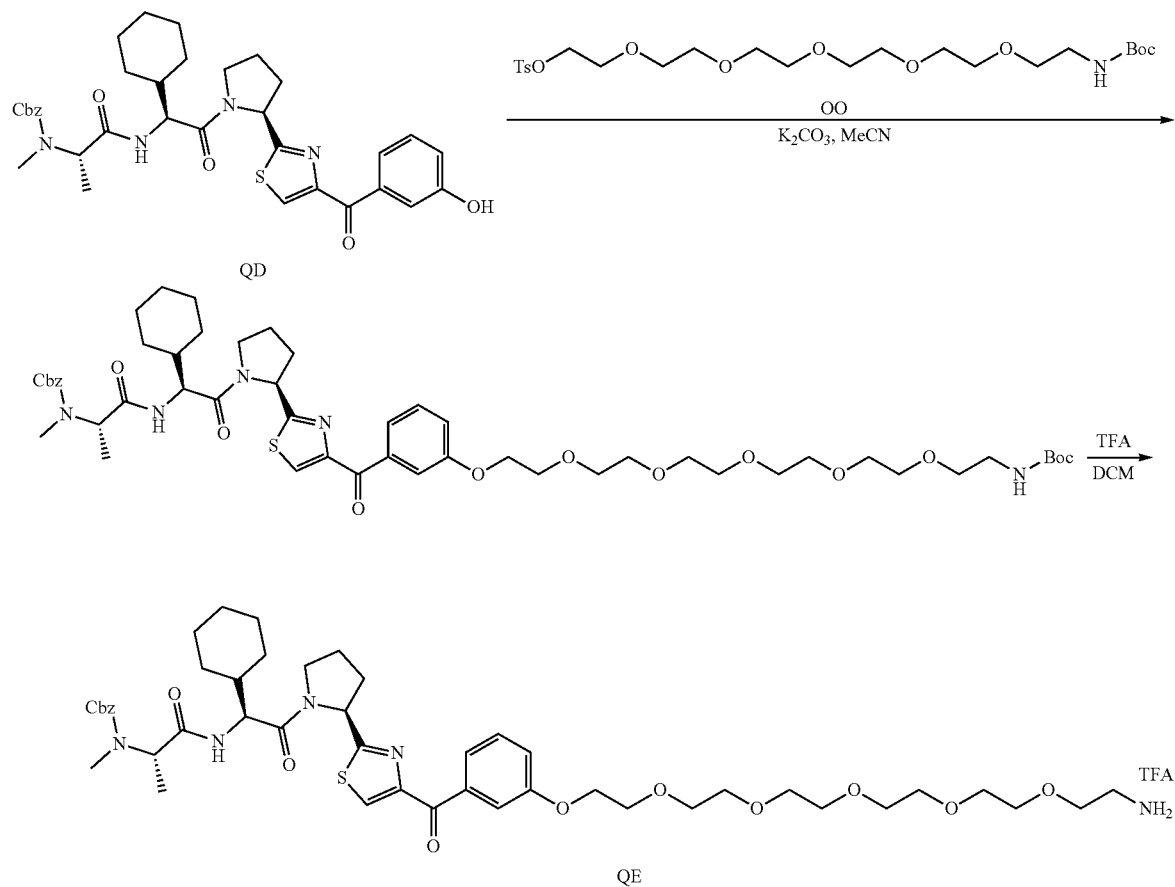

Step 1—benzyl ((S)-1-(((S)-1-cyclohexyl-2-((S)-2-(4-(3-((2,2-dimethyl-4-oxo-3,8,11,14,17,20-hexaoxa-5-azadocosan-22-yl)oxy)benzoyl)thiazol-2-yl)pyrrolidin-1-yl)-2-oxoethyl)amino)-1-oxopropan-2-yl)(methyl)carbamate To a solution of benzyl ((S)-1-(((S)-1-cyclohexyl-2-((S)-2-(4-(3-hydroxybenzoyl)thiazol-2-yl)pyrrolidin-1-yl)-2-oxoethyl)amino)-1-oxopropan-2-yl)(methyl)carbamate (1.3 g, 2.06 mmol, Intermediate QD) in CH₃CN (100 mL) was added 2,2-dimethyl-4-oxo-3,8,11,14,17,20-hexaoxa-5-azadocosan-22-yl 4-methylbenzenesulfonate (1.32 g, 2.47 mmol, Intermediate OO) and K₂CO₃ (340.9 mg, 2.47 mmol) at rt. Then the reaction mixture was stirred at 80° C. for 12 h. The reaction mixture solvent was removed under reduced pressure. The residue was purified via column chromatography (EtOAc/Petroleum ether) to give the title compound (1.71 g, 84% yield) as a pale yellow oil. LC/MS (ESI, m/z): [M+1]⁺=997.56.

Step 2—benzyl ((S)-1-(((S)-2-((S)-2-(4-(3-((17-amino-3,6,9,12,15-pentaoxaheptadecyl)oxy)benzoyl)thiazol-2-yl)pyrrolidin-1-yl)-1-cyclohexyl-2-oxoethyl)amino)-1-oxopropan-2-yl)(methyl)carbamate 2,2,2-trifluoroacetate To a solution of benzyl ((S)-1-(((S)-1-cyclohexyl-2-((S)-2-(4-(3-((2,2-dimethyl-4-oxo-3,8,11,14,17,20-hexaoxa-5-azadocosan-22-yl)oxy)benzoyl)thiazol-2-yl)pyrrolidin-1-yl)-2-oxoethyl)amino)-1-oxopropan-2-yl)(methyl)carbamate (1.6 g, 1.61 mmol) in DCM (30 mL) was added TFA (30 mL) and the reaction mixture was stirred at rt for 3 h. Then the reaction mixture solvent was removed under reduced pressure and the residue was purified via reverse phase column chromatography (ACN/H₂O) to give the title compound (1.4 g, 86% yield) as a pale yellow oil. ¹H NMR (400 MHz, MeOD): 8.32 (s, 1H), 7.86-7.67 (m, 2H), 7.45 (t, J=7.9 Hz, 1H), 7.41-7.13 (m, 6H), 5.62-5.47 (m, 1H), 5.13 (s, 2H), 4.73-4.68 (m, 1H), 4.59-4.34 (m, 1H), 4.24-4.22 (m, 2H), 4.07-3.79 (m, 4H), 3.79-3.52 (m, 18H), 3.19-3.05 (m, 2H), 2.94-2.77 (m, 3H), 2.62-1.91 (m, 4H), 1.88-1.49 (m, 6H), 1.37-1.35 (m, 3H), 1.23-0.82 (m, 5H). LC/MS (ESI, m/z): [M+1]⁺=896.57.

Benzyl N-[(1S)-2-[[(1S)-2-[(2S)-2-[4-[3-[2-[2-[2-(2-aminoethoxy)ethoxy]ethoxy]ethoxy]benzoyl]thiazol-2-yl]pyrrolidin-1-yl]-1-cyclohexyl-2-oxo-ethyl]amino]-1-methyl-2-oxo-ethyl]-N-methyl-carbamate
(Intermediate QF)

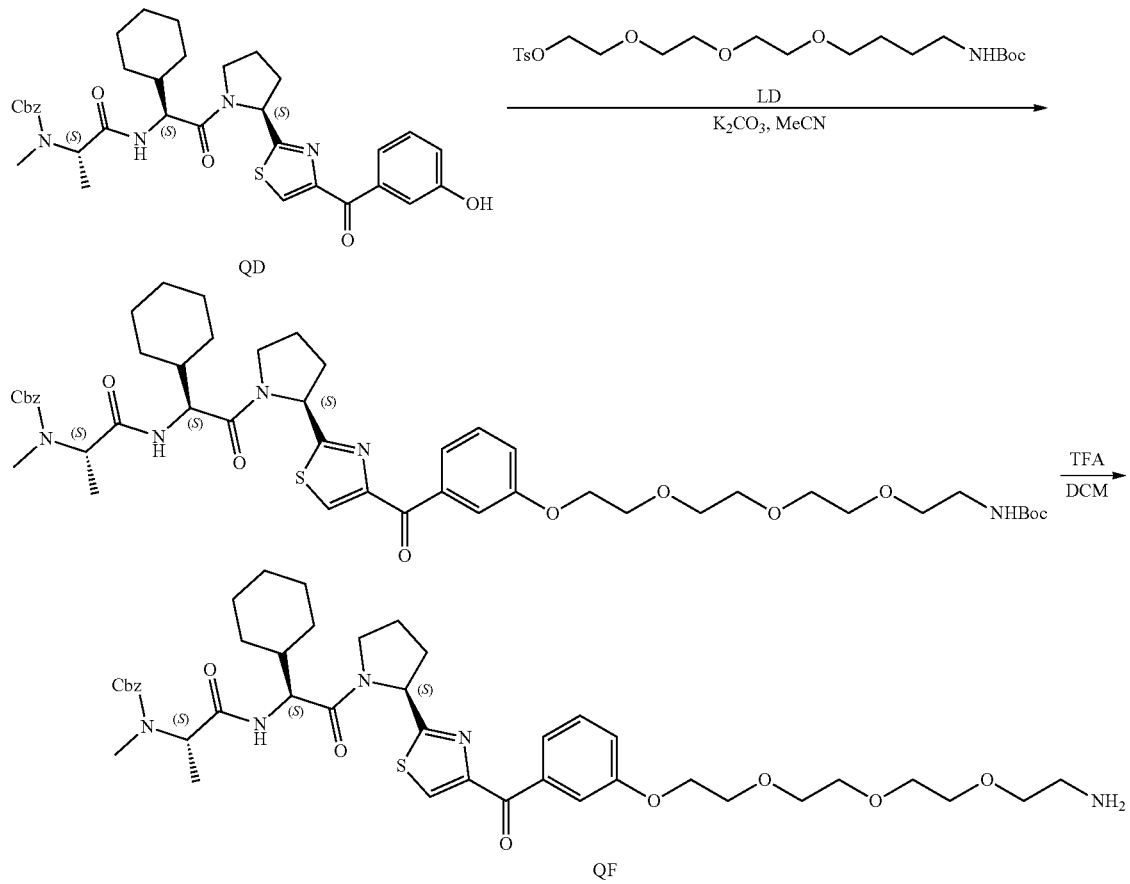

Step 1—benzyl ((S)-1-(((S)-1-cyclohexyl-2-((S)-2-(4-(3-((2,2-dimethyl-4-oxo-3,8,11,14-tetraoxa-5-azahexadecan-16-yl)oxy)benzoyl)thiazol-2-yl)pyrrolidin-1-yl)-2-oxoethyl)amino)-1-oxopropan-2-yl)(methyl)carbamate To a solution of benzyl ((S)-1-(((S)-1-cyclohexyl-2-((S)-2-(4-(3-hydroxybenzoyl)thiazol-2-yl)pyrrolidin-1-yl)-2-oxoethyl)amino)-1-oxopropan-2-yl)(methyl)carbamate (1.50 g, 2.38 mmol, Intermediate QD) in CH₃CN (100 mL) was added 2,2-dimethyl-4-oxo-3,8,11,14-tetraoxa-5-azahexadecan-16-yl 4-methylbenzenesulfonate (1.30 g, 3.09 mmol, Intermediate LD) and K₂CO₃ (346.4 mg, 2.51 mmol) at rt. The reaction mixture was stirred at 80° C. for 12 hours. The reaction mixture was then concentrated under reduced pressure. The residue was purified via column chromatography on silica gel (EtOAc/petroleum ether=1/1-EA) to give the title compound (1.80 g, 80% yield) as a white solid. ¹H NMR (400 MHz, DMSO-d₆) δ 8.49 (s, 1H), 7.97 (d, J=40.8 Hz, 1H), 7.69-7.64 (m, 2H), 7.46 (t, J=7.9 Hz, 1H), 7.39-7.29 (m, 5H), 7.26 (dd, J=8.2, 1.9 Hz, 1H), 6.73 (t, J=5.1 Hz, 1H), 5.40-5.37 (m, 1H), 5.09-5.06 (m, 2H), 4.70-4.65 (m, 1H), 4.38 (t, J=7.5 Hz, 1H), 4.23-4.12 (m, 2H), 3.85-3.73 (m, 4H), 3.62-3.59 (m, 2H), 3.55-3.47 (m, 6H), 3.36 (t, J=6.2 Hz, 2H), 3.05 (q, J=5.9 Hz, 2H), 2.84 (s, 3H), 2.28-2.14 (m, 2H), 2.08-2.01 (m, 2H), 1.66-1.44 (m, 6H), 1.36 (s, 9H), 1.26 (br s, 3H), 1.09-0.86 (m, 5H). LC/MS (ESI, m/z): [M+1]⁺=908.6.

Step 2—benzyl ((S)-1-(((S)-2-((S)-2-(4-(3-(2-(2-(2-(2-aminoethoxy)ethoxy)ethoxy)ethoxy)benzoyl)thiazol-2-yl)pyrrolidin-1-yl)-1-cyclohexyl-2-oxoethyl)amino)-1-oxopropan-2-yl)(methyl)carbamate To a solution of benzyl ((S)-1-(((S)-1-cyclohexyl-2-((S)-2-(4-(3-((2,2-dimethyl-4-oxo-3,8,11,14-tetraoxa-5-azahexadecan-16-yl)oxy)benzoyl)thiazol-2-yl)pyrrolidin-1-yl)-2-oxoethyl)amino)-1-oxopropan-2-yl)(methyl)carbamate (1.8 g, 1.47 mmol) in DCM (30 mL) was added TFA (30 mL) and the reaction mixture was stirred at rt for 3 h. The reaction mixture was concentrated under reduced pressure to give the title compound (1.8 g, 100% yield, TFA salt) as a light yellow oil. ¹H NMR (400 MHz, CD₃OD) δ 8.32 (s, 1H), 7.80 (br s, 1H), 7.76-7.70 (m, 2H), 7.44 (t, J=7.9 Hz, 1H), 7.38-7.30 (m, 5H), 7.26-7.20 (m, 1H), 5.47-5.46 (m, 1H), 5.13 (s, 2H), 4.73-4.65 (m, 1H), 4.53-4.40 (m, 1H), 4.22 (dd, J=5.3, 3.8 Hz, 2H), 4.00-3.94 (m, 1H), 3.89-3.86 (m, 3H), 3.76-3.72 (m, 2H), 3.70-3.66 (m, 8H), 3.12-3.08 (m, 2H), 2.94 (s, 3H), 2.40-2.19 (m, 3H), 2.17-2.09 (m, 1H), 1.72-1.57 (m, 6H), 1.36 (d, J=7.2 Hz, 3H), 1.19-0.94 (m, 5H). LC/MS (ESI, m/z): [M+1]⁺=808.6.

Benzyl N-[(1S)-2-[[(1S)-2-[(2S)-2-[4-[3-[2-[2-[2-[2-(2-aminoethoxy)ethoxy]ethoxy]ethoxy]ethoxy]benzoyl]thiazol-2-yl]pyrrolidin-1-yl]-1-cyclohexyl-2-oxo-ethyl]amino]-1-methyl-2-oxo-ethyl]-N-methyl-carbamate (Intermediate QG)

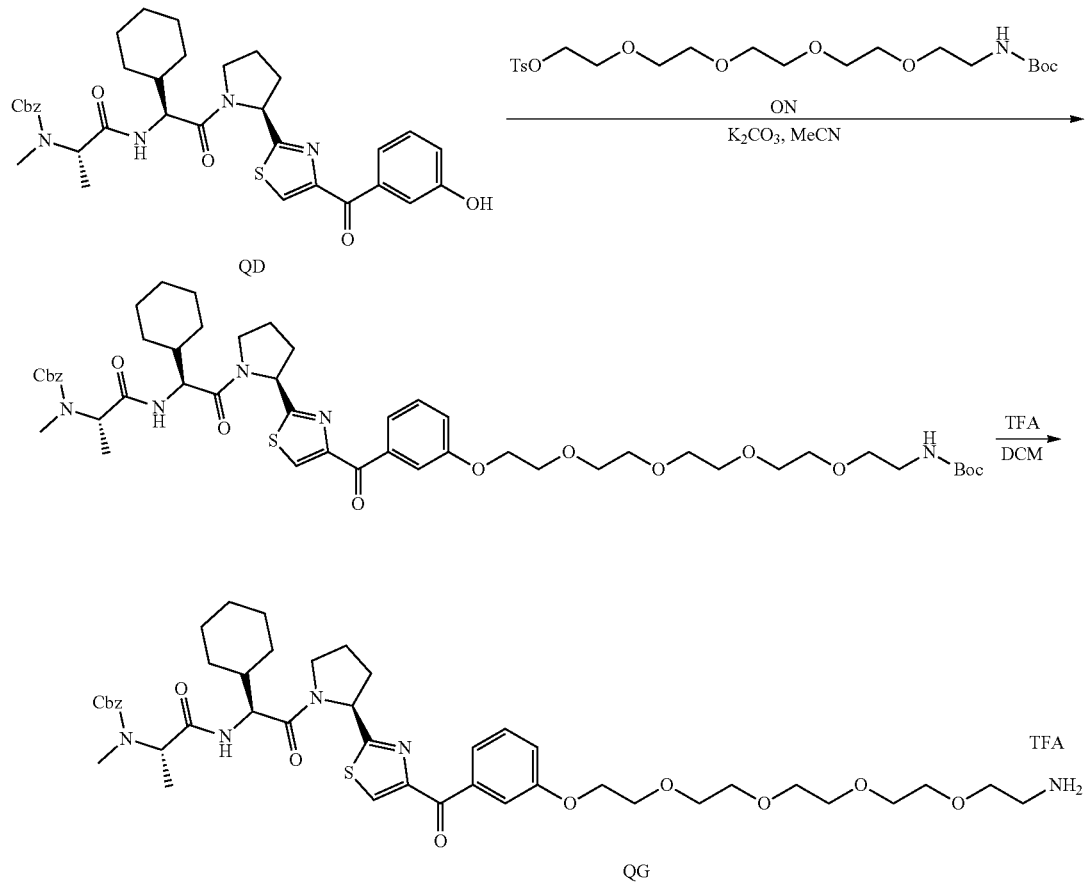

Step 1—benzyl ((S)-1-(((S)-1-cyclohexyl-2-((S)-2-(4-(3-((2,2-dimethyl-4-oxo-3,8,11,14,17-pentaoxa-5-azanonadecan-19-yl)oxy)benzoyl)thiazol-2-yl)pyrrolidin-1-yl)-2-oxoethyl)amino)-1-oxopropan-2-yl)(methyl)carbamate To a solution of benzyl ((S)-1-(((S)-1-cyclohexyl-2-((S)-2-(4-(3-hydroxybenzoyl)thiazol-2-yl)pyrrolidin-1-yl)-2-oxoethyl)amino)-1-oxopropan-2-yl)(methyl)carbamate (1.32 g, 2.09 mmol, Intermediate QD) in $CH_3CN$ (100 mL) was added 2,2-dimethyl-4-oxo-3,8,11,14,17-pentaoxa-5-azanonadecan-19-yl 4-methylbenzenesulfonate (1.23 g, 2.51 mmol, Intermediate ON) and $K_2CO_3$ (346.4 mg, 2.51 mmol) at rt. Then the reaction mixture was stirred at 80° C. for 12 h. The reaction mixture was then concentrated under reduced pressure. The residue was purified via column chromatography on silica gel (EtOAc/petroleum ether) to give the title compound (1.68 g, 85% yield) as a pale yellow oil. LC/MS (ESI, m/z): [M+1]$^+$-953.7.

Step 2—benzyl ((S)-1-(((S)-2-((S)-2-(4-(3-((14-amino-3,6,9,12-tetraoxatetradecyl)oxy)benzoyl)thiazol-2-yl)pyrrolidin-1-yl)-1-cyclohexyl-2-oxoethyl)amino)-1-oxopropan-2-yl)(methyl)carbamate 2,2,2-trifluoroacetate To a solution of benzyl ((S)-1-(((S)-1-cyclohexyl-2-((S)-2-(4-(3-((2,2-dimethyl-4-oxo-3,8,11,14,17-pentaoxa-5-azanonadecan-19-yl)oxy)benzoyl)thiazol-2-yl)pyrrolidin-1-yl)-2-oxoethyl)amino)-1-oxopropan-2-yl)(methyl)carbamate (1.4 g, 1.47 mmol) in DCM (30 mL) was added TFA (30 mL) and the reaction mixture was stirred at rt for 3 h. Then the reaction mixture was concentrated under reduced pressure and the residue was purified via reverse phase column chromatography (ACN/$H_2O$) to give the title compound (1.2 g, 84% yield) as a colorless oil. $^1$H NMR (400 MHz, $CD_3OD$) δ: 8.33 (s, 1H), 7.90-7.68 (m, 3H), 7.50-7.40 (m, 1H), 7.40-7.19 (m, 5H), 5.67-5.30 (m, 1H), 5.13 (s, 2H), 4.73-4.67 (m, 1H), 4.50-4.40 (m, 1H), 4.29-4.12 (m, 2H), 4.05-3.79 (m, 4H), 3.78-3.52 (m, 14H), 3.10-3.07 (m, 2H), 2.94 (s, 3H), 2.57-1.95 (m, 4H), 1.85-1.46 (m, 6H), 1.40-1.29 (m, 3H), 1.27-0.86 (m, 5H). LC/MS (ESI, m/z): [M+1]$^+$=852.7.

Benzyl N-[(1S)-2-[[(1S)-2-[(2S)-2-[4-[3-[2-[2-(2-aminoethoxy)ethoxy]ethoxy]benzoyl]thiazol-2-yl]pyrrolidin-1-yl]-1-cyclohexyl-2-oxo-ethyl]amino]-1-methyl-2-oxo-ethyl]-N-methyl-carbamate (Intermediate QH)

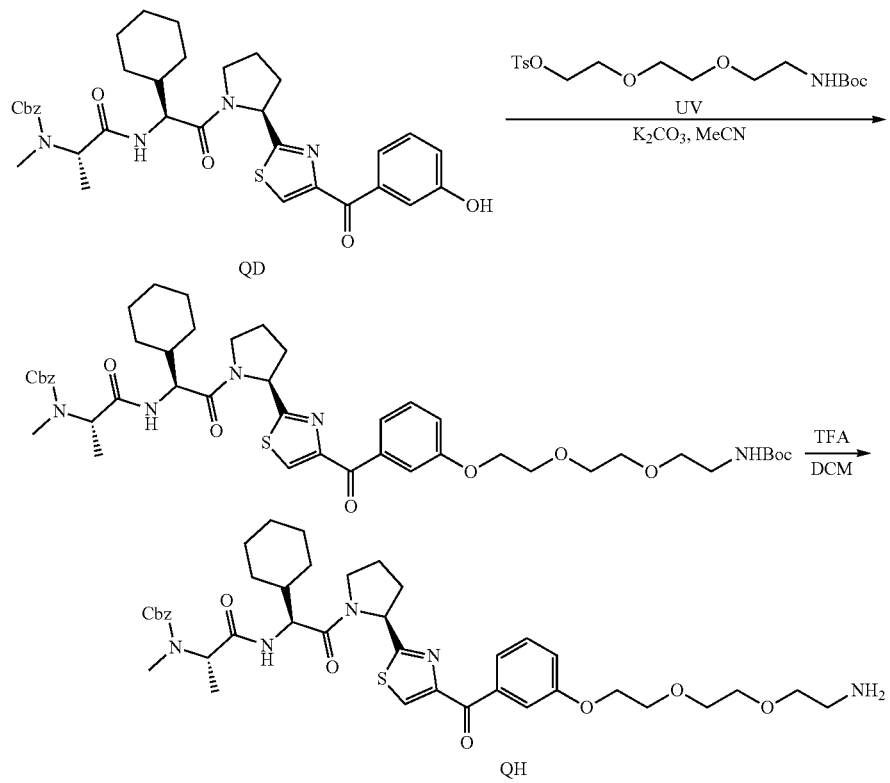

Step 1—benzyl ((S)-1-(((S)-1-cyclohexyl-2-((S)-2-(4-(3-((2,2-dimethyl-4-oxo-3,8,11-trioxa-5-azatridecan-13-yl)oxy)benzoyl)thiazol-2-yl)pyrrolidin-1-yl)-2-oxoethyl)amino)-1-oxopropan-2-yl)(methyl)carbamate To a solution of benzyl ((S)-1-(((S)-1-cyclohexyl-2-((S)-2-(4-(3-hydroxybenzoyl)thiazol-2-yl)pyrrolidin-1-yl)-2-oxoethyl)amino)-1-oxopropan-2-yl)(methyl)carbamate (1.30 g, 2.05 mmol, Intermediate QD) in CH$_3$CN (25 mL) was added 2,2-dimethyl-4-oxo-3,8,11-trioxa-5-azatridecan-13-yl 4-methylbenzenesulfonate (1.20 g, 2.46 mmol, Intermediate UV) and K$_2$CO$_3$ (368 mg, 2.67 mmol) at rt. The reaction mixture was stirred at 80° C. for 12 hours. The reaction mixture was concentrated under reduced pressure. The residue was purified via column chromatography on silica gel (EtOAc/Petroleum ether=1/1-EA) to give the title compound (1.30 g, 68% yield) as a white solid. $^1$H NMR (400 MHz, CD$_3$OD) δ 8.32 (s, 1H), 7.73-7.71 (m, 2H), 7.43 (t, J=8.0 Hz, 1H), 7.39-7.29 (m, 5H), 7.26-7.20 (m, 1H), 5.47-5.46 (m, 1H), 5.13 (s, 2H), 4.69 (br s, 1H), 4.52-4.41 (m, 1H), 4.22-4.18 (m, 2H), 4.00-3.93 (m, 1H), 3.89-3.87 (m, 3H), 3.73-68 (m, 2H), 3.66-3.61 (m, 2H), 3.52-3.49 (m, 2H), 3.23-3.19 (m, 2H), 2.94 (s, 3H), 2.36-2.20 (m, 3H), 2.18-2.06 (m, 1H), 1.76-1.50 (m, 6H), 1.41 (s, 9H), 1.36 (d, J=7.2 Hz, 3H), 1.17-0.96 (m, 5H). LC/MS (ESI, m/z): [M+1]$^+$=864.6.

Step 2—benzyl ((S)-1-(((S)-2-((S)-2-(4-(3-(2-(2-(2-aminoethoxy)ethoxy)ethoxy)benzoyl)thiazol-2-yl)pyrrolidin-1-yl)-1-cyclohexyl-2-oxoethyl)amino)-1-oxopropan-2-yl)(methyl)carbamate To a solution of benzyl ((S)-1-(((S)-1-cyclohexyl-2-((S)-2-(4-(3-((2,2-dimethyl-4-oxo-3,8,11-trioxa-5-azatridecan-13-yl)oxy)benzoyl)thiazol-2-yl)pyrrolidin-1-yl)-2-oxoethyl)amino)-1-oxopropan-2-yl)(methyl)carbamate (1.2 g, 1.39 mmol) in DCM (5 mL) was added TFA (5 mL) and the reaction mixture was stirred at rt for 3 h. The reaction mixture was concentrated under reduced pressure to give the title compound (1.2 g, 100% yield, TFA salt) as a light yellow oil. $^1$H NMR (400 MHz, CD$_3$OD) δ 8.33 (s, 1H), 7.79-7.71 (m, 2H), 7.45 (t, J=8.0 Hz, 1H), 7.38-7.28 (m, 5H), 7.25-7.22 (m, 1H), 5.47-5.46 (m, 1H), 5.13 (s, 2H), 4.73-4.64 (m, 1H), 4.52-4.40 (m, 1H), 4.24-4.21 (m, 2H), 4.01-3.94 (m, 1H), 3.90-3.88 (m, 3H), 3.77-3.74 (m, 2H), 3.72-3.69 (m, 4H), 3.11 (t, J=4.8 Hz, 2H), 2.94 (s, 3H), 2.39-2.11 (m, 4H), 1.75-1.54 (m, 6H), 1.36 (t, J=8.0 Hz, 3H), 1.16-0.99 (m, 5H). LC/MS (ESI, m/z): [M+1]+=764.6.

[3-Methyl-5-[3-[3-(methylamino)propoxy]propyl]-2-oxo-benzimidazol-1-yl]piperidine-2,6-dione (Intermediate QI)

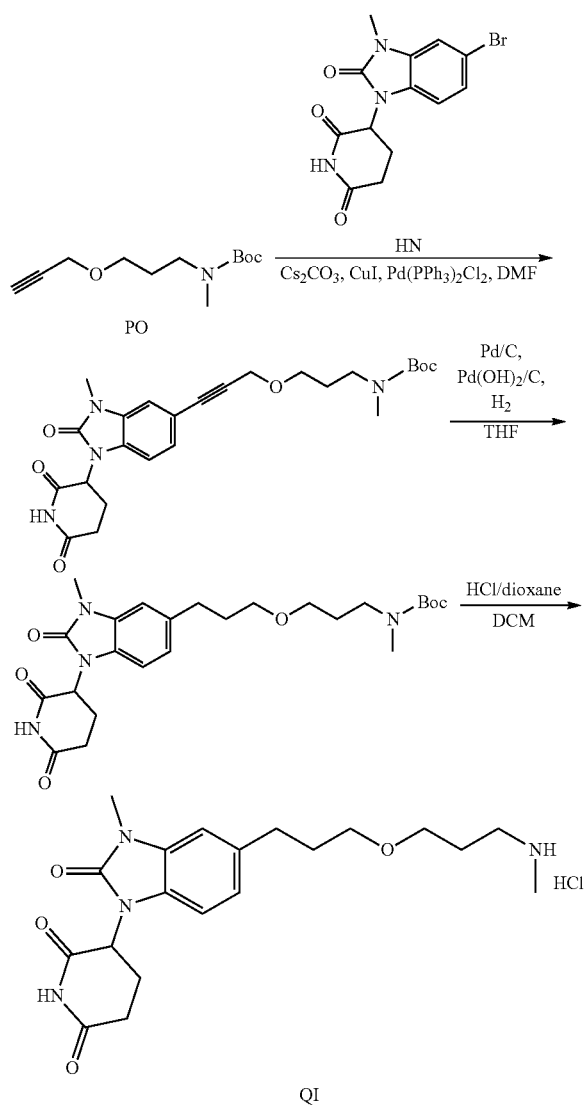

Step 1—Tert-butyl N-[3-[3-[1-(2,6-dioxo-3-piperidyl)-3-methyl-2-oxo-benzimidazol-5-yl]prop-2-ynoxy]propyl]-N-methyl-carbamate To a solution of tert-butyl N-methyl-N-(3-prop-2-ynoxypropyl)carbamate (604 mg, 2.66 mmol, Intermediate PO) and 3-(5-bromo-3-methyl-2-oxo-benzimidazol-1-yl)piperidine-2,6-dione (450 mg, 1.33 mmol, Intermediate HN) in DMF (10 mL) was added Pd(PPh$_3$)$_2$Cl$_2$ (186 mg, 266 umol), CuI (50.6 mg, 266 umol) and Cs$_2$CO$_3$ (2.17 g, 6.65 mmol). The reaction mixture was stirred at 80° C. for 2 hr under N2. On completion, the mixture was filtered, and the filtrate was concentrated in vacuo to give a residue. The residue was purified by reverse phase (0.1% FA condition) to give the title compound (550 mg, 85% yield) as a yellow solid. $^1$H NMR (400 MHz, DMSO-d$_6$) δ 11.13 (s, 1H), 7.65-7.52 (m, 3H), 5.39 (dd, J=5.6, 12.8 Hz, 1H), 4.45-4.18 (m, 2H), 3.62-3.44 (m, 2H), 3.22 (t, J=7.2 Hz, 2H), 2.92-2.83 (m, 1H), 2.80-2.59 (m, 7H), 2.08-2.00 (m, 1H), 1.77-1.70 (m, 2H), 1.38 (s, 9H); LC-MS (ESI$^+$) m/z 507.1 (M+Na)$^+$.

Step 2—Tert-butyl N-[3-[3-[1-(2,6-dioxo-3-piperidyl)-3-methyl-2-oxo-benzimidazol-5-yl]propoxy]propyl]-N-methyl-carbamate To a solution of tert-butyl N-[3-[3-[1-(2,6-dioxo-3-piperidyl)-3-methyl-2-oxo-benzimidazol-5-yl]prop-2-ynoxy]propyl]-N-methyl-carbamate (530 mg, 1.09 mmol) in THF (10 mL) was added Pd(OH)$_2$/C (200 mg, 10 wt %) and Pd/C (200 mg, 10 wt %). The reaction mixture was stirred at 25° C. under H$_2$ (15 Psi) for 12 hrs. On completion, the residue was filtered and the filtrate was concentrated in vacuo to give a residue. The residue was purified by prep-HPLC (column: Phenomenex Synergi C18 150*25*10 um; mobile phase: [water (0.225% FA)-ACN]; B %: 38%-65%, 9 min) to give the title compound (300 mg, 56% yield) as yellow oil. $^1$H NMR (400 MHz, DMSO-d$_6$) δ 11.08 (s, 1H), 7.05-6.98 (m, 2H), 6.87 (d, J=8.0 Hz, 1H), 5.33 (dd, J=5.6, 12.8 Hz, 1H), 3.36-3.33 (m, 4H), 3.32 (s, 3H), 3.22 (t, J=7.2 Hz, 2H), 2.95-2.85 (m, 1H), 2.77 (s, 3H), 2.73-2.60 (m, 4H), 2.03-1.98 (m, 1H), 1.86-1.78 (m, 2H), 1.73-1.69 (m, 2H), 1.38 (s, 9H); LC-MS (ESI$^+$) m/z 389.2 (M+H−100)$^+$.

Step 3—3-[3-Methyl-5-[3-[3-(methylamino)propoxy]propyl]-2-oxo-benzimidazol-1-yl]piperidine-2,6-dione To a solution of tert-butyl N-[3-[3-[1-(2,6-dioxo-3-piperidyl)-3-methyl-2-oxo-benzimidazol-5-yl]propoxy]propyl]-N-methyl-carbamate (50.0 mg, 102 umol) in DCM (3 mL) was added HCl/dioxane (4 M, 2 mL). The reaction mixture was stirred at 25° C. for 2 hrs. On completion, the mixture was concentrated in vacuo to give the title compound (40.0 mg, 92% yield, HCl) as a white solid. $^1$H NMR (400 MHz, DMSO-d$_6$) δ 11.09 (s, 1H), 7.06-6.97 (m, 2H), 6.90-6.84 (m, 1H), 5.34 (dd, J=5.2, 12.8 Hz, 1H), 3.56 (s, 2H), 3.43 (t, J=6.0 Hz, 2H), 3.32 (s, 3H), 2.96-2.86 (m, 3H), 2.72-2.58 (m, 4H), 2.56-2.52 (m, 3H), 2.02-1.97 (m, 1H), 1.90-1.78 (m, 4H); LC-MS (ESI$^+$) m/z 389.2 (M+H)$^+$.

Tert-butyl (2-methyl-4-(prop-2-yn-1-yloxy)butan-2-yl)carbamate (Intermediate QJ)

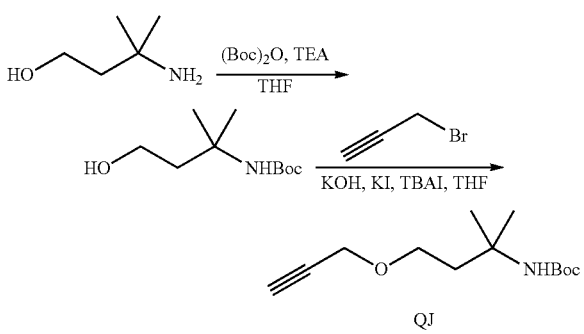

Step 1—Tert-butyl (4-hydroxy-2-methylbutan-2-yl)carbamate

To a solution of 3-amino-3-methylbutan-1-ol (4.0 g, 38.8 mmol, CAS #42514-50-1) and TEA (3.92 g, 38.8 mmol, 5.4 mL) in THF (50 mL) added dropwise (Boc)$_2$O (9.31 g, 9.8 mL, 42.6 mmol) at 20° C. and the mixture was stirred at 20° C. for 16 hours. Once completion, the reaction mixture was quenched by water (15 mL), and then extracted with EA (3×30 mL). The combined organic layers were dried over Na$_2$SO$_4$, filtered and concentrated in vacuo to give a residue. The residue was purified by column chromatography (SiO$_2$, PE/EA=10:1) to give the title compound (1.50 g, 19% yield) as a light yellow oil. $^1$H NMR (400 MHz, CDCl$_3$) δ 4.90 (s, 1H), 3.76 (q, 2H), 2.04 (s, 1H), 1.88 (t, J=6.4 Hz, 2H), 1.43 (s, 9H), 1.32 (s, 6H).

Step 2—Tert-butyl (2-methyl-4-(prop-2-yn-1-yloxy) butan-2-yl)carbamate

To a solution of tert-butyl (4-hydroxy-2-methylbutan-2-yl)carbamate (1.40 g, 6.89 mmol) and 3-bromoprop-1-yne (1.23 g, 10.3 mmol) in THF (20 mL) was added KI (171 mg, 1.03 mmol), TBAI (152 mg, 0.41 mmol) and KOH (463 mg, 8.26 mmol) at 30° C. Then the mixture was stirred at 30° C. for 16 hours. On completion, the reaction mixture was filtered and the filtrate was concentrated in vacuo to give the residue. The residue was purified by column chromatography (SiO$_2$, PE/EA=30:1) to give the title compound (1.40 g, 84% yield) as a light yellow liquid. $^1$H NMR (400 MHz, CDCl$_3$) δ 4.84 (s, 1H), 4.12 (d, J=2.4 Hz, 2H), 3.62 (t, J=6.4 Hz, 2H), 2.42 (t, J=2.4 Hz, 1H), 1.91 (t, J=6.4 Hz, 2H), 1.42 (s, 9H), 1.31 (s, 6H).

3-[7-[3-(3-Amino-3-methyl-butoxy)propyl]-2-oxo-1,3-benzoxazol-3-yl]piperidine-2,6-dione (Intermediate QK)

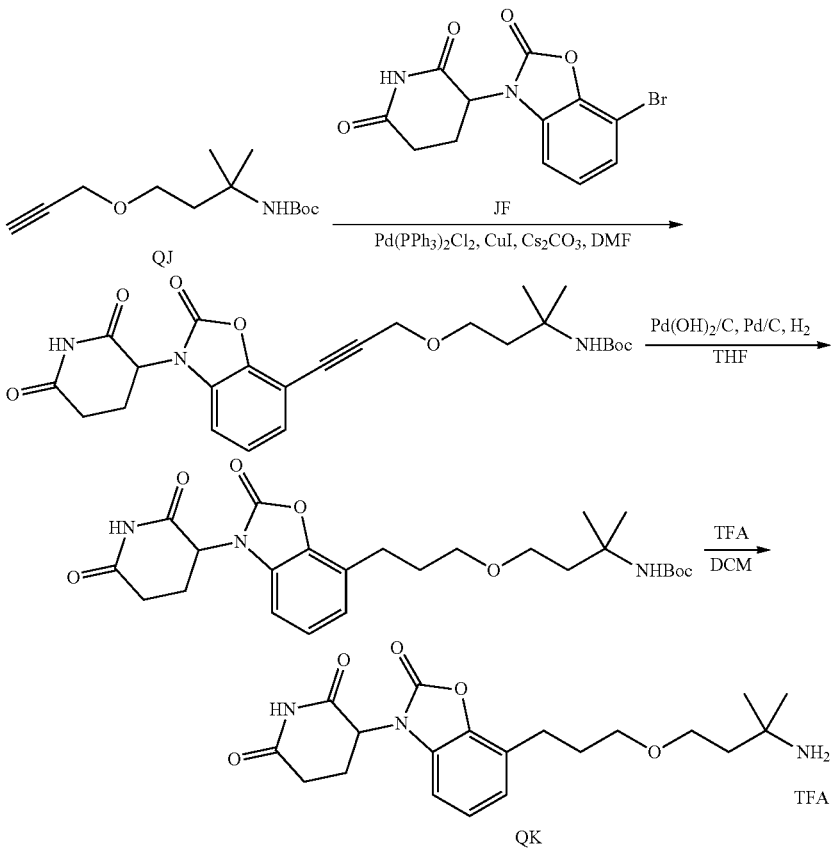

Step 1—Tert-butyl N-[3-[3-[3-(2,6-dioxo-3-piperidyl)-2-oxo-1,3-benzoxazol-7-yl]prop-2-ynoxy]-1,1-dimethyl-propyl]carbamate To a solution of 3-(7-bromo-2-oxo-1,3-benzoxazol-3-yl)piperidine-2,6-dione (320 mg, 0.98 mmol, Intermediate JF) and tert-butyl (2-methyl-4-(prop-2-yn-1-yloxy)butan-2-yl)carbamate (593 mg, 2.46 mmol, Intermediate QJ) in DMF (20 mL) was added Cs$_2$CO$_3$ (1.28 g, 3.94 mmol), CuI (37.49 mg, 0.2 mmol), Pd(PPh$_3$)$_2$Cl$_2$ (138 mg, 0.2 mmol) and 4 Å molecular sieves (80 mg) at 25° C. under N$_2$. Then the reaction mixture was heated to 80° C. and stirred for 2 hours. On completion, the reaction mixture was quenched by addition of water (10 m)L, and then extracted with EA (30 mL, 3×10 mL). The combined organic layers and dried over Na$_2$SO$_4$, filtered and concentrated in vacuo to give a residue. The residue was purified by column chromatography (SiO$_2$, Petroleum ether/Ethyl acetate=2/1 to 1/1) to give the title compound (330 mg, 69% yield) as a white solid. $^1$H NMR (400 MHz, CDCl$_3$) δ 8.18 (s, 1H), 7.25-7.19 (m, 1H), 7.13 (t, J=8.0 Hz, 1H), 6.82-6.75 (m, 1H), 5.08-5.01 (m, 1H), 4.91 (s, 1H), 4.41 (s, 2H), 3.73 (t, J=6.4 Hz, 2H), 3.04-2.95

(m, 1H), 2.91-2.66 (m, 2H), 2.40-2.27 (m, 1H), 1.97 (t, J=6.2 Hz, 2H), 1.41 (s, 9H), 1.35 (s, 6H); LC-MS (ESI+) m/z 386.0 (M+H−100)+.

Step 2—Tert-butyl N-[3-[3-[3-(2,6-dioxo-3-piperidyl)-2-oxo-1,3-benzoxazol-7-yl]propoxy]-1,1-dimethyl-propyl]carbamate To a mixture of tert-butyl N-[3-[3-[3-(2,6-dioxo-3-piperidyl)-2-oxo-1,3-benzoxazol-7-yl]prop-2-ynoxy]-1,1-dimethyl-propyl]carbamate (130 mg, 0.27 mmol) in THF (15 mL) was added Pd/C (10 wt %) and Pd(OH)₂/C (10 wt %) under N₂. The suspension was degassed under vacuum and purged with H₂ gas several times. The mixture was stirred at 25° C. for 16 hours under H₂ (15 psi). On completion, the reaction mixture was filtered and concentrated in vacuo to give the title compound (127 mg, 85% yield) as a white solid. LC-MS (ESI+) m/z 390.2 (M+H−100)+.

Step 3—3-[7-[3-(3-Amino-3-methyl-butoxy)propyl]-2-oxo-1,3-benzoxazol-3-yl]piperidine-2,6-dione To a mixture of tert-butyl N-[3-[3-[3-(2,6-dioxo-3-piperidyl)-2-oxo-1,3-benzoxazol-7-yl]propoxy]-1,1-dimethyl-propyl]carbamate (127 mg, 0.26 mmol) in DCM (5 mL) was added TFA (591 mg, 0.52 mmol, 0.38 mL) at 25° C. The mixture was stirred at 25° C. for 60 min. On completion, the reaction mixture was concentrated in vacuo to give the title compound (126 mg, 96% yield, TFA) as light yellow oil. ¹H NMR (400 MHz, CDCl₃) δ 9.05 (s, 1H), 7.13 (t, J=16 Hz, 1H), 7.03-6.98 (m, 1H), 6.78 (d, J=8.0 Hz, 1H), 5.14-5.09 (m, 1H), 3.67 (t, J=5.6 Hz, 2H), 3.56 (t, J=5.6 Hz, 2H), 2.99-2.71 (m, 6H), 2.37-2.33 (m, 1H), 2.04-1.96 (m, 2H), 1.84 (t, J=5.6 Hz, 2H), 1.40 (s, 6H); LC-MS (ESI+) m/z 390.1 (M+H)+.

2-[2-[2-(Tert-butoxycarbonylamino)ethoxy]ethoxy]ethyl (4-nitrophenyl) carbonate (Intermediate QL)

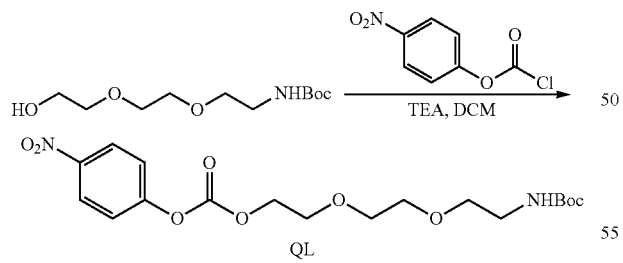

To a solution of (4-nitrophenyl) carbonochloridate (711 mg, 3.53 mmol, CAS #7693-46-1) and tert-butyl N-[2-[2-(2-hydroxyethoxy)ethoxy]ethyl]carbamate (800 mg, 3.21 mmol, CAS #139135-92-7) in DCM (20 mL) was added TEA (812 mg, 8.02 mmol) at 0° C. The reaction mixture was stirred at this temperature for 1 hr. On completion, the mixture was quenched with water (10 mL), and concentrated in vacuo to give the title compound (1.2 g, 90% yield) as a yellow oil. LC-MS (ESI+) m/z 437.2 (M+Na)+.

3-[5-(Aminomethyl)-1-oxo-isoindolin-2-yl]piperidine-2,6-dione (Intermediate QM)

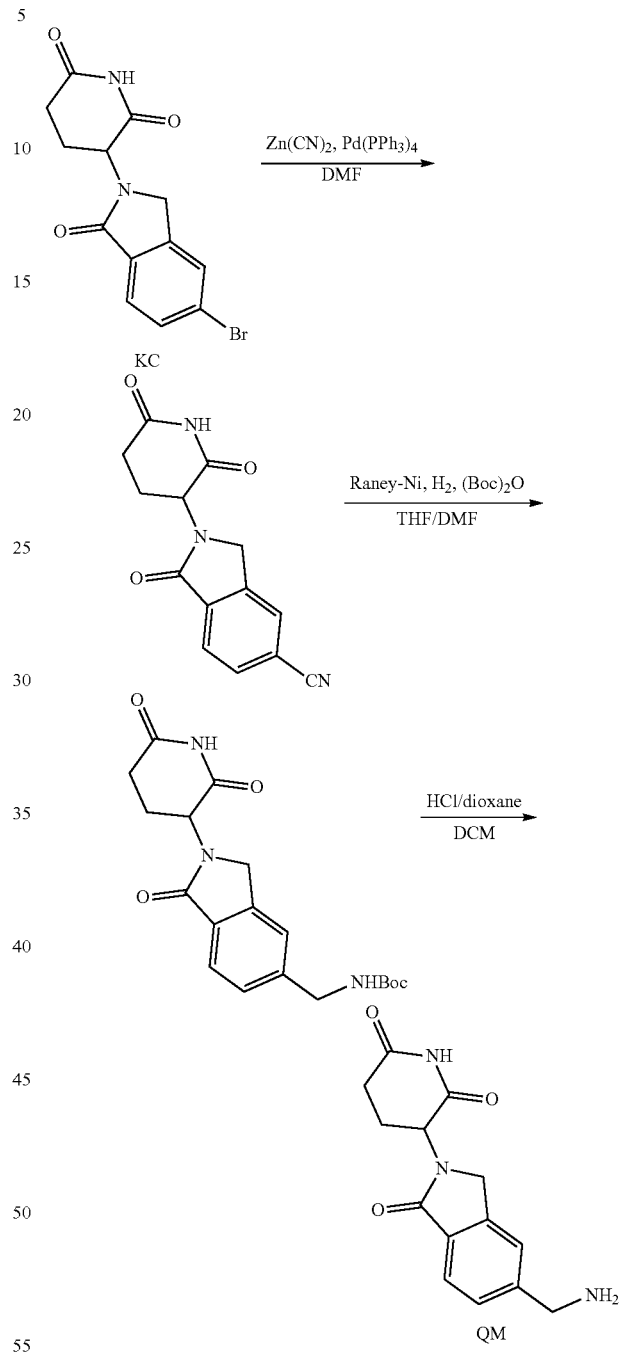

Step 1—2-(2,6-Dioxo-3-piperidyl)-1-oxo-isoindoline-5-carbonitrile

To a solution of 3-(5-bromo-1-oxo-isoindolin-2-yl) piperidine-2,6-dione (1.70 g, 5.26 mmol, Intermediate KC) and Zn(CN)₂ (370 mg, 3.16 mmol) in DMF (30.0 mL) was added Pd(PPh₃)₄ (607 mg, 526 umol). The mixture was stirred at 100° C. for 3 hour under N₂. On completion, the mixture was diluted with H₂O (50 mL), then mixture was filtered and the solid was dried in vacuo. The solid was triturated with PE:EA=5:1 (50 mL), filtered and the solid was dried in vacuo to give the title compound (1.10 g, 77% yield) as purple solid. $^1$H NMR (400 MHz, DMSO-$d_6$) δ 11.02 (s, 1H), 8.16 (s, 1H), 8.01-7.90 (m, 2H), 5.20-5.09 (m, 1H), 4.59-4.37 (m, 2H), 2.99-2.87 (m, 1H), 2.70-2.57 (m, 1H), 2.46-2.37 (m, 1H), 2.11-1.98 (m, 1H).

Step 2—Tert-butyl N-[[2-(2,6-dioxo-3-piperidyl)-1-oxo-isoindolin-5-yl]methyl]carbamate To a solution of 2-(2,6-dioxo-3-piperidyl)-1-oxo-isoindoline-5-carbonitrile (1.50 g, 5.57 mmol) in THF (15.0 mL) and DMF (15.0 mL) was added (Boc)$_2$O (1.34 g, 6.13 mmol) and Raney-Ni (750 mg, 8.75 mmol). The mixture was stirred at 30° C. for 40 hour under H$_2$ (50 psi). On completion, the mixture was concentrated in vacuo. The mixture was purified by silica gel column (PE:EA=1:2) to give the title compound (900 mg, 43% yield) as white solid. $^1$H NMR (400 MHz, DMSO-$d_6$) δ 10.99 (s, 1H), 7.68 (d, J=7.6 Hz, 1H), 7.52 (t, J=6.0 Hz, 1H), 7.45 (s, 1H), 7.38 (d, J=7.6 Hz, 1H), 5.17-5.03 (m, 1H), 4.48-4.27 (m, 2H), 4.24 (d, J=6.0 Hz, 2H), 2.98-2.85 (m, 1H), 2.65-2.55 (m, 1H), 2.44-2.31 (m, 1H), 2.06-1.96 (m, 1H), 1.40 (s, 9H).

Step 3—3-[5-(Aminomethyl)-1-oxo-isoindolin-2-yl]piperidine-2,6-dione

To a solution of tert-butyl N-[[2-(2,6-dioxo-3-piperidyl)-1-oxo-isoindolin-5-yl]methyl]carbamate (200 mg, 535 umol) in DCM (5.00 mL) was added HCl/dioxane (4.00 M, 5.00 mL). The mixture was stirred at rt for 0.5 hour. On completion, the mixture was concentrated in vacuo to give the title compound (160 mg, 90% yield, HCl) as white solid. LC-MS (ESI$^+$) m/z 274.1 (M+H)$^+$.

2-[2-(2-Aminoethoxy)ethoxy]ethyl N-[[2-(2,6-dioxo-3-piperidyl)-1-oxo-isoindolin-5-yl]methyl]carbamate (Intermediate QN)

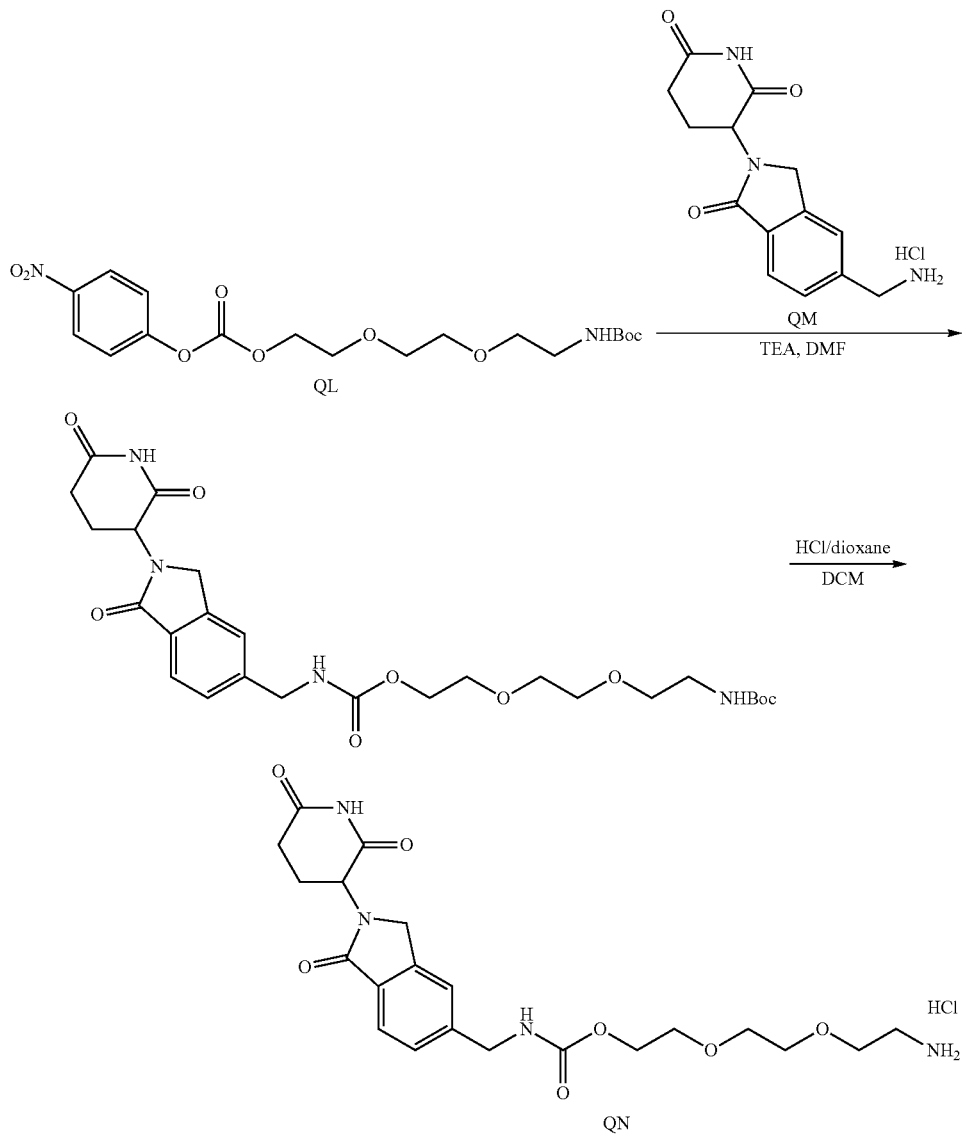

Step 1—2-[2-[2-(Tert-butoxycarbonylamino)ethoxy]ethoxy]ethyl N-[[2-(2,6-dioxo-3-piperidyl)-1-oxo-isoindolin-5-yl]methyl]carbamate To a solution of 3-[5-(aminomethyl)-1-oxo-isoindolin-2-yl]piperidine-2,6-dione (100 mg, 323 umol, HCl, Intermediate QM) and 2-[2-[2-(tert-butoxycarbonylamino)ethoxy]ethoxy]ethyl (4-nitrophenyl) carbonate (268 mg, 646 umol, Intermediate QL) in DMF (3 mL) was added TEA (163 mg, 1.61 mmol) under $N_2$ atmosphere. The reaction mixture was stirred at 25° C. for 1 h. On completion, the mixture was concentrated in vacuo. The residue was purified by reverse phase (0.1% FA condition) to give the title compound (110 mg, 62% yield) as a white solid. $^1$H NMR (400 MHz, DMSO-$d_6$) δ 11.00 (s, 1H), 7.93-7.86 (m, 1H), 7.70-7.65 (m, 1H), 7.47 (s, 1H), 7.42-7.36 (m, 1H), 6.82-6.72 (m, 1H), 5.14-5.06 (m, 1H), 4.47-4.40 (m, 1H), 4.34-4.25 (m, 3H), 4.12-4.03 (m, 2H), 3.60-3.55 (m, 2H), 3.50-3.47 (m, 4H), 3.38-3.36 (m, 2H), 3.05 (q, J=5.6 Hz, 2H), 2.97-2.85 (m, 1H), 2.59-2.53 (m, 2H), 2.04-1.93 (m, 1H), 1.36 (s, 9H); LC-MS (ESI$^+$) m/z 549.3 (M+H)$^+$.

Step 2—2-[2-(2-Aminoethoxy)ethoxy]ethyl N-[[2-(2,6-dioxo-3-piperidyl)-1-oxo-isoindolin-5-yl]methyl]carbamate To a solution of 2-[2-[2-(tert-butoxycarbonylamino)ethoxy]ethoxy]ethyl N-[[2-(2,6-dioxo-3-piperidyl)-1-oxo-isoindolin-5-yl]methyl]carbamate (150 mg, 273 umol) in DCM (3 mL) was added HCl/dioxane (4 M, 5 mL). The reaction mixture was stirred at 25° C. for 2 hrs. On completion, the mixture was concentrated in vacuo to give the title compound (130 mg, 98% yield, HCl) as a white solid. LC-MS (ESI$^+$) m/z 449.2 (M+H)$^+$.

2-(Tert-butoxycarbonylamino)ethyl (4-nitrophenyl) carbonate (Intermediate QO)

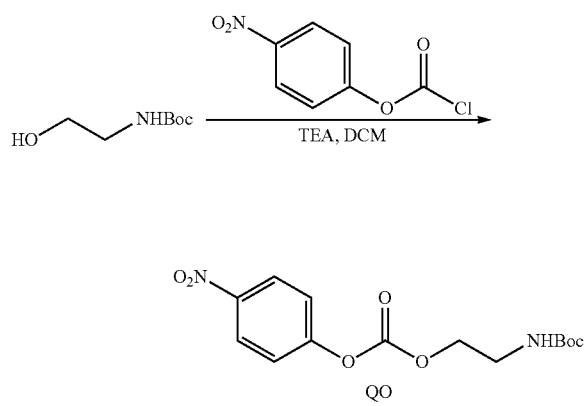

To a solution of tert-butyl N-(2-hydroxyethyl)carbamate (500 mg, 3.10 mmol), (4-nitrophenyl)carbonochloridate (687 mg, 3.41 mmol) in DCM (20.0 mL) was added TEA (784 mg, 7.75 mmol). The mixture was stirred at 0° C. for 1 hour. On completion, the mixture was concentrated in vacuo to give the title compound (1.00 g, 90% yield) as yellow solid. LC-MS (ESI$^+$) m/z 349.1 (M+Na)$^+$.

2-Aminoethyl N-[[2-(2,6-dioxo-3-piperidyl)-1-oxo-isoindolin-5-yl]methyl]carbamate (Intermediate QP)

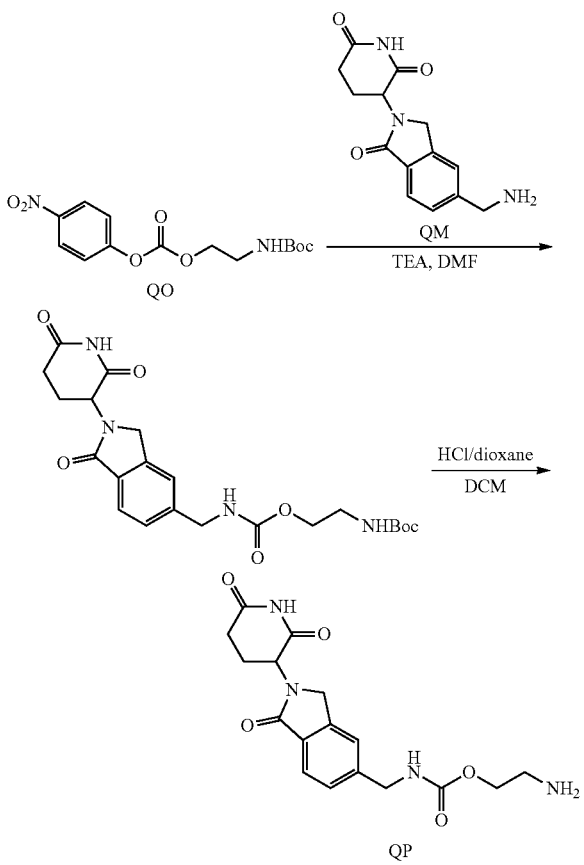

Step 1—2-(Tert-butoxycarbonylamino)ethyl N-[[2-(2,6-dioxo-3-piperidyl)-1-oxo-isoindolin-5-yl]methyl]carbamate To a solution of 3-[5-(aminomethyl)-1-oxo-isoindolin-2-yl]piperidine-2,6-dione (200 mg, 645 umol, HCl, Intermediate QM) and 2-(tertbutoxycarbonylamino)ethyl (4-nitrophenyl) carbonate (421 mg, 1.29 mmol, Intermediate QO) in DMF (10.0 mL) was added TEA (326 mg, 3.23 mmol). The reaction mixture was stirred at 20° C. for 2 hrs. On completion, the mixture was concentrated in vacuo. The mixture was purified by prep-HPLC (column: Phenomenex Synergi C18 150*25*10 um; mobile phase: [water (0.225% FA)-ACN]; B %: 26%-56%, 10 min) to give the title compound (160 mg, 53% yield) as white solid. $^1$H NMR (400 MHz, DMSO-$d_6$) δ 11.00 (s, 1H), 7.82 (t, J=6.0 Hz, 1H), 7.68 (d, J=8.0 Hz, 1H), 7.49 (s, 1H), 7.41 (d, J=8.0 Hz, 1H), 6.94-6.87 (m, 1H), 5.16-5.07 (m, 1H), 4.49-4.31 (m, 2H), 4.30 (d, J=6.4 Hz, 2H), 3.99-3.90 (m, 2H), 3.18-3.09 (m, 2H), 2.97-2.89 (m, 1H), 2.64-2.58 (m, 1H), 2.44-2.35 (m, 1H), 2.05-1.95 (m, 1H), 1.38 (s, 9H).

Step 2—2-Aminoethyl N-[[2-(2,6-dioxo-3-piperidyl)-1-oxo-isoindolin-5-yl]methyl]carbamate To a solution of 2-(tert-butoxycarbonylamino)ethyl N-[[2-(2,6-dioxo-3-piperidyl)-1-oxo-isoindolin-5-yl]

methyl]carbamate (140 mg, 304 umol) in DCM (2.00 mL) was added HCl/dioxane (4.00 M, 14.0 mL). The mixture was stirred at 25° C. for 0.5 hr. On completion, the mixture was concentrated in vacuo to give the title compound (120 mg, 99% yield) as yellow solid. LC-MS (ESI+) m/z 361.2 (M+H)+.

3-[7-[3-(2-Aminoethoxy)propyl]-2-oxo-1,3-benzoxazol-3-yl]piperidine-2,6-dione (Intermediate QR)

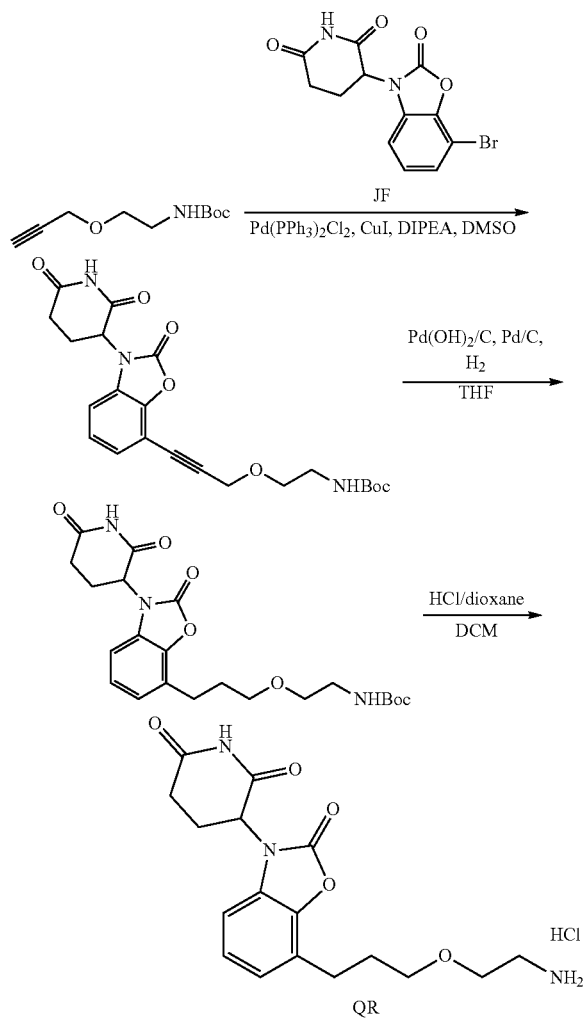

Step 1—Tert-butyl N-[2-[3-[3-(2,6-dioxo-3-piperidyl)-2-oxo-1,3-benzoxazol-7-yl]prop-2-ynoxy]ethyl]carbamate To a solution of tert-butyl N-(2-prop-2-ynoxyethyl)carbamate (689 mg, 3.46 mmol, synthesized via Step 1 on Intermediate CP) and 3-(7-bromo-2-oxo-1,3-benzoxazol-3-yl)piperidine-2,6-dione (450 mg, 1.38 mmol, Intermediate JF) in DMF (10 mL) was added Pd(PPh3)2Cl2 (194 mg, 276 umol), CuI (52.7 mg, 277 umol) and Cs2CO3 (2.25 g, 6.92 mmol). The reaction was stirred at 80° C. for 3 hrs under N2. On completion, the reaction mixture was filtered and the filtrate was concentrated in vacuo to give a residue. The residue was purified by reverse phase (0.1% FA condition) to give the title compound (510 mg, 83% yield) as a brown solid. 1H NMR (400 MHz, DMSO-d6) δ 11.23 (s, 1H), 7.31 (dd, J=7.2 Hz, 1H), 7.26-7.19 (m, 2H), 6.92-6.77 (m, 1H), 5.46-5.32 (m, 1H), 4.45 (s, 2H), 3.52 (t, J=6.0 Hz, 3H), 3.12 (q, J=5.6 Hz, 2H), 2.93-2.82 (m, 1H), 2.66-2.57 (m, 1H), 2.22-2.13 (m, 1H), 1.36 (s, 9H); LC-MS (ESI+) m/z 344.1 (M+H −100)+.

Step 2—Tert-butyl N-[2-[3-[3-(2,6-dioxo-3-piperidyl)-2-oxo-1,3-benzoxazol-7-yl]propoxy]ethyl]carbamate To a solution of tert-butyl N-[2-[3-[3-(2,6-dioxo-3-piperidyl)-2-oxo-1,3-benzoxazol-7-yl]prop-2-ynoxy]ethyl]carbamate (340 mg, 766 umol) in THF (20 mL) was added Pd(OH)2/C (150 mg, 10 wt %) and Pd/C (150 mg, 50 wt %). The reaction mixture was stirred at 25° C. for 2 hrs under H2 (15 psi). On completion, the reaction mixture was filtered through celite and concentrated in vacuo to give the title compound (350 mg, 90% yield) as gray solid. LC-MS (ESI+) m/z 348.1 (M+H−100)+.

Step 3—3-[7-[3-(2-Aminoethoxy)propyl]-2-oxo-1,3-benzoxazol-3-yl]piperidine-2,6-dione To a solution of tert-butyl N-[2-[3-[3-(2,6-dioxo-3-piperidyl)-2-oxo-1,3-benzoxazol-7-yl]propoxy]ethyl]carbamate (70.0 mg, 156 umol) in DCM (2 mL) was added HCl/dioxane (4 M, 1 mL). The reaction mixture was stirred at 25° C. for 2 hrs. On completion, the reaction mixture was filtered and the filter cake was concentrated in vacuo to give the title compound (60.0 mg, 99% yield, HCl) as a white solid. LC-MS (ESI+) m/z 348.1 (M+H)+.

4-[[2-[2-[Tert-butoxycarbonyl(2,2,2-trifluoroethyl)amino]-4-pyridyl]oxazole-4-carbonyl]amino]-1-(4-formylphenyl)pyrazole-3-carboxylic acid (Intermediate QU)

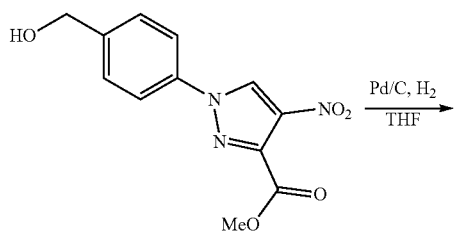

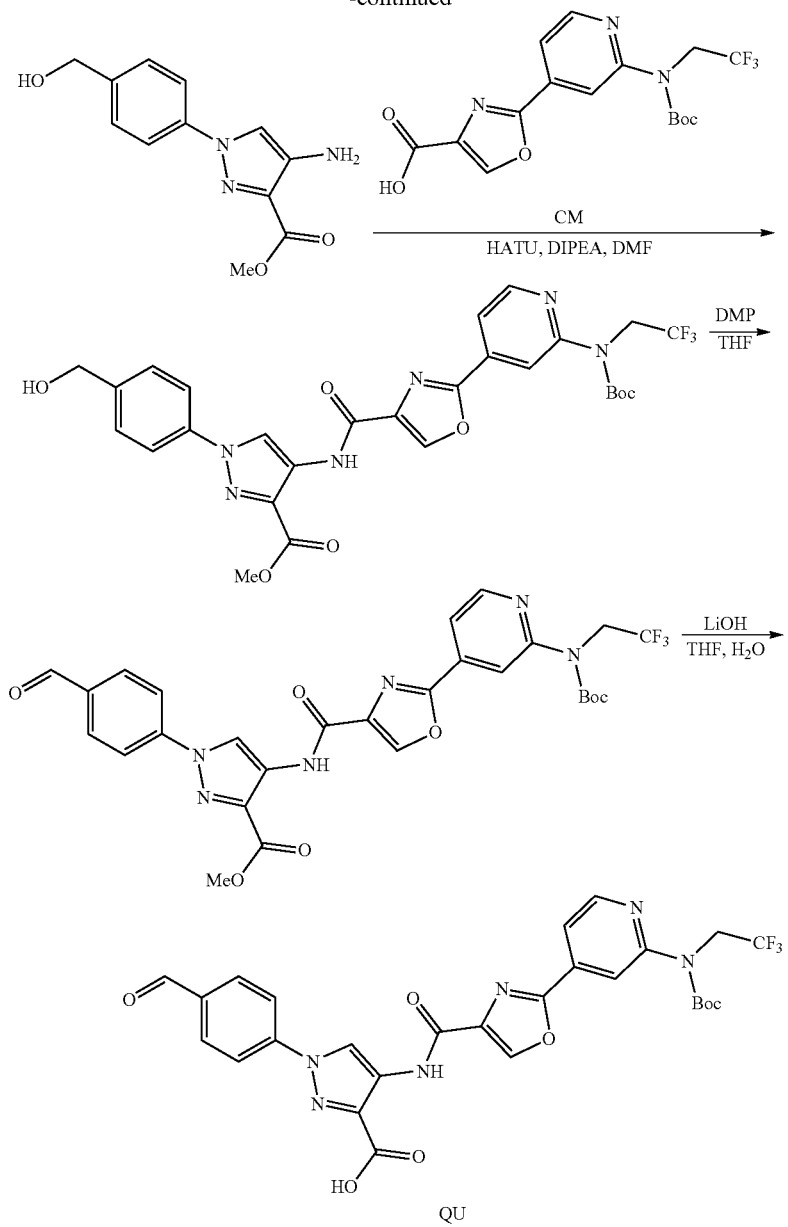

Step 1—Methyl 4-amino-1-[4-(hydroxymethyl)phenyl]pyrazole-3-carboxylate

To a solution of methyl 1-[4-(hydroxymethyl)phenyl]-4-nitro-pyrazole-3-carboxylate (15.0 g, 54.1 mmol, synthesized via Step 1 of Intermediate GB) in MeOH (200 mL) was added Pd/C (5.00 g, 10 wt %). The reaction mixture was stirred at 25° C. for 2 hours under $H_2$ (15 Psi). On completion, the reaction mixture was filtered and the filtrate was concentrated in vacuo to give the title compound (13.0 g, 97% yield) as a light yellow solid. $^1$H NMR (400 MHz, DMSO-$d_6$) δ 7.82 (s, 1H), 7.74 (d, J=8.4 Hz, 2H), 7.42 (d, J=8.4 Hz, 2H), 5.27 (t, J=5.6 Hz, 1H), 4.89 (s, 2H), 4.53 (d, J=5.6 Hz, 2H), 3.83 (s, 3H).

Step 2—Methyl 4-[[2-[2-[tert-butoxycarbonyl(2,2,2-trifluoroethyl)amino]-4-pyridyl]oxazole-4-carbonyl]amino]-1-[4-(hydroxymethyl)phenyl]pyrazole-3-carboxylate To a solution of methyl 4-amino-1-[4-(hydroxymethyl)phenyl]pyrazole-3-carboxylate (4.10 g, 16.5 mmol) and 2-[2-[tert-butoxycarbonyl(2,2,2-trifluoroethyl)amino]-4-pyridyl]oxazole-4-carboxylic acid (5.14 g, 13.2 mmol, Intermediate CM) in DMF (100 mL) was added DIPEA (4.29 g, 33.1 mmol) and HATU (6.31 g, 16.5 mmol). The reaction mixture was stirred at 25° C. for 0.5 hour. On completion, the reaction was quenched with water (500 mL) and the reaction mixture was filtered. The filter cake was washed with water (2×100 mL), MeOH (2×10 mL) and then dried in vacuo to give the title compound (10.0 g, 100% yield) as a yellow solid. LC-MS (ESI$^+$) m/z 639.0 (M+Na)$^+$.

Step 3—Methyl 4-[[2-[2-[tert-butoxycarbonyl(2,2,2-trifluoroethyl)amino]-4-pyridyl]oxazole-4-carbonyl]amino]-1-(4-formylphenyl)pyrazole-3-carboxylate To a solution of methyl 4-[[2-[2-[tert-butoxycarbonyl(2,2,2-trifluoroethyl)amino]-4-pyridyl]oxazole-4-carbonyl]amino]-1-[4-(hydroxymethyl)phenyl]pyrazole-3-carboxylate (7.00 g, 11.3 mmol) in THF (250 mL) was added DMP (5.78 g, 13.6 mmol). The reaction mixture was stirred at 0° C. for 1 hour. On completion, the reaction mixture was diluted with DCM (300 mL) and filtered. The filtrate was concentrated in vacuo to give the title compound (7.00 g, 100% yield) as a yellow solid. $^1$H NMR (400 MHz, DMSO-d$_6$) δ 10.39 (s, 1H), 10.05 (s, 1H), 9.15 (d, J=3.6 Hz, 1H), 8.66 (d, J=5.2 Hz, 1H), 8.33 (s, 1H), 8.19 (d, J=8.8 Hz, 1H), 8.11-8.03 (m, 2H), 8.03-7.95 (m, 1H), 7.78-7.75 (m, 1H), 4.91 (q, J=8.8 Hz, 2H), 1.54 (s, 9H), 1.35 (s, 3H); LC-MS (ESI$^+$) m/z 637.0 (M+Na)$^+$.

Step 4—4-[[2-[2-[Tert-butoxycarbonyl(2,2,2-trifluoroethyl)amino]-4-pyridyl]oxazole-4-carbonyl]amino]-1-(4-formylphenyl)pyrazole-3-carboxylic acid To a solution of methyl 4-[[2-[2-[tert-butoxycarbonyl(2,2,2-trifluoroethyl)amino]-4-pyridyl]oxazole-4-carbonyl]amino]-1-(4-formylphenyl)pyrazole-3-carboxylate (4.00 g, 6.51 mmol) in THF (10 mL) and H$_2$O (2 mL) was added LiOH (467 mg, 19.5 mmol). The reaction mixture was stirred at 25° C. for 3 hours. On completion, the reaction mixture was acidified with HCl (0.5 N) to pH=6 and filtered to give the title compound (3.00 g, 76% yield) as a white solid. LC-MS (ESI$^+$) m/z 601.0 (M+H)$^+$.

Tert-butyl N-[4-[4-[[1-(4-formylphenyl)-3-(4-methylpiperazine-1-carbonyl)pyrazol-4-yl]carbamoyl]oxazol-2-yl]-2-pyridyl]-N-(2,2,2-trifluoroethyl)carbamate (Intermediate QV)

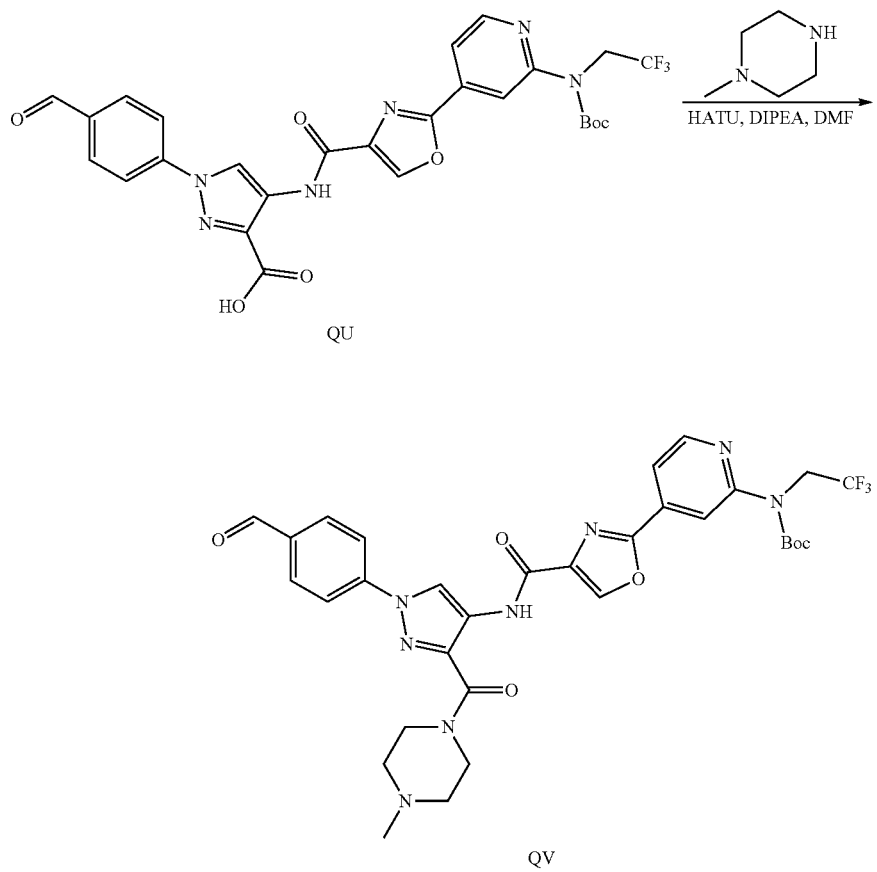

To a solution of 4-[[2-[2-[tert-butoxycarbonyl(2,2,2-trifluoroethyl)amino]-4-pyridyl]oxazole-4-carbonyl]amino]-1-(4-formylphenyl)pyrazole-3-carboxylic acid (1.50 g, 2.50 mmol, Intermediate QU) and 1-methylpiperazine (200 mg, 2.00 mmol, CAS #109-01-3) in DMF (50 mL) was added DIPEA (968 mg, 7.49 mmol) and HATU (949 mg, 2.50 mmol). The reaction mixture was stirred at 25° C. for 1 hour. On completion, the reaction mixture was quenched with water (100 mL), filtered and washed with water (2×30 mL) to give the filter cake. The filter cake was then purified by reverse phase (0.1% FA) to give the title compound (1.00 g, 58% yield) as a white solid. $^1$H NMR (400 MHz, DMSO-d$_6$) δ 11.17-11.06 (m, 1H), 10.05 (s, 1H), 9.15 (s, 1H), 9.11 (s, 1H), 8.66 (d, J=5.2 Hz, 1H), 8.16 (s, 3H), 8.12-8.05 (m, 2H), 7.78-7.74 (m, 1H), 4.91 (q, J=8.8 Hz, 2H), 4.39-4.32 (m, 2H), 3.85-3.70 (m, 2H), 2.48-2.40 (m, 4H), 2.24 (s, 3H), 1.54 (s, 9H); LC-MS (ESI$^+$) m/z 683.1 (M+H)$^+$.

4-[4-[[2-[2-[Tert-butoxycarbonyl(2,2,2-trifluoro-ethyl)amino]-4-pyridyl]oxazole-4-carbonyl]amino]-3-(4-methylpiperazine-1-carbonyl)pyrazol-1-yl]benzoic acid (Intermediate QW)

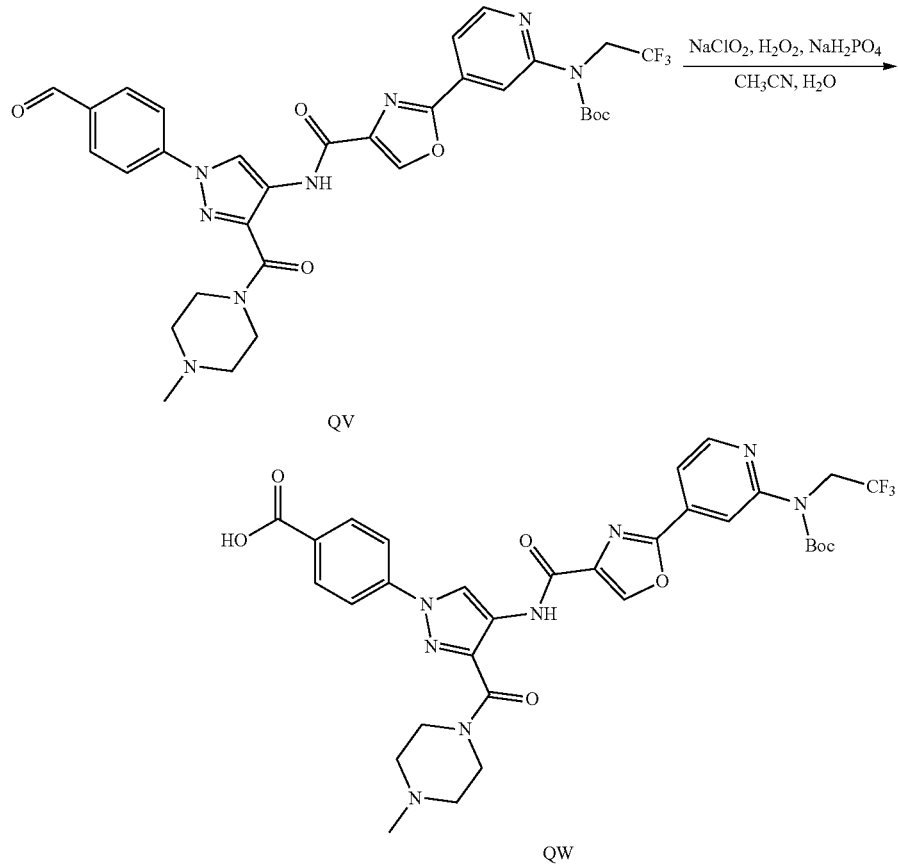

To a solution of tert-butyl N-[4-[4-[[1-(4-formylphenyl)-3-(4-methylpiperazine-1-carbonyl)pyrazol-4-yl]carbamoyl]oxazol-2-yl]-2-pyridyl]-N-(2,2,2-trifluoroethyl)carbamate (100 mg, 146 umol, Intermediate QV) and NaH$_2$PO$_4$ (87.8 mg, 732 umol) in ACN (1 mL) was added H$_2$O$_2$ (33.2 mg, 292 umol, 30% sol) at 0° C. Then sodium chlorite (92.7 mg, 1.03 mmol) in H$_2$O (1 mL) was added dropwise at 0° C. The reaction mixture was stirred at 25° C. for 1 hour. On completion, the reaction mixture was acidified by HCl (0.5 N) to pH=6 and filtered. The filter cake was collected and dried in vacuo to give the title compound (100 mg, 97% yield) as a white solid. LC-MS (ESI$^+$) m/z 699.1 (M+H)$^+$.

Tert-butyl N-[4-[4-[[3-[2-(dimethylamino)ethylcarbamoyl]-1-(4-formylphenyl)pyrazol-4-yl]carbamoyl]oxazol-2-yl]-2-pyridyl]-N-(2,2,2-trifluoroethyl)carbamate (Intermediate QX)

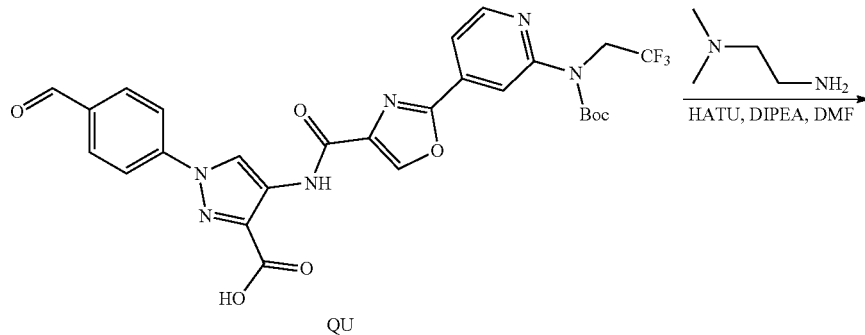

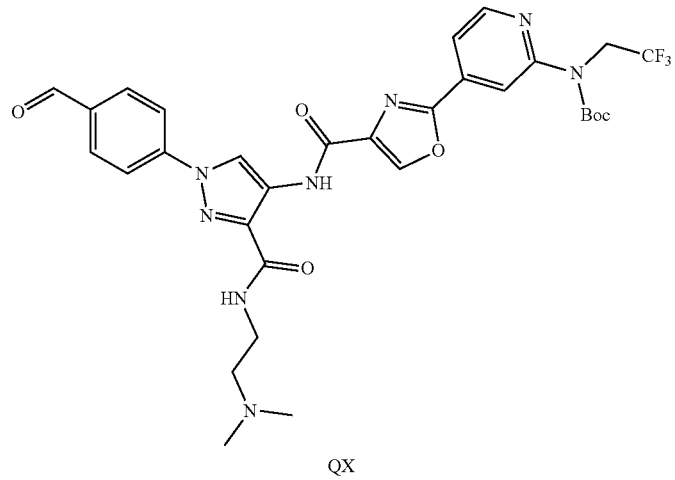

QX

To a solution of 4-[[2-[2-[tert-butoxycarbonyl(2,2,2-trifluoroethyl)amino]-4-pyridyl]oxazole-4-carbonyl]amino]-1-(4-formylphenyl)pyrazole-3-carboxylic acid (800 mg, 1.33 mmol, Intermediate QU) and N',N'-dimethylethane-1,2-diamine (117 mg, 1.33 mmol, 145 uL, CAS #108-00-9) in DMF (10 mL) was added HATU (607 mg, 1.60 mmol) and DIPEA (860 mg, 6.66 mmol, 1.16 mL). The reaction mixture was stirred at 25° C. for 2 hrs. On completion, the reaction mixture was concentrated in vacuo to give a residue. The residue was purified by reverse phase (0.1% FA condition) to give the title compound (230 mg, 25% yield) as a white solid. $^1$H NMR (400 MHz, DMSO-$d_6$) δ 10.99 (s, 1H), 10.05 (s, 1H), 9.12 (s, 1H), 8.70 (t, J=5.2, 1H), 8.66 (d, J=5.2 Hz, 1H), 8.29 (s, 1H), 8.26-8.08 (m, 5H), 7.80-7.74 (m, 1H), 4.90 (q, J=8.8 Hz, 2H), 3.54-3.48 (m, 2H), 2.71-2.63 (m, 2H), 2.36 (s, 6H), 1.54 (s, 9H); LC-MS (ESI$^+$) m/z 671.3 (M+H)$^+$.

4-[4-[[2-[2-Tert-butoxycarbonyl(2,2,2-trifluoroethyl)amino]-4-pyridyl]oxazole-4-carbonyl]amino]-3-[2-(dimethylamino)ethylcarbamoyl pyrazol-1-yl]benzoic acid (Intermediate QY)

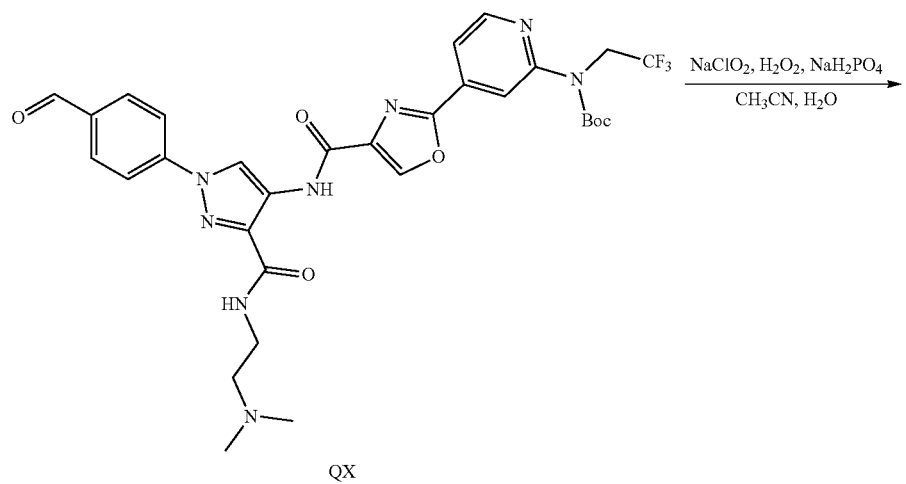

QX

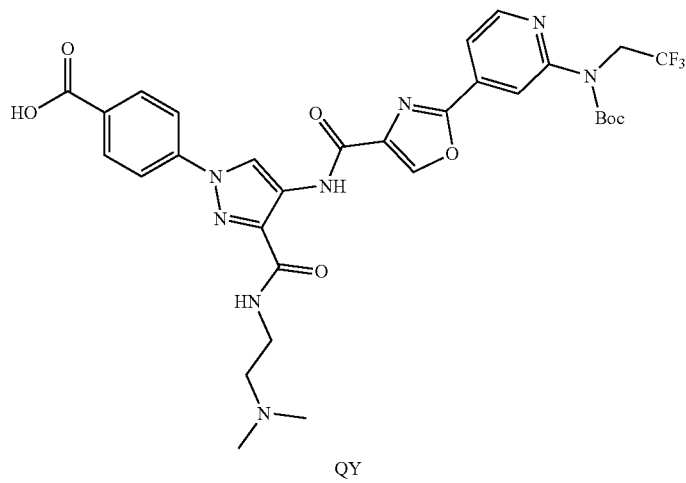

QY

To a solution of tert-butyl N-[4-[4-[[3-[2-(dimethylamino)ethylcarbamoyl]-1-(4-formylphenyl) pyrazol-4-yl]carbamoyl]oxazol-2-yl]-2-pyridyl]-N-(2,2,2-trifluoroethyl)carbamate (150 mg, 223 umol, Intermediate QX) in CH$_3$CN (10 mL) was added a solution of NaH$_2$PO$_4$ (134 mg, 1.12 mmol and NaClO$_2$ (141 mg, 1.57 mmol) in H$_2$O (10 mL) at 0° C., then H$_2$O$_2$ (126 mg, 1.12 mmol, 107 uL, 30% sol) was added to the mixture. The reaction mixture was stirred at 25° C. for 3 hrs. On completion, the mixture was diluted with 0.5N HCl (10 mL) and extracted with EA (2×40 mL). The organic phase was concentrated in vacuo to give the title compound (120 mg, 78% yield) as a white solid. LC-MS (ESI$^+$) m/z 687.2 (M+H)$^+$.

12-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-12-oxododecanoic acid (Intermediate QZ)

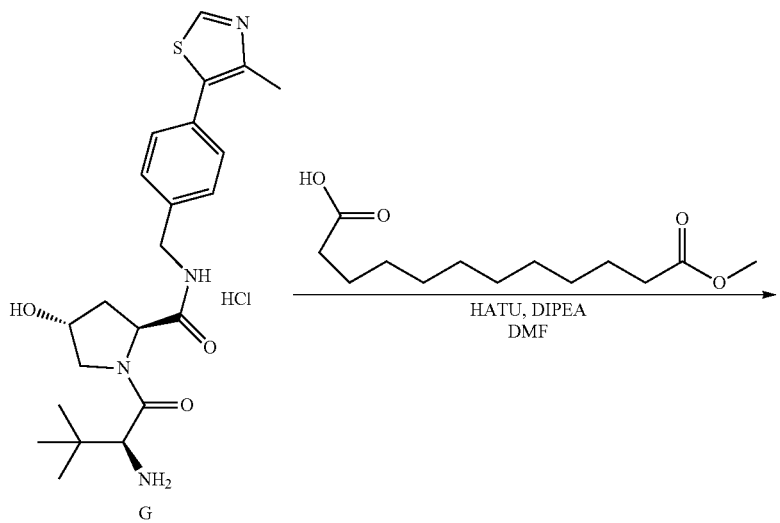

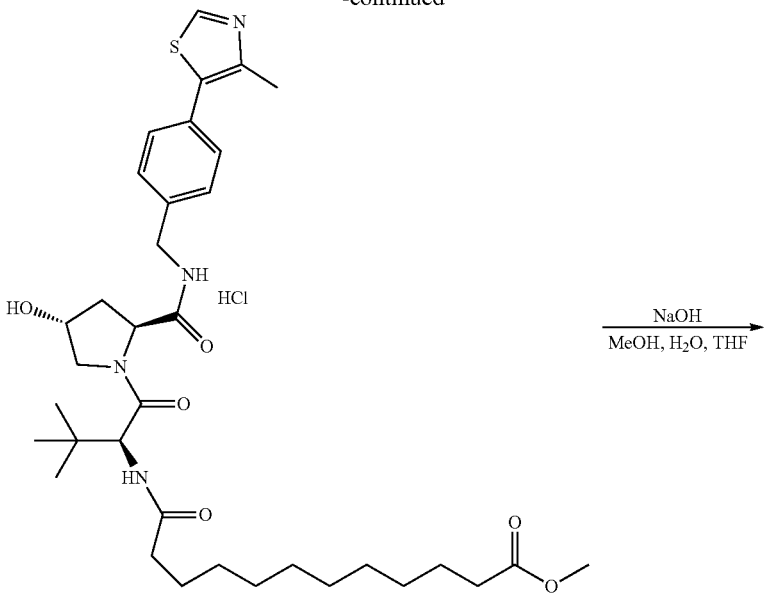

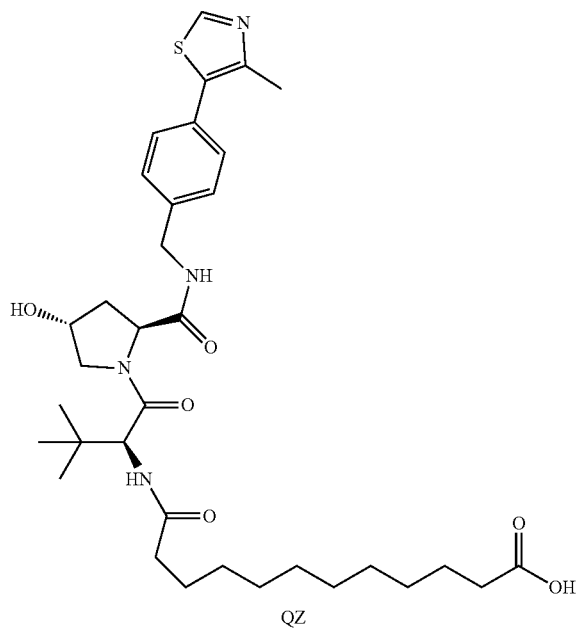

QZ

Step 1—methyl 12-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-12-oxododecanoate To a solution of 12-methoxy-12-oxododecanoic acid (0.623 g, 2.55 mmol, CAS #3909-40-0) in DMF (20 mL) was added HATU (0.989 g, 2.55 mmol) and DIPEA (0.599 g, 4.64 mmol). The mixture was stirred for 10 min at rt. Then to the mixture was added a solution of (2S,4R)-1-((S)-2-amino-3,3-dimethylbutanoyl)-4-hydroxy-N-(4-(4-methylthiazol-5-yl)benzyl)pyrrolidine-2-carboxamide HCl salt (1 g, 2.32 mmol, Intermediate G) in DMF (10 mL) and the mixture was stirred for 3 h at rt. On completion, $H_2O$ (50 mL) was added to the mixture, then extracted with EA (100 mL). The organic layer was washed with brine, dried over $Na_2SO_4$, filtered, concentrated and purified by column (PE/EA=1/1 to EA) to give the title compound (700 mg, 50% yield) as a white solid. $^1$H NMR (400 MHz, $CDCl_3$) δ 8.80 (s, 1H), 7.39-7.31 (m, 5H), 6.10 (d, J=8.8 Hz, 1H), 4.73 (t, J=8.0 Hz, 1H), 4.61-4.48 (m, 3H), 4.34 (dd, J=1.6 Hz, J=14.8 Hz, 1H), 4.15-4.10 (m, 1H), 3.66 (s, 3H), 3.60 (dd, J=3.6 Hz, J=11.6 Hz, 1H), 2.56-2.53 (m, 4H), 2.29 (t, J=7.6

Hz, 2H), 2.21-2.10 (m, 3H), 1.62-1.57 (m, 4H), 1.28-1.26 (m, 11H), 0.93 (s, 9H). LC/MS (ESI, m/z): [M+1]$^+$=657.6.

Step 2—12-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-12-oxododecanoic acid To a solution of methyl 12-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-12-oxododecanoate (2.4 g, 3.65 mmol) in MeOH (30 mL), H$_2$O (30 mL) and THF (30 mL) was added NaOH (877 mg, 21.9 mmol). The mixture was stirred for 3 h at rt. To the mixture was added then added 0.06 N HCl until the pH=6.5, then the mixture was extracted with EA (100 mL). The organic layer was washed with brine (50 mL), dried over Na$_2$SO$_4$, filtered, concentrated to the title compound (2.3 g, 100% yield) as a white solid. $^1$H NMR (400 MHz, CDCl$_3$) δ 8.89 (s, 1H), 7.39 (s, 4H), 7.20 (t, J=7.2 Hz, 1H), 7.12 (d, J=9.2 Hz, 1H), 4.74-4.64 (m, 3H), 4.58 (s, 1H), 4.33 (dd, J=4.8 Hz, J=14.8 Hz, 1H), 4.21 (d, J=11.2 Hz, 1H), 3.69 (dd, J=4.0 Hz, J=12 Hz, 1H), 2.58 (s, 3H), 2.51-2.45 (m, 1H), 2.35 (t, J=6.0 Hz, 2H), 2.26-2.19 (m, 3H), 1.69-1.56 (m, 4H), 1.34-1.28 (m, 12H), 0.95 (s, 9H). LC/MS (ESI, m/z): [M+1]$^+$=643.3.

2-[2-[2-[2-[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethoxy]ethoxy]ethoxy]acetic acid (Intermediate RA)

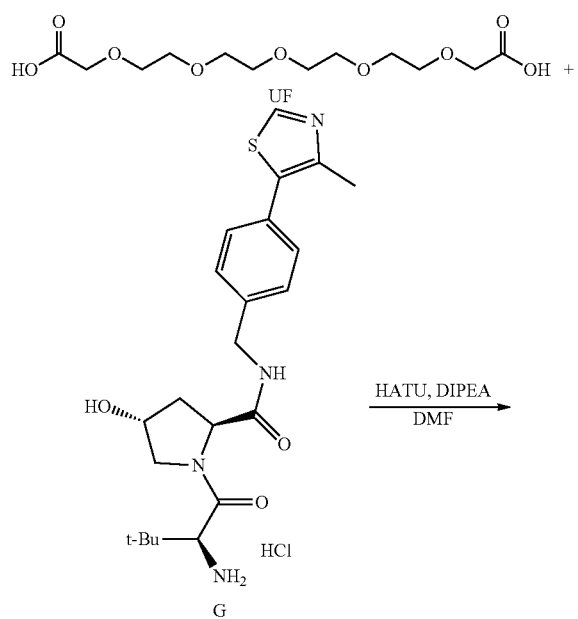

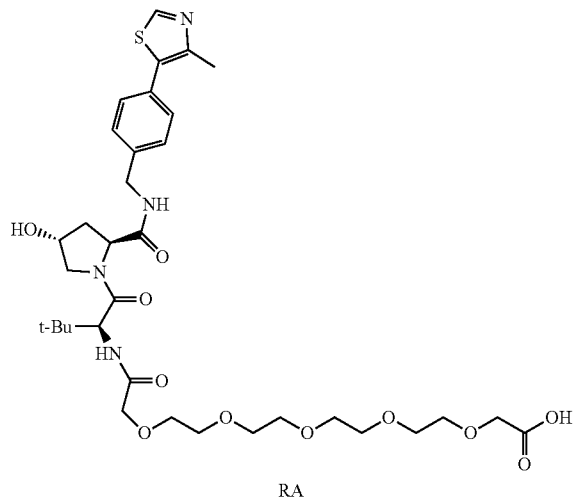

Step 1—(S)-9-((2S,4R)-4-hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosanoic acid To a mixture of 3,6,9,12,15-pentaoxaheptadecanedioic acid (1.04 g, 3.36 mmol, Intermediate UF), DIPEA (289 mg, 2.24 mmol) in DMF (15 mL) was added HATU (511 mg, 1.344 mmol). Then the (2S,4R)-1-((S)-2-amino-3,3-dimethylbutanoyl)-4-hydroxy-N-(4-(4-methylthiazol-5-yl)benzyl)pyrrolidine-2-carboxamide hydrochloride (500 mg, 1.12 mmol, Intermediate G) in DMF (5 mL) was added dropwise to the solution. After the addition, the mixture was stirred at rt for 30 min. Then the mixture was poured into water, acidified to pH<6 by addition of 1M HCl, then extracted with EtOAc (3×30 mL). The combined organic layers was washed with brine (50 mL×2), dried over anhydrous Na$_2$SO$_4$, filtered and concentrated in vacuo. The residue was purified by prep HPLC to give the title compound (311 mg, 38% yield) as a white solid. $^1$H NMR (400 MHz, METHANOL-d$_4$) δ 9.05 (s, 1H), 7.53-7.44 (m, 4H), 4.74-4.70 (m, 1H), 4.61-4.51 (m, 3H), 4.38 (d, J=15.51 Hz, 1H), 4.13 (s, 2H), 4.08 (d, J=3.13 Hz, 2H), 3.90-3.81 (m, 2H), 3.73-3.63 (m, 16H), 2.52 (s, 3H), 2.27-2.08 (m, 2H), 1.07 (s, 9H); LC/MS (ESI, m/z): [M+1]$^+$=723.2.

2-[2-[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethoxy]acetic acid Intermediate RB)

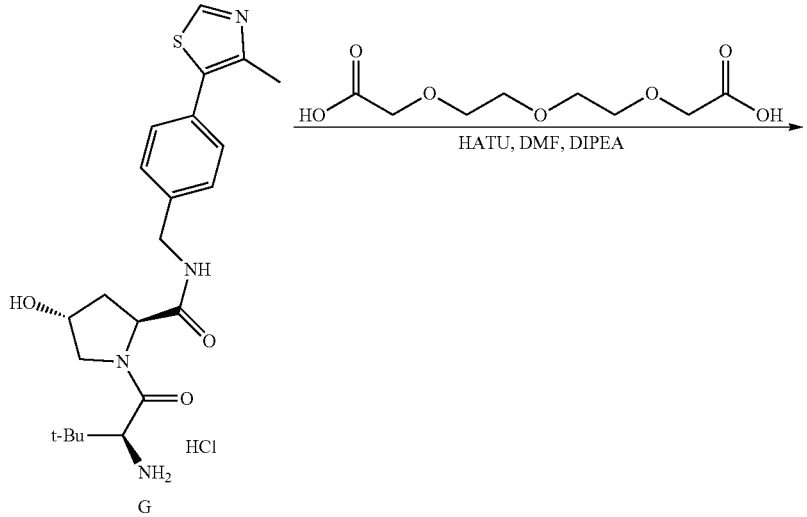

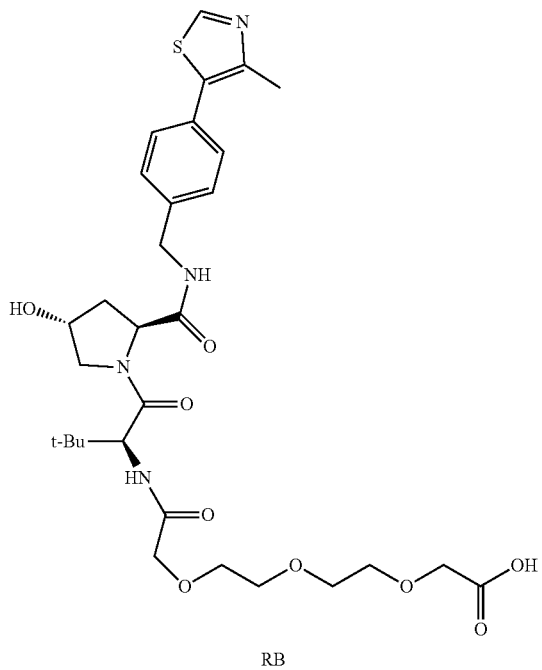

Step 1—(S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecanoic acid To a mixture of 2,2'-((oxybis(ethane-2,1-diyl))bis(oxy)) diacetic acid (1.36 g, 4.3 mmol, CAS #13887-98-4), DIPEA (415 mg, 3.23 mmol) in DMF (5 mL) was added HATU (488 mg, 1.29 mmol). Then (2S,4R)-1-((S)-2-amino-3,3-dimethylbutanoyl)-4-hydroxy-N-(4-(4-methylthiazol-5-yl)benzyl)pyrrolidine-2-carboxamide hydrochloride (500 mg, 1.12 mmol, Intermediate G) in DMF (5 mL) was added dropwise into the mixture. After the addition, the mixture was stirred at rt for 30 min. Then the mixture was poured into water, acidified to pH<6 by the addition of 1M HCl, then extracted with EtOAc (3×30 mL). The combined organic layers was washed with brine (50 mL×2), dried over anhydrous $Na_2SO_4$, filtered and concentrated in vacuo. The residue was purified by prep HPLC to give the title compound (125 mg, 18%) as a white solid. $^1$H NMR (400 MHz, METHANOL-$d_4$) δ 9.10 (br. s., 1H), 7.45-7.25 (m, 4H), 4.60 (s, 1H), 4.50-4.40 (m, 3H), 4.26 (d, J=15.51 Hz, 1H), 4.03-3.94 (m, 4H), 3.79-3.68 (m, 2H), 3.63-3.58 (m, 8H), 2.41 (s, 3H), 2.16-1.93 (m, 2H), 0.94 (s, 9H); LC/MS (ESI, m/z): [M+1]$^+$= 635.1.

5-(4-Tert-butoxycarbonylpiperazin-1-yl)pyrazolo[1,5-a]pyrimidine-3-carboxylic acid (Intermediate RC)

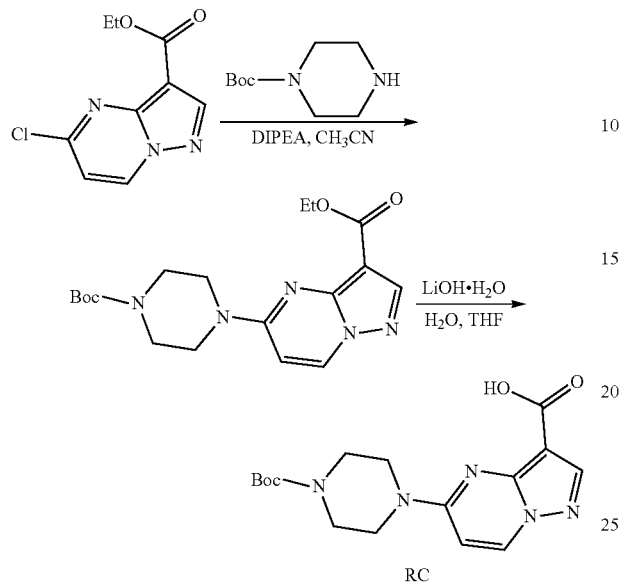

Step 1—Ethyl 5-(4-tert-butoxycarbonylpiperazin-1-yl)pyrazolo[1,5-a]pyrimidine-3-carboxylate To a mixture of ethyl 5-chloropyrazolo[1,5-a]pyrimidine-3-carboxylate (0.50 g, 2.22 mmol, CAS #1224944-77-7) and tert-butyl piperazine-1-carboxylate (619 mg, 3.32 mmol) in MeCN (6 mL) was added DIPEA (857 mg, 6.63 mmol, 1.16 mL), and the resulting mixture was stirred at 60° C. for 2 hours. On completion, the mixture was concentrated in vacuo. The residue was diluted with water (30 mL) and acidified with HCl (1 N) until the pH=5, then the mixture was extracted with EA (3×50 mL). The combined organic layers was dried over Na$_2$SO$_4$, filtered and concentrated in vacuo to give the compound (0.81 g, 97% yield) as white solid; $^1$H NMR (400 MHz, CDCl$_3$) δ 8.32-8.31 (m, 1H), 8.29 (s, 1H), 6.43-6.41 (m, 1H), 4.38-4.32 (m, 2H), 3.90-3.80 (m, 4H), 3.59-3.56 (m, 4H), 1.49 (s, 9H), 1.41-1.37 (m, 3H).

Step 2—5-(4-Tert-butoxycarbonylpiperazin-1-yl)pyrazolor[1,5-a]pyrimidine-3-carboxylic acid To a solution of ethyl 5-(4-tert-butoxycarbonylpiperazin-1-yl)pyrazolo[1,5-a]pyrimidine-3-carboxylate (0.80 g, 2.13 mmol) in THF (16.0 mL) was added a solution of LiOH.H$_2$O (223 mg, 5.33 mmol) in H$_2$O (4.00 mL). The reaction mixture was stirred at 20° C. for 16 hours, then an additional solution of LiOH.H$_2$O (1.00 g, 23.8 mmol) in H$_2$O (4.00 mL) was added, and the reaction mixture was stirred at 20° C. for 8 hours. The mixture was then heated to 45° C. and stirred for 16 hours. On completion, the mixture was concentrated in vacuo. The residue was extracted with EA (20 mL) to remove organic impurities. Then the water phase was acidified with 1 N HCl (aq.) until pH=4, and extracted with EA/MeOH (10/1, 2×20 mL). The combined organic layer was dried over Na$_2$SO$_4$, filtered and concentrated in vacuo to give the title compound (0.72 g, 97% yield) as yellowish solid. $^1$H NMR (400 MHz, CDCl$_3$) δ 8.74-8.72 (m, 1H), 8.17 (s, 1H), 6.84-6.82 (m, 1H), 3.75-3.74 (m, 4H), 3.46-3.43 (m, 4H), 1.42 (s, 9H).

N-[3-(difluoromethyl)-1-methyl-pyrazol-4-yl]-5-piperazin-1-yl-pyrazolo[1,5-a]pyrimidine-3-carboxamide (Intermediate RD)

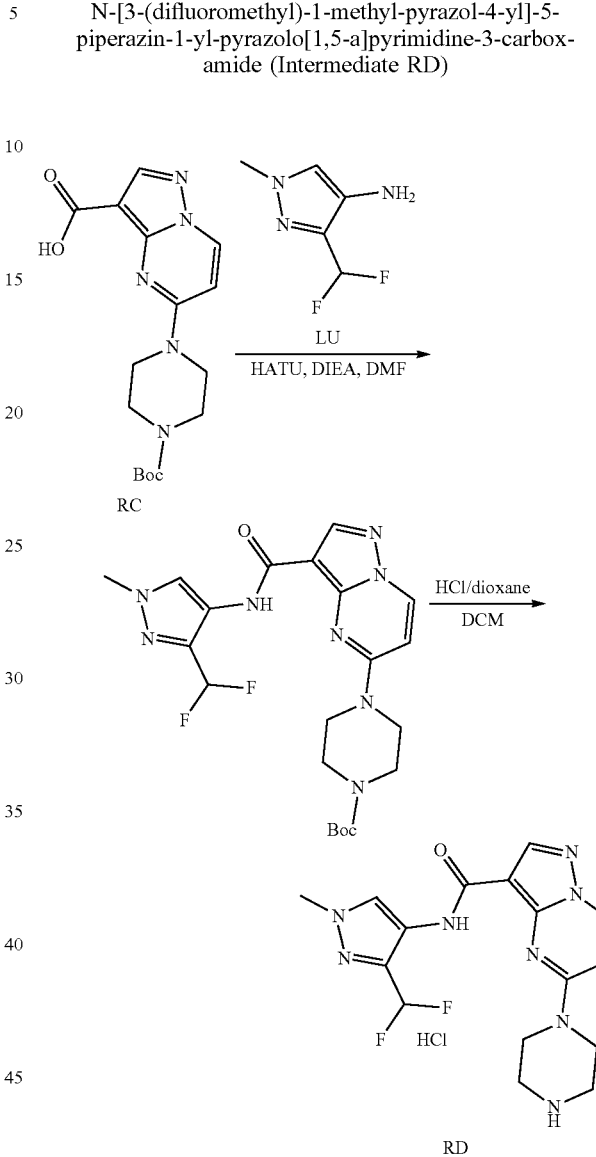

Step 1-Tert-butyl 4-[3-[[3-(difluoromethyl)-1-methyl-pyrazol-4-yl]carbamoyl]pyrazolo[1,5-a]pyrimidin-5-yl]piperazine-1-carboxylate To a mixture of 3-(difluoromethyl)-1-methyl-pyrazol-4-amine (847 mg, 5.76 mmol, Intermediate LU), 5-(4-tert-butoxycarbonylpiperazin-1-yl)pyrazolo[1,5-a]pyrimidine-3-carboxylic acid (2.00 g, 5.76 mmol, Intermediate RC) in DMF (20 mL) was added DIPEA (2.23 g, 17.3 mmol) and HATU (2.63 g, 6.91 mmol). The reaction mixture was stirred at 20° C. for 1 hour. On completion, the reaction mixture was poured into water (60 mL). The aqueous phase was extracted with ethyl acetate (2×30 mL). The combined organic phase was washed with brine (2×30 mL), dried with anhydrous Na$_2$SO$_4$, filtered and concentrated in vacuo. The residue was purified by column chromatography (SiO$_2$, Ethyl acetate) to give the title compound (734 mg, 26% yield) as reddish brown solid. $^1$H NMR (400 MHz, CDCl$_3$) δ 9.42 (s, 1H), 8.37 (s, 1H), 8.32-8.25 (m, 2H), 6.70 (t, J=54.0 Hz, 1H), 6.35 (d, J=8.0 Hz, 1H), 3.83 (s, 3H), 3.75 (s, 4H), 3.59-3.49 (m, 4H), 1.44 (s, 9H).

Step 2-N-[3-(difluoromethyl)-1-methyl-pyrazol-4-yl]-5-piperazin-1-yl-pyrazolo[1,5-a]pyrimidine-3-carboxamide To a mixture of tert-butyl 4-[3-[[3-(difluoromethyl)-1-methyl-pyrazol-4-yl]carbamoyl]pyrazolo[1,5-a]pyrimidin-5-yl]piperazine-1-carboxylate (684 mg, 1.44 mmol) in DCM (2 mL) was added HCl/dioxane (4 M, 717 uL). The reaction mixture was stirred at 25° C. for 1 hour. On completion, the reaction mixture was concentrated in vacuo to give the title compound (575 mg, 91% yield, HCl) as a white solid. $^1$H NMR (400 MHz, DMSO-d$_6$) δ 9.65 (s, 2H), 9.33 (s, 1H), 8.90 (d, J=8.0 Hz, 1H), 8.35 (d, J=12.4 Hz, 1H), 7.13 (t, J=53.6 Hz, 1H), 6.96 (d, J=7.6 Hz, 1H), 4.08 (s, 4H), 3.89 (s, 3H), 3.23 (s, 4H). LC-MS (ESI$^+$) m/z 377.2 (M+H)$^+$.

3-[5-[4-[2-(2-Aminoethoxy)ethyl]piperazin-1-yl]-3-methyl-2-oxo-benzimidazol-1-yl]piperidine-2,6-dione (Intermediate RG)

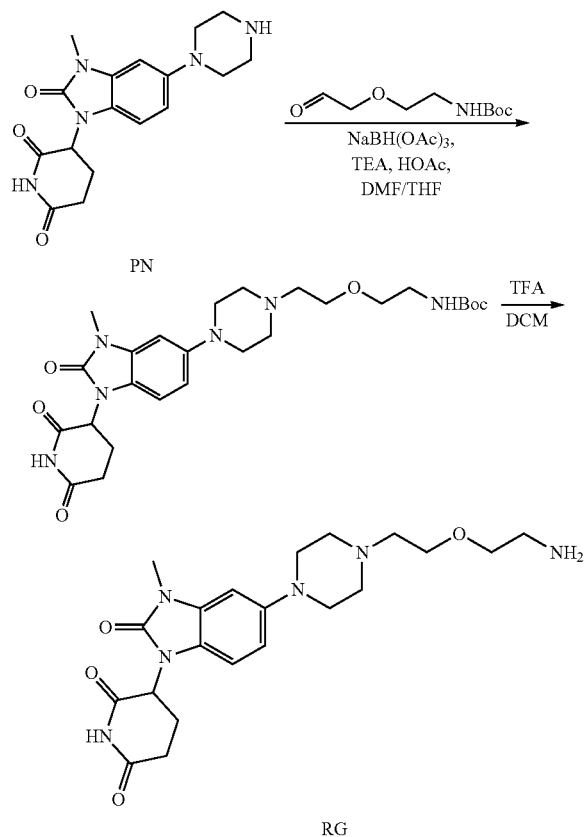

PN

RG

Step 1—Tert-butyl N-[2-[2-[4-[1-(2,6-dioxo-3-piperidyl)-3-methyl-2-oxo-benzimidazol-5-yl]piperazin-1-zyl]ethoxy]ethyl]carbamate To a mixture of 3-(3-methyl-2-oxo-5-piperazin-1-yl-benzimidazol-1-yl)piperidine-2,6-dione (20.0 mg, 582 umol, Intermediate PN) in THF (4 mL) and DMF (4 mL) was added TEA (589 mg, 5.82 mmol, 811 uL). The reaction mixture was stirred at 25° C. for 0.5 hour. Then tert-butyl N-[2-(2-oxoethoxy)ethyl]carbamate (500 mg, 2.46 mmol, synthesized via Step 1 of Intermediate FS) and HOAc (385 mg, 6.41 mmol, 366 uL) were added to the above solution. The reaction mixture was stirred at 25° C. for 0.5 hour. Then NaBH(OAc)$_3$ (247 mg, 1.16 mmol) was added to the reaction mixture. Then the mixture was stirred at 25° C. for 6 hrs under N$_2$ atmosphere. On completion, the mixture was concentrated in vacuo give a residue. The residue was purified by reversed-phase HPLC (0.1% FA condition) to give the title compound (60.0 mg, 19% yield) as a yellow solid. LC-MS (ESI$^+$) m/z 531.3 (M+H)$^+$.

Step 2—3-[5-[4-[2-(2-Aminoethoxy)ethyl]piperazin-1-yl]-3-methyl-2-oxo-benzimidazol-1-yl]piperidine-2,6-dione To a solution of tert-butyl N-[2-[2-[4-[1-(2,6-dioxo-3-piperidyl)-3-methyl-2-oxo-benzimidazol-5-yl]piperazin-1-yl]ethoxy]ethyl]carbamate (60.0 mg, 113 umol) in DCM (10 mL) was added TFA (4.62 g, 40.5 mmol, 3.00 mL). The mixture was stirred at 15° C. for 0.5 hr. On completion, the mixture was concentrated in vacuo to give the title compound (50.0 mg, 95% yield) as yellow oil. LC-MS (ESI$^+$) m/z 431.2 (M+H)$^+$.

3-[5-[3-(2-Aminoethoxy)propyl]-3-methyl-2-oxo-benzimidazol-1-yl]piperidine-2,6-dione (Intermediate RH)

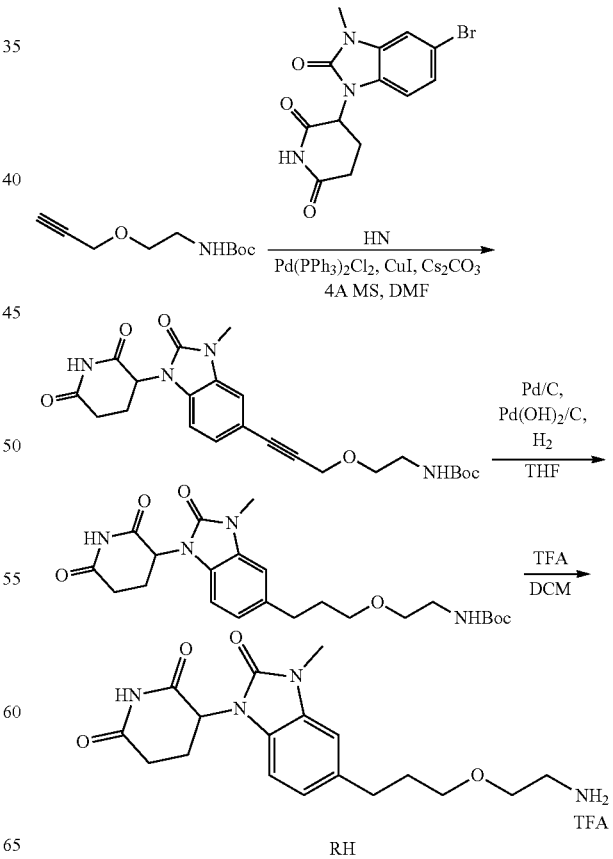

RH

Step 1—Tert-butyl N-[2-[3-[1-(2,6-dioxo-3-piperidyl)-3-methyl-2-oxo-benzimidazol-5-yl]prop-2-ynoxy]ethyl]carbamate To a solution of 3-(5-bromo-3-methyl-2-oxo-benzimidazol-1-yl)piperidine-2,6-dione (600 mg, 1.77 mmol, Intermediate HN) and tert-butyl N-(2-prop-2-ynoxyethyl)carbamate (883 mg, 4.44 mmol, synthesized via Step 1 on Intermediate CP) in DMF (10 mL) was added $Cs_2CO_3$ (2.31 g, 7.10 mmol), CuI (67.5 mg, 354 umol), 4 Å molecular sieve (20 mg) and $Pd(PPh_3)_2Cl_2$ (249 mg, 354. umol). The mixture was heated at 80° C. for 2 hours. On completion, the reaction mixture was filtered and the filtrate was concentrated in vacuo. The residue was diluted with water (30 mL), and then extracted with EA (3×40 mL). The combined organic layers were dried over $Na_2SO_4$, filtered and concentrated in vacuo to give a residue. The residue was purified by prep-HPLC (FA condition) to give the title compound (650 mg, 80% yield) as light yellow solid. $^1$H NMR (400 MHz, DMSO-$d_6$) δ 11.12 (s, 1H), 7.32 (s, 1H), 7.19-7.10 (m, 2H), 6.90-6.78 (m, 1H), 5.39 (dd, J=5.6, 12.8 Hz, 1H), 4.37 (s, 2H), 4.11 (d, J=2.4 Hz, 1H), 3.50 (t, J=6.0 Hz, 2H), 3.34 (s, 3H), 3.18-3.09 (m, 2H), 2.95-2.82 (m, 1H), 2.73-2.55 (m, 2H), 2.09-1.99 (m, 1H), 1.37 (s, 9H); LC-MS (ESI$^+$) m/z 357.2 (M+H−100)$^+$.

Step 2—Tert-butyl N-[2-[3-[1-(2,6-dioxo-3-piperidyl)-3-methyl-2-oxo-benzimidazol-5-yl]propoxy]ethyl]carbamate To a solution of tert-butyl N-[2-[3-[1-(2,6-dioxo-3-piperidyl)-3-methyl-2-oxo-benzimidazol-5-yl]prop-2-ynoxy]ethyl]carbamate (600 mg, 1.31 mmol) in THF (20 mL) was added $Pd(OH)_2$/C (150 mg, 10 wt %) and Pd/C (150 mg, 10 wt %) under $N_2$. The suspension was degassed under vacuum and purged with $H_2$ gas three times. The mixture was stirred at 25° C. for 16 hours under $H_2$ (15 PSI). On completion, the reaction mixture was filtered and the filtrate was concentrated in vacuo to give the title compound (500 mg, 82% yield) as white solid. $^1$H NMR (400 MHz, DMSO-$d_6$) δ 11.07 (s, 1H), 7.08-6.92 (m, 2H), 6.86 (dd, J=1.2, 8.4 Hz, 1H), 6.77 (t, J=5.2 Hz, 1H), 5.33 (dd, J=5.2, 12.8 Hz, 1H), 3.39-3.33 (m, 4H), 3.32 (s, 3H), 3.15-3.03 (m, 2H), 2.97-2.81 (m, 1H), 2.73-2.58 (m, 4H), 2.03-1.95 (m, 1H), 1.86-1.74 (m, 2H), 1.37 (s, 9H); LC-MS (ESI$^+$) m/z 483.1 (M+Na)$^+$.

Step 3—3-[5-[3-(2-Aminoethoxy)propyl]-3-methyl-2-oxo-benzimidazol-1-yl]piperidine-2,6-dione To a solution of tert-butyl N-[2-[3-[1-(2,6-dioxo-3-piperidyl)-3-methyl-2-oxo-benzimidazol-5-yl]propoxy]ethyl]carbamate (150 mg, 325 umol) in DCM (3 mL) was added TFA (1.54 g, 13.5 mmol). The mixture was stirred at 30° C. for 0.5 hour. On completion, the reaction mixture was concentrated in vacuo to give the title compound (150 mg, 97% yield, TFA) as light yellow solid. LC-MS (ESI$^+$) m/z 361.1 (M+H)$^+$.

4-3-[4-[3-(2-Aminoethoxy)propyl]-3-methyl-2-oxo-benzimidazol-1-yl]piperidine-2,6-dione (Intermediate RI)

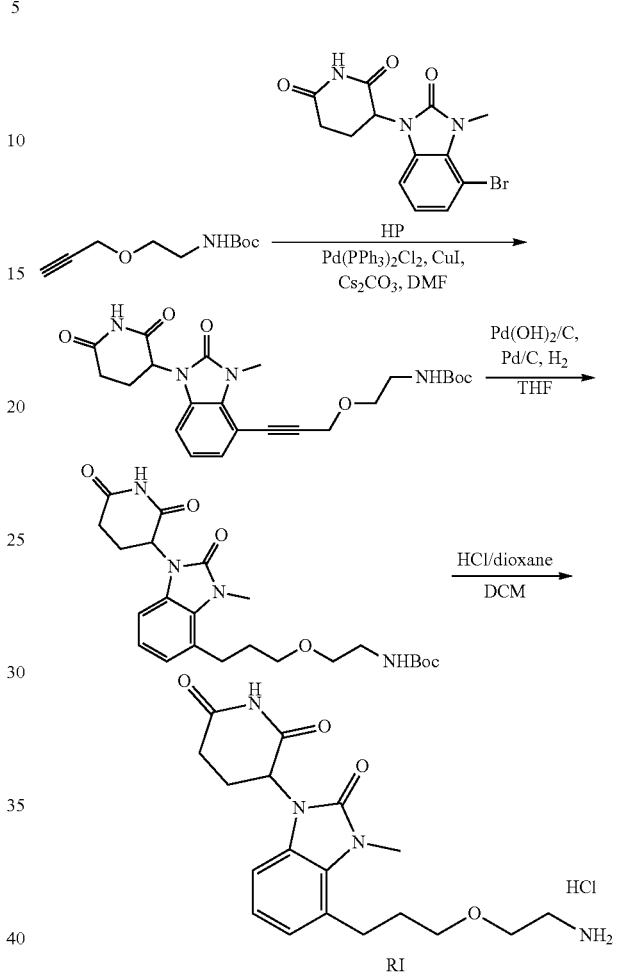

Step 1—Tert-butyl N-[2-[3-[1-(2,6-dioxo-3-piperidyl)-3-methyl-2-oxo-benzimidazol-4-yl]prop-2-ynoxy]ethyl]carbamate To a mixture of tert-butyl N-(2-prop-2-ynoxyethyl)carbamate (4.42 g, 22.1 mmol, synthesized via Step 1 on Intermediate CP) and 3-(4-bromo-3-methyl-2-oxo-benzimidazol-1-yl)piperidine-2,6-dione (3.00 g, 8.87 mmol, Intermediate HP) in DMF (50 mL) was added $Cs_2CO_3$ (14.4 g, 44.3 mmol), CuI (168 mg, 887 umol) and $Pd(PPh_3)_2Cl_2$ (622 mg, 887 umol). The reaction mixture was stirred at 80° C. for 2 hours. On completion, the reaction mixture was filtered and concentrated in vacuo. The residue was diluted with water (50 mL) and extracted with EA (3×100 mL). The combined organic layers was dried over $Na_2SO_4$, filtered and concentrated in vacuo to give a residue. The residue was purified by prep-HPLC (0.1% FA condition) to give the title compound (2.70 g, 66% yield) as brown solid. $^1$H NMR (400 MHz, DMSO-$d_6$) δ 11.13 (s, 1H), 7.23-7.09 (m, 2H), 7.08-6.99 (m, 1H), 6.92-6.82 (m, 1H), 5.45-5.36 (m, 1H), 4.44 (s, 2H), 3.64 (s, 3H), 3.52 (t, J=6.0 Hz, 2H), 3.16-3.08 (m, 2H), 2.96-2.83 (m, 1H), 2.78-2.60 (m, 2H), 2.07-1.95 (m, 1H), 1.36 (s, 9H).

Step 2—Tert-butyl N-[2-[3-[1-(2,6-dioxo-3-piperidyl)-3-methyl-2-oxo-benzimidazol-4-yl]propoxy]ethyl]carbamate To a mixture of tert-butyl N-[2-[3-[1-(2,6-dioxo-3-piperidyl)-3-methyl-2-oxo-benzimidazol-4-yl]prop-2-ynoxy]ethyl]carbamate (200 mg, 438 umol) in THF (5 mL) was added Pd/C (100 mg, 10 wt %) and Pd(OH)$_2$/C (100 mg, 10 wt %). The reaction mixture was stirred at 25° C. for 12 hours under H$_2$ (15 PSI) atmosphere. On completion, the reaction mixture was filtered and concentrated in vacuo to give the title compound (200 mg, 99% yield) as light yellow oil. $^1$H NMR (400 MHz, DMSO-d$_6$) δ 11.08 (s, 1H), 7.00-6.92 (m, 2H), 6.91-6.84 (m, 1H), 6.79 (s, 1H), 5.39-5.32 (m, 1H), 3.56 (s, 3H), 3.44 (t, J=6.0 Hz, 2H), 3.40-3.38 (m, 2H), 3.09 (d, J=5.6 Hz, 2H), 2.98-2.93 (m, 2H), 2.90-2.83 (m, 1H), 2.71-2.60 (m, 2H), 2.03-1.94 (m, 1H), 1.88-1.76 (m, 2H), 1.37 (s, 9H).

Step 3—4-3-[4-[3-(2-Aminoethoxy)propyl]-3-methyl-2-oxo-benzimidazol-1-yl]piperidine-2,6-dione To a mixture of tert-butyl N-[2-[3-[1-(2,6-dioxo-3-piperidyl)-3-methyl-2-oxo-benzimidazol-4-yl]propoxy]ethyl]carbamate (200 mg, 434 umol) in DCM (3 mL) was added HCl/dioxane (4 M, 5 mL). The reaction mixture was stirred at 25° C. for 1 hour. On completion, the reaction mixture was concentrated in vacuo to give the title compound (172 mg, 99% yield) as light yellow solid. LC-MS (ESI$^+$) m/z 361.1 (M+H)$^+$.

3-[5-[3-[(2R)-2-(aminomethyl)morpholin-4-yl]propyl]-3-methyl-2-oxo-benzimidazol-1-yl]piperidine-2,6-dione (Intermediate RJ)

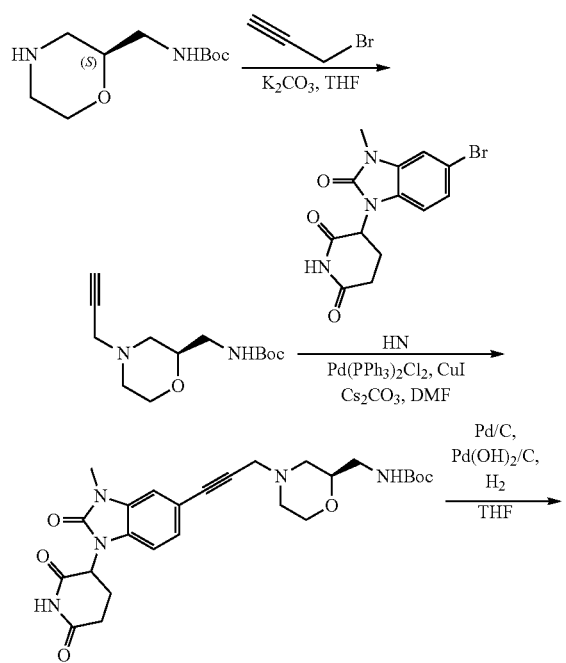

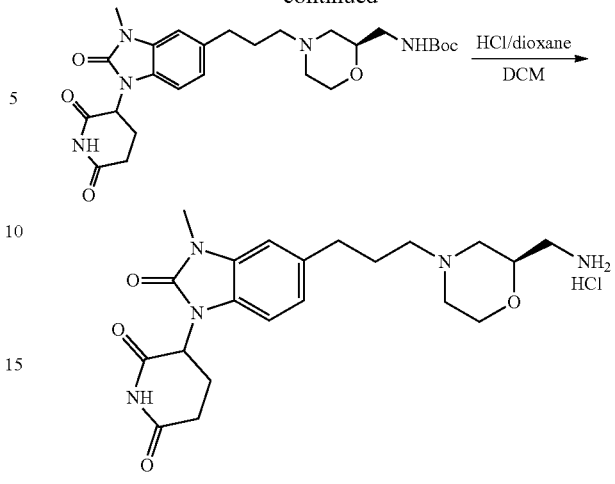

RJ

Step 1—Tert-butyl N-[[(2R)-4-prop-2-ynylmorpholin-2-yl]methyl]carbamate

To a solution of tert-butyl N-[[(2S)-morpholin-2-yl]methyl]carbamate (1.00 g, 4.62 mmol, CAS #875551-59-0) and 3-bromoprop-1-yne (550 mg, 4.62 mmol) in THF (20 mL) was added K$_2$CO$_3$ (1.28 g, 9.25 mmol). The reaction mixture was stirred at 25° C. for 12 hours. On completion, the mixture was diluted with water (30 mL) and extracted with EA (3×80 mL). The combined organic layers was dried over Na$_2$SO$_4$, filtered and concentrated in vacuo to give a residue. The residue was purified by column chromatography (SiO$_2$, Petroleum ether/Ethyl acetate=10/1 to 2/1) to give the title compound (800 mg, 68% yield) as yellow oil. $^1$H NMR (400 MHz, CDCl$_3$) δ 4.93 (s, 1H), 3.93-3.87 (m, 1H), 3.68 (dt, J=2.4, 11.2 Hz, 1H), 3.64-3.57 (m, 1H), 3.31 (d, J=2.4 Hz, 2H), 3.15-3.05 (m, 1H), 2.78-2.72 (m, 1H), 2.70-2.65 (1H), 2.39 (dt, J=3.6, 11.2 Hz, 1H), 2.27 (t, J=2.4 Hz, 1H), 2.13 (t, J=10.8 Hz, 1H), 1.87 (s, 1H), 1.45 (s, 9H).

Step 2—Tert-butyl N-[[(2R)-4-[3-[1-(2,6-dioxo-3-piperidyl)-3-methyl-2-oxo-benzimidazol-5-yl]prop-2-ynyl]morpholin-2-yl]methyl]carbamate To a solution of tert-butyl N-[[(2R)-4-prop-2-ynylmorpholin-2-yl]methyl]carbamate (846 mg, 3.33 mmol) and 3-(5-bromo-3-methyl-2-oxo-benzimidazol-1-yl)piperidine-2,6-dione (450 mg, 1.33 mmol, Intermediate HN) in DMF (15 mL) was added Cs$_2$CO$_3$ (2.17 g, 6.65 mmol), CuI (25.3 mg, 133 umol) and Pd(PPh$_3$)$_2$Cl$_2$ (93.4 mg, 133 umol). The reaction mixture was stirred at 80° C. for 2 hr under N$_2$. On completion, the mixture was filtered, and the filtrate was concentrated in vacuo to give a residue. The residue was purified by reverse phase (0.1% FA condition) to give the title compound (550 mg, 80% yield) as a yellow solid. $^1$H NMR (400 MHz, DMSO-d$_6$) δ 11.11 (s, 1H), 7.28 (s, 1H), 7.16-7.10 (m, 2H), 6.86-6.83 (m, 1H), 5.38 (dd, J=5.2, 12.4 Hz, 1H), 3.79 (t, J=13.2 Hz, 2H), 3.52 (s, 2H), 3.34 (s, 3H), 3.01-2.92 (m, 3H), 2.80-2.70 (m, 2H), 2.69-2.65 (m, 2H), 2.35-2.27 (m, 1H), 2.25-2.15 (m, 1H), 2.06-1.95 (m, 2H), 1.37 (s, 9H); LC-MS (ESI$^+$) m/z 512.2 (M+H)$^+$.

Step 3—Tert-butyl N-[[(2R)-4-[3-[1-(2,6-dioxo-3-piperidyl)-3-methyl-2-oxo-benzimidazol-5-yl]propyl]morpholin-2-yl]methyl]carbamate To a solution of tert-butyl N-[[(2R)-4-[3-[1-(2,6-dioxo-3-piperidyl)-3-methyl-2-oxo-benzimidazol-5-yl]prop-2-ynyl]

morpholin-2-yl]methyl]carbamate (300 mg, 586 umol) in THF (10 mL) was added Pd/C (100 mg, 10 wt %) and Pd(OH)$_2$/C (100 mg, 10 wt %). The reaction mixture was stirred at 25° C. under H$_2$ (15 psi) for 12 hours. On completion, the residue was filtered and the filtrate was concentrated in vacuo to give a residue. The residue was purified by prep-HPLC (column: Phenomenex Synergi C18 150*25*10 um; mobile phase: [water (0.225% FA)-ACN]; B %: 1%-31%, 10 min) to give the title compound (120 mg, 39% yield) as a white solid. $^1$H NMR (400 MHz, DMSO-d$_6$) δ 11.08 (s, 1H), 7.04 (s, 1H), 7.00 (d, J=8.0 Hz, 1H), 6.87 (d, J=8.0 Hz, 1H), 6.82 (t, J=5.6 Hz, 1H), 5.33 (dd, J=5.2, 12.8 Hz, 1H), 3.43-3.40 (m, 3H), 3.32 (s, 3H), 3.03-2.87 (m, 3H), 2.73-2.58 (m, 6H), 2.36-2.25 (m, 2H), 2.03-1.95 (m, 2H), 1.79-1.66 (m, 3H), 1.36 (s, 9H); LC-MS (ESI$^+$) m/z 516.3 (M+H)$^+$.

Step 4—3-[5-[3-[(2R)-2-(aminomethyl)morpholin-4-yl]propyl]-3-methyl-2-oxo-benzimidazol-1-yl]piperidine-2,6-dione To a solution of tert-butyl N-[[(2R)-4-[3-[1-(2,6-dioxo-3-piperidyl)-3-methyl-2-oxo-benzimidazol-5-yl]propyl]morpholin-2-yl]methyl]carbamate (120 mg, 232 umol) in DCM (3 mL) was added HCl/dioxane (4 M, 1 mL). The reaction mixture was stirred at 25° C. for 2 hours. On completion, the mixture was concentrated in vacuo to give the title compound (100 mg, 95% yield) as a white solid. LC-MS (ESI$^+$) m/z 416.2 (M+H)$^+$.

3-[5-[3-[(2S)-2-(aminomethyl)morpholin-4-yl]propyl]-3-methyl-2-oxo-benzimidazol-1-yl]piperidine-2,6-dione (Intermediate RK)

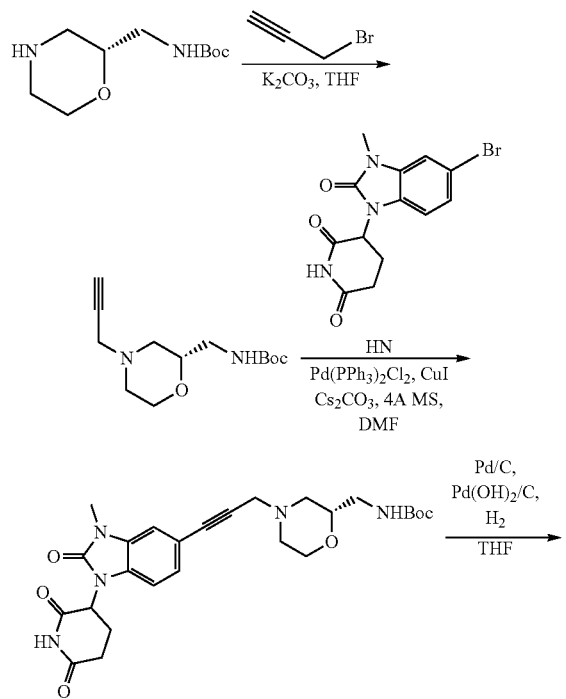

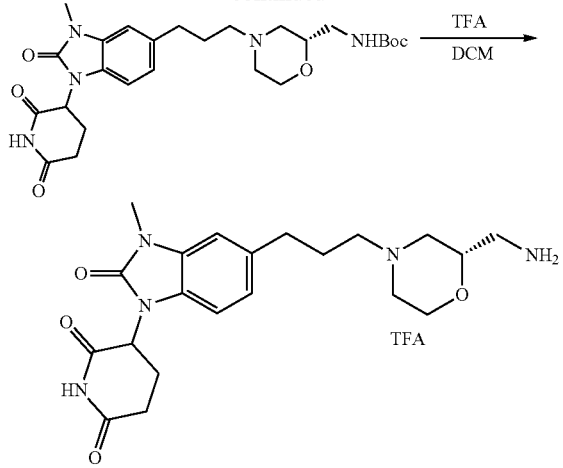

Step 1-Tert-butyl N-[[(2S)-4-prop-2-ynylmorpholin-2-yl]methyl]carbamate

To a mixture of tert-butyl N-[[(2R)-morpholin-2-yl]methyl]carbamate (3 g, 13.8 mmol, CAS #186202-57-3) and 3-bromoprop-1-yne (1.98 g, 16.6 mmol) in THF (60 mL) was added K$_2$CO$_3$ (3.83 g, 27.7 mmol). The reaction mixture was stirred at 25° C. for 16 hours. On completion, the reaction mixture was filtered and concentrated in vacuo to give a residue. The residue was purified by column chromatography (SiO$_2$, petroleum ether/ethyl acetate=4/1) to give the title compound (2.4 g, 68% yield) as light yellow solid. $^1$H NMR (400 MHz, CDCl$_3$) δ 4.90 (s, 1H), 3.96-3.83 (m, 1H), 3.74-3.50 (m, 2H), 3.33-3.25 (m, 3H), 3.13-3.08 (m, 1H), 2.78-2.62 (m, 2H), 2.41-2.33 (m, 1H), 2.26 (t, J=2.4 Hz, 1H), 2.13 (t, J=10.4 Hz, 1H), 1.44 (s, 9H).

Step 2—Tert-butyl N-[[(2S)-4-[3-[1-(2,6-dioxo-3-piperidyl)-3-methyl-2-oxo-benzimidazol-5-yl]prop-2-ynyl]morpholin-2-yl]methyl]carbamate To a solution of 3-(5-bromo-3-methyl-2-oxo-benzimidazol-1-yl)piperidine-2,6-dione (265 mg, 784 umol, Intermediate HN) and tert-butyl N-[[(2S)-4-prop-2-ynylmorpholin-2-yl]methyl]carbamate (299 mg, 1.18 mmol) in DMF (15 mL) was added CuI (29.9 mg, 157 umol), Pd(PPh$_3$)$_2$Cl$_2$ (110 mg, 157 umol), Cs$_2$CO$_3$ (1.02 g, 3.13 mmol) and 4 Å molecular sieves (20 mg) at 25° C. The reaction mixture was stirred at 80° C. for 3 hours. On completion, the reaction mixture was filtered and the filtrate was concentrated in vacuo to give a residue. The residue was diluted with water (30 mL), and then extracted with EA (3×50 mL). The combined organic layers were washed with brine (50 mL), then dried over Na$_2$SO$_4$, filtered and the filtrate was concentrated in vacuo to give a residue. The residue was purified by reverse phase (0.1% FA condition) to give the title compound (270 mg, 67% yield) as a white solid. 1H NMR (400 MHz, CDCl$_3$) δ 8.18 (s, 1H), 7.17 (d, J=1.2 Hz, 1H), 7.10 (s, 1H), 6.73 (d, J=8.4 Hz, 1H), 5.20-5.16 (m, 1H), 4.93-4.89 (m, 1H), 3.95-3.89 (m, 1H), 3.72-3.71 (m, 1H), 3.54-3.49 (m, 2H), 3.43 (s, 3H), 3.15-3.07 (m, 1H), 2.99-2.99 (m, 1H), 2.99-2.92 (m, 1H), 2.89-2.61 (m, 6H), 2.48-2.40 (m, 1H), 2.28-2.22 (m, 1H), 2.17 (t, J=3.6 Hz, 1H), 1.43 (s, 9H); LC-MS (ESI+) m/z 512.3 (M+H)$^+$.

Step 3—Tert-butyl N-[[(2S)-4-[3-[1-(2,6-dioxo-3-piperidyl)-3-methyl-2-oxo-benzimidazol-5-yl]propyl]morpholin-2-yl]methyl]carbamate To a solution of tert-butyl N-[[(2S)-4-[3-[1-(2,6-dioxo-3-piperidyl)-3-methyl-2-oxo-benzimidazol-5-yl]prop-2-ynyl]morpholin-2-yl]methyl]carbamate (270 mg, 528 umol) in THF (15 mL) was added Pd/C (120 mg, 528 umol, 10 wt %) and Pd(OH)$_2$/C (110 mg, 528 umol, 10 wt %) at 25° C. The reaction mixture was stirred at 25° C. for 2 hours under H$_2$ (15 PSI). On completion, the reaction mixture was filtered with celite and the filtrate was concentrated in vacuo to give a residue. The residue was purified by reverse phase (0.1% FA condition) to give the title compound (230 mg, 85% yield) as a brown solid. LC-MS (ESI$^+$) m/z 516.1 (M+H)$^+$.

Step 4—3-[5-[3-[(2S)-2-(aminomethyl)morpholin-4-yl]propyl]-3-methyl-2-oxo-benzimidazol-1-yl]piperidine-2,6-dione To a solution of tert-butyl N-[[(2S)-4-[3-[1-(2,6-dioxo-3-piperidyl)-3-methyl-2-oxo-benzimidazol-5-yl]propyl]morpholin-2-yl]methyl]carbamate (130 mg, 252 umol) in DCM (2 mL) was added TFA (1.67 g, 14.6 mmol). The reaction mixture was stirred at 25° C. for 2 hours. On completion, the reaction mixture was concentrated in vacuo to give the title compound (100 mg, 95% yield, TFA) as a brown oil. LC-MS (ESI$^+$) m/z 416.3 (M+H)$^+$.

2-[(2S)-4-prop-2-ynylmorpholin-2-yl]acetonitrile (Intermediate RL)

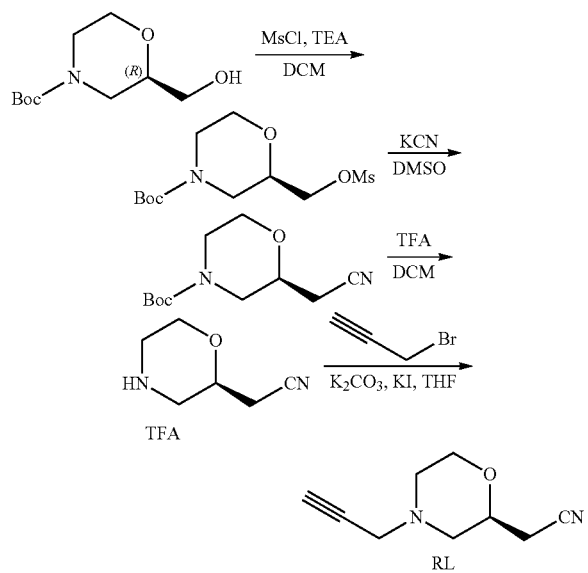

Step 1—Tert-butyl (2R)-2-(methylsulfonyloxymethyl)morpholine-4-carboxylate

To a solution of tert-butyl (2R)-2-(hydroxymethyl)morpholine-4-carboxylate (10.0 g, 46.0 mmol, CAS #135065-71-3) and TEA (9.32 g, 92.0 mmol) in DCM (100 mL) was added MsCl (6.36 g, 55.5 mmol) at 0° C. The reaction mixture was stirred at 25° C. for 2 hours. On completion, the reaction mixture was poured into sat.NaHCO$_3$ (50 mL) and extracted with EA (3×300 mL). The combined organic layers were washed with brine (300 mL), dried with anhydrous Na$_2$SO$_4$, filtered and concentrated in vacuo to give the title compound (13.5 g, 99% yield) as colorless oil. $^1$H NMR (400 MHz, CDCl$_3$) δ 4.23 (d, J=4.8 Hz, 2H), 4.06-3.77 (m, 3H), 3.74-3.64 (m, 1H), 3.59-3.49 (m, 1H), 3.06 (s, 3H), 3.01-2.88 (m, 1H), 2.81-2.67 (m, 1H), 1.49-1.42 (m, 9H).

Step 2—Tert-butyl (2S)-2-(cyanomethyl)morpholine-4-carboxylate

To a solution of tert-butyl (2R)-2-(methylsulfonyloxymethyl)morpholine-4-carboxylate (13.0 g, 44.0 mmol) and KI (10.9 g, 66.0 mmol) in DMSO (200 mL) was added KCN (3.15 g, 48.4 mmol, 2.07 mL). The reaction mixture was stirred at 80° C. for 3 hours. The reaction mixture was then stirred at 100° C. for 4 hours. On completion, the reaction mixture was poured into sat.NaHCO$_3$ (100 mL) and extracted with EA (3×500 mL). The combined organic layers were washed with brine (50 mL), dried with anhydrous Na$_2$SO$_4$, filtered and concentrated in vacuo. The residue was purified by silica column chromatography (PE/EA=10/1 to 6/1) to give the title compound (8.00 g, 80% yield) as a white solid. $^1$H NMR (400 MHz, CDCl$_3$) δ 4.10-3.78 (m, 3H), 3.72-3.62 (m, 1H), 3.60-3.50 (m, 1H), 2.97 (t, J=11.2 Hz, 1H), 2.84-2.65 (s, 1H), 2.62-2.50 (m, 2H), 1.47 (s, 9H).

Step 3—2-[(2S)-Morpholin-2-yl]acetonitrile

To a solution of tert-butyl (2S)-2-(cyanomethyl)morpholine-4-carboxylate (4.50 g, 19.8 mmol) in DCM (10 mL) was added TFA (138 g, 1.22 mol). The reaction mixture was stirred at 25° C. for 1 hour. On completion, the reaction mixture was concentrated in vacuo to give the title compound (4.70 g, 98% yield) as colorless oil. $^1$H NMR (400 MHz, DMSO-d$_6$) δ 9.29-8.83 (m, 2H), 4.05-3.88 (m, 2H), 3.77-3.63 (m, 1H), 3.31-3.15 (m, 2H), 3.03-2.76 (m, 3H), 2.41-2.18 (m, 1H).

Step 4—2-[(2S)-4-prop-2-ynylmorpholin-2-yl]acetonitrile

To a solution of 2-[(2S)-morpholin-2-yl]acetonitrile (4.70 g, 19.5 mmol, TFA) and 3-bromoprop-1-yne (3.49 g, 29.3 mmol) in THF (100 mL) was added KI (324 mg, 1.96 mmol) and K$_2$CO$_3$ (8.11 g, 58.7 mmol). The reaction mixture was stirred at 25° C. for 48 hours. On completion, the reaction mixture was diluted with EA (500 mL) and filtered to give the filtrate. The filtrate was concentrated in vacuo to give a residue. The residue was purified by silica column chromatography (PE/EA=10/1 to 6/1) to give the title compound (1.50 g, 46% yield) as a light yellow oil. $^1$H NMR (400 MHz, CDCl$_3$) δ 3.97-3.90 (m, 1H), 3.87-3.78 (m, 1H), 3.70 (dt, J=2.4, 11.2 Hz, 1H), 3.33 (d, J=2.0 Hz, 2H), 2.85-2.80 (m, 1H), 2.67-2.60 (m, 1H), 2.56 (d, J=6.0 Hz, 2H), 2.44 (dt, J=3.2, 11.2 Hz, 1H), 2.29 (t, J=2.4 Hz, 1H), 2.35 (t, J=10.0 Hz, 1H).

3-[5-[3-[(2S)-2-(2-aminoethyl)morpholin-4-yl]propyl]-3-methyl-2-oxo-benzimidazol-1-yl]piperidine-2,6-dione (Intermediate RM)

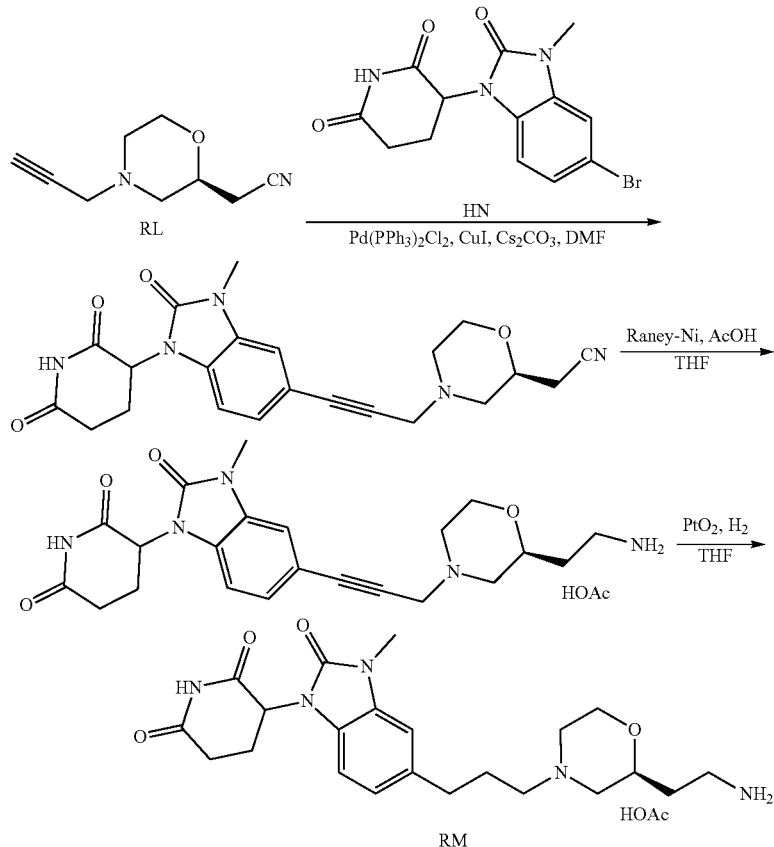

Step 1—2-[(2S)-4-[3-[1-(2,6-dioxo-3-piperidyl)-3-methyl-2-oxo-benzimidazol-5-yl]prop-2-ynyl]morpholin-2-yl]acetonitrile To a solution of 3-(5-bromo-3-methyl-2-oxo-benzimidazol-1-yl)piperidine-2,6-dione (1.00 g, 2.96 mmol, Intermediate HN) and 2-[(2S)-4-prop-2-ynylmorpholin-2-yl]acetonitrile (971 mg, 5.91 mmol, Intermediate RL) in DMSO (50 mL) was added Pd(PPh$_3$)$_2$Cl$_2$ (415 mg, 591 umol), DIPEA (1.91 g, 14.7 mmol) and CuI (112 mg, 591 umol). The reaction mixture was stirred at 85° C. for 2 hours. On completion, the reaction mixture was filtered. The filtrate was diluted with EA (30 mL), poured into water (300 mL) and extracted with EA (2×200 mL). The organic layer was washed with water (2×200 mL), brine (200 mL), dried with anhydrous Na$_2$SO$_4$ and filtered. The filtrate was concentrated in vacuo. The residue was purified by reversed-phase chromatography (FA, 0.1%) to give the title compound (1.00 g, 80% yield) as a yellow solid. LC-MS (ESI$^+$) m/z 422.2 (M+H)$^+$.

Step 2—3-[5-[3-[(2S)-2-(2-aminoethyl)morpholin-4-yl]prop-1-ynyl]-3-methyl-2-oxo-benzimidazol-1-yl]piperidine-2,6-dione To a solution of 2-[(2S)-4-[3-[1-(2,6-dioxo-3-piperidyl)-3-methyl-2-oxo-benzimidazol-5-yl]prop-2-ynyl]morpholin-2-yl]acetonitrile (600 mg, 1.42 mmol) and AcOH (170 mg, 2.85 mmol) in THF (40 mL) was added Raney-Ni (50.0 mg, 583 umol). The reaction mixture was stirred at 25° C. for 4 hours under H$_2$ (50 Psi). On completion, the reaction mixture was filtered. The filter cake was triturated with water (3×30 mL) and filtered to give the filtrate. The filtrate was concentrated in vacuo to give the title compound (600 mg, 100% yield, HOAc) as light yellow oil. LC-MS (ESI$^+$) m/z 426.1 (M+H)$^+$.

Step 3—3-[5-[3-[(2S)-2-(2-aminoethyl)morpholin-4-yl]propyl]-3-methyl-2-oxo-benzimidazol-1-yl]piperidine-2,6-dione To a solution of 3-[5-[3-[(2S)-2-(2-aminoethyl)morpholin-4-yl]prop-1-ynyl]-3-methyl-2-oxo-benzimidazol-1-yl]piperidine-2,6-dione (550 mg, 1.13 mmol, HOAc) in THF (30 mL) was added PtO$_2$ (51.4 mg, 226 umol). The reaction was stirred at 25° C. for 4 hours under H$_2$ (15 Psi). On completion, the reaction mixture was filtered to give the filtrate and concentrated in vacuo to give the title compound (400 mg, 100% yield, HOAc) as yellow oil. LC-MS (ESI$^+$) m/z 430.2 (M+H)$^+$.

2-[(2R)-4-Prop-2-ynylmorpholin-2-yl]acetonitrile (Intermediate RN)

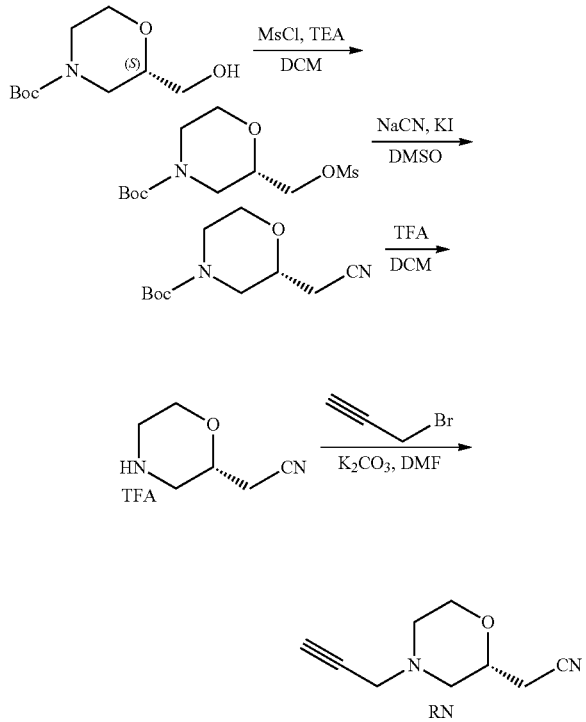

Step 1—Tert-butyl (2S)-2-(methylsulfonyloxymethyl)morpholine-4-carboxylate

To a mixture of tert-butyl (2S)-2-(hydroxymethyl)morpholine-4-carboxylate (5.00 g, 23.0 mmol, CAS #135065-76-8) in DCM (50 mL) was added TEA (3.03 g, 29.9 mmol) and MsCl (6.06 g, 52.9 mmol) at 0° C. Then the reaction mixture was stirred at 25° C. for 2 hours. On completion, the reaction mixture was poured into the ice-water (50 mL), and extracted with DCM (2×30 mL). The combined organic phase was washed with brine (2×50 mL), dried over anhydrous $Na_2SO_4$, filtered and concentrated in vacuo to give the title compound (6.50 g, 95% yield) as a white oil. $^1H$ NMR (400 MHz, $CDCl_3$) δ 4.23 (d, J=4.8 Hz, 2H), 3.92-3.85 (m, 3H), 3.69-3.65 (m, 1H), 3.57-3.51 (m, 1H), 3.06 (s, 3H), 3.01-2.95 (m, 1H), 2.82-2.76 (m, 1H), 1.46 (s, 9H).

Step 2—Tert-butyl (2R)-2-(cyanomethyl)morpholine-4-carboxylate

To a mixture of tert-butyl (2S)-2-(methylsulfonyloxymethyl)morpholine-4-carboxylate (6.50 g, 22.0 mmol) in DMSO (80 mL) was added KCN (1.50 g, 23.1 mmol) and KI (5.48 g, 33.0 mmol) at 25° C. The reaction mixture was then stirred at 100° C. for 4 hours. On completion, the reaction mixture was poured into the ice-water (50 mL), and extracted with DCM (2×30 mL). The combined organic phase was washed with brine (2×50 mL), dried over anhydrous $Na_2SO_4$, filtered and concentrated in vacuo to give a residue. The residue was purified by column chromatography ($SiO_2$, petroleum ether/ethyl acetate=3:1) to give the title compound (2.30 g, 46% yield) as a white solid. $^1H$ NMR (400 MHz, $CDCl_3$) δ 4.04-3.83 (m, 3H), 3.62-3.59 (m, 1H), 3.51-3.48 (m, 1H), 2.93-2.90 (m, 1H), 2.68 (m, 1H), 2.50-2.43 (m, 2H), 1.40 (s, 9H).

Step 3—2-[(2R)-Morpholin-2-yl]acetonitrile

To a solution of tert-butyl (2R)-2-(cyanomethyl) morpholine-4-carboxylate (1.00 g, 4.42 mmol) in DCM (6 mL) was added TFA (3 mL) at 25° C. The mixture was stirred at 25° C. for 1 hour. On completion, the mixture was concentrated in vacuo to give the title compound (1.06 g, 95% yield, TFA) as light yellow gum. $^1H$ NMR (400 MHz, DMSO-$d_6$) δ 9.11 (s, 2H), 4.04-4.01 (m, 1H), 4.00-3.91 (m, 1H), 3.79-3.67 (m, 1H), 3.34-3.16 (m, 2H), 3.07-2.89 (m, 2H), 2.87-2.73 (m, 2H).

Step 4—2-[(2R)-4-Prop-2-ynylmorpholin-2-yl]acetonitrile

To a mixture of 2-[(2R)-morpholin-2-yl]acetonitrile (1.06 g, 4.41 mmol, TFA) and $K_2CO_3$ (1.83 g, 13.2 mmol) in DMF (15 mL) was added 3-bromoprop-1-yne (577 mg, 4.85 mmol) at 25° C. The mixture was stirred at 25° C. for 16 hours. On completion, the mixture was filtered and the cake was washed with EA (20 mL). The filtrate and washing were combined and concentrated in vacuo. The residue was purified by column chromatography ($SiO_2$, PE:EA=20:1-5:1) to give the title compound (650 mg, 89% yield) as light yellow oil. $^1H$ NMR (400 MHz, $CDCl_3$) δ 3.93 (m, 1H), 3.88-3.81 (m, 1H), 3.72 (m, 1H), 3.36-3.30 (m, 2H), 2.88 (s, 1H), 2.68 (m, 1H), 2.57 (d, J=6.0 Hz, 2H), 2.46 (m, 1H), 2.32-2.21 (m, 2H).

3-[5-[3-[(2R)-2-(2-Aminoethyl)morpholin-4-yl]propyl]-3-methyl-2-oxo-benzimidazol-1-yl]piperidine-2,6-dione (Intermediate RO)

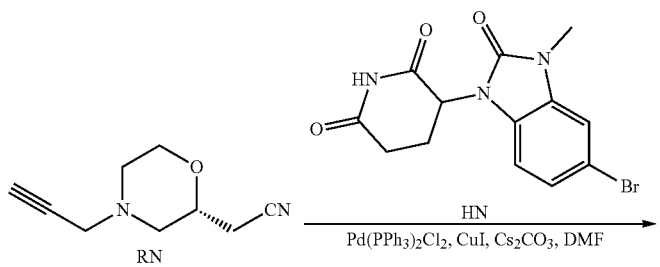

-continued

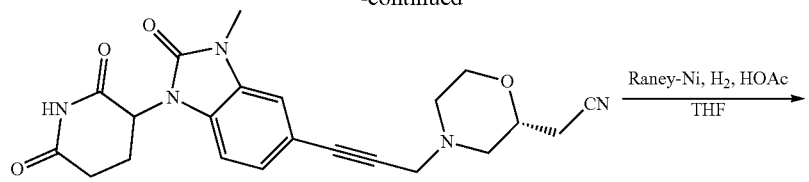

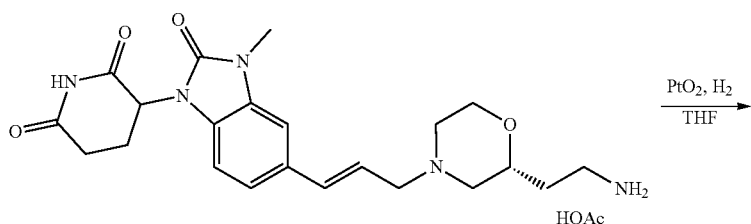

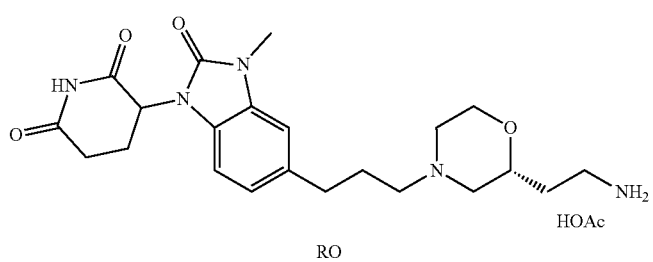

Step 1—2-[(2R)-4-[3-[1-(2,6-Dioxo-3-piperidyl)-3-methyl-2-oxo-benzimidazol-5-yl]prop-2-ynyl]morpholin-2-yl]acetonitrile A mixture of 2-[(2R)-4-prop-2-ynylmorpholin-2-yl]acetonitrile (588 mg, 3.58 mmol, Intermediate RN), 3-(5-bromo-3-methyl-2-oxo-benzimidazol-1-yl)piperidine-2,6-dione (480 mg, 1.42 mmol, Intermediate HN), CuI (58 mg, 304 umol), Pd(PPh$_3$)$_2$Cl$_2$ (201 mg, 286 umol), 4 Å MS (300 mg) and Cs$_2$CO$_3$ (2.31 g, 7.10 mmol) in DMF (15 mL) was stirred at 80° C. for 2 hours under N$_2$. On completion, the mixture was filtered and the filter cake was washed with EA (10 mL). The filtrate and washing were combined and concentrated in vacuo. The residue was purified by reversed phase (FA condition) and prep-HPLC (column: Phenomenex Synergi C18 150*25*10 um; mobile phase: [water (0.1% TFA)-ACN]; B %: 2%-30%, 10 min) to give the title compound (280 mg, 47% yield) as yellow solid. $^1$H NMR (400 MHz, DMSO-d$_6$) δ 11.13 (s, 1H), 7.35 (d, J=1.2 Hz, 1H), 7.27-7.20 (m, 1H), 7.20-7.13 (m, 1H), 5.42-5.38 (m, 1H), 4.17 (s, 2H), 4.08 (d, J=12.4 Hz, 1H), 3.91 m, 1H), 3.77-3.67 (m, 1H), 3.35 (s, 3H), 3.34-3.31 (m, 1H), 3.02-2.81 (m, 5H), 2.77-2.58 (m, 3H), 2.06-1.97 (m, 1H).

Step 2—3-[5-[3-[(2R)-2-(2-Aminoethyl)morpholin-4-yl]prop-1-enyl]-3-methyl-2-oxo-benzimidazol-1-yl]piperidine-2,6-dione A mixture of 2-[(2R)-4-[3-[1-(2,6-dioxo-3-piperidyl)-3-methyl-2-oxo-benzimidazol-5-yl]prop-2-ynyl]morpholin-2-yl]acetonitrile (270 mg, 640 umol), Raney-Ni (100 mg) and HOAc (210 mg, 3.50 mmol) in THF (6 mL) was stirred at 25° C. for 16 hours under H$_2$ (45 Psi). On completion, the mixture was filtered and the cake was washed with THF (10 mL). The combined organic layer was concentrated in vacuo to give the title compound (320 mg, 100% yield, HOAc) as light yellow gum. LC-MS (ESI$^+$) m/z 428.3 (M+H)$^+$.

Step 3—3-[5-[3-[(2R)-2-(2-Aminoethyl)morpholin-4-yl]propyl]-3-methyl-2-oxo-benzimidazol-1-yl]piperidine-2,6-dione A mixture of 3-[5-[3-[(2R)-2-(2-aminoethyl) morpholin-4-yl]prop-1-enyl]-3-methyl-2-oxo-benzimidazol-1-yl]piperidine-2,6-dione (320 mg, 640 umol) and PtO$_2$ (50.0 mg, 220 umol) in THF (10 mL) was stirred at 25° C. for 3 hours under H$_2$ (15 Psi). On completion, the mixture was filtered and the filter cake was washed with THF (10 mL). The filtrate and washing were combined and concentrated in vacuo to give the title compound (280 mg, 98% yield, HOAc) as light yellow gum. LC-MS (ESI⁺) m/z 430.3 (M+H)⁺.

4-[3-(Difluoromethyl)-4-[[2-[2-(2,2,2-trifluoroethyl-amino)-4-pyridyl]oxazole-4-carbonyl]amino]pyrazol-1-yl]benzoic acid (Intermediate RP)

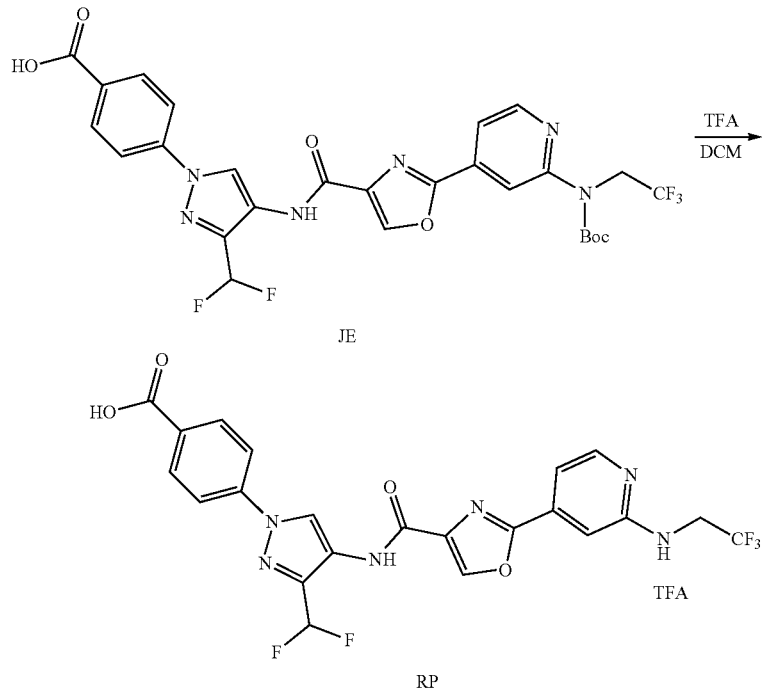

To a solution of 4-[4-[[2-[2-[tert-butoxycarbonyl(2,2,2-trifluoroethyl)amino]-4-pyridyl]oxazole-4-carbonyl]amino]-3-(difluoromethyl)pyrazol-1-yl]benzoic acid (70.0 mg, 112 umol, Intermediate JE) in DCM (4 mL) was added TFA (4 mL). The reaction mixture was stirred at 25° C. for 2 hrs. On completion, the mixture was concentrated in vacuo to give the title compound (71.5 mg, 100% yield, TFA) as a white solid. LC-MS (ESI⁺) m/z 523.2 (M+H)⁺.

1-(4-methoxyphenyl)-N-methyl-N-[[(2S)-4-prop-2-ynylmorpholin-2-yl]methyl]methanamine (Intermediate RQ)

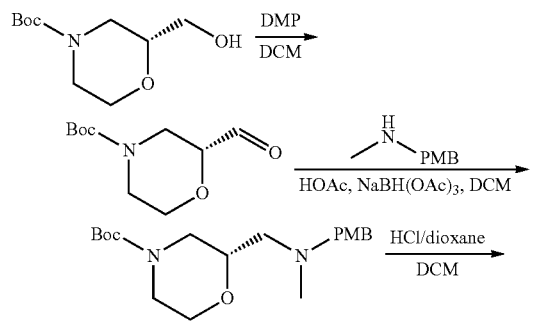

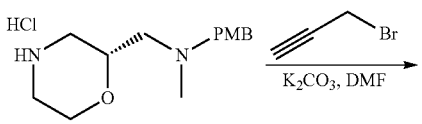

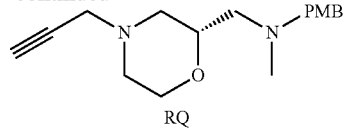

Step 1-Tert-butyl (2R)-2-formylmorpholine-4-carboxylate

To a solution of tert-butyl (2R)-2-(hydroxymethyl)morpholine-4-carboxylate (2.00 g, 9.21 mmol, CAS #135065-71-3) in DCM (40 mL) was added DMP (4.69 g, 11.0 mmol) at 0° C. The reaction mixture was stirred at 25° C. for 2 hours. On completion, the mixture was quenched with aq. Na₂S₂O₃ (50 mL) and aq. NaHCO₃ (50 mL). The mixture was stirred for 15 minutes and extracted with EA (2×50 mL). The organic layer was washed with brine (50 mL), dried with Na₂SO₄, and concentrated in vacuo to give the title compound (1.50 g, 76% yield) as colorless oil. ¹H NMR (400 MHz, CDCl₃) δ 9.65 (s, 1H), 4.08-4.00 (m, 1H), 3.95-3.85 (m, 2H), 3.83-3.75 (m, 1H), 3.68-3.53 (m, 2H), 3.12-3.03 (m, 1H), 1.47 (s, 9H).

Step 2—Tert-butyl (2S)-2-[[(4-methoxyphenyl)methyl-methyl-amino]methyl]morpholine-4-carboxylate To a solution of tert-butyl (2R)-2-formylmorpholine-4-carboxylate (1.5 g, 6.97 mmol) and 1-(4-methoxyphenyl)-

N-methyl-methanamine (1.05 g, 6.97 mmol) in DCM (30 mL) was added HOAc (418 mg, 6.97 mmol) and the reaction was stirred at 25° C. Thirty minutes later, NaBH(OAc)$_3$ (1.77 g, 8.36 mmol) was added and the reaction mixture was stirred at 25° C. for 10 hours. On completion, the mixture was concentrated in vacuo. The residue was purified by reversed phase (0.1% FA) to give the title compound (1.4 g, 57% yield) as a yellow solid. $^1$H NMR (300 MHz, CDCl$_3$) δ 7.22 (d, J=8.4 Hz, 2H), 6.85 (d, J=8.4 Hz, 2H), 4.07-3.94 (m, 1H), 3.93-3.83 (m, 2H), 3.90 (s, 3H), 3.58-3.43 (m, 4H), 3.01-2.80 (m, 1H), 2.62-2.46 (m, 2H), 2.41-2.31 (m, 1H), 2.26 (s, 3H), 1.48 (s, 9H); LC-MS (ESI$^+$) m/z 351.1 (M+H)$^+$.

Step 3—1-(4-Methoxyphenyl)-N-methyl-N-[[(2R)-morpholin-2-yl]methyl]methanamine hydrochloride To a solution of tert-butyl (2S)-2-[[(4-methoxyphenyl)methyl-methyl-amino]methyl]morpholine-4-carboxylate (1.40 g, 3.99 mmol) in HCl/dioxane (10 mL) was added DCM (10 mL). The reaction mixture was stirred at 25° C. for 2 hours. On completion, the mixture was concentrated in vacuo to give the title compound (1.15 g, 100% yield, HCl) as a yellow solid. LC-MS (ESI$^+$) m/z 251.1 (M+H)$^+$.

Step 4—1-(4-methoxyphenyl)-N-methyl-N-[[(2S)-4-prop-2-ynylmorpholin-2-yl]methyl]methanamine To a solution of 1-(4-methoxyphenyl)-N-methyl-N-[[(2R)-morpholin-2-yl]methyl]methanamine (1.15 g, 4.01 mmol, HCl) and 3-bromoprop-1-yne (525 mg, 4.41 mmol) in DMF (20 mL) was added K$_2$CO$_3$ (1.66 g, 12.0 mmol). The reaction mixture was stirred at 25° C. for 12 hours. On completion, the mixture was diluted with water (100 mL), and extracted with EA (2×50 mL). The organic layer was washed with brine (100 mL), then concentrated in vacuo. The residue was purified by reversed phase chromatography (0.1% FA condition) to give the title compound (700 mg, 61% yield) as colourless oil. LC-MS (ESI$^+$) m/z 289.2 (M+H)$^+$.

3-[3-Methyl-5-[3-[(2S)-2-(methylaminomethyl)morpholin-4-yl]propyl]-2-oxo-benzimidazol-1-yl]piperidine-2,6-dione (Intermediate RR)

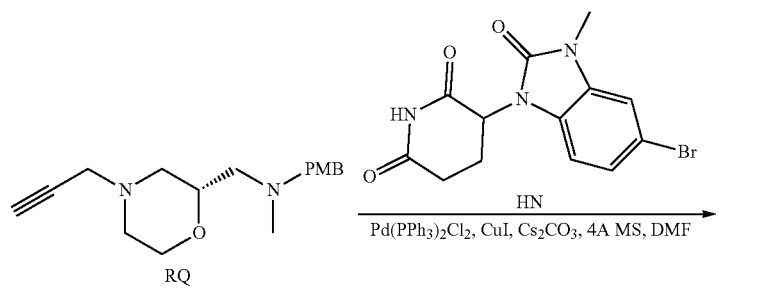

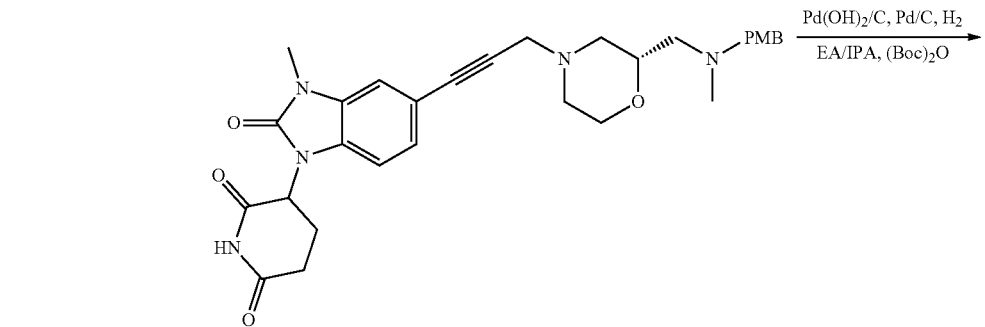

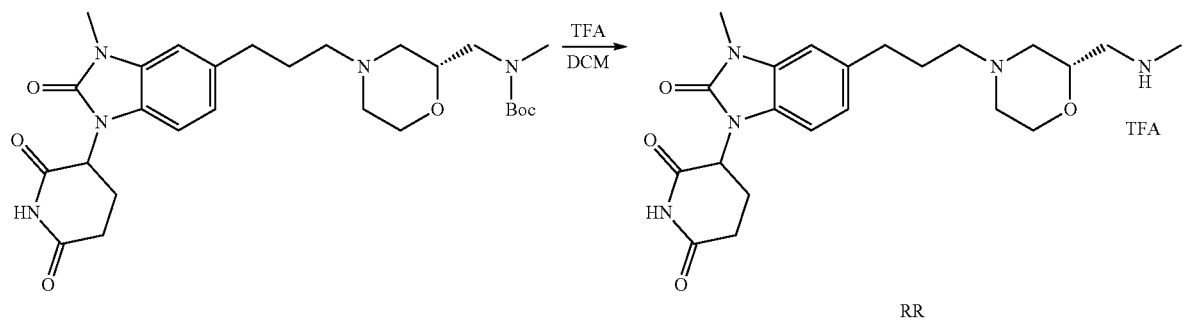

Step 1—3-[5-[3-[(2S)-2-[[(4-methoxyphenyl) methyl-methyl-amino]methyl]morpholin-4-yl]prop-1-ynyl]-3-methyl-2-oxo-benzimidazol-1-yl]piperidine-2,6-dione 1-(4-methoxyphenyl)-N-methyl-N-[[(2S)-4-prop-2-ynylmorpholin-2-yl]methyl]methanamine (1.01 g, 3.51 mmol, Intermediate RQ), 3-(5-bromo-3-methyl-2-oxo-benzimidazol-1-yl)piperidine-2,6-dione (660 mg, 1.95 mmol, Intermediate HN), Pd(PPh$_3$)$_2$Cl$_2$ (274 mg, 390 umol), CuI (74.3 mg, 390 umol), 4 Å molecular sieves (200 mg) and Cs$_2$CO$_3$ (2.54 g, 7.81 mmol) in DMF (12 mL) was degassed with N$_2$ and then heated at 80° C. for 2 hours under N$_2$. On completion, the mixture was filtered and the filtrate was concentrated in vacuo and purified by prep-HPLC (column: Phenomenex luna C18 250*50 mm*10 um; mobile phase: [water (0.225% FA)-ACN]; B %: 5%-35%, 28 mins) to give the title compound (850 mg, 80% yield) as a yellow solid. $^1$H NMR (400 MHz, DMSO-d$_6$) δ 11.13 (s, 1H), 7.33-7.23 (m, 3H), 7.17-7.12 (m, 2H), 6.89-6.84 (m, 2H), 5.44-5.35 (m, 1H), 3.87-3.79 (m, 1H), 3.78-3.72 (m, 1H), 3.71-3.69 (m, 3H), 3.68-3.56 (m, 4H), 3.53 (s, 2H), 3.34 (s, 3H), 2.93-2.80 (m, 1H), 2.74-2.60 (m, 2H), 2.30 (s, 3H), 2.28-2.24 (m, 1H), 2.21-2.18 (m, 1H), 2.18-2.15 (m, 1H), 2.05-2.00 (m, 2H), 1.98-1.96 (m, 1H); LC-MS (ESI$^+$) m/z 546.3 (M+H)$^+$.

Step 2—Tert-butyl N-[[(2R)-4-[3-[1-(2,6-dioxo-3-piperidyl)-3-methyl-2-oxo-benzimidazol-5-yl]propyl]morpholin-2-yl]methyl]-N-methyl-carbamate To a mixture of 3-[5-[3-[(2S)-2-[[(4-methoxyphenyl)methyl-methyl-amino]methyl]morpholin-4-yl]prop-1-ynyl]-3-methyl-2-oxo-benzimidazol-1-yl]piperidine-2,6-dione (200 mg, 367 umol) and (Boc)$_2$O (96.0 mg, 440 umol) in a mixed solvent of IPA (5 mL) and EA (10 mL) was added Pd(OH)$_2$/C (0.1 g, 20 wt %) and Pd/C (0.1 g, 10 wt %). The reaction mixture was stirred at 25° C. for 12 hours under H$_2$ (50 Psi) atmosphere. On completion, the mixture was filtered and the filtrate was concentrated in vacuo. The residue was purified by reversed phase (0.1% FA) to give the title compound (85.0 mg, 44% yield) as a white solid. LC-MS (ESI$^+$) m/z 530.3 (M+H)$^+$.

Step 3—3-[3-Methyl-5-[3-[(2S)-2-(methylaminomethyl)morpholin-4-yl]propyl]-2-oxo-benzimidazol-1-yl]piperidine-2,6-dione To a solution of tert-butyl N-[[(2R)-4-[3-[1-(2,6-dioxo-3-piperidyl)-3-methyl-2-oxo-benzimidazol-5-yl]propyl]morpholin-2-yl]methyl]-N-methyl-carbamate (85.0 mg, 160 umol) in DCM (3 mL) was added TFA (3 mL). The reaction mixture was stirred at 25° C. for 2 hours. On completion, the mixture was concentrated in vacuo to give the title compound (87.0 mg, 100% yield, TFA) as a yellow solid. LC-MS (ESI$^+$) m/z 430.3 (M+H)$^+$.

Tert-butyl N-(4-but-3-ynoxybutyl)-N-methyl-carbamate (Intermediate RS)

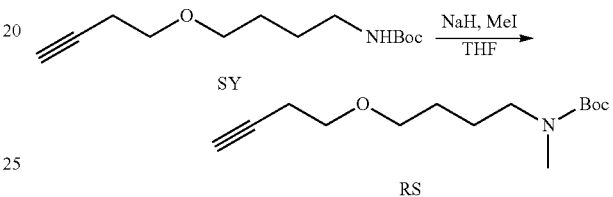

To a solution of tert-butyl N-(4-but-3-ynoxybutyl)carbamate (5.00 g, 20.7 mmol, Intermediate SY) in THF (100 mL) was added NaH (1.24 g, 31.0 mmol, 60% oil dispersion) at 0° C. The mixture was stirred 20° C. for 1 hour. Then MeI (4.41 g, 31.0 mmol) was added. The mixture was stirred at 20° C. for 15 hrs. On completion, the mixture was quenched by water (10 mL) and extracted with EA (2×250 mL). The combined organic layers were concentrated in vacuo to give the title compound (5.00 g, 94% yield) as yellow oil. $^1$H NMR (400 MHz, CDCl$_3$) δ 3.57 (t, J=7.2 Hz, 2H), 3.50 (t, J=6.0 Hz, 2H), 3.24 (s, 2H), 2.85 (s, 3H), 2.48 (dt, J=2.8, 6.8 Hz, 2H), 2.03-1.96 (m, 1H), 1.62-1.56 (m, 4H), 1.47 (s, 9H).

3-[3-Methyl-5-[4-[4-(methylamino)butoxy]butyl]-2-oxo-benzimidazol-1-yl]piperidine-2,6-dione (Intermediate R$^†$)

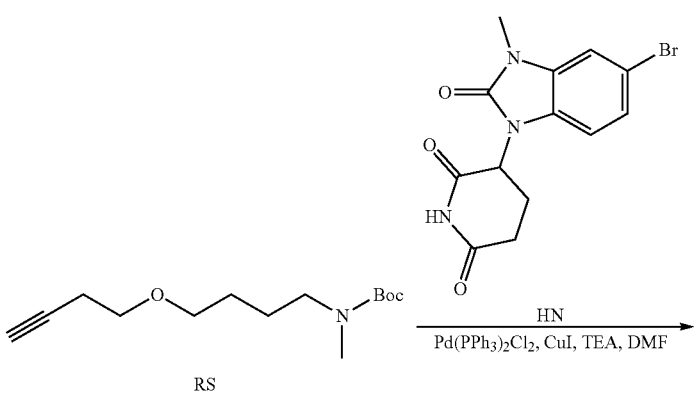

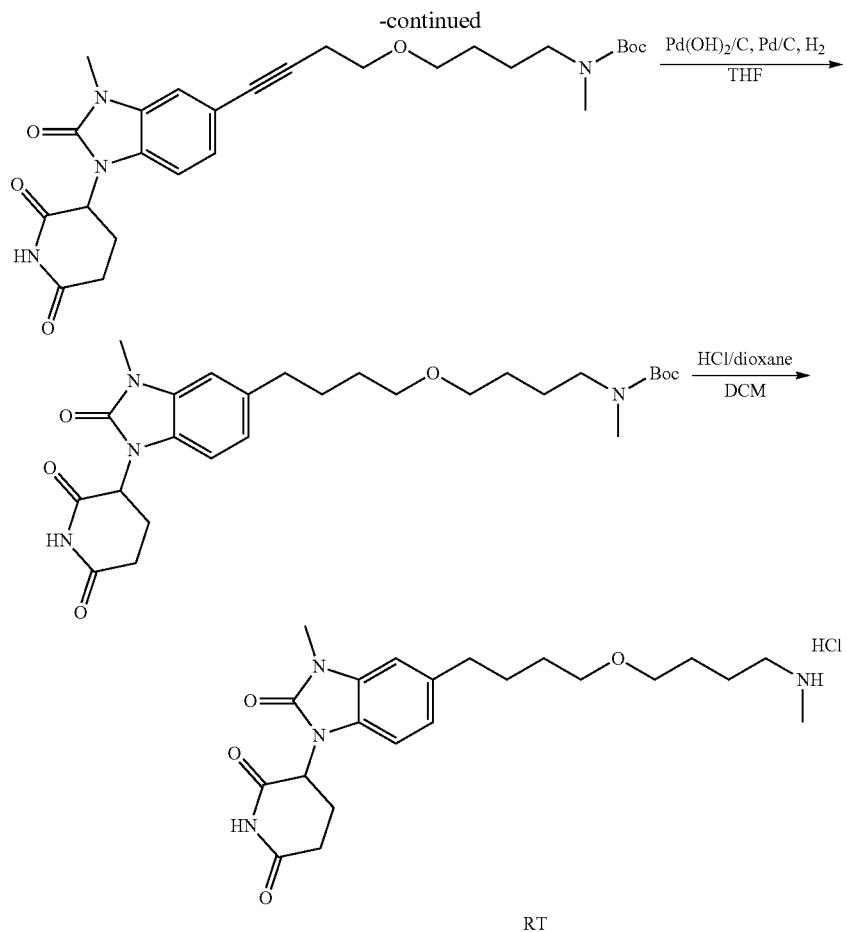

Step 1—Tert-butyl N-[4-[4-[1-(2,6-dioxo-3-piperidyl)-3-methyl-2-oxo-benzimidazol-5-yl]but-3-ynoxy]butyl]-N-methyl-carbamate A mixture of tert-butyl N-(4-but-3-ynoxybutyl)-N-methyl-carbamate (3.06 g, 12.0 mmol, Intermediate RS), 3-(5-bromo-3-methyl-2-oxo-benzimidazol-1-yl)piperidine-2,6-dione (1.50 g, 4.44 mmol, Intermediate HN), Pd(PPh$_3$)$_2$Cl$_2$ (934 mg, 1.33 mmol), CuI (253 mg, 1.33 mmol) and TEA (8.08 g, 79.8 mmol) in DMF (30 mL) was degassed and purged with N$_2$ for 3 times. Then the mixture was stirred at 85° C. for 4 hrs under N$_2$ atmosphere. On completion, the mixture was diluted with water (100 mL) and extracted with EA (2×200 mL). The organic layer was concentrated in vacuo. The residue was purified by reversed phase (0.1% FA) to give the title compound (1.1 g, 46% yield) as yellow solid. $^1$H NMR (400 MHz, DMSO-d$_6$) δ 11.12 (s, 1H), 7.24 (s, 1H), 7.14-7.05 (m, 2H), 5.38 (dd, J=5.2, 12.8 Hz, 1H), 3.56 (t, J=6.8 Hz, 2H), 3.46 (t, J=6.0 Hz, 2H), 3.33 (s, 3H), 3.17 (t, J=6.4 Hz, 2H), 2.93-2.90 (m, 1H), 2.74 (s, 3H), 2.69-2.63 (m, 2H), 2.53-2.51 (m, 2H), 2.08-2.00 (m, 1H), 1.56-1.45 (m, 4H), 1.37 (s, 9H); LC-MS (ESI$^+$) m/z 535.3 (M+Na)$^+$.

Step 2—Tert-butyl N-[4-[4-[1-(2,6-dioxo-3-piperidyl)-3-methyl-2-oxo-benzimidazol-5-yl]butoxy]butyl]-N-methyl-carbamate To a solution of tert-butyl N-[4-[4-[1-(2,6-dioxo-3-piperidyl)-3-methyl-2-oxo-benzimidazol-5-yl]but-3-ynoxy]butyl]-N-methyl-carbamate (1.10 g, 2.15 mmol) in THF (30 mL) was added Pd/C (0.10 g, 10 wt %) and Pd(OH)$_2$/C (0.10 g, 10 wt %). The mixture was stirred at 30° C. for 16 hrs under H$_2$ (15 psi). On completion, the mixture was filtered and the filtrate was concentrated in vacuo to give the title compound (1.10 g, 100% yield) as yellow solid. $^1$H NMR (400 MHz, DMSO-d$_6$) δ 11.09 (s, 1H), 7.06-6.94 (m, 2H), 6.90-6.83 (m, 1H), 5.34 (dd, J=5.2, 12.8 Hz, 1H), 3.40-3.34 (m, 4H), 3.32 (s, 3H), 3.15 (t, J=6.8 Hz, 2H), 2.92-2.88 (m, 1H), 2.74 (s, 3H), 2.64-2.58 (m, 4H), 2.07-1.95 (m, 1H), 1.67-1.58 (m, 2H), 1.57-1.43 (m, 6H), 1.37 (s, 9H); LC-MS (ESI$^+$) m/z 539.2 (M+Na)$^+$.

Step 3—3-[3-Methyl-5-[4-[4-(methylamino)butoxy]butyl]-2-oxo-benzimidazol-1-yl]piperidine-2,6-dione To a solution of tert-butyl N-[4-[4-[1-(2,6-dioxo-3-piperidyl)-3-methyl-2-oxo-benzimidazol-5-yl]butoxy]butyl]-N-methyl-carbamate (1.10 g, 2.13 mmol) in DCM (20 mL) was added HCl/dioxane (4 M, 5 mL). The mixture was stirred at 25° C. for 3 hrs. On completion, the mixture was concentrated in vacuo to give the title compound (1.10 g, 100% yield) as yellow solid. LC-MS (ESI$^+$) m/z 417.2 (M+H)$^+$.

4-(4-(2-(2-(((Cyclopropylmethyl)amino)pyridin-4-yl)
oxazole-4-carboxamido)-3-(difluoromethyl)-1H-
pyrazol-1-yl)benzoic acid (Intermediate RU)

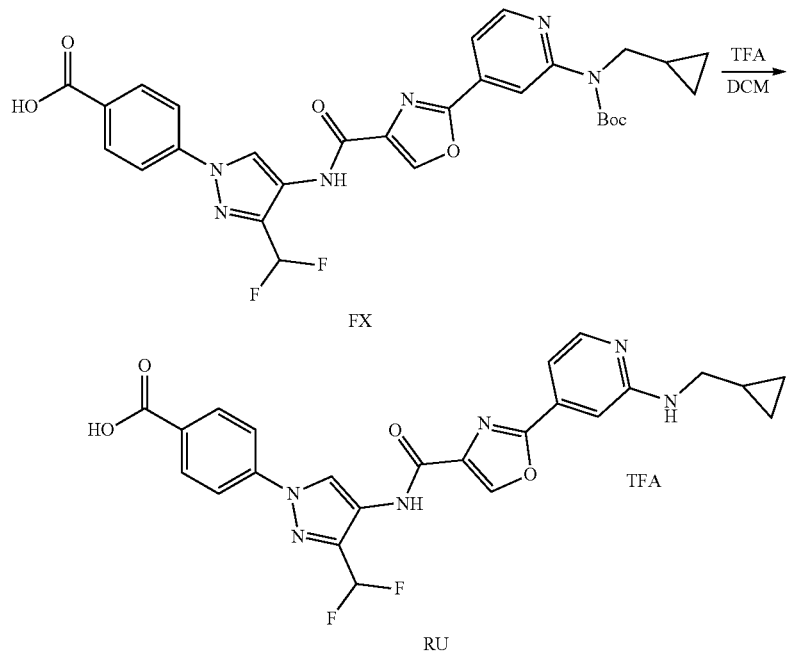

To a solution of 4-[4-[[2-[2-[tert-butoxycarbonyl(cyclopropylmethyl)amino]-4-pyridyl]oxazole-4-carbonyl]amino]-3-(difluoromethyl)pyrazol-1-yl]benzoic acid (44.6 mg, 75.1 umol, Intermediate FX) in DCM (1 mL) was added TFA (770 mg, 6.75 mmol) under N₂ atmosphere. The mixture was stirred at 25° C. for 1 hr. On completion, the reaction mixture was concentrated in vacuo to give the title compound (41.0 mg, 100% yield, TFA) as colorless oil. LC-MS (ESI⁺) m/z 495.2 (M+H)⁺.

(S)-tert-butyl methyl((4-(prop-2-yn-1-yl)morpholin-2-yl)methyl)carbamate (Intermediate RV)

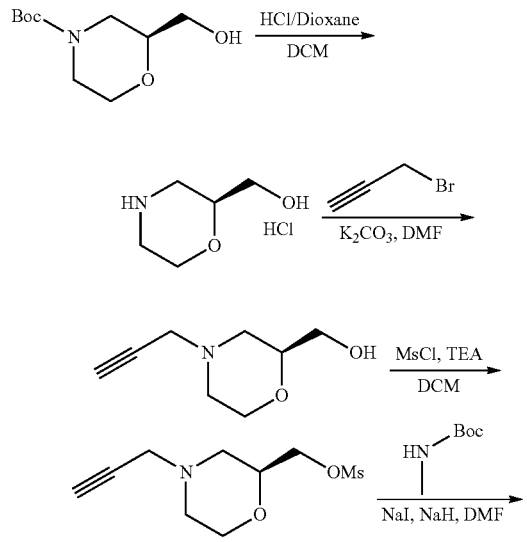

-continued

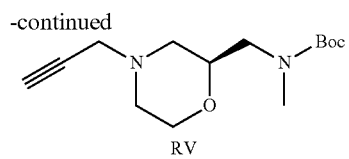

Step 1—(S)-morpholin-2-ylmethanol

To a solution of tert-butyl (2S)-2-(hydroxymethyl)morpholine-4-carboxylate (25.0 g, 115 mmol, CAS #135065-76-8) in DCM (40 mL) was added HCl/dioxane (4 M, 57.5 mL), the reaction mixture was stirred at 25° C. for 2 hrs. On completed, the reaction mixture was concentrated in vacuo to give the title compound (17.0 g, 96% yield, HCl) as yellow oil. ¹H NMR (400 MHz, CDCl₃) δ 4.47 (s, 1H), 3.92-3.89 (m, 1H), 3.75-3.72 (m, 2H), 3.40-3.37 (m, 2H), 3.13 (t, J=2.4, 2H), 2.92-2.6 (m, 2H).

Step 2—(S)-(4-(prop-2-yn-1-yl)morpholin-2-yl)methanol

To a solution of [(2S)-morpholin-2-yl]methanol (12.0 g, 78.1 mmol, HCl) and 3-bromoprop-1-yne (9.29 g, 78.1 mmol) in DMF (200 mL) was added K₂CO₃ (32.4 g, 234 mmol). The reaction mixture was stirred at 25° C. for 12 hrs. On completion, the reaction mixture was diluted with water (300 mL) and extracted with EA (3×80 mL). The combined organic layers was dried over Na₂SO₄, filtered and concentrated in vacuo to give a residue. The residue was purified by silica gel chromatography (petroleum ether/ethyl acetate=10/1 to 2/1) to give the title compound (10.5 g, 86% yield) as a yellow solid. ¹H NMR (400 MHz, CDCl₃) δ

3.98-3.91 (m, 1H), 3.76-3.63 (m, 3H), 3.62-3.56 (m, 1H), 3.31 (d, J=2.4 Hz, 2H), 2.76-2.66 (m, 2H), 2.41 (dt, J=3.6, 11.2 Hz, 1H), 2.28 (t, J=2.4 Hz, 1H), 2.22 (t, J=10.4 Hz, 1H), 1.97-1.66 (m, 1H).

Step 3—(S)-(4-(prop-2-yn-1-yl)morpholin-2-yl)methyl methanesulfonate

To a solution of [(2S)-4-prop-2-ynylmorpholin-2-yl]methanol (2 g, 12.8 mmol) in DCM (30 mL) was added TEA (2.61 g, 25.7 mmol) and MsCl (1.62 g, 14.1 mmol). The mixture was stirred at 25° C. for 2 hrs. On completion, the reaction mixture was quenched with water (2 mL), and then extracted with DCM (3×100 mL). The combined organic layers were washed with brine (2×30 mL), dried over anhydrous sodium sulfate, filtered and concentrated in vacuo to give the title compound (3.00 g, 99% yield) as a yellow oil. $^1$H NMR (400 MHz, CDCl$_3$) δ 4.28-4.20 (m, 2H), 3.99-3.91 (m, 1H), 3.91-3.81 (m, 1H), 3.71 (dt, J=2.4, 11.2 Hz, 1H), 3.33 (d, J=2.4 Hz, 2H), 3.09 (s, 3H), 2.82-2.75 (m, 1H), 2.69 (dd, J=1.2, 11.2 Hz, 1H), 2.51-2.36 (m, 1H), 2.33-2.19 (m, 2H).

Step 4—(S)-tert-butyl methyl((4-(prop-2-yn-1-yl)morpholin-2-yl)methyl)carbamate

To a solution of tert-butyl N-methylcarbamate (1.69 g, 12.8 mmol) and NaI (192 mg, 1.29 mmol) in DMF (30 mL) was added NaH (771 mg, 19.2 mmol, 60% oil dispersion). The reaction mixture was stirred at 25° C. for 0.5 hr. After, [(2S)-4-prop-2-ynylmorpholin-2-yl]methyl methanesulfonate (3.00 g, 12.8 mmol) was added into the mixture. The resulting reaction mixture was stirred 90° C. for 12 hrs. On completion, the reaction mixture was quenched with water (0.1 mL) and concentrated in vacuo. The residue was purified by column chromatography (SiO$_2$, PE:EA=5:1) to give the title compound (250 mg, 7% yield) as a yellow oil. $^1$H NMR (400 MHz, CDCl$_3$) δ 3.95-3.86 (m, 1H), 3.77-3.61 (m, 2H), 3.47-3.38 (m, 1H), 3.32-3.30 (m, 2H), 3.17 (dd, J=2.4, 10.8 Hz, 1H), 2.93 (s, 3H), 2.79-2.65 (m, 2H), 2.39 (dt, J=2.4, 11.2 Hz, 1H), 2.28-2.26 (m, 1H), 2.11 (t, J=10.8 Hz, 1H), 1.46 (s, 9H).

3-(3-Methyl-5-(3-((R)-2-((methylamino)methyl)morpholino)propyl)-2-oxo-2,3-dihydro-1H-benzo[d]imidazol-1-yl)piperidine-2,6-dione (Intermediate RW)

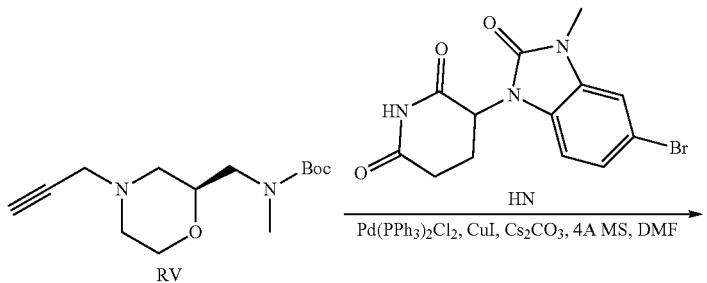

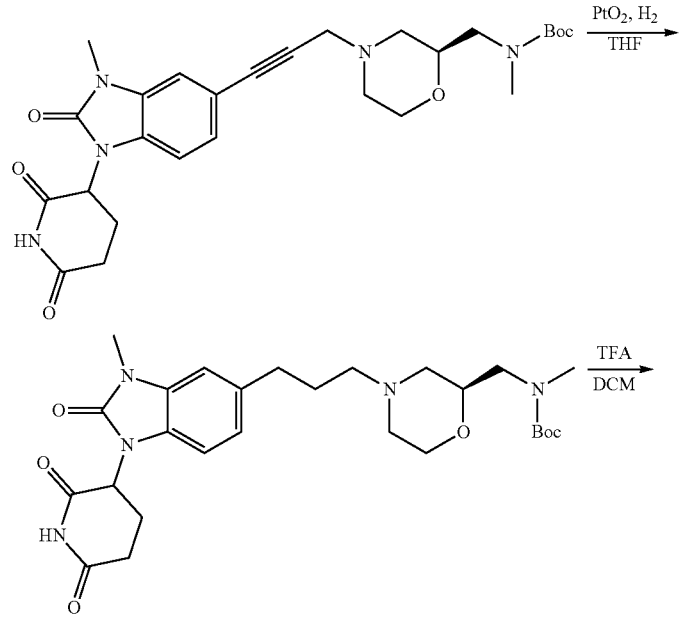

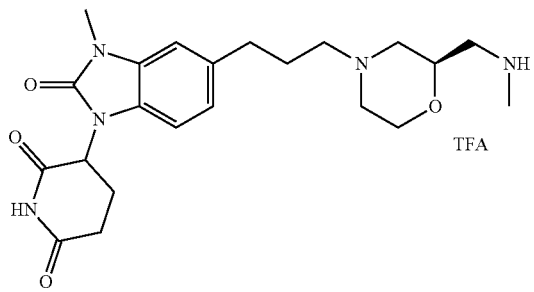

RW

Step 1—Tert-butyl ((((2S)-4-(3-(1-(2,6-dioxopiperidin-3-yl)-3-methyl-2-oxo-2,3-dihydro-1H-benzo[d]imidazol-5-yl)prop-2-yn-1-yl)morpholin-2-yl)methyl)(methyl)carbamate To a mixture of 3-(5-bromo-3-methyl-2-oxo-benzimidazol-1-yl)piperidine-2,6-dione (180 mg, 532 umol, Intermediate HN), tert-butyl N-methyl-N-[[(2S)-4-prop-2-ynylmorpholin-2-yl]methyl]carbamate (214 mg, 798 umol, Intermediate RV), Pd(PPh$_3$)$_2$Cl$_2$ (37.3 mg, 53.2 umol), CuI (10.1 mg, 53.2 umol), 4 Å molecular sieves (200 mg) and Cs$_2$CO$_3$ (693 mg, 2.13 mmol) in DMF (10 mL) was degassed with N$_2$ and then heated to 80° C. for 2 hours under N$_2$. On completion, the reaction mixture was concentrated in vacuo. The residue was purified by reversed-phase HPLC (0.1% FA, condition) to give the title compound (150 mg, 42% yield) as yellow oil. LC-MS (ESI$^+$) m/z 526.1 (M+H).

Step 2—Tert-butyl ((((2S)-4-(3-(1-(2,6-dioxopiperidin-3-yl)-3-methyl-2-oxo-2,3-dihydro-1H-benzo[d]imidazol-5-yl)propyl)morpholin-2-yl)methyl)(methyl)carbamate To a solution of tert-butyl N-[[(2S)-4-[3-[1-(2,6-dioxo-3-piperidyl)-3-methyl-2-oxo-benzimidazol-5-yl]prop-2-ynyl]morpholin-2-yl]methyl]-N-methyl-carbamate (150 mg, 228 umol) in THF (20 mL) was added PtO$_2$ (13.8 mg, 6.10 umol) under N$_2$ atmosphere. The suspension was degassed and purged with H$_2$ seven times. The mixture was stirred under H$_2$ (15 Psi) at 25° C. for 2 hrs. On completion, the reaction mixture was filtered and concentrated in vacuo to give the title compound (40.0 mg, 31% yield) as colorless oil. LC-MS (ESI$^+$) m/z 530.3 (M+H)$^+$.

Step 3—3-(3-Methyl-5-(3-((R)-2-((methylamino)methyl)morpholino)propyl)-2-oxo-2,3-dihydro-1H-benzo[d]imidazol-1-yl)piperidine-2,6-dione To a solution of tert-butyl N-[[(2S)-4-[3-[1-(2,6-dioxo-3-piperidyl)-3-methyl-2-oxo-benzimidazol-5-yl]propyl]morpholin-2-yl]methyl]-N-methyl-carbamate (40.0 mg, 75.5 umol) in DCM (3 mL) was added TFA (308 mg, 2.70 mmol) under N$_2$ atmosphere. The mixture was stirred at 25° C. for 15 minutes. On completion, the reaction mixture was concentrated in vacuo to give the title compound (41.0 mg, 100% yield, TFA) as colorless. LC-MS (ESI$^+$) m/z 430.2 (M+H)$^+$.

2-[2-[2-[2-[3-[1-(2,6-dioxo-3-piperidyl)-3-methyl-2-oxo-benzimidazol-4-yl]propoxy]ethoxy]ethoxy]ethoxy]acetic acid (Intermediate RX)

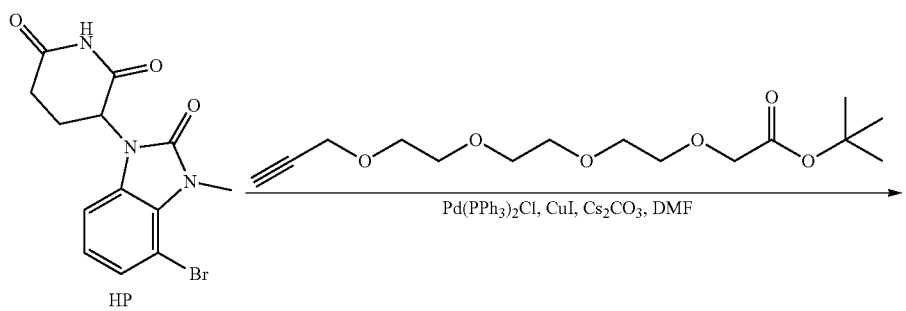

-continued

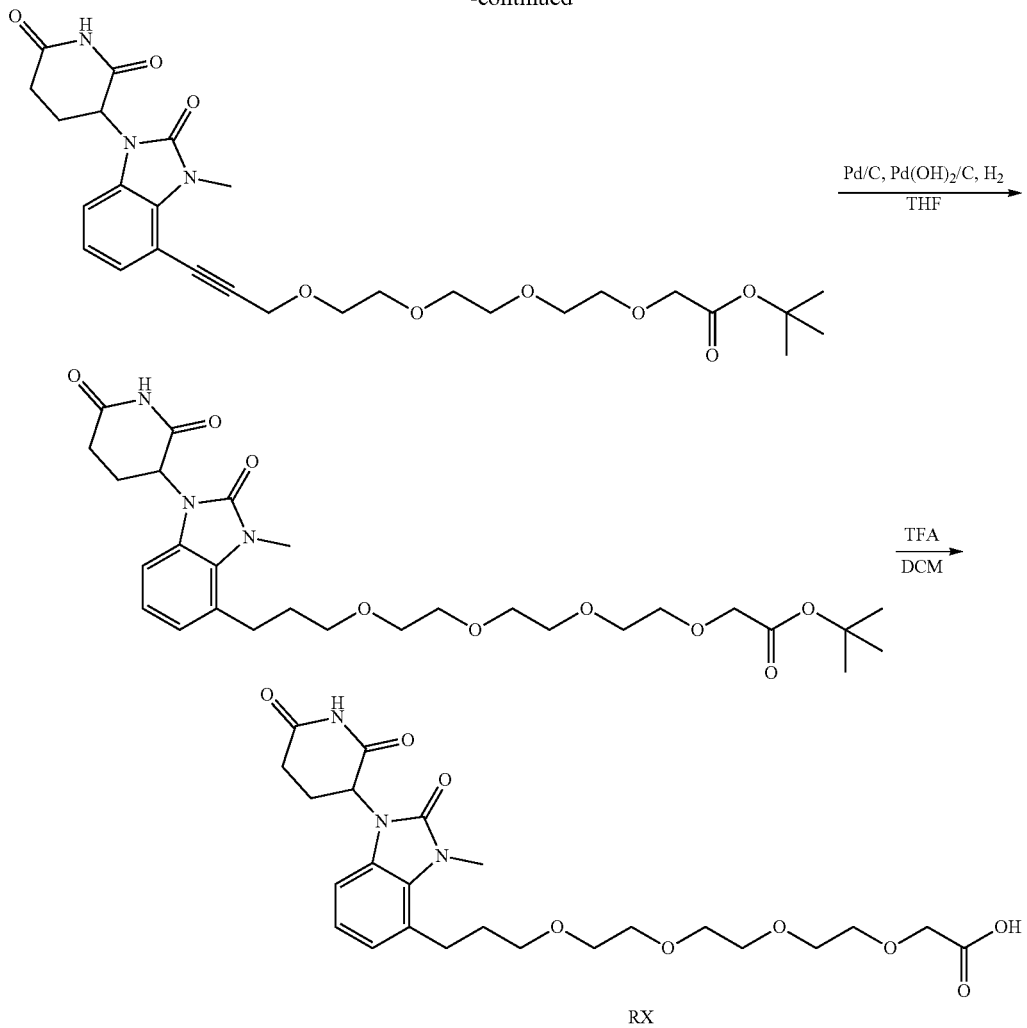

Step 1—Tert-butyl 2-[2-[2-[2-[3-[1-(2,6-dioxo-3-piperidyl)-3-methyl-2-oxo-benzimidazol-4-yl]prop-2-ynoxy]ethoxy]ethoxy]ethoxy]acetate To a mixture of 3-(4-bromo-3-methyl-2-oxo-benzimidazol-1-yl)piperidine-2,6-dione (600 mg, 1.77 mmol, Intermediate HP), tert-butyl 2-[2-[2-(2-prop-2-ynoxyethoxy)ethoxy]ethoxy]acetate (1.07 g, 3.55 mmol, synthesized via Steps 1-2 of Example 441, I-447) in DMF (10 mL) was added CuI (67.6 mg, 355 umol), $Cs_2CO_3$ (2.89 g, 8.87 mmol) and $Pd(PPh_3)_2Cl_2$ (249.08 mg, 355 umol) under $N_2$. The reaction mixture was stirred at 80° C. for 3 hours. On completion, the mixture was poured into water (30 mL). The aqueous phase was extracted with ethyl acetate (2×30 mL). The combined organic phase was washed with brine (2×30 mL), dried with anhydrous $Na_2SO_4$, filtered and concentrated in vacuo to give a residue. The residue was purified by reversed-phase (0.1% FA condition) to give the title compound (598 mg, 60% yield) as brown oil. $^1$H NMR (400 MHz, $CDCl_3$) δ 8.29 (s, 1H), 7.16 (d, J=7.6 Hz, 1H), 6.97 (t, J=8.0 Hz, 1H), 6.75 (d, J=8.0 Hz, 1H), 5.23-5.15 (m, 1H), 4.46 (s, 2H), 4.01 (s, 2H), 3.76 (s, 3H), 3.76-3.66 (m, 12H), 2.99-2.68 (m, 3H), 2.29-2.16 (m, 1H), 1.46 (s, 9H).

Step 2—Tert-butyl 2-[2-[2-[2-[3-[1-(2,6-dioxo-3-piperidyl)-3-methyl-2-oxo-benzimidazol-4-yl]propoxy]ethoxy]ethoxy]ethoxy]acetate To a solution of tert-butyl 2-[2-[2-[2-[3-[1-(2,6-dioxo-3-piperidyl)-3-methyl-2-oxo-benzimidazol-4-yl]prop-2-ynoxy]ethoxy]ethoxy]ethoxy]acetate (578 mg, 1.03 mmol) in THF (5 mL) was added Pd/C (100 mg, 20 wt %) and $Pd(OH)_2$/C (100 mg, 20 wt %) under $N_2$. The suspension was degassed under vacuum and purged with $H_2$ gas three times. The mixture was stirred at 20° C. for 12 hours under $H_2$ (15 psi). On completion, the mixture was filtrated and the filtrate was concentrated in vacuo to give a title compound (540 mg, 92% yield) as brown oil. LC-MS (ESI$^+$) m/z 586.3 (M+Na)$^+$.

Step 3—2-[2-[2-[2-[3-[1-(2,6-Dioxo-3-piperidyl)-3-methyl-2-oxo-benzimidazol-4-yl]propoxy]ethoxy]ethoxy]ethoxy]acetic acid To a mixture of tert-butyl 2-[2-[2-[2-[3-[1-(2,6-dioxo-3-piperidyl)-3-methyl-2-oxo-benzimidazol-4-yl]propoxy]ethoxy]ethoxy]ethoxy]acetate (520 mg, 922 umol) in DCM (2 mL) was added TFA (210 mg, 1.85 mmol). The reaction mixture was stirred at 20° C. for 1 hour. On completion, the mixture was concentrated in vacuo to give a residue. The residue was purified by column chromatography to give the title compound (436 mg, 93% yield) as brown oil. LC-MS (ESI$^+$) m/z 508.3 (M+H)$^+$.

Step 2—Tert-butyl 4-(trans-4-aminocyclohexyl) piperazine-1-carboxylate

A mixture of tert-butyl 4-[4-(benzyloxycarbonylamino) cyclohexyl]piperazine-1-carboxylate (8.00 g, 16.4 mmol) and Pd/C (800 mg, 10 wt %) in MeOH (80 mL) was stirred at 25° C. for 2 hours under H$_2$ (15 Psi). On completion, the mixture was filtered, and the cake was washed with MeOH (50 mL). The filtrate and washings were combined and concentrated in vacuo to give the title compound (5.30 g, 100% crude yield) as white solid. $^1$H NMR (400 MHz, CDCl$_3$) δ 3.49-3.21 (m, 4H), 2.64-2.58 (m, 1H), 2.54 (m, 4H), 2.31-2.20 (m, 1H), 1.88 (t, J=15.2 Hz, 4H), 1.45 (s, 9H), 1.34-1.22 (m, 2H), 1.17-1.05 (m, 2H).

2-[4-[4-[1-(2,6-Dioxo-3-piperidyl)-3-methyl-2-oxo-benzimidazol-5-yl]butoxy]butylamino]acetic acid (Intermediate SB)

Step 1—Tert-butyl 2-[4-[4-[1-(2,6-dioxo-3-piperidyl)-3-methyl-2-oxo-benzimidazol-5-yl]butoxy] butylamino]acetate A mixture of 3-[5-[4-(4-aminobutoxy)butyl]-3-methyl-2-oxo-benzimidazol-1-yl]piperidine-2,6-dione (200 mg, 455 umol, HCl, Intermediate OD), tert-butyl 2-bromoacetate (80.0 mg, 410 umol, CAS #5292-43-3) and TEA (100 mg, 988 umol) in DMF (2 mL) was stirred at 25° C. for 16 hours. On completion, the mixture was purified by reverse phase flash chromatography (FA condition) to give the title compound (100 mg, 31% yield) as light yellow gum. $^1$H NMR (400 MHz, DMSO-d$_6$) δ 11.09 (s, 1H), 7.02-6.98 (m, 2H), 6.86 (d, J=8.0 Hz, 1H), 5.37-5.28 (m, 1H), 3.62-3.57 (m, 2H), 3.34 (s, 3H), 3.32 (m, 4H), 2.91-2.83 (m, 1H), 2.65-2.56 (m, 6H), 2.04-1.95 (m, 1H), 1.77-1.73 (m, 1H), 1.63-1.47 (m, 8H), 1.41 (s, 9H).

Step 2—2-[4-[4-[1-(2,6-Dioxo-3-piperidyl)-3-methyl-2-oxo-benzimidazol-5-yl]butoxy]buty-lamino]acetic acid To a solution of tert-butyl 2-[4-[4-[1-(2,6-dioxo-3-piperidyl)-3-methyl-2-oxo-benzimidazol-5-yl]butoxy]buty-

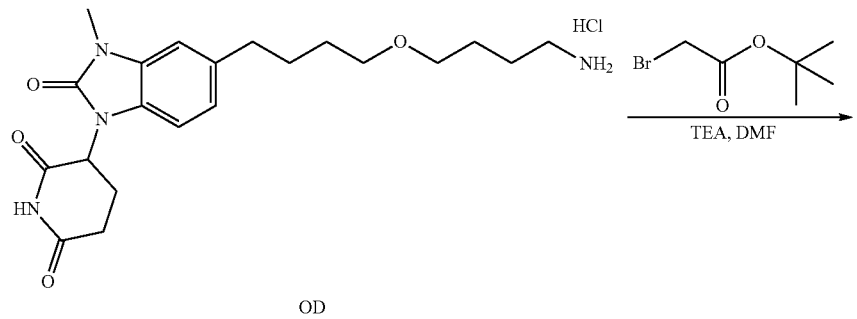

OD

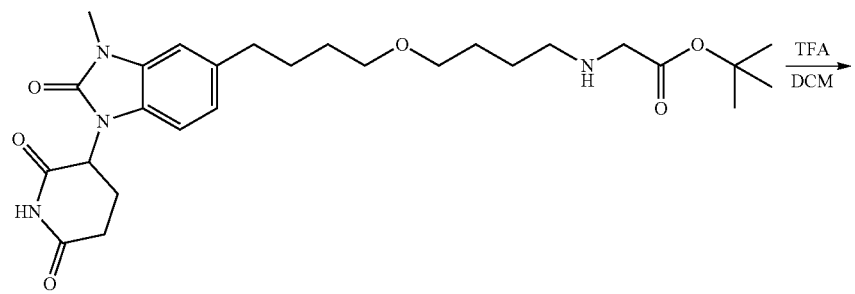

SB lamino]acetate (125 mg, 176 umol) in DCM (2 mL) was added TFA (1 mL) at 25° C. The mixture was stirred at 25° C. for 6 hours. On completion, the mixture was concentrated in vacuo to give the title compound (120 mg, crude, TFA) as yellow gum. LC-MS (ESI+) m/z 461.2 (M+H)+.

Tert-butyl N-(3-but-3-ynoxypropyl)carbamate (Intermediate SD)

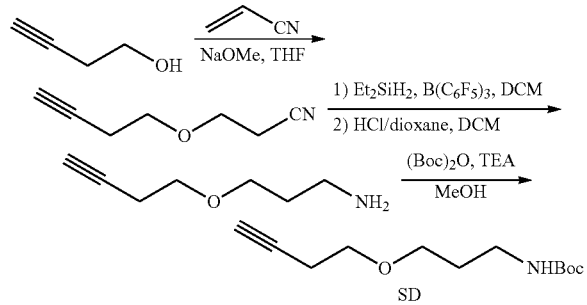

Step 1—3-But-3-ynoxypropanenitrile

To a solution of prop-2-enenitrile (2.00 g, 37.6 mmol) and but-3-yn-1-ol (7.93 g, 113 mmol) in THF (40.0 mL) was added NaOMe (203 mg, 3.77 mmol). The mixture was stirred at 25° C. for 16 hrs. On completion, the mixture was concentrated in vacuo to give the title compound (4.60 g, 99% yield) as yellow oil. $^1$H NMR (400 MHz, CDCl$_3$) δ 3.71 (t, J=6.4 Hz, 2H), 3.63 (t, J=6.8 Hz, 2H), 2.62 (t, J=6.4 Hz, 2H), 2.52-2.45 (m, 2H), 2.00 (t, J=2.4 Hz, 1H).

Step 2—3-But-3-ynoxypropan-1-amine

To a mixture of diethylsilane (3.58 g, 40.6 mmol) and tris(perfluorophenyl)borane (83.1 mg, 162 umol) in DCM (30.0 mL) was added 3-but-3-ynoxypropanenitrile (2.00 g, 16.2 mmol). The mixture was stirred at 25° C. for 16 hours. Then HCl/dioxane (4.00 M, 20.0 mL) was added, and the mixture was stirred for 1 hour. On completion, the mixture was concentrated in vacuo. The residue was dissolved in water (10.0 mL), and then extracted with EA (10.0 mL). The aqueous layer was concentrated in vacuo to give the title compound (2.30 g, 86% yield, HCl) as colorless oil. $^1$H NMR (400 MHz, CDCl$_3$) δ 8.06 (s, 2H), 3.80-3.76 (m, 2H), 3.63-3.59 (m, 2H), 3.24 (s, 2H), 2.64-2.57 (m, 2H), 2.21-2.15 (m, 1H), 2.08-2.04 (m, 2H).

Step 3—Tert-butyl N-(3-but-3-ynoxypropyl)carbamate

To a solution of 3-but-3-ynoxypropan-1-amine (300 mg, 1.83 mmol, HCl) in MeOH (10.0 mL) was added (Boc)$_2$O (1.00 g, 4.58 mmol) and TEA (371 mg, 3.67 mmol). The mixture was stirred at 25° C. for 16 hours. On completion, the mixture was concentrated in vacuo. The residue was purified by silica gel chromatography (PE:EA=5:1) to give the title compound (200 mg, 48% yield) as colorless oil. $^1$H NMR (400 MHz, DMSO-d$_6$) δ 4.85 (s, 1H), 3.51-3.44 (m, 4H), 3.21-3.10 (m, 2H), 2.43-2.38 (m, 2H), 1.95-1.90 (m, 1H), 1.75-1.63 (m, 2H), 1.37 (s, 9H).

3-[(5S)-5-(3-bromophenyl)-2-oxo-oxazolidin-3-yl]piperidine-2,6-dione (Intermediate SE)

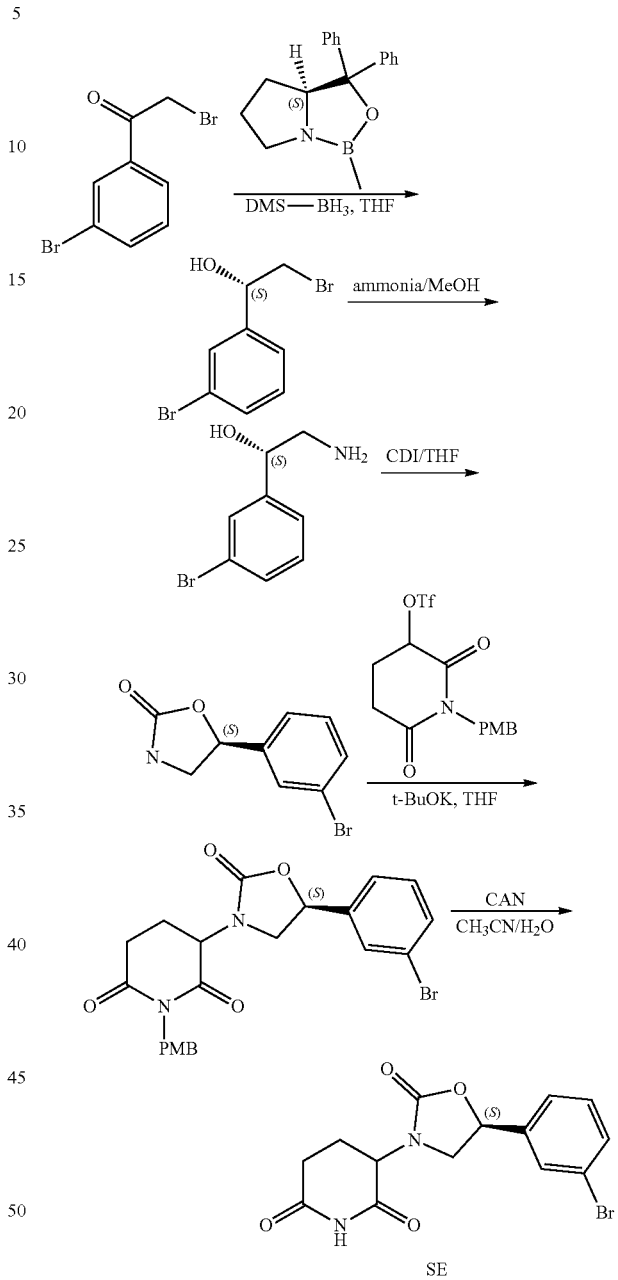

Step 1—(S)-2-bromo-1-(3-bromophenyl)ethanol

To a stirred solution of (S)-1-methyl-3,3-diphenylhexahydropyrrolo[1,2-c][1,3,2]oxazaborole (1 g, 3.61 mmol, CAS #112022-81-8) in THF (50 mL) was added BH$_3$.DMS (10 M, 2.5 mL, 25.3 mmol) at 0° C. The mixture was stirred for 0.5 h at 0° C. To the reaction mixture was added a solution of 2-bromo-1-(3-bromophenyl)ethanone (10 g, 36.1 mmol) in THF (30 mL) dropwise at 0° C. The mixture was stirred for 12 h at rt. To the mixture was added MeOH dropwise, where the mixture released bubbles of gas. Addition of MeOH was halted after bubbling stopped. Then the mixture was concentrated and purified by column (PE/EA=50/1 to 20/1 to 10/1 to 5/1) to give the title compound (10 g, 100% yield) as a white solid. $^1$H NMR (400 MHz, CDCl$_3$) δ 7.56 (t, J=1.8 Hz, 1H), 7.47-7.45 (m, 1H), 7.32-7.30 (m, 1H), 7.26-7.22 (m, 1H), 4.90 (d, J=8.7 Hz, 1H), 3.63 (dd, J=10.5, 3.4 Hz, 1H), 3.51 (dd, J=10.5, 8.8 Hz, 1H), 2.68 (d, J=1.6 Hz, 1H).

Step 2—(S)-2-amino-1-(3-bromophenyl)ethanol

To a solution of (S)-2-bromo-1-(3-bromophenyl)ethanol (11 g, 90.3 mmol) in MeOH (80 mL) was added NH$_3$—H$_2$O (25%, 200 mL) at 0° C. under N$_2$. The reaction mixture was stirred for 12 h under N$_2$ at room temperature. The mixture was concentrated. The solid was washed with EA to give the title compound (6.2 g, 74% yield) as a white solid. $^1$H NMR (400 MHz, DMSO-d$_6$) δ 7.70 (br s, 2H), 7.60 (t, J=1.9 Hz, 1H), 7.54-7.51 (m, 1H), 7.42-7.34 (m, 2H), 6.17 (d, J=3.8 Hz, 1H), 4.81-4.79 (m, 1H), 3.09 (dd, J=12.8, 3.2 Hz, 1H), 2.87 (dd, J=12.8, 9.6 Hz, 1H).

Step 3—(S)-5-(3-bromophenyl)oxazolidin-2-one

A mixture of (S)-2-amino-1-(3-bromophenyl)ethanol (1 g, 4.63 mmol), CDI (1.1 g, 6.94 mmol) and THF (30 mL) was heated to 80° C. and stirred for overnight at 80° C. under N$_2$. To the mixture was added H$_2$O (20 mL), then the mixture was extracted with EA (50 mL). The organic layer was concentracted and purified by column chromatography on silica gel (PE/EA=2/1 to 1/1) to give the title compound (300 mg, 27% yield) as a yellow solid. $^1$H NMR (400 MHz, CDCl$_3$) δ 7.55-7.54 (m, 1H), 7.51 (dt, J=6.9, 2.0 Hz, 1H), 7.32-7.29 (m, 2H), 5.60 (t, J=8.0 Hz, 1H), 5.09 (br s, 1H), 4.00 (dt, J=0.6, 8.7 Hz, 1H), 3.53-3.49 (m, 1H).

Step 4—(R)-3-((S)-5-(3-bromophenyl)-2-oxooxazolidin-3-yl)-1-(4-methoxybenzyl)piperidine-2,6-dione To a solution of (S)-5-(3-bromophenyl)oxazolidin-2-one (8.1 g, 33.5 mmol) in THF (100 mL) was added t-BuOK (5.6 g, 50.3 mmol) at 0° C. under N$_2$. The mixture was stirred for 1 h at 0° C. Then to the mixture was added 1-(4-methoxybenzyl)-2,6-dioxopiperidin-3-yl trifluoromethanesulfonate (14 g, 36.8 mmol) at 0° C. under N$_2$. The mixture was stirred for 2 h at 0° C.~10° C. To the mixture was added EA (100 mL), then the solution was washed with H$_2$O (100 mL), brine (50 mL), dried over Na$_2$SO$_4$, filtered, concentrated and purified by column chromatography on silica gel (PE/EA=2/1) to give a mixture of desired product and starting material. Then the mixture was re-purified by flash column chromatography (210 nm, 30% MeCN in H$_2$O) to give product (R)-3-((S)-5-(3-bromophenyl)-2-oxooxazolidin-3-yl)-1-(4-methoxybenzyl)piperidine-2,6-dione (4.0 g, 25% yield) as a white solid. $^1$H NMR (400 MHz, CDCl$_3$) δ 7.60-7.57 (m, 2H), 7.39-7.36 (m, 2H), 7.32-7.28 (m, 2H), 6.81-6.77 (m, 2H), 5.48 (t, J=8.4 Hz, 1H), 4.87 (s, 2H), 4.69 (dd, J=13.5, 5.2 Hz, 1H), 3.79 (t, J=8.4 Hz, 1H), 3.76 (s, 3H), 3.42 (t, J=8.0 Hz, 1H), 2.95 (ddd, J=17.8, 4.5, 2.4 Hz, 1H), 2.77 (ddd, J=17.8, 13.5, 5.5 Hz, 1H), 2.24-2.07 (m, 2H).

Step 5—(R)-3-((S)-5-(3-bromophenyl)-2-oxooxazolidin-3-yl)piperidine-2,6-dione

To a solution of (R)-3-((S)-5-(3-bromophenyl)-2-oxooxazolidin-3-yl)-1-(4-methoxybenzyl)piperidine-2,6-dione (4.0 g, 8.47 mmol) in MeCN (90 mL) was added dropwise a solution of CAN (18.6 g, 33.9 mmol) in H$_2$O (20 mL) at 0° C. The mixture was stirred for 3 h at 0° C.~10° C. To the mixture was added H$_2$O (50 mL), then the solution was extracted with EA (100 mL). The organic layer was washed with brine (30 mL), dried over Na$_2$SO$_4$, filtered, concentrated to give a yellow solid. The solid was washed with EA (30 mL) to give the title compound (1.2 g, 40% yield) as a white solid. The filtrate was concentrated and purified by flash (210 nm, 30% MeCN in H2O) to give another portion of the title compound (0.2 g, 7% yield) as a white solid, the total yield is 47%. $^1$H NMR (400 MHz, DMSO-d$_6$) δ 11.00 (s, 1H), 7.72 (t, J=1.6 Hz, 1H), 7.63-7.60 (m, 1H), 7.50-7.49 (m, 1H), 7.42 (t, J=8 Hz, 1H), 5.63 (dd, J=7.6, 8.8 Hz, 1H), 4.71 (dd, J=5.2, 13.2 Hz, 1H), 3.94 (t, J=8.8 Hz, 1H), 3.29-3.25 (m, 1H), 2.92-2.82 (m, 1H), 2.59-2.57 (m, 1H), 2.25-2.14 (m, 1H), 2.03-2.01 (m, 1H). LC/MS (ESI, m/z): [M+1]$^+$=355.0.

3-[(5S)-5-[3-[4-(3-aminopropoxy)but-1-ynyl]phenyl]-2-oxo-oxazolidin-3-yl]piperidine-2,6-dione (Intermediate SF)

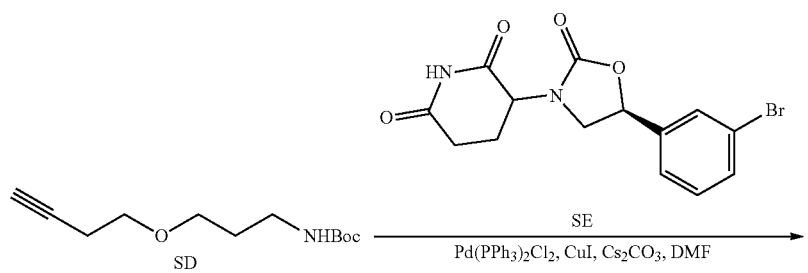

-continued

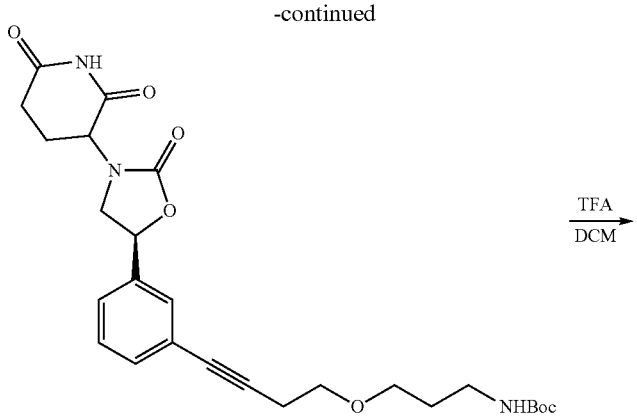

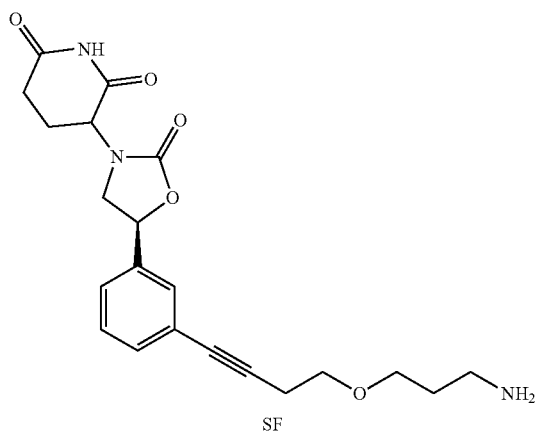

Step 1—Tert-butyl N-[3-[4-[3-[(5S)-3-(2,6-dioxo-3-piperidyl)-2-oxo-oxazolidin-5-yl]phenyl]but-3-ynoxy]propyl]carbamate To a solution of tert-butyl N-(3-but-3-ynoxypropyl)carbamate (146 mg, 645 umol, Intermediate SD) and 3-[(5S)-5-(3-bromophenyl)-2-oxo-oxazolidin-3-yl]piperidine-2,6-dione (190 mg, 537 umol, Intermediate SE) in DMF (8.00 mL) was added Pd(PPh$_3$)$_2$Cl$_2$ (37.7 mg, 53.8 umol), CuI (10.2 mg, 53.8 umol), Cs$_2$CO$_3$ (701 mg, 2.15 mmol) and 4 Å molecular sieves (30 mg) under N$_2$, and the mixture was stirred at 80° C. for 3 hrs. On completion, the mixture was filtered and the filtrate was concentrated in vacuo. The mixture was purified by prep-HPLC (reverse phase: 0.1% FA) to give the title compound (140 mg, 52% yield) as yellow solid. $^1$H NMR (400 MHz, DMSO-d$_6$) δ 11.0 (s, 1H), 7.51-7.39 (m, 4H), 6.79 (s, 1H), 5.73-5.58 (m, 1H), 4.76-4.63 (m, 1H), 3.97-3.84 (m, 1H), 3.59-3.51 (m, 2H), 3.46-3.43 (m, 2H), 3.30-3.22 (m, 1H), 3.03-2.95 (m, 2H), 2.92-2.76 (m, 1H), 2.70-2.67 (m, 2H), 2.61-2.54 (m, 1H), 2.28-2.14 (m, 1H), 2.05-1.93 (m, 1H), 1.68-1.57 (m, 2H), 1.38 (s, 9H).

Step 2—3-[(5S)-5-[3-[4-(3-aminopropoxy)but-1-ynyl]phenyl]-2-oxo-oxazolidin-3-yl]piperidine-2,6-dione To a solution of tert-butyl N-[3-[4-[3-[(5S)-3-(2,6-dioxo-3-piperidyl)-2-oxo-oxazolidin-5-yl]phenyl]but-3-ynoxy]propyl]carbamate (110 mg, 220 umol) in DCM (4.00 mL) was added TFA (6.16 g, 54.0 mmol). The reaction mixture was stirred at 25° C. for 1 hr. On completion, the mixture was concentrated in vacuo to give the title compound (110 mg, 97% yield, TFA) as yellow solid. LC-MS (ESI$^+$) m/z 400.2 (M+H)$^+$.

But-3-ynyl methanesulfonate (Intermediate SG)

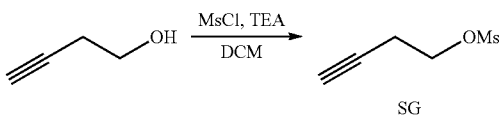

To a solution of but-3-yn-1-ol (10.0 g, 142 mmol, CAS #927-74-2) and TEA (43.3 g, 428 mmol) in DCM (250 mL) was added MsCl (21.2 g, 185 mmol) dropwise at 0° C. The mixture was stirred at 25° C. for 1 hour. On completion, the reaction mixture was quenched by water (150 mL) at 0° C. The organic layers were washed with water (150 mL), dried over Na$_2$SO$_4$, filtered and concentrated in vacuo to give the title compound (20.0 g, 95% yield) as light yellow oil. $^1$H NMR (400 MHz, CDCl$_3$) 4.31 (t, J=6.4 Hz, 2H), 3.06 (s, 3H), 2.68-2.64 (M, 2H), 2.07 (t, J=2.8 Hz, 1H).

1821

Tert-butyl N-[(1-but-3-ynyl-4-piperidyl)methyl]-N-methyl-carbamate (Intermediate SH)

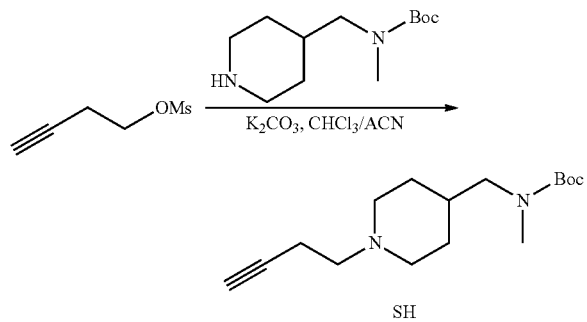

To a solution of tert-butyl N-methyl-N-(4-piperidylmethyl)carbamate (3.00 g, 13.1 mmol, CAS #138200-04-5) in a mixed solvent of CHCl$_3$ (25 mL) and ACN (25 mL) was added K$_2$CO$_3$ (3.63 g, 26.2 mmol) and but-3-ynyl methanesulfonate (2.53 g, 17.0 mmol, Intermediate SG). The mixture was stirred at 70° C. for 16 hours. On completion, the reaction mixture was filtered and concentrated in vacuo to give a residue. The residue was purified by column chromatography (SiO$_2$, PE/EA=6/1) to give the title compound (2.30 g, 62% yield) as light yellow oil. $^1$H NMR (400 MHz, CDCl$_3$) δ 3.09 (d, J=6.8 Hz, 2H), 2.97-2.97 (m, 2H), 2.84 (s, 3H), 2.59 (t, J=8.0 Hz, 2H), 2.45-2.32 (m, 2H), 2.04-1.93 (m, 3H), 1.65-1.55 (m, 3H), 1.45 (s, 9H), 1.30-1.20 (m, 2H).

3-[3-Methyl-5-[4-[4-(methylaminomethyl)-1-piperidyl]but-1-ynyl]-2-oxo-benzimidazol-1-yl]piperidine-2,6-dione (Intermediate SI)

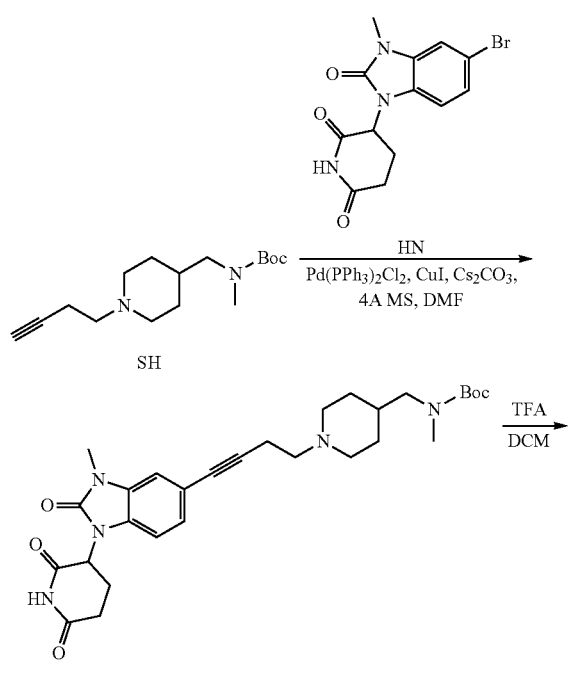

Step 1—Tert-butyl N-[[1-[4-[1-(2,6-dioxo-3-piperidyl)-3-methyl-2-oxo-benzimidazol-5-yl]but-3-ynyl]-4-piperidyl]methyl]-N-methyl-carbamate To a solution of 3-(5-bromo-3-methyl-2-oxo-benzimidazol-1-yl)piperidine-2,6-dione (500 mg, 1.48 mmol, Intermediate HN) and tert-butyl N-[(1-but-3-ynyl-4-piperidyl)methyl]-N-methyl-carbamate (1.04 g, 3.70 mmol, Intermediate SH) in DMF (15 mL) was added Cs$_2$CO$_3$ (1.93 g, 5.91 mmol), CuI (56.3 mg, 295 umol), 4 Å molecular sieves (500 mg) and Pd(PPh$_3$)$_2$Cl$_2$ (207 mg, 295 umol). The mixture was stirred at 80° C. for 2 hours. On completion, the reaction mixture was filtered and concentrated in vacuo; the residue was diluted with water (30 mL), and then extracted with EA (3×40 mL). The combined organic layers were dried over Na$_2$SO$_4$, filtered and concentrated in vacuo to give a residue. The residue was purified by prep-HPLC (FA condition) to give the title compound (80.0 mg, 10% yield) as white solid. $^1$H NMR (400 MHz, DMSO-d$_6$) δ 8.16 (s, 1H), 7.14 (dd, J=1.6, 8.4 Hz, 1H), 7.07 (s, 1H), 6.72 (d, J=8.0 Hz, 1H), 5.19 (dd, J=5.6, 12.8 Hz, 1H), 3.42 (s, 3H), 3.12 (d, J=6.8 Hz, 2H), 3.07-2.92 (m, 3H), 2.89-2.81 (m, 4H), 2.80-2.58 (m, 5H), 2.29-2.21 (m, 1H), 2.19-2.00 (m, 2H), 1.46 (s, 9H), 1.39-1.24 (m, 2H); LC-MS (ESI$^+$) m/z 538.3 (M+H)$^+$.

Step 2—3-[3-Methyl-5-[4-[4-(methylaminomethyl)-1-piperidyl]but-1-ynyl]-2-oxo-benzimidazol-1-yl]piperidine-2,6-dione To a solution of tert-butyl N-[[1-[4-[1-(2,6-dioxo-3-piperidyl)-3-methyl-2-oxo-benzimidazol-5-yl]but-3-ynyl]-4-piperidyl]methyl]-N-methyl-carbamate (60.0 mg, 111 umol) in DCM (3 mL) was added TFA (924 mg, 8.10 mmol). The mixture was stirred at 30° C. for 1 hour. On completion, the reaction mixture was concentrated in vacuo to give the title compound (60.0 mg, 97% yield, TFA) as light yellow oil. LC-MS (ESI$^+$) m/z 438.3 (M+H)$^+$.

Tert-butyl N-[3-(2-piperazin-1-ylethoxy)cyclobutyl]carbamate (Intermediate SJ)

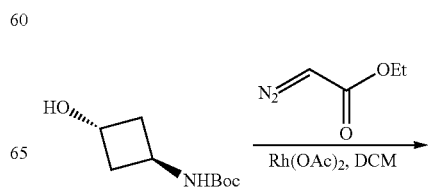

Step 1—Ethyl 2-[3-(tert-butoxycarbonylamino)cyclobutoxy]acetate

To a solution of tert-butyl N-(3-hydroxycyclobutyl)carbamate (8.00 g, 43.0 mmol, CAS #389890-42-0) in DCM (80 mL) was added diacetoxy rhodium (0.38 g, 0.85 mmol), the mixture was stirred at 25° C. for 0.5 hour. Then a solution of ethyl 2-diazoacetate (5.90 g, 51.0 mmol, CAS #623-73-4) in DCM (20 mL) was added to the reaction mixture and stirred at 25° C. for 12 hours. On completion, the reaction mixture was diluted with saturated sodium bicarbonate solution (100 mL) and extracted with DCM (2×150 mL). The combined organic layers were washed with brine (2×200 mL), dried over $Na_2SO_4$, filtered and concentrated in vacuo to give a residue. The residue was purified by column chromatography to give the title compound (9.00 g, 77% yield) as yellow oil. $^1$H NMR (400 MHz, $CDCl_3$) δ 4.23-4.19 (m, 4H), 3.97 (s, 2H), 2.45-2.41 (m, 2H), 2.17-2.14 (m, 2H), 1.43 (m, 9H), 1.30-1.28 (m, 3H).

Step 2—Tert-butyl N-[3-(2-hydroxyethoxy)cyclobutyl]carbamate

To a solution of ethyl 2-[3-(tert-butoxycarbonylamino)cyclobutoxy]acetate (9.00 g, 33.0 mmol) in THF (100 mL) was added $LiBH_4$ (1.20 g, 53.0 mmol) at 0° C. The reaction mixture was stirred at 25° C. for 2 hours. On completion, the reaction mixture was quenched by $H_2O$ (60 mL) at 25° C., and then extracted with ethyl acetate (2×100 mL). The combined organic layers were washed with (2×200 mL), dried over $Na_2SO_4$, filtered and concentrated in vacuo to give the title compound (7.0 g, 92% yield) as colorless oil.

Step 3—2-[3-(Tert-butoxycarbonylamino)cyclobutoxy]ethyl methanesulfonate

To a solution of tert-butyl N-[3-(2-hydroxyethoxy)cyclobutyl]carbamate (2.00 g, 8.70 mmol) in DCM (20 mL) was added $Et_3N$ (1.80 g, 17.0 mmol) and MsCl (1.50 g, 13.0 mmol) at 0° C. Then the reaction mixture was stirred at 25° C. for 1 hour. On completion, the reaction mixture was diluted with $H_2O$ (50 mL) and extracted with DCM (2×50 mL). The combined organic layers were washed with brine (2×100 mL), dried over $Na_2SO_4$, filtered and concentrated in vacuo to give the title compound (2.00 g, 75% yield) as colorless oil.

Step 4—Benzyl 4-[2-[3-(tert-butoxycarbonyl amino)cycl obutoxy]ethyl]piperazine-1-carboxylate To a solution of 2-[3-(tert-butoxycarbonylamino)cyclobutoxy]ethyl methanesulfonate (2.00 g, 6.50 mmol) and benzylpiperazine-1-carboxylate (2.90 g, 13.0 mmol, CAS #31166-44-6) in ACN (40 mL) was added $Et_3N$ (2.00 g, 19.0 mmol) and KI (1.30 g, 7.80 mmol). Then the reaction mixture was stirred at 70° C. for 12 hours. On completion, the reaction mixture was filtered and concentrated in vacuo to give a residue. The crude product was purified by reverse phase HPLC (0.1% FA condition) to give the title compound (2.00 g, 77% yield) as colorless oil. $^1$H NMR (400 MHz, DMSO-$d_6$) δ 7.39-7.33 (m, 5H), 7.18 (d, J=6.0 Hz, 1H), 5.11 (s, 2H), 4.06-4.00 (m, 3H), 3.57 (d, J=4.0 Hz, 2H), 3.31 (s, 3H), 3.11 (d, J=9.2 Hz, 2H), 2.52 (s, 4H), 2.22-2.18 (m, 2H), 2.12-2.08 (m, 2H), 1.37 (s, 9H); LC-MS (ESI$^+$) m/z 434.3 (M+H)$^+$.

Step 5—Tert-butyl N-[3-(2-piperazin-1-ylethoxy)cyclobutyl]carbamate

To a solution of benzyl 4-[2-[3-(tert-butoxycarbonylamino)cyclobutoxy]ethyl]piperazine-1-carboxylate (1.50 g, 3.50 mmol) in MeOH (20 mL) was added Pd/C (0.200 g, 3.50 mmol, 10 wt %). Then the reaction mixture was degassed and purged with $H_2$ gas 3 times and stirred at 25° C. for 12 hours under $H_2$ (15 psi) atmosphere. On completion, the reaction mixture was filtered and concentrated in vacuo to give the title compound (1.0 g, 97% yield) as colorless oil.

1-(2,6-Dioxo-3-piperidyl)-3-methyl-2-oxo-benzimidazole-5-carbaldehyde (Intermediate SK)

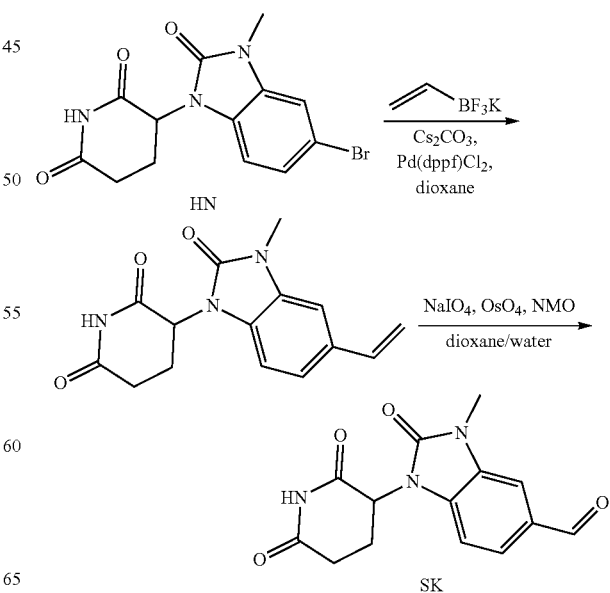

1825

Step 1—3-(3-Methyl-2-oxo-5-vinyl-benzimidazol-1-yl)piperidine-2,6-dione

A mixture of 3-(5-bromo-3-methyl-2-oxo-benzimidazol-1-yl)piperidine-2,6-dione (3.00 g, 8.87 mmol, Intermediate HN), potassium hydride, trifluoro (vinyl)boron (3.57 g, 26.6 mmol), $Cs_2CO_3$ (2 M solution, 8.87 mL), $Pd(dppf)Cl_2$—$CH_2Cl_2$ (724 mg, 887 umol) and in dioxane (30 mL) was degassed and purged with $N_2$ for 3 times, and then the mixture was stirred at 80° C. for 3 hours under $N_2$ atmosphere. On completion, the reaction mixture was concentrated in vacuo to give a residue. The residue was purified by reverse phase (TFA condition) to give the title compound (1.60 g, 58% yield) as a yellow solid. LC-MS (ESI$^+$) m/z 286.0 (M+H)$^+$.

Step 2—1-(2,6-Dioxo-3-piperidyl)-3-methyl-2-oxo-benzimidazole-5-carbaldehyde To a solution of 3-(3-methyl-2-oxo-5-vinyl-benzimidazol-1-yl)piperidine-2,6-dione (0.30 g, 1.05 mmol) in a mixed solvent of dioxane (20 mL) and $H_2O$ (2 mL) was added $NaIO_4$ (449 mg, 2.10 mmol), $OsO_4$ (267 mg, 1.00 mmol) and NMO (61.0 mg, 525 umol). The mixture was stirred at 25° C. for 0.5 hr. On completion, the residue was diluted with water (10 mL) and extracted with ethyl acetate (2×20 mL). The combined organic layers were washed with brine (20 mL), dried over $Na_2SO_4$, filtered and concentrated in vacuo to give a residue. The residue was purified by prep-HPLC (TFA condition) to give the title compound (0.1 g, 32% yield) as a gray solid. LC-MS (ESI+) m/z 288.0 (M+H)$^+$.

3-[5-[[4-[2-(3-Aminocyclobutoxy)ethyl]piperazin-1-yl]methyl]-3-methyl-2-oxo-benzimidazol-1-yl]piperidine-2,6-dione (Intermediate SL)

Step 1—Tert-butyl N-[3-[2-[4-[[1-(2,6-dioxo-3-piperidyl)-3-methyl-2-oxo-benzimidazol-5-yl]methyl]piperazin-1-yl]ethoxy]cyclobutyl]carbamate To a solution of 1-(2,6-dioxo-3-piperidyl)-3-methyl-2-oxo-benzimidazole-5-carbaldehyde (0.20 g, 696 umol, Intermediate SK) and tert-butyl-N-[3-(2-piperazin-1-ylethoxy)cyclobutyl]carbamate (0.420 g, 1.40 mmol, Intermediate SJ) in THF (4 mL) was added HOAc (84.0 mg, 1.40 mmol) and stirred at 40° C. for 1 hour. Then $NaBH(OAc)_3$ (0.440 g, 2.10 mmol) was added to the reaction mixture and stirred at 40° C. for 12 hrs. On completion, the reaction mixture was concentrated in vacuo to give a residue. The residue was purified by prep-HPLC (column: Luna C18 150*25 5 u; mobile phase: [water (0.075% TFA)-ACN]; B %: 15%-45%, 9 min) to give the title compound (0.21 g, 46% yield) as a colorless oil. LC-MS (ESI+) m/z 571.2 (M+H)$^+$.

Step 2—3-[5-[[4-[2-(3-Aminocyclobutoxy)ethyl]piperazin-1-yl]methyl]-3-methyl-2-oxo-Benzimidazol-1-yl]piperidine-2,6-dione To a solution of tert-butyl N-[3-[2-[4-[[1-(2,6-dioxo-3-piperidyl)-3-methyl-2-oxo-benzimidazol-5-yl]methyl]piperazin-1-yl]ethoxy]cyclobutyl]carbamate (0.35 g, 0.61 mmol) in DCM (6 mL) was added HCl/dioxane (4 M, 3.1 mL). Then the reaction mixture was stirred at 25° C. for 0.5 hour. On completion, the reaction mixture was concentrated in vacuo to give the title compound (0.1 g, 34% yield, HCl) as colorless oil. LC-MS (ESI+) m/z 471.2 (M+H)$^+$.

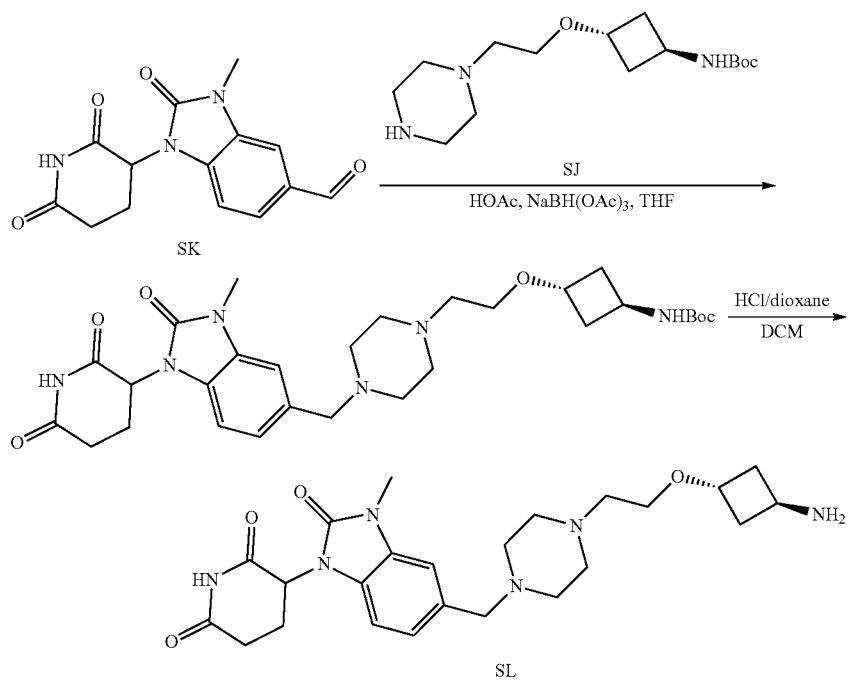

3-[(5S)-5-[3-[3-[(2S)-2-(aminomethyl)morpholin-4-yl]prop-1-ynyl]phenyl]-2-oxo-oxazolidin-3-yl]piperidine-2,6-dione (Intermediate SM)

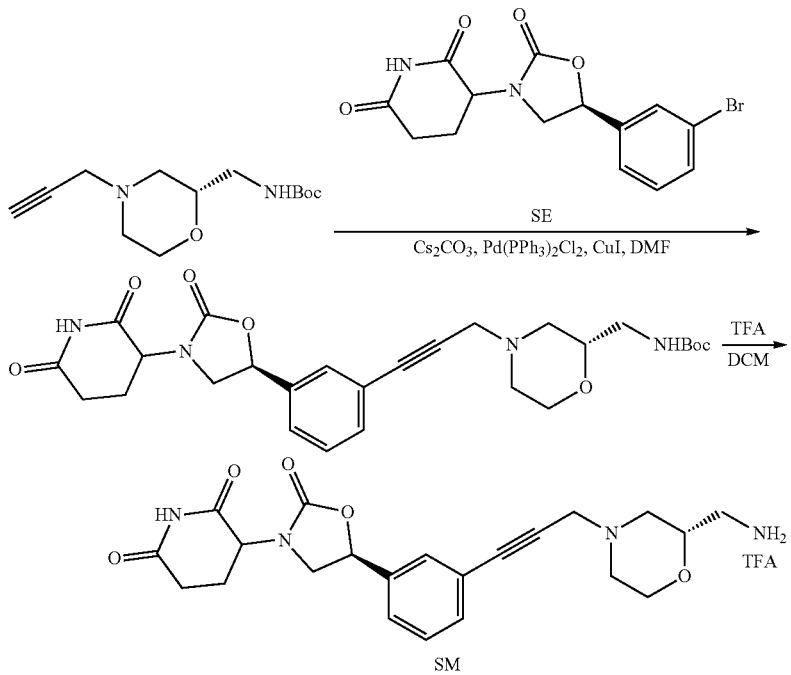

Step 1—Tert-butyl N-[[(2S)-4-[3-[3-[(5S)-3-(2,6-dioxo-3-piperidyl)-2-oxo-oxazolidin-5-yl]phenyl]prop-2-ynyl]morpholin-2-yl]methyl]carbamate To a mixture of tert-butyl N-[[(2S)-4-prop-2-ynylmorpholin-2-yl]methyl]carbamate (540 mg, 2.12 mmol, synthesized via Step 1 of Intermediate RK) and 3-[(5S)-5-(3-bromophenyl)-2-oxo-oxazolidin-3-yl]piperidine-2,6-dione (300 mg, 849 umol, Intermediate SE) in DMF (5 mL) was added Pd(PPh$_3$)$_2$Cl$_2$ (59.6 mg, 84.9 umol), CuI (16.1 mg, 84.9 umol) and Cs$_2$CO$_3$ (1.38 g, 4.25 mmol). The reaction mixture was stirred at 80° C. for 2 hours under N$_2$ atmosphere. On completion, the reaction mixture was filtered and concentrated in vacuo. The residue was diluted with water (30 mL) and extracted with EA (3×30 mL). The combined organic layers was dried over Na$_2$SO$_4$, filtered and concentrated in vacuo to give a residue. The residue was purified by reverse phase (0.1% FA condition) to give the title compound (450 mg, 95% yield) as light yellow solid. LC-MS (ESI$^+$) m/z 527.3 (M+H)$^+$.

Step 2—3-[(5S)-5-[3-[3-[(2S)-2-(aminomethyl)morpholin-4-yl]prop-1-ynyl]phenyl]-2-oxo-oxazolidin-3-yl]piperidine-2,6-dione To a mixture of tert-butyl N-[[(2S)-4-[3-[3-[(5S)-3-(2,6-dioxo-3-piperidyl)-2-oxo-oxazolidin-5-yl]phenyl]prop-2-ynyl]morpholin-2-yl]methyl]carbamate (180 mg, 341 umol) in DCM (3 mL) was added TFA (4.62 g, 40.5 mmol, 3 mL). The reaction mixture was stirred at 25° C. for 0.5 hour. On completion, the reaction mixture was concentrated in vacuo to give the title compound (184 mg, 99% yield, TFA) as red oil. LC-MS (ESI$^+$) m/z 427.1 (M+H)$^+$.

3-[(5S)-5-(4-bromophenyl)-2-oxo-oxazolidin-3-yl]piperidine-2,6-dione (Intermediate SN)

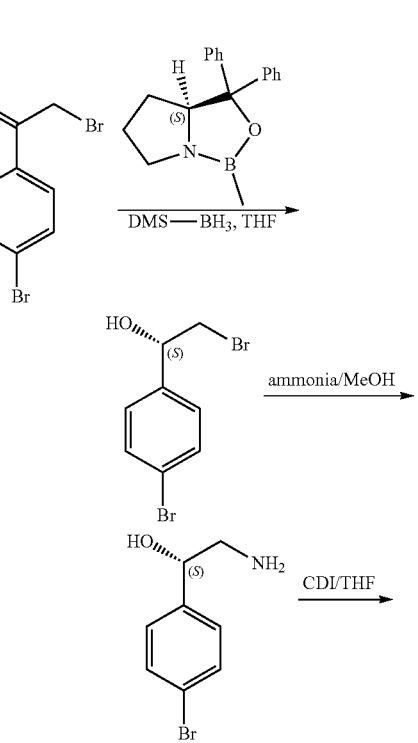

-continued

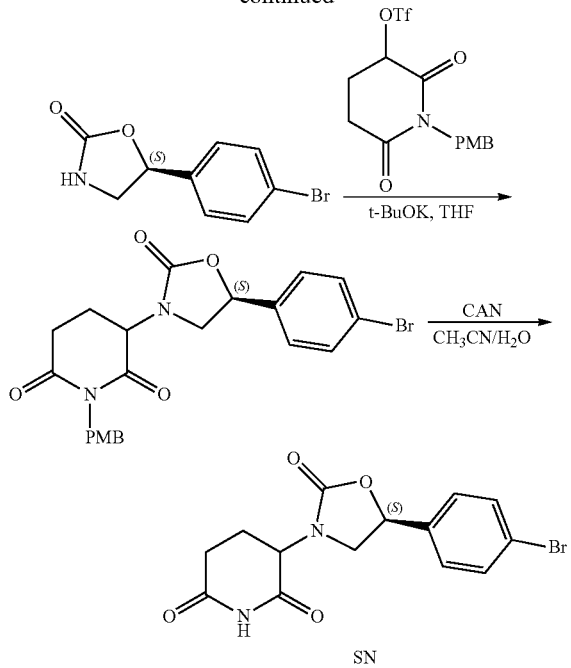

Step 1—(S)-2-bromo-1-(4-bromophenyl)ethanol

To a stirred solution of (S)-1-methyl-3,3-diphenylhexahydropyrrolo[1,2-c][1,3,2]oxazaborole (0.5 g, 1.81 mmol) in THF (25 mL) was added BH$_3$-DMS (10 M, 1.3 mL, 12.7 mmol) at 0° C. The mixture was stirred for 0.5 h at 0° C. To the reaction mixture was then added a solution of 2-bromo-1-(4-bromophenyl)ethanone (5 g, 18.1 mmol) in THF (15 mL) dropwise at 0° C. The mixture was stirred for 12 h at rt. To the mixture was then added MeOH dropwise where gas evolved. MeOH was added until no more bubbling occurred. The mixture was concentrated and purified by column chromatography on silica gel (PE/EA=50/1 to 20/1 to 10/1 to 5/1) to give the title compound (5 g, 100% yield) as a white solid. $^1$H NMR (400 MHz, DMSO-d$_6$) δ 7.55-7.52 (m, 2H), 7.38-7.34 (m, 2H), 5.89 (d, J=4.9 Hz, 1H), 4.82-4.78 (m, 1H), 3.66 (dd, J=10.2, 4.6 Hz, 1H), 3.57 (dd, J=10.2, 6.8 Hz, 1H).

Step 2—(S)-2-amino-1-(4-bromophenyl)ethanol

To a solution of (S)-2-bromo-1-(4-bromophenyl)ethanol (15 g, 123 mmol) in MeOH (100 mL) was added NH$_3$H$_2$O (25%, 250 mL) at 0° C. under N$_2$. The reaction mixture was stirred at rt for 12 h under N$_2$. Then the mixture was concentrated. The solid was washed with EA to give the title compound (8.4 g, 74% yield) as a white solid. $^1$H NMR (400 MHz, DMSO-d$_6$) δ 7.54 (d, J=8.4 Hz, 2H), 7.32 (d, J=8.4 Hz, 2H), 5.51 (br s, 3H), 4.64 (dd, J=8.4, 3.6 Hz, 1H), 2.83 (dd, J=12.8, 3.4 Hz, 1H), 2.69 (dd, J=12.6, 6.8 Hz, 1H).

Step 3—(S)-5-(4-bromophenyl)oxazolidin-2-one

A mixture of (S)-2-amino-1-(4-bromophenyl)ethanol (22 g, 102 mmol), CDI (24.2 g, 153 mmol) and THF (500 mL) was heated to 80° C. and stirred for overnight at 80° C. under N$_2$. To the mixture was then added H$_2$O (200 mL), and the mixture was extracted with EA (300 mL). The organic layer was concentrated and purified by column (PE/EA=2/1 to 1/1) to give the title compound (8.0 g, 33% yield) as a yellow solid.

Step 4—(R)-3-((S)-5-(4-bromophenyl)-2-oxooxazolidin-3-yl)-1-(4-methoxybenzyl)piperidine-2,6-dione To a solution of (S)-5-(3-bromophenyl)oxazolidin-2-one (8.0 g, 30.2 mmol) in THF (100 mL) was added t-BuOK (5.5 g, 49.8 mmol) at 0° C. under N$_2$. The mixture was stirred for 1 h at 0° C. Then to the mixture was added 1-(4-methoxybenzyl)-2,6-dioxopiperidin-3-yl trifluoromethanesulfonate (13.9 g, 36.8 mmol) at 0° C. under N$_2$. The mixture was stirred at 0° C.~10° C. for 2 h. To the mixture was then added EA (100 mL), the solution was then washed with H$_2$O (100 mL), brine (50 mL), dried over Na$_2$SO$_4$, filtered, concentrated and purified by column chromatography on silica gel (PE/EA=2/1) to give a mixture of desired product (R)-3-((S)-5-(4-bromophenyl)-2-oxooxazolidin-3-yl)-1-(4-methoxybenzyl)piperidine-2,6-dione and starting material. Then the mixture was re-purified by flash column chromatography (210 nm, 30% MeCN in H$_2$O) to give the title compound (4.5 g, 28% yield) as a white solid. $^1$H NMR (400 MHz, CDCl$_3$) δ 7.57-7.52 (m, 2H), 7.34-7.29 (m, 2H), 7.26-7.24 (m, 2H), 6.86-6.80 (m, 2H), 5.89 (dd, J=8.7, 7.1 Hz, 1H), 4.89 (s, 2H), 4.58 (dd, J=12.8, 6.0 Hz, 1H), 3.94 (t, J=8.4 Hz, 1H), 3.78 (s, 3H), 3.80 (dd, J=17.9, 7.1 Hz, 1H), 2.97-2.90 (m, 1H), 2.79-2.70 (m, 1H), 2.20-2.04 (m, 2H).

Step 5—(R)-3-((S)-5-(4-bromophenyl)-2-oxooxazolidin-3-yl)piperidine-2,6-dione To a solution of (R)-3-((S)-5-(4-bromophenyl)-2-oxooxazolidin-3-yl)-1-(4-methoxybenzyl)piperidine-2,6-dione (50 mg, 0.106 mmol) in MeCN (5 mL) was added dropwise a solution of CAN (232 mg, 0.424 mmol) in H$_2$O (1 mL) at 0° C. The mixture was stirred for 3 h at 0° C.~10° C. To the mixture was then added H$_2$O (100 mL), and the solution was extracted with EA (200 mL). The organic layer was washed with brine (50 mL), dried over Na$_2$SO$_4$, filtered, concentrated and purified by column (PE/EA=1/1) to give the title compound (5 mg, 14% yield) as a white solid. $^1$H NMR (400 MHz, CDCl$_3$) δ 8.20 (s, 1H), 7.56 (d, J=8.0 Hz, 2H), 7.35 (d, J=8.0 Hz, 2H), 5.49 (t, J=8.2 Hz, 1H), 4.74 (dd, J=13.0, 5.2 Hz, 1H), 3.84 (t, J=8.4 Hz, 1H), 3.48 (t, J=7.8 Hz, 1H), 2.91-2.87 (m, 1H), 2.82-2.73 (m, 1H), 2.22-2.11 (m, 2H). LC/MS (ESI, m/z): [M+1]$^+$=355.0.

Step 6—(S)-3-((S)-5-(4-bromophenyl)-2-oxooxazolidin-3-yl)piperidine-2,6-dione To a solution of (S)-3-((S)-5-(4-bromophenyl)-2-oxooxazolidin-3-yl)-1-(4-methoxybenzyl)piperidine-2,6-dione (80 mg, 0.169 mmol) in MeCN (10 mL) was added dropwise a solution of CAN (372 mg, 0.678 mmol) in H$_2$O (2 mL) at 0° C. The mixture was stirred for 3 h at 0° C.~10° C. To the mixture was added H$_2$O (100 mL), then the mixture was extracted with EA (200 mL). The organic layer was washed with brine (50 mL), dried over Na$_2$SO$_4$, filtered, concentrated and purified by column (PE/EA=1/1) to give the title compound (1.5 mg, 3% yield) as a white solid. $^1$H NMR (400 MHz, CDCl$_3$) δ 7.86 (s, 1H), 7.56 (d, J=8.2 Hz, 2H), 7.26-7.22 (m, 2H), 5.60 (t, J=7.8 Hz, 1H), 4.64 (dd, J=12.0, 5.2 Hz, 1H), 4.00 (t, J=8.2 Hz, 1H), 3.41 (t, J=7.4 Hz, 1H), 2.91-2.86 (m, 1H), 2.78-2.73 (m, 1H), 2.24-2.20 (m, 2H). LC/MS (ESI, m/z): [M+1]$^+$=355.0.

1831

3-[(5S)-5-[4-[3-[(2S)-2-(aminomethyl)morpholin-4-yl]prop-1-ynyl]phenyl]-2-oxo-oxazolidin-3-yl]piperidine-2,6-dione (Intermediate SO)

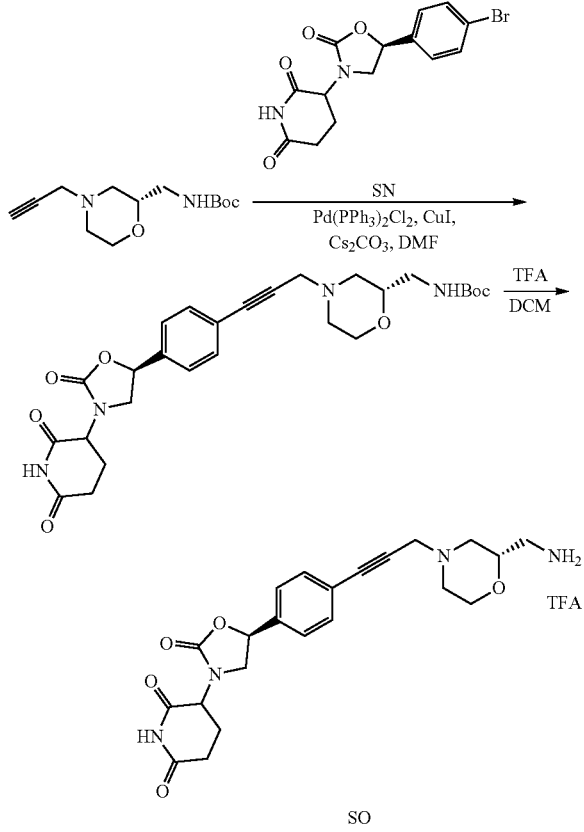

1832

Step 1—Tert-butyl N-[[(2S)-4-[3-[4-[(5S)-3-(2,6-dioxo-3-piperidyl)-2-oxo-oxazolidin-5-yl]phenyl]prop-2-ynyl]morpholin-2-yl]methyl]carbamate To a solution of tert-butyl N-[[(2S)-4-prop-2-ynylmorpholin-2-yl]methyl]carbamate (648 mg, 2.55 mmol, synthesized via Step 1 of Intermediate RK) and 3-[(5S)-5-(4-bromophenyl)-2-oxo-oxazolidin-3-yl]piperidine-2,6-dione (300 mg, 849 umol, Intermediate SN) in DMF (15 mL) was added Pd(PPh$_3$)$_2$Cl$_2$ (119 mg, 169 umol), CuI (32.3 mg, 169 umol) and Cs$_2$CO$_3$ (1.38 g, 4.25 mmol). The reaction mixture was stirred at 80° C. for 2 hours under N$_2$. On completion, the mixture was filtered and the filtrate was concentrated in vacuo to give a residue. The residue was purified by reverse phase (0.1% FA condition) to give the title compound (440 mg, 80% yield) as a yellow solid. $^1$H NMR (400 MHz, DMSO-d$_6$) δ11.00 (d, J=6.0 Hz, 1H), 7.53-7.40 (m, 4H), 6.88-6.84 (m, 1H), 5.73-5.61 (m, 1H), 4.75-4.63 (m, 1H), 3.94 (t, J=8.8 Hz, 1H), 3.89 (t, J=8.8 Hz, 1H), 3.80 (t, J=7.2 Hz, 2H), 3.50-3.40 (m, 4H), 3.30-3.21 (m, 2H), 2.60-2.52 (m, 2H), 2.37-2.15 (m, 3H), 2.02-1.92 (m, 2H), 1.36 (s, 9H); LC-MS (ESI$^+$) m/z 527.3 (M+H)$^+$.

Step 2—3-[(5S)-5-[4-[3-[(2S)-2-(aminomethyl)morpholin-4-yl]prop-1-ynyl]phenyl]-2-oxo-oxazolidin-3-yl]piperidine-2,6-dione To a solution of tert-butyl N-[[(2S)-4-[3-[4-[(5S)-3-(2,6-dioxo-3-piperidyl)-2-oxo-oxazolidin-5-yl]phenyl]prop-2-ynyl]morpholin-2-yl]methyl]carbamate (150 mg, 284 umol) in DCM (3 mL) was added TFA (1.54 g, 13.5 mmol, 1 mL). The reaction mixture was stirred at 25° C. for 2 hours. On completion, the residue concentrated in vacuo to give the title compound (150 mg, 97% yield) as yellow oil. LC-MS (ESI$^+$) m/z 427.2 (M+H)$^+$.

3-[3-Methyl-4-[3-[2-[2-(methylamino)ethoxy]ethoxy]propyl]-2-oxo-benzimidazol-1-yl]piperidine-2,6-dione (Intermediate SP)

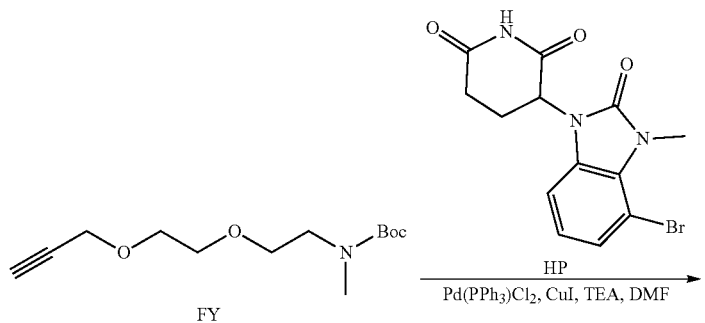

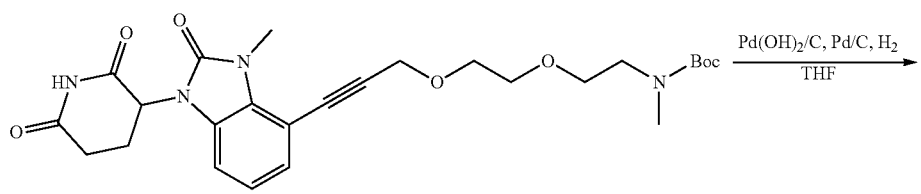

-continued

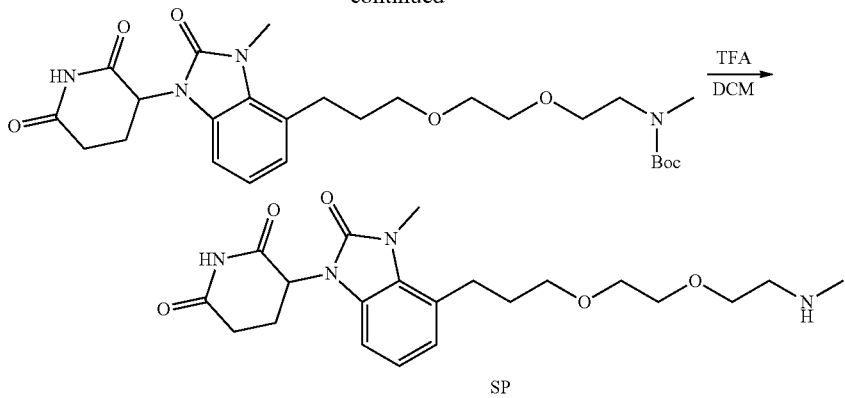

Step 1—Tert-butyl N-[2-[2-[3-[1-(2,6-dioxo-3-piperidyl)-3-methyl-2-oxo-benzimidazol-4-yl]prop-2-ynoxy]ethoxy]ethyl]-N-methyl-carbamate To a mixture of tert-butyl N-methyl-N-[2-(2-prop-2-ynoxyethoxy)ethyl]carbamate (1.37 g, 5.32 mmol, Intermediate FY), 3-(4-bromo-3-methyl-2-oxo-benzimidazol-1-yl) piperidine-2,6-dione (600 mg, 1.77 mmol, Intermediate HP) in DMF (30 mL) was added Cs$_2$CO$_3$ (2.89 g, 8.87 mmol), Pd(PPh$_3$)$_2$Cl$_2$ (249 mg, 354 umol) and CuI (67.5 mg, 354 umol) under N$_2$. The reaction mixture was stirred at 80° C. for 2 hours. On completion, the mixture was filtered, the filtrate was poured into water (100 mL), and the aqueous phase was extracted with ethyl acetate (2×40 mL). The combined organic phase was washed with brine (2×40 mL), dried with anhydrous Na$_2$SO$_4$, filtered and concentrated in vacuo to get residue. The residue was purified by reverse phase (0.1% FA condition) to get title compound (480 mg, 52% yield) as a brown solid. $^1$H NMR (400 MHz, CDCl$_3$) δ 8.29 (s, 1H), 7.22-7.16 (m, 1H), 7.03-7.00 (m, 1H), 6.78 (d, J=8.0 Hz, 1H), 5.28-5.17 (m, 1H), 4.49 (s, 2H), 4.20-4.08 (m, 1H), 3.81-3.78 (m, 3H), 3.71-3.67 (m, 2H), 3.62 (s, 3H), 3.61-3.55 (m, 4H), 2.93 (s, 3H), 2.92 (s, 2H), 2.30-2.20 (m, 1H), 2.03 (s, 1H), 1.47 (s, 9H).

Step 2—Tert-butyl N-[2-[2-[3-[1-(2,6-dioxo-3-piperidyl)-3-methyl-2-oxo-benzimidazol-4-yl]propoxy]ethoxy]ethyl]-N-methyl-carbamate To a mixture of tert-butyl N-[2-[2-[3-[1-(2,6-dioxo-3-piperidyl)-3-methyl-2-oxo-benzimidazol-4-yl]prop-2-ynoxy]ethoxy]ethyl]-N-methyl-carbamate (480 mg, 933 umol) in THF (20 mL) was added Pd/C (100 mg, 1.87 mmol, 10 wt %) and Pd(OH)$_2$/C (100 mg, 1.87 mmol, 10 wt %) under N$_2$. The suspension was degassed in vacuo and purged with H$_2$ gas three times. The mixture was stirred at 20° C. for 12 hours under H$_2$ (15 psi). On completion, the mixture was filtered and concentrated in vacuo to give the title compound (360 mg, 74% yield) as brown oil. LC-MS (ESI$^+$) m/z 541.2 (M+Na)$^+$.

Step 3—3-[3-Methyl-4-[3-[2-[2-(methylamino)ethoxy]ethoxy]propyl]-2-oxo-benzimidazol-1-yl]piperidine-2,6-dione To a mixture of tert-butyl N-[2-[2-[3-[1-(2,6-dioxo-3-piperidyl)-3-methyl-2-oxo-benzimidazol-4-yl]propoxy]ethoxy]ethyl]-N-methyl-carbamate (350 mg, 675 umol) in DCM (2 mL) was added TFA (154 mg, 1.35 mmol). The reaction mixture was stirred at 25° C. for 0.1 hour. On completion, the mixture was concentrated in vacuo to get title compound (365 mg, 100% yield) as brown oil. LC-MS (ESI$^+$) m/z 419.1 (M+H)$^+$.

3-[4-[3-[(2R)-2-(aminomethyl)morpholin-4-yl]propyl]-3-methyl-2-oxo-benzimidazol-1-yl]piperidine-2,6-dione (Intermediate SO)

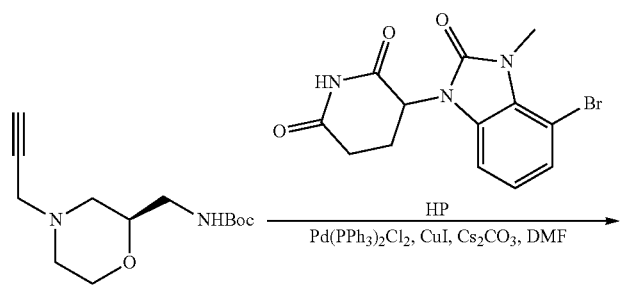

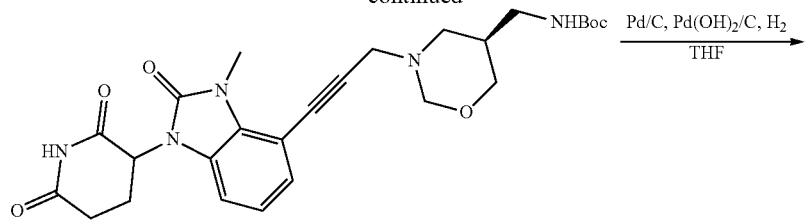

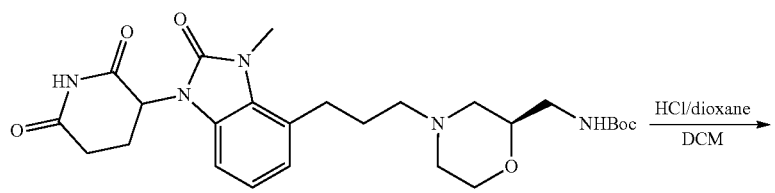

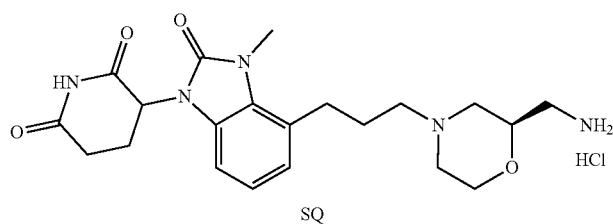

SQ

Step 1—Tert-butyl N-[[(2R)-4-[3-[1-(2,6-dioxo-3-piperidyl)-3-methyl-2-oxo-benzimidazol-5-yl]prop-2-ynyl]morpholin-2-yl]methyl]carbamate To a solution of tert-butyl N-[[(2R)-4-prop-2-ynylmorpholin-2-yl]methyl]carbamate (940 mg, 3.70 mmol, synthesized via Step 1 of Intermediate RJ) and 3-(4-bromo-3-methyl-2-oxo-benzimidazol-1-yl)piperidine-2,6-dione (500 mg, 1.48 mmol, Intermediate HP) in DMF (15 mL) was added $Cs_2CO_3$ (2.41 g, 7.39 mmol), CuI (28.1 mg, 147 umol) and $Pd(PPh_3)_2Cl_2$ (103 mg, 147 umol). The reaction mixture was stirred at 80° C. for 2 hr under $N_2$. On completion, the mixture was filtered, and the filtrate was concentrated in vacuo to give a residue. The residue was purified by reverse phase (0.1% FA condition) to give the title compound (500 mg, 66% yield) as a yellow solid. LC-MS (ESI$^+$) m/z 512.3 (M+H)$^+$.

Step 2—Tert-butyl N-[[(2R)-4-[3-[1-(2,6-dioxo-3-piperidyl)-3-methyl-2-oxo-benzimidazol-4-yl]propyl]morpholin-2-yl]methyl]carbamate To a solution of tert-butyl N-[[(2R)-4-[3-[1-(2,6-dioxo-3-piperidyl)-3-methyl-2-oxo-benzimidazol-4-yl]prop-2-ynyl]morpholin-2-yl]methyl]carbamate (500 mg, 977 umol) in THF (20 mL) was added Pd/C (100 mg, 10 wt %) and Pd(OH)$_2$/C (100 mg, 10 wt %). The reaction mixture was stirred at 25° C. under $H_2$ (15 psi) for 12 hrs. On completion, the residue was filtered and the filtrate was concentrated in vacuo to give a residue. The residue was purified by reverse phase (0.1% FA condition) to give the title compound (370 mg, 73% yield) as a white solid. $^1$H NMR (400 MHz, DMSO-d$_6$) δ 11.09 (s, 1H), 7.04-6.91 (m, 2H), 6.91-6.79 (m, 2H), 5.36 (dd, J=5.2, 12.4 Hz, 1H), 3.76 (d, J=10.4 Hz, 1H), 3.56 (s, 3H), 3.46 (t, J=10.8 Hz, 1H), 3.40-3.35 (m, 1H), 3.02-2.79 (m, 6H), 2.75-2.61 (m, 3H), 2.45-2.31 (m, 2H), 2.06-1.94 (m, 2H), 1.82-1.63 (m, 3H), 1.37 (s, 9H); LC-MS (ESI$^+$) m/z 516.3 (M+H)$^+$.

Step 3—3-[4-[3-[(2R)-2-(aminomethyl)morpholin-4-yl]propyl]-3-methyl-2-oxo-benzimidazol-1-yl]piperidine-2,6-dione To a solution of tert-butyl N-[[(2R)-4-[3-[1-(2,6-dioxo-3-piperidyl)-3-methyl-2-oxo-benzimidazol-4-yl]propyl]morpholin-2-yl]methyl]carbamate (370 mg, 717 umol) in DCM (3 mL) was added HCl/dioxane (4 M, 3.08 mL). The reaction mixture was stirred at 25° C. for 2 hrs. On completion, the mixture was concentrated in vacuo to give the title compound (320 mg, 98% yield, HCl) as a white solid. LC-MS (ESI$^+$) m/z 416.3 (M+H)$^+$.

3-[4-[3-[(2S)-2-(aminomethyl)morpholin-4-yl]propyl]-3-methyl-2-oxo-benzimidazol-1-yl]piperidine-2,6-dione (Intermediate SR)

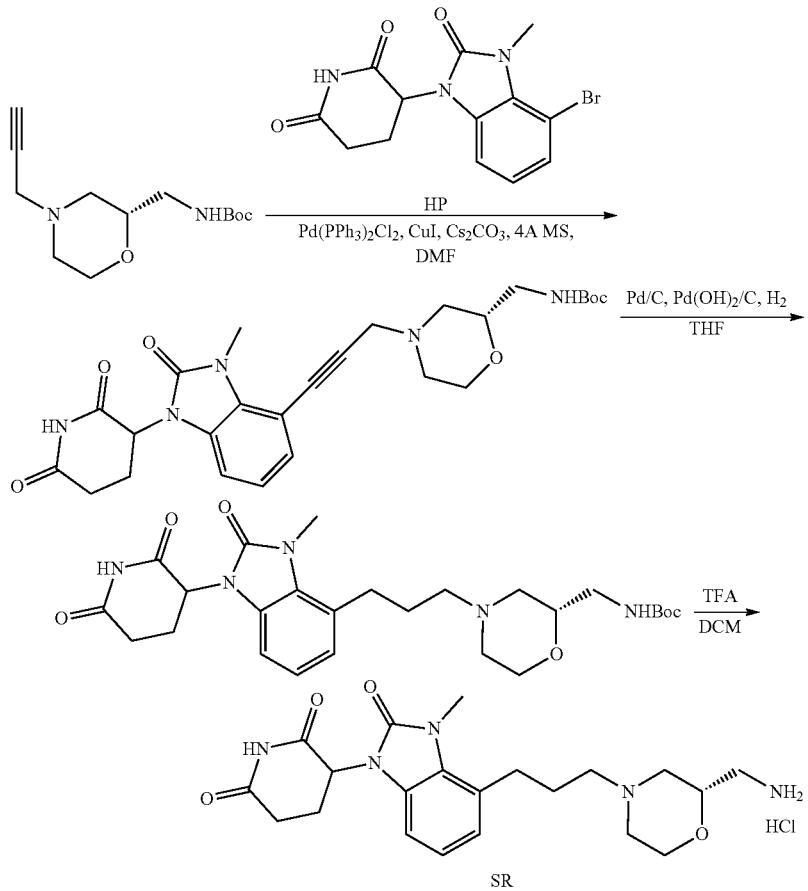

Step 1—Tert-butyl N-[[(2S)-4-[3-[1-(2,6-dioxo-3-piperidyl)-3-methyl-2-oxo-benzimidazol-4-yl]prop-2-ynyl]morpholin-2-yl]methyl]carbamate To a solution of 3-(4-bromo-3-methyl-2-oxo-benzimidazol-1-yl)piperidine-2,6-dione (500 mg, 1.48 mmol, Intermediate HP) and tert-butyl N-[[(2S)-4-prop-2-ynylmorpholin-2-yl]methyl]carbamate (564 mg, 2.22 mmol, synthesized via Step 1 of Intermediate RK) in DMF (20 mL) was added Cs$_2$CO$_3$ (1.93 g, 5.91 mmol), CuI (56.3 mg, 295 umol), 4 Å molecular sieves (20 mg) and Pd(PPh$_3$)$_2$Cl$_2$ (207 mg, 295 umol), and the mixture was heated at 80° C. for 2 hours. On completion, the reaction mixture was filtered and concentrated in vacuo. The residue was diluted with water (40 mL), and then extracted with EA (50 mL×3). The combined organic layers were dried over Na$_2$SO$_4$, filtered and concentrated in vacuo to give a residue. The residue was purified by prep-HPLC (FA condition) to give the title compound (430 mg, 56% yield) as light yellow solid. $^1$H NMR (400 MHz, CDCl$_3$) δ 8.35 (s, 1H), 7.18 (dd, J=0.8, 8.0 Hz, 1H), 7.98 (t, J=8.0 Hz, 1H), 6.77 (dd, J=0.8, 8.0 Hz, 1H), 5.22 (dd, J=5.2, 12.8 Hz, 1H), 4.90 (s, 1H), 3.94 (dd, J=0.8, 11.6 Hz, 1H), 3.77 (s, 3H), 3.74-3.70 (m, 1H), 3.68-3.62 (m, 1H), 3.58 (d, J=2.0 Hz, 2H), 3.40-3.31 (m, 1H), 3.18-3.08 (m, 1H), 3.01-2.91 (m, 1H), 2.90-2.73 (m, 4H), 2.50-2.44 (m, 1H), 2.31-2.17 (m, 2H), 1.44 (s, 9H). LC-MS (ESI$^+$) m/z 512.3 (M+H)$^+$.

Step 2—Tert-butyl N-[[(2S)-4-[3-[1-(2,6-dioxo-3-piperidyl)-3-methyl-2-oxo-benzimidazol-4-yl]propyl]morpholin-2-yl]methyl]carbamate To a solution of tert-butyl N-[[(2S)-4-[3-[1-(2,6-dioxo-3-piperidyl)-3-methyl-2-oxo-benzimidazol-4-yl]prop-2-ynyl]morpholin-2-yl]methyl]carbamate (360 mg, 703 umol) in THF (5 mL) was added Pd(OH)$_2$/C (40.0 mg, 10 wt %) and Pd/C (40.0 mg, 10 wt %) under N$_2$. The suspension was degassed under vacuum and purged with H$_2$ three times. The mixture was stirred under H$_2$ (15 psi) at 25° C. for 4 hours. On completion, the reaction mixture was filtered and concentrated in vacuo to give a residue. The residue was purified by prep-HPLC (FA condition) to give the title compound (280 mg, 77% yield) as light yellow solid. $^1$H NMR (400 MHz, CDCl$_3$) δ 8.32 (s, 1H), 7.89 (t, J=8.4 Hz, 1H), 7.18 (d, J=0.8, 8.0 Hz, 1H), 6.67 (d, J=7.6 Hz, 1H), 5.22 (dd, J=5.2, 12.4 Hz, 1H), 4.90 (s, 1H), 3.87 (d, J=10.8 Hz, 1H), 3.72-3.52 (m, 5H), 3.40-3.25 (m, 1H), 3.17-3.03 (m, 1H), 3.01-2.91 (m, 3H), 2.87-2.66 (m, 4H), 2.41 (t, J=6.8 Hz, 2H), 2.26-2.08 (m, 2H), 1.94-1.83 (m, 3H), 1.45 (s, 9H); LC-MS (ESI$^+$) m/z 516.2 (M+H)$^+$.

Step 3—3-[4-[3-[(2S)-2-(aminomethyl)morpholin-4-yl]propyl]-3-methyl-2-oxo-benzimidazol-1-yl]piperidine-2,6-dione To a solution of tert-butyl N-[[(2S)-4-[3-[1-(2,6-dioxo-3-piperidyl)-3-methyl-2-oxo-benzimidazol-4-yl]propyl]morpholin-2-yl]methyl]carbamate (200 mg, 387 umol) in DCM (3 mL) was added TFA (924 mg, 8.10 mmol). The mixture was stirred at 25° C. for 1 hour. On completion, the reaction mixture was concentrated in vacuo to give the title compound (200 mg, 98% yield, TFA) as light yellow oil. LC-MS (ESI⁺) m/z 416.3 (M+H)⁺.

3-[7-[3-[(2S)-2-(aminomethyl)morpholin-4-yl]propyl]-2-oxo-1,3-benzoxazol-3-yl]piperidine-2,6-dione (Intermediate SS)

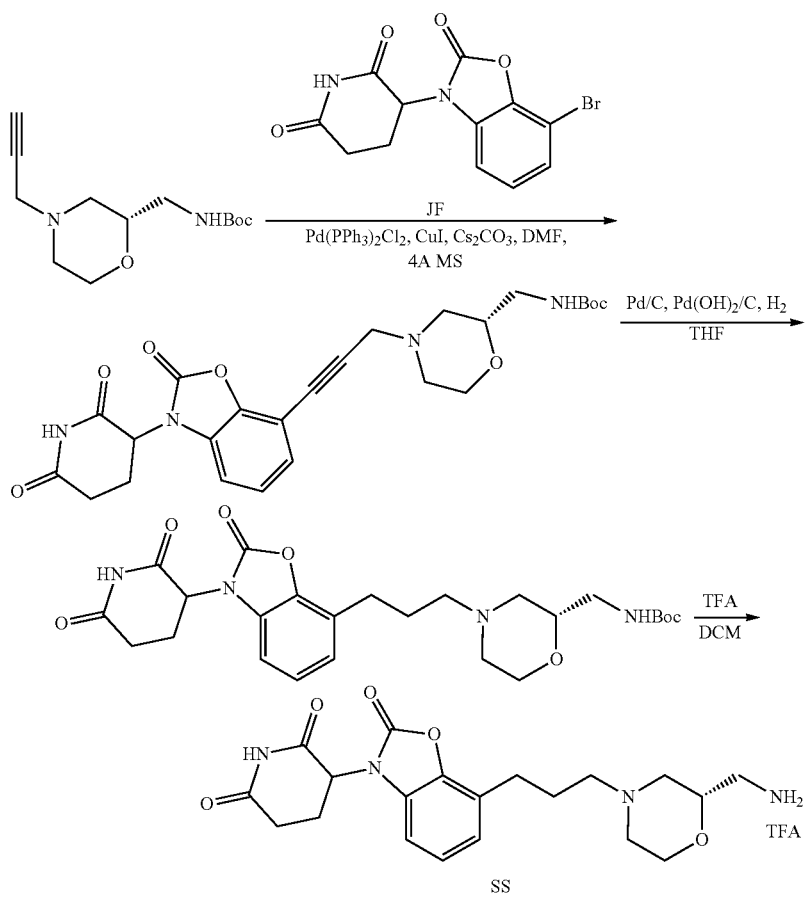

Step 1—Tert-butyl (((2S)-4-(3-(3-(2,6-dioxopiperidin-3-yl)-2-oxo-2,3-dihydrobenzo[d]oxazol-7-yl)prop-2-yn-1-yl)morpholin-2-yl)methyl)carbamate To a solution of 3-(7-bromo-2-oxo-1,3-benzoxazol-3-yl)piperidine-2,6-dione 2 (600 mg, 1.85 mmol, Intermediate JF) and tert-butyl N-[[(2S)-4-prop-2-ynylmorpholin-2-yl]methyl]carbamate (704 mg, 2.77 mmol, synthesized via Step 1 of Intermediate RK) in DMF (15 mL) was added Cs$_2$CO$_3$ (2.41 g, 7.38 mmol), CuI (70.3 mg, 369 mmol), 4 Å molecular sieves (30.0 mg) and Pd(PPh$_3$)$_2$Cl$_2$ (259 mg, 369 umol) at 25° C. under N$_2$. Then the mixture was heated at 80° C. for 2 hours. On completion, the residue was filtered and the filtrate was concentrated in vacuo to give a residue. The residue was purified by column chromatography (SiO$_2$, petroleum ether/ethyl acetate=1:2 to 1:3) to give the title compound (684 mg, 74% yield) as a yellow solid. ¹H NMR (400 MHz, CDCl$_3$) δ 8.18 (s, 1H), 7.43 (s, 1H), 7.23-7.20 (m, 1H), 7.14-7.10 (t, J=8.0 Hz, 1H), 6.80-6.77 (m, 1H), 5.07-5.02 (m, 1H), 4.91-4.90 (m, 1H), 3.96-3.92 (m, 1H), 3.74-3.60 (m, 4H), 3.16-3.09 (m, 1H), 3.02-2.97 (m, 1H), 2.89-2.68 (m, 4H), 2.54-2.47 (m, 1H), 2.37-2.21 (m, 2H), 1.44 (s, 9H); LC-MS (ESI+) m/z 499.1 (M+H)⁺.

Step 2—Tert-butyl N-[[(2S)-4-[3-[3-(2,6-dioxo-3-piperidyl)-2-oxo-1,3-benzoxazol-7-yl]propyl]morpholin-2-yl]methyl]carbamate To a mixture of tert-butyl N-[[(2S)-4-[3-[3-(2,6-dioxo-3-piperidyl)-2-oxo-1,3-benzoxazol-7-yl]prop-2-ynyl]morpholin-2-yl]methyl]carbamate (250 mg, 501 umol) in THF (5 mL) was added Pd/C (75.0 mg, 10 wt %) and Pd(OH)$_2$ (75.0 mg, 10 wt %) under N$_2$. The suspension was degassed in vacuo and purged with H$_2$ three times. The mixture was stirred under H$_2$ (15 psi) at 25° C. for 16 hours. On completion, the reaction mixture was filtered to remove Pd/C and Pd(OH)$_2$/C, and concentrated in vacuo to give a residue. The residue was purified by reverse phase (0.1% FA) to give the title compound (120 mg, 55% yield) as a white solid. ¹H NMR (400 MHz, CDCl$_3$) δ 8.38 (s, 1H), 7.10 (t, J=8.0 Hz, 1H), 7.00 (d, J=7.8 Hz, 1H), 6.70 (d, J=7.8 Hz, 1H), 5.08-5.04 (m, 1H), 4.89 (s, 1H), 3.92-3.76 (m, 3H), 3.34-3.29 (m, 1H), 3.18-3.09 (m, 1H), 3.01-2.69 (m, 8H), 2.57 (d, J=5.4 Hz, 2H), 2.36-2.30 (m, 2H), 2.04-1.99 (m, 2H), 1.45 (s, 9H); LC-MS (ESI+) m/z 503.1 (M+H)+.

Step 3—3-[7-[3-[(2S)-2-(aminomethyl)morpholin-4-yl]propyl]-2-oxo-1,3-benzoxazol-3-yl]piperidine-2,6-dione To a mixture of tert-butyl N-[[(2S)-4-[3-[3-(2,6-dioxo-3-piperidyl)-2-oxo-1,3-benzoxazol-7-yl]propyl]morpholin-2-yl]methyl]carbamate (140 mg, 278 umol) in DCM (2 mL) was added TFA (317 mg, 2.79 mmol) in one portion at 25° C. The mixture was stirred at 25° C. for 0.5 hour. On completion, the reaction mixture was concentrated in vacuo to give the title compound (139 mg, 96% yield, TFA) as light yellow oil. $^1$H NMR (400 MHz, DMSO-d$_6$) δ 11.22 (s, 1H), 8.06 (s, 2H), 7.23-7.12 (m, 2H), 7.10-7.00 (m, 1H), 5.40-5.35 (m, 1H), 5.41-5.34 (m, 1H), 4.11 (d, J=10.4 Hz, 1H), 4.01-3.89 (m, 1H), 3.74 (t, J=12.0 Hz, 1H), 3.64-3.43 (m, 2H), 3.32-3.11 (m, 2H), 3.11-2.98 (m, 2H), 2.97-2.59 (m, 7H), 2.18-2.11 (m, 1H), 2.09-2.00 (m, 2H); LC-MS (ESI+) m/z 403.2 (M+H)+.

3-[7-[3-[(2R)-2-(aminomethyl)morpholin-4-yl]propyl]-2-oxo-1,3-benzoxazol-3-yl]piperidine-2,6-dione (Intermediate ST)

Step 1—Tert-butyl N-[[(2R)-4-[3-[3-(2,6-dioxo-3-piperidyl)-2-oxo-1,3-benzoxazol-7-yl]prop-2-ynyl]morpholin-2-yl]methyl]carbamate To a solution of tert-butyl N-[[(2R)-4-prop-2-ynylmorpholin-2-yl]methyl]carbamate (488 mg, 1.92 mmol, synthesized via Step 1 of Intermediate RJ) and 3-(7-bromo-2-oxo-1,3-benzoxazol-3-yl)piperidine-2,6-dione (250 mg, 768 umol, Intermediate JF) in DMF (15 mL) was added Pd(PPh$_3$)$_2$Cl$_2$ (53.9 mg, 76.9 umol), CuI (14.6 mg, 76.9 umol) and Cs$_2$CO$_3$ (1.25 g, 3.84 mmol). The reaction mixture was stirred at 80° C. for 2 hrs under N$_2$. On completion, the mixture was filtered, and the filtrate was concentrated in vacuo to give a residue. The residue was purified by reverse phase (0.1% FA condition) to give the title compound (350 mg, 91% yield) as a yellow solid. LC-MS (ESI+) m/z 499.2 (M+H)+.

Step 2—Tert-butyl N-[[(2R)-4-[3-[3-(2,6-dioxo-3-piperidyl)-2-oxo-1,3-benzoxazol-7-yl]propyl]morpholin-2-yl]methyl]carbamate To a solution of tert-butyl N-[[(2R)-4-[3-[3-(2,6-dioxo-3-piperidyl)-2-oxo-1,3-benzoxazol-7-yl]prop-2-ynyl]morpholin-2-yl]methyl]carbamate (350 mg, 702 umol) in THF (20

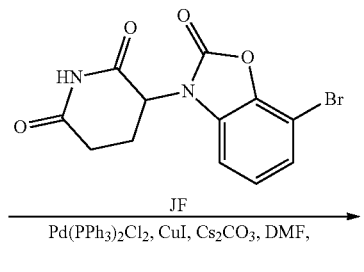

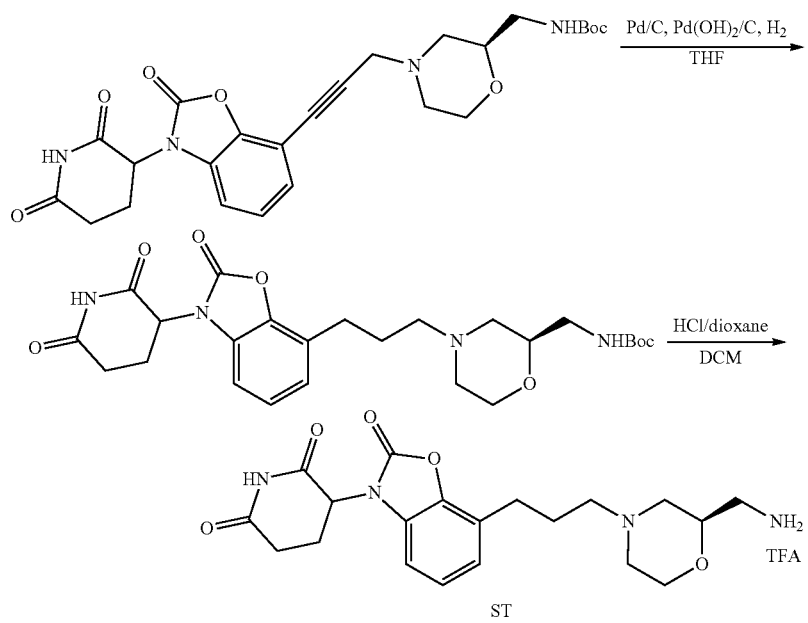

mL) was added Pd/C (100 mg, 10 wt %) and Pd(OH)$_2$/C (100 mg, 10 wt %). The reaction mixture was stirred at 25° C. under H$_2$ (15 psi) for 12 hrs. On completion, the residue was filtered and the filtrate was concentrated in vacuo to give a residue. The residue was purified by reverse phase (0.1% FA condition) to give the title compound (290 mg, 82% yield) as a white solid. $^1$H NMR (400 MHz, DMSO-d$_6$) δ 11.21 (s, 1H), 7.17-7.07 (m, 2H), 7.02 (d, J=6.8 Hz, 1H), 6.82 (t, J=5.6 Hz, 1H), 5.38-5.32 (m, 1H), 3.77 (d, J=10.2 Hz, 1H), 3.47 (d, J=11.2 Hz, 1H), 3.43-3.39 (m, 1H), 2.99-2.87 (m, 3H), 2.79-2.65 (m, 6H), 2.44-2.31 (m, 2H), 2.21-2.07 (m, 2H), 1.87-1.69 (m, 3H), 1.36 (s, 9H); LC-MS (ESI$^+$) m/z 503.3 (M+H)$^+$.

Step 3—3-[7-[3-[(2R)-2-(aminomethyl)morpholin-4-yl]propyl]-2-oxo-1,3-benzoxazol-3-yl]piperidine-2,6-dione To a solution of tert-butyl N-[[(2R)-4-[3-[3-(2,6-dioxo-3-piperidyl)-2-oxo-1,3-benzoxazol-7-yl]propyl]morpholin-2-yl]methyl]carbamate (290 mg, 577 umol) in DCM (3 mL) was added HCl/dioxane (4 M, 2.48 mL). The reaction mixture was stirred at 25° C. for 2 hrs. On completion, the mixture was concentrated in vacuo to give the title compound (250 mg, 98% yield, HCl) as a white solid. LC-MS (ESI$^+$) m/z 403.2 (M+H)$^+$.

3-(6-((2-(2-(2-Aminoethoxy)ethoxy)ethyl)amino)-9H-pyrido[2,3-b]indol-9-yl)piperidine-2,6-dione (Intermediate SU)

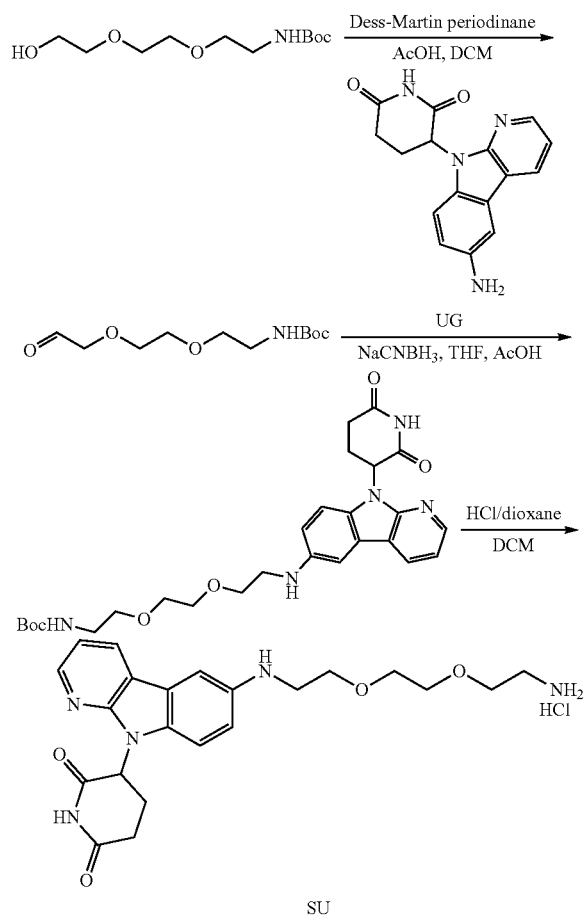

SU

Step 1—tert-butyl (2-(2-(2-oxoethoxy)ethoxy)ethyl)carbamate

To a solution of tert-butyl (2-(2-(2-hydroxyethoxy)ethoxy)ethyl)carbamate (2 g, 8.03 mmol, synthesized via Step 1 on Intermediate AC) in DCM (20 mL) was added Dess-Martin periodinane (5.1 g, 12.04 mmol) and AcOH (1 mL) portion wise. After addition, the mixture was stirred at rt overnight. The mixture was then concentrated in vacuo. The residue was purified by flash chromatography to give the title compound (300 mg, 15%) as an oil. LC/MS (ESI, m/z): [M+1]+=248.2.

Step 2—tert-butyl (2-(2-(2-((9-(2,6-dioxopiperidin-3-yl)-9H-pyrido[2,3-b]indol-6-yl)amino)ethoxy)ethoxy)ethyl)carbamate To a mixture of 3-(6-amino-9H-pyrido[2,3-b]indol-9-yl)piperidine-2,6-dione (200 mg, 0.68 mmol, Intermediate UG), tert-butyl (2-(2-(2-oxoethoxy)ethoxy)ethyl)carbamate (176.3 mg, 0.714 mmol) in THF (5 mL) was added AcOH (5 drops). The mixture was stirred at rt for 2 h. Then sodium cyanoborohydride (85.4 mg, 1.36 mmol) was added, and the mixture was heated to 40° C. and stirred overnight. Then the mixture was poured into water, and extracted with EtOAc (3×30 mL). The combined organic layers were washed with brine (50 mL), dried over anhydrous Na$_2$SO$_4$, filtered and concentrated in vacuo. The residue was purified by prep HPLC to give the title compound (70 mg, 20% yield) as a white solid. $^1$H NMR (400 MHz, DMSO-d$_6$) δ 11.09 (br. s., 1H), 8.52-8.26 (m, 2H), 7.36-7.32 (m, 2H), 7.15 (dd, J=7.63, 4.88 Hz, 1H), 6.93-6.90 (m, 1H), 6.78-6.76 (m, 1H), 5.91 (br. s., 1H), 5.30 (br. s., 1H), 3.64 (t, J=5.82 Hz, 2H), 3.51-3.59 (m, 4H), 3.40 (t, J=6.13 Hz, 2H), 3.30-3.28 (m, 2H), 3.09-2.98 (m, 4H), 2.69-2.66 (m, 1H), 2.00-2.12 (m, 1H), 1.37 (s, 9H); LC/MS (ESI, m/z): [M+1]$^+$=526.55.

Step 3—3-(6-((2-(2-(2-Aminoethoxy)ethoxy)ethyl)amino)-9H-pyrido[2,3-b]indol-9-yl)piperidine-2,6-dione To a solution of tert-butyl N-[2-[2-[2-[[9-(2,6-dioxo-3-piperidyl)pyrido[2,3-b]indol-6-yl]amino]ethoxy]ethoxy]ethyl]carbamate (20.0 mg, 38.0 umol) in DCM (3 mL) was added HCl/dioxane (4 M, 2 mL). The reaction mixture was stirred at 25° C. for 0.5 hr. On completion, the reaction mixture was concentrated in vacuo to give the title compound (17.5 mg, 100% yield, HCl) as a white solid. LC-MS (ESI+) m/z 426.2 (M+H)$^+$.

3-[4-[3-[2-(2-aminoethoxy)ethoxy]propyl]-3-methyl-2-oxo-benzimidazol-1-yl]-1-methyl-piperidine-2,6-dione (Intermediate SV)

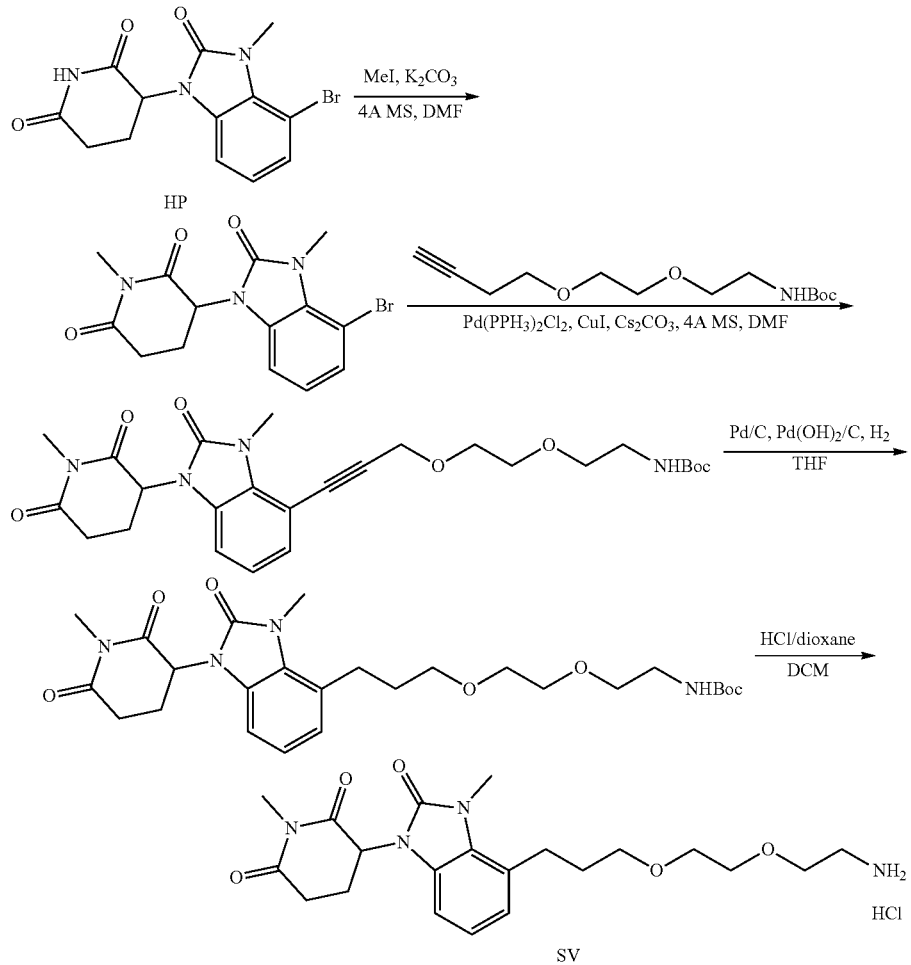

Step 1—3-(4-Bromo-3-methyl-2-oxo-benzimidazol-1-yl)-1-methyl-piperidine-2,6-dione To a solution of 3-(4-bromo-3-methyl-2-oxo-benzimidazol-1-yl)piperidine-2,6-dione (4.00 g, 11.8 mmol, Intermediate HP) and 4 Å molecular sieves (300 mg) in DMF (40 mL) was added MeI (1.68 g, 11.8 mmol) and K2CO3 (1.63 g, 11.8 mmol). The reaction mixture was stirred at 25° C. for 12 hrs. On completion, the mixture was filtered and the filtrate was concentrated in vacuo. The residue was purified by silica gel chromatography to give the title compound (3.70 g, 89% yield) as a white solid. 1H NMR (400 MHz, DMSO-d6) δ 7.24 (d, J=8.0 Hz, 1H), 7.17 (d, J=7.8 Hz, 1H), 7.00-6.94 (m, 1H), 5.46 (dd, J=5.2, 12.8 Hz, 1H), 3.63 (s, 3H), 3.03 (s, 3H), 3.00-2.90 (m, 1H), 2.83-2.66 (m, 2H), 2.08-1.97 (m, 1H).

Step 2—Tert-butyl N-[2-[2-[3-[3-methyl-1-(1-methyl-2,6-dioxo-3-piperidyl)-2-oxo-benzimidazol-4-yl]prop-2-ynoxy]ethoxy]ethyl]carbamate A mixture of 3-(4-bromo-3-methyl-2-oxo-benzimidazol-1-yl)-1-methyl-piperidine-2,6-dione (800 mg, 2.27 mmol), tert-butyl N-[2-(2-prop-2-ynoxyethoxy)ethyl]carbamate (1.38 g, 5.68 mmol, synthesized via Step 1 of Intermediate CQ), Pd(PPh$_3$)$_2$Cl$_2$ (319 mg, 454 umol), CuI (86.5 mg, 454 umol), Cs$_2$CO$_3$ (3.70 g, 11.4 mmol), and 4 Å molecular sieve (800 mg) in DMF (40 mL) was de-gassed and then heated at 80° C. for 2 hrs under N$_2$. On completion, the mixture was filtered and the filtrate was concentrated in vacuo. The residue was purified by reverse phase (0.1% FA condition) to give the title compound (650 mg, 45% yield) as a yellow solid. $^1$H NMR (400 MHz, DMSO-d$_6$) δ 7.18 (d, J=7.6 Hz, 1H), 7.13 (d, J=7.2 Hz, 1H), 7.05-6.98 (m, 1H), 6.82-6.75 (m, 1H), 5.51-5.43 (m, 1H), 4.46 (s, 2H), 3.67-3.64 (m, 2H), 3.64 (s, 3H), 3.57-3.54 (m, 2H), 3.47-3.42 (m, 2H), 3.10-3.06 (m, 2H), 3.03 (s, 3H), 2.99-2.90 (m, 1H), 2.79-2.63 (m, 2H), 2.06-1.92 (m, 1H), 1.36 (s, 9H); LC-MS (ESI$^+$) m/z 537.3 (M+Na)$^+$.

Step 3—Tert-butyl N-[2-[2-[3-[3-methyl-1-(1-methyl-2,6-dioxo-3-piperidyl)-2-oxo-benzimidazol-4-yl]propoxy]ethoxy]ethyl]carbamate To a solution of tert-butyl N-[2-[2-[3-[3-methyl-1-(1-methyl-2,6-dioxo-3-piperidyl)-2-oxo-benzimidazol-4-yl]prop-2-ynoxy]ethoxy]ethyl]carbamate (1.30 g, 2.02 mmol) in THF (20 mL) was added Pd/C (300 mg, 10% wt) and Pd(OH)$_2$/C (300 mg, 10% wt). The reaction mixture was stirred at 25° C. for 10 hrs under H$_2$ (15 psi) atmosphere. On completion, the mixture was filtered and the filtrate was concentrated in vacuo to give the title compound (1.30 g, 99% yield) as a yellow solid. LC-MS (ESI$^+$) m/z 541.3 (M+Na)$^+$.

Step 4—3-[4-[3-[2-(2-Aminoethoxy)ethoxy]propyl]-3-methyl-2-oxo-benzimidazol-1-yl]-1-methyl-piperidine-2,6-dione To a solution of tert-butyl N-[2-[2-[3-[3-methyl-1-(1-methyl-2,6-dioxo-3-piperidyl)-2-oxo-benzimidazol-4-yl]propoxy]ethoxy]ethyl]carbamate (1.20 g, 1.85 mmol) in DCM (10 mL) was added HCl/dioxane (10 mL). The reaction mixture was stirred at 25° C. for 2 hrs. On completion, the mixture was concentrated in vacuo to give the title compound (1.10 g, 98% yield, HCl salt) as a yellow solid. LC-MS (ESI$^+$) m/z 419.2 (M+H)$^+$ Tertbutyl N-methyl-N-[3-(2-piperazin-1-ylethoxy)cyclobutyl]carbamate (Intermediate SW)

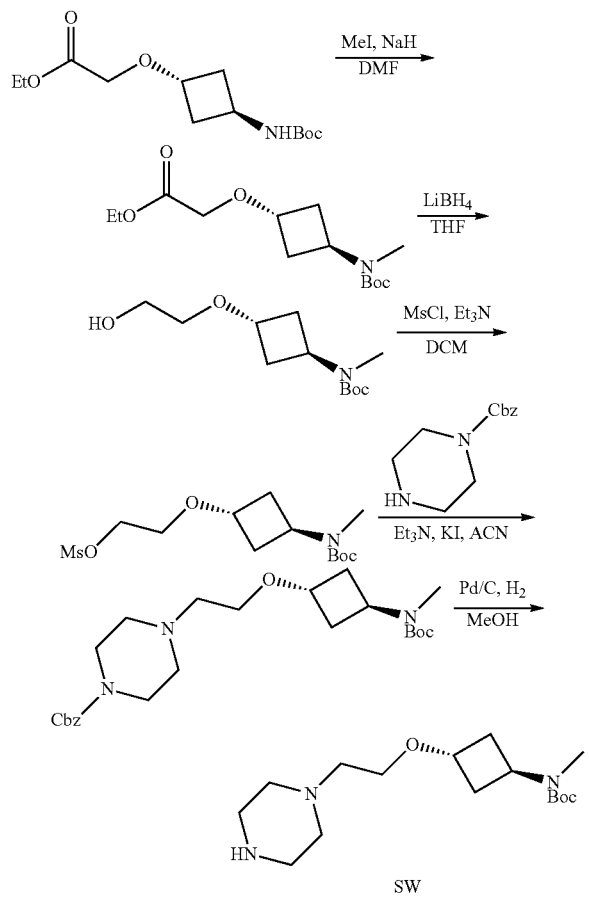

Step 1—Ethyl 2-[3-[tert-butoxycarbonyl(methyl)amino]cyclobutoxy]acetate

To a solution of ethyl 2-[3-(tert-butoxycarbonylamino)cyclobutoxy]acetate (5.00 g, 18 mmol, synthesized via Step 1 of Intermediate SJ) in DMF (50 mL) at 0° C. was added NaH (1.50 g, 36 mmol, 60% oil dispersion) and stirred at 0° C. for 0.5 hour. Then a solution of CH$_3$I (3.10 g, 22 mmol) in DMF (5 mL) was added to the reaction mixture and stirred at 0° C. for 1 hour. On completion, the reaction mixture was quenched by H$_2$O (20 mL) at 0° C., and then extracted with ethyl acetate (2×20 mL). The combined organic layers were washed with brine (2×25 mL), dried over Na$_2$SO$_4$, filtered and concentrated in vacuo to give the title compound (5.00 g, 95% yield) as yellow oil. $^1$H NMR (400 MHz, DMSO-d$_6$) δ 4.66-4.59 (m, 1H), 4.29-4.00 (m, 5H), 2.73 (s, 3H), 2.33-2.28 (m, 2H), 2.15-2.07 (m, 2H), 1.38 (s, 9H), 1.22-1.16 (m, 3H).

Step 2—Tert-butyl N-[3-(2-hydroxyethoxy)cyclobutyl]-N-methyl-carbamate

To a solution of ethyl 2-[3-[tert-butoxycarbonyl(methyl)amino]cyclobutoxy]acetate (2.50 g, 8.7 mmol) in THF (30 mL) was added LiBH$_4$ (0.57 g, 26 mmol) at 0° C., then the reaction mixture was stirred at 25° C. for 2 hour. On completion, the reaction mixture was quenched by water (20 mL) at 25° C., and then extracted with ethyl acetate (2×30 mL). The combined organic layers were washed with brine (2×40 mL), dried over Na$_2$SO$_4$, filtered and concentrated in vacuo to give the title compound (2.00 g, 93% yield) as colorless oil.

Step 3—2-[3-[Tert-butoxycarbonyl(methyl)amino]cyclobutoxy]ethyl methanesulfonate To a solution of tert-butyl N-[3-(2-hydroxyethoxy)cyclobutyl]-N-methyl-carbamate (2.00 g, 8.20 mmol) and Et$_3$N (1.7 g, 16 mmol) in DCM (20 mL) was added MsCl (1.40 g, 12 mmol), then the reaction mixture was stirred at 0° C. for 1 hour. On completion, the reaction mixture was quenched by water (25 mL) at 25° C., and extracted with DCM (2×30 mL). The combined organic layers were washed with brine (2×40 mL), dried over Na$_2$SO$_4$, filtered and concentrated in vacuo to give the title compound (2.50 g, 94% yield) as colorless oil.

Step 4—Benzyl 4-[2-[3-[tert-butoxycarbonyl(methyl)amino]cyclobutoxy]ethyl]piperazine-1-carboxylate To a solution of 2-[3-[tert-butoxycarbonyl(methyl)amino]cyclobutoxy]ethyl methanesulfonate (2.50 g, 7.70 mmol) and benzyl piperazine-1-carboxylate (3.40 g, 15.0 mmol) in ACN (30 mL) was added Et$_3$N (2.4 g) and KI (1.50 g, 9.3 mmol), then the reaction mixture was stirred at 70° C. for 12 hours. On completion, the reaction mixture was filtered and concentrated in vacuo. The crude product was purified by reverse phase HPLC (0.1% FA condition) to give the title compound (0.60 g, 16% yield) as a white solid. LC-MS (ESI$^+$) m/z 448.1 (M+H)$^+$.

Step 5—Tertbutyl N-methyl-N-[3-(2-piperazin-1-ylethoxy)cyclobutyl]carbamate

To a solution of benzyl 4-[2-[3-[tert-butoxycarbonyl(methyl)amino]cyclobutoxy]ethyl]piperazine-1-carboxylate (0.60 g, 1.3 mmol) in MeOH (5 mL) was added Pd/C (60 mg, 10% wt), then the mixture was degassed and purged with H$_2$ gas three times. The mixture was stirred at 25° C. for 2 hours under H$_2$ atmosphere. On completion, the reaction mixture was filtered and concentrated in vacuo to give the title compound (0.40 g, 95% yield) as colorless oil.

3-[3-Methyl-5-[[4-[2-[3-(methylamino)cyclobutoxy]ethyl]piperazin-1-yl]methyl]-2-oxo-benzimidazol-1-yl]piperidine-2,6-dione (Intermediate SX)

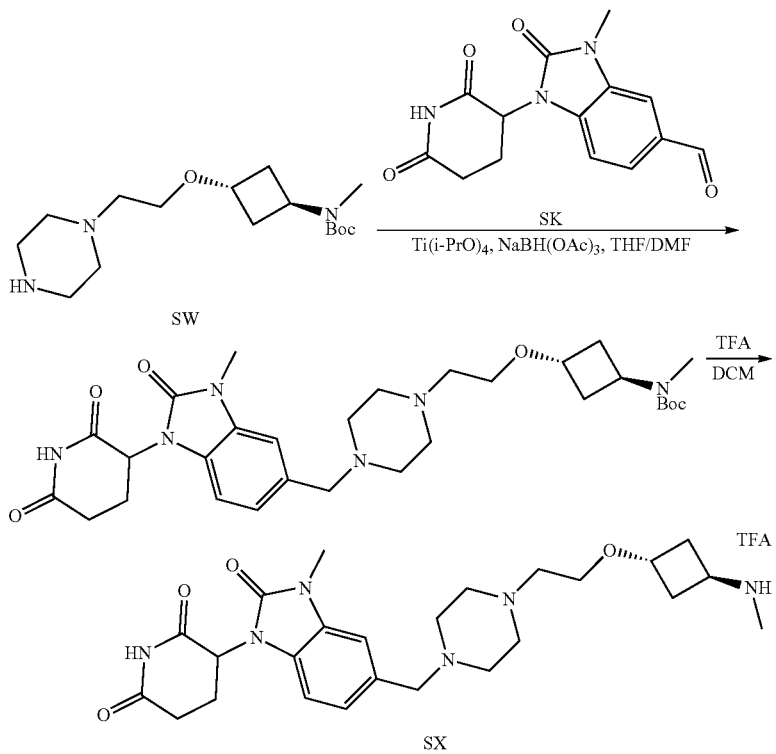

Step 1—Tert-butyl N-[3-[2-[4-[[1-(2,6-dioxo-3-piperidyl)-3-methyl-2-oxo-benzimidazol-5-yl]methyl]piperazin-1-yl]ethoxy]cyclobutyl]-N-methyl-carbamate To a solution of 1-(2,6-dioxo-3-piperidyl)-3-methyl-2-oxo-benzimidazole-5-carbaldehyde (0.15 g, 0.52 mmol, Intermediate SK) and tertbutyl N-methyl-N-[3-(2-piperazin-1-ylethoxy)cyclobutyl]carbamate (0.16 g, 0.52 mmol, Intermediate SW) in a mixed solvent of THF (2 mL) and DMF (2 mL) was added Ti(i-PrO)$_4$ (0.22 g, 0.78 mmol) and stirred at 50° C. for 4 hour, then NaBH(OAc)$_3$ (0.22 g, 1.0 mmol) was added at 25° C. The reaction mixture was stirred at 25° C. for 12 hours. On completion, the mixture was concentrated in vacuo. The crude product was purified by reverse phase HPLC (0.1% TFA condition) to give the title compound (40.0 mg, 8.7% yield) as colorless oil. LC-MS (ESI$^+$) m/z 585.4 (M+H)$^+$.

Step 2—3-[3-Methyl-5-[[4-[2-[3-(methylamino)cyclobutoxy]ethyl]piperazin-1-yl]methyl]-2-oxo-benzimidazol-1-yl]piperidine-2,6-dione To a solution of tert-butyl N-[3-[2-[4-[[1-(2,6-dioxo-3-piperidyl)-3-methyl-2-oxo-benzimidazol-5-yl]methyl]piperazin-1-yl]ethoxy]cyclobutyl]-N-methyl-carbamate (30.0 mg, 51.3 umol) in TFA (1.5 mL) was added DCM (2 mL). The reaction mixture was stirred at 25° C. for 2 hrs. On completion, the mixture was concentrated in vacuo to give the title compound (30.7 mg, 100% yield) as yellow oil. LC-MS (ESI$^+$) m/z 485.3 (M+H)$^+$.

Tert-butyl N-(4-but-3-ynoxybutyl)carbamate (Intermediate SY)

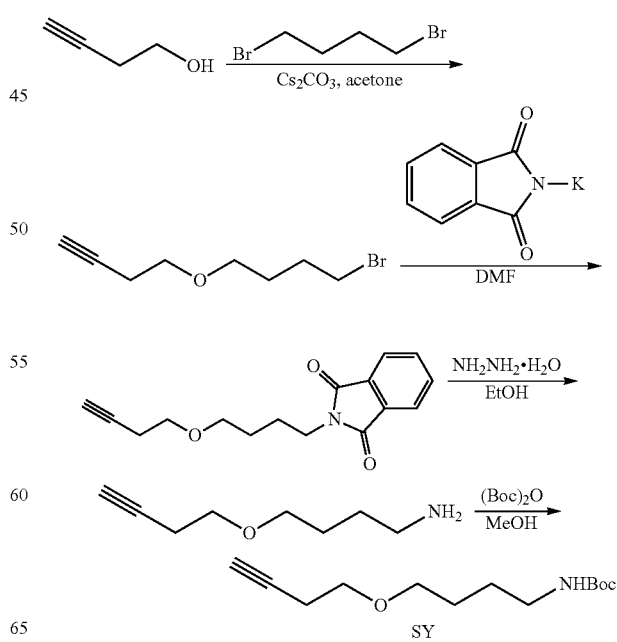

Step 1—1-bromo-4-but-3-ynoxy-butane

A mixture of but-3-yn-1-ol (40 g, 571 mmol, 43.2 mL, CAS #927-74-2), 1,4-dibromobutane (185 g, 856 mmol, 103 mL, CAS #110-52-1), $Cs_2CO_3$ (204 g, 627 mmol) in acetone (500 mL) was degassed and purged with $N_2$ for 3 times. Then the mixture was stirred at 70° C. for 72 hrs under $N_2$ atmosphere. On completion, the mixture was filtered and the filtrate was concentrated in vacuo. The residue was purified by silica gel chromatography to give the title compound (40.0 g, 34% yield) as colorless oil. $^1$H NMR (400 MHz, $CDCl_3$) δ 3.57 (t, J=6.8 Hz, 2H), 3.52 (t, J=6.2 Hz, 2H), 3.49-3.45 (m, 3H), 2.48 (dt, J=2.8, 6.8 Hz, 2H), 2.08-2.04 (m, 1H), 2.03-1.96 (m, 2H), 1.80-1.71 (m, 2H).

Step 2—2-(4-But-3-ynoxybutyl)isoindoline-1,3-dione

To a solution of 1-bromo-4-but-3-ynoxy-butane (27.0 g, 131 mmol) in DMF (300 mL) was added (1,3-dioxoisoindolin-2-yl)potassium (29.3 g, 158 mmol). The mixture was stirred at 60° C. for 6 hrs. On completion, 1500 mL $H_2O$ was added to the mixture, and the mixture was extracted with EA (2×800 mL). The organic layer was washed with brine (300 mL), and then concentrated in vacuo to give the title compound (30.0 g, 84% yield) as white solid. $^1$H NMR (400 MHz, $CDCl_3$) δ 7.87-7.83 (m, 2H), 7.75-7.70 (m, 2H), 3.73 (t, J=7.2 Hz, 2H), 3.53 (td, J=6.8, 19.2 Hz, 4H), 2.45 (dt, J=2.8, 7.2 Hz, 2H), 1.98 (t, J=2.8 Hz, 1H), 1.83-1.71 (m, 2H), 1.69-1.59 (m, 2H).

Step 3—4-But-3-ynoxybutan-1-amine

To a solution of 2-(4-but-3-ynoxybutyl)isoindoline-1,3-dione (50.0 g, 184 mmol) in EtOH (1000 mL) was added $NH_2NH_2 \cdot H_2O$ (92.3 g, 1.84 mol, 89.6 mL). The mixture was stirred at 80° C. for 4 hrs. On completion, the mixture was filtered and the filtrate was concentrated in vacuo to give the title compound (21.0 g, 31% yield) as colorless oil. $^1$H NMR (400 MHz, $CDCl_3$) δ 3.49 (t, J=7.2 Hz, 2H), 3.43-3.38 (m, 2H), 2.65 (t, J=7.2 Hz, 2H), 2.39 (dt, J=2.8, 6.8 Hz, 2H), 1.91 (t, J=2.8 Hz, 1H), 1.89 (s, 2H), 1.60-1.52 (m, 2H), 1.49-1.40 (m, 2H).

Step 4—Tert-butyl N-(4-but-3-ynoxybutyl)carbamate

To a solution of 4-but-3-ynoxybutan-1-amine (30.0 g, 212 mmol) in MeOH (300 mL) was added $(Boc)_2O$ (69.6 g, 318 mmol, 73.2 mL). The mixture was stirred at 25° C. for 4 hrs. On completion, the mixture was concentrated in vacuo. The residue was purified by silica gel chromatography to give the title compound (50.0 g, 97% yield) as colorless oil. $^1$H NMR (400 MHz, $CDCl_3$) δ 4.68 (s, 1H), 3.57 (t, J=6.8 Hz, 2H), 3.49 (t, J=6.0 Hz, 2H), 3.20-3.11 (m, 2H), 2.48 (dt, J=2.8, 6.8 Hz, 2H), 1.99 (t, J=2.8 Hz, 1H), 1.68-1.59 (m, 4H), 1.46 (s, 9H).

3-[3-methyl-5-[3-[(2R)-2-(methylaminomethyl)morpholin-4-yl]propyl]-2-oxo-benzimidazol-1-yl]piperidine-2,6-dione (Intermediate SZ)

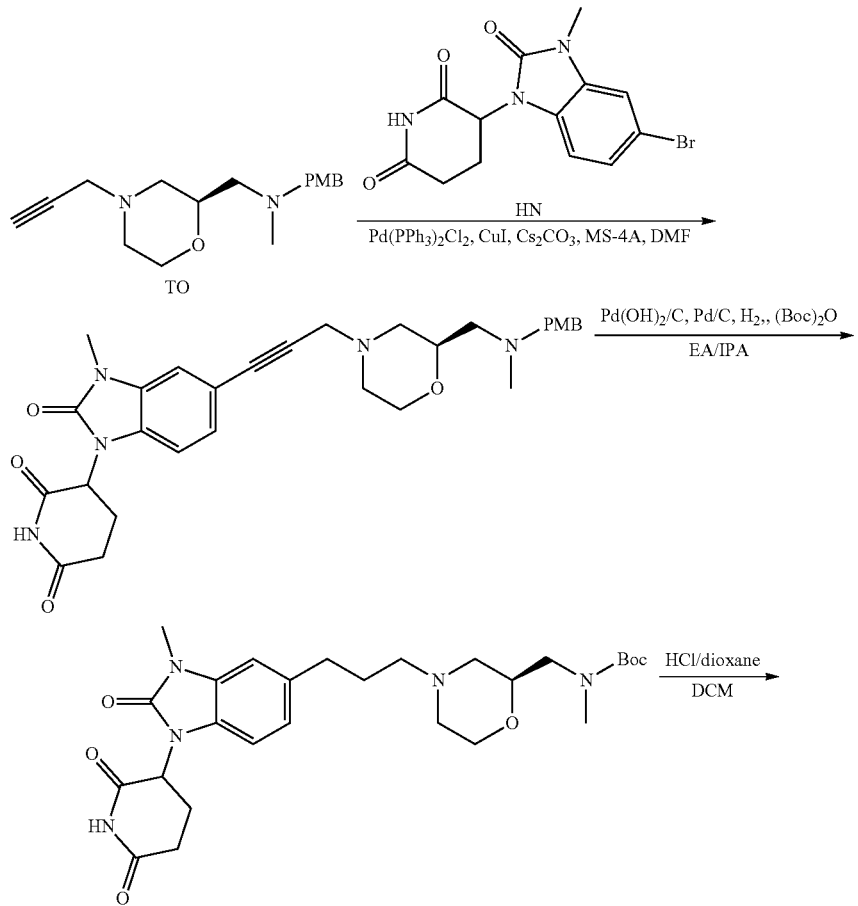

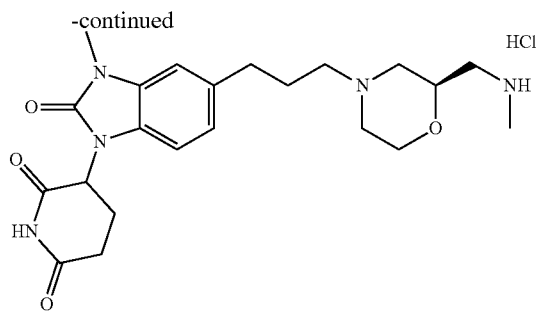

SZ

Step 1—3-[5-[3-[(2R)-2-[[(4-methoxyphenyl)methyl-methyl-amino]methyl]morpholin-4-yl]prop-1-ynyl]-3-methyl-2-oxo-benzimidazol-1-yl]piperidine-2,6-dione To a solution of 1-(4-methoxyphenyl)-N-methyl-N-[[(2R)-4-prop-2-ynylmorpholin-2-yl]methyl]methanamine (900 mg, 3.12 mmol, Intermediate TO) and 3-(5-bromo-3-methyl-2-oxo-benzimidazol-1-yl)piperidine-2,6-dione (703 mg, 2.08 mmol, Intermediate HN) in DMF (20 mL) was added 4 Å molecular sieves (300 mg), Pd(PPh$_3$)$_2$Cl$_2$ (146 mg, 208 umol), Cs$_2$CO$_3$ (2.71 g, 8.32 mmol) and CuI (39.6 mg, 208 umol). The reaction mixture was stirred at 80° C. for 2 hr under N$_2$. On completion, the mixture was filtered, and the filtrate was concentrated in vacuo to give a residue. The residue was purified by reverse phase (0.1% FA condition) to give the title compound (1.10 g, 96% yield) as a yellow solid. LC-MS (ESI$^+$) m/z 546.4 (M+H)$^+$.

Step 2—Tert-butyl N-[[(2S)-4-[3-[1-(2,6-dioxo-3-piperidyl)-3-methyl-2-oxo-benzimidazol-5-yl]propyl]morpholin-2-yl]methyl]-N-methyl-carbamate To a solution of 3-[5-[3-[(2R)-2-[[(4-methoxyphenyl)methyl-methyl-amino]methyl]morpholin-4-yl]prop-1-ynyl]-3-methyl-2-oxo-benzimidazol-1-yl]piperidine-2,6-dione (500 mg, 916 umol) in IPA (15 mL) and EA (30 mL) was added Pd(OH)$_2$/C (200 mg, 10 wt %), Pd/C (200 mg, 10 wt %) and (Boc)$_2$O (300 mg, 1.37 mmol, 315 uL). The reaction mixture was stirred at 25° C. for 48 hr under H$_2$ (50 psi). On completion, the residue was filtered and the filtrate was concentrated in vacuo to give a residue. The residue was purified by reverse phase (0.1% FA condition) to give the title compound (300 mg, 62% yield) as a yellow solid. $^1$H NMR (400 MHz, DMSO-d$_6$) δ 11.08 (s, 1H), 7.08-6.93 (m, 2H), 6.86 (d, J=8.0 Hz, 1H), 5.75 (s, 1H), 5.33 (dd, J=5.2, 12.8 Hz, 1H), 3.63-3.56 (m, 4H), 3.52-3.46 (m, 2H), 3.31 (s, 3H), 3.26-3.12 (m, 3H), 2.93-2.85 (m, 1H), 2.72-2.58 (m, 6H), 2.07-1.96 (m, 2H), 1.81-1.69 (m, 3H), 1.37 (s, 9H); LC-MS (ESI$^+$) m/z 530.3 (M+H)$^+$.

Step 3—3-[3-Methyl-5-[3-[(2R)-2-(methylaminomethyl)morpholin-4-yl]propyl]-2-oxo-benzimidazol-1-yl]piperidine-2,6-dione To a solution of tert-butyl N-[[(2S)-4-[3-[1-(2,6-dioxo-3-piperidyl)-3-methyl-2-oxo-benzimidazol-5-yl]propyl]morpholin-2-yl]methyl]-N-methyl-carbamate (300 mg, 566 umol) in DCM (8 mL) was added HCl/dioxane (4 M, 4 mL). The reaction mixture was stirred at 25° C. for 2 hr. On completion, the mixture was concentrated in vacuo to give the title compound (260 mg, 98% yield, HCl) as a white solid. LC-MS (ESI$^+$) m/z 430.2 (M+H)$^+$.

tert-butyl 4-[3-[[3-(difluoromethyl)-1-(4-formylphenyl)pyrazol-4-yl]carbamoyl]pyrazolo[1,5-a]pyrimidin-5-yl]piperazine-1-carboxylate (Intermediate TA)

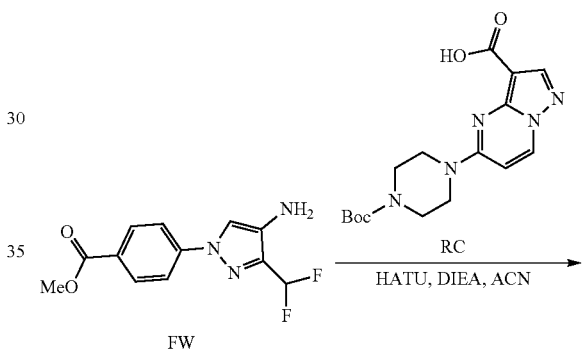

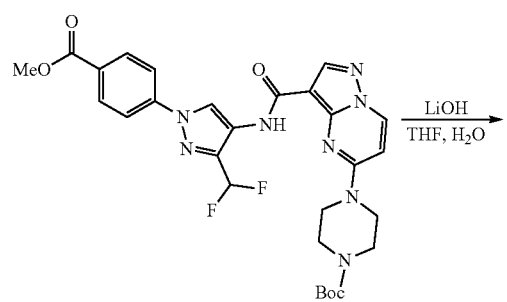

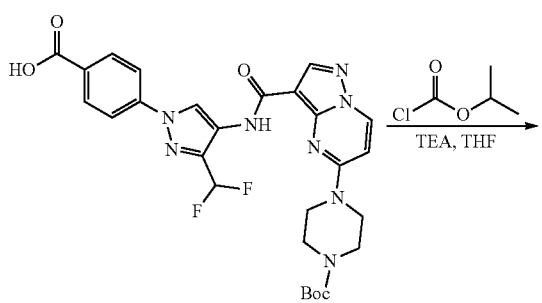

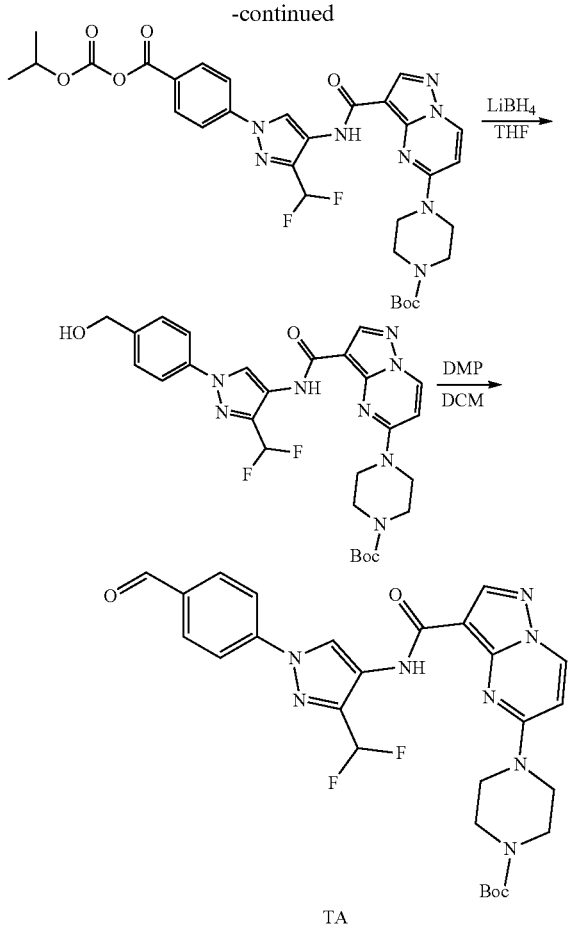

Step 1—Tert-butyl 4-[3-[[3-(difluoromethyl)-1-(4-methoxycarbonylphenyl)pyrazol-4-yl]carbamoyl]pyrazolo[1,5-a]pyrimidin-5-yl]piperazine-1-carboxylate To a solution of methyl 4-[4-amino-3-(difluoromethyl)pyrazol-1-yl]benzoate (650 mg, 2.43 mmol, Intermediate FW), 5-(4-tertbutoxycarbonylpiperazin-1-yl)pyrazolo[1,5-a]pyrimidine-3-carboxylic acid (650 mg, 1.87 mmol, Intermediate RC) in ACN (15.0 mL) was added DIPEA (725 mg, 5.61 mmol), HATU (1.42 g, 3.74 mmol). The mixture was stirred at 60° C. for 16 hrs. On completion, the mixture was concentrated in vacuo. The mixture was purified by reverse phase: (0.1% FA) to give the title compound (700 mg, 62% yield) as yellow solid. $^1$H NMR (400 MHz, CDCl$_3$) δ 9.60 (s, 1H), 9.05 (s, 1H), 8.48 (s, 1H), 8.38 (d, J=8.0 Hz, 1H), 8.17 (d, J=8.8 Hz, 2H), 7.83 (d, J=8.8 Hz, 2H), 7.09-6.76 (m, 1H), 6.46 (d, J=8.0 Hz, 1H), 3.96 (s, 3H), 3.86 (s, 4H), 3.65 (s, 4H), 1.54 (s, 9H).

Step 2—4-[4-[[5-(4-Tert-butoxycarbonylpiperazin-1-yl)pyrazolo[1,5-a]pyrimidine-3-carbonyl]amino]-3-(difluoromethyl)pyrazol-1-yl]benzoic acid To a solution of tert-butyl 4-[3-[[3-(difluoromethyl)-1-(4-methoxycarbonylphenyl)pyrazol-4-yl]carbamoyl]pyrazolo[1,5-a]pyrimidin-5-yl]piperazine-1-carboxylate (1.00 g, 1.68 mmol) in THF (40.0 mL) and H$_2$O (8 mL) was added LiOH (200 mg, 8.38 mmol). The mixture was stirred at 20° C. for 16 hrs. On completion, the mixture was concentrated in vacuo. The mixture was diluted with H$_2$O (30 mL), then the mixture was acidified with 1N HCl solution until the pH=5. The mixture was filtered and the filter cake was dried in vacuo to give the title compound (900 mg, 92% yield) as yellow solid. $^1$H NMR (400 MHz, DMSO-d$_6$) δ 12.01 (s, 1H), 9.48 (s, 1H), 9.08 (s, 1H), 8.82 (d, J=8.0 Hz, 1H), 8.32 (s, 1H), 8.07 (d, J=8.8 Hz, 2H), 7.97 (d, J=8.8 Hz, 2H), 7.52-7.16 (m, 1H), 6.89 (d, J=8.0 Hz, 1H), 3.82 (s, 4H), 3.50 (s, 4H), 1.44 (s, 9H).

Step 3—Tert-butyl 4-[3-[[3-(difluoromethyl)-1-(4-isopropoxycarbonyloxycarbonylphenyl) pyrazol-4-yl]carbamoyl]pyrazolo[1,5-a]pyrimidin-5-yl]piperazine-1-carboxylate To a solution of 4-[4-[[5-(4-tert-butoxycarbonylpiperazin-1-yl)pyrazolo[1,5-a]pyrimidine-3-carbonyl]amino]-3-(difluoromethyl)pyrazol-1-yl]benzoic acid (900 mg, 1.54 mmol), TEA (625 mg, 6.18 mmol) in THF (30.0 mL) was added isopropyl carbonochloridate (473 mg, 3.86 mmol) at −10° C. The mixture was stirred at −10° C. for 1 hrs. On completion, the mixture was filtered and the filtrate was concentrated in vacuo to give the title compound (1.00 g, 90% yield) as yellow solid. LC-MS (ESI$^+$) m/z 669.2 (M+H)$^+$.

Step 4—Tert-butyl 4-[3-[[3-difluoromethyl)-1-[4-(hydroxymethyl)phenyl]pyrazol-4-yl]carbamoyl]pyrazolo[1,5-a]pyrimidin-5-yl]piperazine-1-carboxylate To a solution of tert-butyl 4-[3-[[3-(difluoromethyl)-1-(4-isopropoxycarbonyloxycarbonylphenyl) pyrazol-4-yl]carbamoyl]pyrazolo[1,5-a]pyrimidin-5-yl]piperazine-1-carboxylate (1.00 g, 1.50 mmol) in THF (50.0 mL) and H$_2$O (10.0 mL) was added LiBH$_4$ (195 mg, 8.97 mmol) at 0° C. The mixture was stirred at 0° C. for 1 hr. On completion, the mixture was quenched with H$_2$O (10 mL), then extracted with DCM (2×30 mL). The organic layers were dried with anhydrous Na$_2$SO$_4$, filtered and concentrated in vacuo. The mixture was triturated with DCM (5 mL) to give the title compound (700 mg, 82% yield) as yellow solid. $^1$H NMR (400 MHz, DMSO-d$_6$) δ 9.49 (s, 1H), 8.98 (s, 1H), 8.85 (d, J=8.0 Hz, 1H), 8.33 (s, 1H), 7.80 (d, J=8.4 Hz, 2H), 7.48 (d, J=8.4 Hz, 2H), 7.34-6.96 (m, 1H), 6.91 (d, J=8.0 Hz, 1H), 5.35-5.24 (m, 1H), 4.56 (d, J=4.4 Hz, 2H), 3.84 (s, 4H), 3.50 (s, 4H), 1.45 (s, 9H).

Step 5—Tert-butyl 4-[3-[[3-(difluoromethyl)-1-(4-formylphenyl)pyrazol-4-yl]carbamoyl]pyrazolo[1,5-a]pyrimidin-5-yl]piperazine-1-carboxylate To a solution of tert-butyl 4-[3-[[3-(difluoromethyl)-1-[4-(hydroxymethyl)phenyl]pyrazol-4-yl]carbamoyl]pyrazolo[1,5-a]pyrimidin-5-yl]piperazine-1-carboxylate (700 mg, 1.23 mmol) in THF (30.0 mL) was added DMP (626 mg, 1.48 mmol). The mixture was stirred at 20° C. for 1 hr. On completion, the mixture was quenched with saturated Na$_2$S2O3 (30 mL) and washed with saturated NaHCO$_3$ (2×30 mL). The organic layer was dried over anhydrous Na$_2$SO$_4$, filtered and concentrated in vacuo to give the title compound (680 mg, 90% yield) as yellow solid. $^1$H NMR (400 MHz, DMSO-d$_6$) δ 10.04 (s, 1H), 9.52 (s, 1H), 9.17 (s, 1H), 8.86 (d, J=8.0 Hz, 1H), 8.35 (s, 1H), 8.15-8.10 (m, 2H), 8.09-8.03 (m, 2H), 7.54-7.23 (m, 1H), 6.96-6.86 (m, 1H), 3.85 (s, 4H), 3.51 (s, 4H), 1.45 (s, 9H).

2-[(E)-2-[1-(2,6-Dioxo-3-piperidyl)-3-methyl-2-oxo-benzimidazol-5-yl]vinyloxy]ethyl methanesulfonate (Intermediate TB)

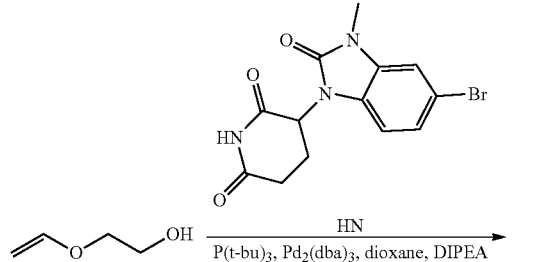

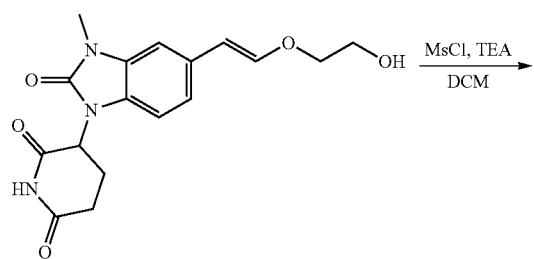

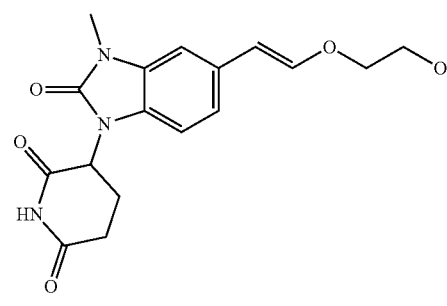

TB

Step 1—3-[5-[(E)-2-(2-Hydroxyethoxy)vinyl]-3-methyl-2-oxo-benzimidazol-1-yl]piperidine-2,6-dione To a solution of 3-(5-bromo-3-methyl-2-oxo-benzimidazol-1-yl)piperidine-2,6-dione (1.00 g, 2.96 mmol, Intermediate HN), 2-vinyloxyethanol (782 mg, 8.88 mmol, CAS #764-48-7) in dioxane (25 mL) was added P(t-Bu)₃ toluene solution (2.08 mL, 591 umol, 10 wt %), Pd₂(dba)₃ (542 mg, 591 umol) and DIPEA (497 mg, 3.84 mmol) under N₂. The mixture was stirred at 25° C. for 16 hours. On completion, the mixture was concentrated in vacuo. The residue was purified by silica gel column to give the title compound (500 mg, 49% yield) as yellow solid. ¹H NMR (400 MHz, DMSO-d₆) δ 11.08 (s, 1H), 7.25-7.19 (m, 1H), 7.19-7.09 (m, 1H), 6.99 (d, J=8.4 Hz, 1H), 6.95-6.90 (m, 1H), 6.35 (d, J=7.2 Hz, 1H), 5.88 (d, J=12.8 Hz, 1H), 5.38-5.29 (m, 1H), 5.25 (d, J=7.2 Hz, 1H), 3.99-3.83 (m, 1H), 3.85 (t, J=5.2 Hz, 1H), 3.69-3.61 (m, 2H), 3.39 (s, 3H), 2.97-2.82 (m, 1H), 2.66-2.58 (m, 1H), 2.53 (d, J=1.6 Hz, 1H), 2.06-1.99 (m, 1H).

Step 2—2-[(E)-2-[1-(2,6-Dioxo-3-piperidyl)-3-methyl-2-oxo-benzimidazol-5-yl]vinyloxy]ethyl methanesulfonate To a solution of 3-[5-[(E)-2-(2-hydroxyethoxy)vinyl]-3-methyl-2-oxo-benzimidazol-1-yl]piperidine-2,6-dione (750 mg, 2.17 mmol) in DCM (100 mL) was added TEA (659 mg, 6.52 mmol) and MsCl (373 mg, 3.26 mmol) at 0° C. The reaction mixture was stirred at 25° C. for 2 hours. On completion, the reaction mixture was poured into water (30 mL) and extracted with DCM (2×100 mL). The combined organic layers were washed with brine (80 mL) and sat. aq. NaHCO₃ (2×70 mL), dried with anhydrous Na₂SO₄, filtered and concentrated in vacuo to give the title compound (800 mg, 70% yield, 75% purity) as a brown solid. LC-MS (ESI⁺) m/z 423.9 (M+H)⁺.

3-[5-[2-[2-[(2S)-2-(Aminomethyl)morpholin-4-yl]ethoxy]ethyl]-3-methyl-2-oxo-benzimidazol-1-yl]piperidine-2,6-dione (Intermediate TC)

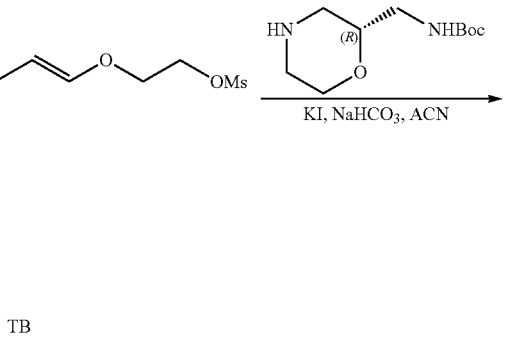

TB

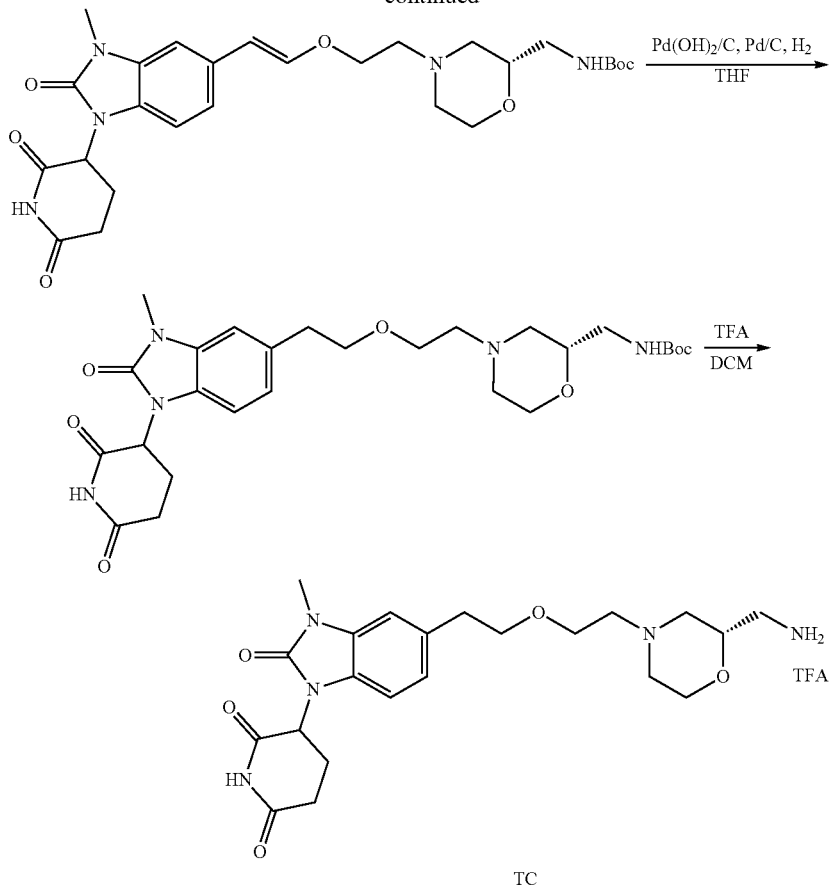

TC

Step 1—Tert-butyl N-[[(2S)-4-[2-[(E)-2-[1-(2,6-dioxo-3-piperidyl)-3-methyl-2-oxo-benzimidazol-5-yl]vinyloxy]ethyl]morpholin-2-yl]methyl]carbamate To a solution of 2-[(E)-2-[1-(2,6-dioxo-3-piperidyl)-3-methyl-2-oxo-benzimidazol-5-yl]vinyloxy]ethyl methanesulfonate (350 mg, 827 umol, Intermediate TB), tert-butyl N-[[(2R)-morpholin-2-yl]methyl]carbamate (268 mg, 1.24 mmol, CAS #186202-57-3) in DMF (5 mL) was added DIPEA (320 mg, 2.48 mmol) at 20° C. The mixture was stirred at 110° C. for 1 hour. On completion, the mixture was concentrated in vacuo. The mixture was purified by prep-HPLC (reverse phase: 0.1% FA) to give the title compound (270 mg, 60% yield) as a yellow solid. $^1$H NMR (400 MHz, CDCl$_3$) δ 8.28 (s, 1H), 6.97-6.82 (m, 2H), 6.82-6.69 (m, 1H), 6.12 (d, J=7.2 Hz, 1H), 5.95 (d, J=12.8 Hz, 1H), 5.43 (d, J=7.1 Hz, 1H), 5.26-5.18 (m, 1H), 4.89 (s, 1H), 4.39-4.18 (m, 2H), 4.06 (d, J=7.2 Hz, 2H), 3.98-3.87 (m, 1H), 3.68-3.54 (m, 2H), 3.46-3.43 (m, 3H), 3.41-3.36 (m, 2H), 3.33-3.24 (m, 2H), 2.99-2.91 (m, 2H), 2.87-2.81 (m, 1H), 2.79-2.75 (m, 1H), 2.74-2.68 (m, 1H), 2.31-2.21 (m, 1H), 1.47 (s, 9H).

Step 2—Tert-butyl N-[[(2S)-4-[2-[2-[1-(2,6-dioxo-3-piperidyl)-3-methyl-2-oxo-benzimidazol-5-yl]ethoxy]ethyl]morpholin-2-yl]methyl]carbamate To a solution of tert-butyl N-[[(2S)-4-[2-[(E)-2-[1-(2,6-dioxo-3-piperidyl)-3-methyl-2-oxo-benzimidazol-5-yl]vinyloxy]ethyl]morpholin-2-yl]methyl]carbamate (270 mg, 496 umol) in THF (20 mL) was added Pd/C (50.0 mg, 10 wt %) and Pd(OH)$_2$/C (50.0 mg, 10 wt %) at 25° C. The mixture was stirred at 25° C. for 2 hours under H$_2$ (15 psi). On completion, the mixture was filtered. The filtrate was concentrated in vacuo. The mixture was purified by prep-HPLC (reverse phase: 0.1% FA) to give the title compound (150 mg, 30% yield) as a yellow solid. $^1$H NMR (400 MHz, DMSO-d$_6$) δ 11.10 (s, 1H), 7.09 (s, 1H), 7.04-6.94 (m, 2H), 6.65 (s, 1H), 5.37-5.33 (m, 1H), 3.68 (s, 3H), 3.65-3.59 (m, 4H), 3.34 (s, 3H), 3.04-2.93 (m, 4H), 2.91-2.79 (m, 4H), 2.75-2.70 (m, 1H), 2.66-2.61 (m, 1H), 2.55-2.53 (m, 1H), 2.04-1.96 (m, 1H), 1.78-1.75 (m, 2H), 1.36 (s, 9H).

Step 3—3-[5-[2-[2-[(2S)-2-(Aminomethyl)morpholin-4-yl]ethoxy]ethyl]-3-methyl-2-oxo-benzimidazol-1-yl]piperidine-2,6-dione To a solution of tert-butyl N-[[(2S)-4-[2-[2-[1-(2,6-dioxo-3-piperidyl)-3-methyl-2-oxo-benzimidazol-5-yl]ethoxy]ethyl]morpholin-2-yl]methyl]carbamate (100 mg, 184 umol) in DCM (2 mL) was added TFA (1 mL) at 15° C. The mixture was stirred at 15° C. for 2 hours. On completion, the mixture was concentrated in vacuo to give the title compound (80.0 mg, 98% yield, TFA salt) as a white solid. LC-MS (ESI$^+$) m/z 446.3 (M+H)$^+$.

3-[6-[3-[2-[2-(Methylamino)ethoxy]ethoxy]propyl]-2-oxo-1,3-benzoxazol-3-yl]piperidine-2,6-dione (Intermediate TF)

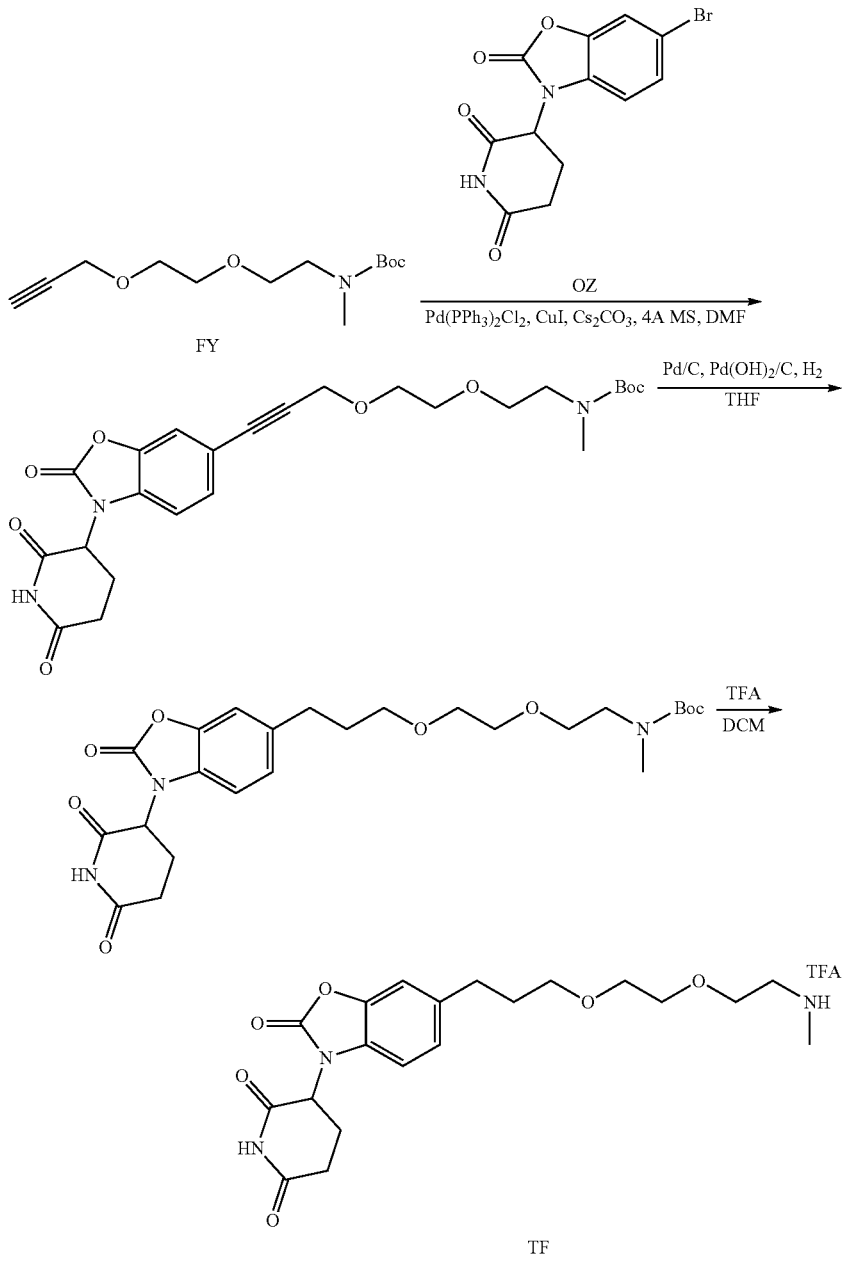

Step 1—Tert-butyl N-[2-[2-[3-[3-(2,6-dioxo-3-piperidyl)-2-oxo-1,3-benzoxazol-6-yl]prop-2-ynoxy]ethoxy]ethyl]-N-methyl-carbamate A mixture of tert-butyl N-methyl-N-[2-(2-prop-2-ynoxyethoxy)ethyl]carbamate (427 mg, 1.66 mmol, Intermediate FY), 3-(6-bromo-2-oxo-1,3-benzoxazol-3-yl)piperidine-2,6-dione (300 mg, 923 umol, Intermediate OZ), 4 Å molecular sieves (40 mg), Pd(PPh₃)₂Cl₂ (129 mg, 185 umol), CuI (35.2 mg, 184 umol) and Cs₂CO₃ (1.50 g, 4.61 mmol) in DMF (10 mL) was de-gassed and then heated at 80° C. for 2 hrs. On completion, the reaction mixture was concentrated in vacuo. The crude product was purified by reversed-phase HPLC (0.1% FA condition) to give the title compound (280 mg, 61% yield) as yellow oil. LC-MS (ESI⁺) m/z 524.3 (M+Na)⁺.

Step 2—Tert-butyl N-[2-[2-[3-[3 (2,6-dioxo-3-piperidyl)-2-oxo-1,3-benzoxazol-6-yl]propoxy]ethoxy]thyl]-N-methyl-carbamate To a solution of tert-butyl-[2-[2-[3-[3-(2,6-dioxo-3-piperidyl)-2-xo-1,3-benzoxazol-6-yl]prop-2-noxy]ethoxyethyl]-N-methyl-carbamate (280 mg, 558 umol) in THF (20 mL) was added Pd/C (50 mg, 10% wt) and Pd(OH)₂/C (50 mg, 10% wt) under N₂ atmosphere. The suspension was degassed under vacuum and purged with H₂ several times. The reaction mixture was stirred at 25° C. for 4 hrs under H₂ (15 psi). On completion, the reaction mixture was filtered and the filtrate was concentrated in vacuo to give the title compound (150 mg, 53% yield) as yellow oil. $^1$H NMR (400 MHz, DMSO-d$_6$) δ 11.19 (s, 1H), 7.25-7.23 (m, 1H), 7.15-7.11 (m, 1H), 7.03 (d, J=7.6 Hz, 1H), 5.34 (dd, J=5.2, 12 Hz, 1H), 3.5-3.48 (m, 4H), 3.42-3.39 (m, 2H), 3.37-3.35 (m, 3H), 3.31-3.27 (m, 4H), 2.81-2.80 (m, 2H), 2.69-2.61 (m, 1H), 2.63-2.61 (m, 2H), 2.13-2.10 (m, 1H), 1.80-1.75 (m, 2H), 1.37 (s, 9H); LC-MS (ESI+) m/z 528.3 (M+Na)$^+$.

Step 3—3-[6-[3-[2-[2-(Methylamino)ethoxy]ethoxy]propyl]-2-oxo-1,3-benzoxazol-3-yl]piperidine-2,6-dione To a solution of tert-butyl N-[2-[2-[3-[3-(2,6-dioxo-3-piperidyl)-2-oxo-1,3-benzoxazol-6-yl]propoxy]ethoxy]ethyl]-N-methyl-carbamate (140 mg, 277 umol) in DCM (3 mL) was added TFA (2 mL). The mixture was stirred at 25° C. for 2 hrs under N$_2$ atmosphere. On completion, the reaction mixture was concentrated in vacuo to give the title compound (11.9 mg, 39% yield) as white solid. LC-MS (ESI+) m/z 406.2 (M+H)$^+$.

3-[6-[3-[3-(Methylamino)propoxy]propyl]pyrido[2,3-b]indol-9-yl]piperidine-2,6-dione (Intermediate TH)

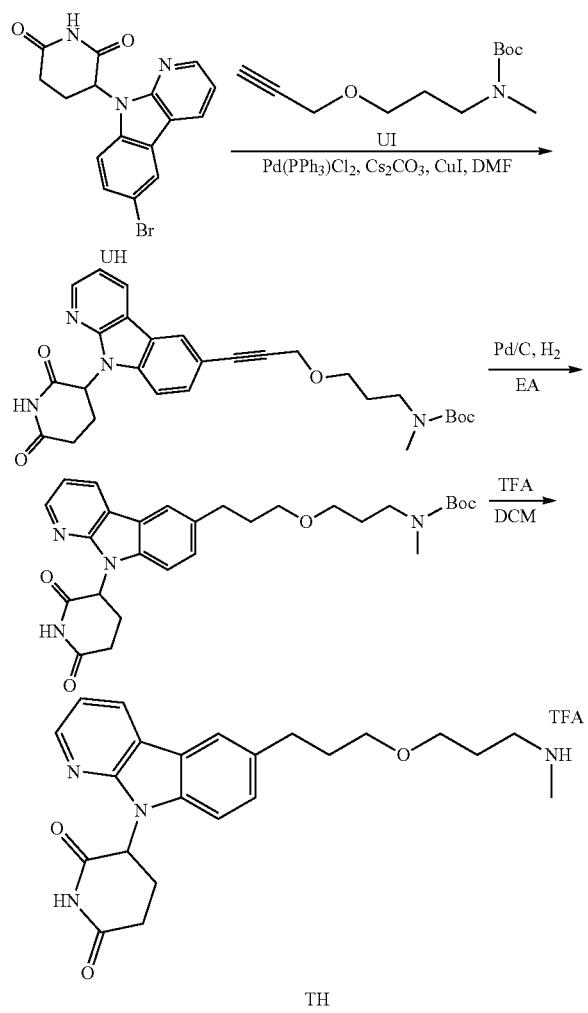

TH

Step 1—tert-butyl (3-(9-(2,6-dioxopiperidin-3-yl)-9H-pyrido[2,3-b]indol-6-yl)prop-2-yn-1-yl)oxy)propyl)(methyl)carbamate A mixture of 3-(6-bromo-9H-pyrido[2,3-b]indol-9-yl)piperidine-2,6-dione (100 mg, 0.279 mmol, Intermediate UH), tert-butyl methyl(3-(prop-2-yn-1-yloxy)propyl)carbamate (190 mg, 0.838 mmol, Intermediate UI), Pd(PPh$_3$)$_2$Cl$_2$ (30 mg, 0.0419 mmol), CuI (4 mg, 0.0223 mmol), Cs$_2$CO$_3$ (455 mg, 1.40 mmol), 4 Å MS (200 mg) and DMF (5 mL) was heated to 80° C. under microwave for 1.5 h under N$_2$. The mixture was then poured into 1N HCl (20 mL), then extracted with EA (3×20 mL). The organic layers were washed with brine (20 mL), dried over Na$_2$SO$_4$, filtered, concentrated and purified by column chromatography on silica gel (PE/EA=10/1 to 5/1 to 2/1) to give the title compound (50 mg, 35% yield) as a white solid. $^1$H NMR (400 MHz, CDCl$_3$) δ 8.57 (d, J=7.2 Hz, 1H), 8.46 (dd, J=1.2 Hz, J=5.6 Hz, 1H), 8.25 (d, J=1.2 Hz, 1H), 8.13 (s, 1H), 7.65 (dd, J=1.6 Hz, J=4.0 Hz, 1H), 7.25-7.19 (m, 2H), 5.90 (dd, J=2.8 Hz, J=6.0 Hz, 1H), 4.41 (s, 2H), 3.63 (t, J=6.4 Hz, 2H), 3.34 (t, J=7.2 Hz, 2H), 3.02-2.91 (m, 3H), 2.89 (s, 3H), 2.50-2.47 (m, 1H), 1.88 (t, J=6.8 Hz, 2H), 1.46 (s, 9H). LC/MS (ESI, m/z): [M+1]$^+$=505.2.

Step 2—tert-butyl (3-(3-(9-(2,6-dioxopiperidin-3-yl)-9H-pyrido[2,3-b]indol-6-yl)propoxy)propyl)(methyl)carbamate A mixture of tert-butyl (3-((3-(9-(2,6-dioxopiperidin-3-yl)-9H-pyrido[2,3-b]indol-6-yl)prop-2-yn-1-yl)oxy)propyl)(methyl)carbamate (320 mg, 0.634 mmol), Pd/C (320 mg) and EA (10 mL) was stirred for overnight at rt under H$_2$. The mixture was filtered, concentrated and purified by column (PE/EA=1/1) to give the title product (170 mg, 53% yield) as a white solid. $^1$H NMR (400 MHz, CDCl$_3$) δ 8.41 (dd, J=1.6 Hz, J=4.8 Hz, 1H), 8.32 (d, J=7.6 Hz, 1H), 8.15 (s, 1H), 7.91 (d, J=0.8 Hz, 1H), 7.33 (dd, J=1.2 Hz, J=8.0 Hz, 1H), 7.22-7.16 (m, 2H), 5.94 (br s, 1H), 3.45 (dd, J=6.4 Hz, J=11.6 Hz, 4H), 3.13 (t, J=5.8 Hz, 2H), 3.07-2.95 (m, 3H), 2.88-2.84 (m, 5H), 2.33-2.29 (m, 1H), 2.01-1.93 (m, 2H), 1.85-1.78 (m, 2H), 1.46 (s, 9H). LC/MS (ESI, m/z): [M−BOC+H]$^+$=409.2 and [M−56+H]=453.2.

Step 3—3-[6-[3-[3-(Methylamino)propoxy]propyl]pyrido[2,3-b]indol-9-yl]piperidine-2,6-dione To a solution of tert-butyl N-[3-[3-[9-(2,6-dioxo-3-piperidyl)pyrido[2,3-b]indol-6-yl]propoxy]propyl]-N-methyl-carbamate (85.0 mg, 167 umol) in DCM (6 mL) was added TFA (381 mg, 3.34 mmol). The mixture was stirred at 25° C. for 2 hrs. On completion, the reaction mixture was concentrated in vacuo to give the title compound (87 mg, 95% yield, TFA salt) as light yellow oil. LC-MS (ESI$^+$) m/z 409.3 (M+H)$^+$.

2-(2-Prop-2-ynoxyethoxy)ethyl 4-methylbenzenesulfonate (Intermediate TI)

-continued

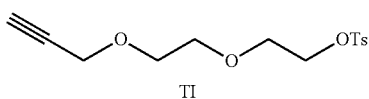

TI

To a solution of 2-(2-prop-2-ynoxyethoxy)ethanol (2.00 g, 13.8 mmol, Intermediate LC), TEA (4.21 g, 41.6 mmol) and DMAP (170 mg, 1.39 mmol) in DCM (60 mL) was added 4-methylbenzenesulfonyl chloride (5.29 g, 27.7 mmol) at 0° C. The mixture was then stirred at 25° C. for 16 hours. On completion, the mixture was washed with 2.0 M aq.HCl (20 mL) and brine (20 mL), dried over $Na_2SO_4$, filtered and concentrated in vacuo. The residue was purified by column chromatography on silica gel to give the title compound (3.40 g, 82% yield) as light yellow oil. $^1$H NMR (400 MHz, $CDCl_3$) δ 7.81 (d, J=8.4 Hz, 2H), 7.35 (m, J=8.0 Hz, 2H), 4.23-4.14 (m, 4H), 3.73-3.68 (m, 2H), 3.67-3.59 (m, 4H), 2.46 (s, 3H), 2.44 (t, J=2.4 Hz, 1H).

N-[6-(1-hydroxy-1-methyl-ethyl)-2H-indazol-5-yl]-6-(trifluoromethyl)pyridine-2-carboxamide (Intermediate TJ)

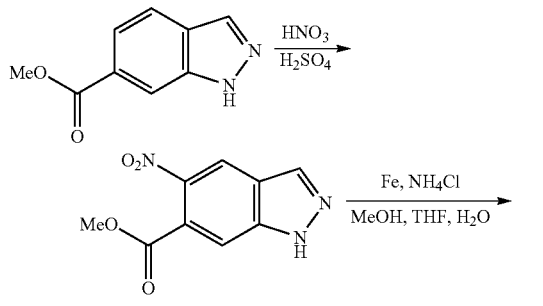

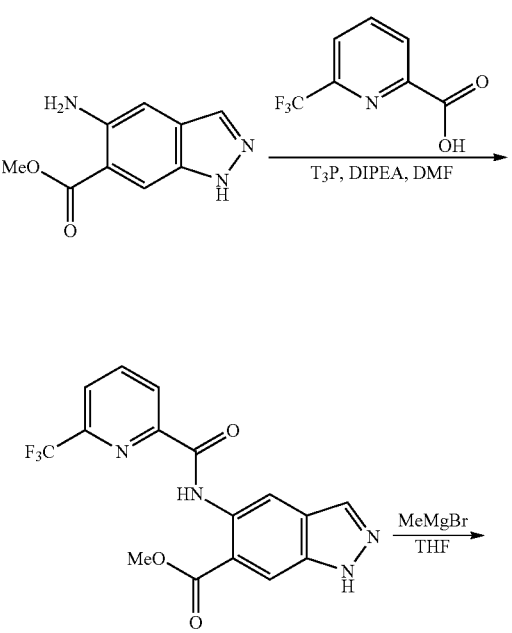

-continued

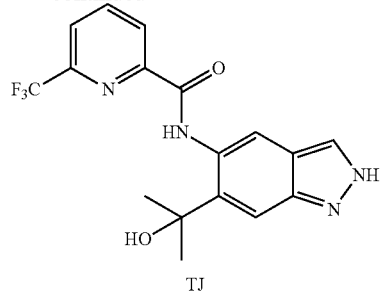

TJ

Step 1—Methyl 5-nitro-1H-indazole-6-carboxylate

To a solution of methyl 1H-indazole-6-carboxylate (10.0 g, 56.7 mmol) in $H_2SO_4$ (100 mL) was added a solution of $HNO_3$ (12.1 g, 125 mmol, 65% purity) in $H_2SO_4$ (20 mL) at −10-0° C. during 30 minutes. The mixture was stirred at −10-0° C. for 1 hour. On completion, the mixture was poured into ice/water (1.0 L) slowly. The mixture was filtered and the filter cake was washed with water (2×200 mL). Then the cake was collected and dried in vacuo to give the title compound (11.9 g, 94% yield) as yellow solid. $^1$H NMR (400 MHz, DMSO-$d_6$) δ 8.69 (s, 1H), 8.44 (s, 1H), 7.97 (s, 1H), 3.86 (s, 3H).

Step 2—Methyl 5-amino-1H-indazole-6-carboxylate

To a solution of methyl 5-nitro-1H-indazole-6-carboxylate (10.9 g, 49.2 mmol) in MeOH (100 mL) and THF (60 mL) was added a solution of $NH_4Cl$ (26.3 g, 492 mmol) in $H_2O$ (100 mL) at 25° C. Then Fe (13.7 g, 245 mmol) was added to the mixture in portions at 70° C., and the mixture was stirred at 70° C. for 1 hour. On completion, the mixture was filtered and the filter cake was washed with EA (200 mL). The filtrate was concentrated in vacuo. The residue was washed with water (100 mL), and extracted with EA (3×100 mL). The combined organic layer was washed with brine (100 mL), dried over $Na_2SO_4$, filtered and concentrated in vacuo to the title compound (7.30 g, 77% yield) as yellow solid. $^1$H NMR (400 MHz, DMSO-$d_6$) δ 12.82 (s, 1H), 7.99 (s, 1H), 7.85 (s, 1H), 6.99 (s, 1H), 6.00 (s, 2H), 3.85 (s, 3H).

Step 3—Methyl 5-[[6-(trifluoromethyl)pyridine-2-carbonyl]amino]-1H-indazole-6-carboxylate To a solution of methyl 5-amino-1H-indazole-6-carboxylate (7.20 g, 37.6 mmol), 6-(trifluoromethyl)pyridine-2-carboxylic acid (6.48 g, 33.9 mmol, CAS #131747-42-7) and DIPEA (7.35 g, 56.8 mmol) in THF (70 mL) was added $T_3P$ (47.9 g, 44.8 mL, 50 wt %) slowly at 0° C. Then the mixture was stirred at 0-5° C. for 2 hours. On completion, the reaction was quenched with cold water (0.1 mL). The mixture was diluted with water (280 mL), and stirred at 25° C. for 0.5 hour. The mixture was filtered and the filter cake was washed with water (30 mL). The filter cake was collected and dried in vacuo to give the title compound (12.3 g, 99% yield) as yellow solid. $^1$H NMR (400 MHz, DMSO-$d_6$) δ 12.58 (s, 1H), 9.15 (s, 1H), 8.47 (d, J=7.6 Hz, 1H), 8.39 (t, J=7.6 Hz, 1H), 8.30 (s, 1H), 8.25 (s, 1H), 8.20 (d, J=8.0 Hz, 1H), 3.97 (s, 3H).

Step 4—N-[6-(1-hydroxy-1-methyl-ethyl)-2H-indazol-5-yl]-6-(trifluoromethyl)pyridine-2-carboxamide To a solution of methyl 5-[[6-(trifluoromethyl)pyridine-2-carbonyl]amino]-1H-indazole-6-carboxylate (4.00 g, 10.9 mmol) in THF (40 mL) was added MeMgBr-Et₂O solution (3.0 M, 29.3 mL) slowly at 0° C. The mixture was stirred at 0-25° C. for 16 hours. On completion, the reaction was quenched with sat.NH₄Cl (40 mL) slowly at 0-10° C. The mixture was extracted with EA (3×40 mL). The combined organic layer was concentrated in vacuo. The residue was purified by reverse phase chromatography (FA condition) to give the title compound (1.50 g, 37% yield) as light yellow solid. ¹H NMR (400 MHz, CDCl₃) δ 12.23 (s, 1H), 8.96 (s, 1H), 8.52 (d, J=7.6 Hz, 1H), 8.12 (t, J=7.6 Hz, 1H), 8.07 (s, 1H), 7.85 (d, J=7.6 Hz, 1H), 7.50 (s, 1H), 1.80 (s, 6H).

N-[6-(1-hydroxy-1-methyl-ethyl)-2-[2-(2-prop-2-ynoxyethoxy)ethyl]indazol-5-yl]-6-(trifluoromethyl)pyridine-2-carboxamide (Intermediate TK)

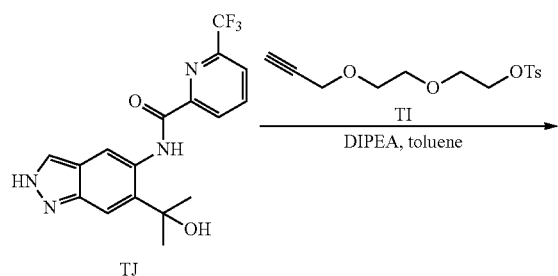

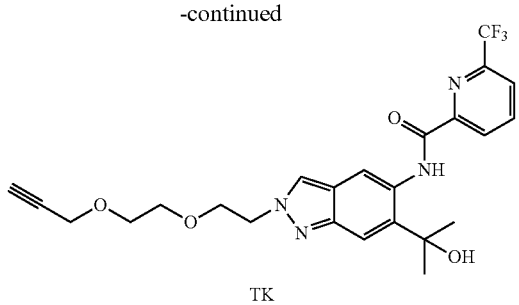

To a solution of N-[6-(1-hydroxy-1-methyl-ethyl)-2H-indazol-5-yl]-6-(trifluoromethyl)pyridine-2-carboxamide (300 mg, 823 umol, Intermediate TJ) and DIPEA (532 mg, 4.12 mmol) in toluene (10 mL) was added a solution of 2-(2-prop-2-ynoxyethoxy)ethyl 4-methylbenzenesulfonate (983 mg, 3.29 mmol, Intermediate TI) in toluene (5 mL) at 110° C. during 1 hour. Then, the mixture was stirred at 110° C. for 35 hours. On completion, after cooled to 25° C., the mixture was concentrated in vacuo. The residue was purified by column chromatography on silica gel to give the title compound (130 mg, 32% yield) as light yellow oil. ¹H NMR (400 MHz, CDCl₃) δ 12.26 (s, 1H), 8.83 (s, 1H), 8.47 (d, J=8.0 Hz, 1H), 8.08 (t, J=8.0 Hz, 1H), 8.00 (s, 1H), 7.82 (m, J=7.6 Hz, 1H), 7.67 (s, 1H), 4.57 (t, J=5.2 Hz, 2H), 4.16 (d, J=2.4 Hz, 2H), 3.97 (t, J=5.2 Hz, 2H), 3.66-3.58 (m, 4H), 2.47 (t, J=2.4 Hz, 1H), 1.79 (s, 6H).

3-[6-[3-[2-(2-Aminoethoxy)ethoxy]propyl]pyrido[2,3-b]indol-9-yl]piperidine-2,6-dione (Intermediate TL)

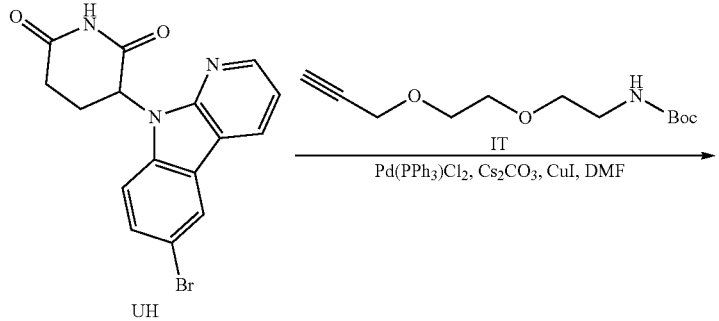

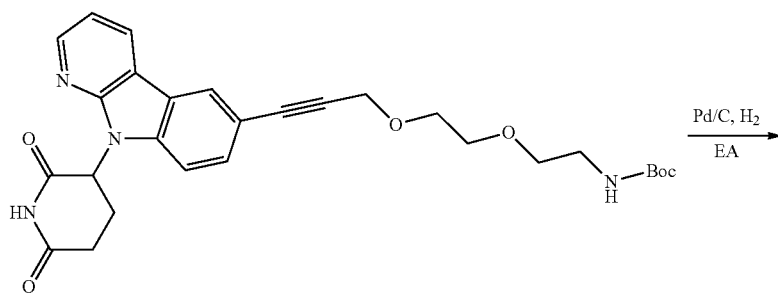

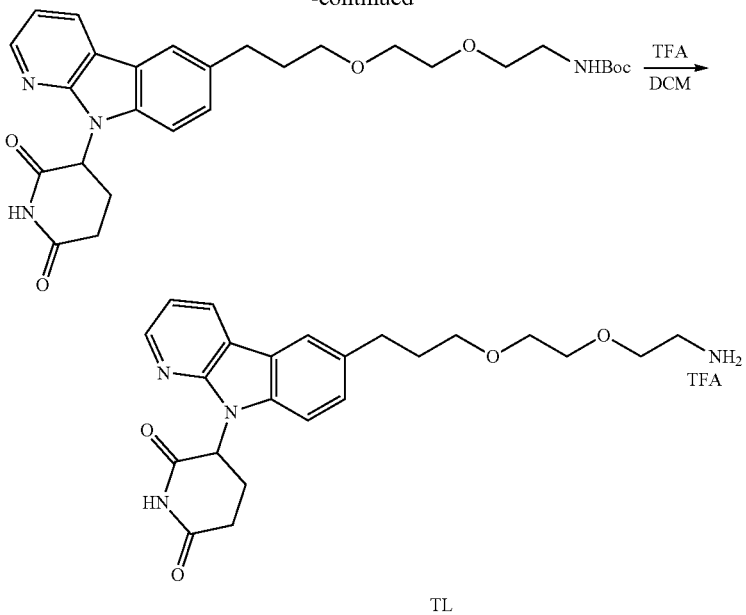

TL

Step 1—tert-butyl (2-(2-((3-(9-(2,6-dioxopiperidin-3-yl)-9H-pyrido[2,3-b]indol-6-yl)prop-2-yn-1-yl)oxy)ethoxy)ethyl)carbamate A mixture of 3-(6-bromo-9H-pyrido[2,3-b]indol-9-yl)piperidine-2,6-dione (600 mg, 1.68 mmol, Intermediate UH), tert-butyl (2-(2-(prop-2-yn-1-yloxy)ethoxy)ethyl)carbamate (1.2 g, 5.03 mmol, Intermediate IT), Pd(PPh₃)₂Cl₂ (179 mg, 0.252 mmol), CuI (26 mg, 0.134 mmol), Cs₂CO₃ (55 g, 16.8 mmol), 4 Å MS (1 g) and DMF (10 mL) was heated to 80° C. under microwave for 1.5 h under N₂. The mixture was then poured into 1N HCl (400 mL), and extracted with EA (100 mL). The organic layer was washed with brine (30 mL), dried over Na₂SO₄, filtered, concentrated and purified by column (PE/EA=10/1 to 5/1 to 2/1) to give the title compound (250 mg, 29% yield) as a white solid. ¹H NMR (400 MHz, CDCl₃) δ 8.45 (dd, J=1.2 Hz, J=4.8 Hz, 1H), 8.34 (dd, J=1.2 Hz, J=7.6 Hz, 1H), 8.21 (d, J=0.8 Hz, 1H), 8.15 (s, 1H), 7.59 (dd, J=1.2 Hz, J=8.4 Hz, 1H), 7.27-7.22 (m, 2H), 5.95 (br s, 1H), 5.01 (br s, 1H), 4.47 (s, 2H), 3.81-3.79 (m, 2H), 3.71-3.69 (m, 2H), 3.58 (t, J=5.2 Hz, 2H), 3.33-3.34 (m, 2H), 3.09-2.96 (m, 2H), 2.35-2.31 (m, 1H), 2.02-1.99 (m, 1H), 1.44 (s, 9H). LC/MS (ESI, m/z): [M-Boc+1]⁺=421.3.

Step 2—tert-butyl (2-(2-(3-(9-(2,6-dioxopiperidin-3-yl)-9H-pyrido[2,3-b]indol-6-yl)propoxy)ethoxy)ethyl)carbamate A mixture of tert-butyl (2-(2-((3-(9-(2,6-dioxopiperidin-3-yl)-9H-pyrido[2,3-b]indol-6-yl)prop-2-yn-1-yl)oxy)ethoxy)ethyl)carbamate (250 mg, 0.481 mmol), Pd/C (100 mg) and EA (15 mL) was stirred for overnight at rt under H₂. The mixture was filtered, concentrated and purified by column (PE/EA=1/1) to give the title compound (150 mg, 60% yield) as a white solid. ¹H NMR (400 MHz, CDCl₃) δ 8.41 (dd, J=1.2 Hz, J=4.8 Hz, 1H), 8.31 (dd, J=1.6 Hz, J=7.6 Hz, 1H), 8.22 (s, 1H), 7.92 (d, J=0.8 Hz, 1H), 7.33 (dd, J=1.6 Hz, J=8.4 Hz, 1H), 7.21-7.16 (m, 2H), 5.92-5.88 (m, 1H), 5.04 (br s, 1H), 3.64-3.50 (m, 8H), 3.33 (d, J=4.8 Hz, 2H), 3.08-2.85 (m, 5H), 2.32-2.28 (m, 1H), 2.04-1.97 (m, 2H), 1.43 (s, 9H); LC/MS (ESI, m/z): [M-Boc+1]⁺=425.2.

Step 3—3-[6-[3-[2-(2-Aminoethoxy)ethoxy]propyl]pyrido[2,3-b]indol-9-yl]piperidine-2,6-dione To a solution of tert-butyl N-[2-[2-[3-[9-(2,6-dioxo-3-piperidyl)pyrido[2,3-b]indol-6-yl]propoxy]ethoxy]ethyl]carbamate (54.0 mg, 102 umol) in DCM (3 mL) was added TFA (352 mg, 3.09 mmol). The mixture was stirred at 25° C. for 1 hr. On completion, the reaction mixture was concentrated in vacuo to give the title compound (55.0 mg, 95% yield, TFA salt) as light yellow oil. LC-MS (ESI⁺) m/z 425.3 (M+H)⁺.

Step 1—Tert-butyl 4-prop-2-ynoxypiperidine-1-carboxylate (Intermediate™)

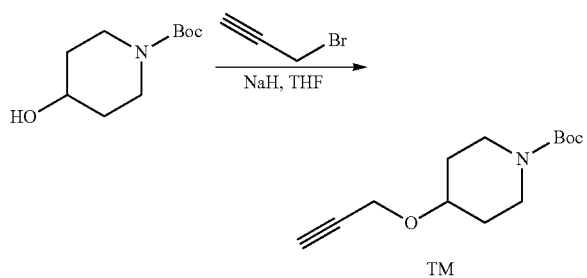

TM

To a solution of tert-butyl 4-hydroxypipenrdine-1-carboxylate 2.00 g, 9.94 mmol, CAS #109384-19-2) in anhydrous THF (10 mL) was cooled to 0° C., and subsequently NaH (477 mg, 11.9 mmol, 60% oil dispersion) was added. The reaction mixture was stirred at 0° C. for 0.5 hr. Then, 3-bromoprop-1-yne (1.18 g, 9.94 mmol, 856 uL) was added. The resulting reaction mixture was stirred at 25° C. for 12 hrs. On completed, the reaction mixture was quenched with water (1 mL), then diluted with ethyl acetate (100 mL). The organic layers were washed with brine (20 mL), dried over anhydrous sodium sulfate, filtered and the filtrate was concentrated in vacuo. The residue was purified by column chromatography to give the title compound (2.38 g, 100% yield) as yellow oil. $^1$H NMR (400 MHz, CDCl$_3$) δ 4.22 (d, J=2.4 Hz, 2H), 3.84-3.75 (m, 2H), 3.73-3.70 (m, 1H), 3.15-3.09 (m, 2H), 2.43 (t, J=2.4 Hz, 1H), 1.93-1.82 (m, 2H), 1.61-1.50 (m, 2H), 1.47 (s, 9H).

3-[3-Methyl-2-oxo-4-[3-(4-piperidyloxy)propyl] benzimidazol-1-yl]piperidine-2,6-dione (Intermediate TN)

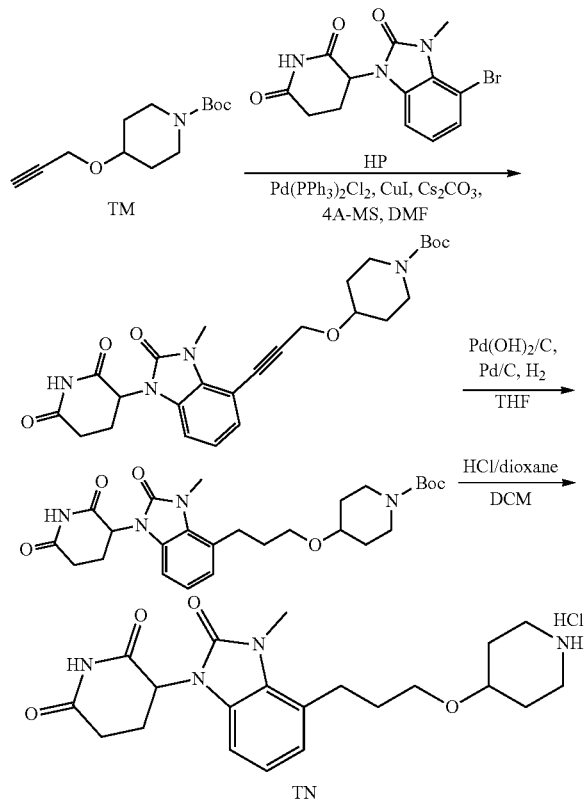

Step 1—Tert-butyl 4-[3-[1-(2,6-dioxo-3-piperidyl)-3-methyl-2-oxo-benzimidazol-4-yl]prop-2-ynoxy] piperidine-1-carboxylate A suspension of 3-(4-bromo-3-methyl-2-oxo-benzimidazol-1-yl)piperidine-2,6-dione (300 mg, 887 umol, Intermediate HP), tert-butyl 4-prop-2-ynoxypiperidine-1-carboxylate (318 mg, 1.33 mmol, Intermediate™), Pd(PPh$_3$)$_2$Cl$_2$ (124 mg, 177 umol), CuI (33.8 mg, 177 umol), 4 Å molecular sieves (400 mg) and Cs$_2$CO$_3$ (1.16 g, 3.55 mmol) in DMF (5 mL) was de-gassed under vacuum and purged with N$_2$ several times and then heated to 80° C. for 2 hours under N$_2$. On completion, the reaction mixture was concentrated in vacuo to remove DMF. The residue was diluted with EA (50 mL) and water (20 mL). After, the organic layer was separated and washed with brine (5 mL×2), dried over anhydrous Na$_2$SO$_4$, filtered and the filtrate was concentrated in vacuo to give a residue. The residue was purified by reverse phase to give the title compound (222 mg, 48% yield) as a yellow solid. $^1$H NMR (400 MHz, CDCl$_3$) δ 8.09 (s, 1H), 7.10 (d, J=8.0 Hz, 1H), 6.92 (t, J=8.0 Hz, 1H), 6.69 (d, J=8.0 Hz, 1H), 5.13 (dd, J=5.2, 12.8 Hz, 1H), 4.39 (s, 2H), 3.76-3.66 (m, 6H), 3.09-3.03 (m, 2H), 2.94-2.84 (m, 1H), 2.82-2.71 (m, 1H), 2.71-2.59 (m, 1H), 2.22-2.11 (m, 1H), 1.83-1.78 (m, 2H), 1.57-1.49 (m, 2H), 1.39 (s, 9H), LC-MS (ESI$^+$) m/z 441.2 (M+H−56)$^+$.

Step 2—Tert-butyl4-[3-[1-(2,6-dioxo-3-piperidyl)-3-methyl-2-oxo-benzimidazol-4-yl]propoxy]piperidine-1-carboxylate To a solution of tert-butyl 4-[3-[1-(2,6-dioxo-3-piperidyl)-3-methyl-2-oxo-benzimidazol-4-yl]prop-2-ynoxy] piperidine-1-carboxylate (370 mg, 745 umol) in THF (10 mL) was added Pd/C (0.1 g, 10% wt) and Pd(OH)$_2$/C (0.1 g, 10% wt). The suspension was degassed under vacuum and purged with H$_2$ several times. The mixture was stirred under H$_2$ (15 psi) at 25° C. for 12 hours. On completion, the reaction mixture was filtered and the filtrate was concentrated in vacuo to give the title compound (330 mg, 88% yield) as a white solid. $^1$H NMR (400 MHz, CDCl$_3$) δ 8.03 (s, 1H), 6.91 (d, J=8.0 Hz, 1H), 6.83 (d, J=8.0 Hz, 1H), 6.59 (t, J=8.0 Hz, 1H), 5.20-5.09 (m, 1H), 3.70-3.64 (m, 2H), 3.62 (s, 3H), 3.44 (t, J=5.6 Hz, 2H), 3.41-3.34 (m, 1H), 3.06-3.04 (m, 2H), 2.98-2.93 (m, 2H), 2.91-2.80 (m, 1H), 2.79-2.63 (m, 2H), 2.19-2.10 (m, 1H), 1.89-1.81 (m, 2H), 1.80-1.73 (m, 2H), 1.47-1.39 (m, 2H), 1.39 (s, 9H); LC-MS (ESI$^+$) m/z 523.1 (M+Na)$^+$.

Step 3—3-[3-Methyl-2-oxo-4-[3-(4-piperidyloxy) propyl]benzimidazol-1-yl]piperidine-2,6-dione To a solution of tert-butyl 4-[3-[1-(2,6-dioxo-3-piperidyl)-3-methyl-2-oxo-benzimidazol-4-yl]propoxy]piperidine-1-carboxylate (100 mg, 199 umol) in DCM (4 mL) was added HCl/dioxane (4 M, 2 mL). The reaction mixture was stirred at 25° C. for 0.5 hr. On completion, the reaction mixture was concentrated in vacuo to give the title compound (87.0 mg, 100% yield, HCl salt) as a white solid. LC-MS (ESI$^+$) m/z 401.1 (M+H)$^+$.

1-(4-Methoxyphenyl)-N-methyl-N-[[(2R)-4-prop-2-ynylmorpholin-2-yl]methyl]methanamine (Intermediate TO)

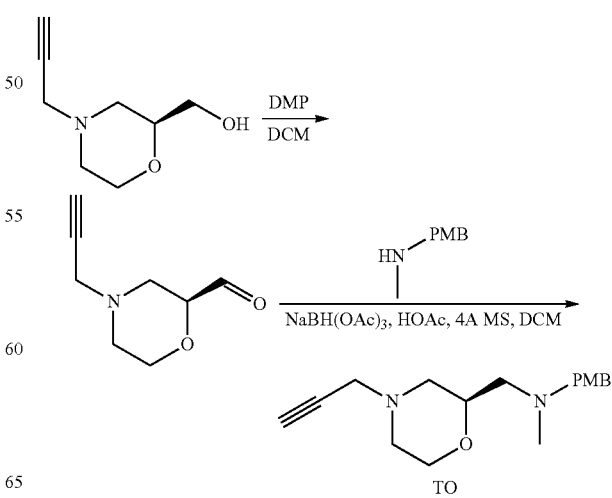

Step 1—(2S)-4-prop-2-ynylmorpholine-2-carbaldehyde

To a solution of [(2S)-4-prop-2-ynylmorpholin-2-yl]methanol (5.00 g, 32.2 mmol, synthesized via Steps 1-2 of Intermediate RV) in DCM (250 mL) was added DMP (17.0 g, 40.0 mmol) at 0° C. The reaction mixture was stirred at 0° C. for 2 hrs. On completion, the reaction mixture was quenched with saturated $NaS_2O_3$ (30 mL), then extracted with DCM (3×100 mL). The combined organic layers was washed with saturated $NaHCO_3$ (50 mL), then washed with brine (50 mL), dried over anhydrous sodium sulfate, and filtered. The filtrate was concentrated in vacuo to give the title compound (2.80 g, 56% yield) as yellow oil.

Step 2—1-(4-Methoxyphenyl)-N-methyl-N-[[(2R)-4-prop-2-ynylmorpholin-2-yl]methyl]methanamine To a solution of (2S)-4-prop-2-ynylmorpholine-2-carbaldehyde (2.80 g, 18.2 mmol) and 1-(4-methoxyphenyl)-N-methylmethanamine (2.76 g, 18.2 mmol, CAS #702-24-9) in DCM (50 mL) was added $NaBH(OAc)_3$ (4.65 g, 21.9 mmol), 4 Å molecular sieves (1g) and HOAc (1.10 g, 18.2 mmol, 1.05 mL). The reaction mixture was stirred at 25° C. for 12 hrs. On completion, the reaction mixture was concentrated in vacuo to give a residue. The residue was purified by reverse phase (0.1% $NH_3.H_2O$ condition) to give the title compound (1.50 g, 25% yield) as yellow oil. $^1H$ NMR (400 MHz, $CDCl_3$) δ 7.25-7.18 (m, 2H), 6.90-6.82 (m, 2H), 3.96-3.88 (m, 1H), 3.81 (s, 3H), 3.78-3.73 (m, 1H), 3.73-3.65 (m, 1H), 3.56-3.44 (m, 2H), 3.31 (t, J=2.4 Hz, 2H), 2.86-2.80 (m, 1H), 2.73-2.67 (m, 1H), 2.55-2.48 (m, 1H), 2.41-2.33 (m, 2H), 2.27 (t, J=2.4 Hz, 1H), 2.25 (s, 3H), 2.09-2.03 (m, 1H); LC-MS (ESI$^+$) m/z 289.2 (M+H)$^+$.

3-[(5S)-5-[4-[4-(3-aminopropoxy)but-1-ynyl]phenyl]-2-oxo-oxazolidin-3-yl]piperidine-2,6-dione (Intermediate TP)

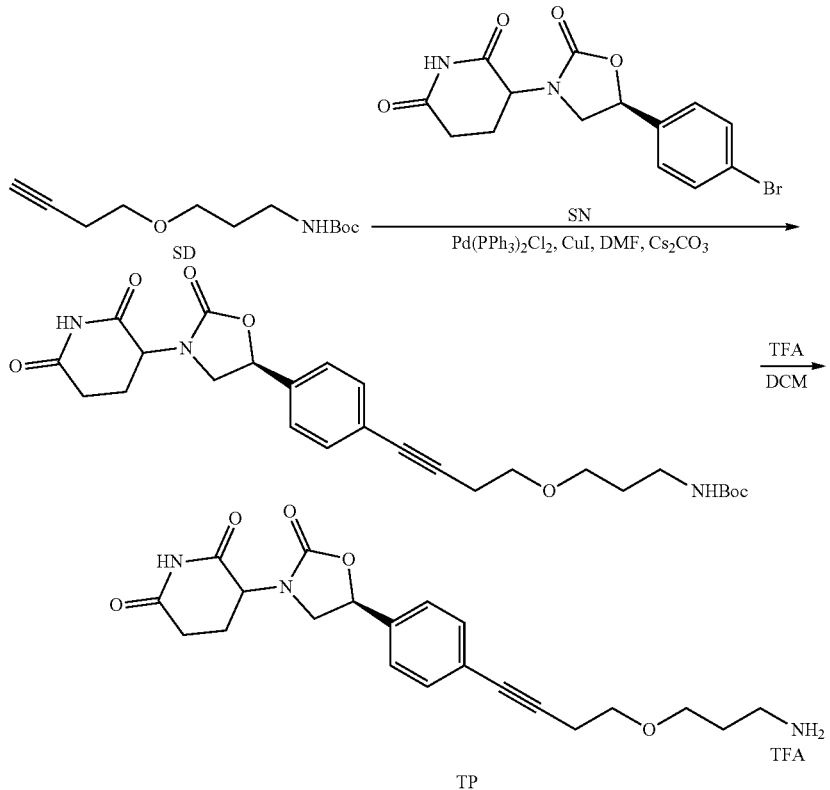

Step 1—Tert-butyl N-[3-[4-[4-[(5S)-3-(2,6-dioxo-3-piperidyl)-2-oxo-oxazolidin-5-yl]phenyl]but-3-ynoxy]propyl]carbamate To a solution of tert-butyl N-(3-but-3-ynoxypropyl)carbamate (250 mg, 1.10 mmol, Intermediate SD) and 3-[(5S)-5-(4-bromophenyl)-2-oxo-oxazolidin-3-yl]piperidine-2,6-dione (323 mg, 916 umol, Intermediate SN) in DMF (15 mL) was added $Pd(PPh_3)_2Cl_2$ (64.3 mg, 91.6 umol), CuI (17.4 mg, 91.6 umol) and $Cs_2CO_3$ (1.19 g, 3.67 mmol). The reaction mixture was stirred at 80° C. for 2 hrs under $N_2$. On completion, the mixture was filtered, and the filtrate was concentrated in vacuo to give a residue. The residue was purified by reverse phase (0.1% FA condition) to give the title compound (250 mg, 54% yield) as a yellow solid. $^1H$ NMR (400 MHz, DMSO-$d_6$) δ $^1H$ NMR (400 MHz, DMSO-$d_6$) δ 11.00 (m, 1H), 7.50-7.35 (m, 4H), 6.79 (t, J=5.2 Hz, 1H), 5.72-5.59 (m, 1H), 4.78-4.61 (m, 1H), 3.97-3.83 (m, 1H), 3.59-3.51 (m, 2H), 3.44 (t, J=6.0 Hz, 2H), 3.25 (t, J=8.4 Hz, 1H), 2.99 (q, J=6.8 Hz, 2H), 2.92-2.77 (m, 1H), 2.70-2.64 (m, 2H), 2.59-2.54 (m, 1H), 2.29-2.14 (m, 1H), 2.05-1.91 (m, 1H), 1.67-1.58 (m, 2H), 1.37 (s, 9H); LC-MS (ESI$^+$) m/z 522.3 (M+Na)$^+$.

Step 2—3-[(5S)-5-[4-[4-(3-aminopropoxy)but-1-ynyl]phenyl]-2-oxo-oxazolidin-3-yl]piperidine-2,6-dione To a solution of tert-butyl N-[3-[4-[4-[(5S)-3-(2,6-dioxo-3-piperidyl)-2-oxo-oxazolidin-5-yl]phenyl]but-3-ynoxy]propyl]carbamate (100 mg, 200 umol) in DCM (3 mL) was added TFA (1.54 g, 13.5 mmol, 1.00 mL). The reaction mixture was stirred at 25° C. for 2 hr. On completion, the residue concentrated in vacuo to give the title compound (100 mg, 97% yield) as yellow oil. LC-MS (ESI+) m/z 400.2 (M+H)+.

3-[3-Methyl-4-[3-[(2S)-2-(methylaminomethyl)morpholin-4-yl]propyl]-2-oxo-benzimidazol-1-yl]piperidine-2,6-dione (Intermediate TT)

$Cs_2CO_3$ (1.45 g, 4.44 mmol), CuI (50.7 mg, 266 umol), $Pd(PPh_3)_2Cl_2$ (187 mg, 266 umol) and 4 Å molecular sieves (20 mg). The reaction mixture was stirred at 80° C. for 2 hours under $N_2$. On completion, the reaction mixture was filtered. The filtrate was washed with water (100 mL) and extracted with ethyl acetate (2×40 mL). The combined organic phase was washed with brine (2×40 mL), dried with anhydrous $Na_2SO_4$, filtered and concentrated in vacuo to give residue. The residue was purified by reverse phase HPLC (0.1% FA condition) to give the title compound (285 mg, 58% yield) as brown solid. $^1$H NMR (400 MHz, DMSO-$d_6$) δ 11.13 (s, 1H), 8.15 (s, 2H), 7.21-7.15 (m, 3H), 7.13-7.09 (m, 1H), 6.83-6.79 (m, 2H), 5.41 (d, J=5.6, 12.8 Hz, 1H), 3.83-3.77 (m, 2H), 3.69 (s, 4H), 3.64 (s, 4H), 3.56-3.51 (m, 5H), 2.39 (d, J=6.0 Hz, 2H), 2.35-2.26 (m, 2H), 2.15 (s, 3H), 2.10-2.05 (m, 1H), 2.03-1.96 (m, 2H).

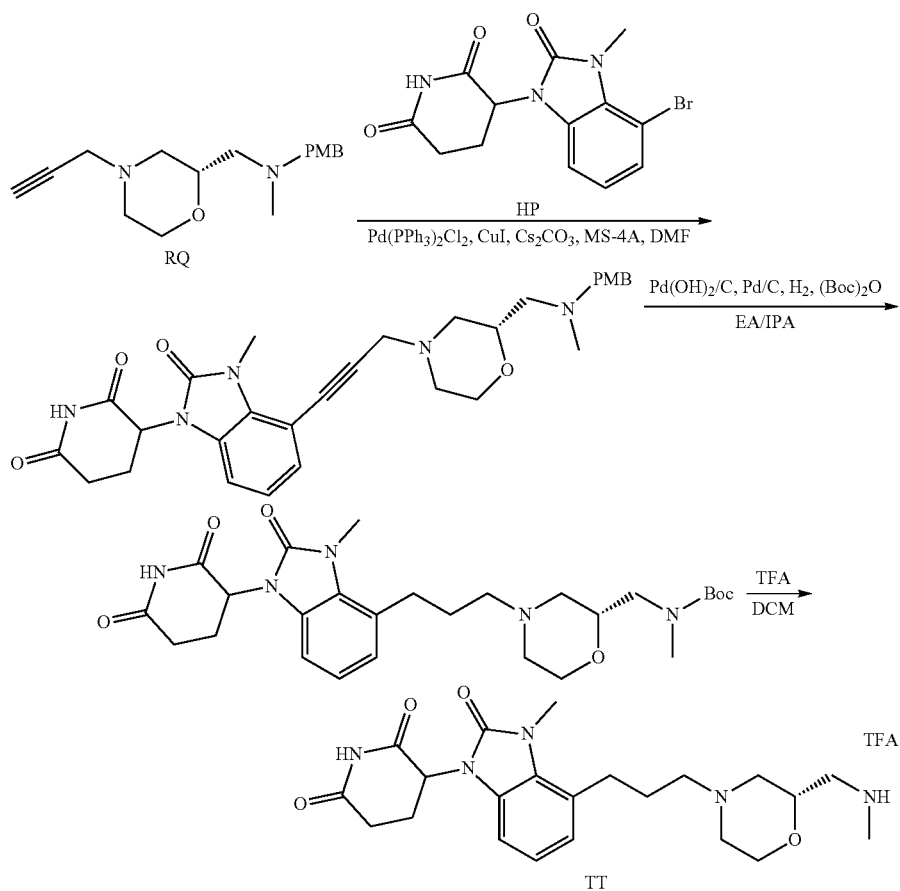

Step 1—3-[4-[3-[(2S)-2-[[(4-Methoxyphenyl)methyl-methyl-amino]methyl]morpholin-4-yl]prop-1-ynyl]-3-methyl-2-oxo-benzimidazol-1-yl]piperidine-2,6-dione To a mixture of 3-(4-bromo-3-methyl-2-oxo-benzimidazol-1-yl)piperidine-2,6-dione (300 mg, 887 umol, Intermediate HP) and 1-(4-methoxyphenyl)-N-methyl-N-[[(2S)-4-prop-2-ynylmorpholin-2-yl]methyl]methanamine (383 mg, 1.33 mmol, Intermediate RQ) in DMF (20 mL) was added

Step 2—Tert-butyl N-[[(2R)-4-[3-[1-(2,6-dioxo-3-piperidyl)-3-methyl-2-oxo-benzimidazol-4-yl]propyl]morpholin-2-yl]methyl]-N-methyl-carbamate To a mixture of 3-[4-[3-[(2S)-2-[[(4-methoxyphenyl)methyl-methyl-amino]methyl]morpholin-4-yl]prop-1-ynyl]-3-methyl-2-oxo-benzimidazol-1-yl]piperidine-2,6-dione (285 mg, 522 umol) in EA (20 mL) and IPA (10 mL) was added Pd/C (50.0 mg, 10 wt %), $Pd(OH)_2$/C (50.0 mg, 10 wt %) and $(Boc)_2O$ (171 mg, 783 umol). The suspension was degassed under vacuum and purged with $H_2$ three times. The mixture was then stirred at 25° C. for 16 hours under $H_2$ (50 psi) atmosphere. On completion, the reaction mixture was filtrated and filtrate was concentrated in vacuo to give residue. The residue was purified by reverse phase HPLC (0.1% FA condition) to give title compound (130 mg, 45% yield) as a brown solid. LC-MS (ESI$^+$) m/z 530.4 (M+H)$^+$.

Step 3—3-[3-Methyl-4-[3-[(2S)-2-(methylaminomethyl)morpholin-4-yl]propyl]-2-oxo-benzimidazol-1-yl]piperidine-2,6-dione To a mixture of tert-butyl N-[[(2R)-4-[3-[1-(2,6-dioxo-3-piperidyl)-3-methyl-2-oxo-benzimidazol-4-yl]propyl]morpholin-2-yl]methyl]-N-methyl-carbamate (130 mg, 245 umol) in DCM (2 mL) was added TFA (83.9 mg, 736 umol). The reaction mixture was stirred at 25° C. for 2 hours. On completion, the reaction mixture was concentrated in vacuo to give title compound (133 mg, 100% yield, TFA salt) as brown oil. LC-MS (ESI$^+$) m/z 430.4 (M+H)$^+$.

3-[3-Methyl-4-[3-[(2R)-2-(methylaminomethyl)morpholin-4-yl]propyl]-2-oxo-benzimidazol-1-yl]piperidine-2,6-dione (Intermediate TU)

methyl-2-oxo-benzimidazol-1-yl) piperidine-2,6-dione (352 mg, 1.04 mmol, Intermediate HP) in DMF (10 mL) was added Cs$_2$CO$_3$ (1.36 g, 4.16 mmol), CuI (39.6 mg, 208 umol), 4 Å molecular sieves (50 mg) and Pd(PPh$_3$)$_2$Cl$_2$ (146.03 mg, 208.1 umol) at 25° C. The reaction mixture was stirred at 80° C. for 2 hrs. On completion, the reaction mixture was filtered and the filtrate was concentrated in vacuo to give a residue. The residue was diluted with water 30 mL, and then extracted with EA (3×50 mL). The combined organic layers were washed with brine and dried over Na$_2$SO$_4$, filtered and the filtrate was concentrated in vacuo to give a residue. The residue was purified by reverse phase (0.1% FA condition) to give the title compound (355 mg, 63% yield) as a yellow solid. $^1$H NMR (400 MHz, DMSO-d$_6$) δ 11.12 (s, 1H), 8.15 (s, 1H), 7.20-7.14 (m, 4H), 7.13-7.08 (m, 1H), 7.02 (t, J=8.0 Hz, 1H), 6.80 (d, J=8.8 Hz, 3H), 5.40 (dd, J=5.2 Hz, 1H), 3.79 (d, J=10.0 Hz, 2H), 3.68 (s, 4H), 3.63 (s, 3H), 3.60 (d, J=7.2 Hz, 2H), 2.91 (d, J=11.6 Hz, 2H), 2.74-2.64 (m, 4H), 2.37 (d, J=6.0 Hz, 2H), 2.30-2.25 (m, 1H), 2.14 (s, 3H), 2.03-1.97 (m, 1H); LC-MS (ESI+) m/z 546.3 (M+H)$^+$.

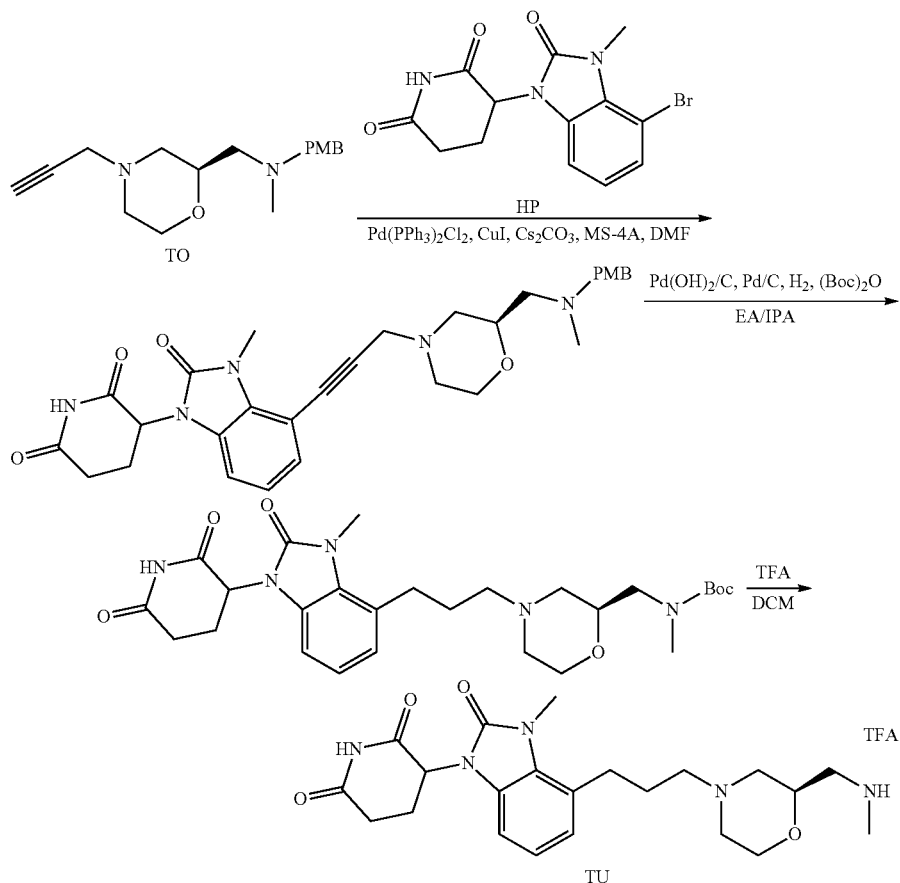

Step 1—3-[4-[3-[(2R)-2-[[(4-methoxyphenyl)methyl-methyl-amino]methyl]morpholin-4-yl]prop-1-ynyl]-3-methyl-2-oxo-benzimidazol-1-yl]piperidine-2,6-dione To a solution of 1-(4-methoxyphenyl)-N-methyl-N-[[(2R)-4-prop-2-ynylmorpholin-2-yl]methyl]methanamine (450 mg, 1.56 mmol, Intermediate TO) and 3-(4-bromo-3-

Step 2—Tert-butyl N-[[(2S)-4-[3-[1-(2,6-dioxo-3-piperidyl)-3-methyl-2-oxo-benzimidazol-4-yl]propyl]morpholin-2-yl]methyl]-N-methyl-carbamate To a solution of 3-[4-[3-[(2R)-2-[[(4-methoxyphenyl)methyl-methyl-amino]methyl]morpholin-4-yl]prop-1-ynyl]-3-methyl-2-oxo-benzimidazol-1-yl]piperidine-2,6-dione (355 mg, 651 umol) in EA (20 mL) and IPA (10 mL) was added Pd/C (180 mg, 20 wt %), Pd(OH)₂/C (dry) (180 mg, 10 wt %) and (Boc)₂O (213 mg, 976 umol, 224 uL) at 25° C. The reaction mixture was stirred at 25° C. for 2 hrs under H₂ (50 Psi) atmosphere. On completion, the reaction mixture was filtered and the filtrate was concentrated in vacuo to give a residue. The residue was purified by reverse phase (0.1% FA) to give the title compound (225 mg, 65% yield) as a white solid. ¹H NMR (400 MHz, DMSO-d₆) δ 11.08 (s, 1H), 7.00-6.91 (m, 2H), 6.89-6.84 (m, 1H), 5.36 (dd, J=5.2 Hz, 1H), 3.78 (d, J=11.2 Hz, 1H), 3.55 (s, 3H), 3.47 (s, 1H), 3.22 (d, J=4.8 Hz, 1H), 3.17 (d, J=6.8 Hz, 1H), 2.96-2.87 (m, 3H), 2.80 (d, J=8.8 Hz, 3H), 2.73-2.58 (m, 4H), 2.42-2.31 (m, 3H), 2.06-1.94 (m, 2H), 1.79-1.68 (m, 3H), 1.37 (s, 9H); LC-MS (ESI+) m/z 530.3 (M+H)⁺.

Step 3—3-[3-Methyl-4-[3-[(2R)-2-(methylaminomethyl)morpholin-4-yl]propyl]-2-oxo-benzimidazol-1-yl]piperidine-2,6-dione To a solution of tert-butyl N-[[(2S)-4-[3-[1-(2,6-dioxo-3-piperidyl)-3-methyl-2-oxo-benzimidazol-4-yl]propyl]morpholin-2-yl]methyl]-N-methyl-carbamate (120 mg, 227 umol) in DCM (2 mL) was added HCl/dioxane (4 M, 1 mL) at 25° C. The reaction mixture was stirred at 25° C. for 2 hrs. On completion, the reaction mixture was concentrated in vacuo to give the title compound (95.0 mg, 98% yield) as a white solid. LC-MS (ESI⁺) m/z 430.3 (M+H)⁺.

Benzyl N-methyl-N-[2-[(2R)-4-prop-2-ynylmorpholin-2-yl]ethyl]carbamate (Intermediate TV)

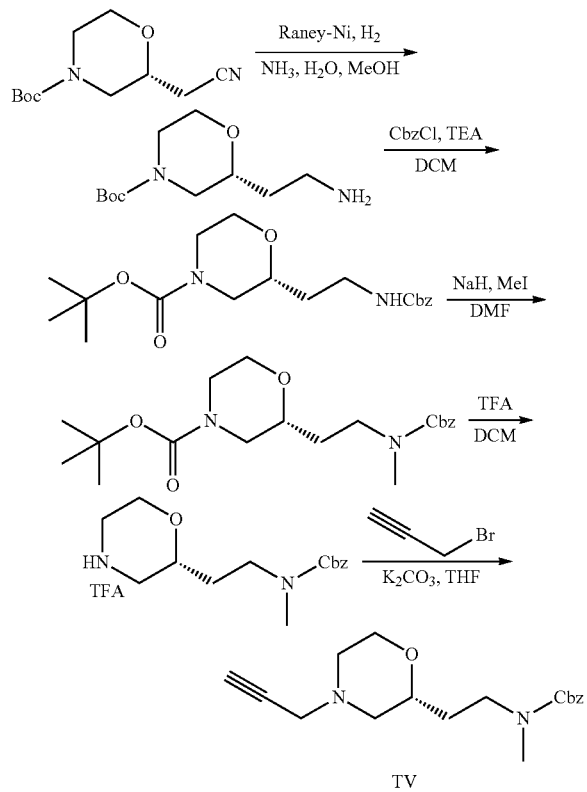

Step 1—Tert-butyl (2R)-2-(2-aminoethyl)morpholine-4-carboxylate

A mixture of tert-butyl (2R)-2-(cyanomethyl)morpholine-4-carboxylate (3.86 g, 17.0 mmol, synthesized via Steps 1-2 of Intermediate RN) and Raney-Ni (3.00 g, 35.0 mmol) in MeOH (120 mL) and NH₃·H₂O (12 mL) was stirred at 25° C. for 4 hours under H₂ (45 Psi). On completion, the mixture was filtered, and the filter cake was washed with MeOH (50 mL). The filtrate and washing were combined and concentrated in vacuo to give the title compound (3.90 g, 99% yield) as light yellow gum. ¹H NMR (400 MHz, CDCl₃) δ 3.87-3.84 (m, 3H), 3.53-3.44 (m, 2H), 2.87-2.81 (m, 3H), 2.65 (m, 1H), 1.65-1.56 (m, 4H), 1.47 (s, 9H).

Step 2—Tert-butyl (2R)-2-[2-(benzyloxycarbonylamino)ethyl]morpholine-4-carboxylate To a solution of tert-butyl (2R)-2-(2-aminoethyl) morpholine-4-carboxylate (3.90 g, 16.9 mmol) and TEA (3.55 g, 35.0 mmol) in DCM (50 mL) was added CbzCl (3.03 g, 17.7 mmol) at 0° C. The mixture was stirred at 0-10° C. for 1 hour. On completion, the mixture was washed with water (20 mL) and concentrated in vacuo. The residue was dissolved in EA (50 mL), washed with brine (20 mL), dried over Na₂SO₄, filtered and concentrated in vacuo to give the title compound (6.00 g, 97% yield) as light yellow oil. ¹H NMR (400 MHz, CDCl₃) δ 7.41-7.33 (m, 5H), 5.18-5.16 (m, 1H), 5.10 (s, 2H), 4.12-3.83 (m, 3H), 3.48-3.40 (m, 4H), 2.90 (m, 1H), 2.62-2.61 (m, 1H), 1.44 (s, 9H).

Step 3—Tert-butyl (2R)-2-[2-[benzyloxycarbonyl (methyl)amino]ethyl]morpholine-4-carboxylate To a solution of tert-butyl (2R)-2-[2-(benzyloxycarbonylamino)ethyl]morpholine-4-carboxylate (6.00 g, 16.4 mmol) in THF (60 mL) was added NaH (1.32 g, 33.0 mmol, 60% oil disperion) at 0° C. The mixture was stirred at 0° C. for 30 minutes. Then MeI (7.01 g, 49.3 mmol) was added to the reaction mixture at 0° C. The mixture was stirred at 0-25° C. for another 3 hours. On completion, the reaction was quenched with sat. aq. NH₄Cl (10 mL). The mixture was diluted with water (50 mL), then extracted with EA (3×50 mL). The combined organic layer was washed with brine (10 mL), dried over Na₂SO₄, filtered and concentrated in vacuo. The residue was purified by column chromatography on silica gel to give the title compound (5.20 g, 83% yield) as light yellow oil. ¹H NMR (400 MHz, CDCl₃) δ 7.37-7.31 (m, 5H), 5.13 (s, 2H), 3.86-3.82 (m, 3H), 3.43-3.40 (m, 4H), 2.99-2.83 (m, 4H), 2.69-2.52 (m, 1H), 1.74-1.62 (m, 2H), 1.47 (s, 9H).

Step 4—Benzyl N-methyl-N-[2-[(2R)-morpholin-2-yl]ethyl]carbamate

To a solution of tert-butyl (2R)-2-[2-[benzyloxycarbonyl (methyl)amino]ethyl]morpholine-4-carboxylate (5.20 g, 13.7 mmol) in DCM (30 mL) was added TFA (10 mL) at 25° C. The mixture was stirred at 25° C. for 2 hours. On completion, the mixture was concentrated in vacuo to give the title compound (5.30 g, 98% yield, TFA salt) as light yellow gum.

Step 5—Benzyl N-methyl-N-[2-[(2R)-4-prop-2-ynylmorpholin-2-yl]ethyl]carbamate

To a mixture of benzyl N-methyl-N-[2-[(2R)-morpholin-2-yl]ethyl]carbamate (5.30 g, 13.5 mmol, TFA salt) and K₂CO₃ (7.59 g, 54.9 mmol) in THF (60 mL) was added 3-bromoprop-1-yne (1.63 g, 13.7 mmol) at 25° C. The mixture was stirred at 25° C. for 16 hours. On completion, the mixture was filtered, and the filter cake was washed with EA (20 mL). The filtrate and washing were combined and concentrated in vacuo. The residue was purified by column chromatography on silica gel to give the title compound (2.90 g, 67% yield) as light yellow oil. ¹H NMR (400 MHz, CDCl₃) δ 7.37-7.31 (m, 5H), 5.13 (d, J=3.2 Hz, 2H), 3.87 (t, J=13.2 Hz, 1H), 3.70-3.46 (m, 2H), 3.40 (t, J=7.6 Hz, 2H), 3.28 (d, J=10.8 Hz, 2H), 2.94 (s, 3H), 2.79-2.63 (m, 2H), 2.44-2.33 (m, 1H), 2.27 (t, J=2.4 Hz, 1H), 2.16-2.06 (m, 1H), 1.76-1.63 (m, 2H).

3-[3-Methyl-5-[3-[(2R)-2-[2-(methylamino)ethyl] morpholin-4-yl]propyl]-2-oxo-benzimidazol-1-yl] piperidine-2,6-dione (Intermediate TW)

zol-1-yl)piperidine-2,6-dione (1.38 g, 4.08 mmol, Intermediate HN), CuI (165 mg, 866 umol), Pd(PPh₃)₂Cl₂ (580 mg, 826 umol), Cs₂CO₃ (6.65 g, 20.4 mmol) and 4 Å molecular sieves (1.00 g) in DMF (30 mL) was stirred at 80° C. for 2 hours under N₂. On completion, the reaction mixture was cooled to 25° C. The mixture was filtered and the filter cake was washed with EA (20 mL). The filtrate and washing were combined and concentrated in vacuo. The residue was purified by reversed phase flash (FA condition) to give the title compound (1.50 g, 64% yield) as light yellow solid. ¹H NMR (400 MHz, DMSO-d₆) δ 11.13 (s, 1H), 7.36-7.29 (m, 6H), 7.17-7.09 (m, 2H), 5.41-5.36 (m, 1H), 5.05 (s, 2H), 3.85-3.76 (m, 1H), 3.49 (s, 3H), 3.42-3.38 (m, 3H), 3.26 (m, 1H), 2.86-2.82 (m, 4H), 2.76-2.68 (m, 2H), 2.65-2.62 (m, 1H), 2.52-2.52 (m, 3H), 2.31-2.25 (m, 1H), 2.06-1.98 (m, 2H), 1.61-1.57 (m, 2H).

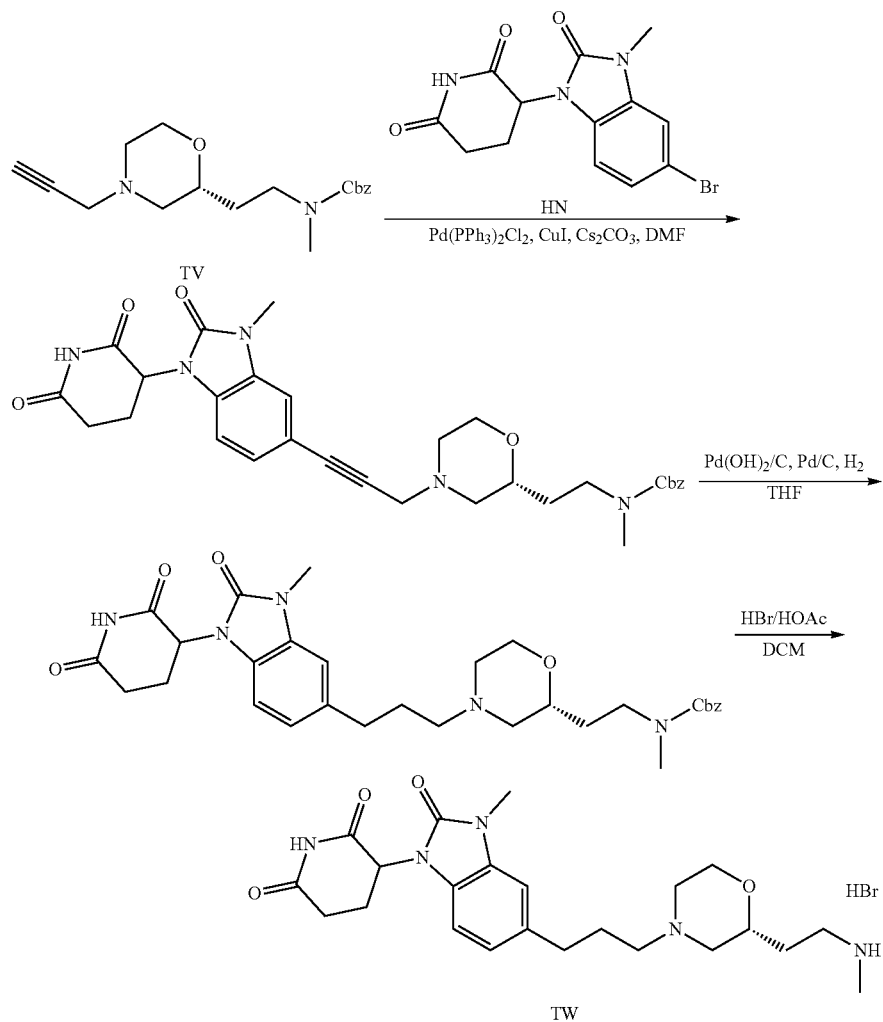

Step 1—Benzyl N-[2-[(2R)-4-[3-[1-(2,6-dioxo-3-piperidyl)-3-methyl-2-oxo-benzimidazol-5-yl]prop-2-ynyl]morpholin-2-yl]ethyl]-N-methyl-carbamate A mixture of benzyl N-methyl-N-[2-[(2R)-4-prop-2-ynylmorpholin-2-yl]ethyl]carbamate (1.93 g, 6.11 mmol, Intermediate TV), 3-(5-bromo-3-methyl-2-oxo-benzimida- Step 2—Benzyl N-[2-[(2R)-4-[3-[1-(2,6-dioxo-3-piperidyl)-3-methyl-2-oxo-benzimidazol-5-yl]propyl]morpholin-2-yl]ethyl]-N-methyl-carbamate A mixture of benzyl N-[2-[(2R)-4-[3-[1-(2,6-dioxo-3-piperidyl)-3-methyl-2-oxo-benzimidazol-5-yl]prop-2-ynyl] morpholin-2-yl]ethyl]-N-methyl-carbamate (1.50 g, 2.61 mmol), Pd/C (400 mg, 10 wt %), and Pd(OH)$_2$/C (400 mg, 10 wt %) in THF (60 mL) was stirred at 25° C. for 2 hours under H$_2$ (15 psi). On completion, the mixture was filtered, and the filter cake was washed with EA (10 mL). The filtrate and washing were combined and concentrated in vacuo. The residue was purified by reversed phase flash chromatography (FA condition) to give the title compound (960 mg, 58% yield) as light yellow solid. $^1$H NMR (400 MHz, CDCl$_3$) δ 8.21 (s, 1H), 7.37-7.31 (m, 5H), 6.92-6.84 (m, 2H), 6.72 (d, J=8.0 Hz, 1H), 5.26-5.18 (m, 1H), 5.13 (s, 2H), 3.92-3.81 (m, 1H), 3.75-3.58 (m, 2H), 3.42 (s, 3H), 3.41-3.35 (m, 2H), 2.93 (s, 3H), 2.80-2.68 (m, 7H), 2.56-2.46 (m, 2H), 2.29-2.19 (m, 2H), 2.08-1.96 (m, 1H), 1.95-1.85 (m, 2H), 1.71-1.58 (m, 2H).

Step 3—3-[3-Methyl-5-[3-[(2R)-2-[2-(methylamino)ethyl]morpholin-4-yl]propyl]-2-oxo-benzimidazol-1-yl]piperidine-2,6-dione To a solution of benzyl N-[2-[(2R)-4-[3-[1-(2,6-dioxo-3-piperidyl)-3-methyl-2-oxo-benzimidazol-5-yl]propyl]morpholin-2-yl]ethyl]-N-methyl-carbamate (950 mg, 1.52 mmol) in DCM (10 mL) was added a solution of hydrogen bromide (2.30 mL, 13.9 mmol, 33% solution) in HOAc at 20° C. The mixture was stirred at 20° C. for 3 hours. On completion, the mixture was concentrated in vacuo at 20° C. The residue was diluted with water and lyophilized to give the title compound (790 mg, 98% yield, HBr salt) as light yellow solid. LC-MS (ESI$^+$) m/z 444.3 (M+H)$^+$.

Benzyl N-methyl-N-[2-[(2S)-4-prop-2-ynylmorpholin-2-yl]ethyl]carbamate (Intermediate TX)

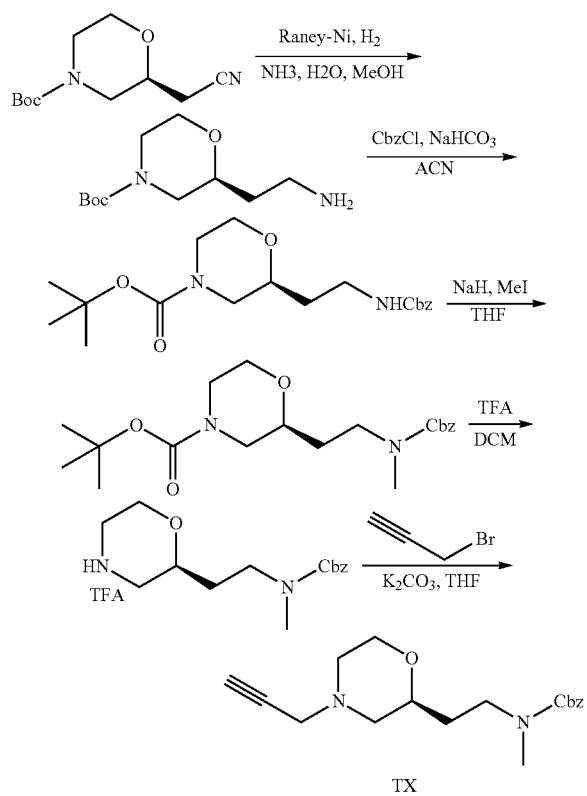

TX

Step 1—Tert-butyl (2S)-2-(2-aminoethyl)morpholine-4-carboxylate

To a solution of tert-butyl (2S)-2-(cyanomethyl)morpholine-4-carboxylate (4.00 g, 17.6 mmol, synthesized via Steps 1-2 of Intermediate RL) in MeOH (20 mL) was added NH$_3$.H$_2$O (2.08 g, 19.5 mmol, 2.29 mL, 33% solution) and Raney-Ni (1.51 g, 17.6 mmol). The reaction mixture was stirred at 25° C. for 12 hours under H$_2$ (50 psi). On completion, the reaction mixture was filtered and the filter cake was washed with MeOH. Then the filtrate was concentrated in vacuo to give the title compound (4.00 g, 98% yield) as colorless oil. $^1$H NMR (400 MHz, DMSO-d$_6$) δ 3.84-3.60 (m, 4H), 3.43-3.33 (m, 4H), 2.90-2.77 (m, 1H), 2.59 (s, 2H), 1.51-1.25 (m, 11H).

Step 2—Tert-butyl (2S)-2-[2-(benzyloxycarbonylamino)ethyl]morpholine-4-carboxylate To a solution of tert-butyl (2S)-2-(2-aminoethyl)morpholine-4-carboxylate (3.50 g, 15.2 mmol) and TEA (3.08 g, 30.3 mmol, 4.23 mL) in DCM (40 mL) was added CbzCl (2.85 g, 16.7 mmol, 2.38 mL). The mixture was stirred at 25° C. for 3 hrs. On completion, the mixture was diluted with H$_2$O (20 mL) and extracted with DCM (2×40 mL). The organic phase was dried over Na$_2$SO$_4$, and then concentrated in vacuo to give the title compound (5.50 g, 99% yield) as yellow oil. $^1$H NMR (400 MHz, CDCl$_3$) δ 7.40-7.32 (m, 5H), 5.25-5.06 (m, 2H), 4.01-3.69 (m, 3H), 3.57-3.34 (m, 3H), 3.34-3.22 (m, 1H), 2.98-2.82 (m, 1H), 2.61 (s, 1H), 2.10-1.78 (m, 1H), 1.76-1.55 (m, 2H), 1.47 (s, 9H).

Step 3—Tert-butyl (2S)-2-[2-[benzyloxycarbonyl(methyl)amino]ethyl]morpholine-4-carboxylate To a solution of tert-butyl (2S)-2-[2-(benzyloxycarbonylamino)ethyl]morpholine-4-carboxylate (2.00 g, 5.49 mmol) in THF (40 mL) was added NaH (439 mg, 10.9 mmol, 60% oil dispersion) at 0° C. The reaction mixture was stirred at 25° C. for 30 minutes, and then MeI (1.95 g, 13.7 mmol, 854 uL) was added to the mixture. The mixture was stirred at 25° C. for 3 hrs. On completion, the reaction mixture was quenched with H$_2$O (20 mL) and extracted with EA (2×40 mL). The organic phase was dried over Na$_2$SO$_4$, filtered and the filtrate was concentrated in vacuo to give a residue. The residue was purified by column chromatography to give the title compound (1.30 g, 62% yield) as yellow oil. $^1$H NMR (400 MHz, CDCl$_3$) δ 7.40-7.28 (m, 5H), 5.14 (s, 2H), 4.02-3.72 (m, 3H), 3.56-3.27 (m, 4H), 3.00-2.81 (m, 4H), 2.71-2.50 (m, 1H), 1.79-1.63 (m, 2H), 1.47 (s, 9H).

Step 4—Benzyl N-methyl-N-[2-[(2S)-morpholin-2-yl]ethyl]carbamate

To a solution of tert-butyl (2S)-2-[2-[benzyloxycarbonyl(methyl)amino]ethyl]morpholine-4-carboxylate (1.20 g, 3.17 mmol) in DCM (10 mL) was added TFA (4.62 g, 40.5 mmol, 3.00 mL). The reaction mixture was stirred at 25° C. for 2 hrs. On completion, the residue was filtered and the filtrate was concentrated in vacuo to give the title compound (1.20 g, 96% yield, TFA) as yellow oil. LC-MS (ESI$^+$) m/z 279.1 (M+H)$^+$.

Step 5—Benzyl N-methyl-N-[2-[(2S)-4-prop-2-ynylmorpholin-2-yl]ethyl]carbamate

To a solution of benzyl N-methyl-N-[2-[(2S)-morpholin-2-yl]ethyl]carbamate (1.30 g, 3.31 mmol, TFA) and 3-bromoprop-1-yne (394 mg, 3.31 mmol, 285 uL) in THF (20 mL) was added K$_2$CO$_3$ (1.37 g, 9.94 mmol). The reaction mixture was stirred at 25° C. for 16 hrs. On completion, the reaction mixture was diluted with water (30 mL) and extracted with EA (3×80 mL). The combined organic layers was dried over Na$_2$SO$_4$, filtered and concentrated in vacuo to give a residue. The residue was purified by column chromatography to give the title compound (900 mg, 85% yield) as a yellow solid. $^1$H NMR (400 MHz, CDCl$_3$) δ 7.42-7.28 (m, 5H), 5.13 (s, 2H), 3.87 (t, J=12.4 Hz, 1H), 3.70-3.47 (m, 2H), 3.40 (t, J=7.2 Hz, 2H), 3.28 (d, J=9.6 Hz, 2H), 2.94 (s, 3H), 2.79-2.62 (m, 2H), 2.39 (t, J=10.8 Hz, 1H), 2.30-2.23 (s, 1H), 2.16-2.06 (m, 1H), 1.75-1.63 (m, 2H).

3-[3-Methyl-5-[3-[(2S)-2-[2-(methylamino)ethyl]morpholin-4-yl]propyl]-2-oxo-benzimidazol-1-yl]piperidine-2,6-dione (Intermediate TY)

Intermediate TX) and 3-(5-bromo-3-methyl-2-oxo-benzimidazol-1-yl)piperidine-2,6-dione (249 mg, 737 umol, Intermediate HN) in DMSO (10 mL) was added DIPEA (476 mg, 3.69 mmol, 642 uL), CuI (14.0 mg, 73.7 umol) and Pd(PPh$_3$)$_2$Cl$_2$ (51.7 mg, 73.7 umol). The reaction mixture was stirred at 80° C. for 2 hrs under N$_2$. On completion, the mixture was filtered, and the filtrate was concentrated in vacuo to give a residue. The residue was purified by reverse phase (0.1% FA condition) to give the title compound (120 mg, 28% yield) as a yellow solid. $^1$H NMR (400 MHz, DMSO-d$_6$) δ 11.14 (s, 1H), 7.38-7.28 (m, 6H), 7.24-7.09 (m, 2H), 5.40 (dd, J=5.2, 12.8 Hz, 1H), 5.06 (s, 2H), 3.72-3.39 (m, 6H), 3.35 (s, 6H), 2.92-2.80 (m, 5H), 2.77-2.71 (m, 1H), 2.66-2.59 (m, 2H), 2.07-2.00 (m, 1H), 1.74-1.55 (m, 2H); LC-MS (ESI$^+$) m/z 574.3 (M+H)$^+$.

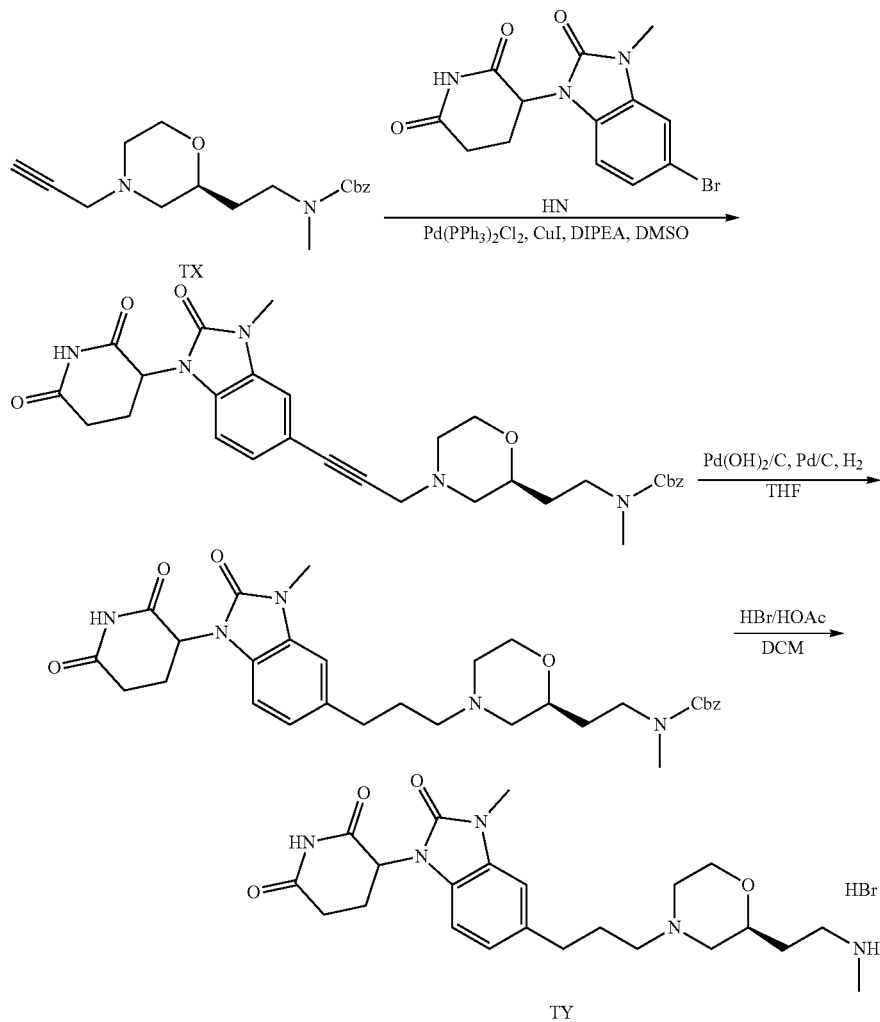

Step 1—Benzyl N-[2-[(2S)-4-[3-[1-(2,6-dioxo-3-piperidyl)-3-methyl-2-oxo-benzimidazol-5-yl]prop-2-ynyl]morpholin-2-yl]ethyl]-N-methyl-carbamate To a solution of benzyl N-methyl-N-[2-[(2S)-4-prop-2-ynylmorpholin-2-yl]ethyl]carbamate (350 mg, 1.11 mmol, Step 2—Benzyl N-[2-[(2S)-4-[3-[1-(2,6-dioxo-3-piperidyl)-3-methyl-2-oxo-benzimidazol-5-yl]propyl]morpholin-2-yl]ethyl]-N-methyl-carbamate To a solution of benzyl N-[2-[(2S)-4-[3-[1-(2,6-dioxo-3-piperidyl)-3-methyl-2-oxo-benzimidazol-5-yl]prop-2-ynyl]

morpholin-2-yl]ethyl]-N-methyl-carbamate (100 mg, 174 umol) in THF (20 mL) was added Pd(OH)$_2$/C (2 mg, 10 wt %) and Pd/C (2 mg, 10 wt %). The reaction mixture was stirred at 25° C. for 12 hrs under H$_2$ (15 psi). On completion, the residue was filtered and the filtrate was concentrated in vacuo to give a residue. The residue was purified by reverse phase (0.1% FA condition) to give the title compound (80.0 mg, 79% yield) as a yellow solid. LC-MS (ESI$^+$) m/z 578.3 (M+H)$^+$.

Step 3—3-[3-Methyl-5-[3-[(2S)-2-[2-(methylamino) ethyl]morpholin-4-yl]propyl]-2-oxo-benzimidazol-1-yl]piperidine-2,6-dione To a solution of benzyl N-[2-[(2S)-4-[3-[1-(2,6-dioxo-3-piperidyl)-3-methyl-2-oxo-benzimidazol-5-yl]propyl]morpholin-2-yl]ethyl]-N-methyl-carbamate (80.0 mg, 138 umol) in DCM (2 mL) was added HBr/CH$_3$COOH (8.66 umol, 1 mL, 35% solution). The reaction mixture was stirred at 20° C. for 4 hrs. On completion, the mixture was concentrated in vacuo to give the title compound (70.0 mg, 96% yield, HBr) as a white solid. LC-MS (ESI$^+$) m/z 444.3 (M+H)$^+$.

1-[4-(1-Amino-2,2,2-trifluoro-ethyl)phenyl]-4-nitro-pyrazole-3-carboxamide (Intermediate TZ)

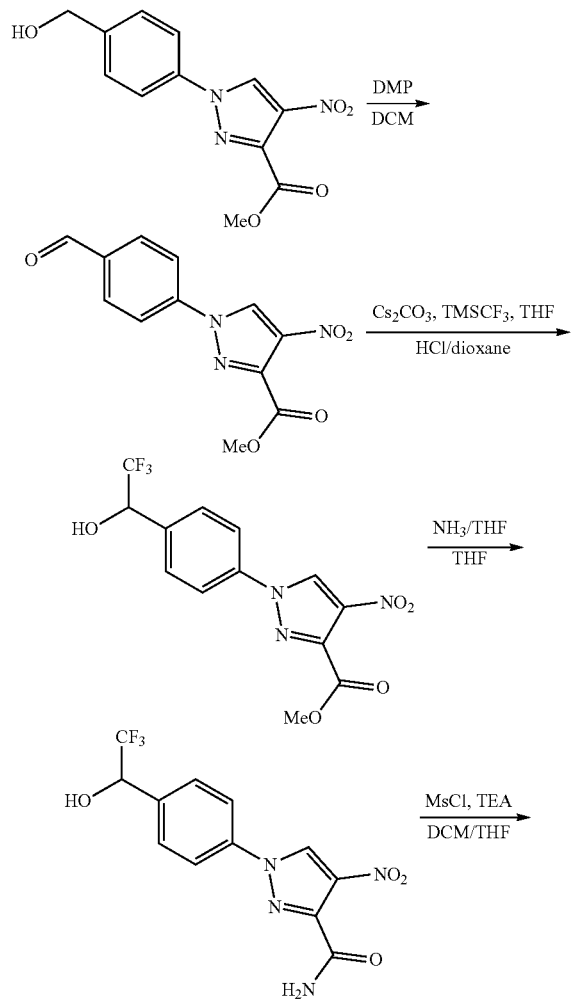

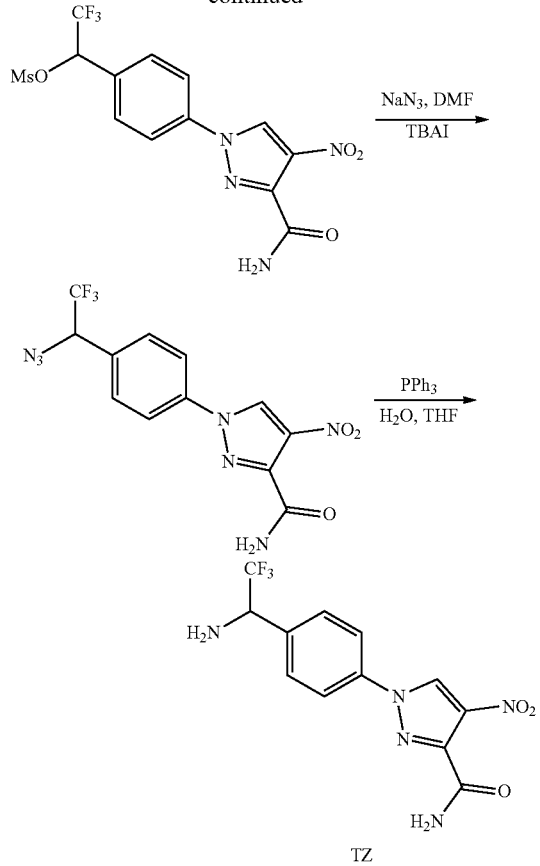

Step 1—Methyl 1-(4-formylphenyl)-4-nitro-pyrazole-3-carboxylate

To a solution of methyl 1-[4-(hydroxymethyl)phenyl]-4-nitro-pyrazole-3-carboxylate (5.00 g, 18.0 mmol, synthesized via Step 1 of Intermediate GB) in DCM (100 mL) was added DMP (9.18 g, 21.6 mmol). The reaction mixture was stirred at 20° C. for 12 hrs. On completion, the mixture was quenched with sat. Na$_2$S$_2$O$_3$ (100 mL) and sat. NaHCO$_3$ (100 mL), stirred and extracted with DCM (2×100 mL). The organic layer was washed with brine (200 mL), dried with Na$_2$SO$_4$, filtered and the filtrate was concentrated in vacuo. The residue was triturated with PE/DCM=2:1 (50 mL), filtered and the filter cake was dried in vacuo to give the title compound (4.30 g, 87% yield) as a yellow solid. $^1$H NMR (400 MHz, DMSO-d$_6$) δ 10.08 (s, 1H), 9.90 (s, 1H), 8.25-8.19 (m, 2H), 8.17-8.09 (m, 2H), 3.96 (s, 3H).

Step 2—Methyl 4-nitro-1-[4-(2,2,2-trifluoro-1-hydroxy-ethyl)phenyl]pyrazole-3-carboxylate To a solution of methyl 1-(4-formylphenyl)-4-nitro-pyrazole-3-carboxylate (4.30 g, 15.6 mmol) in THF (80 mL) was added TMSCF$_3$ (4.44 g, 31.3 mmol) and Cs$_2$CO$_3$ (10.2 g, 31.3 mmol). The reaction mixture was stirred at 20° C. for 2 hrs. Then HCl/dioxane (30 mL) was added and the mixture was stirred at 20° C. for 10 hrs. On completion, the mixture was quenched with water, extracted with EA (2×70 mL). The organic layer was washed with water, then concentrated in vacuo. The residue was purified by silica gel chromatography (SiO$_2$) to give the title compound (1.20 g, 22% yield) as yellow oil. $^1$H NMR (400 MHz, DMSO-$d_6$) δ 9.75 (s, 1H), 8.03-7.97 (m, 2H), 7.70 (d, J=8.8 Hz, 2H), 7.02 (d, J=5.6 Hz, 1H), 5.37-5.27 (m, 1H), 3.95 (s, 3H).

Step 3—4-Nitro-1-[4-(2,2,2-trifluoro-1-hydroxy-ethyl)phenyl]pyrazole-3-carboxamide To a solution of methyl 4-nitro-1-[4-(2,2,2-trifluoro-1-hydroxy-ethyl)phenyl]pyrazole-3-carboxylate (1.20 g, 3.48 mmol) in THF (20 mL) was add NH$_3$.H$_2$O (9.75 g, 69.5 mmol, 25% solution). The reaction mixture was stirred at 75° C. for 10 hrs. On completion, the mixture was diluted with water (40 mL), then extracted with EA (2×40 mL). The organic layer was concentrated in vacuo. The residue was purified by silica gel chromatography (SiO$_2$) to give the title compound (720 mg, 63% yield) as an off-white solid. $^1$H NMR (400 MHz, DMSO-$d_6$) 9.65 (s, 1H), 8.19 (s, 1H), 8.06-7.96 (m, 2H), 7.91 (s, 1H), 7.73-7.65 (m, 2H), 7.00 (d, J=5.6 Hz, 1H), 5.34-5.26 (m, 1H).

Step 4—[1-[4-(3-Carbamoyl-4-nitro-pyrazol-1-yl)phenyl]-2,2,2-trifluoro-ethyl]methanesulfonate To a solution of 4-nitro-1-[4-(2,2,2-trifluoro-1-hydroxy-ethyl)phenyl]pyrazole-3-carboxamide (720 mg, 2.18 mmol) and TEA (662 mg, 6.54 mmol) in a mixed solvent of DCM (10 mL) and THF (10 mL) was added MsCl (500 mg, 4.36 mmol) at 0° C. Then the reaction mixture was stirred at 20° C. for 3 hrs. On completion, the mixture was quenched with water (50 mL), then extracted with DCM (2×50 mL). The organic layer was washed with brine (50 mL), dried with Na$_2$SO$_4$, filtered and concentrated in vacuo. The residue was purified by silica gel chromatography (SiO$_2$) to give the title compound (850 mg, 95% yield) as a yellow solid. $^1$H NMR (400 MHz, DMSO-$d_6$) δ 9.69 (s, 1H), 8.22 (s, 1H), 8.13-8.08 (m, 2H), 7.94 (s, 1H), 7.83-7.74 (m, 2H), 6.70-6.60 (m, 1H), 3.33 (s, 3H).

Step 5—1-[4-(1-Azido-2,2,2-trifluoro-ethyl)phenyl]-4-nitro-pyrazole-3-carboxamide To a solution of [1-[4-(3-carbamoyl-4-nitro-pyrazol-1-yl)phenyl]-2,2,2-trifluoro-ethyl]methanesulfonate (500 mg, 1.22 mmol) and TBAI (45.2 mg, 122 umol) in DMF (10 mL) was added NaN$_3$ (159 mg, 2.45 mmol). The reaction mixture was stirred at 25° C. for 1 hr and then heated at 80° C. for 12 hrs. On completion, the mixture was diluted with water (30 mL), then extracted with DCM (2×30 mL). The organic layer was concentrated in vacuo. The residue was purified by reverse phase (0.1% FA condition) to give the title compound (130 mg, 30% yield) as a white solid. LC-MS (ESI$^+$) m/z 356.1 (M+H)$^+$.

Step 6—1-[4-(1-Amino-2,2,2-trifluoro-ethyl)phenyl]-4-nitro-pyrazole-3-carboxamide To a solution of 1-[4-(1-azido-2,2,2-trifluoro-ethyl)phenyl]-4-nitro-pyrazole-3-carboxamide (130 mg, 366 umol) in a mixed solvent of H$_2$O (0.2 mL) and THF (10 mL) was added PPh$_3$ (192 mg, 732 umol). The mixture was stirred at 20° C. for 2 hrs, then the mixture was heated at 80° C. for 10 hrs. On completion, the mixture was concentrated in vacuo. The residue was purified by silica gel chromatography (SiO$_2$) to give the title compound (90.0 mg, 72% yield) as a white solid. $^1$H NMR (400 MHz, DMSO-$d_6$) δ 9.64 (s, 1H), 8.19 (s, 1H), 8.01-7.94 (m, 2H), 7.91 (s, 1H), 7.74-7.68 (m, 2H), 4.62 (s, 1H), 2.65-2.54 (m, 2H); LC-MS (ESI+) m/z 330.1 (M+H)$^+$.

3-[5-[3-[2-(2-Hydroxyethoxy)ethoxy]propyl]-3-methyl-2-oxo-benzimidazol-1-yl]piperidine-2,6-dione (Intermediate UA)

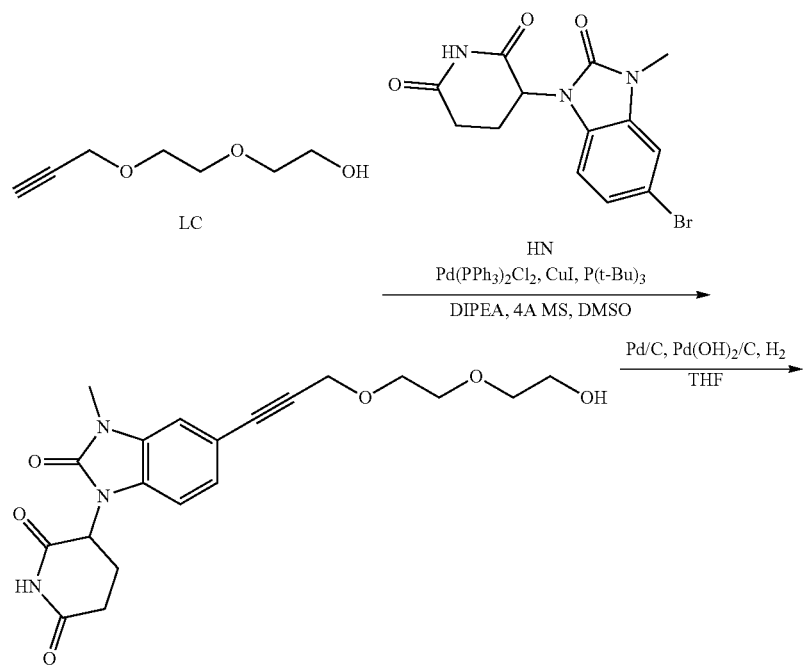

-continued

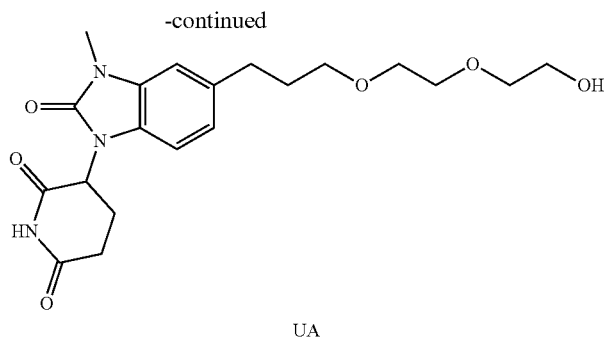

UA

Step 1—3-[5-[3-[2-(2-Hydroxyethoxy)ethoxy]prop-1-ynyl]-3-methyl-2-oxo-benzimidazol-1-yl]piperidine-2,6-dione To a solution of 3-(5-bromo-3-methyl-2-oxo-benzimidazol-1-yl)piperidine-2,6-dione (500 mg, 1.48 mmol, Intermediate HN) and 2-(2-prop-2-ynoxyethoxy)ethanol (639 mg, 4.44 mmol, Intermediate LC) in DMSO (15 mL) was added CuI (56.3 mg, 295 umol), Pd(PPh$_3$)$_2$Cl$_2$ (103 mg, 147 umol), DIPEA (955 mg, 7.39 mmol), 4 Å moleculare sieves (0.5 g) and P(t-Bu)$_3$ (2.30 g, 1.48 mmol, 13 wt %). The reaction mixture was heated at 80° C. for 2 hours. On completion, the reaction mixture was quenched by water (30 mL), and then extracted with EA (3×40 mL). The combined organic layers were dried over Na$_2$SO$_4$, filtered and concentrated in vacuo to give a residue. The residue was purified by prep-HPLC (FA condition) to give the title compound (590 mg, 99% yield) as light yellow solid. $^1$H NMR (400 MHz, DMSO-d$_6$) δ 11.11 (s, 1H), 7.33 (d, J=0.8 Hz, 1H), 7.20-7.09 (m, 2H), 5.40 (dd, J=5.2, 12.4 Hz, 1H), 4.43-4.37 (m, 2H), 3.67-3.62 (m, 2H), 3.61-3.56 (m, 2H), 3.52-3.49 (m, 2H), 3.46-3.42 (m, 3H), 3.34 (s, 3H), 2.96-2.81 (m, 1H), 2.76-2.59 (m, 2H), 2.07-1.94 (m, 1H); LC-MS (ESI$^+$) m/z 402.1 (M+H)$^+$.

Step 2—3-[5-[3-[2-(2-Hydroxyethoxy)ethoxy]propyl]-3-methyl-2-oxo-benzimidazol-1-yl]piperidine-2,6-dione To a solution of 3-[5-[3-[2-(2-hydroxyethoxy)ethoxy]prop-1-ynyl]-3-methyl-2-oxo-benzimidazol-1-yl]piperidine-2,6-dione (650 mg, 1.62 mmol) in THF (20 mL) was added Pd/C (100 mg, 10 wt %) and Pd(OH)$_2$/C (100 mg, 10 wt %) under N$_2$. The suspension was degassed under vacuum and purged with H$_2$ three times. The mixture was stirred under H$_2$ (15 psi) at 25° C. for 16 hours. On completion, the reaction mixture was filtered and concentrated in vacuo to give the title compound (570 mg, 86% yield) as light yellow solid. $^1$H NMR (400 MHz, DMSO-d$_6$) δ 11.08 (s, 1H), 7.04 (s, 1H), 7.00 (d, J=8.0 Hz, 1H), 6.92-6.82 (m, 1H), 5.33 (dd, J=5.2, 12.8 Hz, 1H), 4.58 (t, J=5.2 Hz, 1H), 3.54-3.37 (m, 10H), 2.97-2.82 (m, 1H), 2.76-2.57 (m, 4H), 2.01 (s, 1H), 1.87-1.72 (m, 2H); LC-MS (ESI$^+$) m/z 406.2 (M+H)$^+$.

2-[2-[3-[1-(2,6-dioxo-3-piperidyl)-3-methyl-2-oxo-benzimidazol-5-yl]propoxy]ethoxy]ethyl methanesulfonate (Intermediate UB)

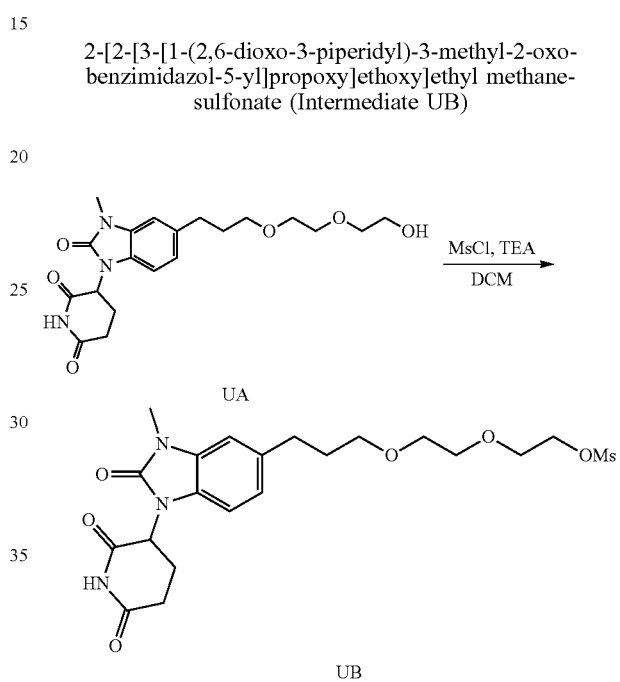

To a solution of 3-[5-[3-[2-(2-hydroxyethoxy)ethoxy]propyl]-3-methyl-2-oxo-benzimidazol-1-yl]piperidine-2,6-dione (100 mg, 246 umol) and TEA (74.8 mg, 739 umol) in DCM (4 mL) was added MsCl (42.3 mg, 369 umol) at 0° C., the mixture was stirred at 25° C. for 1 hour. On completion, the reaction mixture was quenched by water (15 mL), and then extracted with DCM (3×15 mL). The combined organic layers were dried over Na$_2$SO$_4$, filtered and concentrated in vacuo to give the title compound (110 mg, 92% yield) as light yellow oil. LC-MS (ESI$^+$) m/z 484.1 (M+H)$^+$.

2-[2-[3-[1-(2,6-Dioxo-3-piperidyl)-3-methyl-2-oxo-benzimidazol-5-yl]propoxy]ethoxy]acetaldehyde (Intermediate UC)

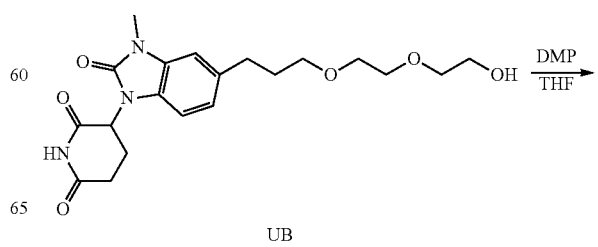

-continued

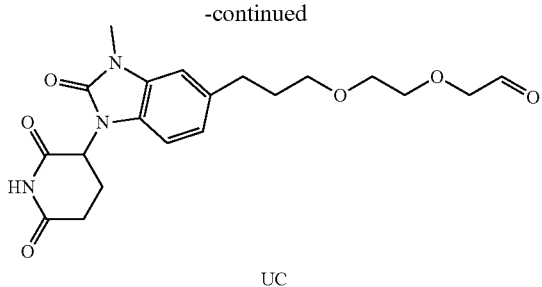

UC

To a solution of 3-[5-[3-[2-(2-hydroxyethoxy)ethoxy]propyl]-3-methyl-2-oxo-benzimidazol-1-yl]piperidine-2,6-dione (270 mg, 666 umol, Intermediate UA) in THF (10 mL) was added DMP (339 mg, 799 umol). The mixture was stirred at 25° C. for 4 hrs. On completion, the reaction mixture was quenched by saturated $Na_2S_2O_3$ (6 mL) and saturated $NaHCO_3$ (6 mL) at 25° C., stirred for 30 minutes. Then the mixture was extracted with DCM (3×30 mL). The combined organic layers dried over $Na_2SO_4$, filtered and the filtrate was concentrated in vacuo to give a residue. The residue was purified by prep-HPLC (0.1% FA condition) to give the title compound (150 mg, 56% yield) as a light yellow solid. $^1$H NMR (400 MHz, DMSO-$d_6$) δ 11.08 (s, 1H), 9.62 (s, 1H), 7.10-6.92 (m, 2H), 6.85-6.72 (s, 1H), 5.41-5.38 (m, 1H), 4.18 (s, 1H), 3.72-3.65 (m, 1H), 3.60-3.35 (m, 6H), 3.34-3.25 (m, 3H), 2.99-2.81 (m, 1H), 2.75-2.55 (m, 4H), 2.05-1.91 (m, 1H), 1.88-1.70 (m, 2H); LC-MS (ESI$^+$) m/z 404.2 (M+H)$^+$.

4-Amino-1-[4-[1-[2-[2-[3-[1-(2,6-dioxo-3-piperidyl)-3-methyl-2-oxo-benzimidazol-5-yl]propoxy]ethoxy]ethylamino]-2,2,2-trifluoro-ethyl]phenyl]pyrazole-3-carboxamide (Intermediate UD)

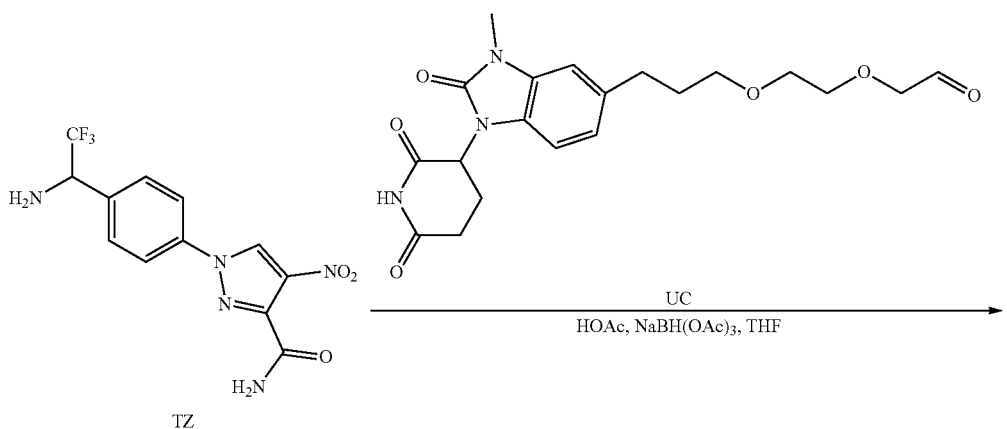

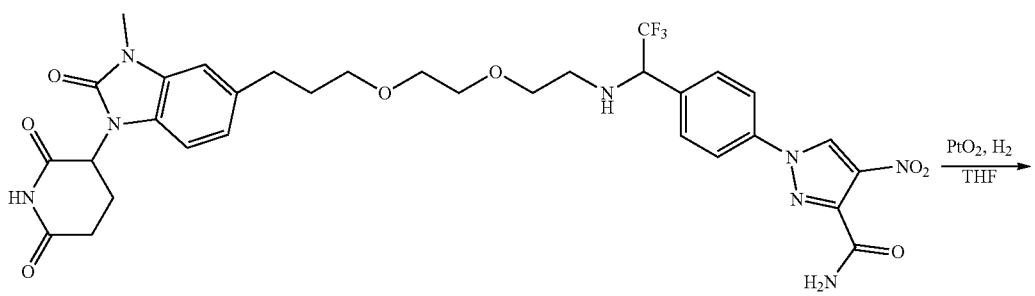

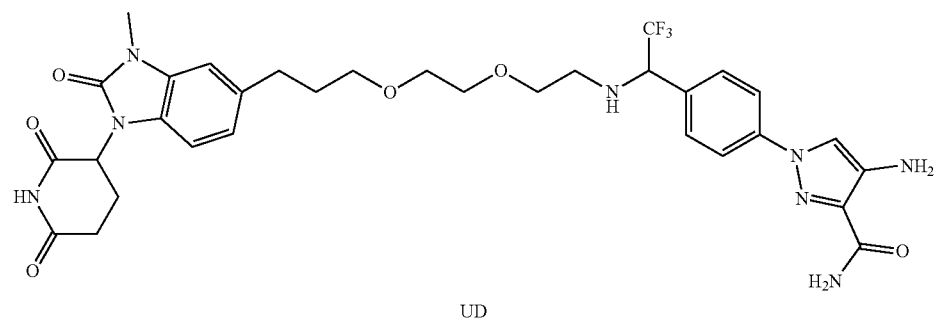

UD

US 10,874,743 B2

1895

Step 1—1-[4-[1-[2-[2-[3-[1-(2,6-Dioxo-3-piperidyl)-3-methyl-2-oxo-benzimidazol-5-yl]propoxy]ethoxy]ethylamino]-2,2,2-trifluoro-ethyl]phenyl]-4-nitro-pyrazole-3-carboxamide To a solution of 2-[2-[3-[1-(2,6-dioxo-3-piperidyl)-3-methyl-2-oxo-benzimidazol-5-yl]propoxy]ethoxy]acetaldehyde (98.0 mg, 243 umol, Intermediate UC) and 1-[4-(1-amino-2,2,2-trifluoro-ethyl)phenyl]-4-nitro-pyrazole-3-carboxamide (80.0 mg, 243 umol, Intermediate TZ) in THF (3 mL) was added HOAc (14.6 mg, 243 umol). The mixture pH was adjusted to 5-6 and NaBH(OAc)$_3$ (103 mg, 486 umol) was added into the mixture. The reaction mixture was stirred at 25° C. for 12 hrs. On completion, the mixture was concentrated in vacuo. The residue was purified by reverse phase (0.1% FA condition) to give the title compound (25.0 mg, 14% yield) as a white solid. $^1$H NMR (400 MHz, DMSO-d$_6$) δ 11.08 (s, 1H), 9.63 (s, 1H), 8.18 (s, 1H), 7.99 (d, J=8.8 Hz, 2H), 7.92 (s, 1H), 7.68 (d, J=8.8 Hz, 2H), 7.02-6.96 (m, 2H), 6.84 (d, J=8.0 Hz, 1H), 6.54 (s, 1H), 5.32 (dd, J=5.2, 12.8 Hz, 1H), 4.70-4.55 (m, 1H), 3.50-3.44 (m, 6H), 3.37 (t, J=6.4 Hz, 2H), 3.30 (s, 3H), 2.93-2.82 (m, 2H), 2.72-2.66 (m, 1H), 2.66-2.62 (m, 4H), 2.03-1.95 (m, 1H), 1.84-1.74 (m, 2H); LC-MS (ESI$^+$) m/z 717.0 (M+H)$^+$.

Step 9—4-Amino-1-[4-[1-[2-[2-[3-[1-(2,6-dioxo-3-piperidyl)-3-methyl-2-oxo-benzimidazol-5-yl]propoxy]ethoxy]ethylamino]-2,2,2-trifluoro-ethyl]phenyl]pyrazole-3-carboxamide To a solution of 1-[4-[1-[2-[2-[3-[1-(2,6-dioxo-3-piperidyl)-3-methyl-2-oxo-benzimidazol-5-yl]propoxy]ethoxy]ethylamino]-2,2,2-trifluoro-ethyl]phenyl]-4-nitro-pyrazole-3-carboxamide (22.0 mg, 29.2 umol) in THF (4 mL) was added PtO$_2$ (6.62 mg, 29.2 umol). The reaction mixture was stirred at 25° C. for 4 hrs under H$_2$ (15 psi) atmosphere. On completion, the mixture was filtered and the filtrate was concentrated in vacuo to give the title compound (20.0 mg, 100% yield) as a yellow solid. LC-MS (ESI$^+$) m/z 687.3 (M+H)$^+$ 4-[2-[2-[2-[2-[2-(2-Aminoethoxy)ethoxy]ethoxy]ethoxy]ethoxy]ethylamino]-2-(2,6-dioxo-3-piperidyl)isoindoline-1,3-dione (Intermediate UE)

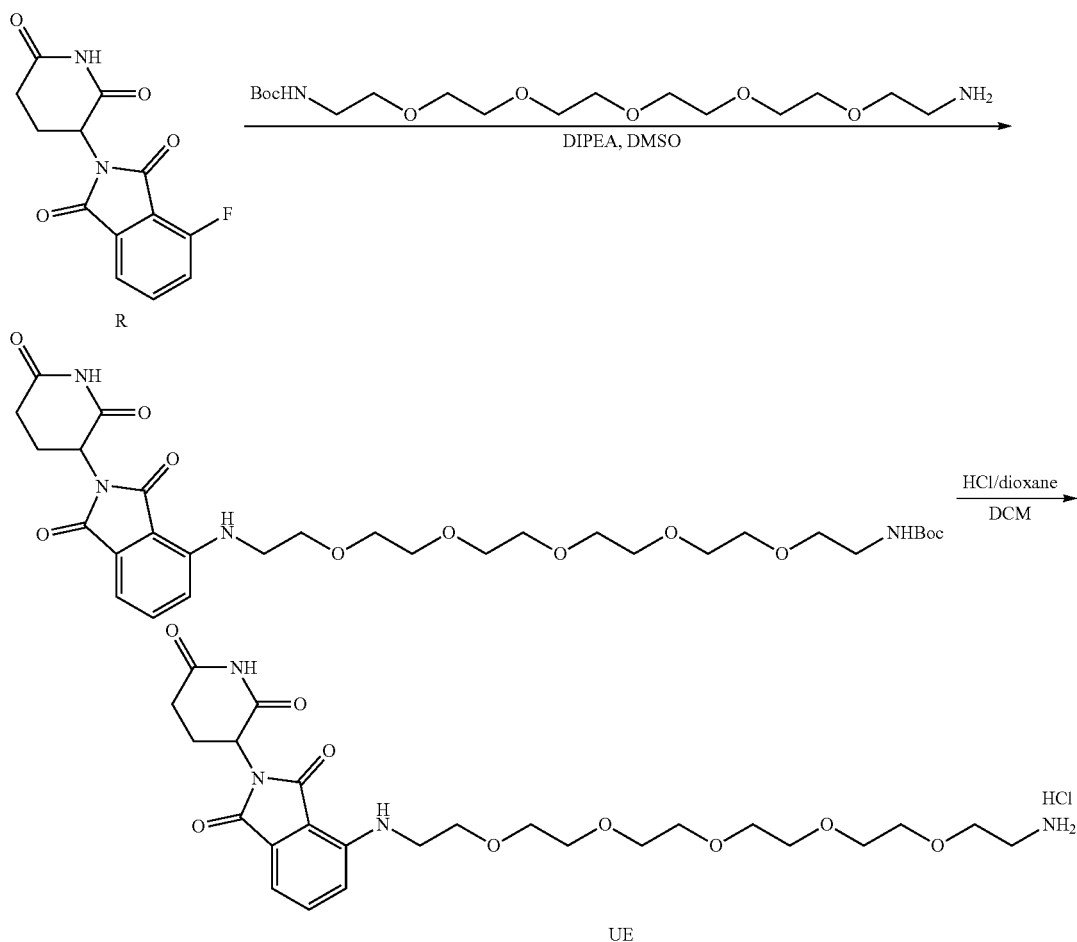

Step 1—Tert-butyl N-[2-[2-[2-[2-[2-[2-[[2-(2,6-dioxo-3-piperidyl)-1,3-dioxo-isoindolin-4-yl]amino]ethoxy]ethoxy]ethoxy]ethoxy]ethoxy]ethyl]carbamate A solution of 2-(2,6-dioxo-3-piperidyl)-4-fluoro-isoindoline-1,3-dione (550 mg, 1.99 mmol, Intermediate R), tert-butyl N-[2-[2-[2-[2-[2-(2-aminoethoxy)ethoxy]ethoxy]ethoxy]ethoxy]ethyl]carbamate (500 mg, 1.31 mmol, CAS

189209-27-6) and DIPEA (1.36 g, 10.5 mmol) in DMSO (20 mL) was stirred at 120-130° C. for 16 hours. On completion, the reaction mixture was cooled to rt and diluted with water (150 mL), then extracted with EA (3×80 mL). The combined organic layer was washed with brine (50 mL), dried over $Na_2SO_4$, filtered and concentrated in vacuo. The residue was purified by column chromatography on silica gel to give crude product (800 mg). The crude product was purified by reversed phase chromatography (phase A: 0.1% FA water, B: $CH_3CN$, 53% $CH_3CN$) to the title compound (490 mg, 58% yield) as yellow gum. $^1$H NMR (400 MHz, $CDCl_3$) δ 8.29 (s, 1H), 7.50 (dd, J=7.2 Hz, J=8.4 Hz, 1H), 7.12 (d, J=7.2 Hz, 1H), 6.93 (d, J=8.4 Hz, 1H), 6.51 (m, 1H), 5.09 (m, 1H), 4.94-4.90 (m, 1H), 3.74-3.63 (m, 18H), 3.55-3.54 (m, 4H), 3.32-3.31 (m, 2H), 2.83-2.77 (m, 3H), 2.15 (m, 1H), 1.45 (s, 9H). LC-MS (ESI$^+$) m/z 659.3 (M+Na), 537.3 (M-Boc+1)$^+$.

Step 2—4-[2-[2-[2-[2-[2-(2-Aminoethoxy)ethoxy]ethoxy]ethoxy]ethoxy]ethylamino]-2-(2,6-dioxo-3-piperidyl)isoindoline-1,3-dione To a solution of tert-butyl N-[2-[2-[2-[2-[2-[2-[[2-(2,6-dioxo-3-piperidyl)-1,3-dioxo-isoindolin-4-yl]amino]ethoxy]ethoxy]ethoxy]ethoxy]ethyl]carbamate (490 mg, 770 umol) in DCM (10 mL) was added 4.0 M HCl/dioxane (5 mL) at rt, and the mixture was stirred at rt for 2 hours. On completion, the mixture was concentrated in vacuo to give the title compound (530 mg, quant. crude yield, HCl) as yellow gum. LC-MS (ESI$^+$) m/z 537.3 (M+H)$^+$.

3,6,9,12,15-pentaoxaheptadecanedioic acid (Intermediate UF)

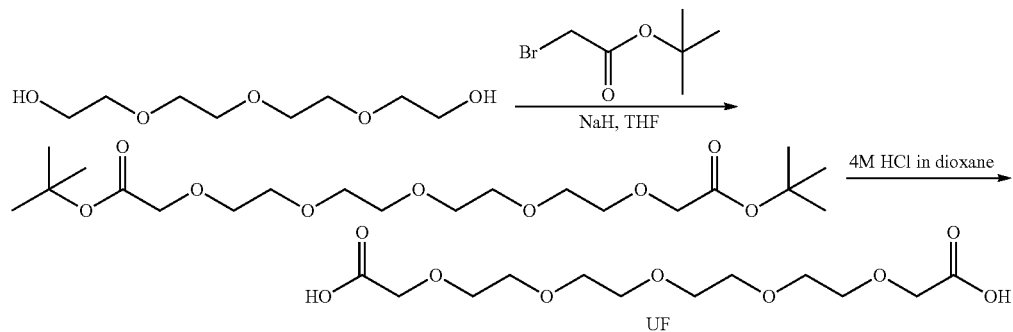

Step 1—di-tert-butyl 3,6,9,12,15-pentaoxaheptadecanedioate

To a solution of NaH (60% dispersion in mineral oil, 4.54 g, 113.4 mmol) in THF (200 mL) was added 2,2'-((oxybis(ethane-2,1-diyl))bis(oxy))diethanol (10 g, 51.5 mmol, CAS #112-60-7) portion wise at 0° C. After addition, the mixture was stirred at 0° C. for 1h, then tert-butyl 2-bromoacetate (22 g, 113.4 mmol) was added. After addition, the mixture was warmed to rt and stirred overnight. The mixture was quenched by addition of water, then extract with EtOAc (3×50 mL). The combined organic layers was washed with brine (100 mL×2), dried over anhydrous $Na_2SO_4$, filtered and concentrated in vacuo. The residue was purified by flash chromatography eluting with PE/EA=4/1 to give the title compound (5.5 g, 25.2%) as an colorless oil. LC/MS (ESI, m/z): [M+1]$^+$=423.1.

Step 2—3,6,9,12,15-pentaoxaheptadecanedioic acid

To a solution of di-tert-butyl 3,6,9,12,15-pentaoxaheptadecanedioate (5.5 g, 13 mmol) in DCM (2 mL) was added 4M HCl in dioxane (18 mL). The mixture was stirred at rt overnight. The mixture was concentrated in vacuo to give the title compound (3.5 g, 87% yield). LC/MS (ESI, m/z): [M+1]$^+$=311.0.

3-(6-Amino-9H-pyrido[2,3-b]indol-9-yl)piperidine-2,6-dione (Intermediate UG)

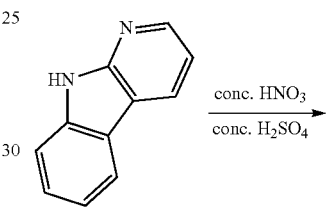

-continued

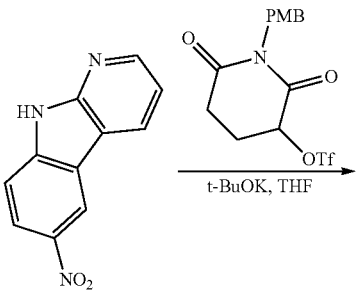

-continued

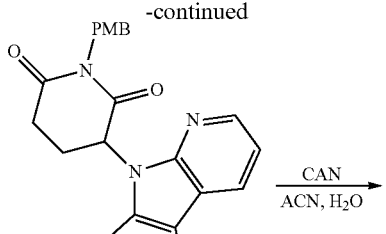

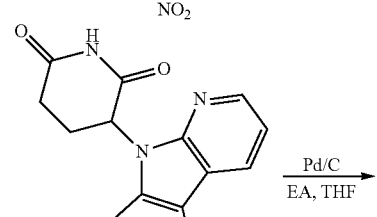

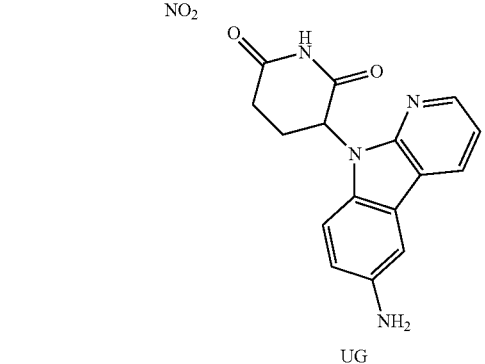

Step 1—6-nitro-9H-pyrido[2,3-b]indole

To a mixture 68%-70% nitric acid in H$_2$O (20 mL) and fuming nitric acid (20 mL) was added 9H-pyrido[2,3-b] indole (2.5 g, 14.88 mmol) in portions at room temperature and the temperature was maintained under 30° C. The mixture was stirred at 25° C. for 1 h. Then the mixture was set aside overnight at 0° C. A lot of solid was formed. The resulting solid was filtered off and stirred with dilute ammonium hydroxide solution (50 mL) (33% in H2O). It was then filtered off and washed with water to leave the crude compound. The crude compound was triturated with EA and filtrated to give 6-nitro-9H-pyrido[2,3-b]indole as a grey solid. (2.6 g, yield: 82%). LC/MS (ESI, m/z): [M+1]$^+$=214.2

Step C: 1-(4-methoxybenzyl)-3-(6-nitro-9H-pyrido [2,3-b]indol-9-yl)piperidine-2,6-dione To a solution of 6-nitro-9H-pyrido[2,3-b]indole (2.6 g, 12.2 mmol) in THF (50 mL) was added t-BuOK (2.05 g, 18.3 mmol) at 0° C. The mixture was stirred at 0-10° C. for 1 hour under N$_2$. Then a solution of [1-[(4-methoxyphenyl) methyl]-2,6-dioxo-3-piperidyl]trifluoromethanesulfonate (6.98 g, 18.3 mmol) in THF (50 mL) was added to the reaction mixture at 0-10° C. during 30 minutes. The mixture was stirred at 0-10° C. for 30 minutes under N$_2$. The reaction was quenched water (40 mL) and extracted with EA (3×50 mL). The combined organic layers were concentrated under reduced pressure. The residue was triturated with EA and filtrated to give 1-(4-methoxybenzyl)-3-(6-nitro-9H-pyrido [2,3-b]indol-9-yl)piperidine-2,6-dione as a grey solid (4.95 g, yield 91%). LC/MS (ESI, m/z): [M+1]$^+$=445.1

Step D: 3-(6-nitro-9H-pyrido[2,3-b]indol-9-yl)piperidine-2,6-dione

To a solution of 1-(4-methoxybenzyl)-3-(6-nitro-9H-pyrido[2,3-b]indol-9-yl)piperidine-2,6-dione (400 mg, 0.90 mmol) in ACN (10 mL) was added CAN (2.46 g, 0.45 mmol) in water (3 mL) at 0° C. After the addition, the mixture was warmed up to room temperature and stirred overnight. The reaction mixture was poured into water (50 mL), extract with EtOAc (3×50 mL), the combined organic layers were concentrated under reduced pressure. The residue was triturated with DMF/EA and filtrated to give 3-(6-nitro-9H-pyrido[2,3-b]indol-9-yl)piperidine-2,6-dione as a grey solid (130 mg, yield: 44.4%). LC/MS (ESI, m/z): [M+1]$^+$=325.1

Step E: 3-(6-amino-9H-pyrido[2,3-b]indol-9-yl) piperidine-2,6-dione

To a solution of 3-(6-nitro-9H-pyrido[2,3-b]indol-9-yl) piperidine-2,6-dione (130 mg, 0.401 mmol) in THF (5 mL) and EA (5 mL) was added Palladium on activated carbon 10% Pd (50 mg). The mixture was stirred at room temperature under H2 balloon overnight. The reaction mixture was filtered, the filtrate was concentrated under reduce pressure, the residue was triturated with DMF/EA and filtrated to give 3-(6-amino-9H-pyrido[2,3-b]indol-9-yl)piperidine-2,6-dione as a grey solid (55 mg, yield: 46.4%). $^1$H NMR (400 MHz, DMSO-d$_6$) δ11.08 (s, 1H), 8.26-8.39 (m, 2H), 7.24-7.36 (m, 2H), 7.14 (dd, J=7.63, 4.88 Hz, 1H), 6.85 (dd, J=8.63, 2.13 Hz, 1H), 5.90 (br. s., 1H), 4.87 (s, 2H), 2.93-3.08 (m, 2H), 2.68 (d, J=12.26 Hz, 1H), 2.01-2.11 (m, 1H). LC/MS (ESI, m/z): [M+1]$^+$=295.1.

3-(6-bromo-9H-pyrido[2,3-b]indol-9-yl)piperidine-2, 6-dione (Intermediate UH)

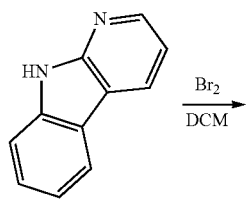

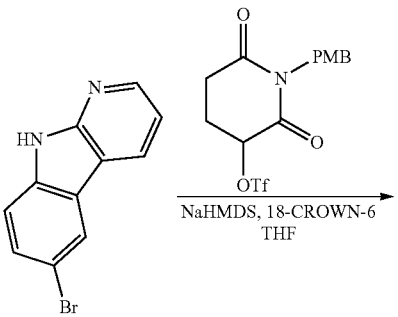

-continued

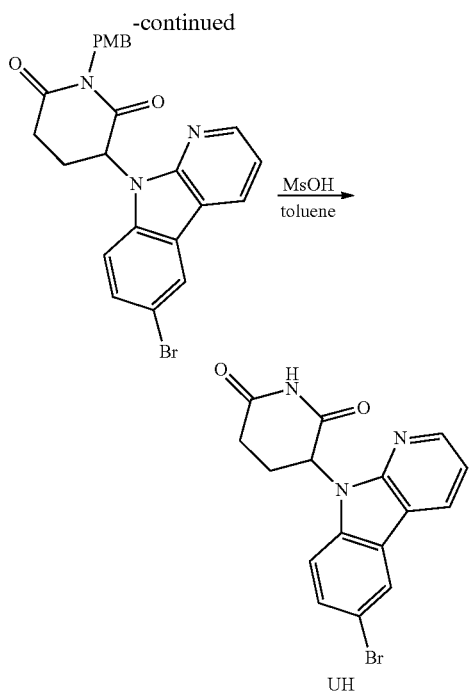

Step 1—6-bromo-9H-pyrido[2,3-b]indole

To a stirred solution of 9H-pyrido[2,3-b]indole (3 g, 17.9 mmol, CAS #26148-68-5) in DCM (50 mL) was added Br$_2$ (3.4 g, 21.4 mmol) dropwise at 0° C. The reaction mixture was stirred at 0° C. for 4 h. To the mixture was added aq. NaHCO$_3$ (100 mL), then the solution was extracted with EA (200 mL). The organic layer was washed with brine (50 mL), dried over Na$_2$SO$_4$, filtered, concentrated to give the title compound (2.7 g, 61% yield) as yellow solid. $^1$H NMR (400 MHz, DMSO-d$_6$) δ 12.02 (s, 1H), 8.60 (dd, J=1.2 Hz, J=7.6 Hz, 1H), 8.48-8.44 (m, 2H), 7.60-7.58 (m, 1H), 7.48 (d, J=8.4 Hz, 1H), 7.26 (dd, J=4.8 Hz, J=7.6 Hz, 1H). LC/MS (ESI, m/z): [M+1]$^+$=247.8

Step 2—3-(6-bromo-9H-pyrido[2,3-b]indol-9-yl)-1-(4-methoxybenzyl)piperidine-2,6-dione To a stirred solution of 6-bromo-9H-pyrido[2,3-b]indole (200 mg, 0.810 mmol) and 18-crown-6 (43 mg, 0.162 mmol) in THF (10 mL) was added NaHMDS (0.6 mL, 2 M in THF) dropwise at −30° C. under N$_2$. The mixture was stirred for 1 h at −30° C. under N$_2$. Then to the mixture was added a solution of 1-(4-methoxybenzyl)-2,6-dioxopiperidin-3-yl trifluoromethanesulfonate (463 mg, 1.21 mmol) in THF (5 mL) dropwise at −30° C. under N$_2$. The mixture was stirred for 2 h at −30° C. The mixture was added to aq. NH$_4$Cl (20 mL), then extracted with EA (50 mL). The organic layer was washed with brine (30 mL), dried over Na$_2$SO$_4$, filtered, concentrated and purified by column (PE/EA/DCM=10/1/1 to 3/1/1) to give the title compound (220 mg, 57% yield) as a yellow oil. $^1$H NMR (400 MHz, CDCl$_3$) δ 8.41 (dd, J=1.6 Hz, J=5.2 Hz, 1H), 8.29 (dd, J=1.2 Hz, J=7.6 Hz, 1H), 8.20 (d, J=1.6 Hz, 1H), 7.45 (dd, J=2.0 Hz, J=8.8 Hz, 1H), 7.40 (d, J=8.8 Hz, 2H), 7.24-7.21 (m, 1H), 6.84 (d, J=8.8 Hz, 3H), 5.90-5.87 (m, 1H), 5.01 (dd, J=13.6 Hz, J=20.4 Hz, 2H), 3.79 (s, 3H), 3.09-2.88 (m, 3H), 3.27-2.24 (m, 1H). LC/MS (ESI, m/z): [M+1]$^+$=479.1.

Step 3—3-(6-bromo-9H-pyrido[2,3-b]indol-9-yl)piperidine-2,6-dione

A mixture of 3-(6-bromo-9H-pyrido[2,3-b]indol-9-yl)-1-(4-methoxybenzyl)piperidine-2,6-dione (1.3 g, 2.72 mmol), MsOH (10 mL) and toluene (20 mL) was heated to 110° C. and stirred for 3 h under N$_2$. The solvent was concentrated to remove toluene. Then to the mixture was added EtOAc (50 mL), and the solution was washed with brine (50 mL) to remove MsOH. The organic layer was dried over Na$_2$SO$_4$. The solid was filter and the filtrate was concentrated. The resulting residue was purified by column chromatography on silica gel (PE/EA=1/1) to give the title compound (500 mg, 51% yield) as a white solid. $^1$H NMR (400 MHz, DMSO-d$_6$) δ 11.17 (s, 1H), 8.64 (dd, J=1.6 Hz, J=7.6 Hz, 1H), 8.52 (d, J=2.0 Hz, 1H), 8.47 (dd, J=1.6 Hz, J=4.8 Hz, 1H), 7.68-7.64 (m, 2H), 7.32 (dd, J=4.8 Hz, J=7.6 Hz, 1H), 6.06 (br s, 1H), 3.16-2.96 (m, 2H), 2.73-2.67 (m, 1H), 2.16-2.13 (m, 1H). LC/MS (ESI, m/z): [M+1]$^+$=358.0.

tert-butyl methyl(3-(prop-2-yn-1-yloxy)propyl)carbamate (Intermediate UI)

To a solution of tert-butyl (3-hydroxypropyl)(methyl) carbamate (2 g, 10.6 mmol, CAS #98642-44-5) in DCM (30 mL) was added aq. NaOH (40%, 20 mL), 3-bromoprop-1-yne (1.9 g, 15.9 mmol) and TBAHS (180 mg, 0.530 mmol) at rt. The mixture was stirred at rt for 3 h. To the mixture was added H$_2$O (100 mL), then the mixture was extracted with DCM (3×30 mL). The organic layers were washed with brine (50 mL), dried over Na$_2$SO$_4$, filtered, concentrated and purified by column (PE/EA=20/1 to 10/1 to 4/1) to give the title compound (1.4 g, 58% yield) as a yellow oil. $^1$H NMR (400 MHz, CDCl$_3$) δ 4.14 (d, J=2.4 Hz, 2H), 3.53 (t, J=6.4 Hz, 2H), 3.29 (t, J=6.8 Hz, 2H), 2.86 (s, 3H), 2.42 (t, J=2.4 Hz, 1H), 1.83-1.80 (m, 2H), 1.46 (s, 9H). LC/MS (ESI, m/z): [M+1]$^+$=227.9.

2-[2-[2-[2-(4-Nitropyrazol-1-yl)ethoxy]ethoxy]ethoxy]ethanamine (Intermediate UJ)

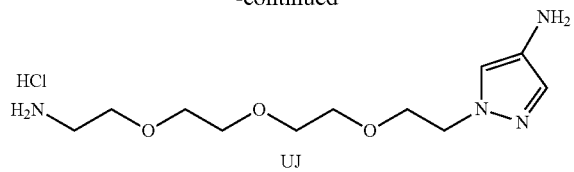

mmol) in DCM (6 mL) was added HCl/dioxane (4 M, 4.50 mL). The reaction mixture was stirred at 20° C. for 1.5 hours. On completion, the reaction mixture was concentrated in vacuo to give the title compound (620 mg, 99% yield, HCl salt) as a yellow solid. LC-MS (ESI$^+$) m/z 289.2 (M+H)$^+$.

Step 1—Tert-butyl N-[2-[2-[2-[2-(4-nitropyrazol-1-yl)ethoxy]ethoxy]ethoxy]ethyl]carbamate To a solution of 2-[2-[2-[2-(tert-butoxycarbonylamino)ethoxy]ethoxy]ethoxy]ethyl methanesulfonate (3 g, 8.08 mmol, Intermediate AO) and 4-nitro-1H-pyrazole (608 mg, 4-[2-[2-[2-[2-(4-Aminopyrazol-1-yl)ethoxy]ethoxy]ethoxy]ethylamino]-2-(2,6-dioxo-3-piperidyl)isoindoline-1,3-dione (Intermediate UK)

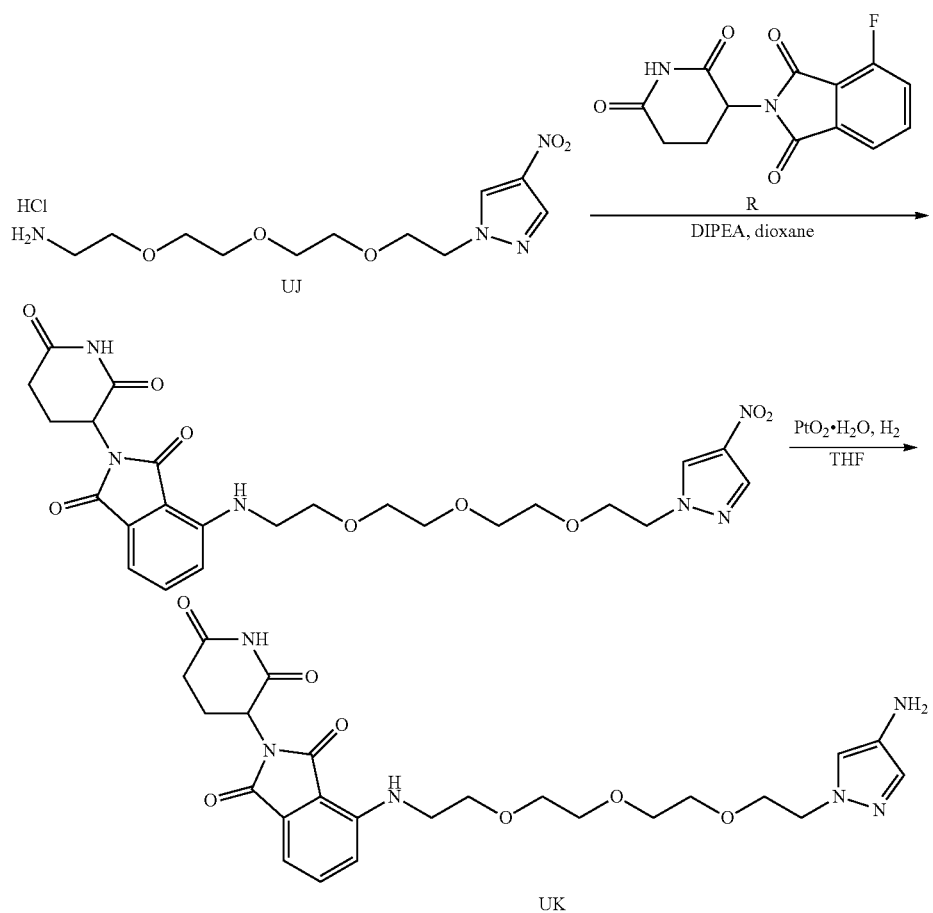

5.38 mmol) in DMF (40 mL) was added Cs$_2$CO$_3$ (3.51 g, 10.7 mmol). The reaction mixture was stirred at 130° C. for 2 hours. On completion, the mixture was filtered, and the filtrate was concentrated in vacuo. The residue was purified by reverse phase (0.1% FA condition) to give the title compound (1.20 g, 57% yield) as yellow oil. LC-MS (ESI$^+$) m/z 411.2 (M+Na)$^+$.

Step 2—2-[2-[2-[2-(4-Nitropyrazol-1-yl)ethoxy]ethoxy]ethoxy]ethanamine

To a solution of tert-butyl N-[2-[2-[2-[2-(4-nitropyrazol-1-yl)ethoxy]ethoxy]ethoxy]ethyl]carbamate (750 mg, 1.93

Step 1—2-(2,6-Dioxo-3-piperidyl)-4-[2-[2-[2-[2-(4-nitropyrazol-1-yl)ethoxy]ethoxy]ethoxy]ethylamino]isoindoline-1,3-dione To a solution of 2-[2-[2-[2-(4-nitropyrazol-1-yl)ethoxy]ethoxy]ethoxy]ethanamine (670 mg, 2.06 mmol, HCl salt, Intermediate UJ) and 2-(2,6-dioxo-3-piperidyl)-4-fluoro-isoindoline-1,3-dione (570 mg, 2.06 mmol, Intermediate R) in dioxane (20 mL) was added DIPEA (1.33 g, 10.3 mmol). The reaction mixture was stirred at 120° C. for 12 hours. On completion, the reaction mixture was concentrated in vacuo. The residue was purified by reversed phase (0.1%, FA condition) to give the title compound (400 mg, 36% yield)

as yellow oil. $^1$H NMR (400 MHz, DMSO-d$_6$) δ 11.11 (s, 1H), 8.82 (s, 1H), 8.26 (s, 1H), 7.62-7.52 (m, 1H), 7.14 (d, J=8.8 Hz, 1H), 7.04 (d, J=7.2 Hz, 1H), 6.59 (t, J=6.0 Hz, 1H), 5.06 (dd, J=5.2, 12.8 Hz, 1H), 4.33 (t, J=5.2 Hz, 2H), 3.79 (t, J=5.2 Hz, 2H), 3.62-3.59 (m, 2H), 3.56-3.46 (m, 10H), 3.56-3.44 (m, 1H), 2.94-2.83 (m, 1H), 2.63-2.56 (m, 1H), 2.57-2.54 (m, 1H), 2.07-1.99 (m, 1H). LC-MS (ESI$^+$) m/z 545.2 (M+H)$^+$.

Step 2—4-[2-[2-[2-[2-(4-Aminopyrazol-1-yl)ethoxy]ethoxy]ethoxy]ethylamino]-2-(2,6-dioxo-3-piperidyl)isoindoline-1,3-dione To a solution of 2-(2,6-dioxo-3-piperidyl)-4-[2-[2-[2-[2-(4-nitropyrazol-1-yl)ethoxy]ethoxy]ethoxy]ethylamino]isoindoline-1,3-dione (400 mg, 735 umol) in THF (40 mL) was added PtO$_2$.H$_2$O (50 mg, 220 umol) under N$_2$. The suspension was degassed under vacuum and purged with H$_2$ several times. The mixture was stirred under H$_2$ (15 psi) at 20° C. for 12 hours. On completion, the reaction mixture was filtered and concentrated in vacuo to give the title compound (370 mg, 98% yield) as yellow oil. $^1$H NMR (400 MHz, DMSO-d$_6$) δ 11.10 (s, 1H), 7.63-7.53 (m, 1H), 7.15 (d, J=8.8 Hz, 1H), 7.07-7.01 (m, 2H), 6.89 (s, 1H), 6.60 (t, J=5.8 Hz, 1H), 5.06 (dd, J=5.2, 12.8 Hz, 1H), 4.03 (t, J=5.6 Hz, 2H), 3.66 (t, J=5.6 Hz, 2H), 3.57-3.54 (m, 2H), 3.54-3.45 (m, 10H), 2.96-2.82 (m, 1H), 2.63-2.60 (m, 1H), 2.59-2.57 (m, 1H), 2.05-1.98 (m, 1H).

2-[2-[2-[2-(2-Tert-butoxy-2-oxo-ethoxy)ethoxy]ethoxy]ethoxy]acetic acid (Intermediate UM)

Step 1-Ethyl 2-[2-[2-[2-(2-tert-butoxy-2-oxo-ethoxy)ethoxy]ethoxy]ethoxy]acetate To a solution of ethyl 2-[2-[2-(2-hydroxyethoxy)ethoxy]ethoxy]acetate (150 mg, 635 umol, synthesized via Step 1 of Intermediate BI) and diacetoxyrhodium (6.00 mg, 13.6 umol) in anhydrous DCM (4 mL) was added a solution of tert-butyl 2-diazoacetate (271 mg, 1.91 mmol, CAS #35059-50-8) in DCM (4 mL) dropwise at 0-10° C. The mixture was stirred at 25° C. for 16 hours under N$_2$. On completion, the reaction was quenched with HOAc (0.1 mL). The mixture was stirred at 25° C. for 15 minutes. The mixture was then concentrated in vacuo. The residue was purified over column chromatography on silica gel (PE:EA=5:1-3:1) to give the title compound (130 mg, 58% yield) as light green oil. $^1$H NMR (400 MHz, CDCl$_3$) δ 4.22 (q, J=7.2 Hz, 2H), 4.16 (s, 2H), 4.03 (s, 2H), 3.74-3.68 (m, 12H), 1.48 (s, 9H), 1.29 (t, J=7.2 Hz, 3H).

Step 2—2-[2-[2-[2-(2-Tert-butoxy-2-oxo-ethoxy)ethoxy]ethoxy]ethoxy]acetic acid To a solution of ethyl 2-[2-[2-[2-(2-tert-butoxy-2-oxo-ethoxy)ethoxy]ethoxy]ethoxy]acetate (130 mg, 371 umol) in THF (3 mL) was added a solution of lithium hydroxide hydrate (17.0 mg, 405 umol) in H$_2$O (1 mL) at 25° C. The mixture was stirred at 25° C. for 16 hours. On completion, the mixture was diluted with water (20 mL), acidified to pH=5 with 1.0 M aq. HCl, then extracted with EA (3×10 mL). The combined organic layer was washed with brine (10 mL), dried over Na$_2$SO$_4$, filtered and concentrated in vacuo to give the title compound (110 mg, 92% yield) as light green oil. $^1$H NMR (400 MHz, CDCl$_3$) δ 4.17 (s, 2H), 4.03 (s, 2H), 3.77-3.70 (m, 12H), 1.48 (s, 9H).

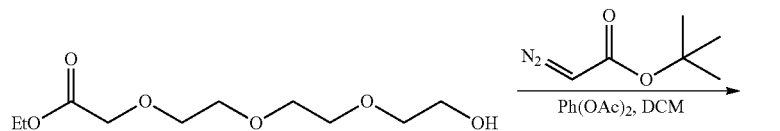

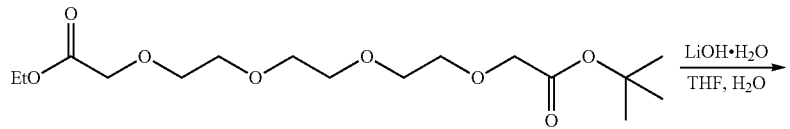

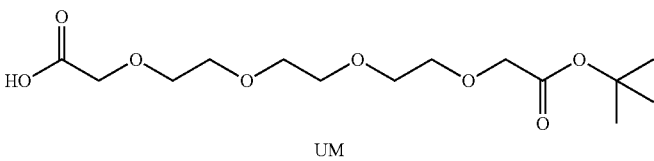

UM

2-[2-[2-[2-[2-[[(1S)-1-[(2S,4R)-4-Hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethoxy]ethoxy]acetic acid
(Intermediate UN)

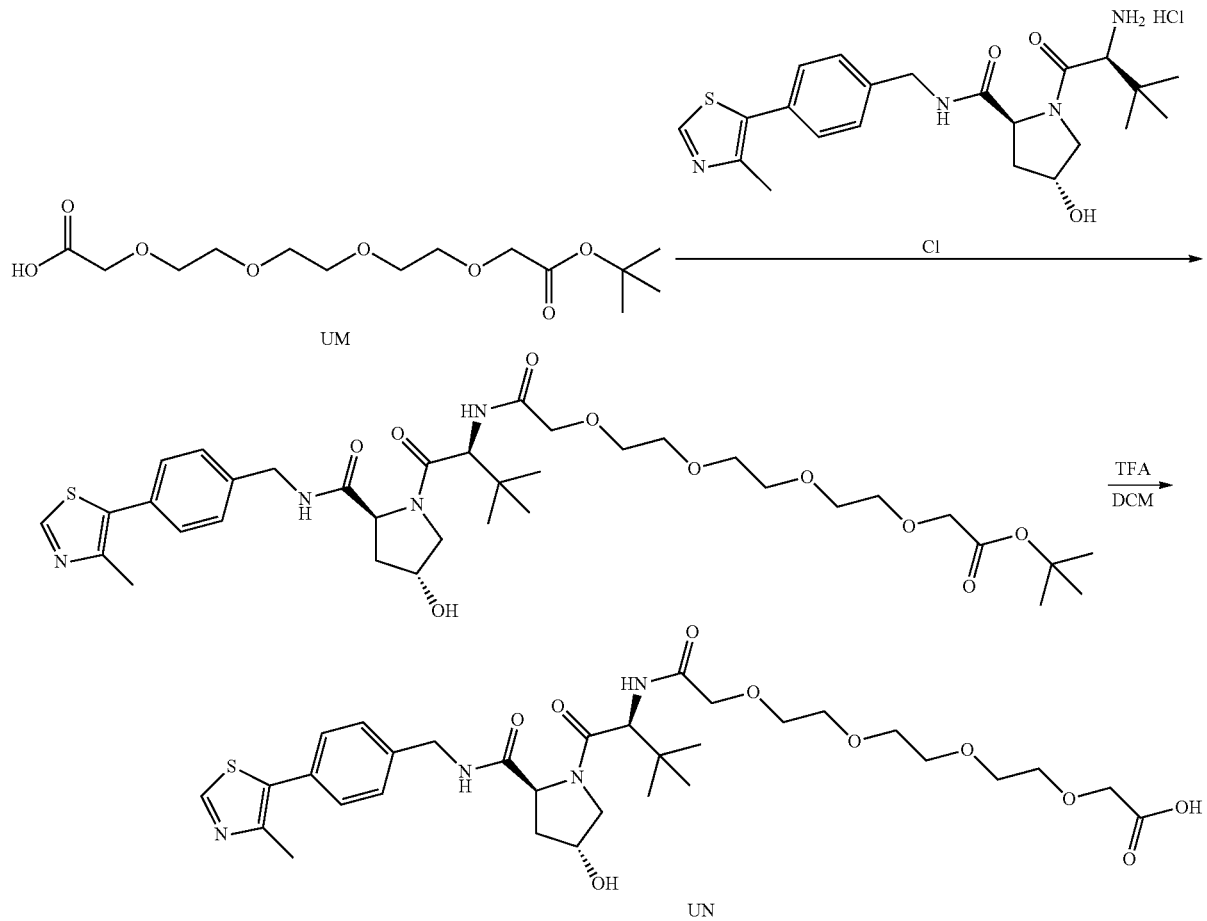

Step 1—Tert-butyl 2-[2-[2-[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethoxy]ethoxy]acetate A mixture of (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide (180 mg, HCl, Intermediate CI), 2-[2-[2-[2-(2-tert-butoxy-2-oxo-ethoxy)ethoxy]ethoxy]ethoxy]acetic acid (100 mg, 310 umol, Intermediate UM), HATU (155 mg, 408 umol) and DIPEA (121 mg, 936 umol) in DMF (5 mL) was stirred at 25° C. for 2 hours. On completion, the reaction mixture was diluted with water (50 mL), then extracted with EA (3×30 mL). The combined organic layer was washed with brine (20 mL), dried over Na$_2$SO$_4$, filtered and concentrated in vacuo. The residue was purified over column chromatography on silica gel (DCM: MeOH=50:1-20:1) to give the title compound (130 mg, 48% yield, 84% purity) as light yellow gum. LC-MS (ESI$^+$) m/z 735.3 (M+H)$^+$, 757.3 (M+Na)$^+$.

Step 2—2-[2-[2-[2-[2-[[(1S)-1-[(2S,4R)-4-Hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethoxy]ethoxy]acetic acid To a solution of tert-butyl 2-[2-[2-[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethoxy]ethoxy]acetate (110 mg, 125 umol) in DCM (4 mL) was added TFA (2 mL) at 25° C. The mixture was stirred at 25° C. for 3 hours. On completion, the mixture was concentrated in vacuo to give the title compound (140 mg, quant. crude yield, TFA) as light yellow gum. LC-MS (ESI$^+$) m/z 679.4 (M+H)$^+$.

2-[2-[2-(2-Tert-butoxy-2-oxo-ethoxy)ethoxy]ethoxy]acetic acid (Intermediate UQ)

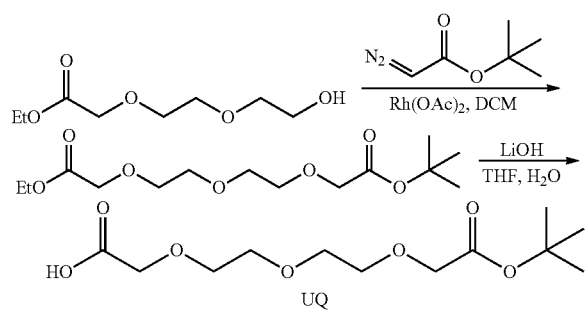

Step 1—Ethyl 2-[2-[2-(2-tert-butoxy-2-oxo-ethoxy)ethoxy]ethoxy]acetate

To a stirring mixture of ethyl 2-[2-(2-hydroxyethoxy)ethoxy]acetate (0.80 g, 4.16 mmol, synthesized via Step 1 of Intermediate BM) and diacetoxyrhodium (33.6 mg, 76.0 umol) in DCM (10 mL) was added a solution of tert-butyl 2-diazoacetate (1.78 g, 12.49 mmol, CAS #35059-50-8) in DCM (10 mL) drop-wise under ice-cooling bath (0° C.). After the addition, the resulting mixture was stirred at 20° C. for 16 hours. Diacetoxyrhodium (33.6 mg, 76.02 umol) and tert-butyl 2-diazoacetate (1.78 g, 12.49 mmol) were supplied subsequently, and the resulting mixture was stirred at 20° C. for another 4 hours. On completion, the mixture was quenched with AcOH (1.2 mL) and concentration in vacuo. The residue was purified by column chromatography (SiO$_2$, Petroleum ether/Ethyl acetate=5/1 to 3/1) to give the title compound (1.11 g, 87% yield) as blue oil. $^1$H NMR (400 MHz, CDCl$_3$) δ 4.28 (q, J=7.2 Hz, 2H), 4.02 (s, 2H), 4.15 (s, 2H), 3.73-3.70 (m, 8H), 1.48 (m, 9H), 1.28 (t, J=7.2 Hz, 3H).

Step 2—2-[2-[2-(2-Tert-butoxy-2-oxo-ethoxy)ethoxy]ethoxy]acetic acid

To a solution of ethyl 2-[2-[2-(2-tert-butoxy-2-oxo-ethoxy)ethoxy]ethoxy]acetate (1 g, 3.26 mmol) in THF (40 mL) was added a solution of LiOH.H$_2$O (170 mg, 4.05 mmol) in H$_2$O (20 mL). The mixture was stirred at 20° C. for 16 hours. On completion, the mixture was diluted with H$_2$O (30 mL), adjusted to pH=4-5 with 1M aq. HCl, extracted with EA (2×50 mL). The organic phases were combined and dried over Na$_2$SO$_4$, filtered and concentrated in vacuo to give the title compound (800 mg, 88% yield) as yellowish oil.

2-[2-[2-[2-[[(1S)-1-[(2S,4R)-4-Hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethoxy]acetic acid (Intermediate UR)

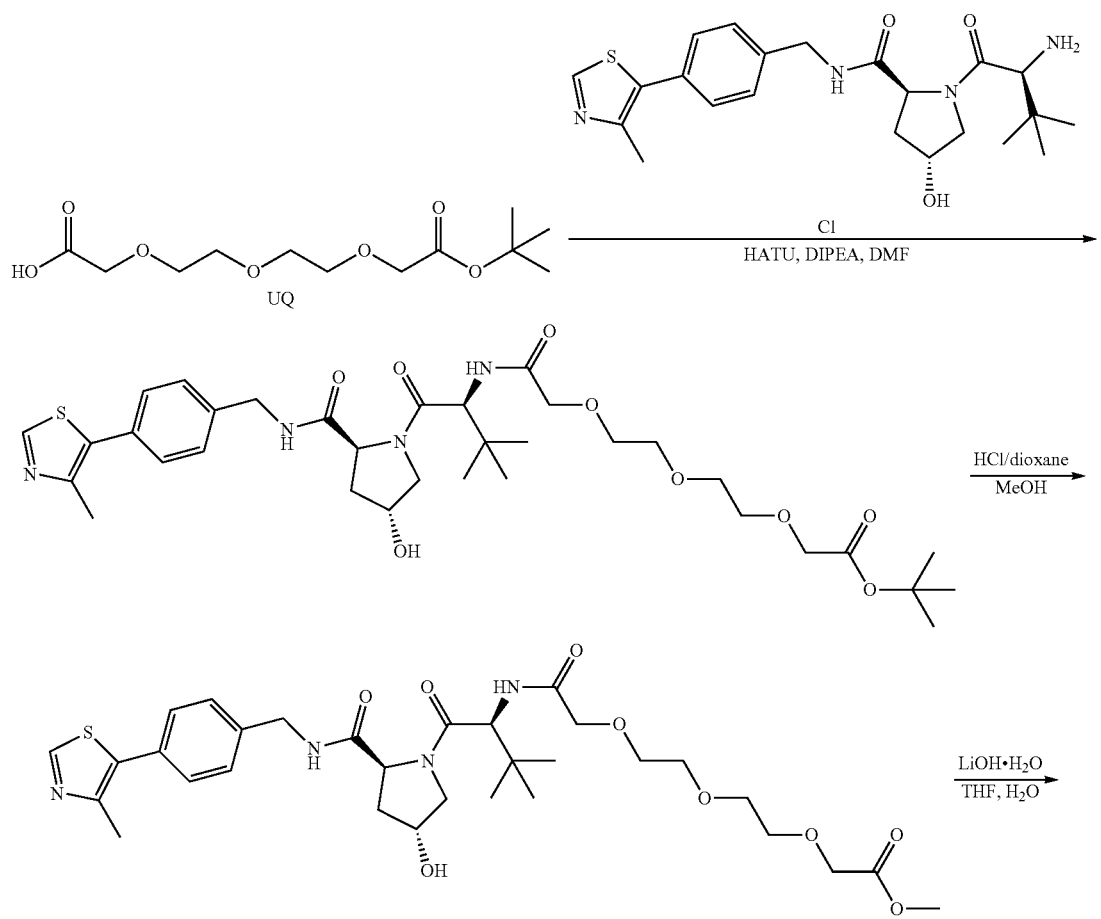

-continued

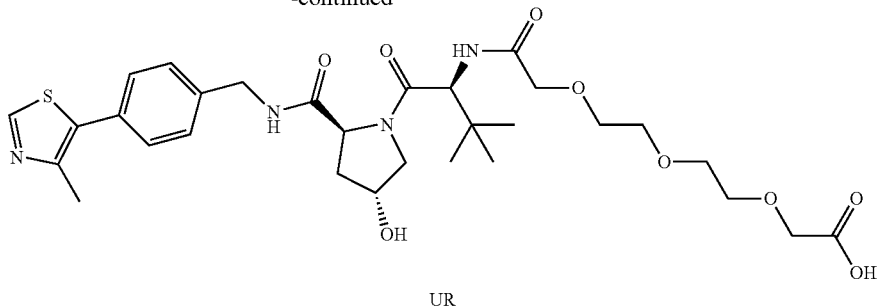

UR

Step 1—Tert-butyl 2-[2-[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethoxy]acetate To a mixture of 2-[2-[2-(2-tert-butoxy-2-oxo-ethoxy)ethoxy]ethoxy]acetic acid (200 mg, 718 umol, Intermediate UQ) and HATU (327 mg, 862 umol) in DMF (20 mL) was added DIPEA (278 mg, 2.16 umol, 375 uL) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide (335 mg, 718 umol, HCl, Intermediate CI) subsequently, then the resulting mixture was stirred at 20° C. for 16 hours. On completion, the mixture was diluted with $H_2O$ (20 mL), then extracted with EA (2×50 mL), the organic phase was concentrated in vacuo. The residue was purified by column chromatography ($SiO_2$, PE/EA=1/1, EA/MeOH=40/1 to 10/1) to give the title compound (400 mg, 70% yield) as yellowish solid. LC-MS ($ESI^+$) m/z 691.3 $(M+H)^+$.

Step 2—(S)-Methyl 13-((2S,4R)-4-hydroxy-2-((4-(4-methylthiazol-5-yl)benzyl)carbamoyl) pyrrolidine-1-carbonyl)-14,14-dimethyl-11-oxo-3,6,9-trioxa-12-azapentadecan-1-oate To a solution of tert-butyl 2-[2-[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethoxy]acetate (100 mg, 144 umol) in MeOH (5 mL) was added HCl/dioxane (4 M, 2 mL). The mixture was stirred at 20° C. for 16 hours. On completion, the reaction mixture was concentrated in vacuo to give the title compound (150 mg, quant. crude yield) as colorless oil. LC-MS ($ESI^+$) m/z 649.3 $(M+H)^+$.

Step 3—2-[2-[2-[2-[[(1S)-1-[(2S,4R)-4-Hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethoxy]acetic acid To a solution of (S)-methyl 13-((2S,4R)-4-hydroxy-2-((4-(4-methylthiazol-5-yl)benzyl)carbamoyl) pyrrolidine-1-carbonyl)-14,14-dimethyl-11-oxo-3,6,9-trioxa-12-azapentadecan-1-oate (150 mg) in THF (10 mL) was added a solution of $LiOH·H_2O$ (200 mg, 4.77 mmol) in $H_2O$ (5 mL). The mixture was stirred at 20° C. for 20 mins. On completion, the mixture was concentrated in vacuo to remove THF, then diluted with $H_2O$ (20 mL) and the pH was adjusted to 5 with 1.0 M aq. HCl, extracted with EA (2×40 mL). The organic phases were concentrated in vacuo to give the title compound (80 mg, 96%) as yellowish oil. LC-MS (ESI+) m/z 635.4 $(M+H)^+$.

Tert-butyl N-[2-[2-[2-(4-aminopyrazol-1-yl)ethoxy]ethoxy]ethyl]carbamate (Intermediate US)

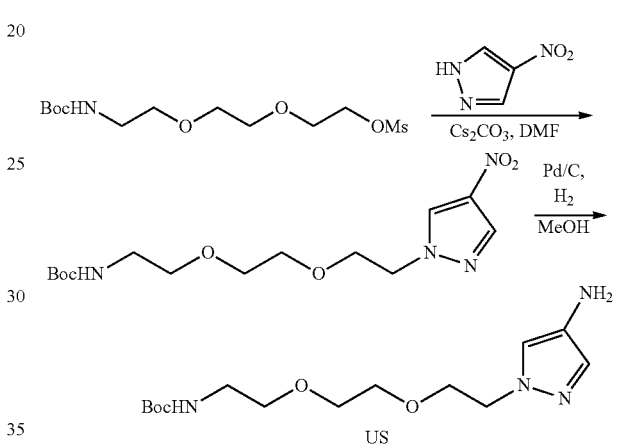

Step 1-Tert-butyl N-[2-[2-[2-(4-nitropyrazol-1-yl)ethoxy]ethoxy]ethyl]carbamate To a solution of 2-[2-[2-(tert-butoxycarbonylamino)ethoxy]ethoxy]ethyl methanesulfonate (2.08 g, 6.37 mmol, synthesized via Step 1 of Intermediate AM) and 4-nitro-1H-pyrazole (0.600 g, 5.31 mmol, CAS #2075-46-9) in DMF (40 mL) was added $Cs_2CO_3$ (3.46 g, 10.6 mmol). The mixture was stirred at 130° C. for 2 hours. On completion, after cooling to 25° C., the mixture was filtered, and the filtrate was concentrated in vacuo. The residue was purified by reverse phase (0.1% FA condition) to give the title compound (1.50 g, 82% yield) as yellow oil. $^1$H NMR (400 MHz, $CDCl_3$) δ 8.29 (s, 1H), 8.00 (s, 1H), 4.90 (s, 1H), 4.28 (t, J=4.8 Hz, 2H), 3.84-3.77 (m, 2H), 3.56-3.50 (m, 4H), 3.46 (t, J=5.2 Hz, 2H), 3.30-3.21 (m, 2H), 1.37 (s, 9H). LC-MS ($ESI^+$) m/z 367.2 $(M+Na)^+$.

Step 2—Tert-butyl N-[2-[2-[2-(4-aminopyrazol-1-yl)ethoxy]ethoxy]ethyl]carbamate To a solution of tert-butyl N-[2-[2-[2-(4-nitropyrazol-1-yl)ethoxy]ethoxy]ethyl]carbamate (500 mg, 1.45 mmol) in MeOH (10 mL) was added Pd/C (220 mg, 10 wt %). The mixture was stirred at 20° C. for 12 hours under $H_2$ (15 psi) atmosphere. On completion, the reaction mixture was filtered and concentrated in vacuo to give the title compound (400 mg, 87.6% yield) as red oil. LC-MS ($ESI^+$) m/z 315.2 $(M+H)^+$.

N5-[1-[2-[2-(2-aminoethoxy)ethoxy]ethyl]pyrazol-4-yl]-1-methyl-N7-(4-morpholinocyclohexyl)pyrazolo[4,3-d]pyrimidine-5,7-diamine (Intermediate UT)

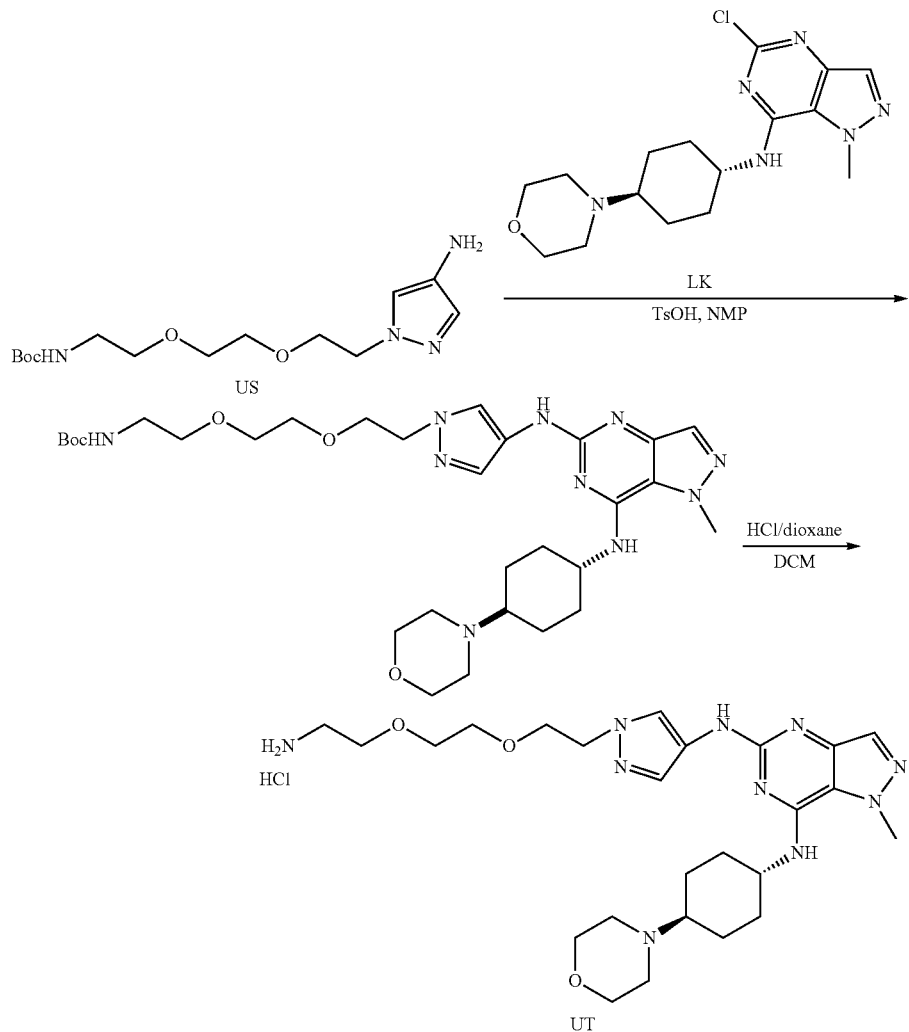

Step 1—Tert-butyl N-[2-[2-[2-[4-[[1-methyl-7-[(4-morpholinocyclohexyl)amino]pyrazolo[4,3-d]pyrimidin-5-yl]amino]pyrazol-1-yl]ethoxy]ethoxy]ethyl]carbamate Tert-butyl N-[2-[2-[2-(4-aminopyrazol-1-yl)ethoxy]ethoxy]ethyl]carbamate (300 mg, 954 umol, Intermediate US), 5-chloro-1-methyl-N-(4-morpholinocyclohexyl)pyrazolo[4,3-d]pyrimidin-7-amine (223 mg, 636 umol, Intermediate LK) and TsOH (21.9 mg, 127 umol) were taken up into a microwave tube in NMP (10 mL). The sealed tube was heated at 150° C. for 2 hours under microwave. On completion, after cooled to 25° C., the reaction mixture was diluted with water (50 mL) and extracted with DCM (2×80 mL). The combined organic layer was concentrated in vacuo. The residue was purified by reverse phase (0.1% FA condition) to give the title compound (100 mg, 25% yield) as a white solid. LC-MS (ESI$^+$) m/z 629.2 (M+H)$^+$.

Step 2—N5-[1-[2-[2-(2-aminoethoxy)ethoxy]ethyl]pyrazol-4-yl]-1-methyl-N7-(4-morpholinocyclohexyl)pyrazolo[4,3-d]pyrimidine-5,7-diamine To a solution of tert-butyl N-[2-[2-[2-[4-[[1-methyl-7-[(4-morpholinocyclohexyl)amino]pyrazolo[4,3-d]pyrimidin-5-yl]amino]pyrazol-1-yl]ethoxy]ethoxy]ethyl]carbamate (80.0 mg, 127 umol) in DCM (2 mL) was added HCl/dioxane (4 M, 1 mL). The reaction mixture was stirred at 25° C. for 14 hours. On completion, the reaction mixture was concentrated in vacuo to give the title compound (70 mg, 97.3%, HCl) as a white solid. LC-MS (ESI$^+$) m/z 529.5 (M+H)$^+$.

1915

(S)-2-((S)-2-(((benzyloxy)carbonyl)(methyl)amino)propanamido)-2-cyclohexylacetic acid (Intermediate UU)

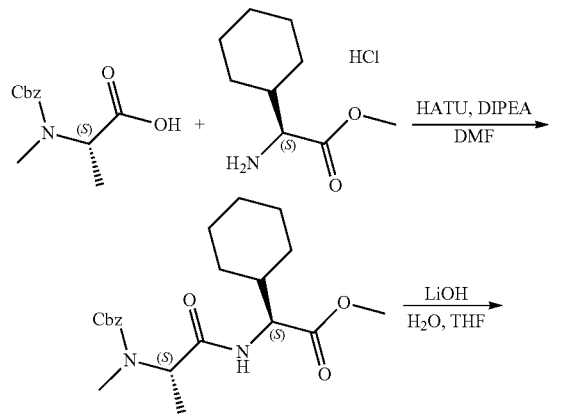

Step 1—methyl (S)-2-((S)-2-(((benzyloxy)carbonyl)(methyl)amino)propanamido)-2-cyclohexylacetate To a solution of N-((benzyloxy)carbonyl)-N-methyl-L-alanine (13.04 g, 55 mmol) and methyl (S)-2-amino-2-cyclohexylacetate hydrochloride (10.4 g, 50 mmol) in DMF (100 mL) was added HATU (24.72 g, 65 mmol) and DIPEA (19.35 g, 150 mmol). The reaction mixture was stirred at room temperature for 8 h. Water (300 mL) was then added, and the mixture was extracted with EtOAc (3×100 mL). The combined organic layers were washed with brine (60 mL), dried over anhydrous $Na_2SO_4$. The solid was filtered and the filtrate was concentrated under reduced pressure, the resulting residue was purified by column chromatography on silica gel to give the title compound as an oil (18 g, 96% yield). $^1$H NMR (400 MHz, CDCl3) δ 7.37-7.27 (m, 5H), 5.19 (s, 2H), 4.81 (br s, 1H), 4.49 (dd, J=10.8, 5.3 Hz, 1H), 3.72 (s, 3H), 2.88 (s, 3H), 1.76-1.50 (m, 6H), 1.36 (d, J=7.1 Hz, 3H), 1.27-1.13 (m, 2H), 1.08-0.90 (m, 3H).

1916

Step 2—(S)-2-((S)-2-(((benzyloxy)carbonyl)(methyl)amino)propanamido)-2-cyclohexylacetic acid To a solution of methyl (S)-2-((S)-2-(((benzyloxy)carbonyl)(methyl)amino)propanamido)-2-cyclohexylacetate (18.0 g, 46.15 mmol) in THF (60 mL) and H2O (12 mL) was added LiOH (1.44 g, 60 mmol) at 0° C. The reaction mixture was stirred at 0° C. for 1 h then at rt for 4 h. THF was removed under reduced pressure, then the mixture was adjusted with critic acid to pH=2-3, and the mixture was extracted with EtOAc (3×200 mL). The combined organic layers were washed with brine (60 mL), dried over anhydrous $Na_2SO_4$. The solid was filtered and the filtrate was concentrated under reduced pressure to give the title compound (14 g, 81% yield). $^1$H NMR (400 MHz, DMSO-$d_6$) δ 12.55 (s, 1H), 7.39-7.28 (m, 5H), 5.07 (d, J=9.3 Hz, 2H), 4.69 (br s, 1H), 4.10-4.07 (m, 1H), 2.85 (s, 3H), 1.65-1.56 (m, 6H), 1.35-1.28 (m, 3H), 1.19-1.08 (m, 5H).

2,2-dimethyl-4-oxo-3,8,11-trioxa-5-azatridecan-13-yl 4-methylbenzenesulfonate (Intermediate UV)

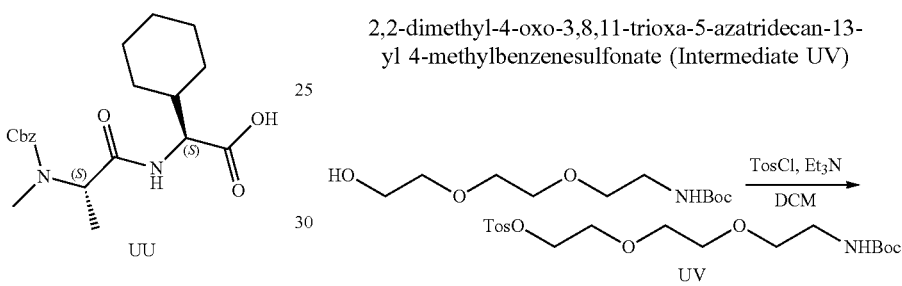

To a solution of tert-butyl (2-(2-(2-hydroxyethoxy)ethoxy)ethyl)carbamate (11 g, 44.12 mmol, CAS #139115-92-7) in DCM (100 mL) was added $Et_3N$ (8.91 g, 88.24 mmol), then TosCl (16.82 g, 88.24 mmol) was added portions at room temperature. The reaction mixture was stirred at room temperature overnight. The reaction mixture was concentrated under reduced pressure, the resulting residue was purified by column chromatography on silica gel to give the product 2,2-dimethyl-4-oxo-3,8,11-trioxa-5-azatridecan-13-yl 4-methylbenzenesulfonate as an oil (17 g, yield 96%). $^1$H NMR (400 MHz, CDCl$_3$) δ 7.81-7.79 (m, 2H), 7.34 (d, J=8.0 Hz, 2H), 4.90 (br s, 1H), 4.19-4.16 (m, 2H), 3.72-3.68 (m, 2H), 3.61-3.57 (m, 2H), 3.56-3.53 (m, 2H), 3.50 (t, J=5.2 Hz, 2H), 3.29 (t, J=5.1 Hz, 2H), 2.45 (s, 3H), 1.42 (s, 9H).

3-[4-[3-[2-[2-[2-(2-Aminoethoxy)ethoxy]ethoxy]ethoxy]propyl]-3-methyl-2-oxo-benzimidazol-1-yl]piperidine-2,6-dione (Intermediate UX)

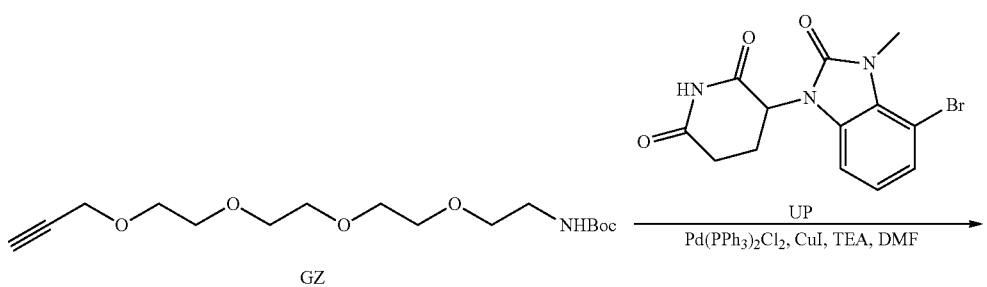

-continued

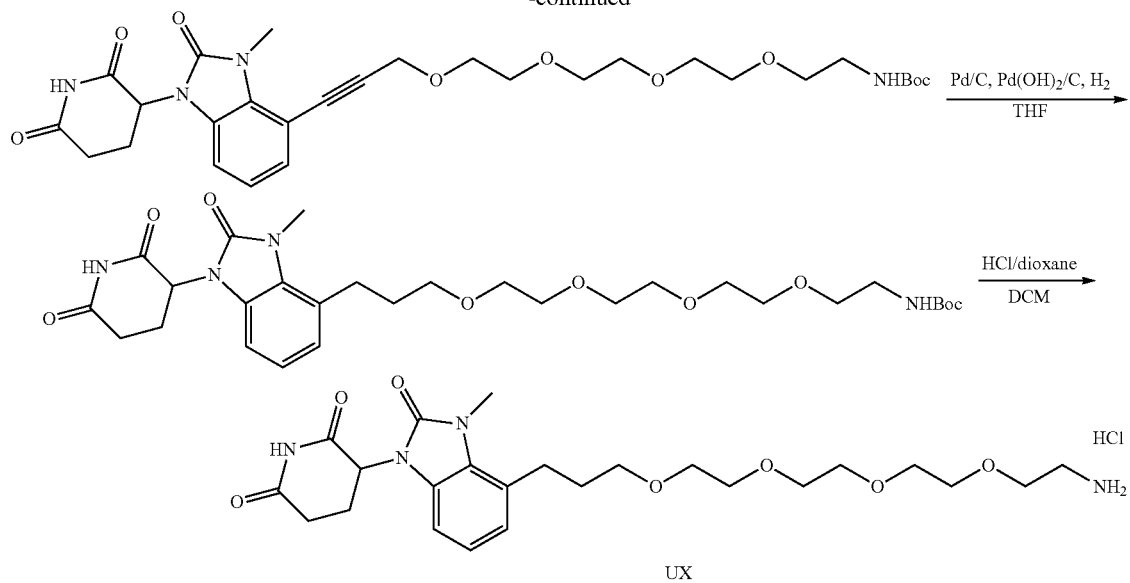

UX

Step 1—Tert-butyl N-[2-[2-[2-[2-[3-[1-(2,6-dioxo-3-piperidyl)-3-methyl-2-oxo-benzimidazol-4-yl]prop-2-ynoxy]ethoxy]ethoxy]ethoxy]ethyl]carbamate To a mixture of tert-butyl N-[2-[2-[2-(2-prop-2-ynoxy-ethoxy)ethoxy]ethoxy]ethyl]carbamate (0.500 g, 1.51 mmol, Intermediate GZ), 3-(4-bromo-3-methyl-2-oxo-benzimidazol-1-yl)piperidine-2,6-dione (170 mg, 502 umol, Intermediate HP), CuI (47.8 mg, 251 umol) and Pd(PPh$_3$)$_2$Cl$_2$ (176 mg, 251 umol) in DMF (10 mL) was added TEA (916 mg, 9.05 mmol, 1.26 mL) in a glove box. Then the resulting mixture was stirred at 80° C. for 2 hours. On completion, the mixture was diluted with water (90 mL), then extracted with EA (2×100 mL). The combined organic layers was dried over Na$_2$SO$_4$, filtered and concentrated in vacuo. The residue was purified by column chromatography to give the title compound (131 mg, 30% yield) as brown liquid. LC-MS (ESI$^+$) m/z 611.1 (M+Na)$^+$.

Step 2—Tert-butyl N-[2-[2-[2-[2-[3-[1-(2,6-dioxo-3-piperidyl)-3-methyl-2-oxo-benzimidazol-4-yl]propoxy]ethoxy]ethoxy]ethoxy]ethyl]carbamate To a mixture tert-butyl N-[2-[2-[2-[2-[3-[1-(2,6-dioxo-3-piperidyl)-3-methyl-2-oxo-benzimidazol-4-yl]prop-2-ynoxy]ethoxy]ethoxy]ethoxy]ethyl]carbamate (110 mg) in THF (15 mL) was added Pd/C (0.04 g, 10 wt %) and Pd(OH)$_2$/C (0.04 g, 284 umol). The reaction mixture was stirred at 20° C. for 40 hours under H$_2$ (15 psi). On completion, the reaction mixture was filtered through celite and concentrated in vacuo. The residue was purified by column chromatography (SiO$_2$, EA) to give the title compound (100 mg, 59% yield) as brown liquid. LC-MS (ESI$^+$) m/z 615.1 (M+Na)$^+$.

Step 3—3-[4-[3-[2-[2-[2-(2-Aminoethoxy)ethoxy]ethoxy]ethoxy]propyl]-3-methyl-2-oxo-benzimidazol-1-yl]piperidine-2,6-dione To a solution of tert-butyl N-[2-[2-[2-[2-[3-[1-(2,6-dioxo-3-piperidyl)-3-methyl-2-oxo-benzimidazol-4-yl]propoxy]ethoxy]ethoxy]ethoxy]ethyl]carbamate (0.10 g, 168 umol)

in DCM (10 mL) was added HCl/dioxane (4 M, 2 mL). The reaction mixture was stirred at 20° C. for 16 hours. On completion, the mixture was concentrated in vacuo. The residue was purified by reverse flash (0.1% FA condition) to give the title compound (25.0 mg, 30% yield) as gray solid. LC-MS (ESI$^+$) m/z 493.3 (M+H)$^+$.

2-[2-[2-(2-Prop-2-ynoxyethoxy)ethoxy]ethoxy]ethanol (Intermediate UY)

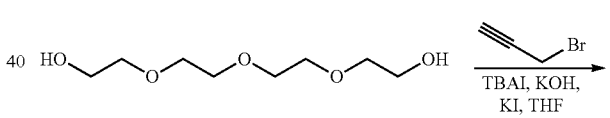

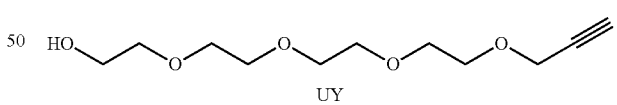

UY

To a mixture of 2-[2-[2-(2-hydroxyethoxy)ethoxy]ethoxy]ethanol (20.0 g, 102 mmol, 17.7 mL, CAS #25322-68-3) and 3-bromoprop-1-yne (14.7 g, 123 mmol) in THF (200 mL) was added TBAI (2.28 g, 6.18 mmol), KI (2.56 g, 15.45 mmol) and KOH (5.78 g, 102 mmol). The mixture was stirred at 25° C. for 12 hours. On completion, the reaction mixture was filtered and concentrated in vacuo. The residue was purified by column chromatography (PE:EA=5/1 to 0/1) to give the title compound (16.0 g, 67% yield) as a light yellow oil. $^1$H NMR (400 MHz, CDCl$_3$) δ 4.18 (d, J=2.4 Hz, 2H), 3.70 (d, J=4.8 Hz, 2H), 3.67 (d, J=3.2 Hz, 2H), 3.69-3.61 (m, 10H), 3.60-3.57 (m, 2H), 2.73 (s, 1H), 2.42 (t, J=2.4 Hz, 1H).

2-[2-[2-[2-[(4-Methoxyphenyl)methyl-methyl-amino]ethoxy]ethoxy]ethoxy]ethanamine (Intermediate UZ)

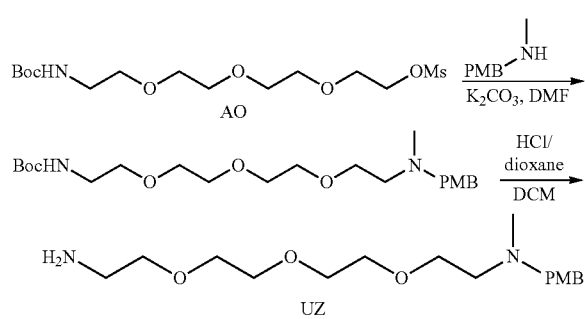

Step 1—Tert-butyl N-[2-[2-[2-[2-[(4-methoxyphenyl)methyl-methyl-amino]ethoxy]ethoxy]ethoxy]ethyl]carbamate To a solution of 2-[2-[2-[2-(tert-butoxycarbonylamino)ethoxy]ethoxy]ethoxy]ethyl methanesulfonate (1.65 g, 4.44 mmol, Intermediate AO), 1-(4-methoxyphenyl)-N-methyl-methanamine (671 mg, 4.44 mmol) in DMF (20.0 mL) was added K₂CO₃ (1.23 g, 8.88 mmol). The mixture was stirred at 20° C. for 15 hours. On completion, the mixture was diluted with H₂O (60 mL), then extracted with EA (3×30 mL). The organic layers were washed with brine (3×30 mL) and dried with anhydrous Na₂SO₄, filtered and concentrated in vacuo. The mixture was purified by reverse phase: (0.1% FA) to give the title compound (700 mg, 36% yield) as yellow oil. 1H NMR (400 MHz, CDCl₃) δ 8.52 (s, 1H), 7.33 (d, J=8.4 Hz, 2H), 6.90 (d, J=8.8 Hz, 2H), 3.87 (s, 2H), 3.83 (s, 3H), 3.81-3.75 (m, 2H), 3.68-3.61 (m, 8H), 3.56-3.48 (m, 2H), 3.38-3.25 (m, 2H), 2.96-2.84 (m, 2H), 2.48 (s, 3H), 1.46 (s, 9H).

Step 2—2-[2-[2-[2-[(4-Methoxyphenyl)methyl-methyl-amino]ethoxy]ethoxy]ethoxy]ethanamine To a solution of tert-butyl N-[2-[2-[2-[2-[(4-methoxyphenyl)methyl-methyl-amino]ethoxy]ethoxy]ethoxy]ethyl]carbamate (700 mg, 1.64 mmol) in DCM (10.0 mL) was added HCl/dioxane (4.00 M, 10.0 mL). The mixture was stirred at 15° C. for 0.5 hour. On completion, the mixture was concentrated in vacuo to give the title compound (590 mg, 90% yield, HCl salt) as yellow oil. LC-MS (ESI⁺) m/z 327.3 (M+H)⁺.

2-(2,6-Dioxo-3-piperidyl)-4-[2-[2-[2-[2-(methylamino)ethoxy]ethoxy]ethoxy]ethylamino]isoindoline-1,3-dione (Intermediate VA)

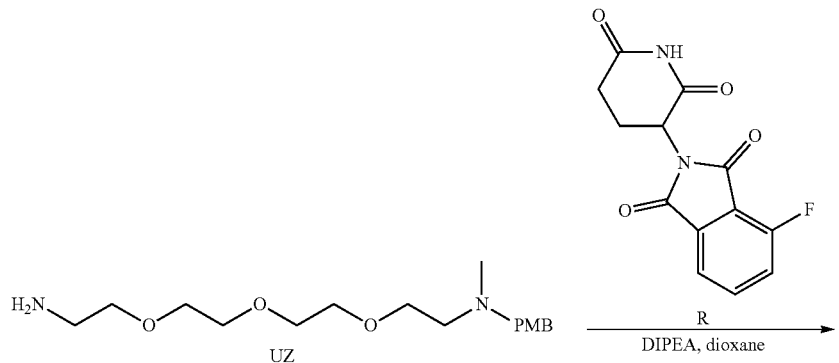

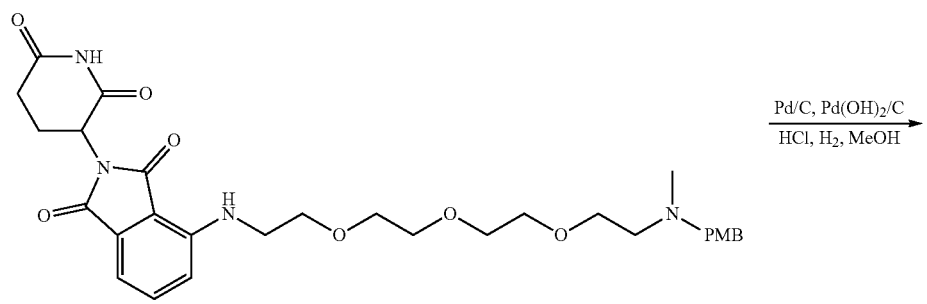

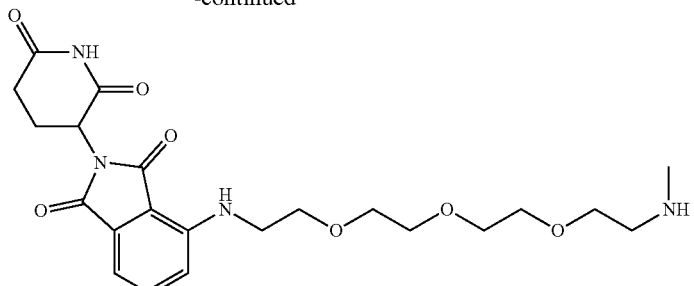

VA

Step 1—2-(2,6-Dioxo-3-piperidyl)-4-[2-[2-[2-[2-[(4-methoxyphenyl)methyl-methylamino]ethoxy]ethoxy]ethoxy]ethylamino]isoindoline-1,3-dione To a solution of 2-[2-[2-[2-[(4-methoxyphenyl)methyl-methyl-amino]ethoxy]ethoxy]ethoxy]ethanamine (590 mg, 1.63 mmol, HCl, Intermediate UZ), 2-(2,6-dioxo-3-piperidyl)-4-fluoro-isoindoline-1,3-dione (494 mg, 1.79 mmol, Intermediate R) in dioxane (10.0 mL) was added DIPEA (2.10 g, 16.2 mmol). The mixture was stirred at 115° C. for 16 hours. On completion, the mixture was concentrated in vacuo. The mixture was purified by reverse phase: (0.1% FA) to give the title compound (500 mg, 52% yield) as yellow solid. LC-MS (ESI+) m/z 583.3 (M+H)+.

Step 2—2-(2,6-Dioxo-3-piperidyl)-4-[2-[2-[2-[2-(methylamino)ethoxy]ethoxy]ethoxy]ethylamino]isoindoline-1,3-dione To a solution of 2-(2,6-dioxo-3-piperidyl)-4-[2-[2-[2-[2-[(4-methoxyphenyl)methyl-methylamino]ethoxy]ethoxy]ethoxy]ethylamino]isoindoline-1,3-dione (400 mg, 686 umol) in MeOH (10.0 mL) was added Pd/C (200 mg) and Pd(OH)2/C (200 mg) and HCl (1.00 M, 686 uL). The mixture was stirred at 15° C. for 1 hour under H2 (15 psi). On completion, the mixture was filtered and the filtrate was concentrated in vacuo. The mixture was purified by reverse phase (0.1% HCl) to give the title compound (160 mg, 50% yield) as yellow solid. LC-MS (ESI+) m/z 463.3 (M+H)+.

3-[4-[3-[2-[2-[2-(2-Hydroxyethoxy)ethoxy]ethoxy]ethoxy]propyl]-3-methyl-2-oxo-benzimidazol-1-yl]piperidine-2,6-dione (Intermediate VB)

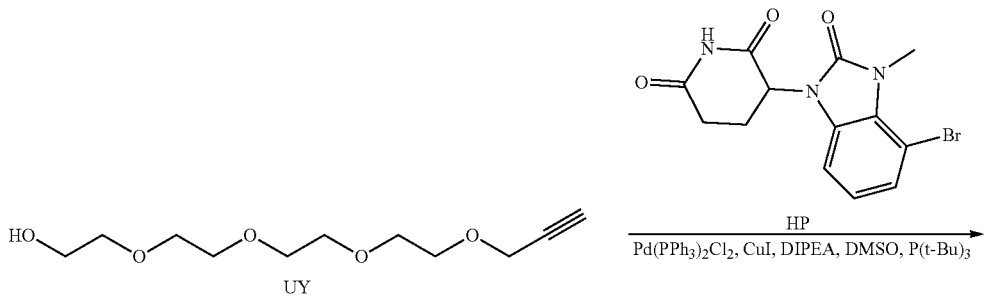

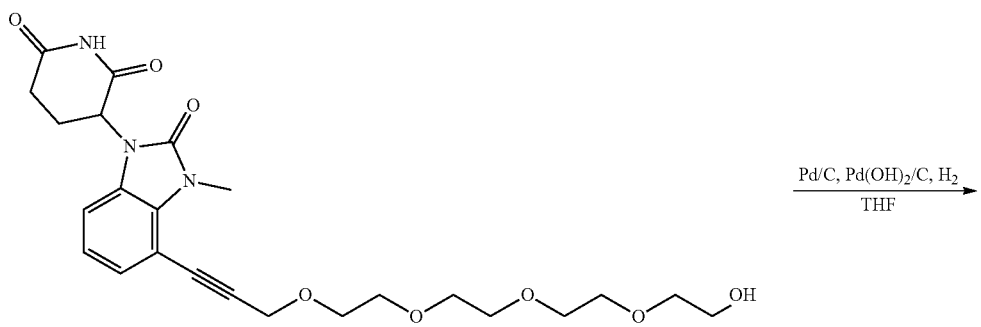

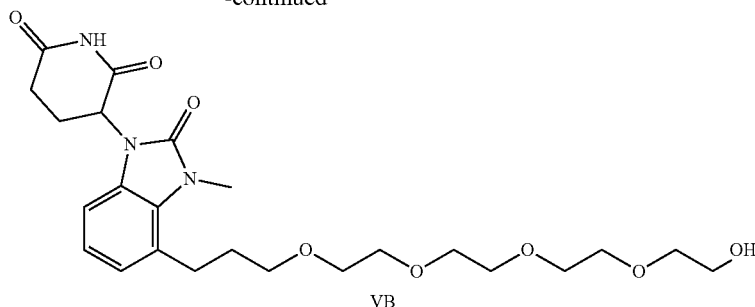

VB

Step 1—3-[4-[3-[2-[2-[2-(2-Hydroxyethoxy)ethoxy]ethoxy]ethoxy]prop-1-ynyl]-3-methyl-2-oxo-benzimidazol-1-yl]piperidine-2,6-dione To a mixture of 2-[2-[2-(2-prop-2-ynoxyethoxy)ethoxy]ethoxy]ethanol (1.03 g, 4.44 mmol, Intermediate UY) and 3-(4-bromo-3-methyl-2-oxo-benzimidazol-1-yl)piperidine-2,6-dione (0.50 g, 1.48 mmol, Intermediate HP) in DMSO (20 mL) was added CuI (56.3 mg, 295 umol), P(t-Bu)$_3$ (2.30 g, 1.48 mmol, 2.67 mL, 13% solution of toluene), DIPEA (955 mg, 7.39 mmol) and Pd(PPh$_3$)$_2$Cl$_2$ (103 mg, 147 umol). The reaction mixture was stirred at 80° C. for 3 hours. On completion, the reaction mixture was diluted with water (60 mL) and extracted with EA (4×60 mL). The combined organic layers was dried over Na$_2$SO$_4$, filtered and concentrated in vacuo to give a residue. The crude product was purified by prep-HPLC (0.1% FA condition) to give the title compound (0.50 g, 69% yield) as brown oil. $^1$H NMR (400 MHz, DMSO-d$_6$) δ 11.11 (s, 1H), 7.17 (d, J=8.0 Hz, 1H), 7.15-7.11 (m, 1H), 7.06-7.00 (m, 1H), 5.40 (dd, J=5.2, 12.8 Hz, 1H), 4.55 (t, J=5.2 Hz, 1H), 4.46 (s, 2H), 3.70-3.61 (m, 5H), 3.60-3.57 (m, 2H), 3.53-3.51 (m, 6H), 3.49-3.47 (m, 4H), 3.41-3.39 (m, 2H), 2.95-2.84 (m, 1H), 2.77-2.58 (m, 2H), 2.07-1.99 (m, 1H).

Step 2—3-[4-[3-[2-[2-[2-(2-Hydroxyethoxy)ethoxy]ethoxy]ethoxy]propyl]-3-methyl-2-oxo-benzimidazol-1-yl]piperidine-2,6-dione To a mixture of 3-[4-[3-[2-[2-[2-(2-hydroxyethoxy)ethoxy]ethoxy]ethoxy]prop-1-ynyl]-3-methyl-2-oxo-benzimidazol-1-yl]piperidine-2,6-dione (200 mg, 408 umol) in THF (10 mL) was added Pd/C (100 mg, 10% wt) and Pd(OH)$_2$/C (100 mg, 10% wt). The reaction mixture was stirred at 25° C. for 12 hours under H$_2$ (15 psi) atmosphere. On completion, the reaction mixture was filtrated and concentrated in vacuo to give the title compound (180 mg, 89% yield) as white solid. $^1$H NMR (400 MHz, DMSO-d$_6$) δ 11.09 (s, 1H), 6.96 (d, J=4.4 Hz, 2H), 6.90-6.86 (m, 1H), 5.36 (dd, J=5.2, 12.4 Hz, 1H), 4.57 (t, J=5.2 Hz, 1H), 4.03 (q, J=7.2 Hz, 1H), 3.56 (s, 3H), 3.52 (d, J=5.6 Hz, 10H), 3.48-3.45 (m, 4H), 3.40 (d, J=5.2 Hz, 2H), 2.98-2.93 (m, 2H), 2.89-2.84 (m, 1H), 2.72-2.63 (m, 2H), 2.61-2.58 (m, 2H), 2.02-1.96 (m, 2H), 1.85-1.81 (m, 1H); LC-MS (ESI$^+$) m/z 494.3 (M+H)$^+$.

2-[[2-[[2-[Benzyloxycarbonyl(methyl)amino]acetyl]-methyl-amino]acetyl]-methyl-amino]acetic acid (Intermediate VC)

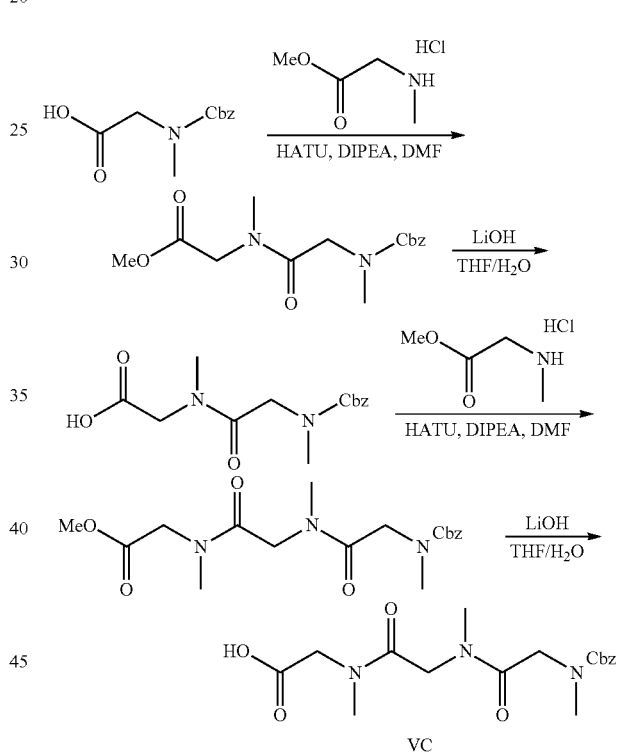

VC

Step 1-Methyl 2-[[2-[benzyloxycarbonyl(methyl)amino]acetyl]-methyl-amino]acetate To a solution of 2-[benzyloxycarbonyl(methyl)amino]acetic acid (4.30 g, 19.2 mmol, CAS #39608-31-6) and methyl 2-(methylamino)acetate (2.69 g, 19.2 mmol, HCl, CAS #5473-12-1) in DMF (25 mL) was added DIPEA (4.98 g, 38.5 mmol) and HATU (8.79 g, 23.1 mmol). The reaction mixture was stirred at 25° C. for 1 hours. On completion, the reaction mixture was quenched with water (100 mL) and extracted with EA (3×200 mL). The combined organic layers were washed with brine (2×200 mL), dried with anhydrous Na$_2$SO$_4$, filtered and concentrated in vacuo. The residue was purified by reverse phase (0.1% FA condition) to give the title compound (5.00 g, 84% yield) as colorless oil. LC-MS (ESI+) m/z 309.1 (M+H)$^+$.

Step 2—2-[[2-[Benzyloxycarbonyl(methyl)amino]acetyl]-methyl-amino]acetic acid To a solution of methyl 2-[[2-[benzyloxycarbonyl(methyl)amino]acetyl]-methyl-amino]acetate (2.00 g, 6.49 mmol) in THF (20 mL) and H$_2$O (4 mL) was added LiOH (310 mg, 12.9 mmol). The reaction mixture was stirred at 25° C. for 12 hours. On completion, the reaction mixture was acidified to pH=5 with 1.0 M aq. HCl and concentrated in vacuo. The residue was purified by flash (0.1%, HCl) to give the title compound (1.80 g, 91% yield) as colorless oil. LC-MS (ESI+) m/z 295.1 (M+H)$^+$.

Step 3—Methyl 2-[[2-[[2-[benzyloxycarbonyl(methyl)amino]acetyl]-methyl-amino]acetyl]-methyl-amino]acetate To a solution of methyl 2-(methylamino)acetate (1.02 g, 7.34 mmol, HCl, CAS #5473-12-1) and 2-[[2-[benzyloxycarbonyl(methyl)amino]acetyl]-methyl-amino]acetic acid (1.80 g, 6.12 mmol) in DMF (20 mL) was added DIPEA (2.37 g, 18.3 mmol) and HATU (2.56 g, 6.73 mmol). The reaction mixture was stirred at 25° C. for 30 minutes. On completion, the reaction mixture was quenched with water (30 mL) and extracted with EA (3×100 mL). The combined organic layers were washed with brine (50 mL), dried with anhydrous Na$_2$SO$_4$, filtered and concentrated in vacuo. The residue was purified by silica column chromatography (PE/EA, 5/1 to 1/1) to give the title compound (1.30 g, 56% yield) as colorless oil. $^1$H NMR (400 MHz, METHANOL-d$_4$) δ 7.40-7.26 (m, 5H), 5.11 (d, J=17.1 Hz, 2H), 4.44-4.00 (m, 6H), 3.81-3.68 (m, 3H), 3.11-2.91 (m, 9H).

Step 4—2-[[2-[[2-[Benzyloxycarbonyl(methyl)amino]acetyl]-methyl-amino]acetyl]-methyl-amino]acetic acid To a solution of methyl 2-[[2-[[2-[benzyloxycarbonyl(methyl)amino]acetyl]-methyl-amino]acetyl]-methyl-amino]acetate (1.00 g, 2.64 mmol) in THF (20 mL) and H$_2$O (4 mL) was added LiOH (126 mg, 5.27 mmol). The reaction mixture was stirred at 25° C. for 2 hours. On completion, the reaction mixture was concentrated in vacuo, diluted with water (30 mL) and acidified to pH=5 with 1.0 M aq.HCl. The reaction mixture was concentrated in vacuo. The residue was purified by flash (0.1%, HCl) to give the title compound (600 mg, 62% yield) as a white solid. $^1$H NMR (400 MHz, DMSO-d$_6$) δ 7.41-7.23 (m, 5H), 5.13-5.01 (m, 2H), 4.35-3.88 (m, 5H), 4.35-3.87 (m, 1H), 3.04-2.74 (m, 9H).

3-[3-Methyl-4-[3-(methylamino)propyl]-2-oxo-benzimidazol-1-yl]piperidine-2,6-dione (Intermediate VD)

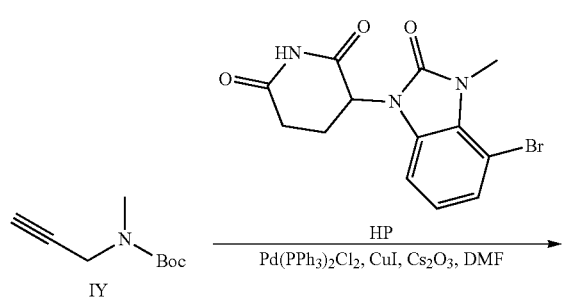

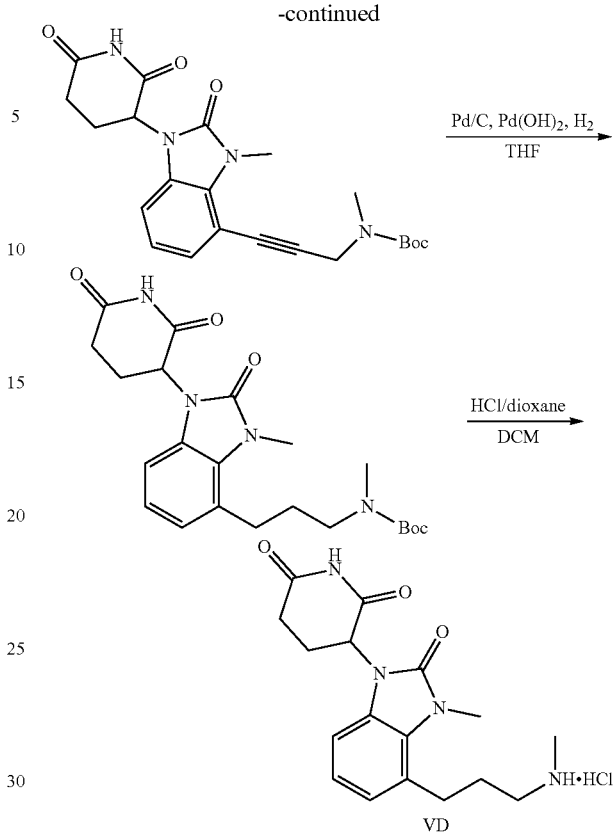

Step 1—Tert-butyl N-[3-[1-(2,6-dioxo-3-piperidyl)-3-methyl-2-oxo-benzimidazol-4-yl]prop-2-ynyl]-N-methyl-carbamate To a solution of tert-butyl N-methyl-N-prop-2-ynyl-carbamate (450 mg, 2.66 mmol, Intermediate IY) and 3-(4-bromo-3-methyl-2-oxo-benzimidazol-1-yl)piperidine-2,6-dione (300 mg, 887 umol, Intermediate HP) in DMF (15 mL) was added Cs$_2$CO$_3$ (1.45 g, 4.44 mmol), CuI (33.7 mg, 177 umol) and Pd(PPh$_3$)$_2$Cl$_2$ (124 mg, 177 umol). The reaction mixture was stirred at 80° C. for 2 hours under N$_2$. On completion, the mixture was filtered, and the filtrate was concentrated in vacuo. The residue was purified by reverse phase (0.1% FA condition) to give the title compound (200 mg, 58% yield) as yellow solid. LC-MS (ESI$^+$) m/z 449.2 (M+Na)$^+$.

Step 2—Tert-butyl N-[3-[1-(2,6-dioxo-3-piperidyl)-3-methyl-2-oxo-benzimidazol-4-yl]propyl]-N-methyl-carbamate To a solution of tert-butyl N-[3-[1-(2,6-dioxo-3-piperidyl)-3-methyl-2-oxo-benzimidazol-4-yl]prop-2-ynyl]-N-methyl-carbamate (220 mg, 515 umol) in THF (20 mL) was added Pd/C (250 mg, 10 wt %) and Pd(OH)$_2$/C (250 mg, 10 wt %). The mixture was stirred at 25° C. under H$_2$ (15 psi) for 2 hours. On completion, the residue was filtered and the filtrate was concentrated in vacuo to give the title compound (210 mg, 94% yield) as a white solid. $^1$H NMR (400 MHz, DMSO-d6) δ 11.08 (s, 1H), 7.00-6.93 (m, 2H), 6.91-6.86 (m, 1H), 5.36 (dd, J=5.2, 12.4 Hz, 1H), 3.55 (s, 3H), 3.28-3.21 (m, 2H), 2.91-2.83 (m, 3H), 2.80 (s, 3H), 2.75-

2.61 (m, 2H), 2.01-1.96 (m, 1H), 1.86-1.72 (m, 2H), 1.36 (s, 9H). LC-MS (ESI⁺) m/z 453.1 (M+Na)⁺.

Step 3—3-[3-Methyl-4-[3-(methylamino)propyl]-2-oxo-benzimidazol-1-yl]piperidine-2,6-dione To a solution of tert-butyl N-[3-[1-(2,6-dioxo-3-piperidyl)-3-methyl-2-oxo-benzimidazol-4-yl]propyl]-N-methyl-carbamate (210 mg, 487 umo) in DCM (3 mL) was added HCl/dioxane (4 M, 3 mL). The mixture was stirred at 25° C. for 2 hours. On completion, the mixture was concentrated in vacuo to give the title compound (178 mg, 99% yield, HCl) as a white solid. LC-MS (ESI⁺) m/z 331.1 (M+H)⁺.

N-[2-[[2-[3-[1-(2,6-dioxo-3-piperidyl)-3-methyl-2-oxo-benzimidazol-4-yl]propyl-methyl-amino]-2-oxo-ethyl]-methyl-amino]-2-oxo-ethyl]-N-methyl-2-(methylamino)acetamide (Intermediate VE)

Step 1—Benzyl N-[2-[[2-[[2-[3-[1-(2,6-dioxo-3-piperidyl)-3-methyl-2-oxo-benzimidazol-4-yl]propyl-methyl-amino]-2-oxo-ethyl]-methyl-amino]-2-oxo-ethyl]-methyl-amino]-2-oxo-ethyl]-N-methyl-carbamate To a solution of 3-[3-methyl-4-[3-(methylamino)propyl]-2-oxo-benzimidazol-1-yl]piperidine-2,6-dione (100 mg, 272 umol, HCl, Intermediate VD) and 2-[[2-[[2-[benzyloxycarbonyl(methyl)amino]acetyl]-methyl-amino]acetyl]-methyl-amino]acetic acid (99.6 mg, 272 umol, Intermediate VC) in DMF (5 mL) was HATU (124 mg, 327 umol) and DIPEA (176 mg, 1.36 mmol, 237 uL). The mixture was stirred at 25° C. for 1.5 hours. On completion, the reaction mixture was diluted with H₂O (5 mL) and then concentrated in vacuo. The residue was purified by reverse phase (0.1% FA condition) to give the title compound (140 mg, 75% yield) as a white solid. ¹H NMR (400 MHz, DMSO-d₆) δ 11.08 (s, 1H), 7.41-7.19 (m, 5H), 7.03-6.81 (m, 3H), 5.36 (dd, J=5.2, 12.4 Hz, 1H), 5.10-4.94 (m, 2H), 4.35-4.13 (m, 4H), 4.08-3.85 (m, 2H), 3.61-3.51 (m, 3H), 3.46-3.26 (m, 5H), 2.98-2.76 (m, 14H), 2.72-2.59 (m, 2H), 2.04-1.71 (m, 3H). LC-MS (ESI⁺) m/z 678.3 (M+H)⁺.

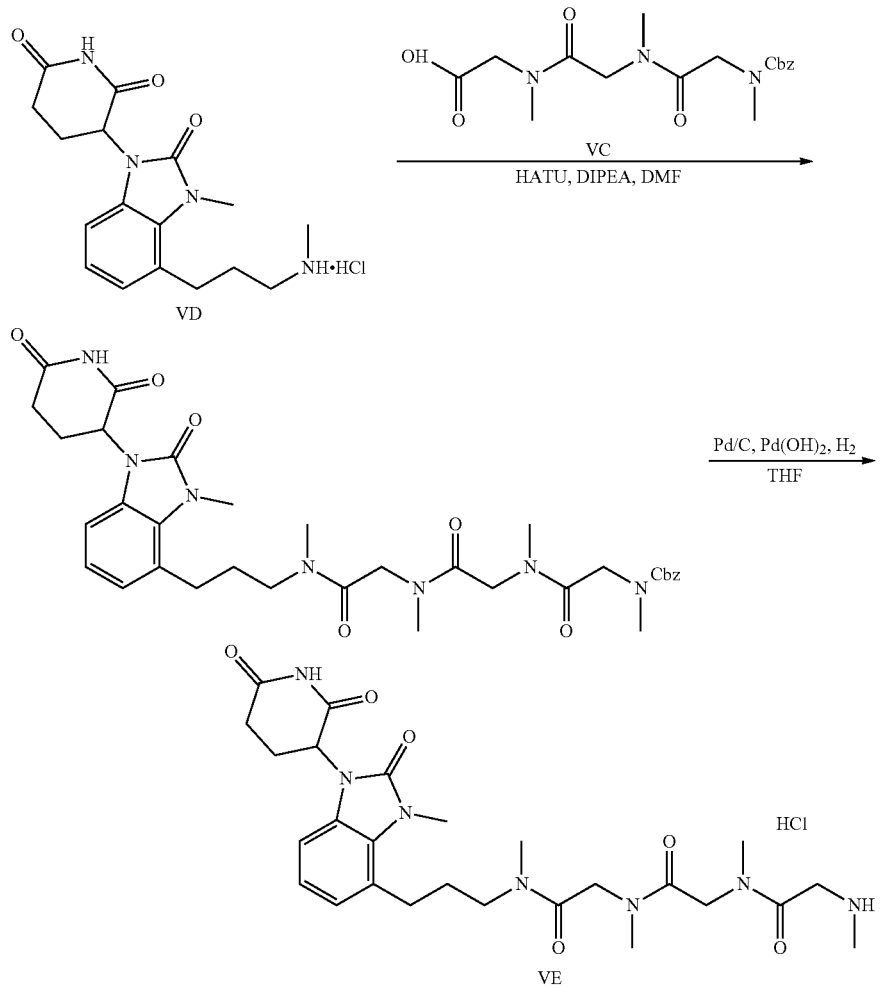

Step 2—N-[2-[[2-[3-[1-(2,6-dioxo-3-piperidyl)-3-methyl-2-oxo-benzimidazol-4-yl]propyl-methyl-amino]-2-oxo-ethyl]-methyl-amino]-2-oxo-ethyl]-N-methyl-2-(methylamino)acetamide To a solution of benzyl N-[2-[[2-[[2-[3-[1-(2,6-dioxo-3-piperidyl)-3-methyl-2-oxo-benzimidazol-4-yl]propyl-methyl-amino]-2-oxo-ethyl]-methyl-amino]-2-oxo-ethyl]-methyl-amino]-2-oxo-ethyl]-N-methyl-carbamate (200 mg, 295 umol) in THF (10 mL) was added Pd/C (100 mg, 915 umol, 10 wt %) and Pd(OH)$_2$/C (100 mg, 915 umol, 10 wt %). The mixture was stirred at 25° C. under H$_2$ (15 psi) for 12 hours. On completion, the residue was filtered and the filtrate was concentrated in vacuo to give the title compound (140 mg, 87% yield) as a white solid. LC-MS (ESI$^+$) m/z 544.3 (M+H)$^+$.

2-[[2-[[2-[Tert-butoxycarbonyl(methyl)amino]acetyl]-methyl-amino]acetyl]-methyl-amino]acetic acid (Intermediate VF)

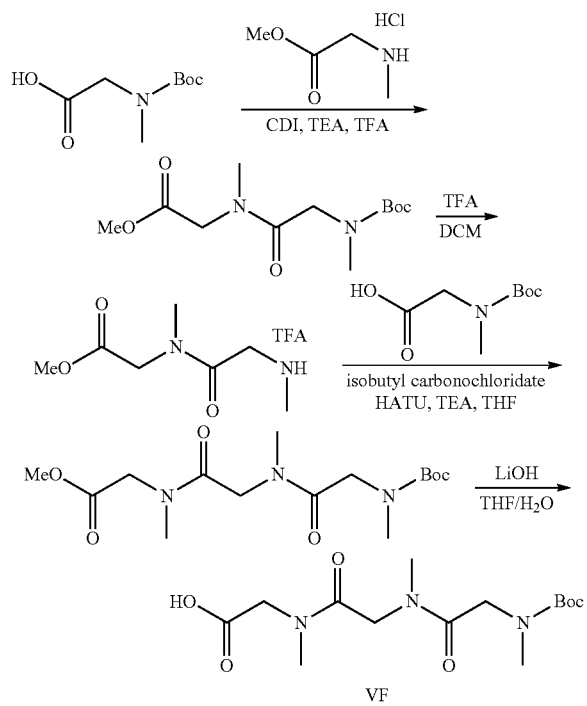

Step 1—Methyl 2-[[2-[Tert-butoxycarbonyl(methyl)amino]acetyl]-methyl-amino]acetate To a solution of 2-[tert-butoxycarbonyl(methyl)amino]acetic acid (5.00 g, 26.4 mmol, CAS #13734-36-6) in THF (25 mL) was added CDI (4.28 g, 26.4 mmol) under ice-cooling bath. The resulting mixture was stirred for 1 hour; then methyl 2-(methylamino)acetate (3.69 g, 26.4 mmol, HCl) was added followed by addition of a solution of TEA (2.94 g, 29.0 mmol, 4.05 mL) in THF (20 mL). The resulting mixture was stirred at 20° C. for 20 hours. On completion, the mixture was concentrated in vacuo. The residue was diluted with EA (100 mL), washed with 10% aq. NaHCO$_3$ and 1 M aq. HCl subsequently; dried with Na$_2$SO$_4$ filtered and concentrated in vacuo to give the title compound (3.73 g, 51% yield) as yellow oil. $^1$H NMR (400 MHz, DMSO-d$_6$) δ 4.35-4.23 (m, 4H), 3.55-3.45 (m, 3H), 3.05 (s, 3H), 2.89-2.93 (m, 3H), 1.47-1.25 (m, 9H).

Step 2—Methyl 2-[methyl-[2-(methylamino)acetyl]amino]acetate

To a solution of methyl 2-[[2-[tert-butoxycarbonyl(methyl)amino]acetyl]-methyl-amino]acetate (3.73 g, 13.60 mmol) in DCM (10 mL) was added TFA (7.70 g, 67.53 mmol, 5 mL) under 0° C. The resulting mixture was stirred at 20° C. for 16 hours. On completion, the mixture was concentrated in vacuo to give to give the title compound (3.85 g, 98% yield, TFA salt) as yellow oil.

Step 3-Methyl 2-[[2-[[2-[tert-butoxycarbonyl(methyl)amino]acetyl]-methyl-amino]acetyl]-methyl-amino]acetate To a solution of 2-[tert-butoxycarbonyl(methyl)amino] acetic acid (1.31 g, 6.94 mmol, CAS #13734-36-6) and TEA (3.51 g, 34.7 mmol, 4.83 mL) in THF (50 mL) was isobutyl carbonochloridate (2.37 g, 17.3 mmol, 2.28 mL, CAS #543-27-1) at 0° C. The mixture was stirred at 25° C. for 0.5 hour, then methyl 2-[methyl-[2-(methylamino)acetyl]amino]acetate (2.00 g, 6.94 mmol, TFA) was added, and the mixture was stirred at 25° C. for 3 hours. On completion, the reaction mixture was diluted with H$_2$O (50 mL), and extracted with EA (2×100 mL), then concentrated in vacuo. The residue was purified by prep-HPLC (column: Kromasil 150*25 mm*10 um; mobile phase: [water (0.225% FA)-ACN]; B %: 17%-47%, 10 min) to give the title compound (400 mg, 16% yield) as yellow oil. $^1$H NMR (400 MHz, CD$_3$C$_1$) δ 4.15-4.12 (m, 3H), 3.78 (s, 1H), 3.82-3.77 (m, 1H), 3.75-3.73 (m, 2H), 3.09-3.05 (m, 5H), 2.99-2.95 (m, 2H), 2.92 (s, 3H), 2.95-2.88 (m, 3H), 1.46 (s, 9H).

Step 4—2-[[2-[[2-[Tert-butoxycarbonyl(methyl)amino]acetyl]-methyl-amino]acetyl]-methyl-amino]acetic acid To a solution of methyl 2-[[2-[[2-[tert-butoxycarbonyl(methyl)amino]acetyl]-methyl-amino]acetyl]-methyl-amino]acetate (200 mg, 579 umol) in THF (4 mL) and H$_2$O (2 mL) was added LiOH (27.7 mg, 1.16 mmol). The reaction mixture was stirred at 25° C. for 12 hr. On completion, the mixture was concentrated in vacuo. The residue was diluted with H$_2$O (4 mL), and then adjusted to pH=5 with 1.0 M aq.HCl to give the title compound (190 mg, 99% yield) as yellow oil. LC-MS (ESI$^+$) m/z 232.1 (M+H)$^+$.

3-[3-Methyl-5-[3-(methylamino)propyl]-2-oxo-benzimidazol-1-yl]piperidine-2,6-dione (Intermediate VG)

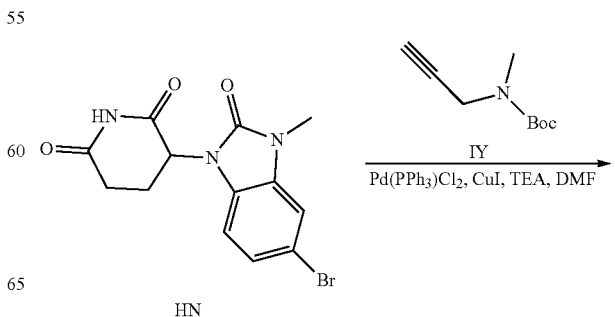

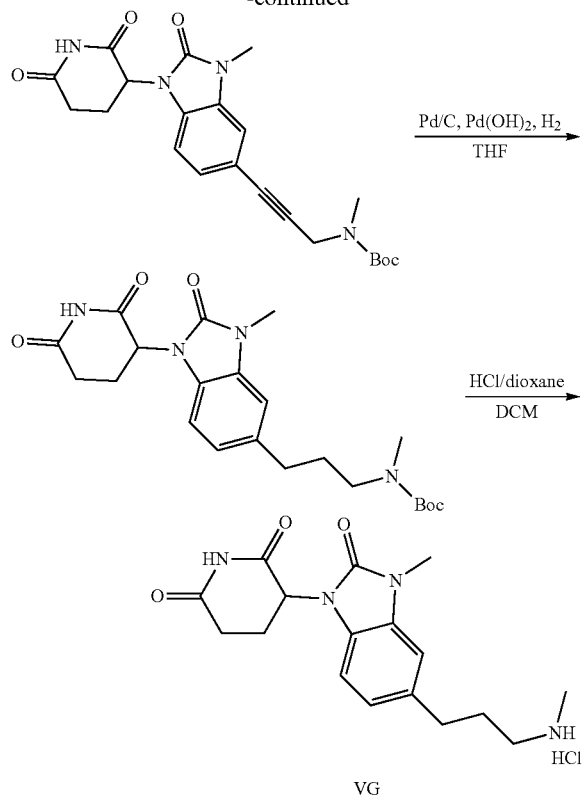

Step 1—Tert-butyl N-[3-[1-(2,6-dioxo-3-piperidyl)-3-methyl-2-oxo-benzimidazol-5-yl]prop-2-ynyl]-N-methyl-carbamate To a solution of 3-(5-bromo-3-methyl-2-oxo-benzimidazol-1-yl)piperidine-2,6-dione (400 mg, 1.18 mmol, Intermediate HN), tert-butyl N-methyl-N-prop-2-ynyl-carbamate (400 mg, 2.37 mmol, Intermediate IY) and Pd(PPh$_3$)$_2$Cl$_2$ (83.0 mg, 118 umol) in DMF (4 mL) was added PPh$_3$ (62.0 mg, 236 umol), TEA (2.15 g, 21.2 mmol) and CuI (22.5 mg, 118 umol). The reaction mixture was stirred at 80° C. for 3 hours under N$_2$. On completion, the reaction mixture was quenched with aq. NH$_4$Cl (30 mL) and extracted with EA (3×50 mL). The combined organic layers were washed with brine (50 mL), dried with anhydrous Na$_2$SO$_4$, filtered and concentrated in vacuo. The residue was purified by flash (0.1%, FA) to give the title compound (200 mg, 37% yield) as a yellow solid. LC-MS (ESI$^+$) m/z 427.1 (M+H)$^+$.

Step 2—Tert-butyl N-[3-[1-(2,6-dioxo-3-piperidyl)-3-methyl-2-oxo-benzimidazol-5-yl]propyl]-N-methyl-carbamate To a solution of tert-butyl N-[3-[1-(2,6-dioxo-3-piperidyl)-3-methyl-2-oxo-benzimidazol-5-yl]prop-2-ynyl]-N-methyl-carbamate (200 mg, 468 umol) in THF (20 mL) was added Pd(OH)$_2$ (25.0 mg, 178 umol) and Pd/C (25.0 mg, 10 wt %). The reaction mixture was stirred at 25° C. for 12 hours under H$_2$ (15 psi). On completion, the reaction mixture was diluted with EA (20 mL), filtered through a short of silica column and washed with EA (2×50 mL). The organic layers were concentrated in vacuo. The residue was purified by flash chromatography (0.1%, FA) to give the title compound (200 mg, 99% yield) as a white solid. LC-MS (ESI$^+$) m/z 331.0 (M-100+H)$^+$.

Step 3—3-[3-Methyl-5-[3-(methylamino)propyl]-2-oxo-benzimidazol-1-yl]piperidine-2,6-dione To a solution of tert-butyl N-[3-[1-(2,6-dioxo-3-piperidyl)-3-methyl-2-oxo-benzimidazol-5-yl]propyl]-N-methyl-carbamate (200 mg, 464 umol) in DCM (5 mL) was added HCl/dioxane (4 M, 5 mL). The reaction mixture was stirred at 25° C. for 20 min. On completion, the reaction mixture was concentrate in vacuo to give the title compound (150 mg, 97% yield) as a white solid. LC-MS (ESI$^+$) m/z 331.1 (M+H)$^+$.

N-[2-[[2-[3-[1-(2,6-dioxo-3-piperidyl)-3-methyl-2-oxo-benzimidazol-5-yl]propyl-methyl-amino]-2-oxo-ethyl]-methyl-amino]-2-oxo-ethyl]-N-methyl-2-(methylamino)acetamide (Intermediate VH)

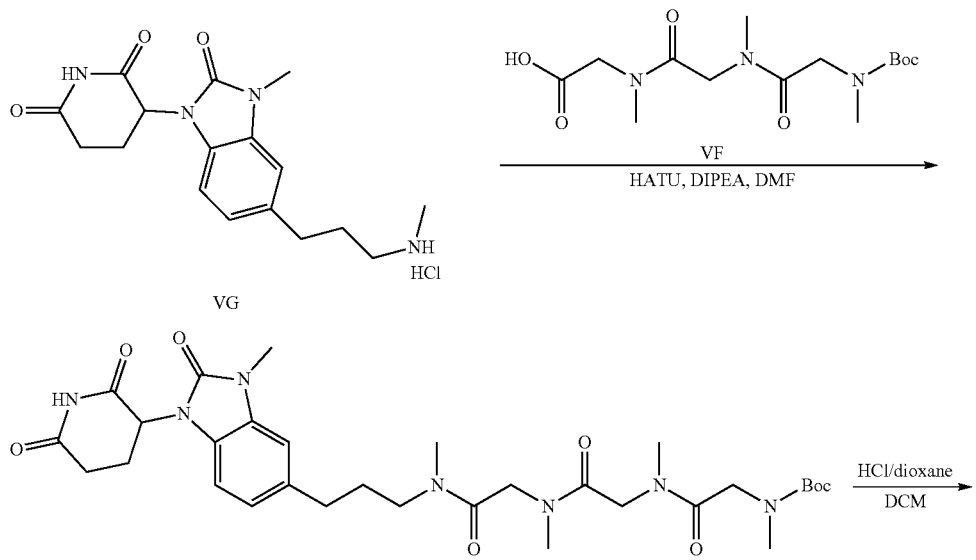

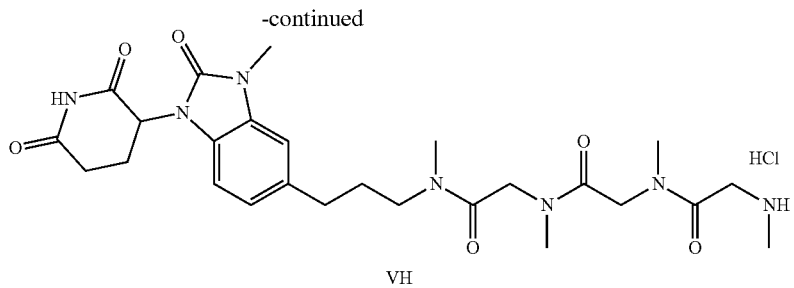

VH

Step 1—Tert-butyl N-[2-[[2-[[2-[3-[1-(2,6-dioxo-3-piperidyl)-3-methyl-2-oxo-benzimidazol-5-yl]propyl-methyl-amino]-2-oxo-ethyl]-methyl-amino]-2-oxo-ethyl]-methyl-amino]-2-oxo-ethyl]-N-methyl-carbamate To a solution of 3-[3-methyl-5-[3-(methylamino)propyl]-2-oxo-benzimidazol-1-yl]piperidine-2,6-dione (100 mg, 272 umol, HCl, Intermediate VG) and 2-[[2-[[2-[tert-butoxycarbonyl(methyl)amino]acetyl]-methyl-amino]acetyl]-methyl-amino]acetic acid (108 mg, 327 umol, Intermediate VF) in DMF (5 mL) was added DIPEA (105 mg, 817 umol) and HATU (124 mg, 327 umol). The reaction mixture was stirred at 25° C. for 30 mines. On completion, the reaction mixture was quenched with water (5 mL), concentrated in vacuo. The residue was purified by flash chromatography (0.1%, FA) to give the title compound (50.0 mg, 28% yield) as a white solid. LC-MS (ESI$^+$) m/z 644.2 (M+H)$^+$.

Step 2—N-[2-[[2-[3-[1-(2,6-dioxo-3-piperidyl)-3-methyl-2-oxo-benzimidazol-5-yl]propyl-methyl-amino]-2-oxo-ethyl]-methyl-amino]-2-oxo-ethyl]-N-methyl-2-(methylamino)acetamide To a solution of tert-butyl N-[2-[[2-[[2-[3-[1-(2,6-dioxo-3-piperidyl)-3-methyl-2-oxo-benzimidazol-5-yl]propyl-methyl-amino]-2-oxo-ethyl]-methyl-amino]-2-oxo-ethyl]-methyl-amino]-2-oxo-ethyl]-N-methyl-carbamate (50.0 mg, 77.6 umol) in DCM (4 mL) was added HCl/dioxane (4 M, 10 mL). The reaction mixture was stirred at 25° C. for 1 hour. On completion, the reaction mixture was concentrated in vacuo to give the title compound (40.0 mg, 88% yield, HCl) as a white solid. LC-MS (ESI$^+$) m/z 544.2 (M+H)$^+$.

N-[3-carbamoyl-1-(4-formylphenyl)pyrazol-4-yl]-4-cyano-pyridine-2-carboxamide (Intermediate VI)

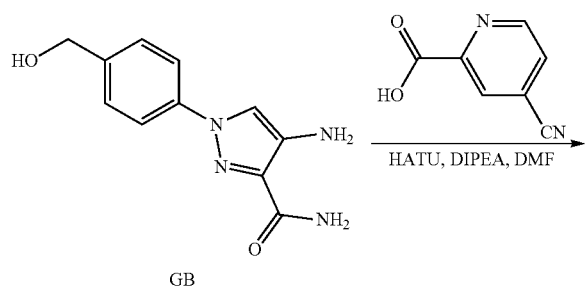

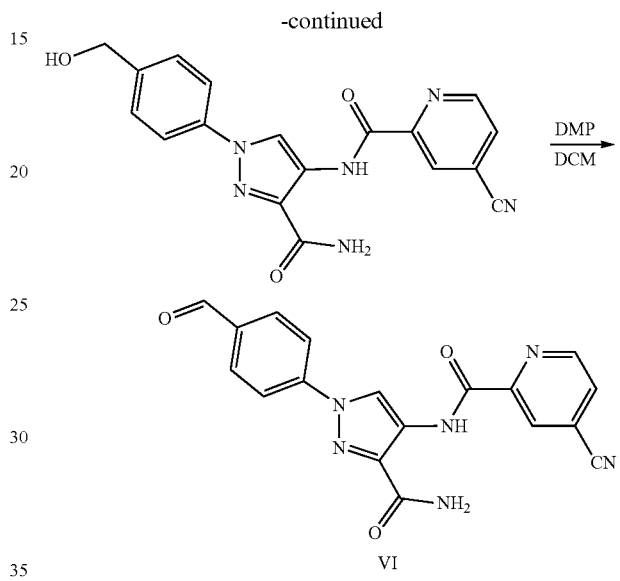

Step 1—N-[3-carbamoyl-1-[4-(hydroxymethyl)phenyl]pyrazol-4-yl]-4-cyano-pyridine-2-carboxamide To a solution of 4-amino-1-[4-(hydroxymethyl)phenyl]pyrazole-3-carboxamide (200 mg, 861 umol, Intermediate GB) and 4-cyanopyridine-2-carboxylic acid (102 mg, 688 umol, CAS #640296-19-1) in DMF (5 mL) was added DIPEA (222 mg, 1.72 mmol) and HATU (327 mg, 861 umol). The reaction mixture was stirred at 25° C. for 1 hour. On completion, the reaction mixture was poured into water (10 mL), the solid was filtered and washed with water (2×5 mL). Then the solid was dried in vacuo to give the title compound (200 mg, 42% yield) as a white solid. LC-MS (ESI$^+$) m/z 385.0 (M+Na)$^+$.

Step 2—N-[3-carbamoyl-1-(4-formylphenyl)pyrazol-4-yl]-4-cyano-pyridine-2-carboxamide To a solution of N-[3-carbamoyl-1-[4-(hydroxymethyl)phenyl]pyrazol-4-yl]-4-cyano-pyridine-2-carboxamide (130 mg, 358 umol) in THF (10 mL) was added DMP (152 mg, 358 umol) at 0° C. Then the reaction mixture was stirred at 25° C. for 2 hours. On completion, the reaction mixture was filtered. The filtrate was concentrated in vacuo to give the title compound (100 mg, 277 umol, 77% yield) as a white solid. LC-MS (ESI$^+$) m/z 383.0 (M+Na)$^+$.

2-[2-[2-[2-[3-[1-(2,6-Dioxo-3-piperidyl)-3-methyl-2-oxo-benzimidazol-4-yl]propoxy]ethoxy]ethoxy]ethoxy]ethyl methanesulfonate (Intermediate VJ)

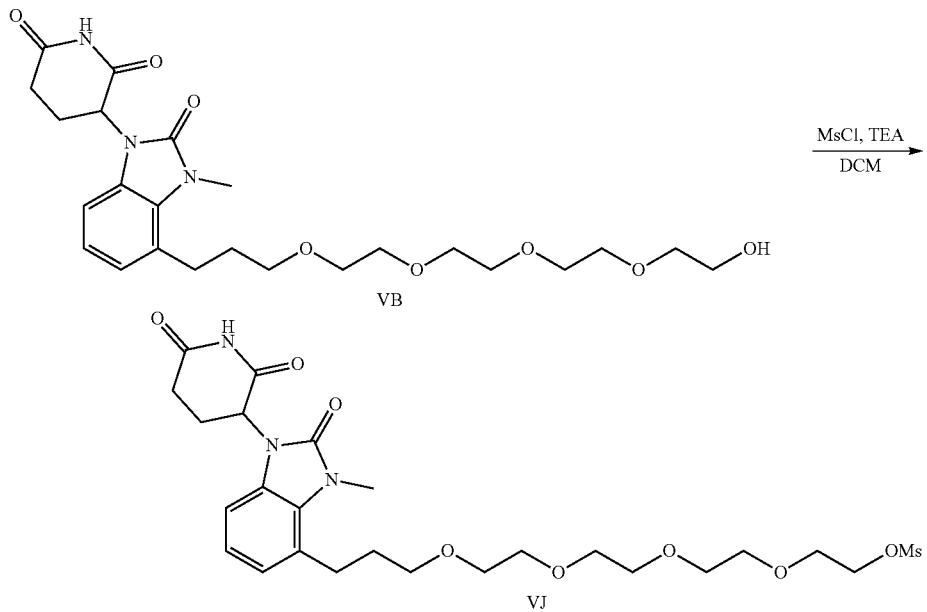

To a solution of 3-[4-[3-[2-[2-[2-(2-hydroxyethoxy)ethoxy]ethoxy]ethoxy]propyl]-3-methyl-2-oxo-benzimidazol-1-yl]piperidine-2,6-dione (150 mg, 304 umol, Intermediate VB) in DCM (10 mL) was added TEA (92 mg, 911 umol) and MsCl (104 mg, 911 umol). The mixture was stirred at 25° C. for 4 hours. On completion, the mixture was concentrated in vacuo to give the title compound (170 mg, 98% yield) as yellow oil. LC-MS (ESI$^+$) m/z 572.3 (M+1)$^+$.

3-[4-[3-[2-[2-[2-[2-(4-Amino-1-piperidyl)ethoxy]ethoxy]ethoxy]ethoxy]propyl]-3-methyl-2-oxo-benzimidazol-1-yl]piperidine-2,6-dione (Intermediate VK)

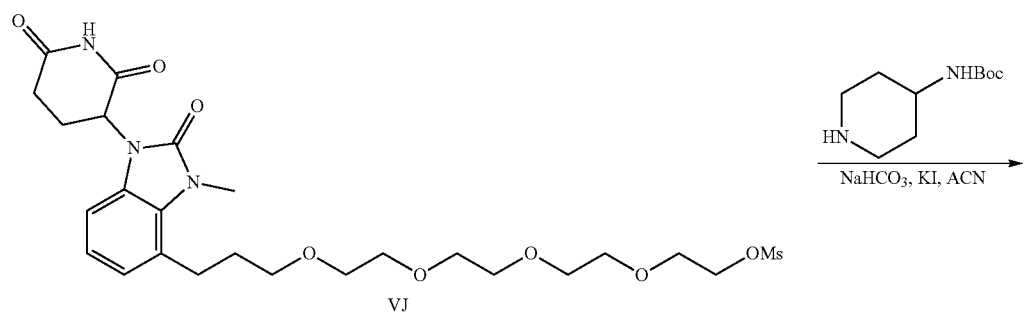

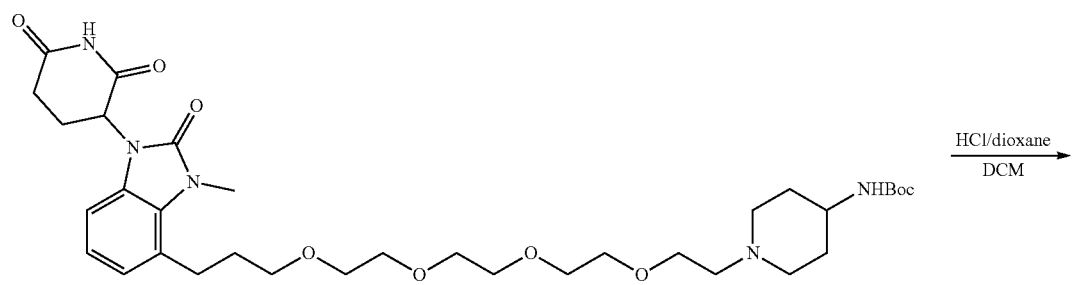

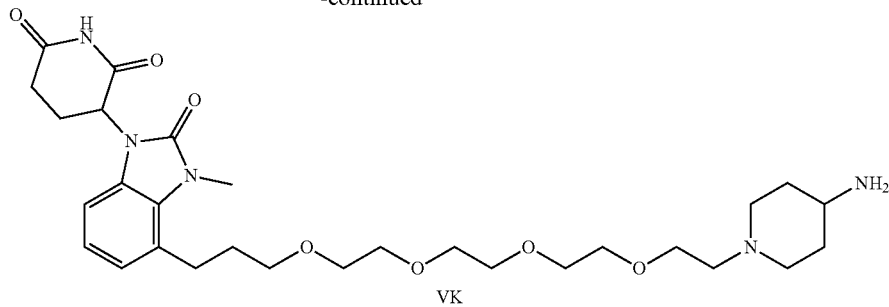

VK

Step 1—Tert-butyl N-[1-[2-[2-[2-[2-[3-[1-(2,6-di-oxo-3-piperidyl)-3-methyl-2-oxo-benzimidazol-4-yl]propoxy]ethoxy]ethoxy]ethoxy]ethyl]-4-piperidyl]carbamate To a solution of 2-[2-[2-[2-[3-[1-(2,6-dioxo-3-piperidyl)-3-methyl-2-oxo-benzimidazol-4-yl]propoxy]ethoxy]ethoxy]ethoxy]ethylmethanesulfonate (250 mg, 437 umol, Intermediate VJ) in ACN (10 mL) was added KI (7.26 mg, 43 umol), NaHCO$_3$ (110 mg, 1.31 mmol) and tert-butyl N-(4-piperidyl)carbamate (175 mg, 875 umol, CAS #73874-95-0). The mixture was stirred at 80° C. for 16 hours. On completion, the mixture was filtered and the filtrate was concentrated in vacuo. The residue was purified by reversed phase flash chromatography to give the title compound (200 mg, 66% yield) as light yellow oil. LC-MS (ESI$^+$) m/z 676.4 (M+1)$^+$.

Step 2—3-[4-[3-[2-[2-[2-[2-(4-Amino-1-piperidyl)ethoxy]ethoxy]ethoxy]ethoxy]propyl]-3-methyl-2-oxo-benzimidazol-1-yl]piperidine-2,6-dione To a solution of tert-butyl N-[1-[2-[2-[2-[2-[3-[1-(2,6-dioxo-3-piperidyl)-3-methyl-2-oxo-benzimidazol-4-yl]propoxy]ethoxy]ethoxy]ethoxy]ethyl]-4-piperidyl]carbamate (200 mg, 295 umol) in DCM (10 mL) was added HCl/dioxane (4 M, 5 mL). The mixture was stirred at 25° C. for 3 hours. On completion, the mixture was concentrated in vacuo to give the title compound (180 mg, 99% yield) as yellow solid. LC-MS (ESI$^+$) m/z 576.4 (M+1)$^+$.

[4-(4,5,6,7-Tetrahydropyrazolo[4,3-b]pyridin-2-yl)phenyl]methanol (Intermediate VL)

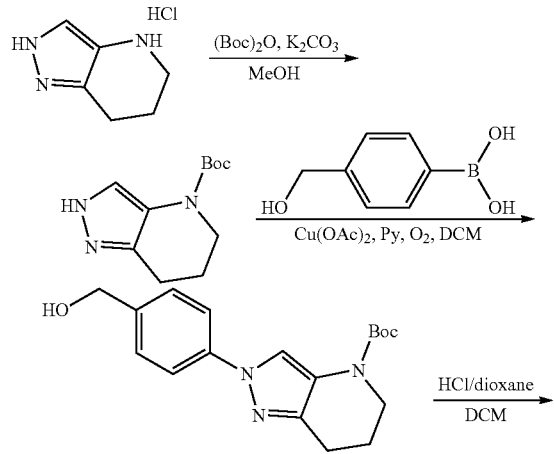

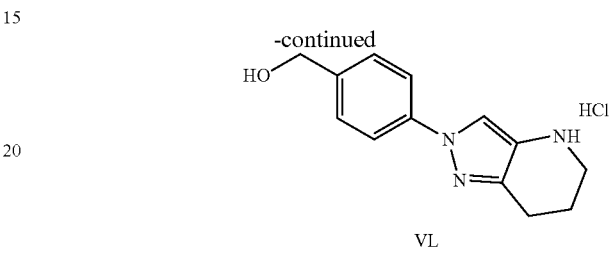

VL

Step 1—Tert-butyl 2,5,6,7-tetrahydropyrazolo[4,3-b]pyridine-4-carboxylate

To a mixture of 4,5,6,7-tetrahydro-2H-pyrazolo[4,3-b]pyridine (500 mg, 3.13 mmol, HCl, CAS #1187830-47-2) and (Boc)$_2$O (752 mg, 3.45 mmol) in MeOH (15 mL) was added aq.K$_2$CO$_3$ (3 M, 2.09 mL). The reaction mixture was stirred at 20° C. for 15 hours. On completion, the mixture was concentrated in vacuo. The residue was purified by silica gel chromatography (SiO$_2$) to give the title compound (500 mg, 71% yield) as a white solid. $^1$H NMR (400 MHz, DMSO-d$_6$) δ 12.05 (s, 1H), 7.55 (s, 1H), 3.66-3.55 (m, 2H), 2.65 (t, J=6.4 Hz, 2H), 1.94-1.82 (m, 2H), 1.51 (s, 9H).

Step 2—Tert-butyl 2-[4-(hydroxymethyl)phenyl]-6,7-dihydro-5H-pyrazolo[4,3-b]pyridine-4-carboxylate To a solution of [4-(hydroxymethyl)phenyl]boronic acid (112 mg, 739 umol, CAS #59016-93-2) and tert-butyl 2,5,6,7-tetrahydropyrazolo[4,3-b]pyridine-4-carboxylate (110 mg, 493 umol) in DCM (5 mL) was added Cu(OAc)$_2$ (179 mg, 985 umol) and pyridine (2 mL). The reaction mixture was stirred at 25° C. for 12 hours under oxygen (15 psi) atmosphere. On completion, the mixture was quenched with ammonia water (20 mL), stirred and separated. The organic layer was acidified to pH=5 with 1N aq.HCl (20 mL), separated and washed with brine (20 mL), then concentrated in vacuo. The mixture was purified by silica gel chromatography (SiO$_2$) to give the title compound (80.0 mg, 49% yield) as colorless oil. $^1$H NMR (400 MHz, DMSO-d$_6$) δ 8.16 (s, 1H), 7.64 (d, J=8.4 Hz, 2H), 7.39 (d, J=8.8 Hz, 2H), 4.93 (t, J=5.6 Hz, 1H), 4.53 (d, J=5.6 Hz, 2H), 3.72-3.62 (m, 2H), 2.78-2.71 (m, 2H), 2.00-1.91 (m, 2H), 1.54 (s, 9H); LC-MS (ESI$^+$) m/z 330.2 (M+H)$^+$.

Step 3—[4-(4,5,6,7-Tetrahydropyrazolo[4,3-b]pyridin-2-yl)phenyl]methanol

To a solution of tert-butyl 2-[4-(hydroxymethyl)phenyl]-6,7-dihydro-5H-pyrazolo[4,3-b]pyridine-4-carboxylate (60.0 mg, 182 umol) in DCM (4 mL) was added HCl/ dioxane (4 mL). The reaction mixture was stirred at 25° C. for 12 hours. On completion, the mixture was concentrated in vacuo to give the title compound (45 mg, 93% yield, HCl) as a yellow solid. LC-MS (ESI⁺) m/z 230.1 (M+H)⁺.

Tert-butyl N-[4-[4-[2-(4-formylphenyl)-6,7-dihydro-5H-pyrazolo[4,3-b]pyridine-4-carbonyl]oxazol-2-yl]-2-pyridyl]-N-(2,2,2-trifluoroethyl)carbamate (Intermediate VM)

Step 2—Tert-butyl N-[4-[4-[2-(4-formylphenyl)-6,7-dihydro-5H-pyrazolo[4,3-b]pyridine-4-carbonyl]oxazol-2-yl]-2-pyridyl]-N-(2,2,2-trifluoroethyl)carbamate To a solution of tert-butyl N-[4-[4-[2-[4-(hydroxymethyl)phenyl]-6,7-dihydro-5H-pyrazolo[4,3-b]pyridine-4-carbonyl]oxazol-2-yl]-2-pyridyl]-N-(2,2,2-trifluoroethyl)carbamate (70.0 mg, 117 umol) in DCM (4 mL) was added DMP (74.4 mg, 175 umol). The reaction mixture was stirred at 25°

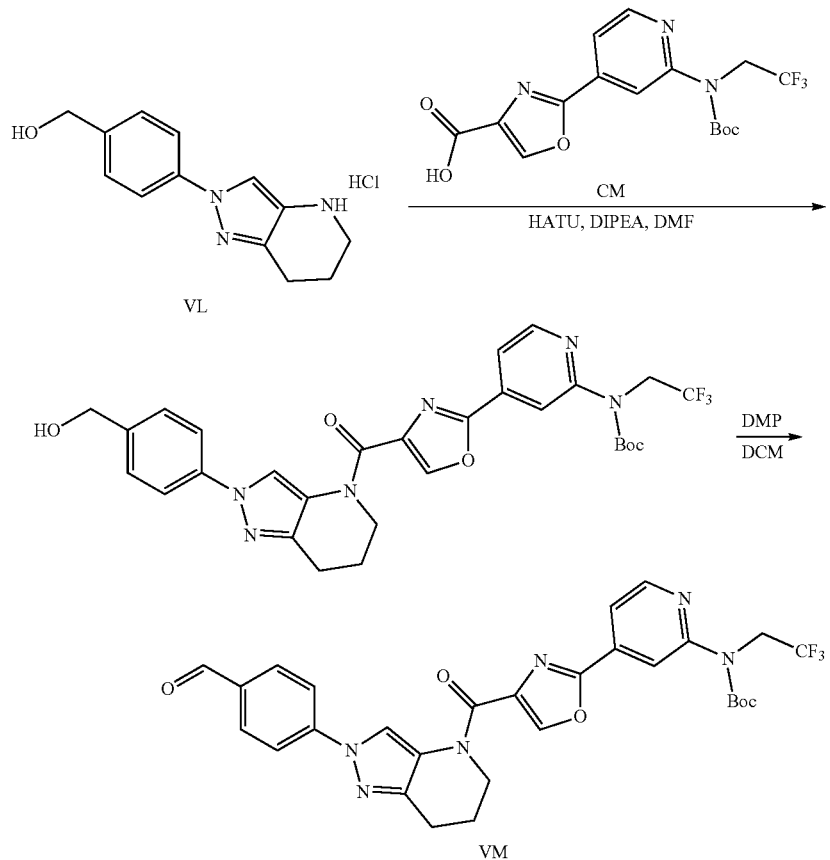

Step 1—Tert-butyl N-[4-[4-[2-[4-(hydroxymethyl)phenyl]-6,7-dihydro-5H-pyrazolo[4,3-b]pyridine-4-carbonyl]oxazol-2-yl]-2-pyridyl]-N-(2,2,2-trifluoroethyl)carbamate To a solution of [4-(4,5,6,7-tetrahydropyrazolo[4,3-b]pyridin-2-yl)phenyl]methanol (45.0 mg, 169 umol, HCl, Intermediate VL) and 2-[2-[tert-butoxycarbonyl(2,2,2-trifluoroethyl)amino]-4-pyridyl]oxazole-4-carboxylic acid (52.5 mg, 135 umol, Intermediate CM) in DMF (4 mL) was added HATU (64.4 mg, 169 umol) and DIPEA (109 mg, 847 umol). The reaction mixture was stirred at 25° C. for 0.5 hour. On completion, the mixture was quenched with water (50 mL), stirred and filtered. The filter cake was dried in vacuo to give the title compound (70 mg, 69% yield) as a brown solid. LC-MS (ESI⁺) m/z 599.3 (M+H)⁺

C. for 2 hours. On completion, the mixture was quenched with sat.NaHCO₃ (20 mL) and sat. Na₂S₂O₃ (20 mL) and extracted with DCM (2×30 mL). The organic layer was washed with brine (40 mL), dried over Na₂SO₄, filtered and the filtrate was concentrated in vacuo to give the title compound (65 mg, 93% yield) as a yellow solid. LC-MS (ESI⁺) m/z 597.3 (M+H)⁺.

(4-Nitrophenyl)N-[2-[2-[2-(tert-butoxycarbonylamino)ethoxy]ethoxy]ethyl]carbamate (Intermediate VN)

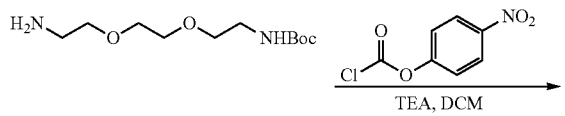

1941

-continued

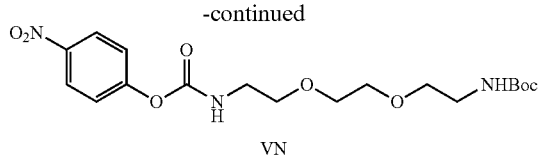

VN

To a solution of tert-butyl N-[2-[2-(2-aminoethoxy)ethoxy]ethyl]carbamate (500 mg, 2.01 mmol, CAS #153086-78-3), (4-nitrophenyl)carbonochloridate (446 mg, 2.21 mmol) in DCM (20.0 mL) was added TEA (509 mg, 5.03 mmol). The mixture was stirred at 0° C. for 1 hour. On completion, the mixture was concentrated in vacuo to give the title compound (800 mg, 90% yield) as yellow solid. LC-MS (ESI$^+$) m/z 314.1 (M+H−100)$^+$ 1-[2-[2-(2-Aminoethoxy)ethoxy]ethyl]-3-[[2-(2,6-dioxo-3-piperidyl)-1-oxo-isoindolin-5-yl]methyl]urea (Intermediate VO)

1942

Step 1—Tert-butyl N-[2-[2-[2-[[2-(2,6-dioxo-3-piperidyl)-1-oxo-isoindolin-5-yl]methylcarbamoylamino]ethoxy]ethoxy]ethyl]carbamate To a solution of 3-[5-(aminomethyl)-1-oxo-isoindolin-2-yl]piperidine-2,6-dione (130 mg, 419 umol, HCl, Intermediate QM), (4-nitrophenyl)N-[2-[2-[2-(tert-butoxycarbonylamino)ethoxy]ethoxy]ethyl]carbamate (347 mg, 839 umol, Intermediate VN) in DMF (15.0 mL) was added TEA (212 mg, 2.10 mmol). The mixture was stirred at 20° C. for 1 hour. On completion, the mixture was concentrated in vacuo. The mixture was purified by reverse phase chromatography (0.1% FA) to give the title compound (170 mg, 73% yield) as white solid. $^1$H NMR (400 MHz, DMSO-d$_6$) δ 10.99 (s, 1H), 7.67 (d, J=7.6 Hz, 1H), 7.45 (s, 1H), 7.38 (d, J 7.6 Hz, 1H), 6.78 (s, 1H), 6.56 (t, J=6.0 Hz, 1H), 6.04 (t, J=5.6 Hz, 1H), 5.16-5.05 (m, 1H), 4.47-4.24 (m, 4H), 3.53-3.36 (m, 8H), 3.24-3.13 (m, 2H), 3.10-3.02 (m, 2H), 2.99-2.85 (m, 1H), 2.65-2.55 (m, 1H), 2.46-2.36 (m, 1H), 2.05-1.94 (m, 1H), 1.37 (s, 9H).

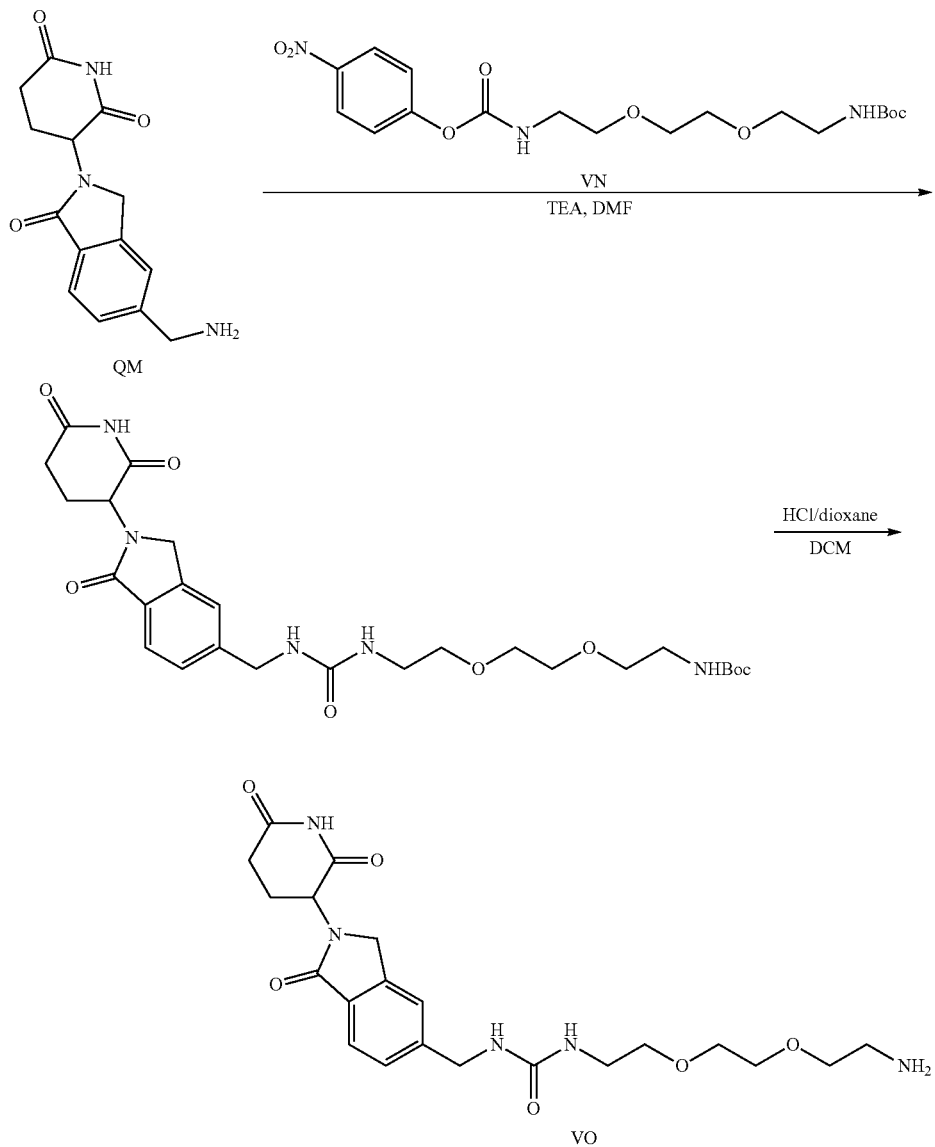

Step 2—1-[2-[2-(2-Aminoethoxy)ethoxy]ethyl]-3-[[2-(2,6-dioxo-3-piperidyl)-1-oxo-isoindolin-5-yl]methyl]urea To a solution of tert-butyl N-[2-[2-[2-[[2-(2,6-dioxo-3-piperidyl)-1-oxo-isoindolin-5-yl]methylcarbamoylamino]ethoxy]ethoxy]ethyl]carbamate (170 mg, 310 umol) in DCM (10.0 mL) was added HCl/dioxane (4.00 M, 8.00 mL). The mixture was stirred at 15° C. for 0.5 hour. On completion, the mixture was concentrated in vacuo to give the title compound (150 mg, 90% yield, HCl) as white solid. LC-MS (ESI+) m/z 448.1 (M+H)+.

Methyl 5-[4-amino-3-(difluoromethyl)pyrazol-1-yl]pyridine-2-carboxylate (Intermediate VP)

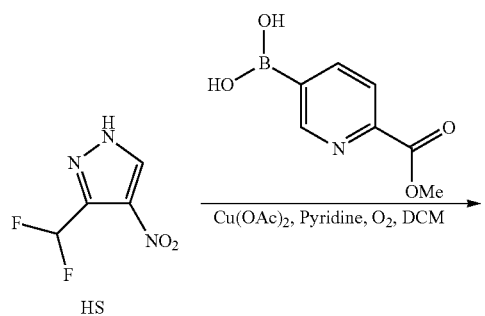

Step 1—Methyl 5-[3-(difluoromethyl)-4-nitro-pyrazol-1-yl]pyridine-2-carboxylate To a solution of 3-(difluoromethyl)-4-nitro-1H-pyrazole (200 mg, 1.23 mmol, Intermediate HS), (6-methoxycarbonyl-3-pyridyl)boronic acid (266 mg, 1.47 mmol, CAS #1072945-86-8) in DCM (20 mL) was added Cu(OAc)$_2$ (334 mg, 1.84 mmol) and pyridine (388 mg, 4.91 mmol). The mixture was stirred at 15° C. for 6 hrs under O$_2$ (15 psi). On completion, the mixture washed with NH$_3$.H$_2$O (100 mL) and then the layers were washed with brine (50 mL), dried over Na$_2$SO$_4$, filtered and concentrated in vacuo. The residue was triturated with PE:EA=1:1 (50 mL) and filtered. The filtered cake was dried in vacuo to give the title compound (100 mg, 27% yield) as a yellow solid. $^1$H NMR (400 MHz, CDCl$_3$) δ 9.23-9.08 (m, 1H), 8.85 (s, 1H), 8.35 (s, 2H), 7.26-7.06 (t, J=5.2 Hz, 1H), 4.08 (s, 3H).

Step 2—Methyl 5-[4-amino-3-(difluoromethyl)pyrazol-1-yl]pyridine-2-carboxylate To a solution of methyl 5-[3-(difluoromethyl)-4-nitro-pyrazol-1-yl]pyridine-2-carboxylate (100 mg, 335 umol) in DCM (10 mL) was added Pd/C (50.0 mg, 50 wt %). The suspension was degassed under vacuum and purged with H$_2$ several times. The mixture was stirred under H$_2$ (15 psi) at 15° C. for 2 hours. On completion, the mixture was filtered through celite. The filtrate was concentrated in vacuo to give the title compound (89.0 mg, 332 umol, 99% yield) as a yellow solid. $^1$H NMR (400 MHz, DMSO-d$_6$) δ 9.13 (d, J=2.0 Hz, 1H), 8.32-8.29 (m, 1H), 8.16 (d, J=8.4 Hz, 1H), 7.29-6.97 (t, J=5.2 Hz, 1H), 8.00 (s, 1H), 3.91 (s, 3H), 4.62 (s, 2H).

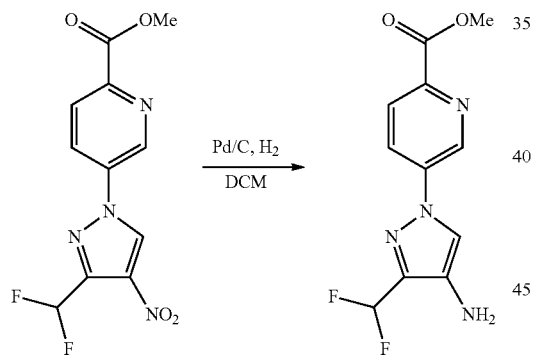

5-[4-[[2-[2-[Tert-butoxycarbonyl(cyclopropylmethyl)amino]-4-pyridyl]oxazole-4-carbonyl]amino]-3-(difluoromethyl)pyrazol-1-yl]pyridine-2-carboxylic acid (Intermediate VQ)

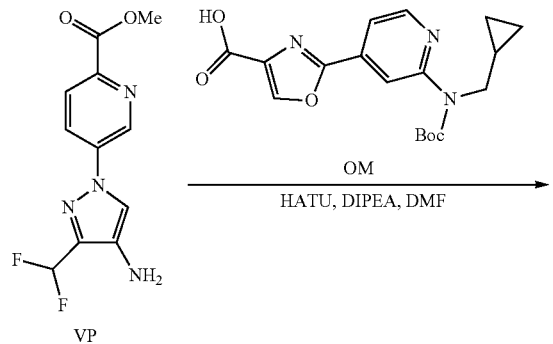

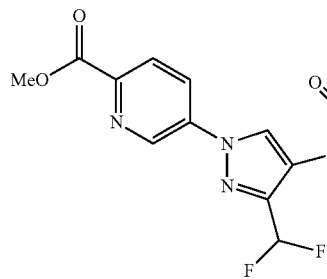
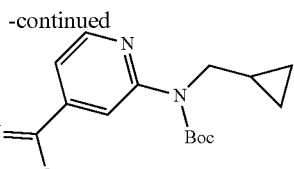

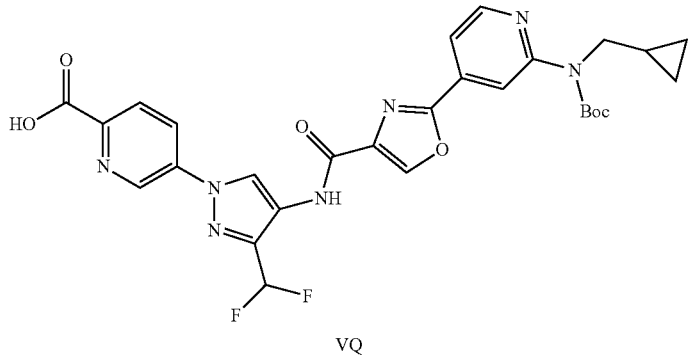

VQ

Step 1—Methyl 5-[4-[[2-[2-[tert-butoxycarbonyl(cyclopropylmethyl)amino]-4-pyridyl]oxazole-4-carbonyl]amino]-3-(difluoromethyl)pyrazol-1-yl]pyridine-2-carboxylate To a solution of methyl 5-[4-amino-3-(difluoromethyl)pyrazol-1-yl]pyridine-2-carboxylate (0.300 g, 1.12 mmol, Intermediate VP) and 2-[2-[tert-butoxycarbonyl(cyclopropylmethyl)amino]-4-pyridyl]oxazole-4-carboxylic acid (402 mg, 1.12 mmol, Intermediate OM) in DMF (2 mL) was added HATU (510 mg, 1.34 mmol) and DIPEA (361 mg, 2.80 mmol). The mixture was stirred at 15° C. for 2 hrs. On completion, to the mixture was added into H$_2$O and a precipitate formed. The mixture was filtered and the filter cake was dried in vacuo to give the title compound (50.0 mg, 820 umol, 73% yield) as a yellow solid. LC-MS (ESI$^+$) m/z 610.3 (M+H)$^+$.

Step 2—5-[4-[[2-[2-[Tert-butoxycarbonyl(cyclopropylmethyl)amino]-4-pyridyl]oxazole-4-carbonyl]amino]-3-(difluoromethyl)pyrazol-1-yl]pyridine-2-carboxylic acid To a solution of methyl 5-[4-[[2-[2-[tert-butoxycarbonyl(cyclopropylmethyl)amino]-4-pyridyl]oxazole-4-carbonyl]amino]-3-(difluoromethyl)pyrazol-1-yl]pyridine-2-carboxylate (500 mg, 820 umol) in THF (50 mL), H$_2$O (50 mL) and MeOH (10 mL) was added LiOH.H$_2$O (172 mg, 4.10 mmol). The mixture was stirred at 15° C. for 6 hrs. On completion, the mixture was adjusted to pH=6-7 with 1.0 M aq.HCl and a precipitate formed. The mixture was filtered and the filter cake was dried in vacuo to give the title compound (500 mg, 90% yield, 90% purity) as a yellow solid. $^1$H NMR (400 MHz, DMSO-d$_6$) δ 10.16 (s, 1H) 9.28 (d, J=2.4 Hz, 1H) 9.07 (s, 2H) 8.60 (d, J=5.2 Hz, 1H) 8.44-8.52 (m, 1H) 8.32 (s, 1H) 8.18-8.25 (m, 1H) 7.64-7.78 (m, 1H) 7.19-7.52 (m, 1H) 1.52 (s, 9H) 1.09-1.28 (m, 1H) 0.35-0.50 (m, 2H) 0.24 (q, J=4.8 Hz, 2H); LC-MS (ESI+) m/z 596.2 (M+H)$^+$.

3-[5-[3-[2-(2-Aminoethoxy)ethoxy]propyl]-3-methyl-2-oxo-benzimidazol-1-yl]piperidine-2,6-dione (Intermediate VR)

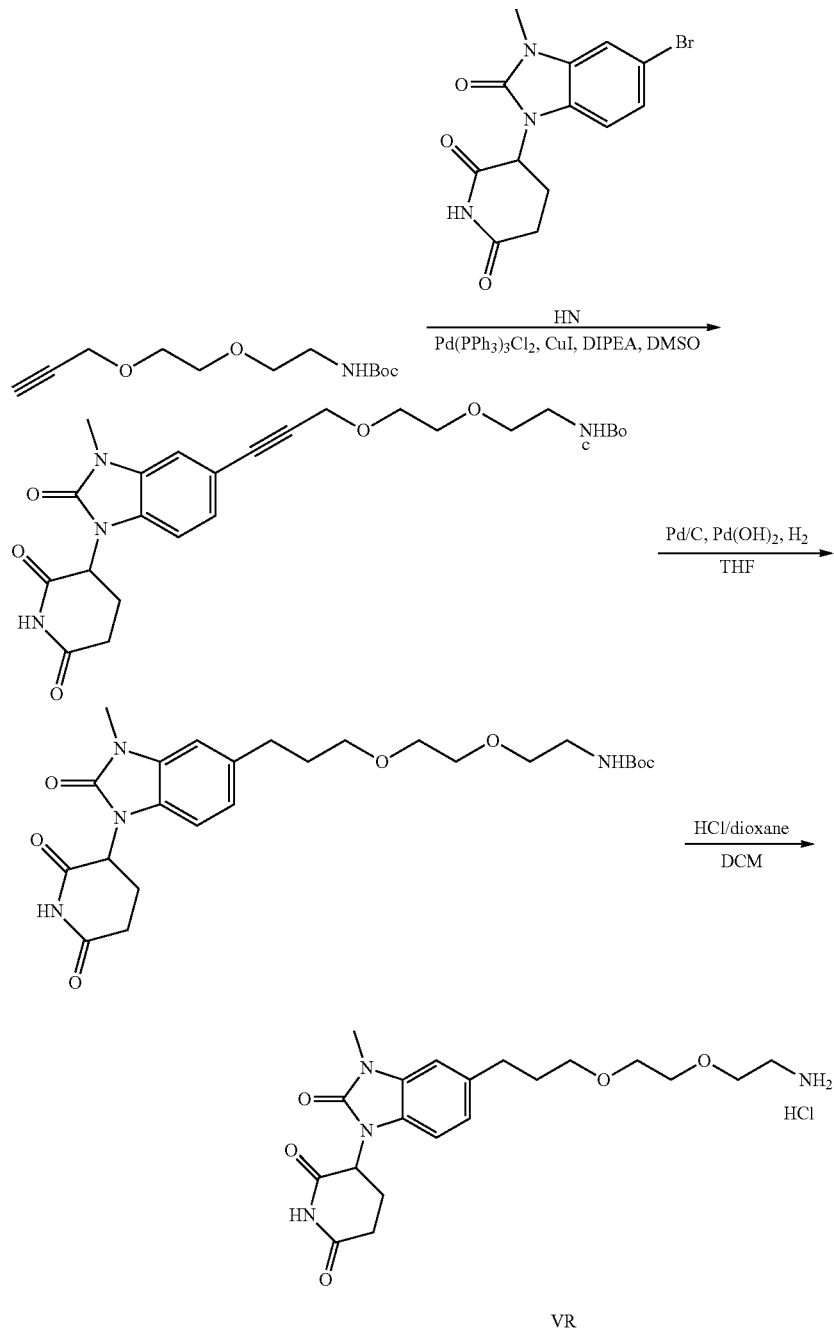

VR

Step 1—Tert-butyl N-[2-[2-[3-[1-(2,6-dioxo-3-piperidyl)-3-methyl-2-oxo-benzimidazol-5-yl]prop-2-ynoxy]ethoxy]ethyl]carbamate To a solution of 3-(5-bromo-3-methyl-2-oxo-benzimidazol-1-yl)piperidine-2,6-dione (250 mg, 739 umol, Intermediate HN) and tert-butyl N-[2-(2-prop-2-ynoxyethoxy)ethyl]carbamate (540 mg, 2.22 mmol, synthesized via Step 1 of Intermediate CQ) in DMSO (10 mL) was added CuI (28.2 mg, 148 umol), DIPEA (478 mg, 3.70 mmol) and Pd(PPh$_3$)$_2$Cl$_2$ (104 mg, 148 umol). The mixture was stirred at 80° C. for 2 hrs in a glove box. On completion, the reaction mixture was purified by reverse phase chromatography (0.1% FA condition) to give the title compound (140 mg, 35% yield) as a yellow solid. $^1$H NMR (400 MHz, DMSO-d6) δ 11.12 (s, 1H), 7.33 (s, 1H), 7.22-7.09 (m, 2H), 6.86-6.71 (m, 1H), 5.42-5.37 (m, 1H), 4.40 (s, 2H), 3.67-3.61 (m, 2H), 3.59-3.53 (m, 2H), 3.08 (m, 2H), 2.95-2.86 (m, 1H), 2.08-2.00 (m, 1H), 1.37 (s, 9H). LC-MS (ESI$^+$) m/z 506.3 (M+4)$^+$.

Step 2—Tert-butyl N-[2-[2-[3-[1-(2,6-dioxo-3-piperidyl)-3-methyl-2-oxo-benzimidazol-5-yl]propoxy]ethoxy]ethyl]carbamate To a solution of tert-butyl N-[2-[2-[3-[1-(2,6-dioxo-3-piperidyl)-3-methyl-2-oxo-benzimidazol-5-yl]prop-2-ynoxy]ethoxy]ethyl]carbamate (120 mg, 240 umol) in THF (20 mL) was added Pd/C (50 mg, 50 wt %) and Pd(OH)$_2$/C (50 mg, 10 wt %) under N$_2$. The suspension was degassed under vacuum and purged with H$_2$ several times. The mixture was stirred under H$_2$ (15 psi) at 15° C. for 2 hours. On completion, the mixture was filtered through celite. The filtrate was concentrated in vacuo to give the title compound (100 mg, 80% yield) as a yellow solid. LC-MS (ESI$^+$) m/z 505.3 (M+H)$^+$.

Step 3—3-[5-[3-[2-(2-Aminoethoxy)ethoxy]propyl]-3-methyl-2-oxo-benzimidazol-1-yl]piperidine-2,6-dione To a solution of tert-butyl N-[2-[2-[3-[1-(2,6-dioxo-3-piperidyl)-3-methyl-2-oxo-benzimidazol-5-yl]propoxy]ethoxy]ethyl]carbamate (100 mg, 198 umol) in DCM (10 mL) was added HCl/dioxane (4 M, 5 mL). The mixture was stirred at 15° C. for 0.5 hr. On completion, the mixture was concentrated in vacuo to give the title compound (80.0 mg, 95% yield) as a yellow solid. LC-MS (ESI$^+$) m/z 405.2 (M+H)$^+$.

Tert-butyl N-[2-[2-(2-prop-2-ynoxyethoxy)ethoxy]ethyl]carbamate (Intermediate VS)

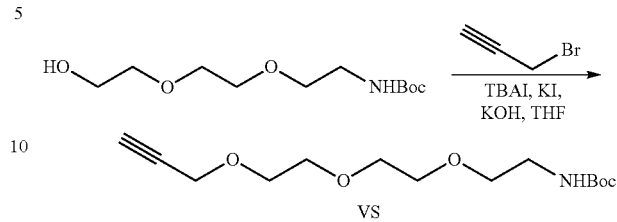

A mixture of tert-butyl N-[2-[2-(2-hydroxyethoxy)ethoxy]ethyl]carbamate (3.00 g, 12.0 mmol), 3-bromoprop-1-yne (1.72 g, 14.4 mmol, 1.24 mL), TBAI (356 mg, 962 umol), KI (299 mg, 1.81 mmol) and KOH (675 mg, 12.0 mmol) in THF (30 mL) was degassed and purged with N$_2$ for 3 times, and then the mixture was stirred at 25° C. for 16 hrs under N$_2$ atmosphere. On completion, the mixture was filtered and the filtrate was concentrated in vacuo. The residue was purified by silica gel chromatography to give the title compound (2.50 g, 72% yield) as light yellow oil. $^1$H NMR (400 MHz, CDCl$_3$) δ 5.05 (s, 1H), 4.22 (d, J=2.4 Hz, 2H), 3.76-3.60 (m, 8H), 3.55 (t, J=5.2 Hz, 2H), 3.35-3.27 (m, 2H), 2.44 (t, J=2.4 Hz, 1H), 1.47 (s, 9H).

3-[5-[3-[2-[2-(2-Aminoethoxy)ethoxy]ethoxy]propyl]-3-methyl-2-oxo-benzimidazol-1-yl]piperidine-2,6-dione (Intermediate VT)

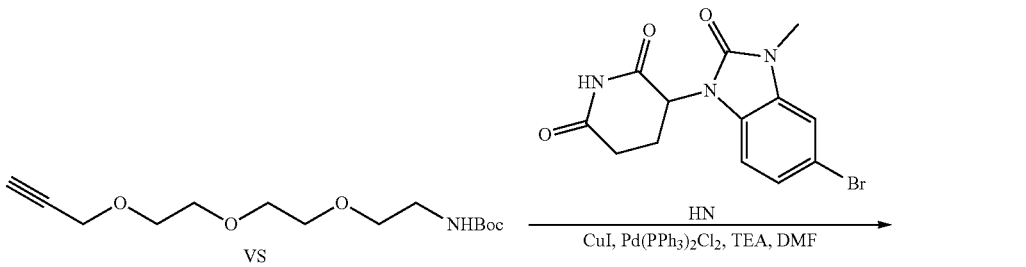

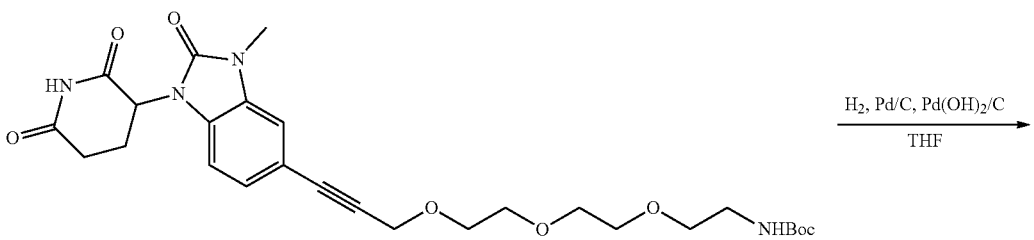

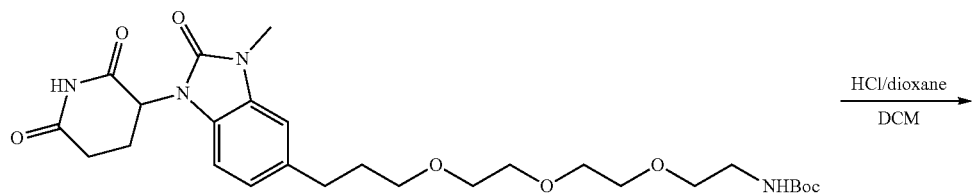

-continued

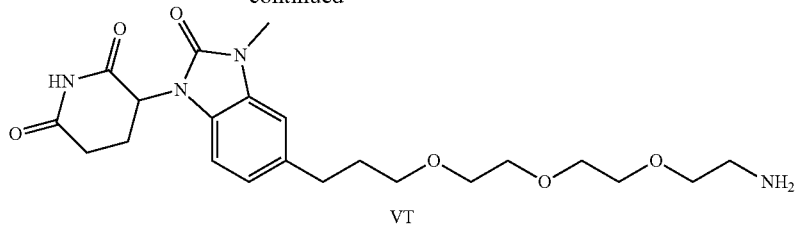

VT

Step 1—Tert-butyl N-[2-[2-[2-[3-[1-(2,6-dioxo-3-piperidyl)-3-methyl-2-oxo-benzimidazol-5-yl]prop-2-ynoxy]ethoxy]ethoxy]ethyl]carbamate A mixture of tert-butyl N-[2-[2-(2-prop-2-ynoxyethoxy)ethoxy]ethyl]carbamate (849 mg, 2.96 mmol, Intermediate VS), 3-(5-bromo-3-methyl-2-oxo-benzimidazol-1-yl)piperidine-2,6-dione (500 mg, 1.48 mmol, Intermediate HN), Pd(PPh$_3$)$_2$Cl$_2$ (311 mg, 443 umol), CuI (84 mg, 443 umol) and TEA (2.69 g, 26.6 mmol, 3.70 mL) in DMF (15 mL) was degassed and purged with N$_2$ for 3 times, and then the mixture was stirred at 80° C. for 3 hrs under N$_2$ atmosphere. On completion, the mixture was concentrated in vacuo to give a residue. The residue was purified by reverse phase chromatography (0.1% FA) to give the title compound (400 mg, 49% yield) as light yellow solid. $^1$H NMR (400 MHz, DMSO-d$_6$) δ 11.12 (s, 1H), 7.33 (s, 1H), 7.21-7.12 (m, 2H), 6.77-6.71 (m, 1H), 5.39 (dd, J=5.2, 12.8 Hz, 1H), 4.40 (s, 2H), 3.68-3.62 (m, 2H), 3.61-3.56 (m, 2H), 3.55-3.47 (m, 6H), 3.35 (s, 3H), 3.07 (q, J=6.0 Hz, 2H), 2.96-2.80 (m, 1H), 2.72-2.58 (m, 2H), 2.08-1.99 (m, 1H), 1.37 (s, 9H).

Step 2—Tert-butyl N-[2-[2-[2-[3-[1-(2,6-dioxo-3-piperidyl)-3-methyl-2-oxo-benzimidazol-5-yl]propoxy]ethoxy]ethoxy]ethyl]carbamate To a solution of tert-butyl N-[2-[2-[2-[3-[1-(2,6-dioxo-3-piperidyl)-3-methyl-2-oxo-benzimidazol-5-yl]prop-2-ynoxy]ethoxy]ethoxy]ethyl]carbamate (400 mg, 734 umol) in THF (100 mL) was added Pd/C (300 mg, 10 wt %) and Pd(OH)$_2$/C (300 mg, 10 wt %). The mixture was stirred at 20° C. for 4 hrs under H$_2$ (15 psi) atmosphere. On completion, the mixture was filtered and the filtrate was concentrated in vacuo to give the title compound (270 mg, 67% yield) as light yellow solid. $^1$H NMR (400 MHz, DMSO-d$_6$) δ 11.07 (s, 1H), 7.08-6.96 (m, 2H), 6.87 (d, J=7.2 Hz, 1H), 6.73 (s, 1H), 5.34 (dd, J=5.2, 12.4 Hz, 1H), 3.69-3.35 (m, 15H), 3.09-3.01 (m, 2H), 2.97-2.81 (m, 1H), 2.77-2.57 (m, 4H), 2.08-1.94 (m, 1H), 1.89-1.71 (m, 2H), 1.37 (s, 9H).

Step 3—3-[5-[3-[2-[2-(2-Aminoethoxy)ethoxy]ethoxy]propyl]-3-methyl-2-oxo-benzimidazol-1-yl]piperidine-2,6-dione To a solution of tert-butyl N-[2-[2-[2-[3-[1-(2,6-dioxo-3-piperidyl)-3-methyl-2-oxo-benzimidazol-5-yl]propoxy]ethoxy]ethoxy]ethyl]carbamate (270 mg, 492 umol) in DCM (10 mL) was added HCl/dioxane (4 M, 5 mL). The mixture was stirred at 25° C. for 3 hrs. On completion, the mixture was concentrated in vacuo to give the title compound (220 mg, 92% yield) as light yellow solid. $^1$H NMR (400 MHz, DMSO-d$_6$) δ 11.08 (s, 1H), 7.86 (s, 3H), 7.07-6.97 (m, 2H), 6.91-6.84 (m, 1H), 5.40-5.29 (m, 1H), 3.61 (t, J=5.2 Hz, 2H), 3.59-3.56 (m, 4H), 3.55-3.53 (m, 2H), 3.52-3.48 (m, 2H), 3.43-3.40 (m, 2H), 3.33 (s, 3H), 3.02-2.84 (m, 3H), 2.76-2.58 (m, 4H), 2.05-1.97 (m, 1H), 1.87-1.73 (m, 2H).

3-[4-[3-[2-[2-(2-Aminoethoxy)ethoxy]ethoxy]propyl]-3-methyl-2-oxo-benzimidazol-1-yl]piperidine-2,6-dione (Intermediate VU)

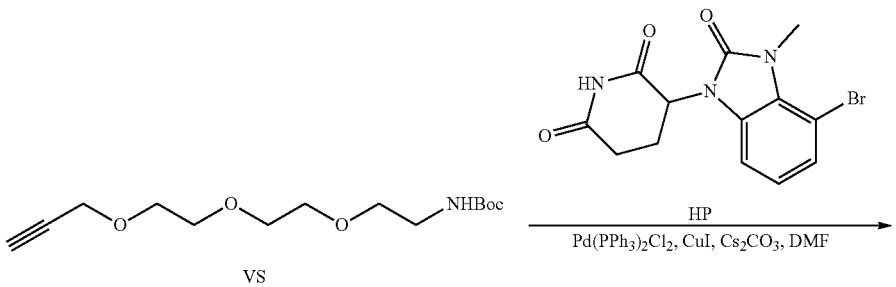

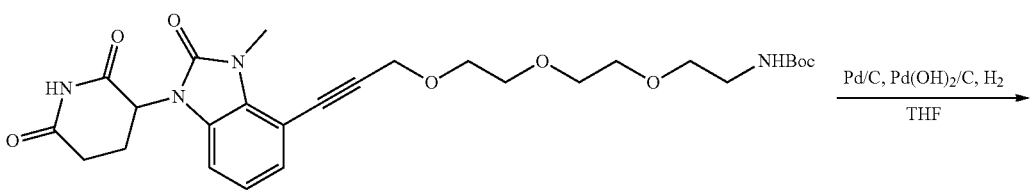

-continued

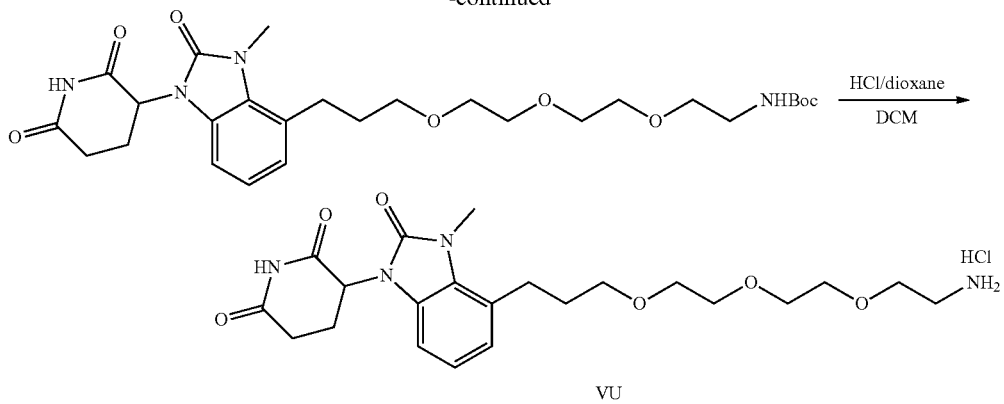

Step 1—Tert-butyl N-[2-[2-[2-[3-[1-(2,6-dioxo-3-piperidyl)-3-methyl-2-oxo-benzimidazol-4-yl]prop-2-ynoxy]ethoxy]ethoxy]ethyl]carbamate A mixture of tert-butyl N-[2-[2-(2-prop-2-ynoxyethoxy)ethoxy]ethyl]carbamate (1.27 g, 4.44 mmol, Intermediate VS), 3-(4-bromo-3-methyl-2-oxo-benzimidazol-1-yl)piperidine-2,6-dione (500 mg, 1.48 mmol, Intermediate HP), CuI (85 mg, 446 umol), Pd(PPh$_3$)$_2$Cl$_2$ (311 mg, 443 umol) and Cs$_2$CO$_3$ (2.41 g, 7.39 mmol) in DMF (12 mL) was stirred at 80° C. for 2 hours under N$_2$ atmosphere. On completion, after cooled to 25° C., the mixture was filtered through a pad of celite and the cake was washed with EA (50 mL). The filtrate and washing were combined, diluted with water (100 mL), and extracted with EA (3×40 mL). The combined organic layer was washed with brine (10 mL), dried over Na$_2$SO$_4$, filtered and concentrated in vacuo. The residue was purified by reversed phase chromatography (0.1% FA condition) to give the title compound (420 mg, 52% yield) as light yellow gum. $^1$H NMR (400 MHz, DMSO-d$_6$) δ 11.11 (s, 1H), 7.17 (d, J=8.0 Hz, 1H), 7.10-7.15 (m, 1H), 7.00-7.06 (m, 1H), 5.39 (dd, J=12.4, 5.6 Hz, 1H), 4.46 (s, 2H), 3.61-3.69 (m, 5H), 3.55-3.60 (m, 2H), 3.46-3.55 (m, 6H), 3.05 (q, J=6.0 Hz, 2H), 2.83-2.93 (m, 1H), 2.58-2.76 (m, 3H), 2.04-2.02 (m, 1H), 1.36 (s, 9H).

Step 2—Tert-butyl N-[2-[2-[2-[3-[1-(2,6-dioxo-3-piperidyl)-3-methyl-2-oxo-benzimidazol-4-yl]propoxy]ethoxy]ethoxy]ethyl]carbamate To a solution of tert-butyl N-[2-[2-[2-[3-[1-(2,6-dioxo-3-piperidyl)-3-methyl-2-oxo-benzimidazol-4-yl]prop-2-ynoxy]ethoxy]ethoxy]ethyl]carbamate (500 mg, 918 umol) in THF (10 mL) was added Pd/C (200 mg, 918 umol, 10 wt %) and Pd(OH)$_2$ (200 mg, 1.42 mmol). The mixture was stirred at 25° C. for 16 hours under H$_2$ (15 psi). On completion, the mixture was filtered through a pad of celite, and the cake was washing with EA (20 mL). The filtrate and washing were combined and concentrated in vacuo to give the title compound (500 mg, 90% yield) as light yellow gum. LC-MS (ESI$^+$) m/z 549.2 (M+H)$^+$.

Step 3—3-[4-[3-[2-[2-(2-Aminoethoxy)ethoxy]ethoxy]propyl]-3-methyl-2-oxo-benzimidazol-1-yl]piperidine-2,6-dione To a mixture of tert-butyl N-[2-[2-[2-[3-[1-(2,6-dioxo-3-piperidyl)-3-methyl-2-oxo-benzimidazol-4-yl]propoxy]ethoxy]ethoxy]ethyl]carbamate (100 mg, 182 umol) in DCM (2 mL) was added HCl/dioxane (4 M, 4.00 mL). The reaction mixture was stirred at 25° C. for 1 hour. On completion, the reaction mixture was concentrated in vacuo to give the title compound (100 mg, 98% yield, HCl) as light yellow solid. LC-MS (ESI$^+$) m/z 449.3 (M+H)$^+$.

Tert-butyl 2-(2-allyloxyethoxy)acetate (Intermediate VV)

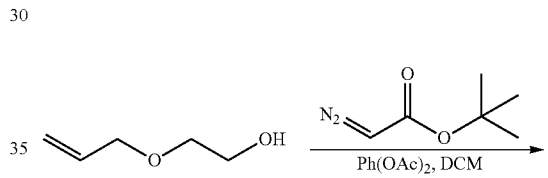

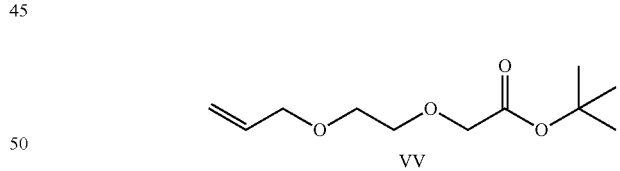

VV

To a mixture of 2-allyloxyethanol (3.00 g, 29.3 mmol) and diacetoxyrhodium (520 mg, 1.18 mmol) in DCM (30 mL) was added a solution of tert-butyl 2-diazoacetate (12.5 g, 88.1 mmol, CAS #35059-50-8) in DCM (30 mL) at 25° C. dropwise during 2 hours. The mixture was stirred at 25° C. for 16 hours under N$_2$. On completion, to the mixture was added HOAc (5.0 mL). Then, the mixture was stirred at 25° C. for 0.5 hour. The mixture was concentrated in vacuo. The residue was purified by column chromatography over silica gel to give the title compound (6.80 g, 100% yield) as light yellow oil. $^1$H NMR (400 MHz, CDCl$_3$) δ 6.00-5.85 (m, 1H), 5.29 (dd, J=17.2, 2.0 Hz, 1H), 5.19 (dd, J=10.4, 1.6 Hz, 1H), 4.07-4.02 (m, 4H), 3.77-3.71 (m, 2H), 3.67-3.59 (m, 2H), 1.49 (s, 9H).

1955

2-[2-[3-[1-(2,6-Dioxo-3-piperidyl)-3-methyl-2-oxo-benzimidazol-5-yl]propoxy]ethoxy]acetic acid (Intermediate VW)

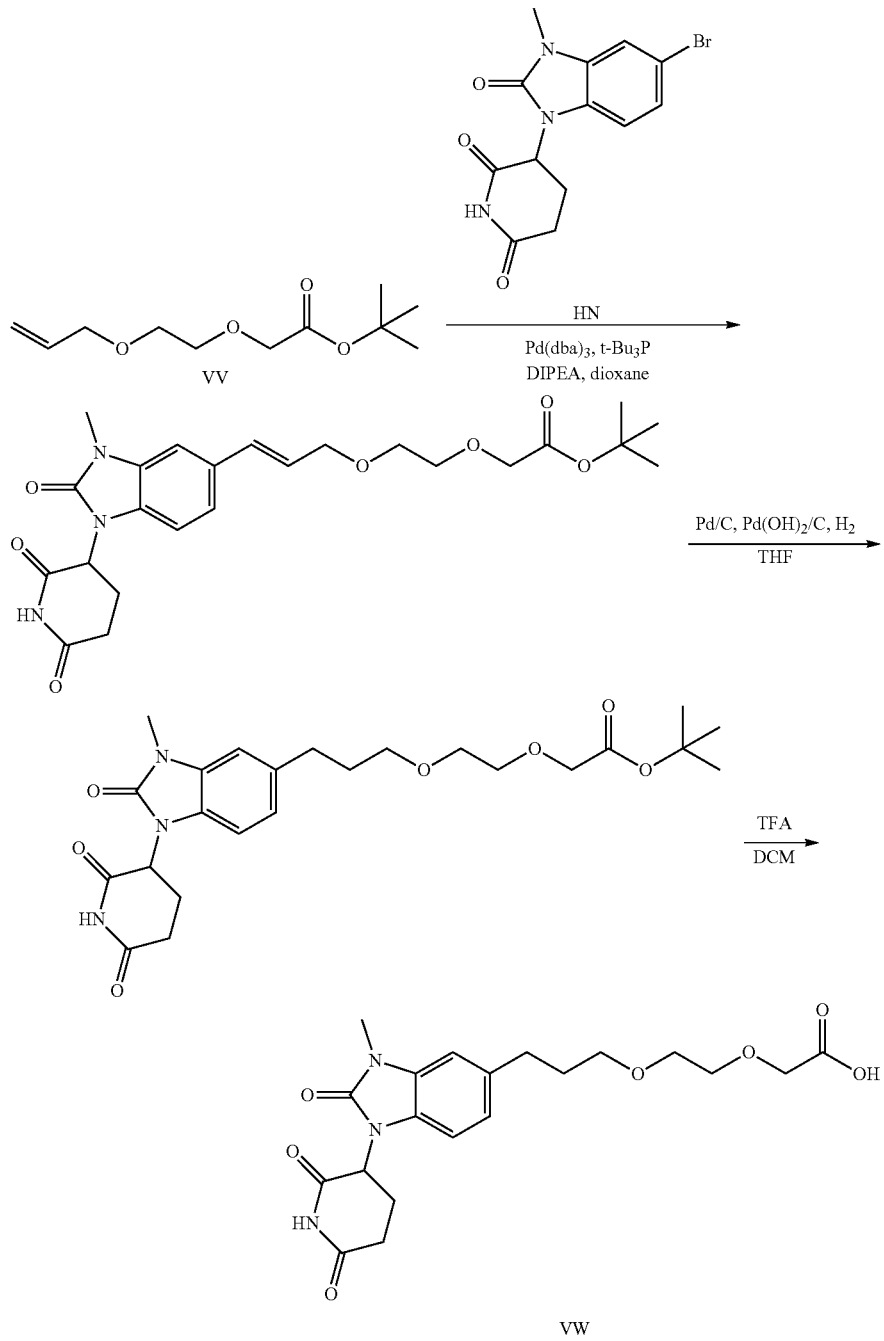

Step 1—Tert-butyl 2-[2-[(E)-3-[1-(2,6-dioxo-3-piperidyl)-3-methyl-2-oxo-benzimidazol-5-yl]allyloxy]ethoxy]acetate A mixture of tert-butyl 2-(2-allyloxyethoxy)acetate (1.50 g, 4.62 mmols, Intermediate VV), 3-(5-bromo-3-methyl-2-oxo-benzimidazol-1-yl)piperidine-2,6-dione (600 mg, 1.77 mmol, Intermediate HN), $Pd_2(dba)_3$ (168 mg, 183 umol), t-$Bu_3P$ (720 mg, 355 umol, 10 wt %) and DIPEA (468 mg,

1956

3.62 mmol) in dioxane (30 mL) was stirred at 25° C. for 16 hours under $N_2$. On completion, the mixture was filtered. The filtrate was concentrated in vacuo. The residue was purified by reversed phase (0.1% FA condition) to give the title compound (500 mg, 59% yield) as light yellow oil. LC-MS (ESI$^+$) m/z 496.1 (M+Na)$^+$.

Step 2-Tert-butyl 2-[2-[3-[1-(2,6-dioxo-3-piperidyl)-3-methyl-2-oxo-benzimidazol-5-yl]propoxy]ethoxy]acetate A mixture of tert-butyl 2-[2-[(E)-3-[1-(2,6-dioxo-3-piperidyl)-3-methyl-2-oxo-benzimidazol-5-yl]allyloxy]ethoxy]

acetate (500 mg), Pd/C (200 mg, 10 wt %) and Pd(OH)₂ (200 mg, 1.42 mmol) in THF (10 mL) was stirred at 25° C. for 16 hours under H₂ (15 psi). On completion, the mixture was filtered, and the cake was washed with EA (20 mL). The filtrate and washings were combined and concentrated in vacuo. The residue was purified by reversed phase (0.1% FA condition) to give the title compound (400 mg) as light yellow oil. ¹H NMR (400 MHz, CDCl₃) δ 8.14 (s, 1H), 6.93-6.87 (m, 2H), 6.72 (d, J=8.0 Hz, 1H), 5.25-5.20 (m, 1H), 4.05 (s, 2H), 3.75-3.72 (m, 2H), 3.66-3.62 (m, 2H), 3.49 (t, J=6.4 Hz, 2H), 3.45 (s, 3H), 2.96-2.83 (m, 2H), 2.76-2.71 (m, 2H), 2.29-2.19 (m, 2H), 1.95-1.90 (m, 2H) 1.49 (s, 9H).

Step 3—2-[2-[3-[1-(2,6-Dioxo-3-piperidyl)-3-methyl-2-oxo-benzimidazol-5-yl]propoxy]ethoxy]acetic acid To a solution of tert-butyl 2-[2-[3-[1-(2,6-dioxo-3-piperidyl)-3-methyl-2-oxo-benzimidazol-5-yl]propoxy]ethoxy]acetate (400 mg, 815 umol) in DCM (4 mL) was added TFA (4 mL) at 25° C. The mixture was stirred at 25° C. for 16 hours. On completion, the mixture was concentrated in vacuo. The residue was purified by reverse phase flash (0.1% TFA condition) to give the title compound (180 mg, 42% yield) as light yellow gum. ¹H NMR (400 MHz, CDCl₃) δ 8.35 (s, 1H), 6.94-6.87 (m, 2H), 6.74 (d, J=8.0 Hz, 1H), 5.26-5.22 (m, 1H), 4.18 (s, 2H), 3.81-3.74 (m, 2H), 3.64-3.62 (m, 2H), 3.55 (t, J=6.4 Hz, 2H), 3.44 (s, 3H), 2.92-2.72 (m, 6H), 2.29-2.19 (m, 1H), 2.00-1.90 (m, 2H).

Methyl 4-[4-amino-3-(difluoromethyl)pyrazol-1-yl]-2-fluoro-benzoate (Intermediate VX)

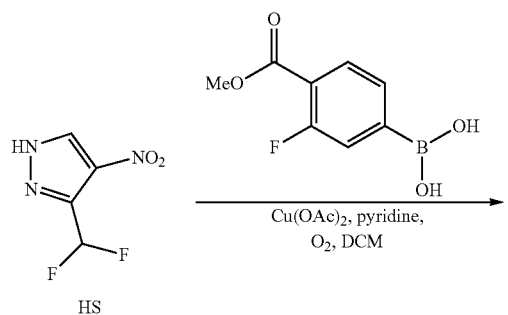

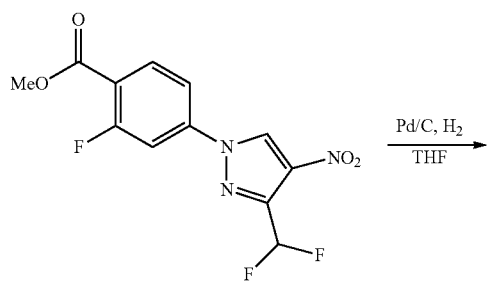

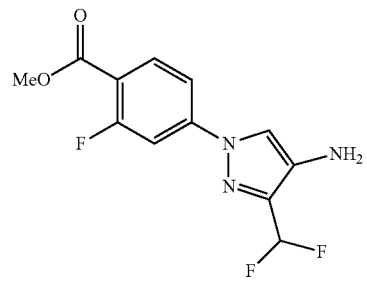

VX

Step 1—Methyl 4-[3-(difluoromethyl)-4-nitro-pyrazol-1-yl]-2-fluoro-benzoate

To a solution of 3-(difluoromethyl)-4-nitro-1H-pyrazole (1.00 g, 6.13 mmol, Intermediate HS) and (3-fluoro-4-methoxycarbonyl-phenyl)boronic acid (1.58 g, 7.97 mmol, CAS #3505083-04-5) in DCM (20 mL) was added Cu(OAc)₂ (2.23 g, 12.3 mmol) and pyridine (10 mL). The reaction mixture was stirred at 25° C. for 12 hrs under oxygen (15 psi) atmosphere. On completion, the mixture was quenched with ammonia water (30 mL), then the mixture was stirred and separated. The organic layer was acidified with 1N HCl (20 mL) to pH<5, separated and washed with brine (20 mL), concentrated in vacuo. The residue was purified by silica gel chromatography (SiO₂), and then triturated with PE/EA=10/1 (50 mL), filtered and the filter cake was concentrated in vacuo to give the title compound (360 mg, 19% yield) as a white solid. ¹H NMR (400 MHz, DMSO-d₆) δ 9.92 (s, 1H), 8.16-8.04 (m, 2H), 8.02-7.94 (m, 1H), 7.61-7.30 (m, 1H), 3.89 (s, 3H).

Step 2—Methyl 4-[4-amino-3-(difluoromethyl)pyrazol-1-yl]-2-fluoro-benzoate

To a solution of methyl 4-[3-(difluoromethyl)-4-nitro-pyrazol-1-yl]-2-fluoro-benzoate (350 mg, 1.11 mmol) in THF (10 mL) was added Pd/C (0.1 g, 10% wt). The reaction mixture was stirred at 25° C. for 10 hrs under H₂ (15 psi) atmosphere. On completion, the mixture was concentrated in vacuo to give the title compound (310 mg, 98% yield) as a white solid. LC-MS (ESI⁺) m/z 286.1 (M+H)⁺.

4-[4-[[2-[2-[Tert-butoxycarbonyl(cyclopropylmethyl)amino]-4-pyridyl]oxazole-4-carbonyl]amino]-3-(difluoromethyl)pyrazol-1-yl]-2-fluoro-benzoic acid (Intermediate VY)

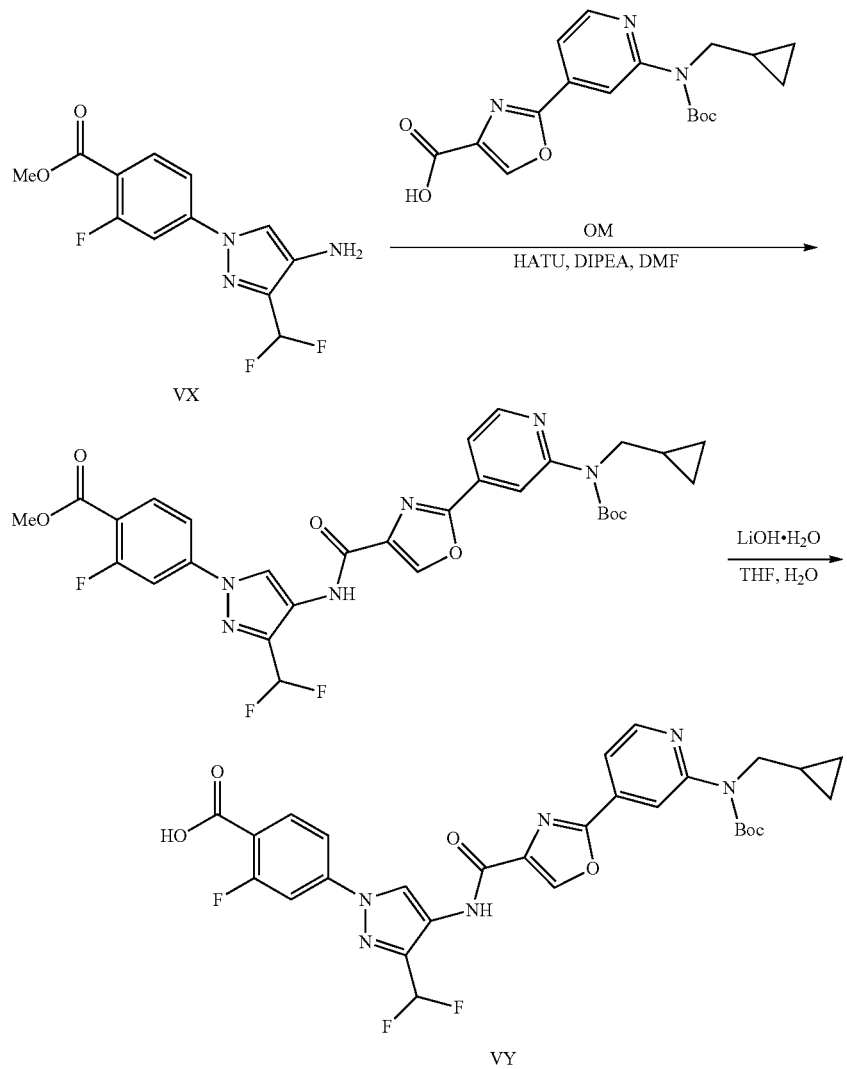

Step 1—Methyl 4-[4-[[2-[2-[tert-butoxycarbonyl(cyclopropylmethyl)amino]-4-pyridyl]oxazole-4-carbonyl]amino]-3-(difluoromethyl)pyrazol-1-yl]-2-fluoro-benzoate To a solution of methyl 4-[4-amino-3-(difluoromethyl)pyrazol-1-yl]-2-fluoro-benzoate (310 mg, 1.09 mmol, Intermediate VX) and 2-[2-[tert-butoxycarbonyl(cyclopropylmethyl)amino]-4-pyridyl]oxazole-4-carboxylic acid (391 mg, 1.09 mmol, Intermediate OM) in DMF (6.00 mL) was added HATU (496 mg, 1.30 mmol) and DIPEA (421 mg, 3.26 mmol). The reaction mixture was stirred at 20° C. for 0.5 hr. On completion, the mixture was quenched with water (50 mL), and filtered. The filter cake was dried in vacuo to give the title compound (600 mg, 88% yield) as a white solid. $^1$H NMR (400 MHz, DMSO-d$_6$) δ 10.15 (s, 1H), 9.06 (s, 1H), 9.01 (s, 1H), 8.60 (d, J=5.2 Hz, 1H), 8.32 (s, 1H), 8.06 (t, J=8.4 Hz, 1H), 8.00-7.94 (m, 1H), 7.94-7.88 (m, 1H), 7.75-7.66 (m, 1H), 7.46-7.16 (m, 1H), 3.88 (s, 3H), 3.86 (s, 2H), 1.52 (s, 9H), 1.22-1.12 (m, 1H), 0.45-0.37 (m, 2H), 0.28-0.21 (m, 2H); LC-MS (ESI$^+$) m/z 627.0 (M+H)$^+$.

Step 2—4-[4-[[2-[2-[Tert-butoxycarbonyl(cyclopropylmethyl)amino]-4-pyridyl]oxazole-4-carbonyl]amino]-3-(difluoromethyl)pyrazol-1-yl]-2-fluoro-benzoic acid To a mixture of methyl 4-[4-[[2-[2-[tert-butoxycarbonyl(cyclopropylmethyl)amino]-4-pyridyl]oxazole-4-carbonyl]amino]-3-(difluoromethyl)pyrazol-1-yl]-2-fluoro-benzoate (600 mg, 958 umol) in a mixed solvent of THF (10 mL) and H$_2$O (2 mL) was added LiOH.H$_2$O (160 mg, 3.83 mmol). The reaction mixture was stirred at 25° C. for 10 hrs. On completion, the mixture was concentrated in vacuo to remove the THF. The residue was diluted with water (30 mL), acidified with 1N HCl to pH=3-5, filtered and the filter cake was dried in vacuo to give the title compound (570 mg, 97% yield) as a yellow solid. $^1$H NMR (400 MHz, DMSO-d$_6$) δ 10.15 (s, 1H), 9.15-8.95 (m, 2H), 8.60 (d, J=5.2 Hz, 1H), 8.32 (s, 1H), 8.03 (t, J=8.0 Hz, 1H), 7.94-7.83 (m, 2H), 7.71 (d, J=4.8 Hz, 1H), 7.47-7.15 (m, 1H), 3.87 (d, J=6.8 Hz, 2H), 1.52 (s, 9H), 0.80-0.69 (m, 1H), 0.49-0.36 (m, 2H), 0.29-0.15 (m, 2H); LC-MS (ESI+) m/z 613.2 (M+H)+.

Tert-butyl N-(cyclopropylmethyl)-N-[4-[4-[[3-(difluoromethyl)-1-(3-fluoro-4-formyl-phenyl) pyrazol-4-yl]carbamoyl]oxazol-2-yl]-2-pyridyl]carbamate (Intermediate NZ)

Step 1—Isopropoxycarbonyl 4-[4-[[2-[2-[tert-butoxycarbonyl(cyclopropylmethyl)amino]-4-pyridyl]oxazole-4-carbonyl]amino]-3-(difluoromethyl)pyrazol-1-yl]-2-fluoro-benzoate To a solution of 4-[4-[[2-[2-[tert-butoxycarbonyl(cyclopropylmethyl)amino]-4-pyridyl]oxazole-4-carbonyl]amino]-3-(difluoromethyl)pyrazol-1-yl]-2-fluoro-benzoic acid (1.00 g, 1.63 mmol, Intermediate VY) and TEA (413 mg, 4.08 mmol) in THF (30 mL) was added isopropyl carbonochloridate (400 mg, 3.27 mmol) dropwise. The reaction mixture was stirred at 0° C. for 2 hrs. On comple-

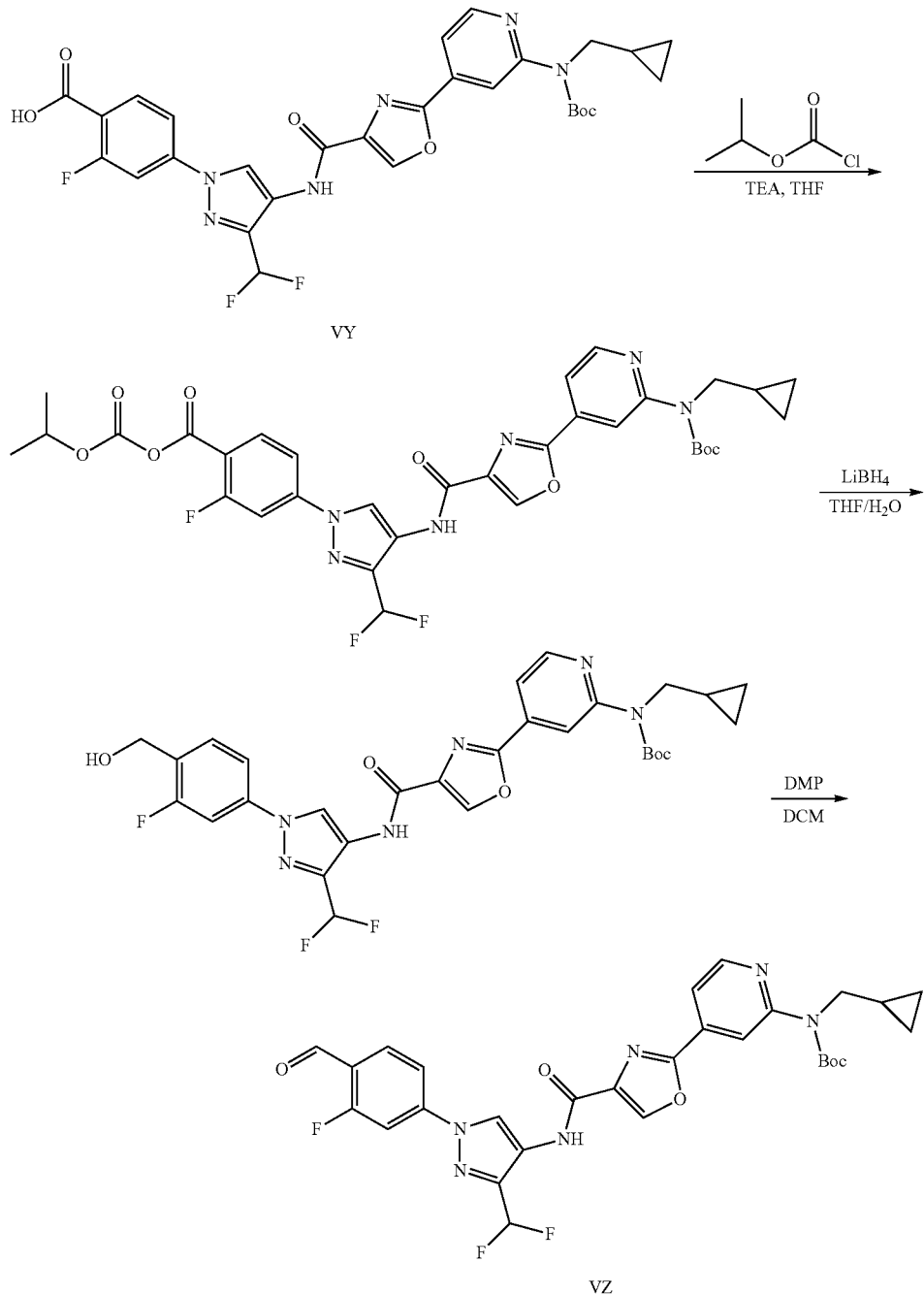

Step 2—Tert-butyl N-(cyclopropylmethyl)-N-[4-[4-[[3-(difluoromethyl)-1-[3-fluoro-4-(hydroxymethyl) phenyl]pyrazol-4-yl]carbamoyl]oxazol-2-yl]-2-pyridyl]carbamate To a solution of isopropoxycarbonyl 4-[4-[[2-[2-[tert-butoxycarbonyl(cyclopropylmethyl)amino]-4-pyridyl]oxazole-4-carbonyl]amino]-3-(difluoromethyl)pyrazol-1-yl]-2-fluoro-benzoate (1.14 g, 1.63 mmol) in a mixed solvent of THF (60 mL) and H₂O (1 mL) was added LiBH₄ (178 mg, 8.16 mmol). The reaction mixture was stirred at 0° C. for 2 hrs. On completion, the mixture was quenched with water (50 mL), then extracted with EA (2×50 mL). The organic layers were washed with brine (50 mL), dried over Na₂SO₄, and concentrated in vacuo. The residue was triturated with DCM/PE=1/10 (50 mL), filtered and the filter cake was dried in vacuo to give the title compound (0.91 g, 93% yield) as a white solid. $^1$H NMR (300 MHz, DMSO-d$_6$) δ 10.09 (s, 1H), 9.05 (s, 1H), 8.87 (s, 1H), 8.60 (d, J=5.1 Hz, 1H), 8.32 (s, 1H), 7.80-7.68 (m, 3H), 7.61 (t, J=8.4 Hz, 1H), 7.30 (t, J=54.3, Hz, 1H), 5.37 (t, J=5.7 Hz, 1H), 4.58 (d, J=5.7 Hz, 2H), 3.86 (d, J=7.2 Hz, 2H), 1.51 (s, 9H), 1.20-1.10 (m, 1H), 0.44-0.37 (m, 2H), 0.27-0.20 (m, 2H); LC-MS (ESI$^+$) m/z 599.2 (M+H)$^+$.

Step 3—Tert-butyl N-(cyclopropylmethyl)-N-[4-[4-[[3-(difluoromethyl)-1-(3-fluoro-4-formyl-phenyl) pyrazol-4-yl]carbamoyl]oxazol-2-yl]-2-pyridyl]carbamate To a solution of tert-butyl N-(cyclopropylmethyl)-N-[4-[4-[[3-(difluoromethyl)-1-[3-fluoro-4-(hydroxymethyl)phenyl]pyrazol-4-yl]carbamoyl]oxazol-2-yl]-2-pyridyl]carbamate (0.91 g, 1.52 mmol) in DCM (20 mL) was added DMP (774 mg, 1.82 mmol). The reaction mixture was stirred at 25° C. for 10 hrs. On completion, the mixture was quenched with Na₂S₂O₃ (30 mL) and NaHCO₃ (30 mL), stirred for 10 minutes, then extracted with DCM (2×30 mL). The organic layers were washed with brine (50 mL), dried with Na₂SO₄, filtered and the filtrate was concentrated in vacuo. The residue was triturated with PE/DCM (10/1, 50 mL), filtered and the filter cake was dried in vacuo to give the title compound (840 mg, 93% yield) as a yellow solid. $^1$H NMR (400 MHz, DMSO-d$_6$) δ 10.43 (s, 1H), 10.20 (s, 1H), 9.07 (s, 1H), 9.05 (s, 1H), 8.59 (d, J=5.2 Hz, 1H), 8.31 (s, 1H), 8.06-7.91 (m, 3H), 7.70 (dd, J=1.2, 5.2 Hz, 1H), 7.35 (t, J=107.6 Hz, 1H), 3.86 (d, J=6.8 Hz, 2H), 1.52 (s, 9H), 1.21-1.14 (m, 1H), 0.44-0.38 (m, 2H), 0.28-0.20 (m, 2H); LC-MS (ESI$^+$) m/z 597.2 (M+H)$^+$.

2-Methyl 4-amino-1-methyl-pyrazole-3-carboxylate (Intermediate WA)

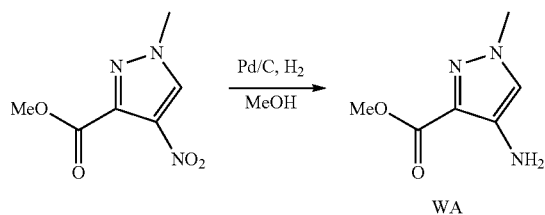

To a mixture of methyl 2-methyl-4-nitro-pyrazole-3-carboxylate (0.5 g, 2.70 mmol, synthesized via Step 1 of Intermediate LK) in MeOH (20 mL) was added Pd/C (300 mg, 10% wt). The reaction mixture was stirred at 25° C. for 12 hours under H₂ (15 psi) atmosphere. On completion, the reaction mixture was filtered and concentrated in vacuo to give the title compound (400 mg, 95% yield) as white solid. $^1$H NMR (400 MHz, DMSO-d$_6$) δ 7.12 (s, 1H), 4.67 (s, 2H), 3.74 (s, 3H), 3.72 (s, 3H).

1-4-[[5-(4-Tert-butoxycarbonylpiperazin-1-yl)pyrazolo[1,5-a]pyrimidine-3-carbonyl]amino]-1-methyl-pyrazole-3-carboxylic acid (Intermediate WB)

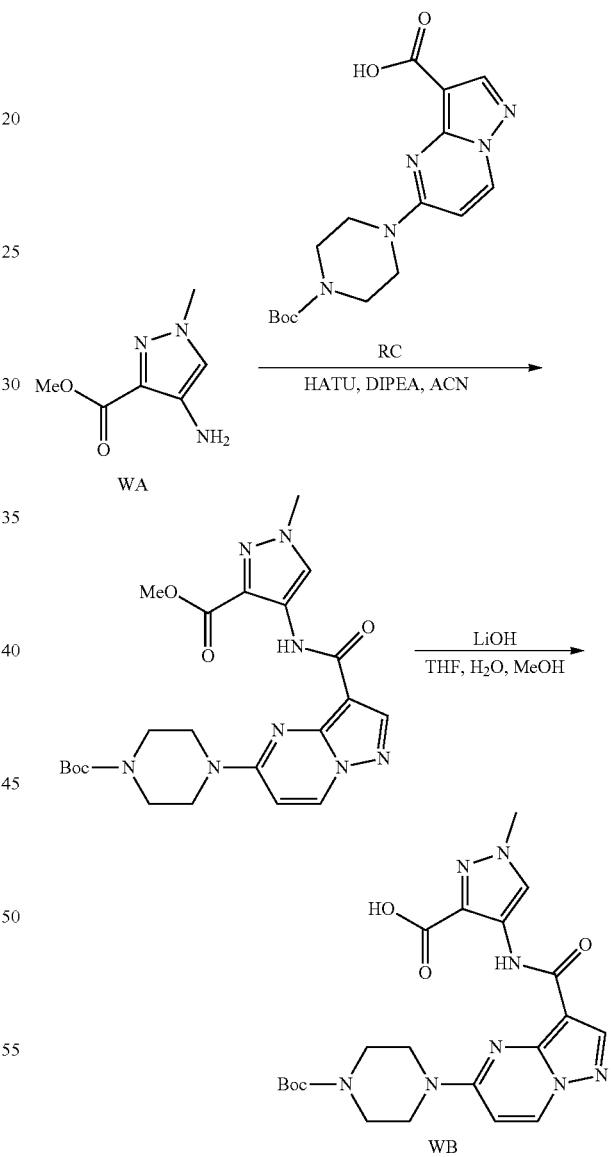

Step 1—Tert-butyl 4-[3-[(3-methoxycarbonyl-1-methyl-pyrazol-4-yl)carbamoyl]pyrazolo[1,5-a]pyrimidin-5-yl]piperazine-1-carboxylate To a mixture of methyl 4-amino-1-methyl-pyrazole-3-carboxylate (232 mg, 1.50 mmol, Intermediate WA) and 5-(4-tert-butoxycarbonylpiperazin-1-yl)pyrazolo[1,5-a]pyrimidine-3-carboxylic acid (400 mg, 1.15 mmol, Intermediate RC) in ACN (10 mL) was added DIPEA (446 mg, 3.45 mmol, 601 uL) and HATU (875 mg, 2.30 mmol). The reaction mixture was stirred at 60° C. for 12 hours. On completion, the reaction mixture was concentrated in vacuo. The residue was purified by prep-HPLC (0.1% FA condition) to give the title compound (250 mg, 44% yield) as white solid. $^1$H NMR (400 MHz, DMSO-$d_6$) δ 10.17 (s, 1H), 8.80 (d, J=8.0 Hz, 1H), 8.44 (s, 1H), 8.29 (s, 1H), 6.88 (d, J=8.0 Hz, 1H), 4.02-3.92 (m, 7H), 3.86 (s, 3H), 3.61-3.49 (m, 4H), 1.42 (s, 9H).

Step 2—1-4-[[5-(4-Tert-butoxycarbonylpiperazin-1-yl)pyrazolo[1,5-a]pyrimidine-3-carbonyl]amino]-1-methyl-pyrazole-3-carboxylic acid To a mixture of tert-butyl 4-[3-[(3-methoxycarbonyl-1-methyl-pyrazol-4-yl)carbamoyl]pyrazolo[1,5-a]pyrimidin-5-yl]piperazine-1-carboxylate (200 mg, 412 umol) in a solution of THF (10 mL), MeOH (2 mL) and H$_2$O (2 mL) was added LiOH (98.8 mg, 4.13 mmol). The reaction mixture was stirred at 25° C. for 12 hours. On compound, the reaction mixture was acidified with HCl (1 N) until pH=5-6, then the mixture was concentrated in vacuo to give the title compound (194 mg, 99% yield) as white solid. $^1$H NMR (400 MHz, DMSO-$d_6$) δ 10.53 (s, 1H), 8.76 (d, J=7.2 Hz, 1H), 8.28 (d, J=17.6 Hz, 2H), 6.85 (d, J=7.6 Hz, 1H), 4.12-3.87 (m, 4H), 3.86 (s, 3H), 3.55-3.49 (m, 4H), 1.43 (s, 9H).

Methyl 5-(4-amino-1-methyl-pyrazol-3-yl)pyridine-3-carboxylate (Intermediate WC)

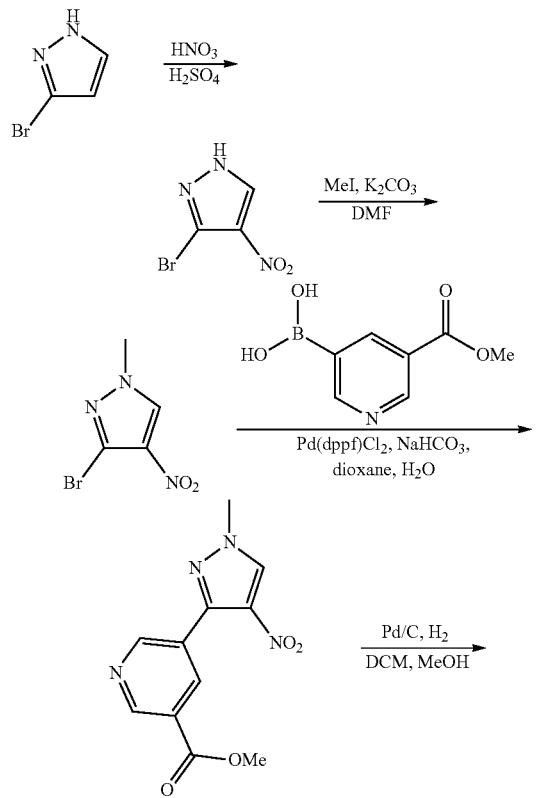

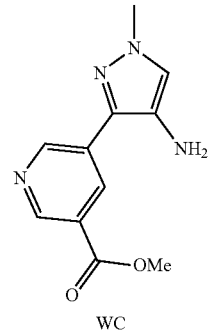

WC

Step 1—3-Bromo-4-nitro-1H-pyrazole

To a solution of 3-bromo-1H-pyrazole (10 g, 68.0 mmol) in H$_2$SO$_4$ (50 mL) was added HNO$_3$ (10.7 g, 170 mmol) at 0-10° C. Then, the mixture was stirred at 80° C. for 2 hours. On completion, the mixture was cooled to 25° C. Then, the mixture was poured into ice/water (300 mL), then extracted with EA (3×150 mL). The combined organic layer was washed with sat. aq. NaHCO$_3$ (100 mL) and brine (100 mL), dried over Na$_2$SO$_4$, and filtered. The filtrate was concentrated in vacuo to give the title compound (11.2 g, 85% yield) as yellow solid. $^1$H NMR (400 MHz, DMSO-$d_6$) δ 8.94 (s, 1H).

Step 2—3-Bromo-1-methyl-4-nitro-pyrazole

To a mixture of 3-bromo-4-nitro-1H-pyrazole (6.20 g, 32.3 mmol) and K$_2$CO$_3$ (5.36 g, 38.7 mmol) in DMF (40 mL) was added MeI (5.50 g, 38.7 mmol) at 0° C. Then, the mixture was stirred at 25° C. for 2 hours. On completion, the mixture was diluted with water (200 mL), then extracted with EA (3×80 mL). The combined organic layer was washed with brine (50 mL), dried over Na$_2$SO$_4$, filtered and concentrated in vacuo. The residue was purified by column chromatography over silica gel (PE:EA=20:1-3:1) to give the title compound (3.90 g, 58% yield) as light yellow solid. $^1$H NMR (400 MHz, CDCl$_3$) δ 8.16 (s, 1H), 3.97 (s, 3H).

Step 3—Methyl 5-(1-methyl-4-nitro-pyrazol-3-yl)pyridine-3-carboxylate

A mixture of 3-bromo-1-methyl-4-nitro-pyrazole (3.80 g, 18.4 mmol), (5-methoxycarbonyl-3-pyridyl)boronic acid (4.67 g, 25.8 mmol, CAS #871329-53-2), Pd(dppf)Cl$_2$.CH$_2$Cl$_2$ (800 mg, 979 umol) and NaHCO$_3$ (3.10 g, 36.8 mmol) in dioxane (50 mL) and H$_2$O (10 mL) was stirred at 80° C. under N$_2$ for 2 hours. On completion, the mixture was cooled to 25° C. The mixture was diluted with water (100 mL), then extracted with EA (3×80 mL). The combined organic layer was washed with brine (50 mL), dried over Na$_2$SO$_4$, filtered and concentrated in vacuo. The residue was purified by column chromatography on silica gel (PE:EA=5:1-DCM:EA=2:1) to give the title compound (2.95 g, 61% yield) as light yellow solid. $^1$H NMR (400 MHz, CDCl$_3$) δ 9.29 (s, 1H), 9.12 (s, 1H), 8.68 (s, 1H), 8.31 (s, 1H), 4.05 (s, 3H), 4.00 (s, 3H).

Step 4—Methyl 5-(4-amino-1-methyl-pyrazol-3-yl)pyridine-3-carboxylate

A mixture of methyl 5-(1-methyl-4-nitro-pyrazol-3-yl)pyridine-3-carboxylate (2.90 g, 11.0 mmol) and Pd/C (500 mg, 11.0 mmol, 10% wt) in DCM (80 mL) and MeOH (40 mL) was stirred at 25° C. for 6 hours under H$_2$ (15 psi). On completion, the mixture was filtered, and the cake was washed with MeOH (50 mL). The filtrate and washing were combined and concentrated in vacuo. The residue was purified by reversed phase flash ($NH_3 \cdot H_2O$ condition) to give crude product (1.8 g). The crude product was purified by prep-HPLC (column: Xbridge BEH C18, 250*50 mm, 10 um; mobile phase: [water (0.05% ammonia hydroxide v/v)-ACN]; B %: 1%-26%, 32MIN; 45% min) to give the title compound (470 mg, 18% yield) as light yellow solid. $^1$H NMR (400 MHz, $CDCl_3$) δ 9.23 (d, J=1.6 Hz, 1H), 9.13 (d, J=1.6 Hz, 1H), 8.70 (t, J=1.6 Hz, 1H), 7.10 (s, 1H), 3.97 (s, 3H), 3.88 (s, 3H).

5-[4-[[2-[2-[Tert-butoxycarbonyl(2,2,2-trifluoroethyl)amino]-4-pyridyl]oxazole-4-carbonyl]amino]-1-methyl-pyrazol-3-yl]pyridine-3-carboxylic acid
(Intermediate WD)

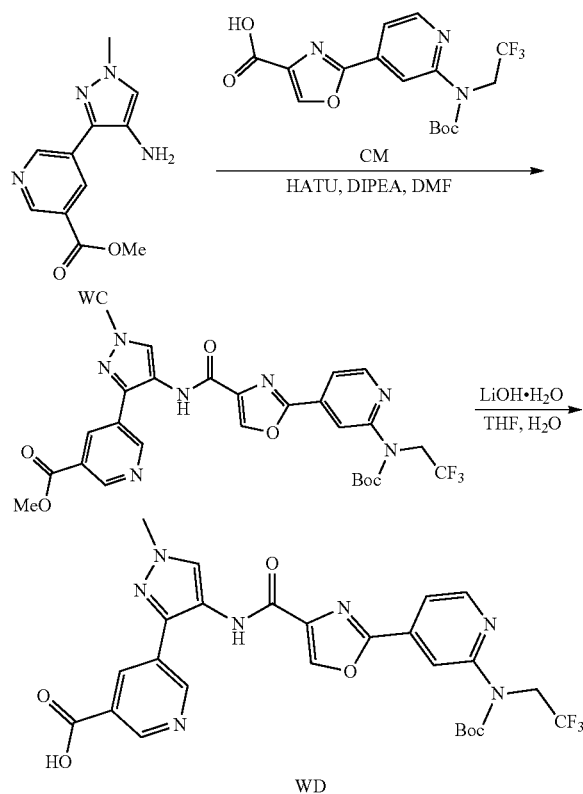

Step 1—5-[4-[[2-[2-[Tert-butoxycarbonyl(2,2,2-trifluoroethyl)amino]-4-pyridyl]oxazole-4-carbonyl]amino]-1-methyl-pyrazol-3-yl]pyridine-3-carboxylate A mixture of methyl 5-(4-amino-1-methyl-pyrazol-3-yl)pyridine-3-carboxylate (90.0 mg, 387 umol, Intermediate WC), 2-[2-[tert-butoxycarbonyl(2,2,2-trifluoroethyl)amino]-4-pyridyl]oxazole-4-carboxylic acid (153 mg, 395 umol, Intermediate CM), HATU (192 mg, 504 umol) and DIPEA (101 mg, 781 umol) in DMF (3 mL) was stirred at 25° C. for 1 hour. On completion, the mixture was combined with another identical batch. The combined mixture quenched with water (1 mL) and purified by reverse phase flash (FA condition) to give the title compound (200 mg, 86% yield) as light yellow solid. $^1$H NMR (400 MHz, $CDCl_3$) δ 9.24 (s, 1H), 9.18 (d, J=1.6 Hz, 1H), 8.83 (s, 1H), 8.69 (s, 1H), 8.51 (d, J=4.8 Hz, 1H), 8.42 (s, 1H), 8.36 (s, 1H), 8.19 (s, 1H), 7.73 (d, J=5.2 Hz, 1H), 4.88 (q, J=8.8 Hz, 2H), 4.02 (s, 3H), 3.97 (s, 3H), 1.55 (s, 9H).

Step 2—5-[4-[[2-[2-[Tert-butoxycarbonyl(2,2,2-trifluoroethyl)amino]-4-pyridyl]oxazole-4-carbonyl]amino]-1-methyl-pyrazol-3-yl]pyridine-3-carboxylic acid To a solution of methyl 5-[4-[[2-[2-[tert-butoxycarbonyl(2,2,2-trifluoroethyl)amino]-4-pyridyl]oxazole-4-carbonyl]amino]-1-methyl-pyrazol-3-yl]pyridine-3-carboxylate (200 mg, 332 umol) in THF (6 mL) was added a solution of $LiOH \cdot H_2O$ (21 mg, 500 umol) in $H_2O$ (2 mL) at 25° C. Then, the mixture was stirred at 25° C. for 16 hours. On completion, the reaction mixture was quenched with TFA (60 mg). The mixture was concentrated in vacuo. The residue was purified by reversed phase flash (TFA condition) to give the title compound (190 mg, 81% yield) as light yellow solid. $^1$H NMR (400 MHz, DMSO-$d_6$) δ 13.47 (s, 1H), 10.11 (s, 1H), 9.08 (d, J=2.0 Hz, 1H), 8.98 (s, 2H), 8.64 (d, J=5.2 Hz, 1H), 8.54 (s, 1H), 8.30 (s, 1H), 8.03 (s, 1H), 7.80 (d, J=5.2 Hz, 1H), 4.89 (q, J=9.2 Hz, 2H), 3.95 (s, 3H), 1.50 (s, 9H).

Benzyl N-[(1S)-2-[[1 (1S)-1-[(3S)-7-[2-[2-[2-[2-(2-aminoethoxy)ethoxy]ethoxy]ethoxy]ethoxy]-3-[[(1R)-tetralin-1-yl]carbamoyl]-3,4-dihydro-1H-isoquinoline-2-carbonyl]-2-2-dimethyl-propyl]amino]-1-methyl-2-oxo-ethyl]-N-methyl-carbamate
(Intermediate WE)

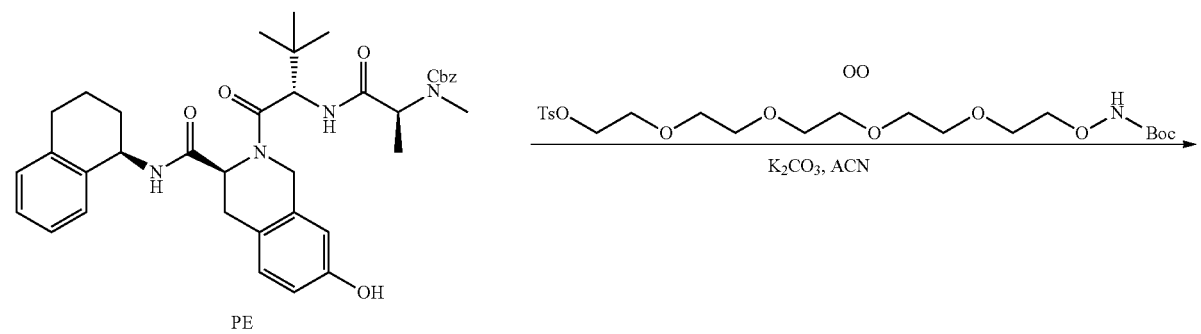

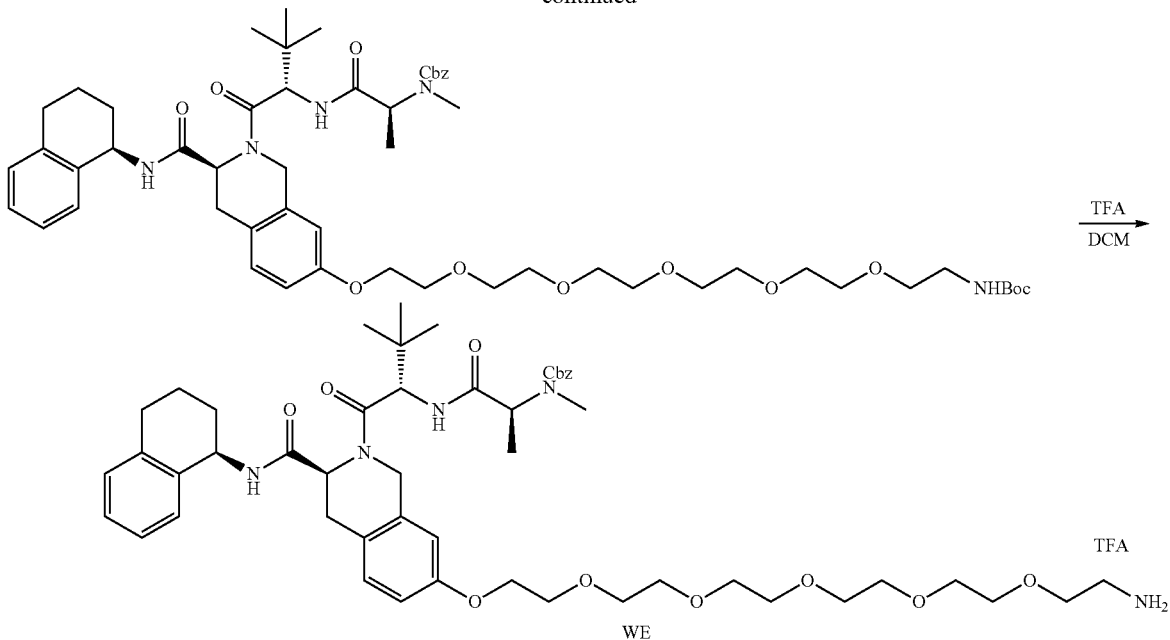

Step 1—benzyl ((S)-1-(((S)-1-((S)-7-((2,2-dimethyl-4-oxo-3,8,11,14,17,20-hexaoxa-5-azadocosan-22-yl)oxy)-3-(((R)-1,2,3,4-tetrahydronaphthalen-1-yl)carbamoyl)-3,4-dihydroisoquinolin-2 (1H)-yl)-3,3-dimethyl-1-oxobutan-2-yl)amino)-1-oxopropan-2-yl)(methyl)carbamate To a solution of benzyl ((S)-1-(((S)-1-((S)-7-hydroxy-3-(((R)-1,2,3,4-tetrahydronaphthalen-1-yl)carbamoyl)-3,4-dihydroisoquinolin-2 (1H)-yl)-3,3-dimethyl-1-oxobutan-2-yl)amino)-1-oxopropan-2-yl)(methyl)carbamate (1.6 g, 2.45 mmol, Intermediate PE) in CH$_3$CN (75 mL) was added 2,2-dimethyl-4-oxo-3,8,11,14,17,20-hexaoxa-5-azadocosan-22-yl 4-methylbenzenesulfonate (1.57 g, 2.94 mmol, Intermediate OO) and K$_2$CO$_3$ (507.2 mg, 3.68 mmol) at rt. Then the reaction mixture was stirred at 80° C. for 12 h. The solid was then filtered, and the filtrate was concentrated under reduced pressure. The residue was purified via column chromatography (DCM/MeOH) to give the title compound (1.58 g, 61% yield) as a colorless oil. LC-MS (ESI$^+$): m/z 510.01 (M+H)$^+$.

Step 2—benzyl ((S)-1-(((S)-1-((S)-7-((17-amino-3,6,9,12,15-pentaoxaheptadecyl)oxy)-3-(((R)-1,2,3,4-tetrahydronaphthalen-1-yl)carbamoyl)-3,4-dihydroisoquinolin-2 (1H)-yl)-3,3-dimethyl-1-oxobutan-2-yl)amino)-1-oxopropan-2-yl)(methyl)carbamate 2,2,2-trifluoroacetate To a solution of benzyl ((S)-1-(((S)-1-((S)-7-((2,2-dimethyl-4-oxo-3,8,11,14,17,20-hexaoxa-5-azadocosan-22-yl)oxy)-3-(((R)-1,2,3,4-tetrahydronaphthalen-1-yl)carbamoyl)-3,4-dihydroisoquinolin-2 (1H)-yl)-3,3-dimethyl-1-oxobutan-2-yl)amino)-1-oxopropan-2-yl)(methyl)carbamate (1.3 g, 1.28 mmol) in DCM (20 mL) was added TFA (20 mL) at rt. The reaction mixture was stirred at rt for 3 h. The reaction mixture was then concentration under reduced pressure and the residue was purified via reverse phase column chromatography (ACN/H$_2$O) to give the title compound (1.05 g, 89% yield) as a white solid. $^1$H NMR (400 MHz, DMSO-d6) δ 8.22 (dd, J=49.8, 8.6 Hz, 1H), 8.00-7.48 (m, 4H), 7.35 (s, 5H), 7.23-6.61 (m, 7H), 5.31-4.23 (m, 9H), 4.11-4.03 (m, 2H), 3.75-3.73 (m, 2H), 3.62-3.27 (m, 18H), 2.99-2.94 (m, 3H), 2.92-2.80 (m, 2H), 2.79-2.62 (m, 3H), 1.96-1.47 (m, 4H), 1.21-1.11 (m, 3H), 0.99 (s, 6H), 0.92 (s, 3H). LC/MS (ESI, m/z): [M+1]$^+$= 918.7.

2-[2-(Tert-butoxycarbonylamino)ethoxy]acetic acid (Intermediate WF)

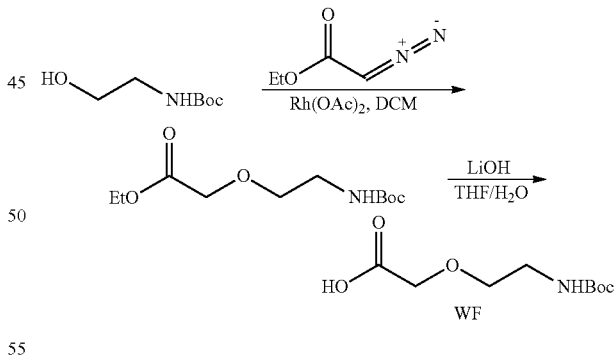

Step 1—Ethyl 2-[2-(tert-butoxycarbonylamino)ethoxy]acetate

To a mixture of tert-butyl N-(2-hydroxyethyl)carbamate (10.0 g, 62.0 mmol, 9.62 mL, CAS #26690-80-2) and Rh(OAc)$_2$ (274 mg, 1.24 mmol) in DCM (200 mL) was added a solution of ethyl 2-diazoacetate (10.6 g, 93.0 mmol, 9.74 mL, CAS #623-73-4) in DCM (250 mL) dropwise slowly. The reaction mixture was stirred at 25° C. for 12 hours. On completion, the reaction mixture was diluted with water (200 mL) and extracted with DCM (2×200 mL). The combined organic layers was dried over anhydrous Na₂SO₄, filtered and concentrated in vacuo. The residue was purified by column chromatography to give the title compound (12.0 g, 78% yield) as light yellow oil. $^1$H NMR (400 MHz, CDCl₃) δ 5.25 (s, 1H), 4.19 (q, J=7.2 Hz, 2H), 4.05 (s, 2H), 3.58 (t, J=5.2 Hz, 2H), 3.31 (q, J=5.2 Hz, 2H), 1.42 (s, 9H), 1.26 (t, J=7.1 Hz, 3H).

Step 2—2-[2-(Tert-butoxycarbonylamino)ethoxy]acetic acid

To a mixture of ethyl 2-[2-(tert-butoxycarbonylamino)ethoxy]acetate (1.00 g, 4.04 mmol) in a mixed solvent of THF (10 mL) and H₂O (5 mL) was added LiOH (193 mg, 8.09 mmol). The reaction mixture was stirred at 25° C. for 2 hours. On completion, the reaction mixture was acidified with HCl (1 N) until the pH=5-6, then the mixture was concentrated in vacuo to removed THF, and the residue was extracted with EA (5×10 mL). The combined organic layer was dried over anhydrous Na₂SO₄, filtered and the filtrate was concentrated in vacuo to give the title compound (886 mg, 99% yield) as light yellow gum. $^1$H NMR (400 MHz, DMSO-d₆) δ 7.37 (s, 1H), 3.57 (s, 2H), 3.43-3.40 (m, 2H), 3.06 (q, J=5.2 Hz, 2H), 1.37 (s, 9H).

3-[5-(aminomethyl)-3-methyl-2-oxo-benzimidazol-1-yl]piperidine-2,6-dione (Intermediate WG)

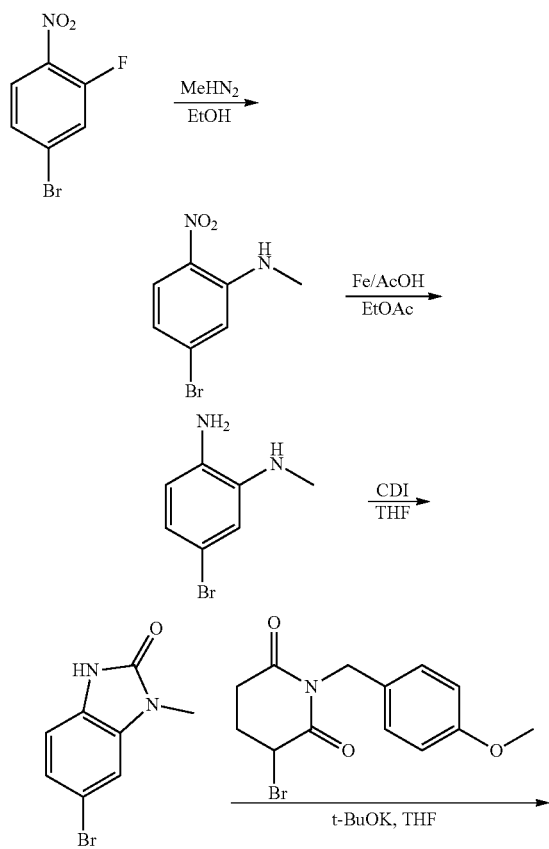

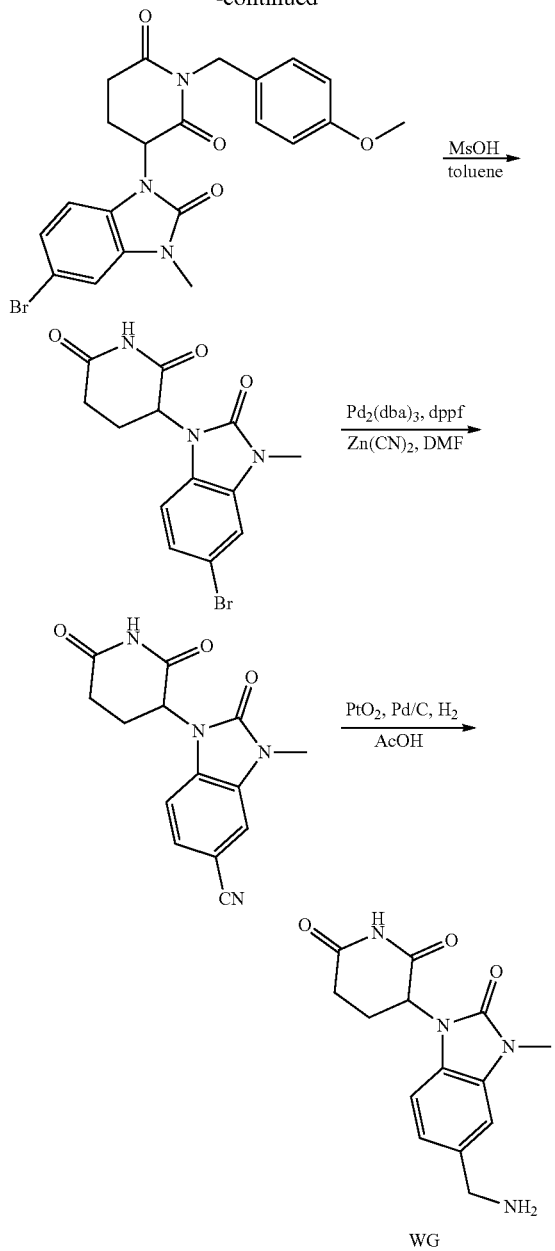

Step 1—5-bromo-N-methyl-2-nitroaniline

To a solution of 4-bromo-2-fluoro-1-nitrobenzene (23 g, 105 mmol) in EtOH (50 mL) was added MeNH₂ (250 ml, 33% in EtOH). After the addition, the mixture was stirred at rt overnight. The reaction mixture was concentrated under reduce pressure. The residue was dissolved in EtOAc (300 mL), washed with water (200 mL×2) and brine (200 mL), dried over anhydrous Na₂SO₄, filtered and concentrated to afford the title compound (23 g, 95% yield) as a yellow solid. $^1$H NMR (400 MHz, CDCl₃) δ 8.03 (d, J=9.2 Hz, 2H), 7.01 (s, 1H), 6.76 (d, J=9.2 Hz, 1H), 3.02 (s, 3H). LC/MS (ESI, m/z): [M+1]⁺=231.1

Step 2—5-bromo-N1-methylbenzene-1,2-diamine

To a solution of 5-bromo-N-methyl-2-nitroaniline (23.0 g, 0.10 mol) in AcOH (230 mL)/EtOAc (230 mL)/(50 mL) was added Fe (20 g, 0.36 mol) at 50° C. After the addition, the reaction mixture was heated to 80° C. and stirred for 1 h. Then the mixture was cooled to rt and filtered. The filtrate was concentrated under reduce pressure. The residue was diluted with EtOAc (300 mL) and $H_2O$ (300 mL). The organic layer was washed with $H_2O$ (500 mL×2) and brine (200 mL), dried over anhydrous $Na_2SO_4$, filtered and concentrated in vacuo. The residue was purified with column (EA:PE=1:2) to afford the title compound (14 g, 70% yield) as a yellow solid. LC/MS (ESI, m/z): $[M+1]^+$=201.1.

Step 3—6-bromo-1-methyl-1,3-dihydro-2H-benzo[d]imidazol-2-one

To a solution of 5-bromo-N1-methylbenzene-1,2-diamine (14 g, 69.3 mmol) in THF (200 mL) was added CDI (13.4 g, 83.2 mmol). The reaction mixture was heated for reflux 2 h under $N_2$ atmosphere. The reaction mixture was cooled to rt and concentrated under reduce pressure. The residue was purified with column (EA:PE=1:2) to afford the title compound (10 g, 63% yield) as a white solid. $^1$H NMR (400 MHz, DMSO-$d_6$) δ11.0 (s, 1H), 7.33 (s, 1H), 7.13 (t, J=8.0 Hz 1H), 6.92 (d, J=8.0 Hz, 1H), 3.26 (s, 3H). LC/MS (ESI, m/z): $[M+1]^+$=227.1.

Step 4—3-(5-bromo-3-methyl-2-oxo-2,3-dihydro-1H-benzo[d]imidazol-1-yl)-1-(4-methoxybenzyl)piperidine-2,6-dione To a solution of 6-bromo-1-methyl-1,3-dihydro-2H-benzo[d]imidazol-2-one (5.0 g, 22.1 mmol) in THF (50 mL) was added t-BuOK (2.48 g, 22.1 mmol) at 0° C. The reaction mixture was stirred at 0° C. for 30 min, then 3-bromo-1-(4-methoxybenzyl)piperidine-2,6-dione (6.9 g, 22.1 mmol) was added. After addition, the reaction mixture was stirred at r.t overnight. The reaction mixture was diluted with sat.aq. Ammonia chloride, extracted with EA (80 mL×2). The combined organic lays were washed with $H_2O$ (80 mL×2) and brine (80 mL), dried over anhydrous $Na_2SO_4$, filtered and concentrated under reduced pressure. The residue was purified with column (EtOAc:DCM=1:1) to afford 3-(5-bromo-3-methyl-2-oxo-2,3-dihydro-1H-benzo[d]imidazol-1-yl)-1-(4-methoxybenzyl)piperidine-2,6-dione (3.7 g, 36.6% yield) as a yellow solid. $^1$H NMR (400 MHz, DMSO-$d_6$) δ 7.47 (d, J=1.9 Hz, 1H), 7.23-7.13 (m, 3H), 7.00 (d, J=8.4 Hz, 1H), 6.88-6.81 (m, 2H), 5.53 (dd, J=13.0, 5.4 Hz, 1H), 4.78 (q, J=14.3 Hz, 2H), 3.72 (s, 3H), 3.33 (s, 3H), 3.12-2.95 (m, 1H), 2.86-2.63 (m, 2H), 2.12-2.01 (m, 1H). LC/MS (ESI, m/z): $[M+1]^+$=458.1.

Step 5—3-(5-bromo-3-methyl-2-oxo-2,3-dihydro-1H-benzo[d]imidazol-1-yl)piperidine-2,6-dione To a solution of 3-(5-bromo-3-methyl-2-oxo-2,3-dihydro-1H-benzo[d]imidazol-1-yl)-1-(4-methoxybenzyl)piperidine-2,6-dione (7.6 g, 16.6 mmol) in toluene (50 mL) was added methanesulfonic acid (20 mL). The reaction solution was heated to 110° C. and stirred for 3 h. The reaction mixture was cooled to rt and concentrated to remove toluene. The residue was diluted with $CH_3CN$ and purified via reverse phase column chromatography ($CH_3CN/H_2O$=5%-80%) to give the title compound (3.4 g, 61% yield) as a white solid. $^1$H NMR (400 MHz, DMSO) δ 11.11 (s, 1H), 7.47 (d, J=1.9 Hz, 1H), 7.21 (dd, J=8.4, 1.9 Hz, 1H), 7.10 (d, J=8.4 Hz, 1H), 5.38 (dd, J=12.8, 5.4 Hz, 1H), 3.34 (s, 3H), 2.93-2.83 (m, 1H), 2.74-2.60 (m, 2H), 2.03-1.97 (m, 1H). LC/MS (ESI, m/z): $[M+1]^+$=338.1.

Step 6—1-(2,6-dioxopiperidin-3-yl)-3-methyl-2-oxo-2,3-dihydro-1H-benzo[d]imidazole-5-carbonitrile A mixture of 3-(5-bromo-3-methyl-2-oxo-2,3-dihydro-1H-benzo[d]imidazol-1-yl)piperidine-2,6-dione (5 g, 14.8 mmol), zinc cyanide (6.9 g, 59.2 mmol), tris(dibenzylideneacetone)dipalladium (1.4 g, 1.5 mmol) and 1,1'-Ferrocenebis(diphenylphosphine) (1.6 g, 3.0 mmol) in DMF (100 mL) was heated to 120° C. and stirred for 19 h under nitrogen atmosphere in sealed tube. The reaction mixture was cooled to rt, filtered and concentrated under reduced pressure. The residue was purified by silica gel column chromatography (EA/DCM=2/1) to give the title compound (3 g, 71%) as a white solid. $^1$H NMR (400 MHz, DMSO-$d_6$) δ 11.16 (s, 1H), 7.75 (d, J=1.5 Hz, 1H), 7.55 (dd, J=8.2, 1.5 Hz, 1H), 7.34 (d, J=8.2 Hz, 1H), 5.46 (dd, J=12.8, 5.4 Hz, 1H), 3.38 (s, 3H), 2.83-2.94 (m, 1H), 2.59-2.78 (m, 2H), 2.01-2.09 (m, 1H). LC/MS (ESI, m/z): $[M+1]^+$=284.9.

Step 7—3-(5-(aminomethyl)-3-methyl-2-oxo-2,3-dihydro-1H-benzo[d]imidazol-1-yl)piperidine-2,6-dione acetate To a solution of 1-(2,6-dioxopiperidin-3-yl)-3-methyl-2-oxo-2,3-dihydro-1H-benzo[d]imidazole-5-carbonitrile (2.3 g, 8.1 mmol) in AcOH (20 mL) was added $PtO_2$ (98.8 mg, 0.41 mmol) and 10 wt % palladium on activated carbon (850 mg, 0.81 mmol). The mixture was hydrogenated for 1 h at 85 psi at rt. The reaction mixture was filtered, the filtrate was concentrated under reduced pressure and dried to give the title compound (2.8 g, quant. yield) as a salt with AcOH. $^1$H NMR (400 MHz, DMSO-$d_6$) δ 7.24 (s, 1H), 7.01-7.10 (m, 2H), 5.36 (dd, J=12.76, 5.38 Hz, 1H), 3.84 (s, 2H), 3.33 (s, 3H), 2.83-2.96 (m, 1H), 2.57-2.78 (m, 2H), 1.97-2.05 (m, 1H), 1.85 (br. s., 6H). LC/MS (ESI, m/z): $[M-NH_2]+$=272.17.

2-(2-Aminoethoxy)-N-[[1-(2,6-dioxo-3-piperidyl)-3-methyl-2-oxo-benzimidazol-5-yl]methyl]acetamide (Intermediate WH)

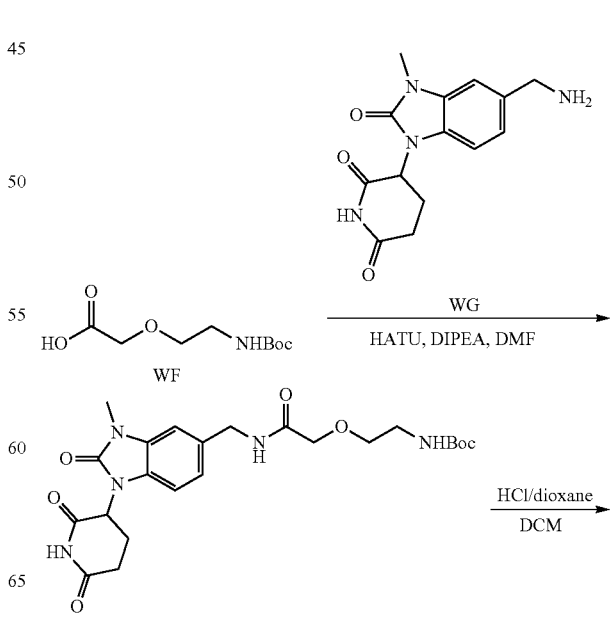

-continued

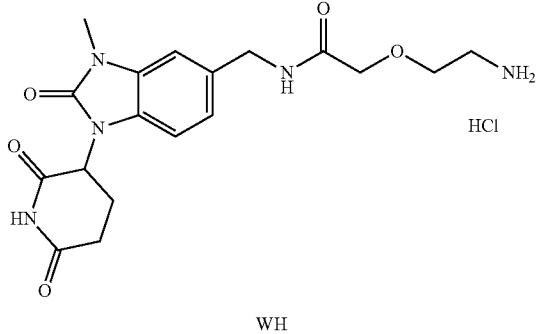

WH

Step 1—Tert-butyl N-[2-[2-[[1-(2,6-dioxo-3-piperidyl)-3-methyl-2-oxo-benzimidazol-5-yl]methyl amino]-2-oxo-ethoxy]ethyl]carbamate To a mixture of 2-[2-(tert-butoxycarbonylamino)ethoxy]acetic acid (405 mg, 1.85 mmol, Intermediate WF) and DIPEA (994 mg, 7.70 mmol, 1.34 mL) in DMF (5 mL) was added HATU (702 mg, 1.85 mmol). The reaction mixture was stirred at 0° C. Then, 3-[5-(aminomethyl)-3-methyl-2-oxo-benzimidazol-1-yl]piperidine-2,6-dione (0.50 g, 1.54 mmol, HCl, Intermediate WG) was added. The reaction mixture was stirred at 25° C. for 0.5 hour. On completion, the reaction mixture was concentrated in vacuo. The residue was purified by prep-HPLC (0.1% FA condition) to give the title compound (500 mg, 66% yield) as white solid. LC-MS (ESI$^+$) m/z 390.2 (M+H−100)$^+$.

Step 2—2-(2-Aminoethoxy)-N-[[1-(2,6-dioxo-3-piperidyl)-3-methyl-2-oxo-benzimidazol-5-yl]methyl]acetamide To a mixture of tert-butyl N-[2-[2-[[1-(2,6-dioxo-3-piperidyl)-3-methyl-2-oxo-benzimidazol-5-yl]methylamino]-2-oxo-ethoxy]ethyl]carbamate (400 mg, 817 umol) in DCM (5 mL) was added HCl/dioxane (4 M, 20 mL). The reaction mixture was stirred at 25° C. for 1 hour. On completion, the reaction mixture was concentrated in vacuo. The residue was purified by prep-HPLC (0.1% FA condition) to give the title compound (240 mg, 75% yield) as white solid. $^1$H NMR (400 MHz, DMSO-d$_6$) δ 11.08 (s, 1H), 8.53 (t, J=6.0 Hz, 1H), 8.03 (s, 2H), 7.12 (s, 1H), 7.08-6.95 (m, 2H), 5.36 (dd, J=5.2, 12.8 Hz, 1H), 4.36 (d, J=6.0 Hz, 2H), 3.98 (s, 2H), 3.65 (t, J=5.2 Hz, 2H), 3.37 (s, 3H), 3.02 (d, J=4.4 Hz, 2H), 2.97-2.85 (m, 1H), 2.77-2.59 (m, 2H), 2.07-1.92 (m, 1H); LC-MS (ESI$^+$) m/z 390.2 (M+H)$^+$.

3-[4-[4-(4-Aminobutoxy)butyl]-3-methyl-2-oxo-benzimidazol-1-yl]piperidine-2,6-dione (Intermediate WI)

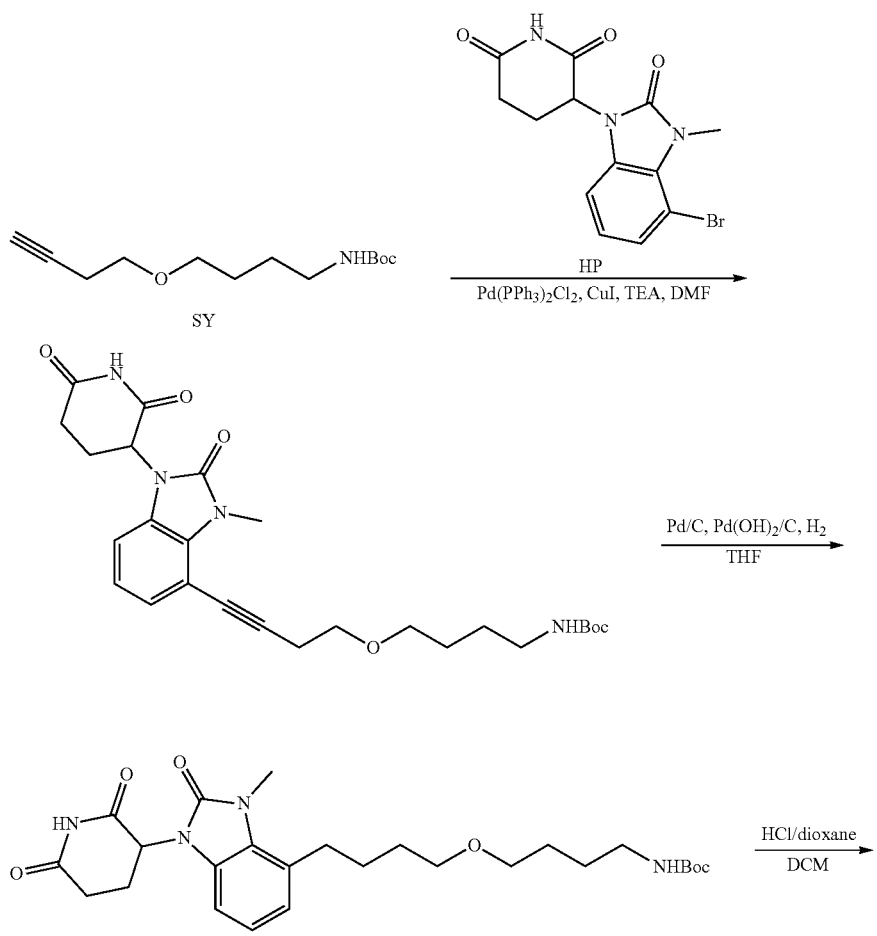

-continued

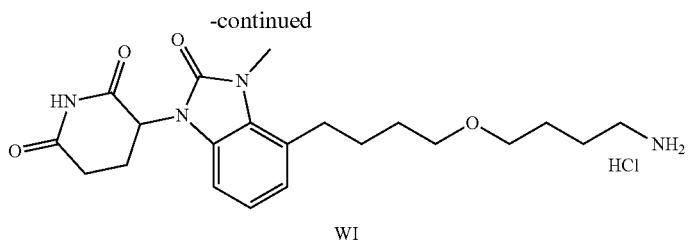

WI

Step 1—Tert-butyl N-[4-[4-[1-(2,6-dioxo-3-piperidyl)-3-methyl-2-oxo-benzimidazol-4-yl]but-3-ynoxy]butyl]carbamate A mixture of 3-(4-bromo-3-methyl-2-oxo-benzimidazol-1-yl)piperidine-2,6-dione (500 mg, 1.48 mmol, Intermediate HP), tert-butyl N-(4-but-3-ynoxybutyl)carbamate (1.07 g, 4.44 mmol, Intermediate SY), CuI (84 mg, 443 umol), Pd(PPh$_3$)$_2$Cl$_2$ (311 mg, 443 umol) and TEA (2.69 g, 26.6 mmol) in DMF (10 mL) was degassed and purged with N$_2$ three times, and then the mixture was stirred at 85° C. for 4 hrs under N$_2$ atmosphere. On completion, the mixture was dilute with H$_2$O (20 mL), then extracted with EA (2×60 mL). The organic layer was washed with brine (30 mL), dried over anhydrous Na$_2$SO$_4$, and then concentrated in vacuo. The residue was purified by reversed phase flash to give the title compound (460 mg, 58% yield) as light yellow solid. $^1$H NMR (400 MHz, DMSO-d$_6$) δ 11.12 (s, 1H), 7.12 (d, J=7.6 Hz, 1H), 7.09-7.04 (m, 1H), 7.02-6.97 (m, 1H), 6.79 (s, 1H), 5.39 (dd, J=5.2, 12.8 Hz, 1H), 3.65 (s, 3H), 3.58 (t, J=6.4 Hz, 2H), 3.43 (t, J=6.0 Hz, 2H), 2.96-2.86 (m, 3H), 2.77-2.58 (m, 4H), 2.06-1.99 (m, 1H), 1.51-1.40 (m, 4H), 1.37 (s, 9H); LC-MS (ESI$^+$) m/z 499.3 (M+1)$^+$.

Step 2—Tert-butyl N-[4-[4-[1-(2,6-dioxo-3-piperidyl)-3-methyl-2-oxo-benzimidazol-4-yl]butoxy]butyl]carbamate To a solution of tert-butyl N-[4-[4-[1-(2,6-dioxo-3-piperidyl)-3-methyl-2-oxo-benzimidazol-4-yl]but-3-ynoxy]butyl]carbamate (460 mg, 922 umol) in THF (50 mL) was added Pd/C (100 mg, 10 wt %) and Pd(OH)$_2$/C (100 mg, 10 wt %). The mixture was stirred at 25° C. for 4 hrs under H$_2$ (15 psi). On completion, the mixture was filtered and the filtrate was concentrated in vacuo to give the title compound (463 mg, 99% yield) as white solid. $^1$H NMR (400 MHz, DMSO-d6) δ 11.09 (s, 1H), 6.99-6.95 (m, 2H), 6.89-6.87 (m, 1H), 6.80-6.75 (m, 1H), 5.37 (dd, J=5.2, 12.4 Hz, 1H), 3.55 (s, 3H), 3.40 (t, J=5.6 Hz, 2H), 3.36-3.33 (m, 2H), 2.96-2.85 (m, 5H), 2.77-2.58 (m, 2H), 2.05-1.96 (m, 1H), 1.69-1.57 (m, 4H), 1.52-1.40 (m, 4H), 1.37 (s, 9H).

Step 3—3-[4-[4-(4-Aminobutoxy)butyl]-3-methyl-2-oxo-benzimidazol-1-yl]piperidine-2,6-dione To a solution of tert-butyl N-[4-[4-[1-(2,6-dioxo-3-piperidyl)-3-methyl-2-oxo-benzimidazol-4-yl]butoxy]butyl]carbamate (460 mg, 915 umol) in DCM (20 mL) was added HCl/dioxane (4 M, 10 mL). The mixture was stirred at 25° C. for 3 hrs. On completion, the mixture was concentrated in vacuo to give the title compound (360 mg, 90% yield) as light yellow solid. $^1$H NMR (400 MHz, DMSO-d$_6$) δ 11.01 (s, 1H), 7.68 (s, 2H), 6.94-6.85 (m, 2H), 6.81-6.79 (m, 1H), 5.30 (dd, J=5.2, 12.8 Hz, 1H), 3.49 (s, 3H), 3.37-3.35 (m, 2H), 3.31-3.28 (m, 2H), 2.89-2.77 (m, 3H), 2.76-2.55 (m, 4H), 1.97-1.88 (m, 1H), 1.61-1.45 (m, 8H); LC-MS (ESI$^+$) m/z 403.1 (M+1)$^+$.

Tert-butyl N-[4-[4-[[3-(5-formyl-3-pyridyl)-1-methyl-pyrazol-4-yl]carbamoyl]oxazol-2-yl]-2-pyridyl]-N-(2,2,2-trifluoroethyl)carbamate (Intermediate WJ)

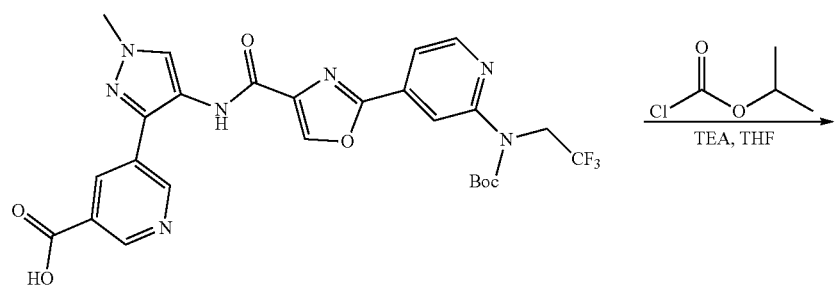

WD

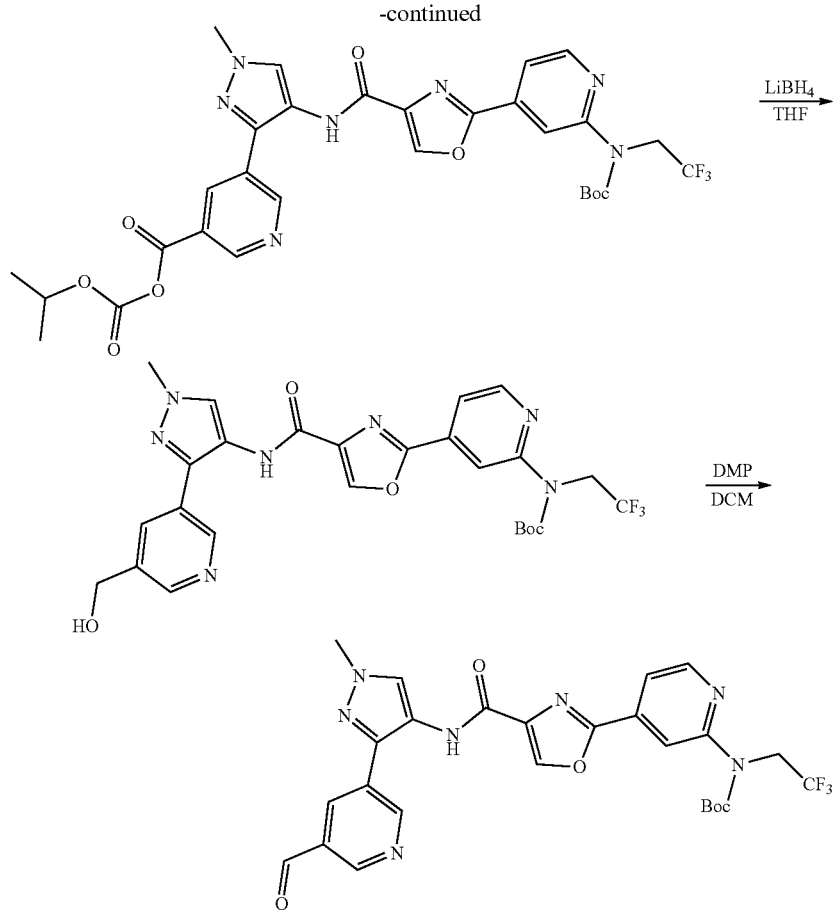

Step 1—Isopropoxycarbonyl 5-[4-[[2-[2-[tert-butoxycarbonyl(2,2,2-trifluoroethyl)amino]-4-pyridyl]oxazole-4-carbonyl]amino]-1-methyl-pyrazol-3-yl]pyridine-3-carboxylate To a solution of 5-[4-[[2-[2-[tert-butoxycarbonyl(2,2,2-trifluoroethyl)amino]-4-pyridyl]oxazole-4-carbonyl]amino]-1-methyl-pyrazol-3-yl]pyridine-3-carboxylic acid (640 mg, 1.09 mmol, Intermediate WD) and TEA (560 mg, 5.53 mmol) in THF (20 mL) was added isopropyl carbonochloridate (340 mg, 2.77 mmol) at 0° C. Then, the mixture was stirred at 0-10° C. for 2 hours. On completion, the mixture was filtered and the filter cake was washed with THF (10 mL). The filtrate and washing were combined and used directly in the next step. LC-MS (ESI+) m/z 674.3 (M+H)+.

Step 2—Tert-butyl N-[4-[4-[[3-[5-(hydroxymethyl)-3-pyridyl]-1-methyl-pyrazol-4-yl]carbamoyl]oxazol-2-yl]-2-pyridyl]-N-(2,2,2-trifluoroethyl)carbamate To a solution of isopropoxycarbonyl 5-[4-[[2-[2-[tert-butoxycarbonyl(2,2,2-trifluoroethyl)amino]-4-pyridyl]oxazole-4-carbonyl]amino]-1-methyl-pyrazol-3-yl]pyridine-3-carboxylate in THF (30 mL) was added LiBH$_4$ (147 mg, 6.75 mmol) at 0° C. Then, the mixture was stirred at 0-10° C. for 1 hour. On completion, the mixture was added water (100 mL). The mixture was extracted with EA (3×60 mL). The combined organic layer was concentrated in vacuo. The residue was purified by reversed phase flash (0.1% FA condition) to give the title compound (380 mg, 60% yield via two steps) as light yellow solid. $^1$H NMR (400 MHz, CDCl$_3$) δ 8.94-8.92 (m, 2H), 8.59 (m, 1H), 8.51 (d, J=5.2 Hz, 1H), 8.41-8.39 (m, 2H), 8.24 (s, 1H), 8.14 (s, 1H), 7.68-7.66 (m, 1H), 4.89 (q, J=8.8 Hz, 2H), 4.81 (s, 2H), 4.01 (s, 3H), 1.59 (s, 9H).

Step 3—Tert-butyl N-[4-[4-[[3-(5-formyl-3-pyridyl)-1-methyl-pyrazol-4-yl]carbamoyl]oxazol-2-yl]-2-pyridyl]-N-(2,2,2-trifluoroethyl)carbamate To a solution of tert-butyl N-[4-[4-[[3-[5-(hydroxymethyl)-3-pyridyl]-1-methyl-pyrazol-4-yl]carbamoyl]oxazol-2-yl]-2-pyridyl]-N-(2,2,2-trifluoroethyl) carbamate (360 mg, 573 umol) in DCM (20 mL) was added Dess-Martin (360 mg, 848 umol) at 0° C. Then, the mixture was stirred at 3 hours at 0-10° C. On completion, the mixture was diluted with DCM (20 mL), washed with sat. aq. Na$_2$S$_2$O$_3$ (10 mL). The organic layer was washed with sat.NaHCO$_3$ (10 mL) and brine (10 mL), dried over Na$_2$SO$_4$, filtered and concentrated in vacuo to give the title compound (320 mg, 97% yield) as light yellow solid. $^1$H NMR (400 MHz, CDCl$_3$) δ 10.21 (s, 1H), 9.26 (d, J=2.0 Hz, 1H), 9.08 (d, J=2.0 Hz, 1H), 8.82 (s, 1H), 8.54-8.52 (m, 2H), 8.41 (s, 1H), 8.38 (s, 1H), 8.18 (s, 1H), 7.73 (d, J=1.6 Hz, 1H), 4.87 (q, J=8.8 Hz, 2H), 4.01 (s, 3H), 1.56 (s, 9H).

2-[2-(Methylamino)ethoxy]ethanol (Intermediate WK)

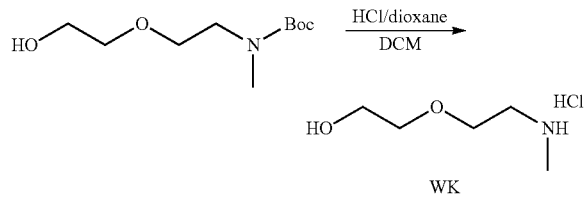

To a solution of tert-butyl N-[2-(2-hydroxyethoxy)ethyl]-N-methyl-carbamate (3.00 g, 13.7 mmol, synthesized via Steps 1-2 of Intermediate FY) in DCM (20 mL) was added HCl/dioxane (4 M, 20 mL). The reaction mixture was stirred at 25° C. for 1 hr. On completion, the mixture was concentrated in vacuo to give the title compound (2.10 g, 99% yield, HCl salt) as a white solid. $^1$H NMR (400 MHz, DMSO-$d_6$) δ 3.67 (t, J=5.2 Hz, 2H), 3.57-3.51 (m, 2H), 3.50-3.46 (m, 2H), 3.13-3.02 (m, 2H), 2.55 (t, J=5.2 Hz, 3H).

Tert-butyl 4-(2-prop-2-ynoxyethoxy)piperidine-1-carboxylate (Intermediate WM)

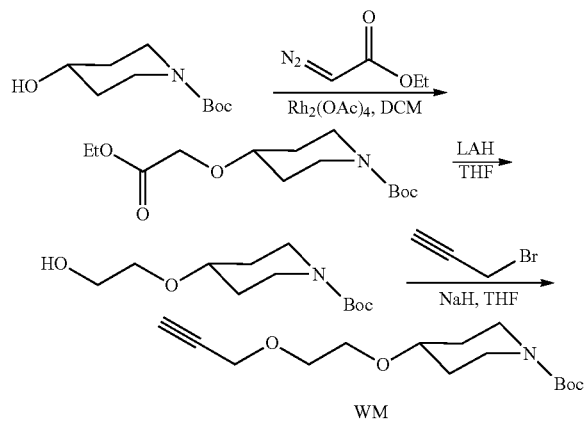

Step 1—Tert-butyl 4-(2-ethoxy-2-oxo-ethoxy)piperidine-1-carboxylate

To a mixture of tert-butyl 4-hydroxypiperidine-1-carboxylate (5.00 g, 24.8 mmol, CAS #109384-19-2) and diacetoxyrhodium (274 mg, 1.24 mmol) in DCM (80 mL) was added a solution of ethyl 2-diazoacetate (8.50 g, 74.5 mmol) in DCM (60 mL) at 0-10° C. during 2 hours. The mixture was stirred at 25° C. for 40 hours. On completion, the mixture was concentrated in vacuo. The residue was purified by column chromatography to give the title compound (7.00 g, 98% yield) as light yellow oil. $^1$H NMR (400 MHz, CDCl$_3$) δ 4.28-4.20 (m, 2H), 4.12 (s, 2H), 3.81-3.75 (m, 2H), 3.57 (m, 1H) 3.12-3.05 (m, 2H), 1.87-1.86 (m, 2H), 1.59-1.52 (m, 2H), 1.46 (s, 9H), 1.33-1.28 (s, 3H).

Step 2—Tert-butyl 4-(2-hydroxyethoxy)piperidine-1-carboxylate

To a suspension of LAH (1.59 g, 41.8 mmol) in THF (40 mL) was added a solution of tert-butyl 4-(2-ethoxy-2-oxo-ethoxy)piperidine-1-carboxylate (6.00 g, 16.5 mmol) in THF (20 mL) slowly at 0-10° C. The mixture was stirred at 0-10° C. for 3 hours. On completion, the reaction was quenched with water (1.60 mL) slowly at 0-10° C. Then 10% aq.NaOH (1.60 mL) and water (4.80 mL) were added to the mixture. The mixture was filtered and the filter cake was washed with EA (50 mL). The filtrate and washing were combined and concentrated in vacuo. The residue was purified by column chromatography on silica gel to give the title compound (4.00 g, 67% yield) as light yellow oil. $^1$H NMR (400 MHz, CDCl$_3$) δ 3.76-3.75 (m, 2H), 3.74-3.73 (m, 2H), 3.60-3.58 (m, 2H), 3.50 (m, 1H), 3.13-3.07 (m, 2H), 1.85-1.84 (m, 2H), 1.57-1.52 (m, 2H), 1.47 (s, 9H).

Step 3—Tert-butyl 4-(2-prop-2-ynoxyethoxy)piperidine-1-carboxylate

To a solution of tert-butyl 4-(2-hydroxyethoxy)piperidine-1-carboxylate (3.80 g, 15.4 mmol) in THF (40 mL) was added NaH (1.86 g, 46.5 mmol, 60% oil dispersion) at 0° C. The mixture was stirred at 25° C. for 0.5 hour. Then 3-bromoprop-1-yne (2.76 g, 23.2 mmol) was added to the mixture at 25° C. The mixture was stirred at 25° C. for 16 hours. On completion, the reaction was quenched with sat.aq.NH$_4$Cl (20 mL). The mixture was diluted with water (100 mL), then extracted with EA (3×80 mL). The combined organic layer was washed with brine (30 mL), dried over Na$_2$SO$_4$, filtered and concentrated in vacuo. The residue was purified by column chromatography to give the title compound (3.70 g, 84% yield) as light yellow oil. $^1$H NMR (400 MHz, CDCl$_3$) δ 4.22 (d, J=2.4 Hz, 2H), 3.86-3.75 (m, 2H), 3.73-3.62 (m, 4H), 3.53-3.45 (m, 1H), 3.10-3.00 (m, 2H), 2.44 (t, J=2.4 Hz, 1H), 1.90-1.80 (m, 2H), 1.56-1.48 (m, 2H), 1.46 (s, 9H).

3-[3-Methyl-2-oxo-5-[3-[2-(4-piperidyloxy)ethoxy]propyl]benzimidazol-1-yl]piperidine-2,6-dione (Intermediate WN)

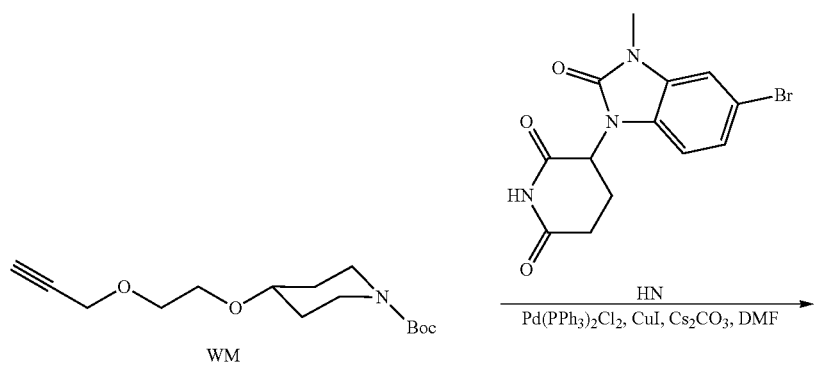

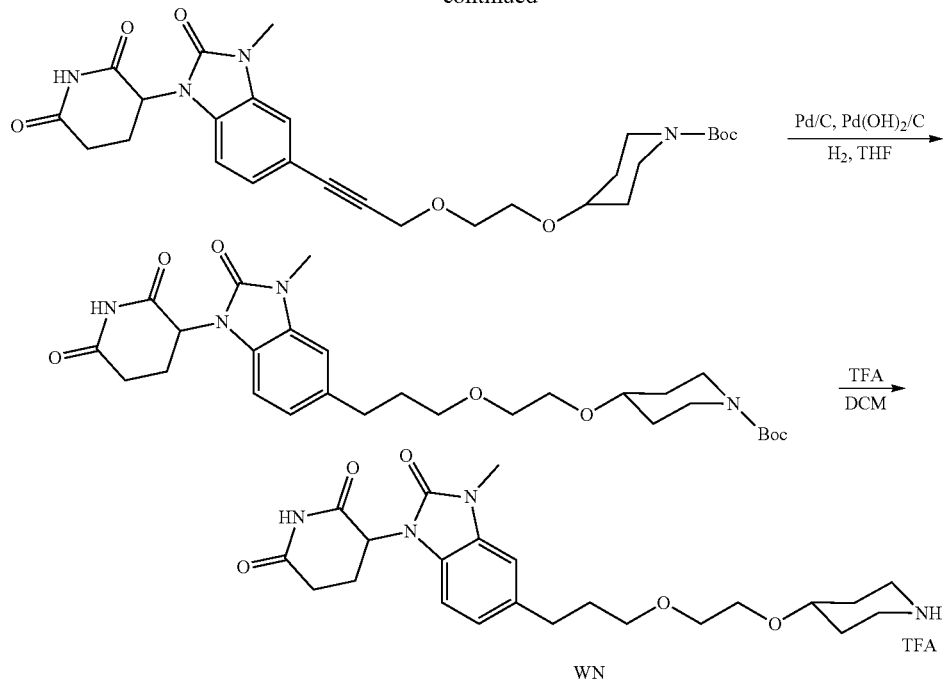

Step 1—Tert-butyl 4-[2-[3-[1-(2,6-dioxo-3-piperidyl)-3-methyl-2-oxo-benzimidazol-5-yl]prop-2-ynoxy]ethoxy]piperidine-1-carboxylate A mixture of tert-butyl 4-(2-prop-2-ynoxyethoxy)piperidine-1-carboxylate (800 mg, 2.82 mmol, Intermediate WM), 3-(5-bromo-3-methyl-2-oxo-benzimidazol-1-yl)piperidine-2,6-dione (400 mg, 1.18 mmol, Intermediate HN), CuI (45.0 mg, 236 umol), Pd(PPh$_3$)$_2$Cl$_2$ (166 mg, 236 umol), Cs$_2$CO$_3$ (1.93 g, 5.91 mmol) and 4 Å MS (400 mg) in DMF (15 mL) was stirred at 80° C. for 2 hours. On completion, the reaction mixture was cooled to 20° C. The mixture was diluted with EA (50 mL), filtered and the cake was washed with EA (30 mL). The filtrate and washing were combined and concentrated in vacuo. The residue was purified by reversed phase flash (FA condition) to give the title compound (420 mg, 65% yield) as light yellow solid. $^1$H NMR (400 MHz, DMSO-d$_6$) δ 11.13 (m, 1H), 7.33 (s, 1H), 7.19-7.08 (m, 2H), 5.41-5.37 (m, 1H), 4.40 (s, 2H), 4.18-4.11 (m, 1H), 3.63-3.59 (m, 4H), 3.56-3.51 (m, 2H), 3.50-3.41 (m, 2H), 3.36 (s, 3H), 2.93-2.83 (m, 1H), 2.76-2.61 (m, 2H), 2.07-1.99 (m, 1H), 1.80-1.75 (m, 2H) 1.38 (s, 9H), 1.35-1.30 (m, 2H).

Step 2—Tert-butyl 4-[2-[3-[1-(2,6-dioxo-3-piperidyl)-3-methyl-2-oxo-benzimidazol-5-yl]propoxy]ethoxy]piperidine-1-carboxylate A mixture of tert-butyl 4-[2-[3-[1-(2,6-dioxo-3-piperidyl)-3-methyl-2-oxo-benzimidazol-5-yl]prop-2-ynoxy]ethoxy]piperidine-1-carboxylate (400 mg, 739 umol), Pd(OH)$_2$/C (100 mg, 739 umol, 10 wt %) and Pd/C (100 mg, 739 umol, 10 wt %) in THF (20 mL) was stirred at 25° C. for 20 hours under H$_2$ (15 psi). On completion, the mixture was filtered, and the cake was washed with EA (10 mL). The filtrate and washing were combined and concentrated in vacuo to give the title compound (400 mg, 99% yield) as light yellow gum. $^1$H NMR (400 MHz, CDCl$_3$) δ 8.11 (s, 1H), 6.94-6.89 (m, 1H), 6.88 (s, 1H), 6.72 (d, J=8.0 Hz, 1H), 5.25-5.18 (m, 1H), 3.75-3.70 (m, 1H), 3.60-3.56 (m, 2H), 3.52-3.46 (m, 4H), 3.43 (s, 3H), 3.11-3.02 (m, 3H), 2.90-2.83 (m, 1H), 2.77-2.70 (m, 3H), 2.27-2.21 (m, 1H), 1.93-1.91 (m, 2H), 1.88-1.81 (m, 3H), 1.64-1.60 (m, 1H), 1.55-1.51 (m, 2H), 1.46 (s, 9H).

Step 3—3-[3-Methyl-2-oxo-5-[3-[2-(4-piperidyloxy)ethoxy]propyl]benzimidazol-1-yl]piperidine-2,6-dione To a solution of tert-butyl 4-[2-[3-[1-(2,6-dioxo-3-piperidyl)-3-methyl-2-oxo-benzimidazol-5-yl]propoxy]ethoxy]piperidine-1-carboxylate (100 mg, 183 umol) in DCM (3.0 mL) was added TFA (1.0 mL) at 20° C. The reaction mixture was stirred at 20° C. for 1 hour. On completion, the mixture was concentrated in vacuo to give the title compound (81.0 mg, 99% yield) as light yellow gum. LC-MS (ESI$^+$) m/z 445.3 (M+H)$^+$.

Tert-butyl N-methyl-N-[[(2R)-4-prop-2-ynylmorpholin-2-yl]methyl]carbamate (Intermediate WP)

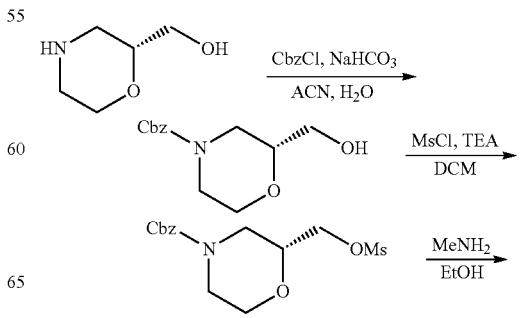

-continued

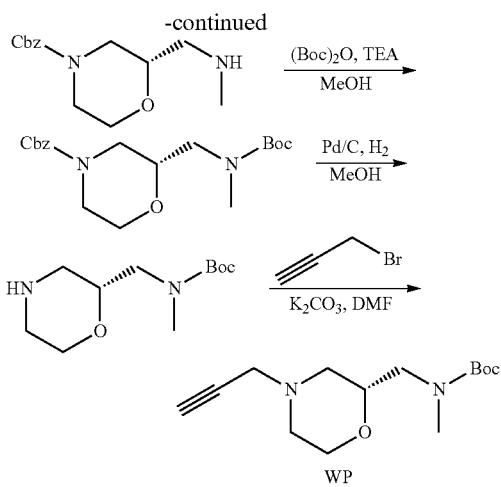

Step 1—Benzyl (2R)-2-(hydroxymethyl)morpholine-4-carboxylate

To a solution of [(2R)-morpholin-2-yl]methanol (2.50 g, 16.2 mmol, HCl, CAS #156925-22-3), NaHCO$_3$ (4.10 g, 48.8 mmol) in a mixed solvent of ACN (80.0 mL) and H$_2$O (80.0 mL) was added CbzCl (4.16 g, 24.4 mmol, 3.47 mL) at 0° C. dropwise. The mixture was then stirred at 25° C. for 16 hrs. On completion, the mixture was concentrated in vacuo to remove ACN. Then the mixture was extracted with EA (2×20 mL), and the combined organic layers were concentrated in vacuo. The residue was purified by silica gel column (PE:EA=1:1) to give the title compound (3.7 g, 90% yield) as colorless oil. $^1$H NMR (400 MHz, CDCl$_3$) δ 7.42-7.33 (m, 5H), 5.17 (d, J=2.0 Hz, 2H), 4.08-3.88 (m, 3H), 3.77-3.65 (m, 1H), 3.63-3.46 (m, 3H), 3.13-2.73 (m, 2H), 2.07-1.96 (m, 1H).

Step 2—Benzyl (2R)-2-(methyl sulfonyloxymethyl)morpholine-4-carboxylate

To a solution of benzyl (2R)-2-(hydroxymethyl)morpholine-4-carboxylate (3.70 g, 14.7 mmol), and TEA (4.47 g, 44.1 mmol) in DCM (40.0 mL) was added MsCl (2.53 g, 22.0 mmol) at 0° C., then the mixture was stirred at 25° C. for 1 hr. On completion, the mixture was diluted with DCM (20 mL) and washed with H$_2$O (3×30 mL). The organic layer was dried over anhydrous Na$_2$SO$_4$, filtered and concentrated in vacuo to give the title compound (4.85 g, 100% yield) as yellow oil. $^1$H NMR (400 MHz, CDCl$_3$) δ 7.43-7.33 (m, 5H), 5.20-5.15 (m, 2H), 4.26 (d, J=4.8 Hz, 2H), 4.10-3.83 (m, 3H), 3.80-3.65 (m, 1H), 3.63-3.48 (m, 1H), 3.08 (s, 3H), 3.07-2.75 (m, 2H).

Step 3—Benzyl (2S)-2-(methylaminomethyl)morpholine-4-carboxylate

To a solution of benzyl (2R)-2-(methylsulfonyloxymethyl)morpholine-4-carboxylate (4.3 g, 13.0 mmol) in EtOH (10.0 mL) was added MeNH$_2$ (40.5 g, 391 mmol, 30% solution in ethanol), and the mixture was stirred at 80° C. for 16 hrs in a 100 mL of autoclave. On completion, the mixture was concentrated in vacuo to give the title compound (3.45 g, 100% yield) as yellow oil. LC-MS (ESI$^+$) m/z 265.1 (M+H)$^+$.

Step 4—Benzyl (2S)-2-[[tert-butoxycarbonyl (methyl)amino]methyl]morpholine-4-carboxylate To a solution of benzyl (2S)-2-(methylaminomethyl)morpholine-4-carboxylate (3.45 g, 13.0 mmol) in MeOH (50.0 mL) was added TEA (1.58 g, 15.6 mmol, 2.18 mL). Then (Boc)$_2$O (4.27 g, 19.5 mmol, 4.50 mL) was added into the above mixture dropwise. The mixture was stirred at 25° C. for 2 hrs. On completion, the mixture was concentrated in vacuo. The residue was purified by silica gel column (PE:EA=5:1) to give the title compound (4.10 g, 86% yield) as yellow oil. $^1$H NMR (400 MHz, CDCl$_3$) δ 7.43-7.30 (m, 5H), 5.24-5.09 (m, 2H), 4.11-3.83 (m, 3H), 3.68-3.34 (m, 3H), 3.30-3.14 (m, 1H), 3.09-2.97 (m, 1H), 2.94 (s, 3H), 2.80-2.62 (m, 1H), 1.47 (s, 9H).

Step 5—Tert-butyl N-methyl-N-[[(2R)-morpholin-2-yl]methyl]carbamate

To a solution of benzyl (2S)-2-[[tert-butoxycarbonyl (methyl)amino]methyl]morpholine-4-carboxylate (4.10 g, 11.2 mmol) in MeOH (40.0 mL) was added Pd/C (1.00 g, 10% wt), and the mixture was stirred at 25° C. for 16 hrs under H$_2$ (15 psi). On completion, the mixture was filtered and the filtrate was concentrated in vacuo to give the title compound (2.54 g, 98% yield) as colorless oil. $^1$H NMR (400 MHz, DMSO-d$_6$) δ 3.75-3.65 (m, 1H), 3.50-3.42 (m, 1H), 3.41-3.37 (m, 1H), 3.24-3.13 (m, 1H), 3.10-3.03 (m, 1H), 2.85-2.75 (m, 3H), 2.70-2.53 (m, 4H), 2.37-2.23 (m, 1H), 1.39 (s, 9H).

Step 6—Tert-butyl N-methyl-N-[[(2R)-4-prop-2-ynylmorpholin-2-yl]methyl]carbamate To a solution of tert-butyl N-methyl-N-[[(2R)-morpholin-2-yl]methyl]carbamate (1.00 g, 4.34 mmol), 3-bromoprop-1-yne (516 mg, 4.34 mmol, CAS #106-96-7) in DMF (10.0 mL) was added K$_2$CO$_3$ (3.00 g, 21.7 mmol). The mixture was stirred at 25° C. for 2 hrs. On completion, the mixture was diluted with H$_2$O (20 mL), then extracted with EA (2×20 mL). The combined organic layers were washed with brine (2×20 mL), dried over anhydrous Na$_2$SO$_4$, filtered and the filtrate was concentrated in vacuo. The residue was purified by silica gel column (PE:EA=5:1) to give the title compound (960 mg, 82% yield) as yellow oil. $^1$H NMR (400 MHz, DMSO-d$_6$) δ 3.85-3.76 (m, 1H), 3.63-3.52 (m, 1H), 3.50-3.40 (m, 1H), 3.30-3.24 (m, 2H), 3.20-3.14 (m, 2H), 2.84-2.78 (m, 3H), 2.68-2.55 (m, 2H), 2.54-2.52 (m, 1H), 2.30-2.16 (m, 1H), 2.03-1.90 (m, 1H), 1.39 (s, 9H).

3-[3-Methyl-5-[3-[(2S)-2-(methylaminomethyl)morpholin-4-yl]prop-1-ynyl]-2-oxo-benzimidazol-1-yl]piperidine-2,6-dione (Intermediate WO)

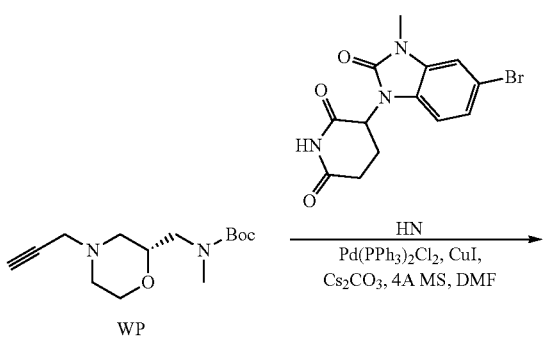

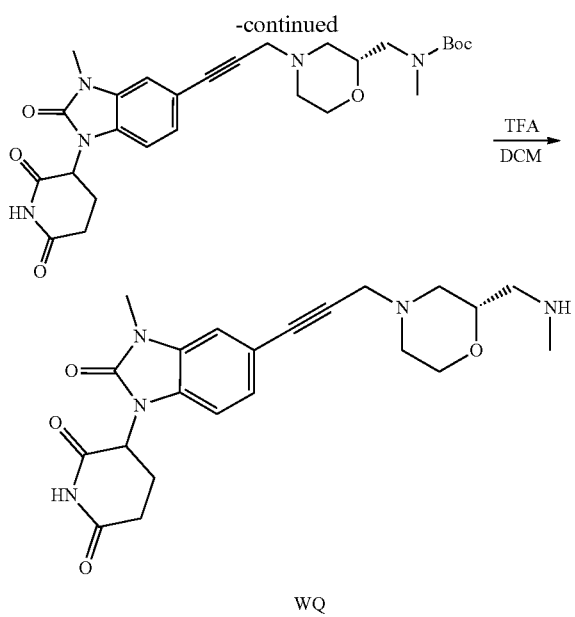

WQ

Step 1—Tert-butyl N-[[(2R)-4-[3-[1-(2,6-dioxo-3-piperidyl)-3-methyl-2-oxo-benzimidazol-5-yl]prop-2-ynyl]morpholin-2-yl]methyl]-Nmethyl-carbamate To a solution of tert-butyl N-methyl-N-[[(2R)-4-prop-2-ynylmorpholin-2-yl]methyl]carbamate (571 mg, 2.13 mmol, Intermediate WP), 3-(5-bromo-3-methyl-2-oxo-benzimidazol-1-yl)piperidine-2,6-dione (400 mg, 1.18 mmol, Intermediate HN) in DMF (15.0 mL) was added Pd(PPh$_3$)$_2$Cl$_2$ (83.0 mg, 118 umol), 4 Å molecular sieves (50.0 mg), Cs$_2$CO$_3$ (1.93 g, 5.91 mmol) and CuI (22.5 mg, 118 umol). The mixture was stirred at 80° C. for 2 hrs under N$_2$. On completion, the mixture was filtered and the filtrate was concentrated in vacuo. The residue was purified by reverse phase (0.1% FA) to give the title compound (400 mg, 64% yield) as yellow solid. $^1$H NMR (400 MHz, CDCl$_3$) δ 8.28 (s, 1H), 7.17 (d, J=8.0 Hz, 1H), 7.10 (s, 1H), 6.74 (d, J=8.0 Hz, 1H), 5.25-5.14 (m, 1H), 3.99-3.90 (m, 1H), 3.82-3.65 (m, 2H), 3.57-3.47 (m, 2H), 3.43 (s, 3H), 3.25-3.14 (m, 1H), 3.00-2.94 (m, 1H), 2.94 (s, 3H), 2.89-2.82 (m, 2H), 2.82-2.74 (m, 2H), 2.74-2.63 (m, 1H), 2.50-2.38 (m, 1H), 2.30-2.21 (m, 1H), 2.20-2.13 (m, 1H), 1.45 (s, 9H).

Step 2—3-[3-Methyl-5-[3-[(2S)-2-(methylaminomethyl)morpholin-4-yl]prop-1-ynyl]-2-oxo-benzimidazol-1-yl]piperidine-2,6-dione To a solution of tert-butyl N-[[(2R)-4-[3-[1-(2,6-dioxo-3-piperidyl)-3-methyl-2-oxo-benzimidazol-5-yl]prop-2-ynyl]morpholin-2-yl]methyl]-N-methyl-carbamate (150 mg, 285 umol) in DCM (5.00 mL) was added TFA (7.70 g, 67.5 mmol, 5.00 mL). The mixture was stirred at 20° C. for 1 hr. On completion, the mixture was concentrated in vacuo to give the title compound (150 mg, 97% yield, TFA salt) as yellow solid. $^1$H NMR (400 MHz, DMSO-d$_6$) δ 11.15 (s, 1H), 8.83 (s, 1H), 7.37 (d, J=1.2 Hz, 1H), 7.27-7.22 (m, 1H), 7.22-7.17 (m, 1H), 5.47-5.37 (m, 1H), 4.39-4.21 (m, 3H), 4.18-4.14 (m, 1H), 4.09-4.03 (m, 1H), 3.84-3.73 (m, 1H), 3.58-3.44 (m, 2H), 3.36 (s, 3H), 3.27-3.17 (m, 1H), 3.12-3.02 (m, 2H), 2.95-2.84 (m, 2H), 2.68-2.62 (m, 1H), 2.60-2.57 (m, 3H), 2.09-2.00 (m, 1H).

3-[3-methyl-4-[4-[4-(methylamino)butoxy]butyl]-2-oxo-benzimidazol-1-yl]piperidine-2,6-dione (Intermediate WR)

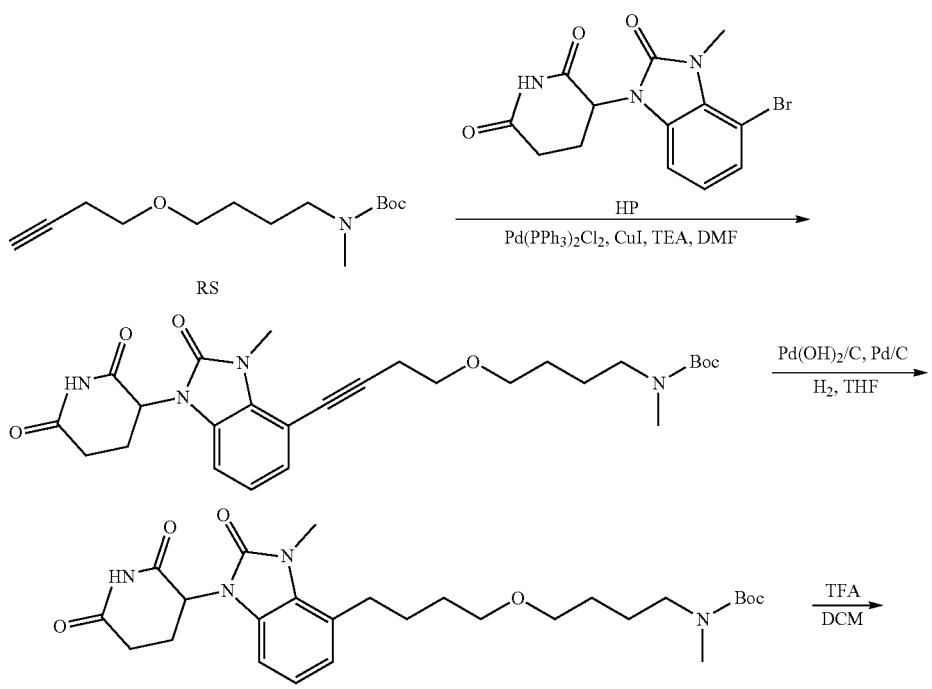

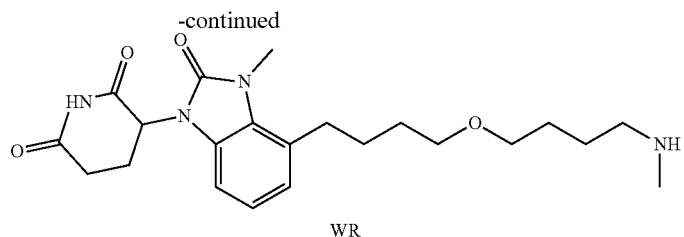

WR

Step 1 Tert-butyl N-[4-[4-[1-(2,6-dioxo-3-piperidyl)-3-methyl-2-oxo-benzimidazol-4-yl]but-3-ynoxy]butyl]-N-methyl-carbamate To a solution of tert-butyl N-(4-but-3-ynoxybutyl)-N-methyl-carbamate (500 mg, 1.96 mmol, Intermediate RS) and 3-(4-bromo-3-methyl-2-oxo-benzimidazol-1-yl)piperidine-2,6-dione (221 mg, 653 umol, Intermediate HP) in DMF (10 mL) was added CuI (24.8 mg, 131 umol), Cs$_2$CO$_3$ (213 mg, 653 umol), Pd(PPh$_3$)$_2$Cl$_2$ (91.6 mg, 131 umol) and 4 Å molecular sieves (200 mg, 653 umol) at 25° C. The reaction mixture was stirred at 80° C. for 2 hours. On completion, the reaction mixture was filtered and concentrated in vacuo. The residue was diluted with water (30 mL), and then extracted with EA (3×50 mL). The combined organic layers were washed with brine (30 mL), dried over Na$_2$SO$_4$, filtered and the filtrate was concentrated in vacuo. The residue was purified by reverse phase (FA condition) to give the title compound (320 mg, 95% yield) as a purple solid. LC-MS (ESI$^+$) m/z 413.2 (M+H−100)$^+$.

Step 2—Tert-butyl N-[4-[4-[1-(2,6-dioxo-3-piperidyl)-3-methyl-2-oxo-benzimidazol-4-yl]butoxy]butyl]-N-methyl-carbamate To a solution of tert-butyl N-[4-[4-[1-(2,6-dioxo-3-piperidyl)-3-methyl-2-oxo-benzimidazol-4-yl]but-3-ynoxy]butyl]-N-methyl-carbamate (300 mg, 585 umol) in THF (20 mL) was added Pd(OH)$_2$/C (500 mg, 585 umol, 20 wt %) and Pd/C (500 mg, 585 umol, 10 wt %) at 25° C. The reaction mixture was stirred at 25° C. for 2 hours under H$_2$ (15 psi). On completion, the reaction mixture was filtered through celite and the filtrate was concentrated in vacuo to give the title compound (280 mg, 92% yield) as colorless oil. LC-MS (ESI$^+$) m/z 417.3 (M+H−100)$^+$.

Step 3—3-[3-methyl-4-[4-[4-(methylamino)butoxy]butyl]-2-oxo-benzimidazol-1-yl]piperidine-2,6-dione To a solution of tert-butyl N-[4-[4-[1-(2,6-dioxo-3-piperidyl)-3-methyl-2-oxo-benzimidazol-4-yl]butoxy]butyl]-N-methyl-carbamate (140 mg, 271 umol) in DCM (10 mL) was added TFA (5 mL) at 25° C. The reaction mixture was stirred at 25° C. for 2 hours. On completion, the reaction mixture was concentrated in vacuo to give the title compound (110 mg, 97% yield) as colorless oil. LC-MS (ESI$^+$) m/z 417.2 (M+H)$^+$.

Tert-butyl (3R)-3-prop-2-ynoxypyrrolidine-1-carboxylate (Intermediate WU)

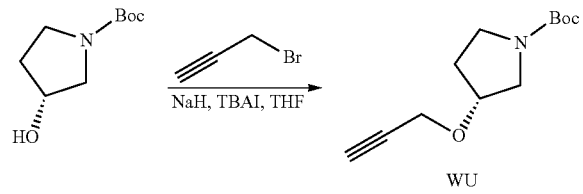

To a mixture of tert-butyl (3R)-3-hydroxypyrrolidine-1-carboxylate (5.00 g, 26.7 mmol, CAS #109431-87-0) and TBAI (493 mg, 1.34 mmol) in THF (50 mL) was added sodium hydride (1.28 g, 32.0 mmol, 60% oil dispersion) in portions at 0° C. After 0.5 hour, 3-bromoprop-1-yne (6.35 g, 53.4 mmol) was added to the mixture. The reaction mixture was stirred at 0-25° C. for 12.5 hours. On completion, the reaction was quenched with water (1.0 mL). The mixture was filtered and the filtrate was concentrated in vacuo. The residue was purified by silica gel chromatography on silica gel to give the title compound (6.00 g, 99% yield) as yellow oil. $^1$H NMR (400 MHz, CDCl$_3$) δ 4.28 (s, 1H), 4.24-4.06 (m, 2H), 3.55-3.32 (m, 4H), 2.44 (t, J=2.4 Hz, 1H), 2.13-1.88 (m, 2H), 1.46 (s, 9H).

3-[3-Methyl-2-oxo-4-[3-[(3R)-pyrrolidin-3-yl]oxypropyl]benzimidazol-1-yl]piperidine-2,6-dione (Intermediate WV)

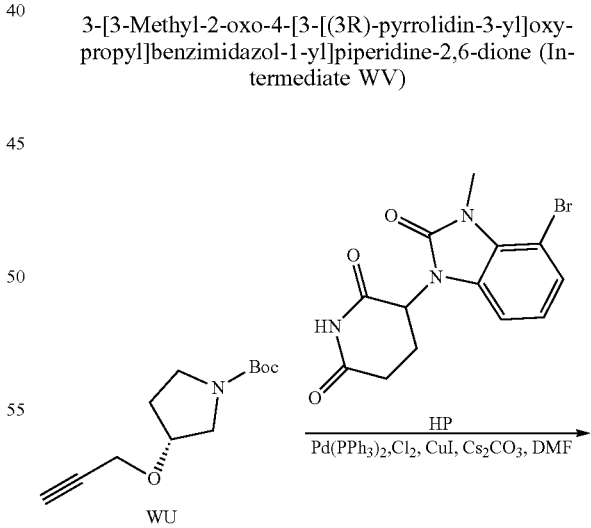

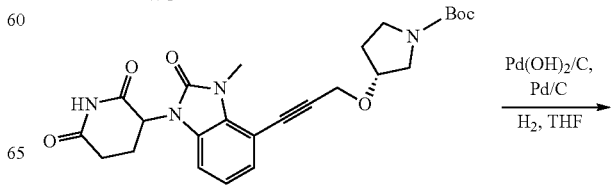

-continued

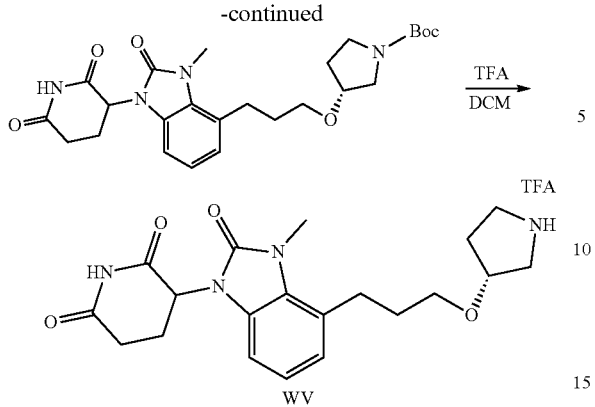

Step 1—Tert-butyl (3R)-3-[3-[1-(2,6-dioxo-3-piperidyl)-3-methyl-2-oxo-benzimidazol-4-yl]prop-2-ynoxy]pyrrolidine-1-carboxylate A mixture of tert-butyl (3R)-3-prop-2-ynoxypyrrolidine-1-carboxylate (666 mg, 2.96 mmol, Intermediate WU), 3-(4-bromo-3-methyl-2-oxo-benzimidazol-1-yl)piperidine-2,6-dione (400 mg, 1.18 mmol, Intermediate HP), Pd(PPh$_3$)$_2$Cl$_2$ (166 mg, 236 umol), CuI (45.0 mg, 236 umol), 4 Å MS (100 mg, 1.18 mmol) and Cs$_2$CO$_3$ (1.93 g, 5.91 mmol) in DMF (8 mL) was stirred at 80° C. for 2 hours under N$_2$. On completion, the reaction mixture was filtered and the filtrate was concentrated in vacuo. The residue was purified by reverse phase (FA condition) to give the title compound (330 mg, 57% yield) as brown solid. $^1$H NMR (400 MHz, DMSO-d$_6$) δ 11.13 (s, 1H), 7.18 (d, J=7.6 Hz, 1H), 7.13 (d, J=7.6 Hz, 1H), 7.06-7.00 (m, 1H), 5.42-5.38 (m, 1H), 4.48 (s, 2H), 4.34-4.24 (m, 1H), 3.63 (s, 3H), 3.37-3.35 (m, 1H), 3.27-3.17 (m, 2H), 2.95-2.82 (m, 1H), 2.77-2.63 (m, 2H), 2.07-1.89 (m, 4H), 1.38 (d, J=9.6 Hz, 9H).

Step 2—Tert-butyl (3R)-3-[3-[1-(2,6-dioxo-3-piperidyl)-3-methyl-2-oxo-benzimidazol-4-yl]propoxy]pyrrolidine-1-carboxylate To a solution of tert-butyl (3R)-3-[3-[1-(2,6-dioxo-3-piperidyl)-3-methyl-2-oxo-benzimidazol-4-yl]prop-2-ynoxy] pyrrolidine-1-carboxylate (300 mg, 621 umol) in THF (10 mL) was added Pd/C (150 mg, 10 wt %) and Pd(OH)$_2$/C (150 mg, 20 wt %) at 20° C. The reaction mixture was stirred at 20° C. for 12 hours under H$_2$ (15 psi). On completion, the reaction mixture was filtered and the filtrate was concentrated in vacuo to give the title compound (300 mg, 99% yield) as brown solid. $^1$H NMR (400 MHz, DMSO-d$_6$) δ 11.09 (s, 1H), 6.99-6.92 (m, 2H), 6.90-6.82 (m, 1H), 5.42-5.38 (m, 1H), 4.06-3.96 (m, 1H), 3.55 (s, 3H), 3.50-3.39 (m, 2H), 3.32-3.30 (m, 1H), 3.30-3.26 (m, 2H), 3.26-3.20 (m, 1H), 2.98-2.91 (m, 2H), 2.90-2.82 (m, 1H), 2.75-2.57 (m, 2H), 2.03-1.95 (m, 1H), 1.94-1.86 (m, 2H), 1.85-1.74 (m, 2H), 1.40 (s, 9H).

Step 3—3-[3-Methyl-2-oxo-4-[3-[(3R)-pyrrolidin-3-yl]oxypropyl]benzimidazol-1-yl]piperidine-2,6-dione To a solution of tert-butyl (3R)-3-[3-[1-(2,6-dioxo-3-piperidyl)-3-methyl-2-oxo-benzimidazol-4-yl]propoxy]pyrrolidine-1-carboxylate (300 mg, 616 umol) in dichloromethane (3 mL) was added TFA (3 mL) at 15° C. The reaction mixture was stirred at 15° C. for 0.5 hour. On completion, the reaction mixture was concentrated in vacuo to give the title compound (330 mg, 100% yield, TFA salt) as yellow semisolid. LC-MS (ESI$^+$) m/z 387.2 (M+H)$^+$.

1-(2,6-dioxo-3-piperidyl)-3-methyl-2-oxo-benzimidazole-4-carbaldehyde (Intermediate WW)

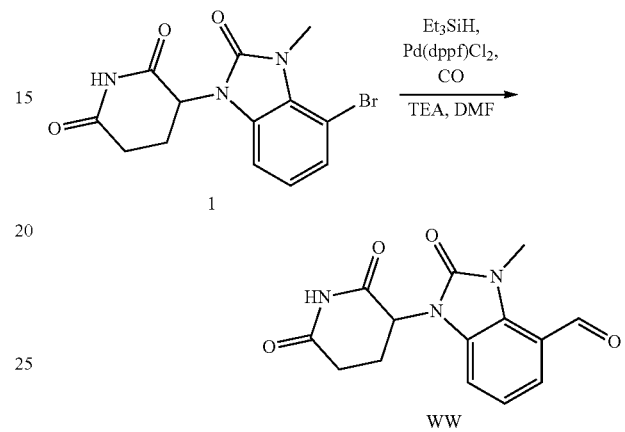

To a solution of 3-(4-bromo-3-methyl-2-oxo-benzimidazol-1-yl)piperidine-2,6-dione (500 mg, 1.48 mmol, Intermediate HP) in DMF (20 mL) was added TEA (448 mg, 4.44 mmol), Pd(dppf)Cl$_2$ (162 mg, 221 umol) and Et$_3$SiH (515 mg, 4.44 mmol). The reaction mixture was stirred at 80° C. for 16 hours under CO (50 Psi). On completion, the reaction mixture was concentrated in vacuo and purified by reverse phase (0.1% FA) to give the title compound (400 mg, 47% yield) as a white solid. LC-MS (ESI$^+$) m/z 288.0 (M+H)$^+$

3-[3-Methyl-4-[[4-(methylamino)-1-piperidyl]methyl]-2-oxo-benzimidazol-1-yl]piperidine-2,6-dione (Intermediate WX)

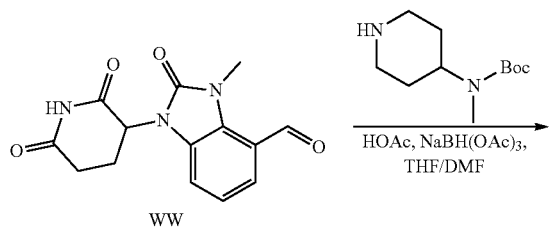

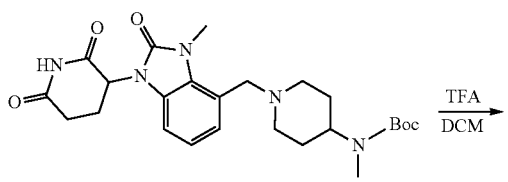

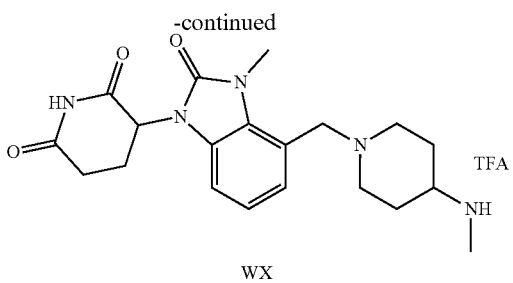

WX

Step 1—Tert-butyl N-[1-[[1-(2,6-dioxo-3-piperidyl)-3-methyl-2-oxo-benzimidazol-4-yl]methyl]-4-piperidyl]-N-methyl-carbamate To a solution of 1-(2,6-dioxo-3-piperidyl)-3-methyl-2-oxo-benzimidazole-4-carbaldehyde (160 mg, 556 umol, Intermediate WW) and tert-butyl N-methyl-N-(4-piperidyl)carbamate (119 mg, 556 umol) in a mixed solvents of THF (3 mL) and DMF (1.5 mL) was added AcOH until the pH=5-7. After the reaction mixture was stirred at 20° C. for 3 hours. NaBH(OAc)$_3$ (177 mg, 835 umol) was added to the reaction mixture. The mixture was stirred at 20° C. for 12 hours. On completion, the reaction mixture was quenched by water (3 drops) and filtered. The filtrate was concentrated in vacuo. The residue was purified by reverse phase (FA condition) to give the title compound (220 mg, 46% yield) as white solid. LC-MS (ESI$^+$) m/z 486.2 (M+H)$^+$.

Step 2—3-[3-Methyl-4-[[4-(methylamino)-1-piperidyl]methyl]-2-oxo-benzimidazol-1-yl]piperidine-2,6-dione To a solution of tert-butyl N-[1-[[1-(2,6-dioxo-3-piperidyl)-3-methyl-2-oxo-benzimidazol-4-yl]methyl]-4-piperidyl]-N-methyl-carbamate (200 mg, 235 umol) in DCM (3 mL) was added TFA (3 mL). The reaction mixture was stirred at 15° C. for 0.5 hour. On completion, the reaction mixture was concentrated in vacuo to give the title compound (220 mg, 100% yield, TFA salt) as yellow oil. LC-MS (ESI$^+$) m/z 386.2 (M+H)$^+$.

3-[3-Methyl-4-[4-[4-(methylaminomethyl)-1-piperidyl]but-1-ynyl]-2-oxo-benzimidazol-1-yl]piperidine-2,6-dione (Intermediate WZ)

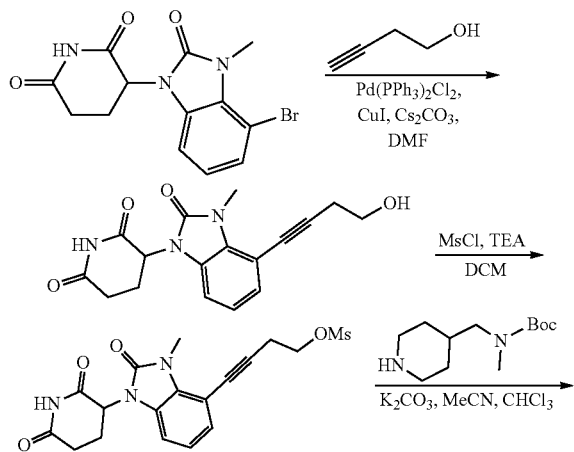

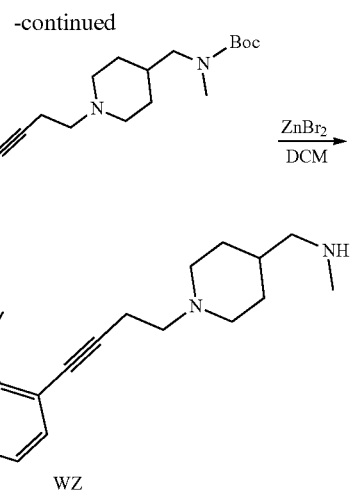

WZ

Step 1—3-[4-(4-Hydroxybut-1-ynyl)-3-methyl-2-oxo-benzimidazol-1-yl]piperidine-2,6-dione To a solution of 3-(4-bromo-3-methyl-2-oxo-benzimidazol-1-yl)piperidine-2,6-dione (1.00 g, 2.96 mmol, Intermediate HP) and but-3-yn-1-ol (518 mg, 7.39 mmol, 559 uL, CAS #927-74-2) in DMSO (15 mL) was added Pd(PPh$_3$)$_2$Cl$_2$ (207 mg, 295 umol), CuI (56.3 mg, 295 umol) and DIPEA (1.91 g, 14.7 mmol, 2.58 mL). The reaction mixture was stirred at 80° C. for 2 hrs under N$_2$. On completion, the mixture was filtered, and the filtrate was concentrated in vacuo to give a residue. The residue was purified by reverse phase (0.1% FA condition) to give the title compound (600 mg, 62% yield) as a white solid. $^1$H NMR (400 MHz, DMSO-d$_6$) δ 11.13 (s, 1H), 7.15-6.97 (m, 3H), 5.39 (dd, J=4.8, 12.4 Hz, 1H), 4.94 (s, 1H), 3.65 (s, 3H), 3.34 (s, 2H), 2.95-2.84 (m, 1H), 2.69-2.59 (m, 4H), 2.06-2.00 (m, 1H); LC-MS (ESI$^+$) m/z 328.1 (M+H)$^+$.

Step 2—4-[1-(2,6-Dioxo-3-piperidyl)-3-methyl-2-oxo-benzimidazol-4-yl]but-3-ynyl methanesulfonate To a solution of 3-[4-(4-hydroxybut-1-ynyl)-3-methyl-2-oxo-benzimidazol-1-yl]piperidine-2,6-dione (600 mg, 1.83 mmol) and TEA (556 mg, 5.50 mmol, 765 uL) in DCM (20 mL) was added MsCl (314 mg, 2.75 mmol, 212 uL) dropwise at 0° C. The reaction mixture was stirred at 25° C. for 2 hrs. On completion, the reaction mixture was quenched with H$_2$O (30 mL), then extracted with DCM (2×50 mL). The organic phase was dried with Na$_2$SO$_4$, filtrated and concentrated in vacuo to give the title compound (500 mg, 67% yield) as a yellow solid. LC-MS (ESI$^+$) m/z 406.2 (M+H)$^+$.

Step 3—Tert-butyl N-[[1-[4-[1-(2,6-dioxo-3-piperidyl)-3-methyl-2-oxo-benzimidazol-4-yl]but-3-ynyl]-4-piperidyl]methyl]-N-methyl-carbamate To a solution of 4-[1-(2,6-dioxo-3-piperidyl)-3-methyl-2-oxo-benzimidazol-4-yl]but-3-ynyl methanesulfonate (400 mg, 986 umol) and tert-butyl N-methyl-N-(4-piperidylmethyl)carbamate (270 mg, 1.18 mmol, CAS #138022-04-5) in MeCN (10 mL) and CHCl$_3$ (10 mL) was added K$_2$CO$_3$ (409 mg, 2.96 mmol). The reaction mixture was stirred at 65° C. for 16 hrs. On completion, the reaction mixture was diluted with water (30 mL) and extracted with EA (3×50 mL). The combined organic layers was dried over Na₂SO₄, filtered and concentrated in vacuo to give a residue. The residue was purified by reverse phase (0.1% FA condition) to give the title compound (140 mg, 26% yield) as a yellow solid. $^1$H NMR (400 MHz, DMSO-$d_6$) δ 11.11 (s, 1H), 7.11 (d, J=7.2 Hz, 1H), 7.07-7.02 (m, 1H), 7.01-6.96 (m, 1H), 5.38 (dd, J=5.2, 12.8 Hz, 1H), 3.67 (s, 3H), 3.05 (d, J=6.4 Hz, 2H), 2.96-2.87 (m, 3H), 2.69-2.58 (m, 9H), 2.05-1.94 (m, 3H), 1.58-1.51 (m, 3H), 1.38 (s, 9H), 1.18-1.08 (m, 2H); LC-MS (ESI⁺) m/z 538.4 (M+H)⁺.

Step 4—3-[3-Methyl-4-[4-[4-(methylaminomethyl)-1-piperidyl]but-1-ynyl]-2-oxo-benzimidazol-1-yl]piperidine-2,6-dione To a solution of tert-butyl N-[[1-[4-[1-(2,6-dioxo-3-piperidyl)-3-methyl-2-oxo-benzimidazol-4-yl]but-3-ynyl]-4-piperidyl]methyl]-N-methyl-carbamate (140 mg, 260 umol) in DCM (3 mL) was added ZnBr₂ (293 mg, 1.30 mmol, 65.1 uL). The reaction mixture was stirred at 20° C. for 48 hrs. On completion, the reaction mixture was concentrated in vacuo to give a residue. The residue was purified by reverse phase (0.1% FA condition) to give the title compound (100 mg, 87% yield) as a white solid. LC-MS (ESI⁺) m/z 438.2 (M+H)⁺.

Tert-butyl (2,2-difluoro-3-(prop-2-yn-1-yloxy)propyl)(methyl)carbamate (Intermediate XA)

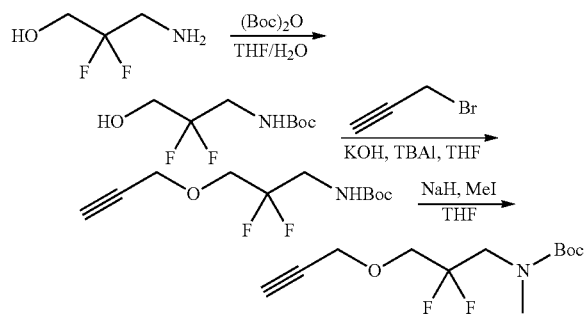

Step 1—Tert-butyl (2,2-difluoro-3-hydroxypropyl)carbamate

To a solution of 3-amino-2,2-difluoro-propan-1-ol (2.00 g, 18.0 mmol, CAS #155310-11-5) in a mixed solvents of THF (75 mL) and H₂O (75 mL) was added Boc₂O (3.93 g, 18.0 mmol) slowly at 0° C. The reaction mixture was stirred at 25° C. for 16 hours. On completion, the reaction mixture was diluted with 1.0 M aq.HCl (100 mL) and extracted with EA (2×150 mL). The combined organic phase was washed with brine (50 mL), dried over Na₂SO₄, filtered and concentrated in vacuo to give the title compound (3.76 g, 98% yield) as white solid. $^1$H NMR (400 MHz, CDCl₃) δ 5.04 (s, 1H), 4.10-3.87 (m, 1H), 3.76-3.63 (m, 2H), 3.60-3.54 (m, 2H), 1.48 (s, 9H).

Step 2—Tert-butyl (2,2-difluoro-3-(prop-2-yn-1-yloxy)propyl)carbamate

To a solution of tert-butyl N-(2,2-difluoro-3-hydroxypropyl)carbamate (5.00 g, 23.7 mmol) in THF (100 mL) was added KOH (1.33 g, 23.7 mmol), KI (393 mg, 2.37 mmol), TBAI (1.31 g, 3.55 mmol) and 3-bromoprop-1-yne (4.22 g, 28.41 mmol) at 25° C. The reaction mixture was stirred at 25° C. for 16 hours. On completion, the reaction mixture was diluted with sat. aq. NH₄Cl (100 mL) and extracted with EA (2×150 mL). The combined organic phase was concentrated in vacuo. The residue was purified by silica gel chromatography (PE:EA=40:1) to give title compound (3.27 g, 55% yield) as colorless oil. $^1$H NMR (400 MHz, CDCl₃) δ 4.95-4.73 (m, 1H), 4.30-4.24 (m, 2H), 3.84-3.74 (m, 2H), 3.72-3.58 (m, 2H), 2.56-2.46 (m, 1H), 1.47 (s, 9H).

Step 3—Tert-butyl (2,2-difluoro-3-(prop-2-yn-1-yloxy)propyl)(methyl)carbamate

To solution of tert-butyl N-(2,2-difluoro-3-prop-2-ynoxy-propyl)carbamate (3.00 g, 12.1 mmol) in THF (50 mL) was added NaH (578 mg, 14.4 mmol, 60% dispersion in mineral oil) at 0° C. The mixture was stirred at 0° C. for 0.5 hour, then MeI (3.42 g, 24.1 mmol) was added. The reaction mixture stirred at 0-25° C. for 2 hours. On completion, the reaction was queched with water (100 mL). The mixture was extracted with EA (2×100 mL). The combined organic phase was concentrated in vacuo to give the title compound (3.00 g, 95% yield) as yellow oil. $^1$H NMR (400 MHz, CDCl₃) δ 4.25-4.18 (m, 2H), 3.72-3.58 (m, 4H), 2.89 (s, 3H), 2.42 (s, 1H), 1.40 (s, 9H).

3-(4-(3-(2,2-Difluoro-3-(methylamino)propoxy)propyl)-3-methyl-2-oxo-2,3-dihydro-1H-benzo[d]imidazol-1-yl)piperidine-2,6-dione (Intermediate XB)

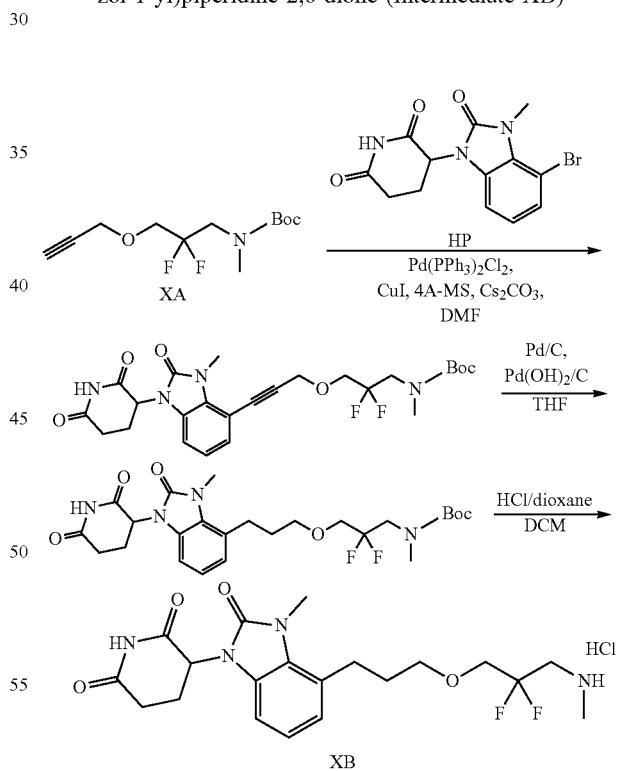

Step 1—Tert-butyl (3-((3-(1-(2,6-dioxopiperidin-3-yl)-3-methyl-2-oxo-2,3-dihydro-1H-benzo[d]imidazol-4-yl)prop-2-yn-1-yl)oxy)-2,2-difluoropropyl)(methyl)carbamate To a solution of tert-butyl N-(2,2-difluoro-3-prop-2-ynoxy-propyl)carbamate (442 mg, 1.77 mmol, Intermediate XA) and 3-(4-bromo-3-methyl-2-oxo-benzimidazol-1-yl)piperidine-2,6-dione (300 mg, 887 umol, Intermediate HP) in DMF (6 mL) was added Pd(PPh$_3$)$_2$Cl$_2$ (125 mg, 177 umol), CuI (33.8 mg, 177 umol), Cs$_2$CO$_3$ (1.45 g, 4.44 mmol) and 4 Å molecular sieves (100 mg) at 20° C. The mixture was stirred at 80° C. for 2 hours under N$_2$. On completion, the reaction mixture was cooled to 20° C. The mixture was diluted with EA (50 mL) and filtered. The filtrate was washed with brine (50 mL), dried over Na$_2$SO$_4$, filtered and concentrated in vacuo. The residue was purified by reverse phase (FA condition) to give the title compound (160 mg, 35% yield) as brown solid. $^1$H NMR (400 MHz, DMSO-d$_6$) δ 11.11 (s, 1H), 7.24-7.17 (m, 1H), 7.17-7.11 (m, 1H), 7.08-7.01 (m, 1H), 5.46-5.35 (m, 1H), 4.58 (s, 2H), 3.89-3.78 (m, 2H), 3.78-3.68 (m, 2H), 3.67-3.59 (m, 3H), 1.38 (s, 9H). LC-MS (ESI$^+$) m/z 543.1 (M+Na)$^+$.

Step 2—Tert-butyl (3-(3-(1-(2,6-dioxopiperidin-3-yl)-3-methyl-2-oxo-2,3-dihydro-1H-benzo[d]imidazol-4-yl)propoxy)-2,2-difluoropropyl)(methyl)carbamate To a solution of tert-butyl N-[3-[3-[1-(2,6-dioxo-3-piperidyl)-3-methyl-2-oxo-benzimidazol-4-yl]prop-2-ynoxy]-2,2-difluoro-propyl]-N-methyl-carbamate (200 mg, 384 umol) in THF (10 mL) was added Pd/C (50.0 mg, 10 wt %) and Pd(OH)$_2$/C (50.0 mg, 10 wt %) at 25° C. The mixture was stirred at 25° C. for 18 hours under H$_2$ (15 psi). On completion, the reaction mixture was diluted with THF (40 mL), filtrated and concentrated in vacuo to give the title compound (195 mg, 97% yield) as yellow solid. $^1$H NMR (400 MHz, DMSO-d$_6$) δ 11.08 (s, 1H), 7.01-6.94 (m, 2H), 6.91-6.84 (m, 1H), 5.40-5.33 (m, 1H), 3.64-3.58 (m, 6H), 3.58-3.56 (m, 3H), 3.02-2.93 (m, 2H), 2.87 (s, 3H), 1.91-1.82 (m, 2H), 1.79-1.74 (m, 4H), 1.40 (s, 9H); LC-MS (ESI$^+$) m/z 547.3 (M+Na)$^+$.

Step 3—3-(4-(3-(2,2-Difluoro-3-(methylamino)propoxy)propyl)-3-methyl-2-oxo-2,3-dihydro-1H-benzo[d]imidazol-1-yl)piperidine-2,6-dione To the solution of tert-butyl N-[3-[3-[1-(2,6-dioxo-3-piperidyl)-3-methyl-2-oxo-benzimidazol-4-yl]propoxy]-2,2-difluoro-propyl]-N-methyl-carbamate (180 mg, 343 umol) in DCM (3 mL) was added HCl/dioxane (3 mL) at 25° C. The reaction mixture was stirred at 25° C. for 2 hours. On completion, the mixture was concentrated in vacuo to give the title compound (155 mg, 98% yield, HCl salt). LC-MS (ESI$^+$) m/z 425.1 (M+H)$^+$.

3-[6-[3-[3-(Methylamino)propoxy]propyl]-2-oxo-1,3-benzoxazol-3-yl]piperidine-2,6-dione (Intermediate XC)

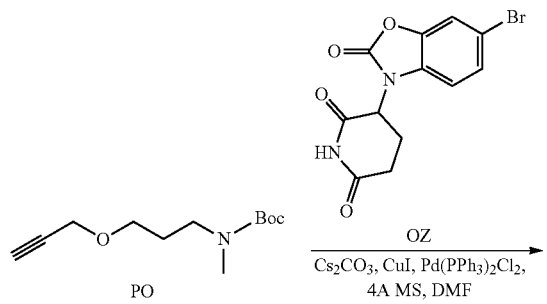

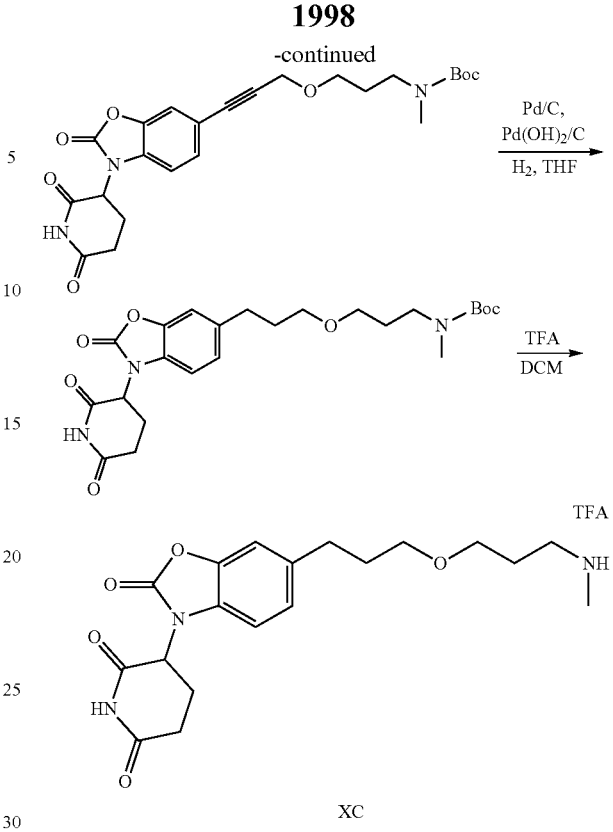

Step 1—Tert-butyl N-[3-[3-[3-(2,6-dioxo-3-piperidyl)-2-oxo-1,3-benzoxazol-6-yl]prop-2-ynoxy]propyl]-N-methyl-carbamate To a mixture of 3-(6-bromo-2-oxo-1,3-benzoxazol-3-yl)piperidine-2,6-dione (450 mg, 1.38 mmol, Intermediate OZ), tert-butyl N-methyl-N-(3-prop-2-ynoxypropyl)carbamate (566 mg, 2.49 mmol, Intermediate PO) in DMF (10 mL) was added Cs$_2$CO$_3$ (2.25 g, 6.92 mmol), CuI (79.08 mg, 415.24 umol), Pd(PPh$_3$)$_2$Cl$_2$ (97.1 mg, 138 umol) and molecular sieves 4 Å (50 mg). The reaction mixture was stirred at 80° C. for 2 hours under N$_2$. On completion, the reaction was filtered. And the filtrate was poured into water (100 mL), then the aqueous phase was extracted with ethyl acetate (2×40 mL). The combined organic phase was washed with brine (2×40 mL), dried with anhydrous Na$_2$SO$_4$, filtered and concentrated in vacuo to give the residue. The residue was purified by reversed-phase HPLC (0.1% FA condition) to give the title compound (350 mg, 49% yield) as a brown solid. $^1$H NMR (300 MHz, CDCl$_3$) δ 8.24-8.11 (m, 1H), 7.35 (s, 2H), 6.78 (d, J=8.4 Hz, 1H), 5.06 (d, J=5.2, 12.8 Hz, 1H), 4.37 (s, 2H), 3.60 (d, J=6.4 Hz, 2H), 3.34 (d, J=6.8 Hz, 2H), 2.89 (s, 3H), 1.94-1.78 (m, 3H), 1.75-1.61 (m, 3H), 1.47 (s, 9H).

Step 2—Tert-butyl N-[3-[3-[3-(2,6-dioxo-3-piperidyl)-2-oxo-1,3-benzoxazol-6-yl]propoxy]propyl]-N-methyl-carbamate To a mixture of tert-butyl N-[3-[3-[3-(2,6-dioxo-3-piperidyl)-2-oxo-1,3-benzoxazol-6-yl]prop-2-ynoxy]propyl]-N-methyl-carbamate (350 mg, 742 umol) in THF (10 mL) was added Pd/C (50 mg, 10 wt %) and Pd(OH)$_2$/C (50 mg, 10 wt %) under N$_2$. The suspension was degassed under vacuum and purged with H$_2$ three times. The mixture was stirred at 25° C. for 12 hours under H$_2$ (15 psi). On completion, the reaction mixture was filtered and the filtrate was concentrated in vacuo to give the title compound (330 mg, 93% yield) as brown oil. $^1$H NMR (400 MHz, CDCl$_3$) δ 8.19 (s, 1H), 7.12 (s, 1H), 7.00 (d, J=8.0 Hz, 1H), 6.73 (d, J=8.0 Hz, 1H), 5.06 (d, J=5.6, 13.2 Hz, 1H), 3.41 (q, J=6.4 Hz, 4H), 3.30 (s, 2H), 3.03-2.94 (m, 1H), 2.89-2.84 (m, 3H), 2.78-2.68 (m, 3H), 2.37-2.26 (m, 1H), 1.94-1.72 (m, 4H), 1.63 (d, J=6.8 Hz, 2H), 1.46 (s, 8H).

Step 3—3-[6-[3-[3-(Methylamino)propoxy]propyl]-2-oxo-1,3-benzoxazol-3-yl]piperidine-2,6-dione To a mixture of tert-butyl N-[3-[3-[3-(2,6-dioxo-3-piperidyl)-2-oxo-1,3-benzoxazol-6-yl]propoxy]propyl]-N-methyl-carbamate (320 mg, 673 umol) in DCM (10 mL) was added TFA (153 mg, 1.35 mmol). The reaction mixture was stirred at 25° C. for 1 hour. On completion, the reaction mixture was concentrated in vacuo to give the title compound (320 mg, 97% yield, TFA salt) as a white solid. LC-MS (ESI$^+$) m/z 376.2 (M+H)$^+$.

3-[3-Methyl-4-[3-[3-(methylamino)propoxy]prop-1-ynyl]-2-oxo-benzimidazol-1-yl]piperidine-2,6-dione (Intermediate XD)

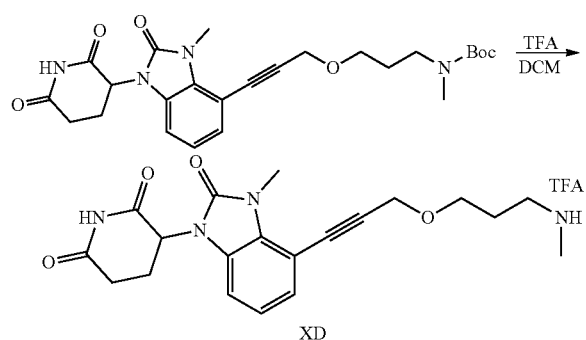

XD

To a mixture of tert-butyl N-[3-[3-[1-(2,6-dioxo-3-piperidyl)-3-methyl-2-oxo-benzimidazol-4-yl]prop-2-ynoxy]propyl]-N-methyl-carbamate (180 mg, 371 umol, synthesized via Step 1 of Intermediate PP) in DCM (5 mL) was added TFA (7.70 g, 67.5 mmol, 5.00 mL). The reaction mixture was stirred at 25° C. for 2 hours. On completion, the reaction mixture was concentrated in vacuo to give the title compound (180 mg, 97% yield, TFA salt) as a yellow solid. $^1$H NMR (400 MHz, DMSO-d$_6$) δ 11.13 (s, 1H), 8.35 (s, 2H), 7.19 (d, J=7.6 Hz, 1H), 7.14-7.11 (m, 1H), 7.06-7.01 (m, 1H), 5.40 (dd, J=12.8 Hz, 1H), 4.45 (s, 3H), 3.65 (s, 3H), 3.60 (s, 2H), 2.97 (m, 2H), 2.91-2.83 (m, 1H), 2.73-2.60 (m, 2H), 2.52-2.50 (m, 2H), 2.06-1.99 (m, 1H), 1.90-1.83 (m, 2H).

2-(Methylamino)ethylN-[[1-(2,6-dioxo-3-piperidyl)-3-methyl-2-oxo-benzimidazol-5-yl]methyl]carbamate (Intermediate XE)

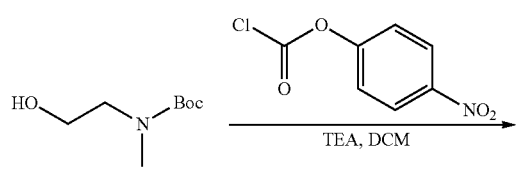

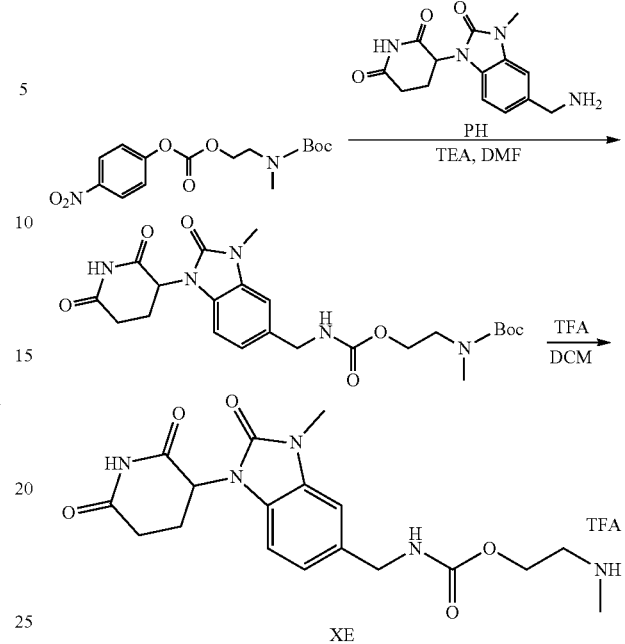

XE

Step 1—2-[Tert-butoxycarbonyl(methyl)amino]ethyl (4-nitrophenyl) carbonate

To a mixture of tert-butyl N-(2-hydroxyethyl)-N-methyl-carbamate (1.00 g, 5.71 mmol, CAS #57561-39-4) and (4-nitrophenyl) carbonochloridate (1.15 g, 5.71 mmol, CAS #7693-46-1) in DCM (20 mL) was added TEA (1.44 g, 14.27 mmol) at 0° C. for 1 hour. On completion, the reaction was poured into the ice-water (50 mL) and extracted with DCM (2×30 mL). The combined organic phase was washed with brine (2×50 mL), dried with anhydrous Na$_2$SO$_4$, filtered and concentrated in vacuo to give the title compound (1.80 g, 92% yield) as a white solid. $^1$H NMR (300 MHz, CDCl$_3$) δ 8.30 (d, J=9.2 Hz, 2H), 7.41 (d, J=9.2 Hz, 2H), 4.41 (t, J=5.6 Hz, 2H), 3.61 (s, 2H), 2.98 (s, 3H), 1.48 (s, 9H).

Step 2—Tert-butyl N-[2-[[1-(2,6-dioxo-3-piperidyl)-3-methyl-2-oxo-benzimidazol-5-yl]methylcarbamoyloxy]ethyl]-N-methyl-carbamate To a mixture of 2-[tert-butoxycarbonyl(methyl)amino]ethyl (4-nitrophenyl) carbonate (172 mg, 507 umol), 3-[5-(aminomethyl)-3-methyl-2-oxo-benzimidazol-1-yl]piperidine-2,6-dione (102 mg, 253 umol, TFA salt, Intermediate PH) in DMF (10 mL) was added TEA (128 mg, 1.27 mmol). The reaction mixture was stirred at 25° C. for 1 hour. On completion, the reaction mixture was concentrated in vacuo to give the residue. The residue was purified by reversed-phase HPLC (0.1% FA condition) to give the title compound (105 mg, 84% yield) as brown solid. $^1$H NMR (400 MHz, DMSO-d$_6$) δ 11.08 (s, 1H), 7.69 (s, 1H), 7.09-7.02 (m, 2H), 6.95 (d, J=8.4 Hz, 1H), 5.39-5.32 (m, 1H), 4.21 (d, J=6.0 Hz, 2H), 4.10-4.03 (m, 2H), 3.36 (t, J=5.6 Hz, 2H), 2.97-2.85 (m, 1H), 2.80 (s, 2H), 2.74 (d, J=4.4, 8.8 Hz, 1H), 2.67-2.59 (m, 1H), 2.10-1.59 (m, 3H), 1.37 (s, 9H).

Step 3—2-(Methylamino)ethylN-[[1-(2,6-dioxo-3-piperidyl)-3-methyl-2-oxo-benzimidazol-5-yl]methyl]carbamate To a mixture of tert-butyl N-[2-[[1-(2,6-dioxo-3-piperidyl)-3-methyl-2-oxo-benzimidazol-5-yl]methylcarbamoyloxy]ethyl]-N-methyl-carbamate (105 mg, 214 umol) in DCM (10 mL) was added TFA (24.4 mg, 214 umol). The reaction mixture was stirred at 25° C. for 0.5 hour. On completion, the reaction mixture was concentrated in vacuo to give the title compound (107 mg, 99% yield, TFA salt) as brown oil. LC-MS (ESI⁺) m/z 390.1 (M+H)⁺.

3-(5-bromo-9H-pyrido[2,3-b]indol-9-yl)piperidine-2,6-dione (Intermediate XF)

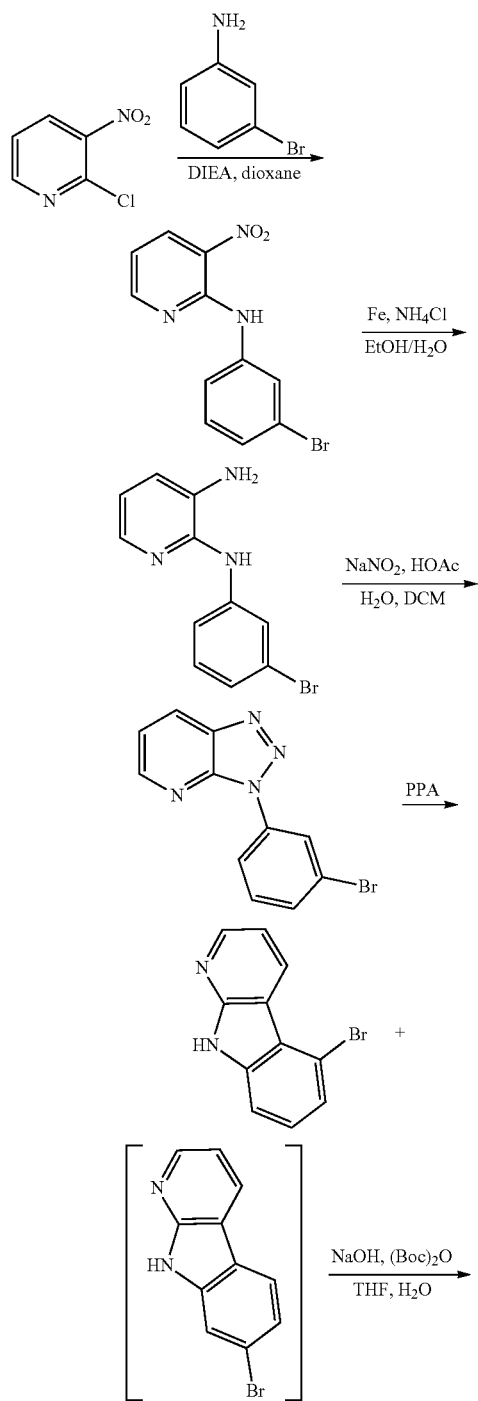

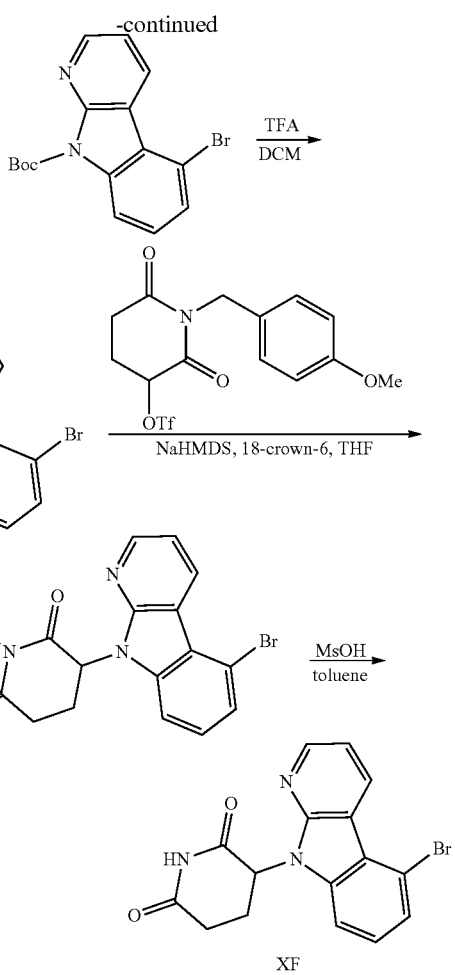

Step 1—N-(3-bromophenyl)-3-nitro-pyridin-2-amine

To a solution of 2-chloro-3-nitro-pyridine (5.00 g, 315 mmol, CAS #34515-82-7) and 3-bromoaniline (5.97 g, 34.7 mmol, CAS #591-19-5) in dioxane (40 mL) was added DIPEA (12.2 g, 94.6 mmol). The reaction mixture was stirred at 115° C. for 2 days. Then the mixture was concentrated under reduced pressure. The residue was purified by silica gel chromatography to give the title compound (8.00 g, 86% yield) as a red solid. LC/MS (ESI, m/z): [M+1]⁺=295.1.

Step 2—N2-(3-bromophenyl)pyridine-2,3-diamine

To a solution of N-(3-bromophenyl)-3-nitro-pyridin-2-amine (5.00 g, 17.0 mmol) and NH₄Cl (9.09 g, 170 mmol) in a mixed solvent of H₂O (80 mL) and EtOH (80 mL) was added Fe (9.49 g, 170 mmol). The reaction mixture was stirred at 80° C. for 1 h. The mixture was then diluted with water (80 mL) and extracted with EA (2×80 mL). The organic layers were washed with brine (2×30 mL), dried with Na₂SO₄, filtered and the filtrate was concentrated under reduced pressure to give the title compound (4.00 g, 89% yield) as a brown solid. LC/MS (ESI, m/z): [M+1]⁺=265.1.

Step 3—3-(3-Bromophenyl)triazolo[4,5-b]pyridine

To a solution of N2-(3-bromophenyl)pyridine-2,3-diamine (4.00 g, 15.1 mmol) in a mixed solvent of HOAc (25 mL) and DCM (25 mL) was added a solution of NaNO$_2$ (1.36 g, 19.7 mmol) in H$_2$O (15 mL) dropwise at 0° C. The reaction mixture was stirred at 25° C. for 30 minutes. On completion, the mixture was diluted with water (50 mL), and extracted with DCM (2×50 mL). The organic layers were washed with brine (2×50 mL), dried with Na$_2$SO$_4$, filtered and the filtrate was concentrated under reduced pressure to give the title compound (4.10 g, 98% yield) as a brown solid. LC/MS (ESI, m/z): [M+1]$^+$=276.1.

Step 4—5-Bromo-9H-pyrido[2,3-b]indole

A mixture of 3-(3-bromophenyl)triazolo[4,5-b]pyridine (3.60 g, 13.1 mmol) in PPA (20 mL) was heated at 170° C. for 3 h. On completion, the mixture was poured into the ice water (200 mL), stirred for 1 h, then filtered. The filter cake was dried under reduced pressure. The filter cake contained two isomers 5-bromo-9H-pyrido[2,3-b]indole and its isomer 7-bromo-9H-pyrido[2,3-b]indole, which were brought on to the next step directly.

Step 5—tert-butyl 5-bromo-9H-pyrido[2,3-b]indole-9-carboxylate

To a mixture of 5-bromo-9H-pyrido[2,3-b]indole and 7-bromo-9H-pyrido[2,3-b]indole (10.0 g, 40.0 mmol) in THF/H$_2$O (100 mL/100 mL) was added Boc$_2$O (17.4 g, 80.0 mmol) and NaOH (4.8 g, 120.0 mmol), and the mixture was stirred at rt for 3 h. On completion, the mixture was poured into the water (200 mL), and extracted with EA (2×100 mL). The organic layers were washed with brine (2×100 mL), dried over Na$_2$SO$_4$, filtered and the filtrate was concentrated to give crude product which was purification by column chromatography to give tert-butyl 5-bromo-9H-pyrido[2,3-b]indole-9-carboxylate (4.10 g, 7% yield for two steps) as brown product. LC/MS (ESI, m/z): [M+1]$^+$=348.2.

Step 6—5-Bromo-9H-pyrido[2,3-b]indole

A mixture of tert-butyl 5-bromo-9H-pyrido[2,3-b]indole-9-carboxylate (9.0 g, 25.9 mmol) in DCM (20 mL) was added TFA (15 mL), and the mixture was stirred at rt for 16 h. On completion, the mixture was concentrated to give the title product (6.0 g, 94% yield) as brown solid.

Step 7—3-(5-Bromopyrido[2,3-b]indol-9-yl)-1-[(4-methoxyphenyl)methyl]piperidine-2,6-dione To a mixture of 5-bromo-9H-pyrido[2,3-b]indole (250 mg, 1.01 mmol) and 18-crown-6 (53 mg, 0.2 mmol) in THF (5 mL) was added NaHMDS (0.75 mL, 1.5 mmol) (2 M in THF) at −30° C. After stirring for 1 h at −30° C., a solution of [1-[(4-methoxyphenyl)methyl]-2,6-dioxo-3-piperidyl]trifluoromethanesulfonate (579 mg, 1.5 mmol) in THF (2 mL) was added into the above mixture dropwise at −30° C. The reaction mixture was stirred at −30° C. for 2 h. On completion, the mixture was quenched with NH$_4$Cl aqueous, then extracted with EA The combined EA layers were concentrated and purified by reverse phase (0.1% FA) to give the title compound (286 mg, 60% yield) as a brown solid. $^1$H NMR (400 MHz, DMSO-d$_6$) δ 8.91 (dd, J=1.2, 7.6 Hz, 1H), 8.59-8.46 (m, 1H), 7.57-7.50 (m, 1H), 7.49-7.42 (m, 1H), 7.41-7.35 (m, 1H), 7.33-7.23 (m, 2H), 7.22-7.05 (m, 1H), 6.94-6.86 (m, 2H), 6.32-5.97 (m, 1H), 4.92-4.75 (m, 2H), 3.75 (s, 3H), 3.24-3.06 (m, 2H), 2.97-2.84 (m, 1H), 2.27-2.15 (m, 1H).

Step 8—3-(5-Bromopyrido[2,3-b]indol-9-yl)piperidine-2,6-dione

To a solution of 3-(5-bromopyrido[2,3-b]indol-9-yl)-1-[(4-methoxyphenyl)methyl]piperidine-2,6-dione (6.0 g, 12.5 mmol) in toluene (50 mL) was added MsOH (10 mL). The reaction mixture was stirred at 110° C. for 4 h. On completion, the mixture was quenched with water (20 mL), then extracted with EA (2×20 mL). The organic layers were concentrated under reduced pressure. The residue was purified by prep-HPLC (column: Phenomenex Synergi C18 150*25*10 um; mobile phase: [water (0.225% FA)-ACN]; B %: 38%-68%, 10 min) to give the title compound (2.8 g, 62% yield) as a white solid. $^1$H NMR (400 MHz, DMSO-d$_6$) δ 11.19 (s, 1H), 8.91 (dd, J=7.8, 1.5 Hz, 1H), 8.53 (dd, J=4.7, 1.3 Hz, 1H), 7.72 (br s, 1H), 7.54-7.53 (m, 1H), 7.49-7.45 (m, 1H), 7.38 (dd, J=7.9, 4.8 Hz, 1H), 6.19-6.00 (m, 1H), 3.16-2.98 (m, 2H), 2.74-2.67 (m, 1H), 2.17-2.14 (m, 1H); LC/MS (ESI, m/z): [M+1]$^+$=358.0/360.0.

3-[5-[3-[2-(2-Aminoethoxy)ethoxy]propyl]pyrido[2,3-b]indol-9-yl]piperidine-2,6-dione (Intermediate XG)

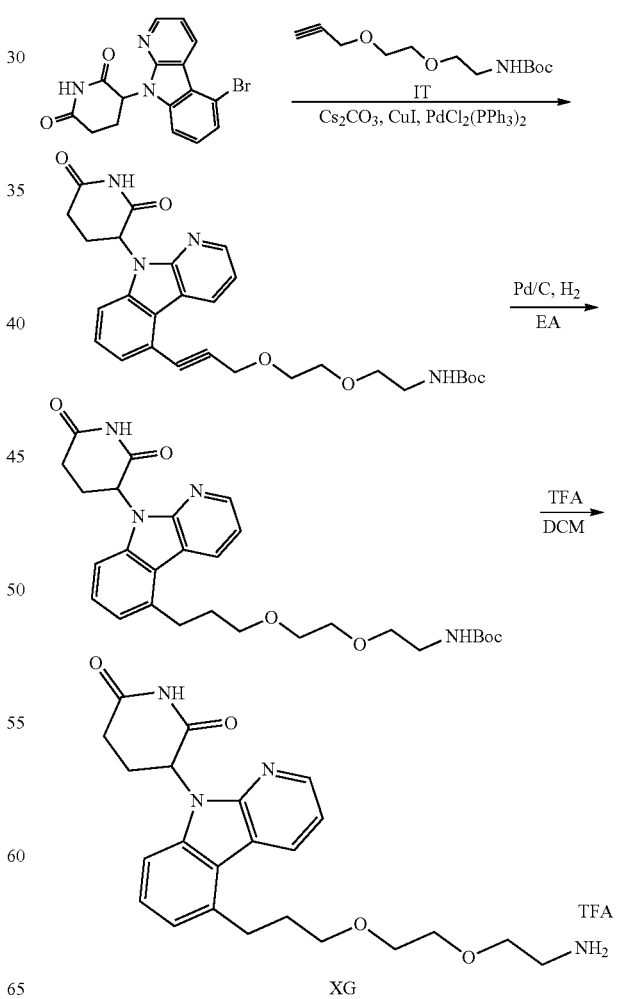

Step 1—tert-butyl (2-(2-((3-(9-(2,6-dioxopiperidin-3-yl)-9H-pyrido[2,3-b]indol-5-yl)prop-2-yn-1-yl)oxy)ethoxy)ethyl)carbamate A mixture of 3-(5-bromo-9H-pyrido[2,3-b]indol-9-yl)piperidine-2,6-dione (270 mg, 0.75 mmol), tert-butyl (2-(2-(prop-2-yn-1-yloxy)ethoxy)ethyl)carbamate (270 mg, 2.25 mmol, Intermediate IT) $Cs_2CO_3$ (270 mg, 2.25 mmol), $PdCl_2(PPh_3)_2$ (105 mg, 0.15 mmol) and CuI (14 mg, 0.075 mmol) in DMF (10 mL) was stirred at 80° C. for 1 h under $N_2$ with microwave. The mixture was cooled to rt, poured into water (100 mL), extracted with EtOAc (3×100 mL). The combined organic layers were concentrated under reduced pressure, the residue was purified by column chromatography on silica gel (petroleum ether:ethyl acetate=2:1) to give the title product (180 mg, 41% yield) as a white solid. LC/MS (ESI, m/z): [M+1]$^+$=360.28. $^1$H NMR (400 MHz, DMSO-$d_6$) δ 11.18 (s, 1H), 8.81 (dd, J=7.8, 1.6 Hz, 1H), 8.50 (dd, J=4.8, 1.7 Hz, 1H), 7.73-7.68 (m, 1H), 7.54 (t, J=7.9 Hz, 1H), 7.45-7.28 (m, 2H), 6.80-6.76 (m, 1H), 6.08 (s, 1H), 4.65 (s, 2H), 3.81-3.70 (m, 2H), 3.62 (dd, J=5.7, 3.6 Hz, 2H), 3.43 (t, J=6.1 Hz, 2H), 3.17-2.96 (m, 3H), 2.76-2.64 (m, 1H), 2.50-2.45 (m, 1H), 2.17-2.13 (m, 1H), 1.35 (s, 9H).

Step 2—tert-butyl (2-(2-(3-(9-(2,6-dioxopiperidin-3-yl)-9H-pyrido[2,3-b]indol-5-yl)propoxy)ethoxy)ethyl)carbamate To a mixture of tert-butyl (2-(2-((3-(9-(2,6-dioxopiperidin-3-yl)-9H-pyrido[2,3-b]indol-5-yl)prop-2-yn-1-yl)oxy)ethoxy)ethyl)carbamate (180 mg, 0.34 mmol), Pd/C (100 mg) in EA (10 mL) was stirred at rt under $H_2$ for 16 h. The mixture was filtered and the solid was washed with EA, the filtrate was concentrated under reduced pressure. Then the residue was purified by column chromatography on silica gel (petroleum ether:ethyl acetate=2:1) to give the title compound (100 mg, 56% yield) as a white solid. LC/MS (ESI, m/z): [M+1]$^+$=525.1. $^1$H NMR (400 MHz, DMSO-$d_6$) δ 11.15 (s, 1H), 8.54 (dd, J=7.9, 1.5 Hz, 1H), 8.42 (dd, J=4.9, 1.5 Hz, 1H), 7.52-7.40 (m, 2H), 7.28 (dd, J=7.8, 4.9 Hz, 1H), 7.11 (d, J=7.4 Hz, 1H), 6.77-6.74 (m, 1H), 6.10-6.00 (m, 1H), 3.61-3.50 (m, 6H), 3.43 (t, J=6.1 Hz, 2H), 3.23-3.20 (m, 2H), 3.12-2.96 (m, 4H), 2.72-2.65 (m, 1H), 2.12-2.06 (m, 1H), 1.99-1.89 (m, 2H), 1.34 (s, 9H).

Step 3—3-[5-[3-[2-(2-Aminoethoxy)ethoxy]propyl]pyrido[2,3-b]indol-9-yl]piperidine-2,6-dione To a solution of tert-butyl N-[2-[2-[3-[9-(2,6-dioxo-3-piperidyl)pyrido[2,3-b]indol-5-yl]propoxy]ethoxy]ethyl]carbamate (100 mg, 190 umol) in DCM (2 mL) was added TFA (1.54 g, 13.5 mmol, 1 mL). The reaction mixture was stirred at 25° C. for 2 hrs. On completion, the mixture was concentrated in vacuo to give the title compound (100 mg, 97% yield, TFA) as a white solid. LC-MS (ESI$^+$) m/z 425.2 (M+H)$^+$.

Tert-butyl N-methyl-N-(1-prop-2-ynyl-4-piperidyl)carbamate (Intermediate XH)

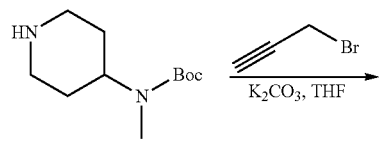

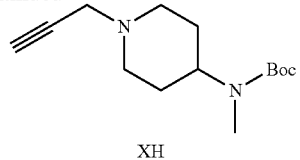

To a solution of tert-butyl N-methyl-N-(4-piperidyl)carbamate (1.50 g, 7.00 mmol, CAS #108612-54-0) and 3-bromoprop-1-yne (915 mg, 7.70 mmol, 663 uL, CAS #106-96-70) in THF (30 mL) was added $K_2CO_3$ (2.90 g, 21.0 mmol). The reaction mixture was stirred at 25° C. for 16 hrs. On completion, the mixture was diluted with water (30 mL) and extracted with EA (3×80 mL). The combined organic layers was dried over $Na_2SO_4$, filtered and concentrated in vacuo to give the title compound (1.50 mg, 85% yield) as yellow solid. $^1$H NMR (400 MHz, CDCl$_3$) δ 4.16-3.61 (m, 1H), 3.29 (d, J=2.0 Hz, 2H), 3.01-2.90 (m, 2H), 2.73 (s, 3H), 2.35-2.21 (m, 3H), 1.81-1.72 (m, 2H), 1.69-1.63 (m, 2H), 1.46 (s, 9H).

3-[3-Methyl-4-[3-[4-(methylamino)-1-piperidyl]propyl]-2-oxo-benzimidazol-1-yl]piperidine-2,6-dione (Intermediate XI)

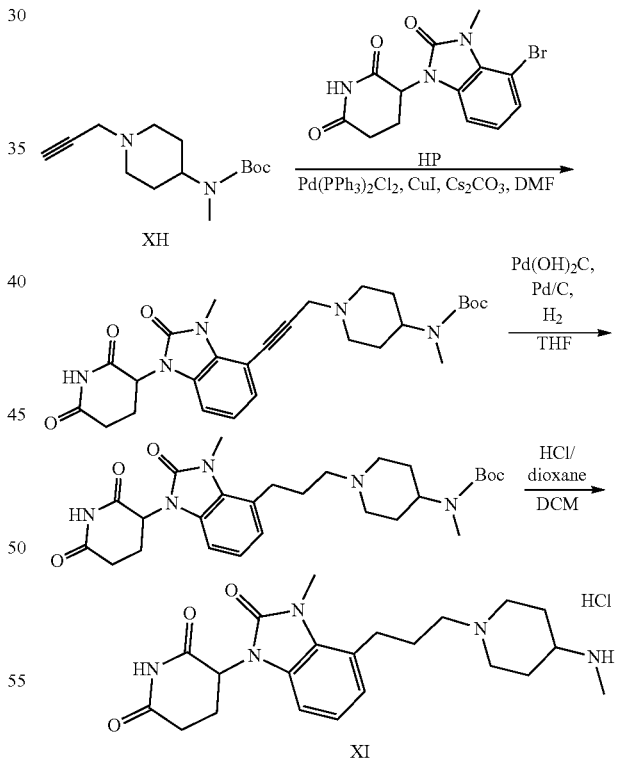

Step 1—Tert-butyl N-[1-[3-[1-(2,6-dioxo-3-piperidyl)-3-methyl-2-oxo-benzimidazol-4-yl]prop-2-ynyl]-4-piperidyl]-N-methyl-carbamate To a solution of tert-butyl N-methyl-N-(1-prop-2-ynyl-4-piperidyl)carbamate (559 mg, 2.22 mmol, Intermediate XH) and 3-(4-bromo-3-methyl-2-oxo-benzimidazol-1-yl)piperidine-2,6-dione (500 mg, 1.48 mmol, Intermediate HP) in DMF (5 mL) was added Pd(PPh$_3$)$_2$Cl$_2$ (103 mg, 147 umol), CuI (28.1 mg, 147 umol) and Cs$_2$CO$_3$ (955 mg, 2.93 mmol, 2.58 mL). The reaction mixture was stirred at 80° C. for 2 hr under N$_2$. On completion, the mixture was filtered and the filtrate was concentrated in vacuo to give a residue. The residue was purified by reverse phase (0.1% FA condition) to give the title compound (700 mg, 93% yield) as a gray solid. $^1$H NMR (400 MHz, DMSO-d$_6$) δ 11.13 (s, 1H), 7.20-6.93 (m, 3H), 5.40 (dd, J=5.2, 12.8 Hz, 1H), 3.66 (s, 3H), 3.58 (s, 2H), 2.98-2.84 (m, 3H), 2.68 (s, 3H), 2.66-2.59 (m, 2H), 2.25 (t, J=10.8 Hz, 2H), 2.07-1.99 (m, 1H), 1.75-1.50 (m, 5H), 1.40 (s, 9H); LC-MS (ESI$^+$) m/z 510.3 (M+H)$^+$.

Step 2—Tert-butyl N-[1-[3-[1-(2,6-dioxo-3-piperidyl)-3-methyl-2-oxo-benzimidazol-4-yl]propyl]-4-piperidyl]-N-methyl-carbamate To a solution of tert-butyl N-[1-[3-[1-(2,6-dioxo-3-piperidyl)-3-methyl-2-oxo-benzimidazol-4-yl]prop-2-ynyl]-4-piperidyl]-N-methyl-carbamate (650 mg, 1.28 mmol) in THF (20 mL) was added Pd/C (150 mg, 1.28 mmol, 10 wt %) and Pd(OH)$_2$/C (150 mg, 10 wt %). The reaction mixture was stirred at 25° C. under H$_2$ (15 psi) for 2 hrs. On completion, the residue was filtered and the filtrate was concentrated in vacuo to give a residue. The residue was purified by reverse phase (0.1% FA condition) to give the title compound (480 mg, 73% yield) as a white solid. $^1$H NMR (400 MHz, DMSO-d$_6$) δ 11.08 (s, 1H), 6.96 (d, J=4.8 Hz, 2H), 6.93-6.86 (m, 1H), 5.36 (dd, J=5.6, 12.8 Hz, 1H), 3.93-3.65 (m, 1H), 3.56 (s, 3H), 3.08-2.97 (m, 2H), 2.96-2.81 (m, 3H), 2.76-2.67 (m, 1H), 2.66 (s, 3H), 2.64-2.58 (m, 1H), 2.49-2.39 (m, 2H), 2.14-2.05 (m, 2H), 2.03-1.94 (m, 1H), 1.83-1.62 (m, 4H), 1.56-1.48 (m, 2H), 1.39 (s, 9H); LC-MS (ESI$^+$) m/z 514.3 (M+H)$^+$.

Step 3—3-[3-Methyl-4-[3-[4-(methylamino)-1-piperidyl]propyl]-2-oxo-benzimidazol-1-yl]piperidine-2,6-dione To a solution of tert-butyl N-[1-[3-[1-(2,6-dioxo-3-piperidyl)-3-methyl-2-oxo-benzimidazol-4-yl]propyl]-4-piperidyl]-N-methyl-carbamate (100 mg, 194 umol) in DCM (2 mL) was added HCl/dioxane (4 M, 1 mL). The reaction mixture was stirred at 20° C. for 2 hrs. On completion, the mixture was concentrated in vacuo to give the title compound (85.0 mg, 97% yield, HCl) as a white solid. LC-MS (ESI$^+$) m/z 414.3 (M+H)$^+$.

Tert-butyl N-methyl-N-[2-(4-piperidylmethoxy)ethyl]carbamate (Intermediate XJ)

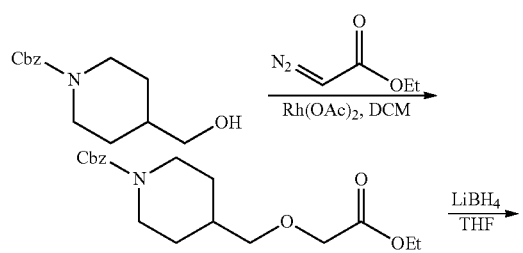

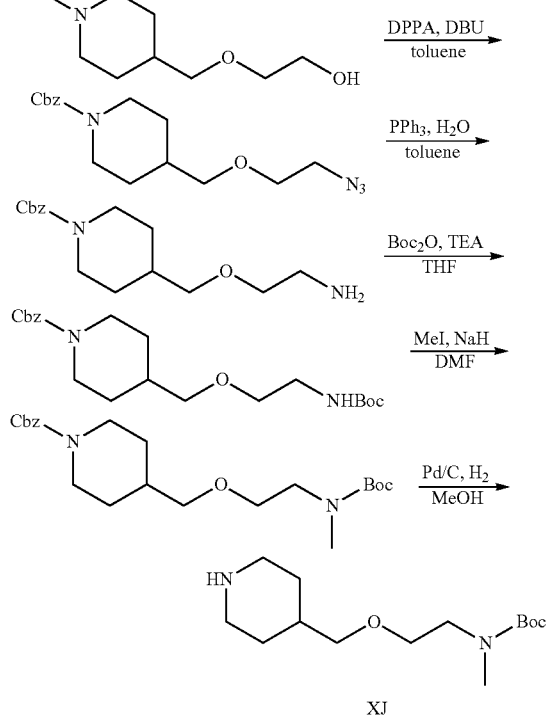

Step 1—Benzyl 4-((2-ethoxy-2-oxoethoxy)methyl)piperidine-1-carboxylate

A solution of benzyl 4-(hydroxymethyl) piperidine-1-carboxylate (15.0 g, 60.2 mmol, CAS #122860-33-7) in DCM (15 mL) was added diacetoxyrhodium (1.33 g, 3.01 mmol, CAS #623-73-4). The mixture was stirred at 25° C. for 0.5 hour. Then ethyl 2-diazoacetate (13.7 g, 120 mmol) in DCM (15 mL) was added dropwise slowly to the solution. The mixture was stirred at 25° C. for 12 hours. On completion, the reaction mixture was quenched by water (10 mL), and extracted with DCM (3×20 mL). The combined organic layers dried over Na$_2$SO$_4$, filtered and concentrated in vacuo to give a residue. The residue was purified by column chromatography to give the title compound (16.8 g, 83% yield) as yellow oil. LC-MS (ESI$^+$) m/z 336.2 (M+H)$^+$.

Step 2—Benzyl 4-((2-hydroxyethoxy)methyl)piperidine-1-carboxylate

To a solution of benzyl 4-[(2-ethoxy-2-oxo-ethoxy)methyl]piperidine-1-carboxylate (16.8 g, 50.1 mmol) in THF (180 mL) was added LiBH$_4$ (2.18 g, 100 mmol) at 0° C. The mixture was stirred at 25° C. for 12 hours. On completion, the reaction mixture was quenched with H$_2$O (200 mL) and then extracted with ethyl acetate (2×300 mL). Then the organic layers were washed with brine (2×150 mL). The combined organic layer was dried over anhydrous Na$_2$SO$_4$, filtered and concentrated in vacuo to give a residue. The residue was purified by column chromatography to give the title compound (13.2 g, 90% yield) as colorless oil. LC-MS (ESI$^+$) m/z 294.2 (M+H)$^+$.

Step 3—Benzyl 4-((2-azidoethoxy)methyl)piperidine-1-carboxylate

To a solution of benzyl 4-(2-hydroxyethoxymethyl)piperidine-1-carboxylate (4.00 g, 13.6 mmol) in toluene (40 mL) was added DPPA (4.50 g, 16.4 mmol) and DBU (2.49 g, 16.4 mmol). The mixture was stirred at 100° C. for 12 hours. On completion, the reaction mixture was diluted with H₂O (50 mL) and extracted with ethyl acetate (3×50 mL). The combined organic layers were dried over anhydrous Na₂SO₄, filtered and concentrated in vacuo to give the title compound (4.34 g, 98% yield) as yellow oil.

Step 4—Benzyl 4-(2-aminoethoxymethyl)piperidine-1-carboxylate

To a solution of benzyl 4-(2-azidoethoxymethyl)piperidine-1-carboxylate (4.34 g, 13.6 mmol) in a mixed solvent of THF (45 mL) and H₂O (5 mL) was added PPh₃ (3.58 g, 13.6 mmol). The mixture was stirred at 66° C. for 12 hours. On completion, the reaction mixture was diluted with H₂O (50 mL) and extracted with ethyl acetate (3×50 mL). The organic layers were dried over anhydrous Na₂SO₄, filtered and concentrated in vacuo to give the title compound (3.99 g, 99% yield) as yellow oil. LC-MS (ESI+) m/z 293.2 (M+H)⁺.

Step 5—Benzyl 4-[2-(tert-butoxycarbonylamino)ethoxmethyl]piperidine-1-carboxylate To a solution of benzyl 4-(2-aminoethoxymethyl)piperidine-1-carboxylate (3.99 g, 13.7 mmol) in THF (40 mL) was added Boc₂O (4.47 g, 20.5 mmol) and TEA (4.14 g, 40.9 mmol). The mixture was stirred at 25° C. for 12 hours. On completion, the reaction mixture was diluted with H₂O (100 mL) and extracted with (2×100 mL). The organic layers were dried over anhydrous Na₂SO₄, filtered and concentrated in vacuo to give a residue. The residue was purified by column chromatography to give the title compound (4.70 g, 80% yield) as yellow oil. LC-MS (ESI⁺) m/z 415.3 (M+Na)⁺.

Step 6—Benzyl 4-[2-[tert-butoxycarbonyl(methyl)amino]ethoxymethyl]piperidine-1-carboxylate To a solution of benzyl 4-[2-(tert-butoxycarbonylamino)ethoxymethyl]piperidine-1-carboxylate (4.60 g, 11.7 mmol) in DMF (50 mL) was added NaH (938 mg, 23.4 mmol, 60% dispersion in oil) at 0° C. Then CH₃I (3.33 g, 23.4 mmol) was added dropwise to the solution. The mixture was stirred at 0-25° C. for 2 hours. On completion, the reaction mixture was quenched with saturated NH₄Cl (20 mL). Then H₂O (50 mL) and ethyl acetate (100 mL) was added. The aqueous layer was extracted with ethyl acetate (2×100 mL). The combined organic layers were washed with brine (50 mL). The organic layer was dried over anhydrous Na₂SO₄, filtered and concentrated in vacuo to give a residue. The residue was purified by column chromatography to give the title compound (3.80 g, 79% yield) as yellow oil.

Step 7—Tert-butyl N-methyl-N-[2-(4-piperidyl-methoxy)ethyl]carbamate

To a solution of benzyl 4-[2-[tert-butoxycarbonyl(methyl)amino]ethoxymethyl]piperidine-1-carboxylate (3.80 g, 9.35 mmol) in MeOH (80 mL) was added Pd/C (400 mg, 377 umol, 10 wt %). The mixture was stirred at 25° C. for 12 hours. On completion, the reaction mixture was filtered and concentrated in vacuo to give the title compound (3.30 g, 98% yield) as yellowish oil. LC-MS (ESI⁺) m/z 273.2 (M+H)⁺.

3-(3-methyl-5-(4-((2-(methylamino)ethoxy)methyl)piperidin-1-yl)-2-oxo-2,3-dihydro-1H-benzo[d]imidazol-1-yl)piperidine-2,6-dione methanesulfonate (Intermediate XK)

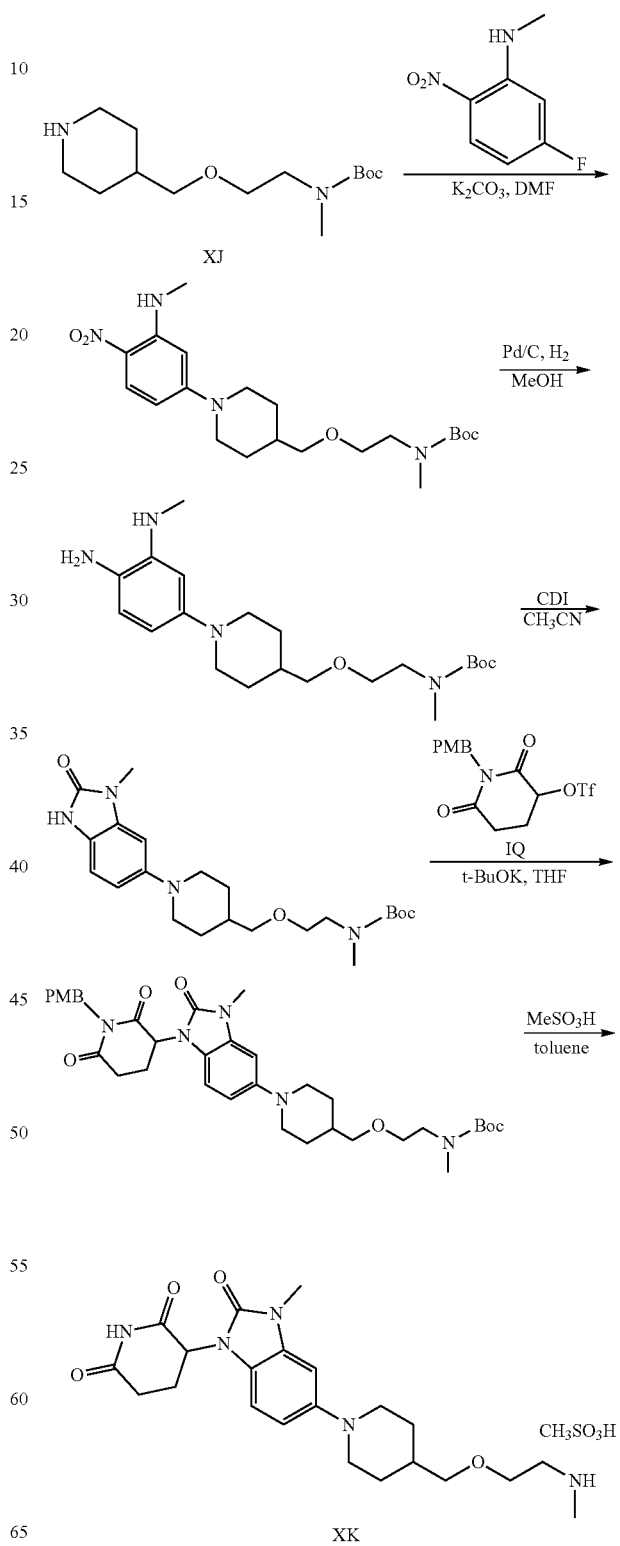

Step 1—Tert-butyl N-methyl-N-[2-[[1-[3-(methylamino)-4-nitro-phenyl]-4-piperidyl]methoxy]ethyl] carbamate To a solution of tert-butyl N-methyl-N-[2-(4-piperidylmethoxy)ethyl]carbamate (3.30 g, 12.1 mmol, Intermediate XJ) in DMF (30 mL) was added 5-fluoro-N-methyl-2-nitroaniline (2.06 g, 12.1 mmol) and $K_2CO_3$ (5.02 g, 36.4 mmol). Then the mixture was stirred at 80° C. for 12 hours. On completion, the reaction mixture was diluted with $H_2O$ (50 mL) and extracted with ethyl acetate (3×100 mL). The organic layers were washed with brine (3×50 mL). Then the organic layer was dried over anhydrous $Na_2SO_4$, filtered and concentrated in vacuo to give a residue. The residue was purified by column chromatography to give the title compound (4.40 g, 85% yield) as orange oil. LC-MS (ESI+) m/z 423.5 (M+H)+.

Step 2—Tert-butyl (2-((1-(4-amino-3-(methylamino)phenyl)piperidin-4-yl)methoxy)ethyl) (methyl)carbamate To a solution of tert-butyl N-methyl-N-[2-[[1-[3-(methylamino)-4-nitro-phenyl]-4-piperidyl]methoxy]ethyl]carbamate (3.6 g, 8.52 mmol) in MeOH (100 mL) was added Pd/C (0.7 g, 10 wt %) under $N_2$. The suspension was degassed in vacuo and purged with $H_2$ three times. The mixture was stirred under $H_2$ (15 Psi) at 25° C. for 4 hours. On completion, the reaction mixture was filtered and concentrated in vacuo to give the title compound (3.2 g, 97% yield) as brown oil. $^1$H NMR (400 MHz, $CDCl_3$) δ 6.63 (d, J=8.2 Hz, 1H), 6.34 (d, J=2.4 Hz, 1H), 6.28 (dd, J=2.6, 8.2 Hz, 1H), 3.52 (d, J=12.0 Hz, 4H), 3.45-3.31 (m, 4H), 2.93 (s, 3H), 2.86 (s, 3H), 2.62 (dt, J=2.0, 11.6 Hz, 2H), 1.83 (d, J=12.6 Hz, 2H), 1.73-1.60 (m, 1H), 1.49-1.40 (m, 11H); LC-MS (ESI+) m/z 393.2 (M+H)+.

Step 3—Tert-butyl (2-((1-(4-amino-3-(methylamino)phenyl)piperidin-4-yl)methoxy)ethyl) (methyl)carbamate To a mixture of tert-butyl N-[2-[[1-[4-amino-3-(methylamino)phenyl]-4-piperidyl]methoxy]ethyl]-N-methyl-carbamate (1.5 g, 3.82 mmol) in MeCN (30 mL) was added CDI (1.24 g, 7.64 mmol) under $N_2$. The mixture was stirred for at 85° C. 16 hours. On completion, the reaction mixture was concentrated in vacuo to remove THF. The residue was diluted with water (20 mL) and extracted with EA (3×20 mL). The combined organic layers was dried over $Na_2SO_4$, filtered and concentrated in vacuo to give a residue. The residue was purified by reverse phase (FA condition) to give the title compound (1.10 g, 69% yield) as a purple solid. $^1$H NMR (400 MHz, $CDCl_3$) δ 9.06 (s, 1H), 6.95 (d, J=8.4 Hz, 1H), 6.74-6.69 (m, 1H), 6.62 (d, J=2.2 Hz, 1H), 3.60-3.52 (m, 4H), 3.39 (s, 3H), 3.37-3.31 (m, 2H), 2.93 (s, 3H), 2.73-2.65 (m, 2H), 1.86 (d, J=11.8 Hz, 2H), 1.77-1.67 (m, 2H), 1.47-1.33 (m, 13H; LC-MS (ESI+) m/z 419.2 (M+H)+.

Step 4—Tert-butyl (2-((1-(4-amino-3-(methylamino)phenyl)piperidin-4-yl)methoxy)ethyl) (methyl)carbamate To a mixture of tert-butyl N-methyl-N-[2-[[1-(3-methyl-2-oxo-1H-benzimidazol-5-yl)-4-piperidyl]methoxy]ethyl]carbamate (1.10 g, 2.63 mmol) in THF (20 mL) was added t-BuOK (442 mg, 3.94 mmol) at 0° C. under $N_2$. Then a solution of [1-[(4-methoxyphenyl)methyl]-2,6-dioxo-3-piperidyl]trifluoromethanesulfonate (1.50 g, 3.94 mmol, Intermediate IQ) in THF (20 mL) was added dropwise at 0° C. The mixture was warmed slowly to 25° C. and stirred at 25° C. for 24 hours. On completion, the reaction mixture was quenched by addition water (10 mL) at 25° C., and then extracted with EA (3×20 mL). The combined organic layers, dried over $Na_2SO_4$, filtered and concentrated in vacuo to give a residue. The residue was purified by column chromatography to give the title compound (800 mg, 24% yield) as brown oil. LC-MS (ESI+) m/z 650.2 (M+H)+.

Step 5—3-(3-methyl-5-(4-((2-(methylamino)ethoxy)methyl)piperidin-1-yl)-2-oxo-2,3-dihydro-1H-benzo[d]imidazol-1-yl)piperidine-2,6-dione methanesulfonate To a mixture of tert-butyl N-[2-[[1-[1-[1-[(4-methoxyphenyl)methyl]-2,6-dioxo-3-piperidyl]-3-methyl-2-oxo-benzimidazol-5-yl]-4-piperidyl]methoxy]ethyl]-N-methyl-carbamate (500 mg, 769 umol) in toluene (10 mL) was added $CH_3SO_3H$ (2.22 g, 23.1 mmol) at 25° C. The mixture was stirred at 120° C. for 3 hours. On completion, the reaction mixture was quenched by addition water (2 mL) at 25° C., and then neutralized by adding $NEt_3$ to pH=5. Then the mixture was filtered and concentrated in vacuo to give a residue. The residue was purified by reverse phase (FA condition) to give the title compound (100 mg, 25% yield, $CH_3SO_3H$) as yellow oil. LC-MS (ESI+) m/z 430.1 (M+H)+.

Tert-butyl 4-(2-prop-2-ynoxyethyl)piperazine-1-carboxylate (Intermediate XL)

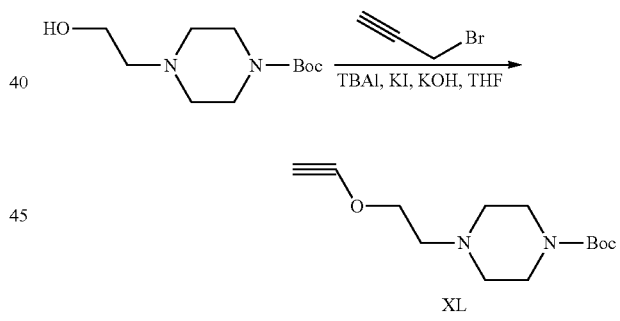

XL

A mixture of tert-butyl 4-(2-hydroxyethyl)piperazine-1-carboxylate (5.00 g, 21.7 mmol, CAS #77279-24-4), 3-bromoprop-1-yne (2.58 g, 21.7 mmol, CAS #106-96-7) in THF (35 mL) was added TBAI (802 mg, 2.17 mmol), KI (541 mg, 3.26 mmol) and KOH (1.22 g, 21.7 mmol). The mixture was stirred at 25° C. for 12 hrs under $N_2$ atmosphere. On completion, the reaction mixture was diluted with water (2×100 mL) and extracted with ethyl acetate (3×100 mL). The combined organic layers were washed with brine, dried over anhydrous sodium sulfate, filtered and concentrated under reduced pressure to give a residue. The residue was purified by column chromatography ($SiO_2$, PE:EA=10:1 to 3:1) to give the title compound (1.30 g, 18% yield) as yellow oil. $^1$H NMR (400 MHz, DMSO-$d_6$) δ 4.12 (d, J=2.4 Hz, 2H), 3.54 (t, J=5.6 Hz, 2H), 3.41 (s, 1H), 3.30-3.26 (m, 4H), 2.49-2.47 (m, 2H), 2.36-2.33 (m, 4H), 1.39 (s, 9H).

3-[3-Methyl-2-oxo-4-[3-(2-piperazin-1-ylethoxy)propyl]benzimidazol-1-yl]piperidine-2,6-dione (Intermediate XM)

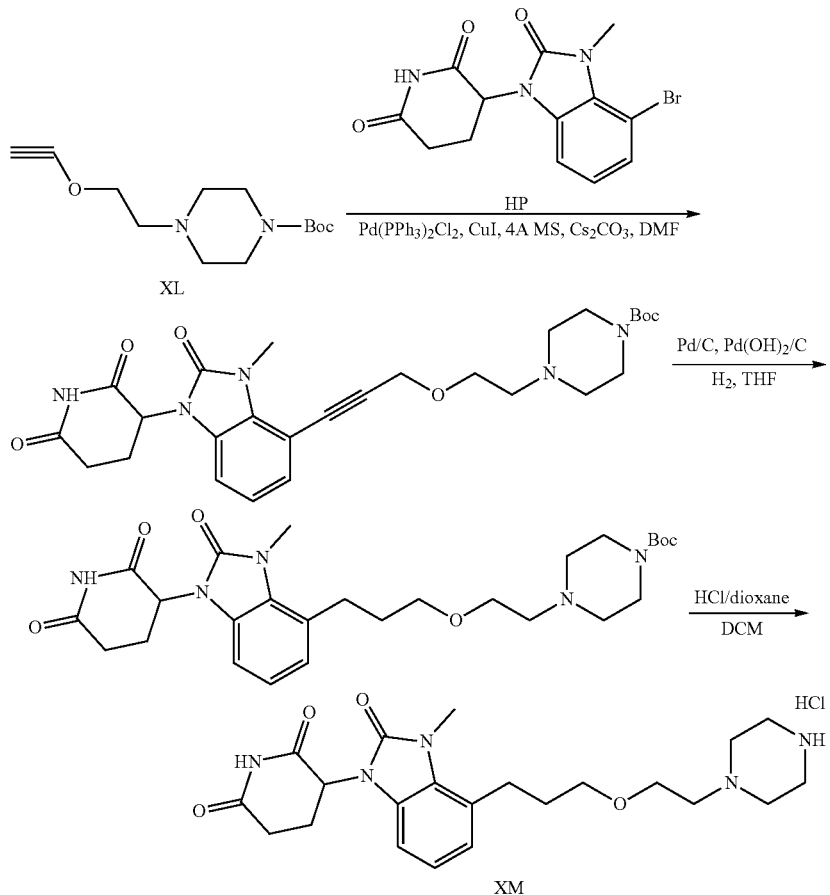

Step 1—Tert-butyl 4-[2-[3-[1-(2,6-dioxo-3-piperidyl)-3-methyl-2-oxo-benzimidazol-4-yl]prop-2-ynoxy]ethyl]piperazine-1-carboxylate A mixture of tert-butyl 4-(2-prop-2-ynoxyethyl)piperazine-1-carboxylate (476 mg, 1.77 mmol, Intermediate XL), 3-(4-bromo-3-methyl-2-oxo-benzimidazol-1-yl)piperidine-2,6-dione (300 mg, 887 umol, Intermediate HP), Cs$_2$CO$_3$ (1.45 g, 4.44 mmol), 4 Å molecular sieves (50 mg), Pd(PPh$_3$)$_2$Cl$_2$ (124 mg, 177 umol) and CuI (33.8 mg, 177 umol) in DMF (8 mL) under N$_2$ atmosphere. The mixture was de-gassed and then heated at 80° C. for 2 hrs. On completion, the reaction mixture was concentrated in vacuo. The crude product was purified by reversed-phase HPLC (0.1% FA condition) to give the title compound (400 mg, 77% yield) as brown oil. $^1$H NMR (400 MHz, DMSO-d$_6$) δ 11.12 (s, 1H), 7.19 (d, J=7.2 Hz, 1H), 7.13 (d, J=7.6 Hz, 1H), 7.06-6.94 (m, 1H), 5.41 (dd, J=4.8, 12.4 Hz, 1H), 4.47 (s, 2H), 3.74 (s, 2H), 3.64 (s, 3H), 3.56-3.52 (m, 4H), 2.94-2.89 (m, 1H), 2.85-2.71 (m, 4H), 2.63-2.58 (m, 4H), 2.09-1.97 (m, 1H), 1.39 (s, 9H); LC-MS (ESI+) m/z 526.3 (M+H)$^+$.

Step 2-Tert-butyl 4-[2-[3-[1-(2,6-dioxo-3-piperidyl)-3-methyl-2-oxo-benzimidazol-4-yl]propoxy]ethyl]piperazine-1-carboxylate To a solution of tert-butyl 4-[2-[3-[1-(2,6-dioxo-3-piperidyl)-3-methyl-2-oxo-benzimidazol-4-yl]prop-2-ynoxy]ethyl]piperazine-1-carboxylate (400 mg, 679 umol) in THF (20 mL) was added Pd/C (50.0 mg, 10 wt %) and Pd(OH)$_2$ (50.0 mg) under N$_2$ atmosphere. The mixture was stirred at 25° C. for 12 hrs under H$_2$ (15 Psi). On completion, the reaction mixture was concentrated in vacuo. The product was filtered under reduced pressure to give the title compound (395 mg, 99% yield) as brown solid. $^1$H NMR (400 MHz, DMSO-d$_6$) δ 11.08 (s, 1H), 6.97 (d, J=5.2 Hz, 2H), 6.90-6.85 (m, 1H), 5.37 (dd, J=5.2, 12.4 Hz, 1H), 4.26 (t, J=7.2 Hz, 1H), 4.15 (t, J=6.5 Hz, 1H), 3.69-3.62 (m, 2H), 3.56 (s, 3H), 3.50-3.45 (m, 4H), 2.98-2.95 (m, 2H), 2.75-2.71 (m, 2H), 2.69-2.66 (m, 2H), 2.65-2.59 (m, 4H), 2.19-2.13 (m, 1H), 1.88-1.82 (m, 2H), 1.77-1.71 (m, 1H), 1.40 (s, 9H). LC-MS (ESI+) m/z 530.3 (M+H)$^+$.

Step 3—3-[3-Methyl-2-oxo-4-[3-(2-piperazin-1-ylethoxy)propyl]benzimidazol-1-yl]piperidine-2,6-dione To a solution of tert-butyl 4-[2-[3-[1-(2,6-dioxo-3-piperidyl)-3-methyl-2-oxo-benzimidazol-4-yl]propoxy]ethyl]

piperazine-1-carboxylate (100 mg, 189 umol) in DCM (4 mL) was added HCl/dioxane (2 mL). The mixture was stirred at 25° C. for 2 hrs. On completion, the reaction mixture was concentrated in vacuo to give the title compound (87 mg, 58% yield, HCl) as brown solid. LC-MS (ESI+) m/z 430.3 (M+H)+.

Tert-butyl N-isopropyl-N-(3-prop-2-ynoxypropyl) carbamate (Intermediate XN)

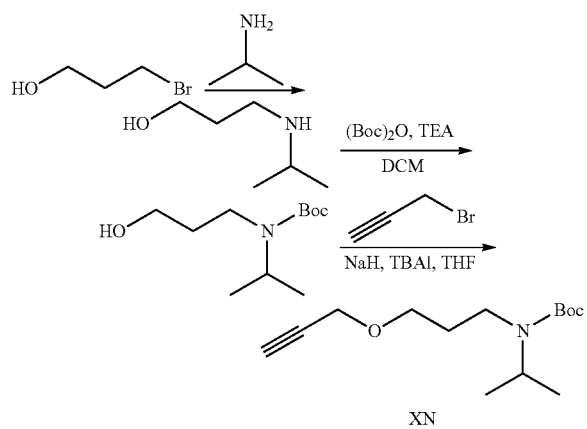

Step 1—3-(Isopropylamino)propan-1-ol

A solution of 3-bromopropan-1-ol (5.00 g, 36.0 mmol) in propan-2-amine (6.19 g, 105 mmol) was stirred at 50° C. for 12 hours. On completion, the mixture was concentrated to give the title compound (7.00 g, 90% yield, 50% purity) as colorless oil. $^1$H NNR (400 MHz, CDCl$_3$) δ 3.84 (t, J=5.6 Hz, 2H), 3.40-3.33 (i, 1H), 3.12 (t, J=6.4 Hz, 2H), 2.11-1.99 (i, 2H), 1.39 (d, J=6.6 Hz, 6H).

Step 2—Tert-butyl N-(3-hydroxypropyl)-N-isopropyl-carbamate

To a solution of 3-(isopropylamino)propan-1-ol (7.00 g, 30.0 mmol, 50% purity) in DCM (10 mL) was added (Boc)$_2$O (13.0 g, 59.7 mmol, 13.7 mL) and Et$_3$N (8.00 g, 79.0 mmol) at 15° C. The mixture was stirred at 15° C. for 6 hours. On completion, the mixture was concentrated in vacuo. The residue was purified by flash silica gel chromatography to give the title compound (3.60 g, 50% yield) as yellow oil. $^1$H NMR (400 MHz, CDCl$_3$) δ 3.58 (m, 2H), 3.35 (m, 2H), 1.67 (m, 2H), 1.48 (s, 9H), 1.16 (d, J=6.8 Hz, 6H), 0.91-0.86 (m, 1H).

Step 3—Tert-butyl N-isopropyl-N-(3-prop-2-ynoxypropyl)carbamate

To a solution of tert-butyl N-(3-hydroxypropyl)-N-isopropyl-carbamate (3.40 g, 15.7 mmol) and TBAI (57.8 mg, 156 umol) in THF (100 mL) was added NaH (750 mg, 18.7 mmol, 60% dispersion in oil) at 0° C. The mixture was stirred at 0° C. for 0.5 hour. 3-bromoprop-1-yne (2.79 g, 23.5 mmol) was added at 0° C. The mixture was stirred at 0-15° C. for 6 hours. On completion, the reaction mixture was quenched with sat. aq. NH$_4$Cl (30 mL) at 0° C. The mixture was extracted with EA (3×100 mL). The combined organic layers were washed with brine (100 ml), dried over Na$_2$SO$_4$, filtered and concentrated in vacuo. The residue was purified by flash silica gel chromatography to give the title compound (3.50 g, 80% yield) as yellow oil. $^1$H NMR (400 MHz, CDCl$_3$) δ 4.13 (d, J=2.4 Hz, 2H), 3.53 (t, J=6.4 Hz, 2H), 3.14 (m, 2H), 2.41 (t, J=2.4 Hz, 1H), 1.86-1.77 (m, 2H), 1.46 (s, 9H), 1.12 (d, J=6.8 Hz, 6H), 0.90-0.80 (m, 1H).

3-[4-[3-[3-(Isopropylamino)propoxy]propyl]-3-methyl-2-oxo-benzimidazol-1-yl]piperidine-2,6-dione (Intermediate XO)

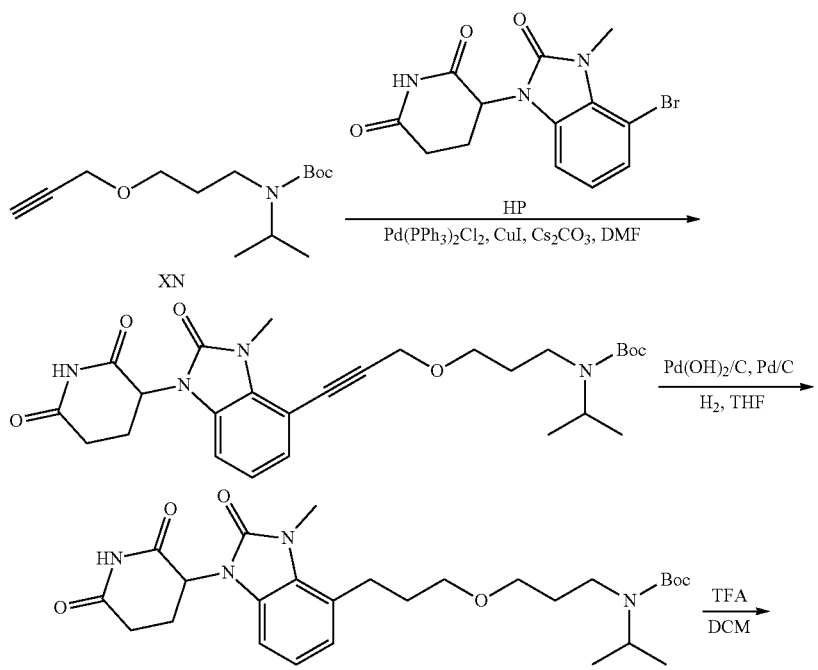

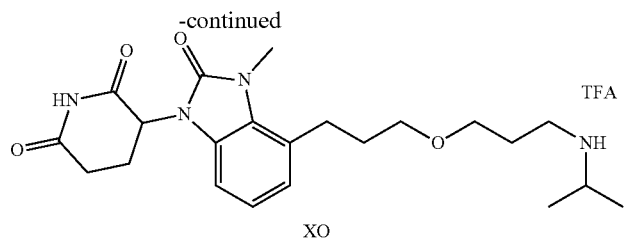

Step 1—Tert-butyl N-[3-[3-[1-(2,6-dioxo-3-piperidyl)-3-methyl-2-oxo-benzimidazol-4-yl]prop-2-ynoxy]propyl]-N-isopropyl-carbamate To a solution of tert-butyl N-isopropyl-N-(3-prop-2-ynoxypropyl)carbamate (755 mg, 2.96 mmol, Intermediate XN) and 3-(4-bromo-3-methyl-2-oxo-benzimidazol-1-yl)piperidine-2,6-dione (400 mg, 1.18 mmol, Intermediate HP) in DMF (10 mL) was added Pd(dppf)Cl$_2$ (173 mg, 237 umol) and Cs$_2$CO$_3$ (1.54 g, 4.73 mmol) and CuI (45.1 mg, 237 umol) at 20° C. The mixture was stirred at 80° C. for 2 hours under N$_2$. On completion, the mixture was filtered through celite and the filtrate was concentrated in vacuo. The residue was purified by reversed-phase HPLC (FA condition) to give the title compound (350 mg, 55% yield) as yellow solid. $^1$H NMR (400 MHz, DMSO-d$_6$) δ 11.14 (s, 1H), 7.18 (d, J=7.6 Hz, 1H), 7.14-7.10 (m, 1H), 7.08-6.99 (m, 1H), 5.43-5.38 (m, 1H), 4.44 (s, 2H), 3.09 (m, 2H), 2.95-2.84 (m, 1H), 2.09-1.97 (m, 1H), 1.82-1.69 (m, 2H), 1.38 (s, 9H), 1.08 (d, J=6.0 Hz, 6H).

Step 2—Tert-butyl N-[3-[3-[1-(2,6-dioxo-3-piperidyl)-3-methyl-2-oxo-benzimidazol-4-yl]propoxy]propyl]-N-isopropyl-carbamate To a solution of tert-butyl N-[3-[3-[1-(2,6-dioxo-3-piperidyl)-3-methyl-2-oxo-benzimidazol-4-yl]prop-2-ynoxy]propyl]-N-isopropyl-carbamate (350 mg, 683 umol) in THF (20 mL) was added Pd(OH)$_2$/C (350 mg, 683 umol, 10 wt %) and Pd/C (350 mg, 682 umol, 10 wt %). The mixture was stirred at 15° C. for 2 hours. On completion, the mixture was filtered with celite and the filtrate was concentrated in vacuo to give the title compound (350 mg, 99% yield) as yellow oil. LC-MS (ESI$^+$) m/z 539.4 (M+23)$^+$

Step 3—3-[4-[3-[3-(Isopropylamino)propoxy]propyl]-3-methyl-2-oxo-benzimidazol-1-yl]piperidine-2,6-dione To a solution of tert-butyl N-[3-[3-[1-(2,6-dioxo-3-piperidyl)-3-methyl-2-oxo-benzimidazol-4-yl]propoxy]propyl]-N-isopropyl-carbamate (320 mg, 619 umol) in DCM (4 mL) was added TFA (10.7 mL) at 15° C. The mixture was stirred at 15° C. for 0.5 hour. On completion, the mixture was concentrated in vacuo to give the title compound (320 mg, 97% yield, TFA salt) as yellow oil. LC-MS (ESI$^+$) m/z 417.3 (M+H)$^+$.

Tert-butyl N-cyclopropyl-N-(3-prop-2-ynoxypropyl)carbamate (Intermediate XP)

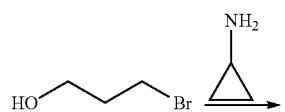

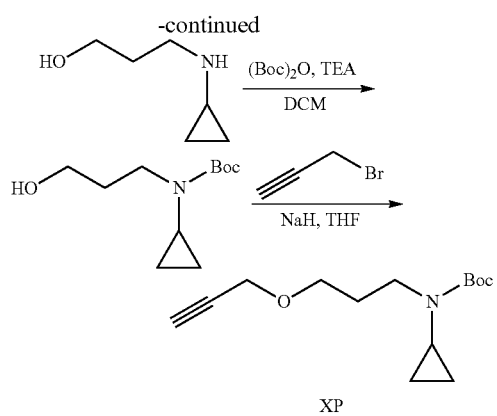

Step 1—3-(Cyclopropylamino)propan-1-ol

A mixture of 3-bromopropan-1-ol (5.00 g, 35.9 mmol, 3.25 mL, CAS #627-18-9) in cyclopropanamine (10.2 g, 179 mmol, 12.4 mL, CAS #765-30-0) was stirred at 50° C. for 12 hours. On completion, the reaction mixture was concentrated in vacuo to give the title compound (4.00 g, 96% yield) as light yellow oil. $^1$H NMR (400 MHz, DMSO-d$_6$) δ 3.45 (t, J=6.0 Hz, 2H), 3.01 (t, J=7.6 Hz, 2H), 2.75-2.68 (m, 1H), 1.81-1.73 (m, 2H), 0.88-0.82 (m, 2H), 0.74-0.70 (m, 2H).

Step 2—Tert-butyl N-cyclopropyl-N-(3-hydroxypropyl)carbamate

To a mixture of 3-(cyclopropylamino)propan-1-ol (4.00 g, 34.7 mmol) in DCM (60 mL) was added TEA (10.5 g, 104 mmol, 14.5 mL) and Boc$_2$O (15.1 g, 69.4 mmol, 15.9 mL). The reaction mixture was stirred at 25° C. for 12 hours. On completion, the reaction mixture was diluted with water (30 mL) and extracted with EA (3×50 mL). The combined organic layers was dried over Na$_2$SO$_4$, filtered and concentrated in vacuo to give a residue. The residue was purified by column chromatography to give the title compound (3.70 g, 49% yield) as light yellow oil. $^1$H NMR (400 MHz, CDCl$_3$) δ 3.54 (d, J=5.0 Hz, 2H), 3.36 (t, J=6.0 Hz, 2H), 2.49-2.41 (m, 1H), 1.74-1.65 (m, 2H), 1.45 (s, 9H), 0.75-0.68 (m, 2H), 0.62-0.55 (m, 2H).

Step 3—Tert-butyl N-cyclopropyl-N-(3-prop-2-ynoxypropyl)carbamate

To a mixture of tert-butyl N-cyclopropyl-N-(3-hydroxypropyl)carbamate (3.20 g, 14.8 mmol) in THF (30 mL) was added NaH (1.19 g, 29.7 mmol, 60% dispersion in oil) at 0° C. for 0.5 hour. Then 3-bromoprop-1-yne (3.54 g, 29.7 mmol, 2.56 mL) was added to the mixture. The reaction mixture was stirred at 25° C. for 12 hours. On completion, the reaction mixture was quenched with sat. NH₄Cl solution (10 mL) under stirring. The mixture was diluted with water (30 mL) and extracted with EA (3×50 mL). The combined organic layers was dried over Na₂SO₄, filtered and concentrated in vacuo to give the title compound (3.70 g, 98% yield) as light yellow oil. ¹H NMR (400 MHz, CDCl₃) δ 4.13 (d, J=2.4 Hz, 2H), 3.53 (t, J=6.4 Hz, 2H), 3.32-3.25 (m, 2H), 2.54-2.46 (m, 1H), 2.41 (t, J=2.4 Hz, 1H), 1.89-1.81 (m, 2H), 1.45 (s, 9H), 0.75-0.70 (m, 2H), 0.61-0.57 (m, 2H).

3-[4-[3-[3-(Cyclopropylamino)propoxy]propyl]-3-methyl-2-oxo-benzimidazol-1-yl]piperidine-2,6-dione (Intermediate XQ)

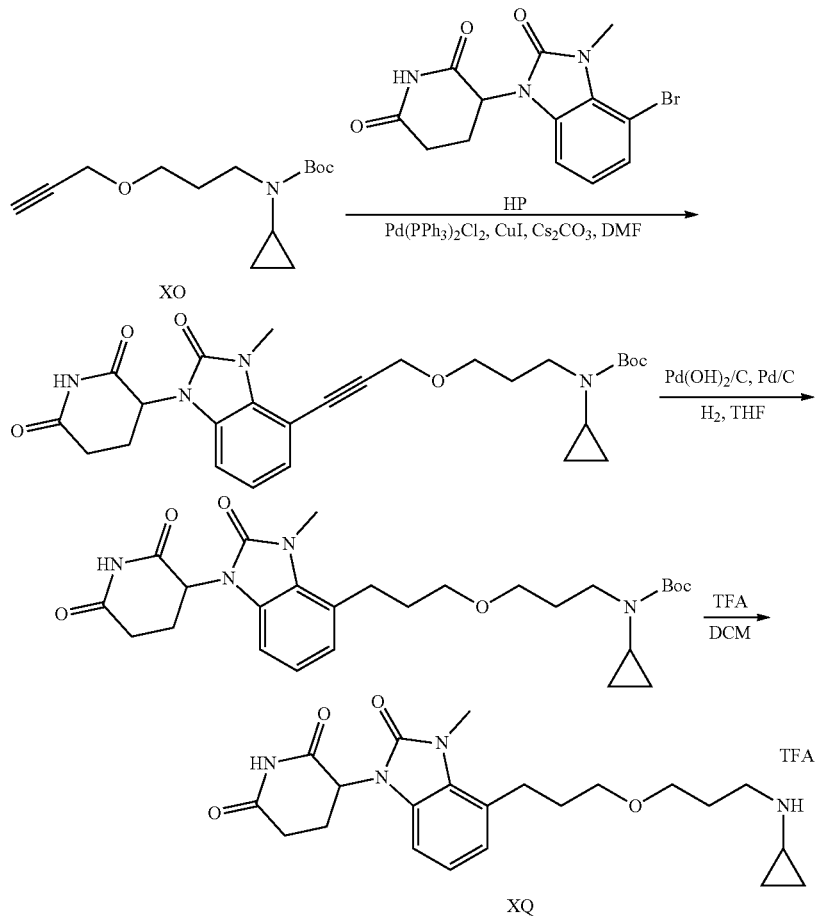

Step 1—Tert-butyl N-cyclopropyl-N-[3-[3-[1-(2,6-dioxo-3-piperidyl)-3-methyl-2-oxo-benzimidazol-4-yl]prop-2-ynoxy]propyl]carbamate To a mixture of tert-butyl N-cyclopropyl-N-(3-prop-2-ynoxypropyl)carbamate (599 mg, 2.37 mmol, Intermediate XP) and 3-(4-bromo-3-methyl-2-oxo-benzimidazol-1-yl)piperidine-2,6-dione (400 mg, 1.18 mmol, Intermediate HP) in DMF (5 mL) was added CuI (22.5 mg, 118 umol), Cs₂CO₃ (1.93 g, 5.91 mmol), Pd(PPh₃)₂Cl₂ (83.0 mg, 118 umol) and 4 Å molecular sieves (10 mg). The reaction mixture was stirred at 80° C. for 2 hours under N₂ atmosphere. On completion, the reaction mixture was filtered and concentrated in vacuo. The residue was purified by reverse phase (0.1% FA condition) to give the title compound (240 mg, 39% yield) as brown solid. ¹H NMR (400 MHz, DMSO-d₆) δ 11.14 (s, 1H), 7.18 (d, J=7.6 Hz, 1H), 7.13-7.09 (m, 1H), 7.05-7.00 (m, 1H), 5.43-5.37 (m, 1H), 4.43 (s, 2H), 3.64 (s, 3H), 3.53 (t, J=6.3 Hz, 2H), 3.44-3.37 (m, 2H), 3.21 (t, J=7.2 Hz, 2H), 2.94-2.83 (m, 1H), 2.75-2.55 (m, 3H), 2.07-1.98 (m, 1H), 1.80-1.70 (m, 2H), 1.39 (s, 2H), 1.37 (s, 9H), 0.70-0.63 (m, 2H), 0.57-0.49 (m, 2H).

Step 2—Tert-butyl N-cyclopropyl-N-[3-[3-[1-(2,6-dioxo-3-piperidyl)-3-methyl-2-oxo-benzimidazol-4-yl]propoxy]propyl]carbamate To a mixture of tert-butyl N-cyclopropyl-N-[3-[3-[1-(2,6-dioxo-3-piperidyl)-3-methyl-2-oxo-benzimidazol-4-yl] prop-2-ynoxy]propyl]carbamate (180 mg, 352 umol) in THF (20 mL) was added Pd(OH)₂/C (30.0 mg, 10 wt %) and Pd/C (30.0 mg, 10 wt %). The reaction mixture was stirred at 25° C. for 2.5 hours under H₂ (15 Psi) atmosphere. On completion, the reaction mixture was filtered and concentrated in vacuo to give the title compound (181 mg, 99% yield) as light yellow solid. The residue was used to the next step directly without further purification. ¹H NMR (400 MHz, DMSO-d₆) δ 11.09 (s, 1H), 6.96 (d, J=4.4 Hz, 2H), 6.89-6.84 (m, 1H), 5.39-5.33 (m, 1H), 3.56 (s, 3H), 3.41 (d, J=6.0 Hz, 2H), 3.38 (t, J=6.0 Hz, 2H), 3.21 (t, J=7.2 Hz, 2H), 2.99-2.93 (m, 2H), 2.91-2.84 (m, 1H), 2.72-2.62 (m, 3H), 2.02-1.99 (m, 1H), 1.85-1.79 (m, 2H), 1.77-1.70 (m, 2H), 1.38 (s, 9H), 0.70-0.64 (m, 2H), 0.56-0.50 (m, 2H).

Step 3—3-[4-[3-[3-(Cyclopropylamino)propoxy]propyl]-3-methyl-2-oxo-benzimidazol-1-yl]piperidine-2,6-dione To a mixture of tert-butyl N-cyclopropyl-N-[3-[3-[1-(2,6-dioxo-3-piperidyl)-3-methyl-2-oxo-benzimidazol-4-yl]propoxy]propyl]carbamate (190 mg, 369 umol) in DCM (1 mL) was added TFA (4.62 g, 40.5 mmol, 3.00 mL). The reaction mixture was stirred at 25° C. for 1 hour. On completion, the reaction mixture was concentrated in vacuo to give the title compound (195 mg, 99% yield, TFA salt) as red oil. LC-MS (ESI⁺) m/z 415.3 (M+H)⁺.

Tert-butyl 4-(4-piperidylmethyl)piperidine-1-carboxylate (Intermediate XS)

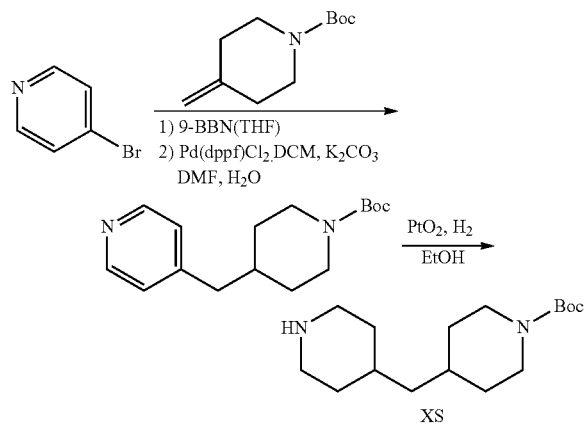

Step 1—Tert-butyl 4-(4-pyridylmethyl)piperidine-1-carboxylate

To a solution of tert-butyl 4-methylenepiperidine-1-carboxylate (6.00 g, 30.4 mmol, CAS #159635-49-1) was added 9-BBN THF solution (0.5 M, 60.5 mL) at 25° C. The reaction mixture was stirred at 80° C. for 1 hour under N₂. After cooling to 25° C., 4-bromopyridine (4.33 g, 27.4 mmol, CAS #1120-87-2), K₂CO₃ (5.04 g, 36.5 mmol), Pd(dppf)Cl₂—CH₂Cl₂ (683 mg, 836 umol), DMF (50 mL) and H₂O (5 mL) were added to the reaction mixture was added. The reaction mixture was stirred at 60° C. for 3 hours. After cooling to 25° C., another charge of Pd(dppf)Cl₂—CH₂Cl₂ (683 mg, 836 umol) was added to the reaction mixture. The mixture was stirred at 60° C. for 24 hours. On completion, the mixture was cooled to 25° C. and poured into water (60 mL). The pH was adjusted to 11 with 10% aq. NaOH. The mixture was extracted with ethyl acetate (2×100 mL). The combined organic layers were dried over NaSO₄, filtered and concentrated in vacuo. The residue was purified by column chromatography to give the title compound (5.80 g, 76% yield) as yellow oil. ¹H NMR (400 MHz, CDCl₃) δ 8.53-8.47 (m, 2H), 7.08 (d, J=6.0 Hz, 2H), 2.64 (t, J=12.0 Hz, 2H), 2.54 (d, J=7.6 Hz, 2H), 1.77-1.64 (m, 2H), 1.63-1.56 (m, 2H), 1.54-1.47 (m, 1H), 1.45 (s, 9H), 1.21-1.09 (m, 2H).

Step 2 Tert-butyl 4-(4-piperidylmethyl)piperidine-1-carboxylate

To a solution of tert-butyl 4-(4-pyridylmethyl)piperidine-1-carboxylate (5.80 g, 20.9 mmol) in EtOH (100 mL) and HOAc (1.26 g, 20.9 mmol) was added PtO₂ (1.02 g, 4.48 mmol) at 20° C. The reaction mixture was stirred at 20° C. for 54 hours under H₂ (50 Psi). On completion, the reaction mixture was filtered with celite and the filtrate was concentrated in vacuo to give the title compound (4.68 g, 79% yield) as black oil. ¹H NMR (400 MHz, CDCl₃) δ 4.26-4.00 (m, 4H), 3.16 (d, J=9.6 Hz, 2H), 2.70-2.60 (m, 3H), 1.69 (d, J=12.8 Hz, 2H), 1.65-1.56 (m, 2H), 1.54-1.46 (m, 2H), 1.44 (s, 9H), 1.29-1.20 (m, 2H), 1.20-1.13 (m, 2H), 1.11-0.97 (m, 2H); LC-MS (ESI⁺) m/z 283.0 (M+H)⁺.

3-[3-methyl-2-oxo-4-[[4-(4-piperidylmethyl)-1-piperidyl]methyl]benzimidazol-1-yl]piperidine-2,6-dione (Intermediate XT)

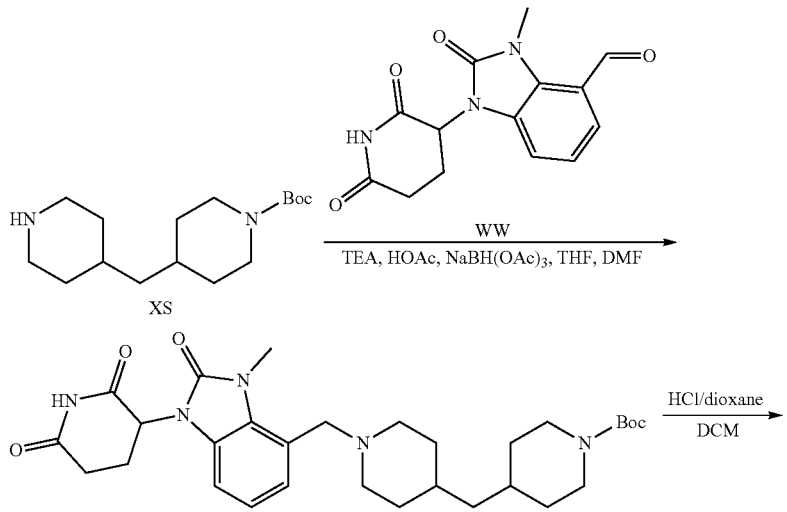

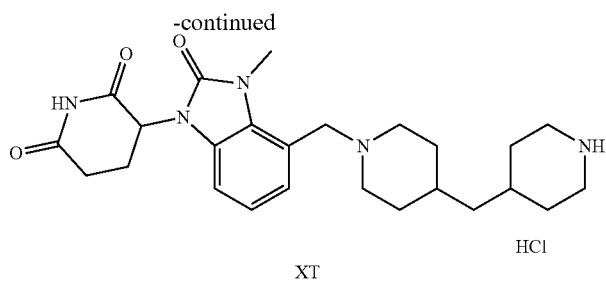

XT · HCl

Step 1—Tert-butyl 4-[[1-[[1-(2,6-dioxo-3-piperidyl)-3-methyl-2-oxo-benzimidazol-4-yl]methyl]-4-piperidyl]methyl]piperidine-1-carboxylate To a solution of tert-butyl 4-(4-piperidylmethyl)piperidine-1-carboxylate (128 mg, 452 umol, Intermediate XS) in THF (10 mL) and DMF (5 mL) was added TEA (45.8 mg, 452 umol). The mixture was stirred at 25° C. for 10 minutes. HOAc (27.2 mg, 452 umol) and 1-(2,6-dioxo-3-piperidyl)-3-methyl-2-oxo-benzimidazole-4-carbaldehyde (195 mg, 679 umol, Intermediate WW) were added to the above mixture. The reaction mixture was stirred at 25° C. for 20 minutes. Then NaBH(OAc)$_3$ (192 mg, 905 umol) was added. The reaction mixture was stirred at 25° C. for 16 hours. On completion, the reaction was quenched with H$_2$O (1 mL). The mixture was concentrated in vacuo. The residue was purified by reverse phase (FA condition) to give the title compound (250 mg, 99% yield) as a yellow solid. $^1$H NMR (400 MHz, DMSO-d$_6$) δ 11.09 (s, 1H), 7.19 (d, J=6.4 Hz, 1H), 6.95 (t, J=7.6 Hz, 1H), 6.86 (d, J=7.2 Hz, 1H), 5.36 (d, J=5.6 Hz, 1H), 3.97-3.81 (m, 2H), 3.66 (s, 3H), 3.60 (s, 2H), 2.96-2.83 (m, 2H), 2.83-2.69 (m, 4H), 2.66-2.58 (m, 3H), 2.06-1.89 (m, 4H), 1.58 (d, J=12.4 Hz, 4H), 1.37 (s, 9H), 1.14-0.98 (m, 4H), 0.96-0.81 (m, 2H); LC-MS (ESI$^+$) m/z 554.4 (M+H)$^+$.

Step 2—3-[3-methyl-2-oxo-4-[[4-(4-piperidylmethyl)-1-piperidyl]methyl]benzimidazol-1-yl]piperidine-2,6-dione To a solution of tert-butyl 4-[[1-[[1-(2,6-dioxo-3-piperidyl)-3-methyl-2-oxo-benzimidazol-4-yl]methyl]-4-piperidyl]methyl]piperidine-1-carboxylate (100 mg, 181 umol) in DCM (2 mL) was added 4 M HCl/dioxane (1 mL) at 25° C. The reaction mixture was stirred at 25° C. for 1 hour. On completion, the reaction mixture was concentrated in vacuo. The residue was purified by reverse phase (FA condition) to give the title compound (65.0 mg, 79% yield) as a white solid. LC-MS (ESI$^+$) m/z 454.5 (M+H)$^+$.

3-(7-bromo-9H-pyrido[2,3-b]indol-9-yl)piperidine-2,6-dione (Intermediate

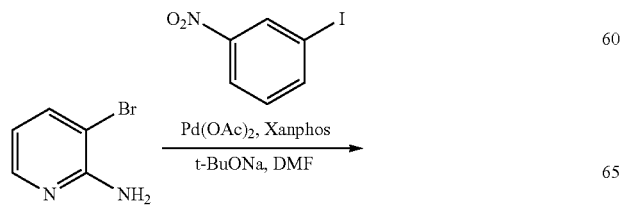

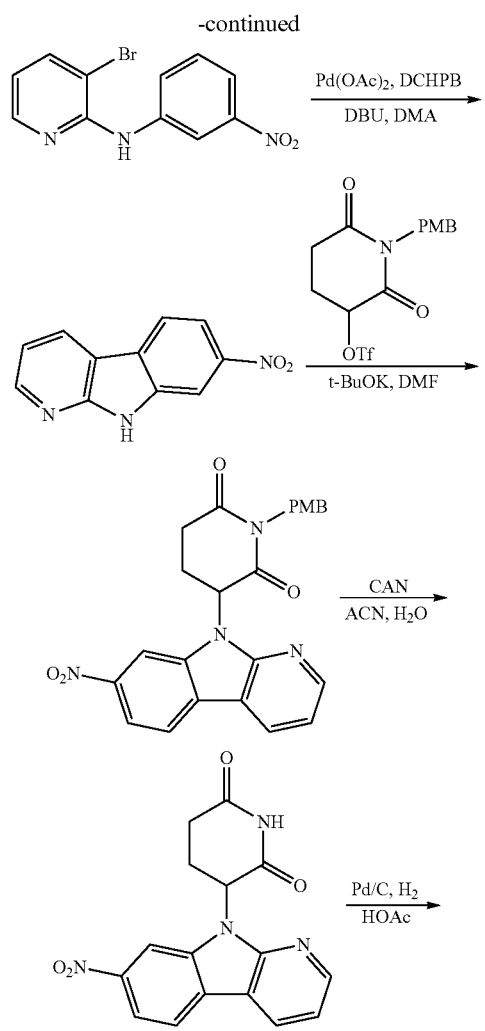

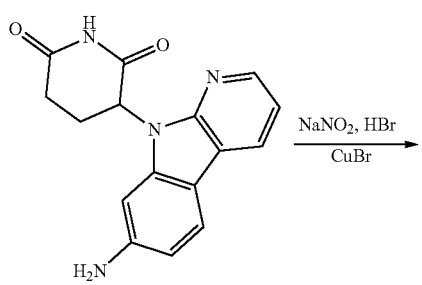

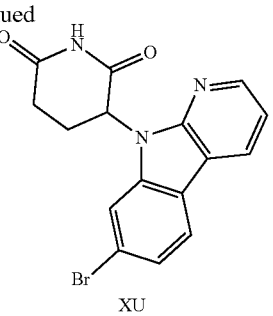

XU

Step 1—3-bromo-N-(3-nitrophenyl)pyridin-2-amine

To a mixture of 3-bromopyridin-2-amine (5 g, 28.9 mmol), 1-iodo-3-nitrobenzene (7.2 g, 28.9 mmol), Xanphos (1.07 g, 2.89 mmol), and $Cs_2CO_3$ (18.9 g, 57.8 mmol) in DMF (50 mL) was added Pd(OAc)$_2$ (323.7 mg, 1.44 mmol). The mixture was degrassed with $N_2$ and stirred at 130° C. overnight. The reaction mixture was cooled to rt, poured into water, and extracted with EtOAc (3×200 mL). The combined organic layers was washed with water (200 mL×2) and brine (200 mL×2), dried over anhydrous $Na_2SO_4$, filtered and concentrated in vacuo. The residue was purified by flash chromatography eluting with EA/PE=20% to give the title compound (5.6 g, 66% yield) as a light yellow solid. LC/MS (ESI, m/z): [M+1]$^+$=294.0, 296.0.

Step 2—7-nitro-9H-pyrido[2,3-b]indole

To a mixture of 3-bromo-N-(3-nitrophenyl)pyridin-2-amine (4 g, 6.78 mmol), DCPHB (474 mg, 1.356 mmol), and DBU (4.12 g, 27.12 mmol) in DMA (12 mL) was added Pd(OAc)$_2$ (152 mg, 0.678 mmol). The mixture was degrassed with $N_2$ and stirred at 170° C. for 1 h. The reaction mixture was cooled to rt, poured into water, and extracted with EtOAc (3×50 mL). The combined organic layers was washed with water (100 mL×2) and brine (100 mL×2), dried over anhydrous $Na_2SO_4$, filtered and concentrated in vacuo. The residue was purified by flash chromatography eluting with EA/PE=1:1 to give the title compound (1 g, 34% yield) as a light yellow solid. $^1$H NMR (400 MHz, DMSO-d$_6$) δ 12.40 (s, 1H), 8.73-8.70 (m, 1H), 8.60-8.58 (m, 1H), 8.44 (d, J=8.63 Hz, 1H), 8.33 (d, J=2.00 Hz, 1H), 8.13-8.10 (m, 1H), 7.35 (dd, J=7.75, 4.75 Hz, 1H); LC/MS (ESI, m/z): [M+1]$^+$=214.1.

Step 3—1-(4-methoxybenzyl)-3-(7-nitro-9H-pyrido[2,3-b]indol-9-yl)piperidine-2,6-dione To a solution of 7-nitro-9H-pyrido[2,3-b]indole (910 mg, 4.27 mmol) in THF (10 mL) and DMF (2 mL) was added t-BuOK (718 mg, 6.41 mmol) portion wise at 0° C. under $N_2$ atmosphere. After addition, the mixture was stirred at 0° C.~5° C. for 1 h. Then 1-(4-methoxybenzyl)-2,6-dioxopiperidin-3-yl trifluoromethanesulfonate (2.44 g, 6.41 mmol) in THF (10 mL) was added dropwise at 0° C.~5° C. over 20 min. After addition, the reaction mixture was stirred at 0° C.~5° C. for an additional 1 h. The reaction mixture was quenched by the addition of water, then extracted with EtOAc (3×20 mL). The combined organic layers was washed with brine (10 mL×2), dried over anhydrous $Na_2SO_4$, filtered and concentrated in vacuo. The residue was triturated with EtOAc and dried to give (1.3 g, 69% yield) as a light yellow solid. LC/MS (ESI, m/z): [M+1]$^+$=445.2.

Step 4—3-(7-nitro-9H-pyrido[2,3-b]indol-9-yl)piperidine-2,6-dione

To a solution of 1-(4-methoxybenzyl)-3-(7-nitro-9H-pyrido[2,3-b]indol-9-yl)piperidine-2,6-dione (1.7 g, 3.83 mmol) in $CH_3CN$ (20 mL) was added CAN (10.5 g, 19.15 mmol) in water (5 mL) at 0° C. dropwise. After addition, the mixture was stirred at rt overnight. The mixture was poured into water (50 mL), then extracted with EtOAc (3×50 mL). The combined organic layers was washed with brine (2×20 mL), dried over anhydrous $Na_2SO_4$, filtered and concentrated in vacuo. The residue was triturated with EtOAc and dried to give the title compound (850 mg, 69% yield) as a light yellow solid. LC/MS (ESI, m/z): [M+1]$^+$=325.2.

Step 5—3-(7-amino-9H-pyrido[2,3-b]indol-9-yl)piperidine-2,6-dione

To a solution of 3-(7-nitro-9H-pyrido[2,3-b]indol-9-yl)piperidine-2,6-dione (850 mg, 2.62 mmol) in EtOAc (15 mL) was added 10% palladium on activated carbon (170 mg). The mixture was hydrogened at rt overnight. The reaction mixture was filtered, the filtrate was concentrated in vacuo to give the title compound (764 mg, 99% yield) as a white solid. LC/MS (ESI, m/z): [M+1]$^+$=295.2.

Step 6—3-(7-bromo-9H-pyrido[2,3-b]indol-9-yl)piperidine-2,6-dione

To a solution of 3-(7-amino-9H-pyrido[2,3-b]indol-9-yl)piperidine-2,6-dione (661 mg, 2.26 mmol) in 40% HBr solution (10 mL) was added $NaNO_2$ (156 mg, 2.26 mmol) portion wise at 0° C. After addition, the mixture was stirred at 0° C. for 30 min. Then the diazonium solution was added dropwise to CuBr (972 mg, 6.78 mmol) in 40% HBr solution (10 mL). The mixture was stirred at rt for 2 h. Then the mixture was poured into water (50 mL), basified to pH>8 with saturated $NaHCO_3$ solution, then extracted with EtOAc (3×50 mL). The combined organic layers was washed with brine (2×30 mL), dried over anhydrous $Na_2SO_4$, filtered and concentrated in vacuo. The residue was purified by prep-HPLC to give the title compound (382 mg, 47% yield) as a yellow solid. LC/MS (ESI, m/z): [M+1]$^+$=358.1, 360.1.

3-[7-[3-[2-(2-Aminoethoxy)ethoxy]propyl]pyrido[2,3-b]indol-9-yl]piperidine-2,6-dione (Intermediate XV)

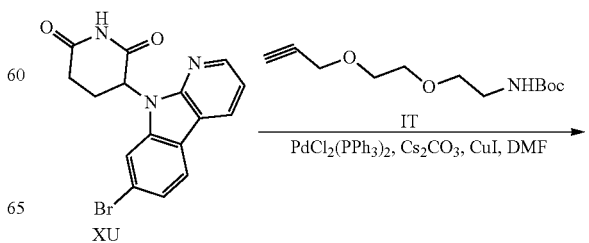

XU

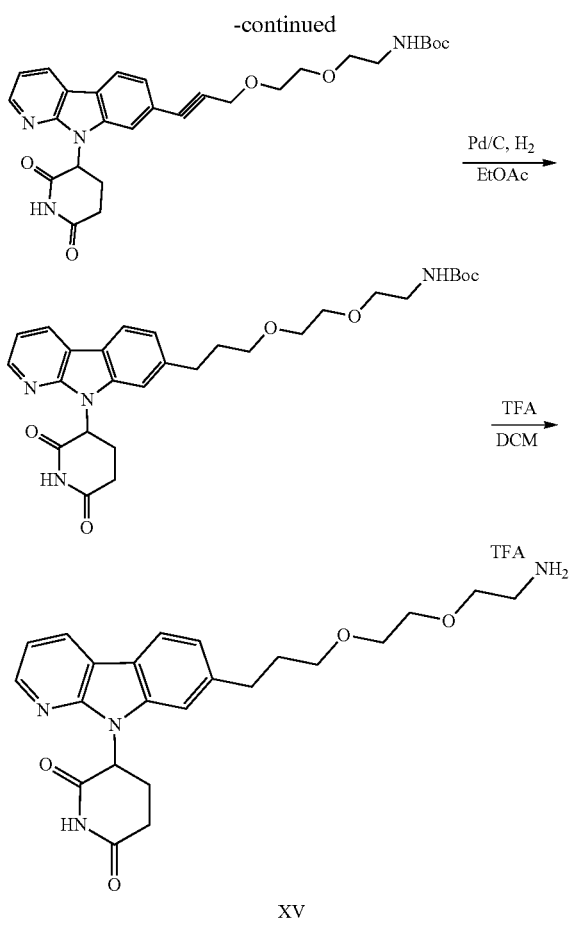

Step 1—tert-butyl (2-(2-((3-(9-(2,6-dioxopiperidin-3-yl)-9H-pyrido[2,3-b]indol-7-yl)prop-2-yn-1-yl)oxy)ethoxy)ethyl)carbamate To a mixture of 3-(7-bromo-9H-pyrido[2,3-b]indol-9-yl)piperidine-2,6-dione (461 mg, 1.29 mmol, Intermediate XU), tert-butyl (2-(2-(prop-2-yn-1-yloxy)ethoxy)ethyl)carbamate (941 mg, 3.87 mmol, Intermediate IT), and $Cs_2CO_3$ (2.1 g, 6.45 mmol) in DMF was added CuI (49 mg, 0.258 mmol) and $PdCl_2(PPh_3)_2$ (181 mg, 0.258 mmol). The mixture was degrassed with $N_2$ and stirred at 80° C. for 1 h under microwave condition. The reaction mixture was cooled to rt, poured into water, then extracted with EtOAc (3×20 mL). The combined organic layers was washed with water (20 mL×2) and brine (2×30 mL), dried over anhydrous $Na_2SO_4$, filtered and concentrated in vacuo. The residue was purified by flash chromatography eluting with EA/DCM=1:1 to the title compound (410 mg, 68% yield) as yellow solid. LC/MS (ESI, m/z): [M−55+H]+=466.1.

Step 2—tert-butyl (2-(2-(3-(9-(2,6-dioxopiperidin-3-yl)-9H-pyrido[2,3-b]indol-7-yl)propoxy)ethoxy)ethyl)carbamate To a solution of tert-butyl (2-(2-((3-(9-(2,6-dioxopiperidin-3-yl)-9H-pyrido[2,3-b]indol-7-yl)prop-2-yn-1-yl)oxy)ethoxy)ethyl)carbamate (400 mg, 0.77 mmol) in EtOAc (5 mL) was added 10% palladium on activated carbon (81 mg). The mixture was hydrogened at rt overnight. The reaction mixture was filtered, the filtrate was concentrated in vacuo. The residue was purified by P-TLC eluting with EA/DCM=1:2 firstly, then the crude compound was purified by prep HPLC to give the title compound (132 mg, 66% yield) as a white solid. $^1$H NMR (400 MHz, DMSO-$d_6$) δ 11.13 (s, 1H), 8.49 (dd, J=7.63, 1.50 Hz, 1H), 8.38-8.35 (m, 1H), 8.11 (d, J=7.88 Hz, 1H), 7.47 (br. s., 1H), 7.24 (dd, J=7.63, 4.88 Hz, 1H), 7.12-7.18 (m, 1H), 6.77-6.74 (m, 1H), 6.01 (br. s., 1H), 3.47-3.55 (m, 4H), 3.45-3.37 (m, 4H), 3.15-3.02 (m, 4H), 2.80 (t, J=7.69 Hz, 2H), 2.73-2.68 (m, 1H), 2.13-2.07 (m, 1H), 1.94-1.88 (m, 2H), 1.36 (s, 9H); LC/MS (ESI, m/z): [M+1]+=525.3.

Step 3—3-[7-[3-[2-(2-Aminoethoxy)ethoxy]propyl]pyrido[2,3-b]indol-9-yl]piperidine-2,6-dione To a solution of tert-butyl N-[2-[2-[3-[9-(2,6-dioxo-3-piperidyl)pyrido[2,3-b]indol-7-yl]propoxy]ethoxy]ethyl]carbamate (95.0 mg, 181 umol) in DCM (3 mL) was added TFA (722 mg, 6.34 mmol). The reaction mixture was stirred at 25° C. for 1 hr. On completion, the reaction mixture was concentrated in vacuo to give the title compound (95 mg, 95% yield, TFA) as light yellow oil. LC-MS (ESI+) m/z 425.2 (M+H)+.

2-[2-(Cyclopropylmethylamino)-4-pyridyl]oxazole-4-carboxylic acid (Intermediate XW)

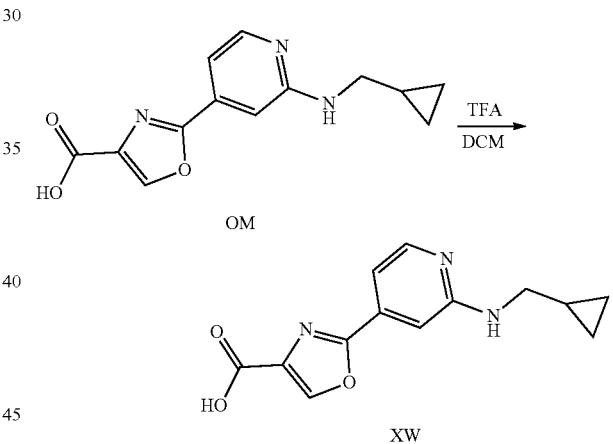

To a mixture of 2-[2-[tert-butoxycarbonyl(cyclopropylmethyl)amino]-4-pyridyl]oxazole-4-carboxylic acid (400 mg, 1.11 mmol, Intermediate OM) in DCM (10 mL) was added TFA (127 mg, 1.11 mmol). The reaction mixture was stirred at 25° C. for 2 hours. On completion, the reaction mixture was concentrated in vacuo to give the title compound (397 mg, 95% yield, TFA salt) as brown oil. LC-MS (ESI+) m/z 260.1 (M+H)+.

3-(4-Bromo-9H-pyrido[2,3-b]indol-9-yl)piperidine-2,6-dione (Intermediate XY)

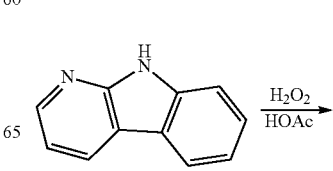

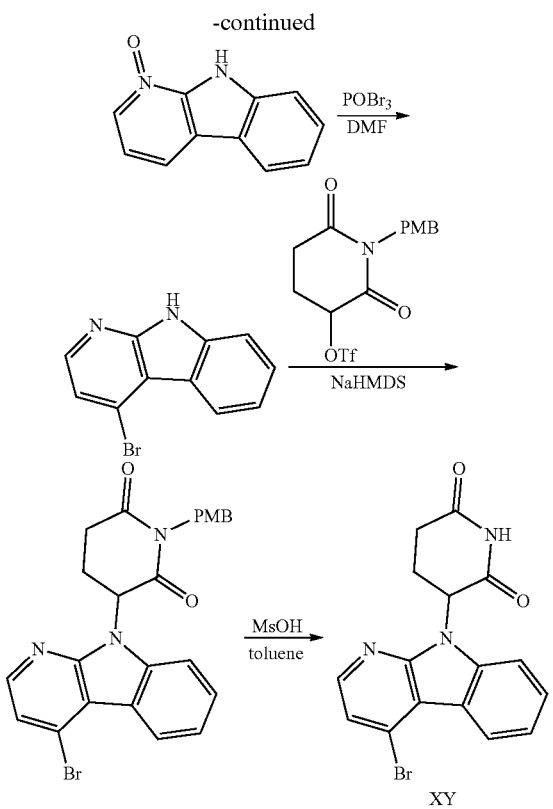

Step 1—9H-pyrido[2,3-b]indole 1-oxide

To a stirred solution of 9H-pyrido[2,3-b]indole (10 g, 59.5 mmol) in AcOH (100 mL) was added 30% $H_2O_2$ (50 mL) dropwise. After the addition, the reaction mixture was heated to 110° C. and stirred for 6 h. Then the reaction mixture was cooled to rt and concentrated in vacuo. To the residue was added sat. aq. $K_2CO_3$ to basify topH=8. The mixture was stirred at rt overnight and filtered. The solid was washed with water and dried to afford the title compound (7.3 g, 67% yield) as a yellow solid. $^1$H NMR (400 MHz, DMSO-$d_6$) δ 12.58 (s, 1H), 8.36-8.34 (m, 1H), 8.25-8.14 (m, 2H), 7.58-7.50 (m, 2H), 7.35-7.18 (m, 2H). LC/MS (ESI, m/z): [M+1]$^+$=185.1

Step 2—4-bromo-9H-pyrido[2,3-b]indole

To a solution of 9H-pyrido[2,3-b]indole 1-oxide (9.3 g, 50.5 mmol) in DMF (100 mL) was added phosphorusoxybromide (29.0 g, 101.1 mmol) at rt. The reaction mixture was stirred at rt overnight and filtered. The solid was washed with water and dried to afford the title compound (9.0 g, 73% yield) as a yellow solid. $^1$H NMR (400 MHz, CDCl$_3$) δ 9.28 (s, 1H), 8.61 (d, J=8.0 Hz, 1H), 8.25 (d, J=5.4 Hz, 1H), 7.59-7.52 (m, 2H), 7.43-7.33 (m, 2H). LC/MS (ESI, m/z): [M+1]$^+$=247.3, 249.3.

Step 3—3-(4-bromo-9H-pyrido[2,3-b]indol-9-yl)-1-(4-methoxybenzyl)piperidine-2,6-dione To a solution of 4-bromo-9H-pyrido[2,3-b]indole (8.8 g, 35.6 mmol) and 18-crown-6 (1.9 g, 7.13 mmol) in THF (100 mL) was added NaHMDS (26.7 mL, 53.4 mmol, 2N in THF) dropwise at −30° C. under $N_2$ atmosphere. After addition, the reaction mixture was stirred at −30° C. for 1 h. Then 1-(4-methoxybenzyl)-2,6-dioxopiperidin-3-yl trifluoromethanesulfonate (20.4 g in 30 mL THF, 53.4 mmol) was added to solution dropwise. After addition, the reaction mixture was stirred at −30° C. for 2 h and quenched by sat. aq. NH$_4$Cl (100 mL), then extracted with EA (150 mL×2). The combined organic layers were washed with brine (100 mL×2), dried over anhydrous Na$_2$SO$_4$, filtered and concentrated in vacuo. The residue was purified by column to give the title compound (10.0 g, 59% yield) as a white solid. LC/MS (ESI, m/z): [M+1]$^+$=478.3.

Step 4—3-(4-bromo-9H-pyrido[2,3-b]indol-9-yl)piperidine-2,6-dione

To a solution of 3-(4-bromo-9H-pyrido[2,3-b]indol-9-yl)-1-(4-methoxybenzyl)piperidine-2,6-dione (10 g, 20.9 mmol) in toluene (50 mL) was added methanesulfonic acid (20 mL). The reaction solution was heated to 110° C. and stirred for 2 h. The reaction mixture was cooled to rt and concentrated to remove toluene. The residue was diluted with CH$_3$CN and purified via reverse phase column chromatography (CH$_3$CN/H$_2$O=5%-80%) to give the title compound (3.7 g, 50% yield) as a white solid. $^1$H NMR (400 MHz, DMSO-$d_6$) δ 11.19 (s, 1H), 8.57 (d, J=7.9 Hz, 1H), 8.30 (d, J=5.3 Hz, 1H), 7.73-7.69 (m, 1H), 7.63 (t, J=7.9 Hz, 1H), 7.56 (d, J=5.3 Hz, 1H), 7.41 (t, J=7.9 Hz, 1H), 6.10 (s, 1H), 3.14-2.98 (m, 2H), 2.73-2.68 (m, 1H), 2.18-2.12 (m, 1H). LC/MS (ESI, m/z): [M+1]$^+$=358.0.

3-[4-[3-[2-(2-Aminoethoxy)ethoxy]propyl]pyrido[2,3-b]indol-9-yl]piperidine-2,6-dione (Intermediate XZ)

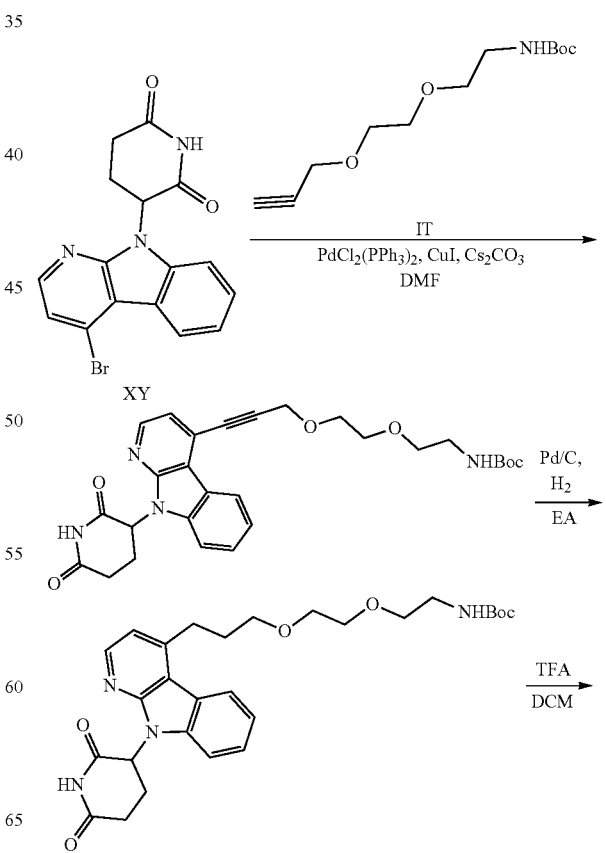

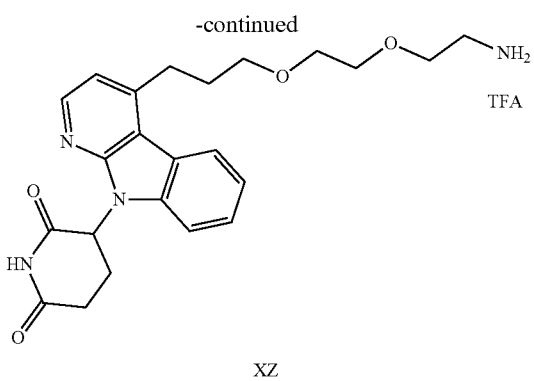

XZ

Step 1—tert-butyl (2-(2-((3-(9-(2,6-dioxopiperidin-3-yl)-9H-pyrido[2,3-b]indol-4-yl)prop-2-yn-1-yl)oxy)ethoxy)ethyl)carbamate To a mixture of 3-(4-bromo-9H-pyrido[2,3-b]indol-9-yl)piperidine-2,6-dione (0.3 g, 0.84 mmol, Intermediate XY), tert-butyl (2-(2-(prop-2-yn-1-yloxy)ethoxy)ethyl)carbamate (0.31 g, 1.26 mmol, Intermediate IT), Cs$_2$CO$_3$ (2.7 g, 8.38 mmol) in DMF (10 mL) was added CuI (16 mg, 0.084 mmol) and PdCl$_2$(PPh$_3$)$_2$ (0.12 g, 0.17 mmol). The mixture was degrassed with N$_2$ and stirred at 80° C. for 1 h under microwave condition. The reaction mixture was cooled to rt, poured into water, then extracted with EtOAc (3×20 mL). The combined organic layers was washed with water (20 mL×2) and brine, dried over anhydrous Na$_2$SO$_4$, filtered and concentrated in vacuo. The residue was purified by flash chromatography eluting with EA/DCM=1:1 to give the title compound (0.16 g, 37% yield) as yellow solid. LC/MS (ESI, m/z): [M −55+H]$^+$=466.1.

Step 2—tert-butyl (2-(2-(3-(9-(2,6-dioxopiperidin-3-yl)-9H-pyrido[2,3-b]indol-4-yl)propoxy)ethoxy)ethyl)carbamate To a solution of tert-butyl (2-(2-((3-(9-(2,6-dioxopiperidin-3-yl)-9H-pyrido[2,3-b]indol-4-yl)prop-2-yn-1-yl)oxy)ethoxy)ethyl)carbamate (0.16 g, 0.31 mmol) in EtOAc (5 mL) was added 10% palladium on activated carbon (32 mg). The mixture was hydrogened at rt overnight. Then the reaction mixture was filtered and the filtrate was concentrated in vacuo. The residue was purified by P-TLC eluting with EA/DCM=1:2 firstly, then the crude compound was purified by prep HPLC to give the title compound (60 mg, 38% yield) as a white solid. $^1$H NMR (400 MHz, CDCl$_3$) δ 8.32 (d, J=5.1 Hz, 1H), 8.20 (d, J=7.9 Hz, 1H), 8.12 (s, 1H), 7.53-7.46 (m, 1H), 7.34-7.28 (m, 2H), 7.06-7.04 (m, 1H), 5.96 (s, 1H), 5.00 (s, 1H), 3.66-3.56 (m, 8H), 3.41-3.24 (m, 4H), 3.09-2.99 (m, 3H), 2.33-2.29 (m, 1H), 2.18-2.11 (m, 2H), 1.43 (s, 9H). LC/MS (ESI, m/z): [M+1]$^+$=525.4.

Step 3—3-[4-[3-[2-(2-Aminoethoxy)ethoxy]propyl]pyrido[2,3-b]indol-9-yl]piperidine-2,6-dione To a solution of tert-butyl N-[2-[2-[3-[9-(2,6-dioxo-3-piperidyl)pyrido[2,3-b]indol-4-yl]propoxy]ethoxy]ethyl]carbamate (66.0 mg, 125 umol) in DCM (2 mL) was added TFA (573 mg, 5.03 mmol). The mixture was stirred at 25° C. for 2 hrs. On completion, the mixture was concentrated in vacuo to give the title compound (67.0 mg, 95% yield, TFA) as light yellow oil. LC-MS (ESI$^+$) m/z 425.0 (M+H)$^+$.

Tert-butyl 3-(prop-2-ynoxymethyl)azetidine-1-carboxylate (Intermediate YA)

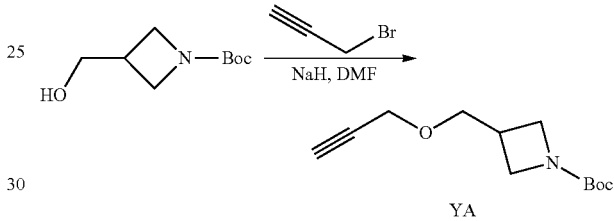

To a solution of tert-butyl 3-(hydroxymethyl)azetidine-1-carboxylate (2.00 g, 10.7 mmol, CAS #142253-56-3) in DMF (20 mL) was added NaH (641 mg, 16.0 mmol, 60% oil dispersion) at 0° C. Thirty minutes later, 3-bromoprop-1-yne (1.40 g, 11.8 mmol, 1.01 mL, CAS #106-96-7) was added and the reaction mixture was stirred at 25° C. for 12 hrs. On completion, the mixture was quenched with water (50 mL), then extracted with EA (2×30 mL). The combined organic layer was washed with brine (50 mL), dried over anhydrous sodium sulfate, filtered and concentrated in vacuo. The residue was purified by silica gel chromatography (SiO$_2$, PE:EA=15:1) to give the title compound (0.60 g, 25% yield) as yellow oil. $^1$H NMR (400 MHz, CDCl$_3$) δ 4.17 (d, J=2.4 Hz, 2H), 4.00 (t, J=8.4 Hz, 2H), 3.71-3.64 (m, 4H), 2.87-2.69 (m, 1H), 2.45 (t, J=2.4 Hz, 1H), 1.44 (s, 9H).

3-[4-[3-(Azetidin-3-ylmethoxy)propyl]-3-methyl-2-oxo-benzimidazol-1-yl]piperidine-2,6-dione (Intermediate YB)

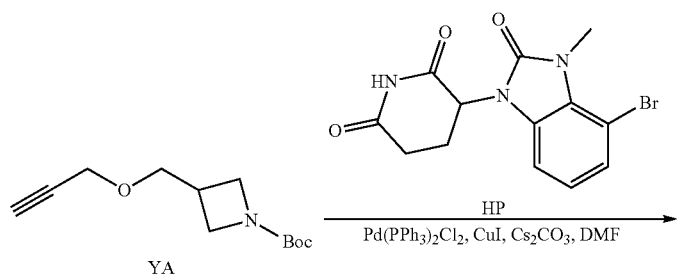

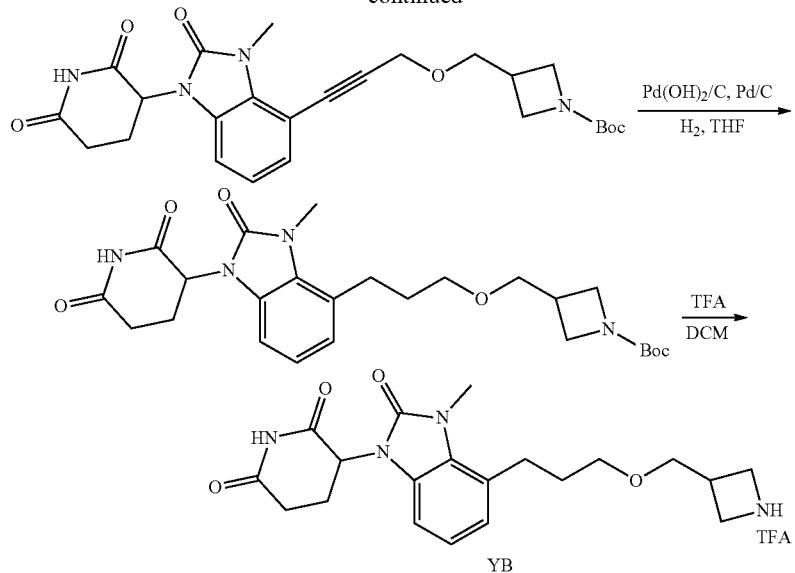

Step 1—Tert-butyl 3-[3-[1-(2,6-dioxo-3-piperidyl)-3-methyl-2-oxo-benzimidazol-4-yl]prop-2-ynoxymethyl]azetidine-1-carboxylate To a solution of tert-butyl 3-(prop-2-ynoxymethyl)azetidine-1-carboxylate (480 mg, 2.13 mmol, Intermediate YA) and 3-(4-bromo-3-methyl-2-oxo-benzimidazol-1-yl)piperidine-2,6-dione (400 mg, 1.18 mmol, Intermediate HP) in DMF (8 mL) was added Pd(PPh$_3$)$_2$Cl$_2$ (166 mg, 236 umol), Cs$_2$CO$_3$ (1.93 g, 5.91 mmol), and CuI (45.1 mg, 236 umol) under N$_2$ atmosphere. The mixture was de-gassed and then heated at 80° C. for 2 hrs under N$_2$ atmosphere. On completion, the mixture was concentrated in vacuo. The residue was washed with ethyl acetate (60 mL), the filtrate was concentrated in vacuo. The residue was purified by reversed-phase HPLC (0.1% FA condition) to give the title compound (450 mg, 63% yield) as brown solid. $^1$H NMR (400 MHz, DMSO-d$_6$) δ 11.12 (m, 1H), 7.20-7.10 (m, 2H), 7.06-6.99 (m, 1H), 5.39 (dd, J=5.6, 12.8 Hz, 1H), 4.47 (s, 2H), 3.64 (s, 3H), 3.60-3.56 (m, 4H), 2.80-2.70 (m, 4H), 2.61-2.59 (m, 2H), 2.06-1.98 (m, 1H), 1.35 (s, 9H); LC-MS (ESI+) m/z 505.2 (M+Na)$^+$.

Step 2—Tert-butyl 3-[3-[1-(2,6-dioxo-3-piperidyl)-3-methyl-2-oxo-benzimidazol-4-yl]propoxymethyl]azetidine-1-carboxylate To a solution of tert-butyl 3-[3-[1-(2,6-dioxo-3-piperidyl)-3-methyl-2-oxo-benzimidazol-4-yl]prop-2-ynoxymethyl]azetidine-1-carboxylate (400 mg, 829 umol) in THF (8 mL) was added Pd/C (80.0 mg, 10% wt) and Pd(OH)$_2$/C (80.0 mg, 10% wt) under N$_2$ atmosphere. The suspension was degassed under vacuum and purged with H$_2$ several times. The mixture was stirred at 25° C. for 12 hrs. On completion, the mixture was filtered and then the filtrate was concentrated in vacuo to give the title compound (400 mg, 79% yield) as brown solid. $^1$H NMR (400 MHz, DMSO-d$_6$) δ 11.09 (s, 1H), 6.99-6.95 (m, 2H), 6.87-6.85 (m, 1H), 5.37 (dd, J=5.2, 12.4 Hz, 1H), 3.56 (s, 3H), 3.52-3.46 (m, 4H), 3.33 (s, 3H), 3.00-2.92 (m, 2H), 2.91-2.84 (m, 1H), 2.78-2.55 (m, 4H), 2.04-1.96 (m, 1H), 1.89-1.77 (m, 2H), 1.38-1.36 (m, 9H). LC-MS (ESI+) m/z 509.3 (M+Na)$^+$.

Step 3—3-[4-[3-(Azetidin-3-ylmethoxy)propyl]-3-methyl-2-oxo-benzimidazol-1-yl]piperidine-2,6-dione To a solution of tert-butyl 3-[3-[1-(2,6-dioxo-3-piperidyl)-3-methyl-2-oxo-benzimidazol-4-yl]propoxymethyl]azetidine-1-carboxylate (313 mg, 514 umol) in DCM (3 mL) was added TFA (3 mL). The mixture was stirred at 25° C. for 2 hrs. On completion, the mixture was concentrated in vacuo to give the title compound (230 mg, 89% yield, TFA salt) as yellow solid. LC-MS (ESI+) m/z 387.2 (M+H)$^+$.

Tert-butyl N-but-3-ynyl-N-methyl-carbamate (Intermediate YC)

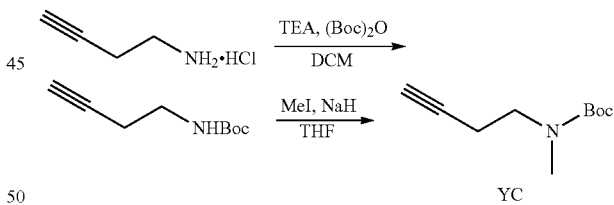

Step 1—Tert-butyl N-but-3-ynylcarbamate

To a solution of but-3-yn-1-amine (4.30 g, 40.7 mmol, HCl) and TEA (4.12 g, 40.7 mmol) in DCM (150 mL) was added (Boc)$_2$O (9.16 g, 41.9 mmol) dropwise at 0° C. The reaction mixture was stirred at 0° C. for 30 minutes. Then TEA (4.12 g, 40.7 mmol) added dropwise at 0° C. The reaction mixture was stirred at 25° C. for 1 hour. On completion, the reaction mixture was diluted with DCM (400 mL) and washed with water (2×100 mL) and HCl (0.5 N, 3×300 mL). The organic layers were dried with anhydrous Na$_2$SO$_4$ and filtered. The filtrate was concentrated in vacuo. The residue was purified by silica column chromatography to give the title compound (4.00 g, 58% yield) as colorless oil. $^1$H NMR (300 MHz, CDCl$_3$) δ 4.93 (s, 1H), 3.25 (q, J=6.0 Hz, 2H), 2.35 (dt, J=2.7, 6.0 Hz, 2H), 1.98 (t, J=2.7 Hz, 1H), 1.41 (s, 9H).

Step 2—Tert-butyl N-but-3-ynyl-N-methyl-carbamate

To a solution of tert-butyl N-but-3-ynylcarbamate (1.00 g, 5.91 mmol) in THF (20 mL) was added NaH (354 mg, 8.86 mmol, 60% oil dispersion) at 0° C. The reaction mixture was stirred at 0° C. for 0.5 hour, then MeI (1.26 g, 8.86 mmol) was added. The reaction mixture was stirred at 25° C. for 12 hours. On completion, the reaction mixture was quenched with sat. NH$_4$Cl (30 mL) and extracted with EA (2×100 mL). The combined organic layers were washed with brine (50 mL), dried with anhydrous Na$_2$SO$_4$ and filtered. The filtrate was concentrated in vacuo. The residue was purified by column chromatography to give the title compound (1.00 g, 92% yield) as colorless oil. $^1$H NMR (300 MHz, CDCl$_3$) δ 3.43-3.28 (m, 2H), 2.87 (s, 3H), 2.44-2.33 (m, 2H), 1.95 (t, J=2.4 Hz, 1H), 1.44 (s, 9H).

3-[3-Methyl-4-[4-(methylamino)butyl]-2-oxo-benzimidazol-1-yl]piperidine-2,6-dione (Intermediate YD)

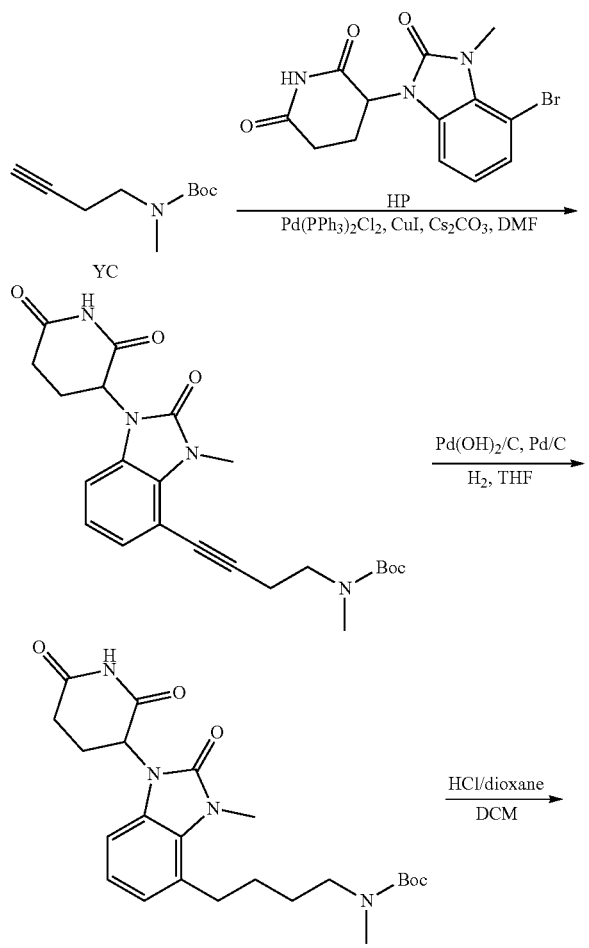

Step 1—Tert-butyl N-[4-[1-(2,6-dioxo-3-piperidyl)-3-methyl-2-oxo-benzimidazol-4-yl]but-3-ynyl]-N-methyl-carbamate To a solution of 3-(4-bromo-3-methyl-2-oxo-benzimidazol-1-yl)piperidine-2,6-dione (500 mg, 1.48 mmol, Intermediate HP) and 4 Å molecular sieves (50 mg) in DMF (5 mL) was added Pd(PPh$_3$)$_2$Cl$_2$ (103 mg, 147 umol), CuI (56.3 mg, 295 umol) and Cs$_2$CO$_3$ (1.93 g, 5.91 mmol). The reaction mixture was degassed with N$_2$ for three times. Then tert-butyl N-but-3-ynyl-N-methyl-carbamate (487 mg, 2.66 mmol, Intermediate YC) was added. The reaction mixture was stirred at 85° C. for 2 hours. On completion, the reaction mixture was filtered. The organic layer was diluted with EA (300 mL), washed with sat.NH$_4$Cl (2×100 mL) and brine (100 mL), dried with anhydrous Na$_2$SO$_4$ and filtered. The filtrate was concentrated in vacuo. The residue was purified by reverse phase flash (0.1%, FA) to give the title compound (400 mg, 61% yield) as a light yellow solid, LC-MS (ESI$^+$) m/z 463.1 (M+Na)$^+$.

Step 2—Tert-butyl N-[4-[1-(2,6-dioxo-3-piperidyl)-3-methyl-2-oxo-benzimidazol-4-yl]butyl]-N-methyl-carbamate To a solution of tert-butyl N-[4-[1-(2,6-dioxo-3-piperidyl)-3-methyl-2-oxo-benzimidazol-4-yl]but-3-ynyl]-N-methyl-carbamate (400 mg, 908 umol) in THF (25 mL) was added Pd/C (200 mg, 10 wt %) and Pd(OH)$_2$/C (1.28 g, 10 wt %). The reaction mixture was stirred at 25° C. under H$_2$ (15 psi) for 12 hours. On completion, the reaction mixture was filtered and concentrated in vacuo to give the title compound (400 mg, 99% yield) as a white solid, $^1$H NMR (400 MHz, DMSO-d$_6$) δ 11.08 (s, 1H), 6.99-6.93 (m, 2H), 6.89-6.84 (m, 1H), 5.40-5.32 (m, 1H), 3.55 (s, 3H), 3.24-3.14 (m, 2H), 2.99-2.82 (m, 3H), 2.75 (s, 3H), 2.72-2.59 (m, 2H), 2.04-1.94 (m, 1H), 1.63-1.48 (m, 4H), 1.36 (s, 9H).

Step 3—3-[3-Methyl-4-[4-(methylamino)butyl]-2-oxo-benzimidazol-1-yl]piperidine-2,6-dione

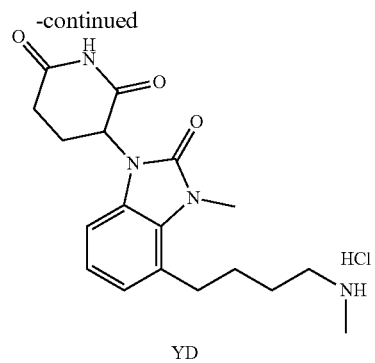

To a solution of tert-butyl N-[4-[1-(2,6-dioxo-3-piperidyl)-3-methyl-2-oxo-benzimidazol-4-yl]butyl]-N-methyl-carbamate (390 mg, 877 umol) in DCM (15 mL) was added HCl/dioxane (4 M, 15 mL). The reaction mixture was stirred at 25° C. for 1 hour. On completion, the reaction mixture was concentrated in vacuo to give the title compound (300 mg, 89% yield, HCl) as a white solid. LC-MS (ESI$^+$) m/z 345.2 (M+H)$^+$.

2-[2-[Tert-butoxycarbonyl(methyl)amino]-4-pyridyl]oxazole-4-carboxylic acid (Intermediate YE)

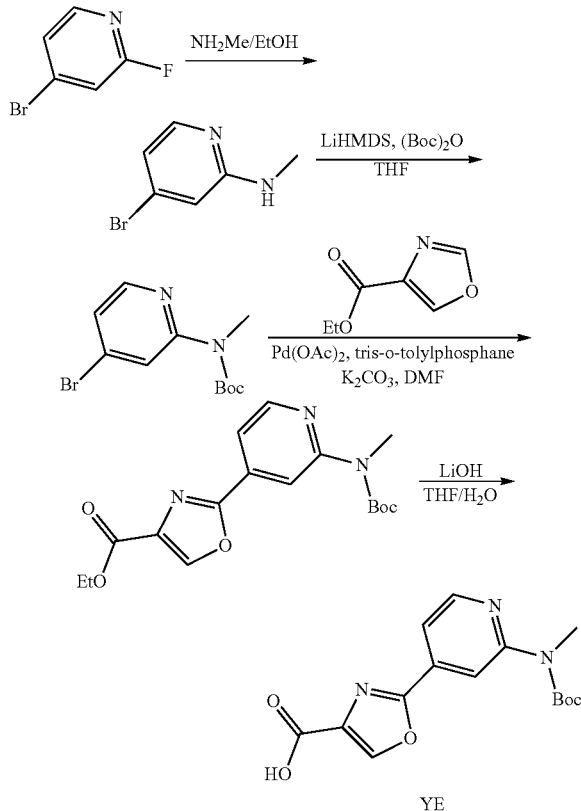

Step 1—4-Bromo-N-methyl-pyridin-2-amine

To a solution of 4-bromo-2-fluoro-pyridine (5.00 g, 28.4 mmol, CAS #128071-98-7) in THF (50.0 mL) was added a solution of MeNH₂ in EtOH (2.00 M, 42.6 mL). The mixture was stirred at 120° C. for 2 hrs under seal tube. The mixture was concentrated in vacuo. The mixture was purified by silica gel column (PE:EA=80:1) to give the title compound (4.50 g, 84% yield) as white solid. ¹H NMR (400 MHz, DMSO-d₆) δ 7.87-7.84 (m, 1H), 6.75-6.74 (m, 1H), 6.66-6.65 (m, 1H), 6.64 (s, 1H), 2.75 (s, 3H).

Step 2—Tert-butyl N-(4-bromo-2-pyridyl)-N-methyl-carbamate

To a solution of 4-bromo-N-methyl-pyridin-2-amine (4.00 g, 21.4 mmol) in THF (30.0 mL) was added LiHMDS (1.00 M, 47.1 mL) dropwise at −5° C. Then a solution of (Boc)₂O (4.67 g, 21.4 mmol, 4.91 mL) in THF (10.0 mL) was added into the above mixture slowly. The reaction mixture was stirred at −5° C. for 10 minutes, then heated to 20° C. and stirred for 1 hr. The reaction mixture was quenched with sat. NH₄Cl (100 ml), extracted with EA (2×50 mL), then concentrated in vacuo to give a residue. The residue was purified by silica gel column chromatography (PE:EA=100:1-8:1) to give the title compound (5.00 g, 81% yield) as a yellow liquid. ¹H NMR (400 MHz, DMSO-d₆) δ 8.16 (d, J=5.6 Hz, 1H), 8.02-8.01 (m, 1H), 7.13 (dd, J=5.2 Hz, J=5.6 Hz, 1H), 3.39 (s, 3H), 1.53 (s, 9H).

Step 3—Ethyl 2-[2-[tert-butoxycarbonyl(methyl)amino]-4-pyridyl]oxazole-4-carboxylate A mixture of tert-butyl N-(4-bromo-2-pyridyl)-N-methyl-carbamate (4.00 g, 13.9 mmol), ethyl oxazole-4-carboxylate (1.97 g, 13.9 mmo, CAS #170487-38-4), Pd(OAc)₂ (313 mg, 1.39 mmol), tris-o-tolylphosphane (848 mg, 2.79 mmol) and K₂CO₃ (5.78 g, 41.8 mmol) in DMF (60.0 mL) was degassed and purged with N₂ three times, and then the mixture was stirred at 70° C. for 16 hrs under N₂ atmosphere. On completion, the reaction mixture was diluted by addition H₂O (30 mL) and extracted with EA (3×50 mL). The combined organic layers were washed with saturated NaCl (2×100 mL), dried over Na₂SO₄, filtered and concentrated in vacuo to give a residue. The crude product was purified by reverse phase (0.1% FA condition) to give the title compound (2.20 g, 45% yield) as a white solid. ¹H NMR (400 MHz, CDCl₃) δ 8.49 (d, J=6.8 Hz, 1H), 8.42 (s, 1H), 8.33 (s, 1H), 7.71-7.69 (m, 1H), 4.47-4.41 (m, 2H), 3.45 (s, 3H), 1.56 (s, 9H), 1.42 (t, J=13.2 Hz, 3H).

Step 4—2-[2-[Tert-butoxycarbonyl(methyl)amino]-4-pyridyl]oxazole-4-carboxylic acid To a solution of ethyl 2-[2-[tert-butoxycarbonyl(methyl)amino]-4-pyridyl]oxazole-4-carboxylate (200 mg, 575 umol) in THF (10.0 mL) and H₂O (2.00 mL) was added LiOH (68.9 mg, 2.88 mmol). The mixture was stirred at 20° C. for 15 hrs. On completion, the reaction mixture was quenched with water (1 mL), and the mixture was acidified with 1N HCl solution until the pH=5. The aqueous phase was extracted with EA (3×10 mL). The combined organic layer was washed with brine (2×10 mL), dried with anhydrous Na₂SO₄, filtered and concentrated in vacuo to give the title compound (160 mg, 87% yield) as an off-white solid. ¹H NMR (400 MHz, DMSO-d₆) δ 8.96 (s, 1H), 8.57 (d, J=5.2 Hz, 1H), 8.35 (s, 1H), 7.65 (dd, J₁=4.8 Hz, J=5.2 Hz, 1H), 3.37 (s, 3H), 1.52 (s, 9H).

Tert-butyl 3-prop-2-ynoxypyrrolidine-1-carboxylate (Intermediate YG)

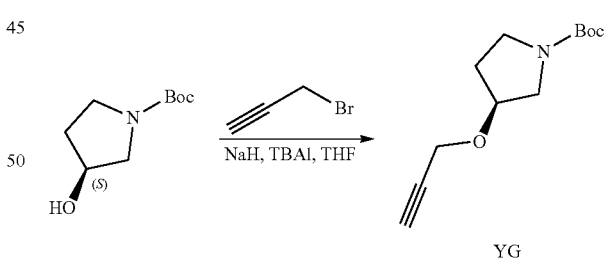

To a solution of tert-butyl (3S)-3-hydroxypyrrolidine-1-carboxylate (5.00 g, 26.7 mmol, CAS #101469-92-5) in THF (150 mL) was added NaH (1.60 g, 40.0 mmol, 60% oil dispersion) at 0° C. The reaction mixture was stirred at 0° C. for 30 minutes. Then TBAI (986 mg, 2.67 mmol) and 3-bromoprop-1-yne (4.37 g, 29.3 mmol, CAS #106-96-7) was added. The reaction mixture was stirred at 25° C. for 12 hours. On completion, the reaction mixture was diluted with EA (300 mL) and quenched with sat. NH₄Cl (100 mL). The organic layer was washed with water (2×30 mL) and brine (50 mL). The organic layer was dried with anhydrous Na₂SO₄ and filtered. The filtrate was concentrated in vacuo.

The residue was purified by silica column chromatography to give the title compound (5.90 g, 98% yield) as light yellow oil, ¹H NMR (300 MHz, CDCl3) δ 4.29-4.21 (m, 1H), 4.17-4.10 (m, 2H), 3.51-3.32 (m, 4H), 2.50-2.34 (s, 1H), 2.02-1.90 (m, 2H), 1.43 (s, 9H).

3-[3-Methyl-2-oxo-4-[3-[(3S)-pyrrolidin-3-yl]oxypropyl]benzimidazol-1-yl]piperidine-2,6-dione (Intermediate YH)

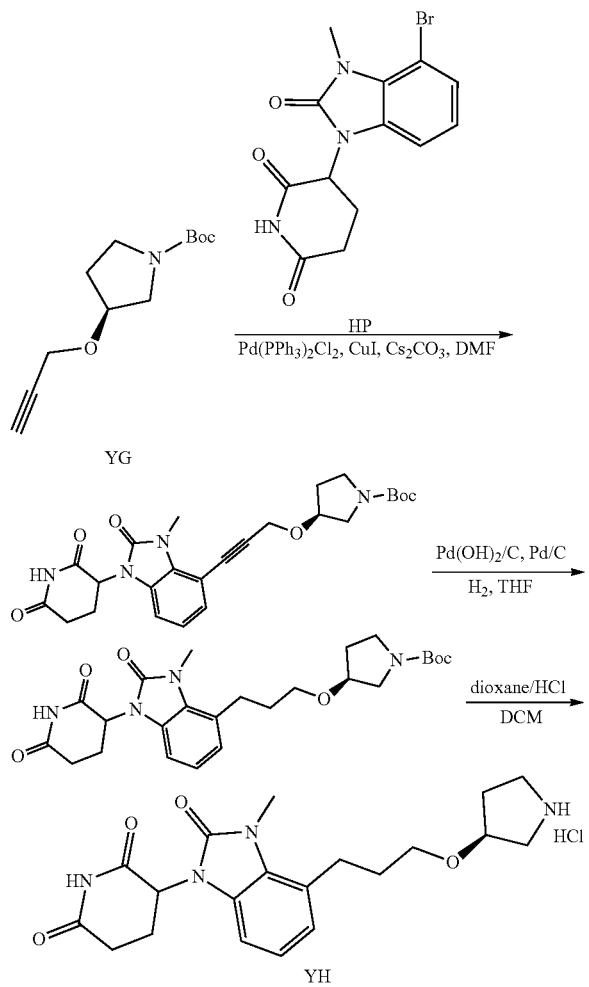

Step 1—Tert-butyl (3S)-3-[3-[1-(2,6-dioxo-3-piperidyl)-3-methyl-2-oxo-benzimidazol-4-yl]prop-2-ynoxy]pyrrolidine-1-carboxylate To a solution of 3-(4-bromo-3-methyl-2-oxo-benzimidazol-1-yl)piperidine-2,6-dione (600 mg, 1.77 mmol, Intermediate HP) in DMF (10 mL) was added Pd(PPh₃)₂Cl₂ (124 mg, 177 umol), CuI (33.7 mg, 177 umol) and Cs₂CO₃ (2.31 g, 7.08 mmol). The reaction mixture was degassed with N₂ three times. Then tert-butyl 3-prop-2-ynoxypyrrolidine-1-carboxylate (598 mg, 2.66 mmol, Intermediate YG) was added. The reaction mixture was stirred at 80° C. for 8 hours. On completion, the reaction mixture was filtered. The filtrate was concentrated in vacuo. The residue was purified by reversed-phase flash (FA, 0.1%) to give the title compound (450 mg, 52% yield) as a yellow solid, ¹H NMR (400 MHz, DMSO-d₆) δ 11.13 (s, 1H), 7.19-7.10 (m, 2H), 7.04 (d, J=8.0 Hz, 1H), 5.44-5.34 (m, 1H), 4.48 (s, 2H), 4.32-4.25 (m, 1H), 3.63 (s, 3H), 3.29-3.07 (m, 4H), 2.94-2.82 (m, 1H), 2.77-2.62 (m, 2H), 2.56-2.52 (m, 1H), 2.04-1.92 (m, 3H), 1.38 (d, J=9.2 Hz, 9H).

Step 2—Tert-butyl (3S)-3-[3-[1-(2,6-dioxo-3-piperidyl)-3-methyl-2-oxo-benzimidazol-4-yl]propoxy]pyrrolidine-1-carboxylate To a solution of tert-butyl (3S)-3-[3-[1-(2,6-dioxo-3-piperidyl)-3-methyl-2-oxo-benzimidazol-4-yl]prop-2-ynoxy]pyrrolidine-1-carboxylate (400 mg, 828 umol) in THF (25 mL) was added Pd/C (200 mg, 10 wt %) and Pd(OH)₂/C (200 mg, 10 wt %). The reaction mixture was stirred at 25° C. for 12 hours under H₂ (15 psi). On completion, the reaction mixture was filtered and concentrated in vacuo to give the title compound (400 mg, 99% yield) as a yellow solid. ¹H NMR (400 MHz, DMSO-d₆) δ 11.08 (s, 1H), 6.98-6.94 (m, 2H), 6.88-6.84 (m, 1H), 5.39-5.31 (m, 1H), 4.05-4.00 (m, 1H), 3.55 (s, 3H), 3.47-3.39 (m, 2H), 3.30-3.22 (m, 4H), 2.96-2.84 (m, 3H), 2.76-2.60 (m, 2H), 2.55-2.52 (m, 2H), 2.02-1.96 (m, 1H), 1.93-1.87 (m, 2H), 1.84-1.78 (m, 2H), 1.40 (s, 10H).

Step 3—3-[3-Methyl-2-oxo-4-[3-[(3S)-pyrrolidin-3-yl]oxypropyl]benzimidazol-1-yl]piperidine-2,6-dione To a solution of tert-butyl (3S)-3-[3-[1-(2,6-dioxo-3-piperidyl)-3-methyl-2-oxo-benzimidazol-4-yl]propoxy]pyrrolidine-1-carboxylate (395 mg, 811 umol) in DCM (15 mL) was added HCl/dioxane (4 M, 15 mL). The reaction mixture was stirred at 25° C. for 1 hour. On completion, the reaction mixture was concentrated in vacuo to give the title compound (300 mg, 87% yield, HCl) as a white solid. LC-MS (ESI⁺) m/z 387.2 (M+H)⁺.

[3-Methyl-4-[[4-(methylaminomethyl)-1-piperidyl]methyl]-2-oxo-benzimidazol-1-yl]piperidine-2,6-dione (Intermediate YI)

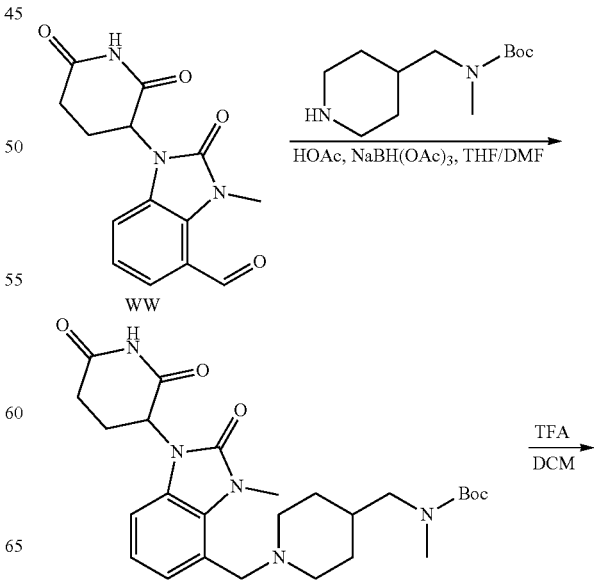

-continued

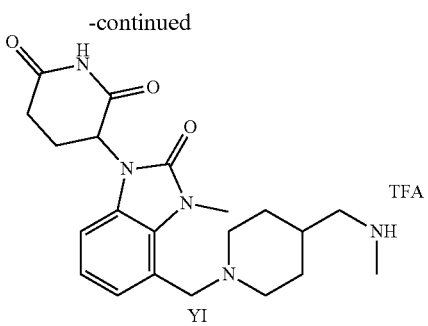

YI

Step 1—Tert-butyl N-[[1-[[1-(2,6-dioxo-3-piperidyl)-3-methyl-2-oxo-benzimidazol-4-yl]methyl]-4-piperidyl]methyl]-N-methyl-carbamate To a solution of 1-(2,6-dioxo-3-piperidyl)-3-methyl-2-oxo-benzimidazole-4-carbaldehyde (150 mg, 522 umol, Intermediate WW) and tert-butyl N-methyl-N-(4-piperidylmethyl)carbamate (119 mg, 522 umol, CAS #138022-04-5) in THF (2 mL) and DMF (0.5 mL) was added HOAc (31.4 mg, 522 umol) at 25° C. The mixture was stirred for 0.5 hour, then NaBH(OAc)$_3$ (221 mg, 1.04 mmol) was added. The mixture was stirred at 25° C. for 2 hours. On completion, the mixture was quenched by water (0.2 mL), and concentrated in vacuo to give a residue. The residue was purified by reverse phase (0.1% FA condition) to give the title compound (180 mg, 69% yield) as a white solid. $^1$H NMR (400 MHz, CDCl$_3$) δ 8.48 (s, 1H), 8.24 (s, 1H), 7.08-6.97 (m, 2H), 6.85-6.72 (m, 1H), 5.28-5.22 (m, 1H), 3.78 (d, J=5.0 Hz, 5H), 3.68-3.51 (m, 2H), 3.10 (s, 2H), 3.04-2.94 (m, 2H), 2.94-2.90 (m, 2H), 2.86 (s, 4H), 2.81-2.72 (m, 1H), 2.27-2.20 (m, 1H), 1.71-1.62 (m, 2H), 1.46 (s, 9H), 1.39-1.21 (m, 2H); LC-MS (ESI$^+$) m/z 500.4 (M+H)$^+$.

Step 2—[3-Methyl-4-[[4-(methylaminomethyl)-1-piperidyl]methyl]-2-oxo-benzimidazol-1-yl]piperidine 2,6-dione To a mixture of tert-butyl N-[[1-[[1-(2,6-dioxo-3-piperidyl)-3-methyl-2-oxo-benzimidazol-4-yl]methyl]-4-piperidyl]methyl]-N-methyl-carbamate (106 mg, 212 umol) in DCM (2 mL) was added TFA (483 mg, 4.24 mmol) at 25° C. The mixture was stirred at 25° C. for 2 hours. On completion, the reaction mixture was concentrated in vacuo give the title compound (108 mg, 99% yield, TFA). LC-MS (ESI+) m/z 399.9 (M+H)$^+$.

3-[3-Methyl-4-[[(2S)-2-(methylaminomethyl)morpholin-4-yl]methyl]-2-oxo-benzimidazol-1-yl]piperidine-2,6-dione (Intermediate YJ)

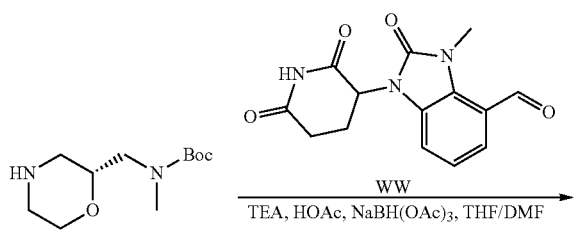

WW
TEA, HOAc, NaBH(OAc)$_3$, THF/DMF

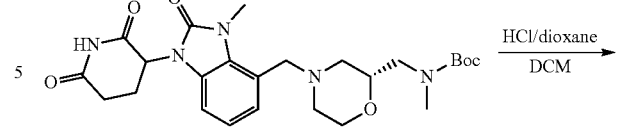

HCl/dioxane
DCM

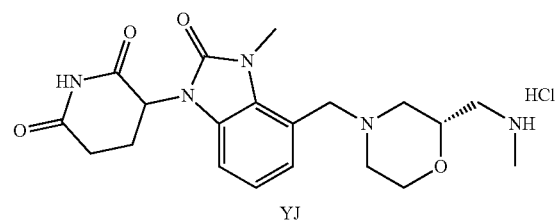

YJ

Step 1—Tert-butyl-N-[[(2R)-4-[[1-(2,6-dioxo-3-piperidyl)-3-methyl-2-oxo-benzimidazol-4-yl]methyl]morpholin-2-yl]methyl]-N-methyl-carbamate To a solution of tert-butyl N-methyl-N-[[(2R)-morpholin-2-yl]methyl]carbamate (158 mg, 689 umol, synthesized via Steps 1-5 of Intermediate WP), 1-(2,6-dioxo-3-piperidyl)-3-methyl-2-oxo-benzimidazole-4-carbaldehyde (180 mg, 626 umol, Intermediate WW) in DMF (3.00 mL) and THF (10.0 mL) was added HOAc (75.2 mg, 1.25 mmol). The mixture was stirred at 20° C. for 0.5 hr, then NaBH(OAc)$_3$ (265 mg, 1.25 mmol) was added, and the mixture was stirred at 20° C. for 14 hrs. On completion, the reaction mixture was quenched with H$_2$O (3 mL) at 20° C., and extracted with EA 60 mL (3×20 mL). The combined organic layers were washed with brine (2×10 mL), dried over Na$_2$SO$_4$, filtered and concentrated in vacuo to give a residue. The residue was purified by reversed-phase HPLC (0.1% FA condition) to give the title compound (215 mg, 68% yield) as a white solid. $^1$H NMR (400 MHz, CDCl$_3$) δ 8.07 (s, 1H), 6.88-6.86 (m, 1H), 6.82-6.80 (m, 1H), 6.69 (d, J=7.6 Hz, 1H), 5.19-5.07 (m, 1H), 3.79-3.72 (m, 1H), 3.72-3.71 (m, 3H), 3.57 (s, 2H), 3.53-3.47 (m, 2H), 3.39-3.36 (m, 2H), 2.87 (s, 2H), 2.83 (s, 3H), 2.73-2.72 (m, 1H), 2.63-2.54 (m, 2H), 2.19-2.12 (m, 2H), 1.87-1.80 (m, 1H), 1.36 (s, 9H).

Step 2—3-[3-Methyl-4-[[(2S)-2-(methylaminomethyl)morpholin-4-yl]methyl]-2-oxo-benzimidazol-1-yl]piperidine-2,6-dione To a solution of tert-butyl N-[[(2R)-4-[[1-(2,6-dioxo-3-piperidyl)-3-methyl-2-oxo-benzimidazol-4-yl]methyl]morpholin-2-yl]methyl]-N-methyl-carbamate (100 mg, 199 umol) in DCM (3.00 mL) was added HCl/dioxane (4.00 M, 5.00 mL). The mixture was stirred at 20° C. for 1 hr. On completion, the reaction mixture was concentrated in vacuo to give the title compound (87.0 mg, quant. crude yield, HCl) as yellow solid. LC-MS (ESI$^+$) m/z 401.2 (M+H)$^+$.

2043

3-[3-Methyl-4-[[(2R)-2-(methylaminomethyl)morpholin-4-yl]methyl]-2-oxo-benzimidazol-1-yl]piperidine-2,6-dione (Intermediate YK)

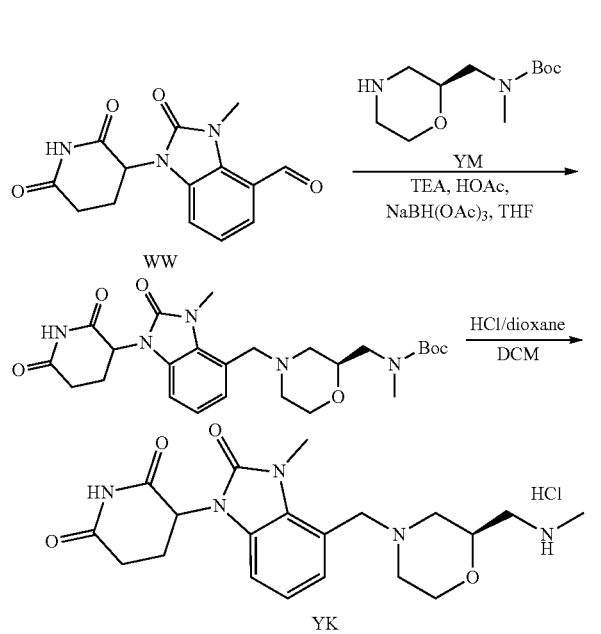

Step 1—N-[[(2S)-4-[[1-(2,6-dioxo-3-piperidyl)-3-methyl-2-oxo-benzimidazol-4-yl]methyl]morpholin-2-yl]methyl]-N-methyl-carbamate To a solution of 1-(2,6-dioxo-3-piperidyl)-3-methyl-2-oxo-benzimidazole-4-carbaldehyde (249 mg, 868 umol, Intermediate WW) and tert-butyl N-methyl-N-[[(2S)-morpholin-2-yl]methyl]carbamate (200 mg, 868 umol, Intermediate YM) in THF (15 mL) was added TEA (87.8 mg, 868 umol). The reaction mixture was stirred at 25° C. for 15 minutes. Then AcOH (156 mg, 2.61 mmol) and NaBH(OAc)$_3$ (552 mg, 2.61 mmol) was added. The reaction mixture was stirred at 25° C. for 12 hours. On completion, the reaction was quenched with water (3 mL) and the reaction mixture was concentrated in vacuo. The residue was purified by reverse phase (0.1% FA) to give the title compound (250 mg, 57% yield) as a white solid. LC-MS (ESI$^+$) m/z 502.1 (M+H)$^+$.

Step 2—3-[3-Methyl-4-[[(2R)-2-(methylaminomethyl)morpholin-4-yl]methyl]-2-oxo-benzimidazol-1-yl]piperidine-2,6-dione To a solution of tert-butyl N-[[(2S)-4-[[1-(2,6-dioxo-3-piperidyl)-3-methyl-2-oxo-benzimidazol-4-yl]methyl]morpholin-2-yl]methyl]-N-methyl-carbamate (100 mg, 199 umol) in DCM (1 mL) was added HCl/dioxane (4 M, 20.0 mL). The reaction mixture was stirred at 25° C. for 30 minutes. On completely, the reaction mixture was concentrated in vacuo to give the title compound (80.0 mg, 91% yield, HCl) as a white solid. LC-MS (ESI$^+$) m/z 402.1 (M+H)$^+$.

2044

3-[3-Methyl-2-oxo-4-[2-(4-piperidyl)ethynyl]benzimidazol-yl]piperidine-2,6-dione (Intermediate YL)

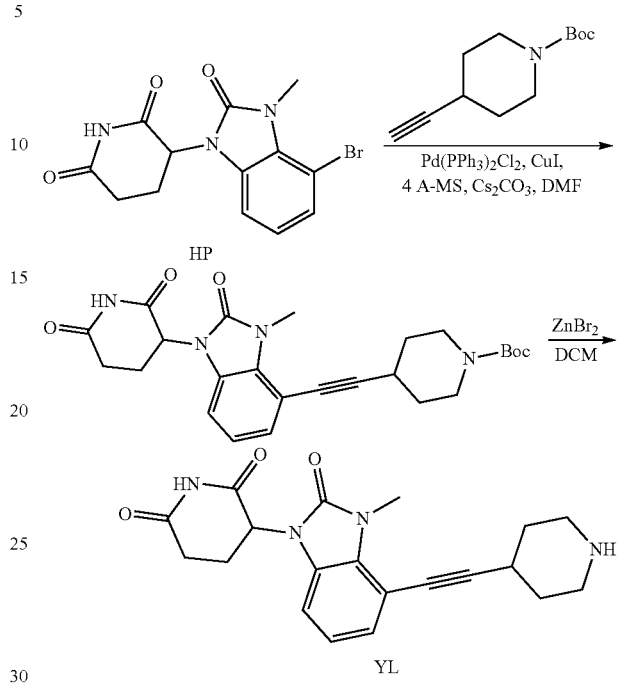

Step 1—Tert-butyl 4-[2-[1-(2,6-dioxo-3-piperidyl)-3-methyl-2-oxo-benzimidazol-4-yl]ethynyl]piperidine-1-carboxylate To a solution of 3-(4-bromo-3-methyl-2-oxobenzimidazol-1-yl)piperidine-2,6-dione (400 mg, 1.18 mmol, Intermediate HP), and tert-butyl 4-ethynylpiperidine-1-carboxylate (446 mg, 2.13 mmol, CAS #287192-97-6) in DMF (5.00 mL) was added Cs$_2$CO$_3$ (1.93 g, 5.91 mmol), 4 Å molecular sieves (100 mg), Pd(PPh$_3$)$_2$Cl$_2$ (83.0 mg, 118 umol) and CuI (22.5 mg, 118 umol). The mixture was stirred at 80° C. for 2 hrs under N$_2$. On completion, the reaction mixture was filtered and the filter cake was washed with ACN (10 mL). The filtrate was concentrated in vacuo to give a residue. The residue was purified by reverse phase (0.1% FA condition) to give the title compound (330 mg, 707 umol, 60% yield) as yellow solid. $^1$H NMR (400 MHz, DMSO-d) δ 11.11 (s, 1H), 7.13-7.11 (m, 1H), 7.07-7.05 (m, 1H), 7.01-6.97 (m, 1H), 5.40-5.36 (m, 1H), 3.72-3.66 (m, 2H), 3.63 (s, 3H), 3.12-3.07 (m, 2H), 2.93-2.87 (m, 2H), 2.75-2.68 (m, 1H), 2.65-2.60 (m, 1H), 2.04-1.99 (m, 1H), 1.88-1.85 (m, 2H), 1.8-1.50 (m, 2H), 1.40 (s, 9H).

Step 2—3-[3-Methyl-2-oxo-4-[2-(4-piperidyl)ethynyl]benzimidazol-1-yl]piperidine-2,6-dione To a solution of tert-butyl 4-[2-[1-(2,6-dioxo-3-piperidyl)-3-methyl-2-oxo-benzimidazol-4-yl]ethynyl]piperidine-1-carboxylate (300 mg, 643 umol) in DCM (3.00 mL) was added ZnBr$_2$ (2.17 g, 9.65 mmol). The mixture was stirred at 20° C. for 20 hrs. On completion, the reaction mixture was concentrated in vacuo to give the title compound (235 mg, 99% yield) as yellow gum. LC-MS (ESI$^+$) m/z 367.2 (M+H)$^+$.

2045

Tert-butyl N-methyl-N-[[(2S)-morpholin-2-yl]methyl]carbamate (Intermediate YM)

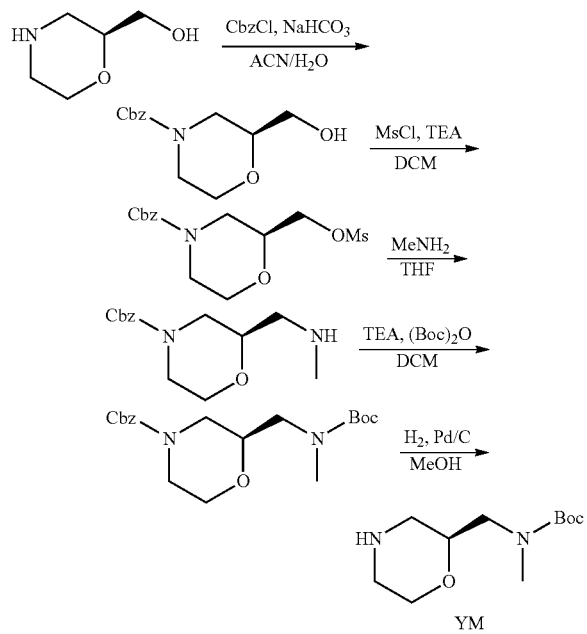

Step 1—Benzyl (2S)-2-(hydroxymethyl)morpholine-4-carboxylate

To a solution of [(2S)-morpholin-2-yl]methanol (5 g, 32.5 mmol, HCl; CAS #132073-83-7) and NaHCO$_3$ (6.84 g, 81.4 mmol) in a mixed solvent of ACN (10 mL) and H$_2$O (10 mL) was added CbzCl (8.33 g, 48.8 mmol). The reaction mixture was stirred at 25° C. for 12 hrs. On completion, the mixture was concentrated in vacuo to remove ACN. The residue was extracted with EA (2×20 mL), then the combined organic layers were concentrated in vacuo. The residue was purified by silica gel column (PE:EA=1:1) to give the title compound (7.1 g, 87% yield) as colorless oil. $^1$H NMR (400 MHz, CDCl$_3$) δ 7.42-7.33 (m, 5H), 5.17 (d, J=2.0 Hz, 2H), 4.08-3.88 (m, 3H), 3.77-3.65 (m, 1H), 3.63-3.46 (m, 3H), 3.13-2.73 (m, 2H), 2.07-1.96 (m, 1H). LC-MS (ESI$^+$) m/z 274.1 (M+Na)$^+$.

Step 2—Benzyl (2S)-2-(methyl sulfonyloxymethyl)morpholine-4-carboxylate

To a solution of benzyl (2S)-2-(hydroxymethyl)morpholine-4-carboxylate (7.1 g, 28.2 mmol) and triethylamine (5.72 g, 56.5 mmol) in dichloromethane (70 mL) was added methanesulfonyl chloride (4.86 g, 42.3 mmol) at 0° C. The reaction mixture was stirred at 25° C. for 1 hr. On completion, the mixture was diluted with dichloromethane (20 mL) and washed with water (3×30 mL). The organic layer was dried over anhydrous sodium sulfate, filtered and concentrated in vacuo to give the title compound (9.31 g, 100% yield) as yellow oil. $^1$H NMR (400 MHz, CDCl$_3$) δ 7.43-7.33 (m, 5H), 5.20-5.15 (m, 2H), 4.26 (d, J=4.8 Hz, 2H), 4.10-3.83 (m, 3H), 3.80-3.65 (m, 1H), 3.63-3.48 (m, 1H), 3.08 (s, 3H), 3.07-2.75 (m, 2H).

2046

Step 3—Benzyl (2R)-2-(methylaminomethyl)morpholine-4-carboxylate

A solution of benzyl (2S)-2-(methyl sulfonyloxymethyl)morpholine-4-carboxylate (9.31 g, 28.2 mmol) in EtOH (10 mL) saturated with methanamine (58.5 g, 565 mmol) was stirred under 50 Psi at 80° C. for 12 hrs in a 100 mL of autoclave. On completion, the mixture was concentrated in vacuo to give the title compound (7.47 g, 100% yield) as yellow oil, which was used for the next step without purification.

Step 4—Benzyl (2R)-2-[[tert-butoxycarbonyl(methyl)amino]methyl]morpholine-4-carboxylate To a solution of benzyl (2R)-2-(methylaminomethyl)morpholine-4-carboxylate (7.47 g, 28.2 mmol) in MeOH (100 mL) was added (Boc)$_2$O (9.25 g, 42.4 mmol, 9.74 mL) and TEA (4.29 g, 42.4 mmol). The reaction mixture was stirred at 25° C. for 12 hrs. On completion, the mixture was concentrated in vacuo. The residue was purified by silica gel column (PE:EA=5:1) to give the title compound (9.10 g, 88% yield) as yellow oil, $^1$H NMR (400 MHz, CDCl$_3$) δ 7.43-7.30 (m, 5H), 5.24-5.09 (m, 2H), 4.11-3.83 (m, 3H), 3.68-3.34 (m, 3H), 3.30-3.14 (m, 1H), 3.09-2.97 (m, 1H), 2.94 (s, 3H), 2.80-2.62 (m, 1H), 1.47 (s, 9H).

Step 5—Tert-butyl N-methyl-N-[[(2S)-morpholin-2-yl]methyl]carbamate

To a solution of benzyl (2R)-2-[[tert-butoxycarbonyl(methyl)amino]methyl]morpholine-4-carboxylate (9.1 g, 24.9 mmol) in THF (100 mL) was added Pd/C (1.00 g, 10% wt) under N$_2$ atmosphere. The suspension was degassed and purged with H$_2$ three times. The mixture was stirred under H$_2$ (15 Psi) at 25° C. for 12 hrs. On completion, the mixture was filtered and the filtrate was concentrated in vacuo to give the title compound (5.7 g, 99% yield) as colorless oil. $^1$H NMR (400 MHz, CDCl$_3$) δ 3.91-3.83 (m, 1H), 3.68-3.55 (m, 2H), 3.48-3.33 (m, 1H), 3.12 (dd, J=6.2, 14.4 Hz, 1H), 2.94 (s, 3H), 2.92-2.88 (m, 1H), 2.86 (dd, J=3.2, 10.8 Hz, 1H), 2.84-2.78 (m, 1H), 2.57 (dd, J=10.3, 12.0 Hz, 1H), 1.47 (s, 9H).

3-[4-(Aminomethyl)-3-methyl-2-oxo-benzimidazol-1-yl]piperidine-2,6-dione (Intermediate YN)

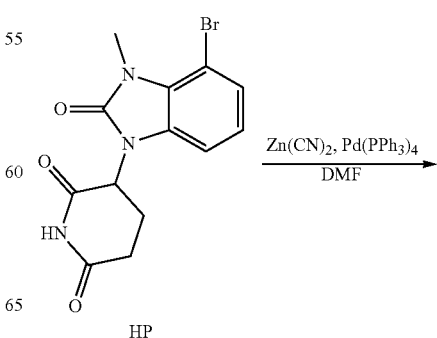

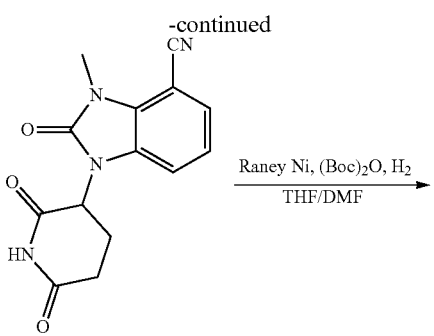

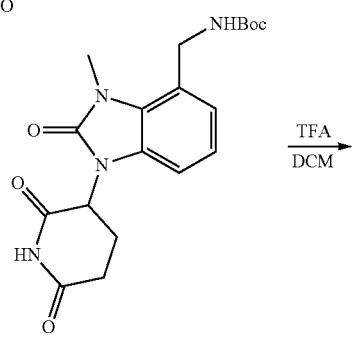

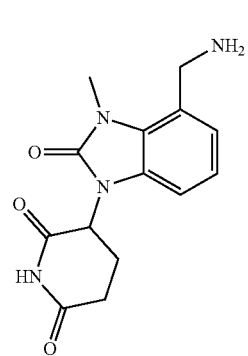

YN

Step 1—1-(2,6-Dioxo-3-piperidyl)-3-methyl-2-oxo-benzimidazole-4-carbonitrile To a solution of 3-(4-bromo-3-methyl-2-oxo-benzimidazol-1-yl)piperidine-2,6-dione (500 mg, 1.48 mmol, Intermediate HP) in DMF (10 mL) was added Zn(CN)$_2$ (190 mg, 1.62 mmol) and Pd(PPh$_3$)$_4$ (180 mg, 155 umol) at 25° C. The mixture was stirred at 100° C. for 3 hours under N$_2$. On completion, the mixture was cooled to 25° C. The mixture was filtered, and the cake was washed with EA (30 mL). The filtrate and washing were combined and concentrated in vacuo. The residue was purified by reversed phase flash (FA condition) to give the title compound (100 mg, 24% yield) as light yellow solid. $^1$H NMR (400 MHz, DMSO-d$_6$) δ 11.17 (s, 1H), 7.48 (d, J=7.6 Hz, 2H), 7.19 (t, J=8.0 Hz, 1H), 5.47-5.44 (m 1H), 3.61 (s, 3H), 2.72-2.69 (m, 1H), 2.66-2.62 (m, 2H), 2.07-2.03 (m, 1H); LC-MS (ESI$^+$) m/z 285.1 (M+H)$^+$.

Step 2—Tert-butyl N-[[1-(2,6-dioxo-3-piperidyl)-3-methyl-2-oxo-benzimidazol-4-yl]methyl]carbamate To a solution of 1-(2,6-dioxo-3-piperidyl)-3-methyl-2-oxo-benzimidazole-4-carbonitrile (100 mg, 351 umol) and Boc$_2$O (85.0 mg, 389 umol) in THF (2 mL) and DMF (2 mL) was added Raney-Ni (100 mg) at 20° C. The mixture was stirred at 30° C. for 16 hours under H$_2$ (50 Psi). On completion, the mixture was filtered, and the filter cake was washed with THF (20 mL). The filtrate and washing were combined and concentrated in vacuo to give the title compound (120 mg, 87% yield) as light yellow gum. LC-MS (ESI$^+$) m/z 411.2 (M+Na)$^+$.

Step 3—3-[4-(Aminomethyl)-3-methyl-2-oxo-benzimidazol-1-yl]piperidine-2,6-dione To a solution of tert-butyl N-[[1-(2,6-dioxo-3-piperidyl)-3-methyl-2-oxo-benzimidazol-4-yl]methyl]carbamate (120 mg, 308 umol) in DCM (2 mL) was added TFA (1 mL) at 20° C. The mixture was stirred at 20° C. for 1 hour. On completion, the mixture was concentrated in vacuo to give the title compound (120 mg, 96% yield, TFA) as light yellow solid. LC-MS (ESI$^+$) m/z 311.2 (M+Na)$^+$.

Tert-butyl N-methyl-N-(3-prop-2-ynoxycyclobutyl)carbamate (Intermediate YO)

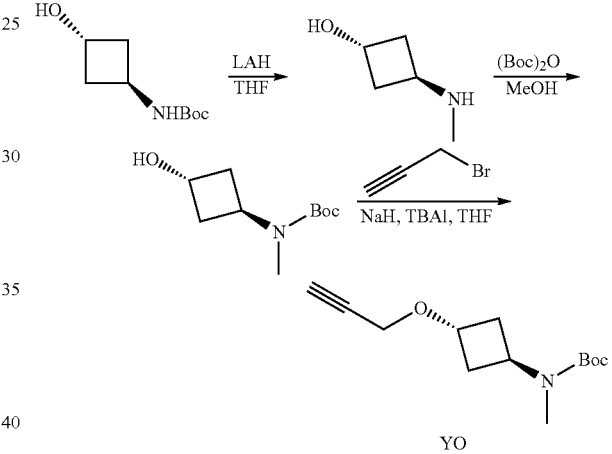

Step 1—3-(Methylamino)cyclobutanol

To a stirred solution of LAH (2.43 g, 64.1 mmol) in THF (100 mL) was added a solution of tert-butyl N-(3-hydroxycyclobutyl)carbamate (10.0 g, 53.4 mmol, CAS #389890-42-0) in THF (100 mL) at 0° C. Then the reaction mixture was stirred at 60° C. for 24 hrs. On completion, the reaction mixture was concentrated in vacuo. On completion, the mixture was cooled to 0° C., quenched with H$_2$O (2.4 mL) and added 15% NaOH (2.4 mL). After stirred for 15 minutes, H$_2$O (2.4 mL×3) was added into the above mixture. Then the mixture was warmed to rt and added anhydrous Na$_2$SO$_4$. The mixture was stirred for 10 minutes, filtered and the filtrate was concentrated in vacuo to give the title compound (4.90 g, 91% yield) as colorless oil. $^1$H NMR (400 MHz, DMSO-d$_6$) δ 5.01 (s, 1H), 4.23-4.20 (m, 1H), 3.13-3.00 (m, 1H), 2.13 (s, 3H), 1.93-1.84 (m, 4H), 1.70-1.47 (m, 1H).

Step 2—Tert-butyl N-(3-hydroxycyclobutyl)-N-methyl-carbamate

To a solution of 3-(methylamino)cyclobutanol (4.90 g, 48.4 mmol) in methyl alcohol (50 mL) was added (Boc)$_2$O (11.6 g, 53.3 mmol, 12.2 mL) for 3 hr at 25° C. Then another batch of (Boc)₂O (10.6 g, 48.4 mmol) was added. The mixture was stirred at 25° C. for another 19 hrs. On completion, the reaction mixture was concentrated in vacuo. The residue was purified by column chromatography (SiO₂, Petroleum ether/Ethyl acetate=1:1) to give the title compound (2.85 g, 30% yield) as yellow oil. ¹H NMR (DMSO-d₆) δ 4.94 (s, 1H), 4.25-4.21 (m, 1H), 4.10-4.19 (m, 1H), 2.72 (s, 3H), 2.23-2.35 (m, 2H), 1.91-2.03 (m, 2H), 1.38 (s, 9H).

Step 3—Tert-butyl N-methyl-N-(3-prop-2-ynoxycyclobutyl)carbamate

To a solution of tert-butyl N-(3-hydroxycyclobutyl)-N-methyl-carbamate (450 mg, 2.24 mmol) in THF (15 mL) was added NaH (107 mg, 2.68 mmol, 60% dispersion in oil), TBAI (82.6 mg, 223 umol) at 0° C., and the mixture was stirred for 30 minutes. Then 3-bromoprop-1-yne (3.35 mmol, 289 uL) was added to the mixture at 0° C. The reaction mixture was stirred at 10° C. for 18 hrs. On completion, the reaction mixture was quenched 30 mL sat.aq NH₄Cl at 10° C. and diluted with 30 mL water. Then the reaction mixture was then extracted with EA (3×50 mL). The combined organic layers were washed with 50 mL brine, dried over Na₂SO₄, filtered and the filtrate was concentrated in vacuo to give the title compound (500 mg, 93% yield) as yellow oil. ¹H NMR (400 MHz, CDCl₃) δ 4.68 (s, 1H), 4.27-4.19 (m, 1H), 4.08 (d, J=2.4 Hz, 2H), 2.83 (s, 3H), 2.41 (t, J=2.4 Hz, 1H), 2.38-2.26 (m, 4H), 1.46 (s, 9H).

3-[3-methyl-4-[3-[3-(methylamino)cyclobutoxy]propyl]-2-oxo-benzimidazol-1-yl]piperidine-2,6-dione (Intermediate YP)

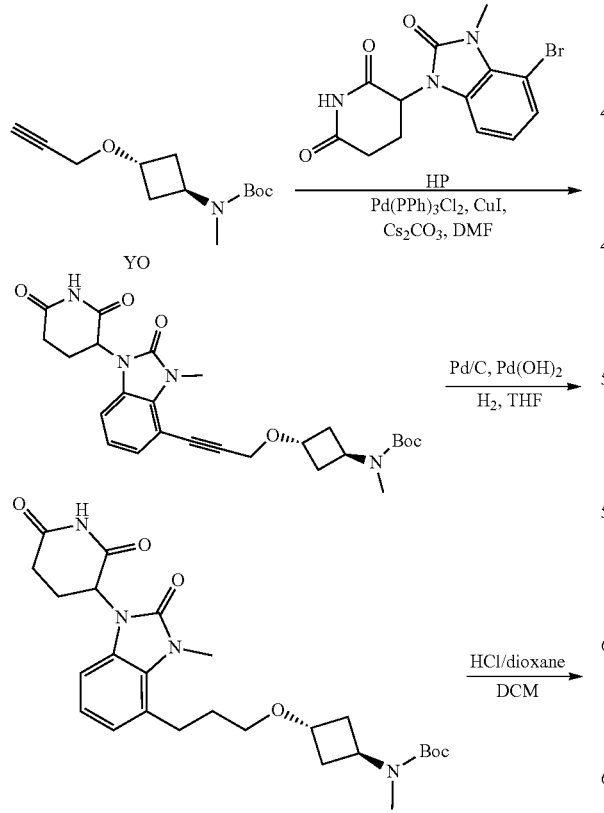

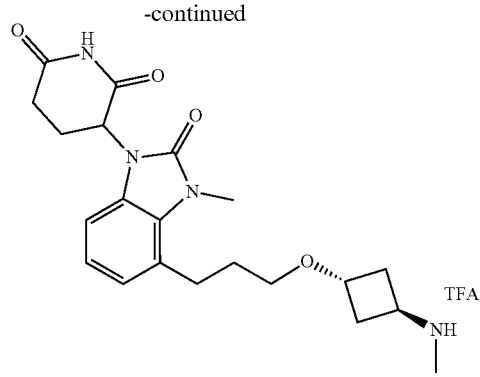

YP

Step 1—Tert-butyl N-[3-[3-[1-(2,6-dioxo-3-piperidyl)-3-methyl-2-oxo-benzimidazol-4-yl]prop-2-ynoxy]cyclobutyl]-N-methyl-carbamate To a solution of tert-butyl N-methyl-N-(3-prop-2-ynoxycyclobutyl)carbamate (500 mg, 2.09 mmol, Intermediate YO) and 3-(4-bromo-3-methyl-2-oxo-benzimidazol-1-yl)piperidine-2,6-dione (353 mg, 1.04 mmol, Intermediate HP) in DMF (15 mL) was added CuI (39.8 mg, 209 umol), Cs₂CO₃ (1.70 g, 5.22 mmol), Pd(PPh₃)₂Cl₂ (153 mg, 209 umol) and 4 Å molecular sieves (600 mg) at 25° C. The reaction mixture was stirred at 80° C. for 2 hrs. On completion, the reaction mixture was filtered and the filtrate was concentrated in vacuo to give a residue. The residue was diluted with 30 mL water, and then extracted with EA (3×30 mL). The combined organic layers were washed with brine (30 mL), and then dried over Na₂SO₄, filtered and the filtrate was concentrated in vacuo to give a residue. The residue was purified by reverse phase (0.1% FA condition) to give the title compound (380 mg, 73% yield) as a white solid. ¹H NMR (400 MHz, DMSO-d₆) δ 11.11 (s, 1H), 7.17 (d, J=7.6 Hz, 1H), 7.12 (d, J=7.6 Hz, 1H), 7.06-7.00 (m, 1H), 5.39 (dd, J=5.2, 12.8 Hz, 1H), 4.39 (s, 2H), 4.22 (t, J=6.8 Hz, 1H), 3.63 (s, 3H), 3.29 (s, 1H), 2.95-2.83 (m, 1H), 2.75 (s, 3H), 2.65-2.64 (m, 1H), 2.70-2.64 (m, 1H), 2.36-2.30 (m, 2H), 2.26-2.16 (m, 2H), 2.09-1.98 (m, 1H), 1.38 (s, 9H); LC-MS (ESI⁺) m/z 397.0 (M+H−100)⁺.

Step 2—Tert-butyl N-[3-[3-[1-(2,6-dioxo-3-piperidyl)-3-methyl-2-oxo-benzimidazol-4-yl]propoxy]cyclobutyl]-N-methyl-carbamate To a solution of tert-butyl N-[3-[3-[1-(2,6-dioxo-3-piperidyl)-3-methyl-2-oxo-benzimidazol-4-yl]prop-2-ynoxy]cyclobutyl]-N-methyl-carbamate (340 mg, 685 umol) in THF (15 mL) was added Pd(OH)₂/C (400 mg, 685 umol, 10 wt %) and Pd/C (400 mg, 685 umol, 20 wt %) at 25° C. The reaction mixture was stirred at 25° C. for 2 hrs under H₂ (15 psi). On completion, the reaction mixture was filtered with celite and the filtrate was concentrated in vacuo to give the title compound (330 mg, 96% yield) as black oil. LC-MS (ESI⁺) m/z 501.2 (M+H)⁺.

Step 3—3-[3-methyl-4-[3-[3-(methylamino)cyclobutoxy]propyl]-2-oxo-benzimidazol-1-yl]piperidine-2,6-dione To a solution of tert-butyl N-[3-[3-[1-(2,6-dioxo-3-piperidyl)-3-methyl-2-oxo-benzimidazol-4-yl]propoxy]cyclobutyl]-N-methyl-carbamate (300 mg, 599 umol) in DCM (8 mL) was added HCl/dioxane (4 M, 5 mL) at 25° C. The reaction mixture was stirred at 25° C. for 1 hr. On completion, the reaction mixture was concentrated in vacuo to give a residue. The residue was purified by reverse phase (0.1% FA condition) to give the title compound (220 mg, 91% yield) as a white solid. $^1$H NMR (400 MHz, DMSO-$d_6$) δ 11.08 (s, 1H), 9.06 (s, 1H), 6.98-6.96 (m, 1H), 6.90-6.87 (m, 1H), 5.37 (dd, J=5.2, 12.8 Hz, 1H), 4.23-4.14 (m, 1H), 3.57 (s, 3H), 3.35 (s, 3H), 3.00-2.92 (m, 3H), 2.91-2.84 (m, 1H), 2.75-2.70 (m, 1H), 2.60 (s, 2H), 2.45 (t, J=5.6 Hz, 4H), 2.27-2.17 (m, 2H), 2.03-1.95 (m, 1H), 1.88-1.77 (m, 2H); LC-MS (ESI$^+$) m/z 401.3 (M+H)$^+$.

3-[3-Methyl-4-[3-[(2S)-2-(methylaminomethyl)morpholin-4-yl]propyl]-2-oxo-benzimidazol-1-yl]piperidine-2,6-dione (Intermediate YQ)

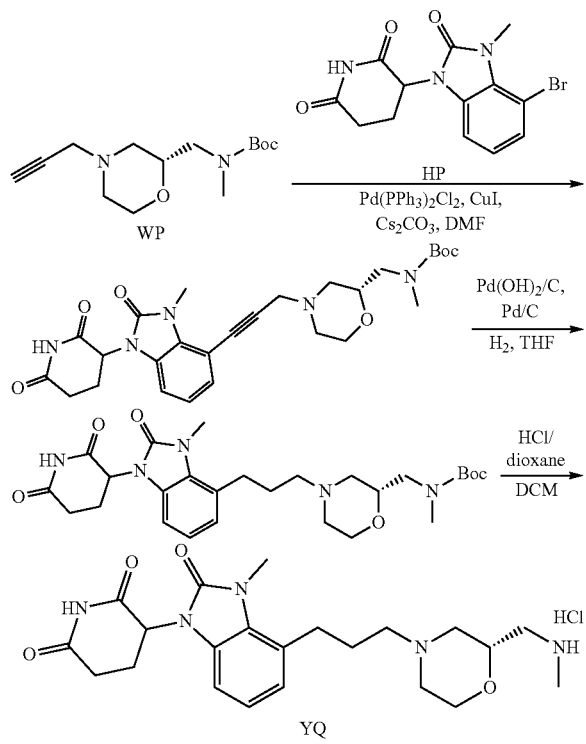

Step 1—Tert-butyl N-[[(2R)-4-[3-[1-(2,6-dioxo-3-piperidyl)-3-methyl-2-oxo-benzimidazol-4-yl]prop-2-ynyl]morpholin-2-yl]methyl]-N-methyl-carbamate To a solution of tert-butyl N-methyl-N-[[(2R)-4-prop-2-ynylmorpholin-2-yl]methyl]carbamate (400 mg, 1.49 mmol, Intermediate WP) and 3-(4-bromo-3-methyl-2-oxo-benzimidazol-1-yl)piperidine-2,6-dione (336 mg, 994 umol, Intermediate HP) in DMF (15 mL) was added Cs$_2$CO$_3$ (1.62 g, 4.97 mmol), 4 Å molecular sieves (500 mg, 994 umol), CuI (37.8 mg, 199 umol) and Pd(PPh$_3$)$_2$Cl$_2$ (139 mg, 199 umol) at 25° C. The reaction mixture was stirred at 80° C. for 2 hrs. On completion, the reaction mixture was filtered and the filtrate was concentrated in vacuo to give a residue. The residue was diluted with water 30 mL, and then extracted with EA (3×20 mL). The combined organic layers were washed with brine (20 mL), and then dried over Na$_2$SO$_4$, filtered and the filtrate was concentrated in vacuo to give a residue. The residue was purified by reverse phase (0.1% FA condition) to give the title compound (340 mg, 65% yield) as a white solid. $^1$H NMR (400 MHz, DMSO-$d_6$) δ 11.10 (s, 1H), 7.18-7.13 (m, 1H), 7.12-7.06 (m, 1H), 7.04-6.99 (m, 1H), 5.39 (dd, J=5.2, 12.4 Hz, 1H), 3.83 (d, J=9.6 Hz, 1H), 3.64 (s, 3H), 3.62-3.46 (m, 4H), 3.34 (s, 3H), 3.15 (s, 1H), 2.86-2.78 (m, 4H), 2.75-2.66 (m, 3H), 2.11-1.98 (m, 2H), 1.35 (s, 9H); LC-MS (ESI$^+$) m/z 526.3 (M+H)$^+$.

Step 2—Tert-butyl N-[[(2R)-4-[3-[1-(2,6-dioxo-3-piperidyl)-3-methyl-2-oxo-benzimidazol-4-yl]propyl]morpholin-2-yl]methyl]-N-methyl-carbamate To a solution of tert-butyl N-[[(2R)-4-[3-[1-(2,6-dioxo-3-piperidyl)-3-methyl-2-oxo-benzimidazol-4-yl]prop-2-ynyl]morpholin-2-yl]methyl]-N-methyl-carbamate (300 mg, 571 umol) in THF (20 mL) and Pd/C (200 mg, 20 wt %) was added Pd(OH)$_2$/C (200 mg, 10 wt %) at 25° C. The reaction mixture was stirred at 25° C. for 2 hrs under H$_2$ (15 psi). On completion, the reaction mixture was filtered with celite and the filtrate was concentrated in vacuo to give a residue. The residue was purified by reverse phase (0.1% FA condition) to give the title compound (130 mg, 43% yield) as a white solid. $^1$H NMR (400 MHz, DMSO-$d_6$) δ 11.10 (s, 1H), 6.99-6.91 (m, 2H), 6.89-6.83 (m, 1H), 5.36 (dd, J=5.2, 12.4 Hz, 1H), 3.77 (d, J=11.2 Hz, 1H), 3.55 (s, 3H), 3.46 (t, J=10.4 Hz, 2H), 3.22 (d, J=5.2 Hz, 1H), 3.18-3.15 (m, 1H), 2.94-2.88 (m, 2H), 2.84-2.76 (m, 3H), 2.72-2.62 (m, 4H), 2.52 (s, 3H), 2.39-2.34 (m, 1H), 2.05-1.95 (m, 2H), 1.77-1.71 (m, 2H), 1.37 (s, 9H); LC-MS (ESI$^+$) m/z 530.4 (M+H)$^+$.

Step 3—3-[3-Methyl-4-[3-[(2S)-2-(methylaminomethyl)morpholin-4-yl]propyl]-2-oxo-benzimidazol-1-yl]piperidine-2,6-dione To a solution of tert-butyl N-[[(2R)-4-[3-[1-(2,6-dioxo-3-piperidyl)-3-methyl-2-oxo-benzimidazol-4-yl]propyl]morpholin-2-yl]methyl]-N-methyl-carbamate (110 mg, 208 umol) in DCM (6 mL) was added HCl/dioxane (4 M, 3 mL) at 25° C. The reaction mixture was stirred at 25° C. for 1 hr. On completion, the reaction mixture was concentrated in vacuo to give the title compound (80.0 mg, 89% yield) as a white solid. LC-MS (ESI$^+$) m/z 430.2 (M+H)$^+$.

3-[3-Methyl-4-[3-[(2S)-2-[2-(methylamino)ethyl]morpholin-4-yl]propyl]-2-oxo-benzimidazol-1-yl]piperidine-2,6-dione (Intermediate YR)

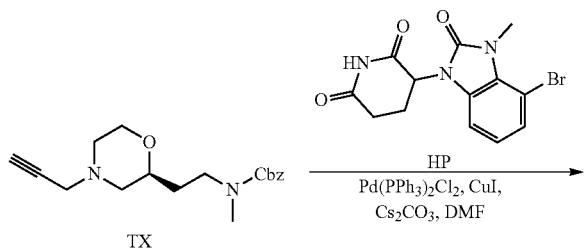

-continued

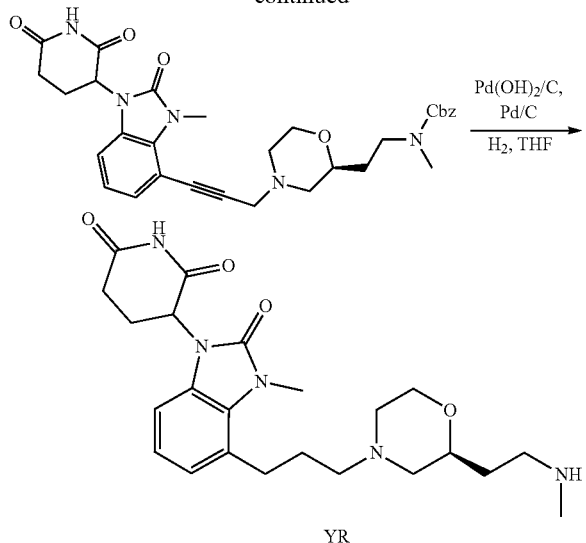

YR

Step 1—Benzyl N-[2-[(2S)-4-[3-[1-(2,6-dioxo-3-piperidyl)-3-methyl-2-oxo-benzimidazol-4-yl]prop-2-ynyl]morpholin-2-yl]ethyl]-N-methyl-carbamate To a solution of benzyl N-methyl-N-[2-[(2S)-4-prop-2-ynylmorpholin-2-yl]ethyl]carbamate (426 mg, 1.35 mmol, Intermediate TX) and 3-(4-bromo-3-methyl-2-oxo-benzimidazol-1-yl)piperidine-2,6-dione (350 mg, 1.04 mmol, Intermediate HP) in DMF (15 mL) was added Cs$_2$CO$_3$ (1.69 g, 5.18 mmol), CuI (39.4 mg, 207 umol), 4 Å molecular sieves (500 mg, 147.86 umol) and Pd(dppf)Cl$_2$ (151 mg, 207 umol) at 25° C. The reaction mixture was stirred at 80° C. for 2 hrs. On completion, the reaction mixture was filtered and the filtrate was concentrated in vacuo to give the residue. The residue was diluted with water 30 mL, and then extracted with EA (3×20 mL). The combined organic layers were washed with brine (20 mL), and then dried over Na$_2$SO$_4$, filtered and the filtrate was concentrated in vacuo to give a residue. The residue was purified by reverse phase (0.1% FA condition) to give the title compound (400 mg, 67% yield) as a white solid. $^1$H NMR (400 MHz, DMSO-d$_6$) δ 11.11 (s, 1H), 7.34 (d, J=2.0 Hz, 5H), 7.18-7.08 (m, 2H), 7.05-6.98 (m, 1H), 5.39 (dd, J=5.2, 12.8 Hz, 1H), 5.05 (s, 2H), 3.84-3.74 (m, 1H), 3.63 (s, 3H), 3.56 (s, 3H), 3.46-3.41 (m, 2H), 2.94-2.87 (m, 1H), 2.88-2.80 (m, 4H), 2.77-2.70 (m, 2H), 2.67-2.58 (m, 2H), 2.31-2.25 (m, 1H), 2.08-1.98 (m, 2H), 1.65-1.55 (m, 2H); LC-MS (ESI$^+$) m/z 574.1 (M+H)$^+$.

Step 2—3-[3-Methyl-4-[3-[(2S)-2-[2-(methylamino)ethyl]morpholin-4-yl]propyl]-2-oxo-benzimidazol-1-yl]piperidine-2,6-dione To a solution of benzyl N-[2-[(2S)-4-[3-[1-(2,6-dioxo-3-piperidyl)-3-methyl-2-oxo-benzimidazol-4-yl]prop-2-ynyl]morpholin-2-yl]ethyl]-N-methyl-carbamate (370 mg, 645 umol) in THF (15 mL) was added Pd/C (300 mg, 20 wt %) and Pd(OH)$_2$/C (300 mg, 10 wt %) at 25° C. The mixture was stirred at 25° C. for 2.5 hrs under H$_2$ (15 psi). On completion, the reaction mixture was filtered with celite and the filtrate was concentrated in vacuo to give a residue. The residue was purified by reverse phase (0.1% FA condition) to give the title compound (140 mg, 48% yield) as a brown solid. LC-MS (ESI$^+$) m/z 444.3 (M+H)$^+$.

Tert-butyl 4-(prop-2-ynoxymethyl)piperidine-1-carboxylate (Intermediate YS)

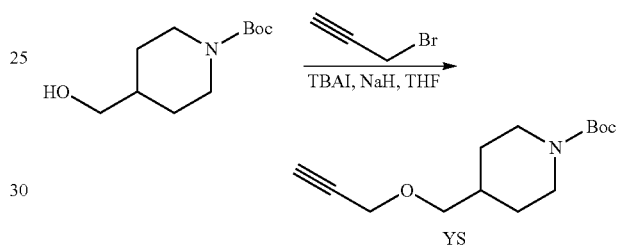

To a mixture of tert-butyl 4-(hydroxymethyl)piperidine-1-carboxylate (5.00 g, 23.2 mmol, CAS #123855-51-6) was added NaH (1.11 g, 27.8 mmol, 60% oil dispersion) at 0° C. for 0.5 hour. Then 3-bromoprop-1-yne (4.14 g, 27.8 mmol, 3.00 mL, CAS #106-96-7) and TBAI (857 mg, 2.32 mmol) was added to the mixture. The reaction mixture was stirred at 25° C. for 12 hours. On completion, the reaction mixture was quenched by addition sat. H$_2$O (10 mL), and extracted with EA (50 mL×2). The combined organic layers were dried over Na$_2$SO$_4$, filtered and concentrated in vacuo to give the title compound (5.00 g, 84% yield) as yellow oil. $^1$H NMR (400 MHz, CDCl$_3$) δ 4.12 (d, J=2.4 Hz, 2H), 3.36 (d, J=6.2 Hz, 2H), 2.69 (t, J=12.2 Hz, 2H), 2.41 (t, J=2.4 Hz, 1H), 1.81-1.74 (m, 1H), 1.73-1.67 (m, 2H), 1.45 (s, 9H), 1.15-1.10 (m, 2H).

3-[3-Methyl-2-oxo-5-[3-(4-piperidylmethoxy)propyl]benzimidazol-1-yl]piperidine-2,6-dione (Intermediate YT)

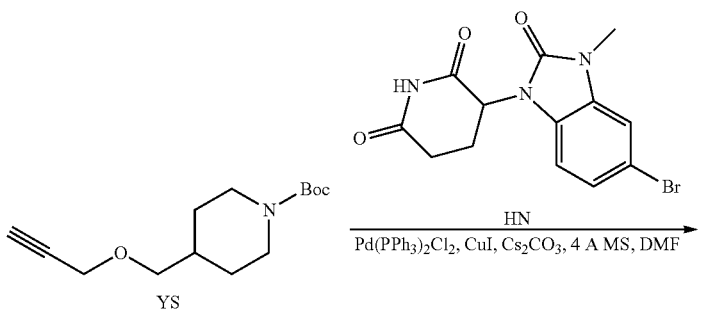

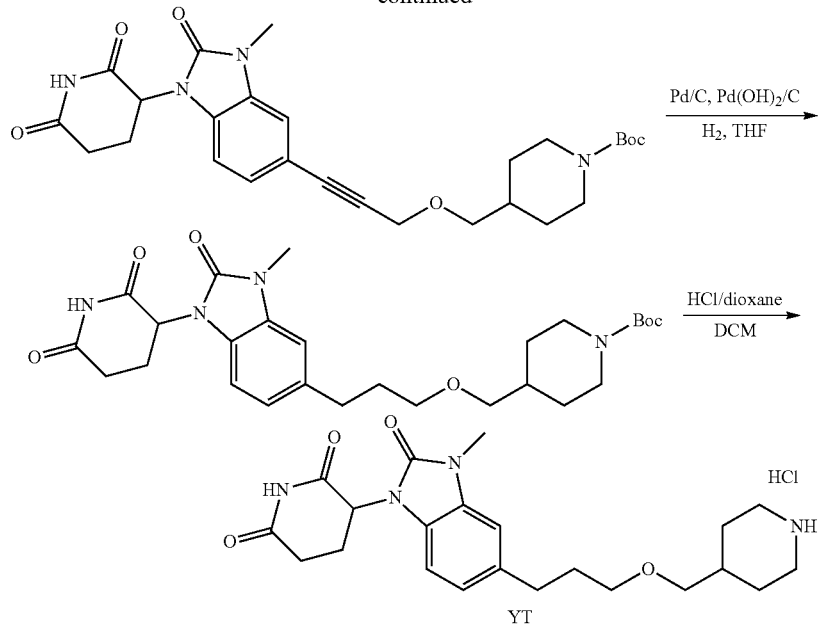

Step 1—Tert-butyl 4-[3-[1-(2,6-dioxo-3-piperidyl)-3-methyl-2-oxo-benzimidazol-5-yl]prop-2-ynoxymethyl]piperidine-1-carboxylate To a mixture of tert-butyl 4-(prop-2-ynoxymethyl)piperidine-1-carboxylate (749 mg, 2.96 mmol, Intermediate YS) and 3-(5-bromo-3-methyl-2-oxo-benzimidazol-1-yl)piperidine-2,6-dione (400 mg, 1.18 mmol, Intermediate HN) in DMF (1 mL) was added Pd(PPh$_3$)$_2$Cl$_2$ (83.0 mg, 118 umol), CuI (22.5 mg, 118 umol), Cs$_2$CO$_3$ (1.93 g, 5.91 mmol) and 4 Å molecular sieves (10.0 mg, 147 umol). The reaction mixture was stirred at 80° C. for 2 hours. On completion, the reaction mixture was filtered and concentrated in vacuo. The residue was purified by reverse phase (0.1% FA condition) to give the title compound (320 mg, 52% yield) as a yellowish solid. $^1$H NMR (400 MHz, DMSO-d$_6$) δ 11.19-11.03 (m, 1H), 7.66-7.52 (m, 1H), 7.32 (d, J=0.8 Hz, 1H), 7.16-7.13 (m, 1H), 5.39 (dd, J=12.8 Hz, 1H), 4.36 (s, 2H), 3.40 (t, J=2.4 Hz, 1H), 3.37 (d, J=6.2 Hz, 2H), 3.34 (s, 3H), 3.30-3.27 (m, 2H), 2.97-2.82 (m, 1H), 2.76-2.64 (m, 4H), 2.11-1.96 (m, 1H), 1.64 (s, 2H), 1.38 (s, 9H), 1.07-1.01 (m, 2H).

Step 2—Tert-butyl 4-[3-[1-(2,6-dioxo-3-piperidyl)-3-methyl-2-oxo-benzimidazol-5-yl]propoxymethyl]piperidine-1-carboxylate To a mixture of tert-butyl 4-[3-[1-(2,6-dioxo-3-piperidyl)-3-methyl-2-oxo-benzimidazol-5-yl]prop-2-ynoxymethyl]piperidine-1-carboxylate (320 mg, 626 umol) in THF (5 mL) was added Pd/C (100 mg, 626 umol, 10% wt) and Pd(OH)$_2$/C (100 mg, 626 umol, 10% wt). The mixture was stirred at 25° C. for 12 hours under H$_2$ (15 psi). On completion, the mixture was filtered and concentrated in vacuo to give the title compound (320 mg, 99 yield) as a white solid. $^1$H NMR (400 MHz, DMSO-d$_6$) δ 11.07 (s, 1H), 7.69-7.50 (m, 1H), 7.03-7.00 (m, 1H), 6.87-6.84 (m, 1H), 5.33 (dd, J=12.8 Hz, 1H), 3.92 (d, J=12.0 Hz, 2H), 3.38-3.34 (m, 3H), 3.31-3.27 (m, 2H), 3.20 (t, J=6.6 Hz, 4H), 1.86-1.76 (m, 2H), 1.73-1.67 (m, 1H), 1.64-1.60 (m, 2H), 1.55-1.44 (m, 2H), 1.38 (s, 9H), 1.35 (s, 2H).

Step 3—3-[3-Methyl-2-oxo-5-[3-(4-piperidylmethoxy)propyl]benzimidazol-1-yl]piperidine-2,6-dione To a mixture of tert-butyl 4-[3-[1-(2,6-dioxo-3-piperidyl)-3-methyl-2-oxo-benzimidazol-5-yl]propoxymethyl]piperidine-1-carboxylate (310 mg, 602 umol) in DCM (5 mL) was added HCl/dioxane (4 M, 4.00 mL). The reaction mixture was stirred at 25° C. for 2 hours. On completion, the reaction mixture was concentrated in vacuo to give the title compound (220 mg, 88% yield) as a white solid. $^1$H NMR (400 MHz, DMSO-d$_6$) δ 11.07 (s, 1H), 7.07-6.97 (m, 2H), 6.89-6.82 (m, 1H), 5.34 (dd, J=12.8 Hz, 1H), 3.57 (s, 4H), 3.40-3.37 (m, 2H), 3.22-3.21 (m, 2H), 2.96-2.70 (m, 6H), 2.67-2.64 (m, 2H), 1.85-1.81 (m, 2H), 1.52-1.47 (m, 1H), 1.41-1.33 (m, 4H), 0.90-0.81 (m, 1H), 0.86 (t, J=7.2 Hz, 1H).

3-[3-Methyl-2-oxo-4-[3-(4-piperidylmethoxy)propyl]benzimidazol-1-yl]piperidine-2,6-dione (Intermediate YU)

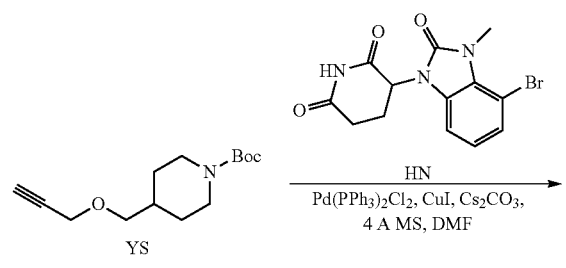

-continued

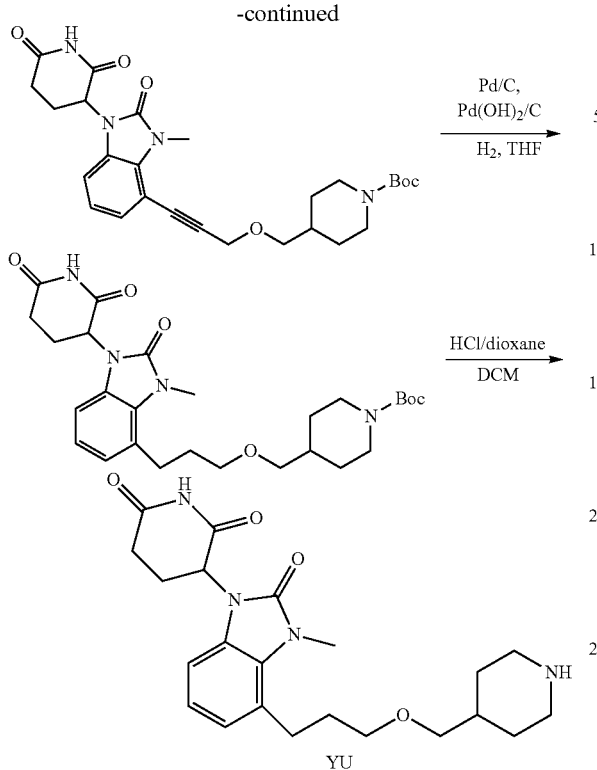

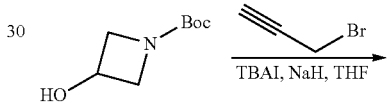

YU

Step 1—Tert-butyl 4-[3-[1-(2,6-dioxo-3-piperidyl)-3-methyl-2-oxo-benzimidazol-4-yl]prop-2-ynoxymethyl]piperidine-1-carboxylate To a mixture of tert-butyl 4-(prop-2-ynoxymethyl)piperidine-1-carboxylate (749 mg, 2.96 mmol, Intermediate YS) and 3-(4-bromo-3-methyl-2-oxo-benzimidazol-1-yl)piperidine-2,6-dione (400 mg, 1.18 mmol, Intermediate HP) in DMF (5 mL) was added CuI (22.5 mg, 118 umol), $Cs_2CO_3$ (1.93 g, 5.91 mmol), $Pd(PPh_3)_2Cl_2$ (83.0 mg, 118 umol) and 4 Å molecular sieves (20.0 mg). The reaction mixture was stirred at 80° C. for 4 hours. On completion, the reaction mixture was filtered and concentrated in vacuo. The residue was purified by reverse phase (0.1% FA condition) to give the title compound (300 mg, 49% yield) as brown solid. $^1$H NMR (400 MHz, DMSO-$d_6$) δ 11.11 (s, 1H), 7.20-7.09 (m, 2H), 7.06-7.00 (m, 1H), 5.43-5.36 (m, 1H), 4.43 (s, 2H), 4.10 (d, J=2.4 Hz, 1H), 3.93 (d, J=10.8 Hz, 2H), 3.64 (s, 3H), 3.40-3.38 (m, 2H), 3.28 (d, J=6.4 Hz, 1H), 2.95-2.83 (m, 1H), 2.70-2.65 (m, 2H), 2.06-1.99 (m, 1H), 1.81-1.70 (m, 1H), 1.67-1.60 (m, 1H), 1.38 (s, 9H), 1.08-1.01 (m, 2H).

Step 2—Tert-butyl 4-[3-[1-(2,6-dioxo-3-piperidyl)-3-methyl-2-oxo-benzimidazol-4-yl]propoxymethyl]piperidine-1-carboxylate To a mixture of tert-butyl 4-[3-[1-(2,6-dioxo-3-piperidyl)-3-methyl-2-oxo-benzimidazol-4-yl]prop-2-ynoxymethyl]piperidine-1-carboxylate (300 mg, 587 umol) in THF (30 mL) was added Pd/C (100 mg, 10 wt %) and $Pd(OH)_2/C$ (100 mg, 10 wt %). The reaction mixture was stirred at 25° C. for 12 hours under $H_2$ (15 psi) atmosphere. On completion, the reaction mixture was filtered and concentrated in vacuo to give the title compound (302 mg, 99% yield) as light yellow solid. $^1$H NMR (400 MHz, DMSO-$d_6$) δ 11.08 (s, 1H), 6.96 (d, J=4.4 Hz, 2H), 6.88-6.83 (m, 1H), 5.41-5.30 (m, 1H), 3.96-3.91 (m, 2H), 3.55 (s, 3H), 3.42 (t, J=5.6 Hz, 2H), 3.28-3.18 (m, 4H), 2.99-2.92 (m, 2H), 2.90-2.83 (m, 1H), 2.71-2.66 (m, 2H), 2.05-1.94 (m, 1H), 1.86-1.78 (m, 2H), 1.66-1.62 (m, 2H), 1.51-1.46 (m, 1H), 1.39 (s, 9H), 1.06-0.99 (m, 2H).

Step 3—3-[3-Methyl-2-oxo-4-[3-(4-piperidylmethoxy)propyl]benzimidazol-1-yl]piperidine-2,6-dione To a mixture of tert-butyl 4-[3-[1-(2,6-dioxo-3-piperidyl)-3-methyl-2-oxo-benzimidazol-4-yl]propoxymethyl]piperidine-1-carboxylate (290 mg, 563 umol) in DCM (2 mL) was added HCl/dioxane (4 M, 29.00 mL). The reaction mixture was stirred at 25° C. for 2 hours. On completion, the reaction mixture was concentrated in vacuo to give the title compound (254 mg, 99% yield, HCl salt) as white solid. LC-MS (ESI$^+$) m/z 415.3 (M+H)$^+$.

Tert-butyl 3-prop-2-ynoxyazetidine-1-carboxylate (Intermediate YV)

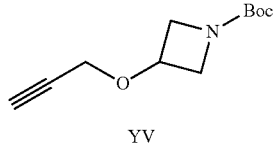

YV

To a mixture of tert-butyl 3-hydroxyazetidine-1-carboxylate (5.00 g, 28.8 mmol, CAS #141699-55-0) in THF (5 mL) was added NaH (1.39 g, 34.6 mmol, 60% oil dispersion) at 0° C. for 0.5 hour. Then 3-bromoprop-1-yne (5.15 g, 34.6 mmol, 3.73 mL) and TBAI (1.07 g, 2.89 mmol) were added to the mixture. The reaction mixture was stirred at 25° C. for 2 hours. On completion, the reaction mixture was quenched with sat. $NH_4Cl$ (50 mL), diluted with water (100 mL) and extracted with EA (2×100 mL). The combined organic layers was dried over $Na_2SO_4$, filtered and concentrated in vacuo to give a residue. The residue was purified by column chromatography to give the title compound (5.70, 93% yield) as a yellow solid. $^1$H NMR (400 MHz, CDCl$_3$) δ 4.45-4.37 (m, 1H), 4.13 (d, J=2.4 Hz, 2H), 4.12-4.07 (m, 2H), 3.89 (dd, J=9.6 Hz, 2H), 2.45-2.43 (m, 1H), 1.43 (s, 9H).

3-[5-[3-(Azetidin-3-yloxy)propyl]-3-methyl-2-oxo-benzimidazol-1-yl]piperidine-2,6-dione (Intermediate YW)

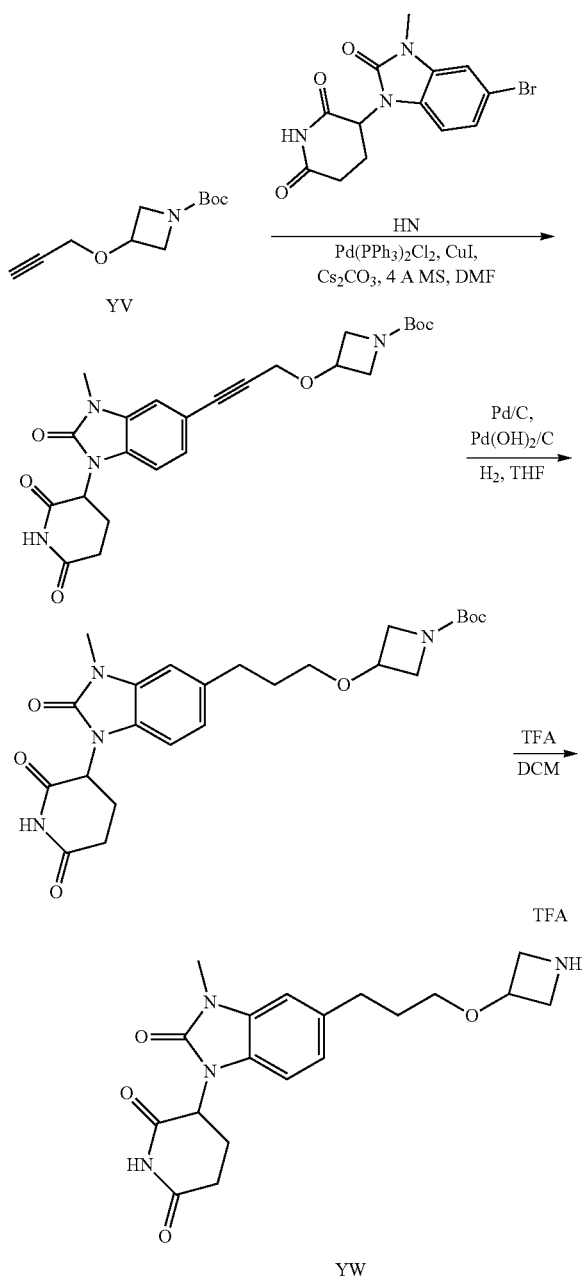

YW

Step 1—Tert-butyl 3-[3-[1-(2,6-dioxo-3-piperidyl)-3-methyl-2-oxo-benzimidazol-5-yl]prop-2-ynoxy]azetidine-1-carboxylate To a mixture of tert-butyl 3-prop-2-ynoxyazetidine-1-carboxylate (499 mg, 2.37 mmol, Intermediate YV) and 3-(5-bromo-3-methyl-2-oxo-benzimidazol-1-yl)piperidine-2,6-dione (400 mg, 1.18 mmol, Intermediate HN) in DMF (20 mL) was added Cs$_2$CO$_3$ (1.93 g, 5.91 mmol), CuI (22.5 mg, 118 umol), Pd(PPh$_3$)$_2$Cl$_2$ (83.0 mg, 118 umol) and 4 Å molecular sieves (100 mg). The reaction mixture was stirred at 80° C. for 2 hours. On completion, the mixture was filtered and concentrated in vacuo. The residue was purified by reverse phase (0.1% FA condition) to give the title compound (300 mg, 54% yield) as colorless oil. $^1$H NMR (400 MHz, DMSO-d$_6$) δ 11.11 (s, 1H), 7.66-7.59 (m, 1H), 7.58-7.49 (m, 1H), 7.18-7.13 (m, 1H), 4.49-4.43 (m, 1H), 4.10-3.97 (m, 4H), 3.77-3.76 (m, 1H), 3.77-3.72 (m, 1H), 3.46 (t, J=2.4 Hz, 1H), 3.34 (s, 3H), 2.97-2.83 (m, 1H), 2.77-2.58 (m, 2H), 2.09-1.94 (m, 1H), 1.37 (s, 9H).

Step 2—Tert-butyl 3-[3-[1-(2,6-dioxo-3-piperidyl)-3-methyl-2-oxo-benzimidazol-5-yl]propoxy]azetidine-1-carboxylate To a solution of tert-butyl 3-[3-[1-(2,6-dioxo-3-piperidyl)-3-methyl-2-oxo-benzimidazol-5-yl]prop-2-ynoxy]azetidine-1-carboxylate (300 mg, 640 umol) in THF (5 mL) was added Pd/C (100 mg, 71.2 mmol, 10% w/t) and Pd(OH)$_2$/C (100 mg, 71.2 mmol, 10% w/t) under N$_2$. The suspension was degassed under vacuum and purged with H$_2$ several times. The mixture was stirred at 25° C. for 17 hours under H$_2$ (15 psi). On completion, the mixture was filtered and concentrated in vacuo to give the title compound (240 mg, 79% yield) as a white solid. $^1$H NMR (400 MHz, DMSO-d$_6$) δ 11.07 (s, 1H), 7.07-6.98 (m, 2H), 6.87 (td, J=8.0 Hz, 1H), 5.33 (dd, J=12.8 Hz, 1H), 4.24-4.17 (m, 2H), 4.06-4.01 (m, 2H), 3.63 (s, 1H), 3.32 (s, 3H), 3.27-3.24 (m, 2H), 2.68-2.64 (m, 2H), 1.99 (s, 2H), 1.86-1.79 (m, 2H), 1.50 (t, J=7.2 Hz, 2H), 1.37 (s, 9H).

Step 3—3-[5-[3-(Azetidin-3-yloxy)propyl]-3-methyl-2-oxo-benzimidazol-1-yl]piperidine-2,6-dione To a mixture of tert-butyl 3-[3-[1-(2,6-dioxo-3-piperidyl)-3-methyl-2-oxo-benzimidazol-5-yl]propoxy]azetidine-1-carboxylate (220 mg, 465 umol) in DCM (5 mL) was added TFA (33.8 g, 297 mmol, 22.0 mL). The reaction mixture was stirred at 25° C. for 2 hours. On completion, the reaction mixture was concentrated in vacuo to give the title compound (150 mg, 86% yield) as a yellow solid. LC-MS (ESI$^+$) m/z 373.2 (M+H)$^+$.

4-(1-(2,6-Dioxopiperidin-3-yl)-3-methyl-2-oxo-2,3-dihydro-1H-benzo[d]imidazol-5-yl)but-3-yn-1-yl methanesulfonate (Intermediate YX)

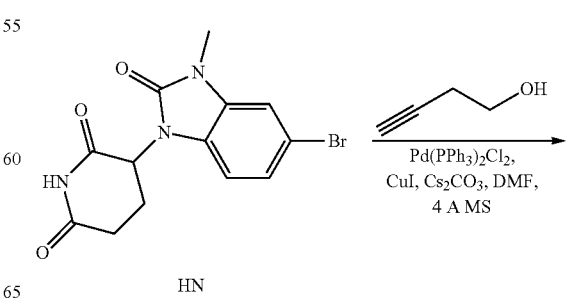

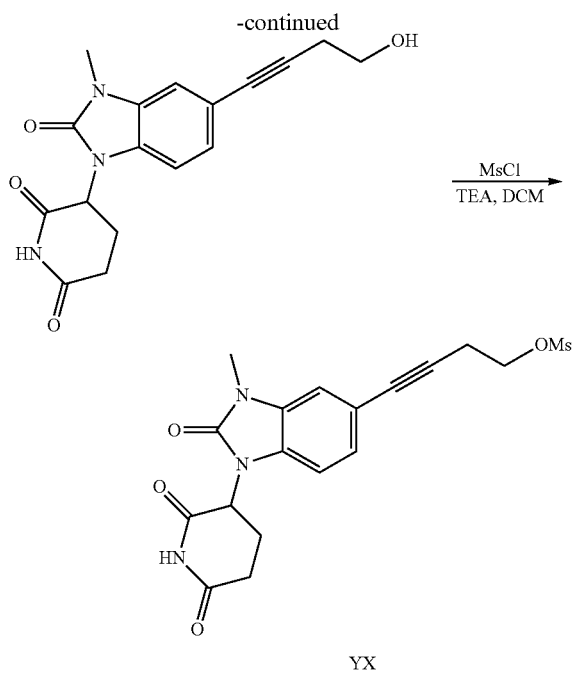

Step 1—3-(5-(4-Hydroxbut-1-yn-1-yl)-3-methyl-2-oxo-2,3-dihydro-1H-benzo[d]imidazol-1-yl) piperidine-2,6-dione To a solution of 3-(5-bromo-3-methyl-2-oxo-benzimidazol-1-yl)piperidine-2,6-dione (500 mg, 1.48 mmol, Intermediate HN) and but-3-yn-1-ol (207 mg, 2.96 mmol, CAS #927-74-2) in DMF (8 mL) was added Pd(PPh$_3$)$_2$Cl$_2$ (207 mg, 295 umol), Cs$_2$CO$_3$ (1.93 g, 5.91 mmol), CuI (56.3 mg, 295 umol) and 4 Å molecular sieves at 25° C. under N$_2$. The mixture was then heated to 80° C. and stirred for 2 hours. On completion, the reaction mixture was quenched by addition water (10 mL) at 25° C., and then diluted with CH$_2$Cl$_2$ (20 mL) and extracted with CH$_2$Cl$_2$ (3×20 mL). The combined organic layers were dried over Na$_2$SO$_4$, filtered and concentrated in vacuo to give a residue. The residue was purified by reverse phase (FA condition) to give the title compound (355 mg, 73% yield) as a yellow solid. $^1$H NMR (400 MHz, DMSO-d$_6$) δ 11.10 (s, 1H), 7.24 (s, 1H), 7.09 (s, 2H), 5.41-5.33 (m, 1H), 4.88 (s, 1H), 3.58 (t, J=7.0 Hz, 2H), 3.33 (s, 3H), 2.91-2.84 (m, 1H), 2.73-2.64 (m, 2H), 2.55 (t, J=7.0 Hz, 2H), 2.05-1.99 (m, 1H); LC-MS (ESI$^+$) m/z 328.1 (M+H)$^+$.

Step 2—4-(1-(2,6-Dioxopiperidin-3-yl)-3-methyl-2-oxo-2,3-dihydro-1H-benzo[d]imidazol-5-yl)but-3-yn-1-yl methanesulfonate To a mixture of 3-[5-(4-hydroxybut-1-ynyl)-3-methyl-2-oxo-benzimidazol-1-yl]piperidine-2,6-dione (350 mg, 1.07 mmol) in DCM (10 mL) was added TEA (324 mg, 3.21 mmol) and MsCl (159 mg, 1.39 mmol) at 0° C. The mixture was stirred at 0° C. for 0.5 hour. On completion, the reaction mixture was quenched by addition water (20 mL) at 25° C., and then extracted with DCM (3×30 mL). The combined organic layers were dried over Na$_2$SO$_4$, filtered and concentrated in vacuo to give the title compound (400 mg, 92% yield) as yellowish oil. $^1$H NMR (400 MHz, CDCl$_3$) δ 8.16 (s, 1H), 7.09-7.06 (m, 1H), 7.00 (s, 1H), 6.67 (d, J=8.2 Hz, 1H), 5.14-5.09 (m, 1H), 4.33 (t, J=6.8 Hz, 2H), 3.35 (s, 3H), 3.00 (s, 3H), 2.82 (t, J=6.8 Hz, 2H); LC-MS (ESI$^+$) m/z 406.3 (M+H)$^+$.

3-[5-[4-[4-(Aminomethyl)-1-piperidyl]but-1-ynyl]-3-methyl-2-oxo-benzimidazol-1-yl]piperidine-2,6-dione (Intermediate YY)

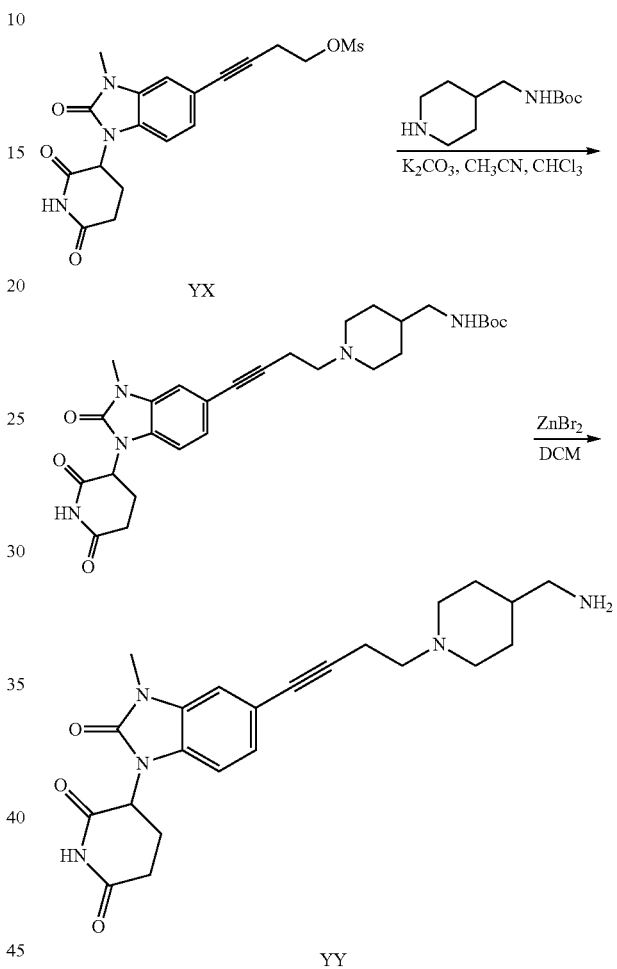

Step 1—Tert-butyl N-[[1-[4-[1-(2,6-dioxo-3-piperidyl)-3-methyl-2-oxo-benzimidazol-5-yl]but-3-ynyl]-4-piperidyl]methyl]carbamate To a solution of 4-[1-(2,6-dioxo-3-piperidyl)-3-methyl-2-oxo-benzimidazol-5-yl]but-3-ynyl methanesulfonate (350 mg, 863 umol, Intermediate YX) and tert-butyl N-(4-piperidylmethyl)carbamate (222 mg, 1.04 mmol, CAS #135632-53-0) in a mixed solvent of CHCl$_3$ (5 mL) and ACN (5 mL) was added K$_2$CO$_3$ (239 mg, 1.73 mmol). The reaction mixture was stirred at 65° C. for 12 hrs. On completion, the mixture was diluted with water (50 mL), then extracted with EA (2×50 mL). The organic layer was washed with brine (50 mL), dried with Na$_2$SO$_4$, filtrated and concentrated in vacuo. The residue was purified by prep-HPLC (column: Phenomenex Synergi Max-RP 150*50 mm*10 um; mobile phase: [water (0.225% FA)-ACN]; B %: 10%-40%, 10 min) to give the title compound (165 mg, 37% yield) as a yellow solid. $^1$H NMR (400 MHz, DMSO-d$_6$) δ

11.11 (s, 1H), 7.23 (s, 1H), 7.11-7.06 (m, 2H), 6.83 (t, J=5.6 Hz, 1H), 5.37 (dd, J=5.2, 12.8 Hz, 1H), 3.32 (s, 3H), 2.95-2.84 (m, 3H), 2.79 (t, J=6.4 Hz, 2H), 2.74-2.54 (m, 6H), 2.06-1.96 (m, 3H), 1.64-1.54 (m, 2H), 1.36 (s, 9H), 1.35-1.31 (m, 1H), 1.17-1.04 (m, 2H).

Step 2—3-[5-[4-[4-(Aminomethyl)-1-piperidyl]but-1-ynyl]-3-methyl-2-oxo-benzimidazol-1-yl]piperidine-2,6-dione To a solution of tert-butyl N-[[1-[4-[1-(2,6-dioxo-3-piperidyl)-3-methyl-2-oxo-benzimidazol-5-yl]but-3-ynyl]-4-piperidyl]methyl]carbamate (90.0 mg, 172 umol) in DCM (5 mL) was added ZnBr$_2$ (387 mg, 1.72 mmol). The reaction mixture was stirred at 20° C. for 10 hrs. On completion, the mixture was concentrated in vacuo to give the title compound (70.0 mg, 96% yield) as a white solid. LC-MS (ESI$^+$) m/z 424.3 (M+H)$^+$.

2-[2-[2-(Methylamino)ethoxy]ethyl]isoindoline-1,3-dione (Intermediate YZ)

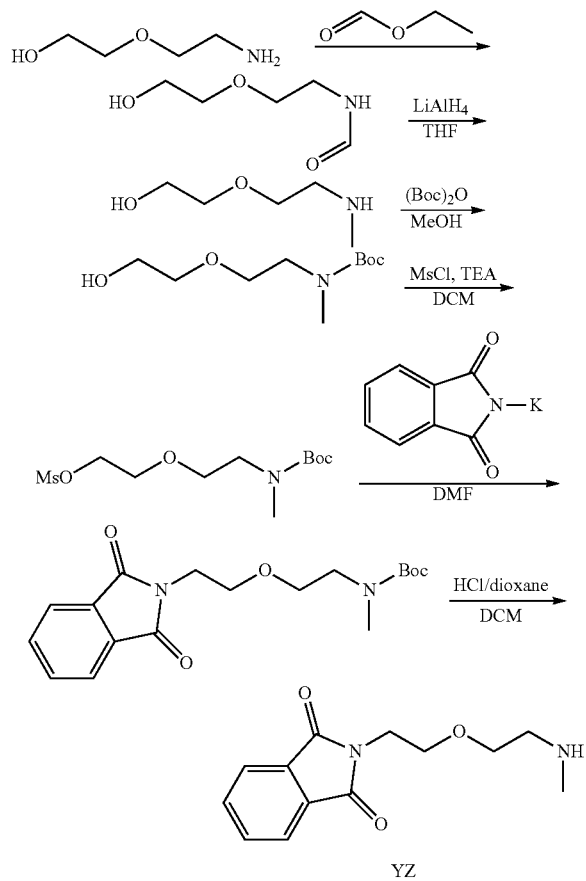

Step 1—N-[2-(2-hydroxyethoxy)ethyl]formamide

A solution of 2-(2-aminoethoxy)ethanol (5.00 g, 47.5 mmol, CAS #929-06-6) in ethyl formate (18.4 g, 248 mmol, CAS #109-94-4) was stirred at 90° C. for 6 hrs. On completion, the mixture was concentrated in vacuo to give the title compound (6.30 g, 99% yield) as yellow oil. LC-MS (ESI$^+$) m/z 134.1 (M+H)$^+$.

Step 2—2-[2-(Methylamino)ethoxy]ethanol

To a solution of LiAlH$_4$ (2.16 g, 56.7 mmol) in THF (30.0 mL) was added a solution of N-[2-(2-hydroxyethoxy)ethyl]formamide (6.30 g, 47.3 mmol) in THF (30.0 mL) dropwise at 0° C. The mixture was stirred at 80° C. for 2 hrs. On completion, the reaction mixture was quenched with a solution of 15% NaOH (20 mL). Thereafter, 50 g anhydrous sodium sulfate was added, and the mixture was filtered. The filtrate was concentrated in vacuo to give the title compound (5.64 g, 100% yield) as yellow oil.

Step 3—Tert-butyl N-[2-(2-hydroxyethoxy)ethyl]-N-methyl-carbamate

To a solution of 2-[2-(methylamino)ethoxy]ethanol (5.60 g, 46.9 mmol) in MeOH (70.0 mL) was added (Boc)$_2$O (15.3 g, 70.4 mmol), the mixture was stirred at 25° C. for 12 hrs. On completion, the mixture was concentrated in vacuo. The residue was purified by silica gel column (PE:EA=2:1) to give the title compound (8.00 g, 77% yield) as colorless oil. $^1$H NMR (400 MHz, CDCl$_3$) δ 3.80-3.68 (m, 2H), 3.67-3.52 (m, 4H), 3.48-3.33 (m, 2H), 2.92 (s, 3H), 1.47 (s, 9H).

Step 4—2-[2-[Tert-butoxycarbonyl(methyl)amino]ethoxy]ethyl methanesulfonate

To a solution of tert-butyl N-[2-(2-hydroxyethoxy)ethyl]-N-methyl-carbamate (1.00 g, 4.56 mmol), TEA (1.38 g, 13.6 mmol) in DCM (10.0 mL) was added MsCl (783 mg, 6.84 mmol) at 0° C. The mixture was stirred at 20° C. for 1 hr. On completion, the mixture was diluted with DCM (20 mL), washed with H$_2$O (3×20 mL). The organic layer was dried over anhydrous Na$_2$SO$_4$, filtered and concentrated in vacuo to give the title compound (1.28 g, 94% yield) as yellow oil. $^1$H NMR (400 MHz, CDCl$_3$) δ 4.33-4.26 (m, 2H), 3.68-3.62 (m, 2H), 3.59-3.48 (m, 2H), 3.39-3.28 (m, 2H), 2.98 (s, 3H), 2.84 (s, 3H), 1.39 (s, 9H).

Step 5-Tert-butyl N-[2-[2-(1,3-dioxoisoindolin-2-yl)ethoxy]ethyl]-N-methyl-carbamate To a solution of 2-[2-[tert-butoxycarbonyl(methyl)amino]ethoxy]ethyl methanesulfonate (1.08 g, 3.63 mmol) in DMF (10.0 mL) was added (1,3-dioxoisoindolin-2-yl)potassium (1.01 g, 5.45 mmol). The mixture was stirred at 80° C. for 3 hrs. On completion, the mixture was diluted with H$_2$O (40 mL), then extracted with EA (3×30 mL). The organic layers were washed with brine (2×30 mL) and dried over anhydrous Na$_2$SO$_4$, filtered and concentrated in vacuo. The residue was purified by silica gel column (PE:EA=5:1) to give the title compound (1.2 g, 94% yield) as white solid. $^1$H NMR (400 MHz, DMSO-d$_6$) δ 7.89-7.83 (m, 4H), 3.81-3.71 (m, 2H), 3.68-3.56 (m, 2H), 3.54-3.42 (m, 2H), 3.28-3.20 (m, 2H), 2.69 (s, 3H), 1.32 (s, 9H).

Step 6—2-[2-[2-(Methylamino)ethoxy]ethyl]isoindoline-1,3-dione

To a solution of tert-butyl N-[2-[2-(1,3-dioxoisoindolin-2-yl)ethoxy]ethyl]-N-methyl-carbamate (200 mg, 574 umol) in DCM (3.00 mL) was added HCl/dioxane (4.00 M, 4.00 mL). The mixture was stirred at 20° C. for 0.5 hr. On completion, the mixture was concentrated in vacuo to give the title compound (160 mg, 97% yield, HCl) as white solid.

$^1$H NMR (400 MHz, DMSO-d$_6$) δ 8.84 (s, 1H), 7.92-7.84 (m, 4H), 3.84-3.76 (m, 2H), 3.73-3.65 (m, 4H), 3.10-2.92 (m, 2H), 2.49 (s, 3H).

Tert-butyl N-[[(2S)-4-(2-aminoethyl)morpholin-2-yl]methyl]-N-methyl-carbamate (Intermediate ZA)

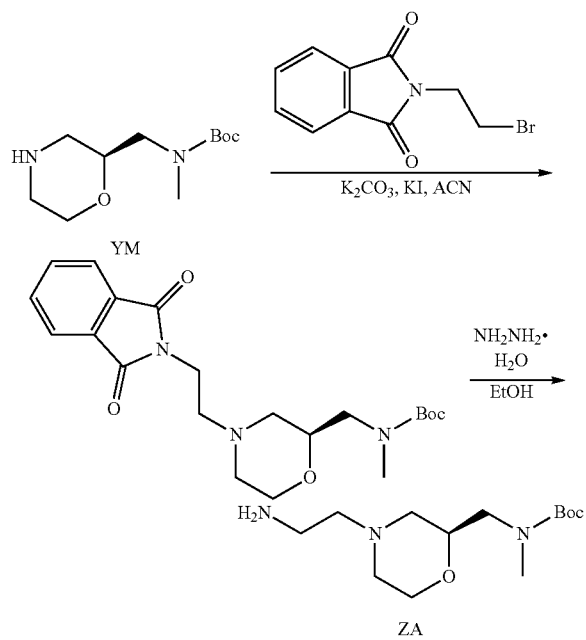

Step 1—Tert-butyl N-[[(2S)-4-[2-(1,3-dioxoisoindolin-2-yl)ethyl]morpholin-2-yl]methyl]-N-methyl-carbamate To a solution of tert-butyl N-methyl-N-[[(2S)-morpholin-2-yl]methyl]carbamate (1.00 g, 4.34 mmol, Intermediate YM) in ACN (30 mL) was added K$_2$CO$_3$ (535 mg, 13.0 mmol) and 2-(2-bromoethyl)isoindoline-1,3-dione (1.21 g, 4.77 mmol, CAS #574-98-1) and KI (72.1 mg, 434 umol). The reaction mixture was stirred at 80° C. for 12 hrs. On completion, the mixture was diluted with H$_2$O (20 mL), then extracted with EA (2×20 mL). The combined organic layers were washed with brine (2×20 mL), dried over anhydrous Na$_2$SO$_4$, filtered and the filtrate was concentrated in vacuo. The residue was purified by silica gel column (PE:EA=1:1) to give the title compound (1.75 g, 100% yield) as yellow oil. $^1$H NMR (400 MHz, CDCl$_3$) δ 7.89-7.81 (m, 2H), 7.77-7.67 (m, 2H), 3.96-3.75 (m, 3H), 3.65-3.48 (m, 2H), 3.42-3.29 (m, 1H), 3.14 (dd, J=6.4, 14.4 Hz, 1H), 2.89 (s, 3H), 2.86-2.73 (m, 2H), 2.70-2.51 (m, 2H), 2.17 (t, J=10.4 Hz, 1H), 1.93-1.90 (m, 1H), 1.45 (s, 9H).

Step 2—Tert-butyl N-[[(2S)-4-(2-aminoethyl)morpholin-2-yl]methyl]-N-methyl-carbamate To a solution of tert-butyl N-[[(2S)-4-[2-(1,3-dioxoisoindolin-2-yl)ethyl]morpholin-2-yl]methyl]-N-methyl-carbamate (1.00 g, 2.48 mmol) in EtOH (10 mL) was added NH$_2$NH$_2$.H$_2$O (633 mg, 12.4 mmol). The reaction mixture was stirred at 80° C. for 2 hrs. On completion, the reaction mixture was filtered and the filtrate was concentrated in vacuo to give the title compound (650 mg, 96% yield) as yellow solid. $^1$H NMR (400 MHz, CDCl$_3$) δ 3.94-3.81 (m, 1H), 3.76-3.60 (m, 2H), 3.53-3.30 (m, 1H), 3.24-3.09 (m, 1H), 2.92 (s, 3H), 2.82-2.78 (m, 2H), 2.75-2.71 (m, 1H), 2.68-2.65 (m, 1H), 2.43 (t, J=6.0 Hz, 2H), 2.51-2.35 (m, 1H), 2.17-2.15 (1H), 1.88 (t, J=10.4 Hz, 1H), 1.46 (s, 9H).

Benzyl N-[[1-(2,6-dioxo-3-piperidyl)-3-methyl-2-oxo-benzimidazol-5-yl]methyl]-N-[2-[(2R)-2-(methylaminomethyl)morpholin-4-yl]ethyl]carbamate (Intermediate ZB)

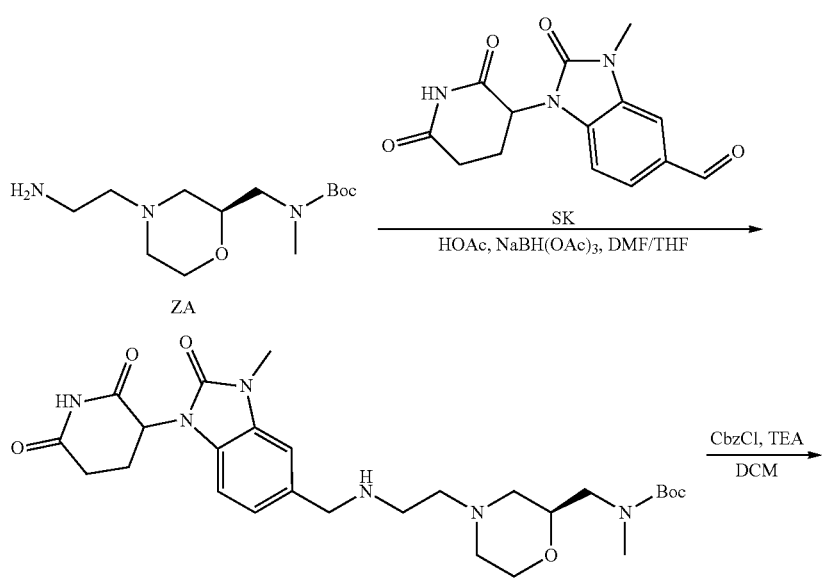

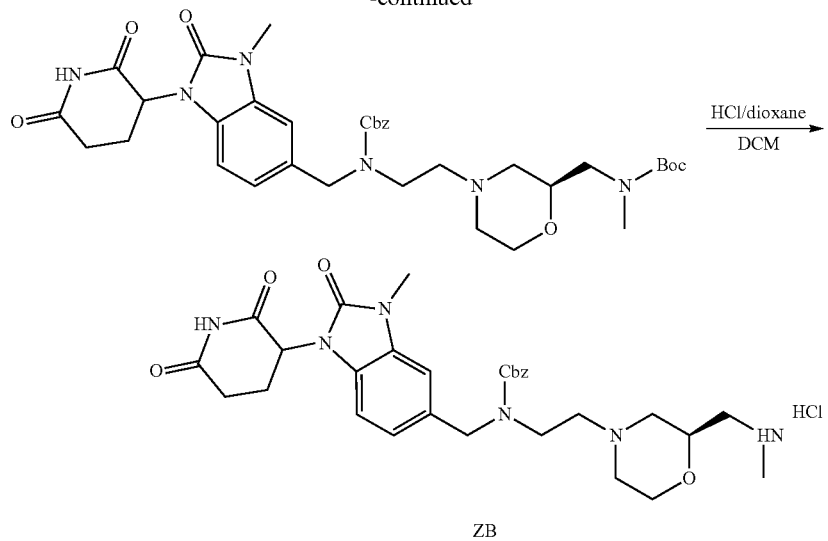

ZB

Step 1—Tert-butyl N-[[(2S)-4-[2-[[1-(2,6-dioxo-3-piperidyl)-3-methyl-2-oxo-benzimidazol-5-yl]methylamino]ethyl]morpholin-2-yl]methyl]-N-methyl-carbamate To a solution of 1-(2,6-dioxo-3-piperidyl)-3-methyl-2-oxo-benzimidazole-5-carbaldehyde (400 mg, 1.04 mmol, Intermediate SK) and tert-butyl N-[[(2S)-4-(2-aminoethyl)morpholin-2-yl]methyl]-N-methyl-carbamate (428 mg, 1.57 mmol, Intermediate ZA) in a mixed solvent of THF (5 mL) and DMF (2 mL) was added HOAc (62 mg, 1.04 mmol). The reaction mixture was stirred at 25° C. for 0.5 hr. Then, NaBH(OAc)₃ (266 mg, 1.25 mmol) was added. The reaction mixture was stirred at 25° C. for 12 hrs. On completion, the mixture was quenched with water (0.5 mL) and concentrated in vacuo. The crude product was purified by reverse phase HPLC (0.1% FA condition) to give the title compound (410 mg, 61% yield) as white solid. $^1$H NMR (400 MHz, DMSO-$d_6$) δ 11.10 (s, 1H), 7.24 (s, 1H), 7.16-7.02 (m, 2H), 5.37 (dd, J=5.6, 12.8 Hz, 1H), 4.53-4.50 (m, 1H), 3.91 (s, 2H), 3.80-3.75 (m, 2H), 3.35 (s, 3H), 3.23-3.17 (m, 2H), 2.92-2.87 (m, 1H), 2.80-2.73 (m, 4H), 2.69-2.58 (m, 7H), 2.06-1.98 (m, 2H), 1.82-1.74 (m, 1H), 1.36 (s, 9H).

Step 2—Tert-butyl N-[[(2S)-4-[2-[benzyloxycarbonyl-[[1-(2,6-dioxo-3-piperidyl)-3-methyl-2-oxo-benzimidazol-5-yl]methyl]amino]ethyl]morpholin-2-yl]methyl]-N-methyl-carbamate To a solution of tert-butyl N-[[(2S)-4-[2-[[1-(2,6-dioxo-3-piperidyl)-3-methyl-2-oxo-benzimidazol-5-yl]methylamino]ethyl]morpholin-2-yl]methyl]-N-methyl-carbamate (100 mg, 184 umol) in THF (5 mL) was added TEA (55.7 mg, 550 umol). Then, CbzCl (47.0 mg, 275 umol) was added. The reaction mixture was stirred at 25° C. for 1 hr. On completion, the reaction mixture was concentrated in vacuo to give the title compound (50.0 mg, 38% yield) as white solid. $^1$H NMR (400 MHz, DMSO-$d_6$) δ 11.09 (s, 1H), 7.49-7.26 (m, 5H), 7.11-6.90 (m, 3H), 5.36 (dd, J=5.2, 12.8 Hz, 1H), 5.13 (s, 2H), 4.52 (s, 2H), 3.75-3.67 (m, 1H), 3.57-3.44 (m, 5H), 3.22-3.11 (m, 4H), 2.96-2.90 (m, 1H), 2.79 (s, 2H), 2.73-2.66 (m, 2H), 2.62-2.55 (m, 3H), 2.43-2.37 (m, 2H), 2.06-1.96 (m, 2H), 1.80-1.68 (m, 1H), 1.37 (s, 9H); LC-MS (ESI$^+$) m/z 679.2 (M+H)$^+$.

Step 3—Benzyl N-[[1-(2,6-dioxo-3-piperidyl)-3-methyl-2-oxo-benzimidazol-5-yl]methyl]-N-[2-[(2R)-2-(methylaminomethyl)morpholin-4-yl]ethyl]carbamate To a solution of tert-butyl N-[[(2S)-4-[2-[benzyloxycarbonyl-[[1-(2,6-dioxo-3-piperidyl)-3-methyl-2-oxo-benzimidazol-5-yl]methyl]amino]ethyl]morpholin-2-yl]methyl]-N-methyl-carbamate (50.0 mg, 73.6 umol) in DCM (2 mL) was added HCl/dioxane (4 M, 1 mL). The reaction mixture was stirred at 20° C. for 1 hr. On completion, the mixture was concentrated in vacuo to give the title compound (45.0 mg, 99% yield) as white solid. LC-MS (ESI$^+$) m/z 579.2 (M+H)$^+$.

3-[3-Methyl-2-oxo-5-[2-(4-piperidyl)ethynyl]benzimidazol-1-yl]piperidine-2,6-dione (Intermediate ZD)

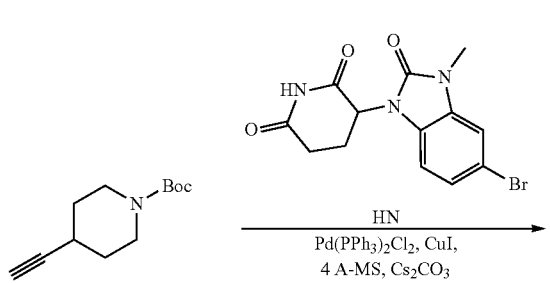

2069
-continued

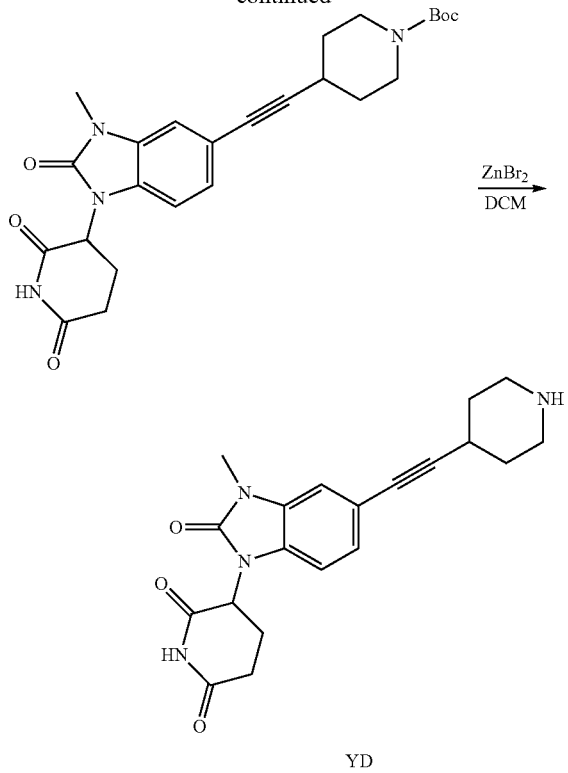

YD

Step 1—Tert-butyl 4-[2-[1-(2,6-dioxo-3-piperidyl)-3-methyl-2-oxo-benzimidazol-5-yl]ethynyl]piperidine-1-carboxylate To a solution of tert-butyl 4-ethynylpiperidine-1-carboxylate (743 mg, 3.55 mmol CAS #287192-97-6) and 3-(5-bromo-3-methyl-2-oxo-benzimidazol-1-yl)piperidine-2,6-dione (600 mg, 1.77 mmol, Intermediate HN) in DMF (20 mL) was added Pd(PPh$_3$)$_2$Cl$_2$ (249 mg, 355 umol), CuI (67.6 mg, 355 umol), 4 Å molecular sieves (80 mg) and Cs$_2$CO$_3$ (2.89 g, 8.87 mmol). The mixture was de-gassed and then heated at 80° C. for 2 hrs. On completion, the reaction mixture was concentrated in vacuo. The crude product was purified by reversed-phase HPLC (0.1% FA condition) to give the title compound (500 mg, 58% yield) as brown solid. $^1$H NMR (400 MHz, DMSO-d$_6$) δ 11.11 (s, 1H), 7.25 (s, 1H), 7.09 (s, 2H), 5.37 (dd, J=5.6, 12.8 Hz, 1H), 3.70-3.59 (m, 2H), 3.33-3.33 (m, 3H), 3.19-3.08 (m, 2H), 2.95-2.80 (m, 2H), 2.75-2.62 (m, 2H), 2.07-1.98 (m, 1H), 2.00-1.81 (m, 2H), 1.56-1.45 (m, 2H), 1.40 (s, 9H); LC-MS (ESI$^+$) m/z 489.3 (M+Na)$^+$.

Step 2—3-[3-Methyl-2-oxo-5-[2-(4-piperidyl)ethynyl]benzimidazol-1-yl]piperidine-2,6-dione To a solution of tert-butyl 4-[2-[1-(2,6-dioxo-3-piperidyl)-3-methyl-2-oxo-benzimidazol-5-yl]ethynyl]piperidine-1-carboxylate (60.0 mg, 129 umol) in DCM (5 mL) was added ZnBr$_2$ (347 mg, 1.54 mmol, 77.2 uL). The mixture was stirred at 25° C. for 24 hrs. On completion, the mixture was concentrated in vacuo to give the title compound (40.0 mg, 68% yield) as yellow solid. LC-MS (ESI+) m/z 367.1 (M+H)$^+$.

2070
Tert-butyl (3R)-3-piperazin-1-ylpyrrolidine-1-carboxylate (Intermediate ZE)

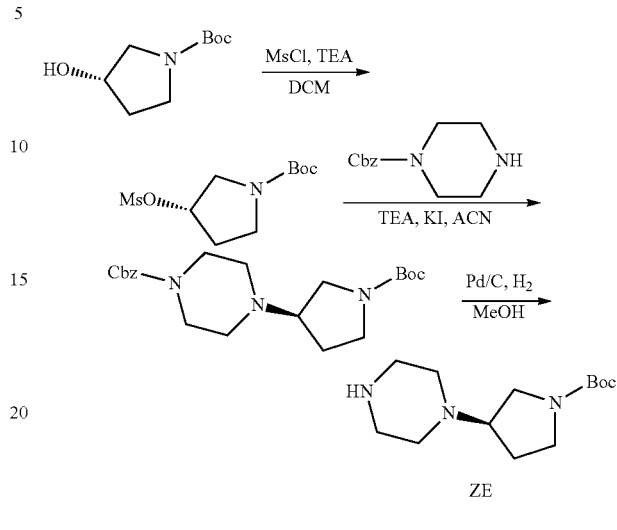

ZE

Step 1—Tert-butyl (3S)-3-methyl sulfonyloxypyrrolidine-1-carboxylate

To a solution of tert-butyl (3S)-3-hydroxypyrrolidine-1-carboxylate (5.00 g, 26.7 mmol, CAS #101469-92-5) in DCM (80 mL) was added TEA (8.11 g, 80.1 mmol) and MsCl (3.98 g, 34.7 mmol) at 0° C. The mixture was then stirred at 25° C. for 0.5 hr. On completion, the reaction mixture was washed with water (3×60 mL). The organic layer was dried over Na$_2$SO$_4$, filtered and concentrated in vacuo to give the title compound (7.00 g, 95% yield) as light yellow oil. $^1$H NMR (400 MHz, CDCl$_3$) δ 5.30-5.23 (m, 1H), 3.70-3.42 (m, 4H), 3.05 (s, 3H), 2.38-2.08 (m, 2H), 1.47 (s, 9H).

Step 2—Benzyl 4-[(3R)-1-tert-butoxycarbonylpyrrolidin-3-yl]piperazine-1-carboxylate To a solution of tert-butyl (3S)-3-methyl sulfonyloxypyrrolidine-1-carboxylate (3 g, 11.3 mmol) and benzyl piperazine-1-carboxylate (4.98 g, 22.61 mmol, CAS #31166-44-6) in ACN (30 mL) was added TEA (3.43 g, 33.9 mmol) and KI (2.82 g, 16.9 mmol). The mixture was stirred as 80° C. for 40 hrs. On completion, the mixture was concentrated in vacuo to give a residue. The reaction mixture was diluted with water (30 mL) and extracted with EA (3×30 mL). The combined organic layers were dried over Na$_2$SO$_4$, filtered and concentrated in vacuo to give a residue. The residue was purified by column chromatography (SiO$_2$, PE/EA=3/1) to give the title compound (1.35 g, 30% yield) as light yellow oil. $^1$H NMR (400 MHz, CDCl$_3$) δ 7.43-7.28 (m, 5H), 5.14 (s, 2H), 3.75-3.38 (m, 6H), 3.34-3.20 (m, 1H), 3.09-3.05 (m, 1H), 2.86-2.70 (m, 1H), 2.61-2.31 (m, 4H), 2.12-2.05 (m, 1H), 1.85-1.75 (m, 1H), 1.46 (s, 9H).

Step 3—Tert-butyl (3R)-3-piperazin-1-ylpyrrolidine-1-carboxylate

To a solution of benzyl 4-[(3R)-1-tert-butoxycarbonylpyrrolidin-3-yl]piperazine-1-carboxylate (1.20 g, 3.08 mmol) in MeOH (20 mL) was added Pd/C (400 mg, 10 wt %) under N$_2$. The suspension was degassed under vacuum and purged with H$_2$ three times. The mixture was stirred at 25° C. for 16 hours under H$_2$ (15 psi). On completion, the mixture was filtered and the filtrate was concentrated in vacuo to give the title compound (780 mg, 96% yield) as colorless oil. $^1$H NMR (400 MHz, CDCl$_3$) δ 3.76-3.48 (m, 2H), 3.30-3.19 (m, 1H), 3.08 (t, J=9.2 Hz, 1H), 2.90 (t, J=4.4 Hz, 3H), 2.83-2.69 (m, 1H), 2.62-2.34 (m, 4H), 2.13-2.02 (m, 1H), 1.73-1.67 (m, 1H), 1.45 (s, 9H).

3-[3-Methyl-2-oxo-5-[[4-[(3R)-pyrrolidin-3-yl]piperazin-1-yl]methyl]benzimidazol-1-yl]piperidine-2,6-dione (Intermediate ZF)

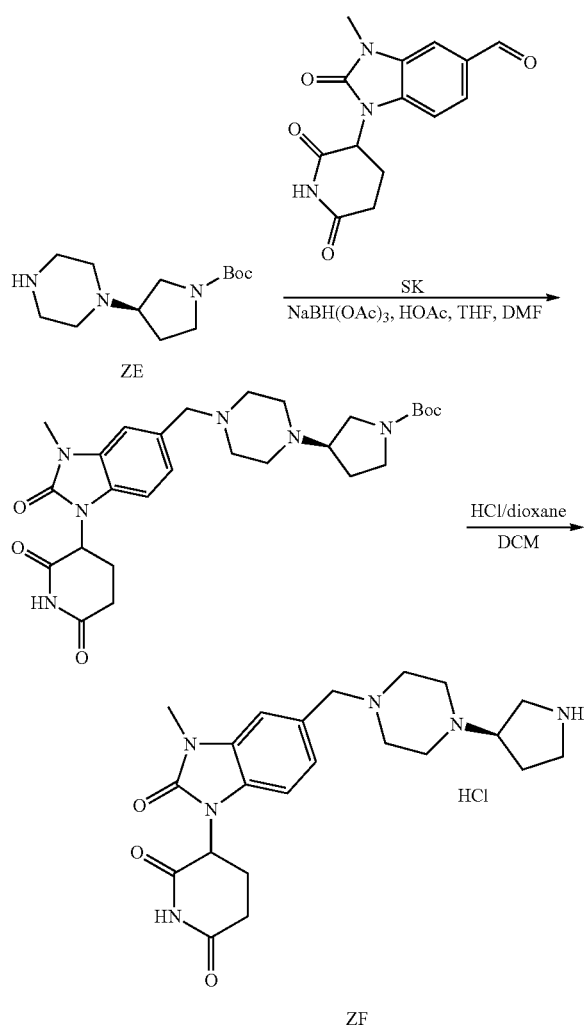

Step 1—Tert-butyl (3R)-3-[4-[[1-(2,6-dioxo-3-piperidyl)-3-methyl-2-oxo-benzimidazol-5-yl]methyl]piperazin-1-yl]pyrrolidine-1-carboxylate To a mixture of tert-butyl (3R)-3-piperazin-1-ylpyrrolidine-1-carboxylate (200 mg, 783 umol, Intermediate ZE) in a mixed solvent of THF (4 mL) and DMF (0.2 mL) was added 1-(2,6-dioxo-3-piperidyl)-3-methyl-2-oxo-benzimidazole-5-carbaldehyde (225 mg, 783 umol, Intermediate SK) and HOAc (9.41 mg, 156 umol). The mixture was stirred at 25° C. for 30 minutes. After that, NaBH(OAc)$_3$ (331 mg, 1.57 mmol) was added. The mixture was stirred 25° C. for 72 hours. On completion, the reaction mixture was quenched by water (10 mL), and then extracted with EA (3×15 mL). The combined organic layers were dried over Na$_2$SO$_4$, filtered and concentrated in vacuo to give a residue. The residue was purified by prep-HPLC (column: Phenomenex Synergi Max-RP 150*50 mm*10 um; mobile phase: [water (0.225% FA)-ACN]) to give the title compound (290 mg, 70% yield) as white solid. $^1$H NMR (400 MHz, DMSO-d$_6$) δ 11.08 (s, 1H), 7.11-6.91 (m, 3H), 5.35 (dd, J=5.2, 12.8 Hz, 1H), 3.48 (s, 2H), 3.45 (s, 1H), 3.42-3.34 (m, 1H), 3.33 (s, 3H), 3.21-3.10 (m, 1H), 2.98-2.84 (m, 2H), 2.75-2.59 (m, 3H), 2.45-2.3 (m, 8H), 2.06-1.93 (m, 2H), 1.71-1.51 (m, 1H), 1.38 (s, 9H); LC-MS (ESI$^+$) m/z 527.2 (M+H)$^+$.

Step 2—3-[3-Methyl-2-oxo-5-[[4-[(3R)-pyrrolidin-3-yl]piperazin-1-yl]methyl]benzimidazol-1-yl]piperidine-2,6-dione To a solution of tert-butyl (3R)-3-[4-[[1-(2,6-dioxo-3-piperidyl)-3-methyl-2-oxo-benzimidazol-5-yl]methyl]piperazin-1-yl]pyrrolidine-1-carboxylate (120 mg, 227 umol) in DCM (5 mL) was added HCl/dioxane (4 M, 2.28 mL). The mixture was stirred at 25° C. for 1 hr. On completion, the reaction mixture was concentrated in vacuo to give the title compound (105 mg, 99% yield, HCl) as white solid. LC-MS (ESI$^+$) m/z 427.5 (M+H)$^+$.

Tert-butyl methyl(3-oxopropyl)carbamate (Intermediate ZG)

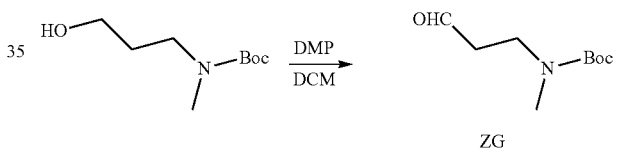

To a solution of tert-butyl N-(3-hydroxypropyl)-N-methyl-carbamate (1.00 g, 5.28 mmol, CAS #98642-44-5) in DCM (20 mL) was added DMP (3.36 g, 7.93 mmol) at 20° C. Then the reaction mixture was stirred at 20° C. for 2 hours. On completion, the reaction mixture was diluted with petroleum ether (10 mL) and stirred for 10 minutes, filtered and concentrated in vacuo. The residue was purified by flash silica gel chromatography to give the title compound (750 mg, 50% yield) as colorless oil. $^1$H NMR (400 MHz, CDCl$_3$) δ 9.78 (s, 1H), 3.53-3.47 (m, 2H), 2.85 (s, 3H), 2.66-2.62 (m, 2H), 1.43 (s, 9H).

3-(3-Methyl-2-oxo-4-(piperidin-4-yl)-2,3-dihydro-1H-benzo[d]imidazol-1-yl)piperidine-2,6-dione hydrochloride (Intermediate ZH)

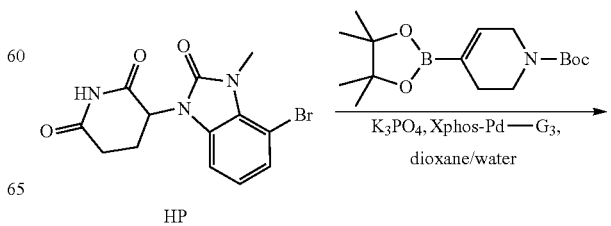

-continued

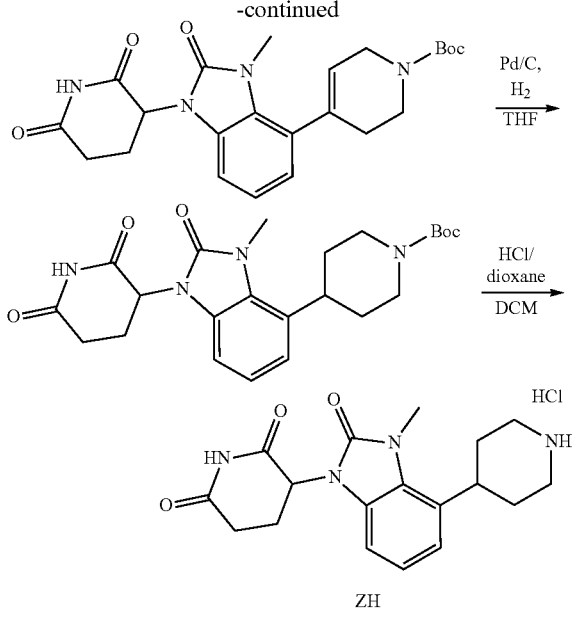

Step 1—Tert-butyl 4-(1-(2,6-dioxopiperidin-3-yl)-3-methyl-2-oxo-2,3-dihydro-1H-benzo[d]imidazol-4-yl)-5,6-dihydropyridine-1 (2H)-carboxylate A mixture of 3-(4-bromo-3-methyl-2-oxo-benzimidazol-1-yl)piperidine-2,6-dione (1.00 g, 2.96 mmol, Intermediate HP), tert-butyl 4-(4,4,5,5-tetramethyl-1,3,2-dioxaborolan-2-yl)-3,6-dihydro-2H-pyridine-1-carboxylate (1.19 g, 3.84 mmol, CAS #286961-14-6), XPhos-Pd-G3 (376 mg, 0.444 mmol), K$_3$PO$_4$ (1.88 g, 8.87 mmol) in dioxane (20 mL) and water (2 mL) was degassed and purged with N$_2$ three times. The mixture was stirred at 60° C. for 3 hours under N$_2$ atmosphere. On completion, the reaction mixture was filtered and the filtrate was concentrated in vacuo. The residue was purified by reverse phase (0.1% FA condition) to give the title compound (1.00 g, 75% yield) as white solid. $^1$H NMR (400 MHz, DMSO-d$_6$) δ 11.09 (s, 1H), 7.10-6.95 (m, 2H), 6.82 (d, J=7.2 Hz, 1H), 5.40-5.35 (m, 1H), 3.99 (s, 3H), 3.67-3.50 (m, 3H), 2.95-2.83 (m, 1H), 2.80-2.55 (m, 3H), 2.43-2.30 (m, 3H), 2.05-1.95 (m, 1H), 1.44 (s, 9H); LC-MS (ESI$^+$) m/z 441.0 (M+H)$^+$.

Step 2—Tert-butyl 4-(1-(2,6-dioxopiperidin-3-yl)-3-methyl-2-oxo-2,3-dihydro-1H-benzo[d]imidazol-4-yl)piperidine-1-carboxylate To a solution of tert-butyl 4-[1-(2,6-dioxo-3-piperidyl)-3-methyl-2-oxo-benzimidazol-4-yl]-3,6-dihydro-2H-pyridine-1-carboxylate (900 mg, 2.04 mmol) in THF (270 mL) was added Pd/C (180 mg, 10 wt %) under N$_2$ atmosphere. The suspension was degassed and purged with H$_2$ three times. The mixture was stirred at 30° C. for 48 hours under H$_2$ (50 Psi.). On completion, the reaction mixture was filtered and concentrated in vacuo to give the title compound (900 mg, 92% yield) as white solid. LC-MS (ESI$^+$) m/z 387.2 (M+H−56)$^+$.

Step 3—3-(3-Methyl-2-oxo-4-(piperidin-4-yl)-2,3-dihydro-1H-benzod[d]imidazol-1-yl)piperidine-2,6-dione hydrochloride To a solution of tert-butyl 4-[1-(2,6-dioxo-3-piperidyl)-3-methyl-2-oxo-benzimidazol-4-yl]piperidine-1-carboxylate (1.00 g, 2.26 mmol) in DCM (10 mL) was added HCl/dioxane (4 mol/L, 5 mL). The reaction mixture was stirred at 25° C. for 1 hour. On completion, the reaction mixture was concentrated in vacuo to give the title compound (900 mg, 88% yield) as white solid. LC-MS (ESI$^+$) m/z 343.2 (M+H)$^+$.

3-(3-Methyl-4-(1-(3-(methylamino)propyl)piperidin-4-yl)-2-oxo-2,3-dihydro-1H-benzo[d]imidazol-1-yl)piperidine-2,6-dione hydrochloride (Intermediate ZI)

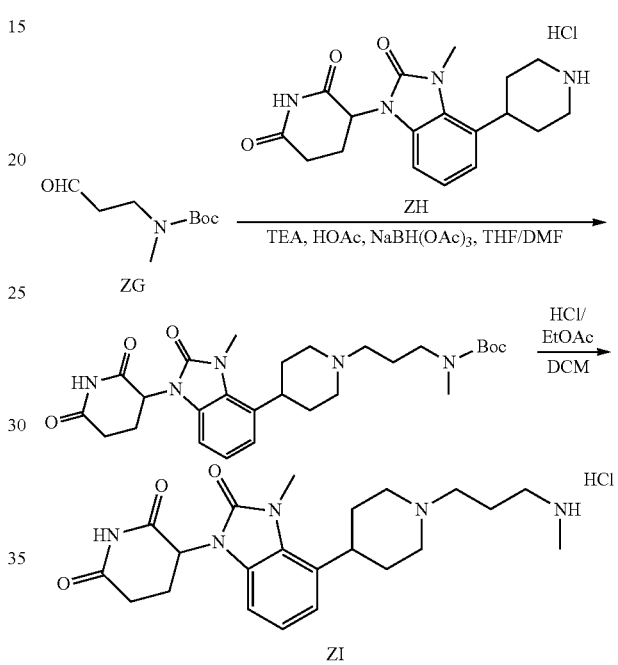

Step 1-Tert-butyl (3-(4-(1-(2,6-dioxopiperidin-3-yl)-3-methyl-2-oxo-2,3-dihydro-1H-benzo[d]imidazol-4-yl)piperidin-1-yl)propyl)(methyl)carbamate To a solution of 3-[3-methyl-2-oxo-4-(4-piperidyl)benzimidazol-1-yl]piperidine-2,6-dione (350 mg, 0.924 mmol, Intermediate ZH) in THF (5 mL) and DMF (1 mL) was added Et$_3$N (140 mg, 1.39 mmol). Then the reaction mixture was stirred at 20° C. for 0.5 hour. Then HOAc (83.2 mg, 1.39 mmol) and tert-butyl N-methyl-N-(3-oxopropyl)carbamate (580 mg, 2.04 mmol, Intermediate ZG) were added to the above mixture. The reaction mixture was stirred at 20° C. for 0.5 hour. NaBH(OAc)$_3$ (392 mg, 1.85 mmol) was added to the reaction mixture and stirred at 20° C. for 16 hours. On completion, the reaction mixture was quenched with water (0.5 mL) and concentrated in vacuo. The residue was purified by reverse phase (0.1% FA condition) to give the title compound (450 mg, 83% yield) as off-white solid. LC-MS (ESI$^+$) m/z 514.4 (M+H)$^+$.

Step 2—3-(3-Methyl-4-(1-(3-(methylamino)propyl)piperidin-4-yl)-2-oxo-2,3-dihydro-1H-benzo[d]imidazol-1-yl)piperidine-2,6-dione hydrochloride To a solution of tert-butyl N-[3-[4-[1-(2,6-dioxo-3-piperidyl)-3-methyl-2-oxo-benzimidazol-4-yl]-1-piperidyl]

propyl]-N-methyl-carbamate (450 mg, 0.876 mmol) in DCM (5 mL) was added HCl/EA (4 mol/L, 2 mL), the reaction mixture was stirred at 20° C. for 1 hour. On completion, the reaction mixture was concentrated in vacuo to give the title compound (390 mg, 99% yield) as a white solid. LC-MS (ESI$^+$) m/z 414.3 (M+H)$^+$.

3-(3-Methyl-4-(3-((R)-2-(2-(methylamino)ethyl) morpholino)propyl)-2-oxo-2,3-dihydro-1H-benzo[d] imidazol-1-yl)piperidine-2,6-dione hydrobromide (Intermediate ZL)

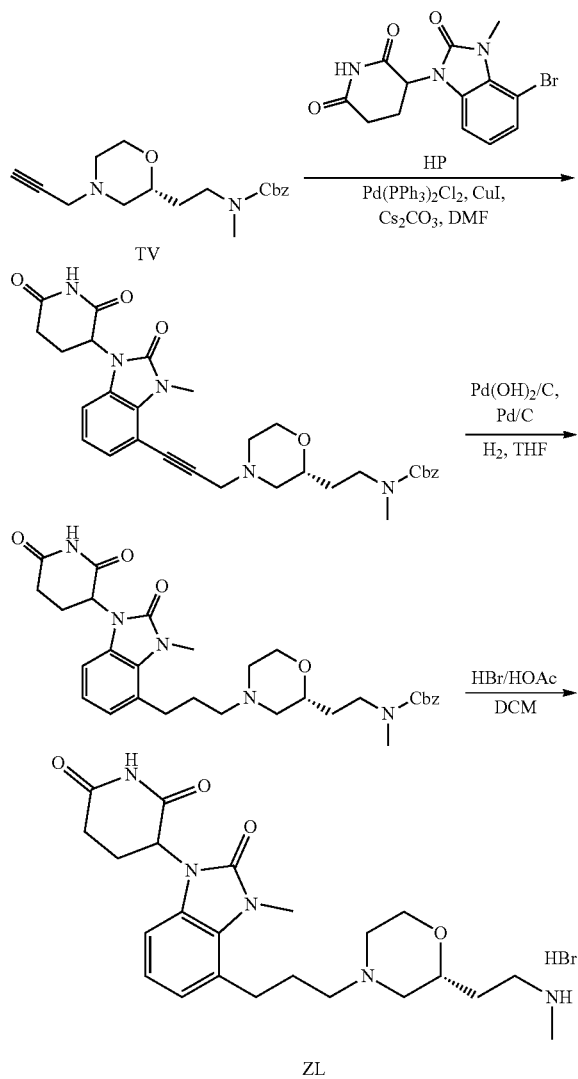

Step 1—Benzyl (2-((2R)-4-(3-(1-(2,6-dioxopiperi-din-3-yl)-3-methyl-2-oxo-2,3-dihydro-1H-benzo[d] imidazol-4-yl)prop-2-yn-1-yl)morpholin-2-yl)ethyl) (methyl)carbamate A mixture of benzyl N-methyl-N-[2-[(2R)-4-prop-2-ynylmorpholin-2-yl]ethyl]carbamate (700 mg, 2.07 mmol, Intermediate TV), 3-(4-bromo-3-methyl-2-oxo-2,3-dihydro-1H-benzo[d]imidazol-1-yl)piperidine-2,6-dione (982 mg, 3.11 mmol, Intermediate HP), Pd(PPh$_3$)$_2$Cl$_2$ (145 mg, 0.207 mmol), CuI (39.4 mg, 0.207 mmol) and Cs$_2$CO$_3$ (1.35 g, 4.14 mmol) in DMF (10 mL) was degassed and purged with N$_2$ three times. Then the mixture was stirred at 80° C. for 2 hours under N$_2$ atmosphere. On completion, the reaction mixture was filtered and the filtrate was concentrated in vacuo. The residue was purified by reverse phase (0.1% of FA condition) to give the title compound (1.10 g, 73% yield) as a yellow solid. $^1$H NMR (400 MHz, CDCl$_3$) δ11.11 (s, 1H), 7.40-7.30 (s, 5H), 7.13 (dd, J=16.0 Hz, J=7.6 Hz, 2H), 7.06-6.95 (m, 1H), 5.47-5.32 (m, 1H), 5.05 (s, 2H), 3.90-3.75 (m, 1H), 3.63 (s, 3H), 3.56 (s, 3H), 3.27-3.15 (m, 2H), 2.90-2.80 (m, 5H), 2.75-2.55 (m, 4H), 2.35-2.25 (m, 1H), 2.10-1.95 (m, 2H), 1.76-1.72 (m, 1H), 1.65-1.55 (m, 2H); LC-MS (ESI$^+$) m/z 574.1 (M+H)$^+$.

Step 2—Benzyl (2-((2R)-4-(3-(1-(2,6-dioxopiperi-din-3-yl)-3-methyl-2-oxo-2,3-dihydro-1H-benzo[d] imidazol-4-yl)propyl)morpholin-2-yl)ethyl)(methyl) carbamate To a solution of benzyl N-[2-[(2R)-4-[3-[1-(2,6-dioxo-3-piperidyl)-3-methyl-2-oxo-benzimidazol-4-yl]prop-2-ynyl]morpholin-2-yl]ethyl]-N-methyl-carbamate (1.00 g, 1.74 mmol) in THF (200 mL) was added Pd/C (200 mg, 5 wt %) and Pd(OH)$_2$/C (200 mg, 10 wt %) under N$_2$ atmosphere. The suspension was degassed and purged with H$_2$ three times. The mixture was stirred at 20° C. for 48 hours under H$_2$ (15 psi). On completion, the reaction mixture was filtered and concentrated in vacuo to give the title compound (1.00 g, 99% yield) as yellow-white solid. LC-MS (ESI$^+$) m/z 578.2 (M+H)$^+$.

Step 3—3-(3-Methyl-4-(3-((R)-2-(2-(methylamino) ethyl)morpholino)propyl)-2-oxo-2,3-dihydro-1H-benzo[d]imidazol-1-yl)piperi dine-2,6-dione hydro-bromide To a solution of benzyl N-[2-[(2R)-4-[3-[1-(2,6-dioxo-3-piperidyl)-3-methyl-2-oxo-benzimidazol-4-yl]propyl]mor-pholin-2-yl]ethyl]-N-methyl-carbamate (1.00 g, 1.73 mmol) in DCM (10 mL) was added HBr/HOAc (4 mL, 40% solution). The mixture was stirred at 20° C. for 3 hours. On completion, the reaction mixture was concentrated in vacuo. Then the residue was purified by reverse phase (0.1% of FA condition) to give the title compound (700 mg, 64% yield) as off-white solid. LC-MS (ESI$^+$) m/z 444.4 (M+H)$^+$.

3-[3-Methyl-2-oxo-5-[3-(4-piperidyloxy)propyl] benzimidazol-1-yl]piperidine-2,6-dione (Intermediate ZM)

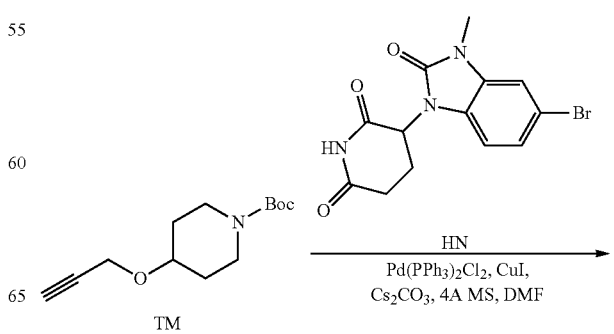

-continued

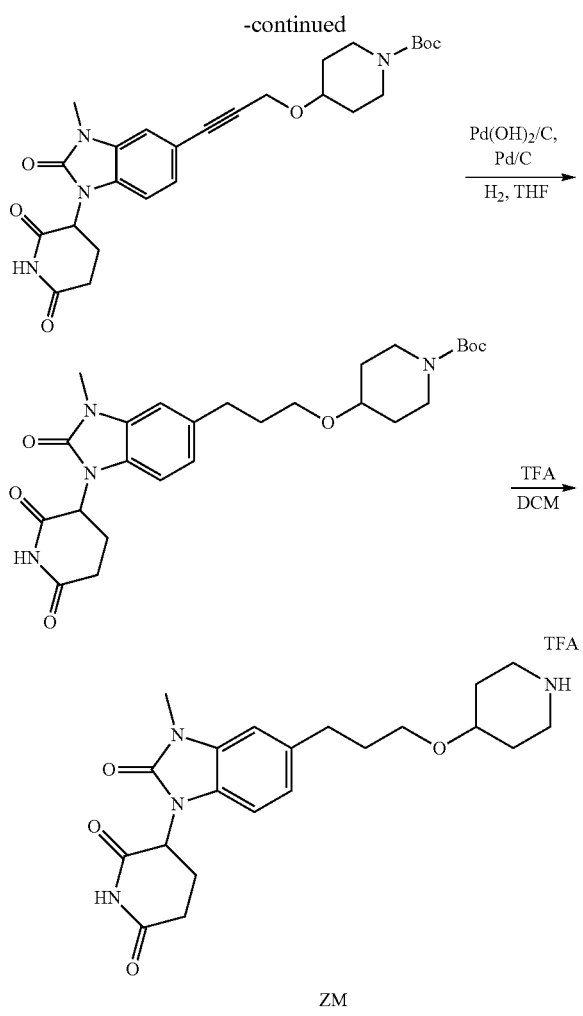

ZM

Step 1—Tert-butyl 4-[3-[1-(2,6-dioxo-3-piperidyl)-3-methyl-2-oxo-benzimidazol-5-yl]prop-2-ynoxy]piperidine-1-carboxylate To a mixture of 3-(5-bromo-3-methyl-2-oxo-benzimidazol-1-yl)piperidine-2,6-dione (350 mg, 1.04 mmol, Intermediate HN) and tert-butyl 4-prop-2-ynoxypiperidine-1-carboxylate (371 mg, 1.55 mmol, Intermediate™) in DMF (20 mL) was added Pd(PPh$_3$)$_2$Cl$_2$ (72.6 mg, 103 umol), CuI (39.4 mg, 207 umol), Cs$_2$CO$_3$ (1.35 g, 4.14 mmol) and 4 Å molecular sieves (200 mg, 1.04 mmol) in one portion at 25° C. under N$_2$. The reaction mixture was stirred at 80° C. for 2 hours. On completion, the reaction mixture was quenched by addition water (0.5 mL) at 25° C., and then extracted with EA (3×20 mL). The combined organic layers were washed with brine (20 mL), dried over Na$_2$SO$_4$, filtered and concentrated in vacuo to give a residue. The residue was purified by reverse phase (FA condition) to give the title compound (300 mg, 58% yield) as a yellow solid. $^1$H NMR (400 MHz, CDCl$_3$) δ 8.14 (s, 1H), 7.23-7.17 (m, 1H), 7.12 (d, J=1.2 Hz, 1H), 6.75 (d, J=8.1 Hz, 1H), 5.24-5.17 (m, 1H), 4.43 (s, 2H), 3.85-3.72 (m, 3H), 3.43 (s, 3H), 3.18-3.09 (m, 2H), 3.01-2.92 (m, 2H), 2.90-2.67 (m, 2H), 2.30-2.20 (m, 1H), 1.94-1.86 (m, 2H), 1.64-1.57 (m, 2H), 1.47 (s, 9H); LC-MS (ESI$^+$) m/z 519.3 (M+Na)$^+$.

Step 2—Tert-butyl 4-[3-[1-(2,6-dioxo-3-piperidyl)-3-methyl-2-oxo-benzimidazol-5-yl]propoxy]piperidine-1-carboxylate To a solution of tert-butyl 4-[3-[1-(2,6-dioxo-3-piperidyl)-3-methyl-2-oxo-benzimidazol-5-yl]prop-2-ynoxy]piperidine-1-carboxylate (300 mg, 604 umol) in THF (4 mL) was added Pd/C (50 mg, 10 wt %) and Pd(OH)$_2$/C (50 mg, 10 wt %) under N$_2$. The suspension was degassed under vacuum and purged with H$_2$ three times. The mixture was stirred at 25° C. for 2 hours under H$_2$ (15 psi). On completion, the reaction mixture was filtered and the filtrate was concentrated in vacuo to give a residue. The residue was purified by reverse phase (FA condition) to give the title compound (300 mg, 84% yield) as a yellow solid. $^1$H NMR (400 MHz, CDCl$_3$) δ 8.24 (s, 1H), 6.95-6.85 (m, 2H), 6.73 (d, J=8.2 Hz, 1H), 5.26-5.18 (m, 1H), 3.81-3.73 (m, 2H), 3.49-3.42 (m, 6H), 3.15-3.05 (m, 2H), 2.99-2.82 (m, 2H), 2.75 (t, J=7.6 Hz, 3H), 2.28-2.19 (m, 1H), 1.95-1.77 (m, 4H), 1.53 (d, J=8.8 Hz, 2H), 1.47 (s, 9H); LC-MS (ESI$^+$) m/z 401.0 (M+H −100)$^+$.

Step 3—3-[3-Methyl-2-oxo-5-[3-(4-piperidyloxy)propyl]benzimidazol-1-yl]piperidine-2,6-dione To a mixture of tert-butyl 4-[3-[1-(2,6-dioxo-3-piperidyl)-3-methyl-2-oxo-benzimidazol-5-yl]propoxy]piperidine-1-carboxylate (270 mg, 539 umol) in DCM (4 mL) was added TFA (1.84 g, 16.2 mmol) at 25° C. The mixture was stirred at 25° C. for 2 hours. On completion, the reaction mixture was concentrated in vacuo to give a residue. The residue was purified by reverse phase (TFA condition) to give the title compound (162 mg, 58% yield, TFA salt) as a yellow solid. LC-MS (ESI+) m/z 401.0 (M+H)$^+$.

3-[4-[3-(Azetidin-3-yloxy)propyl]-3-methyl-2-oxo-benzimidazol-1-yl]piperidine-2,6-dione (Intermediate ZN)

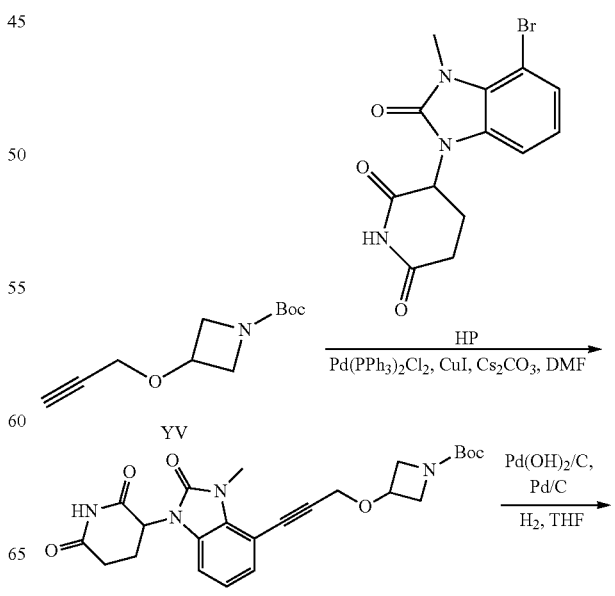

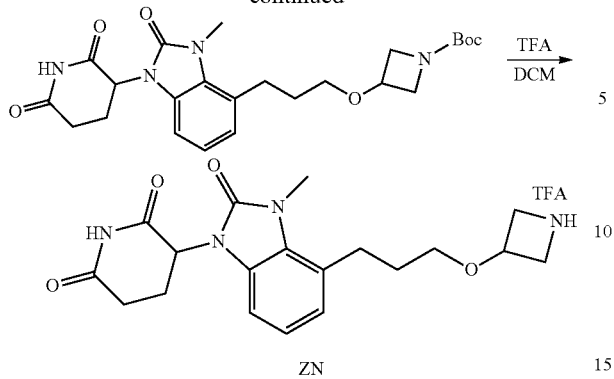

Step 1—Tert-butyl 3-[3-[1-(2,6-dioxo-3-piperidyl)-3-methyl-2-oxo-benzimidazol-4-yl]prop-2-ynoxy]azetidine-1-carboxylate To a mixture of tert-butyl 3-prop-2-ynoxyazetidine-1-carboxylate (499 mg, 2.37 mmol, Intermediate YV) and 3-(4-bromo-3-methyl-2-oxo-benzimidazol-1-yl)piperidine-2,6-dione (400 mg, 1.18 mmol, Intermediate HP) in DMF (3 mL) was added CuI (22.5 mg, 118 umol), $Cs_2CO_3$ (1.93 g, 5.91 mmol), $Pd(PPh_3)_2Cl_2$ (83.0 mg, 118 umol) and 4 Å molecular sieves (100 mg). The reaction mixture was stirred at 80° C. for 4 hours. On completion, the reaction mixture was filtered and concentrated in vacuo. The residue was purified by reverse phase (0.1% FA condition) to give the title compound (400 mg, 72% yield) as brown solid. $^1$H NMR (400 MHz, DMSO-$d_6$) δ 11.11 (s, 1H), 7.21-7.16 (m, 1H), 7.14-7.11 (m, 1H), 7.06-7.01 (m, 1H), 5.42-5.37 (m, 1H), 4.49-4.45 (m, 3H), 4.09-4.04 (m, 2H), 3.77-3.72 (m, 2H), 3.63 (s, 3H), 2.92-2.84 (m, 1H), 2.73-2.62 (m, 2H), 2.07-2.00 (m, 1H), 1.37 (s, 9H).

Step 2—Tert-butyl 3-[3-[1-(2,6-dioxo-3-piperidyl)-3-methyl-2-oxo-benzimidazol-4-yl]propoxy]azetidine-1-carboxylate To a mixture of tert-butyl 3-[3-[1-(2,6-dioxo-3-piperidyl)-3-methyl-2-oxo-benzimidazol-4-yl]prop-2-ynoxy]azetidine-1-carboxylate (400 mg, 853 umol) in THF (10 mL) was added Pd/C (150 mg, 10 wt %) and $Pd(OH)_2$/C (150 mg, 10 wt %). The reaction mixture was stirred at 25° C. for 12 hours under $H_2$ (15 Psi). On completion, the reaction mixture was filtered and concentrated in vacuo to give the title compound (300 mg, 74% yield) as light yellow solid. LC-MS (ESI$^+$) m/z 417.2 (M+H−56)$^+$.

Step 3—3-[4-[3-(Azetidin-3-yloxy)propyl]-3-methyl-2-oxo-benzimidazol-1-yl]piperidine-2,6-dione To a mixture of tert-butyl 3-[3-[1-(2,6-dioxo-3-piperidyl)-3-methyl-2-oxo-benzimidazol-4-yl]propoxy]azetidine-1-carboxylate (290 mg, 613.71 umol) in DCM (3 mL) was added TFA (44.6 g, 391 mmol, 29.0 mL). The reaction mixture was stirred at 25° C. for 1 hour. On completion, the reaction mixture was concentrated in vacuo to give the title compound (298 mg, 99% yield, TFA salt) as red oil. LC-MS (ESI$^+$) m/z 373.2 (M+H)$^+$.

3-[4-[3-(4-Piperidyloxy)propyl]pyrido[2,3-b]indol-9-yl]piperidine-2,6-dione (Intermediate ZO)

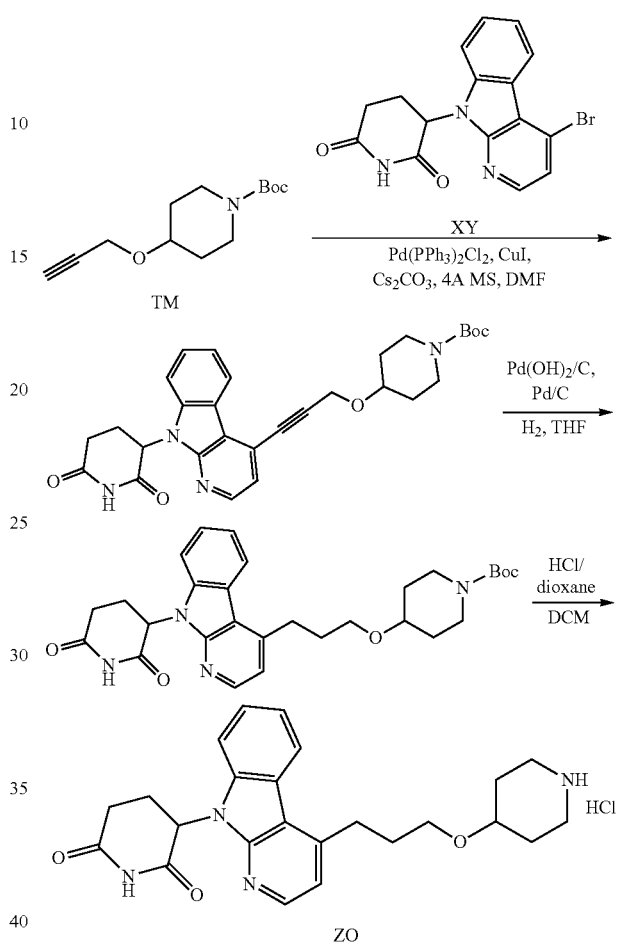

Step 1—Tert-butyl 4-[3-[9-(2,6-dioxo-3-piperidyl)pyrido[2,3-b]indol-4-yl]prop-2-ynoxy]piperidine-1-carboxylate To a solution 3-(4-bromopyrido[2,3-b]indol-9-yl)piperidine-2,6-dione (400 mg, 1.12 mmol, Intermediate XY) and tert-butyl 4-prop-2-ynoxypiperidine-1-carboxylate (534 mg, 2.23 mmol, Intermediate™) in DMF (8 mL) was added $Pd(PPh_3)_2Cl_2$ (157 mg, 223 umol), CuI (42.5 mg, 223 umol), $Cs_2CO_3$ (1.82 g, 5.58 mmol) and 4 Å molecular sieves (40 mg). The mixture was de-gassed and then heated at 80° C. for 2 hrs. On completion, the reaction mixture was concentrated in vacuo. The crude product was purified by reverse phase HPLC (0.1% FA condition) to give the title compound (200 mg, 34% yield) as brown solid. $^1$H NMR (400 MHz, DMSO-$d_6$) δ 11.15 (s, 1H), 8.49 (d, J=7.6 Hz, 1H), 8.42 (d, J=5.2 Hz, 1H), 7.72-7.64 (m, 1H), 7.62-7.56 (m, 1H), 7.36-7.33 (m, 1H), 7.32-7.29 (m, 1H), 6.06 (s, 1H), 4.71 (s, 2H), 3.88-3.84 (m, 1H), 3.70-3.65 (m, 2H), 3.10-3.05 (m, 2H), 3.05-2.95 (m, 1H), 2.77-2.68 (m, 1H), 2.61 (s, 1H), 2.20-2.11 (m, 1H), 1.96-1.88 (m, 2H), 1.52-1.44 (m, 2H), 1.39 (s, 9H); LC-MS (ESI$^+$) m/z 539.3 (M+Na)$^+$.

Step 2—Tert-butyl 4-[3-[9-(2,6-dioxo-3-piperidyl)pyrido[2,3-b]indol-4-yl]propoxy]piperidine-1-carboxylate To a solution of tert-butyl 4-[3-[9-(2,6-dioxo-3-piperidyl)pyrido[2,3-b]indol-4-yl]prop-2-ynoxy]piperidine-1-carboxylate (200 mg, 387 umol in THF (5 mL) was added Pd(OH)$_2$ (40.0 mg, 10 wt %), Pd/C (40.0 mg, 10 wt %) under N$_2$. The suspension was degassed under vacuum and purged with H$_2$ several times. The mixture was stirred at 25° C. for 15 hours under H$_2$ (15 psi). On completion, the reaction mixture was filtered and the filtrate was concentrated in vacuo to give the title compound (120 mg, 59% yield) as white solid. $^1$H NMR (400 MHz, DMSO-d$_6$) δ 11.13 (s, 1H), 8.31 (d, J=5.2 Hz, 1H), 8.24 (d, J=7.6 Hz, 1H), 7.67-7.58 (m, 1H), 7.55-7.47 (m, 1H), 7.28 (t, J=7.6 Hz, 1H), 7.10 (d, J=5.2 Hz, 1H), 6.18-5.92 (m, 1H), 3.67-3.47 (m, 6H), 3.29 (s, 1H), 3.28-3.21 (m, 2H), 3.17-2.93 (m, 4H), 2.15-2.07 (m, 1H), 2.03-1.93 (m, 2H), 1.86-1.76 (m, 2H), 1.39 (s, 9H), 1.35 (s, 1H); LC-MS (ESI$^+$) m/z 521.3 (M+Na)$^+$.

Step 3—3-[4-[3-(4-Piperidyloxy)propyl]pyrido[2,3-b]indol-9-yl]piperidine-2,6-dione To a mixture of tert-butyl 4-[3-[9-(2,6-dioxo-3-piperidyl)pyrido[2,3-b]indol-4-yl]propoxy]piperidine-1-carboxylate (100 mg, 192 umol) in DCM (2 mL) was added HCl/dioxane (2 mL). The reaction mixture was stirred at 25° C. for 2 hrs. On completion, the reaction mixture was concentrated in vacuo to give the title compound (80.0 mg, 91% yield) as brown solid. LC-MS (ESI+) m/z 421.3 (M+H)$^+$.

3-[3-Methyl-4-[3-[2-(methylamino)ethoxy]propyl]-2-oxo-benzimidazol-1-yl]piperidine-2,6-dione (Intermediate ZP)

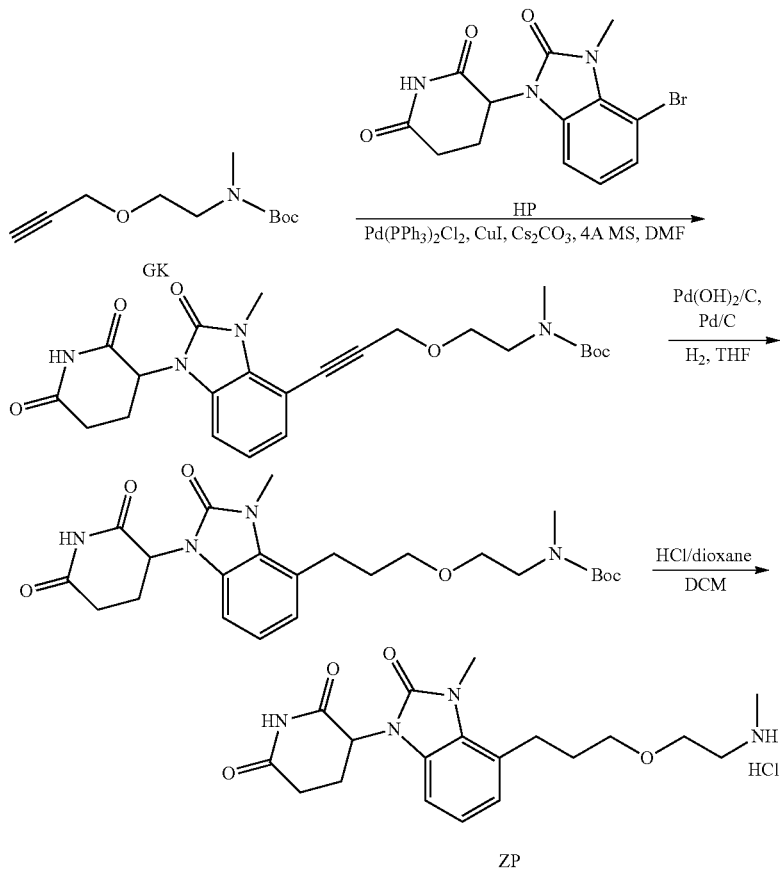

Step 1—Tert-butyl N-[2-[3-[1-(2,6-dioxo-3-piperidyl)-3-methyl-2-oxo-benzimidazol-4-yl]prop-2-ynoxy]ethyl]-N-methyl-carbamate 3-(4-bromo-3-methyl-2-oxo-benzimidazol-1-yl)piperidine-2,6-dione (400 mg, 1.18 mmol, Intermediate HP), tert-butyl N-methyl-N-(2-prop-2-ynoxyethyl)carbamate (440 mg, 2.06 mmol, Intermediate GK), Pd(PPh$_3$)$_2$Cl$_2$ (166 mg, 237 umol), CuI (45.1 mg, 237 umol), 4 Å molecular sieves (400 mg) and Cs$_2$CO$_3$ (1.54 g, 4.73 mmol) in DMF (5 mL) was de-gassed and then heated at 80° C. for 2 hours under N$_2$. On completion, the reaction mixture was filtered and the filtrate was concentrated in vacuo. The residue was purified by reversed-phase (0.1% FA condition) to give the title compound (310 mg, 39% yield) as a yellow solid. LC-MS (ESI$^+$) m/z 415.1 (M+H−56)$^+$.

Step 2—Tert-butyl N-[2-[3-[1-(2,6-dioxo-3-piperidyl)-3-methyl-2-oxo-benzimidazol-4-yl]propoxy]ethyl]-N-methyl-carbamate To a solution of tert-butyl N-[2-[3-[1-(2,6-dioxo-3-piperidyl)-3-methyl-2-oxo-benzimidazol-4-yl]prop-2-ynoxy]

ethyl]-N-methyl-carbamate (390 mg, 829 umol) in THF (10 mL) was added Pd/C (0.1 g, 10% wt) and Pd(OH)$_2$/C (0.1 g, 20% wt). The suspension was degassed under vacuum and purged with H$_2$ several times. The reaction mixture was stirred at 25° C. for 12 hours under H$_2$ (15 psi). On completion, the mixture was filtered and the filtrate was concentrated in vacuo to give the title compound (390 mg, 99% yield) as a yellow solid. $^1$H NMR (400 MHz, DMSO-d$_6$) δ 8.25 (s, 1H), 7.12-6.96 (m, 1H), 6.95-6.86 (m, 1H), 6.72-6.60 (m, 1H), 5.30-5.15 (m, 1H), 3.48 (s, 3H), 3.65-3.58 (m, 2H), 3.52-3.45 (m, 2H), 3.45-3.35 (m, 2H), 3.08-2.95 (m, 3H), 2.92 (s, 3H), 2.85-2.60 (m, 2H), 2.25-2.15 (m, 1H), 1.96-1.85 (m, 2H), 1.50 (s, 1H); LC-MS (ESI$^+$) m/z 375.1 (M+H−100)$^+$.

Step 3—3-[3-Methyl-4-[3-[2-(methylamino)ethoxy]propyl]-2-oxo-benzimidazol-1-yl]piperidine-2,6-dione To a solution of tert-butyl N-[2-[3-[1-(2,6-dioxo-3-piperidyl)-3-methyl-2-oxo-benzimidazol-4-yl]propoxy]ethyl]-N-methyl-carbamate (100 mg, 211 umol) in DCM (2 mL) was added HCl/dioxane (2 mL). The reaction mixture was stirred at 20° C. for 2 hrs. On completion, the mixture was concentrated in vacuo to give the title compound (85.0 mg, 98% yield, HCl salt) as a yellow solid. LC-MS (ESI$^+$) m/z 375.1 (M+H)$^+$.

3-[3-Methyl-5-[3-[3-(methylamino)propoxy]prop-1-ynyl]-2-oxo-benzimidazol-1-yl]piperidine-2,6-dione (Intermediate ZQ)

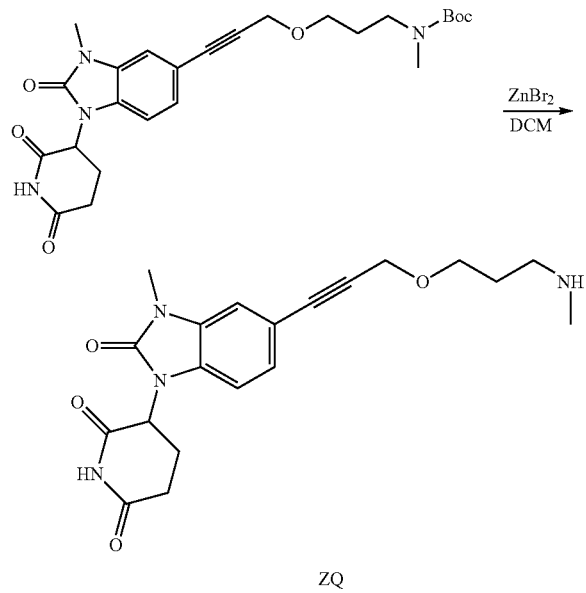

To a solution of tert-butyl N-[3-[3-[1-(2,6-dioxo-3-piperidyl)-3-methyl-2-oxo-benzimidazol-5-yl]prop-2-ynoxy]propyl]-N-methyl-carbamate (200 mg, 412 umol, synthesized via Step 1 of Intermediate QI) in DCM (3.00 mL) was added ZnBr$_2$ (1.39 g, 6.19 mmol). The mixture was stirred at 20° C. for 20 hrs. On completion, the reaction mixture was concentrated in vacuo to give the title compound (158 mg, 99% yield) as yellow solid. LC-MS (ESI$^+$) m/z 385.2 (M+H)$^+$.

3-[3-Methyl-5-[[4-(methylaminomethyl)-1-piperidyl]methyl]-2-oxo-benzimidazol-1-yl]piperidine-2,6-dione (Intermediate ZR)

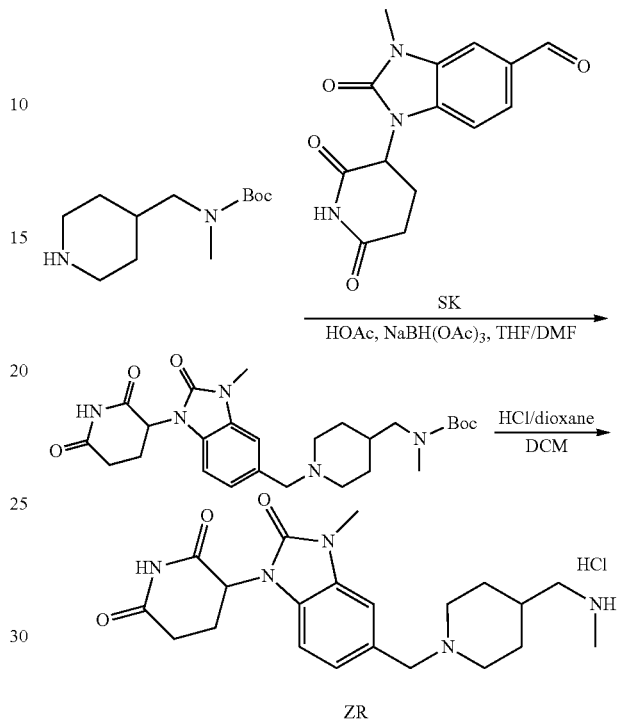

Step 1—Tert-butyl N-[[1-[[1-(2,6-dioxo-3-piperidyl)-3-methyl-2-oxo-benzimidazol-5-yl]methyl]-4-piperidyl]methyl]-N-methylcarbamate To a solution of tert-butyl N-methyl-N-(4-piperidylmethyl)carbamate (119 mg, 522 umol, CAS #138022-04-5) and 1-(2,6-dioxo-3-piperidyl)-3-methyl-2-oxo-benzimidazole-5-carbaldehyde (150 mg, 522 umol, Intermediate SK) in a mixed solvents of DMF (1.2 mL) and THF (2.4 mL) was added HOAc until the pH=5-6. After the reaction mixture was stirred at 10° C. for 1 hr, then NaBH(OAc)$_3$ (221 mg, 1.04 mmol) was added. Then the reaction mixture was stirred at 10° C. for 48 hrs. On completion, the reaction mixture was quenched by H$_2$O (0.5 mL), filtered and the filtrate was concentrated in vacuo to give a residue. The residue was purified by reverse phase (0.1% FA condition) to give the title compound (230 mg, 88% yield) as a white solid. $^1$H NMR (400 MHz, CDCl$_3$) δ 8.53 (s, 1H), 7.21 (d, J=16.0 Hz, 1H), 7.01 (J=8.0 Hz, 1H), 6.76 (d, J=8.0 Hz, 1H), 5.24 (dd, J=5.2, 12.8 Hz, 1H), 4.06-3.80 (m, 2H), 3.43 (s, 3H), 3.24 (d, J=8.0 Hz, 2H), 3.13 (s, 2H), 2.98-2.87 (m, 1H), 2.87 (s, 3H), 2.79 (d, J=4.8 Hz, 1H), 2.77-2.63 (m, 1H), 2.57-2.39 (m, 1H), 2.37-2.16 (m, 2H), 1.91-1.78 (m, 1H), 1.78-1.60 (m, 2H), 1.60-1.48 (m, 1H), 1.44 (s, 9H); LC-MS (ESI$^+$) m/z 500.4 (M+H)$^+$.

Step 2—3-[3-Methyl-5-[[4-(methylaminomethyl)-1-piperidyl]methyl]-2-oxo-benzimidazol-1-yl]piperidine-2,6-dione To a solution of tert-butyl N-[[1-[[1-(2,6-dioxo-3-piperidyl)-3-methyl-2-oxo-benzimidazol-5-yl]methyl]-4-piperidyl]methyl]-N-methyl-carbamate (230 mg, 460 umol) in DCM (3 mL) was added HCl/dioxane (4 M, 3 mL). The reaction mixture was stirred at 20° C. for 2 hrs. On completion, the reaction mixture was concentrated in vacuo to give the title compound (200 mg, 99% yield, HCl) as a white solid. LC-MS (ESI$^+$) m/z 400.3 (M+H)$^+$.

3-[3-Methyl-5-[3-[2-(methylamino)ethoxy]propyl]-2-oxo-benzimidazol-1-yl]piperidine-2,6-dione (Intermediate ZS)

umol) and Cs$_2$CO$_3$ (2.89 g, 8.87 mmol). The reaction mixture was stirred at 80° C. for 4 hrs. On completion, the reaction mixture was concentrated in vacuo. The crude product was purified by reverse phase HPLC (0.1% FA condition) to give the title compound (540 mg, 52% yield) as yellow solid. $^1$H NMR (400 MHz, DMSO-d$_6$) δ 11.10 (s, 1H), 7.31 (s, 1H), 7.18-7.12 (m, 2H), 5.38 (dd, J=5.6, 12.4 Hz, 1H), 4.39 (s, 2H), 3.62 (t, J=5.6 Hz, 2H), 3.38-3.36 (m, 2H), 3.34 (s, 3H), 2.82 (s, 3H), 2.77-2.70 (m, 1H), 2.65-2.58 (m, 2H), 2.08-2.00 (m, 1H), 1.39 (s, 9H); LC-MS (ESI$^+$) m/z 493.3 (M+Na)$^+$.

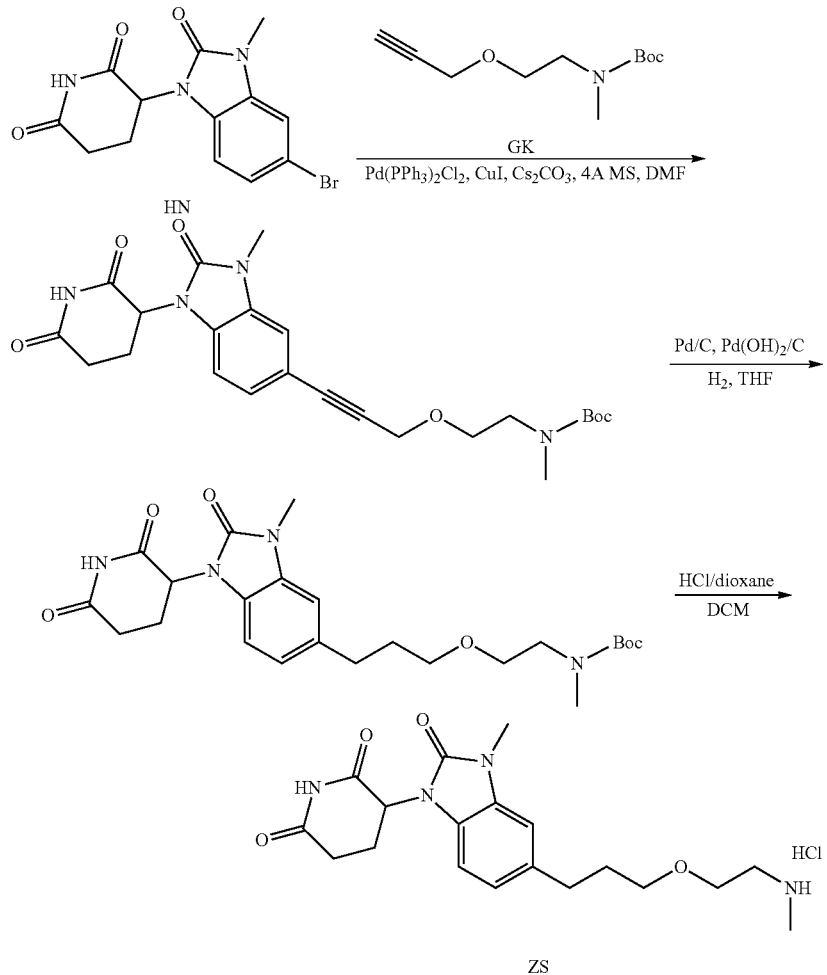

Step 1—Tert-butyl N-[2-[3-[1-(2,6-dioxo-3-piperidyl)-3-methyl-2-oxo-benzimidazol-5-yl]prop-2-ynoxy]ethyl]-N-methyl-carbamate To a solution tert-butyl N-methyl-N-(2-prop-2-ynoxyethyl)carbamate (946 mg, 4.44 mmol, Intermediate GK) and 3-(5-bromo-3-methyl-2-oxo-benzimidazol-1-yl)piperidine-2,6-dione (600 mg, 1.77 mmol, Intermediate HN) in DMF (10 mL) was added Pd(PPh$_3$)$_2$Cl$_2$ (249 mg, 355 umol), CuI (67.6 mg, 355 umol), 4 Å molecular sieves (80.0 mg, 305

Step 2—Tert-butyl N-[2-[3-[1-(2,6-dioxo-3-piperidyl)-3-methyl-2-oxo-benzimidazol-5-yl]propoxy]ethyl]-N-methyl-carbamate To a solution of tert-butyl N-[2-[3-[1-(2,6-dioxo-3-piperidyl)-3-methyl-2-oxo-benzimidazol-5-yl]prop-2-ynoxy]ethyl]-N-methyl-carbamate (530 mg, 1.13 mmol) in THF (5 mL) was added Pd/C (40.0 mg, 10 wt %), Pd(OH)$_2$ (40.0 mg, 10 wt %) under N$_2$. The suspension was degassed under vacuum and purged with H$_2$ several times. The mixture was stirred at 25° C. for 15 hours under H$_2$ (15 psi). On completion, the reaction mixture was filtered and concentrated in vacuo to give the title compound (450 mg, 84% yield) as yellow oil. $^1$H NMR (400 MHz, DMSO-d$_6$) δ 11.07 (s, 1H), 7.04-6.97 (m, 2H), 6.85 (d, J=8.0 Hz, 1H), 5.33 (dd, J=4.8, 12.4 Hz, 1H), 3.48-3.43 (m, 2H), 3.38-3.30 (m, 3H), 2.82 (s, 3H), 2.72-2.61 (m, 4H), 2.33 (s, 1H), 2.07 (s, 4H), 2.04-1.96 (m, 1H), 1.86-1.74 (m, 2H), 1.38 (s, 9H); LC-MS (ESI+) m/z 497.3 (M+Na)+.

Step 3—3-[3-Methyl-5-[3-[2-(methylamino)ethoxy]propyl]-2-oxo-benzimidadazol-1-yl]piperidine-2,6-dione To a solution of tert-butyl N-[2-[3-[1-(2,6-dioxo-3-piperidyl)-3-methyl-2-oxo-benzimidazol-5-yl]propoxy]ethyl]-N-methyl-carbamate (430 mg, 906 umol) in DCM (2 mL) was added HCl/dioxane (2 mL). The mixture was stirred at 25° C. for 2 hrs. On completion, the reaction mixture was concentrated in vacuo to give the title compound (330 mg, 78% yield) as white solid. LC-MS (ESI+) m/z 375.2 (M+H)+.

Tert-butyl N-methyl-N-(3-vinyloxypropyl)carbamate (Intermediate ZT)

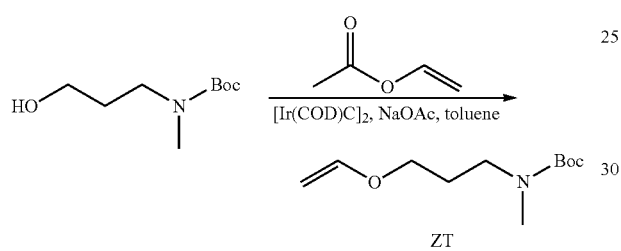

To a mixture of tert-butyl N-(3-hydroxypropyl)-N-methyl-carbamate (5.00 g, 26.4 mmol, CAS #98642-44-5) and vinyl acetate (3.41 g, 39.6 mmol, CAS #108-05-4) in toluene (20 mL) was added chloroiridium (1Z,5Z)-cyclooca-1,5-diene (177 mg, 264 umol, CAS #12112-67-3) and Na₂CO₃ (1.68 g, 15.8 mmol) at 25° C. under N₂ in glove box. The mixture was stirred at 100° C. for 2 hours. On completion, the reaction mixture was quenched with water (20 mL), filtered and the filtrate was extracted with EA (2×25 mL). The combined organic layers were washed with brine (10 mL), dried over Na₂SO₄, filtered and concentrated in vacuo to give a residue. The residue was purified by column chromatography (SiO₂, Petroleum ether/Ethyl acetate=30/1) to afford the title compound (2.40 g, 42% yield) as a yellow oil. $^1$H NMR (400 MHz, CDCl₃) δ 6.51-6.42 (m, 1H), 4.21-4.13 (m, 1H), 4.02-3.96 (m, 1H), 3.69 (t, J=6.2 Hz, 2H), 3.32 (s, 2H), 2.86 (s, 3H), 1.94-1.80 (m, 2H), 1.46 (s, 9H).

3-[3-Methyl-5-[2-[3-(methylamino)propoxy]ethyl]-2-oxo-benzimidazol-1-yl]piperidine-2,6-dione (Intermediate ZU)

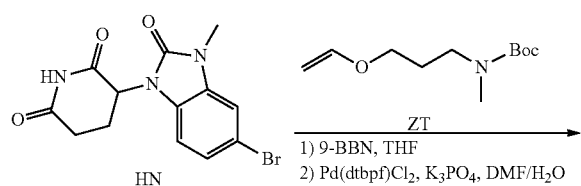

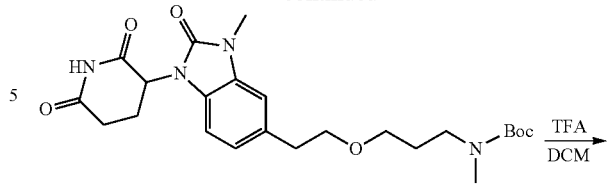

Step 1—Tert-butyl N-[3-[2-[1-(2,6-dioxo-3-piperidyl)-3-methyl-2-oxo-benzimidazol-5-yl]ethoxy]propyl]-N-methyl-carbamate To a solution of tert-butyl N-methyl-N-(3-vinyloxypropyl)carbamate (900 mg, 4.18 mmol, Intermediate ZT) in THF (10 mL) was added 9-BBN (0.5 M, 8.36 mL). The mixture was stirred at 25° C. for 2 hours. Then a solution of 3-(5-bromo-3-methyl-2-oxo-benzimidazol-1-yl)piperidine-2,6-dione (471 mg, 1.39 mmol, Intermediate HN), K₃PO₄ (739 mg, 3.48 mmol) and ditert-butyl(cyclopentyl)phosphane; dichloro palladium; iron (90.8 mg, 139 umol) in DMF (15 mL) and H₂O (3 mL) was added to the above mixture. The reaction mixture was stirred at 75° C. for 20 minutes under N₂. On completion, the reaction mixture was diluted with EA (100 mL), poured into water (50 mL) and extracted with EA (2×50 mL). The combined organic layers were dried with Na₂SO₄, filtrated and concentrated in vacuo. The residue was purified by reverse phase (0.1% FA) to give the title compound (300 mg, 45% yield) as a light yellow solid. LC-MS (ESI+) m/z 375.3 (M+H-100)+.

Step 2—3-[3-Methyl-5-[2-[3-(methylamino)propoxy]ethyl]-2-oxo-benzimidazol-1-yl]piperidine-2,6-dione To a solution of tert-butyl N-[3-[2-[1-(2,6-dioxo-3-piperidyl)-3-methyl-2-oxo-benzimidazol-5-yl]ethoxy]propyl]-N-methyl-carbamate (200 mg, 421 umol) in DCM (2 mL) was added TFA (30.8 g, 270 mmol, 20 mL). The reaction mixture was stirred at 25° C. for 1 hour. On completion, the reaction mixture was concentrated in vacuo to give the title compound (200 mg, 91% yield, 94% purity, TFA) as yellow oil. LC-MS (ESI+) m/z 375.3 (M+H)+.

4-[2-[2-(2-Aminoethoxy)ethoxy]ethylamino]-2-(2,6-dioxo-3-piperidyl)isoindoline-1,3-dione (Intermediate FI)

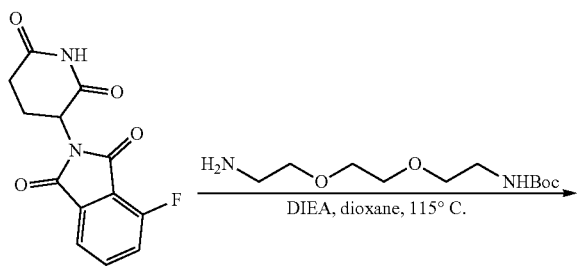

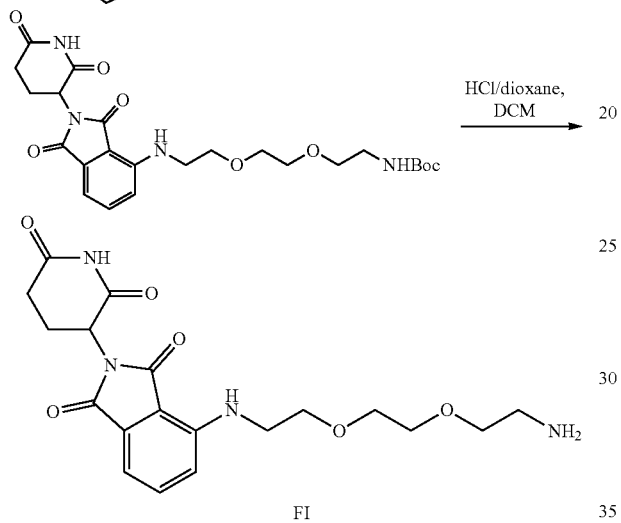

Step 1—Tert-butyl N-[2-[2-[2-[[2-(2,6-dioxo-3-piperidyl)-1,3-dioxo-isoindolin-4-yl]amino]ethoxy]ethoxy]ethyl]carbamate

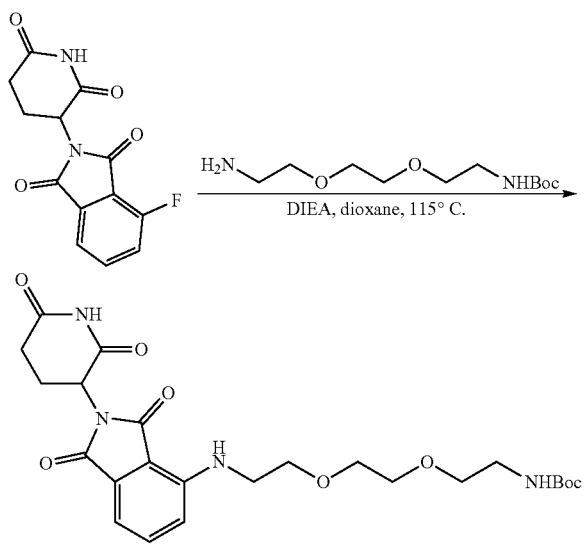

A solution of tert-butyl N-[2-[2-(2-aminoethoxy)ethyl]carbamate (2.50 g, 10.1 mmol), 2-(2,6-dioxo-3-piperidyl)-4-fluoro-isoindoline-1,3-dione (3.34 g, 12.1 mmol) and diisopropyl ethylamine (2.60 g, 20.1 mmol) in dioxane (120 mL) was stirred at 115° C. for 16 hours. On completion, the reaction mixture was concentrated in vacuo. The residue was purified by column chromatography (petroleum ether: ethyl acetate=1:1) to give the title compound (2.10 g, 40% yield) as yellow gum. $^1$H NMR (400 MHz, CDCl$_3$) δ 8.50 (s, 1H), 7.54-7.48 (m, 1H), 7.12 (d, J=7.2 Hz, 1H), 6.92 (d, J=8.4 Hz, 1H), 6.59-6.48 (m, 1H), 5.15-5.00 (m, 1H), 4.95-4.85 (m, 1H), 3.79-3.71 (m, 2H), 3.70-3.62 (m, 4H), 3.60-3.54 (m, 2H), 3.52-3.45 (m, 2H), 3.35-3.25 (m, 2H), 2.92-2.71 (m, 3H), 2.19-2.09 (m, 1H), 1.44 (s, 9H), LC-MS (Est) m/z 527.1 (M+Na)$^+$.

Step 2—4-[2-[2-(2-Aminoethoxy)ethoxy]ethylamino]-2-(2,6-dioxo-3-piperidyl)isoindoline-1,3-dione (Intermediate FI)

To a solution of tert-butyl N-[2-[2-[2-[[2-(2,6-dioxo-3-piperidyl)-1,3-dioxo-isoindolin-4-yl]amino]ethoxy]ethoxy]ethyl]carbamate (200 mg, 396 umol) in DCM (5 mL) was added HCl/dioxane (4 M, 5 mL). The reaction mixture was stirred at 25° C. for 10 minutes. On completion, the reaction mixture was concentrated in vacuo to give the title compound (200 mg, crude) as yellow solid. The crude product was used to next step directly without further purification. LC-MS (Est) m/z 405.2 (M+H)$^+$.

Methods

Example 1 (Method 1): 6-((1,6-naphthyridin-2-yl)amino)-4-(cyclopropylamino)-N-((1R,4R)-4-((1-((2-(2,6-dioxopiperidin-3-yl)-1,3-dioxoisoindolin-4-yl)oxy)-2-oxo-9,12,15-trioxa-3-azaicosan-20-yl)carbamoyl)cyclohexyl)nicotinamide, I-1

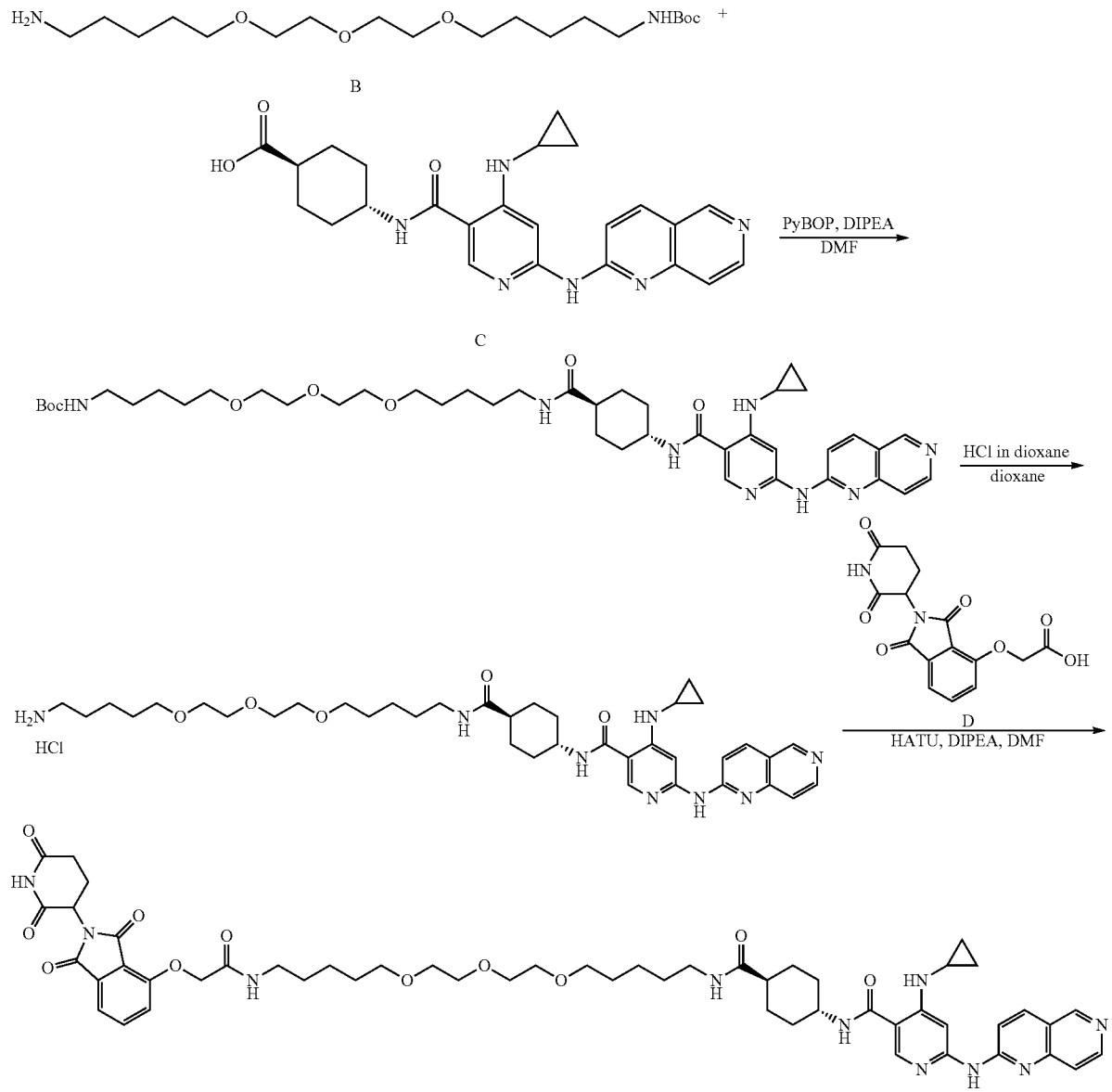

Step 1—tert-butyl (1-(((1R,4R)-4-(6-(((1,6-naphthyridin-2-yl)amino)-4 (cyclopropylamino)-nicotinamido)-cyclohexyl)-1-oxo-8,11,14-trioxa-2-azanonadecan-19-yl)carbamate To a stirred suspension of (1R,4R)-4-(6-((1,6-naphthyridin-2-yl)amino)-4-(cyclopropylamino)nicotinamido)cyclohexane-1-carboxylic acid (0.2 g, 0.5 mmol, Intermediate C) and tert-butyl (5-(2-(2-((5-aminopentyl)oxy)ethoxy)ethoxy)pentyl)carbamate (0.25 g, 0.67 mmol, Intermediate B) in DMF (2 mL) was added DIPEA (0.4 mL, 2.2 mmol) and PyBOP (0.35 g, 0.67 mmol) at rt. The resulting reaction mixture was stirred at rt for 1 h. The reaction mixture was transferred into ice water and the resulting mixture was extracted using ethyl acetate (3×20 mL). The combined organic layers were dried over anhydrous sodium sulfate and filtered. The filtrate was evaporated under reduced pressure and the crude product was purified using silica gel column chromatography (10% MeOH-DCM) to give tert-butyl (1-((1r,4r)-4-(6-((1,6-naphthyridin-2-yl)amino)-4-(cyclopropylamino)nicotinamido)cyclohexyl)-1-oxo-8,11,14-trioxa-2-azanonadecan-19-yl)carbamate as a brown solid (0.18 g, 50%). LC-MS (ESI⁺) m/z 804.1 (M−H)⁻

Step 2—6-((1,6-naphthyridin-2-yl)amino)-N-((1R,4R)-4-((5-(2-(2-((5-aminopentyl)oxy)ethoxy)-ethoxy)-pentyl)carbamoyl)cyclohexyl)-4-(cyclopropylamino)nicotinamide hydrochloride To a stirred solution of tert-butyl (1-((1r,4r)-4-(6-((1,6-naphthyridin-2-yl)amino)-4-(cyclopropylamino)nicotinamido)cyclohexyl)-1-oxo-8,11,14-trioxa-2-azanonadecan-19-yl)-carbamate (0.18 g, 0.22 mmol) in 1,4 dioxane (3 mL) was added 4N HCl in dioxane (1 mL) at 0° C. The resulting reaction mixture was warmed to rt and stirred for 2 h. The reaction mixture was evaporated under vacuum and triturated using diethyl ether to give 6-((1,6-naphthyridin-2-yl)amino)-N-((1r,4r)-4-((5-(2-(2-((5-aminopentyl)oxy)ethoxy)ethoxy)pentyl)carbamoyl)-cyclohexyl)-4-(cyclopropylamino)nicotinamide hydrochloride as yellow solid (0.16 g, 96%). LCMS (ESI$^+$) m/z 706.6 (M+H)$^+$.

Step 3—6-((1,6-naphthyridin-2-yl)amino)-4-(cyclopropylamino)-N-((1R,4R)-4-((1-((2-(2,6-dioxopiperidin-3-yl)-1,3-dioxoisoindolin-4-yl)oxy)-2-oxo-9,12,15-trioxa-3-azaicosan-20-yl)carbamoyl)cyclohexyl)nicotinamide To a solution of 2-((2-(2,6-dioxopiperidin-3-yl)-1,3-dioxoisoindolin-4-yl)oxy)acetic acid (0.085 g, 0.24 mmol, Intermediate D) in DMF (5 mL) was added HATU (0.14 g, 0.36 mmol) at 0° C. and the reaction mixture was stirred for 30 minutes. To this reaction mixture, 6-((1,6-naphthyridin-2-yl)amino)-N-((1r,4r)-4-((5-(2-(2-((5-aminopentyl)oxy)ethoxy)ethoxy)pentyl)-carbamoyl)-cyclohexyl)-4-(cyclopropylamino)nicotinamide hydrochloride (0.18 g, 0.24 mmol) and DIPEA (0.15 mL, 0.72 mmol) was added at 0° C. The resulting reaction mixture was warmed to rt and stirred for 1 h. The reaction mixture was transferred into ice water, and the resulting precipitate was filtered off and washed with water and dried under reduced pressure. The crude product was purified using preparative HPLC (0.1% formic acid in water/ACN) to give 6-((1,6-naphthyridin-2-yl)amino)-4-(cyclopropylamino)-N-((1r,4r)-4-((1-((2-(2,6-dioxopiperidin-3-yl)-1,3-dioxoisoindolin-4-yl)oxy)-2-oxo-9,12,15-trioxa-3-azaicosan-20-yl)carbamoyl)cyclohexyl)-nicotinamide I-1 as off white solid (0.04 g, 16%). $^1$H NMR (400 MHz, DMSO) δ 11.11 (s, 1H), 10.34 (s, 1H), 9.02 (s, 1H), 8.55-8.53 (m, 3H), 8.40 (s, 1H), 8.24 (d, J=9.2 Hz, 1H), 8.13-8.11 (m, 1H), 7.96-7.93 (m, 1H), 7.79 (t, J=7.6 Hz, 1H), 7.78-7.69 (m, 1H), 7.54 (d, J=5.6 Hz, 1H), 7.49-7.46 (m, 2H), 7.36 (d, J=8.4 Hz, 1H), 5.12-5.09 (m, 1H), 4.75 (s, 2H), 3.72 (bs, 1H), 3.48-3.47 (m, 7H), 3.14-3.09 (m, 2H), 2.99-2.98 (m, 2H), 2.96-2.94 (m, 1H), 2.59-2.52 (m, 2H), 2.03-2.0 (m, 2H), 1.85-1.83 (m, 2H), 1.73-1.71 (m, 2H), 1.45-1.42 (m, 6H), 1.40-1.38 (m, 2H), 1.36-1.34 (m, 2H), 1.31-1.28 (m, 1H), 1.25-1.24 (m, 4H), 0.92-0.91 (m, 2H), 0.56 (s, 2H). LC-MS (ESI$^+$) m/z 1020.2 (M+H)$^+$.

TABLE 2

Compounds synthesized via Method 1, with the coupling of various amines with acid Intermediate C in Step 1, followed by coupling with acid Intermediate D in Step 3.

| Ex-# | I-# | Intermediate Amine | LCMS (ES+) m/z (M + H)+ | HNMR (400 MHz, DMSO-d6) δ |
|---|---|---|---|---|
| 2 | I-2 | E | 932.2 | 11.15 (s, 1H), 10.37 (s, 1H), 9.05 (s, 1H), 8.42 (s, 1H), 8.33-8.26 (m, 2H), 8.15 (d, J = 7.6 Hz, 1H), 7.98 (s, 1H), 7.81 (t, J = 8 Hz, 2H), 7.57-7.49 (m, 3H), 7.38 (d, J = 8.4 Hz, 1H), 5.15-5.10 (m, 2H), 4.77 (s, 1H), 3.16-2.87 (m, 6H), 2.05-2.02 (m, 4H), 1.87-1.72 (m, 5H), 1.46-1.23 (m, 18H), 0.94-0.85 (m, 4H), 0.58 (s, 2H) |
| 3 | I-3 | tert-butyl (5-aminopentyl)carbamate (CAS# 51644-96-3) | 845.8 | 11.14 (s, 1H), 10.37 (s, 1H), 9.04 (s, 1H), 8.65-8.45 (m, 3H), 8.40 (s, 1H), 8.23 (d, J = 9.2 Hz, 1H), 8.18-8.05 (m, 2H), 7.98-7.88 (m, 1H), 7.81 (t, J = 8.0 Hz, 1H), 7.75-7.65 (m, 1H), 7.63-7.53 (m, 1H), 7.52-7.42 (m, 2H), 7.38 (d, J = 8.4 Hz, 1H), 5.05-5.15 (m, 1H), 4.76 (s, 2H), 3.75-3.61 (m, 1H), 3.18-3.08 (m, 2H), 3.15-2.95 (m, 2H), 2.94-2.81 (m, 1H), 2.61-2.51 (m, 3H), 2.11-1.97 (m, 2H), 1.90-1.80 (m, 2H), 1.79-1.70 (m, 2H), 1.50-1.20 (m, 10H), 0.92 (d, J = 5.2 Hz, 2H), 0.57 (s, 2H) |
| 4$^a$ | I-4 | tert-butyl (5-aminopentyl)carbamate (CAS# 51644-96-3) | 845.0 | 11.18 (s, 1H), 10.38 (s, 1H), 9.05 (s, 1H), 8.57-8.56 (m, 3H), 8.42 (s, 1H), 8.28 (d, J = 9.2 Hz, 1H), 8.15 (s, 1H), 8.14 (d, J = 2.8 Hz, 1H), 7.96 (t, J = 5.2 Hz, 1H), 7.83 (t, J = 7.2 Hz, 1H), 7.72 (t, J = 5.2 Hz, 1H), 7.57 (d, J = 6 Hz, 1H), 7.51 (d, J = 7.6 Hz, 2H), 7.41 (d, J = 8.8 Hz, 1H), 5.16-5.12 (m, 1H), 4.77 (s, 2H), 3.67 (bs, 2H), 3.41-3.12 (m, 2H), 3.02-2.94 (m, 2H), 2.90-2.86 (m, 2H), 2.60-2.51 (m, 3H), 2.08-2.03 (m, 2H), 1.87 (d, J = 10 Hz, 2H), 1.76 (d, J = 10.4 Hz, 2H), 1.46-1.23 (m, 11H), 0.95-0.93 (m, 2H), 0.59 (s, 2H) |
| 5 | I-5 | F | 976.1 | 11.11 (s, 1H), 10.34 (s, 1H), 9.03 (s, 1H), 8.55-8.53 (m, 3H), 8.40 (s, 1H), 8.25 (d, J = 9.2 Hz, 1H), 8.15 (s, 1H), 8.13 (d, J = 7.6 Hz, 1H), 7.94 (t, J = 5.6 Hz, 1H), 7.79 (t, J = 7.6 Hz, 1H), 7.69 (t, J = 5.2 Hz, 1H), 7.55 (d, J = 5.6 Hz, 1H), 7.49-7.46 (m, 2H), 7.37 (d, J = 8.8 Hz, 1H), 3.70-3.60 (m, 1H), 3.43 (s, 3H), 3.12 (d, J = 6.0 Hz, 2H), 2.99 (d, J = 6.0 Hz, 2H), 2.90-2.80 (m, 1 H), 2.59-2.55 (m, 2H), 2.10-1.95 (m, 2H), 1.90-1.95 (m, 4H), |

TABLE 2-continued

Compounds synthesized via Method 1, with the coupling of various amines with acid Intermediate C in Step 1, followed by coupling with acid Intermediate D in Step 3.

| Ex-# | I-# | Intermediate Amine | LCMS (ES+) m/z (M + H)+ | HNMR (400 MHz, DMSO-d6) δ |
|---|---|---|---|---|
| | | | | 1.50-1.20 (m, 16H), 0.92 (d, J = 5.2 Hz, 2H), 0.56 (s, 2H) |
| 6[b] | I-6 | tert-butyl (2-(2-aminoethoxy)ethyl)carbamate (CAS# 127828-22-2) | 847.8 | 11.1 (s, 1H), 9.51 (s, 1H), 8.94 (s, 1H), 8.81 (d, J = 6.0 Hz, 1H), 8.8-8.7 (m, 1H), 8.65 (d, J = 8.8 Hz, 1H), 8.50 (s, 1H), 8.32-8.22 (m, 1H), 8.05 (d, J = 5.4 Hz, 1H), 7.83-7.78 (m, 2H), 7.61 (d, J = 8.8 Hz, 1H), 7.49 (d, J = 7.6 Hz, 1H), 7.39 (d, J = 8.8 Hz, 2H), 5.12 (dd, J = 12.8 Hz & 5.4 Hz, 1H), 4.79 (s, 2H), 3.7-3.6 (m, 2H), 3.46-3.43 (m, 2H), 3.41-3.37 (m, 2H), 3.33-3.30 (m, 2H), 3.22-3.15 (m, 2H), 3.22-3.15 (m, 2H), 3.95-3.80 (m, 1H), 3.70-3.55 (m, 1H), 2.15-2.01 (m, 2H), 1.90-1.81 (m, 2H), 1.80-1.70 (m, 2H), 1.49-1.22 (m, 4H), 0.93 (d, J = 5.6 Hz, 2H), 0.67 (s, 2H) |
| 7[a] | I-7 | tert-butyl (3-aminopropyl)carbamate (CAS# 75178-96-0) | 816.9 | 11.18 (s, 1H), 9.50 (s, 1H), 8.57-8.56 (m, 3H), 8.42 (s, 1H), 8.27 (d, J = 8.8 Hz, 1H), 8.15-8.13 (m, 2H), 8.00 (t, J = 6 Hz, 1H), 7.82 (t, J = 8 Hz, 1H), 7.75 (t, J = 1.3 Hz, 1H), 7.57 (d, J = 5.6 Hz, 1H), 7.51 (d, J = 7.6 Hz, 1H), 7.41 (d, J = 8.8 Hz, 1H), 5.15-5.10 (m, 1H), 4.79 (s, 2H), 3.68 (bs, 1H), 3.15 (d, J = 1.3 Hz, 2H), 3.05 (d, J = 6 Hz, 2H), 2.94-2.87 (m, 3H), 2.05-2.02 (m, 2H), 1.87-1.85 (m, 2H), 1.77-1.74 (m, 2H), 1.57 (t, J = 6.4 Hz, 2H), 1.47-1.30 (m, 5H), 0.94 (d, J = 5.2 Hz, 2H), 1.94 (s, 2H) |
| 8[b] | I-8 | tert-butyl (2-aminoethyl)carbamate (CAS# 57260-73-8) | (M − H)⁻ 801.8 | 11.14 (s, 1H), 10.36 (s, 1H), 9.05 (s, 1H), 8.65-8.55 (m, 3H), 8.42 (s, 1H), 8.27 (d, J = 9.2 Hz, 1H), 8.18-8.08 (m, 2H), 8.1-8.0 (m, 1H), 7.89-7.79 (m, 2H), 7.57 (d, J = 5.6 Hz, 1H), 7.55-7.45 (m, 1H), 7.40 (d, J = 8.4 Hz, 1H), 5.15-5.10 (m, 1H), 4.78 (s, 2H), 3.19-3.11 (m, 3H), 3.0-2.75 (m, 3H), 2.65-2.55 (m, 1H), 2.11-2.95 (m, 3H), 2.90-2.80 (m, 2H), 2.79-2.70 (m, 2H), 1.50-1.20 (m, 5H), 0.94 (d, J = 5.6 Hz, 2H), 0.58 (s, 2H) |
| 9[b] | I-9 | tert-butyl (4-aminobutyl)carbamate (CAS# 68076-36-8) | 831.7 | 11.12 (s, 1H), 10.34 (s, 1H), 9.03 (s, 1H), 8.86-8.53 (m, 2H), 8.40 (s, 1H), 8.25 (d, J = 9.2 Hz, 1H), 8.15-8.05 (m, 2H), 7.97 (t, J = 5.6 Hz, 1H), 7.81 (t, J = 7.8 Hz, 1H), 7.72 (t, J = 5.6 Hz, 2H), 7.54 (d, J = 6.0 Hz, 1H), 7.49 (d, J = 7.6 Hz, 1H), 7.37 (d, J = 9.6 Hz, 1H), 5.11 (dd, J = 12.8 Hz & 5.2 Hz, 1H), 4.76 (s, 2H), 3.75-3.6 (m, 1H), 3.2-3.11 (m, 2H), 3.1-2.99 (m, 2H), 2.98-2.80 (m, 1H), 2.65-3.5 (m, 3H), 2.10-2.0 (m, 2H), 1.9-1.7 (m, 4H), 1.5-1.2 (m, 8H), 0.92 (d, J = 4.8 Hz, 2H), 0.57 (s, 2H) |

*The intermediate formed in Step 1-2 could be triturated with diethyl ether, MBTE, or n-pentanes. Step 1 was run for 1-2 h.

[a]Step 2 started at 0° C. then run at rt for 6 h; Step 3 was run for 4 h at rt.

[b]Once water was added to quench the reaction in Step 1, the product precipitated out of solution and was collected, dried and used directly in the next step. For Step 3, PyBOP was used as the coupling reagent instead of HATU and the reaction was run at rt for 1 hr.

Example 10 (Method 2): 6-((1,6-naphthyridin-2-yl)amino)-4-(cyclopropylamino)-N-((1S,4r)-4-((7-(((S)-1-((2S,4R)-4-hydroxy-2-((4-(4-methylthiazol-5-yl)benzyl)carbamoyl)-pyrrolidin-1-yl)-3,3-dimethyl-1-oxobutan-2-yl)amino)-7-oxoheptyl)carbamoyl)cyclohexyl)-nicotinamide, I-10

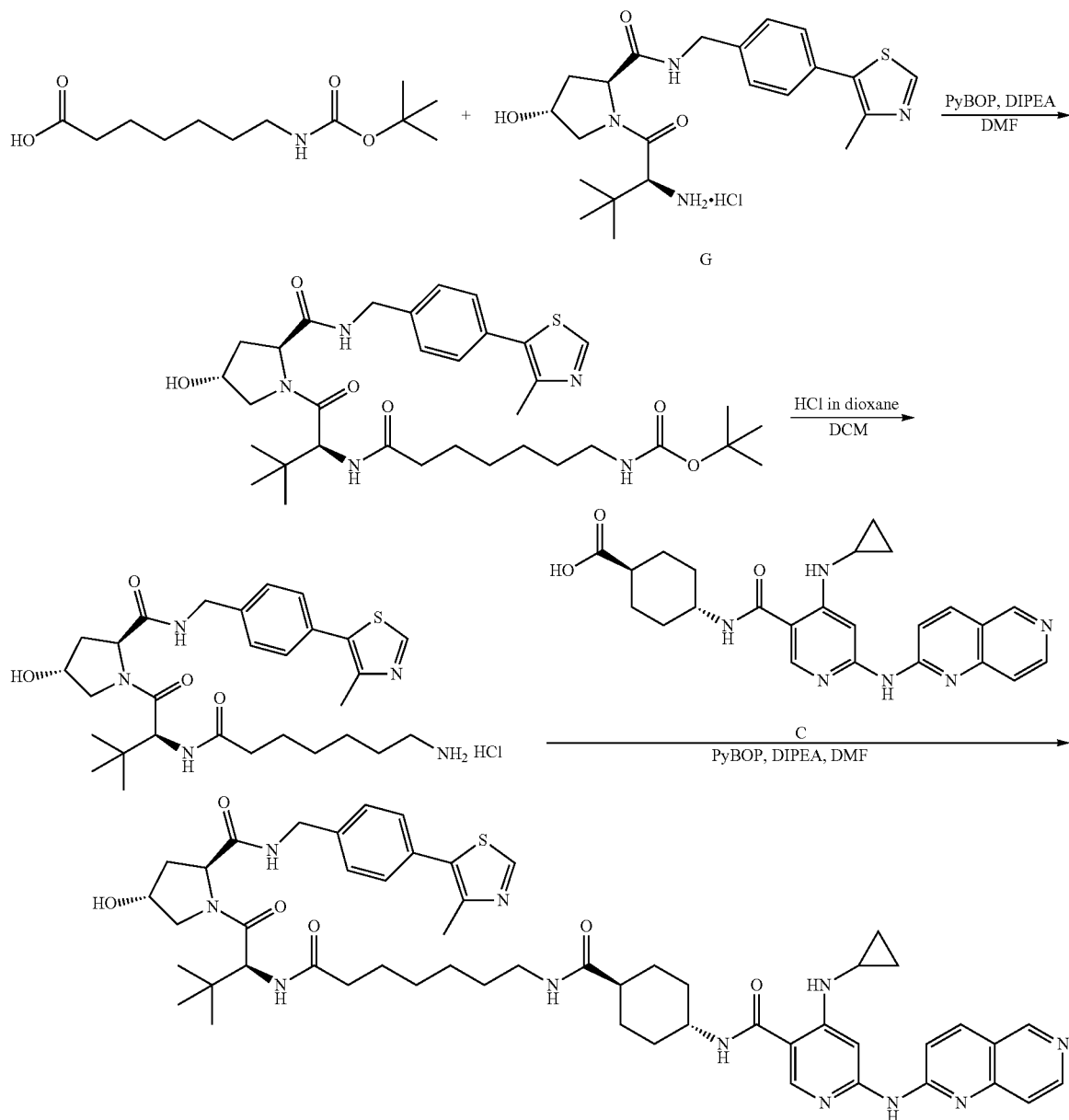

Step 1—tert-butyl (7-(((S)-1-((2S,4R)-4-hydroxy-2-((4-(4-methylthiazol-5-yl)benzyl)carbamoyl)-pyrrolidin-1-yl)-3,3-dimethyl-1-oxobutan-2-yl)amino)-7-oxoheptyl)carbamate To a solution of 7-((tert-butoxycarbonyl)amino)heptanoic acid (0.3 g, 1.2 mmol, CAS #60142-89-4), (2S,4R)-1-((S)-2-amino-3,3-dimethylbutanoyl)-4-hydroxy-N-(4-(4-methylthiazol-5-yl)-benzyl)pyrrolidine-2-carboxamide hydrochloride (0.74 g, 1.59 mmol, Intermediate G) and DIPEA (1.1 mL, 6.1 mmol) in DMF (2 mL) was added PyBOP (0.95 g, 1.5 mmol) at rt and the mixture was stirred for 2 h. The reaction mixture was then transferred into ice water and the resulting mixture was extracted using ethyl acetate (3×20 mL). The combined organic layer was dried over anhydrous sodium sulfate and filtered. The filtrate was evaporated under reduced pressure and the crude product was purified using silica gel column chromatography (4% MeOH-DCM) to give tert-butyl (7-(((S)-1-((2S,4R)-4-hydroxy-2-((4-(4-methylthiazol-5-yl)benzyl)carbamoyl)-pyrrolidin-1-yl)-3,3- dimethyl-1-oxobutan-2-yl)amino)-7-oxoheptyl)carbamate as brownish yellow semisolid (0.8 g, 99%). LC-MS (ESI+) m/z 658.7 (M+H)+.

Step 2—(2S,4R)-1-((S)-2-(7-aminoheptanamido)-3,3-dimethylbutanoyl)-4-hydroxy-N-(4-(4-methylthiazol-5-yl)benzyl)pyrrolidine-2-carboxamide hydrochloride To a stirred solution of tert-butyl (7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-7-oxoheptyl)carbamate (0.8 g, 1.2 mmol) in DCM (10 mL) was added 4N HCl in dioxane (2 mL) at 0° C. The resulting reaction mixture was warmed to rt and stirred for 2 h. The reaction mixture was then evaporated under vacuum and triturated using diethyl ether to give (2S,4R)-1-((S)-2-(7-aminoheptanamido)-3,3-dimethylbutanoyl)-4-hydroxy-N-(4-(4-methylthiazol-5-yl)benzyl)-pyrrolidine-2-carboxamide hydrochloride as yellow solid (0.5 g, 70%). LCMS (ESI+) m/z 558.61 (M+H)+.

Step 3—6-((1,6-naphthyridin-2-yl)amino)-4-(cyclopropylamino)-N-((1S,4r)-4-((7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-7-oxoheptyl)carbamoyl)cyclohexyl)nicotinamide To a stirred suspension of (1R,4R)-4-(6-((1,6-naphthyridin-2-yl)amino)-4-(cyclopropylamino)nicotinamido)cyclohexane-1-carboxylic acid (0.2 g, 0.5 mmol, Intermediate C) and (2S,4R)-1-((S)-2-(7-aminoheptanamido)-3,3-dimethylbutanoyl)-4-hydroxy-N-(4-(4-methylthiazol-5-yl)benzyl)pyrrolidine-2-carboxamide hydrochloride (0.34 g, 0.58 mmol) in DMF (5 mL) was added DIPEA (0.5 mL, 2.3 mmol) and PyBOP (0.35 g, 0.68 mmol) and the reaction mixture was stirred at rt for 1 h. The reaction mixture was then transferred into ice water and the resulting mixture was extracted using ethyl acetate (3×20 mL). The combined organic layer was dried over anhydrous sodium sulfate and filtered. The filtrate was evaporated under reduced pressure and the crude product was purified using preparative HPLC (0.1% formic acid in water/ACN) to give 6-((1,6-naphthyridin-2-yl)amino)-4-(cyclopropylamino)-N-((1S,4r)-4-((7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-7-oxoheptyl)carbamoyl)cyclohexyl)nicotinamide I-10 as light yellow solid (0.21 g, 37%). $^1$H NMR (400 MHz, DMSO) δ 10.36 (s, 1H), 9.05 (s, 1H), 8.99 (s, 1H), 8.63-8.51 (m, 3H), 8.42 (s, 1H), 8.27 (d, J=9.2 Hz, 1H), 8.15 (d, J=7.6 Hz, 1H), 7.88 (d, J=9.2 Hz, 1H), 7.71-7.63 (m, 1H), 7.57 (d, J=5.6 Hz, 1H), 7.51 (d, J=8.8 Hz, 1H), 7.48-7.31 (m, 3H), 4.55 (d, J=9.2 Hz, 1H), 4.49-4.41 (m, 1H), 4.40-4.31 (m, 2H), 4.30-4.15 (m, 1H), 3.75-3.61 (m, 2H), 3.05-2.95 (m, 2H), 2.65-2.55 (m, 1H), 2.45 (s, 3H), 2.41-1.71 (m, 8H), 1.51-1.21 (m, 10H), 0.94 (s, 9H), 0.55 (s, 2H). LC-MS (ESI+) m/z 987.25 (M+H)+.

TABLE 3

Compounds synthesized via Method 2, with the coupling of various amines with acids in Step 1, followed by coupling with acids in Step 3.

| Ex-# | I-# | Step 1 Intermediate Amine | Step 1 Intermediate Acid | Step 3 Acid | LCMS (ES+) m/z (M + H)+ | HNMR (400 MHz, DMSO-d6) δ |
|---|---|---|---|---|---|---|
| 11 | I-11 | tert-butyl (2-(2-(2-(2-aminoethoxy)-ethoxy)-ethoxy)ethyl)carbamate (CAS# 153086-78-3) | D | C | 936.0 | 11.13 (s, 1H), 10.35 (s, 1H), 9.05 (s, 1H), 8.56 (t, J = 4 Hz, 3H), 8.42 (s, 1H), 8.28 (d, J = 8.8 Hz, 1H), 8.17 (s, 1H), 8.14 (d, J = 7.6 Hz, 1H), 8.03 (t, J = 5.6 Hz, 1H), 7.83-7.79 (m, 2H), 7.57 (d, J = 6 Hz, 1H), 7.52 (m, 2H), 7.41 (d, J = 8.4 Hz, 1H) 5.14-5.10 (m, 1H), 4.79 (s, 2H), 3.70 (bs, 1H), 3.52-3.17 (m, 20H), 2.93-2.87 (m, 1H), 2.67-2.50 (m, 4H), 2.08-2.03 (m, 2H), 1.87 (d, J = 10 Hz, 2H), 1.76 (d, J = 12.4 Hz, 2H), 1.46-1.30 (m, 4H), 0.96-0.93 (m, 2H), 0.58 (s, 2H) |
| 12 | I-12 | G | I | C | 1056.8 | 10.37 (s, 1H), 9.05 (s, 1H), 8.99 (s, 1H), 8.61-8.55 (m, 4H), 8.42 (s, 1H), 8.27 (d, J = 8.8 Hz, 1H), 8.2-8.13 (m, 2H), 7.88 (d, J = 9.6 Hz, 1H), 7.75-7.65 (m, 2H), 7.57 (d, J = 5.6 Hz, 1H), 7.50 (d, J = 9.2 Hz 1H) 7.43-7.35 (m, 3H), 5.14 (bs, 1H), 4.60-4.50 (m, 1H), 4.49-4.31 (m, 3H), 4.25-4.15 (m, 2H), 3.80-3.60 (m, 5H), 3.10-2.95 (m, 6H), 2.45 (s, 3H), 2.39-2.01 (m, 5H), 1.95-1.81 (m, 3H), 1.80-1.65 (m, 5H), 1.55-1.15 (m, 24H), 0.94 (s, 10H), 0.58 (s, 2H) |
| 13$^c$ | I-13 | G | EN | C | 1090.7 (M − H)+ | 10.35 (s, 1H), 9.05 (s, 1H), 8.99 (s, 1H), 8.62-8.56 (m, 4H), 8.42 (s, 1H), 8.26 (d, J = 8.8 Hz, 1H), 8.15-8.13 (m, 2H), 7.81 (bs, 1H), 7.57-7.55 (m, 1H), 7.51-7.49 (m, 1H), 7.45-7.43 (m, 5H), 5.16 (bs, |

TABLE 3-continued

Compounds synthesized via Method 2, with the coupling of various
amines with acids in Step 1, followed by coupling with acids in Step 3.

| Ex-# | I-# | Step 1 Intermediate Amine | Step 1 Intermediate Acid | Step 3 Acid | LCMS (ES+) m/z (M + H)+ | HNMR (400 MHz, DMSO-d6) δ |
|---|---|---|---|---|---|---|
| | | | | | | 1H), 4.58-4.56 (m, 1H), 4.46-4.35 (m, 4H) 4.27-4.24 (m, 1H), 3.97 (s, 2H), 3.68-3.66 (m, 2H), 3.66-3.61 (m, 4H), 3.58-3.54 (m, 4H), 3.53-3.48 (m, 4H), 3.37-3.34 (m, 3H), 3.18-3.17 (m, 2H), 2.67-2.60 (m, 1H), 2.44 (s, 3H), 2.08-2.06 (m, 2H), 1.87-1.85 (m, 3H), 1.76-1.73 (m, 2H), 1.46-1.28 (m, 4H), 0.95 (s, 9H), 0.58 (s, 2H) |
| 14[b] | I-14 | AB | C | G | 1087.3 | 10.37 (s, 1H), 9.051-8.991 (m, 2H), 8.57 (s, 4H), 8.42 (s, 1H), 8.27 (bs, 1H), 8.15 (bs, 1H), 7.90 (bs, 1H), 7.72 (bs, 1H), 7.56-7.41 (m' 5H)' 5.16 (bs, 1H), 4.55-4.23 (m, 4H), 3.65 (bs, 3H), 3.0 (bs, 2H), 2.44-2.33 (m, 4H), 2.12-2.04 (m, 3H), 1.92-1.87 (m, 3H), 1.83-1.74 (m, 2H), 1.46-1.25 (m, 19H), 0.93 (s, 10H), 0.58 (s, 2H) |
| 15[c] | I-15 | G | 5-((tert-butoxy-carbonyl)-amino) pentanoic acid (CAS# 27219-07-4) | C | 959.3 | 9.03 (s, 1H), 8.96 (s, 1H), 8.58-8.53 (m, 4H), 8.40 (s, 1H), 8.25 (d, J = 4.8 h, 1H), 8.13-8.11 (m, 1H), 7.87 (d, J = 9.2 h, 1H), 7.71 (t, J = 5.2 Hz, 1H), 7.55 (d, J = 5.6 Hz, 1H), 7.49 (d, J = 9.2 Hz, 1H), 7.41-7.35 ( m, 4H), 5.13 (s, 1H), 4.53 (d, J = 9.2 Hz, 1H), 4.44 (m, 3H), 4.22-4.17 (m, 1H), 3.00 (d, J = 6 Hz, 2H), 2.65-2.58 (m, 1H), 2.48 (s, 3H), 2.31-2.21 (m, 1H), 2.14-2.01 (m, 3H), 1.91-1.71 (m, 5H), 1.46-1.26 (m, 8H), 0.92 (s, 11H), 0.56 (s, 2H) |
| 16[a] | I-16 | tert-butyl (2-(2-(2-aminoethoxy) ethoxy) ethyl) carbamate (CAS# 153086-78-3) | D | O | 863.7 | 12.80 (bs, 1H), 11.12 (s, 1H), 10.35 (s, 1H), 9.03 (s, 1H), 8.54-8.50 (m, 3H), 8.44 (s, 1H), 8.26 (d, J = 8.8 Hz, 1H), 8.11 (s, 1H), 8.01 (t, J = 5.2 Hz, 1H), 7.82-7.77 (m, 2H), 7.55-7.47 (m, 3H), 7.38 (d, J = 8.4 Hz, 1H), 5.12-5.08 ( m, 1H), 4.78 (s, 2H), 4.53-4.47 (m, 1H), 3.50 (s, 3H), 3.46-3.32 (m, 4H), 3.32-3.29 (m, merged with water peak of DMSO, 3H), 3.22-3.17 (m, 2H), 2.91-2.85 (m, 2H), 2.65-2.48 (m, 3H), 2.35-2.30 (m, 2H), 2.26-2.19 (m, 2H), 2.03-2.01 (m, 1H), 0.91 (s, 2H), 0.54 (s, 2H) |
| 17[d] | I-17 | tert-butyl (2-(2-(2-(2-amino-ethoxy) ethoxy) ethoxy) ethyl) carbamate (CAS# 101187-40-0) | D | AG | 934.0 | 11.03 (s, 1H), 9.07-9.04 (m, 2H), 8.67 (s, 1H), 8.60 (s, 1H), 8.55 (s, 1H), 8.40 (d, J = 7.6 Hz, 1H), 8.05-8.02 (m, 1H), 7.84-7.80 (m, 2H), 7.68 (s, 1H), 7.51 (d, J = 7.2 Hz, 1H), 7.41 (d, J = 8.4 Hz, 1H), 5.15-5.11 (m, 1H), 4.80 (s, 2H), 3.73-3.71 (m 1H) 3.53-3.48 (m, 11H), 3.46-3.39 (m, 3H), 3.38-3.35 (m, 1H), 3.20-3.18 (m, 2H), 2.95-2.86 (m, 1H), 2.68-2.63 (m, 2H), 2.63-2.59 (m, 2H), 2.11-2.04 (m, 2H), 1.92-1.89 (m, 2H), 1.78-1.76 (m, 2H), 1.48-1.24 (m, 4H), 0.86 (d, J = 5.2 Hz, 2H), 0.58 (s, 2H) |
| 18 | I-18 | K | D | L | 922.4 | 11.15 (s, 1H), 9.06 (dd, J = 1.6 and 12.8 Hz, 2H), 8.67 (s, 1H), 8.61 (s, 1H), 8.57 (s, 1H), 8.42 (d, J = 7.2 Hz, 1H), 8.08-8.01 (m, 1H), 7.87-7.77 (m, 1H), 7.68 (s, |

TABLE 3-continued

Compounds synthesized via Method 2, with the coupling of various amines with acids in Step 1, followed by coupling with acids in Step 3.

| Ex-# | I-# | Step 1 Intermediate Amine | Step 1 Intermediate Acid | Step 3 Acid | LCMS (ES+) m/z (M + H)+ | HNMR (400 MHz, DMSO-d6) δ |
|---|---|---|---|---|---|---|
| | | | | | | 1H), 7.51 (d, J = 7.2 Hz, 1H), 7.41 (d, J = 8.8 Hz, 1H), 5.16-5.11 (m, 1H), 4.81 (s, 2H), 3.80-3.55 (m, 1H), 3.55-3.45 (m, 11H), 3.35-3.25 (m, 3H), 3.22 (d, J = 6.4 Hz, 2H), 3.0-2.80 (m, 1H), 2.70-2.55 (m, 3H), 2.5-2.4 (m, 2H), 2.10-2.0 (m, 1H), 1.95-1.7 (m, 4H), 1.60-1.45 (m, 1H), 1.4-1.3 (m, 2H), 1.1-0.9 (m, 2H), 0.86 (d, J = 5.2 Hz, 2H), 0.57(s, 2H) |

[a]HATU used instead of PyBOP as the coupling reagent in Step 1 and the reaction was run for 2 h at rt in DCM. In Step 2, the reaction was run for 3 h and the product was triturated with MBTE. Step 3 was run for 3 h.
[b]TFA was used instead of HCl for the deprotection in Step 2 and was added at 0° C., then the reaction was stirred at rt for 16 h. The product triturated using n-pentanes. In Step 3, HATU was used instead of PyBOP as the coupling reagent and the final product was purified using preparative HPLC (0.1% ammonia in water/ACN).
[c]HATU was used as the coupling agent in Step 1 instead of PyBOP. In Step 2, the intermediate was triturated using MTBE.
[d]The final product was purified by silica gel column chromatography (7% MeOH-DCM).

Example 19 (Method 3): 6-((1,6-naphthyridin-2-yl)amino)-4-(cyclopropylamino)-N-(1-(2-((2-(2-(2-((2-(2,6-dioxopiperidin-3-yl)-1,3-dioxoisoindolin-4-yl)amino)ethoxy)ethoxy)ethyl)amino)-2-oxoethyl)piperidin-4-yl)nicotinamide, I-19

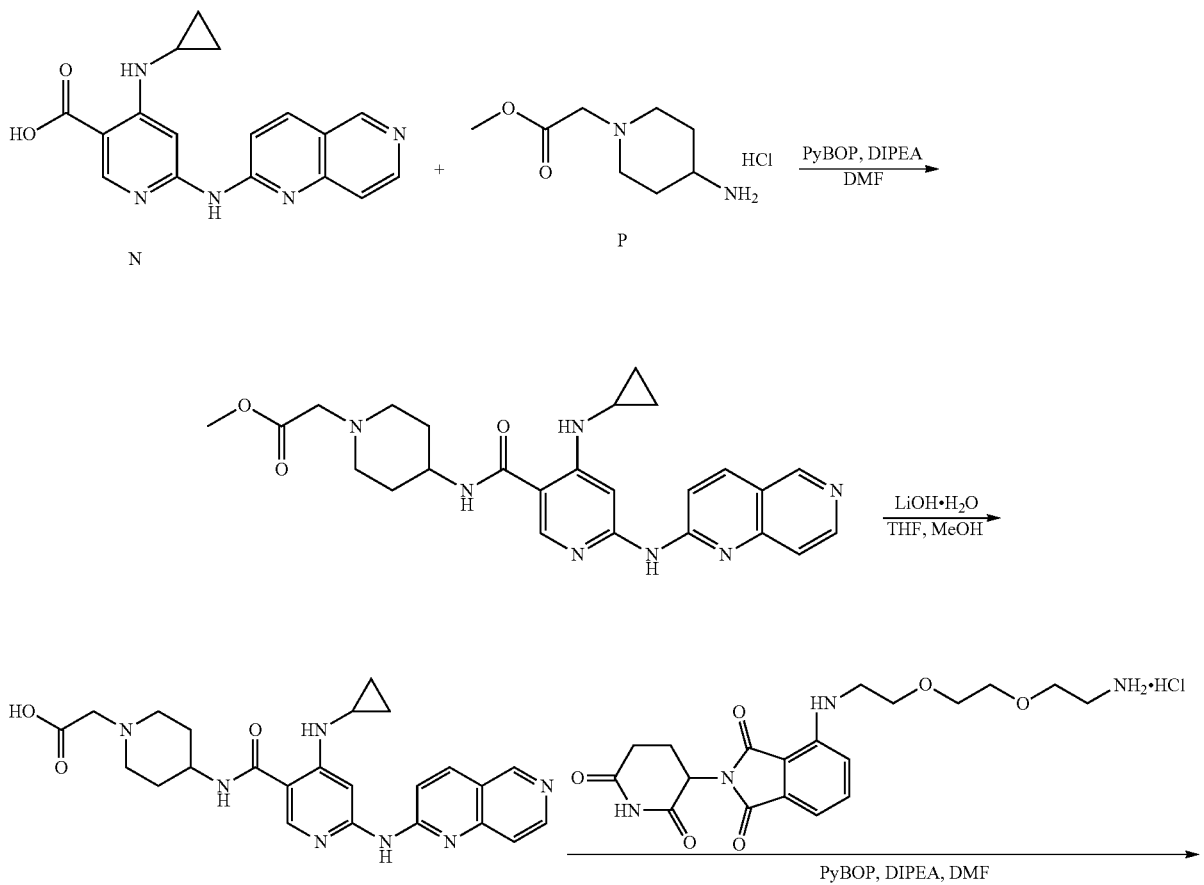

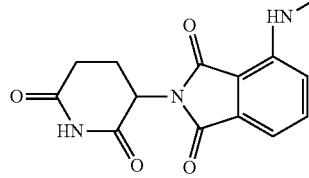 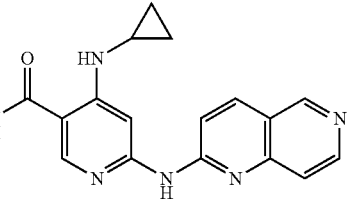

Step 1 Ethyl 2-(4-(6-((1,6-naphthyridin-2-yl)amino)-4-(cyclopropylamino)nicotinamido)-piperidin-1-yl)acetate A solution of 6-((1,6-naphthyridin-2-yl)amino)-4-(cyclopropylamino)nicotinic acid (0.19 g, 0.58 mmol, Intermediate N), ethyl 2-(4-aminopiperidin-1-yl)acetate hydrochloride (0.13 g, 0.58 mmol, Intermediate P), PyBOP (0.45 g, 0.87 mmol) and DIPEA (0.23 mL, 1.73 mmol) in DMF (3 mL) was stirred at rt for 3 h. The reaction mixture was then transferred into ice water and the resulting mixture was extracted using ethyl acetate (3×25 mL). The combined organic layer was dried over anhydrous sodium sulfate and filtered. The filtrate was evaporated under reduced pressure to and the crude product was purified using silica gel column chromatography (50% EtOAc-Hexane) to give ethyl 2-(4-(6-((1,6-naphthyridin-2-yl)amino)-4-(cyclopropylamino) nicotinamido)piperidin-1-yl)acetate as a light yellow solid (0.15 g, 39%). $^1$H NMR (400 MHz, DMSO) δ 10.74 (bs, 1H), 9.11 (s, 1H), 8.61-8.32 (m, 5H), 7.75-7.60 (m, 1H), 7.53 (d, J=8.8 Hz, 1H), 4.22-4.18 (m, 2H), 4.10-3.80 (m, 3H), 3.00-2.93 (m, 2H), 2.67-250 (m, 2H), 2.08-1.65 (m, 4H), 1.26-1.15 (m, 4H), 0.95 (d, J=4.8 Hz, 2H), 0.86-0.81 (m, 1H), 0.59 (s, 2H).

Step 2—2-(4-(6-((1,6-naphthyridin-2-yl)amino)-4-(cyclopropylamino)nicotinamido)-piperidin-1-yl)acetic acid A solution of ethyl 2-(4-(6-((1,6-naphthyridin-2-yl)amino)-4-(cyclopropylamino) nicotinamido)piperidin-1-yl)acetate (0.15 g, 0.31 mmol) and LiOH.H$_2$O (0.04 g, 0.93 mmol) in THF:MeOH (5 mL, 1:1) was stirred at rt for 5 h. The reaction mixture was then adjusted to pH of 4-5 using citric acid solution. The solid precipitate was collected using filtration and the solid was dried under vacuum to give 2-(4-(6-((1,6-naphthyridin-2-yl)amino)-4-(cyclopropylamino)nicotinamido)piperidin-1-yl)acetic acid as a light yellow solid (0.065 g, 53%). LC-MS (ESI$^+$) m/z 462.04 (M+H)$^+$.

Step 3—6-((1,6-naphthyridin-2-yl)amino)-4-(cyclopropylamino)-N-(1-(2-((2-(2-(2-((2-(2,6-dioxopiperidin-3-yl)-1,3-dioxoisoindolin-4-yl)amino)ethoxy)ethoxy)ethyl)amino)-2-oxoethyl)piperidin-4-yl)nicotinamide A solution of 4-((2-(2-(2-aminoethoxy)ethoxy)ethyl)amino)-2-(2,6-dioxopiperidin-3-yl) isoindoline-1,3-dione (0.06 g, 0.14 mmol, synthesized via Method 4, Step 1-2 of Example 23), 2-(4-(6-((1,6-naphthyridin-2-yl)amino)-4-(cyclopropylamino)nicotinamido)piperidin-1-yl)acetic acid (0.06 g, 0.14 mmol), PyBOP (0.11 g, 0.20 mmol) and DIPEA (0.05 mL, 0.4 mmol) in DMF (3 mL) was stirred at rt for 2 h. The reaction mixture was then transferred into ice water and resulting solid was filtered and purified by preparative HPLC (0.1% formic acid in water/ACN) purification to give 6-((1,6-naphthyridin-2-yl)amino)-4-(cyclopropylamino)-N-(1-(2-((2-(2-(2-((2-(2,6-dioxopiperidin-3-yl)-1,3-dioxoisoindolin-4-yl)amino)ethoxy)ethyl)amino)-2-oxoethyl)piperidin-4-yl)nicotinamide I-19 as a light yellow solid (0.022 g, 19%). $^1$H NMR (400 MHz, DMSO) δ 11.10 (s, 1H), 9.67 (bs, 1H), 9.18 (s, 1H), 8.63-8.37 (m, 4H), 7.73 (bs, 1H), 7.59-7.49 (m, 2H), 7.14 (d, J=8.4 Hz, 1H), 7.04 (d, J=7.2 Hz, 1H), 6.59 (s, 1H), 5.06-5.02 (m, 1H), 3.86-3.71 (m, 1H), 3.60-3.54 (m, 6H), 3.46-3.33 (m, 6H), 3.11-3.08 (m, 1H), 2.90-2.83 (m, 1H), 2.59-2.52 (m, 2H), 2.16-1.98 (m, 5H), 1.89-1.82 (m, 3H), 0.94 (d, J=5.6 Hz, 2H), 0.58 (s, 2H); LC-MS (ESI$^+$) m/z (M+H)$^+$=848.93

Example 20: 6-((1,6-naphthyridin-2-yl)amino)-4-(cyclopropylamino)-N-(1-(2-((2-(2-(2-((2-(2,6-dioxopiperidin-3-yl)-1,3-dioxoisoindolin-4-yl)amino)ethoxy)ethoxy)ethyl)amino)-2-oxoethyl)azetidin-3-yl)nicotinamide, I-20

I-20

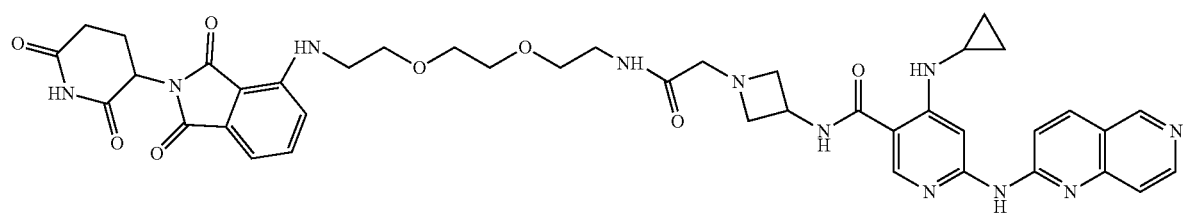

6-((1,6-naphthyridin-2-yl)amino)-4-(cyclopropylamino)-N-(1-(2-((2-(2-(2-((2-(2,6-dioxopiperidin-3-yl)-1,3-dioxoisoindolin-4-yl)amino)ethoxy)ethoxy)ethyl)amino)-2-oxoethyl)azetidin-3-yl)nicotinamide was synthesized via Method 3 starting with Intermediate Q as the amine and Intermediate N as the acid in Step 1. Step 1 was started at 0° C. then allowed to warm to rt and stirred for 16 h. After the water quench, the product was extracted using 5% methanol in DCM and the product was purified by silica gel column chromatography (8-9% MeOH-DCM). Step 2 was run at 0° C. for 2 h. Upon completion, the reaction mixture was acidified with Dowex 50 Resin and the reaction mixture was filtered through celite and used directly in the subsequent step. In Step 3, the amine 4-((2-(2-(2-aminoethoxy) ethoxy)ethyl)amino)-2-(2,6-dioxopiperidin-3-yl) isoindoline-1,3-dione (synthesized via Method 4, Step 1-2 of Example 23) was coupled under the conditions described at 0° C. and stirred for 45 min. Purification by HPLC (5 mM ammonium bicarbonate with 0.1% ammonia in water/ACN) gave the title product I-20. $^1$H NMR (400 MHz, DMSO-$d_6$) δ 11.11 (s, 1H), 10.38 (s, 1H), 9.06 (s, 1H), 8.66 (d, J=6.8 Hz, 1H), 8.65-8.50 (m, 3H), 8.48 (s, 1H), 8.28 (d, J=1.6 Hz, 1H), 7.70-7.55 (m, 3H), 7.51 (d, J=8.8 Hz, 1H), 7.14 (d, J=8.4 Hz, 1H), 7.03 (d, J=7.2 Hz, 1H), 6.69-6.59 (m, 1H), 5.06 (dd, J=12.8 Hz & 5.2 Hz, 1H), 4.55-4.45 (m, 1H), 3.70-3.60 (m, 3H), 3.59-3.40 (m, 8H), 3.30-3.20 (m, 2H), 3.15-2.95 (m, 4H), 2.94-2.80 (m, 2H), 2.65-2.55 (m, 1H), 2.10-1.95 (m, 2H), 1.80-1.70 (m, 1H), 0.94 (d, J=4.8 Hz, 2H), 0.58 (s, 2H), LC-MS (ESI$^+$) m/z 820.21 (M+H+).

Example 21: 6-(5-cyano-1H-pyrazolo[3,4-b]pyridin-1-yl)-4-(cyclopropylamino)-N-((1r,3r)-3-((14-((2-(2,6-dioxopiperidin-3-yl)-1,3-dioxoisoindolin-4-yl) amino)-3,6,9,12-tetraoxatetradecyl)carbamoyl) cyclobutyl)nicotinamide, I-21

I-21

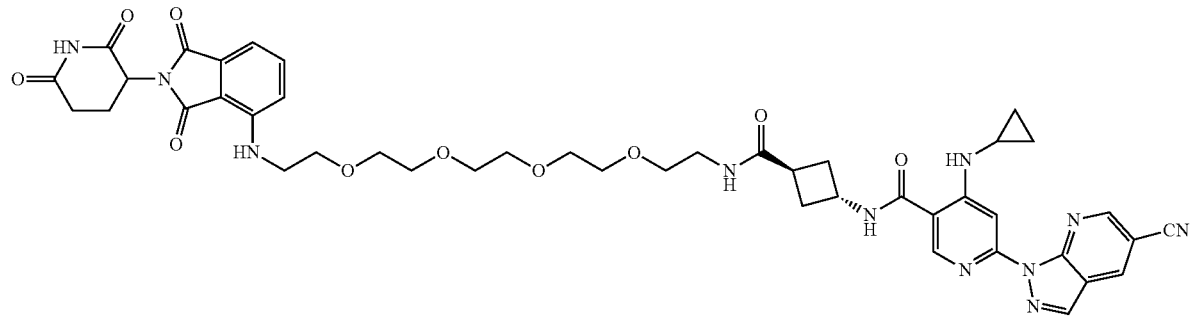

6-(5-cyano-1H-pyrazolo[3,4-b]pyridin-1-yl)-4-(cyclopropylamino)-N-((1r,3r)-3-((14-((2-(2,6-dioxopiperidin-3-yl)-1,3-dioxoisoindolin-4-yl)amino)-3,6,9,12-tetraoxatetradecyl)carbamoyl)cyclobutyl)nicotinamide was synthesized via Method 3 starting with methyl trans-3-aminocyclobutane-1-carboxylate hydrochloride (CAS #74316-29-3) as the amine and Intermediate L as the acid in the first step. In Step 1, HATU was used at the coupling reagent instead of PyBOP and the reaction mixture was stirred with acid Intermediate L for 30 min at 0° C. then the amine and base were added and the reaction was stirred at rt for 1 h. After the aqueous work up, the solid precipitate was collected and used directly in the subsequent reaction. Step 2 was run in a 1:1 mixture of THF:water as the solvent. In Step 3 the starting material amine used was Intermediate Z and the final product was purified using silica gel column chromatography (4% MeOH-DCM) to give the title compound I-21. $^1$H NMR (400 MHz, DMSO) δ 11.12 (s, 1H), 9.07 (d, J=2 Hz, 1H), 9.04 (d, J=2 Hz, 1H), 8.80 (d, J=7.2 Hz, 1H), 8.65 (d, J=11 Hz, 2H), 8.56 (s, 1H), 7.87-7.84 (m, 1H), 7.68 (s 1H), 7.58 (t, J=7.2 Hz, 1H), 7.14 (d, J=8.8 Hz, 1H), 7.03 (d, J=6.8 Hz, 1H), 6.61 (t, J=5.6 Hz, 1H), 5.08-5.03 (m, 1H), 4.56-4.54 (m, 1H), 3.63-3.60 (m, 2H), 3.56-3.55 (m, 13H), 3.47-3.42 (m, 2H), 3.24-3.20 (m, 2H), 2.93-2.85 (m, 2H), 2.60-2.56 (m, 3H), 2.40-2.35 (m, 2H), 2.33-2.30 (m, 2H), 2.26-2.01 (m, 1H), 0.87-0.83 (m, 2H), 0.58-0.56 (m, 2H). LC-MS (ESI$^+$) m/z 892.8 (M+H)$^+$.

Example 22: 6-(5-cyano-1H-pyrazolo[3,4-b]pyridin-1-yl)-4-(cyclopropylamino)-N-((1r,4r)-4-((14-((2-(2,6-dioxopiperidin-3-yl)-1,3-dioxoisoindolin-4-yl)amino)-3,6,9,12-tetraoxatetradecyl)carbamoyl)cyclohexyl)nicotinamide, I-22

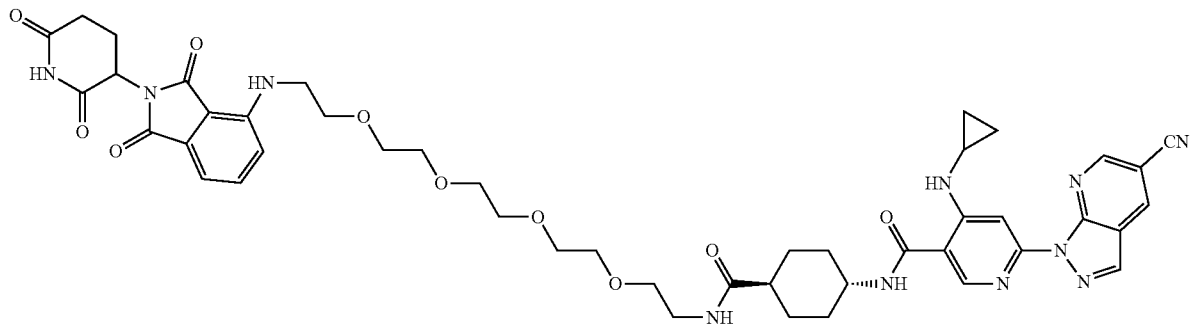 [SMILES: N#Cc1cnc2c(cnn2-c2cc(NC3CC3)c(C(=O)N[C@H]3CC[C@H](C(=O)NCCOCCOCCOCCOCCNc4cccc5c4C(=O)N(C4CCC(=O)NC4=O)C5=O)CC3)cn2)c1]

6-(5-cyano-1H-pyrazolo[3,4-b]pyridin-1-yl)-4-(cyclopropylamino)-N-((1r,4r)-4-((14-((2-(2,6-dioxopiperidin-3-yl)-1,3-dioxoisoindolin-4-yl)amino)-3,6,9,12-tetraoxatetradecyl)carbamoyl)cyclohexyl)nicotinamide I-22 was synthesized via Step 3 of Method 3 starting with acid Intermediate AG and amine Intermediate Z.

$^1$H NMR (400 MHz, DMSO) δ 11.12 (s, 1H), 9.07 (s, 1H), 9.05 (s, 1H), 8.67 (s, 1H), 8.67 (s, 1H), 8.56 (s, 1H), 8.42 (d, J=8 Hz, 1H), 7.81 (d, J=5.2 Hz, 1H), 7.68 (s, 1H), 7.59 (t, J=8 Hz, 1H), 7.17 (d, J=8.4 Hz, 1H), 7.05 (d, J=7.2 Hz, 1H), 6.62 (s, 1H), 5.09-5.04 (m, 1H), 3.73-3.34 (m, 19H), 3.35-3.25 (m, 2H), 3.03-3.02 (m, 2H), 2.94-2.86 (m, 2H), 2.68-2.51 (m, 3H), 2.11-2.02 (m, 3H), 1.98-1.89 (m, 2H), 1.79-1.74 (m, 4H), 1.46-1.33 (m, 4H), 0.87 (d, J=5.2 Hz, 2H), 0.57 (s, 1H). LC-MS (ESI$^+$) m/z 921.5 (M+H)$^+$.

Example 23 (Method 4): 6-((1,6-naphthyridin-2-yl)amino)-4-(cyclopropylamino)-N-((1R,4R)-4-((2-(2-(2-((2-(2,6-dioxopiperidin-3-yl)-1,3-dioxoisoindolin-4-yl)amino)ethoxy)ethoxy)-ethyl)carbamoyl)cyclohexyl)nicotinamide, I-23

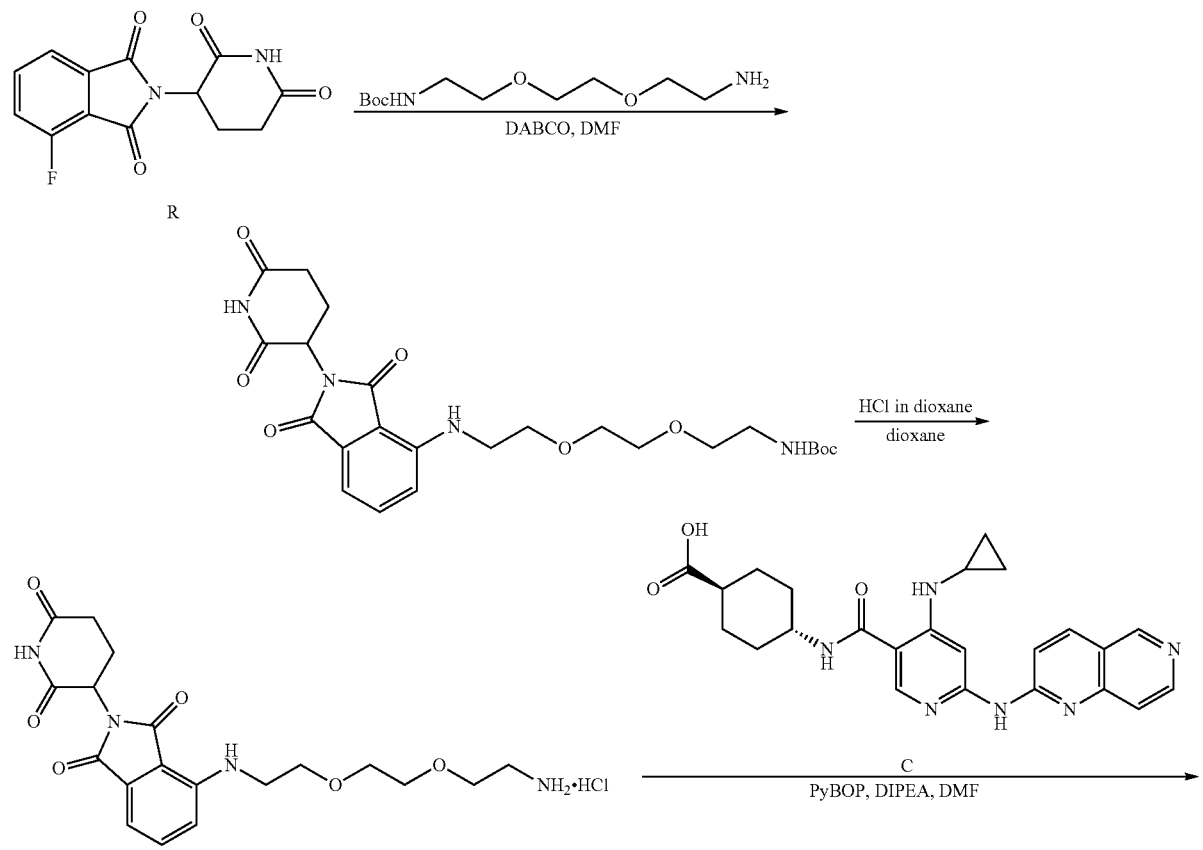

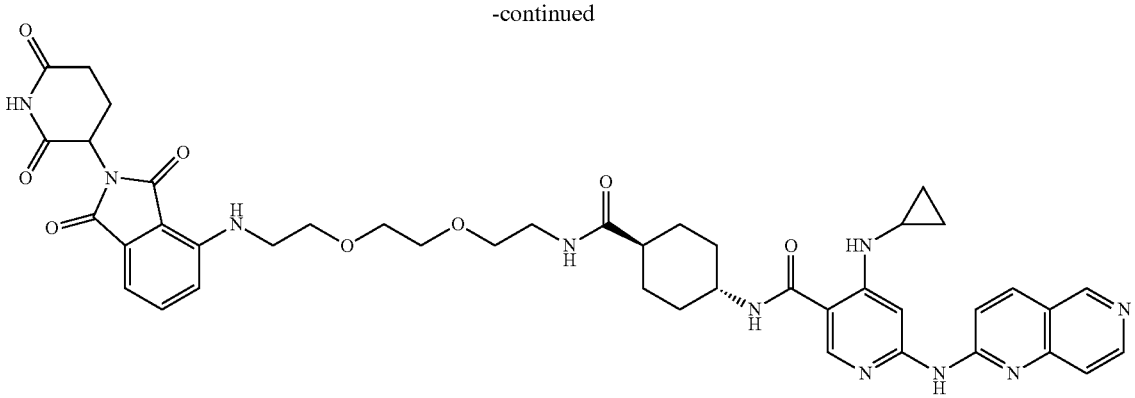

Step 1—tert-butyl (2-(2-(2-((2-(2,6-dioxopiperidin-3-yl)-1,3-dioxoisoindolin-4-yl)amino)ethoxy)ethoxy)ethyl)carbamate To a stirred solution of 2-(2,6-dioxopiperidin-3-yl)-4-fluoroisoindoline-1,3-dione (2.6 g, 9.4 mmol, Intermediate R) and DABCO (1.4 g, 12.2 mmol) in DMF (15 mL) was added tert-butyl (2-(2-(2-aminoethoxy)ethoxy)ethyl)carbamate (2.8 g, 11.3 mmol, CAS #153086-78-3) at rt. The resulting reaction mixture heated to 80° C. and stirred for 2 h. The reaction mixture was then transferred into ice water and the resulting mixture was extracted using ethyl acetate (3×50 mL). The combined organic layer was dried over anhydrous sodium sulfate and filtered. The filtrate was evaporated under reduced pressure and the crude product was purified using silica gel column chromatography (2% MeOH-DCM) to give tert-butyl (2-(2-(2-((2-(2,6-dioxopiperidin-3-yl)-1,3-dioxoisoindol-4-yl)amino)ethoxy)ethoxy)ethyl)carbamate as a yellow oil (0.6 g, 13%). LCMS (ESI$^+$) m/z 505.5 (M+H)$^+$.

Step 2—4-((2-(2-(2-aminoethoxy)ethoxy)ethyl)amino)-2-(2,6-dioxopiperidin-3-yl)isoindoline-1,3-dione hydrochloride To a stirred solution of tert-butyl (2-(2-(2-((2-(2,6-dioxopiperidin-3-yl)-1,3-dioxoisoindolin-4-yl)amino)ethoxy)ethoxy)ethyl)carbamate (0.6 g, 1.2 mmol) in 1,4 dioxane (15 mL) was added 4 M HCl in dioxane (10 mL) at 0° C. The resulting reaction mixture was allowed to warm to rt and stirred for 16 h. The reaction mixture was then evaporated under vacuum and the residue was triturated using MTBE to give 4-((2-(2-(2-aminoethoxy)ethoxy)ethyl)amino)-2-(2,6-dioxopiperidin-3-yl)isoindoline-1,3-dione hydrochloride as yellow solid (0.48 g, 91%). LCMS (ESI$^+$) m/z 405.4 (M+H)$^+$.

Step 3—6-((1,6-naphthyridin-2-yl)amino)-4-(cyclopropylamino)-N-((1R,4R)-4-((2-(2-(2-((2-(2,6-dioxopiperidin-3-yl)-1,3-dioxoisoindolin-4-yl)amino)ethoxy)ethoxy)ethyl)carbamoyl)-cyclohexyl)nicotinamide To a stirred suspension of (1R,4R)-4-(6-((1,6-naphthyridin-2-yl)amino)-4-(cyclopropylamino)nicotinamido)cyclohexane-1-carboxylic acid (0.4 g, 0.9 mmol, Intermediate C) and 4-((2-(2-(2-aminoethoxy)ethoxy)ethyl)amino)-2-(2,6-dioxopiperidin-3-yl)isoindoline-1,3-dione hydrochloride (0.48 g, 1.07 mmol) in DMF (15 mL) was added DIPEA (0.8 mL, 4.5 mmol) and PyBOP (0.7 g, 1.3 mmol) at rt. The resulting reaction mixture was stirred at rt for 1 h. The reaction mixture was then transferred into ice water and the resulting solid was filtered off and dried reduced pressure. The crude product was purified using silica gel column chromatography (6% MeOH-DCM) to give 6-((1,6-naphthyridin-2-yl)amino)-4-(cyclopropylamino)-N-((1R,4R)-4-((2-(2-(2-((2-(2,6-dioxopiperidin-3-yl)-1,3-dioxoisoindolin-4-yl)amino)ethoxy)ethoxy)ethyl)-carbamoyl)cyclohexyl)nicotinamide I-23 as a yellow oil (0.41 g, 55%). $^1$H NMR (400 MHz, DMSO) δ ppm 11.09 (s, 1H), 10.34 (s, 1H), 9.03 (s, 1H), 8.55-8.54 (m, 3H), 8.39 (s, 1H), 8.24 (d, J=8.8 Hz, 1H), 8.12 (d, J=7.6 Hz, 1H), 7.73-7.77 (m, 1H), 7.57-7.53 (m, 2H), 7.49-7.47 (m, 1H), 7.13 (d, J=8.8 Hz, 1H), 7.02 (d, J=7.2 Hz, 1H), 6.60 (m, 1H), 5.03-4.96 (m, 1H), 3.61-3.59 (m, 3H), 3.55-3.54 (m, 2H), 3.51-3.50 (m, 2H), 3.47-3.44 (m, 2H), 3.39-3.36 (m, 2H), 3.16-3.14 (m, 2H), 2.90-2.82 (m, 1H), 2.58-2.55 (m, 1H), 2.03 (m, 2H), 1.84-1.82 (m, 2H), 1.73-1.71 (m, 2H), 1.42-1.38 (m, 2H), 1.35-1.33 (m, 4H), 0.92-0.91 (m, 2H), 0.56 (s, 2H). LC-MS (ESI$^+$) m/z 833.8 (M+H)$^+$.

Example 24: 6-((1,6-naphthyridin-2-yl)amino)-4-(cyclopropylamino)-N-((1R,4R)-4-((2-(2-(2-((2-(2,6-dioxopiperidin-3-yl)-1,3-dioxoisoindolin-4-yl)amino)ethoxy)ethoxy)ethyl)carbamoyl)cyclohexyl)nicotinamide, I-24

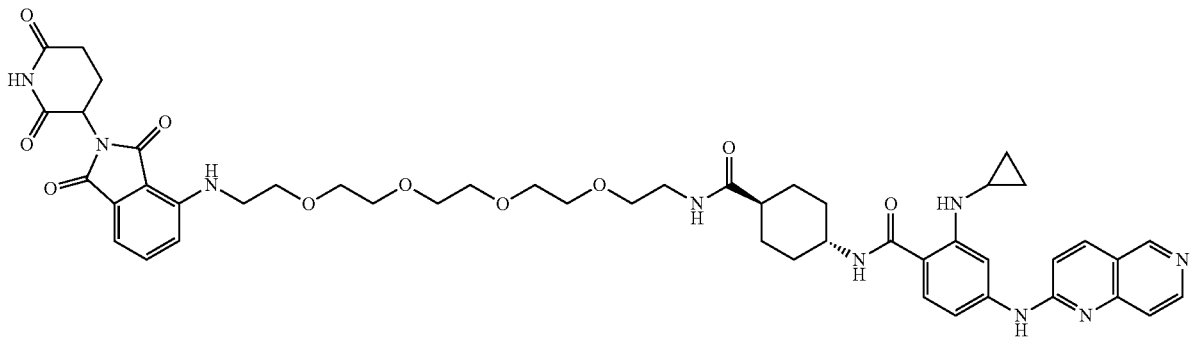 [SMILES: O=C1CCC(N2C(=O)c3cccc(NCCOCCOCCOCCOCCNC(=O)[C@H]4CC[C@H](NC(=O)c5ccc(Nc6ccc7cnccc7n6)cc5NC5CC5)CC4)c3C2=O)C(=O)N1]

6-((1,6-naphthyridin-2-yl)amino)-4-(cyclopropylamino)-N-((1r,4r)-4-((2-(2-(2-((2-(2,6-dioxopiperidin-3-yl)-1,3-dioxoisoindolin-4-yl)amino)ethoxy)ethoxy)ethyl) carbamoyl) cyclohexyl)nicotinamide I-24 was synthesized via Method 4 with Intermediate R as the fluorine and tert-butyl (14-amino-3,6,9,12-tetraoxatetradecyl)carbamate (CAS #811442-84-9) as the amine in Step 1. Intermediate C was used as the acid in Step 3. $^1$H NMR (400 MHz, DMSO) δ ppm 11.09 (s, 1H), 10.34 (s, 1H), 9.03 (s, 1H), 8.55-8.54 (m, 3H), 8.40 (s, 1H), 8.24 (d, J=8.8 Hz, 1H), 8.11 (d, J=7.6 Hz, 1H), 7.81-7.73 (m, 1H), 7.58-7.47 (m, 3H), 7.13 (d, J=8.8 Hz, 1H), 7.02 (d, J=7.2 Hz, 1H), 6.60-6.58 (m, 1H), 4.96 (m, 1H), 3.68-3.61 (m, 3H), 3.60-3.59 (m, 3H), 3.54-3.52 (m, 7H), 3.37-3.34 (m, 2H), 3.17-3.15 (m, 2H), 3.17-3.15 (m, 2H), 2.91-2.82 (m, 1H), 2.65-2.58 (m, 1H), 2.06-1.99 (m, 2H), 1.85-1.82 (m, 2H), 1.74-1.70 (m, 3H), 1.45-1.21 (m, 4H), 0.92-0.84 (m, 2H), 0.56 (s, 2H). LC-MS (ESI$^+$) m/z 922.2 (M+H)$^+$ Example 25: 6-((1,6-naphthyridin-2-yl)amino)-4-(cyclopropylamino)-N-((1r,4r)-4-((2-(2-((2-(2,6-dioxopiperidin-3-yl)-1,3-dioxoisoindolin-4-yl)amino)ethoxy)ethyl)carbamoyl)cyclohexyl) nicotinamide, I-25

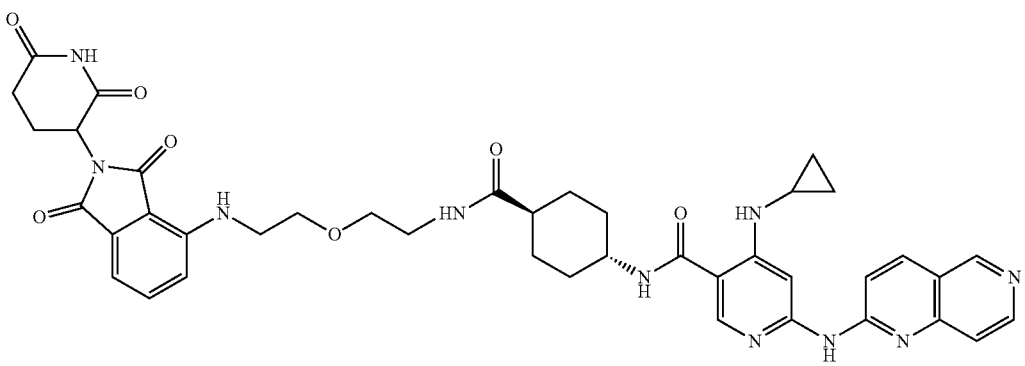 [SMILES: O=C1CCC(N2C(=O)c3cccc(NCCOCCNC(=O)[C@H]4CC[C@H](NC(=O)c5cnc(Nc6ccc7cnccc7n6)cc5NC5CC5)CC4)c3C2=O)C(=O)N1]

6-((1,6-naphthyridin-2-yl)amino)-4-(cyclopropylamino)-N-((1r,4r)-4-((2-(2-((2-(2,6-dioxopiperidin-3-yl)-1,3-dioxoisoindolin-4-yl)amino)ethoxy)ethyl)carbamoyl)cyclohexyl)nicotinamide I-25 was synthesized via Method 4 using Intermediate R as the fluorine and tert-butyl (2-(2-aminoethoxy)ethyl)carbamate (CAS #127828-22-2) as the amine in Step 1. The product of Step 2 was triturated with diethyl ether instead of MBTE. Intermediate C was used as the acid in Step 3 and the final product was purified by HPLC (0.1% formic acid in water/ACN). $^1$H NMR (400 MHz, DMSO-d$_6$) δ 11.1 (s, 1H), 10.34 (s, 1H), 9.03 (s, 1H), 8.56-8.54 (m, 3H), 8.40 (s, 1H), 8.25 (d, J=9.2 Hz, 1H), 8.15-8.05 (m, 2H), 7.81-7.75 (m, 1H), 7.60-7.5 (m, 2H), 7.50 (d, J=8.8 Hz, 1H), 7.14 (d, J=8.4 Hz, 1H), 7.04 (d, J=7.2 Hz, 1H), 6.59 (d, J=6.0 Hz, 1H), 5.04 (dd, J=13.0 Hz & 5.4 Hz, 1H), 3.7-3.55 (m, 3H), 3.50-3.40 (m, 4H), 3.25-3.15 (m, 2H), 2.90-2.80 (m, 1H), 2.55-2.65 (m, 2H), 2.10-1.95 (m, 2H), 1.85-1.65 (m, 4H), 1.45-1.21 (m, 4H), 0.92 (d, J=5.2 Hz, 2H), 0.57 (s, 2H); LC-MS (ESI$^+$) m/z 789.7 (M+H)$^+$.

Example 26: 6-((1,6-naphthyridin-2-yl)amino)-4-(cyclopropylamino)-N-((1r,3r)-3-((2-(2-(2-((2-(2,6-dioxopiperidin-3-yl)-1,3-dioxoisoindolin-4-yl)amino)ethoxy)ethoxy)ethyl) carbamoyl)cyclobutyl)nicotinamide, I-26

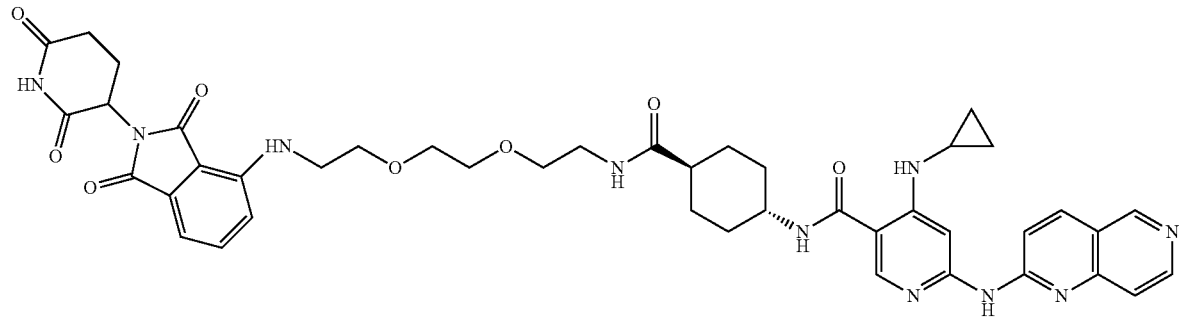 [SMILES: O=C1CCC(N2C(=O)c3cccc(NCCOCCOCCNC(=O)[C@H]4CC[C@H](NC(=O)c5cnc(Nc6ccc7cnccc7n6)cc5NC5CC5)CC4)c3C2=O)C(=O)N1]

6-((1,6-naphthyridin-2-yl)amino)-4-(cyclopropylamino)-N-((1r,3r)-3-((2-(2-(2-((2-(2,6-dioxopiperidin-3-yl)-1,3-dioxoisoindolin-4-yl)amino)ethoxy)ethoxy)ethyl) carbamoyl)cyclobutyl)nicotinamide I-26 was synthesized via Method 4 using Intermediate R as the fluorine and tert-butyl (2-(2-(2-aminoethoxy)ethoxy)ethyl)carbamate (CAS #153086-78-3) as the amine in Step 1. Intermediate O was used as the acid in Step 3. In Step 3, HATU was used as the coupling reagent instead of PyBOP and the reaction was run at rt for 4 h. $^1$H NMR (400 MHz, DMSO) δ 11.09 (s, 1H), 10.36 (s, 1H), 9.03 (s, 1H), 8.55-8.50 (m, 3H), 8.44 (s, 1H), 8.26 (d, J=8.8 Hz, 1H), 7.79 (t, J=5.6 Hz, 1H), 7.58-7.54 (m, 2H), 7.49 (d, J=9.2 Hz, 1H), 7.14 (d, J=8.4 Hz, 1H), 7.00 (d, J=7.2 Hz, 1H), 6.60 (s, 1H), 5.06-5.02 (m, 1H), 4.51-4.49 (m, 1H), 3.62-3.32 (m, 10H), 3.20-3.14 (m, 3H), 2.87-2.83 (m, 2H), 2.58-2.48 (m, 1H), 2.33-2.21 (m, 4H), 2.02-1.97 (m, 2H), 1.21 (m, 1H), 0.92 (d, J=5.2 Hz, 2H), 0.55 (s, 2H). LC-MS (ESI$^+$) m/z 805.68 (M+H)$^+$ Example 27: 6-(5-cyano-1H-pyrazolo[3,4-b]pyridin-1-yl)-4-(cyclopropylamino)-N-((1R,3R)-3-((2-(2-(2-((2-(2,6-dioxopiperidin-3-yl)-1,3-dioxoisoindolin-4-yl)amino)ethoxy)ethoxy)ethyl) carbamoyl)cyclobutyl)nicotinamide, I-27

6-(5-cyano-1H-pyrazolo[3,4-b]pyridin-1-yl)-4-(cyclopropylamino)-N-((1r,3r)-3-((2-(2-(2-((2-(2,6-dioxopiperidin-3-yl)-1,3-dioxoisoindolin-4-yl)amino)ethoxy)ethoxy)ethyl) carbamoyl)cyclobutyl)nicotinamide I-27 was synthesized via Method 4 using Intermediate R as the fluorine and tert-butyl (2-(2-(2-aminoethoxy)ethoxy)ethyl) carbamate (CAS #153086-78-3) as the amine in Step 1. (1R,3R)-3-(6-(5-cyano-1H-pyrazolo[3,4-b]pyridin-1-yl)-4-(cyclopropylamino)nicotinamido)cyclobutane-1-carboxylic acid (synthesized via Steps 1-2 of Method 3 for Example 21) was used as the acid in Step 3 which was run at rt for 2 h. The final compound was purified by prep HPLC (0.1% formic acid in water/ACN). $^1$H NMR (400 MHz, DMSO) δ 11.13 (s, 1H), 9.07 (d, J=2 Hz, 1H), 9.04 (d, J=2 Hz, 1H), 8.81 (d, J=7.2 Hz, 1H), 8.67 (s, 1H), 8.64 (s, 1H), 8.56 (s, 1H), 7.84 (t, J=6 Hz, 1H), 7.68 (s, 1H), 7.59 (t, J=7.2 Hz, 1H), 7.16 (d, J=8.4 Hz, 1H), 7.05 (d, J=7.2 Hz, 1H), 6.62 (t, J=5.6 Hz, 1H), 5.09-5.04 (m, 1H), 4.56-4.52 (m, 1H), 3.64-3.50 (m, 6H), 3.48-3.35 (m, 5H), 3.24-3.20 (m, 2H), 2.92-2.84 (m, 2H), 2.61-2.51 (m, 2H), 2.39-2.23 (m, 4H), 2.04-2.02 (m, 1H). LC-MS (ESI$^+$) m/z 804.5.

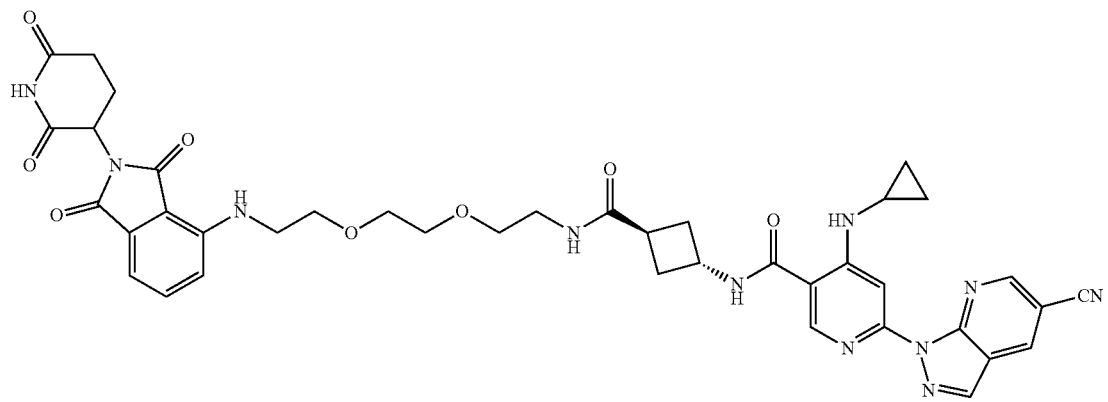 [SMILES: N#Cc1cnc2c(cnn2-c2cc(NC3CC3)c(C(=O)N[C@H]3C[C@H](C(=O)NCCOCCOCCNc4cccc5c4C(=O)N(C4CCC(=O)NC4=O)C5=O)C3)cn2)c1]

Example 29: 6-(5-cyano-1H-pyrazolo[3,4-b]pyridin-1-yl)-4-(cyclopropylamino)-N-((1r,4r)-4-((2-(2-(2-((2-(2,6-dioxopiperidin-3-yl)-1,3-dioxoisoindolin-4-yl)amino)ethoxy)ethoxy)ethyl)carbamoyl)cyclohexyl)nicotinamide, I-29

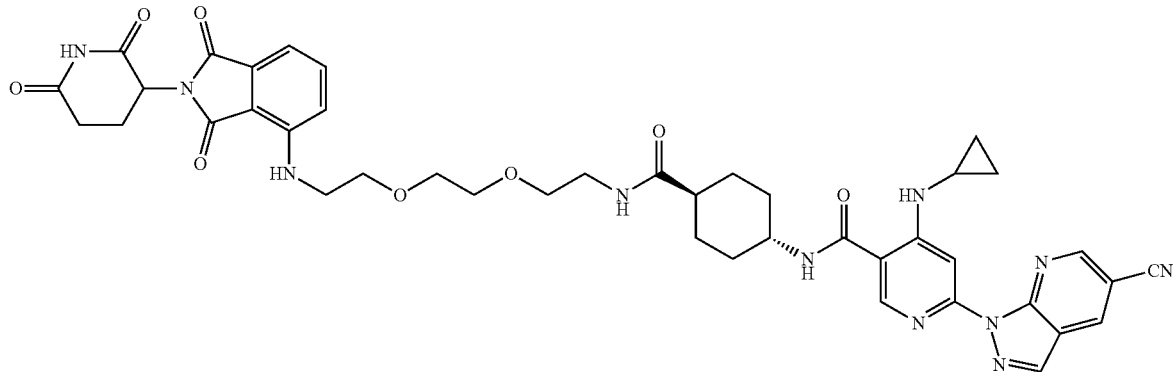 [SMILES: N#Cc1cnc2c(cnn2-c2cc(NC3CC3)c(C(=O)N[C@H]3CC[C@H](C(=O)NCCOCCOCCNc4cccc5c4C(=O)N(C4CCC(=O)NC4=O)C5=O)CC3)cn2)c1]

6-(5-cyano-1H-pyrazolo[3,4-b]pyridin-1-yl)-4-(cyclopropylamino)-N-((1r,4r)-4-((2-(2-(2-((2-(2,6-dioxopiperidin-3-yl)-1,3-dioxoisoindolin-4-yl)amino)ethoxy)ethoxy)ethyl)carbamoyl)cyclohexyl)nicotinamide I-29 was synthesized via Method 4 using Intermediate R as the fluorine and tert-butyl (2-(2-(2-aminoethoxy)ethoxy)ethyl) carbamate (CAS #153086-78-3) as the amine in Step 1. Intermediate AG was used as the acid in Step 3 which was run at rt for 2 h. The final product was purified using preparative HPLC (0.1% formic acid in water/ACN). Characterization of the final product: $^1$H NMR (400 MHz, DMSO) δ 11.13 (s, 1H), 9.08 (dd, $J_1$=2 Hz, $J_2$=13 Hz, 1H), 8.67 (s, 2H), 8.60 (d, J=18.4 Hz, 1H), 8.42 (d, J=7.6 Hz, 1H), 7.82-7.76 (m, 1H), 7.69 (s, 1H), 7.60 (t, J=7.6 Hz, 1H), 7.18 (d, J=8.4 Hz, 1H), 7.07 (d, J=6.8 Hz, 1H), 6.63 (t, J=5.6 Hz, 1H), 5.10-5.05 (m, 1H), 3.71-3.36 (m, 9H) 3.22-3.19 (m, 2H), 3.04-3.00 (m, 1H), 2.94-2.85 (m, 1H), 2.62-2.51 (m, 2H), 2.11-1.91 (m, 2H), 1.88-1.78 (m, 2H), 1.76-1.73 (m, 2H), 1.48-1.24 (m, 3H), 1.39-1.32 (m, 2H), 0.87-0.58 (m, 2H). LC-MS (ESI$^+$) m/z 832.78 (M+H)$^+$.

Example 30 (Method 5): 6-((1,6-naphthyridin-2-yl)amino)-4-(cyclopropylamino)-N-((1R,4R)-4-((3-(3-((2-(2,6-dioxopiperidin-3-yl)-1,3-dioxoisoindolin-4-yl)amino)propoxy)propyl)carbamoyl)cyclohexyl)nicotinamide, I-30

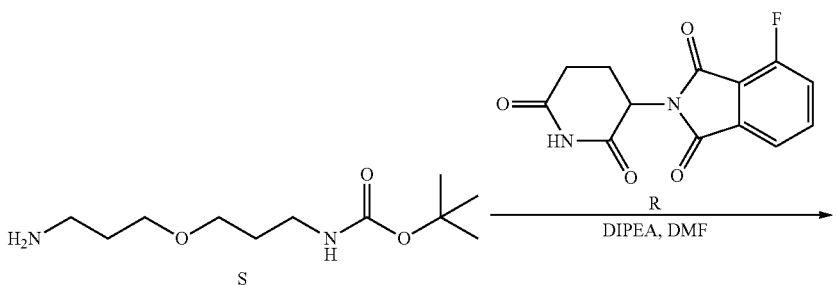

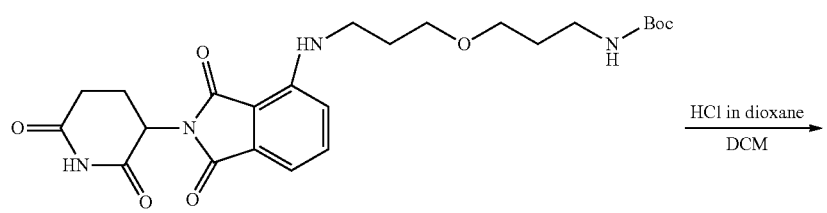

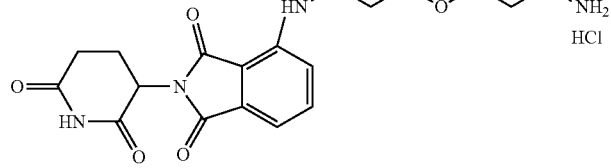

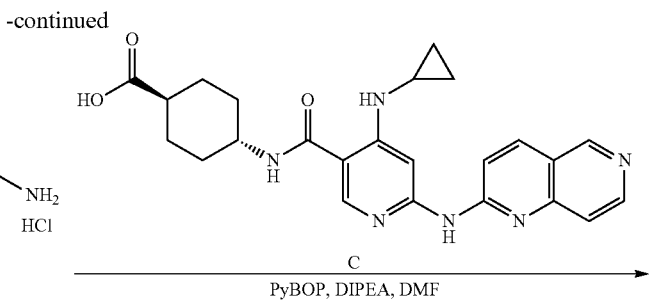

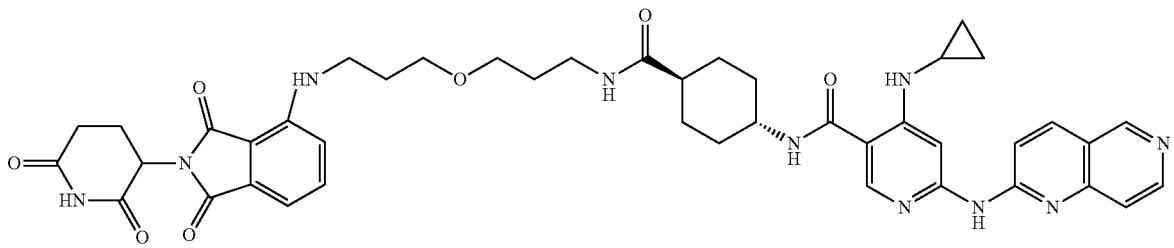

Step 1—tert-butyl (3-(3-((2-(2,6-dioxopiperidin-3-yl)-1,3-dioxoisoindolin-4-yl)amino)propoxy)propyl) carbamate A solution of tert-butyl (3-(3-aminopropoxy)propyl)carbamate (0.36 g, 1.55 mmol, Intermediate S), 2-(2,6-dioxopiperidin-3-yl)-4-fluoroisoindoline-1,3-dione (0.47 g, 1.70 mmol, Intermediate R) and DIPEA (0.4 mL, 2.3 mmol) in DMF (3 mL) was stirred at 80° C. for 1 h. The reaction mixture was then transferred into ice water and the resulting mixture was extracted using ethyl acetate (3×20 mL). The combined organic layer was dried over anhydrous sodium sulfate and filtered. The filtrate was evaporated under reduced pressure. The crude product was purified using silica gel column chromatography (3% MeOH-DCM) to give tert-butyl (3-(3-((2-(2,6-dioxopiperidin-3-yl)-1,3-dioxoisoindolin-4-yl)amino)propoxy)propyl)carbamate as a yellow semi-solid (0.1 g, 13%). LC-MS (ESI$^+$) m/z 489.5 (M+H)$^+$.

Step 2—4-((3-(3-aminopropoxy)propyl)amino)-2-(2,6-dioxopiperidin-3-yl)isoindoline-1,3-dione hydrochloride To a solution of tert-butyl (3-(3-((2-(2,6-dioxopiperidin-3-yl)-1,3-dioxoisoindolin-4-yl)amino)propoxy)propyl)carbamate (0.1 g, 0.2 mmol) in DCM (5 mL) was added 4N HCl in dioxane (2 mL) at 0° C. The reaction mixture was then allowed to come to rt and was stirred for 3 h. The reaction mixture was then evaporated under vacuum to afford the crude product which was triturated using MTBE (5 mL) to give 4-((3-(3-aminopropoxy)propyl)amino)-2-(2,6-dioxopiperidin-3-yl)isoindoline-1,3-dione hydrochloride as a yellow solid (0.06 g, 69%). LC-MS (ESI$^+$) m/z 389.4 (M+H)$^+$.

Step 3—6-((1,6-naphthyridin-2-yl)amino)-4-(cyclopropylamino)-N-((1R,4R)-4-((3-(3-((2-(2,6-dioxopiperidin-3-yl)-1,3-dioxoisoindolin-4-yl)amino) propoxy)propyl)carbamoyl)cyclohexyl)nicotinamide A solution of 4-((3-(3-aminopropoxy)propyl)amino)-2-(2,6-dioxopiperidin-3-yl)isoindoline-1,3-dione hydrochloride (0.06 g, 0.14 mmol), (1R,4R)-4-(6-((1,6-naphthyridin-2-yl)amino)-4-(cyclopropylamino)nicotineamido) cyclohexane-1-carboxylic acid (0.063 g, 0.14 mmol, Intermediate C), PyBOP (0.11 g, 0.21 mmol) and DIPEA (0.1 mL, 0.42 mmol) in DMF (3 mL) was stirred at rt for 2 h. The reaction mixture was then poured in ice water mixture (50 mL) and the solid precipitated was filtered. The crude solid was then purified by prep HPLC (0.1% formic acid in water/ACN) to give 6-((1,6-naphthyridin-2-yl)amino)-4-(cyclopropylamino)-N-((1R,4R)-4-((3-(3-((2-(2,6-dioxopiperidin-3-yl)-d1,3-dioxoisoindolin-4-yl)amino)propoxy) propyl)carbamoyl)cyclohexyl)nicotinamide I-30 as a yellow solid (0.018 g, 16%). $^1$H NMR (400 MHz, DMSO) δ 11.11 (s, 1H), 10.36 (s, 1H), 9.05 (s, 1H), 8.57 (d, J=5.2 Hz, 2H), 8.42 (s, 1H), 8.28 (d, J=8.8 Hz, 1H), 8.15 (d, J=4.4 Hz, 1H), 7.73-7.71 (m, 1H), 7.59-7.49 (m, 3H), 7.12 (d, J=8.8 Hz, 2H), 7.04 (d, J=7.2 Hz, 1H), 6.75-6.65 (m, 1H), 5.14-5.10 (m, 1H), 3.60-3.70 (m, 2H), 3.45 (t, J=5.6 Hz, 2H), 3.39-3.34 (m, 3H), 3.11-3.09 (m, 2H), 3.00-2.80 (m, 2H), 2.67-2.50 (m, 4H), 2.33 (s, 1H), 2.10-2.00 (m, 2H), 2.05-1.63 (m, 7H), 1.45-1.25 (m, 4H), 0.95 (d, J=4.8 Hz, 2H), 0.58 (s, 2H). LC-MS (ESI$^+$) m/z 817.8 (M+H)$^+$.

TABLE 4

Compounds synthesized via Method 5 with the addition of various amines to fluoride Intermediate R in Step 1, followed coupling with various acids in Step 3

| Ex-# | I-# | Step 1 Intermediate Amine | Step 3 Acid | LCMS (ES+) m/z (M + H)+ | HNMR (400 MHz, DMSO-d6) δ |
|---|---|---|---|---|---|
| 31 | I-31 | H | N | 792.4 | 11.13 (s, 1H), 10.38 (s, 1H), 9.06 (s, 1H), 8.58-8.55 (m, 4H), 8.48 (s, 1H), 8.29 (d, J = 9.2 Hz, 1H), 7.61-7.50 (m, 3H), 7.33-7.32 (m, 1H), 7.17 (d, J = 8.8 Hz, 1H), 7.06 (d, J = 7.2 Hz, 1H), 6.64 (t, J = 5.6 Hz, 1H), 5.10-5.05 (m, 1H), 4.51-4.41 (m, 2H), 3.66-3.41 (m, 13H), 2.68-2.57 (m, 2H), 2.37-2.34 (m, 1H), 2.20-2.13 (m, 2H), 2.06-2.20 (m, 3H), 1.24 (m, 1H), 0.95 (d, J = 4.8 Hz, 2H), 0.58 (s, 2H) |
| 32 | I-32 | W | L | 819.8 | 11.11 (s, 1H), 9.08 (d, J = 2 Hz, 1H), 9.04 (d, J = 2 Hz, 1H), 8.68 (s, 1H), 8.63 (s, 1H), 8.59 (s, 1H), 8.43 (d, J = 7.6 Hz, 1H), 7.74 (s, 1 Hz, 1H), 7.61-7.57 (m, 1H), 7.16 (d, J = 8.8 Hz, 1H), 7.05 (d, J = 7.2 Hz, 1H), 6.62 (s, 1H), 5.07-5.04 (m, 1H) 3.71-3.68 (m, 1H), 3.65-3.58 (m, 2H), 3.57-2.53 (m, 11H), 3.21-3.19 (m, 2H), 2.89-2.84 (m, 1H), 2.60-2.57 (m, 2H), 2.05-2.01 (m, 1H), 1.87-1.85 (m, 2H), 1.78-1.75 (m, 2H), 1.47-1.45 (m, 1H), 1.34-1.27 (m, 2H), 1.03-0.97 (m, 2H), 0.87-0.84 (m, 2H), 0.57 (s, 2H) |
| 33 | I-33 | Y | L | 907.8 | 11.11 (s, 1H), 9.08 (s, 1H), 9.04 (s, 1H), 9.89-9.59 (m, 3H), 8.46 (d, J = 5.6 Hz, 1H), 7.76 (s, 1H), 7.58 (t, J = 7.6 Hz, 1H), 7.15-7.03 (m, 2H), 6.61 (s, 1H), 5.06 (d, J = 7.6 Hz, 1H), 3.70-3.56 (m, 9H), 3.50-3.20 (m, 12H), 2.92-2.85 (m, 1H), 2.08-2.02 (m, 2H), 1.88-1.76 (m, 4H), 1.48-1.23 (m, 5H), 1.09-0.98 (m, 2H), 0.88-0.86 (m, 2H), 0.58 (s, 3H) |
| 34 | I-34 | H | N | 791.7 | 11.13 (s, 1H), 9.07 (dd, J₁ = 2 Hz, J₂ = 2 Hz, 2H), 8.81 (d, J = 6.8 Hz, 2H), 8.66 (s, 1H), 8.64 (s, 1H), 8.57 (s, 1H), 7.68 (s, 1H), 8.14 (t, J = 7.2 Hz, 1H), 7.16 (d, J = 8.4 Hz, 1H), 7.05 (d, J = 7.2 Hz, 1H), 6.25 (t, J = 6 Hz, 1H), 5.08-5.04 (m, 1H), 4.48-4.42 (m, 1H) 3.68-3.45 (m, 12H), 2.93-2.84 (m, 1H), 2.60-2.50 (m, 4H), 2.39-2.33 (m, 1H), 2.21-2.01 (m, 3H), 0.87-0.82 (m, 2H), 0.57-0.53 (m, 2H) |
| 35 | I-35 | U | L | 805.7 | 11.13 (s, 1H), 9.07 (d, J = 12 Hz, 1H), 8.68 (s, 1H), 8.63 (s, 1H), 8.54 (s, 1H), 8.50 (d, J = 8 Hz, 1H), 7.68 (s, 1H), 7.59 (t, J = 8 Hz, 1H), 7.15 (d, J = 12 Hz, 1H), 7.05 (d, J = 4 Hz, 1H), 6.63 (s, 1H), 5.07 (d, J = 8 Hz, 1H), 4.25 (d, J = 4 Hz, 1H), 3.65-3.49 (m, 13H), 3.29-3.28 (m, 2H), 2.94-2.87 (m, 1H), 2.62-2.56 (m, 3H), 2.34 (d, J = 8 Hz, 1H), 2.06-1.95 (m, 2H), 1.83 (s, 1H), 1.70-1.58 (m, 3H), 1.25 (s, 1H), 0.87-0.84 (m, 2H), 0.58 (s, 2H) |
| 36ᵃ | I-36 | ES | L | 878.9 | 11.03 (s, 1H), 9.07 (d, J = 4 Hz, 1H), 9.04 (d, J = 4 Hz, 1H), 8.83 (d, J = 8 Hz, 1H), 8.67 (d, J = 8 Hz, 2H), 8.59 (s, 1H), 7.69 (s, 1H), 7.59 (t, J = 8 Hz, 1H), |

TABLE 4-continued

Compounds synthesized via Method 5 with the addition of various
amines to fluoride Intermediate R in Step 1, followed coupling with various acids in Step 3

| Ex-# | I-# | Step 1 Intermediate Amine | Step 3 Acid | LCMS (ES+) m/z (M + H)+ | HNMR (400 MHz, DMSO-d6) δ |
|---|---|---|---|---|---|
| | | | | | 7.15 (d, J = 8 Hz, 1H), 7.04 (d, J = 4 Hz, 1H), 6.63-6.61 (m, 1H), 5.09-5.05 (m, 1H), 4.50-4.44 (m, 1H), 3.64-3.62 (m, 2H), 3.57-3.48 (m, 18H), 2.94-2.85 (m, 1H), 2.62-2.52 (m, 3H), 2.42-2.35 (m, 1H), 2.24-22.19 (m, 2H), 2.11-2.03 (m, 3H), 0.89-0.84 (m, 2H), 0.57 (s, 2H) |
| 37 | I-37 | EP | (1R,3R)-3-(6-(5-cyano-1H-pyrazolo[3,4-b]pyridin-1-yl)-4-(cyclopropyl-amino)-nicotinamido)-cyclobutane-1-carboxylic acid (synthesized via Steps 1-2 of Method 3 for Example 21) | 818.7 | 11.13 (s, 1H), 9.09-9.05 (m, 2H), 8.84 (t, J = 7.2 Hz, 1H), 868 (d, J = 7.6 Hz, 2H), 8.56 (s, 1H), 7.69 (d, J = 2.4 Hz, 1H), 7.59-7.57 (m, 1H), 7.15 (t, J = 9.2 Hz, 1H), 7.04 (t, J = 7.2 Hz, 1H), 6.65-6.60 (m, 1H), 2.10-5.04 (m, 1H), 4.42-4.35 (m, 1H), 3.66-3.28 (m, 11H), 2.93-2.85 (m, 4H), 2.69-2.35 (m, 5H), 2.33-2.26 (m, 2H), 2.06-2.02 (m, 1H), 0.88-0.84 (m, 2H), 0.59 (d, J = 6.8 Hz, 2H) |
| 38 | I-38 | V | AG | 934.9 | 11.11 (s, 1H), 9.08-9.03 (m, 2H), 8.67 (s, 1H), 8.60 (s, 1H), 8.53 (s, 1H), 8.45-8.40 (m, 1H), 7.68 (s, 1H), 7.61-7.54 (m, 1H), 7.17-7.11 (m, 1H), 7.06-7.02 (m, 1H), 6.58-6.55 (m, 1H), 5.05-5.02 (m, 1H), 3.72-3.65 (m, 1H) 3.63-3.61 (m, 2H), 3.60-3.54 (m, 9H), 4.46-3.43 (m, 6H), 3.06 (s, 2H), 2.93-2.86 (m, 2H), 2.68-2.57 (m, 4H), 2.51-2.34 (m, 3H), 2.05-2.03 (m, 1H), 2.02-1.92 (m, 2H), 1.76-1.74 (m, 2H), 1.48-1.42 (m, 4H), 0.97-0.85 (m, 2H), 0.57 (m, 2H) |
| 39 | I-39 | V | (1R,3R)-3-(6-(5-cyano-1H-pyrazolo[3,4-b]pyridin-1-yl)-4-(cyclopropyl-amino)-nicotinamido)-cyclobutane-1-carboxylic acid (synthesized via Step 1-2 of Method 3 for Example 21) | 906.8 | 11.12 (s, 1H), 9.07-9.04 (m, 2H), 8.87-8.84 (m, 1H), 8.68-8.67 (m, 2H), 8.57 (s, 1H), 7.70 (s, 1H), 7.58-7.56 (m, 1H), 7.16-7.12 (m, 1 Hz, 1H), 7.05-7.02 (m, 1H), 6.61-6.59 (m, 1H), 5.08-5.04 (m, 1H), 4.42-4.40 (m, 1H), 3.64-3.62 (m, 2H), 3.61-3.54 (m, 11H), 3.53-3.50 (m, 3H), 2.91 (s, 2H), 2.86 (s, 1H), 2.68-2.57 (m, 4H), 2.51-2.46 (m, 3H), 2.34-2.29 (m, 3H), 2.05-0.02 (m, 1H), 0.87-0.85 (m, 2H), 0.57 (s, 2H) |

*Step 1 was run at 80-90° C. for 1-1.5 h. The intermediate of Step 2 could also be triturated with similar solvents to MBTE, such as diethyl ether. The final product of Step 3 was often purified by silica gel column chromatography (10% MeOH-DCM) first, then preparative HPLC (0.1% formic acid in water/ACN).
[a]Step 2 was run for 16 h at rt and the intermediate was not triturated.

Example 40 (Method 6): 6-((1,6-naphthyridin-2-yl)amino)-4-(cyclopropylamino)-N-((1R,4R)-4-((2-(2-(2-((2-(2,6-dioxopiperidin-3-yl)-1,3-dioxoisoindolin-4-yl)amino)ethoxy)ethoxy)ethyl)(methyl)carbamoyl)cyclohexyl)nicotinamide, I-40 filtered. The filtrate was evaporated under reduced pressure and the crude product which was purified using silica gel column chromatography (5% MeOH-DCM) to give tert-butyl (2-(2-(2-(((1R,4R)-4-(6-(((1,6-naphthyridin-2-yl)amino)-4-(cyclopropylamino)nicotinamido)-N-methylcy-

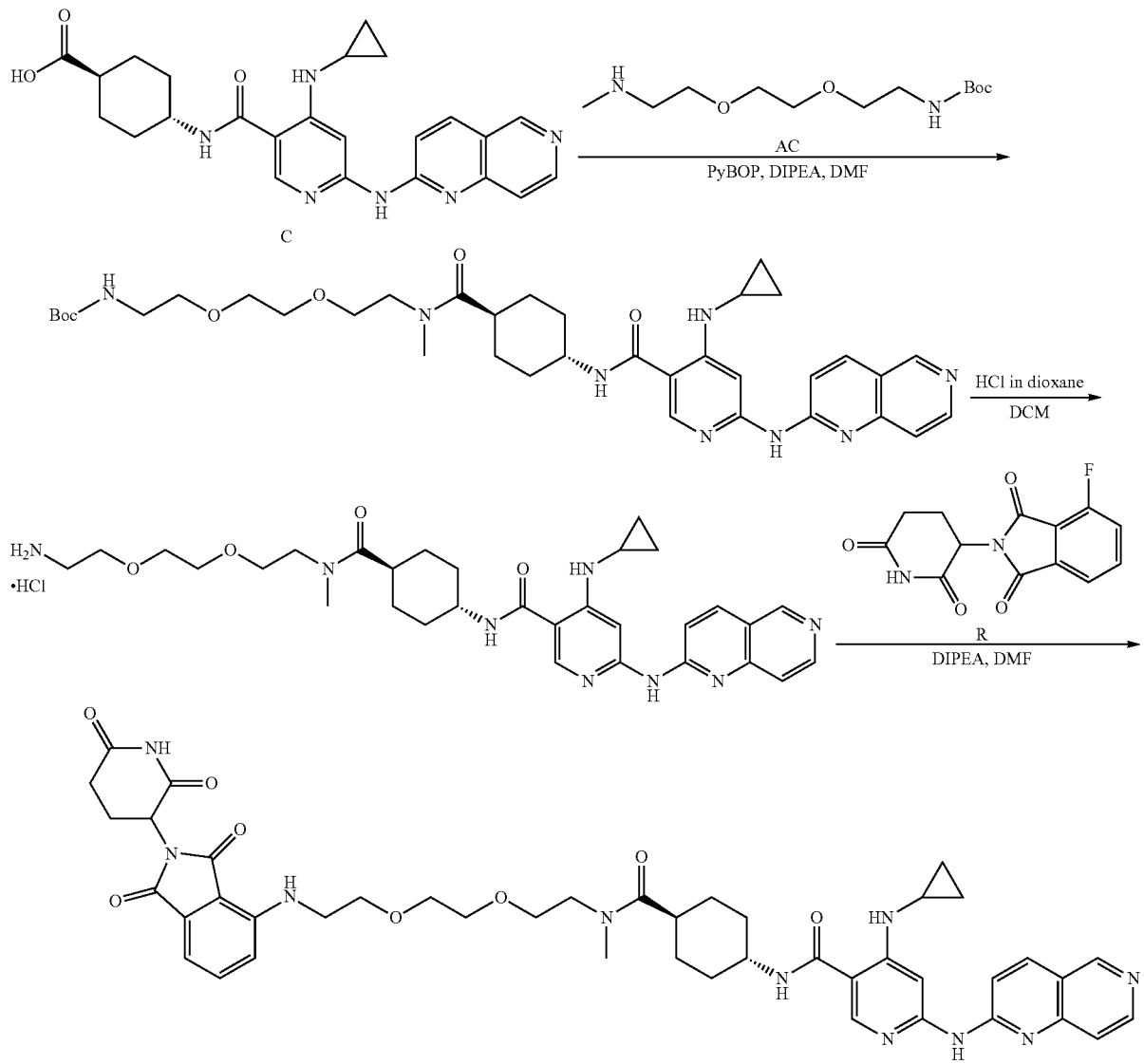

Step 1—tert-butyl (2-(2-(2-(((1R,4R)-4-(6-((1,6-naphthyridin-2-yl)amino)-4-(cyclopropylamino)nicotinamido)-N-methylcyclohexane-1-carboxamido)ethoxy)ethoxy)ethyl)carbamate A solution of (1R,4R)-4-(6-((1,6-naphthyridin-2-yl)amino)-4-(cyclopropylamino) nicotinamido)cyclohexane-1-carboxylic acid (0.7 g, 1.57 mmol, Intermediate C), tert-butyl(2-(2-(2-(methylamino)ethoxy)ethoxy)ethyl)carbamate (0.42 g, 1.57 mmol, Intermediate AC), PyBOP (1.23 g, 2.40 mmol) and DIPEA (0.7 mL, 2.5 mmol) in DMF (10 mL) was stirred at rt for 2 h. The reaction mixture was then transferred into ice water and the resulting mixture was extracted using ethyl acetate (3×30 mL). The combined organic layer was dried over anhydrous sodium sulfate and clohexane-1-carboxamido)ethoxy)ethoxy)ethyl)carbamate as a yellow solid (0.3 g, 24%)
LC-MS (ESI⁺) m/z 494.5 (M+H)⁺.

Step 2—6-((1,6-naphthyridin-2-yl)amino)-N-((1R,4R)-4-((2-(2-(2-aminoethoxy) ethoxy)ethyl)(methyl)carbamoyl)cyclohexyl)-4-(cyclopropylamino)nicotinamide hydrochloride To the solution of tert-butyl (2-(2-(2-(((1R,4R)-4-(6-((1,6-naphthyridin-2-yl)amino)-4-(cyclopropyl amino)nicotinamido)-N-methylcyclohexane-1-carboxamido)ethoxy)ethyl)-carbamate (0.3 g, 0.43 mmol) in DCM (3 mL) was added 4N HCl in dioxane (2 mL) at 0° C. The reaction mixture was allowed to warm to rt and stirred for 3 h. The reaction mixture was then evaporated under vacuum to afford the crude product which was triturated using MTBE (5 mL) to give 6-((1,6-naphthyridin-2-yl)amino)-N-((1R,4R)-4-((2-(2-(2-aminoethoxy)ethoxy)ethyl)-(methyl)carbamoyl)cyclohexyl)-4-(cyclopropyl amino)nicotinamide hydrochloride as a light yellow solid (0.25 g, 97%). LC-MS (ESI$^+$) m/z 591.4 (M+H)$^+$.

Step 3—6-((1,6-naphthyridin-2-yl)amino)-4-(cyclopropylamino)-N-((1R,4R)-4-((2-(2-(2-((2-(2,6-dioxopiperidin-3-yl)-1,3-dioxoisoindolin-4-yl)amino)ethoxy)ethoxy)ethyl)(methyl) carbamoyl) cyclohexyl)nicotinamide A solution of 6-((1,6-naphthyridin-2-yl)amino)-N-((1R,4R)-4-((2-(2-(2-aminoethoxy)ethoxy)ethyl)(methyl)carbamoyl)cyclohexyl)-4-(cyclopropylamino) nicotinamidehydrochloride (0.25 g, 0.42 mmol), 2-(2,6-dioxopiperidin-3-yl)-4-fluoroisoindoline-1,3-dione (0.13 g, 0.46 mmol, Intermediate R) and DIPEA (0.22 mL, 1.26 mmol) in DMF (2 mL) was heated at 90° C. for 1 h. The reaction mixture was then transferred into ice water and the resulting mixture was extracted using ethyl acetate (3×20 mL). The combined organic layer was dried over anhydrous sodium sulfate and filtered. The filtrate was evaporated under reduced pressure and the crude product was purified using preparative HPLC (0.1% formic acid in water/ACN) to give 6-((1,6-naphthyridin-2-yl)amino)-4-(cyclopropylamino)-N-((1R,4R)-4-((2-(2-(((2-(2,6-dioxopiperidin-3-yl)-1,3-dioxoisoindolin-4-yl)amino)ethoxy)ethoxy)ethyl)(methyl) carbamoyl) cyclohexyl)nicotinamide I-40 as yellow solid (0.01 g, 5%). $^1$H NMR (400 MHz, DMSO) δ 11.11 (s, 1H), 10.35 (s, 1H), 9.05 (s, 1H), 8.57-8.56 (m, 3H), 8.42 (d, J=5.2 Hz, 1H), 8.28 (d, J=9.2 Hz, 1H), 7.16 (s, 1H), 8.14-8.11 (m, 1H), 7.61-7.50 (m, 3H), 7.16-7.13 (m, 1H), 7.06-7.03 (m, 1H), 6.62 (t, J=5.6 Hz, 1H), 5.03 (t, J=8.4 Hz, 1H), 3.64-3.34 (m, 11H), 3.03 (s, 2H), 2.85 (s, 2H), 2.67-2.50 (m, 3H), 2.04 (bs, 1H), 1.90-1.80 (m, 2H), 1.46-1.38 (m, 4H), 0.95 (t, J=5.2 Hz, 1H), 0.57 (s, 1H). LC-MS (ESI$^+$) m/z 848 (M+H)$^+$.

Example 41: 6-((1,6-naphthyridin-2-yl)amino)-4-(cyclopropylamino)-N-((1r,4r)-4-((2-((5-((2-((2-(2,6-dioxopiperidin-3-yl)-1,3-dioxoisoindolin-4-yl)amino)ethoxy)methyl)pyridin-2-yl)methoxy)ethyl)carbamoyl)cyclohexyl)nicotinamide, I-41

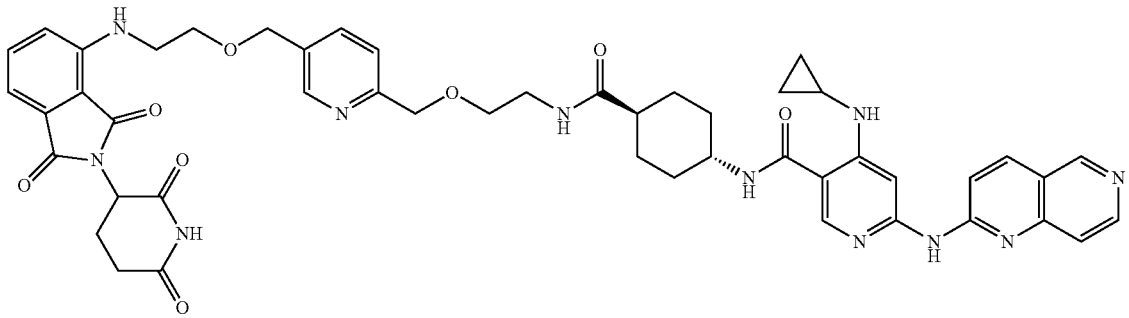 [SMILES: O=C1CCC(N2C(=O)c3cccc(NCCOCc4ccc(COCCNC(=O)[C@H]5CC[C@H](NC(=O)c6cnc(Nc7ccc8cnccc8n7)cc6NC6CC6)CC5)nc4)c3C2=O)C(=O)N1]

6-((1,6-naphthyridin-2-yl)amino)-4-(cyclopropylamino)-N-((1r,4r)-4-((2-((5-((2-((2-(2,6-dioxopiperidin-3-yl)-1,3-dioxoisoindolin-4-yl)amino)ethoxy)methyl)pyridin-2-yl)methoxy)ethyl)carbamoyl)cyclohexyl)nicotinamide I-41 was synthesized via Method 6 using Intermediate AF as the amine and Intermediate C as the acid in Step 1. In Step 3, Intermediate R was used as the fluorine and the reaction was run for 2 h at 90° C. The final product was purified first by silica gel column chromatography (15% MeOH-DCM) followed by preparative HPLC (0.1% formic acid in water/ACN). Characterization of the final product: $^1$H NMR (400 MHz, DMSO-d$_6$) δ 11.13 (s, 1H), 10.37 (s, 1H) 9.06 (s, 1H), 8.60-8.55 (m, 3H), 8.49 (s, 1H), 8.43 (s, 1H), 8.28 (d, J=9.2 Hz, 1H), 8.15 (d, J=8.0 Hz, 1H), 7.91 (t, J=5.2 Hz, 1H), 7.76 (d, J=6.4 Hz, 1H), 7.61-7.55 (m, 2H), 7.52 (d, J=9.2 Hz, 1H), 7.43 (d, J=7.6 Hz, 1H), 7.17 (d, J=8.4 Hz, 1H), 7.05 (d, J=7.2 Hz, 1H), 6.70-6.60 (m, 1H), 5.11-5.06 (m, 1H), 4.65-4.50 (m, 4H), 3.75-3.65 (m, 3H), 3.60-3.50 (m, 4H), 3.33-3.25 (m, 2H), 3.30-2.80 (m, 2H), 2.70-2.60 (m, 2H), 2.22-2.00 (m, 2H), 1.95-1.85 (m, 2H), 1.80-1.60 (m, 2H), 1.50-1.25 (m, 4H), 0.95 (d, J=5.2 Hz, 2H), 0.59 (s, 2H), LC-MS (ESI$^+$) m/z 909.8 (M+H)$^+$.

Example 42: 6-(5-cyano-1H-pyrazolo[3,4-b]pyridin-1-yl)-4-(cyclopropylamino)-N-((1r,4r)-4-((2-(2-(2-((2-(2,6-dioxopiperidin-3-yl)-1,3-dioxoisoindolin-4-yl)amino)ethoxy)ethoxy)ethyl) (methyl)carbamoyl) cyclohexyl)nicotinamide, I-42

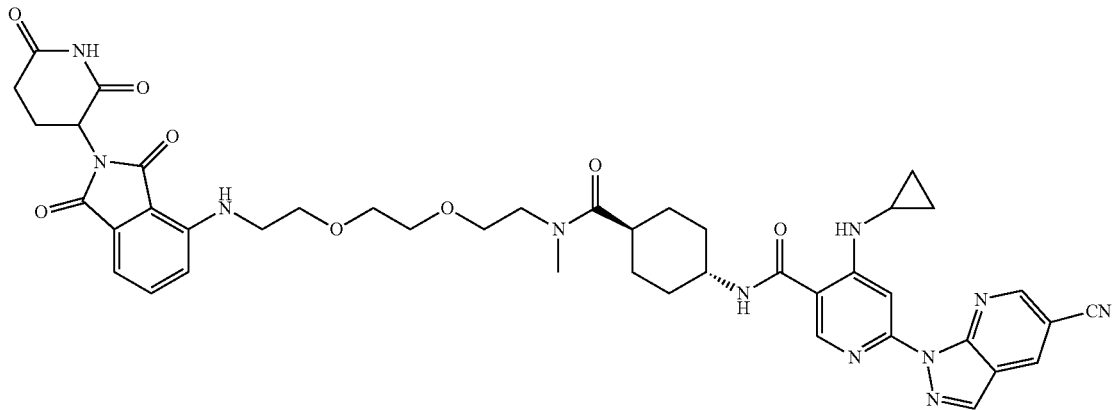 [SMILES: CN(CCOCCOCCNc1cccc2c1C(=O)N(C1CCC(=O)NC1=O)C2=O)C(=O)[C@H]1CC[C@H](NC(=O)c2cnc(-n3ncc4cc(C#N)cnc43)cc2NC2CC2)CC1]

6-(5-cyano-1H-pyrazolo[3,4-b]pyridin-1-yl)-4-(cyclopropylamino)-N-((1r,4r)-4-((2-(2-(2-((2-(2,6-dioxopiperidin-3-yl)-1,3-dioxoisoindolin-4-yl)amino)ethoxy)ethoxy)ethyl) (methyl)carbamoyl)cyclohexyl)nicotinamide I-42 was synthesized via Method 6 using Intermediate AC as the amine and Intermediate AG as the acid in Step 1. In Step 3, Intermediate R was used as the fluorine. Characterization of the final product: $^1$H NMR (400 MHz, DMSO) δ 11.13 (s, 1H), 9.07 (s, 1H), 9.04 (d, J=2 Hz, 1H), 8.67 (s, 1H), 8.60 (t, J=4.4 Hz, 1H), 8.53 (s, 1H), 8.45-8.39 (m, 1H), 7.68 (s, 1H), 7.62-7.57 (m, 1H), 7.18-7.14 (m, 1H), 7.07-7.03 (m, 1H), 6.63 (bs, 1H), 5.10-5.05 (m, 1H), 3.70 (bs, 1H), 3.63-3.39 (m, 11H), 3.04 (s, 2H), 2.93-2.85 (m, 1H), 2.80 (s, 2H), 2.68-2.51 (m, 4H), 2.09-2.04 (m, 1H), 1.92-1.85 (m, 2H), 1.74-1.72 (m, 2H), 1.47-1.40 (m, 4H), 0.87 (d, J=5.2 Hz, 1H), 0.58 (s, 2H). LC-MS (ESI$^+$) m/z 846.2

Example 43: 6-((1,6-naphthyridin-2-yl)amino)-4-(cyclopropylamino)-N-(1-(2-(2-(2-(2-((2-(2,6-dioxopiperidin-3-yl)-1,3-dioxoisoindolin-4-yl)amino)ethoxy)ethoxy)ethoxy)acetyl) piperidin-4-yl) nicotinamide, I-43

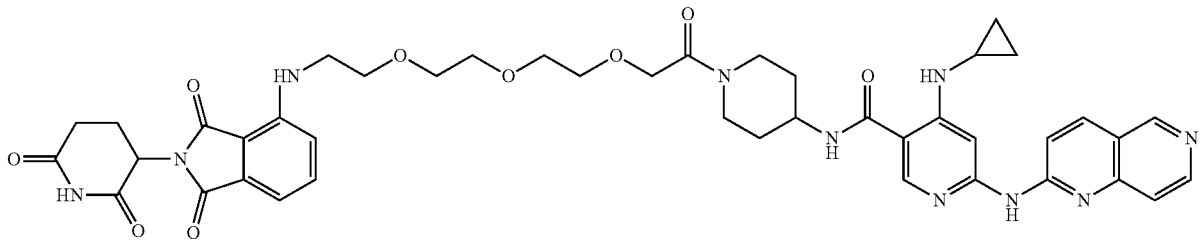 [SMILES: O=C1CCC(N2C(=O)c3cccc(NCCOCCOCCOCC(=O)N4CCC(NC(=O)c5cnc(Nc6ccc7cnccc7n6)cc5NC5CC5)CC4)c3C2=O)C(=O)N1]

6-((1,6-naphthyridin-2-yl)amino)-4-(cyclopropylamino)-N-(1-(2-(2-(2-(2-((2-(2,6-dioxopiperidin-3-yl)-1,3-dioxoisoindolin-4-yl)amino)ethoxy)ethoxy)ethoxy)acetyl) piperidin-4-yl)nicotinamide I-43 was synthesized via Method 6 using Intermediate EO as the amine and 2,2-dimethyl-4-oxo-3,8,11,14-tetraoxa-5-azahexadecan-16-oic acid (CAS #462100-06-7) as the acid in Step 1. In Step 3, Intermediate R was used as the fluorine. Characterization of the final product: $^1$H NMR (400 MHz, DMSO) δ 11.11 (s, 1H), 10.36 (s, 1H), 9.05 (s, 1H), 8.57-8.54 (m, 3H), 8.43 (s, 1H), 8.28 (d, J=9.2 Hz, 1H), 8.22-8.16 (m, 1H), 7.59-7.49 (m, 3H), 7.14 (d, J=8.4 Hz, 1H), 7.04 (d, J=6.8 Hz, 1H), 6.61 (t, J=5.6 Hz, 1H), 5.08-5.03 (m, 1H), 4.30-4.27 (m, 1H), 4.19-4.08 (m, 2H), 3.99-3.97 (m, 1H), 3.83-3.80 (m, 1H), 3.83-3.61 (m, 2H), 3.57-3.33 (m, 8H), 3.10-3.00 (m, 2H), 2.88-2.85 (m, 1H), 2.70-2.50 (m, 5H), 2.04-2.01 (m, 1H), 1.90-1.75 (m, 2H), 1.55-1.30 (m, 2H), 0.95 (d, J=5.2 Hz, 1H), 0.58 (s, 1H). LC-MS (ESI$^+$) m/z 849.4 (M+H)$^+$.

Example 44: 6-(5-cyano-1H-pyrazolo[3,4-b]pyridin-1-yl)-4-(cyclopropylamino)-N-((1r,4r)-4-((2-(2-(2-((2-(2,6-dioxopiperidin-3-yl)-1,3-dioxoisoindolin-4-yl)amino)ethoxy)ethoxy)ethyl)(methyl)carbamoyl)cyclohexyl)nicotinamide, I-44

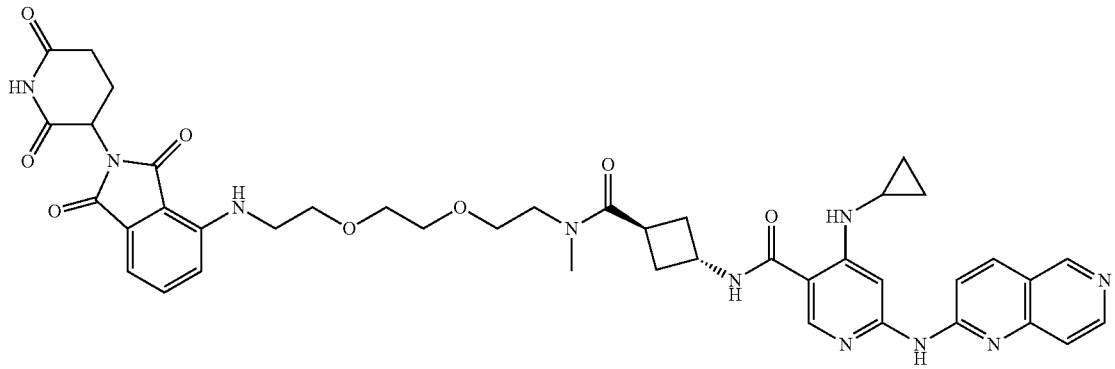 [SMILES: CN(CCOCCOCCNc1cccc2c1C(=O)N(C1CCC(=O)NC1=O)C2=O)C(=O)[C@H]1C[C@H](NC(=O)c2cnc(Nc3ccc4cnccc4n3)cc2NC2CC2)C1]

6-((1,6-naphthyridin-2-yl)amino)-4-(cyclopropylamino)-N-((1r,3r)-3-((2-(2-(2-((2-(2,6-dioxopiperidin-3-yl)-1,3-dioxoisoindolin-4-yl)amino)ethoxy)ethoxy)ethyl)(methyl)carbamoyl)cyclobutyl)nicotinamide I-44 was synthesized via Method 6 using Intermediate AC as the amine and Intermediate O as the acid in Step 1. In Step 3, Intermediate R was used as the fluorine. Characterization of the final product: $^1$H NMR (400 MHz, DMSO) δ 11.10 (s, 1H), 10.36 (d, J=4 Hz, 1H), 9.05 (s, 1H), 8.57-8.56 (m, 3H), 8.47 (s, 1H), 8.28 (d, J=9.2 Hz, 1H), 7.60-7.50 (m, 3H), 7.16 (t, J=8.4 Hz, 1H), 7.05-7.02 (m, 1H), 6.63-6.60 (m, 1H), 5.08-5.03 (m, 1H), 4.38-4.30 (m, 1H), 3.64-3.44 (m, 12H), 2.91 (s, 3H), 2.67-2.54 (m, 3H), 251-2.50 (m, 3H), 2.42-2.24 (m, 3H), 2.04-2.01 (m, 1H), 0.94 (t, J=6.4 Hz, 1H), 0.57 (t, J=6.4 Hz, 1H). LC-MS (ESI$^+$) m/z 818.92 (M+H)$^+$.

Example 45: 6-(5-cyano-1H-pyrazolo[3,4-b]pyridin-1-yl)-4-(cyclopropylamino)-N-((1R,4R)-4-((14-((2-(2,6-dioxopiperidin-3-yl)-1,3-dioxoisoindolin-4-yl)amino)-3,9,12-trioxa-6-azatetradecyl)carbamoyl)cyclohexyl)nicotinamide, I-45

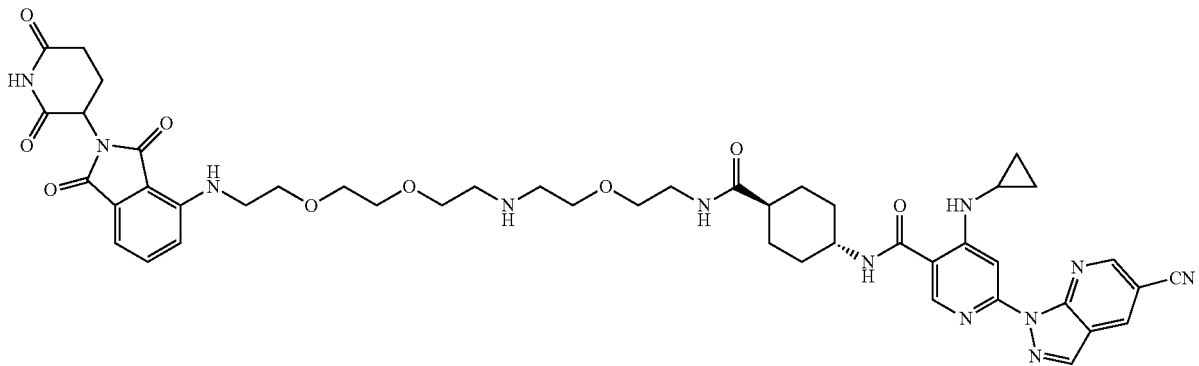 [SMILES: N#Cc1cnc2c(cnn2-c2cc(NC3CC3)c(C(=O)N[C@H]3CC[C@H](C(=O)NCCOCCNCCOCCOCCNc4cccc5c4C(=O)N(C4CCC(=O)NC4=O)C5=O)CC3)cn2)c1]

6-(5-cyano-1H-pyrazolo[3,4-b]pyridin-1-yl)-4-(cyclopropylamino)-N-((1R,4R)-4-((14-((2-(2,6-dioxopiperidin-3-yl)-1,3-dioxoisoindolin-4-yl)amino)-3,9,12-trioxa-6-azatetradecyl)carbamoyl)cyclohexyl)nicotinamide I-45 was prepared via Method 6 using Intermediate ER as the amine and Intermediate AG as the acid in Step 1. In Step 2, the BOC intermediate was deprotected using TFA at rt in DCM for 2 h. In Step 3, Intermediate R was used as the fluorine and the reaction was run at 80° C. for 2 h. Characterization of the final product: $^1$H NMR (400 MHz, DMSO-d$_6$) δ 11.05 (s, 1H), 9.08-9.04 (m, 2H), 8.67 (s, 1H), 8.61 (s, 1H), 8.56 (s, 1H), 8.42 (d, J=7.2 Hz, 1H), 7.86-7.83 (m, 1H), 7.69 (s, 1H), 7.61-7.57 (m, 1H), 7.17-7.15 (m, 1H), 7.06-7.04 (m, 1H), 6.64-6.61 (m, 1H), 5.09-5.05 (m, 1H), 3.74-3.72 (m, 2H), 3.65-3.63 (m, 5H), 3.60-3.59 (m, 6H), 3.41-3.38 (m, 4H), 3.23-3.20 (m, 2H), 2.94-2.90 (m, 1H), 2.76-2.74 (m, 4H), 2.69-2.62 (m, 2H), 2.15-2.09 (m, 2H), 2.03-1.93 (m, 2H), 1.90-1.79 (m, 2H), 1.50-1.31 (m, 5H), 0.89-0.86 (m, 2H), 0.58 (s, 2H). LC-MS (ESI$^+$) m/z 919.09 (M+H)$^+$.

2133

Example 46 (Method 7): 6-(5-Cyanopyrazolo[3,4-b]pyridin-1-yl)-4-(cyclopropylamino)-N-[3-[2-[2-[2-[[2-(2,6-dioxo-3-piperidyl)-1,3-dioxo-isoindolin-4-yl]amino]ethoxy]ethoxy]ethoxy]-2-fluoro-propyl]pyridine-3-carboxamide, I-46

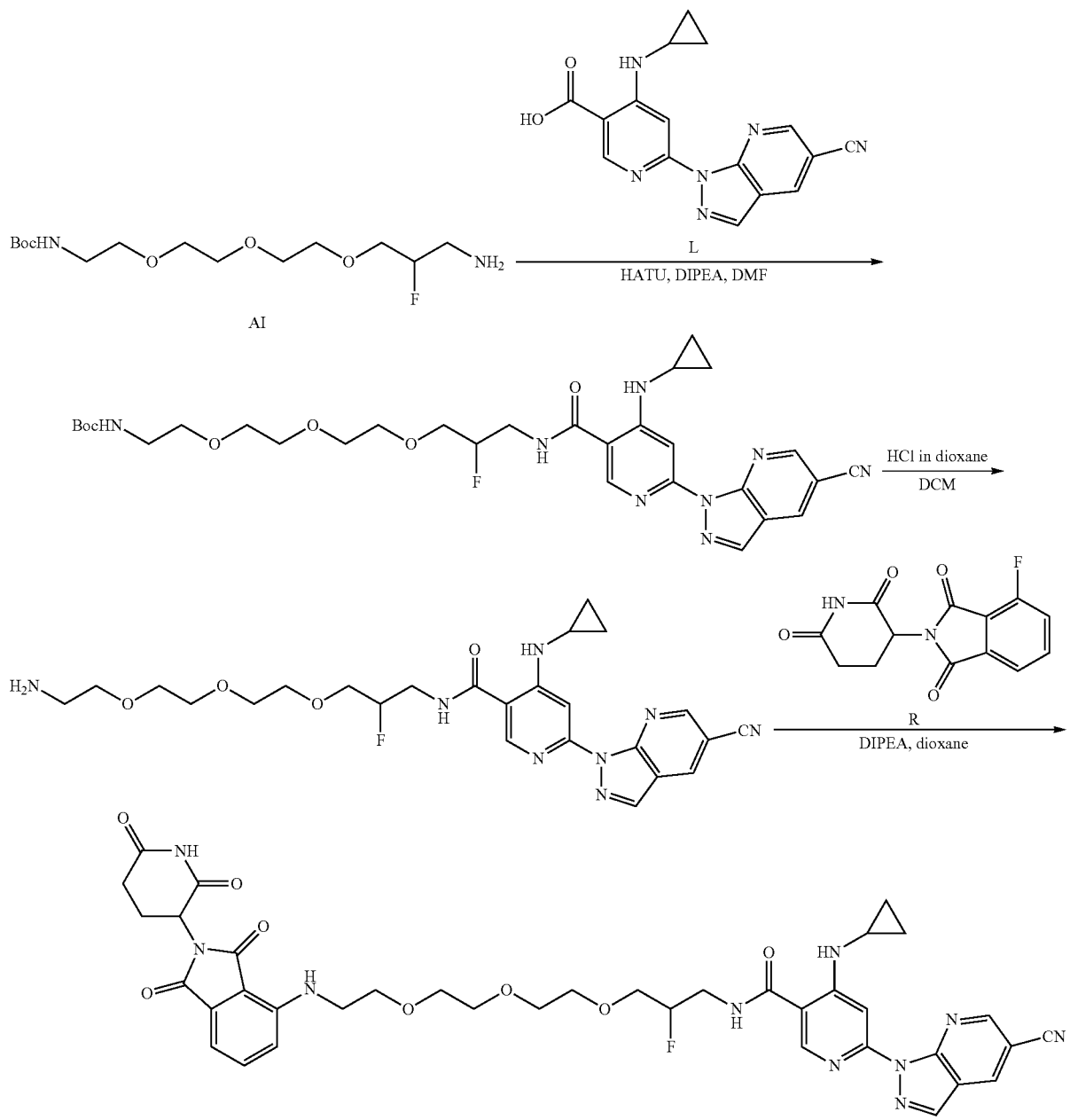

Step 1—Tert-butyl N-[2-[2-[2-[3-[[6-(5-cyanopyrazolo[3,4-b]pyridin-1-yl)-4-(cyclopropylamino) pyridine-3-carbonyl]amino]-2-fluoro-prop oxy]ethoxy]ethoxy]ethyl]carbamate To a solution of tert-butyl N-[2-[2-[2-(3-amino-2-fluoro-propoxy)ethoxy]ethoxy]ethyl]carbamate (200 mg, 617 umol, Intermediate AI), 6-(5-cyanopyrazolo[3,4-b]pyridin-1-yl)-4-(cyclopropylamino)pyridine-3-carboxylic acid (268

2134 mg, 617 umol, Intermediate L, as the TFA salt) and DIPEA (398 mg, 3.08 mmol) in DMF (3 mL) was added HATU (281 mg, 740 umol). The mixture was stirred at rt for 1 h. On completion, the reaction mixture was diluted with $H_2O$ (30 mL), extracted with EA (3×20 mL), dried with $Na_2SO_4$, filtered and concentrated in vacuo. The residue was purified by prep-HPLC (0.1% $NH_3.H_2O$) to give the title compound (82.0 mg, 21% yield) as a yellow oil. LC-MS (ESI$^+$) m/z 627.4 (M+H)$^+$.

Step 2—N-[3-[2-[2-(2-aminoethoxy)ethoxy]ethoxy]-2-fluoro-propyl]-6-(5-cyanopyrazolo[3,4-b]pyridin-1-yl)-4-(cyclopropylamino)pyridine-3-carboxamide To a solution of tert-butyl N-[2-[2-[2-[3-[[6-(5-cyanopyrazolo[3,4-b]pyridin-1-yl)-4-(cyclopropylamino)pyridine- 3-carbonyl]amino]-2-fluoro-propoxy]ethoxy]ethoxy]ethyl]carbamate (90.0 mg, 144 umol) in DCM (2 mL) was added HCl in dioxane (4 M, 2 mL). The mixture was stirred at rt for 15 minutes. On completion, the reaction mixture was concentrated in vacuo to give the title compound (75.0 mg, 93% yield) as a yellow oil. LC-MS (ESI$^+$) m/z 527.4 (M+H)$^+$.

Step 3—6-(5-Cyanopyrazolo[3,4-b]pyridin-1-yl)-4-(cyclopropylamino)-N-[3-[2-[2-[2-[[2-(2,6-dioxo-3-piperidyl)-1,3-dioxo-isoindolin-4-yl]amino]ethoxy]ethoxy]ethoxy]-2-fluoro-propyl]pyridine-3-carboxamide To a solution of N-[3-[2-[2-(2-aminoethoxy)ethoxy]ethoxy]-2-fluoro-propyl]-6-(5-cyanopyrazolo[3,4-b]pyridin-1-yl)-4-(cyclopropylamino)pyridine-3-carboxamide (75.0 mg, 133 umol, HCl salt) in dioxane (4 mL) was added DIPEA (172 mg, 1.33 mmol) and 2-(2,6-dioxo-3-piperidyl)-4-fluoro-isoindoline-1,3-dione (36.8 mg, 133 umol, Intermediate R). The mixture was heated to 115° C. and stirred for 60 h. On completion, the mixture was concentrated in vacuo. The residue was further purification by pre-HPLC (column: Boston Green ODS 150*30 5 u; mobile phase: [water (0.225% FA)-ACN]; B %: 32%-62%, 10 min) to give the title compound I-46 (42.0 mg, 38% yield) as yellow solid. $^1$H NMR (400 MHz, DMSO-d$_6$) δ 11.16-11.08 (m, 1H), 9.09-9.06 (m, 1H), 9.05-9.02 (m, 1H), 8.85 (t, J=5.2 Hz, 1H), 8.68 (s, 1H), 8.64 (s, 1H), 8.59-8.54 (m, 1H), 7.71 (s, 1H), 7.59-7.53 (m, 1H), 7.15 (d, J=8.8 Hz, 1H), 7.04 (d, J=6.8 Hz, 1H), 6.63-6.59 (m, 1H), 5.09-5.02 (m, 1H), 4.87-4.70 (m, 1H), 3.71-3.65 (m, 1H), 3.64-3.61 (m, 2H), 3.60-3.52 (m, 10H), 3.50-3.46 (m, 2H), 2.91-2.83 (m, 1H), 2.63-2.56 (m, 2H), 2.56-2.54 (m, 2H), 2.07-1.99 (m, 1H), 0.90-0.83 (m, 2H), 0.57-0.55 (m, 2H); LC-MS (ESI$^+$) m/z 783.2 (M+H)$^+$.

TABLE 5

Compounds synthesized via Method 7, with the coupling of amines and acids in Step 1, followed by the addition to fluoride Intermediate R in Step 3

| Ex-# | I-# | Intermediate Amine | Intermediate Acid | LCMS (ES+) m/z (M + H)$^+$ | HNMR (400 MHz, DMSO-d6) δ |
|---|---|---|---|---|---|
| 47$^c$ | I-47 | BR | N | 984.6 | 11.11 (s, 1H), 10.37 (s, 1H), 9.05 (s, 1H), 8.58-8.55 (m, 4H), 8.46 (s, 1H), 8.28 (s, 1H), 7.61-7.55 (m, 2H), 7.51 (d, J = 8.8 Hz, 1H), 7.14 (d, J = 8.4 Hz, 1H), 7.04 (d, J = 6.8 Hz, 1H), 6.60 (t, J = 5.6 Hz, 1H), 5.05 (dd, J = 5.6, 12.8 Hz, 1H), 4.83-4.69 (m, 1H), 3.50-3.42 (m, 22H), 2.96-2.78 (m, 2H), 2.61 (s, 2H), 2.55 (d, J = 9.2 Hz, 2H), 2.46 (s, 2H), 2.44-2.41 (m, 4H), 2.39-2.35 (m, 4H), 2.05-1.90 (m, 2H), 1.18-1.06 (m, 1H), 0.96-0.92 (m, 2H), 0.60-0.57 (m, 2H) |
| 48 | I-48 | AK | N | 872.5 | 11.10 (s, 1H), 10.36 (s, 1H), 9.05 (s, 1H), 8.59-8.55 (m, 3H), 8.46 (s, 1H), 8.26 (d, J = 9.2 Hz, 1H), 8.16 (s, 1H), 7.59-7.53 (m, 2H), 7.50 (d, J = 8.8 Hz, 1H), 7.12 (d, J = 8.8 Hz, 1H), 7.02 (d, J = 7.2 Hz, 1H), 6.59 (t, J = 5.6 Hz, 1H), 5.11-5.01 (m, 1H), 4.85-4.66 (m, 1H), 3.72-3.65 (m, 1H), 3.65-3.51 (m, 14H), 3.49-3.40 (m, 8H), 2.93-2.80 (m, 1H), 2.65-2.55 (m, 2H), 2.55-2.51 (m, 2H), 2.07-1.96 (m, 1H), 0.97-0.91 (m, 2H), 0.61-0.55 (m, 2H) |
| 49$^{c,d}$ | I-49 | AI | N | 784.1 | 11.11 (s, 1H), 10.38 (s, 1H), 9.05 (s, 1H), 8.60-8.53 (m, 4H), 8.46 (s, 1H), 8.27 (d, J = 8.8 Hz, 1H), 7.60-7.53 (m, 2H), 7.49 (d, J = 8.8 Hz, 1H), 7.12 (d, J = 8.4 Hz, 1H), 7.02 (d, J = 7.2 Hz, 1H), 6.60 (t, J = 5.6 Hz, 1H), 5.05 (dd, J = 5.6, 12.8 Hz, 1H), 4.83-4.67 (m, 1H), 3.72-3.58 (m, 8H), 3.49-3.42 (m, 6H), 3.01-2.75 (m, 2H), 2.59-2.54 (m, 4H), 2.07-1.97 (m, 1H), 0.97-0.91 (m, 2H), 0.59-0.56 (m, 2H) |
| 50$^d$ | I-50 | BA | N | 828.2 | 11.11 (s, 1H), 10.37 (s, 1H), 9.05 (s, 1H), 8.60-8.52 (m, 4H), 8.45 (s, 1H), 8.27 (d, J = 8.8 Hz, 1H), 7.60-7.53 (m, 2H), 7.49 (d, J = 8.8 Hz, 1H), 7.12 (d, J = 8.8 Hz, 1H), 7.02 (d, J = 7.2 Hz, 1H), 6.59 (s, 1H), 5.05 (dd, J = 5.2, 12.6 Hz, 1H), 4.84-4.66 (m, 1H), 3.70-3.53 (m, 18H), 3.05-2.71 (m, 2H), 2.64-2.57 (m, 2H), 2.57-2.53 (m, 2H), |

TABLE 5-continued

Compounds synthesized via Method 7, with the coupling of amines
and acids in Step 1, followed by the addition to fluoride Intermediate R in Step 3

| Ex-# | I-# | Intermediate Amine | Intermediate Acid | LCMS (ES+) m/z (M + H)+ | HNMR (400 MHz, DMSO-d6) δ |
|---|---|---|---|---|---|
| 51 | I-51 | BP | N | 916.5 | 11.1 (s, 1H), 10.3 (s, 1H), 9.05 (s, 1H), 8.59-8.54 (m, 4H), 8.47 (s, 1H), 8.27 (d, J = 8.8 Hz, 1H), 7.59-7.55 (m, 2H), 7.51 (d, J = 8.8 Hz, 1H), 7.13 (d, J = 7.2 Hz, 1H), 7.03 (d, J = 6.8 Hz, 1H), 6.60 (t, J = 5.6 Hz, 1H), 5.06 (dd, J = 5.2, 8.8 Hz, 1H), 4.84-4.69 (m, 1H), 3.70-3.69 (m, 1H), 3.68-3.53 (m, 26H), 2.94-2.83 (m, 1H), 2.61 (s, 2H), 2.58-2.53 (m, 2H), 2.06-1.99 (m, 1H), 0.95-0.94 (m, 2H), 0.61-0.58 (m, 2H) |
| 52 | I-52 | AK | BY | 877.3 | 11.1 (s, 1H), 9.38 (s, 1H), 9.15 (s, 1H), 8.67 (d, J = 2.0 Hz, 1H), 8.46 (t, J = 5.6 Hz, 1H), 8.30 (s, 1H), 7.95 (d, J = 8.8 Hz, 1H), 7.66-7.51 (m, 2H), 7.13 (d, J = 8.8 Hz, 1H), 7.04 (d, J = 6.8 Hz, 1H), 6.60 (t, J = 5.6 Hz, 1H), 6.41 (s, 1H), 5.06 (dd, J = 5.6, 6.4 Hz, 1H), 4.84-4.65 (m, 1H), 3.55-3.44 (m, 22H), 2.94-2.82 (m, 1H), 2.60-2.56 (m, 1H), 2.55-2.52 (m, 2H), 2.47-2.42 (m, 2H), 2.06-1.98 (m, 1H), 0.83-0.74 (m, 2H), 0.53-0.48 (m, 2H) |
| 53 | I-53 | tert-butyl N-[2-[2-[2-[2-(2-aminoethoxy)ethoxy]-ethoxy]ethoxy]-ethyl]carbamate (CAS# 01187-40-0) | CN | 1012.0ᵃ | 11.10 (s, 1H), 11.01 (s, 1H), 9.03 (d, J = 4.8 Hz, 2H), 8.65 (t, J = 5.2 Hz, 1H), 8.26 (d, J = 5.2 Hz, 1H), 8.18-8.00 (m, 5H), 7.78 (s, 1H), 7.70 (t, J = 6.8 Hz, 1H), 7.61-7.53 (m, 1H), 7.27 (s, 1H) 7.18 (d, J = 6.0 Hz, 1H), 7.12 (d, J = 8.4 Hz, 1H), 7.03 (d, J = 7.2 Hz, 1H), 6.58 (t, J = 6.0 Hz, 1H), 5.05 (dd, J = 5.2, 12.8 Hz, 1H), 4.31-4.19 (m, 2H), 3.69-3.46 (m, 20H), 2.95-2.82 (m, 1H), 2.63-2.57 (m, 2H), 2.10-1.97 (m, 1H) |
| 54ᵇ | I-54 | AI | BY | 789.1 | 11.12 (s, 1H), 9.39 (s, 1H), 9.16 (s, 1H), 8.68 (s, 1H), 8.46 (t, J = 5.6 Hz, 1H), 8.40 (s, 1H), 8.18 (s, 1H), 7.95 (d, J = 8.8 Hz, 1H), 7.64-7.53 (m, 2H), 7.13 (d, J = 8.8 Hz, 1H), 7.04 (d, J = 7.2 Hz, 1H), 6.65-6.56 (m, 1H), 6.41 (s, 1H), 5.06 (dd, J = 5.2, 12.8 Hz, 1H), 4.84-4.62 (m, 1H), 3.69-3.55 (m, 16H), 2.95-2.82 (m, 1H), 2.59-2.44 (m, 3H), 2.07-1.98 (m, 1H), 0.79-0.77 (m, 2H), 0.51-0.49 (m, 2H) |
| 55 | I-55 | BS | N | 869.3 | 11.10 (s, 1H), 10.36 (s, 1H), 9.05 (s, 1H), 8.64 (t, J = 5.2 Hz, 1H), 8.59-8.55 (m, 3H), 8.47 (s, 1H), 8.27 (d, J = 8.8 Hz, 1H), 7.59-7.53 (m, 2H), 7.50 (d, J = 8.4 Hz, 2H), 7.09 (d, J = 8.4 Hz, 1H), 7.01 (d, J = 7.2 Hz, 1H), 6.59 (t, J = 5.6 Hz, 1H), 5.05 (dd, J = 5.2, 12.8 Hz, 1H), 4.61-4.45 (m, 1H), 3.90 (s, 2H), 3.84-3.77 (m, 1H), 3.74-3.59 (m, 10H), 3.30-3.26 (m, 2H), 2.94-2.83 (m, 1H), 2.65-2.56 (m, 2H), 2.50-2.41 (m, 2H), 2.06-1.97 (m, 1H), 1.22 (d, J = 5.2 Hz, 6H), 0.98-0.90 (m, 2H), 0.61-0.54 (m, 2H) |
| 56 | I-56 | AR | N | 812.5 | 11.11 (s, 1H), 10.36 (s, 1H), 9.05 (s, 1H), 8.62-8.51 (m, 4H), 8.27 (d, J = 8.8 Hz, 1H), 8.15 (s, 1H), 7.59-7.52 (m, 2H), 7.49 (d, J = 7.2 Hz, 1H), 7.12 (d, J = 8.8 Hz, 1H), 7.02 (d, J = 7.2 Hz, |

TABLE 5-continued

Compounds synthesized via Method 7, with the coupling of amines
and acids in Step 1, followed by the addition to fluoride Intermediate R in Step 3

| Ex-# | I-# | Intermediate Amine | Intermediate Acid | LCMS (ES+) m/z (M + H)+ | HNMR (400 MHz, DMSO-d6) δ |
|---|---|---|---|---|---|
| | | | | | 1H), 6.60 (t, J = 5.6 Hz, 1H), 5.05 (dd, J = 5.2, 12.4 Hz, 1H), 4.56-4.39 (dd, J = 8.8, 49.6 Hz, 1H), 3.64-3.51 (m, 14H), 2.93-2.81 (m, 1H), 2.64-2.52 (m, 3H), 2.06-1.97 (m, 1H), 1.18 (s, 6H), 0.93 (d, J = 4.8 Hz, 2H), 0.58 (s, 2H) |
| 57 | I-57 | AK | L | 871.4 | 11.1 (s, 1H), 9.06 (d, J = 2.0 Hz, 1H), 9.02 (d, J = 2.0 Hz, 1H), 8.86 (t, J = 5.6 Hz, 1H), 8.66 (s, 1H), 8.63 (s, 1H), 8.56 (s, 1H), 7.72 (s, 1H), 7.57 (t, J = 7.6 Hz, 1H), 7.13 (d, J = 8.4 Hz, 1H), 7.03 (d, J = 7.2 Hz, 1H), 6.59 (t, J = 5.6 Hz, 1H), 5.05 (dd, J = 5.2, 12.8 Hz, 1H), 4.89-4.69 (m, 1H), 3.72-3.66 (m, 1H), 3.59-3.47 (m, 22H), 2.89-2.85 (m, 1H), 2.65-2.59 (m, 2H), 2.58-2.48 (m, 2H), 2.07-1.98 (m, 1H), 0.89-0.83 (m, 2H), 0.60-0.56 (m, 2H) |
| 58 | I-58 | AI | BZ | 776.4 | 11.1 (s, 1H), 9.77 (s, 1H), 8.66-8.56 (m, 2H), 8.50 (s, 1H), 8.43 (s, 1H), 8.18 (d, J = 11.2 Hz, 1H), 7.92 (s, 1H), 7.57 (t, J = 7.6 Hz, 1H), 7.14 (d, J = 8.8 Hz, 1H), 7.03 (d, J = 7.2 Hz, 1H), 6.61 (t, J = 5.6 Hz, 1H), 5.10-5.01 (m, 1H), 4.83-4.63 (m, 1H), 3.66-3.62 (m, 1H), 3.56-3.49 (m, 14H), 2.87 (d, J = 14.8 Hz, 1H), 2.71-2.61 (m, 2H), 2.58-2.56 (m, 2H), 2.06-1.97 (m, 1H), 0.86-0.85 (m, 2H), 0.53-0.47 (m, 2H) |
| 59 | I-59 | AR | L | 811.4 | 11.11 (s, 1H), 9.09-9.06 (m, 1H), 9.03 (d, J = 1.6 Hz, 1H), 8.87-8.82 (m, 1H), 8.67 (s, 1H), 8.63 (s, 1H), 8.61 (s, 1H), 7.71 (s, 1H), 7.56 (t, J = 8.0 Hz, 1H), 7.13 (d, J = 8.8 Hz, 1H), 7.02 (d, J = 6.8 Hz, 1H), 6.63-6.58 (m, 1H), 5.05 (dd, J = 5.6, 12.4 Hz, 1H), 4.60-4.41 (m, 1H), 3.79-3.70 (m, 1H), 3.66-3.62 (m, 2H), 3.60-3.51 (m, 10H), 2.91-2.82 (m, 1H), 2.63-2.55 (m, 2H), 2.55-2.53 (m, 2H), 2.07-1.98 (m, 1H), 1.20 (s, 6H), 0.89-0.82 (m, 2H), 0.60-0.53 (m, 2H) |
| 60 | I-60 | AP | L | 899.7 | 11.10 (br s, 1H), 9.07 (d, J = 2.0 Hz, 1H), 9.03 (d, J = 2.0 Hz, 1H), 8.86 (t, J = 5.6 Hz, 1H), 8.67 (s, 1H), 8.64 (s, 1H), 8.62 (s, 1H), 7.72 (s, 1H), 7.60-7.54 (m, 1H), 7.13 (d, J = 8.8 Hz, 1H), 7.03 (d, J = 7.2 Hz, 1H), 6.60 (t, J = 5.6 Hz, 1H), 5.06 (dd, J = 5.6, 12.8 Hz, 1H), 4.60-4.43 (m, 1H), 3.79-3.64 (m, 1H), 3.63-3.59 (m, 2H), 3.56-3.43 (m, 19H), 2.95-2.83 (m, 1H), 2.63-2.54 (m, 3H), 2.07-1.98 (m, 1H), 1.21 (s, 6H), 0.89-0.83 (m, 2H), 0.60-0.55 (m, 2H) |
| 61 | I-61 | AV | N | 740.3 | 11.11 (s, 1H), 10.38 (s, 1H), 9.06 (s, 1H), 8.60-8.56 (m, 3H), 8.54 (s, 1H), 8.28 (d, J = 9.2 Hz, 1H), 8.21 (s, 1H), 7.61-7.55 (m, 2H), 7.50 (d, J = 9.2 Hz, 1H), 7.15 (d, J = 8.8 Hz, 1H), 7.03 (d, J = 7.2 Hz, 1H), 6.63 (t, J = 6.0 Hz, 1H), 5.06 (dd, J = 5.2, 13.2 Hz, 1H), 4.86-4.66 (m, 1H), 3.74-3.69 (m, 1H), 3.67-3.60 (m, 8H), 3.51-3.49 (m, 2H), 2.92-2.82 (m, 1H), 2.65-2.54 (m, 2H), 2.58-2.53 (m, 2H), 2.07-1.95 (m, 1H), |

TABLE 5-continued

Compounds synthesized via Method 7, with the coupling of amines and acids in Step 1, followed by the addition to fluoride Intermediate R in Step 3

| Ex-# | I-# | Intermediate Amine | Intermediate Acid | LCMS (ES+) m/z (M + H)+ | HNMR (400 MHz, DMSO-d6) δ |
|---|---|---|---|---|---|
| | | | | | 0.98-0.91 (m, 2H), 0.62-0.55 (m, 2H) |
| 62 | I-62 | AM | N | 798.4 | 11.10 (s, 1H), 10.36 (s, 1H), 9.05 (s, 1H), 8.59-8.50 (m, 4H), 8.27 (d, J = 8.8 Hz, 1H), 8.18 (s, 1H), 7.59-7.54 (m, 2H), 7.51 (d, J = 8.8 Hz, 1H), 7.12 (d, J = 8.8 Hz, 1H), 7.02 (d, J = 6.6 Hz, 1H), 6.60 (t, J = 5.6 Hz, 1H), 5.05 (dd, J = 5.6, 12.6 Hz, 1H), 4.65-4.47 (m, 1H), 3.67-3.65 (m, 1H), 3.64-3.54 (m, 14H), 2.93-2.86 (m, 1H), 2.65-2.54 (m, 2H), 2.56-2.54 (m, 1H), 2.06-1.97 (m, 1H), 1.14 (t, J = 5.6 Hz, 3H), 0.97-0.91 (m, 2H), 0.60-0.58 (m, 2H) |
| 63 | I-63 | AM | L | 797.4 | 11.10 (s, 1H), 9.07 (d, J = 1.6 Hz, 1H), 9.02 (d, J = 2.0 Hz, 1H), 8.86-8.78 (m, 1H), 8.66 (s, 1H), 8.63 (d, J = 1.6 Hz, 1H), 8.57 (d, J = 6.4 Hz, 1H), 7.71 (d, J = 2.8 Hz, 1H), 7.56 (t, J = 7.6 Hz, 1H), 7.12 (d, J = 8.4 Hz, 1H), 7.02 (d, J = 7.2 Hz, 1H), 6.59 (t, J = 5.6 Hz, 1H), 5.05 (dd, J = 5.6, 12.8 Hz, 1H), 4.70-4.48 (m, 1H), 3.73-3.66 (m, 1H), 3.63 (t, J = 5.2 Hz, 4H), 3.59-3.50 (m, 8H), 3.48-3.45 (m, 2H), 2.94-2.82 (m, 1H), 2.62-2.55 (m, 2H), 2.55-2.53 (m, 1H), 2.07-1.98 (m, 1H), 1.15-1.12 (m, 3H), 0.90-0.82 (m, 2H), 0.59-0.53 (m, 2H) |
| 64 | I-64 | AP | N | 900.6 | (CD3CN) δ 10.01 (br s, 1H), 9.04 (s, 1H), 8.58 (d, J = 5.6 Hz, 1H), 8.51 (s, 1H), 8.49 (s, 1H), 8.29 (s, 1H), 8.19 (d, J = 8.8 Hz, 1H), 8.11 (s, 1H), 7.65 (d, J = 5.6 Hz, 1H), 7.52 (t, J = 8.0 Hz, 1H), 7.37 (d, J = 8.8 Hz, 1H), 7.34 (s, 1H), 7.03 (s, 1H), 7.01 (d, J = 2.4 Hz, 1H), 6.46 (t, J = 5.6 Hz, 1H), 4.98 (dd, J = 5.6, 12.8 Hz, 1H), 4.56-4.39 (m, 1H), 3.90-3.74 (m, 1H), 3.66 (t, J = 5.2 Hz, 2H), 3.63-3.47 (m, 17H), 3.43 (q, J = 5.2 Hz, 2H), 2.84-2.61 (m, 4H), 2.17-2.10 (m, 1H), 1.26 (s, 6H), 1.02-0.95 (m, 2H), 0.68-0.61 (m, 2H) |
| 65 | I-65 | AR | BY | 817.3 | 11.08 (s, 1H), 9.36 (s, 1H), 9.14 (s, 1H), 8.64 (s, 1H), 8.43 (t, J = 5.6 Hz, 1H), 8.33 (s, 1H), 8.13 (s, 1H), 7.95 (d, J = 8.8 Hz, 1H), 7.63-7.52 (m, 2H), 7.13 (d, J = 8.4 Hz, 1H), 7.03 (d, J = 6.8 Hz, 1H), 6.59 (t, J = 5.6 Hz, 1H), 6.40 (s, 1H), 5.04 (dd, J = 5.2, 12.4 Hz, 1H), 4.55-4.36 (m, 1H), 3.64-3.44 (m, 14H), 2.93-2.82 (m, 1H), 2.63-2.54 (m, 2H), 2.45-2.39 (m, 1H), 2.06-1.97 (m, 1H), 1.17 (s, 6H), 0.80-0.74 (m, 2H), 0.51-0.46 (m, 2H) |
| 66 | I-66 | AS | L | 885.5 | 11.10 (s, 1H), 9.06 (d, J = 1.6 Hz, 1H), 9.02 (d, J = 2.0 Hz, 1H), 8.87-8.80 (m, 1H), 8.66 (s, 1H), 8.63 (s, 1H), 8.58 (d, J = 7.6 Hz, 1H), 7.71 (d, J = 1.6 Hz, 1H), 7.56 (t, J = 8.0 Hz, 1H), 7.12 (d, J = 8.8 Hz, 1H), 7.03 (d, J = 7.2 Hz, 1H), 6.59 (t, J = 5.2 Hz, 1H), 5.05 (dd, J = 5.6, 12.8 Hz, 1H), 4.73-4.49 (m, 1H), 3.74-3.64 (m, 2H), 3.61 (t, J = 5.2 Hz, 2H), 3.58-3.47 (m, 17H), 3.45 (d, J = 5.4 Hz, 2H), 2.97-2.81 (m, 1H), |

TABLE 5-continued

Compounds synthesized via Method 7, with the coupling of amines and acids in Step 1, followed by the addition to fluoride Intermediate R in Step 3

| Ex-# | I-# | Intermediate Amine | Intermediate Acid | LCMS (ES+) m/z (M + H)+ | HNMR (400 MHz, DMSO-d6) δ |
|---|---|---|---|---|---|
| | | | | | 2.63-2.56 (m, 2H), 2.55-2.53 (m, 1H), 2.06-1.96 (m, 1H), 1.19-1.13 (m, 3H), 0.90-0.83 (m, 2H), 0.57-0.55 (m, 2H) |
| 67 | I-67 | AR | BZ | 804.4 | 11.10 (s, 1H), 8.61-8.55 (m, 2H), 8.52 (s, 1H), 8.16 (dd, J = 1.6, 11.2 Hz, 1H), 7.91 (s, 1H), 7.57-7.53 (m, 1H), 7.13 (d, J = 8.8 Hz, 1H), 7.02 (d, J = 6.8 Hz, 1H), 6.59 (t, J = 5.6 Hz, 1H), 5.05 (dd, J = 5.2, 12.8 Hz, 1H), 4.56-4.37 (m, 1H), 3.67-3.49 (m, 14H), 2.94-2.82 (m, 1H), 2.63-2.52 (m, 2H), 2.46-2.42 (m, 1H), 2.07-1.96 (m, 1H), 1.17 (s, 6H), 0.88-0.80 (m, 2H), 0.53-0.46 (m, 2H) |
| 68 | I-68 | AP | BY | 905.4 | 11.10 (s, 1H), 9.37 (s, 1H), 9.15 (s, 1H), 8.66 (d, J = 2.0 Hz, 1H), 8.45 (t, J = 5.6 Hz, 1H), 8.40 (s, 1H), 8.35 (s, 1H), 7.95 (d, J = 8.8 Hz, 1H), 7.65-7.52 (m, 2H), 7.13 (d, J = 8.8 Hz, 1H), 7.04 (d, J = 6.8 Hz, 1H), 6.60 (t, J = 5.6 Hz, 1H), 6.41 (s, 1H), 5.06 (dd, J = 5.2, 12.9 Hz, 1H), 4.63-4.34 (m, 1H), 3.68 (d, J = 14.4 Hz, 1H), 3.63-3.59 (m, 2H), 3.57-3.44 (m, 19H), 2.95-2.80 (m, 1H), 2.64-2.53 (m, 2H), 2.44-2.43 (m, 1H), 2.07-1.98 (m, 1H), 1.19 (s, 6H), 0.83-0.70 (m, 2H), 0.56-0.41 (m, 2H) |
| 69 | I-69 | AP | BZ | 892.4 | 11.11 (s, 1H), 9.73 (s, 1H), 8.66-8.51 (m, 3H), 8.44 (s, 1H), 8.17 (dd, J = 1.6, 11.0 Hz, 1H), 7.92 (s, 1H), 7.58 (dd, J = 7.2, 8.4 Hz, 1H), 7.13 (d, J = 8.4 Hz, 1H), 7.04 (d, J = 7.2 Hz, 1H), 6.60 (t, J = 5.6 Hz, 1H), 5.08-5.03 (m, 1H), 4.62-4.40 (m, 1H), 3.69-3.53 (m, 7H), 3.51-3.33 (m, 15H), 3.00-2.83 (m, 1H), 2.63-2.54 (m, 2H), 2.47 (s, 1H), 2.07-1.95 (m, 1H), 1.19 (s, 6H), 0.93-0.77 (m, 2H), 0.58-0.42 (m, 2H) |
| 70 | I-70 | BT | N | 798.3 | 11.10 (s, 1H), 10.37 (s, 1H), 9.06 (s, 1H), 8.61-8.53 (m, 4H), 8.30-8.25 (m, 2H), 7.61-7.53 (m, 2H), 7.51 (d, J = 8.8 Hz, 1H), 7.13 (d, J = 8.4 Hz, 1H), 7.03 (d, J = 6.4 Hz, 1H), 6.61 (t, J = 5.6 Hz, 1H), 5.05 (dd, J = 5.6, 13.2 Hz, 1H), 4.85-4.66 (m, 1H), 3.60-3.45 (m, 15H), 2.93-2.87 (m, 1H), 2.63-2.56 (m, 2H), 2.56-2.53 (m, 1H), 2.06-1.98 (m, 1H), 1.05 (d, J = 6.4 Hz, 3H), 0.98-0.91 (m, 2H), 0.62-0.54 (m, 2H) |
| 71 | I-71 | BB | L | 841.4 | 11.10 (s, 1H), 9.07 (d, J = 2.0 Hz, 1H), 9.03 (d, J = 2.0 Hz, 1H), 8.86-8.79 (m, 1H), 8.67 (s, 1H), 8.63 (s, 1H), 8.60-8.55 (m, 1H), 7.71 (d, J = 2.0 Hz, 1H), 7.56 (t, J = 7.6 Hz, 1H), 7.12 (d, J = 8.8 Hz, 1H), 7.02 (d, J = 7.2 Hz, 1H), 6.59 (t, J = 5.6 Hz, 1H), 5.06 (dd, J = 5.6, 12.8 Hz, 1H), 4.69-4.48 (m, 1H), 3.71-3.63 (m, 2H), 3.62-3.60 (m, 2H), 3.60-3.50 (m, 13H), 3.48-3.44 (m, 2H), 2.94-2.83 (m, 1H), 2.62-2.55 (m, 2H), 2.55-2.53 (m, 1H), 2.07-1.97 (m, 1H), 1.19-1.13 (m, 3H), 0.89-0.83 (m, 2H), 0.60-0.53 (m, 2H) |
| 72 | I-72 | BA | L | 827.4 | 11.09 (m, 1H), 9.07 (d, J = 2.0 Hz, 1H), 9.03 (d, J = 2.0 Hz, 1H), |

TABLE 5-continued

Compounds synthesized via Method 7, with the coupling of amines and acids in Step 1, followed by the addition to fluoride Intermediate R in Step 3

| Ex-# | I-# | Intermediate Amine | Intermediate Acid | LCMS (ES+) m/z (M + H)+ | HNMR (400 MHz, DMSO-d6) δ |
|---|---|---|---|---|---|
|  |  |  |  |  | 8.85 (t, J = 5.6 Hz, 1H), 8.67 (s, 1H), 8.64 (s, 1H), 8.56 (s, 1H), 7.72 (s, 1H), 7.57 (dd, J = 7.2, 8.4 Hz, 1H), 7.13 (d, J = 8.4 Hz, 1H), 7.03 (d, J = 7.2 Hz, 1H), 6.60 (t, J = 5.6 Hz, 1H), 5.06 (dd, J = 5.6, 13.2 Hz, 1H), 4.88-4.70 (m, 1H), 3.75-3.44 (m, 20H), 2.94-2.83 (m, 1H), 2.63-2.53 (m, 3H), 2.07-1.99 (m, 1H), 0.90-0.83 (m, 2H), 0.60-0.54 (m, 2H) |
| 73 | I-73 | BC | L | 855.3 | 11.07 (s, 1H), 9.06 (d, J = 1.6 Hz, 1H), 9.02 (d, J = 2.0 Hz, 1H), 8.84 (t, J = 5.2 Hz, 1H), 8.66 (s, 1H), 8.63 (s, 1H), 8.60 (s, 1H), 7.71 (s, 1H), 7.55 (t, J = 8.0 Hz, 1H), 7.12 (d, J = 8.4 Hz, 1H), 7.01 (d, J = 6.8 Hz, 1H), 6.59 (t, J = 5.6 Hz, 1H), 5.04 (dd, J = 5.2, 12.8 Hz, 1H), 4.60-4.40 (m, 1H), 3.79-3.57 (m, 4H), 3.55-3.43 (m, 14H), 2.94-2.81 (m, 1H), 2.62-2.52 (m, 3H), 2.06-1.97 (m, 1H), 1.20 (s, 6H), 0.89-0.81 (m, 2H), 0.60-0.52 (m, 2H) |
| 74 | I-74 | AW | N | 724.1 | 11.10 (s, 1H), 10.37 (s, 1H), 9.06 (s, 1H), 8.65-8.54 (m, 4H), 8.28 (d, J = 8.8 Hz, 1H), 8.22 (s, 1H), 7.65-7.55 (m, 2H), 7.50 (d, J = 8.8 Hz, 1H), 7.18 (d, J = 8.8 Hz, 1H), 7.05 (d, J = 7.2 Hz, 1H), 6.62 (t, J = 5.2 Hz, 1H), 5.07 (dd, J = 5.2, 12.8 Hz, 1H), 4.65-4.37 (m, 1H), 3.84-3.60 (m, 3H), 3.49-3.32 (m, 3H), 2.96-2.80 (m, 1H), 2.72-2.55 (m, 3H), 2.09-1.92 (m, 1H), 1.23 (s, 6H), 1.01-0.89 (m, 2H), 0.60-0.57 (m, 2H) |
| 75 | I-75 | AW | L | 723.1 | 11.10 (s, 1H), 9.06 (dd, J = 2.0, 15.6 Hz, 2H), 8.92-8.84 (m, 1H), 8.71-8.58 (m, 3H), 7.72 (s, 1H), 7.66-7.55 (m, 1H), 7.18 (d, J = 8.8 Hz, 1H), 7.05 (d, J = 6.8 Hz, 1H), 6.62 (t, J = 5.6 Hz, 1H), 5.07 (dd, J = 5.6, 12.8 Hz, 1H), 4.65-4.44 (m, 1H), 3.83-3.63 (m, 3H), 3.53-3.40 (m, 3H), 2.93-2.80 (m, 1H), 2.58 (m, 3H), 2.09-1.96 (m, 1H), 1.25 (d, J = 2.8 Hz, 6H), 0.89-0.84 (m, 2H), 0.59-0.55 (m, 2H) |
| 76 | I-76 | AV | L | 739.4 | 11.10 (s, 1H), 9.07 (d, J = 2.0 Hz, 1H), 9.04 (d, J = 2.0 Hz, 1H), 8.84 (s, 1H), 8.67 (s, 1H), 8.63 (s, 1H), 8.55 (s, 1H), 7.71 (s, 1H), 7.59-7.54 (m, 1H), 7.15 (d, J = 8.4 Hz, 1H), 7.02 (d, J = 7.2 Hz, 1H), 6.65-6.60 (m, 1H), 5.05 (m, 1H), 4.87-4.71 (m, 1H), 3.75-3.60 (m, 9H), 3.55 (m, 1H), 3.49 (m, 2H), 2.94-2.80 (m, 1H), 2.59 (s, 3H), 2.03 (m, 1H), 0.89-0.84 (m, 2H), 0.57 (m, 2H) |
| 77 | I-77 | AY | N | 710.3 | 11.10 (s, 1H), 10.36 (s, 1H), 9.06 (s, 1H), 8.61-8.56 (m, 3H), 8.54 (d, J = 5.6 Hz, 1H), 8.27 (d, J = 9.2 Hz, 1H), 8.22 (s, 1H), 7.63-7.55 (m, 2H), 7.51 (d, J = 8.8 Hz, 1H), 7.17 (d, J = 8.4 Hz, 1H), 7.05 (d, J = 7.2 Hz, 1H), 6.63 (s, 1H), 5.06 (dd, J = 5.2, 12.8 Hz, 1H), 4.68-4.49 (m, 1H), 3.69-3.64 (m, 7H), 2.91-2.83 (m, 1H), 2.63-2.58 (m, 2H), 2.54-2.53 (m, 1H), 2.06-1.92 (m, 1H), 1.19 (d, J = 5.2 Hz, 3H), 0.98-0.92 (m, 2H), 0.58 (s, 2H) |

TABLE 5-continued

Compounds synthesized via Method 7, with the coupling of amines and acids in Step 1, followed by the addition to fluoride Intermediate R in Step 3

| Ex-# | I-# | Intermediate Amine | Intermediate Acid | LCMS (ES+) m/z (M + H)+ | HNMR (400 MHz, DMSO-d6) δ |
|---|---|---|---|---|---|
| 78[c] | I-78 | tert-butyl N-[2-[2-[2-[2-(2-aminoethoxy)-ethoxy]-ethoxy]ethoxy]-ethyl]carbamate (CAS# 01187-40-0) | CE | 837.3 | (CD$_3$CN) δ 9.08 (br s, 1H), 8.43 (s, 1H), 8.17 (br s, 1H), 7.89 (d, J = 5.6 Hz, 1H), 7.74 (s, 1H), 7.54-7.48 (m, 1H), 7.34 (d, J = 5.6 Hz, 1H), 7.09 (br s, 1H), 7.03-6.97 (m, 2H), 6.45 (t, J = 5.6 Hz, 1H), 4.98-4.81 (m, 2H), 4.68-4.64 (m, 1H), 4.36 (dd, J = 6.4, 11.2 Hz, 1H), 4.19-4.13 (m, 1H), 4.06 (s, 3H), 3.66-3.52 (m, 18H), 3.42 (q, J = 5.6 Hz, 2H), 2.79-2.59 (m, 4H), 2.13-2.08 (m, 1H), 1.80-1.62 (m, 2H), 1.10 (t, J = 7.2 Hz, 3H) |
| 79 | I-79 | AU | L | 767.4 | 11.09 (s, 1H), 9.07 (s, 1H), 9.03 (s, 1H), 8.85-8.79 (m, 1H), 8.67 (s, 1H), 8.62 (s, 1H), 8.60 (s, 1H), 7.71 (s, 1H), 7.56 (t, J = 7.2 Hz, 1H), 7.15 (d, J = 8.8 Hz, 1H), 7.02 (d, J = 7.2 Hz, 1H), 6.65-6.60 (m, 1H), 5.07-5.01 (m, 1H), 4.57-4.55 (m, 1H), 3.76-3.69 (m, 1H), 3.68-3.63 (m, 2H), 3.57-3.48 (m, 6H), 2.89-2.81 (m, 1H), 2.63-2.55 (m, 4H), 2.05-1.96 (m, 1H), 1.20 (s, 6H), 0.88-0.83 (m, 2H), 0.60-0.53 (m, 2H) |
| 80 | I-80 | AU | N | 768.4 | 11.10 (s, 1H), 10.36 (s, 1H), 9.06 (s, 1H), 8.59-8.51 (m, 4H), 8.28 (d, J = 8.8 Hz, 1H), 8.22 (s, 1H), 7.60-7.54 (m, 2H), 7.50 (d, J = 8.8 Hz, 1H), 7.15 (d, J = 8.4 Hz, 1H), 7.02 (d, J = 7.2 Hz, 1H), 6.63 (t, J = 5.6 Hz, 1H), 5.04 (dd, J = 5.6, 12.8 Hz, 1H), 4.57-4.38 (m, 1H), 3.75-3.70 (m, 1H), 3.68-3.56 (m, 8H), 2.90-2.82 (m, 1H), 2.64-2.58 (m, 2H), 2.57-2.55 (m, 1H), 2.54-2.53 (m, 1H), 2.05-1.96 (m, 1H), 1.19 (s, 6H), 0.97-0.92 (m, 2H), 0.61-0.55 (m, 2H) |
| 81 | I-81 | AX | N | 696.3 | 11.1 (s, 1H), 10.4 (s, 1H), 9.06 (s, 1H), 8.60-8.56 (m, 3H), 8.54 (s, 1H), 8.28 (d, J = 9.2 Hz, 1H), 8.21 (s, 1H), 7.63-7.56 (m, 2H), 7.50 (d, J = 8.8 Hz, 1H), 7.18 (d, J = 8.8 Hz, 1H), 7.05 (d, J = 6.8 Hz, 1H), 6.69-6.61 (m, 1H), 5.08-5.03 (m, 1H), 4.89-4.68 (m, 1H), 3.77-3.56 (m, 8H), 2.92-2.86 (m, 1H), 2.64-2.59 (m, 2H), 2.57-2.55 (m, 1H), 2.05-1.96 (m, 1H), 0.97-0.92 (m, 2H), 0.61-0.57 (m, 2H) |
| 82 | I-82 | AX | L | 695.3 | 11.1 (s, 1H), 9.09 (d, J = 2.0 Hz, 1H), 9.05 (d, J = 2.0 Hz, 1H), 8.90 (t, J = 5.2 Hz, 1H), 8.70 (s, 1H), 8.65 (s, 1H), 8.63 (s, 1H), 7.80 (s, 1H), 7.60 (dd, J = 7.2, 8.4 Hz, 1H), 7.18 (d, J = 8.4 Hz, 1H), 7.05 (d, J = 7.0 Hz, 1H), 6.69-6.61 (m, 1H), 5.06 (dd, J = 5.5, 12.9 Hz, 1H), 4.91-4.72 (m, 1H), 3.75-3.65 (m, 4H), 3.54-3.51 (m, 4H), 2.93-2.82 (m, 1H), 2.71-2.56 (m, 3H), 2.07-1.99 (m, 1H), 0.90-0.84 (m, 2H), 0.62-0.57 (m, 2H) |
| 83 | I-83 | AY | L | 709.3 | 11.09 (s, 1H), 9.07 (d, J = 1.6 Hz, 1H), 9.04 (d, J = 1.6 Hz, 1H), 8.86 (s, 1H), 8.67 (s, 1H), 8.64 (s, 1H), 8.56 (d, J = 8.4 Hz, 1H), 7.71 (s, 1H), 7.60 (t, J = 8.0 Hz, 1H), 7.18 (d, J = 8.8 Hz, 1H), 7.05 (d, J = 6.8 Hz, 1H), 6.64 (s, 1H), 5.06 (dd, J = 5.2, 12.8 Hz, 1H), 4.75-4.51 (m, 1H), 3.83-3.43 (m, 7H), |

TABLE 5-continued

Compounds synthesized via Method 7, with the coupling of amines
and acids in Step 1, followed by the addition to fluoride Intermediate R in Step 3

| Ex-# | I-# | Intermediate Amine | Intermediate Acid | LCMS (ES+) m/z (M + H)+ | HNMR (400 MHz, DMSO-d6) δ |
|---|---|---|---|---|---|
| 84 | I-84 | AZ | N | 754.4 | 2.94-2.81 (m, 1H), 2.62-2.56 (m, 2H), 2.55-2.54 (m, 1H), 2.02 (d, J = 9.6 Hz, 1H), 1.24-1.17 (m, 3H), 0.89-0.84 (m, 2H), 0.60-0.55 (m, 2H) 11.11 (s, 1H), 10.37 (s, 1H), 9.06 (s, 1H), 8.63-8.40 (m, 3H), 8.33-8.18 (m, 2H), 7.60-7.48 (m, 3H), 7.15 (d, J = 8.4 Hz, 1H), 7.02 (d, J = 7.2 Hz, 1H), 6.63 (t, J = 5.6 Hz, 1H), 5.05 (dd, J = 5.6, 12.8 Hz, 1H), 4.66-4.45 (m, 2H), 3.74-3.41 (m, 11H), 2.93-2.82 (m, 1H), 2.69-2.58 (m, 3H),, 2.06-1.97 (m, 1H), 1.23-1.12 (m, 3H), 1.01-0.89 (m, 2H), 0.58 (m, 2H) |
| 85 | I-85 | AZ | L | 753.4 | 11.09 (s, 1H), 9.07 (d, J = 2.0 Hz, 2H), 9.03 (s, 1H), 8.86-8.76 (m, 1H), 8.70-8.61 (m, 2H), 8.60-8.52 (m, 1H), 7.74-7.67 (m, 1H), 7.56 (m, 1H), 7.14 (d, J = 8.8 Hz, 1H), 7.02 (d, J = 7.2 Hz, 1H), 6.62 (t, J = 5.6 Hz, 1H), 5.05 (dd, J = 5.2, 12.8 Hz, 1H), 4.72-4.48 (m, 1H), 3.76-3.45 (m, 11H), 2.97-2.80 (m, 1H), 2.64-2.54 (m, 3H), 2.09-1.96 (m, 1H), 1.24-1.12 (m, 3H), 0.90-0.82 (m, 2H), 0.57 (m, 2H) |
| 86 | I-86 | AT | L | 795.1 | 11.1 (s, 1H), 9.07 (d, J = 2.0 Hz, 1H), 9.02 (d, J = 2.0 Hz, 1H), 8.85 (t, J = 5.6 Hz, 1H), 8.66 (s, 1H), 8.63 (s, 1H), 8.60 (s, 1H), 7.71 (s, 1H), 7.57 (t, J = 8.0 Hz, 1H), 7.08 (d, J = 8.8 Hz, 1H), 7.01 (d, J = 7.2 Hz, 1H), 6.71-6.61 (m, 1H), 5.07-5.00 (m, 1H), 4.57-4.41 (m, 1H), 3.80-3.46 (m, 10H), 2.95-2.80 (m, 1H), 2.63-2.55 (m, 3H), 2.06-1.97 (m, 1H), 1.87-1.78 (m, 2H), 1.77-1.68 (m, 2H), 1.18 (s, 6H), 0.89-0.83 (m, 2H), 0.61-0.53 (m, 2H) |
| 87 | I-87 | tert-butyl N-[2-[2-(2-aminoethoxy)-ethoxy]ethyl]-carbamate (CAS# 153086-78-3) | CE | 749.1 | 11.10 (s, 1H), 8.88 (s, 1H), 8.43 (t, J = 5.6 Hz, 1H), 8.15 (s, 1H), 7.90 (d, J = 5.6 Hz, 1H), 7.72 (s, 1H), 7.58-7.51 (m, 1H), 7.42 (d, J = 5.6 Hz, 1H), 7.10 (d, J = 8.4 Hz, 1H), 6.99 (d, J = 7.2 Hz, 1H), 6.59 (t, J = 5.6 Hz, 1H), 5.05 (dd, J = 5.6, 12.8 Hz, 1H), 4.99-4.82 (m, 1H), 4.54 (dd, J = 3.6, 11.2 Hz, 1H), 4.25 (dd, J = 6.4, 11.2 Hz, 1H), 4.13-4.04 (m, 1H), 3.96 (s, 3H), 3.68-3.56 (m, 8H), 3.50-3.43 (m, 4H), 2.94-2.81 (m, 1H), 2.62-2.53 (m, 3H), 2.07-1.97 (m, 1H), 1.65-1.56 (m, 2H), 1.02 (t, J = 7.2 Hz, 3H) |
| 88 | I-88 | BE | L | 797.3 | 11.05 (s, 1H), 9.07 (d, J = 2.0 Hz, 1H), 9.03 (d, J = 2.0 Hz, 1H), 8.87 (t, J = 5.6 Hz, 1H), 8.66 (d, J = 6.0 Hz, 2H), 8.58 (s, 1H), 7.72 (s, 1H), 7.60-7.51 (m, 1H), 7.12 (d, J = 8.8 Hz, 1H), 7.02 (d, J = 6.8 Hz, 1H), 6.59 (t, J = 6.0 Hz, 1H), 5.05 (dd, J = 5.2, 12.8 Hz, 1H), 4.88-4.67 (m, 1H), 3.65-3.60 (m, 2H), 3.58-3.46 (m, 14H), 2.94-2.83 (m, 1H), 2.63-2.54 (m, 3H), 2.08-1.98 (m, 1H), |

TABLE 5-continued

Compounds synthesized via Method 7, with the coupling of amines and acids in Step 1, followed by the addition to fluoride Intermediate R in Step 3

| Ex-# | I-# | Intermediate Amine | Intermediate Acid | LCMS (ES+) m/z (M + H)+ | HNMR (400 MHz, DMSO-d6) δ |
|---|---|---|---|---|---|
| | | | | | 1.96-1.75 (m, 2H), 0.90-0.80 (m, 2H), 0.61-0.51 (m, 2H) |

Variations of temperature and time for Method 7 were as follows: Step 1 was run a from 0.5-3 hrs; Step 2 was run from 15-60 minutes; Step 3 was run at 110-115° C. for 14-136 hrs, with most complete within 40-60 h.
[a]mass is (M + Na)+.
[b]Step 1 was run at rt for 12 h.
[c]Step 3 was run at 90° C. for 12 h.
[d]The product of Step 1 was purified by silica gel chromatography (DCM:MeOH = 25:1) instead of prep-HPLC.

Further Examples Using Synthetic Methods Similar to Method 7

Example 89: 1-[[(2S,3S,4S)-1-[2-[2-[2-[2-[2-[[2-(2,6-dioxo-3-piperidyl)-1,3-dioxo-isoindolin-4-yl]amino]ethoxy]ethoxy]ethoxy]ethoxy]ethyl]-3-ethyl-4-fluoro-5-oxo-pyrrolidin-2-yl]methoxy]-7-methoxy-isoquinoline-6-carboxamide, I-89

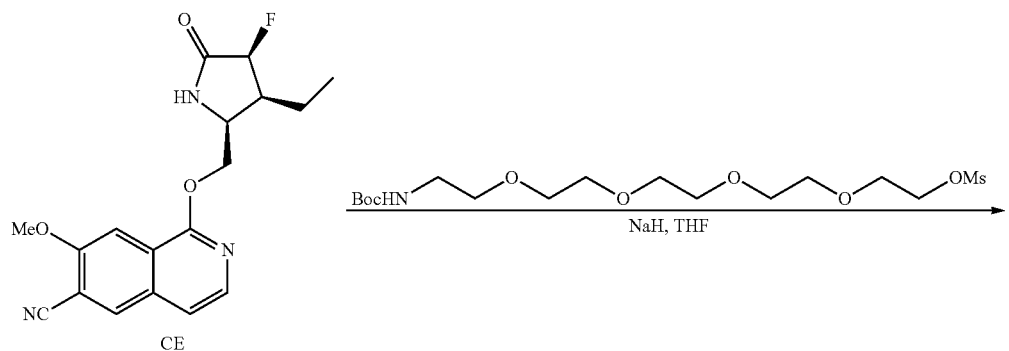

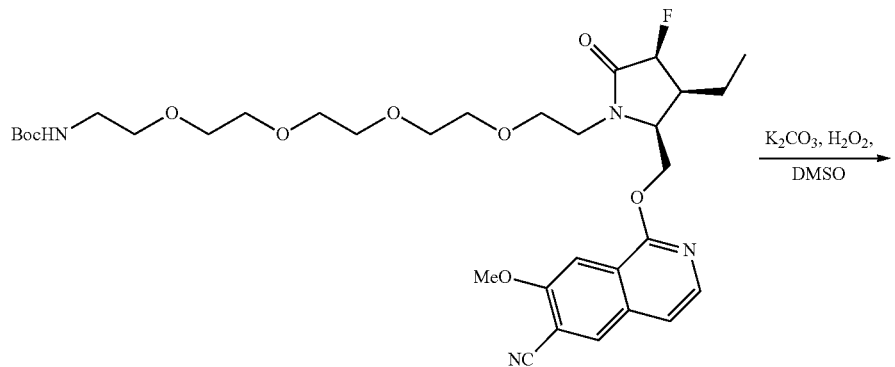

-continued

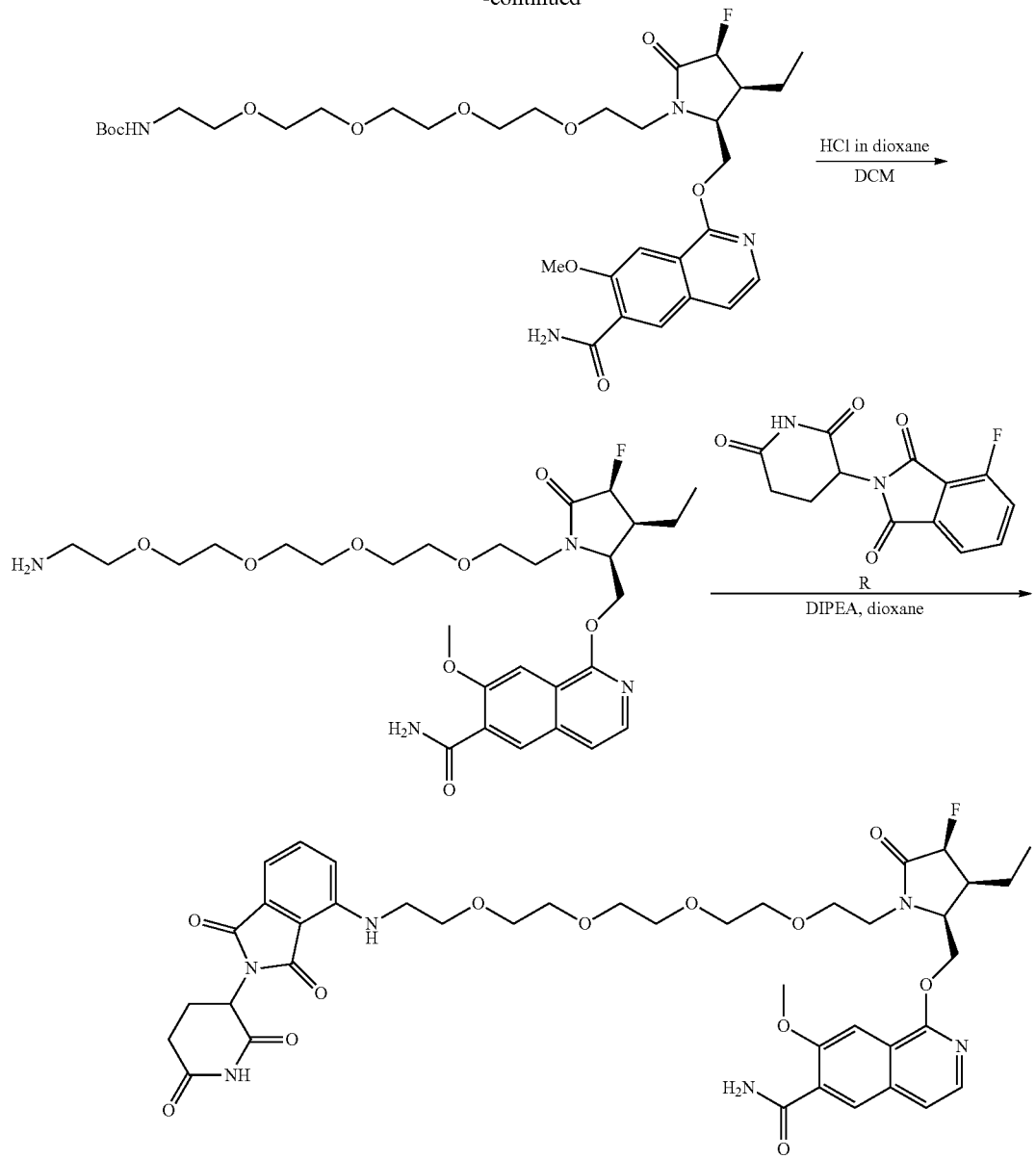

Step 1—Tert-butyl (14-((2S,3S,4S)-2-(((6-cyano-7-methoxyisoquinolin-1-yl)oxy)methyl)-3-ethyl-4-fluoro-5-oxopyrrolidin-1-yl)-3,6,9,12-tetraoxatetradecyl)carbamate To a solution of 1-[[(2S,3S,4S)-3-ethyl-4-fluoro-5-oxopyrrolidin-2-yl]methoxy]-7-methoxy-isoquinoline-6-carbonitrile (50 mg, 145.6 umol, Intermediate CD) in DMF (3 mL) was added NaH (11.7 mg, 291 umol, 60% dispersion in mineral oil) at 0° C. The reaction mixture was stirred at 0° C. for 1 hr. Then, 2-[2-[2-[2-[2-(tert-butoxycarbonyl-amino) ethoxy]ethoxy]ethoxy]ethyl methanesulfonate (90.8 mg, 218 umol, synthesized via Steps 1-2 of Intermediate AK) was added. The resulting reaction mixture was allowed to warm to rt and stirred for 12 h. On completion, the reaction mixture was quenched with water (2 mL) and extracted with ethyl acetate (3×200 mL). The combined organic layers were washed with saturated brine solution (50 mL), dried over with anhydrous sodium sulfate, and filtered. The filtrate was concentrated in vacuo. The residue was purified by prep-HPLC (column: Gemini 150*25 5 u; mobile phase: [water (0.05% ammonia hydroxide v/v)-ACN]; B %: 15%-75%) to give the title compound (25 mg, 25% yield) as a colorless oil. $^1$H NMR (400 MHz, CDCl$_3$) δ 8.03 (s, 1H), 7.93 (d, J=5.6 Hz, 1H), 7.75 (s, 1H), 7.20 (d, J=5.6 Hz, 1H), 5.10-4.92 (m, 2H), 4.85 (dd, J=3.2, 12.4 Hz, 1H), 4.45 (dd, J=2.4, 12.4 Hz, 1H), 4.32-4.25 (m, 1H), 4.03 (s, 3H), 3.68-3.50 (m, 18H), 3.32-3.31 (m, 2H), 2.65-2.42 (m, 1H), 1.88-1.76 (m, 1H), 1.69-1.63 (m, 1H), 1.44 (s, 9H), 1.11 (t, J=7.2 Hz, 3H). LC-MS (ESI$^+$) m/z 663.2 (M+H)$^+$.

Step 2—Tert-butyl (14-((2S,3S,4S)-2-(((6-carbamoyl-7-methoxyisoquinolin-1-yl)oxy)methyl)-3-ethyl-4-fluoro-5-oxopyrrolidin-1-yl)-3,6,9,12-tetraoxatetradecyl)carbamate To a solution of tert-butyl N-[2-[2-[2-[2-[2-[(2S,3S,4S)-2-[(6-cyano-7-methoxy-1-isoquinolyl)oxymethyl]-3-ethyl- 4-fluoro-5-oxo-pyrrolidin-lyl]ethoxy]ethoxy]ethoxy] ethoxy]ethyl]carbamate (20 mg, 30.2 umol) in DMSO (1 mL) was added K$_2$CO$_3$ (4.17 mg, 30.2 umol) at rt. Then, H$_2$O$_2$ (6.84 mg, 60.4 umol, 30% solution) was added slowly. The reaction mixture was stirred at rt for 3 h. On completion, the reaction mixture was diluted with water (3 mL) and extracted with ethyl acetate (3×20 mL). The combined organic layers were washed with brine (10 mL), dried over anhydrous sodium sulfate, filtered and concentrated in vacuo to give the title compound (18 mg, 88% yield) as a colorless oil. LC-MS (ESI$^+$) m/z 703.2 (M+H)$^+$.

Step 3—1-(((2S,3S,4S)-1-(14-amino-3,6,9,12-tetraoxatetradecyl)-3-ethyl-4-fluoro-5-oxopyrrolidin-2-yl)methoxy)-7-methoxyisoquinoline-6-carboxamide To a solution of tert-butyl N-[2-[2-[2-[2-[2-[(2S,3S,4S)-2-[(6-carbamoyl-7-methoxy-1-isoquinolyl)oxymethyl]-3-ethyl-4-fluoro-5-oxo-pyrrolidin-1-yl]ethoxy]ethoxy] ethoxy]ethoxy]-ethyl]carbamate (18.0 mg, 26.44 umol) in DCM (2 mL) was added HCl in dioxane (4 M, 1 mL). The reaction mixture was stirred at rt for 30 min. On completion, the reaction mixture was concentrated in vacuo to give the title compound (16.3 mg, 99% yield, hydrochloride salt). LC-MS (ESI$^+$) m/z 603.2 (M+H)$^+$.

Step 4—1-[[(2S,3S,4S)-1-[2-[2-[2-[2-[2-[[2-(2,6-dioxo-3-piperidyl)-1,3-dioxo-isoindolin-4-yl]amino] ethoxy]ethoxy]ethoxy]ethoxy]ethyl]-3-ethyl-4-fluoro-5-oxo-pyrrolidin-2-yl]methoxy]-7-methoxy-isoquinoline-6-carboxamide To a solution of 1-[[(2S,3S,4S)-1-[2-[2-[2-[2-(2-amino-ethoxy)ethoxy]ethoxy]ethoxy]ethyl]-3-ethyl-4-fluoro-5-oxo-pyrrolidin-2-yl]methoxy]-7-methoxy-isoquinoline-6-carboxamide (16.3 mg, 26.5 umol, HCl salt) and 2-(2,6-dioxo-3-piperidyl)-4-fluoro-isoindoline-1,3-dione (9.50 mg, 34.4 umol, Intermediate R) in dioxane (5 mL) was added DIPEA (34.2 mg, 46 uL, 264 umol). The reaction mixture was stirred at 120° C. for 76 hrs. On completion, the reaction mixture was concentrated in vacuo. The residue was purified by prep-HPLC (column: Phenomenex Synergi C18 150*25*10 um; mobile phase: [water (0.225% FA)-ACN]; B %: 35%-65%) to give the title compound I-89 (10.0 mg, 42% yield) as a yellow solid. $^1$H NMR (400 MHz, CD$_3$CN) δ 9.09 (s, 1H), 8.45 (s, 1H), 7.91 (d, J=6.0 Hz, 1H), 7.73 (s, 1H), 7.64 (s, 1H), 7.57-7.50 (m, 1H), 7.36 (d, J=6.0 Hz, 1H), 7.04 (s, 1H), 7.02 (d, J=1.6 Hz, 1H), 6.48 (t, J=5.2 Hz, 1H), 6.39 (s, 1H), 5.08-4.95 (m, 1H), 4.92 (dd, J=6.0, 8.4 Hz, 1H), 4.81 (dd, J=3.6, 12.4 Hz, 1H), 4.46 (dd, J=3.2, 12.4 Hz, 1H), 4.30-3.80 (m, 1H), 4.02 (s, 3H), 3.82-3.80 (m, 1H), 3.71-3.42 (m, 18H), 3.41-3.33 (m, 1H), 2.84-2.48 (m, 4H), 2.14-2.09 (m, 1H), 1.81-1.63 (m, 2H), 1.08 (t, J=7.2 Hz, 3H). LC-MS (ESI$^+$) m/z 837.1 (M+H)$^+$.

Example 90: (2S)-3-[(8R)-1-[4-[4-[2-[2-[2-[[2-(2,6-dioxo-3-piperidyl)-1,3-dioxo-isoindolin-4-yl]amino] ethoxy]ethoxy]ethyl]piperazin-1-yl]cyclohexoxy]-7,8-dihydro-6H-cyclopenta[4,5]thieno[1,2-c] pyrimidin-8-yl]-2-hydroxy-propanamide, I-90

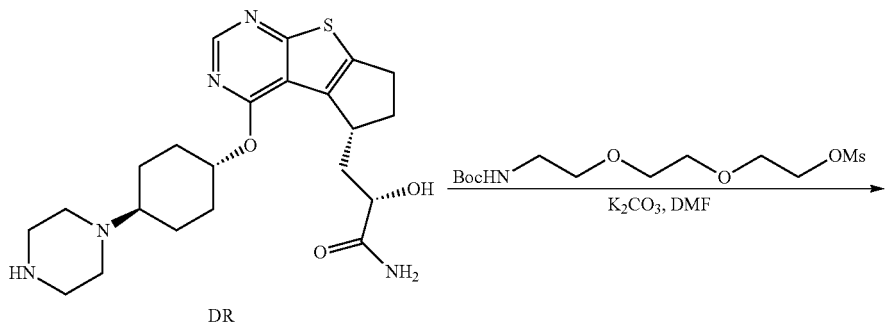

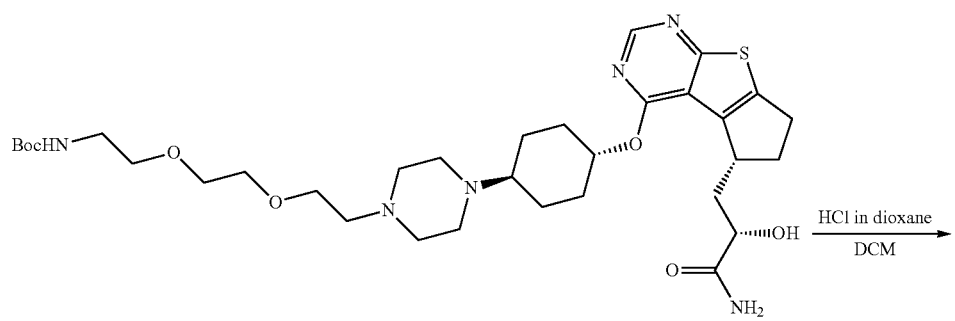

2157

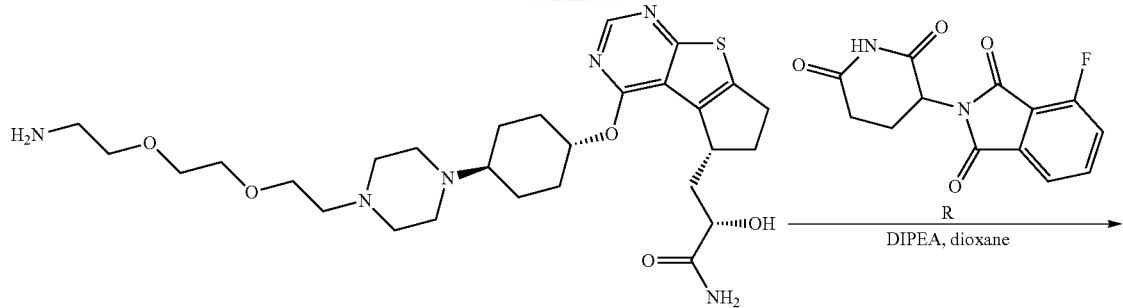

2158

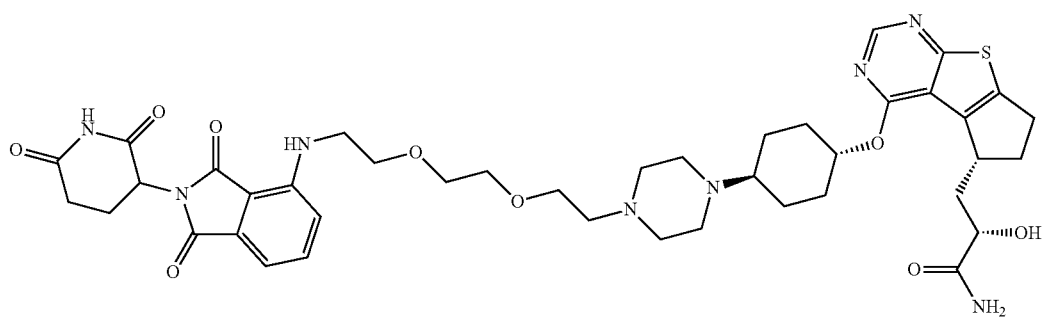

To a solution of (2S)-2-hydroxy-3-[(8R)-1-(4-piperazin-1-ylcyclohexoxy)-7,8-dihydro-6H-cyclopenta[4,5]thieno[1,2-c]pyrimidin-8-yl]propanamide (80.0 mg, 160 umol, HCl salt, Intermediate DR) in DMF (2 mL) was added K$_2$CO$_3$ (89.0 mg, 643 umol) and 2-[2-[2-(tert-butoxycarbonylamino)ethoxy]ethoxy]ethyl methanesulfonate (79.0 mg, 241 umol, synthesized via Step 1 of Intermediate AI), and the mixture was stirred at 60° C. for 20 h. On completion, the reaction mixture was concentrated in vacuo to give a residue. The residue was purified by reverse phase chromatography (0.1% NH3.H2O) to give tert-butyl N-[2-[2-[2-[4-[[(8R)-8-[(2S)-3-amino-2-hydroxy-3-oxo-propyl]-7,8-dihydro-6H-cyclopenta[4,5]thieno[1,2-c]pyrimidin-1-yl]oxy]cyclohexyl]piperazin-1-yl]ethoxy]ethoxy]ethyl]carbamate I-90 (60.0 mg, 53% yield) as a light yellow solid (LC-MS (ESI$^+$) m/z 677.5 (M+H)$^+$). Steps 2 & 3 followed Method 7, where Step 2 was run at rt for 1 h and Step 3 used fluoride Intermediate R for the coupling at 115° C. for 20 h. Characterization of the final product: $^1$H NMR (400 MHz, DMSO-d$_6$) δ 11.13 (s, 1H), 8.52 (m, 1H), 7.59 (dd, J=7.6, 8.4 Hz, 1H), 7.23-7.09 (m, 3H), 7.05 (d, J=7.2 Hz, 1H), 6.60 (t, J=5.6 Hz, 1H), 5.17-5.09 (m, 1H), 5.05 (dd, J=5.2, 12.8 Hz, 1H), 3.91 (t, J=6.8 Hz, 1H), 3.64-3.61 (m, 3H), 3.59-3.53 (m, 7H), 3.18-3.14 (s, 2H), 3.11-2.80 (m, 4H), 2.64-2.54 (m, 3H), 2.43-2.25 (m, 10H), 2.20-1.97 (m, 4H), 1.84-1.81 (m, 2H), 1.70-1.43 (m, 4H), 1.41-1.27 (m, 2H). LC-MS (ESI$^+$) m/z 833.4 (M+H)$^+$.

Example 91: (2R)-3-[(8R)-1-[4-[4-[2-[2-[2-[[2-(2,6-dioxo-3-piperidyl)-1,3-dioxo-isoindolin-4-yl]amino]ethoxy]ethoxy]ethyl]piperazin-1-yl]cyclohexoxy]-7,8-dihydro-6H-cyclopenta[4,5]thieno[1,2-c]pyrimidin-8-yl]-2-hydroxy-propanamide, I-91

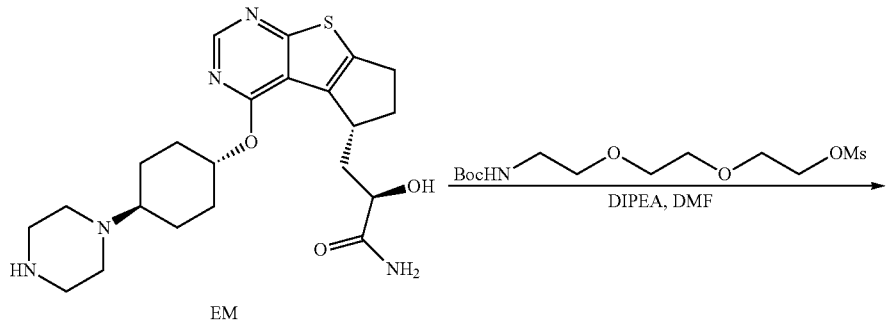

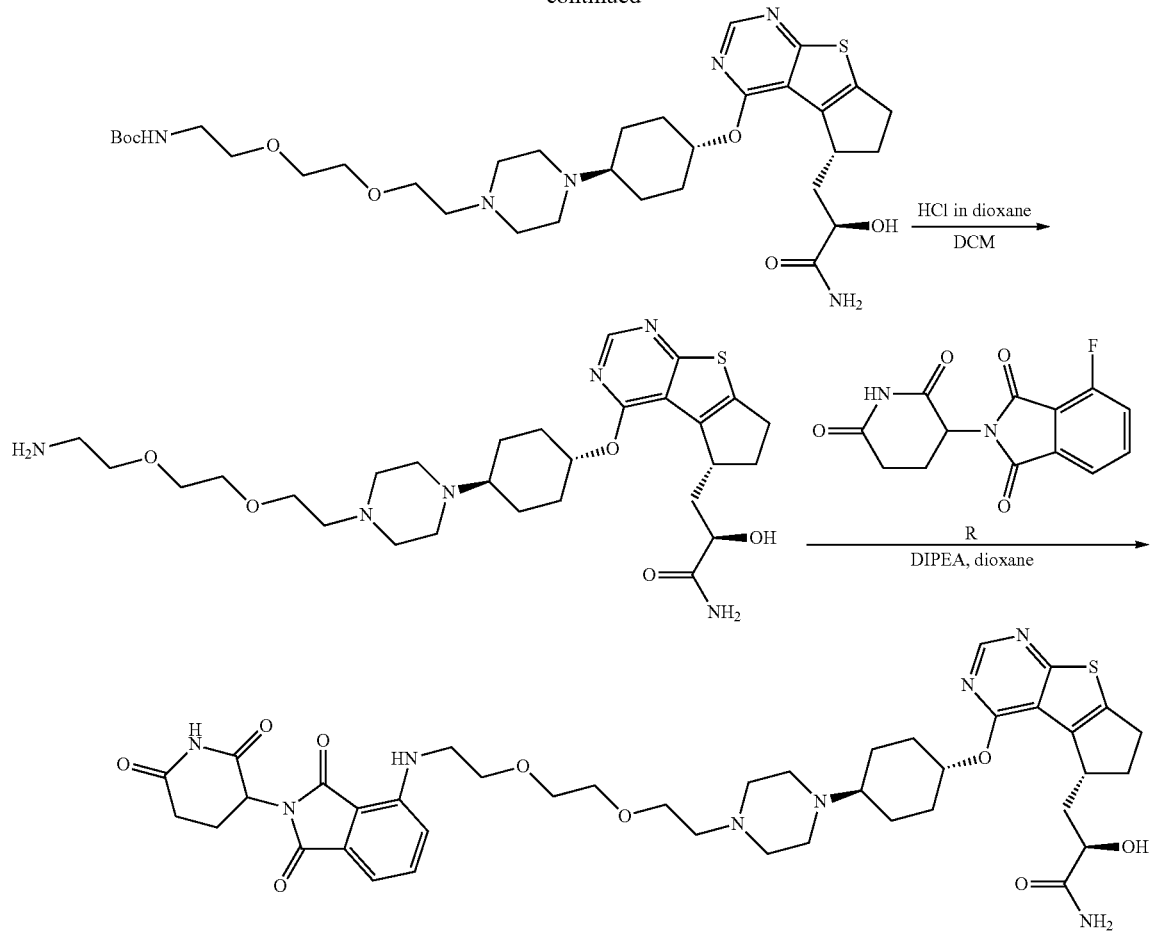

To a mixture of (2R)-2-hydroxy-3-[(8R)-1-(4-piperazin-1-ylcyclohexoxy)-7,8-dihydro-6H-cyclopenta[4,5]thieno[1,2-c]pyrimidin-8-yl]propanamide (60.0 mg, 124 umol, Intermediate EM) in DMF (2 mL) was added K$_2$CO$_3$ (68.8 mg, 497 umol) and 2-[2-[2-(tert-butoxycarbonylamino)ethoxy]ethoxy]ethyl methanesulfonate (81.5 mg, 248 umol, synthesized via Step 1 of Intermediate AI). Then the reaction mixture was stirred at 60° C. for 12 hours. On completion, the reaction mixture was concentrated in vacuo. The crude product was purified by revered phase (FA) to give tert-butyl N-[2-[2-[2-[4-[4-[[(8R)-8-[(2R)-3-amino-2-hydroxy-3-oxopropyl]-7,8-dihydro-6H-cyclopenta[4,5]thieno[1,2-c]pyrimidin-1-yl]oxy]cyclohexyl]piperazin-1-yl]ethoxy]ethoxy]ethyl]carbamate I-91 (75.0 mg, 63% yield) as yellowish oil. LC-MS (ESI$^+$) m/z 677.2 (M+H)$^+$. Steps 2 & 3 followed Method 7, where Step 2 was run at rt for 30 min and Step 3 used fluoride Intermediate R for the coupling at 115° C. for 12 h. Characterization of the final product: $^1$H NMR (400 MHz, DMSO-d$_6$) δ 11.13 (s, 1H), 8.60-8.48 (m, 1H), 7.66-7.50 (m, 1H), 7.21-7.14 (m, 2H), 7.12 (s, 1H), 7.06 (d, J=7.2 Hz, 1H), 6.61 (t, J=5.6 Hz, 1H), 5.19-5.11 (m, 1H), 5.06 (dd, J=5.6, 13.2 Hz, 1H), 3.86-3.84 (m, 1H), 3.72-3.57 (m, 10H), 2.98-2.85 (m, 2H), 2.66-2.55 (m, 2H), 2.48-2.40 (m, 8H), 2.37-2.23 (m, 4H), 2.18-1.99 (m, 4H), 1.85 (d, J=11.6 Hz, 2H), 1.74-1.46 (m, 4H), 1.44-1.26 (m, 2H); LC-MS (ESI$^+$) m/z 833.1 (M+H)$^+$.

Example 92: N-[3-carbamoyl-1-[4-[2-[2-[2-[[2-(2,6-dioxo-3-piperidyl)-1,3-dioxo-isoindolin-4-yl]amino]ethoxy]ethoxy]ethoxymethyl]phenyl]pyrazol-4-yl]-2-[2-(2,2,2-trifluoroethylamino)-4-pyridyl]oxazole-4-carboxamide, I-92

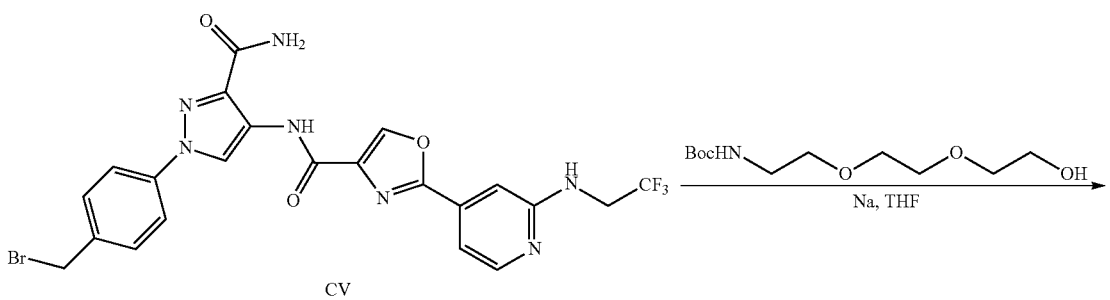

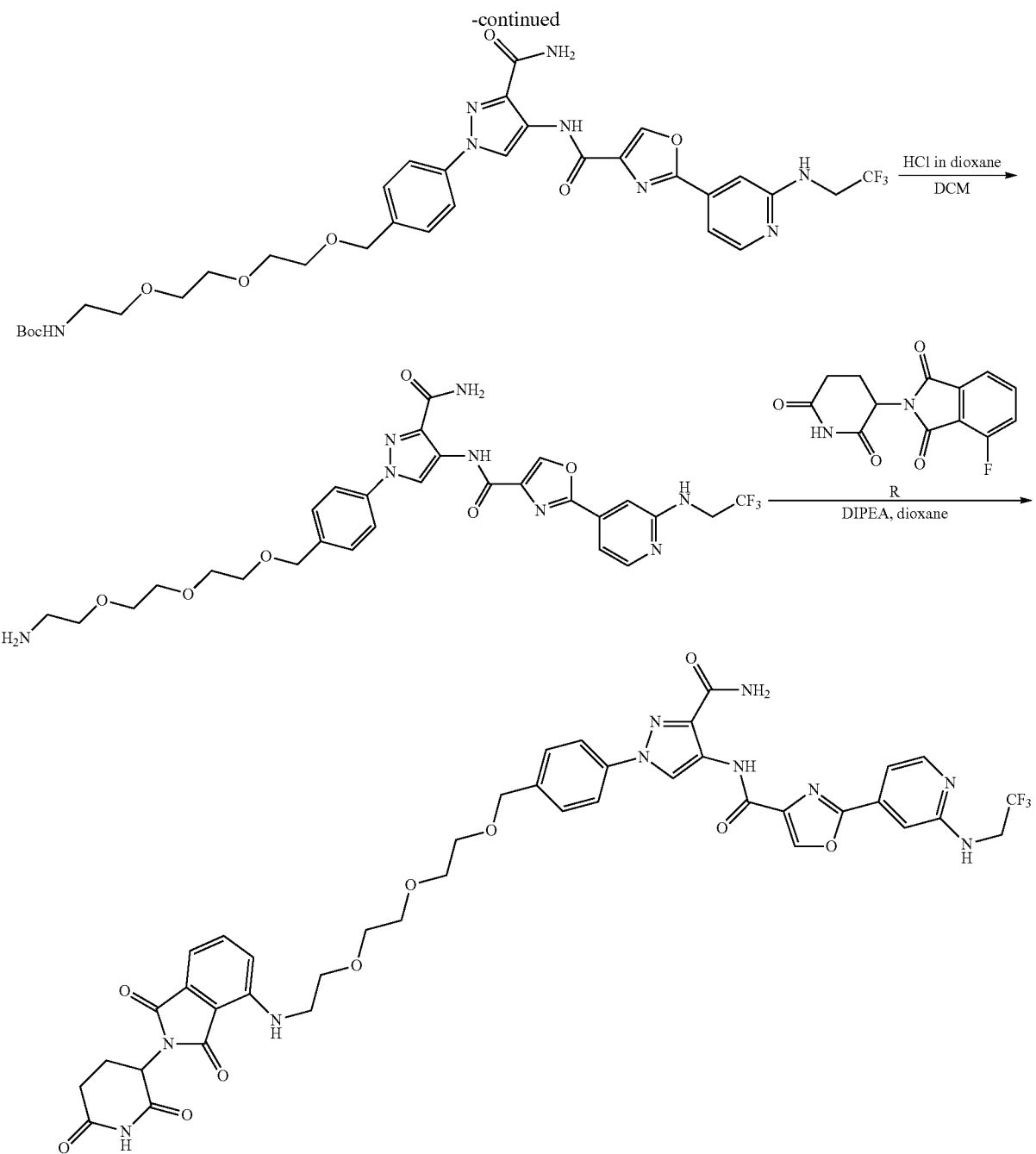

To a solution of tert-butyl N-[2-[2-(2-hydroxyethoxy)ethoxy]ethyl]carbamate (88.0 mg, 354 umol, CAS #139115-92-7) in THF (10 mL) was added Na metal (20 mg, 886 umol). After stirring for 30 minutes at rt, N-[1-[4-(bromomethyl)phenyl]-3-carbamoyl-pyrazol-4-yl]-2-[2-(2,2,2-trifluoroethylamino)-4-pyridyl]oxazole-4-carboxamide (200 mg, 354 umol, Intermediate CV) was added. The mixture was stirred at rt for 30 hours. On completion, the mixture was concentrated in vacuo. The residue was purified by reverse phase chromatography to give tert-butyl N-[2-[2-[2-[[4-[3-carbamoyl-4-[[2-[2-(2,2,2-trifluoroethylamino)-4-pyridyl]oxazole-4-carbonyl]amino]-pyrazol-1-yl]phenyl]methoxy]ethoxy]ethoxy]ethyl]carbamate (30.0 mg, 12% yield) as white solid. LC-MS (ESI$^+$) m/z 733.3 (M+H)$^+$.

Steps 2 & 3 followed Method 7 as described above where the deprotection was run at rt for 2 h. Intermediate R was used as the fluorine coupling partner in the last step, where the reaction was run at 115° C. for 72 hours. The final product was purified by pre-HPLC (column: Phenomenex Synergi C18 150*25*10 um; mobile phase: [water (0.225% FA)-ACN]; B %: 40%-70%, 22 min) to give the title compound I-92 (5.03 mg, 14% yield) as yellow solid. $^1$H NMR (400 MHz, DMSO-d$_6$) δ=11.10 (s, 1H), 11.01 (s, 1H), 9.03 (s, 1H), 8.93 (s, 1H), 8.26 (d, J=5.2 Hz, 1H), 8.06 (s, 1H), 7.99-7.88 (d, J=8.0 Hz, 2H), 7.81-7.66 (m, 2H), 7.57 (t, J=7.6 Hz, 1H), 7.50-7.46 (m, 2H), 7.27 (s, 1H), 7.20-7.12 (m, 2H), 7.03 (d, J=7.2 Hz, 1H), 6.61 (m, 1H), 5.05 (dd, J=5.2, 12.8 Hz, 1H), 4.54 (s, 2H), 4.35-4.16 (m, 2H), 3.69-3.46 (m, 12H), 2.95-2.81 (m, 1H), 2.60-2.57 (m, 2H), 2.06-1.97 (m, 1H); LC-MS (ESI+) m/z 889.8 (M+H)+.

Example 93: 4-(Cyclopropylamino)-N-[3-[2-[2-[2-[[2-(2,6-dioxo-3-piperidyl)-1,3-dioxo-isoindolin-4-yl]amino]-1-methyl-ethoxy]ethoxy]ethoxy]-2-fluoro-propyl]-6-(1,6-naphthyridin-2-ylamino)pyridine-3-carboxamide, I-93

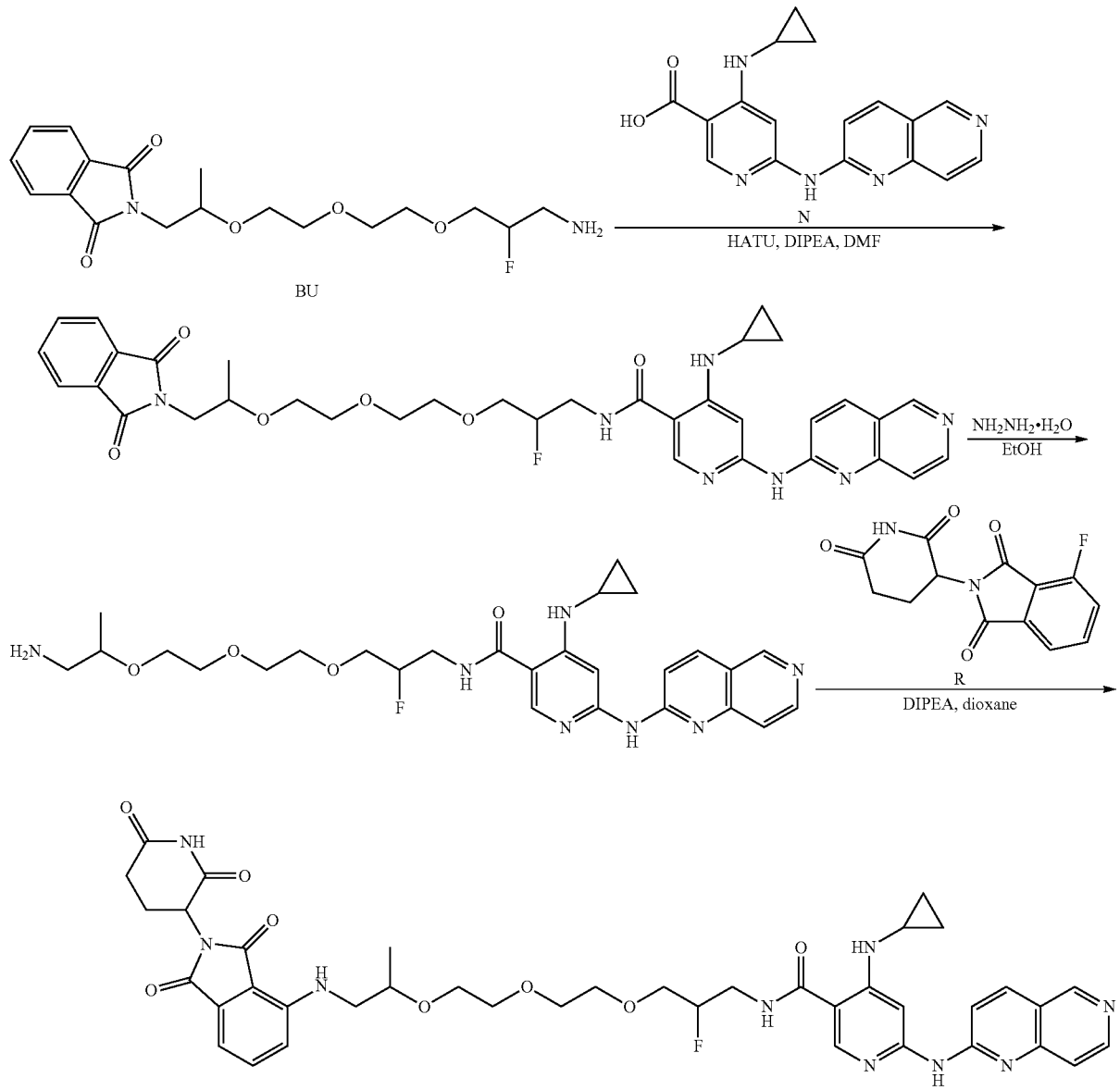

4-(cyclopropylamino)-N-[3-[2-[2-[2-(1,3-dioxoisoindolin-2-yl)-1-methyl-ethoxy]-ethoxy]ethoxy]-2-fluoro-propyl]-6-(1,6-naphthyridin-2-ylamino)pyridine-3-carboxamide was synthesized via Step 1 of Method 7, coupling amine BU with acid Intermediate N. This compound was then deprotected in Step 2 using hydrazine hydrate dissolved in EtOH and stirring at 80° C. for 14 hours. On completion, the reaction mixture was concentrated in vacuo to give a residue. The residue was purified by reversed phase chromatography (0.1% NH$_3$.H$_2$O) to give the title compound I-93 (120 mg, 65% yield) as a brown solid. (LC-MS (ESI)+ m/z 542.3. (M+H)+). Step 3 followed Method 7, where fluoride Intermediate R was utilized. Final product characterization: $^1$H NMR (400 MHz, DMSO-d$_6$) δ 11.10 (br s, 1H), 10.37 (s, 1H), 9.06 (s, 1H), 8.60-8.51 (m, 4H), 8.31-8.24 (m, 2H), 7.60-7.54 (m, 2H), 7.51 (d, J=8.8 Hz, 1H), 7.14 (d, J=8.8 Hz, 1H), 7.03 (d, J=7.2 Hz, 1H), 6.60 (t, J=5.6 Hz, 1H), 5.06 (dd, J=5.6, 12.8 Hz, 1H), 4.83-4.65 (m, 1H), 3.72-3.20 (m, 15H), 2.95-2.84 (m, 1H), 2.65-2.54 (m, 3H), 2.08-1.99 (m, 1H), 1.15 (d, J=6.4 Hz, 3H), 0.98-0.91 (m, 2H), 0.62-0.56 (m, 2H); LC-MS (ESI)+ m/z 798.3. (M+H)+.

Example 94: 6-(5-Cyano-1H-pyrazolo[3,4-b]pyridin-1-yl)-4-(cyclopropylamino)-N-(3-(2-((2-(2-((2-(2,6-dioxopiperidin-3-yl)-1,3-dioxoisoindolin-4-yl)amino)ethoxy)ethyl)amino)ethoxy)-2-fluoropropyl)nicotinamide, I-94
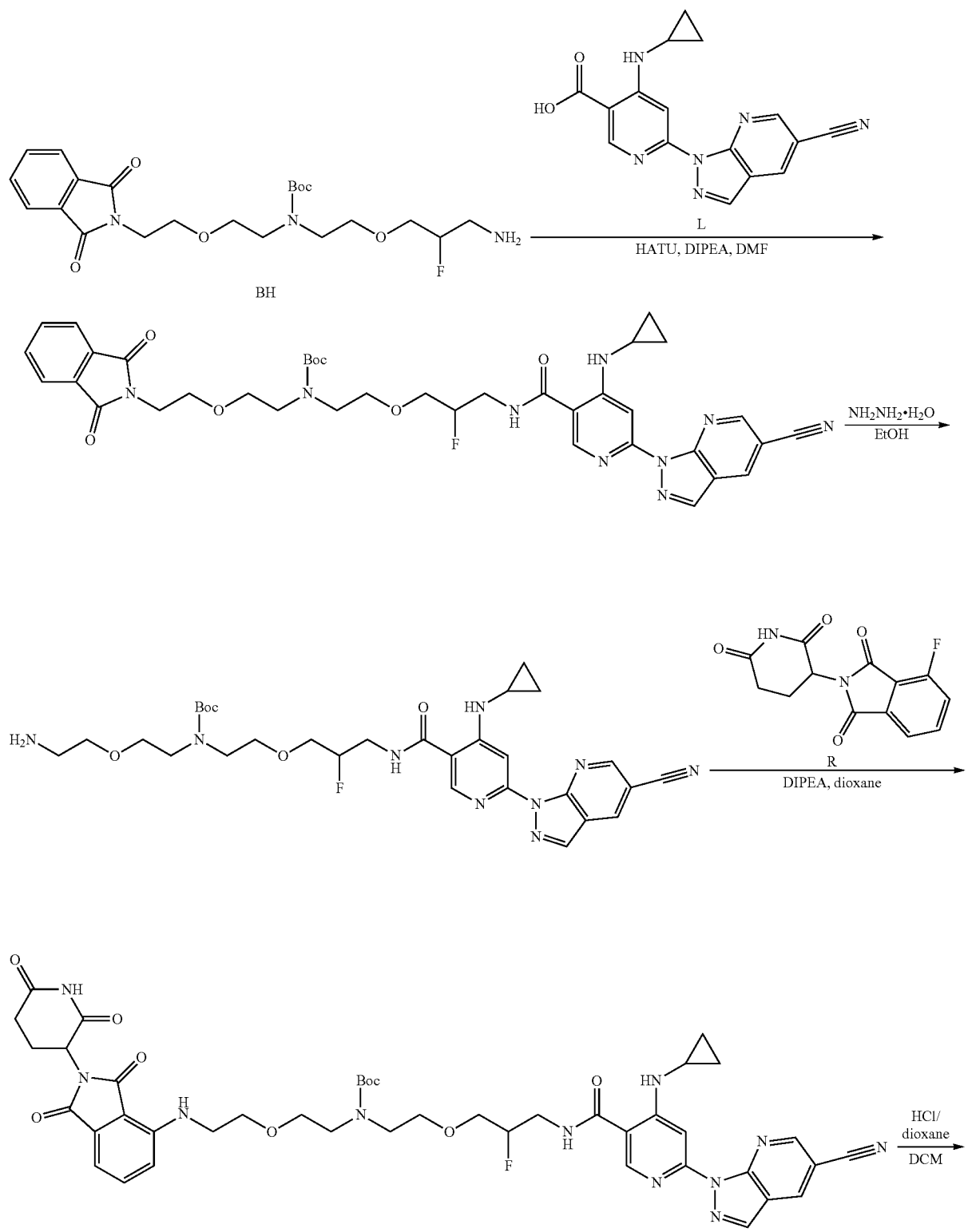

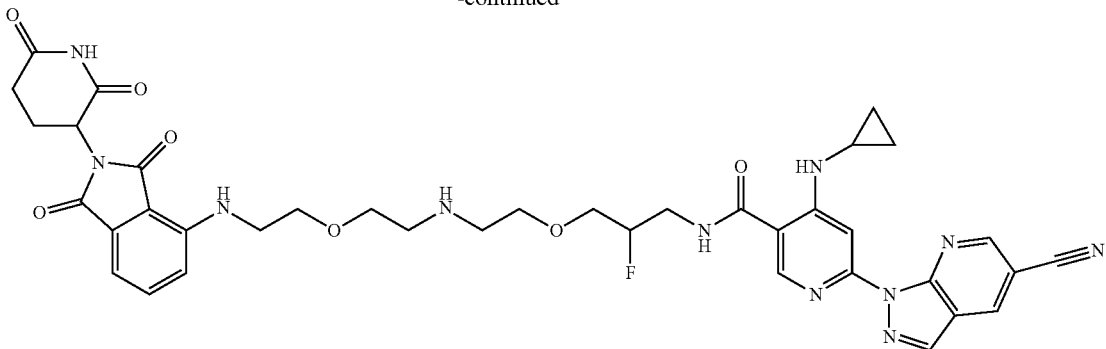

Tert-butyl (2-(3-(6-(5-cyano-1H-pyrazolo[3,4-b]pyridin-1-yl)-4-(cyclopropylamino)nicotinamido)-2-fluoropropoxy)ethyl)(2-(2-(1,3-dioxoisoindolin-2-yl)ethoxy)ethyl)carbamate was synthesized using Step 1 of Method 7 by coupling amine Intermediate BH with acid Intermediate L. For Step 2, the amine was deprotected $N_2H_4 \cdot H_2O$ (54.8 mg, 1.07 mmol) in EtOH (4 mL). The mixture was stirred at 80° C. for 2 hrs. On completion, the reaction mixture was filtered and concentrated under reduced pressure to give a residue. The residue was purified by prep-TLC ($SiO_2$, DCM: MeOH=4/1) to give tert-butyl (2-(2-aminoethoxy)ethyl)(2-(3-(6-(5-cyano-1H-pyrazolo[3,4-b]pyridin-1-yl)-4-(cyclopropylamino)nicotinamido)-2-fluoropropoxy)ethyl)carbamate (45.0 mg, 92.2% yield) as colorless oil (LC-MS (ESI)$^+$ m/z 626.2. (M+H)$^+$). Step 3 coupled Intermediate R as the fluoride under the conditions described for Method 7. The final compound was deprotected by dissolving tert-butyl (2-(3-(6-(5-cyano-1H-pyrazolo[3,4-b]pyridin-1-yl)-4-(cyclopropylamino)nicotin amido)-2-fluoropropoxy)ethyl)(2-(2-((2-(2,6-dioxopiperidin-3-yl)-1,3-dioxoisoindolin-4-yl)amino)ethoxy)ethyl)carbamate (39 mg, 44.2 mg) in DCM (2 mL) and adding HCl in dioxane (4 M, 0.5 mL). The reaction mixture was stirred at 25° C. for 0.5 hr. On completion, the reaction mixture was diluted with MeCN (2 mL) and basified with $NaHCO_3$ solid until the pH=7. After filtration, the mixture was purified directly by prep-HPLC (column: Phenomenex Synergi C18150*25*10 um; mobile phase: [water (0.225% FA)-ACN]) to give the title compound I-94 (2.06 mg, 3.7% yield, FA salt) as a yellow solid. $^1$H NMR (400 MHz, DMSO) δ 11.1 (s, 1H), 9.05 (d, J=2.0 Hz, 1H), 9.01 (d, J=2.0 Hz, 1H), 8.83 (t, J=5.6 Hz, 1H), 8.65 (s, 1H), 8.61 (s, 1H), 8.53 (s, 1H), 8.34 (s, 1H), 7.70 (s, 1H), 7.55 (s, J=7.2 Hz, 1H), 7.11 (d, J=8.8 Hz, 1H), 7.01 (d, J=7.2 Hz, 1H), 6.61 (d, J=6.0 Hz, 1H), 5.09-5.00 (m, 1H), 4.88-4.70 (m, 1H), 3.70-3.50 (m, 5H), 2.95-2.84 (m, 2H), 2.80-2.63 (m, 9H), 2.37-2.30 (m, 4H), 2.05-1.98 (m, 1H), 0.85 (dd, J=6.8, 11.6 Hz, 2H), 0.55 (dd, J=6.8, 11.6 Hz, 2H); LC-MS (ESI)$^+$ m/z 804.2. (M+Na)$^+$.

Example 95 (Method 8): 6-(5-Cyanopyrazolo[3,4-b]pyridin-1-yl)-4-(cyclopropylamino)-N-[3-[2-[2-[[2-[2-(2,6-dioxo-3-piperidyl)-1,3-dioxo-isoindolin-4-yl]oxyacetyl]amino]ethoxy]ethoxy]-2-fluoro-propyl]pyridine-3-carboxamide, I-95

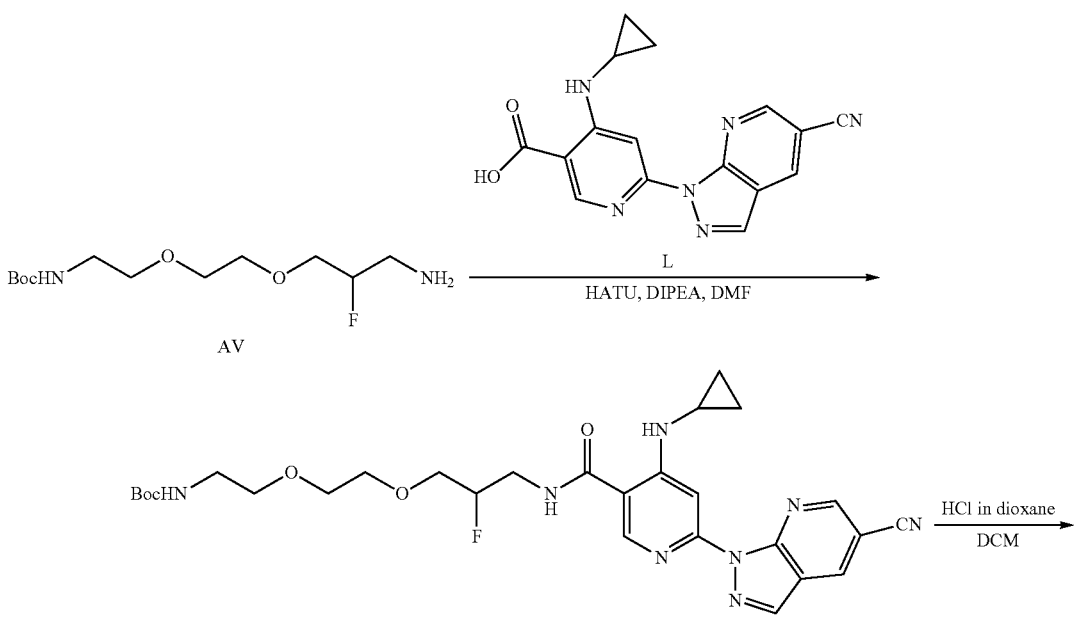

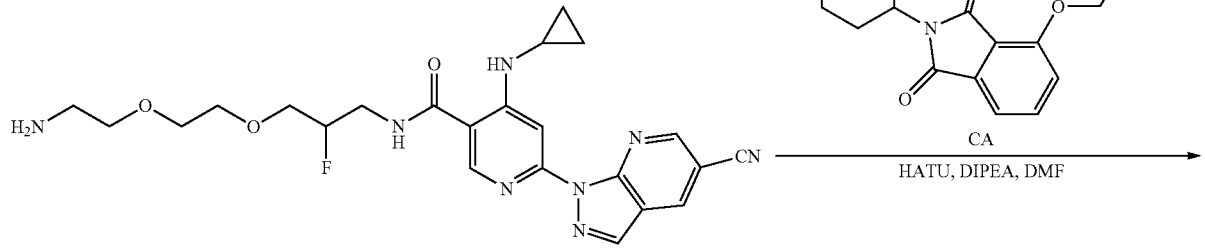

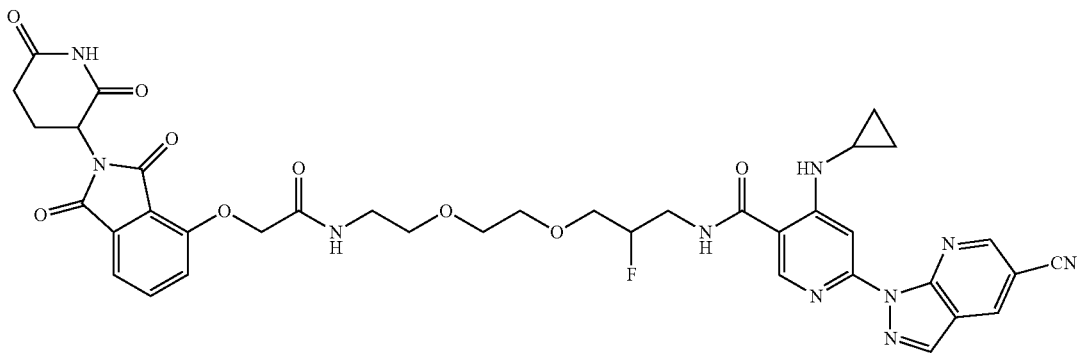

Step 1—Tert-butyl N-[2-[2-[3-[[6-(5-cyanopyrazolo[3,4-b]pyridin-1-yl)-4-(cyclopropylamino)pyridine-3-carbonyl]amino]-2-fluoropropoxy]ethoxy]ethyl]carbamate To a solution of tert-butyl N-[2-[2-(3-amino-2-fluoropropoxy)ethoxy]ethyl]carbamate (100 mg, 356 umol, Intermediate AV) and 6-(5-cyanopyrazolo[3,4-b]pyridin-1-yl)-4-(cyclopropylamino)pyridine-3-carboxylic acid (171 mg, 535 umol, Intermediate L) in DMF (3.00 mL) was added HATU (162 mg, 428 umol) and DIPEA (138 mg, 1.07 mmol, 186 uL). The mixture was stirred at rt for 1 hour. On completion, the mixture was diluted with water (30 mL) and extracted with EA (3×30 mL). The organic layers were dried over anhydrous $Na_2SO_4$, filtered and concentrated in vacuo. The residue was purified by reverse phase (0.1% $NH_3.H_2O$) to give the title compound (80.0 mg, 38% yield) as a yellow oil. LC-MS (ESI$^+$) m/z 583.3 (M+H)$^+$.

Step 2—N-[3-[2-(2-aminoethoxy)ethoxy]-2-fluoropropyl]-6-(5-cyanopyrazolo[3,4-b]pyridin-1-yl)-4-(cyclopropylamino)pyridine-3-carboxamide To a solution of tert-butyl N-[2-[2-[3-[[6-(5-cyanopyrazolo[3,4-b]pyridin-1-yl)-4-(cyclopropylamino)pyridine-3-carbonyl]amino]-2-fluoro-propoxy]ethoxy]ethyl]carbamate (80.0 mg, 137 umol) in DCM (4.00 mL) was added HCl in dioxane (4 M, 2.00 mL) and the mixture was stirred at rt for 30 minutes. On completion, the mixture was concentrated in vacuo to give the title compound (70.0 mg, 98% yield) as white solid. LC-MS (ESI$^+$) m/z 483.2 (M+H)$^+$.

Step 3—6-(5-Cyanopyrazolo[3,4-b]pyridin-1-yl)-4-(cyclopropylamino)-N-[3-[2-[2-[[2-[2-(2,6-dioxo-3-piperidyl)-1,3-dioxo-isoindolin-4-yl]oxyacetyl]amino]ethoxy]ethoxy]-2-fluoro-propyl]pyridine-3-carboxamide To a solution of N-[3-[2-(2-aminoethoxy)ethoxy]-2-fluoro-propyl]-6-(5-cyanopyrazolo[3,4-b]pyridin-1-yl)-4-(cyclopropylamino)pyridine-3-carboxamide (50.0 mg, 96.3 umol, HCl) and 2-[2-(2,6-dioxo-3-piperidyl)-1,3-dioxo-isoindolin-4-yl]oxyacetic acid (32.0 mg, 96.3 umol, Intermediate CA) in DMF (2.00 mL) was added HATU (43.9 mg, 115 umol) and DIPEA (62.2 mg, 481 umol, 83.9 uL). The mixture was stirred at rt for 1 hour. On completion, the mixture was diluted with $H_2O$ (30 mL) and extracted with EA (3×15 mL). The organic layers were dried over anhydrous $Na_2SO_4$, filtered and concentrated in vacuo. The mixture was purified by prep-HPLC (column: Phenomenex Synergi C18 150*25*10 um; mobile phase: [water (0.225% FA)-ACN]; B %: 20%-50%, 10 min) to give the title compound I-95 (35.36 mg, 43% yield, FA) as a white solid. $^1$H NMR (400 MHz, DMSO-$d_6$) δ 11.1 (s, 1H), 9.06 (d, J=1.6 Hz, 1H), 9.02 (d, J=1.6 Hz, 1H), 8.91-8.81 (m, 1H), 8.66 (s, 1H), 8.62 (s, 1H), 8.54 (s, 1H), 8.07-7.98 (m, 1H), 7.82-7.76 (m, 1H), 7.71 (s, 1H), 7.48 (d, J=7.2 Hz, 1H), 7.39 (d, J=8.8 Hz, 1H), 5.13-5.09 (m, 1H), 4.79 (s, 2H), 4.88-4.71 (m, 1H), 3.61-3.46 (m, 12H), 2.95-2.83 (m, 1H), 2.63-2.54 (m, 3H), 2.09-2.02 (m, 1H), 0.89-0.83 (m, 2H), 0.60-0.53 (m, 2H); LC-MS (ESI$^+$) m/z 797.4 (M+H)$^+$.

TABLE 6

Compounds synthesized via Method 8 with the coupling of various amines and acids in Step 1, followed by coupling with acid Intermediate CA in Step 3.

| Ex-# | I-# | Intermediate Amine | Intermediate Acid | LCMS (ES+) m/z (M + H)+ | HNMR (400 MHz, DMSO-d6) δ |
|---|---|---|---|---|---|
| 96 | I-96 | AI | N | 842.4 | 12.08 (s, 1H), 11.14 (s, 1H), 9.61 (s, 1H), 9.13 (s, 1H), 8.95 (s, 1H), 8.86 (d, J = 6.8 Hz, 1H), 8.70 (d, J = 8.8 Hz, 1H), 8.50 (s, 1H), 8.34 (d, J = 6.4 Hz, 1H), 8.02 (t, J = 5.6 Hz, 1H), 7.83-7.79 (m, 1H), 7.55 (d, J = 8.8 Hz, 1H), 7.49 (d, J = 7.2 Hz, 1H), 7.39 (d, J = 8.4 Hz, 1H), 7.14 (s, 1H), 5.12 (dd, J = 5.2, 12.8 Hz, 1H), 4.88-4.73 (m, 3H), 3.75-3.60 (m, 6H), 3.53-3.44 (m, 6H), 3.34-3.30 (m, 2H), 2.97-2.84 (m, 2H), 2.71 (s, 1H), 2.60-2.57 (m, 1H), 2.56-2.52 (m, 2H), 2.10-1.98 (m, 1H), 0.99-0.91 (m, 2H), 0.73-0.69 |
| 97 | I-97 | AK | N | 930.5 | 11.14 (s, 1H), 10.38 (s, 1H), 9.05 (s, 1H), 8.60-8.55 (m, 3H), 8.47 (s, 1H), 8.27 (d, J = 9.0 Hz, 1H), 8.19 (s, 1H), 8.02 (t, J = 5.6 Hz, 1H), 7.80 (dd, J = 7.6, 8.4 Hz, 1H), 7.57 (d, J = 5.6 Hz, 1H), 7.54-7.44 (m, 2H), 7.39 (d, J = 8.4 Hz, 1H), 5.12 (dd, J = 5.6, 12.8 Hz, 1H), 4.87-4.65 (m, 3H), 3.73-3.51 (m, 12H), 3.50-3.40 (m, 10H), 3.37-3.21 (m, 2H), 2.99-2.84 (m, 1H), 2.65-2.56 (m, 2H), 2.55 (d, J = 4.4 Hz, 1H), 2.10-2.02 (m, 1H), 1.04-0.89 (m, 2H), 0.69-0.52 (m, 2H) |
| 98 | I-98 | BA | N | 886.1 | 13.12 (s, 1H), 11.14 (s, 1H), 9.64 (s, 1H), 9.32 (s, 1H), 8.93 (s, 1H), 8.86 (d, J = 6.4 Hz, 1H), 8.73 (d, J = 8.8 Hz, 1H), 8.63 (s, 1H), 8.50 (d, J = 5.6 Hz, 1H), 8.12-8.03 (m, 1H), 7.85-7.73 (m, 2H), 7.48 (d, J = 7.2 Hz, 1H), 7.43 (s, 1H), 7.39 (d, J = 8.2 Hz, 1H), 5.12 (dd, J = 5.2, 12.6 Hz, 1H), 4.90-4.73 (m, 3H), 3.74-3.56 (m, 12H), 3.48-3.44 (m, 4H), 3.38-3.08 (m, 2H), 3.04-2.80 (m, 2H), 2.68-2.62 (m, 2H), 2.55-2.52 (m, 2H), 2.07-1.99 (m, 1H), 0.98-0.90 (m, 2H), 0.74-0.66 (m, 2H) |
| 99 | I-99 | AV | N | 798.3 | 11.15 (s, 1H), 10.38 (s, 1H), 9.06 (s, 1H), 8.61-8.55 (m, 3H), 8.53 (s, 1H), 8.28 (d, J = 9.2 Hz, 1H), 8.22 (s, 1H), 8.04 (t, J = 5.6 Hz, 1H), 7.86-7.72 (m, 1H), 7.57 (d, J = 5.6 Hz, 1H), 7.52-7.44 (m, 2H), 7.39 (d, J = 8.4 Hz, 1H), 5.12 (dd, J = 5.2, 12.8 Hz, 1H), 4.83-4.66 (m, 3H), 3.71-3.68 (m, 1H), 3.66-3.56 (m, 10H), 2.94-2.88 (m, 1H), 2.65-2.58 (m, 2H), 2.57-2.53 (m, 2H), 2.08-2.00 (m, 1H), 0.95 (d, J = 5.2 Hz, 2H), 0.63-0.55 (s, 2H) |
| 100 | I-100 | BV | N | 826.5 | 11.13 (s, 1H), 10.37 (s, 1H), 9.06 (s, 1H), 8.60-8.55 (m, 3H), 8.46 (s, 1H), 8.28 (d, J = 9.2 Hz, 1H), 8.21 (s, 1H), 7.95 (t, J = 5.6 Hz, 1H), 7.85-7.78 (m, 1H), 7.57 (d, J = 6.0 Hz, 1H), 7.53-7.47 (m, 2H), 7.39 (d, J = 8.4 Hz, 1H), 5.14-5.10 (m, 1H), 4.84-4.68 (m, 3H), 3.67-3.57 (m, 2H), 3.55-3.41 (m, 8H), 3.25-3.18 (m, 2H), 2.88 (m, 1H), 2.70-2.61 (m, 2H), 2.37-2.30 (m, 1H), 2.09-2.00 (m, 1H), 1.79-1.63 (m, 4H), 0.98-0.92 (m, 2H), 0.63-0.55 (m, 2H) |
| 101 | I-101 | AU | L | 825.4 | 11.18 (s, 1H), 9.08 (d, J = 2.0 Hz, 1H), 9.04 (d, J = 2.0 Hz, 1H), |

TABLE 6-continued

Compounds synthesized via Method 8 with the coupling of various amines and acids in Step 1, followed by coupling with acid Intermediate CA in Step 3.

| Ex-# | I-# | Intermediate Amine | Intermediate Acid | LCMS (ES+) m/z (M + H)+ | HNMR (400 MHz, DMSO-d6) δ |
|---|---|---|---|---|---|
| | | | | | 8.85-8.80 (m, 1H), 8.67 (s, 1H), 8.61 (s, 1H), 8.60-8.59 (m, 1H), 8.01 (t, J = 5.6 Hz, 1H), 7.80-7.75 (m, 1H), 7.71 (s, 1H), 7.46 (d, J = 7.2 Hz, 1H), 7.39 (d, J = 8.8 Hz, 1H), 5.12 (dd, J = 5.2, 12.8 Hz, 1H), 4.79 (s, 2H), 4.59-4.42 (m, 1H), 3.80-3.62 (m, 2H), 3.58-3.46 (m, 6H), 3.46-3.43 (m, 1H), 2.95-2.83 (m, 1H), 2.65-2.60 (m, 1H), 2.60-2.56 (m, 2H), 2.55-2.54 (m, 1H), 2.07-2.02 (m, 1H), 1.21 (s, 6H), 0.89-0.83 (m, 2H), 0.60-0.55 (m, 2H) |
| 102 | I-102 | BG | L | 795.4 | 11.13 (s, 1H), 9.07 (d, J = 1.6 Hz, 1H), 9.03 (d, J = 2.0 Hz, 1H), 8.88-8.82 (m, 1H), 8.67 (s, 1H), 8.63 (s, 1H), 8.56 (s, 1H), 7.96 (s, 1H), 7.81 (t, J = 7.6 Hz, 1H), 7.72 (s, 1H), 7.49 (d, J = 7.6 Hz, 1H), 7.39 (d, J = 8.4 Hz, 1H), 5.12 (dd, J = 5.2, 12.8 Hz, 1H), 4.89-4.69 (m, 3H), 3.69-3.41 (m, 4H), 3.20-3.12 (m, 2H), 2.96-2.84 (m, 1H), 2.68-2.66 (m, 1H), 2.64-2.56 (m, 3H), 2.34-2.30 (m, 1H), 2.04-2.00 (m, 1H), 1.57-1.43 (m, 4H), 1.33-1.30 (m, 2H), 0.87-0.80 (m, 2H), 0.58-0.56 (m, 2H) |
| 103 | I-103 | tert-butyl N-[2-[2-[2-[2-(2-aminoethoxy)-ethoxy]-ethoxy]ethoxy]-ethyl]carbamate (CAS# 01187-40-0) | CE | 895.4 | 11.12 (br s, 1H), 8.88 (s, 1H), 8.46 (t, J = 5.6 Hz, 1H), 8.16 (s, 1H), 8.01 (t, J = 5.2 Hz, 1H), 7.91 (d, J = 5.6 Hz, 1H), 7.84-7.78 (m, 1H), 7.75 (s, 1H), 7.49 (d, J = 7.2 Hz, 1H), 7.44 (d, J = 5.6 Hz, 1H), 7.39 (d, J = 8.4 Hz, 1H), 5.12 (dd, J = 5.2, 12.8 Hz, 1H), 4.99-4.82 (m, 1H), 4.79 (s, 2H), 4.54 (dd, J = 3.2, 11.2 Hz, 1H), 4.26 (dd, J = 6.4, 11.2 Hz, 1H), 4.10-4.08 (m, 1H), 3.97 (s, 3H), 3.60-3.43 (m, 18H), 3.32-3.27 (m, 2H), 2.96-2.84 (m, 1H), 2.70-2.57 (m, 3H), 2.09-2.00 (m, 1H), 1.66-1.55 (m, 2H), 1.02 (t, J = 7.2 Hz, 3H) |
| 104 | I-104 | CG | CN | 998.1 | 11.11 (s, 1H), 11.02 (s, 1H), 9.04 (d, J = 4.0 Hz, 2H), 8.55 (s, 1H), 8.26 (d, J = 5.2 Hz, 1H), 8.13 (s, 1H), 8.10 (d, J = 8.4 Hz, 2H), 8.04-7.89 (m, 3H), 7.86-7.75 (m, 2H), 7.69 (t, J = 6.0 Hz, 1H), 7.50 (d, J = 7.2 Hz, 1H), 7.40 (d, J = 8.4 Hz, 1H), 7.28 (s, 1H), 7.19 (d, J = 5.2 Hz, 1H), 5.12 (dd, J = 5.6, 12.8 Hz, 1H), 4.83-4.73 (m, 2H), 4.32-4.19 (m, 2H), 3.29-3.26 (m, 2H), 3.14 (d, J = 6.0 Hz, 2H), 2.89 (d, J = 9.2 Hz, 1H), 2.64-2.56 (m, 2H), 2.11-1.98 (m, 1H), 1.61-1.37 (m, 4H), 1.31-1.21 (m, 14H) |

Variations in reaction time for Method 8 were as follows: Step 1 was run anywhere from 0.5-16 h, Step 2 anywhere from 0.5-3 h, Step 3 anywhere from 0.5-12 h.

Further Examples Using Synthetic Methods Similar to Method 8

Example 105: N-[3-carbamoyl-1-[4-[2-[2-[2-[2-[[2-[2-(2,6-dioxo-3-piperidyl)-1,3-dioxo-isoindolin-4-yl]oxyacetyl]amino]ethoxy]ethoxy]ethoxy]ethoxymethyl]phenyl]pyrazol-4-yl]-2-[2-(2,2,2-trifluoroethylamino)-4-pyridyl]oxazole-4-carboxamide, I-105

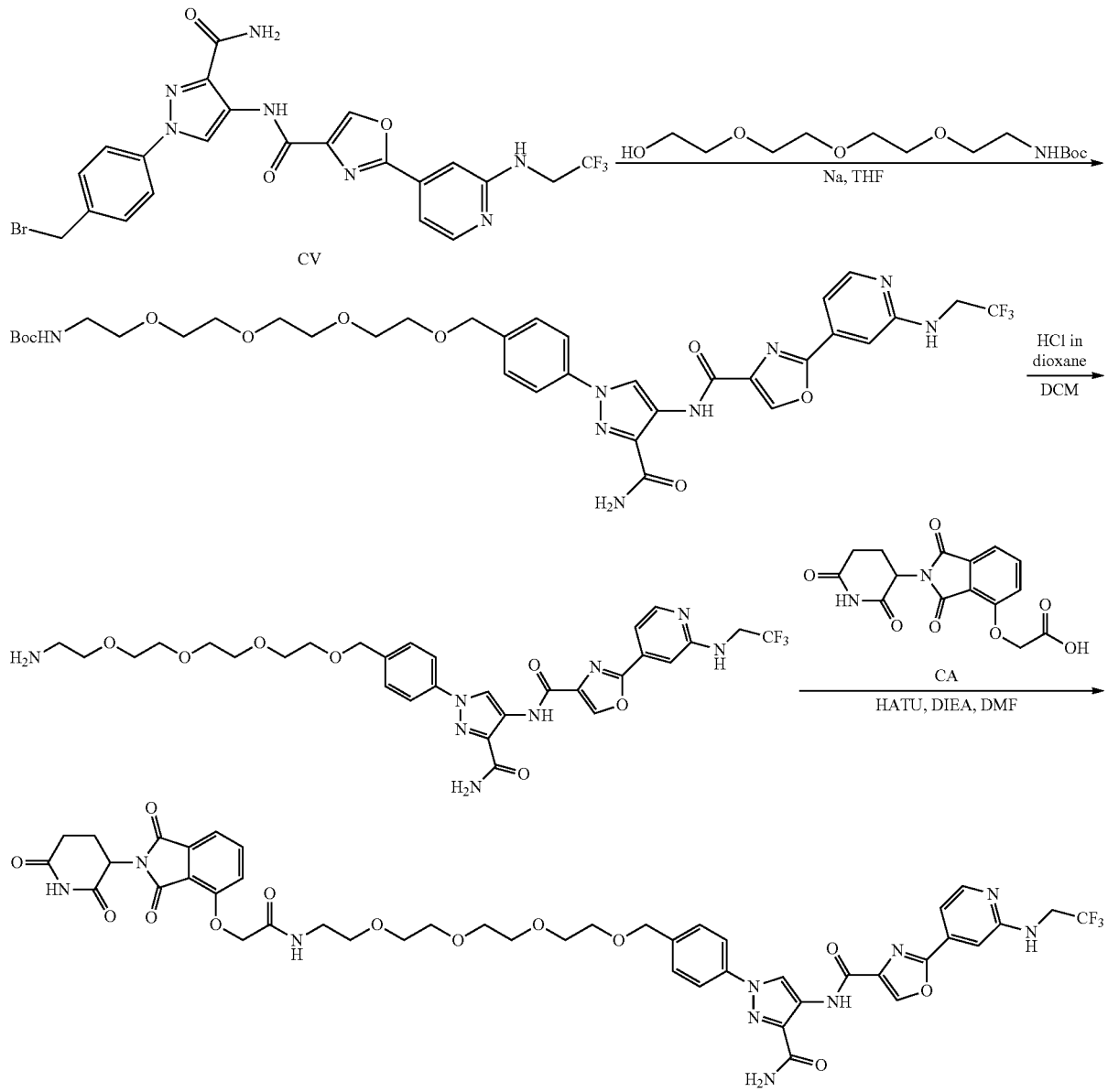

To a mixture of tert-butyl N-[2-[2-[2-(2-hydroxyethoxy)ethoxy]ethoxy]ethyl]carbamate (31.0 mg, 106 umol, synthesized via Steps 1-3 of Intermediate AO) in THF (15 mL) was added Na metal (6.00 mg, 267 umol) and N-[1-[4-(bromomethyl)phenyl]-3-carbamoyl-pyrazol-4-yl]-2-[2-(2,2,2-trifluoroethyl amino)-4-pyridyl]oxazole-4-carboxamide (60.0 mg, 106 umol, Intermediate CV). The mixture was stirred at rt for 18 hours. On completion, the mixture was concentrated in vacuo. The residue was purified by reverse phase chromatography (0.1% FA in water) to give the tert-butyl N-[2-[2-[2-[2-[[4-[3-carbamoyl-4-[[2-[2-(2,2,2-trifluoroethyl amino)-4-pyridyl]oxazole-4-carbonyl]amino]-pyrazol-1-yl]phenyl]methoxy]ethoxy]ethoxy]ethoxy]ethyl]carbamate compound (15.0 mg, 18% yield) as a white solid. LC-MS (ESI$^+$) m/z 799.4 (M+Na)$^+$.

Steps 2 & 3 followed Method 8 as described above where the deprotection was run at rt for 30 min. Intermediate CA was used as the acid coupling partner in the last step, where the reaction was run at rt for 18 h. The final product was purified by Pre-HPLC (column: Phenomenex Synergi C18 150*25*10 um; mobile phase: [water (0.225% FA)-ACN]; B %: 30%-60%, 10 min) to give the title compound I-105 (1.20 mg, 6% yield) as white solid. $^1$H NMR (400 MHz, DMSO-d$_6$) δ 11.08 (s, 1H), 10.99 (s, 1H), 9.01 (s, 1H), 8.93 (s, 1H), 8.26 (d, J=5.2 Hz, 1H), 8.11-7.86 (m, 4H), 7.83-7.76 (m, 1H), 7.74-7.64 (m, 2H), 7.50-7.47 (m, 3H), 7.42-7.34

(m, 2H), 7.27 (s, 1H), 7.18 (d, J=5.2 Hz, 1H), 5.11 (dd, J=5.2, 12.8 Hz, 1H), 4.78 (s, 2H), 4.55 (s, 2H), 4.31-4.19 (m, 2H), 3.61-3.38 (m, 16H), 2.95-2.88 (m, 1H), 2.61-2.58 (m, 2H), 2.06-2.03 (m, 1H); LC-MS (ESI$^+$) m/z 1013.3 (M+Na)$^+$.
Example 106 (Method 9): N-[3-carbamoyl-1-[4-[5-[[2-[2-(2,6-dioxo-3-piperidyl)-1,3-dioxo-isoindolin-4-yl]oxyacetyl]amino]pentylcarbamoyl phenyl]pyrazol-4-yl]-2-[2-(2,2,2-trifluoroethylamino)-4-pyridyl] oxazole-4-carboxamide, I-106
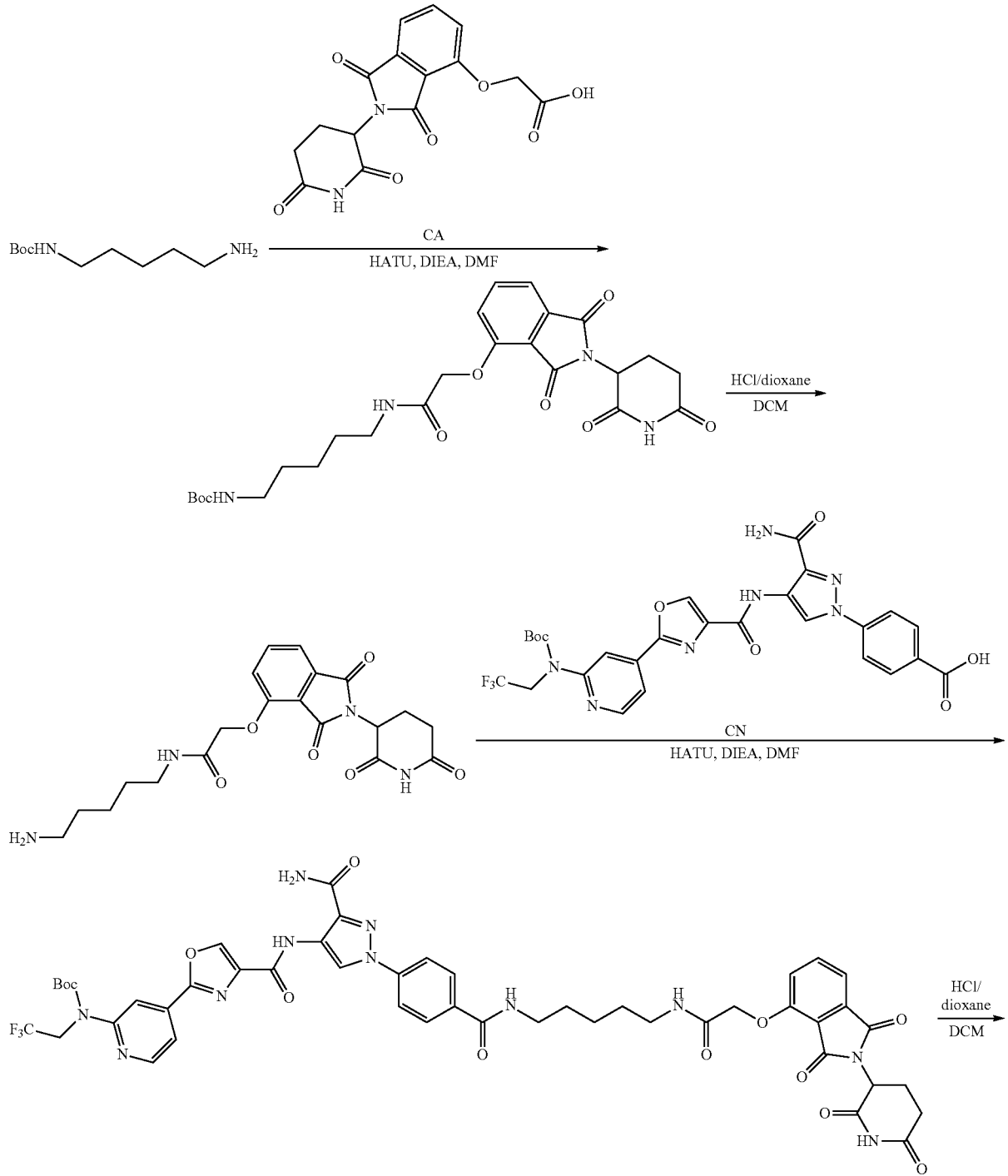

-continued

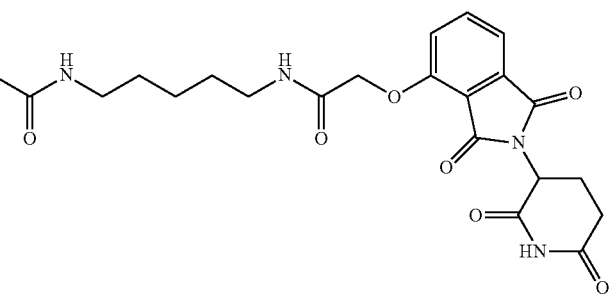

Step 1—Tert-butyl N-[5-[[2-[2-(2,6-dioxo-3-piperidyl)-1,3-dioxo-isoindolin-4-yl]oxyacetyl]amino]pentyl]carbamate To a mixture of tert-butyl N-(5-aminopentyl)carbamate (1.50 g, 7.41 mmol, CAS #51644-96-3) and DIPEA (3.83 g, 29.6 mmol) in DMF (15 mL) was added 2-[2-(2,6-dioxo-3-piperidyl)-1,3-dioxo-isoindolin-4-yl]oxyacetic acid (2.46 g, 7.41 mmol, Intermediate CA) and HATU (3.38 g, 8.90 mmol). The reaction mixture was stirred at rt for 1 hour. On completion, the reaction mixture was concentrated in vacuo. The residue was purified by prep-HPLC (0.1% NH$_3$.H$_2$O) to give the title compound (2.10 g, 54% yield) as a white solid. LC-MS (ESI$^+$) m/z 417.0 (M+H−100)$^+$.

Step 2—N-(5-aminopentyl)-2-[2-(2,6-dioxo-3-piperidyl)-1,3-dioxo-isoindolin-4-yl]oxy-acetamide To a mixture of tert-butyl N-[5-[[2-[2-(2,6-dioxo-3-piperidyl)-1,3-dioxo-isoindolin-4-yl]oxyacetyl]amino]pentyl]carbamate (500 mg, 967 umol) in DCM (4 mL) was added HCl in dioxane (4 M, 2 mL). The reaction mixture was stirred at rt for 0.5 hour. On completion, the reaction mixture was concentrated in vacuo. The residue was purified by prep-HPLC (0.1% NH$_3$.H$_2$O) to give the title compound (400 mg, 99% yield) as white solid. LC-MS (ESI$^+$) m/z 417.1 (M+H)$^+$.

Step 3—Tert-butyl N-[4-[4-[[3-carbamoyl-1-[4-[5-[[2-[2-(2,6-dioxo-3-piperidyl)-1,3-dioxo-isoindolin-4-yl]oxyacetyl]amino]pentylcarbamoyl]phenyl]pyrazol-4-yl]carbamoyl]oxazol-2-yl]-2-pyridyl]-N-(2,2,2-trifluoroethyl)carbamate To a mixture of N-(5-aminopentyl)-2-[2-(2,6-dioxo-3-piperidyl)-1,3-dioxo-isoindolin-4-yl]oxy-acetamide (250 mg, 552 umol, HCl) and DIPEA (356 mg, 2.76 mmol) in DMF (4 mL) was added 4-[4-[[2-[2-[tert-butoxycarbonyl(2, 2,2-trifluoroethyl)amino]-4-pyridyl]oxazole-4-carbonyl]amino]-3-carbamoyl-pyrazol-1-yl]benzoic acid (339 mg, 552 umol, Intermediate CN) and HATU (251 mg, 662 umol). The reaction mixture was stirred at rt for 0.5 hour. On completion, the reaction mixture was diluted with water (5 mL) and filtered and concentrated in vacuo to give the title compound (400 mg, 80% yield) as light yellow solid. LC-MS (ESI$^+$) m/z 1014.3 (M+H)$^+$.

Step 4—N-[3-carbamoyl-1-[4-[5-[[2-[2-(2,6-dioxo-3-piperidyl)-1,3-dioxo-isoindolin-4-yl]oxyacetyl]amino]pentyl carbamoyl]phenyl]pyrazol-4-yl]-2-[2-(2,2,2-trifluoroethylamino)-4-pyridyl]oxazole-4-carboxamide To a mixture of tert-butyl N-[4-[4-[[3-carbamoyl-1-[4-[5-[[2-[2-(2,6-dioxo-3-piperidyl)-1,3-dioxo-isoindolin-4-yl]oxyacetyl]amino]pentylcarbamoyl]phenyl]pyrazol-4-yl]carbamoyl]oxazol-2-yl]-2-pyridyl]-N-(2,2,2-trifluoroethyl)carbamate (400 mg, 394 umol) in DCM (3 mL) was added HCl in dioxane (4 M, 2 mL). The reaction mixture was stirred at rt for 0.5 hour. On completion, the reaction mixture was concentrated in vacuo. The residue was purified by prep-HPLC (column: Phenomenex luna C18 250*50 mm*10 um; mobile phase: [water (0.225% FA)-ACN]) to give the title compound I-106 (79.4 mg, 20% yield) as white solid. $^1$H NMR (400 MHz, DMSO-d$_6$) δ 11.13 (s, 1H), 11.03 (s, 1H), 9.04 (s, 2H), 8.56 (t, J=5.6 Hz, 1H), 8.26 (d, J=5.2 Hz, 1H), 8.15 (s, 1H), 8.12-8.08 (m, 2H), 8.04-7.94 (m, 3H), 7.85-7.76 (m, 2H), 7.71 (t, J=6.4 Hz, 1H), 7.49 (d, J=7.2 Hz, 1H), 7.40 (d, J=8.4 Hz, 1H), 7.28 (s, 1H), 7.21-7.16 (m, 1H), 5.14 (dd, J=5.2, 12.8 Hz, 1H), 4.81 (s, 2H), 4.29-4.21 (m, 2H), 3.30-3.27 (m, 2H), 3.18 (d, J=6.0 Hz, 2H), 2.96-2.86 (m, 1H), 2.66-2.61 (m, 1H), 2.60-2.56 (m, 1H), 2.10-2.01 (m, 1H), 1.60-1.46 (m, 4H), 1.40-1.29 (m, 2H); LC-MS (ESI$^+$) m/z 914.3 (M+H)$^+$.

TABLE 7

Compounds synthesized via Method 9 with the coupling of various
amines and acids in Step 1, followed by coupling with acid Intermediate CN in Step 3

| Ex-# | I-# | Step 1 Intermediate Amine | Step 1 Intermediate Acid | LCMS (ES+) m/z (M + H)+ | HNMR (400 MHz, DMSO-d6) δ |
|---|---|---|---|---|---|
| 107 | I-107 | CI | CH | 1161.2 | 11.01 (s, 1H), 9.07-8.99 (m, 2H), 8.96 (s, 1H), 8.74-8.56 (m, 2H), 8.26 (d, J = 5.6 Hz, 1H), 8.15 (s, 1H), 8.12-8.06 (m, 2H), 8.05-7.99 (m, 2H), 7.78 (s, 1H), 7.72-7.64 (m, 1H), 7.47-7.35 (m, 5H) 7.26 (s, 1H), 7.19 (d, J = 5.4 Hz, 1H), 5.21 (s, 1H), 4.56 (d, J = 9.6 Hz, 1H), 4.48-4.33 (m, 3H), 4.31-4.17 (m, 3H), 4.00-3.90 (m, 2H), 3.71-3.53 (m, 18H), 2.43 (s, 3H), 2.11-2.02 (m, 1H), 1.96-1.86 (m, 1H), 0.96-0.89 (m, 9H) |
| 108 | I-108 | tert-butyl N-[2-[2-[2-(2-aminoethoxy)-ethoxy]ethoxy]-ethyl]carbamate (CAS# 101187-40-0) | CA | 1026.3$^a$ | 11.12 (br s, 1H), 11.01 (s, 1H), 9.04 (d, J = 4.0 Hz, 2H), 8.65 (t, J = 5.2 Hz, 1H), 8.27 (d, J = 5.2 Hz, 1H), 8.19-8.07 (m, 3H), 8.06-7.97 (m, 3H), 7.85-7.75 (m, 2H), 7.70 (t, J = 6.4 Hz, 1H), 7.49 (d, J = 7.2 Hz, 1H), 7.39 (d, J = 8.4 Hz, 1H), 7.28 (s, 1H), 7.19 (d, J = 5.2 Hz, 1H), 5.19-5.05 (m, 1H), 4.78 (s, 2H), 4.35-4.17 (m, 2H), 3.59-3.49 (m, 12H), 3.48-3.45 (m, 4H), 2.97-2.83 (m, 1H), 2.66-2.61 (m, 1H), 2.60-2.56 (m, 1H), 2.07-2.00 (m, 1H) |
| 109 | I-109 | tert-butyl N-(8-aminooctyl)-carbamate (CAS# 88829-82-7) | CA | 956.4 | 11.12 (s, 1H), 11.01 (s, 1H), 9.03 (d, J = 4.8 Hz, 2H), 8.55 (t, J = 5.6 Hz, 1H), 8.26 (d, J = 5.6 Hz, 1H), 8.14 (s, 1H), 8.12-8.07 (m, 2H), 8.05-7.98 (m, 2H), 7.93 (t, J = 5.6 Hz, 1H), 7.85-7.79 (m, 1H), 7.77 (s, 1H), 7.69 (t, J = 6.4 Hz, 1H), 7.50 (d, J = 7.2 Hz, 1H), 7.40 (d, J = 8.4 Hz, 1H), 7.27 (s, 1H), 7.19 (d, J = 5.2 Hz, 1H), 5.14-5.08 (m, 1H), 4.77 (s, 2H), 4.30-4.20 (m, 2H), 3.29-3.22 (m, 2H), 3.18-3.11 (m, 2H), 2.96-2.85 (m, 1H), 2.64-2.56 (m, 2H), 2.08-2.01 (m, 1H), 1.60-1.38 (m, 4H), 1.29 (s, 8H) |
| 110 | I-110 | tert-butyl N-[2-(2-aminoethoxy)-ethyl]carbamate (CAS# 127828-22-2) | CA | 915.9 | 11.12 (s, 1H), 11.03 (s, 1H), 9.05 (s, 1H), 9.03 (s, 1H), 8.60 (t, J = 5.2 Hz, 1H), 8.27 (d, J = 5.2 Hz, 1H), 8.14 (s, 1H), 8.09-8.05 (m, 2H), 8.05-7.98 (m, 3H), 7.83-7.76 (m, 2H), 7.71 (t, J = 6.4 Hz, 1H), 7.47 (d, J = 7.2 Hz, 1H), 7.39 (d, J = 8.8 Hz, 1H), 7.28 (s, 1H), 7.19 (dd, J = 1.6, 5.2 Hz, 1H), 5.15-5.12 (m, 1H), 4.79 (s, 2H), 4.31-4.20 (m, 2H), 3.61-3.56 (m, 2H), 3.55-3.51 (m, 2H), 3.50-3.44 (m, 2H), 3.40-3.37 (m, 2H), 2.95-2.84 (m, 1H), 2.64-2.55 (m, 2H), 2.10-2.01 (m, 1H) |
| 111 | I-111 | tert-butyl N-(4-aminobutyl)-carbamate (CAS# 68076-36-8) | CA | 900.3 | 11.12 (s, 1H), 11.02 (s, 1H), 9.04 (d, J = 4.0 Hz, 2H), 8.59 (t, J = 5.6 Hz, 1H), 8.26 (d, J = 5.2 Hz, 1H), 8.15-8.08 (m, 3H), 8.02 (m, 3H), 7.85-7.80 (m, 1H), 7.78 (s, 1H), 7.70 (t, J = 6.8 Hz, 1H), 7.49 (d, J = 7.2 Hz, 1H), 7.40 (d, J = 8.4 Hz, 1H), 7.28 (s, 1H), 7.21-7.17 (m, 1H), 5.12 (dd, J = 5.6, 13.2 Hz, 1H), 4.79 (s, 2H), 4.31-4.20 (m, 2H), 3.30-3.26 (m, 2H), 3.24-3.18 (m, 2H), 2.95-2.84 (m, 1H), 2.64-2.54 (m, 2H), 2.07-2.00 (m, 1H), 1.53 (m, 4H) |
| 112 | I-112 | tert-butyl N-(3-aminopropyl)-carbamate | CA | 886.5 | 11.12 (s, 1H), 11.02 (s, 1H), 9.04 (d, J = 2 Hz, 2H), 8.59 (t, J = 6 Hz, 1H), 8.26 (d, J = 5.2 Hz, 1H), 8.17-8.07 (m, 3H), 8.07-7.98 (m, 3H), 7.83 (dd, |

TABLE 7-continued

Compounds synthesized via Method 9 with the coupling of various amines and acids in Step 1, followed by coupling with acid Intermediate CN in Step 3

| Ex-# | I-# | Step 1 Intermediate Amine | Step 1 Intermediate Acid | LCMS (ES+) m/z (M + H)+ | HNMR (400 MHz, DMSO-d6) δ |
|---|---|---|---|---|---|
| | | (CAS# 75178-96-0) | | | J = 7.2, 8.4 Hz, 1H), 7.78 (s, 1H), 7.70 (t, J = 6.4 Hz, 1H), 7.50 (d, J = 7.2 Hz, 1H), 7.42 (d, J = 8.4 Hz, 1H), 7.28 (s, 1H), 7.19 (dd, J = 1.6, 5.2 Hz, 1H), 5.13 (dd, J = 5.2, 12.8 Hz, 1H), 4.80 (s, 2H), 4.31-4.19 (m, 2H), 3.27 (m, 2H), 3.25 (m, 2H), 2.98-2.84 (m, 1H), 2.65-2.54 (m, 2H), 2.09-2.00 (m, 1H), 1.78-1.68 (m, 2H) |
| 113 | I-113 | DH | CH | 1071.3 | 11.03 (s, 1H), 9.05 (d, J = 3.2 Hz, 2H), 8.65 (t, J = 5.2 Hz, 1H), 8.31 (t, J = 6.4 Hz, 1H), 8.26 (d, J = 5.2 Hz, 1H), 8.15 (s, 1H), 8.13-8.08 (m, 3H), 8.06-8.00 (m, 2H), 7.78 (br s, 1H), 7.71 (t, J = 6.8 Hz, 1H), 7.66 (d, J = 8.0 Hz, 2H), 7.34 (d, J = 8.0 Hz, 2H), 7.28 (s, 1H), 7.19 (dd, J = 1.2, 5.2 Hz, 1H), 6.72 (d, J = 7.6 Hz, 1H), 6.62 (d, J = 7.6 Hz, 1H), 4.34 (d, J = 6.0 Hz, 2H), 4.30-4.20 (m, 2H), 3.95 (s, 2H), 3.62-3.40 (m, 16H), 2.56-2.54 (m, 3H) |
| 114 | I-114 | DH | DI | 1115.8 | 11.03 (s, 1H), 9.05 (d, J = 3.2 Hz, 2H), 8.65 (br t, J = 5.2 Hz, 1H), 8.31 (br t, J = 6.4 Hz, 1H), 8.26 (d, J = 5.2 Hz, 1H), 8.14 (br s, 1H), 8.13-8.08 (m, 3H), 8.06-8.01 (m, 2H), 7.78 (br s, 1H), 7.71 (br t, J = 6.3 Hz, 1H), 7.66 (d, J = 8.4 Hz, 2H), 7.35 (d, J = 8.4 Hz, 2H), 7.28 (s, 1H), 7.21-7.16 (m, 1H), 6.72 (d, J = 7.6 Hz, 1H), 6.61 (d, J = 7.6 Hz, 1H), 4.34 (br d, J = 6.0 Hz, 2H), 4.30-4.20 (m, 2H), 3.95 (s, 2H), 3.62-3.41 (m, 20H), 2.54-2.53 (s, 3H) |
| 115 | I-115 | CI | DM | 1117.4 | 11.02 (s, 1H), 9.04 (d, J = 4.0 Hz, 2H), 8.97 (s, 1H), 8.64 (t, J = 5.2 Hz, 1H), 8.59 (t, J = 6.0 Hz, 1H), 8.26 (d, J = 5.2 Hz, 1H), 8.13 (s, 1H), 8.11-8.08 (m, 2H), 8.05-8.01 (m, 2H), 7.77 (s, 1H), 7.70 (t, J = 6.4 Hz, 1H), 7.47-7.36 (m, 5H), 7.28 (s, 1H), 7.18 (dd, J = 1.2, 5.2 Hz, 1H), 5.16 (s, 1H), 4.57 (d, J = 9.6 Hz, 1H), 4.49-4.34 (m, 3H), 4.31-4.23 (m, 3H), 3.97 (s, 2H), 3.71-3.65 (m, 1H), 3.61-3.54 (m, 10H), 3.47-3.42 (m, 2H), 2.53 (d, J = 2.0 Hz, 1H), 2.44 (s, 3H), 2.11-2.02 (m, 1H), 1.94-1.87 (m, 1H), 0.96-0.91 (m, 9H) |

Variations in reaction time for Method 9 were as follows: Step 1 was run anywhere from 0.5-12 h, Step 3 anywhere from 0.5-12 h, and Step 4 anywhere from 0.5-12 hr.
[a]mass measured as (M + Na)+.

2185

Further Examples Using Synthetic Methods Similar to Method 9

Example 116: N-(3-carbamoyl-1-(4-((2-((5-(2-(2-((2-(2,6-dioxopiperidin-3-yl)-1,3-dioxoisoindolin-4-yl)oxy) acetamido)ethoxy)pentyl)oxy)ethyl)carbamoyl)phenyl)-1H-pyrazol-4-yl)-2-(2-((2,2,2-trifluoroethyl)amino)pyridin-4-yl)oxazole-4-carboxamide, I-116

2186

(2-((2,2,2-trifluoroethyl)amino)pyridin-4-yl)oxazole-4-carboxamide I-116 was synthesized via Method 9, by coupling amine Intermediate CF with acid Intermediate CN in Step 1. Step 2 was not performed as the amine did not have a BOC group for deprotection. In Step 3, Intermediate CA was employed as the acid for the coupling. Characterization of the final product: $^1$H NMR (400 MHz, DMSO-d6) δ 11.12 (s, 1H), 11.00 (s, 1H), 9.02 (d, J=8.4 Hz, 2H), 8.64 (t, J=5.2 Hz, 1H), 8.26 (d, J=5.2 Hz, 1H), 8.14 (s, 1H), 8.11-8.06 (m, 2H), 8.05-8.00 (m, 2H), 7.97 (t, J=6.4 Hz, 1H),

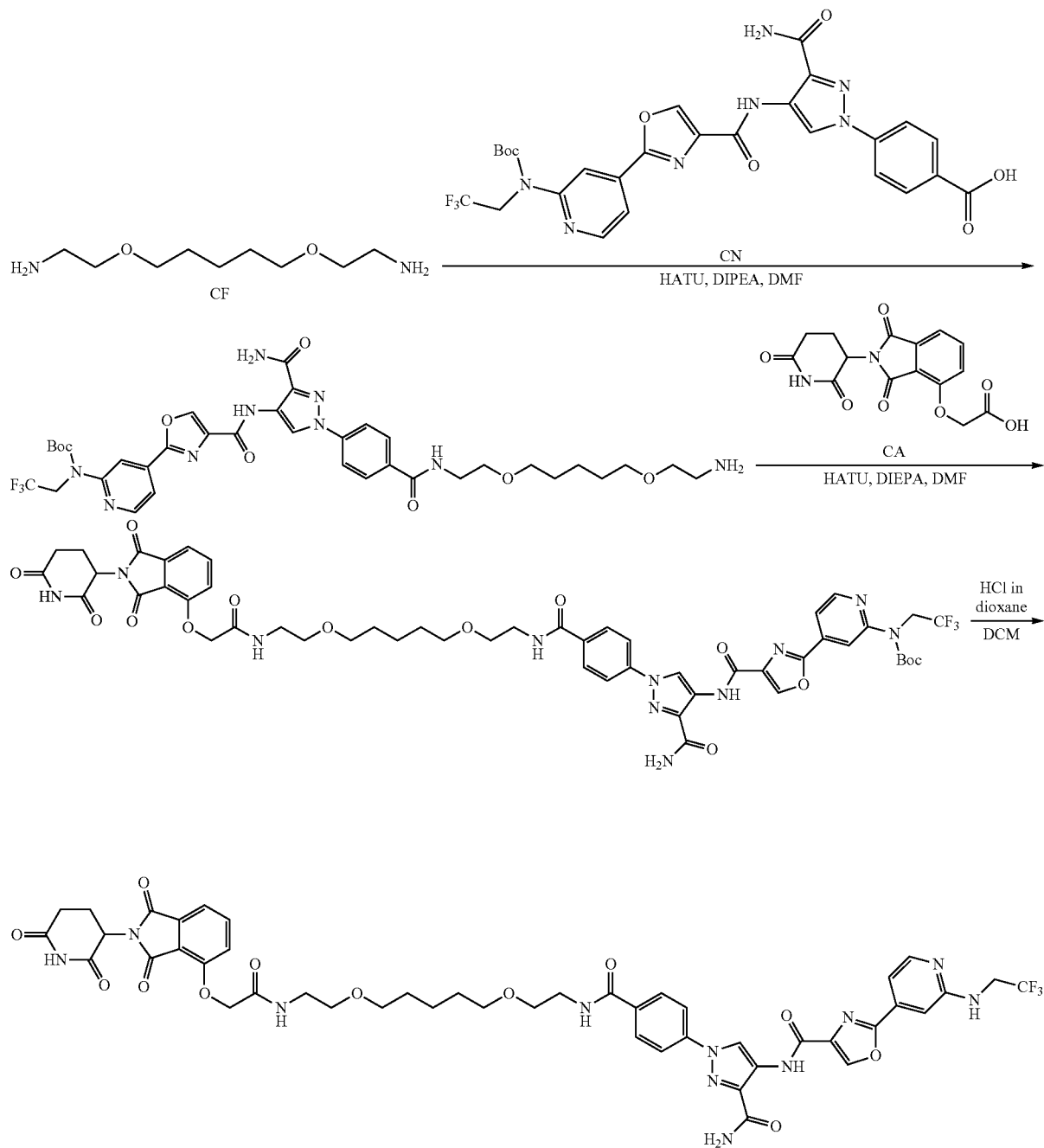

N-(3-carbamoyl-1-(4-((2-((5-(2-(2-((2-(2,6-dioxopiperidin-3-yl)-1,3-dioxoisoindolin-4-yl)oxy) acetamido)ethoxy)pentyl)oxy)ethyl)carbamoyl)phenyl)-1H-pyrazol-4-yl)-2-

7.82-7.75 (m, 2H), 7.69 (t, J=6.4 Hz, 1H), 7.48 (d, J=7.2 Hz, 1H), 7.38 (d, J=8.4 Hz, 1H), 7.26 (s, 1H), 7.20-7.16 (m, 1H), 5.10 (dd, J=5.2, 12.8 Hz, 1H), 4.78 (s, 2H), 4.30-4.18 (m,

2H), 3.40-3.28 (m, 12H), 2.94-2.84 (m, 1H), 2.65-2.60 (m, 1H), 2.52-2.44 (m, 1H), 2.08-2.02 (m, 1H), 1.53-1.44 (m, 4H), 1.35-1.27 (m, 2H). LC-MS (ESI$^+$) m/z 1002.4 (M+H)$^+$.
Example 117: N-(3-carbamoyl-1-(4-((2-(2-(2-((2-(2,6-dioxopiperidin-3-yl)-1-oxoisoindolin-4-yl)amino)ethoxy)ethoxy)ethyl)carbamoyl)phenyl)-1H-pyrazol-4-yl)-2-(2-((2,2,2-trifluoroethyl)amino)pyridin-4-yl)oxazole-4-carboxamide, I-117
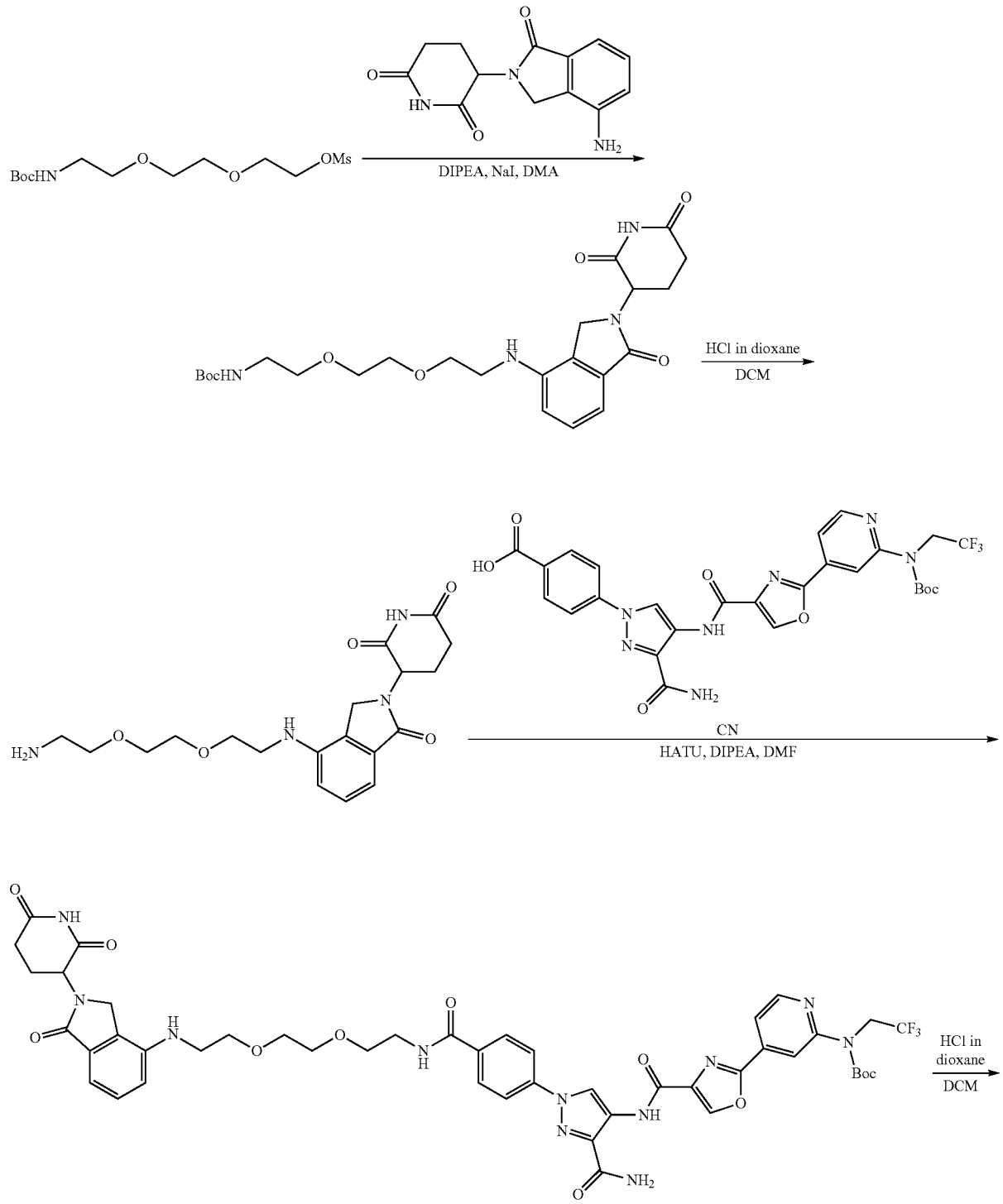

2189 2190
-continued

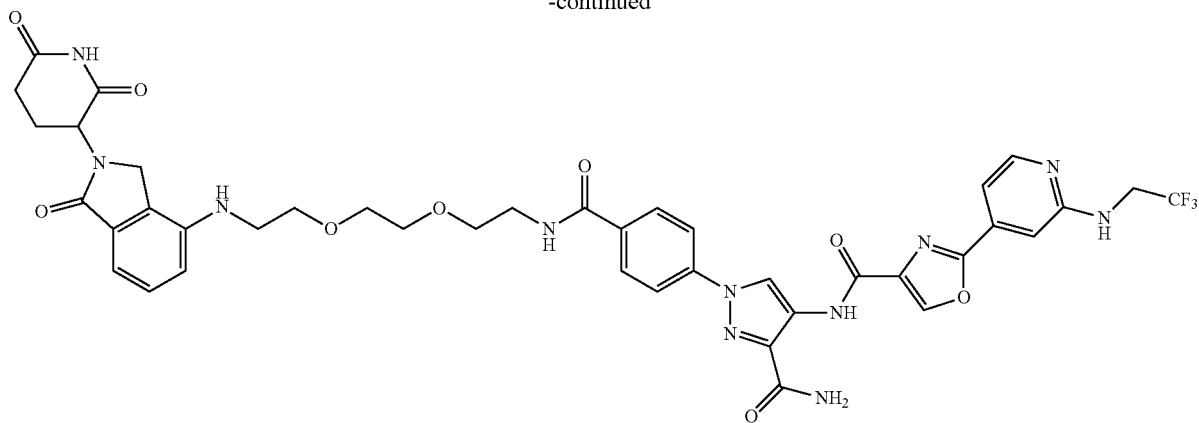

Tert-butyl (2-(2-(2-((2-(2,6-dioxopiperidin-3-yl)-1-oxoisoindolin-4-yl)amino)ethoxy)ethoxy)ethyl)carbamate was synthesized in Step 1 as follows: To a mixture of 3-(4-amino-1-oxo-isoindolin-2-yl)piperidine-2,6-dione (0.10 g, 385 umol, CAS #191732-72-6) in DMA (2 mL) was added 2-[2-[2-(tert-butoxycarbonylamino)ethoxy]ethoxy]ethyl methanesulfonate (151 mg, 462 umol, synthesized via Step 1 of Intermediate AI), NaI (17.3 mg, 115 umol) and DIPEA (149 mg, 1.16 mmol, 201 uL). Then the reaction mixture was stirred at 80° C. for 2 hours. On completion, the reaction mixture was concentrated in vacuo. The residue was purified by prep-TLC (PE:EA=0:1) to give the title compound I-117 (0.18 g, 50% purity, 47% yield) as a yellowish solid (LC-MS (ESI$^+$) m/z 513.1 (M+Na)+).

Steps 2-4 followed Method 9, where Intermediate CN was used as the acid in Step 3 which was coupled with the amine at rt for 12 hours. Characterization of the final product: $^1$H NMR (400 MHz, DMSO-d$_6$) δ 11.13-10.90 (m, 2H), 9.04 (s, 2H), 8.65 (t, J=5.2 Hz, 1H), 8.26 (d, J=5.2 Hz, 1H), 8.16-8.07 (m, 3H), 8.05-7.99 (m, 2H), 7.78 (s, 1H), 7.70 (t, J=6.4 Hz, 1H), 7.32-7.24 (m, 2H), 7.19 (dd, J=1.2, 5.2 Hz, 1H), 6.94 (d, J=7.2 Hz, 1H), 6.79 (d, J=8.0 Hz, 1H), 5.58 (s, 1H), 5.11 (dd, J=5.2, 13.2 Hz, 1H), 4.29-4.11 (m, 4H), 3.77-3.52 (m, 8H), 3.49-3.41 (m, 4H), 2.97-2.87 (m, 1H), 2.64-2.59 (m, 2H), 2.05-2.03 (m, 1H). LC-MS (ESI$^+$) m/z 888.1 (M+H)$^+$.

Example 118 (Method 10): [2-[2-[[(1S)-1-[(4R)-4-hydroxy-2-[[4-(4-methylthiazol-5-yl)phenyl]methylcarbamoyl]pyrrolidine-1-carbonyl]-2,2-dimethylpropyl]amino]-2-oxo-ethoxy]ethoxy]ethoxy]ethoxy]-3-methyl-butyl]pyridine-3-carboxamide, I-118

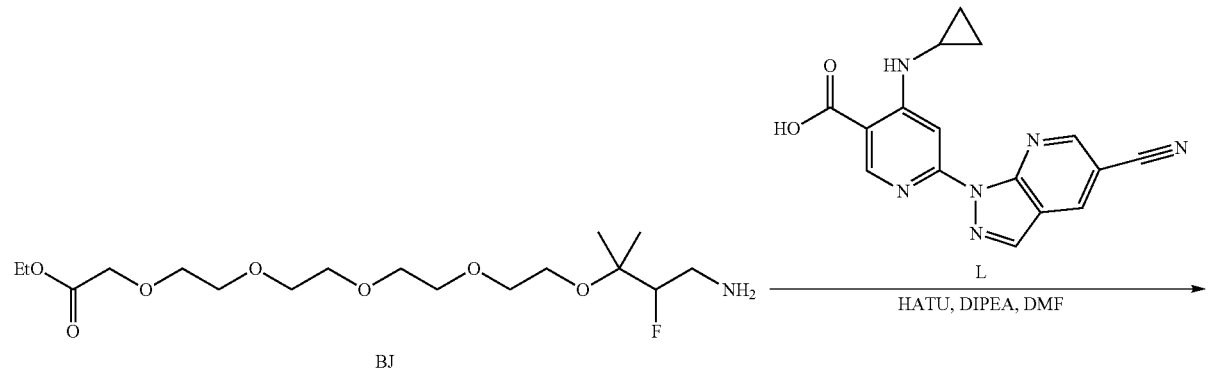

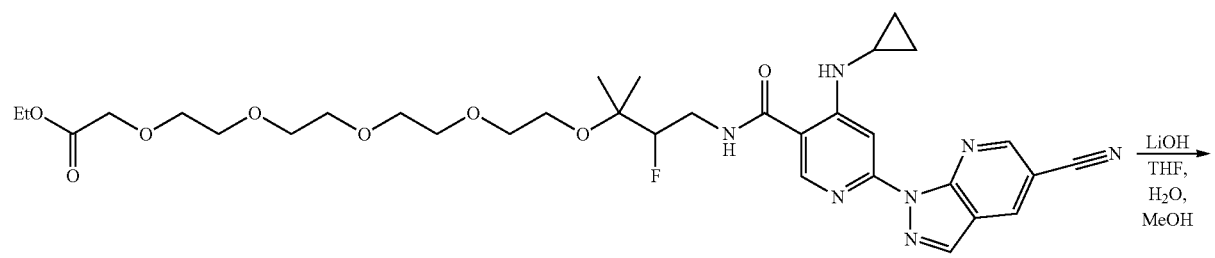

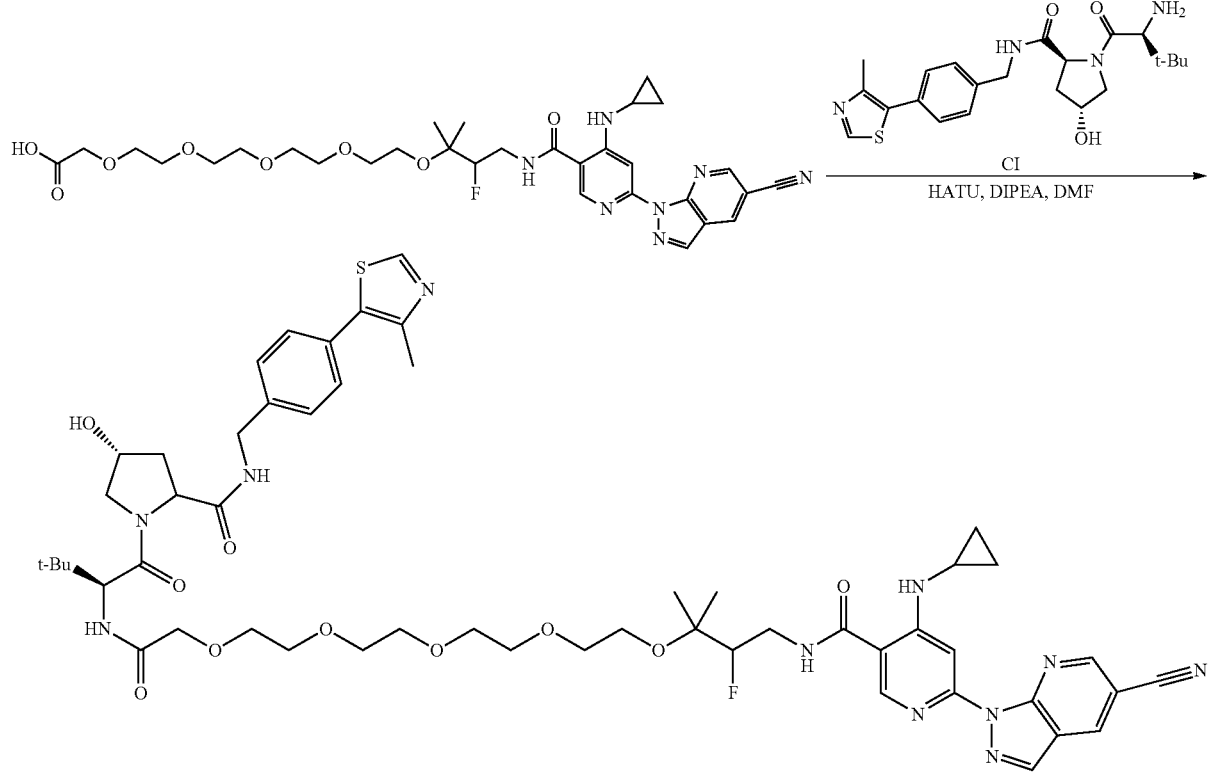

Step 1—Ethyl 2-[2-[2-[2-[2-[3-[[6-(5-cyanopyrazolo[3,4-b]pyridin-1-yl)-4-(cyclopropylamino)pyridine-3-carbonyl]amino]-2-fluoro-1,1-dimethyl-propoxy]ethoxy]ethoxy]ethoxy]ethoxy]acetate To a mixture of ethyl 2-[2-[2-[2-[2-(3-amino-2-fluoro-1,1-dimethyl-propoxy)ethoxy]ethoxy]ethoxy]ethoxy]acetate (200 mg, 521 umol, Intermediate BJ) and DIPEA (337 mg, 2.61 mmol) in DMF (3 mL) was added 6-(5-cyanopyrazolo[3,4-b]pyridin-1-yl)-4-(cyclopropylamino)pyridine-3-carboxylic acid (271 mg, 625 umol, Intermediate L as the TFA salt) and HATU (257 mg, 678 umol). The reaction mixture was stirred at rt for 1 hour. On completion, the reaction mixture was concentrated in vacuo. The residue was purified by prep-HPLC (0.1% FA) to give the title compound (80.0 mg, 22% yield) as a red oil. LC-MS (ESI⁺) m/z 686.6 (M+H)⁺.

Step 2—2-[2-[2-[2-[2-[3-[[6-(5-Cyanopyrazolo[3,4-b]pyridin-1-yl)-4-(cyclopropylamino)pyridine-3-carbonyl]amino]-2-fluoro-1,1-dimethyl-propoxy]ethoxy]ethoxy]ethoxy]ethoxy]acetic acid To a mixture of ethyl 2-[2-[2-[2-[2-[3-[[6-(5-cyanopyrazolo[3,4-b]pyridin-1-yl)-4-(cyclopropylamino)pyridine-3-carbonyl]amino]-2-fluoro-1,1-dimethyl-propoxy]ethoxy]ethoxy]ethoxy]ethoxy]acetate (70.0 mg, 102 umol) in THF (4 mL) and MeOH (1 mL) was added a solution of LiOH (4.89 mg, 204 umol) in H₂O (1 mL). The reaction mixture was stirred at rt for 0.5 hour. On completion, the reaction mixture was acidified with HCl (1 N) until the pH=5-6, then concentrated in vacuo to give a residue. The residue was purified by prep-HPLC (column: Phenomenex Synergi C18 150*30 mm*4 um; mobile phase: [water (0.05% HCl)-ACN]) to give the title compound (20.0 mg, 29% yield) as a light yellow oil. LC-MS (ESI⁺) m/z 658.1 (M+H)⁺.

Step 3—6-(5-Cyanopyrazolo[3,4-b]pyridin-1-yl)-4-(cyclopropylamino)-N-[2-fluoro-3-[2-[2-[2-[2-[[(1S)-1-[(4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethoxy]ethoxy]-3-methyl-butyl]pyridine-3-carboxamide To a mixture of (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide (21.3 mg, 45.6 umol, Intermediate CI, as the HCl salt) and DIPEA (29.4 mg, 228 umol) in DMF (3 mL) was added 2-[2-[2-[2-[2-[3-[[6-(5-cyanopyrazolo[3,4-b]pyridin-1-yl)-4-(cyclopropylamino)pyridine-3-carbonyl]amino]-2-fluoro-1,1-dimethyl-propoxy]ethoxy]ethoxy]ethoxy]ethoxy]acetic acid (30.0 mg, 45.6 umol) and HATU (20.8 mg, 54.7 umol). The reaction mixture was stirred at rt for 0.5 hour. On completion, the reaction mixture was concentrated in vacuo. The residue was purified by prep-HPLC (column: Phenomenex Synergi C18 150*25*10 um; mobile phase: [water (0.225% FA)-ACN]) to give the title compound I-118 (10.9 mg, 21% yield) as a yellow solid. ¹H NMR (400 MHz, DMSO-d₆) δ 9.07 (s, 1H), 9.03 (d, J=2.0 Hz, 1H), 8.98 (s, 1H), 8.87 (t, J=5.2 Hz, 1H), 8.72-8.58 (m, 4H), 7.76 (s, 1H), 7.49-7.34 (m, 5H), 4.57 (d, J=9.6 Hz, 1H), 4.48-4.43 (m, 1H), 4.43-4.37 (m, 1H), 4.35 (s, 1H), 4.30-4.21 (m, 1H), 3.97 (s, 2H), 3.66-3.50 (m, 20H), 2.59 (s, 1H), 2.54-2.53 (m, 1H), 2.44 (s, 3H), 2.10-2.01 (m, 1H), 1.93-1.87 (m, 1H), 1.21 (s, 6H), 0.94 (s, 9H), 0.89-0.84 (m, 2H), 0.58 (d, J=2.0 Hz, 2H). LC-MS (ESI⁺) m/z 1070.1 (M+H)⁺.

TABLE 8

Compounds synthesized via Method 10 with the coupling of various acids and amines in Step 1, followed by coupling with an amine in Step 3.

| Ex-# | I-# | Step 1 Intermediate Amine | Step 1 Intermediate Acid | Step 3 Intermediate Amine | LCMS (ES+) m/z (M + H)+ | HNMR (400 MHz, DMSO-d6) δ |
|---|---|---|---|---|---|---|
| 119 | I-119 | BW | N | CI | 1087.6 | 10.38 (s, 1H), 9.06 (s, 1H), 8.99 (s, 1H), 8.63-8.52 (m, 5H), 8.47 (s, 1H), 8.31 (s, 1H), 8.28 (d, J = 9.2 Hz, 1H), 7.57 (d, J = 5.6 Hz, 1H), 7.51 (d, J = 8.8 Hz, 1H), 7.46-7.37 (m, 5H), 4.84-4.68 (m, 1H), 4.57 (d, J = 9.6 Hz, 1H), 4.48-4.43 (m, 1H), 4.42-4.37 (m, 1H), 4.36 (s, 1H), 4.29-4.22 (m, 1H), 3.97 (s, 2H), 3.56-3.48 (m, 24H), 2.62 (s, 2H), 2.46-2.45 (m, 1H), 2.44 (s, 3H), 2.09-2.02 (m, 1H), 1.96-1.85 (m, 1H), 0.95 (s, 9H), 0.93 (s, 2H), 0.59 (s, 2H) |
| 120 | I-120 | BX | N | CI | 955.5 | 10.4 (s, 1H), 9.06 (s, 1H), 8.97 (s, 1H), 8.63-8.52 (m, 3H), 8.47 (s, 1H), 8.27 (d, J = 8.8 Hz, 1H), 7.57 (d, J = 6.0 Hz, 1H), 7.51 (d, J = 8.8 Hz, 1H), 7.45 (d, J = 9.6 Hz, 1H), 7.40 (s, 4H), 4.85-4.65 (m, 1H), 1H), 4.48-4.37 (m, 2H), 4.36 (s, 1H), 4.30-4.23 (m, 1H), 3.98 (s, 2H), 3.73-3.52 (m, 15H), 3.32-3.25 (m, 1H), 2.69-2.65 (m, 1H), 2.71-2.60 (m, 1H), 2.43(s, 3H), 2.05 (m, 1H), 1.90 (m, 1H), 0.98-0.92 (m, 11H), 0.59 (s, 2H) |
| 121 | I-121 | BL | L | CI | 1056.6 | 9.06 (d, J = 2.0 Hz, 1H), 9.02 (d, J = 2.0 Hz, 1H), 8.98 (s, 1H), 8.86-8.80 (m, 1H), 8.66 (s, 1H), 8.63 (s, 1H), 8.62-8.55 (m, 2H), 7.72 (s, 1H), 7.45-7.38 (m, 5H), 5.20-5.15 (m, 1H), 4.70-4.61 (m, 1H), 4.56-4.5 (m, 1H), 4.47-4.33 (m, 3H), 4.29-4.21 (m, 1H), 3.96 (s, 2H), 3.72-3.48 (m, 16H), 2.62-2.57 (m, 1H), 2.55-2.52 (m, 4H), 2.43 (s, 3H), 2.07-2.00 (m, 1H), 1.94-1.86 (m, 1H), 1.27-1.22 (m, 1H), 1.19-1.14 (m, 3H), 0.94 (s, 9H), 0.88-0.84 (m, 2H), 0.59-0.54 (m, 2H) |
| 122ᵃ | I-122 | BM | L | CI | 968.1 | 9.05 (s, 1H), 9.01 (d, J = 2.0 Hz, 1H), 8.96 (s, 1H), 8.83 (d, J = 5.6 Hz, 1H), 8.66 (s, 1H), 8.65-8.53 (m, 3H), 7.72 (s, 1H), 7.46-7.36 (m, 5H), 5.19 (s, 1H), 4.69-4.61 (m, 1H), 4.69- |

TABLE 8-continued

Compounds synthesized via Method 10 with the coupling of various acids and amines in Step 1, followed by coupling with an amine in Step 3.

| Ex-# | I-# | Step 1 Intermediate Amine | Step 1 Intermediate Acid | Step 3 Intermediate Amine | LCMS (ES+) m/z (M + H)+ | HNMR (400 MHz, DMSO-d6) δ |
|---|---|---|---|---|---|---|
| | | | | | | 4.61 (m, 1H), 4.59-4.50 (m, 2H), 4.49-4.40 (m, 2H), 4.39-4.33 (m, 2H), 4.29-4.22 (m, 1H), 3.98 (s, 2H), 3.63-3.60 (m, 10H), 2.59-2.56 (m, 2H), 2.43 (s, 3H), 2.10-2.02 (m, 1H), 1.92-1.90 (m, 1H), 1.17-1.11 (m, 3H), 0.94 (s, 9H), 0.89-0.83 (m, 2H), 0.56 (s, 2H) |
| 123 | I-123 | CI | DT | DR | 1150.6 | 8.98 (s, 1H), 8.60 (br t, J = 6.0 Hz, 1H), 8.52 (s, 1H), 7.45-7.39 (m, 5H), 7.19-7.16 (m, 1H), 7.13-7.10 (m, 1H), 5.48-5.42 (m, 1H), 5.21-5.11 (m, 2H), 4.60-4.54 (m, 1H), 4.48-4.38 (m, 2H), 4.37-4.34 (m, 1H), 4.28-4.23 (m, 1H), 4.16-4.10 (m, 2H), 3.97 (s, 2H), 3.94-3.66 (m, 1H), 3.63-3.53 (m, 16H), 3.49 (s, 7H), 3.06-3.00 (m, 1H), 2.95-2.88 (m, 1H), 2.61-2.54 (m, 2H), 2.44 (s, 3H), 2.42-2.38 (m, 3H), 2.37-2.02 (m, 4H), 1.95-1.89 (m, 1H), 1.88-1.81 (m, 2H), 1.71-1.35 (m, 6H), 0.94 (s, 9H) |

Variations in reaction time for Method 10 were as follows: Step 1 was run anywhere from 0.5-12 h, Step 2 anywhere from 0.5-3.5 h, and Step 3 anywhere from 0.5-3 hr.
<sup>a</sup>Product isolated as the FA salt.

Further Examples Using Synthetic Methods Similar to Method 10

Example 124: (2S,4R)-1-[(2S)-2-[[2-[2-[2-[2-[2-[2-[4-[4-[[(8R)-8-[(2S)-3-amino-2-hydroxy-3-oxo-propyl]-7,8-dihydro-6H-cyclopenta[4,5]thieno[1,2-c]pyrimidin-1-yl]oxy]cyclohexyl]piperazin-1-yl]ethoxy]ethoxy]ethoxy]ethoxy]ethoxy]acetyl]amino]-3,3-dimethyl-butanoyl]-4-hydroxy-N-[[4-(4-methylthiazol-5-yl)phenyl]methyl]pyrrolidine-2-carboxamide, I-124

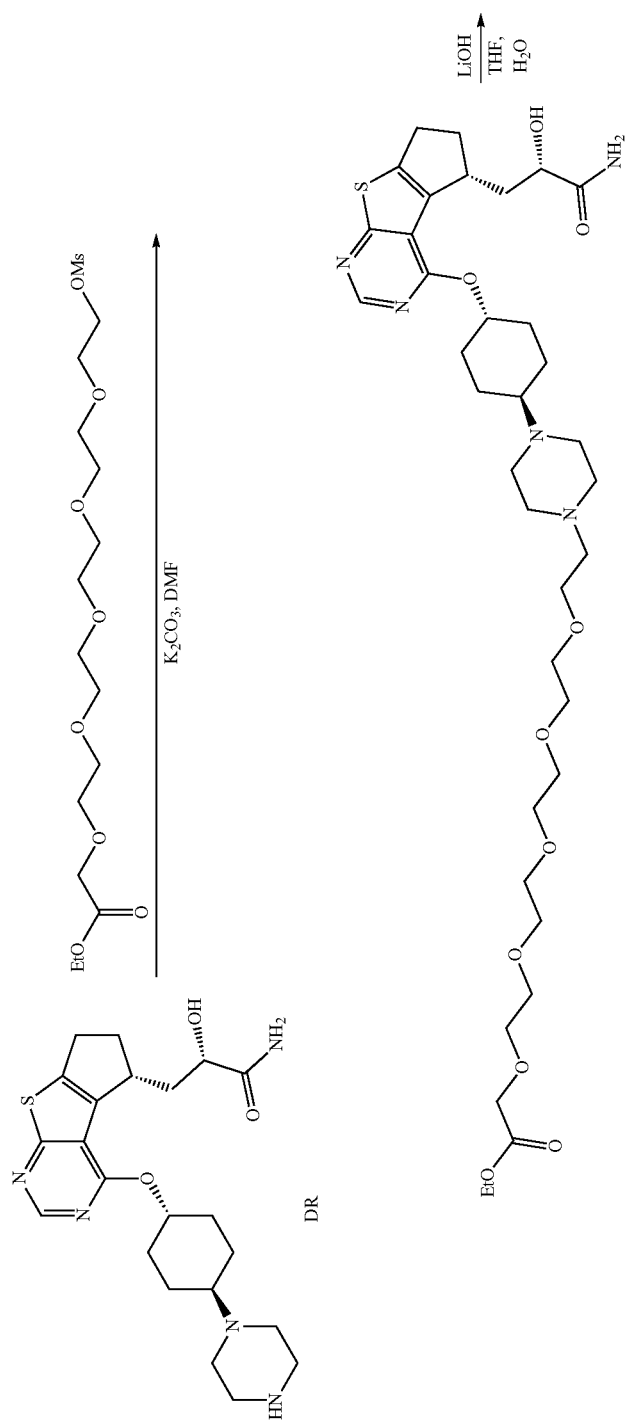

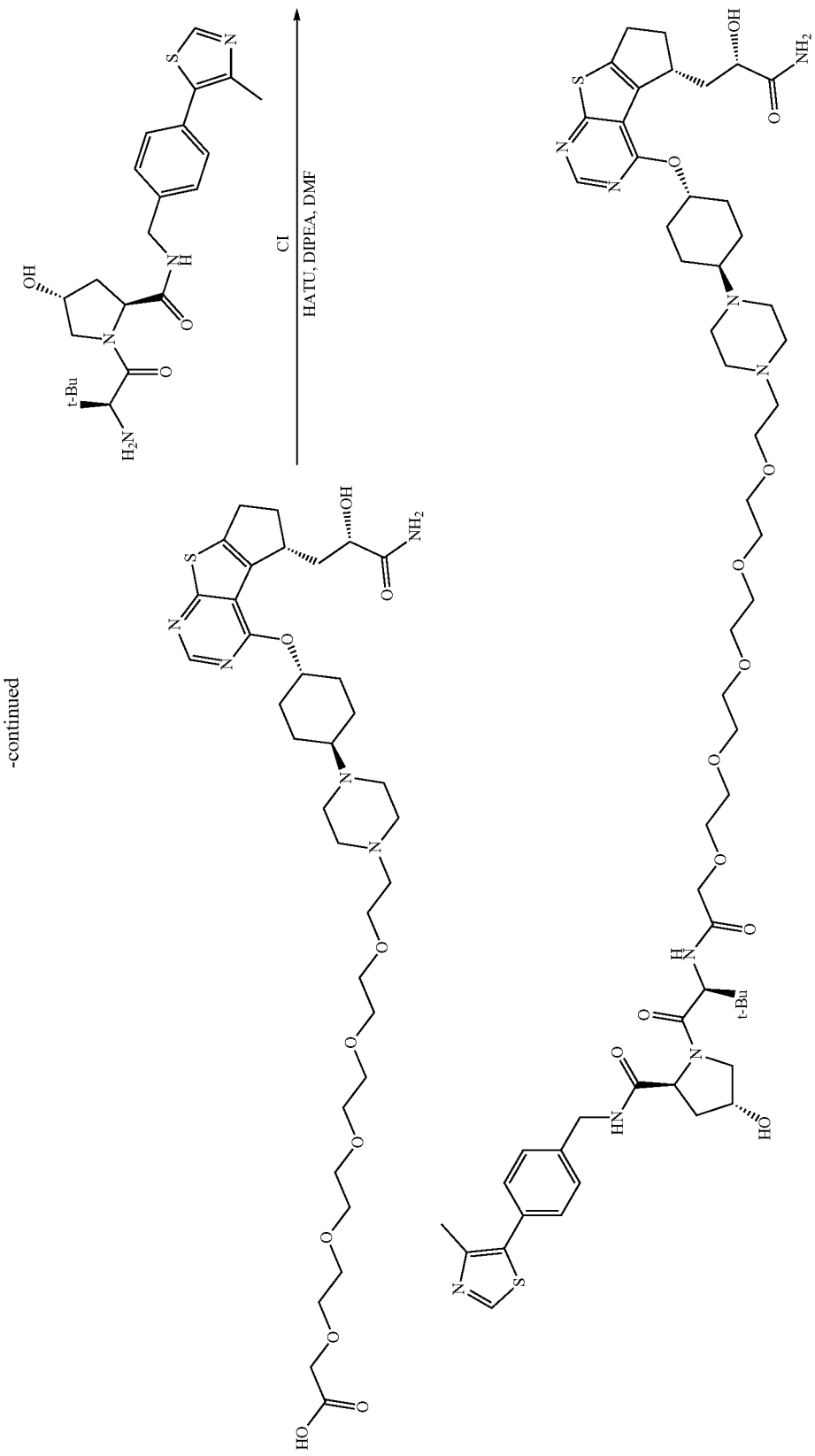

Ethyl 2-[2-[2-[2-[2-[2-[4-[4-[[(8R)-8-[(2S)-3-amino-2-hydroxy-3-oxo-propyl]-7,8-dihydro-6H-cyclopenta[4,5]thieno[1,2-c]pyrimidin-1-yl]oxy]cyclohexyl]piperazin-1-yl]ethoxy]ethoxy]ethoxy]ethoxy]acetate was synthesized as follows: to a solution of (2S)-2-hydroxy-3-[(8R)-1-(4-piperazin-1-ylcyclohexoxy)-7,8-dihydro-6H-cyclopenta[4,5]thieno[1,2-c]pyrimidin-8-yl]propanamide (90.0 mg, 187 umol, Intermediate DR) in DMF (5 mL) was added K$_2$CO$_3$ (129 mg, 933 umol) and ethyl 2-[2-[2-[2-[2-(2-methylsulfonyloxyethoxy)ethoxy]ethoxy]ethoxy]ethoxy]acetate (113 mg, 280 umol, synthesized via Steps 1-2 of Intermediate BW). The reaction mixture was stirred at 60° C. for 25 h. On completion, the reaction mixture was concentrated in vacuo to give the title compound (130 mg, 92% yield) as a yellow solid (LC-MS (ESI$^+$) m/z 752.4 (M+H)$^+$). The final product was then synthesized via Steps 2-3 of Method 10, where Step 2 was run for 15 h at rt and Step 3 was run for 3 h at rt using acid Intermediate CI. Characterization of the final product I-124: $^1$H NMR (400 MHz, DMSO-d$_6$) δ 8.98 (s, 1H), 8.60 (t, J=6.0 Hz, 1H), 8.52 (s, 1H), 8.22 (s, 1H), 7.42 (d, J=9.6 Hz, 2H), 7.39 (s, 2H), 7.15 (s, 1H), 7.11 (s, 1H), 5.18-5.12 (m, 1H), 4.57 (d, J=9.6 Hz, 1H), 4.47-4.40 (m, 2H), 4.40-4.33 (m, 2H), 4.25 (dd, J=5.6, 15.8 Hz, 2H), 3.97 (s, 2H), 3.95-3.90 (m, 2H), 3.68-3.48 (m, 20H), 3.05-2.98 (m, 1H), 2.94-2.87 (m, 1H), 2.61-2.53 (m, 2H), 2.44 (s, 12H), 2.16-2.04 (m, 3H), 1.92-1.83 (m, 3H), 1.69-1.58 (m, 2H), 1.57-1.41 (m, 2H), 1.41-1.32 (m, 2H), 0.94 (s, 9H); LC-MS (ESI$^+$) m/z 1136.1 (M+H)$^+$.

Example 125: N-[3-carbamoyl-1-[4-[8-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]octylcarbamoyl]phenyl]pyrazol-4-yl]-2-[2-(2,2,2-trifluoroethylamino)-4-pyridyl]oxazole-4-carboxamide, I-125

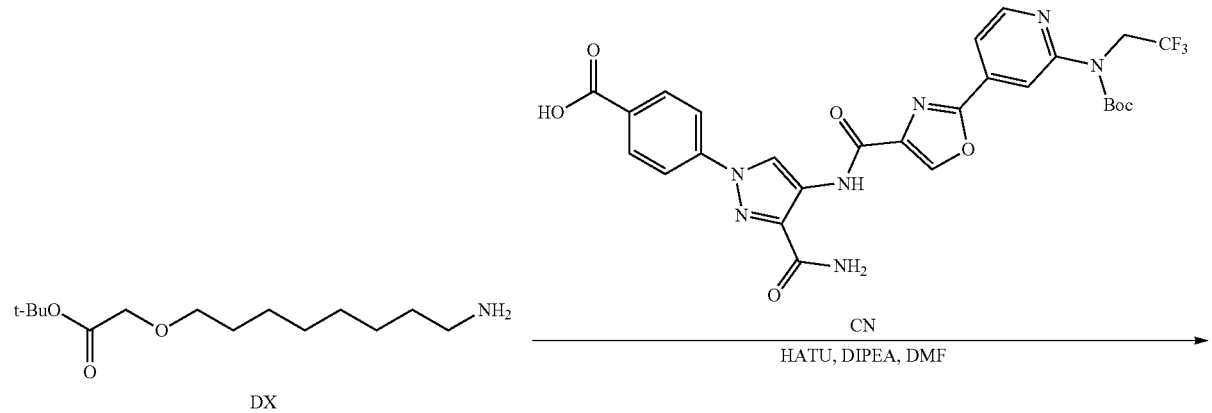

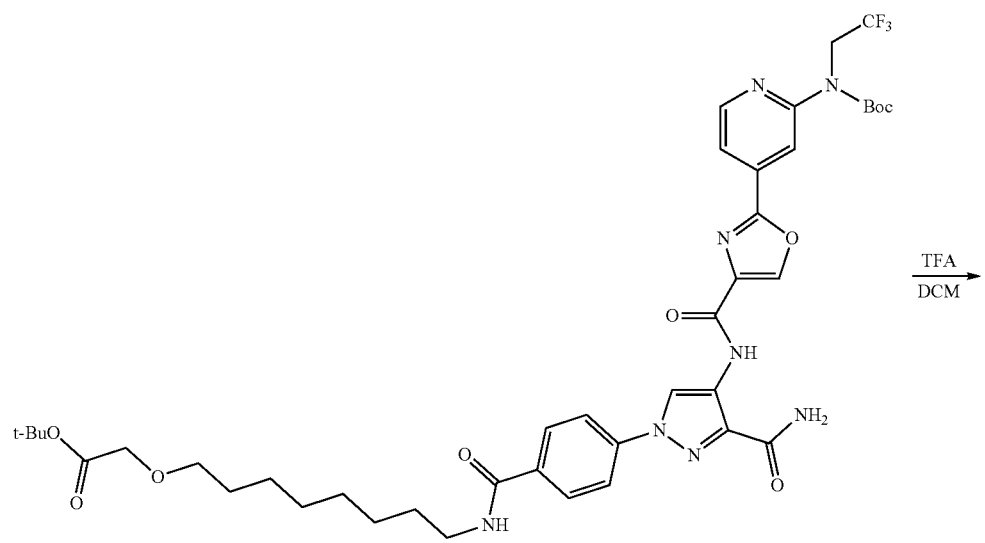

2203

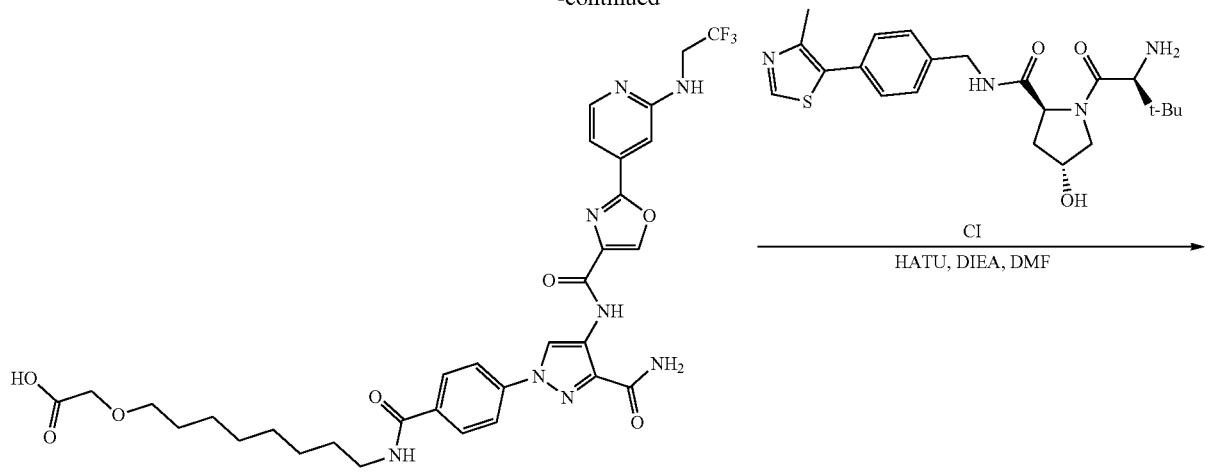

2204

Tert-butyl 2-[8-[[4-[4-[[2-[2-[tert-butoxycarbonyl(2,2,2-trifluoroethyl)amino]-4-pyridyl]oxazole-4-carbonyl]amino]-3-carbamoyl-pyrazol-1-yl]benzoyl]amino]octoxy]acetate was synthesized via Method 10, Step1, where amine Intermediate DX and acid Intermediate CN were coupled at rt for 2 hours. In Step 2, the Boc groups were removed as follows: to a solution of tert-butyl 2-[8-[[4-[4-[[2-[2-[tert-butoxycarbonyl(2,2,2-trifluoroethyl)amino]-4-pyridyl]oxazole-4-carbonyl]amino]-3-carbamoyl-pyrazol-1-yl]benzoyl]amino]octoxy]acetate (120 mg, 134 umol) in DCM (3 mL) was added TFA (760 mg, 6.75 mmol). The mixture was stirred at rt for 3 hours. On completion, the reaction mixture was concentrated in vacuo to give the title compound (110 mg, 100% yield, TFA salt) as light yellow oil (LC-MS (ESI$^+$) m/z 701.4 (M+H)$^+$). The third step followed Method 10, where amine Intermediate CI was coupled with the acid at rt for 3 hours. Characterization of the final product I-125: $^1$H NMR (400 MHz, DMSO-d$_6$) δ 11.02 (s, 1H), 9.04 (d, J=2.0 Hz, 2H), 8.97 (s, 1H), 8.61 (t, J=6.0 Hz, 1H), 8.54 (t, J=6.0 Hz, 1H), 8.25 (d, J=5.6 Hz, 1H), 8.13 (s, 1H), 8.08 (d, J=8.8 Hz, 2H), 8.02 (d, J=8.8 Hz, 2H), 7.77 (s, 1H), 7.70 (t, J=6.4 Hz, 1H), 7.47-7.31 (m, 5H), 7.27 (s, 1H), 7.20-7.16 (m, 1H), 5.16 (d, J=3.6 Hz, 1H), 4.56 (d, J=9.6 Hz, 1H), 4.48-4.32 (m, 3H), 4.29-4.19 (m, 3H), 3.91 (s, 2H), 3.71-3.57 (m, 2H), 3.49-3.44 (m, 2H), 3.29-3.21 (m, 2H), 2.43 (s, 3H), 2.11-2.01 (m, 1H), 1.95-1.84 (m, 1H), 1.59-1.47 (m, 4H), 1.36-1.23 (m, 8H), 0.93 (s, 9H); LC-MS (ESI$^+$) m/z 1113.5 (M+H)$^+$.

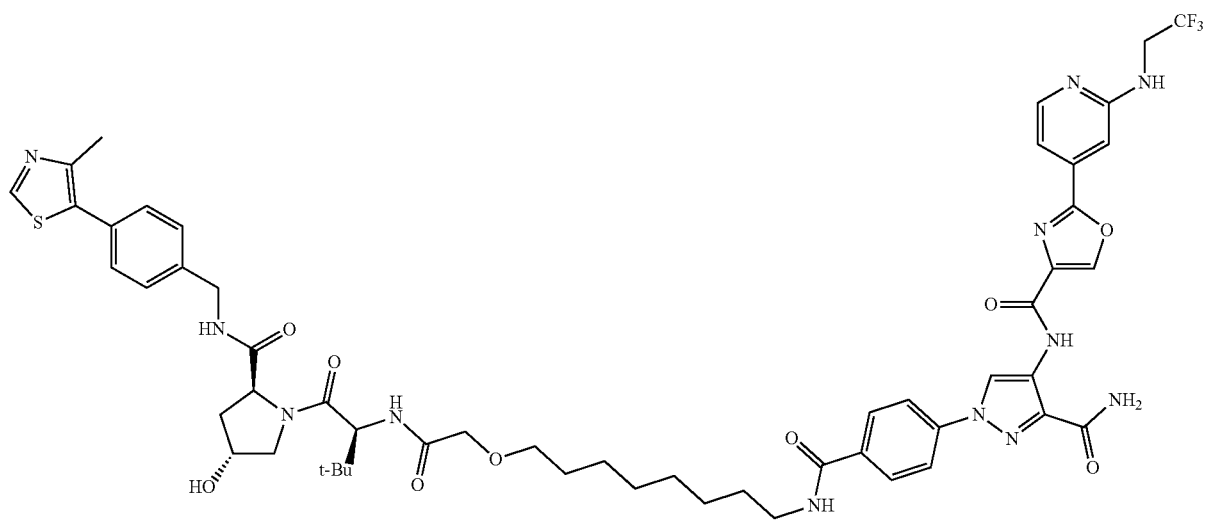 [SMILES: Cc1ncsc1-c1ccc(CNC(=O)[C@@H]2C[C@@H](O)CN2C(=O)[C@@H](NC(=O)COCCCCCCCCNC(=O)c2ccc(-n3cc(NC(=O)c4coc(-c5ccnc(NCC(F)(F)F)c5)n4)c(C(N)=O)n3)cc2)C(C)(C)C)cc1]

Example 126: 4-[2-[4-[2-[2-[2-[2-[[2-(2,6-Dioxo-3-piperidyl)-1,3-dioxo-isoindolin-4-yl]amino]ethoxy]ethoxy]ethoxy]ethylcarbamoyl]phenyl]ethynyl]-1-[[1 (2S,3S,4S)-3-ethyl-4-fluoro-5-oxo-pyrrolidin-2-yl]methoxy]-7-methoxy-isoquinoline-6-carboxamide, I-126
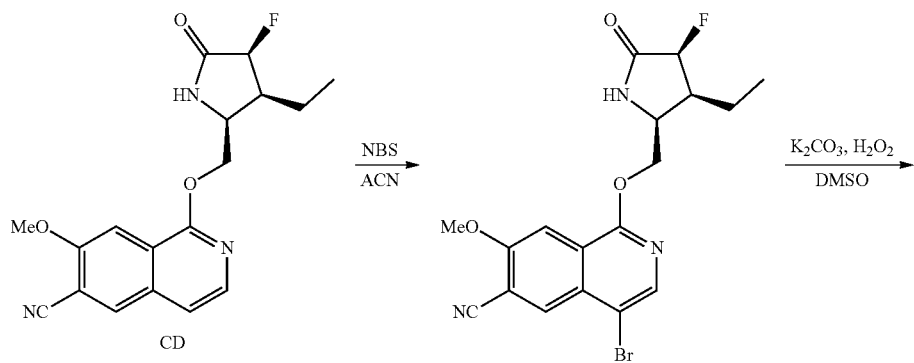
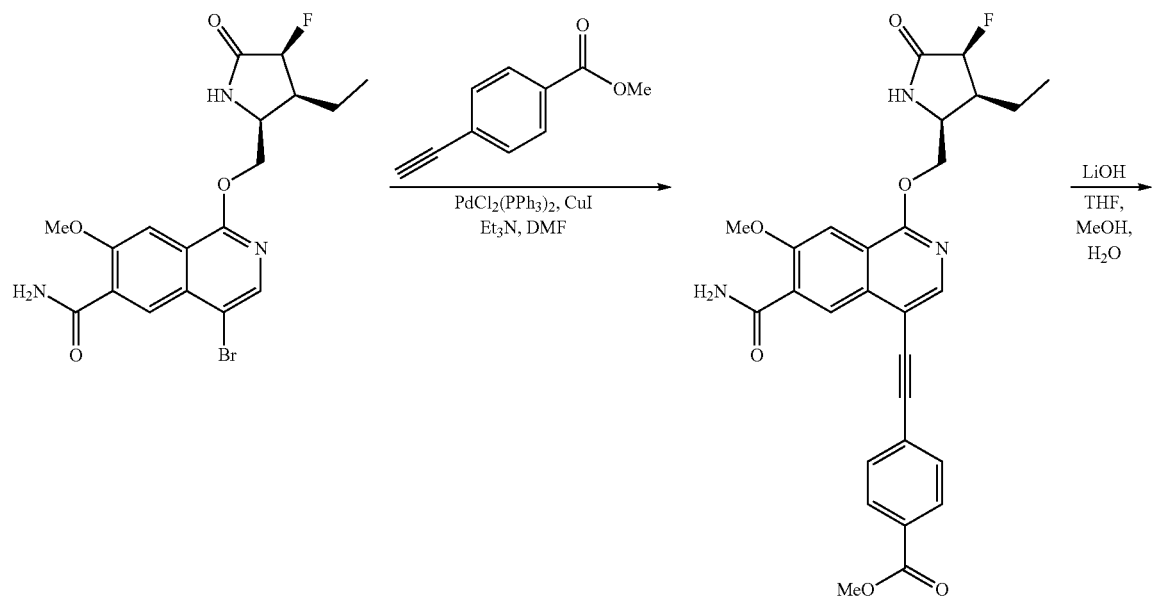

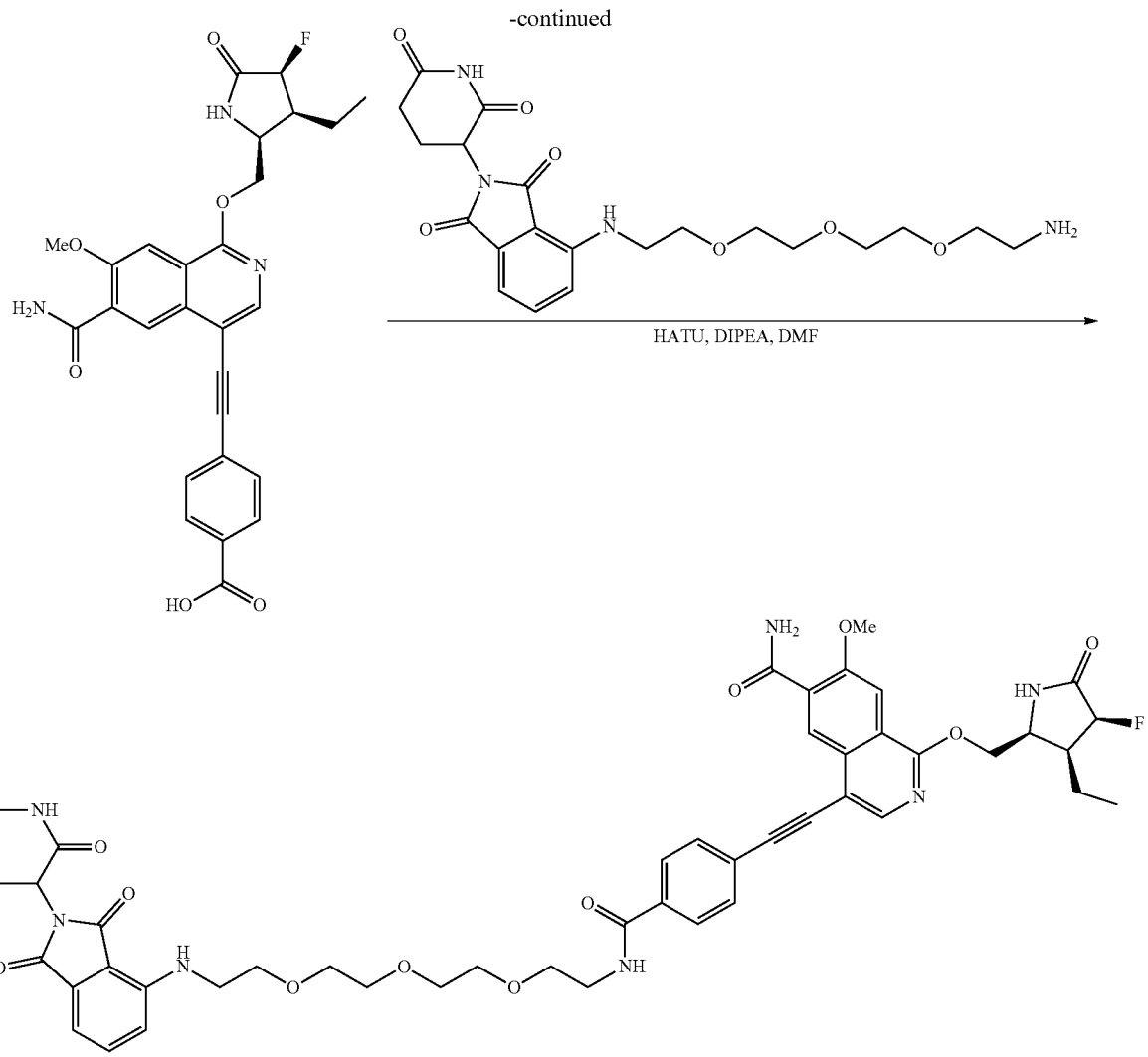

Step 1—4-bromo-1-[[(2S,3S,4S)-3-ethyl-4-fluoro-5-oxo-prrolidin-2-yl]methoxy]-7-methox-iso quinoline-6-carbonitrile To a solution of 1-[[(2S,3S,4S)-3-ethyl-4-fluoro-5-oxo-pyrrolidin-2-yl]methoxy]-7-methoxy-isoquinoline-6-carbonitrile (200 mg, 582 umol, Intermediate CD) in ACN (7.00 mL) was added NBS (228 mg, 1.28 mmol), and the mixture was stirred at 60° C. for 2 hours. On completion, the mixture was concentrated in vacuo. The mixture was purified by prep-TLC (EA) to give the title compound (130 mg, 52% yield) as a yellow solid. H NMR (400 MHz, CDCN$_3$) 8.31 (s, 1H), 8.06 (s, 1H), 7.68 (s, 1H), 7.57 (s, 1H), 4.99-4.79 (m, 1H), 4.71 (d, J=11.6 Hz, 1H), 4.41-4.32 (m, 1H), 4.21-4.14 (m, 1H), 4.07 (s, 3H), 2.70-2.47 (m, 1H), 1.86-1.66 (m, 2H), 1.13 (t, J=7.2 Hz, 3H).

Step 2—4-Bromo-1-[[(2S,3S,4S)-3-ethyl-4-fluoro-5-oxo-pyrrolidin-2-yl]methoxy]-7-methoxy-isoquinoline-6-carboxamide To a solution of 4-bromo-1-[[(2S,3S,4S)-3-ethyl-4-fluoro-5-oxo-pyrrolidin-2-yl]methoxy]-7-methoxy-isoquinoline-6-carbonitrile (300 mg, 710 umol) in DMSO (3.00 mL) was added K$_2$CO$_3$ (39.2 mg, 284 umol) and H$_2$O$_2$ (241 mg, 2.13 mmol, 30% solution). The mixture was stirred at rt for 16 hours. On completion, the mixture was diluted with H$_2$O (30 mL) and extracted with EA (3×30 mL). The organic layers were dried over anhydrous Na$_2$SO$_4$, filtered and concentrated in vacuo to give the title compound (300 mg, 80% yield) as a white solid. $^1$H NMR (400 MHz, DMSO-d$_6$) δ 8.88 (s, 1H), 8.24 (s, 1H), 8.16 (s, 1H), 7.95 (s, 1H), 7.85 (s, 1H), 7.80 (s, 1H), 5.00-4.82 (m, 1H), 4.56-4.50 (m, 1H), 4.30-4.23 (m, 1H), 4.10 (s, 1H), 4.00 (s, 3H), 1.64-1.53 (m, 2H), 1.02 (t, J=7.2 Hz, 3H).

Step 3—Methyl 4-[2-[6-carbamoyl-1-[[(2S,3S,4S)-3-ethyl-4-fluoro-5-oxo-pyrrolidin-2-yl]methoxy]-7-methoxy-4-isoquinolyl]ethynyl]benzoate 4-bromo-1-[[(2S,3S,4S)-3-ethyl-4-fluoro-5-oxo-pyrrolidin-2-yl]methoxy]-7-methoxy-isoquinoline-6-carboxamide (100 mg, 227 umol), Pd(PPh$_3$)$_2$Cl$_2$ (15.9 mg, 22.7 umol) and CuI (8.65 mg, 45.4 umol) were placed in a microwave tube. Then methyl 4-ethynylbenzoate (72.7 mg, 454 umol, CAS #10602-03-6), TEA (229 mg, 2.27 mmol) and DMF (2.00 mL) were added into the above tube. The mixture was degassed with nitrogen for 5 minutes. The sealed tube was heated at 120° C. for 3 hours under microwave. On completion, the mixture was concentrated in vacuo. The mixture was purified by reverse phase chromatography (0.1% FA) to give the title compound (40.0 mg, 33% yield) as a black solid. LC-MS (ESI$^+$) m/z 520.3 (M+H)$^+$.

Step 4—4-[2-[6-Carbamoyl-1-[[(2S,3S,4S)-3-ethyl-4-fluoro-5-oxo-pyrrolidin-2-yl]methoxy]-7-methoxy-4-isoquinolyl]ethynyl]benzoic acid To a solution of methyl 4-[2-[6-carbamoyl-1-[[(2S,3S,4S)-3-ethyl-4-fluoro-5-oxo-pyrrolidin-2-yl]methoxy]-7-methoxy-4-isoquinolyl]ethynyl]benzoate (40.0 mg, 76.9 umol) in a mixed solvent of THF (3.00 mL), MeOH (1.00 mL) and H$_2$O (1.00 mL) was added LiOH (9.22 mg, 384 umol). The mixture was stirred at rt for 16 hours. On completion, the mixture was acidified with 1N HCl solution until the pH=5. The mixture was concentrated in vacuo to give the title compound (38.0 mg, 85% yield) as a black solid. LC-MS (ESI$^+$) m/z 506.2 (M+H)$^+$.

Step 5—4-[2-[4-[2-[2-[2-[2-[[2-(2,6-Dioxo-3-piperidyl)-1,3-dioxo-isoindolin-4-yl]amino]ethoxy]ethoxy]ethoxy]ethylcarbamoyl]phenyl]ethynyl]-1-[[(2S,3S,4S)-3-ethyl-4-fluoro-5-oxo-pyrrolidin-2-yl]methoxy]-7-methoxy-isoquinoline-6-carboxamide To a solution of 4-[2-[6-carbamoyl-1-[[(2S,3S,4S)-3-ethyl-4-fluoro-5-oxo-pyrrolidin-2-yl]methoxy]-7-methoxy-4-isoquinolyl]ethynyl]benzoic acid (28.0 mg, 55.3 umol)

and 4-[2-[2-[2-(2-aminoethoxy)ethoxy]ethoxy]ethylamino]-2-(2,6-dioxo-3-piperidyl)isoindoline-1,3-dione (26.8 mg, 55.3 umol, HCl, synthesized via Steps 1-2 of Example 128) in DMF (2.00 mL) was added HATU (25.2 mg, 66.4 umol) and DIPEA (28.6 mg, 221 umol). The mixture was stirred at rt for 30 minutes. On completion, the mixture was quenched with H$_2$O (2 mL), and the mixture was concentrated in vacuo. The mixture was purified by prep-HPLC (column: Boston Green ODS 150*30 5 u; mobile phase: [water (0.225% FA)-ACN]; B %: 37%-67%, 10 min) to give the title compound I-126 (13.3 mg, 25% yield) as yellow solid. $^1$H NMR (400 MHz, DMSO-d$_6$) δ 11.10 (s, 1H), 8.91 (s, 1H), 8.65 (t, J=5.2 Hz, 1H), 8.39 (s, 1H), 8.27 (s, 1H), 7.95 (s, 2H), 7.93 (s, 1H), 7.82 (s, 1H), 7.80 (s, 1H), 7.74 (s, 1H), 7.71 (s, 1H), 7.60-7.54 (m, 1H), 7.13 (d, J=8.4 Hz, 1H), 7.03 (d, J=8.0 Hz, 1H), 6.60 (t, J=5.6 Hz, 1H), 5.09-5.02 (m, 1H), 5.01-4.84 (m, 1H), 4.63-4.57 (m, 1H), 4.35-4.28 (m, 1H), 4.16-4.09 (m, 1H), 4.00 (s, 3H), 3.63-3.59 (m, 2H), 3.56-3.44 (m, 14H), 2.89-2.85 (m, 1H), 2.63-2.61 (m, 1H), 2.58-2.58 (m, 1H), 2.57-2.56 (m, 1H), 2.05-2.00 (m, 1H), 1.65-1.58 (m, 2H), 1.03 (t, J=7.2 Hz, 3H); LC-MS (ESI$^+$) m/z 936.2 (M+H)$^+$.

Example 127 (Method 11): N-[3-carbamoyl-1-[4-[2-[2-[2-[[2-(2,6-dioxo-3-piperidyl)-1,3-dioxo-isoindolin-4-yl]amino]ethoxy]ethoxy]ethyl]carbamoyl]phenyl]pyrazol-4-yl]-2-[2-(2,2,2-trifluoroethylamino)-4-pyridyl]oxazole-4-carboxamide, I-127

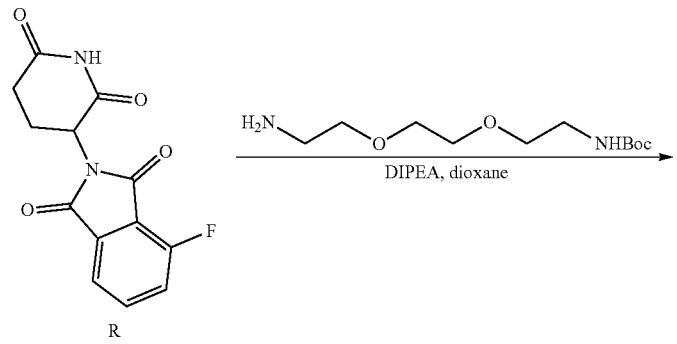

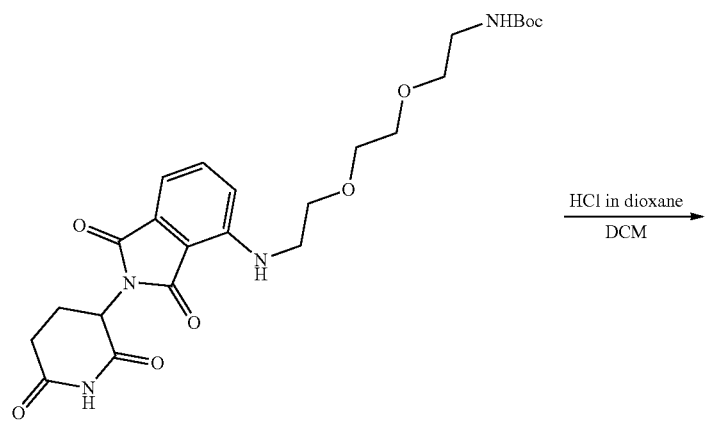

2211
2212
-continued
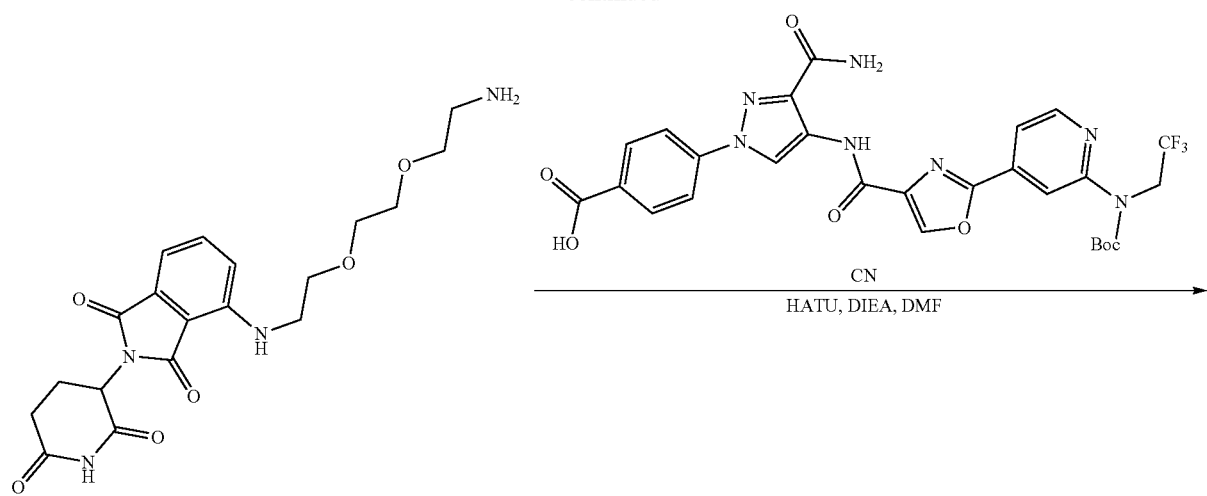
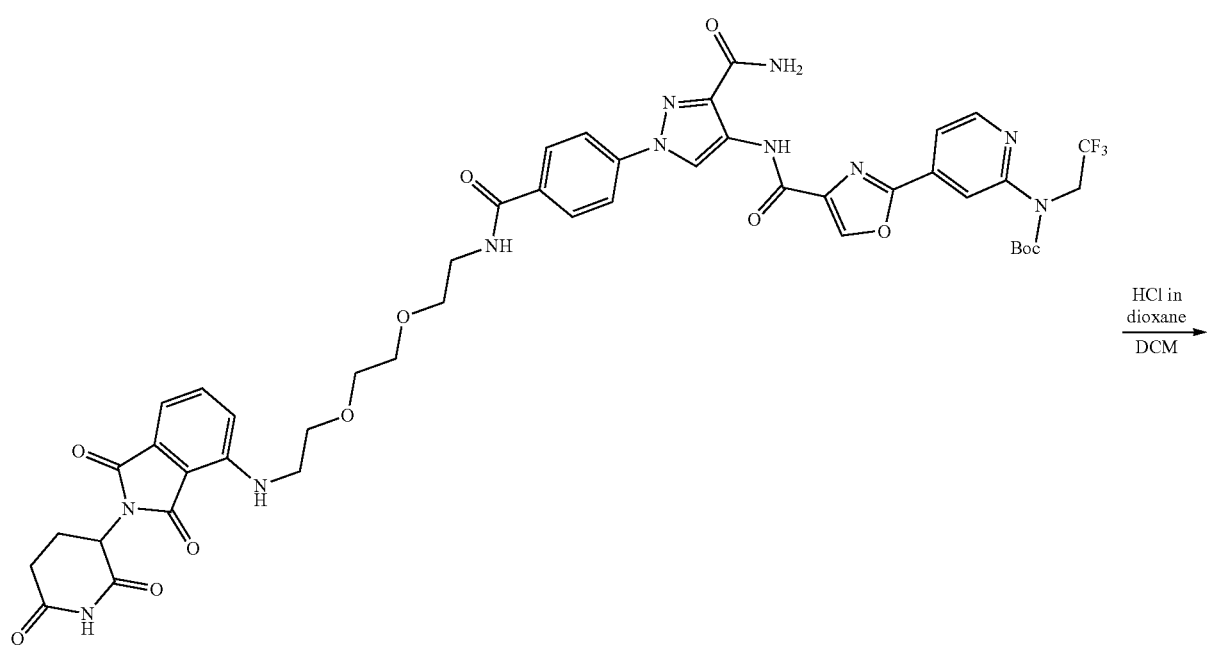

-continued

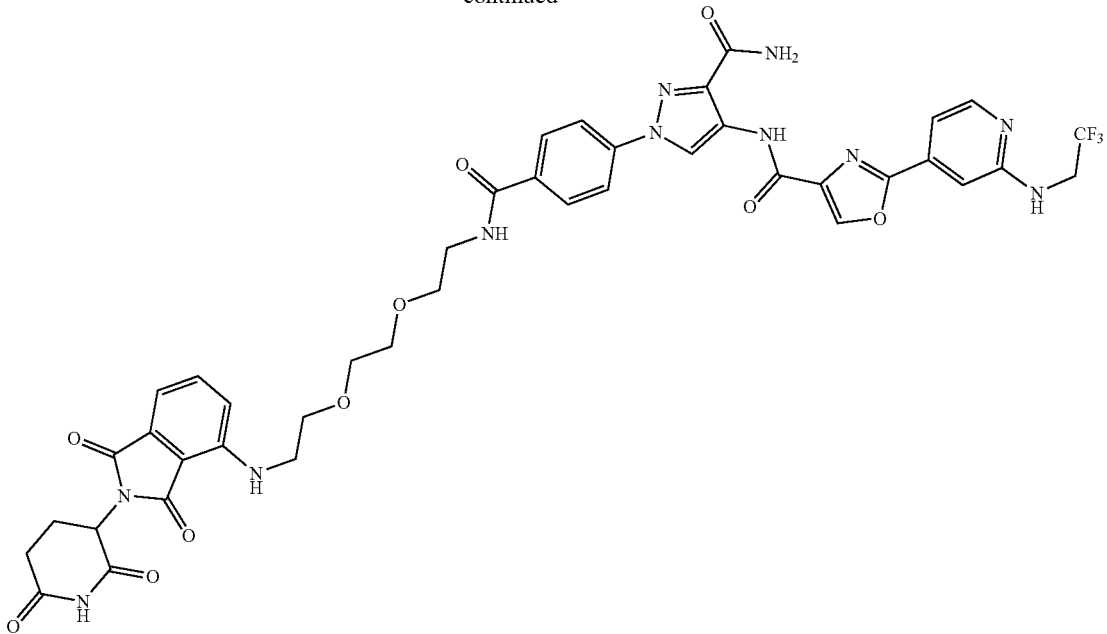

Step 1—Tert-butyl n-[2-[2-[2-[[2-(2,6-dioxo-3-piperidyl)-1,3-dioxo-isoindolin-4-N-yl]amino]ethoxy]ethoxy]ethyl]carbamate A solution of tert-butyl N-[2-[2-(2-aminoethoxy)ethoxy]ethyl]carbamate (2.50 g, 10.1 mmol, CAS #153086-78-3), 2-(2,6-dioxo-3-piperidyl)-4-fluoro-isoindoline-1,3-dione (3.34 g, 12.1 mmol, Intermediate R) and diisopropyl ethylamine (2.60 g, 20.1 mmol) in dioxane (120 mL) was stirred at 115° C. for 16 hours. On completion, the reaction mixture was concentrated in vacuo. The residue was purified by column chromatography (petroleum ether:ethyl acetate=1:1) to give the title compound (2.10 g, 40% yield) as a yellow gum. $^1$H NMR (400 MHz, CDCl$_3$) δ 8.50 (s, 1H), 7.54-7.48 (m, 1H), 7.12 (d, J=7.2 Hz, 1H), 6.92 (d, J=8.4 Hz, 1H), 6.59-6.48 (m, 1H), 5.15-5.00 (m, 1H), 4.95-4.85 (m, 1H), 3.79-3.71 (m, 2H), 3.70-3.62 (m, 4H), 3.60-3.54 (m, 2H), 3.52-3.45 (m, 2H), 3.35-3.25 (m, 2H), 2.92-2.71 (m, 3H), 2.19-2.09 (m, 1H), 1.44 (s, 9H); LC-MS (ESI$^+$) m/z 527.1 (M+Na)$^+$.

Step 2—4-[2-[2-(2-Aminoethoxy)ethoxy]ethyl amino]-2-(2,6-dioxo-3-piperidyl)isoindoline-1,3-dione To a solution of tert-butyl N-[2-[2-[2-[[2-(2,6-dioxo-3-piperidyl)-1,3-dioxo-isoindolin-4-yl]amino]ethoxy]ethoxy]ethyl]carbamate (200 mg, 396 umol) in DCM (5 mL) was added HCl in dioxane (4 M, 5 mL). The reaction mixture was stirred at rt for 10 minutes. On completion, the reaction mixture was concentrated in vacuo to give the title compound (200 mg, 90% yield) as a yellow solid. LC-MS (ESI$^+$) m/z 405.2 (M+H)$^+$.

Step 3—Tert-butyl N-[4-[4-[[3-carbamoyl-1-[4-[2-[2-[2-[[2-(2,6-dioxo-3-piperidyl)-1,3-dioxo-isoindolin-4-yl]amino]ethoxy]ethoxy]ethylcarbamoyl]phenyl]pyrazol-4-yl]carbamoyl]oxazol-2-yl]-2-pyridyl]-N-(2,2,2-trifluoroethyl)carbamate To a solution of 4-[2-[2-(2-aminoethoxy)ethoxy]ethylamino]-2-(2,6-dioxo-3-piperidyl)isoindoline-1,3-dione (200 mg, 418 umol) and 4-[4-[[2-[2-[tert-butoxycarbonyl(2,2,2-trifluoroethyl)amino]-4-pyridyl]oxazole-4-carbonyl]amino]-3-carbamoyl-pyrazol-1-yl]benzoic acid (257 mg, 418 umol, Intermediate CN) in DMF (5 mL) was added DIPEA (270 mg, 2.09 mmol, 364 uL). The mixture was stirred at rt for 12 minutes, and then HATU (191 mg, 502 umol) was added to the mixture. The reaction mixture was stirred at rt for 12 hours. On completion, the mixture was quenched with H$_2$O (10 mL) and filtered. The filter cake was dried in vacuo to give the title compound (400 mg, 95% yield) as a yellow solid. LC-MS (ESI$^+$) m/z 902.2 (M+H–100)$^+$.

Step 4—N-[3-carbamoyl-1-[4-[2-[2-[2-[[2-(2,6-dioxo-3-piperidyl)-1,3-dioxo-isoindolin-4-yl]amino]ethoxy]ethoxy]ethylcarbamoyl]phenyl]pyrazol-4-yl]-2-[2-(2,2,2-trifluoroethylamino)-4-pyridyl]oxazole-4-carboxamide To a solution of tert-butyl N-[4-[4-[[3-carbamoyl-1-[4-[2-[2-[2-[[2-(2,6-dioxo-3-piperidyl)-1,3-dioxo-isoindolin-4-yl]amino]ethoxy]ethoxy]ethylcarbamoyl]phenyl]pyrazol-4-yl]carbamoyl]oxazol-2-yl]-2-pyridyl]-N-(2,2,2-trifluoroethyl)carbamate (400 mg, 399 umol) in DCM (3 mL) was added HCl in dioxane (4 M, 3 mL). The reaction mixture was stirred at rt for 20 minutes. On completion, the reaction mixture was concentrated in vacuo. The residue was purified by prep-HPLC (column: Phenomenex Synergi Max-RP 250*50 mm*10 um; mobile phase: [water (0.225% FA)-ACN]; B %: 35 ACN %-63 ACN %) to give the title compound I-127 (121 mg, 31% yield) as a yellow solid. $^1$H NMR (400 MHz, DMSO-d$_6$) δ 11.10 (s, 1H), 11.02 (s, 1H), 9.05 (s, 1H), 9.04 (s, 1H), 8.63 (t, J=5.2 Hz, 1H), 8.26 (d, J=5.2 Hz, 1H), 8.14 (m, 1H), 8.11-8.06 (m, 2H), 8.05-7.99 (m, 2H), 7.79 (m, 2H), 7.56 (dd, J=7.2, 8.4 Hz, 1H), 7.29 (s, 1H), 7.19 (dd, J=1.2, 5.2 Hz, 1H), 7.12 (d, J=8.4 Hz, 1H), 7.02 (d, J=7.2 Hz, 1H), 6.60 (s, 1H), 5.06 (dd, J=5.6, 13.2 Hz, 1H), 4.34-4.20 (m, 2H), 3.67-3.52 (m, 12H), 2.96-2.82 (m, 1H), 2.64-2.58 (m, 1H), 2.57-2.55 (m, 1H), 2.13-1.96 (m, 1H); LC-MS (ESI$^+$) m/z 902.3 (M+H)$^+$.

TABLE 9

Compounds synthesized via Method 11 with the addition of various amines to fluoride Intermediate R in Step 1, followed by coupling with various acids in Step 3.

| Ex-# | I-# | Step 1 Intermediate Amine | Step 3 Intermediate Acid | LCMS (ES+) m/z (M + H)+ | 1HNMR (400 MHz, DMSO-d6) δ |
|---|---|---|---|---|---|
| 128[a] | I-128 | tert-butyl N-[2-[2-[2-(2-aminoethoxy)ethoxy]-ethoxy]ethyl]-carbamate (CAS# 101187-40-0) | CN | 946.5 | 11.15-11.04 (s, 1H), 11.02 (s, 1H), 9.04 (s, 2H), 8.64 (t, J = 5.2 Hz, 1H), 8.27 (d, J = 5.2 Hz, 1H), 8.14 (s, 1H), 8.12 (s, 1H), 8.10 (s, 1H), 8.04 (s, 1H), 8.02 (s, 1H), 7.78 (s, 1H), 7.71 (t, J = 6.4 Hz, 1H), 7.60-7.55 (m, 1H), 7.28 (s, 1H), 7.19 (dd, J = 5.2 Hz, 1H), 7.12 (d, J = 8.4 Hz, 1H), 7.03 (d, J = 7.2 Hz, 1H), 6.59 (t, J = 5.6 Hz, 1H), 5.09-5.03 (m, 1H), 4.30-4.21 (m, 2H), 3.63-3.41 (m, 16H), 2.94-2.83 (m, 1H), 2.64-2.55 (m, 2H), 2.07-1.98 (m, 1H) |
| 129[g] | I-129 | BF | L | 810.4 | 11.12 (s, 1H), 9.09 (d, J = 2.0 Hz, 1H), 9.05 (d, J = 2.0 Hz, 1H), 8.97 (br s, 1H), 8.70 (s, 1H), 8.65-8.63 (m, 2H), 7.79 (s, 1H), 7.59 (dd, J = 7.2, 8.4 Hz, 1H), 7.16 (d, J = 8.4 Hz, 1H), 7.05 (d, J = 7.2 Hz, 1H), 6.63 (br s, 1H), 5.06 (dd, J = 5.2, 12.8 Hz, 1H), 4.64-4.47 (m, 1H), 3.76-3.70 (m, 10H), 3.44-3.33 (m, 1H), 3.24-3.13 (m, 4H), 2.94-2.83 (m, 1H), 2.60-2.57 (m, 3H), 2.08-1.99 (m, 1H), 1.24 (d, J = 3.6 Hz, 6H), 0.92-0.85 (m, 2H), 0.58-0.55 (m, 2H) |
| 130[b] | I-130 | tert-butyl N-[2-(2-aminoethoxy)-ethyl]carbamate (CAS# 127828-22-2) | CN | 858.0 | 11.09 (s, 1H), 11.02 (s, 1H), 9.04 (d, J = 1.6 Hz, 2H), 8.63 (t, J = 5.2 Hz, 1H), 8.26 (d, J = 5.2 Hz, 1H), 8.15 (s, 1H), 8.11-8.06 (m, 2H), 8.03-7.97 (m, 2H), 7.79 (s, 1H), 7.71 (t, J = 6.4 Hz, 1H), 7.60-7.54 (m, 1H), 7.28 (s, 1H), 7.21-7.14 (m, 2H), 7.02 (d, J = 6.8 Hz, 1H), 6.64 (t, J = 5.6 Hz, 1H), 5.04 (dd, J = 5.6, 12.8 Hz, 1H), 4.31-4.19 (m, 2H), 4.12 (s, 2H), 3.70-3.59 (m, 4H), 3.52-3.49 (m, 2H), 2.90-2.83 (m, 1H), 2.63-2.52 (m, 2H), 2.06-1.97 (m, 1H) |
| 131[f] | I-131 | BD | L | 854.1 | 11.10 (s, 1H), 9.14-8.98 (m, 2H), 8.86 (s, 1H), 8.65 (d, J = 8.8 Hz, 2H), 8.62-8.58 (m, 1H), 7.72 (s, 1H), 7.56 (t, J = 8.0 Hz, 1H), 7.12 (d, J = 8.8 Hz, 1H), 7.07-6.99 (m, 1H), 6.60 (t, J = 5.6 Hz, 1H), 5.05 (dd, J = 5.2, 13.2 Hz, 1H), 4.61-4.42 (m, 1H), 3.75-3.59 (m, 14H), 2.95-2.84 (m, 1H), 2.82-2.74 (m, 4H), 2.62-2.57 (m, 2H), 2.56-2.53 (m, 1H), 2.49-2.39 (m, 1H), 2.06-1.97 (m, 1H), 1.21 (s, 6H), 0.90-0.82 (m, 2H), 0.60-0.53 (m, 2H) |
| 132[c] | I-132 | tert-butyl N-(8-aminooctyl)-carbamate (CAS# 88829-82-7) | CN | 898.3 | 11.08 (s, 1H), 11.02 (s, 1H), 9.04 (d, J = 3.2 Hz, 2H), 8.56 (t, J = 5.6 Hz, 1H), 8.26 (d, J = 5.2 Hz, 1H), 8.13 (s, 1H), 8.11-8.07 (m, 2H), 8.06-7.99 (m, 2H), 7.77 (s, 1H), 7.70 (t, J = 6.4 Hz, 1H), 7.62-7.54 (m, 1H), 7.27 (s, 1H), 7.18 (dd, J = 1.2, 5.2 Hz, 1H), 7.09 (d, J = 8.4 Hz, 1H), 7.02 (d, J = 7.2 Hz, 1H), 6.52 (t, J = 5.6 Hz, 1H), 5.05 (dd, J = 5.2, 12.8 Hz, 1H), 4.31-4.20 (m, 2H), 3.31-3.25 (m, 4H), 2.94-2.83 (m, 1H), 2.63-2.58 (m, 1H), 2.56-2.53 (m, 1H), 2.08-1.98 (m, 1H), 1.61-1.52 (m, 4H), 1.33 (s, 8H) |

TABLE 9-continued

Compounds synthesized via Method 11 with the addition of various amines to fluoride Intermediate R in Step 1, followed by coupling with various acids in Step 3.

| Ex-# | I-# | Step 1 Intermediate Amine | Step 3 Intermediate Acid | LCMS (ES+) m/z (M + H)+ | 1HNMR (400 MHz, DMSO-d6) δ |
|---|---|---|---|---|---|
| 133[d] | I-133 | undecane-1,11-diamine-(CAS# 822-08-2) | CN | 940.0 | 11.09 (br s, 1H), 11.01 (s, 1H), 9.06-8.99 (m, 2H), 8.56 (t, J = 5.6 Hz, 1H), 8.26 (d, J = 5.6 Hz, 1H), 8.13 (s, 1H), 8.11-8.06 (m, 2H), 8.01 (d, J = 8.8 Hz, 2H), 7.77 (s, 1H), 7.69 (t J = 6.4 Hz, 1H), 7.61-7.53 (m, 1H), 7.27 (s, 1H), 7.21-7.16 (m, 1H), 7.08 (d, J = 8.4 Hz, 1H), 7.01 (d, J = 7.2 Hz, 1H), 6.50 (t, J = 5.6 Hz, 1H), 5.04 (dd, J = 5.6, 12.8 Hz, 1H), 4.30-4.20 (m, 2H), 3.30-3.14 (m, 2H), 2.94-2.80 (m, 1H), 2.63-2.54 (m, 2H), 2.09-1.97 (m, 1H), 1.55-1.50 (m, 4H), 1.35-1.19 (m, 16H) |
| 134 | I-134 | tert-butyl N-[2-[2-(2-aminoethoxy)-ethoxy]-ethyl]-carbamate (CAS# 153086-78-3) | DE | 926.9 | 1H NMR (400 MHz, DMSO-d$_6$) δ 11.09 (s, 1H), 9.98 (s, 1H), 8.99 (d, J = 4.8 Hz, 2H), 8.63 (s, 1H), 8.24 (d, J = 4.8 Hz, 1H), 8.10-7.92 (m, 4H), 7.68-7.49 (m, 2H), 7.25 (s, 1H), 7.21 (d, J = 4.0 Hz, 1H), 7.10 (d, J = 8.8 Hz, 1H), 7.01 (d, J = 6.4 Hz, 1H), 6.58 (s, 1H), 5.05 (d, J = 7.2 Hz, 1H), 4.34-4.15 (m, 2H), 3.65-3.44 (m, 12H), 2.92-2.82 (m, 1H), 2.61-2.59 (m, 1H), 2.57-2.54 (m, 1H), 2.10-1.95 (m, 1H) |
| 135 | I-135 | tert-butyl N-[2-[2-(2-aminoethoxy)-ethoxy]ethyl]-carbamate (CAS# 153086-78-3) | DD | 902.7 | 11.07 (s, 1H), 11.02 (s, 1H), 9.03 (s, 1H), 9.00 (s, 1H), 8.74 (s, 1H), 8.35 (s, 1H), 8.26 (d, J = 5.2 Hz, 1H), 8.12 (d, J = 8.0 Hz, 1H), 8.07 (s, 1H), 7.85 (d, J = 8.0 Hz, 1H), 7.74 (s, 1H), 7.70-7.60 (m, 2H), 7.55-7.50 (m, 1H), 7.27 (s, 1H), 7.18 (d, J = 4.4 Hz, 1H), 7.06 (d, J = 8.8 Hz, 1H), 7.00 (d, J = 6.8 Hz, 1H), 6.56 (s, 1H), 5.07-4.98 (m, 1H), 4.31-4.19 (m, 2H), 3.66-3.52 (m, 12H), 2.88-2.80 (m, 1H), 2.63-2.57 (m, 1H), 2.57-2.55 (m, 1H), 2.03-1.99 (m, 1H) |
| 136 | I-136 | tert-butyl (14-amino-3,6,9,12-tetraoxa-tetradecyl)-carbamate (CAS# 811442-84-9) | DD | 990.3 | 11.08 (s, 1H), 11.03 (s, 1H), 9.05 (s, 1H), 9.02 (s, 1H), 8.76 (s, 1H), 8.37 (s, 1H), 8.26 (d, J = 5.2 Hz, 1H), 8.14 (d, J = 7.2 Hz, 1H), 8.08 (s, 1H), 7.87 (d, J = 7.2 Hz, 1H), 7.75 (s, 1H), 7.70-7.61 (m, 2H), 7.58-7.52 (m, 1H), 7.27 (s, 1H), 7.18 (d, J = 4.4 Hz, 1H), 7.11 (d, J = 8.4 Hz, 1H), 7.02 (d, J = 6.8 Hz, 1H), 6.57 (s, 1H), 5.07-5.01 (m, 1H), 4.28-4.21 (m, 2H), 3.55-3.43 (m, 20H), 2.94-2.80 (m, 1H), 2.62-2.59 (m, 1H), 2.59-2.57 (m, 1H), 2.02-1.97 (m, 1H) |
| 137 | I-137 | tert-butyl N-[2-[2-(2-aminoethoxy)-ethoxy]ethyl]-carbamate (CAS# 153086-78-3) | CU | 912.4 | 12.09 (s, 1H), 11.08 (s, 1H), 9.12 (s, 1H), 8.63-8.60 (m, 1H), 8.28-8.21 (m, 4H), 8.14 (s, 1H), 8.13-8.09 (m, 2H), 8.03 (d, J = 8.8 Hz, 2H), 7.88 (s, 1H), 7.65 (d, J = 5.6 Hz, 1H), 7.60-7.53 (m, 1H), 7.50 (s, 1H), 7.19 (t, J = 6.8 Hz, 1H), 7.12 (d, J = 8.4 Hz, 1H), 7.02 (d, J = 7.2 Hz, 1H), 6.60 (t, J = 5.6 Hz, 1H), 5.06 (dd, J = 5.2, 13.2 Hz, 1H), 4.41-4.22 (m, 2H), 3.65-3.60 (m, 2H), 3.61-3.56 (m, 6H), 3.45 (d, J = 5.6 Hz, 4H), 2.93-2.82 (m, 1H), 2.63-2.55 (m, 1H), 2.55-2.53 (m, 1H), 2.08-1.99 (m, 1H) |

TABLE 9-continued

Compounds synthesized via Method 11 with the addition of various
amines to fluoride Intermediate R in Step 1, followed by coupling with various acids in Step 3.

| Ex-# | I-# | Step 1 Intermediate Amine | Step 3 Intermediate Acid | LCMS (ES+) m/z (M + H)+ | $^1$HNMR (400 MHz, DMSO-d6) δ |
|---|---|---|---|---|---|
| 138[e] | I-138 | tert-butyl N-[2-[2-(2-aminoethoxy)-ethoxy]ethyl]-carbamate (CAS# 153086-78-3) | DF | 874.4 | 10.84 (s, 1H), 10.77 (s, 1H), 8.79 (s, 1H), 8.77 (s, 1H), 8.40-8.36 (m, 1H), 7.93 (d, J = 5.6 Hz, 1H), 7.90-7.82 (m, 3H), 7.80-7.76 (m, 2H), 7.53 (s, 1H), 7.35-7.30 (m, 1H), 6.94-6.86 (m, 3H), 6.80-6.75 (m, 2H), 6.35 (t, J = 6.0 Hz, 1H), 4.81 (dd, J = 5.6, 13.2 Hz, 1H), 3.42-3.30 (m, 8H), 3.23-3.19 (m, 2H), 2.99-2.92 (m, 2H), 2.69-2.58 (m, 1H), 2.37-2.28 (m, 4H), 1.83-1.75 (m, 1H), 0.87-0.77 (m, 1H), 0.26-0.18 (m, 2H), 0.02-0.04 (m, 2H) |
| 139 | I-139 | tert-butyl N-[2-[2-(2-aminoethoxy)-ethoxy]ethyl]-carbamate (CAS# 153086-78-3) | CW | 908.4 | 11.09 (s, 1H), 10.94 (d, J = 3.6 Hz, 1H), 8.96 (d, J = 6.4 Hz, 1H), 8.34 (d, J = 16.8 Hz, 1H), 8.25 (d, J = 5.2 Hz, 1H), 7.87-7.74 (m, 1H), 7.72-7.61 (m, 2H), 7.61-7.55 (m, 1H), 7.51 (s, 1H), 7.26 (s, 1H), 7.19-7.10 (m, 2H), 7.04 (t, J = 7.2 Hz, 1H), 6.65-6.56 (m, 1H), 5.06-5.04 (m, 1H), 4.35-4.27 (m, 1H), 4.26-4.19 (m, 2H), 3.66-3.53 (m, 6H), 3.51-3.44 (m, 4H), 3.30-3.14 (m, 2H), 2.94-2.83 (m, 1H), 2.64-2.57 (m, 1H), 2.56-2.53 (m, 1H), 2.46-2.37 (s, 1H), 2.24-2.17 (m, 1H), 2.13-2.02 (m, 2H), 1.94-1.76 (m, 4H), 1.66-1.53 (m, 2H) |
| 140[h] | I-140 | tert-butyl N-[2-[2-(2-aminoethoxy)-ethoxy]ethyl]-carbamate (CAS# 153086-78-3) | EE | 805.4 | 11.18-11.06 (m, 2H), 9.10 (s, 1H), 9.03 (s, 1H), 8.85 (d, J = 6.0 Hz, 2H), 8.62 (t, J = 5.4 Hz, 1H), 8.15 (s, 1H), 8.11-8.06 (m, 2H), 8.05-8.00 (m, 2H), 7.97 (d, J = 6.0 Hz, 2H), 7.82 (s, 1H), 7.60-7.52 (m, 1H), 7.12 (d, J = 8.4 Hz, 1H), 7.02 (d, J = 7.2 Hz, 1H), 6.59 (t, J = 6.0 Hz, 1H), 5.05 (dd, J = 5.4, 12.8 Hz, 1H), 3.65-3.53 (m, 8H), 3.43-3.41 (m, 4H), 2.94-2.82 (m, 1H), 2.63-2.57 (m, 1H), 2.58-2.56 (m, 1H), 2.03-1.99 (m, 1H) |
| 141 | I-141 | EF | CN | 886.3 | 11.08 (s, 1H), 11.02 (s, 1H), 9.03 (s, 2H), 8.57 (t, J = 4.8 Hz, 1H), 8.25 (d, J = 5.6 Hz, 1H), 8.13 (s, 1H), 8.09 (d, J = 8.8 Hz, 2H), 8.02 (d, J = 8.8 Hz, 2H), 7.77 (s, 1H), 7.70 (t, J = 6.4 Hz, 1H), 7.57 (t, J = 7.6 Hz, 1H), 7.27 (s, 1H), 7.18 (d, J = 5.2 Hz, 1H), 7.10 (d, J = 8.4 Hz, 1H), 7.01 (d, J = 6.8 Hz, 1H), 6.67 (t, J = 5.6 Hz, 1H), 5.04 (dd, J = 5.6, 13.2 Hz, 1H), 4.32-4.18 (m, 2H), 3.50-3.44 (m, 4H), 3.41-3.37 (m, 4H), 2.94-2.80 (m, 1H), 2.59-2.53 (m, 2H), 2.06-1.97 (m, 1H), 1.87-1.78 (m, 4H) |
| 142 | I-142 | tert-butyl N-[2-[2-(2-aminoethoxy)-ethoxy]ethyl]-carbamate (CAS# 153086-78-3) | EC | 854.1 | 9.12 (s, 1H), 8.62 (t, J = 5.6 Hz, 1H), 8.48 (d, J = 7.2 Hz, 1H), 8.37 (s, 1H), 8.05-7.98 (m, 4H), 7.83 (d, J = 5.6 Hz, 1H), 7.67-7.35 (m, 2H), 7.11 (d, J = 8.4 Hz, 1H), 7.01 (d, J = 7.2 Hz, 1H), 6.59 (t, J = 5.6 Hz, 1H), 6.45 (d, J = 7.2 Hz, 1H), 6.31 (s, 1H), 5.08-5.01 (m, 1H), 4.33-4.24 (m, 1H), 3.65-3.62 (m, 2H), 3.57-3.54 (m, 11H), 2.92-2.81 (m, 1H), 2.62-2.55 (m, 1H), 2.54-2.52 (m, 1H), 2.07-1.97 (m, |

TABLE 9-continued

Compounds synthesized via Method 11 with the addition of various amines to fluoride Intermediate R in Step 1, followed by coupling with various acids in Step 3.

| Ex-# | I-# | Step 1 Intermediate Amine | Step 3 Intermediate Acid | LCMS (ES+) m/z (M + H)+ | 1HNMR (400 MHz, DMSO-d6) δ |
|---|---|---|---|---|---|
| 143 | I-143 | tert-butyl N-[2-[2-(2-aminoethoxy)-ethoxy]ethyl]-carbamate (CAS# 153086-78-3) | DZ | 903.0 | 1H), 1.83-1.73 (m, 2H), 1.70-1.53 (m, 4H), 1.46-1.30 (m, 2H) 11.09 (s, 1H), 11.03 (s, 1H), 9.24 (d, J = 2.4 Hz, 1H), 9.14 (s, 1H), 9.05 (s, 1H), 8.71 (t, J = 5.6 Hz, 1H), 8.56 (dd, J = 2.8, 8.4 Hz, 1H), 8.26 (d, J = 5.6 Hz, 1H), 8.20 (s, 1H), 8.16 (d, J = 8.4 Hz, 1H), 7.84 (s, 1H), 7.71 (t, J = 6.4 Hz, 1H), 7.54 (t, J = 7.6 Hz, 1H), 7.27 (s, 1H), 7.18 (d J = 5.2 Hz, 1H), 7.11 (d, J = 8.8 Hz, 1H), 6.99 (d J = 7.2 Hz, 1H), 6.58 (t, J = 5.6 Hz, 1H), 5.04 (dd, J = 5.2, 12.8 Hz, 1H), 4.28-4.22 (m, 2H), 3.64 (d, J = 5.6 Hz, 2H), 3.61-3.58 (m, 6H), 3.51-3.46 (m, 4H), 2.92-2.82 (m, 1H), 2.61-2.59 (m, 1H), 2.57-2.55 (m, 1H), 2.03-2.01 (m, 1H) |

Variations in reaction time for Method 11 were as follows: Step 1 was run anywhere from 12-16 h, Step 2 anywhere from 10 min-12 h, Step 3 anywhere from 0.5-12 h, and Step 4 was run anywhere from 20 min-10 h. The product of Step 3 was also extracted with EtOAc when it did not precipitate out of solution.
<sup>a</sup>The product of Step 1 was purified by prep-TLC (SiO₂, PE:EA = 1:2).
<sup>b</sup>The product of Step 3 was purified by prep-HPLC (column: Gemini 150*25 5u; mobile phase: [water (0.05% ammonia hydroxide v/v)-ACN]; B %: 55%-85%).
<sup>c</sup>The final product was purified by prep-HPLC under basic conditions (column: Phenomenex Luna Phenyl-Hexyl 150_30_5 um; mobile phase: [water (10 mM NH₄HCO₃)-ACN]; B %: 45%-90%).
<sup>d</sup>Step 2, the first deprotection step with HCl was skipped as there was no BOC group to deprotect from the amine intermediate.
<sup>e</sup>Step 4 was run in a mixed solvent of DCM (1 mL) and DMF (2 mL).
<sup>f</sup>The deprotection of the CBZ group in Step 2 was achieved with a hydrogenation using Pd(OH)₂/C and hydrogen gas (15 psi pressure) in THF at rt for 16 h.
<sup>g</sup>The deprotection of the benzyl groups in Step 2 was achieved with a hydrogenation using Pd(OH)₂/C, Pd/C and hydrogen gas (15 psi pressure) in THF and a catalytic amount of HCl at rt for 20 h. After filtration and concentration, the intermediate was purified by reversed phase chromatography (0.1% NH₃•H₂O). The final product was also purified by reversed phase chromatography using TFA not FA as the acidic modifier.
<sup>h</sup>Step 4 was skipped as no deprotection was required.

Further Examples Using Synthetic Methods Similar to Method 11

Example 144: N-[3-carbamoyl-1-[4-[2-[5-[[2-(2,6-dioxo-3-piperidyl)-1,3-dioxo-isoindolin-4-yl]amino]pentylamino]ethylcarbamoyl]phenyl]pyrazol-4-yl]-2-[2-(2,2,2-trifluoroethylamino)-4-pyridyl]oxazole-4-carboxamide, I-144

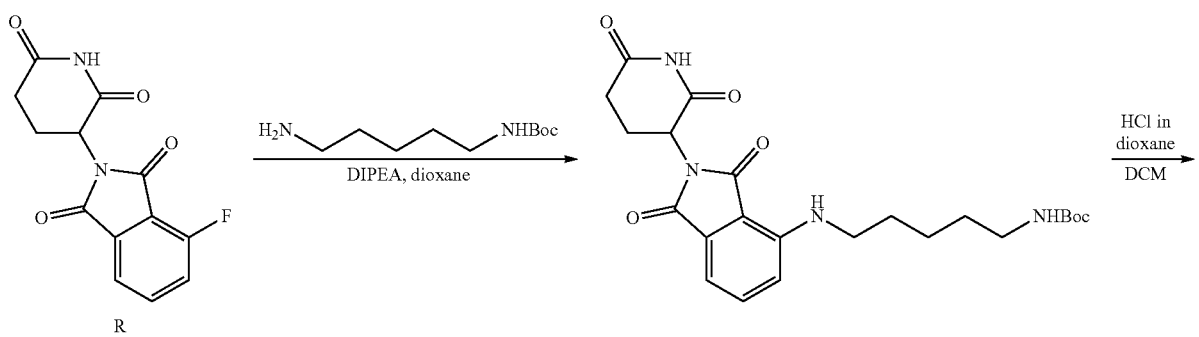

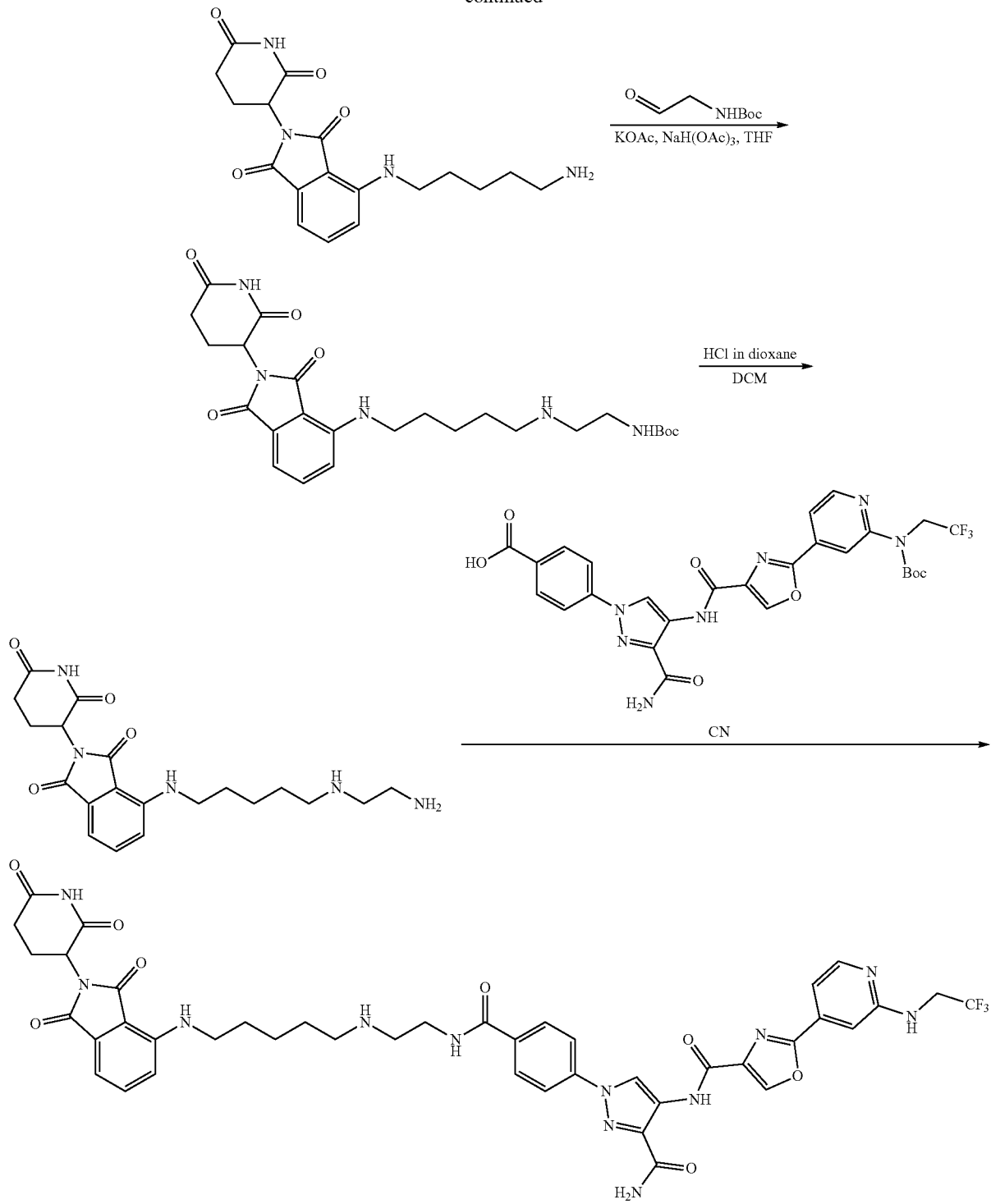

4-(5-aminopentylamino)-2-(2,6-dioxo-3-piperidyl)isoindoline-1,3-dione was synthesized via Steps 1-2 of Method 11, where fluoride Intermediate R was coupled with amine tert-butyl N-(5-aminopentyl)carbamate (CAS #51644-96-3) in the first step, and Step 2 was run at rt for 1 hr. Step 3 involved a reductive amination performed as follows: to a solution of 4-(5-aminopentylamino)-2-(2,6-dioxo-3-piperidyl)isoindoline-1,3-dione (300 mg, 759 umol, HCl) and tert-butyl N-(2-oxoethyl)carbamate (193 mg, 1.22 mmol, CAS #89711-08-0) in THF (60 mL) was added KOAc (149 mg, 1.52 mmol) and NaBH(OAc)₃ (402 mg, 1.90 mmol). The mixture was stirred at rt for 20 hours. On completion, the reaction mixture was added to ice water (100 mL) and extracted with DCM (3×60 mL). The organic phase was collected, dried over anhydrous Na₂SO₄, filtered and concentrated in vacuo. The residue was purified by prep-HPLC (0.1% FA) to give tert-butyl N-[2-[5-[[2-(2,6-dioxo-3-piperidyl)-1,3-dioxo-isoindolin-4-yl]amino]pentylamino]ethyl]

carbamate (180 mg, 42% yield) as a yellow solid gum (LC-MS (ESI+) m/z 502.2 (M+H)+).

Step 4 followed Method 11 with deprotection of the Boc group with HCl in dioxane. This intermediate was carried on without purification to the final step which was performed as follows: to a mixture of 4-[5-(2-aminoethylamino)pentylamino]-2-(2,6-dioxo-3-piperidyl)isoindoline-1,3-dione (110 mg, 251 umol, HCl salt) and DIPEA (162 mg, 1.26 mmol) in DMF (3 mL) was added 4-[4-[[2-[2-[tert-butoxycarbonyl(2,2,2-trifluoroethyl)amino]-4-pyridyl]oxazole-4-carbonyl]amino]-3-carbamoyl-pyrazol-1-yl]benzoic acid (123 mg, 200 umol, Intermediate CN) and HATU (114 mg, 301 umol). The reaction mixture was stirred at rt for 0.5 hour. On completion, the reaction mixture was concentrated in vacuo. The residue was purified by reverse phase (0.1% HCl), then it was purified by prep-HPLC (column: Phenomenex Synergi C18 150*25*10 um; mobile phase: [water (0.225% FA)-ACN]) to give the title compound I-144 (11.4 mg, 4% yield, FA) as yellow solid. $^1$H NMR (400 MHz, DMSO-$d_6$) δ 11.02 (s, 1H), 9.05 (d, J=2.4 Hz, 2H), 8.70 (s, 1H), 8.33 (s, 1H), 8.27 (d, J=5.6 Hz, 1H), 8.14 (s, 1H), 8.13-8.00 (m, 4H), 7.78 (s, 1H), 7.71 (t, J=6.4 Hz, 1H), 7.61-7.55 (m, 1H), 7.28 (s, 1H), 7.20-7.16 (m, 1H), 7.10 (d, J=8.4 Hz, 1H), 7.04-6.99 (m, 1H), 6.54 (t, J=5.8 Hz, 1H), 5.06 (dd, J=5.5, 13.2 Hz, 1H), 4.32-4.21 (m, 2H), 3.40-3.27 (m, 4H), 2.95-2.84 (m, 3H), 2.81 (t, J=6.0 Hz, 2H), 2.66-2.61 (m, 3H), 2.06-2.00 (m, 1H), 1.64-1.47 (m, 4H), 1.44-1.35 (m, 2H); LC-MS (ESI+) m/z 899.4 (M+H)+.

Example 145: N-[3-carbamoyl-1-[1-[2-[2-[2-[[2-(2,6-dioxo-3-piperidyl)-1,3-dioxo-isoindolin-4-yl]amino]ethoxy]ethoxy]ethylcarbamoyl]-4-piperidyl]pyrazol-4-yl]-2-[2-(2,2,2-trifluoroethylamino)-4-pyridyl]oxazole-4-carboxamide, I-145

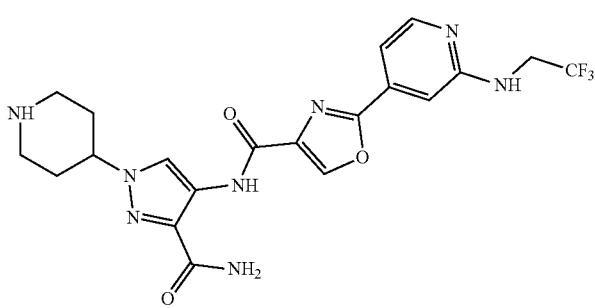

CX

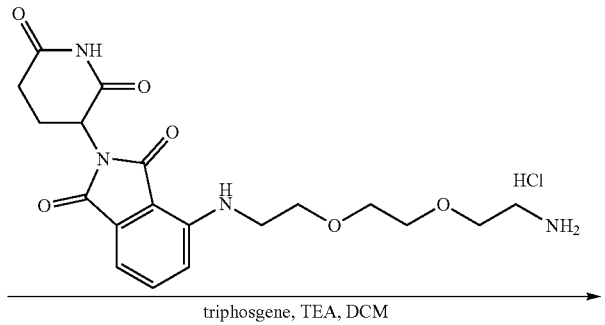

triphosgene, TEA, DCM

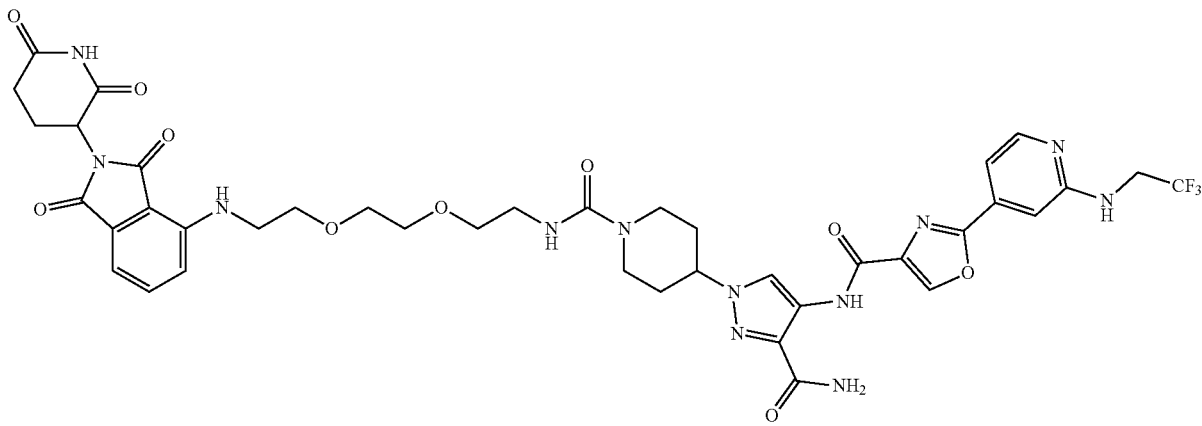

To a solution of triphosgene (14.4 mg, 48.5 umol) in DCM (2 mL) was added a solution of 4-[2-[2-(2-aminoethoxy)ethoxy]ethylamino]-2-(2,6-dioxo-3-piperidyl)isoindoline-1,3-dione (42.8 mg, 97.1 umol, HCl salt, synthesized via Steps 1-2 of Example 127) in DCM (3 mL) at 0° C. Then TEA (49.1 mg, 485 umol) was added to the solution dropwise at 0° C., followed by N-[3-carbamoyl-1-(4-piperidyl)pyrazol-4-yl]-2-[2-(2,2,2-tri fluoroethylamino)-4-pyridyl]oxazole-4-carboxamide (50.0 mg, 97.1 umol, HCl salt, Intermediate CX), The reaction mixture was then stirred at 0° C. for 1 hour. On completion, the reaction mixture was concentrated in vacuo. The residue was purified by prep-HPLC (column: Boston Green ODS 150*30 5 u; mobile phase: [water (0.225% FA)-ACN]) to give the title compound I-445 (20.4 mg, 22% yield, FA) as a yellow solid. $^1$H NMR (400 MHz, DMSO-d$_6$) δ 11.10 (s, 1H), 10.95 (s, 1H), 8.98 (s, 1H), 8.39 (s, 1H), 8.25 (d, J=5.2 Hz, 1H), 7.75-7.67 (m, 2H), 7.62-7.55 (m, 1H), 7.52 (s, 1H), 7.26 (s, 1H), 7.17 (d, J=1.2 Hz, 1H), 7.16-7.13 (m, 1H), 7.12-7.12 (m, 1H), 7.04 (d, J=7.2 Hz, 1H), 6.62-6.60 (m, 2H), 5.07 (dd, J=5.6, 12.8 Hz, 1H), 4.50-4.41 (m, 1H), 4.30-4.19 (m, 2H), 4.09 (d, J=12.8 Hz, 2H), 3.65-3.61 (m, 2H), 3.59-3.52 (m, 4H), 3.48-3.45 (m, 2H), 3.44-3.41 (m, 2H), 3.24-3.13 (m, 2H), 2.95-2.86 (m, 1H), 2.86-2.78 (m, 2H), 2.62-2.57 (m, 1H), 2.56 m 2.53 (m, 1H), 2.05-1.96 (m, 3H), 1.89-1.78 (m, 2H); LC-MS (ESI$^+$) m/z 909.1 (M+H)$^+$.

Example 146 (Method 12): N-(3-carbamoyl-1-(4-((2-(3-(2-(2,6-dioxopiperidin-3-yl)-1,3-dioxoisoindolin-5-yl)propoxy)ethyl)carbamoyl)phenyl)-1H-pyrazol-4-yl)-2-(2-((2,2,2-trifluoroethyl)amino)pyridin-4-yl)oxazole-4-carboxamide, I-146

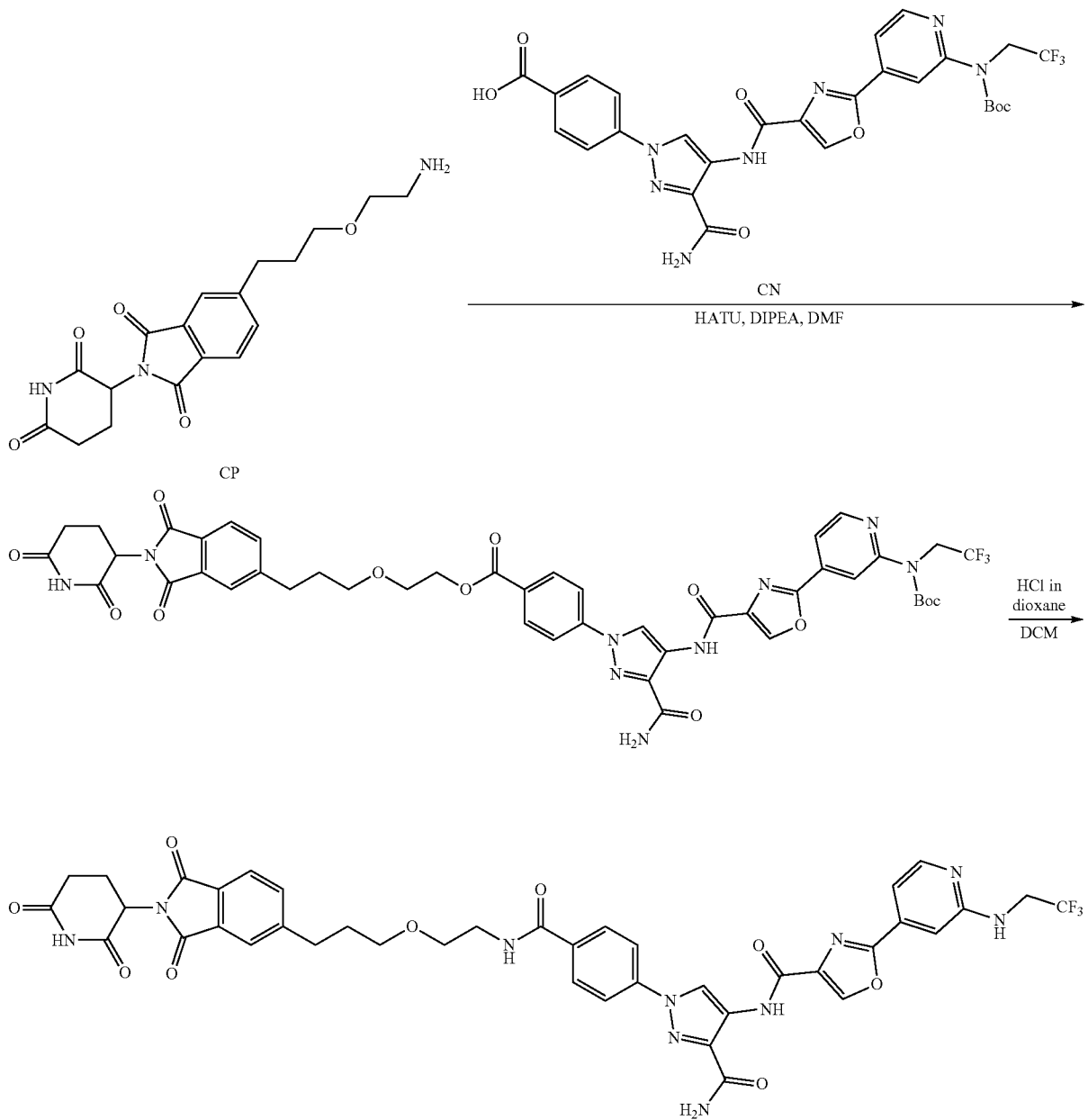

Step 1—Tert-butyl (4-(4-((3-carbamoyl-1-(4-((2-(3-(2-(2,6-dioxopiperidin-3-yl)-1,3-dioxoisoindolin-5-yl)propoxy)ethyl)carbamoyl)phenyl)-1H-pyrazol-4-yl)carbamoyl)oxazol-2-yl)pyridin-2-yl)(2,2,2-trifluoroethyl)carbamate To a solution of 4-[3-(2-aminoethoxy)propyl]-2-(2,6-dioxo-3-piperidyl)isoindoline-1,3-dione (90 mg, 250 umol, Intermediate CP) and (154 mg, 250 umol, Intermediate CN) in DMF (2 mL) was added DIPEA (162 mg, 1.25 mmol). Ten minutes later, HATU (114 mg, 300 umol) was added into the above mixture. The reaction mixture was stirred at rt for 0.5 h. On completion, the mixture was diluted was water (30 mL), stirred and filtered. The filter cake was dried in vacuo to give the title compound (110 mg, 43% yield) as a white solid. LC-MS (ESI$^+$) m/z 957.3 (M+H)$^+$.

Step 2—N-(3-carbamoyl-1-(4-((2-(3-(2-(2,6-dioxopiperidin-3-yl)-1,3-dioxoisoindolin-5-yl)propoxy)ethyl)carbamoyl)phenyl)-1H-pyrazol-4-yl)-2-(2-((2,2,2-trifluoroethyl)amino)pyridin-4-yl)oxazole-4-carboxamide To a solution of tert-butyl N-[4-[4-[[3-carbamoyl-1-[4-[2-[3-[2-(2,6-dioxo-3-piperidyl)-1,3-dioxo-isoindolin-4-yl]propoxy]ethylcarbamoyl]phenyl]pyrazol-4-yl]carbamoyl]oxazol-2-yl]-2-pyridyl]-N-(2,2,2-trifluoroethyl)carbamate (110 mg, 115 umol) in DCM (2 mL) was added HCl in dioxane (4 M, 2 mL). The reaction mixture was stirred at rt for 17 h. On completion, the mixture was concentrated in vacuo. The residue was purified by prep-HPLC (column: Phenomenex Synergi C18 150*25*10 um; mobile phase: [water (0.225% FA)-ACN]; B %: 32%-62%) to give the title compound I-146 (13.3 mg, 13% yield, FA) as a white solid. $^1$H NMR (400 MHz, DMSO-d$_6$) δ 11.11 (s, 1H), 11.02 (s, 1H), 9.04 (d, J=5.2 Hz, 2H), 8.71-8.62 (m, 1H), 8.26 (d, J=5.2 Hz, 1H), 8.15-8.07 (m, 3H), 8.07-8.02 (m, 2H), 7.84-7.75 (m, 3H), 7.73-7.67 (m, 2H), 7.28 (s, 1H), 7.19 (d, J=5.2 Hz, 1H), 5.14 (dd, J=5.2, 13.2 Hz, 1H), 4.32-4.19 (m, 2H), 3.54 (t, J=5.2 Hz, 2H), 3.48-3.43 (m, 4H), 2.96-2.87 (m, 1H), 2.86-2.83 (m, 2H), 2.63-2.59 (m, 2H), 2.11-2.02 (m, 1H), 1.93-1.84 (m, 2H); LC-MS (ESI$^+$) m/z 857.3 (M+H)$^+$

TABLE 10

Compounds synthesized via Method 12 with the coupling of various amines and acids in Step 1.

| Ex-# | I-# | Step 1 Intermediate Amine | Step 1 Intermediate Acid | LCMS (ES+) m/z (M + H)$^+$ | $^1$HNMR (400 MHz, DMSO-d6) δ |
|---|---|---|---|---|---|
| 147 | I-147 | CQ | CN | 901.3 | 11.10 (s, 1H), 11.01 (s, 1H), 9.02 (d, J = 5.6 Hz, 2H), 8.64 (t, J = 5.6 Hz, 1H), 8.26 (d, J = 5.2 Hz, 1H), 8.14-8.06 (m, 3H), 8.05-7.99 (m, 2H), 7.82-7.73 (m, 3H), 7.72-7.66 (m, 2H), 7.28 (s, 1H), 7.19 (d, J = 5.2 Hz, 1H), 5.12 (dd, J = 5.2, 12.8 Hz, 1H), 4.30-4.21 (m, 2H), 3.60-3.45 (m, 10H), 2.81-2.76 (m, 1H), 2.79 (t, J = 7.2 Hz, 2H), 2.63-2.60 (m, 1H), 2.63-2.60 (m, 1H), 2.58-2.56 (m, 1H), 2.09-2.03 (m, 1H), 1.87-1.80 (m, 1H) |
| 148 | I-148 | CT | CN | 989.9 | 11.12 (s, 1H), 11.01 (s, 1H), 9.04 (d, J = 2.4 Hz, 2H), 8.64 (t, J = 5.2 Hz, 1H), 8.26 (d, J = 5.2 Hz, 1H), 8.18-8.07 (m, 3H), 8.07-8.00 (m, 2H), 7.84-7.74 (m, 3H), 7.74-7.67 (m, 2H), 7.27 (s, 1H), 7.18 (d, J = 5.2 Hz, 1H), 5.13 (dd, J = 5.2, 12.8 Hz, 1H), 4.33-4.20 (m, 2H), 3.59-3.37 (m, 18H), 2.95-2.76 (m, 3H), 2.65-2.57 (m, 2H), 2.11-1.99 (m, 1H), 1.90-1.82 (m, 2H) |
| 149 | I-149 | CS | CN | 985.9 | 11.12 (s, 1H), 11.01 (s, 1H), 9.04 (s, 2H), 8.65 (t, J = 5.2 Hz, 1H), 8.26 (d, J = 5.2 Hz, 1H), 8.16-8.08 (m, 3H), 8.07-8.00 (m, 2H), 7.95-7.89 (m, 3H), 7.77 (s, 1H), 7.71 (t, J = 6.4 Hz, 1H), 7.27 (s, 1H), 7.18 (dd, J = 1.6, 5.2 Hz, 1H), 5.16 (dd, J = 5.2, 12.8 Hz, 1H), 4.46 (s, 2H), 4.31-4.19 (m, 2H), 3.68-3.62 (m, 2H), 3.61-3.50 (m, 12H), 3.49-3.41 (m, 2H), 2.95-2.82 (m, 1H), 2.64-2.54 (m, 2H), 2.11-2.02 (m, 1H) |
| 150 | I-150 | EL | EG | 896.0 | 10.87 (s, 1H), 9.74 (s, 1H), 8.77 (s, 1H), 8.75 (s, 1H), 8.34 (t, J = 5.2 Hz, |

| Ex-# | I-# | Step 1 Intermediate Amine | Step 1 Intermediate Acid | LCMS (ES+) m/z (M + H)+ | ¹HNMR (400 MHz, DMSO-d6) δ |
|---|---|---|---|---|---|
| | | | | | 1H), 8.07 (s, 1H), 7.93 (d, J = 5.2 Hz, 1H), 7.83-7.72 (m, 4H), 7.38-7.32 (m, 1H), 6.91-6.77 (m, 5H), 6.56 (t, J = 4.8 Hz, 1H), 4.82 (dd, J = 5.6, 12.8 Hz, 1H), 3.06-3.03 (m, 2H), 2.97-2.94 (m, 1H), 2.72-2.53 (m, 4H), 2.40-2.30 (m, 4H), 2.29-2.28 (m, 2H), 1.83-1.75 (m, 1H), 1.36-1.22 (m, 4H), 1.18-1.11 (m, 2H), 0.88-0.80 (m, 1H), 0.26-0.20 (m, 2H), 0.02--0.03 (m, 2H) |
| 151 | I-151 | EJ | CN | 957.3 | 11.10 (s, 1H), 11.02 (s, 1H), 9.04 (s, 2H), 8.66-8.64 (m, 1H), 8.26 (d, J = 5.2 Hz, 1H), 8.15 (s, 1H), 8.12-8.06 (m, 3H), 7.78 (s, 1H), 7.71 (t, J = 6.8 Hz, 1H), 7.61-7.54 (m, 1H), 7.27 (s, 1H), 7.19 (d, J = 5.2 Hz, 1H), 7.14 (d, J = 8.4 Hz, 1H), 7.03 (d, J = 7.2 Hz, 1H), 6.60 (s, 1H), 5.06 (dd, J = 12.0, 5.2 Hz, 1H), 4.33-4.17 (m, 4H), 3.76-3.70 (m, 12H), 2.97-2.90 (m, 1H), 2.34-2.30 (m, 2H), 2.12-1.95 (m, 4H) |

Variations in reaction time for Method 12 were as follows: Step 1 was run anywhere from 0.5-12 h, and Step 2 anywhere from 10 min-17 h. If the product of Step 1 was not a precipitate, a standard work up with water and extraction with ethyl acetate was used to isolate the product.

Example 152 (Method 13): N-[3-carbamoyl-1-[1-[2-[2-[2-[2-[[2-(2,6-dioxo-3-piperidyl)-1,3-dioxo-isoindolin-4-yl]amino]ethoxy]ethoxy]ethoxy]acetyl]-4-piperidyl]pyrazol-4-yl]-2-[2-(2,2,2-trifluoroethylamino)-4-pyridyl]oxazole-4-carboxamide, I-152

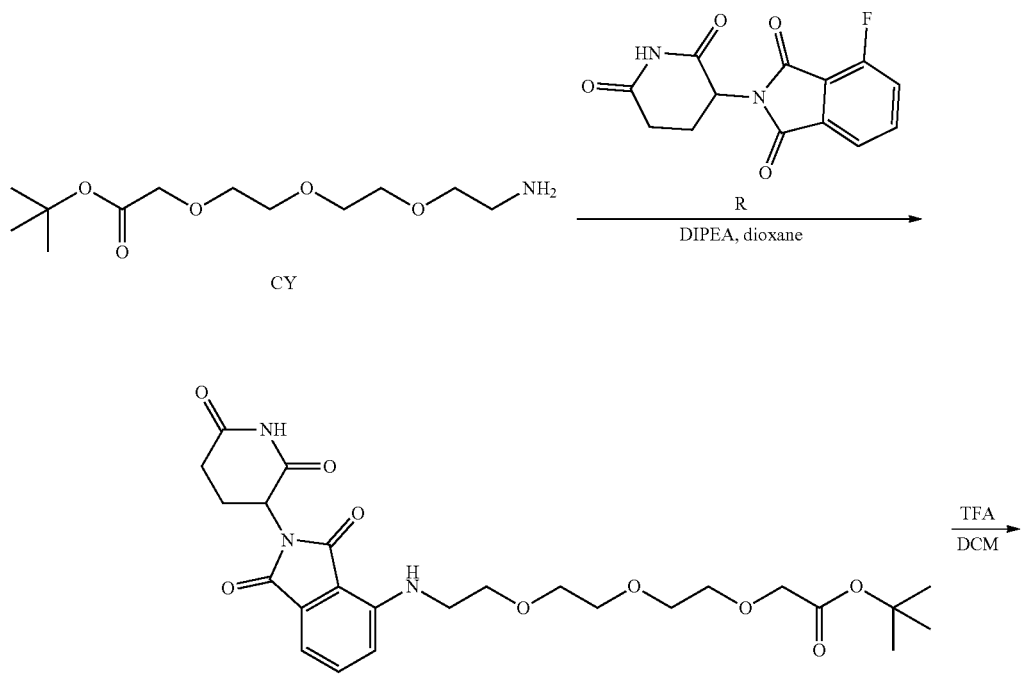

2233

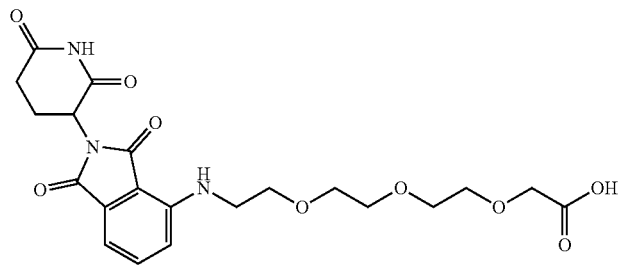

2234

-continued

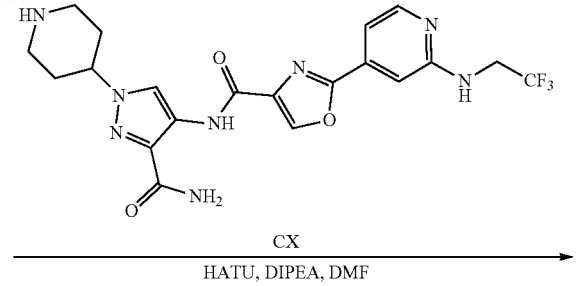

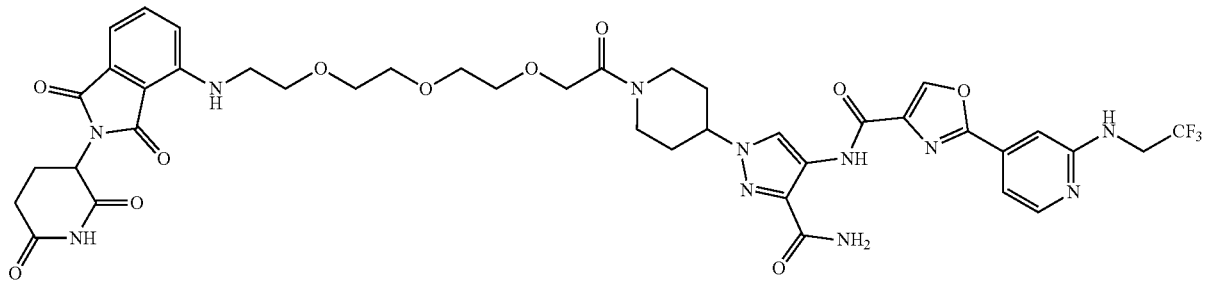

Step 1—Tert-butyl 2-(2-(2-(2-((2-(2,6-Dioxopiperidin-3-yl)-1,3-dioxoisoindolin-4-yl)amino)ethoxy)ethoxy)ethoxy)acetate To a solution of tert-butyl 2-[2-[2-(2-aminoethoxy)ethoxy]ethoxy]acetate (6.40 g, 24.3 mmol, Intermediate CY) and 2-(2,6-dioxo-3-piperidyl)-4-fluoro-isoindoline-1,3-dione (6.71 g, 24.3 mmol, Intermediate R) in dioxane (100 mL) was added DIPEA (9.42 g, 72.9 mmol). The reaction mixture was stirred at 115° C. for 24 hours. On completion, the reaction mixture was concentrated in vacuo to give yellow oil. The yellow oil was purified by prep-HPLC (water (0.1% FA)-ACN) to give the title compound (6.00 g, 48% yield) as a yellow oil. $^1$H NMR (400 MHz, CDCl$_3$) δ 8.19 (s, 1H), 7.54-7.45 (m, 1H), 7.11 (d, J=8.4 Hz, 1H), 6.93 (d, J=8.4 Hz, 1H), 6.52-6.48 (m, 1H), 4.99-4.87 (m, 1H), 4.02 (s, 2H), 3.75-3.68 (m, 10H), 3.50-3.46 (m, 2H), 2.93-2.69 (m, 3H), 2.17-2.10 (m, 1H), 1.49 (s, 9H).

Step 2—2-(2-(2-(2-(2-((2-(2,6-Dioxopiperidin-3-yl)-1,3-dioxoisoindolin-4-yl)amino)ethoxy)ethoxy)ethoxy)acetic acid To a solution of tert-butyl 2-[2-[2-[2-[[2-(2,6-dioxo-3-piperidyl)-1,3-dioxo-isoindolin-4-yl]amino]ethoxy]ethoxy]ethoxy]acetate (6.00 g, 11.6 mmol) in DCM (30 mL) was added TFA (30.8 g, 270 mmol). The reaction mixture was stirred at rt for 12 hours. On completion, the reaction mixture was concentrated in vacuo to give the title compound (5.60 g, 99% yield) as a yellow oil. LC-MS (ESI$^+$) m/z 464.0 (M+H)$^+$.

Step 3—N-[3-carbamoyl-1-[1-[2-[2-[2-[2-[[2-(2,6-dioxo-3-piperidyl)-1,3-dioxo-isoindolin-4-yl]amino]ethoxy]ethoxy]ethoxy]acetyl]-4-piperidyl]pyrazol-4-yl]-2-[2-(2,2,2-trifluoroethylamino)-4-pyridyl]oxazole-4-carboxamide To a mixture of N-[3-carbamoyl-1-(4-piperidyl)pyrazol-4-yl]-2-[2-(2,2,2-trifluoroethylamino)-4-pyridyl]oxazole-4-carboxamide (50.0 mg, 97.1 umol, Intermediate CX) and DIPEA (125 mg, 971 umol) in DMF (5 mL) was added 2-[2-[2-[2-[[2-(2,6-dioxo-3-piperidyl)-1,3-dioxo-isoindolin-4-yl]amino]ethoxy]ethoxy]ethoxy]acetic acid (54.0 mg, 116 umol) and HATU (44.3 mg, 116 umol). The reaction mixture was stirred at rt for 0.5 hour. On completion, the reaction mixture was concentrated in vacuo. The residue was purified by prep-HPLC (column: Phenomenex Synergi C18 150*25*10 um; mobile phase: [water (0.225% FA)-ACN]) to give the title compound I-152 (55.7 mg, 59% yield, FA) as a yellow solid. $^1$H NMR (400 MHz, DMSO-d$_6$) δ 11.10 (s, 1H), 10.94 (s, 1H), 8.96 (s, 1H), 8.39 (s, 1H), 8.25 (d, J=5.6 Hz, 1H), 7.74-7.66 (m, 2H), 7.62-7.54 (m, 1H), 7.51 (s, 1H), 7.26 (s, 1H), 7.16 (d, J=5.2 Hz, 1H), 7.13 (d, J=8.4 Hz, 1H), 7.03 (d, J=7.2 Hz, 1H), 6.59 (s, 1H), 5.05 (dd, J=5.6, 12.8 Hz, 1H), 4.61-4.39 (m, 2H), 4.32-4.21 (m, 2H), 4.20-4.12 (m, 2H), 3.94 (d, J=13.6 Hz, 1H), 3.63-3.59 (m, 2H), 3.58-3.53 (s, 8H), 3.46 (d, J=5.2 Hz, 2H), 3.18-3.10 (m, 1H), 2.94-2.83 (m, 1H), 2.83-2.71 (m, 1H), 2.63-2.56 (m, 1H), 2.56-2.53 (m, 1H), 2.07-1.92 (m, 4H), 1.85 (d, J=9.6 Hz, 1H); LC-MS (ESI$^+$) m/z 924.3 (M+H)$^+$.

TABLE 11

Compounds synthesized via Method 13 with the addition of various
amines to fluoride Intermediate R in Step 1, followed by coupling with various amines in Step 3.

| Ex-# | I-# | Step 1 Intermediate Amine | Step 3 Intermediate Amine | LCMS (ES+) m/z (M + H)+ | 1HNMR (400 MHz, DMSO-d6) δ |
|---|---|---|---|---|---|
| 153 | I-153 | DS | DR | 803.3 | 11.11 (br s, 1H), 8.53 (s, 1H), 7.65-7.55 (m, 1H), 7.21-7.13 (m, 2H), 7.11 (s, 1H), 7.06 (d, J = 6.8 Hz, 1H), 6.68 (t, J = 5.6 Hz, 1H), 5.20-5.11 (m, 1H), 5.07 (dd, J = 5.6, 12.8 Hz, 1H), 4.20 (s, 2H), 3.93 (t, J = 6.4 Hz, 1H), 3.71-3.60 (m, 2H), 3.53-3.49 (m, 3H), 3.47-3.44 (m, 3H), 3.14-2.99 (m, 2H), 2.96-2.88 (m, 2H), 2.66-2.54 (m, 4H), 2.44-2.40 (m, 5H), 2.32-2.25 (m, 1H), 2.18-2.02 (m, 3H), 1.81-1.79 (m, 2H), 1.69-1.48 (m, 3H), 1.42-1.27 (m, 2H) |
| 154[a] | I-154 | CZ | CX | 880.4 | 11.11 (s, 1H), 10.93 (s, 1H), 8.97 (s, 1H), 8.39 (s, 1H), 8.25 (d, J = 5.6 Hz, 1H), 7.71 (s, 1H), 7.69 (s, 1H), 7.57 (t, J = 7.6 Hz, 1H), 7.52 (s, 1H), 7.25 (s, 1H), 7.19-7.11 (m, 2H), 7.03 (d, J = 7.2 Hz, 1H), 6.60 (s, 1H), 5.06 (dd, J = 5.2, 13.2 Hz, 1H), 4.58-4.41 (m, 2H), 4.30-4.22 (m, 2H), 4.20 (s, 2H), 3.92 (d, J = 12.8 Hz, 1H), 3.70-3.53 (m, 8H), 3.47 (d, J = 4.8 Hz, 4H), 3.25-3.04 (m, 1H), 2.91-2.80 (m, 1H), 2.77-2.71 (m, 1H), 2.61 (s, 1H), 2.58-2.56 (m, 1H), 2.04 (s, 4H), 1.85 (d, J = 9.2 Hz, 1H) |
| 155 | I-155 | DA | CX | 968.5 | 11.10 (s, 1H), 10.94 (s, 1H), 8.97 (s, 1H), 8.40 (s, 1H), 8.24 (d, J = 5.2 Hz, 1H), 7.72 (s, 1H), 7.69 (s, 1H), 7.60-7.55 (m, 1H), 7.52 (s, 1H), 7.25 (s, 1H), 7.17-7.14 (m, 1H), 7.13 (d, J = 8.4 Hz, 1H), 7.03 (d, J = 6.8 Hz, 1H), 6.62-6.55 (m, 1H), 5.05 (dd, J = 5.6, 13.2 Hz, 1H), 4.63-4.39 (m, 2H), 4.24 (dd, J = 6.4, 9.6 Hz, 2H), 4.18 (d, J = 6.8 Hz, 2H), 3.94 (d, J = 13.2 Hz, 1H), 3.60 (d, J = 5.2 Hz, 2H), 3.57-3.49 (m, 12H), 3.48-3.44 (m, 2H), 3.21-3.07 (m, 1H), 2.93-2.85 (m, 1H), 2.80-2.73 (m, 1H), 2.64-2.59 (m, 1H), 2.58-2.56 (m, 1H), 2.08-1.91 (m, 4H), 1.86 (d, J = 14.4 Hz, 1H) |
| 156[a] | I-156 | CZ | DB | 852.4 | 11.10 (s, 1H), 10.91 (s, 1H), 8.97 (s, 1H), 8.48 (s, 1H), 8.25 (d, J = 5.2 Hz, 1H), 7.84 (s, 1H), 7.69 (t, J = 6.4 Hz, 1H), 7.58 (s, 1H), 7.57-7.51 (m, 1H), 7.25 (s, 1H), 7.17 (d, J = 5.2 Hz, 1H), 7.10 (d, J = 8.8 Hz, 1H), 6.99 (d, J = 6.8 Hz, 1H), 6.55 (s, 1H), 5.45-5.34 (m, 1H), 5.08-5.01 (m, 1H), 4.70-4.63 (m, 1H), 4.60-4.53 (m, 1H), 4.41-4.33 (m, 1H), 4.29-4.20 (m, 3H), 4.11-4.03 (m, 2H), 3.63-3.46 (m, 8H), 2.91-2.82 (m, 1H), 2.64-2.57 (m, 1H), 2.57-2.55 (m, 1H), 2.06-2.00 (m, 1H) |
| 157 | I-157 | DA | DB | 940.5 | 11.10 (s, 1H), 10.95 (s, 1H), 8.97 (s, 1H), 8.52 (s, 1H), 8.24 (d, J = 5.2 Hz, 1H), 7.88 (s, 1H), 7.68 (t, J = 6.8 Hz, 1H), 7.59 (s, 1H), 7.55 (d, J = 8.4 Hz, 1H), 7.24 (s, 1H), 7.15 (d, J = 4.4 Hz, 1H), 7.11 (d, J = 8.8 Hz, 1H), 7.02 (d, J = 7.2 Hz, 1H), 6.60-6.55 (m, 1H), 5.47-5.37 (m, 1H), 5.08-5.01 (m, 1H), 4.72-4.62 (m, 1H), 4.58-4.50 (m, |

TABLE 11-continued

Compounds synthesized via Method 13 with the addition of various amines to fluoride Intermediate R in Step 1, followed by coupling with various amines in Step 3.

| Ex-# | I-# | Step 1 Intermediate Amine | Step 3 Intermediate Amine | LCMS (ES+) m/z (M + H)+ | 1HNMR (400 MHz, DMSO-d6) δ |
|---|---|---|---|---|---|
| 158 | I-158 | CY | DB | 896.4 | 1H), 4.41-4.32 (m, 1H), 4.30-4.19 (m, 3H), 4.04 (s, 2H), 3.61-3.49 (m, 16H), 2.93-2.87 (m, 1H), 2.63-2.60 (m, 1H), 2.58-2.57 (m, 1H), 2.06-2.00 (m, 1H) 11.11 (s, 1H), 10.94 (s, 1H), 8.97 (s, 1H), 8.51 (s, 1H), 8.24 (d, J = 5.2 Hz, 1H), 7.89 (s, 1H), 7.74-7.65 (m, 1H), 7.60 (s, 1H), 7.57-7.50 (m, 1H), 7.24 (s, 1H), 7.16 (d, J = 4.8 Hz, 1H), 7.09 (d, J = 8.4 Hz, 1H), 7.01 (d, J = 6.8 Hz, 1H), 6.61-6.52 (m, 1H), 5.48-5.35 (m, 1H), 5.08-5.02 (m, 1H), 4.73-4.62 (m, 1H), 4.59-4.49 (m, 1H), 4.40-4.33 (m, 1H), 4.30-4.21 (m, 3H), 4.03 (s, 2H), 3.61-3.58 (m, 2H), 3.57-3.53 (m, 10H), 2.91-2.85 (m, 1H), 2.63-2.59 (m, 1H), 2.57-2.55 (m, 1H), 2.05-1.97 (m, 1H) |

Variations in reaction time for Method 13 were as follows: Step 1 was run anywhere from 16-24 h and Step 2 was run anywhere from 0.5-16 h.
<sup>a</sup>Since the product of Step 1 was the ethyl ester, not BOC ester, the deprotection for Step 2 used (Bu₃Sn)₂O in toluene and the reaction mixture was stirred at 115° C. for 4 hours. This intermediate was then purified by prep-HPLC (0.1% FA.)

Further Examples Using Synthetic Methods Similar to Method 13

Example 159: N-[3-carbamoyl-1-[4-[2-[2-[2-[[2-(2,6-dioxo-3-piperidyl)-1,3-dioxo-isoindolin-4-yl]amino]ethoxy]ethoxy]ethyl-methyl-carbamoyl]phenyl]pyrazol-4-yl]-2-[2-(2,2,2-trifluoroethylamino)-4-pyridyl]oxazole-4-carboxamide, I-159

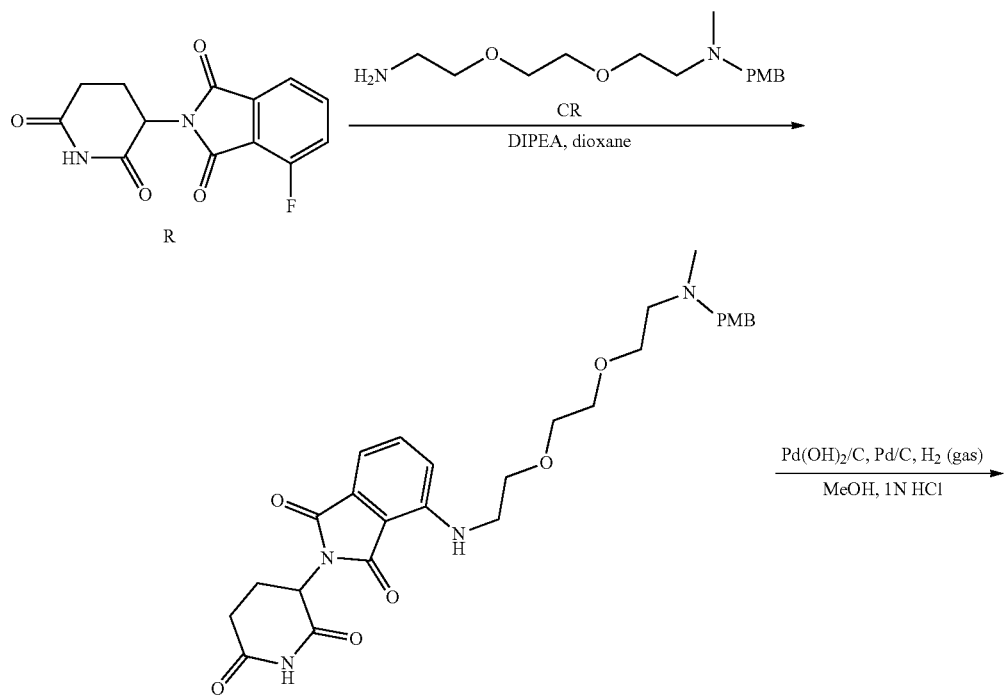

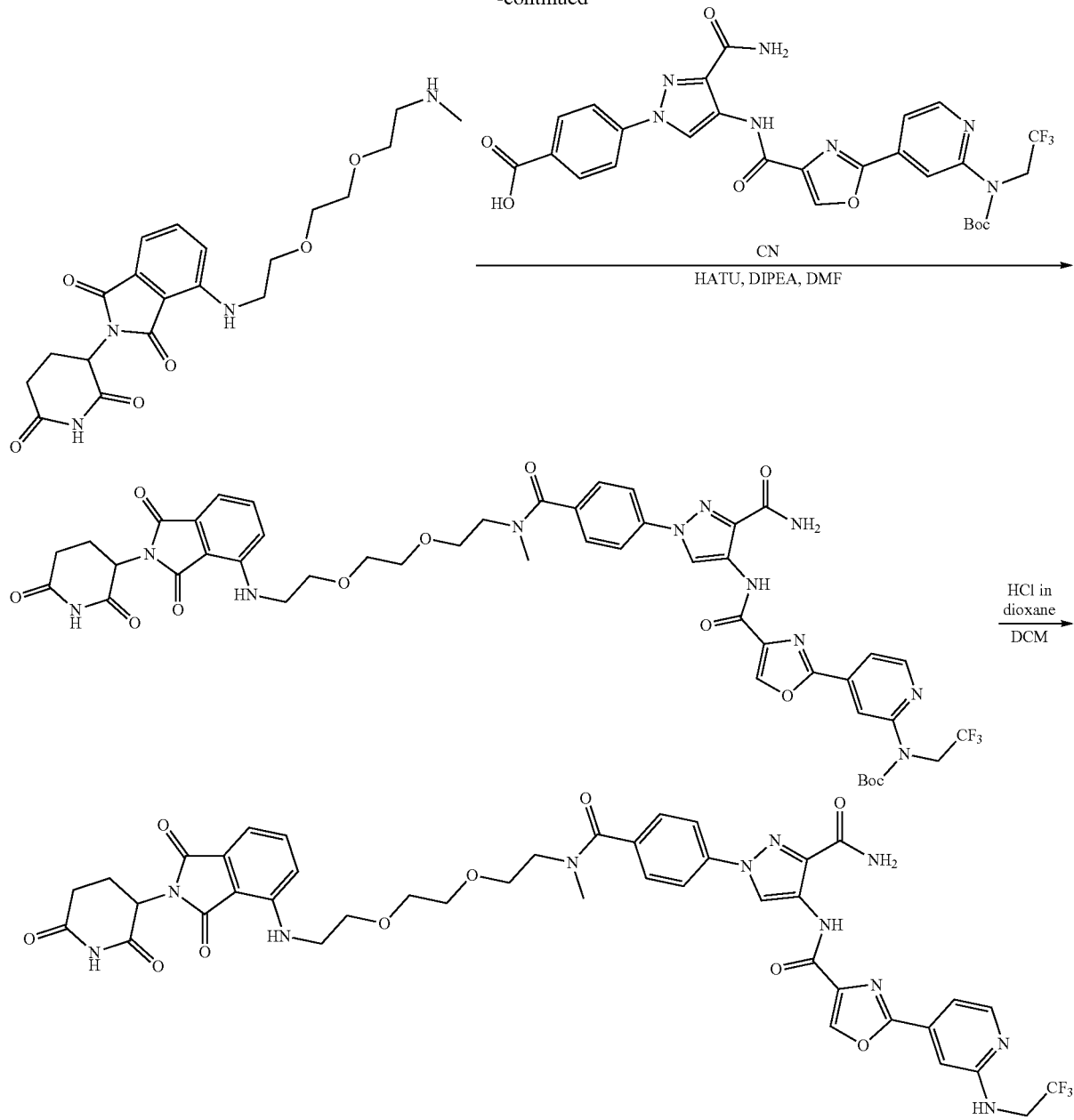

Step 1—2-(2,6-Dioxo-3-piperidyl)-4-[2-[2-[2-[(4-methoxyphenyl)methyl-methyl-amino]ethoxy]ethoxy]ethylamino]isoindoline-1,3-dione To a solution of 2-[2-[2-[(4-methoxyphenyl)methyl-methyl-amino]ethoxy]ethoxy]ethanamine (350 mg, 1.24 mmol, Intermediate CR) and 2-(2,6-dioxo-3-piperidyl)-4-fluoro-isoindoline-1,3-dione (342 mg, 1.24 mmol, Intermediate R) in dioxane (5 mL) was added DIPEA (1.60 g, 12.3 mmol, 2.16 mL). The reaction mixture was stirred at 115° C. for 16 hours. On completion, the mixture was concentrated in vacuo to give a residue. The residue was purified by reverse phase (0.1% NH$_3$.H$_2$O) to give the title compound (600 mg, 89% yield) as a yellow oil. LC-MS (ESI$^+$) m/z 539.4 (M+H)$^+$.

Step 2—2-(2,6-Dioxo-3-piperidyl)-4-[2-[2-[2-(methylamino)ethoxy]ethoxy]ethyl amino]isoindoline-1,3-dione To a mixture of 2-(2,6-dioxo-3-piperidyl)-4-[2-[2-[2-[(4-methoxyphenyl)methyl-methyl-amino]ethoxy]ethoxy]ethylamino]isoindoline-1,3-dione (0.10 g, 185 umol) in MeOH (3 mL) and IN HCl (0.05 mL) was added Pd/C (0.05 g, 10 wt %) and Pd(OH)$_2$/C (0.05 g, 10 wt %). Then the reaction mixture was stirred at rt for 2 hours under hydrogen atmosphere (15 psi pressure). On completion, the mixture was filtered and the filtrate was concentrated in vacuo to give the title compound (60.0 mg, 77% yield) as a yellowish oil. LC-MS (ESI$^+$) m/z 419.1 (M+H)$^+$.

Step 3—Tert-butyl N-[4-[4-[[3-carbamoyl-1-[4-[2-[2-[2-[[2-(2,6-dioxo-3-piperidyl)-1,3-dioxo-isoindolin-4-yl]amino]ethoxy]ethoxy]ethyl-methyl-carbamoyl]phenyl]pyrazol-4-yl]carbamoyl]oxazol-2-yl]-2-pyridyl]-N-(2,2,2-trifluoroethyl)carbamate To a mixture of 2-(2,6-dioxo-3-piperidyl)-4-[2-[2-[2-(methylamino)ethoxy]ethoxy]ethylamino]isoindoline-1,3-dione (77.0 mg, 169 umol, HCl) and 4-[4-[[2-[2-[tert-butoxycarbonyl(2,2,2-trifluoroethyl)amino]-4-pyridyl]oxazole-4-carbonyl]amino]-3-carbamoyl-pyrazol-1-yl]benzoic acid (88.5 mg, 143 umol, Intermediate CN) in DMF (3 mL) was added DIPEA (109 mg, 846 umol, 147 uL). Then HATU (83.6 mg, 220 umol) was added to the mixture. The reaction mixture was stirred at rt for 12 hours. On completion, the mixture was concentrated in vacuo to give a residue. The residue was purified by prep-HPLC (column: Phenomenex Synergi C18 150*25*10 um; mobile phase: [water (0.225% FA)-ACN]; B %: 50%-80%) to give the title compound (0.05 g, 23% yield) as white solid. LC-MS (ESI+) m/z 1016.0 (M+H)+.

Step 4—N-[3-carbamoyl-1-[4-[2-[2-[2-[[2-(2,6-dioxo-3-piperidyl)-1,3-dioxo-isoindolin-4-yl]amino]ethoxy]ethoxy]ethyl-methyl-carbamoyl]phenyl]pyrazol-4-yl]-2-[2-(2,2,2-trifluoroethylamino)-4-pyridyl]oxazole-4-carboxamide To a mixture of tert-butyl N-[4-[4-[[3-carbamoyl-1-[4-[2-[2-[2-[[2-(2,6-dioxo-3-piperidyl)-1,3-dioxo-isoindolin-4-yl]amino]ethoxy]ethoxy]ethyl-methyl-carbamoyl]phenyl]pyrazol-4-yl]carbamoyl]oxazol-2-yl]-2-pyridyl]-N-(2,2,2-trifluoroethyl)carbamate (42.0 mg, 41.3 umol) in DCM (3 mL) was added HCl in dioxane (4 M, 0.3 mL). Then the reaction mixture was stirred at rt for 0.5 hour. On completion, the mixture was concentrated in vacuo to give a residue. The residue was purified by prep-HPLC (column: Phenomenex Synergi C18 150*25*10 um; mobile phase: [water (0.225% FA)-ACN]; B %: 31%-61%) to give the title compound I-159 (20.0 mg, 50% yield) as a white solid. 1H NMR (400 MHz, DMSO-d6) δ11.15-10.96 (m, 2H), 9.18-8.78 (m, 2H), 8.27 (s, 1H), 8.12-7.96 (m, 3H), 7.78-7.50 (m, 5H), 7.31-7.00 (m, 4H), 6.58 (s, 1H), 5.05 (s, 1H), 4.25 (s, 2H), 3.70-3.62 (s, 8H), 3.55-3.49 (m, 4H), 2.98 (s, 3H), 2.87 (s, 1H), 2.65-2.58 (m, 2H), 2.02-2.00 (m, 1H); LC-MS (ESI+) m/z 916.3 (M+H)+.

Example 160: (2S)-3-[(8R)-1-[4-[4-[2-[2-[2-[[2-(2,6-dioxo-3-piperidyl)-1,3-dioxo-isoindolin-4-yl]amino]ethoxy]ethoxy]acetyl]piperazin-1-yl]cyclohexoxyl-7,8-dihydro-6H-cyclopenta[4,5]thieno 1,2-c]pyrimidin-8-yl]-2-hydroxy-propanamide, I-160

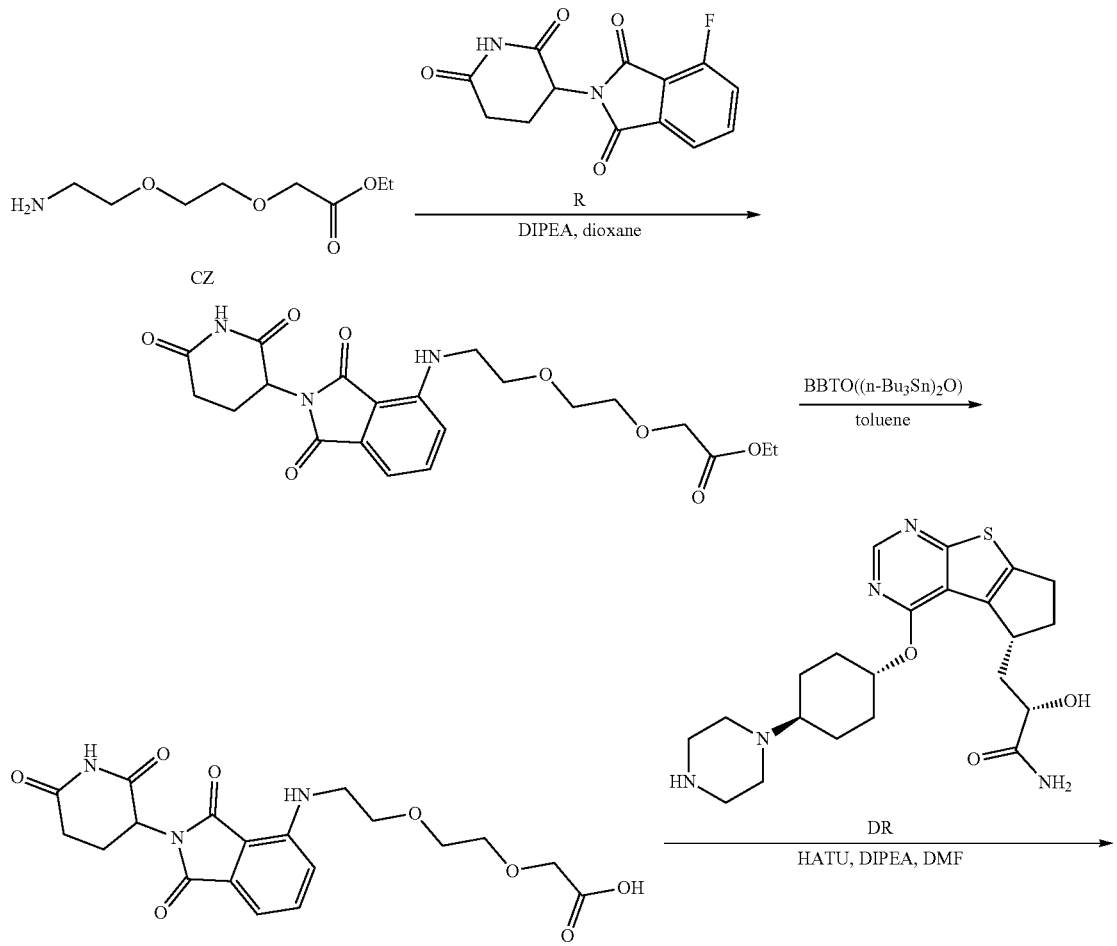

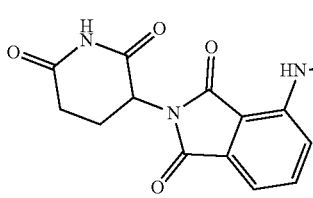
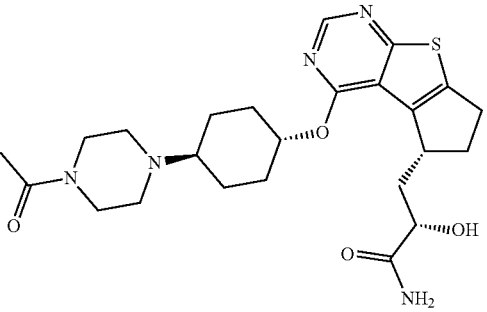

The title compound was synthesized via Method 13, using fluoride Intermediate R and amine intermediate CZ in the first step which was run at 115° C. for 18 hours. In Step 2, the ester was deprotected as follows: to a mixture of (Bu₃Sn)₂O (1.17 g, 1.97 mmol) in toluene (5 mL) was added ethyl 2-[2-[2-[[2-(2,6-dioxo-3-piperidyl)-1,3-dioxo-isoindolin-4-yl]amino]ethoxy]ethoxy]acetate (440 mg, 983 umol). The reaction mixture was stirred at 115° C. for 4 hours. On completion, the reaction mixture was concentrated in vacuo. The residue was purified by prep-HPLC (0.1% FA) to give 2-[2-[2-[[2-(2,6-Dioxo-3-piperidyl)-1,3-dioxo-isoindolin-4-yl]amino]ethoxy]ethoxy]acetic acid (230 mg, 55% yield) as a yellow solid (LC-MS (ESI⁺) m/z 420.1 (M+H)⁺; ¹H NMR (400 MHz, DMSO-d₆) δ=13.39-11.73 (m, 1H), 11.10 (s, 1H), 7.65-7.52 (m, 1H), 7.16 (d, J=8.4 Hz, 1H), 7.05 (d, J=7.2 Hz, 1H), 7.08-7.02 (m, 1H), 6.62 (t, J=5.6 Hz, 1H), 5.06 (dd, J=5.2, 12.8 Hz, 1H), 4.02 (s, 2H), 3.67-3.56 (m, 6H), 3.52-3.46 (m, 2H), 2.95-2.81 (m, 2H), 2.69-2.54 (m, 2H), 2.07-1.99 (m, 1H)). Intermediate DR was used as the amine in Step 3 to give the final compound I-160. Characterization data: ¹H NMR (400 MHz, DMSO-d₆) δ=11.12 (s, 1H), 8.52 (s, 1H), 7.59 (t, J=7.6 Hz, 1H), 7.15 (dd, J=9.6, 18.4 Hz, 3H), 7.05 (d, J=6.8 Hz, 1H), 6.60 (s, 1H), 5.11 (d, J=11.2 Hz, 1H), 5.06 (dd, J=5.2, 12.8 Hz, 1H), 4.14 (s, 2H), 3.95-3.90 (m, 5H), 3.64 (d, J=4.8 Hz, 2H), 3.59-3.55 (m, 4H), 3.52-3.34 (m, 8H), 3.02 (dd, J=8.4, 16.0 Hz, 1H), 2.94-2.86 (m, 2H), 2.65-2.54 (m, 3H), 2.41 (d, J=9.6 Hz, 2H), 2.33-2.26 (m, 1H), 2.16-2.04 (m, 3H), 1.82 (d, J=10.0 Hz, 2H), 1.64-1.47 (m, 3H), 1.43-1.31 (m, 2H). LC-MS (ESI⁺) m/z 847.1 (M+H)⁺.

Example 161: (2S)-3-[(8R)-1-[4-[4-[2-[2-[2-[2-[2-[[2-(2,6-dioxo-3-piperidyl)-1,3-dioxo-isoindolin-4-yl]amino]ethoxy]ethoxy]ethoxy]ethoxy]acetyl]piperazin-1-yl]cyclohexoxy]-7,8-dihydro-6H-cyclopenta[4,5]thieno[1,2-c]pyrimidin-8-yl]-2-hydroxy-propanamide, I-161

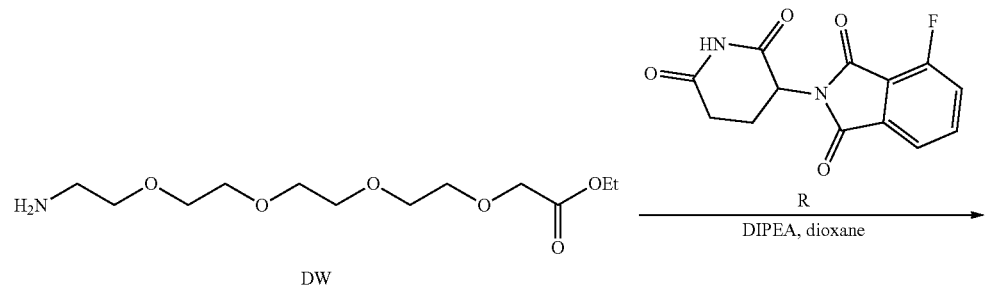

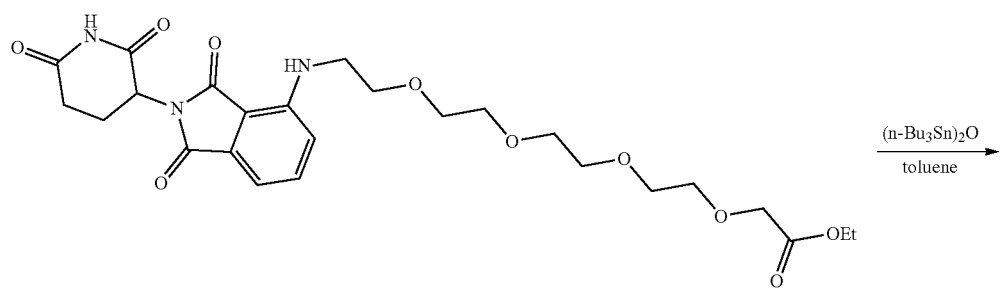

-continued

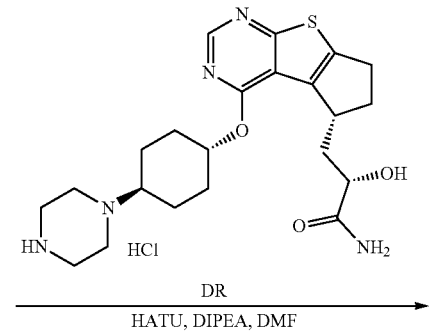

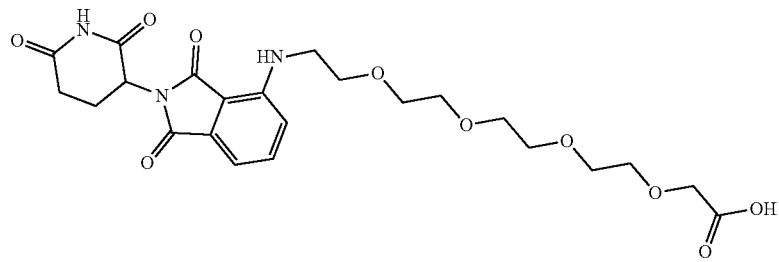

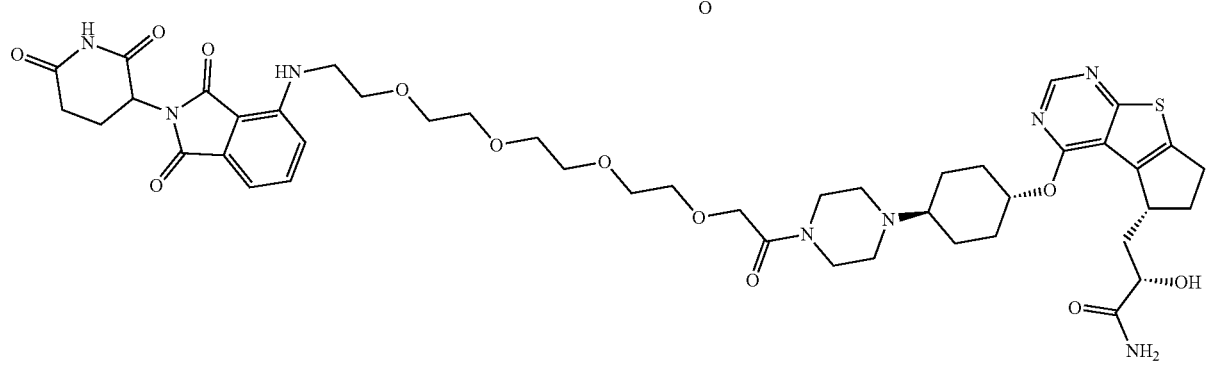

The title compound was synthesized via Method 13, using fluoride Intermediate R and amine Intermediate DW in the first step which was run at 115° C. for 16 hours. In Step 2, the ester was deprotected as follows: to a solution of (Bu$_3$Sn)$_2$O (779 mg, 1.31 mmol) in toluene (20 mL) was added ethyl 2-[2-[2-[2-[2-[[2-(2,6-dioxo-3-piperidyl)-1,3-dioxo-isoindolin-4-yl]amino]ethoxy]ethoxy]ethoxy]ethoxy] acetate (0.35 g, 654 umol). The reaction mixture was stirred at 115° C. for 12 hours. On completion, the reaction mixture was quenched with 1 N sodium fluoride solution. The mixture was extracted with DCM (100 mL), then dried and concentrated in vacuo. The crude was purified by reverse phase flash chromatography (0.1% FA) to give 2-[2-[2-[2-[2-[[2-(2,6-dioxo-3-piperidyl)-1,3-dioxo-isoindolin-4-yl] amino]ethoxy]ethoxy]ethoxy]ethoxy]acetic acid (0.175 g, 53% yield) as yellow oil (LCMS (M+1)+: 508.2). Intermediate DR was used as the amine in Step 3 to give the final compound I-161. Characterization data: $^1$H NMR (400 MHz, DMSO-d$_6$) δ 11.10 (s, 1H), 8.52 (s, 1H), 7.58 (t, J=7.6 Hz, 1H), 7.21-7.07 (m, 3H), 7.04 (d, J=7.2 Hz, 1H), 6.61 (t, J=5.6 Hz, 1H), 5.21-5.11 (m, 1H), 5.10-5.01 (m, 1H), 4.12 (s, 2H), 3.93 (t, J=6.4 Hz, 1H), 3.66-3.62 (m, 2H), 3.60-3.49 (m, 20H), 3.07-3.00 (m, 1H), 2.94-2.84 (m, 2H), 2.63-2.56 (m, 2H), 2.55-2.53 (m, 2H), 2.47-2.36 (m, 5H), 2.32-2.26 (m, 1H), 2.20-2.08 (m, 2H), 2.06-1.99 (m, 1H), 1.90-1.79 (m, 2H), 1.70-1.57 (m, 2H), 1.56-1.47 (m, 1H), 1.45-1.33 (m, 2H); LC-MS (ESI$^+$) m/z 957.4 (M+Na)$^+$.

Example 162 (Method 14): 5-[[(1S,2R)-2-aminocyclohexyl]amino]-7-[3-[2-[2-[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethylpropyl]amino]-2-oxo-ethoxy]ethoxy]ethoxy]ethoxy]-5-methoxy-anilino]imidazo[1,2-c]pyrimidine-8-carboxamide, I-162

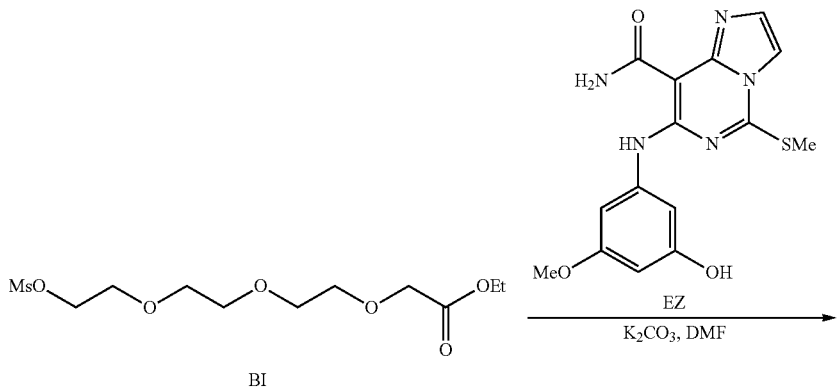

2247 2248
-continued
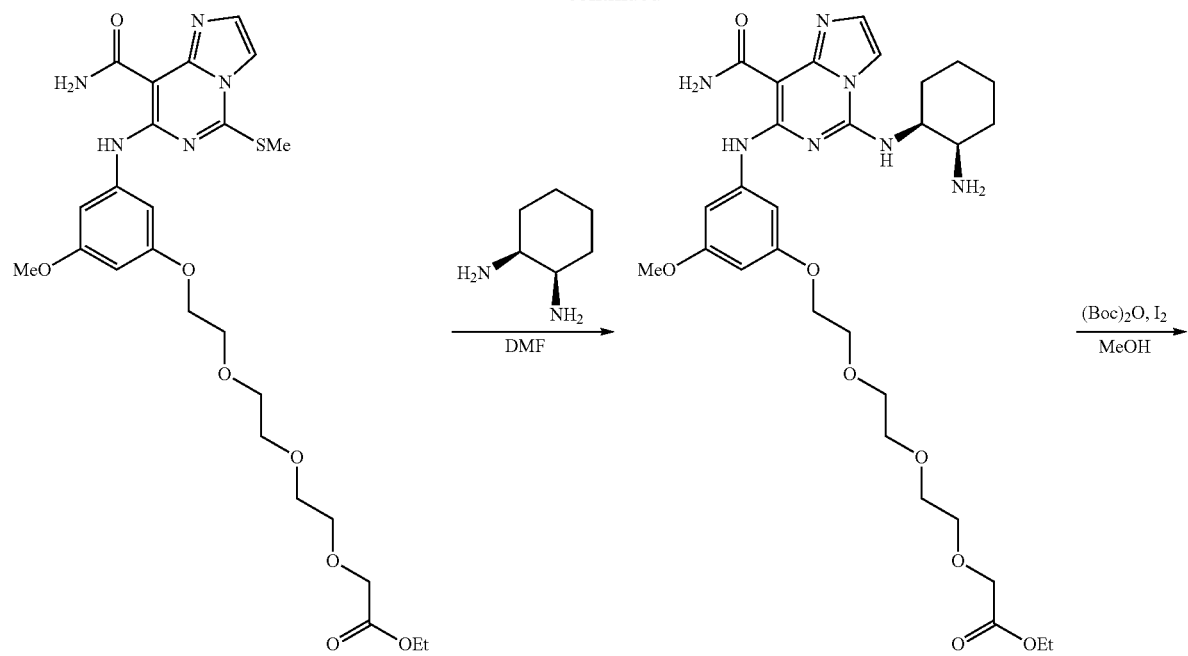
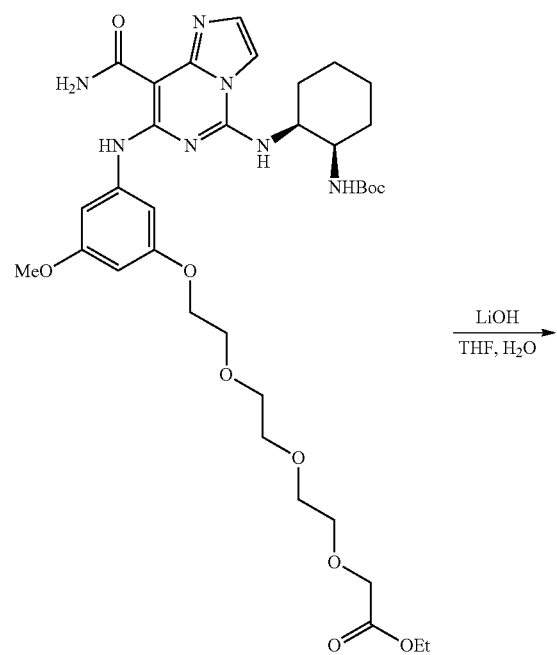

2249
2250
-continued
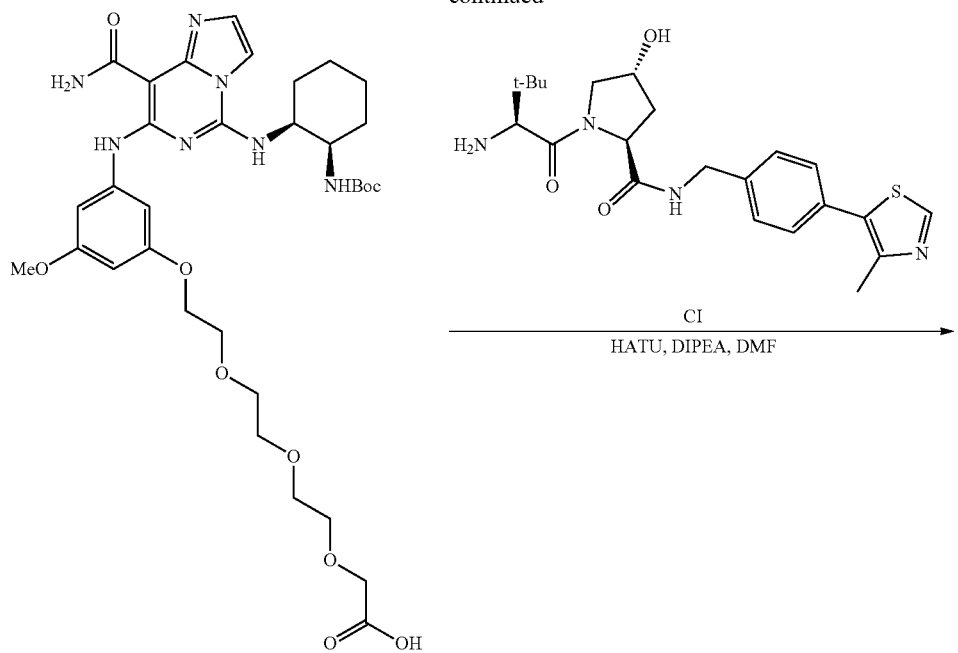
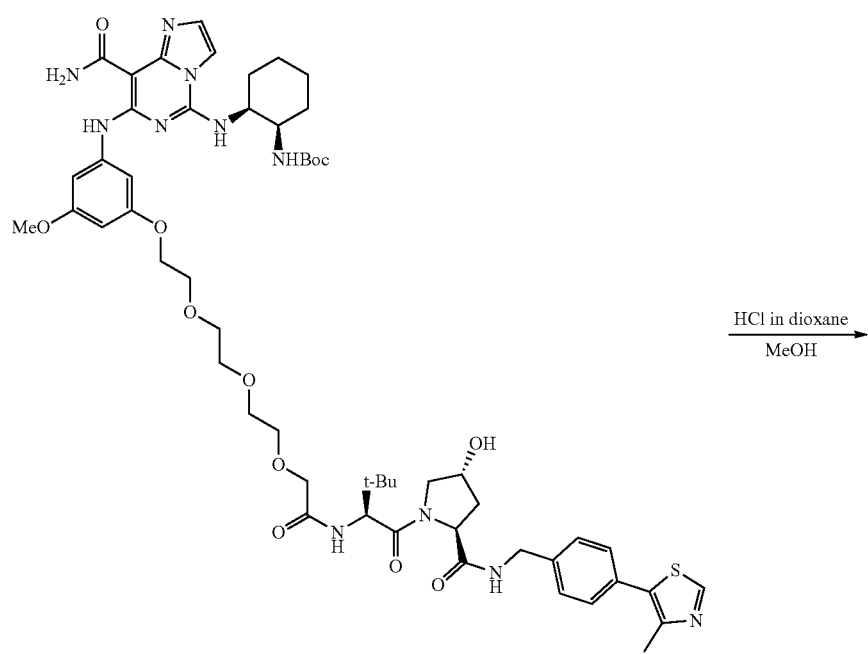

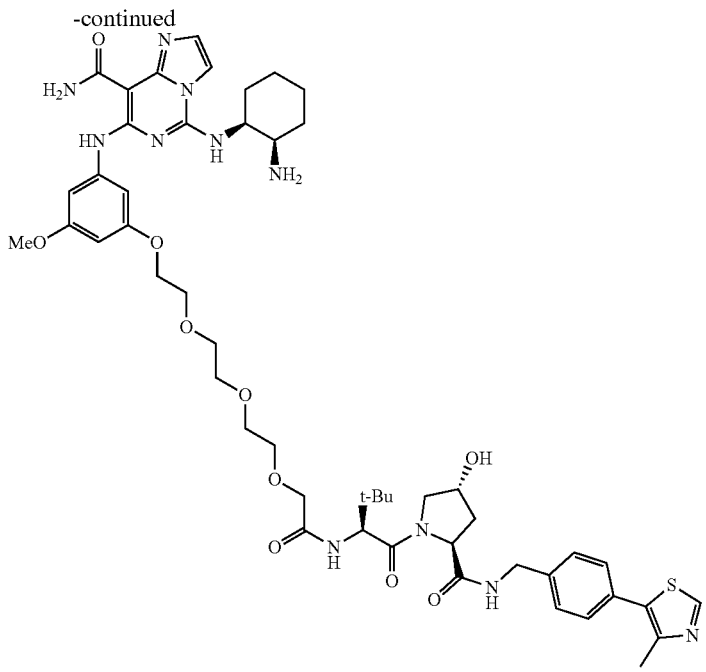

Step 1—Ethyl 2-[2-[2-[2-[3-[(8-carbamoyl-5-methylsulfanyl-imidazo[1,2-c]pyrimidin-7-yl)amino]-5-methoxy-phenoxy]ethoxy]ethoxy]ethoxy]acetate To a solution of ethyl 2-[2-[2-(2-methylsulfonyloxyethoxy)ethoxy]ethoxy]acetate (819 mg, 2.61 mmol, Intermediate BI) and 7-(3-hydroxy-5-methoxy-anilino)-5-methylsulfanyl-imidazo[1,2-c]pyrimidine-8-carboxamide (300 mg, 868 umol, Intermediate EZ) in DMF (10 mL) was added $K_2CO_3$ (360 mg, 2.61 mmol). The mixture was stirred at 50° C. for 12 hours. On completion, the reaction mixture was concentrated in vacuo to remove solvent. The residue was diluted with water (5 mL) and extracted with DCM (3×10 mL). The combined organic layer was dried over sodium sulfate, filtered and concentrated in vacuo to give the title compound (320 mg, 65% yield) as a yellowish oil. LC-MS (ESI+) m/z 564.0 (M+H)+.

Step 2—Ethyl 2-[2-[2-[2-[3-[[5-[[(1S,2R)-2-aminocyclohexyl]amino]-8-carbamoyl-imidazo[1,2-c]pyrimidin-7-yl]amino]-5-methoxy-phenoxy]ethoxy]ethoxy]ethoxy]acetate A solution of ethyl 2-[2-[2-[2-[3-[(8-carbamoyl-5-methylsulfanyl-imidazo[1,2-c]pyrimidin-7-yl)amino]-5-methoxy-phenoxy]ethoxy]ethoxy]ethoxy]acetate (220 mg, 390 umol) and (1R,2S)-cyclohexane-1,2-diamine (89.1 mg, 781 umol, CAS #1436-59-5) in DMF (2 mL) was stirred at 90° C. for 3 hours. On completion, the reaction mixture was concentrated in vacuo to give a residue. The residue was diluted with water (5 mL) and extracted with DCM (3×10 mL). The combined organic layer was dried over anhydrous sodium sulfate, filtered and concentrated in vacuo to give the title compound (220 mg, 65% yield) as a yellowish oil. LC-MS (ESI+) m/z 630.1 (M+H)+.

Step 3—Ethyl 2-[2-[2-[2-[3-[[5-[[(1S,2R)-2-(tert-butoxycarbonylamino)cyclohexyl]amino]-8-carbamoyl-imidazo[1,2-c]pyrimidin-7-yl]amino]-5-methoxy-phenoxy]ethoxy]ethoxy]ethoxy]acetate To a solution of ethyl 2-[2-[2-[2-[3-[[5-[[(1S,2R)-2-aminocyclohexyl]amino]-8-carbamoyl-imidazo[1,2-c]pyrimidin-7-yl]amino]-5-methoxy-phenoxy]ethoxy]ethoxy]ethoxy]acetate (220 mg, 349 umol) and (Boc)$_2$O (152 mg, 699 umol) in MeOH (3 mL) was added $I_2$ (17.7 mg, 69.9 umol). The reaction mixture was stirred rt for 12 hours. On completion, the reaction mixture was concentrated in vacuo to remove solvent. The residue was diluted with water (5 mL) and extracted with DCM (3×5 mL). The combined organic layer was dried over sodium sulfate, filtered and concentrated in vacuo to give a residue. The residue was purified by silica gel column chromatography (DCM:MeOH=20:1) to give the title compound (150 mg, 58% yield) as a yellowish solid. LC-MS (ESI+) m/z 730.1 (M+H)+.

Step 4—2-[2-[2-[2-[3-[[5-[[(1S,2R)-2-(tert-butoxycarbonylamino)cyclohexyl]amino]-8-carbamoyl-imidazo[1,2-c]pyrimidin-7-yl]amino]-5-methoxy-phenoxy]ethoxy]ethoxy]ethoxy]acetic acid To a solution of ethyl 2-[2-[2-[2-[3-[[5-[[(1S,2R)-2-(tert-butoxycarbonylamino)cyclohexyl]amino]-8-carbamoyl-imidazo[1,2-c]pyrimidin-7-yl]amino]-5-methoxy-phenoxy]ethoxy]ethoxy]ethoxy]acetate (150 mg, 205 umol) in a mixed solvent of THF (2 mL) and H$_2$O (2 mL) was added LiOH (19.7 mg, 822 umol). Then the mixture was stirred at rt for 0.5 hour. On completion, saturated citric acid aqueous solution was added to the mixture to adjust the pH=5.0. The residue was diluted with water (3 mL) and extracted with DCM (3×5 mL). The combined organic layer was dried over sodium sulfate, filtered and concentrated in vacuo to give the title compound (135 mg, 94% yield) as white solid. LC-MS (ESI+) m/z 702.3 (M+H)+.

Step 5—Tert-butyl N-[(1R,2S)-2-[[8-carbamoyl-7-[3-[2-[2-[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethoxy]ethoxy]-5-methoxy-anilino]imidazo[1,2-c]pyrimidin-5-yl]amino]cyclohexyl]carbamate A solution of 2-[2-[2-[2-[3-[[5-[[(1S,2R)-2-(tert-butoxycarbonylamino)cyclohexyl]amino]-8-carbamoyl-imidazo[1,2-c]pyrimidin-7-yl]amino]-5-methoxy-phenoxy]ethoxy]ethoxy]ethoxy]acetic acid (135 mg, 192 umol) in DMF (2 mL) was cooled to 0° C. Then, DIPEA (67.8 mg, 525 umol), (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide (75.3 mg, 175 umol, Intermediate CI) and HATU (79.8 mg, 210 umol) were added. Then the mixture allowed to warm to rt and stirred for 6 hours. On completion, the mixture was diluted with water (5 mL) and extracted with EA (3×5 mL). The combined organic layer was dried over sodium sulfate, filtered and concentrated in vacuo to give a residue. The residue was purified by reverse phase chromatography (0.1% FA in water) to give the title compound (90.0 mg, 46% yield) as a yellowish solid. LC-MS (ESI$^+$) m/z 1114.2 (M+H)$^+$.

Step 6—5-[[(1S,2R)-2-aminocyclohexyl]amino]-7-[3-[2-[2-[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethoxy]ethoxy]-5-methoxy-anilino]imidazo[1,2-c]pyrimidine-8-carboxamide To a solution of tert-butyl N-[(1R,2S)-2-[[8-carbamoyl-7-[3-[2-[2-[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethoxy]ethoxy]-5-methoxy-anilino]imidazo[1,2-c]pyrimidin-5-yl]amino]cyclohexyl]carbamate (90.0 mg, 80.8 umol) in MeOH (2 mL) was added HCl in dioxane (4 M, 2 mL). Then the mixture was stirred at rt for 1 hour. On completion, the reaction mixture was concentrated in vacuo to give a residue. The residue was purified by prep-HPLC (column: Boston Green ODS 150*30 5 u; mobile phase: [water (0.225% FA)-ACN]) to give the title compound I-162 (20.0 mg, 24% yield, FA salt) as white solid. $^1$H NMR (400 MHz, DMSO-d$_6$) δ 12.39 (s, 1H), 9.56 (d, J=3.2 Hz, 1H), 8.96 (s, 1H), 8.59 (t, J 5.6 Hz, 1H), 8.14 (s, 1H), 7.48-7.36 (m, 6H), 7.32 (s, 1H), 6.92 (s, 1H), 6.67 (s, 1H), 6.21 (s, 1H), 4.59-4.52 (d, J=9.6 Hz, 1H), 4.45-4.31 (m, 4H), 4.29-4.18 (m, 2H), 4.12-4.00 (m, 3H), 3.96 (s, 2H), 3.74 (s, 4H), 3.72-3.64 (m, 7H), 3.61-3.57 (m, 10H), 2.53-2.51 (m, 2H), 2.43 (s, 3H), 2.10-1.98 (m, 2H), 1.92-1.80 (m, 2H), 1.76-1.70 (m, 2H), 1.47-1.34 (m, 2H), 0.94 (s, 9H); LC-MS (ESI$^+$) m/z 1014.2 (M+H)$^+$.

TABLE 12

Compounds synthesized via Method 14 with the displacement of various mesylates with alcohols in Step 1, followed by coupling of various amines in Step 5.

| Ex-# | I-# | Step 1 Mesylate | Step 1 Alcohol | Step 5 Amine | LCMS (ES+) m/z (M + H)$^+$ | $^1$HNMR (400 MHz, DMSO-d6) δ |
|---|---|---|---|---|---|---|
| 163 | I-163 | ethyl 2-[2-[2-[2-[2-(2-methylsulfonyloxyethoxy)ethoxy]ethoxy]ethoxy]acetate (synthesized via Steps 1-2 of Intermediate BW) | EZ | CI | 1124.6$^a$ | 12.39 (s, 1H), 9.56 (s, 1H), 8.96 (s, 1H), 8.59 (t, J = 5.6 Hz, 1H), 8.14 (s, 1H), 7.48-7.34 (m, 6H), 7.31 (s, 1H), 6.93 (s, 1H), 6.66 (s, 1H), 6.21 (s, 1H), 4.57-4.55 (d, J = 9.6 Hz, 1H), 4.48-4.31 (m, 3H), 4.29-4.19 (m, 2H), 4.06 (s, 3H), 3.95 (s, 2H), 3.80-3.74 (m, 4H), 3.73-3.65 (m, 8H), 3.58 (m, 18H), 2.43 (s, 3H), 2.10-1.98 (m, 2H), 1.94-1.83 (m, 2H), 1.73-1.65 (m, 3H), 1.59-1.35 (m, 3H), 0.93 (s, 9H) |
| 164 | I-164 | BK | FA | CI | 1110.4$^a$ | 12.19 (s, 1H), 9.54 (s, 1H), 8.97 (s, 1H), 8.60 (t, J = 5.6 Hz, 1H), 8.37 (s, 1H), 8.16 (s, 1H), 7.47-7.34 (m, 6H), 7.33-7.28 (m, 1H), 6.83 (s, 2H), 4.57 (d, J = 9.6 Hz, 1H), 4.55-4.51 (m, 4H), 4.50-4.33 (m, 3H), 4.31-4.19 (m, 3H), 3.80 (s, 6H), 3.69-3.61 (m, 14H), 2.44 (s, 3H), 2.08-1.80 (m, 4H), 1.67 (s, 2H), 1.58-1.36 (m, 3H), 1.35-1.20 (m, 1H), 0.95 (s, 9H) |
| 165 | I-165 | BI | FA | CI | 1044.5 | 12.18 (s, 1H), 9.53 (br s, 1H), 9.00-8.90 (m, 1H), 8.59-8.56 (m, 1H), 8.15 (s, 1H), 7.49-7.27 (m, 7H), 6.82 (s, 2H), 4.74-4.14 (m, 7H), 4.02-3.85 (m, 4H), 3.78 (s, 6H), 3.62-3.58 (m, 10H), 2.45-2.41 (m, 3H), |

TABLE 12-continued

Compounds synthesized via Method 14 with the displacement of various
mesylates with alcohols in Step 1, followed by coupling of various amines in Step 5.

| Ex-# | I-# | Step 1 Mesylate | Step 1 Alcohol | Step 5 Amine | LCMS (ES+) m/z (M + H)+ | 1HNMR (400 MHz, DMSO-d6) δ |
|---|---|---|---|---|---|---|
| | | | | | | 2.10-1.19 (m, 12H), 0.98 (d, J = 8.4 Hz, 9H) |

Variations in temperature and time for Method 14 were as follows: Step 1 was run at 50-90 C. for anywhere from 4-24 h, Step 3 was run at rt anywhere from 2-12 hours, Step 4 was run at rt anywhere from 0.5-2.5 h, Step 5 was run at rt anywhere from 6-16 h, and Step 6 was run at rt for anywhere from 0.5-1 h.
<sup>a</sup>LCMS measure as (M + Na)+.

Example 166 (Method 15) 4-[2-[2-[2-[2-[4-[[7-[[(1R,2S)-2-aminocyclohexyl]amino]-4-oxo-3H-pyrido[4,3-d]pyrimidin-5-yl]amino]indol-1-yl]ethoxy]ethoxy]ethoxy]ethylamino]-2-(2,6-dioxo-3-piperidyl)isoindoline-1,3-dione, I-166

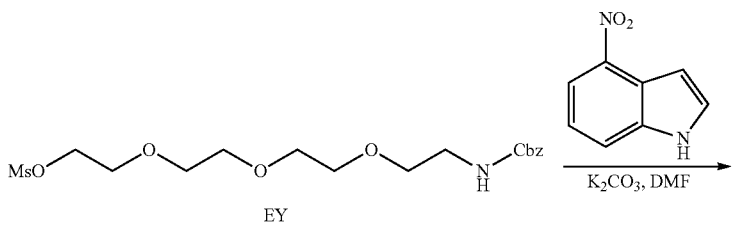

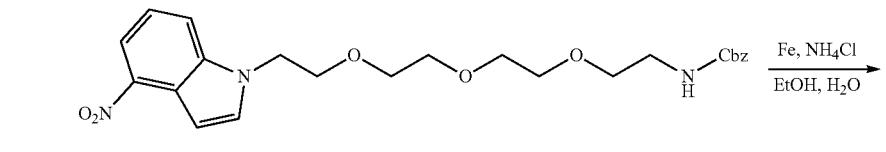

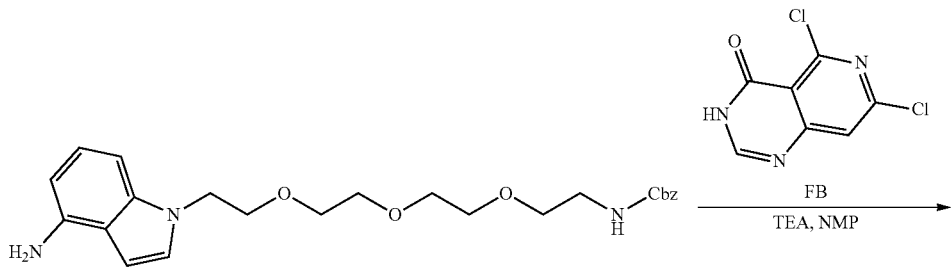

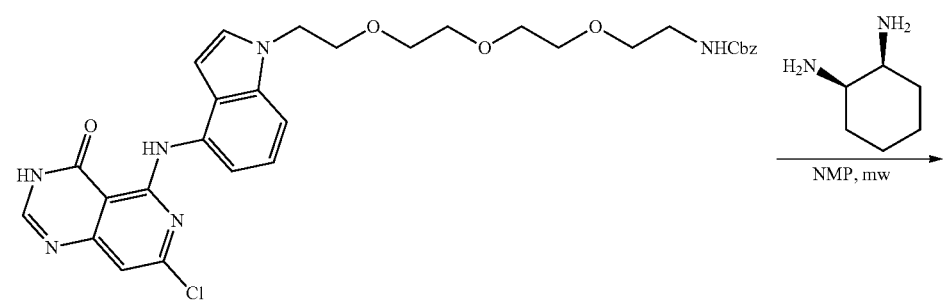

2257
-continued
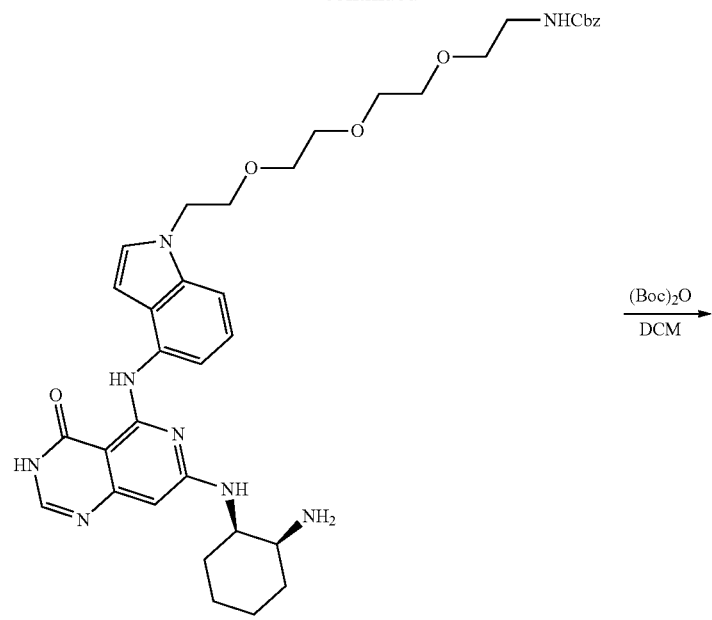
2258
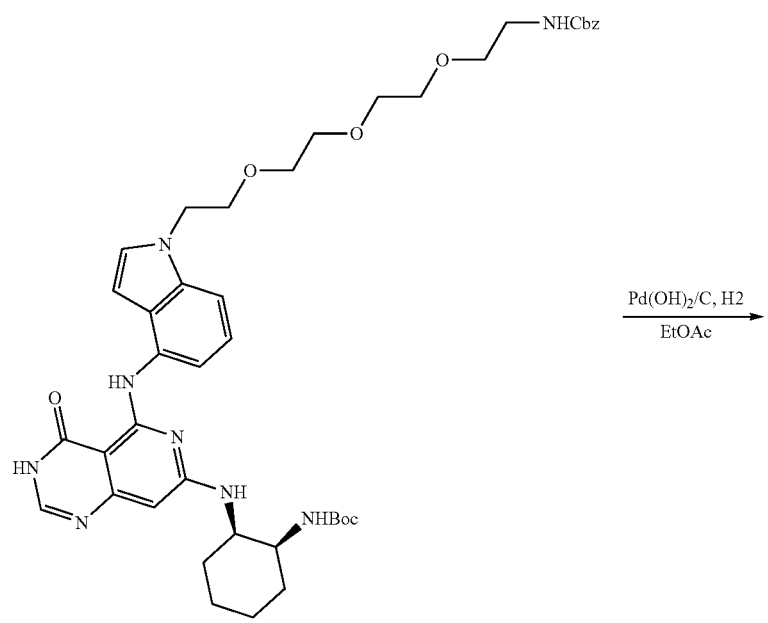

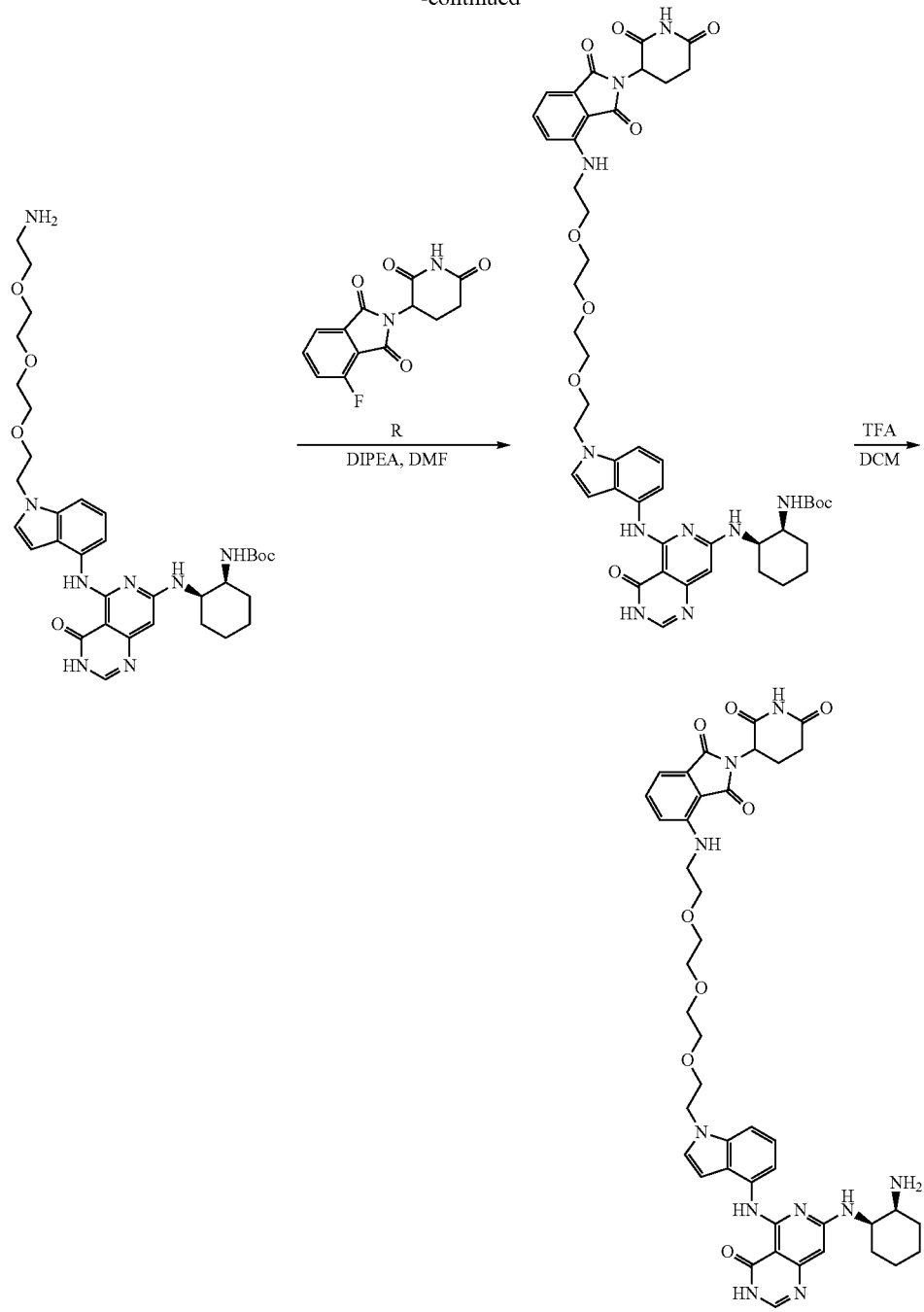

Step 1—Benzyl N-[2-[2-[2-[2-(4-nitroindol-1-yl)ethoxy]ethoxy]ethoxy]ethyl]carbamate To a mixture of 2-[2-[2-[2-(benzyloxycarbonylamino)ethoxy]ethoxy]ethoxy]ethyl methanesulfonate (100 mg, 246 umol, Intermediate EY) in DMF (2 mL) was added $K_2CO_3$ (68.1 mg, 493 umol) and 4-nitro-1H-indole (39.9 mg, 246 umol). The reaction mixture was stirred at 100° C. for 3 hours. On completion, the reaction mixture was concentrated in vacuo to remove DMF. The residue was diluted with water (4 mL) and extracted with dichloromethane (2×6 mL). The combined organic layer was dried over $Na_2SO_4$, filtered and concentrated in vacuo to give a residue. The residue was purified by prep-TLC (PE:EA=1:1) to give the title compound (67.0 mg, 57% yield) as a light yellow oil. LC-MS (ESI$^+$) m/z 494.1 (M+Na)$^+$.

Step 2—Benzyl N-[2-[2-[2-[2-(4-aminoindol-1-yl)ethoxy]ethoxy]ethoxy]ethyl]carbamate To a mixture of benzyl N-[2-[2-[2-[2-(4-nitroindol-1-yl)ethoxy]ethoxy]ethoxy]ethyl]carbamate (1.30 g, 2.76 mmol) in EtOH (10 mL) and $H_2O$ (4 mL) was added $NH_4Cl$ (1.48 g, 27.6 mmol) and Fe (1.54 g, 27.6 mmol) under nitrogen atmosphere. The reaction mixture was stirred at 80° C. for 3 hours. On completion, the reaction mixture was filtered and concentrated in vacuo to remove EtOH. The residue was diluted with water (10 mL) and neutralized with sat. NaHCO$_3$ until the pH=8-9. The residue was diluted with water (10 mL) and extracted with ethyl acetate (2×20 mL). The combined organic layer was dried over Na$_2$SO$_4$, filtered and concentrated in vacuo to give the title compound (1.14 g, 93% yield) as a light yellow oil. LC-MS (ESI$^+$) m/z 442.1 (M+H)$^+$.

Step 3—Benzyl N-[2-[2-[2-[2-[4-[(7-chloro-4-oxo-3H-pyrido[4,3-d]pyrimidin-5-yl)amino]indol-1-yl]ethoxy]ethoxy]ethoxy]ethyl]carbamate To a mixture of benzyl N-[2-[2-[2-[2-(4-aminoindol-1-yl)ethoxy]ethoxy]ethoxy]ethyl]carbamate (1.14 g, 2.58 mmol) and 5,7-dichloro-3H-pyrido[4,3-d]pyrimidin-4-one (550 mg, 2.55 mmol, Intermediate FB) in NMP (10 mL) was added TEA (774 mg, 7.65 mmol) under a nitrogen atmosphere. The reaction mixture was stirred at 140° C. for 1 hour. On completion, the reaction mixture was concentrated in vacuo to remove the NMP. The residue was diluted with water (8 mL) and extracted with ethyl acetate (2×10 mL). The combined organic layer was dried over Na$_2$SO$_4$, filtered and concentrated in vacuo to give a residue. The residue was purified by reverse phase chromatography (0.1% FA in water) to give the title compound (800 mg, 50% yield) as a yellow solid. $^1$H NMR (400 MHz, MeOD) δ 8.26 (dd, J=2.4, 6.0 Hz, 1H), 8.15 (s, 1H), 7.34-7.25 (m, 6H), 7.20-7.17 (m, 2H), 6.78 (s, 1H), 6.68 (d, J=3.2 Hz, 1H), 5.03 (s, 2H), 4.63 (s, 1H), 4.34 (t, J=5.2 Hz, 2H), 3.83 (t, J=5.2 Hz, 2H), 3.53 (s, 4H), 3.49-3.44 (m, 5H), 3.25 (t, J=5.6 Hz, 2H); LC-MS (ESI$^+$) m/z 621.1 (M+H)$^+$.

Step 4—Benzyl N-[2-[2-[2-[2-[4-[[7-[[(1R,2S)-2-aminocyclohexyl]amino]-4-oxo-3H-pyrido[4,3-d]pyrimidin-5-yl]amino]indol-1-yl]ethoxy]ethoxy]ethoxy]ethyl]carbamate A mixture of benzyl N-[2-[2-[2-[2-[4-[(7-chloro-4-oxo-3H-pyrido[4,3-d]pyrimidin-5-yl)amino]indol-1-yl]ethoxy]ethoxy]ethoxy]ethyl]carbamate (550 mg, 886 umol) and (1R,2S)-cyclohexane-1,2-diamine (1.01 g, 8.86 mmol) in NMP (3 mL) was heated in a microwave at 150° C. for 1.5 hours. On completion, the reaction mixture was filtered and concentrated in vacuo to remove the NMP. The residue was purified by prep-HPLC (column: Phenomenex Synergi Max-RP 250*50 mm*10 um; mobile phase: [water (0.225% FA)-ACN]) to give the title compound (200 mg, 32% yield) as a yellowish solid. LC-MS (ESI$^+$) m/z 699.6 (M+H)$^+$.

Step 5—Tert-butyl N-[(1S,2R)-2-[[5-[[1-[2-[2-[2-[2-(benzyloxycarbonylamino)ethoxy]ethoxy]ethoxy]ethyl]indol-4-yl]amino]-4-oxo-3H-pyrido[4,3-d]pyrimidin-7-yl]amino]cyclohexyl]carbamate To a mixture of benzyl N-[2-[2-[2-[2-[4-[[7-[[(1R,2S)-2-aminocyclohexyl]amino]-4-oxo-3H-pyrido[4,3-d]pyrimidin-5-yl]amino]indol-1-yl]ethoxy]ethoxy]ethoxy]ethyl]carbamate (200 mg, 286 umol) in dichloromethane (1 mL) was added (Boc)$_2$O (62.4 mg, 286 umol) under a nitrogen atmosphere. The reaction mixture was stirred at rt for 12 hours. On completion, the reaction mixture was diluted with water (5 mL) and extracted with dichloromethane (2×10 mL). The combined organic layer was dried over Na$_2$SO$_4$, filtered and concentrated in vacuo to give a residue. The residue was purified by prep-TLC (dichloromethane:methanol=20:1) to give the title compound (150 mg, 65% yield) as a yellowish solid. LC-MS (ESI$^+$) m/z 799.5 (M+H)$^+$.

Step 6—Tert-butyl N-[(1S,2R)-2-[[5-[[1-[2-[2-[2-(2-aminoethoxy)ethoxy]ethoxy]ethyl]indol-4-yl]amino]-4-oxo-3H-pyrido[4,3-d]pyrimidin-7-yl]amino]cyclohexyl]carbamate To a mixture of tert-butyl N-[(1S,2R)-2-[[5-[[1-[2-[2-[2-[2-(benzyloxycarbonylamino)ethoxy]ethoxy]ethoxy]ethyl]indol-4-yl]amino]-4-oxo-3H-pyrido[4,3-d]pyrimidin-7-yl]amino]cyclohexyl]carbamate (10.0 mg, 12.5 umol) in EtOAc (5 mL) was added Pd(OH)$_2$/C (17.5 mg, 12.5 umol, 10 wt) under a hydrogen atmosphere (50 psi pressure). The reaction mixture was stirred at rt for 2 hours. On completion, the reaction mixture was filtered and concentrated in vacuo to give the title compound (3.00 mg, 36% yield) as a yellowish solid. LC-MS (ESI$^+$) m/z 665.3 (M+H)$^+$.

Step 7—Tert-butyl N-[(1S,2R)-2-[[5-[[1-[2-[2-[2-[2-[[2-(2,6-dioxo-3-piperidyl)-1,3-dioxo-isoindolin-4-yl]amino]ethoxy]ethoxy]ethoxy]ethyl]indol-4-yl]amino]-4-oxo-3H-pyrido[4,3-d]pyrimidin-7-yl]amino]cyclohexyl]carbamate To a mixture of tert-butyl N-[(1S,2R)-2-[[5-[[1-[2-[2-[2-(2-aminoethoxy)ethoxy]ethoxy]ethyl]indol-4-yl]amino]-4-oxo-3H-pyrido[4,3-d]pyrimidin-7-yl]amino]cyclohexyl]carbamate (50.0 mg, 75.2 umol) and 2-(2,6-dioxo-3-piperidyl)-4-fluoro-isoindoline-1,3-dione (24.9 mg, 90.2 umol, Intermediate R) in DMF (2 mL) was added DIPEA (19.4 mg, 150 umol) under a nitrogen atmosphere. The reaction mixture was stirred at 90° C. for 12 hours. On completion, the reaction mixture was purified by prep-HPLC (Boston Green ODS 150*30 5 u; mobile phase: [water (0.225% FA)-ACN]) to give the title compound (18.0 mg, 25% yield) as a yellow solid. LC-MS (ESI$^+$) m/z 921.2 (M+H)$^+$.

Step 8—4-[2-[2-[2-[2-[4-[[7-[[(1R,2S)-2-aminocyclohexyl]amino]-4-oxo-3H-pyrido[4,3-d]pyrimidin-5-yl]amino]indol-1-yl]ethoxy]ethoxy]ethoxy]ethylamino]-2-(2,6-dioxo-3-piperidyl)isoindoline-1,3-dione To a mixture of tert-butyl N-[(1S,2R)-2-[[5-[[1-[2-[2-[2-[2-[[2-(2,6-dioxo-3-piperidyl)-1,3-dioxo-isoindolin-4-yl]amino]ethoxy]ethoxy]ethoxy]ethyl]indol-4-yl]amino]-4-oxo-3H-pyrido[4,3-d]pyrimidin-7-yl]amino]cyclohexyl]carbamate (33.0 mg, 35.8 umol) in dichloromethane (8 mL) was added TFA (3.08 g, 27.0 mmol). The reaction mixture was stirred at rt for 0.5 hour. On completion, the reaction mixture was concentrated in vacuo to remove the dichloromethane. The residue was purified by prep-HPLC (column: Phenomenex Synergi C18 150*25*10 um; mobile phase: [water (0.1% TFA)-ACN]) to give the title compound I-166 (24.8 mg, 84% yield) as a yellow solid. $^1$H NMR (400 MHz, DMSO-d$_6$) δ 11.69 (s, 1H), 11.11 (s, 1H), 8.16 (s, 1H), 8.03 (s, 1H), 7.79 (s, 3H), 7.54 (t, J=7.2 Hz, 1H), 7.39 (s, 1H), 7.20-7.16 (m, 1H), 7.15-7.06 (m, 3H), 7.02 (d, J=6.0 Hz, 1H), 6.56 (s, 2H), 6.06 (s, 1H), 5.05 (d, J=8.0 Hz, 1H), 4.32 (s, 4H), 3.74 (s, 2H), 3.64-3.53 (m, 13H), 2.85 (d, J=12.8 Hz, 1H), 2.62-2.59 (m, 1H), 2.01 (s, 1H), 1.88-1.57 (m, 6H), 1.47 (s, 2H); LC-MS (ESI+) m/z 821.2 (M+H)+.

Example 167: 4-[2-[2-[2-[2-[2-[4-[[7-[[(1R,2S)-2-Aminocyclohexyl]amino]-4-oxo-3H-pyrido[4,3-d]pyrimidin-5-yl]amino]indol-1-yl]ethoxy]ethoxy]ethoxy]ethoxy]ethylamino]-2-(2,6-dioxo-3-piperidyl)isoindoline-1,3-dione, I-167

Example 168: 4-[2-[2-[2-[4-[[7-[[(1R,2S)-2-Aminocyclohexyl]amino]-4-oxo-3H-pyrido[4,3-d]pyrimidin-5-yl]amino]indol-1-yl]ethoxy]ethoxy]ethylamino]-2-(2,6-dioxo-3-piperidyl)isoindoline-1,3-dione, I-168

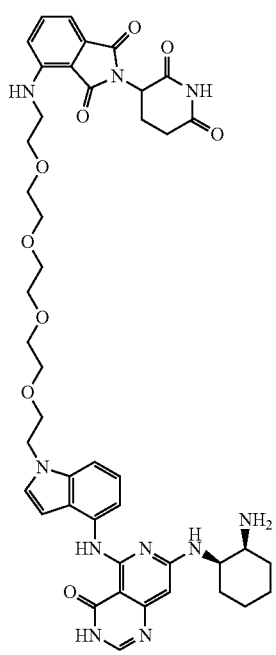 [SMILES: N[C@H]1CCCC[C@H]1Nc1cc2nc[nH]c(=O)c2c(Nc2cccc3c2ccn3CCOCCOCCOCCOCCNc2cccc3c2C(=O)N(C2CCC(=O)NC2=O)C3=O)n1]

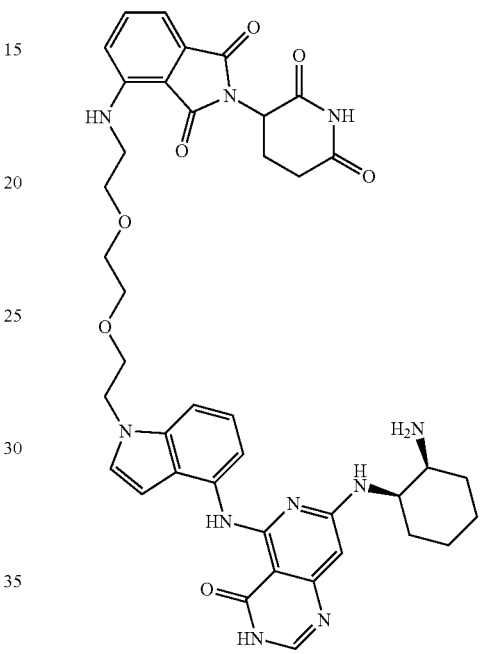

4-[2-[2-[2-[2-[2-[4-[[7-[[(1R,2S)-2-Aminocyclohexyl]amino]-4-oxo-3H-pyrido[4,3-d]pyrimidin-5-yl]amino]indol-1-yl]ethoxy]ethoxy]ethoxy]ethoxy]ethylamino]-2-(2,6-dioxo-3-piperidyl)isoindoline-1,3-dione I-167 was synthesized via Method 15, using Intermediate FC as the mesylate in Step 1. Variations in time and temperature were as follows: Step 3 was run at 140° C. for 4 h, Step 5 was run at rt for 7 h, Step 6 was run at rt for 4 h with 15 psi pressure of hydrogen, Step 7 was run at 100° C. for 8 h, and Step 8 was run at rt for 1 h. The intermediate formed from Step 5 was purified by prep-HPLC (column: Phenomenex luna C18 250*50 mm*10 um; mobile phase: [water (0.225% FA)-ACN]; B %: 35 ACN %-65 ACN %, 33 min). Characterization of the final product: $^1$H NMR (400 MHz, DMSO-$d_6$) δ 11.7 (s, 1H), 11.1 (s, 1H), 8.18 (br s, 1H), 7.99 (s, 1H), 7.78-7.76 (m, 3H), 7.56 (dd, J=7.2, 8.4 Hz, 1H), 7.39 (d, J=3.2 Hz, 1H), 7.22-7.16 (m, 1H), 7.16-7.06 (m, 3H), 7.03 (d, J=7.0 Hz, 1H), 6.64-6.50 (m, 2H), 6.06 (s, 1H), 5.05 (dd, J=5.6, 12.8 Hz, 1H), 4.47-4.17 (m, 4H), 3.67-3.65 (m, 2H), 3.63-3.56 (m, 4H), 3.55-3.53 (m, 4H), 3.52-3.47 (m, 10H), 2.96-2.80 (m, 1H), 2.06-1.95 (m, 1H), 1.94-1.55 (m, 6H), 1.47-1.45 (m, 2H); LC-MS (ESI+) m/z 865.2 (M+H)+.

4-[2-[2-[2-[4-[[7-[[(1R,2S)-2-Aminocyclohexyl]amino]-4-oxo-3H-pyrido[4,3-d]pyrimidin-5-yl]amino]indol-1-yl]ethoxy]ethoxy]ethylamino]-2-(2,6-dioxo-3-piperidyl)isoindoline-1,3-dione I-168 was synthesized via Method 15, using Intermediate FD as the mesylate in Step 1. Variations in time and temperature were as follows: Step 1 & 2 were run at 70° C. for 2 h, and Step 6 was run at rt for 6 h with 15 psi pressure of hydrogen. Characterization of the final product: $^1$H NMR (400 MHz, DMSO-$d_6$) δ 11.72 (s, 1H), 8.38 (s, 1H), 8.24 (d, J=5.2 Hz, 1H), 7.93 (s, 1H), 7.53 (dd, J=7.2, 8.4 Hz, 1H), 7.36 (d, J=3.2 Hz, 1H), 7.18-7.12 (m, 1H), 7.11-7.05 (m, 2H), 7.02 (d, J=7.2 Hz, 1H), 6.60-6.53 (m, 2H), 6.02 (s, 1H), 5.05 (dd, J=5.6, 12.8 Hz, 1H), 4.31 (t, J=5.2 Hz, 2H), 3.75 (t, J=5.2 Hz, 2H), 3.64-3.58 (m, 10H), 3.40-3.11 (m, 2H), 2.91-2.81 (m, 2H), 2.59-2.58 (m, 1H), 2.53-2.52 (m, 1H), 2.46-2.43 (m, 1H), 2.05-1.96 (m, 1H), 1.89-1.82 (m, 2H), 1.75-1.57 (m, 4H), 1.45-1.33 (m, 2H); LC-MS (ESI+) m/z 777.3 (M+H)+.

2265

Further Examples

Example 169: N-[3-carbamoyl-1-[1-[2-[2-[2-[2-[[2-(2,6-dioxo-3-piperidyl)-1,3-dioxo-isoindolin-4-yl]amino]ethoxy]ethoxy]ethoxy]ethyl]azetidin-3-yl]pyrazol-4-yl]-2-[2-(2,2,2-trifluoroethylamino)-4-pyridyl]oxazole-4-carboxamide, I-169

2266

2-(2,6-dioxo-3-piperidyl)-4-fluoro-isoindoline-1,3-dione (721 mg, 2.61 mmol, Intermediate R). The reaction mixture was stirred at 115° C. for 24 hours. On completion, the reaction mixture was concentrated in vacuo. The residue was purified by silica gel chromatography (petroleum ether:ethyl acetate=0:1) to give the title compound (0.80 g, 68% yield) as a brown solid. $^1$H NMR (400 MHz, DMSO-d$_6$) δ 11.11 (s,

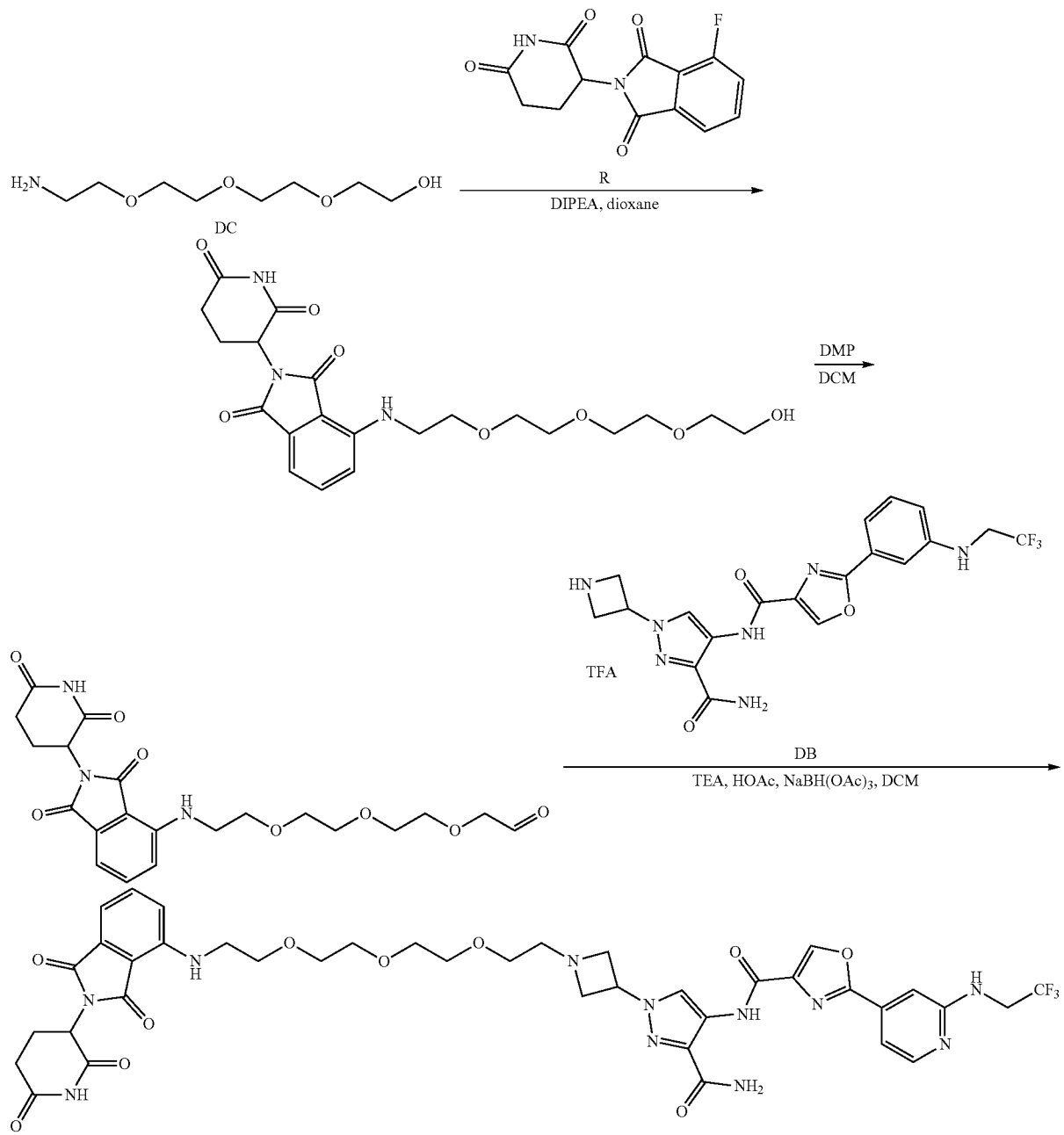

Step 1—2-(2,6-Dioxo-3-piperidyl)-4-[2-[2-[2-(2-hydroxyethoxy)ethoxy]ethoxy]ethylamino]isoindoline-1,3-dione To a mixture of 2-[2-[2-(2-aminoethoxy)ethoxy]ethoxy]ethanol (0.60 g, 2.61 mmol, HCl salt, Intermediate DC) and DIPEA (2.70 g, 20.9 mmol) in dioxane (15 mL) was added 1H), 7.59 (dd, J=3.2, 4.4 Hz, 1H), 7.16 (d, J=8.4 Hz, 1H), 7.05 (d, J=7.2 Hz, 1H), 6.61 (t, J=5.6 Hz, 1H), 5.06 (dd, J=5.2, 12.8 Hz, 1H), 4.58-4.56 (m, 1H), 3.62 (t, J=5.6 Hz, 2H), 3.59-3.56 (m, 2H), 3.55-3.53 (m, 2H), 3.51-3.44 (m, 8H), 3.42-3.38 (m, 2H), 2.95-2.81 (m, 1H), 2.64-2.53 (m, 2H), 2.09-2.00 (m, 1H).

Step 2—2-[2-[2-[2-[[2-(2,6-Dioxo-3-piperidyl)-1,3-dioxo-isoindolin-4-yl]amino]ethoxy]ethoxy]ethoxy]acetaldehyde To a solution of 2-(2,6-dioxo-3-piperidyl)-4-[2-[2-[2-(2-hydroxyethoxy)ethoxy]ethoxy]ethylamino]isoindoline-1,3-dione (250 mg, 556 umol) in DCM (10 mL) was added DMP (471 mg, 1.11 mmol) at 0° C. Then the mixture was allowed to warm to rt and stirred for 2 hours. On completion, the reaction mixture was quenched with saturated NaHCO$_3$ (10 mL) and saturated Na$_2$S$_2$O$_3$ (10 mL) at rt, and then stirred for an additional 30 minutes. The mixture was then extracted with DCM (3×20 mL). The combined organic layer was dried with Na$_2$SO$_4$, filtered and concentrated in vacuo to give the title compound (226 mg, 91% yield) as a yellow solid. LC-MS (ESI$^+$) m/z 448.0 (M+H)$^+$.

Step 3—N-[3-carbamoyl-1-[1-[2-[2-[2-[2-[[2-(2,6-dioxo-3-piperidyl)-1,3-dioxo-isoindolin-4-yl]amino]ethoxy]ethoxy]ethoxy]ethyl]azetidin-3-yl]pyrazol-4-yl]-2-[2-(2,2,2-trifluoroethylamino)-4-pyridyl]oxazole-4-carboxamide To a mixture of N-[1-(azetidin-3-yl)-3-carbamoyl-pyrazol-4-yl]-2-[2-(2,2,2-trifluoroethylamino)-4-pyridyl]oxazole-4-carboxamide (44.1 mg, 78.2 umol, TFA salt, Intermediate DB) in DCM (2 mL) was added TEA (11.8 mg, 117 umol), HOAc (9.39 mg, 156 umol) and 2-[2-[2-[2-[[2-(2,6-dioxo-3-piperidyl)-1,3-dioxo-isoindolin-4-yl]amino]ethoxy]ethoxy]ethoxy]acetaldehyde (35.0 mg, 78.2 umol), and the mixture was stirred for 30 minutes at rt. Then NaBH(OAc)$_3$ (24.8 mg, 117 umol) was added and the mixture was stirred rt for 16 hours. On completion, the reaction mixture was concentrated in vacuo to give a residue. The residue was purified by prep-HPLC (column: Kromasil 150*25 mm*10 um; mobile phase: [water (0.225% FA)-ACN]) to give the title compound I-169 (16.4 mg, 21% yield) as a yellow solid. $^1$H NMR (400 MHz, DMSO-d$_6$) δ 11.10 (s, 1H), 10.93 (s, 1H), 8.96 (s, 1H), 8.28-8.20 (m, 2H), 7.76 (s, 1H), 7.68 (t, J=6.4 Hz, 1H), 7.61-7.49 (m, 2H), 7.25 (s, 1H), 7.18-7.08 (m, 2H), 7.02 (d, J=6.8 Hz, 1H), 6.58 (t, J=5.6 Hz, 1H), 5.07 (dd, J=6.4, 12.8 Hz, 2H), 4.25-4.21 (m, 2H), 3.70 (t, J=7.6 Hz, 2H), 3.61 (t, J=5.2 Hz, 2H), 3.57-3.47 (m, 14H), 2.92-2.84 (m, 1H), 2.68-2.64 (m, 2H), 2.62-2.54 (m, 2H), 2.06-1.99 (m, 1H). LC-MS (ESI$^+$) m/z 904.3 (M+Na)$^+$.

Example 170: N-[3-carbamoyl-1-[1-[2-[2-[2-[2-[[2-(2,6-dioxo-3-piperidyl)-1,3-dioxo-isoindolin-4-yl]amino]ethoxy]ethoxy]ethoxy]ethyl]-4-piperidyl]pyrazol-4-yl]-2-[2-(2,2,2-trifluoroethylamino)-4-pyridyl]oxazole-4-carboxamide, I-170

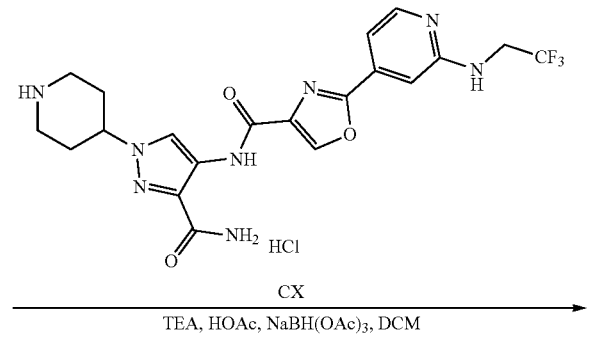

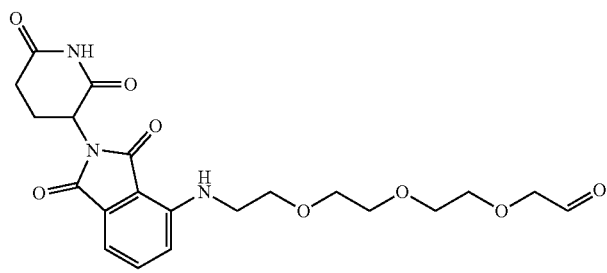

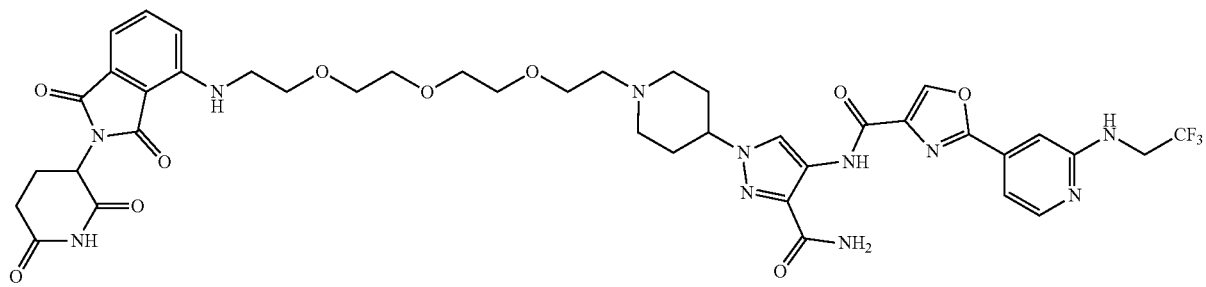

To a mixture of N-[3-carbamoyl-1-(4-piperidyl)pyrazol-4-yl]-2-[2-(2,2,2-trifluoroethylamino)-4-pyridyl]oxazole-4-carboxamide (100 mg, 194 umol, HCl salt, Intermediate CX) in DCM (4 mL) was added TEA (29.4 mg, 291 umol), HOAc (23.3 mg, 388 umol) and 2-[2-[2-[2-[[2-(2,6-dioxo- 3-n piperidyl)-1,3-dioxo-isoindolin-4-yl]amino]ethoxy]ethoxy]ethoxy]acetaldehyde (86.9 mg, 194 umol, synthesized via Steps 1-2 of Example 169) and the reaction was stirred at rt for 30 minutes. Then, NaBH(OAc)$_3$ (61.7 mg, 291 umol) was added to the reaction mixture and the mixture was stirred at rt for an additional 16 hours. On completion, the reaction mixture was concentrated in vacuo to give a residue. The residue was purified by prep-HPLC (column: Phenomenex Synergi C18 150*25*10 um; mobile phase: [water (0.1% TFA)-ACN]) to give the title compound I-170 (31.4 mg, 15% yield) as a yellow solid. $^1$H NMR (400 MHz, DMSO-d$_6$) δ=11.11 (s, 1H), 10.92 (m, 1H), 9.64 (s, 1H), 8.97 (s, 1H), 8.39 (m, 1H), 8.24 (d, J=5.2 Hz, 1H), 7.76 (t, J=5.2 Hz, 1H), 7.61-7.54 (m, 2H), 7.26 (s, 1H), 7.20-7.14 (m, 1H), 7.14-7.08 (m, 1H), 7.07-6.99 (m, 1H), 6.57 (s, 1H), 5.05 (dd, J=6.4, 12.8 Hz, 1H), 4.80-4.48 (m, 1H), 4.37-4.15 (m, 2H), 3.76-3.53 (m, 14H), 3.49-3.37 (m, 4H), 3.35-3.29 (m, 1H), 3.22-3.11 (s, 1H), 2.99-2.78 (m, 1H), 2.62-2.51 (m, 2H), 2.41-2.17 (m, 4H), 2.09-1.97 (m, 1H). LC-MS (ESI$^+$) m/z 910.0 (M+H)$^+$.

Example 171: N-[3-carbamoyl-1-[4-[[2-[2-[2-[[2-(2,6-dioxo-3-piperidyl)-1,3-dioxo-isoindolin-4-yl]amino]ethoxy]ethoxy]ethylamino]methyl]phenyl]pyrazol-4-yl]-2-[2-[(2,2,2-trifluoroethylamino)-4-pyridyl]oxazole-4-carboxamide, I-171

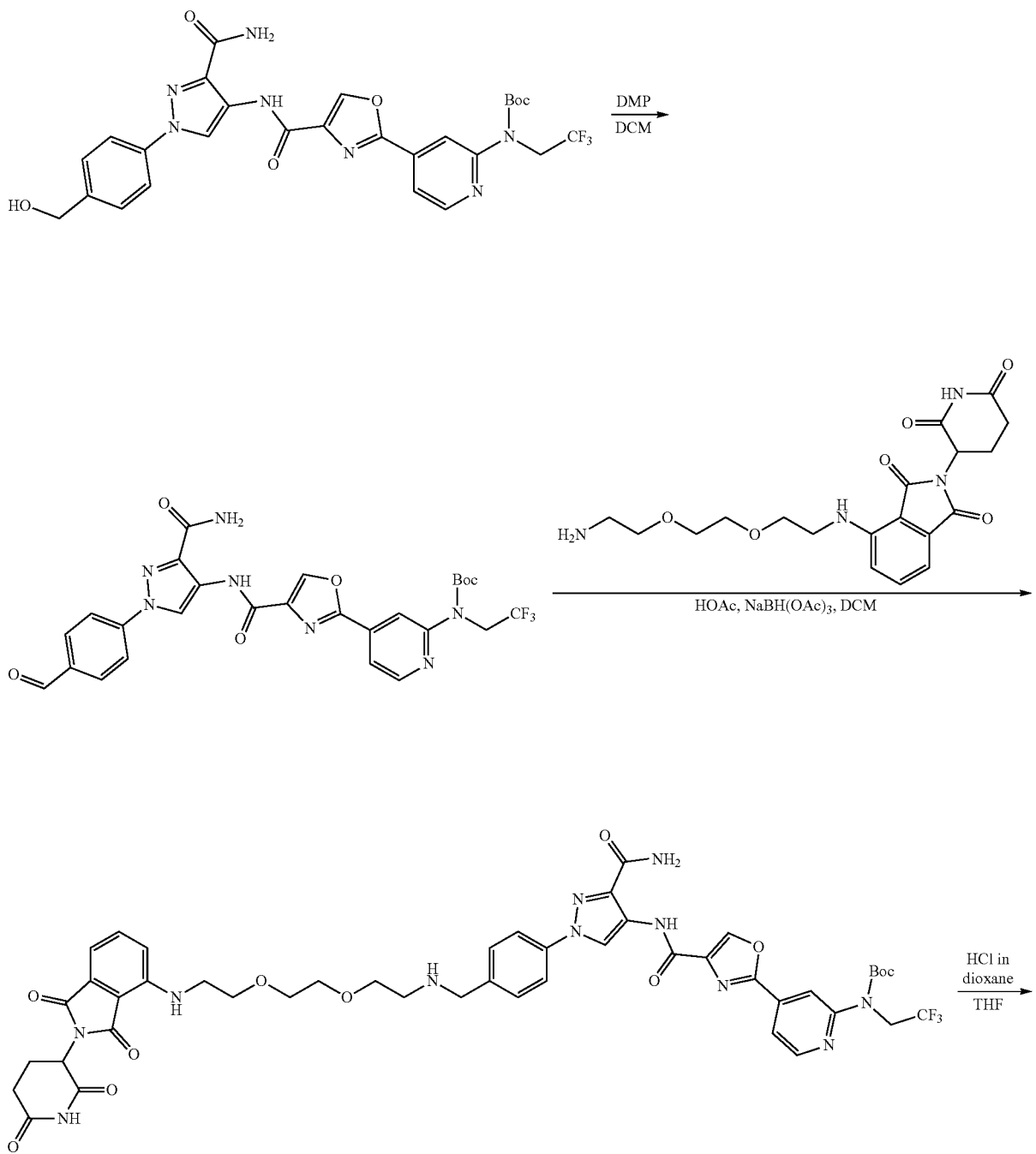

-continued

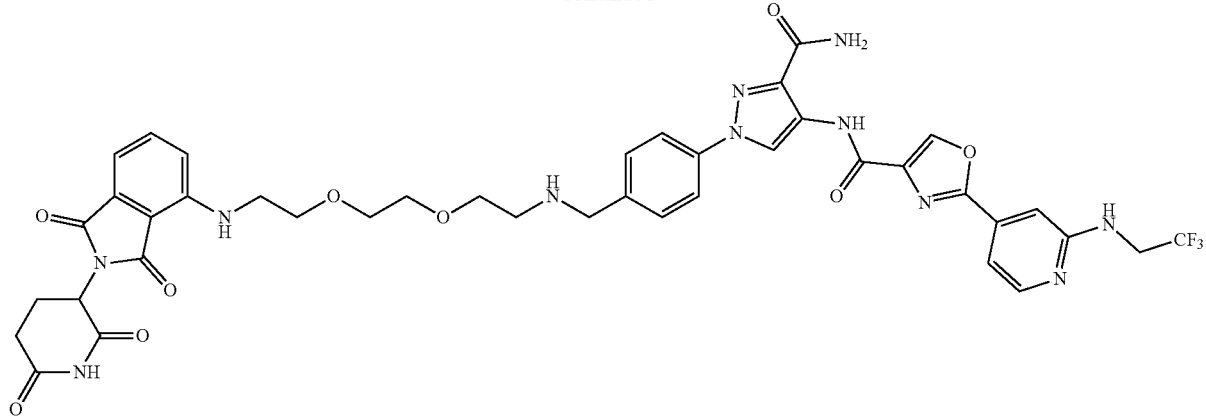

Step 1—Tert-butyl N-[4-[4-[[3-carbamoyl-1-(4-formylphenyl)pyrazol-4-yl]carbamoyl]oxazol-2-yl]-2-pyridyl]-N-(2,2,2-trifluoroethyl)carbamate To a solution of tert-butyl N-[4-[4-[[3-carbamoyl-1-[4-(hydroxymethyl)phenyl]pyrazol-4-yl]carbamoyl]oxazol-2-yl]-2-pyridyl]-N-(2,2,2-trifluoroethyl)carbamate (200 mg, 332 umol, synthesized via Step 1 of Intermediate CV) in THF (5 mL) and DCM (5 mL) was added DMP (282 mg, 665 umol) at 0° C. and the mixture was stirred at 0° C. for 2 hours. On completion, the mixture was quenched with saturated NaHCO$_3$/Na$_2$S2O3 (1:1, 30 mL) and stirred for an additional 30 min. The aqueous layer was then separated from the organic and extracted with DCM (3×20 mL). The combined organic solutions were washed with H$_2$O (3×20 mL) and brine (20 mL), dried over MgSO$_4$, filtered and concentrated in vacuo. The residue was purified by reverse phase flash chromatography (0.1% FA in water) to give the title compound (100 mg, 48% yield) as a white solid. LC-MS (ESI$^+$) m/z 600.4 (M+H)$^+$.

Step 2—Tert-butyl N-[4-[4-[[3-carbamoyl-1-[4-[[2-[2-[2-[[2-(2,6-dioxo-3-piperidyl)-1,3-dioxo-isoindolin-4-yl]amino]ethoxy]ethoxy]ethylamino]methyl]phenyl]pyrazol-4-yl]carbamoyl]oxazol-2-yl]-2-pyridyl]-N-(2,2,2-trifluoroethyl)carbamate A mixture of tert-butyl N-[4-[4-[[3-carbamoyl-1-(4-formylphenyl)pyrazol-4-yl]carbamoyl]oxazol-2-yl]-2-pyridyl]-N-(2,2,2-trifluoroethyl)carbamate (40.5 mg, 66.7 umol), 4-[2-[2-(2-amino ethoxy)ethoxy]ethylamino]-2-(2,6-dioxo-3-piperidyl)isoindoline-1,3-dione (40.0 mg, 100 umol, synthesized via Steps 1-2 of Example 127) in a mixed solvent of DCM (5 mL) and THF (5 mL) was added HOAc (6.01 mg, 100 umol) and NaBH(OAc)$_3$ (42.4 mg, 200 umol). The mixture was stirred at rt for 72 hours under nitrogen atmosphere. On completion, the mixture was concentrated in vacuo and the residue was purified by reverse phase flash chromatography (0.1% FA in water) to give the title compound (50.0 mg, 76% yield) as a yellow solid. LC-MS (ESI$^+$) m/z 988.5 (M+H)$^+$.

Step 3—N-[3-carbamoyl-1-[4-[[2-[2-[2-[[2-(2,6-dioxo-3-piperidyl)-1,3-dioxo-isoindolin-4-yl]amino]ethoxy]ethoxy]ethylamino]methyl]phenyl]pyrazol-4-yl]-2-[2-(2,2,2-trifluoroethylamino)-4-pyridyl]oxazole-4-carboxamide To a solution of tert-butyl N-[4-[4-[[3-carbamoyl-1-[4-[[2-[2-[2-[[2-(2,6-dioxo-3-piperidyl)-1,3-dioxo-isoindolin-4-yl]amino]ethoxy]ethoxy]ethylamino]methyl]phenyl]pyrazol-4-yl]carbamoyl]oxazol-2-yl]-2-pyridyl]-N-(2,2,2-trifluoroethyl)carbamate (50.0 mg, 50.6 umol) in THF (5 mL) was added HCl in dioxane (4 N, 2 mL). The mixture was stirred at rt for 2 hours. On completion, the mixture was concentrated in vacuo, and the residue was purified Pre-HPLC (column: Boston Green ODS 150*30 5 u; mobile phase: [water (0.225% FA)-ACN]; B %: 25%-52%, 10 min) to give the title compound I-171 (23.0 mg, 51% yield) as a yellow solid. $^1$H NMR (400 MHz, DMSO-d$_6$) δ 11.00 (s, 1H), 9.01 (s, 1H), 8.91 (s, 1H), 8.29-8.21 (m, 2H), 8.03 (s, 1H), 7.89 (d, J=8.4 Hz, 2H), 7.76-7.66 (m, 2H), 7.61-7.54 (m, 1H), 7.49 (d, J=8.4 Hz, 2H), 7.27 (s, 1H), 7.18 (d, J=5.2 Hz, 1H), 7.13 (d, J=8.8 Hz, 1H), 7.02 (d, J=7.2 Hz, 1H), 6.59 (t, J=5.6 Hz, 1H), 5.05 (dd, J=5.2, 12.8 Hz, 1H), 4.32-4.19 (m, 2H), 3.81 (s, 2H), 3.72-3.53 (m, 10H), 2.93-2.80 (m, 1H), 2.75-2.67 (m, 2H), 2.56-2.53 (m, 3H), 2.09-1.97 (m, 1H); LC-MS (ESI$^+$) m/z 888.4 (M+H)$^+$.

Example 172: N-[3-carbamoyl-1-[4-[5-[2-[[2-(2,6-dioxo-3-piperidyl)-1,3-dioxo-isoindolin-4-yl]amino]ethylamino]pentylcarbamoyl]phenyl]pyrazol-4-yl]-2-[2-(2,2,2-trifluoroethylamino)-4-pyridyl]oxazole-4-carboxamide, I-172
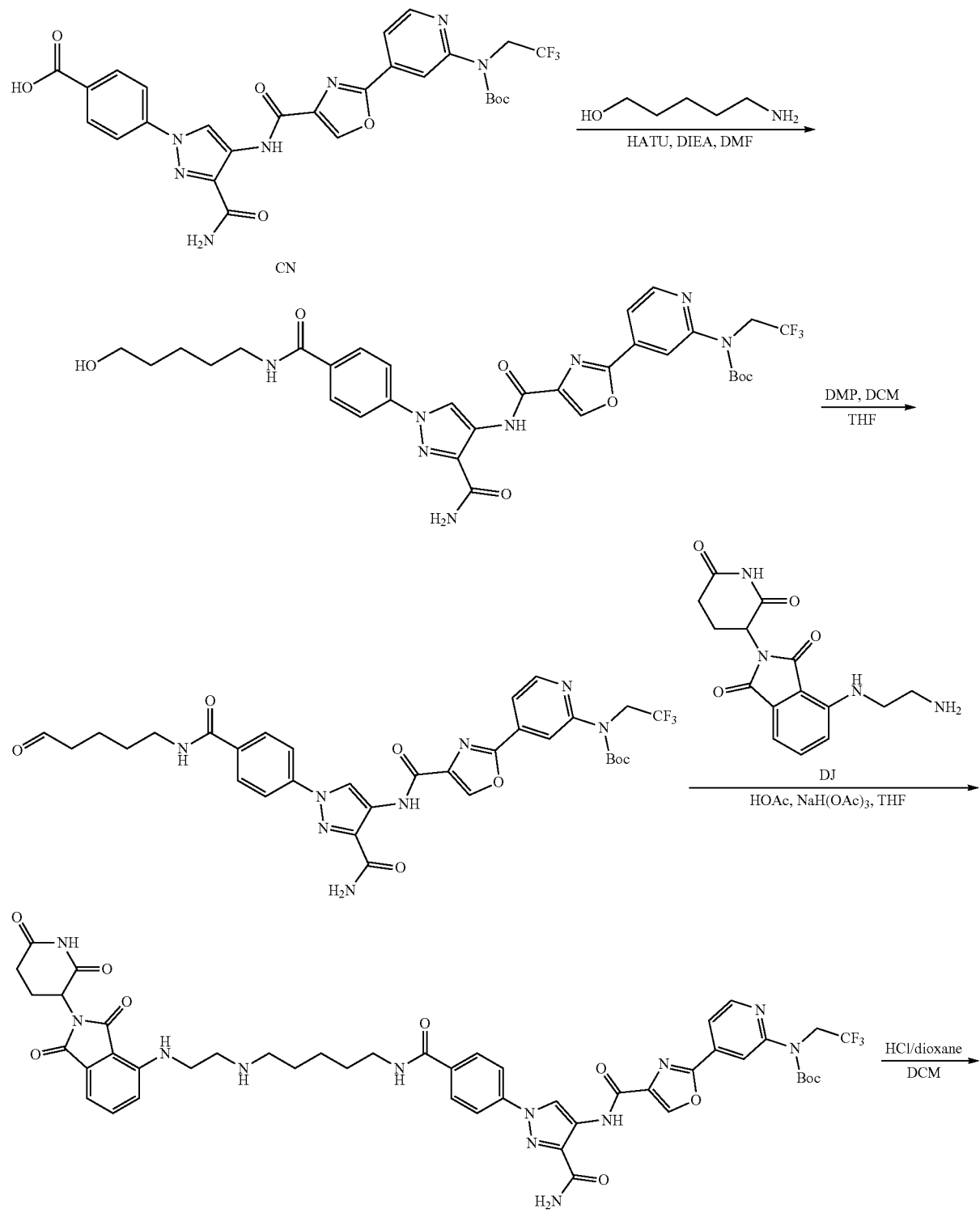

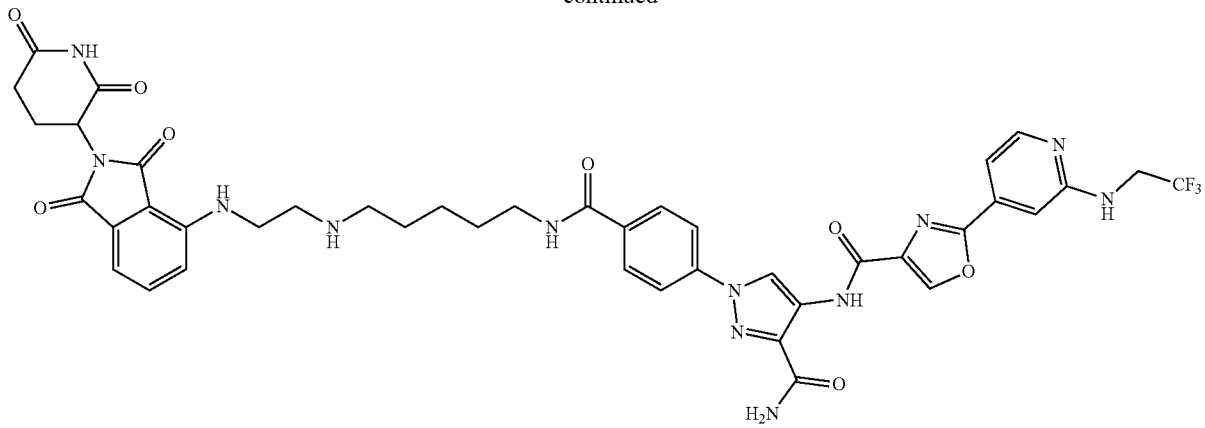

Step 1—Tert-butyl N-[4-[4-[[3-carbamoyl-1-[4-(5-hydroxypentylcarbamoyl)phenyl]pyrazol-4-yl]carbamoyl]oxazol-2-yl]-2-pyridyl]-N-(2,2,2-trifluoroethyl)carbamate To a mixture of 4-[4-[[2-[2-[tert-butoxycarbonyl(2,2,2-trifluoroethyl)amino]-4-pyridyl]oxazole-4-carbonyl]amino]-3-carbamoyl-pyrazol-1-yl]benzoic acid (100 mg, 162 umol, Intermediate CN) and 5-aminopentan-1-ol (22.0 mg, 211 umol) in DMF (5 mL) was added DIPEA (63.0 mg, 487 umol, 85 uL) and HATU (74.0 mg, 195 umol). The mixture was stirred at rt for 2 hours. On completion, the mixture was quenched by water (15 mL), and then filtered. The filter cake was dried in vacuo. The residue was purified by reverse phase flash chromatography (0.1% FA in water) to give the title compound (80.0 mg, 67% yield) as a white solid. LC-MS (ESI$^+$) m/z 701.3 (M+H)$^+$.

Step 2—Tert-butyl N-[4-[4-[[3-carbamoyl-1-[4-(5-oxopentylcarbamoyl)phenyl]pyrazol-4-yl]carbamoyl]oxazol-2-yl]-2-pyridyl]-N-(2,2,2-trifluoroethyl)carbamate To a solution of tert-butyl N-[4-[4-[[3-carbamoyl-1-[4-(5-hydroxypentylcarbamoyl)phenyl]pyrazol-4-yl]carbamoyl]oxazol-2-yl]-2-pyridyl]-N-(2,2,2-trifluoroethyl)carbamate (80.0 mg, 114 umol) in THF (5.0 mL) and DCM (5.0 mL) was added DMP (54.0 mg, 125. umol) at 0° C. The mixture was stirred at 0° C. for 2 hours. On completion, the reaction mixture was quenched with saturated NaHCO$_3$/Na$_2$S$_2$O$_3$ solution (1:1, 10 mL) and stirred for 30 minutes. The aqueous layer was separated from the organic and extracted with DCM (3×20 mL). The combined organic layers were washed with H$_2$O (3×10 mL) and brine (20 mL), dried over MgSO$_4$, then filtered and concentrated in vacuo to give the title compound (80.0 mg, crude) as a yellowish solid. LC-MS (ESI$^+$) m/z 599.2 (M+H-100)$^+$.

Step 3—Tert-butyl N-[4-[4-[[3-carbamoyl-1-[4-[5-[2-[[2-(2,6-dioxo-3-piperidyl)-1,3-dioxo-isoindolin-4-yl]amino]ethylamino]pentylcarbamoyl]phenyl]pyrazol-4-yl]carbamoyl]oxazol-2-yl]-2-pyridyl]-N-(2,2,2-trifluoroethyl)carbamate To a mixture of tert-butyl N-[4-[4-[[3-carbamoyl-1-[4-(5-oxopentylcarbamoyl)phenyl]pyrazol-4-yl]carbamoyl]oxazol-2-yl]-2-pyridyl]-N-(2,2,2-trifluoroethyl)carbamate (60.0 mg, 86.0 umol) and 4-(2-aminoethylamino)-2-(2,6-dioxo-3-piperidyl)isoindoline-1,3-dione (34.0 mg, 95.0 umol, HCl salt, Intermediate DJ) in THF (5 mL) was added AcOH (7.00 mg, 112 umol) and NaBH(OAc)$_3$ (27.0 mg, 128 umol). The mixture was stirred at rt for 24 hours under nitrogen atmosphere. On completion, the mixture was concentrated in vacuo. The residue was purified by reverse phase flash chromatography (0.1% FA in water) to give the title compound (30.0 mg, 35% yield) as a yellow solid. LC-MS (ESI$^+$) m/z 999.0 (M+H)$^+$.

Step 4—N-[3-carbamoyl-1-[4-[5-[2-[[2-(2,6-dioxo-3-piperidyl)-1,3-dioxo-isoindolin-4-yl]amino]ethylamino]pentylcarbamoyl]phenyl]pyrazol-4-yl]-2-[2-(2,2,2-trifluoroethylamino)-4-pyridyl]oxazole-4-carboxamide To a solution of tert-butyl N-[4-[4-[[3-carbamoyl-1-[4-[5-[2-[[2-(2,6-dioxo-3-piperidyl)-1,3-dioxo-isoindolin-4-yl]amino]ethylamino]pentylcarbamoyl]phenyl]pyrazol-4-yl]carbamoyl]oxazol-2-yl]-2-pyridyl]-N-(2,2,2-trifluoroethyl)carbamate (40.0 mg, 40.0 umol) in THF (5 mL) was added HCl in dioxane (4 N, 2 mL). The mixture was stirred at rt for 1 hour. On completion, the mixture was concentrated in vacuo, and the residue was purified by Pre-HPLC (column: Boston Green ODS 150*30 5 u; mobile phase: [water (0.225% FA)-ACN]; B %: 27%-57%, 10 min). to give the title compound I-172 (20.0 mg, 56% yield) as a yellow solid. $^1$H NMR (400 MHz, DMSO-d$_6$) δ 11.01 (s, 1H), 9.03 (d, J=5.6 Hz, 2H), 8.65-8.54 (m, 1H), 8.38-8.23 (m, 2H), 8.16-7.98 (m, 5H), 7.82-7.73 (m, 1H), 7.69 (t, J=6.4 Hz, 1H), 7.59 (t, J=7.6 Hz, 1H), 7.27 (s, 1H), 7.21-7.12 (m, 2H), 7.05 (d, J=7.2 Hz, 1H), 6.82 (m, 1H), 5.06 (dd, J=5.2, 12.8 Hz, 1H), 4.32-4.16 (m, 2H), 3.48-3.47 (m, 2H), 3.29 (m, 2H), 2.97-2.85 (m, 3H), 2.77-2.66 (m, 2H), 2.64-2.53 (m, 3H), 2.09-1.98 (m, 1H), 1.56 (m, 4H), 1.38 (m, 2H); LC-MS (ESI$^+$) m/z 899.4 (M+H)$^+$.

Example 173: 6-(5-Cyanopyrazolo[3,4-b]pyridin-1-yl)-4-(cyclopropylamino)-N-[3-[2-(2,6-dioxo-3-piperidyl)-1,3-dioxo-isoindolin-4-yl]oxy-2-fluoro-propyl]pyridine-3-carboxamide, I-173

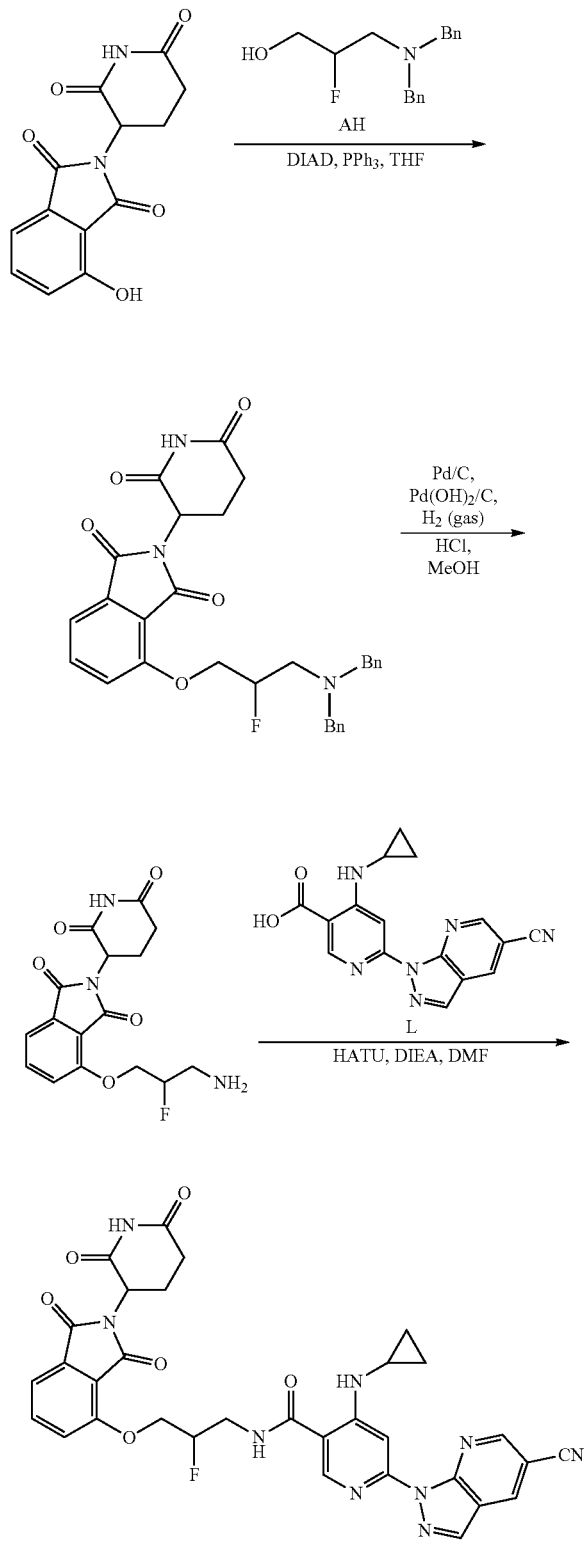

Step 1—4-[3-(Dibenzylamino)-2-fluoro-propoxy]-2-(2,6-dioxo-3-piperidyl)isoindoline-1,3-dione To a mixture of 2-(2,6-dioxo-3-piperidyl)-4-hydroxy-isoindoline-1,3-dione (2.00 g, 7.29 mmol, synthesized via Step 1 of Intermediate CA) in THF (200 mL) was added 3-(dibenzylamino)-2-fluoro-propan-1-ol (1.99 g, 7.29 mmol, Intermediate AH) and PPh$_3$ (3.83 g, 14.5 mmol). Then DIAD (2.21 g, 10.9 mmol) was added to the mixture dropwise at 0° C. The reaction mixture was allowed to warm to rt and stirred for 12 hours. On completion, the reaction mixture was concentrated in vacuo. The crude product was purified by prep-HPLC (column: Phenomenex Synergi Max-RP 250*50 mm*10 um; mobile phase: [water (0.225% FA)-ACN]; B %: 25 ACN %-50 ACN %, 30 min, 50% min) to give the title compound (2.70 g, 60% yield) as a white solid. $^1$H NMR (400 MHz, DMSO-d$_6$) δ 11.13 (s, 1H), 7.97-7.73 (m, 1H), 7.47 (d, J=7.2 Hz, 1H), 7.41 (d, J=8.4 Hz, 1H), 7.37-7.21 (m, 8H), 7.21-7.08 (m, 2H), 5.21-4.88 (m, 2H), 4.47-4.17 (m, 2H), 3.73-3.53 (m, 4H), 3.06-2.75 (m, 3H), 2.70-2.54 (m, 2H), 2.14-1.92 (m, 1H); LC-MS (ESI$^+$) m/z 530.0 (M+H)$^+$.

Step 2—4-(3-Amino-2-fluoro-propoxy)-2-(2,6-dioxo-3-piperidyl)isoindoline-1,3-dione To a mixture of 4-[3-(dibenzylamino)-2-fluoro-propoxy]-2-(2,6-dioxo-3-piperidyl)isoindoline-1,3-dione (100 mg, 188 umol), Pd(OH)$_2$/C (60.0 mg, 10 wt %) and Pd/C (60.0 mg, 10 wt %) in MeOH (6 mL) was added HCl (1 M, 100 uL) under hydrogen atmosphere (15 psi pressure). The reaction mixture was stirred at rt for 18 hours. On completion, the reaction mixture was filtered and concentrated in vacuo to give the compound (68.0 mg, HCl salt, 95% yield) as a colorless solid. LC-MS (ESI$^+$) m/z 350.0 (M+H)$^+$.

Step 3—6-(5-Cyanopyrazolo[3,4-b]pyridin-1-yl)-4-(cyclopropylamino)-N-[3-[2-(2,6-dioxo-3-piperidyl)-1,3-dioxo-isoindolin-4-yl]oxy-2-fluoro-propyl]pyridine-3-carboxamide To a mixture of 4-(3-amino-2-fluoro-propoxy)-2-(2,6-dioxo-3-piperidyl)isoindoline-1,3-dione (48.0 mg, 124 umol, HCl salt) in DMF (2 mL) was added 6-(5-cyanopyrazolo[3,4-b]pyridin-1-yl)-4-(cyclopropylamino)pyridine-3-carboxylic acid (64.8 mg, 149 umol, TFA salt, Intermediate L) and DIPEA (96.4 mg, 746 umol). Then HATU (70.9 mg, 186 umol) was added to the mixture and the mixture was stirred at rt for 2 hours. On completion, the reaction mixture was concentrated in vacuo. The crude product was purified by prep-HPLC (column: Phenomenex Synergi C18 150*25*10 um; mobile phase: [water (0.225% FA)-ACN]) to give the title compound I-173 (24.0 mg, 28% yield) as a white solid. $^1$H NMR (400 MHz, DMSO-d$_6$) δ 11.13 (s, 1H), 9.08 (d, J=2.0 Hz, 1H), 9.04 (d, J=2.0 Hz, 1H), 8.95 (t, J=5.6 Hz, 1H), 8.72-8.62 (m, 2H), 8.55 (s, 1H), 7.88-7.84 (m, 1H), 7.72 (s, 1H), 7.57-7.50 (m, 2H), 5.18-5.01 (m, 2H), 4.69-4.44 (m, 2H), 3.80-3.66 (m, 2H), 2.93-2.82 (m, 1H), 2.71-2.56 (m, 3H), 2.09-1.99 (m, 1H), 0.99-0.81 (m, 2H), 0.58-0.56 (m, 2H); LC-MS (ESI$^+$) m/z 652.2 (M+H)$^+$.

Example 174: 4-(Cyclopropylamino)-N-[3-[2-(2,6-dioxo-3-piperidyl)-1,3-dioxo-isoindolin-4-yl]oxy-2-fluoro-propyl]-6-(1,6-naphthyridin-2-ylamino)pyridine-3-carboxamide, I-174

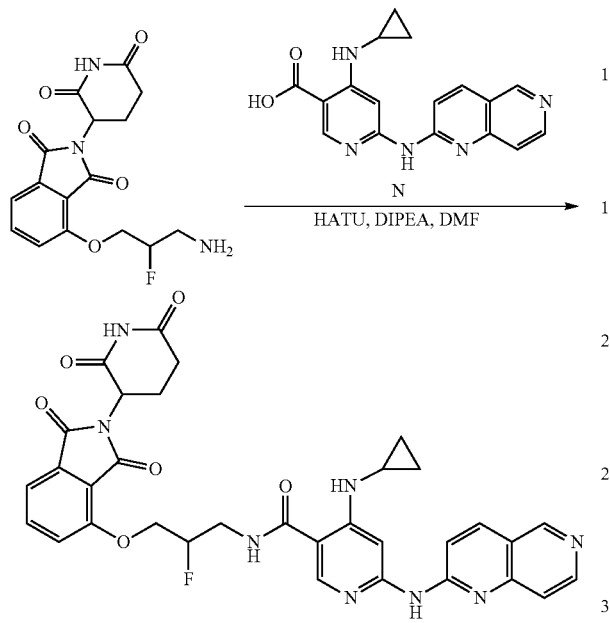

To a mixture of 4-(3-amino-2-fluoro-propoxy)-2-(2,6-dioxo-3-piperidyl)isoindoline-1,3-dione (100 mg, 259 umol, HCl salt, synthesized via Steps 1-2 of Example 173) and DIPEA (167 mg, 1.30 mmol) in DMF (2 mL) was added 4-(cyclopropylamino)-6-(1,6-naphthyridin-2-ylamino)pyridine-3-carboxylic acid (83.3 mg, 259 umol, Intermediate N) and HATU (118 mg, 311 umol). The reaction mixture was stirred at rt for 1 hour. On completion, the reaction mixture was concentrated in vacuo. Then the residue was purified by prep-HPLC (column: Phenomenex Synergi C18 150*25*10 um; mobile phase: [water (0.225% FA)-ACN]) to give the title compound I-174 (44.7 mg, 26% yield) as a white solid. $^1$H NMR (400 MHz, DMSO-d$_6$) δ 11.13 (s, 1H), 10.37 (s, 1H), 9.06 (s, 1H), 8.67 (t, J=5.2 Hz, 1H), 8.62-8.56 (m, 2H), 8.49 (s, 1H), 8.28 (d, J=8.8 Hz, 1H), 8.18 (s, 1H), 7.86 (t, J=7.6 Hz, 1H), 7.65-7.44 (m, 4H), 5.15-4.98 (m, 2H), 4.60-4.43 (m, 2H), 3.76-3.70 (m, 2H), 2.97-2.86 (m, 1H), 2.71-2.56 (m, 3H), 2.08-2.00 (m, 1H), 1.01-0.87 (m, 21H), 0.60-0.58 (min, 21-1). LC-MS (ESI$^+$) m/z 653.2 (M+H)$^+$.

Example 175: 1-[4-(cyclopropylamino)-5-[1-[2-[2-[2-[2-[[2-(2,6-dioxo-3-piperidyl)-1,3-dioxo-isoindolin-4-yl]amino]ethoxy]ethoxy]ethoxy]ethyl]triazol-4-yl]-2-pyridyl]pyrazolo[3,4-b]pyridine-5-carbonitrile, I-175

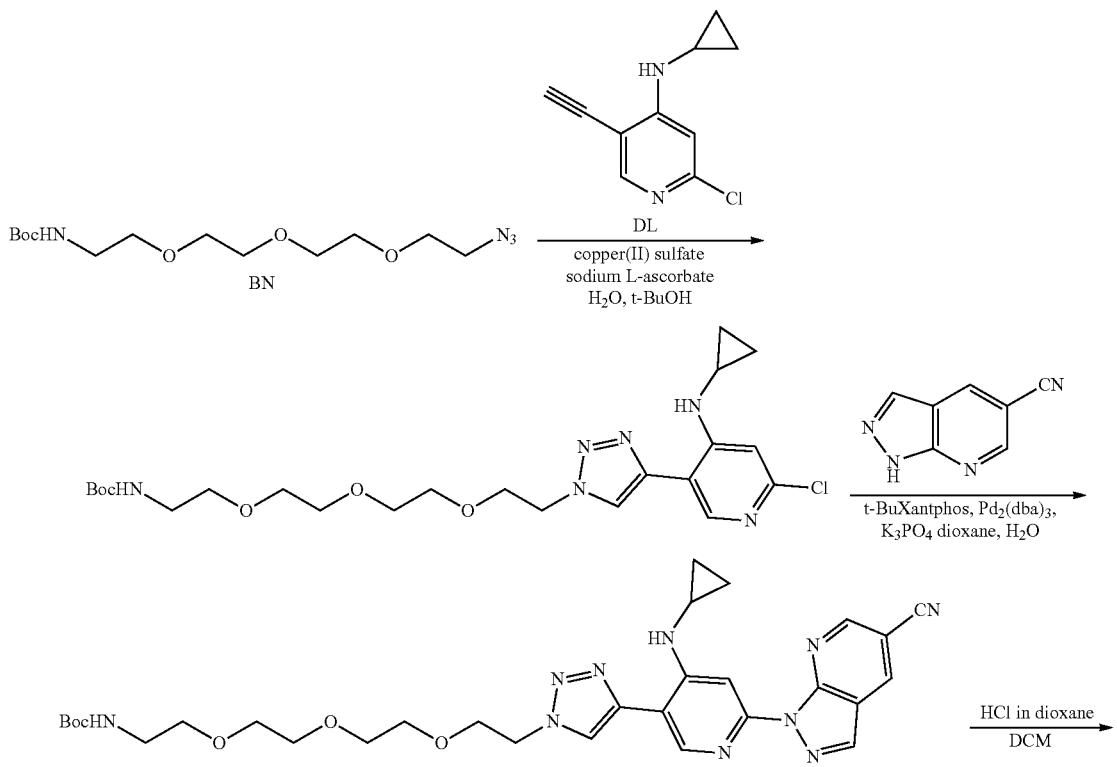

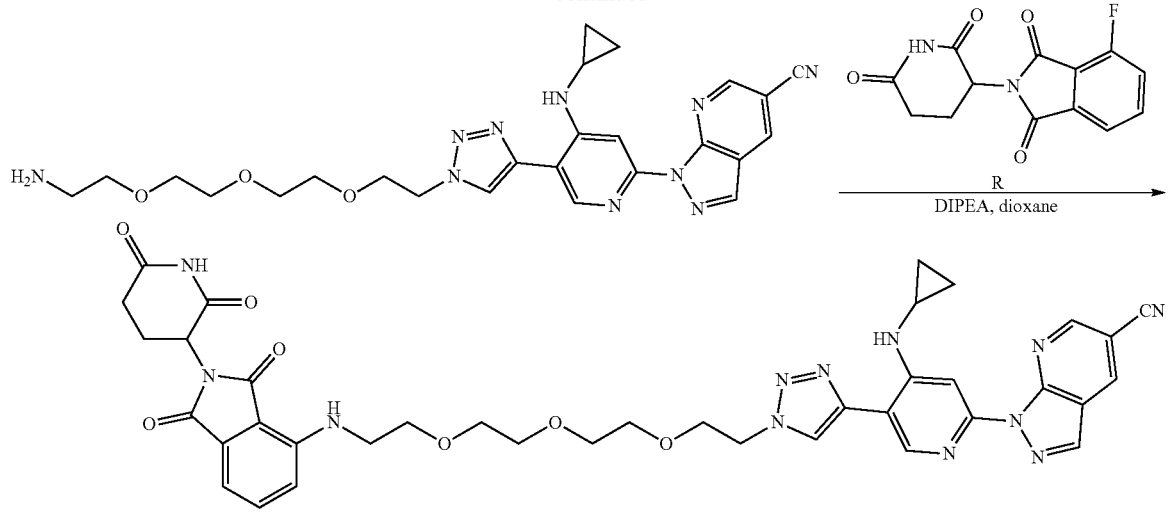

Step 1—Tert-butyl N-[2-[2-[2-[2-[4-[6-chloro-4-(cyclopropylamino)-3-pyridyl]triazol-1-yl]ethoxy]ethoxy]ethoxy]ethyl]carbamate To a solution of tert-butyl N-[2-[2-[2-(2-azidoethoxy)ethoxy]ethoxy]ethyl]carbamate (1.65 g, 5.19 mmol, Intermediate BN), $CuSO_4$ (4.14 mg, 26.0 umol) and sodium (2R)-2-[(1S)-1,2-dihydroxyethyl]-4-hydroxy-5-oxo-2H-furan-3-olate (10.3 mg, 51.9 umol) in a mixed solvent of $H_2O$ (5 mL) and t-BuOH (5 mL) was added 2-chloro-N-cyclopropyl-5-ethynyl-pyridin-4-amine (500 mg, 2.60 mmol, Intermediate DL). The reaction mixture was stirred at 60° C. for 2 h. On completion, the mixture was diluted with $H_2O$ (20 mL) and extracted with EA (2×30 mL). The organic layer was washed with brine (50 mL), dried with $Na_2SO_4$, filtered and concentrated in vacuo. The residue was purified by reverse phase chromatography (0.1% $NH_3.H_2O$) to give the title compound (1.02 g, 77% yield) as a yellow oil. LC-MS (ESI$^+$) m/z 511.4 (M+H)$^+$.

Step 2—Tert-butyl N-[2-[2-[2-[2-[4-[6-(5-cyanopyrazolo[3,4-b]pyridin-1-yl)-4-(cyclopropylamino)-3-pyridyl]triazol-1-yl]ethoxy]ethoxy]ethoxy]ethyl]carbamate Tert-butyl N-[2-[2-[2-[2-[4-[6-chloro-4-(cyclopropylamino)-3-pyridyl]triazol-1-yl]ethoxy]ethoxy]ethoxy]ethyl]carbamate (250 mg, 489 umol), 1H-pyrazolo[3,4-b]pyridine-5-carbonitrile (177 mg, 1.22 mmol, CAS #1234616-67-1), $Pd_2(dba)_3$ (179 mg, 196 umol), $K_3PO_4$ (312 mg, 1.47 mmol) and t-Bu Xphos (83.1 mg, 196 umol) were taken up into a microwave tube. Then dioxane (5 mL) and $H_2O$ (0.5 mL) were added into the microwave tube. The mixture was degassed and purged with nitrogen gas three times, and then the sealed tube was heated to 100° C. and stirred for 8 hrs under microwave. On completion, the mixture was filtered and the filtrate was concentrated in vacuo. The residue was purified by pre-HPLC (column: Gemini 150*25 5 u; mobile phase: [water (0.05% ammonia hydroxide v/v)-ACN]; B %: 36%-66%) to give the title compound (30 mg, 9.4% yield) as a white solid. LC-MS (ESI$^+$) m/z 619.0 (M+H)$^+$.

Step 3—1-[5-[1-[2-[2-[2-(2-aminoethoxy)ethoxy]ethoxy]ethyl]triazol-4-yl]-4-(cyclopropylamino)-2-pyridyl]pyrazolo[3,4-b]pyridine-5-carbonitrile To a solution of tert-butyl N-[2-[2-[2-[2-[4-[6-(5-cyanopyrazolo[3,4-b]pyridin-1-yl)-4-(cyclopropylamino)-3-pyridyl]triazol-1-yl]ethoxy]ethoxy]ethoxy]ethyl]carbamate (30 mg, 48.5 umol) in DCM (1.5 mL) was added HCl in dioxane (4 M, 1.5 mL). The reaction mixture was stirred at rt for 0.5 hr. On completion, the mixture was concentrated in vacuo to give the title compound (26.9 mg, 100% yield, HCl salt). LC-MS (ESI$^+$) m/z 519.3 (M+H)$^+$ Step 4—1-[4-(cyclopropylamino)-5-[1-[2-[2-[2-[2-[[2-(2,6-dioxo-3-piperidyl)-1,3-dioxo-isoindolin-4-yl]amino]ethoxy]ethoxy]ethoxy]ethyl]triazol-4-yl]-2-pyridyl]pyrazolo[3,4-b]pyridine-5-carbonitrile To a solution of 1-[5-[1-[2-[2-[2-(2-aminoethoxy)ethoxy]ethoxy]ethyl]triazol-4-yl]-4-(cyclopropylamino)-2-pyridyl]pyrazolo[3,4-b]pyridine-5-carbonitrile (26.9 mg, 48.5 umol, HCl salt) and 2-(2,6-dioxo-3-piperidyl)-4-fluoro-isoindoline-1,3-dione (14.7 mg, 53.3 umol, Intermediate R) in dioxane (3 mL) was added DIPEA (62.6 mg, 485 umol). The reaction mixture was stirred at 115° C. for 60 hrs. On completion, the reaction mixture was concentrated in vacuo to give a residue. The residue was purified by prep-HPLC (column: Phenomenex Synergi C18 150*25*10 um; mobile phase: [water (0.225% FA)-ACN]; B %: 20%-50%) to give the title compound I-175 (13 mg, 35% yield) as a yellow solid. $^1$H NMR (400 MHz, DMSO-d$_6$) δ 11.16-11.03 (m, 1H), 9.06-9.03 (m, 1H), 9.03-9.00 (m, 1H), 8.75 (s, 1H), 8.64 (s, 1H), 8.60 (s, 1H), 8.44-8.41 (m, 1H), 7.69 (s, 1H), 7.57-7.43 (m, 1H), 7.07-7.02 (m, 1H), 7.01-6.97 (m, 1H), 6.57-6.48 (m, 1H), 5.07-5.00 (m, 1H), 4.66-4.59 (m, 2H), 3.92-3.86 (m, 2H), 3.58-3.54 (m, 4H), 3.53-3.49 (m, 6H), 3.42-3.40 (m, 2H), 2.96-2.81 (m, 1H), 2.62-2.59 (m, 1H), 2.57-2.55 (m, 2H), 2.06-1.99 (m, 1H), 0.94-0.87 (m, 2H), 0.65-0.57 (m, 2H); LC-MS (ESI$^+$) m/z 775.4 (M+H)$^+$.

Example 176: 1-[4-(Cyclopropylamino)-5-[1-[2-[2-[2-[2-[2-[2-[[2-(2,6-dioxo-3-piperidyl)-1,3-dioxo-isoindolin-4-yl]amino]ethoxy]ethoxy]ethoxy]ethoxy]ethyl]triazol-4-yl]-2-pyridyl]pyrazolo[3,4-b]pyridine-5-carbonitrile, I-176

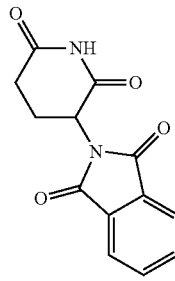
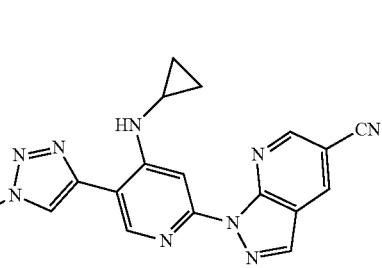

1-[4-(Cyclopropylamino)-5-[1-[2-[2-[2-[2-[2-[2-[[2-(2,6-dioxo-3-piperidyl)-1,3-dioxo-isoindolin-4-yl]amino]ethoxy]ethoxy]ethoxy]ethoxy]ethyl]triazol-4-yl]-2-pyridyl]pyrazolo[3,4-b]pyridine-5-carbonitrile I-176 was synthesized as described above for Example 175 except that Intermediate BQ was used as the azide in Step 1. $^1$H NMR (400 MHz, CD$_3$CN) δ 9.07 (s, 1H), 8.92 (d, J=2.0 Hz, 1H), 8.70 (d, J=2.0 Hz, 1H), 8.56 (s, 1H), 8.49 (s, 1H), 8.45 (s, 1H), 8.39 (s, 1H), 7.82 (s, 1H), 7.55-7.50 (m, 1H), 7.02 (dd, J=4.0, 5.2 Hz, 2H), 6.49-6.40 (m, 1H), 5.00-4.90 (m, 1H), 4.63 (t, J=4.8 Hz, 2H), 3.95-3.92 (m, 2H), 3.66-3.55 (m, 8H), 3.54-3.50 (m, 10H), 3.45-3.38 (m, 2H), 2.75-2.67 (m, 3H), 2.14-2.13 (m, 1H), 1.82-1.77 (m, 1H), 0.95-0.90 (m, 2H), 0.72-0.63 (m, 2H); LC-MS (ESI$^+$) m/z 863.4 (M+H)$^+$.

Example 177: N-[3-carbamoyl-1-[4-[6-[[2-(2,6-dioxo-3-piperidyl)-1,3-dioxo-isoindolin-4-yl]amino]hexa-2,4-diynylcarbamoyl]phenyl]pyrazol-4-yl]-2-[2-(2,2,2-trifluoroethylamino)-4-pyridyl]oxazole-4-carboxamide, I-177

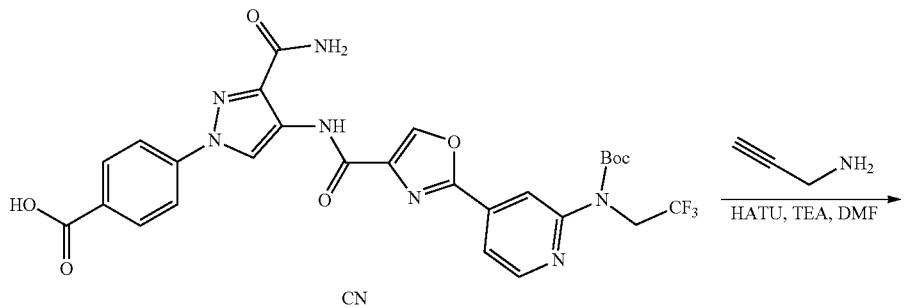
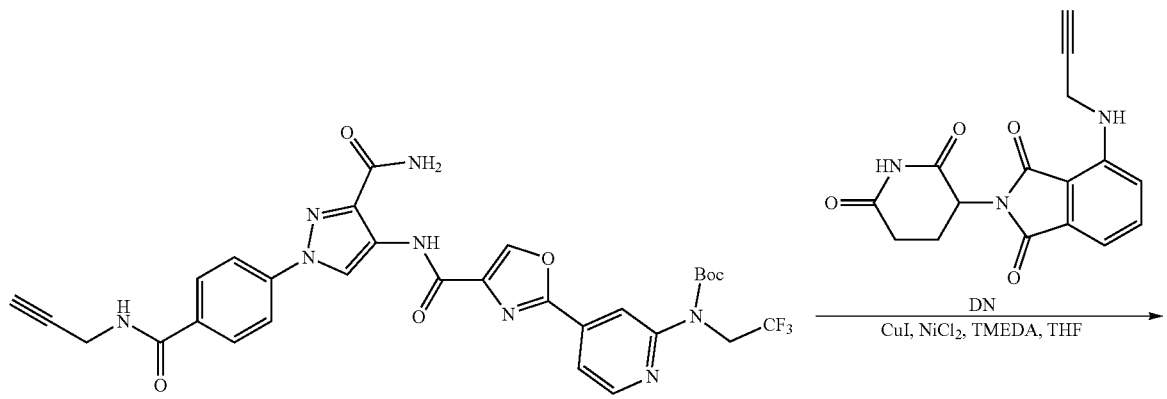

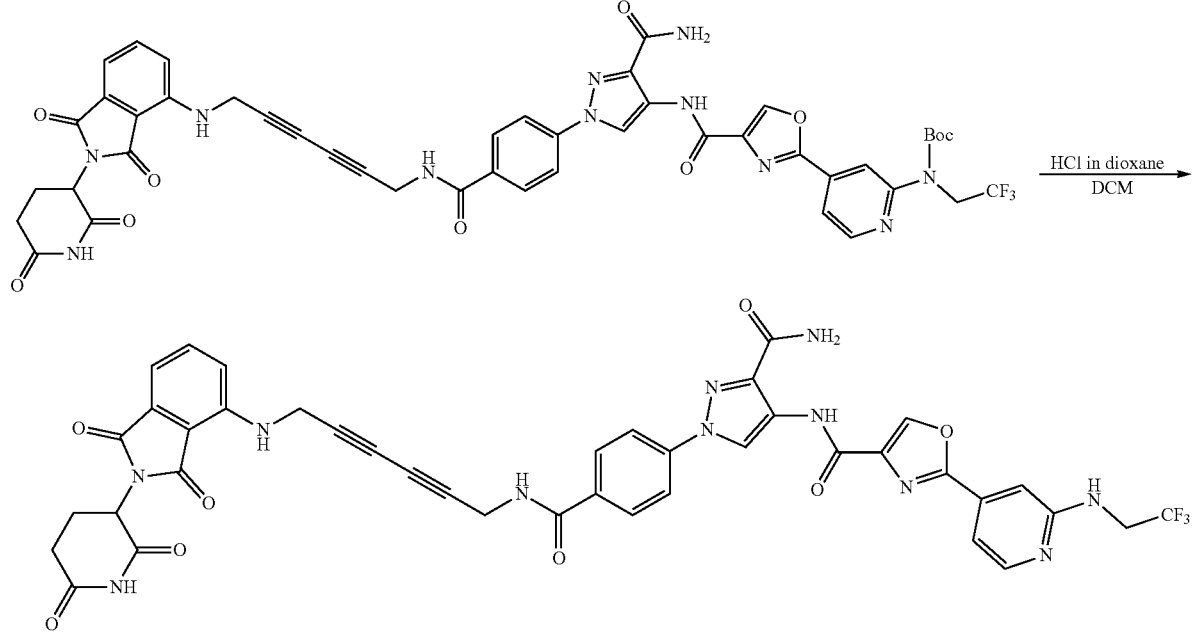

Step 1—Tert-butyl N-[4-[4-[[3-carbamoyl-1-[4-(prop-2-ynylcarbamoyl)phenyl]pyrazol-4-yl]carbamoyl]oxazol-2-yl]-2-pyridyl]-N-(2,2,2-trifluoroethyl)carbamate To a solution of 4-[4-[[2-[2-[tert-butoxycarbonyl(2,2,2-trifluoroethyl)amino]-4-pyridyl]oxazole-4-carbonyl]amino]-3-carbamoyl-pyrazol-1-yl]benzoic acid (200 mg, 324 umol, Intermediate CN) and prop-2-yn-1-amine (21.4 mg, 389 umol, 24.9 uL) in DMF (5.00 mL) was added HATU (148 mg, 389 umol) and DIPEA (125 mg, 974 umol, 169 uL), and the mixture was stirred at rt for 1 hr. On completion, the mixture was diluted with $H_2O$ (30 mL) and extracted with EA (3×15 mL). The organic layers were dried over anhydrous $Na_2SO_4$, filtered and concentrated in vacuo to give the title compound (210 mg, 99% yield) as a white solid. $^1$H NMR (400 MHz, MeOD-$d_4$) δ 11.04 (s, 1H), 9.07 (s, 1H), 9.04-8.99 (m, 2H), 8.63 (d, J=5.2 Hz, 1H), 8.22 (s, 1H), 8.12-8.06 (m, 3H), 8.03-7.98 (m, 2H), 7.77-7.73 (m, 2H), 4.92-4.82 (m, 2H), 4.08-4.03 (m, 2H), 3.11 (t, J=2.4 Hz, 1H), 1.50 (s, 9H).

Step 2—Tert-butyl N-[4-[4-[[3-carbamoyl-1-[4-[6-[[2-(2,6-dioxo-3-piperidyl)-1,3-dioxo-isoindolin-4-yl]amino]hexa-2,4-diynylcarbamoyl]phenyl]pyrazol-4-yl]carbamoyl]oxazol-2-yl]-2-pyridyl]-N-(2,2,2-trifluoroethyl)carbamate A solution of CuI (5.84 mg, 30.6 umol), $NiCl_2 \cdot 6H_2O$ (1.82 mg, 7.66 umol) and N,N,N',N'-tetramethylethane-1,2-diamine (356 ug, 3.06 umol) were dissolved in THF (4.00 mL) and stirred at rt for 5 min. Tert-butyl N-[4-[4-[[3-carbamoyl-1-[4-(prop-2-ynylcarbamoyl)phenyl]pyrazol-4-yl]carbamoyl]oxazol-2-yl]-2-pyridyl]-N-(2,2,2-trifluoroethyl)carbamate (100 mg, 153 umol) and 2-(2,6-dioxo-3-piperidyl)-4-(prop-2-ynylamino)isoindoline-1,3-dione (238 mg, 766 umol, Intermediate DN) in THF (4.00 mL) was then added and the reaction mixture was stirred at rt for 16 h. On completion, the reaction mixture was filtered through a pad of celite, and the celite layer was washed with AcOEt (30 mL). The combined filtrate was concentrated in vacuo. The mixture was purified by prep-HPLC (column: Phenomenex Synergi C18 150*25*10 um; mobile phase: [water (0.225% FA)-ACN]; B %: 50%-80%) to give the title compound (25.0 mg, 16% yield) as a yellow solid. LC-MS (ESI$^+$) m/z 962.0 (M+H)$^+$.

Step 3—N-[3-carbamoyl-1-[4-[6-[[2-(2,6-dioxo-3-piperidyl)-1,3-dioxo-isoindolin-4-yl]amino]hexa-2,4-diynylcarbamoyl]phenyl]pyrazol-4-yl]-2-[2-(2,2,2-trifluoroethyl amino)-4-pyridyl]oxazole-4-carboxamide To a solution of tert-butyl N-[4-[4-[[3-carbamoyl-1-[4-[6-[[2-(2,6-dioxo-3-piperidyl)-1,3-dioxo-isoindolin-4-yl]amino]hexa-2,4-diynylcarbamoyl]phenyl]pyrazol-4-yl]carbamoyl]oxazol-2-yl]-2-pyridyl]-N-(2,2,2-trifluoroethyl)carbamate (20.0 mg, 19.75 umol) in DCM (2.00 mL) was added HCl in dioxane (4 M, 2.00 mL), and the mixture was stirred at rt for 30 min. On completion, the mixture was concentrated in vacuo. The mixture was purified by prep-HPLC (column: Phenomenex Synergi C18 150*25*10 um; mobile phase: [water (0.225% FA)-ACN]; B %: 40%-70%, 13 min) to give the title compound I-177 (2.94 mg, 16% yield, FA) as a yellow solid. $^1$H NMR (400 MHz, DMSO-$d_6$) δ 11.11 (s, 1H), 11.01 (s, 1H), 9.14-9.08 (m, 1H), 9.05 (s, 1H), 9.03 (s, 1H), 8.26 (d, J=5.2 Hz, 1H), 8.16 (s, 1H), 8.11 (d, J=8.8 Hz, 2H), 8.01 (d, J=8.8 Hz, 2H), 7.78 (s, 1H), 7.72-7.65 (m, 2H), 7.27 (s, 1H), 7.20-7.12 (m, 3H), 7.02 (t, J=6.2 Hz, 1H), 5.12-5.02 (m, 1H), 4.36-4.30 (m, 2H), 4.28-4.22 (m, 2H), 4.21-4.17 (m, 2H), 2.99-2.81 (m, 1H), 2.64-2.56 (m, 2H), 2.09-1.99 (m, 1H), LC-MS (ESI$^+$) m/z 862.1 (M+H)$^+$.

Example 178: N-[3-carbamoyl-1-[4-[7-[[2-(2,6-dioxo-3-piperidyl)-1,3-dioxo-isoindolin-4-yl]amino]hepta-2,4-diynylcarbamoyl]phenyl]pyrazol-4-yl]-2-[2-(2,2,2-trifluoroethylamino)-4-pyridyl]oxazole-4-carboxamide, I-178

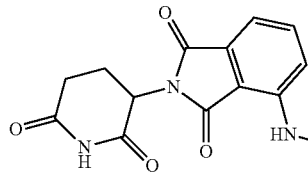
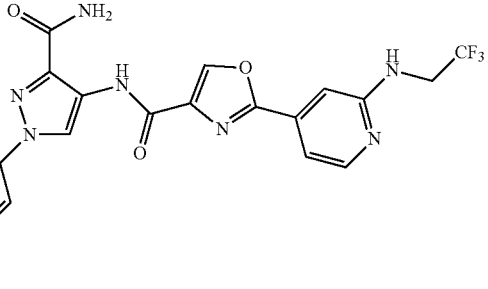

N-[3-carbamoyl-1-[4-[7-[[2-(2,6-dioxo-3-piperidyl)-1,3-dioxo-isoindolin-4-yl]amino]hepta-2,4-diynylcarbamoyl]phenyl]pyrazol-4-yl]-2-[2-(2,2,2-trifluoroethylamino)-4-pyridyl]oxazole-4-carboxamide I-178 was synthesized as described for Example 177, using Intermediate CN as the acid and prop-2-yn-1-amine as the alkyne in Step 1 and Intermediate DO as the alkyne in Step 2, which was run for 80 h at rt. Characterization of the final product: $^1$H NMR (400 MHz, DMSO-$d_6$) δ 11.10 (s, 1H), 11.02 (s, 1H), 9.12 (t, J=5.2 Hz, 1H), 9.06 (d, J=7.6 Hz, 2H), 8.26 (d, J=5.2 Hz, 1H), 8.16 (s, 1H), 8.14 (d, J=8.8 Hz, 2H), 8.04 (d, J=8.8 Hz, 2H), 7.79 (s, 1H), 7.70 (t, J=6.4 Hz, 1H), 7.62-7.56 (m, 1H), 7.28 (s, 1H), 7.19 (s, 1H), 7.19-7.17 (m, 1H), 7.06 (d, J=7.2 Hz, 1H), 6.76 (t, J=6.0 Hz, 1H), 5.10-5.04 (m, 1H), 4.28-4.22 (m, 2H), 4.20 (d, J=5.2 Hz, 2H), 3.73-3.45 (m, 2H), 2.95-2.81 (m, 1H), 2.65 (s, 1H), 2.61-2.58 (m, 1H), 2.57-2.50 (m, 2H), 2.07-1.97 (m, 1H); LC-MS (ESI$^+$) m/z 876.2 (M+H)$^+$.

Example 179: N-[3-carbamoyl-1-[4-[8-[[2-(2,6-dioxo-3-piperidyl)-1,3-dioxo-isoindolin-4-yl]amino]octa-3,5-diynylcarbamoyl]phenyl]pyrazol-4-yl]-2-[2-(2,2,2-trifluoroethylamino)-4-pyridyl]oxazole-4-carboxamide, I-179

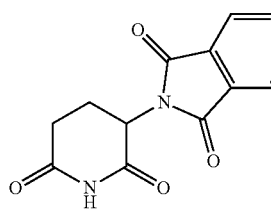
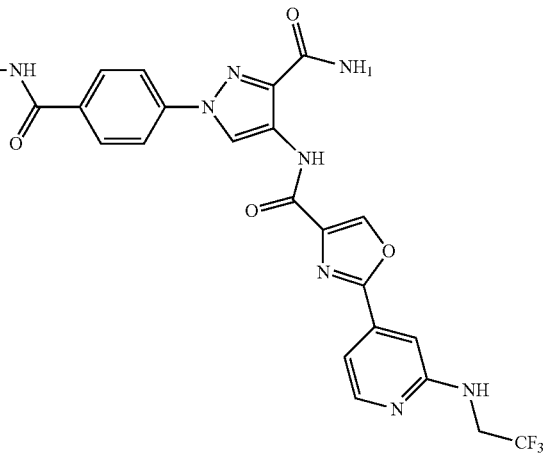

N-[3-carbamoyl-1-[4-[8-[[2-(2,6-dioxo-3-piperidyl)-1,3-dioxo-isoindolin-4-yl]amino]octa-3,5-diynylcarbamoyl]phenyl]pyrazol-4-yl]-2-[2-(2,2,2-trifluoroethylamino)-4-pyridyl]oxazole-4-carboxamide I-179 was synthesized as described for Example 177, using Intermediate CN as the acid and but-3-yn-1-amine(hydrochloride salt) as the alkyne in Step 1 and Intermediate DO as the alkyne in Step 2, which was run for 80 h at rt. Characterization of the final product: $^1$H NMR (400 MHz, DMSO-$d_6$) δ 11.10 (s, 1H), 11.02 (s, 1H), 9.05 (d, J=6.8 Hz, 2H), 8.83 (t, J=5.6 Hz, 1H), 8.26 (d, J=5.6 Hz, 1H), 8.13 (d, J=8.8 Hz, 3H), 8.03 (d, J=8.8 Hz, 2H), 7.78 (s, 1H), 7.70 (t, J=6.4 Hz, 1H), 7.62-7.55 (m, 1H), 7.28 (s, 1H), 7.18 (d, J=8.8 Hz, 2H), 7.05 (d, J=7.2 Hz, 1H), 6.74 (t, J=6.0 Hz, 1H), 5.07 (dd, J=5.2, 13.2 Hz, 1H), 4.30-4.21 (m, 2H), 3.53-3.48 (m, 4H), 2.93-2.86 (m, 1H), 2.65-2.60 (m, 6H), 2.03 (d, J=7.6 Hz, 1H); LC-MS (ESI$^+$) m/z 890.2 (M+H)$^+$.

2289

Example 180: N-[3-carbamoyl-1-[4-[[1-[3-[[2-(2,6-dioxo-3-piperidyl)-1,3-dioxo-isoindolin-4-yl]amino]propyl]triazol-4-yl]methylcarbamoyl]phenyl]pyrazol-4-yl]-2-[2-(2,2,2-trifluoroethylamino)-4-pyridyl]oxazole-4-carboxamide, I-180

2290

(2R)-2-[(1S)-1,2-dihydroxyethyl]-4-hydroxyl-5-oxo-2H-furan-3-olate (728 ug, 3.68 umol) and CuSO$_4$ (293 ug, 1.84 umol). The reaction mixture was heated to 60° C. and stirred for 12 hours. On completion, the mixture was concentrated in vacuo to give a residue, and the residue was triturated with H$_2$O (50 mL). Then the solid the filtered and dried in vacuo.

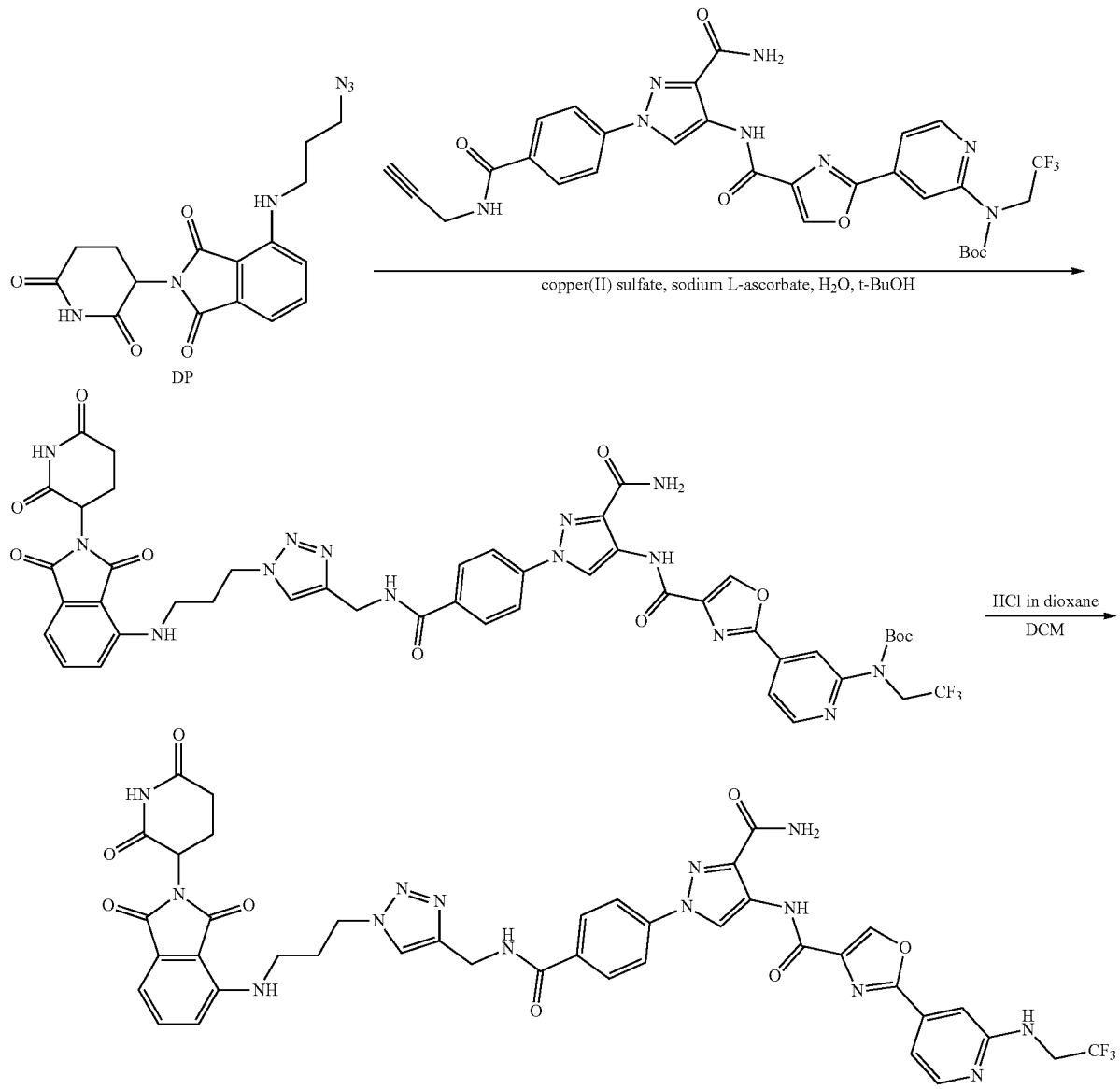

Step 1—Tert-butyl N-[4-[4-[[3-carbamoyl-1-[4-[[1-[3-[[2-(2,6-dioxo-3-piperidyl)-1,3-dioxo-isoindolin-4-yl]amino]propyl]triazol-4-yl]methylcarbamoyl]phenyl]pyrazol-4-yl]carbamoyl]oxazol-2-yl]-2-pyridyl]-N-(2,2,2-trifluoroethyl)carbamate To a solution of 4-(3-azidopropylamino)-2-(2,6-dioxo-3-piperidyl)isoindoline-1,3-dione (131 mg, 368 umol, Intermediate DP) and tert-butyl N-[4-[4-[[3-carbamoyl-1-[4-(prop-2-ynylcarbamoyl)phenyl]pyrazol-4-yl]carbamoyl]oxazol-2-yl]-2-pyridyl]-N-(2,2,2-trifluoroethyl)carbamate (120 mg, 184 umol, synthesized via Step 1 of Example 177) in tert-butanol (4 mL) and H$_2$O (4 mL) was added sodium The crude product was purified by prep-HPLC (column: Phenomenex Synergi C18 150*25*10 um; mobile phase: [water (0.225% FA)-ACN]; B %: 48%-78%, 10 min) to give the title compound (60.0 mg, 32% yield) as a yellow solid. LC-MS (ESI$^+$) m/z 1009.5 (M+H)$^+$.

Step 2—N-[3-carbamoyl-1-[4-[[1-[3-[[2-(2,6-dioxo-3-piperidyl)-1,3-dioxo-isoindolin-4-yl]amino]propyl]triazol-4-yl]methylcarbamoyl]phenyl]pyrazol-4-yl]-2-[2-(2,2,2-trifluoroethylamino)-4-pyridyl]oxazole-4-carboxamide To a solution of tert-butyl N-[4-[4-[[3-carbamoyl-1-[4-[[1-[3-[[2-(2,6-dioxo-3-piperidyl)-1,3-dioxo-isoindolin-4- yl]amino]propyl]triazol-4-yl]methylcarbamoyl]phenyl]pyrazol-4-yl]carbamoyl]oxazol-2-yl]-2-pyridyl]-N-(2,2,2-trifluoroethyl)carbamate (60.0 mg, 59.5 umol) in DCM (2 mL) was added HCl in dioxane (4 M, 2 mL). The reaction mixture was stirred at rt for 30 minutes. On completion, the reaction mixture was concentrated in vacuo to give a residue. The residue was purified by prep-HPLC (column: Boston Green ODS 150*30 5 u; mobile phase: [water (0.225% FA)-ACN]; B %: 35%-65%, 10 min) to give the title compound I-180 (14.2 mg, 24% yield) as yellow solid. $^1$H NMR (400 MHz, DMSO-d$_6$) δ 11.02 (s, 1H), 9.20-9.20 (m, 1H), 9.05 (d, J=4.4 Hz, 2H), 8.26 (d, J=5.2 Hz, 1H), 8.23-7.98 (m, 7H), 7.79 (s, 1H), 7.75-7.68 (m, 1H), 7.57 (t, J=8.0 Hz, 1H), 7.27 (s, 1H), 7.18 (d, J=4.8 Hz, 1H), 7.04 (t, J=8.0 Hz, 2H), 6.72 (m, 1H), 5.05 (dd, J=4.8, 12.8 Hz, 1H), 4.54 (d, J=4.8 Hz, 2H), 4.44 (t, J=6.8 Hz, 2H), 4.30-4.20 (m, 2H), 3.49-3.43 (m, 2H), 2.95-2.83 (m, 1H), 2.61 (m, 1H), 2.58-2.56 (m, 1H), 2.15-2.09 (m, 2H), 2.05-2.00 (m, 1H); LC-MS (ESI$^+$) m/z 909.4 (M+H)$^+$.

Example 181: N-[3-carbamoyl-1-[4-[2-[1-[3-[[2-(2,6-dioxo-3-piperidyl)-1,3-dioxo-isoindolin-4-yl]amino]propyl]triazol-4-yl]ethylcarbamoyl]phenyl]pyrazol-4-yl]-2-[2-(2,2,2-trifluoroethylamino)-4-pyridyl]oxazole-4-carboxamide, I-181

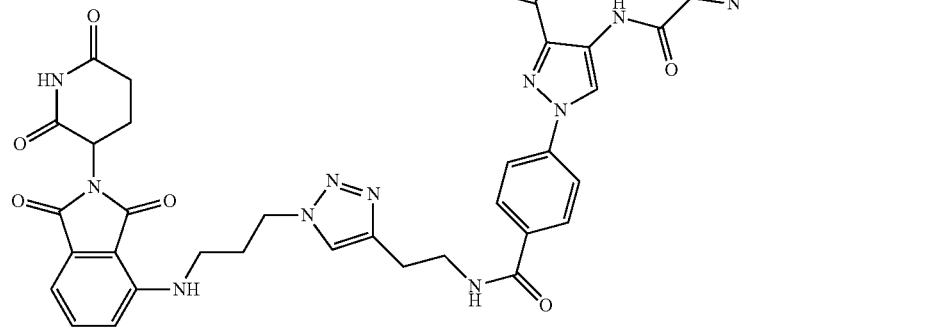

N-[3-carbamoyl-1-[4-[2-[1-[3-[[2-(2,6-dioxo-3-piperidyl)-1,3-dioxo-isoindolin-4-yl]amino]propyl]triazol-4-yl]ethylcarbamoyl]phenyl]pyrazol-4-yl]-2-[2-(2,2,2-trifluoroethylamino)-4-pyridyl]oxazole-4-carboxamide I-181 was synthesized as described for Example 180, using azide Intermediate DP and alkyne tert-butyl N-[4-[4-[[1-[4-(but-3-ynylcarbamoyl)phenyl]-3-carbamoyl-pyrazol-4-yl]carbamoyl]oxazol-2-yl]-2-pyridyl]-N-(2,2,2-trifluoroethyl)carbamate (synthesized via Step 1 of Example 179) in the first step. Characterization of the final product: $^1$H NMR (400 MHz, DMSO-d$_6$) δ 11.11 (s, 1H), 11.03 (s, 1H), 9.05 (s, 1H), 9.04 (s, 1H), 8.74 (t, J=5.6 Hz, 1H), 8.27 (d, J=5.2 Hz, 1H), 8.15 (s, 1H), 8.12-8.08 (m, 2H), 8.02 (s, 2H), 8.00 (s, 1H), 7.79 (s, 1H), 7.74-7.68 (m, 1H), 7.60-7.54 (m, 1H), 7.28 (s, 1H), 7.21-7.17 (m, 1H), 7.06-7.01 (m, 2H), 6.69 (t, J=6.0 Hz, 1H), 5.10-5.02 (m, 1H), 4.46-4.41 (m, 4H), 4.34-4.28 (m, 2H), 3.57-3.53 (m, 2H), 2.95-2.91 (m, 2H), 2.89-2.84 (m, 1H), 2.64-2.59 (m, 2H), 2.13-2.08 (m, 2H), 2.07-2.05 (m, 1H); LC-MS (ESI$^+$) m/z 923.4 (M+H)$^+$.

Example 182: N-[3-carbamoyl-1-[4-[3-[4-[2-[[2-(2,6-dioxo-3-piperidyl)-1,3-dioxo-isoindolin-4-yl]amino]ethyl]triazol-1-yl]propylcarbamoyl]phenyl]pyrazol-4-yl]-2-[2-(2,2-trifluoroethylamino)-4-pyridyl]oxazole-4-carboxamide, I-182
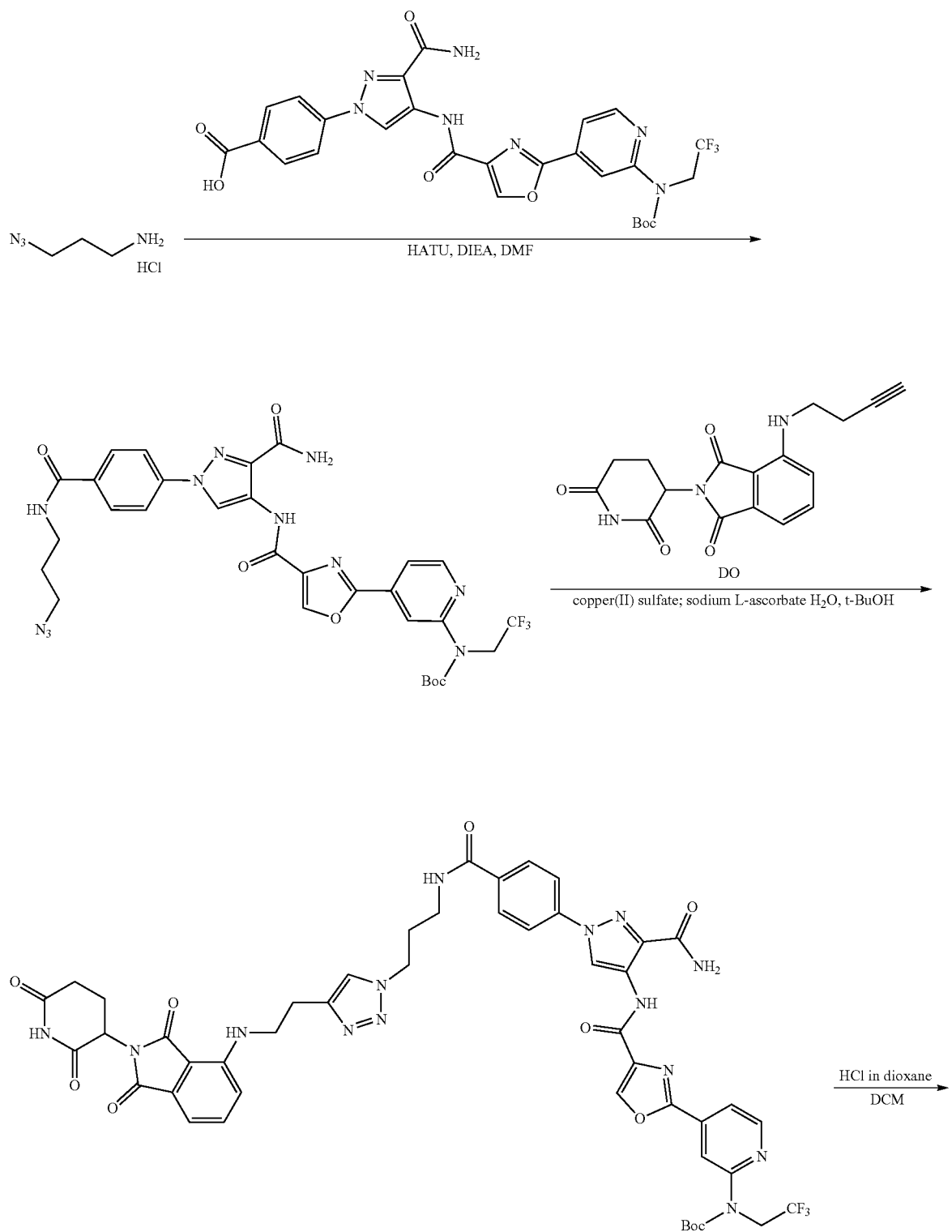

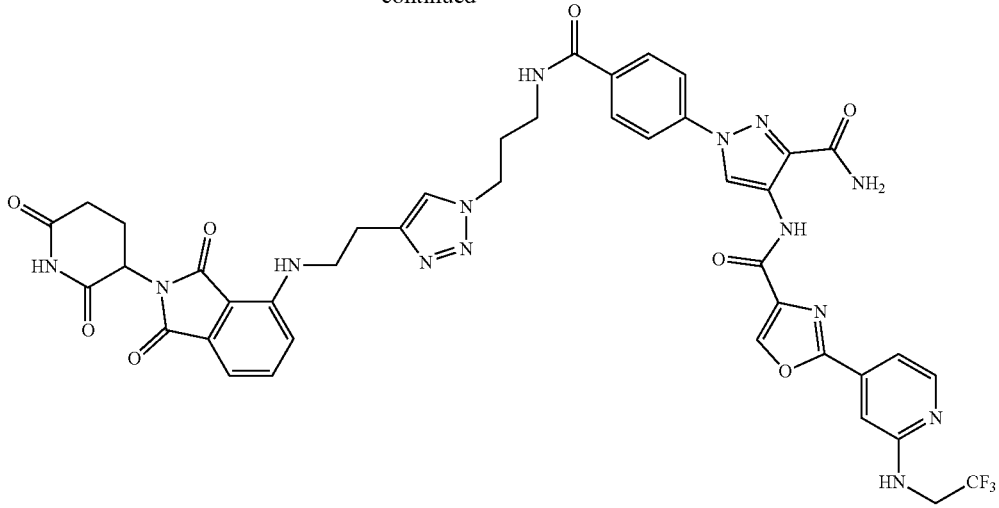

Step 1—Tert-butyl N-[4-[4-[[1-[4-(3-azidopropyl-carbamoyl)phenyl]-3-carbamoyl-pyrazol-4-yl]carbamoyl]oxazol-2-yl]-2-pyridyl]-N-(2,2,2-trifluoroethyl)carbamate To a solution of 3-azidopropan-1-amine (44.3 mg, 324 umol, HCl salt) and 4-[4-[[2-[2-[tert-butoxycarbonyl(2,2,2-trifluoroethyl)amino]-4-pyridyl]oxazole-4-carbonyl]amino]-3-carbamoyl-pyrazol-1-yl]benzoic acid (0.20 g, 324 umol, Intermediate CN) in DMF (4 mL) was added DIPEA (209 mg, 1.62 mmol, 282 uL). The mixture was stirred at rt for 12 minutes, and then HATU (148 mg, 389 umol) was added to the mixture. The reaction mixture was stirred at rt for 2 hours. On completion, the reaction mixture was concentrated in vacuo to give a residue. The residue was purified by reverse phase chromatography (NH$_3$.H$_2$O) to give the title compound (180 mg, 77% yield) as a white solid. LC-MS (ESI$^+$) m/z 698.2 (M+H)$^+$.

Step 2—Tert-butyl N-[4-[4-[[3-carbamoyl-1-[4-[3-[4-[2-[[2-(2,6-dioxo-3-piperidyl)-1,3-dioxo-isoindolin-4-yl]amino]ethyl]triazol-1-yl]propylcarbamoyl]phenyl]pyrazol-4-yl]carbamoyl]oxazol-2-yl]-2-pyridyl]-N-(2,2,2-trifluoroethyl)carbamate To a solution of 4-(but-3-ynylamino)-2-(2,6-dioxo-3-piperidyl)isoindoline-1,3-dione (35.0 mg, 107 umol, Intermediate DO) and tert-butyl N-[4-[4-[[1-[4-(3-azidopropylcarbamoyl)phenyl]-3-carbamoyl-pyrazol-4-yl]carbamoyl]oxazol-2-yl]-2-pyridyl]-N-(2,2,2-trifluoroethyl)carbamate (112 mg, 161 umol) in H$_2$O (1.00 mL) and tert-butanol (3.00 mL) was added CuSO$_4$ (171 ug, 1.08 umol) and sodium (2R)-2-[(1S)-1,2-dihydroxyethyl]-4-hydroxy-5-oxo-2H-furan-3-olate (426 ug, 2.15 umol), and the mixture was heated to 60° C. and stirred for 16 hr. On completion, the mixture was concentrated in vacuo. The mixture was purified by prep-HPLC (column: Boston Green ODS 150*30 5 u; mobile phase: [water (0.225% FA)-ACN]; B %: 50%-80%, 10 min) to give the title compound (30.0 mg, 27% yield) as a yellow solid. LC-MS (ESI$^+$) m/z 1045.2 (M+Na)$^+$.

Step 3—N-[3-carbamoyl-1-[4-[3-[4-[2-[[2-(2,6-dioxo-3-piperidyl)-1,3-dioxo-isoindolin-4-yl]amino]ethyl]triazol-1-yl]propylcarbamoyl]phenyl]pyrazol-4-yl]-2-[2-(2,2,2-trifluoroethylamino)-4-pyridyl]oxazole-4-carboxamide To a solution of tert-butyl N-[4-[4-[[3-carbamoyl-1-[4-[3-[4-[2-[[2-(2,6-dioxo-3-piperidyl)-1,3-dioxo-isoindolin-4-yl]amino]ethyl]triazol-1-yl]propylcarbamoyl]phenyl]pyrazol-4-yl]carbamoyl]oxazol-2-yl]-2-pyridyl]-N-(2,2,2-trifluoroethyl)carbamate (30.0 mg, 29.3 umol) in DCM (2.00 mL) was added HCl in dioxane (4 M, 5.00 mL), and the mixture was stirred at rt for 30 min. On completion, the mixture was concentrated in vacuo. The mixture was purified by prep-HPLC (column: Boston Green ODS 150*30 5 u; mobile phase: [water (0.225% FA)-ACN]; B %: 35%-65%) to give the title compound I-182 (11.8 mg, 43% yield) as a yellow solid. $^1$H NMR (400 MHz, DMSO-d$_6$) δ 11.10 (s, 1H), 11.02 (s, 1H), 9.08-9.05 (m, 1H), 9.04 (s, 1H), 8.68 (s, 1H), 8.26 (d, J=5.2 Hz, 1H), 8.13 (d, J=3.2 Hz, 2H), 8.10 (s, 1H), 8.03 (s, 1H), 8.02-8.01 (m, 2H), 7.79 (s, 1H), 7.74-7.68 (m, 1H), 7.61-7.57 (m, 1H), 7.27 (s, 1H), 7.20-7.17 (m, 1H), 7.12 (d, J=8.8 Hz, 1H), 7.03 (d, J=7.2 Hz, 1H), 6.75-6.71 (m, 1H), 5.06-5.02 (m, 1H), 4.43-4.39 (m, 2H), 4.32-4.21 (m, 2H), 3.64-3.57 (m, 2H), 3.30-3.28 (m, 2H), 2.97-2.93 (m, 2H), 2.88-2.84 (m, 1H), 2.62-2.59 (m, 1H), 2.57-2.56 (m, 1H), 2.12-2.07 (m, 2H), 2.04-1.98 (m, 1H), LC-MS (ESI$^+$) m/z 944.9 (M+Na)$^+$.

Example 183: N-[3-carbamoyl-1-[4-[3-[4-[[[2-(2,6-dioxo-3-piperidyl)-1,3-dioxo-isoindolin-4-yl]amino]methyl]triazol-1-yl]propylcarbamoyl]phenyl]pyrazol-4-yl]-2-[2-(2,2,2-trifluoroethylamino)-4-pyridyl]oxazole-4-carboxamide, I-183

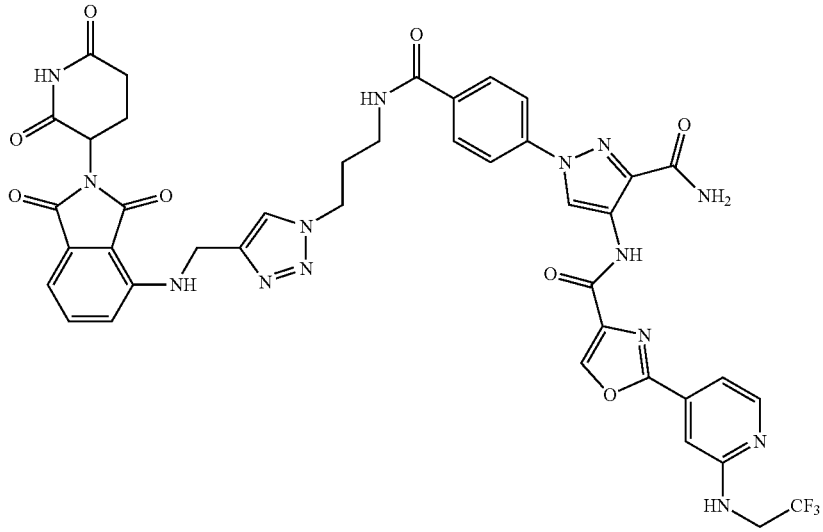 [SMILES: NC(=O)c1nn(-c2ccc(C(=O)NCCCn3cc(CNc4cccc5c4C(=O)N(C4CCC(=O)NC4=O)C5=O)nn3)cc2)cc1NC(=O)c1coc(-c2ccnc(NCC(F)(F)F)c2)n1]

N-[3-carbamoyl-1-[4-[3-[4-[[[2-(2,6-dioxo-3-piperidyl)-1,3-dioxo-isoindolin-4-yl]amino]methyl]triazol-1-yl]propylcarbamoyl]phenyl]pyrazol-4-yl]-2-[2-(2,2,2-trifluoroethylamino)-4-pyridyl]oxazole-4-carboxamide I-183 was synthesized as described above for Example 182, using alkyne Intermediate DN in the second step. Characterization of the final product: $^1$H NMR (400 MHz, DMSO-$d_6$) δ 11.09 (s, 1H), 11.02 (s, 1H), 9.04 (d, J=5.2 Hz, 2H), 8.64 (t, J=5.2 Hz, 1H), 8.26 (d, J=5.2 Hz, 1H), 8.15-8.07 (m, 4H), 8.02 (d, J=8.8 Hz, 2H), 7.77 (s, 1H), 7.70 (t, J=6.4 Hz, 1H), 7.63-7.55 (m, 1H), 7.28 (s, 1H), 7.21-7.14 (m, 2H), 7.12-7.02 (m, 2H), 5.07 (dd, J=5.6, 12.8 Hz, 1H), 4.61 (d, J=6.0 Hz, 2H), 4.43 (t, J=7.2 Hz, 2H), 4.25 (dd, J=6.4, 9.8 Hz, 2H), 3.29-3.24 (m, 2H), 2.95-2.82 (m, 1H), 2.64-2.55 (m, 2H), 2.13-2.00 (m, 3H); LC-MS (ESI$^+$) m/z 909.2 (M+H)$^+$.

Example 184: T(2R)-3-[(8R)-1-[4-[4-[2-[2-[[2-(2,6-dioxo-3-piperidyl)-1,3-dioxo-isoindolin-4-yl]amino]V ethoxy]ethyl]piperazin-1-yl]cyclohexoxy]-7,8-dihydro-6H-cyclopenta[4,5]thieno[1,2-c]pyrimidin-8-yl]-2-hydroxy-propanamide, I-184

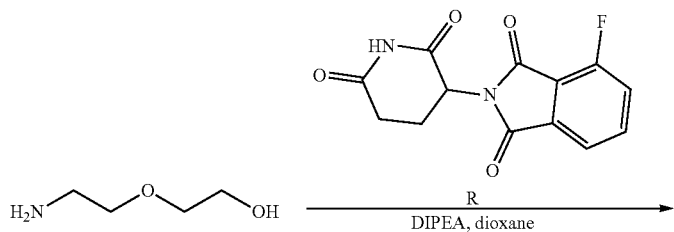

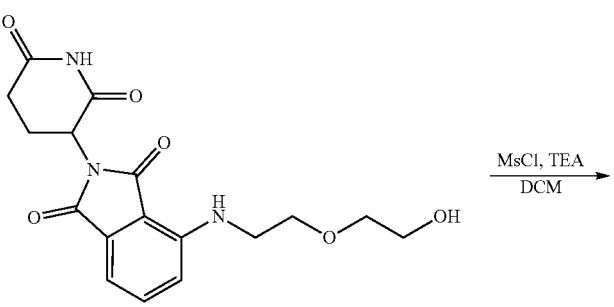

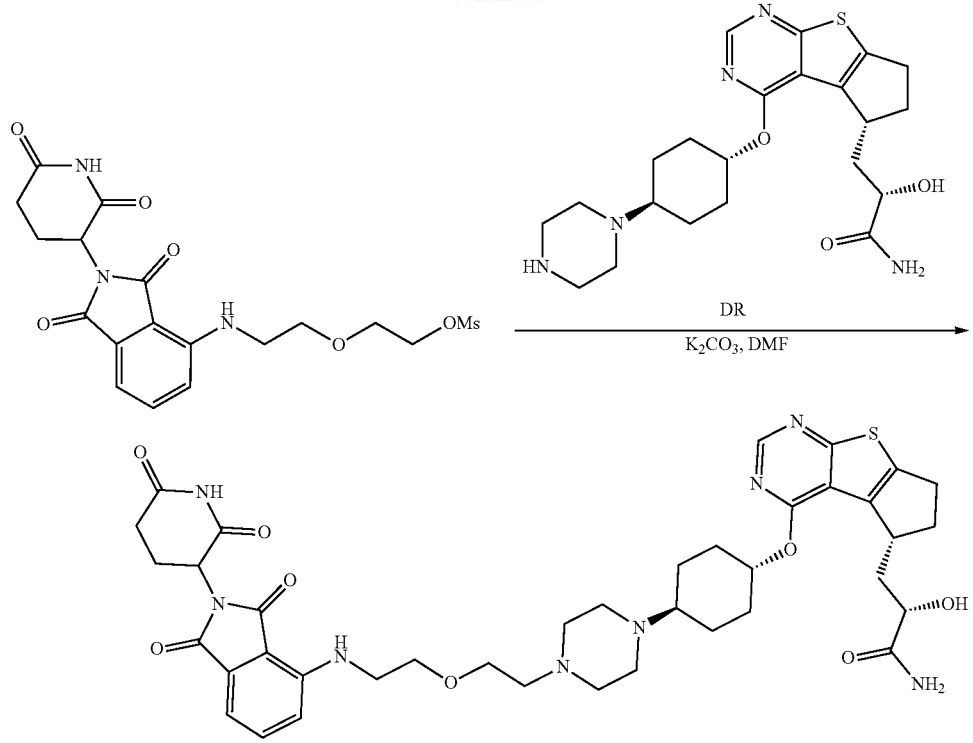

Step 1—2-(2,6-Dioxo-3-piperidyl)-4-[2-(2-hydroxy-ethoxy)ethyl amino]isoindoline-1,3-dione To a solution of 2-(2-aminoethoxy)ethanol (500 mg, 3.53 mmol, HCl salt) in dioxane (15 mL) was added DIPEA (3.65 g, 28.2 mmol) and 2-(2,6-dioxo-3-piperidyl)-4-fluoro-isoindoline-1,3-dione (1.07 g, 3.88 mmol, Intermediate R), and the mixture was stirred at 115° C. for 16 h. On completion, the reaction mixture was concentrated in vacuo to give a residue. The residue was purified by silica gel chromatography (PE:EA=1:1) to give the title compound (500 mg, 37% yield) as a yellow solid. $^1$H NMR (400 MHz, DMSO-$d_6$) δ 11.10 (s, 1H), 7.59 (dd, J=7.6, 8.4 Hz, 1H), 7.15 (d, J=8.8 Hz, 1H), 7.04 (d, J=6.8 Hz, 1H), 6.61 (t, J=5.6 Hz, 1H), 5.06 (dd, J=5.6, 12.8 Hz, 1H), 4.63 (t, J=5.6 Hz, 1H), 3.61 (t, J=5.6 Hz, 2H), 3.55-3.44 (m, 6H), 2.94-2.80 (m, 1H), 2.64-2.52 (m, 2H), 2.08-1.97 (m, 1H); LC-MS (ESI$^+$) m/z 362.0 (M+H)$^+$.

Step 2—2-[2-[[2-(2,6-Dioxo-3-piperidyl)-1,3-dioxo-isoindolin-4-yl]amino]ethoxy]ethyl methanesulfonate To a solution of 2-(2,6-dioxo-3-piperidyl)-4-[2-(2-hydroxyethoxy)ethylamino]isoindoline-1,3-dione (200 mg, 525 umol) and TEA (159 mg, 1.58 mmol) in DCM (20 mL) was added MsCl (120 mg, 1.05 mmol) at 0° C. Then the mixture was allowed to warm to rt and stirred for 3 h. On completion, the reaction mixture was quenched by adding water (30 mL) at 0° C., and then the mixture was extracted with DCM (3×40 mL). The combined organic layers were washed with saturated citric acid (2×20 mL), dried over Na$_2$SO$_4$, filtered and concentrated in vacuo to give the title compound (200 mg, 86% yield) as a yellow solid. LC-MS (ESI$^+$) m/z 440.0 (M+H)$^+$.

Step 3—T(2R)-3-[(8R)-1-[4-[4-[2-[2-[[2-(2,6-dioxo-3-piperidyl)-1,3-dioxo-isoindolin-4-yl]amino]V ethoxy]ethyl]piperazin-1-yl]cyclohexoxy]-7,8-dihydro-6H-cyclopenta[4,5]thieno[1,2-c]pyrimidin-8-yl]-2-hydroxy-propanamide To a solution of (2R)-2-hydroxy-3-[(8R)-1-(4-piperazin-1-ylcyclohexoxy)-7,8-dihydro-6H-cyclopenta[4,5]thieno[1,2-c]pyrimidin-8-yl]propanamide (40 mg, 82.9 umol HCl salt, Intermediate DR) in DMF (3 mL) was added K$_2$CO$_3$ (45.8 mg, 331 umol) and 2-[2-[[2-(2,6-dioxo-3-piperidyl)-1,3-dioxo-isoindolin-4-yl]amino]ethoxy]ethyl methanesulfonate (48.6 mg, 99.5 umol), and the mixture was stirred at 60° C. for 24 h. On completion, the reaction mixture was concentrated in vacuo to give a residue. The residue was purified by prep-HPLC (column: Phenomenex Gemini 150*25 mm*10 um; mobile phase: [water (0.05% ammonia hydroxide v/v)-ACN]) to give the title compound I-184 (23.5 mg, 35% yield, FA salt) as a yellow solid. $^1$H NMR (400 MHz, DMSO-$d_6$) δ 11.11 (s, 1H), 8.53 (s, 1H), 7.64-7.53 (m, 1H), 7.20-7.13 (m, 2H), 7.11 (s, 1H), 7.05 (d, J=6.8 Hz, 1H), 6.60 (t, J=5.6 Hz, 1H), 5.20-5.11 (m, 1H), 5.07 (dd, J=5.6, 12.8 Hz, 1H), 3.93 (t, J=6.4 Hz, 1H), 3.60-3.55 (m, 6H), 3.10-2.99 (m, 2H), 2.95-2.87 (m, 2H), 2.72-2.56 (m, 3H), 2.48-2.39 (m, 10H), 2.38-2.26 (m, 4H), 2.20-2.01 (m, 3H), 1.85-1.82 (m, 2H), 1.63-1.49 (m, 3H), 1.41-1.30 (m, 2H); LC-MS (ESI$^+$) m/z 789.3 (M+H)$^+$.

Example 185: 3-2-(2-((Cyclopropylmethyl)amino)pyridin-4-yl)-N-(1-(4-(((2-(2-(2-((2-(2,6-dioxopiperidin-3-yl)-1,3-dioxoisoindolin-4-yl)amino)ethoxy)ethoxy)ethyl)amino)methyl)phenyl)-3-(trifluoromethyl)-1H-pyrazol-4-yl)oxazole-4-carboxamide, I-185
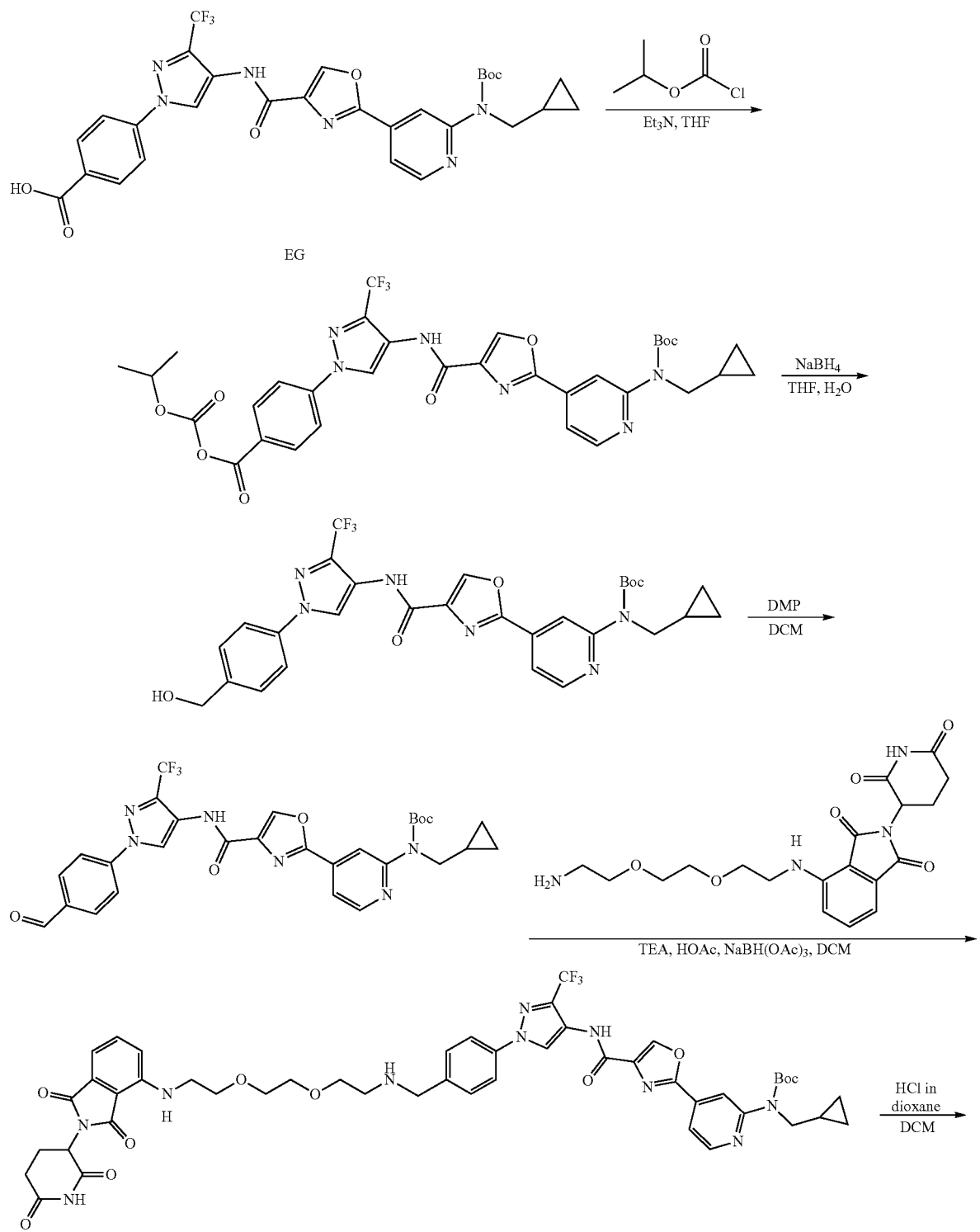

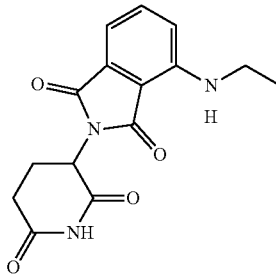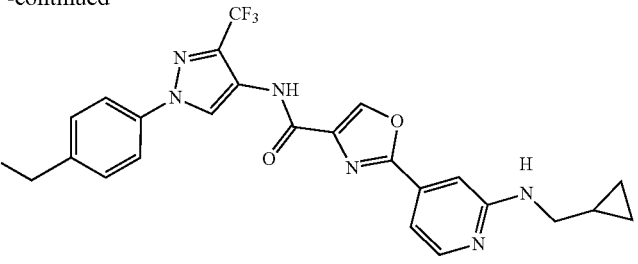

Step 1—4-(4-(2-(2-((Tert-butoxycarbonyl)(cyclopropylmethyl)amino)pyridin-4-yl)oxazole-4-carboxamido)-3-(trifluoromethyl)-1H-pyrazol-1-yl)benzoic (isopropylcarbonic)anhydride To a solution of 4-[4-[[2-[2-[tert-butoxycarbonyl(cyclopropylmethyl)amino]-4-pyridyl]oxazole-4-carbonyl]amino]-3-(trifluoromethyl)pyrazol-1-yl]benzoic acid (700 mg, 960 umol, Intermediate EG) in THF (10 mL) was added TEA (194 mg, 1.92 mmol). Then, the reaction mixture was cooled to −10° C. Next, isopropyl carbonochloridate (235 mg, 1.92 mmol) was added and the reaction mixture was stirred at −10° C. for 2 hours. On completion, the reaction mixture was filtered. The filtrate was concentrated in vacuo to give the title compound (720 mg, 91% yield) as white solid. LC-MS (ESI$^+$) m/z 699.0 (M+H)$^+$.

Step 2—Tert-butyl (cyclopropylmethyl)(4-(4-((1-(4-(hydroxymethyl)phenyl)-3-(trifluoromethyl)-1H-pyrazol-4-yl)carbamoyl)oxazol-2-yl)pyridin-2-yl)carbamate To a solution of isopropoxycarbonyl 4-[4-[[2-[2-[tert-butoxycarbonyl(cyclopropylmethyl)amino]-4-pyridyl]oxazole-4-carbonyl]amino]-3-(trifluoromethyl)pyrazol-1-yl]benzoate (720 mg, 876 umol) in THF (20 mL) was added NaBH$_4$ (66.3 mg, 1.75 mmol) and water (63.1 mg, 3.50 mmol) at 0° C. The reaction mixture was stirred at 0° C. for 1 hour. On completion, the reaction mixture was quenched with water (5 mL) and the mixture was extracted with DCM (3×50 mL). The combined organic layer was washed with brine (20 mL), dried over anhydrous sodium sulfate, filtered and concentrated in vacuo to give the title compound (520 mg, 99% yield) as a white solid. $^1$H NMR (400 MHz, CDCl$_3$) δ 9.06 (s, 1H), 8.88 (s, 1H), 8.54 (d, J=5.2 Hz, 1H), 8.42 (s, 1H), 8.36 (s, 1H), 7.76 (d, J=8.4 Hz, 2H), 7.64 (d, J=4.8 Hz, 1H), 7.51 (d, J=8.4 Hz, 2H), 4.78 (s, 2H), 3.96 (d, J=7.2 Hz, 2H), 1.59 (s, 9H), 0.93-0.81 (m, 1H), 0.47-0.42 (m, 2H), 0.30-0.26 (m, 2H); LC-MS (ESI$^+$) m/z 599.2 (M+H)$^+$.

Step 3—Tert-butyl (cyclopropylmethyl)(4-(4-((1-(4-formylphenyl)-3-(trifluoromethyl)-1H-pyrazol-4-yl)carbamoyl)oxazol-2-yl)pyridin-2-yl)carbamate To a solution of tert-butyl N-(cyclopropylmethyl)-N-[4-[4-[[1-[4-(hydroxymethyl)phenyl]-3-(trifluoromethyl)pyrazol-4-yl]carbamoyl]oxazol-2-yl]-2-pyridyl]carbamate (320 mg, 535 umol) in DCM (10 mL) was added DMP (454 mg, 1.07 mmol). The reaction mixture was stirred at rt for 5 hours. On completion, the reaction mixture was quenched with saturated Na$_2$S$_2$O$_3$ (20 mL) and extracted with DCM (3×30 mL). The combined organic layers were washed with saturated NaHCO$_3$ (2×20 mL), then washed with brine (30 mL), dried over anhydrous sodium sulfate, filtered and concentrated in vacuo. The residue was purified by prep-HPLC (0.1% HCl) to give the title compound (123 mg, 39% yield) as a white solid. $^1$H NMR (400 MHz, CDCl$_3$) δ 10.08 (s, 1H), 9.08 (s, 1H), 9.01 (d, J=5.2 Hz, 1H), 8.98 (s, 1H), 8.57 (s, 1H), 8.06 (d, J=8.4 Hz, 2H), 7.95 (d, J=8.8 Hz, 2H), 7.45 (s, 1H), 7.39 (s, 1H), 3.35 (s, 2H), 1.67 (s, 9H), 1.15-1.05 (m, 1H), 0.78-0.76 (m, 2H), 0.45-0.44 (m, 2H).

Step 4—Tert-butyl (cyclopropylmethyl)(4-(4-(((2-(2-(2-((2-(2,6-dioxopiperidin-3-yl)-1,3-dioxoisoindolin-4-yl)amino)ethoxy)ethoxy)ethyl)amino)methyl)phenyl)-3-(trifluoromethyl)-1H-pyrazol-4-yl)carbamoyl)oxazol-2-yl)pyridin-2-yl)carbamate To a solution of 4-[2-[2-(2-aminoethoxy)ethoxy]ethylamino]-2-(2,6-dioxo-3-piperidyl)isoindoline-1,3-dione (67.8 mg, 154 umol, HCl) in a mixed solvent of DCM (30 mL) and THF (30 mL) was added TEA (17.0 mg, 168 umol). The reaction mixture was stirred at rt for 0.5 hour. Then, tert-butyl N-(cyclopropylmethyl)-N-[4-[4-[[1-(4-formylphenyl)-3-(trifluoromethyl)pyrazol-4-yl]carbamoyl]oxazol-2-yl]-2-pyridyl]carbamate (100 mg, 168 umol, synthesized via Steps 1-2 of Example 127), HOAc (20.1 mg, 335 umol, 19.2 uL) and NaBH(OAc)$_3$ (71.1 mg, 335 umol) were added to the mixture. The resulting reaction mixture was stirred at rt for 12 hours. On completion, the reaction mixture was quenched with water (2 mL) and extracted with ethyl acetate (3×50 mL). The combined organic layers were washed with brine, dried over with anhydrous sodium sulfate, filtered and concentrated in vacuo to give the title compound (150 mg, 91% yield) as a yellow solid. LC-MS (ESI$^+$) m/z 885.1 (M+H−100)$^+$.

Step 5—3-2-(2-(((Cyclopropylmethyl)amino)pyridin-4-yl)-N-(1-(4-(((2-(2-(2-((2-(2,6-dioxopiperidin-3-yl)-1,3-dioxoisoindolin-4-yl)amino)ethoxy)ethoxy)ethyl)amino)methyl)phenyl)-3-(trifluoromethyl)-1H-pyrazol-4-yl)oxazole-4-carboxamide To a solution of tert-butyl N-(cyclopropylmethyl)-N-[4-[4-[[1-[4-[[2-[2-[2-[[2-(2,6-dioxo-3-piperidyl)-1,3-dioxoisoindolin-4-yl]amino]ethoxy]ethoxy]ethylamino]methyl]phenyl]-3-(trifluoromethyl)pyrazol-4-yl]carbamoyl]oxazol-2-yl]-2-pyridyl]carbamate (150 mg, 152 umol) in DCM (4 mL) was added HCl in dioxane (4 M, 4 mL). The reaction mixture was stirred at rt for 0.5 hour. On completion, the reaction mixture was filtered and concentrated in vacuo to give a residue. The residue was purified by prep-HPLC (column: Phenomenex Synergi C18 150*25*10 um; mobile phase: [water (0.225% FA)-ACN]; B %: 10%-40%) to give the title compound I-185 (61.0 mg, 45% yield) as a yellow solid. $^1$H NMR (400 MHz, DMSO-d$_6$) δ 10.88 (s, 1H), 9.70 (s, 1H), 8.75 (s, 1H), 8.63 (s, 1H), 8.03 (s, 1H), 7.94 (d, J=5.2 Hz, 1H), 7.58 (d, J=8.4 Hz, 2H), 7.37-7.30 (m, 1H), 7.27 (d, J=8.4 Hz, 2H), 6.92-6.89 (m, 2H), 6.87 (t, J=5.6 Hz, 1H), 6.83-6.77 (m, 2H), 6.38 (t, J=5.6 Hz, 1H), 4.83 (dd, J=5.6, 12.8 Hz, 1H), 3.55 (s, 2H), 3.43-3.39 (m, 2H), 3.38-3.35 (m, 2H), 3.33-3.30 (m, 2H), 3.29-3.27 (m, 2H), 3.24 (d, J=5.6 Hz, 2H), 2.96 (t, J=5.6 Hz, 2H), 2.72-2.59 (m, 1H), 2.48-2.42 (m, 2H), 2.38-2.31 (m, 1H), 2.30-2.85 (m, 1H), 1.83-1.76 (m, 1H), 0.89-0.81 (m, 1H), 0.27-0.21 (m, 2H), 0.01 (m, 2H); LC-MS (ESI$^+$) m/z 885.1 (M+H)$^+$.

Example 186: 2-[2-(Cyclopropylmethylamino)-4-pyridyl]-N-[1-[3-[[2-[2-[2-[[2-(2,6-dioxo-3-piperidyl)-1,3-dioxo-isoindolin-4-yl]amino]ethoxy]ethoxy]ethylamino]methyl]phenyl]-3-(trifluoromethyl)pyrazol-4-yl]oxazole-4-carboxamide, I-186

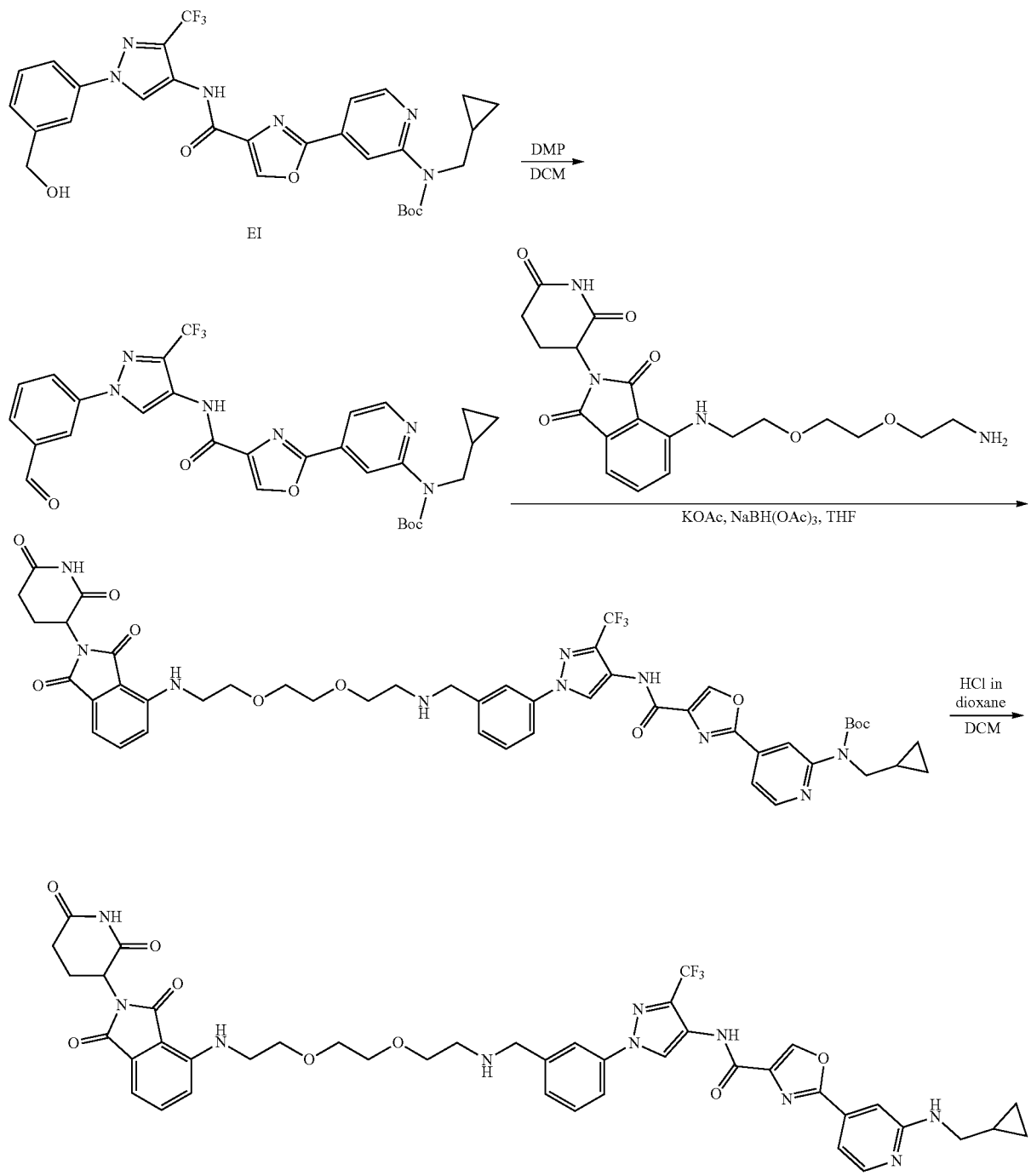

Step 1—Tert-butyl N-(cyclopropylmethyl)-N-[4-[4-[[1-(3-formylphenyl)-3-(trifluoromethyl)pyrazol-4-yl]carbamoyl]oxazol-2-yl]-2-pyridyl]carbamate To a solution of tert-butyl N-(cyclopropylmethyl)-N-[4-[4-[[1-[3-(hydroxymethyl)phenyl]-3-(trifluoro methyl)pyrazol-4-yl]carbamoyl]oxazol-2-yl]-2-pyridyl]carbamate (320 mg, 534 umol. Intermediate EI) in DCM (8.00 mL) was added DMP (105 mg, 249 umol), and the mixture was stirred at 25° C. for 20 hours. On completion, the mixture was quenched with saturated $Na_2S_2O_3$ (2×30 mL) and extracted with DCM (30 mL). The organic layer was washed with saturated $NaHCO_3$ (2×30 mL), dried over anhydrous $Na_2SO_4$, filtered and concentrated in vacuo to give the title compound (280 mg, 87% yield) as a red solid. $^1$H NMR (400 MHz, $CDCl_3$) δ 10.04 (s, 1H), 9.01 (s, 1H), 8.92 (s, 1H), 8.46 (d, J=5.2 Hz, 1H), 8.36 (s, 1H), 8.30 (s, 1H), 8.22 (s, 1H), 8.03-7.98 (m, 1H), 7.83 (d, J=7.6 Hz, 1H), 7.66-7.60 (m, 1H), 7.56 (dd, J=1.2, 5.2 Hz, 1H), 3.88 (d, J=7.2 Hz, 2H), 1.51 (s, 9H), 1.18-1.11 (m, 1H), 0.39-0.34 (m, 2H), 0.24-0.20 (m, 2H).

Step 2—Tert-butyl N-(cyclopropylmethyl)-N-[4-[4-[[1-[3-[[2-[2-[2-[[2-(2,6-dioxo-3-piperidyl)-1,3-dioxo-isoindolin-4-yl]amino]ethoxy]ethoxy]ethylamino]methyl]phenyl]-3-(trifluoromethyl)pyrazol-4-yl]carbamoyl]oxazol-2-yl]-2-pyridyl]carbamate To a solution of tert-butyl N-(cyclopropylmethyl)-N-[4-[4-[[1-(3-formylphenyl)-3-(trifluoromethyl) pyrazol-4-yl]carbamoyl]oxazol-2-yl]-2-pyridyl]carbamate (100 mg, 167 umol) and 4-[2-[2-(2-amino ethoxy)ethoxy]ethylamino]-2-(2,6-dioxo-3-piperidyl)isoindoline-1,3-dione (88.6 mg, 201 umol, HCl, synthesized via Steps 1-2 of Example 127) in THF (30.0 mL) was added KOAc (32.9 mg, 335 umol) and $NaBH(OAc)_3$ (71.0 mg, 335 umol). The mixture was stirred at rt for 16 hours. On completion, the mixture was quenched with water (2 mL) and extracted with ethyl acetate (3×50 mL). The combined organic layers were washed with brine, dried over anhydrous sodium sulfate, filtered and concentrated in vacuo. The mixture was purified by reverse phase prep-HPLC (0.1% FA) to give the title compound (80.0 mg, 48% yield) as a yellow solid. LC-MS (ESI$^+$) m/z 985.4 (M+H)$^+$.

Step 3—2-[2-(Cyclopropylmethylamino)-4-pyridyl]-N-[1-[3-[[2-[2-[2-[[2-(2,6-dioxo-3-piperidyl)-1,3-dioxo-isoindolin-4-yl]amino]ethoxy]ethoxy]ethylamino]methyl]phenyl]-3-(trifluoromethyl)pyrazol-4-yl]oxazole-4-carboxamide To a solution of tert-butyl N-(cyclopropylmethyl)-N-[4-[4-[[1-[3-[[2-[2-[2-[[2-(2,6-dioxo-3-piperidyl)-1,3-dioxo-isoindolin-4-yl]amino]ethoxy]ethoxy]ethylamino]methyl]phenyl]-3-(trifluoromethyl)pyrazol-4-yl]carbamoyl]oxazol-2-yl]-2-pyridyl]carbamate (80.0 mg, 81.2 umol) in DCM (2.00 mL) was added HCl in dioxane (4 M, 2.00 mL). The mixture was stirred at rt for 15 minutes. On completion, the mixture was concentrated in vacuo. The mixture was purified by prep-HPLC (column: Phenomenex Synergi C18 150*25*10 um; mobile phase: [water (0.225% FA)-ACN]; B %: 10%-40%, 10 min) to give the title compound I-186 (41.2 mg, 57% yield) as a yellow solid. $^1$H NMR (400 MHz, DMSO-$d_6$) δ 11.11 (s, 1H), 9.92 (s, 1H), 8.98 (s, 1H), 8.88 (s, 1H), 8.23 (s, 1H), 8.16 (d, J=5.2 Hz, 1H), 7.86 (s, 1H), 7.73 (d, J=8.4 Hz, 1H), 7.55 (dd, J=7.2, 8.4 Hz, 1H), 7.48 (t, J=8.0 Hz, 1H), 7.37 (d, J=7.6 Hz, 1H), 7.13-7.08 (m, 3H), 7.06-7.01 (m, 2H), 6.64-6.54 (m, 1H), 5.08-5.01 (m, 1H), 3.82 (s, 2H), 3.59-3.53 (m, 10H), 3.23-3.16 (m, 2H), 2.92-2.84 (m, 1H), 2.69-2.66 (m, 2H), 2.62-2.58 (m, 1H), 2.57-2.55 (m, 1H), 2.06-1.94 (m, 1H), 1.12-1.01 (m, 1H), 0.50-0.43 (m, 2H), 0.27-0.20 (m, 2H); LC-MS (ESI$^+$) m/z 885.1 (M+H)$^+$.

Example 187: 2-[2-(Cyclopropylmethylamino)-4-pyridyl]-N-[1-[4-[[2-[2-[3-[2-(2,6-dioxo-3-piperidyl)-1,3-dioxo-isoindolin-5-yl]propoxy]ethoxy]ethylamino]methyl]phenyl]-3-(trifluoromethyl)pyrazol-4-yl]oxazole-4-carboxamide, I-187

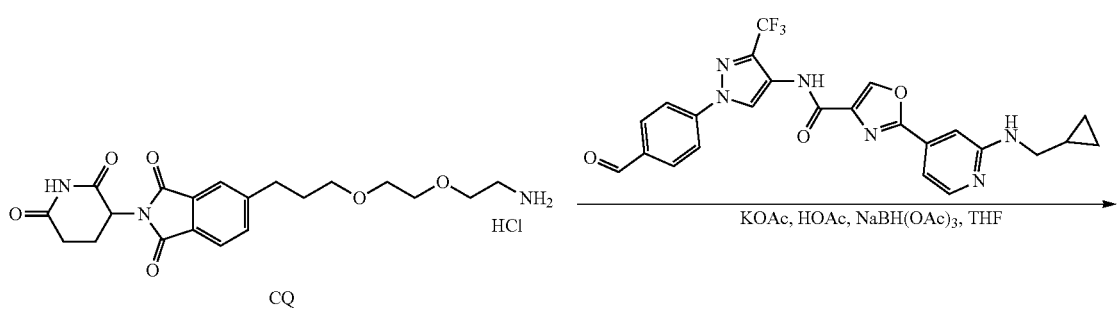

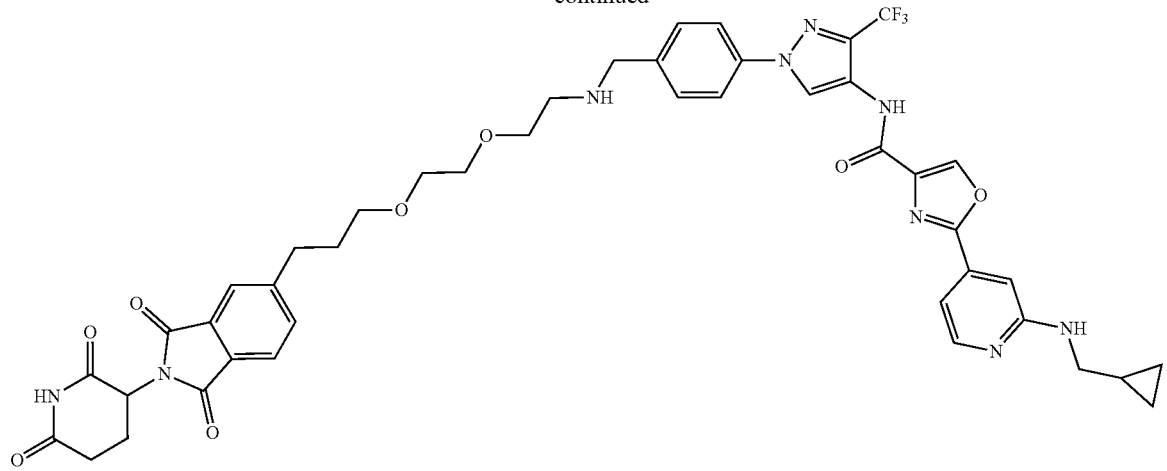

To a solution of 5-[3-[2-(2-aminoethoxy)ethoxy]propyl]-2-(2,6-dioxo-3-piperidyl)isoindoline-1,3-dione (45.0 mg, 102 umol, HCl salt, Intermediate CQ) and 2-[2-(cyclopropylmethylamino)-4-pyridyl]-N-[1-(4-formylphenyl)-3-(trifluoromethyl)pyrazol-4-yl]oxazole-4-carboxamide (54.5 mg, 102 umol, synthesized via Steps 1-3 of Example 185) in THF (10 mL) was added KOAc (20.1 mg, 205 umol) and the reaction mixture was stirred for 30 minutes at rt. Then NaBH(OAc)₃ (54.2 mg, 256 umol) was added in portions and the mixture was stirred at rt for 2 hours. Then HOAc (1.23 g, 20.5 mmol, 1.17 mL) was added and the mixture was stirred for 30 minutes. Finally, more NaBH(OAc)₃ (54.2 mg, 256 umol) was added and the reaction was stirred for 2 hours. On completion, the reaction mixture was quenched by addition water (2 mL), and then concentrated in vacuo. The residue was purified by prep-HPLC (reserve phase (ACN-water/0.1% FA)) and lyophilized to give the title compound I-187 (21.5 mg, 22% yield) as a white solid. ¹H NMR (400 MHz, DMSO-$d_6$) δ 11.12 (s, 1H), 9.92 (s, 1H), 8.98 (s, 1H), 8.86 (s, 1H), 8.26 (s, 1H), 8.16 (d, J=5.2 Hz, 1H), 7.84-7.79 (m, 3H), 7.77 (s, 1H), 7.70 (d, J=7.6 Hz, 1H), 7.51 (d, J=8.4 Hz, 2H), 7.14-7.07 (m, 2H), 7.06-7.02 (m, 1H), 5.14 (dd, J=5.6, 13.2 Hz, 1H), 3.79 (s, 2H), 3.53-3.50 (m, 4H), 3.41-3.75 (m, 2H), 3.19 (t, J=6.4 Hz, 2H), 2.95-2.76 (m, 4H), 2.71-2.60 (m, 4H), 2.59-2.53 (m, 2H), 2.08-2.01 (m, 1H), 1.90-1.81 (m, 2H), 1.11-1.04 (m, 1H), 0.49-0.43 (m, 2H), 0.26-0.20 (m, 2H); LC-MS (ESI⁺) m/z 884.0 (M+H)⁺.

Example 188: N-(3-carbamoyl-1-(4-((5-(2-((5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)pentyl)oxy)ethoxy)pentyl)carbamoyl)phenyl)-1H-pyrazol-4-yl)-2-(2-((2,2,2-trifluoroethyl)amino)pyridin-4-yl)oxazole-4-carboxamide, I-188

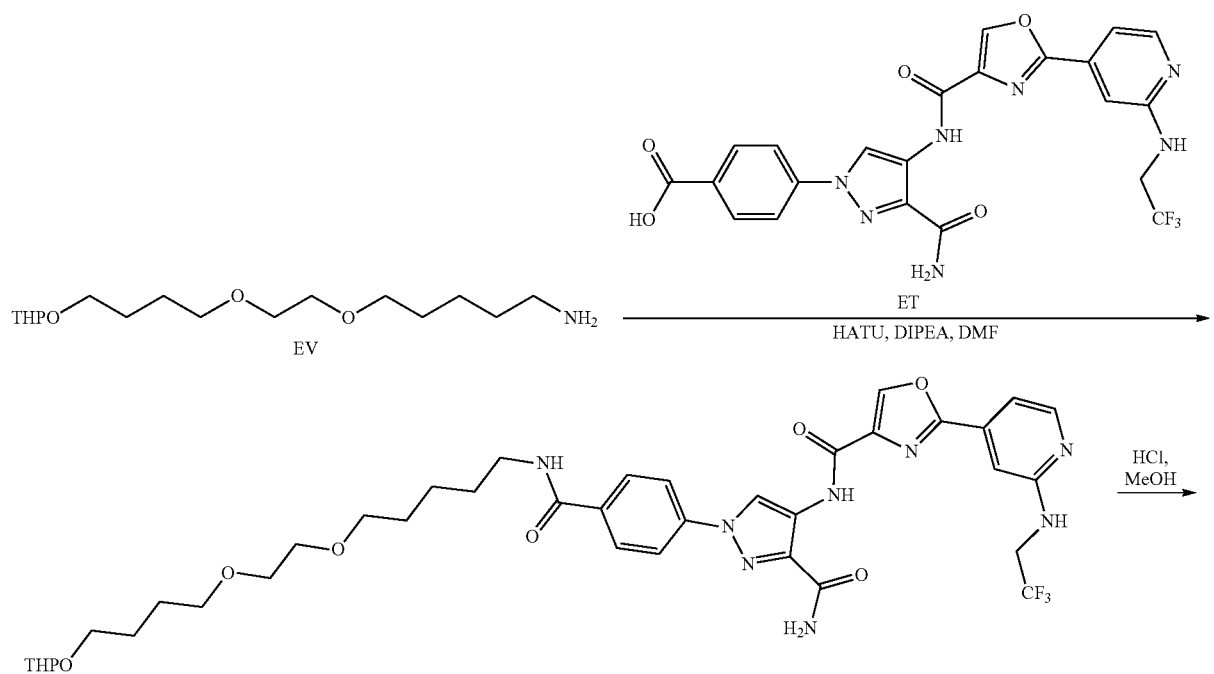

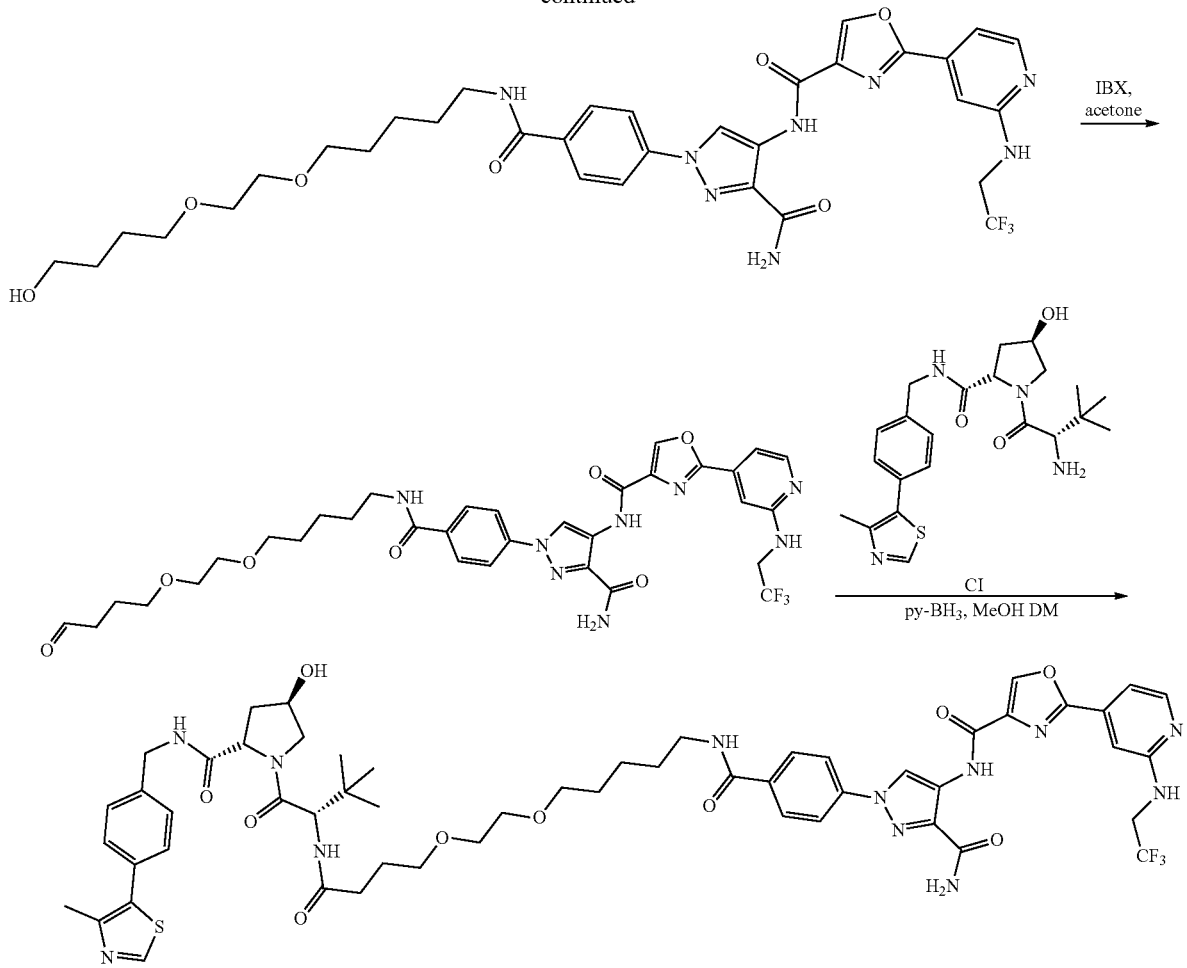

Step 1—N-(3-carbamoyl-1-(4-((5-(2-(4-((tetrahydro-2H-pyran-2-yl)oxy)butoxy)ethoxy)pentyl)carbamoyl)phenyl)-1H-pyrazol-4-yl)-2-(2-((2,2,2-trifluoroethyl)amino)pyridin-4-yl)oxazole-4-carboxamide 5-(2-(4-((tetrahydro-2H-pyran-2-yl)oxy)butoxy)ethoxy)pentan-1-amine (122 mg, 0.38 mmol, Intermediate EV) was dissolved in DMF (2 mL). 4-(3-carbamoyl-4-(2-(2-((2,2,2-trifluoroethyl)amino)pyridin-4-yl)oxazole-4-carboxamido)-1H-pyrazol-1-yl)benzoic acid (198 mg, 0.38 mmol, Intermediate ET), HATU (159 mg, 0.42 mmol) and N,N-diisopropylethylamine (0.13 mL, 0.76 mmol) were then added and the reaction mixture was stirred at rt for 16 h. The reaction mixture was then diluted with a saturated aqueous solution of NaHCO$_3$ and extracted with Ethyl Acetate (3 times). The combined organic was washed with water, dried over magnesium sulfate and filtered. The mixture was then concentrated in vacuo and the residue was purified by silica gel chromatography (gradient of 0-10% methanol in dichloromethane) to give the title compound (161 mg, 50%) as a yellow powder.

Step 2—N-(3-carbamoyl-1-(4-((5-(2-(4-hydroxybutoxy)ethoxy)pentyl)carbamoyl)phenyl)-1H-pyrazol-4-yl)-2-(2-((2,2,2-trifluoroethyl)amino)pyridin-4-yl)oxazole-4-carboxamide N-(3-carbamoyl-1-(4-((5-(2-(4-((tetrahydro-2H-pyran-2-yl)oxy)butoxy)ethoxy)pentyl)carbamoyl)phenyl)-1H-pyrazol-4-yl)-2-(2-((2,2,2-trifluoroethyl)amino)pyridin-4-yl)oxazole-4-carboxamide (161 mg, 0.19 mmol) was dissolved in a 1.25 M solution of HCl in methanol (1.6 mL) and the reaction mixture was stirred at rt for 2 hours. The reaction mixture was then concentrated in vacuo to give the title compound as an orange solid (142 mg, quantitative yield). LC-MS (ESI$^+$) m/z 731.4 (M+H)$^+$.

Step 3—N-(3-carbamoyl-1-(4-((5-(2-(4-oxobutoxy)ethoxy)pentyl)carbamoyl)phenyl)-1H-pyrazol-4-yl)-2-(2-((2,2,2-trifluoroethyl)amino)pyridin-4-yl)oxazole-4-carboxamide To a suspension of N-(3-carbamoyl-1-(4-((5-(2-(4-hydroxybutoxy)ethoxy)pentyl)carbamoyl)phenyl)-1H-pyrazol-4-yl)-2-(2-((2,2,2-trifluoroethyl)amino)pyridin-4-yl)oxazole-4-carboxamide (142 mg, 0.19 mmol) in acetone (10 mL) was added 2-iodoxybenzoic acid (156 mg, 0.57 mmol) and the reaction mixture was heated at 55° C. in a sealed tube for 16 h. The reaction mixture was then quenched with a saturated aqueous solution of NaHCO$_3$ and extracted with Ethyl Acetate. The organic layer was dried over magnesium sulfate, filtered and concentrated in vacuo to give the title compound which was used directly in the subsequent step. LC-MS (ESI$^+$) m/z 729.4 (M+H)$^+$.

Step 4—N-(3-carbamoyl-1-(4-((5-(2-((5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)pentyl)oxy)ethoxy)pentyl)carbamoyl)phenyl)-1H-pyrazol-4-yl)-2-(2-((2,2,2-trifluoroethyl)amino)pyridin-4-yl)oxazole-4-carboxamide N-(3-carbamoyl-1-(4-((5-(2-(4-oxobutoxy)ethoxy)pentyl)carbamoyl)phenyl)-1H-pyrazol-4-yl)-2-(2-((2,2,2-trifluoroethyl)amino)pyridin-4-yl)oxazole-4-carboxamide (177 mg, 0.24 mmol) and (2S,4R)-1-[(2S)-2-amino-3,3-dimethyl-butanoyl]-4-hydroxy-N-[[4-(4-methylthiazol-5-yl)-phenyl]methyl]pyrrolidine-2-carboxamide (125 mg, 0.29 mmol, Intermediate CI) was dissolved in a mixture of methanol (1.4 mL) and dichloromethane (0.8 mL) and stirred for 5 minutes before the addition of borane pyridine complex (49 µL, 0.48 mmol). The reaction mixture was stirred at rt until completion. The reaction mixture was then concentrated in vacuo, diluted in Ethyl Acetate and partitioned with a saturated aqueous solution of NaHCO₃. The precipitate was filtered off and the mixture was extracted with Ethyl Acetate (3 times). The combined organic layer was concentrated in vacuo. Purification with silica gel chromatography (gradient mixture of 0-60% methanol in dichloromethane) gave 74 mg of the impure product. A second purification was performed using silica gel chromatography (gradient of 10-40% methanol in dichloromethane) to give the title compound I-188 (20 mg, 7%) as a yellow powder. ¹H NMR (400 MHz, DMSO): δ 11.00 (s; 1H); 9.02 (d; J=2.46 Hz; 2H); 8.95-8.96 (m; 1H); 8.52-8.56 (m; 2H); 8.24 (d; J=5.29 Hz; 1H); 8.12 (s; 1H); 8.08 (d; J=8.51 Hz; 2H); 7.99 (d; J=8.39 Hz; 2H); 7.76 (s; 1H); 7.68 (t; J=6.53 Hz; 1H); 7.34-7.42 (m; 4H); 7.25 (s; 1H); 7.16 (d; J=5.39 Hz; 1H); 5.02 (d; J=3.19 Hz; 1H); 4.50 (t; J=8.16 Hz; 1H); 4.30-4.39 (m; 3H); 4.17-4.28 (m; 4H); 3.48-3.57 (m; 2H); 3.44 (s; 4H); 3.20-3.40 (m; 6H); 2.99 (s; 1H); 2.41-2.43 (m; 4H); 2.22-2.32 (m; 2H); 1.41-1.57 (m; 6H); 1.28-1.37 (m; 6H); 0.88 (s; 9H). LC-MS (ESI⁺) m/z [M+2H]²⁺: 572.3.

Example 189: (2S,4R)-1-[(2S)-2-[[2-[2-[2-[4-[[7-[[(1R,2S)-2-aminocyclohexyl]amino]-4-oxo-3H-pyrido[4,3-d]pyrimidin-5-yl]amino]indol-1-yl]ethoxy]ethoxy]acetyl]amino]-3,3-dimethyl-butanoyl]-4-hydroxy-N-[[4-(4-methylthiazol-5-yl)phenyl]methyl]pyrrolidine-2-carboxamide, I-189

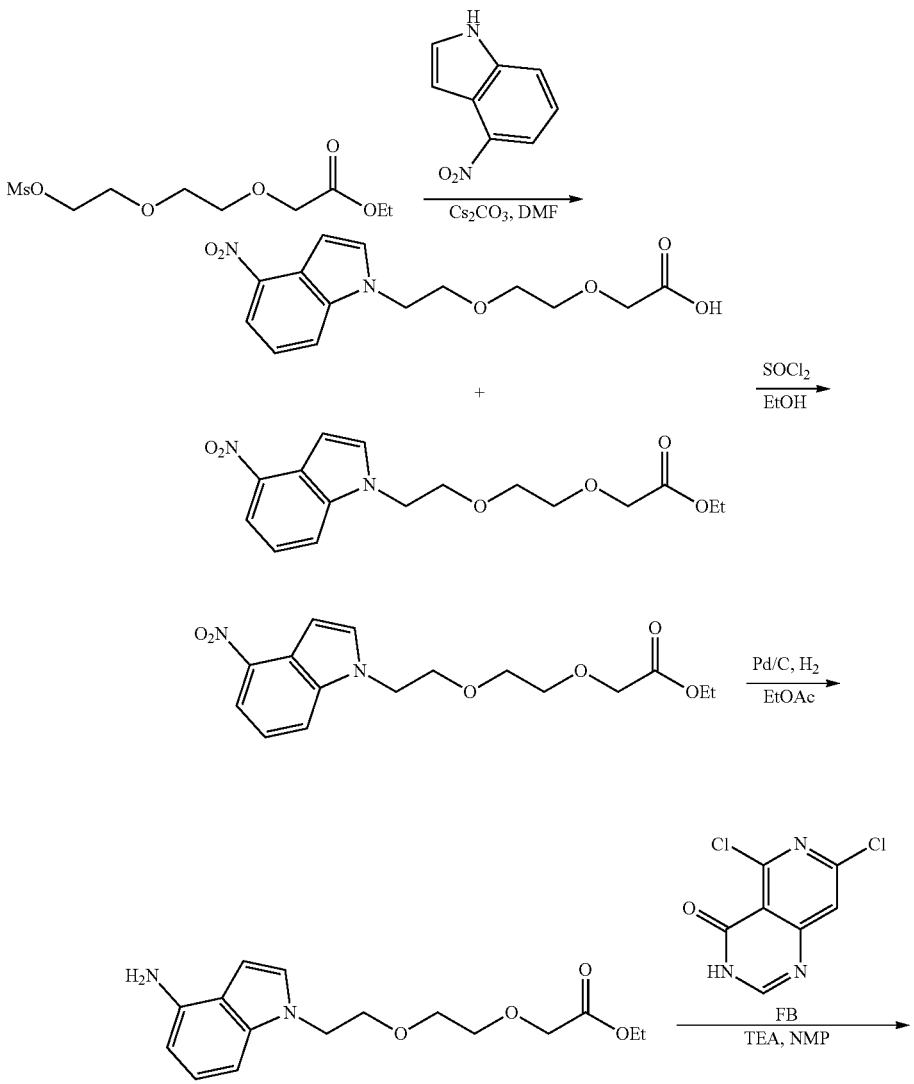

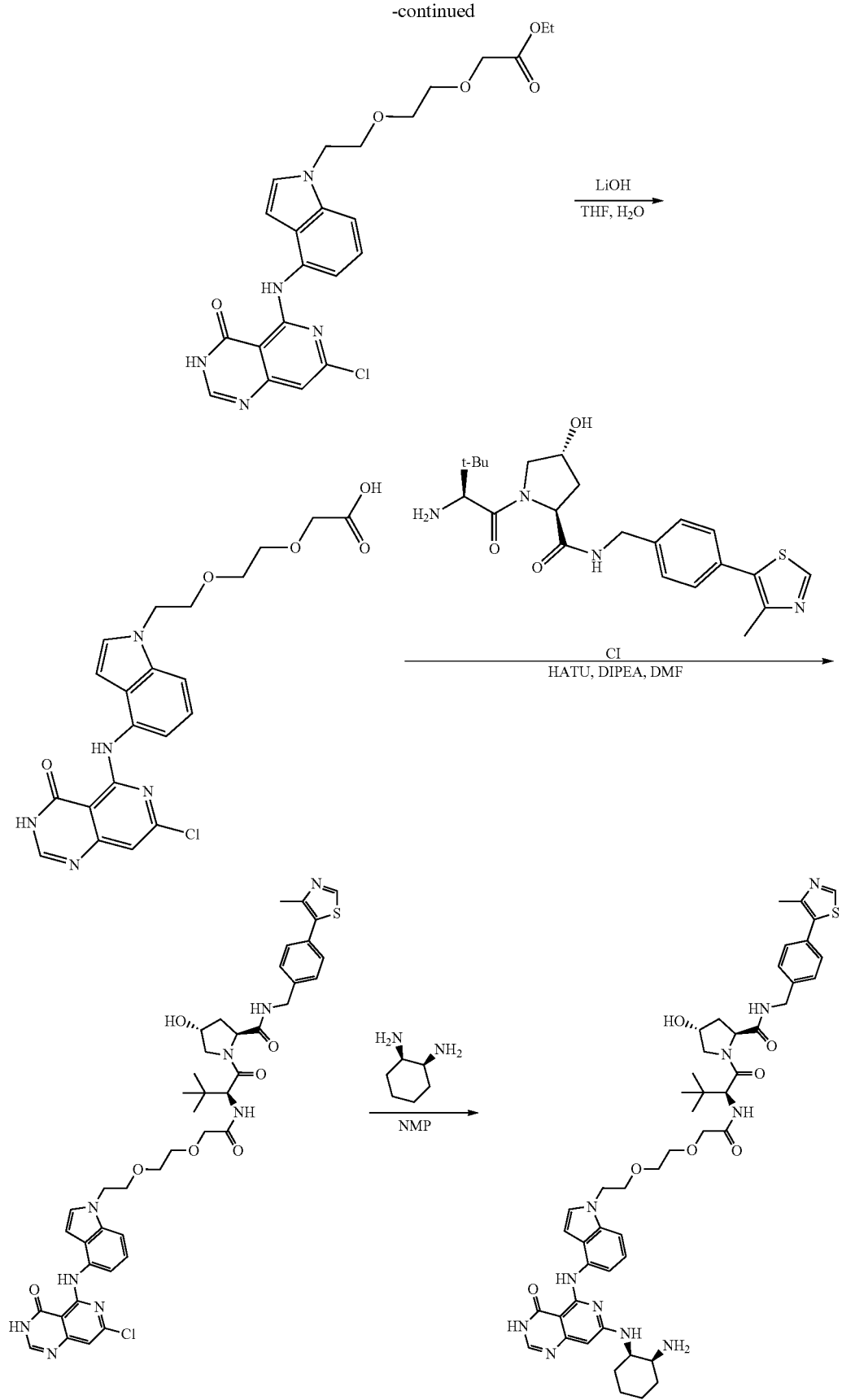

Step 1—Ethyl 2-[2-[2-(4-nitroindol-1-yl)ethoxy]ethoxy]acetate and 2-[2-[2-(4-nitroindol-1-yl)ethoxy]ethoxy]acetic acid To a solution of 4-nitro-1H-indole (649 mg, 4.01 mmol) and Cs₂CO₃ (3.26 g, 10.0 mmol) in DMF (15.0 mL) was added ethyl 2-[2-(2-methylsulfonyloxyethoxy)ethoxy]acetate (1.30 g, 4.81 mmol, synthesized via Steps 1-2 of Intermediate BM), then the reaction mixture was stirred at 80° C. for 12 hours. On completion, the reaction mixture was concentrated in vacuo to give a residue, the residue was diluted with water (40 mL) and acidified with the saturated citric acid aqueous solution (10 mL) until the pH=2. Then the mixture was extracted with EA (30 mL×5). The combined organic layers were dried over sodium sulfate, filtered and concentrated in vacuo to give a mixture of ethyl 2-[2-[2-(4-nitroindol-1-yl) ethoxy]ethoxy]acetate (800 mg, 59% yield) and 2-[2-[2-(4-nitroindol-1-yl)ethoxy]ethoxy]acetic acid (500 mg, 40% yield). LC-MS (ESI⁺) m/z 359.0 (M+Na)⁺ and LC-MS (ESI⁺) m/z 309.0 (M+H)⁺.

Step 2—Ethyl 2-[2-[2-(4-nitroindol-1-yl)ethoxy]ethoxy]acetate

To a mixture of ethyl 2-[2-[2-(4-nitroindol-1-yl) ethoxy]ethoxy]acetate (800 mg, 2.38 mmol) and 2-[2-[2-(4-nitroindol-1-yl)ethoxy]ethoxy]acetic acid (500 mg, 1.62 mmol) in EtOH (10.0 mL) was added SOCl₂ (1.00 g, 8.44 mmol), and the reaction mixture was stirred at 80° C. for 2 hours. On completion, the reaction mixture was concentrated in vacuo to give a residue. The residue was diluted water (15 mL) and extracted with EA (20 mL×3). The combined organic layers were dried over sodium sulfate, filtered and concentrated in vacuo to give the title compound (950 mg, 66% yield). ¹H NMR (400 MHz, CDCl₃) δ 8.12 (d, J=8.0 Hz, 1H), 7.71 (d, J=8.0 Hz, 1H), 7.44 (d, J=3.2 Hz, 1H), 7.25 (d, J=1.6 Hz, 1H), 7.22 (d, J=3.2 Hz, 1H), 4.38 (t, J=5.6 Hz, 2H), 4.19 (q, J=7.2 Hz, 2H), 4.01 (s, 2H), 3.82 (t, J=5.2 Hz, 2H), 3.64-3.60 (m, 2H), 3.59-3.54 (m, 2H), 1.26 (t, J=7.2 Hz, 3H); LC-MS (ESI⁺) m/z 337.1 (M+H)⁺.

Step 3—Ethyl 2-[2-[2-(4-aminoindol-1-yl)ethoxy]ethoxy]acetate

To a solution of ethyl 2-[2-[2-(4-nitroindol-1-yl)ethoxy]ethoxy]acetate (950 mg, 2.82 mmol) in EA (12.0 mL) was added Pd/C (600 mg, 2.82 mmol) under nitrogen atmosphere. The suspension was degassed and purged with hydrogen gas 3 times. The mixture was stirred under hydrogen atmosphere (15 psi pressure) at rt for 2 hours. On completion, the reaction mixture was filtered and concentrated in vacuo to give the title compound (850 mg, 98% yield). ¹H NMR (400 MHz, CDCl₃) δ 7.09 (d, J=3.6 Hz, 1H), 7.03 (t, J=8 Hz, 1H), 6.83 (d, J=8.0 Hz, 1H), 6.41-6.39 (m, 2H), 4.27 (t, J=6.0 Hz, 2H), 4.23 (q, J=7.2 Hz, 2H), 4.09 (s, 2H), 3.91 (s, 2H), 3.81 (t, J=6.0 Hz, 2H), 3.69-3.64 (m, 2H), 3.60-3.56 (m, 2H), 1.30 (t, J=7.2 Hz, 3H); LC-MS (ESI⁺) m/z 307.1 (M+H)⁺.

Step 4-Ethyl 2-[2-[2-[4-[(7-chloro-4-oxo-3H-pyrido[4,3-d]pyrimidin-5-yl)amino]indol-1-yl]ethoxy]ethoxy]acetate To a solution of ethyl 2-[2-[2-(4-aminoindol-1-yl)ethoxy]ethoxy]acetate (500 mg, 1.63 mmol) and 5,7-dichloro-3H-pyrido[4,3-d]pyrimidin-4-one (352 mg, 1.63 mmol, Intermediate FB) in NMP (4 mL) was added TEA (329 mg, 3.26 mmol), and the reaction mixture was stirred at 140° C. for 2 hours. On completion, the reaction mixture was concentrated in vacuo to give a residue. The residue was purified by silica gel chromatography (PE/EA=1/2) to give the title compound (500 mg, 63% yield) as a yellow solid. ¹H NMR (400 MHz, DMSO-d₆) δ 12.95 (s, 1H), 11.75 (s, 1H), 8.31 (s, 1H), 8.17 (d, J=7.6 Hz, 1H), 7.44 (d, J=3.2 Hz, 1H), 7.28 (d, J=8.0 Hz, 1H), 7.17 (t, J=8.0 Hz, 2H), 6.91 (s, 1H), 6.56 (d, J=3.2 Hz, 1H), 4.36 (t, J=5.6 Hz, 2H), 4.10 (q, J=7.2 Hz, 2H), 4.05 (s, 2H), 3.76 (t, J=5.2 Hz, 2H), 3.53 (d, J=3.6 Hz, 4H), 1.18 (t, J=7.2 Hz, 3H); LC-MS (ESI⁺) m/z 486.0 (M+H)⁺.

Step 5—2-[2-[2-[4-[(7-Chloro-4-oxo-3H-pyrido[4,3-d]pyrimidin-5-yl)amino]indol-1-yl]ethoxy]ethoxy]acetic acid To a solution of ethyl 2-[2-[2-[4-[(7-chloro-4-oxo-3H-pyrido[4,3-d]pyrimidin-5-yl)amino]indol-1-yl]ethoxy]ethoxy]acetate (260 mg, 535 umol) in THF (3.00 mL) and H₂O (3.00 mL) was added LiOH (51.2 mg, 2.14 mmol), and the mixture was stirred at rt for 2 hours. On completion, the mixture was acidified with 1N HCl solution (1 mL) until the pH=3, then diluted with water (5 mL) and extracted with DCM (50 mL×3). The combined organic layers were dried over sodium sulfate, filtrated and concentrated in vacuo to give the product (230 mg, 93% yield) as a light yellow solid. LC-MS (ESI⁺) m/z 458.1 (M+H)⁺.

Step 6—(2S,4R)-1-[(2S)-2-[[2-[2-[2-[4-[(7-chloro-4-oxo-3H-pyrido[4,3-d]pyrimidin-5-yl)amino]indol-1-yl]ethoxy]ethoxy]acetyl]amino]-3,3-dimethyl-butanoyl]-4-hydroxy-N-[[4-(4-methylthiazol-5-yl)phenyl]methyl]pyrrolidine-2-carboxamide A solution of 2-[2-[2-[4-[(7-chloro-4-oxo-3H-pyrido[4,3-d]pyrimidin-5-yl)amino]indol-1-yl]ethoxy]ethoxy]acetic acid (180 mg, 393 umol) in DMF (3.00 mL) was cooled to 0° C. Then, (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide (166 mg, 357 umol, HCl salt, Intermediate CI), DIPEA (277 mg, 2.14 mmol) and HATU (163 mg, 428 umol) were added. Then the mixture was stirred at rt for 6 hours. On completion, the reaction mixture was concentrated in vacuo to remove the DMF. The residue was diluted with water (40 mL) and extracted with EA (40 mL×3). The combined organic layers were dried over sodium sulfate and concentrated in vacuo to give a residue. The residue was purified by silica gel chromatography (reverse phase (0.1% FA)) to give the title compound to (255 mg, 81% yield) as light yellow solid. LC-MS (ESI⁺) m/z 870.4 (M+H)⁺.

Step 7—(2S,4R)-1-[(2S)-2-[[2-[2-[2-[4-[[7-[[(1R,2S)-2-aminocyclohexyl]amino]-4-oxo-3H-pyrido[4,3-d]pyrimidin-5-yl]amino]indol-1-yl]ethoxy]ethoxy]acetyl]amino]-3,3-dimethyl-butanoyl]-4-hydroxy-N-[[4-(4-methylthiazol-5-yl)phenyl]methyl]pyrrolidine-2-carboxamide A mixture of (2S,4R)-1-[(2S)-2-[[2-[2-[2-[4-[(7-chloro-4-oxo-3H-pyrido[4,3-d]pyrimidin-5-yl)amino]indol-1-yl]ethoxy]ethoxy]acetyl]amino]-3,3-dimethyl-butanoyl]-4-hydroxy-N-[[4-(4-methylthiazol-5-yl)phenyl]methyl]pyrrolidine-2-carboxamide (100 mg, 114 umol) and (1R,2S)-cyclohexane-1,2-diamine (52.4 mg, 459 umol) in NMP (2 mL) were placed in a sealed tube and stirred at 140° C.

for 1.5 hours under microwave. On completion, the mixture was purified by prep-HPLC (column: Boston Green ODS 150*30 5 u; mobile phase: [water (0.225% FA)-ACN]) to give the title compound I-189 (21.0 mg, 18% yield) as a white solid. $^1$H NMR (400 MHz, DMSO-d$_6$) δ 11.71 (s, 1H), 8.94 (s, 1H), 8.61 (t, J=5.6 Hz, 1H), 8.35 (s, 2H), 8.30-8.24 (m, 1H), 7.91 (s, 1H), 7.47-7.30 (m, 6H), 7.17 (d, J=8.0 Hz, 1H), 7.08 (t, J=5.6 Hz, 1H), 6.57 (d, J=3.2 Hz, 1H), 6.00 (s, 1H), 4.60 (d, J=9.6 Hz, 1H), 4.46 (t, J=8.0 Hz, 1H), 4.39-4.31 (m, 4H), 4.27-4.22 (m, 1H), 3.99-3.94 (m, 2H), 3.77 (t, J=5.4 Hz, 2H), 3.71-3.65 (m, 2H), 3.63-3.60 (m, 2H), 3.58-3.56 (m, 2H), 3.54-3.53 (m, 2H), 2.53-2.52 (m, 2H), 2.41 (s, 3H), 2.07 (s, 1H), 1.97-1.87 (m, 2H), 1.80-1.74 (m, 2H), 1.68-1.60 (m, 4H), 1.44-1.36 (m, 2H), 1.00-0.92 (s, 9H). LC-MS (ESI$^+$) m/z 948.3 (M+H)$^+$.

Example 190: (2S,4R)-1-[(2S)-2-[[2-[2-[2-[2-[4-[[7-[[(1R,2S)-2-aminocyclohexyl]amino]-4-oxo-3H-pyrido[4,3-d]pyrimidin-5-yl]amino]indol-1-yl]ethoxy]ethoxy]ethoxy]ethoxy]acetyl]amino]-3,3-dimethyl-butanoyl]-4-hydroxy-N-[[4-(4-methylthiazol-5-yl)phenyl]methyl]pyrrolidine-2-carboxamide, I-190

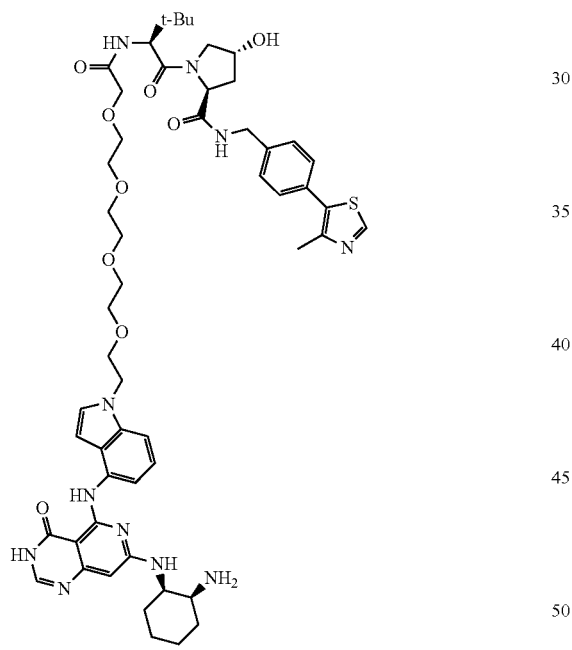

The title compound I-190 was synthesized as described in the method above for Example 189, using Intermediate BK as the mesylate in the first step which was run at 80° C. for 8 h. Time and temperature variations were as follows: Step 2 was run at 80° C. for 6 h, Step 3 was run at rt for 6 h and Step 7 was run at 150° C. for 1.5 h. Characterization data of the final compound: $^1$H NMR (400 MHz, DMSO-d$_6$) δ 11.25 (s, 1H), 9.18 (s, 1H), 9.09 (s, 1H), 8.68 (t, J=5.6 Hz, 1H), 8.30-8.28 (m, 3H), 8.20 (s, 1H), 8.10 (d, J=7.2 Hz, 1H), 7.46-7.35 (m, 6H), 7.24 (d, J=7.6 Hz, 1H), 7.12 (t, J=7.6 Hz, 1H), 6.51 (d, J=2.8 Hz, 1H), 6.33 (s, 1H), 4.44-4.17 (m, 10H), 3.90 (s, 2H), 3.79-3.37 (m, 18H), 2.44 (s, 3H), 2.13-1.83 (m, 4H), 1.79-1.56 (m, 4H), 1.48-1.34 (m, 2H), 0.92 (s, 9H); LC-MS (ESI$^+$) m/z 1036.3 (M+H)$^+$.

Example 191: N-[2-[[5-chloro-2-[5-[2-[2-[2-[2-[2-[[2-(2,6-dioxo-3-piperidyl)-1,3-dioxo-isoindolin-4-yl]amino]ethoxy]ethoxy]ethoxy]ethoxy]ethoxy]-4-methoxy-2-methyl-anilino]pyrimidin-4-yl]amino]-5-methoxy-phenyl]methanesulfonamide, I-191
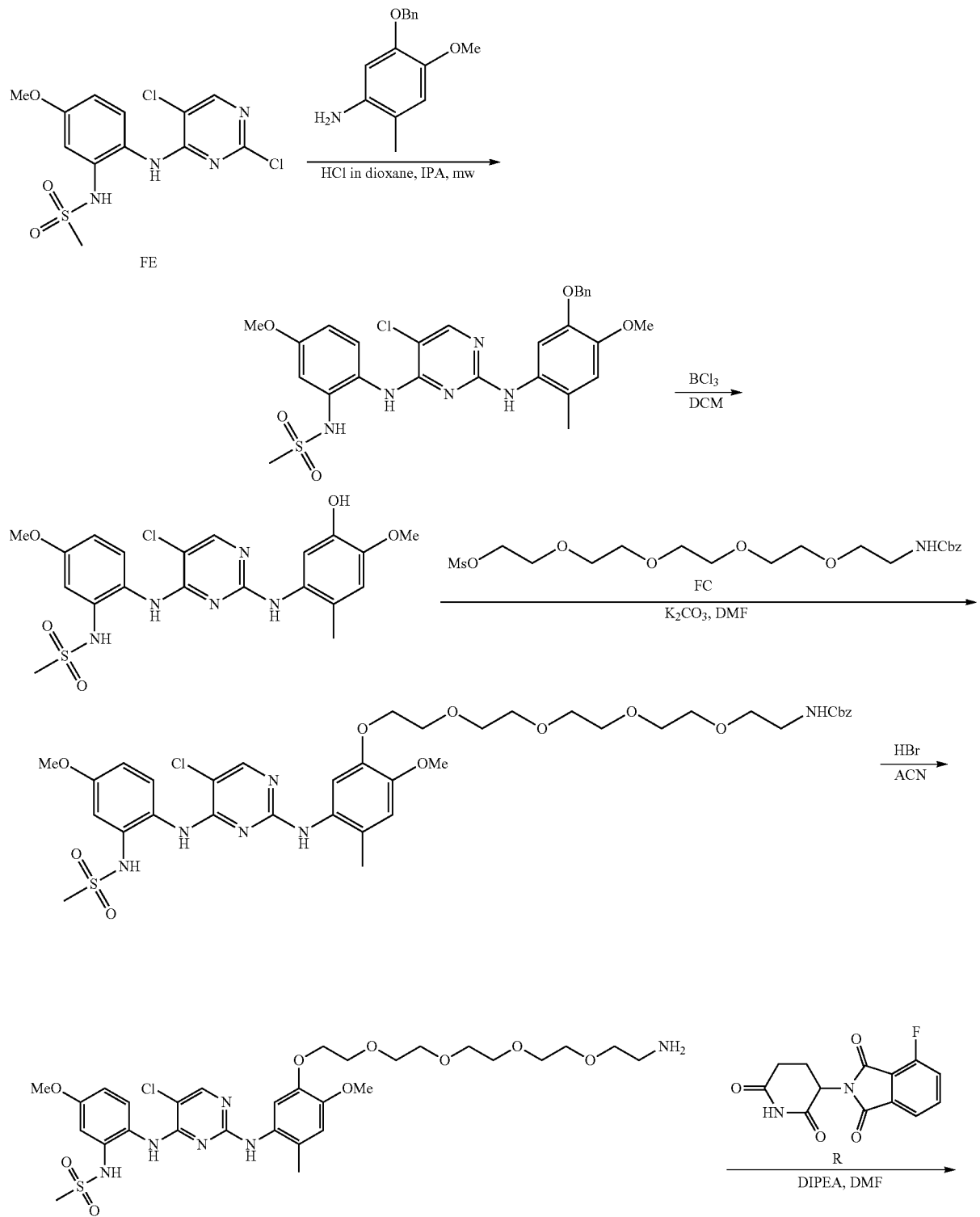

2323

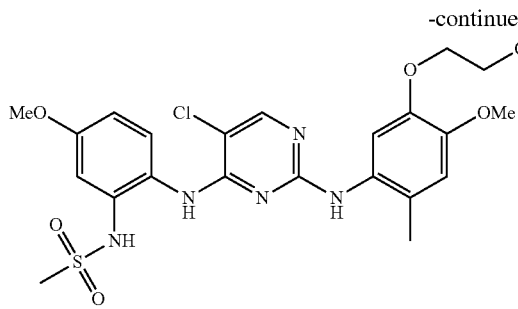

-continued

2324

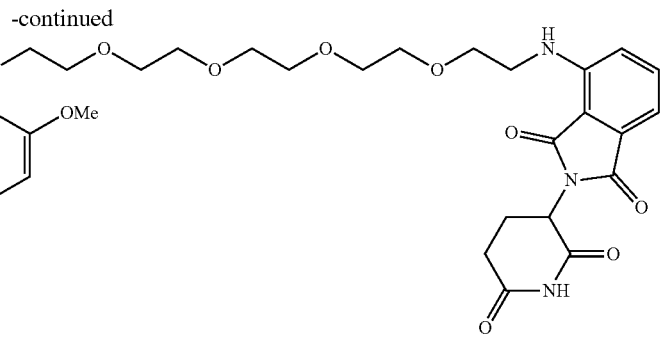

Step 1—N-[2-[[2-(5-benzyloxy-4-methoxy-2-methyl-anilino)-5-chloro-pyrimidin-4-yl]amino]-5-methoxy-phenyl]methanesulfonamide A mixture of N-[2-[(2,5-dichloropyrimidin-4-yl)amino]-5-methoxy-phenyl]methanesulfonamide (1.00 g, 2.75 mmol, Intermediate FE), 5-benzyloxy-4-methoxy-2-methyl-aniline (735 mg, 3.03 mmol, synthesized via Steps 1-3 of Intermediate FE), HCl in dioxane (4 M, 996 uL) and IPA (10 mL) was heated in a microwave at 120° C. for 1 hour. On completion, the reaction mixture was concentrated in vacuo. The residue was purified by prep-column chromatography to give the title compound (1.50 g, 95% yield) as a yellowish solid. LC-MS (ESI$^+$) m/z 570.0 (M+H)$^+$.

Step 2—N-[2-[[5-chloro-2-(5-hydroxy-4-methoxy-2-methyl-anilino)pyrimidin-4-yl]amino]-5-methoxy-phenyl]methanesulfonamide To a mixture of N-[2-[[2-(5-benzyloxy-4-methoxy-2-methyl-anilino)-5-chloro-pyrimidin-4-yl]amino]-5-methoxyphenyl]methanesulfonamide (2.50 g, 4.39 mmol) in DCM (20 mL) was added BCl$_3$.DCM (1 M, 26.34 mL) dropwise at rt. Then the reaction mixture was stirred at rt for 2 hours. On completion, the reaction mixture was concentrated in vacuo. The residue was washed with sat.NaHCO$_3$ (100 mL) and extracted with DCM (3×200 mL). Then the combined organic layer was dried with Na$_2$SO$_4$, filtered and concentrated in vacuo. The residue was purified by prep-column chromatography to give the title compound (1.70 g, 80% yield) as a pale solid. LC-MS (ESI$^+$) m/z 480.1 (M+H)$^+$.

Step 3—Benzyl N-[2-[2-[2-[2-[5-[[5-chloro-4-[2-(methanesulfonamido)-4-methoxy-anilino]pyrimidin-2-yl]amino]-2-methoxy-4-methyl-phenoxy]ethoxy]ethoxy]ethoxy]ethyl]carbamate To a mixture of N-[2-[[5-chloro-2-(5-hydroxy-4-methoxy-2-methyl-anilino)pyrimidin-4-yl]amino]-5-methoxy-phenyl]methanesulfonamide (150 mg, 312 umol) and 2-[2-[2-[2-(benzyloxycarbonyl amino)ethoxy]ethoxy]ethoxy]ethyl methanesulfonate (168 mg, 375 umol, Intermediate FC) in DMF (10 mL) was added K$_2$CO$_3$ (64.7 mg, 468 umol). Then the reaction mixture was stirred at 100° C. for 12 hours. On completion, the reaction mixture was concentrated in vacuo. Then the reaction mixture was purified by reverse phase chromatography to give the title compound (120 mg, 46% yield) as a yellowish oil. LC-MS (ESI$^+$) m/z 833.4 (M+H)$^+$.

Step 4—N-[2-[[2-[5-[2-[2-[2-[2-(2-aminoethoxy) ethoxy]ethoxy]ethoxy]-4-methoxy-2-methyl-anilino]-5-chloro-pyrimidin-4-yl]amino]-5-methoxy-phenyl]methanesulfonamide To a mixture of benzyl N-[2-[2-[2-[2-[5-[[5-chloro-4-[2-(methanesulfonamido)-4-methoxy-anilino]pyrimidin-2-yl]amino]-2-methoxy-4-methyl-phenoxy]ethoxy]ethoxy] ethoxy]ethoxy]-ethyl]carbamate (90.0 mg, 108 umol) in ACN (500 uL) was added 40% HBr solution (4.47 g, 55.2 mmol, 3.00 mL). Then the reaction mixture was stirred at 60° C. for 6 hours. On completion, the reaction mixture was concentrated in vacuo. The residue was washed with sat-.NaHCO$_3$ (30 mL) and extracted with DCM (3×50 mL). The organic layer was dried with Na$_2$SO$_4$, filtered and concentrated in vacuo to give the title compound (55.0 mg, 62% yield) as a yellowish oil. LC-MS (ESI$^+$) m/z 699.1 (M+H)$^+$.

Step 5—N-[2-[[5-chloro-2-[5-[2-[2-[2-[2-[[2-(2,6-dioxo-3-piperidyl)-1,3-dioxo-isoindolin-4-yl] amino]ethoxy]ethoxy]ethoxy]ethoxy]-4-methoxy-2-methyl-anilino]pyrimidin-4-yl]amino]-5-methoxy-phenyl]methanesulfonamide To a mixture of N-[2-[[2-[5-[2-[2-[2-[2-(2-aminoethoxy) ethoxy]ethoxy]ethoxy]-4-methoxy-2-methyl-anilino]-5-chloro-pyrimidin-4-yl]amino]-5-methoxy-phenyl] methanesulfonamide (50.0 mg, 71.5 umol) and 2-(2,6-dioxo-3-piperidyl)-4-fluoro-isoindoline-1,3-dione (23.7 mg, 85.8 umol, Intermediate R) in DMF (2 mL) was added DIPEA (27.7 mg, 214 umol, 37.4 uL). Then the reaction mixture was stirred at 90° C. for 12 hours. On completion, the reaction mixture was concentrated in vacuo. The residue was purified by prep-HPLC (column: Boston Green ODS 150*30 5 u; mobile phase: [water (0.225% FA)-ACN]) to give the title compound I-191 (14.0 mg, 19% yield) as a white solid. $^1$H NMR (400 MHz, DMSO-d$_6$) δ 11.11 (s, 1H), 8.66 (s, 1H), 8.40 (s, 1H), 8.23 (s, 1H), 7.96 (s, 1H), 7.81 (d, J=8.8 Hz, 1H), 7.62-7.54 (m, 1H), 7.13 (d, J=8.8 Hz, 1H), 7.04 (d, J=7.2 Hz, 1H), 6.90 (s, 1H), 6.83 (d, J=2.8 Hz, 1H), 6.80 (s, 1H), 6.60 (t, J=5.6 Hz, 1H), 6.31 (s, 1H), 5.08-4.99 (m, 1H), 3.93-3.86 (m, 2H), 3.76 (s, 3H), 3.68 (s, 3H), 3.67-3.63 (m, 3H), 3.62-3.58 (m, 4H), 3.56-3.52 (m, 8H), 3.50 (s, 3H), 3.05 (s, 1H), 2.95-2.84 (m, 2H), 2.79 (s, 3H), 2.09 (s, 3H), 2.04-2.00 (m, 1H); LC-MS (ESI$^+$) m/z 955.4 (M+H)$^+$.

Example 192: (2S,4R)-1-[(2S)-2-[[2-[2-[2-[2-[2-[5-[[5-chloro-4-[2-(methanesulfonamido)-4-methoxy-anilino]pyrimidin-2-yl]amino]-2-methoxy-4-methyl-phenoxy]ethoxy]ethoxy]ethoxy]ethoxy]acetyl]amino]-3,3-dimethyl-butanoyl]-4-hydroxy-N-[[4-(4-methylthiazol-5-yl)phenyl]methyl]pyrrolidine-2-carboxamide, I-192
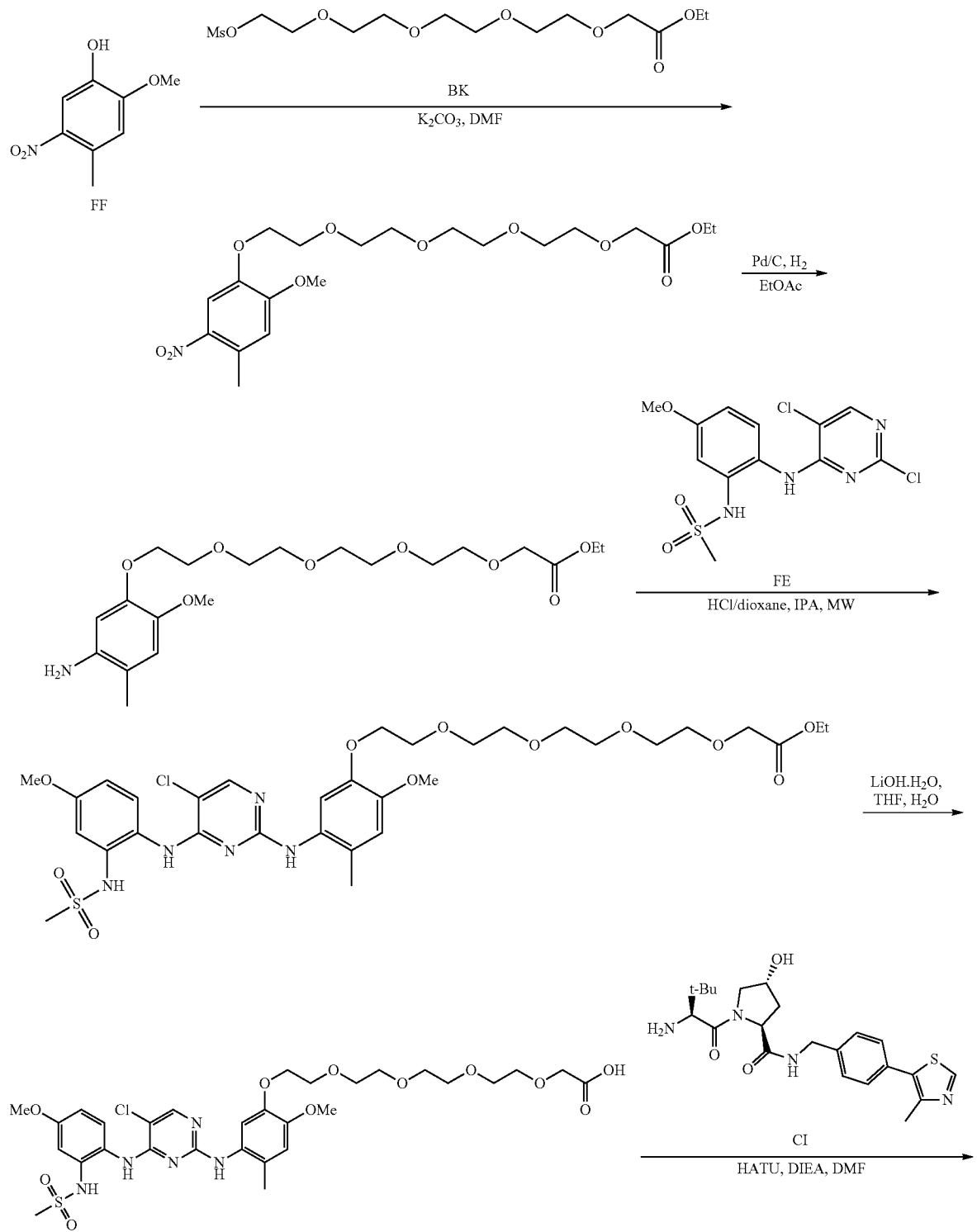

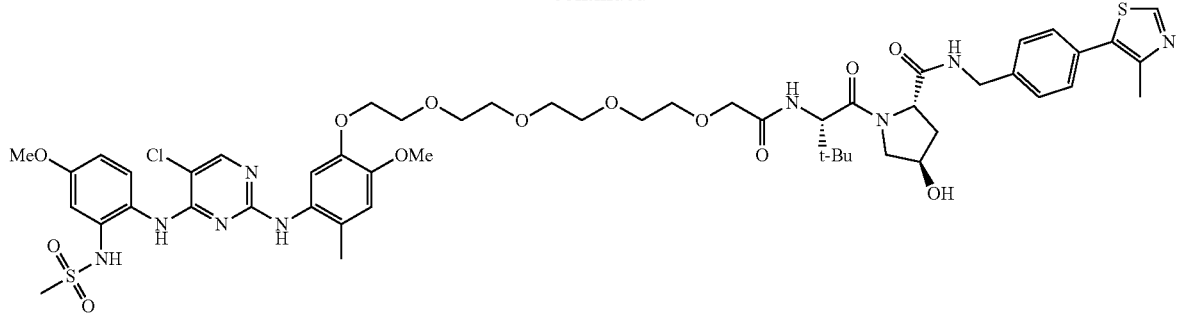

Step 1—Ethyl 2-[2-[2-[2-[2-(2-methoxy-4-methyl-5-nitro-phenoxy)ethoxy]ethoxy]ethoxy]ethoxy]acetate To a mixture of 2-methoxy-4-methyl-5-nitro-phenol (500 mg, 2.73 mmol, Intermediate FF) and K₂CO₃ (1.13 g, 8.19 mmol) in DMF (15 mL) was added ethyl 2-[2-[2-[2-(2-methylsulfonyloxyethoxy)ethoxy]ethoxy]ethoxy]acetate (978 mg, 2.73 mmol, Intermediate BK) at rt. The reaction mixture was then heated to 100° C. and stirred for 1 hour. On completion, the reaction mixture was poured into water (50 mL) and extracted with ethyl acetate (3×50 mL). The combined layer was washed with brine (50 mL), dried over Na₂SO₄, filtered and the filtrate was concentrated in vacuo to give a residue. The residue was purified by silica gel chromatography (petroleum ether:ethyl acetate=5:1) to give the title compound (900 mg, 74% yield) as a yellow oil. ¹H NMR (400 MHz, CDCl₃) δ 7.73 (s, 1H), 6.71 (s, 1H), 4.27-4.18 (m, 4H), 4.15 (s, 2H), 3.94 (s, 3H), 3.93-3.88 (m, 2H), 3.76-3.66 (m, 12H), 2.62 (s, 3H), 1.29 (t, J=7.2 Hz, 3H).

Step 2—Ethyl 2-[2-[2-[2-[2-(5-amino-2-methoxy-4-methyl-phenoxy)ethoxy]ethoxy]ethoxy]ethoxy]acetate To a mixture of ethyl 2-[2-[2-[2-[2-(2-methoxy-4-methyl-5-nitro-phenoxy)ethoxy]ethoxy]ethoxy]ethoxy]acetate (550 mg, 1.23 mmol) in EtOAc (10 mL) was added Pd/C (450 mg, 10 wt %) under hydrogen atmosphere (15 psi pressure). The reaction mixture was stirred at rt for 12 hours. On completion, the reaction mixture was filtered and concentrated in vacuo to give the title compound (470 mg, 91% yield) as a light yellow oil. LC-MS (ESI⁺) m/z 416.2 (M+H)⁺.

Step 3—Isopropyl 2-[2-[2-[2-[2-[5-[[5-chloro-4-[2-(methanesulfonamido)-4-methoxy-anilino]pyrimidin-2-yl]amino]-2-methoxy-4-methyl-phenoxy]ethoxy]ethoxy]ethoxy]ethoxy]acetate To a mixture of ethyl 2-[2-[2-[2-[2-(5-amino-2-methoxy-4-methyl-phenoxy)ethoxy]ethoxy]ethoxy]ethoxy]acetate (470 mg, 1.13 mmol) and N-[2-[(2,5-dichloropyrimidin-4-yl)amino]-5-methoxy-phenyl]methanesulfonamide (410 mg, 1.13 mmol, Intermediate FE) in IPA (10 mL) was added HCl in dioxane (4 M, 409 uL). The reaction mixture was stirred at 120° C. for 1 hour in a microwave. On completion, the reaction mixture was concentrated in vacuo to remove the IPA. The residue was poured into 5 mL of water and basified with sat. Na₂CO₃ until the pH=7-8, then the mixture was extracted with dichloromethane (2×10 mL). The combined organic layers were dried over Na₂SO₄, filtered and concentrated in vacuo to give a residue. The residue was purified by column chromatography (dichloromethane: methanol=100:1) to give the title compound (226 mg, 26% yield) as a light yellow oil. LC-MS (ESI⁺) m/z 742.1 (M+H)⁺.

Step 4—2-[2-[2-[2-[2-[5-[[5-Chloro-4-[2-(methanesulfonamido)-4-methoxy-anilino]pyrimidin-2-yl]amino]-2-methoxy-4-methyl-phenoxy]ethoxy]ethoxy]ethoxy]ethoxy]acetic acid To a mixture of ethyl 2-[2-[2-[2-[2-[5-[[5-chloro-4-[2-(methanesulfonamido)-4-methoxy-anilino]pyrimidin-2-yl]amino]-2-methoxy-4-methyl-phenoxy]ethoxy]ethoxy]ethoxy]ethoxy]acetate (226 mg, 304 umol) in THF (4 mL) and H₂O (2 mL) was added LiOH.H₂O (51.1 mg, 1.22 mmol). The reaction mixture was stirred at rt for 12 hours. On completion, the reaction mixture was concentrated in vacuo to remove THF. The residue was poured into 5 mL of water and acidified with HCl until the pH=6-7, then the mixture was extracted with dichloromethane (3×10 mL). The combined organic layers were dried over Na₂SO₄, filtered and concentrated in vacuo to give the title compound (162 mg, 74% yield) as a yellowish solid. ¹H NMR (400 MHz, CDCl₃) δ 8.23 (s, 1H), 7.92 (s, 1H), 7.70 (s, 1H), 7.38 (d, J=8.8 Hz, 1H), 6.99 (s, 1H), 6.94 (d, J=2.4 Hz, 1H), 6.70 (dd, J=2.8, 8.8 Hz, 1H), 6.64 (s, 1H), 4.12 (s, 2H), 3.82-3.80 (m, 8H), 3.75-3.71 (m, 4H), 3.69-3.61 (m, 10H), 2.87 (s, 3H), 2.10 (s, 3H); LC-MS (ESI⁺) m/z 714.1 (M+H)⁺.

Step 5—(2S,4R)-1-[(2S)-2-[[2-[2-[2-[2-[2-[5-[[5-chloro-4-[2-(methanesulfonamido)-4-methoxy-anilino]pyrimidin-2-yl]amino]-2-methoxy-4-methyl-phenoxy]ethoxy]ethoxy]ethoxy]ethoxy]acetyl]amino]-3,3-dimethyl-butanoyl]-4-hydroxy-N-[[4-(4-methylthiazol-5-yl)phenyl]methyl]pyrrolidine-2-carboxamide To a mixture of 2-[2-[2-[2-[2-[5-[[5-chloro-4-[2-(methanesulfonamido)-4-methoxy-anilino]pyrimidin-2-yl]amino]-2-methoxy-4-methyl-phenoxy]ethoxy]ethoxy]ethoxy]ethoxy]acetic acid (80.0 mg, 112 umol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide (48.2 mg, 103 umol HCl, Intermediate CI) in DMF (3 mL) was added HATU (51.1 mg, 134 umol) and DIPEA (72.3 mg, 560 umol) under nitrogen atmosphere. The reaction mixture was stirred at rt for 3.5 hours. On completion, the reaction mixture was purified prep-HPLC (Gemini 150*25 5 u; mobile phase: [water (0.05% ammonia hydroxide v/v)-ACN]) to give the title compound I-192 (24.5 mg, 19% yield) as a white solid. $^1$H NMR (400 MHz, DMSO-$d_6$) δ 9.00 (s, 1H), 8.62 (t, J=5.6 Hz, 1H), 8.55 (s, 1H), 8.40 (s, 1H), 7.97 (s, 1H), 7.77 (d, J=8.8 Hz, 1H), 7.47-7.35 (m, 6H), 6.88 (s, 1H), 6.84 (d, J=2.4 Hz, 1H), 6.79 (s, 1H), 6.40 (s, 1H), 5.18 (d, J=2.4 Hz, 1H), 4.56 (d, J=9.6 Hz, 1H), 4.46-4.42 (m, 1H), 4.41-4.33 (m, 2H), 4.28-4.22 (m, 1H), 3.96 (s, 2H), 3.87 (s, 2H), 3.75 (s, 3H), 3.69 (s, 3H), 3.65 (d, J=3.2 Hz, 2H), 3.59 (s, 2H), 3.55-3.49 (m, 11H), 3.03-2.96 (m, 1H), 2.82 (s, 3H), 2.44 (s, 3H), 2.08 (s, 3H), 1.92-1.90 (m, 1H), 1.66-1.54 (m, 1H), 0.94 (s, 9H); LC-MS (ESI$^+$) m/z 1148.2 (M+H)$^+$.
Example 193: 3-[[(1R,2S)-2-aminocyclohexyl]amino]-5-[[1-[2-[2-[2-[2-[[2-(2,6-dioxo-3-piperidyl)-1,3-dioxo-isoindolin-4-yl]amino]ethoxy]ethoxy]ethoxy]ethyl]indol-4-yl]amino]-1,2,4-triazine-6-carboxamide, I-193
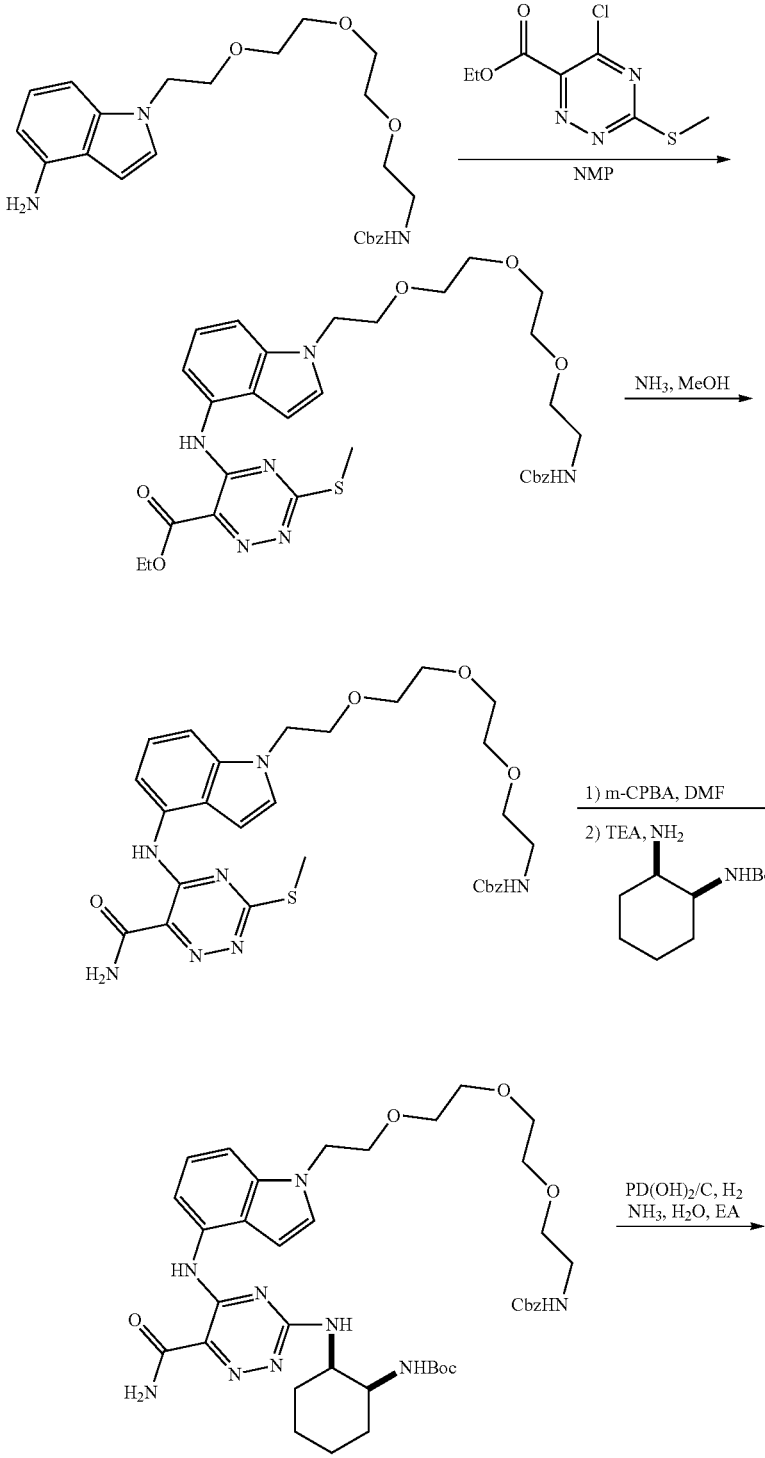

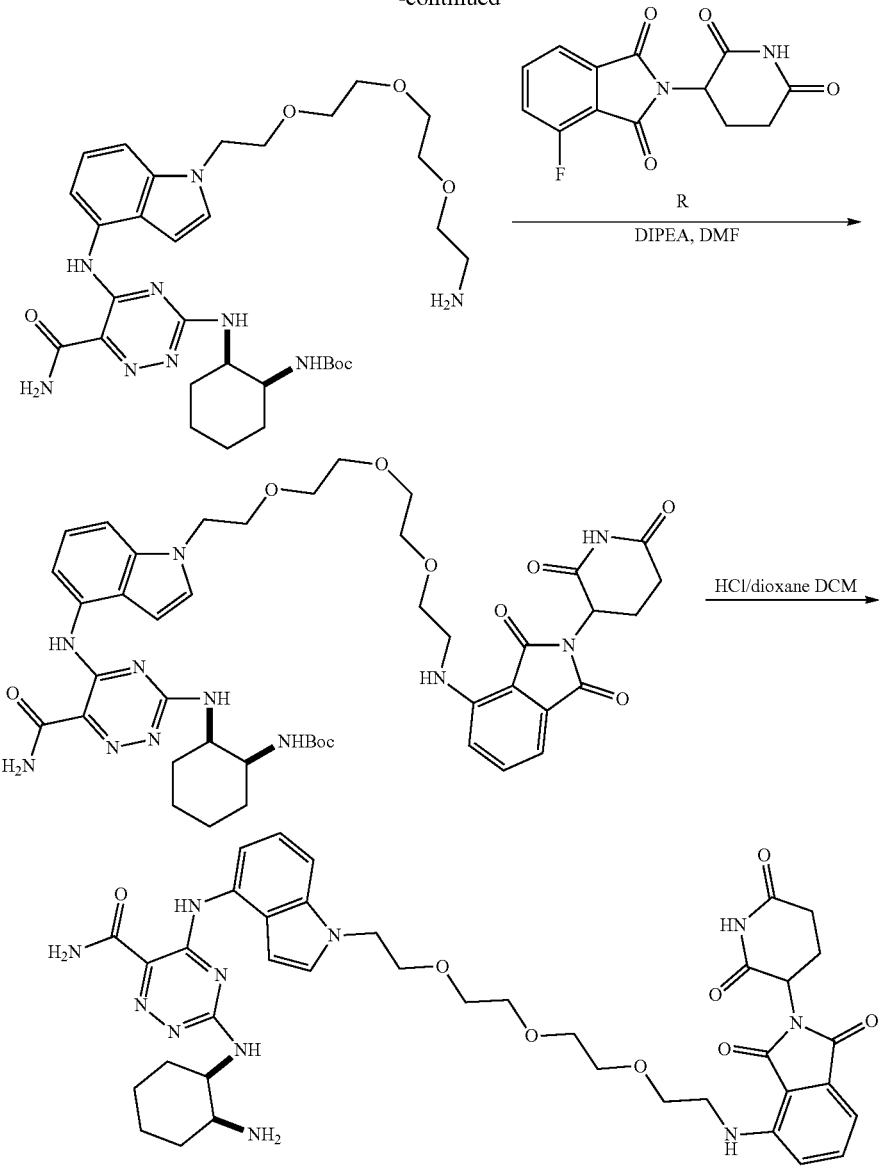

Step 1—Ethyl 5-[[1-[2-[2-[2-[2-(benzyloxycarbonylamino)ethoxy]ethoxy]ethoxy]ethyl]indol-4-yl]amino]-3-methyl sulfanyl-1,2,4-triazine-6-carboxylate A mixture of benzyl N-[2-[2-[2-[2-(4-aminoindol-1-yl)ethoxy]ethoxy]ethoxy]ethyl]carbamate (250 mg, 566 umol, synthesized via Steps 1-2 of Example 166) and ethyl 5-chloro-3-methylsulfanyl-1,2,4-triazine-6-carboxylate (140 mg, 599 umol, CAS #75824-03-2) in NMP (3 mL) was stirred at rt for 1 hour. On completion, the residue was purified by reverse phase chromatography (0.1% FA) to afford the title compound (220 mg, 56% yield) as a yellow oil. LC-MS (ESI+) m/z 639.1 (M+H)+.

Step 2—Benzyl N-[2-[2-[2-[2-[4-[(6-carbamoyl-3-methylsulfanyl-1,2,4-triazin-5-yl)amino]indol-1-yl]ethoxy]ethoxy]ethoxy]ethyl]carbamate A mixture of ethyl 5-[[1-[2-[2-[2-[2-(benzyloxycarbonylamino)ethoxy]ethoxy]ethoxy]ethyl]indol-4-yl]amino]-3-methylsulfanyl-1,2,4-triazine-6-carboxylate (220 mg, 344 umol) in MeOH (15 mL) and 70 N NH₃ in MeOH (15 mL) was stirred at −40° C. for 1 hour. On completion, the mixture was concentrated in vacuo at 45° C. to afford the title compound (180 mg, 81% yield) as a yellow solid. LC-MS (ESI+) m/z 610.2 (M+H)+.

Step 3—Tert-butyl N-[(1S,2R)-2-[[5-[[1-[2-[2-[2-[2-(benzyloxycarbonylamino)ethoxy]ethoxy]ethoxy]ethyl]indol-4-yl]amino]-6-carbamoyl-1,2,4-triazin-3-yl]amino]cyclohexyl]carbamate To a mixture of benzyl N-[2-[2-[2-[2-[4-[(6-carbamoyl-3-methylsulfanyl-1,2,4-triazin-5-yl)amino]indol-1-yl]ethoxy]ethoxy]ethoxy]ethyl]carbamate (180 mg, 295 umol) in DMF (3 mL) was added m-CPBA (150 mg, 869 umol) in one portion at 0° C. under nitrogen. The mixture was stirred at rt for 1 hour. On completion, TEA (255 mg, 2.52 mmol) and tert-butyl N-[(1S,2R)-2-aminocyclohexyl]carbamate (100 mg, 466 umol) was added to above solution. Then the reaction mixture was heated to 65° C. and stirred for 0.5 hour. On completion, the mixture was poured into water (50 mL) and stirred for 2 minutes. The aqueous phase was extracted with ethyl acetate (3×50 mL). The combined organic phase was washed with brine (1×50 mL), dried with anhydrous $Na_2SO_4$, filtered and concentrated in vacuo. The residue was purified by reverse phase chromatography (0.1% FA) to afford the title compound (120 mg, 49% yield) as yellow solid. LC-MS (ESI$^+$) m/z 776.5 (M+H)$^+$.

Step 4—Tert-butyl N-[(1S,2R)-2-[[5-[[1-[2-[2-[2-(2-aminoethoxy)ethoxy]ethoxy]ethyl]indol-4-yl]amino]-6-carbamoyl-1,2,4-triazin-3-yl]amino]cyclohexyl]

To a mixture of tert-butyl N-[(1S,2R)-2-[[5-[[1-[2-[2-[2-[2-(benzyloxycarbonylamino)ethoxy]ethoxy]ethoxy]ethyl]indol-4-yl]amino]-6-carbamoyl-1,2,4-triazin-3-yl]amino]cyclohexyl]carbamate (120 mg, 154 umol) in EA (10 mL) was added Pd(OH)$_2$/C (270 mg, 10 wt %) and $NH_3 \cdot H_2O$ (100 uL) in one portion at rt under a hydrogen atmosphere (15 psi pressure). The mixture was stirred at rt for 16 hours. LCMS showed 30% starting material was not consumed. More Pd(OH)$_2$/C (150 mg, 10 wt %) was added to above solution, and the mixture was stirred at rt under a hydrogen atmosphere (15 psi pressure) for another 16 hours. On completion, the mixture was filtered and the filtrate was concentrated in vacuo to afford the title compound (100 mg, 70% yield) as a yellow solid. LC-MS (ESI$^+$) m/z 642.3 (M+H)$^+$.

Step 5—Tert-butyl N-[(1S,2R)-2-[[6-carbamoyl-5-[[1-[2-[2-[2-[2-[[2-(2,6-dioxo-3-piperidyl)-1,3-dioxo-isoindolin-4-yl]amino]ethoxy]ethoxy]ethoxy]ethyl]indol-4-yl]amino]-1,2,4-triazin-3-yl]amino]cyclohexyl]carbamate To a solution of tert-butyl N-[(1S,2R)-2-[[5-[[1-[2-[2-[2-(2-aminoethoxy)ethoxy]ethoxy]ethyl]indol-4-yl]amino]-6-carbamoyl-1,2,4-triazin-3-yl]amino]cyclohexyl]carbamate (82.0 mg, 128 umol) and 2-(2,6-dioxo-3-piperidyl)-4-fluoroisoindoline-1,3-dione (38.8 mg, 141 umol, Intermediate R)

in DMF (3 mL) was added DIPEA (33.0 mg, 256 umol) under nitrogen atmosphere. The reaction mixture was stirred at 90° C. for 7 hours. On completion, the reaction mixture was concentrated in vacuo. The residue was purified by prep-TLC (DCM:MeOH=10:1) to afford the title compound (100 mg, 57% yield) as a yellow solid. LC-MS (ESI$^+$) m/z 898.3 (M+H)$^+$.

Step 6—3-[[(1R,2S)-2-aminocyclohexyl]amino]-5-[[1-[2-[2-[2-[2-[[2-(2,6-dioxo-3-piperidyl)-1,3-dioxo-isoindolin-4-yl]amino]ethoxy]ethoxy]ethoxy]ethyl]indol-4-yl]amino]-1,2,4-triazine-6-carboxamide To a solution of tert-butyl N-[(1S,2R)-2-[[6-carbamoyl-5-[[1-[2-[2-[2-[2-[[2-(2,6-dioxo-3-piperidyl)-1,3-dioxo-isoindolin-4-yl]amino]ethoxy]ethoxy]ethoxy]ethyl]indol-4-yl]amino]-1,2,4-triazin-3-yl]amino]cyclohexyl]carbamate (100 mg, 111 umol) in DCM (3 mL) was added HCl in dioxane (4N, 2 mL) under a nitrogen atmosphere. The reaction mixture was stirred at rt for 2 hours. On completion, the reaction mixture was concentrated in vacuo. The residue was purified by prep-HPLC (column: Boston Green ODS 150*30 5 u; mobile phase [water (0.225% FA)-ACN]; B %: 24%-48%, 10 min) to afford the title compound I-193 (10.0 mg, 11% yield). $^1$H NMR (400 MHz, DMSO-d$_6$) δ 12.92 (s, 1H), 8.39 (d, J=12.8 Hz, 3H), 7.95-7.85 (m, 1H), 7.79-7.71 (m, 1H), 7.69-7.52 (m, 1H), 7.45-7.32 (m, 1H), 7.31-7.21 (m, 1H), 7.20-7.09 (m, 2H), 7.09-7.01 (m, 1H), 6.62-6.50 (m, 1H), 6.49-6.40 (m, 1H), 5.10-5.01 (m, 1H), 4.45-4.32 (m, 2H), 3.95-3.82 (m, 1H), 3.80-3.60 (m, 2H), 3.55-3.45 (m, 14H), 2.93-2.81 (m, 1H), 2.59-2.63 (m, 2H), 2.06-1.95 (m, 1H), 1.89-1.72 (m, 2H), 1.68-1.49 (m, 4H), 1.45-1.25 (m, 3H); LC-MS (ESI$^+$) m/z 798.6 (M+H)$^+$.

Example 194: 3-[[(1R,2S)-2-aminocyclohexyl]amino]-5-[[1-[2-[2-[2-[2-[[2-(2,6-dioxo-3-piperidyl)-1,3-dioxo-isoindolin-4-yl]amino]ethoxy]ethoxy]ethoxy]ethyl]indol-4-yl]amino]-1,2,4-triazine-6-carboxamide, I-194

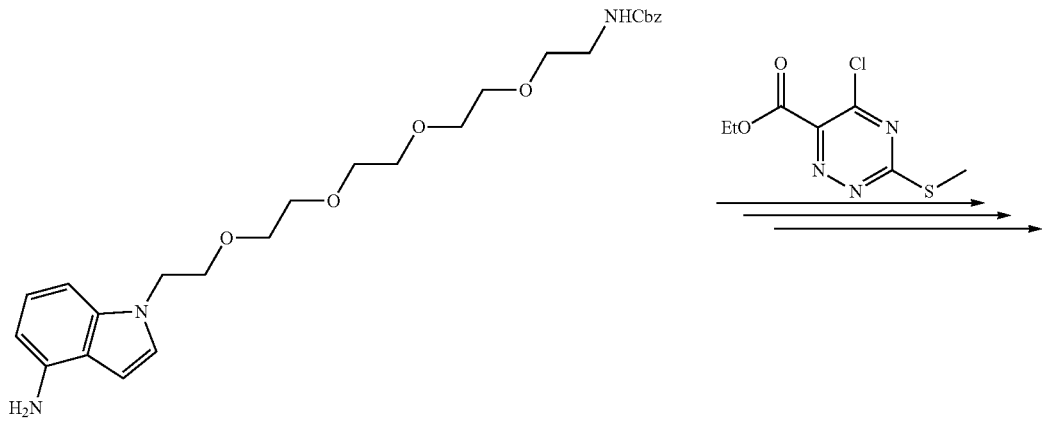

2335

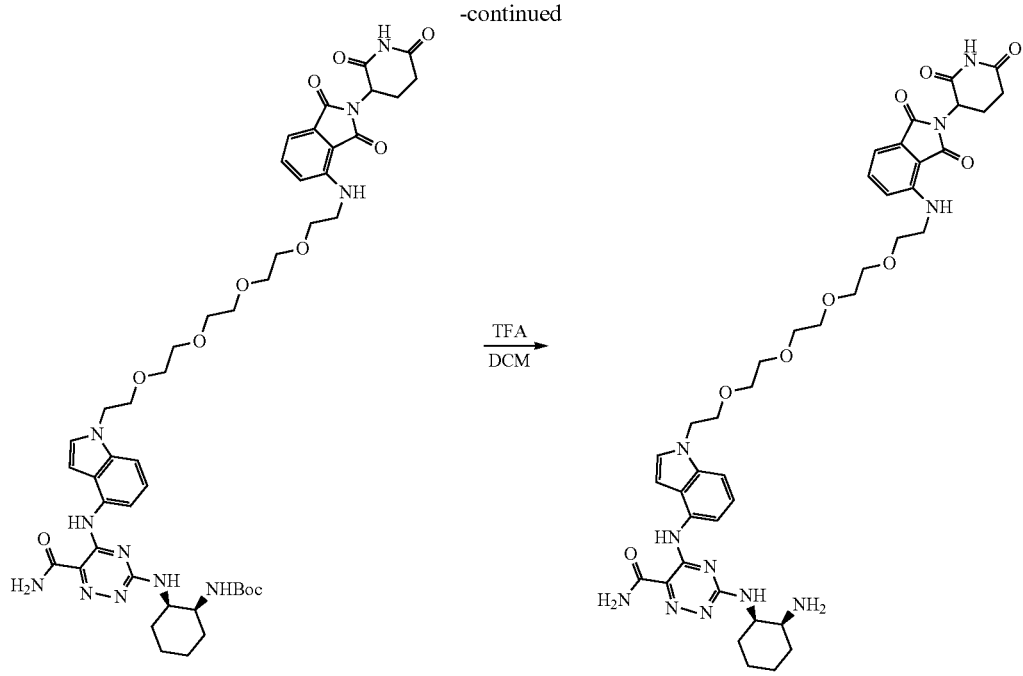

3-[[(1R,2S)-2-aminocyclohexyl]amino]-5-[[1-[2-[2-[2-[2-[2-[[2-(2,6-dioxo-3-piperidyl)-1,3-dioxo-isoindolin-4-yl]amino]ethoxy]ethoxy]ethoxy]ethoxy]ethyl]indol-4-yl]amino]-1,2,4-triazine-6-carboxamide was synthesized as described for Example 193, using benzyl N-[2-[2-[2-[2-[2-(4-aminoindol-1-yl)ethoxy]ethoxy]ethoxy]ethoxy]ethyl] carbamate (synthesized via Steps 1-2 of Example 167) as the starting material in the first step. In Step 4, the hydrogenation was run at rt with 50 psi pressure of hydrogen. In Step 6, TFA not HCl was used for the Boc deprotection. The procedure was as follows:

A mixture of tert-butyl N-[(1S,2R)-2-[[6-carbamoyl-5-[[1-[2-[2-[2-[2-[2-[[2-(2,6-dioxo-3-piperidyl)-1,3-dioxo-isoindolin-4-yl]amino]ethoxy]ethoxy]ethoxy]ethoxy]ethyl]indol-4-yl]amino]-1,2,4-triazin-3-yl]amino]cyclohexyl]carbamate (72 mg, 76.4 umol) in TFA (300 uL) and DCM (500 uL) was stirred at rt for 0.5 hour. On completion, the mixture was concentrated in vacuo. The residue was purified by column (Phenomenex Synergi C18 150*25*10 um;

mobile phase: [water (0.05% HCCOH)-ACN]; B %: 10%-40%, 12 min) to afford the title compound I-194 (20 mg, 30% yield) as a yellow solid. $^1$H NMR (400 MHz, CD$_3$OD) δ 8.53 (br s, 1H), 7.45 (dd, J=7.2, 8.8 Hz, 1H), 7.33 (d, J=3.2 Hz, 1H), 7.27 (d, J=8.0 Hz, 1H), 7.21-7.12 (m, 1H), 7.00-6.95 (m, 2H), 6.55 (d, J=3.2 Hz, 1H), 4.34 (t, J=4.8 Hz, 2H), 3.81 (t, J=5.2 Hz, 2H), 3.63 (t, J=5.6 Hz, 2H), 3.60-3.55 (m, 4H), 3.55-3.49 (m, 6H), 3.50-3.47 (m, 2H), 3.39 (t, J=5.2 Hz, 2H), 2.85-2.64 (m, 2H), 2.16-1.93 (m, 2H), 1.90-1.75 (m, 5H), 1.73-1.47 (m, 3H), 1.41-1.25 (m, 2H). LC-MS (ESI$^+$) m/z 842.5 (M+H)$^+$.

Example 195: (2S,4R)-1-[(2S)-2-[2-[2-[2-[2-[2-[[2-[4-[[7-[[(1R,2S)-2-Aminocyclohexyl amino]-4-oxo-3H-pyrido[4,3-d]pyrimidin-5-yl]amino]indol-1-yl]acetyl]amino]ethoxy]ethoxy]ethoxy]ethoxy]acetyl]amino]-3,3-dimethyl-butanoyl]-4-hydroxy-N-[[4-(4-methylthiazol-5-yl)phenyl]methyl]pyrrolidine-2-carboxamide, I-195

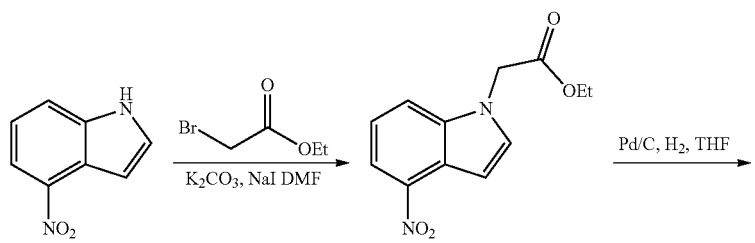

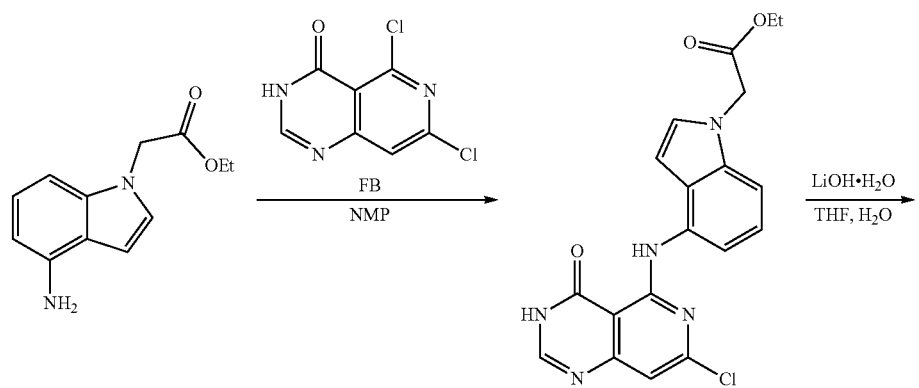
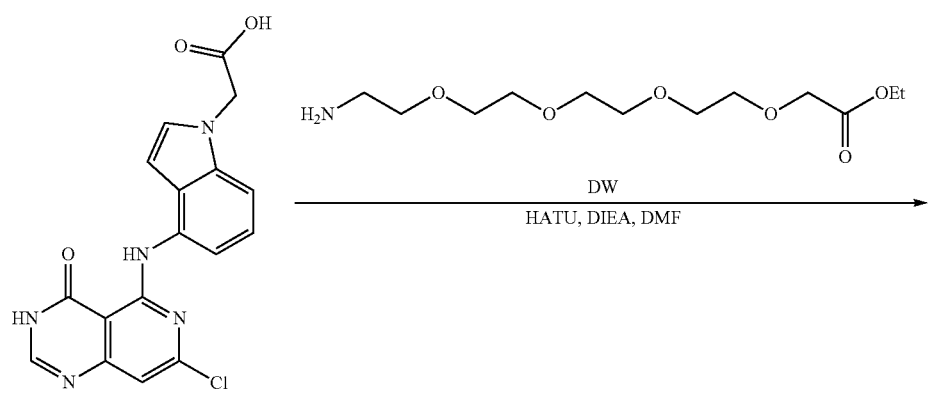
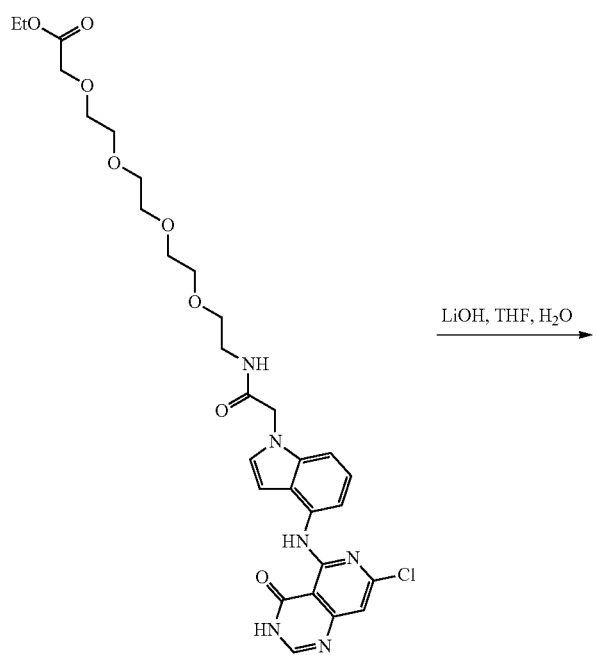

2339
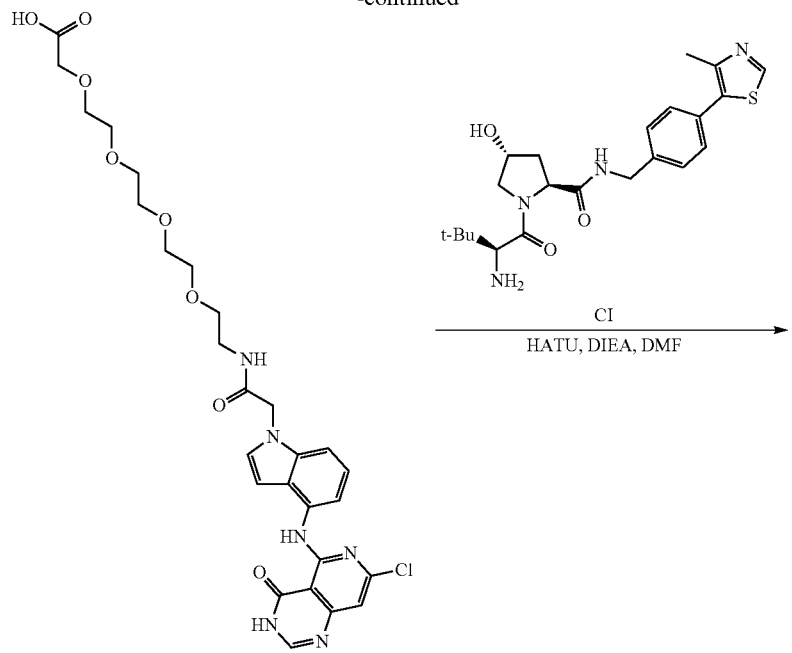
2340
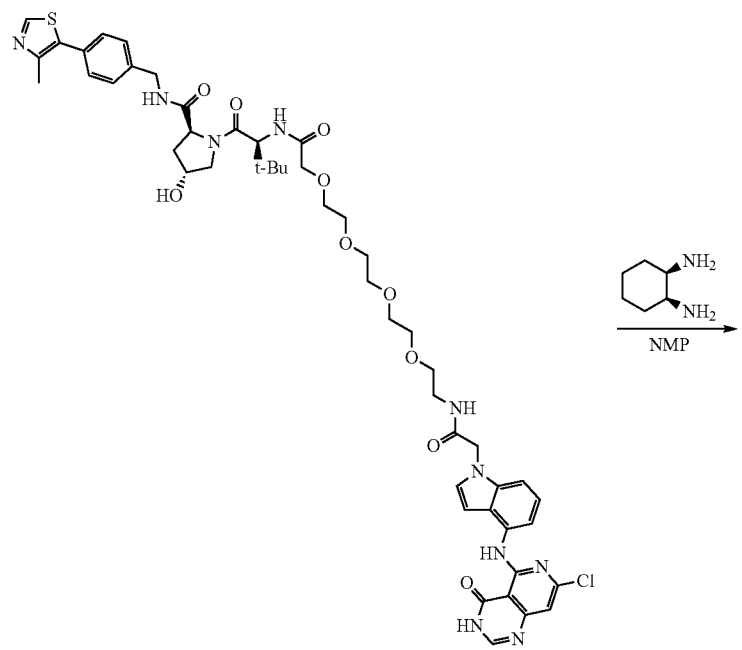

-continued

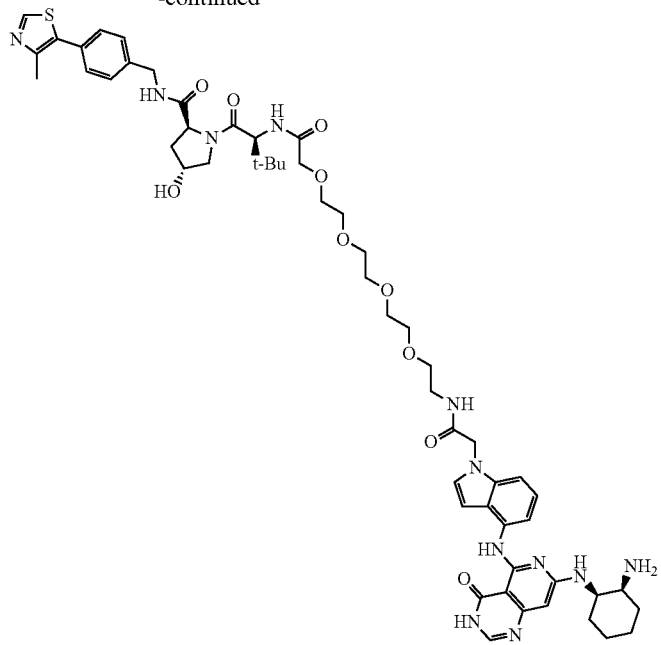

Step 1—Ethyl 2-(4-nitroindol-1-yl)acetate

To a solution of 4-nitro-1H-indole (5.00 g, 30.8 mmol, CAS #4769-97-5) in DMF (100 mL) was added ethyl 2-bromoacetate (7.73 g, 46.3 mmol, 5.12 mL), $K_2CO_3$ (12.8 g, 92.5 mmol) and NaI (462 mg, 3.08 mmol). The reaction mixture was stirred at 40° C. for 12 hrs. On completion, the reaction mixture was diluted with water (100 mL) and extracted with dichloromethane (3×200 mL). The combined organic layer was washed with brine (200 mL), dried over anhydrous sodium sulfate, filtered and concentrated in vacuo. The residue was triturated with ethyl acetate (30 mL) to give the title compound (6.50 g, 85% yield) as a yellow solid. $^1$H NMR (400 MHz, $CDCl_3$) δ 8.17 (dd, J=0.8, 8.2 Hz, 1H), 7.59 (d, J=8.2 Hz, 1H), 7.38-7.36 (m, 1H), 7.35-7.29 (m, 2H), 4.94 (s, 2H), 4.24 (q, J=7.2 Hz, 2H), 1.28 (t, J=7.2 Hz, 3H).

Step 2—Ethyl 2-(4-aminoindol-1-yl)acetate

To a solution of ethyl 2-(4-nitroindol-1-yl)acetate (2.60 g, 10.5 mmol) in THF (20 mL) was added Pd/C (260 mg, 10 wt %), and the suspension was degassed and purged with hydrogen gas three times. The mixture was stirred under hydrogen (15 psi pressure) at rt for 12 hrs. On completion, the reaction was filtered and concentrated in vacuo to give the title compound (2.20 g, 96% yield) as a colorless oil. $^1$H NMR (400 MHz, $CDCl_3$) δ 7.06 (t, J=8.0 Hz, 1H), 7.02 (d, J=3.2 Hz, 1H), 6.72 (d, J=8.0 Hz, 1H), 6.49 (dd, J=0.8, 3.2 Hz, 1H), 6.43 (dd, J=0.8, 8.0 Hz, 1H), 4.81 (s, 2H), 4.22 (q, J=7.2 Hz, 2H), 1.27 (t, J=7.2 Hz, 3H).

Step 3—Ethyl 2-[4-[(7-chloro-4-oxo-3H-pyrido[4,3-d]pyrimidin-5-yl)amino]indol-1-yl]acetate To a solution of ethyl 2-(4-aminoindol-1-yl)acetate (2.20 g, 10.1 mmol) in NMP (40 mL) was added 5,7-dichloro-3H-pyrido[4,3-d]pyrimidin-4-one (2.18 g, 10.1 mmol, Intermediate FB) under nitrogen. The reaction mixture was stirred at 140° C. for 1 hr. On completion, the reaction mixture was concentrated in vacuo. The residue was triturated with DMF/MeOH=(5 mL/10 mL) to give the title compound (3.20 g, 80% yield) as a yellow oil. $^1$H NMR (400 MHz, DMSO-$d_6$) δ 12.95 (s, 1H), 11.76 (s, 1H), 8.32 (s, 1H), 8.22-8.15 (m, 1H), 7.41 (d, J=3.2 Hz, 1H), 7.21-7.15 (m, 2H), 6.92 (s, 1H), 6.60 (d, J=3.2 Hz, 1H), 5.16 (s, 2H), 4.16 (q, J=7.2 Hz, 2H), 1.22 (t, J=7.2 Hz, 3H).

Step 4—2-[4-[(7-Chloro-4-oxo-3H-pyrido[4,3-d]pyrimidin-5-yl)amino]indol-1-yl]acetic acid To a solution of ethyl 2-[4-[(7-chloro-4-oxo-3H-pyrido[4,3-d]pyrimidin-5-yl)amino]indol-1-yl]acetate (2.00 g, 5.03 mmol) in THF (30 mL) and $H_2O$ (10 mL) was added LiOH.$H_2O$ (633 mg, 15.0 mmol). The reaction mixture was stirred at rt for 12 hours. On completion, the reaction mixture was concentrated in vacuo. The residue was acidified with HCl (2 N, 20 mL) to pH=3. The precipitate was collected by filtration and the solid was dried in vacuo to give the title compound (1.80 g, 87% yield) as a yellow solid. $^1$H NMR (400 MHz, DMSO-$d_6$) δ 12.98 (s, 2H), 11.78 (s, 1H), 8.31 (s, 1H), 8.22-8.13 (m, 1H), 7.41 (d, J=3.2 Hz, 1H), 7.22-7.13 (m, 2H), 6.91 (s, 1H), 6.59 (d, J=3.2 Hz, 1H), 5.04 (s, 2H); LC-MS (ESI$^+$) m/z 370.0 (M+H)$^+$.

Step 5—Ethyl 2-[2-[2-[2-[2-[[2-[4-[(7-chloro-4-oxo-3H-pyrido[4,3-d]pyrimidin-5-yl)amino]indol-1-yl]acetyl]amino]ethoxy]ethoxy]ethoxy]ethoxy]acetate To a solution of ethyl 2-[2-[2-[2-(2-aminoethoxy)ethoxy]ethoxy]ethoxy]acetate (287 mg, 1.03 mmol, Intermediate DW) and 2-[4-[(7-chloro-4-oxo-3H-pyrido[4,3-d]pyrimidin-5-yl)amino]indol-1-yl]acetic acid (380 mg, 1.03 mmol) in DMF (10 mL) was added DIPEA (398 mg, 3.08 mmol). After stirring for 30 minutes, HATU (430 mg, 1.13 mmol) was added. The mixture was stirred at rt for 2 hours. On completion, 50 mL water was added to the mixture. A large quantity of yellow precipitate formed, which was collected by filtration to give the title compound (575 mg, 88% yield) as a yellow solid. LC-MS (ESI⁺) m/z 631.2 (M+H)⁺.

Step 6—2-[2-[2-[2-[2-[[2-[4-[(7-Chloro-4-oxo-3H-pyrido[4,3-d]pyrimidin-5-yl)amino]indol-1-yl] acetyl]amino]ethoxy]ethoxy]ethoxy]ethoxy]acetic acid To a mixture of ethyl 2-[2-[2-[2-[2-[[2-[4-[(7-chloro-4-oxo-3H-pyrido[4,3-d]pyrimidin-5-yl)amino]indol-1-yl] acetyl]amino]ethoxy]ethoxy]ethoxy]ethoxy]acetate (600 mg, 950 umol) in THF (10 mL) and H₂O (10 mL), was added LiOH (228 mg, 9.51 mmol). Then, the mixture was stirred at rt for 5 hours. On completion, the mixture was adjusted to pH=5 with HCl (1N), then the mixture was extracted with DCM (2×20 mL). The combined organic layer was dried over anhydrous Na₂SO₄, filtered and concentrated in vacuo to give the title compound (400 mg, 69% yield) as a yellow solid. LC-MS (ESI⁺) m/z 603.1 (M+H)⁺.

Step 7—(2S,4R)-1-[(2S)-2-[[2-[2-[2-[2-[2-[[2-[4-[(7-Chloro-4-oxo-3H-pyrido[4,3-d]pyrimidin-5-yl) amino]indol-1-yl]acetyl]amino]ethoxy]ethoxy] ethoxy]ethoxy]acetyl]amino]-3,3-dimethyl-butanoyl]-4-hydroxy-N-[[4-(4-methylthiazol-5-yl) phenyl]methyl]pyrrolidine-2-carboxamide A mixture of 2-[2-[2-[2-[2-[[2-[4-[(7-chloro-4-oxo-3H-pyrido[4,3-d]pyrimidin-5-yl)amino]indol-1-yl]acetyl] amino]ethoxy]ethoxy]ethoxy]ethoxy]acetic acid (400 mg, 597 umol), (2S,4R)-1-[(2S)-2-amino-3,3-dimethyl-butanoyl]-4-hydroxy-N-[[4-(4-methylthiazol-5-yl)phenyl] methyl]pyrrolidine-2-carboxamide (279 mg, 597 umol, HCl salt, Intermediate CI), and DIPEA (308 mg, 2.39 mmol) in DMF (20 mL) was degassed and purged with nitrogen gas three times. Then HATU (249 mg, 657 umol) was added, and the mixture was stirred at rt for 2 hours under a nitrogen atmosphere. On completion, the mixture was poured into water (50 mL) and extracted with DCM (2×40 mL). The organic layer was dried over anhydrous Na₂SO₄, filtered and concentrated in vacuo to give a residue. The residue was purified by silica column chromatography to give the title compound (110 mg, 18% yield) as a yellow solid. LC-MS (ESI⁺) m/z 1037.6 (M+Na)⁺.

Step 8—(2S,4R)-1-[(2S)-2-[[2-[2-[2-[2-[2-[[2-[4-[[7-[[(1R,2S)-2-Aminocyclohexyl amino]-4-oxo-3H-pyrido[4,3-d]pyrimidin-5-yl)amino]indol-1-yl] acetyl]amino]ethoxy]ethoxy]ethoxy]ethoxy]acetyl] amino]-3,3-dimethyl-butanoyl]-4-hydroxy-N-[[4-(4-methylthiazol-5-yl)phenyl]methyl]pyrrolidine-2-carboxamide A mixture of (2S,4R)-1-[(2S)-2-[[2-[2-[2-[2-[2-[[2-[4-[(7-chloro-4-oxo-3H-pyrido[4,3-d]pyrimidin-5-yl)amino] indol-1-yl]acetyl]amino]ethoxy]ethoxy]ethoxy]ethoxy] acetyl]amino]-3,3-dimethyl-butanoyl]-4-hydroxy-N-[[4-(4-methylthiazol-5-yl)phenyl]methyl]pyrrolidine-2-carboxamide (60.0 mg, 59.0 umol) and (1R,2S)-cyclohexane-1,2-diamine (67.4 mg, 590 umol) in NMP (0.5 mL) was heated under microwave irradiation at 150° C. for 1.5 hours. On completion, the mixture was purified by prep-HPLC (column: Phenomenex Synergi C18 150*25*10 um; mobile phase: [water (0.225% FA)-ACN]) to give the title compound I-195 (26.0 mg, 40% yield) as a yellow solid. ¹H NMR (400 MHz, DMSO-d₆) δ 11.75 (s, 1H), 9.06-8.91 (m, 1H), 8.62 (t, J=6.0 Hz, 1H), 8.39-8.32 (m, 2H), 7.93 (s, 1H), 7.49-7.29 (m, 6H), 7.14-6.99 (m, 2H), 6.58 (d, J=3.2 Hz, 1H), 6.03 (s, 1H), 4.83 (s, 2H), 4.57 (d, J=9.6 Hz, 1H), 4.49-4.33 (m, 3H), 4.25 (m, 2H), 3.97 (s, 2H), 3.71-3.40 (m, 17H), 3.25 (m, 2H), 2.57-2.52 (m, 4H), 2.45 (s, 3H), 2.12-2.01 (m, 1H), 1.96-1.78 (m, 3H), 1.65 (d, J=11.2 Hz, 4H), 1.41 (s, 2H), 1.00-0.88 (m, 9H); LC-MS (ESI⁺) m/z 1093.2 (M+H)⁺.

Example 196: 3-[[(1R,2S)-2-aminocyclohexyl] amino]-5-[[1-[2-[2-[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethoxy]ethyl] indol-4-yl]amino]-1,2,4-triazine-6-carboxamide, I-196

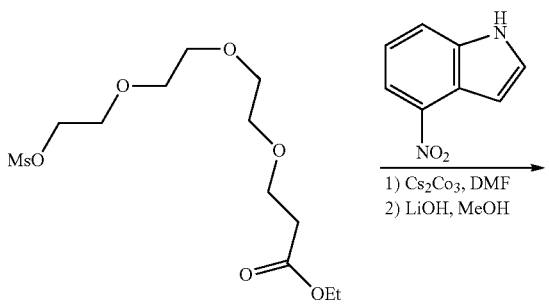

2345
2346
-continued
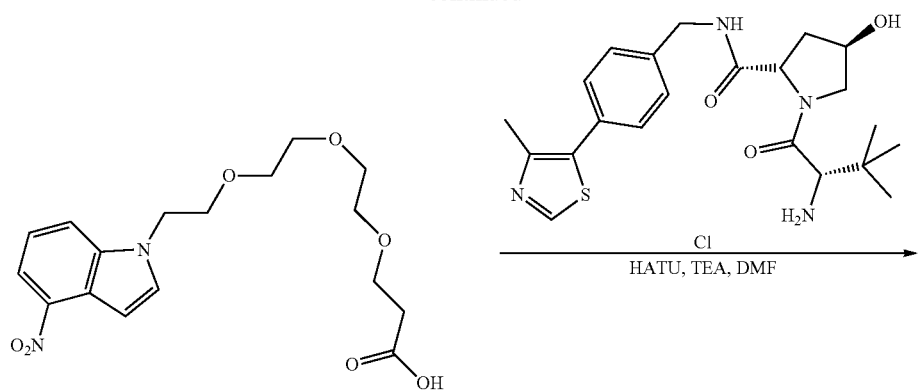
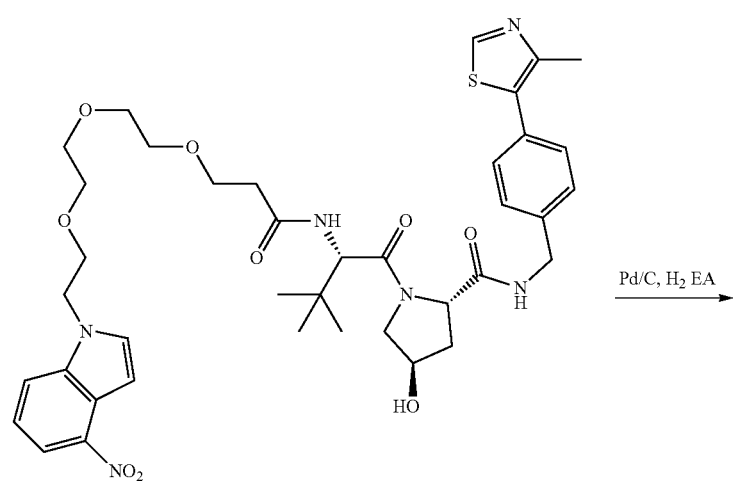
Pd/C, H₂ EA
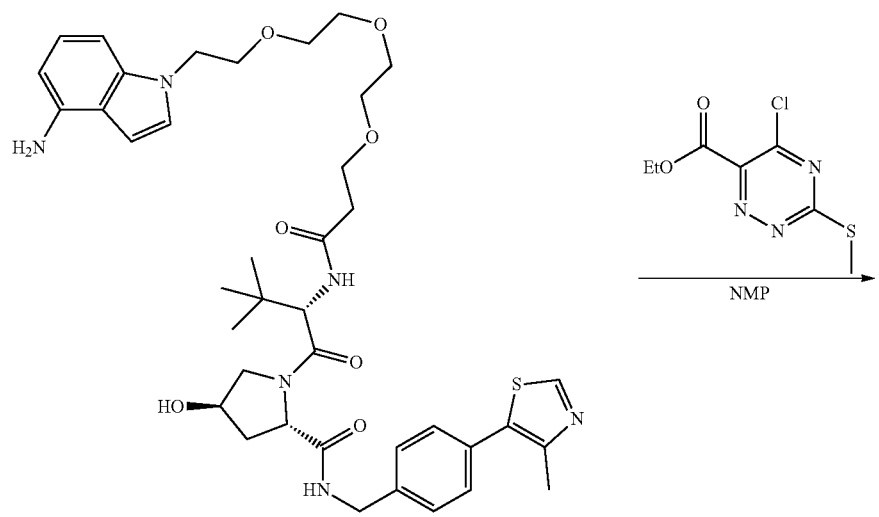

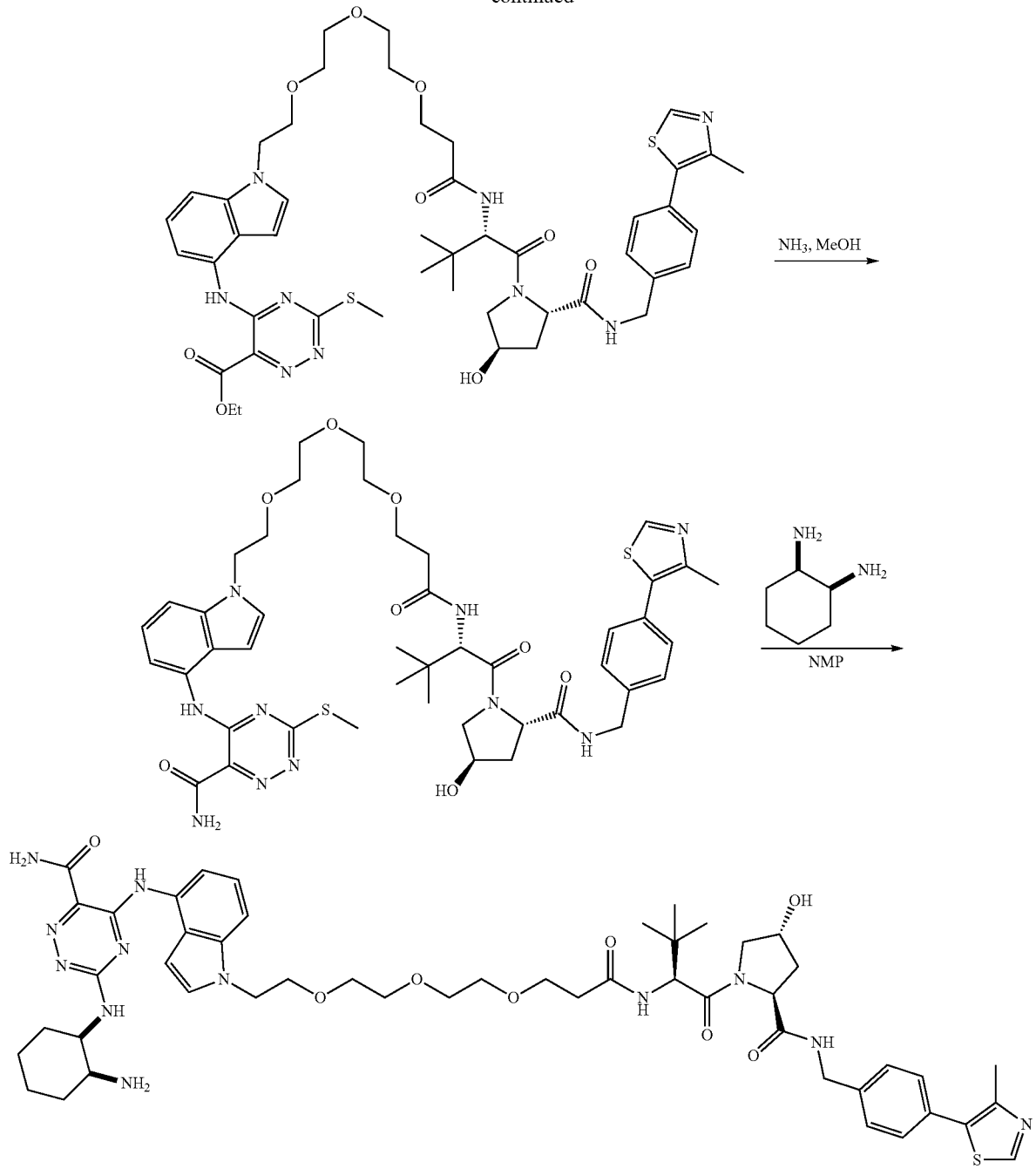

Step 1—2-[2-[2-[2-(4-Nitroindol-1-yl)ethoxy]ethoxy]ethoxy]acetic acid

To a mixture of ethyl 2-[2-[2-(2-methylsulfonyloxyethoxy)ethoxy]ethoxy]acetate (1.10 g, 3.51 mmol, Intermediate BI) and 4-nitro-1H-indole (500 mg, 3.08 mmol) in DMF (10 mL) was added $Cs_2CO_3$ (2.51 g, 7.70 mmol) in one portion at rt under nitrogen. The mixture was stirred at 100° C. for 16 hours. Next, $LiOH \cdot H_2O$ (129 mg, 3.08 mmol) in MeOH (3 mL) was then added to above solution, and the solution was stirred at rt for 4 hours. On completion, the mixture was poured into water (50 mL) and stirred for 2 minutes. The aqueous phase was extracted with ethyl acetate (4×50 mL). The combined organic phase was washed with $H_2O$ (2×20 mL), the combined aqueous phase was adjusted to pH=5 with citric acid. The aqueous phase was then extracted with ethyl acetate (4×50 mL). The combined organic phase was washed with brine (2×50 mL), dried with anhydrous $Na_2SO_4$, filtered and concentrated in vacuo to afford the title compound (1.00 g, 92% yield) as a brown oil. $^1$H NMR (400 MHz, $CDCl_3$) δ 8.15 (d, J=8.0 Hz, 1H), 7.75 (d, J=8.0 Hz, 1H), 7.47 (d, J=3.2 Hz, 1H), 7.31-7.28 (m, 1H), 7.27-7.23 (m, 1H), 4.41 (t, J=5.6 Hz, 2H), 4.15 (s, 2H), 3.84 (t, J=5.6 Hz, 2H), 3.72-3.64 (m, 2H), 3.63-3.47 (m, 6H).

Step 2—(2S,4R)-1-[(2S)-3,3-dimethyl-2-[[2-[2-[2-[2-(4-nitroindol-1-yl)ethoxy]ethoxy]ethoxy]acetyl]amino]butanoyl]-4-hydroxy-N-[[4-(4-methylthiazol-5-yl)phenyl]methyl]pyrrolidine-2-carboxamide To a mixture of 2-[2-[2-[2-(4-nitroindol-1-yl)ethoxy]ethoxy]ethoxy]acetic acid (171 mg, 484 umol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide (200 mg, 428 umol, HCl, Intermediate CI) in DMF (2 mL) was added TEA (183 mg, 1.80 mmol) and HATU (299 mg, 787 umol) in one portion at rt. The mixture was stirred at rt for 3 hours. On completion, the mixture was poured into water (30 mL) and stirred for 2 minutes. The aqueous phase was extracted with ethyl acetate (3×30 mL). The combined organic phase was washed with brine (1×20 mL), dried with anhydrous $Na_2SO_4$, filtered and concentrated in vacuo to afford the title compound (270 mg, 82% yield) as a yellow solid. $^1$H NMR (400 MHz, $CDCl_3$) δ 8.68 (s, 1H), 8.14 (d, J=7.2 Hz, 1H), 7.69 (d, J=8.0 Hz, 1H), 7.45 (d, J=3.2 Hz, 1H), 7.34 (q, J=8.4 Hz, 5H), 7.24 (d, J=4.0 Hz, 2H), 4.73 (t, J=8.0 Hz, 1H), 4.59-4.51 (m, 2H), 4.48 (d, J=8.4 Hz, 1H), 4.41-4.29 (m, 3H), 4.18-4.11 (m, 1H), 4.05-3.94 (m, 2H), 3.81 (t, J=5.2 Hz, 2H), 3.77-3.68 (m, 1H), 3.63-3.53 (m, 8H), 2.82 (br s, 1H), 2.63-2.55 (m, 1H), 2.52 (s, 3H), 2.12 (dd, J=8.0, 13.6 Hz, 1H), 0.94 (s, 9H).

Step 3—(2S,4R)-1-[(2S)-2-[[2-[2-[2-[2-(4-aminoindol-1-yl)ethoxy]ethoxy]ethoxy]acetyl]amino]-3,3-dimethyl-butanoyl]-4-hydroxy-N-[[4-(4-methylthiazol-5-yl)phenyl]methyl]pyrrolidine-2-carboxamide To a mixture of (2S,4R)-1-[(2S)-3,3-dimethyl-2-[[2-[2-[2-[2-(4-nitroindol-1-yl)ethoxy]ethoxy]ethoxy]acetyl]amino]butanoyl]-4-hydroxy-N-[[4-(4-methylthiazol-5-yl)phenyl]methyl]pyrrolidine-2-carboxamide (270 mg, 353 umol) in EA (10 mL) was added Pd/C (100 mg, 10 wt %) in one portion at rt under hydrogen (15 psi pressure). The mixture was stirred at rt for 16 hours. On completion, the mixture was filtered and concentrated in vacuo to afford the title compound (200 mg, 77.1% yield) as a yellow solid. LC-MS (ESI$^+$) m/z 757.1 (M+Na)$^+$.

Step 4—Ethyl 5-[[1-[2-[2-[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethoxy]ethyl]indol-4-yl]amino]-3-methyl sulfanyl-1,2,4-triazine-6-carboxylate A mixture of (2S,4R)-1-[(2S)-2-[[2-[2-[2-[2-(4-aminoindol-1-yl)ethoxy]ethoxy]ethoxy]acetyl]amino]-3,3-dimethyl-butanoyl]-4-hydroxy-N-[[4-(4-methylthiazol-5-yl)phenyl]methyl]pyrrolidine-2-carboxamide (200 mg, 272 umol) and ethyl 5-chloro-3-methylsulfanyl-1,2,4-triazine-6-carboxylate (64.8 mg, 278 umol) in NMP (2 mL) was stirred at rt for 1 hour. On completion, the mixture was purified by reverse phase flash column (0.1% FA) to afford the title compound (200 mg, 79% yield) as a blue oil. LC-MS (ESI$^+$) m/z 932.7 (M+H)$^+$.

Step 5—5-[[1-[2-[2-[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethoxy]ethyl]indol-4-yl]amino]-3-methylsulfanyl-1,2,4-triazine-6-carboxamide To a mixture of ethyl 5-[[1-[2-[2-[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethoxy]ethyl]indol-4-yl]amino]-3-methylsulfanyl-1,2,4-triazine-6-carboxylate (200 mg, 215 umol) in MeOH (300 uL) was added 17 N $NH_3$ in MeOH (300 uL) in one portion at −40° C. under nitrogen. The mixture was stirred at −40° C. for 1 hour. On completion, the mixture was concentrated at reduced pressure at 45° C. The residue was purified by reverse phase flash column (0.1% FA) to afford the title compound (160 mg, 78% yield) as a yellow solid. LC-MS (ESI$^+$) m/z 903.4 (M+H)$^+$.

Step 6—3-[[(1R,2S)-2-aminocyclohexyl]amino]-5-[[1-[2-[2-[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethoxy]ethyl]indol-4-yl]amino]-1,2,4-triazine-6-carboxamide 5-[[1-[2-[2-[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethoxy]ethyl]indol-4-yl]amino]-3-methylsulfanyl-1,2,4-triazine-6-carboxamide (150 mg, 166 umol) and (1R,2S)-cyclohexane-1,2-diamine (200 mg, 1.75 mmol) dissolved in a microwave tube in NMP (3 mL). The sealed tube was heated at 150° C. for 1.5 hours under microwave. On completion, the residue was purified by column (Phenomenex Synergi C18 150*25*10 um; mobile phase: [water (0.05% HCl)-ACN]; B %: 10%-40%, 12 min) to afford the title compound I-196 (107 mg, 60% yield) as a red solid. $^1$H NMR (400 MHz, DMSO-$d_6$) δ 12.91 (s, 1H), 9.24 (d, J=7.2 Hz, 1H), 9.15-9.08 (m, 1H), 8.90-8.70 (m, 1H), 8.70-8.60 (m, 1H), 8.49-8.39 (m, 1H), 8.44-8.34 (m, 2H), 7.94 (d, J=7.6 Hz, 1H), 7.51-7.37 (m, 7H), 7.27-7.18 (m, 1H), 6.52 (d, J=2.4 Hz, 1H), 4.55 (d, J=10.8 Hz, 1H), 4.44 (t, J=8.2 Hz, 2H), 4.40-4.34 (m, 5H), 4.30-4.24 (m, 1H), 4.20-1.12 (m, 1H), 3.73 (d, J=4.8 Hz, 2H), 3.66-3.60 (m, 2H), 3.59-3.47 (m, 12H), 2.43 (s, 3H), 2.11-2.03 (m, 1H), 1.93-1.80 (m, 4H), 1.70-1.60 (m, 3H), 1.45-1.30 (m, 2H), 0.93 (s, 9H); LC-MS (ESI$^+$) m/z 969.5 (M+H)$^+$.

Example 197: 3-[[(1R,2S)-2-aminocyclohexyl]amino]-5-[[1-[2-[2-[2-[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethoxy]ethoxy]ethyl]indol-4-yl]amino-]-1,2,4-triazine-6-carboxamide, I-197

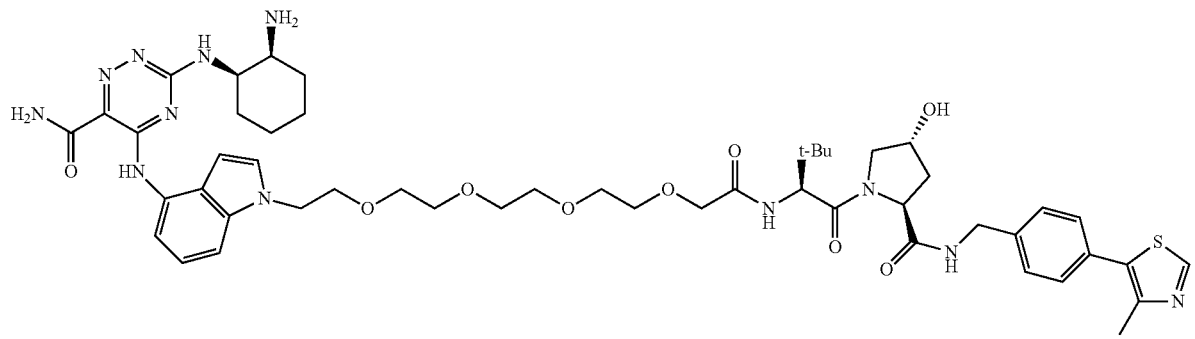 [SMILES: Cc1ncsc1-c1ccc(CNC(=O)[C@@H]2C[C@@H](O)CN2C(=O)[C@@H](NC(=O)COCCOCCOCCOCCn2ccc3c(Nc4nc(N[C@@H]5CCCC[C@@H]5N)nnc4C(N)=O)cccc32)C(C)(C)C)cc1]

3-[[(1R,2S)-2-aminocyclohexyl]amino]-5-[[1-[2-[2-[2-[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethoxy]ethoxy]ethyl]indol-4-yl]amino]-1,2,4-triazine-6-carboxamide I-197 was synthesized as described for Example 196, using Intermediate BK as the mesylate in the first step. Characterization of the final compound: $^1$H NMR (400 MHz, DMSO-$d_6$) δ 12.93 (s, 1H), 9.26 (d, J=8.0 Hz, 1H), 9.21-9.17 (m, 1H), 8.77-8.65 (m, 1H), 8.67 (t, J=5.6 Hz, 1H), 8.45 (br s, 1H), 8.36 (br s, 2H), 7.94 (d, J=7.6 Hz, 1H), 7.52-7.42 (m, 4H), 7.40 (s, 5H), 7.37-7.27 (m, 1H), 6.52 (d, J=2.8 Hz, 1H), 4.55 (d, J=9.6 Hz, 1H), 4.46-4.38 (m, 2H), 3.95 (s, 2H), 3.73 (d, J=5.2 Hz, 2H), 3.71-3.65 (m, 1H), 3.68-3.26 (m, 20H), 2.46-2.40 (m, 3H), 2.10-2.03 (m, 1H), 1.95-1.75 (m, 5H), 1.68-1.58 (m, 4H), 1.45-1.25 (m, 2H), 0.92 (s, 9H); LC-MS (ESI$^+$) m/z 1013.3 (M+H)$^+$.

Example 198: 5-[[(1S,2R)-2-aminocyclohexyl]amino]-7-[3-[2-[2-[2-[2-[[2-(2,6-dioxo-3-piperidyl)-1,3-dioxo-isoindolin-4-yl]amino]ethoxy]ethoxy]ethoxy]ethoxy]-5-methoxy-anilino]imidazo[1,2-c]pyrimidine-8-carboxamide, I-198

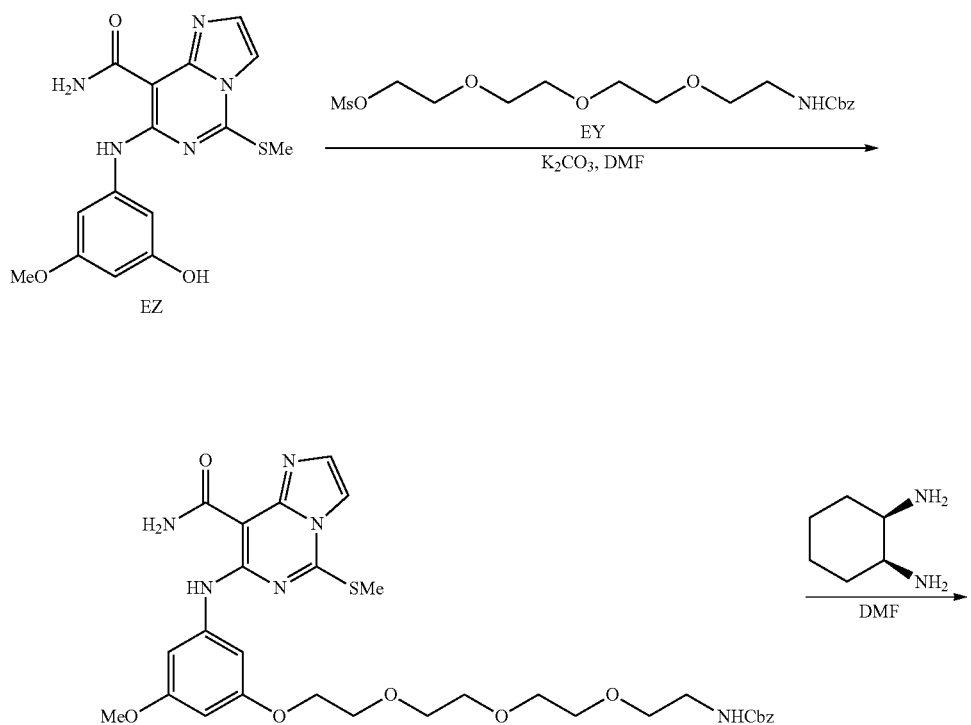

-continued
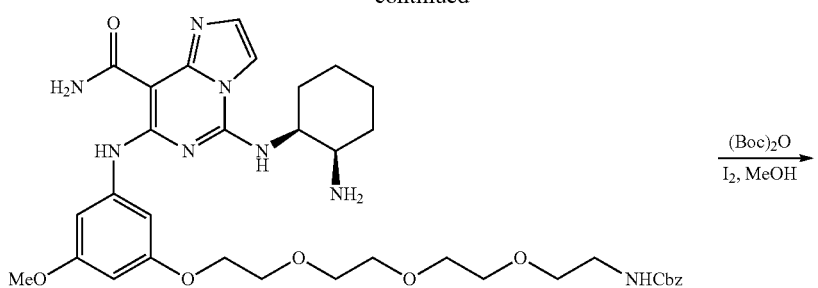
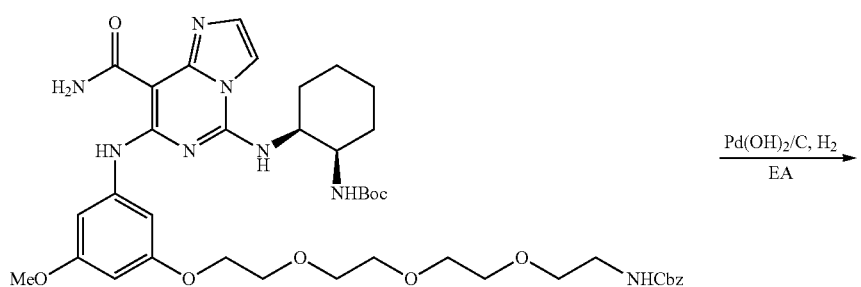
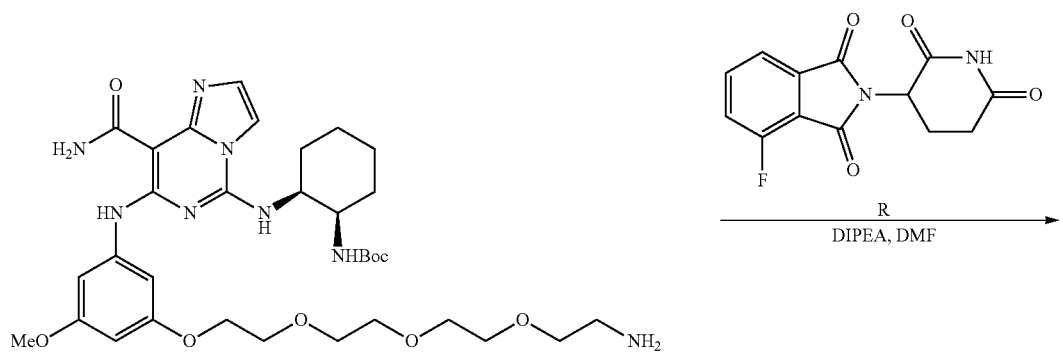
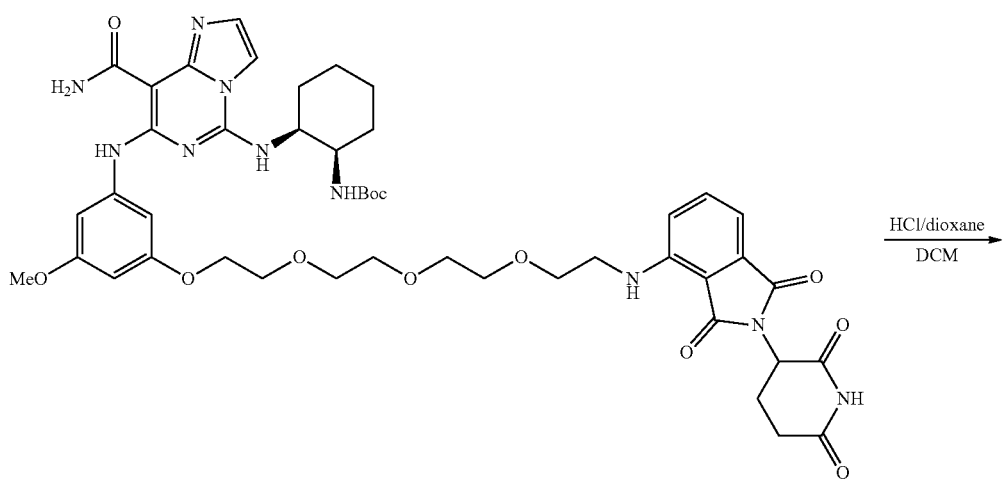

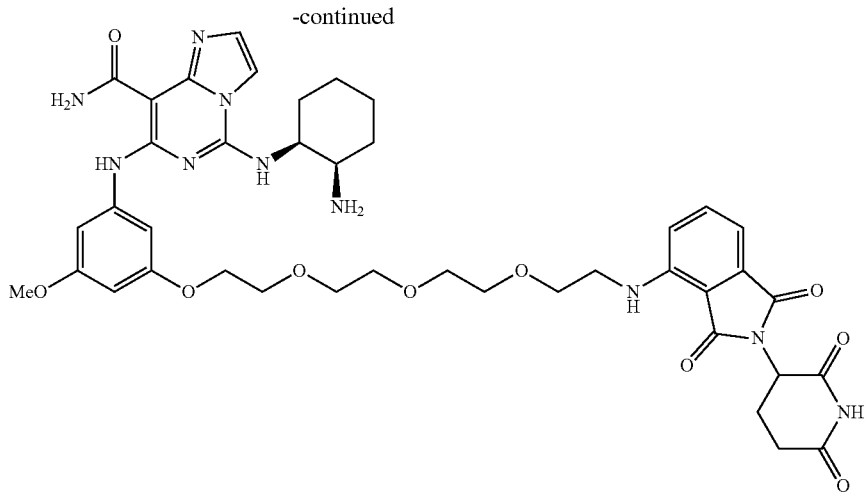

Step 1—Benzyl (2-(2-(2-(2-(3-((8-carbamoyl-5-(methylthio)imidazo[1,2-c]pyrimidin-7-yl)amino)-5-methoxyphenoxy)ethoxy)ethoxy)ethyl)carbamate To a solution of 7-(3-hydroxy-5-methoxy-anilino)-5-methylsulfanyl-imidazo[1,2-c]pyrimidine-8-carboxamide (300 mg, 869 umol, Intermediate EZ) in DMF (10 mL) was added $K_2CO_3$ (480 mg, 3.47 mmol) and 2-[2-[2-[2-(benzyloxycarbonylamino)ethoxy]ethoxy]ethoxy]ethyl methanesulfonate (1.76 g, 4.34 mmol, Intermediate EY) under nitrogen atmosphere. The reaction mixture was stirred at 100° C. for 12 hrs. On completion, the reaction mixture was concentrated in vacuo. The residue was extracted with ethyl acetate (100 mL) and filtered. The filtrate was concentrated in vacuo. The residue was purified by reverse phase chromatography (0.1% $NH_3.H_2O$) to give the title compound (380 mg, 67% yield) as a yellow oil. LC-MS (ESI$^+$) m/z 655.1 (M+H)$^+$.

Step 2—Benzyl (2-(2-(2-(2-(3-((5-(((1S,2R)-2-aminocyclohexyl)amino)-8-carbamoylimidazo[1,2-c]pyrimidin-7-yl)amino)-5-methoxyphenoxy)ethoxy)ethoxy)ethyl)carbamate A solution of benzyl N-[2-[2-[2-[2-[3-[(8-carbamoyl-5-methylsulfanyl-imidazo[1,2-c]pyrimidin-7-yl)-amino]-5-methoxy-phenoxy]ethoxy]ethoxy]ethoxy]ethyl]carbamate (200 mg, 305 umol) and (1R,2S)-cyclohexane-1,2-diamine (38.4 mg, 336 umol) in DMF (5 mL) was heated to 90° C. for 12 hrs. On completion, the reaction mixture was concentrated in vacuo to give the title compound (220 mg, 100% yield) as a yellow oil. LC-MS (ESI$^+$) m/z 721.1 (M+H)$^+$.

Step 3—Tert-butyl N-[(1R,2S)-2-[[7-[3-[2-[2-[2-[2-(benzyloxycarbonylamino)ethoxy]ethoxy]ethoxy]ethoxy]-5-methoxy-anilino]-8-carbamoyl-imidazo[1,2-c]pyrimidin-5-yl]amino]cyclohexyl]carbamate To a solution of benzyl N-[2-[2-[2-[2-[3-[[5-[[(1S,2R)-2-aminocyclohexyl]amino]-8-carbamoyl-imidazo[1,2-c]pyrimidin-7-yl]amino]-5-methoxy-phenoxy]ethoxy]ethoxy]ethoxy]ethyl]carbamate (220 mg, 305 umol) in methanol (3 mL) was added $I_2$ (7.75 mg, 30.5 umol) and (Boc)$_2$O (133 mg, 610 umol) at rt. The reaction mixture was stirred at rt for 6 hrs. On completion, the reaction mixture was concentrated in vacuo. The residue was purified by silica gel chromatography (dichloromethane:methanol=20:1) to give the title compound (230 mg, 91% yield) as a yellow oil. LC-MS (ESI$^+$) m/z 821.1 (M+H)$^+$.

Step 4—Tert-butyl N-[(1R,2S)-2-[[7-[3-[2-[2-[2-(2-aminoethoxy)ethoxy]ethoxy]ethoxy]-5-methoxy-anilino]-8-carbamoyl-imidazo[1,2-c]pyrimidin-5-yl]amino]cyclohexyl]carbamate To a solution of tert-butyl N-[(1R,2S)-2-[[7-[3-[2-[2-[2-[2-(benzyloxycarbonylamino)ethoxy]ethoxy]ethoxy]ethoxy]-5-methoxy-anilino]-8-carbamoyl-imidazo[1,2-c]pyrimidin-5-yl]amino]cyclohexyl]carbamate (230 mg, 280 umol) in ethyl acetate (3 mL) was added Pd(OH)$_2$/C (120 mg, 280 umol, 10 wt %) under nitrogen atmosphere. The suspension was degassed and purged with hydrogen three times. The mixture was stirred under hydrogen gas (15 psi pressure) at rt for 12 h. On completion, the reaction mixture was filtered and the filtrate was concentrated in vacuo to give the title compound (130 mg, 65% yield) as yellow oil. LC-MS (ESI$^+$) m/z 687.2 (M+H)$^+$.

Step 5—Tert-butyl N-[(1R,2S)-2-[[8-carbamoyl-7-[3-[2-[2-[2-[2-[[2-(2,6-dioxo-3-piperidyl)-1,3-dioxo-isoindolin-4-yl]amino]ethoxy]ethoxy]ethoxy]ethoxy]-5-methoxy-anilino]imidazo[1,2-c]pyrimidin-5-yl]amino]cyclohexyl]carbamate To a solution of tert-butyl N-[(1R,2S)-2-[[7-[3-[2-[2-[2-(2-aminoethoxy)ethoxy]ethoxy]ethoxy]-5-methoxy-anilino]-8-carbamoyl-imidazo[1,2-c]pyrimidin-5-yl]amino]cyclohexyl]carbamate (130 mg, 189 umol) and 2-(2,6-dioxo-3-piperidyl)-4-fluoro-isoindoline-1,3-dione (57.5 mg, 208 umol, Intermediate R) in DMF (4 mL) was added DIPEA (73.4 mg, 568 umol) under nitrogen. The reaction mixture was stirred at 90° C. for 12 h. On completion, the reaction mixture was concentrated in vacuo. The residue was purified by reverse phase chromatography to give the title compound (70.0 mg, 39% yield) as a yellow solid. LC-MS (ESI$^+$) m/z 943.1 (M+H)$^+$.

Step 6—5-[[(1S,2R)-2-aminocyclohexyl]amino]-7-[3-[2-[2-[2-[2-[[2-(2,6-dioxo-3-piperidyl)-1,3-dioxo-isoindolin-4-yl]amino]ethoxy]ethoxy]ethoxy]ethoxy]-5-methoxy-anilino]imidazo[1,2-c]pyrimidine-8-carboxamide To a solution of tert-butyl N-[(1R,2S)-2-[[8-carbamoyl-7-[3-[2-[2-[2-[2-[[2-(2,6-dioxo-3-piperidyl)-1,3-dioxo-isoindolin-4-yl]amino]ethoxy]ethoxy]ethoxy]ethoxy]-5-methoxy-anilino]imidazo[1,2-c]pyrimidin-5-yl]amino]cyclohexyl]carbamate (70.0 mg, 74.2 umol) in DCM (4 mL) was added HCl in dioxane (4 M, 4.00 mL) at rt. The reaction mixture was stirred at rt for 1 hour. On completion, the reaction mixture was concentrated in vacuo. The residue was purified by prep-HPLC (column: Boston pH-lex 150*25 10 um; mobile phase: [water (0.225% FA)-ACN]; B %: 20%-50%) to give the title compound I-198 (13.5 mg, 21% yield) as a white solid. $^{1}$H NMR (400 MHz, DMSO-d$_6$) δ 12.39 (s, 1H), 9.55 (d, J=3.2 Hz, 1H), 8.36 (s, 1H), 8.12 (s, 1H), 7.57-7.53 (m, 1H), 7.40 (d, J=3.6 Hz, 1H), 7.32 (d, J=1.6 Hz, 1H), 7.10 (d, J=8.4 Hz, 1H), 7.01 (d, J=6.8 Hz, 1H), 6.93 (s, 1H), 6.67 (s, 1H), 6.58 (t, J=5.6 Hz, 1H), 6.20 (s, 1H), 5.06-5.02 (m, 1H), 4.20 (d, J=11.2 Hz, 1H), 4.08-4.04 (m, 2H), 3.74 (s, 3H), 3.71 (s, 2H), 3.62 (s, 2H), 3.59-3.50 (m, 12H), 2.92-2.81 (m, 1H), 2.62-2.58 (m, 2H), 2.28-2.26 (m, 1H), 2.04-1.94 (m, 2H), 1.82-1.64 (m, 4H), 1.56-1.53 (m, 2H), 1.46-1.33 (m, 2H); LC-MS (ESI$^+$) m/z 843.4 (M+H)$^+$.

Example 199: Tert-butyl ((1R,2S)-2-((8-carbamoyl-7-((3-((14-((2-(2,6-dioxopiperidin-3-yl)-1,3-dioxoisoindolin-4-yl)amino)-3,6,9,12-tetraoxatetradecyl)oxy)-5-methoxyphenyl)amino)imidazo[1,2-c]pyrimidin-5-yl)amino)cyclohexyl)carbamate, I-199

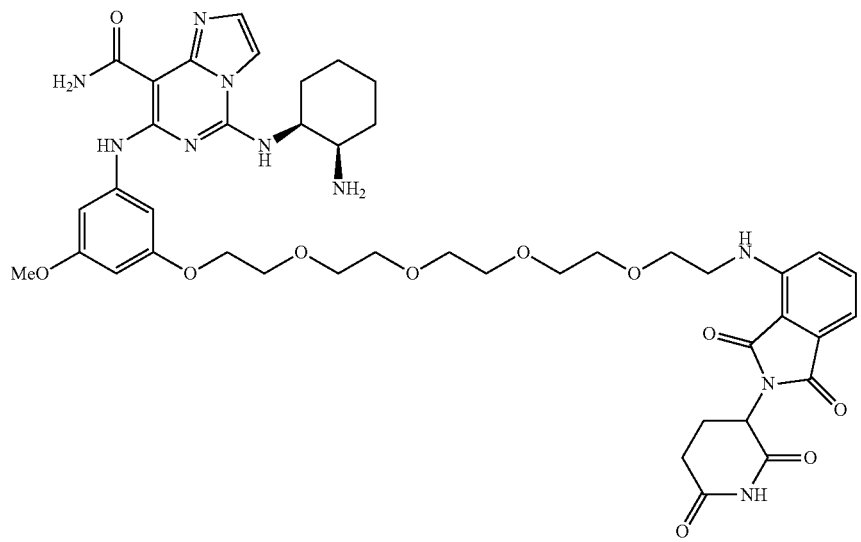 [SMILES: COc1cc(Nc2nc(N[C@H]3CCCC[C@H]3N)n3ccnc3c2C(N)=O)cc(OCCOCCOCCOCCOCCNc2cccc3c2C(=O)N(C2CCC(=O)NC2=O)C3=O)c1]

Tert-butyl ((1R,2S)-2-((8-carbamoyl-7-((3-((14-((2-(2,6-dioxopiperidin-3-yl)-1,3-dioxoiso indolin-4-yl)amino)-3,6,9,12-tetraoxatetradecyl)oxy)-5-methoxyphenyl)amino)imidazo[1,2-c]pyrimidin-5-yl)amino)cyclohexyl)carbamate I-199 was synthesized as described above for Example 198 using Intermediate FC as the mesylate. Step 1 was run at 60 C for 12 h. Characterization of the final product: $^{1}$H NMR (400 MHz, DMSO-d$_6$) δ 12.39 (s, 1H), 9.55 (s, 1H), 8.36 (s, 2H), 8.13 (s, 1H), 7.58-7.53 (m, 1H), 7.39 (s, 1H), 7.32 (s, 1H), 7.11 (d, J=8.4 Hz, 1H), 7.02 (d, J=6.8 Hz, 1H), 6.93 (s, 1H), 6.67 (s, 1H), 6.58 (s, 1H), 6.21 (s, 1H), 5.04 (dd, J=5.2, 13.2 Hz, 1H), 4.22 (d, J=10.4 Hz, 1H), 4.07 (s, 2H), 3.74 (s, 3H), 3.71 (s, 2H), 3.64-3.56 (m, 18H), 2.89-2.85 (m, 2H), 2.63-2.60 (m, 2H), 2.27-2.65 (m, 1H), 1.80-1.72 (m, 1H), 1.71-1.65 (m, 4H), 1.56-1.52 (m, 2H), 1.45-1.51 (m, 2H); LC-MS (ESI$^+$) m/z 887.4 (M+H)$^+$.

Example 200: 5-(((1S,2R)-2-aminocyclohexyl)amino)-7-((4-(2-(2-(2-(2-((2-(2,6-dioxopiperidin-3-yl)-1,3-dioxoisoindolin-4-yl)amino)ethoxy)ethoxy)ethoxy)ethoxy)-3,5-dimethoxyphenyl)amino)imidazo[1,2-c]pyrimidine-8-carboxamide, I-200
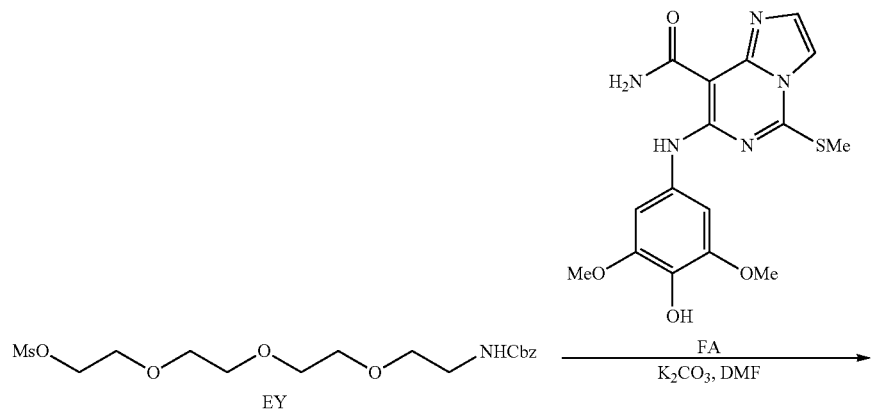
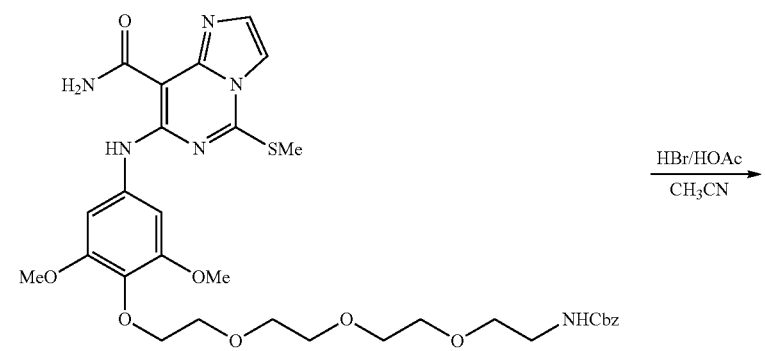
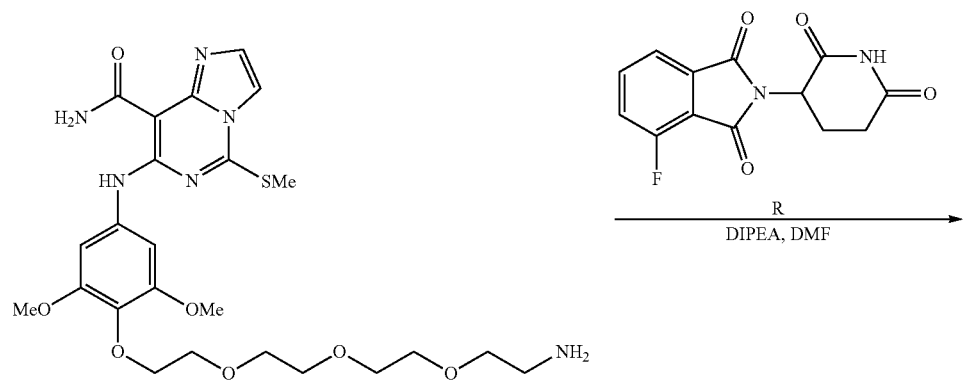

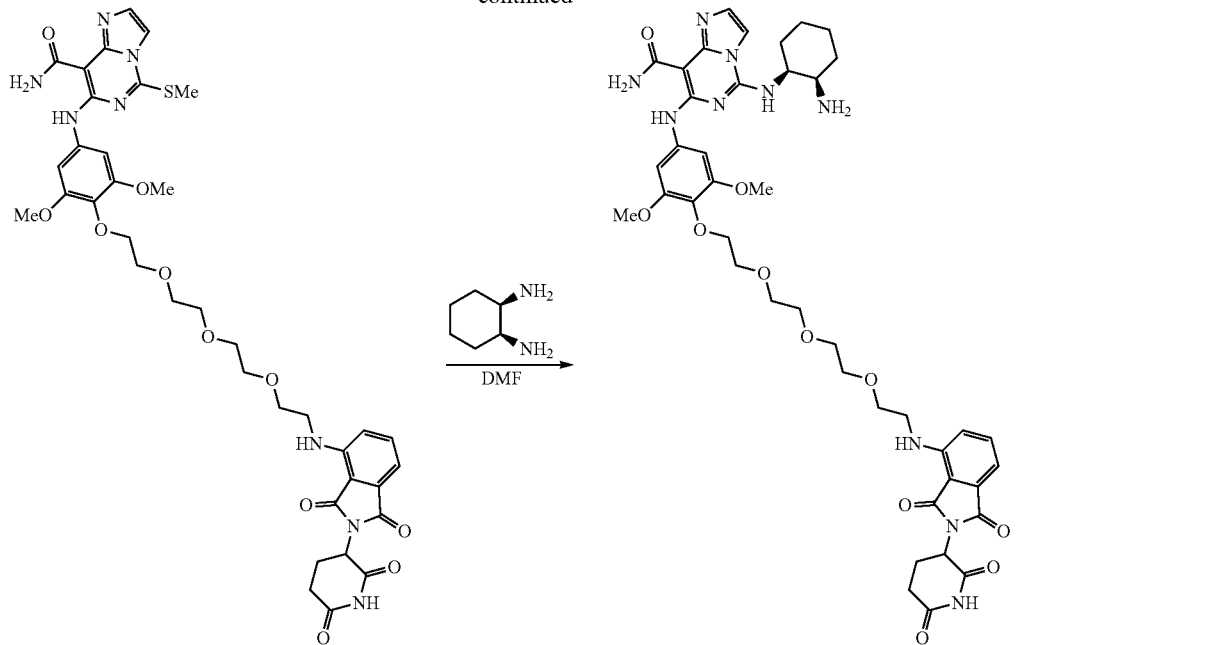

Step 1—Benzyl (2-(2-(2-(2-(4-((8-carbamoyl-5-(methylthio)imidazo[1,2-c]pyrimidin-7-yl)amino)-2,6-dimethoxyphenoxy)ethoxy)ethoxy)ethoxy)ethyl)carbamate To a mixture of 7-(4-hydroxy-3,5-dimethoxy-anilino)-5-methylsulfanyl-imidazo[1,2-c]pyrimidine-8-carboxamide (200 mg, 532 umol, Intermediate FA) in DMF (3 mL) was added 2-[2-[2-[2-(benzyloxycarbonylamino) ethoxy]ethoxy]ethoxy]ethylmethanesulfonate (237 mg, 586 umol, Intermediate EY) and $K_2CO_3$ (220 mg, 1.60 mmol). Then the reaction mixture was stirred at 70° C. for 12 hours. On completion, the reaction mixture was washed with water (50 mL) and extracted with ethyl acetate (2×50 mL). The combined organic layer was dried with $Na_2SO_4$, filtrated and concentrated in vacuo. The residue was purified by prep-column chromatography (PE:EA=3:1 to DCM:MeOH=20:1) to give the title compound (172 mg, 47% yield) as a yellow oil. LC-MS (ESI$^+$) m/z 685.0 (M+H)$^+$.

Step 2—7-((4-(2-(2-(2-(2-Aminoethoxy)ethoxy)ethoxy)ethoxy)-3,5-dimethoxyphenyl)amino)-5-(methylthio)imidazo[1,2-c]pyrimidine-8-carboxamide To a mixture of benzyl N-[2-[2-[2-[2-[4-[(8-carbamoyl-5-methylsulfanyl-imidazo[1,2-c]pyrimidin-7-yl)amino]-2,6-dimethoxyphenoxy]ethoxy]ethoxy]ethoxy]ethyl]carbamate (200 mg, 292 umol) in $CH_3CN$ (2 mL) was added HBr in HOAc (32.9 mg, 292 umol, 1 mL). Then the reaction mixture was stirred at 50° C. for 1 hour. On completion, the reaction mixture was quenched with sat. $NaHCO_3$ (3×30 mL) and extracted with DCM (3×30 mL). The organic layer was dried with $Na_2SO_4$, filtrated and concentrated in vacuo. The residue was purified by reverse phase chromatography (0.1% FA in water) to give the title compound (70.0 mg, 43% yield) as a yellowish oil.

Step 3—7-((4-(2-(2-(2-(2-((2-(2,6-Dioxopiperidin-3-yl)-1,3-dioxoisoindolin-4-yl)amino)ethoxy)ethoxy)ethoxy)ethoxy)-3,5-dimethoxyphenyl)amino)-5-(methylthio)imidazo[1,2-c]pyrimidine-8-carboxamide To a mixture of 7-[4-[2-[2-[2-(2-aminoethoxy)ethoxy]ethoxy]ethoxy]-3,5-dimethoxy-anilino]-5-methylsulfanyl-imidazo[1,2-c]pyrimidine-8-carboxamide (70.0 mg, 127 umol) and 2-(2,6-dioxo-3-piperidyl)-4-fluoro-isoindoline-1,3-dione (38.6 mg, 139 umol, Intermediate R) in DMF (1.5 mL) was added DIPEA (32.8 mg, 254 umol). Then the reaction mixture was stirred at 90° C. for 8 hours. On completion, the reaction mixture was concentrated in vacuo. The residue was purified by prep-TLC (PE:EA=0:1) to give the title compound (30.0 mg, 23% yield) as a yellowish solid. LC-MS (ESI$^+$) m/z 829.1 (M+Na)$^+$.

Step 4—5-(((1S,2R)-2-aminocyclohexyl)amino)-7-((4-(2-(2-(2-(2-((2-(2,6-dioxopiperidin-3-yl)-1,3-dioxoisoindolin-4-yl)amino)ethoxy)ethoxy)ethoxy)ethoxy)-3,5-dimethoxyphenyl)amino)imidazo[1,2-c]pyrimidine-8-carboxamide To a mixture of 7-[4-[2-[2-[2-[2-[[2-(2,6-dioxo-3-piperidyl)-1,3-dioxo-isoindolin-4-yl]amino]ethoxy]ethoxy]ethoxy]ethoxy]-3,5-dimethoxy-anilino]-5-methylsulfanyl-imidazo[1,2-c]pyrimidine-8-carboxamide (30.0 mg, 37.1 umol) in DMF (1 mL) was added (1R,2S)-cyclohexane-1,2-diamine (8.49 mg, 74.3 umol). Then the reaction mixture was stirred at 90° C. for 8 hours. On completion, the reaction mixture was concentrated in vacuo. The residue was purified by prep-HPLC (column: Boston Green ODS 150*30 5 u; mobile phase: [water (0.225% FA)-ACN]; B %: 20%-44%, 10 min) to give the title compound I-200 (6.00 mg, 18% yield) as a yellowish oil. $^1$H NMR (400 MHz, DMSO-$d_6$) δ 12.19 (s, 1H), 9.53 (d, J=2.8 Hz, 1H), 8.36 (s, 1H), 8.12 (s, 1H), 7.57 (t, J=7.6 Hz, 1H), 7.37 (d, J=3.2 Hz, 1H), 7.32 (s, 1H), 7.14 (d, J=8.4 Hz, 1H), 7.03 (d, J=7.2 Hz, 1H),

2363
6.91-6.76 (m, 2H), 6.61 (t, J=5.6 Hz, 1H), 5.05 (dd, J=5.6, 12.0 Hz, 1H), 4.19 (d, J=10.4 Hz, 1H), 4.12-4.06 (m, 1H), 4.05-3.99 (m, 1H), 3.93 (d, J=4.8 Hz, 1H), 3.79 (s, 6H), 3.64-3.63 (m, 4H), 3.56-3.50 (m, 8H), 2.94-2.88 (m, 2H), 2.08-1.85 (m, 3H), 1.76-1.19 (m, 9H); LC-MS (ESI$^+$) m/z 873.1 (M+H)$^+$.
2364
Example 201: (±)-2-(2,6-Dioxo-3-piperidyl)-4-[2-[2-[2-[2-[2-[5-[[4-[6-(3-ethylpiperazin-1-yl)-3-pyridyl]pyrimidin-2-yl]amino]-2,3-dimethoxyphenoxy]ethoxy]ethoxy]ethoxy]ethoxy]ethylamino]isoindoline-1,3-dione, I-201
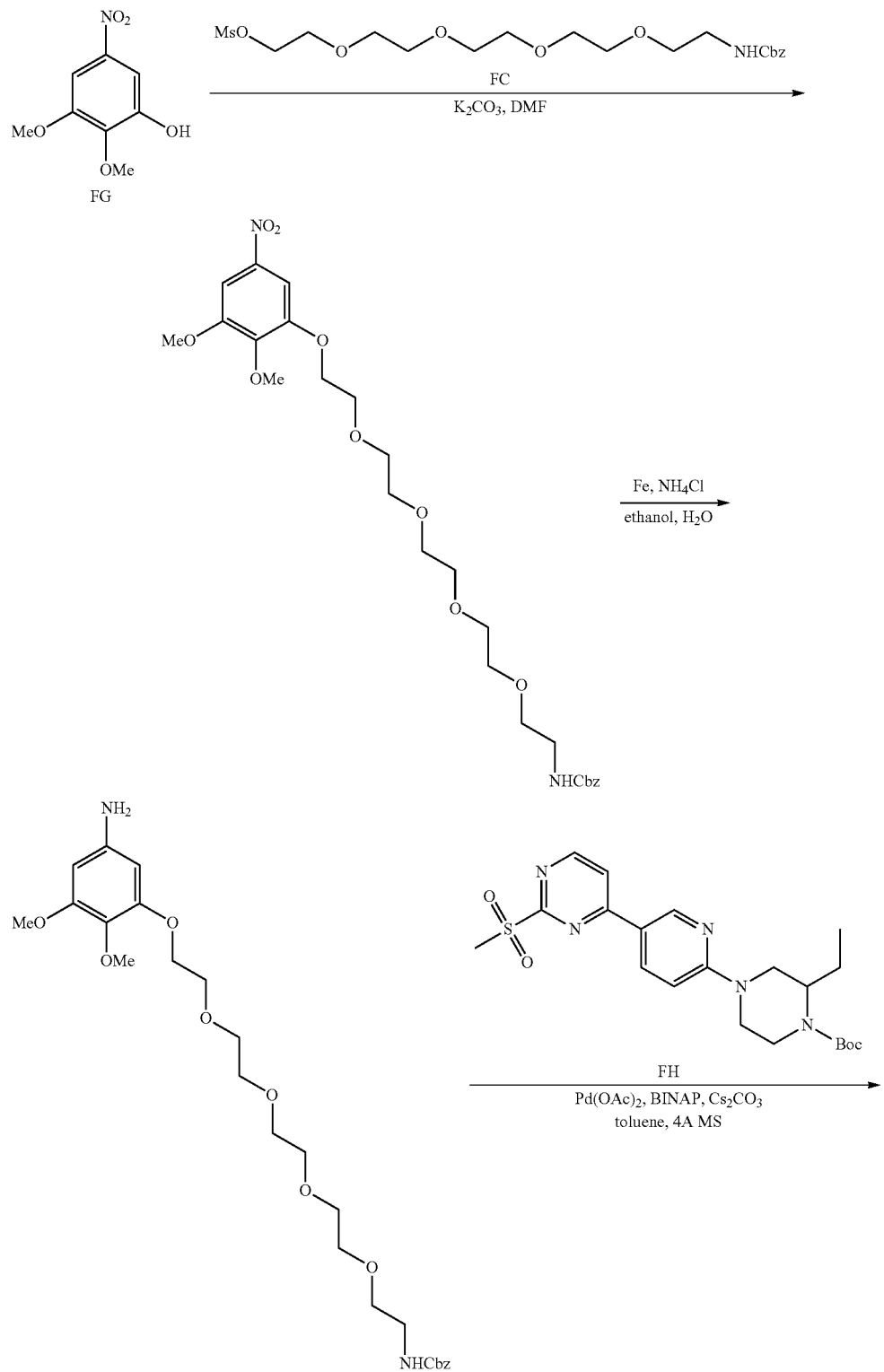

-continued
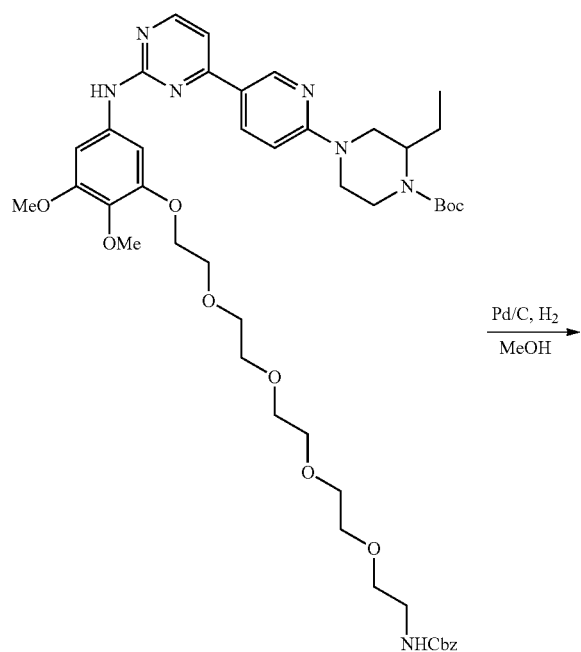
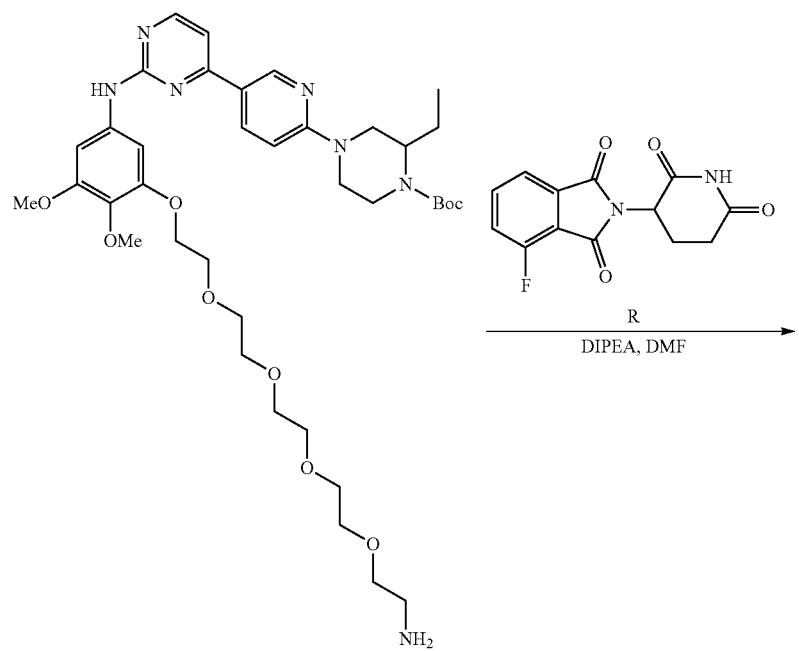

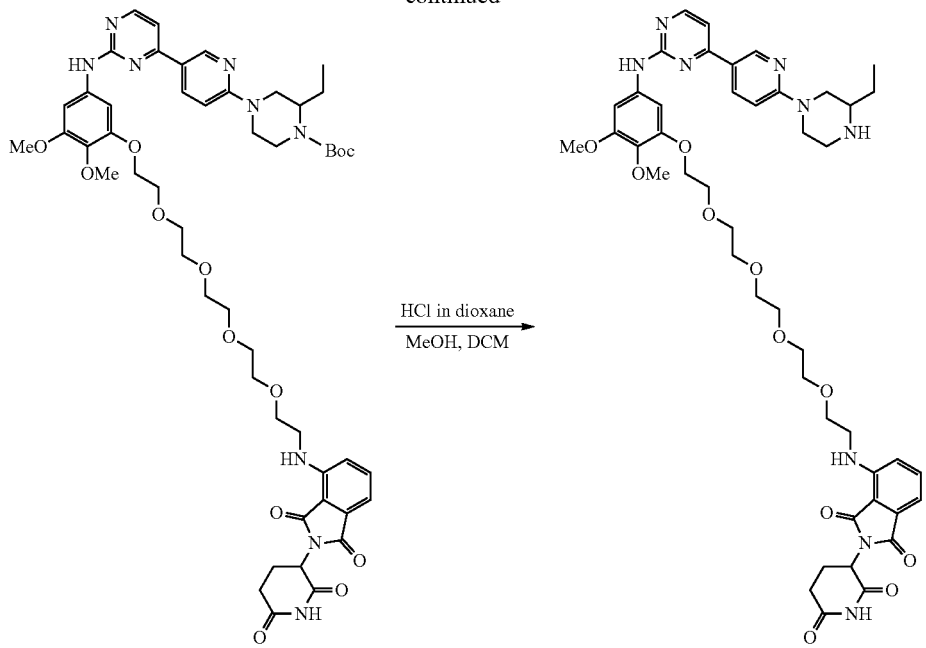

Step 1—Benzyl N-[2-[2-[2-[2-[2-(2,3-dimethoxy-5-nitro-phenoxy)ethoxy]ethoxy]ethoxy]ethoxy]ethyl] carbamate To a mixture of 2-[2-[2-[2-[2-(benzyloxycarbonylamino) ethoxy]ethoxy]ethoxy]ethoxy]ethyl methane sulfonate (606 mg, 1.35 mmol, Intermediate FC) in DMF (10 mL) was added 2,3-dimethoxy-5-nitro-phenol (268 mg, 1.35 mmol, Intermediate FG) and potassium carbonate (559 mg, 4.05 mmol). Then the reaction mixture was stirred at 70° C. for 12 hours. On completion, the reaction mixture was washed with water (20 mL) and extracted with ethyl acetate (3×30 mL). The combined organic layer was dried with anhydrous sodium sulfate, filtered and concentrated in vacuo. The residue was purified by column (petroleum ether:ethyl acetate=1:1 to dichloromethane:methanol=20:1) to give the title compound (610 mg, 74% yield) as a yellowish oil. LC-MS (ESI$^+$) m/z 553.1 (M+H)$^+$.

Step 2—Benzyl N-[2-[2-[2-[2-[2-(5-amino-2,3-dimethoxy-phenoxy)ethoxy]ethoxy]ethoxy]ethoxy] ethyl]carbamate To a solution of benzyl N-[2-[2-[2-[2-[2-(2,3-dimethoxy-5-nitro-phenoxy)ethoxy]ethoxy]ethoxy]ethoxy]ethyl]carbamate (460 mg, 832 umol) in water (2 mL) and ethanol (8 mL) was added ammonium chloride (445 mg, 8.32 mmol) and Fe (464 mg, 8.32 mmol). The reaction mixture was stirred at 78° C. for 1 hour. On completion, the reaction mixture was filtered and concentrated in vacuo. The residue was purified by silica gel chromatography (dichloromethane:methanaol=50:1) to give the title compound (430 mg, 98% yield) as a yellow oil. $^1$H NMR (400 MHz, CDCl$_3$) δ 7.37-7.35 (m, 5H), 6.03-5.82 (m, 2H), 5.52 (br s, 1H), 5.16-5.07 (m, 2H), 4.19-4.08 (m, 2H), 3.84 (d, J=5.6 Hz, 2H), 3.81 (s, 3H), 3.77 (s, 3H), 3.74-3.70 (m, 2H), 3.68-3.63 (m, 10H), 3.59-3.55 (m, 3H), 3.44-3.39 (m, 2H); LC-MS (ESI$^+$) m/z 523.1 (M+H)$^+$.

Step 3—(±)-Tert-butyl 4-[5-[2-[3-[2-[2-[2-[2-[2-(benzyloxycarbonylamino)ethoxy]ethoxy]ethoxy]ethoxy]ethoxy]-4,5-dimethoxyanilino]pyrimidin-4-yl]-2-pyridyl]-2-ethyl-piperazine-1-carboxylate To a solution of (±)-tert-butyl 2-ethyl-4-[5-(2-methylsulfonylpyrimidin-4-yl)-2-pyridyl]piperazine-1-carboxylate (200 mg, 446 umol, Intermediate FH) and benzyl N-[2-[2-[2-[2-[2-(5-amino-2,3-dimethoxyphenoxy)ethoxy]ethoxy]ethoxy]ethoxy]ethyl]carbamate (233 mg, 446 umol) in toluene (3 mL) was added Pd(OAc)$_2$ (10.0 mg, 44.6 umol), BINAP (41.7 mg, 67.0 umol), cesium carbonate (436 mg, 1.34 mmol) and 4 AMS (1.00 g, 446 umol) under nitrogen. The reaction mixture was stirred at 100° C. for 12 hours. On completion, the reaction mixture was filtered and concentrated in vacuo. The residue was purified by reverse phase chromatography (0.1% FA in water) to give the title compound (160 mg, 32% yield) as a yellow oil. $^1$H NMR (400 MHz, CDCl$_3$) δ 8.87 (d, J=2.4 Hz, 1H), 8.34 (d, J=5.2 Hz, 1H), 8.20 (dd, J=2.4, 9.2 Hz, 1H), 7.37-7.29 (m, 5H), 7.19 (d, J=2.0 Hz, 1H), 7.03 (d, J=5.2 Hz, 1H), 6.92 (s, 1H), 6.65 (d, J=9.2 Hz, 1H), 5.59 (br s, 1H), 5.09 (s, 2H), 4.36-4.24 (m, 2H), 4.20 (t, J=4.8 Hz, 2H), 4.16-3.97 (m, 2H), 3.91 (s, 3H), 3.87 (t, J=4.8 Hz, 2H), 3.84 (s, 3H), 3.72 (d, J=4.8 Hz, 2H), 3.63-3.61 (m, 10H), 3.57-3.53 (m, 2H), 3.42-3.36 (m, 2H), 3.24 (dd, J=4.0, 13.2 Hz, 1H), 3.18-3.01 (m, 2H), 1.66-1.56 (m, 2H), 1.50 (s, 9H), 0.92 (t, J=7.2 Hz, 3H).

Step 4—(±)-Tert-butyl 4-[5-[2-[3-[2-[2-[2-[2-(2-aminoethoxy)ethoxy]ethoxy]ethoxy]ethoxy]-4,5-dimethoxy-anilino]pyrimidin-4-yl]-2-pyridyl]-2-ethyl-piperazine-1-carboxylate To a mixture of (±)-tert-butyl 4-[5-[2-[3-[2-[2-[2-[2-[2-(benzyloxycarbonylamino)ethoxy]ethoxy]ethoxy]ethoxy]ethoxy]-4,5-dimethoxy-anilino]pyrimidin-4-yl]-2-pyridyl]-2-ethyl-piperazine-1-carboxylate (160 mg, 179 umol) in NH$_3$.H$_2$O (50 uL) and methanol (6 mL) was added Pd(OH)$_2$/C (60.0 mg, 10 wt %). Then the reaction mixture was stirred at rt for 10 hours under hydrogen (50 psi pressure). On completion, the reaction mixture was concentrated in vacuo to give the title compound (130 mg, 95% yield) as a yellowish oil. LC-MS (ESI⁺) m/z 756.4 (M+H)⁺.

Step 5—(±)-Tert-butyl 4-[5-[2-[3-[2-[2-[2-[2-[[2-(2,6-dioxo-3-piperidyl)-1,3-dioxo-isoindolin-4-yl]amino]ethoxy]ethoxy]ethoxy]ethoxy]-4,5-dimethoxy-anilino]pyrimidin-4-yl]-2-pyridyl]-2-ethyl-piperazine-1-carboxylate To a mixture of (±)-tert-butyl 4-[5-[2-[3-[2-[2-[2-[2-(2-aminoethoxy)ethoxy]ethoxy]ethoxy]ethoxy]-4,5-dimethoxyanilino]pyrimidin-4-yl]-2-pyridyl]-2-ethyl-piperazine-1-carboxylate (70.0 mg, 92.6 umol) in DMF (2 mL) was added (+)-2-(2,6-dioxo-3-piperidyl)-4-fluoro-isoindoline-1,3-dione (28.1 mg, 101 umol, Intermediate R) and DIPEA (29.9 mg, 231 umol, 40.4 uL). Then the reaction mixture was stirred at 90° C. for 12 hours. On completion, the reaction mixture was concentrated in vacuo. The residue was purified by prep-TLC (dichloromethane:methanaol=20:1) to give the title compound (40.0 mg, 40% yield) as a yellowish solid. LC-MS (ESI⁺) m/z 1012.2 (M+H)⁺.

Step 6—(±)-2-(2,6-Dioxo-3-piperidyl)-4-[2-[2-[2-[2-[2-[5-[[4-[6-(3-ethylpiperazin-1-yl)-3-pyridyl]pyrimidin-2-yl]amino]-2,3-dimethoxyphenoxy]ethoxy]ethoxy]ethoxy]ethyl amino]isoindoline-1,3-dione To a mixture of (±)-tert-butyl 4-[5-[2-[3-[2-[2-[2-[2-[[2-(2,6-dioxo-3-piperidyl)-1,3-dioxo-iso indolin-4-yl]amino]ethoxy]ethoxy]ethoxy]ethoxy]-4,5-dimethoxy-anilino]pyrimidin-4-yl]-2-pyridyl]-2-ethyl-piperazine-1-carboxylate (73.0 mg, 72.1 umol) in a mixture of methanol (1 mL) and dichloromethane (1 mL) was added 4M HCl in dioxane (72.1 umol, 1.00 mL) at 0° C. Then the reaction mixture was allowed to warm to rt and stirred for 2 hours. On completion, the reaction mixture was concentrated in vacuo. The residue was purified by prep-HPLC (column: Boston Green ODS 150*30 5 u; mobile phase: [water (0.225% FA)-ACN]; B %: 27%-48%, 10 min) to give the title compound I-201 (35.0 mg, 53% yield) as a yellowish solid. ¹H NMR (400 MHz, DMSO-d₆) δ 11.12 (s, 1H), 9.39 (s, 1H), 8.93 (s, 1H), 8.42 (d, J=5.6 Hz, 1H), 8.26 (d, J=9.2 Hz, 1H), 7.56 (t, J=7.6 Hz, 1H), 7.34-7.22 (m, 3H), 7.16-7.09 (m, 1H), 7.06-6.99 (m, 1H), 6.98-6.88 (m, 1H), 6.67-6.54 (m, 1H), 6.58 (t, J=5.6 Hz, 1H), 5.05 (dd, J=5.2, 13.2 Hz, 1H), 4.39-4.19 (m, 2H), 4.11 (d, J=3.6 Hz, 2H), 3.79 (s, 3H), 3.65 (s, 3H), 3.63-3.57 (m, 6H), 3.56-3.52 (m, 2H), 3.54-3.50 (m, 6H), 3.47-3.41 (m, 4H), 3.00 (d, J=11.6 Hz, 2H), 2.86 (d, J=12.0 Hz, 3H), 2.75-2.64 (m, 3H), 2.10-1.95 (m, 1H), 1.50-1.34 (m, 2H), 0.95 (t, J=7.6 Hz, 3H); LC-MS (ESI⁺) m/z 912.2 (M+H)⁺.

Example 202: (2S,4R)-1-[(2S)-2-[[2-[2-[2-[2-[2-[5-[[4-[6-(3-ethylpiperazin-1-yl)-3-pyridyl]pyrimidin-2-yl]amino]-2,3-dimethoxy-phenoxy]ethoxy]ethoxy]ethoxy]ethoxy]acetyl]amino]-3,3-dimethylbutanoyl]-4-hydroxy-N-[[4-(4-methylthiazol-5-yl)phenyl]methyl]pyrrolidine-2-carboxamide, I-202

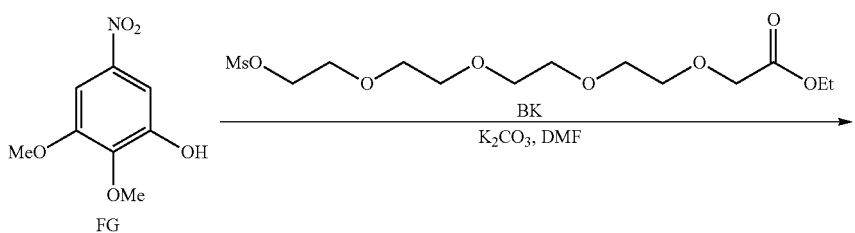

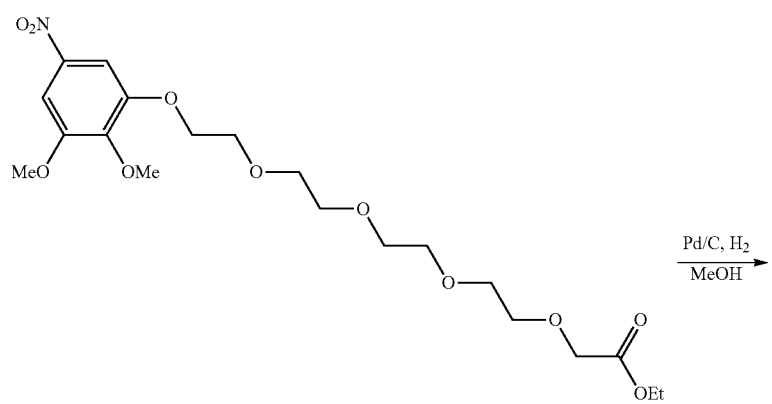

2371
-continued
2372
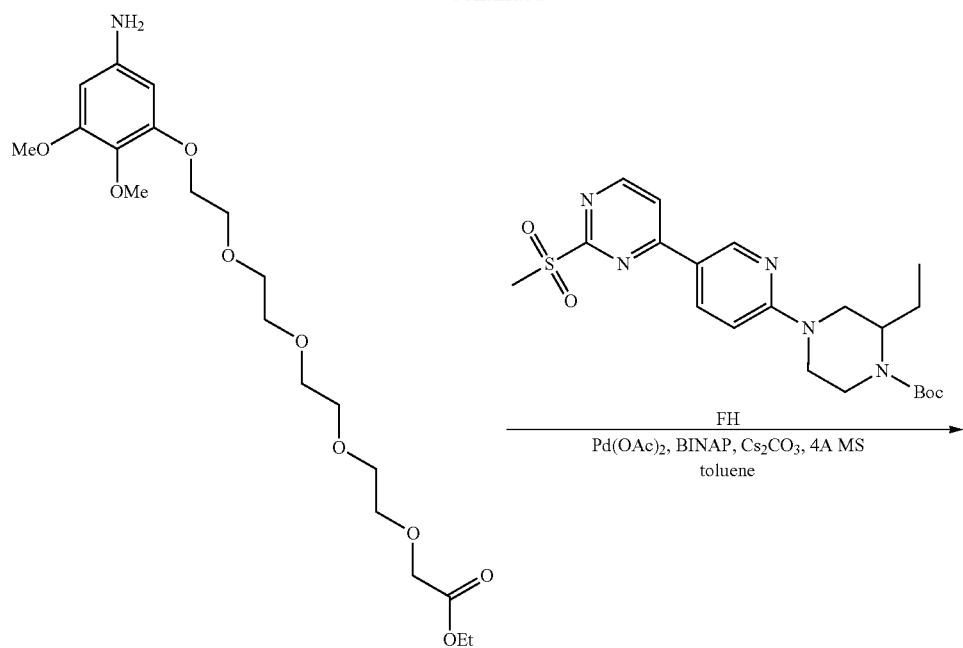
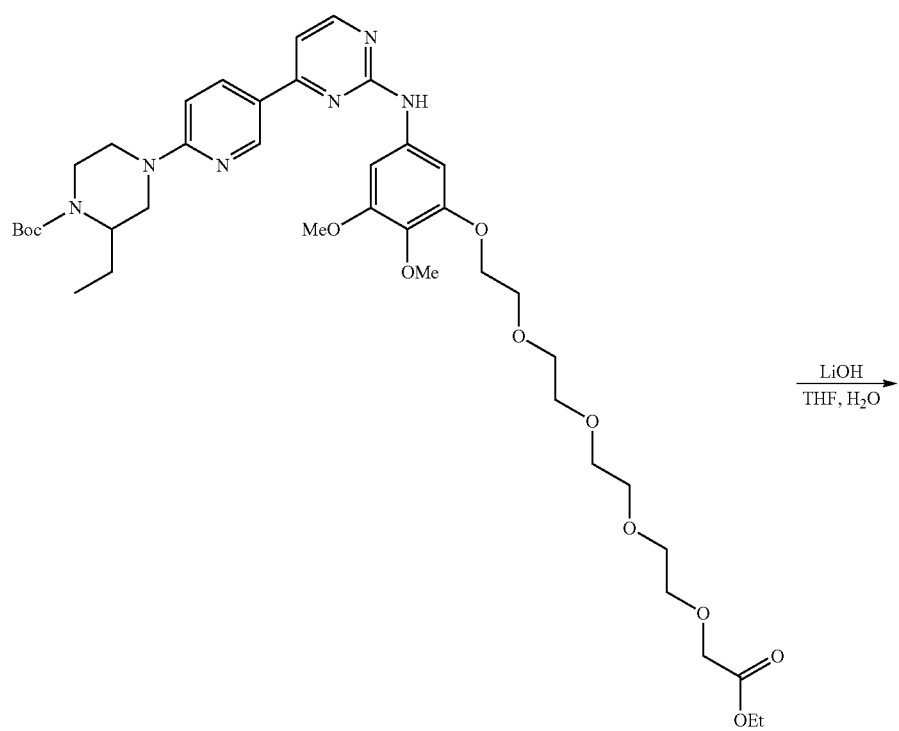

2373
2374
-continued
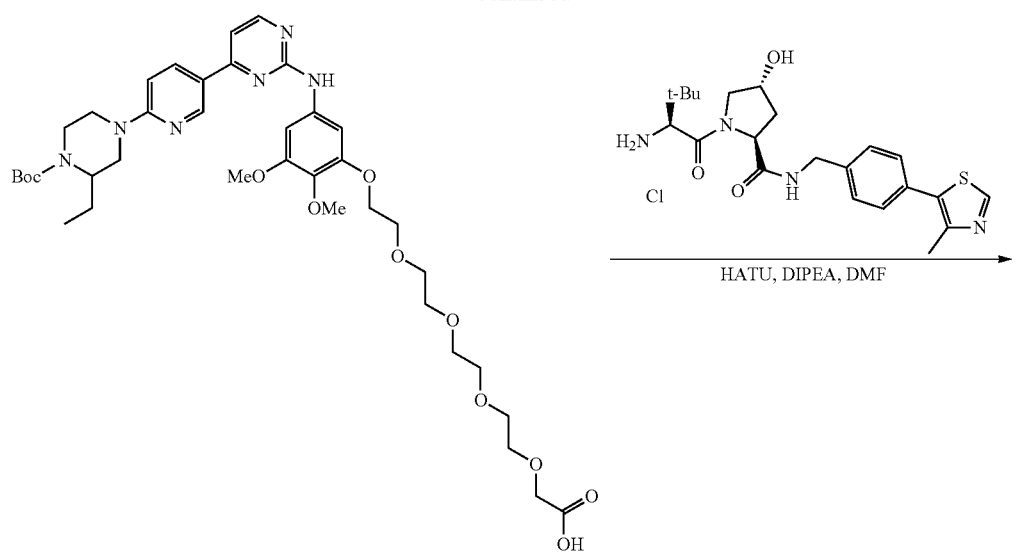
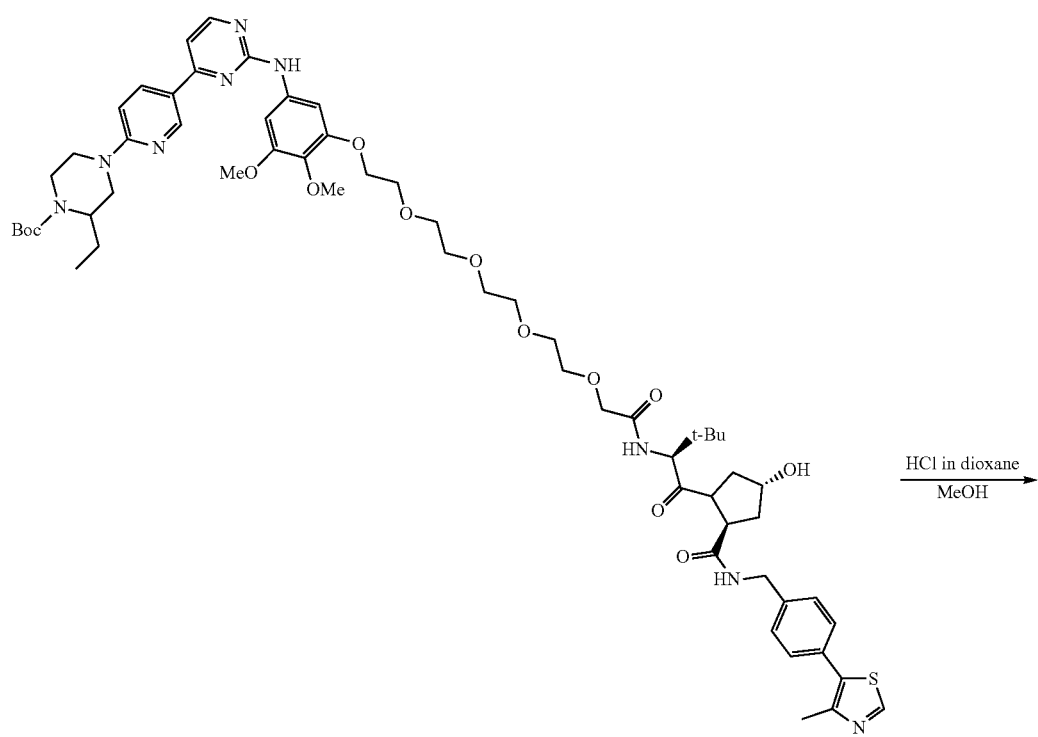

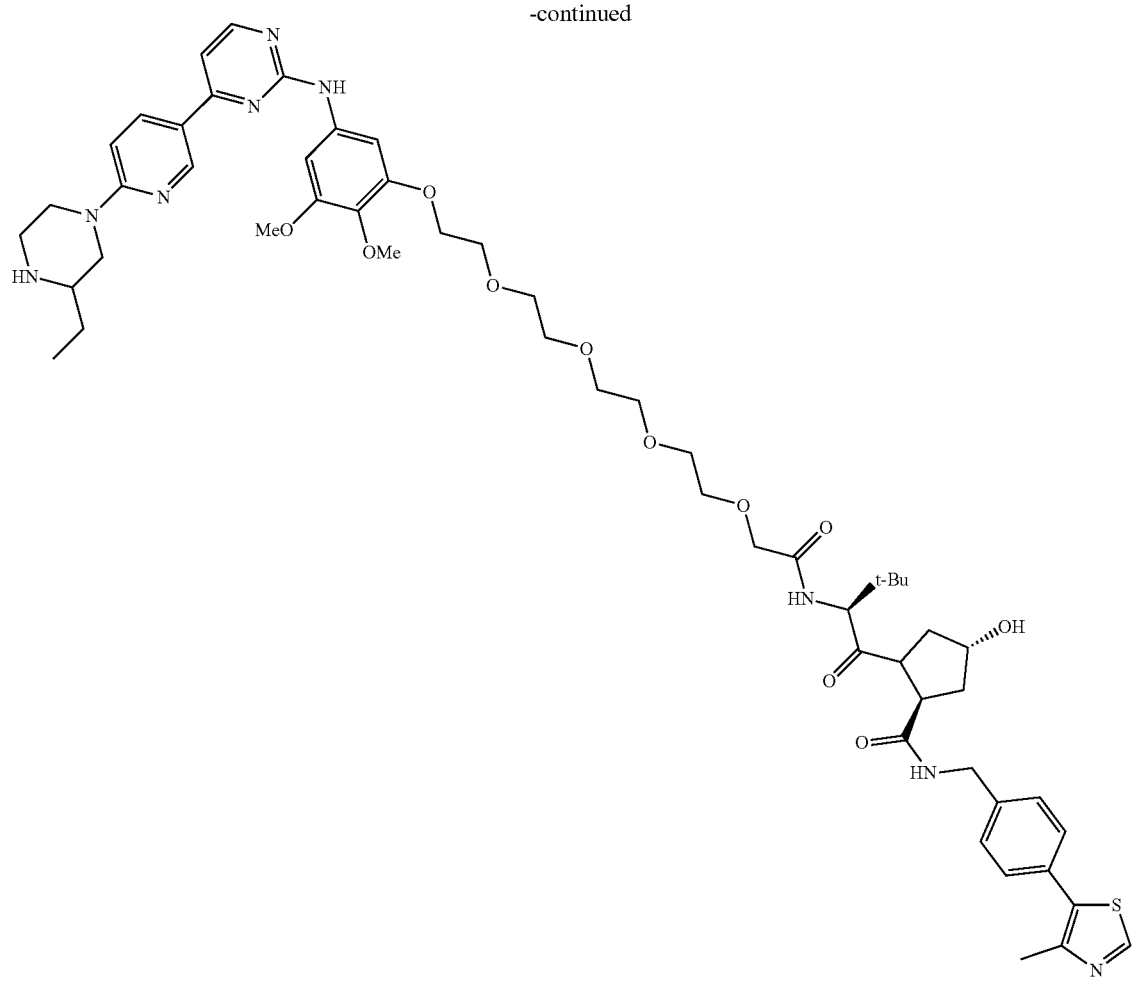

Step 1—Ethyl2-[2-[2-[2-[2-[2-[3-[(8-carbamoyl-5-methylsulfanyl-imidazo[1,2-c]pyrimidin-7-yl)amino]-5-methoxy-phenoxy]ethoxy]ethoxy]ethoxy]ethoxy]ethoxy]acetate To a solution of 2,3-dimethoxy-5-nitro-phenol (510 mg, 2.56 mmol, Intermediate FG) and ethyl 2-[2-[2-[2-(2-methylsulfonyloxyethoxy)ethoxy]ethoxy]ethoxy]acetate (1.10 g, 3.07 mmol, Intermediate BK) in DMF (15 mL) was added $K_2CO_3$ (1.06 g, 7.68 mmol). The mixture was stirred at 50° C. for 12 hours. On completion, the reaction mixture was diluted with water (20 mL) and extracted with DCM (3×30 mL). The combined organic layer was dried over sodium sulfate, filtered and concentrated in vacuo to give a residue. The residue was purified by column chromatography (PE:EA=1:1) to give the title compound (1.10 g, 93% yield) as a light yellow oil. $^1$H NMR (400 MHz, CDCl$_3$) δ 7.55 (d, J=2.4 Hz, 1H), 7.50 (d, J=2.4 Hz, 1H), 4.26-4.16 (m, 4H), 4.13 (s, 2H), 3.95 (s, 3H), 3.92 (s, 3H), 3.90 (m, 2H), 3.74-3.63 (m, 12H), 1.27 (t, J=14.4 Hz, 3H); LC-MS (ESI$^+$) m/z 431.1 (M+18)$^+$.

Step 2—ethyl 2-[2-[2-[2-[2-(5-amino-2,3-dimethoxy-phenoxy)ethoxy]ethoxy]ethoxy]ethoxy]acetate To a solution of ethyl 2-[2-[2-[2-[2-(2,3-dimethoxy-5-nitro-phenoxy)ethoxy]ethoxy]ethoxy]ethoxy]acetate (600 mg, 1.30 mmol) in MeOH (8 mL) was added Pd/C (300 mg, 10 wt %) under nitrogen atmosphere. The suspension was degassed and purged with hydrogen gas three times. The mixture was stirred under hydrogen (15 psi pressure) at rt for 12 hours. On completion, the reaction mixture was filtered and concentrated in vacuo to give the title compound (400 mg, 71% yield) as a red oil. $^1$H NMR (400 MHz, CDCl$_3$) δ 5.97 (s, 1H), 5.94 (s, 1H), 4.26-4.18 (m, 1H), 4.22 (q, J=7.2 Hz, 1H), 4.16-4.09 (m, 4H), 3.87-3.83 (m, 2H), 3.80 (s, 3H), 3.76 (s, 3H), 3.74-3.65 (m, 12H), 1.31-1.27 (t, J=7.2 Hz, 3H); LC-MS (ESI$^+$) m/z 432.1 (M+H)$^+$.

Step 3—Ethyl-2-[2-[2-[2-[2-[2-[3-[[5-[[(1S,2R)-2-(tert-butoxycarbonylamino)cyclohexyl]amino]-8-carbamoyl-imidazo[1,2-c]pyrimidin-7-yl]amino]-5-methoxy-phenoxy]ethoxy]ethoxy]ethoxy]ethoxy]ethoxy]acetate To a solution of ethyl 2-[2-[2-[2-[2-(5-amino-2,3-dimethoxy-phenoxy)ethoxy]ethoxy]ethoxy]ethoxy]acetate (300 mg, 695 umol) and tert-butyl 2-ethyl-4-[5-(2-methylsulfonylpyrimidin-4-yl)-2-pyridyl]piperazine-1-carboxylate (311 mg, 695 umol, Intermediate FH) in toluene (10 mL) was added 4 AMS (600 mg), $Cs_2CO_3$ (679 mg, 2.09 mmol), BINAP (64.9 mg, 104 umol) and Pd(OAc)$_2$ (15.6 mg, 69.5 umol) under nitrogen atmosphere. The suspension was degassed and purged with nitrogen three times. The mixture was stirred at rt for 1 h, and then heated to 100° C. for 12 hours. On completion, the reaction mixture was concentrated under reduced pressure to remove the toluene. The residue was diluted with water (5 mL) and extracted with DCM (3×6 mL). The combined organic layers were dried over sodium sulfate, filtered and concentrated in vacuo to give a residue. The residue was purified by reverse phase chromatography (0.1% FA in water) to give the title compound (400 mg, 72% yield) as a yellowish solid. LC-MS (ESI$^+$) m/z 799.2 (M+H)$^+$.

Step 4—2-[2-[2-[2-[2-[5-[[4-[6-(4-tert-butoxycarbonyl-3-ethyl-piperazin-1-yl)-3-pyridyl]pyrimidin-2-yl]amino]-2,3-dimethoxy-phenoxy]ethoxy]ethoxy]ethoxy]ethoxy]acetic acid To a solution of tert-butyl 4-[5-[2-[3-[2-[2-[2-[2-(2-ethoxy-2-oxo-ethoxy)ethoxy]ethoxy]ethoxy]ethoxy]-4,5-dimethoxy-anilino]pyrimidin-4-yl]-2-pyridyl]-2-ethyl-piperazine-1-carboxylate (200 mg, 250 umol) in THF (6 mL) was added a solution of LiOH (52.5 mg, 1.25 mmol) in H$_2$O (1 mL). The reaction mixture was stirred at rt for 3 hours. On completion, the mixture saturated citric acid aqueous solution (0.3 mL) was added to the mixture to adjust the pH to 5. The residue was diluted with 3 mL water and extracted with DCM (3×5 mL). The combined organic layers were dried over sodium sulfate, filtered and concentrated under reduced pressure to give title compound (193 mg, 100% yield) as a yellowish oil.

Step 5—Tert-butyl 2-ethyl-4-[5-[2-[3-[2-[2-[2-[2-[[(1S)-1-[(2S,4R)-4-hydroxy-2-[[4-(4-methyl thiazol-5-yl)phenyl]methyl carbamoyl]pyrrolidine-1-carbonyl]-2,2-dimethyl-propyl]amino]-2-oxo-ethoxy]ethoxy]ethoxy]ethoxy]ethoxy]-4,5-dimethoxy-anilino]pyrimidin-4-yl]-2-pyridyl]piperazine-1-carboxylate To a solution of 2-[2-[2-[2-[2-[5-[[4-[6-(4-tert-butoxycarbonyl-3-ethyl-piperazin-1-yl)-3-pyridyl]pyrimidin-2-yl]amino]-2,3-dimethoxy-phenoxy]ethoxy]ethoxy]ethoxy]acetic acid (192 mg, 250 umol), (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide (129 mg, 300 umol, Intermediate CI), and DIPEA (96.9 mg, 750 umol) in DMF (5 mL) was added HATU (114 mg, 300 umol) at 0° C. The reaction mixture was then allowed to warm to rt and stirred for 16 hours. On completion, the reaction mixture was concentrated under reduced pressure to remove DMF, then diluted with water (15 mL) and extracted with DCM (3×10 mL). The combined organic layers were dried over sodium sulfate, and concentrated in vacuo to give a residue. The residue was purified by reverse phase chromatography (0.1% FA in water) to give the title compound (210 mg, 71% yield). LC-MS (ESI$^+$) m/z 1183.2 (M+H)$^+$.

Step 6—(2S,4R)-1-[(2S)-2-[[2-[2-[2-[2-[2-[5-[[4-[6-(3-ethylpiperazin-1-yl)-3-pyridyl]pyrimidin-2-yl]amino]-2,3-dimethoxy-phenoxy]ethoxy]ethoxy]ethoxy]ethoxy]acetyl]amino]-3,3-dimethyl-butanoyl]-4-hydroxy-N-[[4-(4-methylthiazol-5-yl)phenyl]methyl]pyrrolidine-2-carboxamide To a solution of tert-butyl 2-ethyl-4-[5-[2-[3-[2-[2-[2-[2-[[(1S)-1-[(2S,4R)-4-hydroxy-2-[[4-(4-methylthiazol-5-yl)phenyl]methyl]carbamoyl]pyrrolidine-1-carbonyl]-2,2-dimethyl-propyl]amino]-2-oxo-ethoxy]ethoxy]ethoxy]ethoxy]ethoxy]-4,5-dimethoxy-anilino]pyrimidin-4-yl]-2-pyridyl]piperazine-1-carboxylate (210 mg, 177 umol) in MeOH (3 mL) was added HCl in dioxane (4 M, 5 mL). Then the mixture was stirred at rt for 15 mins. On completion, the reaction mixture was concentrated under reduced pressure to remove solvent to give a residue. The residue was purified by prep-HPLC (column: Luna C18 150*25 5 u; mobile phase: [water (0.225% FA)-ACN]) to give the title compound I-202 (118 mg, 61% yield). $^1$H NMR (400 MHz, DMSO-d$_6$) δ 9.40 (s, 1H), 8.95 (s, 1H), 8.93 (d, J=1.6 Hz, 1H), 8.61 (J=4.0 Hz, 1H), 8.42 (d, J=5.6 Hz, 1H), 8.32-8.22 (m, 2H), 7.47-7.34 (m, 5H), 7.29 (d, J=5.6 Hz, 1H), 7.25 (d, J=6.4 Hz, 2H), 6.97 (d, J=9.6 Hz, 1H), 4.55 (d, J=9.6 Hz, 1H), 4.47-4.32 (m, 4H), 4.29-4.19 (m, 2H), 4.13-4.04 (m, 2H), 3.94 (s, 2H), 3.81-3.72 (m, 6H), 3.68-3.58 (m, 14H), 3.13-3.04 (m, 1H), 2.98 (m, 1H), 2.83-2.73 (m, 1H), 2.67 (d, J=6.4 Hz, 2H), 2.42 (3H), 2.10-2.01 (m, 1H), 1.94-1.84 (m, 1H), 1.49-1.43 (m, 2H), 1.01-0.85 (m, 12H); LC-MS (ESI$^+$) m/z 1083.2 (M+H)$^+$.

Example 203: PBMC Degradation Assay

Protocol summary of PBMC degradation studies from compound treatment through quantitation.

TABLE 13

| Cell Culture Materials | | |
|---|---|---|
| Reagent | Vendor | Catalogue no. |
| 6 well plate | Falcon | 353046 |
| Frozen PBMCs | AllCells | PB006F, PB005F or PB004F |
| RPMI | Gibco | 11875-093 |
| FBS, certified one-shot | Gibco | A31604-02 |
| Pen/Strep 1000 units/mL | Gibco | 10378016 |
| DMSO | Sigma | D8418-50 mL |
| 2.0 mL centrifuge tubes | Corning | 311-10-051 |
| PBS | Gibco | 10010-023 |

PBMC culture medium: Human peripheral blood mononuclear cells (PBMCs): RPMI+10% FBS (Heat-inactivated)+1% P/S.

TABLE 14

| Lysate preparation and Western Reagents. | | |
|---|---|---|
| Reagent | Vendor | Catalogue no. |
| LDS Sample Buffer (4x) | Life Technologies | NP0008 |
| Reducing Agent (10x) | Invitrogen | NP0009 |
| Molecular Grade diH2O | Corning | 46-000-CV |
| 96 well PCR plate | Eppendorf | 951020346_EA |
| SDS-Page protein gel (4-12% Bis-Tris) 20 well | Invitrogen | WG1402BOX |
| 20x MES running buffer (20x) | Invitrogen | NP0002 |
| TransBlot Turbo RTA Midi LF PVDF transfer kit, for 40 blots | BioRad | 1704275 |
| 10x RIPA buffer | Cell Signaling Technologies | 9806 |
| HALT Protease and Phosphatase Inhibitor Cocktail (100x) | Thermo Scientific | 1861281 |
| Odyssey Blocking buffer (TBS) | Licor | 927-50000 |

TABLE 14-continued

Lysate preparation and Western Reagents.

| Reagent | Vendor | Catalogue no. |
|---|---|---|
| TBST 10x | Cell Signaling Technologies | 9997 |
| Molecular Weight Markers | Licor | 928-40000 |

TABLE 15

Antibodies.

| Antibody | Vendor | Catalogue no. |
|---|---|---|
| IRAK1 | Cell Signaling Technologies | 4504S |
| IRAK4 | Cell Signaling Technologies | 4363S |
| IRAK3 | Cell Signaling Technologies | 4369S |
| MYD88 | Abcam | 133739 |
| Actin | Licor | 926-42212 |
| Goat anti-rabbit IRDye 800CW | Licor | 926-32211 |
| Goat anti-mouse IRDye 680CW | Licor | 926-68070 |

TABLE 16

Equipment.

| Equipment | Vendor | Catalogue no. |
|---|---|---|
| XCell Surelock Midi Cell | Invitrogen | WR0100 |
| TransBlot Turbo transfer system | BioRad | 1704150 |
| Odyssey CLx | Licor | |

Protocol Summary

Frozen human PBMCs were thawed into culture medium.

A cell count/viability assessment by trypan blue exclusion was performed. Cells were cultured at a minimum of $2.5 \times 10^6$ c/mL.

PBMCs were incubated @ 37° C./5% $CO_2$ and allowed to rest overnight.

Following overnight recovery, a cell count/viability assessment by trypan blue exclusion was performed. Cells densities were adjusted back to $2.5 \times 10^6$ c/mL (proceed with plating only if viability >80%).

In a 6 well plate, 2.0 mL of cells were added to each well for a minimum of $5 \times 10^6$ CT per treatment condition. Compounds dilutions were prepared from 20 mM stock and were added at a final 1000x dilution (0.1% DMSO concentration).

At the end of treatment, cells were harvested and spun @ 1800 rpm for 5 min. 1xPBS wash and spun again @ 1800 rpm for 5 min. Cell pellets were frozen and stored at −80° C. until further processing.

Lysates were generated by resuspending in lysis buffer. Protein quantification was performed with a BCA kit. 20 μg of protein were loaded per lane and run on a 26-well 4-12% Bis-Tris SDS-page gel.

Transfers were performed on PVDF membranes using the BioRad Mixed MW turbo program for 7 min.

Membranes were blocked for one hour on a rocker at room temperature.

Primary antibodies were incubated overnight at 4° C. on a rocker.

Membranes were washed 3xTBST, 5 min each.

Secondaries were added and incubated for one hour on a rocker at room temperature.

Membranes were washed 3xTBST, 5 min each and rinsed well with deionized $H_2O$. Membranes were scanned using the Licor Odessey CLx and bands were quantified using Image Studio Lite Version 5.2 software.

PBMC results at 4 hours. The letter codes indicate the percentage of IRAK4 degraded after 4 hours: A (>50% degradation), B (>20-50% degradation) and C (<20% degradation)

TABLE 17

PBMC % IRAK4 Degradation Results.

| Compound Number | PBMC % IRAK4 Degradation |
|---|---|
| I-53 | A |
| I-104 | C |
| I-106 | A |
| I-108 | C |
| I-109 | B |
| I-109 | B |
| I-110 | A |
| I-111 | B |
| I-112 | A |
| I-116 | A |
| I-117 | A |
| I-127 | A |
| I-128 | A |
| I-130 | A |
| I-132 | B |
| I-132 | C |
| I-133 | B |
| I-134 | C |
| I-141 | A |
| I-144 | A |
| I-145 | C |
| I-146 | A |
| I-150 | A |
| I-152 | C |
| I-154 | B |
| I-155 | C |
| I-156 | C |
| I-157 | C |
| I-158 | C |
| I-159 | A |
| I-171 | A |
| I-172 | A |
| I-179 | C |
| I-180 | A |
| I-181 | B |
| I-182 | B |
| I-183 | B |
| I-185 | A |
| I-186 | C |

Example 204: THP-1 and OCI-LY-10 Degradation Assay

Methods

Compound Treatment:

Compounds were reconstituted in DMSO to make stock solutions at concentration of 60 mM. THP-1 and OCI-LY10 cells were maintained in RPMI-1640 medium containing 10% FBS, 0.5 μM 2-ME or 20% FBS, 55 μM 2-ME, and 1% L-Glutamine respectively.

Cells were seeded into 6-well plates with 5e6 cells per well. 200 μL of diluted compounds were added to cells to the final concentration of 0.003-10 μM. After 4 or 24 hour-incubation at 37° C., cells were collected into 2 mL Eppendorf tubes and centrifuged at 1,000 rpm for 5 min. The cell pellets were washed with 1×DPBS once and resuspended in 60 μL lysis buffer. The cells were lysed on ice for 10 min, then centrifuged at 14,000 rpm for 10 min at 4° C. and the supernatants were collected for western blots. For THP-1 cells, the lysis buffer contained 40 mM pH 7.4 HEPES, 140 mM NaCl, 2.5 mM EDTA, 1% NP-40, 0.1% SDS, and protease inhibitor cocktail (Roche, Cat. No. 05892791001). For OCI-LY10 cells, RIPAbuffer (Thermo Fisher, 89900) with Halt Protease and Phosphatase Inhibitor Cocktail (Thermo Fisher, 78446) was applied.

Protein Concentration Determination:

The protein concentration of cell lysates was quantified with Pierce™ BCA Protein Assay Kit (Pierce, 23227). Albumin standards at different concentrations were prepared, involving 2,000 ug/mL, 1,500 ug/mL, 1,000 ug/mL, 750 ug/mL, 500 ug/mL, 250 ug/mL, 125 ug/mL, and 25 ug/mL. BCA working reagents were prepared by mixing BCA reagent A with reagent B in 50:1 ratio. 200 μL of the BCA working reagents were added to 25 μL of BCA standard or cell lysates in microplate, and mixed thoroughly on a plate shaker for 30 seconds. After incubation at 37° C. for 30 min, the absorbance of samples at 562 nm were measured with EnVision Plate Reader.

Western Blot Assay:

Protein lysates were prepared in NuPAGE™ LDS sample buffer and NuPAGE™ sample reducing agent, and incubated at 95° C. for 5 min. For western blots, 20-25 μg of total proteins were resolved in 4-12% Bis-Tris gels (Introgen, WG1403A) or 10% Bis-Tris Midi gels (Invitrogen, WG1202BOX) running with 1×MOPS SDS running buffer (Invitrogen, NP0001) or 1×MES SDS running buffer (Invitrogen, NP0002). The proteins were transferred to low fluorescence PVDF membranes using the Trans-Blot Turbo Transfer System. Membranes were then blocked in Odyssey blocking buffer at RT for 1 h followed by primary incubation at 4° C. overnight. The primary antibodies were IRAK1 rabbit monoclonal antibody (CST, #4504S, 1:500), IRAK3 rabbit polyclonal antibody (CST, #4369, 1:500), IRAK4 rabbit polyclonal antibody (CST, #4363S, 1:1,000), MyD88 rabbit monoclonal antibody (Abcam, Ab133739, 1:2,000), j3-actin mouse monoclonal antibody (Sigma, A5441, 10,000), and Gapdh mouse monoclonal antibody (Millipore, MAB374, 1:5,000). Membranes were washed three times with 1×TBST, and then incubated with IR Dye 800 CW Goat anti-rabbit (Licor, #926-32211) and IR Dye 700 CW Goat anti-mouse (Licor, #926-68070) secondary antibodies in 1:10,000 dilution at RT for 1 h. The western blot images were obtained using Odyssey Imaging System.

THP-1 results at 24 hours. The letter codes indicate the percentage of IRAK4 degraded after 24 hours: A (>50% degradation), B (>20-50% degradation) and C (<20% degradation)

TABLE 18

THP-1 % IRAK4 Degradation Results.

| Compound Name | THP-1 24 h % IRAK4 Degradation |
|---|---|
| I-1 | B |
| I-2 | C |
| I-3 | C |
| I-4 | A |
| I-5 | B |
| I-6 | B |
| I-7 | B |
| I-8 | C |
| I-10 | C |

TABLE 18-continued

THP-1 % IRAK4 Degradation Results.

| Compound Name | THP-1 24 h % IRAK4 Degradation |
|---|---|
| I-11 | C |
| I-12 | C |
| I-13 | C |
| I-14 | C |
| I-15 | A |
| I-16 | C |
| I-19 | C |
| I-25 | B |
| I-30 | C |
| I-40 | C |
| I-43 | C |
| I-47 | B |
| I-48 | B |
| I-49 | B |
| I-50 | B |
| I-51 | C |
| I-52 | C |
| I-55 | C |
| I-58 | C |
| I-96 | C |
| I-97 | B |
| I-98 | B |
| I-99 | C |
| I-100 | B |
| I-119 | B |
| I-120 | C |
| I-122 | C |
| I-162 | A |
| I-163 | C |
| I-164 | C |
| I-165 | C |
| I-189 | C |
| I-194 | C |
| I-195 | C |
| I-198 | C |
| I-199 | C |
| I-200 | C |
| I-203 | B |

OCI-LY-10 results at 4 hours. The letter codes indicate the percentage of IRAK4 degraded after 4 hours: A (>50% degradation), B (>20-50% degradation) and C (<20% degradation)

TABLE 19

OCI-LY-10 % IRAK4 Degradation Results.

| Compound Name | OCI-LY10 % IRAK4 Degradation |
|---|---|
| I-9 | C |
| I-17 | C |
| I-18 | B |
| I-21 | C |
| I-22 | C |
| I-26 | C |
| I-27 | C |
| I-29 | C |
| I-31 | C |
| I-32 | C |
| I-33 | C |
| I-34 | C |
| I-35 | C |
| I-36 | C |
| I-37 | C |
| I-38 | C |
| I-39 | C |
| I-41 | C |
| I-42 | C |
| I-44 | B |
| I-45 | C |
| I-46 | C |

TABLE 19-continued

OCI-LY-10 % IRAK4 Degradation Results.

| Compound Name | OCI-LY10 % IRAK4 Degradation |
| --- | --- |
| I-54 | C |
| I-56 | C |
| I-57 | C |
| I-59 | C |
| I-60 | C |
| I-61 | C |
| I-62 | C |
| I-63 | C |
| I-64 | C |
| I-65 | C |
| I-66 | C |
| I-67 | C |
| I-68 | C |
| I-69 | C |
| I-70 | C |
| I-71 | C |
| I-72 | C |
| I-73 | C |
| I-74 | C |
| I-75 | C |
| I-76 | C |
| I-77 | C |
| I-78 | C |
| I-79 | C |
| I-80 | C |
| I-81 | C |
| I-82 | C |
| I-83 | C |
| I-84 | C |
| I-85 | C |
| I-86 | C |
| I-87 | C |
| I-88 | C |
| I-89 | C |
| I-90 | B |
| I-91 | C |
| I-92 | A |
| I-93 | C |
| I-94 | B |
| I-95 | C |
| I-101 | C |
| I-102 | C |
| I-103 | C |
| I-105 | A |
| I-107 | C |
| I-113 | C |
| I-114 | C |
| I-115 | B |
| I-118 | C |
| I-121 | C |
| I-123 | C |
| I-124 | C |
| I-125 | C |
| I-126 | B |
| I-129 | C |
| I-131 | C |
| I-135 | B |
| I-136 | B |
| I-137 | B |
| I-138 | A |
| I-139 | B |
| I-140 | B |
| I-142 | B |
| I-143 | B |
| I-147 | A |
| I-148 | B |
| I-149 | A |
| I-151 | A |
| I-153 | C |
| I-160 | C |
| I-161 | C |
| I-169 | C |
| I-170 | B |
| I-173 | C |
| I-174 | C |
| I-175 | C |
| I-176 | C |
| I-177 | C |
| I-178 | C |
| I-184 | C |
| I-187 | B |
| I-188 | C |
| I-204 | C |
| I-205 | C |
| I-207 | C |
| I-208 | C |
| I-209 | C |
| I-210 | A |

OCI-LY-10 results at 4 hours. The letter codes for % IRAK4 degradation indicate the percentage of IRAK4 degraded after 4 hours across three different concentrations: A (>50% degradation), B (>20-50% degradation) and C (<20% degradation).

TABLE 19a

OCI-LY-10 % IRAK4 Degradation

| Compound Name | OCI-LY10 % IRAK4 Degradation (0.01 uM) | OCI-LY10 % IRAK4 Degradation (0.1 uM) | OCI-LY10 % IRAK4 Degradation (1 uM) |
| --- | --- | --- | --- |
| I-210 | C | B | A |
| I-211 | B | B | B |
| I-212 | B | A | A |
| I-215 | A | A | A |
| I-219 | A | A | A |
| I-220 | B | B | B |
| I-221 | B | B | A |
| I-222 | A | A | A |
| I-224 | B | A | A |
| I-225 | C | A | A |
| I-226 | B | A | A |
| I-227 | B | A | A |
| I-228 | A | A | A |
| I-229 | C | C | C |
| I-230 | C | C | C |
| I-231 | A | A | A |
| I-233 | C | A | A |
| I-234 | C | B | B |
| I-235 | C | A | A |
| I-236 | C | B | A |
| I-238 | C | B | A |
| I-239 | C | C | C |
| I-240 | B | B | B |
| I-241 | B | A | A |
| I-242 | B | A | A |
| I-243 | C | C | C |
| I-244 | C | B | B |
| I-245 | C | B | A |
| I-246 | C | A | A |
| I-247 | B | A | A |
| I-248 | B | A | A |
| I-249 | C | A | A |
| I-250 | C | A | A |
| I-252 | B | A | A |
| I-254 | C | C | B |
| I-255 | C | C | C |
| I-256 | B | A | A |
| I-257 | C | C | C |
| I-258 | C | B | C |
| I-259 | C | C | C |
| I-260 | C | C | C |
| I-262 | C | B | B |
| I-263 | C | C | C |

TABLE 19a-continued

OCI-LY-10 % IRAK4 Degradation

| Compound Name | OCI-LY10 % IRAK4 Degradation (0.01 uM) | OCI-LY10 % IRAK4 Degradation (0.1 uM) | OCI-LY10 % IRAK4 Degradation (1 uM) |
|---|---|---|---|
| I-264 | C | C | C |
| I-265 | B | A | A |
| I-266 | C | A | A |
| I-267 | C | A | B |
| I-269 | C | B | A |
| I-270 | C | B | A |
| I-272 | C | B | A |
| I-275 | C | B | A |
| I-276 | C | B | A |
| I-277 | C | A | A |
| I-278 | C | B | A |
| I-279 | C | A | A |
| I-281 | C | A | A |
| I-282 | C | C | C |
| I-283 | A | A | A |
| I-284 | C | C | C |
| I-285 | C | C | B |
| I-287 | C | C | B |
| I-288 | C | C | A |
| I-290 | B | B | B |
| I-297 | C | C | C |
| I-302 | B | A | A |
| I-303 | B | A | A |
| I-304 | C | C | C |
| I-305 | A | A | A |
| I-306 | C | B | B |
| I-307 | C | C | C |
| I-308 | B | A | A |
| I-309 | B | A | A |
| I-310 | C | A | A |
| I-311 | C | A | A |
| I-312 | C | A | A |
| I-313 | C | B | C |
| I-313 | B | A | A |
| I-314 | C | B | B |
| I-315 | C | C | B |
| I-316 | B | B | B |
| I-317 | C | C | B |
| I-318 | C | A | B |
| I-319 | B | A | A |
| I-320 | C | B | B |
| I-321 | B | A | A |
| I-322 | C | C | A |
| I-323 | B | A | A |
| I-324 | B | A | B |
| I-325 | B | A | A |
| I-326 | B | C | C |
| I-327 | C | B | A |
| I-328 | A | A | A |
| I-329 | B | A | A |
| I-330 | C | A | A |
| I-331 | C | B | C |
| I-332 | A | A | A |
| I-333 | C | C | C |
| I-335 | C | C | A |
| I-336 | C | C | B |
| I-337 | C | A | A |
| I-338 | C | B | B |
| I-339 | C | B | A |
| I-340 | C | A | A |
| I-341 | C | A | A |
| I-342 | C | B | A |
| I-343 | C | B | A |
| I-344 | C | A | A |
| I-345 | C | A | A |
| I-346 | B | A | A |
| I-347 | C | A | A |
| I-348 | C | C | A |
| I-349 | C | B | A |
| I-350 | C | C | B |
| I-351 | C | C | A |
| I-352 | C | C | C |
| I-353 | C | C | C |
| I-354 | C | A | A |
| I-355 | B | B | C |
| I-356 | C | C | C |
| I-357 | C | C | C |
| I-358 | C | C | C |
| I-359 | C | C | C |
| I-360 | B | C | C |
| I-361 | C | C | C |
| I-362 | C | B | A |
| I-363 | C | C | C |
| I-364 | C | C | C |
| I-365 | C | C | C |
| I-366 | C | C | C |
| I-367 | B | B | A |
| I-369 | B | B | B |
| I-370 | C | B | B |
| I-371 | C | C | B |
| I-372 | C | C | C |
| I-372 | C | C | C |
| I-374 | C | B | B |
| I-375 | B | B | B |
| I-376 | B | A | A |
| I-377 | C | C | B |
| I-378 | C | C | A |
| I-380 | C | C | C |
| I-381 | B | A | A |
| I-382 | C | C | B |
| I-383 | C | C | A |
| I-385 | C | B | B |
| I-386 | C | B | A |
| I-387 | C | C | B |
| I-389 | C | C | A |
| I-392 | B | A | A |
| I-393 | C | A | A |
| I-394 | C | A | A |
| I-395 | C | B | B |
| I-397 | B | A | A |
| I-424 | B | B | B |
| I-425 | B | A | A |
| I-426 | C | C | C |
| I-427 | B | A | A |
| I-434 | C | C | C |
| I-435 | C | C | C |

Example 204a: OCI-LY-10 $DC_{50}$

A MSD assay was run to determine the concentration of compound required to degrade 50% of protein ($DC_{50}$).

MSD Assay $DC_{50}$ Protocol

Day 1

Compounds were reconstituted to 10 mM in stock solutions. The stock solutions were diluted to 5 mM and 45 µL of each dilution was transferred to a 384 pp-plate. A 3 fold, 8-point serial dilution was performed by transferring 15 µL of compound into 30 µL DMSO using Janus.

20 nL of each compounds were added into each well of a 96-well plate (Corning3799).

OCI-Ly10 cells were seeded into the 96-well plate at $3.0*10e^5$ cells/100 µL/well.

The cell plate was shaken at 720 rpm for 5 min and incubated for 4 hr.

The 100 µL of cells were transferred into the 96-PCR plate and spun down at high speed for 5 mins.

The supernatant was discarded and 100 µL of RIPA lysis buffer with proteinase inhibitors was added per well. The plate was then sealed and shaken at 600 rpm and 4° C. for about 20 min.

The plate was then spun down at high speed (about 3200 g) for 30 min and then frozen in a −80° C. fridge.

A bare MSD plate (L15XA-3) was coated with 2 μg/mL of capture antibody (mouse Anti-IRAK4 antibody [2H9], ab119942) in PBS to 40 μL/well and incubated overnight at 4° C.

Day 2

The MSD coated plate was washed 3× (150 μL/well) with 1×TBST (CST #9997S).

The MSD plate was then blocked with 150 μL of blocking buffer [3% Blocker A (MSD, R93BA-4) in TBST]/well and shaken for 1 hr at R$^\dagger$ and 600 rpm.

The MSD plate was washed 3× (150 μL/well) with 1×TBST. The sample RIPA lysates were then added to the MSD plate (50 μL/well) and shaken for 1 hr at R$^\dagger$ and 600 rpm.

The MSD plate was washed 3× (150 μL/well) with 1×TBST and the primary detection antibody (Rabbit Anti-IRAK4 antibody [Y279], ab32511) was added to a final concentration of 1 μg/ml with 25 μL/well. The plate was then shaken for 1 hr at RT and 600 rpm.

The MSD plate was washed 3× (150 μL/well) with 1×TBST and the secondary detection antibody, SULFO-TAG anti-species antibody (Anti Rabbit Antibody (R32AB-5) MSD, R32AB-1) was added to a volume of 25 μL/well at a final concentration of 1 jag/ml. The plate was then shaken for 1 hr at RT and 600 rpm.

The MSD plate was then washed 3× (150 μL/well) with 1×TBST.

lx MSD reading buffer was then added (150 μL/well) and the plate was diluted with 4× water. (MSD, R92TC-2)

The MSD instrument was then read.

Data Analysis

The remaining activity was calculated following the formula below:

Calculate

The DC$_{50}$ was calculated by fitting the Curve using Xlfit (v5.3.1.3), equation 201:

$$Y=Bottom+(Top-Bottom)/(1+10^{\wedge}((Log\ IC50-X)*HillSlope))$$

OCI-LY-10 DC$_{50}$ results. The letter codes for IRAK4 DC$_{50}$ indicate the concentration of compound required to degrade 50% of protein: A (<0.05 μM), B (0.05-0.1 μM), C (0.1-0.5 μM), D (0.5-1.0 μM), and E (>1.0 μM).

TABLE 19b

OCI-LY-10 % IRAK4 DC$_{50}$ Results

| Compound Name | OCI-LY10 IRAK4 DC$_{50}$ (μM) |
|---|---|
| I-213 | A |
| I-214 | E |
| I-218 | E |
| I-219 | A |
| I-224 | A |
| I-225 | A |
| I-227 | A |
| I-228 | A |
| I-231 | A |
| I-235 | B |
| I-240 | E |
| I-241 | A |
| I-242 | A |
| I-251 | A |
| I-252 | A |
| I-253 | A |
| I-255 | E |
| I-258 | E |
| I-261 | C |
| I-262 | E |
| I-265 | A |
| I-266 | A |
| I-267 | B |
| I-268 | A |
| I-269 | A |
| I-270 | C |
| I-271 | C |
| I-272 | C |
| I-273 | B |
| I-274 | C |
| I-276 | B |
| I-277 | B |
| I-278 | B |
| I-279 | B |
| I-280 | A |
| I-281 | B |
| I-283 | A |
| I-284 | E |
| I-286 | E |
| I-287 | E |
| I-288 | B |
| I-289 | E |
| I-290 | E |
| I-292 | E |
| I-293 | E |
| I-294 | E |
| I-295 | E |
| I-296 | E |
| I-297 | E |
| I-299 | E |
| I-300 | E |
| I-301 | E |
| I-302 | A |
| I-305 | A |
| I-308 | B |
| I-313 | A |
| I-319 | A |
| I-320 | E |
| I-321 | A |
| I-332 | A |
| I-334 | B |
| I-344 | B |
| I-350 | E |
| I-351 | C |
| I-352 | E |
| I-360 | E |
| I-366 | E |
| I-371 | E |
| I-381 | A |
| I-384 | D |
| I-386 | C |
| I-387 | E |
| I-389 | D |
| I-390 | C |
| I-391 | C |
| I-392 | B |
| I-393 | C |
| I-394 | C |
| I-395 | E |
| I-396 | B |
| I-397 | A |
| I-398 | C |
| I-399 | A |
| I-400 | A |
| I-401 | A |
| I-402 | E |
| I-403 | B |
| I-404 | A |
| I-405 | A |
| I-405 | A |
| I-406 | A |
| I-407 | A |

TABLE 19b-continued

OCI-LY-10 % IRAK4 DC$_{50}$ Results

| Compound Name | OCI-LY10 IRAK4 DC$_{50}$ (μM) |
|---|---|
| I-408 | E |
| I-411 | A |
| I-412 | E |
| I-413 | E |
| I-414 | C |
| I-415 | E |
| I-416 | E |
| I-417 | E |
| I-419 | C |
| I-420 | E |
| I-421 | C |
| I-422 | E |
| I-423 | E |
| I-427 | A |
| I-428 | A |
| I-429 | E |
| I-432 | E |
| I-436 | E |
| I-437 | E |
| I-438 | E |
| I-440 | E |
| I-441 | E |
| I-442 | E |
| I-444 | B |
| I-445 | B |
| I-446 | C |
| I-447 | B |
| I-449 | E |
| I-456 | E |
| I-459 | A |
| I-460 | A |
| I-461 | A |
| I-462 | A |
| I-463 | E |
| I-470 | A |
| I-472 | E |
| I-473 | A |
| I-475 | A |
| I-476 | A |
| I-477 | A |
| I-478 | B |
| I-479 | A |
| I-487 | A |
| I-488 | A |
| I-489 | A |
| I-490 | A |
| I-491 | B |
| I-495 | A |
| I-504 | A |
| I-506 | A |
| I-508 | A |
| I-509 | A |
| I-513 | A |
| I-514 | A |
| I-517 | A |
| I-522 | E |
| I-523 | B |
| I-524 | E |
| I-525 | E |
| I-529 | B |
| I-530 | A |
| I-532 | A |
| I-534 | A |
| I-535 | A |
| I-536 | A |
| I-537 | A |
| I-539 | D |
| I-542 | A |
| I-543 | A |
| I-545 | A |
| I-548 | A |
| I-549 | A |
| I-550 | A |
| I-551 | A |
| I-552 | A |
| I-553 | D |
| I-554 | E |
| I-555 | D |
| I-556 | D |
| I-558 | A |
| I-559 | E |
| I-564 | C |
| I-567 | A |
| I-568 | A |
| I-572 | A |
| I-574 | A |
| I-576 | A |
| I-579 | C |
| I-580 | B |
| I-583 | A |
| I-584 | A |
| I-585 | A |
| I-587 | A |
| I-588 | A |
| I-589 | A |
| I-590 | A |
| I-592 | A |
| I-593 | A |
| I-599 | C |
| I-614 | B |
| I-692 | E |
| I-684 | A |
| I-685 | A |
| I-699 | C |
| I-700 | A |
| I-689 | A |
| I-690 | A |
| I-519 | D |
| I-520 | D |
| I-521 | E |
| I-680 | E |
| I-681 | D |
| I-682 | E |

Example 204b: OCI-LY-10 EC$_{50}$

A CTG cell viability assay using OCI-LY-10 cells was run to determine compound-mediated cell viability (EC$_{50}$).

Cell Viability Protocol

Compound-mediated viability effect on OCI-LY10 was quantitatively determined using the CellTiter-Glo® Luminescent Cell Viability Assay kit from Promega (Catalog number G7570) following manufacturer's recommended procedures. Briefly, OCI-LY10 cells were seeded into 384 well plates (Grenier Bio-One, Catalog number 781080) with a density of 10,000 cells per well. Compounds were then added to the assay plate with final top concentration of 10 μM and 1:3 dilution series with total of 9 doses. The final DMSO concentration was normalized to 0.2%. The assay plates were incubated at 37° C. for 4 days under 5% CO$_2$. Then the assay plate was equilibrated at room temperature for 10 minutes. To determine cell viability, 30 μL CellTiter Glo reagent was added to each well and the assay plate was centrifuged at 1000 rpm for 30 second, incubated at room temperature for 10 min, and analyzed by detecting the luminescence using a multimode plate reader (EnVision 2105, PerkinElmer). The data was then analyzed by software Prism 7.0 from GraphPad and the dose response curves were fit using a three-parameter logistic equation to calculate EC$_{50}$.

OCI-LY-10 EC$_{50}$ results. The letter codes for IRAK4 EC$_{50}$ indicate the concentration of compound required to affect 50% of cells: A (<0.05 μM), B (0.05-0.1 μM), C (0.1-0.5 μM), D (0.5-1.0 μM), and E (>1.0 μM).

TABLE 19c

OCI-LY-10 IRAK4 EC$_{50}$ Results

| Compound Name | OCI-LY10 IRAK4 EC$_{50}$ (μM) |
|---|---|
| I-448 | C |
| I-449 | E |
| I-455 | E |
| I-456 | E |
| I-457 | E |
| I-458 | B |
| I-459 | A |
| I-460 | A |
| I-461 | A |
| I-462 | A |
| I-463 | E |
| I-464 | E |
| I-465 | E |
| I-466 | E |
| I-467 | E |
| I-468 | E |
| I-469 | E |
| I-470 | A |
| I-471 | E |
| I-472 | E |
| I-473 | B |
| I-475 | A |
| I-476 | C |
| I-477 | A |
| I-478 | C |
| I-479 | A |
| I-481 | B |
| I-482 | C |
| I-483 | E |
| I-484 | E |
| I-485 | E |
| I-487 | B |
| I-488 | A |
| I-489 | D |
| I-490 | A |
| I-491 | A |
| I-494 | E |
| I-495 | D |
| I-504 | A |
| I-506 | A |
| I-508 | B |
| I-509 | A |
| I-513 | A |
| I-514 | A |
| I-515 | D |
| I-517 | E |
| I-522 | E |
| I-523 | A |
| I-524 | E |
| I-525 | E |
| I-526 | E |
| I-527 | E |
| I-528 | E |
| I-529 | B |
| I-530 | A |
| I-531 | A |
| I-532 | D |
| I-533 | D |
| I-534 | E |
| I-535 | E |
| I-536 | A |
| I-537 | A |
| I-538 | E |
| I-539 | A |
| I-540 | A |
| I-541 | E |
| I-542 | A |
| I-543 | A |
| I-544 | E |
| I-545 | A |
| I-548 | A |

TABLE 19c-continued

OCI-LY-10 IRAK4 EC$_{50}$ Results

| Compound Name | OCI-LY10 IRAK4 EC$_{50}$ (μM) |
|---|---|
| I-549 | A |
| I-550 | A |
| I-551 | A |
| I-552 | A |
| I-553 | E |
| I-555 | E |
| I-556 | E |
| I-558 | A |
| I-559 | D |
| I-560 | E |
| I-563 | E |
| I-564 | E |
| I-567 | D |
| I-568 | C |
| I-572 | C |
| I-573 | E |
| I-574 | A |
| I-575 | C |
| I-576 | A |
| I-578 | D |
| I-579 | E |
| I-580 | A |
| I-581 | C |
| I-582 | A |
| I-583 | A |
| I-584 | B |
| I-585 | A |
| I-587 | A |
| I-588 | A |
| I-589 | A |
| I-590 | A |
| I-592 | A |
| I-593 | C |
| I-595 | B |
| I-596 | E |
| I-597 | C |
| I-598 | A |
| I-599 | A |
| I-614 | C |
| I-617 | D |
| I-691 | E |
| I-692 | E |
| I-694 | E |
| I-684 | A |
| I-685 | A |
| I-699 | A |
| I-700 | B |
| I-688 | E |
| I-689 | D |
| I-690 | E |
| I-519 | D |
| I-520 | E |
| I-521 | E |
| I-680 | E |
| I-682 | E |

TABLE 20

Compounds synthesized via Method 11 with the addition of various amines to fluoride Intermediate R in Step 1, followed by coupling with various acids in Step 3.

| Ex-# | I-# | Step 1 Intermediate Amine | Step 3 Intermediate Acid | LCMS (ES+) m/z (M + H)+ | 1HNMR (400 MHz, DMSO-d$_6$) δ |
|---|---|---|---|---|---|
| 205[a] | I-210 | FQ | EG | 905.0 | 11.10 (s, 1H), 9.98 (s, 1H), 9.04-8.95 (m, 2H), 8.65 (t, J = 5.2 Hz, 1H), 8.16 (d, J = 5.2 Hz, 1H), 8.05-8.00 (m, 4H), 7.66 (s, 1H), 7.58 (t, J = 7.6 Hz, 1H), 7.20-7.15 (m, 2H), 7.13-7.07 (m, 2H), 7.04 (d, J = 6.8 Hz, 2H), 6.88 (t, J = 5.6 Hz, 1H), 5.05 (dd, J = 5.4, 12.8 Hz, 1H), 4.37 (d, J = 5.6 Hz, 2H), 4.00 (t, J = 6.8 Hz, 2H), 3.26-3.25 (m, 2H), 3.18 (t, J = 6.0 Hz, 2H), 2.94-2.83 (m, 1H), 2.60-2.54 (m, 2H), 2.05-1.94 (m, 3H), 1.10-1.02 (m, 1H), 0.48-0.43 (m, 2H), 0.24-0.21 (m, 2H) |
| 206 | I-211 | tert-butyl N-[2-(2-aminoethoxy)-ethyl]carbamate CAS# 127828-22-2) | FX | 837.5 | 11.08 (s, 1H), 10.03 (s, 1H), 8.98 (s, 1H), 8.91 (s, 1H), 8.62 (t, J = 5.6 Hz, 1H), 8.16 (d, J = 5.2 Hz, 1H), 8.04-7.92 (m, 4H), 7.59-7.53 (m, 1H), 7.47-7.18 (m, 1H), 7.17-7.00 (m, 5H), 6.63 (t, J = 5.6 Hz, 1H), 5.10-4.98 (m, 1H), 3.69-3.63 (m, 2H), 3.63-3.58 (m, 2H), 3.53-3.43 (m, 4H), 3.19 (t, J = 6.0 Hz, 2H), 2.95-2.79 (m, 1H), 2.61-2.52 (m, 2H), 2.08-1.96 (m, 1H), 1.12-1.01 (m, 1H), 0.49-0.42 (m, 2H), 0.27-0.19 (m, 2H) |
| 207 | I-212 | tert-butyl N-[2-[2-[2-[2-(2-aminoethoxy)-ethoxy]-ethoxy]ethoxy]-ethyl]carbamate (CAS# 811442-84-9) | FX | 991.0 (M + 23)+ | 11.08 (s, 1H), 10.03 (s, 1H), 8.98 (s, 1H), 8.92 (s, 1H), 8.63 (t, J = 5.2 Hz, 1H), 8.16 (d, J = 5.2 Hz, 1H), 8.07-7.95 (m, 4H), 7.61-7.53 (m, 1H), 7.47-7.17 (m, 1H), 7.15-7.06 (m, 3H), 7.06-7.00 (m, 2H), 6.59 (t, J = 5.6 Hz, 1H), 5.05 (dd, J = 5.6, 12.8 Hz, 1H), 3.63-3.58 (m, 2H), 3.56-3.48 (m, 14H), 3.47-3.42 (m, 4H), 3.18 (t, J = 6.0 Hz, 2H), 2.94-2.82 (m, 1H), 2.63-2.52 (m, 2H), 2.06-1.97 (m, 1H), 1.12-1.02 (m, 1H), 0.50-0.41 (m, 2H), 0.27-0.20 (m, 2H) |
| 208 | I-213 | KN | DF | 888.5 | 11.10 (s, 1H), 11.01 (s, 1H), 9.04 (s, 1H), 9.02 (s, 1H), 8.63 (t, J = 5.2 Hz, 1H), 8.17 (d, J = 5.2 Hz, 1H), 8.14 (s, 1H), 8.08 (d, J = 8.8 Hz, 2H), 8.03 (d, J = 8.8 Hz, 2H), 7.79 (s, 1H), 7.57 (dd, J = 7.2, 8.4 Hz, 1H), 7.18 (t, J = 5.2 Hz, 1H), 7.15-7.09 (m, 2H), 7.06-6.99 (m, 2H), 6.60 (t, J = 5.2 Hz, 1H), 5.06 (dd, J = 5.2, 12.8 Hz, 1H), 3.53 (t, J = 5.2 Hz, 2H), 3.53-3.47 (m, 8H), 3.20 (t, J = 6.0 Hz, 2H), 2.93-2.83 (m, 1H), 2.63-2.53 (m, 2H), 2.09-1.98 (m, 1H), 1.79-1.72 (m, 2H), 1.13-1.00 (m, 1H), 0.49-0.42 (m, 2H), 0.25-0.21 (m, 2H) |
| 209 | I-214 | tert-butyl N-[2-[2-[2-[2-[2-(2-aminoethoxy)ethoxy]-ethoxy]ethoxy]-ethoxy]ethyl]-carbamate (CAS# 189209-27-6) | KR | 929.1 | 11.09 (s, 1H), 10.82 (s, 1H), 9.02 (s, 1H), 8.44-8.38 (m, 2H), 8.25-8.23 (m, 2H), 7.56 (dd, J = 7.2 Hz, J = 8.4 Hz, 1H), 7.41 (s, 1H), 7.25 (d, J = 5.6 Hz, 1H), 7.11 (d, J = 8.4 Hz, 1H), 7.01 (d, J = 6.8 Hz, 1H), 6.58 (bs, 1H), 5.06-5.03 (m, 1H), 4.37-4.36 (m, 2H), 3.93-3.91 (m, 6H), 3.53-3.44 (m, 22H), 2.88 (m, 1H), 2.60-2.54 (m, 2H), 2.03-2.01 (m, 1H) |

[a] For varations in Method 11, see Table 9 footnotes.

TABLE 21

Compounds synthesized via Method 12 with the coupling of various amines and acids in Step 1.

| Ex-# | I-# | Step 1 Intermediate Amine | Step 1 Intermediate Acid | LCMS (ES+) m/z (M + H)+ | 1HNMR (400 MHz, DMSO-d6) δ |
|---|---|---|---|---|---|
| 210[a] | I-215 | OK | FI | 888.4 | 11.1 (s, 1H), 10.3 (s, 1H), 9.00 (s, 1H), 8.84 (s, 1H), 8.61 (t, J = 5.2 Hz, 1H), 8.33 (s, 3H), 8.26 (d, J = 5.2 Hz, 1H), 8.05-8.00 (m, 2H), 7.99-7.95 (m, 2H), 7.68-7.62 (m, 1H), 7.60-7.54 (m, 1H), 7.24 (s, 1H), 7.12 (d, J = 8.4 Hz, 1H), 7.03 (d, J = 7.2 Hz, 1H), 6.61 (s, 1H), 5.11-5.00 (m, 1H), 4.28-4.19 (m, 4H), 3.54-3.46 (m, 12H), 2.95-2.81 (m, 1H), 2.63-2.57 (m, 1H), 2.56-2.54 (m, 1H), 2.07-1.99 (m, 1H) |
| 211 | I-216 | CT | CN | 989.9 | 11.12 (s, 1H), 11.01 (s, 1H), 9.04 (d, J = 2.4 Hz, 2H), 8.64 (t, J = 5.2 Hz, 1H), 8.26 (d, J = 5.2 Hz, 1H), 8.18-8.07 (m, 3H), 8.07-8.00 (m, 2H), 7.84-7.74 (m, 3H), 7.74-7.67 (m, 2H), 7.27 (s, 1H), 7.18 (d, J = 5.2 Hz, 1H), 5.13 (dd, J = 5.2, 12.8 Hz, 1H), 4.33-4.20 (m, 2H), 3.59-3.37 (m, 18H), 2.95-2.76 (m, 3H), 2.65-2.57 (m, 2H), 2.11-1.99 (m, 1H), 1.90-1.82 (m, 2H) |
| 212 | I-217 | CS | CN | 985.6 | 11.14 (s, 1H), 11.00 (s, 1H), 9.03 (m, 2H), 8.65 (t, J = 5.2 Hz, 1H), 8.26 (d, J = 5.6 Hz, 1H), 8.18-8.08 (m, 3H), 8.06-8.00 (m, 2H), 7.98-7.87 (m, 3H), 7.77 (s, 1H), 7.70 (t, J = 6.8 Hz, 1H), 7.27 (s, 1H), 7.22-7.10 (m, 1H), 5.16 (dd, J = 5.2, 12.8 Hz, 1H), 4.45 (s, 2H), 4.31-4.19 (m, 2H), 3.69-3.50 (m, 16H), 2.93-2.84 (m, 1H), 2.62 (m, 1H), 2.57 (m, 1H), 2.10-2.02 (m, 1H) |
| 213 | I-218 | FP | EG | 896.1 | 11.11 (s, 1H), 9.99 (s, 1H), 9.01 (s, 1H), 8.98 (s, 1H), 8.75-8.74 (m, 1H), 8.16 (d, J = 5.2 Hz, 1H), 8.06-7.99 (m, 4H), 7.63-7.52 (m, 1H), 7.14-7.08 (m, 3H), 7.06-7.00 (m, 2H), 6.64-6.52 (m, 1H), 5.08-5.02 (m, 1H), 3.30-3.26 (m, 6H), 3.22-3.13 (m, 2H), 2.92-2.83 (m, 1H), 2.74-2.70 (m, 2H), 2.62-2.52 (m, 2H), 2.05-2.00 (m, 1H), 1.80-1.72 (m, 2H), 1.65-1.54 (m, 4H), 1.10-1.04 (m, 1H), 0.48-0.43 (m, 2H), 0.25-0.20 (m, 2H) |
| 214 | I-219 | FR | CN | 955.6 | 11.11 (s, 1H), 11.03 (s, 1H), 9.05 (s, 1H), 9.02 (s, 1H), 8.37 (s, 1H), 8.26 (d, J = 5.2 Hz, 1H), 8.21 (s, 1H), 8.06 (d, J = 8.8 Hz, 2H), 7.97 (d, J = 8.8 Hz, 2H), 7.80 (s, 1H), 7.72 (t, J = 6.4 Hz, 1H), 7.57-7.50 (m, 1H), 7.28 (s, 1H), 7.18 (dd, J = 1.2, 5.2 Hz = 1H) 7.11 (dd, J = 2.8, 8.8 Hz, 1H), 7.00 (dd, J = 2.0, 7.2 Hz, 1H), 6.60-6.59 (m, 1H), 5.07-5.02 (m, 1H), 4.32-4.20 (m, 2H), 3.63-3.25 (m, 10H), 2.97-2.80 (m, 4H), 2.64-2.57 (m, 2H), 2.08-1.96 (m, 1H), 1.63-1.61 (m, 2H), 1.51-1.39 (m, 2H), 1.32-1.21 (m, 2H) |
| 215 | I-220 | OK | EG | 899.1 | 11.08 (s, 1H), 9.96 (s, 1H), 9.00-8.96 (m, 1H), 8.98 (d, J = 4.4 Hz, 2H), 8.63 (t, J = 5.2 Hz, 1H), 8.16 (d, J = 5.2 Hz, 1H), 8.05-7.97 (m, 4H), 7.55 (t, J = 7.6 Hz, 1H), 7.12-6.99 (m, 5H), 6.59 (t, J = 5.6 Hz, 1H), 5.05 (dd, J = 5.2, 12.8 Hz, 1H), 3.65-3.54 (m, 8H), 3.46-3.43 (m, 4H), 3.18 (t, J = 6.0 Hz, |

TABLE 21-continued

Compounds synthesized via Method 12 with the coupling of various amines and acids in Step 1.

| Ex-# | I-# | Step 1 Intermediate Amine | Step 1 Intermediate Acid | LCMS (ES+) m/z (M + H)+ | 1HNMR (400 MHz, DMSO-d6) δ |
|---|---|---|---|---|---|
| | | | | | 2H), 2.92-2.83 (m, 1H), 2.60-2.54 (m, 2H), 2.07-1.99 (m, 1H), 1.11-1.03 (m, 1H), 0.48-0.43 (m, 2H), 0.25-0.20 (m, 2H) |
| 216 | I-221 | FV | EG | 895.5 | 11.19 (s, 1H), 10.00 (s, 1H), 9.03-8.97 (m, 2H), 8.61 (t, J = 5.2 Hz, 1H), 8.36 (s, 1H), 8.16 (d, J = 5.2 Hz, 1H), 8.06-7.98 (m, 4H), 7.81-7.74 (m, 2H), 7.72-7.68 (m, 1H), 7.14-7.07 (m, 2H), 7.04 (d, J = 5.2 Hz, 1H), 5.13 (dd, J = 5.2, 12.8 Hz, 1H), 3.31-3.32 (m, 4H), 3.18 (t, J = 6.0 Hz, 2H), 3.06 (t, J = 7.2 Hz, 2H), 2.93-2.85 (m, 1H), 2.64-2.61 (m, 2H), 2.59-2.56 (m, 1H), 2.55-2.53 (m, 1H), 2.10-2.02 (m, 1H), 1.86-1.76 (m, 2H), 1.59-1.46 (m, 4H), 1.36-1.35 (m, 2H), 1.12-1.02 (m, 1H), 0.49-0.42 (m, 2H), 0.25-0.21 (m, 2H) |
| 217 | I-222 | FS | EG | 898.1 | 11.10 (s, 1H), 9.97 (s, 1H), 9.00-8.96 (m, 2H), 8.71-8.68 (m, 1H), 8.18 (s, 1H), 8.16 (d, J = 5.2 Hz, 1H), 8.06-7.96 (m, 4H), 7.55 (t, J = 8.0 Hz, 1H), 7.13-6.97 (m, 5H), 6.77-6.71 (m, 1H), 5.09-5.99 (m, 1H), 3.57-3.52 (m, 4H), 3.49-3.44 (m, 4H), 3.21-3.16 (m, 2H), 2.93-2.86 (m, 1H), 2.85-2.74 (m, 4H), 2.62-2.55 (m, 2H), 2.05-1.96 (m, 1H), 1.11-1.03 (m, 1H), 0.48-0.42 (m, 2H), 0.25-0.20 (m, 2H) |
| 218 | I-223 | EL | FX | 878.2 | 11.11 (s, 1H), 10.08 (s, 1H), 9.00 (s, 1H), 8.93 (s, 1H), 8.57 (t, J = 5.2 Hz, 1H), 8.30 (s, 1H), 8.20-8.14 (m, 1H), 8.05-7.95 (m, 4H), 7.59 (t, J = 7.8 Hz, 1H), 7.46-7.19 (m, 1H), 7.16-7.11 (m, 2H), 7.07-7.01 (m, 2H), 6.82 (t, J = 5.2 Hz, 1H), 5.06 (dd, J = 5.4, 12.8 Hz, 1H), 3.37-3.19 (m, 8H), 2.95-2.80 (m, 4H), 2.67-2.62 (m, 2H), 2.08-2.00 (m, 1H), 1.61-1.47 (m, 4H), 1.38 (d, J = 7.2 Hz, 2H), 1.14-1.02 (m, 1H), 0.51-0.43 (m, 2H), 0.23 (q, J = 4.8 Hz, 2H) |
| 219 | I-224 | FZ | DF | 887.5 | 11.12 (s, 1H), 10.98 (s, 1H), 9.00 (s, 1H), 8.98-8.93 (m, 1H), 8.16 (d, J = 5.2 Hz, 1H), 8.09 (s, 1H), 8.01 (d, J = 8.0 Hz, 2H), 7.80-7.69 (m, 3H), 7.63 (s, 1H), 7.60-7.52 (m, 2H), 7.17 (t, J = 5.2 Hz, 1H), 7.12 (s, 1H), 7.04-6.97 (m, 1H), 5.15-5.07 (m, 1H), 3.61-3.49 (m, 10H), 3.18 (t, J = 6.0 Hz, 2H), 3.09-3.02 (m, 2H), 2.99 (s, 3H), 2.93-2.81 (m, 1H), 2.64-2.55 (m, 2H), 2.09-2.00 (m, 1H), 1.90-1.76 (m, 2H), 1.12-1.01 (m, 1H), 0.48-0.42 (m, 2H), 0.26-0.20 (m, 2H) |
| 220 | I-225 | FZ | FX | 894.6 | 11.1 (s, 1H), 10.0 (s, 1H), 8.98 (s, 1H), 8.86 (s, 1H), 8.16 (d, J = 5.2 Hz, 1H), 7.91 (d, J = 7.2 Hz, 2H), 7.73 (s, 2H), 7.66 (s, 1H), 7.57 (d, J = 6.4 Hz, 2H), 7.46-7.16 (m, 1H), 7.15-7.08 (m, 2H), 7.05 (d, J = 5.2 Hz, 1H), 5.17-5.06 (m, 1H), 3.67-3.49 (m, 10H), 3.22-3.16 (m, 2H), 3.10-3.02 (m, 2H), 3.00 (s, 3H), 2.94-2.82 (m, 1H), 2.64-2.57 (m, 1H), 2.57-2.53 (m, 1H), 2.12-1.99 (m, 1H), 1.92-1.80 (m, 2H), |

TABLE 21-continued

Compounds synthesized via Method 12 with the coupling of various amines and acids in Step 1.

| Ex-# | I-# | Step 1 Intermediate Amine | Step 1 Intermediate Acid | LCMS (ES+) m/z (M + H)+ | 1HNMR (400 MHz, DMSO-d6) δ |
|---|---|---|---|---|---|
| 221[b] | I-226 | FZ | EE | 818.4 | 1.15-1.01 (m, 1H), 0.52-0.43 (m, 2H), 0.28-0.19 (m, 2H) 11.12 (s, 2H), 9.11 (s, 1H), 8.97 (s, 1H), 8.87 (d, J = 5.6 Hz, 2H), 8.15-8.06 (m, 1H), 8.06-7.95 (m, 4H), 7.80 (s, 1H), 7.73 (s, 2H), 7.66 (s, 1H), 7.58 (d, J = 7.2 Hz, 2H), 5.12 (dd, J = 5.2, 12.8 Hz, 1H), 3.66-3.49 (m, 10H), 3.06 (s, 2H), 3.01 (s, 3H), 2.95-2.82 (m, 1H), 2.65-2.54 (m, 2H), 2.11-2.00 (m, 1H), 1.85 (s, 2H) |
| 222[b] | I-227 | GD | EE | 818.4 | 11.14-11.05 (m, 2H), 9.10 (d, J = 2.0 Hz, 1H), 8.97 (s, 1H), 8.86 (d, J = 5.2 Hz, 2H), 8.09 (s, 1H), 8.03 (s, 2H), 7.97 (d, J = 4.4 Hz, 2H), 7.82-7.63 (m, 4H), 7.58 (d, J = 7.6 Hz, 2H), 5.12 (dd, J = 5.2, 12.8 Hz, 1H), 3.68-3.39 (m, 10H), 3.01 (s, 3H), 2.94-2.78 (m, 3H), 2.61-2.53 (m, 2H), 2.10-2.01 (m, 1H), 1.86 (s, 2H) |
| 223 | I-228 | GD | DF | 887.5 | 11.13 (s, 1H), 10.99 (s, 1H), 9.10-8.87 (m, 2H), 8.24-7.97 (m, 4H), 7.82-7.53 (m, 6H), 7.20 (t, J = 5.2 Hz, 1H), 7.13 (s, 1H), 7.01 (d, J = 5.6 Hz, 1H), 5.12 (d, J = 8.8 Hz, 1H), 3.68-3.39 (m, 12H), 3.01 (s, 3H), 2.90-2.72 (m, 3H), 2.64-2.54 (m, 2H), 2.10-2.01 (m, 1H), 1.85 (s, 2H), 1.07 (d, J = 6.4 Hz, 1H), 0.62-0.35 (m, 2H), 0.23 (d, J = 4.8 Hz, 2H) |
| 224 | I-229 | GL | DF | 843.6 | 10.88 (s, 1H), 10.77 (s, 1H), 8.76 (s, 2H), 7.93 (d, J = 5.2 Hz, 1H), 7.89-7.76 (m, 3H), 7.58-7.41 (m, 4H), 7.34 (d, J = 8.0 Hz, 2H), 6.96-6.85 (m, 2H), 6.77 (d, J = 4.8 Hz, 1H), 6.81-6.74 (m, 1H), 4.89 (dd, J = 5.2, 12.8 Hz, 1H), 3.31-3.45 (m, 4H), 3.22-3.21 (m, 2H), 2.95 (t, J = 6.0 Hz, 2H), 2.89-2.81 (m, 1H), 2.77 (s, 3H), 2.70-2.58 (m, 1H), 2.40-2.30 (m, 2H), 1.87-1.76 (m, 1H), 1.71-1.55 (m, 2H), 0.89-0.77 (m, 1H), 0.22 (d, J = 8.0 Hz, 2H), 0.00 (d, J = 4.8 Hz, 2H) |
| 225 | I-230 | GS | DF | 883.6 | 10.89 (s, 1H), 10.82-10.65 (m, 1H), 8.86-8.66 (m, 2H), 7.93 (d, J = 5.2 Hz, 1H), 7.87 (s, 1H), 7.81 (d, J = 8.4 Hz, 2H), 7.54-7.28 (m, 6H), 6.94 (t, J = 5.2 Hz, 1H), 6.88 (s, 1H), 6.77 (d, J = 5.6 Hz, 1H), 4.94-4.81 (m, 1H), 3.25-3.18 (m, 2H), 2.95 (t, J = 6.0 Hz, 3H), 2.82-2.72 (m, 2H), 2.72-2.68 (m, 2H), 2.66-2.62 (m, 1H), 2.40-2.31 (m, 2H), 1.88-1.76 (m, 1H), 1.42-1.19 (m, 4H), 1.14-0.83 (m, 10H), 0.81-0.76 (m, 1H), 0.25-0.18 (m, 2H), 0.03-0.00 (q, J = 4.8 Hz, 2H) |
| 226 | I-231 | GV | CN | 874.1 | 11.11 (s, 1H), 11.03 (s, 1H), 9.04 (d, J = 1.2 Hz, 2H), 8.64 (t, J = 5.6 Hz, 1H), 8.26 (d, J = 5.6 Hz, 1H), 8.15 (s, 1H), 8.12-8.07 (m, 2H), 8.05-8.00 (m, 2H), 7.79 (s, 1H), 7.71 (t, J = 6.4 Hz, 1H), 7.29-7.24 (m, 2H), 7.18 (dd, J = 1.2, 5.2 Hz, 1H), 7.11 (d, J = 8.0 Hz, 1H), 7.08-7.00 (m, 2H), 5.38 (dd, J = 5.6, 12.8 Hz, 1H), 4.28-4.20 (m, 2H), 4.02-3.98 (m, 1H), 4.00 (t, J = 5.6 Hz, 1H), 3.69 (t, J = 5.6 Hz, 2H), |

TABLE 21-continued

Compounds synthesized via Method 12 with the coupling of various amines and acids in Step 1.

| Ex-# | I-# | Step 1 Intermediate Amine | Step 1 Intermediate Acid | LCMS (ES+) m/z (M + H)+ | 1HNMR (400 MHz, DMSO-d6) δ |
|---|---|---|---|---|---|
| | | | | | 3.58-3.49 (m, 8H), 2.96-2.84 (m, 1H), 2.78-2.70 (m, 1H), 2.64-2.60 (m, 1H), 2.03-1.99 (m, 1H) |
| 227 | I-232 | GU | CN | 843.4 | 11.01 (s, 1H), 11.0 (s, 1H), 9.04 (s, 2H), 8.70-8.62 (m, 1H), 8.25 (d, J = 5.2 Hz, 1H), 8.15 (s, 1H), 8.10 (s, 1H), 8.08 (s, 1H), 8.03 (s, 1H), 8.01 (s, 1H), 7.78 (s, 1H), 7.76-7.70 (m, 1H), 7.47-7.73 (m, 1H), 7.46-7.40 (m, 2H), 7.27 (s, 1H), 7.19-7.15 (m, 1H), 5.16-5.08 (m, 1H), 4.49-4.40 (m, 1H), 4.34-4.23 (m, 3H), 3.57-3.50 (m, 2H), 3.49-3.40 (m, 4H), 2.98-2.85 (m, 1H), 2.72-2.67 (m, 2H), 2.63-2.55 (m, 1H), 2.45-2.38 (m, 1H), 2.05-1.93 (m, 1H), 1.89-1.79 (m, 2H) |
| 228 | I-233 | GX | CN | 923.4 (M + Na)+ | 11.12 (s, 1H), 11.02 (s, 1H), 9.03 (d, J = 8.0 Hz, 2H), 8.69-8.61 (m, 1H), 8.26 (d, J = 4.8 Hz, 1H), 8.12 (s, 1H), 8.10-8.05 (m, 2H), 8.05-8.00 (m, 2H), 7.79-7.65 (m, 5H), 7.28 (s, 1H), 7.19 (d, J = 5.2 Hz, 1H), 5.12 (dd, J = 4.4, 12.0 Hz, 1H), 4.30-4.21 (m, 2H), 3.58-3.39 (m, 10H), 3.03 (t, J = 7.2 Hz, 2H), 2.95-2.83 (m, 1H), 2.64-2.57 (m, 1H), 2.56-2.54 (m, 1H), 2.10-2.01 (m,, 1H), 1.86-1.78 (m, 2H) |
| 229 | I-234 | GW | CN | 857.0 | 11.12 (s, 1H), 11.01 (s, 1H), 9.07-9.00 (m, 2H), 8.70-8.63 (m, 1H), 8.28-8.23 (m, 1H), 8.14 (s, 1H), 8.12-8.07 (m, 2H), 8.06-8.01 (m, 2H), 7.77 (s, 1H), 7.76-7.65 (m, 4H), 7.27 (s, 1H), 7.18 (d, J = 5.2 Hz, 1H), 5.16-5.08 (m, 1H), 4.31-4.19 (m, 2H), 3.56-3.50 (m, 2H), 3.49-3.43 (m, 4H), 3.08 (t, J = 7.2 Hz, 2H), 2.93-2.82 (m, 1H), 2.64-2.54 (m, 2H), 2.11-2.00 (m, 1H), 1.93-1.79 (m, 2H) |
| 230 | I-235 | HA | CN | 1011.5 (M + Na)+ | 11.12 (s, 1H), 11.01 (s, 1H), 9.04 (d, J = 3.2 Hz, 2H), 8.64 (t, J = 5.2 Hz, 1H), 8.26 (d, J = 5.2 Hz, 1H), 8.14 (s, 1H), 8.12-8.08 (m, 2H), 8.06-8.00 (m, 2H), 7.79-7.66 (m, 5H), 7.28 (s, 1H), 7.18 (dd, J = 1.2, 5.2 Hz, 1H), 5.13 (dd, J = 5.2, 12.8 Hz, 1H), 4.33-4.19 (m, 2H), 3.58-3.44 (m, 16H), 3.40 (t, J = 6.4 Hz, 2H), 3.05 (t, J = 7.6 Hz, 2H), 2.94-2.84 (m, 1H), 2.63-2.55 (m, 2H), 2.10-2.02 (m, 1H), 1.88-1.78 (m, 2H) |
| 231 | I-236 | MN | CN | 985.5 | 11.14 (s, 1H), 11.00 (s, 1H), 9.03 (d, J = 2.4 Hz, 2H), 8.65 (s, 1H), 8.52 (s, 1H), 8.26 (d, J = 5.2 Hz, 1H), 8.15-8.07 (m, 3H), 8.06-8.01 (m, 2H), 7.92-7.83 (m, 3H), 7.77 (s, 1H), 7.71 (t, J = 6.8 Hz, 1H), 7.27 (s, 1H), 7.18 (dd, J = 1.2, 5.2 Hz, 1H), 5.15 (dd, J = 5.2, 12.8 Hz, 1H), 4.48 (s, 2H), 4.31-4.20 (m, 2H), 3.71 (dd, J = 3.6, 5.6 Hz, 2H), 3.56-3.53 (m, 8H), 3.50-3.40 (m, 5H), 2.95-2.88 (m, 1H), 2.70-2.55 (m, 5H), 2.36-2.31 (m, 1H), 2.11-2.04 (m, 1H) |
| 232 | I-237 | HB | DF | 859.5 | 11.04-10.97 (m, 2H), 9.03 (s, 1H), 9.01 (s, 1H), 8.65 (t, J = 5.2 Hz, 1H), 8.20-8.12 (m, 2H), 8.11-8.05 (d, J = 8.8 Hz, 2H), |

TABLE 21-continued

Compounds synthesized via Method 12 with the coupling of various amines and acids in Step 1.

| Ex-# | I-# | Step 1 Intermediate Amine | Step 1 Intermediate Acid | LCMS (ES+) m/z (M + H)+ | 1HNMR (400 MHz, DMSO-d6) δ |
|---|---|---|---|---|---|
| | | | | | 8.04-7.98 (d, J = 8.8 Hz, 2H), 7.79 (s, 1H), 7.58-7.52 (m, 1H), 7.43 (d, J = 4.4 Hz, 2H), 7.17 (t, J = 5.2 Hz, 1H), 7.12 (s, 1H), 7.00 (dd, J = 1.2, 5.2 Hz, 1H), 5.13 (dd, J = 4.8, 13.2 Hz, 1H), 4.49-4.40 (d, J = 17.2 Hz, 1H), 4.34-4.24 (d, J = 17.2 Hz,, 1H), 3.58-3.54 (m, 4H), 3.51-3.48 (m, 2H), 3.47-3.44 (m, 2H), 3.39 (t, J = 6.4 Hz, 2H), 3.19 (t, J = 6.4 Hz, 2H), 2.97-2.87 (m, 1H), 2.66-2.52 (m, 4H), 2.06-1.95 (m, 1H), 1.84-1.77 (m, 2H), 1.14-1.01 (m, 1H), 0.53-0.40 (m, 2H), 0.29-0.19 (m, 2H) |
| 233 | I-238 | HC | DF | 925.5 (M + Na)+ | 11.01 (s, 1H), 10.99 (s, 1H), 9.04 (s, 1H), 9.01 (s, 1H), 8.64 (s, 1H), 8.21-8.13 (m, 2H), 8.12-8.07 (m, 2H), 8.05-7.99 (m, 2H), 7.78 (s, 1H), 7.58-7.52 (m, 1H), 7.44 (d, J = 4.0 Hz, 2H), 7.20-7.14 (m, 1H), 7.13 (s, 1H), 7.01 (d, J = 4.8 Hz, 1H), 5.17-5.08 (m, 1H), 4.47-4.40 (m, 1H), 4.32-4.27 (m, 1H), 3.57-3.52 (m, 8H), 3.48-3.44 (m, 6H), 3.25-3.09 (m, 2H), 3.04-2.90 (m, 1H), 2.66-2.55 (m, 1H), 2.55-2.54 (m, 1H), 2.42-2.41 (m, 2H), 2.04-1.99 (m, 1H), 1.85-1.80 (m, 2H), 1.11-1.04 (m, 1H), 0.49-0.43 (m, 2H), 0.26-0.20 (m, 2H) |
| 234 | I-239 | HE | OM | 799.4 | 10.87 (s, 1H), 10.71 (s, 1H), 8.69 (s, 1H), 8.16 (s, 1H), 7.91 (d, J = 5.2 Hz, 1H), 7.52 (s, 1H), 7.34-7.29 (m, 1H), 7.28 (s, 1H), 6.95-6.90 (m, 1H), 6.88-6.85 (m, 2H), 6.78 (d, J = 7.2 Hz, 1H), 6.75-6.73 (m, 1H), 6.36-6.30 (m, 1H), 4.84-4.78 (m, 1H), 4.13-4.08 (m, 2H), 3.60-3.55 (m, 2H), 3.37-3.34 (m, 2H), 3.29-3.26 (m, 6H), 3.24-3.17 (m, 4H), 2.97-2.93 (m, 2H), 2.66-2.59 (m, 1H), 2.40-2.35 (m, 1H), 2.33-2.31 (m, 1H), 1.82-1.74 (m, 1H), 0.86-0.80 (m, 1H), 0.24-0.21 (m, 2H), 0.02-0.01 (m, 2H) |
| 235 | I-240 | HI | OM | 843.5 | 11.09 (s, 1H), 10.94 (s, 1H), 8.93 (s, 1H), 8.39 (s, 1H), 8.14 (s, 1H), 7.74 (s, 1H), 7.59-7.53 (m, 1H), 7.51 (s, 1H), 7.14 (t, J = 5.2 Hz, 1H), 7.12-7.08 (m, 2H), 7.00-6.95 (m, 2H), 6.57 (t, J = 5.6 Hz, 1H), 5.10-5.00 (m, 1H), 4.35 (t, J = 5.2 Hz, 2H), 3.81 (t, J = 5.2 Hz, 2H), 3.62-3.56 (m, 2H), 3.54-3.41 (m, 14H), 3.18 (t, J = 6.0 Hz, 2H), 2.93-2.82 (m, 1H), 2.62-2.53 (m, 2H), 2.07-1.97 (m, 1H), 1.11-1.01 (m, 1H), 0.49-0.42 (m, 2H), 0.25-0.20 (m, 2H) |
| 236[b] | I-241 | OK | MP | 819.1 | 11.18-11.00 (m, 2H), 9.09 (s, 1H), 9.02 (s, 1H), 8.70 (d, J = 5.6 Hz, 1H), 8.62 (t, J = 5.6 Hz, 1H), 8.19-8.11 (m, 1H), 8.11-7.98 (m, 4H), 7.86-7.79 (m, 2H), 7.76 (d, J = 4.8 Hz, 1H), 7.56 (t, J = 8.0 Hz, 1H), 7.11 (d, J = 8.8 Hz, 1H), 7.01 (d, J = 7.2 Hz, 1H), 6.59 (t, J = 6.0 Hz, 1H), 5.10-4.97 (m, 1H), 3.65-3.52 (m, 8H), 3.48-3.42 (m, 4H), 2.93-2.81 (m, 1H), 2.61 (s, 3H), |

TABLE 21-continued

Compounds synthesized via Method 12 with the coupling of various amines and acids in Step 1.

| Ex-# | I-# | Step 1 Intermediate Amine | Step 1 Intermediate Acid | LCMS (ES+) m/z (M + H)+ | 1HNMR (400 MHz, DMSO-d6) δ |
|---|---|---|---|---|---|
| 237 | I-242 | EL | FX | 878.1 | 2.58-2.53 (m, 2H), 2.09-1.98 (m, 1H)<br>11.09 (s, 1H), 10.05 (s, 1H), 8.98 (s, 1H), 8.92 (s, 1H), 8.59-8.50 (m, 1H), 8.27 (s, 2H), 8.16 (d, J = 5.2 Hz, 1H), 8.03-7.9 (m, 4H), 7.62-7.55 (m, 1H), 7.47-7.17 (t, J = 50.0 Hz, 1H), 7.15-7.01 (m, 5H), 6.85-6.78 (m, 1H), 5.0-5.1 (m, 1H), 3.40 (s, 2H), 3.30-3.24 (m, 1H), 3.21-3.15 (m, 2H), 2.97-2.87 (m, 1H), 2.86-2.79 (m, 2H), 2.71-2.56 (m, 4H), 2.07-1.96 (m, 1H), 1.64-1.44 (m, 4H), 1.40-1.30 (m, 2H), 1.14-1.01 (m, 1H), 0.48-0.42 (m, 2H), 0.27-0.18 (m, 2H) |
| 238 | I-243 | GW | FX | 836.4 | 11.12 (s, 1H), 10.06 (s, 1H), 8.99 (s, 1H), 8.92 (s, 1H), 8.66 (t, J = 5.2 Hz, 1H), 8.16 (d, J = 5.2 Hz, 1H), 8.01 (d, J = 8.8 Hz, 2H), 7.95 (d, J = 8.8 Hz, 2H), 7.78-7.71 (m, 2H), 7.70-7.64 (m, 1H), 7.32 (t, J = 54.0 Hz, 1H), 7.14-7.08 (m, 2H), 7.04 (dd, J = 1.2, 5.2 Hz, 1H), 5.12 (dd, J = 5.6, 12.8 Hz, 1H), 3.52 (t, J = 6.4 Hz, 2H), 3.45 (t, J = 6.0 Hz, 4H), 3.18 (t, J = 6.0 Hz, 2H), 3.08 (t, J = 6.8 Hz, 2H), 2.94-2.82 (m, 1H), 2.64-2.54 (m, 2H), 2.11-1.99 (m, 1H), 1.92-1.80 (m, 2H), 1.13-1.02 (m, 1H), 0.50-0.41 (m, 2H), 0.27-0.18 (m, 2H) |
| 239 | I-244 | GX | FX | 880.5 | 10.89 (s, 1H), 9.82 (s, 1H), 8.76 (s, 1H), 8.67 (s, 1H), 8.45-8.37 (m, 1H), 7.93 (d, J = 5.2 Hz, 1H), 7.81-7.75 (m, 2H), 7.74-7.69 (m, 2H), 7.53-7.47 (m, 2H), 7.45-7.41 (m, 1H), 7.24-6.94 (m, 1H), 6.91-6.85 (m, 2H), 6.83-6.77 (m, 1H), 4.89 (dd, J = 5.6, 12.8 Hz, 1H), 3.37-3.20 (m, 10H), 2.95 (t, J = 6.8 Hz, 2H), 2.79 (t, J = 7.2 Hz, 2H), 2.71-2.62 (m, 1H), 2.41-2.38 (m, 1H), 2.36-2.34 (m, 1H), 1.86-1.77 (m, 1H), 1.62-1.53 (m, 2H), 0.89-0.80 (m, 1H), 0.26-0.19 (m, 2H), 0.03-0.00 |
| 240 | I-245 | tert-butyl N-[2-[5-[[2-(2,6-dioxo-3-piperidyl)-1,3-dioxo-isoindolin-4-yl]amino]-pentylamino]-ethyl]carbamate (synthesized via Steps 1-4 of Example 144) | FX | 878.2 | 11.24-11.01 (m, 1H), 10.09 (s, 1H), 9.00 (s, 1H), 8.93 (s, 1H), 8.69 (s, 1H), 8.34 (s, 1H), 8.17 (d, J = 5.2 Hz, 1H), 8.02 (d, J = 10.4 Hz, 3H), 7.58 (s, 1H), 7.33 (s, 1H), 7.21-7.03 (m, 4H), 6.55 (s, 1H), 5.05 (s, 1H), 3.19 (s, 6H), 2.95-2.91 (m, 1H), 2.87 (d, J = 14.8 Hz, 2H), 2.83-2.80 (m, 1H), 2.78-2.74 (m, 1H), 2.68-2.65 (m, 2H), 2.04-2.02 (m, 1H), 1.66-1.33 (m, 6H), 1.08-1.05 (m, 1H), 0.47 (d, J = 7.2 Hz, 2H), 0.24 (s, 2H) |
| 241 | I-246 | OK | FX | 881.5 | 11.10 (s, 1H), 10.05 (s, 1H), 8.99 (s, 1H), 8.92 (s, 1H), 8.61 (t, J = 5.6 Hz, 1H), 8.17 (d, J = 5.6 Hz, 1H), 8.08-7.92 (m, 4H), 7.61-7.50 (m, 1H), 7.49-7.16 (m, 1H), 7.15-6.99 (m, 5H), 6.60 (t, J = 5.6 Hz, 1H), 5.06 (dd, J = 5.6, 12.8 Hz, 1H), 3.64-3.56 (m, 7H), 3.46-3.43 (m, 5H), 3.20 (t, J = 6.0 Hz, 2H), 2.94-2.83 (m, 1H), 2.69-2.56 (m, 2H), 2.09-1.99 (m, 1H), |

TABLE 21-continued

Compounds synthesized via Method 12 with the coupling of various amines and acids in Step 1.

| Ex-# | I-# | Step 1 Intermediate Amine | Step 1 Intermediate Acid | LCMS (ES+) m/z (M + H)+ | 1HNMR (400 MHz, DMSO-d6) δ |
|---|---|---|---|---|---|
| 242 | I-247 | HK | FX | 936.1 | 1.17-1.02 (m, 1H), 0.52-0.43 (m, 2H), 0.29-0.18 (m, 2H) 11.10 (s, 1H), 10.04 (s, 1H), 8.98 (s, 1H), 8.92 (s, 1H), 8.67-8.60 (m, 1H), 8.16 (d, J = 5.4 Hz, 1H), 8.06-8.00 (m, 2H), 7.99-7.93 (m, 2H), 7.57 (t, J = 7.6 Hz, 1H), 7.47-7.17 (m, 1H), 7.16-6.98 (m, 5H), 6.63-6.55 (m, 1H), 5.11-5.01 (m, 1H), 3.75 (d, J = 10.8 Hz, 1H), 3.65-3.51 (m, 6H), 3.50-3.36 (m, 4H), 3.35-3.27 (m, 2H), 3.18 (t, J = 6.0 Hz, 2H), 2.95-2.80 (m, 2H), 2.75-2.65 (m, 1H), 2.58-2.53 (m, 2H), 2.13-2.06 (m, 1H), 2.04-1.97 (m, 1H), 1.91-1.80 (m, 1H), 1.13-1.02 (m, 1H), 0.50-0.40 (m, 2H), 0.26-0.19 (m, 2H) |
| 243 | I-248 | HO | CN | 902.5 | 11.08 (s, 1H), 11.03 (s, 1H), 9.04 (s, 2H), 8.66 (t, J = 5.6 Hz, 1H), 8.27 (d, J = 4.8 Hz, 1H), 8.18-8.08 (m, 3H), 8.07-8.00 (m, 2H), 7.78 (s, 1H), 7.71 (t, J = 6.4 Hz, 1H), 7.28 (s, 1H), 7.19 (d, J = 5.2 Hz, 1H), 7.04-6.96 (m, 2H), 6.86 (d, J = 8.0 Hz, 1H), 5.33 (dd, J = 4.8, 12.4 Hz, 1H), 4.31-4.21 (m, 2H), 3.62-3.57 (m, 4H), 3.55-3.10 (m, 2H), 3.50-3.45 (m, 2H), 3.41 (t, J = 6.4 Hz, 2H), 3.32 (s, 3H), 2.96-2.84 (m, 1H), 2.70-2.58 (m, 4H), 2.04-1.97 (m, 1H), 1.85-1.76 (m, 2H) |
| 244 | I-249 | HQ | CN | 902.4 | 11.08 (s, 1H), 11.03 (s, 1H), 9.03 (d, J = 4.8 Hz, 2H), 8.66 (t, J = 5.2 Hz, 1H), 8.27 (d, J = 5.2 Hz, 1H), 8.14 (s, 1H), 8.09-8.01 (m, 4H), 7.78 (s, 1H), 7.71 (t, J = 6.4 Hz, 1H), 7.28 (s, 1H), 7.19 (d, J = 5.2 Hz, 1H), 6.96-6.91 (m, 2H), 6.87-6.82 (m, 1H), 5.36 (dd, J = 5.2, 12.5 Hz, 1H), 4.31-4.21 (m, 2H), 3.60-3.45 (m, 13H), 2.97-2.84 (m, 3H), 2.65-2.55 (m, 2H), 2.03-1.96 (m, 1H), 1.84-1.77 (m, 2H) |
| 245 | I-250 | HR | FX | 936.2 | 11.10 (s, 1H), 10.06 (s, 1H), 8.99 (s, 1H), 8.92 (s, 1H), 8.65 (s, 1H), 8.16 (d, J = 5.2 Hz, 1H), 8.04-8.00 (m, 2H), 7.99-7.94 (m, 2H), 7.61-7.53 (m, 1H), 7.46-7.17 (m, 1H), 7.15-7.08 (m, 3H), 7.06-7.00 (m, 2H), 6.59 (s, 1H), 5.09-5.03 (m, 1H), 3.77-3.72 (m, 1H), 3.64-3.45 (m, 6H), 3.30-3.26 (m, 6H), 3.22-3.12 (m, 2H), 2.87-2.81 (m, 2H), 2.75-2.69 (m, 1H), 2.61-2.58 (m, 1H), 2.56-2.55 (m, 1H), 2.10-1.97 (m, 2H), 1.92-1.79 (m, 1H), 1.12-1.00 (m, 1H), 0.48-0.43 (m, 2H), 0.25-0.20 (m, 2H) |
| 246 | I-251 | GV | FX | 853.6 | 11.10 (s, 1H), 10.05 (s, 1H), 8.99 (s, 1H), 8.92 (s, 1H), 8.62 (t, J = 5.2 Hz, 1H), 8.17 (d, J = 5.2 Hz, 1H), 8.06-7.95 (m, 4H), 7.32 (s, 1H), 7.28-7.23 (m, 1H), 7.15-6.99 (m, 6H), 5.38 (dd, J = 5.2, 12.8 Hz, 1H), 4.00 (t, J = 5.6 Hz, 2H), 3.69 (t, J = 5.6 Hz, 2H), 3.59-3.44 (m, 8H), 3.20-3.17 (m, 2H), 2.97-2.83 (m, 1H), 2.77-2.58 (m, 2H), 2.11-1.93 (m, 1H), 1.18-0.98 (m, |

TABLE 21-continued

Compounds synthesized via Method 12 with the coupling of various amines and acids in Step 1.

| Ex-# | I-# | Step 1 Intermediate Amine | Step 1 Intermediate Acid | LCMS (ES+) m/z (M + H)+ | 1HNMR (400 MHz, DMSO-d6) δ |
|---|---|---|---|---|---|
| | | | | | 1H), 0.54-0.38 (m, 2H), 0.30-0.16 (m, 2H) |
| 247 | I-252 | HO | FX | 881.6 | 11.08 (s, 1H), 10.03 (s, 1H), 8.99 (s, 1H), 8.92 (s, 1H), 8.65 (t, J = 5.2 Hz, 1H), 8.17 (d, J = 5.6 Hz, 1H), 8.07-8.01 (m, 2H), 8.00-7.94 (m, 2H), 7.47-7.17 (m, 1H), 7.15-7.07 (m, 2H), 7.07-7.04 (m, 1H), 7.03-6.96 (m, 2H), 6.89-6.81 (m, 1H), 5.33 (dd, J = 5.6, 12.8 Hz, 1H), 3.61-3.55 (m, 4H), 3.54-3.50 (m, 2H), 3.49-3.44 (m, 2H), 3.40 (t, J = 6.4 Hz, 2H), 3.31 (s, 3H), 3.19 (t, J = 6.0 Hz, 2H), 2.94-2.85 (m, 1H), 2.65-2.61 (m, 4H), 2.03-1.97 (m, 1H), 1.83-1.76 (m, 2H), 1.12-1.04 (m, 1H), 0.50-0.41 (m, 2H), 0.28-0.19 (m, 2H) |
| 248 | I-253 | HQ | FX | 881.5 | 11.08 (s, 1H), 10.04 (s, 1H), 8.99 (s, 1H), 8.90 (s, 1H), 8.65 (t, J = 5.6 Hz, 1H), 8.48 (s, 1H), 8.17 (d, J = 5.2 Hz, 1H), 8.04-8.00 (m, 2H), 7.98-7.93 (m, 2H), 7.47-7.45 (m, 1H), 7.46 (s, 1H), 7.34-7.31 (m, 1H), 7.14-7.08 (m, 2H), 7.05 (d, J = 1.2, 5.3 Hz, 1H), 6.96-6.92 (m, 2H), 6.84 (dd, J = 2.8, 6.0 Hz, 1H), 5.36 (dd, J = 5.2, 12.4 Hz, 1H), 3.61-3.57 (m, 4H), 3.55 (s, 5H), 3.49-3.43 (m, 5H), 3.19 (t, J = 6.0 Hz, 2H), 2.96-2.90 (m, 3H), 2.69-2.66 (m, 2H), 2.35-2.32 (m, 2H), 2.03-1.94 (m, 1H), 1.85-1.76 (m, 2H), 1.12-1.04 (m, 1H), 0.49-0.43 (m, 2H), 0.26-0.21 (m, 2H) |
| 249 | I-254 | HU | OM | 850.1 | 11.13-11.08 (m, 1H), 11.11 (s, 1H), 9.72 (s, 1H), 8.93 (s, 1H), 8.19 (s, 1H), 8.16-8.12 (m, 1H), 8.14 (d, J = 5.2 Hz, 1H), 7.57 (dd, J = 7.2, 8.4 Hz, 1H), 7.32-7.00 (m, 6H), 6.59 (t, J = 5.6 Hz, 1H), 5.05 (dd, J = 5.2, 12.8 Hz, 1H), 4.32 (t, J = 5.2 Hz, 2H), 3.79 (t, J = 5.2 Hz, 2H), 3.59 (t, J = 5.2 Hz, 2H), 3.54-3.47 (m, 14H), 3.18 (t, J = 6.4 Hz, 2H), 2.93-2.84 (m, 1H), 2.64-2.53 (m, 2H), 2.07-1.98 (m, 1H), 2.07-1.98 (m, 1H), 1.11-1.00 (m, 1H), 0.48-0.43 (m, 2H), 0.25-0.20 (m, 2H) |
| 250[b] | I-255 | FU | JL | 723.0 | 11.20 (s, 1H), 10.14 (s, 1H), 9.08 (s, 1H), 8.92 (s, 1H), 8.86 (d, J = 5.2 Hz, 2H), 8.62 (s, 1H), 8.09-7.93 (m, 7H), 7.78 (d, J = 2.0 Hz, 2H), 7.48-7.16 (m, 1H), 5.14 (dd, J = 5.2, 12.8 Hz, 1H), 4.22 (s, 1H), 3.35 (d, J = 6.0 Hz, 2H), 3.16-3.12 (m, 1H), 2.98-2.83 (m, 1H), 2.65-2.53 (m, 4H), 2.17-2.01 (m, 1H), 1.97-1.89 (m, 1H) |
| 251 | I-256 | JG | JE | 896.6 | 11.19 (s, 1H), 10.02 (s, 1H), 9.00 (s, 1H), 8.91 (s, 1H), 8.63 (t, J = 5.6 Hz, 1H), 8.26 (d, J = 5.6 Hz, 1H), 8.06-8.00 (m, 2H), 7.99-7.93 (m, 2H), 7.61 (t, J = 6.4 Hz, 1H), 7.46-7.18 (m, 3H), 7.14-7.06 (m, 2H), 7.01-6.97 (m, 1H), 5.35 (dd, J = 5.2, 12.8 Hz, 1H), 4.32-4.18 (m, 2H), 3.61-3.55 (m, 4H), 3.55-3.50 (m, 2H), 3.49-3.41 (m, 4H), |

US 10,874,743 B2

TABLE 21-continued

Compounds synthesized via Method 12 with the coupling of various amines and acids in Step 1.

| Ex-# | I-# | Step 1 Intermediate Amine | Step 1 Intermediate Acid | LCMS (ES+) m/z (M + H)+ | 1HNMR (400 MHz, DMSO-d6) δ |
|---|---|---|---|---|---|
| | | | | | 2.94-2.83 (m, 1H), 2.75-2.70 (m, 2H), 2.69-2.66 (m, 1H), 2.57-2.53 (m, 1H), 2.20-2.11 (m, 1H), 1.88-1.79 (m, 2H) |
| 252 | I-257 | NK | OM | 786.4 | 10.88 (s, 1H), 9.47 (s, 1H), 8.69 (s, 1H), 8.00 (s, 1H), 7.98-7.94 (m, 1H), 7.92 (d, J = 5.6 Hz, 1H), 7.57-7.54 (m, 2H), 7.06-6.82 (m, 3H), 6.80-7.80 (m, 1H), 4.91 (dd, J = 5.2, 12.8 Hz, 1H), 3.96-3.90 (m, 1H), 3.54-3.31 (m, 10H), 2.97-2.94 (m, 2H), 2.72-2.63 (m, 3H), 2.42-2.32 (m, 2H), 1.93-1.81 (m, 2H), 1.71-1.63 (m, 3H), 0.87-0.80 (m, 1H), 0.26-0.19 (m, 2H), 0.02-0.03 (m, 2H) |
| 253 | I-258 | NL | OM | 784.4 | 11.13 (s, 1H), 9.72 (s, 1H), 8.93 (s, 1H), 8.19 (s, 1H), 8.15 (d, J = 5.2 Hz, 1H), 7.80-7.70 (m, 3H), 7.31-7.04 (m, 3H), 7.03-7.00 (m, 1H), 5.13 (dd, J = 5.2, 12.8 Hz, 1H), 4.26-4.17 (m, 1H), 3.17 (t, J = 6.0 Hz, 2H), 3.05 (t, J = 7.6 Hz, 2H), 2.96-2.91 (m, 2H), 2.91-2.83 (m, 1H), 2.64-2.54 (m, 1H), 2.53-2.51 (m, 1H), 2.33-2.27 (m, 2H), 2.10-1.89 (m, 7H), 1.69-1.58 (m, 2H), 1.53-1.44 (m, 2H), 1.39-1.31 (m, 2H), 1.10-1.02 (m, 1H), 0.47-0.42 (m, 2H), 0.24-0.20 (m, 2H) |
| 254 | I-259 | NN | OM | 756.4 | 11.08 (s, 1H), 9.68 (s, 1H), 8.89 (s, 1H), 8.35 (s, 1H), 8.16 (s, 1H), 8.12 (d, J = 5.2 Hz, 1H), 7.78-7.67 (m, 3H), 7.28-7.10 (m, 1H), 7.09-7.03 (m, 2H), 7.00-6.97 (m, 1H), 5.11 (dd, J = 5.6, 12.8 Hz, 1H), 4.19 (t, J = 11.2 Hz, 1H), 3.17-3.12 (m, 3H), 3.05 (t, J = 7.6 Hz, 2H), 2.96-2.82 (m, 3H), 2.65-2.63 (m, 1H), 2.56-2.51 (m, 1H), 2.35-2.29 (m, 3H), 2.02-1.93 (m, 5H), 1.81-1.73 (m, 2H), 1.03 (t, J = 6.8 Hz, 1H), 0.45-0.39 (m, 2H), 0.21-0.16 (m, 2H) |
| 255[b] | I-260 | JI | JL | 723.3 | 11.10 (s, 1H), 10.14 (s, 1H), 9.06 (s, 1H), 8.91 (s, 1H), 8.84 (d, J = 5.6 Hz, 2H), 8.58 (s, 6H), 7.98 (s, 6H), 7.87-7.81 (m, 2H), 7.79-7.73 (m, 1H), 7.47-7.16 (m, 1H), 5.13 (dd, J = 5.2, 12.8 Hz, 1H), 2.87 (t, J = 7.2 Hz, 3H), 2.65-2.52 (m, 4H), 2.09-2.00 (m, 1H), 1.99-1.88 (m, 2H) |
| 256 | I-261 | OK | JE | 909.3 | 10.26 (s, 1H), 9.22 (s, 1H), 8.20 (s, 1H), 8.10 (s, 1H), 7.78 (t, J = 5.6 Hz, 1H), 7.44 (d, J = 5.2 Hz, 1H), 7.23-7.12 (m, 4H), 6.83-6.71 (m, 2H), 6.65-6.36 (m, 3H), 6.30 (d, J = 8.8 Hz, 1H), 6.21 (d, J = 7.2 Hz, 1H), 5.78 (t, J = 5.6 Hz, 1H), 4.24 (dd, J = 5.2, 12.8 Hz, 1H), 3.49-3.38 (m, 2H), 2.84-2.80 (m, 2H), 2.80-2.74 (m, 6H), 2.63 (q, J = 5.2 Hz, 4H), 2.15-2.00 (m, 1H), 1.81-1.72 (m, 2H), 1.25-1.18 (m, 1H) |
| 257 | I-262 | JQ | OM | 786.4 | 11.11 (s, 1H), 9.72 (s, 1H), 8.91 (s, 1H), 8.18 (s, 1H), 8.14 (d, J = 5.2 Hz, 1H), 7.87-7.83 (m, 2H), 7.79-7.75 (m, 1H), 7.30-7.11 (m, 1H), 7.11-7.06 (m, 2H), 7.03-6.99 (m, 1H), 5.19 5.11 (m, 1H), 4.20-4.13 (m, 1H), 3.83-3.60 (m, 2H), |

TABLE 21-continued

Compounds synthesized via Method 12 with the coupling of various amines and acids in Step 1.

| Ex-# | I-# | Step 1 Intermediate Amine | Step 1 Intermediate Acid | LCMS (ES+) m/z (M + H)+ | 1HNMR (400 MHz, DMSO-d6) δ |
|---|---|---|---|---|---|
| | | | | | 3.20-3.14 (m, 2H), 3.06-3.00 (m, 2H), 2.96-2.90 (m, 2H), 2.89-2.82 (m, 1H), 2.63-2.57 (m, 1H), 2.57-2.54 (m, 1H), 2.54-2.51 (m, 4H), 2.15-2.08 (m, 2H), 2.04-1.98 (m, 1H), 1.96-1.86 (m, 4H), 1.10-1.02 (m, 1H), 0.48-0.42 (m, 2H), 0.26-0.18 (m, 2H) |
| 258 | I-263 | NP | OM | 784.5 | 11.12 (s, 1H), 10.36 (s, 1H), 9.87 (s, 1H), 9.02 (s, 1H), 8.24 (s, 1H), 8.15-8.13 (m, 1H), 7.87 (d, J = 7.6 Hz, 1H), 7.82 (s, 1H), 7.76 (d, J = 7.6 Hz, 1H), 7.39-7.08 (m, 3H), 5.15 (dd, J = 5.2, 12.8 Hz, 1H), 4.64-4.53 (m, 1H), 3.67-3.59 (m, 2H), 3.27-3.25 (m, 2H), 3.12-3.02 (m, 4H), 2.96-2.79 (m, 3H), 2.70-2.58 (m, 2H), 2.40-2.24 (m, 4H), 2.10-2.02 (m, 1H), 1.82-1.65 (m, 4H), 1.39-1.30 (m, 2H), 1.14-1.05 (m, 1H), 0.53-0.47 (m, 2H), 0.30-0.24 (m, 2H) |
| 259 | I-264 | NR | OM | 756.4 | 11.10 (s, 1H), 9.69 (s, 1H), 8.92 (s, 1H), 8.24-8.17 (m, 1H), 8.16-8.12 (m, 1H), 7.89-7.80 (m, 2H), 7.76-7.73 (m, 1H), 7.33-6.97 (m, 4H), 5.14 (dd, J = 5.2, 12.8 Hz, 1H), 4.29-4.17 (m, 1H), 3.18 (t, J = 6.0 Hz, 2H), 3.00-2.91 (m, 2H), 2.91-2.79 (m, 3H), 2.65-2.55 (m, 2H), 2.37-2.29 (m, 2H), 2.14-1.90 (m, 7H), 1.87-1.73 (m, 2H), 1.10-1.01 (m, 1H), 0.53-0.40 (m, 2H), 0.30-0.16 (m, 2H) |
| 260 | I-265 | JG | FX | 868.4 | 11.18 (s, 1H), 10.02 (s, 1H), 8.97 (s, 1H), 8.90 (s, 1H), 8.63 (t, J = 5.6 Hz, 1H), 8.16 (d, J = 5.2 Hz, 1H), 8.05-7.99 (m, 2H), 7.98-7.92 (m, 2H), 7.46-7.17 (m, 1H), 7.15-7.02 (m, 5H), 7.01-6.96 (m, 1H), 5.34 (dd, J = 5.2, 12.8 Hz, 1H), 3.61-3.55 (m, 4H), 3.54-3.51 (m, 2H), 3.47-3.42 (m, 4H), 3.19 (t, J = 6.0 Hz, 2H), 2.92-2.82 (m, 1H), 2.74-2.69 (m, 2H), 2.53-2.52 (m, 2H), 2.19-2.10 (m, 1H), 1.88-1.79 (m, 2H), 1.12-1.01 (m, 1H), 0.49-0.41 (m, 2H), 0.25-0.19 (m, 2H) |
| 261 | I-266 | JG | CN | 889.4 | 11.18 (s, 1H), 11.02 (s, 1H), 9.03 (d, J = 2.8 Hz, 2H), 8.64 (t, J = 6.0 Hz, 1H), 8.27 (d, J = 5.2 Hz, 1H), 8.14-8.00 (m, 5H), 7.81-7.66 (m, 2H), 7.28 (s, 1H), 7.22-7.16 (m, 1H), 7.14-7.06 (m, 2H), 6.99 (d, J = 7.2 Hz, 1H), 5.35 (dd, J = 5.6, 12.8 Hz, 1H), 4.35-4.14 (m, 2H), 3.60-3.57 (m, 4H), 3.56-3.51 (m, 2H), 3.50-3.41 (m, 4H), 2.91-2.81 (m, 1H), 2.76-2.65 (m, 4H), 2.19-2.12 (m, 1H), 1.89-1.78 (m, 2H) |
| 262 | I-267 | KK | FX | 964.2 | 11.08 (s, 1H), 10.00 (s, 1H), 8.97 (s, 1H), 8.92 (s, 1H), 8.65-8.60 (m, 1H), 8.29 (s, 1H), 8.17 (d, J = 5.2 Hz, 1H), 8.06-8.02 (m, 2H), 8.00-7.96 (m, 2H), 7.59-7.54 (m, 1H), 7.46-7.17 (m, 1H), 7.15-7.11 (m, 2H), 7.10-7.01 (m, 4H), 6.22 (d, J = 8.0 Hz, 1H), 5.05 (J = 5.2, 12.8 Hz, 1H), 3.58-3.51 (m, 10H), 3.45 (d, J = 5.6 Hz, 3H), 3.22-3.18 (m, 2H), 2.77 (d, J = 11.6 Hz, 2H), 2.63-2.55 (m, 2H), |

TABLE 21-continued

Compounds synthesized via Method 12 with the coupling of various amines and acids in Step 1.

| Ex-# | I-# | Step 1 Intermediate Amine | Step 1 Intermediate Acid | LCMS (ES+) m/z (M + H)+ | 1HNMR (400 MHz, DMSO-d6) δ |
|---|---|---|---|---|---|
| 263 | I-268 | NU | FX | 920.0 | 2.19 (t, J = 10.4 Hz, 2H), 2.07-1.99 (m, 1H), 1.90 (d, J = 10.4 Hz, 2H), 1.51-1.43 (m, 2H), 1.12-1.04 (m, 1H), 0.48-0.45 (m, 2H), 0.26-0.21 (m, 2H) 10.85 (s, 1H), 9.78 (s, 1H), 8.74 (s, 1H), 8.67 (s, 1H), 8.39 (t, J = 5.4 Hz, 1H), 7.98 (s, 1H), 7.93 (d, J = 5.2 Hz, 1H), 7.82-7.77 (m, 2H), 7.76-7.72 (m, 2H), 7.34-7.26 (m, 1H), 7.23-6.93 (m, 1H), 6.90-6.72 (m, 6H), 5.98 (d, J = 8.2 Hz, 1H), 4.81 (dd, J = 5.6, 12.8 Hz, 1H), 3.35-3.28 (m, 5H), 3.25-3.18 (m, 2H), 2.95 (t, J = 6.0 Hz, 2H), 2.69-2.54 (m, 3H), 2.36-2.29 (m, 3H), 2.01 (t, J = 10.4 Hz, 3H), 1.84-1.74 (m, 1H), 1.64 (d, J = 10.4 Hz, 2H), 1.29-1.18 (m, 2H), 0.91-0.79 (m, 1H), 0.28-0.19 (m, 2H), 0.03-0.04 (m, 2H) |
| 264 | I-269 | JY | FX | 1008.7 | 11.07 (s, 1H), 10.00 (s, 1H), 8.96 (s, 1H), 8.92 (s, 1H), 8.64-8.58 (m, 1H), 8.16 (d, J = 5.2 Hz, 1H), 8.05-8.00 (m, 2H), 7.99-7.95 (m, 2H), 7.59-7.53 (m, 1H), 7.45-7.17 (m, 1H), 7.15-7.11 (m, 2H), 7.15-7.10 (m, 1H), 7.04-7.01 (m, 2H), 6.25-6.19 (m, 1H), 5.08-4.99 (m, 1H), 3.56-3.50 (m, 15H), 3.21-3.14 (m, 2H), 2.90-2.83 (m, 1H), 2.79-2.73 (m, 2H), 2.62-2.57 (m, 1H), 2.57-2.53 (m, 1H), 2.45-2.43 (m, 2H), 2.21-2.15 (m, 2H), 2.05-1.98 (m, 1H), 1.92-1.86 (m, 2H), 1.51-1.42 (m, 2H), 1.10-1.04 (m, 1H), 0.47-0.43 (m, 2H), 0.24-0.21 (m, 2H) |
| 265 | I-270 | HZ | FX | 964.5 | 11.04 (s, 1H), 10.00 (s, 1H), 8.97 (s, 1H), 8.92 (s, 1H), 8.63 (t, J = 5.6 Hz, 1H), 8.16 (d, J = 5.2 Hz, 1H), 8.05-7.96 (m, 4H), 7.53 (d, J = 8.4 Hz, 1H), 7.46-7.16 (m, 1H), 7.12 (s, 1H), 7.07 (t, J = 5.6 Hz, 1H), 7.04 (dd, J = 1.2, 5.2 Hz, 1H), 6.99-6.93 (m, 2H), 6.85 (dd, J = 1.6, 8.8 Hz, 1H), 5.01 (dd, J = 5.6, 12.8 Hz, 1H), 3.62-3.36 (m, 13H), 3.19 (t, J = 6.0 Hz, 2H), 2.92-2.80 (m, 3H), 2.61-2.53 (m, 2H), 2.14 (t, J = 10.8 Hz, 2H), 2.03-1.94 (m, 1H), 1.87 (d, J = 11.2 Hz, 2H), 1.45-1.35 (m, 2H), 1.11-1.03 (m, 1H), 0.50-0.41 (m, 2H), 0.26-0.19 (m, 2H) |
| 266 | I-271 | JZ | FX | 920.5 | 11.03 (s, 1H), 9.99 (s, 1H), 8.97 (s, 1H), 8.90 (s, 1H), 8.62 (t, J = 5.6 Hz, 1H), 8.16 (d, J = 5.2 Hz, 1H), 8.05-8.00 (m, 2H), 7.99-7.95 (m, 2H), 7.52 (d, J = 8.4 Hz, 1H), 7.45-7.16 (m, 1H), 7.12 (s, 1H), 7.09-7.05 (m, 1H), 7.04 (d, J = 6.4 Hz, 1H), 6.98-6.93 (m, 2H), 6.84 (d, J = 8.4 Hz, 1H), 5.06-4.96 (m, 1H), 3.58-3.52 (m, 4H), 3.48-3.38 (m, 5H), 3.21-3.15 (m, 2H), 2.91-2.81 (m, 3H), 2.64-2.54 (m, 1H), 2.53-2.52 (m, 1H), 2.20-2.12 (m, 2H), 2.03-1.95 (m, 1H), 1.90-1.82 (m, 2H), 1.44-1.34 (m, 2H), 1.11-1.00 (m, 1H), 0.48-0.43 (m, 2H), 0.25-0.20 (m, 2H) |

TABLE 21-continued

Compounds synthesized via Method 12 with the coupling of various amines and acids in Step 1.

| Ex-# | I-# | Step 1 Intermediate Amine | Step 1 Intermediate Acid | LCMS (ES+) m/z (M + H)+ | 1HNMR (400 MHz, DMSO-d6) δ |
|---|---|---|---|---|---|
| 267 | I-272 | KA | FX | 1008.7 | 11.04 (s, 1H), 10.01 (s, 1H), 8.97 (s, 1H), 8.92 (s, 1H), 8.62 (t, J = 5.2 Hz, 1H), 8.16 (d, J = 5.2 Hz, 1H), 8.04-7.96 (m, 4H), 7.53 (d, J = 8.4 Hz, 1H), 7.45-7.17 (m, 1H), 7.11 (s, 1H), 7.07 (t, J = 5.6 Hz, 1H), 7.04 (d, J = 5.6 Hz, 1H), 6.99-6.93 (m, 2H), 6.88-6.83 (m, 1H), 5.01 (dd, J = 5.2, 12.8 Hz, 1H), 3.52-3.43 (m, 14H), 3.19 (t, J = 6.0 Hz, 2H), 2.92-2.81 (m, 3H), 2.58-2.61 (m, 1H), 2.57-2.54 (m, 2H), 2.46-2.44 (m, 2H), 2.13 (t, J = 10.8 Hz, 2H), 2.01-1.94 (m, 1H), 1.91-1.83 (m, 2H), 1.46-1.35 (m, 2H), 1.11-1.03 (m, 1H), 0.48-0.43 (m, 2H), 0.25-0.20 (m, 2H) |
| 268 | I-273 | KL | FX | 950.5 | 11.06 (s, 1H), 10.00 (s, 1H), 8.97 (s, 1H), 8.90 (s, 1H), 8.62 (t, J = 5.6 Hz, 1H), 8.16 (d, J = 5.2 Hz, 1H), 8.06-7.94 (m, 4H), 7.66 (dd, J = 7.2, 8.4 Hz, 1H), 7.46-7.16 (m, 3H), 7.12 (s, 1H), 7.07 (t, J = 5.2 Hz, 1H), 7.04 (dd, J = 1.2, 5.2 Hz, 1H), 5.08 (dd, J = 5.2, 12.8 Hz, 1H), 3.59-3.53 (m, 8H), 3.48-3.41 (m, 2H), 3.27-3.22 (m, 4H), 3.19 (t, J = 6.0 Hz, 2H), 2.90-2.81 (m, 1H), 2.62-2.57 (m, 4H), 2.57-2.54 (m, 2H), 2.54-2.52 (m, 2H), 2.08-1.97 (m, 1H), 1.12-1.01 (m, 1H), 0.49-0.41 (m, 2H), 0.25-0.20 (m, 2H) |
| 269 | I-274 | NY | FX | 906.4 | 11.07 (s, 1H), 10.02 (s, 1H), 8.99 (s, 1H), 8.91 (s, 1H), 8.62 (t, J = 5.6 Hz, 1H), 8.27 (s, 1H), 8.17 (d, J = 5.2 Hz, 1H), 8.09-8.02 (m, 2H), 8.01-7.94 (m, 2H), 7.69-7.61 (m, 1H), 7.33 (d, J = 5.2 Hz, 1H), 7.24 (d, J = 8.8 Hz, 1H), 7.20-7.11 (m, 1H), 7.10-7.02 (m, 2H), 5.08 (dd, J = 5.6, 12.8 Hz, 1H), 3.62-3.55 (m, 8H), 3.21 (d, J = 6.0 Hz, 4H), 2.93-2.82 (m, 2H), 2.64-2.57 (m, 6H), 2.07-1.98 (m, 1H), 1.12-1.04 (m, 1H), 0.50-0.43 (m, 2H), 0.24 (q, J = 4.8 Hz, 2H) |
| 270 | I-275 | KB | FX | 994.6 | 10.84 (s, 1H), 9.77 (s, 1H), 8.74 (s, 1H), 8.68 (s, 1H), 8.38 (t, J = 5.6 Hz, 1H), 7.93 (d, J = 5.2 Hz, 1H), 7.85-7.68 (m, 4H), 7.53-7.32 (m, 1H), 7.24-6.92 (m, 3H), 6.91-6.74 (m, 3H), 4.85 (dd, J = 5.6, 12.8 Hz, 1H), 3.37-3.17 (m, 15H), 3.03 (s, 4H), 2.95 (t, J = 6.0 Hz, 2H), 2.72-2.56 (m, 1H), 2.36 (d, J = 4.4 Hz, 5H), 2.24-2.20 (m, 2H), 2.20-1.84 (m, 1H), 1.83-1.74 (m, 1H), 0.96-0.71 (m, 1H), 0.27-0.15 (m, 2H), 0.05-0.07 (m, 2H) |
| 271 | I-276 | OA | FX | 950.5 | 10.85 (s, 1H), 9.81 (s, 1H), 8.75 (s, 1H), 8.68 (s, 1H), 8.42 (t, J = 5.6 Hz, 1H), 8.06 (s, 1H), 7.93 (d, J = 5.6 Hz, 1H), 7.84-7.70 (m, 4H), 7.42 (d, J = 8.8 Hz, 1H), 7.25-6.93 (m, 3H), 6.91-6.83 (m, 2H), 6.81 (dd, J = 1.2, 5.2 Hz, 1H), 4.83 (dd, J = 5.2, 12.8 Hz, 1H), 3.40-3.29 (m, 8H), 3.26-3.19 (m, 2H), 3.15 (s, 4H), 2.95 (t, J = 6.0 Hz, 2H), |

TABLE 21-continued

Compounds synthesized via Method 12 with the coupling of various amines and acids in Step 1.

| Ex-# | I-# | Step 1 Intermediate Amine | Step 1 Intermediate Acid | LCMS (ES+) m/z (M + H)+ | 1HNMR (400 MHz, DMSO-d6) δ |
|---|---|---|---|---|---|
| 272 | I-277 | KF | FX | 906.4 | 2.71-2.58 (m, 1H), 2.36 (s, 2H), 2.31-2.29 (m, 6H), 1.84-1.70 (m, 1H), 0.85-0.81 (m, 1H), 0.28-0.14 (m, 2H), 0.03-0.15 (m, 2H) 11.06 (s, 1H), 10.00 (s, 1H), 8.97 (s, 1H), 8.92 (s, 1H), 8.63 (t, J = 5.6 Hz, 1H), 8.16 (d, J = 5.2 Hz, 1H), 8.02 (d, J = 8.8 Hz, 2H), 7.99 (d, J = 8.8 Hz, 2H), 7.63 (d, J = 8.4 Hz, 1H), 7.46-7.15 (m, 3H), 7.12 (s, 1H), 7.11-7.01 (m, 2H), 5.05 (dd, J = 5.2, 12.8 Hz, 1H), 3.61-3.53 (m, 4H), 3.50-3.44 (m, 2H), 3.39-3.34 (m, 4H), 3.19 (t, J = 6.0 Hz, 2H), 2.95-2.81 (m, 1H), 2.61-2.53 (m, 8H), 2.06-1.95 (m, 1H), 1.12-1.01 (m, 1H), 0.51-0.42 (m, 2H), 0.28-0.18 (m, 2H) |
| 273 | I-278 | NZ | FX | 994.5 | 11.07 (s, 2H), 10.21 (s, 1H), 9.17 (s, 1H), 8.92 (s, 1H), 8.68 (t, J = 5.2 Hz, 1H), 8.13-7.92 (m, 5H), 7.73 (d, J = 8.4 Hz, 1H), 7.65 (s, 1H), 7.50-7.18 (m, 4H), 5.08 (dd, J = 5.2, 12.8 Hz, 1H), 4.19 (d, J = 13.6 Hz, 2H), 3.90-3.78 (m, 2H), 3.62-3.52 (m, 12H), 3.50-3.29 (m, 8H), 3.19-3.17 (m, 2H), 2.95-2.80 (m, 1H), 2.69-2.53 (m, 2H), 2.08-1.96 (m, 1H), 1.23-1.09 (m, 1H), 0.61-0.51 (m, 2H), 0.35-0.31 (m, 2H) |
| 274 | I-279 | GD | JE | 922.1 | 11.09 (s, 1H), 10.01 (s, 1H), 9.00 (s, 1H), 8.86 (s, 1H), 8.25 (d, J = 5.2 Hz, 1H), 7.90 (d, J = 6.4 Hz, 2H), 7.80 (d, J = 7.2 Hz, 1H), 7.74 (s, 1H), 7.68 (s, 1H), 7.63-7.53 (m, 3H), 7.45-7.14 (m, 3H), 5.12 (dd, J = 5.2, 12.8 Hz, 1H), 4.31-4.18 (m, 2H), 3.66-3.38 (m, 10H), 3.00 (s, 3H), 2.93-2.76 (m, 3H), 2.64-2.52 (m, 2H), 2.09-1.99 (m, 1H), 1.85 (t, J = 7.2 Hz, 2H) |
| 275 | I-280 | HQ | JE | 909.5 | 11.07 (s, 1H), 10.03 (s, 1H), 9.00 (s, 1H), 8.93-8.89 (m, 1H), 8.66-8.61 (m, 1H), 8.25 (d, J = 5.2 Hz, 1H), 8.03-7.94 (m, 4H), 7.61 (t, J = 6.4 Hz, 1H), 7.46-7.18 (m, 3H), 7.08-6.75 (m, 3H), 5.41-5.30 (m, 1H), 4.30-4.20 (m, 2H), 3.62-3.43 (m, 13H), 2.98-2.81 (m, 3H), 2.66-2.53 (m, 2H), 2.03-1.95 (m, 1H), 1.86-1.75 (m, 2H) |
| 276 | I-281 | HR | JE | 964.4 | 11.11 (s, 1H), 10.07 (s, 1H), 9.02 (s, 1H), 8.93 (s, 1H), 8.65 (s, 1H), 8.26 (d, J = 5.2 Hz, 1H), 8.06-8.00 (m, 2H), 8.00-7.94 (m, 2H), 7.63 (t, J = 6.4 Hz, 1H), 7.57 (t, J = 8.0 Hz, 1H), 7.54-7.30 (m, 1H), 7.27 (s, 1H), 7.22 (d, J = 5.2 Hz, 1H), 7.14 (d, J = 8.8 Hz, 1H), 7.03 (d, J = 6.8 Hz, 1H), 6.60 (s, 1H), 5.11-5.01 (m, 1H), 4.32-4.21 (m, 2H), 3.80-3.70 (m, 1H), 3.59-3.45 (m, 10H), 2.95-2.87 (m, 1H), 2.87-2.72 (m, 2H), 2.71-2.63 (m, 1H), 2.63-2.57 (m, 1H), 2.56-2.53 (m, 2H), 2.13-1.99 (m, 2H), 1.92-1.80 (m, 1H) |
| 277 | I-282 | HK | JE | 964.1 | 11.08 (s, 1H), 10.03 (s, 1H), 9.01 (s, 1H), 8.92 (s, 1H), 8.62 (t, J = 5.6 Hz, 1H), 8.25 (d, J = 5.2 Hz, 1H), 8.06-8.00 (m, 2H), 8.00-7.94 (m, 2H), 7.64-7.55 (m, 2H), |

TABLE 21-continued

Compounds synthesized via Method 12 with the coupling of various amines and acids in Step 1.

| Ex-# | I-# | Step 1 Intermediate Amine | Step 1 Intermediate Acid | LCMS (ES+) m/z (M + H)+ | 1HNMR (400 MHz, DMSO-d6) δ |
|---|---|---|---|---|---|
| | | | | | 7.47-7.17 (m, 3H), 7.13 (d, J = 8.8 Hz, 1H), 7.03 (d, J = 7.2 Hz, 1H), 6.59 (t, J = 6.0 Hz, 1H), 5.09-5.03 (m, 1H), 4.31-4.20 (m, 2H), 3.80-3.72 (m, 1H), 3.65-3.54 (m, 6H), 3.50-3.42 (m, 4H), 3.31 (t, J = 5.6 Hz, 2H), 2.94-2.86 (m, 1H), 2.85-2.81 (m, 1H), 2.75-2.68 (m, 1H), 2.62-2.54 (m, 2H), 2.12-1.99 (m, 2H), 1.87 (t, J = 10.4 Hz, 1H) |
| 278 | I-283 | KK | JE | 992.5 | 11.09 (s, 1H), 10.02 (s, 1H), 9.00 (s, 1H), 8.92 (s, 1H), 8.63 (t, J = 5.2 Hz, 1H), 8.26 (d, J = 5.2 Hz, 1H), 8.19 (s, 1H), 8.06-7.96 (m, 4H), 7.64-7.53 (m, 2H), 7.27 (s, 1H), 7.46-7.25 (m, 1H), 7.24-7.20 (m, 1H), 7.13 (d, J = 8.8 Hz, 1H), 7.03 (d, J = 7.2 Hz, 1H), 6.22 (d, J = 8.0 Hz, 1H), 5.05 (dd, J = 5.6, 12.8 Hz, 1H), 4.30-4.20 (m, 2H), 3.48-3.43 (m, 1H), 3.60-3.42 (m, 1H), 2.95-2.74 (m, 3H), 2.63-2.52 (m, 5H), 2.21 (t, J = 10.4 Hz, 2H), 2.07-1.98 (m, 1H), 1.90 (d, J = 11.2 Hz, 2H), 1.47 (q, J = 10.0 Hz, 2H) |
| 279[b] | I-284 | KH | OL | 1152.1 | 11.10 (s, 1H), 10.10 (s, 1H), 9.14 (s, 1H), 8.79 (s, 1H), 8.63 (t, J = 6.4 Hz, 1H), 8.10 (d, J = 6.4 Hz, 1H), 7.84-7.72 (m, 2H), 7.65-7.40 (m, 5H), 7.43-7.16 (m, 2H), 7.12-7.09 (m, 1H), 7.03-7.01 (m, 1H), 6.59 (s, 1H), 5.05 (dd, J = 5.2, 12.8 Hz, 1H), 4.58 (d, J = 9.6 Hz, 1H), 4.48-4.21 (m, 4H), 4.01-3.92 (m, 2H), 3.77-3.60 (m, 15H), 3.35-3.30 (m, 2H), 2.96-2.82 (m, 1H), 2.60-2.58 (m, 2H), 2.12-1.97 (m, 2H), 1.96-1.85 (m, 1H), 1.19-1.10 (m, 1H), 1.00-0.88 (m, 9H), 0.59-0.56 (m, 2H), 0.34-0.32 (m, 2H) |
| 280[b] | I-285 | OC | OL | 1193.8 | 10.86-10.84 (m, 1H), 10.85 (s, 1H), 9.76 (s, 1H), 8.80-8.74 (m, 1H), 8.77 (s, 1H), 8.55 (s, 1H), 8.39 (t, J = 6.4 Hz, 1H), 7.90 (d, J = 4.8 Hz, 1H), 7.53 (d, J = 8.4 Hz, 2H), 7.34-7.29 (m, 1H), 7.24-7.19 (m, 3H), 7.18-6.90 (m, 3H), 6.87 (d, J = 8.4 Hz, 2H), 6.78 (d, J = 6.8 Hz, 1H), 6.35 (t, J = 5.6 Hz, 1H), 5.03 (s, 1H), 4.81 (dd, J = 5.2, 12.8 Hz, 1H), 4.27-4.14 (m, 3H), 4.08-4.00 (m, 1H), 4.08-4.00 (m, 1H), 3.71 (m, 2H), 3.68 (m, 1H), 3.63-3.56 (m, 1H), 3.38-3.33 (m, 10H), 3.21 (d, J = 5.2 Hz, 2H), 2.97 (m, 2H), 2.70-2.58 (m, 1H), 2.38-2.34 (m, 1H), 2.34-2.30 (m, 1H), 2.05-1.99 (m, 1H), 1.90-1.86 (m, 1H), 1.79 (m, 1H), 1.76 (s, 3H), 1.77-1.74 (m, 1H), 0.90-0.84 (m, 1H), 0.72 (s, 9H), 0.26 (m, 2H), 0.04--0.01 (m, 2H) |
| 282[b] | I-287 | KG | OL | 1160.5 (M + 23)+ | 11.09 (s, 1H), 10.09 (s, 1H), 9.12 (s, 1H), 8.80 (s, 1H), 8.51 (t, J = 6.4 Hz, 1H), 8.10 (d, J = 6.4 Hz, 1H), 7.86-7.76 (m, 2H), 7.64-7.50 (m, 2H), 7.43 (d, J = 8.4 Hz, 2H), 7.33-6.98 (m, 4H), 6.60 (s, 1H), 5.05 (dd, J = 5.2, 13.2 Hz, 1H), 4.41-4.29 (m, 4H), 4.09 (s, 2H), 3.70-3.23 (m, 18H), 2.94-2.82 (m, 1H), 2.60-2.56 (m, 2H), 2.09-1.97 (m, |

TABLE 21-continued

Compounds synthesized via Method 12 with the coupling of various amines and acids in Step 1.

| Ex-# | I-# | Step 1 Intermediate Amine | Step 1 Intermediate Acid | LCMS (ES+) m/z (M + H)+ | 1HNMR (400 MHz, DMSO-d6) δ |
|---|---|---|---|---|---|
| | | | | | 2H), 1.92-1.82 (m, 1H), 1.19-1.09 (m, 1H), 0.58-0.54 (m, 2H), 0.34-0.30 (m, 2H) |
| 283[b] | I-288 | OB | OL | 1080.7 | 11.09 (s, 1H), 9.98 (s, 1H), 8.95 (s, 1H), 8.78 (s, 1H), 8.58 (s, 1H), 8.15 (d, J = 4.8 Hz, 1H), 7.80 (d, J = 8.4 Hz, 2H), 7.86-7.76 (m, 1H), 7.62-7.52 (m, 1H), 7.48-7.12 (m, 4H), 7.12-6.98 (m, 4H), 6.59 (s, 1H), 5.25 (s, 1H), 5.04 (d, J = 8.4 Hz, 1H), 4.44-4.40 (m, 1H), 4.36-4.62 (m, 2H), 4.12-4.10 (m, 2H), 3.86-3.70 (m, 1H), 3.65-3.51 (m, 14H), 3.19 (d, J = 6.0 Hz, 2H), 2.88-2.82 (m, 1H), 2.62-2.60 (m, 1H), 2.58-2.57 (m, 1H), 2.28-2.22 (m, 1H), 2.10-2.04 (m, 1H), 2.01 (s, 3H) 1.10-1.02 (m, 1H), 0.50-0.40 (m, 2H), 0.25-0.21 (m, 2H) |
| 285 | I-290 | KK | DF | 957.6 | 11.11 (s, 1H), 11.04 (s, 1H), 9.17 (s, 1H), 9.02 (s, 1H), 8.75-8.71 (m, 1H), 8.14 (s, 1H), 8.12-8.03 (m, 6H), 7.79 (s, 1H), 7.66 (s, 1H), 7.63-7.56 (m, 1H), 7.27-7.19 (m, 2H), 7.10-7.03 (m, 1H), 6.20 (d, J = 7.6 Hz, 1H), 5.06 (dd, J = 5.2, 12.8 Hz, 1H), 3.83 (d, J = 4.0 Hz, 3H), 3.64-3.54 (m, 7H), 3.38-3.32 (m, 5H), 3.28 (s, 3H), 3.11 (d, J = 12.0 Hz, 1H), 2.93-2.85 (m, 1H), 2.70-2.55 (m, 3H), 2.14 (d, J = 12.8 Hz, 2H), 2.08-1.98 (m, 2H), 1.87-1.84 (m, 1H), 1.19-1.13 (m, 1H), 0.60-0.55 (m, 2H), 0.36-0.32 (m, 2H) |
| 286 | I-291 | KP | 2-[2-[2-[[2-(2,6-dioxo-3-piperidyl)-1,3-dioxo-isoindolin-4-yl]amino]-ethoxy]ethoxy]acetic acid (synthesized via Steps 1-2 of Example 160) | 860.4 | 11.1 (s, 1H), 10.3 (s, 1H), 9.88 (s, 1H), 8.98 (s, 1H), 8.37 (s, 1H), 8.22 (s, 1H), 8.17 (d, J = 5.6 Hz, 1H), 7.78 (d, J = 8.8 Hz, 2H), 7.58 (t, J = 7.6 Hz, 1H), 7.43 (d, J = 8.8 Hz, 2H), 7.16 (d, J = 8.8 Hz, 1H), 7.14-7.08 (m, 2H), 7.05-7.01 (m, 2H), 6.69-6.59 (m, 1H), 5.10-5.00 (m, 1H), 4.13 (s, 2H), 3.75-3.63 (m, 6H), 3.56-3.51 (m, 2H), 3.25-3.02 (m, 2H), 2.93-2.86 (m, 1H), 2.63-2.59 (m, 1H), 2.59-2.56 (m, 1H), 2.03-1.99 (m, 1H), 1.13-1.07 (m, 1H), 0.49-0.43 (m, 2H), 0.27-0.21 (m, 2H) |
| 287 | I-292 | 4-[2-[2-[2-(2-aminoethoxy)-ethoxy]ethoxy]-ethylamino]-2-(2,6-dioxo-3-piperidyl)-isoindoline-1,3-dione (synthesized via Steps 1-2 of Example 128) | KR | 841.1 | 11.08 (s, 1H), 10.81 (s, 1H), 8.97 (s, 1H), 8.38 (s, 1H), 8.25 (d, J = 5.6 Hz, 1H), 8.21 (s, 1H), 7.71-7.65 (m, 1H), 7.56 (t, J = 8.0 Hz, 1H), 7.25 (s, 1H), 7.17 (d, J = 5.6 Hz, 1H), 7.11 (d, J = 8.4 Hz, 1H), 7.02 (d, J = 7.2 Hz, 1H), 6.58 (s, 1H), 5.04 (dd, J = 5.6, 12.8 Hz, 1H), 4.33-4.17 (m, 2H), 3.93 (s, 3H), 3.61 (t, J = 5.2 Hz, 2H), 3.55 (d, J = 4.8 Hz, 10H), 3.46 (d, J = 4.8 Hz, 4H), 2.91-2.83 (m, 1H), 2.60-2.56 (m, 1H), 2.56-2.52 (m, 1H), 2.08-2.00-(m, 1H) |
| 288 | I-293 | LP | CW | 1109.6 | 10.95 (s, 1H), 9.01-8.93 (m, 2H), 8.60-8.54 (m, 1H), 8.37-8.32 (s, 1H), 8.25-8.23 (m, 1H), 8.18 (s, 1H), 7.89-7.77 (m, 1H), 7.74-7.61 (m, 2H), 7.51 (s, 1H), 7.46-7.33 (m, 4H), 7.25 (s, 1H), 7.16 (d, J = 5.2 Hz, 1H), 4.58-4.18 (m, 7H), 3.69-3.51 (m, 16H), 3.24-3.17 (m, 3H), 3.11-3.08 (m, 1H), |

TABLE 21-continued

Compounds synthesized via Method 12 with the coupling of various amines and acids in Step 1.

| Ex-# | I-# | Step 1 Intermediate Amine | Step 1 Intermediate Acid | LCMS (ES+) m/z (M + H)+ | 1HNMR (400 MHz, DMSO-d6) δ |
|---|---|---|---|---|---|
| 289 | I-294 | LR | KR | 839.4 | 2.67-2.57 (m, 1H), 2.47-2.41 (m, 4H), 2.25-2.17 (m, 1H), 2.13-2.02 (m, 2H), 1.97-1.78 (m, 4H), 1.68-1.50 (m, 2H), 0.90 (s, 9H) 11.08 (s, 1H), 10.84 (s, 1H), 8.97 (s, 1H), 8.37 (s, 1H), 8.35 (t, J = 5.6 Hz, 1H), 8.25 (d, J = 5.6 Hz, 1H), 7.68 (t, J = 6.4 Hz, 1H), 7.59-7.53 (m, 1H), 7.25 (s, 1H), 7.17 (dd, J = 1.2, 5.2 Hz, 1H), 7.05 (d, J = 8.8 Hz, 1H), 7.00 (d, J = 7.2 Hz, 1H), 6.63 (t, J = 5.6 Hz, 1H), 5.04 (dd, J = 5.2, 12.8 Hz, 1H), 4.30-4.19 (m, 2H), 3.93 (s, 3H), 3.54-3.39 (m, 12H), 2.93-2.83 (m, 1H), 2.60 (d, J = 2.4 Hz, 1H), 2.58-2.54 (m, 1H), 2.07-1.97 (m, 1H), 1.85-1.73 (m, 6H) |
| 290 | I-295 | LP | KR | 1020.1 (M + Na)+ | 10.82 (s, 1H), 8.97 (d, J = 1.6 Hz, 2H), 8.57 (t, J = 6.0 Hz, 1H), 8.38 (s, 1H), 8.27-8.22 (m, 2H), 7.70 (t, J = 6.4 Hz, 1H), 7.46-7.30 (m, 4H), 7.25 (s, 1H), 7.17 (dd, J = 1.2, 5.2 Hz, 1H), 4.52 (t, J = 8.0 Hz, 1H), 4.44-4.31 (m, 2H), 4.29-4.19 (m, 3H), 3.94 (s, 3H), 3.74-3.52 (m, 14H), 3.20 (d, J = 6.0 Hz, 2H), 3.08 (s, 1H), 2.61 (td, J = 6.0, 12.0 Hz, 1H), 2.46-2.38 (m, 4H), 2.11-1.99 (m, 1H), 1.95-1.80 (m, 1H), 0.90 (s, 9H) |
| 291 | I-296 | LX | FX | 1204.2 | 10.04 (s, 1H), 8.98 (s, 1H), 8.92 (s, 1H), 8.64 (br t, J = 5.4 Hz, 1H), 8.20-8.14 (m, 2H), 8.06-7.95 (m, 5H), 7.47-7.42 (m, 1H), 7.33-7.29 (m, 1H), 7.14-7.02 (m, 9H), 6.93 (d, J = 2.0 Hz, 1H), 6.82-6.74 (m, 2H), 5.03 (d, J = 9.6 Hz, 1H), 4.93-4.85 (m, 2H), 4.71-4.61 (m, 2H), 4.36 (t, J = 5.2 Hz, 4H), 4.14-4.03 (m, 3H), 3.85 (d, J = 9.2 Hz, 2H), 3.73 (t, J = 4.4 Hz, 3H), 3.46-3.43 (m, 8H), 3.20-3.16 (m, 6H), 3.03-2.94 (m, 2H), 2.70-2.65 (m, 2H), 2.36-2.32 (m, 1H), 1.91-1.75 (m, 2H), 1.68 (d, J = 5.6 Hz, 1H), 1.62-1.50 (m, 2H), 1.04 (d, J = 3.6 Hz, 9H), 0.49-0.43 (m, 2H), 0.26-0.21 (m, 2H) |
| 292 | I-297 | LZ | KR | 853.4 | 11.09 (s, 1H), 10.85 (s, 1H), 8.96 (s, 1H), 8.36 (s, 1H), 8.34-8.20 (m, 2H), 7.71-7.66 (m, 1H), 7.25 (s, 1H), 7.17 (d, J = 4.4 Hz, 1H), 6.99-6.86 (m, 2H), 6.86-6.76 (m, 1H), 5.42-5.28 (m, 1H), 4.31-4.18 (m, 2H), 3.91 (s, 3H), 3.54 (s, 3H), 3.48-3.44 (m, 4H), 3.24-3.17 (m, 4H), 2.97-2.85 (m, 3H), 2.73-2.63 (m, 2H), 2.62-2.55 (m, 2H), 2.02-1.97 (m, 1H), 1.86-1.72 (m, 4H), 0.90 (s, 6H) |
| 293[b] | I-298 | MD | MC | 1144.5 | 10.82 (s, 1H), 8.99-8.96 (m, 2H), 8.61-8.56 (m, 1H), 8.38 (s, 1H), 8.27-8.22 (m, 2H), 7.73-7.65 (m, 1H), 7.43-7.37 (m, 5H), 7.25 (s, 1H), 7.18-7.15 (m, Hz, 1H), 5.16-5.12 (m, 1H), 4.55 (d, J = 9.6 Hz, |

TABLE 21-continued

Compounds synthesized via Method 12 with the coupling of various amines and acids in Step 1.

| Ex-# | I-# | Step 1 Intermediate Amine | Step 1 Intermediate Acid | LCMS (ES+) m/z (M + H)+ | 1HNMR (400 MHz, DMSO-d6) δ |
|---|---|---|---|---|---|
| | | | | | 1H), 4.46-4.41 (m, 1H), 4.36-4.32 (m, 1H), 4.27-4.23 (m, 2H), 3.95 (s, 2H), 3.93 (s, 3H), 3.70-3.40 (m, 26H), 2.53-2.52 (m, 1H), 2.45-2.41 (m, 4H), 2.06-2.00 (m, 1H), 1.93-1.85 (m, 1H), 0.95-0.90 (m, 9H) |
| 294 | I-299 | ME | KR | 1056.4 | 10.82 (s, 1H), 8.98 (s, 2H), 8.59 (t, J = 5.6 Hz, 1H), 8.39 (s, 1H), 8.28-8.20 (m, 2H), 7.69 (t, J = 6.4 Hz, 1H), 7.46-7.36 (m, 5H), 7.26 (s, 1H), 7.17 (d, J = 5.6 Hz, 1H), 5.16 (d, J = 3.2 Hz, 1H), 4.56 (d, J = 9.2 Hz, 1H), 4.48-4.42 (m, 1H), 4.42-4.31 (m, 2H), 4.30-4.27 (m, 1H), 4.26-4.19 (m, 2H), 3.96 (s, 2H), 3.94 (s, 3H), 3.70-3.43 (m, 16H), 2.56-2.52 (m, 2H), 2.44 (s, 3H), 2.09-2.03 (m, 1H), 1.96-1.84 (m, 1H), 0.94 (s, 9H) |
| 295[b] | I-300 | 4-[2-[2-[2-(2-aminoethoxy)-ethoxy]ethoxy]ethylamino]-2-(2,6-dioxo-3-piperidyl)-isoindoline-1,3-dione (synthesized via Steps 1-2 of Example 128) | MF | 667.3 | 11.10 (s, 1H), 10.82 (s, 1H), 8.82 (d, J = 0.8 Hz, 1H), 8.60 (d, J = 0.8 Hz, 1H), 8.33 (s, 1H), 8.21 (t, J = 5.6 Hz, 1H), 7.56 (dd, J = 7.2, 8.4 Hz, 1H), 7.11 (d, J = 8.4 Hz, 1H), 7.02 (d, J = 7.2 Hz, 1H), 6.59 (t, J = 5.6 Hz, 1H), 5.05 (dd, J = 5.2, 12.8 Hz, 1H), 3.91 (s, 3H), 3.63-3.57 (m, 2H), 3.57-3.49 (m, 10H), 3.47-3.39 (m, 4H), 2.93-2.82 (m, 1H), 2.63-2.52 (m, 2H), 2.08-1.97 (m, 1H) |
| 296[b] | I-301 | 4-[2-[2-[2-(2-aminoethoxy)-ethoxy]ethoxy]-ethylamino]-2-(2,6-dioxo-3-piperidyl)-isoindoline-1,3-dione (synthesized via Steps 1-2 of Example 128) | MI | 744.1 | 11.08 (s, 1H), 10.89 (s, 1H), 9.07 (s, 1H), 8.83 (d, J = 6.4 Hz, 2H), 8.38 (s, 1H), 8.25-8.22 (m, 1H), 7.94 (d, J = 6.0 Hz, 2H), 7.57-7.53 (m, 1H), 7.10 (d, J = 8.8 Hz, 1H), 7.01 (d, J = 6.4 Hz, 1H), 6.59-6.56 (m, 1H), 5.07-5.02 (m, 1H), 3.93 (s, 3H), 3.61-3.59 (m, 2H), 3.55-3.54 (m, 10H), 3.46-3.43 (m, 4H), 2.87-2.86 (m, 1H), 2.82-2.56 (m, 2H), 2.04-2.01 (m, 1H) |

[a]For variations on Method 12, see Table 10.
[b]No deprotection Step 2 was required.

Further Examples Using Synthetic Methods Similar to Method 12

Example 281: [(3R,5S)-5-[[4-[4-[[2-[2-(cyclopropylmethylamino)-4-pyridyl]oxazole-4-carbonyl]amino]-3-(difluoromethyl)pyrazol-1-yl]phenyl]methylcarbamoyl]-1-[(2S)-2-[[2-[2-[2-[2-[[2-(2,6-dioxo-3-piperidyl)-1,3-dioxo-isoindolin-4-yl]amino]ethoxy]ethoxy]ethoxy]acetyl]amino]-3,3-dimethyl-butanoyl]pyrrolidin-3-yl](2S)-pyrrolidine-2-carboxylate, I-286

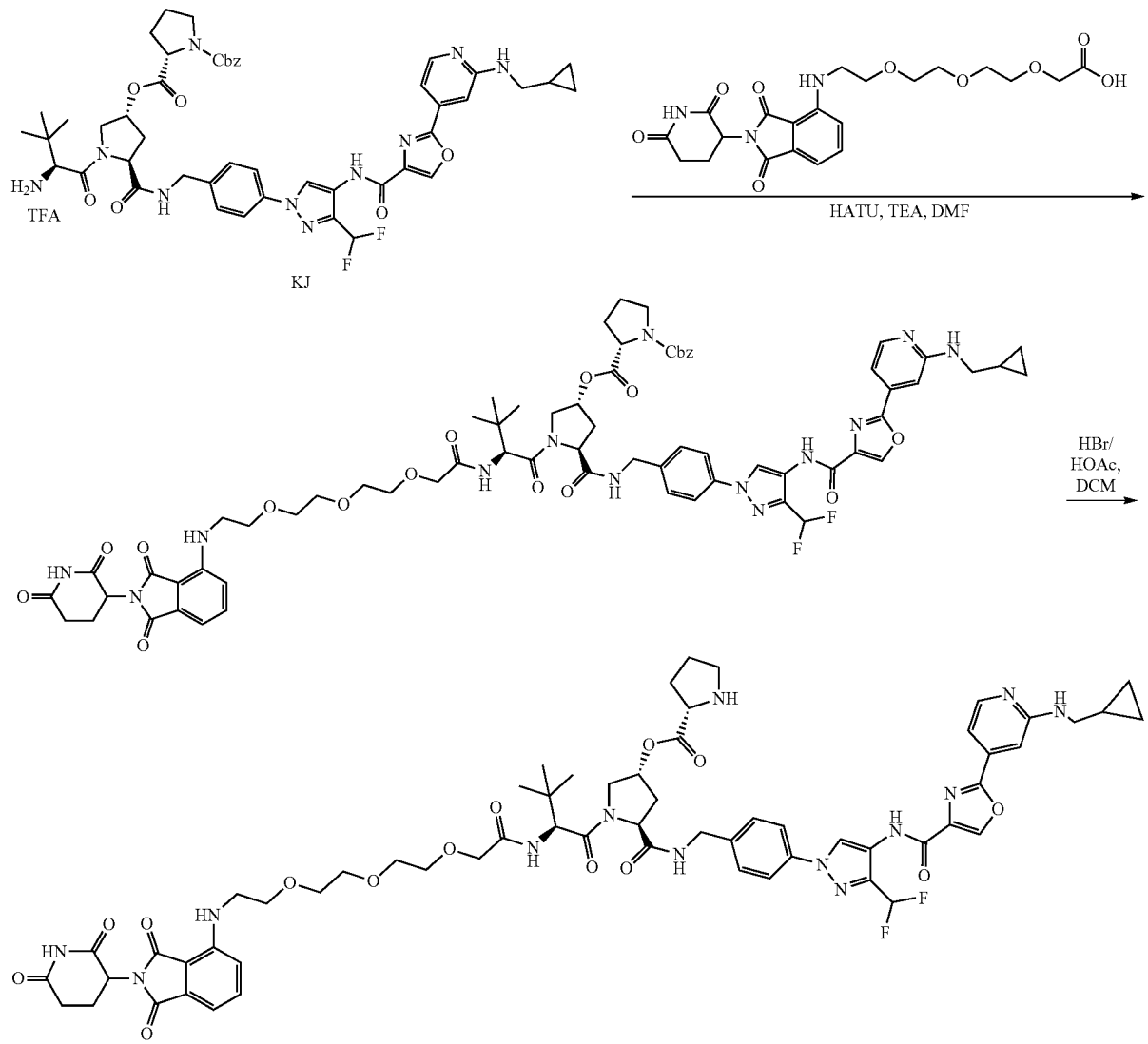

To a solution of O1-benzyl O2-[(3R,5S)-5-[[4-[4-[[2-[2-(cyclopropylmethylamino)-4-pyridyl]oxazole-4-carbonyl]amino]-3-(difluoromethyl)pyrazol-1-yl]phenyl]methylcarbamoyl]-1-[(2S)-2-[[2-[2-[2-[2-[[2-(2,6-dioxo-3-piperidyl)-1,3-dioxo-isoindolin-4-yl]amino]ethoxy]ethoxy]ethoxy]acetyl]amino]-3,3-dimethyl-butanoyl]pyrrolidin-3-yl] (2S)-pyrrolidine-1,2-dicarboxylate (140 mg, 101 umol, synthesized via Method 12 with Intermediate KJ as the amine and 2-(2-(2-(2-((2-(2,6-dioxopiperidin-3-yl)-1,3-dioxoisoindolin-4-yl)amino)ethoxy)ethoxy)ethoxy)acetic acid, synthesized via Steps 1-2 of Example 152, as the acid in Step 1) in DCM (4 mL) was added HBr/HOAc (101 umol, 2 mL, 33% solution), and the reaction mixture was stirred at rt for 1.5 hr. On completion, the reaction mixture was concentrated in vacuo to give a residue. The residue was purified by prep-HPLC (column: Phenomenex Synergi C18 150*25*10 um; mobile phase: [water (0.225% FA)-ACN]; B %: 21%-41%, 8 min) to give the title compound (42.9 mg, 32% yield) as a white solid. $^1$H NMR (400 MHz, DMSO-$d_6$) 11.07 (s, 1H), 9.95 (s, 1H), 8.96 (s, 1H), 8.78 (s, 1H), 8.64 (t, J=6.0 Hz, 1H), 8.16 (d, J=5.2 Hz, 1H), 7.85-7.71 (m, 2H), 7.55 (t, J=8.0 Hz, 1H), 7.48-7.14 (m, 4H), 7.14-7.09 (m, 2H), 7.08-7.05 (m, 1H), 7.04-6.98 (m, 2H), 6.62-6.53 (m, 1H), 5.30 (s, 1H), 5.04 (dd, J=5.2, 12.8 Hz, 1H), 4.54-4.35 (m, 3H), 4.32-4.24 (m, 1H), 3.98-3.89 (m, 3H), 3.87-3.82 (m, 1H), 3.70-3.58 (m, 11H), 3.48-3.40 (m, 2H), 3.19 (t, J=6.0 Hz, 2H), 2.93-2.83 (m, 2H), 2.80-2.72 (m, 1H), 2.63-2.54 (m, 2H), 2.29-2.22 (m, 1H), 2.18-1.87 (m, 4H), 1.77-1.69 (m, 1H), 1.68-1.53 (m, 1H), 1.09-1.02 (m, 1H), 1.00-0.90 (m, 9H), 0.49-0.41 (m, 2H), 0.26-0.19 (m, 2H); LC-MS (ESI+) m/z 1248.3 (M+H)+.

Example 284: (3R,5S)-5-[[4-[4-[[2-[2-(cyclopropyl-methylamino)-4-pyridyl]oxazole-4-carbonyl]amino]-3-(difluoromethyl)pyrazol-1-yl]phenyl]methylcarbamoyl]-1-[2-[2-[2-[2-[[2-(2,6-dioxo-3-piperidyl)-1,3-dioxo-isoindolin-4-yl]amino]ethoxy]ethoxy]ethoxy]acetyl]pyrrolidin-3-yl](2S)-pyrrolidine-2-carboxylate, I-289

55.1 umol, synthesized via Step 1 of Method 12, coupling amine intermediate KI with 2-(2-(2-(2-((2-(2,6-Dioxopiperidin-3-yl)-1,3-dioxoisoindolin-4-yl)amino)ethoxy)ethoxy)ethoxy)acetic acid (synthesized via Steps 1-2 of Example 152) as the acid) in DCM (2 mL) was added HBr/AcOH (4 M, 1 mL, 33 wt %), and the reaction mixture was stirred at rt for 4 hrs. On completion, the reaction mixture was concentrated in vacuo to give a residue. The residue was purified by prep-HPLC (column: Phenomenex Synergi C18 150*25*10 um; mobile phase: [water (0.225% FA)-ACN]; B %: 10%-37%, 2 min) to give the title compound (40.7 mg, 61% yield) as a yellow solid. 1H NMR (400 MHz, DMSO-d6) δ 1H NMR (400 MHz, DMSO-d6) δ 11.07 (s, 1H), 9.95 (s, 1H), 8.96 (s, 1H), 8.79 (s, 1H), 8.57 (t, J=5.6 Hz, 1H), 8.16 (d, J=5.2 Hz, 1H), 7.85-7.76 (m, 2H), 7.61-7.53 (m, 1H), 7.43 (d, J=8.4 Hz, 2H), 7.41-7.09 (m, 3H), 7.09-6.97 (m, 3H), 6.64-6.52 (m, 1H), 5.29 (s, 1H), 5.04 (dd, J=5.6, 12.8 Hz, 1H), 4.42 (t, J=7.6 Hz, 1H), 4.38-4.30 (m, 2H),

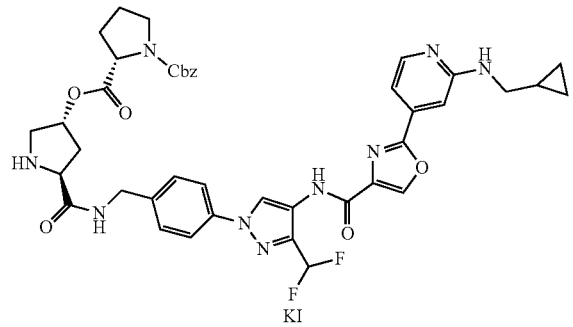

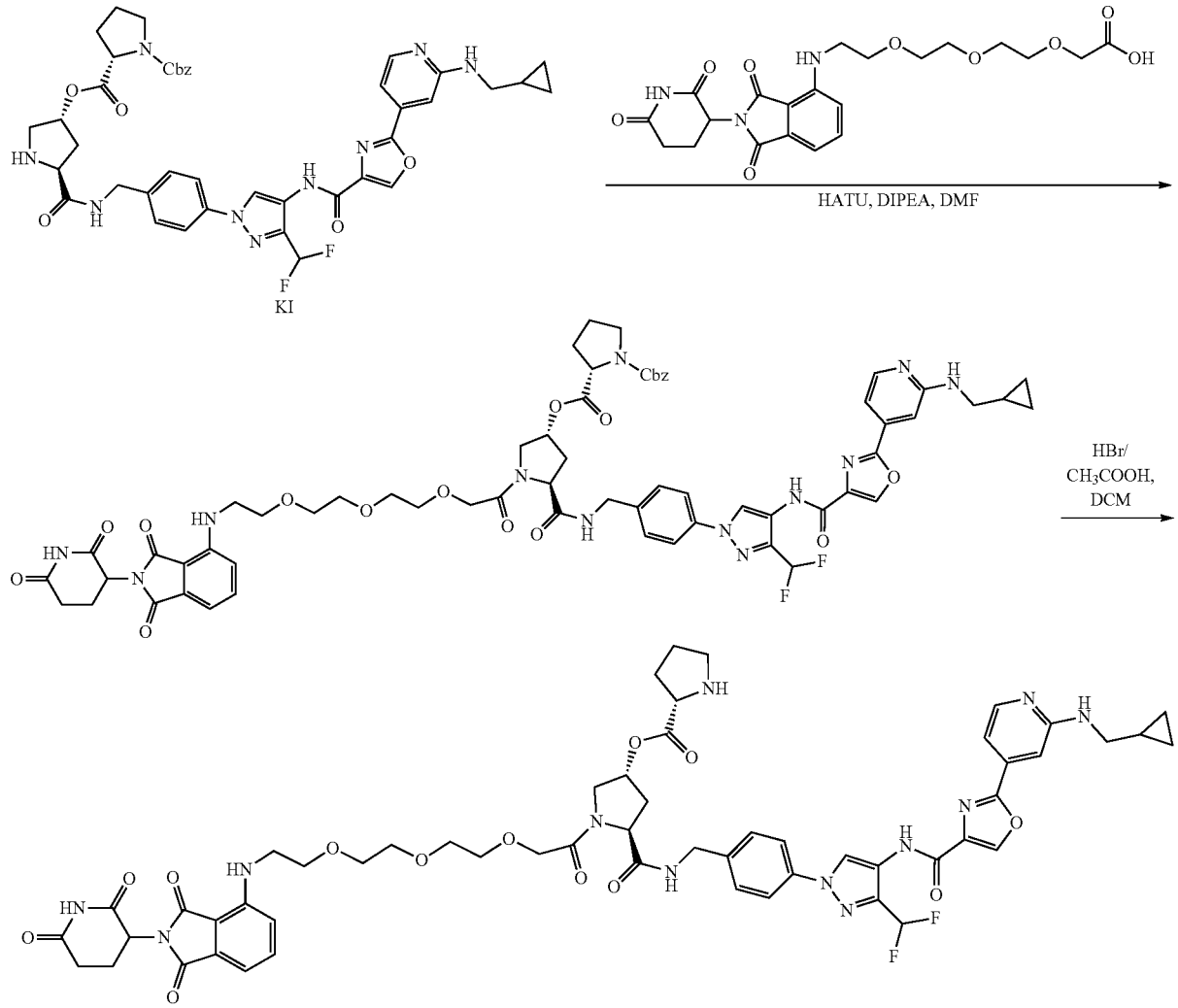

To a solution of O1-benzyl O2-[(3R,5S)-5-[[4-[4-[[2-[2-(cyclopropylmethylamino)-4-pyridyl]oxazole-4-carbonyl]amino]-3-(difluoromethyl)pyrazol-1-yl]phenyl]methylcarbamoyl]-1-[2-[2-[2-[2-[[2-(2,6-dioxo-3-piperidyl)-1,3-dioxo-isoindolin-4-yl]amino]ethoxy]ethoxy]ethoxy]acetyl]pyrrolidin-3-yl](2S)-pyrrolidine-1,2-dicarboxylate (70 mg, 4.14-4.03 (m, 2H), 3.85-3.64 (m, 4H), 3.63-3.59 (m, 4H), 3.51-3.41 (m, 8H), 3.22-3.02 (m, 2H), 2.92-2.84 (m, 2H), 2.80-2.74 (m, 1H), 2.64-2.55 (m, 2H), 2.27-2.20 (m, 1H), 2.15-2.06 (m, 1H), 2.04-1.92 (m, 2H), 1.77-1.69 (m, 1H), 1.68-1.57 (m, 2H), 1.11-1.01 (m, 1H), 0.49-0.42 (m, 2H), 0.23 (q, J=4.8 Hz, 2H); LC-MS (ESI+) m/z 1135.7 (M+1)+.

Example 297: N-[3-carbamoyl-1-[4-[[4-[2-[2-[[2-(2,6-dioxo-3-piperidyl)-1,3-dioxo-isoindolin-4-yl]amino]ethoxy]ethyl]morpholin-2-yl]methoxymethyl]phenyl]pyrazol-4-yl]-2-[2-(2,2,2-trifluoroethylamino)-4-pyridyl]oxazole-4-carboxamide, I-302

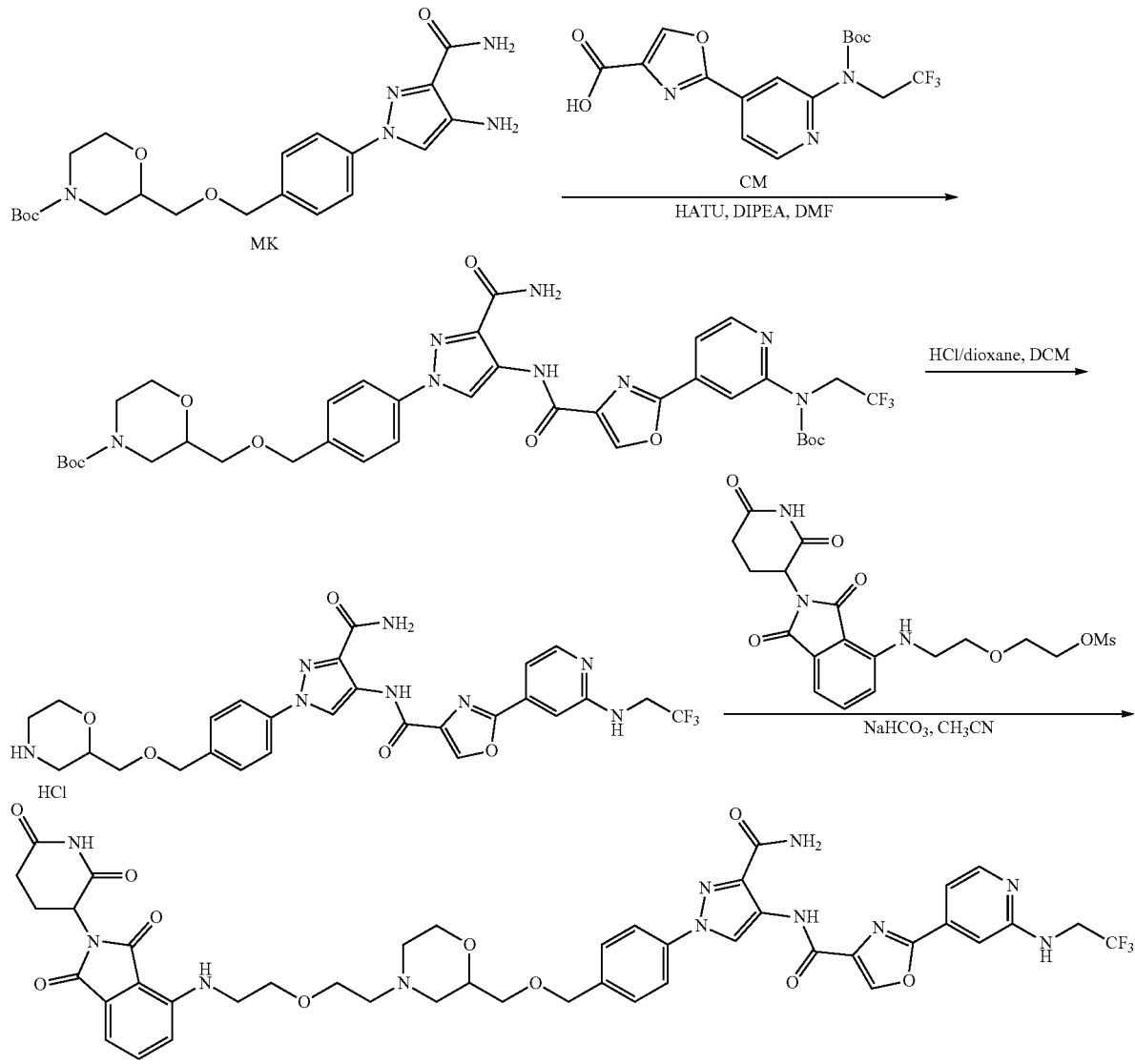

To a mixture of N-[3-carbamoyl-1-[4-(morpholin-2-ylmethoxymethyl)phenyl]pyrazol-4-yl]-2-[2-(2,2,2-trifluoroethylamino)-4-pyridyl]oxazole-4-carboxamide (70.0 mg, 109.89 umol, HCl, synthesized via Steps 1-2 of Method 12 coupling amine tert-butyl 2-[[4-(4-amino-3-carbamoyl-pyrazol-1-yl)phenyl]methoxymethyl]morpholine-4-carboxylate, Intermediate MK, and acid 2-[2-[tert-butoxycarbonyl(2,2,2-trifluoroethyl)amino]-4-pyridyl]oxazole-4-carboxylic acid, Intermediate CM, in Step 1) in MeCN (10 mL) was added NaHCO₃ (36.93 mg, 439.55 umol). Then 2-[2-[[2-(2,6-dioxo-3-piperidyl)-1,3-dioxo-isoindolin-4-yl]amino]ethoxy]ethyl methanesulfonate (48.29 mg, 109.89 umol, synthesized via Steps 1-2 of Example 184) was added into the mixture. The mixture was stirred at 80° C. for 12 hours. On completion, the reaction mixture was concentrated in vacuo. The residue was purified by prep-HPLC (column: Phenomenex Synergi C18 150*25*10 um; mobile phase: [water (0.225% FA)-ACN]; B %: 25%-42%, 6 min) to give the title compound (42.0 mg, 35% yield) as a yellow solid. $^1$H NMR (400 MHz, DMSO-$d_6$) δ 11.09 (s, 1H), 11.00 (s, 1H), 9.02 (s, 1H), 8.92 (s, 1H), 8.24 (s, 1H), 8.06-8.02 (m, 1H), 8.04 (s, 1H), 7.94 (d, J=8.4 Hz, 2H), 7.74-7.66 (m, 2H), 7.60-7.53 (m, 1H), 7.46 (d, J=8.4 Hz, 2H), 7.26 (s, 1H), 7.19-7.10 (m, 2H), 7.02 (d, J=7.2 Hz, 1H), 6.59 (t, J=5.6 Hz, 1H), 5.09-5.01 (m, 1H), 4.51 (s, 2H), 4.29-4.18 (m, 2H), 3.79-3.68 (m, 1H), 3.58 (d, J=5.6, 15.2 Hz, 9H), 3.39 (d, J=4.8 Hz, 4H), 2.92-2.75 (m, 2H), 2.72-2.53 (m, 3H), 2.33 (td, J=1.8, 9.2 Hz, 1H), 2.08-1.97 (m, 1H), 2.10-1.97 (m, 1H); LC-MS (ESI⁺) m/z 944.1 (M+H)⁺.

Example 298: N-[3-carbamoyl-1-[4-[[1-[2-[2-[[2-(2,6-dioxo-3-piperidyl)-1,3-dioxo-isoindolin-4-yl]amino]ethoxy]ethyl]-2-piperidyl]methoxymethyl]phenyl]pyrazol-4-yl]-2-[2-(2,2,2-trifluoroethylamino)-4-pyridyl]oxazole-4-carboxamide, I-303
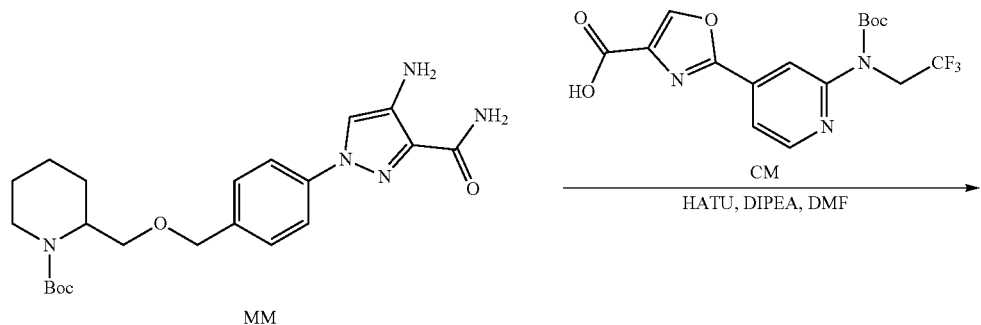
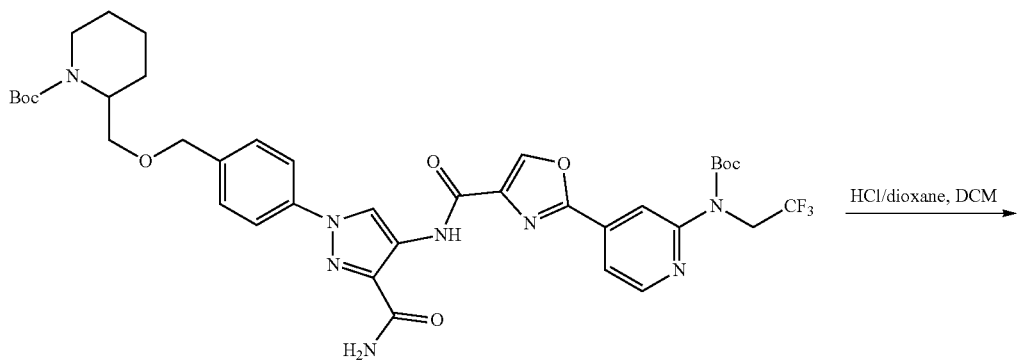
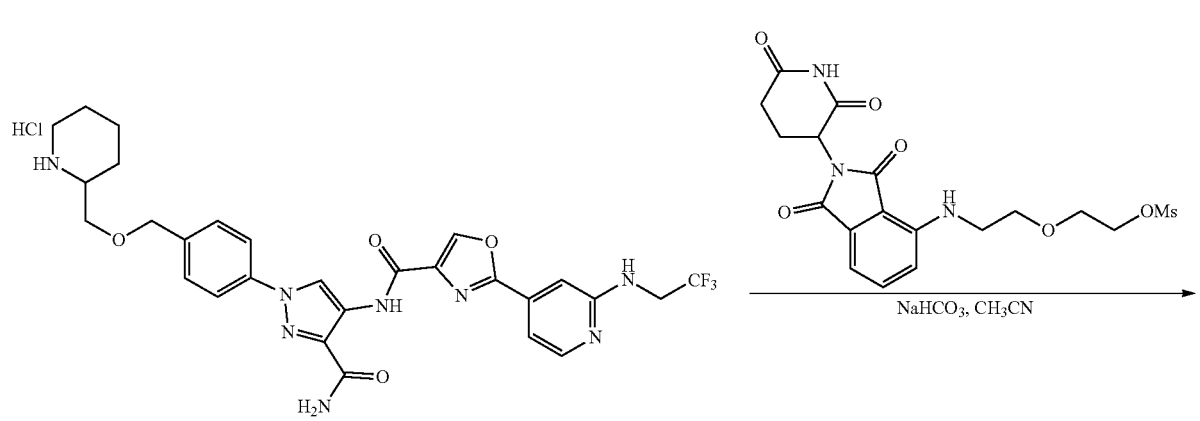

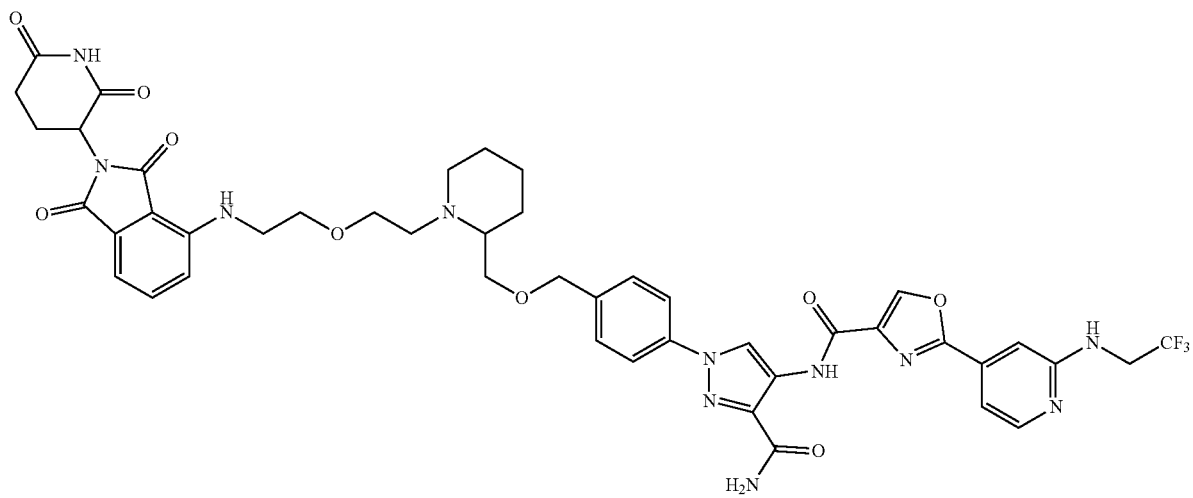

To a mixture of N-[3-carbamoyl-1-[4-(2-piperidyl-methoxymethyl)phenyl]pyrazol-4-yl]-2-[2-(2,2,2-trifluoro-ethylamino)-4-pyridyl]oxazole-4-carboxamide (70.0 mg, 110.2 umol, HCl, synthesized via Method 12 coupling amine tert-butyl 2-[[4-(4-amino-3-carbamoyl-pyrazol-1-yl)phenyl] methoxymethyl]piperidine-1-carboxylate, Intermediate MM and acid 2-[2-[tert-butoxycarbonyl(2,2,2-trifluoroethyl) amino]-4-pyridyl]oxazole-4-carboxylic acid, Intermediate CM in Step 1) in CH$_3$CN (10 mL) was added NaHCO$_3$ (37.0 mg, 441 umol). Then 2-[2-[[2-(2,6-dioxo-3-piperidyl)-1,3-dioxo-isoindolin-4-yl]amino]ethoxy]ethyl methanesulfonate (48.4 mg, 110 umol, synthesized via Steps 1-2 of Example 184) was added into the mixture. The mixture was stirred at 80° C. for 24 hrs. On completion, the reaction mixture was concentrated in vacuo. The residue was purified by prep-HPLC (column: Phenomenex Synergi C18 150*25*10 um; mobile phase: [water (0.225% FA)-ACN]; B %: 22%-42%, 7 min) to give the title compound (32.8 mg, 30% yield) as a yellow solid. $^1$H NMR (400 MHz, DMSO-d$_6$) δ 11.09 (s, 1H), 11.00 (s, 1H), 9.03 (s, 1H), 8.92 (s, 1H), 8.28-8.25 (m, 3H), 8.04 (s, 1H), 7.93 (d, J=8.4 Hz, 2H), 7.74-7.66 (m, 2H), 7.59-7.53 (m, 1H), 7.46 (d, J=8.4 Hz, 2H), 7.28 (s, 1H), 7.19 (d, J=4.0 Hz, 1H), 7.12 (d, J=8.4 Hz, 1H), 7.02 (d, J=7.2 Hz, 1H), 6.58 (s, 1H), 5.05 (dd, J=5.6, 12.8 Hz, 1H), 4.49 (s, 2H), 4.25 (dd, J=6.0, 9.2 Hz, 2H), 3.60-3.55 (m, 6H), 3.51 (s, 7H), 2.87-2.85 (m, 4H), 2.70-2.64 (m, 3H), 2.34-2.14 (m, 2H), 1.60 (s, 3H), 1.36-1.24 (m, 1H). LC-MS (ESI$^+$) m/z 942.2 (M+H)$^+$.

Example 299: N-[3-carbamoyl-1-[[1-[2-[2-[2-[[2-(2, 6-dioxo-3-piperidyl)-1,3-dioxo-isoindolin-4-yl] amino]ethoxy]ethoxy]ethyl]triazol-4-yl]methyl]pyrazol-4-yl]-2-[2-(cyclopropylmethylamino)-4-pyridyl] oxazole-4-carboxamide, I-304

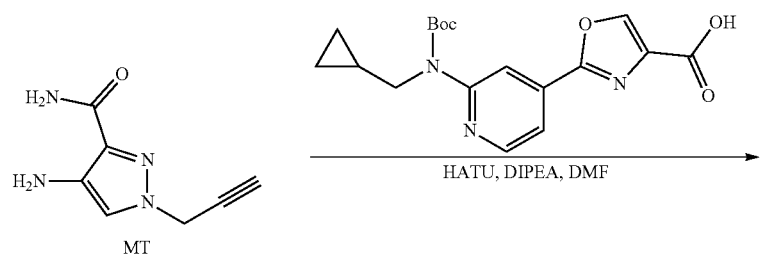

2439
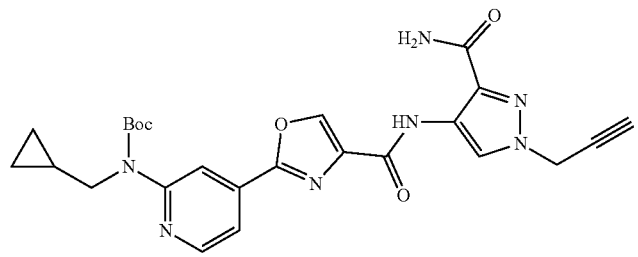
2440
-continued
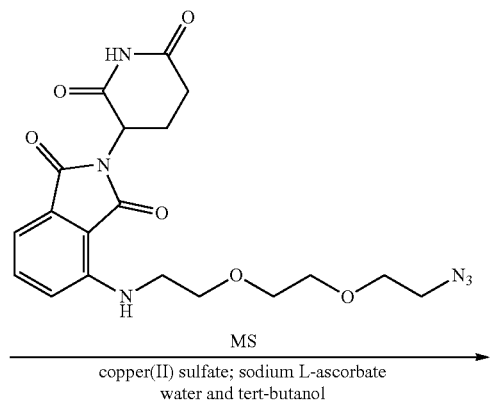
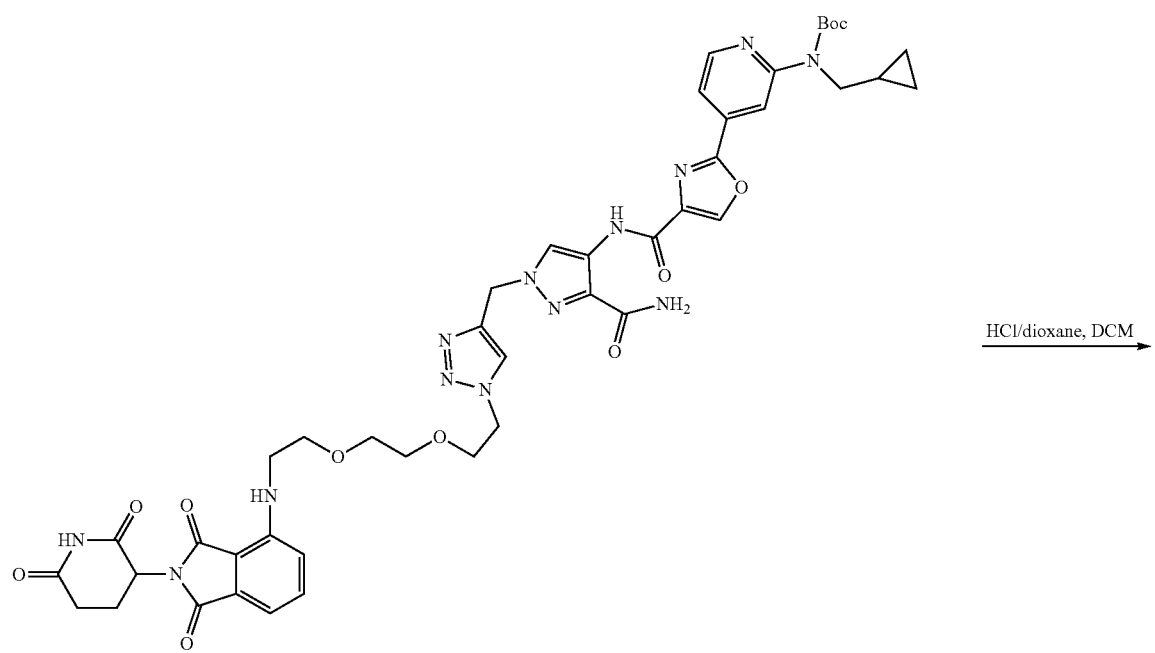

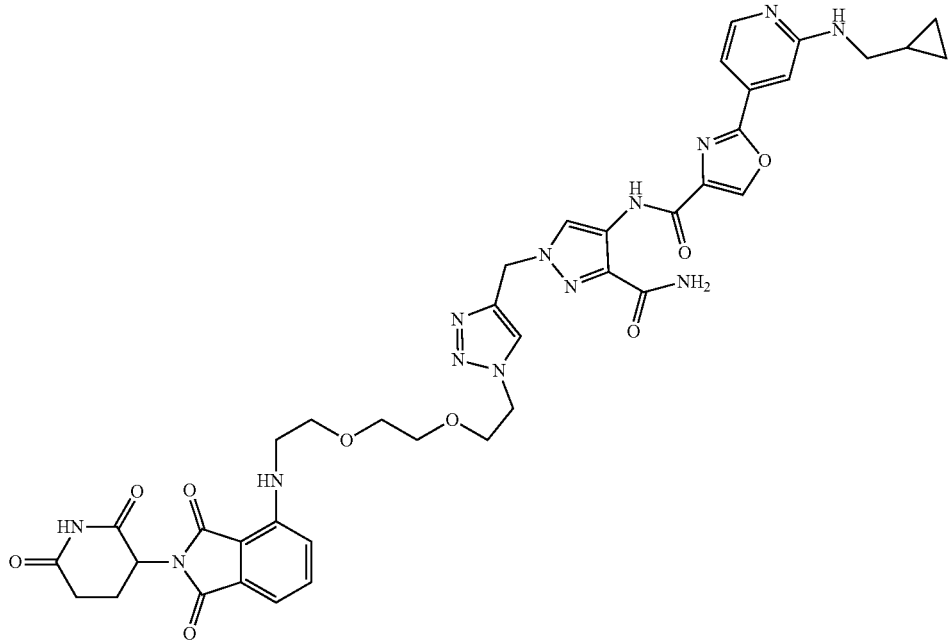 [SMILES: NC(=O)c1nn(Cc2cn(CCOCCOCCNc3cccc4c3C(=O)N(C3CCC(=O)NC3=O)C4=O)nn2)cc1NC(=O)c1coc(-c2ccnc(NCC3CC3)c2)n1]

Step 2—Tert-butyl N-[4-[4-[[3-carbamoyl-1-[[1-[2-[2-[2-[[2-(2,6-dioxo-3-piperidyl)-1,3-dioxo-isoindolin-4-yl]amino]ethoxy]ethoxy]ethyl]triazol-4-yl]methyl]pyrazol-4-yl]carbamoyl]oxazol-2-yl]-2-pyridyl]-N-(cyclopropylmethyl)carbamate To a solution of tert-butyl N-[4-[4-[(3-carbamoyl-1-prop-2-ynyl-pyrazol-4-yl)carbamoyl]oxazol-2-yl]-2-pyridyl]-N-(cyclopropylmethyl)carbamate (106 mg, 209 umol, synthesized via Step 1 of Method 12 coupling amine 4-amino-1-prop-2-ynyl-pyrazole-3-carboxamide, Intermediate MT with acid 2-[2-[tert-butoxycarbonyl(cyclopropylmethyl)amino]-4-pyridyl]oxazole-4-carboxylic acid, synthesized via Steps 1-4 of Intermediate DF) and 4-[2-[2-(2-azidoethoxy)ethoxy]ethylamino]-2-(2,6-dioxo-3-piperidyl)isoindoline-1,3-dione (60.0 mg, 139 umol, Intermediate MS) in t-BuOH (5 mL) was added CuSO₄ (4.6 mg, 28.8 umol, 4.42 uL) and sodium; (2R)-2-[(1S)-1,2-dihydroxyethyl]-4-hydroxy-5-oxo-2H-furan-3-olate (11.1 mg, 55.8 umol) in H₂O (5 mL). The reaction mixture was stirred at 60° C. for 2 hours under nitrogen. On completion, the reaction mixture was poured into brine (30 mL) and extracted with EA (3×50 mL). The combined organic layers were washed with brine (50 mL), dried with anhydrous Na₂SO₄, filtered and concentrated in vacuo to give the title compound (140 mg, 99% yield) as a light yellow solid. LC-MS (ESI⁺) m/z 936.5 (M+H)⁺.

Step 3—N-[3-carbamoyl-1-[[1-[2-[2-[2-[[2-(2,6-dioxo-3-piperidyl)-1,3-dioxo-isoindolin-4-yl]amino]ethoxy]ethoxy]ethyl]triazol-4-yl]methyl]pyrazol-4-yl]-2-[2-(cyclopropylmethylamino)-4-pyridyl]oxazole-4-carboxamide To a solution of tert-butyl N-[4-[4-[[3-carbamoyl-1-[[1-[2-[2-[2-[[2-(2,6-dioxo-3-piperidyl)-1,3-dioxo-isoindolin-4-yl]amino]ethoxy]ethoxy]ethyl]triazol-4-yl]methyl]pyrazol-4-yl]carbamoyl]oxazol-2-yl]-2-pyridyl]-N-(cyclopropylmethyl)carbamate (140 mg, 150 umol) in DCM (5 mL) was added HCl/dioxane (4 M, 10 mL). The reaction mixture was stirred at rt for 1 hour. On completion, the reaction mixture was concentrated in vacuo and purified by prep-HPLC (column: Phenomenex Synergi C18 150*25*10 um; mobile phase: [water (0.225% FA)-ACN]; B %: 18%-35%, 6 min). The purity of product was only 85%. Then the impure product was purified by prep-HPLC (column: Phenomenex Synergi C18 150*25*10 um; mobile phase: [water (0.05% HCl)-ACN]; B %: 16%-36%, 7.8 min) to give the title compound (6.40 mg, 5% yield) as a yellow solid. ¹H NMR (400 MHz, DMSO-d₆) δ 11.09 (s, 1H), 10.99 (s, 1H), 9.47 (s, 1H), 9.09 (s, 1H), 8.44 (s, 1H), 8.13 (s, 1H), 8.06 (d, J=6.0 Hz, 1H), 7.81 (s, 1H), 7.63 (s, 1H), 7.58-7.50 (m, 2H), 7.18-7.23 (m, 1H), 7.07 (d, J=8.8 Hz, 1H), 6.99 (d, J=6.4 Hz, 1H), 6.54 (s, 1H), 5.50 (s, 2H), 5.10-4.94 (m, 1H), 4.51 (t, J=4.8 Hz, 2H), 3.93-3.66 (m, 2H), 3.55-3.52 (m, 6H), 3.45-3.28 (m, 4H), 2.90-2.78 (m, 1H), 2.61-2.56 (m, 1H), 2.05-1.96 (m, 1H), 1.19-1.09 (m, 1H), 0.60-0.53 (m, 2H), 0.36-0.29 (m, 2H). LC-MS (ESI⁺) m/z 836.1 (M+H)⁺.

Example 300: (Method 16) N-[3-carbamoyl-1-[4-[[[4-[2-[2-[[2-(2,6-dioxo-3-piperidyl)-1,3-dioxo-isoindolin-4-yl]amino]ethoxy]ethyl]morpholin-2-yl]methylamino]methyl]phenyl]pyrazol-4-yl]-2-[2-(2,2,2-trifluoroethylamino)-4-pyridyl]oxazole-4-carboxamide, I-305

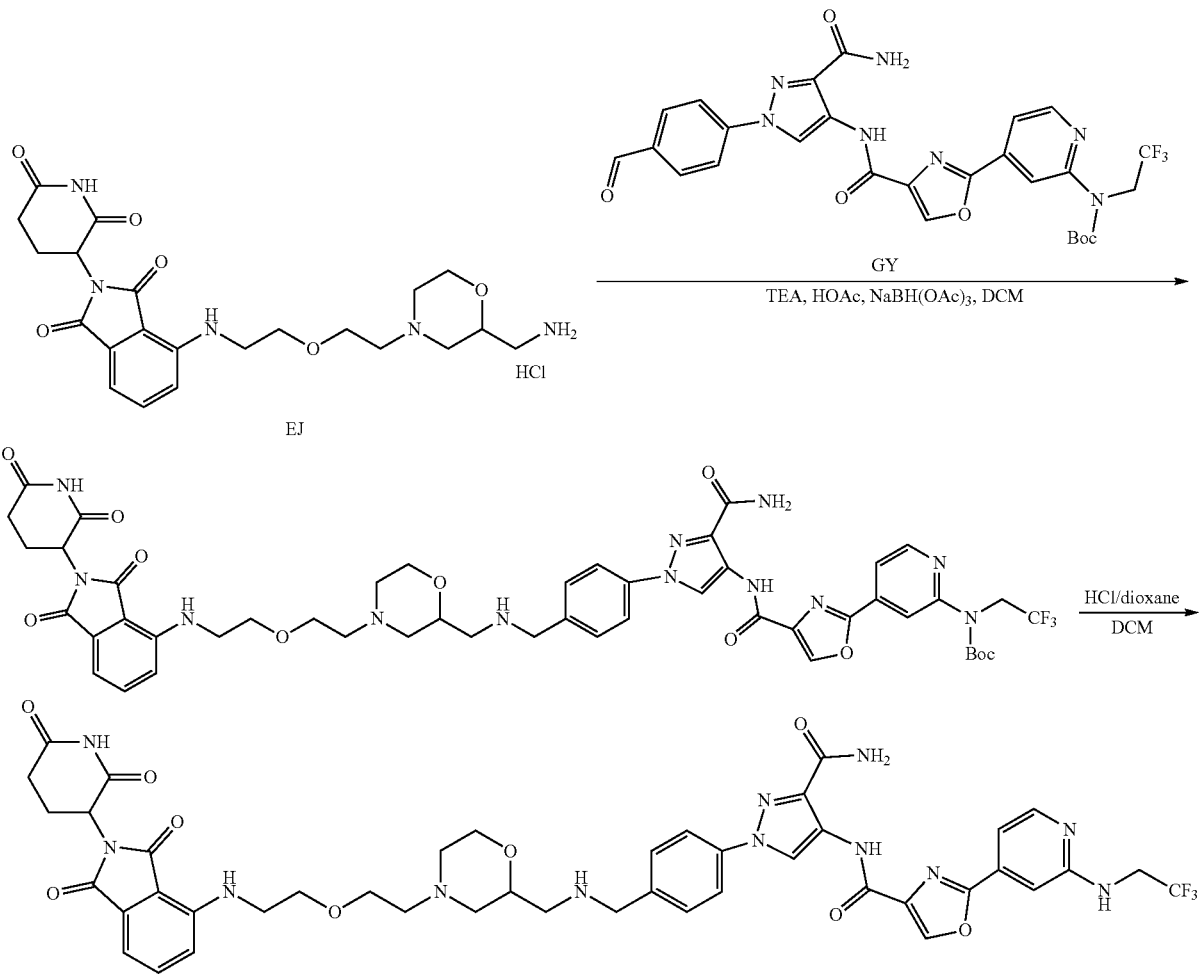

Step 1—Tert-butyl N-[4-[4-[[3-carbamoyl-1-[4-[[[4-[2-[2-[[2-(2,6-dioxo-3-piperidyl)-1,3-dioxo-isoindolin-4-yl]amino]ethoxy]ethyl]morpholin-2-yl]methylamino]methyl]phenyl]pyrazol-4-yl]carbamoyl]oxazol-2-yl]-2-pyridyl]-N-(2,2,2-trifluoroethyl)carbamate To a mixture of 4-[2-[2-[2-(aminomethyl)morpholin-4-yl]ethoxy]ethylamino]-2-(2,6-dioxo-3-piperidyl)isoindoline-1,3-dione (60.0 mg, 120 umol, HCl salt, Intermediate EJ) in DCM (5 mL) was added TEA (18.3 mg, 181 umol), HOAc (14.5 mg, 241 umol) and tert-butyl N-[4-[4-[[3-carbamoyl-1-(4-formylphenyl)pyrazol-4-yl]carbamoyl]oxazol-2-yl]-2-pyridyl]-N-(2,2,2-trifluoroethyl)carbamate (96.7 mg, 120 umol, Intermediate GY). The mixture was stirred for 30 minutes, and then NaBH(OAc)$_3$ (51.2 mg, 241 umol) was added. The mixture was then stirred rt for 16 hours. On completion, the reaction mixture was quenched by addition water (0.4 mL), and then concentrated in vacuo to give the title compound (120 mg, 95% yield) as yellow solid. LC-MS (ESI$^+$) m/z 1043.6 (M+H)$^+$.

Step 2—N-[3-carbamoyl-1-[4-[[[4-[2-[2-[[2-(2,6-dioxo-3-piperidyl)-1,3-dioxo-isoindolin-4-yl]amino]ethoxy]ethyl]morpholin-2-yl]methylamino]methyl]phenyl]pyrazol-4-yl]-2-[2-(2,2,2-trifluoroethylamino)-4-pyridyl]oxazole-4-carboxamide To a solution of tert-butyl N-[4-[4-[[3-carbamoyl-1-[4-[[[4-[2-[2-[[2-(2,6-dioxo-3-piperidyl)-1,3-dioxo-isoindolin-4-yl]amino]ethoxy]ethyl]morpholin-2-yl]methylamino]methyl]phenyl]pyrazol-4-yl]carbamoyl]oxazol-2-yl]-2-pyridyl]-N-(2,2,2-trifluoroethyl)carbamate (120 mg, 115 umol) in DCM (4 mL) was added HCl/dioxane (4 M, 1.03 mL). The mixture was stirred at rt for 1 hour. On completion, the reaction mixture was concentrated in vacuo to give a residue. The residue was purified by prep-HPLC (column: Phenomenex Synergi C18 150*25*10 um; mobile phase: [water (0.225% FA)-ACN]) to give the title compound (72.2 mg, 63% yield) as yellow solid. $^1$H NMR (400 MHz, DMSO-d$_6$) δ 11.01 (s, 1H), 9.03 (s, 1H), 8.92 (s, 1H), 8.25 (d, J=5.2 Hz, 1H), 8.20 (s, 1H), 8.06 (s, 1H), 7.91 (d, J=8.4 Hz, 2H), 7.73-7.69 (m, 1H), 7.59-7.55 (m, 1H), 7.49 (d, J=8.4 Hz, 2H), 7.26 (s, 1H), 7.20-7.11 (m, 2H), 7.03 (d, J=6.8 Hz, 1H), 6.60 (t, J=5.6 Hz, 1H), 5.05 (dd, J=5.6, 12.8 Hz, 1H), 4.33-4.19 (m, 2H), 3.78 (s, 2H), 3.72 (d, J=12 Hz, 2H), 3.59 (t, J=5.2 Hz, 2H), 3.55 (t, J=6.0 Hz, 2H), 3.48-3.44 (m, 3H), 2.89-2.77 (m, 2H), 2.70 (d, J=12.4 Hz, 1H), 2.62-2.55 (m, 2H), 2.49-2.43 (m, 4H), 2.07-1.97 (m, 2H), 1.80 (t, J=10.8 Hz, 1H); LC-MS (ESI$^+$) m/z 943.1 (M+H)$^+$.

TABLE 22

Compounds synthesized via Method 16 with the reductive amination of various amines with aldehydes in Step 1.

| Ex-#$^{a,e}$ | I-# | Step 1 Intermediate Amine | Step 1 Intermediate Aldehyde | LCMS (ES+) m/z (M + H)$^+$ | 1HNMR (400 MHz, DMSO-d6) δ |
|---|---|---|---|---|---|
| 301 | I-306 | FR | GY | 941.6 | 11.09 (s, 1H), 11.00 (s, 1H), 9.03 (s, 1H), 8.89 (s, 1H), 8.29-8.21 (m, 2H), 8.02 (s, 1H), 7.87 (d, J = 8.0 Hz, 2H), 7.77-7.64 (m, 2H), 7.57-7.43 (m, 3H), 7.28 (s, 1H), 7.19 (d, J = 5.6 Hz, 1H), 7.08 (m, 1H), 7.04-6.97 (m, 1H), 6.60-6.51 (m, 1H), 5.06 (dd, J = 4.8, 13.2 Hz, 1H), 4.34-4.17 (m, 2H), 3.76 (s, 2H), 3.62-3.47 (m, 5H), 3.42-3.38 (m, 3H), 2.95-2.79 (m, 3H), 2.72-2.57 (m, 5H), 2.02 (m, 1H), 1.60 (m, 2H), 1.53-1.20 (m, 4H) |
| 302 | I-307 | FS | HM | 884.1 | 11.11 (s, 1H), 9.92 (s, 1H), 8.96 (s, 1H), 8.85 (s, 1H), 8.19-8.11 (m, 1H), 7.81 (d, J = 8.4 Hz, 2H), 7.59-7.47 (m, 3H), 7.14-6.97 (m, 5H), 6.75 (t, J = 5.2 Hz, 1H), 5.04 (dd, J = 5.2, 13.2 Hz, 1H), 3.87 (s, 2H), 3.38-3.26 (m, 6H), 3.18 (t, J = 6.0 Hz, 2H), 2.93-2.85 (m, 1H), 2.84-2.79 (m, 2H), 2.73 (t, J = 5.6 Hz, 2H), 2.69-2.66 (m, 2H), 2.57-2.52 (m, 2H), 2.05-1.95 (m, 1H), 1.11-1.00 (m, 1H), 0.48-0.42 (m, 2H), 0.25-0.19 (m, 2H) |
| 303 | I-308 | GD | GC | 873.5 | 11.11 (s, 1H), 10.98 (s, 1H), 8.98 (s, 1H), 8.88 (s, 1H), 8.16 (d, J = 5.2 Hz, 1H), 8.01 (s, 1H), 7.88 (d, J = 8.4 Hz, 2H), 7.79 (d, J = 7.6 Hz, 1H), 7.75-7.70 (m, 2H), 7.67 (d, J = 7.6 Hz, 1H), 7.45 (d, J = 8.4 Hz, 2H), 7.16 (t, J = 6.0 Hz, 1H), 7.12 (s, 1H), 7.00 (dd, J = 1.2, 5.2 Hz, 1H), 5.12 (dd, J = 5.2, 12.8 Hz, 1H), 3.57-5.55 (m, 4H), 3.51-5.50 (m, 4H), 3.39 (t, J = 6.0 Hz, 2H), 3.19 (t, J = 6.0 Hz, 2H), 2.93-2.83 (m, 1H), 2.79 (t, J = 7.6 Hz, 2H), 2.63-2.55 (m, 2H), 2.54 (s, 2H), 2.19 (s, 3H), 2.09-1.99 (m, 1H), 1.89-1.78 (m, 2H), 1.13-0.99 (m, 1H), 0.50-0.39 (m, 2H), 0.27-0.17 (m, 2H) |
| 304 | I-309 | GD | GE | 804.4 | 11.14-11.11 (m, 1H), 11.09 (s, 1H), 9.08 (s, 1H), 8.89 (s, 1H), 8.85 (d, J = 5.6 Hz, 2H), 8.29 (s, 1H), 8.03 (s, 1H), 7.97 (d, J = 6.0 Hz, 2H), 7.89 (d, J = 8.4 Hz, 2H), 7.79 (d, J = 7.6 Hz, 1H), 7.78-7.73 (m, 2H), 7.68 (d, J = 7.2 Hz, 1H), 7.46 (d, J = 8.4 Hz, 2H), 5.13 (dd, J = 5.4, 12.8 Hz, 1H), 3.62-3.58 (m, 2H), 2.93-2.86 (m, 1H), 2.80 (t, J = 7.2 Hz, 2H), 2.61 (s, 1H), 2.56 (d, J = 5.6 Hz, 4H), 2.20 (s, 3H), 2.06 (dd, J = 5.2, 10.3 Hz, 1H), 1.89-1.80 (m, 2H) |
| 305 | I-310 | GD | GF | 880.5 | 11.1 (s, 1H), 9.98 (s, 1H), 8.97 (s, 1H), 8.78 (s, 1H), 8.16 (d, J = 5.2 Hz, 1H), 7.82-7.73 (m, 4H), 7.69 (d, J = 7.2 Hz, 1H), 7.45 (d, J = 8.4 Hz, 2H), 7.42-7.14 (m, 1H), 7.13-7.07 (m, 2H), 7.04 (d, J = 5.2 Hz, |

TABLE 22-continued

Compounds synthesized via Method 16 with the reductive amination
of various amines with aldehydes in Step 1.

| Ex-#[a,e] | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| | | | | | 1H), 5.17-5.09 (m, 1H), 3.57-3.55 (m, 4H), 3.52-3.48 (m, 8H), 3.24-3.04 (m, 2H), 2.84-2.80 (m, 1H), 2.63-2.58 (m, 1H), 2.57-2.55 (m, 1H), 2.44-2.41 (m, 2H), 2.19 (s, 3H), 2.08-2.02 (m, 1H), 1.87-1.81 (m, 2H), 1.11-1.03 (m, 1H), 0.50-0.43 (m, 2H), 0.25-0.20 (m, 2H) |
| 306 | I-311 | GH | GC | 857.5 | 10.99 (s, 1H), 8.99 (s, 1H), 8.93 (s, 1H), 8.25 (s, 1H), 8.16 (d, J = 5.2 Hz, 1H), 8.03 (s, 1H), 7.94 (d, J = 8.8 Hz, 2H), 7.80-7.71 (m, 3H), 7.70-7.64 (m, 1H), 7.54 (d, J = 8.4 Hz, 2H), 7.16 (t, J = 5.2 Hz, 1H), 7.12 (s, 1H), 7.00 (dd, J = 1.2, 5.2 Hz, 1H), 5.12 (dd, J = 5.2, 12.8 Hz, 1H), 3.87 (d, J = 6.4 Hz, 1H), 3.38-3.36 (m, 2H), 3.34-3.31 (m, 2H), 3.18 (t, J = 6.4 Hz, 2H), 3.06 (t, J = 7.2 Hz, 2H), 2.93-2.83 (m, 1H), 2.64-2.52 (m, 6H), 2.09-2.00 (m, 1H), 1.88-1.78 (m, 2H), 1.55-1.43 (m, 4H), 1.38-1.27 (m, 2H), 1.11-1.01 (m, 1H), 0.49-0.42 (m, 2H), 0.26-0.20 (m, 2H) |
| 307 | I-312 | GJ | GC | 871.2 | 11.13 (s, 1H), 10.98 (s, 1H), 8.98 (s, 1H), 8.89 (s, 1H), 8.16 (d, J = 5.2 Hz, 1H), 8.03 (s, 1H), 7.90 (d, J = 8.4 Hz, 2H), 7.79-7.68 (m, 3H), 7.68-7.61 (m, 1H), 7.46 (d, J = 8.4 Hz, 2H), 7.16 (t, J = 5.2 Hz, 1H), 7.12 (s, 1H), 7.00 (dd, J = 1.2, 5.2 Hz, 1H), 5.12 (dd, J = 5.2, 12.8 Hz, 1H), 3.55 (s, 2H), 3.36 (t, J = 6.4 Hz, 2H), 3.32 (t, J = 6.4 Hz, 2H), 3.19 (t, J = 6.4 Hz, 2H), 3.04 (t, J = 6.4 Hz, 2H), 3.08-3.00 (m, 1H), 2.95-2.81 (m, 1H), 2.64-2.53 (m, 2H), 2.37 (t, J = 7.2 Hz, 2H), 2.16 (s, 3H), 2.10-2.00 (m, 1H), 1.88-1.76 (m, 2H), 1.52-1.43 (m, 4H), 1.34-1.24 (m, 2H), 1.12-1.03 (m, 1H), 0.49-0.43 (m, 2H), 0.24-2.2 (m, 2H) |
| 308 | I-313 | GL | GC | 829.5 | δ11.14 (s, 1H), 11.01 (s, 1H), 9.01 (s, 1H), 8.92 (s, 1H), 8.17 (d, J = 5.2 Hz, 1H), 8.05 (s, 1H), 7.91 (d, J = 8.4 Hz, 2H), 7.79-7.68 (m, 4H), 7.47 (d, J = 8.4 Hz, 2H), 7.22-7.14 (m, 1H), 7.13 (s, 1H), 7.01 (d, J = 5.2 Hz, 1H), 5.14 (dd, J = 5.2, 12.8 Hz, 1H), 3.58 (s, 2H), 3.54-3.50 (m, 2H), 3.45-3.41 (m, 2H), 3.20 (t, J = 5.6 Hz, 2H), 3.09 (t, J = 7.2 Hz, 2H), 2.93-2.86 (m, 1H), 2.65-2.61 (m, 1H), 2.59-2.57 (m, 1H), 2.48-2.42 (m, 2H), 2.20 (s, 3H), 2.10-2.01 (m, 1H), 1.91-1.82 (m, 2H), 1.12-1.03 (m, 1H), 0.51-0.42 (m, 2H), 0.28-0.20 (m, 2H) |
| 309 | I-314 | GN | GC | 827.5 | 11.12 (s, 1H), 10.99 (s, 1H), 8.98 (s, 1H), 8.91 (s, 1H), 8.17-8.14 (m, 1H), 8.03 (s, 1H), 7.94-7.88 (m, 2H), 7.78-7.70 (m, 3H), 7.67-7.64 (m, 1H), 7.48-7.43 (m, 2H), 7.18-7.13 (m, 1H), 7.11 (s, 1H), 7.02-6.98 (m, 1H), 5.15-5.08 (m, 1H), 3.56 (s, 2H), 3.18 (t, J = 6.0 Hz, 2H), 3.00 (t, J = 7.6 Hz, 2H), 2.93-2.83 (m, 1H), 2.64-2.52 (m, 2H), 2.38 (t, J = 7.2 Hz, 2H), |

TABLE 22-continued

Compounds synthesized via Method 16 with the reductive amination
of various amines with aldehydes in Step 1.

| Ex-#[a,e] | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| | | | | | 2.16 (s, 3H), 2.09-2.01 (m, 1H), 1.65-1.53 (m, 2H), 1.52-1.42 (m, 2H), 1.36-1.25 (m, 4H), 1.10-1.02 (m, 1H), 0.48-0.41 (m, 2H), 0.25-0.19 (m, 2H) |
| 310 | I-315 | GO | GP | 884.5 | 10.76 (s, 1H), 8.76 (s, 2H), 8.12 (s, 1H), 7.93 (d, J = 4.8 Hz, 1H), 7.87 (s, 1H), 7.81 (d, J = 8.0 Hz, 2H), 7.54 (m, 4H), 7.32 (m, 2H), 6.93 (m, 1H), 6.88 (s, 1H), 6.77 (d, J = 4.8 Hz, 1H), 4.91-4.87 (m, 1H), 3.26-3.16 (m, 2H), 2.95 (t, J = 5.6 Hz, 3H), 2.88-2.77 (m, 2H), 2.73-2.68 (m, 4H), 2.65-2.52 (m, 3H), 2.39-2.34 (m, 2H), 1.89-1.77 (m, 1H), 1.75-1.51 (m, 2H), 1.44-1.34 (m, 2H), 1.24-1.08 (m, 4H), 0.84-0.82 (m, 1H), 0.23-0.21 (m, 2H), 0.00-0.02 (m, 2H); |
| 311 | I-316 | GS | GC | 869.6 | 10.89 (s, 1H), 9.82 (s, 1H), 8.76 (s, 1H), 8.67 (s, 1H), 8.45-8.45 (m, 1H), 7.93 (d, J = 5.2 Hz, 1H), 7.81-7.75 (m, 2H), 7.74-7.69 (m, 2H), 7.53-7.47 (m, 2H), 7.45-7.40 (m, 1H), 7.24-6.94 (m, 1H), 6.91-6.85 (m, 2H), 6.83-6.78 (m, 1H), 4.89 (dd, J = 5.6, 12.8 Hz, 1H), 3.37-3.20 (m, 10H), 2.95 (t, J = 6.8 Hz, 2H), 2.79 (t, J = 7.2 Hz, 2H), 2.71-2.62 (m, 1H), 2.41-2.38 (m, 1H), 2.36-2.34 (m, 1H), 1.86-1.76 (m, 1H), 1.62-1.53 (m, 2H), 0.89-0.80 (m, 1H), 0.26-0.19 (m, 2H), 0.03-0.00 (m, 2H) |
| 312 | I-317 | GT | GC | 855.2 | 11.00 (s, 1H), 9.00 (s, 1H), 8.93 (s, 1H), 8.28 (s, 1H), 8.17 (d, J = 5.2 Hz, 1H), 8.04 (s, 1H), 7.93 (d, J = 8.8 Hz, 2H), 7.79-7.71 (m, 3H), 7.71-7.67 (m, 1H), 7.52 (d, J = 8.8 Hz, 2H), 7.17 (t, J = 5.6 Hz, 1H), 7.13 (s, 1H), 7.01 (dd, J = 1.6, 5.2 Hz, 1H), 5.13 (dd, J = 5.6, 12.8 Hz, 1H), 3.81 (s, 2H), 3.20 (t, J = 6.0 Hz, 2H), 3.06-2.98 (m, 2H), 2.96-2.81 (m, 1H), 2.65-2.52 (m, 4H), 2.09-2.03 (m, 1H), 1.65-1.55 (m, 2H), 1.51-1.40 (m, 2H), 1.33-1.23 (m, 10H), 1.13-1.02 (m, 1H), 0.51-0.44 (m, 2H), 0.28-0.20 (m, 2H) |
| 313 | I-318 | GU | GY | 829.5 | 11.02 (s, 2H), 9.04 (s, 1H), 8.93 (s, 1H), 8.25 (d, J = 5.2 Hz, 1H), 8.20 (s, 1H), 8.06 (s, 1H), 7.92 (d, J = 8.4 Hz, 2H), 7.77-7.68 (m, 2H), 7.58-7.56 (m, 1H), 7.53-7.44 (m, 4H), 7.26 (s, 1H), 7.17 (dd, J = 1.2, 5.2 Hz, 1H), 5.14 (dd, J = 5.2, 13.6 Hz, 1H), 4.53-4.41 (m, 1H), 4.30 (d, J = 17.2 Hz, 1H), 4.26-4.22 (m, 2H), 3.81 (s, 2H), 3.47 (d, J = 6.0 Hz,, 2H), 3.39 (d, J = 6.0 Hz, 2H), 2.96-2.87 (m, 1H), 2.75-2.68 (m, 4H), 2.62-2.53 (m, 2H), 2.03-1.95 (m, 1H), 1.90-1.82 (m, 2H) |
| 314 | I-319 | GV | GC | 832.5 | 11.00 (s, 2H), 9.07-8.85 (m, 2H), 8.23 (s, 1H), 8.16 (d, J = 5.2 Hz, 1H), 8.05 (s, 1H), 7.92 (d, J = 8.0 Hz, 2H), 7.74 (s, 1H), 7.50 (d, J = 8.0 Hz, 2H), 7.25 (d, J = 7.2 Hz, 1H), 7.17 (t, J = 5.2 Hz, 1H), 7.14-6.98 (m, 5H), 5.37 (m, 1H), 4.04-3.94 (m, 2H), 3.82 (s, 2H), |

TABLE 22-continued

Compounds synthesized via Method 16 with the reductive amination of various amines with aldehydes in Step 1.

| Ex-#[a,e] | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| | | | | | 3.73-3.63 (m, 8H), 3.20-3.15 (m, 2H), 2.96-2.81 (m, 1H), 2.75-2.61 (m, 4H), 2.06-1.95 (m, 1H), 1.19-0.96 (m, 1H), 0.46-0.41 (m, 2H), 0.23-0.18 (m, 2H) |
| 315 | I-320 | GW | GY | 843.4 | 11.13 (s, 1H), 11.01 (s, 1H), 9.02 (s, 1H), 8.92 (s, 1H), 8.25 (d, J = 5.2 Hz, 1H), 8.22 (s, 1H), 8.04 (s, 1H), 7.92 (d, J = 8.4 Hz, 2H), 7.81-7.65 (m, 5H), 7.51 (d, J = 8.4 Hz, 2H), 7.26 (s, 1H), 7.17 (dd, J = 1.2, 5.6 Hz, 1H), 5.12 (dd, J = 5.2, 12.8 Hz, 1H), 4.30-4.21 (m, 2H), 3.82 (s, 2H), 3.48 (t, J = 5.6 Hz, 2H), 3.42 (t, J = 6.4 Hz, 2H), 3.08 (t, J = 7.2 Hz, 2H), 2.92-2.83 (m, 1H), 2.75-2.67 (t, J = 5.6 Hz, 2H), 2.64-2.53 (m, 2H), 2.11-2.00 (m, 1H), 1.92-1.80 (m, 2H) |
| 316 | I-321 | GX | GY | 887.4 | 11.50 (s, 1H), 11.02 (s, 1H), 9.04 (s, 1H), 8.90 (s, 1H), 8.27 (d, J = 5.2 Hz, 1H), 8.21 (s, 1H), 8.04 (s, 1H), 7.89 (d, J = 8.8 Hz, 2H), 7.77-7.70 (m, 4H), 7.69-7.66 (m, 1H), 7.49 (d, J = 8.8 Hz, 2H), 7.28 (s, 1H), 7.19 (dd, J = 1.2, 5.2 Hz, 1H), 5.13 (dd, J = 5.2, 12.4 Hz, 1H), 4.31-4.21 (m, 2H), 3.79 (s, 2H), 3.57-3.41 (m, 8H), 3.05 (t, J = 6.8 Hz, 2H), 2.94-2.84 (m, 1H), 2.72-2.68 (m, 2H), 2.64-2.57 (m, 1H), 2.57-2.54 (m, 1H), 2.09-2.03 (m, 1H), 1.87-1.79 (m, 2H) |
| 317 | I-322 | HA | GY | 975.2 | 11.09 (s, 1H), 11.00 (s, 1H), 9.02 (s, 1H), 8.91 (s, 1H), 8.29-8.24 (m, 2H), 8.03 (s, 1H), 7.91 (d, J = 8.4 Hz, 2H), 7.77-7.67 (m, 5H), 7.49 (d, J = 8.8 Hz, 2H), 7.27 (s, 1H), 7.18 (dd, J = 1.6, 5.2 Hz, 1H), 5.13 (dd, J = 5.6, 12.8 Hz, 1H), 4.30-4.21 (m, 2H), 3.79 (s, 2H), 3.52-3.46 (m, 14H), 3.40 (t, J = 6.4 Hz, 2H), 3.05 (t, J = 7.6 Hz, 2H), 2.95-2.83 (m, 1H), 2.68 (t, J = 5.6 Hz, 2H), 2.60-2.52 (m, 2H), 2.10-2.03 (m, 1H), 1.86-1.79 (m, 2H) |
| 318 | I-323 | MN | GY | 971.5 | 11.00 (s, 1H), 9.02 (s, 1H), 8.91 (s, 1H), 8.26 (d, J = 5.6 Hz, 2H), 8.04 (s, 1H), 7.93-7.83 (m, 5H), 7.74-7.68 (m, 2H), 7.49 (d, J = 8.4 Hz, 2H), 7.27 (s, 1H), 7.18 (d, J = 5.2 Hz, 1H), 5.15 (dd, J = 5.6, 12.8 Hz, 1H), 4.49 (s, 2H), 4.31-4.21 (m, 2H), 3.78 (s, 2H), 3.75-3.68 (m, 3H), 3.61-3.57 (m, 3H), 3.53-3.48 (m, 9H), 2.96-2.84 (m, 1H), 2.71-2.57 (m, 5H), 2.34 (s, 1H), 2.12-2.02 (m, 1H) |
| 319 | I-324 | HB | GC | 845.5 | 10.99 (s, 1H), 8.99 (s, 1H), 8.90 (s, 1H), 8.25 (s, 1H), 8.16 (d, J = 5.2 Hz, 1H), 8.03 (, 1H), 7.89 (d, J = 8.8 Hz, 2H), 7.72 (s, 1H), 7.58-7.53 (t, J = 4.4 Hz, 1H), 7.49 (d, J = 8.4 Hz, 2H), 7.46-7.39 (m, 2H), 7.16 (t, J = 5.6 Hz, 1H), 7.12 (s, 1H), 7.00 (dd, J = 1.2, 5.2 Hz, 1H), 5.13 (dd, J = 5.2, 13.2 Hz, 1H), 4.43 (d, J = 17.2 Hz, 1H), 4.29 (d, J = 17.2 Hz, 1H), 3.81 (s, 2H), 3.54-3.47 (m, 6H), 3.39 (t, J = 6.4 Hz, 2H), 3.19 (t, J = 6.4 Hz, 2H), |

TABLE 22-continued

Compounds synthesized via Method 16 with the reductive amination
of various amines with aldehydes in Step 1.

| Ex-#[a,e] | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| | | | | | 2.98-2.86 (m, 1H), 2.75-2.63 (m, 4H), 2.63-2.52 (m, 2H), 2.05-1.96 (m, 1H), 1.87-1.77 (m, 2H), 1.13-1.02 (m, 1H), 0.49-0.41 (m, 2H), 0.26-0.20 (m, 2H) |
| 320 | I-325 | HC | GC | 889.5 | 10.99 (s, 1H), 8.99 (s, 1H), 8.91 (s, 1H), 8.16 (d, J = 5.2 Hz, 1H), 8.04 (s, 1H), 7.92 (s, 1H), 7.89 (s, 1H), 7.73 (s, 1H), 7.58-7.53 (m, 1H), 7.50 (s, 1H), 7.48 (s, 1H), 7.44 (d, J = 4.4 Hz, 2H), 7.19-7.13 (m, 1H), 7.12 (s, 1H), 7.02-6.98 (m, 1H), 5.17-5.09 (m, 1H), 4.47-4.40 (m, 1H), 4.32-4.26 (m, 1H), 3.81 (s, 2H), 3.54-3.52 (m, 10H), 3.39-3.37 (m, 2H), 3.27-3.14 (m, 2H), 2.97-2.86 (m, 1H), 2.73-2.68 (m, 2H), 2.67-2.63 (m, 2H), 2.53-2.51 (m, 1H), 2.44-2.37 (m, 1H), 2.06-1.96 (m, 1H), 1.85-1.76 (m, 2H), 1.11-1.02 (m, 1H), 0.49-0.43 (m, 2H), 0.25-0.20 (m, 2H) |
| 321 | I-326 | OK | HG | 798.2 | 11.09 (s, 1H), 10.98 (s, 1H), 9.18 (s, 2H), 9.12 (s, 1H), 8.47 (s, 1H), 8.07 (d, J = 6.4 Hz, 1H), 7.99 (s, 1H), 7.64 (d, J = 15.6 Hz, 2H), 7.57 (t, J = 8.0 Hz, 1H), 7.23 (d, J = 6.8 Hz, 1H), 7.11 (d, J = 8.8 Hz, 1H), 7.02 (d, J = 6.8 Hz, 1H), 6.57 (s, 1H), 5.05 (dd, J = 5.6, 12.8 Hz, 1H), 4.58 (t, J = 5.2 Hz, 2H), 3.74 (t, J = 5.2 Hz,, 2H), 3.63-3.59 (m, 10H), 3.36 (d, J = 6.8 Hz, 2H), 3.22-3.14 (m, 2H), 2.94-2.82 (m, 1H), 2.64-2.53 (m, 2H), 2.07-1.99 (m, 1H), 1.21-1.10 (m, 1H), 0.61-0.52 (m, 2H), 0.36-0.30 (m, 2H) |
| 322 | I-327 | HK | GF | 922.2 | 11.09 (s, 1H), 9.99 (s, 1H), 8.98 (s, 1H), 8.79 (s, 1H), 8.21 (s, 1H), 8.16 (d, J = 5.2 Hz, 1H), 7.80 (d, J = 8.4 Hz, 2H), 7.62-7.55 (m, 1H), 7.48 (d, J = 8.4 Hz, 2H), 7.44-7.17 (m, 1H), 7.17-7.08 (m, 3H), 7.07-7.01 (m, 2H), 6.60 (t, J = 5.6 Hz, 1H), 5.06 (dd, J = 5.2, 12.8 Hz, 1H), 3.79-3.68 (m, 3H), 3.63-3.54 (m, 4H), 3.51-3.41 (m, 4H), 3.21-3.16 (m, 2H), 2.94-2.78 (m, 3H), 2.73-2.55 (m, 6H), 2.10-1.98 (m, 2H), 1.84-1.79 (m, 1H), 1.14-1.02 (m, 1H), 0.51-0.41 (m, 2H), 0.26-0.21 (m, 2H) |
| 323 | I-328 | HO | GY | 888.4 | 11.07 (s, 1H), 11.01 (s, 1H), 9.02 (s, 1H), 8.90 (s, 1H), 8.32-8.22 (m, 2H), 8.03 (s, 1H), 7.89 (d, J = 8.4 Hz, 2H), 7.75-7.66 (m, 2H), 7.49 (d, J = 8.4 Hz, 2H), 7.28 (s, 1H), 7.22-7.15 (m, 1H), 7.04-6.96 (m, 2H), 6.86 (d, J = 8.4 Hz, 1H), 5.33 (dd, J = 5.2, 12.4 Hz, 1H), 4.30-4.21 (m, 2H), 3.79 (s, 2H), 3.55-3.48 (m, 10H), 3.31 (s, 3H), 2.93-2.85 (m, 1H), 2.70-2.64 (m, 4H), 2.04-1.96 (m, 1H), 1.85-1.76 (m, 2H) |
| 324 | I-329 | HQ | GY | 888.5 | 11.07 (s, 1H), 11.00 (s, 1H), 9.01 (s, 1H), 8.89 (s, 1H), 8.29 (s, 1H), 8.25 (d, J = 5.2 Hz, 1H), 8.02 (s, 1H), 7.87 (d, J = 8.4 Hz, 2H), 7.73-7.66 (m, 2H), 7.47 (d, J = 8.8 Hz, 2H), 7.26 (s, 1H), 7.17 (dd, J = 1.2, 5.2 Hz, 1H), 6.97-6.90 (m, 2H), |

TABLE 22-continued

Compounds synthesized via Method 16 with the reductive amination
of various amines with aldehydes in Step 1.

| Ex-#[a,e] | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| | | | | | 6.86-6.82 (m, 1H), 5.35 (dd, J = 5.2, 12.8 Hz, 1H), 4.29-4.19 (m, 2H), 3.77 (s, 2H), 3.55-3.50 (m, 11H), 2.95-2.84 (m, 3H), 2.71-2.61 (m, 4H), 2.03-1.91 (m, 1H), 1.85-1.75 (m, 2H) |
| 325 | I-330 | HR | GF | 922.1 | 11.09 (s, 1H), 10.00 (s, 1H), 8.97 (s, 1H), 8.79 (s, 1H), 8.23 (s, 1H), 8.16 (d, J = 5.2 Hz, 1H), 7.80 (d, J = 8.4 Hz, 2H), 7.60-7.53 (m, 1H), 7.48 (d, J = 8.4 Hz, 2H), 7.43-7.16 (m, 1H), 7.15-7.07 (m, 3H), 7.06-7.00 (m, 2H), 6.59 (t, J = 5.2 Hz, 1H), 5.05 (dd, J = 5.2, 12.8 Hz, 1H), 3.77 (s, 3H), 3.56 (dd, J = 6.0, 11.6 Hz, 4H), 3.51-3.43 (m, 4H), 3.18 (t, J = 6.0 Hz, 2H), 2.94-2.83 (m, 1H), 2.80 (d, J = 10.8 Hz, 1H), 2.69 (d, J = 11.2 Hz, 1H), 2.60 (d, J = 2.4 Hz, 1H), 2.54-2.58 (m, 1H), 2.55-2.52 (m, 2H), 2.48-2.44 (m, 2H), 2.09-1.96 (m, 2H), 1.78-1.82 (m, 1H), 1.12-1.02 (m, 1H), 0.50-0.41 (m, 2H), 0.29-0.16 (m, 2H) |
| 326 | I-331 | HO | GF | 867.5 | 10.84 (s, 1H), 9.74 (s, 1H), 8.73 (s, 1H), 8.54 (s, 1H), 7.99 (s, 1H), 7.93 (d, J = 5.2 Hz, 1H), 7.55 (d, J = 8.8 Hz, 2H), 7.25 (d, J = 8.4 Hz, 2H), 7.20-6.91 (m, 1H), 6.89-6.83 (m, 2H), 6.82-6.78 (m, 2H), 6.76 (d, J = 8.0 Hz, 1H), 6.62 (d, J = 8.4 Hz, 1H), 5.09 (dd, J = 5.6, 12.8 Hz, 1H), 3.55 (s, 2H), 3.31-3.23 (m, 10H), 3.07 (s, 3H), 3.01-2.89 (m, 2H), 2.69-2.62 (m, 1H), 2.46-2.41 (m, 4H), 1.78-1.74 (m, 1H), 1.61-1.53 (m, 2H), 0.88-0.79 (m, 1H), 0.25-0.19 (m, 2H), −0.01 (q, J = 4.8 Hz, 2H) |
| 327 | I-332 | HQ | GF | 867.5 | 11.08 (s, 1H), 9.98 (s, 1H), 8.97 (s, 1H), 8.78 (s, 1H), 8.21 (s, 1H), 8.16 (d, J = 5.2 Hz, 1H), 7.79 (d, J = 8.4 Hz, 2H), 7.49 (d, J = 8.8 Hz, 2H), 7.43-7.16 (m, 1H), 7.12 (s, 1H), 7.09 (t, J = 5.6 Hz, 1H), 7.06-7.02 (m, 1H), 6.98-6.91 (m, 2H), 6.88-6.82 (m, 1H), 5.36 (dd, J = 5.6, 12.4 Hz, 1H), 3.81 (s, 2H), 3.56-3.54 (m, 7H), 3.47-3.45 (m, 4H), 3.19 (t, J = 6.0 Hz, 2H), 2.99-2.85 (m, 3H), 2.77-2.63 (m, 4H), 2.02-1.95 (m, 1H), 1.87-1.77 (m, 2H), 1.13-1.01 (m, 1H), 0.50-0.40 (m, 2H), 0.26-0.19 (m, 2H) |
| 328 | I-333 | HV | Tert-butyl N-[4-[4-[[3-carbamoyl-1-[4-(5-oxopentyl-carbamoyl)-phenyl]-pyrazol-4-yl]carbamoyl]-oxazol-2-yl]-2-pyridyl]-N-(2,2,2-trifluoroethyl)-carbamate (synthesized via Steps 1-2 of Example 172) | 885.1 | 11.02 (s, 1H), 9.03 (s, 2H), 8.56 (t, J = 5.6 Hz, 1H), 8.29-8.23 (m, 2H), 8.13 (s, 1H), 8.10 (d, J = 8.8 Hz, 2H), 8.02 (d, J = 8.8 Hz, 2H), 7.79 (d, J = 15.2 Hz, 2H), 7.70 (t, J = 6.0 Hz, 1H), 7.60-7.52 (m, 1H), 7.27 (s, 1H), 7.18 (dd, J = 1.2 Hz, 1H), 7.09 (d, J = 8.2 Hz, 1H), 6.99 (d, J = 7.2 Hz, 1H), 6.78 (t, J = 5.6 Hz, 1H), 4.51 (dd, J = 6.0, 12.0 Hz, 1H), 4.30-4.20 (m, 2H), 3.42-3.16 (m, 6H), 2.83 (t, J = 5.6 Hz, 2H), 2.69-2.59 (m, 2H), 2.27-2.17 (m, 1H), 2.03-1.82 (m, 3H), 1.61-1.45 (m, 4H), 1.42-1.34 (m, 2H) |

TABLE 22-continued

Compounds synthesized via Method 16 with the reductive amination
of various amines with aldehydes in Step 1.

| Ex-#[a,e] | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| 329 | I-334 | KK | GF | 950.3 | 10.87 (s, 1H), 9.76-9.70 (m, 1H), 8.79-8.67 (m, 1H), 8.56 (s, 1H), 7.97-7.91 (m, 3H), 7.58 (d, J = 8.4 Hz, 2H), 7.36-7.24 (m, 3H), 7.05 (s, 1H), 6.93-6.84 (m, 3H), 6.83-6.76 (m, 2H), 5.99 (d, J = 7.6 Hz, 1H), 4.81 (d, J = 4.8, 12.8 Hz, 1H), 3.58 (s, 3H), 3.20-3.08 (m, 12H), 2.98-2.92 (m, 2H), 2.53 (s, 2H), 2.51-2.42 (m, 4H), 2.10 (s, 2H), 1.96 (t, J = 10.0 Hz, 2H), 1.78 (d, J = 4.4 Hz, 1H), 1.66 (d, J = 10.0 Hz, 2H), 1.23 (d, J = 11.2 Hz, 2H), 0.84 (s, 1H), 0.26-0.19 (m, 2H), 0.02-0.04 (m, 2H) |
| 330 | I-335 | HZ | GF | 950.4 | 11.03 (s, 1H), 9.95 (s, 1H), 8.95 (s, 1H), 8.79 (s, 1H), 8.20 (s, 1H), 8.16 (d, J = 5.2 Hz, 1H), 7.82 (d, J = 7.6 Hz, 2H), 7.56-7.48 (m, 3H), 7.43-7.14 (m, 1H), 7.11 (s, 1H), 7.07 (t, J = 5.6 Hz, 1H), 7.03 (d, J = 5.6 Hz, 1H), 7.00-6.93 (m, 2H), 6.85 (d, J = 8.4 Hz, 1H), 5.01 (dd, J = 5.2, 12.8 Hz, 1H), 3.86-3.83 (m, 2H), 3.60-3.45 (m, 10H), 3.44-3.34 (m, 2H), 3.18 (t, J = 6.0 Hz, 2H), 2.92-2.81 (m, 3H), 2.85 (br d, J = 12.5 Hz, 1H), 2.75-2.73 (m, 1H), 2.61-2.54 (m, 1H), 2.53-2.52 (m, 1H), 2.21-2.14 (m, 2H), 2.01-1.94 (m, 1H), 1.90-1.84 (m, 2H), 1.46-1.37 (m, 2H), 1.10-1.03 (m, 1H), 0.48-0.43 (m, 2H), 0.25-0.20 (m, 2H) |
| 331 | I-336 | IA | GF | 936.5 | 11.09 (s, 1H), 9.99 (s, 1H), 8.97 (s, 1H), 8.77 (s, 1H), 8.25 (s, 1H), 8.16 (d, J = 5.2 Hz, 1H), 7.79 (d, J = 8.4 Hz, 2H), 7.69-7.64 (m, 1H), 7.49 (d, J = 8.8 Hz, 2H), 7.47-7.33 (m, 1H), 7.31 (d, J = 10.4 Hz, 1H), 7.28 (d, J = 5.2 Hz, 1H), 7.15-7.09 (m, 2H), 7.04 (d, J = 5.2 Hz, 1H), 5.12-5.05 (m, 1H), 3.80 (s, 2H), 3.55-3.51 (m, 8H), 3.27-3.22 (m, 4H), 3.20-3.16 (m, 2H), 2.91-2.81 (m, 1H), 2.75-2.65 (m, 4H), 2.61-2.57 (m, 4H), 2.57-2.55 (m, 1H), 2.54-2.53 (m, 1H), 2.05-1.98 (m, 1H), 1.60-1.50 (m, 1H), 0.48-0.43 (m, 2H), 0.25-0.20 (m, 2H) |
| 332 | I-337 | IB | GF | 936.2 | 11.06 (s, 1H), 9.95 (s, 1H), 8.96 (s, 1H), 8.78 (s, 1H), 8.16 (d, J = 5.2 Hz, 1H), 7.80 (d, J = 8.4 Hz, 2H), 7.65 (d, J = 8.4 Hz, 1H), 7.50 (d, J = 8.4 Hz, 2H), 7.43-7.14 (m, 3H), 7.12 (s, 1H), 7.08 (t, J = 5.2 Hz, 1H), 7.06-7.02 (m, 1H), 5.06 (dd, J = 5.2, 12.8 Hz, 1H), 3.81 (s, 2H), 3.60-3.53 (m, 4H), 3.53-3.50 (m, 4H), 3.43-3.35 (m, 4H), 3.19 (t, J = 6.0 Hz, 2H), 2.93-2.82 (m, 1H), 2.71 (t, J = 5.6 Hz, 2H), 2.63-2.55 (m, 2H), 2.54 (m, 6H), 2.05-1.97 (m, 1H), 1.13-1.03 (m, 1H), 0.49-0.43 (m, 2H), 0.26-0.20 (m, 2H) |
| 333 | I-338 | MX | GF | 922.2 | 11.10 (s, 1H), 9.96 (s, 1H), 8.97 (s, 1H), 8.80 (s, 1H), 8.21 (s, 1H), 8.17 (d, J = 5.4 Hz, 1H), 7.83 (d, J = 8.4 Hz, 2H), 7.62-7.49 (m, 3H), 7.45-7.15 (m, 1H), 7.12 (s, 1H), 7.10-7.02 (m, 3H), 6.97 (d, J = 8.4 Hz, |

TABLE 22-continued

Compounds synthesized via Method 16 with the reductive amination
of various amines with aldehydes in Step 1.

| Ex-#[a,e] | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| | | | | | 1H), 6.61 (d, J = 7.2 Hz, 1H), 5.06 (dd, J = 5.2, 12.8 Hz, 1H), 4.30-4.19 (m, 1H), 3.87 (s, 2H), 3.72 (t, J = 6.8 Hz, 2H), 3.55 (t, J = 5.4 Hz, 2H), 3.54-3.50 (m, 4H), 3.41 (t, J = 5.6 Hz, 2H), 3.20 (t, J = 6.4 Hz, 2H), 3.10-2.97 (m, 2H), 2.96-2.83 (m, 1H), 2.82-2.72 (m, 2H), 2.63 (t, J = 4.8 Hz, 2H), 2.60-2.52 (m, 1H), 2.48-2.44 (m, 1H), 2.07-1.99 (m, 1H), 1.13-1.02 (m, 1H), 0.50-0.43 (m, 2H), 0.27-0.20 (m, 2H) |
| 334 | I-339 | IC | GF | 922.5 | 11.05 (s, 1H), 9.97 (s, 1H), 8.97 (s, 1H), 8.79 (s, 1H), 8.28-8.26 (m, 1H), 8.16 (d, J = 5.2 Hz, 1H), 7.85-7.76 (m, 2H), 7.59-7.45 (m, 4H), 7.43-7.15 (m, 1H), 7.14-7.02 (m, 3H), 6.87 (s, 1H), 6.78 (d, J = 8.2 Hz, 1H), 5.03 (dd, J = 5.2, 12.8 Hz, 1H), 3.84 (s, 3H), 3.70-3.60 (m, 2H), 3.57-3.45 (m, 8H), 3.44-3.38 (m, 2H), 3.19 (t, J = 6.0 Hz, 2H), 3.00-2.83 (m, 3H), 2.62-2.56 (m, 4H), 2.04-1.93 (m, 1H), 1.12-1.02 (m, 1H), 0.51-0.42 (m, 2H), 0.28-0.19 (m, 2H) |
| 335 | I-340 | IE | GF | 948.2 | 11.08 (s, 1H), 9.97 (s, 1H), 8.97 (s, 1H), 8.78 (s, 1H), 8.31 (s, 1H), 8.17 (d, J = 5.2 Hz, 1H), 7.99 (s, 1H), 7.79 (d, J = 8.4 Hz, 2H), 7.62-7.53 (m, 1H), 7.47 (d, J = 8.4 Hz, 2H), 7.29 (t, J = 14.0 Hz, 1H), 7.15 (d, J = 14.0 Hz,, 2H), 7.10-7.01 (m, 4H), 5.06 (dd, J = 5.2, 12.8 Hz, 1H), 4.58 (d, J = 6.0 Hz, 2H), 4.49 (t, J = 5.2 Hz, 2H), 3.80 (t, J = 5.2 Hz, 2H), 3.75 (s, 2H), 3.51-3.48 (m, 6H), 3.19 (d, J = 6.0 Hz, 2H), 2.94-2.83 (m, 1H), 2.66-2.55 (m, 4H), 2.06-1.98 (m, 1H), 1.16-1.00 (m, 1H), 0.49-0.43 (m, 2H), 0.26-0.19 (m, 2H) |
| 336 | I-341 | IG | GF | 948.1 | 11.04 (s, 1H), 9.97 (s, 1H), 8.97 (s, 1H), 8.80 (s, 1H), 8.16 (d, J = 5.2 Hz, 1H), 7.99 (s, 1H), 7.82 (d, J = 8.4 Hz, 2H), 7.61-7.54 (m, 2H), 7.50 (d, J = 8.4 Hz, 2H), 7.45-7.15 (m, 1H), 7.12 (s, 1H), 7.10-7.01 (m, 3H), 6.95 (dd, J = 2.0, 8.4 Hz, 1H), 5.03 (dd, J = 5.2, 12.8 Hz, 1H), 4.50 (t, J = 5.2 Hz, 2H), 4.46 (d, J = 5.6 Hz, 2H), 3.83 (s, 2H), 3.80 (t, J = 5.2 Hz, 2H), 3.53-3.44 (m, 6H), 3.19 (t, J = 6.0 Hz, 2H), 2.92-2.80 (m, 1H), 2.72 (t, J = 5.6 Hz, 2H), 2.61-2.53 (m, 2H), 2.03-1.93 (m, 1H), 1.13-1.02 (m, 1H), 0.49-0.42 (m, 2H), 0.26-0.20 (m, 2H) |
| 337 | I-342 | IH | GF | 962.1 | 11.07 (s, 1H), 9.97 (s, 1H), 8.96 (s, 1H), 8.78 (s, 1H), 8.21 (s, 1H), 8.16 (d, J = 5.2 Hz, 1H), 7.78 (d, J = 8.4 Hz, 2H), 7.63-7.53 (m, 2H), 7.45 (d, J = 8.4 Hz, 2H), 7.42-7.11 (m, 3H), 7.07 (d, J = 5.2 Hz, 1H), 7.04 (d, J = 6.0 Hz, 2H), 6.74 (t, J = 6.0 Hz, 1H), 5.05 (dd, J = 5.2, 12.8 Hz, 1H), 4.52-4.44 (m, 2H), 3.79 (t, J = 4.8 Hz, 2H), 3.75-3.73 (m, 1H), 3.74 (s, 2H), 3.60 (d, J = 6.8 Hz, 2H), 3.47 (d, J = 4.8 Hz, 2H), |

TABLE 22-continued

Compounds synthesized via Method 16 with the reductive amination
of various amines with aldehydes in Step 1.

| Ex-#[a,e] | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| | | | | | 3.41 (d, J = 6.4 Hz, 4H), 3.19 (t, J = 5.6 Hz, 2H), 3.01 (t, J = 6.8 Hz, 2H), 2.93-2.81 (m, 1H), 2.63-2.61 (m, 2H), 2.58-2.54 (m, 2H), 2.02-1.99 (m, 1H), 1.10-1.02 (m, 1H), 0.46-2.44 (m, 2H), 0.23-2.22 (m, 2H) |
| 338 | I-343 | MY | GF | 962.1 | 11.04 (s, 1H), 9.96 (s, 1H), 8.97 (s, 1H), 8.79 (s, 1H), 8.20 (s, 1H), 8.17 (d, J = 5.2 Hz, 1H), 7.80 (d, J = 8.4 Hz, 2H), 7.62-7.56 (m, 2H), 7.47 (d, J = 8.0 Hz, 2H), 7.44-7.28 (m, 1H), 7.23 (s, 1H), 7.13 (s, 1H), 7.09-7.01 (m, 3H), 6.91 (d, J = 8.3 Hz, 1H), 5.04 (dd, J = 5.2, 12.8 Hz, 1H), 4.46 (t, J = 4.8 Hz, 2H), 3.82-3.74 (m, 4H), 3.55-3.40 (m, 6H), 3.23-3.17 (m, 2H), 3.00 (t, J = 6.8 Hz, 2H), 2.93-2.81 (m, 2H), 2.69-2.55 (m, 5H), 2.37-2.32 (m, 1H), 2.02-1.96 (m, 1H), 1.08 (s, 1H), 0.49-0.44 (m, 2H), 0.25-0.21 (m, 2H) |
| 339 | I-344 | II | GF | 949.1 | 11.11 (s, 1H), 10.00 (s, 1H), 8.98 (s, 1H), 8.79 (s, 1H), 8.30-8.20 (m, 2H), 8.17 (d, J = 5.2 Hz, 1H), 7.86-7.76 (m, 3H), 7.73 (d, J = 8.4 Hz, 1H), 7.51-7.44 (m, 3H), 7.44-7.15 (m, 1H), 7.14-7.08 (m, 2H), 7.05 (dd, J = 1.2, 5.2 Hz, 1H), 5.41 (s, 2H), 5.11-5.03 (m, 1H), 4.56 (t, J = 5.2 Hz, 2H), 3.83 (t, J = 5.2 Hz, 2H), 3.77 (s, 2H), 3.56-3.51 (m, 2H), 3.50-3.43 (m, 4H), 3.19 (t, J = 6.0 Hz, 2H), 2.94-2.81 (m, 1H), 2.69-2.63 (m, 2H), 2.58-2.52 (m, 2H), 2.06-1.95 (m, 1H), 1.13-1.02 (m, 1H), 0.50-0.42 (m, 2H), 0.26-0.20 (m, 2H) |
| 340 | I-345 | NB | GF | 949.5 | 10.88 (s, 1H), 9.71 (s, 1H), 8.72 (s, 1H), 8.53 (s, 1H), 8.01 (s, 1H), 7.92 (d, J = 5.4 Hz, 1H), 7.60 (d, J = 8.2 Hz, 1H), 7.54 (d, J = 8.4 Hz, 2H), 7.35 (s, 1H), 7.25-7.16 (m, 2H), 7.05 (s, 1H), 6.91-6.87 (m, 1H), 6.86-6.78 (m, 2H), 5.12 (s, 2H), 4.88 (dd, J = 5.2, 12.8 Hz, 1H), 4.32 (t, J = 5.2 Hz, 2H), 3.63-3.56 (m, 2H), 3.50 (s, 2H), 3.30 (s, 2H), 3.24 (d, J = 5.4 Hz, 4H), 2.96 (d, J = 6.0 Hz, 2H), 2.71-2.61 (m, 2H), 2.47-2.41 (m, 4H), 1.86-1.71 (m, 2H), 0.83 (d, J = 5.6 Hz, 1H), 0.27-0.19 (m, 2H), 0.01 (d, J = 4.4 Hz, 2H) |
| 341 | I-346 | IJ | GF | 963.1 | 11.08 (s, 1H), 9.96 (s, 1H), 8.97 (s, 1H), 8.78 (s, 1H), 8.16 (d, J = 5.2 Hz, 1H), 7.83-7.76 (m, 3H), 7.75 (s, 1H), 7.53-7.44 (m, 4H), 7.43-7.15 (m, 1H), 7.12 (s, 1H), 7.08 (t, J = 5.6 Hz, 1H), 7.06-7.02 (m, 1H), 5.10 (dd, J = 5.2, 12.8 Hz, 1H), 4.58 (t, J = 5.2 Hz, 2H), 4.41 (t, J = 6.0 Hz, 2H), 3.81 (t, J = 5.2 Hz, 2H), 3.77 (s, 2H), 3.52-3.49 (m, 2H), 3.46-3.42 (m, 4H), 3.25 (t, J = 6.0 Hz, 2H), 3.19 (t, J = 6.0 Hz, 2H), 2.94-2.84 (m, 1H), 2.65 (t, J = 5.6 Hz, 2H), 2.59-2.54 (m, 2H), 2.09-1.98 (m, 1H), 1.13-1.01 (m, 1H), 0.49-0.43 (m, 2H), 0.26-0.21 |

TABLE 22-continued

Compounds synthesized via Method 16 with the reductive amination
of various amines with aldehydes in Step 1.

| Ex-#[a,e] | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| 342 | I-347 | ND | GF | 963.1 | 11.09 (s, 1H), 9.95 (s, 1H), 8.97 (s, 1H), 8.78 (s, 1H), 8.22 (d, J = 6.8 Hz, 2H), 8.17 (d, J = 5.2 Hz, 1H), 7.81-7.76 (m, 3H), 7.63 (s, 1H), 7.50-7.44 (m, 3H), 7.36 (dd, J = 2.0, 8.4 Hz, 1H), 7.29 (s, 1H), 7.12 (s, 1H), 7.10-7.03 (m, 2H), 5.12 (dd, J = 5.6, 12.8 Hz, 1H), 4.54 (t, J = 5.2 Hz, 2H), 4.43 t, J = 6.4 Hz, 2H), 3.82 (t, J = 5.2 Hz, 3H), 3.75 (s, 3H), 3.52-3.48 (m, 5H), 3.45 (s, 2H), 2.95-2.84 (m, 1H), 2.69-2.60 (m, 5H), 2.34-2.33 (m, 1H), 2.08-2.00 (m, 1H), 1.12-1.03 (m, 1H), 0.48-0.44 (m, 2H), 0.26-0.21 (m, 2H) |
| 343 | I-348 | IN | GF | 979.5 | 11.07 (s, 1H), 9.95 (s, 1H), 8.96 (s, 1H), 8.79 (s, 1H), 8.24-8.21 (m, 1H), 8.16 (d, J = 5.2 Hz, 1H), 7.81 (d, J = 8.0 Hz, 2H), 7.56 (t, J = 8.4 Hz, 1H), 7.53-7.45 (m, 2H), 7.43-7.15 (m, 1H), 7.14-7.10 (m, 2H), 7.07 (t, J = 5.6 Hz, 1H), 7.05-7.00 (m, 2H), 6.57 (t, J = 5.6 Hz, 1H), 5.05 (dd, J = 5.2, 12.8 Hz, 1H), 3.57-3.47 (m, 16H), 3.19 (t, J = 6.0 Hz, 2H), 2.94-2.83 (m, 1H), 2.75-2.68 (m, 2H), 2.62-2.55 (m, 2H), 2.44-2.41 (m, 4H), 2.37-2.34 (m, 4H), 2.05-1.99 (m, 1H), 1.12-1.03 (m, 1H), 0.49-0.42 (m, 2H), 0.26-0.19 (m, 2H) |
| 344 | I-349 | NE | GF | 979.2 | 11.04 (s, 1H), 9.97 (s, 1H), 8.96 (s, 1H), 8.79 (s, 1H), 8.22 (s, 2H), 8.16 (d, J = 5.2 Hz, 1H), 7.81 (d, J = 8.4 Hz, 2H), 7.55 (d, J = 8.4 Hz, 1H), 7.50 (d, J = 8.4 Hz, 2H), 7.45-7.15 (m, 1H), 7.14-7.03 (m, 4H), 7.00 (s, 1H), 6.88 (d, J = 8.4 Hz, 1H), 5.03 (dd, J = 5.2, 12.8 Hz, 1H), 3.81 (s, 2H), 3.59-3.50 (m, 10H), 3.19 (t, J = 6.4 Hz, 2H), 2.93-2.84 (m, 1H), 2.71-2.68 (m, 2H), 2.60-2.56 (m, 2H), 2.44 (t, J = 5.6 Hz, 4H), 2.41-2.29 (m, 8H), 2.04-1.93 (m, 1H), 1.05-0.94 (m, 1H), 0.51-0.40 (m, 2H), 0.25-0.22 (m, 2H) |
| 345[b] | I-350 | IO | GF | 991.6 | 11.13 (s, 2H), 10.32 (s, 1H), 10.11 (s, 1H), 9.11 (s, 1H), 9.04 (s, 1H), 8.90 (s, 1H), 8.16 (d, J = 6.0 Hz, 1H), 7.99 (d, J = 8.4 Hz, 2H), 7.69 (d, J = 8.4 Hz, 2H), 7.64-7.58 (m, 1H), 7.34-7.25 (m, 1H), 7.20-7.05 (m, 3H), 6.64-6.55 (m, 1H), 5.08 (dd, J = 5.4, 13.0 Hz, 1H), 4.48-4.14 (m, 10H), 3.71 (d, J = 5.2 Hz, 4H), 3.64 (d, J = 4.8 Hz, 9H), 3.37 (s, 2H), 3.23 (d, J = 6.8 Hz, 2H), 3.16 (s, 2H), 2.97-2.85 (m, 1H), 2.64 (s, 1H), 2.59 (s, 1H), 2.11-1.99 (m, 1H), 1.11 (s, 1H), 0.51 (d, J = 8.4 Hz, 2H), 0.27 (d, J = 4.4 Hz, 2H) |
| 346 | I-351 | NG | GF | 991.3 | 11.07 (s, 1H), 10.33 (s, 2H), 10.12 (s, 1H), 9.17 (s, 1H), 9.05 (s, 1H), 8.89 (s, 1H), 8.15 (d, J = 6.0 Hz, 1H), 7.98 (d, J = 8.4 Hz, 2H), 7.68 (d, J = 8.4 Hz, 2H), 7.59 (d, J = 8.4 Hz, 1H), 7.47-7.07 (m, 4H), 7.02 (d, J = 1.6 Hz, 1H), 6.91 (dd, J = 1.6, 8.4 Hz, 1H), 5.04 (dd, J = 5.2, |

TABLE 22-continued

Compounds synthesized via Method 16 with the reductive amination
of various amines with aldehydes in Step 1.

| Ex-#[a,e] | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| | | | | | 12.8 Hz, 1H), 4.46-4.19 (m, 10H), 3.70 (d, J = 5.2 Hz, 10H), 3.37 (s, 4H), 3.23 (d, J = 6.8 Hz, 2H), 3.16 (d, J = 5.6 Hz, 2H), 2.93-2.83 (m, 1H), 2.64-2.52 (m, 2H), 2.04-1.94 (m, 1H), 1.15-1.05 (m, 1H), 0.60-0.47 (m, 2H), 0.33-0.26 (m, 2H) |
| 347[c] | I-352 | OK | IW | 801.1 | 11.09 (s, 1H), 9.97 (s, 1H), 9.40-9.38 (m, 2H), 8.82 (s, 1H), 8.80 (s, 1H), 8.43 (s, 1H), 8.00 (s, 1H), 7.90 (d, J = 8.8 Hz, 2H), 7.71 (d, J = 8.8 Hz, 2H), 7.59-7.52 (m, 1H), 7.31 (t, J = 56.0 Hz, 1 H), 7.12 (d, J = 8.4 Hz, 1H), 7.02 (d, J = 7.2 Hz, 1H), 5.08-5.02 (m, 1H), 4.12-4.30 (m, 2H), 3.95 (s, 3H), 3.75 (t, J = 5.2 Hz, 2H), 3.59-3.68 (m, 6H), 3.47 (t, J = 5.2 Hz, 2H), 3.20-3.00 (s, 2H), 2.96-2.78 (m, 1H), 2.64-2.56 (m, 2H), 2.08-1.97 (m, 1H) |
| 348[c] | I-353 | IX | IW | 801.4 | 11.04 (s, 1H), 9.88 (s, 1H), 8.78-8.74 (m, 2H), 8.43 (s, 1H), 8.24 (s, 1H), 8.00 (s, 1H), 7.78 (d, J = 8.4 Hz, 2H), 7.57-7.53 (m, 1H), 7.47 (d, J = 8.8 Hz, 2H), 7.43-7.12 (m, 2H), 7.00 (d, J = 2.0 Hz, 1H), 6.89 (dd, J = 2.0, 8.4 Hz, 1H), 5.02 (dd, J = 5.2, 12.8 Hz, 1H), 3.94 (s, 3H), 3.77 (s, 2H), 3.62-3.54 (m, 8H), 3.35 (d, J = 5.6 Hz, 2H), 2.92-2.81 (m, 1H), 2.67 (t, J = 5.6 Hz, 2H), 2.60-2.52 (m, 2H), 2.03-1.93 (m, 1H) |
| 349 | I-354 | IX | GF | 867.5 | 11.05 (s, 1H), 9.98 (s, 1H), 8.96 (s, 1H), 8.77 (s, 1H), 8.28 (s, 1H), 8.15 (d, J = 5.3 Hz, 1H), 7.78 (d, J = 8.8 Hz, 2H), 7.54 (d, J = 8.4 Hz, 1H), 7.47 (d, J = 8.8 Hz, 2H), 7.42-7.17 (m, 1H), 7.15 (d, J = 3.6 Hz, 1H), 7.11 (s, 1H), 7.08 (t, J = 5.5 Hz, 1H), 7.03 (dd, J = 1.2, 5.2 Hz, 1H), 7.00 (d, J = 1.6 Hz, 1H), 6.88 (dd, J = 2.0, 8.4 Hz, 1H), 5.02 (dd, J = 5.6, 12.8 Hz, 1H), 3.76 (s, 2H), 3.62-3.55 (m, 8H), 3.22-3.15 (m, 4H), 2.95-2.81 (m, 1H), 2.67-2.64 (m, 2H), 2.57-2.53 (m, 2H), 2.02-1.92 (m, 1H), 1.11-1.02 (m, 1H), 0.47-0.43 (m, 2H), 0.24-0.20 (m, 2H) |
| 350 | I-355 | IZ | GF | 792.1 | 11.12 (s, 1H), 9.99 (s, 1H), 8.97 (s, 1H), 8.78 (s, 1H), 8.16 (d, J = 5.6 Hz, 1H), 7.83-7.77 (d, J = 8.4 Hz, 2H), 7.76-7.72 (m, 2H), 7.72-7.67 (m, 1H), 7.45 (d, J = 8.4 Hz, 2H), 7.29 (t, J = 14.0 Hz, 1H), 7.14-7.07 (m, 2H), 7.04 (dd, J = 1.2, 5.6 Hz, 1H), 5.13 (dd, J = 5.2, 12.4 Hz, 1H), 3.52 (s, 2H), 3.18 (t, J = 6.0 Hz, 2H), 3.07 (t, J = 7.6 Hz, 2H), 2.94-2.83 (m, 1H), 2.64-2.53 (m, 2H), 2.41 (t, J = 6.8 Hz, 2H), 2.15 (s, 3H), 2.09-2.02 (m, 1H), 1.87-1.75 (m, 2H), 1.13-1.02 (m, 1H), 0.49-0.40 (m, 2H), 0.26-0.19 (m, 2H) |
| 351[c] | I-356 | IZ | JA | 716.0 | 11.13 (d, J = 7.6 Hz, 2H), 11.05 (s, 1H), 9.17 (s, 1H), 9.01 (s, 1H), 8.94 (d, J = 6.0 Hz, 2H), 8.15-8.01 (m, 5H), 7.89-7.72 (m, 6H), 5.15 (dd, |

TABLE 22-continued

Compounds synthesized via Method 16 with the reductive amination
of various amines with aldehydes in Step 1.

| Ex-#[a,e] | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| | | | | | J = 3.6, 12.4 Hz, 1H), 4.48-4.26 (m, 2H), 3.12 (d, J = 6.8 Hz, 3H), 2.69 (d, J = 4.8 Hz, 3H), 2.62-2.54 (m, 3H), 2.22-1.98 (m, 4H) |
| 352 | I-357 | FU | GF | 778.1 | 11.11 (s, 1H), 9.98 (s, 1H), 8.97 (s, 1H), 8.78 (s, 1H), 8.29 (s, 2H), 8.16 (d, J = 4.8 Hz, 1H), 7.65-7.89 (m, 5H), 7.56-7.46 (m, 2H), 7.45-7.15 (m, 1H), 7.14-7.00 (m, 3H), 5.30-4.98 (m, 1H), 3.76 (s, 2H), 3.19 (t, J = 5.6 Hz, 2H), 3.05-3.13 (m, 2H), 2.83-2.95 (m, 1H), 2.65-2.56 (m, 4H), 2.00-2.12 (m, 1H), 1.72-1.86 (m, 2H), 0.98-1.15 (m, 1H), 0.38-0.51 (m, 2H), 0.15-0.27 (m, 2H) |
| 353[c] | I-358 | FU | JA | 702.4 | 11.15-11.03 (m, 2H), 9.09 (s, 1H), 8.91 (s, 1H), 8.87-8.83 (m, 2H), 8.33 (s, 1H), 8.03 (s, 1H), 7.99-7.94 (m, 2H), 7.93-7.87 (m, 2H), 7.79-7.73 (m, 3H), 7.72-7.69 (m, 1H), 7.52-7.46 (m, 2H), 5.16-5.10 (m, 1H), 3.76 (s, 2H), 3.14-3.04 (m, 2H), 2.93-2.87 (m, 1H), 2.64-2.61 (m, 1H), 2.60-2.57 (m, 1H), 2.57-2.55 (m, 1H), 2.09-2.03 (m, 1H), 1.85-1.76 (m, 2H) |
| 354[c] | I-359 | NH | JD | 681.1 | 11.13 (s, 1H), 10.35-10.17 (m, 1H), 10.16-9.81 (m, 2H), 9.27-9.05 (m, 1H), 8.94-8.84 (m, 3H), 8.23-8.07 (m, 3H), 8.00-7.90 (m, 4H), 7.84-7.66 (m, 2H), 7.49-7.15 (m, 1H), 5.23-5.08 (m, 1H), 4.72-4.56 (m, 2H), 4.33 (s, 2H), 3.10-2.80 (m, 1H), 2.68-2.52 (m, 2H), 2.09-1.97 (m, 1H) |
| 355 | I-360 | IZ | JC | 920.2 | 11.10 (s, 1H), 9.98 (s, 1H), 8.99 (s, 1H), 8.79 (s, 1H), 8.25 (d, J = 5.2 Hz, 1H), 7.79 (d, J = 8.4 Hz, 2H), 7.77-7.71 (m, 2H), 7.70-7.66 (m, 1H), 7.61 (t, J = 6.4 Hz, 1H), 7.45 (d, J = 8.4 Hz, 2H), 7.43-7.14 (m, 3H), 5.13 (dd, J = 5.2, 12.8 Hz, 1H), 4.30-4.18 (m, 2H), 3.52 (s, 2H), 3.07 (t, J = 7.2 Hz, 2H), 2.96-2.82 (m, 1H), 2.65-2.51 (m, 2H), 2.42 (t, t, J = 7.2 Hz, 2H), 2.16 (s, 3H), 2.09-2.01 (m, 1H), 1.86-1.79 (m, 2H) |
| 356 | I-361 | FU | JC | 806.3 | 11.11 (s, 1H), 9.99 (s, 1H), 9.00 (s, 1H), 8.79 (s, 1H), 8.28-8.24 (m, 2H), 7.82-7.75 (m, 4H), 7.73-7.69 (m, 1H), 7.61 (t, J = 6.4 Hz, 1H), 7.50 (d, J = 8.4 Hz, 2H), 7.27 (s, 1H), 7.22 (d, J = 5.2 Hz, 1H), 7.16 (s, 1H), 5.14 (dd, J = 5.2, 12.8 Hz, 1H), 4.25 (dd, J = 6.8, 9.6 Hz, 2H), 3.77 (s, 2H), 3.10 (t, J = 7.6 Hz, 2H), 2.96-2.83 (m, 1H), 2.68-2.63 (m, 1H), 2.60-2.57 (m, 3H), 2.34 (s, 1H), 2.11-2.02 (m, 1H), 1.86-1.77 (m, 2H) |
| 357 | I-362 | GL | GF | 836.1 | 11.13 (s, 1H), 10.00 (s, 1H), 8.97 (s, 1H), 8.78 (s, 1H), 8.16 (d, J = 5.2 Hz, 1H), 7.85-7.73 (m, 4H), 7.72-7.66 (m, 1H), 7.46 (d, J = 8.4 Hz, 2H), 7.43-7.15 (m, 1H), 7.14-7.07 (m, 2H), 7.05 (dd, J = 1.2, 5.2 Hz, 1H), 5.13 (dd, J = 5.2, 12.8 Hz, 1H), 3.57 (s, 2H), 3.54-3.50 (m, 4H), 3.19 (t, J = 6.0 Hz, 2H), 3.08 (t, J = 7.6 Hz, 2H), 2.93-2.84 (m, |

TABLE 22-continued

Compounds synthesized via Method 16 with the reductive amination
of various amines with aldehydes in Step 1.

| Ex-#[a,e] | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| | | | | | 1H), 2.64-2.58 (m, 1H), 2.58-2.56 (m, 1H), 2.55-2.53 (m, 2H), 2.19 (s, 3H), 2.09-2.01 (m, 1H), 1.91-1.81 (m, 2H), 1.13-1.03 (m, 1H), 0.50-0.42 (m, 2H), 0.27-0.19 (m, 2H) |
| 358 | I-363 | GL | JD | 767.4 | 11.10 (s, 1H), 10.09 (s, 1H), 9.05 (s, 1H), 8.90-8.81 (m, 2H), 8.78 (s, 1H), 8.03-7.93 (m, 2H), 7.83-7.78 (m, 2H), 7.77-7.72 (m, 2H), 7.71-7.66 (m, 1H), 7.46 (d, J = 8.4 Hz, 2H), 7.43-7.13 (m, 1H), 5.12 (dd, J = 5.2, 12.8 Hz, 1H), 3.56 (s, 2H), 3.51 (t, J = 6.0 Hz, 2H), 3.42 (t, J = 6.4 Hz, 2H), 3.08 (t, J = 7.6 Hz, 2H), 2.94-2.83 (m, 1H), 2.63-2.57 (m, 1H), 2.56-2.53 (m, 2H), 2.53-2.52 (m, 1H), 2.19 (s, 3H), 2.08-2.01 (m, 1H), 1.90-1.80 (m, 2H) |
| 359[c] | I-364 | FU | JM | 780.1 | 11.11 (s, 1H), 10.29-10.23 (m, 1H), 9.20-9.16 (m, 1H), 9.09 (s, 1H), 9.01-8.92 (m, 3H), 8.89 (s, 1H), 8.24-8.14 (m, 2H), 8.01-7.90 (m, 2H), 7.84-7.77 (m, 2H), 7.74-7.66 (m, 1H), 7.62-7.54 (m, 1H), 7.42-7.29 (m, 1H), 5.30-5.08 (m, 1H), 3.77 (s, 2H), 3.36-3.09 (m, 3H), 3.04-2.97 (m, 3H), 2.92-2.83 (m, 1H), 2.64-2.56 (m, 2H), 2.14-1.96 (m, 2H) |
| 360[c] | I-365 | IZ | JD | 723.3 | 11.10 (s, 1H), 10.09 (s, 1H), 9.05 (s, 1H), 8.84 (d, J = 6.0 Hz 2H), 8.78 (s, 1H), 7.99 (d, J = 6.0 Hz 2H), 7.79 (d, J = 8.4 Hz, 2H), 7.77-7.71 (m, 2H), 7.71-7.66 (m, 1H), 7.45 (d, J = 8.8 Hz, 2H), 7.29 (d, J = 54 Hz, 1H), 5.13 (dd, J = 5.2, 12.8 Hz, 1H), 3.52 (s, 2H), 3.14-3.02 (m, 2H), 2.93-2.84 (m, 1H), 2.65-2.52 (m, 2H), 2.41 (t, J = 7.2 Hz, 2H), 2.15 (s, 3H), 2.10-2.02 (m, 1H), 1.86-1.79 (m, 2H) |
| 361[c] | I-366 | FU | JD | 709.1 | 11.12 (s, 1H), 10.23 (s, 1H), 9.41 (s, 2H), 8.90 (d, J = 6.0 Hz, 2H), 8.86 (s, 1H), 8.11 (d, J = 6.4 Hz, 2H), 7.94 (d, J = 8.8 Hz, 2H), 7.87-7.67 (m, 5H) 7.32 (t, J = 14.0 Hz,, 1H), 5.14 (dd, J = 5.2, 12.8 Hz, 1H), 4.19 (t, J = 5.2 Hz, 2H), 3.12 (t, J = 7.2 Hz, 2H), 3.04-2.81 (m, 3H), 2.66-2.53 (m, 2H), 2.14-1.97 (m, 3H) |
| 362 | I-367 | GW | GF | 822.4 | 10.89 (s, 1H), 9.77 (s, 1H), 8.74 (s, 1H), 8.56 (s, 1H), 8.00 (s, 1H), 7.93 (d, J = 5.2 Hz, 1H), 7.57 (d, J = 8.4 Hz, 2H), 7.54-7.50 (m, 2H), 7.49-7.45 (m, 1H), 7.26 (d, J = 8.8 Hz, 2H), 7.20-6.91 (m, 1H), 6.91-6.85 (m, 2H), 6.78-6.82 (m, 1H), 4.90 (dd, J = 5.2, 12.8 Hz, 1H), 3.56 (s, 2H), 3.23 (t, J = 5.6 Hz, 2H), 3.19 (t, J = 6.0 Hz, 2H), 2.95 (t, J = 6.0 Hz, 2H), 2.85 (t, J = 7.2 Hz, 2H), 2.71-2.59 (m, 1H), 2.46-2.42 (m, 2H), 2.40-2.33 (m, 1H), 2.32-2.29 (m, 1H), 1.86-1.78 (m, 1H), 1.66-1.59 (m, 2H), 0.88-0.79 (m, 1H), 0.25-0.20 (m, 2H), 0.02--0.03 (m, 2H) |
| 363[c] | I-368 | GW | JD | 753.3 | 11.12 (s, 1H), 10.12 (s, 1H), 9.06 (s, 1H), 8.84 (d, J = 6.0 Hz, 2H), |

TABLE 22-continued

Compounds synthesized via Method 16 with the reductive amination
of various amines with aldehydes in Step 1.

| Ex-#[a,e] | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| | | | | | 8.79 (s, 1H), 8.01-7.95 (m, 2H), 7.85-7.80 (m, 2H), 7.79-7.72 (m, 2H), 7.71-7.68 (m, 1H), 7.54-7.47 (m, 2H), 7.43-7.14 (m, 1H), 5.13 (dd, J = 5.6, 12.8 Hz, 1H), 3.83 (s, 2H), 3.48 (t, J = 5.6 Hz, 2H), 3.42 (t, J = 6.4 Hz, 2H), 3.08 (t, J = 7.6 Hz, 2H), 2.94-2.83 (m, 1H), 2.71 (t, J = 5.6 Hz, 2H), 2.64-2.51 (m, 2H), 2.09-2.01 (m, 1H), 1.90-1.82 (m, 2H) |
| 364 | I-369 | JH | GF | 792.1 | 11.12 (s, 1H), 10.01 (s, 1H), 8.98 (s, 1H), 8.79 (s, 1H), 8.16 (d, J = 5.2 Hz, 1H), 7.84-7.77 (m, 4H), 7.77-7.71 (m, 1H), 7.49-7.44 (m, 2H), 7.44-7.16 (m, 1H), 7.12 (s, 1H), 7.11-7.08 (m, 1H), 7.04 (dd, J = 1.2, 5.2 Hz, 1H), 5.14 (dd, J = 5.6, 13.0 Hz, 1H), 3.51 (s, 2H), 3.19 (t, J = 6.0 Hz, 2H), 2.95-2.86 (m, 1H), 2.85-2.80 (m, 2H), 2.64-2.55 (m, 2H), 2.39 (d, J = 6.8 Hz, 2H), 2.14 (s, 3H), 2.09-2.00 (m, 1H), 1.90-1.80 (m, 2H), 1.12-1.03 (m, 1H), 0.49-0.43 (m, 2H), 0.26-0.21 (m, 2H) |
| 365[c] | I-370 | JH | GE | 716.4 | 11.11 (s, 2H), 9.10-9.07 (m, 1H), 8.93-8.91 (m, 1H), 8.85 (d, J = 6.0 Hz, 2H), 8.04 (s, 1H), 7.96 (d, J = 6.0 Hz, 2H), 7.90 (d, J = 8.4 Hz, 2H), 7.83-7.76 (m, 3H), 7.71 (d, J = 7.6 Hz, 1H), 7.45 (d, J = 8.4 Hz, 2H), 5.14 (dd, J = 5.6, 13.2 Hz, 1H), 3.51 (s, 2H), 2.94-2.86 (m, 1H), 2.83 (d, J = 7.2 Hz, 2H), 2.64-2.54 (m, 2H), 2.39-2.35 (m, 2H), 2.15 (s, 3H), 2.08-2.00 (m, 1H), 1.89-1.81 (m, 2H) |
| 366 | I-371 | JI | GF | 778.4 | 11.14 (s, 1H), 10.03 (s, 1H), 8.98 (s, 1H), 8.79 (s, 1H), 8.30 (s, 1H), 8.16 (d, J = 5.2 Hz, 1H), 7.87-7.77 (m, 4H), 7.72 (d, J = 7.2 Hz, 1H), 7.51 (d, J = 8.4 Hz, 2H), 7.46-7.15 (m, 1H), 7.15-7.08 (m, 2H), 7.05 (d, J = 5.2 Hz, 1H), 5.15 (dd, J = 5.2, 12.8 Hz, 1H), 3.78 (s, 2H), 3.19 (t, J = 6.0 Hz, 2H), 2.95-2.81 (m, 3H), 2.71-2.55 (m, 4H), 2.09-2.01 (m, 1H), 1.89-1.75 (m, 2H), 1.07-1.06 (m, 1H), 0.51-0.41 (m, 2H), 0.23-0.22 (m, 2H) |
| 367[c] | I-372 | JI | GE | 702.3 | 11.10 (s, 2H), 9.08 (s, 1H), 8.92 (s, 1H), 8.85 (d, J = 5.6 Hz, 2H), 8.29 (s, 1H), 8.06 (s, 1H), 7.99-7.89 (m, 4H), 7.83 (d, J = 7.6 Hz, 1H), 7.81-7.75 (m, 2H) 7.72 (d, J = 7.6 Hz, 1H), 7.52 (d, J = 8.2 Hz, 2H), 5.14 (dd, J = 5.2, 12.8 Hz, 1H), 3.86-3.75 (m, 2H), 2.95-2.83 (m, 3H), 2.65-2.54 (m, 4H), 2.10-2.01 (m, 1H), 1.89-1.81 (m, 1H) |
| 368[c] | I-373 | JJ | JD | 681.3 | 11.11 (s, 1H), 10.09 (s, 1H), 9.06 (s, 1H), 8.85 (d, J = 6.0 Hz, 2H), 8.79 (s, 1H), 8.39 (s, 1H), 7.99 (d, J = 6.0 Hz, 2H), 7.95 (s, 1H), 7.90-7.86 (m, 2H), 7.82 (d, J = 8.4 Hz, 2H), 7.53 (d, J = 8.4 Hz, 2H), 7.43-7.15 (m, 1H), 5.20-5.08 (m, 1H), 3.91 (s, 2H), 3.76 (s, 2H), 2.94-2.87 (m, 1H), 2.65-2.61 (m, 1H), 2.60-2.57 (m, 1H), 2.09-2.00 (m, 1H) |

TABLE 22-continued

Compounds synthesized via Method 16 with the reductive amination
of various amines with aldehydes in Step 1.

| Ex-#[a,e] | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| 369 | I-374 | JH | JC | 820.4 | 11.09 (s, 1H), 9.98 (s, 1H), 8.99 (s, 1H), 8.79 (s, 1H), 8.25 (d, J = 5.2 Hz, 1H), 7.83-7.78 (m, 4H), 7.75-7.71 (m, 1H), 7.60 (t, J = 6.4 Hz, 1H), 7.47-7.43 (m, 2H), 7.30-7 16 (m, 3H) 5.13 (dd, J = 5.2, 13.2 Hz, 1H), 4.30-4.20 (m, 2H), 3.51 (s, 2H), 2.95-2.85 (m, 1H), 2.83 (t, J = 7.2 Hz, 2H), 2.64-2.56 (m, 2H), 2.38 (t, J = 6.8 Hz, 2H), 2.14 (s, 3H), 2.09-2.01 (m, 1H), 1.89-1.82 (m, 2H) |
| 370 | I-375 | JI | JC | 806.3 | 11.11 (s, 1H), 10.01 (s, 1H), 9.00 (s, 1H), 8.82 (s, 1H), 8.26 (d, J = 5.2 Hz, 1H), 8.19 (s, 1H), 7.89-7.80 (m, 4H), 7.75-7.72 (m, 1H), 7.62 (t, J = 6.4 Hz, 1H), 7.56 (d, J = 8.4 Hz, 2H), 7.44-7.17 (m, 1H), 7.27 (s, 1H), 7.22 (dd, J = 1.2, 5.2 Hz, 1H), 5.15 (dd, J = 5.2, 12.8 Hz, 1H), 4.32-4.20 (m, 2H), 3.90 (s, 2H), 2.95-2.82 (m, 3H), 2.70-2.53 (m, 4H), 2.11-2.01 (m, 1H), 1.94-1.83 (m, 2H) |
| 371 | I-376 | JK | GF | 836.4 | 11.12 (s, 1H), 9.99 (s, 1H), 8.97 (s, 1H), 8.78 (s, 1H), 8.16 (d, J = 5.2 Hz, 1H), 7.84-7.81 (m, 2H), 7.78 (d, J = 6.0 Hz, 2H), 7.71 (d, J = 8.0 Hz, 1H), 7.46 (d, J = 8.4 Hz, 2H), 7.42-7.14 (m, 1H), 7.12-7.08 (m, 2H), 7.06-7.01 (m, 1H), 5.18-5.08 (m, 1H), 3.56 (s, 2H), 3.53-3.48 (m, 4H), 3.21-3.14 (m, 2H), 2.92-2.86 (m, 1H), 2.84-2.80 (m, 2H), 2.63-2.59 (m, 1H), 2.58-2.57 (m, 1H), 2.56-2.54 (m, 2H), 2.19 (s, 3H), 2.07-2.02 (m, 1H), 1.89-1.84 (m, 2H), 1.11-1.04 (m, 1H), 0.47-0.42 (m, 2H), 0.24-0.20 (m, 2H) |
| 372[c] | I-377 | JK | JD | 767.4 | 11.11 (s, 1H), 10.09 (s, 1H), 9.06 (s, 1H), 8.87-8.82 (m, 2H), 8.79 (s, 1H), 8.01-7.97 (m, 2H), 7.86-7.77 (m, 4H), 7.72 (d, J = 7.2 Hz, 1H), 7.47 (d, J = 8.4 Hz, 2H), 7.44-7.12 (m, 1H), 5.18-5.11 (m, 1H), 3.58 (s, 2H), 3.54-3.51 (m, 2H), 3.41-3.40 (m, 2H), 2.95-2.88 (m, 1H), 2.87-2.82 (m, 2H), 2.64-2.58 (m, 1H), 2.57-2.54 (m, 2H), 2.54-2.52 (m, 1H), 2.21 (s, 3H), 2.08-2.01 (m, 1H), 1.92-1.84 (m, 2H) |
| 373[c] | I-378 | JI | JM | 780.3 | 11.09 (s, 1H), 10.20 (s, 1H), 9.08 (s, 1H), 8.93-8.80 (m, 3H), 8.30 (s, 1H), 8.03-7.97 (m, 2H), 7.95-7.93 (m, 2H), 7.84-7.72 (m, 2H), 7.65-7.54 (m, 3H), 7.47-7.16 (m, 1H), 5.15 (dd, J = 5.2, 12.8 Hz, 1H), 3.73-3.46 (m, 2H), 3.45-3.20 (m, 2H), 3.03-2.85 (m, 4H), 2.84-2.52 (m, 6H), 2.10-1.96 (m, 1H), 1.90-1.68 (m, 2H) |
| 374[c] | I-379 | JH | JD | 723.3 | 11.10 (s, 1H), 10.11 (s, 1H), 9.03 (s, 1H), 8.83 (d, J = 5.6 Hz, 2H), 8.76 (s, 1H), 7.99 (d, J = 5.6 Hz, 2H), 7.84-7.76 (m, 4H), 7.75-7.67 (m, 1H), 7.49-7.42 (m, 2H), 7.42-7.14 (m, 1H), 5.13 (dd, J = 5.5, 13.0 Hz, 1H), 3.50 (s, 2H), 2.96-2.85 (m, 1H), 2.83 (d, J = 7.2 Hz, 2H), 2.63-2.53 (m, 2H), |

TABLE 22-continued

Compounds synthesized via Method 16 with the reductive amination
of various amines with aldehydes in Step 1.

| Ex-#[a,e] | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| | | | | | 2.37 (t, J = 6.8 Hz, 2H), 2.14 (s, 3H), 2.08-2.00 (m, 1H), 1.89-1.81 (m, 2H) |
| 375[c] | I-380 | JI | JD | 709.3 | 11.11 (s, 1H), 10.10 (s, 1H), 9.06 (s, 1H), 8.89-8.82 (m, 2H), 8.79 (s, 1H), 8.25 (s, 1H), 8.02-7.97 (m, 2H), 7.87-7.77 (m, 4H), 7.73-7.71 (m, 1H), 7.51 (d, J = 8.4 Hz, 2H), 7.44-7.14 (m, 1H), 5.14 (dd, J = 5.2, 12.8 Hz, 1H), 3.79 (s, 2H), 2.96-2.78 (m, 3H), 2.69-2.52 (m, 4H), 2.12-2.02 (m, 1H), 1.88-1.77 (m, 2H) |
| 376 | I-381 | JR | GF | 822.1 | 11.13 (s, 1H), 10.01 (s, 1H), 8.98 (s, 1H), 8.80 (s, 1H), 8.21-8.10 (m, 2H), 7.87-7.78 (m, 4H), 7.73 (d, J = 7.6 Hz, 1H), 7.52 (d, J = 7.6 Hz, 2H), 7.46-7.15 (m, 1H), 7.14-7.08 (m, 2H), 7.08-7.01 (m, 1H), 5.20-5.10 (m, 1H), 3.91-3.79 (m, 2H), 3.52-3.45 (m, 2H), 3.44-3.35 (m, 2H), 3.24-3.22 (m, 2H), 2.97-2.81 (m, 3H), 2.77-2.58 (m, 4H), 2.12-2.01 (m, 1H), 1.94-1.82 (m, 2H), 1.14-1.02 (m, 1H), 0.53-0.41 (m, 2H), 0.29-0.19 (m, 2H) |
| 377[c] | I-382 | JR | JD | 753.3 | 11.11 (s, 1H), 10.28 (s, 1H), 9.48 (s, 2H), 9.18 (s, 1H), 8.95 (d, J = 6.4 Hz, 2H), 8.87 (s, 1H), 8.20 (d, J = 6.0 Hz, 2H), 8.04-7.90 (m, 2H), 7.85 (d, J = 7.6 Hz, 1H), 7.81-7.73 (m, 3H), 7.49-7.19 (m, 1H), 5.16-5.11 (m, 1H), 4.23 (t, J = 5.2 Hz, 2H), 3.70 (t, J = 5.2 Hz, 2H), 3.45 (t, J = 6.4 Hz, 2H), 3.10 (s, 2H), 2.95-2.78 (m, 3H), 2.65-2.51 (m, 2H), 2.10-2.00 (m, 1H), 1.95-1.86 (m, 2H) |
| 378 | I-383 | II | GF | 949.2 | 9.96 (s, 1H), 8.96 (s, 1H), 8.78 (s, 1H), 8.16 (d, J = 5.2 Hz, 1H), 7.87-7.81 (m, 2H), 7.79 (d, J = 8.4 Hz, 2H), 7.65 (d, J = 8.4 Hz, 1H), 7.52-7.44 (m, 3H), 7.43-7.15 (m, 1H), 7.12 (s, 1H), 7.07 (t, J = 5.6 Hz, 1H), 7.05-7.02 (m, 1H), 5.58 (s, 2H), 5.09 (dd, J = 5.6, 12.8 Hz, 1H), 4.66 (t, J = 5.2 Hz, 2H), 3.84 (t, J = 5.2 Hz, 2H), 3.75 (s, 2H), 3.51-3.47 (m, 2H), 3.45-3.40 (m, 4H), 3.19 (t, J = 6.0 Hz, 2H), 2.93-2.81 (m, 1H), 2.63 (t, J = 5.6 Hz, 2H), 2.60-2.54 (m, 2H), 2.06-1.97 (m, 1H), 1.15-1.00 (m, 1H), 0.49-0.42 (m, 2H), 0.26-0.19 (m, 2H) |
| 379 | I-384 | NT | GF | 936.4 | 11.01 (s, 1H), 9.99 (s, 1H), 8.96 (s, 1H), 8.82 (s, 1H), 8.17 (d, J = 5.2 Hz, 1H), 7.85 (d, J = 8.8 Hz, 2H), 7.56 (d, J = 8.8 Hz, 2H), 7.46-7.16 (m, 2H), 7.12 (s, 1H), 7.10-7.02 (m, 2H), 6.93 (d, J = 7.2 Hz, 1H), 6.79 (d, J = 8.0 Hz, 1H), 5.31 (s, 1H), 5.12 (dd, J = 5.2, 13.2 Hz, 1H), 4.35-4.08 (m, 2H), 3.94 (s, 2H), 3.67-3.46 (m, 8H), 3.36-3.30 (m, 1H), 3.19 (t, J = 6.0 Hz, 2H), 2.96-2.94 (m, 2H), 2.83 (t, J = 5.2 Hz, 2H), 2.62-2.55 (m, 2H), 2.69-2.54 (m, 1H), 2.36-2.19 (m, 3H), 2.11-2.00 (m, 1H), 1.93-1.91 (m, 2H), 1.57-1.39 (m, 2H), |

TABLE 22-continued

Compounds synthesized via Method 16 with the reductive amination
of various amines with aldehydes in Step 1.

| Ex-#[a,e] | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| | | | | | 1.14-0.96 (m, 1H), 0.54-0.40 (m, 2H), 0.28-0.12 (m, 2H) |
| 380 | I-385 | NU | GF | 906.2 | 11.08 (s, 1H), 9.97 (s, 1H), 8.96 (s, 1H), 8.79 (s, 1H), 8.16 (d, J = 5.2 Hz, 1H), 7.83 (d, J = 8.8 Hz, 2H), 7.60-7.50 (m, 3H), 7.43-7.12 (m, 2H), 7.11 (s, 1H), 7.07 (t, J = 5.2 Hz, 1H), 7.05-7.00 (m, 2H), 6.23 (d, J = 8.0 Hz, 1H), 5.04 (dd, J = 5.2, 12.8 Hz, 1H), 3.88 (s, 2H), 3.66-3.56 (m, 1H), 3.55-3.49 (m, 4H), 3.19 (t, J = 6.0 Hz, 2H), 2.93-2.85 (m, 1H), 2.85-2.79 (m, 2H), 2.79-2.73 (m, 2H), 2.63-2.55 (m, 2H), 2.55-2.53 (m, 2H), 2.25 (t, J = 10.4 Hz, 2H), 2.08-1.97 (m, 1H), 1.96-1.84 (m, 2H), 1.56-1.41 (m, 2H), 1.13-1.01 (m, 1H), 0.50-0.41 (m, 2H), 0.25-0.18 (m, 2H) |
| 381 | I-386 | JY | GF | 994.2 | 11.08 (s, 1H), 9.97 (s, 1H), 8.96 (s, 1H), 8.80 (s, 1H), 8.16 (d, J = 5.2 Hz, 1H), 7.88-7.80 (m, 2H), 7.60-7.49 (m, 3H), 7.44-7.15 (m, 1H), 7.15-7.10 (m, 2H), 7.07 (t, J = 5.2 Hz, 1H), 7.05-7.01 (m, 2H), 6.22 (d, J = 8.0 Hz, 1H), 5.05 (dd, J = 5.2, 12.8 Hz, 1H), 3.88 (s, 2H), 3.62-3.55 (m, 1H), 3.55-3.47 (m, 12H), 3.19 (t, J = 6.0 Hz, 2H), 2.94-2.84 (m, 1H), 2.83-2.74 (m, 4H), 2.63-2.52 (m, 2H), 2.48-2.42 (m, 2H), 2.26-2.17 (m, 2H), 2.07-1.98 (m, 1H), 1.96-1.85 (m, 2H), 1.48-1.42 (m, 2H), 1.13-1.01 (m, 1H), 0.49-0.42 (m, 2H), 0.26-0.20 (m, 2H) |
| 382 | I-387 | NX | GF | 936.4 | 10.92 (s, 1H), 9.99 (s, 1H), 8.97 (s, 1H), 8.80 (s, 1H), 8.20 (s, 1H), 8.17 (d, J = 5.6 Hz, 1H), 7.82 (d, J = 8.4 Hz, 2H), 7.50 (d, J = 8.4 Hz, 2H), 7.43-7.16 (m, 2H), 7.13-7.08 (m, 2H), 7.05 (d, J = 5.2 Hz, 1H), 6.69-6.63 (m, 2H), 6.26-6.19 (m, 1H), 6.22 (d, J = 7.6 Hz, 1H), 5.00 (dd, J = 5.2, 13.2 Hz, 1H), 4.26-4.10 (m, 2H), 3.81 (s, 2H), 3.64-3.48 (m, 8H), 3.26-3.24 (m, 2H), 3.22-3.15 (m, 2H), 2.94-2.90 (m, 1H), 2.88-2.82 (m, 3H), 2.74-2.86 (m, 2H), 2.61-2.58 (m, 1H), 2.57-2.55 (m, 1H), 2.15-2.11 (m, 2H), 1.91-1.89 (m, 3H), 1.41-1.38 (m, 2H), 1.10-1.06 (m, 1H), 0.49-0.44 (m, 2H), 0.26-0.21 (m, 2H) |
| 383 | I-388 | JZ | GF | 906.4 | 11.03 (s, 1H), 9.95 (s, 1H), 8.96 (s, 1H), 8.79 (s, 1H), 8.22 (s, 1H), 8.16 (d, J = 5.2 Hz, 1H), 7.81 (d, J = 8.4 Hz, 2H), 7.54 (d, J = 8.4 Hz, 1H), 7.51 (d, J = 8.8 Hz, 2H), 7.44-7.14 (m, 1H), 7.12 (s, 1H), 7.09-7.05 (m, 1H), 7.04 (d, J = 6.4 Hz, 1H), 6.99-6.95 (m, 2H), 6.89-6.84 (m, 1H), 5.07-4.98 (m, 1H), 3.81 (s, 2H), 3.55-3.47 (m, 6H), 3.42-3.35 (m, 2H), 3.21-3.18 (m, 2H), 2.89-2.80 (m, 3H), 2.72-2.67 (m, 2H), 2.60-2.54 (m, 1H), 2.54-2.53 (m, 1H), 2.21-2.14 (m, 2H), 2.03-1.96 (m, 1H), 1.94-1.86 (m, 2H), 1.46-1.38 (m, 2H), |

TABLE 22-continued

Compounds synthesized via Method 16 with the reductive amination
of various amines with aldehydes in Step 1.

| Ex-#[a,e] | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| | | | | | 1.12-1.04 (m, 1H), 0.48-0.44 (m, 2H), 0.25-0.21 (m, 2H) |
| 384 | I-389 | KA | GF | 994.6 | 11.04 (s, 1H), 9.98 (s, 1H), 8.95 (s, 1H), 8.78 (s, 1H), 8.29 (s, 1H), 8.15 (d, J = 5.6 Hz, 1H), 7.80 (d, J = 8.4 Hz, 2H), 7.57-7.44 (m, 3H), 7.43-7.15 (m, 1H), 7.11 (s, 1H), 7.09-7.01 (m, 2H), 7.00-6.90 (m, 2H), 6.85 (d, J = 8.0 Hz, 1H), 5.01 (dd, J = 5.2, 12.8 Hz, 1H), 3.56-3.45 (m, 16H), 3.21-3.15 (m, 2H), 2.90-2.78 (m, 3H), 2.71 (t, J = 5.6 Hz, 2H), 2.62-2.54 (m, 2H), 2.26-2.03 (m, 3H), 2.02-1.95 (m, 1H), 1.92-1.82 (m, 2H), 1.47-1.35 (m, 2H), 1.09-1.04 (m, 1H), 0.41-0.50 (m, 2H), 0.27-0.18 (m, 2H) |
| 385 | I-390 | NY | GF | 892.1 | 11.07 (s, 1H), 9.96 (s, 1H), 8.97 (s, 1H), 8.78 (s, 1H), 8.24 (s, 1H), 8.17 (d, J = 5.2 Hz, 1H), 7.80 (d, J = 8.4 Hz, 2H), 7.70-7.64 (m, 1H), 7.52 (s, 1H), 7.46-7.33 (m, 1H), 7.31-7.24 (m, 1H), 7.18-7.10 (m, 1H), 7.09-7.04 (m, 1H), 5.08 (dd, J = 5.2, 13.0 Hz, 1H), 3.81 (s, 2H), 3.59 (s, 1H), 3.27-3.19 (m, 3H), 2.73-2.71 (m, 1H), 2.69-2.67 (m, 1H), 2.61 (s, 4H), 2.58-2.54 (m, 4H), 2.06-1.99 (m, 1H), 1.12-1.04 (m, 1H), 0.50-0.44 (m, 2H), 0.27-0.18 (m, 2H) |
| 386 | I-391 | KB | GF | 980.5 | 11.06 (s, 1H), 9.95 (s, 1H), 8.96 (s, 1H), 8.78 (s, 1H), 8.29 (s, 1H), 8.16 (d, J = 5.2 Hz, 1H), 7.79 (d, J = 8.8 Hz, 2H), 7.67 (dd, J = 7.2, 8.3 Hz, 1H), 7.48 (d, J = 8.8 Hz, 2H), 7.43-7.15 (m, 3H), 7.11 (s, 1H), 7.07 (t, J = 5.6 Hz, 1H), 7.03 (dd, J = 1.2, 5.2 Hz, 1H), 5.08 (dd, J = 5.6, 12.8 Hz, 1H), 3.77 (s, 2H), 3.57-3.46 (m, 14H), 3.27 (s, 4H), 3.19 (t, J = 6.0 Hz, 2H), 2.92-2.81 (m, 1H), 2.67 (t, J = 5.6 Hz, 2H), 2.62-2.58 (m, 4H), 2.54-2.52 (m, 2H), 2.06-1.99 (m, 1H), 1.12-1.03 (m, 1H), 0.48-0.43 (m, 2H), 0.25-0.21 (m, 2H) |
| 387 | I-392 | KE | GF | 922.7 | 10.93 (s, 1H), 9.98 (s, 1H), 8.97 (s, 1H), 8.78 (s, 1H), 8.20 (s, 1H), 8.16 (d, J = 5.2 Hz, 1H), 7.80 (d, J = 8.4 Hz, 2H), 7.50 (d, J = 8.8 Hz, 3H), 7.43-7.14 (m, 1H), 7.13-7.07 (m, 2H), 7.04-7.00 (m, 3H), 5.09-4.96 (m, 1H), 4.33-4.17 (m, 2H), 3.79 (s, 2H), 3.55-3.51 (m, 6H), 3.25-3.23 (m, 8H), 3.20-2.18 (m, 2H), 2.94-2.84 (m, 1H), 2.72-2.68 (m, 2H), 2.61-2.56 (m, 1H), 2.56-2.54 (m, 4H), 2.41-2.34 (m, 1H), 2.00-1.86 (m, 1H), 1.13-1.00 (m, 1H), 0.48-0.42 (m, 2H), 0.26-0.20 (m, 2H) |
| 388 | I-393 | KF | GF | 892.5 | 11.06 (s, 1H), 9.95 (s, 1H), 8.96 (s, 1H), 8.78 (s, 1H), 8.22 (s, 1H), 8.16 (d, J = 5.2 Hz, 1H), 7.81 (d, J = 8.4 Hz, 2H), 7.65 (d, J = 8.4 Hz, 1H), 7.52 (d, J = 8.4 Hz, 2H), 7.44-7.14 (m, 3H), 7.12 (s, 1H), 7.10-7.00 (m, 2H), 5.06 (dd, J = 5.2, 12.8 Hz, 1H), 3.83 (s, 2H), 3.60-3.47 (m, 4H), 3.44-3.35 (m, 4H), 3.19 (t, J = 6.0 Hz, 2H), 2.94-2.80 (m, 1H), |

TABLE 22-continued

Compounds synthesized via Method 16 with the reductive amination
of various amines with aldehydes in Step 1.

| Ex-#[a,e] | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| | | | | | 2.72 (t, J = 5.6 Hz, 2H), 2.60-2.52 (m, 8H), 2.04-1.97 (m, 1H), 1.12-1.01 (m, 1H), 0.50-0.38 (m, 2H), 0.29-0.17 (m, 2H) |
| 389 | I-394 | NZ | GF | 980.5 | 11.06 (s, 1H), 9.98 (s, 1H), 8.96 (s, 1H), 8.78 (s, 1H), 8.35-8.32 (m, 1H), 8.32 (s, 1H), 8.15 (d, J = 5.2 Hz, 1H), 7.79 (d, J = 8.4 Hz, 2H), 7.65 (d, J = 8.4 Hz, 1H), 7.52-7.45 (m, 1H), 7.48 (d, J = 8.4 Hz, 1H), 7.45-7.14 (m, 3H) 7.13-7.02 (m, 3H), 5.06 (dd, J = 5.2, 12.8 Hz, 1H), 3.77 (s, 2H), 3.59-3.27 (m, 18H), 3.18 (t, J = 6.0 Hz, 2H), 2.95-2.83 (m, 1H), 2.73-2.63 (m, 2H), 2.62-2.51 (m, 6H), 2.07-1.96 (m, 1H), 1.10-1.03 (m, 1H), 0.50-0.40 (m, 2H), 0.26-0.15 (m, 2H) |
| 390 | I-395 | KK | GC | 943.5 | 10.86 (s, 1H), 10.74 (s, 1H), 8.74 (s, 1H), 8.68 (s, 1H), 8.01 (s, 3H), 7.93 (d, J = 5.2 Hz, 1H), 7.80 (s, 1H), 7.70 (d, J = 8.4 Hz, 2H), 7.49 (s, 1H), 7.33-7.28 (m, 3H), 6.88 (s, 2H), 6.79-6.75 (m, 2H), 5.97 (d, J = 8.0 Hz, 1H), 4.81 (dd, J = 5.2, 12.8 Hz, 1H), 3.90 (s, 9H), 3.64 (s, 2H), 3.34-3.30 (m, 3H), 2.95 (t, J = 6.0 Hz, 3H), 2.69-2.60 (m, 1H), 2.58-2.51 (m, 5H), 2.39-2.31 (m, 1H), 1.97 (t, J = 10.4 Hz, 2H), 1.82-1.76 (m, 1H), 1.65 (d, J = 10.4 Hz, 2H), 1.25-1.18 (m, 2H), 0.86-0.79 (m, 1H), 0.24-0.19 (m, 2H), 0.01-0.03 (m, 2H) |
| 391 | I-396 | KL | GC | 929.5 | 11.10 (s, 1H), 10.98 (s, 1H), 8.98 (s, 1H), 8.92 (s, 1H), 8.17 (d, J = 5.2 Hz, 1H), 8.04 (s, 1H), 7.96 (d, J = 8.4 Hz, 2H), 7.74 (s, 1H), 7.70-7.63 (m, 1H), 7.56 (d, J = 8.4 Hz, 2H), 7.30 (dd, J = 7.6, 18.4 Hz, 2H), 7.16 (t, J = 5.2 Hz, 1H), 7.12 (s, 1H), 7.00 (dd, J = 1.2, 5.2 Hz, 1H), 5.08 (dd, J = 5.2, 12.8 Hz, 1H), 3.94 (s, 2H), 3.62-3.53 (m, 8H), 3.30-3.21 (m, 4H), 3.19 (t, J = 6.0 Hz, 2H), 2.93-2.86 (m, 1H), 2.84 (t, J = 5.2 Hz, 2H), 2.64-2.52 (m, 8H), 2.07-1.98 (m, 1H), 1.14-1.02 (m, 1H), 0.49-0.43 (m, 2H), 0.26-0.20 (m, 2H) |
| 392 | I-397 | JI | KM | 842.4 | 11.23-10.96 (m, 2H), 9.00 (s, 2H), 8.22 (s, 1H), 8.16 (d, J = 5.2 Hz, 1H), 8.13-8.00 (m, 3H), 7.89-7.65 (m, 4H), 7.60 (s, 2H), 7.16 (t, J = 5.6 Hz, 1H), 7.12 (s, 1H), 7.00 (dd, J = 1.2, 5.2 Hz, 1H), 5.14 (dd, J = 4.4, 12.8 Hz, 1H), 3.89-3.65 (m, 4H), 3.19 (t, J = 6.0 Hz, 2H), 2.98 (s, 3H), 2.94-2.82 (m, 3H), 2.72 (s, 2H), 2.64-2.52 (m, 2H), 2.09-2.01 (m, 1H), 1.94-1.67 (m, 1H), 1.92-1.66 (m, 1H), 1.11-1.01 (m, 1H), 0.48-0.41 (m, 2H), 0.25-0.19 (m, 2H) |
| 393 | I-398 | LR | GC | 902.5 | 10.75 (s, 1H), 8.75 (s, 1H), 8.67 (s, 1H), 8.05 (s, 2H), 7.93 (d, J = 5.2 Hz, 1H), 7.79 (s, 1H), 7.67 (d, J = 8.8 Hz, 2H), 7.48 (s, 1H), 7.37-7.29 (m, 1H), 7.25 (d, J = 8.8 Hz, 2H), 6.92 (t, J = 5.2 Hz, 1H), 6.88 (s, 1H), 6.83 (d, J = 8.8 Hz, 1H), 6.77 (d, J = 6.8 Hz, 2H), 4.80 (dd, J = 5.2, |

TABLE 22-continued

Compounds synthesized via Method 16 with the reductive amination
of various amines with aldehydes in Step 1.

| Ex-#[a,e] | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| | | | | | 12.8 Hz, 1H), 3.52 (s, 2H), 3.24-3.21 (m, 6H), 2.98-2.92 (m, 2H), 2.70-2.59 (m, 1H), 2.45-2.42 (m, 1H), 2.38-2.30 (m, 5H), 2.11-2.08 (m, 1H), 1.82-1.74 (m, 1H), 1.59-1.38 (m, 8H), 0.88-0.79 (m, 1H), 0.26-0.18 (m, 2H), 0.02-0.03 (m, 2H) |
| 394 | I-399 | KS | GC | 844.4 | 10.99 (s, 1H), 8.99 (s, 1H), 8.91 (s, 1H), 8.24 (s, 1H), 8.16 (d, J = 5.2 Hz, 1H), 8.02 (s, 1H), 7.92 (d, J = 8.4 Hz, 2H), 7.73 (s, 1H), 7.59-7.49 (m, 3H), 7.17 (t, J = 5.6 Hz, 1H), 7.12 (s, 1H), 7.08-6.96 (m, 3H), 6.63 (t, J = 5.6 Hz, 1H), 5.04 (dd, J = 5.6, 12.8 Hz, 1H), 3.85 (s, 2H), 3.49-3.40 (m, 4H), 3.33 (q, J = 6.4 Hz, 2H), 3.19 (t, J = 6.0 Hz, 2H), 2.93-2.81 (m, 1H), 2.71-2.65 (m, 2H), 2.57-2.51 (m, 2H), 2.09-1.97 (m, 1H), 1.84-1.71 (m, 4H), 1.12-1.01 (m, 1H), 0.49-0.42 (m, 2H), 0.25-0.21 (m, 2H) |
| 395 | I-400 | OK | KT | 902.4 | 11.34-11.04 (m, 1H), 10.96 (s, 1H), 9.04 (s, 1H), 8.92 (s, 1H), 8.61 (d, J = 4.4 Hz, 1H), 8.28 (d, J = 4.8 Hz, 1H), 8.20 (d, J = 2.8 Hz, 1H), 7.89 (d, J = 8.8 Hz, 2H), 7.73 (t, J = 6.4 Hz, 1H), 7.60-7.53 (m, 1H), 7.48 (d, J = 8.4 Hz, 2H), 7.28 (s, 1H), 7.22-7.17 (m, 1H), 7.13 (d, J = 8.8 Hz, 1H), 7.03 (d, J = 6.8 Hz, 1H), 6.61 (s, 1H), 5.10-5.00 (m, 1H), 4.31-4.22 (m, 2H), 3.78 (s, 2H), 3.66-3.51 (m, 10H), 2.88 (d, J = 4.8 Hz, 3H), 2.71-2.68 (m, 1H), 2.66-2.57 (m, 1H), 2.57-2.53 (m, 1H), 2.53-2.52 (m, 2H), 2.05-1.97 (m, 1H) |
| 396 | I-401 | HQ | KV[d] | 881.5 | 11.09 (s, 1H), 9.99 (s, 1H), 8.97 (s, 1H), 8.77 (s, 1H), 8.23-8.14 (m, 2H), 7.79 (d, J = 8.4 Hz, 2H), 7.51 (d, J = 8.4 Hz, 2H), 7.44-7.15 (m, 1H), 7.13-7.07 (m, 2H), 7.05 (d, J = 5.2 Hz, 1H), 6.95 (d, J = 6.0 Hz, 2H), 6.86 (dd, J = 2.8, 6.0 Hz, 1H), 5.36 (dd, J = 5.2, 12.6 Hz, 1H), 3.89-3.83 (m, 1H), 3.55 (s, 9H), 3.23-3.15 (m, 2H), 2.99-2.83 (m, 1H), 2.99-2.81 (m, 5H), 2.76-2.57 (m, 5H), 2.03-1.95 (m, 1H), 1.86-1.77 (m, 2H), 1.30 (d, J = 6.8 Hz, 3H), 1.12-1.04 (m, 1H), 0.49-0.42 (m, 2H), 0.25-0.23 (m, 2H) |
| 397 | I-402 | OK | KY | 903.4 | 11.13 (s, 1H), 9.97 (s, 1H), 8.93 (s, 1H), 8.58 (s, 1H), 8.28-8.20 (m, 2H), 7.72 (d, J = 8.4 Hz, 2H), 7.63-7.53 (m, 2H), 7.42 (d, J = 8.4 Hz, 2H), 7.28-7.22 (m, 2H), 7.13 (d, J = 8.8 Hz, 1H), 7.03 (d, J = 7.2 Hz, 1H), 6.60 (t, J = 5.2 Hz, 1H), 5.05 (dd, J = 5.2, 13.2 Hz, 1H), 4.29-4.20 (m, 2H), 3.76 (s, 2H), 3.65-3.62 (m, 2H), 3.60-3.50 (m, 10H), 2.92-2.86 (m, 1H), 2.75 (t, J = 7.2 Hz, 2H), 2.71-2.68 (m, 2H), 2.64-2.56 (m, 1H), 2.56-2.54 (m, 1H), 2.04-1.98 (m, 1H), 1.87-1.80 (m, 2H) |
| 398[c] | I-403 | LB | LE | 893.5 | 11.17 (s, 1H), 9.96 (s, 1H), 8.95 (s, 1H), 8.75 (s, 1H), 8.16 (d, J = 4.8 Hz, 1H), 7.75 (d, J = 8.4 Hz, 2H), |

TABLE 22-continued

Compounds synthesized via Method 16 with the reductive amination
of various amines with aldehydes in Step 1.

| Ex-#[a,e] | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| | | | | | 7.46 (d, J = 8.4 Hz, 2H), 7.42-7.13 (m, 1H), 7.12-6.84 (m, 6H), 5.40-5.30 (m, 1H), 3.54 (s, 3H), 3.50-3.44 (m, 8H), 3.23-3.15 (m, 2H), 2.98-2.94 (m, 2H), 2.89-2.82 (m, 1H), 2.65-2.55 (m, 4H), 2.04-1.95 (m, 1H), 1.86-1.79 (m, 2H), 1.12-1.04 (m, 1H), 1.03-0.83 (m, 4H), 0.53-0.40 (m, 2H), 0.26-0.18 (m, 2H) |
| 399 | I-404 | LF | GF | 837.5 | 11.07 (s, 1H), 9.96 (s, 1H), 8.96 (s, 1H), 8.77 (s, 1H), 8.25 (s, 1H), 8.16 (d, J = 5.2 Hz, 1H), 7.81 (d, J = 8.8 Hz, 2H), 7.52 (d, J = 8.8 Hz, 2H), 7.28 (t, J = 52 Hz, 1H), 7.12 (s, 1H), 7.09-7.02 (m, 2H), 6.97-6.91 (m, 2H), 6.84 (dd, J = 3.2, 5.6 Hz, 1H), 5.35 (dd, J = 5.2, 12.8 Hz, 1H), 3.82 (s, 2H), 3.54 (s, 3H), 3.47-3.45 (m, 4H), 3.21-3.17 (m, 2H), 2.95-2.90 (m, 2H), 2.88-2.83 (m, 1H), 2.75-2.68 (m, 1H), 2.66 (d, J = 7.2 Hz, 2H), 2.63-2.56 (m, 1H), 2.03-1.95 (m, 1H), 1.86-1.77 (m, 2H), 1.74-1.69 (m, 2H), 1.13-1.02 (m, 1H), 0.49-0.43 (m, 2H), 0.25-0.20 (m, 2H) |
| 400 | I-405 | LG | GF | 836.4 | 10.84 (s, 1H), 9.75 (s, 1H), 8.73 (s, 1H), 8.54 (s, 1H), 8.06 (s, 1H), 7.93 (d, J = 5.2 Hz, 1H), 7.57 (d, J = 8.4 Hz, 2H), 7.26 (d, J = 8.8 Hz, 2H), 7.18-6.89 (m, 1H), 6.89-6.87 (m, 1H), 6.86-6.79 (m, 2H), 6.79-6.72 (m, 2H), 6.61 (dd, J = 1.2, 8.0 Hz, 1H), 5.09 (dd, J = 5.2, 12.8 Hz, 1H), 3.54 (s, 2H), 3.24-3.18 (m, 8H), 2.98-2.91 (m, 2H), 2.72-2.60 (m, 1H), 2.52-2.45 (m, 1H), 2.42-2.33 (m, 5H), 1.80-1.73 (m, 1H), 1.61-1.53 (m, 2H), 1.48-1.44 (m, 2H), 0.88-0.80 (m, 1H), 0.26-0.19 (m, 2H), 0.03--0.04 (m, 2H) |
| 401 | I-406 | LH | GF | 895.5 | 11.10 (s, 1H), 10.01 (s, 1H), 8.98 (s, 1H), 8.80 (s, 1H), 8.21 (s, 1H), 8.17 (d, J = 4.8 Hz, 1H), 7.83 (d, J = 8.0 Hz, 2H), 7.52 (d, J = 8.0 Hz, 2H), 7.45-7.15 (m, 1H), 7.14-7.08 (m, 2H), 7.06-7.03 (m, 1H), 6.98-6.93 (m, 2H), 6.88-6.83 (m, 1H), 5.40-5.33 (m, 1H), 3.82 (s, 2H), 3.56 (s, 3H), 3.45-3.41 (m, 8H), 3.22-3.13 (m, 2H), 2.96-2.90 (m, 2H), 2.90-2.84 (m, 1H), 2.76-2.70 (m, 1H), 2.66-2.60 (m, 2H), 2.60-2.55 (m, 1H), 2.04-1.92 (m, 1H), 1.86-1.77 (m, 2H), 1.76-1.68 (m, 4H), 1.13-1.00 (m, 1H), 0.49-0.44 (m, 2H), 0.25-0.21 (m, 2H) |
| 402 | I-407 | LI | GF | 895.5 | 11.06 (s, 1H), 10.02 (s, 1H), 8.96 (s, 1H), 8.80 (s, 1H), 8.29 (s, 1H), 8.15 (d, J = 5.2 Hz, 1H), 7.85-7.76 (m, 2H), 7.54 (d, J = 8.4 Hz, 2H), 7.43-7.15 (m, 1H), 7.11 (s, 1H), 7.08 (t, J = 5.2 Hz, 1H), 7.05-7.02 (m, 1H), 7.02-6.95 (m, 2H), 6.85 (d, J = 7.6 Hz, 1H), 5.32 (dd, J = 5.2, 12.8 Hz, 1H), 3.89 (s, 2H), 3.42-3.32 (m, 8H), 3.31 (s, 3H), 3.18 (t, J = 6.0 Hz, 2H), 2.95-2.83 (m, 1H), 2.74-2.58 (m, 6H), |

TABLE 22-continued

Compounds synthesized via Method 16 with the reductive amination
of various amines with aldehydes in Step 1.

| Ex-#[a,e] | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| | | | | | 2.04-1.94 (m, 1H), 1.84-1.65 (m, 6H), 1.11-1.01 (m, 1H), 0.49-0.41 (m, 2H), 0.22 (q, J = 4.8 Hz, 2H) |
| 403 | I-408 | 4-[2-[2-[2-(2-aminoethoxy)-ethoxy]ethoxy]-ethylamino]-2-(2,6-dioxo-3-piperidyl)-isoindoline-1,3-dione (synthesized via Steps 1-2 of Example 128) | LS | 827.5 | 11.08 (s, 1 H), 10.09 (s, 1 H), 8.92 (s, 1 H), 8.88 (s, 2 H), 8.23 (d, J = 5.2 Hz, 1 H), 8.03 (s, 1 H), 7.63-7.55 (m, 2 H), 7.24-7.21 (m, 2 H), 7.11 (d, J = 8.8 Hz, 1 H), 7.03 (d, J = 6.8 Hz, 1 H), 6.56 (s, 1 H), 5.06-5.01 (m, 1 H), 4.30-4.13 (m, 5 H), 3.87 (s, 2 H), 3.70-3.67 (m, 3 H), 3.60-3.57 (m, 3 H), 3.54-3.52 (m, 4 H), 3.46-3.36 (m, 3 H), 3.18 (m, 2 H), 2.94-2.83 (m, 1 H), 2.63-2.53 (m, 2 H), 2.05-1.96 (m, 1 H) |
| 404 | I-409 | 4-[2-[3-(2-aminoethoxy)-propoxy]-ethylamino]-2-(2,6-dioxo-3-piperidyl)-isoindoline-1,3-dione (synthesized via Steps 1-2 of Example 208, I-213) | GC | 874.3 | 10.99 (s, 1 H), 8.99 (s, 1 H), 8.94-8.89 (m, 1H), 8.23 (s, 1H), 8.16 (d, J = 5.2 Hz, 1H), 8.03 (s, 1H), 7.90 (d, J = 8.4 Hz, 2H), 7.72 (s, 1H), 7.59-7.54 (m, 1H), 7.48 (d, J = 8.4 Hz, 2H), 7.19-7.11 (m, 3H), 7.05-6.98 (m, 2H), 6.59 (m, 1H), 5.05 (m, 1H), 3.78 (s, 2H), 3.59-3.54 (m, 11H), 3.19 (m, 2H), 2.92-2.83 (m, 1H), 2.67 (m, 2 H), 2.61-2.55 (m, 2 H), 2.06-1.98 (m, 1 H), 1.74 (t, J = 6.36 Hz, 2 H), 1.11-1.03 (m, 1H), 0.46-0.43 (m, 2H), 0.23-0.22 (m, 2H) |
| 405 | I-410 | LN | GF | 865.5 | 11.09 (s, 1H), 10.03 (s, 1H), 8.96 (s, 1H), 8.80 (s, 1H), 8.28 (s, 1H), 8.15 (d, J = 5.2 Hz, 1H), 7.85 (d, J = 8.0 Hz, 2H), 7.56 (d, J = 7.6 Hz, 2H), 7.42-7.15 (m, 1H), 7.11 (s, 1H), 7.08 (t, J = 5.2 Hz, 1H), 7.05-7.03 (m, 1H), 7.00-6.91 (m, 2H), 6.88-6.83 (m, 1H), 5.35 (dd, J = 5.2, 12.4 Hz, 1H), 3.95-3.91 (m, 2H), 3.54 (s, 3H), 3.41-3.38 (m, 2H), 3.36-3.32 (m, 2H), 3.18 (t, J = 5.6 Hz, 2H), 2.92-2.87 (m, 2H), 2.87-2.83 (m, 1H), 2.71-2.68 (m, 2H), 2.65-2.58 (m, 2H), 2.03-1.94 (m, 1H), 1.64-1.50 (m, 8H), 1.11-1.02 (m, 1H), 0.48-0.41 (m, 2H), 0.22 (q, J = 4.4 Hz, 2H) |
| 406 | I-411 | OD | GF | 865.6 | 11.08 (s, 1H), 10.01 (s, 1H), 8.97 (s, 1H), 8.80 (s, 1H), 8.27 (s, 1H), 8.16 (d, J = 5.2 Hz, 1H), 7.82 (d, J = 8.4 Hz, 2H), 7.52 (d, J = 8.0 Hz, 2H), 7.43-7.15 (m, 1H), 7.14-7.07 (m, 2H), 7.06-6.96 (m, 3H), 6.85 (d, J = 8.0 Hz, 1H), 5.41-5.25 (m, 1H), 3.76 (s, 2H), 3.78-3.69 (m, 1H), 3.83 (s, 2H), 3.35-3.33 (m, 2H), 3.31 (s, 3H), 3.21-3.15 (m, 2H), 2.91-2.82 (m, 1H), 2.75-2.68 (m, 1H), 2.64-2.58 (m, 5H), 2.02-1.95 (m, 1H), 1.66-1.55 (m, 2H), 1.54-1.47 (m, 6H), 1.13-0.97 (m, 1H), 0.48-0.41 (m, 2H), 0.25-0.19 (m, 2H) |
| 407 | I-412 | LR | LS | 825.2 | 11.10 (s, 1H), 10.87 (s, 1H), 8.89 (s, 1H), 8.24 (s, 1H), 8.21 (d, J = 5.2 Hz, 1H), 8.10 (s, 1H), 7.58-7.52 (m, 2H), 7.58-7.52 (m, 1H), 7.22-7.17 (m, 2H), 7.07-6.98 (m, 2H), 6.62 (t, J = 5.6 Hz, 1H), 5.04 (dd, J = 5.2, 12.8 Hz, 1H), 4.23 (dd, J = 6.8, 9.2 Hz, 2H), 3.92 (s, 1H), 3.95-3.90 (m, 1H), 3.79 (s, 3H), |

TABLE 22-continued

Compounds synthesized via Method 16 with the reductive amination
of various amines with aldehydes in Step 1.

| Ex-#[a,e] | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| | | | | | 3.34-3.27 (m, 10H), 2.90-2.84 (m, 1H), 2.65 (t, J = 7.2 Hz, 2H), 2.62-2.58 (m, 1H), 2.58-2.54 (m, 1H), 2.06-1.97 (m, 1H), 1.82 (t, J = 6.8 Hz, 2H), 1.80-1.72 (m, 2H), 1.68-1.60 (m,, 2H) |
| 408 | I-413 | LP | LS | 984.3 | 10.83 (s, 1H), 8.97 (s, 1H), 8.90 (s, 1H), 8.56 (s, 1H), 8.22 (s, 2H), 8.10 (s, 1H), 7.56 (s, 1H), 7.40 (s, 5H), 7.21 (s, 2H), 4.58-4.49 (m, 1H), 4.43-4.36 (m, 1H), 4.34 (s, 1H), 4.26-4.24 (m, 2H) 3.95 (s, 2H), 3.85-3.75 (m, 1H), 3.79 (s, 3H), 3.70-3.58 (m, 14H), 3.20-3.16 (m, 1H), 3.07 (s, 2H), 3.15-2.98 (m, 1H), 2.77 (s, 2H), 2.64-2.59 (m, 1H), 2.48-2.40 (m, 4H), 1.93-1.89 (m, 1H), 0.89 (s, 9H) |
| 409 | I-414 | LO | GY | 1103.2 | 11.01 (s, 1H), 9.02 (s, 1H), 8.97 (s, 1H), 8.92 (s, 1H), 8.61 (t, J = 6.0 Hz, 1H), 8.29-8.19 (m, 2H), 8.04 (s, 1H), 7.92 (d, J = 8.4 Hz, 2H), 7.78-7.63 (m, 2H), 7.50 (br d, J = 8.4 Hz, 2H), 7.46-7.35 (m, 5H), 7.26 (s, 1H) 7.17 (dd, J = 1.2, 5.2 Hz, 1H), 4.56 (d, J = 9.6 Hz, 1H), 4.49-4.34 (m, 3H), 4.32-4.16 (m, 4H), 3.96 (s, 2H), 3.82 (s, 2H), 3.56-3.44 (m, 11H), 2.70 (J = 6.0 Hz, 2H), 2.43 (s, 3H), 2.11-2.01 (m, 1H), 1.93-1.86 (m, 1H), 0.93 (s, 9H) |
| 410 | I-415 | LP | GY | 1089.2 | 11.00 (s, 1H), 9.01 (s, 1H), 8.98-8.95 (m, 1H), 8.93 (s, 1H), 8.56 (t, J = 6.0 Hz, 1H), 8.33-8.17 (m, 3H), 8.04 (s, 1H), 7.98-7.88 (m, 2H), 7.77-7.63 (m, 2H), 7.52 (d, J = 8.4 Hz, 2H), 7.43-7.34 (m, 4H), 7.26 (s, 1H), 7.17 (dd, J = 1.2, 5.2 Hz, 1H), 4.57-4.18 (m, 6H), 4.05-3.78 (m, 2H), 3.50-3.34 (m, 14H), 3.24-3.13 (m, 1H), 3.08 (s, 1H), 2.77-2.72 (m, 2H), 2.64-2.58 (m, 1H), 2.55-2.52 (m, 1H), 2.44-2.42 (m, 3H), 2.10-2.00 (m, 1H), 1.97-1.86 (m, 1H), 0.93-0.84 (m, 9H) |
| 411 | I-416 | OE | GF | 1233.7 | 9.96 (s, 1H), 8.96 (s, 1H), 8.79 (s, 1H), 8.22-8.13 (m, 2H), 7.81 (d, J = 8.8 Hz, 2H), 7.50 (d, J = 8.8 Hz, 2H), 7.44-7.42 (m, 1H), 7.32-6.90 (m, 10H), 6.83-6.74 (m, 2H), 5.12-4.63 (m, 5H), 4.07-4.01 (m, 2H), 3.87-3.81 (m, 4H), 3.74-3.71 (m, 2H), 3.58-3.49 (m, 20H), 3.29 (s, 3H), 3.20-3.17 (m, 2H), 3.06-2.90 (m, 2H), 2.75-2.65 (m, 2H), 1.90-1.49 (m, 4H), 1.03 (s, 7H), 0.94 (s, 3H), 0.51-0.41 (m, 2H), 0.24-0.20 (m, 2H) |
| 412 | I-417 | LY | GF | 1145.2 | 9.99 (s, 1H), 8.97 (s, 1H), 8.78 (s, 1H), 8.22-8.17 (m, 1H), 8.17-8.13 (m, 1H), 7.80-7.76 (m, 2H), 7.52-6.72 (m, 15H), 5.08-4.96 (m, 1H), 4.92-4.58 (m, 4H), 4.12 (s, 2H) 3.90-3.81 (m, 2H), 3.77-3.71 (m, 4H), 3.56-3.50 (m, 9H), 3.31-3.27 (m, 5H), 3.20-3.16 (m, 2H), 3.09-2.91 (m, 3H), 2.69-2.64 (m, 3H), 1.89-1.51 (m, 4H), 1.12 (s, 9H), 0.49-0.42 (m, 2H), 0.25-0.20 (m, 2H) |

TABLE 22-continued

Compounds synthesized via Method 16 with the reductive amination
of various amines with aldehydes in Step 1.

| Ex-#[a,e] | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| 413 | I-418 | LX | GF | 1189.7 | 9.75 (s, 1H), 8.73 (s, 1H), 8.55 (s, 1H), 8.13 (s, 1H), 7.99-7.91 (m, 2H), 7.56 (d, J = 8.4 Hz, 2H), 7.27-7.18 (m, 4H), 7.06 (s, 1H), 6.91-6.79 (m, 9H), 6.69 (d, J = 2.3 Hz, 1H), 6.59-6.52 (m, 2H), 4.79 (d, J = 9.4 Hz, 1H), 4.69-4.61 (m, 2H), 4.47-4.36 (m, 2H), 3.82 (s, 2H), 3.67-3.59 (m, 2H), 3.54-3.48 (m, 5H), 3.36-3.29 (m, 6H), 2.99-2.92 (m, 4H), 2.46-2.39 (m, 5H), 2.12-2.07 (m, 1H), 1.65-1.48 (m, 3H), 1.43-1.31 (m, 2H), 0.73-0.65 (m, 2H), 0.25-0.19 (m, 2H), 0.02--0.03 (m, 2H) |
| 414 | I-419 | LZ | GF | 923.5 | 11.07 (s, 1H), 9.96 (s, 1H), 8.96 (s, 1H), 8.77 (s, 1H), 8.29 (s, 1H), 8.16 (d, J = 5.2 Hz, 1H), 7.78 (d, J = 8.8 Hz, 2H), 7.47 (d, J = 8.4 Hz, 2H), 7.42-7.15 (m, 1H), 7.12 (s, 1H), 7.08 (t, J = 5.6 Hz, 1H), 7.04 (d, J = 5.2 Hz, 1H), 6.99-6.90 (m, 2H), 6.87-6.81 (m,, 1H), 5.35 (dd, J = 5.2, 12.4 Hz, 1H) 3.75 (s, 2H), 3.56 (s, 3H), 3.44-3.42 (m, 2H), 3.19 (t, J = 6.4, 2H), 3.12 (d, J = 2.0 Hz, 4H), 2.98-2.90 (m, 2H), 2.89-2.84 (m, 1H), 2.67-2.56 (m, 6H), 2.03-1.94 (m, 1H), 1.83-1.75 (m, 2H), 1.72-1.64 (m, 2H), 1.10-1.03 (m, 1H), 0.84 (s, 6H), 0.48-0.43 (m, 2H), 0.23 (q, J = 4.8 Hz, 2H) |
| 415 | I-420 | LZ | LS | 839.4 | 11.08 (s, 1H), 10.93 (s, 1H), 8.86 (s, 1H), 8.27 (s, 1H), 8.20 (d, J = 4.8 Hz, 1H), 8.10 (s, 1H), 7.53 (t, J = 6.4 Hz, 1H), 7.21-7.13 (m, 2H), 7.00-6.88 (m, 2H), 6.83-6.75 (m, 1H), 5.35 (dd, J = 5.6, 12.4 Hz, 1H), 4.26-4.19 (m, 2H), 3.90 (s, 2H), 3.76 (s, 3H), 3.51 (s, 3H), 3.46-3.42 (m, 4H), 2.98 (d, J = 7.2 Hz, 4H), 2.91-2.83 (m, 3H), 2.65-2.58 (m, 4H), 2.04-1.95 (m, 1H), 1.88-1.79 (m, 2H), 1.77-1.69 (m, 2H), 0.71 (s, 6H) |
| 416 | I-421 | MA | GF | 923.5 | 11.08 (s, 1H), 10.19 (s, 1H), 9.33-9.23 (m, 2H), 9.14 (s, 1H), 8.87 (s, 1H), 8.11 (d, J = 6.4 Hz, 1H), 7.95 (d, J = 7.6 Hz, 2H), 7.73 (d, J = 8.0 Hz, 2H), 7.57 (s, 1H), 7.48-7.19 (m, 1H), 7.27-7.17 (m, 1H), 7.02 (s, 2H), 6.85 (d, J = 8.0 Hz, 1H), 5.42-5.30 (m, 1H), 4.20 (s, 2H), 3.45-3.43 (m, 6H), 3.32 (s, 3H), 3.14 (s, 2H), 3.09 (s, 2H), 3.01-2.93 (m, 2H), 2.92-2.85 (m, 1H), 2.72-2.65 (m, 2H), 2.62-2.57 (m, 1H), 2.57-2.55 (m, 1H), 2.57-2.55 (m, 1H), 1.96-1.88 (m, 1H), 1.96-1.88 (m, 2H), 1.86-1.74 (m, 2H), 1.20-1.10 (m, 1H), 0.85 (s, 6H), 0.60-0.53 (m, 2H), 0.36-0.30 (m, 2H) |
| 417[c] | I-422 | HQ | MB | 714.3 | 11.08 (s, 1H), 10.88 (s, 1H), 8.98 (s, 2H), 8.88 (s, 1H), 8.66 (s, 1H), |

TABLE 22-continued

Compounds synthesized via Method 16 with the reductive amination
of various amines with aldehydes in Step 1.

| Ex-#[a,e] | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| | | | | | 8.06 (d, J = 8.8 Hz, 2H), 8.01 (s, 1H), 7.81 (s, 1H), 7.67 (d, J = 8.8 Hz, 2H), 6.99-6.92 (m, 2H), 6.86-6.83 (m, 1H), 5.41-5.30 (m, 1H), 4.26 (s, 2H), 3.74-3.70 (m, 2H), 3.66-3.60 (m, 2H), 3.60-3.57 (m, 2H), 3.55 (s, 3H), 3.50-3.46 (m, 2H), 3.16 (s, 2H), 2.99-2.91 (m, 2H), 2.90-2.81 (m, 1H), 2.76-2.68 (m, 1H), 2.68-2.62 (m, 1H), 2.05-1.94 (m, 1H), 1.89-1.77 (m, 2H) |
| 418 | I-423 | MG | GF | 779.1 | 11.10 (s, 1H), 10.00 (s, 1H), 8.97 (s, 1H), 8.80 (s, 1H), 8.28 (s, 1H), 8.16 (d, J = 5.2 Hz, 1H), 7.82 (d, J = 8.8 Hz, 2H), 7.52 (d, J = 8.8 Hz, 2H), 7.45-7.15 (m, 1H), 7.12 (s, 1H), 7.09 (t, J = 5.6 Hz, 1H), 7.05 (dd, J = 1.2, 5.2 Hz, 1H), 6.99-6.92 (m, 2H), 6.87 (dd, J = 2.8, 6.0 Hz, 1H), 5.36 (dd, J = 5.2, 12.8 Hz, 1H), 3.81 (s, 2H), 3.58 (s, 3H), 3.19 (t, J = 6.0 Hz, 2H), 2.99-2.94 (m, 2H), 2.90-2.85 (m, 1H), 2.73-2.68 (m, 1H), 2.66-2.63 (m, 2H), 2.62-2.58 (m, 1H), 2.04-1.96 (m, 1H), 1.85-1.76 (m, 2H), 1.12-1.03 (m, 1H), 0.50-0.42 (m, 2H), 0.25-0.21 (m, 2H) |

[a] For Method 16, when the amine is the HCl salt, TEA was added to free base the salt, followed by HOAc to adjust the pH to 3-4. KOAc could also be used in place of the TEA/HOAc combination.
[b] TFA not HCl was used for the deprotection in Step 2.
[c] No deprotection Step 2 required.
[d] Coupling partner was a ketone not aldehyde.
[e] Steps 1-2 was run anywhere from 0.5-48 hrs.

Further Examples

Example 419: N-[3-carbamoyl-1-[4-[2-[2-[2-[[2-(2,6-dioxo-3-piperidyl)-1,3-dioxo-isoindolin-4-yl]amino]ethoxy]ethoxy]ethyl]carbamoyl]phenyl]pyrazol-4-yl]-2-(2-cyclopropyl-4-pyridyl)oxazole-4-carboxamide, I-424

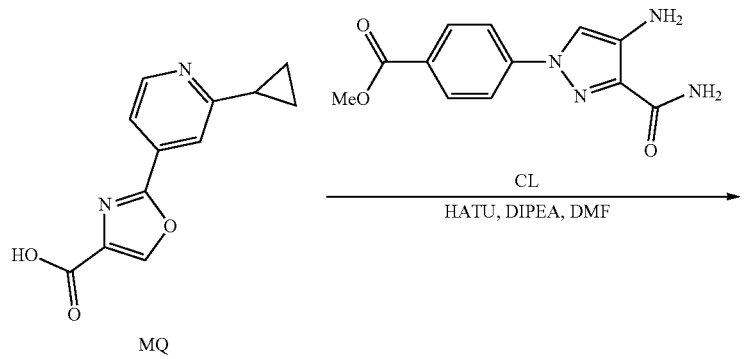

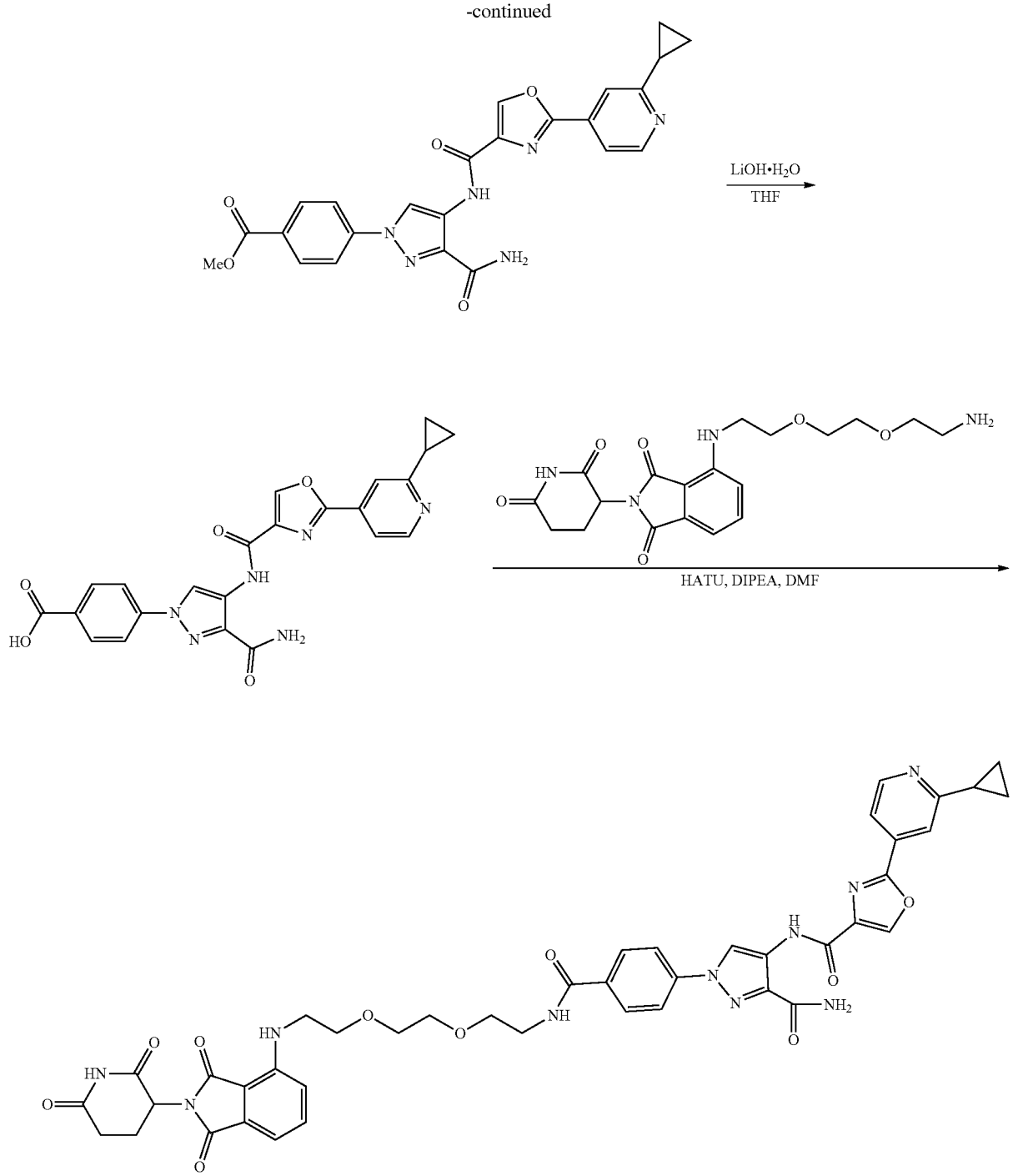

N-[3-carbamoyl-1-[4-[2-[2-[2-[[2-(2,6-dioxo-3-piperidyl)-1,3-dioxo-isoindolin-4-yl]amino]ethoxy]ethoxy]ethyl]carbamoyl]phenyl]pyrazol-4-yl]-2-(2-cyclopropyl-4-pyridyl)oxazole-4-carboxamide was synthesized via Method 10, coupling amine methyl 4-(4-amino-3-carbamoyl-pyrazol-1-yl)benzoate (Intermediate CL) and acid 2-(2-cyclopropyl-pyridyl)oxazole-4-carboxylic acid (Intermediate MQ) in Step 1, and coupling amine 4-[2-[2-(2-aminoethoxy)ethoxy]ethylamino]-2-(2,6-dioxo-3-piperidyl)isoindoline-1,3-dione (synthesized via Steps 1-2 of Example 127) in Step 3. The final product was purified by prep-HPLC (column: Phenomenex Synergi C18 150*25*10 um; mobile phase: [water (0.225% FA)-ACN]; B %: 33%-53%, 7 min) to give the title compound (29.0 mg, 14% yield) as a yellow solid. $^1$H NMR (400 MHz, DMSO-$d_6$) δ 11.14-11.04 (m, 2H), 9.10 (s, 1H), 9.03 (s, 1H), 8.66-8.61 (m, 2H), 8.15 (s, 1H), 8.11-8.06 (m, 2H), 8.04-7.98 (m, 2H), 7.88-7.81 (m, 2H), 7.69 (dd, J=1.2, 5.6 Hz, 1H), 7.58-7.52 (m, 1H), 7.11 (d, J=8.8 Hz, 1H), 7.01 (d, J=6.8 Hz, 1H), 6.60 (t, J=5.6 Hz, 1H), 5.11-4.90 (m, 1H), 3.64-3.53 (m, 8H), 3.49-3.40 (m, 5H), 2.92-2.83 (m, 1H), 2.68-2.53 (m, 1H), 2.34-2.26 (m, 2H), 2.15-1.89 (m, 2H), 1.07-0.96 (m, 4H). LC-MS (ESI$^+$) m/z 845.2 (M+H)$^+$.

Example 420: 4-[2-[4-[2-[2-[2-[2-[[2-(2,6-Dioxo-3-piperidyl)-1,3-dioxo-isoindolin-4-yl]amino]ethoxy]ethoxy]ethoxy]ethoxy]phenyl]ethynyl]-1-[[(2S,3S,4S)-3-ethyl-4-fluoro-5-oxo-pyrrolidin-2-yl]methoxy]-7-methoxy-isoquinoline-6-carboxamide, I-425
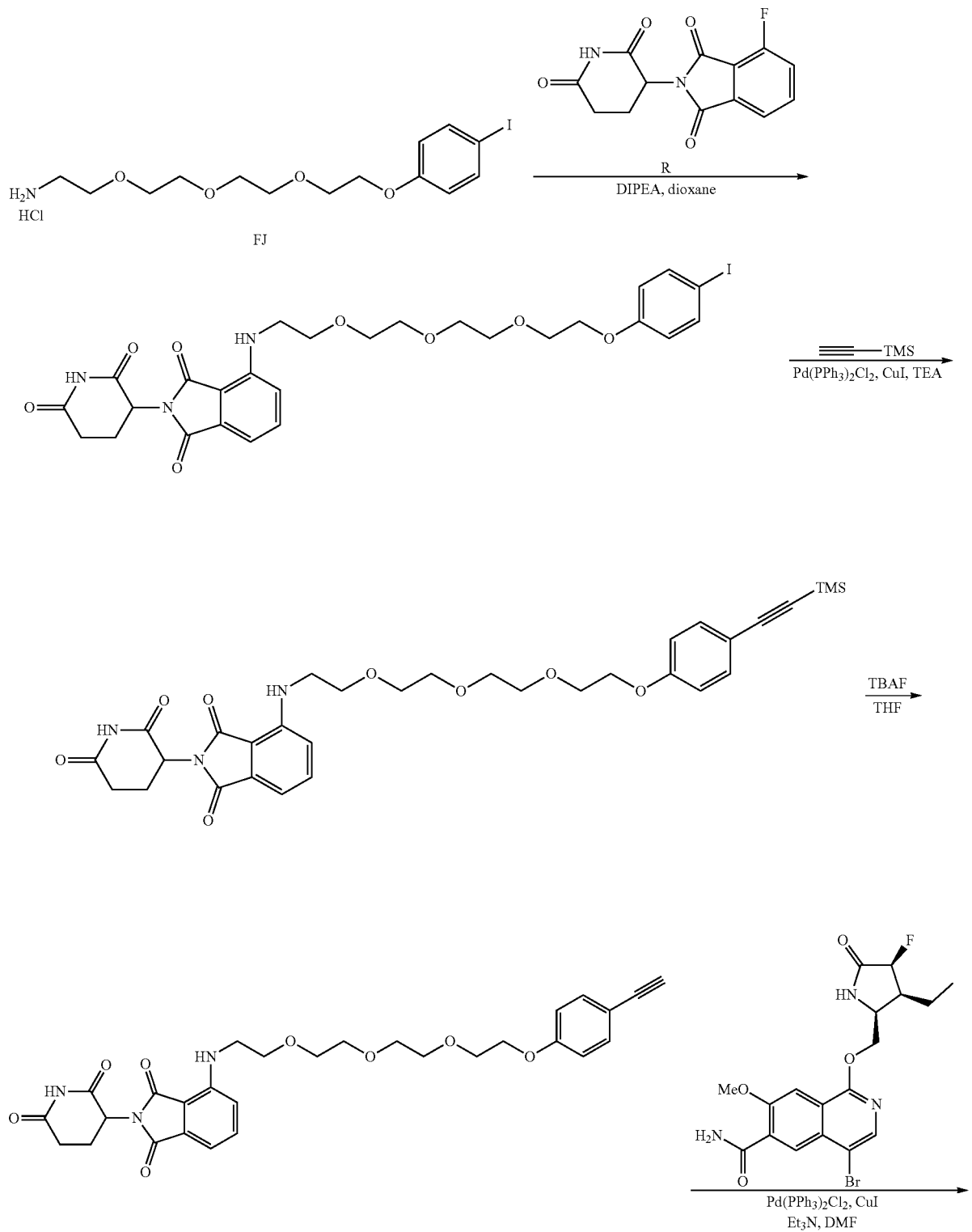

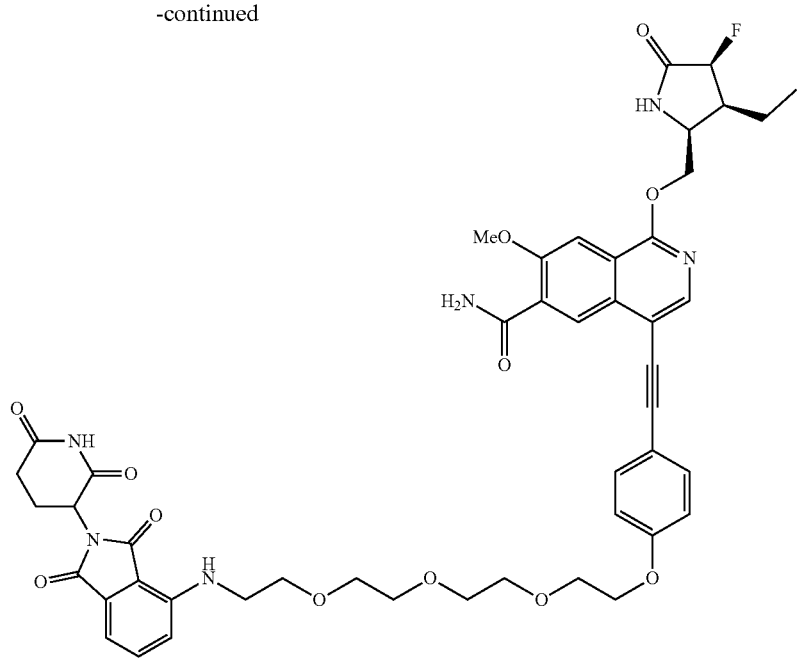

Step 1—2-(2,6-Dioxo-3-piperidyl)-4-[2-[2-[2-[2-(4-iodophenoxy)ethoxy]ethoxy]ethoxy]ethylamino]isoindoline-1,3-dione To a solution of 2-[2-[2-[2-(4-iodophenoxy)ethoxy]ethoxy]ethoxy]ethanamine (800 mg, 1.85 mmol, HCl, Intermediate FJ) and 2-(2,6-dioxo-3-piperidyl)-4-fluoro-isoindoline-1,3-dione (511 mg, 1.85 mmol, Intermediate R) in dioxane (10 mL) was added DIPEA (1.20 g, 9.27 mmol, 1.61 mL), and the reaction mixture was stirred at 115° C. for 16 hr. On completion, the mixture was concentrated in vacuo to give a residue. The residue was purified by column chromatography to give the title compound (900 mg, 75% yield) as yellow solid. LC-MS (ESI⁺) m/z 652.3 (M+H)⁺.

Step 2—2-(2,6-Dioxo-3-piperidyl)-4-[2-[2-[2-[2-[4-(2-trimethylsilylethynyl)phenoxy]ethoxy]ethoxy]ethoxy]ethyl amino]isoindoline-1,3-dione To a solution of 2-(2,6-dioxo-3-piperidyl)-4-[2-[2-[2-[2-(4-iodophenoxy)ethoxy]ethoxy]ethoxy]ethylamino]isoindoline-1,3-dione (800 mg, 1.23 mmol), Pd(PPh₃)₂Cl₂ (25.8 mg, 36.8 umol) and CuI (7.02 mg, 36.8 umol) in TEA (10 mL) was added ethynyl(trimethyl)silane (241 mg, 2.46 mmol, 340 Ul, CAS #1066-54-2), and the reaction mixture was stirred at 80° C. for 12 hr. On completion, the mixture was filtered and the filtrate was concentrated in vacuo to give a residue. The residue was purified by column chromatography to give the title compound (800 mg, 93% yield) as yellow oil. LC-MS (ESI⁺) m/z 622.2 (M+H)⁺.

Step 3—2-(2,6-Dioxo-3-piperidyl)-4-[2-[2-[2-[2-(4-ethynylphenoxy)ethoxy]ethoxy]ethoxy]ethyl amino]isoindoline-1,3-dione To a solution of 2-(2,6-dioxo-3-piperidyl)-4-[2-[2-[2-[2-[4-(2-trimethylsilylethynyl)phenoxy]ethoxy]ethoxy]ethoxy]ethyl amino]isoindoline-1,3-dione (700 mg, 1.13 mmol) in THF (10 mL) was added TBAF (883 mg, 3.38 mmol), and the reaction mixture was stirred at 20° C. for 2 hours. On completion, the reaction mixture was concentrated in vacuo to give a residue. The residue was purified by column chromatography to give the title compound (500 mg, 81% yield) as a yellow solid. LC-MS (ESI⁺) m/z 550.3 (M+1)⁺.

Step 4—4-[2-[4-[2-[2-[2-[2-[[2-(2,6-Dioxo-3-piperidyl)-1,3-dioxo-isoindolin-4-yl]amino]ethoxy]ethoxy]ethoxy]phenyl]ethynyl]-1-[[(2S,3S,4S)-3-ethyl-4-fluoro-5-oxo-pyrrolidin-2-yl]methoxy]-7-methoxy-isoquinoline-6-carboxamide To a solution of 4-bromo-1-[[(2S,3S,4S)-3-ethyl-4-fluoro-5-oxo-pyrrolidin-2-yl]methoxy]-7-methoxy-isoquinoline-6-carboxamide (20.0 mg, 45.4 umol, synthesized via Steps 1-2 of Example 126), CuI (4.33 mg, 22.7 umol), Pd(PPh₃)₂Cl₂ (15.9 mg, 22.7 umol) in DMF (2 mL) was added 2-(2,6-dioxo-3-piperidyl)-4-[2-[2-[2-[2-(4-ethynylphenoxy)ethoxy]ethoxy]ethoxy]ethylamino]-isoindoline-1,3-dione (50.0 mg, 90.9 umol) and TEA (82.8 mg, 818 umol, 113 uL). The reaction mixture was degassed with N₂ for 5 minutes, and then heated at 120° C. for 3 hours under microwave. On completion, the reaction mixture was filtered and the filtrate was concentrated in vacuo to give a residue. The residue was dissolved in DCM (20 mL) and thiourea (resin) (50 mg) was added. The mixture was stirred at 20° C. for 2 hours. Then the reaction mixture was filtered and the filtrate was concentrated in vacuo to give a residue. The residue was purified by prep-HPLC (column: Phenomenex Synergi C18 150*25*10 um; mobile phase: [water (0.225% FA)-ACN]; B %: 35%-65%, 10 min) to give the title compound (4.19 mg, 9.85% yield) as yellow solid. ¹H NMR (400 MHz, DMSO-d₆) δ 11.10 (s, 1H), 8.89 (s, 1H), 8.18 (s, 1H), 7.95 (s, 1H), 7.79 (s, 2H), 7.61-7.40 (m, 4H), 7.12 (d, J=8.4 Hz, 1H), 7.01 (d, J=8.0 Hz, 3H), 6.61-6.54 (m, 1H), 5.04 (dd, J=4.8, 12.4 Hz, 1H), 4.99-4.82 (m, 1H), 4.60-4.52 (m, 1H), 4.30 (dd, J=5.6, 10.8 Hz, 1H), 4.16-4.06 (m, 3H), 3.98 (s, 3H), 3.75-3.68 (m, 3H), 3.60-3.55 (m, 12H), 2.93-2.75 (m, 1H), 2.63-2.60 (m, 1H), 2.59-2.57 (m, 1H), 2.08-1.94 (m, 1H), 1.67-1.50 (m, 2H), 1.01 (t, J=7.2 Hz, 3H); LC-MS (ESI+) m/z 909.5 (M+H)+.

Example 421: 2-[2-(Cyclopropylmethylamino)-4-pyridyl]-N-[1-[2-[2-[2-[2-[[2-(2,6-dioxo-3-piperidyl)-1,3-dioxo-isoindolin-4-yl]amino]ethoxy]ethoxy]ethyl]isoindolin-5-yl]-3-(trifluoromethyl)pyrazol-4-yl]oxazole-4-carboxamide, I-426

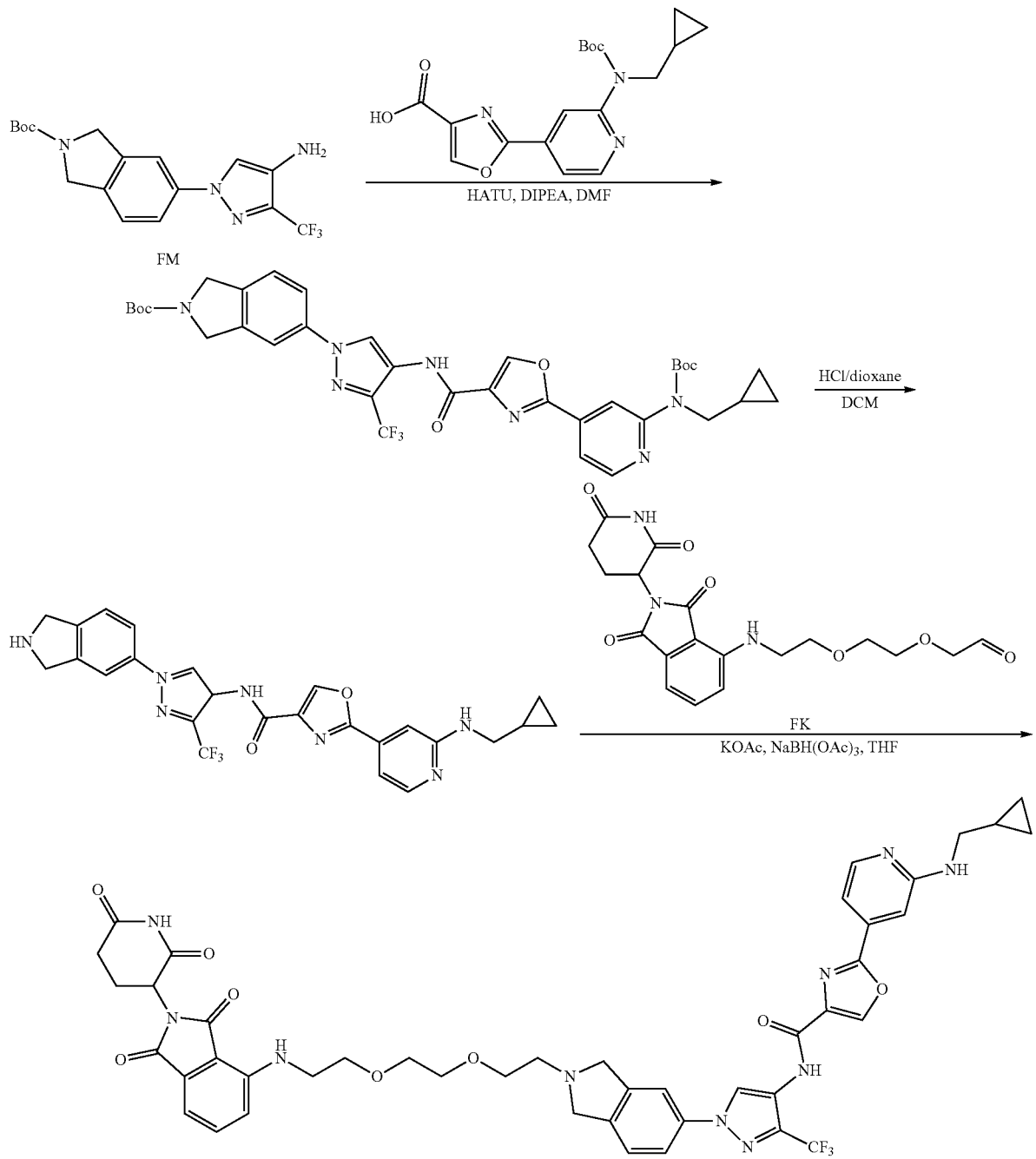

To a solution of 2-[2-(cyclopropylmethylamino)-4-pyridyl]-N-[1-isoindolin-5-yl-3-(trifluoromethyl) pyrazol-4-yl]oxazole-4-carboxamide (190 mg, 348 umol, HCl, synthe-sized via Method 12 coupling 5-[4-amino-3-(trifluoromethyl)pyrazol-1-yl]isoindoline-2-carboxylate (Intermediate FM) and 2-[2-[tert-butoxycarbonyl(cyclopropylmethyl)amino]-4-pyridyl]oxazole-4-carboxylic acid (from Steps 1-4 of Intermediate DF) in Step 1), 2-[2-[2-[[2-(2,6-dioxo-3-piperidyl)-1,3-dioxo-isoindolin-4-yl]amino]ethoxy]ethoxy]acetaldehyde (116 mg, 290 umol, Intermediate FK) in THF (30.0 mL) was added KOAc (56.9 mg, 580 umol) and NaBH(OAc)3 (122 mg, 580 umol). The reaction mixture was stirred at 25° C. for 16 hours. On completion, the mixture was diluted with H2O (1 mL) and then concentrated in vacuo. The mixture was purified by prep-HPLC (column: Phenomenex Synergi C18 150*25*10 um; mobile phase: [water (0.225% FA)-ACN]; B %: 10%-40%, 10 min) to give the title compound (16.1 mg, 5.9% yield) as yellow solid. $^1$H NMR (400 MHz, DMSO-$d_6$) δ 11.1 (s, 1H), 9.94 (s, 1H), 8.97 (s, 1H), 8.83 (s, 1H), 8.15 (d, J=5.2 Hz, 1H), 7.72 (s, 1H), 7.68 (d, J=8.4 Hz, 1H), 7.57 (t, J=7.8 Hz, 1H), 7.37 (d, J=8.4 Hz, 1H), 7.17-7.08 (m, 3H), 7.06-7.00 (m, 2H), 6.69-6.53 (m, 1H), 5.08-5.00 (m, 1H), 4.00-3.85 (m, 4H), 3.68-3.55 (m, 6H), 3.50-3.47 (m, 4H), 3.20-3.15 (m, 2H), 2.95-2.86 (m, 1H), 2.86-2.80 (m, 2H), 2.61-2.55 (m, 1H), 2.54-2.53 (m, 1H), 2.05-1.92 (m, 1H), 1.08-1.00 (m, 1H), 0.49-0.43 (m, 2H), 0.25-0.20 (m, 2H); LC-MS (ESI$^+$) m/z 897.4 (M+H)$^+$.
Example 422: 2-(2-Amino-4-pyridyl)-N-[3-carbamoyl-1-[4-[2-[2-[2-[[2-(2,6-dioxo-3-piperidyl)-1,3-dioxo-isoindolin-4-yl]amino]ethoxy]ethoxy]ethyl]carbamoyl]phenyl]pyrazol-4-yl]oxazole-4-carboxamide, I-427
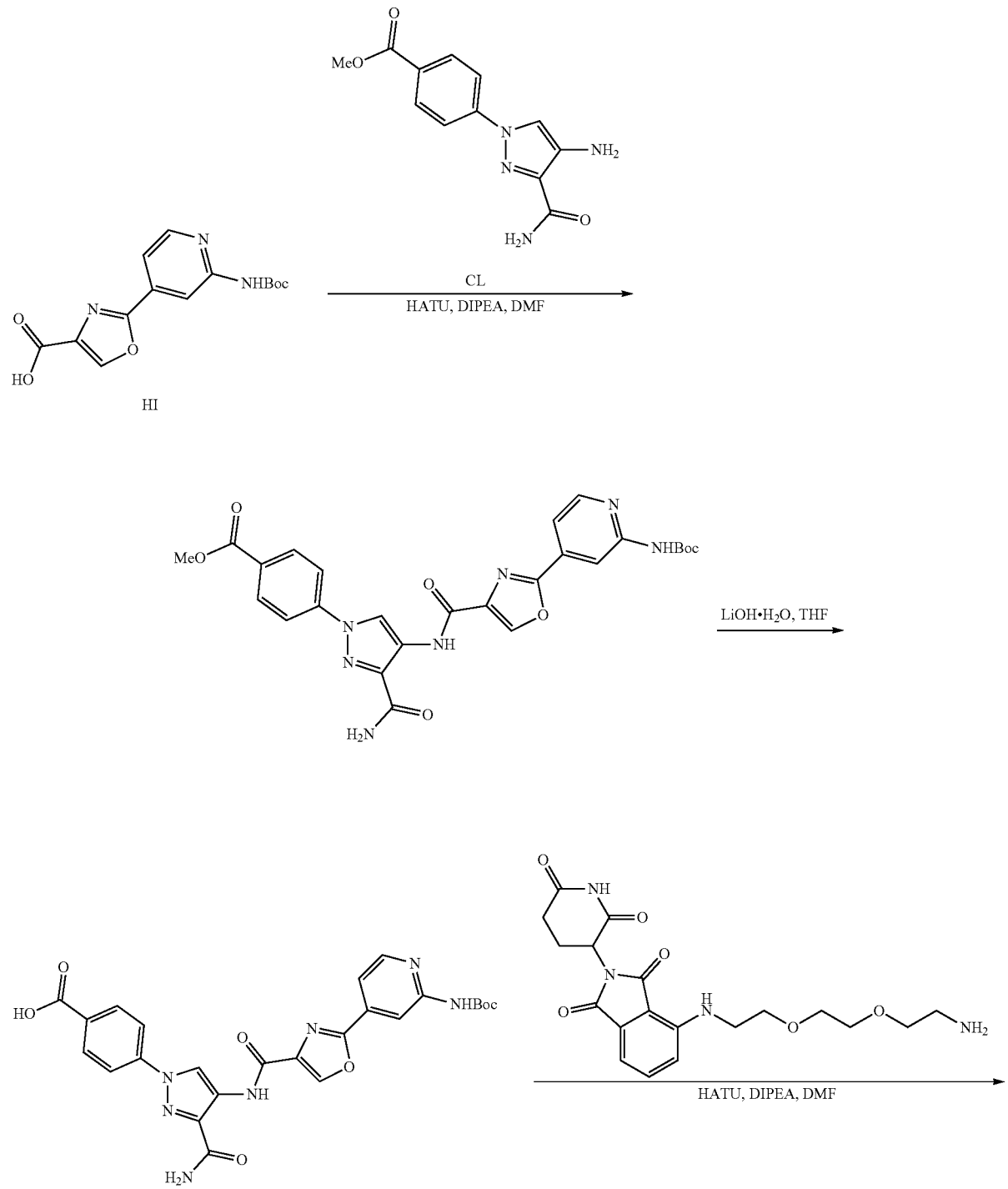

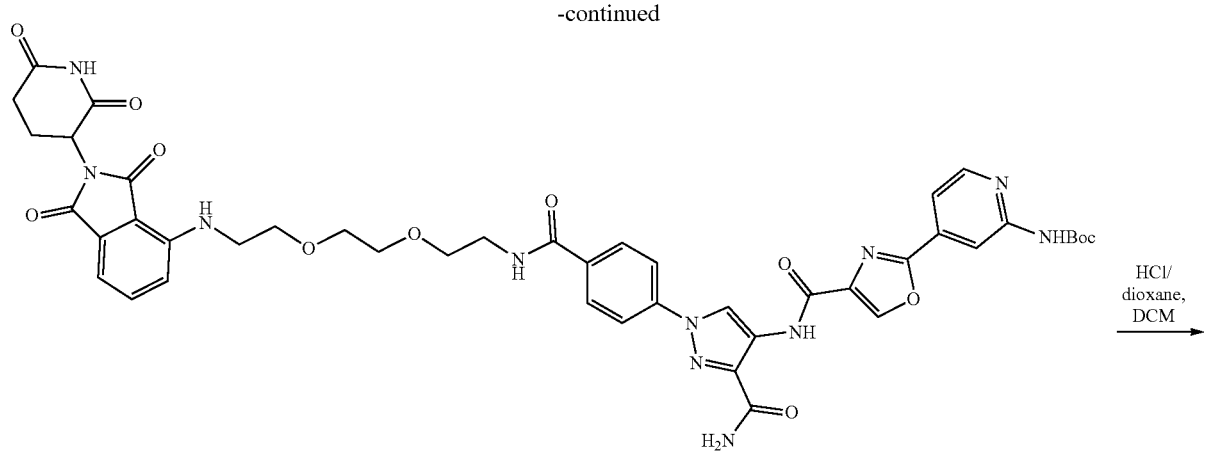

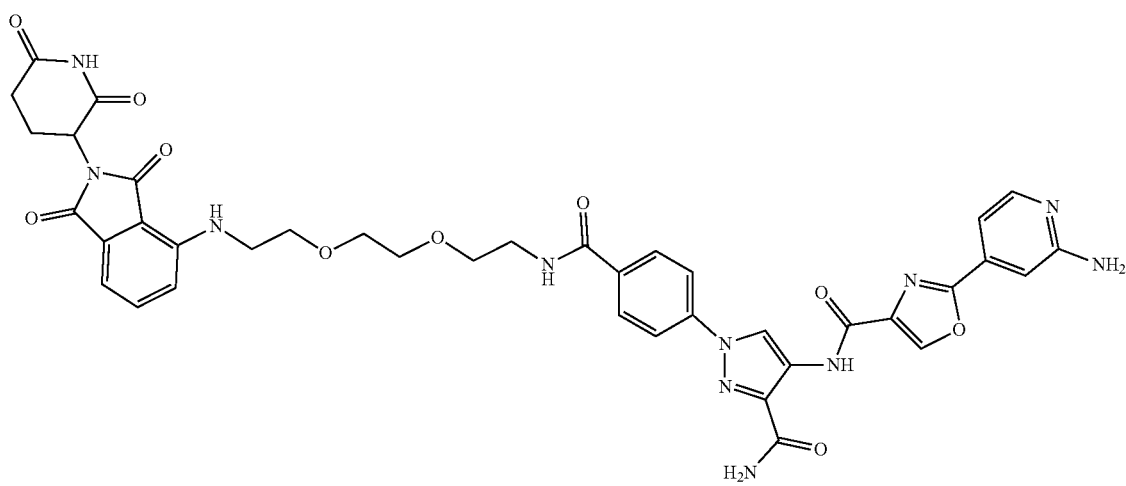 [SMILES: NC(=O)c1nn(-c2ccc(C(=O)NCCOCCOCCNc3cccc4c3C(=O)N(C3CCC(=O)NC3=O)C4=O)cc2)cc1NC(=O)c1coc(-c2ccnc(N)c2)n1]

To a solution of tert-butyl N-[4-[4-[[3-carbamoyl-1-[4-[2-[2-[2-[[2-(2,6-dioxo-3-piperidyl)-1,3-dioxo-isoindolin-4-yl]amino]ethoxy]ethoxy]ethylcarbamoyl]phenyl]pyrazol-4-yl]carbamoyl]oxazol-2-yl]-2-pyridyl]carbamate (50.0 mg, 54.4 umol, synthesized via Method 10, coupling acid Intermediate HI and amine Intermediate CL in Step 1, and coupling amine 4-[2-[2-(2-aminoethoxy)ethoxy]ethyl amino]-2-(2,6-dioxo-3-piperidyl)isoindoline-1,3-dione synthesized via Steps 1-2 of Example 127 in Step 3) in DCM (5 mL) was added HCl/dioxane (4 M, 13.6 uL). The mixture was stirred at 15° C. for 30 minutes. On completion, the mixture was concentrated in vacuo. The residue was purified by prep-HPLC (column: Luna C18 150*25 5 u; mobile phase: [water (0.225% FA)-ACN]; B %: 29%-49%, 7.8 min) to give the title compound (22.0 mg, 44% yield) as a yellow solid. $^1$H NMR (400 MHz, DMSO-d$_6$) δ 11.11 (s, 1H), 11.01 (s, 1H), 9.04 (s, 1H), 9.02 (s, 1H), 8.63 (t, J=5.2 Hz, 1H), 8.17-8.14 (m, 1H), 8.17-8.14 (m, 1H), 8.13 (d, J=5.6 Hz, 1H), 8.11-8.06 (m, 2H), 8.05-8.00 (m, 2H), 7.80 (s, 1H), 7.59-7.54 (m, 1H), 7.59-7.54 (m, 1H), 7.12 (d, J=8.8 Hz, 1H), 7.07 (s, 1H), 7.05 (s, 1H), 7.03-7.01 (m, 1H), 7.03-7.01 (m, 1H), 7.02 (d, J=7.2 Hz, 1H), 6.60 (t, J=5.6 Hz, 1H), 6.42 (s, 2H), 5.06 (dd, J=5.2, 12.8 Hz, 1H), 3.65-3.61 (m, 2H), 3.61-3.55 (m, 6H), 3.48-3.43 (m, 2H), 3.43 (s, 2H), 2.92-2.85 (m, 1H), 2.61 (s, 1H), 2.56 (s, 1H), 2.06-2.00 (m, 1H); LC-MS (ESI$^+$) m/z 820.5 (M+H)$^+$.

Example 423: N-[1-[4-[2-[2-[2-[[2-(2,6-dioxo-3-piperidyl)-1,3-dioxo-isoindolin-4-yl]amino]ethoxy]ethoxy]ethyl]carbamoyl]phenyl]-3-[3-(2-hydroxy-ethyl)-2-oxo-imidazolidin-1-yl]pyrazol-4-yl]-2-[2-(2,2,2-trifluoroethylamino)-4-pyridyl]oxazole-4-carboxamide, I-428
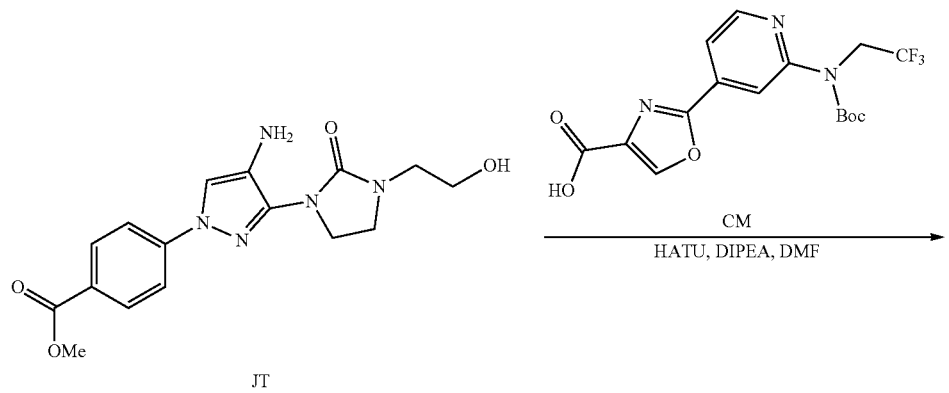
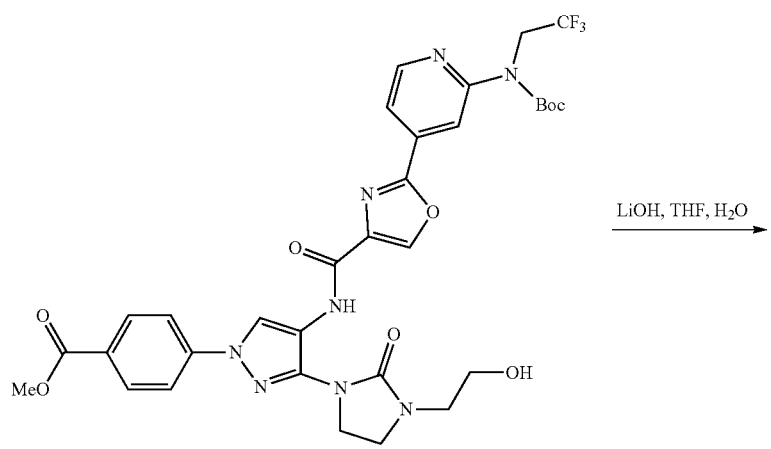
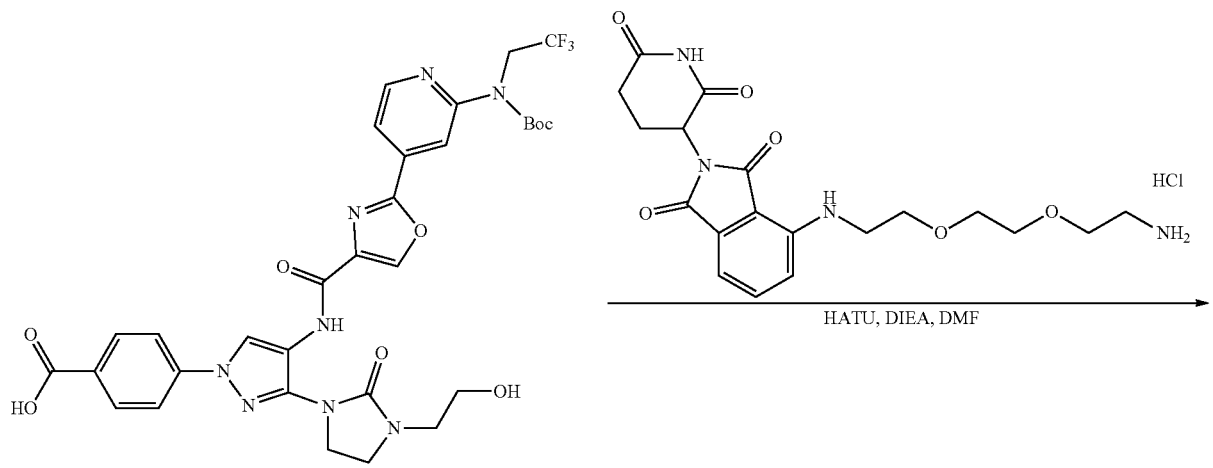

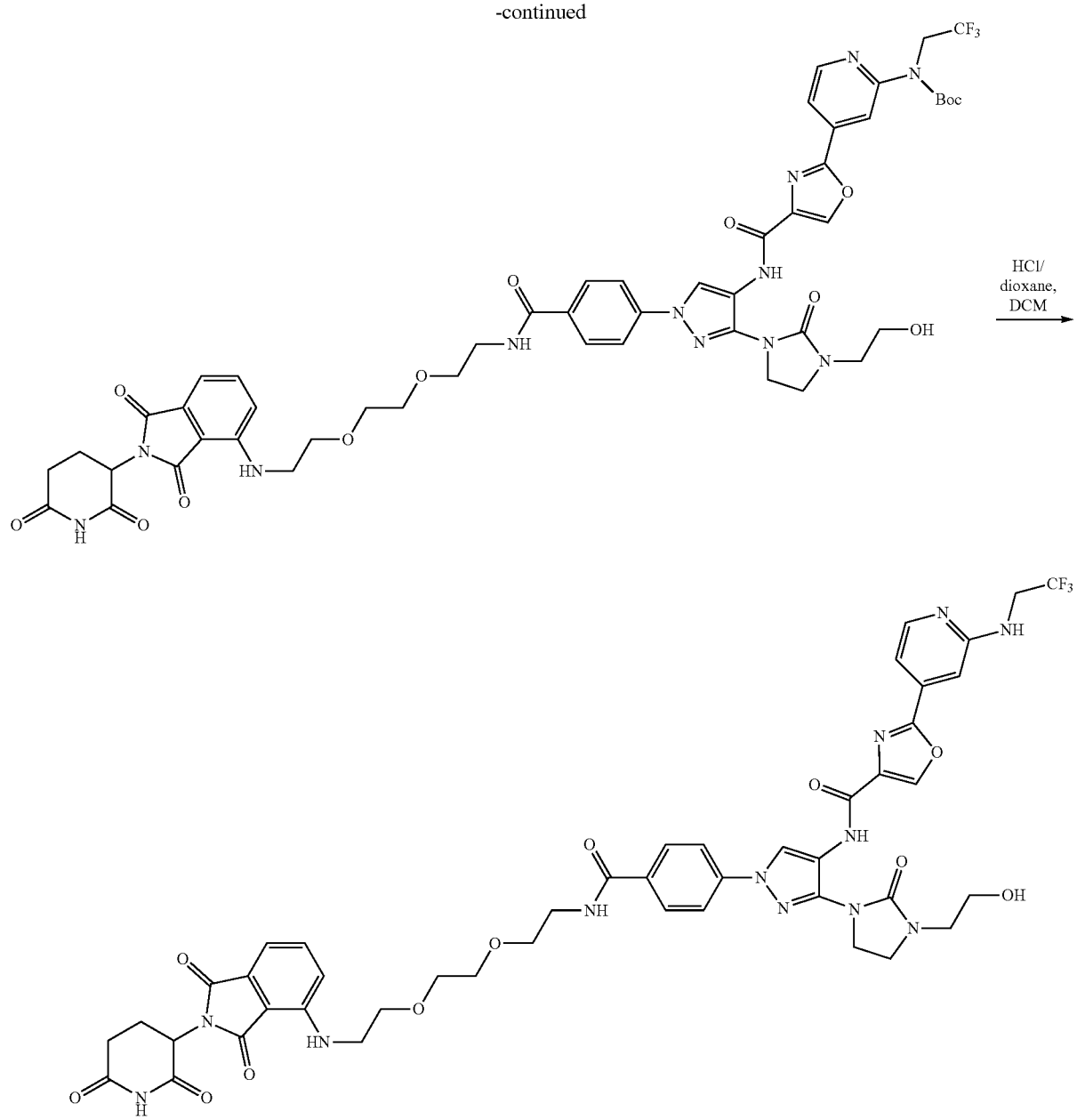

Tert-butyl N-[4-[4-[[1-[4-[2-[2-[2-[[2-(2,6-dioxo-3-piperidyl)-1,3-dioxo-isoindolin-4-yl]amino]ethoxy]ethoxy]ethyl]carbamoyl]phenyl]-3-[3-(2-hydroxyethyl)-2-oxo-imidazolidin-1-yl]pyrazol-4-yl]carbamoyl]oxazol-2-yl]-2-pyridyl]-N-(2,2,2-trifluoroethyl)carbamate was synthesized via Method 10 with methyl 4-[4-amino-3-[3-(2-hydroxyethyl)-2-oxo-imidazolidin-1-yl]pyrazol-1-yl]benzoate (Intermediate JT) as the amine and 2-[2-[tert-butoxycarbonyl (2,2,2-trifluoroethyl)amino]-4-pyridyl]oxazole-4-carboxylic acid (Intermediate CM) as the acid in Step 1, and 4-[2-[2-(2-aminoethoxy)ethyl]ethylamino]-2-(2,6-dioxo-3-piperidyl)isoindoline-1,3-dione (50.3 mg, 114 umol, HCl, synthesized via Steps 1-2 of Example 127) as the amine in Step 3. In the final step, to a solution of tert-butyl N-[4-[4-[[1-[4-[2-[2-[2-[[2-(2,6-dioxo-3-piperidyl)-1,3-dioxo-isoindolin-4-yl]amino]ethoxy]ethoxy]ethyl]carbamoyl]phenyl]-3-[3-(2-hydroxyethyl)-2-oxo-imidazolidin-1-yl]pyrazol-4-yl]carbamoyl]oxazol-2-yl]-2-pyridyl]-N-(2,2,2-trifluoroethyl) carbamate (100 mg, 91.9 umol) in DCM (10 mL) was added HCl/dioxane (4 M, 2 mL). The mixture was stirred at 20° C. for 3 hours. On completion, the reaction mixture was concentrated in vacuo. The residue was purified by Pre-HPLC (column: Phenomenex Synergi C18 150*30 mm*4 um; mobile phase: [water (0.225% FA)-ACN]) to give the title compound (30 mg, 33% yield) as yellow solid. $^1$H NMR (400 MHz, DMSO-$d_6$) δ 11.65 (s, 1H), 11.09 (s, 1H), 8.97-8.93 (m, 2H), 8.54 (s, 1H), 8.25-8.24 (d, J=5.6 Hz, 1H), 7.98 (d, J=8.8 Hz, 2H), 7.88 (d, J=8.8 Hz, 2H), 7.60-7.50 (m, 2H), 7.23 (d, J=8.4 Hz, 2H), 7.12 (d, J=8.4 Hz, 1H), 7.01 (d, J=7.2 Hz, 1H), 6.59 (s, 1H), 5.05 (dd, J=5.2, 13.2 Hz, 1H), 4.95 (s, 1H), 4.27-4.24 (m, 2H), 4.06-3.96 (m, 2H), 3.64-3.54 (m, 10H), 3.44-3.40 (m, 6H), 2.95-2.85 (m, 1H), 2.60-2.54 (m, 2H), 2.04-2.01 (m, 1H); LC-MS (ESI$^+$) m/z 987.8 (M+H)$^+$.

Example 424: N-[3-(3,3-dimethyl-2-oxo-pyrrolidin-1-yl)-1-[4-[2-[2-[2-[[2-(2,6-dioxo-3-piperidyl)-1,3-dioxo-isoindolin-4-yl]amino]ethoxy]ethoxy]ethyl]carbamoyl]phenyl]pyrazol-4-yl-2-[2-(2,2,2-trifluoroethylamino)-4-pyridyl]oxazole-4-carboxamide, I-429
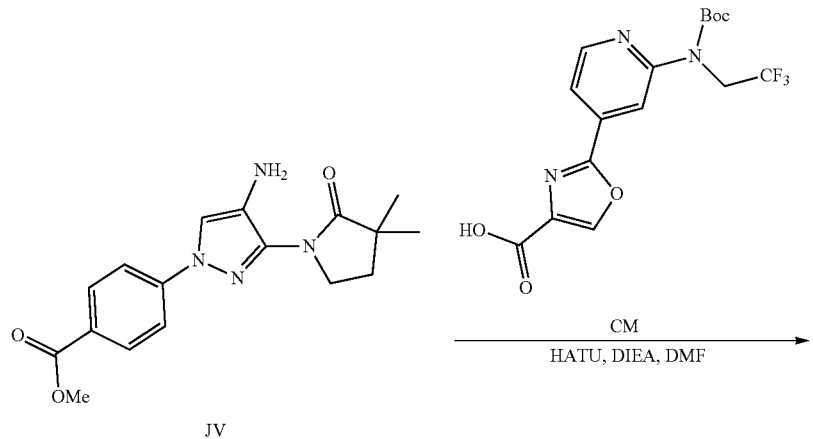
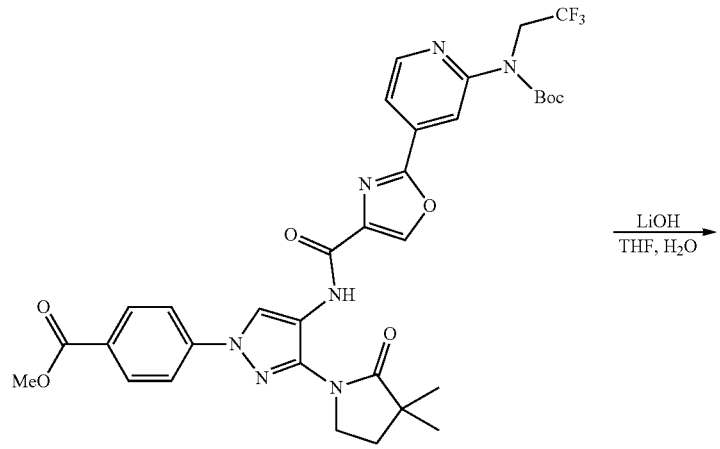
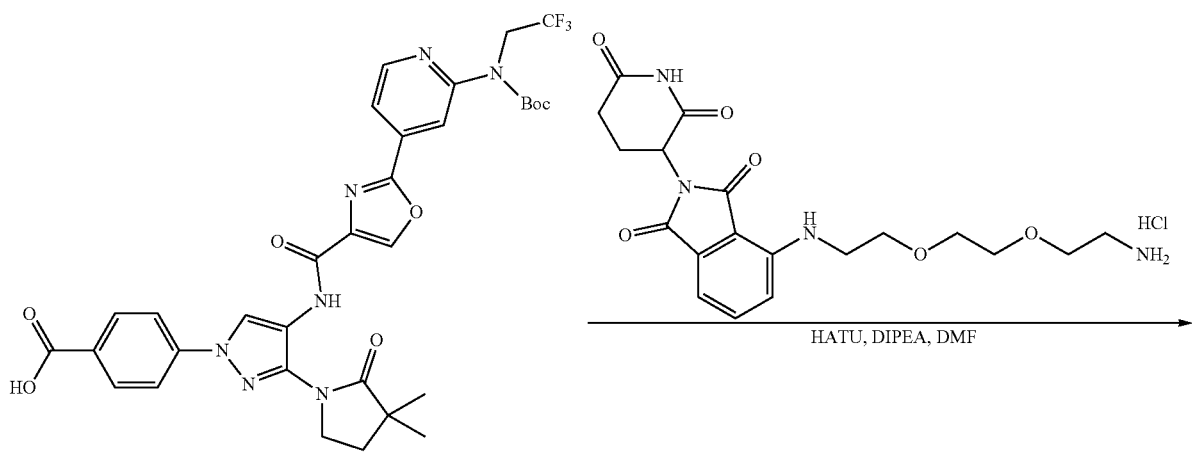

2513 2514

-continued

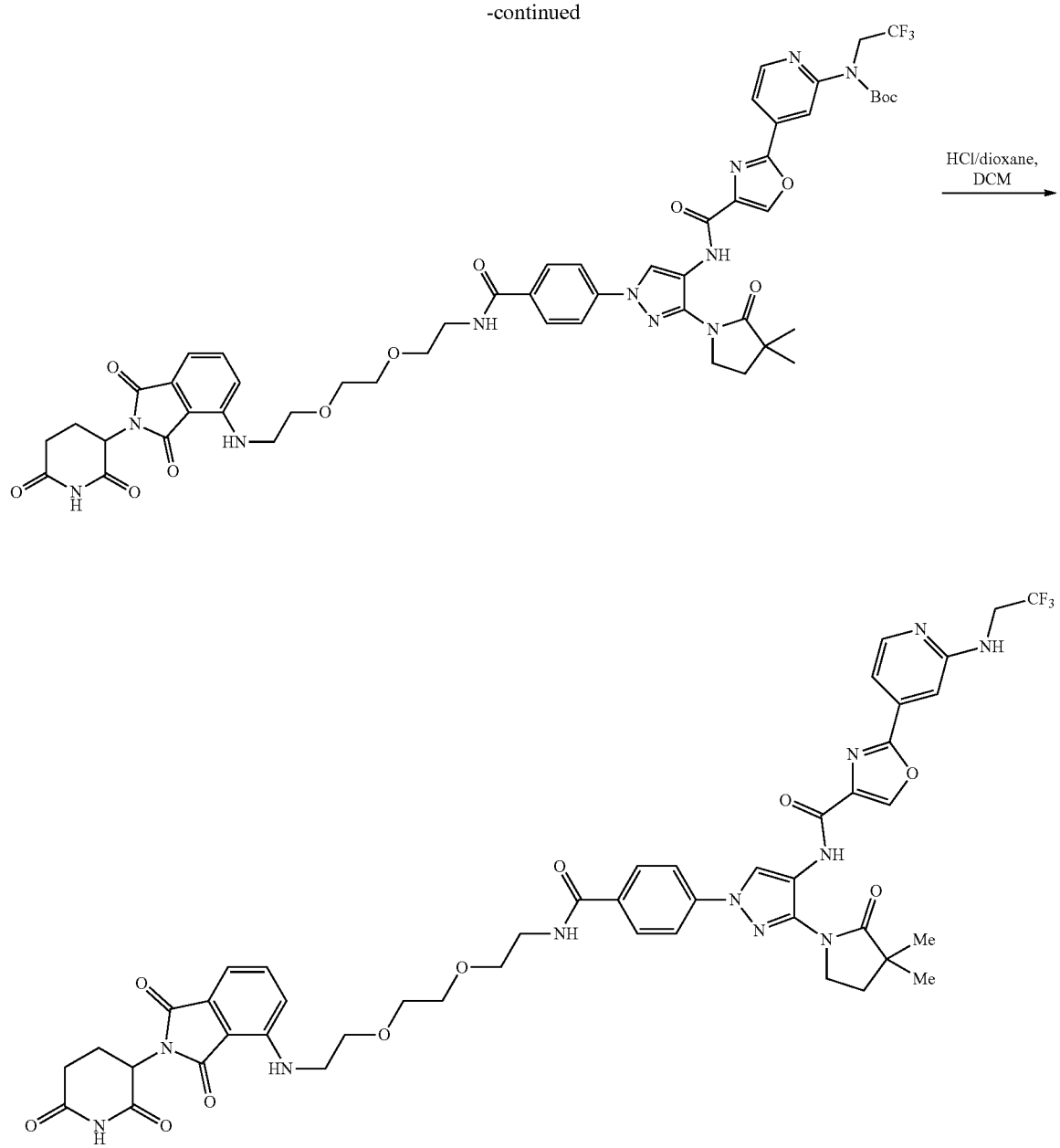

HCl/dioxane, DCM

Tert-butyl N-[4-[4-[[3-(3,3-dimethyl-2-oxo-pyrrolidin-1-yl)-1-[4-[2-[2-[2-[[2-(2,6-dioxo-3-piperidyl)-1,3-dioxo-isoindolin-4-yl]amino]ethoxy]ethoxy]ethyl]carbamoyl]phenyl]pyrazol-4-yl]carbamoyl]oxazol-2-yl]-2-pyridyl]-N-(2,2,2-trifluoroethyl)carbamate was synthesized via Method 10, with methyl 4-[4-amino-3-(3,3-dimethyl-2-oxo-pyrrolidin-1-yl)pyrazol-1-yl]benzoate (Intermediate JV) as the amine and 2-[2-[tert-butoxycarbonyl(2,2,2-trifluoroethyl)amino]-4-pyridyl]oxazole-4-carboxylic acid (Intermediate CM) as the acid in Step 1, and 4-[2-[2-(2-aminoethoxy)ethoxy]ethylamino]-2-(2,6-dioxo-3-piperidyl)isoindoline-1,3-dione (synthesized via Steps 1-2 of Example 127) as the amine in Step 3. In the final step, to a solution of tert-butyl N-[4-[4-[[3-(3,3-dimethyl-2-oxo-pyrrolidin-1-yl)-1-[4-[2-[2-[2-[[2-(2,6-dioxo-3-piperidyl)-1,3-dioxo-isoindolin-4-yl]amino]ethoxy]ethoxy]ethyl]carbamoyl]phenyl]pyrazol-4-yl]carbamoyl]oxazol-2-yl]-2-pyridyl]-N-(2,2,2-trifluoroethyl)carbamate (42 mg, 39.2 umol) in DCM (2 mL) was added HCl/dioxane (4 M, 196 uL). The mixture was stirred at 20° C. for 3 hours. On completion, the reaction mixture was concentrated in vacuo. The residue was purified by prep-HPLC (column: Phenomenex Synergi C18 150*25*10 um; mobile phase: [water (0.05% HCl)-ACN]) to give the title compound (11.6 mg, 29% yield) as yellow solid. $^1$H NMR (400 MHz, DMSO-$d_6$) δ 11.14 (s, 1H), 11.08 (s, 1H), 8.99 (s, 1H), 8.96 (s, 1H), 8.55 (s, 1H), 8.26 (d, J=5.2 Hz, 1H), 7.98 (d, J=8.4 Hz, 2H), 7.88 (d, J=8.4 Hz, 2H), 7.78 (s, 1H), 7.55 (t, J=7.6 Hz, 1H), 7.26 (s, 1H), 7.22 (d, J=5.2 Hz, 1H), 7.11 (d, J=8.8 Hz, 1H), 7.01 (d, J=7.2 Hz, 1H), 6.59 (s, 1H), 5.05 (dd, J=5.2, 13.2 Hz, 1H), 4.32-4.23 (m, 2H), 3.98 (t, J=6.8 Hz, 2H), 3.64-3.54 (m, 6H), 3.51-3.47 (m, 4H), 2.94-2.81 (m, 1H), 2.62-2.53 (m, 4H), 2.11 (t, J=6.8 Hz, 2H), 2.02 (d, J=11.2 Hz, 1H), 1.27 (s, 6H); LC-MS (ESI$^+$) m/z 970.5 (M+H)$^+$.

Example 427: N-[3-(difluoromethyl)-1-methyl-pyrazol-4-yl]-2-[2-[2-[2-[2-[2-[[2-(2,6-dioxo-3-piperidyl)-1,3-dioxo-isoindolin-4-yl]amino]ethoxy]ethoxy]ethoxy]ethylamino]-3-pyridyl]oxazole-4-carboxamide, I-432

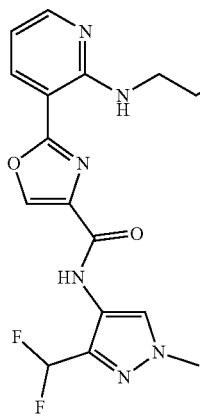

LW

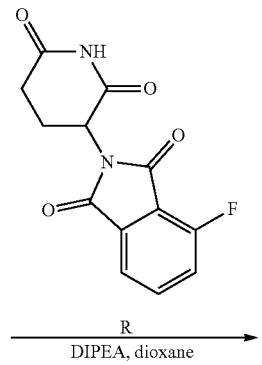

completion, the mixture was concentrated in vacuo. The residue was purified by prep-HPLC (column: Phenomenex luna C18 150*25 10 u; mobile phase: [water (0.225% FA)-ACN]; B %: 22%-52%, 10 min) to give the title compound (60 mg, 26% yield) as a yellow solid. $^1$H NMR (400 MHz, DMSO-d$_6$) δ 11.10 (s, 1H), 9.98 (s, 1H), 8.86 (s,

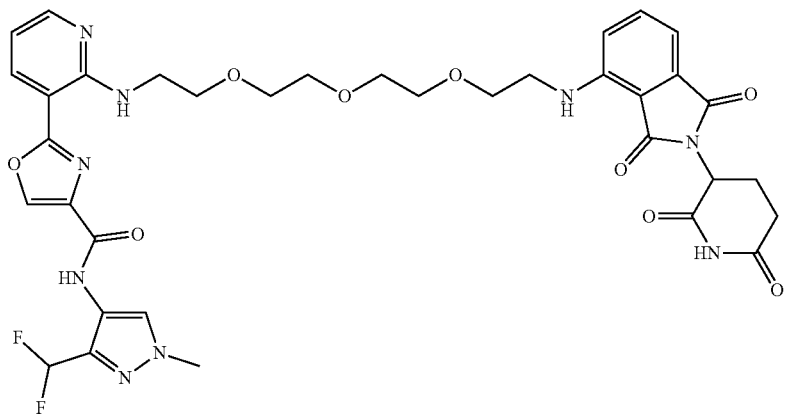

To a solution of 2-[2-[2-[2-[2-(2-aminoethoxy)ethoxy]ethoxy]ethylamino]-3-pyridyl]-N-[3-(difluoromethyl)-1-methyl-pyrazol-4-yl]oxazole-4-carboxamide (160 mg, 293 umol, HCl, Intermediate LW) in dioxane (20 mL) was added DIPEA (379 mg, 2.93 mmol) and 2-(2,6-dioxo-3-piperidyl)-4-fluoro-isoindoline-1,3-dione (121 mg, 440 umol, Intermediate R). The mixture was stirred at 115° C. for 48 hours. On 1H), 8.40-8.32 (m, 1H), 8.26-8.22 (m, 1H), 8.18-8.12 (m, 2H), 7.60-7.49 (m, 1H), 7.25-6.98 (m, 3H), 6.75-6.68 (m, 1H), 6.60-6.52 (m, 1H), 5.08-4.92 (m, 1H), 3.90 (s, 3H), 3.82-3.69 (m, 2H), 3.68-3.58 (m, 2H), 3.57-3.35 (m, 12H), 2.94-2.78 (m, 1H), 2.60-2.52 (m, 2H), 2.08-1.94 (M, 1H); LC-MS (ESI$^+$) m/z 766.3 (M+H)$^+$.

Example 429: N-[3-carbamoyl-1-[6-[2-[2-[[2-(2,6-dioxo-3-piperidyl)-1,3-dioxo-isoindolin-4-yl]amino]ethoxy]ethoxy]hexa-2,4-diynyl]pyrazol-4-yl]-2-[2-(cyclopropylmethylamino)-4-pyridyl]oxazole-4-carboxamide, I-434
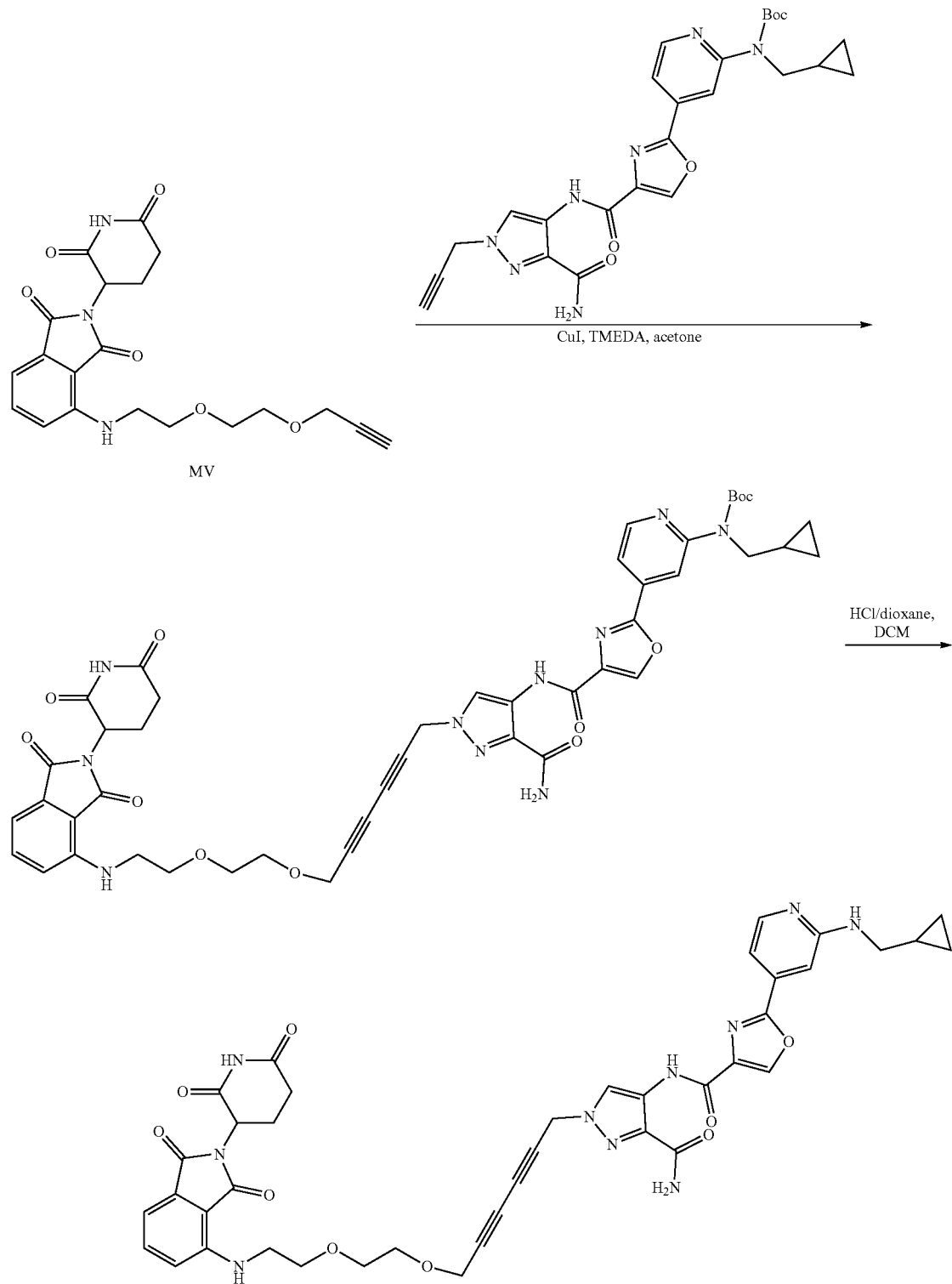

Step 1—Tert-butyl N-[4-[4-[[3-carbamoyl-1-[6-[2-[2-[[2-(2,6-dioxo-3-piperidyl)-1,3-dioxo-isoindolin-4-yl]amino]ethoxy]ethoxy]hexa-2,4-diynyl]pyrazol-4-yl]carbamoyl]oxazol-2-yl]-2-pyridyl]-N-(cyclopropylmethyl)carbamate To a solution of CuI (6.33 mg, 33.2 umol), TMEDA (1.38 mg, 11.87 umol) in acetone (2 mL) was added 2-(2,6-dioxo-3-piperidyl)-4-[2-(2-prop-2-ynoxyethoxy)ethylamino]isoindoline-1,3-dione (118 mg, 297 umol, Intermediate MV) and tert-butyl N-[4-[4-[(3-carbamoyl-1-prop-2-ynyl-pyrazol-4-yl)carbamoyl]oxazol-2-yl]-2-pyridyl]-N-(cyclopropylmethyl)carbamate (15.0 mg, 29.7 umol, synthesized via Step 1 of of Example 299, 1-304). The reaction mixture was stirred at rt for 48 hrs under an oxygen atmosphere. On completion, the mixture was concentrated in vacuo. The residue was purified by reverse phase (0.1% FA) to give title compound (20.0 mg, 74% yield) as a yellow solid. LC-MS (ESI$^+$) m/z 903.1 (M+H)$^+$.

Step 2—N-[3-carbamoyl-1-[6-[2-[2-[[2-(2,6-dioxo-3-piperidyl)-1,3-dioxo-isoindolin-4-yl]amino]ethoxy]ethoxy]hexa-2,4-diynyl]pyrazol-4-yl]-2-[2-(cyclopropylmethylamino)-4-pyridyl]oxazole-4-carboxamide To a mixture of tert-butyl N-[4-[4-[[3-carbamoyl-1-[6-[2-[2-[[2-(2,6-dioxo-3-piperidyl)-1,3-dioxo-isoindolin-4-yl] amino]ethoxy]ethoxy]hexa-2,4-diynyl]pyrazol-4-yl]carbamoyl]oxazol-2-yl]-2-pyridyl]-N-(cyclopropylmethyl) carbamate (20.0 mg, 22.1 umol) in DCM (2 mL) was added HCl/dioxane (4 M, 5.54 uL) and the reaction mixture was stirred at rt for 0.5 hr. On completion, the mixture was concentrated in vacuo. The residue was purified by prep-HPLC (column: Phenomenex Synergi C18 150*25*10 um; mobile phase: [water (0.225% FA)-ACN]; B %: 15%-45%, 10 min) to give the title compound (2.00 mg, 14% yield, FA) as a yellow solid. $^1$H NMR (400 MHz, DMSO-d$_6$) δ 11.09 (s, 1H), 10.97 (s, 1H), 8.95 (s, 1H), 8.49-8.44 (m, 2H), 8.15 (d, J=5.6 Hz, 1H), 7.84 (s, 1H), 7.60-7.54 (m, 2H), 7.16-7.09 (m, 3H), 7.05-6.97 (m, 2H), 6.60 (t, J=5.6 Hz, 1H), 5.35 (s, 2H), 5.05 (dd, J=5.6, 13.2 Hz, 1H), 4.30 (s, 2H), 3.62-3.58 (m, 3H), 3.49-3.43 (m, 2H), 3.18 (t, J=6.0 Hz, 2H), 2.94-2.81 (m, 1H), 2.69-2.65 (m, 2H), 2.34-2.31 (m, 2H), 2.08-1.98 (m, 2H), 1.06 (s, 1H), 0.48-0.42 (m, 2H), 0.22 (d, J=4.8 Hz, 2H); LC-MS (ESI$^+$) m/z 803.3 (M+H)$^+$.

Example 430: N-[3-carbamoyl-1-[6-[2-[2-[[2-(2,6-dioxo-3-piperidyl)-1,3-dioxo-isoindolin-4-yl]amino]ethoxy]ethoxy]hexyl]pyrazol-4-yl]-2-[2-(cyclopropylmethylamino)-4-pyridyl]oxazole-4-carboxamide, I-435

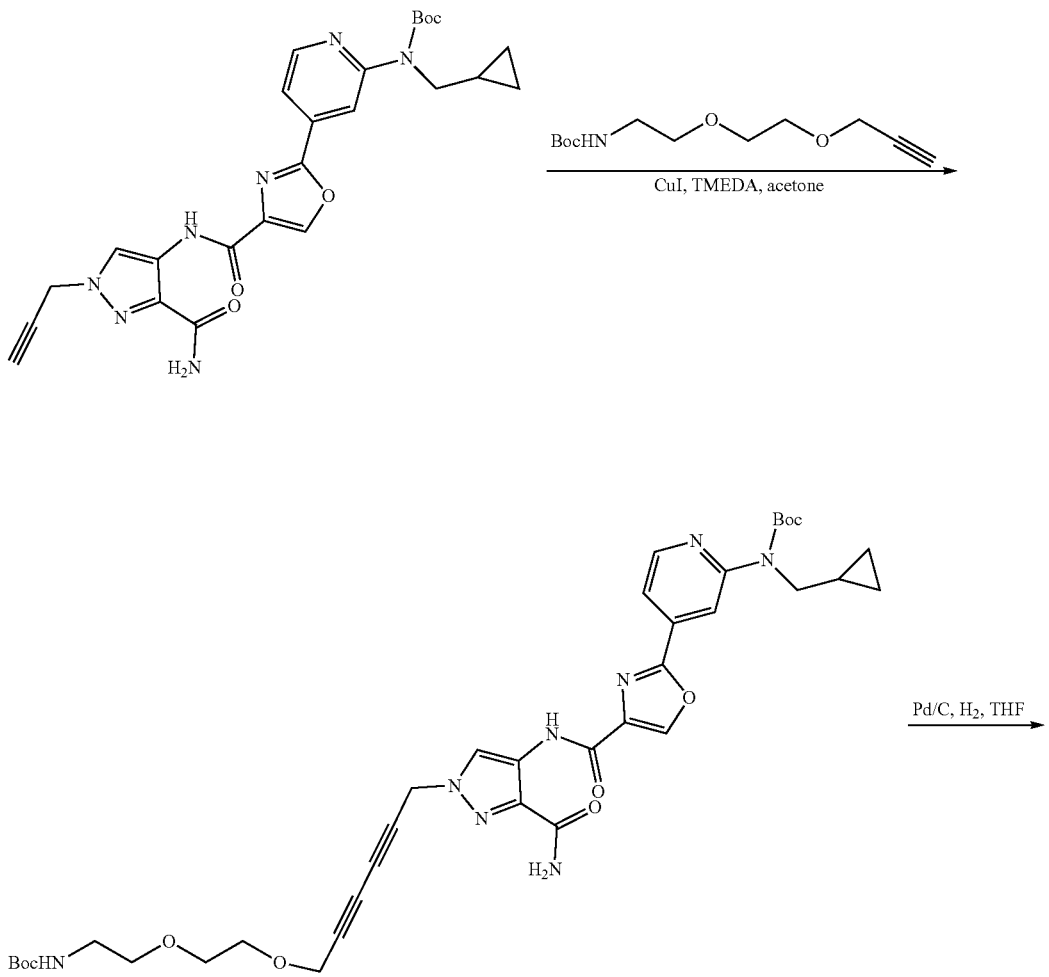

-continued
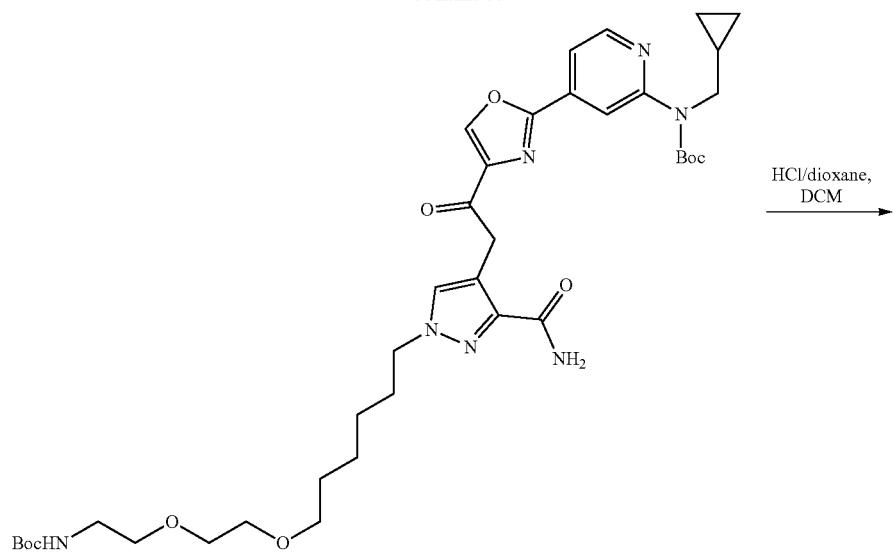
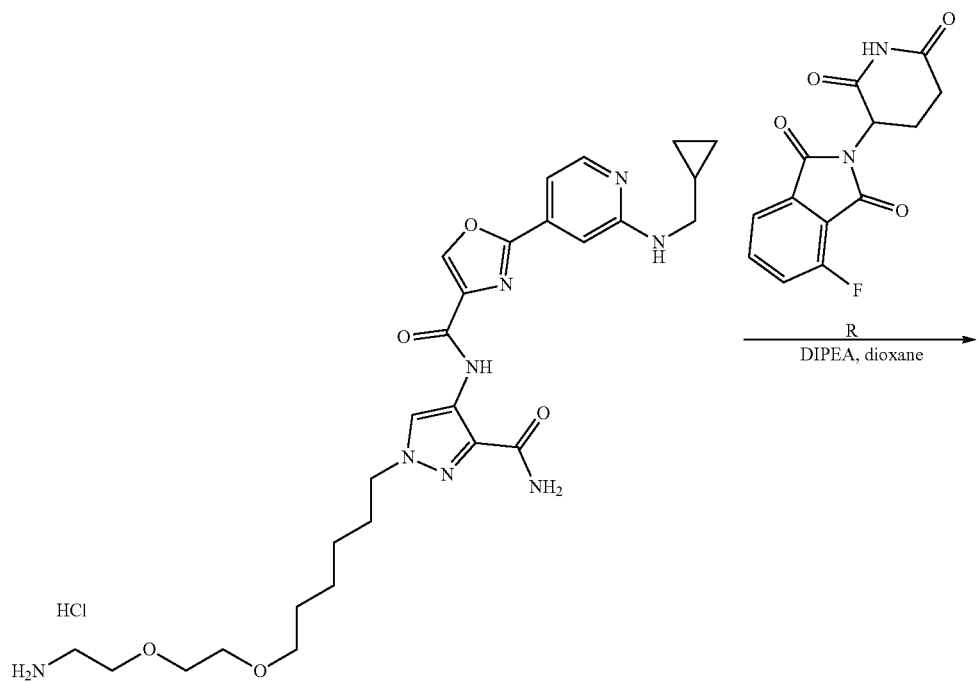

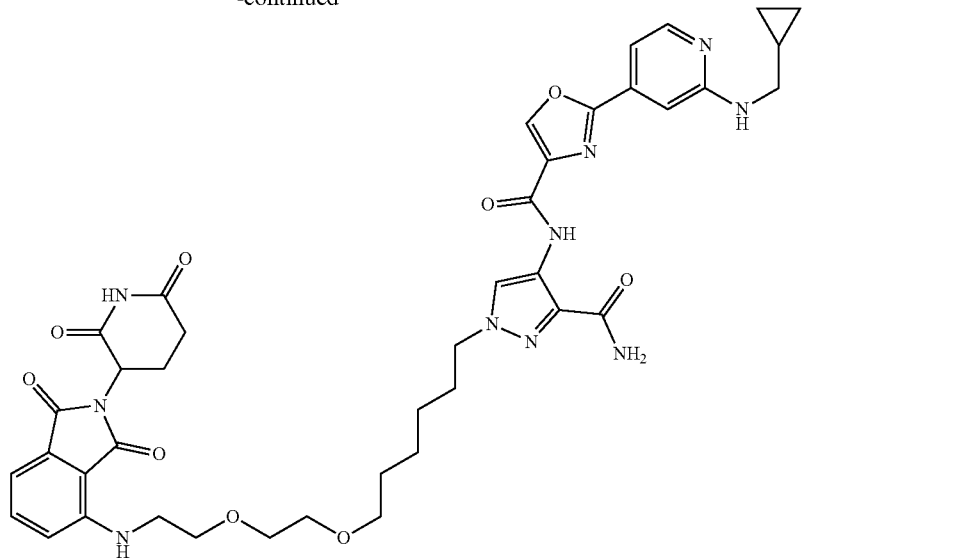

Step 1—Tert-butyl N-[4-[4-[[1-[6-[2-[2-(tert-butoxycarbonylamino)ethoxy]ethoxy]hexa-2,4-diynyl]-3-carbamoyl-pyrazol-4-yl]carbamoyl]oxazol-2-yl]-2-pyridyl]-N-(cyclopropylmethyl)carbamate To a solution of CuI (84.4 mg, 443 umol), TMEDA (18.4 mg, 158 umol) in acetone (5 mL) was added tert-butyl N-[4-[4-[(3-carbamoyl-1-prop-2-ynyl-pyrazol-4-yl)carbamoyl]oxazol-2-yl]-2-pyridyl]-N-(cyclopropylmethyl)carbamate (200 mg, 396 umol, synthesized via Step 1 of Example 299, I-304) and tert-butyl N-[2-(2-prop-2-ynoxyethoxy)ethyl]carbamate (962 mg, 3.96 mmol, synthesized via Step 1 of Intermediate CQ). The reaction mixture was stirred for 12 hours under an oxygen atmosphere. On completion, the mixture was concentrated in vacuo to give the title compound (1.80 g, 97% yield, HCl) as a brown solid. LC-MS (ESI$^+$) m/z 747.2 (M+H)$^+$.

Step 2—Tert-butyl N-[4-[4-[[1-[6-[2-[2-(tert-butoxycarbonylamino)ethoxy]ethoxy]hexyl]-3-carbamoyl-pyrazol-4-yl]carbamoyl]oxazol-2-yl]-2-pyridyl]-N-(cyclopropylmethyl)carbamate To a mixture of tert-butyl N-[4-[4-[[1-[6-[2-[2-(tert-butoxycarbonylamino)ethoxy]ethoxy]hexa-2,4-diynyl]-3-carbamoyl-pyrazol-4-yl]carbamoyl]oxazol-2-yl]-2-pyridyl]-N-(cyclopropylmethyl)carbamate (160 mg, 214 umol) in THF (10 mL) was added Pd/C (428.49 umol) and the suspension was degassed under vacuum and purged with H$_2$ gas 3 times. The mixture was stirred at rt for 1 hr under H$_2$ (15 Psi). On completion, the mixture was concentrated in vacuo to give the title compound (160 mg, 99% yield) as a brown solid. $^1$H NMR (400 MHz, DMSO-d$_6$) δ 11.01 (s, 1H), 9.02 (s, 1H), 8.60 (d, J=5.2 Hz, 1H), 8.38 (s, 1H), 8.25 (s, 1H), 7.73-7.64 (m, 2H), 7.49 (s, 1H), 6.87 (s, 1H), 5.31 (s, 1H), 4.57 (t, J=5.6 Hz, 1H), 4.18 (t, J=6.8 Hz, 2H), 3.86 (d, J=6.4 Hz, 2H), 2.18 (s, 1H), 1.82 (d, J=6.8 Hz, 3H), 1.46 (s, 19H), 0.91-0.82 (m, 2H), 0.41 (d, J=7.6 Hz, 2H), 0.24 (d, J=4.0 Hz, 2H), −0.06 (s, 4H).

Step 3—N-[1-[6-[2-(2-aminoethoxy)ethoxy]hexyl]-3-carbamoyl-pyrazol-4-yl]-2-[2-(cyclopropyl methyl amino)-4-pyridyl]oxazole-4-carboxamide To a mixture of tert-butyl N-[4-[4-[[1-[6-[2-[2-(tert-butoxycarbonylamino)ethoxy]ethoxy]hexyl]-3-carbamoyl-pyrazol-4-yl]carbamoyl]oxazol-2-yl]-2-pyridyl]-N-(cyclopropylmethyl)carbamate (100 mg, 132 umol) in DCM (2 mL) was added HCl/dioxane (4 M, 6.7 mL). The reaction mixture was stirred at rt for 0.5 hr. On completion, the mixture was concentrated in vacuo to give the title compound (75.0 mg, 95% yield, HCl) as brown oil. LC-MS (ESI$^+$) m/z 555.2 (M+H)$^+$.

Step 4—N-[3-carbamoyl-1-[6-[2-[2-[[2-(2,6-dioxo-3-piperidyl)-1,3-dioxo-isoindolin-4-yl]amino]ethoxy]ethoxy]hexyl]pyrazol-4-yl]-2-[2-(cyclopropylmethylamino)-4-pyridyl]oxazole-4-carboxamide To a mixture of N-[1-[6-[2-(2-aminoethoxy)ethoxy]hexyl]-3-carbamoyl-pyrazol-4-yl]-2-[2-(cyclo propylmethylamino)-4-pyridyl]oxazole-4-carboxamide (45.0 mg, 76.1 umol, HCl), 2-(2,6-dioxo-3-piperidyl)-4-fluoro-isoindoline-1,3-dione (21.0 mg, 76.1 umol, Intermediate R) in DMSO (2 mL) was added DIEA (98.4 mg, 761 umol). The mixture was stirred at 130° C. for 0.5 hr. On completion, the mixture was concentrated in vacuo. The residue was purified by prep-HPLC (column: Phenomenex Synergi C18 150*25*10 um; mobile phase: [water (0.225% FA)-ACN]; B %: 23%-43%, 7 min and column: Phenomenex Synergi C18 150*25*10 um; mobile phase: [water (0.05% HCl)-ACN]; B %: 25%-45%, 9 min) to give the title compound (8.50 mg, 12% yield) as a yellow solid. $^1$H NMR (400 MHz, DMSO-d$_6$) δ 11.14-11.09 (m, 1H), 11.00 (s, 1H), 9.08 (s, 1H), 8.38 (s, 1H), 8.10 (d, J=6.4 Hz, 1H), 7.76 (s, 1H), 7.61-7.48 (m, 3H), 7.24-7.11 (m, 2H), 7.03 (d, J=7.2 Hz, 1H), 6.60 (s, 1H), 5.10-5.00 (m, 1H), 4.17 (t, J=7.2 Hz, 2H), 3.65-3.44 (m, 12H), 3.28 (d, J=6.8 Hz, 4H), 2.95-2.82 (m, 1H), 2.71-2.65 (m, 1H), 2.37-2.31 (m, 1H), 2.08-1.98 (m, 1H), 1.86-1.69 (m, 2H), 1.52-1.39 (m, 2H), 1.35-1.08 (m, 5H), 0.56 (d, J=6.8 Hz, 2H), 0.39-0.25 (m, 2H); LC-MS (ESI$^+$) m/z 811.1 (M+H)$^+$.

Example 431: 3-[3-Methyl-2-oxo-5-[3-[3-[4-[4-[(5-tetrahydropyran-4-ylpyrrolo[2,1-f][1,2,4]triazin-4-yl)amino]cyclohexyl]piperazin-1-yl]propoxy]propyl]benzimidazol-1-yl]piperidine-2,6-dione (I-436)
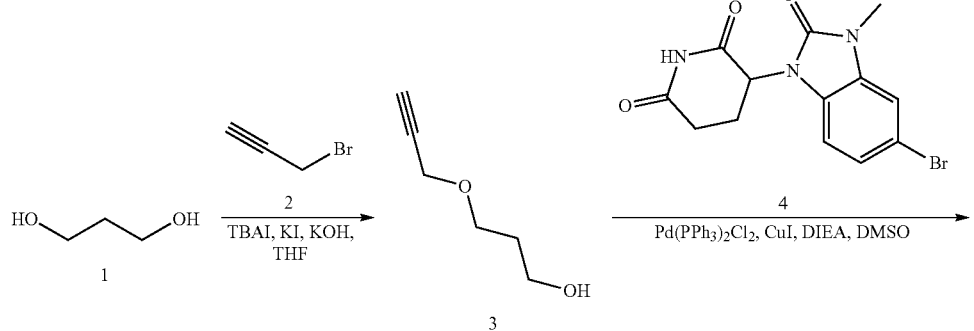
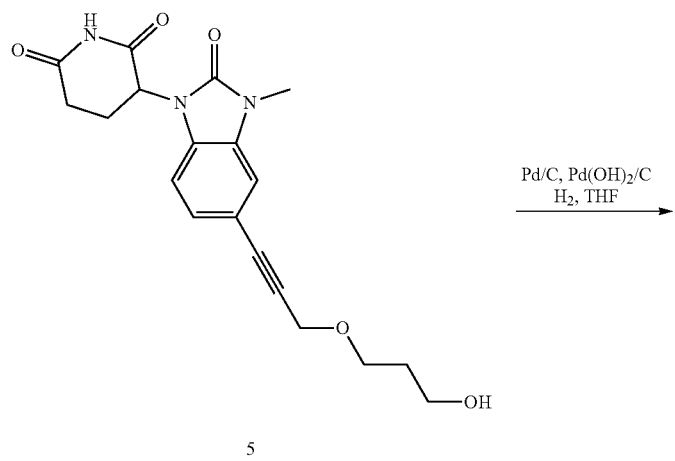
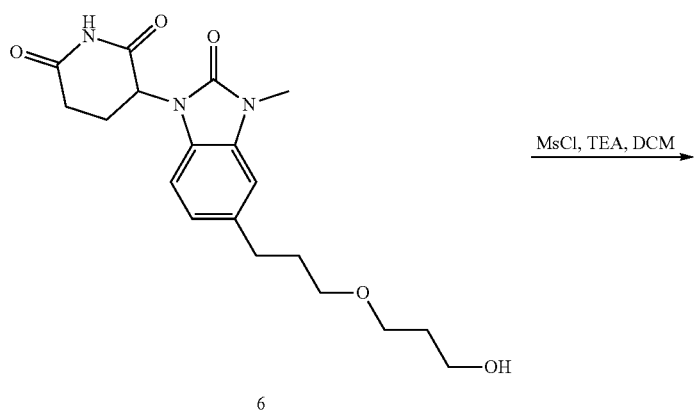

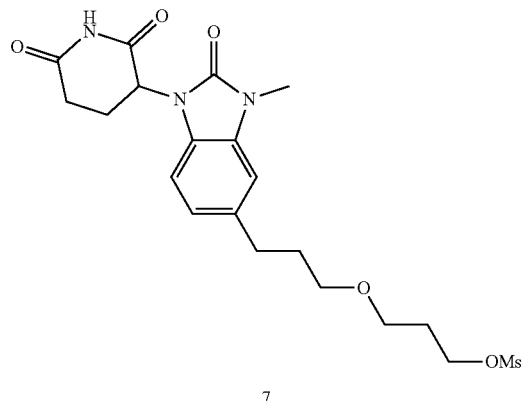

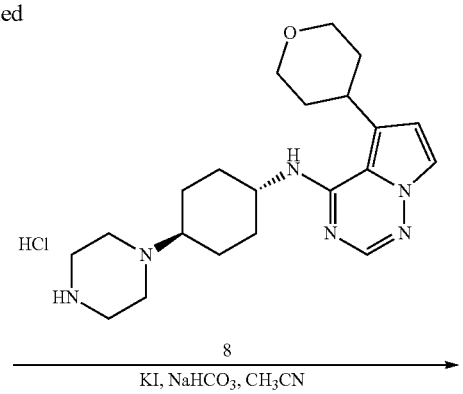

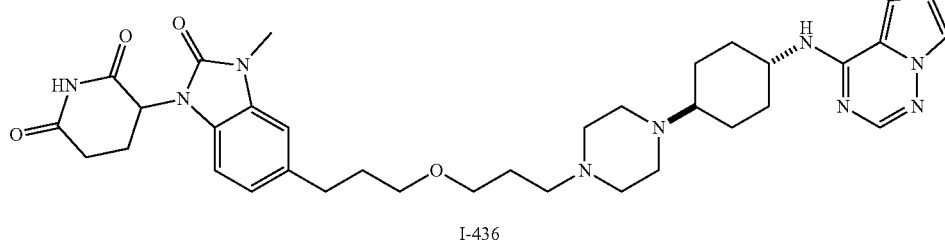

I-436

Step 1—3-Prop-2-ynoxypropan-1-ol (3)

To a solution of propane-1,3-diol (10.0 g, 131 mmol, 9.52 mL, CAS #126-30-7) and 3-bromoprop-1-yne (15.6 g, 131 mmol, 11.3 mL, CAS #106-96-7) in THF (250 mL) was added KOH (7.37 g, 131 mmol), KI (3.27 g, 19.7 mmol) and TBAI (2.91 g, 7.88 mmol). The reaction mixture was stirred at 25° C. for 16 hrs. On completion, the mixture was filtered, and the filter was concentrated in vacuo to give a residue, the residue was diluted with $H_2O$ (50 mL), and then extracted with EA (2×100 mL). The organic phase was concentrated in vacuo to give a residue. The residue was purified by flash silica gel chromatography to give the title compound (8.00 g, 53% yield) as yellow oil. $^1$H NMR (400 MHz, DMSO-$d_6$) δ 4.14 (d, J=2.4 Hz, 2H), 3.75 (t, J=5.6 Hz, 2H), 3.68 (t, J=5.6 Hz, 2H), 2.44 (t, J=2.4 Hz, 1H), 2.23 (s, 1H), 1.88-1.81 (m, 2H).

Step 2—3-[5-[3-(3-Hydroxypropoxy)prop-1-ynyl]-3-methyl-2-oxo-benzimidazol-1-yl]piperidine-2,6-dione (5)

To a solution of 3-prop-2-ynoxypropan-1-ol (506 mg, 4.44 mmol) and 3-(5-bromo-3-methyl-2-oxo-benzimidazol-1-yl)piperidine-2,6-dione (500 mg, 1.48 mmol, Intermediate HN) in DMSO (10 mL) was added DIEA (955 mg, 7.39 mmol, 1.29 mL), CuI (56.3 mg, 295 umol) and Pd(PPh$_3$)$_2$Cl$_2$ (207 mg, 295 umol). The reaction mixture was stirred at 80° C. for 2 hr under N$_2$. On completion, the mixture was filtered; the filtrate was concentrated in vacuo to give a residue. The residue was purified by reverse phase column (0.1% FA condition) to give the title compound (370 mg, 67% yield) as a yellow solid. LC-MS (ESI$^+$) m/z 372.1 (M+H)$^+$.

Step 3—3-[5-[3-(3-Hydroxypropoxy)propyl]-3-methyl-2-oxo-benzimidazol-1-yl]piperidine-2,6-dione (6)

To a solution of 3-[5-[3-(3-hydroxypropoxy)prop-1-ynyl]-3-methyl-2-oxo-benzimidazol-1-yl]piperidine-2,6-dione (370 mg, 996 umol) in THF (20 mL) was added Pd/C (100 mg, 10% purity) and Pd(OH)$_2$/C (100 mg, 10% purity). The reaction mixture was stirred at 25° C. for 12 hrs under H$_2$ (15 psi). On completion, the residue was filtered and the filtrate was concentrated in vacuo to give the title compound (340 mg, 90% yield) as a white solid. $^1$H NMR (400 MHz, DMSO-$d_6$) δ 11.07 (s, 1H), 7.06-6.96 (m, 2H), 6.86 (d, J=8.0 Hz, 1H), 5.33 (dd, J=5.2, 12.8 Hz, 1H), 4.36 (s, 1H), 3.47 (t, J=6.4 Hz, 2H), 3.43-3.40 (m, 2H), 3.37-3.34 (m, 2H), 3.34 (s, 3H), 2.95-2.85 (m, 1H), 2.76-2.57 (m, 4H), 2.04-1.96 (m, 1H), 1.85-1.76 (m, 2H), 1.69-1.62 (m, 2H); LC-MS (ESI$^+$) m/z 376.2 (M+H)$^+$.

Step 4—3-[3-[1-(2,6-Dioxo-3-piperidyl)-3-methyl-2-oxo-benzimidazol-5-yl]propoxy]propyl methanesulfonate (7)

To a solution of 3-[5-[3-(3-hydroxypropoxy)propyl]-3-methyl-2-oxo-benzimidazol-1-yl]piperidine-2,6-dione (100 mg, 266 umol) and TEA (80.8 mg, 799 umol, 111 uL) in DCM (5 mL) was added MsCl (36.6 mg, 319 umol, 24.7 uL) at 0° C. The reaction mixture was stirred at 20° C. for 1 hr.

On completion, the mixture was quenched by water (20 mL), and then extracted with DCM (2×50 mL). The organic phase was concentrated in vacuo to give the title compound (100 mg, 83% yield) as yellow oil. ¹H NMR (400 MHz, DMSO-d₆) δ 11.09 (s, 1H), 7.03 (s, 1H), 7.00 (d, J=8.0 Hz, 1H), 6.90-6.84 (m, 1H), 5.34 (dd, J=5.2, 12.8 Hz, 1H), 4.27 (t, J=6.4 Hz, 2H), 3.47-3.43 (m, 2H), 3.38 (t, J=6.4 Hz, 2H), 3.34 (m, 3H), 3.17 (s, 3H), 2.95-2.84 (m, 1H), 2.73-2.57 (m, 4H), 2.04-1.96 (m, 1H), 1.94-1.88 (m, 2H), 1.86-1.78 (m, 2H); LC-MS (ESI⁺) m/z 454.2 (M+H)⁺.

Step 5—3-[3-Methyl-2-oxo-5-[3-[3-[4-[4-[(5-tetrahydropyran-4-ylpyrrolo[2,1-f][1,2,4]triazin-4-yl)amino]cyclohexyl]piperazin-1-yl]propoxy]propyl]benzimidazol-1-yl]piperidine-2,6-dione. (I-436)

To a solution of 3-[3-[1-(2,6-dioxo-3-piperidyl)-3-methyl-2-oxo-benzimidazol-5-yl]propoxy]propyl methanesulfonate (90.4 mg, 199 umol) and N-(4-piperazin-1-ylcyclohexyl)-5-tetrahydropyran-4-yl-pyrrolo[2,1-f][1,2,4]triazin-4-amine (70.0 mg, 166 umol, Intermediate OP) in CH₃CN (10 mL) was added KI (276 ug, 1.66 umol) and NaHCO₃ (41.9 mg, 498 umol). The reaction mixture was stirred at 130° C. for 12 hrs. On completion, the residue was purified by prep-HPLC (column: Phenomenex Synergi C18 150*25*10 um; mobile phase: [water (0.225% FA)-ACN]; B %: 11%-35%, 8 min) to give the title compound (20.8 mg, 16% yield) as a yellow solid. ¹H NMR (400 MHz, DMSO-d₆) δ 11.10 (s, 1H), 7.79 (s, 1H), 7.54 (d, J=2.4 Hz, 1H), 7.08-6.97 (m, 2H), 6.87 (d, J=8.0 Hz, 1H), 6.53 (d, J=2.8 Hz, 1H), 6.21 (d, J=8.0 Hz, 1H), 5.34 (dd, J=5.2, 12.8 Hz, 1H), 4.12-3.99 (m, 1H), 3.94-3.86 (m, 2H), 3.59-3.50 (m, 2H), 3.46-3.33 (m, 6H), 3.33 (s, 3H), 2.95-2.85 (m, 1H), 2.72-2.67 (m, 1H), 2.66-2.62 (m, 2H), 2.61-2.57 (m, 1H), 2.56-2.51 (m, 4H), 2.44-2.34 (m, 3H), 2.34-2.30 (m, 2H), 2.29-2.25 (m, 1H), 2.04-1.94 (m, 3H), 1.88-1.73 (m, 6H), 1.70-1.61 (m, 4H), 1.51 (q, J=12.0 Hz, 2H), 1.33 (q, J=11.6 Hz, 2H); LC-MS (ESI⁺) m/z 742.5 (M+H)⁺.

Example 432: 3-[3-Methyl-2-oxo-5-[3-[3-oxo-3-[4-[4-[(5-tetrahydropyran-4-ylpyrrolo[2,1-f][1,2,4]triazin-4-yl)amino]cyclohexyl]piperazin-1-yl]propoxy]propyl]benzimidazol-1-yl]piperidine-2,6-dione (I-437)

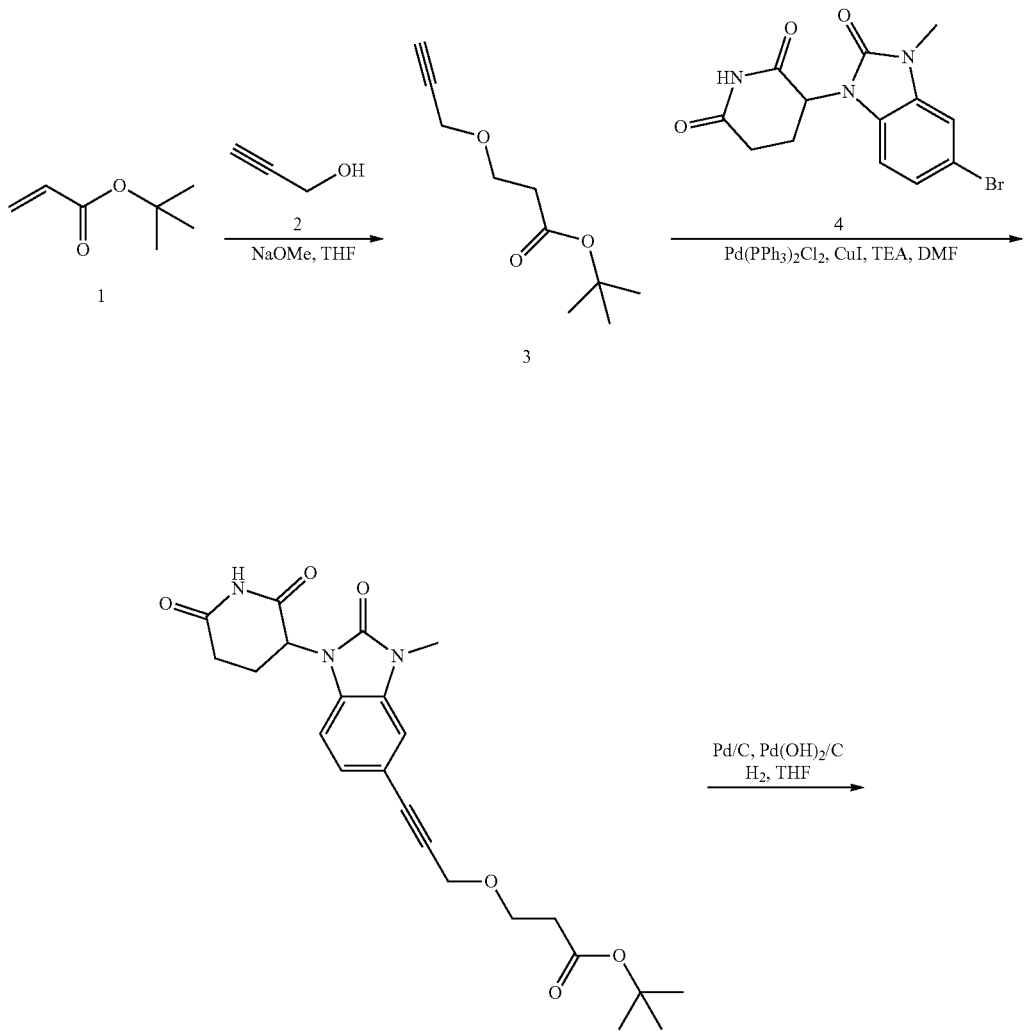

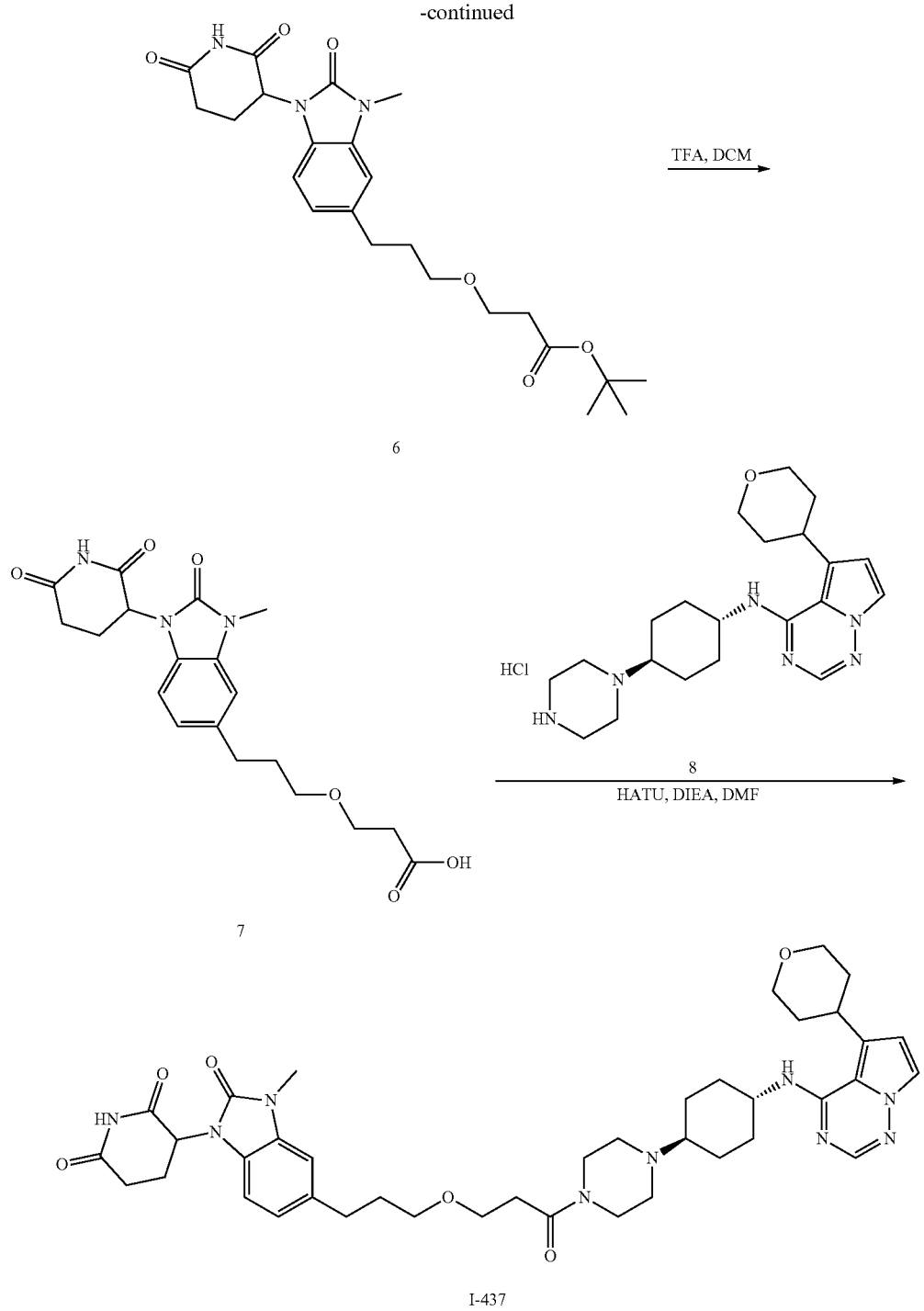

Step 1—Tert-butyl 3-prop-2-ynoxypropanoate (3)

A mixture of tert-butyl prop-2-enoate (2 g, 15.6 mmol, 2.27 mL, CAS #1663-39-4), prop-2-yn-1-ol (2.62 g, 46.8 mmol, 2.77 mL, CAS #107-19-7) in THF (10 mL) was added NaOMe (84.3 mg, 1.56 mmol), and then the mixture was stirred at 25° C. for 16 hrs under $N_2$ atmosphere. On completion, the mixture was diluted with water (30 mL), and then extracted with EA (2×100 mL). The organic layer was dried with $Na_2SO_4$, filtrated and concentrated in vacuo to give the title compound (1.80 g, 63% yield) as light yellow oil. $^1$H NMR (400 MHz, $CDCl_3$) δ 4.18 (d, J=2.4 Hz, 2H), 3.78 (t, J=6.4 Hz, 2H), 2.54 (t, J=6.4 Hz, 2H), 2.45 (s, 1H), 1.47 (s, 9H).

Step 2—Tert-butyl 3-[3-[1-(2,6-dioxo-3-piperidyl)-3-methyl-2-oxo-benzimidazol-5-yl]prop-2-ynoxy] propanoate (5)

A mixture of 3-(5-bromo-3-methyl-2-oxo-benzimidazol-1-yl)piperidine-2,6-dione (400 mg, 1.18 mmol, Intermediate HN), tert-butyl 3-prop-2-ynoxypropanoate (654 mg, 3.55 mmol), Pd(PPh$_3$)$_2$Cl$_2$ (166 mg, 236 umol), CuI (45.0 mg, 236 umol) and TEA (2.15 g, 21.0 mmol, 2.96 mL) in DMF (15 mL) was degassed and purged with N$_2$ for 3 times, and then the mixture was stirred at 85° C. for 4 hrs under N$_2$ atmosphere. On completion, the mixture was diluted with water (50 mL), and then extracted with EA (2×100 mL). The organic layer was washed with brine (20 mL), dried with Na$_2$SO$_4$, filtrated and concentrated in vacuo. The residue was purified by reverse phase flash to give the title compound (300 mg, 49% yield) as light yellow solid. LC-MS (ESI$^+$) m/z 386.1 (M+1−56)$^+$.

Step 3—Tert-butyl 3-[3-[1-(2,6-dioxo-3-piperidyl)-3-methyl-2-oxo-benzimidazol-5-yl]propoxy]propanoate (6)

To a solution of tert-butyl 3-[3-[1-(2,6-dioxo-3-piperidyl)-3-methyl-2-oxo-benzimidazol-5-yl]prop-2-ynoxy]propanoate (250 mg, 566 umol) in THF (50 mL) was added Pd/C (50 mg, 10% purity) and Pd(OH)$_2$/C (50 mg, 10% purity). The mixture was stirred at 25° C. for 5 hrs under H$_2$ atmosphere (15 psi). On completion, the mixture was filtered and the filtrate was concentrated in vacuo to give the title compound (200 mg, 79% yield) as white solid. $^1$H NMR (400 MHz, DMSO-d$_6$) δ 11.09 (s, 1H), 7.07-6.98 (m, 2H), 6.90-6.83 (m, 1H), 5.34 (dd, J=5.2, 12.8 Hz, 1H), 3.63-3.53 (m, 2H), 3.39-3.37 (m, 2H), 3.33 (s, 3H), 3.02-2.83 (m, 1H), 2.78-2.58 (m, 4H), 2.43 (t, J=6.0 Hz, 2H), 2.07-1.94 (m, 1H), 1.85-1.74 (m, 2H), 1.41 (s, 9H).

Step 4—3-[3-[1-(2,6-Dioxo-3-piperidyl)-3-methyl-2-oxo-benzimidazol-5-yl]propoxy]propanoic acid (7)

To a solution of tert-butyl 3-[3-[1-(2,6-dioxo-3-piperidyl)-3-methyl-2-oxo-benzimidazol-5-yl]propoxy]propanoate (150 mg, 336 umol) in DCM (4 mL) was added TFA (4.62 g, 40.0 mmol, 3.00 mL). The mixture was stirred at 25° C. for 2 hrs. On completion, the mixture was concentrated in vacuo to give the title compound (120 mg, 91% yield) as brown solid. $^1$H NMR (400 MHz, DMSO-d$_6$) δ 11.08 (s, 1H), 7.11-6.95 (m, 2H), 6.87 (dd, J=1.2, 8.0 Hz, 1H), 5.34 (dd, J=5.2, 12.8 Hz, 1H), 3.58 (t, J=6.4 Hz, 2H), 3.38 (t, J=6.4 Hz, 2H), 3.33 (s, 3H), 2.99-2.84 (m, 1H), 2.76-2.57 (m, 4H), 2.46 (t, J=6.4 Hz, 2H), 2.03-1.98 (m, 1H), 1.86-1.74 (m, 2H).

Step 5—3-[3-Methyl-2-oxo-5-[3-[3-oxo-3-[4-[4-[(5-tetrahydropyran-4-ylpyrrolo[2,1-f][1,2,4]triazin-4-yl)amino]cyclohexyl]piperazin-1-yl]propoxy]propyl]benzimidazol-1-yl]piperidine-2,6-dione (I-437)

A mixture of 3-[3-[1-(2,6-dioxo-3-piperidyl)-3-methyl-2-oxo-benzimidazol-5-yl]propoxy]propanoic acid (120 mg, 308 umol), N-(4-piperazin-1-ylcyclohexyl)-5-tetrahydropyran-4-yl-pyrrolo[2,1-f][1,2,4]triazin-4-amine (129 mg, 308 umol, HCl, Intermediate OP), DIEA (119 mg, 924 umol), HATU (140 mg, 369 umol) in DMF (3 mL) was degassed and purged with N$_2$ for 3 times, and then the mixture was stirred at 25° C. for 2 hrs under N$_2$ atmosphere. On completion, the mixture was concentrated in vacuo. The residue was purified by Pre-HPLC (column: Phenomenex Synergi C18 150*25*10 um; mobile phase: [water (0.225% FA)-ACN]; B %: 11%-39%, 9 min) to give the title compound (55.0 mg, 24% yield) as white solid. $^1$H NMR (400 MHz, DMSO-d$_6$) δ 11.09 (s, 1H), 7.79 (s, 1H), 7.55 (d, J=2.8 Hz, 1H), 7.08-6.97 (m, 2H), 6.87 (d, J=7.6 Hz, 1H), 6.54 (d, J=2.4 Hz, 1H), 6.21 (d, J=7.6 Hz, 1H), 5.34 (dd, J=5.2, 12.8 Hz, 1H), 4.10-4.01 (m, 1H), 3.95-3.85 (m, 2H), 3.64-3.48 (m, 8H), 3.34-3.30 (m, 7H), 2.96-2.86 (m, 1H), 2.70-2.54 (m, 7H), 2.48-2.42 (m, 2H), 2.38-2.28 (m, 1H), 2.03-1.96 (m, 3H), 1.88-1.71 (m, 6H), 1.71-1.59 (m, 2H), 1.57-1.46 (m, 2H), 1.43-1.27 (m, 2H), LC-MS (ESI$^+$) m/z 756.5 (M+1)$^+$.

Example 433: 3-[3-Methyl-2-oxo-5-[7-oxo-7-[4-[4-(5-tetrahydropyran-4-ylpyrrolo[2,1-f][1,2,4]triazin-4-yl)amino]cyclohexyl]piperazin-1-yl]heptyl]benzimidazol-1-yl]piperidine-2,6-dione (I-438)

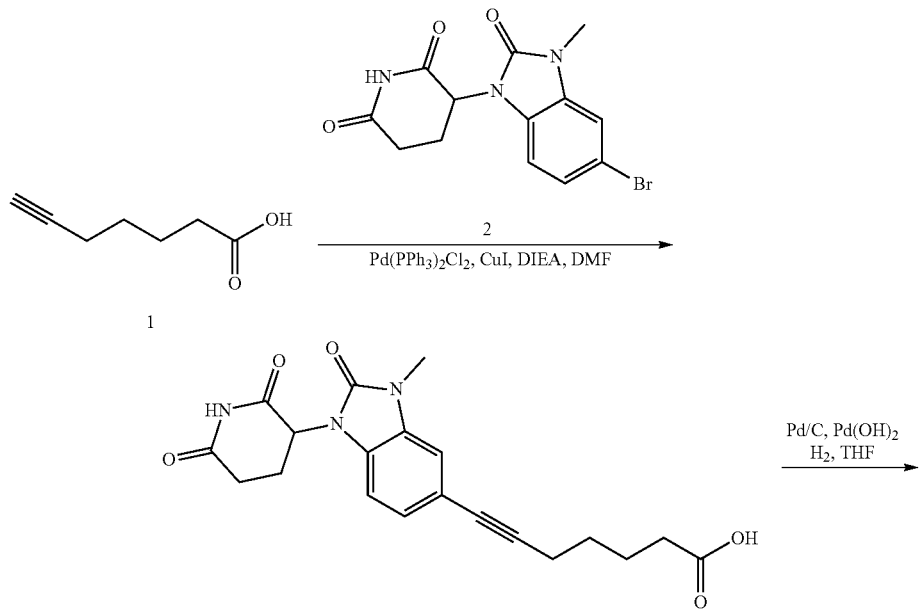

-continued

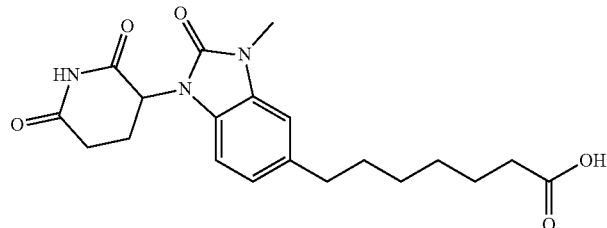

4

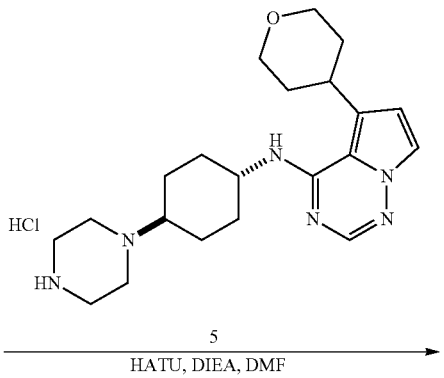

5

→ HATU, DIEA, DMF

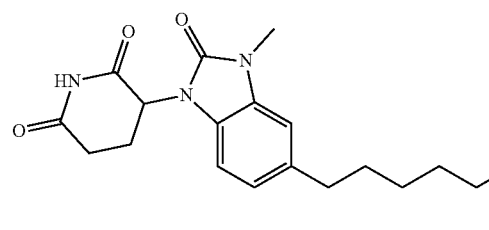

I-438

Step 1—7-[1-(2,6-Dioxo-3-piperidyl)-3-methyl-2-oxo-benzimidazol-5-yl]hept-6-ynoic acid (3)

A mixture of hept-6-ynoic acid (224 mg, 1.77 mmol, CAS #30964-00-2), 3-(5-bromo-3-methyl-2-oxo-benzimidazol-1-yl)piperidine-2,6-dione (200 mg, 591 umol, Intermediate HN), Pd(PPh$_3$)$_2$Cl$_2$ (12.5 mg, 17.7 umol), CuI (1.13 mg, 5.91 umol) and DIEA (1.53 g, 11.8 mmol) in DMSO (5 mL) was degassed and purged with N$_2$ for 3 times in glove box. The mixture was stirred at 80° C. for 2 hrs under N$_2$ atmosphere. On completion, the crude product was purified by reverse phase column (0.1% FA condition) to give the title compound (180 mg, 60% yield) as a yellow solid. $^1$H NMR (400 MHz, DMSO-d$_6$) δ=11.12 (s, 1H), 7.97-7.67 (m, 1H), 7.29-7.18 (m, 1H), 7.17-7.03 (m, 2H), 5.37 (d, J=13.2 Hz, 1H), 3.43-3.38 (m, 3H), 2.93-2.81 (m, 2H), 2.74-2.65 (m, 1H), 2.46-2.39 (m, 2H), 2.30-2.23 (m, 2H), 2.02 (d, J=4.4 Hz, 1H), 1.72-1.43 (m, 4H).

Step 2—Tert-butyl 6-[2-[2-[[2-(2,6-dioxo-3-piperidyl)-1,3-dioxo-isoindolin-4-yl]amino]ethoxy]ethyl]-2,6-diazaspiro[3.3]heptane-2-carboxylate (4)

To a solution of 7-[1-(2,6-dioxo-3-piperidyl)-3-methyl-2-oxo-benzimidazol-5-yl]hept-6-ynoic acid (160 mg, 417 umol) in THF (50 mL) was added Pd/C (200 mg, 417 umol, 50% purity) and Pd(OH)$_2$/C (200 mg, 417 umol, 10% purity) under N$_2$. The suspension was degassed under vacuum and purged with H$_2$ several times. The mixture was stirred at 15° C. for 2 hours under H$_2$ (15 psi). On completion, the mixture was filtered with Clite and the filtrate was concentrated in vacuo to give the title compound (100 mg, 40% yield) as a yellow solid. LC-MS (ESI$^+$) m/z 388.2 (M+H)$^+$.

Step 3—3-[3-Methyl-2-oxo-5-[7-oxo-7-[4-[4-[(5-tetrahydropyran-4-ylpyrrolo[2,1-f][1,2,4]triazin-4-yl)amino]cyclohexyl]piperazin-1-yl]heptyl]benzimidazol-1-yl]piperidine-2,6-dione (I-438)

To a solution of 7-[1-(2,6-dioxo-3-piperidyl)-3-methyl-2-oxo-benzimidazol-5-yl]heptanoic acid (100 mg, 258 umol) and N-(4-piperazin-1-ylcyclohexyl)-5-tetrahydropyran-4-yl-pyrrolo[2,1-f][1,2,4]triazin-4-amine (100 mg, 258 umol, Intermediate OP) in DMF (5 mL) was added HATU (118 mg, 310 umol) and DIEA (83.4 mg, 645 umol, 112 uL). The mixture was stirred at 25° C. for 6 hrs. On completion, the residue was purified by prep-HPLC (column: Phenomenex Synergi C18 150*25*10 um; mobile phase: [water (0.05% HCl)-ACN]; B %: 17%-35%, 9 min) to give the title compound (26.0 mg, 12.0% yield) as a light yellow solid. $^1$H NMR (400 MHz, DMSO-d$_6$) δ 11.16 (s, 1H), 11.10 (s, 1H), 7.97 (s, 1H), 7.80 (s, 1H), 7.05-7.00 (m, 2H), 6.87 (d, J=8.0 Hz, 1H), 6.71 (d, J=2.4 Hz, 1H), 5.35 (dd, J=5.6, 12.8 Hz, 1H), 4.49 (d, J=14.4 Hz, 1H), 4.06 (d, J=11.2 Hz, 2H), 3.92 (d, J=8.0 Hz, 4H), 3.50-3.48 (m, 3H), 3.33 (s, 3H), 3.21-3.06 (m, 4H), 2.98-2.84 (m, 2H), 2.70-2.67 (m, 1H), 2.66-2.59 (m, 4H), 2.40-2.34 (m, 2H), 2.25 (s, 2H), 2.09 (s, 2H), 2.04-1.97 (m, 1H), 1.80-1.64 (m, 10H), 1.50 (s, 2H), 1.33-1.30 (m, 4H); LC-MS (ESI$^+$) m/z 754.5 (M+H)$^+$.

Example 434: 3-[3-Methyl-4-[3-[2-[2-[2-[2-[methyl-[4-[(5-tetrahydropyran-4-yl-7H-pyrrolo[2,3-d]pyrimidin-4-yl)amino]cyclohexyl]amino]ethoxy]ethoxy]ethoxy]ethoxy]propyl]-2-oxo-benzimidazol-1-yl]piperidine-2,6-dione (I-439)

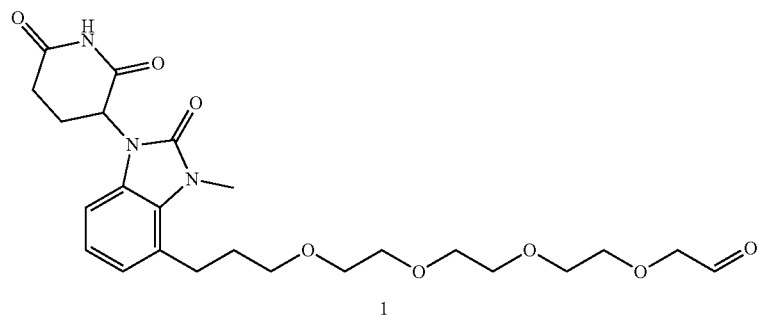

1

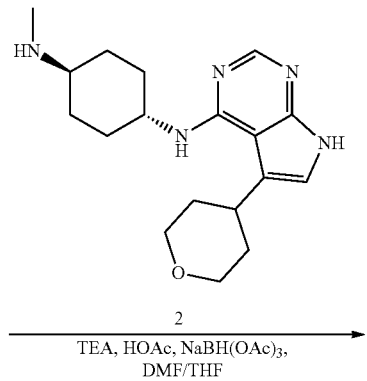

2
——————→
TEA, HOAc, NaBH(OAc)₃, DMF/THF

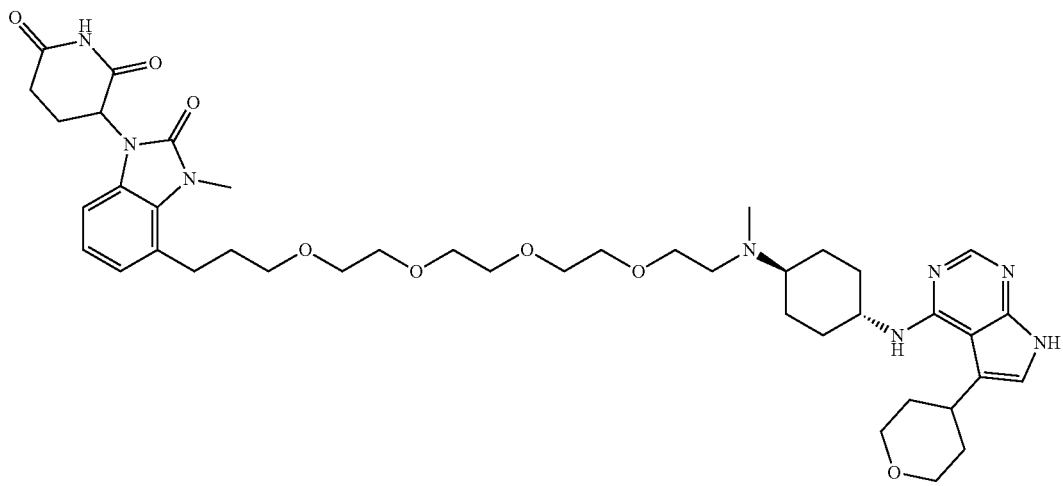

I-439

To a mixture of N1-methyl-N4-(5-tetrahydropyran-4-yl-7H-pyrrolo[2,3-d]pyrimidin-4-yl)cyclohexane-1,4-diamine (80.0 mg, 242 umol, Intermediate OQ) in a mixed solvent of THF (6 mL) and DMF (1.5 mL) was added TEA (36.8 mg, 364 umol), HOAc (21.8 mg, 364 umol) and 2-[2-[2-[2-[3-[1-(2,6-dioxo-3-piperidyl)-3-methyl-2-oxo-benzimidazol-4-yl]propoxy]ethoxy]ethoxy]ethoxy]acetaldehyde (119 mg, 242 umol, from Example 437). The mixture was stirred for 30 minutes, and then NaBH(OAc)₃ (102 mg, 485 umol) was added. The mixture was stirred 25° C. for 48 hours. On completion, the reaction mixture was quenched by water (15 mL), and then extracted with EA (3×30 mL). The combined organic layers were dried over Na₂SO₄, filtered and concentrated in vacuo to give a residue. The residue was purified by prep-HPLC (column: Phenomenex Synergi C18 150*25*10 um; mobile phase: [water (0.05% HCl)-ACN]) to give the title compound (6.12 mg, 2% yield) as yellow solid. ¹H NMR (400 MHz, DMSO-d₆+D₂O) δ 8.30 (s, 1H), 7.19 (s, 1H), 6.96 (d, J=4.8 Hz, 2H), 6.91-6.83 (m, 1H), 5.30 (dd, J=5.6, 12.4 Hz, 1H), 3.89-3.86 (m, 2H), 3.69-3.34 (m, 24H), 3.24-3.16 (m, 2H), 2.98-2.79 (m, 3H), 2.74 (s, 3H), 2.70-2.57 (m, 2H), 2.15-1.94 (m, 5H), 1.85-1.75 (m, 4H), 1.71-1.49 (m, 6H); LC-MS (ESI⁺) m/z 805.6 (M+H)⁺.

Example 435: 2-[2-[2-[2-[3-[1-(2,6-Dioxo-3-piperidyl)-3-methyl-2-oxo-benzimidazol-4-yl]propoxy]ethoxy]ethoxy]ethoxy]-N-[4-[(5-tetrahydropyran-4-yl-7H-pyrrolo[2,3-d]pyrimidin-4-yl)amino]cyclohexyl]acetamide (I-440)

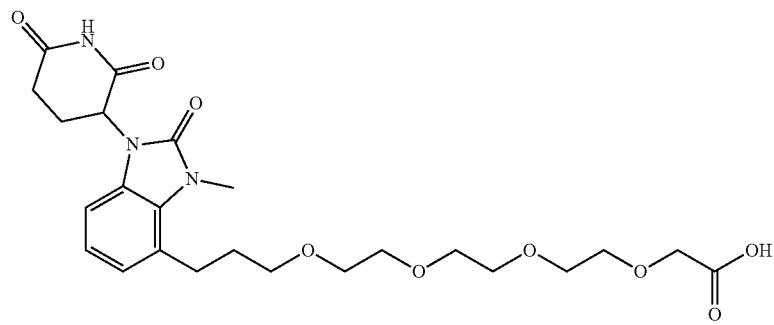

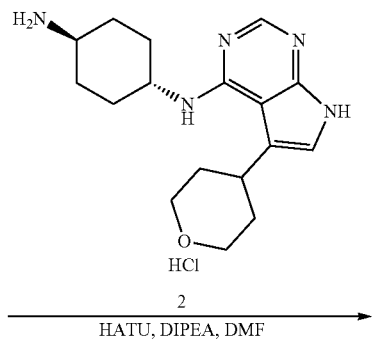

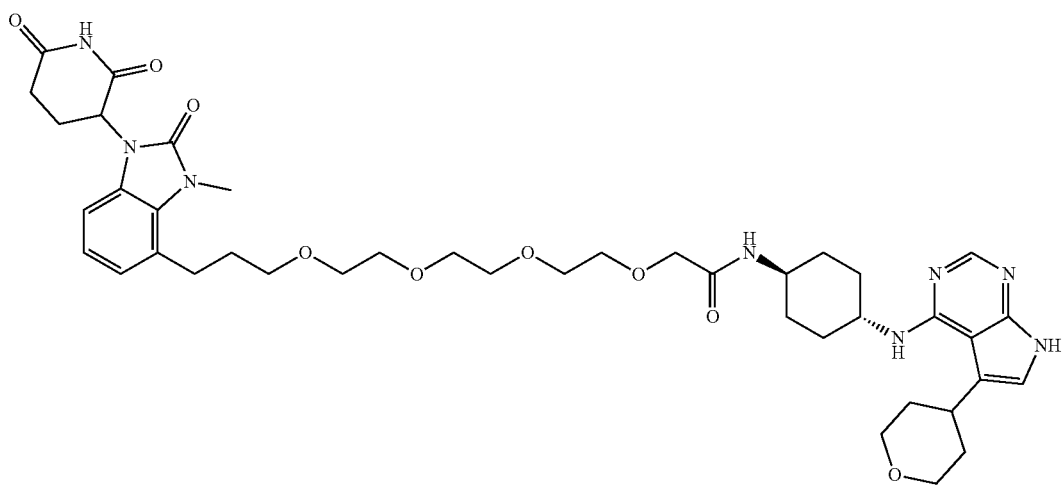

I-440

To a solution of 2-[2-[2-[2-[3-[1-(2,6-dioxo-3-piperidyl)-3-methyl-2-oxo-benzimidazol-4-yl]propoxy]ethoxy]ethoxy]ethoxy]acetic acid (70.7 mg, 113 umol, from Example 447) and N4-(5-tetrahydropyran-4-yl-7H-pyrrolo[2,3-d]pyrimidin-4-yl)cyclohexane-1,4-diamine (40.0 mg, 113 umol, HCl, from I-442) in DMF (5 mL) was HATU (51.9 mg, 136 umol) and DIPEA (73.5 mg, 568 umol, 99.0 uL). The mixture was stirred at 25° C. for 1.5 hrs. On completion, the mixture was quenched with H$_2$O (5 mL), then concentrated in vacuo to give a residue. The residue was purified by prep-HPLC (column: Phenomenex Synergi C18 150*25*10 um; mobile phase: [water (0.225% FA)-ACN]; B %: 7%-37%, 10 min) to give the title compound (33.2 mg, 36% yield) as a white solid. $^1$H NMR (400 MHz, DMSO-d$_6$) δ 11.31 (s, 1H), 11.10 (s, 1H), 8.06 (s, 1H), 7.47 (d, J=8.4 Hz, 1H), 6.99-6.90 (m, 2H), 6.90-6.81 (m, 2H), 5.57 (d, J=8.0 Hz, 1H), 5.35 (dd, J=5.2, 12.4 Hz, 1H), 4.15-4.00 (m, 1H), 3.93-3.87 (m, 2H), 3.85 (s, 2H), 3.60-3.52 (m, 17H), 3.47-3.44 (m, 2H), 3.28-3.19 (m, 2H), 2.96-2.91 (m, 2H), 2.90-2.83 (m, 1H), 2.71-2.58 (m, 2H), 2.03-1.93 (m, 3H), 1.87-1.76 (m, 6H), 1.59-1.36 (m, 6H); LC-MS (ESI+) m/z 805.5 (M+H)$^+$.

Example 436: N-[3-(difluoromethyl)-1-[4-[[4-[4-[1-(2,6-dioxo-3-piperidyl)-3-methyl-2-oxo-benzimidazol-5-yl]butoxy]butylamino]methyl]phenyl]pyrazol-4-yl]-5-piperazin-1-yl-pyrazolo[1,5-a]pyrimidine-3-carboxamide (I-441)
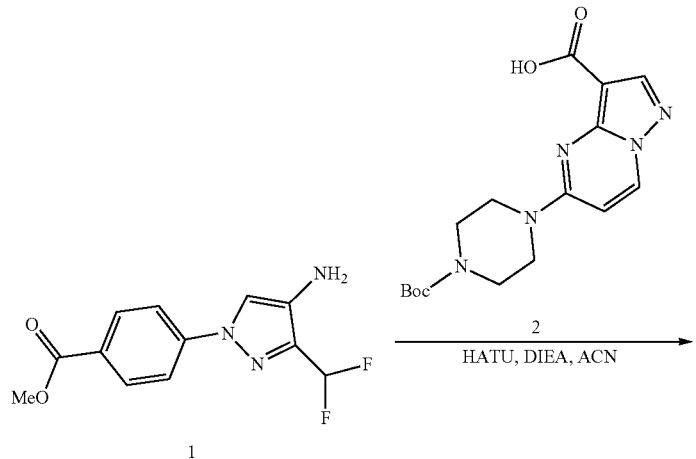
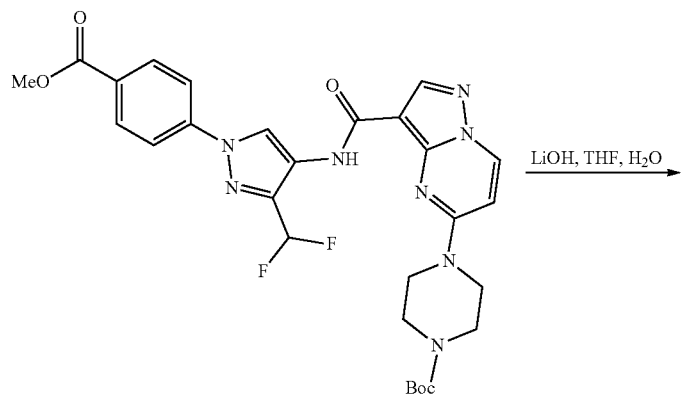
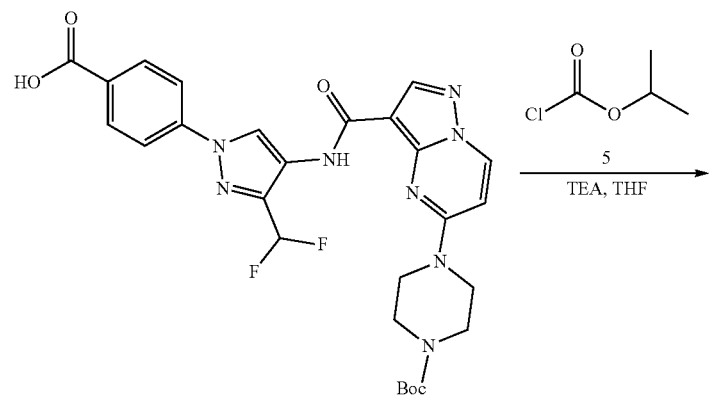

-continued
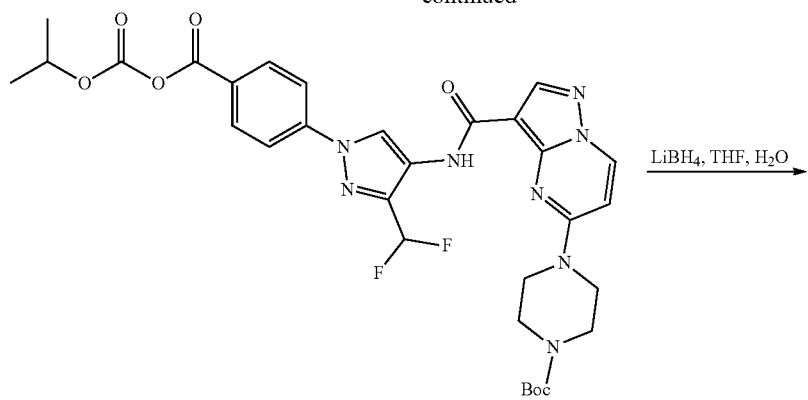
6
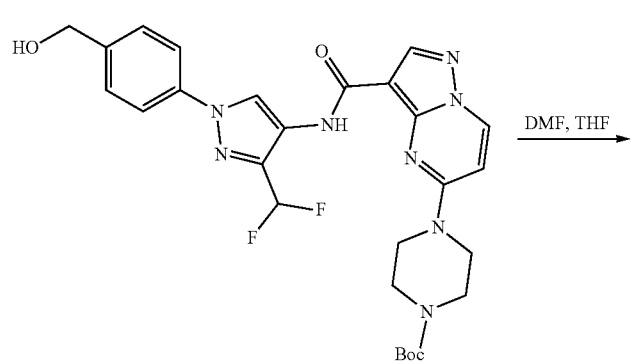
7
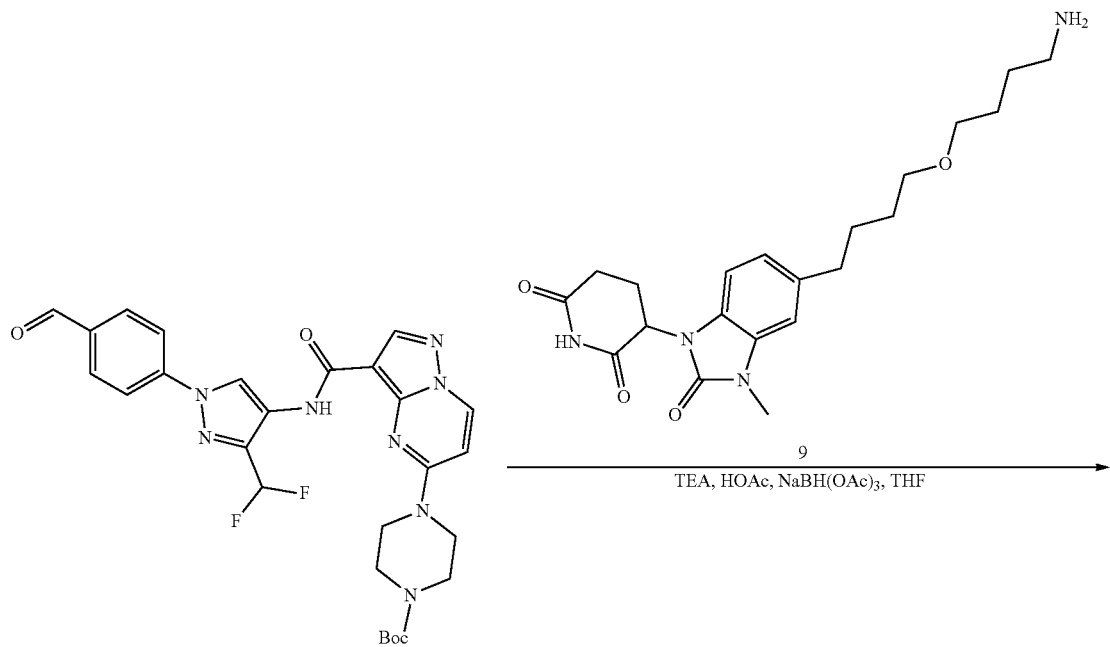
8

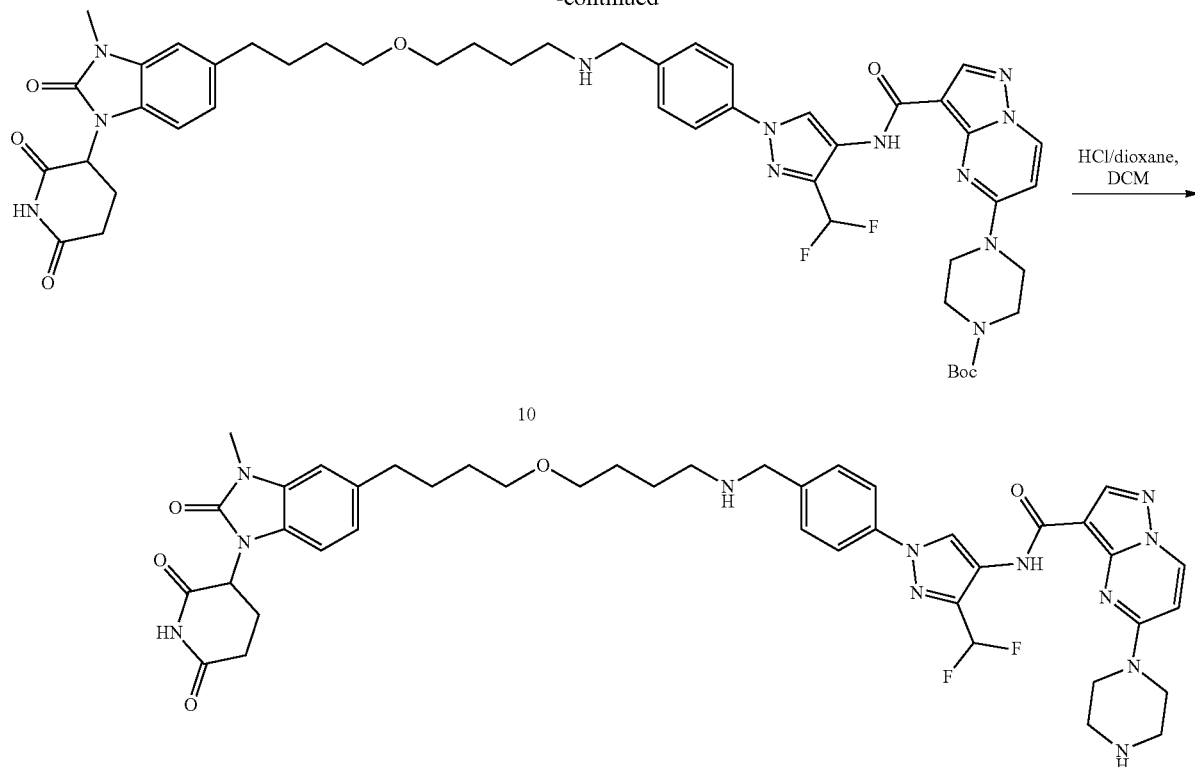

I-441

Step 1—Tert-butyl 4-[3-[[3-(difluoromethyl)-1-(4-methoxycarbonylphenyl)pyrazol-4-yl]carbamoyl]pyrazolo[1,5-a]pyrimidin-5-yl]piperazine-1-carboxylate (3)

To a solution of methyl 4-[4-amino-3-(difluoromethyl)pyrazol-1-yl]benzoate (650 mg, 2.43 mmol, Intermediate FW), 5-(4-tertbutoxycarbonylpiperazin-1-yl)pyrazolo[1,5-a]pyrimidine-3-carboxylic acid (650 mg, 1.87 mmol) in ACN (15.0 mL) was added DIEA (725 mg, 5.61 mmol), HATU (1.42 g, 3.74 mmol). The mixture was stirred at 60° C. for 16 hrs. On completion, the mixture was concentrated in vacuo. The mixture was purified by reverse phase: (0.1% FA) to give the title compound (700 mg, 62% yield) as yellow solid. $^1$H NMR (400 MHz, CDCl$_3$) δ 9.60 (s, 1H), 9.05 (s, 1H), 8.48 (s, 1H), 8.38 (d, J=8.0 Hz, 1H), 8.17 (d, J=8.8 Hz, 2H), 7.83 (d, J=8.8 Hz, 2H), 6.92 (t, J=54.0 Hz, 1H), 6.46 (d, J=8.0 Hz, 1H), 3.96 (s, 3H), 3.91-3.80 (m, 4H), 3.70-3.60 (m, 4H), 1.54 (s, 9H).

Step 2—4-[4-[[5-(4-Tert-butoxycarbonylpiperazin-1-yl)pyrazolo[1,5-a]pyrimidine-3-carbonyl]amino]-3-(difluoromethyl)pyrazol-1-yl]benzoic acid (4)

To a solution of tert-butyl 4-[3-[[3-(difluoromethyl)-1-(4-methoxycarbonylphenyl) pyrazol-4-yl]carbamoyl]pyrazolo[1,5-a]pyrimidin-5-yl]piperazine-1-carboxylate (1.00 g, 1.68 mmol) in THF (40.0 mL) and H$_2$O (8 mL) was added LiOH (200 mg, 8.38 mmol). The mixture was stirred at 20° C. for 16 hrs. On completion, the mixture was concentrated in vacuo. The mixture was diluted with H$_2$O (30 mL). The mixture was acidified with 1N HCl solution till pH=5, filtered and the filter cake was dried in vacuo to give the title compound (900 mg, 92% yield) as yellow solid. $^1$H NMR (400 MHz, DMSO-d$_6$) δ 12.01 (s, 1H), 9.48 (s, 1H), 9.08 (s, 1H), 8.82 (d, J=8.0 Hz, 1H), 8.32 (s, 1H), 8.07 (d, J=8.8 Hz, 2H), 7.97 (d, J=8.8 Hz, 2H), 7.35 (t, J=53.6 Hz, 1H), 6.89 (d, J=8.0 Hz, 1H), 3.90-3.75 (m, 4H), 3.50-3.45 (m, 4H), 1.44 (s, 9H).

Step 3—Tert-butyl 4-[3-[[3-(difluoromethyl)-1-(4-isopropoxycarbonyloxycarbonylphenyl)pyrazol-4-yl]carbamoyl]pyrazolo[1,5-a]pyrimidin-5-yl]piperazine-1-carboxylate (6)

To a solution of 4-[4-[[5-(4-tert-butoxycarbonylpiperazin-1-yl)pyrazolo[1,5-a]pyrimidine-3-carbonyl]amino]-3-(difluoromethyl)pyrazol-1-yl]benzoic acid (900 mg, 1.54 mmol), TEA (625 mg, 6.18 mmol) in THF (30.0 mL) was added isopropyl carbonochloridate (473 mg, 3.86 mmol) at −10° C. The mixture was stirred at −10° C. for 1 hr. On completion, the mixture was filtered and the filtrate was concentrated in vacuo to give the title compound (1.00 g, 90% yield) as yellow solid. LC-MS (ESI$^+$) m/z 669.2 (M+H)$^+$.

Step 4—Tert-butyl 4-[3-[[3-(difluoromethyl)-1-[4-(hydroxymethyl)phenyl]pyrazol-4-yl]carbamoyl]pyrazolo[1,5-a]pyrimidin-5-yl]piperazine-1-carboxylate (7)

To a solution of tert-butyl 4-[3-[[3-(difluoromethyl)-1-(4-isopropoxycarbonyloxycarbonylphenyl) pyrazol-4-yl]carbamoyl]pyrazolo[1,5-a]pyrimidin-5-yl]piperazine-1-carboxylate (1.00 g, 1.50 mmol) in THF (50.0 mL) and H$_2$O (10.0 mL) was added LiBH$_4$ (195 mg, 8.97 mmol) at 0° C. The mixture was stirred at 0° C. for 1 hr. On completion, the mixture was quenched with H$_2$O (10 mL), then extracted with DCM (2×30 mL). The organic layers were dried with anhydrous Na$_2$SO$_4$, filtered and concentrated in vacuo. The mixture was triturate with DCM (5 mL) to give the title compound (700 mg, 82% yield) as yellow solid. $^1$H NMR (400 MHz, DMSO-d$_6$) δ 9.49 (s, 1H), 8.98 (s, 1H), 8.85 (d, J=8.0 Hz, 1H), 8.33 (s, 1H), 7.80 (d, J=8.4 Hz, 2H), 7.48 (d, J=8.4 Hz, 2H), 7.20 (t, J=53.2 Hz, 1H), 6.91 (d, J=8.0 Hz, 1H), 5.35-5.24 (m, 1H), 4.56 (d, J=4.4 Hz, 2H), 3.95-3.75 (m, 4H), 3.55-3.45 (m, 4H), 1.45 (s, 9H).

Step 5—Tert-butyl 4-[3-[[3-(difluoromethyl)-1-(4-formylphenyl)pyrazol-4-yl]carbamoyl]pyrazolo[1,5-a]pyrimidin-5-yl]piperazine-1-carboxylate (8)

To a solution of tert-butyl 4-[3-[[3-(difluoromethyl)-1-[4-(hydroxymethyl)phenyl]pyrazol-4-yl]carbamoyl]pyrazolo[1,5-a]pyrimidin-5-yl]piperazine-1-carboxylate (700 mg, 1.23 mmol) in THF (30.0 mL) was added DMP (626 mg, 1.48 mmol). The mixture was stirred at 20° C. for 1 hour. On completion, the mixture was quenched with saturated Na$_2$S2O3 (30 mL) and washed with saturated NaHCO$_3$ (2×30 mL). The organic layer was dried over anhydrous Na$_2$SO$_4$, filtered and concentrated in vacuo to give the title compound (680 mg, 90% yield) as yellow solid. $^1$H NMR (400 MHz, DMSO-d$_6$) δ 10.04 (s, 1H), 9.52 (s, 1H), 9.17 (s, 1H), 8.86 (d, J=8.0 Hz, 1H), 8.35 (s, 1H), 8.15-8.10 (m, 2H), 8.09-8.03 (m, 2H), 7.39 (t, J=52.8 Hz, 1H), 6.96-6.86 (m, 1H), 3.90-3.80 (m, 4H), 3.50-3.40 (m, 4H), 1.45 (s, 9H).

Step 6—Tert-butyl 4-[3-[[3-(difluoromethyl)-1-[4-[[4-[4-[1-(2,6-dioxo-3-piperidyl)-3-methyl-2-oxo-benzimidazol-5-yl]butoxy]butylamino]methyl]phenyl]pyrazol-4-yl]carbamoyl]pyrazolo[1,5-a]pyrimidin-5-yl]piperazine-1-carboxylate (10)

To a solution of tert-butyl 4-[3-[[3-(difluoromethyl)-1-(4-formylphenyl)pyrazol-4-yl]carbamoyl]pyrazolo[1,5-a]pyrimidin-5-yl]piperazine-1-carboxylate (129 mg, 227 umol), 3-[5-[4-(4-aminobutoxy)butyl]-3-methyl-2-oxo-benzimidazol-1-yl]piperidine-2,6-dione (100 mg, 227 umol, HCl, Intermediate OD) in THF (40.0 mL) was added TEA (46.1 mg, 455 umol) and HOAc (41.0 mg, 683 umol). The mixture was stirred at 20° C. for 0.5 hr, then NaBH(OAc)$_3$ (144 mg, 683 umol) was added. The mixture was stirred at 20° C. for 16 hrs. On completion, the mixture was diluted with H$_2$O (2 mL) and concentrated in vacuo. The mixture was purified by reverse phase column (0.1% FA) to give the title compound (60.0 mg, 27% yield) as yellow solid. LC-MS (ESI$^+$) m/z 953.4 (M+H)$^+$.

Step 7—N-[3-(difluoromethyl)-1-[4-[[4-[4-[1-(2,6-dioxo-3-piperidyl)-3-methyl-2-oxo-benzimidazol-5-yl]butoxy]butylamino]methyl]phenyl]pyrazol-4-yl]-5-piperazin-1-yl-pyrazolo[1,5-a]pyrimidine-3-carboxamide (I-441)

To a solution of tert-butyl 4-[3-[[3-(difluoromethyl)-1-[4-[[4-[4-[1-(2,6-dioxo-3-piperidyl)-3-methyl-2-oxo-benzimidazol-5-yl]butoxy]butylamino]methyl]phenyl]pyrazol-4-yl]carbamoyl]pyrazolo[1,5-a]pyrimidin-5-yl]piperazine-1-carboxylate (60.0 mg, 62.9 umol) in DCM (3.00 mL) was added HCl/dioxane (4.00 M, 5.00 mL). The mixture was stirred at 20° C. for 0.5 hr. On completion, the mixture was concentrated in vacuo. The mixture was purified by prep-HPLC (column: Phenomenex Synergi C18 150*25*10 um; mobile phase: [water (0.225% FA)-ACN]; B %: 8%-32%, 8 min) to give the title compound (31.2 mg, 54% yield) as white solid. $^1$H NMR (400 MHz, DMSO-d$_6$) δ 11.00 (s, 1H), 9.51 (s, 1H), 9.01 (s, 1H), 8.80 (d, J=8.0 Hz, 1H), 8.32 (s, 1H), 8.28 (s, 1H), 7.83 (d, J=8.4 Hz, 2H), 7.54 (d, J=8.4 Hz, 2H), 7.29 (t, J=53.6 Hz, 1H), 7.04-6.96 (m, 2H), 6.92 (d, J=8.0 Hz, 1H), 6.86 (d, J=8.0 Hz, 1H), 5.42-5.26 (m, 1H), 3.90-3.86 (m, 4H), 3.67-3.54 (m, 4H), 3.40-3.33 (m, 4H), 3.31 (s, 3H), 2.88 (s, 4H), 2.75-2.70 (m, 1H), 2.70-2.65 (m, 2H), 2.65-2.61 (m, 1H), 2.61-2.59 (m, 1H), 2.05-1.95 (m, 1H), 1.66-1.48 (m, 8H); LC-MS (ESI$^+$) m/z 853.3 (M+H)$^+$.

Example 437: 3-[3-Methyl-2-oxo-4-[3-[2-[2-[2-[2-[[4-[(5-tetrahydropyran-4-yl-7H-pyrrolo[2,3-d]pyrimidin-4-yl)amino]cyclohexyl]amino]ethoxy]ethoxy]ethoxy]ethoxy]propyl]benzimidazol-1-yl]piperidine-2,6-dione (I-442)

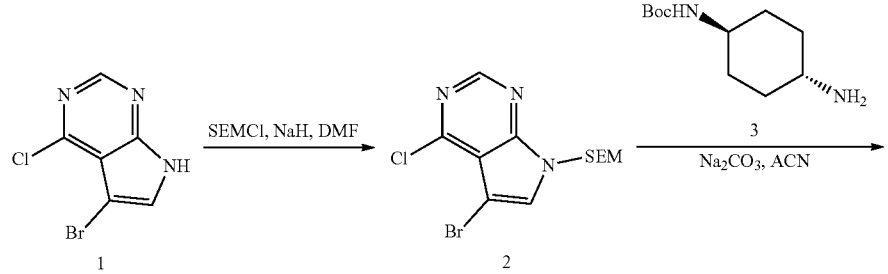

-continued
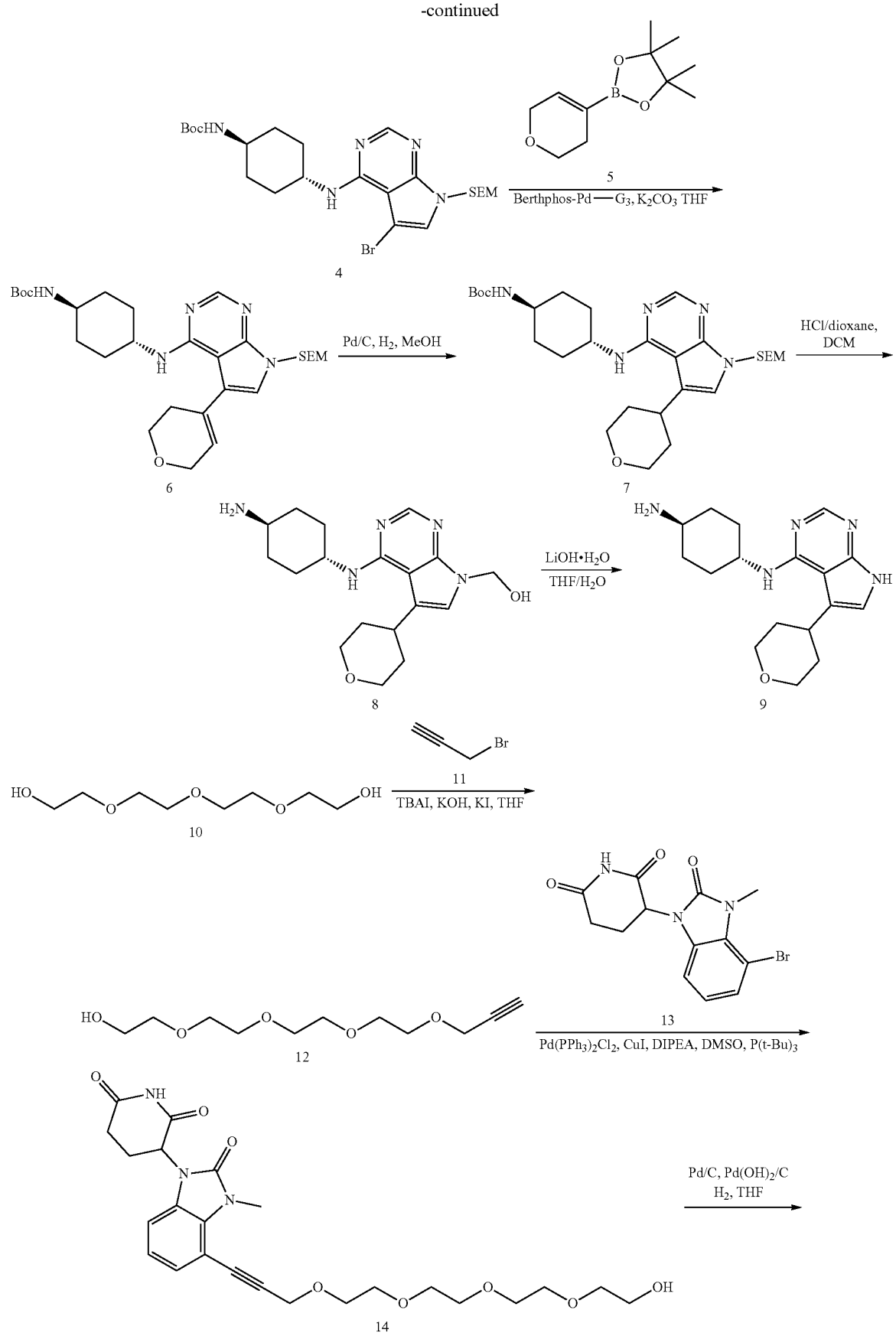

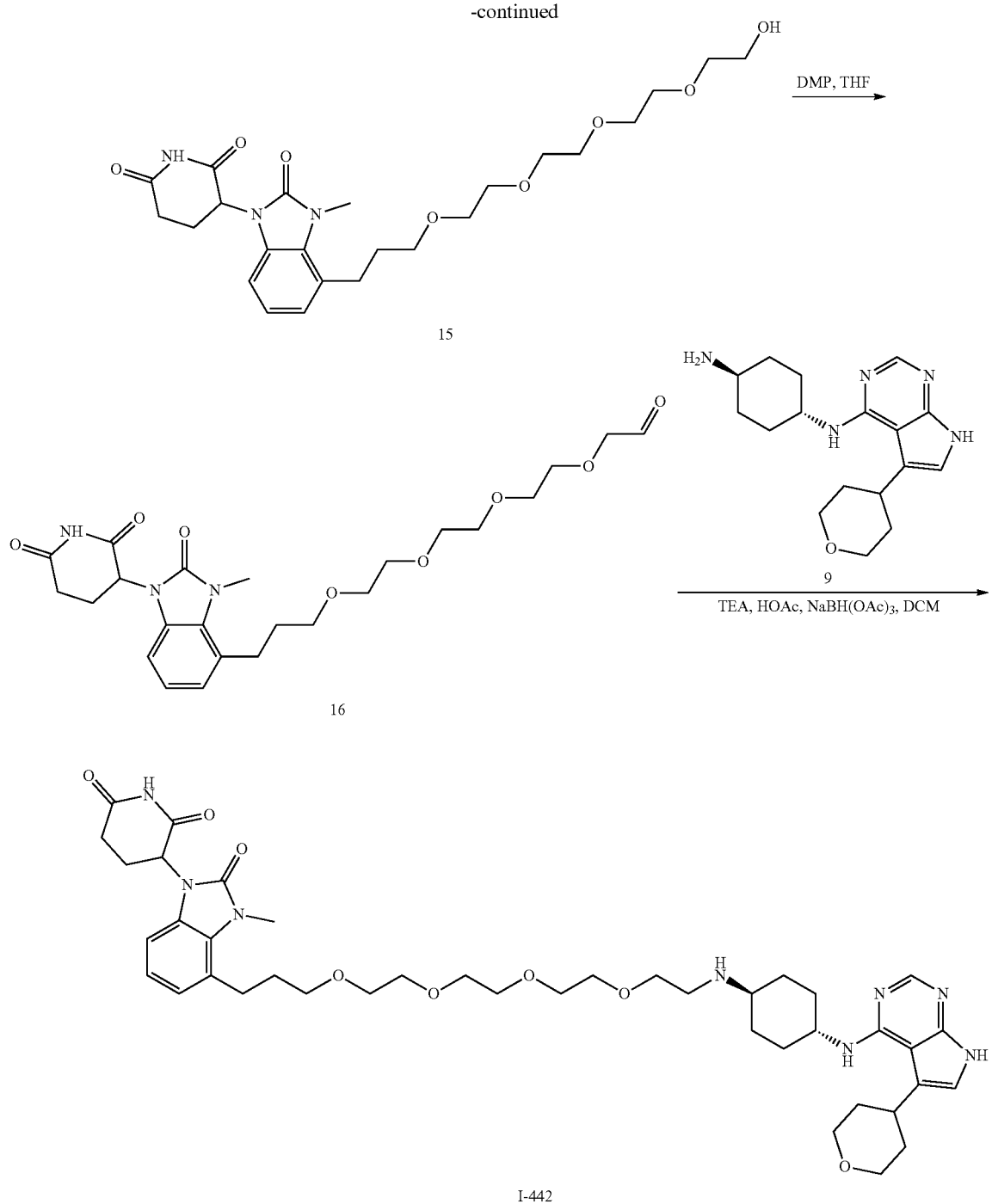

Step 1—2-[(5-Bromo-4-chloro-pyrrolo[2,3-d]pyrimidin-7-yl)methoxy]ethyl-trimethyl-silane (2)

NaH (2.1 g, 52.5 mmol, 60% purity) was suspended in dimethylformamide (50 mL). The mixture was stirred for 10 min and then cooled at 0° C. with an ice bath. 5-bromo-4-chloro-7H-pyrrolo[2,3-d]pyrimidine (10 g, 43.0 mmol) dissolved in dimethylformamide (50 mL) was added drop-wise and the mixture was stirred for 30 min. At the same temperature 2-(chloromethoxy)ethyl-trimethyl-silane (9.00 g, 53.9 mmol, 9.55 mL) dissolved in dimethylformamide (50 mL) was added drop-wise and stirred for 30 min at 0° C. On completed, the mixture was quenched with water (30 mL), extracted with ethyl acetate (3×30 mL). The combined organic layers was washed with brine (2×10 mL), dried over anhydrous sodium sulfate, filtered and concentrated in vacuo. The reaction mixture was purified by silica gel chromatography (PE:EA=30:1) to give the title compound (13.2 g, 85% yield) as a white solid. $^1$H NMR (400 MHz, CD$_3$OD) δ 8.71-8.50 (m, 1H), 7.81 (s, 1H), 5.67 (s, 2H), 3.69-3.54 (m, 2H), 0.94-0.83 (m, 3H), −0.06 (s, 9H), LC-MS (ESI$^+$) m/z 361.9 (M+H)$^+$

Step 2—Tert-butyl N-[4-[[5-bromo-7-(2-trimethylsilylethoxymethyl)pyrrolo[2,3-d]pyrimidin-4-yl]amino]cyclohexyl]carbamate (4)

To a solution of 2-[(5-bromo-4-chloro-pyrrolo[2,3-d]pyrimidin-7-yl)methoxy]ethyl-trimethyl-silane (1 g, 2.76 mmol) and tert-butyl N-(4-aminocyclohexyl)carbamate (591 mg, 2.76 mmol, CAS #177906-48-8) in ACN (20 mL) was added $Na_2CO_3$ (585 mg, 5.52 mmol). The reaction mixture was stirred at 80° C. for 12 hrs. On completion, the reaction mixture was filtered and concentrated in vacuo. The crude product was triturated with ethyl acetate (10 mL) to give the title compound (1.48 g, 95% yield) as a white solid. $^1$H NMR (400 MHz, $CDCl_3$) δ 8.33 (s, 1H), 7.06 (s, 1H), 5.91 (d, J=7.2 Hz, 1H), 5.52 (s, 2H), 4.45 (s, 1H), 4.14 (d, J=7.2 Hz, 1H), 3.60-3.46 (m, 3H), 2.25 (d, J=9.8 Hz, 2H), 2.16-2.05 (m, 2H), 1.47 (s, 9H), 1.44-1.34 (m, 4H), 0.98-0.86 (m, 2H), −0.03 (s, 9H). LC-MS (ESI$^+$) m/z 540.1; 542.1 (M+H, M+3)$^+$.

Step 3—Tert-butyl N-[4-[[5-(3,6-dihydro-2H-pyran-4-yl)-7-(2-trimethylsilylethoxymethyl)pyrrolo[2,3-d]pyrimidin-4-yl]amino]cyclohexyl]carbamate (6)

A mixture of tert-butyl N-[4-[[5-bromo-7-(2-trimethylsilylethoxymethyl)pyrrolo[2,3-d]pyrimidin-4-yl]amino]cyclohexyl]carbamate (1.34 g, 2.48 mmol), 2-(3,6-dihydro-2H-pyran-4-yl)-4,4,5,5-tetramethyl-1,3,2-dioxaborolane (1.56 g, 7.44 mmol, CAS #287944-16-5), Berttphos-Pd-$G_3$ (224 mg, 247 umol, CAS #1470372-59-8) and $K_2CO_3$ (685 mg, 4.96 mmol) in a mixed solvent of THF (20 mL) and $H_2O$ (4 mL) was degassed and purged with $N_2$ for 3 times, and then the mixture was stirred at 55° C. for 3 hrs under $N_2$ atmosphere. On completion, the reaction mixture was concentrated in vacuo. The residue was washed with ethyl acetate (50 mL). After, the organic layer was concentrated in vacuo. The crude product was purified by reversed-phase HPLC (0.1% FA condition) to give the title compound (1.06 g, 78% yield) as a yellow solid. $^1$H NMR (400 MHz, DMSO-$d_6$) δ 8.28 (s, 1H), 7.44 (s, 1H), 6.81 (d, J=7.6 Hz, 1H), 5.89 (s, 1H), 5.68 (d, J=7.6 Hz, 1H), 5.55 (s, 2H), 4.32 (d, J=2.0 Hz, 2H), 4.04 (s, 1H), 3.92 (t, J=5.2 Hz, 2H), 3.58 (t, J=8.0 Hz, 2H), 3.37-3.30 (m, 1H), 2.52 (s, 2H), 2.10 (d, J=8.0 Hz, 2H), 1.90 (s, 2H), 1.46 (s, 9H), 1.45-1.36 (m, 4H), 0.90 (t, J=8.0 Hz, 2H), 0.00 (s, 9H); LC-MS (ESI$^+$) m/z 544.4 (M+H)$^+$.

Step 4—Tert-butyl N-[4-[[5-tetrahydropyran-4-yl-7-(2-trimethylsilylethoxymethyl)pyrrolo[2,3-d]pyrimidin-4-yl]amino]cyclohexyl]carbamate (7)

To a solution of tert-butyl N-[4-[[5-(3,6-dihydro-2H-pyran-4-yl)-7-(2-trimethylsilylethoxymethyl) pyrrolo[2,3-d]pyrimidin-4-yl]amino]cyclohexyl]carbamate (1.06 g, 1.95 mmol) in methanol (5 mL) was added Pd/C (100 mg, 163 umol, 10%, wt) under $N_2$. The suspension was degassed under vacuum and purged with $H_2$ several times. The mixture was stirred under $H_2$ (15 psi) at 20° C. for 36 hrs. On completion, the mixture was filtered and the filtrate was concentrated in vacuo to give the title compound (1.00 g, 94% yield) as a white solid. $^1$H NMR (400 MHz, DMSO-$d_6$) δ 8.23 (s, 1H), 7.12 (s, 1H), 6.83 (d, J=7.6 Hz, 1H), 5.81 (d, J=7.6 Hz, 1H), 5.52 (s, 2H), 4.13 (d, J=7.6 Hz, 1H), 4.00 (dd, J=2.8, 11.2 Hz, 2H), 3.65 (t, J=11.2 Hz, 2H), 3.56 (t, J=8.0 Hz, 2H), 3.38-3.32 (m, 1H), 2.04 (d, J=10.8 Hz, 2H), 1.98-1.92 (m, 3H), 1.70-1.54 (m, 4H), 1.48 (s, 9H), 1.46-1.27 (m, 4H), 0.91-0.83 (m, 2H), 0.00 (s, 9H); LC-MS (ESI$^+$) m/z 546.4 (M+H)$^+$.

Step 5—[4-[(4-Aminocyclohexyl)amino]-5-tetrahydropyran-4-yl-pyrrolo[2,3-d]pyrimidin-7-yl]methanol (8)

To a solution of tert-butyl N-[4-[[5-tetrahydropyran-4-yl-7-(2-trimethylsilylethoxymethyl)pyrrolo[2,3-d]pyrimidin-4-yl]amino]cyclohexyl]carbamate (1.00 g, 1.83 mmol) in DCM (20 mL) was added HCl/dioxane (4 M, 30 mL). The reaction mixture was stirred at 20° C. for 12 hrs. On completion, the reaction mixture was concentrated in vacuo to give the title compound (633 mg, 100% yield) as a white solid. LC-MS (ESI$^+$) m/z 346.2 (M+H)$^+$.

Step 6—N4-(5-tetrahydropyran-4-yl-7H-pyrrolo[2,3-d]pyrimidin-4-yl)cyclohexane-1,4-diamine (9)

To a solution of [4-[(4-aminocyclohexyl)amino]-5-tetrahydropyran-4-yl-pyrrolo[2,3-d]pyrimidin-7-yl]methanol (633 mg, 1.83 mmol) in a mixed solvent of THF (3 mL), $H_2O$ (1 mL) and MeOH (1 mL) was added LiOH.$H_2O$ (384 mg, 9.16 mmol). The reaction mixture was stirred at 20° C. for 12 hrs. On completion, the reaction mixture was acidified with HCl (2 N) to pH=2. The reaction mixture was concentrated in vacuo. The crude product was purified by reversed-phase HPLC (0.1% $NH_3$.$H_2O$ condition) to give the title compound (250 mg, 43% yield) was added as a green solid. LC-MS (ESI$^+$) m/z 316.2 (M+H)$^+$.

Step 7—2-[2-[2-(2-Prop-2-ynoxyethoxy)ethoxy]ethoxy]ethanol (12)

To a mixture of 2-[2-[2-(2-hydroxyethoxy)ethoxy]ethoxy]ethanol (20.0 g, 102 mmol, 17.7 mL) and 3-bromoprop-1-yne (14.7 g, 123 mmol) in THF (200 mL) was added TBAI (2.28 g, 6.18 mmol), KI (2.56 g, 15.45 mmol) and KOH (5.78 g, 102 mmol). The mixture was stirred at 25° C. for 12 hours. On completion, the reaction mixture was filtered and concentrated in vacuo. The residue was purified by column chromatography (PE:EA=5/1 to 0/1) to give the title compound (16.0 g, 67% yield) as a light yellow oil. $^1$H NMR (400 MHz, $CDCl_3$) δ 4.18 (d, J=2.4 Hz, 2H), 3.70 (d, J=4.8 Hz, 2H), 3.67 (d, J=3.2 Hz, 2H), 3.69-3.61 (m, 10H), 3.60-3.57 (m, 2H), 2.73 (s, 1H), 2.42 (t, J=2.4 Hz, 1H).

Step 8—3-[4-[3-[2-[2-[2-(2-Hydroxyethoxy)ethoxy]ethoxy]prop-1-ynyl]-3-methyl-2-oxo-benzimidazol-1-yl]piperidine-2,6-dione (14)

To a mixture of 2-[2-[2-(2-prop-2-ynoxyethoxy)ethoxy]ethoxy]ethanol (1.03 g, 4.44 mmol) and 3-(4-bromo-3-methyl-2-oxo-benzimidazol-1-yl)piperidine-2,6-dione (0.50 g, 1.48 mmol, Intermediate HP) in DMSO (20 mL) was added CuI (56.3 mg, 295 umol), P(t-Bu)$_3$ (2.30 g, 1.48 mmol, 2.67 mL, 13% purity, a solution of toluene), DIEA (955 mg, 7.39 mmol) and Pd(PPh$_3$)$_2$Cl$_2$ (103 mg, 147 umol). The reaction mixture was stirred at 80° C. for 3 hours. On completion, the reaction mixture was diluted with water (60 mL) and extracted with EA (4×60 mL). The combined organic layers was dried over $Na_2SO_4$, filtered and concentrated in vacuo to give a residue. The crude product was purified by prep-HPLC (0.1% FA condition) to give the title compound (0.50 g, 69% yield) as brown oil. $^1$H NMR (400 MHz, DMSO-$d_6$) δ=11.11 (s, 1H), 7.17 (d, J=8.0 Hz, 1H), 7.15-7.11 (m, 1H), 7.06-7.00 (m, 1H), 5.40 (dd, J=5.2, 12.8 Hz, 1H), 4.55 (t, J=5.2 Hz, 1H), 4.46 (s, 2H), 3.70-3.61 (m, 5H), 3.60-3.57 (m, 2H), 3.53-3.51 (m, 6H), 3.49-3.47 (m, 4H), 3.41-3.39 (m, 2H), 2.95-2.84 (m, 1H), 2.77-2.58 (m, 2H), 2.07-1.99 (m, 1H).

Step 9—3-[4-[3-[2-[2-[2-(2-Hydroxethoxy)ethoxy]ethoxy]ethoxy]propl]-3-methyl-2-oxo-benzimidazol-1-yl]piperidine-2,6-dione (15)

To a mixture of 3-[4-[3-[2-[2-[2-(2-hydroxyethoxy)ethoxy]ethoxy]ethoxy]prop-1-ynyl]-3-methyl-2-oxo-benzimidazol-1-yl]piperidine-2,6-dione (200 mg, 408 umol) in THF (10 mL) was added Pd/C (100 mg, 10% wt) and Pd(OH)$_2$/C (100 mg, 10% wt). The reaction mixture was stirred at 25° C. for 12 hours under H$_2$ (15 Psi) atmosphere. On completion, the reaction mixture was concentrated in vacuo to give the title compound (180 mg, 89% yield) as white solid which was used for the next step without purification. $^1$H NMR (400 MHz, DMSO-d$_6$) δ 11.09 (s, 1H), 6.96 (d, J=4.4 Hz, 2H), 6.90-6.86 (m, 1H), 5.36 (dd, J=5.2, 12.4 Hz, 1H), 4.57 (t, J=5.2 Hz, 1H), 4.03 (q, J=7.2 Hz, 1H), 3.56 (s, 3H), 3.52 (d, J=5.6 Hz, 10H), 3.48-3.45 (m, 4H), 3.40 (d, J=5.2 Hz, 2H), 2.98-2.93 (m, 2H), 2.89-2.84 (m, 1H), 2.72-2.63 (m, 2H), 2.61-2.58 (m, 2H), 2.02-1.96 (m, 2H), 1.85-1.81 (m, 1H); LC-MS (ESI$^+$) m/z 494.3 (M+H)$^+$.

Step 10—2-[2-[2-[2-[3-[1-(2,6-Dioxo-3-piperidyl)-3-methyl-2-oxo-benzimidazol-4-yl]propoxy]ethoxy]ethoxy]ethoxy]acetaldehyde (16)

To a mixture of 3-[4-[3-[2-[2-[2-(2-hydroxyethoxy)ethoxy]ethoxy]propyl]-3-methyl-2-oxo-benzimidazol-1-yl]piperidine-2,6-dione (180 mg, 364 umol) in THF (20 mL) was added DMP (309 mg, 729 umol). The reaction mixture was stirred at 25° C. for 1.5 hours. On completion, the reaction mixture was quenched by saturated Na$_2$S$_2$O$_3$ (15 mL) and saturated NaHCO$_3$ (15 mL) at 25° C., and then stirred for 30 minutes, then the organic layers were separated and concentrated in vacuo to give the title compound (179 mg, 100% yield) as a red oil. $^1$H NMR (400 MHz, DMSO-d$_6$) δ 11.07 (s, 1H), 9.56 (s, 1H), 6.96 (d, J=8.8 Hz, 2H), 6.88 (d, J=8.8 Hz, 1H), 5.41-5.31 (m, 1H), 4.16 (s, 2H), 3.60-3.43 (m, 15H), 3.01-2.92 (m, 2H), 2.90-2.84 (m, 1H), 2.74-2.54 (m, 4H), 2.04-1.96 (m, 1H), 1.85-1.81 (m, 2H). LC-MS (ESI$^+$) m/z 492.3 (M+H)$^+$.

Step 11—3-[3-Methyl-2-oxo-4-[3-[2-[2-[2-[2-[[4-[(5-tetrahydropyran-4-yl-7H-pyrrolo[2,3-d]pyrimidin-4-yl)amino]cyclohexyl]amino]ethoxy]ethoxy]ethoxy]propyl]benzimidazol-1-yl]piperidine-2,6-dione (I-442)

To a solution of N4-(5-tetrahydropyran-4-yl-7H-pyrrolo[2,3-d]pyrimidin-4-yl)cyclohexane-1,4-diamine (50.0 mg, 158 umol) and 2-[2-[2-[2-[3-[1-(2,6-dioxo-3-piperidyl)-3-methyl-2-oxo-benzimidazol-4-yl]propoxy]ethoxy]ethoxy]ethoxy]acetaldehyde (77.9 mg, 158 umol) in a mixed solvent of THF (5 mL) and DMF (1 mL) was added HOAc (9.52 mg, 158. umol) and NaBH(OAc)$_3$ (40.3 mg, 190 umol). The reaction mixture was stirred at 20° C. for 12 hrs. On completion, the reaction mixture was concentrated in vacuo. The crude product was purified by prep-HPLC (column: Phenomenex Synergi C18 150*25*10 um; mobile phase: [water (0.225% FA)-ACN]; B %: 13%-31%, 6 min) to give the title compound (11.0 mg, 8% yield) as white solid. $^1$H NMR (400 MHz, DMSO-d$_6$) δ 11.35 (s, 2H), 8.35 (s, 1H), 8.08 (s, 1H), 7.05-6.80 (m, 4H), 5.60 (d, J=7.6 Hz, 1H), 5.36 (dd, J=4.8, 12.0 Hz, 1H), 4.05 (s, 1H), 3.90 (d, J=8.4 Hz, 2H), 3.59-3.49 (m, 20H), 3.45 (t, J=5.6 Hz, 2H), 3.26-3.21 (m, 1H), 3.01-2.91 (m, 4H), 2.90-2.84 (m, 1H), 2.76-2.67 (m, 1H), 2.62 (m, 1H), 2.13-1.78 (m, 9H), 1.60-1.34 (m, 6H). LC-MS (ESI$^+$) m/z 791.5 (M+H)$^+$.

Example 438: 3-[3-Methyl-2-oxo-4-[3-[2-[2-[2-[2-oxo-2-[4-[4-[(5-tetrahydropyran-4-yl-7H-pyrrolo[2,3-d]pyrimidin-4-yl)amino]cyclohexyl]piperazin-1-yl]ethoxy]ethoxy]ethoxy]ethoxy]propyl]benzimidazol-1-yl]piperidine-2,6-dione (I-444)

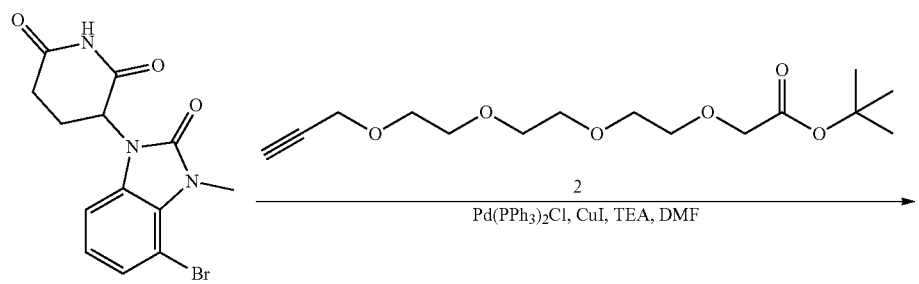

-continued
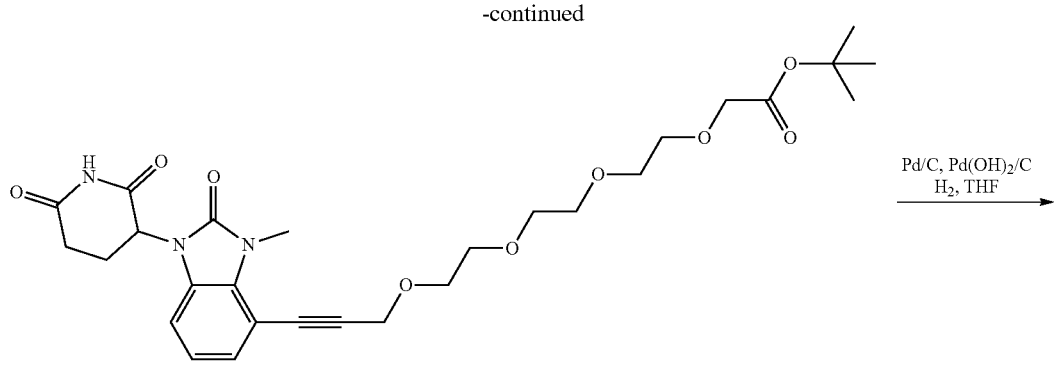
3
Pd/C, Pd(OH)₂/C
H₂, THF
→
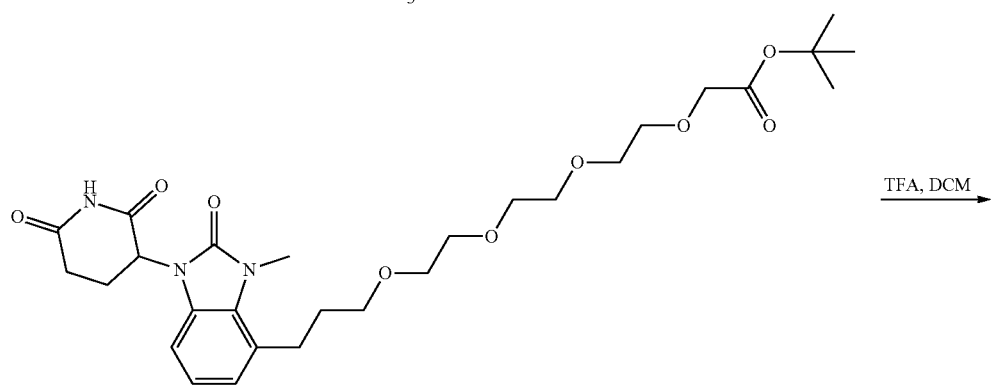
4
TFA, DCM
→
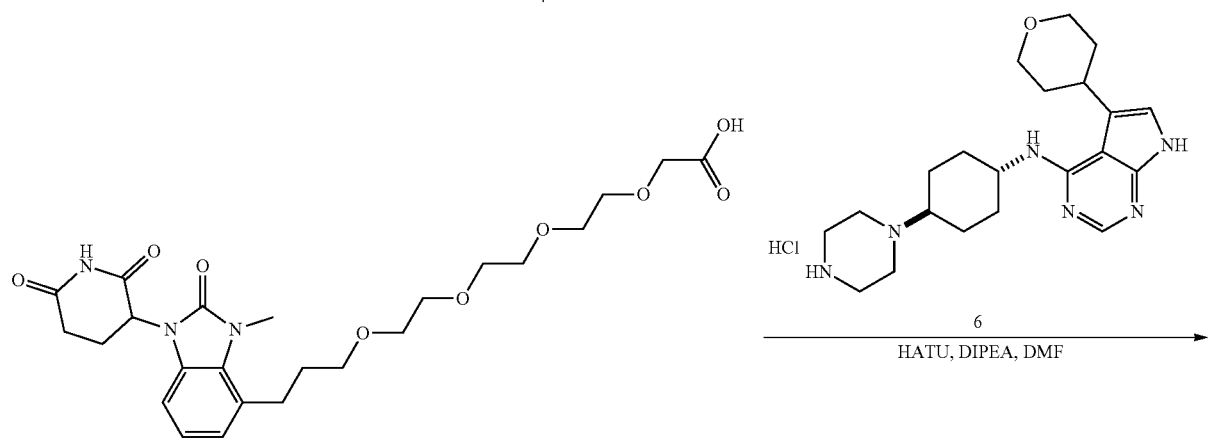
5
6
HATU, DIPEA, DMF
→
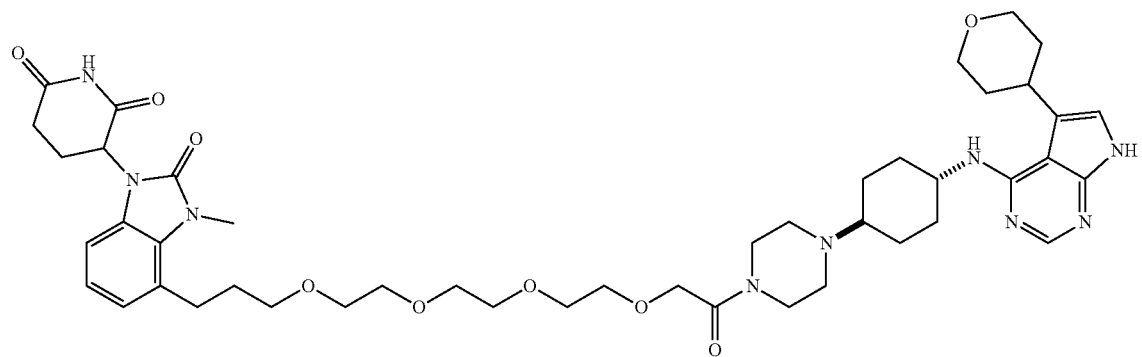
I-444

Step 1—Tert-butyl 2-[2-[2-[2-[3-[1-(2,6-dioxo-3-piperidyl)-3-methyl-2-oxo-benzimidazol-4-yl]prop-2-ynoxy]ethoxy]ethoxy]ethoxy]acetate (3)

To a mixture of 3-(4-bromo-3-methyl-2-oxo-benzimidazol-1-yl)piperidine-2,6-dione (600 mg, 1.77 mmol, Intermediate HP), tert-butyl 2-[2-[2-(2-prop-2-ynoxyethoxy)ethoxy]ethoxy]acetate (1.07 g, 3.55 mmol, from Example 441) in DMF (10 mL) was added CuI (67.6 mg, 355 umol), $Cs_2CO_3$ (2.89 g, 8.87 mmol) and $Pd(PPh_3)_2Cl_2$ (249 mg, 355 umol) under $N_2$. The reaction mixture was stirred at 80° C. for 3 hours. On completion, the mixture was poured into water (30 mL). The aqueous phase was extracted with ethyl acetate (2×30 mL). The combined organic phase was washed with brine (2×30 mL), dried with anhydrous $Na_2SO_4$, filtered and concentrated in vacuo to give a residue. The residue was purified by reversed-phase (0.1% FA condition) to give the title compound (598 mg, 60% yield) as brown oil. $^1$H NMR (400 MHz, $CDCl_3$) δ 8.29 (s, 1H), 7.16 (d, J=7.6 Hz, 1H), 6.97 (t, J=8.0 Hz, 1H), 6.75 (d, J=8.0 Hz, 1H), 5.23-5.15 (m, 1H), 4.46 (s, 2H), 4.01 (s, 2H), 3.76 (s, 3H), 3.76-3.66 (m, 12H), 2.99-2.68 (m, 3H), 2.29-2.16 (m, 1H), 1.46 (s, 9H).

Step 2—Tert-butyl 2-[2-[2-[2-[3-[1-(2,6-dioxo-3-piperidyl)-3-methyl-2-oxo-benzimidazol-4-yl]propoxy]ethoxy]ethoxy]ethoxy]acetate (4)

To a solution of tert-butyl 2-[2-[2-[2-[3-[1-(2,6-dioxo-3-piperidyl)-3-methyl-2-oxo-benzimidazol-4-yl]prop-2-ynoxy]ethoxy]ethoxy]ethoxy]acetate (578 mg, 1.03 mmol) in THF (5 mL) was added Pd/C (100 mg, 20% purity) and $Pd(OH)_2/C$ (100 mg, 20% purity) under $N_2$. The suspension was degassed under vacuum and purged with $H_2$ 3 times. The mixture was stirred at 20° C. for 12 hours under $H_2$ (15 psi). On completion, the mixture was concentrated in vacuo to give a title compound (540 mg, 92% yield) as brown oil. LC-MS (ESI$^+$) m/z 586.3 (M+Na)$^+$.

Step 3—2-[2-[2-[2-[3-[1-(2,6-Dioxo-3-piperidyl)-3-methyl-2-oxo-benzimidazol-4-yl]propoxy]ethoxy]ethoxy]ethoxy]acetic acid (5)

To a mixture of tert-butyl 2-[2-[2-[2-[3-[1-(2,6-dioxo-3-piperidyl)-3-methyl-2-oxo-benzimidazol-4-yl]propoxy]ethoxy]ethoxy]ethoxy]acetate (520 mg, 922 umol) in DCM (2 mL) was added TFA (210 mg, 1.85 mmol). The reaction mixture was stirred at 20° C. for 1 hour. On completion, the mixture was concentrated in vacuo to give a residue. The residue was purified by column chromatography to give the title compound (436 mg, 93% yield) as brown oil. LC-MS (ESI$^+$) m/z 508.3 (M+H)$^+$.

Step 4—3-[3-Methyl-2-oxo-4-[3-[2-[2-[2-[2-oxo-2-[4-[4-[(5-tetrahydropyran-4-yl-7H-pyrrolo[2,3-d]pyrimidin-4-yl)amino]cyclohexyl]piperazin-1-yl]ethoxy]ethoxy]ethoxy]ethoxy]propyl]benzimidazol-1-yl]piperidine-2,6-dione (I-444)

To a mixture of 2-[2-[2-[2-[3-[1-(2,6-dioxo-3-piperidyl)-3-methyl-2-oxo-benzimidazol-4-yl]propoxy]ethoxy]ethoxy]ethoxy]acetic acid (39.6 mg, 78.0 umol), N-(4-piperazin-1-ylcyclohexyl)-5-tetra hydropyran-4-yl-7H-pyrrolo[2,3-d]pyrimidin-4-amine (30.0 mg, 78.0 umol, Intermediate OP) in DMF (1.5 mL) was added DIEA (30.2 mg, 234 umol) and HATU (35.6 mg, 93.6 umol). The reaction mixture was stirred at 20° C. for 1 hr. On completion, water (1.5 mL) was added into the reaction mixture and the mixture was concentrated in vacuo to give a residue. The residue was purified by prep-HPLC (column: Phenomenex Synergi C18 150*25*10 um; mobile phase: [water (0.05% HCl)-ACN]; B %: 7%-27%) to give the title compound (2.00 mg, 2% yield) as a white solid. $^1$H NMR (400 MHz, DMSO-$d_6$) δ 11.08 (s, 1H), 9.07 (s, 1H), 8.10 (s, 1H), 7.07-6.80 (m, 4H), 5.36 (d, J=5.2, 12.4 Hz, 1H), 4.18 (s, 2H), 3.90 (d, J=10.4 Hz, 2H), 3.66-3.50 (m, 22H), 3.48-3.40 (m, 6H), 3.17-3.06 (m, 4H), 3.00-2.83 (m, 5H), 2.75-2.56 (m, 3H), 2.25-1.94 (m, 4H), 1.84 (d, J=8.0 Hz, 4H), 1.60-1.46 (m, 4H); LC-MS (ESI$^+$) m/z 874.5 (M+H)$^+$.

Example 439: N-[3-(difluoromethyl)-1-[4-[4-[1-(2,6-dioxo-3-piperidyl)-3-methyl-2-oxo-benzimidazol-5-yl]butoxyl butyl]carbamoyl]phenyl]pyrazol-4-yl]-5-piperazin-1-yl-pyrazolo[1,5-a]pyrimidine-3-carboxamide (I-445)

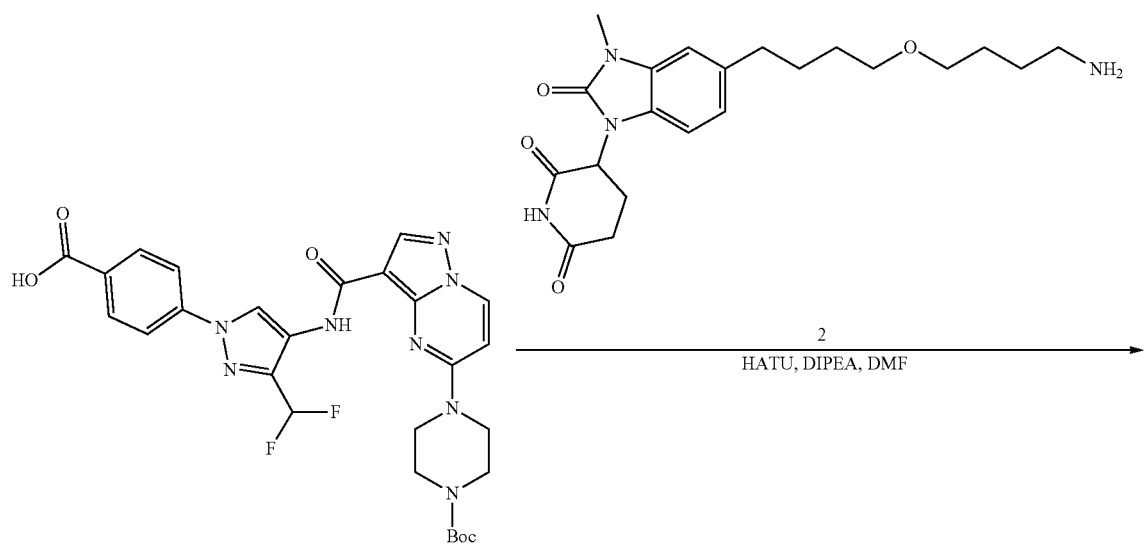

-continued

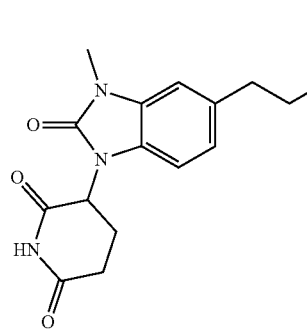
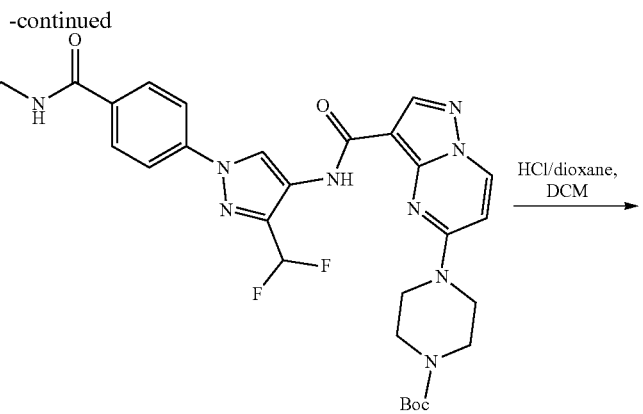

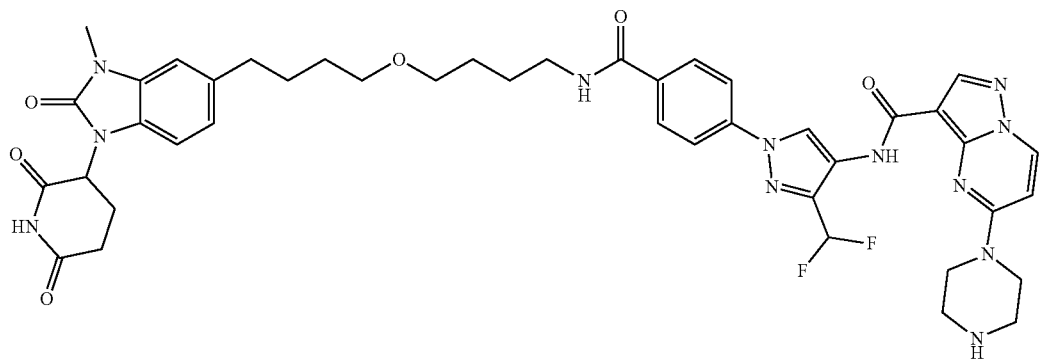

I-445

Step 1—Tert-butyl 4-[3-[[3-(difluoromethyl)-1-[4-[4-[4-[1-(2,6-dioxo-3-piperidyl)-3-methyl-2-oxo-benzimidazol-5-yl]butoxy]butylcarbamoyl]phenyl]pyrazol-4-yl]carbamoyl]pyrazolo[1,5-a]pyrimidin-5-yl]piperazine-1-carboxylate (3)

To a solution of 4-[4-[[5-(4-tert-butoxycarbonylpiperazin-1-yl)pyrazolo[1,5-a]pyrimidine-3-carbonyl]amino]-3-(difluoromethyl)pyrazol-1-yl]benzoic acid (66.3 mg, 113 umol, from Example 436), 3-[5-[4-(4-aminobutoxy)butyl]-3-methyl-2-oxobenzimidazol-1-yl]piperidine-2,6-dione (50.0 mg, 113 umol, HCl, Intermediate OD) in DMF (3.00 mL) was added HATU (51.9 mg, 136 umol) and DIEA (73.6 mg, 569 umol). The mixture was stirred at 20° C. for 0.5 hr. On completion, the mixture was diluted with H₂O (15 mL), filtered and the filter cake was concentrated in vacuo to give the title compound (90.0 mg, 81% yield) as yellow solid. LC-MS (ESI⁺) m/z 967.4 (M+H)⁺.

Step 2—N-[3-(difluoromethyl)-1-[4-[4-[4-[1-(2,6-dioxo-3-piperidyl)-3-methyl-2-oxo-benzimidazol-5-yl]butoxy]butyl]carbamoyl]phenyl]pyrazol-4-yl]-5-piperazin-1-yl-pyrazolo[1,5-a]pyrimidine-3-carboxamide (I-445)

To a solution of tert-butyl 4-[3-[[3-(difluoromethyl)-1-[4-[4-[4-[1-(2,6-dioxo-3-piperidyl)-3-methyl-2-oxo-benzimidazol-5-yl]butoxy]butyl]carbamoyl]phenyl]pyrazol-4-yl]carbamoyl]pyrazolo[1,5-a]pyrimidin-5-yl]piperazine-1-carboxylate (150 mg, 155 umol) in DCM (5.00 mL) was added HCl/dioxane (4 M, 7.50 mL). The mixture was stirred at 20° C. for 0.5 hr. On completion, the mixture was concentrated in vacuo. The mixture was purified by prep-HPLC (column: Phenomenex Synergi C18 150*25*10 um; mobile phase: [water (0.225% FA)-ACN]; B %: 17%-41%, 8 min) to give the title compound (67.5 mg, 49% yield) as off-white solid. ¹H NMR (400 MHz, DMSO-d₆) δ 11.07 (s, 1H), 9.53 (s, 1H), 9.10 (s, 1H), 8.79 (d, J=8.0 Hz, 1H), 8.56 (t, J=5.6 Hz, 1H), 8.32 (s, 1H), 8.26 (s, 1H), 8.04-7.98 (m, 2H), 7.97-7.92 (m, 2H), 7.31 (t, J=5.6 Hz, 1H), 7.02 (s, 1H), 7.00 (d, J=8.0 Hz, 1H), 6.91 (d, J=8.0 Hz, 1H), 6.88-6.83 (m, 1H), 5.37-5.28 (m, 1H), 3.77-3.70 (m, 4H), 3.33-3.29 (m, 9H), 2.93-2.88 (m, 1H), 2.86-2.83 (m, 4H), 2.75-2.68 (m, 1H), 2.65-2.62 (m, 2H), 2.61-2.57 (m, 1H), 2.06-1.97 (m, 1H), 1.64-1.52 (m, 8H); LC-MS (ESI$^+$) m/z 867.3 (M+H)$^+$.

Example 440: N-[3-(difluoromethyl)-1-[4-[[2-[2-[3-[1-(2,6-dioxo-3-piperidyl)-3-methyl-2-oxo-benzimidazol-4-yl]propoxy]ethoxy]ethylamino]methyl]phenyl]pyrazol-4-yl]-5-piperazin-1-yl-pyrazolo[1,5-a]pyrimidine-3-carboxamide (I-446)

Step 1—Tert-butyl 4-[3-[[3-(difluoromethyl)-1-[4-[[2-[2-[3-[1-(2,6-dioxo-3-piperidyl)-3-methyl-2-oxo-benzimidazol-4-yl]propoxy]ethoxy]ethylamino]methyl]phenyl]pyrazol-4-yl]carbamoyl]pyrazolo[1,5-a]pyrimidin-5-yl]piperazine-1-carboxylate (3)

To a solution of tert-butyl 4-[3-[[3-(difluoromethyl)-1-(4-formylphenyl)pyrazol-4-yl]carbamoyl]pyrazolo[1,5-a]pyrimidin-5-yl]piperazine-1-carboxylate (128 mg, 226 umol, from Example 436), 3-[4-[3-[2-(2-aminoethoxy)ethoxy]propyl]-3-methyl-2-oxobenzimidazol-1-yl]piperidine-2,6-di-

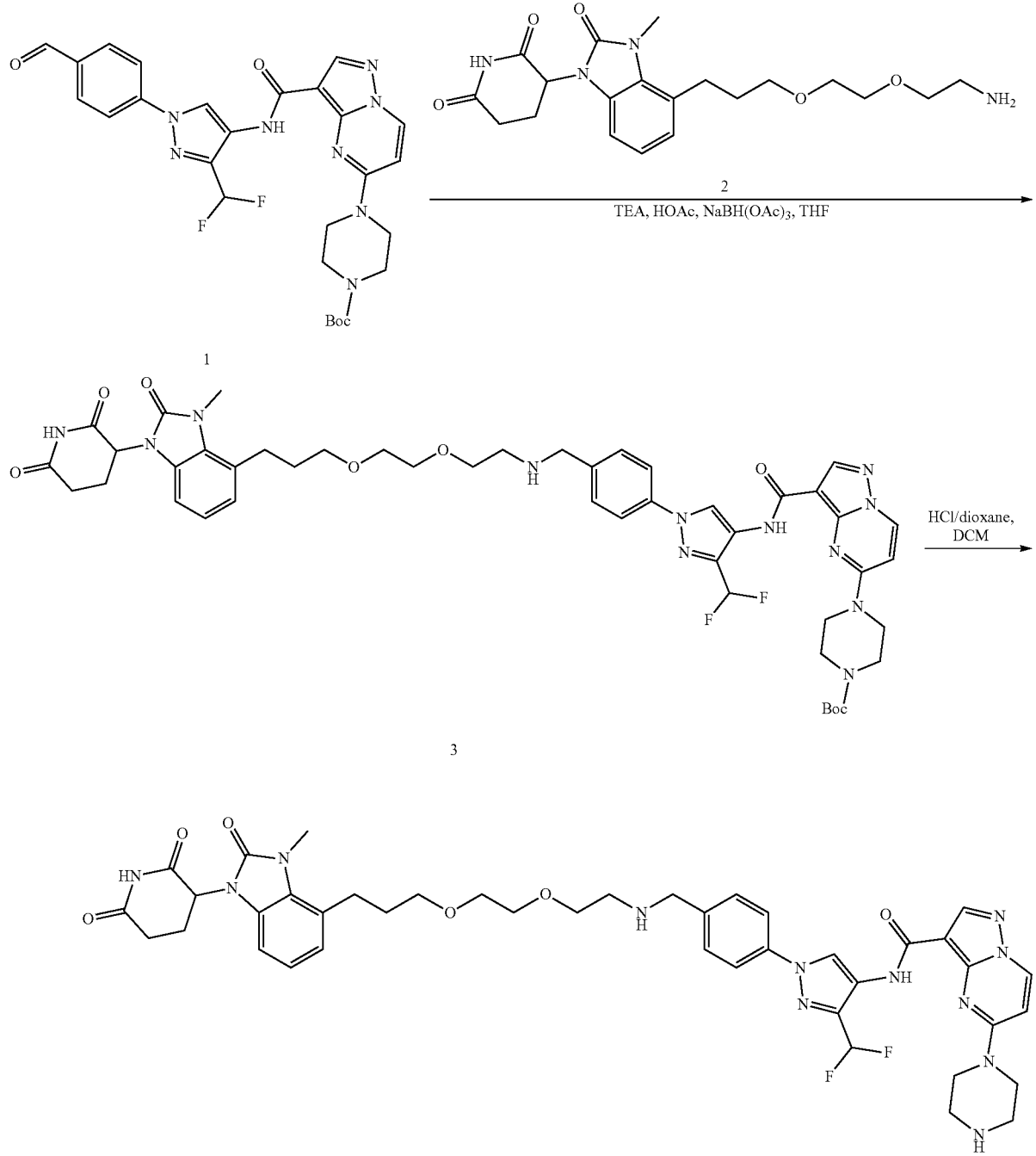

I-446 one (100 mg, 226 umol, HCl, from Intermediate IQ) in THF (20.0 mL) was added TEA (45.9 mg, 453 umol) and HOAc (40.8 mg, 680 umol). The mixture was stirred at 20° C. for 0.5 hr, then NaBH(OAc)$_3$ (144 mg, 680 umol) was added. The mixture was stirred at 20° C. for 16 hrs. On completion, the mixture was diluted with H$_2$O (2.00 mL). The mixture was concentrated in vacuo. The mixture was purified by reverse phase column (0.1% FA) to give the title compound (180 mg, 83% yield) as yellow solid. LC-MS (ESI$^+$) m/z 955.3 (M+H)$^+$.

Step 2—N-[3-(difluoromethyl)-1-[4-[[2-[2-[3-[1-(2,6-dioxo-3-piperidyl)-3-methyl-2-oxo-benzimidazol-4-yl]propoxy]ethoxy]ethylamino]methyl]phenyl]pyrazol-4-yl]-5-piperazin-1-yl-pyrazolo[1,5-a]pyrimidine-3-carboxamide (I-446)

To a solution of tert-butyl 4-[3-[[3-(difluoromethyl)-1-[4-[[2-[2-[3-[1-(2,6-dioxo-3-piperidyl)-3-methyl-2-oxo-benzimidazol-4-yl]propoxy]ethoxy]ethylamino]methyl]phenyl]pyrazol-4-yl]carbamoyl]pyrazolo[1,5-a]pyrimidin-5-yl]piperazine-1-carboxylate (180 mg, 188 umol) in DCM (2 mL) was added HCl/dioxane (4 M, 6 mL). The mixture was stirred at 20° C. for 0.5 hr. On completion, the mixture was concentrated in vacuo. The mixture was purified by prep-HPLC (column: Phenomenex Synergi C18 150*25*10 um; mobile phase: [water (0.225% FA)-ACN]; B %: 12%-33%, 7 min) to give the title compound (89.5 mg, 53% yield) as white solid. $^1$H NMR (400 MHz, DMSO-d$_6$) δ 11.10 (s, 1H), 9.50 (s, 1H), 9.50 (s, 1H), 8.98 (s, 1H), 8.82 (d, J=8.0 Hz, 1H), 8.33 (s, 1H), 8.23 (s, 1H), 7.79 (d, J=8.4 Hz, 2H), 7.51 (d, J=8.4 Hz, 2H), 7.29 (t, J=54 Hz, 1H), 6.95 (d, J=6.4 Hz, 2H), 6.92 (s, 1H), 6.88-6.83 (m, 1H), 5.43-5.29 (m, 1H), 3.89 (s, 3H), 3.84 (s, 4H), 3.59-3.54 (m, 8H), 3.49-3.44 (m, 2H), 2.94 (s, 4H), 2.94-2.91 (m, 2H), 2.91-2.85 (m, 1H), 2.83-2.77 (m, 2H), 2.76-2.66 (m, 1H), 2.66-2.58 (m, 1H), 2.04-1.94 (m, 1H), 1.89-1.76 (m, 2H); LC-MS (ESI$^+$) m/z 855.5 (M+H)$^+$.

Example 441: 3-[3-Methyl-2-oxo-5-[3-[2-[2-[2-[2-oxo-2-[4-[4-[(5-tetrahydropyran-4-yl-7H-pyrrolo[2,3-d]pyrimidin-4-yl)amino]cyclohexyl]piperazin-1-yl]ethoxy]ethoxy]ethoxy]propyl]benzimidazol-1-yl]piperidine-2,6-dione (I-447)

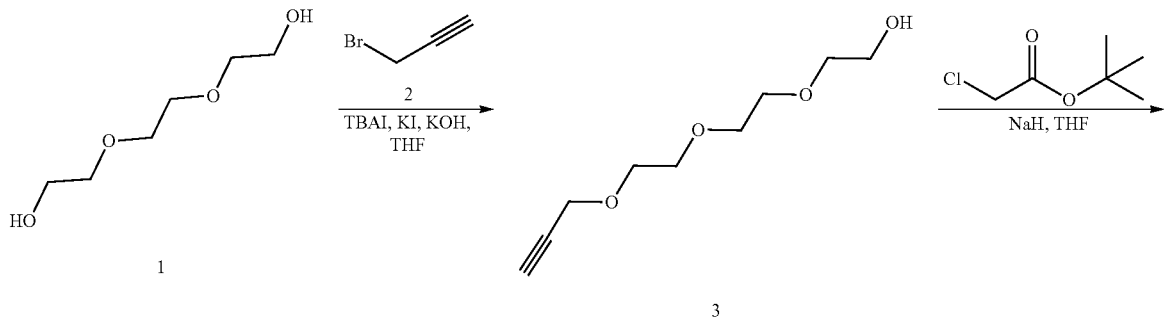

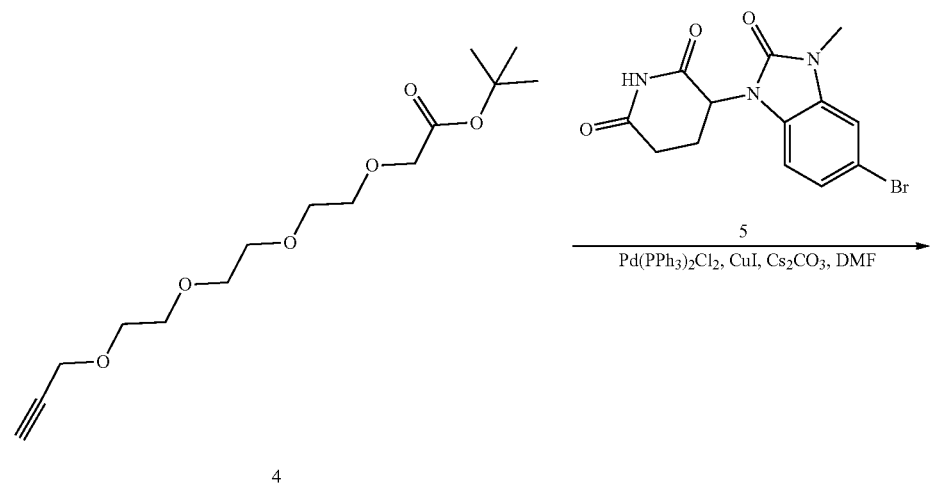

-continued
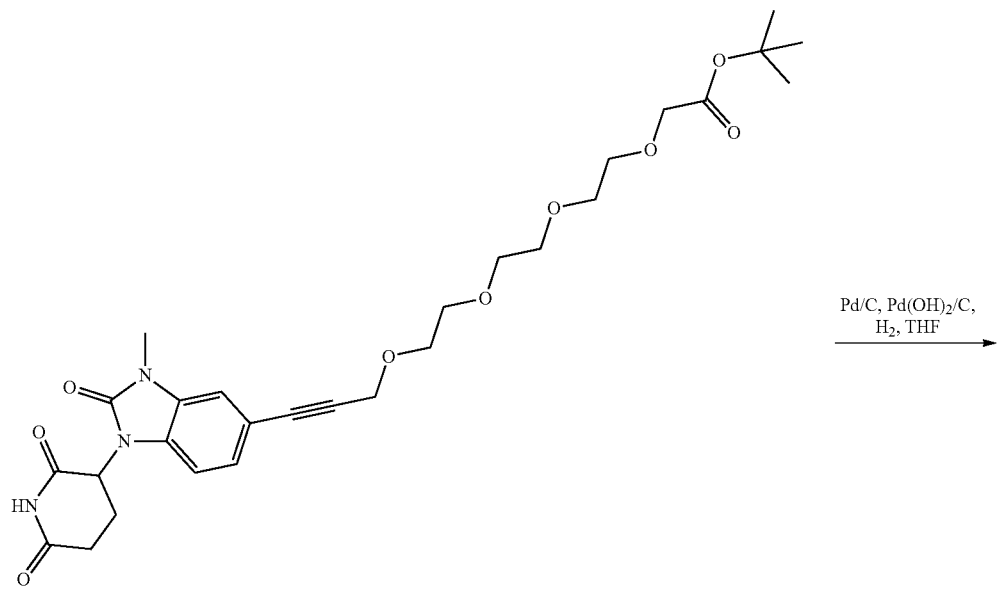
6
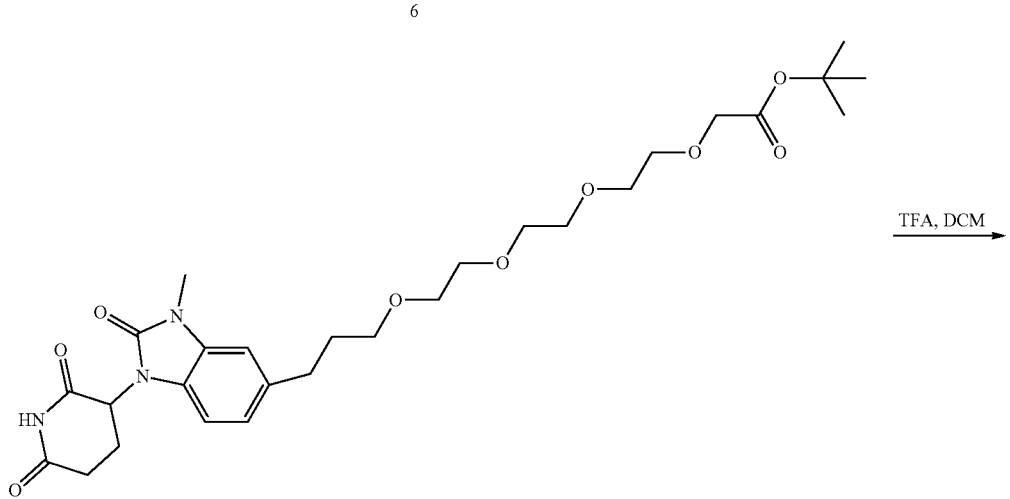
7
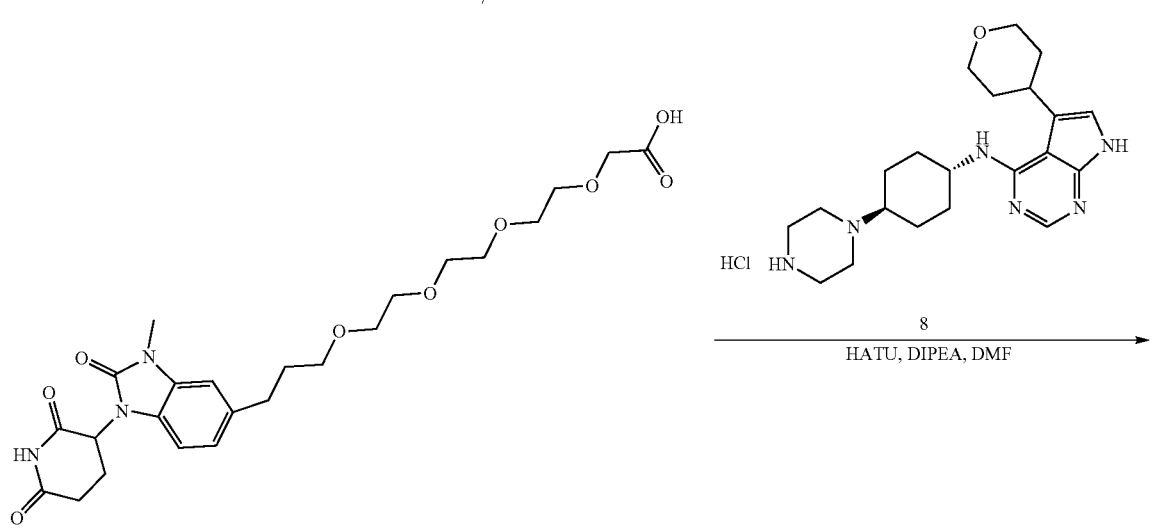

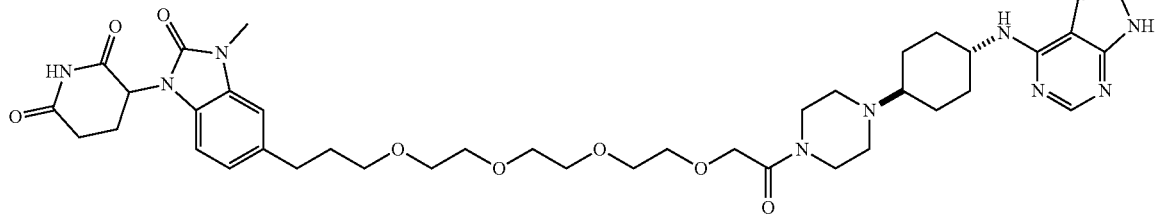

I-447

Step 1—2-[2-(2-Prop-2-ynoxyethoxy)ethoxy]ethanol (3)

To a solution of 2-[2-(2-hydroxyethoxy)ethoxy]ethanol (10.0 g, 66.5 mmol, 8.93 mL/C, CAS #112-27-6) and 3-bromoprop-1-yne (7.92 g, 66.5 mmol, 5.74 mL, CAS #106-96-7) in THF (100 mL) was added KI (1.66 g, 9.99 mmol), TBAI (1.48 g, 4.00 mmol) and KOH (3.74 g, 66.5 mmol). The reaction mixture was stirred at 25° C. for 16 hrs. On completion, the mixture was filtered, and the filtrate was concentrated in vacuo to give a residue, the residue was diluted with $H_2O$ (50 mL), and then extracted with EA (2×80 mL), the organic phase was concentrated in vacuo to give a residue. The residue was purified by column chromatography to give the title compound (10.0 g, 79% yield) as yellow oil. 1H NMR (400 MHz, CDCl3) δ 4.19-4.12 (m, 2H), 3.74-3.57 (m, 10H), 3.57-3.52 (m, 2H), 2.42 (s, 1H), 2.38 (t, J=2.4 Hz, 1H).

Step 2—Tert-butyl 2-[2-[2-(2-prop-2-ynoxyethoxy)ethoxy]ethoxy]acetate (5)

To a solution of 2-[2-(2-prop-2-ynoxyethoxy)ethoxy]ethanol (4.0 g, 21.25 mmol) in THF (50 mL) was added NaH (1.28 g, 31.8 mmol, 60% purity) at 0° C., the mixture was stirred at 25° C. for 30 min, then tert-butyl 2-chloroacetate (6.40 g, 42.5 mmol, 6.10 mL, CAS #107-59-5) was added to the mixture, the reaction mixture was stirred at 25° C. for 12 hrs. On completion, the reaction mixture was quenched by $H_2O$ (50 mL), and extracted with EA (2×100 mL). The organic phase was concentrated in vacuo to give a residue. The residue was purified by column chromatography to give the title compound (3.60 g, 56% yield) as yellow oil. $^1H$ NMR (400 MHz, $CDCl_3$) δ 4.20 (d, J=2.4 Hz, 2H), 4.01 (s, 2H), 3.72-3.65 (m, 12H), 2.42 (t, J=2.4 Hz, 1H), 1.47 (s, 9H).

Step 3—Tert-butyl 2-[2-[2-[2-[3-[1-(2,6-dioxo-3-piperidyl)-3-methyl-2-oxo-benzimidazol-5-yl]prop-2-ynoxy]ethoxy]ethoxy]ethoxy]acetate (6)

To a solution of tert-butyl 2-[2-[2-(2-prop-2-ynoxyethoxy)ethoxy]ethoxy]acetate (1.16 g, 3.84 mmol) and 3-(5-bromo-3-methyl-2-oxo-benzimidazol-1-yl)piperidine-2,6-dione (650 mg, 1.92 mmol, Intermediate HN) in DMF (10 mL) was added CuI (73.2 mg, 384 umol), $Pd(PPh_3)_2Cl_2$ (269 mg, 384 umol) and $Cs_2CO_3$ (3.13 g, 9.61 mmol). The reaction mixture was stirred at 80° C. for 2 hrs under $N_2$. On completion, the mixture was filtered and the filtrate was concentrated in vacuo to give a residue. The residue was purified by reverse phase (0.1% FA condition) to give the title compound (550 mg, 51% yield) as a yellow solid. $^1H$ NMR (400 MHz, DMSO-$d_6$) δ 11.11 (s, 1H), 7.33 (s, 1H), 7.21-7.09 (m, 2H), 5.39 (dd, J=5.2, 12.8 Hz, 1H), 4.39 (s, 2H), 3.97 (s, 2H), 3.68-3.61 (m, 2H), 3.59-3.52 (m, 10H), 3.34 (s, 3H), 2.97-2.82 (m, 1H), 2.76-2.57 (m, 2H), 2.06-2.00 (m, 1H), 1.41 (s, 9H); LC-MS (ESI$^+$) m/z 582.3 (M+Na)$^+$.

Step 4—Tert-butyl 2-[2-[2-[2-[3-[1-(2,6-dioxo-3-piperidyl)-3-methyl-2-oxo-benzimidazol-5-yl]propoxy]ethoxy]ethoxy]ethoxy]acetate (7)

To a solution of tert-butyl 2-[2-[2-[2-[3-[1-(2,6-dioxo-3-piperidyl)-3-methyl-2-oxo-benzimidazol-5-yl]prop-2-ynoxy]ethoxy]ethoxy]ethoxy]acetate (550 mg, 982 umol) in THF (20 mL) was added Pd(OH)$_2$/C (250 mg, 915 umol, 10% purity) and Pd/C (250 mg, 915 umol, 10% purity), the reaction mixture was stirred at 25° C. for 12 hrs under $H_2$ (15 Psi). On completion, the residue was filtered and the filtrate was concentrated in vacuo to give the title compound (500 mg, 90% yield) as a white solid. LC-MS (ESI$^+$) m/z 508.2 (M+H-56)$^+$.

Step 5—2-[2-[2-[2-[3-[1-(2,6-Dioxo-3-piperidyl)-3-methyl-2-oxo-benzimidazol-5-yl]propoxy]ethoxy]ethoxy]ethoxy]acetic acid To a solution of tert-butyl 2-[2-[2-[2-[3-[1-(2,6-dioxo-3-piperidyl)-3-methyl-2-oxo-benzimidazol-5-yl]propoxy]ethoxy]ethoxy]ethoxy]acetate (100 mg, 177 umol) in DCM (3 mL) was added TFA (1.54 g, 13.5 mmol, 1 mL), the reaction mixture was stirred at 25° C. for 12 hrs. On completion, the mixture was concentrated in vacuo to give the title compound (110 mg, 95% yield) as colorless oil. LC-MS (ESI$^+$) m/z 508.3 (M+H)$^+$.

Step 6—3-[3-Methyl-2-oxo-5-[3-[2-[2-[2-[2-oxo-2-[4-[4-[(5-tetrahydropyran-4-yl-7H-pyrrolo[2,3-d]pyrimidin-4-yl)amino]cyclohexyl]piperazin-1-yl]ethoxy]ethoxy]ethoxy]ethoxy]propyl]benzimidazol-1-yl]piperidine-2,6-dione (I-447)

To a solution of 2-[2-[2-[2-[3-[1-(2,6-dioxo-3-piperidyl)-3-methyl-2-oxo-benzimidazol-5-yl]propoxy]ethoxy]ethoxy]ethoxy]acetic acid (15.0 mg, 24.1 umol) and N-(4-piperazin-1-ylcyclohexyl)-5-tetrahydropyran-4-yl-7H-pyrrolo[2,3-d]pyrimidin-4-amine (9.28 mg, 24.1 umol, Intermediate OP) in DMF (5 mL) was DIPEA (15.5 mg, 120 umol, 21.0 uL) and HATU (11.0 mg, 28.9 umol). The mixture was stirred at 25° C. for 1.5 hrs. On completion, the mixture was quenched with H₂O (5 mL), then concentrated in vacuo to give a residue. The residue was purified by prep-HPLC (column: Phenomenex Synergi C18 150*25*10 um; mobile phase: [water (0.225% FA)-ACN]; B %: 8%-32%, 8 min) to give the title compound (6.09 mg, 28% yield) as a white solid. $^1$H NMR (400 MHz, DMSO-d$_6$) δ 11.29 (s, 1H), 11.07 (s, 1H), 8.06 (s, 1H), 7.05-6.96 (m, 2H), 6.92-6.78 (m, 2H), 5.51 (d, J=8.0 Hz, 1H), 5.32 (dd, J=5.2, 12.8 Hz, 1H), 4.12 (s, 2H), 4.08-3.98 (m, 1H), 3.94-3.85 (m, 2H), 3.61-3.45 (m, 18H), 3.31 (s, 3H), 3.29-3.18 (m, 3H), 2.92-2.84 (m, 1H), 2.71-2.57 (m, 4H), 2.49-2.39 (m, 4H), 2.36-2.28 (m, 1H), 2.07-1.94 (m, 3H), 1.89-1.69 (m, 6H), 1.63-1.28 (m, 6H); LC-MS (ESI+) m/z 874.5 (M+H)⁺.

TABLE 23

Compounds synthesized via Method 12 with the coupling of various amines and acids in Step 1.

| Ex-#$^a$ | I-# | Step 1 Intermediate Amine | Step 1 Intermediate Acid | LCMS (ES+) m/z (M + H)⁺ | $^1$HNMR (400 MHz, DMSO-d$_6$) δ |
|---|---|---|---|---|---|
| 443 | I-448 | UD | OM | 928.6 | 11.05 (s, 1H), 10.98 (s, 1H), 8.99 (s, 1H), 8.95 (s, 1H), 8.16 (d, J = 5.2 Hz, 1H), 8.05-7.98 (m, 3H), 7.74 (s, 1H), 7.64 (d, J = 8.0 Hz, 2H), 7.18-7.10 (m, 2H), 7.02-6.95 (m, 3H), 6.83 (d, J = 8.0 Hz, 1H), 5.35-5.27 (m, 1H), 4.65-4.55 (m, 1H), 4.36 (s, 1H), 3.52-3.45 (m, 8H), 3.29 (s, 3H), 3.21-3.17 (m, 2H), 2.91-2.80 (m, 2H), 2.68-2.61 (m, 5H), 2.03-1.94 (m, 1H), 1.85-1.74 (m, 2H), 0.50-0.42 (m, 2H), 0.27-0.20 (m, 2H) |
| 444 | I-449 | UE | KR | 929.1 | 11.09 (s, 1H), 10.82 (s, 1H), 9.02 (s, 1H), 8.44-8.38 (m, 2H), 8.25-8.23 (m, 2H), 7.56 (dd, J = 7.2 Hz, J = 8.4 Hz, 1H), 7.41 (s, 1H), 7.25 (d, J = 5.6 Hz, 1H), 7.11 (d, J = 8.4 Hz, 1H), 7.01 (d, J = 6.8 Hz, 1H), 6.58 (bs, 1H), 5.06-5.03 (m, 1H), 4.37-4.36 (m, 2H), 3.93-3.91 (m, 6H), 3.53-3.44 (m, 22H), 2.88 (m, 1H), 2.60-2.54 (m, 2H), 2.03-2.01 (m, 1H) |
| 450 | I-455 | UX | KR | 885.4 | 11.07 (s, 1H), 10.81 (s, 1H), 8.97 (s, 1H), 8.46 (s, 1H), 8.38 (s, 1H), 8.26-8.21 (m, 2H), 7.69 (t, J = 5.6 Hz, 1H), 7.25 (s, 1H), 7.16 (d, J = 5.2 Hz, 1H), 6.94 (d, J = 5.6 Hz, 1H), 6.84 (d, J = 8.8 Hz, 1H), 5.41-5.30 (M, 1H), 4.27-4.21 (m, 2H), 3.93 (s, 3H), 3.55-3.41 (m, 21H), 2.98-2.82 (m, 3H), 2.63 (s, 1H), 2.60-2.57 (m, 1H), 2.02-1.95 (m, 1H), 1.85-1.74 (m, 2H) |
| 451 | I-456 | VA | KR | 855.4 | 11.08 (s, 1H), 11.03 (s, 1H), 8.96 (s, 1H), 8.41 (s, 1H), 8.25 (d, J = 5.2 Hz, 1H), 7.70-7.62 (m, 1H), 7.58-7.53 (m, 1H), 7.24 (s, 1H), 7.16 (d, J = 4.8 Hz, 1H), 7.10 (d, J = 8.4 Hz, 1H), 7.02 (d, J = 6.8 Hz, 1H), 6.61-6.53 (m, 1H), 5.10-5.00 (m, 1H), 4.27-4.20 (m, 2H), 3.93 (s, 3H), 3.69-3.41 (m, 16H), 3.28 (s, 3H), 2.93-2.82 (m, 1H), 2.63-2.57 (m, 1H), 2.57-2.55 (m, 1H), 2.07-1.97 (m, 1H) |
| 452 | I-457 | VK | KR | 968.4 | 11.09 (s, 1H), 10.85 (s, 1H), 8.97 (s, 1H), 8.38 (s, 1H), 8.26-8.18 (m, 2H), 7.68 (t, J = 6.4 Hz, 1H), 7.25 (s, 1H), 7.17 (d, J = 5.2 Hz, 1H), 7.00-6.92 (m, 2H), 6.90-6.83 (m, 1H), 5.36 (dd, J = 5.2, 12.8 Hz, 1H), 4.31-4.19 (m, 2H), 3.93 (s, 3H), 3.89-3.82 (m, 1H), 3.57-3.50 (m, 19H), 2.98-2.86 (m, 5H), 2.73-2.59 (m, 2H), 2.50-2.46 (m, 2H), |

TABLE 23-continued

Compounds synthesized via Method 12 with the coupling of various amines and acids in Step 1.

| Ex-#[a] | I-# | Step 1 Intermediate Amine | Step 1 Intermediate Acid | LCMS (ES+) m/z (M + H)+ | $^1$HNMR (400 MHz, DMSO-$d_6$) δ |
|---|---|---|---|---|---|
| 453 | I-458 | VO | FX | 924.5 | 2.11-1.95 (m, 3H), 1.88-1.78 (m, 2H), 1.73-1.64 (m, 4H) 10.97 (s, 1H), 10.03 (s, 1H), 8.98 (s, 1H), 8.92 (s, 1H), 8.65 (s, 1H), 8.41 (s, 1H), 8.16 (d, J = 5.6 Hz, 1H), 8.03-7.97 (m, 4H), 7.66 (d, J = 7.6 Hz, 1H), 7.44 (s, 1H), 7.38 (d, J = 8.0 Hz, 1H), 7.33-7.10 (m, 2H), 7.07-7.04 (m, 1H), 6.57 (s, 1H), 6.04 (s, 1H), 5.15-5.06 (m, 1H), 4.42-4.29 (m, 4H), 3.57-3.55 (m, 4H), 3.47-3.40 (m, 8H), 3.21-3.18 (m, 2H), 2.96-2.85 (m, 1H), 2.64-2.55 (m, 1H), 2.42-2.38 (m, 1H), 2.01-1.97 (m, 1H), 1.12-1.05 (m, 1H), 0.49-0.44 (m, 2H), 0.25-0.22 (m, 2H) |
| 454 | I-459 | LG | FX | 851.1 | 11.07 (s, 1H), 10.02 (s, 1H), 8.98 (s, 1H), 8.92 (s, 1H), 8.57 (t, J = 5.2 Hz, 1H), 8.16 (d, J = 5.2 Hz, 1H), 8.03-7.96 (m, 4H), 7.32 (t, J = 53.6 Hz, 1H), 7.12 (s, 1H), 7.08 (t, J = 5.6 Hz, 1H), 7.06-7.02 (m, 2H), 7.01-6.97 (m, 1H), 6.90-6.85 (m, 1H), 5.33 (dd, J = 5.6, 12.8 Hz, 1H), 3.45 (t, J = 6.0 Hz, 2H), 3.41-3.35 (m, 4H), 3.31-3.31 (m, 3H), 3.19 (t, J = 6.0 Hz, 2H), 2.94-2.84 (m, 1H), 2.71-2.57 (m, 4H), 2.03-1.96 (m, 1H), 1.87-1.76 (m, 4H), 1.12-1.02 (m, 1H), 0.49-0.43 (m, 2H), 0.26-0.19 (m, 2H) |
| 455 | I-460 | LF | FX | 851.5 | 10.84 (s, 1H), 9.79 (s, 1H), 8.74 (s, 1H), 8.68 (s, 1H), 8.34 (d, J = 5.6 Hz, 1H), 7.93 (d, J = 5.2 Hz, 1H), 7.83-7.64 (m, 4H), 7.26-6.94 (m, 1H), 6.89 (s, 1H), 6.87-6.80 (m, 2H), 6.75-6.70 (m, 2H), 6.65-6.61 (m, 1H), 5.15-5.10 (m, 1H), 3.34 (s, 3H), 3.23 (d, J = 6.4 Hz, 6H), 2.95 (d, J = 6.4 Hz, 2H), 2.77-2.70 (m, 2H), 2.47-2.39 (m, 2H), 2.11-2.07 (m, 1H), 1.80-1.72 (m, 1H), 1.65-1.54 (m, 4H), 0.87-0.80 (m, 1H), 0.25-0.19 (m, 2H), 0.02-0.04 (m, 2H) |
| 456 | I-461 | VR | VQ | 882.4 | 11.06 (s, 1H), 10.07 (s, 1H), 9.14 (d, J = 2.4 Hz, 1H), 9.02 (s, 1H), 8.98 (s, 1H), 8.80-8.69 (m, 1H), 8.45 (dd, J = 8.8 Hz, 1H), 8.20-8.13 (m, 2H), 7.49-7.19 (m, 1H), 7.12 (s, 1H), 7.08 (t, J = 5.60 Hz, 1H), 7.04 (dd, J = 5.6, 1.6 Hz, 1H), 7.00 (s, 1H), 6.97 (d, J = 8.4 Hz, 1H), 6.83 (d, J = 7.8 Hz, 1H), 5.36-5.27 (m, 1H), 3.62-3.56 (m, 4H), 3.54-3.49 (m, 4H), 3.42-3.39 (m, 2H), 3.26 (s, 3H), 3.19 (d, J = 6.4 Hz, 2H), 2.91-2.84 (m, 1H), 2.64-2.61 (m, 2H), 2.03-1.96 (m, 1H), 1.85-1.74 (m, 2H), 1.24 (d, J = 0.8 Hz, 1H), 1.11-1.04 (m, 1H), 0.50-0.41 (m, 2H), 0.27-0.17 (m, 2H) |
| 457 | I-462 | PA | FX | 868.4 | 11.20 (s, 1H), 10.05 (s, 1H), 8.98 (s, 1H), 8.91 (s, 1H), 8.66 (t, J = 5.6 Hz, 1H), 8.17 (d, J = 5.6 Hz, 1H), 8.04-8.01 (m, 2H), 7.99-7.96 (m, 2H), 7.45-7.18 (m, 2H), 7.16-7.12 (m, 2H), |

TABLE 23-continued

Compounds synthesized via Method 12 with the coupling of various amines and acids in Step 1.

| Ex-#[a] | I-# | Step 1 Intermediate Amine | Step 1 Intermediate Acid | LCMS (ES+) m/z (M + H)+ | 1HNMR (400 MHz, DMSO-d6) δ |
|---|---|---|---|---|---|
| | | | | | 7.11-7.07 (m, 1H), 7.05 (d, J = 6.4 Hz, 1H), 7.02 (d J = 8.0 Hz, 1H), 5.34 (dd, J = 5.2, 13.2 Hz, 1H), 3.57 (d, J = 5.6 Hz, 8H), 3.53-3.51 (m, 2H), 3.19 (t, J = 5.6 Hz, 2H), 2.88-2.85 (m, 1H), 2.75-2.58 (m, 4H), 2.15-2.14 (m, 1H), 1.81-1.74 (m, 2H), 1.09-1.06 (m, 1H), 0.49-0.44 (m, 2H), 0.26-0.22 (m, 2H) |
| 458 | I-463 | VT | KR | 841.4 | 11.08 (s, 1H), 10.82 (s, 1H), 8.97 (s, 1H), 8.37 (s, 1H), 8.29-8.21 (m, 2H), 7.69 (t, J = 6.4 Hz, 1H), 7.25 (s, 1H), 7.16 (d, J = 5.6 Hz, 1H), 7.04-6.94 (m, 2H), 6.84 (d, J = 8.0 Hz, 1H), 5.32 (dd, J = 5.2, 12.8 Hz, 1H), 4.31-4.17 (m, 2H), 3.92 (s, 3H), 3.57-3.50 (m, 8H), 3.48-3.40 (m, 4H), 3.30 (s, 3H), 3.25 (s, 2H), 2.95-2.83 (m, 1H), 2.75-2.60 (m, 4H), 2.02-1.97 (m, 1H), 1.85-1.72 (m, 2H) |
| 459 | I-464 | VU | KR | 841.3 | 11.08 (s, 1H), 10.82 (s, 1H), 8.97 (s, 1H), 8.37 (s, 1H), 8.28-8.23 (m, 2H), 7.70 (t, J = 6.4 Hz, 1H), 7.25 (s, 1H), 7.16 (d, J = 5.2 Hz, 1H), 6.97-6.89 (m, 2H), 6.83 (dd, J = 2.8, 5.9 Hz, 1H), 5.35 (dd, J = 5.2, 12.4 Hz, 1H), 4.30-4.19 (m, 2H), 3.91 (s, 3H), 3.57-3.40 (m, 17H), 2.91 (t, J = 7.6 Hz, 2H), 2.88-2.83 (m, 1H), 2.75-2.57 (m, 2H), 2.04-1.93 (m, 1H), 1.84-1.75 (m, 2H) |
| 460[b] | I-465 | RD | RX | 866.4 | 11.07 (d, J = 4.4 Hz, 1H), 9.39 (s, 1H), 8.82 (d, J = 8.0 Hz, 1H), 8.36 (s, 1H), 8.30 (s, 1H), 7.29-6.98 (m, 1H), 6.97-6.84 (m, 4H), 5.36 (d, J = 5.6, 12.8 Hz, 1H), 4.22 (s, 2H), 3.88 (s, 3H), 3.85 (s, 3H), 3.66-3.45 (m, 22H), 2.96-2.84 (m, 3H), 2.73-2.58 (m, 2H), 2.04-1.95 (m, 1H), 1.85-1.74 (m, 2H) |
| 461[b] | I-466 | RD | 2-[2-[2-[2-[3-[1-(2,6-dioxo-3-piperidyl)-3-methyl-2-oxo-benzimidazol-5-yl]propoxy]-ethoxy]ethoxy]-ethoxy]acetic acid (synthesized via Steps 1-5 of Example 441, I-447) | 866.1 | 11.07 (s, 1H), 9.38 (s, 1H), 8.79 (d, J = 8.0 Hz, 1H), 8.35 (s, 1H), 8.29 (s, 1H), 7.26-6.95 (m, 3H), 6.88 (d, J = 8.0 Hz, 1H), 6.85-6.80 (m, 1H), 5.32 (dd, J = 5.2, 12.8 Hz, 1H), 4.21 (s, 2H), 3.87 (s, 3H), 3.84-3.81 (m, 2H), 3.63-3.55 (m, 8H), 3.53-3.48 (m, 6H), 3.46-3.40 (m, 4H), 3.34-3.32 (m, 2H), 3.30 (s, 3H), 2.96-2.82 (m, 1H), 2.74-2.57 (m, 4H), 2.05-1.95 (m, 1H), 1.82-1.70 (m, 2H) |
| 462[b] | I-467 | RD | 2-[2-[2-[2-[2-[[2-(2,6-dioxo-3-piperidyl)-1,3-dioxo-isoindolin-4-yl]amino]ethoxy]-ethoxy]ethoxy]-ethoxy]acetic acid (synthesized via Steps 1-2 | 866.4 | 11.08 (s, 1H), 9.39 (s, 1H), 8.82 (d, J = 7.6 Hz, 1H), 8.42-8.26 (m, 2H), 7.65-7.50 (m, 1H), 7.21-6.85 (m, 4H), 6.58 (d, J = 5.2 Hz, 1H), 5.05 (d, J = 5.2, 12.8 Hz, 1H), 4.22 (s, 2H), 3.94-3.81 (m, 7H), 3.64-3.51 (m, 18H), 3.44 (d, J = 5.6 Hz, 2H), 2.99-2.77 (m, 1H), 2.61 (d, J = 2.4 Hz, 2H), 2.14-1.92 (m, 1H) |

TABLE 23-continued

Compounds synthesized via Method 12 with the coupling of various amines and acids in Step 1.

| Ex-#[a] | I-# | Step 1 Intermediate Amine | Step 1 Intermediate Acid | LCMS (ES+) m/z (M + H)+ | $^1$HNMR (400 MHz, DMSO-d$_6$) δ |
|---|---|---|---|---|---|
| 463[b] | I-468 | RD | 2-[2-[2-[2-[[2-(2,6-dioxo-3-piperidyl)-1,3-dioxo-isoindolin-4-yl]amino]-ethoxy]ethoxy]-ethoxy]acetic acid (synthesized via Steps 1-2 of Example 152, I-152) of Example 161, I-161) | 822.2 | 11.08 (s, 1H), 9.37 (s, 1H), 8.80 (d, J = 8.0 Hz, 1H), 8.36 (s, 1H), 8.29 (s, 1H), 7.53 (d, J = 7.2, 8.4 Hz, 1H), 7.15-6.96 (m, 3H), 6.89 (d, J = 8.0 Hz, 1H), 6.57 (t, J = 5.6 Hz, 1H), 5.05 (d, J = 5.6, 12.8 Hz, 1H), 4.21 (s, 2H), 3.89 (s, 3H), 3.84 (s, 2H), 3.63-3.55 (m, 14H), 3.44 (d, J = 5.6 Hz, 2H), 3.29 (s, 2H), 2.93-2.82 (m, 1H), 2.62-2.53 (m, 2H), 2.06-1.98 (m, 1H) |
| 464[b] | I-469 | RD | VW | 778.3 | 11.07 (s, 1H), 9.37 (s, 1H), 8.77 (d, J = 8.0 Hz, 1H), 8.35 (s, 1H), 8.28 (s, 1H), 7.27-6.90 (m, 3H), 6.87-6.81 (m, 2H), 5.33-5.29 (m, 1H), 4.24 (s, 2H), 3.96-3.75 (m, 7H), 3.61 (m, 6H), 3.54-3.53 (m, 2H), 3.44-3.39 (m, 2H), 3.29 (s, 3H), 2.95-2.84 (m, 1H), 2.74-2.57 (m, 4H), 2.04-1.96 (m, 1H), 1.84-1.73 (m, 2H) |
| 465 | I-470 | VR | VY | 899.3 | 11.08 (s, 1H), 10.07 (s, 1H), 8.98 (s, 1H), 8.95 (s, 1H), 8.43-8.33 (m, 1H), 8.15 (d, J = 5.4 Hz, 1H), 7.91-7.74 (m, 3H), 7.50-7.12 (m, 1H), 7.12-7.07 (m, 2H), 7.05-6.96 (m, 3H), 6.90-6.82 (m, 1H), 5.32 (dd, J = 5.2, 12.8 Hz, 1H), 3.59-3.40 (m, 10H), 3.30 (s, 3H), 3.18 (t, J = 6.0 Hz, 2H), 2.97-2.81 (m, 1H), 2.76-2.68 (m, 1H), 2.66-2.61 (m, 2H), 2.58-2.52 (m, 1H), 2.05-1.94 (m, 1H), 1.85-1.74 (m, 2H), 1.15-0.98 (m, 1H), 0.49-0.41 (m, 2H), 0.26-0.18 (m, 2H) |
| 466 | I-471 | 4-[2-[2-[2-(2-aminoethoxy)-ethoxy]ethoxy]-ethylamino]-2-(2,6-dioxo-3-piperidyl)isoindoline-1,3-dione (synthesized via Steps 1-2) | WB | 801.1 | 10.5 (s, 1H), 8.71 (d, J = 8.0 Hz, 1H), 8.38 (s, 1H), 8.28-8.20 (m, 2H), 8.05 (t, J = 5.6 Hz, 1H), 7.54 (dd, J = 7.2, 8.4 Hz, 1H), 7.08 (d, J = 8.8 Hz, 1H), 7.01 (d, J = 7.2 Hz, 1H), 6.83 (d, J = 8.0 Hz, 1H), 6.57 (t, J = 5.6 Hz, 1H), 5.04 (dd, J = 5.6, 12.8 Hz, 1H), 4.05-3.85 (m, 7H), 3.61-3.57 (m, 2H), 3.55-3.50 (m, 10H), 3.45-3.38 (m, 4H), 2.93-2.88 (m, 4H), 2.87-2.80 (m, 1H), 2.62-2.52 (m, 2H), 2.06-1.98 (m, 1H) |
| 467 | I-472 | HQ | WD | 874.4 | 11.07 (s, 1H), 9.98 (s, 1H), 8.97 (d, J = 1.6 Hz, 1H), 8.92 (d, J = 1.6 Hz, 1H), 8.88 (s, 1H), 8.81 (t, J = 5.2 Hz, 1H), 8.49 (s, 1H), 8.22 (d, J = 5.2 Hz, 1H), 8.02 (s, 1H), 7.55 (t, J = 6.4 Hz, 1H), 7.29-7.16 (m, 2H), 6.98-6.88 (m, 2H), 6.84-6.82 (m, 1H), 5.36-5.32 (m, 1H), 4.29-4.17 (m, 2H), 3.93 (s, 3H), 3.57-3.44 (m, 13H), 2.95-2.85 (m, 3H), 2.71-2.56 (m, 2H), 2.03-1.92 (m, 1H), 1.84-1.71 (m, 2H) |
| 468 | I-473 | PP | FX | 865.8 | 11.09 (s, 1H), 10.11-9.93 (m, 1H), 8.97 (s, 1H), 8.95-8.77 (m, 1H), 8.15 (d, J = 5.2 Hz, 1H), 7.92 (d, J = 8.4 Hz, 2H), 7.63-7.52 (m, 2H), 7.47-7.14 (m, 1H), |

TABLE 23-continued

Compounds synthesized via Method 12 with the coupling of various amines and acids in Step 1.

| Ex-#[a] | I-# | Step 1 Intermediate Amine | Step 1 Intermediate Acid | LCMS (ES+) m/z (M + H)+ | $^1$HNMR (400 MHz, DMSO-$d_6$) δ |
|---|---|---|---|---|---|
| | | | | | 7.14-7.07 (m, 2H), 7.04 (dd, J = 1.2, 5.2 Hz, 1H), 6.98-6.84 (m, 2H), 5.40-5.25 (m, 1H), 3.62-3.50 (m, 4H), 3.45 (s, 3H), 3.27 (s, 3H), 3.18 (t, J = 6.4 Hz, 2H), 3.03-2.92 (m, 4H), 2.74 (s, 1H), 2.65-2.52 (m, 2H), 2.09-1.92 (m, 1H), 1.90-1.60 (m, 4H), 1.12-1.01 (m, 1H), 0.49-0.41 (m, 2H), 0.26-0.19 (m, 2H) |
| 470 | I-475 | PY | FX | 838.4 | 11.20 (s, 1H), 10.03 (s, 1H), 8.97 (s, 1H), 8.91 (s, 1H), 8.57 (t, J = 5.6 Hz, 1H), 8.16 (d, J = 5.2 Hz, 1H), 8.04-7.94 (m, 4H), 7.31 (t, J = 56 Hz, 1H), 7.15-7.06 (m, 4H), 7.06-7.00 (m, 2H), 5.39-5.31 (m, 1H), 3.49-3.40 (m, 6H), 3.18 (t, J = 6.0 Hz, 2H), 2.93-2.82 (m, 1H), 2.76 (t, J = 7.6 Hz, 2H), 2.68-2.60 (m, 2H), 2.20-2.10 (m, 1H), 1.91-1.84 (m, 2H), 1.83-1.76 (m, 2H), 1.13-1.01 (m, 1H), 0.49-0.42 (m, 2H), 0.26-0.19 (m, 2H) |
| 471 | I-476 | QA | FX | 852.5 | 11.18 (s, 1H), 10.12-9.91 (m, 1H), 8.98 (s, 1H), 8.85 (d, J = 17.2 Hz, 1H), 8.16 (d, J = 5.2 Hz, 1H), 7.92 (d, J = 8.4 Hz, 2H), 7.62-7.51 (m, 2H), 7.44-6.82 (m, 7H), 5.41-5.26 (m, 1H), 3.55-3.40 (m, 4H), 3.39-3.36 (m, 3H), 3.28-3.23 (m, 2H), 3.18 (t, J = 6.0 Hz, 2H), 2.99-2.92 (m, 3H), 2.89-2.75 (m, 2H), 2.20-2.08 (m, 1H), 1.93-1.65 (m, 4H), 1.11-1.02 (m, 1H), 0.49-0.41 (m, 2H), 0.26-0.19 (m, 2H) |
| 472 | I-477 | QI | FX | 865.4 | 11.07 (s, 1H), 10.12-9.87 (m, 1H), 8.97 (s, 1H), 8.92-8.72 (m, 1H), 8.16 (d, J = 5.2 Hz, 1H), 7.93 (d, J = 8.8 Hz, 2H), 7.65-7.48 (m, 2H), 7.44-6.70 (m, 7H), 5.40-5.23 (m, 1H), 3.61-3.42 (m, 6H), 3.32-3.23 (m, 6H), 3.21-3.18 (m, 2H), 2.98-2.94 (m, 2H), 2.91-2.81 (m, 1H), 2.69-2.60 (m, 2H), 2.04-1.93 (m, 1H), 1.92-1.61 (m, 4H), 1.12-1.02 (m, 1H), 0.49-0.42 (m, 2H), 0.27-0.19 (m, 2H) |
| 473 | I-478 | QK | FX | 866.3 | (CDCl$_3$) 9.36 (s, 1H), 9.17 (s, 1H), 8.86 (s, 1H), 8.51 (s, 1H), 8.24 (d, J = 5.2 Hz, 1H), 7.78 (d, J = 8.8 Hz, 2H), 7.65 (d, J = 8.8 Hz, 2H), 7.59 (s, 1H), 7.24-7.19 (m, 1H), 7.10-6.81 (m, 4H), 6.71 (d, J = 7.2 Hz, 1H), 5.20-5.12 (m, 1H), 3.74 (t, J = 5.3 Hz, 2H), 3.57-3.49 (m, 2H), 3.25 (d, J = 5.6 Hz, 2H), 3.06-2.93 (m, 1H), 2.92-2.69 (m, 4H), 2.41-2.27 (m, 1H), 2.03-1.92 (m, 4H), 1.61 (s, 6H), 1.23-1.08 (m, 1H), 0.69-0.57 (m, 2H), 0.39-0.29 (m, 2H) |
| 474 | I-479 | PY | FX | 839.5 | 11.18 (s, 1H), 10.08 (s, 1H), 9.11 (d, J = 2.4 Hz, 1H), 9.02 (s, 1H), 8.98 (s, 1H), 8.87 (t, J = 6.0 Hz, 1H), 8.46 (dd, J = 2.4, 8.8 Hz, 1H), 8.21-8.14 (m, 2H), 7.34 (d, J = 53.6 Hz, 1H), 7.14-7.00 (m, 6H), 5.34 (dd, J = 5.6, 13.2 Hz, |

TABLE 23-continued

Compounds synthesized via Method 12 with the coupling of various amines and acids in Step 1.

| Ex-#[a] | I-# | Step 1 Intermediate Amine | Step 1 Intermediate Acid | LCMS (ES+) m/z (M + H)+ | $^1$HNMR (400 MHz, DMSO-d$_6$) δ |
|---|---|---|---|---|---|
| | | | | | 1H), 3.47-3.41 (m, 6H), 3.20-3.17 (m, 2H), 2.89-2.81 (m, 1H), 2.77 (t, J = 7.6 Hz, 2H), 2.70-2.64 (m, 2H), 2.17-2.09 (m, 1H), 1.93-1.86 (m, 2H), 1.86-1.77 (m, 2H), 1.11-1.02 (m, 1H), 0.48-0.43 (m, 2H), 0.25-0.20 (m, 2H) |
| 476 | I-481 | OD | QW | 983.3 | 11.07 (s, 1H), 10.98 (s, 1H), 9.08 (s, 1H), 9.02 (s, 1H), 8.56 (t, J = 5.6 Hz, 1H), 8.26 (d, J = 4.8 Hz, 1H), 8.00 (s, 4H), 7.67 (t, J = 6.4 Hz, 1H), 7.26 (s, 1H), .18 (dd, J = 1.2, 5.2 Hz, 1H), 7.01 (s, 1H), 6.99 (d, J = 7.6 Hz, 1H), 6.85 (d, J = 8.0 Hz, 1H), 5.38-5.21 (m, 1H), 4.41-4.31 (s, 2H), 4.30-4.19 (m, 2H), 3.81-3.80 (m, 2H), 3.32-3.26 (m, 11H), 2.96-2.81 (m, 1H), 2.64-2.60 (m, 2H), 2.55-2.52 (m, 5H), 2.47-2.42 (m, 4H), 2.23 (s, 3H), 2.07-1.95 (m, 1H), 1.66-1.48 (m, 8H) |
| 477 | I-482 | OD | QY | 971.5 | 11.07 (s, 1H), 10.91 (s, 1H), 9.06 (s, 1H), 9.03 (s, 1H), 8.62-8.53 (m, 2H), 8.27 (d, J = 5.2 Hz, 1H), 8.12-8.05 (m, 2H), 8.04-7.99 (m, 2H), 7.69 (t, J = 6.4 Hz, 1H), 7.27 (s, 1H), 7.19 (d, J = 5.2 Hz, 1H), 7.03-6.97 (m, 2H), 6.86 (d, J = 8.4 Hz, 1H), 5.32 (dd, J = 5.2, 12.8 Hz, 1H), 4.30-4.21 (m, 2H), 3.35-3.27 (m, 11H), 3.35-3.27 (m, 1H), 2.93-2.87 (m, 1H), 2.65-2.58 (m, 4H), 2.57-2.54 (m, 2H), 2.22 (s, 6H), 2.05-1.96 (m, 1H), 1.65-1.50 (m, 8H) |
| 478 | I-483 | RD | QZ | 1001.6 | 9.36 (s, 1H), 8.93 (s, 1H), 8.78 (d, J = 8.0 Hz, 1H), 8.52 (t, J = 6.0 Hz, 1H), 8.32 (s, 1H), 8.25 (s, 1H), 7.80 (d, J = 9.6 Hz, 1H), 7.35 (q, J = 8.4 Hz, 4H), 7.09 (t, J = 56 Hz, 1H), 6.86 (d, J = 8.0 Hz, 1H), 5.08 (s, 1H), 4.49 (d, J = 9.6 Hz, 1H) 4.44-4.33 (m, 2H), 4.30 (s, 1H), 4.16 (dd, J = 5.6, 16.0 Hz, 1H), 3.83 (s, 3H), 3.78 (s, 4H), 3.65-3.50 (m, 6H), 2.39 (s, 3H), 2.35-2.28 (m, 2H), 2.27-2.15 (m, 1H), 2.10-1.94 (m, 2H), 1.90-1.80 (m, 1H), 1.52-1.33 (m, 4H), 1.27-1.13 (m, 12H), 0.88 (s, 9H) |
| 479[b] | I-484 | RD | RA | 1103.6 (M + Na)+ | 9.39 (s, 1H), 8.97 (s, 1H), 8.83 (d, J = 8.0 Hz, 1H), 8.59 (s, 1H), 8.36 (s, 1H), 8.30 (s, 1H), 7.43-7.36 (m, 5H), 7.27-6.97 (m, 1H), 6.91 (d, J = 7.6 Hz, 1H), 5.16 (d, J = 3.6 Hz, 1H), 4.55 (d, J = 9.2 Hz, 1H), 4.42 (m, 2H), 4.37 (m, 2H), 4.26 (m, 1H), 4.21 (s, 2H), 3.95 (s, 2H), 3.89-3.82 (m, 7H), 3.66-3.48 (m, 20H), 2.43 (s, 4H), 2.05 (m, 1 H), 1.89 (m, 1H), 1.23 (m, 1H), 0.93 (s, 9H) |
| 480[b] | I-485 | RD | RB | 993.5 | 9.35 (s, 1H), 8.97-8.89 (m, 1H), 8.78 (d, J = 8.0 Hz, 1H), 8.56 (t, J = 6.0 Hz, 1H), 8.32 (s, 1H), 8.29-8.23 (m, 1H), 7.43-7.37 (m, 1H), 7.34 (s, 4H), 7.24-6.94 (m, 1H), 6.86 (d, J = 8.0 Hz, 1H), 5.13 (d, J = 3.2 Hz, 1H), 4.51 (d, J = 9.6 Hz, |

TABLE 23-continued

Compounds synthesized via Method 12 with the coupling of various amines and acids in Step 1.

| Ex-#[a] | I-# | Step 1 Intermediate Amine | Step 1 Intermediate Acid | LCMS (ES+) m/z (M + H)+ | ¹HNMR (400 MHz, DMSO-d$_6$) δ |
|---|---|---|---|---|---|
| | | | | | 1H), 4.43-4.28 (m, 3H), 4.26-4.14 (m, 3H), 3.91 (s, 2H), 3.83 (s, 3H), 3.79 (s, 4H), 3.61-3.50 (m, 15H), 2.40-2.38 (m, 3H), 2.07-1.95 (m, 1H), 1.88-1.85 (m, 1H), 0.86 (s, 9H) |
| 482[b] | I-487 | RR | RP | 934.4 | 11.07 (s, 1H), 10.04 (s, 1H), 9.00 (s, 1H), 8.88 (s, 1H), 8.25 (d, J = 5.2 Hz, 1H), 7.93 (d, J = 7.6 Hz, 2H), 7.61 (t, J = 6.4 Hz, 1H), 7.56 (d, J = 8.4 Hz, 2H), 7.46-7.30 (m, 1H), 7.26 (s, 1H), 7.21 (dd, J = 1.2, 5.2 Hz, 1H), 7.08-6.96 (m, 2H), 6.92-6.83 (m, 1H), 5.37-5.28 (m, 1H), 4.30-4.19 (m, 2H), 3.88-3.69 (m, 2H), 3.70-3.58 (m, 1H), 3.57-3.46 (m, 3H), 3.31 (s, 3H), 3.00 (s, 3H), 2.95-2.84 (m, 1H), 2.82-2.70 (m, 1H), 2.69-2.56 (m, 4H), 2.36-2.31 (m, 1H), 2.27-2.20 (m, 1H), 2.09-1.91 (m, 2H), 1.83-1.47 (m, 3H) |
| 483[b] | I-488 | RW | RU | 906.2 | 11.08 (s, 1H), 10.05 (s, 1H), 8.97 (s, 1H), 8.87 (s, 1H), 8.16 (d, J = 5.2 Hz, 1H), 7.92 (s, 2H), 7.56 (d, J = 8.4 Hz, 2H), 7.30 (t, J = 54.8, 1H), 7.13-7.11 (m, 1H), 7.11-7.07 (m, 1H), 7.06-6.95 (m, 3H), 6.90-6.83 (m, 1H), 5.43-5.20 (m, 1H), 3.88-3.67 (m, 4H), 3.28-3.22 (m, 5H), 3.19-3.17 (m, 2H), 2.99 (s, 3H), 2.94-2.75 (m, 3H), 2.64-2.62 (m, 2H), 2.59-2.57 (m, 2H), 2.31-2.18 (m, 2H), 2.10-1.93 (m, 2H), 1.79-1.67 (m, 2H), 1.11-1.03 (m, 1H), 0.48-0.43 (m, 2H), 0.24-0.20 (m, 2H) |
| 484 | I-489 | RT | CN | 914.8 | 11.07 (s, 1H), 11.01 (s, 1H), 9.01 (d, J = 8.4 Hz, 2H), 8.26 (d, J = 4.8 Hz, 1H), 8.16-8.00 (m, 3H), 7.81-7.65 (m, 2H), 7.54 (s, 2H), 7.27 (s, 1H), 7.18 (d, J = 4.8 Hz, 1H), 7.07-6.93 (m, 2H), 6.86-6.80 (m, 1H), 5.37-5.27 (m, 1H), 4.40-4.15 (m, 2H), 3.45-3.27 (m, 10H), 3.06-2.80 (m, 4H), 2.65-2.55 (m, 4H), 2.03-1.96 (m, 1H), 1.68-1.36 (m, 8H) |
| 485[b] | I-490 | RR | RU | 906.5 | 11.07 (s, 1H), 10.03 (s, 1H), 8.98 (s, 1H), 8.88 (s, 1H), 8.16 (d, J = 5.2 Hz, 1H), 7.93 (d, J = 7.6 Hz, 2H), 7.56 (d, J = 8.4 Hz, 2H), 7.30 (t, J = 8.4 Hz, 1H), 7.12 (s, 1H), 7.08 (t, J = 5.6 Hz, 1H), 7.06-6.95 (m, 3H), 6.92-6.82 (m, 1H), 5.37-5.28 (m, 1H), 3.88-3.76 (m, 2H), 3.72-3.63 (m, 2H), 3.62-3.58 (m, 1H), 3.31 (s, 3H), 3.19 (t, J = 6.0 Hz, 2H), 3.00 (s, 3H), 2.96-2.85 (m, 1H), 2.83-2.74 (m, 1H), 2.72-2.65 (m, 2H), 2.63-2.57 (m, 2H), 2.36-2.28 (m, 2H), 2.27-2.14 (m,, 1H), 2.12-1.94 (m, 2H), 1.86-1.53 (m, 3H), 1.17-0.95 (m, 1H), 0.49-0.43 (m, 2H), 0.25-0.18 (m, 2H) |
| 486 | I-491 | RT | FX | 893.5 | 11.08 (s, 1H), 10.04 (s, 1H), 8.98 (s, 1H), 8.88 (s, 1H), 8.17 (d, J = 5.2 Hz, 1H), 7.93 (d, J = 8.4 Hz, |

TABLE 23-continued

Compounds synthesized via Method 12 with the coupling of various amines and acids in Step 1.

| Ex-#[a] | I-# | Step 1 Intermediate Amine | Step 1 Intermediate Acid | LCMS (ES+) m/z (M + H)+ | ¹HNMR (400 MHz, DMSO-d$_6$) δ |
|---|---|---|---|---|---|
| | | | | | 2H), 7.59-7.49 (m, 2H), 7.31 (t, J = 54 Hz, 1H), 7.13 (s, 1H), 7.09 (t, J = 5.6 Hz, 1H), 7.06-7.04 (m, 1H), 6.99 (d, J = 7.6 Hz, 2H), 6.85 (s, 1H), 5.40-5.25 (m, 1H), 3.52-3.39 (m, 4H), 3.31 (s, 6H), 3.22-3.17 (m, 2H), 2.99-2.84 (m, 4H), 2.77-2.69 (m, 1H), 2.65-2.62 (m, 1H), 2.61-2.57 (m, 1H), 2.06-1.94 (m, 1H), 1.67-1.47 (m, 6H), 1.42-1.16 (m, 2H), 1.10-1.01 (m, 1H), 0.49-0.44 (m, 2H), 0.26-0.21 (m, 2H) |
| 489 | I-494 | QI | CN | 886.6 | 11.14-10.87 (m, 2H), 9.09-8.83 (m, 2H), 8.27 (d, J = 5.2 Hz, 1H), 8.14-8.00 (m, 3H), 7.78-7.67 (m, 2H), 7.54-7.63 (m, 2H), 7.27 (s, 1H), 7.19 (d, J = 5.2 Hz, 1H), 7.12-6.94 (m, 1H), 6.93-6.66 (m, 2H), 5.40-5.17 (m, 1H), 4.31-4.21 (m, 2H), 3.57-3.37 (m, 6H), 3.32-3.23 (m, 6H), 3.05-2.92 (m, 3H), 2.68-2.91 (m, 2H), 2.08-1.98 (s, 1H), 1.89-1.59 (m, 4H) |
| 490 | I-495 | QA | CN | 873.6 | 11.19 (s, 1H), 10.99 (s, 1H), 9.04 (s, 1H), 9.02-8.91 (m, 1H), 8.27 (d, J = 5.2 Hz, 1H), 8.16-8.00 (m, 3H), 7.80-7.66 (m, 2H), 7.62-7.53 (m, 2H), 7.28 (s, 1H), 7.19 (d, J = 5.6 Hz, 1H), 7.16-6.75 (m, 3H), 5.42-5.24 (m, 1H), 4.31-4.20 (m, 2H), 3.59-3.38 (m, 6H), 3.28-3.21 (m, 3H), 3.01-2.92 (m, 3H), 2.90-2.73 (m, 2H), 2.20-2.12 (m, 1H), 1.91-1.64 (m, 4H) |
| 499[b] | I-504 | SI | RU | 914.1 | 11.10 (s, 1H), 10.03 (s, 1H), 8.98 (s, 1H), 8.88 (s, 1H), 8.16 (s, 1H), 7.93 (d, J = 8.4 Hz, 2H), 7.62-7.48 (m, 2H), 7.46-7.17 (m, 2H), 7.14-7.00 (m, 5H), 5.37 (dd, J = 4.8, 12.0 Hz, 1H), 3.40-3.35 (m, 4H), 3.33 (s, 3H), 3.18 (t, J = 6.4 Hz, 2H), 2.95 (d, J = 13.2 Hz, 4H), 2.88-2.69 (m, 2H), 2.71-2.57 (m, 4H), 2.12-1.93 (m, 3H), 1.80-1.62 (m, 2H), 1.51-1.48 (m, 1H), 1.25 (d, J = 12.0 Hz, 1H), 1.11-1.02 (m, 1H), 0.95-0.80 (m, 1H), 0.49-0.42 (m, 2H), 0.26-0.19 (m, 2H) |
| 501 | I-506 | SL | FX | 947.5 | 11.14-11.04 (m, 1H), 10.05 (s, 1H), 8.98 (s, 1H), 8.93 (s, 1H), 8.76 (d, J = 6.8 Hz, 1H), 8.16 (d, J = 5.2 Hz, 1H), 8.06-7.95 (m, 4H), 7.47-7.17 (m, 1H), 7.12 (s, 1H), 7.10-7.09 (m, 2H), 7.06-7.04 (m, 1H), 7.03 (s, 1H), 6.96 (d, J = 8.4 Hz, 1H), 5.39-5.32 (m, 1H), 4.43 (d, J = 7.2 Hz, 1H), 4.14-4.10 (m, 1H) 3.47 (s, 2H), 3.42-3.41 (m, 2H), 3.33 (s, 3H), 3.16-3.18 (m, 2H), 2.92-2.85 (m, 1H), 2.77-2.70 (m, 1H), 2.70-2.66 (m, 1H), 2.64-2.62 (m, 1H), 2.61-2.57 (m, 2H), 2.56-2.53 (m, 3H), 2.47-2.44 (m, 4H), 2.30-2.24 (m, 4H), 2.06-1.97 (m, 1H), 2.05-1.97 (m, 1H), 1.12-1.02 (m, 1H), 0.48-0.42 (m, 2H), 0.25-0.20 (m, 2H) |

TABLE 23-continued

Compounds synthesized via Method 12 with the coupling of various amines and acids in Step 1.

| Ex-#[a] | I-# | Step 1 Intermediate Amine | Step 1 Intermediate Acid | LCMS (ES+) m/z (M + H)+ | 1HNMR (400 MHz, DMSO-$d_6$) δ |
|---|---|---|---|---|---|
| 503[b] | I-508 | SM | RU | 903.4 | 10.98 (d, J = 8.0 Hz, 1H), 10.03 (s, 1H), 8.97 (s, 1H), 8.92 (s, 1H), 8.70 (s, 1H), 8.16 (d, J = 5.2 Hz, 1H), 8.06-7.94 (m, 4H), 7.55-7.17 (m, 5H), 7.12 (s, 1H), 7.08 (t, J = 5.6 Hz, 1H), 7.04 (d, J = 5.2 Hz, 1H), 5.72-5.57 (m, 1H), 4.76-4.61 (m, 1H), 3.97-3.82 (m, 2H), 3.69-3.63 (m, 1H), 3.59-3.50 (m, 4H), 3.28-3.24 (m, 2H), 3.18 (t, J = 6.0 Hz, 2H), 2.91-2.79 (m, 2H), 2.71 (s, 1H), 2.60-2.53 (m, 2H), 2.40-2.33 (m, 1H), 2.26-2.17 (m, 1H), 2.11 (t, J = 9.6 Hz, 1H), 2.04-1.92 (m, 1H), 1.11-1.03 (m, 1H), 0.48-0.42 (m, 2H), 0.25-0.20 (m, 2H) |
| 504[b] | I-509 | SO | RU | 903.4 | 10.99 (d, J = 5.6 Hz, 1H), 10.04 (s, 1H), 8.98 (s, 1H), 8.93 (s, 1H), 8.71 (, J = 5.6 Hz, 1H), 8.16 (d, J = 5.2 Hz, 1H), 8.06-8.02 (m, 2H), 8.00-7.96 (m, 2H), 7.50-7.41 (m, 4H), 7.40-7.18 (m, 1H), 7.12-7.07 (m, 2H), 7.04 (dd, J = 1.2, 5.2 Hz, 1H), 5.72-5.58 (m, 1H), 4.75-4.61 (m, 1H), 3.94-3.84 (m, 2H), 3.68-3.63 (m, 1H), 3.57 (s, 2H), 3.55-3.51 (m, 1H), 3.26-3.21 (m, 2H), 3.18 (t, J = 6.0 Hz, 2H), 2.88-2.81 (m, 2H), 2.79-2.69 (m, 1H), 2.58-2.55 (m, 2H), 2.43-2.35 (m, 1H), 2.26-2.17 (m, 1H), 2.14-2.07 (m, 1H), 2.02-1.92 (m, 1H), 1.10-1.03 (m, 1H), 0.48-0.43 (m, 2H), 0.24-0.21 (m, 2H) |
| 508[b] | I-513 | TT | RU | 906.6 | 11.08 (s, 1H), 10.02 (s, 1H), 8.97 (s, 1H), 8.88 (s, 1H), 8.18-8.15 (m, 1H), 7.93-7.91 (m, 2H), 7.56-7.55 (m, 2H), 7.47-7.15 (m, 1H), 7.14-7.02 (m, 3H), 7.00-6.82 (m, 3H), 5.37-5.33 (m, 1H), 3.88-3.68 (m, 3H), 3.57 (d, J = 2.8 Hz, 6H), 3.00 (s, 3H), 2.97-2.75 (m, 5H), 2.74-2.56 (m, 4H), 2.35-2.26 (m, 2H), 2.05-1.92 (m, 2H), 1.83-1.66 (m, 2H), 1.13-1.02 (m, 1H), 0.50-0.40 (m, 2H), 0.26-0.18 (m, 2H) |
| 509 | I-514 | TU | FX | 906.3 | 11.07 (s, 1H), 10.01 (s, 1H), 8.96 (s, 1H), 8.87 (s, 1H), 8.18-8.11 (m, 1H), 8.01-7.84 (m, 2H), 7.57 (s, 2H), 7.30 (t, J = 54.4 Hz, 1H), 7.11 (s, 1H), 7.07 (t, J = 4.8 Hz, 1H), 7.03 (dd, J = 1.6 Hz, 1H), 7.00-6.80 (m, 3H), 5.43-5.27 (m, 1H), 3.57 (s, 6H), 3.28 (s, 3H), 3.21-3.15 (t, J = 6.0 Hz, 3H), 3.00 (s, 3H), 2.96-2.83 (m, 4H), 2.51 (s, 6H), 2.04-1.92 (m, 2H), 1.11-1.01 (m, 1H), 0.50-0.39 (m, 2H), 0.26-0.17 (m, 2H) |
| 510[b] | I-515 | SV | RU | 895.5 | 10.02 (s, 1H), 8.97 (s, 1H), 8.89 (s, 1H), 8.64 (t, J = 5.6 Hz, 1H), 8.16 (d, J = 5.2 Hz, 1H), 8.04-7.98 (m, 2H), 7.97-7.91 (m, 2H), 7.31 (t, J = 54.4 Hz, 1H), 7.14-7.06 (m, 2H), 7.04 (d, J = 5.2 Hz, 1H), 6.96-6.89 (m, 2H), 6.83 (dd, J = 1.6, 6.9 Hz, 1H), 5.41 (dd, J = 5.2, 13.0 Hz, 1H), 3.60-3.56 (m, 4H), 3.55-3.53 (m, 4H), |

TABLE 23-continued

Compounds synthesized via Method 12 with the coupling of various amines and acids in Step 1.

| Ex-#[a] | I-# | Step 1 Intermediate Amine | Step 1 Intermediate Acid | LCMS (ES+) m/z (M + H)+ | 1HNMR (400 MHz, DMSO-d6) δ |
|---|---|---|---|---|---|
| | | | | | 3.48-3.44 (m, 4H), 3.18 (t, J = 6.0 Hz, 2H), 3.02 (s, 3H), 2.92 (dd, J = 7.2, 8.7 Hz, 3H), 2.80-2.73 (m, 1H), 2.03-1.95 (m, 1H), 1.84-1.76 (m, 2H), 1.11-1.02 (m, 1H), 0.49-0.42 (m, 2H), 0.23 (q, J = 4.8 Hz, 2H), −0.02−−0.12 (m, 2H) |
| 512 | I-517 | WN | FX | 921.5 | 11.07 (s, 1H), 10.03 (s, 1H), 8.98 (s, 1H), 8.87 (s, 1H), 8.16 (d, J = 5.4 Hz, 1H), 7.93 (d, J = 8.8 Hz, 2H), 7.56 (d, J = 8.8 Hz, 2H), 7.31 (t, J = 54 Hz, 1H), 7.12-6.98 (m, 5H), 6.87 (d, J = 8.0 Hz, 1H), 5.35-5.31 (m, 1H), 4.06-3.85 (m, 1H), 3.62-3.55 (m, 3H), 3.53-3.49 (m, 2H), 3.44-3.39 (m, 2H), 3.35 (s, 3H), 3.27 (m, 2H), 3.19 (t, J = 6.0 Hz, 2H), 2.93-2.84 (m, 1H), 2.77-2.69 (m, 1H), 2.64 (m, 2H), 2.54 (m, 2H), 2.03-1.95 (m, 1H), 1.91-1.77 (m, 4H), 1.55-1.40 (m, 2H), 1.11-1.01 (m, 1H), 0.50-0.40 (m, 2H), 0.24-0.21 (m, 2H) |

[a]Variations in reaction time for Method 12 were as follows: Step 1 was run anywhere from 0.5-12 h, and Step 2 anywhere from 10 min-17 h. If the product of Step 1 was not a precipitate, a standard work up with water and extraction with ethyl acetate was used to isolate the product. Step 2 deprotection could also be achieved under a variety of standard conditions if not with HCl/dioxane in DCM, including with TFA in DCM at rt.
[b]No Step 2 deprotection required. cStep 2 deprotection was achieved using HBr/HOAc in DCM at rt for 12 h.

Further Examples Using Synthetic Methods Similar to Method 12

Example 514: 2-[2-(Cyclopropylmethylamino)-4-pyridyl]-N-[3-(difluoromethyl)-1-[4-[2-[2-[2-[2-[2-[[(3S)-2-[(2S)-3,3-dimethyl-2-[[(2S)-2-(methylamino)propanoyl]amino]butanoyl]-3-[[(1R)-tetralin-1-yl]carbamoyl]-3,4-dihydro-1H-isoquinolin-7-yl]oxy]ethoxy]ethoxy]ethoxy]ethoxy]ethylcarbamoyl]phenyl]pyrazol-4-yl]oxazole-4-carboxamide, I-519

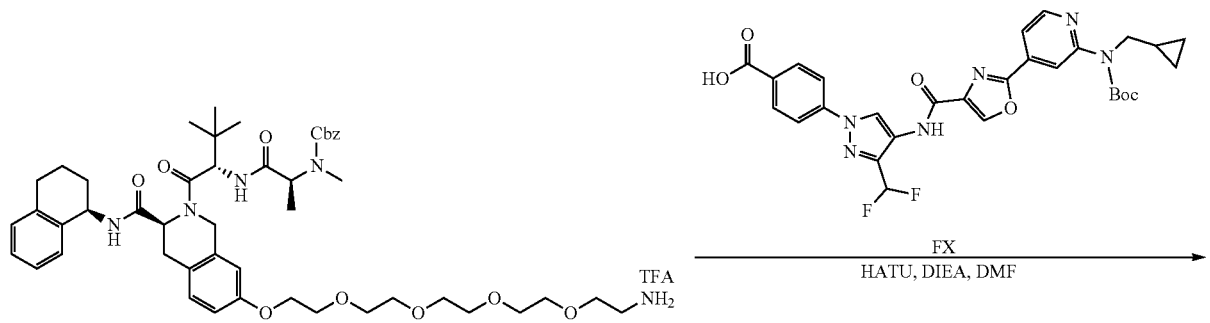

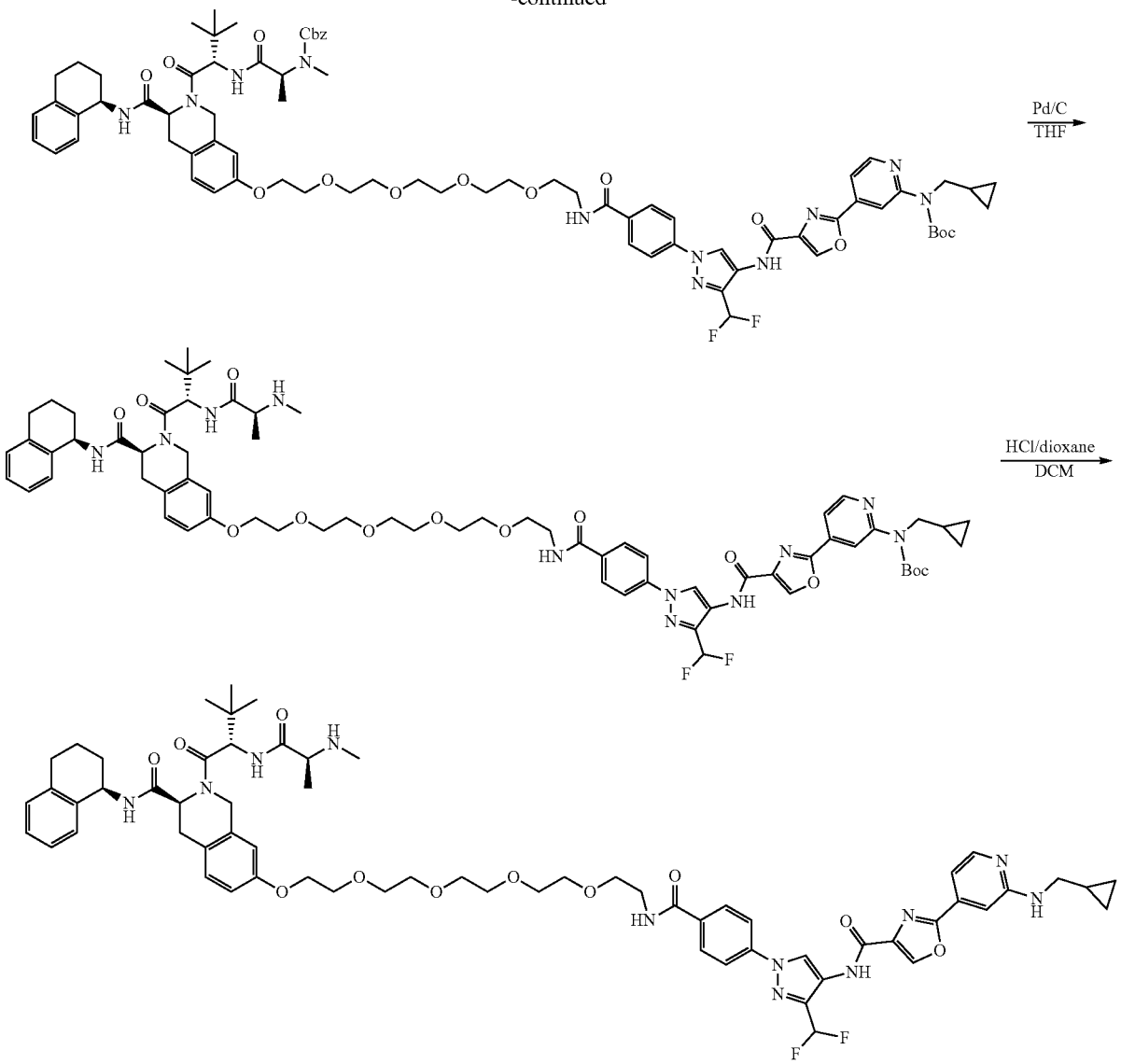

Step 1—Tert-butyl N-[4-[4-[[1-[4-[2-[2-[2-[2-[2-[[(3S)-2-[(2S)-2-[[(2S)-2-[benzyloxycarbonyl(methyl)amino]propanoyl]amino]-3,3-dimethyl-butanoyl]-3-[[(1R)-tetralin-1-yl]carbamoyl]-3,4-dihydro-1H-isoquinolin-7-yl]oxy]ethoxy]ethoxy]ethoxy]ethoxy]ethylcarbamoyl]phenyl]-3-(difluoromethyl)pyrazol-4-yl]carbamoyl]oxazol-2-yl]-2-pyridyl]-N-(cyclopropylmethyl)carbamate To a mixture of benzyl N-[(1S)-2-[[(1S)-1-[(3S)-7-[2-[2-[2-[2-(2-aminoethoxy)ethoxy]ethoxy]ethoxy]-3-[[(1R)-tetralin-1-yl]carbamoyl]-3,4-dihydro-1H-isoquinoline-2-carbonyl]-2,2-dimethyl-propyl]amino]-1-methyl-2-oxo-ethyl]-N-methyl-carbamate (30.0 mg, 30.3 umol, TFA, Intermediate PJ) and DIPEA (19.6 mg, 151 umol, 26.4 uL) in DMF (2 mL) was added 4-[4-[[2-[2-[tert-butoxycarbonyl(cyclopropylmethyl)amino]-4-pyridyl]oxazole-4-carbonyl]amino]-3-(difluoromethyl)pyrazol-1-yl]benzoic acid (18.0 mg, 30.3 umol, Intermediate FX) and HATU (13.8 mg, 36.4 umol). The reaction mixture was stirred at 25° C. for 0.5 hour. On completion, the reaction mixture was concentrated in vacuo. The residue was purified by prep-HPLC (0.1% FA condition) to give the title compound (25.0 mg, 56% yield) as white solid. LC-MS (ESI$^+$) m/z 1451.8 (M+H)$^+$.

Step 2—Tert-butyl N-(cyclopropylmethyl)-N-[4-[4-[[3-(difluoromethyl)-1-[4-[2-[2-[2-[2-[2-[[(3S)-2-[(2S)-3,3-dimethyl-2-[[(2S)-2-(methylamino)propanoyl]amino]butanoyl]-3-[[(1R)-tetralin-1-yl]carbamoyl]-3,4-dihydro-1H-isoquinolin-7-yl]oxy]ethoxy]ethoxy]ethoxy]ethoxy]ethyl]carbamoyl]phenyl]pyrazol-4-yl]carbamoyl]oxazol-2-yl]-2-pyridyl]carbamate To a mixture of tert-butyl N-[4-[4-[[1-[4-[2-[2-[2-[2-[2-[[(3S)-2-[(2S)-2-[[(2S)-2-[benzyloxycarbonyl(methyl)amino]propanoyl]amino]-3,3-dimethyl-butanoyl]-3-[[(1R)-tetralin-1-yl]carbamoyl]-3,4-dihydro-1H-isoquinolin-7-yl]oxy]ethoxy]ethoxy]ethoxy]ethoxy]ethyl]carbamoyl]phenyl]-3-(difluoromethyl)pyrazol-4-yl]carbamoyl]oxazol-2-yl]-2-pyridyl]-N-(cyclopropylmethyl)carbamate (30.0 mg, 20.6 umol) in THF (3 mL) was added Pd/C (30 mg, 10% wt). The reaction mixture was stirred at 25° C. for 2 hours under $H_2$ (15 psi) atmosphere. On completion, the reaction mixture was filtered and the filtrate concentrated in vacuo to give the title compound (27.0 mg, 99% yield) as light yellow oil. LC-MS (ESI$^+$) m/z 1316.6 (M+H)$^+$.

Step 3—2-[2-(Cyclopropylmethylamino)-4-pyridyl]-N-[3-(difluoromethyl)-1-[4-[2-[2-[2-[2-[2-[[(3S)-2-[(2S)-3,3-dimethyl-2-[[(2S)-2-(methylamino)propanoyl]amino]butanoyl]-3-[[(1R)-tetralin-1-yl]carbamoyl]-3,4-dihydro-1H-isoquinolin-7-yl]oxy]ethoxy]ethoxy]ethoxy]ethoxy]ethyl]carbamoyl]phenyl]pyrazol-4-yl]oxazole-4-carboxamide To a mixture of tert-butyl N-(cyclopropylmethyl)-N-[4-[4-[[3-(difluoromethyl)-1-[4-[2-[2-[2-[2-[2-[[(3S)-2-[(2S)-3,3-dimethyl-2-[[(2S)-2-(methylamino)propanoyl]amino]butanoyl]-3-[[(1R)-tetralin-1-yl]carbamoyl]-3,4-dihydro-1H-isoquinolin-7-yl]oxy]ethoxy]ethoxy]ethoxy]ethoxy]ethyl]carbamoyl]phenyl]pyrazol-4-yl]carbamoyl]oxazol-2-yl]-2-pyridyl]carbamate (27.0 mg, 20.5 umol) in DCM (3 mL) was added HCl/dioxane (4 M, 5.13 uL). The reaction mixture was stirred at 25° C. for 1 hour. On completion, the reaction mixture was concentrated in vacuo. The residue was purified by prep-HPLC (column: Phenomenex Synergi C18 150*25*10 um; mobile phase: [water (0.225% FA)-ACN]; B %: 13%-43%, 10 min) to give the title compound (10.7 mg, 42% yield) as white solid. $^1$H NMR (400 MHz, DMSO-$d_6$) δ 10.06 (s, 1H), 8.98 (s, 1H), 8.92 (s, 1H), 8.65 (t, J=5.2 Hz, 1H), 8.33 (s, 1H), 8.20-8.15 (m, 2H), 8.06-7.95 (m, 4H), 7.95-7.84 (m, 1H), 7.48-7.16 (m, 1H), 7.13-6.97 (m, 7H), 6.91 (d, J=2.4 Hz, 1H), 6.81-6.75 (m, 1H), 4.99-4.81 (m, 2H), 4.79-4.61 (m, 2H), 4.08-4.01 (m, 2H), 3.73 (d, J=3.6 Hz, 2H), 3.61-3.47 (m, 17H), 3.18 (t, J=6.0 Hz, 2H), 3.02-2.90 (m, 3H), 2.74-2.62 (m, 2H), 2.16 (s, 1H), 2.12 (s, 2H), 1.89-1.73 (m, 2H), 1.72-1.62 (m, 1H), 1.60-1.50 (m, 1H), 1.12-0.99 (m, 10H), 0.98-0.88 (m, 3H), 0.48-0.43 (m, 2H), 0.26-0.20 (m, 2H). LC-MS (ESI$^+$) m/z 1216.6 (M+H)$^+$.

Example 515: 2-[2-(Cyclopropylmethylamino)-4-pyridyl]-N-[3-(difluoromethyl)-1-[4-[2-[2-[2-[2-[2-[2-[[(3S)-2-[(2S)-3,3-dimethyl-2-[[(2S)-2-(methylamino)propanoyl]amino]butanoyl]-3-[[(1R)-tetralin-1-yl]carbamoyl]-3,4-dihydro-1H-isoquinolin-7-yl]oxy]ethoxy]ethoxy]ethoxy]ethoxy]ethylcarbamoyl]phenyl]-pyrazol-4-yl]oxazole-4-carboxamide, I-520

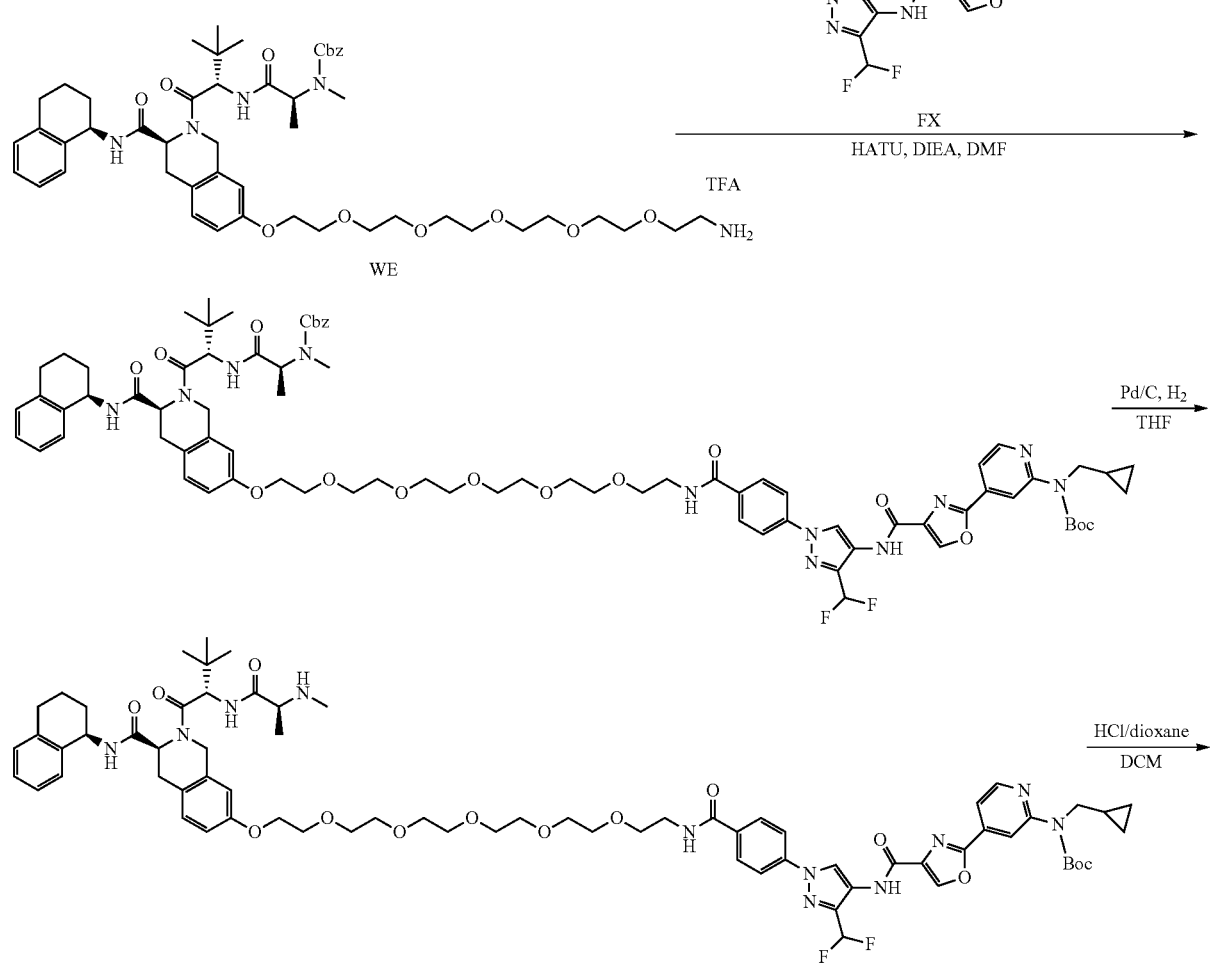

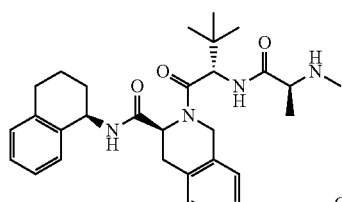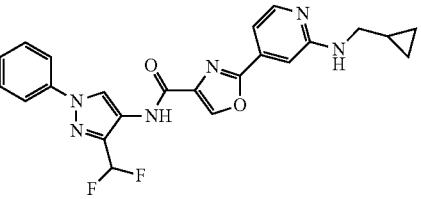

Step 1—Tert-butyl N-[4-[4-[[1-[4-[2-[2-[2-[2-[2-[2-[[(3S)-2-[(2S)-2-[[(2S)-2-[benzyloxycarbonyl(methyl)amino]propanoyl]amino]-3,3-dimethyl-butanoyl]-3-[[(1R)-tetralin-1-yl]carbamoyl]-3,4-dihydro-1H-isoquinolin-7-yl]oxy]ethoxy]ethoxy]ethoxy]ethoxy]ethoxy]ethylcarbamoyl]phenyl]-3-(difluoromethyl)pyrazol-4-yl]carbamoyl]oxazol-2-yl]-2-pyridyl]-N-(cyclopropylmethyl)carbamate To a mixture of benzyl N-[(1S)-2-[[(1S)-1-[(3S)-7-[2-[2-[2-[2-[2-(2-aminoethoxy)ethoxy]ethoxy]ethoxy]ethoxy]ethoxy]-3-[[(1R)-tetralin-1-yl]carbamoyl]-3,4-dihydro-1H-isoquinoline-2-carbonyl]-2-2-dimethyl-propyl]amino]-1-methyl-2-oxo-ethyl]-N-methyl-carbamate (70.0 mg, 76.2 umol, Intermediate WE), 4-[4-[[2-[2-[tert-butoxycarbonyl(cyclopropylmethyl)amino]-4-pyridyl]oxazole-4-carbonyl]amino]-3-(difluoromethyl)pyrazol-1-yl]benzoic acid (45.3 mg, 76.2 umol, Intermediate FX) in DMF (2 mL) was added DIPEA (29.6 mg, 229 umol) and HATU (34.8 mg, 91.5 umol). The reaction mixture was stirred at 20° C. for 1 hour. On completion, the reaction mixture was poured into water (20 mL). The aqueous phase was extracted with ethyl acetate (2×20 mL). The combined organic phase was washed with brine (2×30 mL), dried with anhydrous $Na_2SO_4$, filtered and concentrated in vacuo to give residue. The residue was purified by reverse phase (0.1% FA condition) to give the title compound (70 mg, 57% yield) as black solid. LC-MS (ESI+) m/z 1494.9 (M+H)+.

Step 2-Tert-butyl N-(cyclopropylmethyl)-N-[4-[4-[[3-(difluoromethyl)-1-[4-[2-[2-[2-[2-[2-[2-[[(3S)-2-[(2S)-3,3-dimethyl-2-[[(2S)-2-(methylamino)propanoyl]amino]butanoyl]-3-[[(1R)-tetralin-1-yl]carbamoyl]-3,4-dihydro-1H-isoquinolin-7-yl]oxy]ethoxy]ethoxy]ethoxy]ethoxy]ethoxy]ethyl]carbamoyl]phenyl]pyrazol-4-yl]carbamoyl]oxazol-2-yl]-2-pyridyl]carbamate To a mixture of tert-butyl N-[4-[4-[[1-[4-[2-[2-[2-[2-[2-[2-[[(3S)-2-[(2S)-2-[[(2S)-2-[benzyl oxycarbonyl(methyl)amino]propanoyl]amino]-3,3-dimethyl-butanoyl]-3-[[(1R)-tetralin-1-yl]carbamoyl]-3,4-dihydro-1H-isoquinolin-7-yl]oxy]ethoxy]ethoxy]ethoxy]ethoxy]ethoxy]-ethyl]carbamoyl]phenyl]-3-(difluoromethyl)pyrazol-4-yl]carbamoyl]oxazol-2-yl]-2-pyridyl]-N-(cyclopropylmethyl) carbamate (35.0 mg, 23.4 umol) in THF (2 mL) was added Pd/C (20 mg, 20% wt). The suspension was degassed under vacuum and purged with $H_2$ three times. The reaction mixture was stirred under $H_2$ (15 psi) at 20° C. for 1 hour. On completion, the reaction mixture was filtered and concentrated in vacuo to give the title compound (32.0 mg, crude quant. yield) as brown solid. LC-MS (ESI+) m/z 1360.6 (M+H)+.

Step 3—2-[2-(Cyclopropylmethylamino)-4-pyridyl]-N-[3-(difluoromethyl)-1-[4-[2-[2-[2-[2-[2-[2-[[(3S)-2-[(2S)-3,3-dimethyl-2-[[(2S)-2-(methylamino)propanoyl]amino]butanoyl]-3-[[(1R)-tetralin-1-yl]carbamoyl]-3,4-dihydro-1H-isoquinolin-7-yl]oxy]ethoxy]ethoxy]ethoxy]ethoxy]-ethoxy]ethyl]carbamoyl]phenyl pyrazol-4-yl]oxazole-4-carboxamide To a mixture of tert-butyl N-(cyclopropylmethyl)-N-[4-[4-[[3-(difluoromethyl)-1-[4-[2-[2-[2-[2-[2-[2-[[(3S)-2-[(2S)-3,3-dimethyl-2-[[(2S)-2-(methylamino)propanoyl]amino]butanoyl]-3-[[(1R)-tetralin-1-yl]carbamoyl]-3,4-dihydro-1H-isoquinolin-7-yl]oxy]ethoxy]ethoxy]ethoxy]ethoxy]ethoxy]ethyl]carbamoyl]phenyl]pyrazol-4-yl]carbamoyl]oxazol-2-yl]-2-pyridyl]carbamate (32.0 mg, 23.5 umol) in DCM (5 mL) was added HCl/dioxane (4 M, 2 mL). The reaction mixture was stirred at 20° C. for 1 hour. On completion, the reaction mixture was concentrated in vacuo to give the residue. The residue was purified by prep-HPLC (column: Phenomenex Synergi C18 150*25*10 um; mobile phase: [water (0.225% FA)-ACN]; B %: 16%-46%, 10 min) to give the title compound (8 mg, 6.17 umol, 26% yield) as a green solid. LC-MS (ESI+) m/z 1260.9 (M+H)+. $^1$H NMR (400 MHz, DMSO-$d_6$) δ 10.07 (s, 1H), 9.03-8.90 (m, 2H), 8.66 (s, 1H), 8.25-8.13 (m, 2H), 8.07-7.85 (m, 5H), 7.48-7.17 (m, 1H), 7.16-6.99 (m, 8H), 6.92 (s, 1H), 6.82-6.77 (m, 1H), 5.01-4.82 (m, 2H), 4.80-4.61 (m, 2H), 4.05 (s, 2H), 3.73 (s, 2H), 3.58-3.51 (m, 18H), 3.19-3.17 (m, 4H), 3.00-2.97 (m, 4H), 2.69-2.68 (m, 3H), 2.22-2.04 (m, 3H), 1.92-1.74 (m, 2H), 1.73-1.51 (m, 3H), 1.14-1.00 (m, 10H), 0.94 (s, 2H), 0.47-0.45 (m, 2H), 0.23-0.22 (m, 2H).

Example 516: 2-[2-(Cyclopropylmethylamino)-4-pyridyl]-N-[3-(difluoromethyl)-1-[4-[2-[2-[2-[2-[[(3S)-2-[(2S)-3,3-dimethyl-2-[[(2S)-2-(methylamino)propanoyl]amino]butanoyl]-3-[[(1R)-tetralin-1-yl]carbamoyl]-3,4-dihydro-1H-isoquinolin-7-yl]oxy]ethoxy]ethoxy]ethyl]carbamoyl]-phenyl]pyrazol-4-yl]oxazole-4-carboxamide, I-521
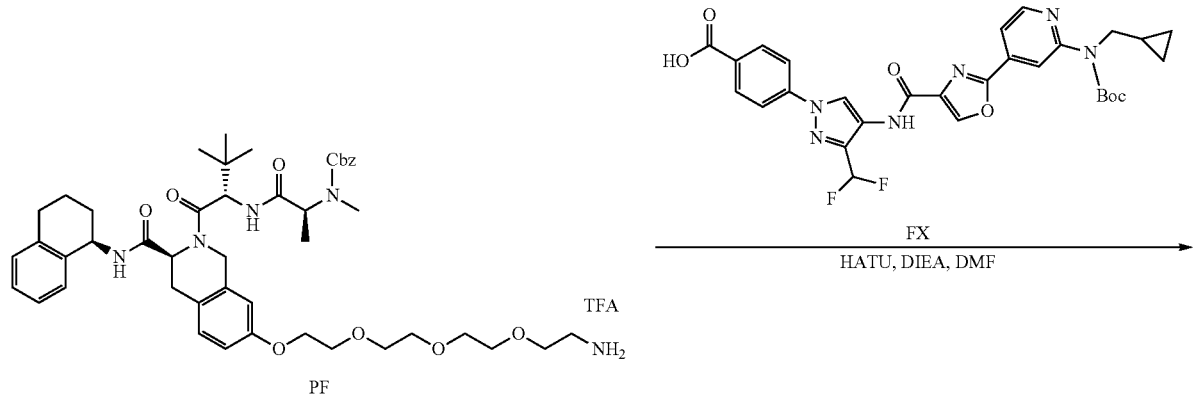
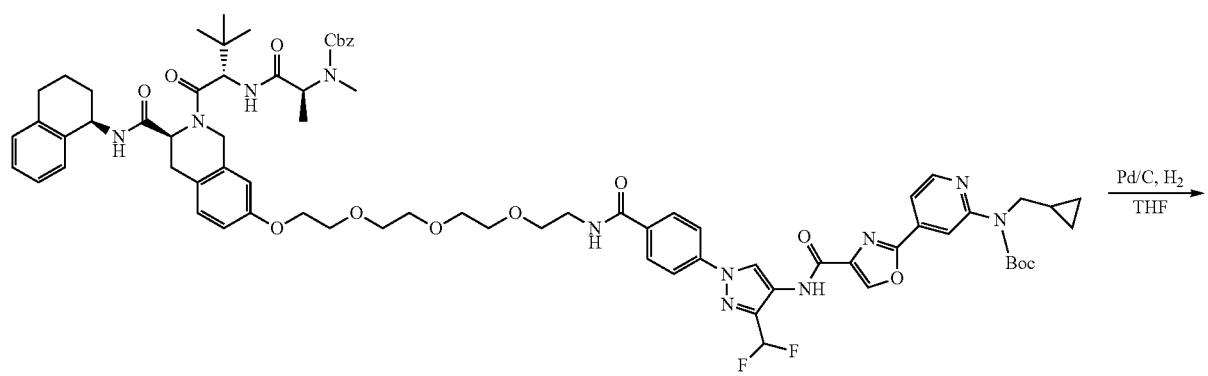
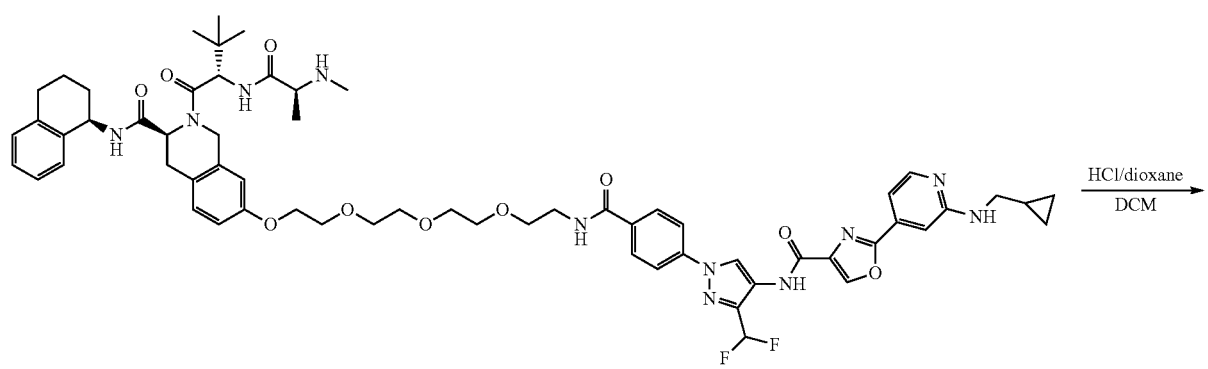

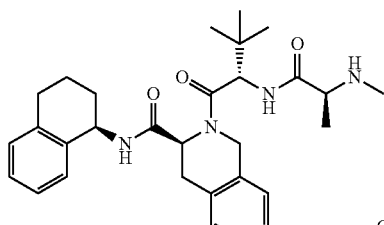
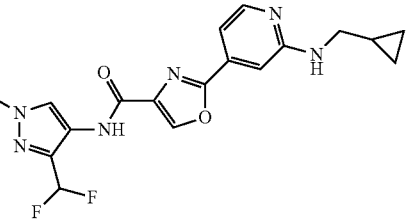

Step 1—Tert-butyl N-[4-[4-[[1-[2-[2-[2-[2-[[(3S)-2-[(2S)-2-[[(2S)-2-[benzyloxycarbonyl(methyl)amino]propanoyl]amino]-3,3-dimethyl-butanoyl]-3-[[(1R)-tetralin-1-yl]carbamoyl]-3,4-dihydro-1H-isoquinolin-7-yl]oxy]ethoxy]ethoxy]ethoxy]ethyl carbamoyl]phenyl]-3-(difluoromethyl)pyrazol-4-yl]carbamoyl]oxazol-2-yl]-2-pyridyl]-N-(cyclopropylmethyl)carbamate To a solution of benzyl N-[(1S)-2-[[(1S)-1-[(3S)-7-[2-[2-[2-(2-aminoethoxy)ethoxy]ethoxy]ethoxy]-3-[[(1R)-tetralin-1-yl]carbamoyl]-3,4-dihydro-1H-isoquinoline-2-carbonyl]-2,2-dimethyl-propyl]amino-1-methyl-2-oxo-ethyl]-N-methyl-carbamate (50 mg, 52.9 umol, TFA, Intermediate PF) and 4-[4-[[2-[2-[tert-butoxycarbonyl(cyclopropylmethyl)amino]-4-pyridyl]oxazole-4-carbonyl]amino]-3-(difluoromethyl)pyrazol-1-yl]benzoic acid (31.5 mg, 52.9 umol, Intermediate FX) in DMF (3 mL) was added DIPEA (34.2 mg, 264 umol, 46.1 uL) and HATU (24.1 mg, 63.5 umol). The mixture was stirred at 25° C. for 1.5 hr. On completion, the reaction mixture was quenched with H₂O (1 mL) and then concentrated in vacuo to give a residue. The residue was purified by reverse phase (0.1% FA condition) to give the title compound (40 mg, 53% yield) as a white solid. LC-MS (ESI⁺) m/z 1406.7 (M+H)⁺.

Step 2—Tert-butyl N-(cyclopropylmethyl)-N-[4-[4-[[3-(difluoromethyl)-1-[4-[2-[2-[2-[2-[[(3S)-2-[(2S)-3,3-dimethyl-2-[[(2S)-2-(methylamino)propanoyl]amino]butanoyl]-3-[[(1R)-tetralin-1-yl]carbamoyl]-3,4-dihydro-1H-isoquinolin-7-yl]oxy]ethoxy]ethoxy]ethoxy]ethyl]carbamoyl]-phenyl]pyrazol-4-yl]carbamoyl]oxazol-2-yl]-2-pyridyl]carbamate To a solution of tert-butyl N-[4-[4-[[1-[4-[2-[2-[2-[2-[[(3S)-2-[(2S)-2-[[(2S)-2-[benzyloxycarbonyl(methyl)amino]propanoyl]amino]-3,3-dimethyl-butanoyl]-3-[[(1R)-tetralin-1-yl]carbamoyl]-3,4-dihydro-1H-isoquinolin-7-yl]oxy]ethoxy]ethoxy]ethoxy]ethyl]carbamoyl]-phenyl]-3-(difluoromethyl)pyrazol-4-yl]carbamoyl]oxazol-2-yl]-2-pyridyl]-N-(cyclopropylmethyl)carbamate (40.0 mg, 28.4 umol) in THF (5 mL) was added Pd/C (20 mg, 10% wt), the reaction mixture was stirred at 25° C. for 40 mins under H₂. On completion, the mixture was filtered. The filtrate was concentrated in vacuo to give the title compound (35 mg, 96% yield) as a yellow solid. LC-MS (ESI⁺) m/z 1272.8 (M+H)⁺.

Step 3—2-[2-(Cyclopropylmethylamino)-4-pyridyl]-N-[3-(difluoromethyl)-1-[4-[2-[2-[2-[2-[[(3S)-2-[(2S)-3,3-dimethyl-2-[[(2S)-2-(methylamino)propanoyl]amino]butanoyl]-3-[[(1R)-tetralin-1-yl]carbamoyl]-3,4-dihydro-1H-isoquinolin-7-yl]oxy]ethoxy]ethoxy]ethoxy]ethyl]carbamoyl]-phenyl]pyrazol-4-yl]oxazole-4-carboxamide To a solution of tert-butyl N-(cyclopropylmethyl)-N-[4-[4-[[3-(difluoromethyl)-1-[4-[2-[2-[2-[2-[[(3S)-2-[(2S)-3,3-dimethyl-2-[[(2S)-2-(methylamino)propanoyl]amino]butanoyl]-3-[[(1R)-tetralin-1-yl]carbamoyl]-3,4-dihydro-1H-isoquinolin-7-yl]oxy]ethoxy]ethoxy]ethoxy]ethyl carbamoyl]phenyl]pyrazol-4-yl]carbamoyl]oxazol-2-yl]-2-pyridyl]carbamate (35.0 mg, 27.5 umol) in DCM (2 mL) was added HCl/dioxane (4 M, 2 mL), the reaction mixture was stirred at 20° C. for 1 hr. On completion, the reaction mixture was concentrated in vacuo to give a residue. The residue was purified by prep-HPLC (column: Phenomenex Synergi C18 150*25*10 um; mobile phase: [water (0.225% FA)-ACN]; B %: 15%-45%, 10 min) to give the title compound (23.0 mg, 71% yield, FA) as a white solid. $^1$H NMR (400 MHz, DMSO-$d_6$) δ 10.05 (s, 1H), 8.97 (s, 1H), 8.91 (s, 1H), 9.71-8.60 (m, 1H), 8.21-8.13 (m, 2H), 8.04-8.00 (m, 2H), 7.99-7.95 (m, 2H), 7.94-7.85 (m, 1H), 7.45-7.17 (m, 1H), 7.14-7.00 (m, 8H), 6.91-6.76 (m, 2H), 5.09-4.47 (m, 6H), 4.06-4.01 (m, 2H), 3.74-3.68 (m, 2H), 3.55 (s, 9H), 3.48-3.45 (m, 2H), 3.18 (t, J=6.0 Hz, 2H), 3.03-2.91 (m, 4H), 2.73-2.64 (m, 2H), 2.16 (s, 1H), 2.11 (s, 2H), 1.88-1.73 (m, 2H), 1.70-1.63 (m, 1H), 1.60-1.50 (m, 1H), 1.11-1.02 (m, 10H), 0.93 (s, 3H), 0.47-0.42 (m, 2H), 0.24-0.20 (m, 2H); LC-MS (ESI⁺) m/z 1172.8 (M+H)⁺.

TABLE 23

Compounds synthesized via Method 16 with the reductive amination of various amines with aldehydes in Step 1

| Ex-# | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| 517 | I-522 | UE | LS | 915.4 | 11.08 (s, 1H), 10.8 (s, 1H), 8.89 (s, 1H), 8.29-8.20 (m, 2H), 8.10 (s, 1H), 7.61-7.50 (m, 2H), 7.25-7.16 (m, 2H), 7.12 (d, J = 8.8 Hz, 1H), 7.03 (d, J = 7.2 Hz, 1H), 6.59 (t, J = 5.6 Hz, 1H), 5.07-5.04 (m, 1H), 4.32-4.16 (m, 2H), 3.95 (s, 2H), 3.79 (s, 3H), 3.53-3.41 (m, 22H), 2.94-2.82 (m, 1H), 2.77 (t, J = 5.6 Hz, 2H), 2.64-2.53 (m, 2H), 2.08-1.97 (m, 1H) |
| 518 | I-523 | WI | GF | 865.4 | 11.10 (s, 1H), 10.01 (s, 1H), 8.98 (s, 1H), 8.80 (s, 1H), 8.24 (s, 1H), 8.17 (d, J = 5.2 Hz, 1H), 7.82 (d, J = 8.4 Hz, 2H), 7.51 (d, J = 8.4 Hz, 2H), 7.45-7.15 (m, 1H), 7.14-7.08 (m, 2H), 7.07-7.02 (m, 1H), 6.99-6.92 (m, 2H), 6.88-6.85 (m, 1H), 5.37 (dd, J = 5.6, 12.8 Hz, 1H), 3.81 (s, 2H), 3.56 (s, 3H), 3.34-3.29 (m, 4H), 3.27-3.15 (m, 2H), 2.96-2.86 (m, 3H), 2.77-2.58 (m, 4H), 2.04-1.94 (m, 1H), 1.68-1.49 (m, 8H), 1.13-1.00 (m, 1H), 0.50-0.42 (m, 2H), 0.27-0.19 (m, 2H) |
| 519 | I-524 | LP | LS | 984.3 | 10.83 (s, 1H), 8.97 (s, 1H), 8.90 (s, 1H), 8.56 (s, 1H), 8.22 (s, 2H), 8.10 (s, 1H), 7.56 (s, 1H), 7.40 (s, 5H), 7.21 (s, 2H), 4.58-4.49 (m, 1H), 4.43-4.36 (m, 1H), 4.34 (s, 1H), 4.26-4.24 (m, 2H), 3.95 (s, 2H), 3.85-3.75 (m, 1H), 3.79 (s, 3H), 3.70-3.58 (m, 14H), 3.20-3.16 (m, 1H), 3.07 (s, 2H), 3.15-2.98 (m, 1H), 2.77 (s, 2H), 2.64-2.59 (m, 1H), 2.48-2.40 (m, 4H), 1.93-1.89 (m, 1H), 0.89 (s, 9H) |
| 520 | I-525 | VE | LS | 922.4 | 11.10 (s, 1H), 10.75-10.60 (m, 1H), 8.97-8.83 (m, 1H), 8.25-8.13 (m, 2H), 7.60-7.38 (m, 1H), 7.30-7.10 (m, 2H), 7.02-6.81 (m, 3H), 5.41-5.30 (m, 1H), 4.39-4.04 (m, 6H), 3.78 (s, 3H), 3.64-3.54 (m, 4H), 3.52-3.49 (m, 3H), 2.99-2.77 (m, 13H), 2.72-2.62 (m, 2H), 2.28-2.16 (m, 3H), 2.08 (s, 1H), 2.02-1.94 (m, 1H), 1.91-1.72 (m, 2H) |
| 521 | I-526 | VH | GY | 1027.5 | 11.06-10.07 (m, 1H), 10.16-9.95 (m, 1H), 9.01 (d, J = 2.4 Hz, 2H), 8.25 (d, J = 5.2 Hz, 1H), 8.16-7.97 (m, 3H), 7.83-7.67 (m, 3H), 7.50-7.37 (m, 1H), 7.35-7.24 (m, 2H), 7.22-7.15 (m, 1H), 7.13-6.95 (m, 2H), 6.92-6.81 (m, 1H), 5.38-5.27 (m, 1H), 4.50-3.99 (m, 6H), 3.27-3.20 (m, 4H), 3.02-2.65 (m, 15H), 2.37-1.69 (m, 3H), 1.58-1.39 (m, 1H), 1.23 (s, 4H), 1.20-1.14 (m, 1H), 0.85 (t, J = 6.4 Hz, 1H) |
| 522[b] | I-527 | HQ | VI | 749.0 | 11.70-11.64 (m, 1H), 11.06 (s, 1H), 9.24 (s, 2H), 9.07 (s, 1H), 9.01 (d, J = 4.8 Hz, 1H), 8.50 (s, 1H), 8.18 (d, J = 4.8 Hz, 1H), 8.06-8.04 (m, 2H), 7.80-7.68 (m, 3H), 7.00-6.89 (m, 2H), 6.85-6.82 (m, 1H), 5.38-5.30 (m, 1H), 4.28-4.20 (m, 2H), 3.80-3.70 (m, 2H), 3.65-3.51 (m, 9H), 3.19-3.08 (m, 2H), 2.99-2.82 (m, 3H), 2.74-2.57 (m, 2H), 2.04-1.91 (m, 1H), 1.88-1.77 (m, 2H) |
| 523 | I-528 | HQ | VM | 885.4 | 11.07 (s, 1H), 8.84 (s, 1H), 8.77 (s, 1H), 8.22 (d, J = 1.6 Hz, 1H), |

TABLE 23-continued

Compounds synthesized via Method 16 with the reductive amination
of various amines with aldehydes in Step 1

| Ex-# | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| | | | | | 7.73-7.67 (m, 2H), 7.56 (t, J = 6.4 Hz, 1H), 7.41 (d, J = 8.6 Hz, 2H), 7.25 (s, 1H), 7.18 (dd, J = 1.2, 5.2 Hz, 1H), 6.98-6.91 (m, 2H), 6.92-6.82 (m, 1H), 5.39-5.32 (m, 1H), 4.28-4.17 (m, 4H), 3.77 (s, 2H), 3.55 (s, 3H), 3.54-3.51 (m, 6H), 3.47-3.44 (m, 2H), 2.97-2.92 (m, 2H), 2.92-2.85 (m, 1H), 2.82 (t, J = 6.4 Hz, 2H), 2.70 (t, J = 5.6 Hz, 2H), 2.68-2.56 (m, 2H), 2.08-2.01 (m, 2H), 2.01-1.95 (m, 1H), 1.86-1.77 (m, 2H) |
| 524 | I-529 | VO | GF | 910.5 | 10.99 (s, 1H), 10.01 (s, 1H), 8.97 (s, 1H), 8.79 (s, 1H), 8.32 (s, 1H), 8.16 (d, J = 5.2 Hz, 1H), 7.80 (d, J = 8.4 Hz, 2H), 7.66 (d, J = 8.0 Hz, 1H), 7.49 (d, J = 8.8 Hz, 2H), 7.44-7.38 (m, 2H), 7.31-7.15 (m, 1H), 7.13-7.08 (m, 2H), 7.05 (d, J = 5.2 Hz, 1H), 6.59 (, J = 5.6 Hz, 1H), 6.09-6.04 (m, 1H), 5.15-5.05 (m, 1H), 4.42-4.30 (m, 4H), 3.77 (s, 2H), 3.56-3.52 (m, 12H), 3.22-3.17 (m, 2H), 2.95-2.90 (m, 1H), 2.69-2.66 (m, 1H), 2.43-2.30 (m, 1H), 2.05-1.94 (m, 1H), 1.27-1.11 (m, 1H), 0.49-0.43 (m, 2H), 0.26-0.21 (m, 2H) |
| 525 | I-530 | RI | GF | 823.1 | 11.07 (s, 1H), 9.97 (s, 1H), 8.96 (s, 1H), 8.79 (s, 1H), 8.19 (s, 1H), 8.16 (d, J = 5.2 Hz, 1H), 7.82 (d, J = 8.4 Hz, 2H), 7.51 (d, J = 8.4 Hz, 2H), 7.44-7.14 (m, 1H), 7.12 (s, 1H), 7.08 (t, J = 5.6 Hz, 1H), 7.04 (dd, J = 1.6, 5.2 Hz, 1H), 6.99-6.93 (m, 2H), 6.90-6.84 (m, 1H), 5.36 (dd, J = 5.2, 12.4 Hz, 1H), 3.84 (s, 2H), 3.56 (s, 3H), 3.52-3.48 (m, 2H), 3.47-3.44 (m, 2H), 3.18 (t, J = 6.0 Hz, 2H), 2.99-2.94 (m, 2H), 2.90-2.82 (m, 1H), 2.74 (t, J = 5.2 Hz, 2H), 2.70-2.57 (m, 2H), 2.03-1.94 (m, 1H), 1.90-1.79 (m, 2H), 1.12-1.02 (m, 1H), 0.49-0.43 (m, 2H), 0.26-0.20 (m, 2H) |
| 526 | I-531 | RH | GF | 823.4 | 11.09 (s, 1H), 10.01 (s, 1H), 8.96 (s, 1H), 8.79 (s, 1H), 8.21 (s, 1H), 8.15 (d, J = 5.2 Hz, 1H), 7.83 (d, J = 8.4 Hz, 2H), 7.53 (d, J = 8.4 Hz, 2H), 7.44-7.14 (m, 1H), 7.13-7.07 (m, 2H), 7.06-7.02 (m, 2H), 7.00 (d, J = 8.0 Hz, 1H), 6.87 (d, J = 8.0 Hz, 1H), 5.37-5.28 (m, 1H), 3.86 (s, 2H), 3.40-3.38 (m, 4H), 3.31 (s, 3H), 3.18 (t, J = 6.0 Hz, 2H), 2.94-2.84 (m, 1H), 2.76 (t, J = 5.6 Hz, 2H), 2.71-2.66 (m, 2H), 2.65-2.54 (m, 2H), 2.05-1.94 (m, 1H), 1.89-1.77 (m, 2H), 1.13-1.00 (m, 1H), 0.50-0.41 (m, 2H), 0.25-0.20 (m, 2H) |
| 527 | I-532 | RH | JC | 951.4 | 11.07 (s, 1H), 9.98 (s, 1H), 8.99 (s, 1H), 8.79 (s, 1H), 8.25 (d, J = 5.6 Hz, 1H), 7.81 (d, J = 7.6 Hz, 2H), 7.61 (t, J = 6.4 Hz, 1H), 7.50 (d, J = 7.2 Hz, 2H), 7.43-7.15 (m, 3H), 7.06-6.97 (m, 2H), 6.87 (d, J = 7.6 Hz, 1H), 5.33 (dd, J = 5.2, 12.8 Hz, 1H), 4.30-4.19 (m, 2H), 3.81 (s, 2H), 3.55-3.44 (m, 7H), 2.96-2.83 (m, 1H), 2.71-2.64 (m, 4H), |

TABLE 23-continued

Compounds synthesized via Method 16 with the reductive amination
of various amines with aldehydes in Step 1

| Ex-# | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| | | | | | 2.60-2.53 (m, 2H), 2.04-1.96 (m, 1H), 1.90-1.85 (m, 2H) |
| 528 | I-533 | RI | JC | 851.1 | 11.08 (s, 1H), 9.99 (s, 1H), 8.99 (s, 1H), 8.80 (s, 1H), 8.25 (d, J = 5.2 Hz, 1H), 8.16 (s, 1H), 7.83 (d, J = 8.4 Hz, 2H), 7.61 (t, J = 6.8 Hz, 1H), 7.53 (d, J = 8.4 Hz, 2H), 7.44-7.15 (m, 3H), 6.99-6.93 (m, 2H), 6.90-6.84 (m, 1H), 5.36 (dd, J = 5.2, 12.4 Hz, 1H), 4.32-4.19 (m, 2H), 3.87 (s, 2H), 3.56 (s, 3H), 3.52 (t, J = 5.2 Hz, 2H), 3.49-3.46 (t, J = 6.4 Hz, 2H), 3.01-2.94 (m, 2H), 2.91-2.82 (m, 1H), 2.77 (t, J = 5.6 Hz, 2H), 2.72-2.58 (m, 2H), 2.03-1.94 (m, 1H), 1.90-1.78 (m, 2H) |
| 529 | I-534 | LG | JC | 865.4 | 11.07 (s, 1H), 9.99 (s, 1H), 8.99 (s, 1H), 8.78 (s, 1H), 8.25 (d, J = 5.2 Hz, 1H), 7.81 (d, J = 8.4 Hz, 2H), 7.61 (t, J = 6.4 Hz, 1H), 7.51 (d, J = 8.4 Hz, 2H), 7.43-7.14 (m, 3H), 7.05-6.94 (m, 2H), 6.84 (d, J = 8.2 Hz, 1H), 5.32 (dd, J = 5.2, 12.8 Hz, 1H), 4.29-4.20 (m, 2H), 3.81 (s, 2H), 3.43 (t, J = 6.0 Hz, 2H), 3.36 (t, J = 6.0 Hz, 2H), 3.31 (s, 3H), 2.93-2.83 (m, 1H), 2.75-2.57 (m, 6H), 2.05-1.95 (m, 1H), 1.86-1.75 (m, 2H), 1.75-1.65 (m, 2H) |
| 530 | I-535 | LF | JC | 865.4 | 11.08 (s, 1H), 10.10 (d, J = 2.0 Hz, 1H), 9.06 (s, 1H), 8.87 (s, 1H), 8.26 (d, J = 5.6 Hz, 1H), 8.09-7.91 (m, 3H), 7.81-7.76 (m, 2H), 7.48-7.17 (m, 3H), 7.02-6.91 (m, 2H), 6.89-6.78 (m, 1H), 5.39-5.35 (m, 1H), 4.37-4.29 (m, 2H), 4.22 (m, 3H), 3.56 (d, J = 4.8 Hz, 3H), 3.50-3.44 (m, 4H), 3.13-2.79 (m, 5H), 2.70 (d, J = 4.8 Hz, 2H), 2.62 (d, J = 8.8 Hz, 1H), 2.07-1.93 (m, 3H), 1.88-1.75 (m, 2H) |
| 531ᶜ | I-536 | OS | GF | 934.5 | 11.08 (s, 1H), 10.16 (s, 1H), 8.95 (s, 1H), 8.77 (s, 1H), 8.30 (s, 2H), 8.16 (d, J = 5.2 Hz, 1H), 7.79 (d, J = 8.0 Hz, 2H), 7.49 (d, J = 8.0 Hz, 2H), 7.43-7.14 (m, 2H), 7.11 (s, 1H), 7.10-6.93 (m, 4H), 6.88 (d, J = 3.6 Hz, 1H), 5.35-5.33 (m, 1H), 4.31 (s, 2H), 3.81-3.79 (m, 11H), 3.22-3.12 (m, 2H), 2.93-2.91 (m, 4H), 2.72-2.59 (m, 2H), 2.59-2.58 (m, 2H), 2.59-2.57 (m, 1H), 2.39-2.36 (m, 1H), 2.29-2.26 (m, 2H), 2.01-1.98 (m, 1H), 1.79 1.76 (m, 2H), 1.9-1.06 (m, 1H), 0.48-0.44 (m, 2H), 0.50-0.40 (m, 1H), 0.24-0.21 (m, 2H) |
| 532ᶜ | I-537 | OV | GF | 934.5 | 11.10 (s, 1H), 10.23 (s, 1H), 9.55 (s, 1H), 9.14 (s, 1H), 9.07 (s, 1H), 8.89 (s, 1H), 8.11 (d, J = 6.4 Hz, 1H), 7.96 (d, J = 8.8 Hz, 2H), 7.77 (d, J = 8.8 Hz, 2H), 7.56 (s, 1H), 7.49-7.18 (m, 3H), 7.13-7.02 (m, 2H), 6.91 (d, J = 8.0 Hz, 1H), 5.43-5.30 (m, 1H), 4.55-4.43 (m, 2H), 4.30-4.17 (m, 2H), 3.94-3.81 (m, 2H), 3.76-3.46 (m, 2H), 3.34 (s, 3H), 3.30-3.21 (m, 4H), 3.05-2.95 (m, 2H), 2.94-2.85 (m, 4H), 2.85-2.80 (m, 1H), 2.75-2.69 (m, 2H), 2.65-2.59 (m, 2H), 2.06-1.92 (m, 3H), |

TABLE 23-continued

Compounds synthesized via Method 16 with the reductive amination
of various amines with aldehydes in Step 1

| Ex-# | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| 533 | I-538 | PA | OX | 829.3 | 1.20-1.07 (m, 1H), 0.60-0.50 (m, 2H), 0.35-0.27 (m, 2H) 11.22 (s, 1H), 10.70 (s, 1H), 9.02 (s, 1H), 8.88-8.78 (m, 1H), 8.24 (s, 1H), 8.17 (d, J = 5.2 Hz, 1H), 7.83 (d, J = 8.4 Hz, 2H), 7.52 (d, J = 8.8 Hz, 2H), 7.25 (s, 1H), 7.18-7.01 (m, 5H), 5.34 (d, J = 5.6, 13.2 Hz, 1H), 3.79 (s, 2H), 3.57-3.47 (m, 5H), 3.24-3.15 (m, 2H), 2.70-2.61 (m, 7H), 2.37-2.31 (m, 2H), 2.21-2.08 (m, 1H), 2.21-2.07 (m, 2H), 1.78 (d, J = 7.2 Hz, 2H), 1.12-0.98 (m, 1H), 0.52-0.40 (m, 2H), 0.29-0.17 (m, 2H) |
| 534 | I-539 | VR | VZ | 885.5 | 11.09 (s, 1H), 9.99 (s, 1H), 8.97 (s, 1H), 8.84 (s, 1H), 8.16 (d, J = 5.2 Hz, 1H), 7.75-7.67 (m, 2H), 7.64-7.55 (m, 1H), 7.29 (t, J = 54.0 Hz, 1H), 7.12 (s, 1H), 7.10-7.06 (m, 1H), 7.05-7.03 (m, 1H), 7.02-7.00 (m, 1H), 7.00-6.96 (m, 1H), 6.85 (d, J = 8.0 Hz, 1H), 5.32 (dd, J = 5.2, 12.8 Hz, 1H), 3.80 (s, 2H), 3.56-3.47 (m, 6H), 3.42-3.37 (m, 2H), 3.30 (s, 3H), 3.19 (t, J = 6.0 Hz, 2H), 2.94-2.83 (m, 1H), 2.74-2.57 (m, 6H), 2.03-1.95 (m, 1H), 1.85-1.74 (m, 2H), 1.12-1.02 (m, 1H), 0.49-0.42 (m, 2H), 0.26-0.20 (m, 2H) |
| 535[b] | I-540 | PD | PB | 865.3 | 10.85 (s, 1H), 9.78 (s, 1H), 8.73 (s, 1H), 8.57 (s, 1H), 8.07 (s, 1H), 7.93 (d, J = 5.2 Hz, 1H), 7.61 (d, J = 8.0 Hz, 2H), 7.32 (d, J = 8.0 Hz, 2H), 7.05 (t, J = 54 Hz, 1H), 6.88 (s, 1H), 6.85-6.80 (m, 2H), 6.80-6.74 (m, 2H), 6.63 (d, J = 7.2 Hz, 1H), 5.15-5.05 (m, 1H), 3.67 (s, 2H), 3.09 (s, 3H), 3.00-2.92 (m, 2H), 2.72-2.60 (m, 1H), 2.49-2.37 (m, 4H), 2.36-2.31 (m, 2H), 1.82-1.71 (m, 1H), 1.40-1.21 (m, 4H), 1.18-1.07 (m, 4H), 1.02-0.84 (m, 1H), 0.79 (s, 3H), 0.25-0.19 (m, 2H), 0.02-0.04 (m, 2H) |
| 536 | I-541 | HQ | WJ | 860.4 | 11.10 (s, 1H), 9.87 (s, 1H), 8.90 (s, 1H), 8.73 (d, J = 2.0 Hz, 1H), 8.43 (s, 1H), 8.32 (s, 1H), 8.22 (d, J = 5.2 Hz, 1H), 8.03 (s, 1H), 7.99 (s, 1H), 7.58 (t, J = 6.8 Hz, 1H), 7.22 (s, 1H), 7.19 (d, J = 5.26 Hz, 1H), 6.94 (d, J = 6.4 Hz, 2H), 6.86-6.81 (m, 1H), 5.37-5.34 (m, 1 H), 4.27-4.17 (m, 2H), 3.91 (s, 3H), 3.75 (s, 2H), 3.52 (s, 3H), 3.46-3.42 (m, 8H), 2.91-2.89 (m, 3H), 2.64-2.58 (m, 4H), 1.99-1.98 (m, 1H), 1.79 (m, 2H) |
| 537 | I-542 | PH | PG | 836.5 | 11.61-10.80 (m, 1H), 10.02 (s, 1H), 8.97 (s, 1H), 8.80 (s, 1H), 8.29 (s, 2H), 8.16 (d, J = 5.2 Hz, 1H), 7.83 (d, J = 8.4 Hz, 2H), 7.53 (d, J = 8.4 Hz, 2H), 7.43-7.15 (m, 2H), 7.13-7.02 (m, 5H), 5.42-5.30 (dd, J = 5.4, 12.7 Hz, 1H), 3.91 (s, 2H), 3.85-3.83 (m, 2H), 3.39-3.28 (m, 3H), 3.18 (t, J = 6.4 Hz, 2H), 2.96-2.84 (m, 1H), 2.77-2.68 (m, 2H), 2.68-2.64 (m, 2H), 2.64-2.58 (d, J = 6.8 Hz, 2H), 2.04-1.94 (m, 1H), 1.58-1.42 (m, 4H), 1.38-1.26 (m, 2H), |

TABLE 23-continued

Compounds synthesized via Method 16 with the reductive amination
of various amines with aldehydes in Step 1

| Ex-# | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| 538 | I-543 | WH | GF | 852.3 | 1.17-0.97 (m, 1H), 0.50-0.41 (m, 2H), 0.28-0.19 (m, 2H) 11.09 (s, 1H), 10.00 (s, 1H), 8.97 (s, 1H), 8.79 (s, 1H), 8.55 (t, J = 6.0 Hz, 1H), 8.20-8.12 (m, 2H), 7.80 (d, J = 8.4 Hz, 2H), 7.49 (d, J = 8.4 Hz, 2H), 7.43-7.15 (m, 1H), 7.13-7.08 (m, 2H), 7.07-7.02 (m, 3H), 6.95 (d, J = 8.4 Hz, 1H), 5.34 (dd, J = 5.6, 12.8 Hz, 1H), 4.34 (d, J = 6.0 Hz, 2H), 3.95 (s, 2H), 3.82 (s, 2H), 3.59-3.57 (m, 2H), 3.30 (s, 3H), 3.21-3.14 (m, 2H), 2.93-2.84 (m, 1H), 2.77 (t, J = 5.2 Hz, 2H), 2.71-2.57 (m, 2H), 2.04-1.93 (m, 1H), 1.13-1.01 (m, 1H), 0.49-0.41 (m, 2H), 0.27-0.19 (m, 2H) |
| 539 | I-544 | SV | GY | 902.5 | 11.02 (s, 1H), 9.03 (s, 1H), 8.96 (s, 1H), 8.26 (d, J = 5.2 Hz, 1H), 8.06 (s, 1H), 8.00 (d, J = 8.4 Hz, 2H), 7.76 (s, 1H), 7.71 (t, J = 6.4 Hz, 1H), 7.60 (d, J = 8.4 Hz, 2H), 7.27 (s, 1H), 7.17 (dd, J = 1.2, 5.2 Hz, 1H), 6.98-6.89 (m, 2H), 6.84 (dd, J = 1.2, 7.2 Hz, 1H), 5.47-5.38 (m, 1H), 4.31-4.19 (m, 2H), 4.09 (s, 2H), 3.65 (t, J = 5.2 Hz, 2H), 3.61-3.58 (m, 2H), 3.58-3.56 (m, 2H), 3.55 (s, 3H), 3.47 (t, J = 6.0 Hz, 2H), 3.01 (s, 3H), 2.99-2.91 (m, 4H), 2.80-2.74 (m, 1H), 2.72-2.52 (m, 2H), 2.05-1.95 (m, 1H), 1.88-1.75 (m, 2H) |
| 540 | I-545 | PL | GF | 852.4 | 11.09 (s, 1H), 9.99 (s, 1H), 8.97 (s, 1H), 8.79 (s, 1H), 8.16 (d, J = 5.2 Hz, 1H), 7.81 (d, J = 8.4 Hz, 2H), 7.63 (t, J = 5.6 Hz, 1H), 7.50 (d, J = 8.4 Hz, 2H), 7.27 (t, J = 7.6 Hz, 1H), 7.11 (s, 1H), 7.10-7.01 (m, 4H), 6.94 (d, J = 7.6 Hz, 1H), 5.34 (dd, J = 5.2, 12.8 Hz, 1H), 4.19 (d, J = 5.6 Hz, 2H), 4.04 (t, J = 6.4 Hz, 2H), 3.80 (s, 2H), 3.31 (s, 3H), 3.18 (t, J = 6.0 Hz, 2H), 2.94-2.86 (m, 1H), 2.73-2.60 (m, 2H), 2.55-2.52 (m, 2H), 2.04-1.94 (m, 1H), 1.81-1.70 (m, 2H), 1.11-1.02 (m, 1H), 0.48-0.42 (m, 2H), 0.25-0.19 (m, 2H) |
| 544 | I-549 | PZ | GF | 824.2 | 11.15 (s, 1H), 9.93 (s, 1H), 8.91 (s, 1H), 8.72 (s, 1H), 8.21 (s, 1H), 8.11 (d, J = 5.2 Hz, 1H), 7.75 (d, J = 8.8 Hz, 2H), 7.45 (d, J = 8.8 Hz, 2H), 7.38-7.17 (m, 2H), 7.12-7.03 (m, 3H), 7.01-6.94 (m, 2H), 5.28 (d, J = 5.2, 12.8 Hz, 1H), 3.72 (s, 2H), 3.19-3.09 (m, 8H), 2.89-2.76 (m, 2H), 2.62 (d, J = 2.0, 3.6 Hz, 4H), 2.58-2.52 (m, 5H), 2.32-2.25 (m, 2H), 2.09 (td, J = 5.2, 10.4 Hz, 1H), 1.78-1.68 (m, 2H), 1.64 (d, J = 6.5 Hz, 2H), 1.07-0.96 (m, 1H), 0.45-0.37 (m, 2H), 0.21-0.14 (m, 2H) |
| 545 | I-550 | PA | GF | 854.4 | 11.16 (s, 1H), 9.97 (s, 1H), 8.95 (s, 1H), 8.77 (s, 1H), 8.20 (s, 1H), 8.15 (d, J = 5.2 Hz, 1H), 7.80 (d, J = 8.4 Hz, 2H), 7.50 (d, J = 8.4 Hz, 2H), 7.42-7.10 (m, 4H), 7.08-6.99 (m, 3H), 5.32 (dd, J = 5.2, 12.8 Hz, 1H), 3.83 (s, 2H), 3.55-3.52 (m, 2H), 3.50-3.48 (m, 6H), 3.18 (t, J = 6.0 Hz, 2H), 2.95-2.81 (m, 1H), 2.75-2.70 (m, 2H), 2.68-2.60 (m, 4H), |

TABLE 23-continued

Compounds synthesized via Method 16 with the reductive amination of various amines with aldehydes in Step 1

| Ex-# | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| 546 | I-551 | JG | GF | 854.3 | 11.21 (s, 1H), 10.00 (s, 1H), 8.97 (s, 1H), 8.77 (s, 1H), 8.25 (s, 1H), 8.16 (d, J = 5.2 Hz, 1H), 7.78 (d, J = 8.4 Hz, 2H), 7.54-7.45 (m, 2H), 7.29 (t, J = 54 Hz 1H), 7.14-7.06 (m, 4H), 7.05-7.02 (m, 1H), 7.01-6.97 (m, 1H), 5.35 (dd, J = 5.2, 12.8 Hz, 1H), 3.80 (s, 2H), 3.53-3.49 (m, 8H), 3.18 (t, J = 6.0 Hz, 2H), 2.91-2.84 (m, 1H), 2.75-2.65 (m, 6H), 2.19-2.08 (m, 1H), 1.82-1.73 (m, 2H), 1.08-1.06 (m, 1H), 0.51-0.40 (m, 2H), 0.24-0.20 (m, 2H) |
| 547 | I-552 | QC | GF | 839.4 | 11.08 (s, 1H), 9.97 (s, 1H), 8.95 (s, 1H), 8.78 (s, 1H), 8.15 (d, J = 5.2 Hz, 1H), 7.79 (d, J = 8.4 Hz, 2H), 7.48 (d, J = 8.8 Hz, 2H), 7.42-7.14 (m, 2H), 7.12-6.98 (m, 6H), 5.39-5.32 (m, 1H), 3.99 (t, J = 5.6 Hz, 2H), 3.78 (s, 2H), 3.69 (t, J = 5.6 Hz, 2H), 3.55-3.52 (m, 2H), 3.47-3.45 (m, 4H), 3.18 (t, J = 6.0 Hz, 2H), 2.95-2.83 (m, 1H), 2.69-2.58 (m, 4H), 2.06-1.96 (m, 1H), 2.17-2.10 (m, 1H), 1.88-1.77 (m, 2H), 1.12-1.01 (m, 1H), 0.49-0.42 (m, 2H), 0.26-0.19 (m, 2H) |
| 548[d] | I-553 | QE | GF | 1224.5 | 10.22 (s, 1H), 9.34 (s, 1H), 9.14 (s, 1H), 8.88 (s, 2H), 8.75 (d, J = 8.0 Hz, 1H), 8.49 (s, 1H), 8.10 (d, J = 6.4 Hz, 1H), 7.95 (d, J = 8.4 Hz, 2H), 7.73 (d, J = 8.4 Hz, 2H), 7.71-7.53 (m, 3H), 7.50-7.19 (m, 5H), 5.39 (dd, J = 3.2, 7.6 Hz, 1H), 4.47 (t, J = 7.6 Hz, 1H), 4.26-4.20 (m, 2H), 4.18-4.14 (m, 2H), 3.92-3.72 (m, 7H), 3.61-3.55 (m, 7H), 3.55-3.48 (m, 14H), 3.14-3.07 (m, 2H), 2.31-2.17 (m, 2H), 2.11-1.95 (m, 3H), 1.79-1.52 (m, 4H), 1.36 (d, J = 6.8 Hz, 2H), 1.26-1.23 (m, 3H), 1.19-1.00 (m, 5H), 0.58-0.52 (m, 2H), 0.35-0.29 (m, 2H) |
| 549[d] | I-554 | QF | GF | 1136.5 | 10.00 (s, 1H), 8.95 (s, 1H), 8.78 (s, 1H), 8.47 (s, 1H), 8.26 (s, 1H), 8.15 (d, J = 4.8 Hz, 1H), 8.11 (s, 1H), 7.80 (d, J = 6.4 Hz, 2H), 7.71-7.60 (m, 2H), 7.55-7.14 (m, 6H), 7.13-6.99 (m, 3H), 5.38 (d, J = 5.2 Hz, 1H), 4.52-4.44 (m, 1H), 4.14 (s, 2H), 4.05-3.60 (m, 16H), 3.21-3.15 (m, 2H), 2.72 (s, 2H), 2.28-2.12 (m, 5H), 2.08-1.98 (m, 2H), 1.71-1.58 (m, 4H), 1.56-1.48 (m, 2H), 1.15 (s, 3H), 1.11-0.84 (m, 7H), 0.45 (d, J = 7.2 Hz, 2H), 0.22 (d, J = 3.2 Hz, 2H) |
| 550[d] | I-555 | QG | GF | 1180.5 | 9.99 (s, 1H), 8.96 (s, 1H), 8.79 (s, 1H), 8.48 (s, 1H), 8.26 (s, 1H), 8.16 (d, J = 5.2 Hz, 1H), 8.11 (d, J = 8.8 Hz, 1H), 7.81 (d, J = 8.4 Hz, 2H), 7.67 (d, J = 8.0 Hz, 1H), 7.64 (s, 1H), 7.51 (d, J = 8.4 Hz, 2H), 7.49-7.40 (m, 2H), 7.31-7.17 (m, 2H), 7.16-7.07 (m, 2H), 7.04 (d, J = 5.6 Hz, 1H), 5.41-5.35 (m, 1H), 4.55-4.45 (m, 1H), 4.17-4.12 (m, 2H), 3.81-3.73 (m, 14H), 3.59-3.57 (m, 2H), 3.55-3.53 (m, 2H), 3.49 (s, 3H), 3.22-3.16 (m, 2H), |

TABLE 23-continued

Compounds synthesized via Method 16 with the reductive amination
of various amines with aldehydes in Step 1

| Ex-# | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| | | | | | 2.76-2.70 (m, 2H), 2.25 (s, 3H), 2.23-2.14 (m, 2H), 2.11-2.01 (m, 2H), 1.68-1.62 (m, 2H), 1.58-1.52 (m, 2H), 1.35-0.84 (m, 11H), 0.50-0.43 (m, 2H), 0.26-0.20 (m, 2H) |
| 551[d] | I-556 | QH | GF | 1114.6 (M + Na)+ | 9.95 (s, 1H), 8.96 (s, 1H), 8.76 (s, 1H), 8.47 (s, 1H), 8.16 (d, J = 5.2 Hz, 1H), 7.89 (d, J = 8.8 Hz, 1H), 7.77 (d, J = 8.4 Hz, 2H), 7.69-7.41 (m, 6H), 7.30-7.20 (m, 2H), 7.17-7.01 (m, 4H), 5.38 (dd, J = 2.4, 7.6 Hz, 1H), 4.54-4.43 (m, 1H), 4.18-4.15 (m, 2H), 3.81-3.73 (m, 6H), 3.63-3.59 (m, 2H), 3.56-3.48 (m, 4H), 3.18 (t, J = 6.4 Hz, 2H), 2.99-2.93 (m, 1H), 2.66-2.62 (m, 2H), 2.19-2.16 (m, 4H), 2.10-1.90 (m, 2H), 1.63-1.52 (m, 6H), 1.23 (s, 3H), 1.10-1.06 (m, 5H), 0.90-0.85 (m, 1H), 0.47-0.43 (m, 2H), 0.25-0.21 (m, 2H) |
| 552 | I-557 | QN | GF | 911.5 | 10.97 (s, 1H), 10.00 (s, 1H), 8.97 (s, 1H), 8.78 (s, 1H), 8.15 (d, J = 5.2 Hz, 1H), 7.90 (t, J = 6.4 Hz, 1H), 7.80 (d, J = 8.8 Hz, 2H), 7.66 (d, J = 7.6 Hz, 1H), 7.48 (d, J = 8.4 Hz, 2H), 7.45 (s, 1H), 7.40 (d, J = 12.4 Hz, 1H), 7.37-7.14 (m, 1H), 7.13-7.06 (m, 2H), 7.03 (dd, J = 1.2, 5.2 Hz, 1H), 5.15-5.02 (m, 1H), 4.45-4.38 (m, 1H), 4.31-4.29 (m, 1H), 4.27 (d, J = 6.4 Hz, 2H), 4.10-4.04 (m, 2H), 3.78 (s, 2H), 3.63-3.54 (m, 8H), 3.20-3.14 (m, 2H), 2.98-2.85 (m, 1H), 2.70-2.67 (m, 2H), 2.60 (s, 2H), 2.02-1.93 (m, 1H), 1.12-1.01 (m, 1H), 0.49-0.42 (m, 2H), 0.25-0.19 (m, 2H) |
| 553 | I-558 | QP | GF | 823.4 | 10.96 (s, 1H), 9.98 (s, 1H), 8.95 (s, 1H), 8.77 (s, 1H), 8.24 (s, 1H), 8.15 (d, J = 5.6 Hz, 1H), 7.79 (d, J = 8.0 Hz, 3H), 7.67 (d, J = 7.6 Hz, 1H), 7.52-7.46 (m, 3H), 7.42-7.39 (m, 1H), 7.39-7.15 (m, 1H), 7.11 (s, 1H), 7.08-7.02 (m, 2H), 5.12-5.05 (m, 1H), 4.50-4.35 (m, 2H), 4.31-4.27 (m, 2H), 4.09-4.03 (m, 2H), 3.78 (s, 2H), 3.20-3.16 (m, 2H), 2.95-2.83 (m, 1H), 2.79-2.68 (m, 2H), 2.64-2.58 (m, 1H), 2.42-2.38 (m, 1H), 2.03-1.92 (m, 1H), 1.10-1.02 (m, 1H), 0.49-0.43 (m, 2H), 0.25-0.18 (m, 2H) |
| 554 | I-559 | OD | QV | 969.4 | 10.99 (s, 1H), 9.00 (s, 1H), 8.97 (s, 1H), 8.26 (d, J = 5.6 Hz, 1H), 7.90-7.78 (m, 2H), 7.70-7.63 (m, 1H), 7.57-7.48 (m, 2H), 7.26 (s, 1H), 7.18 (d, J = 5.2 Hz, 1H), 7.03-6.96 (m, 2H), 6.88-6.81 (m, 1H), 5.37-5.26 (m, 1H), 4.44-4.32 (m, 2H), 4.31-4.11 (m, 4H), 3.84-3.80 (m, 2H), 3.78-3.69 (m, 4H), 3.31-3.30 (m, 3H), 2.94-2.82 (m, 1H), 2.65-2.56 (m, 6H), 2.46-2.40 (m, 4H), 2.22 (s, 3H), 2.09-1.93 (s, 1H), 1.64-1.55 (m, 2H), 1.54-1.44 (m, 6H) |
| 555 | I-560 | OD | QX | 957.4 | 11.07 (s, 1H), 10.88 (s, 1H), 9.02 (s, 1H), 8.95 (s, 1H), 8.47 (t, J = 5.6 Hz, 1H), 8.29-8.23 (m, 2H), 7.94 (d, J = 8.8 Hz, 2H), 7.69 (t, J = 6.4 Hz, 1H), 7.54 (d, J = 8.4 Hz, 2H), |

TABLE 23-continued

Compounds synthesized via Method 16 with the reductive amination
of various amines with aldehydes in Step 1

| Ex-# | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| | | | | | 7.27 (s, 1H), 7.22-7.15 (m, 1H), 7.05-6.94 (m, 2H), 6.85 (d, J = 8.4 Hz, 1H), 5.32 (dd, J = 5.2, 12.4 Hz, 1H), 4.30-4.20 (m, 2H), 3.89 (s, 2H), 3.42-3.32 (m, 8H), 3.31 (s, 3H), 2.95-2.84 (m, 1H), 2.68-2.55 (m, 6H), 2.23 (s, 6H), 2.03-1.94 (m, 1H), 1.66-1.44 (m, 8H) |
| 558 | I-563 | PL | GY | 873.5 | 11.10 (s, 1H), 11.00 (s, 1H), 9.01 (s, 1H), 8.91 (s, 1H), 8.24 (d, J = 2.0 Hz, 1H), 8.04 (s, 1H), 7.91 (d, J = 8.4 Hz, 2H), 7.74-7.66 (m, 2H), 7.74-7.66 (m, 1H), 7.62 (t, J = 6.4 Hz, 1H), 7.50 (d, J = 8.4 Hz, 2H), 7.26 (s, 1H), 7.18 (dd, J = 1.2, 5.6 Hz, 1H), 7.08-7.00 (m, 2H), 6.94 (d, J = 8.0 Hz, 1H), 5.37-5.30 (m, 1H), 4.30-4.16 (m, 4H), 4.04 (t, J = 6.4 Hz, 2H), 3.78 (s, 2H), 3.31 (s, 3H), 2.94-2.84 (m, 1H), 2.70-2.58 (m, 4H), 2.05-1.92 (m, 1H), 1.81-1.68 (m, 2H) |
| 559 | I-564 | RG | GY | 914.2 | 11.13-10.94 (m, 2H), 9.00 (s, 1H), 8.90 (s, 1H), 8.31-8.20 (m, 3H), 8.03 (s, 1H), 7.90 (d, J = 8.4 Hz, 2H), 7.75-7.65 (m, 2H), 7.50 (d, J = 8.4 Hz, 2H), 7.26 (s, 1H), 7.20-7.13 (m, 1H), 6.90 (d, J = 8.6 Hz, 1H), 6.80 (d, J = 1.6 Hz, 1H), 6.59 (dd, J = 2.4, 8.6 Hz, 1H), 5.25 (dd, J = 5.2, 13.2 Hz, 1H), 4.24 (dd, J = 6.8, 9.6 Hz, 2H), 3.80 (s, 2H), 3.52-3.50 (m, 4H), 3.28 (s, 2H), 3.05-3.02 (m, 4H), 2.91-2.82 (m, 1H), 2.68-2.66 (m, 2H), 2.64-2.60 (m, 2H), 2.57-2.56 (m, 6H), 2.06 (s, 3H), 2.01-1.94 (m, 1H) |
| 562 | I-567 | PZ | GY | 845.3 | 11.01 (s, 1H), 9.03 (s, 1H), 8.92 (s, 1H), 8.33-8.22 (m, 2H), 8.04 (s, 1H), 7.92 (d, J = 8.4 Hz, 2H), 7.76-7.66 (m, 2H), 7.51 (d, J = 8.2 Hz, 2H), 7.27 (s, 1H), 7.24 (d, J = 1.2 Hz, 1H), 7.18 (d, J = 1.6, 5.2 Hz, 1H), 7.14 (d, J = 8.0 Hz, 1H), 7.02 (d, J = 1.2, 8.4 Hz, 1H), 5.33 (dd, J = 5.2, 13.2 Hz, 1H), 4.31-4.20 (m, 2H), 3.79 (s, 2H), 2.94-2.82 (m, 1H), 2.70-2.65 (m, 4H), 2.62 (d, J = 4.8 Hz, 5H), 2.36-2.31 (m, 2H), 2.15 (dd, J = 5.2, 10.4 Hz, 1H), 1.82-1.74 (m, 2H), 1.73-1.66 (m, 2H) |
| 563 | I-568 | PA | GY | 875.4 | 11.18 (s, 1H), 11.00 (s, 1H), 9.01 (s, 1H), 8.89 (s, 1H), 8.25 (d, J = 5.2 Hz, 1H), 8.01 (s, 1H), 7.89 (d, J = 8.4 Hz, 2H), 7.75-7.64 (m, 2H), 7.48 (d, J = 8.4 Hz, 2H), 7.25 (d, J = 12.4 Hz, 2H), 7.20-7.12 (m, 2H), 7.02 (d, J = 8.0 Hz, 1H), 5.33 (dd, J = 5.2, 12.8 Hz, 1H), 4.28-4.19 (m, 2H), 3.79 (s, 2H), 3.52-3.50 (m, 6H), 3.38 (t, J = 6.4 Hz, 2H), 2.91-2.83 (m, 1H), 2.74-2.60 (m, 6H), 2.18-2.07 (m, 1H), 1.84-1.73 (m, 2H) |
| 567 | I-572 | RJ | GY | 899.4 | 11.09 (s, 1H), 11.01 (s, 1H), 9.03 (s, 1H), 8.92 (s, 1H), 8.25 (d, J = 4.8 Hz, 1H), 8.18 (s, 1H), 8.06 (s, 1H), 7.97-7.86 (m, 2H), 7.80-7.65 (m, 2H), 7.53-7.46 (m, 2H), 7.26 (s, 1H), 7.17 (d, J = 4.8 Hz, 1H), 7.04 (s, 1H), 6.99 (d, J = 8.0 Hz, 1H), 6.87 (d, J = 8.0 Hz, 1H), 5.33 (dd, J = 5.2, |

TABLE 23-continued

Compounds synthesized via Method 16 with the reductive amination
of various amines with aldehydes in Step 1

| Ex-# | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| | | | | | 12.8 Hz, 1H), 4.29-4.20 (m, 2H), 3.85-3.73 (m, 3H), 3.59-3.55 (m, 2H), 3.31 (s, 3H), 2.95-2.77 (m, 2H), 2.69-2.56 (m, 7H), 2.27 (t, J = 6.4 Hz, 2H), 2.02-1.93 (m, 2H), 1.79-1.68 (m, 3H) |
| 568 | I-573 | RJ | GF | 878.5 | 11.07 (s, 1H), 9.98 (s, 1H), 8.95 (s, 1H), 8.78 (s, 1H), 8.16 (d, J = 1.6 Hz, 1H), 7.81 (d, J = 8.4 Hz, 2H), 7.50 (d, J = 8.4 Hz, 2H), 7.28 (t, J = 54.4 Hz, 1H), 7.11 (s, 1H), 7.09-7.03 (m, 3H), 6.99 (d, J = 8.0 Hz, 1H), 6.87 (d, J = 7.6 Hz, 1H), 5.35-5.29 (m, 1H), 3.82 (s, 2H), 3.78 (d, J = 11.6 Hz, 1H), 3.55-3.53 (m, 1H), 3.31 (s, 3H), 3.20-3.17 (m, 2H), 2.93-2.86 (m, 1H), 2.81 (d, J = 11.2 Hz, 1H), 2.72-2.57 (m, 9H), 2.28 (t, J = 7.2 Hz, 2H), 2.03-1.93 (m, 2H), 1.79-1.70 (m, 3H), 1.12-1.01 (m, 1H), 0.49-0.42 (m, 2H), 0.25-0.19 (m, 2H) |
| 569 | I-574 | RK | GF | 878.2 | 11.08 (s, 1H), 10.00 (s, 1H), 8.97 (s, 1H), 8.79 (s, 1H), 8.19-8.14 (m, 2H), 7.81 (d, J = 8.4 Hz, 2H), 7.49 (d, J = 8.4 Hz, 2H), 7.44-7.14 (m, 1H), 7.13-7.07 (m, 2H), 7.06-7.01 (m, 2H), 6.99 (d, J = 8.0 Hz, 1H), 6.90-6.83 (m, 1H), 5.37-5.28 (m, 1H), 3.79 (s, 2H), 3.76 (s, 1H), 3.31 (s, 3H), 3.17 (d, J = 6.2 Hz, 2H), 2.94-2.79 (m, 3H), 2.72-2.56 (m, 9H), 2.28 (t, J = 7.2 Hz, 2H), 2.03-1.92 (m, 2H), 1.79-1.67 (m, 3H), 1.12-0.98 (m, 1H), 0.49-0.38 (m, 2H), 0.26-0.17 (m, 2H) |
| 570 | I-575 | RM | GY | 913.5 | 11.22-10.08 (m, 2H), 9.02 (s, 1H), 8.92 (s, 1H), 8.31-8.23 (m, 3H), 7.91 (d, J = 8.8 Hz, 2H), 7.76-7.67 (m, 2H), 7.50 (d, J = 8.8 Hz, 2H), 7.27 (s, 1H), 7.20-7.15 (m, 1H), 7.08-6.96 (m, 2H), 6.89-6.84 (d, 1H), 5.42-5.27 (m, 1H), 4.29-4.17 (m, 2H), 3.96-3.67 (m, 3H), 3.35-3.33 (m, 2H), 3.31 (s, 3H), 3.25-3.18 (m, 2H), 2.91-2.84 (m, 1H), 2.90-2.84 (m, 2H), 2.63-2.59 (m, 4H), 2.26 (t, J = 6.8 Hz, 1H), 2.12-1.88 (m, 2H), 1.79-1.66 (m, 2H), 1.62-1.50 (m, 2H) |
| 571 | I-576 | RO | GY | 913.5 | 11.08 (s, 1H), 11.00 (s, 1H), 9.02 (s, 1H), 8.93 (s, 1H), 8.25 (d, J = 5.2 Hz, 1H), 8.18 (s, 1H), 8.04 (s, 1H), 7.94 (d, J = 8.4 Hz, 2H), 7.74-7.66 (m, 2H), 7.52 (d, J = 8.4 Hz, 2H), 7.26 (s, 1H), 7.19-7.16 (m, 1H), 7.04 (s, 1H), 6.99 (d, J = 8.0 Hz, 1H), 6.87 (d, J = 8.0 Hz, 1H), 5.35-5.30 (m, 1 H), 4.28-4.21 (m, 2H), 3.83 (s, 2H), 3.75-3.73 (m, 1H), 3.45-3.44 (m, 3H), 3.31 (s, 3H), 2.91-2.87 (m, 1H), 2.72 (m, 2H), 2.65-2.59 (m, 5H), 2.27-2.25 (m, 2H), 2.06-1.88 (m, 3H), 1.77-1.65 (m, 3 H), 1.59 (m, 2H) |
| 573 | I-578 | RT | GY | 900.5 | 11.08 (s, 1H), 11.01 (s, 1H), 9.03 (s, 1H), 8.92 (s, 1H), 8.26 (d, J = 5.2 Hz, 1H), 8.05 (s, 1H), 7.91 (d, J = 8.8 Hz, 2H), 7.76-7.67 (m, 2H), 7.44 (d, J = 8.8 Hz, 2H), 7.27 (s, 1H), 7.18 (dd, J = 1.2, 5.2 Hz, 1H), 7.06-6.96 (m, 2H) 6.89-6.81 (m, |

TABLE 23-continued

Compounds synthesized via Method 16 with the reductive amination
of various amines with aldehydes in Step 1

| Ex-# | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| | | | | | 1H), 5.33 (dd, J = 5.2, 12.8 Hz, 1H), 4.31-4.19 (m, 2H), 3.49 (s, 2H), 3.31 (s, 3H), 2.95-2.83 (m, 1H), 2.77-2.53 (m, 8H), 2.38-2.30 (m, 2H), 2.13 (s, 3H), 2.04-1.96 (m, 1H), 1.67-1.58 (m, 2H), 1.55-1.46 (m, 6H) |
| 574 | I-579 | QN | GY | 932.4 | 11.00 (s, 1H), 11.00-10.87 (m, 1H), 9.01 (s, 1H), 8.91 (s, 1H), 8.25 (d, J = 5.2 Hz, 1H), 8.02 (s, 1H), 7.95-7.84 (m, 3H), 7.68 (dd, J = 7.2, 11.2 Hz, 3H), 7.53-7.43 (m, 3H), 7.38 (d, J = 7.6 Hz, 1H), 7.27 (s, 1H), 7.18 (d, J = 5.2 Hz, 1H), 5.14-5.06 (m, 1H), 4.48-4.37 (m, 1H), 4.33-4.17 (m, 5H), 4.12-4.04 (m, 2H), 3.77 (s, 2H), 3.59 (s, 2H), 3.51 (dd, J = 5.6, 9.2 Hz, 6H), 2.98-2.84 (m, 1H), 2.67 (d, J = 5.2 Hz, 2H), 2.59 (d, J = 19.6 Hz, 2H), 2.43-2.35 (m, 1H), 2.03-1.93 (m, 1H) |
| 575 | I-580 | TP | GF | 862.4 | 10.99 (s, 1H), 10.03 (s, 1H), 8.93 (m, 1H), 8.81 (s, 1H), 8.33-8.08 (m, 2H), 7.88 (d, J = 7.6 Hz, 2H), 7.59 (d, J = 7.2 Hz, 2H), 7.46-7.02 (m, 8H), 5.70-5.57 (m, 1H), 4.69-4.60 (m, 1H), 4.05 (s, 2H), 3.94-3.86 (m, 4H), 3.23 (t, J = 8.0 Hz, 2H), 3.19-3.15 (m, 2H), 2.92-2.87 (m, 2H), 2.82-2.77 (m, 1H), 2.68-2.64 (m, 2H), 2.59-2.56 (m, 1H), 2.23-2.16 (m, 1H), 2.00-1.92 (m, 1H), 1.88-1.80 (m, 2H), 1.10-1.01 (m, 1H), 0.49-0.41 (m, 2H), 0.26-0.17 (m, 2H) |
| 576 | I-581 | SF | GF | 862.4 | 10.02 (s, 1H), 8.97 (s, 1H), 8.80 (s, 1H), 8.25 (s, 1H), 8.16 (d, J = 5.2 Hz, 1H), 7.82 (d, J = 8.4 Hz, 2H), 7.58-7.46 (m, 3H), 7.46-7.39 (m, 4H), 7.32-7.13 (m, 1H), 7.13-7.08 (m, 2H), 7.05 (d, J = 5.2 Hz, 1H), 5.71-5.58 (m, 1H), 4.76-4.73 (m, 1H), 3.90-3.84 (m, 2H), 3.52-3.50 (m, 4H), 3.27-3.21 (m, 2H), 3.20-3.17 (m, 2H), 2.91-2.77 (m, 1H), 2.70-2.64 (m, 4H), 2.60-2.56 (m, 1H), 2.28-2.16 (m, 1H), 2.03-1.93 (m, 1H), 1.78-1.71 (m, 2H), 1.12-1.03 (m, 1H), 0.49-0.44 (m, 2H), 0.25-0.21 (m, 2H) |
| 577[b] | I-582 | YY | PB | 886.6 | 11.11 (s, 1H), 9.98 (s, 1H), 8.96 (s, 1H), 8.78 (s, 1H), 8.16 (d, J = 5.2 Hz, 1H), 7.79 (d, J = 8.4 Hz, 2H), 7.49 (d, J = 8.4 Hz, 2H), 7.31-7.00 (m, 7H), 5.41-5.31 (m, 1H), 3.74 (s, 3H), 3.30-3.25 (m, 2H), 3.20-3.16 (m, 2H), 2.95-2.82 (m, 3H), 2.65-2.54 (m, 7H), 2.39-2.35 (m, 2H), 2.00-1.91 (m, 2H), 1.76-1.65 (m, 2H), 1.46-1.31 (m, 1H), 1.18-1.01 (m, 3H), 0.50-0.40 (m, 2H), 0.26-0.18 (m, 2H) |
| 578 | I-583 | SL | GF | 933.6 | 11.09 (s, 1H), 9.99 (s, 1H), 8.96 (s, 1H), 8.78 (s, 1H), 8.15 (d, J = 5.2 Hz, 1H), 7.79 (d, J = 8.4 Hz, 2H), 7.47 (d, J = 8.4 Hz, 2H), 7.42-7.14 (m, 1H), 7.09 (d, J = 10 Hz, 3H), 7.05-7.01 (m, 2H), 6.98-6.92 (m, 1H), 5.34 (dd, J = 5.2, 12.8 Hz, 1H), 4.11-4.01 (m, 2H), 3.65 (s, 3H), 3.45-3.45 (m, 2H), 3.29-3.28 (m, 2H), 3.19-3.16 (m, 4H), |

TABLE 23-continued

Compounds synthesized via Method 16 with the reductive amination of various amines with aldehydes in Step 1

| Ex-# | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| | | | | | 2.96-2.83 (m, 3H), 2.75-2.69 (m, 1H), 2.64-2.57 (m, 4H), 2.44-2.41 (m, 6H), 2.29-2.25 (m, 1H), 2.01-1.99 (m, 4H), 1.09-1.02 (m, 1H), 0.49-0.42 (m, 2H), 0.26-0.19 (m, 2H) |
| 579 | I-584 | SM | GF | 889.4 | 11.00 (s, 1H), 9.97 (s, 1H), 8.97 (s, 1H), 8.78 (s, 1H), 8.23 (s, 1H), 8.16 (d, J = 5.6 Hz, 1H), 7.79 (d, J = 8.4 Hz, 2H), 7.55-7.43 (m, 6H), 7.28 (t, J = 54.4 Hz, 2H), 7.12 (s, 1H), 7.08 (t, J = 5.2 Hz, 1H), 7.04 (d, J = 5.2 Hz, 1H), 5.71-5.59 (m, 1H), 4.73-4.62 (m, 1H), 3.93 (t, J = 8.8 Hz, 1H), 3.86 (d, J = 8.8 Hz, 1H), 3.82 (d, J = 10.8 Hz, 1H), 3.76 (s, 2H), 3.61-3.52 (m, 2H), 3.28-3.23 (m, 2H), 3.18 (t, J = 6.0 Hz, 2H), 2.90-2.77 (m, 2H), 2.69-2.66 (m, 1H), 2.65-2.55 (m, 2H), 2.35-2.32 (m, 1H), 2.31-2.12 (m, 2H), 2.07 (t, J = 10.4 Hz, 1H), 2.01-1.92 (m, 1H), 1.12-1.02 (m, 1H), 0.49-0.42 (m, 2H), 0.26-0.20 (m, 2H) |
| 580 | I-585 | SO | GF | 889.4 | 11.00 (s, 1H), 10.02 (s, 1H), 8.96 (s, 1H), 8.77 (s, 1H), 8.15 (d, J = 5.6 Hz, 1H), 7.79 (d, J = 8.4 Hz, 2H), 7.52-7.45 (m, 5H), 7.43-7.14 (m, 2H), 7.12-7.08 (m, 2H), 7.04 (d, J = 4.8 Hz, 1H), 5.72-5.59 (m, 1H), 4.73-4.61 (m, 1H), 3.96-3.78 (m, 3H), 3.76 (s, 2H), 3.58-3.52 (m, 2H), 3.26-3.14 (m, 5H), 2.92-2.73 (m, 3H), 2.64-2.57 (m, 2H), 2.31-2.25 (m, 1H), 2.23-2.14 (m, 1H), 2.09-2.02 (m, 1H), 2.01-1.91 (m, 1H), 1.10-1.02 (m, 1H), 0.48-0.43 (m, 2H), 0.24-0.19 (m, 2H) |
| 582 | I-587 | SQ | GF | 878.4 | 11.08 (s, 1H), 9.99 (s, 1H), 8.96 (s, 1H), 8.79 (s, 1H), 8.18-8.15 (m, 2H), 7.86-7.77 (m, 2H), 7.50 (d, J = 8.4 Hz, 2H), 7.43-7.14 (m, 1H), 7.11 (s, 1H), 7.08 (t, J = 5.6 Hz, 1H), 7.05-7.02 (m, 1H), 6.99-6.85 (m, 3H), 5.36 (dd, J = 5.6, 12.0 Hz, 1H), 3.84-3.78 (m, 3H), 3.77-3.74, 3.57 (s, 3H), 3.18 (t, J = 6.0 Hz, 2H), 2.95-2.83 (m, 4H), 2.71-2.54 (m, 6H), 2.36-2.32 (m, 2H), 2.04-1.93 (m, 2H), 1.82-1.67 (m, 3H), 1.14-1.00 (m, 1H), 0.51-0.37 (m, 2H), 0.25-0.19 (m, 2H) |
| 583 | I-588 | SR | GF | 878.2 | 11.09 (s, 1H), 9.99 (s, 1H), 8.97 (s, 1H), 8.80 (s, 1H), 8.16 (d, J = 5.6 Hz, 1H), 7.82 (d, J = 8.4 Hz, 2H), 7.51 (d, J = 8.4 Hz, 2H), 7.45-7.13 (m, 1H), 7.13-7.06 (m, 2H), 7.04 (dd, J = 1.2, 5.2 Hz, 1H), 6.98-6.92 (m, 2H), 6.91-6.85 (m, 1H), 5.37 (dd, J = 5.2, 12.4 Hz, 1H), 3.87-3.69 (m, 4H), 3.62-3.45 (m, 6H), 3.18 (t, J = 6.0 Hz, 2H), 3.04-2.79 (m, 4H), 2.76-2.58 (m, 4H), 2.42-2.23 (m, 2H), 2.04-1.93 (m, 2H), 1.81-1.71 (m, 3H), 1.13-1.01 (m, 1H), 0.51-0.40 (m, 2H), 0.26-0.18 (m, 2H) |
| 584 | I-589 | SS | GF | 865.0 | 11.20 (s, 1H), 9.98 (s, 1H), 8.96 (s, 1H), 8.78 (s, 1H), 8.16 (d, J = 5.4 Hz, 1H), 7.80 (d, J = 8.6 Hz, 2H), 7.48 (d, J = 8.7 Hz, 2H), 7.29 (s, 1H), 7.16-7.06 (m, 4H), 7.05-7.01 (m, 2H), 5.40-5.28 (m, 1H), |

TABLE 23-continued

Compounds synthesized via Method 16 with the reductive amination of various amines with aldehydes in Step 1

| Ex-# | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| | | | | | 3.76 (s, 2H), 3.51 (d, J = 2.4 Hz, 2H), 3.20-3.15 (m, 3H), 2.90-2.78 (m, 2H), 2.75-2.61 (m, 6H), 2.56 (d, J = 6.5 Hz, 1H), 2.36-2.26 (m, 3H), 2.18-2.11 (m, 1H), 2.01-1.92 (m, 1H), 1.83-1.69 (m, 3H), 1.11-1.02 (m, 1H), 0.49-0.42 (m, 2H), 0.25-0.19 (m, 2H) |
| 585 | I-590 | ST | GF | 865.4 | δ 11.20 (s, 1H), 9.99 (s, 1H), 8.96 (s, 1H), 8.78 (s, 1H), 8.19-8.15 (m, 2H), 7.86-7.75 (m, 2H), 7.50 (d, J = 8.0 Hz, 2H), 7.44-6.99 (m, 7H), 5.42-5.30 (m, 1H), 3.84-3.72 (m, 4H), 3.18 (t, J = 6.0 Hz, 2H), 2.90-2.79 (m, 2H), 2.75-2.54 (m, 8H), 2.34-2.31 (m, 2H), 2.18-2.12 (m, 1H), 2.01-1.94 (m, 1H), 1.85-1.69 (m, 3H), 1.12-1.02 (m, 1H), 0.49-0.41 (m, 2H), 0.26-0.18 (m, 2H) |
| 586 | I-591 | TW | GF | 906.5 | 11.08 (s, 1H), 9.99 (s, 1H), 8.98 (s, 1H), 8.80 (s, 1H), 8.16 (d, J = 5.2 Hz, 1H), 8.13 (s, 1H), 7.82 (d, J = 8.8 Hz, 2H), 7.47 (d, J = 8.4 Hz, 2H), 7.29 (s, 1H), 7.13-7.07 (m, 2H), 7.05-7.02 (m, 2H), 6.99 (d, J = 8.0 Hz, 1H), 6.87 (d, J = 8.0 Hz, 1H), 5.36-5.30 (m, 1H), 3.77-3.71 (m, 1H), 3.63-3.53 (m, 2H), 3.51-3.43 (m, 3H), 3.31 (s, 3H), 3.20-3.16 (m, 2H), 2.94-2.83 (m, 1H), 2.80-2.68 (m, 2H), 2.65-2.58 (m, 3H), 2.55-2.53 (m, 2H), 2.32-2.25 (m, 2H), 2.24-2.13 (m, 3H), 2.04-1.92 (m, 2H), 1.82-1.69 (m, 3H), 1.68-1.55 (m, 2H), 1.12-1.00 (m, 1H), 0.50-0.42 (m, 2H), 0.26-0.19 (m, 2H) |
| 587 | I-592 | TY | GF | 906.2 | 11.09 (s, 1H), 10.01 (s, 1H), 8.97 (s, 1H), 8.78 (s, 1H), 8.15 (d, J = 5.2 Hz, 1H), 7.80 (d, J = 8.4 Hz, 2H), 7.47-7.14 (m, 3H), 7.14-7.07 (m, 2H), 7.07-7.01 (m, 2H), 7.01-6.94 (m, 1H), 6.86 (d, J = 8.0 Hz, 1H), 5.32 (dd, J = 5.2, 12.8 Hz, 1H), 3.77-3.68 (m, 2H), 3.49 (s, 2H), 3.31 (s, 3H), 3.18 (t, J = 6.0 Hz, 2H), 2.92-2.84 (m, 1H), 2.77-2.68 (m, 2H), 2.64-2.56 (m, 5H), 2.43-2.39 (m, 2H), 2.25 (t, J = 7.2 Hz, 2H), 2.12 (s, 3H), 2.01-1.89 (m, 2H), 1.78-1.64 (m, 3H), 1.61-1.51 (m, 2H), 1.09-1.03 (m, 1H), 0.51-0.38 (m, 2H), 0.27-0.17 (m, 2H) |
| 588 | I-593 | SQ | GY | 899.4 | 11.08 (s, 1H), 11.00 (s, 1H), 9.02 (s, 1H), 8.97 (s, 1H), 8.25 (d, J = 5.2 Hz, 1H), 8.13 (s, 1H), 8.09-7.96 (m, 3H), 7.75 (s, 1H), 7.69 (t, J = 6.4 Hz, 1H), 7.59 (d, J = 8.4 Hz, 2H), 7.26 (s, 1H), 7.17 (dd, J = 5.2 Hz, 1H), 6.95 (d, J = 4.8 Hz, 2H), 6.90-6.85 (m, 1H), 5.39-5.32 (m, 1H), 4.29-4.19 (m, 2H), 4.03 (s, 1H), 3.88-3.79 (m, 1H), 3.73-3.61 (m, 2H), 3.57 (s, 3H), 3.53-3.50 (m, 1H), 2.95-2.80 (m, 7H), 2.76-2.68 (m, 2H), 2.65-2.62 (m, 1H), 2.61-2.58 (m, 1H), 2.41-2.35 (m, 2H), 2.10-1.94 (m, 2H), 1.78-1.73 (m, 2H) |
| 590 | I-595 | SU | GF | 888.4 | 10.86 (s, 1H), 9.75 (s, 1H), 8.73 (s, 1H), 8.53 (s, 1H), 8.17 (dd, J = 1.6, 8.0 Hz, 1H), 8.09 (dd, J = 1.6, 4.8 Hz, |

TABLE 23-continued

Compounds synthesized via Method 16 with the reductive amination of various amines with aldehydes in Step 1

| Ex-# | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| | | | | | 1H), 8.05 (s, 1H), 7.93 (d, J = 5.2 Hz, 1H), 7.55 (d, J = 8.8 Hz, 2H), 7.24 (d, J = 8.8 Hz, 2H), 7.20-7.04 (m, 3H), 6.94-6.88 (m, 3H), 6.85 (t, J = 5.6 Hz, 1H), 6.83-6.79 (m, 1H), 6.68 (dd, J = 2.0, 8.8 Hz, 1H), 5.73-5.59 (m, 1H), 3.54 (s, 2H), 3.44-3.40 (m, 2H), 3.38-3.32 (m, 8H), 3.06-3.02 (m, 2H), 2.96-29.4 (m, 2H), 2.77-2.73 (m, 1H), 2.48-2.46 (m, 1H), 2.43-2.40 (m, 1H), 1.84-1.82 (m, 1H), 0.26-0.20 (m, 2H), 0.10-0.02 (m, 2H) |
| 591 | I-596 | SV | GF | 881.5 | 9.97 (s, 1H), 8.95 (s, 1H), 8.75 (s, 1H), 8.15 (d, J = 5.6 Hz, 1H), 7.76 (d, J = 8.6 Hz, 2H), 7.45-7.51 (m, 2H), 7.13-7.42 (t, J = 5.2 Hz, 1H), 7.06-7.12 (m, 2H), 7.03 (dd, J = 5.2 Hz, 1H), 6.89-6.97 (m, 2H), 6.83 (s, 1H), 5.41-5.38 (m, 1H), 3.78 (s, 2H), 3.54 (s, 3H), 3.51-3.53 (m, 6H), 3.45-3.40 (m, 4H), 3.17 (d, J = 6.4 Hz, 2H), 3.01 (s, 3H), 2.94 (d, J = 6.4 Hz, 2H), 2.73-2.80 (m, 2H), 2.69-2.71 (m, 2H), 2.66-2.68 (m, 2H), 1.95-2.02 (m, 1H), 1.77-1.84 (m, 2H), 1.03-1.10 (m, 1H), 0.42-0.47 (m, 2H), 0.19-0.23 (m, 2H) |
| 592 | I-597 | 2-(2-methoxy-ethoxy)-ethan-amine (CAS# 31576-51-9) | GF | 603.3 | 11.01 (s, 1H), 9.03 (s, 1H), 8.99 (s, 1H), 8.26 (d, J = 5.2 Hz, 1H), 8.06 (d, J = 8.4 Hz, 3H), 7.77 (s, 1H), 7.70 (t, J = 6.4 Hz, 1H), 7.64 (d, J = 8.8 Hz, 2H), 7.26 (s, 1H), 7.18 (d, J = 5.2 Hz, 1H), 4.28-4.20 (m, 2H), 4.15 (s, 2H), 3.65 (t, J = 5.2 Hz, 2H), 3.59-3.56 (m, 2H), 3.49-3.47 (m, 2H), 3.26 (s, 3H), 3.05 (t, J = 5.2 Hz, 2H) |
| 593 | I-598 | RR | GF | 892.5 | 11.09 (s, 1H), 10.02 (s, 1H), 8.97 (s, 1H), 8.82 (s, 1H), 8.16 (d, J = 5.2 Hz, 1H), 7.86 (d, J = 8.4 Hz, 2H), 7.51 (d, J = 8.4 Hz, 2H), 7.30 (t, J = 8.4 Hz, 1H), 7.14-7.08 (m, 2H), 7.07-7.00 (m, 3H), 6.92-6.86 (m, 1H), 5.34 (dd, J = 5.2, 12.4 Hz, 1H), 3.90-3.85 (m, 1H), 3.82-3.76 (m, 2H), 3.64-3.59 (m, 2H), 3.32 (s, 3H), 3.20-3.17 (m, 2H), 3.07-3.03 (m, 1H), 2.97-2.92 (m, 1H), 2.91-2.85 (m, 1H), 2.76-2.70 (m, 1H), 2.69-2.57 (m, 7H), 2.57-2.53 (m, 2H), 2.33 (s, 3H), 2.03-1.96 (m, 1H), 1.89-1.80 (m, 2H), 1.12-1.02 (m, 1H), 0.49-0.43 (m, 2H), 0.25-0.20 (m, 2H) |
| 594 | I-599 | SZ | GF | 892.2 | 11.08 (s, 1H), 10.00 (s, 1H), 8.96 (s, 1H), 8.78 (s, 1H), 8.22 (s, 1H), 8.16 (d, J = 5.2 Hz, 1H), 7.80 (d, J = 8.4 Hz, 2H), 7.45 (d, J = 0.8 Hz, 2H), 7.12 (t, J = 14.8 Hz, 1H), 7.10-7.06 (m, 1H), 7.05-7.03 (m, 2H), 7.00 (d, J = 8.0 Hz, 1H), 6.87 (m, |

TABLE 23-continued

Compounds synthesized via Method 16 with the reductive amination
of various amines with aldehydes in Step 1

| Ex-# | I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|---|
| | | | | | 1H), 5.35-5.30 (m, 1H), 3.75 (d, J = 11.6 Hz, 1H), 3.61 (s, 1H), 3.58 (s, 2H), 3.31 (s, 3H), 3.18 (t, J = 6.0 Hz, 3H), 2.95-2.84 (m, 2H), 2.81 (d, J = 10.8 Hz, 1H), 2.76-2.68 (m, 1H), 2.69-2.66 (m, 1H), 2.63 (d, J = 6.4 Hz, 3H), 2.40-2.38 (m, 1H), 2.35-2.31 (m, 1H), 2.31-2.24 (m, 2H), 2.18 (s, 3H), 2.02-1.96 (m, 1H), 1.95-1.89 (m, 1H), 1.78-1.72 (m, 2H), 1.68 (t, J = 10.8 Hz, 1H), 1.12-1.01 (m, 1H), 0.48-0.42 (m, 2H), 0.25-0.19 (m, 2H) |
| 609 | I-614 | RK | JC | 906.5 | 11.09 (s, 1H), 10.08 (s, 1H), 9.00 (s, 1H), 8.87 (s, 1H), 8.25 (d, J = 5.6 Hz, 1H), 7.95 (d, J = 8.8 Hz, 2H), 7.69-7.61 (m, 3H), 7.44-7.17 (m, 3H), 7.07-6.98 (m, 2H), 6.87 (d, J = 8.8 Hz, 1H), 5.33 (dd, J = 5.2, 12.8 Hz, 1H), 4.28-4.16 (m, 4H), 3.94-3.77 (m, 2H), 3.68-3.9 (m, 2H), 3.32 (s, 3H), 3.06-3.04 (m, 2H), 3.00-2.78 (m, 5H), 2.74-2.55 (m, 6H), 2.03-1.95 (m, 1H), 1.82-1.74 (m, 2H) |
| 612 | I-617 | RK | TA | 866.5 | 11.07 (s, 1H), 9.49 (s, 1H), 8.97 (s, 1H), 8.80 (d, J = 8.0 Hz, 1H), 8.31 (s, 1H), 8.20 (s, 1H), 7.79 (d, J = 8.4 Hz, 2H), 7.49 (d, J = 8.4 Hz, 2H), 7.43-7.10 (m, 1H), 7.03 (s, 1H), 6.99 (d, J = 8.0 Hz, 1H), 6.91 (d, J = 8.0 Hz, 1H), 6.87 (d, J = 8.0 Hz, 1H), 5.35-5.26 (m, 1H), 3.84-3.75 (m, 7H), 3.48-3.46 (m, 4H), 3.31 (s, 3H), 2.94-2.89 (m, 4H), 2.88-2.79 (m, 2H), 2.70-2.66 (m, 1H), 2.64-2.59 (m, 4H), 2.58-2.55 (m, 1H), 2.54-2.52 (m, 1H), 2.31-2.22 (m, 2H), 2.04-1.92 (m, 2H), 1.78-1.67 (m, 3H) |

[a]For Method 16, when the amine is the HCl salt, TEA was added to free base the salt, followed by HOAc to adjust the pH to 3-4. KOAc could also be used in place of the TEA/HOAc combination. Other standard deprotections conditions could be used for the deprotection in Step 2, including often with TFA. Steps 1-2 was run anywhere from 0.5-48 hrs.

[b]No deprotection Step 2 required.

[c]In Step 1, Intermediates OS and were heated at 80° C. for 1 hr with HOAc and 4A MS, then NaBH3CN was added and the reaction mixture was stirred at rt for 1 h.

[d]In Step 2, the deprotection was achieved using HBr/HOAc in THF at rt for 96-160 hrs. For Example 617, I-622 the reaction was run in DCM with HBr/HOAc for 12 hr.

[e]In Step 2, the deprotection was achieved using ZnBr2 in DCM at rt.

Further Examples Using Synthetic Methods Similar to Method 16
Example 675: 2-[2-(Cyclopropylmethylamino)-4-pyridyl]-N-[3-(difluoromethyl)-1-[4-[[2-[2-[2-[2-[2-[2-[[(3S)-2-[(2S)-3,3-dimethyl-2-[[(2S)-2-(methylamino)propanoyl]amino]butanoyl]-3-[[(1R)-tetralin-1-yl]carbamoyl]-3,4-dihydro-1H-isoquinolin-7-yl]oxy]ethoxy]ethoxy]ethoxy]ethoxy]ethylamino]methyl-phenyl]pyrazol-4-yl]oxazole-4-carboxamide, I-680
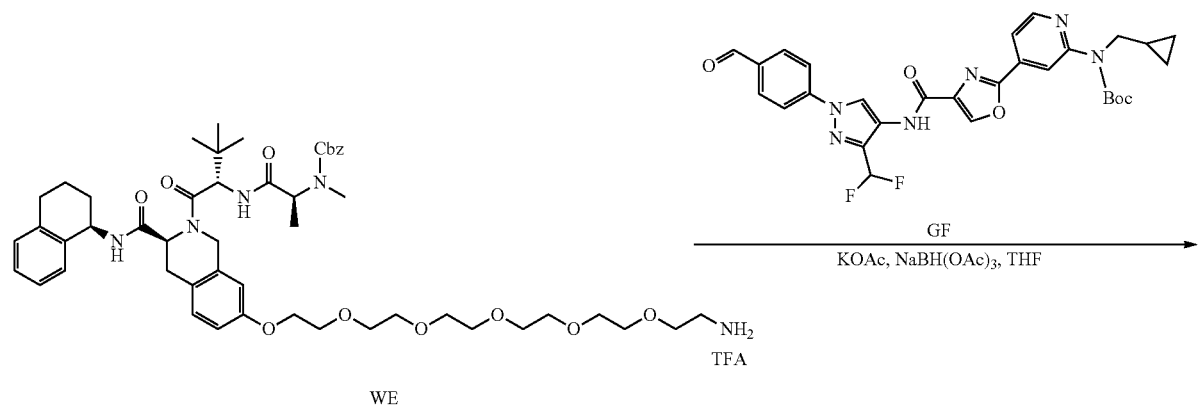
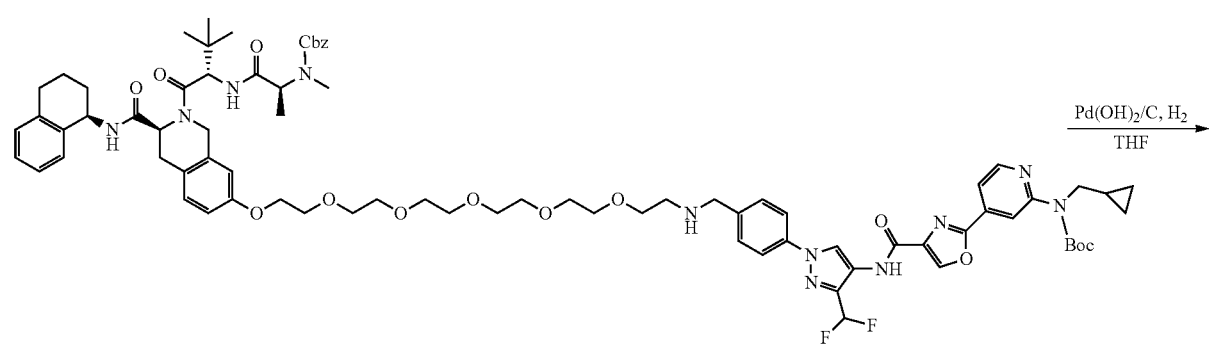
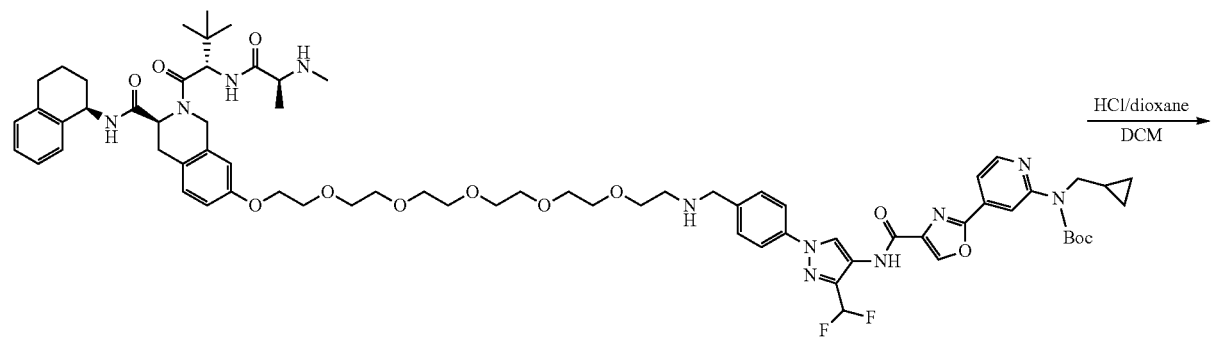

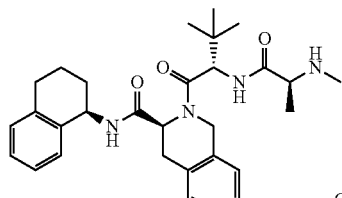
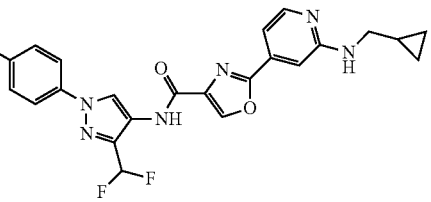

Step 1—Tert-butyl N-[4-[4-[[1-[4-[[2-[2-[2-[2-[2-[2-[[(3S)-2-[(2S)-2-[[(2S)-2-[benzyloxycarbonyl(methyl)amino]propanoyl]amino]-3,3-dimethyl-butanoyl]-3-[[(1R)-tetralin-1-yl]carbamoyl]-3,4-dihydro-1H-isoquinolin-7-yl]oxy]ethoxy]ethoxy]ethoxy]ethoxy]ethoxy]-ethylamino]methyl]phenyl]-3-(difluoromethyl)pyrazol-4-yl]carbamoyl]oxazol-2-yl]-2-pyridyl]-N-(cyclopropylmethyl)carbamate To a solution of benzyl-N-[(1S)-2-[[(1S)-1-[(3S)-7-[2-[2-[2-[2-[2-(2-aminoethoxy)ethoxy]ethoxy]ethoxy]ethoxy]-3-[[(1R)-tetralin-1-yl]carbamoyl]-3,4-dihydro-1H-isoquinoline-2-carbonyl]-2,2-dimethyl-propyl]amino]-1-methyl-2-oxo-ethyl]-N-methyl-carbamate (100 mg, 96.9 umol, TFA, Intermediate WE) and tert-butyl-N-(cyclopropylmethyl)-N-[4-[4-[[3-(difluoromethyl)-1-(4-formylphenyl)pyrazol-4-yl]carbamoyl]oxazol-2-yl]-2-pyridyl]carbamate (56.1 mg, 96.9 umol; Intermediate GF) in THF (4 mL) was added KOAc (19.0 mg, 194 umol) and NaBH(OAc)$_3$ (41.1 mg, 194 umol). The reaction mixture was stirred at 25° C. for 17 hrs. On completion, the mixture was concentrated in vacuo. The residue was purified by reverse phase (0.1% FA condition) to give the title compound (90.0 mg, 63% yield) as a white solid. LC-MS (ESI$^+$) m/z 1481.7 (M+H)$^+$.

Step 2—Tert-butyl N-(cyclopropylmethyl)-N-[4-[4-[[3-(difluoromethyl)-1-[4-[[2-[2-[2-[2-[2-[2-[[(3S)-2-[(2S)-3,3-dimethyl-2-[[(2S)-2-(methylamino)propanoyl]amino]butanoyl]-3-[[(1R)-tetralin-1-yl]carbamoyl]-3,4-dihydro-1H-isoquinolin-7-yl]oxy]ethoxy]ethoxy]ethoxy]ethoxy]-ethoxy]ethylamino]methyl]phenyl]pyrazol-4-yl]carbamoyl]oxazol-2-yl]-2-pyridyl]carbamate To a solution of tert-butyl N-[4-[4-[[1-[4-[[2-[2-[2-[2-[2-[2-[[(3S)-2-[(2S)-2-[[(2S)-2-[benzyloxycarbonyl(methyl)amino]propanoyl]amino]-3,3-dimethyl-butanoyl]-3-[[(1R)-tetralin-1-yl]oxy]ethoxy]ethoxy]ethoxy]ethoxy]ethoxy]-ethylamino]methyl]phenyl]-3-(difluoromethyl)pyrazol-4-yl]carbamoyl]oxazol-2-yl]-2-pyridyl]-N-(cyclopropylmethylcarbamate (40 mg, 27.0 umol) in THF (5 mL) was added Pd(OH)$_2$/C (0.1 g, 20% wt). The reaction mixture was stirred at 25° C. for 2 hrs under H$_2$ (15 psi) atmosphere. On completion, the mixture was filtered and the filtrate was concentrated in vacuo. The residue was purified by reverse phase (0.1% FA condition) to give the title compound (35.0 mg, 96% yield) as a white solid. LC-MS (ESI$^+$) m/z 1346.8 (M+H)$^+$.

Step 3—2-[2-(Cyclopropylmethylamino)-4-pyridyl]-N-[3-(difluoromethyl)-1-[4-[[2-[2-[2-[2-[2-[2-[[(3S)-2-[(2S)-3,3-dimethyl-2-[[(2S)-2-(methylamino)propanoyl]amino]butanoyl]-3-[[(1R)-tetralin-1-yl]carbamoyl]-3,4-dihydro 1H-isoquinolin-7-yl]oxy]ethoxy]ethoxy]ethoxy]ethoxy]-ethoxy]ethylamino]methyl]phenyl]pyrazol-4-yl]oxazole-4-carboxamide To a solution of tert-butyl N-(cyclopropylmethyl)-N-[4-[4-[[3-(difluoromethyl)-1-[4-[[2-[2-[2-[2-[2-[2-[[(3S)-2-[(2S)-3,3-dimethyl-2-[[(2S)-2-(methylamino)propanoyl]amino]butanoyl]-3-[[(1R)-tetralin-1-yl]carbamoyl]-3,4-dihydro-1H-isoquinolin-7-yl]oxy]ethoxy]ethoxy]ethoxy]ethoxy]ethoxy]ethylamino]methyl]phenyl]pyrazol-4-yl]carbamoyl]oxazol-2-yl]-2-pyridyl]carbamate (30.0 mg, 22.3 umol) in DCM (2 mL) was added HCl/dioxane (2 mL). The reaction mixture was stirred at 25° C. for 2 hrs. On completion, the mixture was concentrated in vacuo. The residue was purified by prep-HPLC (column: Phenomenex Synergi C18 150*25*10 um; mobile phase: [water (0.225% FA)-ACN]; B %: 12%-39%, 9 min) to give the title compound (4.00 mg, 14% yield, FA) as a brown solid. $^1$H NMR (400 MHz, DMSO-d$_6$) δ 10.00 (s, 1H), 8.96 (s, 1H), 8.78 (s, 1H), 8.28-8.25 (m, 1H), 8.20-8.10 (m, 2H), 8.03-7.89 (m, 1H), 7.80 (d, J=8.4 Hz, 2H), 7.49 (d, J=8.4 Hz, 2H), 7.29 (t, J=54.8 Hz 1H), 7.12-7.01 (m, 7H), 6.90 (s, 1H), 6.80-6.77 (m, 1H), 5.19-4.86 (m, 2H), 4.78-4.62 (m, 2H), 4.10-4.00 (m, 2H), 3.80 (s, 2H), 3.75-3.70 (m, 2H), 3.61-3.50 (m, 21H), 3.18 (t, J=6.0 Hz, 2H), 3.09-3.02 (m, 1H), 3.01-2.92 (m, 2H), 2.76-2.63 (m, 4H), 2.21-2.12 (m, 3H), 1.92-1.72 (m, 2H), 1.70-1.49 (m, 2H), 1.10 (d, J=6.8 Hz, 3H), 1.07-1.05 (m, 1H), 1.05-0.91 (m, 9H), 0.50-0.41 (m, 2H), 0.27-0.18 (m, 2H); LC-MS (ESI$^+$) m/z 1246.8 (M+H)$^+$.

Example 676: 2-[2-(Cyclopropylmethylamino)-4-pyridyl]-N-[3-(difluoromethyl)-1-[4-[[2-[2-[2-[2-[[(3S)-2-[(2S)-3,3-dimethyl-2-[[(2S)-2-(methylamino)propanoyl]amino]butanoyl]-3-[[(1R)-tetralin-1-yl]carbamoyl]-3,4-dihydro-1H-isoquinolin-7-yl]oxy]ethoxy]ethoxy]ethoxy]ethylamino]methyl]phenyl]pyrazol-4-yl]oxazole-4-carboxamide, I-681
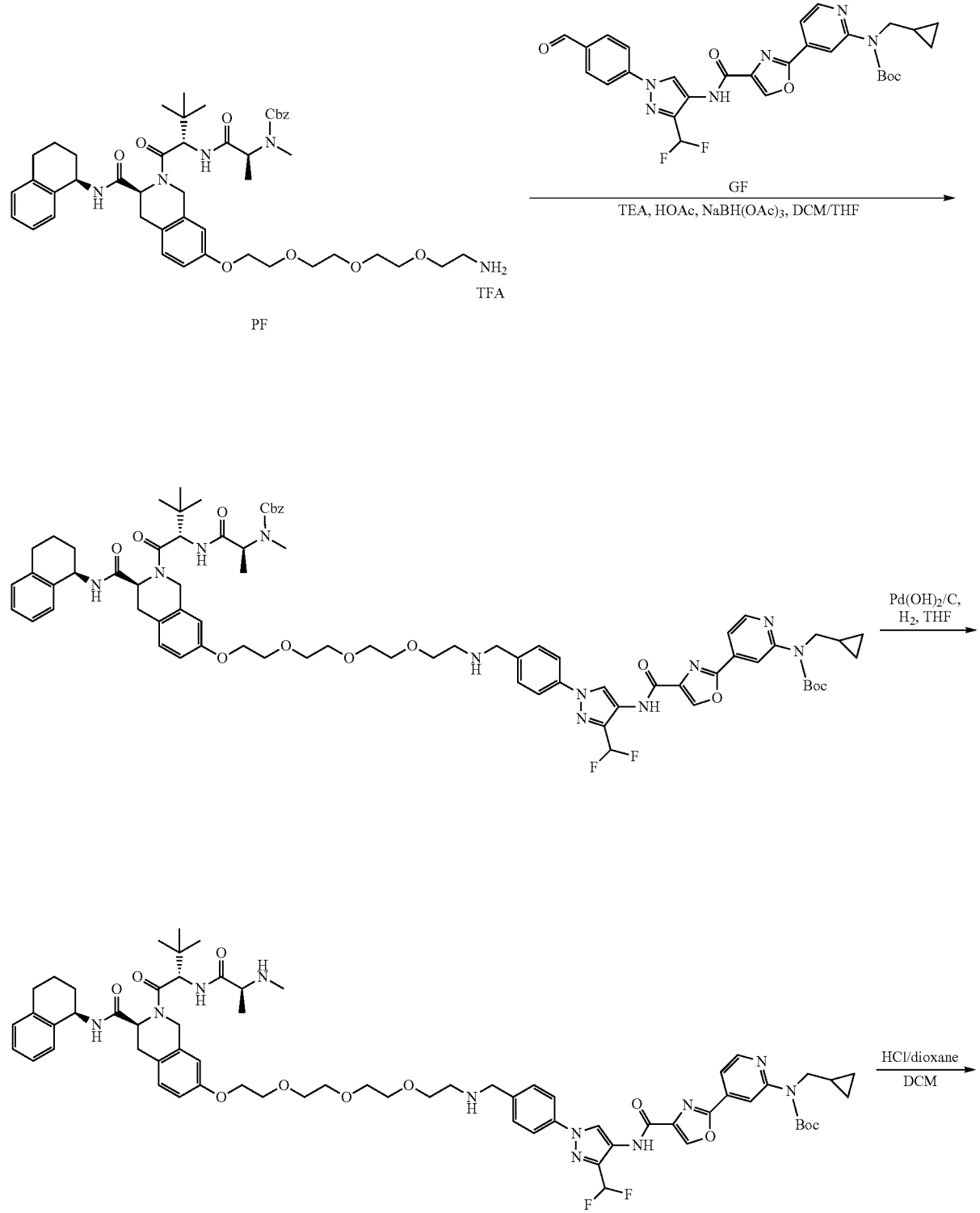

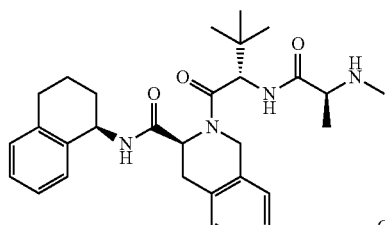
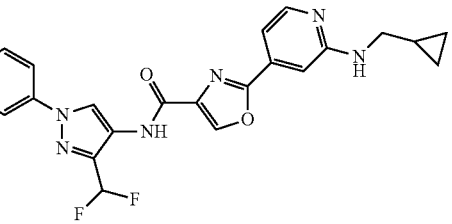

Step 1—Tert-butyl N-[4-[4-[[1-[4-[[2-[2-[2-[2-[[(3S)-2-[(2S)-2-[[(2S)-2-[benzyloxycarbonyl(methyl)amino]propanoyl]amino]-3,3-dimethyl-butanoyl]-3-[[(1R)-tetralin-1-yl]carbamoyl]-3,4-dihydro-1H-isoquinolin-7-yl]oxy]ethoxy]ethoxy]ethoxy]ethylamino]methyl]phenyl]-3-(difluoromethyl)pyrazol-4-yl]carbamoyl]oxazol-2-yl]-2-pyridyl]-N-(cyclopropylmethyl)carbamate To a solution of benzyl N-[(1S)-2-[[(1S)-1-[(3S)-7-[2-[2-[2-(2-aminoethoxy)ethoxy]ethoxy]ethoxy]-3-[[(1R)-tetralin-1-yl]carbamoyl]-3,4-dihydro-1H-isoquinoline-2-carbonyl]-2,2-dimethyl-propyl]amino]-1-methyl-2-oxo-ethyl]-N-methyl-carbamate (150 mg, 158 umol, TFA, Intermediate PF) and tert-butyl N-(cyclopropylmethyl)-N-[4-[4-[[3-(difluoromethyl)-1-(4-formylphenyl)pyrazol-4-yl]carbamoyl]oxazol-2-yl]-2-pyridyl]carbamate (91.9 mg, 158 umol, Intermediate GF) in THF (30 mL) was added TEA (16.0 mg, 158 umol, 22.1 uL). The mixture was stirred at 20° C. for 30 mins, then HOAc (25.6 mg, 426 umol, 24.3 uL) and NaBH(OAc)$_3$ (67.3 mg, 317 umol) was added into the mixture, and the reaction mixture was stirred at 20° C. for 48 hrs. On completion, the reaction mixture was quenched with H$_2$O (0.5 mL) and then concentrated in vacuo to give a residue. The residue was purified by reverse phase chromatography (0.1% FA condition) to give the title compound (90 mg, 40% yield) as a white solid. LC-MS (ESI+) m/z 1392.3 (M+H)$^+$.

Step 2—Tert-butyl N-(cyclopropylmethyl)-N-[4-[4-[[3-(difluoromethyl)-1-[4-[[2-[2-[2-[2-[[(3S)-2-[(2S)-3,3-dimethyl-2-[[(2S)-2-(methylamino)propanoyl]amino]butanoyl]-3-[[(1R)-tetralin-1-yl]carbamoyl]-3,4-dihydro-1H-isoquinolin-7-yl]oxy]ethoxy]ethoxy]ethoxy]ethylamino]methyl]phenyl]pyrazol-4-yl]carbamoyl]oxazol-2-yl]-2-pyridyl]carbamate To a solution of tert-butyl N-[4-[4-[[1-[4-[[2-[2-[2-[2-[[(3S)-2-[(2S)-2-[[(2S)-2-[benzyloxycarbonyl(methyl)amino]propanoyl]amino]-3,3-dimethyl-butanoyl]-3-[[(1R)-tetralin-1-yl]carbamoyl]-3,4-dihydro-1H-isoquinolin-7-yl]oxy]ethoxy]ethoxy]ethoxy]ethylamino]methyl]phenyl]-3-(difluoromethyl)pyrazol-4-yl]carbamoyl]oxazol-2-yl]-2-pyridyl]-N-(cyclopropylmethyl)carbamate (70.0 mg, 50.2 umol) in THF (1 mL) was added Pd(OH)$_2$/C (50 mg, 3.59 umol, 10% wt), and the reaction mixture was stirred at 25° C. for 40 min under H$_2$ gas (15 Psi). On completion, the mixture was filtered, the filtrate was concentrated in vacuo to give the residue, and the residue was purified by prep-HPLC (column: Phenomenex Synergi C18 150*25*10 um; mobile phase: [water (0.225% FA)-ACN]; B %: 32%-50%, 6 min) to give the title compound (20 mg, 31% yield) as a yellow solid. LC-MS (ESI$^+$) m/z 1258.8 (M+H)$^+$.

Step 3—2-[2-(Cyclopropylmethylamino)-4-pyridyl]-N-[3-(difluoromethyl)-1-[4-[[2-[2-[2-[2-[[(3S)-2-[(2S)-3,3-dimethyl-2-[[(2S)-2-(methylamino)propanoyl]amino]butanoyl]-3-[[(1R)-tetralin-1-yl]carbamoyl]-3,4-dihydro-1H-isoquinolin-7-yl]oxy]ethoxy]ethoxy]ethoxy]ethylamino]methyl]phenyl]pyrazol-4-yl]oxazole-4-carboxamide To a solution of tert-butyl N-(cyclopropylmethyl)-N-[4-[4-[[3-(difluoromethyl)-1-[4-[[2-[2-[2-[2-[[(3S)-2-[(2S)-3,3-dimethyl-2-[[(2S)-2-(methylamino)propanoyl]amino]butanoyl]-3-[[(1R)-tetralin-1-yl]carbamoyl]-3,4-dihydro-1H-isoquinolin-7-yl]oxy]ethoxy]ethoxy]ethoxy]ethylamino]methyl]phenyl]pyrazol-4-yl]carbamoyl]oxazol-2-yl]-2-pyridyl]carbamate (20 mg, 15.8 umol) in DCM (2 mL) was added HCl/dioxane (4 M, 1 mL), and the reaction mixture was stirred at 25° C. for 1 hr. On completion, the reaction mixture was concentrated in vacuo to give a residue. The residue was purified by prep-HPLC (column: Shim-pack C18 150*25*10 um; mobile phase: [water (0.225% FA)-ACN]; B %: 12%-42%, 10 min) to give the title compound (1.57 mg, 8.0% yield) as a white solid. $^1$H NMR (400 MHz, DMSO-d$_6$) δ 10.01 (s, 1H), 8.92 (s, 1H), 8.74 (s, 1H), 8.33 (s, 2H), 8.20-8.09 (m, 2H), 8.02-7.87 (m, 1H), 7.78 (d, J=8.4 Hz, 2H), 7.52-7.42 (m, 2H), 7.25 (t, J=54.8 Hz, 1H), 7.11-6.92 (m, 8H), 6.90-6.73 (m, 2H), 4.96-4.82 (m, 2H), 4.74-4.58 (m, 2H), 4.05-3.99 (m, 2H), 3.78 (s, 3H), 3.73-3.69 (m, 4H), 3.67-3.61 (m, 9H), 3.16 (t, J=6.0 Hz, 2H), 3.05-2.91 (m, 3H), 2.70-2.65 (m, 4H), 2.20-2.15 (m, 1H), 2.13 (s, 2H), 1.89-1.71 (m, 2H), 1.70-1.61 (m, 1H), 1.59-1.52 (m, 1H), 1.11-1.05 (m, 3H), 1.04-0.89 (m, 9H), 0.47-0.41 (m, 2H), 0.24-0.18 (m, 2H); LC-MS (ESI$^+$) m/z 1158.7 (M+H)$^+$.

Example 677: N-[3-[[2-[2-[2-[2-[2-[1 (3S)-2-(2S)-3,
3-dimethyl-2-[[(2S)-2-(methylamino)propanoyl]
amino]butanoyl]-3-[[(1R)-tetralin-1-yl]carbamoyl]-
3,4-dihydro-1H-isoquinolin-7-yl]oxy]ethoxy]
ethoxy]ethoxy]ethylamino]methyl]-1-methyl-
pyrazol-4-yl]-2-[2-(2,2,2-trifluoroethylamino)-4-
pyridyl]oxazole-4-carboxamide, I-682
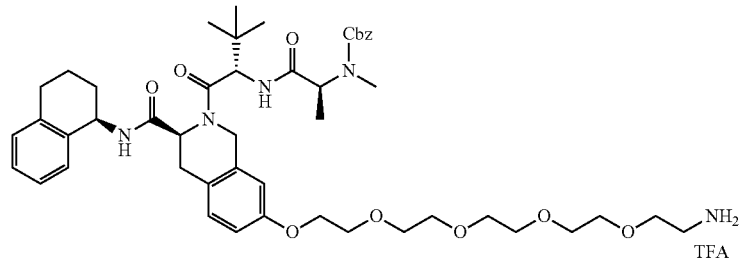
PJ
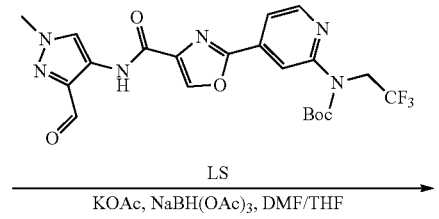
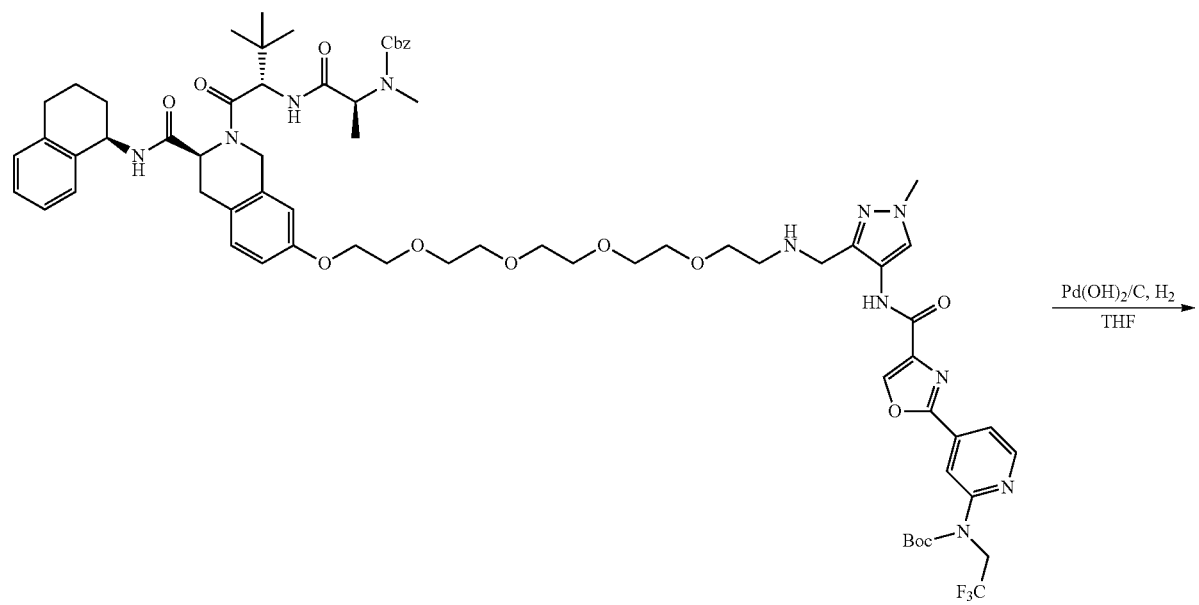

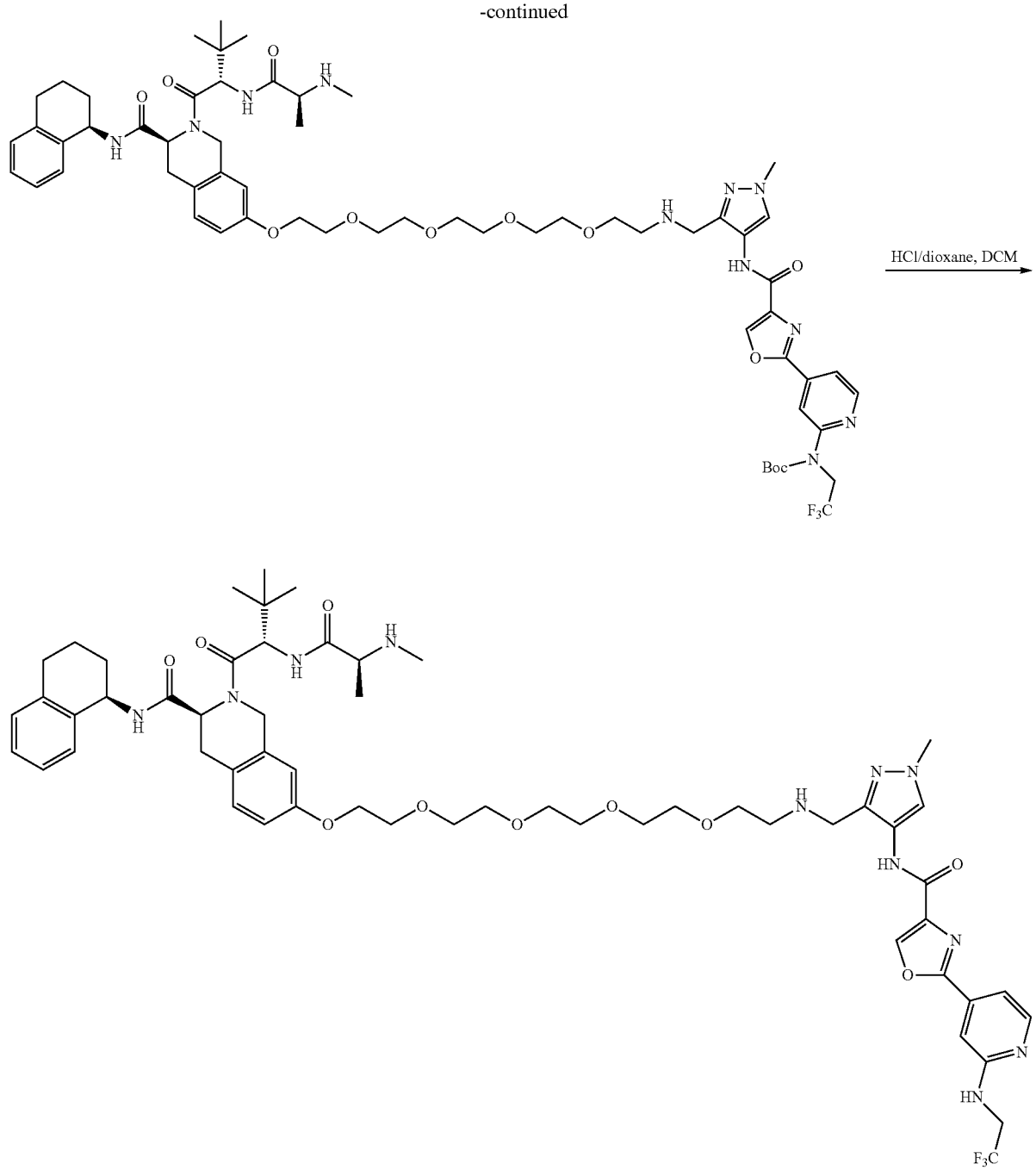

Step 1—Tert-butyl N-[4-[4-[[3-[[2-[2-[2-[2-[2-[[(3S)-2-[(2S)-2-[[(2S)-2-[benzyloxycarbonyl(methyl)amino]propanoyl]amino]-3,3-dimethyl-butanoyl]-3-[[(1R)-tetralin-1-yl]carbamoyl]-3,4-dihydro-1H-isoquinolin-7-yl]oxy]ethoxy]ethoxy]ethoxy]ethoxy]ethylamino]methyl]-1-methyl-pyrazol-4-yl]carbamoyl]oxazol-2-yl]-2-pyridyl]-N-(2,2,2-trifluoroethyl)carbamate To a solution of benzyl N-[(1S)-2-[[(1S)-1-[(3S)-7-[2-[2-[2-[2-(2-aminoethoxy)ethoxy]ethoxy]ethoxy]ethoxy]-3-[[(1R)-tetralin-1-yl]carbamoyl]-3,4-dihydro-1H-isoquinoline-2-carbonyl]-2,2-dimethyl-propyl]amino]-1-methyl-2-oxo-ethyl]-N-methyl-carbamate (55.0 mg, 55.7 umol, TFA, Intermediate PJ) and tert-butyl N-[4-[4-[(3-formyl-1-methyl-pyrazol-4-yl)carbamoyl]oxazol-2-yl]-2-pyridyl]-N-(2,2,2-trifluoroethyl)carbamate (27.5 mg, 55.7 umol, Intermediate LS) in a mixed solvent of DMF (1 mL) and THF (5 mL) was added KOAc (10.9 mg, 111 umol). The mixture was stirred at 25° C. for 0.5 hour. NaBH(OAc)₃ (23.6 mg, 111 umol) was then added into the mixture and the reaction mixture was stirred at 25° C. for 24 hours. On completion, the mixture was concentrated in vacuo. The residue was purified by reverse phase chromatography (0.1% FA condition) to give the title compound (35.0 mg, 46% yield) as a brown solid. LC-MS (ESI⁺) m/z 1352.7 (M+H)⁺.

Step 2—Tert-butyl N-[4-[4-[[3-[[2-[2-[2-[2-[2-[[(3S)-2-[(2S)-3,3-dimethyl-2-[[(2S)-2-(methylamino) propanoyl]amino]butanoyl]-3-[[(1R)-tetralin-1-yl]carbamoyl]-3,4-dihydro-1H-isoquinolin-7-yl]oxy]ethoxy]ethoxy]ethoxy]ethoxy]ethylamino]methyl]-1-methyl-pyrazol-4-yl]carbamoyl]oxazol-2-yl]-2-pyridyl]-N-(2,2,2-trifluoroethyl)carbamate To a solution of tert-butyl N-[4-[4-[[3-[[2-[2-[2-[2-[2-[[(3S)-2-[(2S)-2-[[(2S)-2-[benzyloxycarbonyl(methyl)amino]propanoyl]amino]-3,3-dimethyl-butanoyl]-3-[[(1R)-tetralin-1-yl]carbamoyl]-3,4-dihydro-1H-isoquinolin-7-yl]oxy]ethoxy]ethoxy]ethoxy]ethoxy]ethylamino]methyl]-1-methyl-pyrazol-4-yl]carbamoyl]oxazol-2-yl]-2-pyridyl]-N-(2,2,2-trifluoroethyl)carbamate (30.0 mg, 22.2 umol) in THF (3 mL) was added Pd(OH)$_2$/C (0.05 g, 20% wt). The reaction mixture was stirred at 25° C. for 1 hour under H$_2$ (15 Psi) atmosphere. On completion, the mixture was filtered and the filtrate was concentrated in vacuo. The residue was purified by reverse phase chromatography (0.1% FA condition) to give the title compound (15.0 mg, 56% yield) as a yellow solid. LC-MS (ESI$^+$) m/z 1218.8 (M+H)$^+$.

Step 3—N-[3-[[2-[2-[2-[2-[2-[[(3S)-2-[(2S)-3,3-dimethyl-2-[[(2S)-2-(methylamino)propanoyl amino]butanoyl]-3-[[(1R)-tetralin-1-yl]carbamoyl]-3,4-dihydro-1H-isoquinolin-7-yl]oxy]ethoxy]ethoxy]ethoxy]ethoxy]ethylamino]methyl]-1-methyl-pyrazol-4-yl]-2-[2-(2,2,2-trifluoroethylamino)-4-pyridyl]oxazole-4-carboxamide To a solution of tert-butyl N-[4-[4-[[3-[[2-[2-[2-[2-[2-[[(3S)-2-[(2S)-3,3-dimethyl-2-[[(2S)-2-(methylamino)propanoyl]amino]butanoyl]-3-[[(1R)-tetralin-1-yl]carbamoyl]-3,4-dihydro-1H-isoquinolin-7-yl]oxy]ethoxy]ethoxy]ethoxy]ethylamino]methyl]-1-methyl-pyrazol-4-yl]carbamoyl]oxazol-2-yl]-2-pyridyl]-N-(2,2,2-trifluoroethyl)carbamate (14.0 mg, 11.5 umol) in DCM (3 mL) was added HCl/dioxane (3 mL). The reaction mixture was stirred at 25° C. for 2 hours. On completion, the mixture was concentrated in vacuo. The residue was purified by prep-HPLC (column: Phenomenex Synergi C18 150*25*10 um; mobile phase: [water (0.225% FA)-ACN]; B %: 17%-41%, 8 min) to give the title compound (2.00 mg, 15% yield, FA) as a yellow solid. $^1$H NMR (400 MHz, DMSO-d$_6$) δ 10.92 (s, 1H), 8.88 (s, 1H), 8.25-8.18 (m, 2H), 8.13-8.10 (m, 1H), 7.98-7.88 (m, 1H), 7.61-7.54 (m, 1H), 7.20 (s, 1H), 7.18-7.16 (m, 1H), 7.12-7.07 (m, 2H), 7.07-7.01 (m, 2H), 6.89 (s, 1H), 6.82-6.72 (m, 2H), 5.23-4.92 (m, 2H), 4.90-4.80 (m, 2H), 4.71-4.60 (m, 2H), 4.29-4.18 (m, 3H), 4.05-3.97 (m, 2H), 3.92 (s, 2H), 3.79-3.56 (m, 16H), 3.00-2.93 (m, 3H), 2.75-2.71 (m, 2H), 2.20-2.04 (m, 6H), 1.90-1.73 (m, 2H), 1.71-1.60 (m, 2H), 1.57-1.49 (m, 1H), 1.13-1.07 (m, 3H), 1.07-1.04 (m, 1H), 1.03-0.92 (m, 9H); LC-MS (ESI$^+$) m/z 1118.7 (M+H)$^+$.

Further Examples

Example 679: 2-[2-(cyclopropylmethylamino)-4-pyridyl]-N-[3-(difluoromethyl)-1-[4-[[2-[2-[[1-(2,6-dioxo-3-piperidyl)-3-methyl-2-oxo-benzimidazol-5-yl]methylamino]ethoxy]ethylamino]methyl]phenyl]pyrazol-4-yl]oxazole-4-carboxamide, I-684

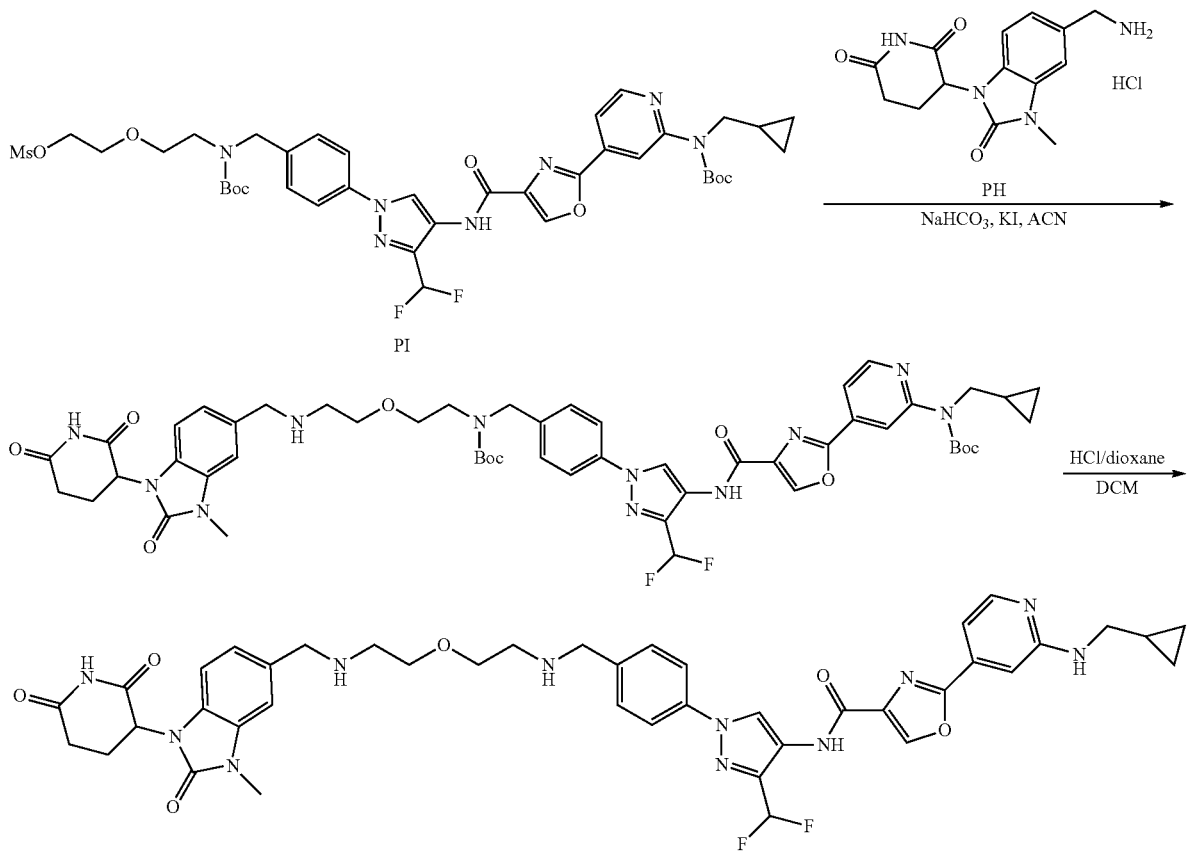

Step 1—Tert-butyl N-[[4-[4-[[2-[2-[tert-butoxycarbonyl(cyclopropylmethyl)amino]-4-pyridyl]oxazole-4-carbonyl]amino]-3-(difluoromethyl)pyrazol-1-yl]phenyl]methyl]-N-[2-[2-[[1-(2,6-dioxo-3-piperidyl)-3-methyl-2-oxo-benzimidazol-5-yl]methylamino]ethoxy]ethyl]carbamate To a solution of 2-[2-[tert-butoxycarbonyl-[[4-[4-[[2-[2-[tert-butoxycarbonyl(cyclopropylmethyl)amino]-4-pyridyl]oxazole-4-carbonyl]amino]-3-(difluoromethyl)pyrazol-1-yl]phenyl]methyl]amino]ethoxy]ethyl methanesulfonate (200 mg, 236 umol, Intermediate PI) and 3-[5-(aminomethyl)-3-methyl-2-oxo-benzimidazol-1-yl]piperidine-2,6-dione (160 mg, 492 umol, HCl, Intermediate PH) in ACN (10 mL) was added KI (39.2 mg, 236 umol) and NaHCO₃ (59.5 mg, 709 umol). The reaction mixture was stirred at 25° C. for 48 hours. On completion, the reaction mixture was diluted with ACN (100 mL) and filtered. The filtrate was concentrated in vacuo and the residue was purified by reversed-phase flash chromatography (FA, 0.1%) to give the title compound (60.0 mg, 24% yield) as a white solid. LC-MS (ESI⁺) m/z 1038.6 (M+H)⁺.

Step 2—2-[2-(cyclopropylmethylamino)-4-pyridyl]-N-[3-(difluoromethyl)-1-[4-[[2-[2-[[1-(2,6-dioxo-3-piperidyl)-3-methyl-2-oxo-benzimidazol-5-yl]methylamino]ethoxy]ethylamino]methyl]phenyl]pyrazol-4-yl]oxazole-4-carboxamide To a solution of tert-butyl N-[[4-[4-[[2-[2-[tert-butoxycarbonyl(cyclopropylmethyl)amino]-4-pyridyl]oxazole-4-carbonyl]amino]-3-(difluoromethyl)pyrazol-1-yl]phenyl]methyl]-N-[2-[2-[[1-(2,6-dioxo-3-piperidyl)-3-methyl-2-oxo-benzimidazol-5-yl]methylamino]ethoxy]ethyl]carbamate (50.0 mg, 48.1 umol) in DCM (2 mL) was added HCl/dioxane (4 M, 10 mL). The reaction mixture was stirred at 25° C. for 1 hour. On completion, the reaction mixture was concentrated in vacuo. The residue was purified by prep-HPLC (column: Phenomenex Synergi C18 150*25*10 um; mobile phase: [water (0.05% HCl)-ACN]; B %: 9%-29%, 10 min) to give the title compound (6.50 mg, 14% yield, HCl) as a yellow solid. ¹H NMR (400 MHz, DMSO-d₆) δ 11.12 (s, 1H), 10.16 (s, 1H), 9.50 (s, 2H), 9.37 (s, 2H), 9.12 (s, 1H), 8.88 (s, 1H), 8.16-8.06 (m, 1H), 7.98-7.88 (m, 2H), 7.78 (d, J=6.8 Hz, 2H), 7.54 (s, 1H), 7.36-7.12 (m, 4H), 5.47-5.32 (m, 1H), 4.27-4.22 (m, 2H), 3.73 (s, 3H), 3.30-3.23 (m, 6H), 3.16-3.06 (m, 4H), 2.97-2.83 (m, 1H), 2.62-2.58 (m, 2H), 2.04-1.90 (m, 1H), 1.18-1.07 (s, 1H), 0.62-0.48 (m, 2H), 0.36-0.25 (m, 2H); LC-MS (ESI⁺) m/z 838.4 (M+H)⁺.

Example 680: 2-[2-(Cyclopropylmethylamino)-4-pyridyl]-N-[3-(difluoromethyl)-1-[4-[[2-[2-[4-[1-(2,6-dioxo-3-piperidyl)-3-methyl-2-oxo-benzimidazol-5-yl]piperazin-1-yl]ethoxy]ethylamino]methyl]phenylpyrazol-4-yl]oxazole-4-carboxamide, I-685

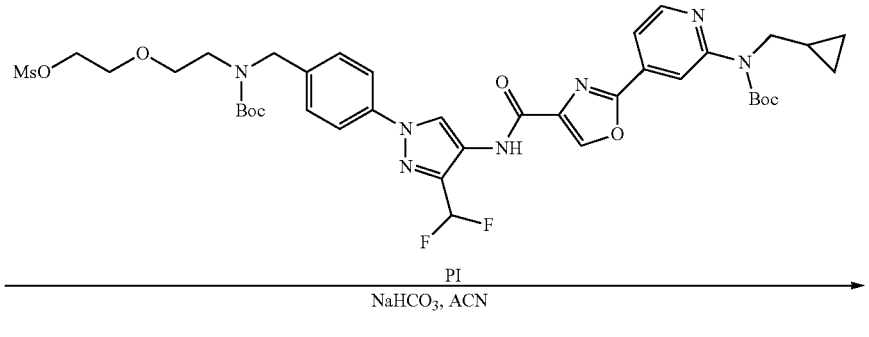

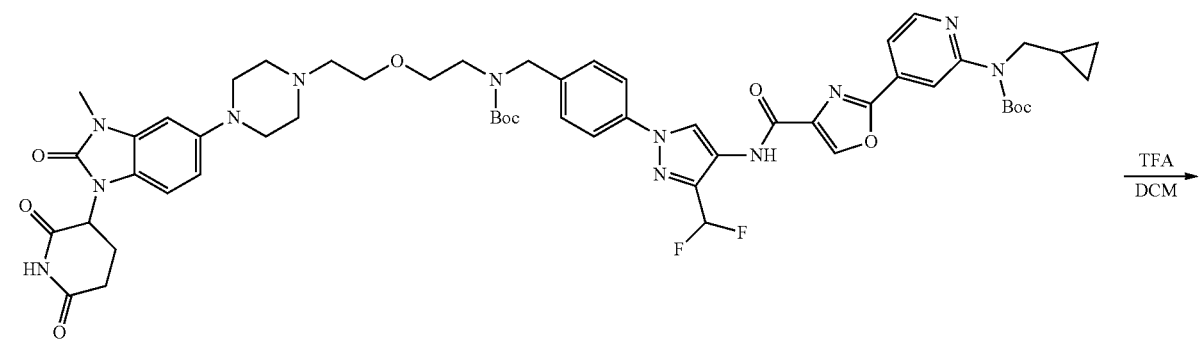

2645

2646

-continued

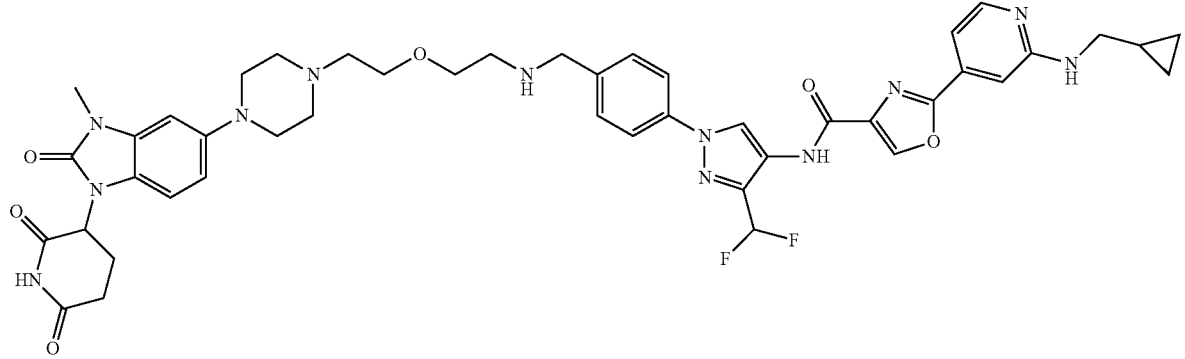

Step 1—Tert-butyl N-[[4-[4-[[2-[2-[tert-butoxycarbonyl(cyclopropylmethyl)amino]-4-pyridyl]oxazole-4-carbonyl]amino]-3-(difluoromethyl)pyrazol-1-yl]phenyl]methyl-N-[2-[2-[4-[1-(2,6-dioxo-3-piperidyl)-3-methyl-2-oxo-benzimidazol-5-yl]piperazin-1-yl]ethoxy]ethyl]carbamate To a solution of 3-(3-methyl-2-oxo-5-piperazin-1-yl-benzimidazol-1-yl)piperidine-2,6-dione (50.0 mg, 146 umol, Intermediate PN), 2-[2-[tert-butoxycarbonyl-[[4-[4-[[2-[2-[tert-butoxycarbonyl(cyclopropylmethyl)amino]-4-pyridyl]oxazole-4-carbonyl]amino]-3-(difluoromethyl)pyrazol-1-yl]phenyl]methyl]amino]ethoxy]ethyl methanesulfonate (148 mg, 175 umol, Intermediate PI) in $CH_3CN$ (8 mL) was added $NaHCO_3$ (36.7 mg, 437 umol), and then the mixture was stirred at 80° C. for 6 hrs under $N_2$ atmosphere. On completion, the mixture was concentrated in vacuo, and the residue was purified by reversed-phase HPLC (0.1% FA condition) to give the title compound (30.0 mg, 15% yield) as a yellow solid. LC-MS (ESI+) m/z 1093.6 $(M+H)^+$.

Step 2—2-[2-(Cyclopropylmethylamino)-4-pyridyl]-N-[3-(difluoromethyl)-1-[4-[[2-[2-[4-[1-(2,6-dioxo-3-piperidyl)-3-methyl-2-oxo-benzimidazol-5-yl]piperazin-1-yl]ethoxy]ethylamino]methyl]phenylpyrazol-4-yl]oxazole-4-carboxamide To a solution of tert-butyl N-[[4-[4-[[2-[2-[tert-butoxycarbonyl(cyclopropylmethyl)amino]-4-pyridyl]oxazole-4-carbonyl]amino]-3-(difluoromethyl)pyrazol-1-yl]phenyl]methyl]-N-[2-[2-[4-[1-(2,6-dioxo-3-piperidyl)-3-methyl-2-oxo-benzimidazol-5-yl]piperazin-1-yl]ethoxy]ethyl]carbamate (20.0 mg, 18.3 umol) in DCM (2 mL) was added TFA (1.54 g, 13.5 mmol, 1.00 mL). The mixture was stirred at 15° C. for 0.5 hr. The mixture was then concentrated in vacuo, and the residue was purified by prep-HPLC (column: Phenomenex Synergi C18 150*25*10 um; mobile phase: [water (0.225% FA)-ACN]; B %: 1%-31%, 10 min) to give the title compound (13.6 mg, 83% yield) as a yellow solid. $^1$H NMR (400 MHz, DMSO-$d_6$) δ 10.96-11.11 (m, 2H), 9.01 (s, 1H), 8.91 (s, 1H), 8.23-8.34 (m, 3H), 8.04 (s, 1H), 7.91 (d, J=8.4 Hz, 2H), 7.65-7.77 (m, 2H), 7.51 (d, J=8.4 Hz, 2H), 7.27 (s, 1H), 7.14-7.21 (m, 1H), 6.91 (d, J=8.6 Hz, 1H), 6.80 (d, J=1.6 Hz, 1H), 6.60 (dd, J=8.4, 2.20 Hz, 1H), 5.26 (dd, J=13.2 Hz, 1H), 4.23-4.30 (m, 2H), 3.81 (s, 2H), 3.55 (s, 4H), 3.29 (s, 3H), 3.06 (m, 4H), 2.83-2.91 (m, 1H), 2.70 (m, 2H), 2.67-2.69 (m, 2H), 2.61-2.65 (m, 2H), 2.58 (m, 4H), 2.07 (s, 3H), 1.96-2.01 (m, 1H), LC-MS (ESI+) m/z 893.5 $(M+H)^+$.

Example 683: N-[2-[2-[2-[3-[1-(2,6-dioxo-3-piperidyl)-3-methyl-2-oxo-benzimidazol-4-yl]prop-2-ynoxy]ethoxy]ethyl]-6-(1-hydroxy-1-methyl-ethyl)indazol-5-yl]-6-(trifluoromethyl)pyridine-2-carboxamide, I-688

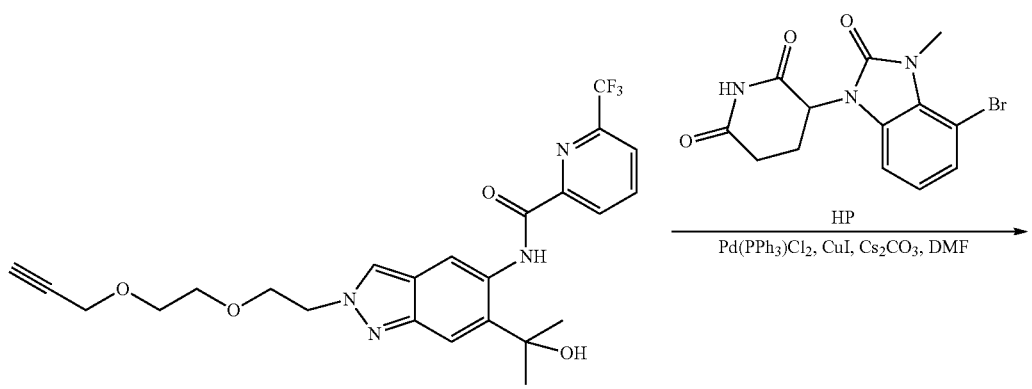

TK

-continued

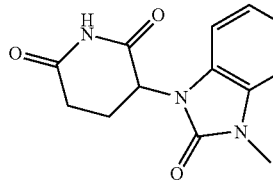 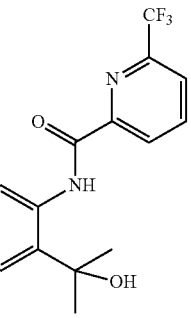

A mixture of N-[6-(1-hydroxy-1-methyl-ethyl)-2-[2-(2-prop-2-ynoxyethoxy)ethyl]indazol-5-yl]-6-(trifluoromethyl)pyridine-2-carboxamide (300 mg, 611 umol, Intermediate TK), 3-(4-bromo-3-methyl-2-oxo-benzimidazol-1-yl)piperidine-2,6-dione (130 mg, 384 umol, Intermediate HP), CuI (15.0 mg, 78.7 umol), Pd(PPh$_3$)$_2$Cl$_2$ (54.0 mg, 76.9 umol), Cs$_2$CO$_3$ (630 mg, 1.93 mmol) and 4 Å molecular sieves (100 mg) in DMF (4 mL) was stirred at 80° C. for 2 hours under N$_2$. On completion, the reaction mixture was cooled to 20° C. and then filtered. The filter cake was washed with EA (10 mL) and the filtrate was concentrated in vacuo. The residue was purified by prep-HPLC (column: Phenomenex Synergi C18 150*25*10 um; mobile phase: [water (0.225% FA)-ACN]; B %: 35%-65%, 10 min) to give the title compound (74.2 mg, 25% yield) as yellow solid. $^1$H NMR (400 MHz, DMSO-d$_6$) δ 12.36 (s, 1H), 11.12 (s, 1H), 8.72 (m, 1H), 8.44 (d, J=8.0 Hz, 1H), 8.37 (d, J=7.6 Hz, 1H), 8.34 (s, 1H), 8.16 (d, J=8.0 Hz, 1H), 7.57 (s, 1H), 7.15 (d, J=7.6 Hz, 1H), 7.11 (d, J=7.6 Hz, 1H), 7.00 (t, J=8.0 Hz, 1H), 5.95 (s, 1H), 5.41-5.36 (m, 1H), 4.57 (t, J=5.2 Hz, 2H), 4.41 (s, 2H), 3.93 (t, J=5.2 Hz, 2H), 3.65-3.55 (m, 7H), 2.93-2.82 (m, 1H), 2.74-2.68 (m, 1H), 2.65-2.57 (m, 1H), 2.06-1.96 (m, 1H), 1.61 (s, 6H); LC-MS (ESI$^+$) m/z 748.1 (M+H)$^+$.

Example 684 & 685: N-[3-carbamoyl-1-[4-[[2-[2-[3-[(1R)-1-(2,6-dioxo-3-piperidyl)-3-methyl-2-oxo-benzimidazol-4-yl]propoxy]ethoxy]ethylamino]methyl]phenyl]pyrazol-4-yl]-2-[2-(2,2,2-trifluoroethylamino)-4-pyridyl]oxazole-4-carboxamide, I-686 and N-[3-carbamoyl-1-[4-[[2-[2-[3-[(1S)-1-(2,6-dioxo-3-piperidyl)-3-methyl-2-oxo-benzimidazol-4-yl]propoxy]ethoxy]ethylamino]methyl]phenyl]pyrazol-4-yl]-2-[2-(2,2,2-trifluoroethylamino)-4-pyridyl]oxazole-4-carboxamide, I-690

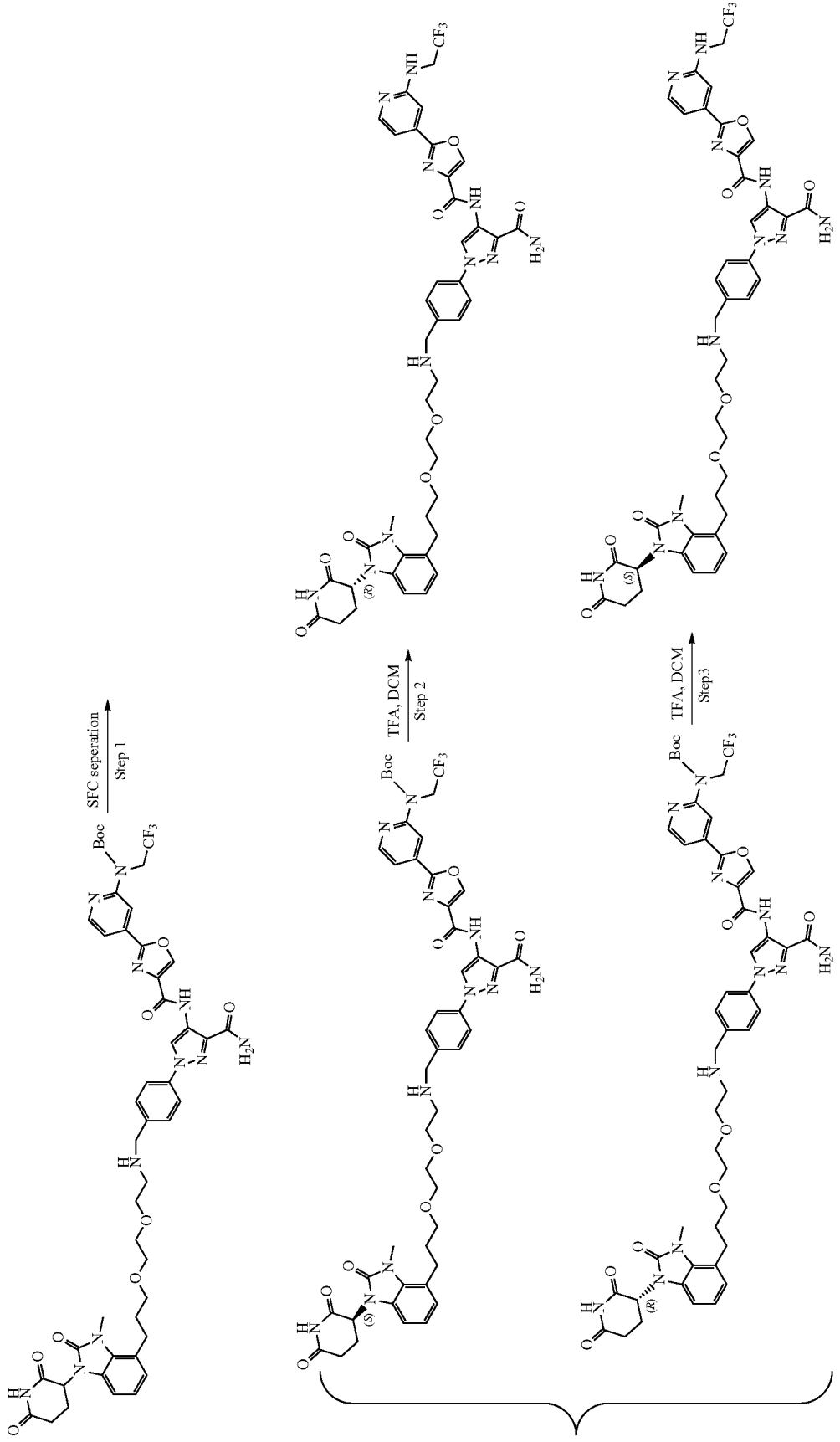

Step 1—Tert-butyl N-[4-[4-[[3-carbamoyl-1-[4-[[2-[2-[3-[(1S)-1-(2,6-dioxo-3-piperidyl)-3-methyl-2-oxo-benzimidazol-4-yl]propoxy]ethoxy]ethylamino]methyl]phenyl]pyrazol-4-yl]carbamoyl]oxazol-2-yl]-2-pyridyl]-N-(2,2,2-trifluoroethyl)carbamate & Tert-butyl N-[4-[4-[[3-carbamoyl-1-[4-[[2-[2-[3-[(1R)-1-(2,6-dioxo-3-piperidyl)-3-methyl-2-oxo-benzimidazol-4-yl]propoxy]ethoxy]ethylamino]methyl]phenyl]pyrazol-4-yl]carbamoyl]oxazol-2-yl]-2-pyridyl]-N-(2,2,2-trifluoroethyl)carbamate Tert-butyl N-[4-[4-[[3-carbamoyl-1-[4-[[2-[2-[3-[1-(2,6-dioxo-3-piperidyl)-3-methyl-2-oxo-benzimidazol-4-yl]propoxy]ethoxy]ethylamino]methyl]phenyl]pyrazol-4-yl]carbamoyl]oxazol-2-yl]-2-pyridyl]-N-(2,2,2-trifluoroethyl)carbamate (190 mg, 192 umol, Example 324, 1-329) was separated by SFC (column: DAICEL CHIRALPAK IC (250 mm*30 mm, 10 um); mobile phase: [0.1% DEA, IPA]; B %: 70%-70%, 5.7 min; 100 min) to give the title compound tert-butyl N-[4-[4-[[3-carbamoyl-1-[4-[[2-[2-[3-[(1S)-1-(2,6-dioxo-3-piperidyl)-3-methyl-2-oxo-benzimidazol-4-yl]propoxy]ethoxy]ethylamino]methyl]phenyl]pyrazol-4-yl]carbamoyl]oxazol-2-yl]-2-pyridyl]-N-(2,2,2-trifluoroethyl)carbamate (95 mg, 50% yield) as a white solid and tert-butyl N-[4-[4-[[3-carbamoyl-1-[4-[[2-[2-[3-[(1R)-1-(2,6-dioxo-3-piperidyl)-3-methyl-2-oxo-benzimidazol-4-yl]propoxy]ethoxy]ethylamino]methyl]phenyl]pyrazol-4-yl]carbamoyl]oxazol-2-yl]-2-pyridyl]-N-(2,2,2-trifluoroethyl)carbamate (95 mg, 50% yield) as a white solid. LC-MS (ESI$^+$) m/z 988.5 (M+H)$^+$ for both isomers.

Step 2—N-[3-carbamoyl-1-[4-[[2-[2-[3-[(1R)-1-(2,6-dioxo-3-piperidyl)-3-methyl-2-oxo-benzimidazol-4-yl]propoxy]ethoxy]ethylamino]methyl]phenyl]pyrazol-4-yl]-2-[2-(2,2,2-trifluoroethylamino)-4-pyridyl]oxazole-4-carboxamide To a solution of tert-butyl N-[4-[4-[[3-carbamoyl-1-[4-[[2-[2-[3-[(1R)-1-(2,6-dioxo-3-piperidyl)-3-methyl-2-oxo-benzimidazol-4-yl]propoxy]ethoxy]ethylamino]methyl]phenyl]pyrazol-4-yl]carbamoyl]oxazol-2-yl]-2-pyridyl]-N-(2,2,2-trifluoroethyl)carbamate (75.0 mg, 75.9 umol) in DCM (1 mL) was added TFA (1.15 g, 10.1 mmol). The reaction mixture was stirred at 25° C. for 0.5 hr. On completion, the reaction mixture was concentrated in vacuo. The crude product was purified by prep-HPLC (column: Phenomenex Synergi C18 150*25*10 um; mobile phase: [water (0.225% FA)-ACN]; B %: 16%-43%, 9 min) to give the title compound (36.6 mg, 52% yield, ee 81%, FA salt) as a white solid. $^1$H NMR (400 MHz, DMSO-d$_6$) δ 11.09 (s, 1H), 11.01 (s, 1H), 9.02 (s, 1H), 8.90 (s, 1H), 8.26 (d, J=5.2 Hz, 1H), 8.04 (s, 1H), 7.89 (d, J=8.8 Hz, 2H), 7.76-7.67 (m, 2H), 7.49 (d, J=8.8 Hz, 2H), 7.27 (s, 1H), 7.18 (dd, J=1.2, 5.2 Hz, 1H), 6.99-6.91 (m, 2H), 6.89-6.83 (m, 1H), 5.36 (dd, J=5.2, 12.8 Hz, 1H), 4.32-4.19 (m, 2H), 3.81 (s, 2H), 3.63-3.52 (m, 11H), 2.98-2.91 (m, 2H), 2.91-2.83 (m, 1H), 2.72 (t, J=5.6 Hz, 2H), 2.69-2.65 (m, 1H), 2.64-2.58 (m, 1H), 2.04-1.95 (m, 1H), 1.87-1.77 (m, 2H); LC-MS (ESI$^+$) m/z 888.2 (M+H)$^+$.

Step 3—N-[3-carbamoyl-1-[4-[[2-[2-[3-[(1S)-1-(2,6-dioxo-3-piperidyl)-3-methyl-2-oxo-benzimidazol-4-yl]propoxy]ethoxy]ethylamino]methyl]phenyl]pyrazol-4-yl]-2-[2-(2,2,2-trifluoroethylamino)-4-pyridyl]oxazole-4-carboxamide To a solution of tert-butyl N-[4-[4-[[3-carbamoyl-1-[4-[[2-[2-[3-[(1S)-1-(2,6-dioxo-3-piperidyl)-3-methyl-2-oxo-benzimidazol-4-yl]propoxy]ethoxy]ethylamino]methyl]phenyl]pyrazol-4-yl]carbamoyl]oxazol-2-yl]-2-pyridyl]-N-(2,2,2-trifluoroethyl)carbamate (75.0 mg, 75.9 umol) in DCM (1 mL) was added TFA (1.15 g, 10.1 mmol). The reaction mixture was stirred at 25° C. for 0.5 hr. On completion, the reaction mixture was concentrated in vacuo. The crude product was purified by prep-HPLC (column: Phenomenex Synergi C18 150*25*10 um; mobile phase: [water (0.225% FA)-ACN]; B %: 16%-46%, 10 min) to give the title compound (38.0 mg, 51% yield, ee value=85%, FA salt) as a white solid. $^1$H NMR (400 MHz, DMSO-d$_6$) δ 11.09 (s, 1H), 11.01 (s, 1H), 9.02 (s, 1H), 8.90 (s, 1H), 8.26 (d, J=5.2 Hz, 1H), 8.04 (s, 1H), 7.89 (d, J=8.8 Hz, 2H), 7.76-7.67 (m, 2H), 7.49 (d, J=8.8 Hz, 2H), 7.27 (s, 1H), 7.18 (dd, J=1.2, 5.2 Hz, 1H), 6.99-6.91 (m, 2H), 6.89-6.83 (m, 1H), 5.36 (dd, J=5.2, 12.8 Hz, 1H), 4.32-4.19 (m, 2H), 3.81 (s, 2H), 3.63-3.52 (m, 11H), 2.98-2.91 (m, 2H), 2.91-2.83 (m, 1H), 2.72 (t, J=5.6 Hz, 2H), 2.69-2.65 (m, 1H), 2.64-2.58 (m, 1H), 2.04-1.95 (m, 1H), 1.87-1.77 (m, 2H); LC-MS (ESI$^+$) m/z 888.2 (M+H)$^+$.

Example 686: 2-(2,6-Dioxo-3-piperidyl)-4-[2-[2-[2-[2-[4-[[1-methyl-7-[(4-morpholinocyclohexyl)amino]pyrazolo[4,3-d[pyrimidin-5-yl]amino]pyrazol-1-yl]ethoxy]ethoxy]ethoxy]ethylamino]isoindoline-1,3-dione, I-691

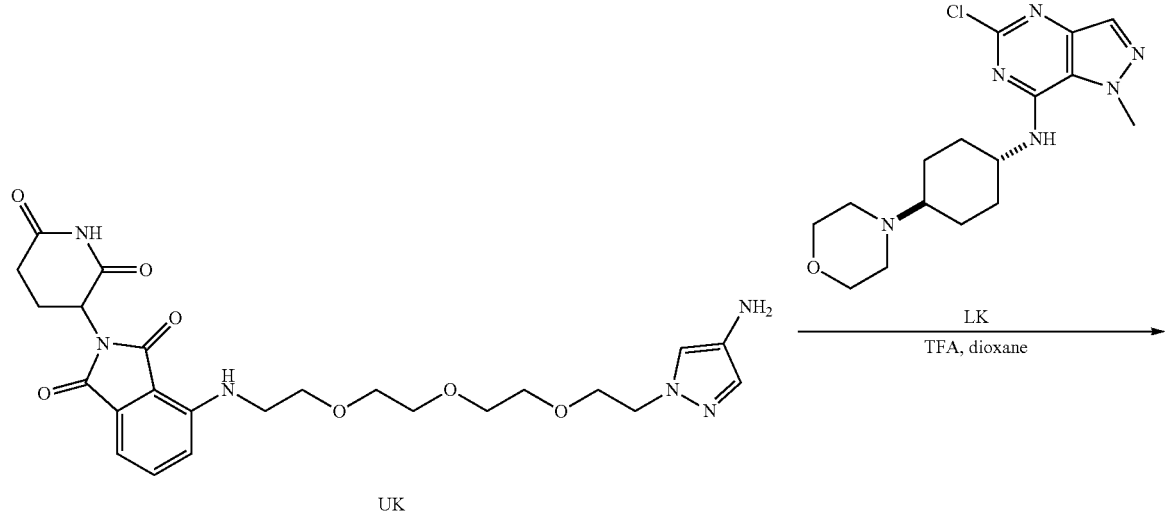

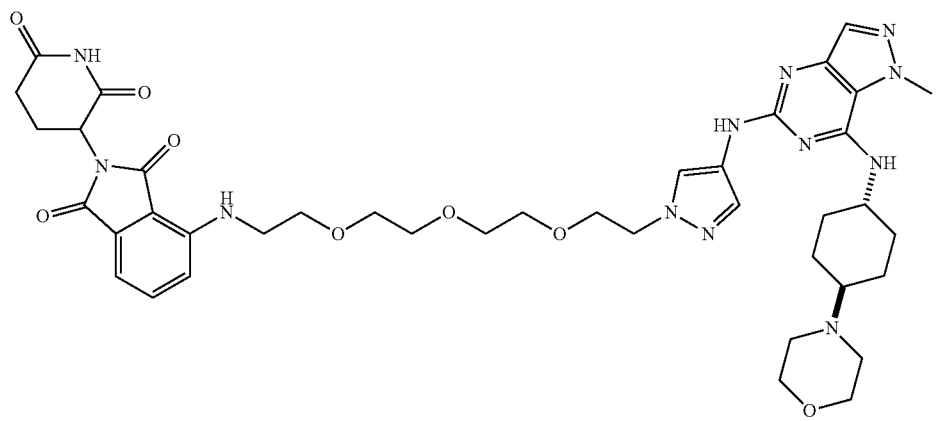

To a solution of 5-chloro-1-methyl-N-(4-morpholinocyclohexyl)pyrazolo[4,3-d]pyrimidin-7-amine (100 mg, 285 umol, Intermediate LK), 4-[2-[2-[2-[2-(4-aminopyrazol-1-yl)ethoxy]ethoxy]ethoxy]ethylamino]-2-(2,6-dioxo-3-piperidyl)isoindoline-1,3-dione (220 mg, 427 umol, Intermediate UK) in dioxane (6 mL) was added TFA (650 mg, 5.70 mmol). The reaction mixture was stirred at 120° C. for 2 hours. On completion, the reaction mixture was concentrated in vacuo. The residue was purified by prep-HPLC (column: Phenomenex Synergi C18 150*25*10 um; mobile phase: [water (0.225% FA)-ACN]; B %: 7%-28%, 7 min) to give the title compound (26.0 mg, 11% yield) as yellow solid. $^1$H NMR (400 MHz, DMSO-$d_6$) δ 11.10 (s, 1H), 8.57 (s, 1H), 7.91 (s, 1H), 7.57 (s, 1H), 7.57-7.51 (m, 1H), 7.47 (s, 1H), 7.07 (d, J=8.8 Hz, 1H), 7.02 (d, J=6.8 Hz, 1H), 6.56 (t, J=5.6 Hz, 1H), 6.45 (d, J=6.8 Hz, 1H), 5.04 (dd, J=5.2, 12.8 Hz, 1H), 4.16 (t, J=5.6 Hz, 2H), 4.13 (s, 3H), 4.07 (d, J=8.0 Hz, 1H), 3.72 (t, J=5.6 Hz, 2H), 3.63-3.59 (m, 4H), 3.57-3.49 (m, 12H), 2.92-2.81 (m, 1H), 2.62-2.58 (m, 4H), 2.57-2.53 (m, 2H), 2.39-2.35 (m, 1H), 2.10-2.06 (m, 2H), 2.03-1.99 (m, 1H), 1.96-1.92 (m, 2H), 1.55-1.46 (m, 2H), 1.42-1.32 (m, 2H). LC-MS (ESI$^+$) m/z 829.5 (M+H)$^+$.

Example 687: 2-(2,6-Dioxo-3-piperidyl)-4-[2-[2-[2-[4-[[1-methyl-7-[(4-morpholinocyclohexyl)amino]pyrazolo[4,3-d]pyrimidin-5-yl]amino]pyrazol-1-yl ethoxy]ethoxy]ethylamino]isoindoline-1,3-dione, II-692

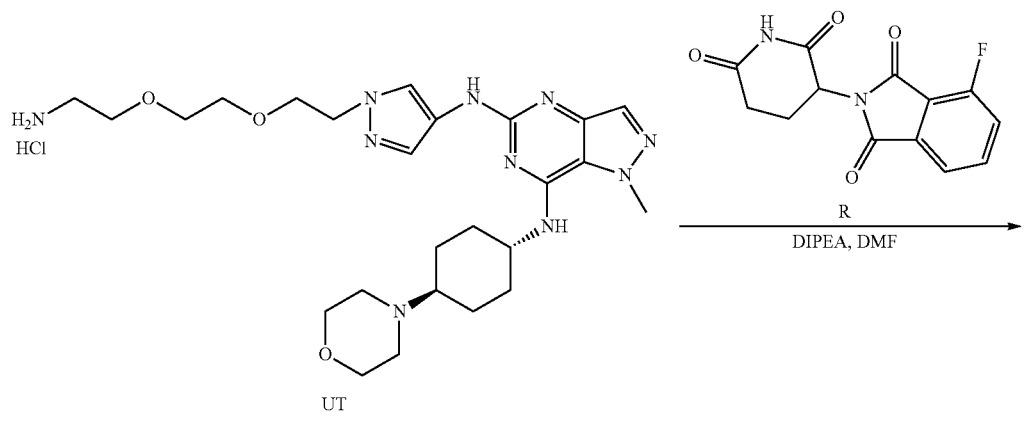

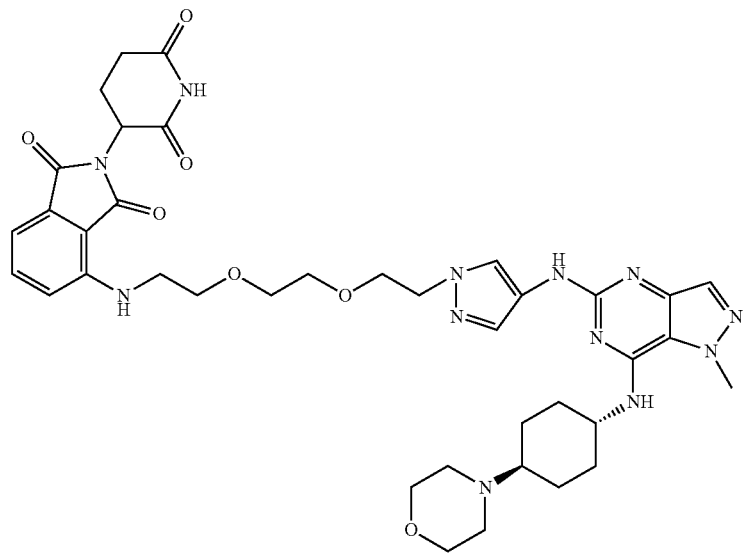

To a solution of N5-[1-[2-[2-(2-aminoethoxy)ethoxy]ethyl]pyrazol-4-yl]-1-methyl-N7-(4-morpholinocyclohexyl)pyrazolo[4,3-d]pyrimidine-5,7-diamine (60.0 mg, 106 umol, HCl, Intermediate UT) and 2-(2,6-dioxo-3-piperidyl)-4-fluoro-isoindoline-1,3-dione (29.3 mg, 106 umol, Intermediate R) in DMF (2 mL) was added DIPEA (68.6 mg, 530 umol, 92.4 uL). The mixture was stirred at 90° C. for 16 hours. On completion, the reaction mixture was concentrated in vacuo. The residue was purified by prep-HPLC (column: Phenomenex Synergi C18 150*25*10 um; mobile phase: [water (0.225% FA)-ACN]; B %: 9%-30%, 7 min) to give the title compound (13.2 mg, 15% yield, FA) as yellow solid. $^1$H NMR (400 MHz, DMSO-$d_6$) δ 11.09 (s, 1H), 8.55 (s, 1H), 7.92 (s, 1H), 7.56 (s, 1H), 7.54-7.43 (m, 2H), 7.05-6.96 (m, 2H), 6.55 (t, J=5.6 Hz, 1H), 6.43 (d, J=7.6 Hz, 1H), 5.04 (dd, J=5.2, 12.8 Hz, 1H), 4.17 (t, J=5.2 Hz, 2H), 4.12 (s, 3H), 4.10-4.04 (m, 1H), 3.74 (t, J=5.2 Hz, 2H), 3.57-3.51 (m, 14H), 2.94-2.78 (m, 2H), 2.63-2.58 (m, 1H), 2.57-2.54 (m, 1H), 2.28-2.21 (m, 1H), 2.13-1.82 (m, 6H), 1.56-1.45 (m, 2H), 1.39-1.29 (m, 2H); LC-MS (ESI$^+$) m/z 785.4 (M+H)$^+$.

Example 688: (2S,4R)-1-[(2S)-3,3-dimethyl-2-[[2-[2-[2-[2-[2-[[1-methyl-7-[(4-morpholinocyclohexyl)amino]pyrazolo[4,3-d]pyrimidin-5-yl]amino]ethoxy]ethoxy]ethoxy]ethoxy]acetyl]amino]butanoyl]-4-hydroxy-N-[[4-(4-methylthiazol-5-yl)phenyl]methyl]pyrrolidine-2-carboxamide, 1I-693

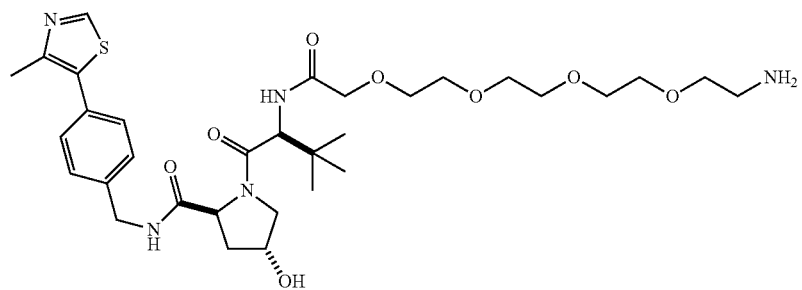
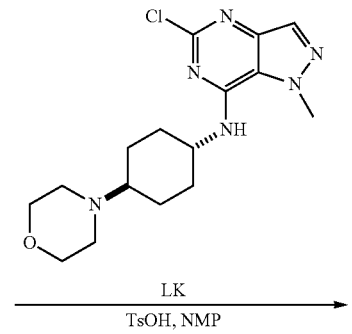

To a solution of (2S,4R)-1-[(2S)-2-[[2-[2-[2-[2-(2-aminoethoxy)ethoxy]ethoxy]ethoxy]acetyl]amino]-3,3-dimethylbutanoyl]-4-hydroxy-N-[[4-(4-methylthiazol-5-yl)phenyl]methyl]pyrrolidine-2-carboxamide (30.0 mg, 45.1 umol, Intermediate ME), 5-chloro-1-methyl-N-(4-morpholinocyclohexyl)pyrazolo[4,3-d]pyrimidin-7-amine (14.4 mg, 41.0 umol, Intermediate LK) in NMP (2.00 mL) was added TsOH (707 ug, 4.11 umol). The mixture was stirred at 150° C. for 6 hours under microwave. On completion, the mixture was concentrated in vacuo. The mixture was purified by prep-HPLC (column: Phenomenex Gemini 150*25 mm*10 um; mobile phase: [water (0.04% NH$_3$.H$_2$O+10 mM NH$_4$HCO$_3$)-ACN]; B %: 30%-58%, min). The residue was re-purified by prep-HPLC (column: Phenomenex Gemini 150*25 mm*10 um; mobile phase: [water (0.04% NH$_3$.H$_2$O+10 mM NH$_4$HCO$_3$)-ACN]; B %: 30%-54%, min) to give the title compound (2.39 mg, 5% yield) as brown solid. $^1$H NMR (400 MHz, DMSO-d$_6$) δ 8.97 (s, 1H), 8.59 (t, J=5.6 Hz, 1H), 7.49 (s, 1H), 7.42 (s, 1H), 7.39 (m, 4H), 6.31 (d, J=8.0 Hz, 1H), 5.96 (t, J=5.6 Hz, 1H), 5.16 (d, J=3.2 Hz, 1H), 4.56 (d, J=9.6 Hz, 1H), 4.48-4.38 (m, 2H), 4.37-4.32 (m, 1H), 4.29-4.23 (m, 1H), 4.10 (s, 3H), 4.05-3.98 (m, 1H), 3.96 (s, 2H), 3.66-3.57 (m, 6H), 3.56-3.48 (m, 14H), 2.49-2.45 (m, 6H), 2.44 (s, 3H), 2.26-2.16 (m, 1H), 2.07-1.98 (m, 3H), 1.95-1.83 (m, 3H), 1.54-1.40 (m, 2H), 1.34-1.22 (m, 2H), 0.94 (s, 9H), LC-MS (ESI$^+$) m/z 978.7 (M+H)$^+$.

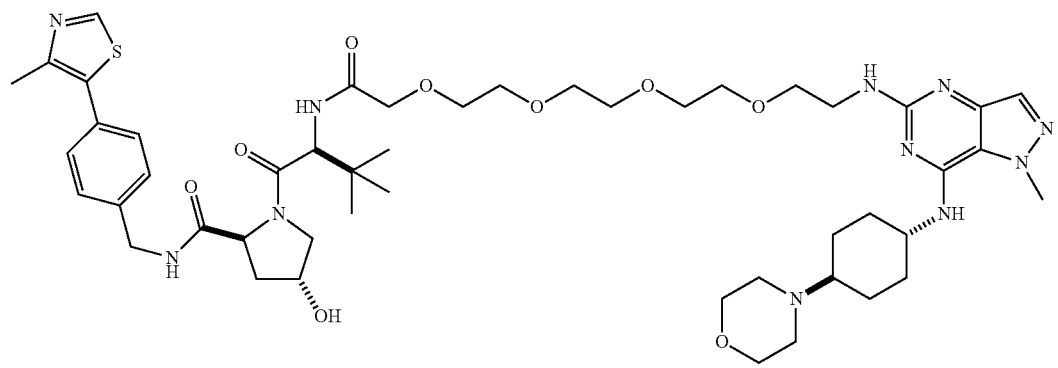

Example 689: N-[3-(difluoromethyl)-1-methyl-pyrazol-4-yl]-5-[4-[2-[2-[3-[1-(2,6-dioxo-3-piperidyl)-3-methyl-2-oxo-benzimidazol-5-yl]propoxy]ethoxy]ethyl]piperazin-1-yl]pyrazolo[1,5-a]pyrimidine-3-carboxamide, I-694

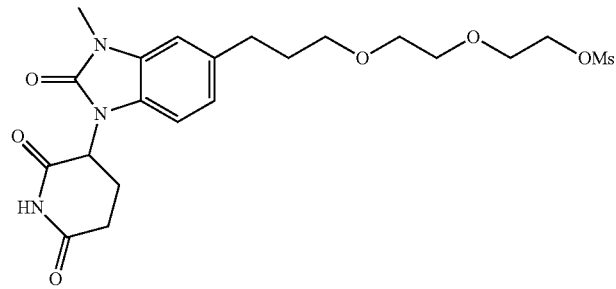

UB

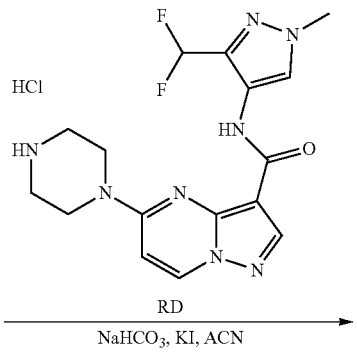

RD
NaHCO₃, KI, ACN

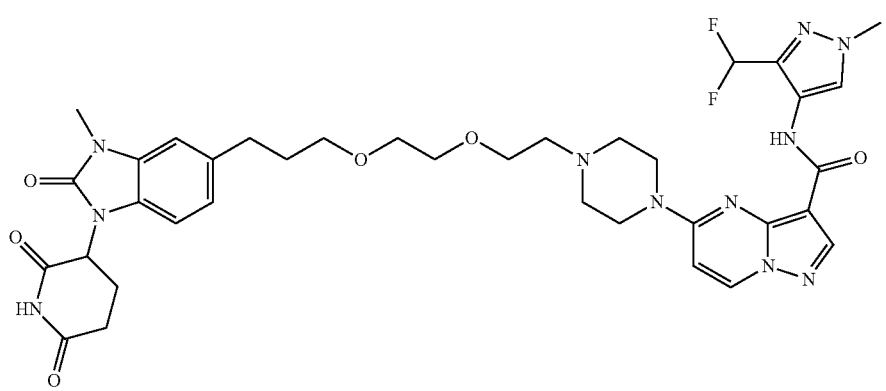

To a mixture of 2-[2-[3-[1-(2,6-dioxo-3-piperidyl)-3-methyl-2-oxo-benzimidazol-5-yl]propoxy]ethoxy]ethyl methanesulfonate (70 mg, 144 umol, Intermediate UB) and N-[3-(difluoromethyl)-1-methyl-pyrazol-4-yl]-5-piperazin-1-yl-pyrazolo[1,5-a]pyrimidine-3-carboxamide (59.7 mg, 144 umol, HCl, Intermediate RD) in ACN (3 mL) was added NaHCO₃ (36.4 mg, 434 umol) and KI (2.40 mg, 14.4 umol), and the mixture was stirred at 80° C. for 16 hours. On completion, the reaction mixture was quenched with water (15 mL), and then extracted with EA (4×20 mL). The combined organic layers were dried over Na₂SO₄, filtered and concentrated in vacuo to give a residue. The residue was purified by prep-HPLC (column: Phenomenex luna C18 150*25 10 u; mobile phase: [water (0.225% FA)-ACN]) to give the title compound (8.68 mg, 10.7 umol, 7% yield, FA) as yellow solid. $^1$H NMR (400 MHz, DMSO-$d_6$) δ 11.07 (s, 1H), 9.39 (s, 1H), 8.74 (d, J=7.6 Hz, 1H), 8.34 (s, 1H), 8.26 (s, 1H), 7.22-6.91 (m, 3H), 6.88-6.74 (m, 2H), 5.32 (dd, J=5.2, 12.8 Hz, 1H), 3.87 (s, 3H), 3.84-3.70 (m, 4H), 3.58 (t, J=5.6 Hz, 2H), 3.55-3.50 (m, 4H), 3.30 (s, 3H), 2.94-2.82 (m, 1H), 2.74-2.53 (m, 10H), 2.05-1.92 (m, 1H), 1.88-1.71 (m, 2H); LC-MS (ESI$^+$) m/z 764.1 (M+H)$^+$.

Examples 694 and 695: 2-[2-(Cyclopropylmethyl-amino)-4-pyridyl]-N-[3-(difluoromethyl)-1-[4-[[4-[4-[1-[(3S)-2,6-dioxo-3-piperidyl]-3-methyl-2-oxo-benzimidazol-5-yl]butoxy]butylamino]methyl]phenyl]pyrazol-4-yl]oxazole-4-carboxamide, I-699 & 2-[2-(cyclopropylmethylamino)-4-pyridyl]-N-[3-(difluoromethyl)-1-[4-[[4-[4-[1-[(3R)-2,6-dioxo-3-piperidyl]-3-methyl-2-oxo-benzimidazol-5-yl]butoxy]butylamino]methyl]phenyl]pyrazol-4-yl]oxazole-4-carboxamide, I-700 methyl]phenyl]pyrazol-4-yl]oxazole-4-carboxamide (3.80 mg, 14% yield, ee value=77%) as a white solid. The absolute configuration of the enantiomers was arbitrarily assigned. Characterization of 2-[2-(cyclopropylmethylamino)-4-pyridyl]-N-[3-(difluoromethyl)-1-[4-[[4-[4-[1-[(3S)-2,6-dioxo-3-piperidyl]-3-methyl-2-oxo-benzimidazol-5-yl]butoxy]butylamino]methyl]phenyl]pyrazol-4-yl]oxazole-4-carboxamide: $^1$H NMR (400 MHz, DMSO-$d_6$) δ 11.22 (s, 1H), 9.99 (s, 1H), 8.97 (s, 1H), 8.78 (s, 1H), 8.36 (s, 1H), 8.16 (d, J=5.2 Hz, 1H), 7.79 (d, J=8.8 Hz, 2H), 7.47 (d, J=8.8 Hz, 2H), 7.42-7.15 (m, 1H), 7.13-7.07 (m, 2H), 7.06-6.96

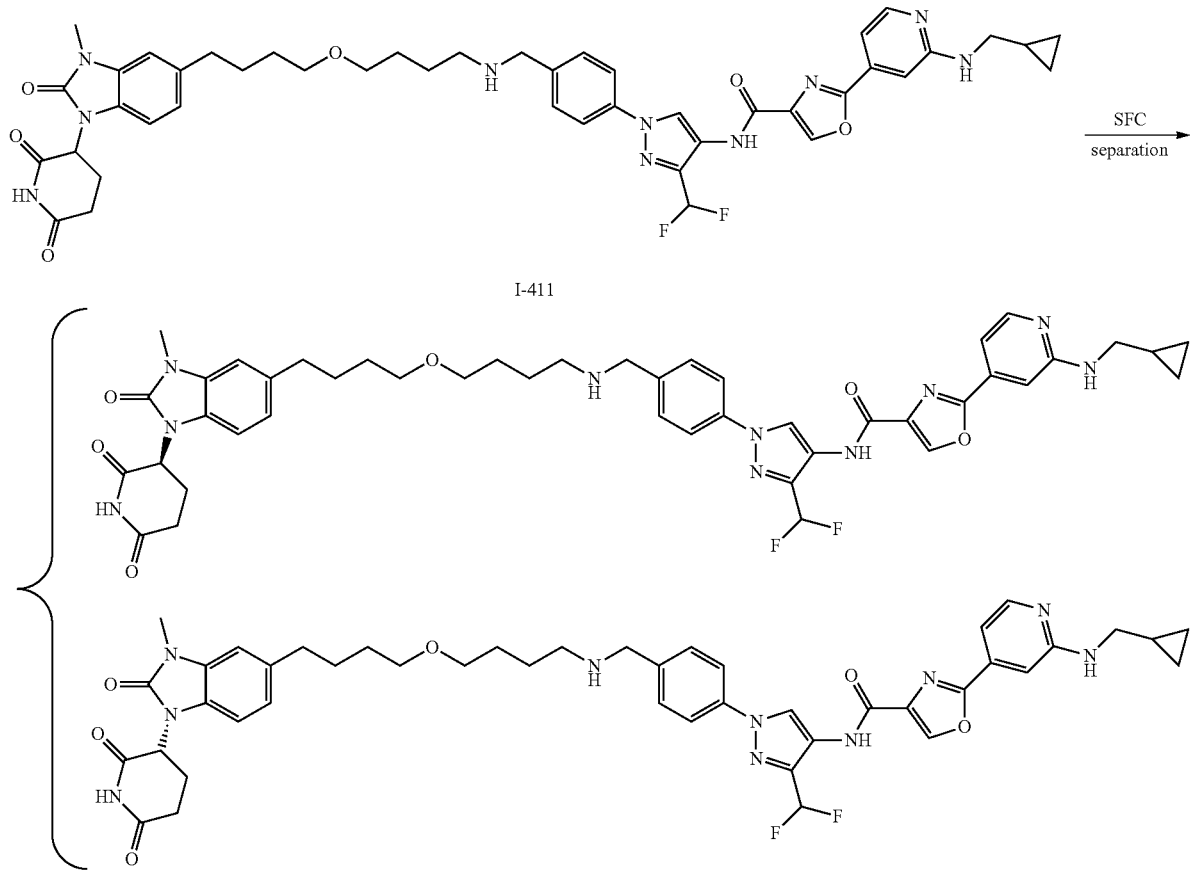

The 2-[2-(cyclopropylmethylamino)-4-pyridyl]-N-[3-(difluoromethyl)-1-[4-[[4-[4-[1-(2,6-dioxo-3-piperidyl)-3-methyl-2-oxo-benzimidazol-5-yl]butoxy]butylamino]methyl]phenyl]pyrazol-4-yl]oxazole-4-carboxamide (50.0 mg, 54.9 umol, FA salt, Example 406, I-411) was separated by SFC (column: DAICEL CHIRALPAK IC (250 mm*30 mm, 10 um); mobile phase: [0.1% NH$_3$H$_2$O MeOH]; B %: 70%-70%, 13.7 min; 160 min) to give the two enantiomers. Then the two enantiomers were purified by prep-HPLC (column: Shim-pack C18 150*25*10 um; mobile phase: [water (0.225% FA)-ACN]; B %: 11%-41%) respectively to give 2-[2-(cyclopropylmethylamino)-4-pyridyl]-N-[3-(difluoromethyl)-1-[4-[[4-[4-[1-[(3S)-2,6-dioxo-3-piperidyl]-3-methyl-2-oxo-benzimidazol-5-yl]butoxy]butylamino]methyl]phenyl]pyrazol-4-yl]oxazole-4-carboxamide (3.40 mg, 12% yield, ee value=91%) as a white solid and 2-[2-(cyclopropylmethylamino)-4-pyridyl]-N-[3-(difluoromethyl)-1-[4-[[4-[4-[1-[(3R)-2,6-dioxo-3-piperidyl]-3-methyl-2-oxo-benzimidazol-5-yl]butoxy]butylamino]

(m, 3H), 6.88-6.82 (m, 1H), 5.33 (d, J=5.2, 12.8 Hz, 1H), 3.73 (s, 2H), 3.31 (s, 6H), 3.21-3.16 (m, 3H), 2.97-2.82 (m, 1H), 2.75-2.55 (m, 6H), 2.03-1.94 (m, 1H), 1.66-1.57 (m, 2H), 1.55-1.43 (m, 6H), 1.11-1.03 (m, 1H), 0.49-0.41 (m, 2H), 0.26-0.19 (m, 2H); LC-MS (ESI$^+$) m/z 865.5 (M+H)$^+$. Characterization of 2-[2-(cyclopropylmethylamino)-4-pyridyl]-N-[3-(difluoromethyl)-1-[4-[[4-[4-[1-[(3R)-2,6-dioxo-3-piperidyl]-3-methyl-2-oxo-benzimidazol-5-yl]butoxy]butylamino]methyl]phenyl]pyrazol-4-yl]oxazole-4-carboxamide: $^1$H NMR (400 MHz, DMSO-$d_6$) δ 11.05 (s, 1H), 9.96 (s, 1H), 8.95 (s, 1H), 8.76 (s, 1H), 8.35 (s, 1H), 8.14 (d, J=5.2 Hz, 1H), 7.76 (d, J=8.8 Hz, 2H), 7.45 (d, J=8.4 Hz, 2H), 7.40-7.12 (m, 1H), 7.11-7.05 (m, 2H), 7.04-6.94 (m, 3H), 6.83 (d, J=8.0 Hz, 1H), 5.30 (d, J=5.2, 12.8 Hz, 1H), 3.70 (s, 2H), 3.29 (s, 6H), 3.16 (d, J=6.4 Hz, 3H), 2.93-2.81 (m, 1H), 2.73-2.55 (m, 6H), 2.02-1.92 (m, 1H), 1.65-1.55 (m, 2H), 1.53-1.40 (m, 6H), 1.11-0.99 (m, 1H), 0.47-0.39 (m, 2H), 0.23-0.17 (m, 2H); LC-MS (ESI$^+$) m/z 865.5 (M+H)$^+$.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

Example 205: AlphaLISA Assay to Determine Ternary Complex Formation

The assay mixture contains 100 nM CRBN-DDB1, 100 nM GST-IRAK4, 20 µg/mL Nickle Chelate Donor Bead (Perkin Elmer Catalog # AS101D) and 20 µg/mL GSH Acceptor Bead (Perkin Elmer Catalog # AL109C) in a buffer containing 50 mM HEPES, pH 7.5, 100 mM NaCl, 0.1% BSA, 2 mM TCEP, 0.05% Tween-20. Various amount of heterobifunctional degrader compounds were titrated into the assay mixture ranging from 6.26 nM to 12.8 µM (final concentration) in a two-fold dilution series. AlphaLISA signals (Excitation 680 nm and emission 615 nM) were recorded on a Perkin Elmer EnVision 2104 Multilabel reader. The raw data was converted to the relative amount of ternary complex formation by normalization to the signal generated by His-tagged GST protein only. The final data points were plotted and the curves were fit using non-linear regression using GraphPad Prism software.

The ternary complex formation (as a percentage of total IRAK4) mediated by I-127 is depicted in FIG. 1.

Figure 2:
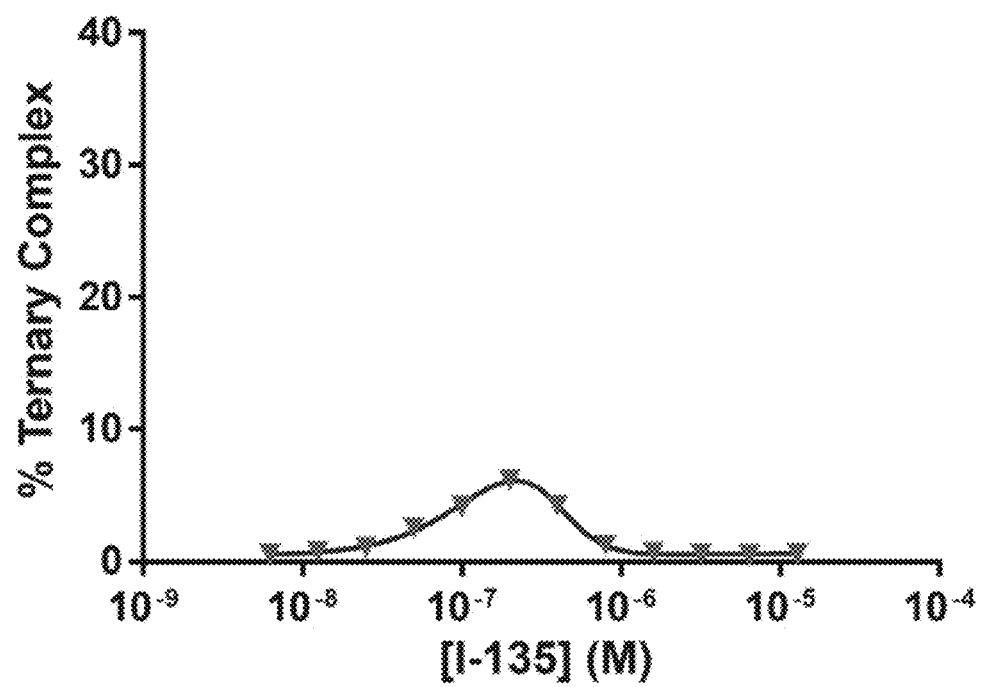
FIG. 2 depicts the ternary complex formation (as a percentage of total IRAK4) mediated by I-135.

The ternary complex formation (as a percentage of total IRAK4) mediated by I-135 is depicted in FIG. 2.

The raw data used for generating FIG. 1 is shown in Table 20.

TABLE 20

Raw data used for generating FIG. 1.

| [I-127] (M) | Average % Ternary Complex (N = 2) | Standard Deviation |
|---|---|---|
| 1.28E−05 | 1.58 | 0.05 |
| 6.40E−06 | 3.36 | 0.1 |
| 3.20E−06 | 6.74 | 0.53 |
| 1.60E−06 | 12.53 | 0.89 |
| 8.00E−07 | 17.79 | 1.04 |
| 4.00E−07 | 25.83 | 1.28 |
| 2.00E−07 | 28.96 | 0.34 |
| 1.00E−07 | 31.29 | 0.17 |
| 5.00E−08 | 23.14 | 1.86 |
| 2.50E−08 | 12.66 | 0.05 |
| 1.25E−08 | 5.89 | 0.59 |
| 6.25E−09 | 2.71 | 0.19 |

The raw data used for generating FIG. 2 is shown in Table 21.

TABLE 21

Raw data used for generating FIG. 2.

| [I-135] (M) | Average % Ternary Complex (N = 2) | Standard Deviation |
|---|---|---|
| 1.28E−05 | 0.61 | 0.1 |
| 6.40E−06 | 0.5 | 0 |
| 3.20E−06 | 0.57 | 0.06 |
| 1.60E−06 | 0.67 | 0.03 |
| 8.00E−07 | 1.25 | 0.03 |
| 4.00E−07 | 4.22 | 0.18 |
| 2.00E−07 | 6.15 | 0.68 |
| 1.00E−07 | 4.16 | 0.05 |
| 5.00E−08 | 2.54 | 0.32 |
| 2.50E−08 | 1.05 | 0.03 |
| 1.25E−08 | 0.76 | 0.12 |
| 6.25E−09 | 0.55 | 0.04 |

Example 206: ABC-DLBCL Cell Viability Assay

The human ABC-DLBCL cell line SU-DHL-2 (MyD88 S222R, from DSMZ) was maintained in IMDM media containing 20% fetal bovine serum and 55 µM 2-mercaptoethanol. Cells were harvested by centrifugation, resuspended in fresh media and added to each well of a 384 well plate at 6000 cells/well in 30 µL volume. 30 µL of test compound diluted in media were added to each well for assay. Final concentration of test compound was varied from a high of 10 µM to a low of 0.0015 µM using a 3-fold, 8 step serial dilution. Final DMSO concentration was 0.2% for all wells in 60 µL final volume. Plates containing cells plus test compounds were incubated for 4 days at 37° C. in an incubator containing 5% $CO_2$.

Cell viability was determined using CellTiter Glo reagent (Promega). Assay plates were equilibrated to room temperature for 10 minutes. CellTiter Glo was prepared according to manufacturer's instructions, 30 µL was added to every well of each assay plate and plates were centrifuged for 30 seconds at 1000 rpm. Plates were shaken for 1 minute, centrifuged for 30 seconds at 1000 rpm and incubated for 10 minutes at room temperature to stabilize luminescent signal. Luminescent signal per well was determined using a Perkin Elmer Envision plate reader.

Data were normalized to DMSO treatment as 100% viability and 0.5 µM paclitaxel treatment as 0% viability. Data were plotted in GraphPad Prism as log(10) of compound concentration vs Viability and IC50 calculated as the inflection point of the logistic curve.

Figure 3:
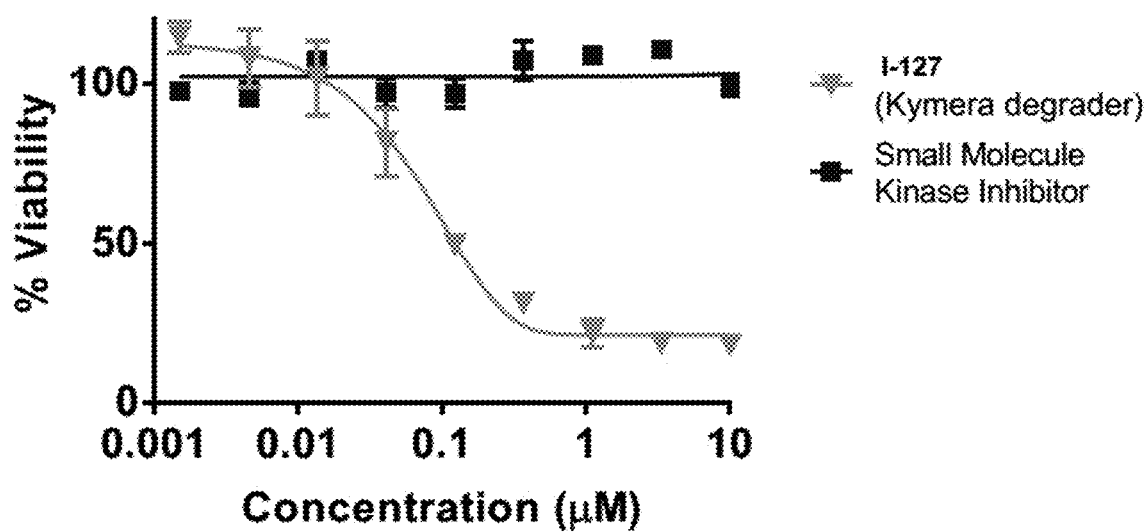
FIG. 3 depicts ABL-DLBCL cell viability assay results for I-127.

ABC-DLBCL cell viability results for I-127 are depicted in FIG. 3.

Example 207: Human PBMC Cytokine Release Assays

Frozen PBMCs were thawed and rested overnight at 37° C., 5% $CO_2$. Viable cells were plated at 125,000 per well. Cells were pre-incubated with compounds for 20 hours (degraders) or 1 hour (kinase inhibitors). Following compound incubation, cells were stimulated with 1 µg/mL of the TLR7/8 agonist R848 (Invivogen # tlrl-r848) or 100 ng/mL of the TLR4 agonist LPS (Sigma # L2637) for an additional 4 hours. At the end of the assay, supernatants were harvested and TNFα levels were quantified by Meso Scale Discovery immuno assay (# K151A0H).

Figure 4:
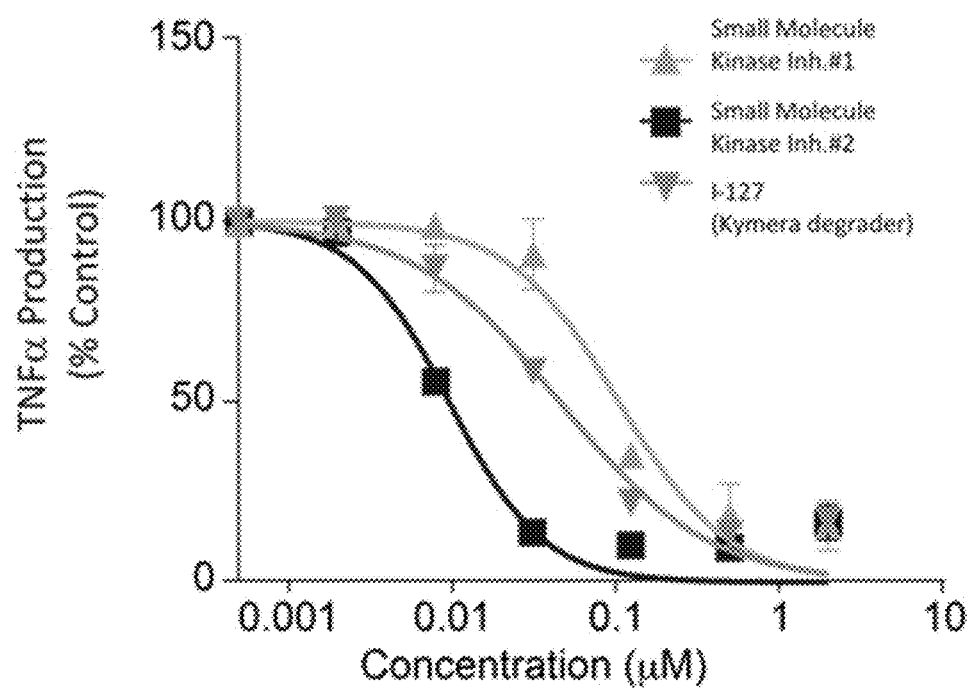
FIG. 4 depicts human PBMC cytokine release assays results, R848 (TLR7/8) activation, for I-127.

R848 (TLR7/8) activation results for I-127 are depicted in FIG. 4.

Figure 5:
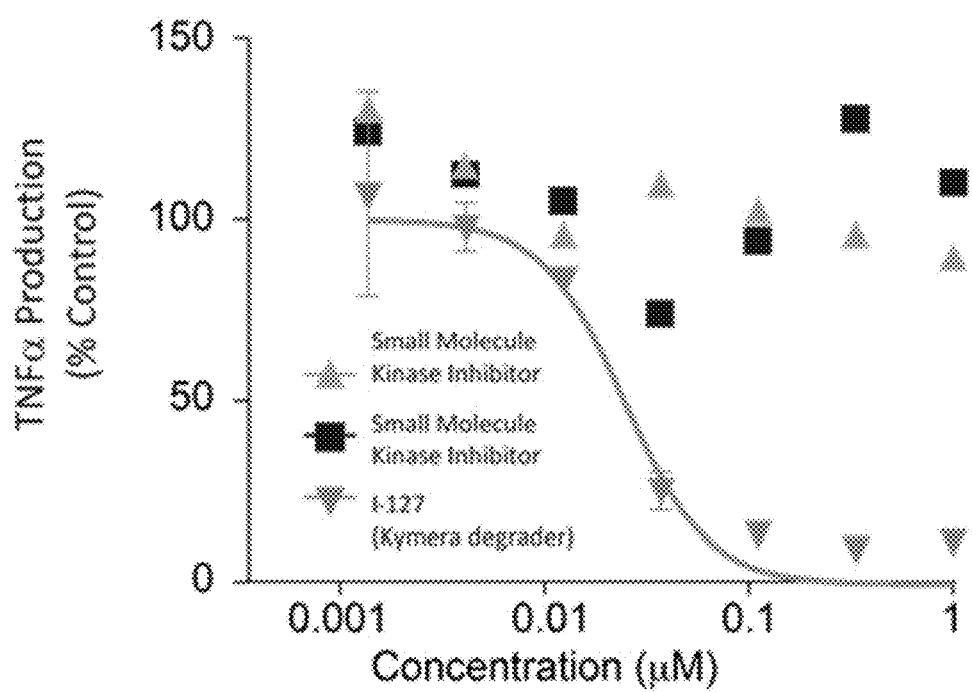
FIG. 5 depicts human PBMC cytokine release assays results, LPS (TLR4) stimulation, for I-127.

LPS (TLR4) stimulation results for I-127 are depicted in FIG. 5.

Example 208: In Vivo Degradation in Sprague Dawley Rats

Male Sprague Dawley rats aged 7-9 weeks (SLAC Laboratory Animal Co. Ltd., Shanghai, China; or SIPPR-B&K Laboratory Animal Co. Ltd., Shanghai, China) were assessed as to their general health by a member of the veterinary staff or other authorized personnel. Animals were acclimated for at least 3 days (upon arrival at WuXi AppTec) before being placed on study.

Animals were group housed during acclimation and individually housed during the study. The animal room environment was controlled (target conditions: temperature 20 to 26° C., relative humidity 30 to 70%, 12 hours artificial light and 12 hours dark). Temperature and relative humidity were monitored daily.

Animals were fasted at least 12 hours prior to the administration. Animals had access to water ad libitum and had access to Certified Rodent Diet (Beijing KEAO XIELI Feed Co., Ltd. Beijing, P.R. China) ad libitum after finishing infusion.

The lot number and specifications of each lot used was archived at WuXi AppTec. Water was autoclaved before provided to the animals ad libitum. Periodic analyses of the water was performed and the results archived at WuXi AppTec.

There were no known contaminants in the diet or water that, at the levels of detection, are expected to interfere with the purpose, conduct or outcome of the study.

I-171 was formulated as a clear solution in 10% DMSO: 90% PEG400 at 5 mg/mL (for 5 mg/kg), 10 mg/mL (for 10 mg/kg) or 20 mg/ml (for 20 mg/kg). Vehicle control received 10% DMSO:90% PEG400.

Groups of 5 animals per condition were dosed intravenously with 1 mL of I-171 solution or vehicle via the catheter indwelled in jugular vein following facility SOPs. Final dosing was 5 mg/kg, 10 mg/kg, 20 mg/kg or vehicle control. Six hours or 24 hours after dosing, animals were humanely sacrificed following facility SOP and spleens were removed and divided in two equal portions.

Splenocytes were prepared by physical dissociation of spleen tissue in ice cold phosphate buffered saline (PBS) and passing through a 40 μm cell strainer (Corning). After rinsing the strainer, cells were collected, transferred to complete media (DMEM, Invitrogen 11995) in a 15 mL conical tube and centrifuged at 165×g for 5 minutes to collect. Medium was aspirated and cell pellet was resuspended with 4 mL of ACK lysis buffer (Invitrogen A1049201). 2 mL (half the volume) was immediately transferred to a new 15 mL conical tube, resulting in 2×15 mL conical tubes per spleen half. Cells were incubated in the dark at room temperature for 10 minutes. 13 mL of complete medium was added to each tube and cells were collected by centrifugation for 5 minutes at 235×g. Media was aspirated without disturbing cell pellets, cells were resuspended in 1 mL PBS, and cells from same spleen were combined and passed through 40 μm cell strainer (Corning). Cells were collected by centrifugation for 5 min at 300×g, PBS was aspirated and cell pellets were flash frozen and stored at −80° C.

Figure 6:
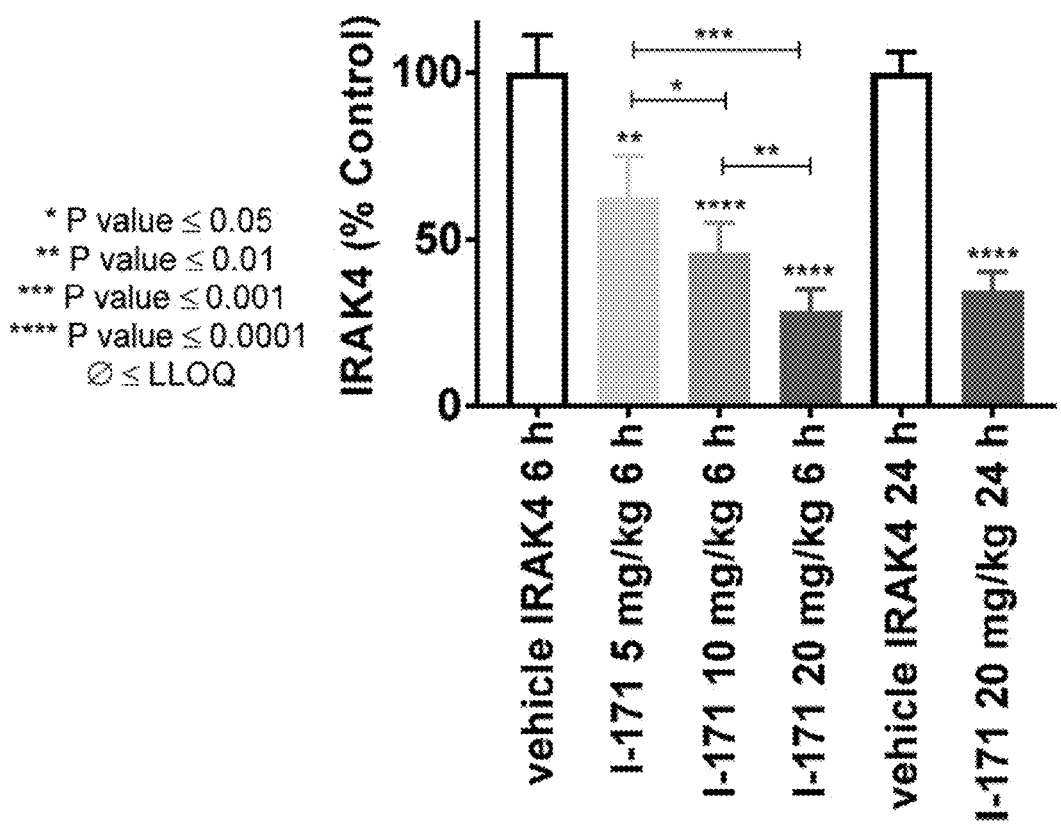
FIG. 6 depicts in vivo degradation in Sprague Dawley rat splenocytes for I-171.

IRAK4 and actin (as a loading control) were quantified in splenocyte samples by HPLC MS/MS using isotope labeled internal peptide standard. Total protein per splenocyte sample was determined by BCA protein assay. Background signal for IRAK4 was determined as the level present in IRAK4 null patient fibroblasts relative to total protein, and this value was subtracted from all experimental samples. Ratio of IRAK4 to actin was determined for all samples. Treated samples were normalized to time matched vehicle treated control and expressed as percent of control. Data were plotted and analyzed in GraphPad Prism software package. Unpaired, two tailed t tests P values are reported as noted by asterisks in the legend of FIG. 6.

Example 209: Pharmacokinetics in Sprague Dawley Rats and CD-1 Mice

Pharmacokinetics for I-127, I-172 and I-210 were determined in Sprague Dawley rats or CD-1 mice by dosing intravenous (IV), subcutaneous (SC) or per oral (PO) using facility SOPs and sampling plasma at required time points. Species, formulation, route of administration and time points samples are listed below for each compound.

Compounds were extracted from plasma, injected on reverse phase HPLC, eluted with a gradient from 5% to 95% acetonitrile in water and quantified by mass spectrometry with internal standard. Data are expressed in ng compound per mL of plasma.

I-210

Figure 7:
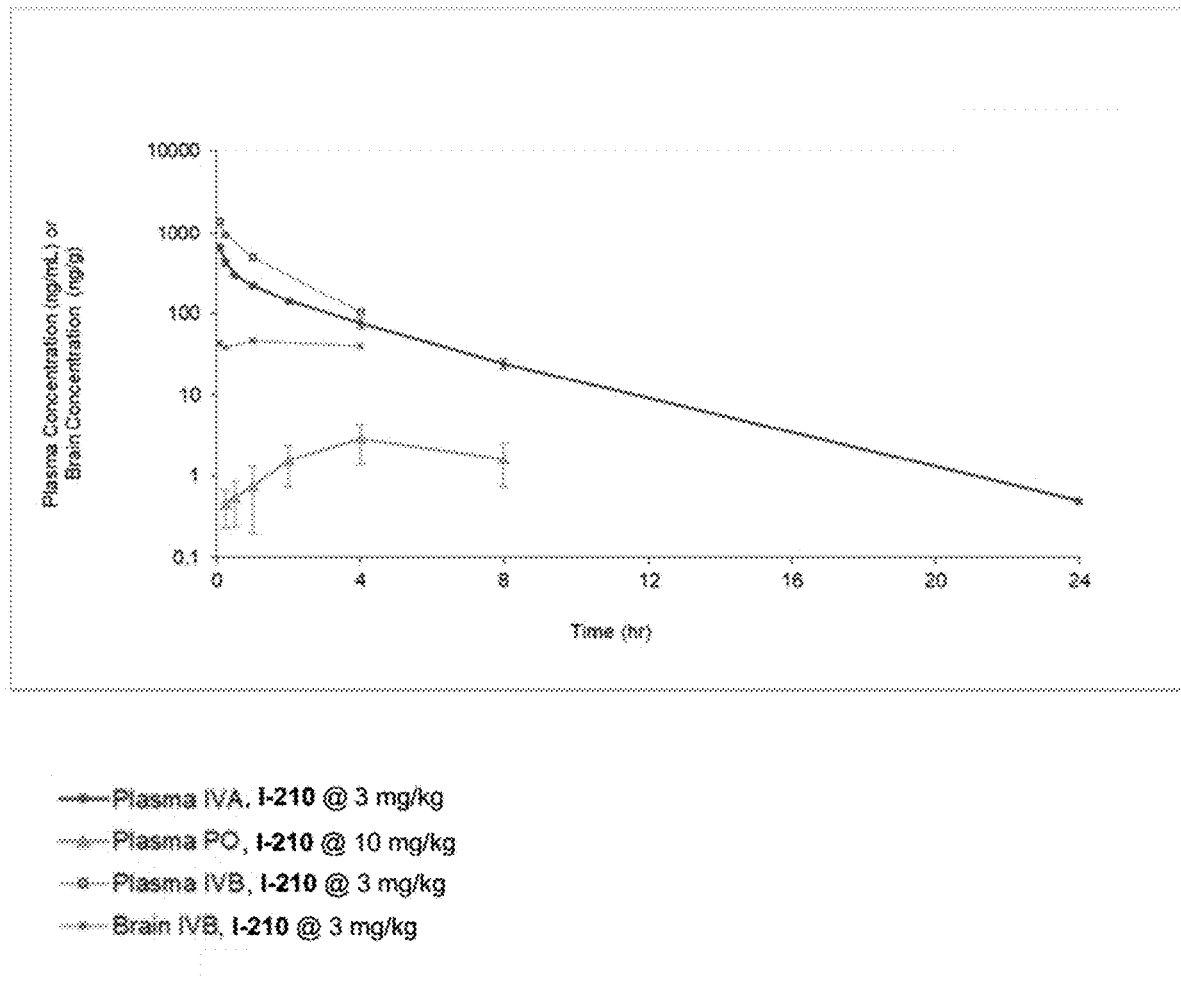
FIG. 7 depicts the plasma and brain concentration versus time profile for I-210 after 3 mg·kg IV and 10 mg/kg PO in Sprague Dawley rat.

Rat (Sprague Dawley) iv pk @ 3 mg/kg (IVA depicted in FIG. 7)

Formulation: 5% DMSO and 2% Cremphor in 20% HP-β-CD in saline

TABLE 22

I-210 concentrations dosed iv @ 3 mg/kg

| Time | Concentration (ng/mL) | | | Mean | SD | CV |
|---|---|---|---|---|---|---|
| (h) | Rat 1 | Rat 2 | Rat 3 | (ng/mL) | (ng/mL) | (%) |
| 0 | BLOQ | BLOQ | BLOQ | NA | NA | NA |
| 0.0833 | 671 | 652 | 700 | 674 | 24 | 3.58 |
| 0.25 | 396 | 418 | 469 | 428 | 37 | 8.76 |
| 0.5 | 307 | 292 | 312 | 304 | 10 | 3.43 |
| 1 | 236 | 232 | 207 | 225 | 16 | 6.98 |
| 2 | 141 | 159 | 132 | 144 | 14 | 9.55 |
| 4 | 86.0 | 77.7 | 64.5 | 76.1 | 10.8 | 14.3 |
| 8 | 27.5 | 24.8 | 20.3 | 24.2 | 3.6 | 15.0 |
| 24 | 0.454 | 0.545 | 0.488 | 0.496 | 0.046 | 9.28 |

TABLE 23

I-210 PK parameters dosed iv @ 3 mg/kg

| PK parameters | Unit | Rat 1 | Rat 2 | Rat 3 | Mean | SD | CV (%) |
|---|---|---|---|---|---|---|---|
| Cl_obs | mL/min/kg | 40.2 | 41.2 | 45.7 | 42A | 2.9 | 6.95 |
| $T_{1/2}$ | h | 2.66 | 2.83 | 2.88 | 2.79 | 0.11 | 4.05 |
| $C_0$ | ng/mL | 873 | 814 | 855 | 848 | 30 | 3.57 |
| $AUC_{last}$ | h * ng/mL | 1243 | 1210 | 1091 | 1181 | 80 | 6.74 |
| $AUC_{Inf}$ | h * ng/mL | 1245 | 1212 | 1094 | 1183 | 80 | 6.73 |
| $AUC\_\%Extrap\_obs$ | % | 0.140 | 0.183 | 0.185 | 0.169 | 0.026 | 15.1 |
| $MRT_{Inf}\_obs$ | h | 3.26 | 3.15 | 2.92 | 3.11 | 0.17 | 5.57 |
| $AUC_{last}/D$ | h * mg/mL | 414 | 403 | 364 | 394 | 27 | 6.74 |
| $V_{ss}\_obs$ | L/kg | 7.85 | 7.79 | 8.00 | 7.88 | 0.11 | 1.38 |

I-210
Rat (Sprague Dawley) po pk @ 10 mg/kg (PO depicted in FIG. 7)
Formulation: 0.5% CMC and 0.25% Tween 80 in water

TABLE 24

| Rat po pk @ 10 mg/kg for I-210 | | | | | | |
|---|---|---|---|---|---|---|
| Time | Concentration (ng/mL) | | | Mean | SD | CV |
| (h) | Rat 4 | Rat 5 | Rat 6 | (ng/mL) | (ng/mL) | (%) |
| 0 | BLOQ | BLOQ | BLOQ | NA | NA | NA |
| 0.25 | 0.716 | 0.359 | 0.300 | 0.458 | 0.225 | 49.1 |
| 0.5 | 0.914 | 0.366 | 0.377 | 0.552 | 0.313 | 56.7 |
| 1 | 1.39 | 0.438 | 0.426 | 0.75 | 0.55 | 73.6 |
| 2 | 1.55 | 2.39 | 0.737 | 1.56 | 0.83 | 53.0 |
| 4 | 3.50 | 4.02 | 1.20 | 2.91 | 1.50 | 51.6 |
| 8 | 1.66 | 2.46 | 0.710 | 1.61 | 0.88 | 54.4 |
| 24 | BLOQ | BLOQ | BLOQ | NA | NA | NA |

TABLE 25

| Rat PK parameters dosed po @ 10 mg/kg for I-210 | | | | | | | |
|---|---|---|---|---|---|---|---|
| PK parameters | Unit | Rat 4 | Rat 5 | Rat 6 | Mean | SD | CV (%) |
| $T_{1/2}$ | h | 3.72 | 5.65 | 5.28 | 4.88 | 1.02 | 21.0 |
| $T_{max}$ | h | 4 | 4 | 4 | 4.00 | 0.00 | 0.00 |
| $C_{max}$ | ng/mL | 3.50 | 4.02 | 1.20 | 2.91 | 1.50 | 51.6 |
| $AUC_{last}$ | h * ng/mL | 17.7 | 21.1 | 6.66 | 15.2 | 7.6 | 49.8 |
| $AUC_{Inf}$ | h * ng/mL | 26.6 | 41.2 | 12.1 | 26.6 | 14.5 | 54.6 |
| $AUC_{\%Extrap\_obs}$ | % | 33.5 | 48.7 | 44.8 | 42.3 | 7.9 | 18.7 |
| $MRT_{Inf\_obs}$ | h | 7.27 | 10.2 | 9.35 | 8.9 | 1.5 | 16.8 |
| $AUC_{last}/D$ | h * mg/mL | 1.77 | 2.11 | 0.666 | 1.52 | 0.76 | 49.8 |
| F | % | 0.450 | 0.536 | 0.169 | 0.385 | 0.192 | 49.8 |

I-210
Rat (Sprague Dawley) iv pk @ 3 mg/kg (IVB depicted in FIG. 7)
Formulation: 5% DMSO and 2% Cremphor in 20% HP-β-CD in saline

TABLE 26

| I-210 brain concentration/time data for I-210 | | | | | |
|---|---|---|---|---|---|
| Time | Detected Conc. (ng/mL) | | Actual Conc. (ng/g) | | Mean |
| (h) | Group 1 | Group 2 | Group 1 | Group 2 | (ng/g) |
| 0.083 | 17.2 | 11.8 | 51.6 | 35.4 | 43.5 |
| 0.25 | 13.2 | 12.9 | 39.6 | 38.7 | 39.2 |
| 1 | 13.3 | 17.5 | 39.9 | 52.5 | 46.2 |
| 4 | 14.2 | 12.4 | 42.6 | 37.2 | 39.9 |

All of the brain samples were added with PBS by brain weight (g) to PBS volume (mL) Ratio 1:2 for homogenating. The actual concentration (ng/g) is the detected value (ng/mL) multiplied by 3.

Figure 8:
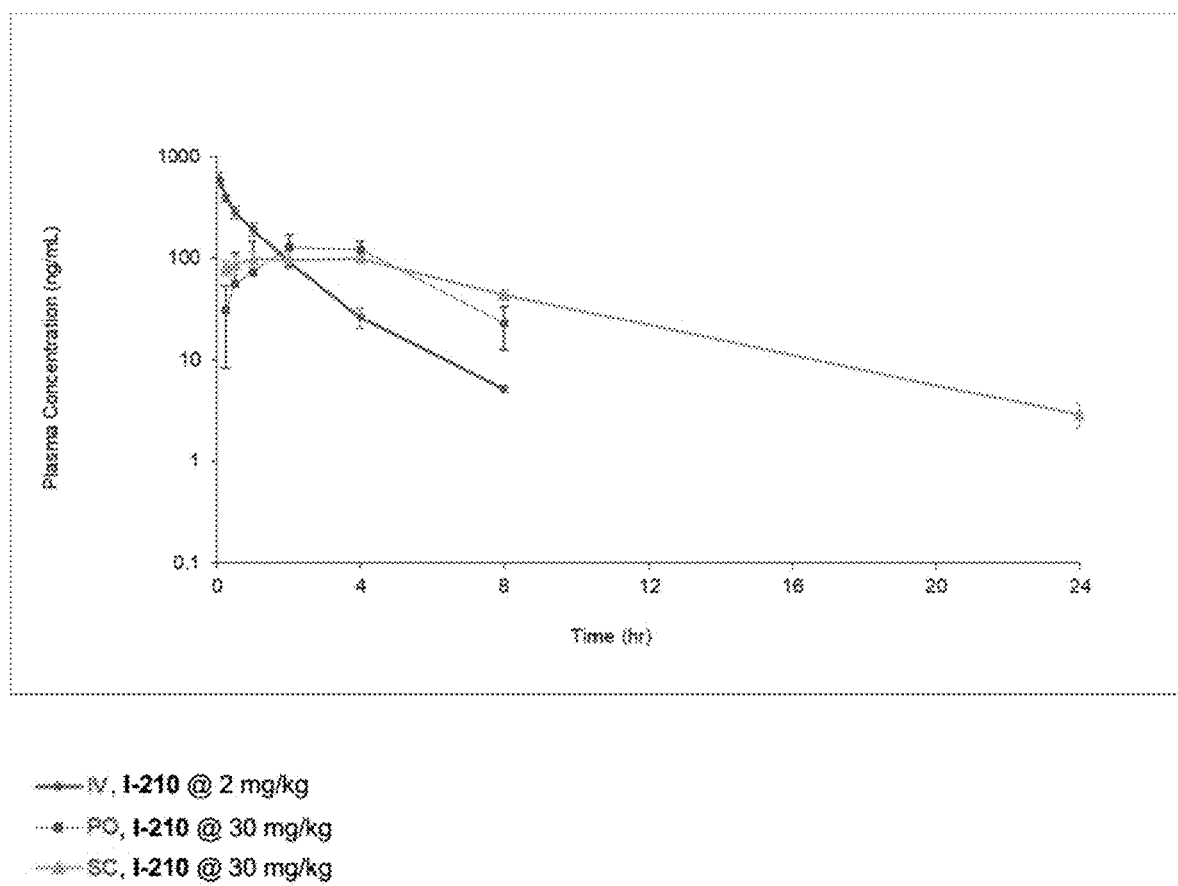
FIG. 8 depicts the plasma concentration versus time profile for I-210 after 2 mg/kg IV, 30 mg/kg PO and 30 mg/kg SC in CD1 mouse.

I-210
Mouse (CD1) iv pk @ 2 mg/kg (IV depicted in FIG. 8)
Formulation: 20% DMSO and 10% PEG400 in water for injection

TABLE 27

| I-210 concentrations dosed iv @ 2 mg/kg in mouse (CD1) | | | | | | |
|---|---|---|---|---|---|---|
| Time | Concentration (ng/mL) | | | Mean | SD | CV |
| (h) | Mouse 1 | Mouse 2 | Mouse 3 | (ng/mL) | (ng/mL) | (%) |
| 0 | BLOQ | BLOQ | BLOQ | NA | NA | NA |
| 0.0833 | 579 | 495 | 692 | 589 | 99 | 16.8 |
| 0.25 | 364 | 382 | 424 | 390 | 31 | 7.89 |
| 0.5 | 306 | 238 | 306 | 283 | 39 | 13.9 |
| 1 | 220 | 164 | 195 | 193 | 28 | 14.5 |
| 2 | 89.3 | 92.5 | 90.7 | 90.8 | 1.6 | 1.77 |
| 4 | 32.5 | 20.2 | 25.6 | 26.1 | 6.2 | 23.6 |
| 8 | 5.72 | 4.92 | 4.93 | 5.19 | 0.46 | 8.84 |
| 24 | BLOQ | BLOQ | BLOQ | NA | NA | NA |

TABLE 28

I-210 PK parameters dosed iv @ 2 mg/kg in mouse (CD1)

| PK parameters | Unit | Mouse 1 | Mouse 2 | Mouse 3 | Mean | SD | CV(%) |
|---|---|---|---|---|---|---|---|
| $Cl\_obs$ | mL/min/kg | 46.7 | 55.8 | 47.2 | 49.9 | 5.1 | 10.3 |
| $T_{1/2}$ | h | 1.52 | 1.48 | 1.46 | 1.49 | 0.03 | 2.27 |
| $C_0$ | ng/mL | 730 | 563 | 884 | 726 | 160 | 22.1 |
| $AUC_{last}$ | h * ng/mL | 701 | 586 | 695 | 661 | 65 | 9.79 |
| $AUC_{Inf}$ | h * ng/mL | 714 | 597 | 706 | 672 | 65 | 9.72 |
| $AUC\_{\%Extrap}\_obs$ | % | 1.76 | 1.76 | 1.47 | 1.66 | 0.17 | 10.0 |
| $MRT_{Inf}\_obs$ | h | 1.58 | 1.50 | 1.41 | 1.50 | 0.08 | 5.52 |
| $AUC_{last}/D$ | h * mg/mL | 351 | 293 | 348 | 331 | 32 | 9.79 |
| $V_{ss}\_obs$ | L/kg | 4.42 | 5.04 | 4.00 | 4.48 | 0.52 | 11.7 |

I-210
Mouse (CD1) po pk @ 30 mg/kg (PO depicted in FIG. 8)
Formulation: 0.5% CMC and 0.25% Tween 80 in water

TABLE 29

I-210 concentrations dosed po @ 30 mg/kg in mouse (CD1)

| Time | Concentration (ng/mL) | | | Mean | SD | CV |
|---|---|---|---|---|---|---|
| (h) | Mouse 4 | Mouse 5 | Mouse 6 | (ng/mL) | (ng/mL) | (%) |
| 0 | BLOQ | BLOQ | BLOQ | NA | NA | NA |
| 0.25 | 55.9 | 23.7 | 12.8 | 30.8 | 22.4 | 72.8 |
| 0.5 | 120 | 23.0 | 22.2 | 55 | 56 | 102 |
| 1 | 153 | 16.9 | 45.1 | 72 | 72 | 100 |
| 2 | 177 | 91.1 | 112 | 127 | 45 | 35.4 |
| 4 | 92.5 | 143 | 123 | 120 | 25 | 21.3 |
| 8 | 34.8 | 17.1 | 16.4 | 22.8 | 10.4 | 45.8 |
| 24 | BLOQ | BLOQ | BLOQ | NA | NA | NA |

TABLE 30

I-210 PK parameters dosed po @ 30 mg/kg in mouse (CD1)

| PK parameters | Unit | Mouse 4 | Mouse 5 | Mouse 6 | Mean | SD | CV(%) |
|---|---|---|---|---|---|---|---|
| $T_{1/2}$ | h | 2.59 | 2.20 | 2.00 | 2.27 | 0.30 | 13.3 |
| $T_{max}$ | h | 2 | 4 | 4 | 3.33 | 1.15 | 34.6 |
| $C_{max}$ | ng/mL | 177 | 143 | 123 | 148 | 27 | 18.5 |
| $AUC_{last}$ | h * ng/mL | 786 | 627 | 615 | 676 | 96 | 14.1 |
| $AUC_{Inf}$ | h * ng/mL | 917 | 681 | 662 | 753 | 142 | 18.8 |
| $AUC\_{\%Extrap}\_obs$ | % | 14.2 | 7.97 | 7.15 | 9.8 | 3.9 | 39.5 |
| $MRT_{Inf}\_obs$ | h | 4.22 | 4.24 | 3.97 | 4.14 | 0.15 | 3.65 |
| $AUC_{last}/D$ | h * mg/mL | 26.2 | 20.9 | 20.5 | 22.5 | 3.2 | 14.1 |
| F | % | 9.09 | 6.76 | 6.57 | 7.47 | 1.40 | 18.8 |

I-210

Mouse (CD1) sc pk @ 30 mg/kg (SC depicted in FIG. 8)
Formulation: 20% DMSO and 10% PEG400 in water for injection

TABLE 31

I-210 concentrations dosed sc @ 30 mg/kg in mouse (CD1)

| Time | Concentration (ng/mL) | | | Mean | SD | CV |
|---|---|---|---|---|---|---|
| (h) | Mouse 7 | Mouse 8 | Mouse 9 | (ng/mL) | (ng/mL) | (%) |
| 0 | BLOQ | BLOQ | BLOQ | NA | NA | NA |
| 0.25 | 74.8 | 93.0 | 70.1 | 79.3 | 12.1 | 15.3 |
| 0.5 | 88.8 | 101 | 66.6 | 85 | 17 | 20.4 |
| 1 | 107 | 107 | 76.5 | 97 | 18 | 18.2 |
| 2 | 90.0 | 115 | 81.1 | 95 | 18 | 18.4 |
| 4 | 95.9 | 91.8 | 105 | 98 | 7 | 6.92 |
| 8 | 39.6 | 49.0 | 42.0 | 43.5 | 4.9 | 11.2 |
| 24 | 3.62 | 2.88 | 2.05 | 2.85 | 0.79 | 27.6 |

TABLE 32

I-210 PK parameters dosed sc @ 30 mg/kg in mouse (CD1)

| PK parameters | Unit | Mouse 7 | Mouse 8 | Mouse 9 | Mean | SD | CV(%) |
|---|---|---|---|---|---|---|---|
| $T_{1/2}$ | h | 4.34 | 3.98 | 3.56 | 3.96 | 0.39 | 9.80 |
| $T_{max}$ | h | 1 | 2 | 4 | 2.33 | 1.53 | 65.5 |
| $C_{max}$ | ng/mL | 107 | 115 | 105 | 109 | 5 | 4.85 |
| $AUC_{last}$ | h * ng/mL | 980 | 1102 | 973 | 1018 | 73 | 7.15 |
| $AUC_{Inf}$ | h * ng/mL | 1003 | 1119 | 983 | 1035 | 73 | 7.08 |
| $AUC_{\%Extrap\_obs}$ | % | 2.26 | 1.48 | 1.07 | 1.60 | 0.60 | 37.7 |
| $MRT_{Inf}\_obs$ | h | 6.06 | 5.82 | 5.73 | 5.87 | 0.17 | 2.83 |
| $AUC_{last}/D$ | h * mg/mL | 32.7 | 36.7 | 32.4 | 33.9 | 2.4 | 7.15 |
| F | % | 9.94 | 11.1 | 9.75 | 10.3 | 0.7 | 7.08 |

I-127

Figure 9:
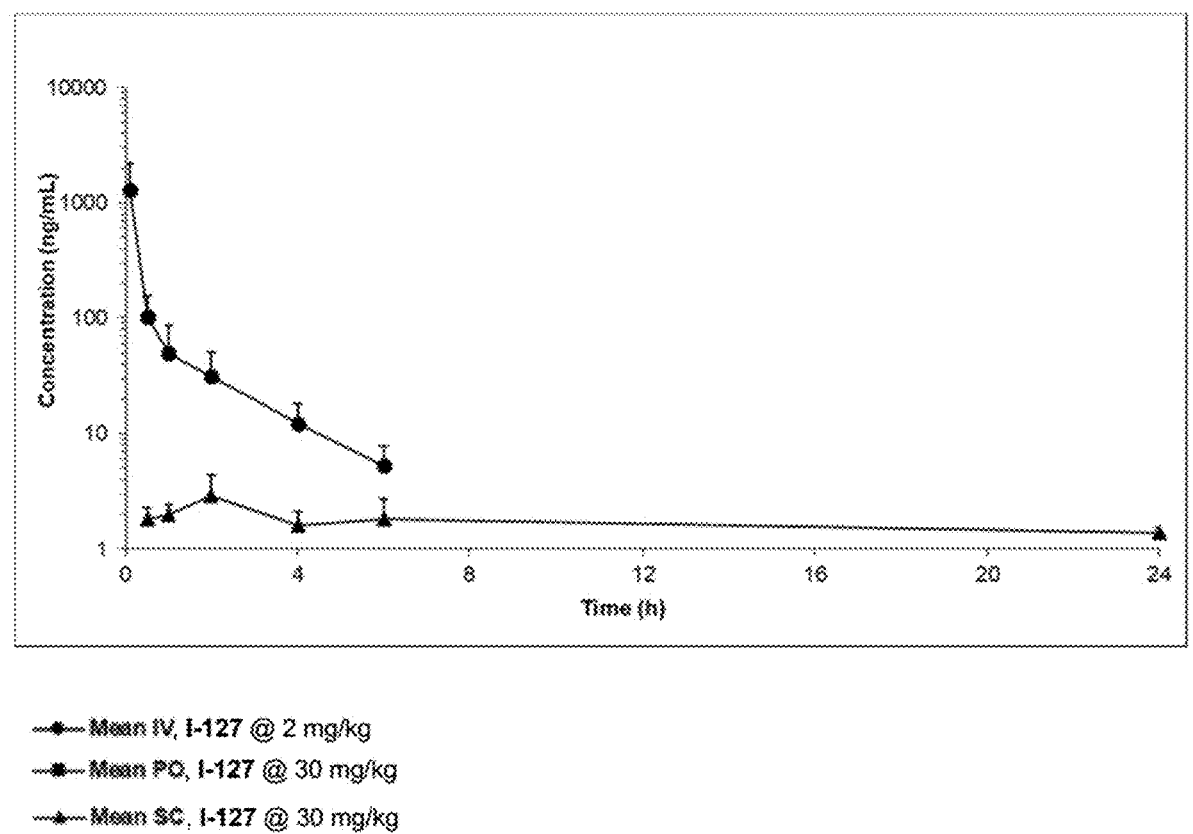
FIG. 9 depicts the mean plasma concentration of I-127 after IV, PO and SC dosing.

Mouse (CD1) iv pk @ 2 mg/kg (IV depicted in FIG. 9)
Formulation: 10% DMSO/40% PEG400/10% cremophor RH40/40% water

TABLE 33

I-127 concentrations dosed iv @ 2 mg/kg in mouse (CD1)

| IV Time (h) | M01 | M02 | M03 | Mean IV | | SD | CV (%) |
|---|---|---|---|---|---|---|---|
| 0.0833 | 2310 | 831 | 738 | 1293 | ± | 882 | 68.2 |
| 0.500 | 166 | 58.7 | 82.1 | 102 | ± | 56.4 | 55.2 |
| 1.00 | 91.0 | 22.3 | 35.8 | 49.7 | ± | 36.4 | 73.2 |
| 2.00 | 51.5 | 12.7 | 30.9 | 31.7 | ± | 19.4 | 61.2 |
| 4.00 | 18.6 | 7.08 | 10.9 | 12.2 | ± | 5.87 | 48.1 |
| 6.00 | 8.13 | 3.38 | 4.42 | 5.31 | ± | 2.50 | 47.0 |
| 24.0 | 2.20 | BQL | BQL | ND | ± | ND | ND |

TABLE 34

I-127 PK parameters dosed iv @ 2 mg/kg in mouse (CD1)

| PK Parameters | M01 | M02 | M03 | Mean IV | | SD | CV (%) |
|---|---|---|---|---|---|---|---|
| Rsq_adj | 0.821 | 0.991 | 0.997 | — | ± | — | — |
| No. points used for $T_{1/2}$ | 3.00 | 3.00 | 3.00 | 3.00 | ± | — | — |
| $C_0$ (ng/mL) | 3910 | 1412 | 1145 | 2155 | ± | 1525 | 70.8 |
| $T_{1/2}$ (h) | 7.43 | 2.09 | 1.43 | 3.65 | ± | 3.29 | 90.2 |
| $Vd_{ss}$ (L/kg) | 5.73 | 6.36 | 6.67 | 6.25 | ± | 0.480 | 7.68 |
| Cl (mL/min/kg) | 36.3 | 116 | 103 | 84.9 | ± | 42.6 | 50.2 |
| $T_{last}$ (h) | 24.0 | 6.00 | 6.00 | ND | ± | | |
| $AUC_{0-last}$ (ng · h/mL) | 896 | 278 | 316 | 496 | ± | 346 | 69.8 |
| $AUC_{0-inf}$ (ng · h/mL) | 919 | 288 | 325 | 511 | ± | 354 | 69.4 |
| $MRT_{0-last}$ (h) | 1.79 | 0.618 | 0.882 | 1.10 | ± | 0.614 | 56.0 |
| $MRT_{0-inf}$ (h) | 2.63 | 0.916 | 1.08 | 1.54 | ± | 0.947 | 61.3 |
| $AUC_{Extra}$ (%) | 2.57 | 3.55 | 2.80 | 2.97 | ± | 0.512 | 17.2 |
| $AUMC_{Extra}$ (%) | 33.8 | 34.9 | 20.8 | 29.9 | ± | 7.84 | 26.2 |

I-127

Mouse (CD1) po pk @ 30 mg/kg (PO depicted in FIG. 9)
Formulation: 0.5% MC/0.5% Tween80

TABLE 35

I-127 concentrations dosed po @ 30 mg/kg in mouse (CD1)

| PO Time (h) | M04 | M05 | M06 | Mean PO | | SD | CV (%) |
|---|---|---|---|---|---|---|---|
| 0.500 | BQL | BQL | BQL | ND | ± | ND | ND |
| 1.00 | BQL | BQL | BQL | ND | ± | ND | ND |
| 2.00 | BQL | BQL | BQL | ND | ± | ND | ND |
| 4.00 | BQL | BQL | BQL | ND | ± | ND | ND |
| 6.00 | BQL | BQL | BQL | ND | ± | ND | ND |
| 24.0 | BQL | BQL | BQL | ND | ± | ND | ND |

TABLE 36

I-127 PK parameters dosed po @ 30 mg/kg in mouse (CD1)

| PK Parameters | M04 | M05 | M06 | Mean PO | | SD | CV (%) |
|---|---|---|---|---|---|---|---|
| Rsq_adj | ND | ND | ND | — | ± | — | — |
| No. points used for $T_{1/2}$ | ND | ND | ND | ND | ± | — | — |
| $C_{max}$ (ng/mL) | ND | ND | ND | ND | ± | ND | ND |
| $T_{max}$ (h) | ND | ND | ND | ND | ± | ND | ND |
| $T_{1/2}$ (h) | ND | ND | ND | ND | ± | ND | ND |
| $T_{last}$ (h) | ND | ND | ND | ND | ± | — | — |
| $AUC_{0-last}$ (ng · h/mL) | ND | ND | ND | ND | ± | ND | ND |
| $AUC_{0-inf}$ (ng · h/mL) | ND | ND | ND | ND | ± | ND | ND |
| $MRT_{0-last}$ (h) | ND | ND | ND | ND | ± | ND | ND |

TABLE 36-continued

I-127 PK parameters dosed po @ 30 mg/kg in mouse (CD1)

| PK Parameters | M04 | M05 | M06 | Mean PO | | SD | CV (%) |
|---|---|---|---|---|---|---|---|
| $MRT_{0\text{-}inf}$ (h) | ND | ND | ND | ND | ± | ND | ND |
| $AUC_{Extra}$ (%) | ND | ND | ND | ND | ± | ND | ND |
| $AUMC_{Extra}$ (%) | ND | ND | ND | ND | ± | ND | ND |
| Bioavailability (%)[a] | — | — | — | ND | ± | — | — |

I-127

Mouse (CD1) sc pk @ 30 mg/kg (SC depicted in FIG. 9)
Formulation: 0.5% MC/0.5% Tween80

TABLE 37

I-127 concentrations dosed sc @ 30 mg/kg in mouse (CD1)

| SC Time (h) | M07 | M08 | M09 | Mean SC | | SD | CV (%) |
|---|---|---|---|---|---|---|---|
| 0.500 | 1.29 | 2.28 | 1.85 | 1.81 | ± | 0.496 | 27.5 |
| 1.00 | 1.87 | 2.51 | 1.61 | 2.00 | ± | 0.463 | 23.2 |
| 2.00 | 2.21 | 4.61 | 1.82 | 2.88 | ± | 1.51 | 52.5 |
| 4.00 | 1.01 | 1.86 | 1.90 | 1.59 | ± | 0.503 | 31.6 |
| 6.00 | 1.41 | 2.82 | 1.18 | 1.80 | ± | 0.888 | 49.2 |
| 24.0 | 1.30 | 1.58 | 1.26 | 1.38 | ± | 0.174 | 12.6 |

TABLE 38

I-127 PK parameters dosed sc @ 30 mg/kg in mouse (CD1)

| PK Parameters | M07 | M08 | M09 | Mean SC | | SD | CV (%) |
|---|---|---|---|---|---|---|---|
| Rsq_adj | ND | -0.152 | ND | — | ± | — | — |
| No. points used for $T_{1/2}$ | 0 | 3.00 | 0 | ND | ± | — | — |
| $C_{max}$ (ng/mL) | 2.21 | 4.61 | 1.90 | 2.91 | ± | 1.48 | 51.0 |
| $T_{max}$ (h) | 2.00 | 2.00 | 4.00 | 2.67 | ± | 1.15 | 43.3 |
| $T_{1/2}$ (h) | ND | 39.2 | ND | ND | ± | ND | ND |
| $T_{last}$ (h) | 24.0 | 24.0 | 24.0 | 24.0 | ± | — | — |
| $AUC_{0\text{-}last}$ (ng · h/mL) | 33.0 | 54.5 | 31.7 | 39.8 | ± | 12.8 | 32.2 |
| $AUC_{0\text{-}inf}$ (ng · h/mL) | ND | 144 | ND | ND | ± | ND | ND |
| $MRT_{0\text{-}last}$ (h) | 11.7 | 10.9 | 11.4 | 11.3 | ± | 0.444 | 3.92 |
| $MRT_{0\text{-}inf}$ (h) | ND | 54.2 | ND | ND | ± | ND | ND |
| $AUC_{Extra}$ (%) | ND | 62.1 | ND | ND | ± | ND | ND |
| $AUMC_{Extra}$ (%) | ND | 92.4 | ND | ND | ± | ND | ND |
| Bioavailability (%)[a] | — | — | — | 0.534 | ± | — | — |

I-172

Figure 10:
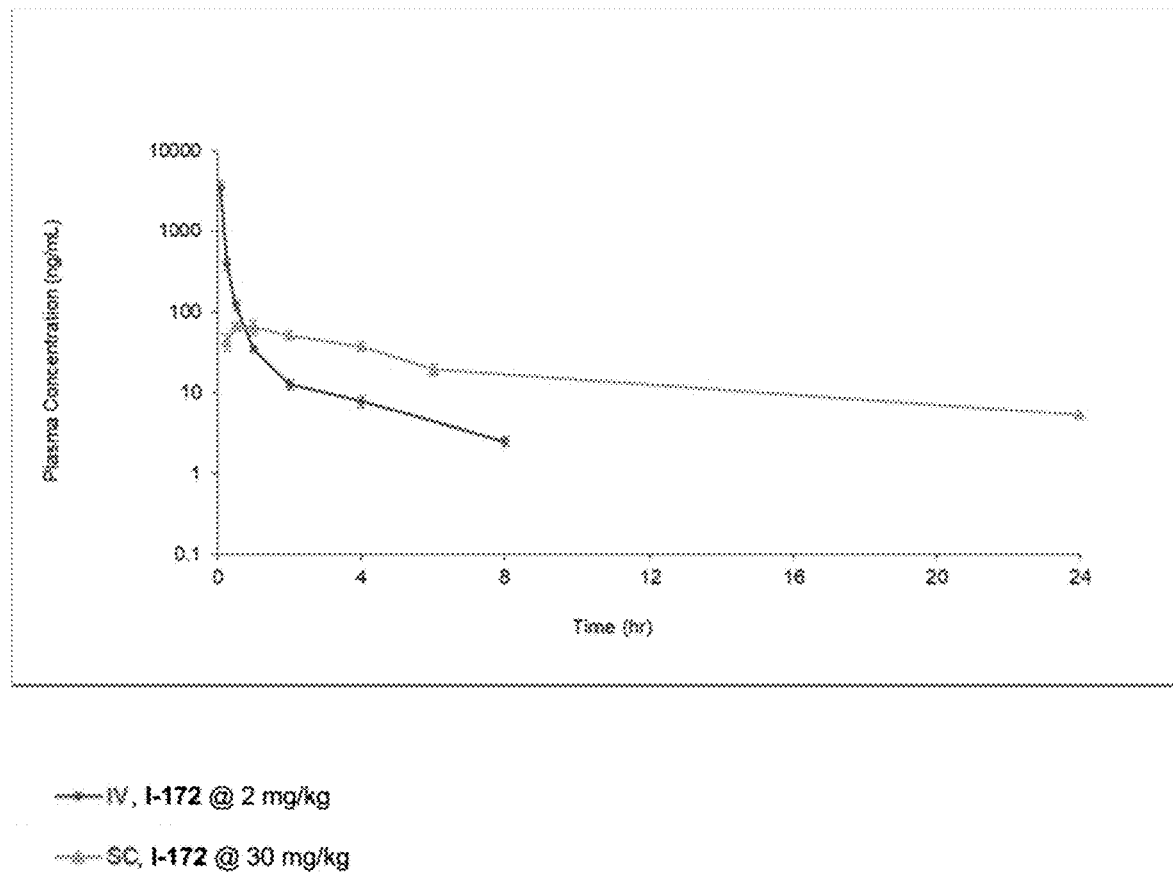
FIG. 10 depicts the plasma concentration versus time profile for I-172 after 2 mg/kg IV and 30 mg/kg SC in CD1 mouse.

Mouse (CD1) iv pk @ 2 mg/kg (IV depicted in FIG. 10)
Formulation: 10% DMSO and 2% Cremphor in water

TABLE 39

I-172 concentrations dosed iv @ 2 mg/kg in mouse (CD1)

| | Concentration (ng/mL) | | | | | |
|---|---|---|---|---|---|---|
| Time (h) | Mouse 1 | Mouse 2 | Mouse 3 | Mean (ng/mL) | SD (ng/mL) | CV (%) |
| 0 | BLOQ | BLOQ | BLOQ | NA | NA | NA |
| 0.0833 | 4150 | 2810 | 3290 | 3417 | 679 | 19.9 |
| 0.25 | 444 | 314 | 404 | 387 | 67 | 17.2 |
| 0.5 | 130 | 102 | 136 | 123 | 18 | 14.8 |
| 1 | 34.3 | 31.5 | 38.2 | 34.7 | 3.4 | 9.71 |
| 2 | 11.5 | 11.7 | 14.6 | 12.6 | 1.7 | 13.8 |
| 4 | 9.04 | 6.56 | 7.70 | 7.77 | 1.24 | 16.0 |
| 8 | 2.62 | 2.07 | 2.69 | 2.46 | 0.34 | 13.8 |
| 24 | BLOQ | BLOQ | 2.55 | NA | NA | NA |

TABLE 40

I-172 PK parameters dosed iv @ 2 mg/kg in mouse (CD1)

| PK | Unit | Mouse 1 | Mouse 2 | Mouse 3 | Mean | SD | CV(%) |
|---|---|---|---|---|---|---|---|
| Cl_obs | mL/min/kg | 26.2 | 38.0 | 31.2 | 31.8 | 5.9 | 18.7 |
| $T_{1/2}$ | h | 2.71 | 2.40 | 2.48 | 2.53 | 0.16 | 6.37 |
| $C_0$ | ng/mL | 12679 | 8401 | 9383 | 10154 | 2241 | 22.1 |
| $AUC_{last}$ | h * ng/mL | 1263 | 870 | 1058 | 1064 | 197 | 18.5 |
| $AUC_{Inf}$ | h * ng/mL | 1274 | 877 | 1067 | 1073 | 198 | 18.5 |
| $AUC_{\_\%Extrap}$_obs | % | 0.805 | 0.818 | 0.856 | 0.826 | 0.026 | 3.20 |
| $MRT_{Inf}$_obs | h | 0.332 | 0.362 | 1.13 | 0.61 | 0.45 | 74.2 |
| $AUC_{last}/D$ | h * mg/mL | 632 | 435 | 529 | 532 | 98 | 18.5 |
| $V_{ss}$_obs | L/kg | 0.522 | 0.826 | 2.11 | 1.15 | 0.84 | 73.2 |

I-172

Mouse (CD1) po pk @ 30 mg/kg
Formulation: 0.5% CMC and 0.25% Tween 80 in water

TABLE 41

I-172 concentrations dosed po @ 30 mg/kg in mouse (CD1)

| | Concentration (ng/mL) | | | Mean | SD | CV |
|---|---|---|---|---|---|---|
| Time (h) | Mouse 4 | Mouse 5 | Mouse 6 | (ng/mL) | (ng/mL) | (%) |
| 0 | BLOQ | BLOQ | BLOQ | NA | NA | NA |
| 0.25 | BLOQ | BLOQ | BLOQ | NA | NA | NA |
| 0.5 | BLOQ | BLOQ | BLOQ | NA | NA | NA |
| 1 | BLOQ | BLOQ | BLOQ | NA | NA | NA |
| 2 | BLOQ | BLOQ | BLOQ | NA | NA | NA |
| 4 | BLOQ | BLOQ | BLOQ | NA | NA | NA |
| 8 | BLOQ | BLOQ | BLOQ | NA | NA | NA |
| 24 | BLOQ | BLOQ | BLOQ | NA | NA | NA |

TABLE 42

| PK parameters | Unit | Mouse 4 | Mouse 5 | Mouse 6 | Mean | SD | CV (%) |
|---|---|---|---|---|---|---|---|
| I-172 PK parameters dosed po @ 30 mg/kg in mouse (CD1) | | | | | | | |
| $T_{1/2}$ | h | NA | NA | NA | NA | NA | NA |
| $T_{max}$ | h | NA | NA | NA | NA | NA | NA |
| $C_{max}$ | ng/mL | NA | NA | NA | NA | NA | NA |
| $AUC_{last}$ | h * ng/mL | NA | NA | NA | NA | NA | NA |
| $AUC_{Inf}$ | h * ng/mL | NA | NA | NA | NA | NA | NA |
| $AUC\_\%Extrap\_obs$ | % | NA | NA | NA | NA | NA | NA |
| $MRT_{Inf}\_obs$ | h | NA | NA | NA | NA | NA | NA |
| $AUC_{last}/D$ | h * mg/mL | NA | NA | NA | NA | NA | NA |
| F | % | NA | NA | NA | NA | NA | NA |

I-172

Mouse (CD1) sc pk @ 30 mg/kg (SC depicted in FIG. 10)
Formulation: 20% DMSO and 10% Cremphor in water

TABLE 43

I-172 concentrations dosed sc @ 30 mg/kg in mouse (CD1)

| Time (h) | Concentration (ng/mL) | | | Mean (ng/mL) | SD (ng/mL) | CV (%) |
|---|---|---|---|---|---|---|
| | Mouse 7 | Mouse 8 | Mouse 9 | | | |
| 0 | BLOQ | BLOQ | BLOQ | NA | NA | NA |
| 0.25 | 34.6 | 40.0 | 54.6 | 43.1 | 10.3 | 24.0 |
| 0.5 | 71.9 | 57.6 | 64.8 | 64.8 | 7.2 | 11.0 |
| 1 | 52.6 | 63.0 | 78.7 | 64.8 | 13.1 | 20.3 |
| 2 | 48.0 | 46.5 | 58.0 | 50.8 | 6.3 | 12.3 |
| 4 | 33.3 | 37.0 | 41.6 | 37.3 | 4.2 | 11.1 |
| 6 | 16.0 | 20.7 | 21.5 | 19.4 | 3.0 | 15.3 |
| 24 | 5.40 | 4.74 | 5.85 | 5.33 | 0.56 | 10.5 |

TABLE 44

PK parameters dosed sc @ 30 mg/kg in mouse (CD1)

| PK parameters | Unit | Mouse 7 | Mouse 8 | Mouse 9 | Mean | SD | CV (%) |
|---|---|---|---|---|---|---|---|
| $T_{1/2}$ | h | 8.79 | 7.34 | 7.89 | 8.00 | 0.74 | 9.18 |
| $T_{max}$ | h | 0.5 | 1 | 1 | 0.833 | 0.289 | 34.6 |
| $C_{max}$ | ng/mL | 71.9 | 63.0 | 78.7 | 71.2 | 7.9 | 11.1 |
| $AUC_{last}$ | h*ng/mL | 422 | 472 | 535 | 476 | 56 | 11.8 |
| $AUC_{Inf}$ | h*ng/mL | 491 | 522 | 601 | 538 | 57 | 10.6 |
| $AUC\_\%Extrap\_obs$ | % | 14.0 | 9.60 | 11.1 | 11.5 | 2.2 | 19.2 |
| $MRT_{Inf}\_obs$ | h | 10.4 | 8.61 | 9.13 | 9.4 | 0.9 | 9.84 |
| $AUC_{last}/D$ | h*mg/mL | 14.1 | 15.7 | 17.8 | 15.9 | 1.9 | 11.8 |
| F | % | 3.05 | 3.25 | 3.74 | 3.34 | 0.35 | 10.6 |

Example 210: Synthesis of 2-[2-(Cyclopropylmethylamino)-4-pyridyl]-N-[3-(difluoromethyl)-1-[4-[[2-[2-[2-[[2-(2,6-dioxo-3-piperidyl)-1,3-dioxoisoindolin-4-yl]amino]ethoxy]ethoxy]ethylamino]methyl]phenyl]pyrazol-4-yl]oxazole-4-carboxamide, I-210
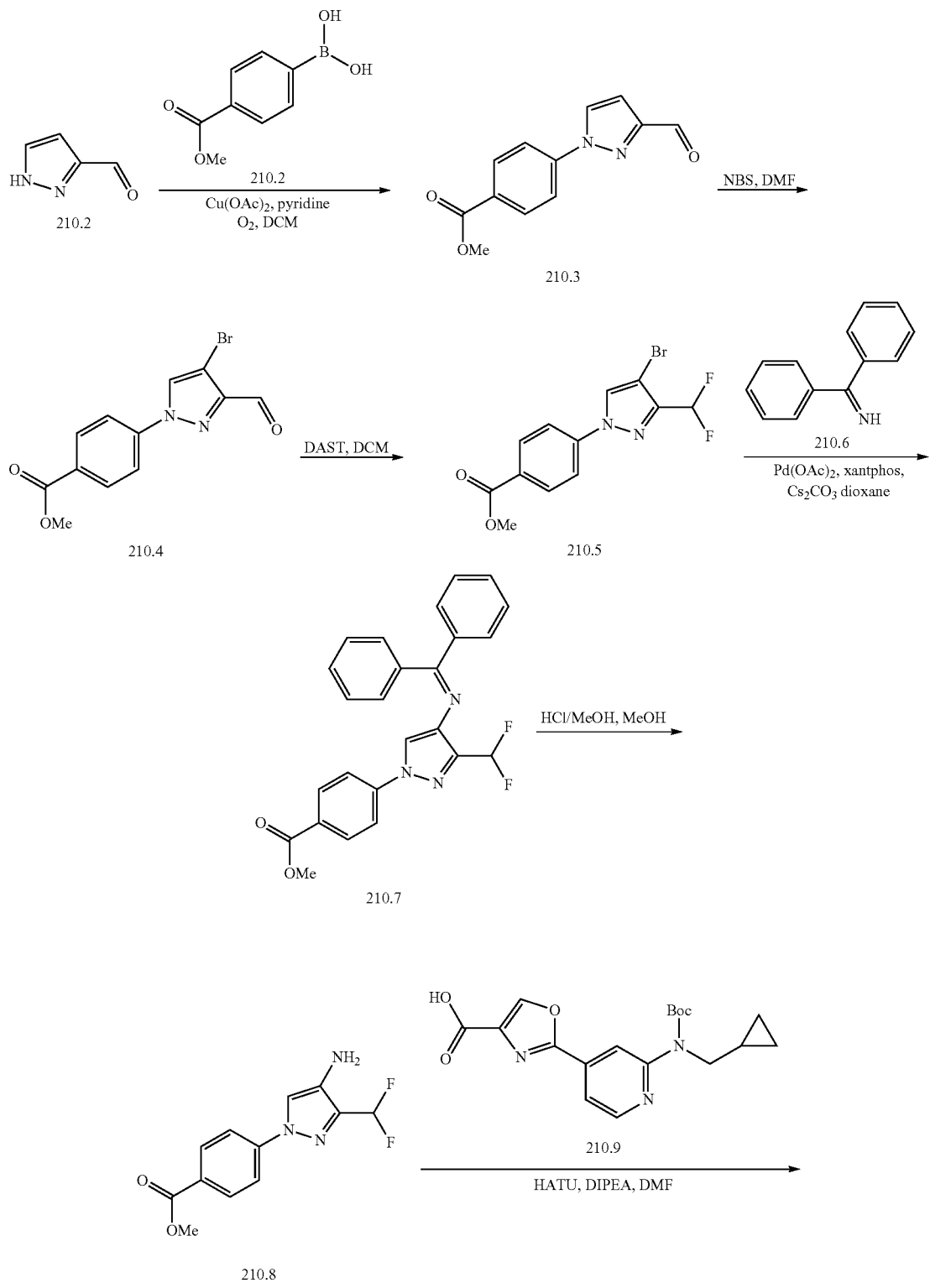

-continued
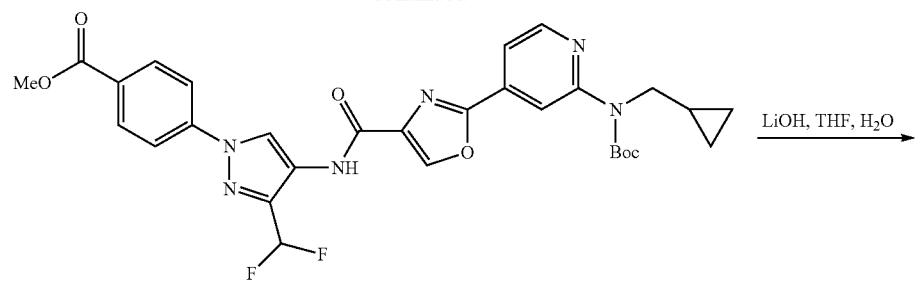
210.10
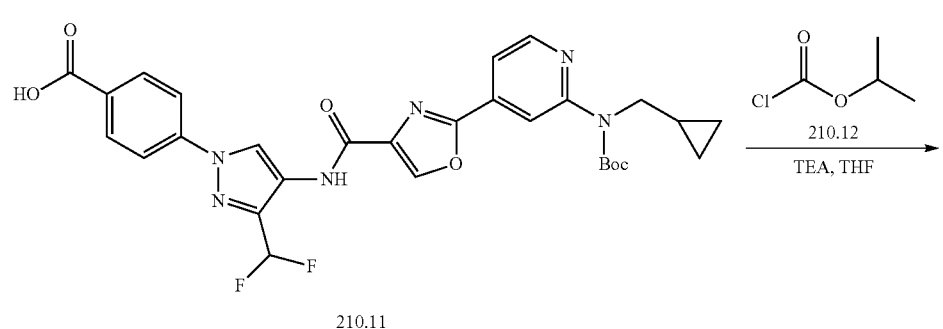
210.11
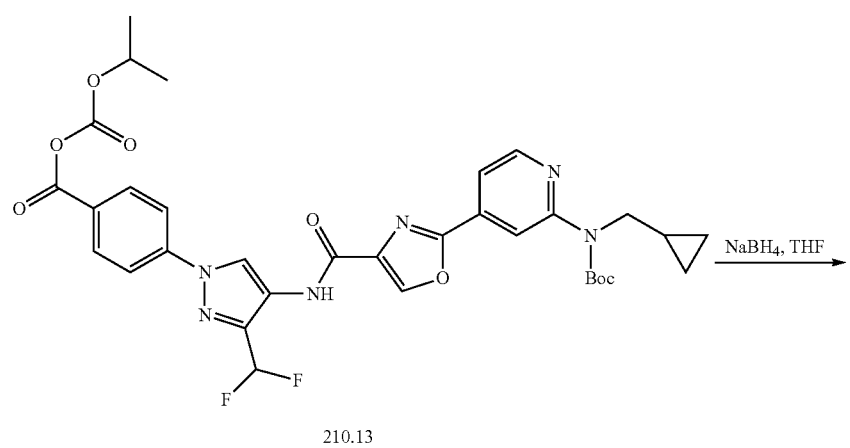
210.13
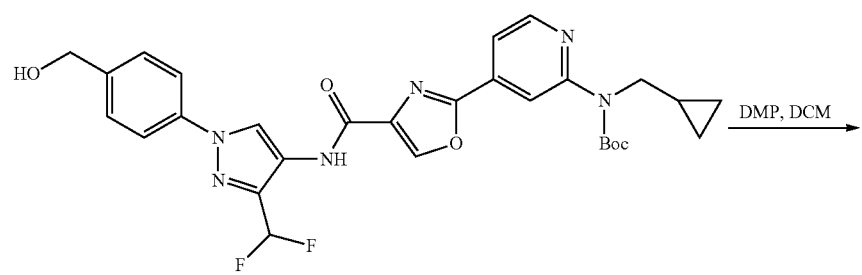
210.14

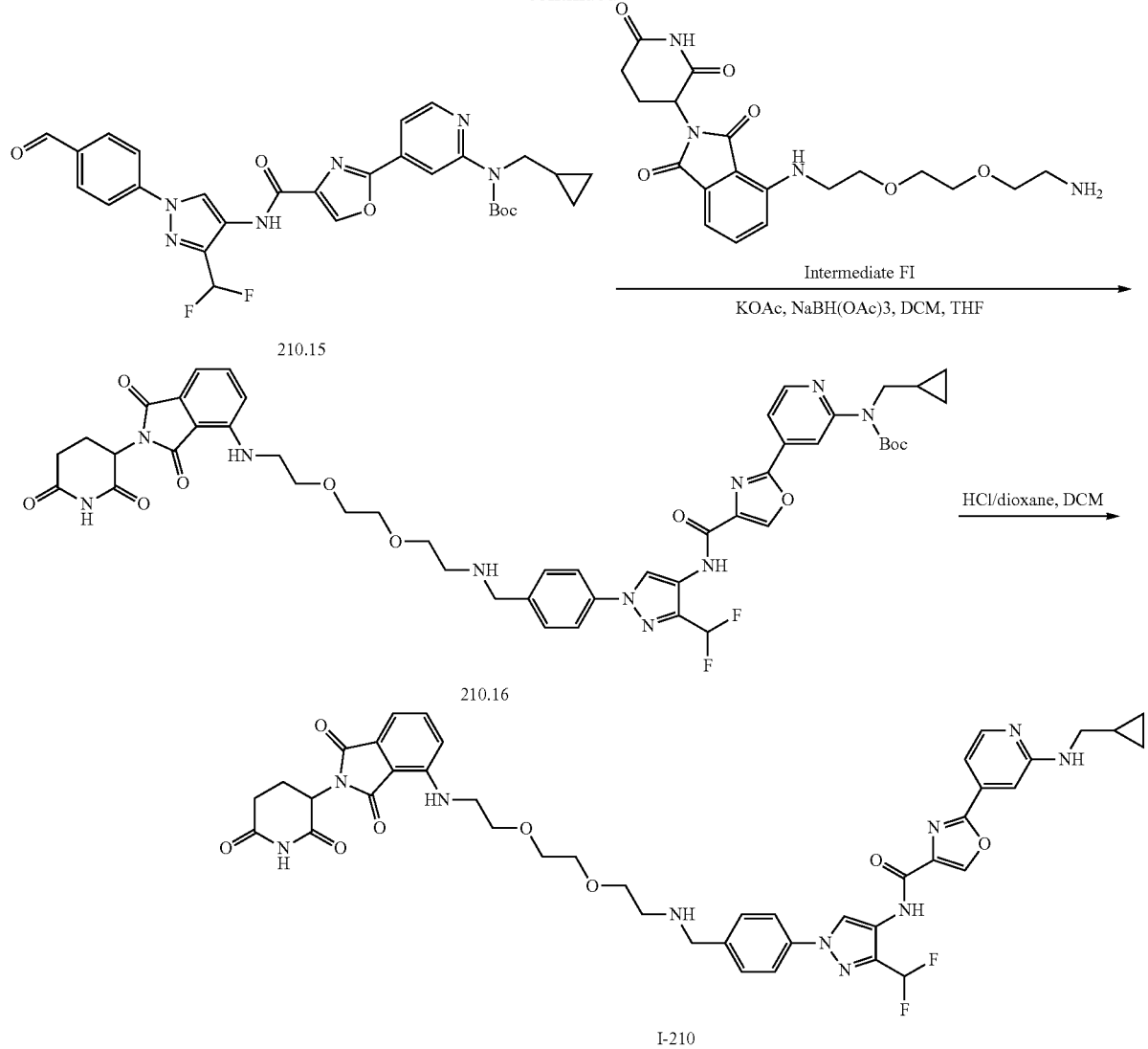

Step 1—Methyl 4-(3-formyl-1H-pyrazol-1-yl)benzoate (210.3)

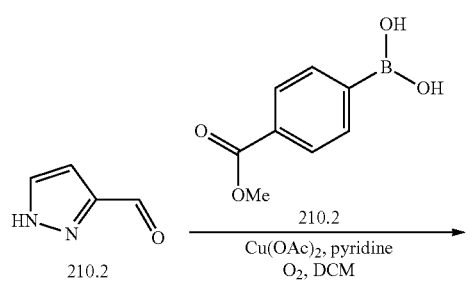

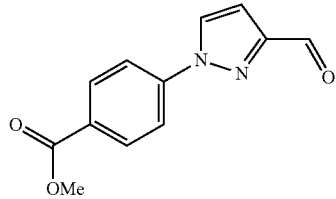

To a solution of 1H-pyrazole-3-carbaldehyde (10.0 g, 104 mmol, CAS: 3920-20-1) and (4-methoxy carbonyl-phenyl) boronic acid (22.5 g, 125 mmol, CAS: 99768-12-4) in DCM (50 mL) was added Cu(OAc)$_2$ (22.7 g, 125 mmol) and pyridine (32.9 g, 416 mmol). The reaction mixture was stirred at 25° C. for 18 hours under O2. On completion, the mixture was concentrated in vacuo. The residue was purified by silica gel chromatography to give the title compound (12.0 g, 50% yield) as a white solid. $^1$H NMR (400 MHz, CDCl₃) δ 10.10 (s, 1H), 8.24-8.14 (m, 2H), 8.06 (d, J=2.4 Hz, 1H), 7.90-7.82 (m, 2H), 7.02 (d, J=2.4 Hz, 1H), 3.95 (s, 3H).

Step 2—Methyl 4-(4-bromo-3-formyl-1H-pyrazol-1-yl)benzoate (210.4)

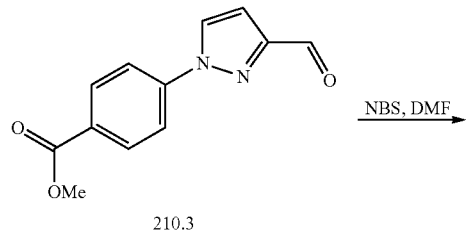

To a solution of methyl 4-(3-formylpyrazol-1-yl)benzoate (4.00 g, 17.4 mmol) in DMF (40 mL) was added NBS (6.18 g, 34.8 mmol). The reaction mixture was stirred at 25° C. for 1 hour. Then, the reaction mixture was heated to 50° C. for 12 hours. On completion, the mixture was concentrated in vacuo. The residue was purified by prep-HPLC (0.1% FA condition) to give the title compound (4.50 g, 82% yield) as a white solid. ¹H NMR (400 MHz, CDCl₃) δ 10.02 (s, 1H), 8.12 (d, J=8.4 Hz, 2H) 8.04 (s, 1H), 7.75 (d, J=8.4 Hz, 2H), 3.89 (s, 3H); LC-MS (Est) m/z 310.9 (M+3)⁺.

Step 3—Methyl 4-(4-bromo-3-(difluoromethyl)-1H-pyrazol-1-yl)benzoate (210.5)

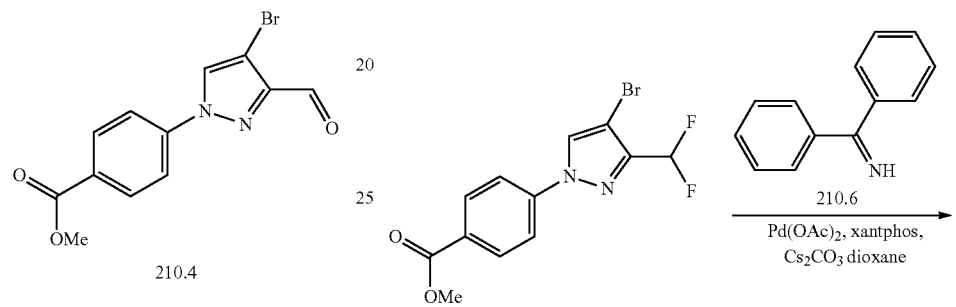

To a solution of methyl 4-(4-bromo-3-formyl-pyrazol-1-yl)benzoate (1.70 g, 5.50 mmol) in DCM (100 mL) was added DAST (7.98 g, 49.5 mmol) at 0° C. The reaction mixture was stirred at 25° C. for 5 hours. On completion, the mixture was quenched with methanol (30 mL) at 0° C. After that, the mixture was concentrated in vacuo. The residue was purified by prep-HPLC (0.1% HCl condition) to give the title compound (1.44 g, 78% yield) as a white solid. 1H NMR (400 MHz, CDCl3) δ 8.17 (d, J=8.8 Hz, 2H), 8.07 (s, 1H), 7.76 (d, J=8.8 Hz, 2H), 6.80 (t, J=53.2 Hz, 1H), 3.96 (s, 3H); LC-MS (ESI+) m/z 330.9 (M+H)+.

Step 4—Methyl 4-[4-(benzhydrylideneamino)-3-(difluoromethyl)pyrazol-1-yl]benzoate (210.7)

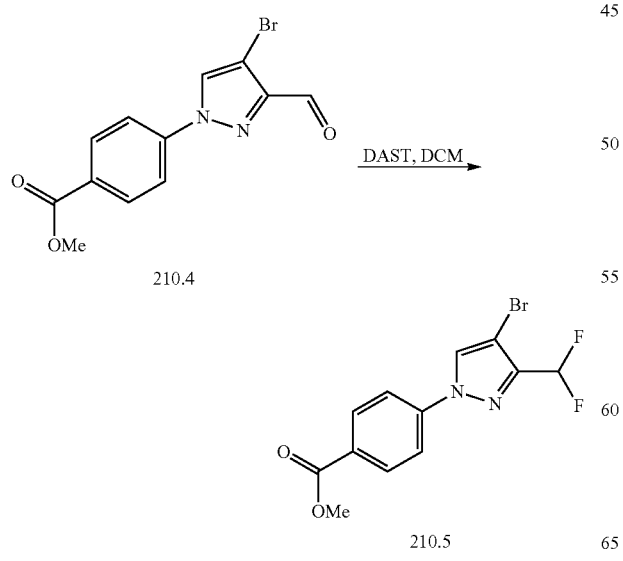

To a mixture of methyl 4-[4-bromo-3-(difluoromethyl)pyrazol-1-yl]benzoate (0.15 g, 453 umol) and diphenyl-methanimine (205 mg, 1.13 mmol) in dioxane (3 mL) was added Pd(OAc)₂ (20.8 mg, 92.4 umol), Xantphos (26.2 mg, 45.3 umol) and Cs₂CO₃ (448 mg, 1.38 mmol). The mixture was degassed and purged with N₂ for 3 times. Then the mixture was stirred at 120° C. for 3 hr under N₂ atmosphere. On completion, the mixture was concentrated, then was added H₂O (30 mL), extracted with EtOAc (3×30 mL). The organic phase was dried with Na₂SO₄, filtrated and concentrated in vacuo. The residue was purified by flash silica gel chromatography to give the title compound (0.24 g, 50% yield) as a yellow solid. 1H NMR (400 MHz, CDCl₃) δ 8.02-7.95 (m, 2H), 7.80-7.73 (m, 2H), 7.51-7.45 (m, 3H), 7.43-7.31 (m, 5H), 7.22-7.19 (m, 2H), 7.12-6.82 (m, 1H), 6.37 (s, 1H), 3.85 (s, 3H); LC-MS (Est) m/z 432.1 (M+H)⁺.

Step 5—Methyl 4-[4-amino-3-(difluoromethyl)pyrazol-1-yl]benzoate (210.8)

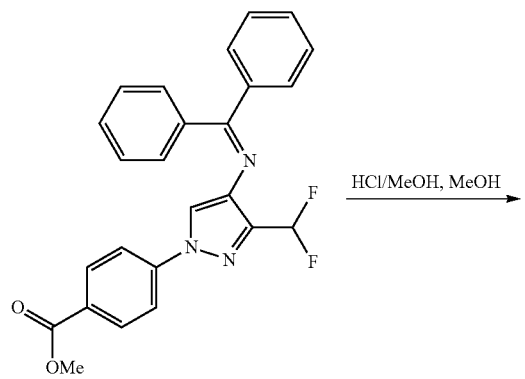

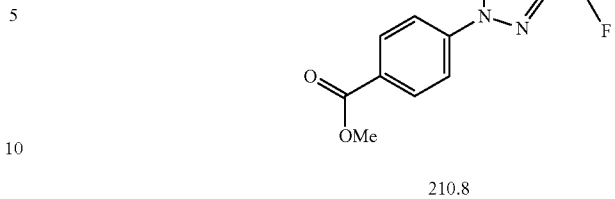

To a solution of methyl 4-[4-(benzhydrylideneamino)-3-(difluoromethyl)pyrazol-1-yl]benzoate (215 mg, 498 umol) in THF (2 mL) and MeOH (20 mL) was added HCl/MeOH (4 M, 124 uL). The mixture was stirred at 25° C. for 30 minutes. On completion, the mixture was concentrated to give the title compound (0.20 g, 90% yield) as a yellow solid. The crude product was used for next without purification. LC-MS (Esi) m/z 268.1 (M+H)+.

Step 6—Methyl 4-[4-[[2-[2-[tert-butoxycarbonyl(cyclopropylmethyl)amino]-4-pyridyl]oxazole-4-carbonyl]amino]-3-(difluoromethyl)pyrazol-1-yl]benzoate (210.10)

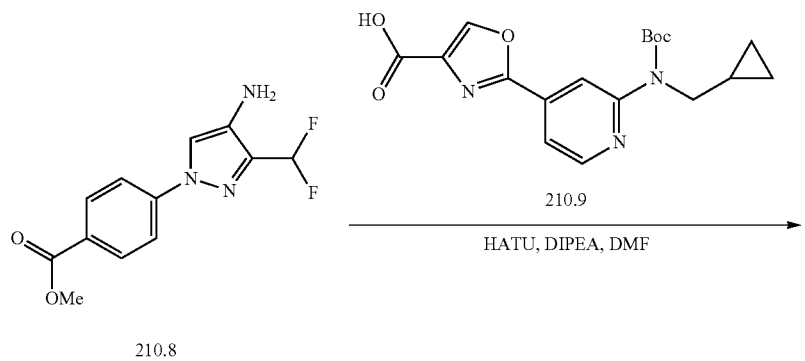

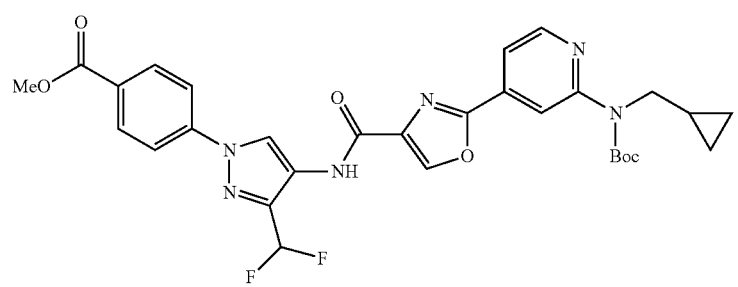

A mixture of methyl 4-[4-amino-3-(difluoromethyl)pyrazol-1-yl]benzoate (340 mg, 1.27 mmol), 2-[2-[tert-butoxycarbonyl(cyclopropylmethyl)amino]-4-pyridyl]oxazole-4-carboxylic acid (412 mg, 1.15 mmol), HATU (484 mg, 1.27 mmol), DIEA (411 mg, 3.18 mmol, 554 uL) in DMF (10 mL) was degassed and purged with $N_2$ for 3 times, and then the mixture was stirred at 25° C. for 6 hrs. On completion, the mixture was poured into 50 mL $H_2O$ and then filtered to give the residue. The solid was dried in vacuo to give the title compound (260 mg, 27% yield) as a yellow solid. LC-MS (Esi) m/z 609.2 (M+H)+.

Step 7—4-[4-[[2-[2-(Cyclopropylmethylamino)-4-pyridyl]oxazole-4-carbonyl]amino]-3-(difluoromethyl)pyrazol-1-yl]benzoic acid (210.11)

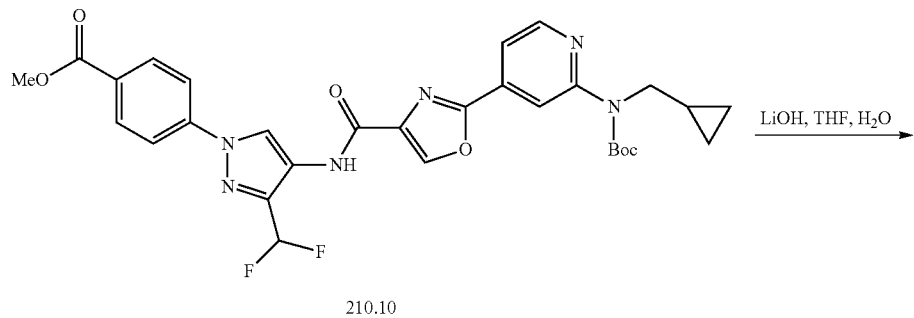

210.10

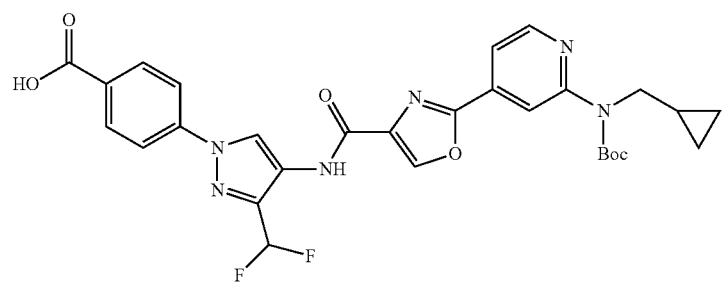

210.11

To a solution of methyl 4-[4-[[2-[2-[tert-butoxycarbonyl(cyclopropylmethyl)amino]-4-pyridyl]oxazole-4-carbonyl]amino]-3-(difluoromethyl)pyrazol-1-yl]benzoate (200 mg, 329 umol) in THF (5 mL) and H₂O (5 mL) and MeOH (1 mL) was added LiOH (39.4 mg, 1.64 mmol). The mixture was stirred at 25° C. for 6 hrs. On completion, the mixture was concentrated, the residue was diluted with H₂O (50 mL) and added 1M HCl to adjust pH=5-6, extracted with EA (3×30 mL). The combined organic layers were washed with brine (50 mL), dried over Na₂SO₄, filtered and concentrated in vacuo to give the title compound (0.13 g, 95% yield) as a yellow solid. LC-MS (ESI+) m/z 595.4 (M+H)⁺.

Step 8—Isopropoxycarbonyl 4-[4-[[2-[2-[tert-butoxycarbonyl(cyclopropylmethyl)amino]-4-pyridyl]oxazole-4-carbonyl]amino]-3-(difluoromethyl)pyrazol-1-yl]benzoate (210.13)

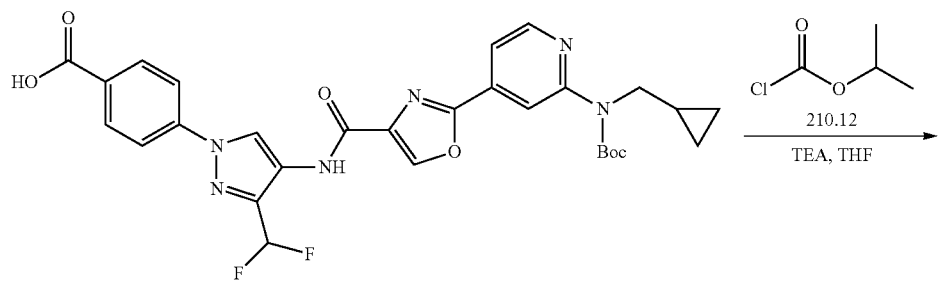

210.11

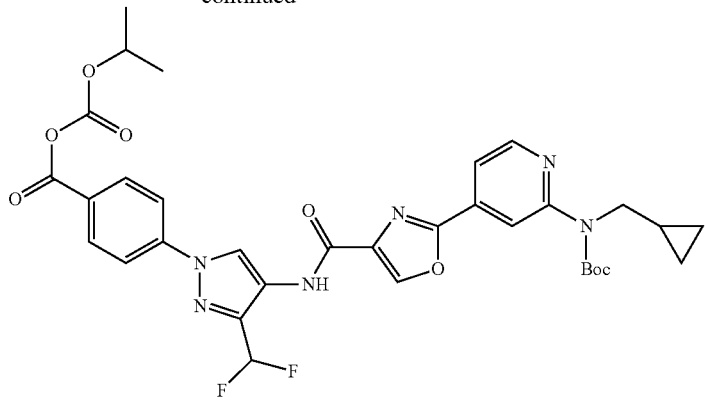

210.13

To a solution of 4-[4-[[2-[2-[tert-butoxycarbonyl(cyclopropylmethyl)amino]-4-pyridyl]oxazole-4-carbonyl]amino]-3-(difluoromethyl)pyrazol-1-yl]benzoic acid (250 mg, 420 umol) in THF (10 mL) was added TEA (170 mg, 1.68 mmol) and isopropyl carbonochloridate (128 mg, 1.05 mmol). The mixture was stirred at −10° C. for 1 hour. On completion, the mixture was filtered and the filtrate was concentrated in vacuo to give the title compound (280 mg, 90% yield) as yellow solid. LC-MS (ESt) m/z 681.3 (M+H)$^+$.

Step 9—Tert-butyl N-(cyclopropylmethyl)-N-[4-[4-[[3-(difluoromethyl)-1-[4-(hydroxymethyl)phenyl]pyrazol-4-yl]carbamoyl]oxazol-2-yl]-2-pyridyl]carbamate (210.14)

To a solution of isopropoxycarbonyl 4-[4-[[2-[2-[tert-butoxycarbonyl(cyclopropylmethyl)amino]-4-pyridyl]oxazole-4-carbonyl]amino]-3-(difluoromethyl)pyrazol-1-yl]benzoate (280 mg, 411 umol) in THF (30.0 mL) and H$_2$O (4.00 mL) was added NaBH$_4$ (62.2 mg, 1.65 mmol). The mixture was stirred at 0° C. for 1 hour. On completion, the mixture was diluted with H$_2$O (50 mL) extracted with EtOAc (3×30 mL). The organic layers were dried over anhydrous Na$_2$SO$_4$ filtered and concentrated in vacuo. The mixture was triturated with DCM:PE=1:5 (30 mL), filtered. The filter cake was dried in vacuo to give the title compound (200 mg, 83% yield) as white solid. LC-MS (Est) m/z 581.3 (M+H)$^+$.

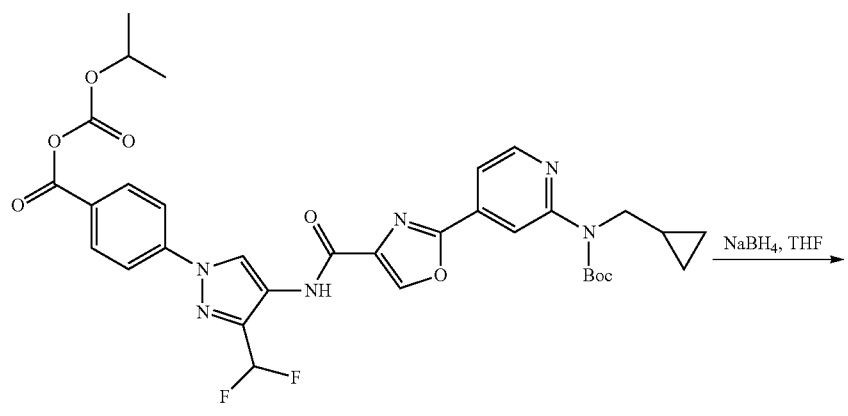

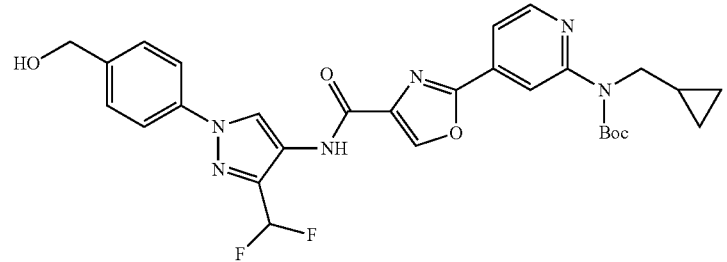

210.14

Step 10—Tert-butyl N-(cyclopropylmethyl)-N-[4-[4-[[3-(difluoromethyl)-1-(4-formylphenyl)pyrazol-4-yl]carbamoyl]oxazol-2-yl]-2-pyridyl]carbamate (210.15)

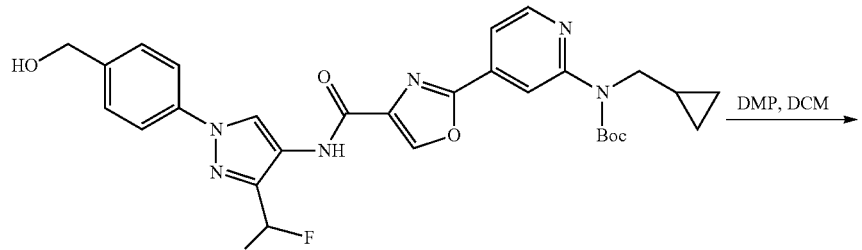

210.14

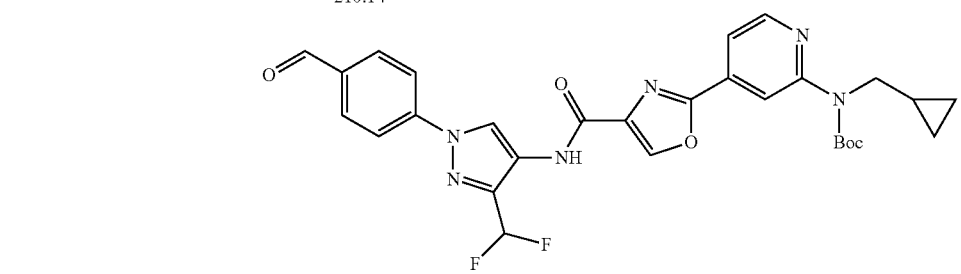

210.15

To a solution of tert-butyl N-(cyclopropylmethyl)-N-[4-[4-[[3-(difluoromethyl)-1-[4-(hydroxymethyl)phenyl]pyrazol-4-yl]carbamoyl]oxazol-2-yl]-2-pyridyl]carbamate (140 mg, 241 umol) in DCM (10.0 mL) was added DMP (204 mg, 482 umol). The mixture was stirred at 15° C. for 2 hours. On completion, the mixture was diluted with DCM (30 mL), extracted with saturated Na$_2$S$_2$O$_3$ (2×30 mL) and saturated NaHCO$_3$ (2×30 mL). The organic layer was dried over anhydrous Na$_2$SO$_4$, filtered and concentrated in vacuo to give the title compound (80.0 mg, 57% yield) as white solid. LC-MS (Est) m/z 579.1 (M+H)$^+$.

Step 11—Tert-butyl N-(cyclopropylmethyl)-N-[4-[4-[[3-(difluoromethyl)-1-[4-[[2-[2-[2-[[2-(2,6-dioxo-3-piperidyl)-1,3-dioxoisoindolin-4-yl]amino]ethoxy]ethoxy]ethylamino]methyl]phenyl]pyrazol-4-yl]carbamoyl]oxazol-2-yl]-2-pyridyl]carbamate (210.16)

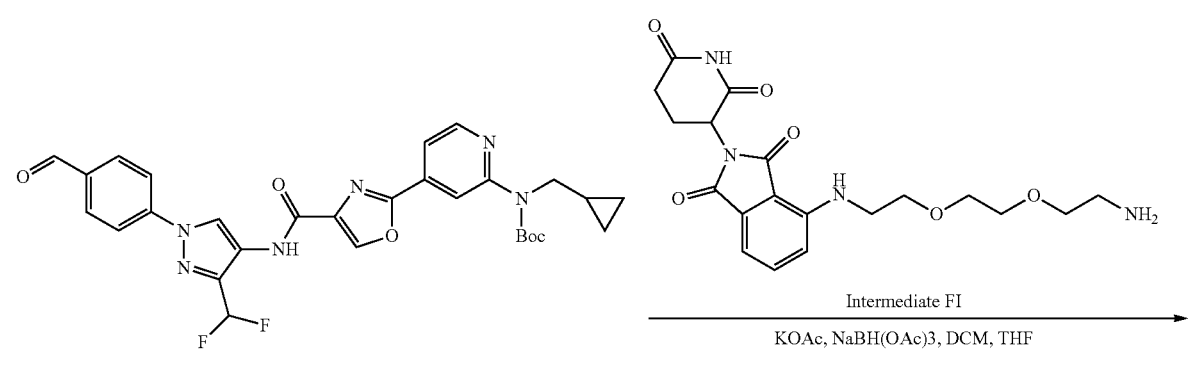

210.15

Intermediate FI
KOAc, NaBH(OAc)3, DCM, THF

-continued

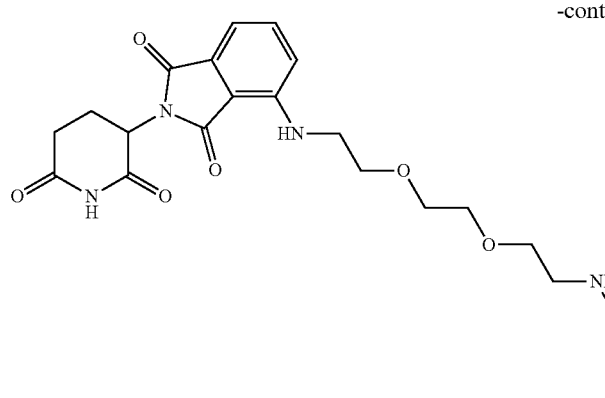

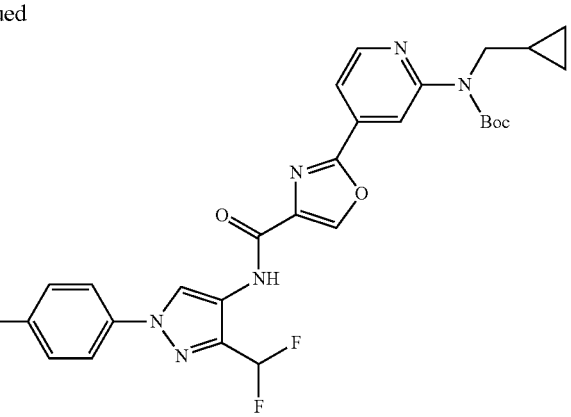

Step 12—2-[2-(Cyclopropylmethylamino)-4-pyridyl]-N-[3-(difluoromethyl)-1-[4-[[2-[2-[2-[[2-(2,6-dioxo-3-piperidyl)-1,3-dioxoisoindolin-4-yl]amino]ethoxy]ethoxy]ethylamino]methyl]phenyl]pyrazol-4-yl]oxazole-4-carboxamide, I-210

To a solution of tert-butyl N-(cyclopropylmethyl)-N-[4-[4-[[3-(difluoromethyl)-1-(4-formylphenyl) pyrazol-4-yl]carbamoyl]oxazol-2-yl]-2-pyridyl]carbamate (150 mg, 259 umol) and 4-[2-[2-(2-amino ethoxy)ethoxy]ethylamino]-2-(2,6-dioxo-3-piperidyl)isoindoline-1,3-dione (137 mg, 311 umol, HCl) in DCM (10.0 mL) and THF (10.0 mL) was added KOAc (76.3 mg, 777 umol) and NaBH(OAc)₃ (164 mg, 777 umol). The mixture was stirred at 15° C. for 6 hours. On completion, the reaction mixture was quenched by 10 mL H2O, and extracted with EA (3×10 mL). The combined organic layers were washed with brine (20 mL), dried over Na2SO4, filtered and concentrated in vacuo. The residue was purified by reverse phase (HCl condition H2O:ACN 0-100%) to give the title compound (150 mg, 59% yield) as yellow solid. LC-MS (ESI+) m/z 967.6 (M+H)+.

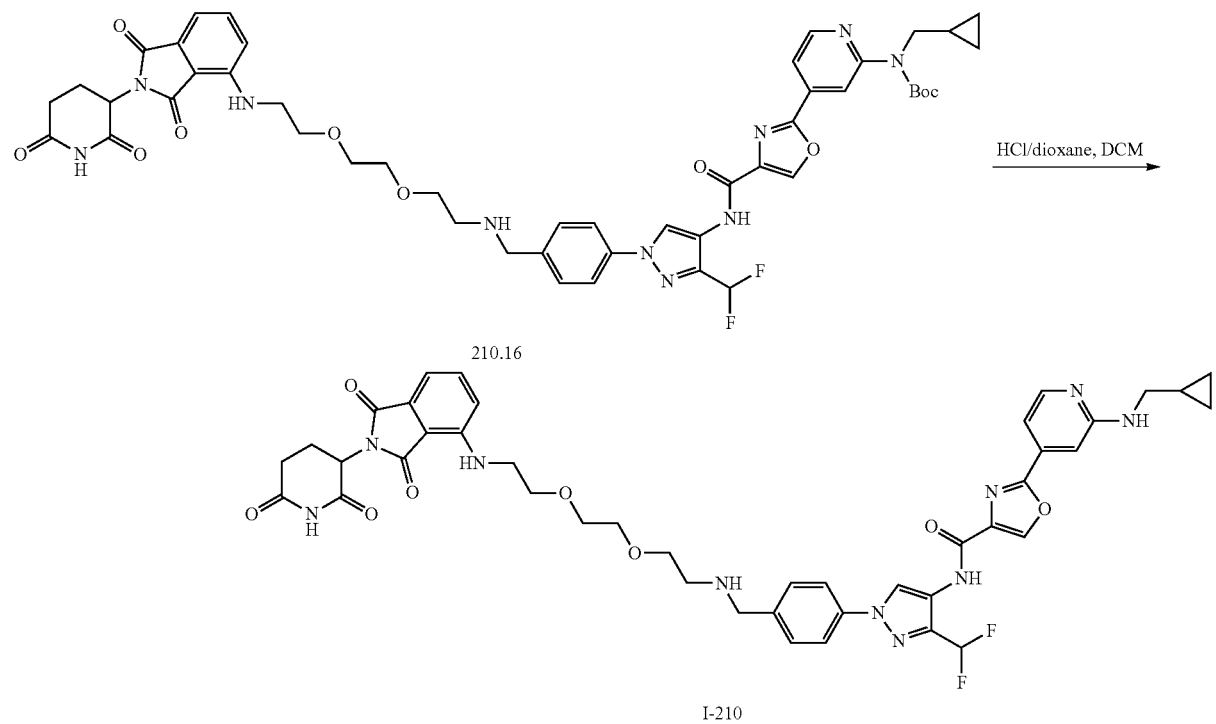

To a solution of tert-butyl N-(cyclopropylmethyl)-N-[4-[4-[[3-(difluoromethyl)-1-[4-[[2-[2-[2-[[2-(2,6-dioxo-3-piperidyl)-1,3-dioxo-isoindolin-4-yl]amino]ethoxy]ethoxy]ethylamino]methyl]phenyl]pyrazol-4-yl]carbamoyl]oxazol-2-yl]-2-pyridyl]carbamate (150 mg, 155 umol) in DCM (2.00 mL) was added HCl/dioxane (4 M, 2.00 mL). The mixture was stirred at 15° C. for 0.5 hour. On completion, the mixture was concentrated in vacuo. The mixture was purified by prep-HPLC (column: Phenomenex Synergi C18 150*25*10 um; mobile phase: [water (0.225% FA)-ACN];

B %: 13%-37%, 10 min) to give the title compound (85.1 mg, 60% yield, FA) as yellow solid. 1H NMR (400 MHz, DMSO-d6) δ 11.07 (s, 1H), 9.97 (s, 1H), 8.96 (s, 1H), 8.77 (s, 1H), 8.19 (s, 1H), 8.15 (d, J=5.6 Hz, 1H), 7.78 (d, J=8.8 Hz, 2H), 7.58-7.72 (m, 1H), 7.47 (d, J=8.8 Hz, 2H), 7.42-7.14 (m, 1H), 7.13-7.10 (m, 2H), 7.10-7.05 (m, 1H), 7.04-7.00 (m, 2H), 6.62-6.55 (m, 1H), 5.07-5.00 (m, 1H), 3.79 (s, 2H), 3.61-3.51 (m, 8H), 3.46-3.43 (m, 2H), 3.20-3.15 (m, 2H), 2.90-2.82 (m, 1H), 2.72-2.67 (m, 2H), 2.61-2.56 (m, 1H), 2.55-2.53 (m, 1H), 2.04-1.96 (m, 1H), 1.10-1.01 (m, 1H), 0.48-0.41 (m, 2H), 0.24-0.19 (m, 2H), LC-MS (ESI+) m/z 867.1 (M+H)+.

We claim:
1. A compound of formula I:

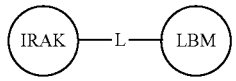
I or a pharmaceutically acceptable salt thereof, wherein:
IRAK is an IRAK binding moiety capable of binding to IRAK4, said compound of formula I is a compound of formula I-vv-2:

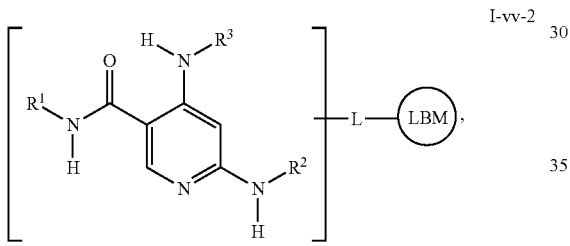
I-vv-2 or a pharmaceutically acceptable salt thereof, wherein:
$R^1$ is:
  (a) $C_{2-3}$ hydroxyalkyl substituted with zero to 4 $R^{1a}$ wherein $R^{1a}$ is independently selected from F, Cl, —OH, —CHF$_2$, —CN, —CF$_3$, —OCH$_3$, and cyclopropyl;
  (b) $C_{1-3}$ alkyl substituted with —O($C_{1-3}$ alkyl) and zero to 4 $R^{1a}$ wherein $R^{1a}$ is independently selected from F, Cl, —OH, —CHF$_2$, —CN, —CF$_3$, and cyclopropyl;
  (c) $C_{4-8}$ alkyl substituted with zero to 7 $R^{1a}$ wherein $R^{1a}$ is independently selected from F, Cl, —OH, —CHF$_2$, —CF$_3$, —CN—OCH$_3$, cyclopropyl, and —OP(O)(OH)$_2$;
  (d) —(CH$_2$)$_{2-4}$NHC(O)($C_{1-6}$ alkyl), —(CH$_2$)$_2$CH(CH$_3$)NHC(O)($C_{1-6}$alkyl), (CH$_2$)$_2$CH(CH$_3$)NHC(O)(CH$_2$)$_{0-1}$NH($C_{1-6}$ alkyl), or (CH$_2$)$_2$CH(CH$_3$)NHC(O)(CH$_2$)$_{0-1}$N($C_{1-4}$ alkyl)$_2$;
  (e) cyclohexyl substituted with zero to 2 substituents independently selected from —OH, —OCH$_3$, $C_{1-6}$ alkyl, $C_{1-6}$hydroxyalkyl, —C(O)NH$_2$, —C(O)NH($C_{1-3}$ alkyl), —C(O)NH($C_{1-6}$hydroxyalkyl), —C(O)NH($C_{3-6}$ cycloalkyl), —C(O)NH($C_{3-6}$ fluoro cycloalkyl), —NHC(O)($C_{1-3}$ alkyl), —NHC(O)O($C_{1-3}$ alkyl), —NHS(O)$_2$CH$_3$, —S(O)$_2$NH$_2$, —S(O)$_2$($C_{1-3}$ alkyl), —S($C_{1-3}$ alkyl), thiazolyl, methyl pyrazolyl, and $C_{1-3}$ alkyl substituted with —OH and cyclopropyl;
  (f) —(CH$_2$)$_2$(phenyl) wherein said phenyl is substituted with —C(O)NH$_2$, —C(O)NH($C_{1-3}$ alkyl), or —S(O)$_2$ NH$_2$; or
  (g) piperidinyl substituted with —C(O)($C_{1-3}$ alkyl);
$R^2$ is phenyl, pyridinyl, pyridazinyl, pyrimidinyl, pyrazolyl, thiazolyl, or triazolyl, each substituted with zero to 2 substituents independently selected from F, Cl, —OH, —CN, $C_{1-3}$ alkyl, —CH$_2$C(O)OCH$_3$, —O($C_{1-3}$ alkyl), —NH$_2$, —NH($C_{1-3}$ alkyl), —NH(cyclopropyl), —C(O)NH$_2$, —NHC(O)($C_{1-3}$ alkyl), —NH(tetrahydropyranyl), hydroxypyrrolidinyl, =O, —O(piperidinyl), and pyridinyl; and
$R^3$ is:
  (a) $C_{1-6}$ alkyl substituted with zero to 4 substituents independently selected from F, —OH, —CH$_3$, —CF$_3$, and $C_{3-6}$cycloalkyl;
  (b) $C_{3-6}$ cycloalkyl substituted with zero to 2 substituents independently selected from F, —OH, $C_{1-3}$ hydroxyalkyl, —CH$_3$, —CF$_2$H, —NH$_2$, and —C(O)OCH$_2$CH$_3$;
  (c) oxetanyl, tetrahydropyranyl, or fluoro tetrahydropyranyl;
  (d) phenyl substituted with zero to 2 substituents independently selected from —OH, CN, —O($C_{1-3}$ alkyl), $C_{1-3}$ hydroxyalkyl, —C(O)NH$_2$, —S(O)$_2$NH$_2$, —NHS(O)$_2$($C_{1-3}$ alkyl), pyrazolyl, imidazolyl, and methyl tetrazolyl; or
  (e)

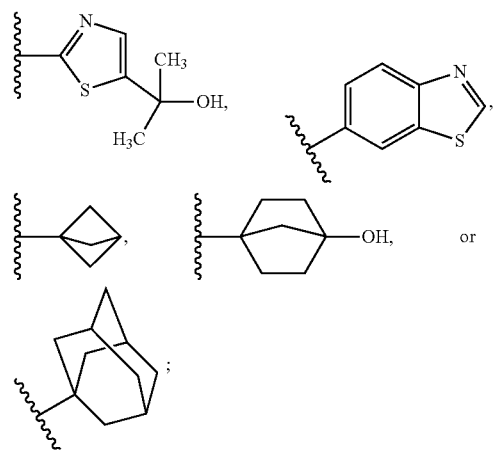

L is a covalent bond or a bivalent, saturated or unsaturated, straight or branched $C_{1-50}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

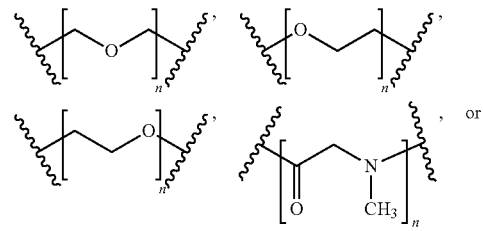

-continued

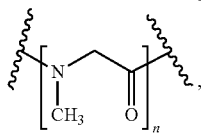

wherein:

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur; and each of n is independently 1, 2, 3, 4, 5, 6, 7, 8, 9, or 10;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur; and LBM is a ligase binding moiety selected from a cereblon E3 ubiquitin ligase binding moiety and a VHL E3 ubiquitin ligase binding moiety.

2. The compound according to claim 1, wherein the cereblon E3 ubiquitin ligase binding moiety is selected from:

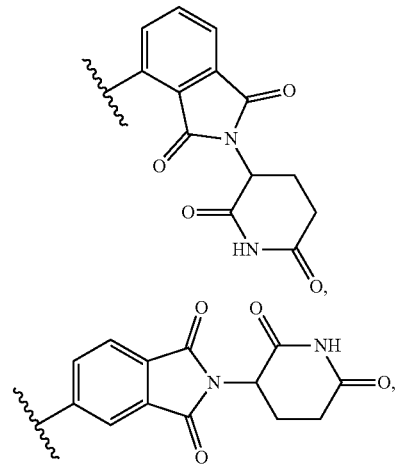

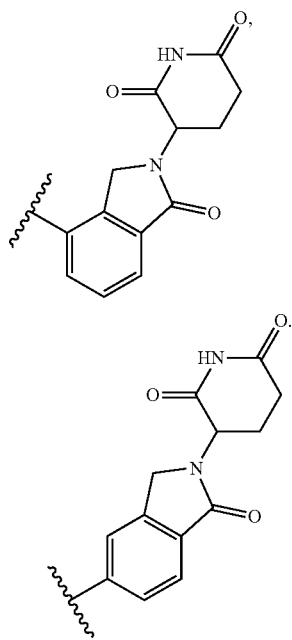

and

3. The compound according to claim 1, wherein the IRAK4 binding moiety is selected from:

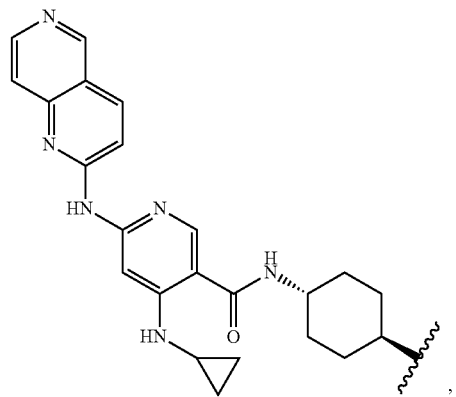

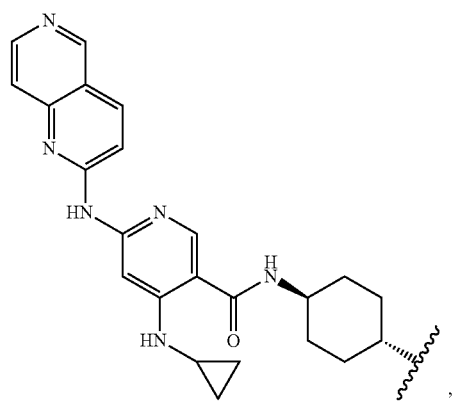

2699
-continued
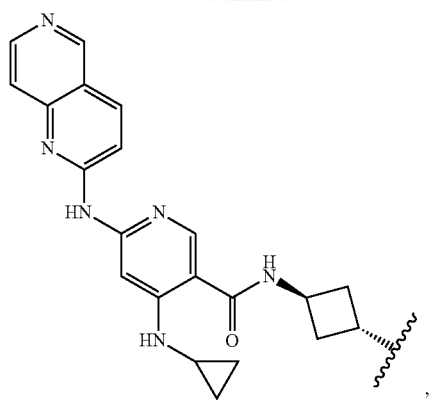
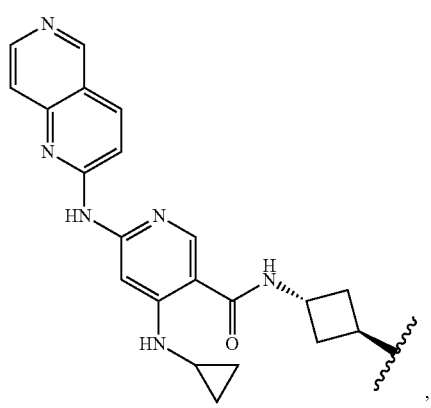
2700
-continued
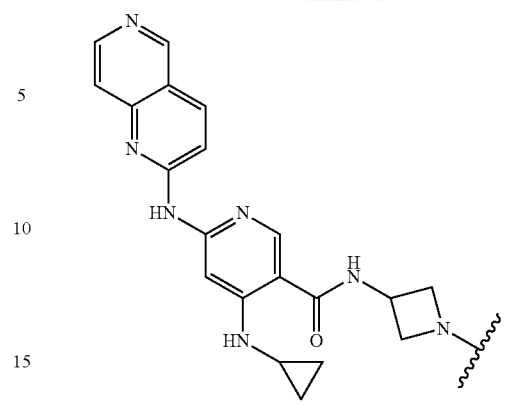
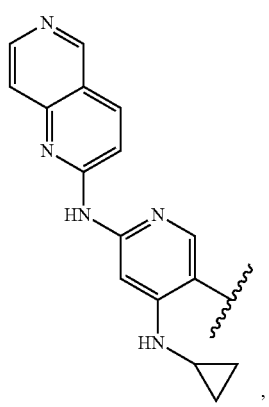
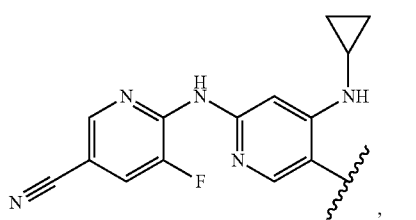
, and
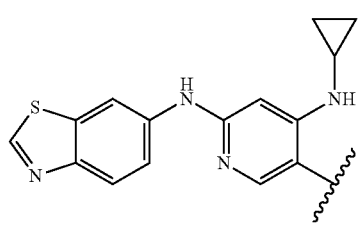
.

4. The compound of claim 1, wherein L is selected from:
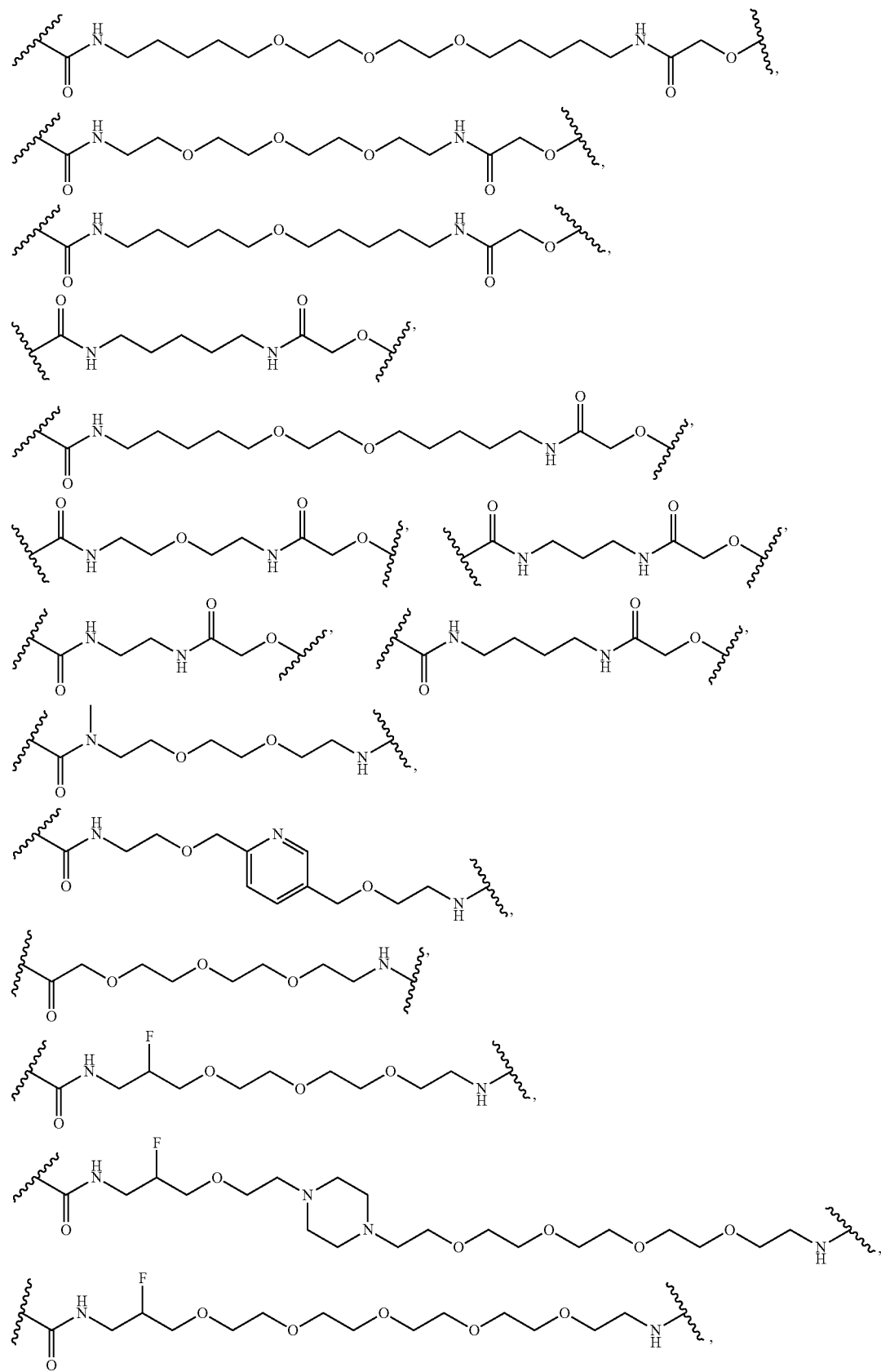

-continued
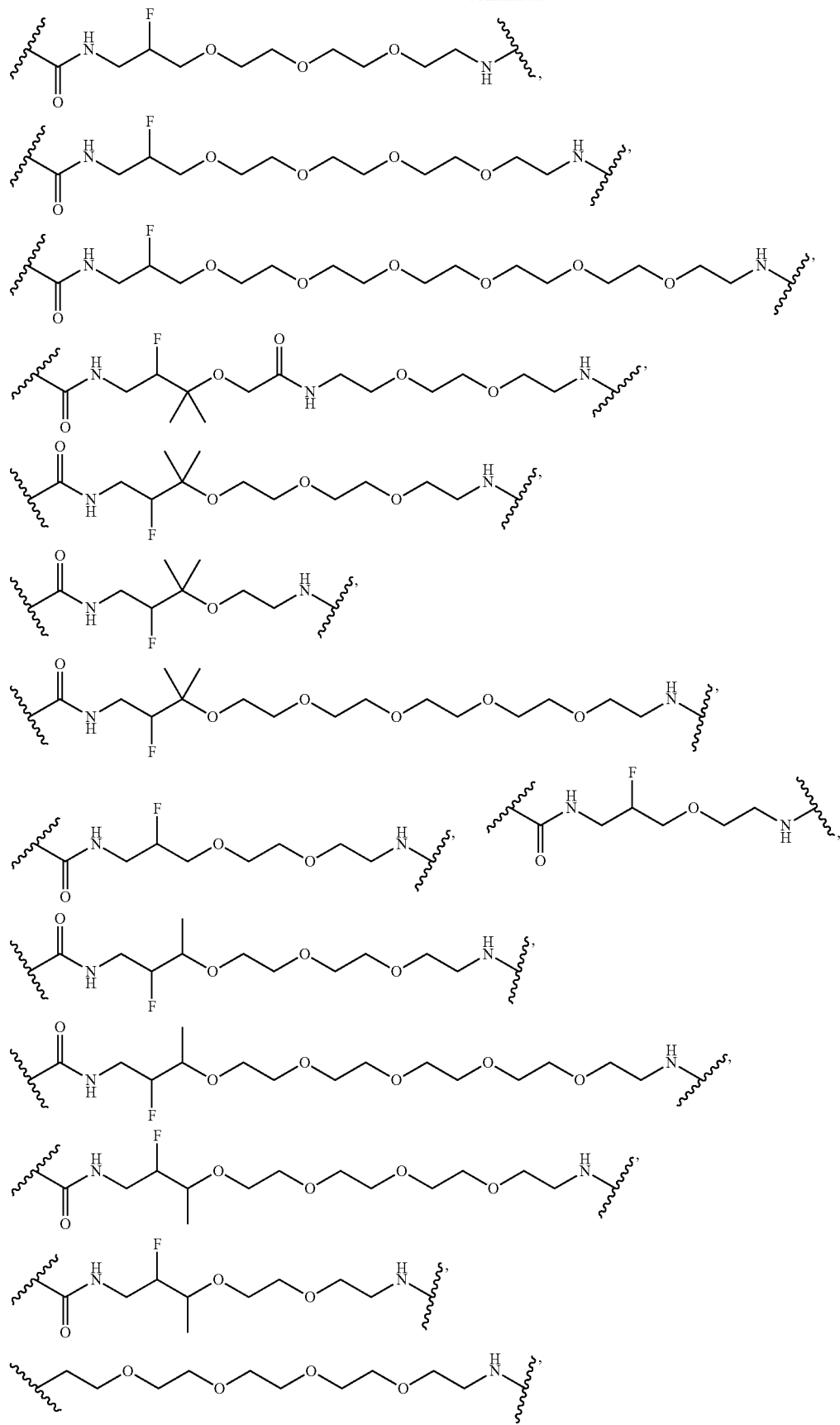

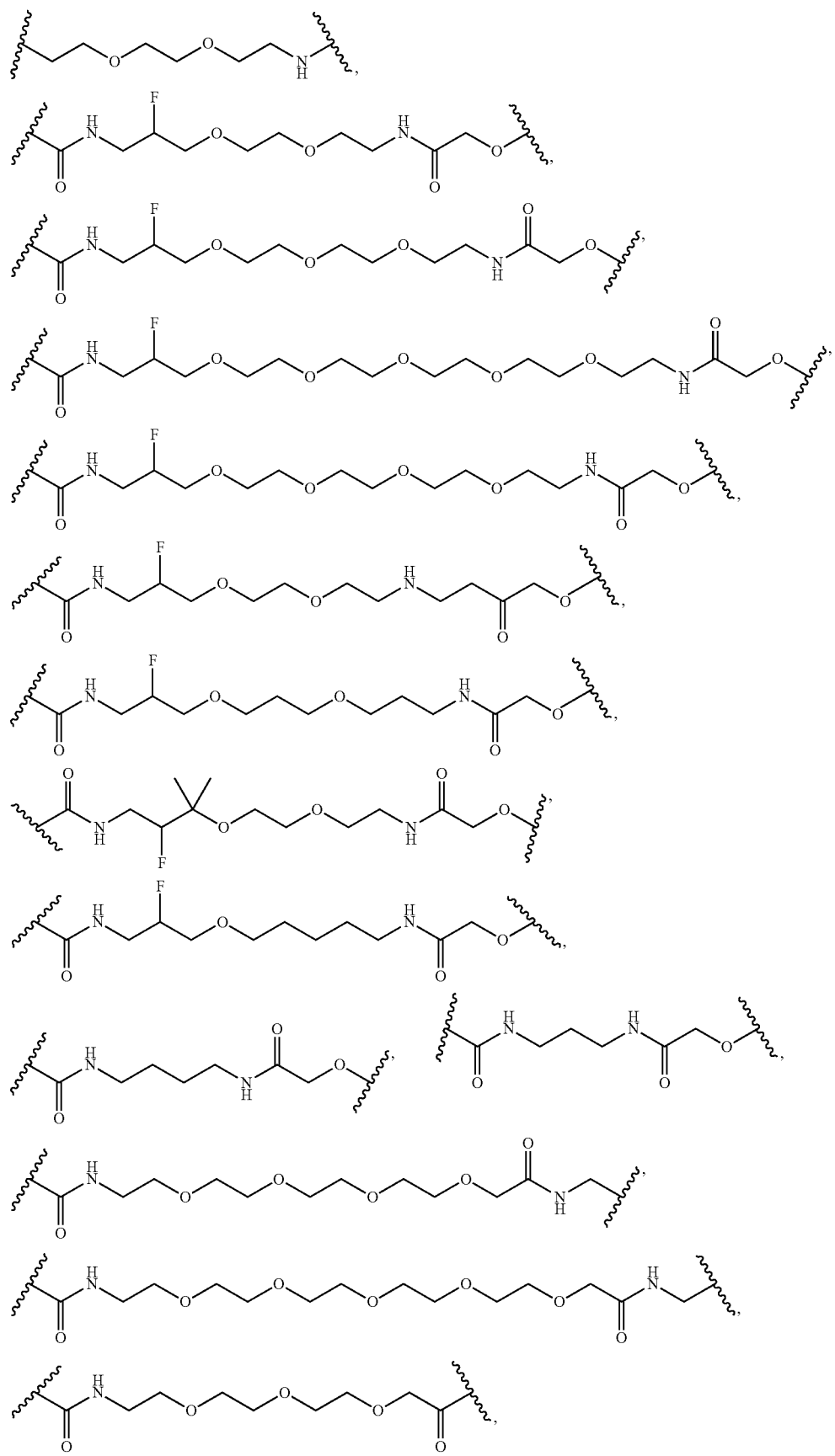

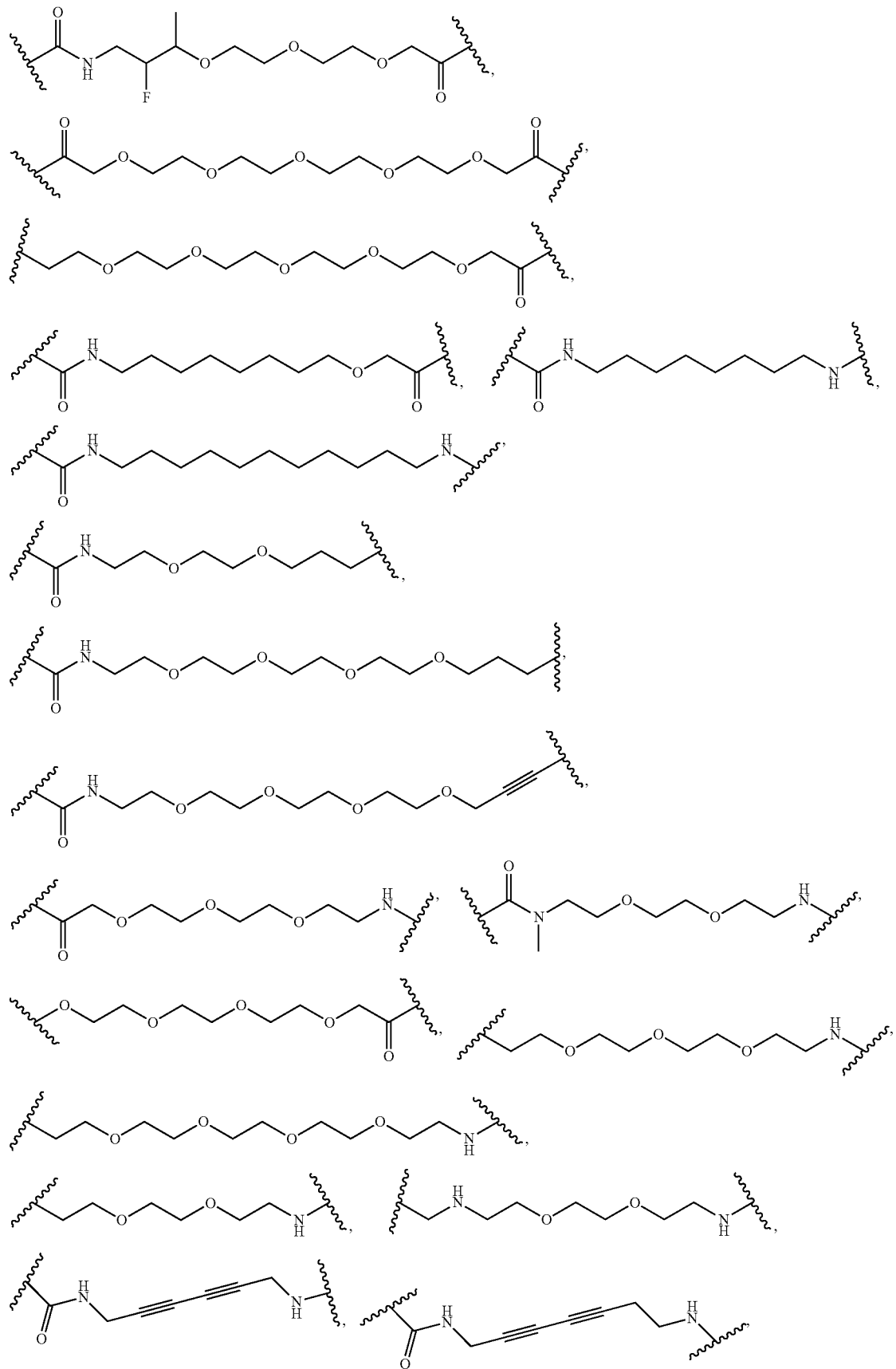

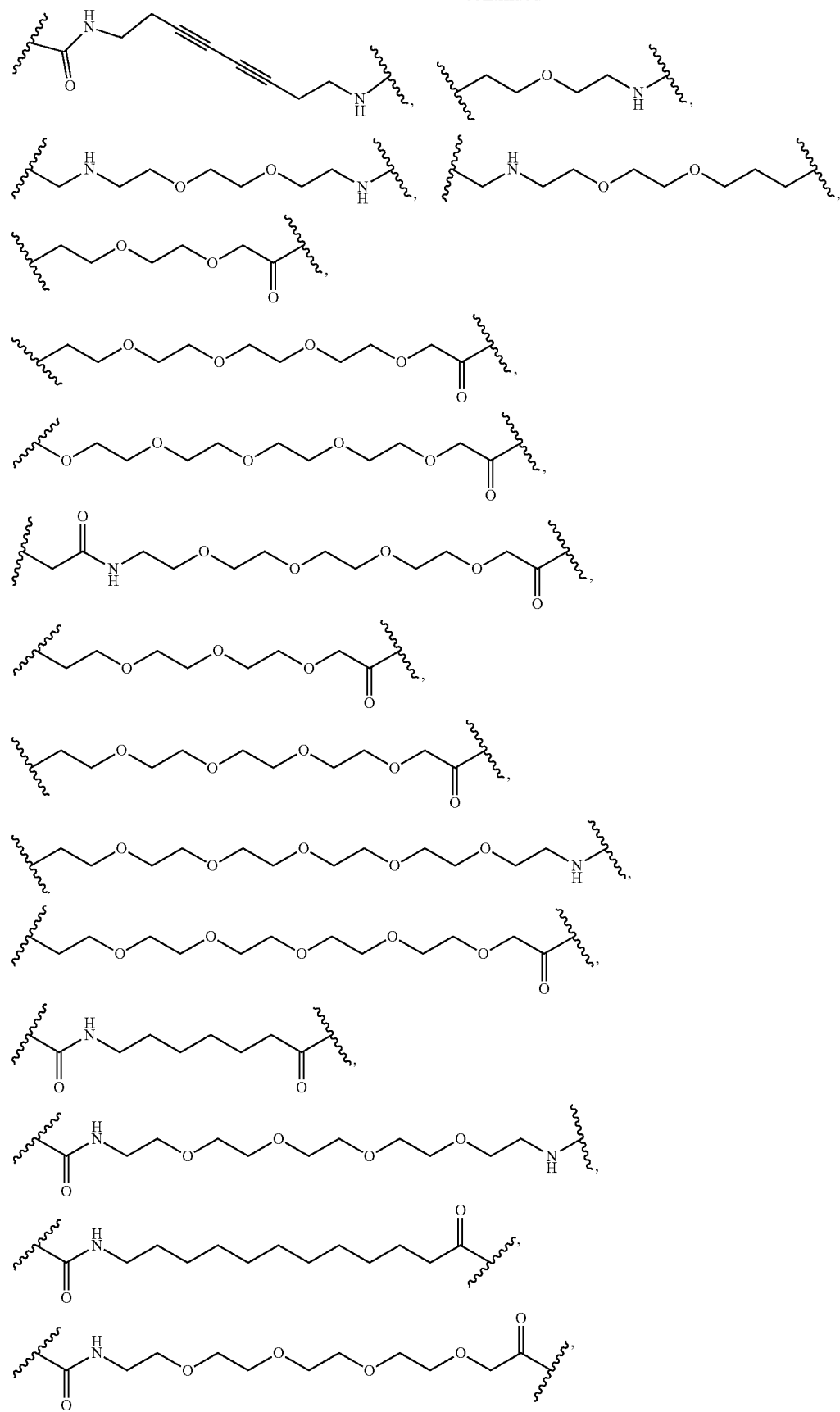

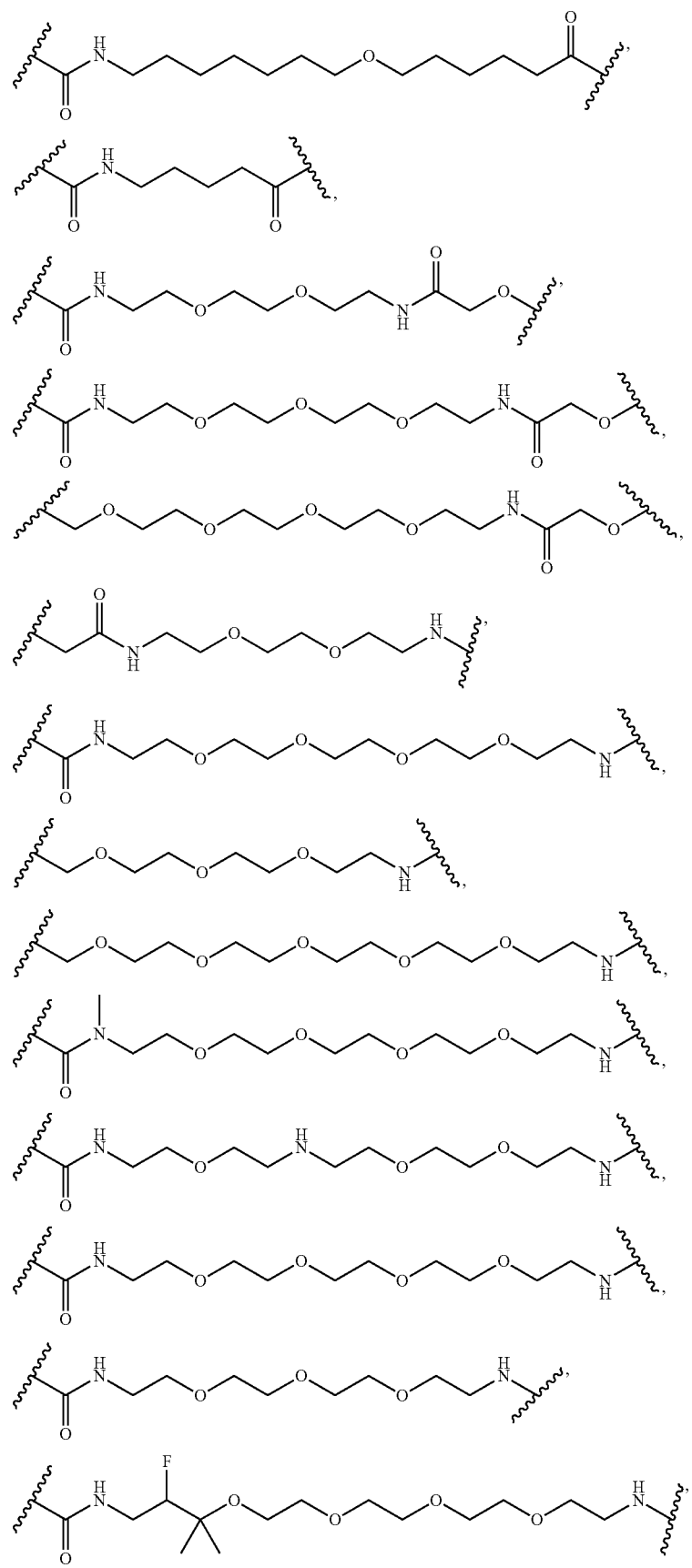

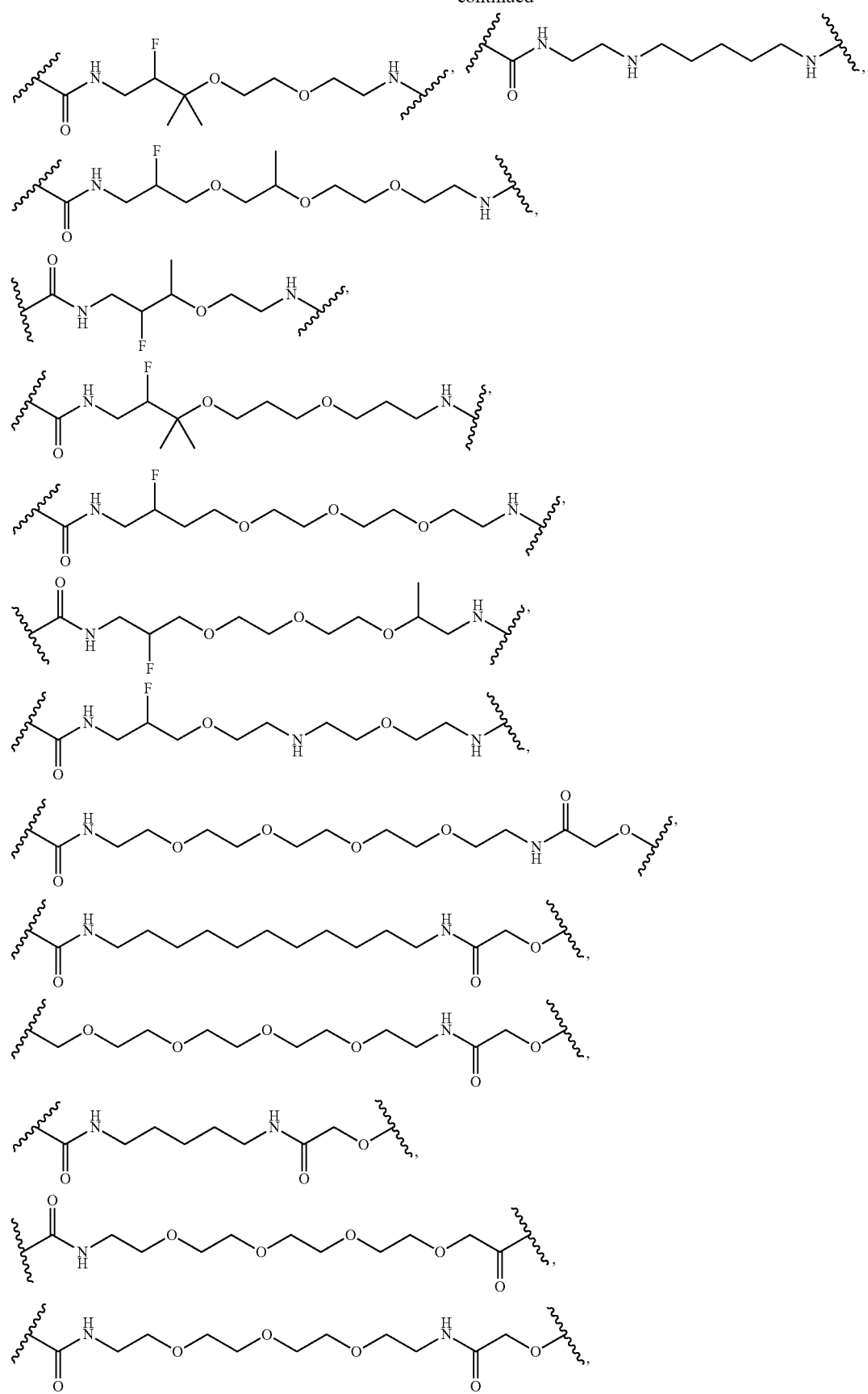

2715 2716
-continued
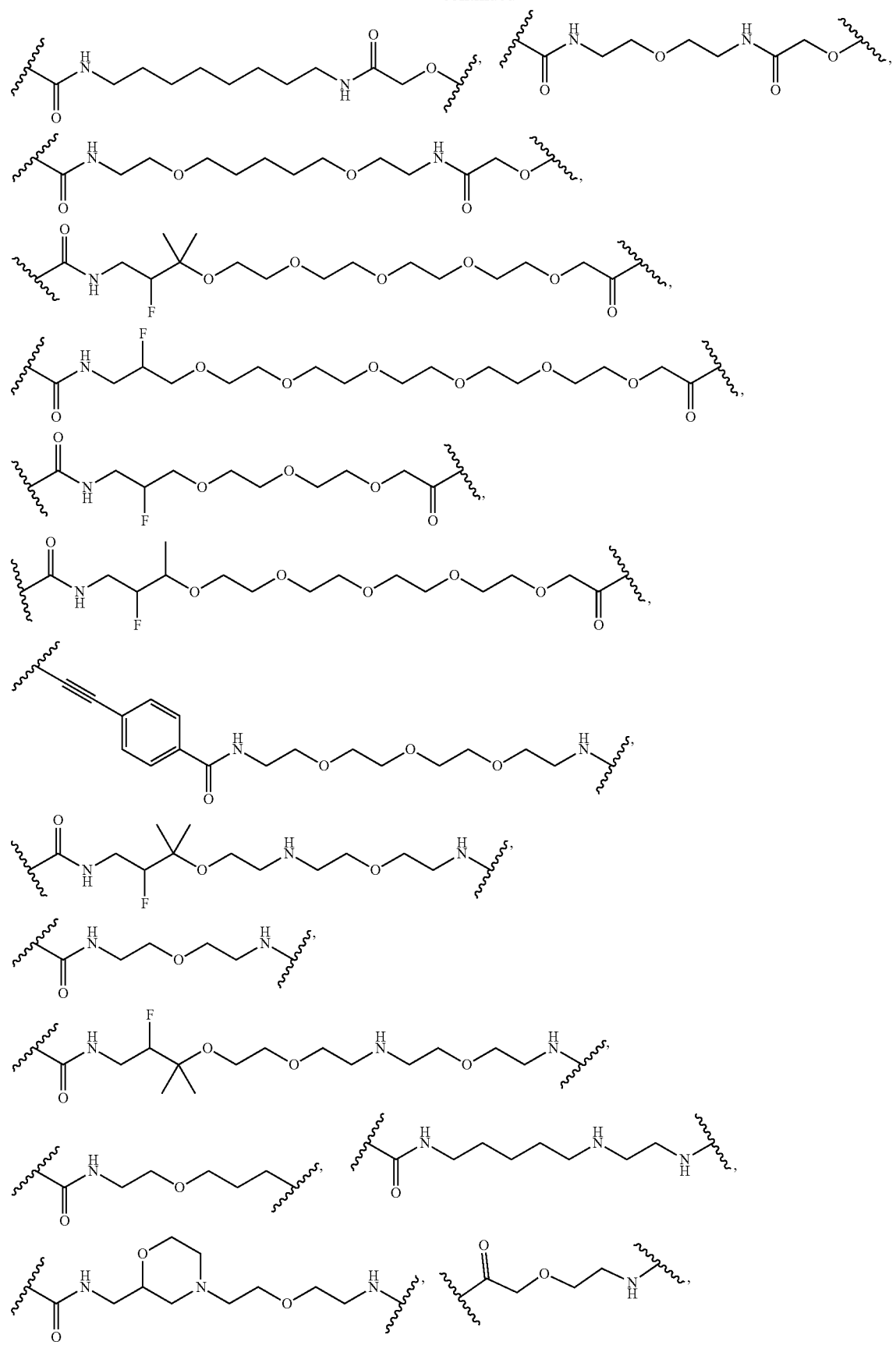

-continued
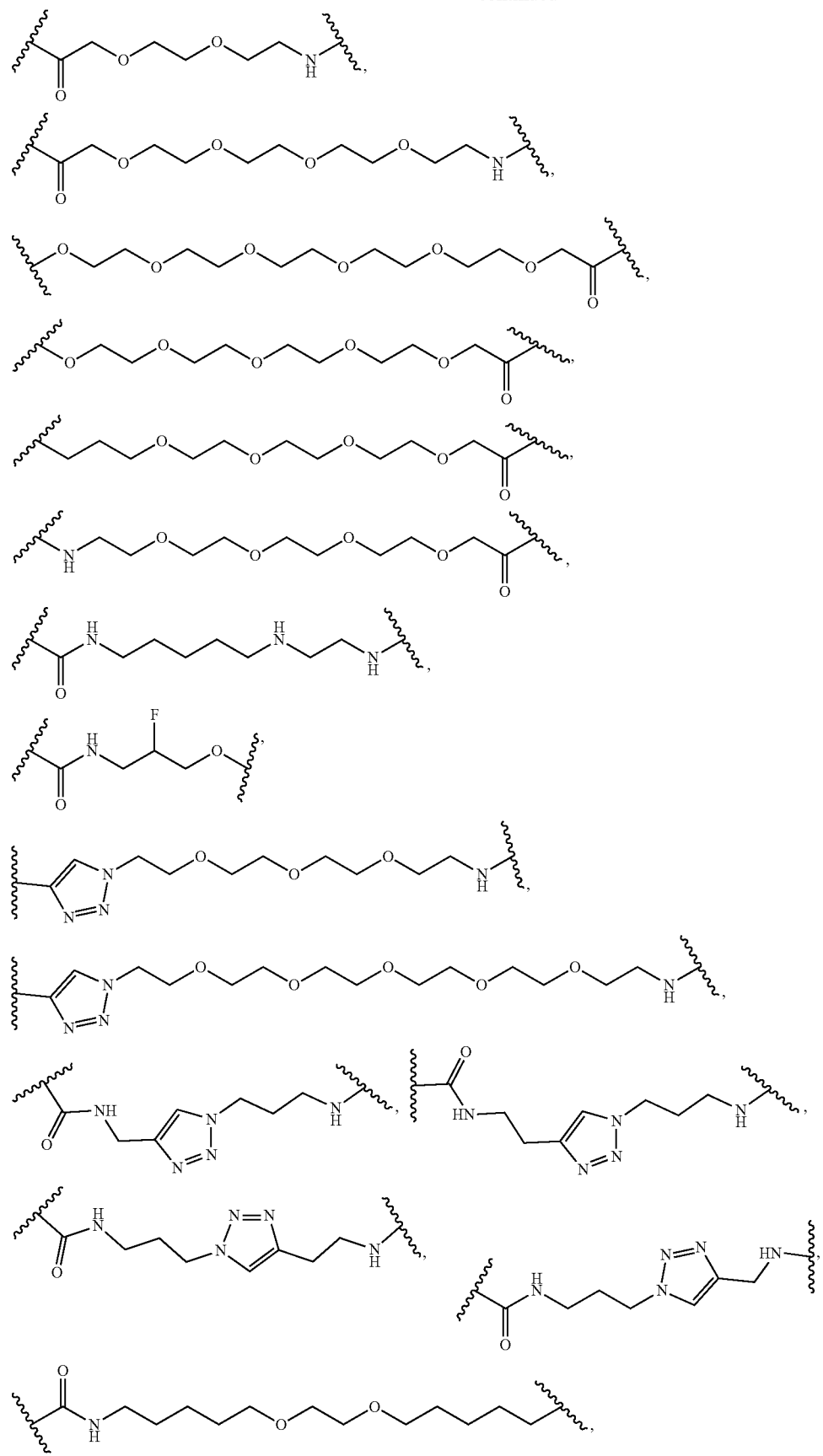

-continued
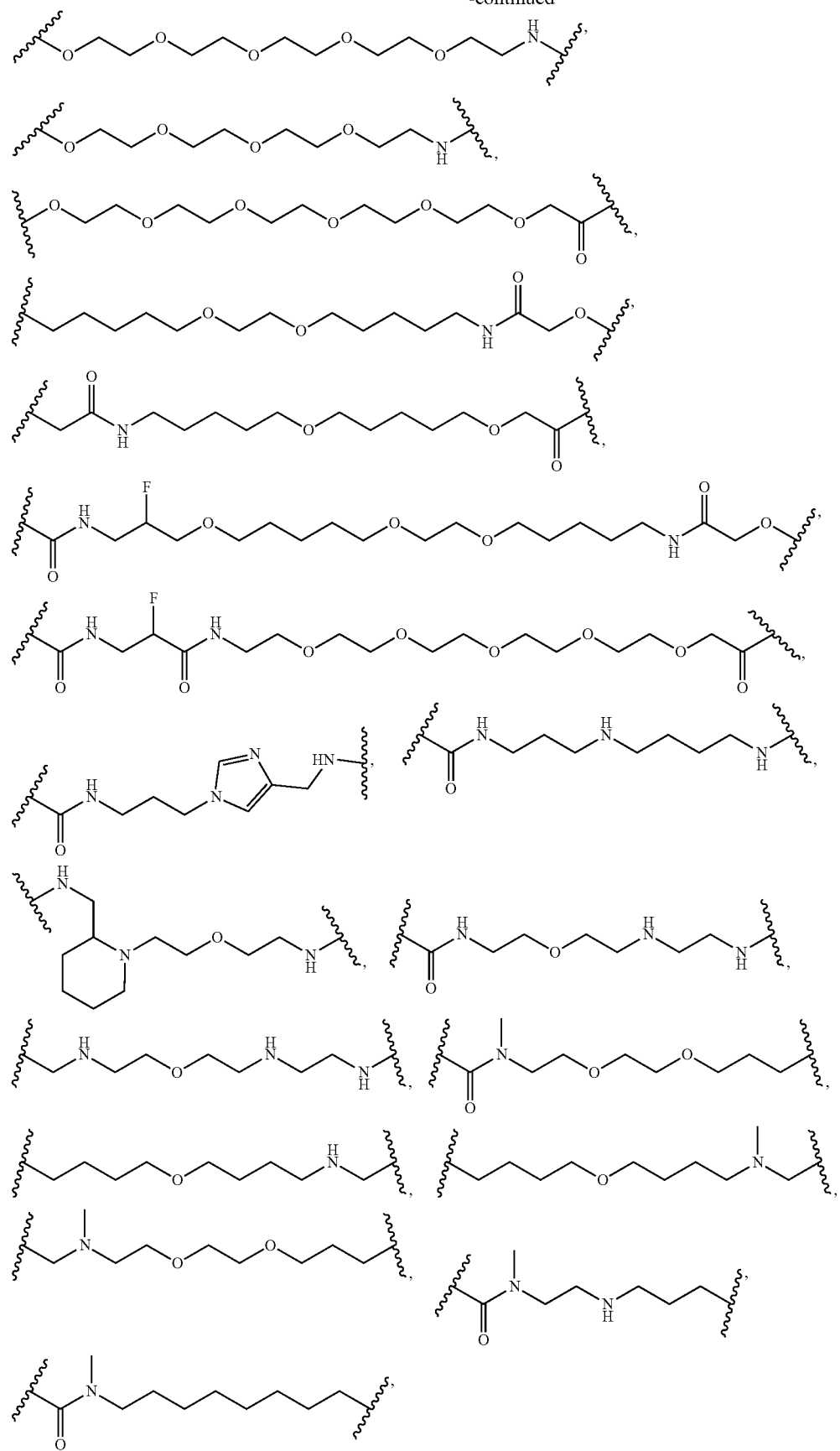

-continued
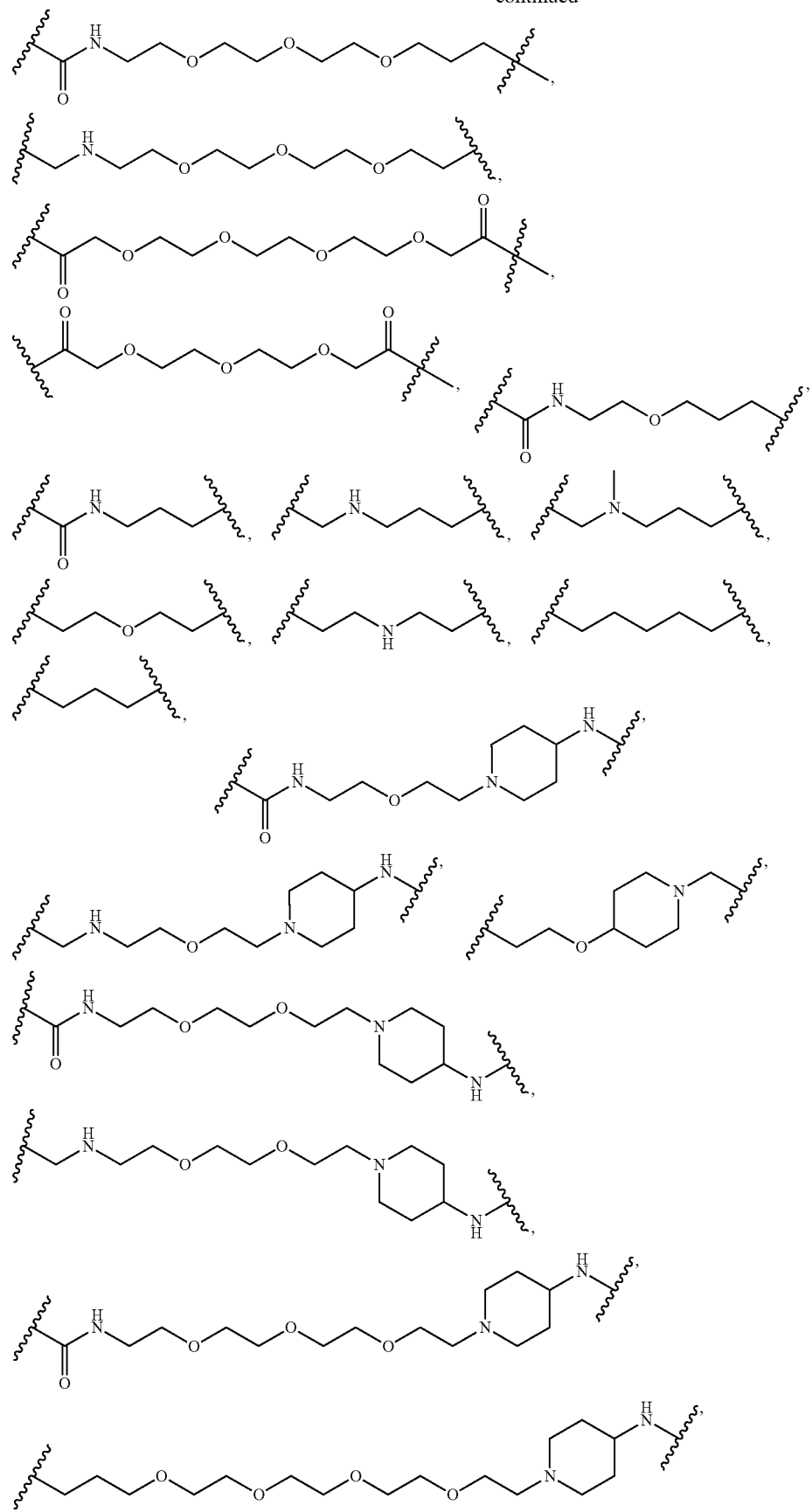

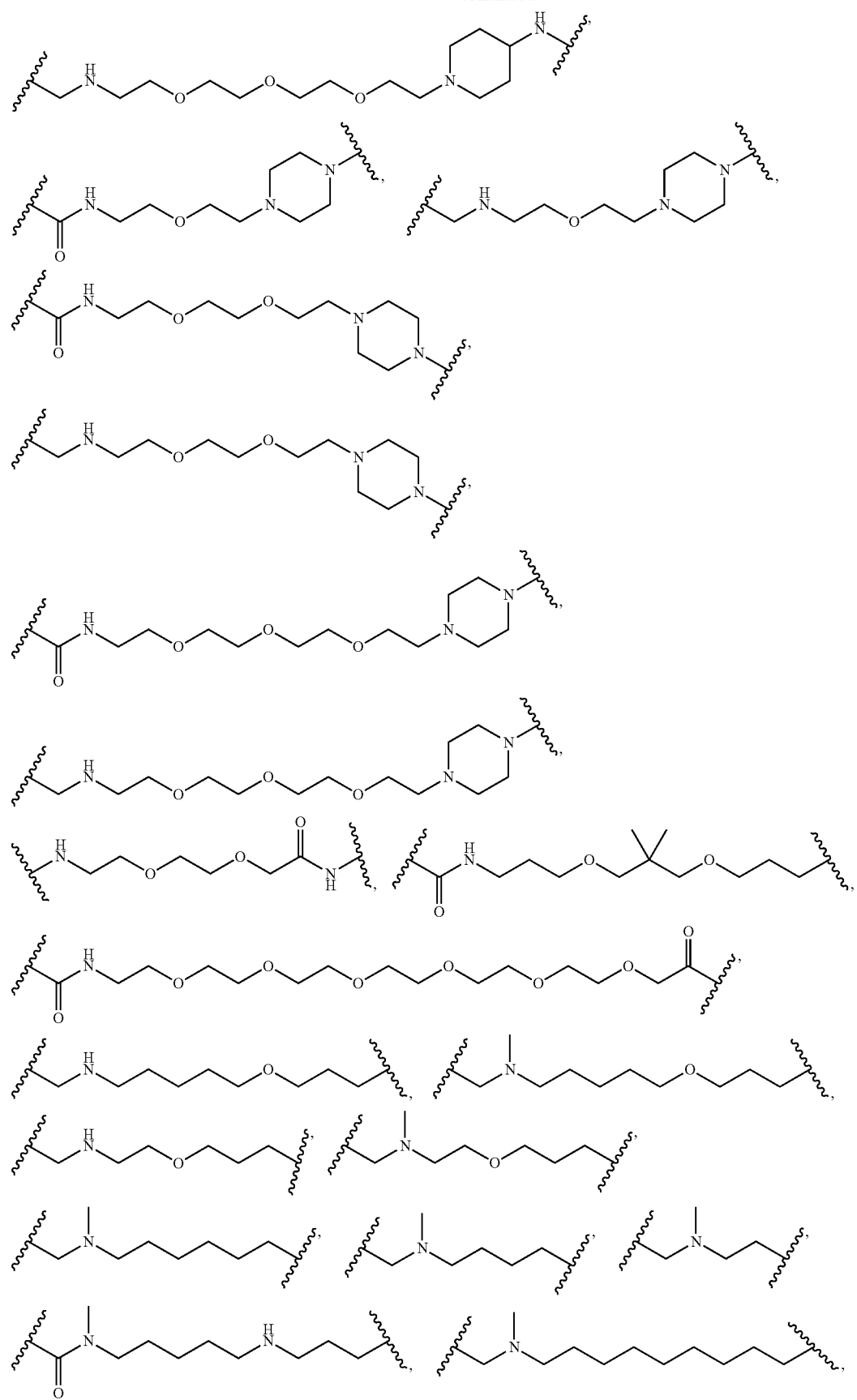

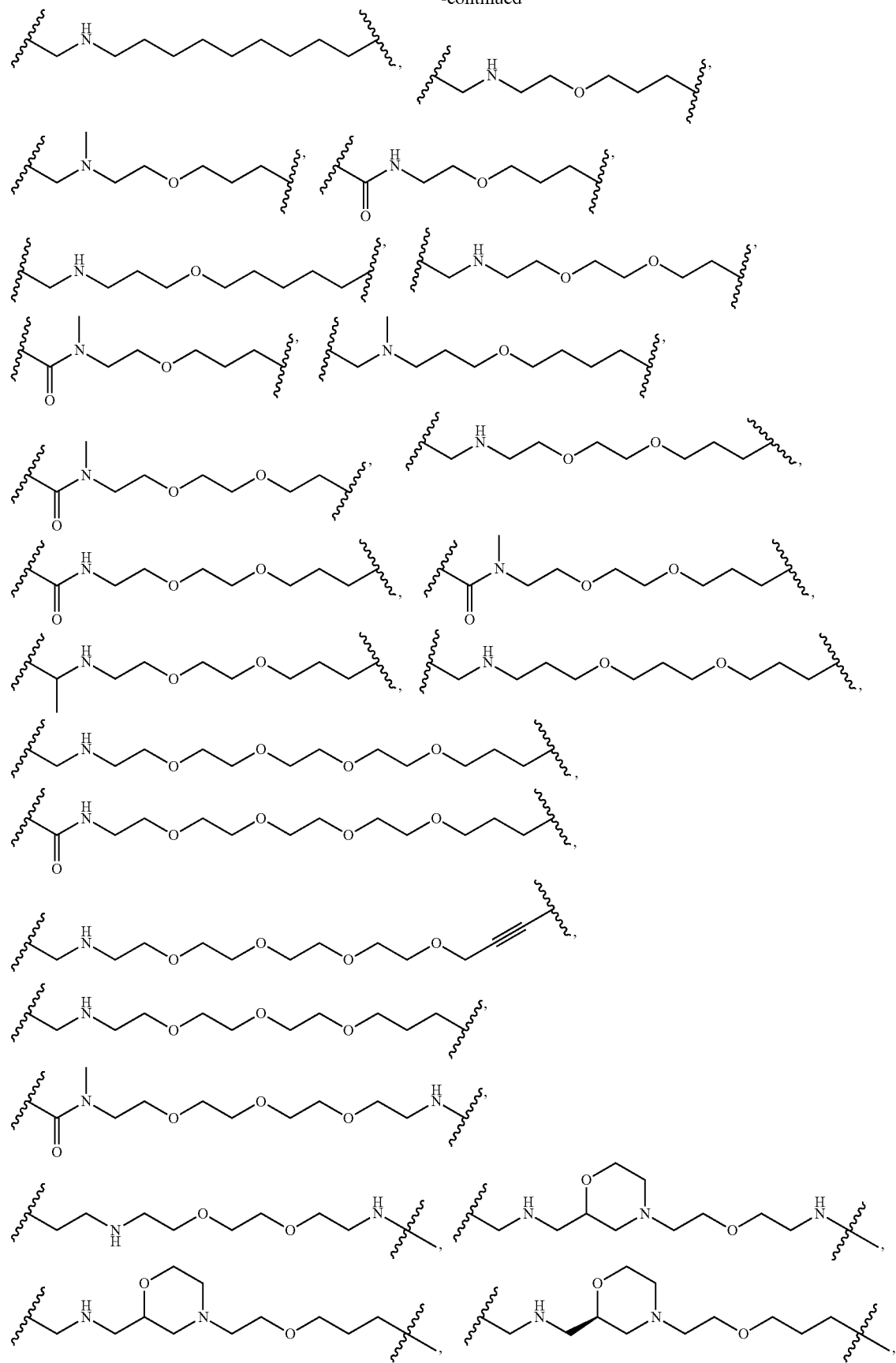

2727 2728
-continued
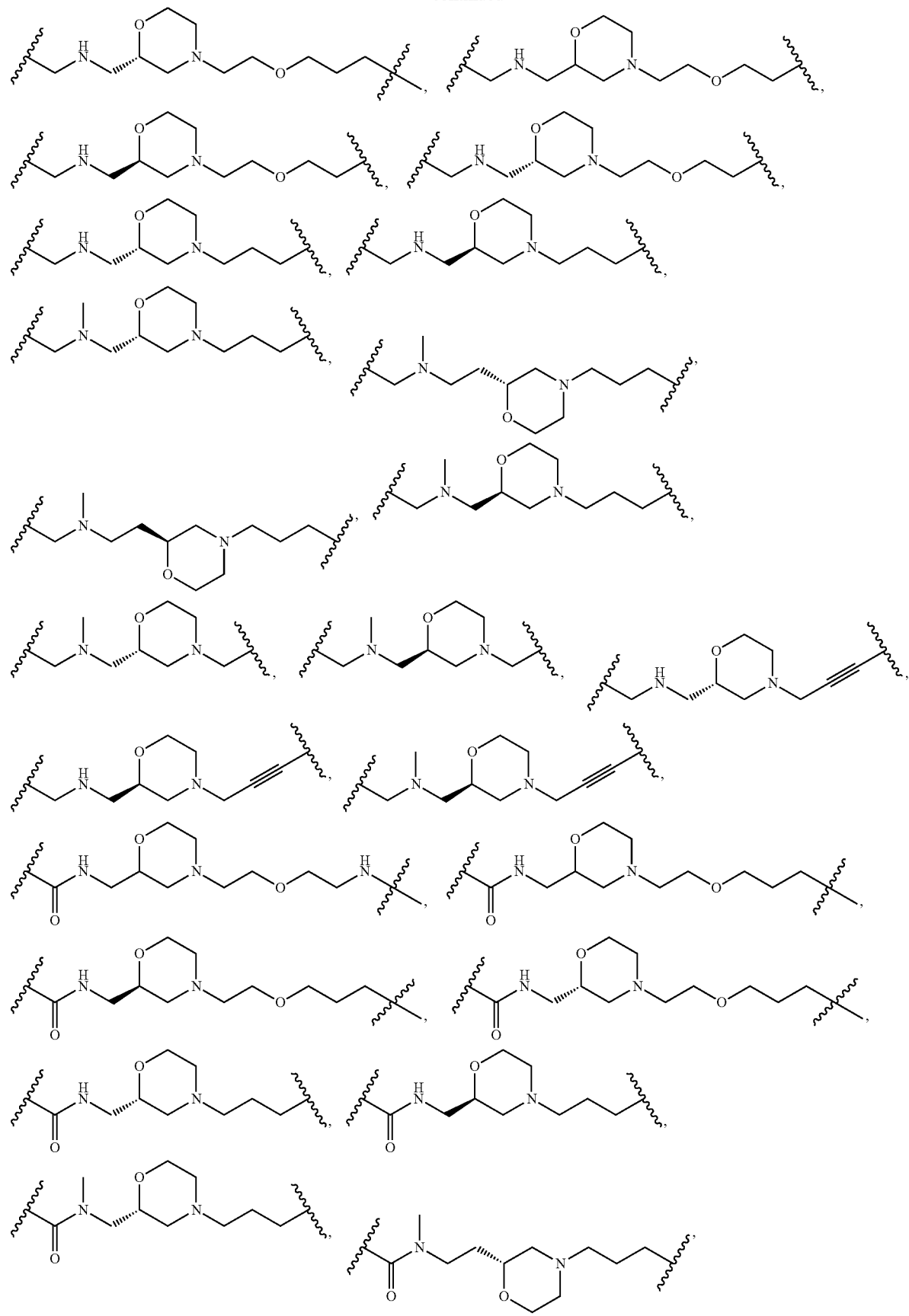

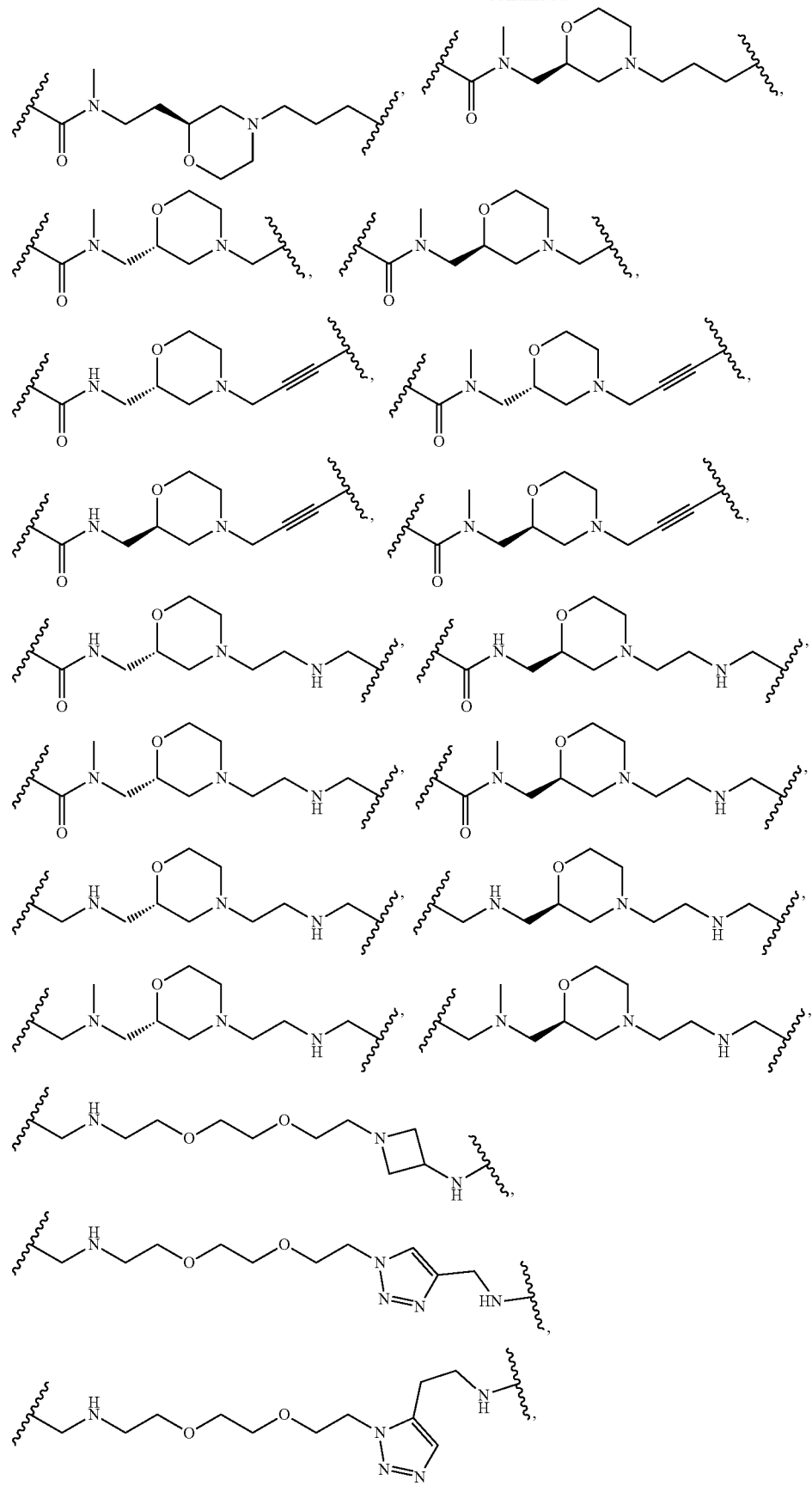

-continued
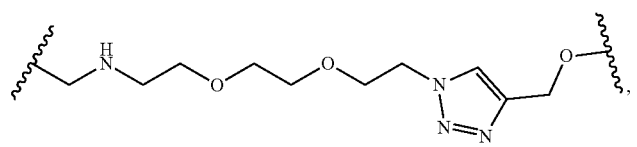
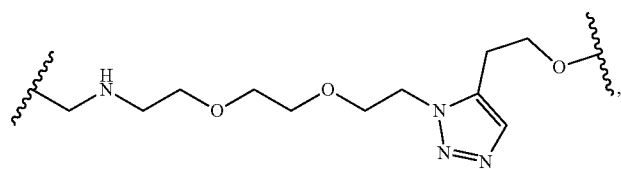
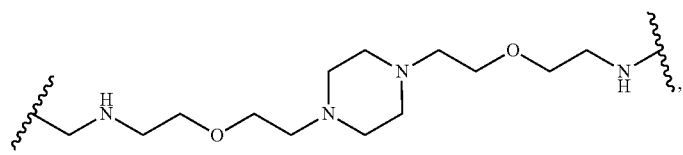
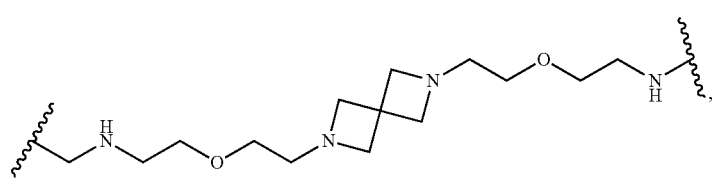
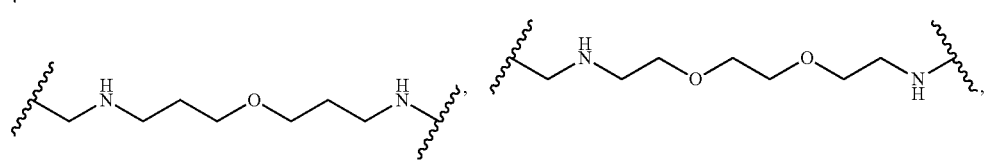
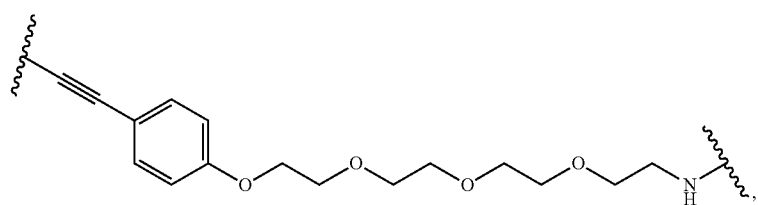
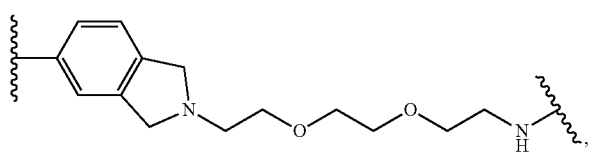
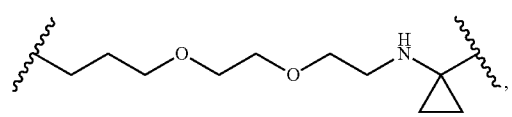
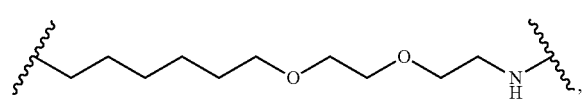
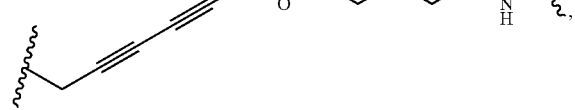
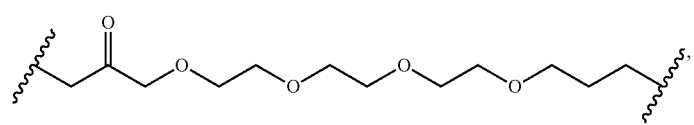
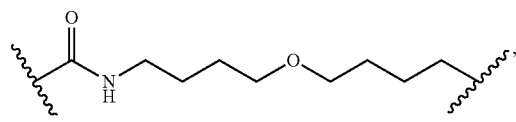
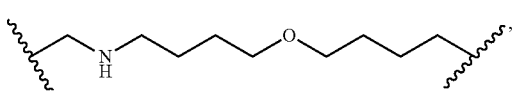

2733    2734
-continued
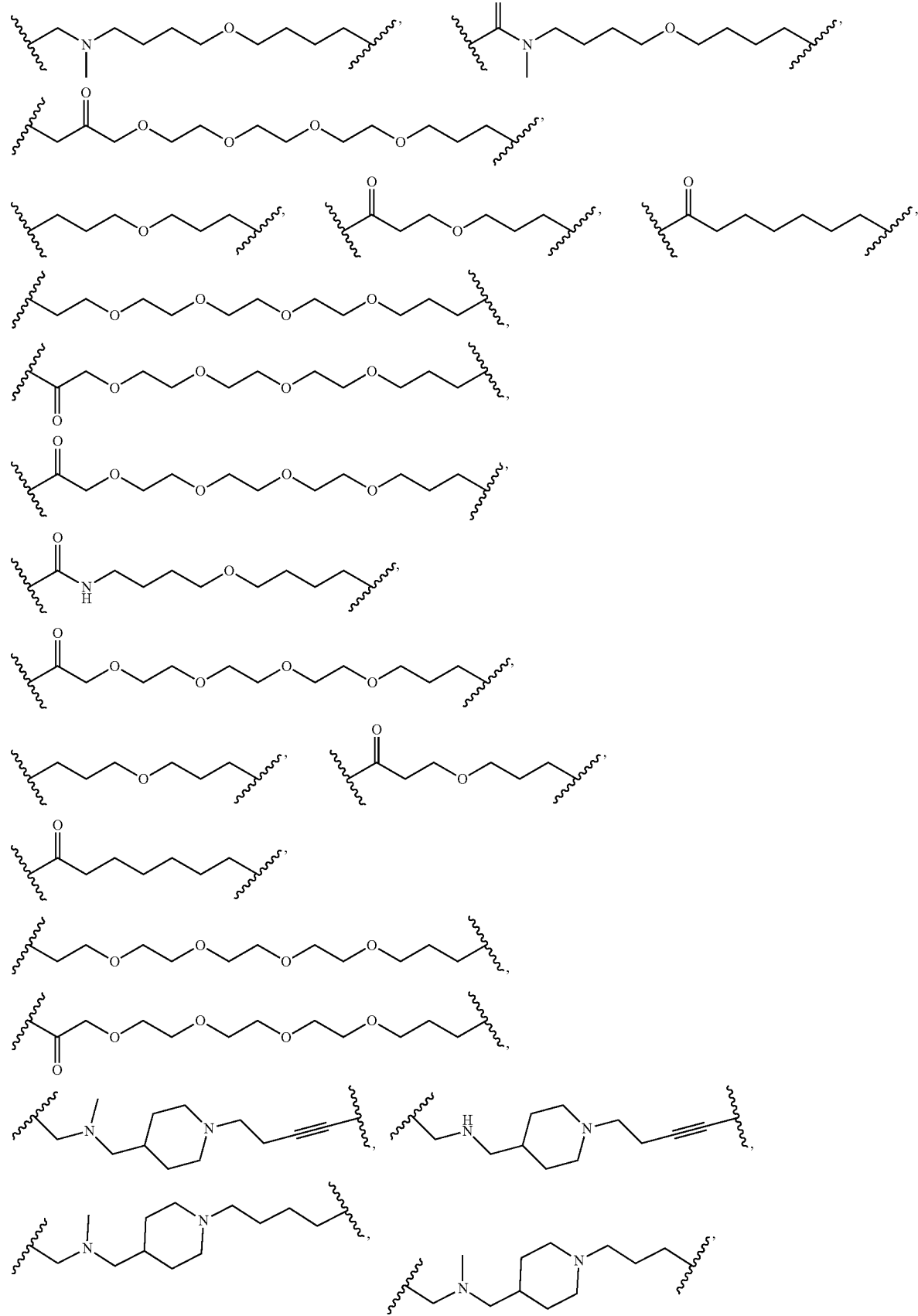

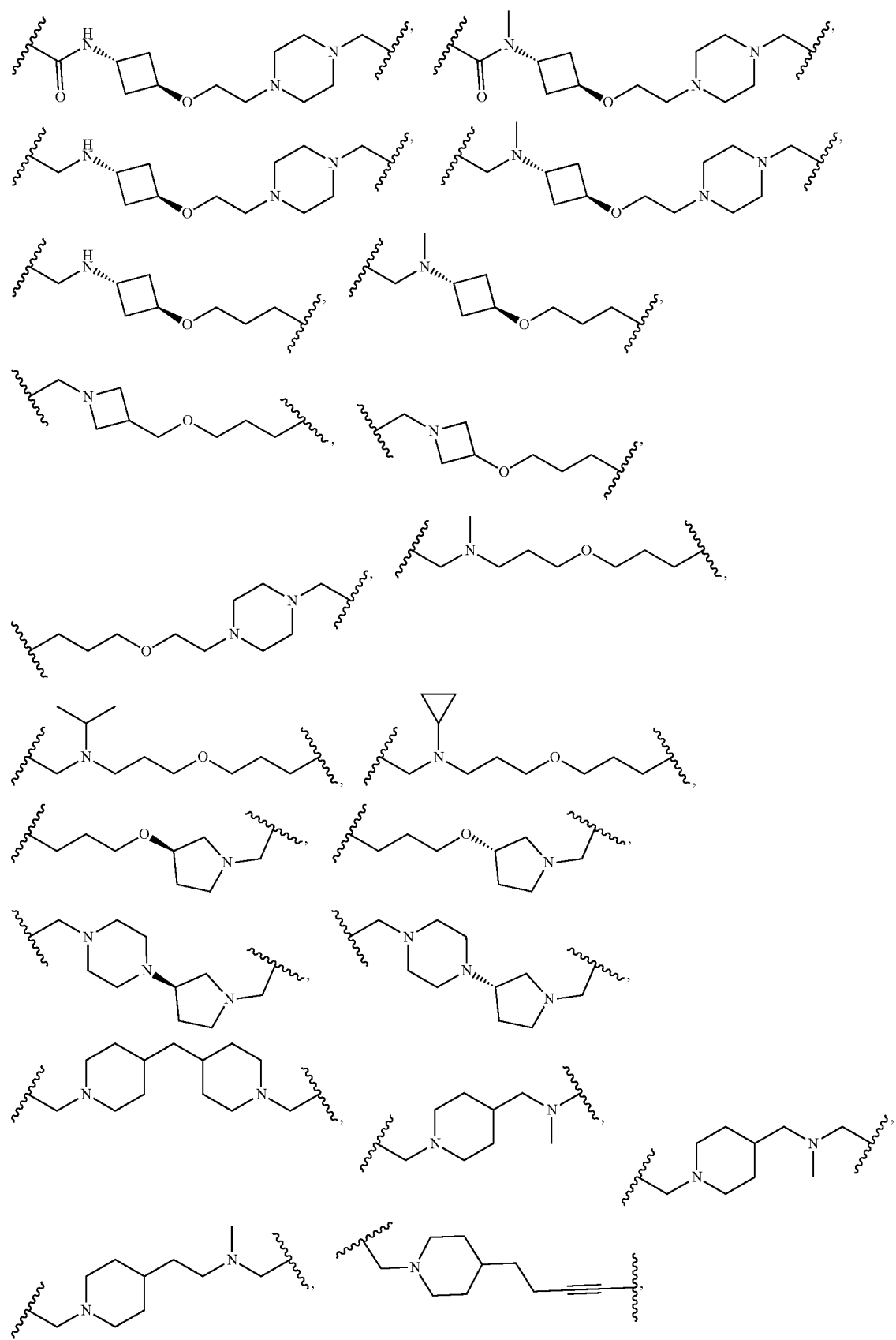

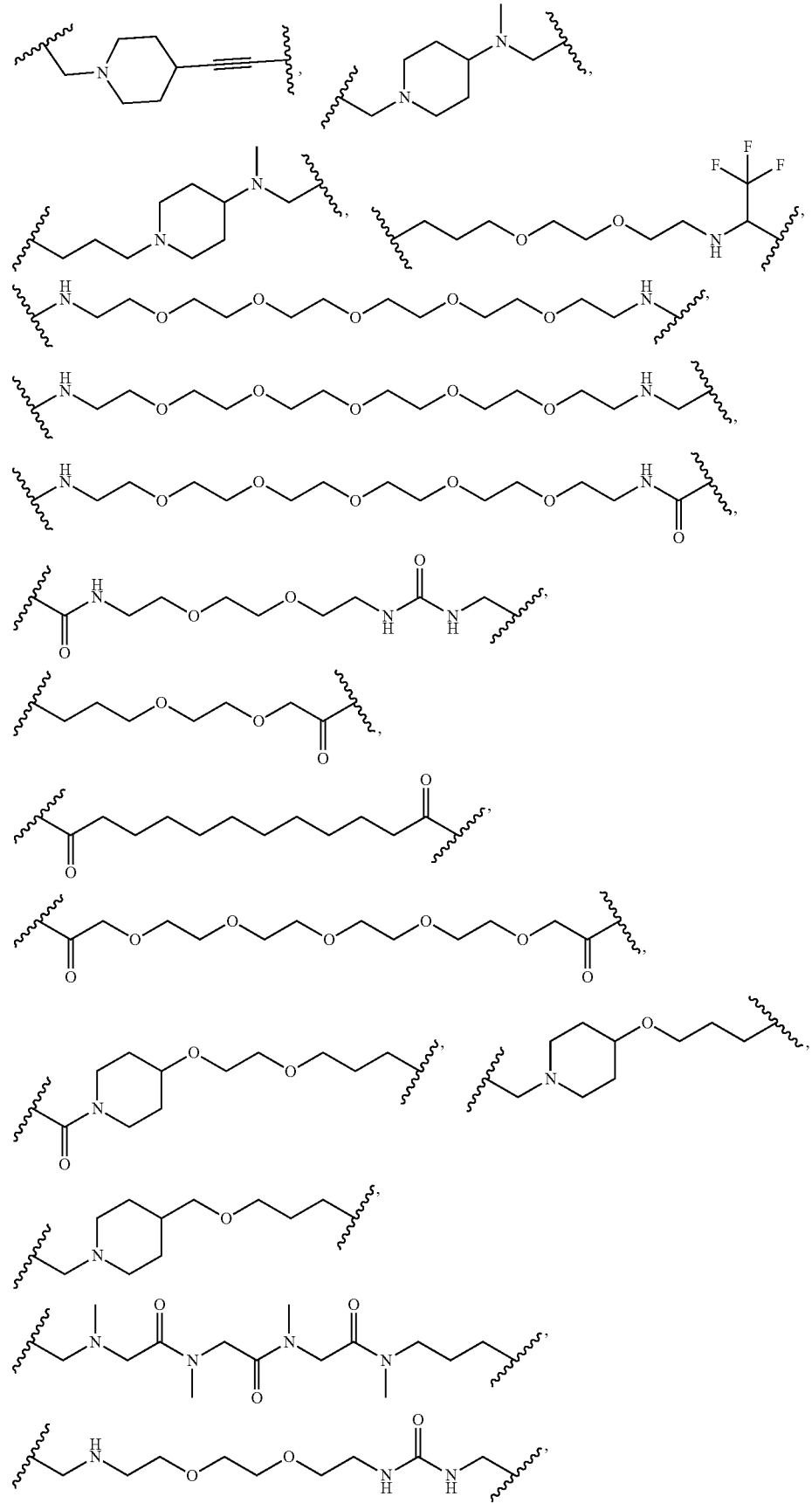

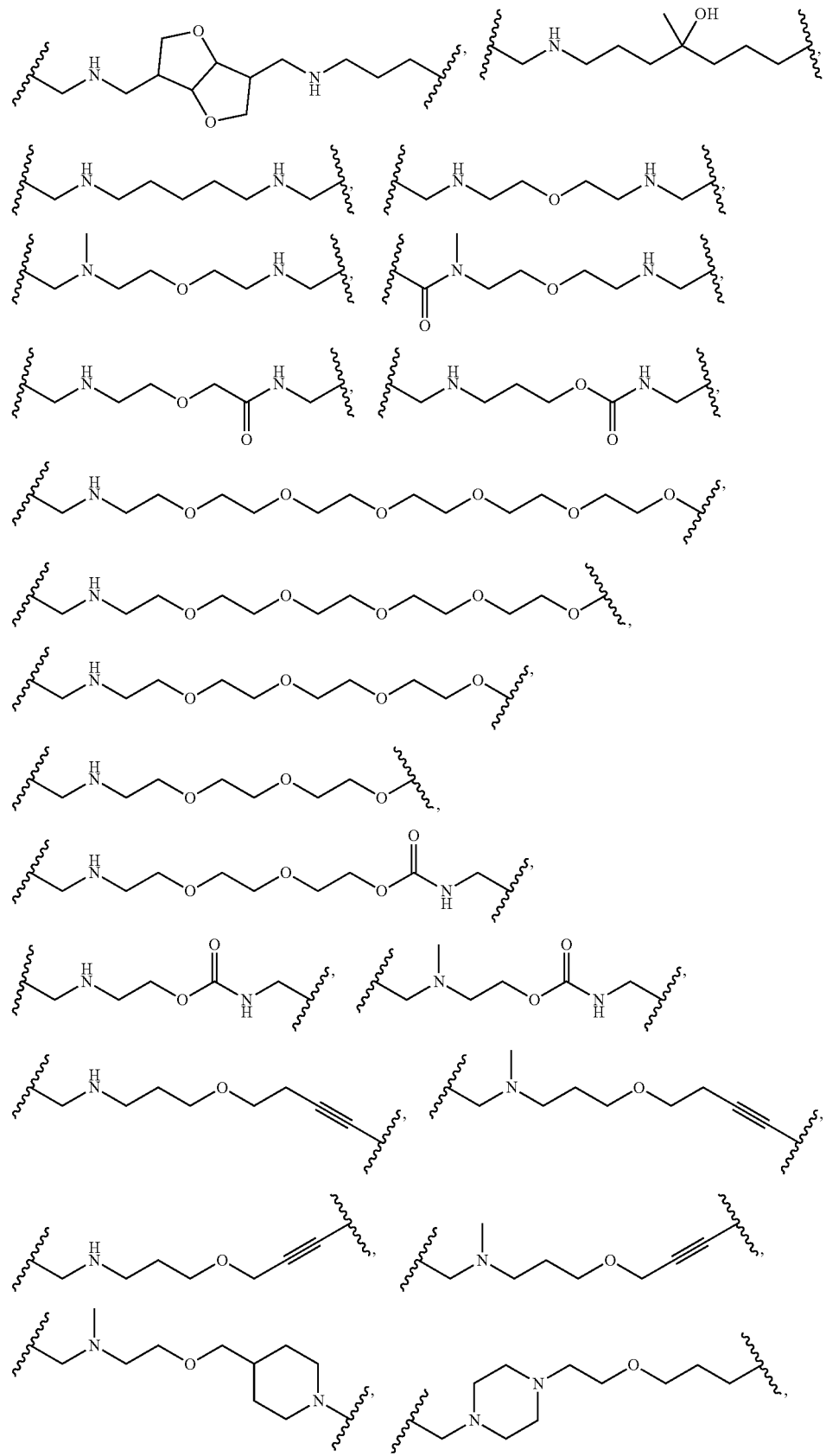

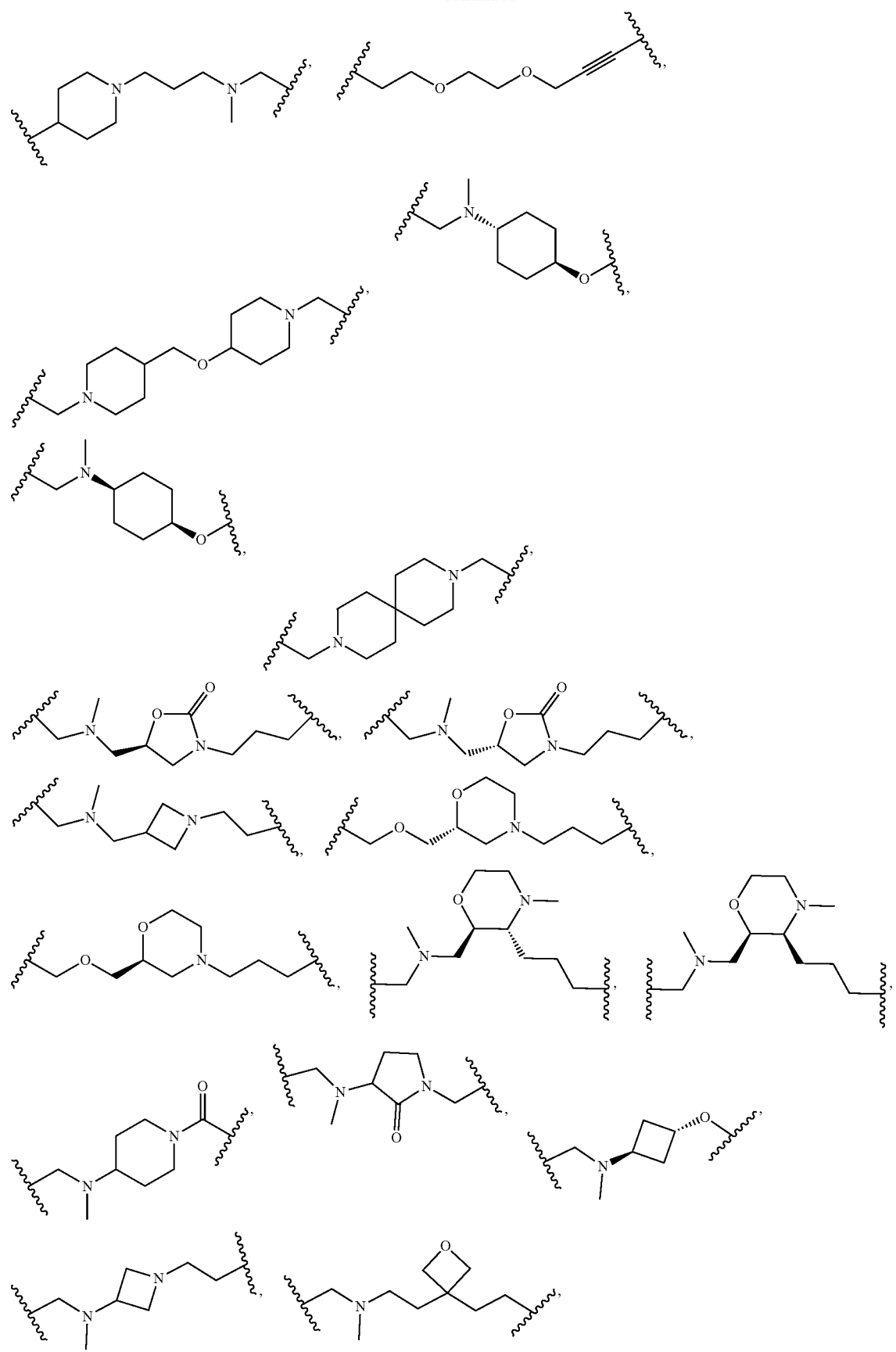

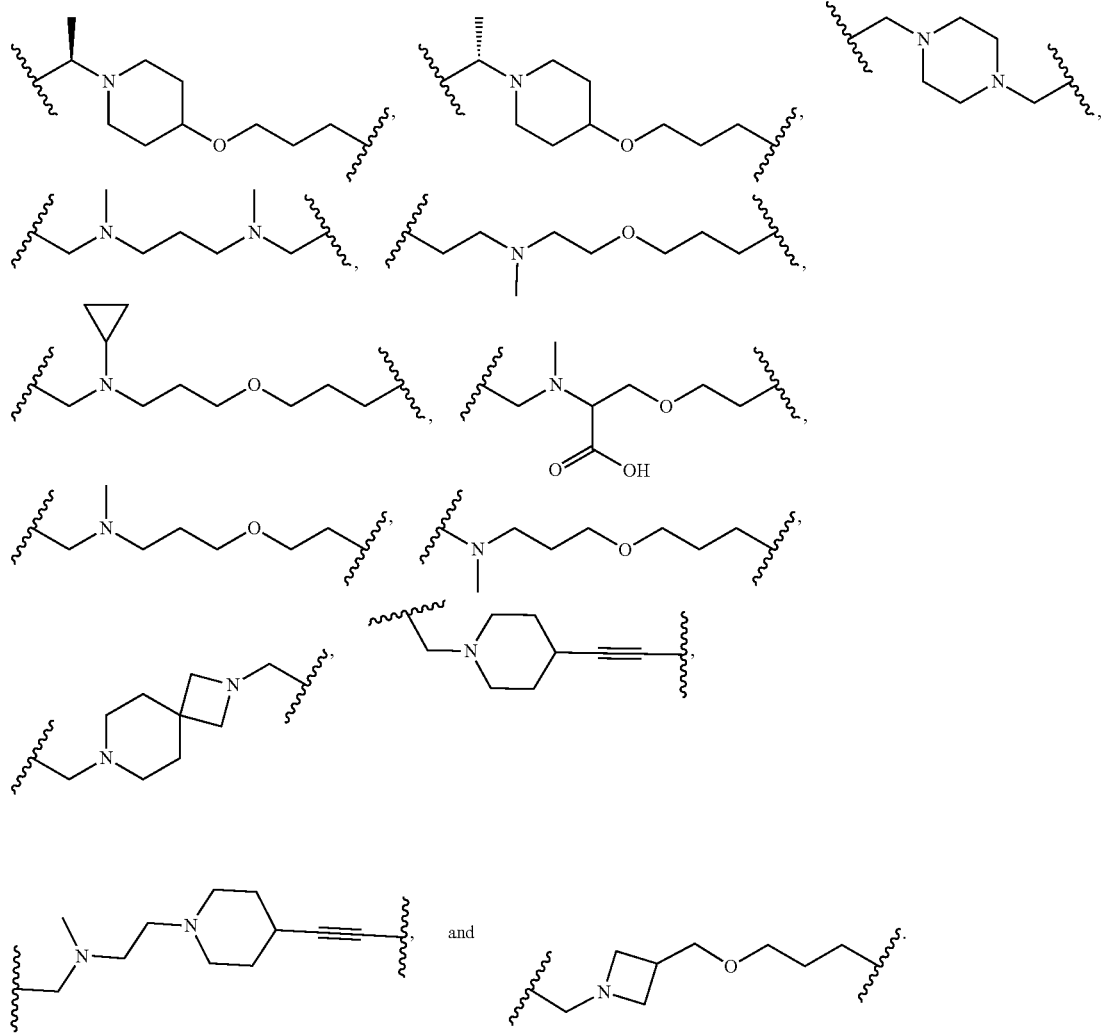
5. The compound of claim 1, wherein said compound is selected from any one of the following compounds, or a pharmaceutically acceptable salt thereof.
| I-# | Structure |
|---|---|
| I-1 | 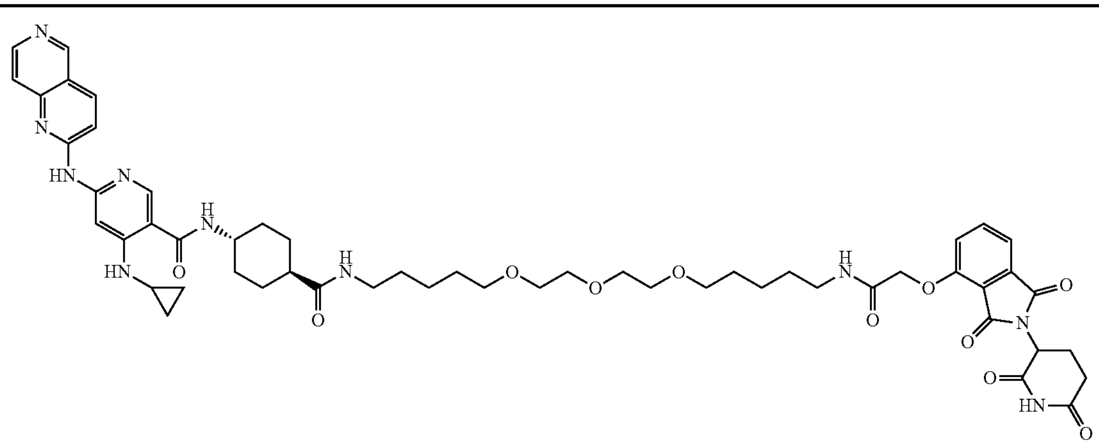 |

| I-# | Structure |
|---|---|
| I-2 | 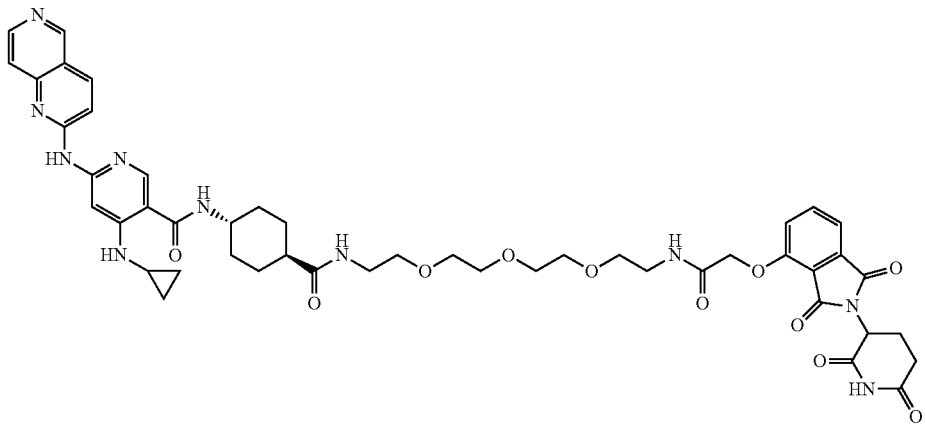 [SMILES: O=C(COc1cccc2c1C(=O)N(C1CCC(=O)NC1=O)C2=O)NCCOCCOCCOCCNC(=O)[C@H]1CC[C@H](NC(=O)c2cnc(Nc3ccc4cnccc4n3)cc2NC2CC2)CC1] |
| I-3 | 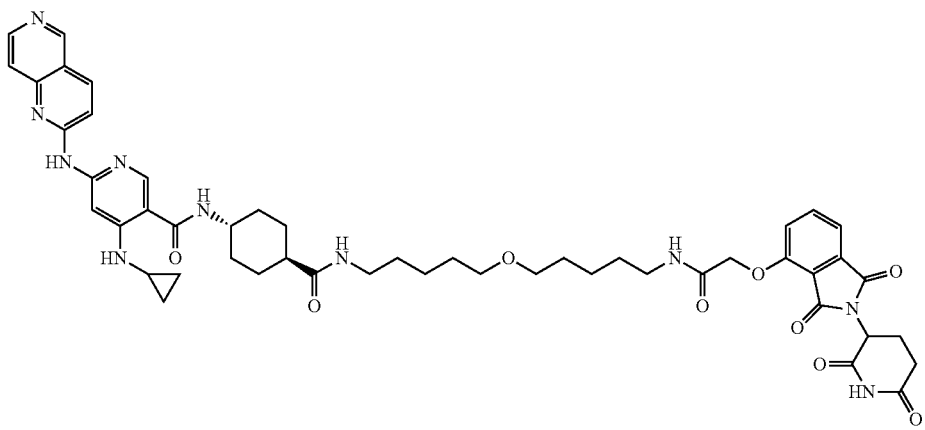 [SMILES: O=C(COc1cccc2c1C(=O)N(C1CCC(=O)NC1=O)C2=O)NCCCCCOCCCCCNC(=O)[C@H]1CC[C@H](NC(=O)c2cnc(Nc3ccc4cnccc4n3)cc2NC2CC2)CC1] |
| I-4 | 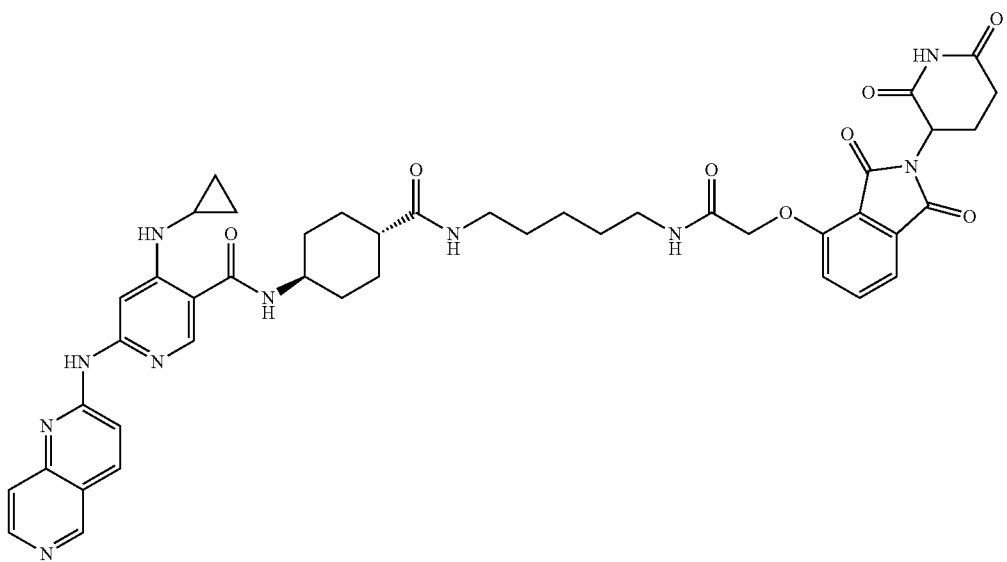 |

| I-# | Structure |
|---|---|
| I-5 | 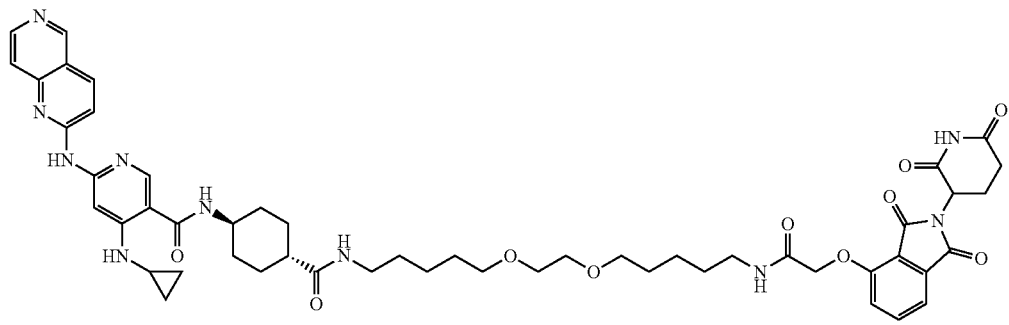 [SMILES: O=C(COc1cccc2c1C(=O)N(C1CCC(=O)NC1=O)C2=O)NCCCCCOCCOCCCCCNC(=O)[C@H]1CC[C@H](NC(=O)c2cnc(Nc3ccc4cnccc4n3)cc2NC2CC2)CC1] |
| I-6 | 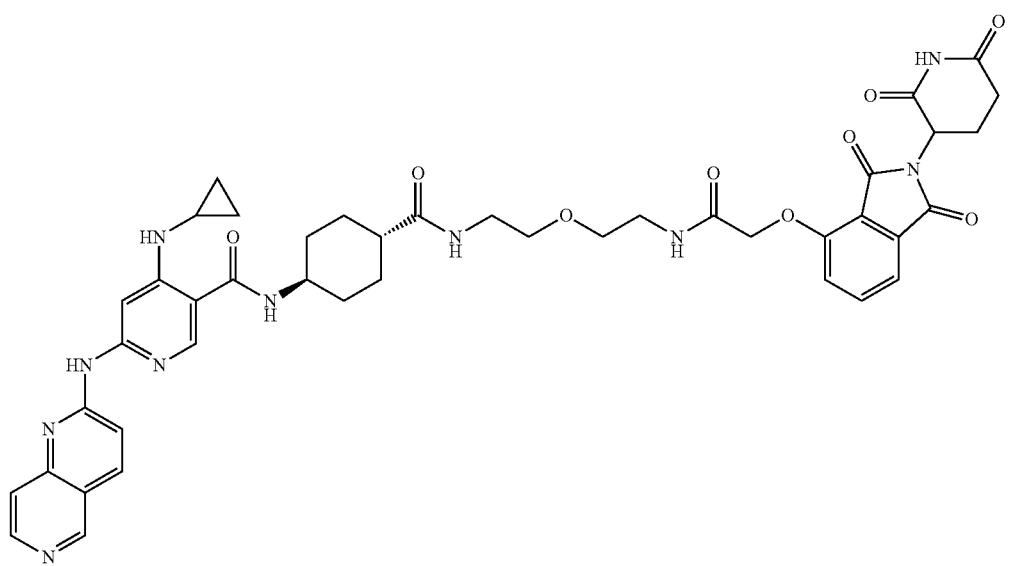 [SMILES: O=C(COc1cccc2c1C(=O)N(C1CCC(=O)NC1=O)C2=O)NCCOCCNC(=O)[C@H]1CC[C@H](NC(=O)c2cnc(Nc3ccc4cnccc4n3)cc2NC2CC2)CC1] |
| I-7 | 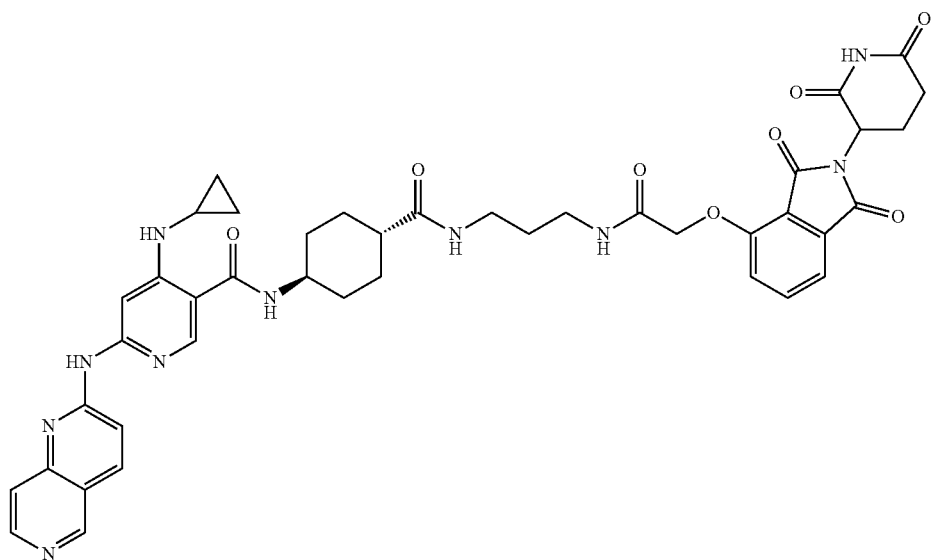 [SMILES: O=C(COc1cccc2c1C(=O)N(C1CCC(=O)NC1=O)C2=O)NCCCNC(=O)[C@H]1CC[C@H](NC(=O)c2cnc(Nc3ccc4cnccc4n3)cc2NC2CC2)CC1] |

| I-# | Structure |
|---|---|
| I-8 | 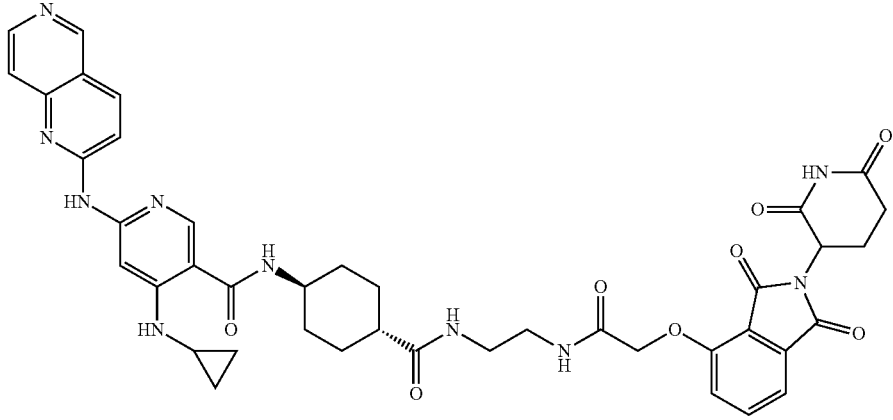 [SMILES: O=C(COc1cccc2c1C(=O)N(C1CCC(=O)NC1=O)C2=O)NCCNC(=O)[C@H]1CC[C@H](NC(=O)c2cnc(Nc3ccc4cnccc4n3)cc2NC2CC2)CC1] |
| I-9 | 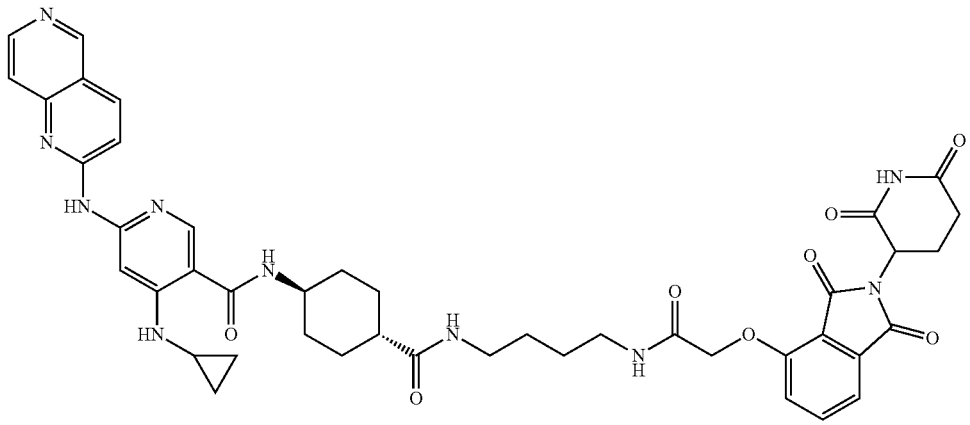 [SMILES: O=C(COc1cccc2c1C(=O)N(C1CCC(=O)NC1=O)C2=O)NCCCCNC(=O)[C@H]1CC[C@H](NC(=O)c2cnc(Nc3ccc4cnccc4n3)cc2NC2CC2)CC1] |
| I-10 | 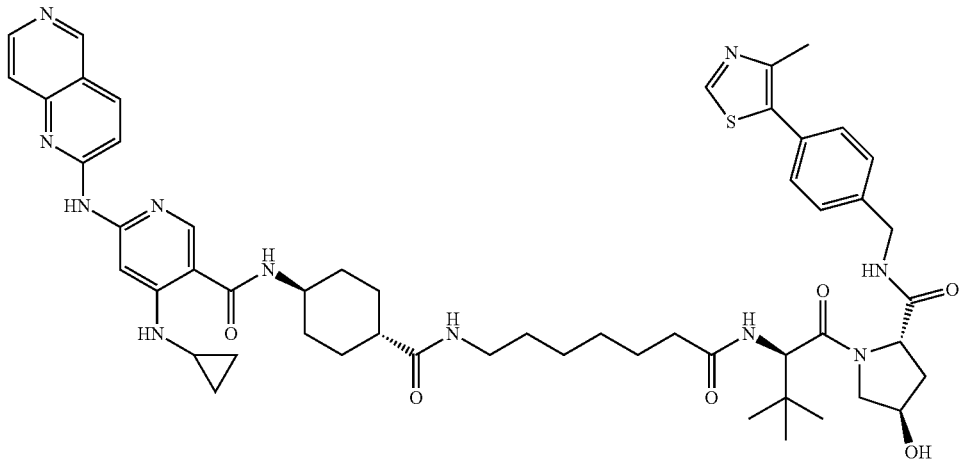 [SMILES: Cc1ncsc1-c1ccc(CNC(=O)[C@@H]2C[C@@H](O)CN2C(=O)[C@H](NC(=O)CCCCCCNC(=O)[C@H]2CC[C@H](NC(=O)c3cnc(Nc4ccc5cnccc5n4)cc3NC3CC3)CC2)C(C)(C)C)cc1] |

| I-# | Structure |
|---|---|
| I-11 | 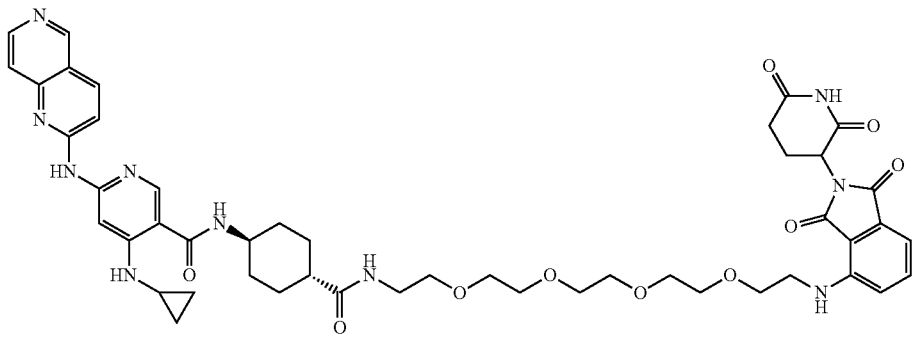 [SMILES: O=C1CCC(N2C(=O)c3cccc(NCCOCCOCCOCCOCCNC(=O)[C@H]4CC[C@H](NC(=O)c5cnc(Nc6ccc7cnccc7n6)cc5NC5CC5)CC4)c3C2=O)C(=O)N1] |
| I-12 | 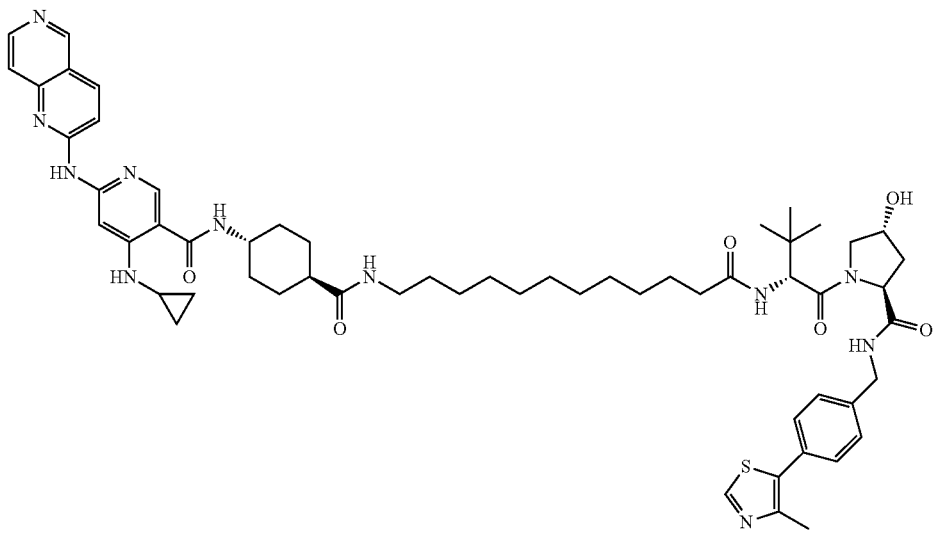 [SMILES: Cc1ncsc1-c1ccc(CNC(=O)[C@@H]2C[C@@H](O)CN2C(=O)[C@H](NC(=O)CCCCCCCCCCCNC(=O)[C@H]2CC[C@H](NC(=O)c3cnc(Nc4ccc5cnccc5n4)cc3NC3CC3)CC2)C(C)(C)C)cc1] |
| I-13 | 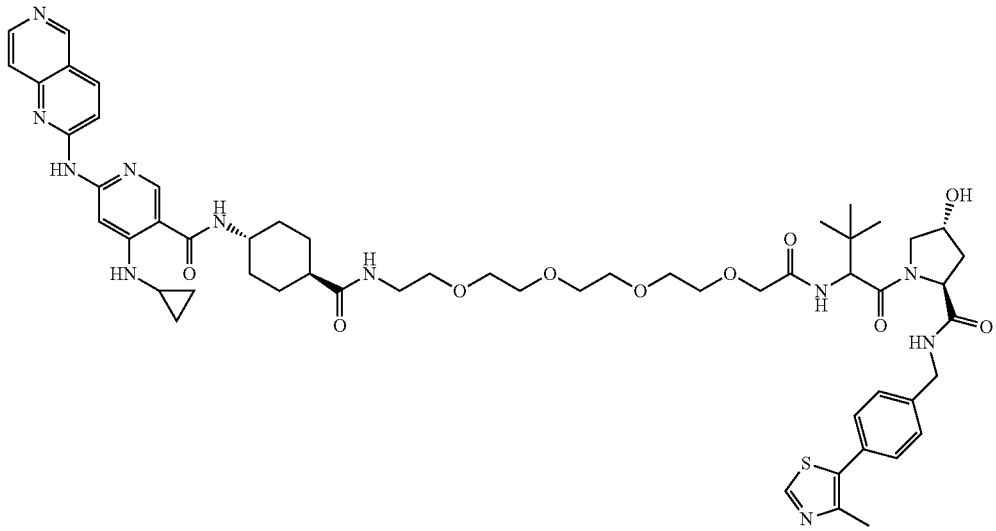 [SMILES: Cc1ncsc1-c1ccc(CNC(=O)[C@@H]2C[C@@H](O)CN2C(=O)C(NC(=O)COCCOCCOCCOCCNC(=O)[C@H]2CC[C@H](NC(=O)c3cnc(Nc4ccc5cnccc5n4)cc3NC3CC3)CC2)C(C)(C)C)cc1] |

-continued
| I-# | Structure |
|---|---|
| I-14 | 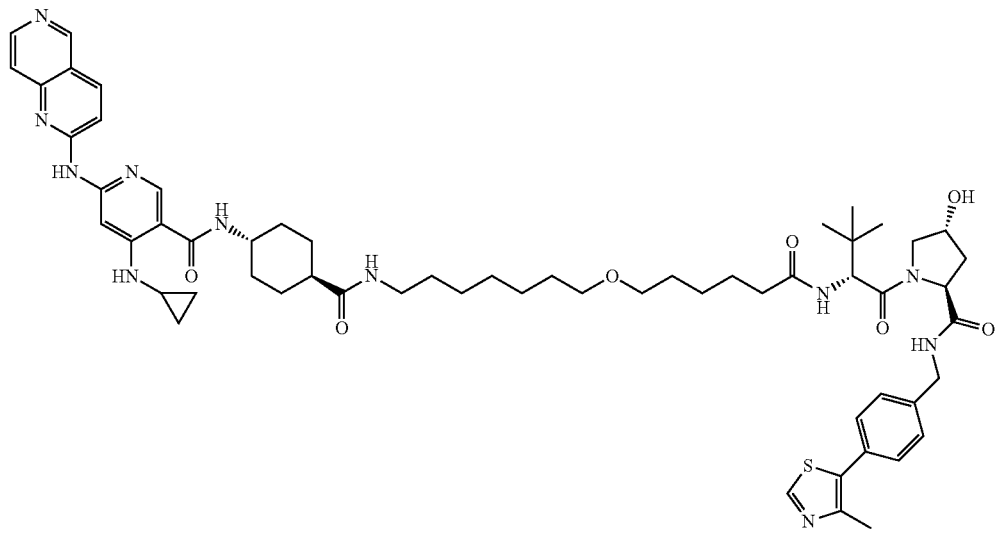 [SMILES: Cc1ncsc1-c1ccc(CNC(=O)[C@@H]2C[C@@H](O)CN2C(=O)[C@H](NC(=O)CCCCCOCCCCCCCNC(=O)[C@H]2CC[C@H](NC(=O)c3cnc(Nc4ccc5cnccc5n4)cc3NC3CC3)CC2)C(C)(C)C)cc1] |
| I-15 | 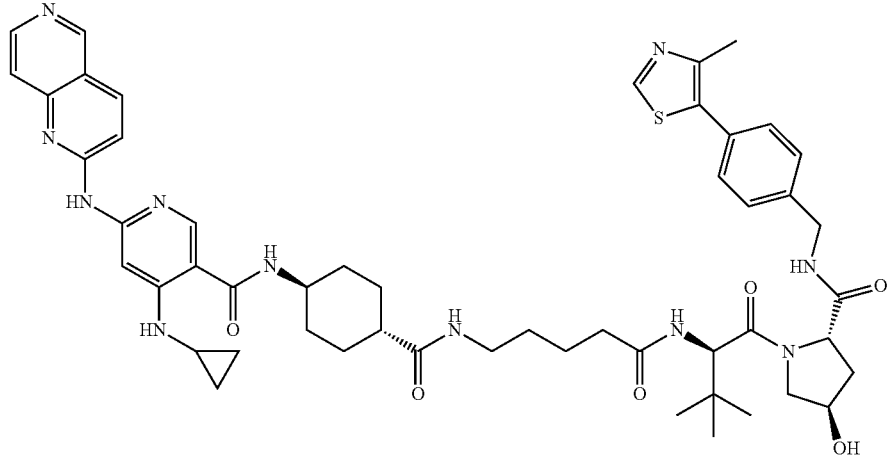 [SMILES: Cc1ncsc1-c1ccc(CNC(=O)[C@@H]2C[C@@H](O)CN2C(=O)[C@H](NC(=O)CCCCNC(=O)[C@H]2CC[C@H](NC(=O)c3cnc(Nc4ccc5cnccc5n4)cc3NC3CC3)CC2)C(C)(C)C)cc1] |
| I-16 | 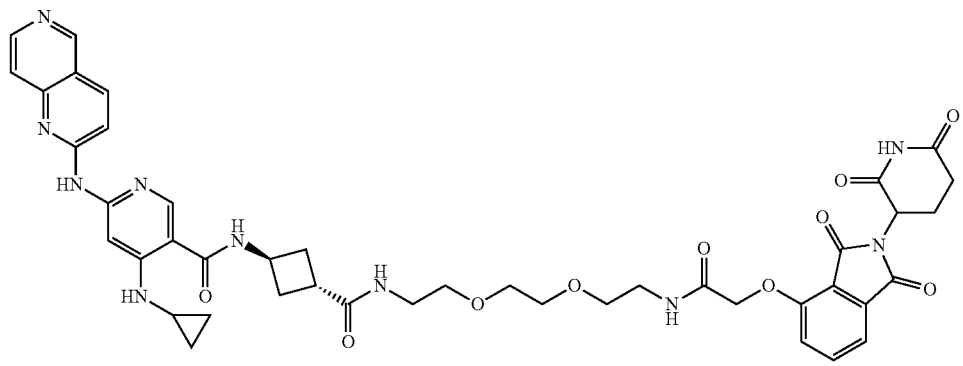 [SMILES: O=C(COc1cccc2c1C(=O)N(C1CCC(=O)NC1=O)C2=O)NCCOCCOCCNC(=O)[C@H]1C[C@H](NC(=O)c2cnc(Nc3ccc4cnccc4n3)cc2NC2CC2)C1] |

| I-# | Structure |
|---|---|
| I-19 | 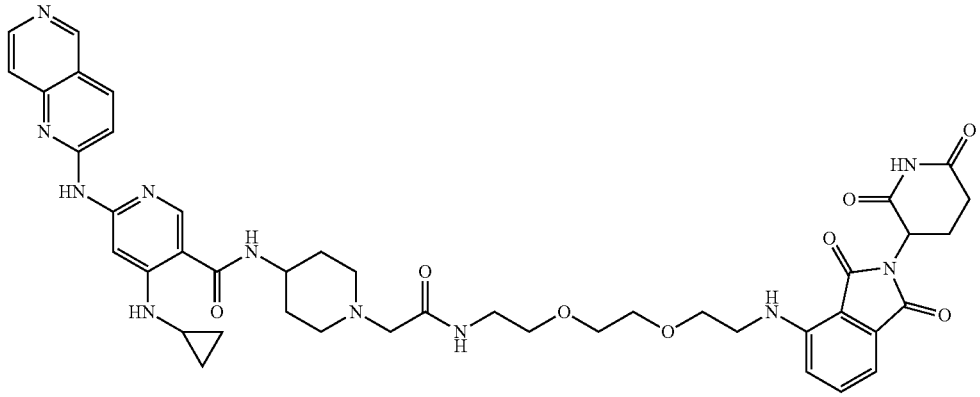 [SMILES: O=C(CN1CCC(NC(=O)c2cnc(Nc3ccc4cnccc4n3)cc2NC2CC2)CC1)NCCOCCOCCNc1cccc2c1C(=O)N(C1CCC(=O)NC1=O)C2=O] |
| I-20 | 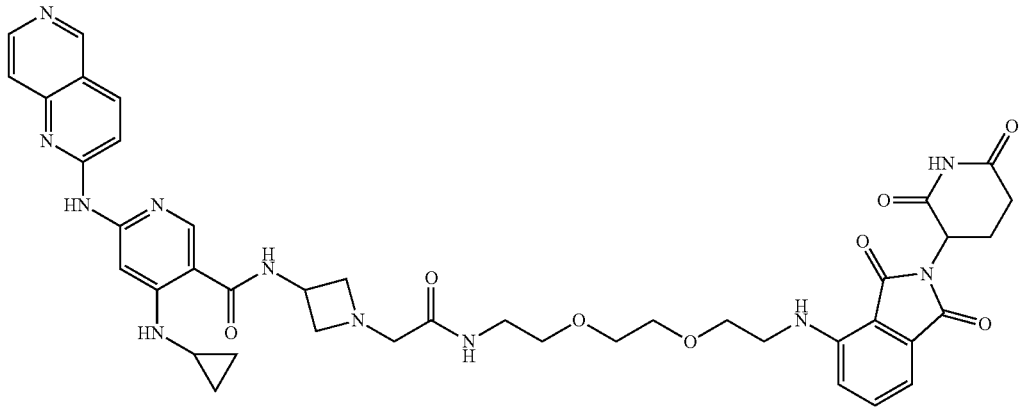 [SMILES: O=C(CN1CC(NC(=O)c2cnc(Nc3ccc4cnccc4n3)cc2NC2CC2)C1)NCCOCCOCCNc1cccc2c1C(=O)N(C1CCC(=O)NC1=O)C2=O] |
| I-23 | 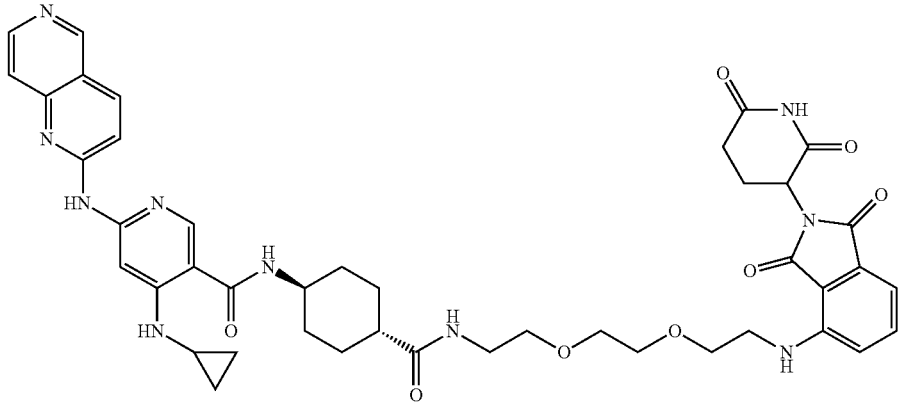 [SMILES: O=C1CCC(N2C(=O)c3cccc(NCCOCCOCCNC(=O)[C@H]4CC[C@H](NC(=O)c5cnc(Nc6ccc7cnccc7n6)cc5NC5CC5)CC4)c3C2=O)C(=O)N1] |
| I-24 | 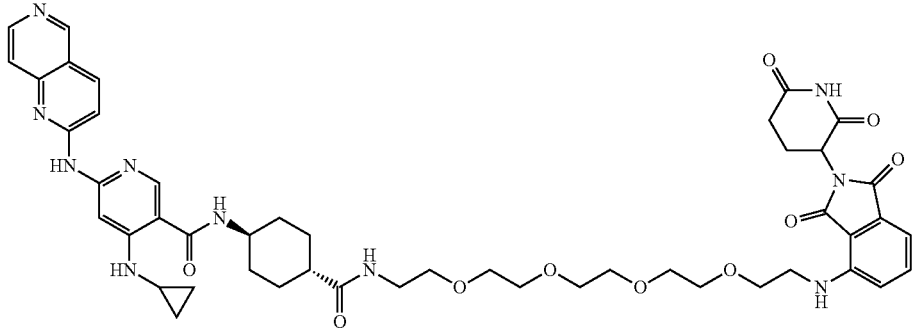 [SMILES: O=C1CCC(N2C(=O)c3cccc(NCCOCCOCCOCCOCCNC(=O)[C@H]4CC[C@H](NC(=O)c5cnc(Nc6ccc7cnccc7n6)cc5NC5CC5)CC4)c3C2=O)C(=O)N1] |

| I-# | Structure |
|---|---|
| I-25 | 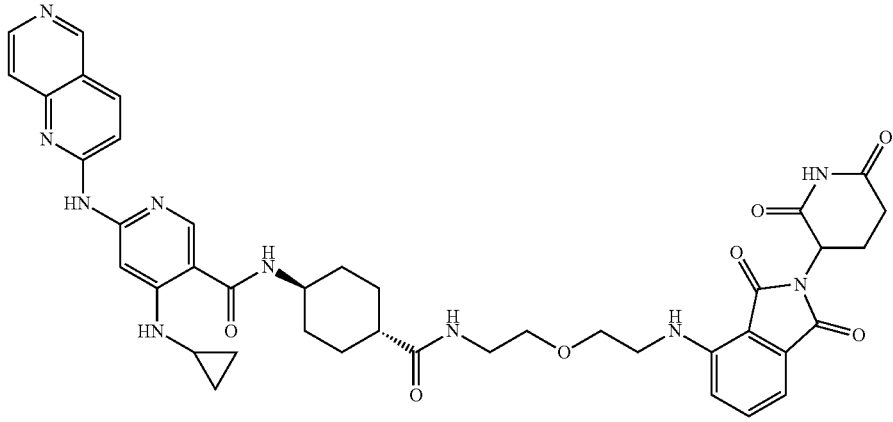 [SMILES: O=C1CCC(N2C(=O)c3cccc(NCCOCCNC(=O)[C@H]4CC[C@H](NC(=O)c5cnc(Nc6ccc7cnccc7n6)cc5NC5CC5)CC4)c3C2=O)C(=O)N1] |
| I-26 | 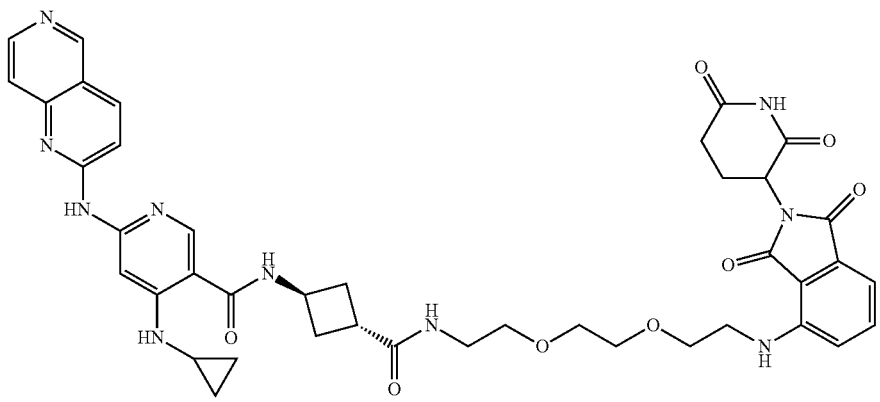 [SMILES: O=C1CCC(N2C(=O)c3cccc(NCCOCCOCCNC(=O)[C@H]4C[C@H](NC(=O)c5cnc(Nc6ccc7cnccc7n6)cc5NC5CC5)C4)c3C2=O)C(=O)N1] |
| I-30 | 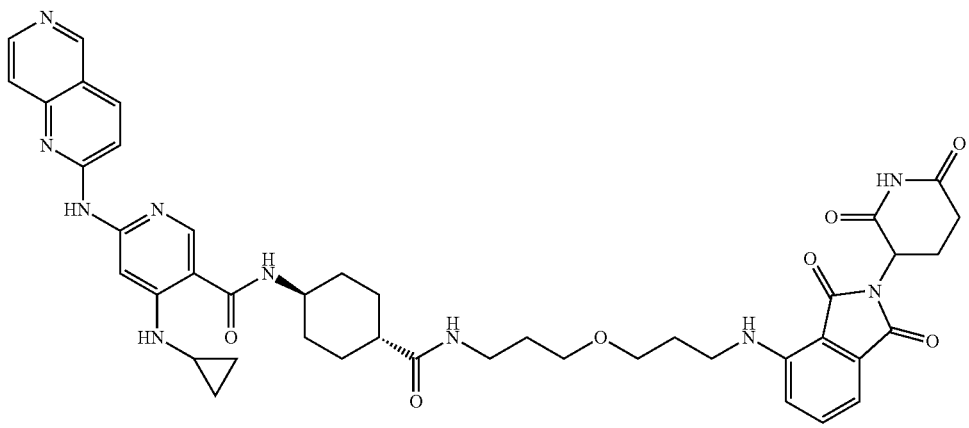 [SMILES: O=C1CCC(N2C(=O)c3cccc(NCCCOCCCNC(=O)[C@H]4CC[C@H](NC(=O)c5cnc(Nc6ccc7cnccc7n6)cc5NC5CC5)CC4)c3C2=O)C(=O)N1] |

| I-# | Structure |
|---|---|
| I-31 | 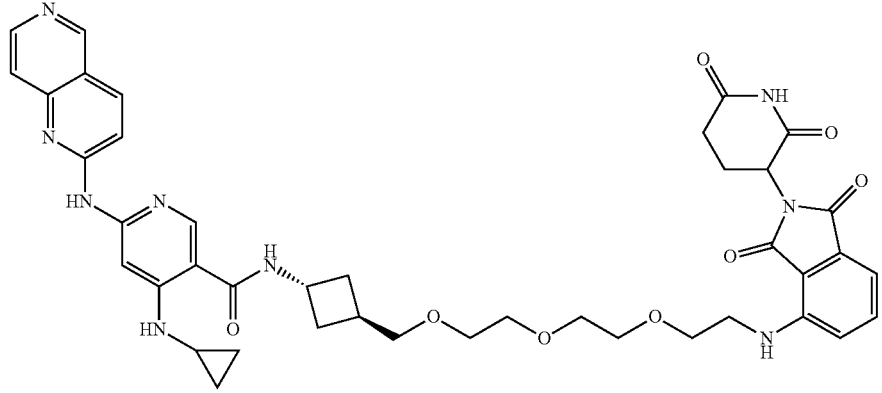 [SMILES: O=C1CCC(N2C(=O)c3cccc(NCCOCCOCCOC[C@H]4C[C@H](NC(=O)c5cnc(Nc6ccc7cnccc7n6)cc5NC5CC5)C4)c3C2=O)C(=O)N1] |
| I-40 | 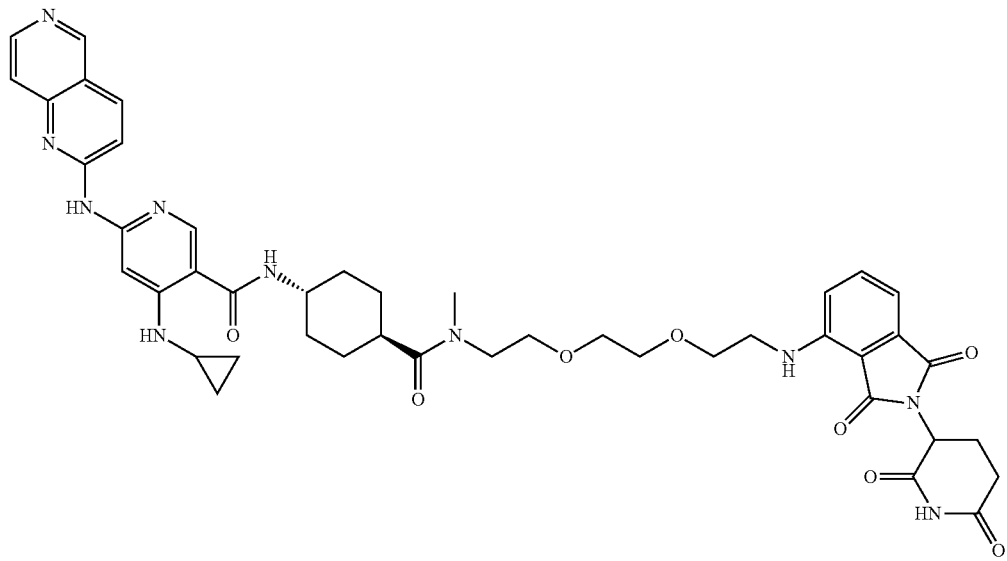 [SMILES: CN(CCOCCOCCNc1cccc2c1C(=O)N(C1CCC(=O)NC1=O)C2=O)C(=O)[C@H]1CC[C@H](NC(=O)c2cnc(Nc3ccc4cnccc4n3)cc2NC2CC2)CC1] |
| I-41 | 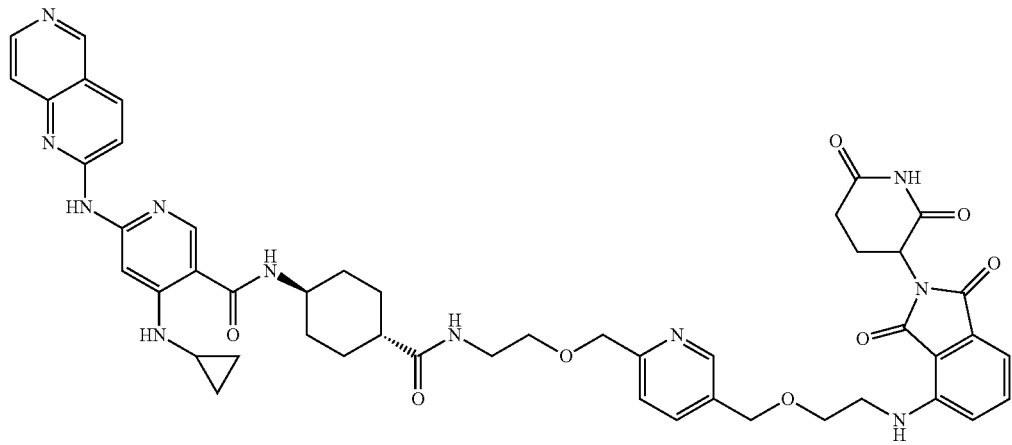 [SMILES: O=C1CCC(N2C(=O)c3cccc(NCCOCc4ccc(COCCNC(=O)[C@H]5CC[C@H](NC(=O)c6cnc(Nc7ccc8cnccc8n7)cc6NC6CC6)CC5)nc4)c3C2=O)C(=O)N1] |

| I-# | Structure |
|---|---|
| I-43 | 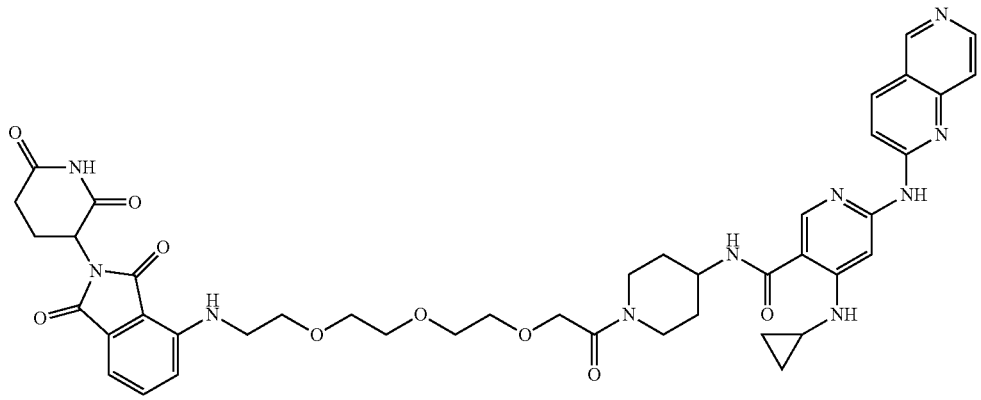 [SMILES: O=C1CCC(N2C(=O)c3cccc(NCCOCCOCCOCC(=O)N4CCC(NC(=O)c5cnc(Nc6ccc7cnccc7n6)cc5NC5CC5)CC4)c3C2=O)C(=O)N1] |
| I-44 | 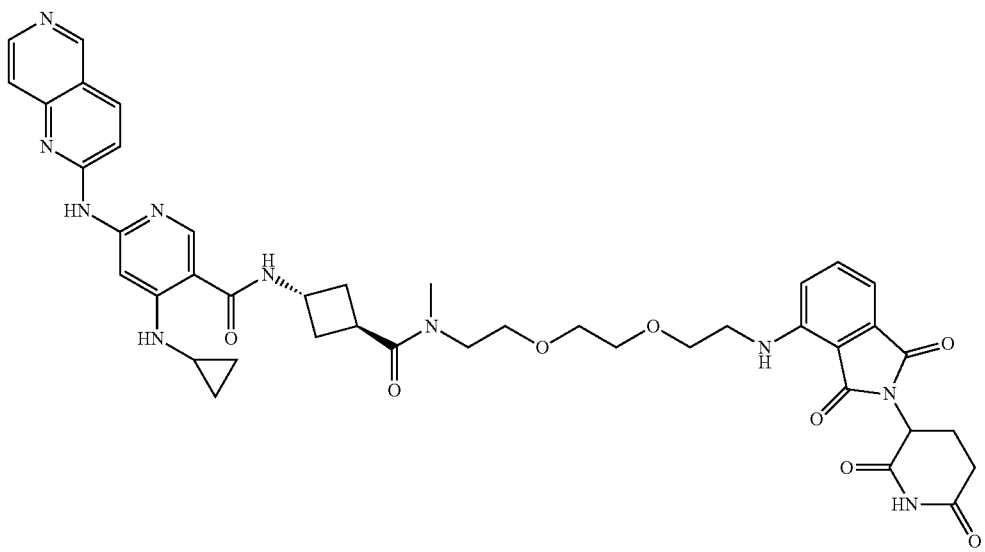 [SMILES: CN(CCOCCOCCNc1cccc2c1C(=O)N(C1CCC(=O)NC1=O)C2=O)C(=O)[C@H]1C[C@H](NC(=O)c2cnc(Nc3ccc4cnccc4n3)cc2NC2CC2)C1] |
| I-47 | 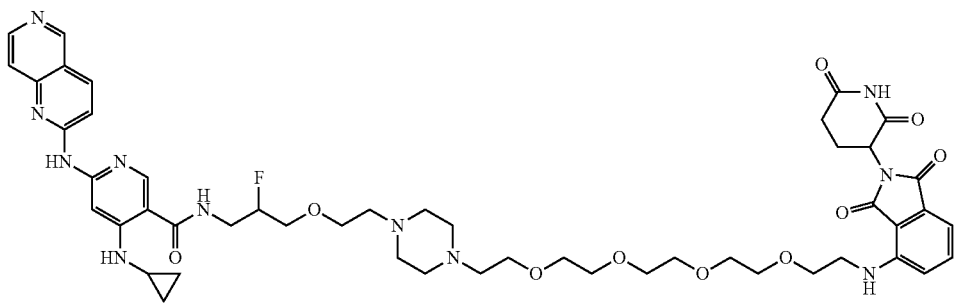 [SMILES: O=C1CCC(N2C(=O)c3cccc(NCCOCCOCCOCCOCCN4CCN(CCOCC(F)CNC(=O)c5cnc(Nc6ccc7cnccc7n6)cc5NC5CC5)CC4)c3C2=O)C(=O)N1] |
| I-48 | 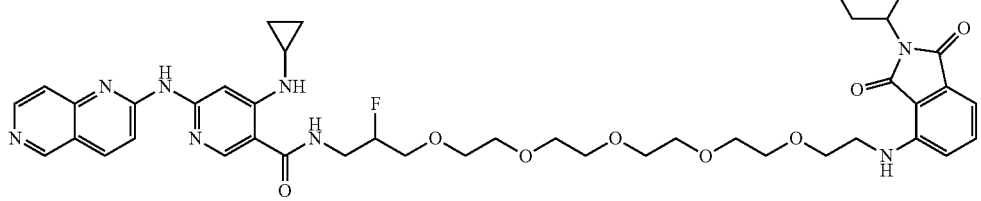 |

| I-# | Structure |
|---|---|
| I-49 | 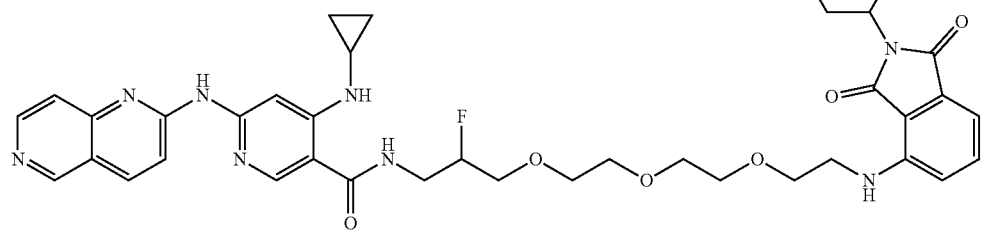 |
| I-50 | 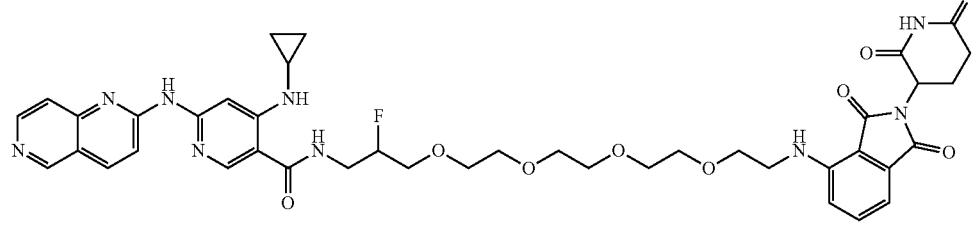 |
| I-51 | 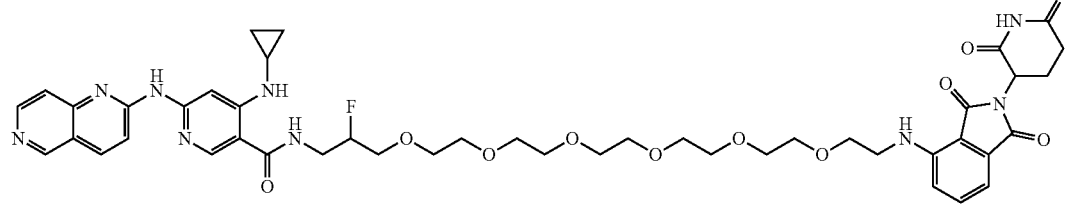 |
| I-52 | 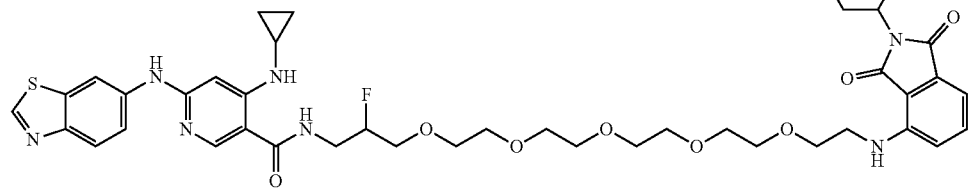 |
| I-54 | 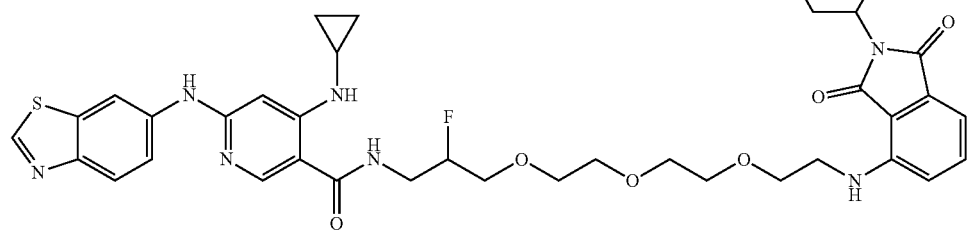 |

-continued
| I-# | Structure |
|---|---|
| I-55 | 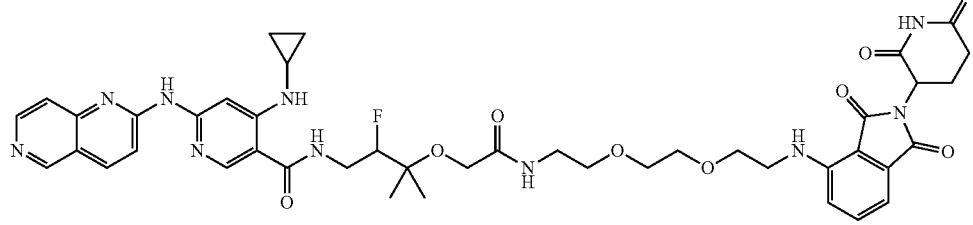 |
| I-56 | 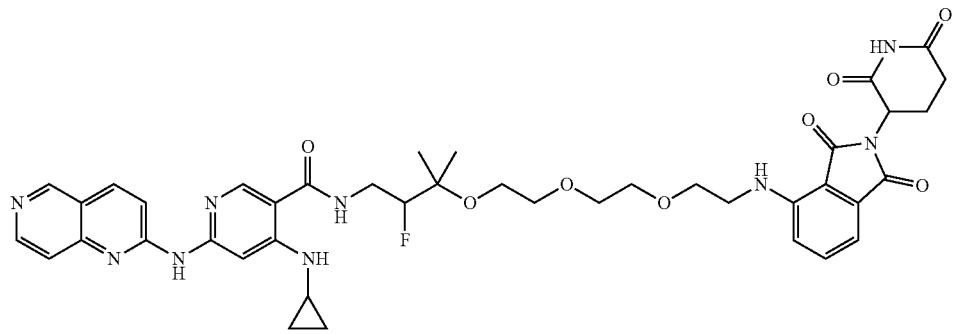 [SMILES: CC(C)(OCCOCCOCCNc1cccc2c1C(=O)N(C1CCC(=O)NC1=O)C2=O)C(F)CNC(=O)c1cnc(Nc2ccc3cnccc3n2)cc1NC1CC1] |
| I-58 | 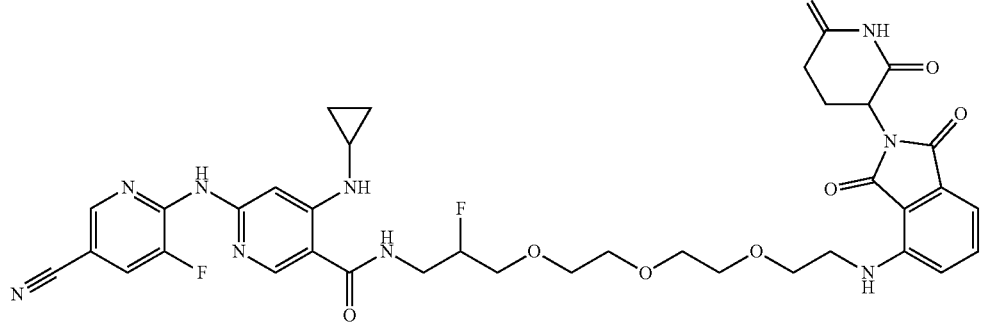 |
| I-61 | 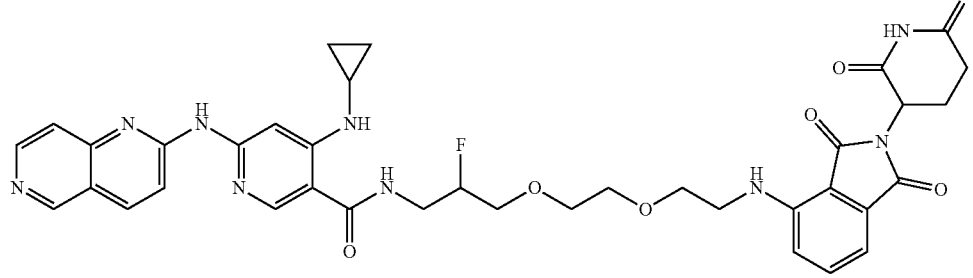 |
| I-62 | 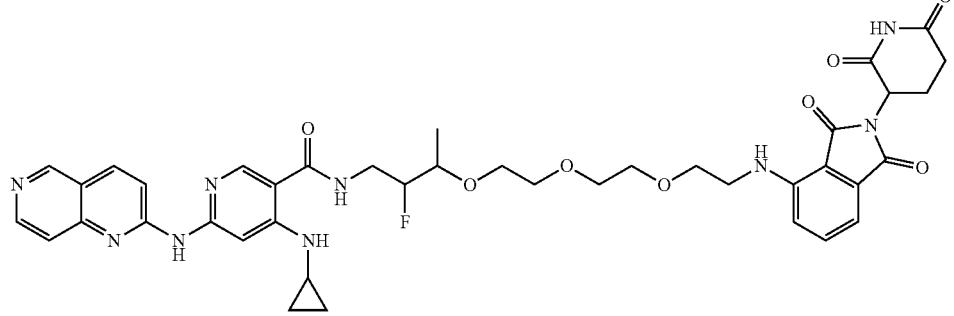 |

| I-# | Structure |
|---|---|
| I-64 | 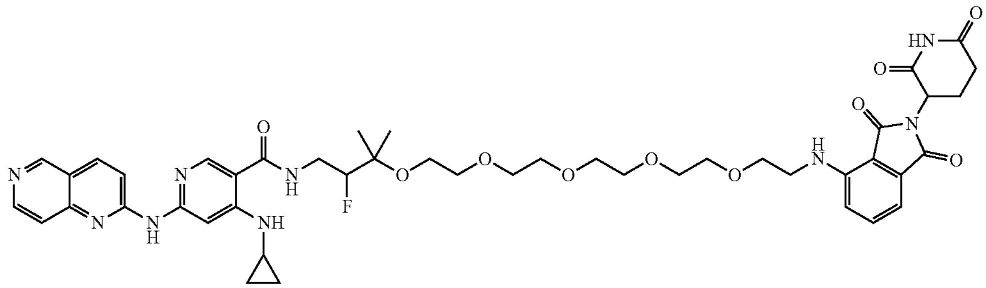 [SMILES: CC(C)(OCCOCCOCCOCCOCCNc1cccc2c1C(=O)N(C1CCC(=O)NC1=O)C2=O)C(F)CNC(=O)c1cnc(Nc2ccc3cnccc3n2)cc1NC1CC1] |
| I-65 | 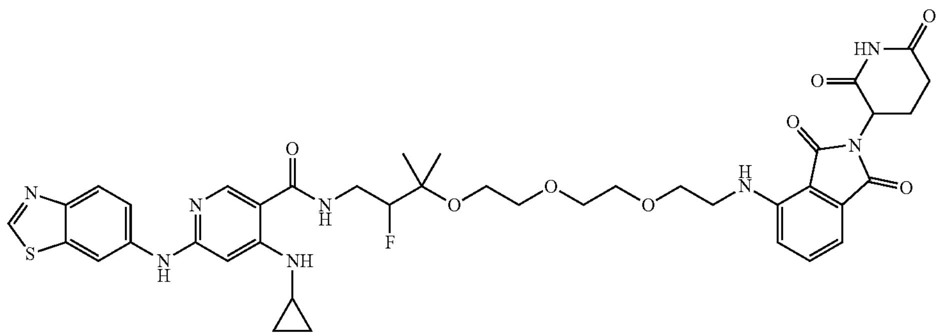 [SMILES: CC(C)(OCCOCCOCCNc1cccc2c1C(=O)N(C1CCC(=O)NC1=O)C2=O)C(F)CNC(=O)c1cnc(Nc2ccc3ncsc3c2)cc1NC1CC1] |
| I-67 | 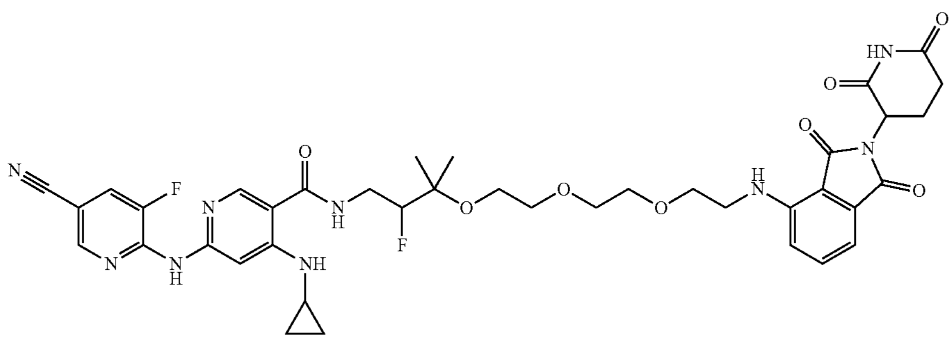 [SMILES: CC(C)(OCCOCCOCCNc1cccc2c1C(=O)N(C1CCC(=O)NC1=O)C2=O)C(F)CNC(=O)c1cnc(Nc2ncc(C#N)cc2F)cc1NC1CC1] |
| I-68 | 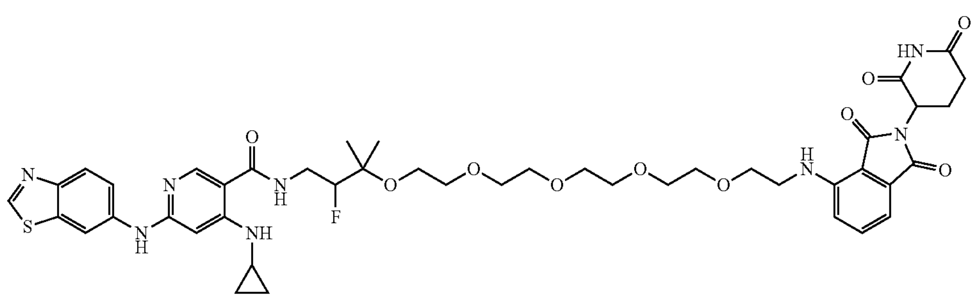 [SMILES: CC(C)(OCCOCCOCCOCCOCCNc1cccc2c1C(=O)N(C1CCC(=O)NC1=O)C2=O)C(F)CNC(=O)c1cnc(Nc2ccc3ncsc3c2)cc1NC1CC1] |
| I-69 | 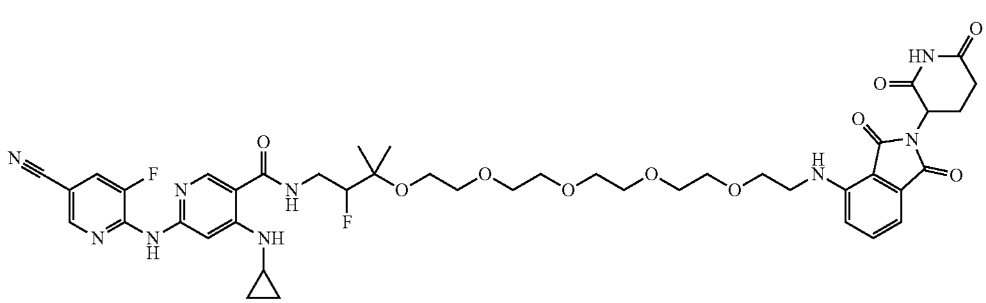 [SMILES: CC(C)(OCCOCCOCCOCCOCCNc1cccc2c1C(=O)N(C1CCC(=O)NC1=O)C2=O)C(F)CNC(=O)c1cnc(Nc2ncc(C#N)cc2F)cc1NC1CC1] |

| I-# | Structure |
|---|---|
| I-70 | 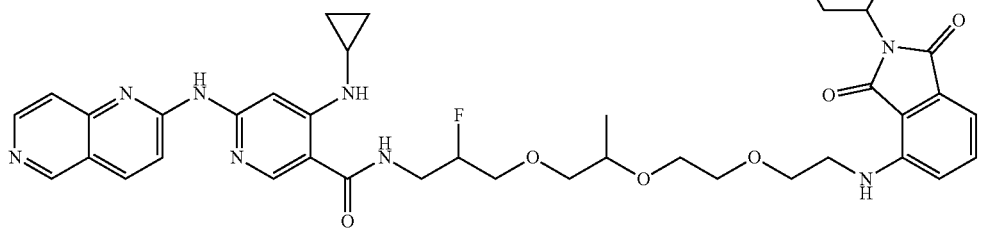 |
| I-74 | 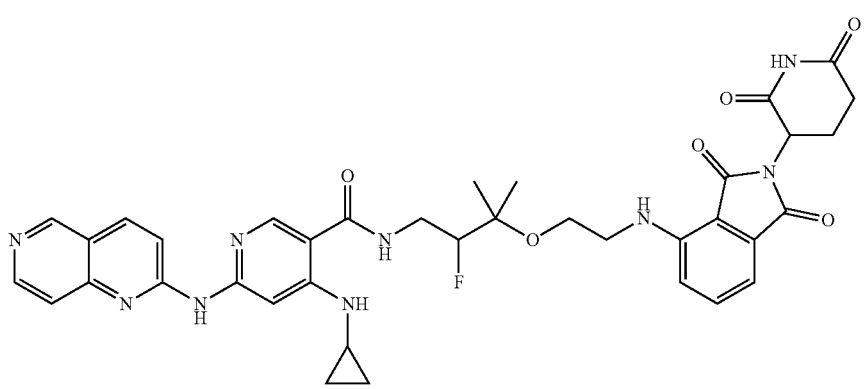 [SMILES: CC(C)(OCCNc1cccc2c1C(=O)N(C1CCC(=O)NC1=O)C2=O)C(F)CNC(=O)c1cnc(Nc2ccc3cnccc3n2)cc1NC1CC1] |
| I-77 | 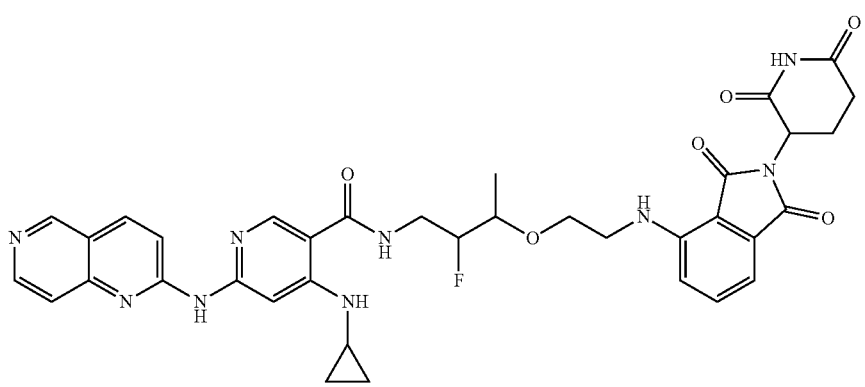 [SMILES: CC(OCCNc1cccc2c1C(=O)N(C1CCC(=O)NC1=O)C2=O)C(F)CNC(=O)c1cnc(Nc2ccc3cnccc3n2)cc1NC1CC1] |
| I-80 | 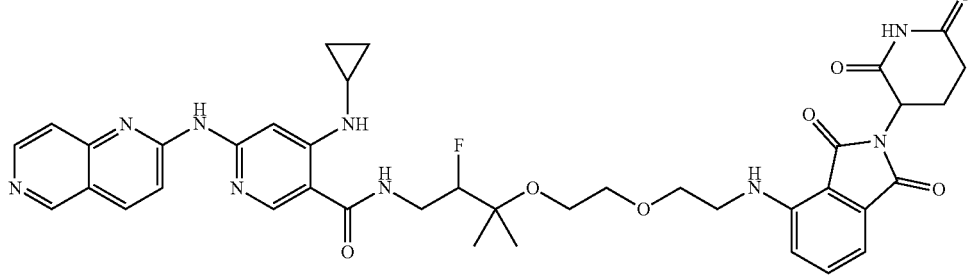 |

| I-# | Structure |
|---|---|
| I-81 | 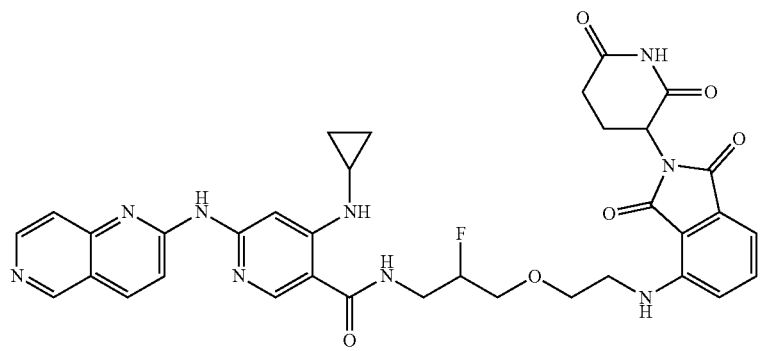 [SMILES: O=C1CCC(N2C(=O)c3cccc(NCCOCC(F)CNC(=O)c4cnc(Nc5ccc6cnccc6n5)cc4NC4CC4)c3C2=O)C(=O)N1] |
| I-84 | 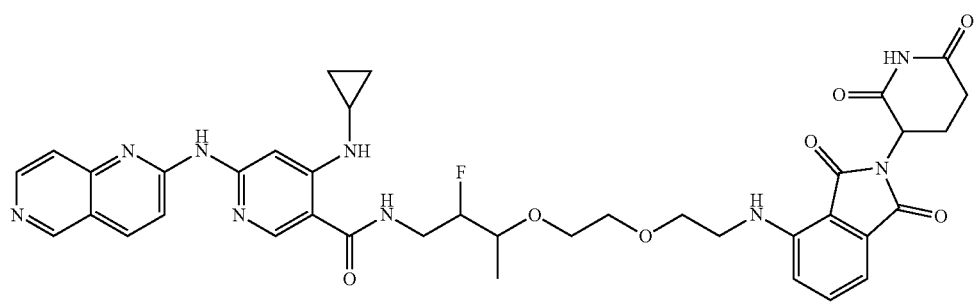 [SMILES: CC(OCCOCCNc1cccc2c1C(=O)N(C1CCC(=O)NC1=O)C2=O)C(F)CNC(=O)c1cnc(Nc2ccc3cnccc3n2)cc1NC1CC1] |
| I-93 | 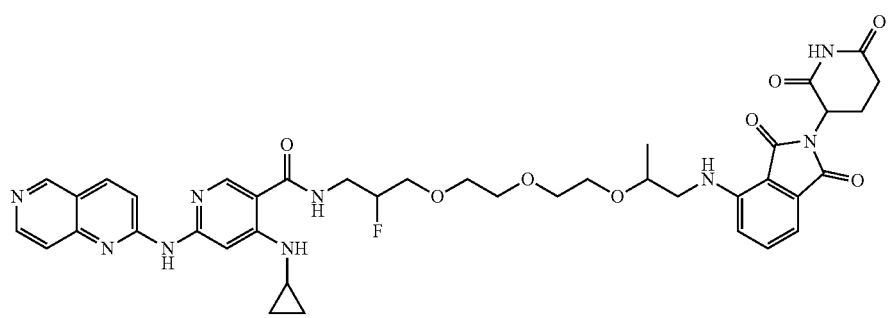 [SMILES: CC(CNc1cccc2c1C(=O)N(C1CCC(=O)NC1=O)C2=O)OCCOCCOCC(F)CNC(=O)c1cnc(Nc2ccc3cnccc3n2)cc1NC1CC1] |
| I-96 | 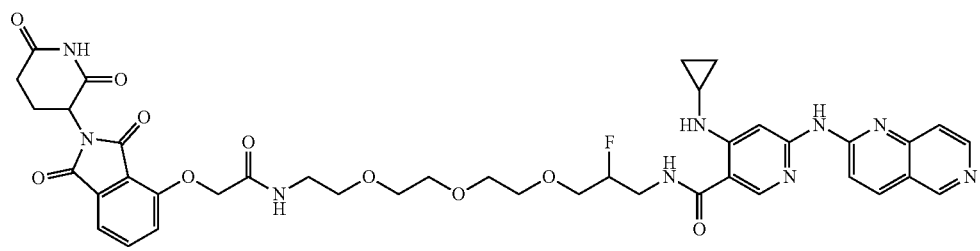 [SMILES: O=C(COc1cccc2c1C(=O)N(C1CCC(=O)NC1=O)C2=O)NCCOCCOCCOCC(F)CNC(=O)c1cnc(Nc2ccc3cnccc3n2)cc1NC1CC1] |
| I-97 | 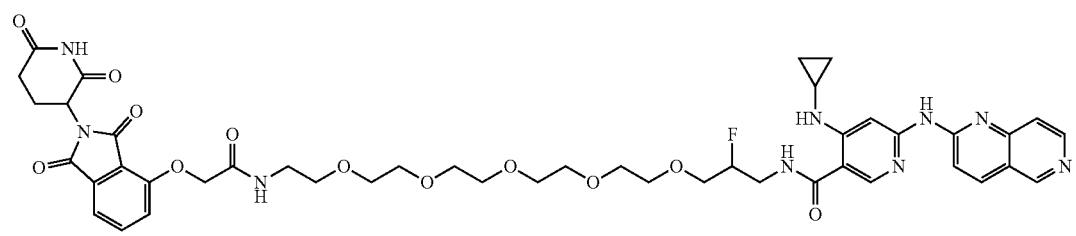 [SMILES: O=C(COc1cccc2c1C(=O)N(C1CCC(=O)NC1=O)C2=O)NCCOCCOCCOCCOCCOCC(F)CNC(=O)c1cnc(Nc2ccc3cnccc3n2)cc1NC1CC1] |

| I-# | Structure |
|---|---|
| I-98 | 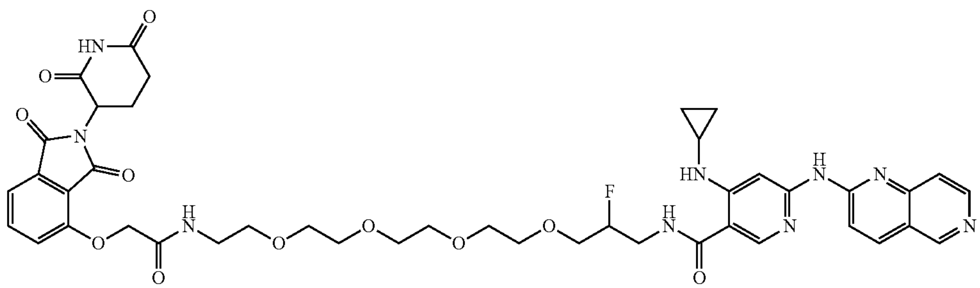 [SMILES: O=C(COc1cccc2c1C(=O)N(C1CCC(=O)NC1=O)C2=O)NCCOCCOCCOCCOCC(F)CNC(=O)c1cnc(Nc2ccc3cnccc3n2)cc1NC1CC1] |
| I-99 | 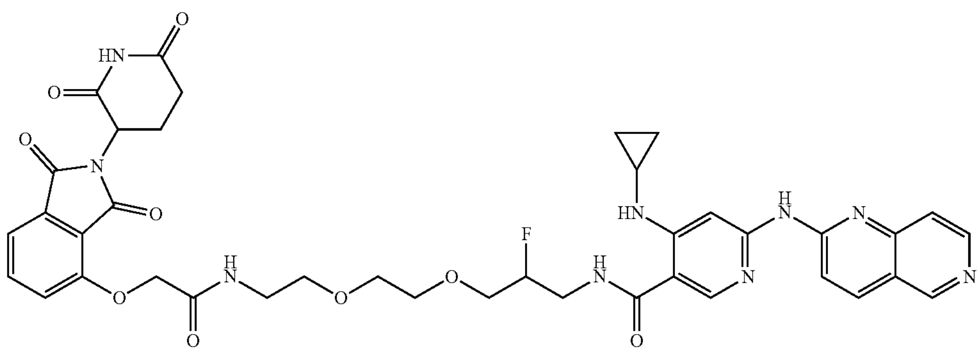 [SMILES: O=C(COc1cccc2c1C(=O)N(C1CCC(=O)NC1=O)C2=O)NCCOCCOCC(F)CNC(=O)c1cnc(Nc2ccc3cnccc3n2)cc1NC1CC1] |
| I-100 | 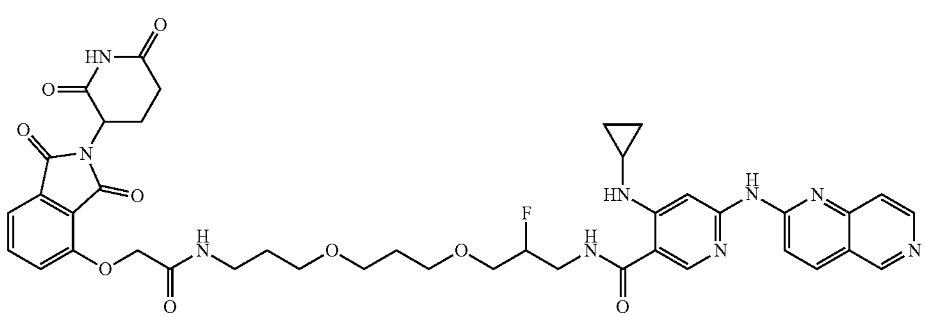 [SMILES: O=C(COc1cccc2c1C(=O)N(C1CCC(=O)NC1=O)C2=O)NCCCOCCCOCC(F)CNC(=O)c1cnc(Nc2ccc3cnccc3n2)cc1NC1CC1] |
| I-119 | 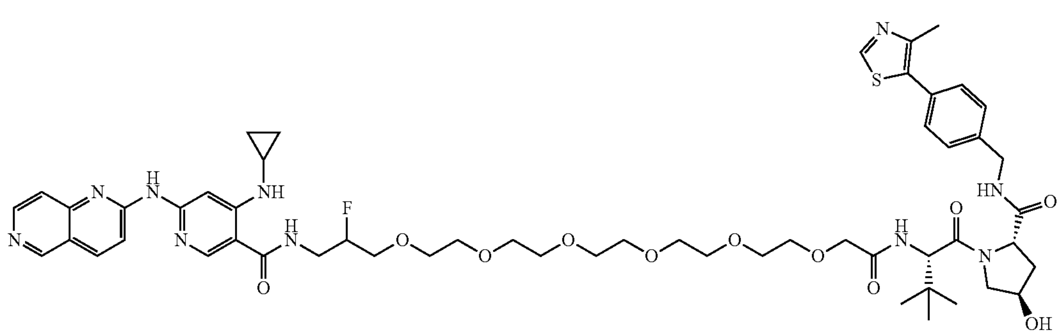 [SMILES: Cc1ncsc1-c1ccc(CNC(=O)[C@@H]2C[C@@H](O)CN2C(=O)[C@@H](NC(=O)COCCOCCOCCOCCOCCOCC(F)CNC(=O)c2cnc(Nc3ccc4cnccc4n3)cc2NC2CC2)C(C)(C)C)cc1] |

| I-# | Structure |
|---|---|
| I-120 | 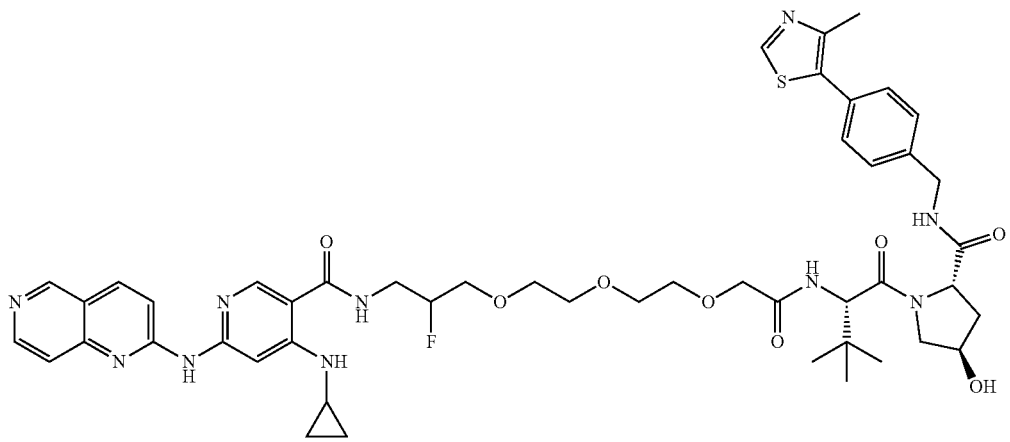 [SMILES: Cc1ncsc1-c1ccc(CNC(=O)[C@@H]2C[C@@H](O)CN2C(=O)[C@@H](NC(=O)COCCOCCOCC(F)CNC(=O)c2cnc(Nc3ccc4cnccc4n3)cc2NC2CC2)C(C)(C)C)cc1] |
| I-174 | 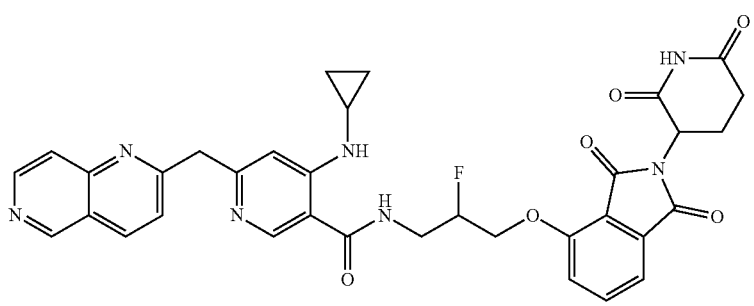 [SMILES: O=C1CCC(N2C(=O)c3cccc(OCC(F)CNC(=O)c4cnc(Cc5ccc6cnccc6n5)cc4NC4CC4)c3C2=O)C(=O)N1] |
| I-206 | 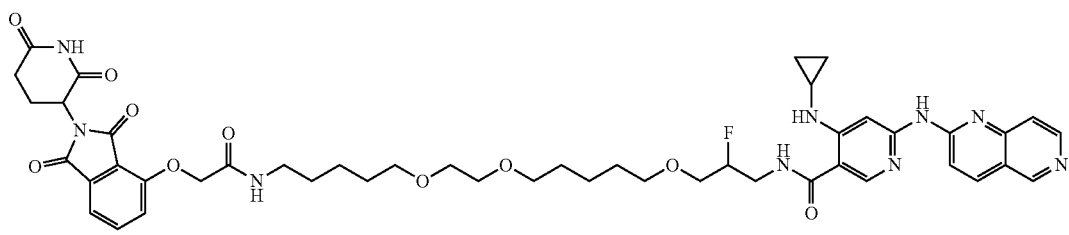 [SMILES: O=C(COc1cccc2c1C(=O)N(C1CCC(=O)NC1=O)C2=O)NCCCCCOCCOCCCCCOCC(F)CNC(=O)c1cnc(Nc2ccc3cnccc3n2)cc1NC1CC1] |
| I-207 | 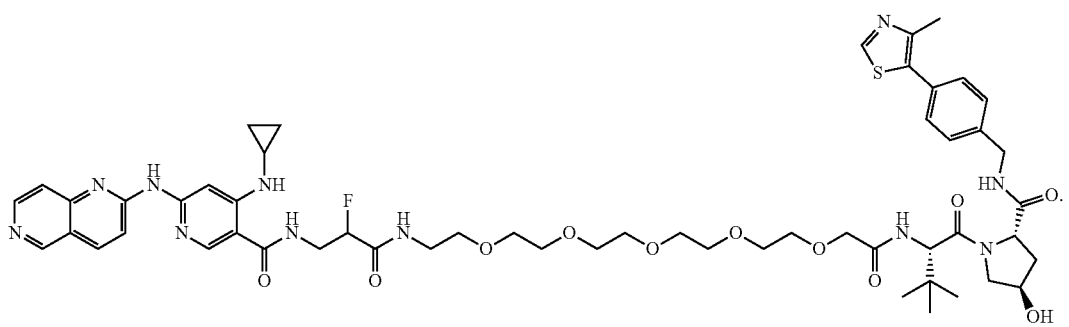 [SMILES: Cc1ncsc1-c1ccc(CNC(=O)[C@@H]2C[C@@H](O)CN2C(=O)[C@@H](NC(=O)COCCOCCOCCOCCOCCNC(=O)C(F)CNC(=O)c2cnc(Nc3ccc4cnccc4n3)cc2NC2CC2)C(C)(C)C)cc1] |

6. A pharmaceutical composition comprising a compound according to claim 1, and a pharmaceutically acceptable carrier, adjuvant, or vehicle.

7. The pharmaceutical composition according to claim 6, further comprising an additional therapeutic agent.

8. The compound according to claim 1, wherein the cereblon E3 ubiquitin ligase binding moiety is

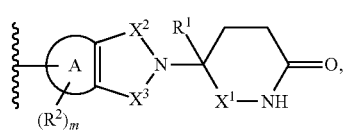

wherein:

each of $X^1$, $X^2$, and $X^3$ is independently a bivalent moiety selected from a covalent bond, —$CH_2$—, —C(O)—, —C(S)—, or

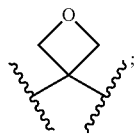 [SMILES: *C1(*)COC1]

R¹ is hydrogen, deuterium, halogen, —CN, —OR, —SR, —S(O)R, —S(O)₂R, —NR₂, or an optionally substituted C₁₋₄ aliphatic;

each R² is hydrogen, —R⁶, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

R⁵ is hydrogen or C₁₋₆ aliphatic;

each R⁶ is independently an optionally substituted group selected from C₁₋₆ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur;

m is 0, 1, 2, 3 or 4.

9. The compound according to claim 1, wherein the VHL E3 ubiquitin ligase binding moiety is

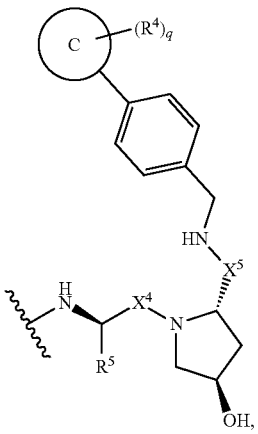

wherein:
each of X⁴ and X⁵ is independently a bivalent moiety selected from —CH₂—, —C(O)—, —C(S)—, or

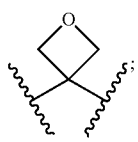

each R⁴ is independently hydrogen, —R⁶, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

each R⁶ is independently an optionally substituted group selected from C₁₋₆ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring C is a selected from 6-membered aryl containing 0-2 nitrogen atoms or a 5-membered heteroaryl with 1-3 heteroatoms independently selected from nitrogen, oxygen or sulfur; and q is 0, 1, 2, 3 or 4.

10. The compound according to claim 1, wherein the VHL E3 ubiquitin ligase binding moiety is

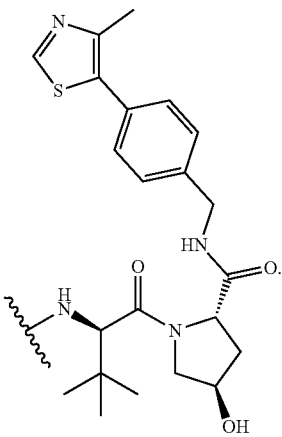 [SMILES: *N[C@@H](C(=O)N1C[C@H](O)C[C@H]1C(=O)NCc1ccc(-c2scnc2C)cc1)C(C)(C)C]

11. A compound of formula I:

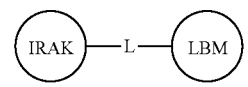

or a pharmaceutically acceptable salt thereof, wherein:
IRAK is an IRAK binding moiety capable of binding to IRAK4, said compound of formula I is a compound of formula I-hhh-1:

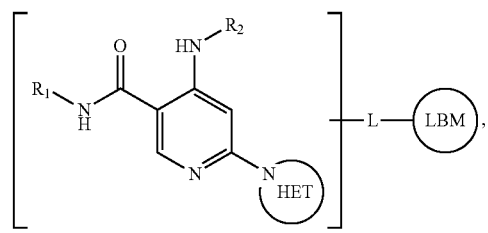

or a pharmaceutically acceptable salt thereof, wherein:
HET is a heteroaryl selected from pyrazolyl, indolyl, pyrrolo[2,3-b]pyridinyl, pyrrolo[2,3-d]pyrimidinyl, pyrazolo[3,4-b]pyridinyl, pyrazolo[3,4-d]pyrimidinyl, 2,3-dihydro-1H-pyrrolo[2,3-b]pyridinyl, imidazo[4,5-b]pyridinyl, and purinyl, wherein said heteroaryl is substituted with $R_a$ and $R_b$;

$R_a$ is H, F, Cl, Br, —CN, —OH, $C_{1-4}$ alkyl, $C_{1-4}$ fluoroalkyl, $C_{1-4}$hydroxyalkyl, $C_{1-4}$ alkoxy, —NH$_2$, —NH($C_{1-4}$ alkyl), —N($C_{1-4}$ alkyl)$_2$, —NH($C_{1-4}$ hydroxyalkyl), —NH($C_{1-4}$ fluoroalkyl), NH($C_{1-6}$ hydroxyfluoroalkyl), —C(O)NH$_2$, —CH$_2$NHC(O)($C_{1-6}$ alkyl), —CH$_2$NHC(O)($C_{1-6}$hydroxyalkyl), —CH$_2$NHC(O)NH($C_{1-6}$ alkyl), —CH$_2$NHC(O)NHCH$_2$(phenyl), CH$_2$NHC(O)N($C_{1-4}$ alkyl)$_2$, —CH$_2$NHC(O)O($C_{1-4}$ alkyl), —CH$_2$NHC(O)($C_{3-6}$ cycloalkyl), —CH$_2$NHC(O)(tetrahydrofuranyl), —CH$_2$NHC(O)CH$_2$($C_{3-6}$ cycloalkyl), —CH$_2$NHC(O)CH$_2$(tetrahydropyranyl), —CH$_2$NHC(O)CH$_2$(phenyl), —NHC(O)($C_{1-4}$ alkyl), pyrrolidinyl, hydroxypyrrolidinyl, or pyridazinyl;

$R_b$ is H or —NH$_2$;

$R_1$ is:
(i) $C_{1-6}$ alkyl, $C_{1-6}$ fluoroalkyl, $C_{1-6}$ hydroxyalkyl, $C_{1-8}$ hydroxy-fluoroalkyl, —($C_{1-6}$ alkylenyl)O($C_{1-4}$ alkyl), —($C_{1-6}$ alkylenyl)O($C_{1-4}$fluoroalkyl), —($C_{1-6}$ fluoroalkylenyl)O($C_{1-4}$ alkyl), —($C_{1-6}$fluoroalkylenyl)O($C_{1-4}$ deuteroalkyl), —($C_{1-6}$ fluoroalkylenyl)O($C_{1-4}$fluoroalkyl), —($C_{1-4}$ fluoroalkylenyl)C($C_{3-6}$ cycloalkyl)$_2$(OH), —($C_{1-4}$alkylenyl)NHC(O)($C_{1-4}$ alkylenyl)OC(O)($C_{1-3}$ alkyl), ($C_{1-6}$alkylenyl)NHS(O)$_2$($C_{1-4}$ alkyl), —($C_{1-6}$ alkylenyl)P(O)($C_{1-4}$ alkoxy)$_2$, —($C_{1-6}$ fluoroalkylenyl)NH($C_{1-4}$ alkyl), —($C_{1-6}$ alkylenyl)C(O)NH($C_{1-4}$ alkyl), —($C_{1-6}$ fluoroalkylenyl)C(O)NH($C_{1-4}$ alkyl), —($C_{1-6}$fluoroalkylenyl)C(O)NH($C_{1-4}$ hydroxyalkyl), or —($C_{1-6}$ fluoroalkylenyl)OP(O)(OH)$_2$;

(ii) —($C_{1-3}$ alkylenyl)$R_x$, —($C_{1-3}$ fluoroalkylenyl)$R_x$, —($C_{1-3}$alkylenyl)C(O)$R_x$, —($C_{1-3}$ alkylenyl)C(O)NHR$_x$, —($C_{1-3}$fluoroalkylenyl)C(O)$R_x$, or CH$_2$CF=(tetrahydropyranyl), wherein $R_x$ is a cyclic group selected from $C_{3-6}$ cycloalkyl, tetrazolyl, 1,1-dioxidotetrahydrothiophenyl, 1,1-dioxidothiomorpholinyl, oxadiazolyl, piperidinyl, piperazinyl, pyrrolidinyl, oxetanyl, tetrahydrofuranyl, tetrahydropyranyl, pyridinyl, imidazolyl, morpholinyl, phenyl, and triazinyl, wherein each cyclic group is substituted with zero to 3 substituents independently selected from F, —OH, —CH$_3$, —C(CH$_2$)$_2$OH, —OCH$_3$, —C(O)CH$_2$CN, —S(O)$_2$CH$_3$, —S(O)$_2$NH$_2$, —NHC(O)CH$_3$, —N(S(O)$_2$CH$_3$)$_2$, —CH$_2$CH$_2$(acetamidophenyl), —CH$_2$CH$_2$(methoxyphenyl), —CH$_2$CH$_2$(sulfamoylphenyl), oxetanyl, benzyl, and morpholinyl;

(iii) $C_{3-6}$ cycloalkyl or $C_{4-6}$ cycloalkenyl, each substituted with zero to 3 substituents independently selected from F, —OH, —CN, $C_{1-3}$alkyl, $C_{1-3}$ alkoxy, —S($C_{1-3}$ alkyl), NO$_2$, —S(O)$_2$($C_{1-3}$ alkyl), $C_{1-4}$hydroxyalkyl, —C($C_{1-3}$ alkyl)(OH)($C_{3-6}$ cycloalkyl), —CH$_2$C(O)NH($C_{1-3}$ alkyl), —NHC(O)($C_{1-3}$ alkyl), —NHC(O)($C_{1-4}$hydroxyalkyl), —C(O)NH($C_{1-3}$ alkyl), —C(O)NH($C_{1-3}$ deuteroalkyl), —C(O)NH($C_{3-6}$ cycloalkyl), —NHC(O)O($C_{1-3}$ alkyl), —NHS(O)$_2$($C_{1-3}$alkyl), pyridinyl, imidazolyl, pyrazolyl, methylimidazolyl, methylpyrazolyl, and thiazolyl;

(iv) tetrahydropyranyl, piperidinyl, pyrazolyl, phenyl, pyridinyl, or pyrimidinyl, each substituted with zero to 1 substituent selected from —OH, $C_{1-3}$ alkyl, $C_{1-3}$ fluoroalkyl, $C_{1-4}$ hydroxyalkyl, $C_{1-3}$alkoxy, —C(O)($C_{1-4}$ alkyl), —S(O)$_2$($C_{1-4}$ alkyl), —S(O)$_2$NH($C_{1-4}$ alkyl), —NH($C_{1-3}$ alkyl), —N($C_{1-3}$ alkyl)$_2$, —O($C_{1-3}$ alkylenyl)N($C_{1-3}$ alkyl)$_2$, —CH$_2$(morpholinyl), azetidinyl, oxetanyl, tetrahydropyranyl, morpholinyl, piperazinyl, piperidinyl, methylpiperazinyl, methoxypiperidinyl, pyridinyl, pyrimidinyl, methyl sulfonyl azetidinyl, and —C(O)(methylsulfonyl azetidinyl); or (v) pyrrolo[2,3-c]pyridinyl, bicyclo[2.2.1]heptan-1-ol, tetrahydrobenzo[d]thiazol-2-amine, or 1,3-diazaspiro[4.5]decane-2,4-dione; and $R_2$ is:
(i) $C_{1-7}$ alkyl or $C_{2-6}$ alkenyl, each substituted with zero to three substituents independently selected from F, —OH, and —CN; —($C_{1-4}$ alkylenyl)O($C_{1-4}$ alkyl), ($C_{1-4}$ alkylenyl)O($C_{1-4}$ fluoroalkyl), —($C_{1-6}$ alkylenyl)NH$_2$, —($C_{1-6}$ alkylenyl)S(O)$_2$($C_{1-3}$ alkyl), —($C_{1-6}$fluoroalkylenyl)NH($C_{1-3}$ alkyl), or —($C_{1-6}$ alkylenyl)NHC(O)($C_{1-4}$fluoroalkyl);

(ii) —($C_{1-4}$ alkylenyl)$R_y$, wherein $R_y$ is $C_{3-6}$ cycloalkyl, azetidinyl, oxetanyl, oxazolyl, pyridinyl, tetrahydropyranyl, or morpholinyl, each substituted with zero to 2 substituents independently selected from F, —OH, and $C_{1-3}$ alkyl;

(iii) $C_{3-6}$ cycloalkyl, azetidinyl, oxetanyl, furanyl, tetrahydrofuranyl, pyrrolidinyl, piperidinyl, or tetrahydropyranyl, each substituted with zero to 3 substituents independently selected from F, —OH, $C_{1-3}$alkyl, $C_{1-3}$ hydroxyalkyl, —C(O)($C_{1-3}$ alkyl), —C(O)($C_{1-3}$ fluoroalkyl), —C(O)($C_{1-3}$ cyanoalkyl), —C(O)O($C_{1-3}$ alkyl), C(O)NH$_2$, —C(O)NH($C_{1-3}$ alkyl), —C(O)(difluorophenyl), —NH$_2$, —NH($C_{1-3}$ alkyl), —NH($C_{1-3}$ fluoroalkyl), —NH(oxetanyl), —NHC(O)($C_{1-3}$ alkyl), —NHC(O)($C_{1-3}$ fluoroalkyl), —NHC(O)($C_{3-6}$ cycloalkyl), —NHC(O)(fluorophenyl), —S(O)$_2$($C_{1-3}$ alkyl), imidazolyl, phenyl, pyrimidinyl, fluoropyrimidinyl, chloropyrimidinyl, and methoxypyrimidinyl;

(iv) adamantanyl, hydroxyadamantanyl, benzo[d]imidazolyl, benzo[d]oxazolyl, benzo[d]triazolyl, benzothiazolyl, bicyclo[1.1.1]pentanyl, or hydroxy-bicyclo[2.2.1]heptanyl; or (v) phenyl, pyrazolyl, thiazolyl, thiadiazolyl, or indazolyl, each substituted with 0 to 2 substituents independently selected from F, $C_1$, —OH, —CN, $C_{1-4}$ alkyl, $C_{1-4}$ hydroxyalkyl, $C_{1-4}$ fluoroalkyl, $C_{1-4}$cyanoalkyl, $C_{1-3}$ alkoxy, $C_{3-6}$ cycloalkyl, —($C_{1-3}$ alkylenyl)O($C_{1-3}$alkyl), —($C_{1-3}$ alkylenyl)O($C_{1-3}$ fluoroalkyl), —C(O)NH$_2$, C(O)NH($C_{1-3}$ alkyl), —NHC(O)($C_{1-3}$ alkyl), —NHC(O)S(O)$_2$($C_{1-3}$alkyl), —S(O)$_2$NH$_2$, —S(O)$_2$($C_{1-3}$ alkyl), pyrazolyl, methyl pyrazolyl, imidazolyl, triazolyl, methyl tetrazolyl, ethyl tetrazolyl, phenyl, pyrimidinyl, fluoropyrimidinyl, and tetrahydropyranyl;

L is a covalent bond or a bivalent, saturated or unsaturated, straight or branched $C_{1-50}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

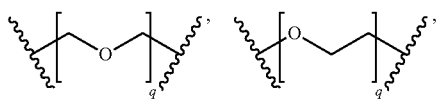

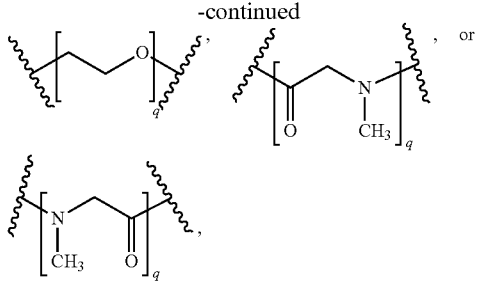

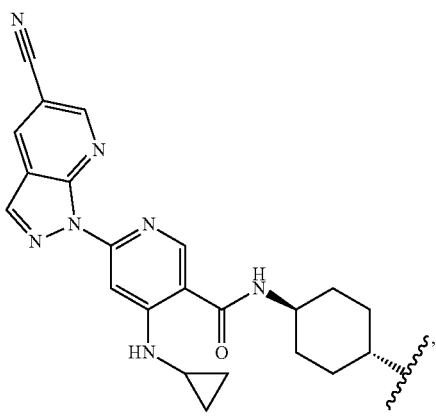

wherein:
each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur; and each of n is independently 1, 2, 3, 4, 5, 6, 7, 8, 9, or 10;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur;

LBM is a ligase ligase binding moiety selected from a cereblon E3 ubiquitin ligase binding moiety and a VHL E3 ubiquitin ligase binding moiety.

12. The compound according to claim 11, wherein the IRAK4 binding moiety is selected from:

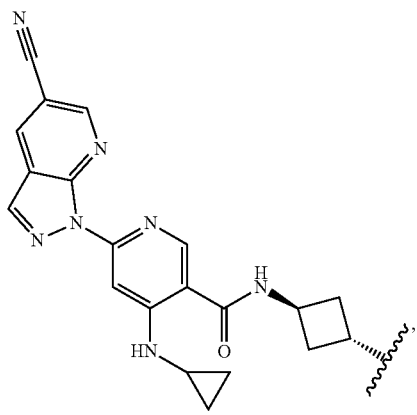

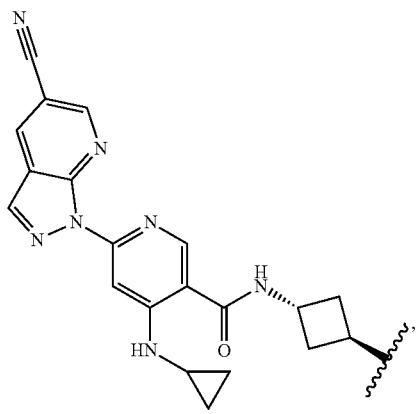

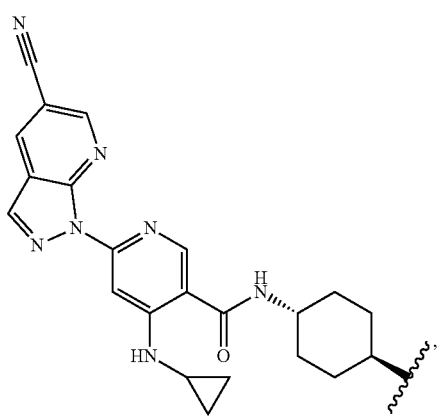

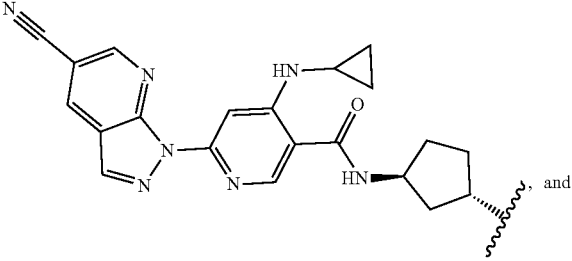

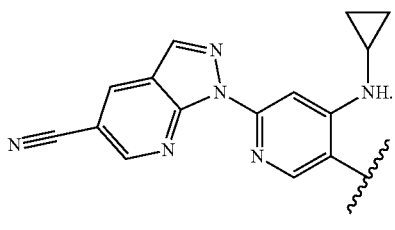

13. The compound according to claim 11, wherein the cereblon E3 ubiquitin ligase binding moiety is

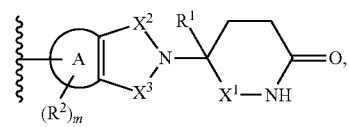

wherein:
each of $X^1$, $X^2$, and $X^3$ is independently a bivalent moiety selected from a covalent bond, —$CH_2$—, —C(O)—, —C(S)—, or

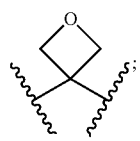 [SMILES: *C1(*)COC1]

$R^1$ is hydrogen, deuterium, halogen, —CN, —OR, —SR, —S(O)R, —S(O)$_2$R, —NR$_2$, or an optionally substituted $C_{1-4}$ aliphatic;

each $R^2$ is hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur;

m is 0, 1, 2, 3 or 4.

14. The compound according to claim 11, wherein the cereblon E3 ubiquitin ligase binding moiety is selected from:

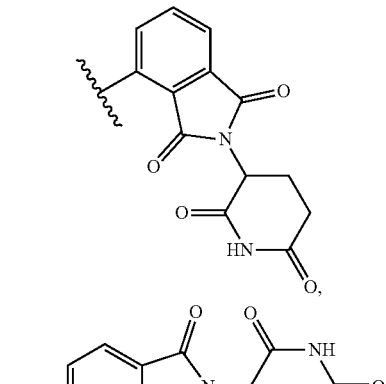

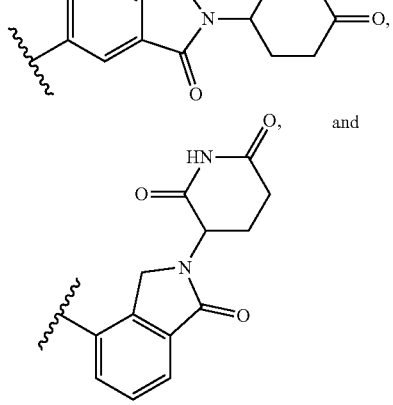

and

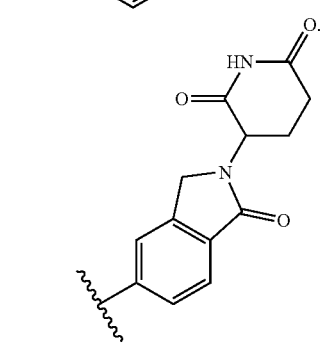

15. The compound according to claim 11, wherein the VHL E3 ubiquitin ligase binding moiety is

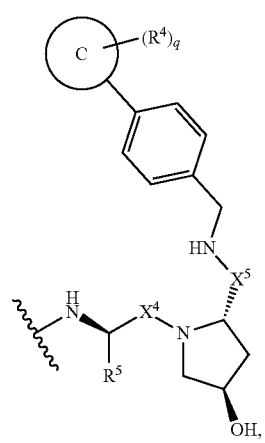

wherein:
  each of $X^4$ and $X^5$ is independently a bivalent moiety selected from —$CH_2$—, —C(O)—, —C(S)—, or

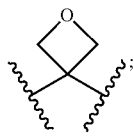 [SMILES: *C1(*)COC1]

each $R^4$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —N(R)C(O)NR2, or —$N(R)S(O)_2R$;
  $R^5$ is hydrogen or $C_{1-6}$ aliphatic;
  each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
  Ring C is a selected from 6-membered aryl containing 0-2 nitrogen atoms or a 5-membered heteroaryl with 1-3 heteroatoms independently selected from nitrogen, oxygen or sulfur; and
  q is 0, 1, 2, 3 or 4.

16. The compound according to claim 11, wherein the VHL E3 ubiquitin ligase binding moiety is

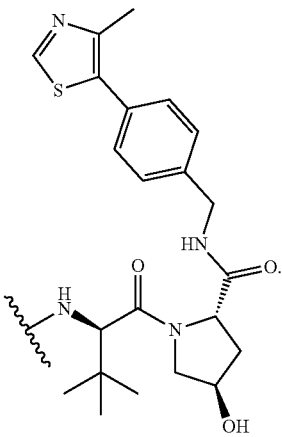 [SMILES: *N[C@@H](C(=O)N1C[C@H](O)C[C@H]1C(=O)NCc1ccc(-c2scnc2C)cc1)C(C)(C)C]

17. The compound according to claim 11, wherein L is selected from:

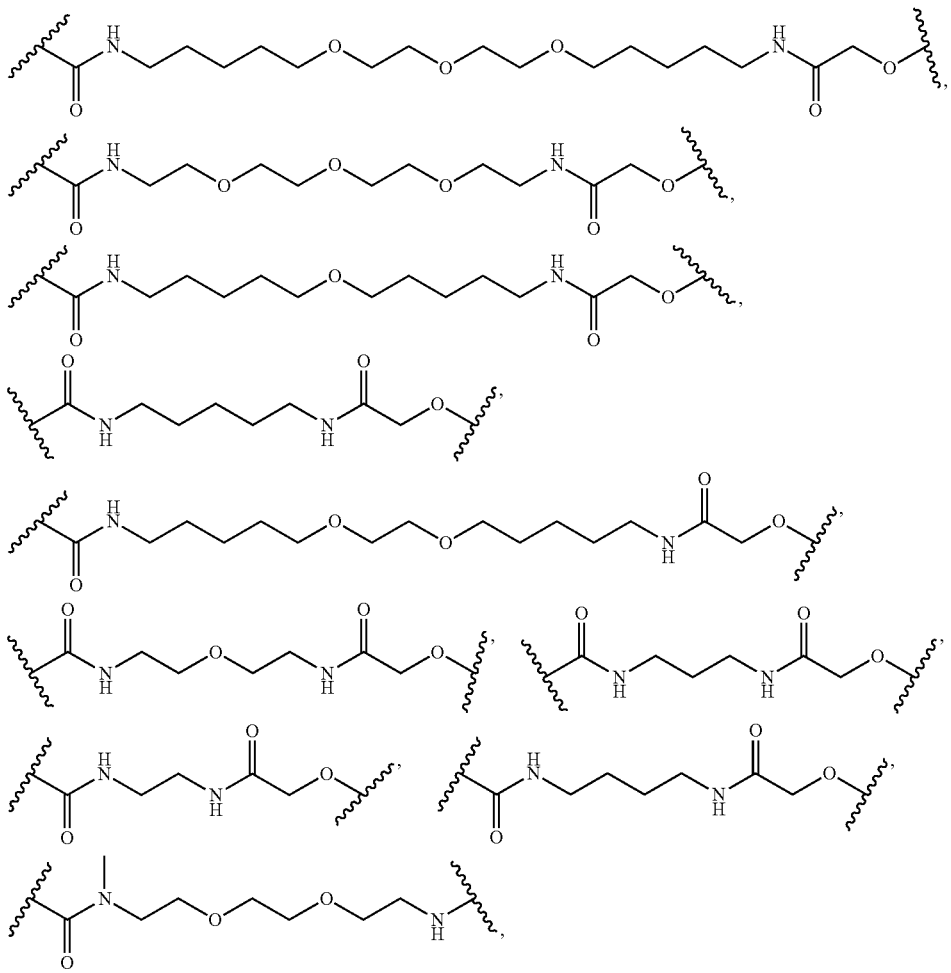

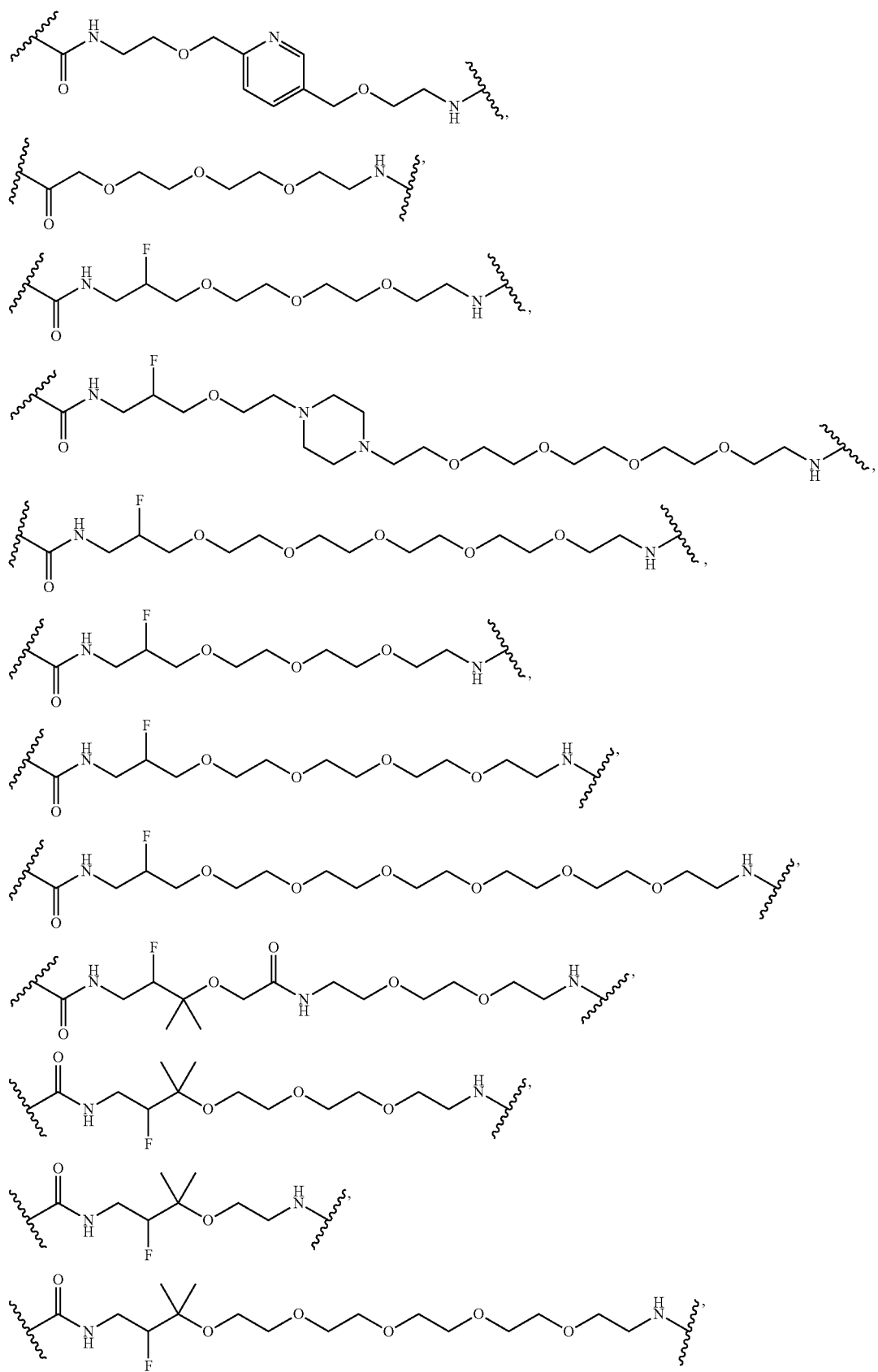

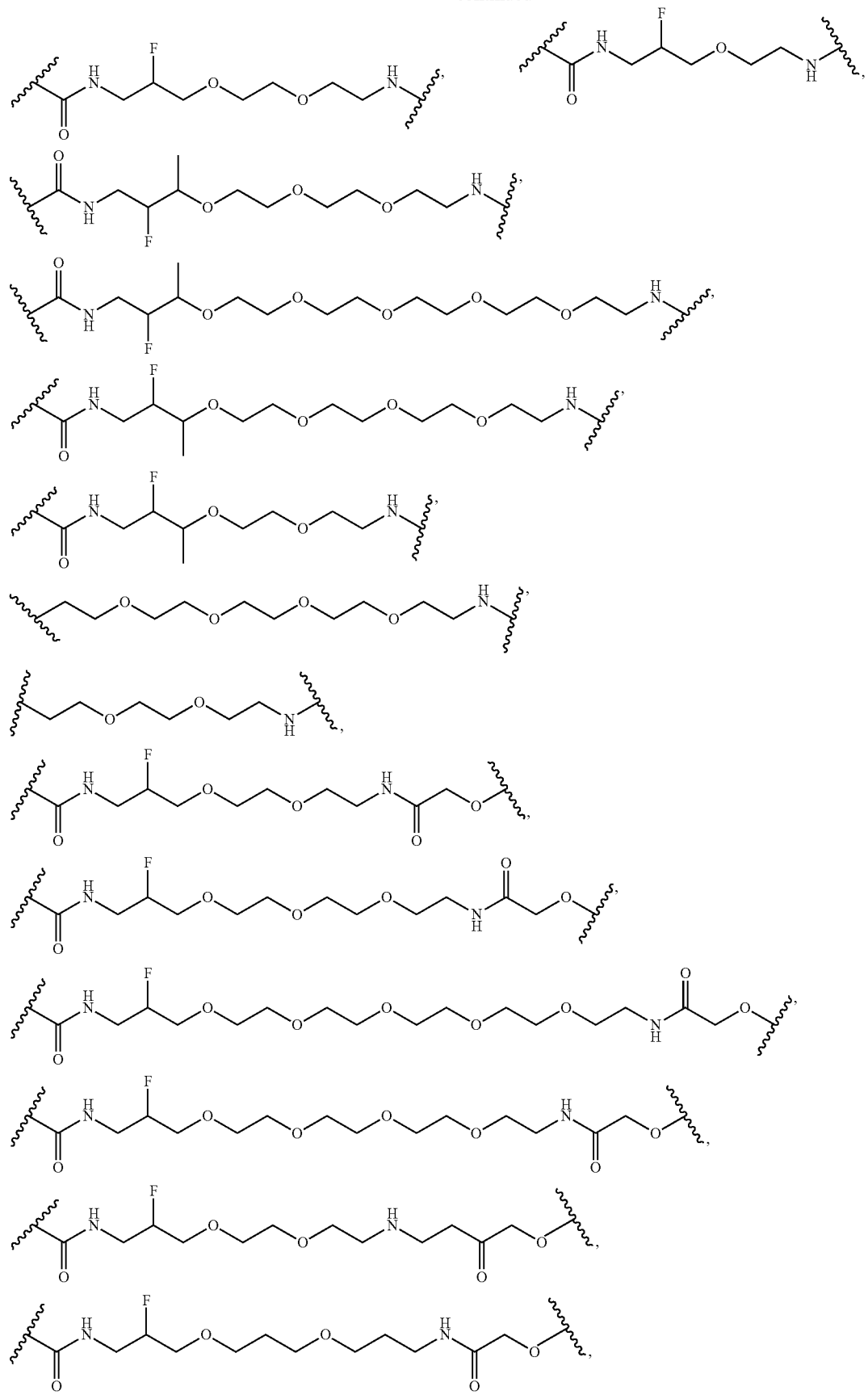

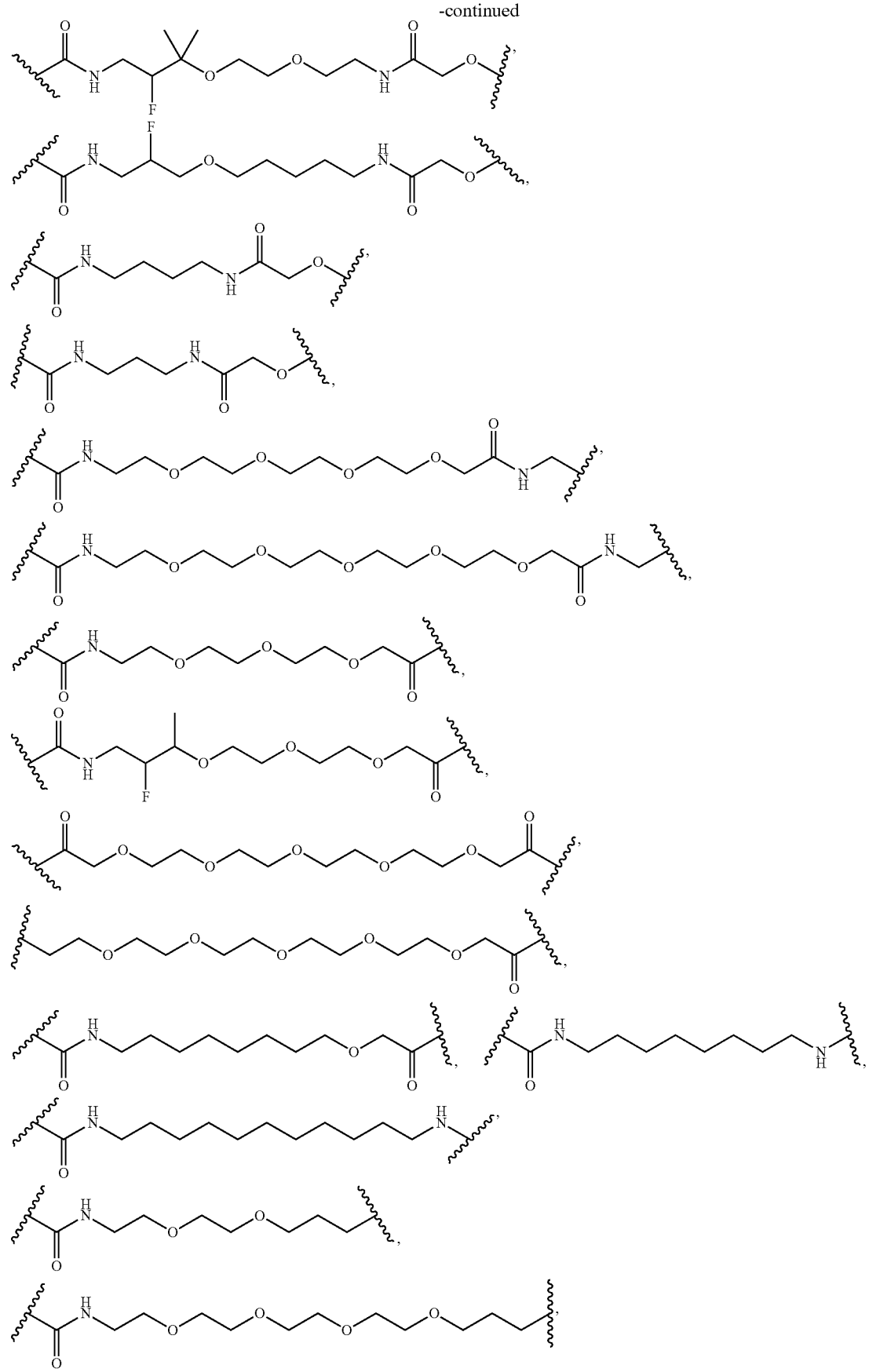

-continued
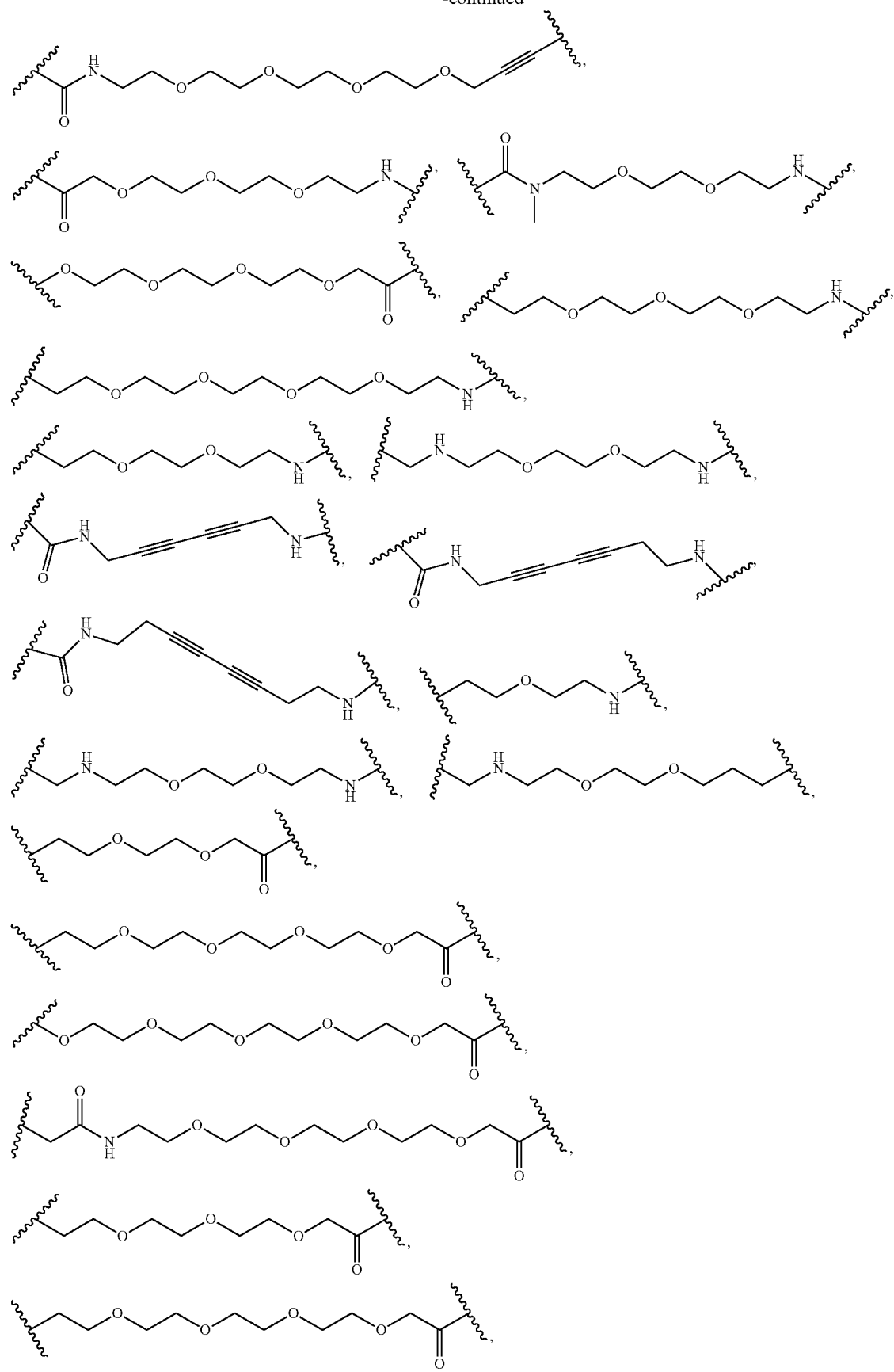

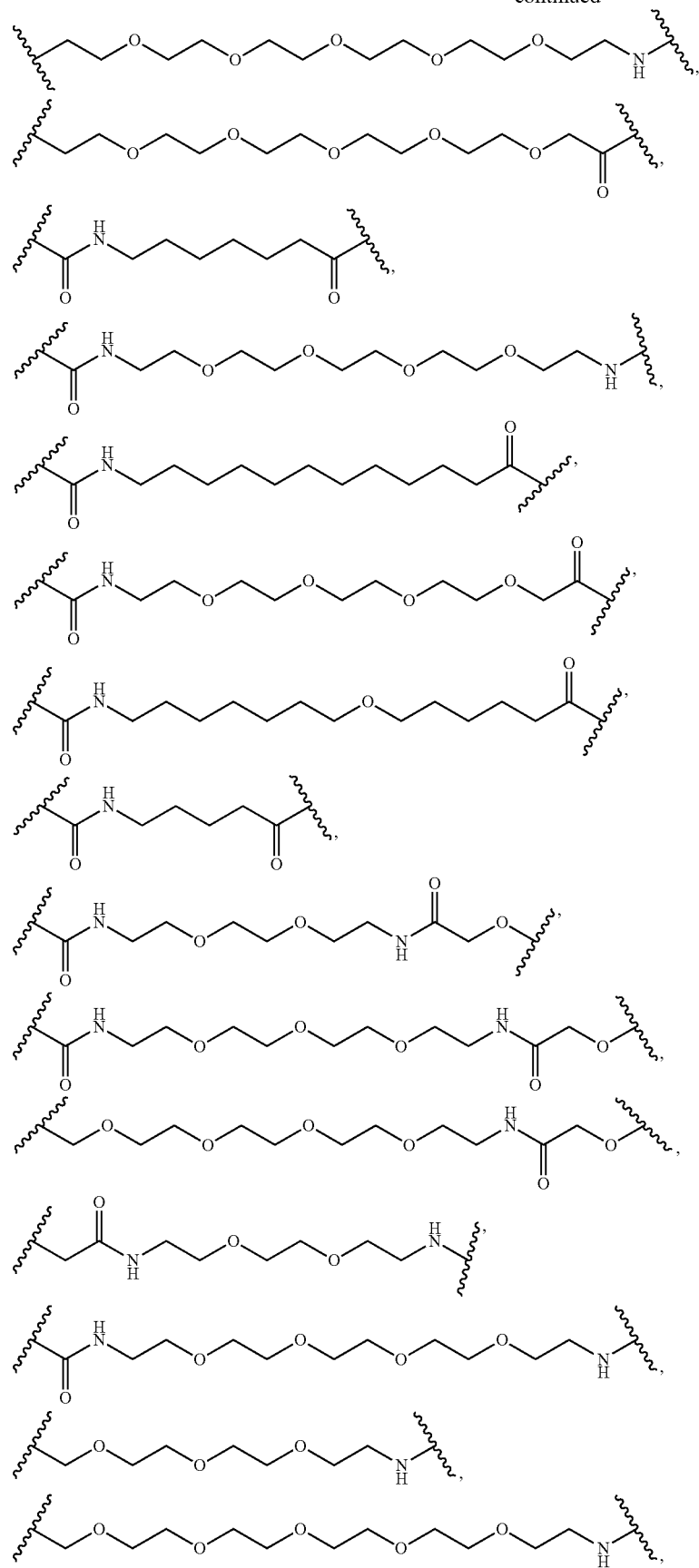

-continued
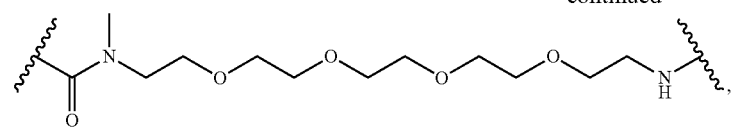
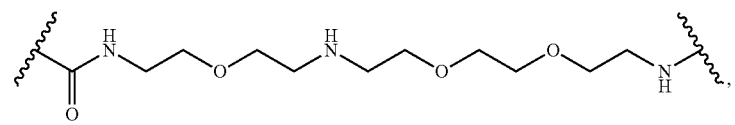
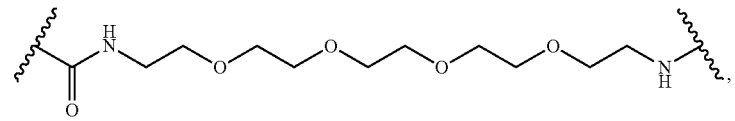
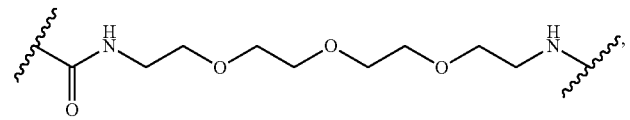
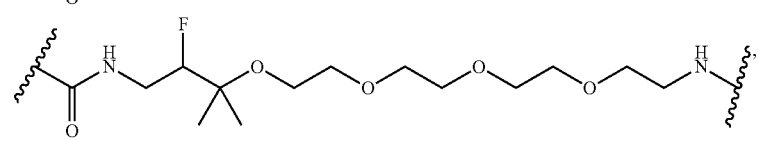
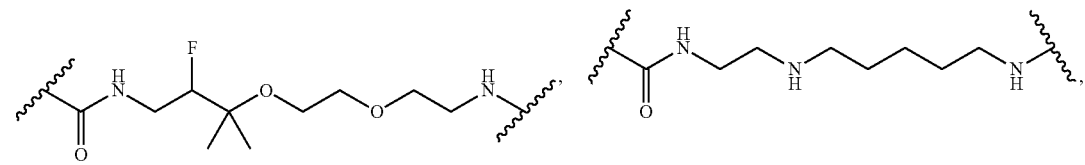
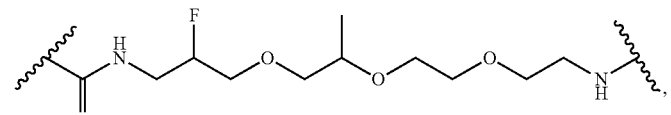
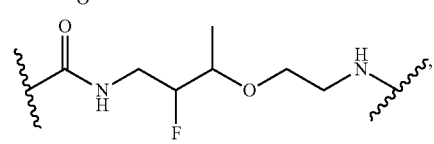
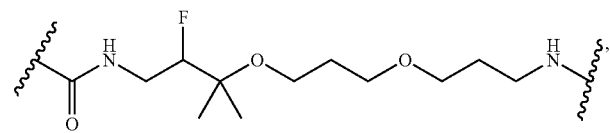
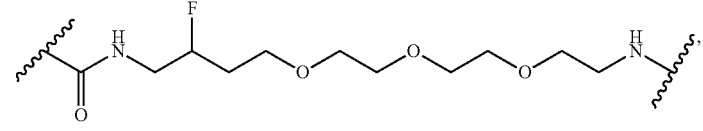
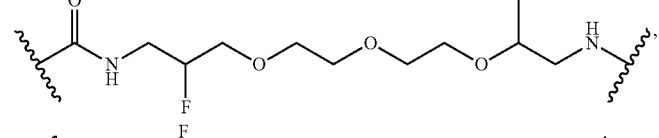
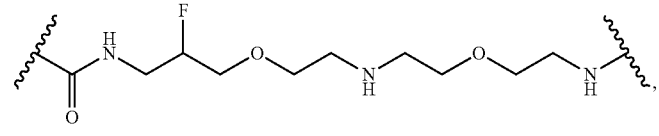
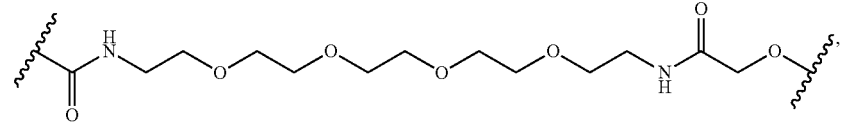

-continued
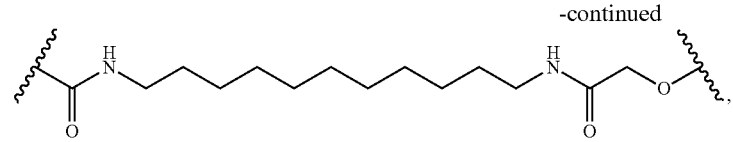
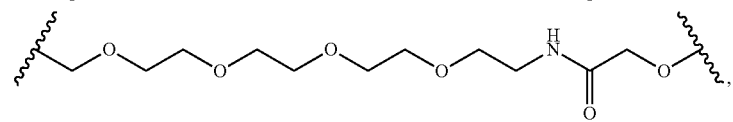
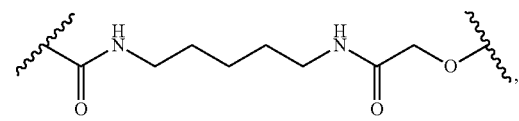
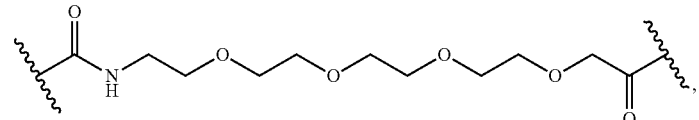
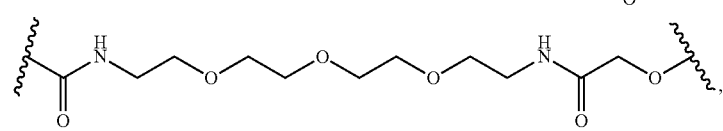
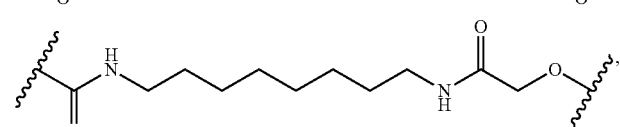
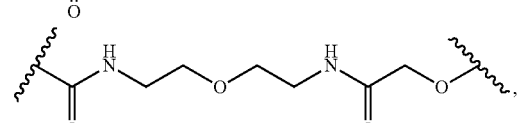
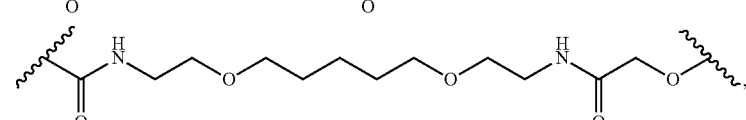
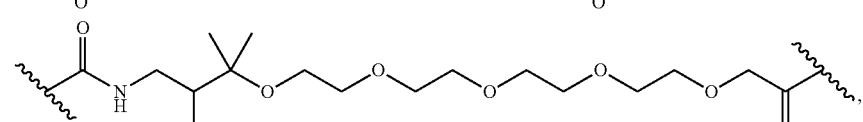
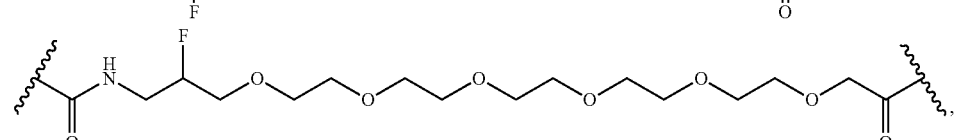
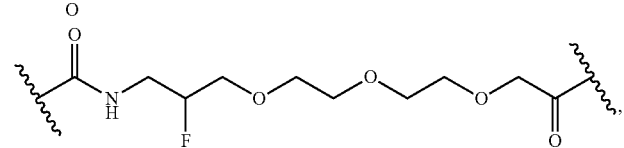
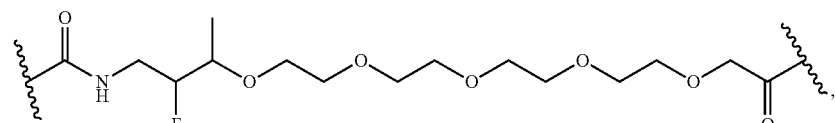
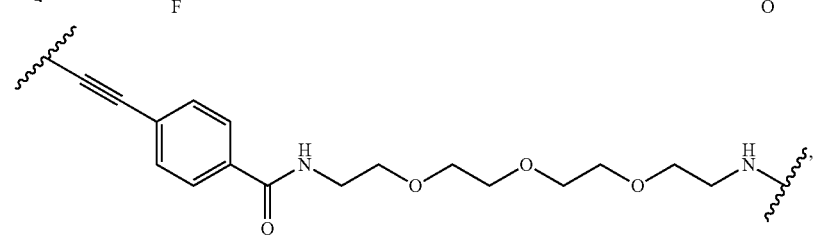

-continued
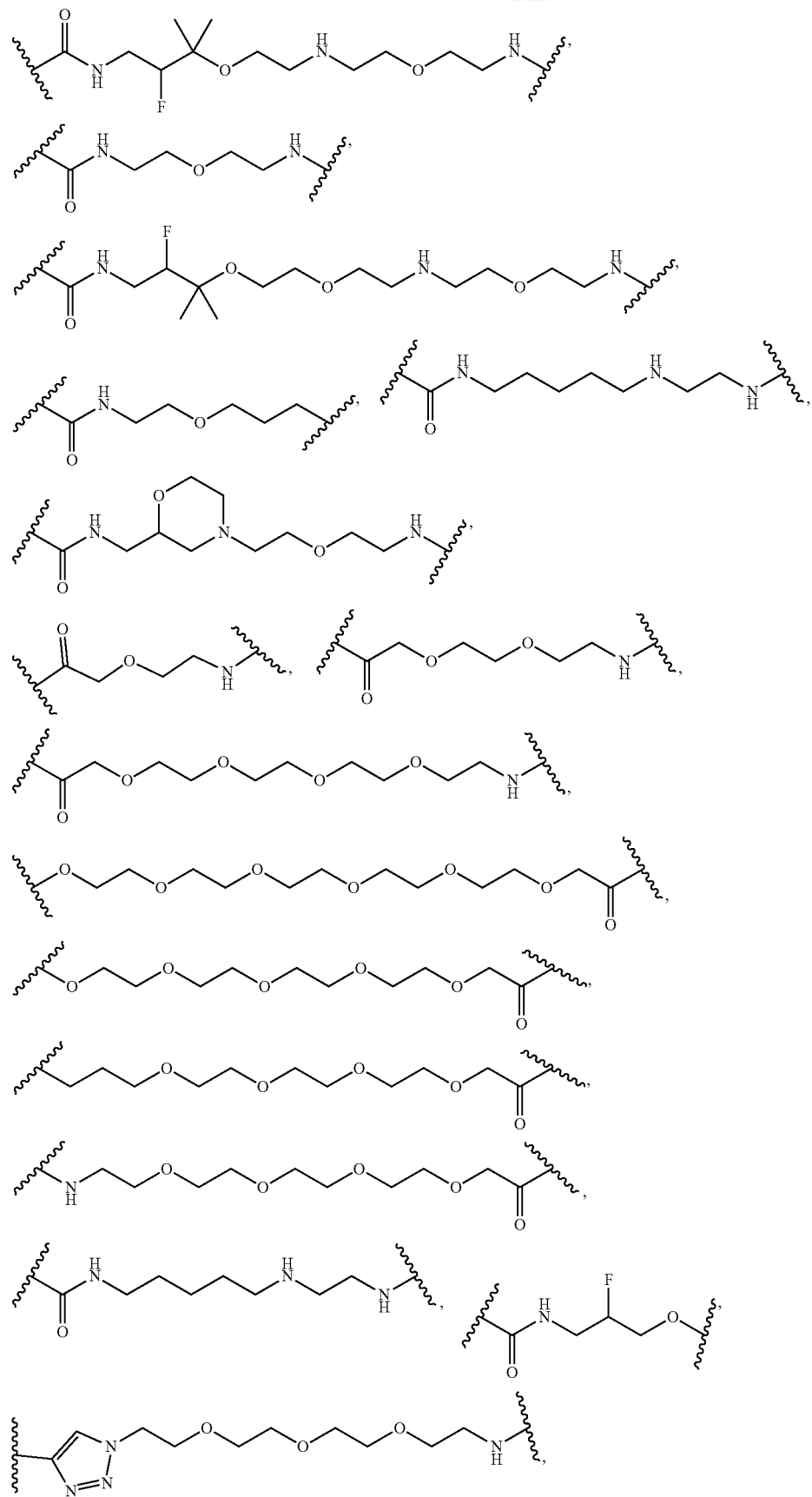

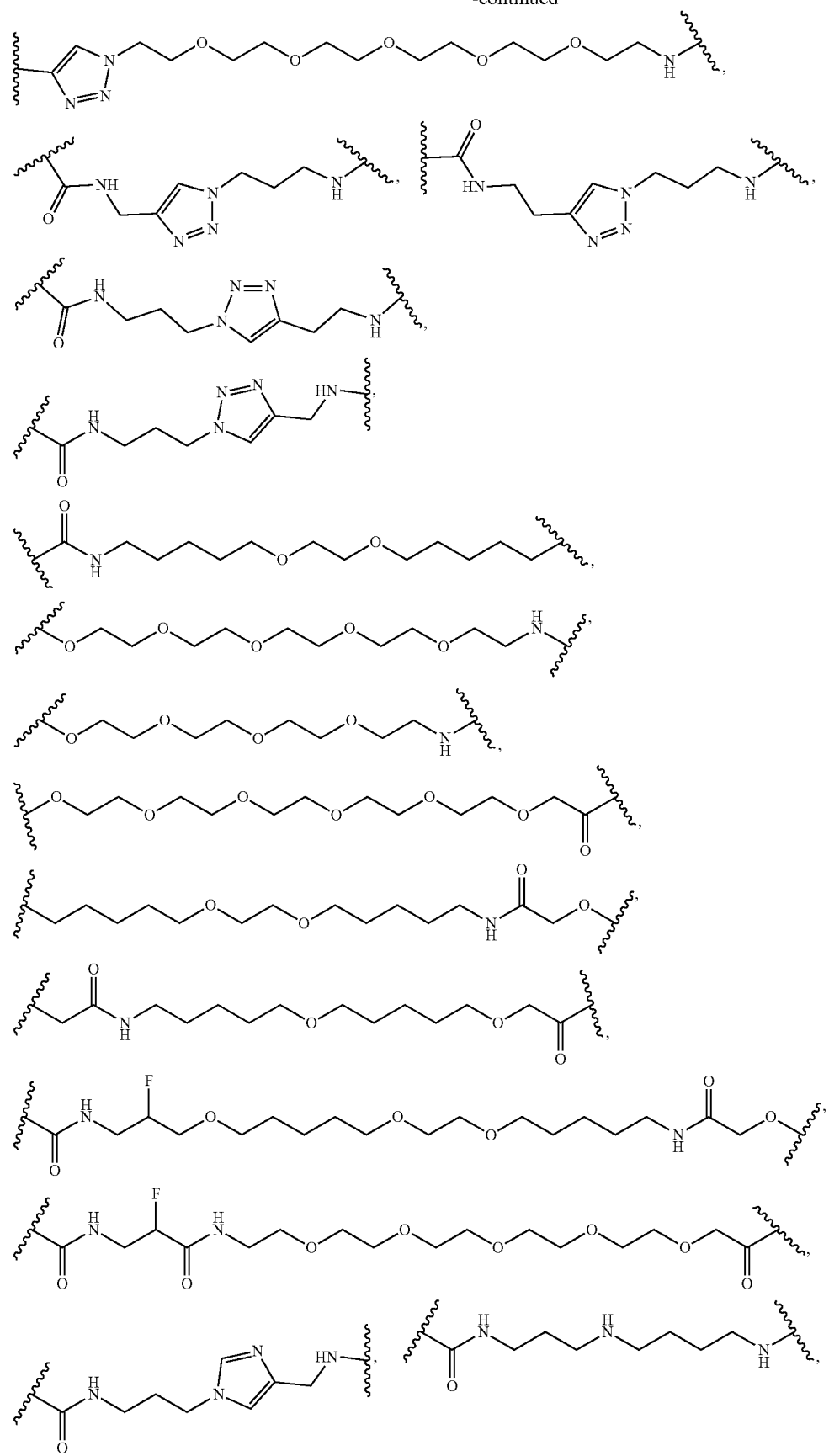

-continued
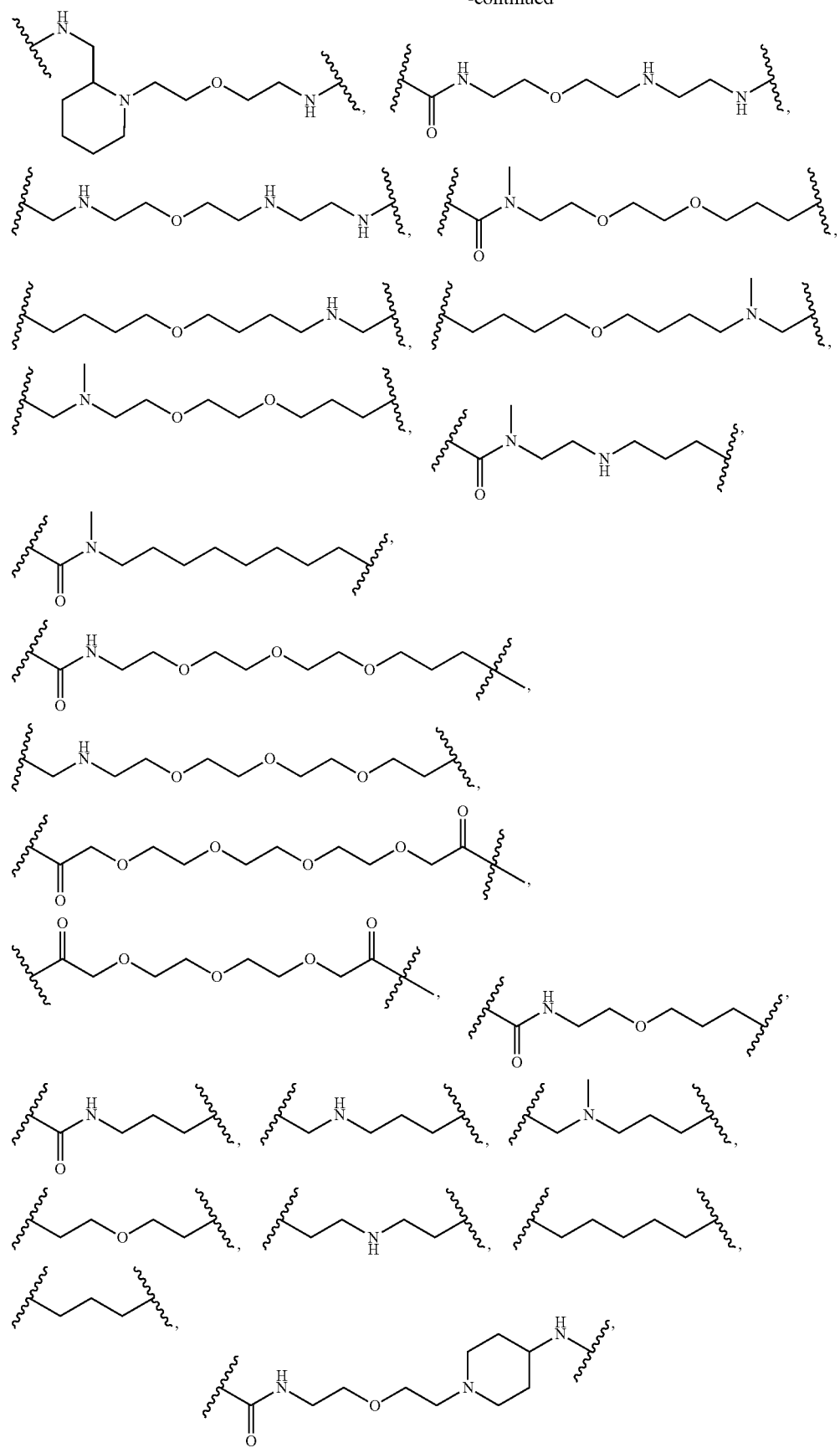

2807 2808
-continued
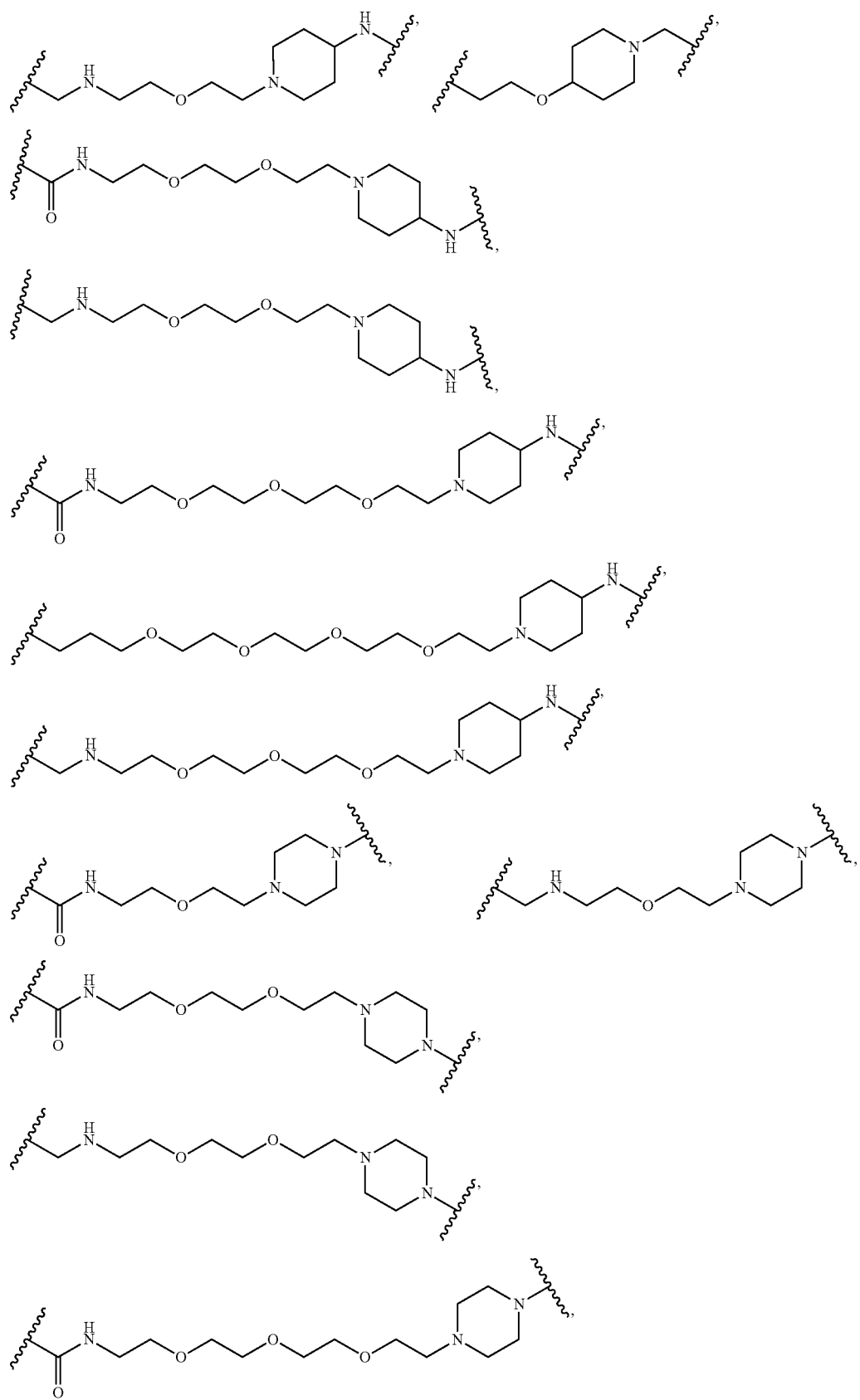

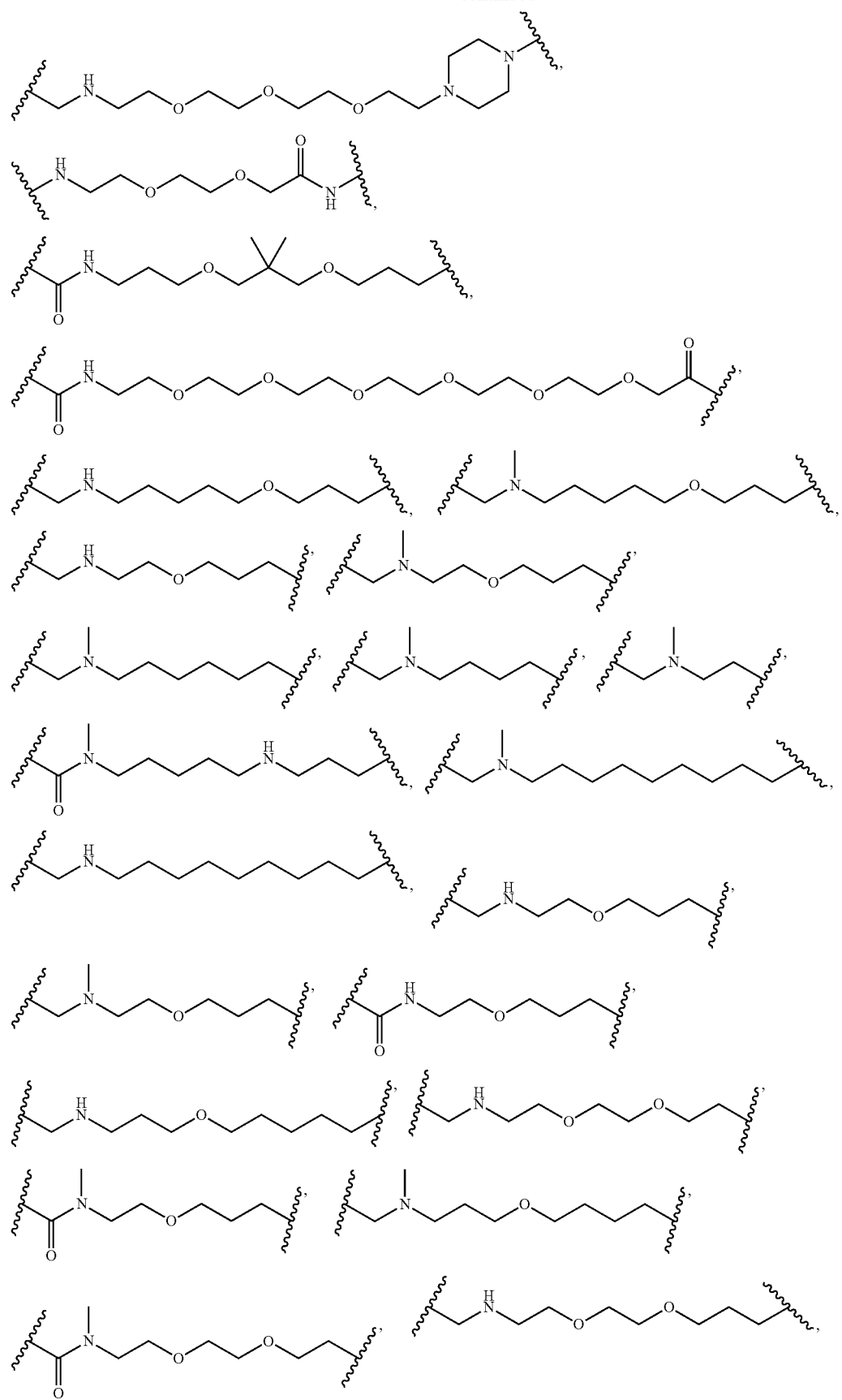

2811 2812
-continued
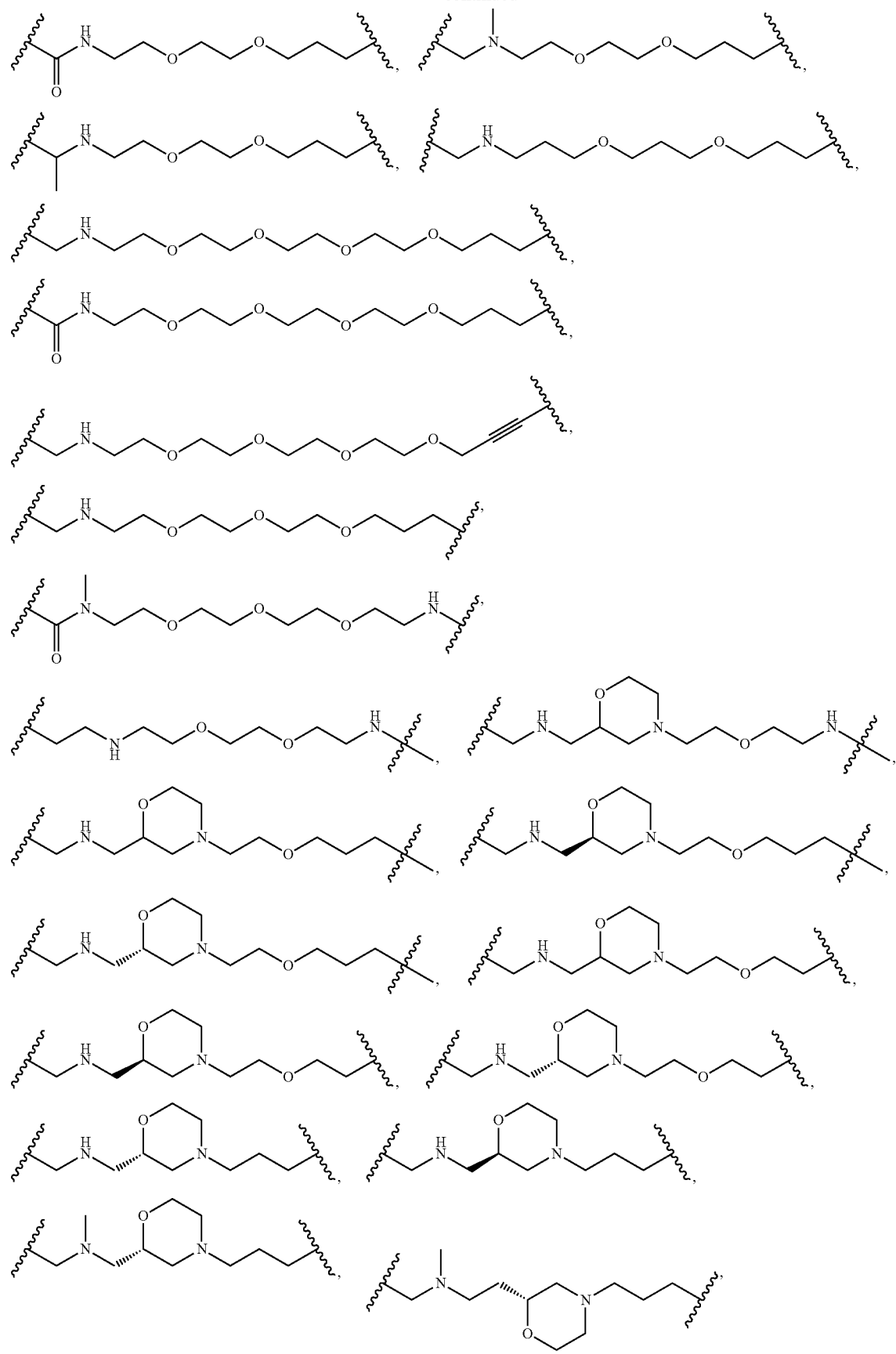

-continued
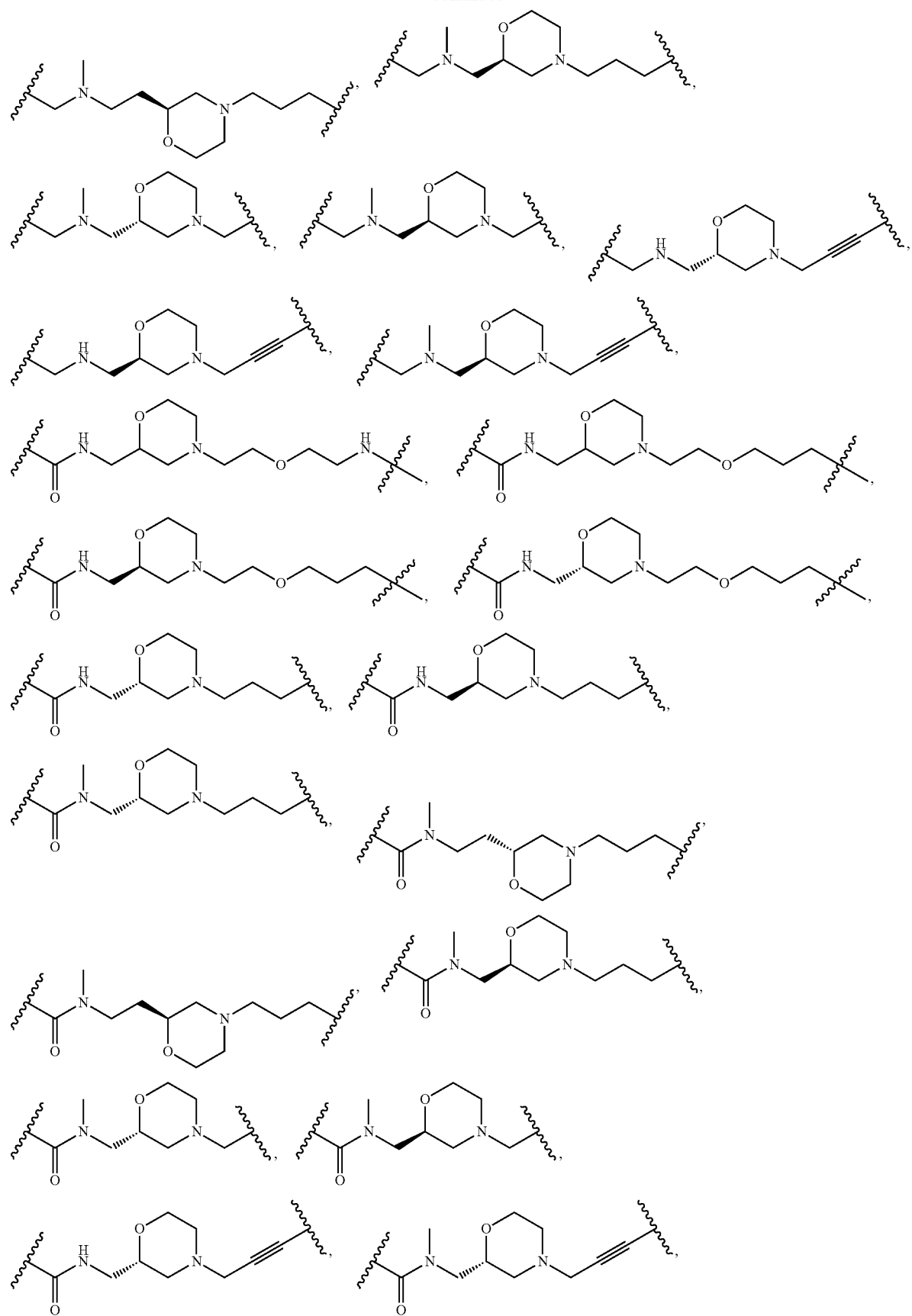

2815                                    2816
-continued
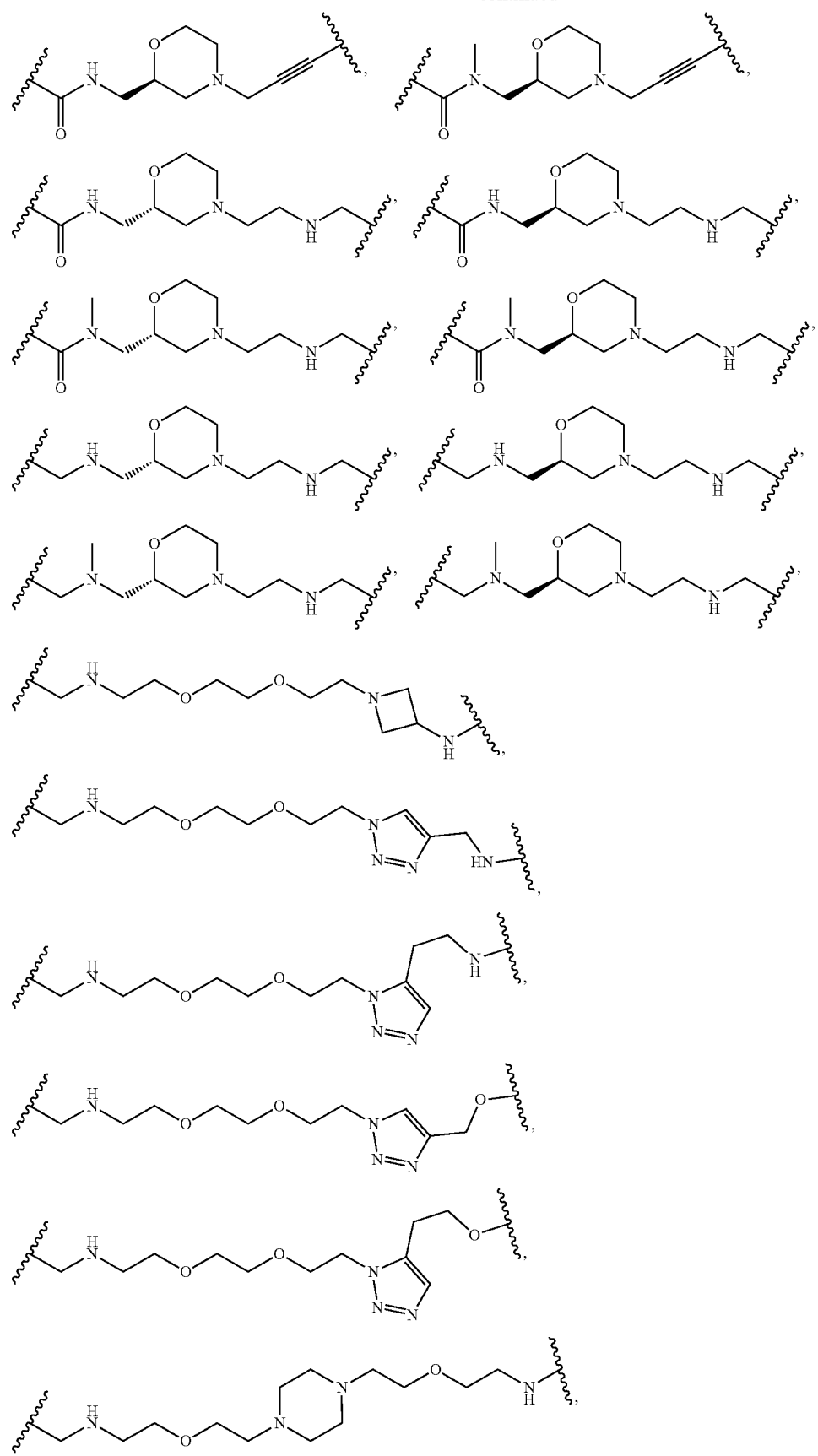

-continued
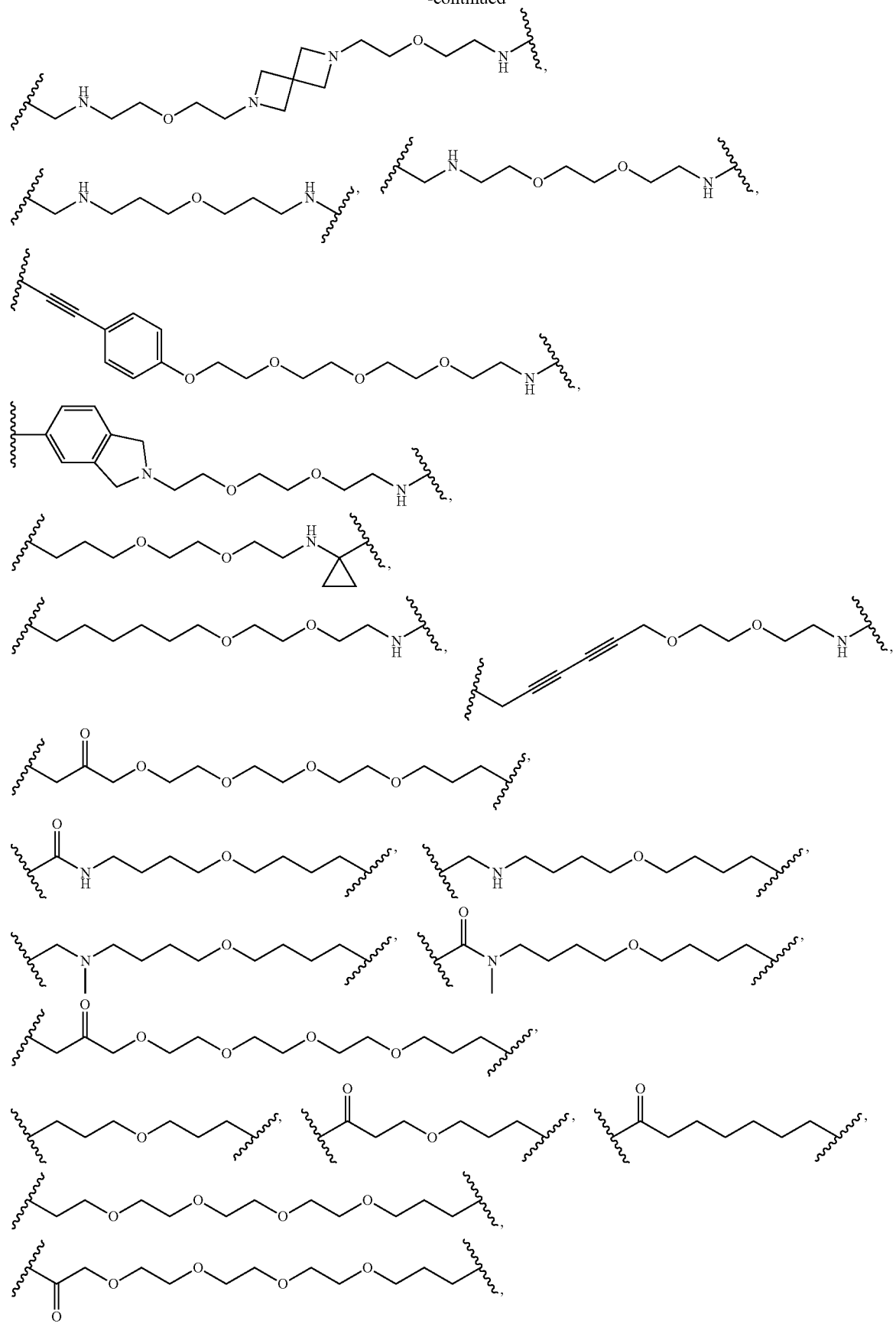

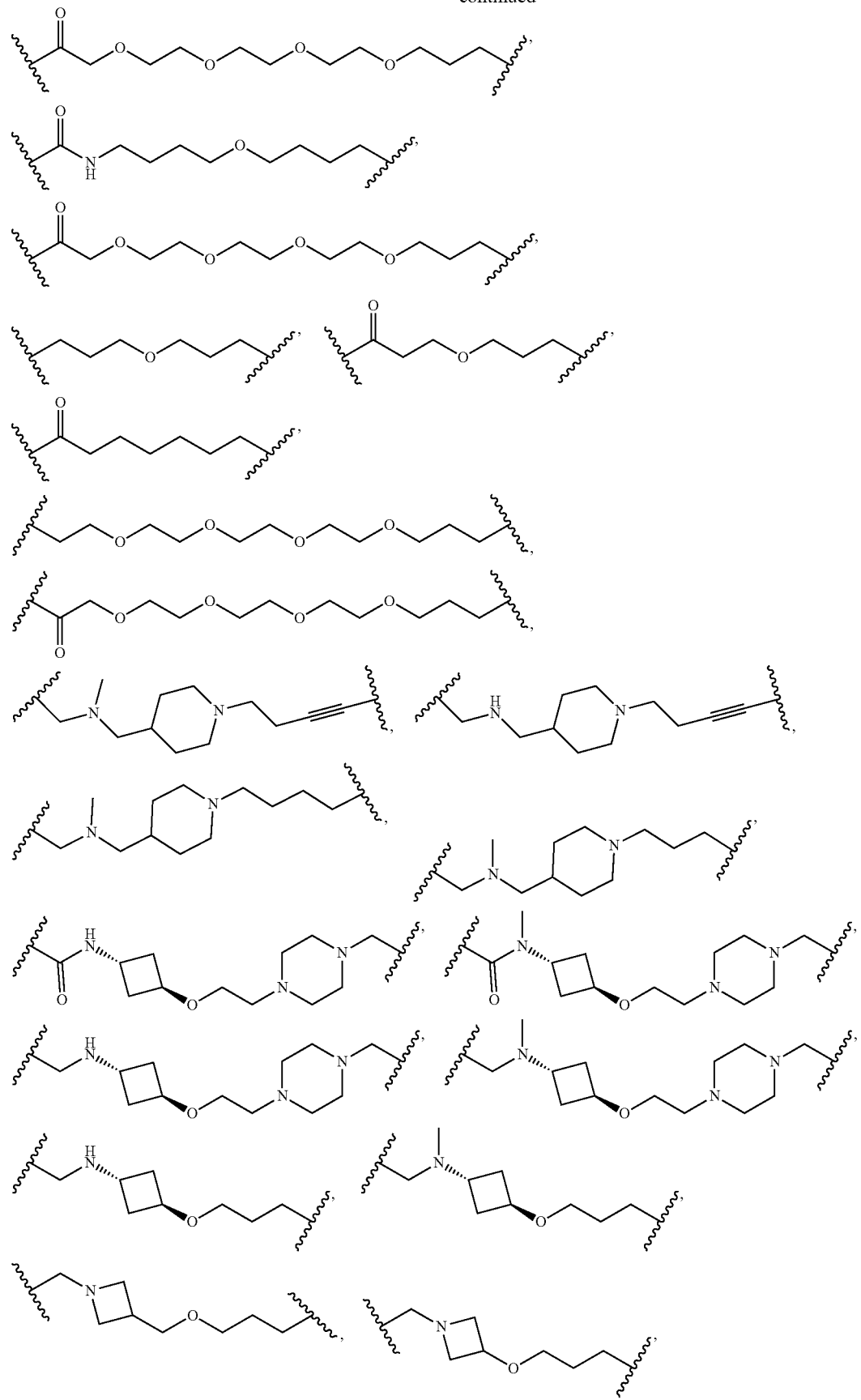

-continued
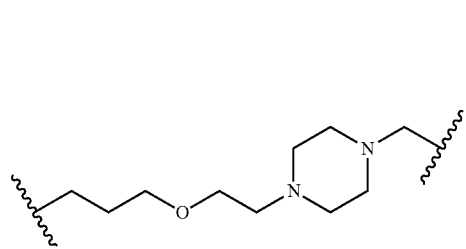
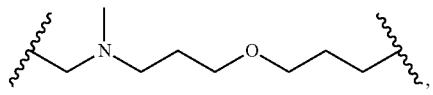
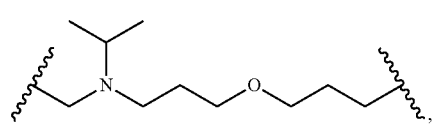
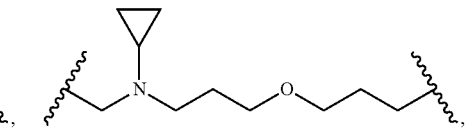
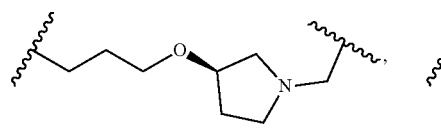
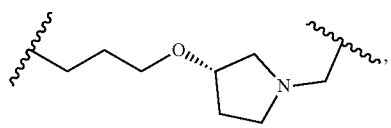
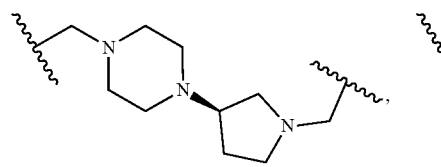
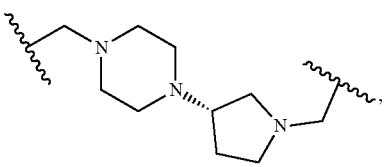
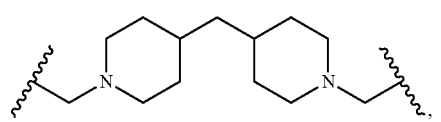
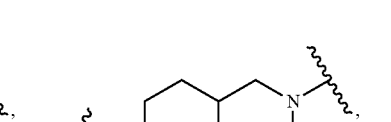
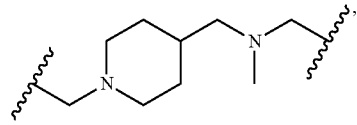
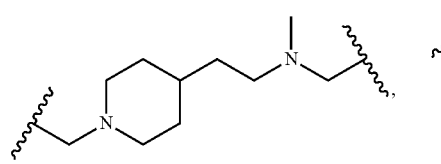
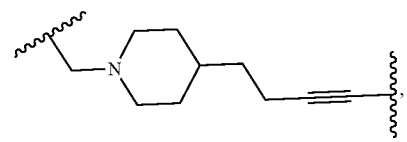
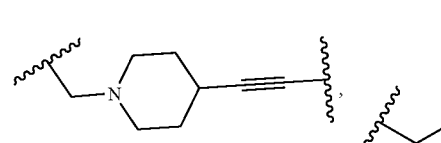
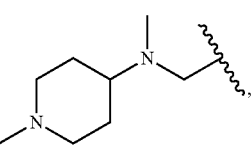
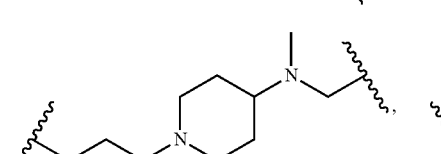
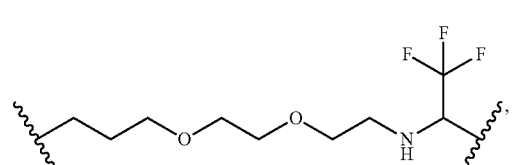
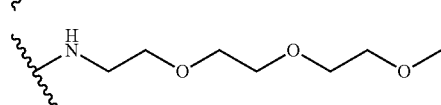
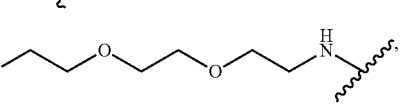
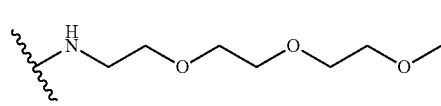
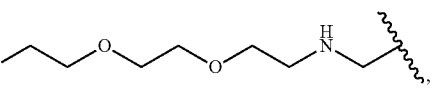
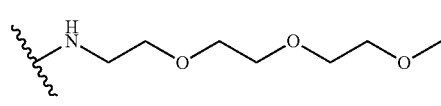
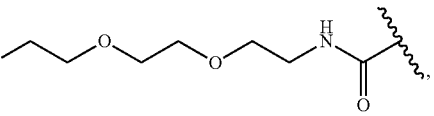

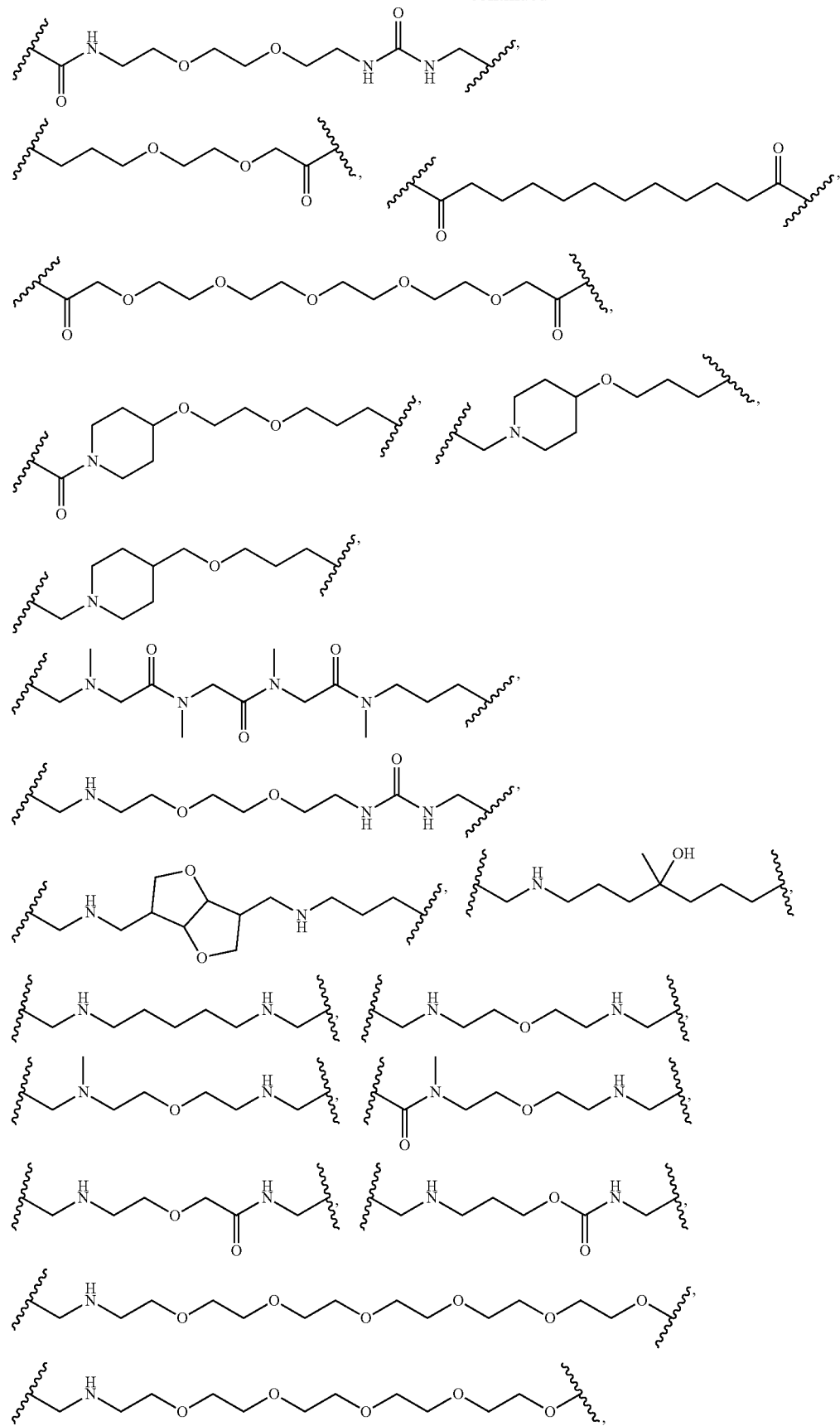

-continued
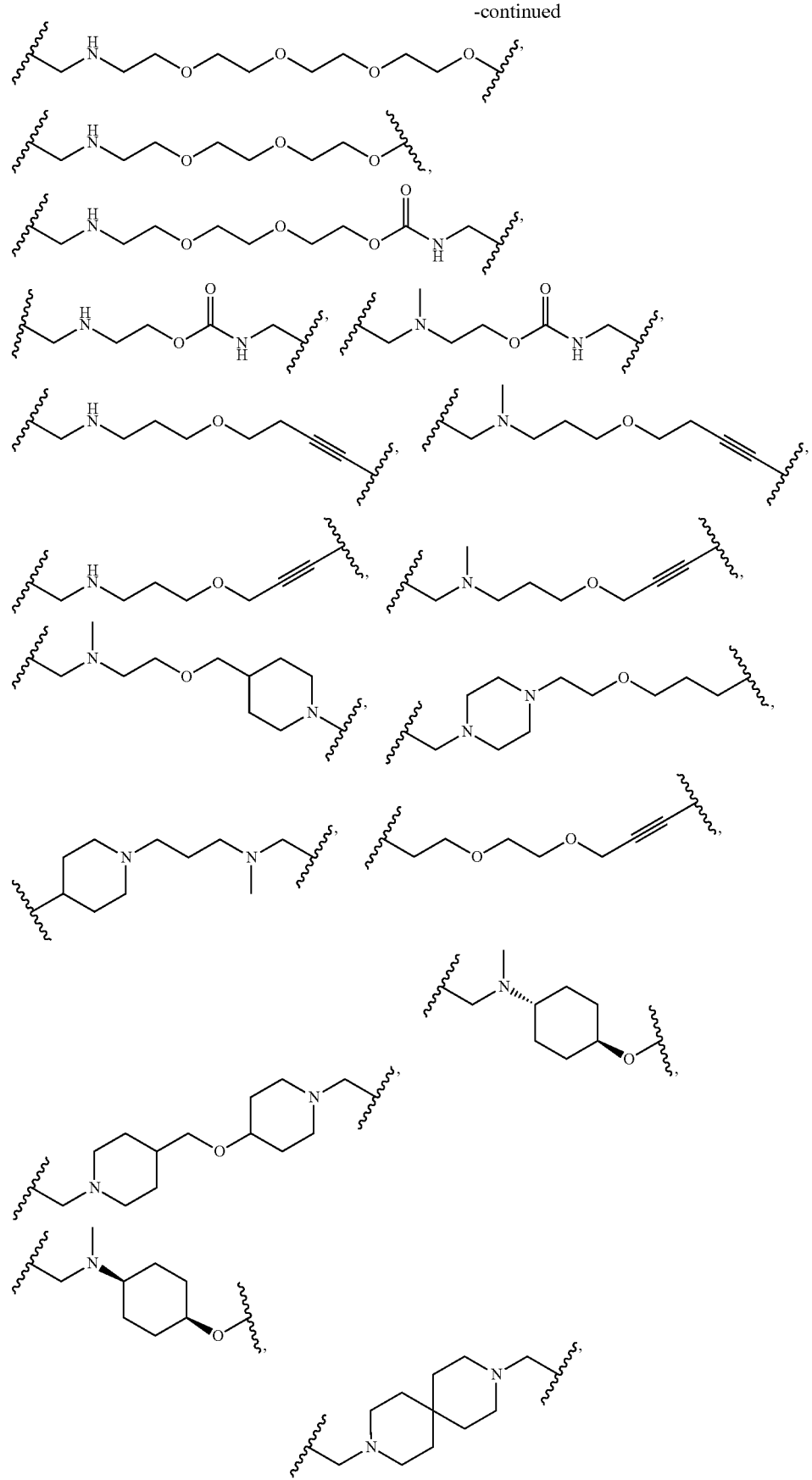

2827 2828
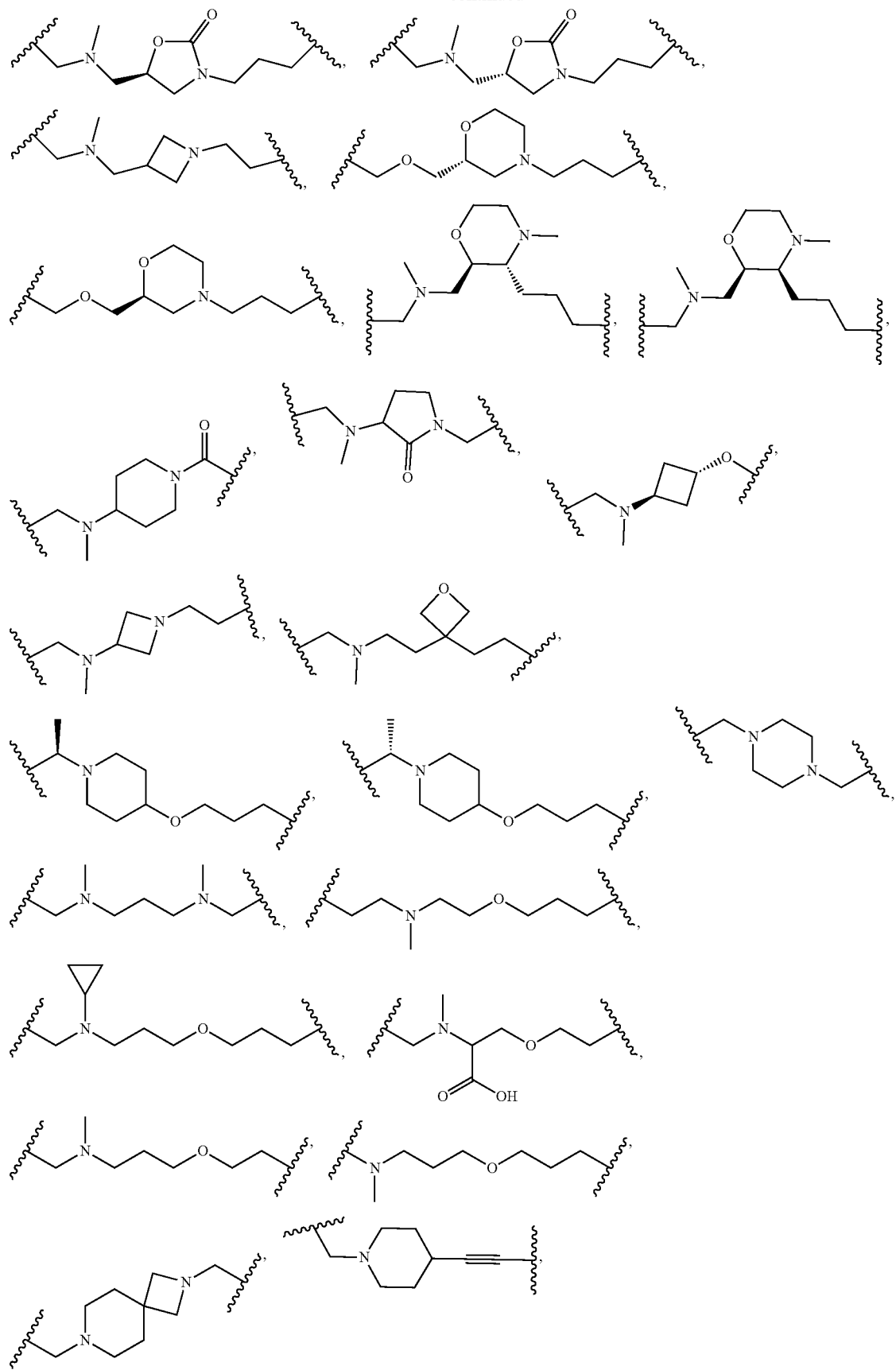

-continued
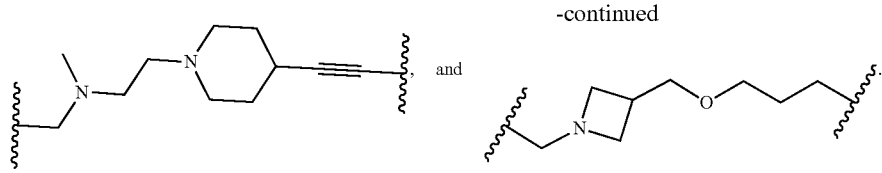
18. The compound according to claim 11, wherein said compound is selected from any one of the following compounds, or a pharmaceutically acceptable salt thereof
| I-# | Structure |
|---|---|
| I-17 | 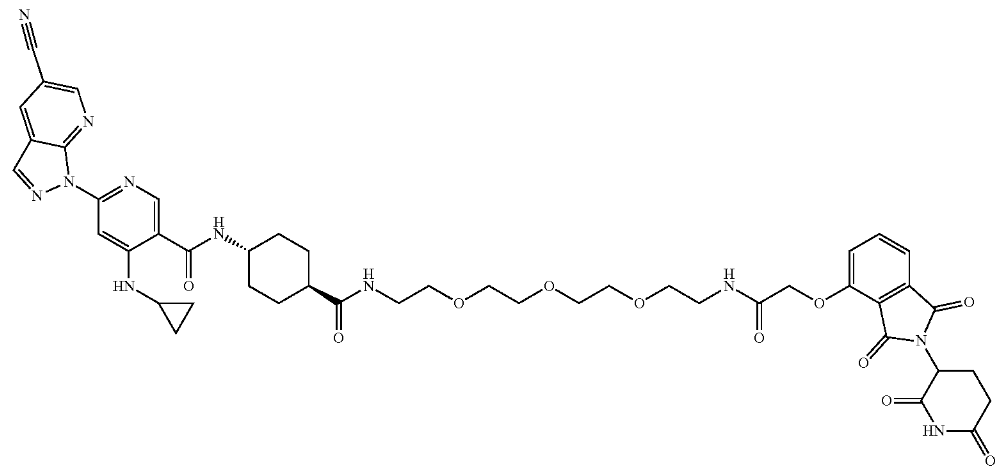 [SMILES: N#Cc1cnc2c(cnn2-c2cc(NC3CC3)c(C(=O)N[C@H]3CC[C@H](C(=O)NCCOCCOCCOCCNC(=O)COc4cccc5c4C(=O)N(C4CCC(=O)NC4=O)C5=O)CC3)cn2)c1] |
| I-18 | 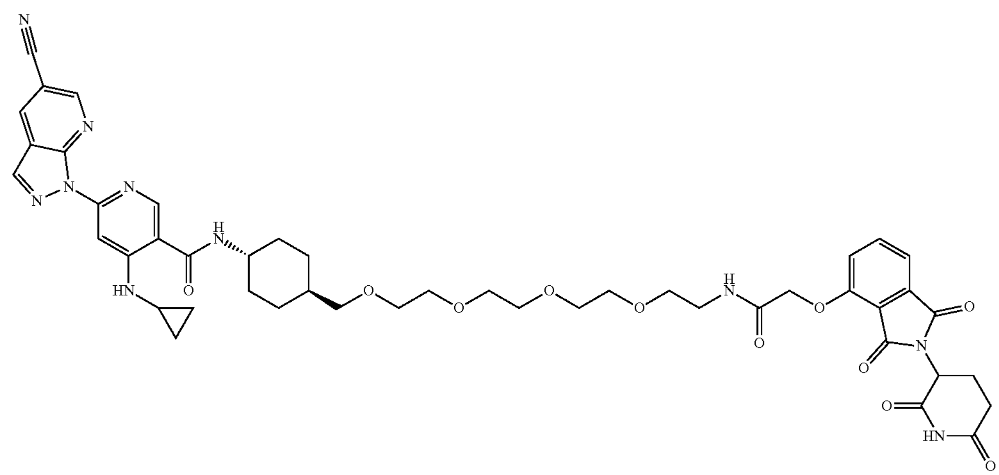 [SMILES: N#Cc1cnc2c(cnn2-c2cc(NC3CC3)c(C(=O)N[C@H]3CC[C@H](COCCOCCOCCOCCNC(=O)COc4cccc5c4C(=O)N(C4CCC(=O)NC4=O)C5=O)CC3)cn2)c1] |
| I-21 | 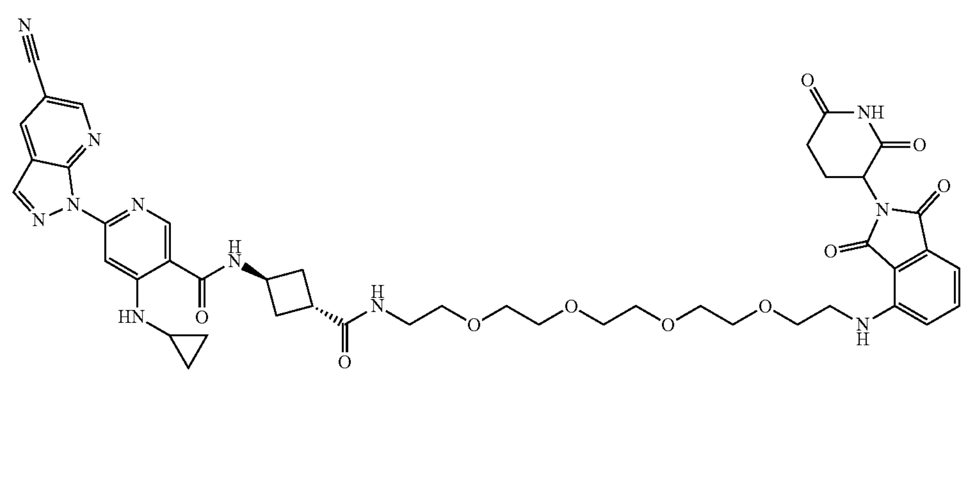 [SMILES: N#Cc1cnc2c(cnn2-c2cc(NC3CC3)c(C(=O)N[C@H]3C[C@H](C(=O)NCCOCCOCCOCCOCCNc4cccc5c4C(=O)N(C4CCC(=O)NC4=O)C5=O)C3)cn2)c1] |

| I-# | Structure |
|---|---|
| I-22 | 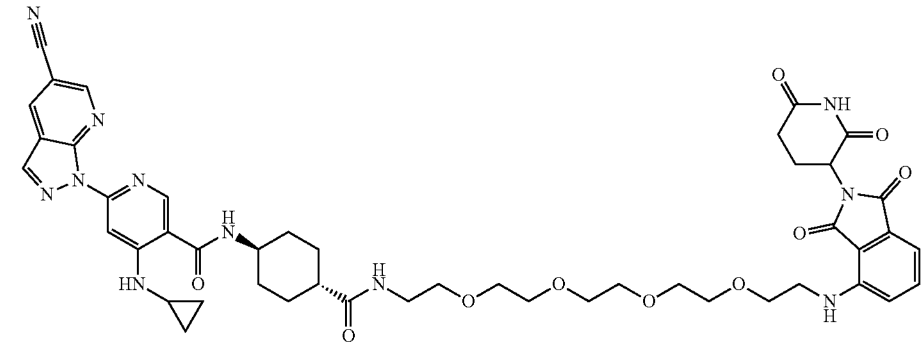 [SMILES: N#Cc1cnc2c(cnn2-c2cc(NC3CC3)c(C(=O)N[C@H]3CC[C@H](C(=O)NCCOCCOCCOCCOCCNc4cccc5c4C(=O)N(C4CCC(=O)NC4=O)C5=O)CC3)cn2)c1] |
| I-27 | 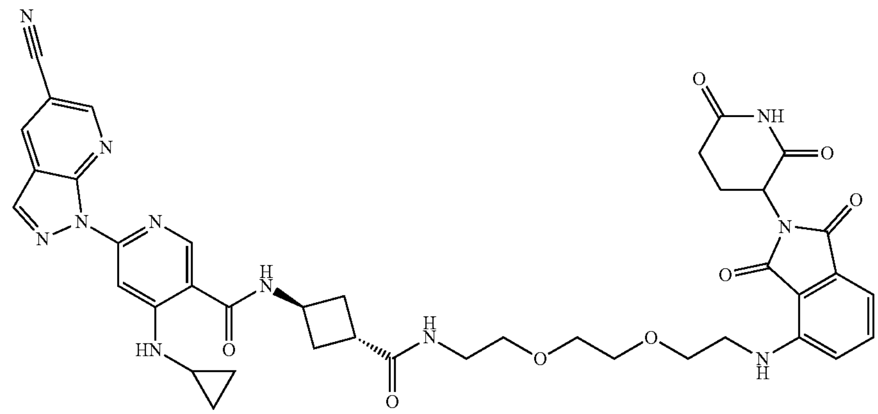 [SMILES: N#Cc1cnc2c(cnn2-c2cc(NC3CC3)c(C(=O)N[C@H]3C[C@H](C(=O)NCCOCCOCCNc4cccc5c4C(=O)N(C4CCC(=O)NC4=O)C5=O)C3)cn2)c1] |
| I-29 | 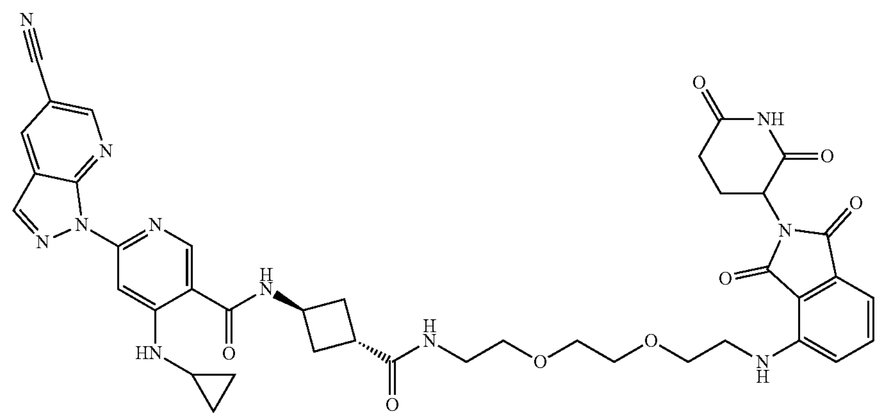 [SMILES: N#Cc1cnc2c(cnn2-c2cc(NC3CC3)c(C(=O)N[C@H]3C[C@H](C(=O)NCCOCCOCCNc4cccc5c4C(=O)N(C4CCC(=O)NC4=O)C5=O)C3)cn2)c1] |
| I-32 | 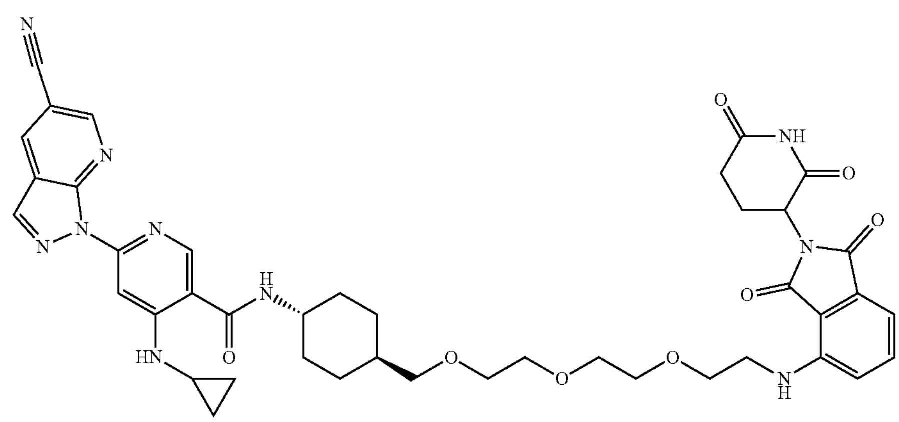 [SMILES: N#Cc1cnc2c(cnn2-c2cc(NC3CC3)c(C(=O)N[C@H]3CC[C@H](COCCOCCOCCNc4cccc5c4C(=O)N(C4CCC(=O)NC4=O)C5=O)CC3)cn2)c1] |

| I-# | Structure |
|---|---|
| I-33 | 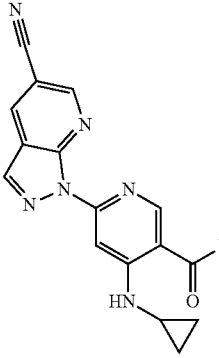 |
| I-34 | 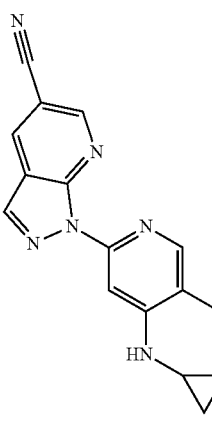 |
| I-35 | 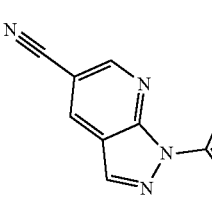 |
| I-36 | 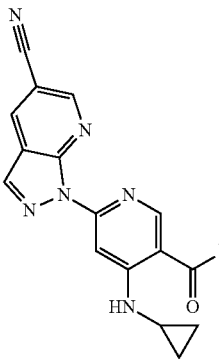 |

-continued
| I-# | Structure |
|---|---|
| I-37 | 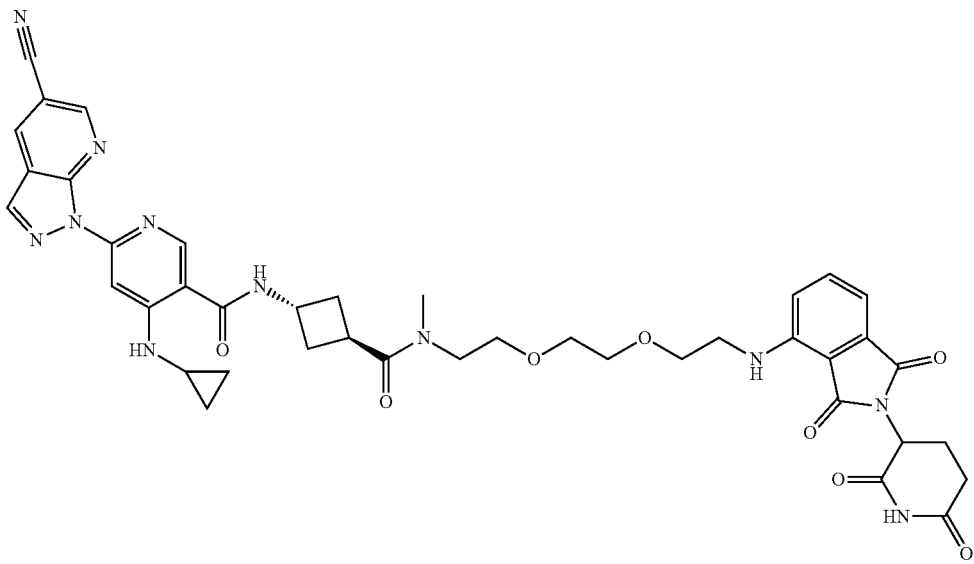 [SMILES: CN(CCOCCOCCNc1cccc2c1C(=O)N(C1CCC(=O)NC1=O)C2=O)C(=O)[C@H]1C[C@H](NC(=O)c2cnc(-n3ncc4cc(C#N)cnc43)cc2NC2CC2)C1] |
| I-38 | 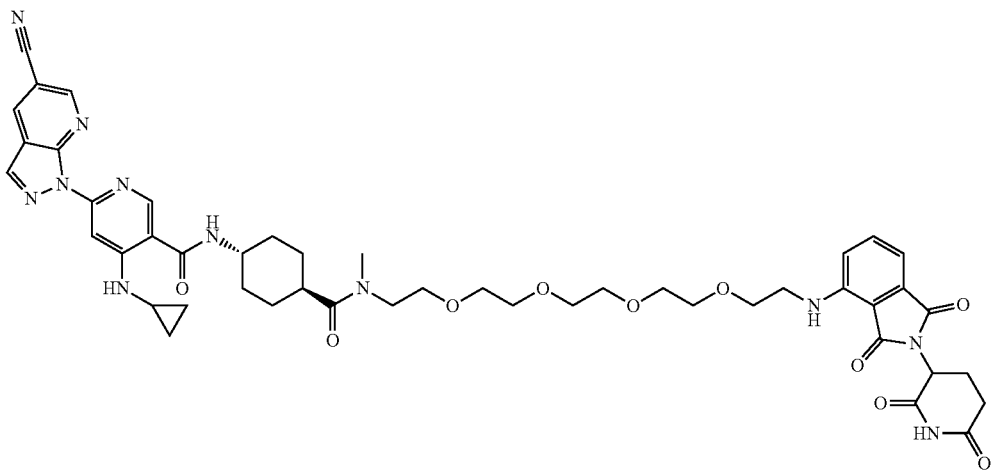 [SMILES: CN(CCOCCOCCOCCOCCNc1cccc2c1C(=O)N(C1CCC(=O)NC1=O)C2=O)C(=O)[C@H]1CC[C@H](NC(=O)c2cnc(-n3ncc4cc(C#N)cnc43)cc2NC2CC2)CC1] |
| I-39 | 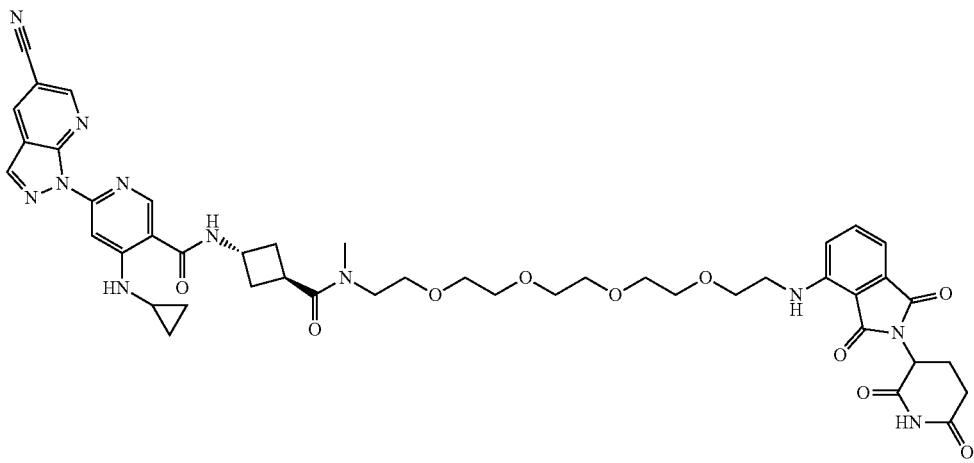 [SMILES: CN(CCOCCOCCOCCOCCNc1cccc2c1C(=O)N(C1CCC(=O)NC1=O)C2=O)C(=O)[C@H]1C[C@H](NC(=O)c2cnc(-n3ncc4cc(C#N)cnc43)cc2NC2CC2)C1] |

| I-# | Structure |
|---|---|
| I-42 | 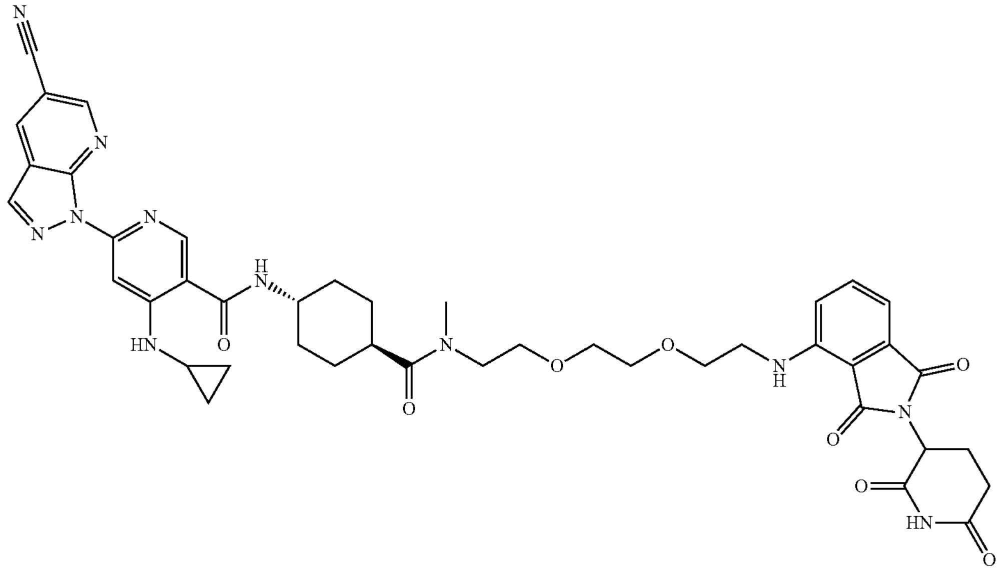 [SMILES: CN(CCOCCOCCNc1cccc2c1C(=O)N(C1CCC(=O)NC1=O)C2=O)C(=O)[C@H]1CC[C@H](NC(=O)c2cnc(-n3ncc4cc(C#N)cnc43)cc2NC2CC2)CC1] |
| I-45 | 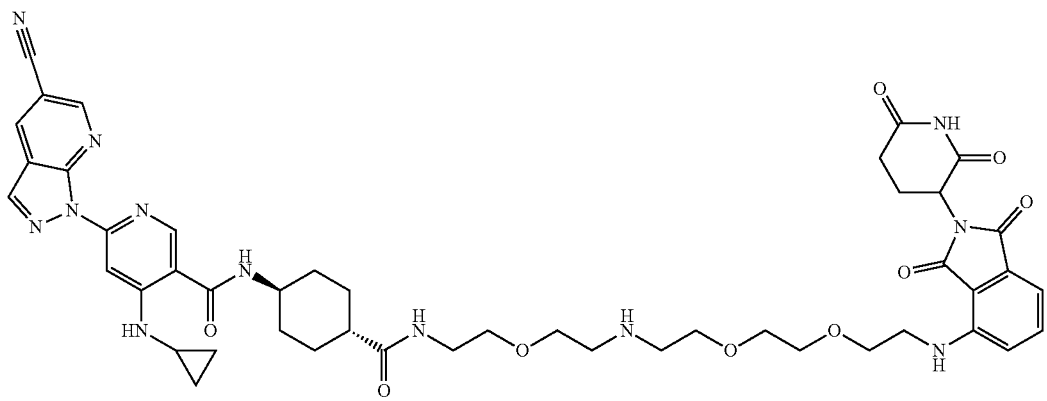 [SMILES: N#Cc1cnc2c(cnn2-c2cc(NC3CC3)c(C(=O)N[C@H]3CC[C@H](C(=O)NCCOCCNCCOCCOCCNc4cccc5c4C(=O)N(C4CCC(=O)NC4=O)C5=O)CC3)cn2)c1] |
| I-46 | 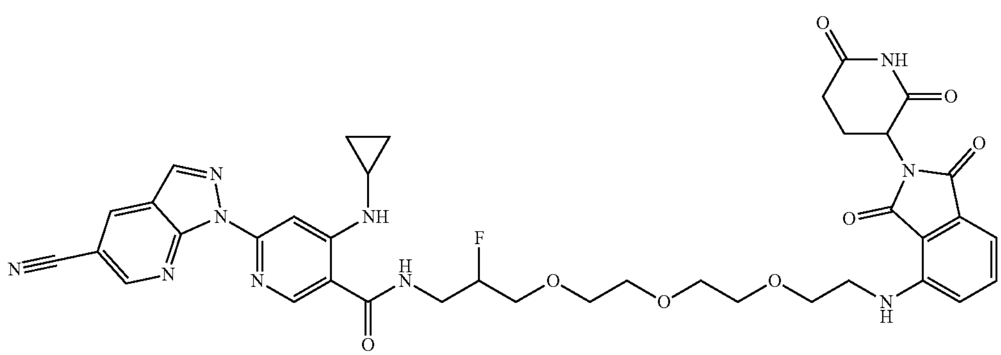 [SMILES: N#Cc1cnc2c(cnn2-c2cc(NC3CC3)c(C(=O)NCC(F)COCCOCCOCCNc3cccc4c3C(=O)N(C3CCC(=O)NC3=O)C4=O)cn2)c1] |
| I-57 | 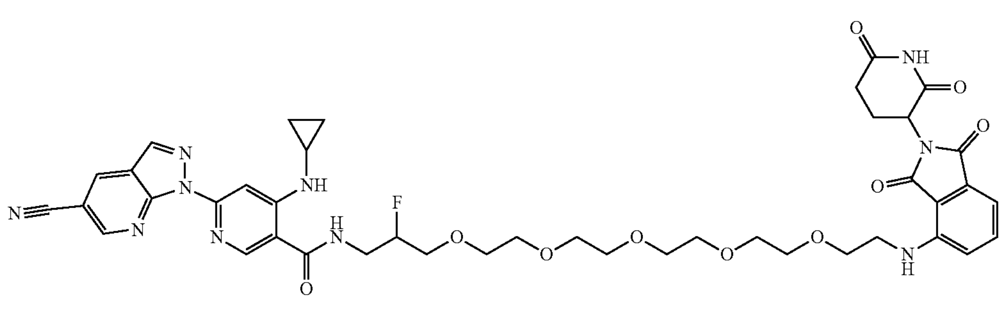 [SMILES: N#Cc1cnc2c(cnn2-c2cc(NC3CC3)c(C(=O)NCC(F)COCCOCCOCCOCCOCCNc3cccc4c3C(=O)N(C3CCC(=O)NC3=O)C4=O)cn2)c1] |

| I-# | Structure |
|---|---|
| I-59 | 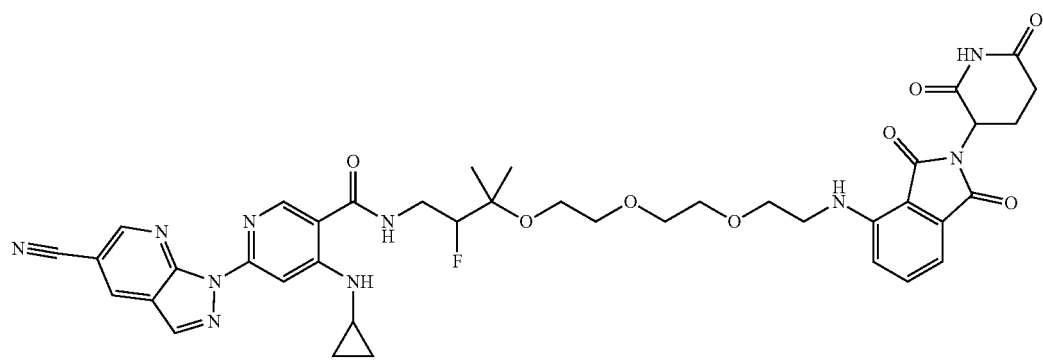 [SMILES: CC(C)(OCCOCCOCCNc1cccc2c1C(=O)N(C1CCC(=O)NC1=O)C2=O)C(F)CNC(=O)c1cnc(-n2ncc3cc(C#N)cnc32)cc1NC1CC1] |
| I-60 | 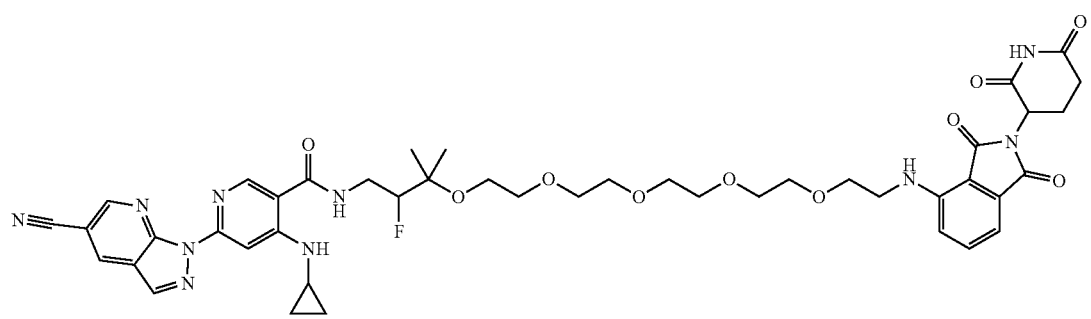 [SMILES: CC(C)(OCCOCCOCCOCCOCCNc1cccc2c1C(=O)N(C1CCC(=O)NC1=O)C2=O)C(F)CNC(=O)c1cnc(-n2ncc3cc(C#N)cnc32)cc1NC1CC1] |
| I-63 | 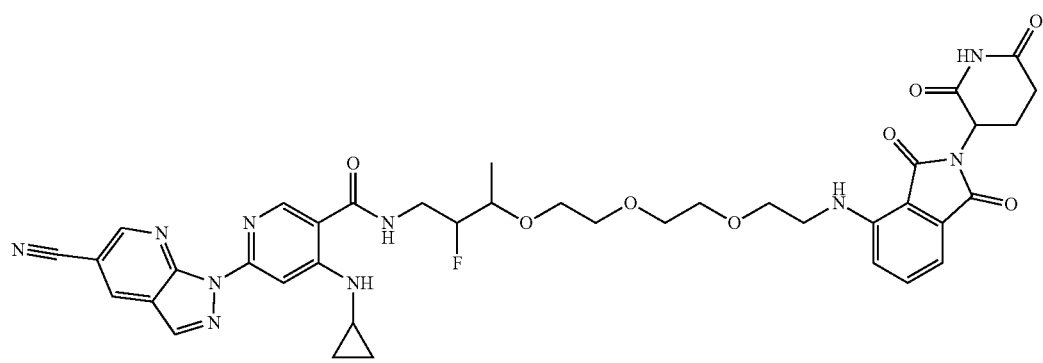 [SMILES: CC(OCCOCCOCCNc1cccc2c1C(=O)N(C1CCC(=O)NC1=O)C2=O)C(F)CNC(=O)c1cnc(-n2ncc3cc(C#N)cnc32)cc1NC1CC1] |
| I-66 | 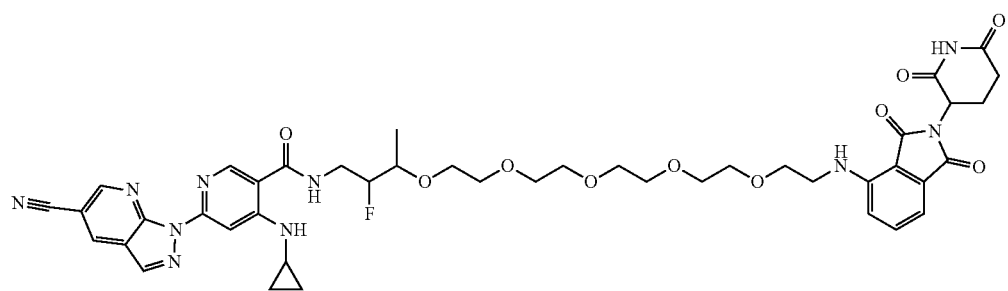 [SMILES: CC(OCCOCCOCCOCCOCCNc1cccc2c1C(=O)N(C1CCC(=O)NC1=O)C2=O)C(F)CNC(=O)c1cnc(-n2ncc3cc(C#N)cnc32)cc1NC1CC1] |
| I-71 | 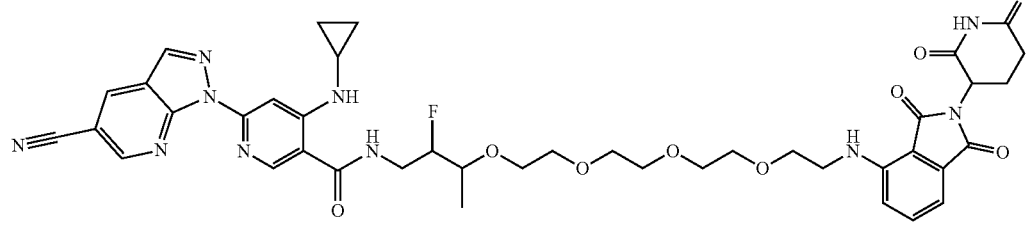 |

| I-# | Structure |
|---|---|
| I-72 | 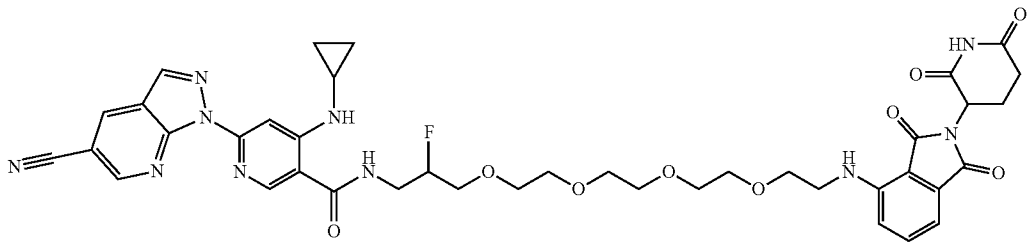 [SMILES: N#Cc1cnc2c(cnn2-c2cc(NC3CC3)c(C(=O)NCC(F)COCCOCCOCCOCCNc3cccc4c3C(=O)N(C3CCC(=O)NC3=O)C4=O)cn2)c1] |
| I-73 | 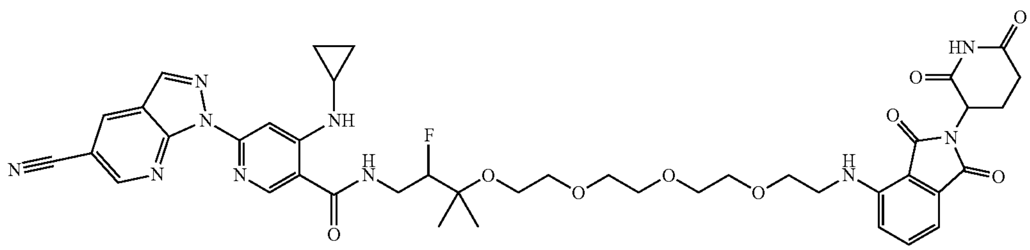 [SMILES: CC(C)(OCCOCCOCCOCCNc1cccc2c1C(=O)N(C1CCC(=O)NC1=O)C2=O)C(F)CNC(=O)c1cnc(-n2ncc3cc(C#N)cnc32)cc1NC1CC1] |
| I-75 | 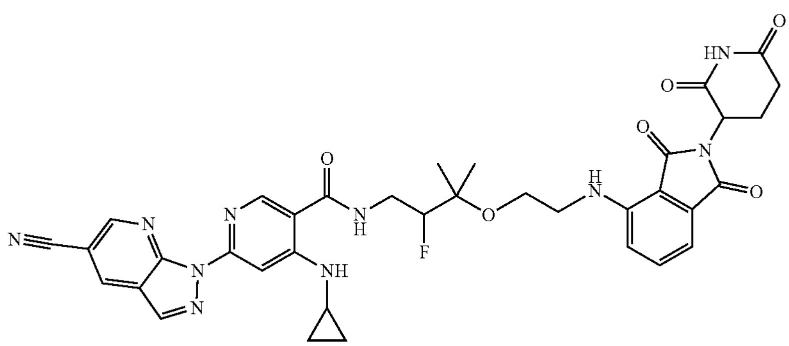 [SMILES: CC(C)(OCCNc1cccc2c1C(=O)N(C1CCC(=O)NC1=O)C2=O)C(F)CNC(=O)c1cnc(-n2ncc3cc(C#N)cnc32)cc1NC1CC1] |
| I-76 | 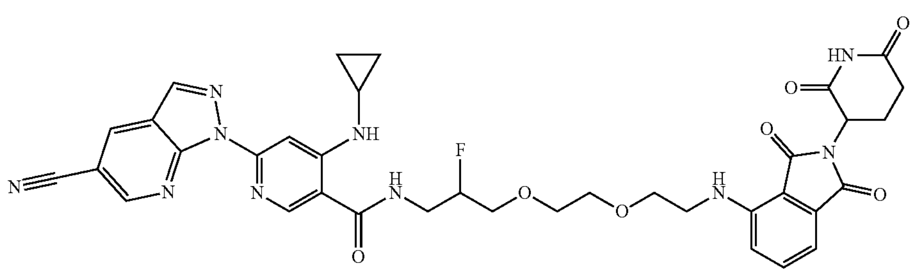 [SMILES: N#Cc1cnc2c(cnn2-c2cc(NC3CC3)c(C(=O)NCC(F)COCCOCCNc3cccc4c3C(=O)N(C3CCC(=O)NC3=O)C4=O)cn2)c1] |
| I-79 | 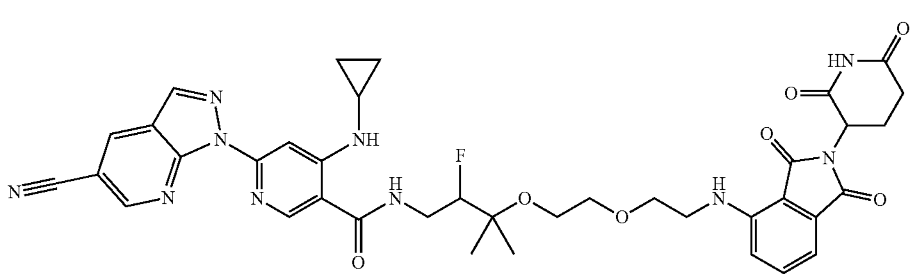 [SMILES: CC(C)(OCCOCCNc1cccc2c1C(=O)N(C1CCC(=O)NC1=O)C2=O)C(F)CNC(=O)c1cnc(-n2ncc3cc(C#N)cnc32)cc1NC1CC1] |

| I-# | Structure |
|---|---|
| I-82 | 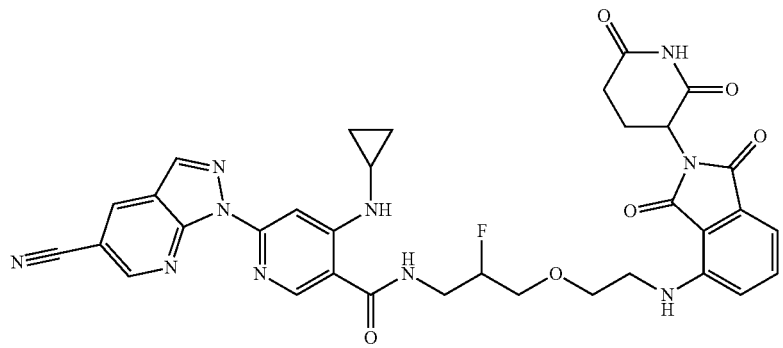 [SMILES: N#Cc1cnc2c(cnn2-c2cc(NC3CC3)c(C(=O)NCC(F)COCCNc3cccc4c3C(=O)N(C3CCC(=O)NC3=O)C4=O)cn2)c1] |
| I-83 | 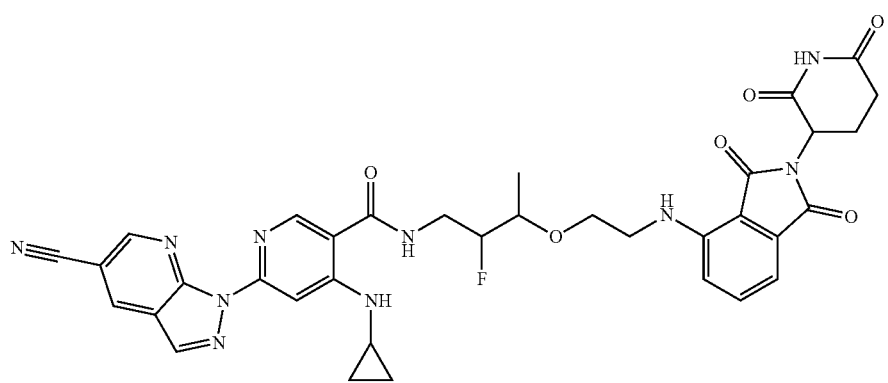 [SMILES: CC(OCCNc1cccc2c1C(=O)N(C1CCC(=O)NC1=O)C2=O)C(F)CNC(=O)c1cnc(-n2ncc3cc(C#N)cnc32)cc1NC1CC1] |
| I-85 | 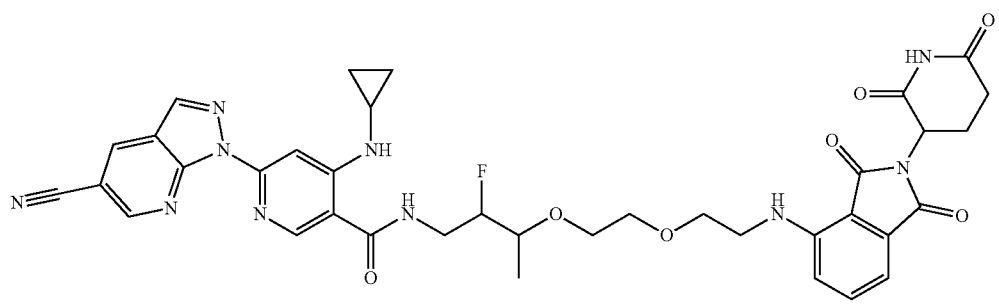 [SMILES: CC(OCCOCCNc1cccc2c1C(=O)N(C1CCC(=O)NC1=O)C2=O)C(F)CNC(=O)c1cnc(-n2ncc3cc(C#N)cnc32)cc1NC1CC1] |
| I-86 | 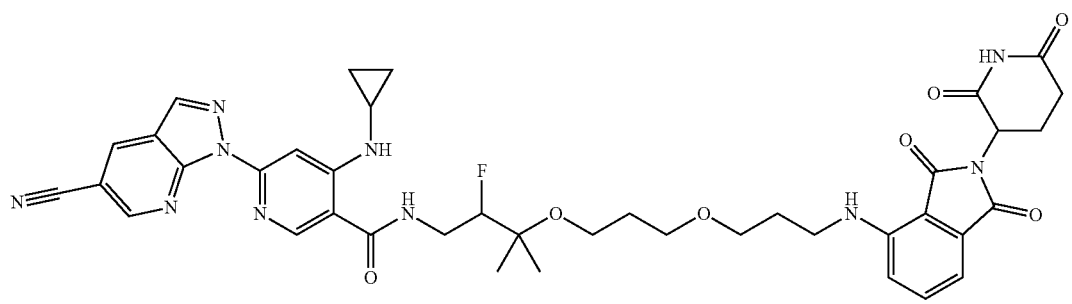 [SMILES: CC(C)(OCCCOCCCNc1cccc2c1C(=O)N(C1CCC(=O)NC1=O)C2=O)C(F)CNC(=O)c1cnc(-n2ncc3cc(C#N)cnc32)cc1NC1CC1] |
| I-88 | 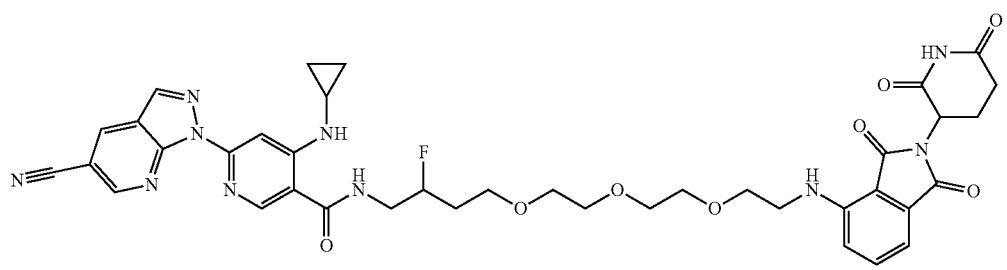 [SMILES: N#Cc1cnc2c(cnn2-c2cc(NC3CC3)c(C(=O)NCC(F)CCOCCOCCOCCNc3cccc4c3C(=O)N(C3CCC(=O)NC3=O)C4=O)cn2)c1] |

| I-# | Structure |
|---|---|
| I-94 | 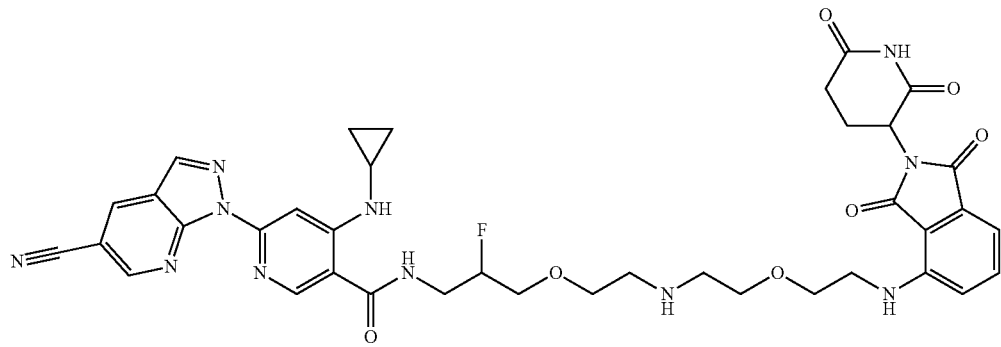 [SMILES: N#Cc1cnc2c(cnn2-c2cc(NC3CC3)c(C(=O)NCC(F)COCCNCCOCCNc3cccc4c3C(=O)N(C3CCC(=O)NC3=O)C4=O)cn2)c1] |
| I-95 | 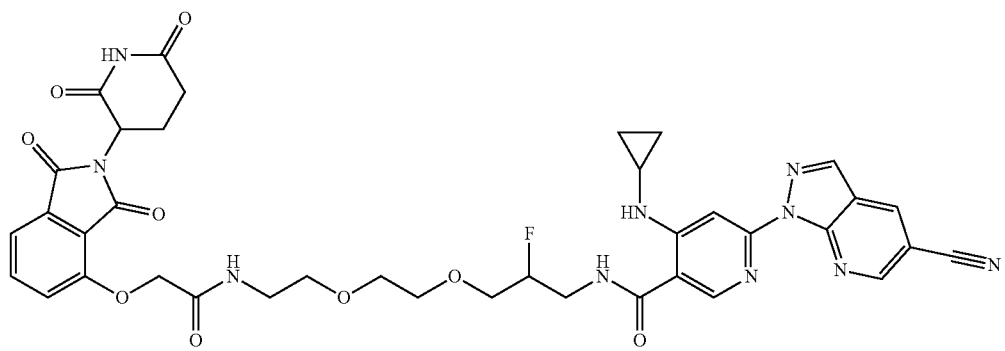 [SMILES: N#Cc1cnc2c(cnn2-c2cc(NC3CC3)c(C(=O)NCC(F)COCCOCCNC(=O)COc3cccc4c3C(=O)N(C3CCC(=O)NC3=O)C4=O)cn2)c1] |
| I-101 | 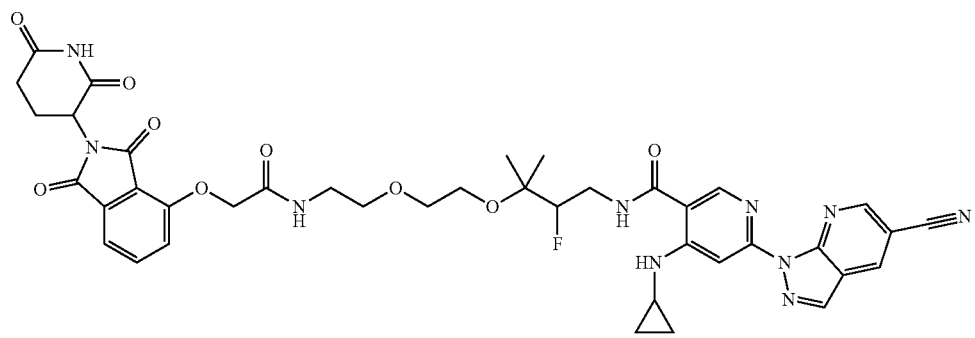 [SMILES: CC(C)(OCCOCCNC(=O)COc1cccc2c1C(=O)N(C1CCC(=O)NC1=O)C2=O)C(F)CNC(=O)c1cnc(-n2ncc3cc(C#N)cnc32)cc1NC1CC1] |
| I-102 | 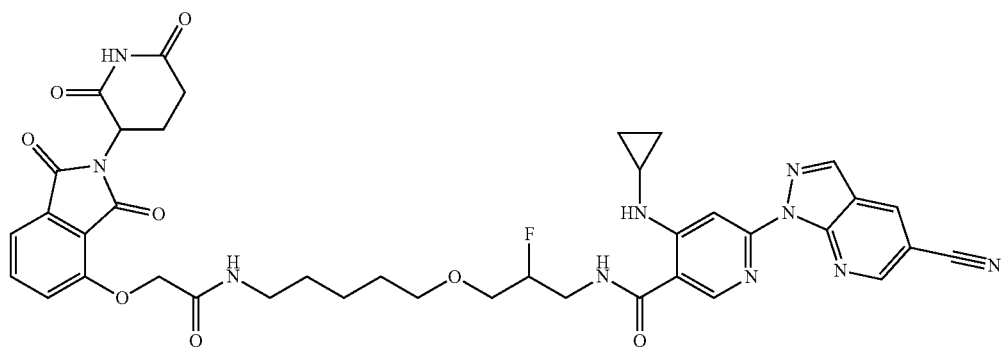 [SMILES: N#Cc1cnc2c(cnn2-c2cc(NC3CC3)c(C(=O)NCC(F)COCCCCCNC(=O)COc3cccc4c3C(=O)N(C3CCC(=O)NC3=O)C4=O)cn2)c1] |

-continued

| I-# | Structure |
|---|---|
| I-118 | 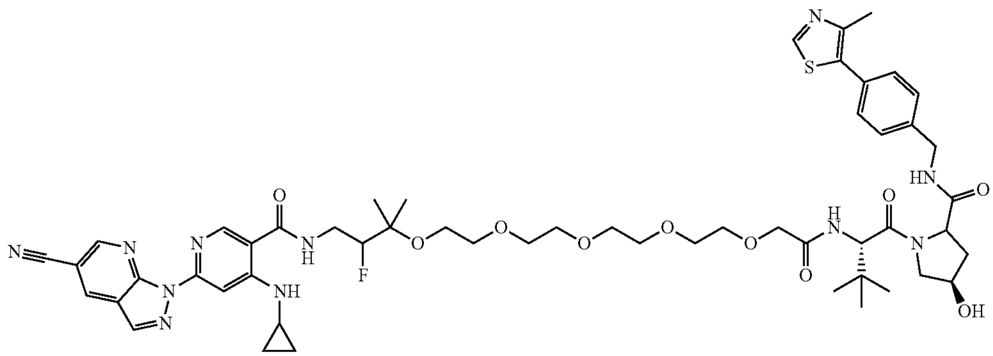 [SMILES: Cc1ncsc1-c1ccc(CNC(=O)C2C[C@@H](O)CN2C(=O)[C@@H](NC(=O)COCCOCCOCCOCCOC(C)(C)C(F)CNC(=O)c2cnc(-n3ncc4cc(C#N)cnc43)cc2NC2CC2)C(C)(C)C)cc1] |
| I-121 | 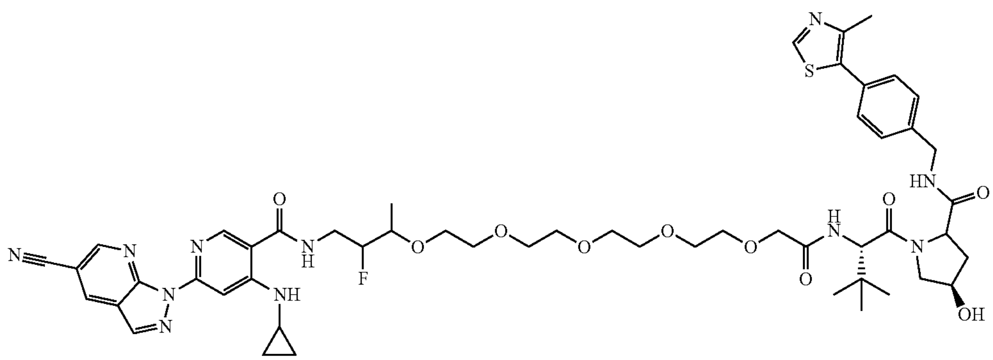 [SMILES: Cc1ncsc1-c1ccc(CNC(=O)C2C[C@@H](O)CN2C(=O)[C@@H](NC(=O)COCCOCCOCCOCCOC(C)C(F)CNC(=O)c2cnc(-n3ncc4cc(C#N)cnc43)cc2NC2CC2)C(C)(C)C)cc1] |
| I-122 | 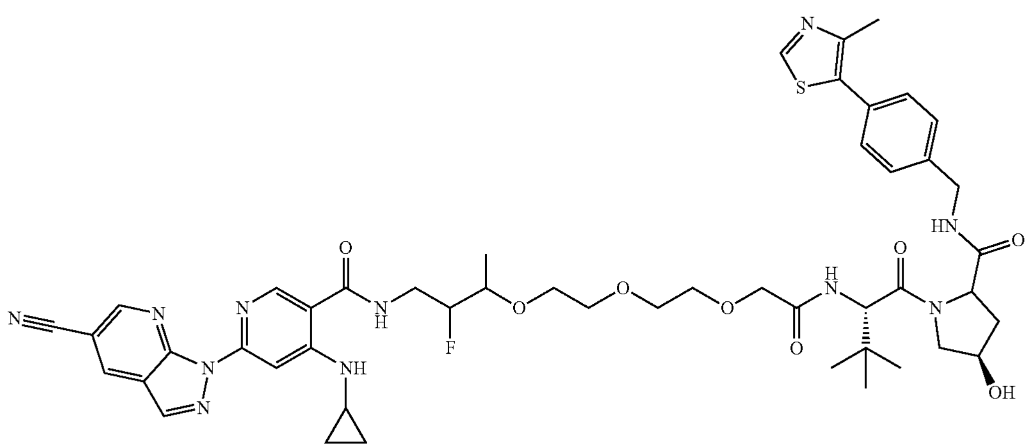 [SMILES: Cc1ncsc1-c1ccc(CNC(=O)C2C[C@@H](O)CN2C(=O)[C@@H](NC(=O)COCCOCCOC(C)C(F)CNC(=O)c2cnc(-n3ncc4cc(C#N)cnc43)cc2NC2CC2)C(C)(C)C)cc1] |
| I-129 | 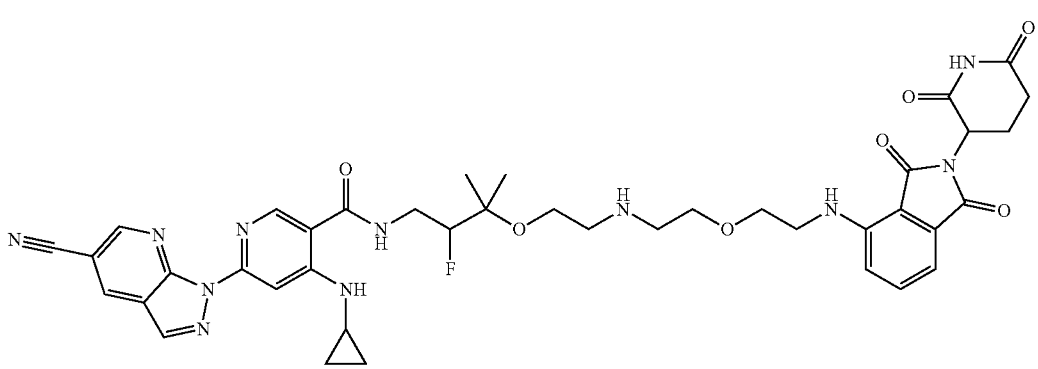 [SMILES: CC(C)(OCCNCCOCCNc1cccc2c1C(=O)N(C1CCC(=O)NC1=O)C2=O)C(F)CNC(=O)c1cnc(-n2ncc3cc(C#N)cnc32)cc1NC1CC1] |

| I-# | Structure |
|---|---|
| I-131 | 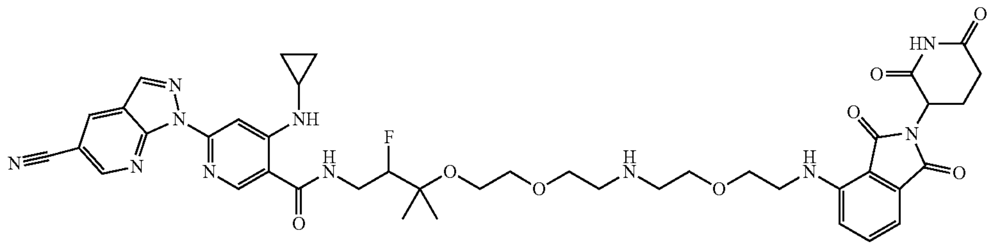 [SMILES: CC(C)(OCCOCCNCCOCCNc1cccc2c1C(=O)N(C1CCC(=O)NC1=O)C2=O)C(F)CNC(=O)c1cnc(-n2ncc3cc(C#N)cnc32)cc1NC1CC1] |
| I-173 | 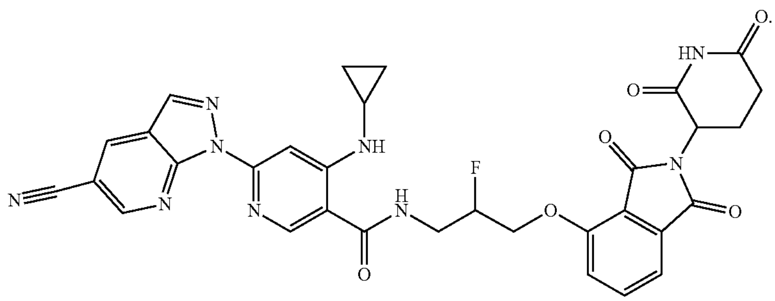 [SMILES: N#Cc1cnc2c(cnn2-c2cc(NC3CC3)c(C(=O)NCC(F)COc3cccc4c3C(=O)N(C3CCC(=O)NC3=O)C4=O)cn2)c1] |

19. A pharmaceutical composition comprising a compound according to claim 11, and a pharmaceutically acceptable carrier, adjuvant, or vehicle.

20. The pharmaceutical composition according to claim 19, further comprising an additional therapeutic agent.

* * * * *